(12) United States Patent
Sato

(10) Patent No.: US 11,244,760 B2
(45) Date of Patent: Feb. 8, 2022

(54) PREDICTION DEVICE BASED ON INTER-ORGAN CROSS TALK SYSTEM

(71) Applicant: KARYDO THERAPEUTIX, INC., Tokyo (JP)

(72) Inventor: Narutoku Sato, Kyoto (JP)

(73) Assignee: KARYDO THERAPEUTIX, INC., Tokyo (JP)

(*) Notice: Subject to any disclaimer, the term of this patent is extended or adjusted under 35 U.S.C. 154(b) by 967 days.

(21) Appl. No.: 15/738,924

(22) PCT Filed: Jun. 24, 2016

(86) PCT No.: PCT/JP2016/069564
§ 371 (c)(1),
(2) Date: Dec. 21, 2017

(87) PCT Pub. No.: WO2016/208776
PCT Pub. Date: Dec. 29, 2016

(65) Prior Publication Data
US 2019/0272924 A1    Sep. 5, 2019

(30) Foreign Application Priority Data

Jun. 25, 2015  (JP) .............................. JP2015-128041
Nov. 19, 2015  (JP) .............................. JP2015-226435

(51) Int. Cl.
| | | |
|---|---|---|
| *G16H 50/20* | (2018.01) | |
| *G16H 50/30* | (2018.01) | |
| *G16H 50/70* | (2018.01) | |
| *A61B 5/02* | (2006.01) | |
| *A61B 5/00* | (2006.01) | |
| *G16B 20/00* | (2019.01) | |
| *G01N 33/50* | (2006.01) | |
| *C12Q 1/6883* | (2018.01) | |
| *G01N 33/48* | (2006.01) | |
| *C12Q 1/6886* | (2018.01) | |
| *G16B 25/00* | (2019.01) | |
| *G16B 50/30* | (2019.01) | |
| *G16B 40/00* | (2019.01) | |

(52) U.S. Cl.
CPC .............. *G16H 50/20* (2018.01); *A61B 5/02* (2013.01); *A61B 5/4088* (2013.01); *C12Q 1/6883* (2013.01); *C12Q 1/6886* (2013.01); *G01N 33/48* (2013.01); *G01N 33/50* (2013.01); *G16B 20/00* (2019.02); *G16H 50/30* (2018.01); *G16H 50/70* (2018.01); *G16B 25/00* (2019.02); *G16B 40/00* (2019.02); *G16B 50/30* (2019.02); *Y02A 90/10* (2018.01)

(58) Field of Classification Search
CPC ........ G16H 50/20; G16H 50/30; G16H 50/70; G16B 20/00; A61B 5/02; A61B 5/4088; C12Q 1/6883; C12Q 1/6886; G01N 33/48; G01N 33/50

USPC .......................................................... 702/19
See application file for complete search history.

(56) References Cited

U.S. PATENT DOCUMENTS

| | | |
|---|---|---|
| 9,970,946 B2 | 5/2018 | Uchiyama et al. |
| 2003/0017481 A1 | 1/2003 | Golub et al. |
| 2004/0091498 A1 | 5/2004 | Zhang et al. |
| 2004/0185503 A1 | 9/2004 | Yamanouchi et al. |
| 2005/0079514 A1 | 4/2005 | Liew |
| 2005/0112701 A1 | 5/2005 | Arndt et al. |
| 2005/0159896 A1 | 7/2005 | Ishikawa et al. |
| 2006/0008804 A1 | 1/2006 | Chibout et al. |
| 2006/0088876 A1 | 4/2006 | Bauer |
| 2007/0161125 A1 | 7/2007 | Rosenfeld et al. |
| 2009/0061454 A1 | 3/2009 | Brody et al. |
| 2009/0291434 A1 | 11/2009 | Cowens et al. |
| 2010/0322850 A1 | 12/2010 | Eizirik et al. |
| 2013/0023054 A1 | 1/2013 | Meikle et al. |
| 2013/0045494 A1 | 2/2013 | Anderberg et al. |
| 2013/0045873 A1 | 2/2013 | Hood et al. |
| 2013/0157883 A1 | 6/2013 | Keller et al. |
| 2013/0230871 A1 | 9/2013 | Anderberg et al. |
| 2013/0259879 A1 | 10/2013 | Baumhof et al. |
| 2014/0100125 A1 | 4/2014 | Vanburen et al. |
| 2014/0170677 A1 | 6/2014 | Klinguer-Hamour et al. |
| 2014/0286953 A1 | 9/2014 | Sasu et al. |
| 2015/0285821 A1 | 10/2015 | Uchiyama et al. |
| 2019/0250170 A1 | 8/2019 | Anderberg et al. |

FOREIGN PATENT DOCUMENTS

| | | |
|---|---|---|
| CN | 101611319 | 12/2009 |
| CN | 102558336 | 7/2012 |
| CN | 102884205 | 1/2013 |

(Continued)

OTHER PUBLICATIONS

Partial Supplementary European Search Report dated Dec. 12, 2019 in European Patent Application No. 17775147.6.

(Continued)

*Primary Examiner* — Jerry Lin

(74) *Attorney, Agent, or Firm* — Wenderoth, Lind & Ponack, L.L.P.

(57) ABSTRACT

An apparatus 1 comprises a subject data obtaining unit 11 for obtaining subject data M4 of an inter-organ cross talk indicator in each organ other than a specific organ, a pattern similarity calculation unit 12 for calculating, by comparing the subject data M4 with standard data 1 of the inter-organ cross talk indicator, similarity of patterns of the inter-organ cross talk indicators, and a prediction unit 13 for predicting the presence of a specific disease and/or the stage of the specific disease by using the similarity as a measure.

15 Claims, 1853 Drawing Sheets

Specification includes a Sequence Listing.

(56) References Cited

FOREIGN PATENT DOCUMENTS

| | | |
|---|---|---|
| CN | 103717620 | 4/2014 |
| CN | 105004864 | 10/2015 |
| DE | 44 00 745 | 7/1995 |
| EP | 1 124 572 | 8/2001 |
| EP | 1 466 925 | 10/2004 |
| EP | 2 479 572 | 7/2012 |
| EP | 3 316 159 | 5/2018 |
| EP | 3 438 282 | 2/2019 |
| JP | 2001-17171 | 1/2001 |
| JP | 2001-37486 | 2/2001 |
| JP | 2002-516107 | 6/2002 |
| JP | 2004-187620 | 7/2004 |
| JP | 2005-500803 | 1/2005 |
| JP | 2005-508505 | 3/2005 |
| JP | 2005-510240 | 4/2005 |
| JP | 2005-518810 | 6/2005 |
| JP | 2005-229834 | 9/2005 |
| JP | 2005-323573 | 11/2005 |
| JP | 2007-521799 | 8/2007 |
| JP | 2008-512104 | 4/2008 |
| JP | 2008-518626 | 6/2008 |
| JP | 2011-50250 | 3/2011 |
| JP | 2012-507012 | 3/2012 |
| JP | 2013-126427 | 6/2013 |
| JP | 2013-215201 | 10/2013 |
| JP | 2013-538565 | 10/2013 |
| JP | 2013-541323 | 11/2013 |
| JP | 2014-122170 | 7/2014 |
| WO | 99/61622 | 12/1999 |
| WO | 00/23100 | 4/2000 |
| WO | 02/20718 | 3/2002 |
| WO | 03/040404 | 5/2003 |
| WO | 03/046180 | 6/2003 |
| WO | 03/057874 | 7/2003 |
| WO | 03/074731 | 9/2003 |
| WO | 03/085548 | 10/2003 |
| WO | 2004/005934 | 1/2004 |
| WO | 2005/045044 | 5/2005 |
| WO | 2005/106493 | 11/2005 |
| WO | 2005/114207 | 12/2005 |
| WO | 2006/027265 | 3/2006 |
| WO | 2007/011412 | 1/2007 |
| WO | 2008/008430 | 1/2008 |
| WO | 2010/048670 | 5/2010 |
| WO | 2010/100633 | 9/2010 |
| WO | 2012/012693 | 1/2012 |
| WO | 2012/012725 | 1/2012 |
| WO | 2013/011059 | 1/2013 |
| WO | 2013/011063 | 1/2013 |
| WO | 2014/093622 | 6/2014 |
| WO | 2015/069900 | 5/2015 |
| WO | 2015/184011 | 12/2015 |

OTHER PUBLICATIONS

Extended European Search Report dated Jan. 7, 2020 in European Patent Application No. 17775337.3.

Han et al., "Apelin: A novel inhibitor of vascular calcification in chronic kidney disease", Atherosclerosis, 2015, vol. 244, pp. 1-8.

Sagiroglu et al., "Effects of apelin and leptin on renal functions following renal ischemia/reperfusion: An experimental study", Experimental and Therapeutic Medicine, 2012, vol. 3, No. 5, pp. 908-914.

Chen et al., "Apelin protects against acute renal injury by inhibiting TGF-β1", Biochimica et Biophysica Acta, 2015, vol. 1852, No. 7, pp. 1278-1287.

Clarkson et al., "Serum and Urinary Fibrin/Fibrinogen Degradation Products in Glomerulonephritis", British Medical Journal, 1971, vol. 3, pp. 447-451.

Crotti et al., "Osteoimmunology: Major and Costimulatory Pathway Expression Associated with Chronic Inflammatory Induced Bone Loss", Journal of Immunology Research, 2015, vol. 2015, pp. 1-13.

Goettsch et al., "The Osteoclast-Associated Receptor (OSCAR) Is a Novel Receptor Regulated by Oxidized Low-Density Lipoprotein in Human Endothelial Cells", Endocrinology, 2011, vol. 152, No. 12, pp. 4915-4926.

Ndongo-Thiam et al., "Levels of soluble osteoclast-associated receptor (sOSCAR) in rheumatoid arthritis: link to disease severity and cardiovascular risk", Annals of the Rheumatic Diseases, 2014, vol. 73, No. 6, pp. 1276-1277.

Partial Supplementary European Search Report dated Mar. 13, 2019 in corresponding European Application No. 16814543.1.

Keen et al., "The Genotype-Tissue Expression (GTEx) Project: Linking Clinical Data with Molecular Analysis to Advance Personalized Medicine", Journal of Personalized Medicine, 2015, vol. 5, No. 1, pp. 22-29.

Uhlén et al., "Tissue-based map of the human proteome", SCIENCE, Jan. 2015, vol. 347, Issue No. 6220, pp. 1260419-1 to 1260419-9.

Kim et al., "A draft map of the human proteome", vol. 509, No. 7502, NATURE, May 2014, pp. 575-581.

Uhlén et al., "Transcriptomics resources of human tissues and organs", Molecular Systems Biology, 2016, vol. 12:862, No. 4, pp. 1-12.

Kozawa et al., "The Body-wide Transcriptome Landscape of Disease Models", iScience, vol. 2, 2018, pp. 238-268.

International Search Report dated Mar. 21, 2017 in International (PCT) Application No. PCT/JP2017/002406.

Oh et al., "Profile of Human β-Defensins 1,2 and Proinflammatory Cytokines (TNF-α, IL-6) in Patients with Chronic Kidney Disease", Kidney & Blood Pressure Research, vol. 37, 2013, pp. 602-610.

Koike et al., "Identification of α-HNP-3 defensin in diabetes mellitus patient's urine—Potential marker for early diagnosis of diabetic nephropathy-", Journal of Analytical Bio-science, vol. 30, No. 4, 2007, pp. 334-339, with English summary, cited in ISR.

Orita, "Recent progress in protein restriction therapy for chronic renal insufficiency", Journal of Clinical and Experimental Medicine, vol. 171, No. 6, 1994, pp. 607-610, cited in ISR.

Mikiko Funakoshi et al., "Proline-rich Protein (PRP) Levels In Inflammatory Diseases", The Journal Japan Atherosclerosis Society, vol. 14, No. 6, 1987, pp. 1249-1250, with English summary, cited in ISR.

Lu et al., "Inductively coupled mass spectrometry analysis of biometals in conditional Hamp1 and Hamp1 and Hamp2 transgenic mouse models", Transgenic Res., vol. 24, 2015, pp. 765-773.

Lysaght, "Maintenance Dialysis Population Dynamics: Current Trends and Long-Term Implications", J Am Soc Nephrol, vol. 13, 2002, pp. S37-S40.

Sata et al., "New protein in human blood plasma, rich in proline, with lipid-binding properties", Proc. Nat. Acad. Sci. USA, vol. 73, No. 4, Apr. 1976, pp. 1063-1067.

Matsuguch et al., "Molecular Cloning of the cDNA Coding for Proline-Rich Protein (PRP): Identity of PRP as C4b-Binding Protein", Biochemical and Biophysical Research Communications, vol. 165, No. 1, Nov. 30, 1989, pp. 138-144.

International Preliminary Report on Patentability dated Apr. 6, 2017 in International (PCT) Application No. PCT/JP2017/002406, with English translation.

International Preliminary Report on Patentability dated Jun. 5, 2017 in International (PCT) Application No. PCT/JP2016/069564, with English translation.

Extended European Search Report dated Jul. 16, 2019 in corresponding European Application No. 16814543.1.

Tothill et al., "An Expression-Based Site of Origin Diagnostic Method Designed for Clinical Application to Cancer of Unknown Origin", Cancer Res., vol. 65, No. 10, May 15, 2005, pp. 4031-4040.

Talantov et al., "A Quantitative Reverse Transcriptase-Polymerase Chain Reaction Assay to Identify Metastatic Carcinoma Tissue of Origin", Journal of Molecular Diagnostics, vol. 8, No. 3, Jul. 2006, pp. 320-329.

Greene et al., "Understanding multicellular function and disease with human tissue-specific networks", Nat Genet., vol. 47, No. 6, Jun. 2015, pp. 569-576.

Supplementary Extended European Search Report dated Apr. 6, 2020 in European Patent Application No. 17775147.6.

(56) References Cited

OTHER PUBLICATIONS

Eulitz et al., "Inhibition of deoxyribonuclease I by actin is to protect cells from premature cell death", Apoptosis, 2007, vol. 12, No. 8, pp. 1511-1521.
Isern et al., "Functional analysis and androgen-regulated expression of mouse organic anion transporting polypeptide 1 (Oatp1) in the kidney", Biochimica et Biophysica Acta, 2001, vol. 1518, No. 1-2, pp. 73-78.
Saraheimo et al., "Increased levels of α-defensin (-1, -2 and -3) in type 1 diabetic patients with nephropathy", Nephrology Dialysis Transplantation, 2008, vol. 23, No. 3, pp. 914-918.
Young et al., "Hepcidin for Clinicians", Clinical Journal of the American Society of Nephrology, 2009, vol. 4, No. 8, pp. 1384-1387.
Ruchala et al., "The pathophysiology and pharmacology of hepcidin", Trends in Pharmacological Sciences, 2014, vol. 35, No. 3, pp. 155-161.
International Search Report dated Jul. 4, 2017 in International (PCT) Application No. PCT/JP2017/012761.
International Search Report dated May 9, 2017 in International (PCT) Application No. PCT/JP2017/013124.
Husain-Syed et al., "Cardio-Pulmonary-Renal Interactions", Journal of the American College of Cardiology, 2015, vol. 65, No. 22, pp. 2433-2448.
White et al., "Inflammatory Mechanisms of Organ Crosstalk during Ischemic Acute Kidney Injury", International Journal of Nephrology, 2012, Article ID 505197, pp. 1-8.
Zoccali et al., "Chronic Kidney Disease (CKD) as a Systemic Disease: Whole Body Autoregulation and Inter-Organ Cross-Talk", Kidney & Blood Pressure Research, 2014, vol. 39, pp. 134-141.
White et al., "Surgical Sepsis and Organ Crosstalk: The Role of the Kidney", Journal of Surgical Research, 2011, vol. 167, pp. 306-315.
Lysaght, "Maintenance Dialysis Population Dynamics: Current Trends and Long-Term Implications", Journal of the American Society of Nephrology, 2002, vol. 13, pp. S37-S40.
Hu et al., "Klotho Deficiency Causes Vascular Calcification in Chronic Kidney Disease", Journal of the American Society of Nephrology, 2011, vol. 22, pp. 124-136.
Manconi et al., "The intriguing heterogeneity of human salivary proline-rich proteins; Short title: Salivary proline-rich protein species", Journal of Proteomics, 2015, vol. 134, pp. 47-56.
Hoffmann et al., "Fibrinogen Excretion in the Urine and Immunoreactivity in the Kidney Serves as a Translational Biomarker for Acute Kidney Injury", The American Journal of Pathology, 2012, vol. 181, No. 3, pp. 818-828.
Prinsen et al., "Increased albumin and fibrinogen synthesis rate in patients with chronic renal failure", Kidney International, 2003, vol. 64, pp. 1495-1504.
Zhang et al., "Urinary biomarkers track the progression of nephropathy in hypertensive and obese rats", Biomarkers in Medicine, 2014, vol. 8, No. 1, pp. 85-94.
Craciun et al., "Pharmacological and genetic depletion of fibrinogen protects from kidney fibrosis", American Journal of Physiology, 2014, vol. 307, pp. F471-F484.
International Search Report dated Sep. 27, 2016 in International (PCT) Application No. PCT/JP2016/069564.
Takeda, "Senescence-Accelerated Mouse (SAM): With Special Reference to Age-associated Pathologies and Their Modulation", vol. 51, Jpn. J. Hyp., 1996, pp. 569-578, with English abstract.
Machine translation of reference CN 102558336 submitted with the IDS filed on Apr. 7, 2021.
Office Action dated Nov. 4, 2020 in U.S. Appl. No. 16/089,648.
Intel et al., "Fibroblast Growth Factor 23: Roles in Health and Disease", Journal of the American Society of Nephrology, 2005, vol. 16, pp. 2565-2575.
Karn et al., "Shared and Unique Proteins in Human, Mouse and Rat Saliva Proteomes: Footprints of Functional Adaptation", Proteomes, 2013, vol. 1, pp. 275-289.
Abstract of Isemura et al., "Tissue distribution and nucleotide sequence of bovine mRNA for salivary proline-rich protein P-B", Archives of Oral Biology, 2004, vol. 49, No. 11, pp. 881-887.
Hao et al., "Effects of Valsartan on Ventricular Hypertrophy and Expression of Proline-rich Tyrosine Kinase 2 in Myocardium of Re-novascular Hypertensive Rats", Chin J Hypertension, 2008, vol. 16, No. 3, pp. 249-252, with Abstract.
Qisheng et al., "Gene Editing Tools Mediated by CRISPR-Cas", Biotechnology Bulletin, 2014, Issue No. 7, pp. 37-43.
Bing et al., "Significance of change of renal tubule markers before and after treatment in chronic glomerulonephritis", Lab Med Clin, 2012, vol. 9, No. 19, pp. 2436-2439.
Notice of First Office Action dated Sep. 3, 2020 in corresponding Chinese Patent Application No. 201780032992.8, with English Translation.
Office Action dated May 25, 2021 in corresponding Chinese Patent Application No. 201680049081.1, with English Machine Translation.
Tsuchiya, K, et al., Hepcidin is a Potential Regulator of Iron Status in Chronic Kidney Disease, Therapeutic Apheresis and Dialysis, 2013, vol. 17, No. 1, pp. 1-8.
Srai, S.K., et al., "Erythropoietin regulates intestinal iron absorption in rat model of chronic renal failure", Kidney International, 2010, vol. 78, pp. 660-667.

Fig. 4
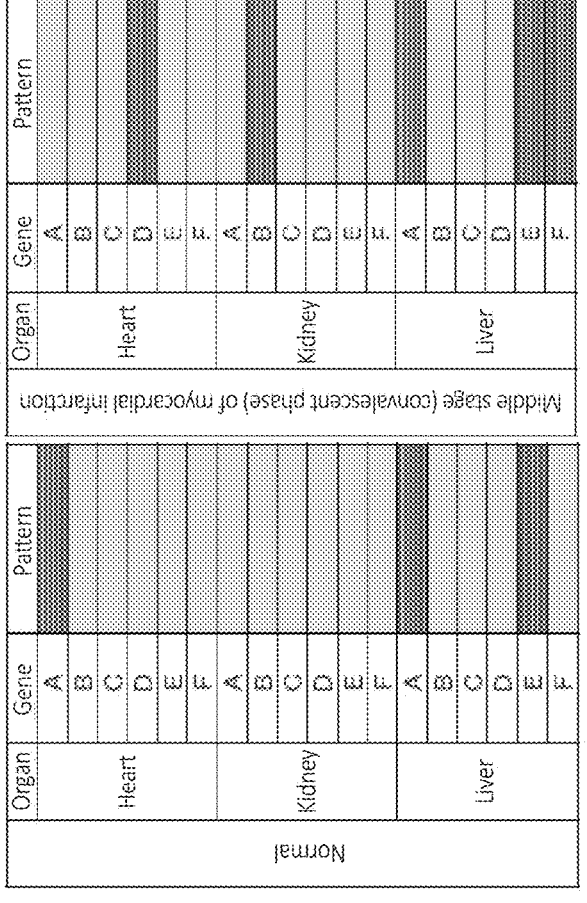
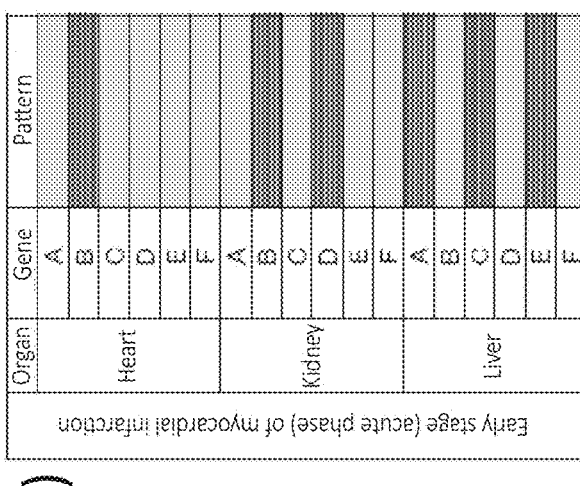
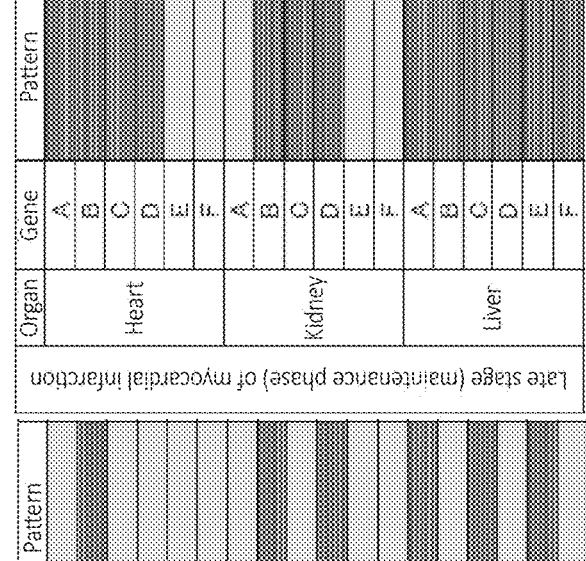

Fig.5
(a)
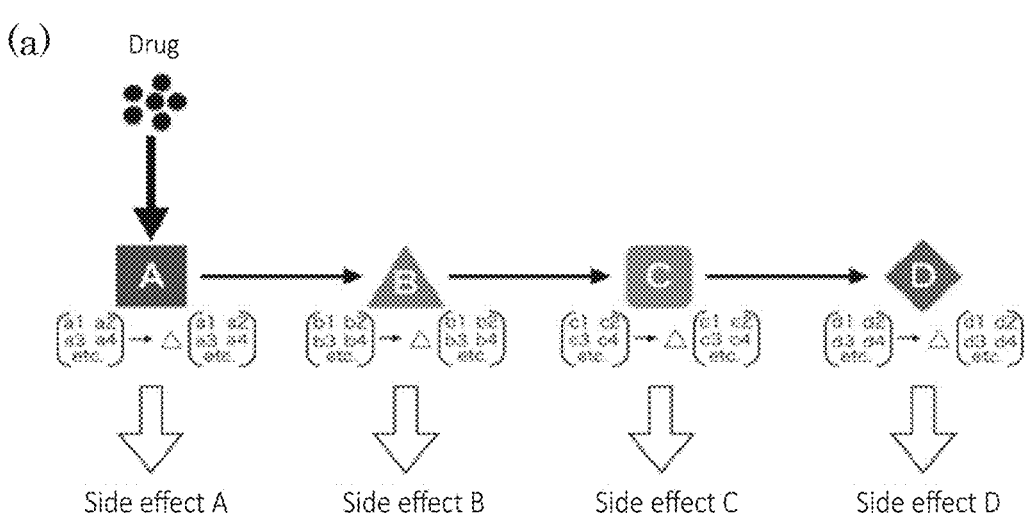
A, B, C, and D: organs
(b)
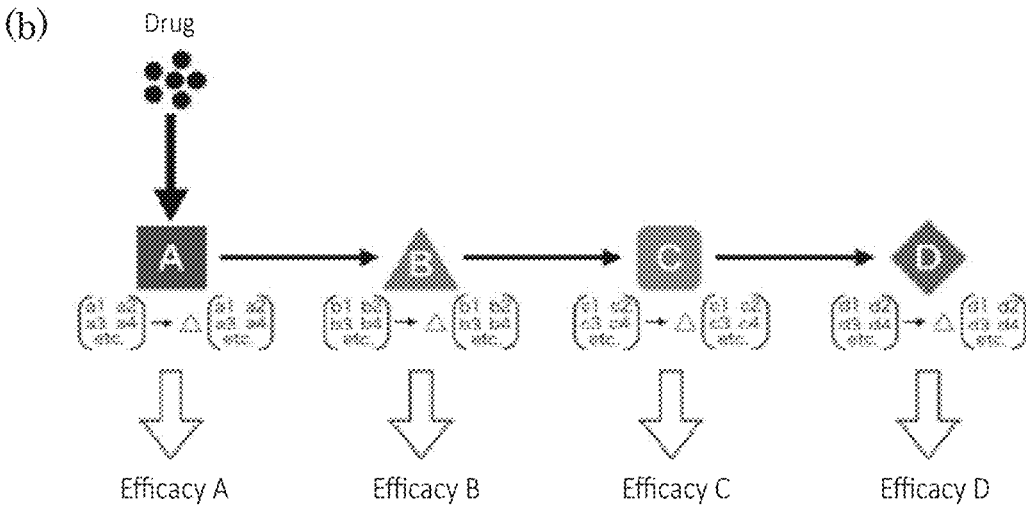
A, B, C, and D: organs

| Collected organ | Gene | Standard data 1 | | |
|---|---|---|---|---|
| | | Healthy individual | Model individual having precancerous lesion of colorectal cancer | Model individual having colorectal cancer |
| Testis | A | | | |
| | B | | | |
| | C | | | |
| | D | | | |
| | E | | | |
| | F | | | |
| Kidney | A | | | |
| | B | | | |
| | C | | | |
| | D | | | |
| | E | | | |
| | F | | | |
| Skin | A | | | |
| | B | | | |
| | C | | | |
| | D | | | |
| | E | | | |
| | F | | | |
| Colon | A | | | |
| | B | | | |
| | C | | | |
| | D | | | |
| | E | | | |
| | F | | | |

(b)

| Subject data X of colon of individual to which a test substance has been administered | |
|---|---|
| A | |
| B | |
| C | |
| D | |
| E | |
| F | |

(c)

| Subject data X of skin of individual to which test substance has been administered | |
|---|---|
| A | |
| B | |
| C | |
| D | |
| E | |
| F | |

Fig. 25 - 1

| Line No. | Gene Name | Reference Seq. ID | Chromosome Locus |
|---|---|---|---|
| 1 | 0610005C13Rik | NR_038165.1 | chr7:52823164-52845080 |
| 2 | 0610005C13Rik | NR_038166.1 | chr7:52823164-52845080 |
| 3 | 0610007P14Rik | NM_021446.2 | chr12:87156404-87165495 |
| 4 | 0610009B22Rik | NM_025319.2 | chr11:51498886-51502136 |
| 5 | 0610009L18Rik | NR_038126.1 | chr11:120209991-120212504 |
| 6 | 0610009O20Rik | NM_024179.5 | chr18:38409903-38422283 |
| 7 | 0610010B08Rik | NM_001177543.1 | chr2:174952492-175261278 |
| 8 | 0610010B08Rik | NM_001177543.1 | chr2:174952492-175261278 |
| 9 | 0610010B08Rik | NM_001177543.1 | chr2:175594788-176850107 |
| 10 | 0610010F05Rik | NM_027860.2 | chr11:23473775-23533631 |
| 11 | 0610010K14Rik | NM_001177601.1 | chr11:70048705-70051416 |
| 12 | 0610010K14Rik | NM_001177603.1 | chr11:70048705-70051416 |
| 13 | 0610010K14Rik | NM_001177606.1 | chr11:70048705-70051416 |
| 14 | 0610010K14Rik | NM_001177607.1 | chr11:70048705-70051416 |
| 15 | 0610010K14Rik | NM_026757.2 | chr11:70048705-70051416 |
| 16 | 0610010K14Rik | NM_145758.1 | chr11:70048705-70051416 |
| 17 | 0610011F06Rik | NM_026686.2 | chr17:26012444-26014108 |
| 18 | 0610012G03Rik | NR_027897.1 | chr16:31947136-31948607 |
| 19 | 0610030E20Rik | NM_026696.1 | chr6:72297310-72303154 |
| 20 | 0610031J06Rik | NM_020003.1 | chr3:88128944-88132553 |
| 21 | 0610031O16Rik | NR_045760.1 | chr3:137873681-137902627 |
| 22 | 0610037L13Rik | NM_028754.2 | chr4:107562503-107570407 |
| 23 | 0610038B21Rik | NR_028125.1 | chr8:80040955-80042477 |
| 24 | 0610039K10Rik | NR_028113.1 | chr2:163470586-163471536 |
| 25 | 0610040B10Rik | NR_027874.2 | chr5:144090986-144094383 |
| 26 | 0610040F04Rik | NR_040757.1 | chr6:108527029-108616919 |
| 27 | 0610040F04Rik | NR_040758.1 | chr6:108527029-108616919 |
| 28 | 0610040F04Rik | NR_104577.1 | chr6:108527029-108616919 |
| 29 | 0610040J01Rik | NM_029554.4 | chr5:64203733-64290858 |
| 30 | 0610043K17Rik | NR_040640.1 | chr4:101026388-101071790 |
| 31 | 1010001N08Rik | NR_105022.1 | chr18:11042034-11085633 |
| 32 | 1010001N08Rik | NR_105023.1 | chr18:11042034-11085633 |
| 33 | 1100001G20Rik | NM_183249.3 | chr11:83560441-83566148 |
| 34 | 1110001J03Rik | NM_025363.3 | chr6:38484860-38489449 |
| 35 | 1110002L01Rik | NR_030694.1 | chr12:3403883-3426747 |
| 36 | 1110004E09Rik | NM_026502.3 | chr16:90926055-90935094 |
| 37 | 1110004F10Rik | NM_019772.3 | chr7:123136893-123248724 |
| 38 | 1110006O24Rik | NR_027810.1 | chr5:116081057-116081825 |
| 39 | 1110007C09Rik | NM_026738.3 | chr13:49298319-49311395 |
| 40 | 1110008F13Rik | NM_026124.3 | chr2:156688858-156699298 |
| 41 | 1110008L16Rik | NM_025373.3 | chr2:56403624-56483478 |
| 42 | 1110008P14Rik | NM_198001.3 | chr2:32234620-32237435 |
| 43 | 1110012L19Rik | NM_026787.3 | chrX:67639087-67642591 |
| 44 | 1110015O18Rik | NR_045272.1 | chr3:4798707-4814911 |
| 45 | 1110017D15Rik | NM_001048005.1 | chr4:41452041-41464366 |
| 46 | 1110017D15Rik | NM_001253777.1 | chr4:41452041-41464366 |
| 47 | 1110017D15Rik | NM_001253778.1 | chr4:41452041-41464366 |
| 48 | 1110017D15Rik | NM_001253780.1 | chr4:41452041-41464366 |
| 49 | 1110017D15Rik | NM_001253788.1 | chr4:41452041-41464366 |
| 50 | 1110017D15Rik | NM_028624.1 | chr4:41452041-41464366 |
| 51 | 1110017D15Rik | NR_045549.2 | chr4:41452041-41464366 |
| 52 | 1110017D15Rik | NR_045551.2 | chr4:41452041-41464366 |
| 53 | 1110019D14Rik | NR_045995.1 | chr6:13821568-13846421 |
| 54 | 1110020A21Rik | NR_027929.1 | chr17:85316521-85423332 |
| 55 | 1110020A21Rik | NR_027930.1 | chr17:85316521-85423332 |
| 56 | 1110025L11Rik | NM_001276278.1 | chr16:89063654-89064247 |
| 57 | 1110028F11Rik | NR_045139.1 | chr11:87513026-87518829 |
| 58 | 1110028F18Rik | NR_045470.1 | chr8:109111042-109118720 |
| 59 | 1110032A03Rik | NM_023483.3 | chr9:50570932-50576257 |
| 60 | 1110032F04Rik | NM_001167996.1 | chr3:68673507-68676085 |
| 61 | 1110034G24Rik | NM_028637.1 | chr2:132516018-132576791 |
| 62 | 1110036E04Rik | NR_040713.1 | chr9:63897635-63901907 |
| 63 | 1110037F02Rik | NM_001081183.1 | chr4:11413104-11478290 |
| 64 | 1110038B12Rik | NR_015536.1 | chr17:35087180-35089416 |
| 65 | 1110038B12Rik | NR_027943.1 | chr17:35087180-35089416 |
| 66 | 1110038F14Rik | NM_054099.2 | chr15:76778973-76781161 |
| 67 | 1110046J04Rik | NR_040707.1 | chr13:34027901-34052050 |
| 68 | 1110051M20Rik | NM_175123.4 | chr2:91117984-91284799 |
| 69 | 1110054M08Rik | NR_037954.1 | chr16:24392642-24393741 |
| 70 | 1110057K04Rik | NM_001177767.1 | chr12:8214912-8292565 |
| 71 | 1110057K04Rik | NM_001167768.1 | chr12:8214912-8292565 |
| 72 | 1110057K04Rik | NM_172401.4 | chr12:8214912-8292565 |
| 73 | 1110058L19Rik | NM_026503.3 | chr1:24002777-24012479 |
| 74 | 1110059E24Rik | NM_025423.2 | chr19:21671802-21727281 |
| 75 | 1110059G10Rik | NM_025419.4 | chr9:122854206-122860118 |
| 76 | 1110065P20Rik | NM_001142727.1 | chr4:124526729-124527974 |
| 77 | 1190002F15Rik | NR_037955.1 | chr6:134879109-134901736 |
| 78 | 1190002F15Rik | NR_037956.1 | chr6:134879109-134901736 |
| 79 | 1190002N15Rik | NM_001033145.2 | chr9:94418282-94438500 |
| 80 | 1190003K10Rik | NM_001195435.1 | chr3:64582553-64599100 |
| 81 | 1190005I06Rik | NM_197988.1 | chr8:123132501-123158282 |
| 82 | 1190007I07Rik | NM_001135567.1 | chr10:82082595-82085973 |
| 83 | 1190007I07Rik | NM_001135568.1 | chr10:82082595-82085973 |
| 84 | 1190007I07Rik | NM_001135569.1 | chr10:82082595-82085973 |
| 85 | 1200014J11Rik | NM_025818.3 | chr17:72861368-72897081 |
| 86 | 1300002E11Rik | NR_037957.1 | chr16:21794419-21809112 |
| 87 | 1300002E11Rik | NR_037958.1 | chr16:21794419-21809112 |
| 88 | 1300002K09Rik | NM_028788.4 | chr4:45861818-45899880 |
| 89 | 1300017J02Rik | NM_027918.2 | chr9:103152859-103190627 |
| 90 | 1500004A13Rik | NR_015498.2 | chr3:88625932-88636409 |
| 91 | 1500009C09Rik | NR_037697.1 | chr15:82082826-82091183 |
| 92 | 1500009C09Rik | NR_037698.1 | chr15:82082826-82091183 |
| 93 | 1500009L16Rik | NM_001145198.1 | chr10:83185609-83225500 |
| 94 | 1500011B03Rik | NR_027817.1 | chr5:115258204-115263985 |
| 95 | 1500011B03Rik | NR_027818.1 | chr5:115258204-115263985 |
| 96 | 1500011K16Rik | NR_015476.1 | chr2:127617113-127618224 |
| 97 | 1500012F01Rik | NM_001081005.1 | chr2:166888434-166891362 |
| 98 | 1500012K07Rik | NR_045812.1 | chr7:82259780-82476305 |
| 99 | 1500012K07Rik | NR_045814.1 | chr7:82259780-82476305 |
| 100 | 1500015A07Rik | NR_029432.1 | chr18:61886043-61887907 |
| 101 | 1500015L24Rik | NR_045817.2 | chr19:20479777-20497275 |
| 102 | 1500015O10Rik | NM_024283.3 | chr1:43787446-43799409 |
| 103 | 1500017E21Rik | NR_033510.1 | chr19:36693908-36763969 |
| 104 | 1600002D24Rik | NR_040484.1 | chr16:96052729-96150684 |
| 105 | 1600002D24Rik | NR_040485.1 | chr16:96052729-96150684 |
| 106 | 1600002H07Rik | NM_028056.1 | chr17:24352600-24357714 |
| 107 | 1600002K03Rik | NM_027207.2 | chr10:79635688-79637864 |
| 108 | 1600010M07Rik | NR_037959.1 | chr7:117141890-117150160 |
| 109 | 1600012H06Rik | NM_001083880.1 | chr17:15080188-15098237 |
| 110 | 1600012H06Rik | NM_001083881.1 | chr17:15080188-15098237 |
| 111 | 1600012H06Rik | NM_001083882.1 | chr17:15080188-15098237 |
| 112 | 1600012H06Rik | NM_026451.2 | chr17:15080188-15098237 |
| 113 | 1600014C10Rik | NM_001085385.1 | chr7:38968235-38982584 |
| 114 | 1600014C10Rik | NM_028166.3 | chr7:38968235-38982584 |
| 115 | 1600014C23Rik | NM_028164.1 | chr17:45869812-45870793 |
| 116 | 1600014K23Rik | NM_028046.1 | chrX:82495015-82515630 |
| 117 | 1600015I10Rik | NM_001081273.2 | chr6:48879894-48883686 |
| 118 | 1600016N20Rik | NM_028050.2 | chr7:148395942-148399979 |
| 119 | 1600019K03Rik | NR_040481.1 | chr16:35503255-35509505 |
| 120 | 1600020E01Rik | NR_037960.1 | chr6:86477323-86514443 |
| 121 | 1600020E01Rik | NR_037961.1 | chr6:86477323-86514443 |
| 122 | 1600023N17Rik | NR_073433.1 | chr5:46059939-46060947 |
| 123 | 1600025M17Rik | NR_038168.1 | chr2:53570784-53573841 |
| 124 | 1600027J07Rik | NR_036588.1 | chr8:105867777-105871434 |
| 125 | 1600029I14Rik | NR_028123.1 | chr9:99370840-99375170 |
| 126 | 1600029O15Rik | NR_033522.1 | chr9:58050704-58056615 |
| 127 | 1700001C02Rik | NM_029285.1 | chr5:30768449-30786460 |
| 128 | 1700001C19Rik | NM_001172091.1 | chr17:47549682-47607587 |
| 129 | 1700001C19Rik | NM_029296.2 | chr17:47549682-47607587 |
| 130 | 1700001D01Rik | NR_045475.1 | chr8:63760319-63767669 |
| 131 | 1700001F09Rik | NM_027940.2 | chr14:44020916-44026344 |
| 132 | 1700001G11Rik | NR_038077.1 | chr14:66914166-66915966 |
| 133 | 1700001G17Rik | NR_033199.1 | chr1:33728668-33727557 |
| 134 | 1700001J03Rik | NM_001008547.1 | chr5:146994025-146996880 |
| 135 | 1700001J11Rik | NR_033613.1 | chr9:39858142-39860610 |
| 136 | 1700001K19Rik | NM_025488.2 | chr12:111905898-111920829 |
| 137 | 1700001K23Rik | NR_036590.1 | chr19:53323225-53329695 |
| 138 | 1700001L05Rik | NR_027980.1 | chr15:83184276-83197727 |
| 139 | 1700003L19Rik | NM_027035.1 | chr13:68736315-68753108 |
| 140 | 1700001O22Rik | NM_198000.3 | chr2:30651082-30659184 |
| 141 | 1700001O22Rik | NR_028486.2 | chr2:30651082-30659184 |
| 142 | 1700001O22Rik | NR_028487.1 | chr2:30651082-30659184 |
| 143 | 1700001P01Rik | NM_028156.2 | chr11:97632794-97637232 |
| 144 | 1700003C15Rik | NR_045478.1 | chr5:11749832-11769308 |
| 145 | 1700003D09Rik | NR_045477.1 | chr11:98212032-98219597 |
| 146 | 1700003E16Rik | NM_027948.1 | chr6:83106397-83112969 |
| 147 | 1700003E24Rik | NR_103799.1 | chrX:90401492-90402210 |
| 148 | 1700003E24Rik | NR_103799.1 | chrX:90428565-90429283 |
| 149 | 1700003F12Rik | NM_029305.2 | chr2:154374640-154375784 |
| 150 | 1700003G13Rik | NR_040720.1 | chr9:45126349-45130162 |
| 151 | 1700003G18Rik | NR_029433.1 | chr7:123225275-123236663 |
| 152 | 1700003H04Rik | NR_015460.1 | chr3:124268808-124284009 |
| 153 | 1700003L19Rik | NR_040507.1 | chr16:12811482-12848746 |
| 154 | 1700003M02Rik | NM_027041.4 | chr4:34658580-34677455 |
| 155 | 1700003M07Rik | NR_040647.1 | chr4:129637617-129642382 |
| 156 | 1700003M07Rik | NR_040648.1 | chr4:129637617-129642382 |
| 157 | 1700003P14Rik | NR_045982.1 | chr13:119344974-119377436 |
| 158 | 1700006A11Rik | NM_027939.1 | chr3:124104072-124128946 |
| 159 | 1700006E09Rik | NM_029287.1 | chr11:101848369-101853578 |
| 160 | 1700006F04Rik | NR_045621.1 | chr14:120148449-120150786 |
| 161 | 1700006H21Rik | NR_045900.2 | chr13:108477476-108482248 |
| 162 | 1700007B14Rik | NM_001164235.1 | chr8:77972592-78508406 |
| 163 | 1700007B14Rik | NM_027944.1 | chr8:77972592-78508406 |
| 164 | 1700007F19Rik | NR_040538.1 | chr3:57945628-57967729 |
| 165 | 1700007G11Rik | NM_001024614.1 | chr5:98758323-99231038 |
| 166 | 1700007J10Rik | NR_045476.1 | chr11:59539419-59553656 |
| 167 | 1700007K09Rik | NM_027037.2 | chr7:138469444-138473013 |
| 168 | 1700007K13Rik | NM_027040.1 | chr2:28317520-28321844 |
| 169 | 1700007L15Rik | NR_045709.1 | chr16:33379939-33380822 |
| 170 | 1700007P06Rik | NR_040554.1 | chr1:188949017-188951731 |
| 171 | 1700008F21Rik | NM_001168369.1 | chr8:131591033-131707632 |
| 172 | 1700008F21Rik | NM_029292.3 | chr8:131591033-131707632 |
| 173 | 1700008I05Rik | NR_027952.3 | chrX:132189236-132228329 |
| 174 | 1700008J07Rik | NR_024331.1 | chr7:134653951-134656383 |
| 175 | 1700008K24Rik | NR_038141.1 | chr17:49251588-49252858 |
| 176 | 1700008K24Rik | NR_038142.1 | chr17:49251588-49252858 |
| 177 | 1700008K24Rik | NR_038143.1 | chr17:49251588-49252858 |
| 178 | 1700008K24Rik | NR_038144.2 | chr17:49251588-49252858 |
| 179 | 1700008K24Rik | NR_038145.2 | chr17:49251588-49252858 |
| 180 | 1700008O03Rik | NM_027049.1 | chr7:51615414-51630400 |
| 181 | 1700008P02Rik | NR_027048.1 | chr3:6615412-6620443 |
| 182 | 1700009C05Rik | NR_046040.1 | chr8:81850458-81860794 |
| 183 | 1700009J07Rik | NR_015547.1 | chr10:77356164-77358856 |
| 184 | 1700009N14Rik | NM_001081095.1 | chr4:39397325-39398811 |
| 185 | 1700009P17Rik | NM_001081275.1 | chr1:173051791-173057098 |
| 186 | 1700010B08Rik | NM_029308.1 | chr2:173544915-173547587 |
| 187 | 1700010D01Rik | NM_029590.3 | chrX:92927929-92928604 |
| 188 | 1700010I02Rik | NR_040587.1 | chr3:7925302-7954887 |

Fig. 25 - 2

| | | | |
|---|---|---|---|
| 189 | 1700010I14Rik | NM_025851.3 | chr17:9181197-9201184 |
| 190 | 1700010J16Rik | NR_040579.1 | chr10:112163981-112222655 |
| 191 | 1700010K23Rik | NR_040512.1 | chr16:66657363-66664871 |
| 192 | 1700011A15Rik | NM_025487.3 | chr15:101278175-101284340 |
| 193 | 1700011B04Rik | NR_045616.1 | chr13:35273491-35279883 |
| 194 | 1700011E24Rik | NM_029298.1 | chr17:87788910-87827081 |
| 195 | 1700011H14Rik | NM_025956.5 | chr14:49846033-49865103 |
| 196 | 1700011I03Rik | NM_029290.3 | chr18:57693480-57890719 |
| 197 | 1700011L22Rik | NM_026315.1 | chr8:81734328-81772482 |
| 198 | 1700011M02Rik | NR_073044.1 | chrX:100104243-100104990 |
| 199 | 1700012A03Rik | NM_029587.3 | chr6:32000287-32008915 |
| 200 | 1700012B07Rik | NM_001162428.1 | chr11:109649604-109689360 |
| 201 | 1700012B07Rik | NM_027038.1 | chr11:109649604-109689360 |
| 202 | 1700012B09Rik | NM_029306.3 | chr9:14562637-14575474 |
| 203 | 1700012D01Rik | NR_045171.1 | chr10:127104178-127105907 |
| 204 | 1700012D14Rik | NR_015573.2 | chr7:118261186-118266189 |
| 205 | 1700012I11Rik | NR_045140.1 | chr15:67058330-67208656 |
| 206 | 1700012L04Rik | NM_029588.3 | chrX:8860890-8861414 |
| 207 | 1700012P22Rik | NM_027056.1 | chr4:144008093-144028675 |
| 208 | 1700013D24Rik | NM_001177502.1 | chr6:124297611-124307104 |
| 209 | 1700013F07Rik | NM_029314.1 | chr3:108340501-108347615 |
| 210 | 1700013G24Rik | NM_027063.2 | chr4:137009210-137011376 |
| 211 | 1700013H16Rik | NM_001200013.1 | chrX:51046077-51061008 |
| 212 | 1700015E13Rik | NM_001039593.1 | chr1:172238991-172242256 |
| 213 | 1700015F17Rik | NM_001200025.1 | chr5:5437826-5479143 |
| 214 | 1700015G11Rik | NM_001195601.1 | chr7:59267049-59271086 |
| 215 | 1700016C15Rik | NM_027077.2 | chr1:179659944-179683436 |
| 216 | 1700016D06Rik | NM_024271.1 | chr8:11654923-11678750 |
| 217 | 1700016G22Rik | NR_045891.1 | chr13:5854754-5857338 |
| 218 | 1700016H13Rik | NM_001163550.1 | chr5:104077605-104084751 |
| 219 | 1700016H13Rik | NM_028824.1 | chr5:104077605-104084751 |
| 220 | 1700016K19Rik | NM_198637.2 | chr11:75813413-75817071 |
| 221 | 1700016L04Rik | NR_045824.1 | chr10:14425415-14478825 |
| 222 | 1700016L21Rik | NR_040460.1 | chr1:80442506-80472235 |
| 223 | 1700016P04Rik | NR_038149.1 | chr6:13363336-13365996 |
| 224 | 1700017B05Rik | NM_028820.2 | chr9:57100128-57110406 |
| 225 | 1700017D01Rik | NM_027058.1 | chr19:11171305-11205368 |
| 226 | 1700017G19Rik | NR_040445.1 | chr3:40403786-40421834 |
| 227 | 1700017J07Rik | NR_040326.1 | chr2:168803768-168804406 |
| 228 | 1700017N19Rik | NM_001081246.1 | chr10:100055019-100081025 |
| 229 | 1700018A04Rik | NM_029439.1 | chr3:31657360-31674382 |
| 230 | 1700018B08Rik | NM_029597.1 | chr8:124054683-124065854 |
| 231 | 1700018B24Rik | NR_003617.1 | chr3:48409652-48413022 |
| 232 | 1700018C11Rik | NM_029324.2 | chr4:63268124-63283463 |
| 233 | 1700018E24Rik | NM_027069.3 | chr5:145803858-145806547 |
| 234 | 1700018G05Rik | NR_045422.1 | chrX:100123710-100124446 |
| 235 | 1700018L02Rik | NR_028360.1 | chr19:29121973-29123219 |
| 236 | 1700019A02Rik | NM_027070.1 | chr1:53215420-53244461 |
| 237 | 1700019B03Rik | NM_029598.1 | chr8:3470861-3487178 |
| 238 | 1700019B21Rik | NR_045442.1 | chrX:59763713-59780186 |
| 239 | 1700019B21Rik | NR_045443.1 | chrX:59763713-59780186 |
| 240 | 1700019D03Rik | NM_144953.2 | chr1:52981970-53009684 |
| 241 | 1700019E08Rik | NR_040497.1 | chr2:45552124-45553967 |
| 242 | 1700019G17Rik | NM_001145895.1 | chr6:85849043-85854932 |
| 243 | 1700019G17Rik | NM_029331.3 | chr6:85849043-85854932 |
| 244 | 1700019G24Rik | NR_040255.1 | chr6:5913897-5927393 |
| 245 | 1700019L03Rik | NM_025619.1 | chr2:32632933-32639925 |
| 246 | 1700019M22Rik | NR_103800.1 | chr12:97284830-97285432 |
| 247 | 1700019N19Rik | NM_026028.2 | chr19:58860292-58868904 |
| 248 | 1700019O17Rik | NM_027966.1 | chr1:88322903-88324624 |
| 249 | 1700020A23Rik | NM_001163483.1 | chr2:130230994-130231810 |
| 250 | 1700020A23Rik | NM_029375.1 | chr2:130230994-130231810 |
| 251 | 1700020D05Rik | NM_023781.5 | chr19:5502769-5503787 |
| 252 | 1700020G17Rik | NR_045979.1 | chr10:110238229-110333563 |
| 253 | 1700020I14Rik | NR_015473.1 | chr2:119420031-119426480 |
| 254 | 1700020I14Rik | NR_027832.1 | chr2:119420031-119426480 |
| 255 | 1700020L24Rik | NM_025492.3 | chr11:83251195-83254734 |
| 256 | 1700020M21Rik | NR_040742.1 | chr9:120822891-120824358 |
| 257 | 1700020N01Rik | NR_027968.1 | chr10:21312950-21342181 |
| 258 | 1700020N15Rik | NM_029334.1 | chrX:67198456-67199155 |
| 259 | 1700020N18Rik | NR_026924.1 | chr1:93301456-93302606 |
| 260 | 1700021F05Rik | NM_026411.1 | chr10:43244926-43260800 |
| 261 | 1700021F07Rik | NM_028158.1 | chr2:173348092-173354003 |
| 262 | 1700021K19Rik | NM_001200038.1 | chr16:32821787-32868452 |
| 263 | 1700021K19Rik | NM_172615.4 | chr16:32821787-32868452 |
| 264 | 1700021N21Rik | NR_045880.1 | chr4:134004679-134006086 |
| 265 | 1700022A21Rik | NR_003953.1 | chr5:24151270-24154678 |
| 266 | 1700022A22Rik | NR_045509.1 | chr15:46156130-46205445 |
| 267 | 1700022E09Rik | NR_040668.1 | chr16:59466697-59469064 |
| 268 | 1700022H16Rik | NR_045488.1 | chr12:9572041-9577391 |
| 269 | 1700022I11Rik | NM_026088.3 | chr4:42982817-42987197 |
| 270 | 1700023C21Rik | NR_045909.1 | chr1:109707191-109709790 |
| 271 | 1700023E05Rik | NM_027970.1 | chr5:77445048-77490547 |
| 272 | 1700023F02Rik | NR_038039.1 | chr10:65583356-65586812 |
| 273 | 1700023F06Rik | NM_001054724.2 | chr11:103060258-103069862 |
| 274 | 1700023L04Rik | NR_040263.1 | chr6:29935328-29943531 |
| 275 | 1700023L04Rik | NR_001034037.1 | chr6:29935328-29943531 |
| 276 | 1700024B18Rik | NR_045479.1 | chr14:124386857-124414906 |
| 277 | 1700024F13Rik | NR_045363.1 | chr13:3497295-3500639 |
| 278 | 1700024G13Rik | NM_001034087.1 | chr14:33189687-33201559 |
| 279 | 1700024P04Rik | NM_027064.1 | chr13:99754044-99754520 |
| 280 | 1700024P16Rik | NM_001162980.1 | chr4:104586060-104689468 |
| 281 | 1700024P16Rik | NM_001285952.1 | chr4:104586060-104689468 |
| 282 | 1700024P16Rik | NM_001285953.1 | chr4:104586060-104689468 |
| 283 | 1700024P16Rik | NR_104376.1 | chr4:104586060-104689468 |
| 284 | 1700025B11Rik | NR_040310.1 | chr15:77388869-77392322 |
| 285 | 1700025C18Rik | NR_033448.1 | chr2:164904192-164916250 |
| 286 | 1700025F22Rik | NM_027074.3 | chr19:11214172-11239810 |
| 287 | 1700025F24Rik | NR_040578.1 | chr10:118850499-118863920 |
| 288 | 1700025G04Rik | NM_197990.3 | chr1:153731653-153937450 |
| 289 | 1700025K24Rik | NR_045825.1 | chr17:54491907-54509399 |
| 290 | 1700025M24Rik | NR_040687.1 | chr5:73659818-73675423 |
| 291 | 1700025M24Rik | NR_040668.1 | chr5:73659818-73675423 |
| 292 | 1700025M24Rik | NR_040689.1 | chr5:73659818-73675423 |
| 293 | 1700025N23Rik | NR_040523.1 | chr6:39013878-39017585 |
| 294 | 1700026D08Rik | NM_029335.3 | chr7:90924126-90943349 |
| 295 | 1700026D11Rik | NR_028286.1 | chr2:132316463-132349793 |
| 296 | 1700026F02Rik | NR_045487.1 | chr8:73530626-73550654 |
| 297 | 1700026L03Rik | NM_027283.2 | chr2:28547599-28555171 |
| 298 | 1700027A15Rik | NR_038001.1 | chr1:73062609-73072082 |
| 299 | 1700027A15Rik | NR_038002.1 | chr1:73062609-73072082 |
| 300 | 1700027F09Rik | NR_040681.1 | chr5:64846051-64859181 |
| 301 | 1700027H10Rik | NR_040594.1 | chr3:45220506-45243231 |
| 302 | 1700027I24Rik | NR_040741.1 | chr9:36476440-36500774 |
| 303 | 1700027J07Rik | NR_040581.2 | chr10:43465963-43485642 |
| 304 | 1700028B04Rik | NR_033605.1 | chr7:29281959-29282511 |
| 305 | 1700028D13Rik | NR_045377.1 | chr5:112635782-112639022 |
| 306 | 1700028D13Rik | NR_045378.1 | chr5:112635782-112639022 |
| 307 | 1700028E10Rik | NR_045699.1 | chr5:152171249-152216658 |
| 308 | 1700028E10Rik | NR_045700.1 | chr5:152171249-152216658 |
| 309 | 1700028I16Rik | NR_038042.1 | chr10:82274867-82286987 |
| 310 | 1700028J19Rik | NR_029436.1 | chr7:51485299-51491492 |
| 311 | 1700028K03Rik | NM_175241.1 | chr5:107963729-108090872 |
| 312 | 1700028K03Rik | NR_182745.2 | chr5:107963729-108090872 |
| 313 | 1700028M03Rik | NR_036591.1 | chr3:83359288-83378040 |
| 314 | 1700028P14Rik | NM_026188.2 | chr19:23633249-23727302 |
| 315 | 1700028P15Rik | NR_040509.1 | chr2:171782378-171788299 |
| 316 | 1700029B22Rik | NR_040531.1 | chr7:138289952-138294092 |
| 317 | 1700029F12Rik | NM_001080777.2 | chr13:97791818-97805209 |
| 318 | 1700029F12Rik | NM_001284205.1 | chr13:97791818-97805209 |
| 319 | 1700029F12Rik | NR_045225.3 | chr13:97791818-97805209 |
| 320 | 1700029F12Rik | NR_104276.1 | chr13:97791818-97805209 |
| 321 | 1700029H14Rik | NM_001080781.2 | chr8:13550721-13562461 |
| 322 | 1700029H14Rik | NM_025585.3 | chr8:13550721-13562461 |
| 323 | 1700029I15Rik | NM_183112.3 | chr2:92223074-92223760 |
| 324 | 1700029J03Rik | NR_040494.1 | chr16:93397959-93459117 |
| 325 | 1700029J07Rik | NM_001033148.3 | chr8:47038959-47060606 |
| 326 | 1700029M20Rik | NR_015613.1 | chr4:135182569-135186113 |
| 327 | 1700029M20Rik | NR_027909.1 | chr4:135182569-135186113 |
| 328 | 1700029N11Rik | NR_045489.1 | chr13:44535095-44552936 |
| 329 | 1700029P11Rik | NM_025503.4 | chr15:81810969-81811993 |
| 330 | 1700030A11Rik | NR_045457.1 | chr17:29042210-29043716 |
| 331 | 1700030C10Rik | NR_015521.1 | chr12:20810252-20821640 |
| 332 | 1700030F04Rik | NR_045731.1 | chr6:117629224-117701787 |
| 333 | 1700030F18Rik | NM_028180.3 | chr15:99748779-99762089 |
| 334 | 1700030J22Rik | NM_027103.2 | chr8:119493488-119502843 |
| 335 | 1700030K09Rik | NM_028170.2 | chr8:74967779-74984440 |
| 336 | 1700030L20Rik | NR_040592.1 | chr3:136098233-136112313 |
| 337 | 1700030M09Rik | NR_045903.1 | chr8:124068287-124071552 |
| 338 | 1700030N03Rik | NR_045304.1 | chr19:3153798-3197703 |
| 339 | 1700030O20Rik | NR_045435.1 | chr10:116160122-116166233 |
| 340 | 1700031A10Rik | NR_045439.1 | chr17:37060736-37070377 |
| 341 | 1700031F05Rik | NM_028496.1 | chrX:100054525-100061692 |
| 342 | 1700031M16Rik | NR_015496.1 | chr15:98228875-98246566 |
| 343 | 1700031P21Rik | NR_045910.1 | chr12:53709970-53703309 |
| 344 | 1700034E13Rik | NM_030097.1 | chr16:52805873-52823385 |
| 345 | 1700034F02Rik | NM_001163521.1 | chr11:29445841-29478352 |
| 346 | 1700034F02Rik | NM_028504.1 | chr11:29445841-29478352 |
| 347 | 1700034G24Rik | NR_045396.1 | chr5:113011955-113019016 |
| 348 | 1700034G24Rik | NR_045397.1 | chr5:113011955-113019016 |
| 349 | 1700034H15Rik | NR_030669.1 | chr1:193717951-193731406 |
| 350 | 1700034I23Rik | NR_045380.1 | chr3:40704121-40706465 |
| 351 | 1700034J05Rik | NM_001164236.1 | chr6:146837015-146980545 |
| 352 | 1700034J05Rik | NM_028509.1 | chr6:146837015-146980545 |
| 353 | 1700034K08Rik | NR_040756.1 | chr8:92874753-92900571 |
| 354 | 1700034O15Rik | NM_029671.2 | chr6:41634429-41635716 |
| 355 | 1700034P13Rik | NR_040462.1 | chr1:9737729-9761337 |
| 356 | 1700036G14Rik | NR_040647.1 | chr3:85121440-85135949 |
| 357 | 1700037C18Rik | NM_028484.2 | chr16:3905797-3908689 |
| 358 | 1700037H04Rik | NM_026091.2 | chr2:130972060-130985756 |
| 359 | 1700039E13Rik | NM_001033176.1 | chr7:52538242-52544363 |
| 360 | 1700039E22Rik | NR_045315.1 | chr19:44902983-44910428 |
| 361 | 1700040L02Rik | NM_028491.1 | chr10:67893703-68004623 |
| 362 | 1700041L12Rik | NR_033784.1 | chr9:57023081-57033915 |
| 363 | 1700041M19Rik | NR_040573.1 | chr16:77004472-77011126 |
| 364 | 1700042B14Rik | NM_001081671.1 | chrX:151559523-151582392 |
| 365 | 1700042G07Rik | NM_001099295.2 | chr4:115845976-115846902 |
| 366 | 1700042G15Rik | NR_038178.1 | chr4:57372663-57377164 |
| 367 | 1700042G15Rik | NR_038179.1 | chr4:57372663-57377164 |
| 368 | 1700042O10Rik | NR_045178.1 | chr11:11768126-11785324 |
| 369 | 1700044C05Rik | NR_045624.1 | chr14:118765099-118797387 |
| 370 | 1700044K03Rik | NR_033785.1 | chr18:49682942-49684094 |
| 371 | 1700045H11Rik | NR_040649.1 | chr4:150202333-150229058 |
| 372 | 1700046C09Rik | NR_045918.1 | chr11:14460338-14499228 |
| 373 | 1700047A11Rik | NR_110583.1 | chr8:27193081-27206992 |
| 374 | 1700047E10Rik | NR_073363.1 | chr14:44769271-44790902 |
| 375 | 1700047G03Rik | NR_040447.1 | chr15:118896816-118899838 |
| 376 | 1700047I17Rik2 | NM_001100116.1 | chr12:56225514-56243069 |
| 377 | 1700047I17Rik2 | NR_001100116.1 | chr12:56256090-56365681 |
| 378 | 1700047L14Rik | NR_040691.1 | chr5:109192860-109197936 |

Fig. 25 - 3

| | | | | | | | |
|---|---|---|---|---|---|---|---|
| 379 | 1700047M11Rik | NR_015458.1 | chr1:184230964-184233420 | 473 | 1700102H20Rik | NR_045302.1 | chr17:3557823-3559863 |
| 380 | 1700048M11Rik | NR_045300.1 | chr16:92308961-92312711 | 474 | 1700102H20Rik | NR_045303.1 | chr17:3557823-3559863 |
| 381 | 1700048O20Rik | NR_033553.1 | chr9:121846392-121856134 | 475 | 1700102P08Rik | NM_053216.2 | chr9:108295164-108300098 |
| 382 | 1700049E15Rik | NR_033636.1 | chr6:147638762-147650896 | 476 | 1700104L18Rik | NR_108033.1 | chr12:55334601-55343307 |
| 383 | 1700049E22Rik | NR_040525.1 | chr6:100477393-100483420 | 477 | 1700105P06Rik | NR_045703.1 | chr19:7457493-7458047 |
| 384 | 1700049G17Rik | NM_028538.1 | chr7:28692410-28714449 | 478 | 1700106J16Rik | NM_028859.1 | chr11:88107544-88108763 |
| 385 | 1700049L16Rik | NR_003644.1 | chr10:71442632-71443438 | 479 | 1700108F19Rik | NR_015485.1 | chr14:77077374-77086915 |
| 386 | 1700051A21Rik | NR_045922.1 | chr11:72080345-72082058 | 480 | 1700108J01Rik | NR_015532.1 | chr14:122629127-122632860 |
| 387 | 1700052J22Rik | NR_033786.1 | chr12:82024418-82025434 | 481 | 1700109G14Rik | NR_033788.1 | chr14:61911819-61924171 |
| 388 | 1700052K11Rik | NR_027956.1 | chr11:105040334-105042747 | 482 | 1700109G15Rik | NR_046197.1 | chr11:84530477-84533934 |
| 389 | 1700052N19Rik | NM_024261.2 | chr10:5891400-5913936 | 483 | 1700109H08Rik | NM_029843.2 | chr5:3571716-3584341 |
| 390 | 1700054A03Rik | NR_045320.1 | chr19:53150741-53158882 | 484 | 1700109I08Rik | NR_045936.1 | chr14:40468950-40498581 |
| 391 | 1700054K19Rik | NR_027865.1 | chr6:112160701-112162512 | 485 | 1700109K24Rik | NR_108037.1 | chr15:76914828-76926744 |
| 392 | 1700054M17Rik | NR_045919.1 | chr2:118130650-118133902 | 486 | 1700110C19Rik | NR_045641.1 | chr17:10517466-10522177 |
| 393 | 1700054O13Rik | NM_026096.1 | chrX:9424072-9424626 | 487 | 1700110I01Rik | NR_038059.1 | chr14:3262412-3305642 |
| 394 | 1700055C04Rik | NR_040726.1 | chr9:63886271-63889272 | 488 | 1700110I01Rik | NR_038059.1 | chr14:3500819-3668805 |
| 395 | 1700055N04Rik | NM_028545.2 | chr19:3958807-3970438 | 489 | 1700110I01Rik | NR_038059.1 | chr14:3740222-3906698 |
| 396 | 1700056E22Rik | NM_028516.1 | chr1:185856910-185857877 | 490 | 1700110K17Rik | NR_040728.1 | chr9:40141057-40150922 |
| 397 | 1700057G04Rik | NM_001033184.3 | chr9:92204214-92252714 | 491 | 1700111N16Rik | NR_033213.2 | chrX:67182435-67396763 |
| 398 | 1700057H15Rik | NR_040774.1 | chr4:124126868-124163202 | 492 | 1700112E06Rik | NM_028275.1 | chr14:22838934-23875310 |
| 399 | 1700060C16Rik | NR_045732.1 | chr6:143541872-143599808 | 493 | 1700112H15Rik | NR_040472.1 | chr1:186351719-186381570 |
| 400 | 1700060C20Rik | NR_036606.2 | chr2:158017744-158021470 | 494 | 1700112J05Rik | NR_077218.1 | chr5:77435467-77447888 |
| 401 | 1700061F12Rik | NR_038180.1 | chr2:9111141-9119111 | 495 | 1700113A16Rik | NR_045997.1 | chr3:87975481-87981707 |
| 402 | 1700061G19Rik | NM_030141.1 | chr17:57015055-57028261 | 496 | 1700113H08Rik | NM_029685.1 | chr10:86520790-86693344 |
| 403 | 1700061I17Rik | NR_038029.1 | chr3:116763439-116780683 | 497 | 1700119H24Rik | NR_040536.1 | chr16:34935941-34939415 |
| 404 | 1700063A18Rik | NR_040467.1 | chr1:97887235-97918335 | 498 | 1700120C14Rik | NR_045627.2 | chr15:99082219-99092472 |
| 405 | 1700063D05Rik | NR_040392.1 | chr9:41014237-41025710 | 499 | 1700120E14Rik | NR_045368.1 | chr18:74655332-74690778 |
| 406 | 1700063O14Rik | NR_045383.1 | chr5:92195267-92196326 | 500 | 1700120G07Rik | NR_046050.1 | chr7:142383447-142387685 |
| 407 | 1700064J06Rik | NR_045348.1 | chr10:118529960-118540163 | 501 | 1700120K04Rik | NR_027915.1 | chr7:134747416-134747959 |
| 408 | 1700064M15Rik | NR_045268.1 | chr12:100864262-100866184 | 502 | 1700121L16Rik | NR_045453.1 | chrX:102012114-102037794 |
| 409 | 1700065D16Rik | NM_001271569.1 | chr9:95755836-95852063 | 503 | 1700121N20Rik | NR_036593.1 | chr12:107680861-107685876 |
| 410 | 1700065D16Rik | NR_073361.1 | chr9:95755836-95852063 | 504 | 1700122O11Rik | NM_029689.1 | chr17:48173694-48175243 |
| 411 | 1700065E16Rik | NR_040315.2 | chr15:63648742-63651095 | 505 | 1700123I01Rik | NM_001165919.1 | chr19:6184409-6224219 |
| 412 | 1700065H16Rik | NR_108057.1 | chr15:63648742-63651095 | 506 | 1700123K08Rik | NM_029693.2 | chr5:139003067-139005922 |
| 413 | 1700065I11Rik | NR_040526.1 | chr6:35280845-35286829 | 507 | 1700123L14Rik | NR_003643.1 | chr6:96114497-96116199 |
| 414 | 1700065J18Rik | NR_040468.1 | chr1:194667898-194668933 | 508 | 1700123M08Rik | NR_040577.1 | chrX:11893720-11921442 |
| 415 | 1700065L07Rik | NR_108032.1 | chr6:73386959-73421015 | 509 | 1700123O12Rik | NR_045185.1 | chr4:10435177-10724949 |
| 416 | 1700065O20Rik | NR_045386.1 | chr18:49962985-49977610 | 510 | 1700123O20Rik | NM_021437.2 | chr14:55305008-55309579 |
| 417 | 1700066B17Rik | NR_040465.1 | chr7:39899272-39904175 | 511 | 1700123O21Rik | NR_045799.1 | chr16:5975680-5998589 |
| 418 | 1700066B19Rik | NM_001033168.2 | chr18:35888642-35890523 | 512 | 1700124L16Rik | NR_105027.1 | chr6:83711752-83712502 |
| 419 | 1700066M21Rik | NM_028546.1 | chr1:57434463-57442266 | 513 | 1700125G02Rik | NR_040651.1 | chr4:124568132-124572026 |
| 420 | 1700066N21Rik | NR_045924.1 | chr5:88337613-88408376 | 514 | 1700125G22Rik | NR_040548.1 | chr3:27052947-27055941 |
| 421 | 1700066O22Rik | NR_015541.2 | chr18:57664075-57693406 | 515 | 1700125H03Rik | NR_038181.1 | chr8:70880679-71259045 |
| 422 | 1700067G17Rik | NR_040471.1 | chr1:90912687-90918785 | 516 | 1700125H03Rik | NR_038189.1 | chr8:70880679-71259045 |
| 423 | 1700067K01Rik | NM_183097.1 | chr8:86525604-86528669 | 517 | 1700125H20Rik | NM_018589.1 | chr11:84984597-84994656 |
| 424 | 1700067P10Rik | NM_026625.2 | chr17:48226582-48227870 | 518 | 1700126H18Rik | NR_040695.1 | chr5:66557845-66582574 |
| 425 | 1700069L16Rik | NR_033216.1 | chr5:114142432-114174781 | 519 | 1700128E03Rik | NR_045938.2 | chr14:106816403-106885737 |
| 426 | 1700069P05Rik | NR_040527.1 | chr6:118196712-118198472 | 520 | 1700128F08Rik | NR_033618.2 | chr9:8221888-8241987 |
| 427 | 1700071K01Rik | NM_001033765.2 | chr1:81386004-81387041 | 521 | 1700129C05Rik | NM_026461.2 | chr14:59751876-59761730 |
| 428 | 1700071M16Rik | NR_045444.1 | chr7:43705399-43749150 | 522 | 1810006J19Rik | NR_040439.1 | chr1:100028043-100041232 |
| 429 | 1700071M16Rik | NR_045445.1 | chr7:43705399-43749150 | 523 | 1810007C17Rik | NR_045472.1 | chr12:50577979-50581849 |
| 430 | 1700072B07Rik | NR_040727.1 | chr9:58218310-58221990 | 524 | 1810007D17Rik | NR_038136.1 | chr19:58680818-58704243 |
| 431 | 1700072O05Rik | NR_045733.1 | chr6:120504813-120524222 | 525 | 1810008I18Rik | NR_045301.1 | chr7:72948937-72951109 |
| 432 | 1700073E17Rik | NR_003625.1 | chr6:145336144-145340743 | 526 | 1810009A15Rik | NR_025463.3 | chr19:8958367-8965249 |
| 433 | 1700074H08Rik | NR_045296.1 | chr13_random:141204-142745 | 527 | 1810009A15Rik | NR_104416.1 | chr19:8958367-8965249 |
| 434 | 1700074H08Rik | NR_045296.1 | chr13_random:335114-336655 | 528 | 1810009J06Rik | NM_023707.2 | chr6:40914770-40918426 |
| 435 | 1700074P13Rik | NM_028550.3 | chr6:40870458-40890856 | 529 | 1810010D01Rik | NR_033626.1 | chr7:152391722-152394024 |
| 436 | 1700080E11Rik | NM_028562.3 | chr9:105045673-105047412 | 530 | 1810010H24Rik | NM_001163473.1 | chr11:106889536-106891756 |
| 437 | 1700080N15Rik | NR_040500.1 | chr2:4053110-4062187 | 531 | 1810011H11Rik | NM_001163616.1 | chr14:33599148-33631154 |
| 438 | 1700080O16Rik | NM_028851.1 | chrX:49321871-49325949 | 532 | 1810011O10Rik | NM_026931.2 | chr8:25548087-25549418 |
| 439 | 1700081H04Rik | NR_040693.1 | chr5:119558244-119564552 | 533 | 1810012K16Rik | NR_045473.1 | chr8:23509192-23510863 |
| 440 | 1700084C01Rik | NM_001033185.2 | chr1:171859069-171864784 | 534 | 1810013A23Rik | NR_045427.1 | chr17:28408653-28410108 |
| 441 | 1700084E18Rik | NR_028299.1 | chr2:30092717-30093151 | 535 | 1810013L24Rik | NM_001081400.3 | chr16:8830192-8859017 |
| 442 | 1700084F23Rik | NR_045965.1 | chr13:70142927-70167226 | 536 | 1810014B01Rik | NR_015572.2 | chr10:86148271-86152699 |
| 443 | 1700084J12Rik | NR_033608.1 | chr15:33334964-33335694 | 537 | 1810018F18Rik | NR_038140.1 | chr19:58773406-58775813 |
| 444 | 1700085C21Rik | NR_046045.1 | chr12:84033507-84040142 | 538 | 1810019D21Rik | NR_040344.1 | chr8:108655082-108662622 |
| 445 | 1700086L19Rik | NR_030733.1 | chr12:75385262-75396937 | 539 | 1810019D21Rik | NR_040345.1 | chr8:108655082-108662622 |
| 446 | 1700086L19Rik | NR_030734.1 | chr12:75385262-75396937 | 540 | 1810019D21Rik | NR_040346.1 | chr8:108655082-108662622 |
| 447 | 1700086L19Rik | NR_030735.1 | chr12:75385262-75396937 | 541 | 1810020O05Rik | NR_045482.1 | chr6:87625586-87640841 |
| 448 | 1700086O06Rik | NR_015475.1 | chr18:38398058-38422283 | 542 | 1810021B22Rik | NR_040417.1 | chr15:88901627-88906284 |
| 449 | 1700086O06Rik | NR_027903.1 | chr18:38398058-38422283 | 543 | 1810022K09Rik | NM_001099674.1 | chr3:14606289-14611256 |
| 450 | 1700086O06Rik | NR_027388.1 | chr18:38398058-38422283 | 544 | 1810024B03Rik | NM_198630.2 | chr2:127012090-127034016 |
| 451 | 1700088E04Rik | NM_138581.2 | chr15:78965085-78971681 | 545 | 1810026B05Rik | NR_037569.1 | chr7:80684684-80703281 |
| 452 | 1700091H14Rik | NR_073362.1 | chr4:42668556-42674084 | 546 | 1810026J23Rik | NM_178619.4 | chr9:21397166-21400414 |
| 453 | 1700092C02Rik | NR_045467.1 | chr8:80484070-80152855 | 547 | 1810030O07Rik | NM_175141.5 | chrX:12232009-12250672 |
| 454 | 1700092C10Rik | NR_045931.1 | chr4:69782856-69789900 | 548 | 1810032O08Rik | NR_027819.1 | chr11:116532973-116537112 |
| 455 | 1700092E19Rik | NR_045933.1 | chr13:26375027-26404275 | 549 | 1810032O08Rik | NR_027820.1 | chr11:116532973-116537112 |
| 456 | 1700092K14Rik | NR_045930.1 | chr7:114059571-114060513 | 550 | 1810032O08Rik | NR_027821.1 | chr11:116532973-116537112 |
| 457 | 1700092M07Rik | NM_001177347.1 | chr19:8815207-8815715 | 551 | 1810034E14Rik | NR_045798.1 | chr13:64350008-64369453 |
| 458 | 1700093K21Rik | NM_001110133.1 | chr11:23416202-23419942 | 552 | 1810037H17Rik | NM_024461.2 | chr3:122627314-122629112 |
| 459 | 1700093K21Rik | NR_026105.3 | chr11:23416202-23419942 | 553 | 1810041L15Rik | NM_001163145.1 | chr15:84209632-84277527 |
| 460 | 1700094D03Rik | NM_028567.1 | chr3:89866718-88872269 | 554 | 1810043G02Rik | NM_026431.2 | chr10:77441394-77448183 |
| 461 | 1700094J05Rik | NR_040580.1 | chr10:75851760-75864252 | 555 | 1810043H04Rik | NM_001110242.1 | chr11:119960247-119961738 |
| 462 | 1700094M24Rik | NR_046049.1 | chr6:52442444-52450079 | 556 | 1810044D09Rik | NR_038153.1 | chr6:91390980-91391749 |
| 463 | 1700095A21Rik | NR_045468.1 | chr4:145651166-145679000 | 557 | 1810046K07Rik | NM_027217.1 | chr9:51097790-51137022 |
| 464 | 1700095I08Rik | NR_040676.1 | chr5:113117895-113325382 | 558 | 1810053B23Rik | NR_040486.1 | chr16:93343960-93359788 |
| 465 | 1700095I08Rik | NR_040676.1 | chr5:113117895-113325382 | 559 | 1810053B23Rik | NR_040487.1 | chr16:93343960-93359788 |
| 466 | 1700096J18Rik | NR_027883.1 | chr11:109208180-109214965 | 560 | 1810053B23Rik | NR_040488.1 | chr16:93343960-93359788 |
| 467 | 1700096K18Rik | NR_027388.1 | chr5:25035835-25037284 | 561 | 1810053B23Rik | NR_040489.1 | chr16:93343960-93359788 |
| 468 | 1700097N02Rik | NR_045287.1 | chr17:30759385-30763850 | 562 | 1810053B23Rik | NR_040490.1 | chr16:93343960-93359788 |
| 469 | 1700100L14Rik | NR_045934.1 | chr13:70712118-70714982 | 563 | 1810053B23Rik | NR_040491.1 | chr16:93343960-93359788 |
| 470 | 1700101E03Rik | NM_001166705.1 | chr2:28811000-28910586 | 564 | 1810055G02Rik | NM_028077.2 | chr19:3708332-3717881 |
| 471 | 1700101I11Rik | NR_045270.1 | chr6:129482202-129483302 | 565 | 1810058I24Rik | NR_015608.1 | chr6:35202698-35212059 |
| 472 | 1700101O22Rik | NR_045045.1 | chr12:7378844-7387136 | 566 | 1810058I24Rik | NR_027875.1 | chr6:35202698-35212059 |
| | | | | 567 | 1810062G17Rik | NM_028183.1 | chr3:36374858-36381221 |

Fig. 25 - 4

| | | | | | | | |
|---|---|---|---|---|---|---|---|
| 568 | 1810062O18Rik | NR_033571.1 | chr14:21365515-21389902 | 663 | 2310022A10Rik | NM_001122767.1 | chr7:28338308-28367117 |
| 569 | 1810064F22Rik | NR_027981.1 | chr9:22011229-22018304 | 664 | 2310022A10Rik | NM_175107.5 | chr7:28338308-28367117 |
| 570 | 1810065E05Rik | NM_027239.2 | chr11:58234612-58239525 | 665 | 2310022B05Rik | NM_175149.4 | chr8:127159655-127187269 |
| 571 | 2010001E11Rik | NM_001163503.1 | chr10:39640187-39646729 | 666 | 2310030A07Rik | NR_040603.1 | chr1:152167811-152193901 |
| 572 | 2010002M12Rik | NM_053227.1 | chr19:34691540-34715233 | 667 | 2310030G06Rik | NM_025865.2 | chr9:50547795-50554626 |
| 573 | 2010003K11Rik | NM_027237.1 | chr19:4496787-4498583 | 668 | 2310033P09Rik | NM_024210.2 | chr11:59021862-59024236 |
| 574 | 2010005H15Rik | NM_029733.3 | chr16:36221647-36257513 | 669 | 2310034C09Rik | NM_054100.2 | chr16:88759091-88760034 |
| 575 | 2010009K17Rik | NR_040609.1 | chr2:157896100-157917533 | 670 | 2310034G01Rik | NR_040418.1 | chr19:46422690-46423478 |
| 576 | 2010010A06Rik | NR_045393.1 | chr18:75448313-75456983 | 671 | 2310034O05Rik | NR_040679.1 | chr5:100639710-100647068 |
| 577 | 2010010A06Rik | NR_045394.1 | chr18:75448313-75456983 | 672 | 2310035C23Rik | NM_029349.1 | chr1:107560437-107651708 |
| 578 | 2010012G05Rik | NM_025563.3 | chr19:46764395-46777872 | 673 | 2310035C23Rik | NM_173187.3 | chr1:107560437-107651708 |
| 579 | 2010015L04Rik | NM_001166029.1 | chr4:154775077-154817219 | 674 | 2310036O22Rik | NM_026760.2 | chr8:875550731-87554185 |
| 580 | 2010015L04Rik | NM_177674.5 | chr4:154775077-154817219 | 675 | 2310039H08Rik | NM_025966.3 | chr17:46909583-46910356 |
| 581 | 2010016L18Rik | NR_033207.1 | chr3:106284904-106288831 | 676 | 2310039N15Rik | NR_045337.1 | chr10:94798909-94825850 |
| 582 | 2010106C02Rik | NR_045435.1 | chr17:86684507-86686518 | 677 | 2310040G24Rik | NR_040292.1 | chr6:86433369-86438221 |
| 583 | 2010106E10Rik | NM_001168590.1 | chrX:109608882-109671952 | 678 | 2310040G24Rik | NR_040293.1 | chr6:86433369-86438221 |
| 584 | 2010106E10Rik | NM_026333.4 | chrX:109608882-109671952 | 679 | 2310042E22Rik | NM_025634.3 | chr16:21152731-21154017 |
| 585 | 2010107E04Rik | NM_027360.2 | chr12:113199586-113205188 | 680 | 2310043L19Rik | NR_037994.1 | chr1:179571672-179573074 |
| 586 | 2010107G12Rik | NM_001025573.2 | chr6:34895294-34927999 | 681 | 2310043O21Rik | NR_045757.1 | chr15:38479098-38524689 |
| 587 | 2010107G23Rik | NM_027251.3 | chr10:61570403-61573761 | 682 | 2310045N01Rik | NM_001145521 | chr8:72663611-72671159 |
| 588 | 2010109A12Rik | NM_029363.1 | chr5:93635543-93642500 | 683 | 2310047M10Rik | NM_028005.3 | chr11:68873276-68875078 |
| 589 | 2010109J03Rik | NM_025929.2 | chr15:74708785-74712134 | 684 | 2310050O09Rik | NM_025621.2 | chr3:92672280-92674127 |
| 590 | 2010111I01Rik | NM_001289924.1 | chr13:63066252-63533053 | 685 | 2310057J18Rik | NM_026336.3 | chr10:28692093-28706112 |
| 591 | 2010111I01Rik | NM_001289926.1 | chr13:63066252-63533053 | 686 | 2310057M21Rik | NM_026655.3 | chr7:138486231-138506212 |
| 592 | 2010111I01Rik | NR_110520.1 | chr13:63066252-63533053 | 687 | 2310057N15Rik | NM_027170.1 | chr6:88773425-88774451 |
| 593 | 2010111I01Rik | NR_110521.1 | chr13:63066252-63533053 | 688 | 2310061I04Rik | NM_001033630.1 | chr17:36029621-36034323 |
| 594 | 2010204K13Rik | NM_027924.1 | chrX:6988942-7000114 | 689 | 2310061J03Rik | NR_027965.1 | chr16:55973381-55974730 |
| 595 | 2010204K13Rik | NR_027925.1 | chrX:6988942-7000114 | 690 | 2310061N02Rik | NM_027155.1 | chr6:88707415-88708207 |
| 596 | 2010300C02Rik | NM_028096.1 | chr1:37668520-37776656 | 691 | 2310065F04Rik | NR_038055.1 | chr11:66925962-66933582 |
| 597 | 2010308F09Rik | NM_045429.1 | chrX:12811766-12824859 | 692 | 2310067B10Rik | NM_028014.3 | chr11:115626747-115660347 |
| 598 | 2010308F09Rik | NM_045430.1 | chrX:12811766-12824859 | 693 | 2310068L16Rik | NR_024124.1 | chr15:99802598-99803718 |
| 599 | 2010310C07Rik | NR_045169.1 | chr6:42320670-42330557 | 694 | 2310069B03Rik | NR_040520.1 | chr6:82827859-82831847 |
| 600 | 2010315B03Rik | NM_001243117.1 | chr9_random:202786-223677 | 695 | 2310069G16Rik | NR_040309.1 | chr15:44619309-44637375 |
| 601 | 2010315B03Rik | NM_001243118.1 | chr9_random:202786-223677 | 696 | 2310079G19Rik | NM_027173.1 | chr16:88627032-88627911 |
| 602 | 2010315B03Rik | NM_001243119.1 | chr9_random:202786-223677 | 697 | 2310081J21Rik | NR_045474.1 | chr13:50774538-50775593 |
| 603 | 2010320M18Rik | NM_029440.1 | chr8:73300760-73301505 | 698 | 2310081I21Rik | NR_045474.1 | chr13:50357183-50358238 |
| 604 | 2200002D01Rik | NM_028179.1 | chr7:30032540-30033486 | 699 | 2410002F23Rik | NM_025880.4 | chr7:51502092-51507689 |
| 605 | 2200002J24Rik | NM_026961.2 | chr7:31483944-31485553 | 700 | 2410003L11Rik | NR_045496.1 | chr11:97459824-97484207 |
| 606 | 2210010C04Rik | NM_023333.4 | chr6:40980266-40985508 | 701 | 2410004A01Rik | NR_045455.4 | chr3:145600995-145607239 |
| 607 | 2210011C24Rik | NM_001291292.1 | chr8:86534127-86535619 | 702 | 2410004I01Rik | NR_037963.1 | chr11:102819613-102825468 |
| 608 | 2210013O21Rik | NM_027327.1 | chrX:150158096-150175839 | 703 | 2410004N09Rik | NR_038151.1 | chr18:33954545-33955643 |
| 609 | 2210015D19Rik | NR_015577.1 | chr11:5662153-5684713 | 704 | 2410004N09Rik | NR_038152.1 | chr18:33954545-33955643 |
| 610 | 2210016F16Rik | NM_027335.1 | chr13:58481406-58486586 | 705 | 2410004P03Rik | NM_001201332.1 | chr12:17011763-17018533 |
| 611 | 2210016L21Rik | NM_028211.1 | chr5:115392210-115398549 | 706 | 2410004P03Rik | NM_001201333.1 | chr12:17011763-17018533 |
| 612 | 2210018M11Rik | NM_172280.2 | chr7:105739115-105805079 | 707 | 2410006H16Rik | NR_030738.1 | chr1:62416379-62418308 |
| 613 | 2210019H11Rik | NR_038157.1 | chr5:148040174-148083097 | 708 | 2410007B07Rik | NR_040539.1 | chr3:75451362-75459653 |
| 614 | 2210039B01Rik | NR_044985.1 | chr12:74649469-74652973 | 709 | 2410012E07Rik | NR_045939.1 | chr14:71252739-71273761 |
| 615 | 2210404O09Rik | NM_001256493.1 | chr17:22016536-22046893 | 710 | 2410020J08Rik | NM_028003.1 | chr9:98765185-98766999 |
| 616 | 2210407C18Rik | NM_144544.2 | chr11:58421707-58426994 | 711 | 2410015M20Rik | NR_153152.3 | chr7:56746874-56749194 |
| 617 | 2210408F21Rik | NR_040257.1 | chr6:31170350-31287394 | 712 | 2410016O06Rik | NM_023633.1 | chr12:85291557-85293903 |
| 618 | 2210408F21Rik | NR_040258.1 | chr6:31170350-31287394 | 713 | 2410017J17Rik | NR_033517.1 | chr17:36281962-36299319 |
| 619 | 2210408F21Rik | NR_040259.1 | chr6:31170350-31287394 | 714 | 2410018L13Rik | NR_015504.1 | chr12:22990696-23046943 |
| 620 | 2210408F21Rik | NR_040260.1 | chr6:31170350-31287394 | 715 | 2410021I03Rik | NR_045428.1 | chr17:69624702-69626546 |
| 621 | 2210408F21Rik | NR_040261.1 | chr6:31170350-31287394 | 716 | 2410076I21Rik | NM_028598.1 | chr9:58500663-58589366 |
| 622 | 2210408F21Rik | NR_040262.1 | chr6:31170350-31287394 | 717 | 2410088K16Rik | NR_040493.1 | chr1:90651464-90652308 |
| 623 | 2210408I21Rik | NM_001081353.1 | chr13:77274796-77752940 | 718 | 2410089E03Rik | NM_001162906.1 | chr15:8119105-8221158 |
| 624 | 2210408I21Rik | NM_001145676.1 | chr13:77274796-77752940 | 719 | 2410114N07Rik | NR_040652.1 | chr4:34857037-34858730 |
| 625 | 2210409D07Rik | NR_045360.1 | chr18:57791733-57798239 | 720 | 2410124H12Rik | NM_029740.1 | chr18:92478986-92497610 |
| 626 | 2210409E12Rik | NR_038492.2 | chr11:88833951-88834328 | 721 | 2410127L17Rik | NM_026120.4 | chr19:18745269-18779282 |
| 627 | 2210414B05Rik | NR_040643.1 | chr4:3583652-3590255 | 722 | 2410131K14Rik | NM_001081236.1 | chr5:118695235-118713123 |
| 628 | 2210416G15Rik | NR_045499.1 | chr11:87911560-87913609 | 723 | 2410137M14Rik | NM_029747.3 | chr17:37114645-37118182 |
| 629 | 2210417A02Rik | NR_028285.1 | chr5:149553415-149554715 | 724 | 2410141K09Rik | NM_001209196.1 | chr13:66519049-66542054 |
| 630 | 2210420H20Rik | NR_045389.1 | chr18:82923896-82928431 | 725 | 2410141K09Rik | NM_183119.3 | chr13:66519049-66542054 |
| 631 | 2300002M23Rik | NM_175148.3 | chr17:35704429-35705890 | 726 | 2500004C02Rik | NR_040318.1 | chr2:153166892-153171546 |
| 632 | 2300003K06Rik | NM_001195383.1 | chr9:99698461-99699380 | 727 | 2510002D24Rik | NM_001033164.2 | chr16:18836672-18840206 |
| 633 | 2300005B03Rik | NM_001081961.1 | chr15:74573268-74577117 | 728 | 2510003E04Rik | NM_028197.2 | chr10:62021217-62041205 |
| 634 | 2300009A05Rik | NM_027090.1 | chr9:63242253-63247051 | 729 | 2510009E07Rik | NM_001001881.2 | chr16:21649117-21694738 |
| 635 | 2310001H17Rik | NR_040265.1 | chr6:129182640-129188500 | 730 | 2510039O18Rik | NM_029841.1 | chr4:147315003-147321423 |
| 636 | 2310001H17Rik | NR_040266.1 | chr6:129182640-129188500 | 731 | 2510049J12Rik | NM_001101431.1 | chr6:115533564-115542594 |
| 637 | 2310001H17Rik | NR_040268.1 | chr6:129182640-129188500 | 732 | 2610001J05Rik | NM_024619.1 | chr6:13819073-13821483 |
| 638 | 2310001K24Rik | NR_028122.1 | chr2:163298281-163298739 | 733 | 2610002J02Rik | NM_001190445.1 | chr4:154624074-154630796 |
| 639 | 2310002D06Rik | NR_045490.1 | chr12:81608192-81618943 | 734 | 2610002J02Rik | NR_033802.1 | chr4:154624074-154630796 |
| 640 | 2310002F09Rik | NR_077063.1 | chr7:51000835-51011306 | 735 | 2610002M06Rik | NM_025921.3 | chrX:104978091-105011673 |
| 641 | 2310002J15Rik | NM_026415.3 | chr2:25094338-25095417 | 736 | 2610005L07Rik | NM_028428.1 | chr8:19981360-20020392 |
| 642 | 2310002L09Rik | NM_027104.3 | chr4:73585274-73596750 | 737 | 2610008E11Rik | NM_001004362.2 | chr10:78527118-78560345 |
| 643 | 2310002L09Rik | NM_027104.3 | chr4:73585274-73596750 | 738 | 2610015P09Rik | NM_027801.1 | chr16:43890014-43964427 |
| 644 | 2310003H01Rik | NM_027980.2 | chr11:120230875-120240060 | 739 | 2610016A17Rik | NR_045347.1 | chr19:25745623-25746729 |
| 645 | 2310005A03Rik | NR_040634.1 | chr2:154923526-154925815 | 740 | 2610018G03Rik | NM_133729.1 | chrX:48194612-48245027 |
| 646 | 2310005E16Rik | NR_045498.1 | chr13:99194084-99205020 | 741 | 2610020C07Rik | NR_038156.1 | chr16:11203476-11225889 |
| 647 | 2310005G13Rik | NM_183281.2 | chr16:57037079-57071459 | 742 | 2610020H08Rik | NM_001004187.1 | chr7:126937643-126992455 |
| 648 | 2310007B03Rik | NM_001159940.1 | chr1:95047931-95057525 | 743 | 2610020H08Rik | NM_028129.2 | chr7:126937643-126992455 |
| 649 | 2310007B03Rik | NM_172411.4 | chr1:95047931-95057525 | 744 | 2610027F03Rik | NR_077059.1 | chr11:85605162-85645890 |
| 650 | 2310007L24Rik | NM_029345.1 | chr11:106236139-106238428 | 745 | 2610028E06Rik | NR_015560.1 | chr4:125565094-125599554 |
| 651 | 2310008N11Rik | NR_045904.1 | chr8:27925068-27934895 | 746 | 2610028H24Rik | NM_029816.2 | chr10:75911826-75923963 |
| 652 | 2310009A05Rik | NR_040377.1 | chr9:72887524-72890582 | 747 | 2610034B18Rik | NM_027420.4 | chr7:87070244-87080150 |
| 653 | 2310009B15Rik | NM_001081226.1 | chr1:140748555-140753431 | 748 | 2610034M16Rik | NM_027001.1 | chr17:59018230-59130798 |
| 654 | 2310010J17Rik | NR_046006.1 | chr7:97273345-97278446 | 749 | 2610035D17Rik | NR_015561.1 | chr11:112905219-113063152 |
| 655 | 2310010J17Rik | NR_046007.1 | chr7:97273345-97278446 | 750 | 2610035F20Rik | NR_045046.1 | chr14:122869598-122874421 |
| 656 | 2310011J03Rik | NM_025521.3 | chr10:79781000-79783293 | 751 | 2610037D02Rik | NR_040423.1 | chr15:96020905-96028405 |
| 657 | 2310014L17Rik | NM_029809.2 | chr7:13512764-13516421 | 752 | 2610044O15Rik 8 | NM_153780.3 | chr17:95213817-95234160 |
| 658 | 2310015A10Rik | NR_033514.1 | chr12:81221532-81233831 | 753 | 2610100L16Rik | NR_033490.1 | chr3:17689921-17700071 |
| 659 | 2310015B20Rik | NR_038041.1 | chr10:69667414-69682459 | 754 | 2610203C20Rik | NR_015483.1 | chr9:41389336-41400912 |
| 660 | 2310015D24Rik | NR_037997.1 | chr16:13514223-13520512 | 755 | 2610203C22Rik | NR_015470.1 | chr1:9550914-9621173 |
| 661 | 2310016D03Rik | NR_045491.1 | chr2:131095423-31152223 | 756 | 2610206C17Rik | NR_038175.1 | chr7:91838149-91925059 |
| 662 | 2310020H05Rik | NR_045495.1 | chr13:99846482-99857876 | | | | |

Fig. 25 - 5

| | | | | | | | | |
|---|---|---|---|---|---|---|---|---|
| 757 | 2610207O16Rik | NR_110495.1 | chr1:42763907-42770299 | | 851 | 2900079G21Rik | NR_033431.1 | chr9:111967594-112251429 |
| 758 | 2610301B20Rik | NM_026005.3 | chr4:10801644-10826570 | | 852 | 2900079G21Rik | NR_033432.1 | chr9:111967594-112251429 |
| 759 | 2610305D13Rik | NM_145078.2 | chr4:146986044-147016617 | | 853 | 2900079G21Rik | NR_033433.1 | chr9:111967594-112251429 |
| 760 | 2610306M01Rik | NR_028298.1 | chr6:86798400-86799434 | | 854 | 2900092C05Rik | NM_028434.3 | chr7:13097899-13141670 |
| 761 | 2610307P16Rik | NR_045053.1 | chr13:28551902-28977291 | | 855 | 2900092D14Rik | NR_027891.1 | chr1:42757180-42760021 |
| 762 | 2610307P16Rik | NR_045054.1 | chr13:28551902-28977291 | | 856 | 2900097C17Rik | NR_024329.1 | chr2:156213798-156218715 |
| 763 | 2610316D01Rik | NR_045172.1 | chr3:45084360-45182182 | | 857 | 3000002C10Rik | NR_033215.1 | chr9:109792667-109733945 |
| 764 | 2610318N02Rik | NM_183287.2 | chr16:17113491-17125199 | | 858 | 3010001F23Rik | NR_045451.1 | chrX:148803114-148851245 |
| 765 | 2610507B11Rik | NM_001002004.2 | chr1:78075255-78104127 | | 859 | 3010001F23Rik | NR_045452.1 | chrX:148803114-148851245 |
| 766 | 2610507I01Rik | NR_037964.1 | chr11:59011294-59015933 | | 860 | 3010026O09Rik | NM_026543.3 | chr11:49988352-50013617 |
| 767 | 2610524H06Rik | NM_181075.3 | chr5:115271945-115273477 | | 861 | 3010033K07Rik | NR_077224.1 | chr8:111077151-111108577 |
| 768 | 2610528A11Rik | NM_001206684.1 | chr14:37915325-37923287 | | 862 | 3100003L05Rik | NR_045907.1 | chr7:131769183-131852449 |
| 769 | 2610528J11Rik | NM_025572.2 | chr4:118199879-118202822 | | 863 | 3110001I22Rik | NM_025653.2 | chr16:13672113-13678478 |
| 770 | 2700029M09Rik | NM_028299.1 | chr8:63369247-63386369 | | 864 | 3110002H16Rik | NM_029623.2 | chr18:12327239-12348478 |
| 771 | 2700038G22Rik | NR_045040.1 | chr5:23356414-23360851 | | 865 | 3110007F17Rik | NM_028426.1 | chrX:120217167-120256902 |
| 772 | 2700038G22Rik | NR_045042.1 | chr5:23356414-23380851 | | 866 | 3110009E18Rik | NM_001172074.1 | chr1:122017763-122084766 |
| 773 | 2700046A07Rik | NR_037693.1 | chr18:62911327-62916001 | | 867 | 3110009E18Rik | NM_028439.2 | chr1:122017763-122084766 |
| 774 | 2700046G09Rik | NR_033198.1 | chr19:32463705-32465674 | | 868 | 3110009F21Rik | NR_045466.1 | chr12:111389863-111396283 |
| 775 | 2700049A03Rik | NM_001163378.1 | chr12:72237834-72344290 | | 869 | 3110015O05Rik | NR_045908.1 | chr13:112001676-112019639 |
| 776 | 2700049A03Rik | NM_029818.1 | chr12:72237834-72344290 | | 870 | 3110021A11Rik | NR_030776.1 | chr6:119798210-119799034 |
| 777 | 2700054A10Rik | NR_045436.1 | chr17:13679886-13746960 | | 871 | 3110021N24Rik | NM_001254730.1 | chr4:108392254-108454509 |
| 778 | 2700054A10Rik | NR_045437.1 | chr17:13679886-13746960 | | 872 | 3110035E14Rik | NM_178399.4 | chr1:9591348-9617223 |
| 779 | 2700060E02Rik | NM_026528.3 | chr14:20630624-20643045 | | 873 | 3110039I08Rik | NR_040725.2 | chr9:41184643-41240162 |
| 780 | 2700062C07Rik | NM_026529.4 | chr18:24629371-24626268 | | 874 | 3110039M20Rik | NR_026733.1 | chr12:50490638-50508333 |
| 781 | 2700069J18Rik | NR_045905.2 | chr3:5177824-5220823 | | 875 | 3110040N11Rik | NM_026077.3 | chr7:88927072-88934339 |
| 782 | 2700070H01Rik | NR_046019.1 | chr14:63673909-63676986 | | 876 | 3110043O21Rik | NM_001081343.1 | chr4:35138530-35173129 |
| 783 | 2700081O15Rik | NM_175381.6 | chr19:7492115-7500394 | | 877 | 3110045C21Rik | NR_040438.1 | chr1:171899540-171902527 |
| 784 | 2700086A05Rik | NR_015611.2 | chr6:52151123-52163596 | | 878 | 3110052M02Rik | NM_001166497.1 | chr17:21787577-21801933 |
| 785 | 2700089E24Rik | NM_001183445.2 | chr6:133055256-133060917 | | 879 | 3110056K07Rik | NR_045055.1 | chr12:72075609-72116810 |
| 786 | 2700089E24Rik | NM_001271582.1 | chr6:133055256-133060917 | | 880 | 3110056K07Rik | NR_045056.1 | chr12:72075609-72116810 |
| 787 | 2700089E24Rik | NM_001271583.1 | chr6:133055256-133060917 | | 881 | 3110057O12Rik | NM_026622.3 | chr3:40698199-40740229 |
| 788 | 2700089E24Rik | NR_073368.1 | chr6:133055256-133060917 | | 882 | 3110062M04Rik | NM_001135611.1 | chr6:34813145-34828065 |
| 789 | 2700089J24Rik | NR_045308.1 | chr19:59567625-59635294 | | 883 | 3110062M04Rik | NM_199145.2 | chr6:34813145-34828065 |
| 790 | 2700094K13Rik | NM_001133166.2 | chr2:84509377-84510865 | | 884 | 3110070M22Rik | NR_027974.1 | chr13:120276064-120277191 |
| 791 | 2700094K13Rik | NM_001037279.1 | chr2:84509377-84510865 | | 885 | 3110079O15Rik | NM_028473.1 | chr1:89366838-89372034 |
| 792 | 2700097O09Rik | NM_028314.2 | chr12:56146647-56181097 | | 886 | 3110082I17Rik | NM_028469.3 | chr5:139835693-139936488 |
| 793 | 2700097O09Rik | NR_030764.1 | chr12:56146647-56181097 | | 887 | 3110082J24Rik | NM_001256263.1 | chr5:30430124-30432626 |
| 794 | 2700099C18Rik | NR_024720.1 | chr17:95149440-95174469 | | 888 | 3110099E03Rik | NR_030712.1 | chr2:115319248-115337937 |
| 795 | 2810001G20Rik | NR_033780.1 | chr11:63892985-63896761 | | 889 | 3200001D21Rik | NR_045884.2 | chr12:89603758-89615767 |
| 796 | 2810002D19Rik | NR_027831.1 | chr2:94246863-94251837 | | 890 | 3300002I08Rik | NM_027017.1 | chr2:150136672-150188501 |
| 797 | 2810004N23Rik | NM_025615.2 | chr8:127363254-127386929 | | 891 | 3300005D01Rik | NR_045079.1 | chr17:5798656-5803242 |
| 798 | 2810006K23Rik | NM_001134712.2 | chr5:124778097-124791861 | | 892 | 3300005D01Rik | NR_045080.1 | chr17:5798656-5803242 |
| 799 | 2810006K23Rik | NM_028310.3 | chr5:124778097-124791861 | | 893 | 3300005D01Rik | NR_045081.1 | chr17:5798656-5803242 |
| 800 | 2810007J24Rik | NM_001199306.1 | chr7:14996034-15031936 | | 894 | 3425401B19Rik | NM_001195097.1 | chr14:33472304-33498458 |
| 801 | 2810007J24Rik | NM_175250.5 | chr7:14996034-15031936 | | 895 | 3632451O06Rik | NM_026742.4 | chr14:50301693-50403042 |
| 802 | 2810008D09Rik | NR_027059.1 | chr11:116938097-116940269 | | 896 | 3632454L22Rik | NR_040281.1 | chrX:131556960-131594875 |
| 803 | 2810013P06Rik | NR_045268.1 | chr8:125566474-125568502 | | 897 | 3632454L22Rik | NR_040282.1 | chrX:131556960-131594875 |
| 804 | 2810021J22Rik | NR_027984.1 | chr11:58680741-58697840 | | 898 | 3632454L22Rik | NR_040283.1 | chrX:131556960-131594875 |
| 805 | 2810025M15Rik | NR_027984.1 | chr1:159342483-159350367 | | 899 | 3830403N18Rik | NM_027510.2 | chr5:53389748-53406673 |
| 806 | 2810029C07Rik | NR_045295.1 | chr12:112810527-112812613 | | 900 | 3830406C13Rik | NM_001284383.1 | chr14:13116716-13135745 |
| 807 | 2810032G03Rik | NR_015579.1 | chr12:5383307-5422938 | | 901 | 3830406C13Rik | NM_001284384.1 | chr14:13116716-13135745 |
| 808 | 2810047C21Rik | NR_015598.1 | chr7:10034292-10041283 | | 902 | 3830406C13Rik | NM_001284385.1 | chr14:13116716-13135745 |
| 809 | 2810049E08Rik | NR_036594.1 | chr13:84030812-84068315 | | 903 | 3830406C13Rik | NM_001284386.1 | chr14:13116716-13135745 |
| 810 | 2810055G20Rik | NR_015543.2 | chr16:77329572-77558673 | | 904 | 3830406C13Rik | NM_001284387.1 | chr14:13116716-13135745 |
| 811 | 2810403A07Rik | NM_028814.3 | chr3:88489715-88516855 | | 905 | 3830406C13Rik | NM_146051.3 | chr14:13116716-13135745 |
| 812 | 2810403D21Rik | NR_015493.2 | chrX:106029816-106082235 | | 906 | 3830406C13Rik | NM_178141.3 | chr14:13116716-13135745 |
| 813 | 2810404M03Rik | NR_045497.1 | chr8:42912620-43131556 | | 907 | 3830408C21Rik | NR_015471.1 | chr13:107812649-107823598 |
| 814 | 2810405F15Rik | NR_033447.1 | chr2:115900283-115901832 | | 908 | 3830417A13Rik | NM_027512.2 | chrX:61426722-61431953 |
| 815 | 2810408A11Rik | NM_027419.3 | chr11:69710859-69714488 | | 909 | 3930402G23Rik | NR_030715.1 | chr8:10924426-10928457 |
| 816 | 2810408J11Rik | NR_038009.1 | chr1:64726442-64737233 | | 910 | 4430402I18Rik | NM_198651.2 | chr19:28997554-29038644 |
| 817 | 2810408M09Rik | NM_001007581.1 | chr2:165315611-165318814 | | 911 | 4631405J19Rik | NR_110333.1 | chr2:92869505-92873602 |
| 818 | 2810410L24Rik | NR_036682.1 | chr1:120047963-120051170 | | 912 | 4632415L05Rik | NR_027985.1 | chr3:19794870-19798984 |
| 819 | 2810417H13Rik | NM_026054.1 | chr9:65738130-65751358 | | 913 | 4632427E13Rik | NR_015510.1 | chr7:99889215-99889969 |
| 820 | 2810428I15Rik | NM_025577.2 | chr8:73028194-73030638 | | 914 | 4632428C04Rik | NR_033631.1 | chr16:30008752-30021516 |
| 821 | 2810429J04Rik | NR_015522.1 | chr13:3477548-3491644 | | 915 | 4632428N05Rik | NM_001159572.1 | chr10:59765497-60159238 |
| 822 | 2810433D01Rik | NR_133424.1 | chr1:102480820-102485730 | | 916 | 4632428N05Rik | NM_028732.4 | chr10:59765497-60159238 |
| 823 | 2810442I21Rik | NR_110421.1 | chr11:16834711-16851285 | | 917 | 4632434I11Rik | NM_001080995.1 | chr7:100006036-100022742 |
| 824 | 2810442I21Rik | NR_110422.1 | chr11:16834711-16851285 | | 918 | 4732416N19Rik | NR_015615.1 | chr6:148160810-148184185 |
| 825 | 2810442I21Rik | NR_110423.1 | chr11:16834711-16851285 | | 919 | 4732456N10Rik | NM_177717.4 | chr15:101382787-101393381 |
| 826 | 2810442I21Rik | NR_110424.1 | chr11:16834711-16851285 | | 920 | 4732471J01Rik | NR_015569.3 | chr7:26161837-26351436 |
| 827 | 2810442I21Rik | NR_110425.1 | chr11:16834711-16851285 | | 921 | 4732471J01Rik | NR_073027.1 | chr7:26161837-26351436 |
| 828 | 2810442N19Rik | NR_040562.1 | chr1:163935100-163946616 | | 922 | 4732471J01Rik | NR_073028.1 | chr7:26161837-26351436 |
| 829 | 2810454H06Rik | NR_029441.1 | chr6:134847978-134850803 | | 923 | 4732490B19Rik | NR_040276.1 | chr11:113064628-113070983 |
| 830 | 2810459M11Rik | NM_001144993.1 | chr1:87942437-87952031 | | 924 | 4732491K20Rik | NR_045290.1 | chr17:12511718-12520116 |
| 831 | 2810459M11Rik | NM_001144993.1 | chr1:87942437-87952031 | | 925 | 4831440E17Rik | NR_030700.1 | chr5:25005614-25010291 |
| 832 | 2810468N07Rik | NR_045176.1 | chr17:25707755-25711988 | | 926 | 4833403I15Rik | NM_029008.1 | chr16:47009692-47065100 |
| 833 | 2810471M01Rik | NR_045036.1 | chr13:28581563-28593276 | | 927 | 4833411C07Rik | NR_102285.1 | chr8:10899921-10902334 |
| 834 | 2810474O19Rik | NM_001289661.1 | chr6:149257935-149284185 | | 928 | 4833412C05Rik | NR_045954.1 | chr7:74929423-74948382 |
| 835 | 2810474O19Rik | NM_001289662.1 | chr6:149257935-149284185 | | 929 | 4833417C18Rik | NR_045187.1 | chr11:95720130-95722360 |
| 836 | 2810474O19Rik | NM_026054.3 | chr6:149257935-149284185 | | 930 | 4833418N02Rik | NR_015506.2 | chr17:87674225-87682154 |
| 837 | 2900005L15Rik | NR_027851.1 | chr5:24606792-24608825 | | 931 | 4833419F23Rik | NR_040328.1 | chr18:4353544-4368943 |
| 838 | 2900008C10Rik | NR_045434.1 | chrX:11711580-11737472 | | 932 | 4833420G17Rik | NM_001113550.1 | chr13:120251565-120274924 |
| 839 | 2900009J06Rik | NR_045298.1 | chr1:129650194-129670631 | | 933 | 4833420G17Rik | NM_026127.4 | chr13:120251565-120274924 |
| 840 | 2900011O08Rik | NM_144518.3 | chr16:13986730-14101587 | | 934 | 4833422C13Rik | NR_015501.1 | chr13:91600701-91925753 |
| 841 | 2900026A02Rik | NM_172884.3 | chr5:113515342-113592333 | | 935 | 4833422C13Rik | NR_028313.1 | chr13:91600701-91925753 |
| 842 | 2900041M22Rik | NR_015689.2 | chr11:117472560-117474731 | | 936 | 4833422C13Rik | NR_028314.1 | chr13:91600701-91925753 |
| 843 | 2900052N01Rik | NR_015805.1 | chr9:46721685-46735449 | | 937 | 4833423C13Rik | NM_001081664.2 | chr2:85324248-85359092 |
| 844 | 2900055J20Rik | NR_045177.1 | chr18:40416615-40417341 | | 938 | 4833424O15Rik | NM_029425.3 | chr3:117278378-117392424 |
| 845 | 2900056M20Rik | NR_040269.2 | chrX:148729366-148762036 | | 939 | 4833427F10Rik | NR_045459.1 | chr17:35909394-35917632 |
| 846 | 2900056M20Rik | NR_040270.2 | chrX:148729366-148762036 | | 940 | 4833427G06Rik | NM_177702.3 | chr9:50889417-50910183 |
| 847 | 2900057B20Rik | NR_045365.1 | chr18:76251211-76258125 | | 941 | 4833428L15Rik | NR_040732.1 | chr9:45224709-45239315 |
| 848 | 2900060I14Rik | NR_027901.1 | chr1:120355246-120355842 | | 942 | 4833439L19Rik | NM_001252645.1 | chr13:54605165-54666743 |
| 849 | 2900076A07Rik | NR_045299.1 | chr7:88668436-88676984 | | 943 | 4833439L19Rik | NM_001252646.1 | chr13:54605165-54666743 |
| 850 | 2900079G21Rik | NR_015468.1 | chr9:111967594-112251429 | | 944 | 4833439L19Rik | NM_001252647.1 | chr13:54605165-54666743 |
| | | | | | 945 | 4833439L19Rik | NM_001252648.1 | chr13:54605165-54666743 |

Fig. 25 - 6

| | | | | | | | |
|---|---|---|---|---|---|---|---|
| 946 | 4833439L19Rik | NM_133797.4 | chr13:54605165-54666743 | 1041 | 4930432M17Rik | NM_001033814.1 | chr3:121373680-121385900 |
| 947 | 4921501E09Rik | NM_001009544.2 | chr17:33201087-33205003 | 1042 | 4930433B08Rik | NR_040443.1 | chr3:18368284-18380477 |
| 948 | 4921504A21Rik | NR_102341.1 | chr5:18708185-18732373 | 1043 | 4930433I11Rik | NR_207248.3 | chr7:48242978-48250203 |
| 949 | 4921504A21Rik | NR_102342.1 | chr5:18708185-18732373 | 1044 | 4930433N12Rik | NR_027988.1 | chr9:3190268-3199813 |
| 950 | 4921504E06Rik | NM_027600.4 | chr2:19384463-19475537 | 1045 | 4930434J06Rik | NR_046274.1 | chr14:72256515-72320245 |
| 951 | 4921506M07Rik | NM_001037743.1 | chr12:58665101-58723096 | 1046 | 4930435E12Rik | NR_029042.1 | chr16:38812317-38828862 |
| 952 | 4921507L20Rik | NR_045827.1 | chr2:93820191-93823732 | 1047 | 4930438E09Rik | NR_045961.1 | chr14:67950879-68016579 |
| 953 | 4921507P07Rik | NM_027564.3 | chr6:50523303-50546589 | 1048 | 4930440C22Rik | NR_040473.1 | chr1:96694018-96699049 |
| 954 | 4921508D12Rik | NR_045802.1 | chr2:132250476-132278235 | 1049 | 4930440I19Rik | NR_108098.1 | chr2:77889233-78034587 |
| 955 | 4921509C19Rik | NM_198655.2 | chr2:151296277-151301887 | 1050 | 4930441J16Rik | NR_040501.1 | chr2:74136996-74145774 |
| 956 | 4921509G07Rik | NR_045501.1 | chr13:114236495-114293052 | 1051 | 4930442J19Rik | NR_040747.1 | chr2:151127774-151141739 |
| 957 | 4921511C10Rik | NR_045502.1 | chr3:79016840-79057835 | 1052 | 4930442L01Rik | NR_015596.1 | chr3:96633749-96635993 |
| 958 | 4921511C20Rik | NR_003646.1 | chrX:123928824-123930430 | 1053 | 4930443O20Rik | NR_040504.1 | chr2:84913770-84926618 |
| 959 | 4921511H03Rik | NM_027603.2 | chr5:7304164-7311491 | 1054 | 4930444F06Rik | NR_038034.1 | chr10:18517104-18551736 |
| 960 | 4921511I17Rik | NR_045829.1 | chr12:12358328-12399281 | 1055 | 4930444F02Rik | NR_038035.1 | chr10:18517104-18551736 |
| 961 | 4921513I03Rik | NR_038000.1 | chr10:120202787-120215942 | 1056 | 4930444F02Rik | NR_102728.1 | chr10:18517104-18551736 |
| 962 | 4921513I03Rik | NR_038003.1 | chr10:120202787-120215942 | 1057 | 4930444G20Rik | NM_053264.2 | chr10:21786114-21787885 |
| 963 | 4921515E04Rik | NR_045711.1 | chr15:18007891-18299382 | 1058 | 4930444M15Rik | NR_045660.1 | chr14:76914364-76920662 |
| 964 | 4921517D22Rik | NM_183290.2 | chr13:59788762-59795462 | 1059 | 4930444P10Rik | NM_001243238.2 | chr1:16056059-16083122 |
| 965 | 4921524J17Rik | NM_025722.3 | chr8:87932657-87956740 | 1060 | 4930447A16Rik | NR_029113.1 | chr15:37355309-37370399 |
| 966 | 4921524J17Rik | NR_033144.1 | chr8:87932657-87956740 | 1061 | 4930447C04Rik | NM_029464.2 | chr12:73982095-74018752 |
| 967 | 4921524L21Rik | NM_027598.1 | chr18:6603630-6638964 | 1062 | 4930447J18Rik | NR_045959.1 | chr14:48518538-48563864 |
| 968 | 4921525O09Rik | NR_045661.1 | chr13:52192109-52219529 | 1063 | 4930447K03Rik | NR_046184.1 | chr13:34176023-34205141 |
| 969 | 4921529L05Rik | NR_110484.1 | chr6:53928684-53967377 | 1064 | 4930447N08Rik | NR_045168.1 | chr3:122498009-122504898 |
| 970 | 4921530L21Rik | NM_025733.2 | chr14:96280484-96281994 | 1065 | 4930448C13Rik | NR_045960.1 | chr12:15003194-15057195 |
| 971 | 4921531C22Rik | NR_033782.1 | chr2:179711557-179713718 | 1066 | 4930448F12Rik | NR_046032.1 | chr13:18176780-18192036 |
| 972 | 4921531P14Rik | NR_045361.1 | chr18:83462183-83495276 | 1067 | 4930448H16Rik | NR_040700.1 | chr5:143988670-143996427 |
| 973 | 4921533I20Rik | NR_038027.1 | chr18:17392991-17393991 | 1068 | 4930448I06Rik | NR_040475.1 | chr1:41224404-41238097 |
| 974 | 4921534H16Rik | NR_110443.1 | chr9:97903839-97912594 | 1069 | 4930448I18Rik | NR_040696.1 | chr5:50542571-50547331 |
| 975 | 4921536K21Rik | NR_026150.3 | chr1:3786090-3795129 | 1070 | 4930448K20Rik | NR_004448.2 | chr4:9843111-9844544 |
| 976 | 4921539E11Rik | NM_001160494.1 | chr4:102903050-102963468 | 1071 | 4930449E01Rik | NR_045921.1 | chr14:105898004-105904845 |
| 977 | 4921539E11Rik | NM_027612.1 | chr4:102903050-102963468 | 1072 | 4930449E18Rik | NR_045319.1 | chr19:57348449-57351542 |
| 978 | 4922502D21Rik | NM_199034.3 | chr6:129272182-129281799 | 1073 | 4930449I24Rik | NM_026136.2 | chr5:147313975-147316759 |
| 979 | 4922502H24Rik | NR_046187.1 | chr13:102161825-102167535 | 1074 | 4930451C15Rik | NM_001145435.1 | chr16:17544557-17561340 |
| 980 | 4922502N22Rik | NR_045149.1 | chr6:139264117-139271097 | 1075 | 4930451C15Rik | NM_029053.3 | chr16:17544557-17561340 |
| 981 | 4930401C15Rik | NR_045349.1 | chr10:25499119-25557243 | 1076 | 4930451G09Rik | NM_001271586.1 | chr16:4964380-4979055 |
| 982 | 4930401O10Rik | NR_045942.1 | chr11:71741972-71753624 | 1077 | 4930451G09Rik | NR_073370.1 | chr16:4964380-4979055 |
| 983 | 4930401O12Rik | NR_045957.1 | chr13:31305278-31332955 | 1078 | 4930451H11Rik | NM_183131.2 | chr7:133973987-133975010 |
| 984 | 4930402F06Rik | NM_001080789.1 | chr2:35231081-35252694 | 1079 | 4930452L24Rik | NR_045433.1 | chr17:9943616-9968731 |
| 985 | 4930402F06Rik | NM_001272040.1 | chr2:35231081-35252694 | 1080 | 4930452B06Rik | NM_028934.3 | chr14:9263685-9498804 |
| 986 | 4930402F11Rik | NR_045940.1 | chr7:76640979-76644575 | 1081 | 4930452G13Rik | NR_045060.1 | chr14:80102726-80112737 |
| 987 | 4930402H24Rik | NM_029432.1 | chr2:130533589-130665846 | 1082 | 4930452N14Rik | NR_040629.1 | chr1:156068651-156104036 |
| 988 | 4930402K13Rik | NM_001270700.1 | chrX:8681687-8683468 | 1083 | 4930453H23Rik | NM_001252013.1 | chr1:20783705-20798791 |
| 989 | 4930404A05Rik | NR_040495.1 | chr16:52799620-52815857 | 1084 | 4930453L07Rik | NR_073360.1 | chr8:9144668-9149050 |
| 990 | 4930404A10Rik | NM_029105.2 | chr14:54184153-54240257 | 1085 | 4930453N24Rik | NM_026273.2 | chr16:64765930-64770765 |
| 991 | 4930404H11Rik | NR_045941.1 | chr12:72641593-72657120 | 1086 | 4930455B14Rik | NR_045968.1 | chr14:9498903-9505892 |
| 992 | 4930404I05Rik | NR_028368.1 | chr16:91011494-91016748 | 1087 | 4930455C13Rik | NR_045352.1 | chr10:21038894-21061861 |
| 993 | 4930404N11Rik | NM_001014836.3 | chr10:80826769-80828565 | 1088 | 4930455D15Rik | NR_045381.1 | chr3:32823296-32996941 |
| 994 | 4930405A10Rik | NR_046307.1 | chr14:23326396-23362020 | 1089 | 4930455F16Rik | NR_040570.1 | chr16:4219911-4229116 |
| 995 | 4930405A21Rik | NR_040505.1 | chr2:156540275-156546645 | 1090 | 4930455F16Rik | NR_040571.1 | chr16:4219911-4229116 |
| 996 | 4930405D11Rik | NR_045953.1 | chr11:90666004-90756466 | 1091 | 4930455F16Rik | NR_040572.1 | chr16:4219911-4229116 |
| 997 | 4930405I17Rik | NR_045350.1 | chr10:19919053-19921660 | 1092 | 4930455H04Rik | NR_040596.1 | chr3:116671185-116687324 |
| 998 | 4930405L22Rik | NR_110478.1 | chr5:46318060-46323648 | 1093 | 4930455I16Rik | NR_045469.1 | chr13:58842434-58863672 |
| 999 | 4930406I18Rik | NR_040543.1 | chr3:100230327-100241677 | 1094 | 4930456L15Rik | NR_045887.1 | chr4:102963563-102984437 |
| 1000 | 4930407I10Rik | NM_001166475.1 | chr15:81889580-81896968 | 1095 | 4930459C07Rik | NR_110448.1 | chr10:95688840-95711342 |
| 1001 | 4930412B13Rik | NR_040631.1 | chr2:117647663-117734872 | 1096 | 4930459O17Rik | NR_046190.1 | chr5:58834478-58844237 |
| 1002 | 4930412C18Rik | NR_030693.1 | chr4:9697731-9750558 | 1097 | 4930461G14Rik | NR_040736.1 | chr9:58302979-58317430 |
| 1003 | 4930412D23Rik | NM_001281537.1 | chrX:124255709-124271086 | 1098 | 4930463O16Rik | NR_108059.1 | chr10:83951037-83960421 |
| 1004 | 4930412G13Rik | NR_024257.1 | chr2:9802873-9808394 | 1099 | 4930465K10Rik | NR_027978.1 | chr18:77952922-77954184 |
| 1005 | 4930413E15Rik | NR_040694.1 | chr5:119402347-119411270 | 1100 | 4930465M20Rik | NR_045973.1 | chr12:108961952-108973698 |
| 1006 | 4930413F20Rik | NR_045883.2 | chr15:34604828-34608959 | 1101 | 4930467D21Rik | NR_045981.1 | chr5:97821436-98017145 |
| 1007 | 4930413G21Rik | NR_046364.1 | chr7:130112571-130113973 | 1102 | 4930467F23Rik | NM_001039553.2 | chr8:19729576-19753602 |
| 1008 | 4930413M19Rik | NR_045759.1 | chr14:51123444-51140618 | 1103 | 4930467K11Rik | NR_045353.1 | chr10:57198188-57206159 |
| 1009 | 4930414L22Rik | NR_046011.1 | chr6:72388677-72390609 | 1104 | 4930468A15Rik | NM_001201395.1 | chrX:73827948-73848263 |
| 1010 | 4930414N06Rik | NR_040294.1 | chr19:45046607-45050040 | 1105 | 4930469G21Rik | NM_001195189.1 | chr1:163086974-163089445 |
| 1011 | 4930415F15Rik | NR_028669.1 | chr11:11389268-11415193 | 1106 | 4930470H14Rik | NR_045764.1 | chr17:4044657-4082995 |
| 1012 | 4930415L06Rik | NM_001033880.3 | chrX:87175435-87178191 | 1107 | 4930470P17Rik | NR_027825.1 | chr2:170404917-170427517 |
| 1013 | 4930415O20Rik | NM_001201522.1 | chr15:98401434-98420019 | 1108 | 4930471J04Rik | NR_046192.1 | chr14:64718131-64723072 |
| 1014 | 4930417O13Rik | NR_015527.1 | chr6:125215542-125223795 | 1109 | 4930471I03Rik | NR_015571.1 | chr18:36265857-36269608 |
| 1015 | 4930417O22Rik | NR_045806.1 | chr11:101813734-101821888 | 1110 | 4930471M09Rik | NR_045980.1 | chr6:91380453-91390848 |
| 1016 | 4930419G24Rik | NR_040595.1 | chr3:32923699-32987529 | 1111 | 4930473A02Rik | NR_040348.1 | chr2:130369527-130389485 |
| 1017 | 4930423M02Rik | NR_038183.1 | chr4:5559474-5569431 | 1112 | 4930473O22Rik | NR_045356.1 | chr10:97053677-97059565 |
| 1018 | 4930425K10Rik | NR_038182.1 | chr5:68324851-68334320 | 1113 | 4930474G06Rik | NR_045398.1 | chr18:28718664-29156677 |
| 1019 | 4930425O10Rik | NR_040545.1 | chr3:138874498-138889948 | 1114 | 4930474H20Rik | NR_045712.1 | chr14:90526697-90669567 |
| 1020 | 4930426D05Rik | NM_001271580.1 | chr18:21810066-21814608 | 1115 | 4930474M22Rik | NR_027986.1 | chr17:14526114-14535949 |
| 1021 | 4930426L09Rik | NR_024323.1 | chr2:18919945-18921431 | 1116 | 4930474N05Rik | NM_175008.3 | chr14:36908150-36910041 |
| 1022 | 4930427A07Rik | NM_134041.3 | chr12:114394631-114403669 | 1117 | 4930474N09Rik | NR_038130.1 | chr12:100399486-100401018 |
| 1023 | 4930428D18Rik | NM_001033799.2 | chrX:73636688-73643318 | 1118 | 4930478L05Rik | NR_040569.1 | chr16:78560561-78565114 |
| 1024 | 4930428E07Rik | NR_045943.1 | chr12:39279396-39341108 | 1119 | 4930478P22Rik | NR_046060.1 | chr5:35704201-35710326 |
| 1025 | 4930428G15Rik | NR_040730.1 | chr9:115245278-115251042 | 1120 | 4930479D17Rik | NR_046277.1 | chr6:146605739-146613925 |
| 1026 | 4930428O21Rik | NR_045871.1 | chr5:108127230-108132499 | 1121 | 4930480E11Rik | NM_001177966.2 | chrX:75614981-75616467 |
| 1027 | 4930429B21Rik | NR_027966.1 | chr3:32264411-32266360 | 1122 | 4930480G23Rik | NR_045977.1 | chr4:19806591-19932886 |
| 1028 | 4930429D17Rik | NR_040699.1 | chr5:103659393-103728048 | 1123 | 4930480K15Rik | NR_045463.1 | chr17:91260509-91266442 |
| 1029 | 4930429F24Rik | NR_033463.1 | chr17:79874963-79877225 | 1124 | 4930480M12Rik | NR_046278.1 | chr12:26896131-26925572 |
| 1030 | 4930429F24Rik | NR_040734.1 | chr9:79641447-79651042 | 1125 | 4930481L15Rik | NR_015545.2 | chr19:5406814-5424979 |
| 1031 | 4930430A15Rik | NM_026248.3 | chr2:111033410-111069757 | 1126 | 4930481A15Rik | NR_027938.2 | chr19:5406814-5424979 |
| 1032 | 4930430D24Rik | NM_001046856.2 | chrX:35591375-35396291 | 1127 | 4930482G09Rik | NR_108044.1 | chr3:152810906-152815072 |
| 1033 | 4930430F08Rik | NM_175128.2 | chr10:100034908-100051893 | 1128 | 4930483I18Rik | NR_015603.1 | chr15:81021282-81023187 |
| 1034 | 4930430F21Rik | NR_045186.1 | chr15:30968880-30973086 | 1129 | 4930483K19Rik | NR_045354.1 | chr10:76008616-76024971 |
| 1035 | 4930430J02Rik | NR_040729.1 | chr9:57238876-57248171 | 1130 | 4930483O08Rik | NR_046279.1 | chr7:140319933-140334140 |
| 1036 | 4930431F12Rik | NR_073013.1 | chr5:45357439-45370044 | 1131 | 4930486F22Rik | NR_038024.1 | chr10:85558599-85576330 |
| 1037 | 4930431P03Rik | NR_045059.1 | chr14:45574574-45580982 | 1132 | 4930486I03Rik | NR_045734.1 | chr1:20346535-20382381 |
| 1038 | 4930432J09Rik | NR_045953.1 | chr14:104376844-104426359 | 1133 | 4930486L24Rik | NM_178098.2 | chr13:60943972-60965777 |
| 1039 | 4930432K21Rik | NM_001163752.1 | chr8:86671936-86696496 | 1134 | 4930487D11Rik | NR_046191.1 | chr5:38735627-38740436 |
| 1040 | 4930432K21Rik | NM_029045.2 | chr8:86671936-86696496 | 1135 | 4930487H11Rik | NR_040601.1 | chr1:62837492-62841306 |

Fig. 25 - 7

| | | | | | | | |
|---|---|---|---|---|---|---|---|
| 1136 | 4930488B22Rik | NR_040627.1 | chr1:186536375-186542868 | 1231 | 4930545E07Rik | NR_045374.1 | chr18:17727254-17739499 |
| 1137 | 4930488L21Rik | NR_026888.1 | chr8:96335594-96337455 | 1232 | 4930545H06Rik | NR_045357.1 | chr10:67781812-67783890 |
| 1138 | 4930500F04Rik | NR_045758.1 | chr5:150650321-150666855 | 1233 | 4930545L23Rik | NR_040517.1 | chr2:134995309-135041352 |
| 1139 | 4930500J02Rik | NR_040322.1 | chr2:104399340-104411586 | 1234 | 4930546C10Rik | NR_038051.1 | chr18:69049140-69111182 |
| 1140 | 4930500J02Rik | NR_040323.1 | chr2:104399340-104411586 | 1235 | 4930546K05Rik | NR_040754.1 | chr9:41990320-42017314 |
| 1141 | 4930500L23Rik | NR_040701.1 | chr5:139999704-140017293 | 1236 | 4930547E08Rik | NR_040514.1 | chr2:103644608-103650779 |
| 1142 | 4930502A04Rik | NR_040737.1 | chr9:68318708-68368007 | 1237 | 4930547E14Rik | NR_040564.1 | chr16:59636771-59672819 |
| 1143 | 4930502E09Rik | NR_046281.1 | chr11:84642679-84644370 | 1238 | 4930548G14Rik | NR_045811.1 | chr15:46454850-46471404 |
| 1144 | 4930502E18Rik | NM_029142.1 | chrX:51028007-51041399 | 1239 | 4930548H24Rik | NM_026296.3 | chr5:31788231-31790635 |
| 1145 | 4930503B20Rik | NM_029144.3 | chr3:146309223-146314281 | 1240 | 4930548J01Rik | NR_045462.1 | chr17:4119445-4122102 |
| 1146 | 4930503E14Rik | NM_029131.3 | chr14:44740831-44749036 | 1241 | 4930548K13Rik | NR_040656.1 | chr4:26562966-26632596 |
| 1147 | 4930503E24Rik | NR_028310.1 | chr10:123906129-123961544 | 1242 | 4930549C01Rik | NM_026300.2 | chr4:136166351-136169128 |
| 1148 | 4930503H13Rik | NR_033598.1 | chrX:152974025-152974660 | 1243 | 4930549G23Rik | NR_045376.1 | chr18:67935687-67959597 |
| 1149 | 4930503L19Rik | NM_172967.2 | chr18:70612794-70632134 | 1244 | 4930550C14Rik | NM_029247.3 | chr9:53213390-53240908 |
| 1150 | 4930503O07Rik | NR_040477.1 | chr1:196038380-196048953 | 1245 | 4930550L24Rik | NM_023774.3 | chrX:56164637-56173481 |
| 1151 | 4930504O13Rik | NM_207527.3 | chr11:58259644-58266468 | 1246 | 4930552N02Rik | NR_040661.1 | chr4:52827476-52841141 |
| 1152 | 4930505A04Rik | NM_001100394.1 | chr1:30326005-30371829 | 1247 | 4930552P12Rik | NR_045318.1 | chr19:55715078-55776694 |
| 1153 | 4930505G20Rik | NR_045761.1 | chr14:115795773-115808774 | 1248 | 4930553E22Rik | NR_040567.1 | chr16:84371387-84375750 |
| 1154 | 4930506C21Rik | NR_073374.1 | chr17:8486231-8503983 | 1249 | 4930554C24Rik | NR_040739.1 | chr9:84668004-84677958 |
| 1155 | 4930506M07Rik | NM_001114312.1 | chr19:59047847-59150559 | 1250 | 4930555B11Rik | NR_040633.1 | chr2:57034241-57040668 |
| 1156 | 4930506M07Rik | NM_175172.4 | chr19:59047847-59150559 | 1251 | 4930555G01Rik | NM_175393.4 | chr14:5153653-5182268 |
| 1157 | 4930507D05Rik | NR_027926.1 | chr10:61911908-61914101 | 1252 | 4930556C24Rik | NR_040506.1 | chr16:85819455-85827017 |
| 1158 | 4930507D10Rik | NR_110449.1 | chr11:80663882-80671802 | 1253 | 4930556G01Rik | NR_040655.1 | chr4:30591745-30782894 |
| 1159 | 4930509E16Rik | NR_045735.1 | chr9:72366056-72379665 | 1254 | 4930556J02Rik | NR_045714.1 | chr14:62111524-62119219 |
| 1160 | 4930509J09Rik | NR_040547.1 | chr3:73155128-73285573 | 1255 | 4930556M19Rik | NR_045063.1 | chr15:10644590-10719878 |
| 1161 | 4930509L18Rik | NR_040663.1 | chr4:40260264-40264752 | 1256 | 4930556M19Rik | NR_045064.1 | chr15:10644590-10719878 |
| 1162 | 4930511A02Rik | NR_045966.1 | chr12:11445038-11451618 | 1257 | 4930556M19Rik | NR_045065.1 | chr15:10644590-10719878 |
| 1163 | 4930511E03Rik | NR_040761.1 | chr6:94893827-94901539 | 1258 | 4930556N09Rik | NR_045358.1 | chr10:96498401-96523693 |
| 1164 | 4930511M06Rik | NR_015494.1 | chr18:57693479-57890719 | 1259 | 4930557A04Rik | NM_029229.1 | chrX:9426828-9427378 |
| 1165 | 4930511M06Rik | NR_027944.1 | chr18:57693479-57890719 | 1260 | 4930557J02Rik | NR_040703.1 | chr5:34461389-34477988 |
| 1166 | 4930511M06Rik | NR_027945.1 | chr18:57693479-57890719 | 1261 | 4930558C23Rik | NR_015490.1 | chr3:95190379-95206763 |
| 1167 | 4930512B01Rik | NR_033573.1 | chr12:70891331-70942867 | 1262 | 4930558G05Rik | NR_045441.1 | chrX:125586059-125601682 |
| 1168 | 4930513D17Rik | NR_045416.1 | chr5:39852987-39994813 | 1263 | 4930558J18Rik | NR_037999.1 | chr1:57416065-57434388 |
| 1169 | 4930513N10Rik | NR_015574.2 | chr8:98330730-98345628 | 1264 | 4930558K02Rik | NM_001204904.1 | chr1:163872219-163909767 |
| 1170 | 4930513O06Rik | NM_029174.1 | chrX:135620781-135627942 | 1265 | 4930558K02Rik | NM_001204905.1 | chr1:163872219-163909767 |
| 1171 | 4930515B02Rik | NR_040654.1 | chr4:140428607-140433972 | 1266 | 4930562C15Rik | NM_030192.1 | chr16:4835415-4867691 |
| 1172 | 4930515G01Rik | NR_027872.1 | chr5:115223741-115224992 | 1267 | 4930562F07Rik | NR_038030.1 | chr1:161974510-162008717 |
| 1173 | 4930515G16Rik | NR_003100.1 | chr6:67515227-67515693 | 1268 | 4930562F07Rik | NR_038031.1 | chr1:161974510-162008717 |
| 1174 | 4930515L03Rik | NR_040632.1 | chr2:16840304-16935353 | 1269 | 4930563B23Rik | NM_029252.2 | chr16:92319007-92321686 |
| 1175 | 4930515L19Rik | NR_045440.1 | chrX:43620735-43682088 | 1270 | 4930563E18Rik | NR_045379.1 | chr18:10706857-10711830 |
| 1176 | 4930517E11Rik | NR_040611.1 | chr2:123949372-123955692 | 1271 | 4930563E22Rik | NM_001163728.1 | chr11:72028640-72031952 |
| 1177 | 4930518P08Rik | NR_045364.1 | chr13:50848761-50850617 | 1272 | 4930563F08Rik | NR_040704.1 | chr5:132356139-132359638 |
| 1178 | 4930519D14Rik | NR_045975.1 | chr13:30706911-30716127 | 1273 | 4930563M20Rik | NR_046193.1 | chr8:119305611-119325312 |
| 1179 | 4930519F09Rik | NR_033601.1 | chr10:28641768-28643313 | 1274 | 4930564B18Rik | NM_029230.1 | chr14:76042065-76066944 |
| 1180 | 4930519F16Rik | NM_029170.1 | chrX:100427619-100451945 | 1275 | 4930564C03Rik | NM_029257.1 | chr17:45016653-45017834 |
| 1181 | 4930519F24Rik | NR_040763.1 | chr9:99922718-99935089 | 1276 | 4930564D02Rik | NM_029228.1 | chr3:104889761-104881724 |
| 1182 | 4930519G04Rik | NM_026263.2 | chr5:115303722-115333888 | 1277 | 4930565D16Rik | NR_040752.1 | chr8:84153297-84183843 |
| 1183 | 4930519H02Rik | NR_045974.1 | chr5:15369745-15389584 | 1278 | 4930565N06Rik | NR_040476.1 | chr16:36880605-36897275 |
| 1184 | 4930520O04Rik | NR_040383.1 | chr9:114277441-114299830 | 1279 | 4930567H12Rik | NR_015535.2 | chr8:128108537-128140570 |
| 1185 | 4930520O04Rik | NR_040384.1 | chr9:114277441-114299830 | 1280 | 4930567H17Rik | NM_001033807.2 | chrX:67647075-67647915 |
| 1186 | 4930520P13Rik | NR_036596.1 | chr13:70371699-70387000 | 1281 | 4930567J20Rik | NR_040574.1 | chr16:71250148-71267421 |
| 1187 | 4930521E06Rik | NR_040602.1 | chr1:44796520-44801794 | 1282 | 4930567K20Rik | NR_046010.1 | chr10:10470844-10477929 |
| 1188 | 4930522H14Rik | NM_001199090.1 | chr4:109177936-109203902 | 1283 | 4930568D16Rik | NM_029463.1 | chr2:35209737-35223249 |
| 1189 | 4930522H14Rik | NM_026291.1 | chr4:109177936-109203902 | 1284 | 4930568E12Rik | NR_040755.1 | chr9:13091266-13105855 |
| 1190 | 4930522O17Rik | NR_040665.1 | chr4:53259067-53263992 | 1285 | 4930568G15Rik | NR_040480.1 | chr1:166996747-167022061 |
| 1191 | 4930523C07Rik | NM_001162896.1 | chr1:161974510-162008717 | 1286 | 4930570G19Rik | NR_040398.1 | chr3:156209716-156224710 |
| 1192 | 4930523C07Rik | NR_028111.1 | chr1:161974510-162008717 | 1287 | 4930570G19Rik | NR_040399.1 | chr3:156209716-156224710 |
| 1193 | 4930523D13Rik | NR_040451.1 | chr15:46267411-46327725 | 1288 | 4930570G19Rik | NR_040400.1 | chr3:156209716-156224710 |
| 1194 | 4930524B15Rik | NM_026262.1 | chr1:31865632-31879651 | 1289 | 4930571K23Rik | NM_001145759.1 | chr7:132512374-132514527 |
| 1195 | 4930524C18Rik | NR_045661.1 | chr14:115231186-115260549 | 1290 | 4930571O06Rik | NR_110476.1 | chr8:116041181-116074708 |
| 1196 | 4930524N10Rik | NM_001256259.1 | chrX:150773767-150777935 | 1291 | 4930572K03Rik | NR_045371.1 | chr5:127650934-127664726 |
| 1197 | 4930524O05Rik | NR_045316.1 | chr19:10720184-10722543 | 1292 | 4930572O03Rik | NR_073011.1 | chr5:15158105-15162877 |
| 1198 | 4930524O08Rik | NR_040735.1 | chr9:89721356-89758866 | 1293 | 4930572O13Rik | NR_045718.1 | chr14:25959280-25962727 |
| 1199 | 4930525D18Rik | NR_040738.1 | chr9:114250228-114273745 | 1294 | 4930573O16Rik | NR_040620.1 | chr2:52146522-52170760 |
| 1200 | 4930525G20Rik | NR_045194.1 | chr13:67897531-67931922 | 1295 | 4930577N17Rik | NR_073429.1 | chr3:51080683-51082329 |
| 1201 | 4930525M21Rik | NM_001243943.1 | chrX:35367084-35371992 | 1296 | 4930578C19Rik | NM_175228.3 | chrX:17995552-18038400 |
| 1202 | 4930526I15Rik | NR_015516.2 | chr9_random:46928-56293 | 1297 | 4930578E11Rik | NR_045391.1 | chr18:29556370-29656070 |
| 1203 | 4930526I15Rik | NR_027950.2 | chr9_random:46928-56293 | 1298 | 4930578I06Rik | NM_026619.3 | chr14:64589958-64606617 |
| 1204 | 4930526I15Rik | NR_102721.1 | chr9_random:46928-56293 | 1299 | 4930578M01Rik | NR_045991.1 | chr15:98816395-98819712 |
| 1205 | 4930526L06Rik | NR_045783.1 | chr19:11271307-11374374 | 1300 | 4930578N16Rik | NR_040575.1 | chr16:76122857-76156331 |
| 1206 | 4930527F14Rik | NR_045809.1 | chr14:46163384-46182551 | 1301 | 4930579F01Rik | NM_001163385.1 | chr3:137827098-137849677 |
| 1207 | 4930527G23Rik | NR_045395.1 | chr18:29601854-29625761 | 1302 | 4930579F01Rik | NM_001163386.1 | chr3:137827098-137849677 |
| 1208 | 4930528A17Rik | NR_028384.1 | chr4:21773474-21775695 | 1303 | 4930579G18Rik | NR_038053.1 | chr14:55269348-55273937 |
| 1209 | 4930528D03Rik | NR_045977.1 | chr13:59835010-59838831 | 1304 | 4930579G24Rik | NM_029482.1 | chr3:79433000-79436741 |
| 1210 | 4930528P14Rik | NR_040516.1 | chr2:115155001-115170016 | 1305 | 4930579K19Rik | NR_029444.1 | chr9:98462878-98464030 |
| 1211 | 4930529C04Rik | NR_033593.1 | chr3:90875583-90879114 | 1306 | 4930581F22Rik | NR_029475.1 | chr9:34924313-34938507 |
| 1212 | 4930529K09Rik | NR_040457.1 | chr4:86645775-86661849 | 1307 | 4930583K01Rik | NR_027879.1 | chr7:125387420-125389065 |
| 1213 | 4930529L06Rik | NR_040537.1 | chr16:84680033-84685392 | 1308 | 4930583P06Rik | NR_040612.1 | chr2:124043415-124048094 |
| 1214 | 4930529M08Rik | NM_175280.3 | chr2:145760519-145789962 | 1309 | 4930584F24Rik | NR_029452.1 | chr5:26786609-26819854 |
| 1215 | 4930532M18Rik | NR_108050.1 | chr1:156102819-156117546 | 1310 | 4930590D08Rik | NM_198668.2 | chr8:91854226-91900719 |
| 1216 | 4930533B01Rik | NR_040614.1 | chr2:113531210-113548707 | 1311 | 4930590L20Rik | NR_040604.1 | chr1:142466753-142552979 |
| 1217 | 4930533P14Rik | NR_040478.1 | chr1:98508633-98559150 | 1312 | 4930591A17Rik | NM_026896.2 | chr2:179149640-179151585 |
| 1218 | 4930538K18Rik | NM_029198.3 | chr4:118877659-118890822 | 1313 | 4930592A05Rik | NR_045070.1 | chr15:33523636-33583191 |
| 1219 | 4930539C22Rik | NR_040600.1 | chr3:134067106-134086599 | 1314 | 4930592I03Rik | NR_033307.1 | chr18:83087797-83089952 |
| 1220 | 4930539E08Rik | NM_172450.3 | chr17:29033340-29052269 | 1315 | 4930593A02Rik | NR_045167.1 | chr3:58496510-58592446 |
| 1221 | 4930539J05Rik | NR_030689.1 | chr3:135099186-135101629 | 1316 | 4930593C16Rik | NR_040753.1 | chr9:120833572-120839920 |
| 1222 | 4930539M17Rik | NR_024017.1 | chr3:9061963-9071076 | 1317 | 4930594C11Rik | NR_024044.1 | chr7:37542696-37545450 |
| 1223 | 4930539N22Rik | NR_040598.1 | chr3:13597139-13652865 | 1318 | 4930595M18Rik | NM_173435.3 | chrX:78664913-78703461 |
| 1224 | 4930540M03Rik | NR_040746.1 | chr9:15424301-15445664 | 1319 | 4930596D02Rik | NM_001033766.3 | chr14:36622671-36625164 |
| 1225 | 4930542C21Rik | NR_040565.1 | chr16:38017408-38054612 | 1320 | 4930596J03Rik | NR_108103.1 | chr1:140874234-140875823 |
| 1226 | 4930542D17Rik | NR_040566.1 | chr8:50590616-50654279 | 1321 | 4930597G03Rik | NR_045736.1 | chr14:51937009-51965164 |
| 1227 | 4930543E12Rik | NR_045978.1 | chr7:120243749-120285529 | 1322 | 4930598F16Rik | NR_040479.1 | chr1:97597760-97613095 |
| 1228 | 4930544D05Rik | NM_001145537.1 | chr17:70429396-70430392 | 1323 | 4930599N23Rik | NR_045813.1 | chr6:39068472-39098311 |
| 1229 | 4930544G11Rik | NM_001161773.1 | chr6:65902564-65904008 | 1324 | 4931402G19Rik | NR_040608.1 | chr2:120281434-120295103 |
| 1230 | 4930544M13Rik | NR_045976.1 | chr13:115397435-115488030 | 1325 | 4931403E22Rik | NR_045306.1 | chr19:26843291-26898397 |

Fig. 25 - 8

| | | | |
|---|---|---|---|
| 1326 | 4931403G20Rik | NR_038172.1 | chr12:70847834-71087989 |
| 1327 | 4931403G20Rik | NR_038173.1 | chr12:70847834-71087989 |
| 1328 | 4931406B18Rik | NM_028737.2 | chr7:50747413-50761308 |
| 1329 | 4931406C07Rik | NM_001199484.1 | chr9:15087780-15162232 |
| 1330 | 4931406C07Rik | NM_001199485.1 | chr9:15087780-15162232 |
| 1331 | 4931406C07Rik | NM_133732.3 | chr9:15087780-15162232 |
| 1332 | 4931406H21Rik | NR_033492.1 | chr14:26406290-26410147 |
| 1333 | 4931406P16Rik | NM_172741.2 | chr7:35021732-35070628 |
| 1334 | 4931408C20Rik | NM_001033764.3 | chr1:26738645-26744305 |
| 1335 | 4931408D14Rik | NR_040298.1 | chr19:37332918-37338585 |
| 1336 | 4931408D14Rik | NR_040299.1 | chr19:37332918-37338585 |
| 1337 | 4931409K22Rik | NM_177676.6 | chr5:24049251-24061287 |
| 1338 | 4931409K22Rik | NR_033188.1 | chr5:24049251-24061287 |
| 1339 | 4931412M21 | NR_110487.1 | chr12:10453193-10538109 |
| 1340 | 4931414P19Rik | NM_028890.2 | chr14:55202499-55224745 |
| 1341 | 4931417E11Rik | NR_025737.3 | chr6:73418567-73419661 |
| 1342 | 4931419H13Rik | NR_040593.1 | chr3:54859163-54887924 |
| 1343 | 4931420L22Rik | NR_040561.1 | chr16:71131320-71139274 |
| 1344 | 4931423N10Rik | NM_027635.1 | chr2:23062995-23122649 |
| 1345 | 4931428F04Rik | NM_001166394.1 | chr8:107800346-107813428 |
| 1346 | 4931428F04Rik | NM_028888.2 | chr8:107800346-107813428 |
| 1347 | 4931428L18Rik | NR_033445.1 | chr1:31197923-31279501 |
| 1348 | 4931429I11Rik | NM_001081121.1 | chr9:40702931-40772195 |
| 1349 | 4931429L15Rik | NM_183104.2 | chr9:46111443-46128069 |
| 1350 | 4931429P17Rik | NR_038004.1 | chr13:48055698-48113977 |
| 1351 | 4931430N09Rik | NR_046053.1 | chr6:118830176-118835561 |
| 1352 | 4931431B13Rik | NR_045183.1 | chr7:135335564-135346842 |
| 1353 | 4931431C16Rik | NR_046807.1 | chr5:35923876-35931412 |
| 1354 | 4931431F19Rik | NM_027634.1 | chr7:111276426-111278337 |
| 1355 | 4931440F15Rik | NM_176829.2 | chr11:29722395-29725668 |
| 1356 | 4931440I10Rik | NR_045503.1 | chr14:63379338-63448963 |
| 1357 | 4931440L10Rik | NM_001145300.2 | chr1:136437517-136446259 |
| 1358 | 4931440L10Rik | NM_001291015.1 | chr1:136437517-136446259 |
| 1359 | 4931440L10Rik | NM_026896.1 | chr1:136437517-136446259 |
| 1360 | 4931440P22Rik | NR_027955.1 | chr3:65331407-65333336 |
| 1361 | 4932411E22Rik | NM_172534.2 | chr1:89251536-89280262 |
| 1362 | 4932411N23Rik | NM_177705.3 | chrX:123346993-123350397 |
| 1363 | 4932412D23Rik | NR_040521.1 | chr16:42725814-42875875 |
| 1364 | 4932412D23Rik | NR_040522.1 | chr16:42725814-42875875 |
| 1365 | 4932413F04Rik | NR_040764.1 | chr9:103459420-103468221 |
| 1366 | 4932414J04Rik | NM_028259.1 | chr11:21394732-21411183 |
| 1367 | 4932414N04Rik | NM_183113.1 | chr2:68495940-68586522 |
| 1368 | 4932415M13Rik | NR_073205.1 | chr17:53855833-53873168 |
| 1369 | 4932416H05Rik | NR_029452.1 | chr2:129624105-129627195 |
| 1370 | 4932416K20Rik | NM_001002775.2 | chr8:107319136-107322692 |
| 1371 | 4932418E24Rik | NM_177841.3 | chr2:26127166-26150077 |
| 1372 | 4932429P05Rik | NM_001085511.1 | chrX:86997606-87000830 |
| 1373 | 4932435O22Rik | NR_027643.2 | chr11:114274718-114310174 |
| 1374 | 4932438A13Rik | NM_172679.2 | chr3:36762027-36951955 |
| 1375 | 4932438H23Rik | NM_001163695.1 | chr16:91054179-91069390 |
| 1376 | 4932438H23Rik | NM_028905.3 | chr16:91054179-91069390 |
| 1377 | 4932441J04Rik | NR_015588.2 | chr5:57961322-58109158 |
| 1378 | 4932441J19Rik | NM_001101519.1 | chr1:13705888-13743066 |
| 1379 | 4932702P03Rik | NR_045182.1 | chr13:24992469-25003649 |
| 1380 | 4933400A11Rik | NR_003635.1 | chrX:166214310-166217567 |
| 1381 | 4933400B14Rik | NR_045432.1 | chr17:89719568-89726673 |
| 1382 | 4933400C23Rik | NR_040770.1 | chr9:92613553-92690549 |
| 1383 | 4933400F21Rik | NR_015540.1 | chr1:91573082-91580467 |
| 1384 | 4933400L20Rik | NR_045730.1 | chr8:106127698-106204282 |
| 1385 | 4933401B06Rik | NR_033580.1 | chrX:104737920-104739139 |
| 1386 | 4933401D09Rik | NR_045431.1 | chr17:15768751-15778066 |
| 1387 | 4933401H08Rik | NR_040540.1 | chr3:135496658-135503233 |
| 1388 | 4933402C06Rik | NR_045504.1 | chr7:47930106-47946630 |
| 1389 | 4933402D24Rik | NM_001256158.1 | chr1:63801482-63815841 |
| 1390 | 4933402E13Rik | NM_001199496.1 | chrX:59536673-59545253 |
| 1391 | 4933402E13Rik | NM_001199997.1 | chrX:59536673-59545253 |
| 1392 | 4933402J07Rik | NM_177901.3 | chr8:90087805-90113096 |
| 1393 | 4933402J10Rik | NR_040637.1 | chr5:60354357-60377241 |
| 1394 | 4933402J10Rik | NR_040683.1 | chr5:60354357-60377241 |
| 1395 | 4933402J15Rik | NR_046059.1 | chr14:74755333-74769548 |
| 1396 | 4933402N03Rik | NM_173409.4 | chr7:138281866-138289797 |
| 1397 | 4933402N22Rik | NM_001177510.1 | chr5:11918042-11922804 |
| 1398 | 4933402P03Rik | NM_175368.3 | chr11:69630067-69631942 |
| 1399 | 4933403O08Rik | NM_001177389.1 | chrX:109352657-109357461 |
| 1400 | 4933404G15Rik | NR_045920.1 | chr16:16707779-16718214 |
| 1401 | 4933404K08Rik | NR_046038.1 | chr3:23370218-23374136 |
| 1402 | 4933404O12Rik | NR_015555.1 | chr5:137395015-137412979 |
| 1403 | 4933405D12Rik | NR_046036.1 | chr3:122585510-122627034 |
| 1404 | 4933405E24Rik | NR_045506.1 | chr11:53991273-54026790 |
| 1405 | 4933405L10Rik | NM_027655.1 | chr8:108232202-108234068 |
| 1406 | 4933405O20Rik | NM_172901.2 | chr7:57854560-57855898 |
| 1407 | 4933406C10Rik | NR_044986.1 | chr12:33604248-33638654 |
| 1408 | 4933406D12Rik | NR_040502.1 | chr2:146368666-146371844 |
| 1409 | 4933406G16Rik | NR_015568.2 | chr14:8244986-8255199 |
| 1410 | 4933406G16Rik | NR_046037.1 | chr11:18965277-18975743 |
| 1411 | 4933406I18Rik | NR_029437.1 | chr7:121458992-121558675 |
| 1412 | 4933406I18Rik | NR_029438.1 | chr7:121458992-121558675 |
| 1413 | 4933406J08Rik | NM_028914.1 | chr7:122012007-122032129 |
| 1414 | 4933406I10Rik | NR_046004.1 | chr7:89891856-89904154 |
| 1415 | 4933406K04Rik | NR_015512.2 | chr12:107923816-107954534 |
| 1416 | 4933406M09Rik | NM_173771.4 | chr1:136282516-136287560 |
| 1417 | 4933407E24Rik | NR_045819.1 | chr4:124246421-124252781 |
| 1418 | 4933407G14Rik | NR_045841.1 | chr10:74912254-74925849 |
| 1419 | 4933407H05Rik | NR_040731.1 | chr9:51722533-51735108 |
| 1420 | 4933407K13Rik | NR_029443.1 | chrX:72970796-73010038 |
| 1421 | 4933407L21Rik | NR_037692.1 | chr1:87825057-87828331 |
| 1422 | 4933408B17Rik | NM_177773.4 | chr18:34739499-34757122 |
| 1423 | 4933408J17Rik | NR_045810.1 | chr10:93052158-93067990 |
| 1424 | 4933408N05Rik | NR_045831.2 | chr8:116865061-116875378 |
| 1425 | 4933409G03Rik | NM_176651.3 | chr2:68420469-68454520 |
| 1426 | 4933409K07Rik | NR_033123.1 | chr4:42452732-42476567 |
| 1427 | 4933409K07Rik | NR_033123.1 | chrUn_random:588638-612480 |
| 1428 | 4933409K07Rik | NR_033123.1 | chr4:41763293-42104673 |
| 1429 | 4933411E08Rik | NR_045342.1 | chr10:117362514-117385363 |
| 1430 | 4933411G06Rik | NR_045158.1 | chr10:51475979-51477000 |
| 1431 | 4933411G11Rik | NM_177880.4 | chr5:143942695-143966747 |
| 1432 | 4933411K16Rik | NM_025752.2 | chr19:42126718-42128118 |
| 1433 | 4933411K20Rik | NR_025747.3 | chr8:47254909-47280944 |
| 1434 | 4933412E12Rik | NR_038025.1 | chr10:116387617-116400335 |
| 1435 | 4933412E12Rik | NR_038026.1 | chr10:116387617-116400335 |
| 1436 | 4933412E24Rik | NM_027668.1 | chr15:59846420-59848173 |
| 1437 | 4933412O06Rik | NR_045507.1 | chr13:15873496-15894463 |
| 1438 | 4933413G19Rik | NM_027697.1 | chr6:128325528-128335162 |
| 1439 | 4933413J09Rik | NR_038005.1 | chr14:27177032-27239942 |
| 1440 | 4933413L06Rik | NR_045508.1 | chr13:118495571-118508818 |
| 1441 | 4933415F23Rik | NM_025746.2 | chr1:23107312-23109092 |
| 1442 | 4933416C03Rik | NM_001161855.1 | chr10:115548720-115550973 |
| 1443 | 4933416E03Rik | NR_040498.1 | chr2:159773076-159807025 |
| 1444 | 4933416I08Rik | NM_027700.1 | chrX:50989668-50994509 |
| 1445 | 4933416M06Rik | NR_045846.2 | chr13:102024273-102063351 |
| 1446 | 4933416M07Rik | NR_045840.1 | chr8:28253382-28260178 |
| 1447 | 4933417A18Rik | NM_025750.3 | chr13:35016278-35045065 |
| 1448 | 4933417D19Rik | NR_045849.1 | chr8:125758991-125766259 |
| 1449 | 4933417E11Rik | NR_040454.1 | chr7:72005571-72051769 |
| 1450 | 4933417G07Rik | NR_033592.1 | chr3:55651027-55651987 |
| 1451 | 4933417O13Rik | NR_045842.1 | chr7:150508677-150516555 |
| 1452 | 4933421J07Rik | NM_027702.2 | chr7:49700831-49703450 |
| 1453 | 4933421O10Rik | NR_036602.1 | chr4:33114113-33118298 |
| 1454 | 4933422A05Rik | NR_040715.1 | chr9:35088689-35093008 |
| 1455 | 4933422H20Rik | NM_001033775.3 | chr11:115301859-115309582 |
| 1456 | 4933424G05Rik | NR_045372.1 | chr18:15147504-15206496 |
| 1457 | 4933424G06Rik | NR_040290.1 | chr1:36771382-36814805 |
| 1458 | 4933425B07Rik | NR_046460.1 | chr14:47222480-47257098 |
| 1459 | 4933425L06Rik | NM_025751.3 | chr13:105872201-105911862 |
| 1460 | 4933426M11Rik | NM_001242419.1 | chr12:81891518-81981820 |
| 1461 | 4933426M11Rik | NR_178682.4 | chr12:81891518-81981820 |
| 1462 | 4933427D06Rik | NM_175017.3 | chr6:89046108-89060031 |
| 1463 | 4933427D14Rik | NM_028963.2 | chr11:71967598-72016873 |
| 1464 | 4933427E11Rik | NR_033197.1 | chr15:74539591-74540804 |
| 1465 | 4933427E13Rik | NR_045853.1 | chr11:25226106-25267137 |
| 1466 | 4933427G17Rik | NM_028955.1 | chr7:128128022-128158301 |
| 1467 | 4933427I22Rik | NR_045159.1 | chr4:139482025-139499434 |
| 1468 | 4933427I22Rik | NR_045160.1 | chr4:139482025-139499434 |
| 1469 | 4933428C19Rik | NR_040644.1 | chr4:40429872-40472581 |
| 1470 | 4933428G20Rik | NM_001289118.1 | chr11:97352097-97361654 |
| 1471 | 4933429K18Rik | NR_045307.1 | chr19:45801044-45805048 |
| 1472 | 4933429O19Rik | NR_045311.1 | chr14:49498547-49506787 |
| 1473 | 4933430H16Rik | NR_045855.1 | chr7:90086447-90119901 |
| 1474 | 4933430I17Rik | NM_177607.3 | chr4:62186402-62209027 |
| 1475 | 4933430M04Rik | NR_045857.2 | chr11:24381908-24469951 |
| 1476 | 4933430N04Rik | NR_045854.1 | chr3:9125411-9132288 |
| 1477 | 4933431E20Rik | NR_015459.1 | chr3:107691768-107699131 |
| 1478 | 4933431G14Rik | NR_045163.1 | chr6:72047601-72104564 |
| 1479 | 4933431G14Rik | NR_045165.1 | chr6:72047601-72104564 |
| 1480 | 4933432G23Rik | NR_040716.1 | chr9:118338956-118346166 |
| 1481 | 4933432I03Rik | NR_045657.1 | chr14:103386628-103433020 |
| 1482 | 4933432I09Rik | NR_015575.1 | chr16:18209778-18213956 |
| 1483 | 4933432I09Rik | NR_027843.1 | chr16:18209778-18213956 |
| 1484 | 4933432K03Rik | NR_102286.1 | chr7:128730899-128733350 |
| 1485 | 4933433C11Rik | NM_028961.1 | chr2:25068078-25070150 |
| 1486 | 4933433F19Rik | NR_045856.1 | chr8:31678866-31686045 |
| 1487 | 4933433G08Rik | NR_105026.1 | chr9:60950818-60953193 |
| 1488 | 4933433G15Rik | NR_040719.1 | chr9:75257990-75263344 |
| 1489 | 4933433G19Rik | NR_045851.1 | chr13:67097754-67133341 |
| 1490 | 4933433H22Rik | NR_045458.1 | chr17:84477999-84489215 |
| 1491 | 4933434E20Rik | NM_001287086.1 | chr3:89802681-89872269 |
| 1492 | 4933434E20Rik | NM_001287087.1 | chr3:89802681-89872269 |
| 1493 | 4933434E20Rik | NM_025762.3 | chr3:89802681-89872269 |
| 1494 | 4933434E20Rik | NM_027500.4 | chr3:89802681-89872269 |
| 1495 | 4933434I20Rik | NR_026233.2 | chr8:85872370-85903301 |
| 1496 | 4933436E23Rik | NR_040455.1 | chr1:141276028-141299429 |
| 1497 | 4933436H12Rik | NR_046208.1 | chr7:75562309-75571019 |
| 1498 | 4933436I01Rik | NM_025763.1 | chrX:65173036-65174625 |
| 1499 | 4933438B17Rik | NR_040685.1 | chr5:127511158-127568899 |
| 1500 | 4933438K21Rik | NR_045446.1 | chr4:146437474-146442545 |
| 1501 | 4933439C10Rik | NR_015585.1 | chr11:59319187-59324569 |
| 1502 | 4933439K11Rik | NR_040558.1 | chr1:174471751-174480937 |
| 1503 | 4933440O02Rik | NR_045344.1 | chr10:111023774-111031329 |
| 1504 | 4933440M02Rik | NR_045803.1 | chr7:132475295-132493300 |
| 1505 | 4933440M02Rik | NR_045804.1 | chr7:132475295-132493300 |
| 1506 | 5031410I06Rik | NM_207667.3 | chr5:26425208-26431854 |
| 1507 | 5031414D18Rik | NM_198642.2 | chr14:75415833-75452339 |
| 1508 | 5031425E22Rik | NR_040469.1 | chr5:29937625-29940171 |
| 1509 | 5031425F14Rik | NR_015558.2 | chr2:166272950-166284270 |
| 1510 | 5031426D15Rik | NR_027890.1 | chr2:6843748-6849768 |
| 1511 | 5031434C07Rik | NR_045986.1 | chr6:112223751-112280417 |
| 1512 | 5031434C07Rik | NR_045987.1 | chr6:112223751-112280417 |
| 1513 | 5031434O11Rik | NR_033624.1 | chr3:51363679-51371038 |
| 1514 | 5031439G07Rik | NM_001033273.2 | chr15:84776150-84818401 |

Fig. 25 - 9

| | | | | | | | |
|---|---|---|---|---|---|---|---|
| 1515 | 5033403H07Rik | NR_040413.1 | chr5:53364250-53383531 | 1610 | 6330409D20Rik | NM_027529.1 | chr2:32588141-32596536 |
| 1516 | 5033404E19Rik | NR_033600.1 | chr1:187321184-187321893 | 1611 | 6330410L21Rik | NR_040589.1 | chr3:129456676-129466800 |
| 1517 | 5033406O09Rik | NR_029464.1 | chr12:113180201-113182693 | 1612 | 6330415B21Rik | NR_045141.1 | chr6:77330251-77332469 |
| 1518 | 5133400J02Rik | NR_110444.1 | chr11:51003334-51033920 | 1613 | 6330416G13Rik | NM_144905.3 | chr4:63221393-63247387 |
| 1519 | 5330411J11Rik | NR_040510.1 | chr2:59220549-59224739 | 1614 | 6330418K02Rik | NR_045821.1 | chr5:138705273-138707889 |
| 1520 | 5330413P13Rik | NR_029381.1 | chr2:131645741-131673392 | 1615 | 6330419J24Rik | NR_028086.1 | chrX:53627752-53631647 |
| 1521 | 5330417C22Rik | NM_001033304.1 | chr3:108260986-108339440 | 1616 | 6330549D23Rik | NR_003619.2 | chr3:96410585-96433742 |
| 1522 | 5330426P16Rik | NR_028300.1 | chr16:50726864-50732886 | 1617 | 6430411K18Rik | NR_002848.3 | chr12:110829747-110831061 |
| 1523 | 5330434G04Rik | NR_015552.1 | chrX:102568332-102587093 | 1618 | 6430503K07Rik | NR_108091.1 | chr2:147013160-147014218 |
| 1524 | 5330439B14Rik | NR_037679.1 | chr6:142563115-142574982 | 1619 | 6430531B16Rik | NM_001033465.2 | chr7:147158201-147164654 |
| 1525 | 5330401F13Rik | NM_001244628.1 | chr6:131493779-131503775 | 1620 | 6430548M08Rik | NR_001163760.1 | chr8:122638051-122689207 |
| 1526 | 5430402E10Rik | NM_027768.3 | chrX:75233629-75238906 | 1621 | 6430548M08Rik | NR_001163761.1 | chr8:122638051-122689207 |
| 1527 | 5430402O13Rik | NR_015581.1 | chr6:50516641-50546589 | 1622 | 6430548M08Rik | NM_001163762.1 | chr8:122638051-122689207 |
| 1528 | 5430402O13Rik | NR_027892.1 | chr6:50516641-50546589 | 1623 | 6430548M08Rik | NM_172286.4 | chr8:122638051-122689207 |
| 1529 | 5430403N17Rik | NR_046181.1 | chr8:36927138-36946011 | 1624 | 6430550D23Rik | NM_001145351.1 | chr2:155826178-155833713 |
| 1530 | 5430405H02Rik | NR_015591.1 | chr2:156665742-156688681 | 1625 | 6430550D23Rik | NM_001145352.1 | chr2:155826178-155833713 |
| 1531 | 5430405H02Rik | NR_027914.1 | chr2:156665742-156688681 | 1626 | 6430562O15Rik | NR_015515.2 | chr13:100180791-100182781 |
| 1532 | 5430416N02Rik | NR_034038.1 | chr5:100849860-100858554 | 1627 | 6430571L13Rik | NM_175486.3 | chr9:107242970-107252014 |
| 1533 | 5430416O09Rik | NR_033355.1 | chr4:43742905-43747406 | 1628 | 6430573F11Rik | NM_176286.4 | chr8:37552244-37576067 |
| 1534 | 5430417L22Rik | NR_030716.1 | chr2:118571497-118574543 | 1629 | 6430584L05Rik | NR_046179.1 | chr6:55346880-55362279 |
| 1535 | 5430419D17Rik | NM_175166.3 | chr7:138317915-138394459 | 1630 | 6430706D22Rik | NR_040291.1 | chr1:90159688-90165983 |
| 1536 | 5430421F17Rik | NR_040352.1 | chr8:26413121-26416742 | 1631 | 6430710C18Rik | NR_102348.1 | chr2:72583902-72651774 |
| 1537 | 5430421N21Rik | NM_001201323.1 | chr15:101315560-101321943 | 1632 | 6430710C18Rik | NR_102349.1 | chr2:72583902-72651774 |
| 1538 | 5430425K12Rik | NR_103550.1 | chr13:81079663-81087858 | 1633 | 6530402F18Rik | NR_029460.1 | chr2:29100636-29108513 |
| 1539 | 5430427M07Rik | NR_045858.1 | chr12:92284288-92295075 | 1634 | 6530411M01Rik | NR_027881.1 | chr17:9340583-9360887 |
| 1540 | 5430427O19Rik | NM_001163539.1 | chrX:83115611-83136838 | 1635 | 6720416L17Rik | NR_110445.1 | chr2:74586479-74600953 |
| 1541 | 5430428K19Rik | NR_045426.1 | chrX:6029494-6151781 | 1636 | 6720468P15Rik | NR_040306.1 | chr19:57583053-57587278 |
| 1542 | 5430434I15Rik | NR_040541.1 | chr3:38102072-38107041 | 1637 | 6720468P15Rik | NR_040307.1 | chr19:57583053-57587278 |
| 1543 | 5430435G22Rik | NM_145509.2 | chr1:133585271-133610041 | 1638 | 6720483E21Rik | NR_040492.1 | chr1:20878730-20880554 |
| 1544 | 5430437J10Rik | NR_045274.1 | chr15:5446317-5544983 | 1639 | 6720489N17Rik | NM_173381.1 | chr13:62704374-62725542 |
| 1545 | 5430440P10Rik | NR_045859.1 | chr14:105826775-105836933 | 1640 | 6820400D15Rik | NM_001289738.1 | chr2:152241322-152270066 |
| 1546 | 5530400C23Rik | NM_027784.1 | chr6:133242233-133245808 | 1641 | 6820408C15Rik | NR_177656.4 | chr2:152241322-152270066 |
| 1547 | 5530401A14Rik | NR_038010.1 | chr11:81674179-81708084 | 1642 | 6820408C15Rik | NR_110367.1 | chr2:152241322-152270066 |
| 1548 | 5530601H04Rik | NR_015467.1 | chrX:102236192-102265463 | 1643 | 6820408C15Rik | NR_110368.1 | chr2:152241322-152270066 |
| 1549 | 5730403I07Rik | NR_040378.1 | chr9:77214218-77247223 | 1644 | 6820431F20Rik | NR_030708.1 | chr8:19863863-19893010 |
| 1550 | 5730405O15Rik | NR_038158.1 | chrX:12619140-12622421 | 1645 | 6820431F20Rik | NR_030708.1 | chr8:19981359-20020392 |
| 1551 | 5730408K05Rik | NR_027866.1 | chr19:8962877-8963260 | 1646 | 7420426K07Rik | NM_001033983.1 | chr9:98803537-98805041 |
| 1552 | 5730409E04Rik | NM_001013755.3 | chr4:126287097-126291615 | 1647 | 7420461P10Rik | NM_001177581.1 | chr1:164577374-164588350 |
| 1553 | 5730409E04Rik | NM_001145950.1 | chr4:126287097-126291615 | 1648 | 7420700N18Rik | NR_046272.1 | chr3:32478220-32492910 |
| 1554 | 5730412P04Rik | NR_045424.1 | chrX:132639141-132649959 | 1649 | 7420701I03Rik | NR_045860.1 | chr12:11054618-11085547 |
| 1555 | 5730412P04Rik | NR_045425.1 | chrX:132639141-132649959 | 1650 | 7530416G11Rik | NM_001256072.1 | chr15:85323165-85333657 |
| 1556 | 5730416F02Rik | NR_033596.1 | chrX:106196823-106197635 | 1651 | 7630403G23Rik | NR_040744.1 | chr9:33849955-33866604 |
| 1557 | 5730420D15Rik | NR_045338.1 | chr10:94880008-94891274 | 1652 | 8030411F24Rik | NR_030135.2 | chr2:148607744-148611672 |
| 1558 | 5730420D15Rik | NR_045339.1 | chr10:94880008-94891274 | 1653 | 8030423F21Rik | NR_045738.1 | chr5:52998788-53010250 |
| 1559 | 5730422E09Rik | NR_015478.2 | chr5:149991141-149993612 | 1654 | 8030423J24Rik | NM_029872.1 | chr13:71021825-71023381 |
| 1560 | 5730435G14Rik | NR_045341.1 | chr10:41287822-41296282 | 1655 | 8030442B05Rik | NR_040615.1 | chr2:11259993-11320127 |
| 1561 | 5730455P16Rik | NM_027472.3 | chr11:80173993-80191517 | 1656 | 8030443J20Rik | NR_040664.1 | chr4:108615448-108644682 |
| 1562 | 5730457N03Rik | NR_038163.1 | chr6:52258383-52264826 | 1657 | 8030462N17Rik | NM_178670.3 | chr18:77872019-77952749 |
| 1563 | 5730460C07Rik | NR_045801.1 | chr3:153452268-153455051 | 1658 | 8430408G22Rik | NM_001166580.1 | chr6:116583025-116623854 |
| 1564 | 5730480H06Rik | NR_045500.1 | chr5:48786812-48805533 | 1659 | 8430408G22Rik | NM_145980.2 | chr6:116583025-116623854 |
| 1565 | 5730488B01Rik | NR_073462.1 | chr4:44715672-44717982 | 1660 | 8430419N10Rik | NM_028082.4 | chr5:135148040-135186258 |
| 1566 | 5730507C01Rik | NM_001033157.4 | chr12:18521315-18542060 | 1661 | 8430422H06Rik | NR_045373.1 | chr18:14390814-14437051 |
| 1567 | 5730507C01Rik | NM_001201330.1 | chr12:18521315-18542060 | 1662 | 8430423G03Rik | NR_040686.1 | chr5:149761825-149763234 |
| 1568 | 5730508B09Rik | NM_027482.3 | chr3:127572605-127599241 | 1663 | 8430426J06Rik | NR_077229.1 | chr15:81073083-81082292 |
| 1569 | 5730522E02Rik | NR_027973.1 | chr1:25516846-26110576 | 1664 | 8430426J06Rik | NR_077230.1 | chr15:81073083-81082292 |
| 1570 | 5730529C18Rik | NM_028872.3 | chr1:138110098-138130857 | 1665 | 8430426J06Rik | NR_077231.1 | chr15:81073083-81082292 |
| 1571 | 5830403L16Rik | NM_178243.3 | chr1:155696671-155698325 | 1666 | 8430427H17Rik | NM_001001986.2 | chr2:153233196-153355707 |
| 1572 | 5830411N06Rik | NM_001128145.1 | chr7:147433199-147485690 | 1667 | 8430427H17Rik | NM_001134300.2 | chr2:153233196-153355707 |
| 1573 | 5830411N06Rik | NM_001128146.1 | chr7:147433199-147485690 | 1668 | 8430429P09Rik | NR_028317.1 | chr11:3315975-3379834 |
| 1574 | 5830411N06Rik | NM_175533.2 | chr7:147433199-147485690 | 1669 | 8430429K09Rik | NR_045275.1 | chr11:3315975-3379834 |
| 1575 | 5830415F09Rik | NM_029086.2 | chr4:46389846-46402295 | 1670 | 8430429K09Rik | NR_045276.1 | chr11:3315975-3379834 |
| 1576 | 5830416I19Rik | NR_045384.1 | chr5:64436211-64441465 | 1671 | 8430431X17Rik | NR_002849.1 | chr19:31288033-31290886 |
| 1577 | 5830416P10Rik | NR_028427.1 | chr19:53515701-53539286 | 1672 | 8430436N08Rik | NR_040645.1 | chr4:7487834-7500948 |
| 1578 | 5830417J10Rik | NR_028359.1 | chr3:88580979-88633293 | 1673 | 8430437L04Rik | NR_040503.1 | chr2:72541566-72567525 |
| 1579 | 5830418K08Rik | NM_176976.4 | chr9:15121358-15162232 | 1674 | 9030025P20Rik | NM_001123370.1 | chr17:15115827-15128541 |
| 1580 | 5830418P13Rik | NR_040466.1 | chr2:103325908-103363590 | 1675 | 9030204H09Rik | NR_040618.1 | chr3:35674710-35678905 |
| 1581 | 5830428M24Rik | NR_038060.1 | chr12:70565773-70576537 | 1676 | 9030404E10Rik | NR_045878.1 | chr16:30021927-30039565 |
| 1582 | 5830428M24Rik | NR_038061.1 | chr12:70565773-70576537 | 1677 | 9030612L09Rik | NR_102361.1 | chr10:42894504-42896371 |
| 1583 | 5830432E09Rik | NR_015548.1 | chr7:142840140-142843997 | 1678 | 9030617O03Rik | NR_145448.4 | chr12:102017332-102110820 |
| 1584 | 5830444B04Rik | NR_102283.1 | chr4:154775077-154817219 | 1679 | 9030619P08Rik | NR_108041.1 | chr15:75258035-75262259 |
| 1585 | 5830444B04Rik | NR_102284.1 | chr4:154775077-154817219 | 1680 | 9030624G23Rik | NM_001256489.1 | chr12:24728066-24782134 |
| 1586 | 5830444B04Rik | NR_102287.1 | chr4:154775077-154817219 | 1681 | 9030624J02Rik | NM_027815.4 | chr7:125883784-125985005 |
| 1587 | 5830454E08Rik | NR_073359.1 | chr9:120486447-120487190 | 1682 | 9030625G05Rik | NR_110446.1 | chr18:75132417-75141201 |
| 1588 | 5830473C10Rik | NM_001252661.1 | chr5:90990234-91026932 | 1683 | 9130008F23Rik | NM_027834.3 | chr17:41012430-41017507 |
| 1589 | 5930403L14Rik | NR_045643.1 | chr4:154004800-154010476 | 1684 | 9130011E15Rik | NM_198296.2 | chr19:45892633-46072978 |
| 1590 | 5930412G12Rik | NR_015517.2 | chr5:129085004-129106562 | 1685 | 9130015A21Rik | NR_045050.1 | chr12:36356962-36379790 |
| 1591 | 5930430L01Rik | NR_102383.1 | chr5:149801631-149806791 | 1686 | 9130015A21Rik | NR_045051.1 | chr12:36356962-36379790 |
| 1592 | 5930430L01Rik | NR_102384.1 | chr5:149801631-149806791 | 1687 | 9130015L21Rik | NR_040499.1 | chr2:159842388-159866356 |
| 1593 | 5930438M14Rik | NR_046158.1 | chr13:102002081-102017506 | 1688 | 9130019O22Rik | NM_030226.3 | chr7:134525773-134530680 |
| 1594 | 6030407O03Rik | NR_045311.1 | chr1:73664955-73911040 | 1689 | 9130019P16Rik | NR_033635.1 | chr5:54219675-54380215 |
| 1595 | 6030408B16Rik | NR_033803.1 | chr15:101123642-101127857 | 1690 | 9130023H24Rik | NM_177001.3 | chr7:135377965-135381545 |
| 1596 | 6030419C18Rik | NM_176921.1 | chr9:58336409-58347549 | 1691 | 9130024F11Rik | NR_024325.1 | chr1:57028312-57032040 |
| 1597 | 6030440G07Rik | NR_036598.1 | chr2:112232607-112252082 | 1692 | 9130024F11Rik | NR_024326.1 | chr1:57028312-57032040 |
| 1598 | 6030443J06Rik | NR_102315.1 | chr5:22056230-22063989 | 1693 | 9130204L05Rik | NM_001101461.2 | chr3:90892058-90894727 |
| 1599 | 6030458C11Rik | NM_001166360.1 | chr5:12737931-12754412 | 1694 | 9130209O04Rik | NR_033453.1 | chr18:47612321-47630522 |
| 1600 | 6030458C11Rik | NM_029998.3 | chr5:12737931-12754412 | 1695 | 9130221F21Rik | NR_046180.1 | chr7:71963889-71992522 |
| 1601 | 6030466F02Rik | NR_040702.1 | chr8:126257857-126263841 | 1696 | 9130223H24Rik | NR_046001.1 | chr1:26013742-26015283 |
| 1602 | 6030468B19Rik | NM_029964.1 | chr11:117658973-117668622 | 1697 | 9130227L01Rik | NR_045837.1 | chr1:55988084-56028942 |
| 1603 | 6030469F06Rik | NR_102715.1 | chr2:81853726-81870787 | 1698 | 9130230L23Rik | NR_027961.1 | chr5:66379166-66395524 |
| 1604 | 6030498E09Rik | NM_183126.2 | chrX:36125956-36315865 | 1699 | 9130401M01Rik | NM_029418.4 | chr15:57853826-57865849 |
| 1605 | 6230400D17Rik | NR_029446.1 | chr14:21521234-21522321 | 1700 | 9130409J23Rik | NM_001033819.2 | chr1:182981367-182990798 |
| 1606 | 6330403A02Rik | NM_001081227.2 | chr1:182362503-182413635 | 1701 | 9230009I02Rik | NR_045865.1 | chr11:50898588-50905337 |
| 1607 | 6330403K07Rik | NM_134022.2 | chr1:70845442-70847119 | 1702 | 9230102K24Rik | NR_028438.1 | chr10:110037705-110053017 |
| 1608 | 6330407A03Rik | NR_028126.1 | chr4:3642111-3643953 | 1703 | 9230102O04Rik | NR_040511.1 | chr2:9804668-9811167 |
| 1609 | 6330408A02Rik | NM_177312.4 | chr7:13844316-13864070 | 1704 | 9230104L09Rik | NM_029960.3 | chr2:148672449-148676670 |

Fig. 25 - 10

| | | | |
|---|---|---|---|
| 1705 | 9230105E05Rik | NR_040626.1 | chr10:119826579-119829849 |
| 1706 | 9230110C19Rik | NM_199017.2 | chr9:8021671-8042823 |
| 1707 | 9230110F15Rik | NM_029863.1 | chr9:35645913-35651735 |
| 1708 | 9230112D13Rik | NM_030062.1 | chr14:35324808-35335987 |
| 1709 | 9230112J17Rik | NR_040463.1 | chr9:60371773-60393689 |
| 1710 | 9230112J17Rik | NR_040464.1 | chr9:60371773-60393689 |
| 1711 | 9230114K14Rik | NR_015537.2 | chr5:52581919-52589223 |
| 1712 | 9230116L04Rik | NR_110486.1 | chr12:80189692-80204926 |
| 1713 | 9230116N13Rik | NR_024328.1 | chr1:138308493-138312096 |
| 1714 | 9330020H09Rik | NR_028442.1 | chr15:98397755-98401295 |
| 1715 | 9330102E08Rik | NR_077223.1 | chr6:128119717-128133821 |
| 1716 | 9330111N05Rik | NR_015587.2 | chr13:81103334-81218856 |
| 1717 | 9330117O12Rik | NR_045400.1 | chr18:54771397-54799524 |
| 1718 | 9330133O14Rik | NR_045696.1 | chr8:124967556-124970376 |
| 1719 | 9330151J19Rik | NR_033222.1 | chr12:70298198-70300855 |
| 1720 | 9330158H04Rik | NR_015589.1 | chr6:36283138-36338234 |
| 1721 | 9330159F19Rik | NM_001162537.2 | chr10:28931448-28950585 |
| 1722 | 9330159M07Rik | NR_037982.1 | chr9:88734001-88753708 |
| 1723 | 9330159M07Rik | NR_037983.1 | chr9:88734001-88753708 |
| 1724 | 9330162O12Rik | NR_102323.1 | chr3:25029270-25030918 |
| 1725 | 9330162B11Rik | NR_038007.1 | chr1:189830455-189832869 |
| 1726 | 9330175E14Rik | NR_015514.2 | chr8:96957026-96959903 |
| 1727 | 9330175M20Rik | NR_045151.2 | chr1:51275230-51390623 |
| 1728 | 9330178D15Rik | NR_040553.1 | chr3:155639317-155671556 |
| 1729 | 9330179D12Rik | NR_040273.1 | chr6:127075726-127162437 |
| 1730 | 9330179D12Rik | NR_040274.1 | chr6:127075726-127162437 |
| 1731 | 9330179D12Rik | NR_040275.1 | chr6:127075726-127162437 |
| 1732 | 9330182L06Rik | NM_172706.3 | chr9:9266193-9480717 |
| 1733 | 9330182O14Rik | NM_001256056.1 | chr15:39965910-39981556 |
| 1734 | 9330188P03Rik | NR_102319.1 | chr14:105988765-105993146 |
| 1735 | 9430007A20Rik | NM_198662.3 | chr4:144109724-144119256 |
| 1736 | 9430008C03Rik | NR_015463.1 | chr2:158179435-158187258 |
| 1737 | 9430008C03Rik | NR_027887.1 | chr2:158179435-158187258 |
| 1738 | 9430014N10Rik | NR_045737.1 | chr5:93735286-93757542 |
| 1739 | 9430015G10Rik | NM_145557.3 | chr4:155484106-155501372 |
| 1740 | 9430015G10Rik | NM_177205.3 | chr4:155484106-155501372 |
| 1741 | 9430016H08Rik | NM_001081181.2 | chr1:57463392-57472802 |
| 1742 | 9430018G01Rik | NR_045988.1 | chr6:43392428-43424317 |
| 1743 | 9430019J16Rik | NR_040635.1 | chr2:75274113-75282236 |
| 1744 | 9430020K01Rik | NM_001081963.1 | chr18:4634926-4682867 |
| 1745 | 9430021M05Rik | NR_033569.1 | chr2:162486898-162500940 |
| 1746 | 9430037G07Rik | NR_040766.1 | chr9:88490162-88494081 |
| 1747 | 9430038I01Rik | NM_029886.2 | chr7:144567251-144602439 |
| 1748 | 9430041J12Rik | NR_033568.1 | chr7:4025727-4072330 |
| 1749 | 9430060I03Rik | NR_015525.1 | chr1:94830120-94847167 |
| 1750 | 9430066H07Rik | NM_001256161.1 | chr15:34276806-34287627 |
| 1751 | 9430076C15Rik | NR_015553.2 | chr6:53237288-53347210 |
| 1752 | 9430083A17Rik | NR_029463.1 | chr13:51193106-51196096 |
| 1753 | 9430091E24Rik | NR_040363.1 | chr8:113618644-113669398 |
| 1754 | 9430091E24Rik | NR_040364.1 | chr8:113618644-113669398 |
| 1755 | 9530002B09Rik | NM_023865.3 | chr4:122366501-122382378 |
| 1756 | 9530003J23Rik | NM_029906.3 | chr10:116670808-116675737 |
| 1757 | 9530026F06Rik | NR_040483.1 | chr1:61435275-61452748 |
| 1758 | 9530026P05Rik | NR_015530.2 | chr6:92890575-93061743 |
| 1759 | 9530027J09Rik | NR_045916.1 | chrX:45629969-45638603 |
| 1760 | 9530036O11Rik | NR_015562.1 | chr5:28793524-29045749 |
| 1761 | 9530051G07Rik | NR_040272.1 | chrX:149471171-149507458 |
| 1762 | 9530052E02Rik | NR_046017.1 | chr8:11007850-11054541 |
| 1763 | 9530053A07Rik | NM_001164655.1 | chr7:28914484-28949830 |
| 1764 | 9530059O14Rik | NR_015610.1 | chr9:122481618-122489765 |
| 1765 | 9530068E07Rik | NM_153117.2 | chr11:52209929-52222225 |
| 1766 | 9530077C05Rik | NM_028739.1 | chr9:22216020-22249123 |
| 1767 | 9530080O11Rik | NR_045776.1 | chr4:95626401-95690965 |
| 1768 | 9530080O11Rik | NR_045777.1 | chr4:95626401-95690965 |
| 1769 | 9530082P21Rik | NR_015472.1 | chr17:23886202-23891032 |
| 1770 | 9530091C08Rik | NR_033299.1 | chr9:68613153-68621129 |
| 1771 | 9630010O16Rik | NR_102378.1 | chr5:46030514-46036708 |
| 1772 | 9630013A20Rik | NR_015539.1 | chr14:84858645-84876231 |
| 1773 | 9630028B13Rik | NR_038006.1 | chr1:187253235-187265698 |
| 1774 | 9630028H03Rik | NR_015544.2 | chr2:135406265-135408956 |
| 1775 | 9630033F20Rik | NM_177003.5 | chr6:127035133-127059570 |
| 1776 | 9830107B12Rik | NM_001177896.1 | chr7:48262554-48283257 |
| 1777 | 9830107B12Rik | NM_001177897.1 | chr7:48262554-48283257 |
| 1778 | 9830107B12Rik | NM_177824.4 | chr7:48262554-48283257 |
| 1779 | 9830132P13Rik | NR_040552.1 | chr3:127619088-127658138 |
| 1780 | 9830147E19Rik | NM_001242388.1 | chr7:49864895-49897974 |
| 1781 | 9830166K06Rik | NR_045314.1 | chr19:8726285-8737825 |
| 1782 | 9930012K11Rik | NM_001004155.2 | chr14:70554211-70559309 |
| 1783 | 9930012K11Rik | NM_001112735.1 | chr14:70554211-70559309 |
| 1784 | 9930014A18Rik | NR_030696.1 | chr15:60654520-60662955 |
| 1785 | 9930021J03Rik | NM_172836.3 | chr19:29788891-29880499 |
| 1786 | 9930104L06Rik | NM_177573.3 | chr4:124614291-124621905 |
| 1787 | 9930111H07Rik | NR_108086.1 | chr1:87671845-87681269 |
| 1788 | 9930111J21Rik1 | NM_001114679.1 | chr1:48759652-48792883 |
| 1789 | 9930111J21Rik1 | NR_173434.1 | chr1:48758850-48792900 |
| 1790 | 9930111J21Rik2 | NR_173434.1 | chr1:48851161-48948889 |
| 1791 | a | NM_015770.3 | chr2:154839305-154876748 |
| 1792 | A130010J15Rik | NM_001160359.1 | chr1:194999662-195027740 |
| 1793 | A130010J15Rik | NM_001160360.1 | chr1:194999662-195027740 |
| 1794 | A130010J15Rik | NM_181048.2 | chr1:194999662-195027740 |
| 1795 | A130077B15Rik | NR_040616.1 | chr10:122002078-122006947 |
| 1796 | A1bg | NM_001081067.1 | chr15:60749143-60752825 |
| 1797 | A1cf | NM_001081074.1 | chr19:31943250-32023896 |
| 1798 | A230001M10Rik | NR_040391.1 | chr3:102066327-102092694 |
| 1799 | A230009B12Rik | NR_077237.1 | chr17:10595877-11033057 |
| 1800 | A230009B12Rik | NR_077238.1 | chr17:10595877-11033057 |
| 1801 | A230009B12Rik | NR_077239.1 | chr17:10595877-11033057 |
| 1802 | A230020J21Rik | NR_027298.1 | chr1:192849230-192853660 |
| 1803 | A230022O05Rik | NR_040374.1 | chr16:25059724-25069144 |
| 1804 | A230046K03Rik | NM_001033375.1 | chr10:83006685-83059218 |
| 1805 | A230050P20Rik | NM_175687.2 | chr9:20673086-20678751 |
| 1806 | A230056J06Rik | NR_045633.1 | chr13:59681536-59686584 |
| 1807 | A230056P14Rik | NR_015495.2 | chr7:63217901-63235466 |
| 1808 | A230057O06Rik | NR_015533.2 | chr7:68850736-69072460 |
| 1809 | A230065H16Rik | NM_001101503.1 | chr12:112645019-112650288 |
| 1810 | A230070E04Rik | NR_045897.1 | chr14:68741809-68749428 |
| 1811 | A230072C01Rik | NR_027445.1 | chrX:20528790-20564475 |
| 1812 | A230072C01Rik | NR_027446.1 | chrX:20528790-20564475 |
| 1813 | A230072E10Rik | NR_015602.2 | chrX:147747878-147776422 |
| 1814 | A230073K19Rik | NR_033229.1 | chr7:66,537,249-66,544,536 |
| 1815 | A230077H06Rik | NR_040329.1 | chr7:48104522-48153654 |
| 1816 | A230103J11Rik | NR_110581.1 | chr8:87560813-87591019 |
| 1817 | A230103J11Rik | NR_110582.1 | chr8:87560813-87591019 |
| 1818 | A230108P19Rik | NR_040333.1 | chr2:6114297-6242657 |
| 1819 | A2m | NM_175628.3 | chr6:121586190-121629256 |
| 1820 | A330009N23Rik | NR_045326.1 | chr15:101051621-101063187 |
| 1821 | A330009N23Rik | NR_045327.1 | chr15:101051621-101063187 |
| 1822 | A330009N23Rik | NR_045328.1 | chr15:101051621-101063187 |
| 1823 | A330021E22Rik | NM_172447.2 | chr5:5580981-5664232 |
| 1824 | A330023F24Rik | NR_015546.2 | chr1:196843593-196864102 |
| 1825 | A330032B11Rik | NR_045329.1 | chr19:37248333-37271031 |
| 1826 | A330033J07Rik | NR_102303.1 | chr13:48139600-48357992 |
| 1827 | A330035P11Rik | NR_015586.2 | chr14:122497160-122506196 |
| 1828 | A330040F15Rik | NR_015503.2 | chr19:12660358-12671056 |
| 1829 | A330041J22Rik | NR_045835.1 | chr9:86589475-86595286 |
| 1830 | A330048O09Rik | NR_045162.1 | chr13:48367786-48369253 |
| 1831 | A330049N07Rik | NR_040646.1 | chr10:72436050-72549453 |
| 1832 | A330050F15Rik | NM_001145192.1 | chr17:69788665-69838573 |
| 1833 | A330069E16Rik | NR_015464.1 | chr2:91077302-91078514 |
| 1834 | A330070K13Rik | NM_198665.1 | chr5:130854721-130860501 |
| 1835 | A330074K22Rik | NR_110450.1 | chr8:122728333-122752130 |
| 1836 | A330076C08Rik | NR_045088.1 | chr13:44288957-44311856 |
| 1837 | A330076H08Rik | NR_015599.2 | chr7:69088787-69127189 |
| 1838 | A330093E20Rik | NR_040342.1 | chr18:45843141-46204914 |
| 1839 | A330102J10Rik | NR_045073.1 | chr13:29106282-29132205 |
| 1840 | A330102J10Rik | NR_045074.1 | chr13:29106282-29132205 |
| 1841 | A330102J10Rik | NR_045075.1 | chr13:29106282-29132205 |
| 1842 | A330102J10Rik | NR_045077.1 | chr13:29106282-29132205 |
| 1843 | A3galt2 | NM_001009819.2 | chr4:128436501-128446542 |
| 1844 | A430005L14Rik | NM_001163019.1 | chr4:153331345-153336033 |
| 1845 | A430005L14Rik | NM_175287.4 | chr4:153331345-153336033 |
| 1846 | A430033K04Rik | NM_183025.2 | chr5:139064086-139090054 |
| 1847 | A430035B10Rik | NR_040452.1 | chr6:8457058-8459161 |
| 1848 | A430078G23Rik | NM_001033378.3 | chr8:3353414-3390299 |
| 1849 | A430088P11Rik | NR_045309.1 | chr15:80502276-80530855 |
| 1850 | A430088P11Rik | NR_045310.1 | chr15:80502276-80530855 |
| 1851 | A430089J19Rik | NM_177913.4 | chr5:94731543-94735821 |
| 1852 | A430089J19Rik | NM_177913.4 | chr5:95380098-95384376 |
| 1853 | A430089J19Rik | NM_177913.4 | chrUn_random:1585650-1589928 |
| 1854 | A430090L17Rik | NR_045836.1 | chr13:114914556-114941800 |
| 1855 | A430093F15Rik | NR_027805.1 | chr19:10815436-10860533 |
| 1856 | A430105J19Rik | NM_001001982.2 | chr2:118579880-118588397 |
| 1857 | A430107P09Rik | NR_001205242.1 | chr14:54285614-54288010 |
| 1858 | A4galt | NM_001004150.3 | chr15:83057151-83082204 |
| 1859 | A4galt | NM_001170954.1 | chr15:83057151-83082204 |
| 1860 | A4gnt | NM_001077424.2 | chr9:99512920-99522786 |
| 1861 | A530006G24Rik | NR_046014.1 | chr2:147536428-147543368 |
| 1862 | A530013C23Rik | NM_000500.3 | chr2:167516258-167522913 |
| 1863 | A530013C23Rik | NR_110334.1 | chr2:167516258-167522913 |
| 1864 | A530016L24Rik | NM_177039.4 | chr12:113727658-113738138 |
| 1865 | A530032D15Rik | NM_213615.2 | chr1:85084713-85106428 |
| 1866 | A530046M15Rik | NR_046131.1 | chr13:15899075-15919370 |
| 1867 | A530050N04Rik | NR_045419.1 | chr18:61629878-61644261 |
| 1868 | A530053G22Rik | NR_015565.2 | chr6:60229036-60353701 |
| 1869 | A530054K11Rik | NR_183146.3 | chr13:67717937-67738690 |
| 1870 | A530058N18Rik | NR_028423.1 | chr2:113839301-113858028 |
| 1871 | A530064D06Rik | NM_001113556.1 | chr7:48288845-48304207 |
| 1872 | A530064D06Rik | NM_178796.6 | chr7:48288845-48304207 |
| 1873 | A530065N20Rik | NR_046142.1 | chr13:60131071-60218030 |
| 1874 | A530072M11Rik | NR_045765.2 | chr4:16091256-16193372 |
| 1875 | A530088E08Rik | NR_029458.1 | chr17:32539959-32541753 |
| 1876 | A530099J19Rik | NM_175688.4 | chr13:19819285-19824820 |
| 1877 | A630001G21Rik | NM_177055.3 | chr1:87613657-87633181 |
| 1878 | A630007B06Rik | NM_170757.1 | chr19:56865452-56888173 |
| 1879 | A630010A05Rik | NR_033556.1 | chr16:14562409-14621377 |
| 1880 | A630012P03Rik | NR_045367.2 | chrX:49929020-49972224 |
| 1881 | A630019J02Rik | NR_046182.1 | chr13:93864788-93868923 |
| 1882 | A630020A06 | NR_045740.1 | chr15:3946038-3965858 |
| 1883 | A630023A22Rik | NM_001251843.1 | chr14:34864316-34915940 |
| 1884 | A630023P12Rik | NR_102290.1 | chr5:110943941-110954998 |
| 1885 | A630033B20Rik | NM_001122595.1 | chrX:104344265-104369000 |
| 1886 | A630033H20Rik | NM_001122596.1 | chrX:104344265-104369000 |
| 1887 | A630033H20Rik | NM_175442.4 | chrX:104344265-104369000 |
| 1888 | A630066F11Rik | NR_030699.1 | chr10:7383169-7384421 |
| 1889 | A630072M18Rik | NR_030699.1 | chr5:20456807-20462216 |
| 1890 | A630073D07Rik | NM_001142969.1 | chr6:132575128-132577529 |
| 1891 | A630075F10Rik | NR_033632.1 | chr2:169886739-169896278 |
| 1892 | A630075F10Rik | NR_033634.1 | chr2:169886739-169896278 |
| 1893 | A630076J17Rik | NM_001256174.1 | chr3:107033531-107036949 |

Fig. 25 - 11

| | | | | | | | |
|---|---|---|---|---|---|---|---|
| 1894 | A630077J23Rik | NR_040667.1 | chr4:43764730-43772336 | 1989 | Aak1 | NM_177762.6 | chr6:86799510-86953221 |
| 1895 | A630089N07Rik | NR_015491.1 | chr16:98283676-98303604 | 1990 | Aamdc | NM_001177945.1 | chr7:104698840-104728007 |
| 1896 | A630095E13Rik | NM_001033325.2 | chr9:36443338-36446187 | 1991 | Aamdc | NM_001177946.1 | chr7:104698840-104728007 |
| 1897 | A630095N17Rik | NM_001243090.1 | chr1:75216669-75228668 | 1992 | Aamdc | NM_001177947.1 | chr7:104698840-104728007 |
| 1898 | A630095N17Rik | NM_001243091.1 | chr1:75216669-75228668 | 1993 | Aamdc | NM_183251.3 | chr7:104698840-104728007 |
| 1899 | A730006G06Rik | NR_110485.1 | chr17:48201739-48227328 | 1994 | Aamp | NM_001190444.1 | chr1:74326413-74331312 |
| 1900 | A730008H23Rik | NM_172505.4 | chr1:90161403-90174132 | 1995 | Aamp | NM_146110.3 | chr1:74326413-74331312 |
| 1901 | A730017C20Rik | NM_001167925.2 | chr18:59222034-59236614 | 1996 | Aanat | NM_009591.3 | chr11:116455000-116458994 |
| 1902 | A730017C20Rik | NM_173759.5 | chr18:59222034-59236614 | 1997 | Aanat | NR_033223.1 | chr11:116455000-116458994 |
| 1903 | A730017C20Rik | NR_033764.1 | chr18:59222034-59236614 | 1998 | Aar2 | NM_001164818.1 | chr2:156373311-156394708 |
| 1904 | A730017C20Rik | NR_033765.1 | chr18:59222034-59236614 | 1999 | Aar2 | NM_026661.4 | chr2:156373311-156394708 |
| 1905 | A730017L22Rik | NR_015523.2 | chr2:130698276-130732132 | 2000 | Aard | NM_175503.3 | chr15:51871652-51877269 |
| 1906 | A730018C14Rik | NR_036459.1 | chr12:113649233-113661409 | 2001 | Aars | NM_146217.4 | chr8:113557741-113579469 |
| 1907 | A730020E08Rik | NR_040287.1 | chr6:61125598-61130804 | 2002 | Aars2 | NM_198608.2 | chr17:45643789-45657792 |
| 1908 | A730020M07Rik | NR_036456.1 | chr3:121337855-121349371 | 2003 | Aarsd1 | NM_144829.1 | chr11:101268153-101278747 |
| 1909 | A730020M07Rik | NR_036457.1 | chr3:121337855-121349371 | 2004 | Aasdh | NM_173765.3 | chr5:77304959-77334539 |
| 1910 | A730020M07Rik | NR_036458.1 | chr3:121337855-121349371 | 2005 | Aasdhppt | NM_026276.3 | chr9:4294792-4309494 |
| 1911 | A730036H17Rik | NR_045838.1 | chr2:129044704-129061342 | 2006 | Aass | NM_013930.4 | chr6:23022172-23082986 |
| 1912 | A730043L09Rik | NR_040769.1 | chr9:62090402-62091907 | 2007 | Aatf | NM_019816.1 | chr11:84236357-84327003 |
| 1913 | A730046J19Rik | NR_040271.1 | chrX:140588237-140600817 | 2008 | Aatk | NM_001198785.1 | chr11:119868631-119908459 |
| 1914 | A730056A06Rik | NR_040324.1 | chr7:80455265-80564785 | 2009 | Aatk | NM_001198787.1 | chr11:119868631-119908459 |
| 1915 | A730056A06Rik | NR_040325.1 | chr7:80455265-80564785 | 2010 | Aatk | NM_007377.4 | chr11:119868631-119908459 |
| 1916 | A730082K24Rik | NR_040317.1 | chr7:122092163-122127481 | 2011 | AB041803 | NR_110469.1 | chr6:31043562-31168474 |
| 1917 | A730082K24Rik | NR_040319.1 | chr7:122092163-122127481 | 2012 | AB041803 | NR_110470.1 | chr6:31043562-31168474 |
| 1918 | A730085K08Rik | NR_045967.1 | chr9:122291139-122307919 | 2013 | AB041803 | NR_110471.1 | chr6:31043562-31168474 |
| 1919 | A730090H04Rik | NR_040279.1 | chr11:95006367-95020361 | 2014 | AB124611 | NM_001198794.1 | chr9:21330620-21349775 |
| 1920 | A730090N16Rik | NR_040390.1 | chr3:65127942-65153351 | 2015 | AB124611 | NM_206536.2 | chr9:21330620-21349775 |
| 1921 | A730098P11Rik | NR_038089.1.1 | chr16:24529400-24534558 | 2016 | Abat | NM_001170978.1 | chr16:8513521-8621660 |
| 1922 | A830009L08Rik | NR_045161.1 | chr13:91508594-91527690 | 2017 | Abat | NM_172961.3 | chr16:8513521-8621660 |
| 1923 | A830010M20Rik | NM_001007574.2 | chr5:107926763-107941575 | 2018 | Abca1 | NM_013454.3 | chr4:53043660-53172767 |
| 1924 | A830010M20Rik | NM_001168557.1 | chr5:107926763-107941575 | 2019 | Abca12 | NM_175234.3 | chr1:71289663-71461484 |
| 1925 | A830018L16Rik | NM_001160369.2 | chr1:11404185-11965983 | 2020 | Abca13 | NM_178259.3 | chr11:9091944-9584262 |
| 1926 | A830018L16Rik | NM_001160370.2 | chr1:11404185-11965983 | 2021 | Abca14 | NM_026458.4 | chr7:127347477-127468866 |
| 1927 | A830018L16Rik | NM_001160371.2 | chr1:11404185-11965983 | 2022 | Abca15 | NM_177213.3 | chr7:127472197-127551201 |
| 1928 | A830018L16Rik | NM_177173.6 | chr1:11404185-11965983 | 2023 | Abca16 | NM_001278943.1 | chr7:127553160-127688327 |
| 1929 | A830019L24Rik | NR_040551.1 | chr3:142906018-142920960 | 2024 | Abca16 | NM_001198944.1 | chr7:127553160-127688327 |
| 1930 | A830052D11Rik | NR_045403.1 | chr18:32518711-32537938 | 2025 | Abca17 | NM_001031621.2 | chr17:24401223-24484197 |
| 1931 | A830080D01Rik | NM_001033472.2 | chrX:155970599-156031013 | 2026 | Abca2 | NM_007379.2 | chr2:25284194-25304059 |
| 1932 | A830082K12Rik | NR_045195.1 | chr13:78337278-78375825 | 2027 | Abca3 | NM_001059581.2 | chr17:24488967-24551458 |
| 1933 | A830082N09Rik | NR_015526.2 | chr10:33707021-33714861 | 2028 | Abca3 | NM_013855.3 | chr17:24488967-24551458 |
| 1934 | A930001A20Rik | NR_040549.1 | chr3:14971200-15002727 | 2029 | Abca4 | NM_007378.1 | chr3:121747377-121882979 |
| 1935 | A930001A20Rik | NR_040550.1 | chr3:14971200-15002727 | 2030 | Abca5 | NM_147219.2 | chr11:110130682-110199030 |
| 1936 | A930001C03Rik | NR_045989.1 | chr19:4425456-4477143 | 2031 | Abca6 | NM_001166556.1 | chr11:110038135-110113090 |
| 1937 | A930001C03Rik | NR_045990.1 | chr19:4425456-4477143 | 2032 | Abca6 | NM_001166557.1 | chr11:110038135-110113090 |
| 1938 | A930003A15Rik | NR_015488.1 | chr16:19876660-19884367 | 2033 | Abca6 | NM_147218.2 | chr11:110038135-110113090 |
| 1939 | A930003A15Rik | NR_027896.1 | chr16:19876660-19884367 | 2034 | Abca7 | NM_013850.1 | chr10:79460359-79478317 |
| 1940 | A930003O13Rik | NR_027362.1 | chr5:22244729-22252702 | 2035 | Abca8a | NM_153145.4 | chr11:109886947-109957251 |
| 1941 | A930004D18Rik | NR_028376.1 | chr2:17946815-17959368 | 2036 | Abca8b | NM_013845.2 | chr11:109794719-109857130 |
| 1942 | A930004D18Rik | NR_028377.1 | chr2:17946815-17959368 | 2037 | Abca9 | NM_147220.2 | chr11:109962135-110029467 |
| 1943 | A930005H10Rik | NR_015487.1 | chr3:115584496-115591048 | 2038 | Abcb10 | NM_019552.2 | chr8:126476358-126507022 |
| 1944 | A930005H10Rik | NR_027894.1 | chr3:115584496-115591048 | 2039 | Abcb11 | NM_021022.3 | chr2:69076338-69180673 |
| 1945 | A930005H10Rik | NR_027895.1 | chr3:115584496-115591048 | 2040 | Abcb1a | NM_011076.2 | chr5:8660691-8748570 |
| 1946 | A930006I01Rik | NR_040332.1 | chr2:103178757-103212931 | 2041 | Abcb1b | NM_011075.2 | chr5:8798146-8866314 |
| 1947 | A930006K02Rik | NR_077219.1 | chr16:91465348-91470368 | 2042 | Abcb4 | NM_008830.2 | chr5:8893720-8959226 |
| 1948 | A930007J19Rik | NR_015567.2 | chr19:29578152-29596477 | 2043 | Abcb5 | NM_029961.2 | chr12:120106296-120204894 |
| 1949 | A930009A15Rik | NM_029692.1 | chr10:115007042-115019510 | 2044 | Abcb6 | NM_023732.2 | chr1:75168214-75176857 |
| 1950 | A930011G23Rik | NR_030692.1 | chr5:99726262-100158079 | 2045 | Abcb7 | NM_009592.1 | chrX:101475903-101609185 |
| 1951 | A930011O12Rik | NR_040709.1 | chr14:65206952-65212798 | 2046 | Abcb8 | NM_029020.2 | chr5:23899973-23915765 |
| 1952 | A930012I18Rik | NR_026853.1 | chr18:44821319-44835925 | 2047 | Abcb9 | NM_019715.2 | chr5:124511865-124545807 |
| 1953 | A930013F10Rik | NR_027886.1 | chr8:23744857-23747281 | 2048 | Abcc1 | NM_008576.3 | chr16:14361650-14474971 |
| 1954 | A930015D03Rik | NR_015618.2 | chr17:36131449-36175119 | 2049 | Abcc10 | NM_145140.2 | chr17:46434431-46464972 |
| 1955 | A930016O22Rik | NR_073014.1 | chr7:19996442-20006932 | 2050 | Abcc10 | NM_170680.2 | chr17:46434431-46464972 |
| 1956 | A930016O22Rik | NR_073015.1 | chr7:19996442-20006932 | 2051 | Abcc12 | NM_172912.4 | chr8:89028739-89090489 |
| 1957 | A930017M01Rik | NR_033609.2 | chr16:44712939-44716289 | 2052 | Abcc2 | NM_013806.2 | chr19:43856797-43912708 |
| 1958 | A930018P22Rik | NM_026634.2 | chr2:103962925-103964903 | 2053 | Abcc3 | NM_029600.3 | chr11:94204608-94254290 |
| 1959 | A930019D19Rik | NR_040619.1 | chr2:146085022-146092896 | 2054 | Abcc4 | NM_001033336.3 | chr14:118881913-119105441 |
| 1960 | A930024E05Rik | NR_045820.1 | chr5:123439362-123448350 | 2055 | Abcc4 | NM_001163675.1 | chr14:118881913-119105441 |
| 1961 | A930041C12Rik | NR_046195.1 | chr5:108059269-108062869 | 2056 | Abcc4 | NM_001163676.1 | chr14:118881913-119105441 |
| 1962 | AA387883 | NR_030678.1 | chr19:52997670-53001421 | 2057 | Abcc5 | NM_013790.2 | chr16:20331376-20426467 |
| 1963 | AA388235 | NR_033305.1 | chr17:34118436-34122303 | 2058 | Abcc5 | NM_176839.1 | chr16:20331376-20426467 |
| 1964 | AA413626 | NR_102683.1 | chr11:4818519-4818921 | 2059 | Abcc6 | NM_018795.2 | chr7:53231749-53285656 |
| 1965 | AA414768 | NM_001272033.1 | chrX:12513998-12515667 | 2060 | Abcc8 | NM_011510.3 | chr7:53359892-53435403 |
| 1966 | AA415398 | NM_001004178.1 | chr4:119202922-119211374 | 2061 | Abcc9 | NM_001004720.1 | chr6:142536381-142650794 |
| 1967 | AA465934 | NR_028363.1 | chr11:83105201-83108139 | 2062 | Abcc9 | NM_011511.2 | chr6:142536381-142650794 |
| 1968 | AA467197 | NM_001004174.1 | chr2:122463623-122466812 | 2063 | Abcc9 | NM_021041.2 | chr6:142536381-142650794 |
| 1969 | AA474331 | NR_033628.1 | chr10:39612565-39619044 | 2064 | Abcc9 | NM_172212.2 | chr6:142536381-142650794 |
| 1970 | AA536875 | NR_045143.1 | chr14:123567724-123575398 | 2065 | Abcd1 | NM_007435.1 | chrX:70961935-70983626 |
| 1971 | AA536875 | NR_045144.1 | chr14:123567724-123575398 | 2066 | Abcd2 | NM_011994.2 | chr15:90976301-91022238 |
| 1972 | AA536875 | NR_045145.1 | chr14:123567724-123575398 | 2067 | Abcd3 | NM_008991.2 | chr3:121461827-121518133 |
| 1973 | AA543186 | NR_027448.1 | chr2:25187969-25188091 | 2068 | Abcd4 | NM_008992.2 | chr12:85943480-85958416 |
| 1974 | AA543401 | NR_102273.1 | chr9:107095138-107096392 | 2069 | Abce1 | NM_015751.2 | chr8:82207340-82235639 |
| 1975 | AA545190 | NR_033776.1 | chr6:10921467-10924378 | 2070 | Abcf1 | NM_013854.1 | chr17:36093764-36106695 |
| 1976 | AA619741 | NR_033627.1 | chr1:34690379-34693055 | 2071 | Abcf2 | NM_001190443.1 | chr5:24071158-24083285 |
| 1977 | AA792892 | NM_178894.4 | chr5:94806364-94813359 | 2072 | Abcf2 | NM_013853.2 | chr5:24071158-24083285 |
| 1978 | AA986860 | NR_128288.1 | chr1:132628552-132641199 | 2073 | Abcf3 | NM_013852.2 | chr16:20548675-20561676 |
| 1979 | AA987161 | NM_001163246.2 | chr13:67690375-67710644 | 2074 | Abcg1 | NM_009593.2 | chr17:31194638-31254926 |
| 1980 | Aaas | NM_153416.2 | chr15:102168677-102181190 | 2075 | Abcg2 | NM_011920.3 | chr6:58546665-58642445 |
| 1981 | Aacs | NM_030210.1 | chr5:125956242-125997773 | 2076 | Abcg3 | NM_030239.2 | chr5:105384075-105411736 |
| 1982 | Aadac | NM_023383.1 | chr3:59835709-59844679 | 2077 | Abcg4 | NM_138955.3 | chr9:44081272-44096327 |
| 1983 | Aadacl2 | NM_001128091.1 | chr3:59810664-59829342 | 2078 | Abcg5 | NM_031884.1 | chr17:85057574-85082263 |
| 1984 | Aadacl3 | NM_001085503.2 | chr4:144043673-144053659 | 2079 | Abcg8 | NM_001286005.1 | chr17:85057573-85099673 |
| 1985 | Aadat | NM_011834.2 | chr8:62984920-63024474 | 2080 | Abcg8 | NM_026180.3 | chr17:85057573-85099673 |
| 1986 | Aaed1 | NM_025370.2 | chr13:64393143-64414018 | 2081 | Abcg8 | NR_104382.1 | chr17:85057573-85099673 |
| 1987 | Aagab | NM_025857.2 | chr9:63450461-63489696 | 2082 | Abhd1 | NM_021304.3 | chr5:31235515-31651218 |
| 1988 | Aak1 | NM_001040106.2 | chr6:86799510-86953221 | 2083 | Abhd1 | NR_003522.1 | chr5:31235515-31651218 |

Fig. 25 - 12

| | | | |
|---|---|---|---|
| 2084 | Abhd10 | NM_001272070.1 | chr10:45729837-45743068 |
| 2085 | Abhd10 | NM_172511.4 | chr10:45729837-45743068 |
| 2086 | Abhd10 | NR_073572.1 | chr10:45729837-45743068 |
| 2087 | Abhd11 | NM_001190437.1 | chr5:135485021-135489027 |
| 2088 | Abhd11 | NM_145215.2 | chr5:135485021-135489027 |
| 2089 | Abhd11 | NR_033794.1 | chr5:135485021-135489027 |
| 2090 | Abhd11os | NR_026688.1 | chr5:135487992-135489027 |
| 2091 | Abhd12 | NM_024465.3 | chr2:150658250-150730467 |
| 2092 | Abhd12b | NM_001195033.1 | chr12:71255157-71284193 |
| 2093 | Abhd13 | NM_001081119.1 | chr8:9977716-9992154 |
| 2094 | Abhd13 | NM_026868.1 | chr8:9977716-9992154 |
| 2095 | Abhd14a | NM_001110271.1 | chr9:106342381-106350009 |
| 2096 | Abhd14a | NM_001110272.1 | chr9:106342381-106350009 |
| 2097 | Abhd14a | NM_145919.2 | chr9:106342381-106350009 |
| 2098 | Abhd14b | NM_029631.3 | chr9:106350970-106355249 |
| 2099 | Abhd15 | NM_026185.4 | chr11:77328618-77334130 |
| 2100 | Abhd16a | NM_178592.3 | chr17:35226235-35239932 |
| 2101 | Abhd16b | NM_183181.2 | chr2:181227910-181229685 |
| 2102 | Abhd17a | NM_145421.2 | chr10:80046393-80053086 |
| 2103 | Abhd17b | NM_146096.3 | chr19:21727798-21760127 |
| 2104 | Abhd17c | NM_133722.2 | chr7:91257865-91300403 |
| 2105 | Abhd2 | NM_018811.6 | chr7:86418151-86506487 |
| 2106 | Abhd3 | NM_134130.1 | chr18:10644408-10706694 |
| 2107 | Abhd4 | NM_001205181.1 | chr14:54873803-54888844 |
| 2108 | Abhd4 | NM_134076.2 | chr14:54873803-54888844 |
| 2109 | Abhd5 | NM_026179.2 | chr9:122260733-122290641 |
| 2110 | Abhd6 | NM_025341.3 | chr14:8835415-8889069 |
| 2111 | Abhd8 | NM_022419.3 | chr8:73980598-73987556 |
| 2112 | Abi1 | NM_001077190.2 | chr2:22751041-22895761 |
| 2113 | Abi1 | NM_001077192.2 | chr2:22751041-22895761 |
| 2114 | Abi1 | NM_001077193.2 | chr2:22751041-22895761 |
| 2115 | Abi1 | NM_007380.3 | chr2:22751041-22895761 |
| 2116 | Abi1 | NM_145994.2 | chr2:22751041-22895761 |
| 2117 | Abi2 | NM_001198570.1 | chr1:60466462-60538007 |
| 2118 | Abi2 | NM_001198571.1 | chr1:60466462-60538007 |
| 2119 | Abi2 | NM_198127.2 | chr1:60466462-60538007 |
| 2120 | Abi3 | NM_001163464.1 | chr11:95685813-95707045 |
| 2121 | Abi3 | NM_025659.4 | chr11:95685813-95707045 |
| 2122 | Abi3bp | NM_001014399.2 | chr16:56477958-56690248 |
| 2123 | Abi3bp | NM_001014422.2 | chr16:56477958-56690248 |
| 2124 | Abi3bp | NM_001014423.2 | chr16:56477958-56690248 |
| 2125 | Abi3bp | NM_001014424.2 | chr16:56477958-56690248 |
| 2126 | Abi3bp | NM_178790.4 | chr16:56477958-56690248 |
| 2127 | Abl1 | NM_001112703.2 | chr2:31544056-31659882 |
| 2128 | Abl1 | NM_001283045.1 | chr2:31544056-31659882 |
| 2129 | Abl1 | NM_001283046.1 | chr2:31544056-31659882 |
| 2130 | Abl1 | NM_001283047.1 | chr2:31544056-31659882 |
| 2131 | Abl1 | NM_009594.4 | chr2:31544056-31659882 |
| 2132 | Abl2 | NM_001136104.1 | chr1:158488917-158579750 |
| 2133 | Abl2 | NM_009595.3 | chr1:158488917-158579750 |
| 2134 | Ablim1 | NM_001103177.2 | chr19:57107753-57290522 |
| 2135 | Ablim1 | NM_001103178.2 | chr19:57107753-57290522 |
| 2136 | Ablim1 | NM_001290813.1 | chr19:57107753-57290522 |
| 2137 | Ablim1 | NM_001290815.1 | chr19:57107753-57290522 |
| 2138 | Ablim1 | NM_001290816.1 | chr19:57107753-57290522 |
| 2139 | Ablim1 | NM_178688.3 | chr19:57107753-57290522 |
| 2140 | Ablim2 | NM_001177696.1 | chr5:36100528-36227628 |
| 2141 | Ablim2 | NM_001177697.1 | chr5:36100528-36227628 |
| 2142 | Ablim2 | NM_001177698.1 | chr5:36100528-36227628 |
| 2143 | Ablim2 | NM_001177699.1 | chr5:36100528-36227628 |
| 2144 | Ablim2 | NM_001177700.1 | chr5:36100528-36227628 |
| 2145 | Ablim2 | NM_177678.7 | chr5:36100528-36227628 |
| 2146 | Ablim3 | NM_001164491.1 | chr18:61959046-62071506 |
| 2147 | Ablim3 | NM_198649.3 | chr18:61959046-62071506 |
| 2148 | Abo | NM_001290444.1 | chr2:26698022-26720515 |
| 2149 | Abo | NM_030718.5 | chr2:26698022-26720515 |
| 2150 | Abr | NM_001291186.1 | chr11:76230233-76391241 |
| 2151 | Abr | NM_198018.2 | chr11:76230233-76391241 |
| 2152 | Abr | NM_198894.2 | chr11:76230233-76391241 |
| 2153 | Abr | NM_198895.2 | chr11:76230233-76391241 |
| 2154 | Abra | NM_175456.4 | chr15:41696838-41701266 |
| 2155 | Abracl | NM_028840.1 | chr10:17731086-17743058 |
| 2156 | Abt1 | NM_013924.3 | chr13:23510229-23515735 |
| 2157 | Abtb1 | NM_030251.3 | chr6:88785907-88791929 |
| 2158 | Abtb2 | NM_178890.3 | chr2:103406466-103558580 |
| 2159 | Acaa1a | NM_130864.3 | chr9:119250411-119259413 |
| 2160 | Acaa1b | NM_146230.3 | chr9:119057160-119066211 |
| 2161 | Acaa2 | NM_177470.3 | chr18:74938865-74965861 |
| 2162 | Acaca | NM_133360.2 | chr11:84008939-84215153 |
| 2163 | Acacb | NM_133904.2 | chr5:114615526-114700767 |
| 2164 | Acad10 | NM_028037.4 | chr5:122071037-122110519 |
| 2165 | Acad11 | NM_175324.3 | chr9:103966033-104029976 |
| 2166 | Acad12 | NM_178799.3 | chr5:122048289-122068947 |
| 2167 | Acad8 | NM_025862.2 | chr9:26781725-26807134 |
| 2168 | Acad9 | NM_172678.3 | chr3:35964921-35991779 |
| 2169 | Acadl | NM_007381.4 | chr1:66877412-66909883 |
| 2170 | Acadm | NM_007382.5 | chr3:153585316-153607607 |
| 2171 | Acads | NM_007383.3 | chr5:115560307-115569355 |
| 2172 | Acadsb | NM_025826.4 | chr7:138554114-138589725 |
| 2173 | Acadvl | NM_017366.3 | chr11:69823685-69828930 |
| 2174 | Acan | NM_007424.2 | chr7:86198368-86259985 |
| 2175 | Acap1 | NM_153788.3 | chr11:69695069-69709041 |
| 2176 | Acap2 | NM_030138.2 | chr16:31092499-31201324 |
| 2177 | Acap3 | NM_207223.1 | chr4:155265983-155281360 |
| 2178 | Acat1 | NM_144784.3 | chr9:53388626-53418455 |

| | | | |
|---|---|---|---|
| 2179 | Acat2 | NM_009338.3 | chr17:13135907-13153591 |
| 2180 | Acat3 | NM_153151.3 | chr17:13116825-13133262 |
| 2181 | Acbd3 | NM_133225.3 | chr1:182656173-182684335 |
| 2182 | Acbd4 | NM_025988.2 | chr11:102963001-102973513 |
| 2183 | Acbd5 | NM_001102436.1 | chr2:22923720-22970032 |
| 2184 | Acbd5 | NM_001102437.1 | chr2:22923720-22970032 |
| 2185 | Acbd5 | NM_001102438.1 | chr2:22923720-22970032 |
| 2186 | Acbd5 | NM_028793.3 | chr2:22923720-22970032 |
| 2187 | Acbd6 | NM_001145781.1 | chr1:157405249-157534363 |
| 2188 | Acbd6 | NM_026683.1 | chr1:157405249-157534363 |
| 2189 | Acbd6 | NM_028250.1 | chr1:157405249-157534363 |
| 2190 | Acd7 | NM_030063.2 | chr3:3253439-3258269 |
| 2191 | Accs | NM_001290782.1 | chr2:93673623-93690100 |
| 2192 | Accs | NM_183220.3 | chr2:93673623-93690100 |
| 2193 | Accsl | NM_001033452.4 | chr2:93695516-93709314 |
| 2194 | Acd | NM_001012638.1 | chr8:108222059-108224995 |
| 2195 | Ace | NM_001281819.1 | chr11:105826920-105851278 |
| 2196 | Ace | NM_009598.2 | chr11:105826920-105851278 |
| 2197 | Ace | NM_207624.5 | chr11:105826920-105851278 |
| 2198 | Ace2 | NM_001130513.1 | chrX:160577273-160626350 |
| 2199 | Ace2 | NM_027286.4 | chrX:160577273-160626350 |
| 2200 | Ace3 | NM_001101453.2 | chr11:105855988-105866757 |
| 2201 | Acer1 | NM_175731.4 | chr17:57092912-57121549 |
| 2202 | Acer2 | NM_001290541.1 | chr4:86520317-86578394 |
| 2203 | Acer2 | NM_001290543.1 | chr4:86520317-86578394 |
| 2204 | Acer2 | NM_139306.3 | chr4:86520317-86578394 |
| 2205 | Acer3 | NM_025408.2 | chr7:105362169-105458037 |
| 2206 | Ache | NM_001290010.1 | chr5:137729481-137735694 |
| 2207 | Ache | NM_009599.4 | chr5:137729481-137735694 |
| 2208 | Acin1 | NM_001085472.1 | chr14:55260997-55309579 |
| 2209 | Acin1 | NM_001085473.2 | chr14:55260997-55309579 |
| 2210 | Acin1 | NM_001242605.1 | chr14:55260997-55309579 |
| 2211 | Acin1 | NM_001242606.1 | chr14:55260997-55309579 |
| 2212 | Acin1 | NM_019567.1 | chr14:55260997-55309579 |
| 2213 | Acin1 | NM_023190.3 | chr14:55260997-55309579 |
| 2214 | Ackr1 | NM_010045.2 | chr1:175262016-175263634 |
| 2215 | Ackr2 | NM_001276719.1 | chr9:121807472-121820189 |
| 2216 | Ackr2 | NM_021609.4 | chr9:121807472-121820189 |
| 2217 | Ackr3 | NM_001271607.1 | chr1:92100554-92112297 |
| 2218 | Ackr3 | NM_007222.4 | chr1:92100554-92112297 |
| 2219 | Ackr4 | NM_145700.2 | chr9:104000468-104028973 |
| 2220 | Acly | NM_001199296.1 | chr11:100337665-100389314 |
| 2221 | Acly | NM_134037.3 | chr11:100337665-100389314 |
| 2222 | Acmsd | NM_001033041.2 | chr1:129625990-129664141 |
| 2223 | Acn9 | NM_001077713.1 | chr6:6906017-6989220 |
| 2224 | Acnat1 | NM_001164565.1 | chr4:49456403-49463981 |
| 2225 | Acnat2 | NM_145368.2 | chr4:49392716-49421023 |
| 2226 | Aco1 | NM_007386.2 | chr4:40090297-40146042 |
| 2227 | Aco2 | NM_080633.2 | chr15:81702893-81745567 |
| 2228 | Acot1 | NM_012006.2 | chr12:85350451-85358619 |
| 2229 | Acot10 | NM_022816.2 | chr15:20594968-20596505 |
| 2230 | Acot11 | NM_025590.4 | chr4:106417166-106472436 |
| 2231 | Acot12 | NM_028790.3 | chr13:91881126-91925753 |
| 2232 | Acot13 | NM_025790.2 | chr13:24909823-24923358 |
| 2233 | Acot2 | NM_134188.3 | chr12:85328810-85334825 |
| 2234 | Acot3 | NM_134246.3 | chr12:85393100-85400514 |
| 2235 | Acot4 | NM_134247.3 | chr12:85379328-85385673 |
| 2236 | Acot5 | NM_145444.3 | chr12:85410274-85416969 |
| 2237 | Acot6 | NM_172580.1 | chr12:85441603-85450733 |
| 2238 | Acot7 | NM_001146057.1 | chr4:151552208-151645964 |
| 2239 | Acot7 | NM_001146058.1 | chr4:151552208-151645964 |
| 2240 | Acot7 | NM_133348.2 | chr4:151552208-151645964 |
| 2241 | Acot8 | NM_133240.2 | chr2:164618268-164630381 |
| 2242 | Acot9 | NM_019736.3 | chrX:151697042-151732050 |
| 2243 | Acox1 | NM_001271898.1 | chr11:116033196-116076632 |
| 2244 | Acox1 | NM_015729.3 | chr11:116033196-116076632 |
| 2245 | Acox2 | NM_001161667.1 | chr14:9058024-9091533 |
| 2246 | Acox2 | NM_053115.2 | chr14:9058024-9091533 |
| 2247 | Acox3 | NM_030721.2 | chr5:35925709-35956450 |
| 2248 | Acoxl | NM_028765.3 | chr2:127680363-127949628 |
| 2249 | Acp1 | NM_001110239.1 | chr12:31569188-31596477 |
| 2250 | Acp1 | NM_021330.4 | chr12:31569188-31596477 |
| 2251 | Acp2 | NM_007387.2 | chr2:91043669-91054255 |
| 2252 | Acp5 | NM_001102404.1 | chr9:21931170-21940190 |
| 2253 | Acp5 | NM_001102405.1 | chr9:21931170-21940190 |
| 2254 | Acp5 | NM_007388.3 | chr9:21931170-21940190 |
| 2255 | Acp6 | NM_019800.4 | chr3:96962699-96980499 |
| 2256 | Acpp | NM_019807.2 | chr9:104190569-104240052 |
| 2257 | Acpp | NM_207668.2 | chr9:104190569-104240052 |
| 2258 | Acpt | NM_001195034.1 | chr7:51508456-51512574 |
| 2259 | Acr | NM_001205049.1 | chr15:89398756-89405016 |
| 2260 | Acr | NM_001277245.1 | chr15:89398756-89405016 |
| 2261 | Acr | NM_001277246.1 | chr15:89398756-89405016 |
| 2262 | Acr | NM_001277247.1 | chr15:89398756-89405016 |
| 2263 | Acr | NM_001277248.1 | chr15:89398756-89405016 |
| 2264 | Acr | NM_013455.3 | chr15:89398756-89405016 |
| 2265 | Acrbp | NM_001127340.1 | chr6:124999944-125013283 |
| 2266 | Acrbp | NM_016845.2 | chr6:124999944-125013283 |
| 2267 | Acrv1 | NM_007391.2 | chr9:36500804-36506422 |
| 2268 | Acsbg1 | NM_053178.2 | chr9:54452803-54509692 |
| 2269 | Acsbg2 | NM_001039114.1 | chr17:56982526-57013870 |
| 2270 | Acsf2 | NM_153807.2 | chr11:94418416-94463100 |
| 2271 | Acsf3 | NM_144932.3 | chr8:125299404-125341781 |
| 2272 | Acsl1 | NM_007981.4 | chr8:47556395-47621404 |
| 2273 | Acsl3 | NM_001033606.2 | chr1:78654399-78704318 |

Fig. 25 - 13

| | | | |
|---|---|---|---|
| 2274 | Acsl3 | NM_001136222.1 | chr1:78654399-78704318 |
| 2275 | Acsl3 | NM_028817.2 | chr1:78654399-78704318 |
| 2276 | Acsl4 | NM_001033600.1 | chrX:138752535-138825078 |
| 2277 | Acsl4 | NM_019477.3 | chrX:138752535-138825078 |
| 2278 | Acsl4 | NM_207625.2 | chrX:138752535-138825078 |
| 2279 | Acsl5 | NM_027976.2 | chr19:55327858-55371118 |
| 2280 | Acsl6 | NM_001033597.1 | chr11:54117325-54175041 |
| 2281 | Acsl6 | NM_001033598.1 | chr11:54117325-54175041 |
| 2282 | Acsl6 | NM_001033599.1 | chr11:54117325-54175041 |
| 2283 | Acsl6 | NM_144823.4 | chr11:54117325-54175041 |
| 2284 | Acsm1 | NM_054094.5 | chr7:126761341-126806029 |
| 2285 | Acsm2 | NM_001177977.1 | chr7:126697853-126744208 |
| 2286 | Acsm2 | NM_001177978.1 | chr7:126697853-126744208 |
| 2287 | Acsm2 | NM_146197.4 | chr7:126697853-126744208 |
| 2288 | Acsm3 | NM_016870.3 | chr7:126904436-126937572 |
| 2289 | Acsm3 | NM_212441.2 | chr7:126904436-126937572 |
| 2290 | Acsm3 | NM_212442.2 | chr7:126904436-126937572 |
| 2291 | Acsm4 | NM_178414.3 | chr7:126833539-126858080 |
| 2292 | Acsm5 | NM_178758.3 | chr7:126669778-126686874 |
| 2293 | Acss1 | NM_080575.2 | chr2:150443847-150493976 |
| 2294 | Acss2 | NM_019811.3 | chr2:155343779-155386479 |
| 2295 | Acss2os | NR_040613.1 | chr2:155372776-155382666 |
| 2296 | Acss3 | NM_001142804.1 | chr10:106373219-106560720 |
| 2297 | Acss3 | NM_198636.3 | chr10:106373219-106560720 |
| 2298 | Acta1 | NM_001272041.1 | chr8:126415657-126418675 |
| 2299 | Acta1 | NM_009606.3 | chr8:126415657-126418675 |
| 2300 | Acta2 | NM_007392.3 | chr19:34314825-34329863 |
| 2301 | Actb | NM_054094.5 | chr5:143664794-143668403 |
| 2302 | Actbl2 | NM_175497.3 | chr13:112045220-112047957 |
| 2303 | Actc1 | NM_009608.3 | chr2:113873024-113878547 |
| 2304 | Actg1 | NM_009609.2 | chr11:120207004-120209798 |
| 2305 | Actg2 | NM_009610.2 | chr6:83462902-83486245 |
| 2306 | Actl10 | NM_001171640.1 | chr2:154377512-154379012 |
| 2307 | Actl11 | NM_026338.3 | chr9:107830799-107834792 |
| 2308 | Actl6a | NM_019673.2 | chr3:32607467-32625893 |
| 2309 | Actl6b | NM_031404.4 | chr5:137994782-138010801 |
| 2310 | Actl7a | NM_009613.3 | chr4:56756293-56757797 |
| 2311 | Actl7b | NM_025271.2 | chr4:56752876-56754297 |
| 2312 | Actl9 | NM_183282.2 | chr17:33568843-33571212 |
| 2313 | Actn1 | NM_134156.2 | chr12:81268528-81361358 |
| 2314 | Actn2 | NM_033268.4 | chr13:12361693-12432999 |
| 2315 | Actn3 | NM_013456.2 | chr19:4861215-4877909 |
| 2316 | Actn4 | NM_021895.2 | chr7:29678273-29747299 |
| 2317 | Actr10 | NM_019785.2 | chr12:72038843-72065704 |
| 2318 | Actr1a | NM_016860.1 | chr19:46451303-46470225 |
| 2319 | Actr1b | NM_146107.2 | chr1:36756046-36766770 |
| 2320 | Actr2 | NM_146243.2 | chr11:19962306-20012954 |
| 2321 | Actr3 | NM_001205385.1 | chr1:127289481-127332304 |
| 2322 | Actr3 | NM_001205386.1 | chr1:127289481-127332304 |
| 2323 | Actr3 | NM_023735.2 | chr1:127289481-127332304 |
| 2324 | Actr3b | NM_001004365.1 | chr5:25265843-25356159 |
| 2325 | Actr5 | NM_175419.4 | chr2:158450649-158464947 |
| 2326 | Actr6 | NM_026574.2 | chr10:89174717-89195040 |
| 2327 | Actr8 | NM_027493.3 | chr14:30791523-30806407 |
| 2328 | Actrt1 | NM_028514.3 | chrX:43682183-43683522 |
| 2329 | Actrt2 | NM_028513.3 | chr4:154040536-154041976 |
| 2330 | Actrt3 | NM_029690.2 | chr3:30495994-30498792 |
| 2331 | Acvr1 | NM_001110204.1 | chr2:58298848-58419239 |
| 2332 | Acvr1 | NM_001110205.1 | chr2:58298848-58419239 |
| 2333 | Acvr1 | NM_007394.3 | chr2:58298848-58419239 |
| 2334 | Acvr1b | NM_007395.3 | chr15:101004456-101043032 |
| 2335 | Acvr1c | NM_001033869.3 | chr2:58119863-58210169 |
| 2336 | Acvr1c | NM_001111030.1 | chr2:58119863-58210169 |
| 2337 | Acvr2a | NM_007396.4 | chr2:48669629-48758784 |
| 2338 | Acvr2b | NM_007397.2 | chr9:119311618-119342624 |
| 2339 | Acvrl1 | NM_001277255.1 | chr15:100958952-100975767 |
| 2340 | Acvrl1 | NM_001277257.1 | chr15:100958952-100975767 |
| 2341 | Acvrl1 | NM_001277258.1 | chr15:100958952-100975767 |
| 2342 | Acvrl1 | NM_001277259.1 | chr15:100958952-100975767 |
| 2343 | Acvrl1 | NM_009612.3 | chr15:100958952-100975767 |
| 2344 | Acy1 | NM_001276442.1 | chr9:106335311-106340567 |
| 2345 | Acy1 | NM_025371.3 | chr9:106335311-106340567 |
| 2346 | Acy3 | NM_027687.3 | chr19:3986660-3990005 |
| 2347 | Acyp1 | NM_025421.2 | chr12:86613347-86621385 |
| 2348 | Acyp2 | NM_029344.3 | chr11:30405991-30549396 |
| 2349 | Ada | NM_001272052.1 | chr2:163525386-163575975 |
| 2350 | Ada | NM_007398.4 | chr2:163552306-163575975 |
| 2351 | Adad1 | NM_009350.3 | chr3:36962577-37010434 |
| 2352 | Adad2 | NM_029428.1 | chr8:122138646-122140826 |
| 2353 | Adal | NM_001290811.1 | chr2:120963027-120982416 |
| 2354 | Adal | NM_001290812.1 | chr2:120963027-120982416 |
| 2355 | Adal | NM_029419.3 | chr2:120963027-120982416 |
| 2356 | Adam10 | NM_007399.3 | chr9:70526807-70628036 |
| 2357 | Adam11 | NM_001110778.1 | chr11:102622752-102641576 |
| 2358 | Adam11 | NM_009613.2 | chr11:102622752-102641576 |
| 2359 | Adam12 | NM_007400.2 | chr7:141074882-141416780 |
| 2360 | Adam15 | NM_001037722.2 | chr3:89143561-89153932 |
| 2361 | Adam15 | NM_009614.2 | chr3:89143561-89153932 |
| 2362 | Adam17 | NM_001277266.1 | chr12:21322252-21379493 |
| 2363 | Adam17 | NM_001291871.1 | chr12:21322252-21379493 |
| 2364 | Adam17 | NM_009615.6 | chr12:21322252-21379493 |
| 2365 | Adam17 | NR_102380.1 | chr12:21322252-21379493 |
| 2366 | Adam17 | NR_120376.1 | chr12:21322252-21379493 |
| 2367 | Adam18 | NM_010084.2 | chr8:25712717-25785227 |
| 2368 | Adam19 | NM_001291890.1 | chr11:45868003-45960849 |
| 2369 | Adam19 | NM_001291891.1 | chr11:45868003-45960849 |
| 2370 | Adam19 | NM_009616.4 | chr11:45868003-45960849 |
| 2371 | Adam1a | NM_172126.2 | chr5:121968612-121971704 |
| 2372 | Adam1b | NM_172125.2 | chr5:121950105-121952989 |
| 2373 | Adam2 | NM_009618.2 | chr14:66646165-66696570 |
| 2374 | Adam20 | NM_001009548.2 | chr8:41878626-41882657 |
| 2375 | Adam21 | NM_020330.4 | chr12:82659570-82669461 |
| 2376 | Adam22 | NM_001007220.2 | chr5:8072351-8368081 |
| 2377 | Adam22 | NM_001007221.2 | chr5:8072351-8368081 |
| 2378 | Adam22 | NM_001098225.1 | chr5:8072351-8368081 |
| 2379 | Adam23 | NM_001177600.1 | chr1:63492477-63643089 |
| 2380 | Adam23 | NM_011780.2 | chr1:63492477-63643089 |
| 2381 | Adam24 | NM_010086.4 | chr8:41760447-41767553 |
| 2382 | Adam25 | NM_011781.2 | chr8:41837561-41841530 |
| 2383 | Adam26a | NM_010085.2 | chr8:44653629-44662061 |
| 2384 | Adam26b | NM_001009547.2 | chr8:44605217-44613491 |
| 2385 | Adam28 | NM_001048175.2 | chr14:69223054-69273899 |
| 2386 | Adam28 | NM_010082.2 | chr14:69223054-69273899 |
| 2387 | Adam28 | NM_183366.3 | chr14:69223054-69273899 |
| 2388 | Adam28 | NR_102399.1 | chr14:69223054-69273899 |
| 2389 | Adam29 | NM_175939.3 | chr8:58349708-58385761 |
| 2390 | Adam3 | NM_009619.4 | chr8:25787705-25836297 |
| 2391 | Adam30 | NM_027665.1 | chr3:97964734-97967096 |
| 2392 | Adam32 | NM_153397.2 | chr8:25946614-26059276 |
| 2393 | Adam33 | NM_001163529.1 | chr2:130876552-130889550 |
| 2394 | Adam33 | NM_033615.2 | chr2:130876552-130889550 |
| 2395 | Adam34 | NM_145745.2 | chr8:44735662-44750914 |
| 2396 | Adam39 | NM_001025380.3 | chr8:41908362-41912215 |
| 2397 | Adam4 | NM_009620.1 | chr12:82520535-82522865 |
| 2398 | Adam5 | NM_001272057.1 | chr8:25837564-25934841 |
| 2399 | Adam5 | NM_001272058.1 | chr8:25837564-25934841 |
| 2400 | Adam5 | NM_001272059.1 | chr8:25837564-25934841 |
| 2401 | Adam5 | NM_007401.3 | chr8:25837564-25934841 |
| 2402 | Adam6a | NM_174885.3 | chr12:114782118-114784625 |
| 2403 | Adam6b | NM_001009545.1 | chr12:114727775-114730046 |
| 2404 | Adam7 | NM_007402.2 | chr14:69115393-69151746 |
| 2405 | Adam8 | NM_001291066.2 | chr7:147164836-147178408 |
| 2406 | Adam8 | NM_007403.3 | chr7:147164836-147178408 |
| 2407 | Adam9 | NM_001270996.1 | chr8:26060082-26127394 |
| 2408 | Adam9 | NM_007404.2 | chr8:26060082-26127394 |
| 2409 | Adamdec1 | NM_021475.2 | chr14:69181443-69200129 |
| 2410 | Adamts1 | NM_009621.4 | chr16:85794072-85803360 |
| 2411 | Adamts10 | NM_172619.3 | chr17:33661140-33690727 |
| 2412 | Adamts10 | NR_037707.1 | chr17:33661140-33690727 |
| 2413 | Adamts10 | NR_037708.1 | chr17:33661140-33690727 |
| 2414 | Adamts12 | NM_175501.2 | chr15:10994544-11276622 |
| 2415 | Adamts13 | NM_001001322.2 | chr2:26828935-26865145 |
| 2416 | Adamts13 | NM_001290463.1 | chr2:26828935-26865145 |
| 2417 | Adamts13 | NM_001290464.1 | chr2:26828935-26865145 |
| 2418 | Adamts13 | NM_001290465.1 | chr2:26828935-26865145 |
| 2419 | Adamts14 | NM_001081127.1 | chr10:60659859-60736186 |
| 2420 | Adamts15 | NM_001024139.1 | chr9:30706739-30730037 |
| 2421 | Adamts16 | NM_172053.2 | chr13:70866685-70980688 |
| 2422 | Adamts17 | NM_001033877.4 | chr7:73984620-74297511 |
| 2423 | Adamts18 | NM_172466.2 | chr8:116222036-116327739 |
| 2424 | Adamts19 | NM_175506.3 | chr18:58996417-59213332 |
| 2425 | Adamts2 | NM_001277305.1 | chr11:50415586-50621075 |
| 2426 | Adamts2 | NM_175643.3 | chr11:50415586-50621075 |
| 2427 | Adamts20 | NM_001164785.1 | chr15:94100593-94234781 |
| 2428 | Adamts20 | NM_001164786.1 | chr15:94100593-94234781 |
| 2429 | Adamts20 | NM_177431.4 | chr15:94100593-94234781 |
| 2430 | Adamts3 | NM_001081401.2 | chr5:90102865-90312359 |
| 2431 | Adamts3 | NM_177872.2 | chr5:90102865-90312359 |
| 2432 | Adamts4 | NM_172845.2 | chr1:173180552-173190053 |
| 2433 | Adamts5 | NM_011782.2 | chr16:85858401-85901370 |
| 2434 | Adamts6 | NM_001081020.1 | chr13:105077952-105284843 |
| 2435 | Adamts7 | NM_001003911.2 | chr9:90057815-90094940 |
| 2436 | Adamts8 | NM_013906.2 | chr9:30750147-30770443 |
| 2437 | Adamts9 | NM_175314.3 | chr6:92722692-92851435 |
| 2438 | Adamtsl1 | NM_029967.3 | chr4:85699818-86074286 |
| 2439 | Adamtsl2 | NM_029981.1 | chr2:26934900-26964133 |
| 2440 | Adamtsl3 | NM_001190374.1 | chr7:89484203-89762958 |
| 2441 | Adamtsl4 | NM_144899.3 | chr3:95480126-95491781 |
| 2442 | Adamtsl5 | NM_001285435.1 | chr10:79802537-79811193 |
| 2443 | Adamtsl5 | NR_104339.1 | chr10:79802537-79811193 |
| 2444 | Adamtsl5 | NR_104340.1 | chr10:79802537-79811193 |
| 2445 | Adap1 | NM_172723.4 | chr5:139747829-139801418 |
| 2446 | Adap2 | NM_172133.1 | chr11:79967663-79992329 |
| 2447 | Adar | NM_001038587.4 | chr3:89518943-89568554 |
| 2448 | Adar | NM_001146296.1 | chr3:89518943-89568554 |
| 2449 | Adar | NM_019655.3 | chr3:89518943-89568554 |
| 2450 | Adarb1 | NM_001024837.2 | chr10:76753471-76881018 |
| 2451 | Adarb1 | NM_130895.3 | chr10:76753471-76881018 |
| 2452 | Adarb1 | NR_004429.1 | chr10:76753471-76881018 |
| 2453 | Adarb1 | NR_021486.1 | chr10:76753471-76881018 |
| 2454 | Adarb2 | NM_001289530.1 | chr13:8202111-8768008 |
| 2455 | Adarb2 | NM_052977.5 | chr13:8202111-8768008 |
| 2456 | Adarb2 | NR_110345.1 | chr13:8202111-8768008 |
| 2457 | Adat1 | NM_039925.4 | chr8:114490807-114516202 |
| 2458 | Adat2 | NM_025748.4 | chr10:13272713-13283182 |
| 2459 | Adat3 | NM_001100606.1 | chr10:80065625-80070399 |
| 2460 | Adc | NM_172875.4 | chr4:128609389-128639661 |
| 2461 | Adck1 | NM_001277296.1 | chr12:89598957-89700170 |
| 2462 | Adck1 | NM_001277297.1 | chr12:89598957-89700170 |
| 2463 | Adck1 | NM_028105.4 | chr12:89598957-89700170 |

Fig. 25 - 14

| | | | |
|---|---|---|---|
| 2464 | Adck2 | NM_178873.3 | chr6:39523874-39538768 |
| 2465 | Adck3 | NM_001163019.1 | chr1:181891219-182126151 |
| 2466 | Adck3 | NM_023341.3 | chr1:181891219-182126151 |
| 2467 | Adck4 | NM_133770.2 | chr7:28018031-28042968 |
| 2468 | Adck5 | NM_172960.5 | chr15:76406788-76438021 |
| 2469 | Adck5 | NR_073123.1 | chr15:76406788-76438021 |
| 2470 | Adcy1 | NM_009622.1 | chr11:6963491-7078508 |
| 2471 | Adcy10 | NM_173029.3 | chr1:167415313-167506904 |
| 2472 | Adcy2 | NM_153534.2 | chr13:68758919-69138419 |
| 2473 | Adcy3 | NM_001159536.1 | chr12:4133396-4240123 |
| 2474 | Adcy3 | NM_001159537.1 | chr12:4133396-4240123 |
| 2475 | Adcy3 | NM_138305.3 | chr12:4133396-4240123 |
| 2476 | Adcy4 | NM_080435.1 | chr14:56387928-56402856 |
| 2477 | Adcy5 | NM_001012765.4 | chr16:35155721-35304635 |
| 2478 | Adcy6 | NM_007405.2 | chr15:98420420-98438064 |
| 2479 | Adcy7 | NM_001037723.3 | chr8:90796301-90853861 |
| 2480 | Adcy7 | NM_001037724.4 | chr8:90796301-90853861 |
| 2481 | Adcy7 | NM_001109756.1 | chr8:90796301-90853861 |
| 2482 | Adcy7 | NM_007406.2 | chr8:90796301-90853861 |
| 2483 | Adcy8 | NM_001291903.1 | chr15:64530596-64753858 |
| 2484 | Adcy8 | NM_009623.2 | chr15:64530596-64753858 |
| 2485 | Adcy9 | NM_001291910.1 | chr16:4284885-4420498 |
| 2486 | Adcy9 | NM_009624.3 | chr16:4284885-4420498 |
| 2487 | Adcyap1 | NM_009625.2 | chr17:93598761-93604829 |
| 2488 | Adcyap1r1 | NM_001025372.2 | chr6:55401971-55451449 |
| 2489 | Adcyap1r1 | NM_007407.4 | chr6:55401971-55451449 |
| 2490 | Add1 | NM_001024458.3 | chr5:34916362-34974954 |
| 2491 | Add1 | NM_001102444.1 | chr5:34916362-34974954 |
| 2492 | Add1 | NM_013457.3 | chr5:34916362-34974954 |
| 2493 | Add2 | NM_001271857.1 | chr6:85978674-86074403 |
| 2494 | Add2 | NM_001271858.1 | chr6:85978674-86074403 |
| 2495 | Add2 | NM_001271859.1 | chr6:85978674-86074403 |
| 2496 | Add2 | NM_001271860.1 | chr6:85978674-86074403 |
| 2497 | Add2 | NM_001271861.1 | chr6:85978674-86074403 |
| 2498 | Add2 | NM_013458.5 | chr6:85978674-86074403 |
| 2499 | Add3 | NM_001164099.2 | chr19:53214932-53321816 |
| 2500 | Add3 | NM_001164100.2 | chr19:53214932-53321816 |
| 2501 | Add3 | NM_001164101.2 | chr19:53214932-53321816 |
| 2502 | Add3 | NM_001277100.1 | chr19:53214932-53321816 |
| 2503 | Add3 | NM_013758.4 | chr19:53214932-53321816 |
| 2504 | Adgb | NM_001127353.2 | chr10:10055500-10192112 |
| 2505 | Adh1 | NM_007409.4 | chr3:137940608-137953655 |
| 2506 | Adh4 | NM_011996.2 | chr3:138078460-138093856 |
| 2507 | Adh5 | NM_001288578.1 | chr3:138100163-138118463 |
| 2508 | Adh5 | NM_007410.3 | chr3:138100163-138118463 |
| 2509 | Adh6a | NM_026945.1 | chr3:137976249-137994098 |
| 2510 | Adh6-ps1 | NR_033581.1 | chr3:138037084-138051255 |
| 2511 | Adh7 | NM_009626.4 | chr3:137880737-137895006 |
| 2512 | Adhfe1 | NM_175236.4 | chr1:9538126-9621173 |
| 2513 | Adhfe1 | NR_027664.1 | chr1:9538126-9621173 |
| 2514 | Adi1 | NM_134052.2 | chr12:29360072-29367039 |
| 2515 | Adig | NM_145635.2 | chr2:158328347-158333934 |
| 2516 | Adipoq | NM_009605.4 | chr16:23146608-23158041 |
| 2517 | Adipor1 | NM_028320.4 | chr1:136312043-136328918 |
| 2518 | Adipor2 | NM_197985.3 | chr6:119303167-119367501 |
| 2519 | Adk | NM_001243041.1 | chr14:21871795-22267791 |
| 2520 | Adk | NM_134079.4 | chr14:21871795-22267791 |
| 2521 | Adm | NM_009627.1 | chr7:117771182-117773333 |
| 2522 | Adm2 | NM_182928.4 | chr15:89153329-89155161 |
| 2523 | Adnp | NM_009628.2 | chr2:168006464-168032562 |
| 2524 | Adnp2 | NM_175028.1 | chr18:80323873-80348221 |
| 2525 | Ado | NM_001005419.2 | chr10:67007258-67011703 |
| 2526 | Adora1 | NM_001008533.3 | chr1:136090024-136132034 |
| 2527 | Adora1 | NM_001039510.2 | chr1:136090024-136132034 |
| 2528 | Adora1 | NM_001282945.1 | chr1:136090024-136132034 |
| 2529 | Adora1 | NM_001291928.1 | chr1:136090024-136132034 |
| 2530 | Adora1 | NM_001291930.1 | chr1:136090024-136132034 |
| 2531 | Adora2a | NM_009630.3 | chr10:74779621-74797537 |
| 2532 | Adora2b | NM_007413.4 | chr11:62062485-62079954 |
| 2533 | Adora3 | NM_001174169.2 | chr3:105673775-105726962 |
| 2534 | Adora3 | NM_009631.4 | chr3:105673775-105726962 |
| 2535 | Adora3 | NM_027025.4 | chr3:105673775-105726962 |
| 2536 | Adpgk | NM_028121.2 | chr9:59139378-59164007 |
| 2537 | Adprh | NM_007414.3 | chr16:38445478-38452769 |
| 2538 | Adprhl1 | NM_172750.3 | chr8:13235661-13254162 |
| 2539 | Adprhl2 | NM_133883.2 | chr4:125993594-125998947 |
| 2540 | Adprm | NM_025510.3 | chr11:66851381-66866120 |
| 2541 | Adra1a | NM_001271759.1 | chr14:67254087-67390005 |
| 2542 | Adra1a | NM_001271760.1 | chr14:67254087-67390005 |
| 2543 | Adra1a | NM_001271761.1 | chr14:67254087-67390005 |
| 2544 | Adra1a | NM_013461.4 | chr14:67254087-67390005 |
| 2545 | Adra1b | NM_001284380.1 | chr11:43588106-43714739 |
| 2546 | Adra1b | NM_001284381.1 | chr11:43588106-43714739 |
| 2547 | Adra1b | NM_007416.4 | chr11:43588106-43714739 |
| 2548 | Adra1d | NM_013460.4 | chr2:131371092-131388021 |
| 2549 | Adra2a | NM_007417.4 | chr19:54119671-54123472 |
| 2550 | Adra2b | NM_009633.3 | chr2:127189021-127192957 |
| 2551 | Adra2c | NM_007418.3 | chr5:35621214-35624412 |
| 2552 | Adrb1 | NM_007419.2 | chr19:56796861-56799352 |
| 2553 | Adrb2 | NM_007420.3 | chr18:62337386-62339635 |
| 2554 | Adrb3 | NM_013462.3 | chr8:28336247-28340060 |
| 2555 | Adrbk1 | NM_001290818.1 | chr19:4285998-4306222 |
| 2556 | Adrbk1 | NM_130863.2 | chr19:4285998-4306222 |
| 2557 | Adrbk2 | NM_001285806.1 | chr5:113339497-113444558 |
| 2558 | Adrbk2 | NM_177078.4 | chr5:113339497-113444558 |
| 2559 | Adrm1 | NM_019822.3 | chr2:179906292-179910988 |
| 2560 | Adsl | NM_009634.6 | chr15:80778919-80801377 |
| 2561 | Adss | NM_007422.3 | chr1:179693308-179726640 |
| 2562 | Adssl1 | NM_007421.2 | chr12:113858257-113879566 |
| 2563 | Adtrp | NM_001145875.1 | chr13:41858516-41942985 |
| 2564 | Adtrp | NM_175417.4 | chr13:41858516-41942985 |
| 2565 | Aebp1 | NM_001291857.2 | chr11:5761868-5778259 |
| 2566 | Aebp1 | NM_009636.3 | chr11:5761868-5778259 |
| 2567 | Aebp2 | NM_001005605.1 | chr6:140571183-140625939 |
| 2568 | Aebp2 | NM_009637.3 | chr6:140571183-140625939 |
| 2569 | Aebp2 | NM_178803.2 | chr6:140571183-140625939 |
| 2570 | Aen | NM_001162939.1 | chr7:86040812-86053719 |
| 2571 | Aen | NM_026531.4 | chr7:86040812-86053719 |
| 2572 | Aes | NM_001276288.1 | chr10:81022188-81029116 |
| 2573 | Aes | NM_010347.4 | chr10:81022188-81029116 |
| 2574 | Aes | NR_074087.1 | chr10:81022188-81029116 |
| 2575 | AF067063 | NM_001001449.2 | chrUn_random:125697-127960 |
| 2576 | AF251705 | NM_134158.1 | chr11:114858082-114863194 |
| 2577 | AF357355 | NR_028433.2 | chr12:110892837-110892907 |
| 2578 | AF357359 | NR_028434.1 | chr12:110888919-110888948 |
| 2579 | AF357399 | NR_028129.1 | chr7:29136559-29136652 |
| 2580 | AF357425 | NR_046302.1 | chr12:110874222-110874290 |
| 2581 | AF357426 | NR_046303.1 | chr12:110881048-110881114 |
| 2582 | AF366264 | NM_153093.3 | chr8:13835230-13838089 |
| 2583 | AF529169 | NM_153509.2 | chr9:89484871-89517824 |
| 2584 | Afap1 | NM_027373.2 | chr5:36235967-36346571 |
| 2585 | Afap1l1 | NM_178928.4 | chr18:61889915-61946316 |
| 2586 | Afap1l2 | NM_001177796.1 | chr19:56986843-57083065 |
| 2587 | Afap1l2 | NM_001177797.1 | chr19:56986843-57083065 |
| 2588 | Afap1l2 | NM_146102.2 | chr19:56986843-57083065 |
| 2589 | Aff1 | NM_001080798.1 | chr5:104183180-104284341 |
| 2590 | Aff1 | NM_133919.3 | chr5:104183180-104284341 |
| 2591 | Aff2 | NM_008032.3 | chrX:66613505-67121212 |
| 2592 | Aff3 | NM_001290814.1 | chr1:38232835-38721800 |
| 2593 | Aff3 | NM_010678.2 | chr1:38232835-38721800 |
| 2594 | Aff4 | NM_033565.2 | chr11:53164269-53235332 |
| 2595 | Afg3l1 | NM_054070.3 | chr8:126001761-126027816 |
| 2596 | Afg3l1 | NR_028260.1 | chr8:126001761-126027816 |
| 2597 | Afg3l2 | NM_027130.1 | chr18:67564417-67608790 |
| 2598 | Afm | NM_145146.2 | chr5:90947974-90982570 |
| 2599 | Afmid | NM_027827.3 | chr11:117687233-117701222 |
| 2600 | Afp | NM_007423.4 | chr5:90919739-90937933 |
| 2601 | Aftph | NM_001252503.2 | chr11:20585087-20641559 |
| 2602 | Aftph | NM_001290545.1 | chr11:20585087-20641559 |
| 2603 | Aftph | NM_181411.4 | chr11:20585087-20641559 |
| 2604 | Aga | NM_001005847.2 | chr8:54597055-54608776 |
| 2605 | Aga | NM_001208054.1 | chr8:54597055-54608776 |
| 2606 | Agap1 | NM_001037136.1 | chr1:91351385-91791857 |
| 2607 | Agap1 | NM_178119.3 | chr1:91351385-91791857 |
| 2608 | Agap2 | NM_001033263.5 | chr10:126515962-126530225 |
| 2609 | Agap3 | NM_001256431.1 | chr5:23957994-24007865 |
| 2610 | Agap3 | NM_139153.2 | chr5:23957994-24007865 |
| 2611 | Agbl1 | NM_001199224.1 | chr7:83374772-84269584 |
| 2612 | Agbl2 | NM_178755.3 | chr2:90622900-90656388 |
| 2613 | Agbl3 | NM_001289656.1 | chr6:34730431-34809459 |
| 2614 | Agbl3 | NM_001289657.1 | chr6:34730431-34809459 |
| 2615 | Agbl3 | NM_001289658.1 | chr6:34730431-34809459 |
| 2616 | Agbl3 | NM_178630.4 | chr6:34730431-34809459 |
| 2617 | Agbl4 | NM_001048189.4 | chr4:110070302-111335629 |
| 2618 | Agbl4 | NM_001284190.1 | chr4:110070302-111335629 |
| 2619 | Agbl4 | NM_030231.3 | chr4:110070302-111335629 |
| 2620 | Agbl5 | NM_001048192.2 | chr5:31191224-31210161 |
| 2621 | Agbl5 | NM_174849.3 | chr5:31191224-31210161 |
| 2622 | Ager | NM_001271422.1 | chr17:34734794-34737882 |
| 2623 | Ager | NM_001271423.1 | chr17:34734794-34737882 |
| 2624 | Ager | NM_001271424.1 | chr17:34734794-34737882 |
| 2625 | Ager | NM_007425.3 | chr17:34734794-34737882 |
| 2626 | Ager | NR_073173.1 | chr17:34734794-34737882 |
| 2627 | Ager | NR_073175.1 | chr17:34734794-34737882 |
| 2628 | Ager | NR_073176.1 | chr17:34734794-34737882 |
| 2629 | Agfg1 | NM_010472.2 | chr1:82836057-82892850 |
| 2630 | Agfg2 | NM_145566.1 | chr5:138092081-138125921 |
| 2631 | Agfg2 | NM_178162.3 | chr5:138092081-138125921 |
| 2632 | Aggf1 | NM_025630.3 | chr13:96120637-96145312 |
| 2633 | Agk | NM_023538.2 | chr6:40275476-40346761 |
| 2634 | Agl | NM_001081326.1 | chr3:116442916-116511084 |
| 2635 | Agmat | NM_001081408.1 | chr4:141302589-141315178 |
| 2636 | Agmo | NM_178767.5 | chr12:37968225-38308519 |
| 2637 | Ago1 | NM_153403.2 | chr4:126112256-126145665 |
| 2638 | Ago2 | NM_153178.4 | chr15:72932054-73015377 |
| 2639 | Ago3 | NM_153402.2 | chr4:126017921-126106786 |
| 2640 | Ago4 | NM_153177.3 | chr4:126186786-126210702 |
| 2641 | Agpat1 | NM_001163179.1 | chr17:34742805-34752916 |
| 2642 | Agpat1 | NM_018862.3 | chr17:34742805-34752916 |
| 2643 | Agpat2 | NM_026212.2 | chr2:26448576-26459937 |
| 2644 | Agpat3 | NM_053014.3 | chr10:77734308-77814445 |
| 2645 | Agpat4 | NM_026644.2 | chr17:12312149-12412506 |
| 2646 | Agpat5 | NM_026792.3 | chr8:18846278-18884413 |
| 2647 | Agpat6 | NM_018743.4 | chr8:24283417-24318925 |
| 2648 | Agpat9 | NM_172715.3 | chr5:101275247-101328121 |
| 2649 | Agps | NM_172666.3 | chr2:75670233-75769407 |
| 2650 | Agr2 | NM_011783.2 | chr12:36719511-36730668 |
| 2651 | Agr3 | NM_207531.3 | chr12:36652207-36676317 |
| 2652 | Agrn | NM_021604.3 | chr4:155539398-155571597 |

Fig. 25 - 15

| | | | |
|---|---|---|---|
| 2653 | Agrp | NM_001271806.1 | chr8:108090594-108103745 |
| 2654 | Agrp | NM_007427.3 | chr8:108090594-108103745 |
| 2655 | Agt | NM_007428.3 | chr8:127080486-127093607 |
| 2656 | Agtpbp1 | NM_001048008.2 | chr13:59550895-59658708 |
| 2657 | Agtpbp1 | NM_001284218.1 | chr13:59550895-59658708 |
| 2658 | Agtpbp1 | NM_001284219.1 | chr13:59550895-59658708 |
| 2659 | Agtpbp1 | NM_001284221.1 | chr13:59550895-59658708 |
| 2660 | Agtpbp1 | NM_023328.3 | chr13:59550895-59658708 |
| 2661 | Agtr1a | NM_177322.3 | chr13:30428224-30474736 |
| 2662 | Agtr1b | NM_175086.3 | chr3:20213394-20266099 |
| 2663 | Agtr2 | NM_007429.5 | chrX:21061749-21065959 |
| 2664 | Agtrap | NM_009642.2 | chr4:147451169-147462173 |
| 2665 | Agxt | NM_016702.3 | chr1:95031816-95041998 |
| 2666 | Agxt2 | NM_001031851.1 | chr15:10288333-10339493 |
| 2667 | Ahctf1 | NM_026375.2 | chr1:181675034-181734146 |
| 2668 | Ahcy | NM_016661.3 | chr2:154885047-154900233 |
| 2669 | Ahcyl1 | NM_145542.3 | chr3:107466037-107499466 |
| 2670 | Ahcyl2 | NM_001171000.2 | chr6:29718442-29862310 |
| 2671 | Ahcyl2 | NM_001171001.1 | chr6:29718442-29862310 |
| 2672 | Ahcyl2 | NM_021414.6 | chr6:29718442-29862310 |
| 2673 | Ahdc1 | NM_146155.3 | chr4:132567420-132634025 |
| 2674 | Ahi1 | NM_001177776.1 | chr10:20672352-20800235 |
| 2675 | Ahi1 | NM_026203.3 | chr10:20672352-20800235 |
| 2676 | Ahnak | NM_001039959.2 | chr19:9063773-9151416 |
| 2677 | Ahnak | NM_001286518.1 | chr19:9063773-9151416 |
| 2678 | Ahnak | NM_009643.2 | chr19:9063773-9151416 |
| 2679 | Ahnak | NR_104460.1 | chr19:9063773-9151416 |
| 2680 | Ahr | NM_013464.4 | chr12:36182650-36219661 |
| 2681 | Ahrr | NM_009644.2 | chr13:74348565-74429757 |
| 2682 | Ahsa1 | NM_146036.1 | chr12:88607677-88614902 |
| 2683 | Ahsa2 | NM_001290654.1 | chr11:23206894-23398039 |
| 2684 | Ahsa2 | NM_001290655.1 | chr11:23206894-23398039 |
| 2685 | Ahsa2 | NM_172391.4 | chr11:23206894-23398039 |
| 2686 | Ahsg | NM_001276449.1 | chr16:22857917-22899524 |
| 2687 | Ahsg | NM_001276450.1 | chr16:22857917-22899524 |
| 2688 | Ahsg | NM_013465.2 | chr16:22857917-22899524 |
| 2689 | Ahsg | NR_075099.1 | chr16:22857917-22899524 |
| 2690 | AI115009 | NR_040386.1 | chr3:152329877-152344396 |
| 2691 | AI118078 | NM_172923.3 | chr9:55174755-55286151 |
| 2692 | AI182371 | NM_001243102.1 | chr2:34937380-34956205 |
| 2693 | AI182371 | NM_001243103.1 | chr2:34937380-34956205 |
| 2694 | AI182371 | NM_178885.4 | chr2:34937380-34956205 |
| 2695 | AI197445 | NR_045083.1 | chr13:108259901-108269268 |
| 2696 | AI197445 | NR_045084.1 | chr13:108259901-108269268 |
| 2697 | AI314180 | NM_172381.2 | chr4:58812902-58925597 |
| 2698 | AI314278 | NR_102276.1 | chr7:96574815-96580587 |
| 2699 | AI317395 | NM_144821.4 | chr10:39721378-39745074 |
| 2700 | AI413582 | NM_001002895.2 | chr17:27700713-27702672 |
| 2701 | AI414108 | NR_027907.1 | chr9:27160269-27185128 |
| 2702 | AI427809 | NR_033139.1 | chr4:53274227-53283104 |
| 2703 | AI427809 | NR_033140.1 | chr4:53274227-53283104 |
| 2704 | AI429214 | NM_001039220.3 | chr8:38056628-38058587 |
| 2705 | AI450353 | NR_028364.1 | chr11:83106932-83108431 |
| 2706 | AI462493 | NM_001160356.1 | chr19:8954503-8955423 |
| 2707 | AI463170 | NR_046044.1 | chr12:77647959-77648912 |
| 2708 | AI464131 | NM_001085515.2 | chr4:41442633-41450108 |
| 2709 | AI467606 | NM_178901.3 | chr7:134234949-134237563 |
| 2710 | AI504432 | NR_033498.1 | chr3:106842421-106857240 |
| 2711 | AI506816 | NR_015554.2 | chr5:23198078-23218485 |
| 2712 | AI506816 | NR_038090.1 | chr5:23198078-23218485 |
| 2713 | AI507597 | NR_033566.1 | chr4:141170285-141171519 |
| 2714 | AI593442 | NM_001286641.1 | chr9:52481136-52487885 |
| 2715 | AI593442 | NM_178906.5 | chr9:52481136-52487885 |
| 2716 | AI597479 | NM_133818.1 | chr1:43155554-43172791 |
| 2717 | AI606473 | NM_040387.1 | chr3:153969784-153997651 |
| 2718 | AI607873 | NM_001204910.1 | chr1:175653558-175671940 |
| 2719 | AI646519 | NR_040330.1 | chr2:147147278-147188529 |
| 2720 | AI661453 | NM_145489.2 | chr7:47573588-47607587 |
| 2721 | AI662270 | NR_015519.1 | chr11:83037677-83040086 |
| 2722 | AI747448 | NM_001033199.3 | chr3:144573884-144595493 |
| 2723 | AI837181 | NM_001256515.1 | chr19:5425143-5427316 |
| 2724 | AI837181 | NM_134149.2 | chr19:5425143-5427316 |
| 2725 | AI839979 | NR_102275.1 | chr5:31871964-31873770 |
| 2726 | AI846148 | NM_001033139.3 | chr19:7430953-7458047 |
| 2727 | AI846148 | NM_001167831.1 | chr19:7430953-7458047 |
| 2728 | AI847159 | NR_045264.1 | chr2:129038863-129006409 |
| 2729 | AI848285 | NM_001207021.1 | chr15:82037381-82043245 |
| 2730 | AI854517 | NR_040311.1 | chr7:86644911-86679289 |
| 2731 | AI854517 | NR_040312.1 | chr7:86644911-86679289 |
| 2732 | AI854517 | NR_040313.1 | chr7:86644911-86679289 |
| 2733 | AI854517 | NR_040314.1 | chr7:86644911-86679289 |
| 2734 | AI854703 | NR_027236.1 | chr6:48578165-48583687 |
| 2735 | AI987944 | NM_001199330.1 | chr7:48628299-48648749 |
| 2736 | AI987944 | NM_183167.4 | chr7:48628299-48648749 |
| 2737 | Aicda | NM_009645.2 | chr6:122503826-122514198 |
| 2738 | Aida | NM_181732.4 | chr1_random:270407-297849 |
| 2739 | Aif1 | NM_019467.2 | chr17:35307936-35312946 |
| 2740 | Aif1l | NM_145144.1 | chr2:31805822-31828962 |
| 2741 | Aifm1 | NM_001290364.1 | chrX:45828120-45866740 |
| 2742 | Aifm1 | NM_012019.3 | chrX:45828120-45866740 |
| 2743 | Aifm2 | NM_001039194.3 | chr10:61178010-61246612 |
| 2744 | Aifm2 | NM_001284300.1 | chr10:61178010-61246612 |
| 2745 | Aifm2 | NM_153779.2 | chr10:61178010-61246612 |
| 2746 | Aifm2 | NM_178058.4 | chr10:61178010-61246612 |
| 2747 | Aifm3 | NM_001291070.1 | chr16:17489769-17507578 |
| 2748 | Aifm3 | NM_175178.4 | chr16:17489769-17507578 |
| 2749 | Aig1 | NM_025446.3 | chr10:13372514-13588636 |
| 2750 | Aim1 | NM_172393.2 | chr10:43670112-43724652 |
| 2751 | Aim1l | NM_001162970.1 | chr4:133624366-133648419 |
| 2752 | Aim2 | NM_001013779.2 | chr1:175350734-175396167 |
| 2753 | Aimp1 | NM_007926.2 | chr3:132323461-132346843 |
| 2754 | Aimp2 | NM_001172146.1 | chr5:144578660-144670708 |
| 2755 | Aimp2 | NM_146165.2 | chr5:144578660-144670708 |
| 2756 | Aip | NM_001276284.1 | chr19:4099997-4125858 |
| 2757 | Aip | NM_016666.3 | chr19:4099997-4125858 |
| 2758 | Aip1 | NM_053245.2 | chr11:71842223-71851011 |
| 2759 | Aire | NM_001271549.1 | chr10:77492766-77526367 |
| 2760 | Aire | NM_001271550.1 | chr10:77492766-77526367 |
| 2761 | Aire | NM_001271551.1 | chr10:77492766-77526367 |
| 2762 | Aire | NM_001271552.1 | chr10:77492766-77526367 |
| 2763 | Aire | NM_001271553.1 | chr10:77492766-77526367 |
| 2764 | Aire | NM_001271554.1 | chr10:77492766-77526367 |
| 2765 | Aire | NM_001271555.1 | chr10:77492766-77526367 |
| 2766 | Aire | NM_001271556.1 | chr10:77492766-77526367 |
| 2767 | Aire | NM_001271557.1 | chr10:77492766-77526367 |
| 2768 | Aire | NM_001271558.1 | chr10:77492766-77526367 |
| 2769 | Aire | NM_001271559.1 | chr10:77492766-77526367 |
| 2770 | Aire | NM_009646.2 | chr10:77492766-77526367 |
| 2771 | Aire | NR_073358.1 | chr10:77492766-77526367 |
| 2772 | Airn | NR_002853.2 | chr17:12875271-13061009 |
| 2773 | Airn | NR_027772.1 | chr17:12875271-13061009 |
| 2774 | Airn | NR_027773.1 | chr17:12875271-13061009 |
| 2775 | Airn | NR_027784.1 | chr17:12875271-13061009 |
| 2776 | Ajap1 | NM_001099299.1 | chr4:152747329-152856939 |
| 2777 | Ajuba | NM_010590.5 | chr14:55186305-55196498 |
| 2778 | AK010878 | NM_001142938.1 | chr12:103991485-103996020 |
| 2779 | Ak1 | NM_001198790.1 | chr2:32477277-32490578 |
| 2780 | Ak1 | NM_001198791.1 | chr2:32477277-32490578 |
| 2781 | Ak1 | NM_001198792.1 | chr2:32477277-32490578 |
| 2782 | Ak1 | NM_021515.3 | chr2:32477277-32490578 |
| 2783 | AK129341 | NM_001045524.1 | chr9:8076632-8134294 |
| 2784 | Ak2 | NM_001033966.4 | chr4:128670467-128688773 |
| 2785 | Ak2 | NM_016895.4 | chr4:128670467-128688773 |
| 2786 | Ak3 | NM_021299.3 | chr19:29095322-29122392 |
| 2787 | Ak4 | NM_001177602.1 | chr4:101091893-101140376 |
| 2788 | Ak4 | NM_001177604.1 | chr4:101091893-101140376 |
| 2789 | Ak4 | NM_001177605.1 | chr4:101091893-101140376 |
| 2790 | Ak4 | NM_009647.5 | chr4:101091893-101140376 |
| 2791 | Ak5 | NM_001081277.1 | chr3:152125779-152331104 |
| 2792 | Ak6 | NM_027592.3 | chr13:101421298-101436370 |
| 2793 | Ak7 | NM_030187.1 | chr12:106944191-107020657 |
| 2794 | Ak8 | NM_001033874.2 | chr2:28555681-28668685 |
| 2795 | Akap1 | NM_001042541.1 | chr11:88692105-88725900 |
| 2796 | Akap1 | NM_009648.2 | chr11:88692105-88725900 |
| 2797 | Akap1 | NR_104310.1 | chr11:88692105-88725900 |
| 2798 | Akap10 | NM_019921.3 | chr11:61684808-61743759 |
| 2799 | Akap11 | NM_001164503.1 | chr14:78892052-78936667 |
| 2800 | Akap12 | NM_031185.3 | chr10:5987069-6080212 |
| 2801 | Akap13 | NM_029332.1 | chr7:82600419-82899495 |
| 2802 | Akap14 | NM_001033785.2 | chrX:34690693-34708837 |
| 2803 | Akap17b | NM_001081956.1 | chrY:34148177-34185409 |
| 2804 | Akap2 | NM_001035532.2 | chr4:57858119-57909856 |
| 2805 | Akap2 | NM_001035533.2 | chr4:57858119-57909856 |
| 2806 | Akap2 | NM_009649.3 | chr4:57858119-57909856 |
| 2807 | Akap3 | NM_009650.2 | chr6:126803115-126824326 |
| 2808 | Akap4 | NM_001042542.2 | chrX:6644640-6655732 |
| 2809 | Akap4 | NM_009651.4 | chrX:6644640-6655732 |
| 2810 | Akap5 | NM_001101471.1 | chr12:77425877-77435138 |
| 2811 | Akap6 | NM_198111.2 | chr12:53800369-54252002 |
| 2812 | Akap7 | NM_018747.4 | chr10:24888895-25018969 |
| 2813 | Akap8 | NM_019774.5 | chr17:32440620-32458098 |
| 2814 | Akap8l | NM_017476.2 | chr17:32458368-32487522 |
| 2815 | Akap9 | NM_194462.2 | chr5:3928185-4080204 |
| 2816 | Akip1 | NM_020616.1 | chr7:116847251-116855695 |
| 2817 | Akirin1 | NM_023423.3 | chr4:123412437-123427542 |
| 2818 | Akirin2 | NM_001007589.3 | chr4:34497864-34514157 |
| 2819 | Akna | NM_001045514.3 | chr4:63028161-63064479 |
| 2820 | Aknad1 | NM_177859.3 | chr3:108542575-108585227 |
| 2821 | Akp3 | NM_007432.2 | chr1:89021582-89024487 |
| 2822 | Akr1a1 | NM_021473.1 | chr4:116309114-116324279 |
| 2823 | Akr1b10 | NM_172398.3 | chr6:34334246-34346949 |
| 2824 | Akr1b3 | NM_009658.3 | chr6:34253930-34267489 |
| 2825 | Akr1b7 | NM_009731.2 | chr6:34362361-34373137 |
| 2826 | Akr1b8 | NM_008012.1 | chr6:34304163-34318454 |
| 2827 | Akr1c12 | NM_013777.2 | chr13:4267417-4278645 |
| 2828 | Akr1c13 | NM_013778.2 | chr13:4190432-4204849 |
| 2829 | Akr1c14 | NM_134072.1 | chr13:4058836-4089668 |
| 2830 | Akr1c18 | NM_134066.2 | chr13:4131872-4149877 |
| 2831 | Akr1c19 | NM_001013785.3 | chr13:4232985-4247605 |
| 2832 | Akr1c20 | NM_054080.1 | chr13:4506404-4522579 |
| 2833 | Akr1c21 | NM_029901.2 | chr13:4573320-4585789 |
| 2834 | Akr1c6 | NM_030611.3 | chr13:4433568-4456776 |
| 2835 | Akr1cl | NM_027582.3 | chr1:65059659-65079322 |
| 2836 | Akr1d1 | NM_145364.2 | chr6:37480172-37518815 |
| 2837 | Akr1e1 | NM_018859.2 | chr13:4591735-4608410 |
| 2838 | Akr7a5 | NM_025337.3 | chr4:138866658-138874701 |
| 2839 | Akt1 | NM_001165894.1 | chr12:113892031-113912487 |
| 2840 | Akt1 | NM_009652.3 | chr12:113892031-113912487 |
| 2841 | Akt1s1 | NM_001253920.1 | chr7:52104593-52110791 |
| 2842 | Akt1s1 | NM_001290694.1 | chr7:52104593-52110791 |

Fig. 25 - 16

| # | Gene | Accession | Location |
|---|---|---|---|
| 2843 | Akt1s1 | NM_001290695.1 | chr7:52104593-52110791 |
| 2844 | Akt1s1 | NM_026270.4 | chr7:52104593-52110791 |
| 2845 | Akt2 | NM_001110208.1 | chr7:28376578-28424472 |
| 2846 | Akt2 | NM_007434.3 | chr7:28376578-28424472 |
| 2847 | Akt3 | NM_011785.3 | chr1:178952245-179178898 |
| 2848 | Aktip | NM_010741.5 | chr18:93647398-93659393 |
| 2849 | Alad | NM_001276446.1 | chr4:62167017-62181097 |
| 2850 | Alad | NM_008525.4 | chr4:62167017-62181097 |
| 2851 | Alas1 | NM_001291835.1 | chr9:106135785-106150285 |
| 2852 | Alas1 | NM_020559.2 | chr9:106135785-106150285 |
| 2853 | Alas2 | NM_001102446.1 | chrX:146981927-147005165 |
| 2854 | Alas2 | NM_009653.3 | chrX:146981927-147005165 |
| 2855 | Alb | NM_009654.3 | chr5:90889914-90905629 |
| 2856 | Alcam | NM_009655.2 | chr16:52249108-52453110 |
| 2857 | Aldh16a1 | NM_145954.1 | chr7:52397210-52409908 |
| 2858 | Aldh18a1 | NM_019808.2 | chr19:40624746-40662953 |
| 2859 | Aldh18a1 | NM_153554.2 | chr19:40624746-40662953 |
| 2860 | Aldh1a1 | NM_013467.3 | chr19:20676471-20717952 |
| 2861 | Aldh1a2 | NM_009022.4 | chr9:71063595-71144050 |
| 2862 | Aldh1a3 | NM_053080.3 | chr7:73535778-73572363 |
| 2863 | Aldh1a7 | NM_011921.2 | chr19:20767442-20802046 |
| 2864 | Aldh1b1 | NM_028270.4 | chr4:45811893-45817480 |
| 2865 | Aldh1l1 | NM_027406.1 | chr6:90500841-90549165 |
| 2866 | Aldh1l2 | NM_153543.2 | chr10:82950191-82996885 |
| 2867 | Aldh2 | NM_009656.4 | chr5:122017695-122043833 |
| 2868 | Aldh3a1 | NM_001112725.1 | chr11:61022243-61031918 |
| 2869 | Aldh3a1 | NM_007436.2 | chr11:61022243-61031918 |
| 2870 | Aldh3a2 | NM_007437.5 | chr11:61058256-61080629 |
| 2871 | Aldh3b1 | NM_026316.2 | chr19:3913490-3929716 |
| 2872 | Aldh3b2 | NM_001177438.1 | chr19:3972327-3981665 |
| 2873 | Aldh4a1 | NM_175438.4 | chr4:139178809-139205606 |
| 2874 | Aldh5a1 | NM_172532.3 | chr13:24999448-25029530 |
| 2875 | Aldh6a1 | NM_134042.2 | chr12:85771668-85791900 |
| 2876 | Aldh7a1 | NM_001127338.1 | chr18:56685389-56747366 |
| 2877 | Aldh7a1 | NM_138600.4 | chr18:56685389-56747366 |
| 2878 | Aldh8a1 | NM_178713.4 | chr10:21097105-21116384 |
| 2879 | Aldh9a1 | NM_019993.3 | chr1:169280121-169298661 |
| 2880 | Aldoa | NM_001177307.1 | chr7:133938747-133943961 |
| 2881 | Aldoa | NM_001177303.1 | chr7:133938747-133943961 |
| 2882 | Aldoa | NM_007438.4 | chr7:133938747-133943961 |
| 2883 | Aldoart1 | NM_001199270.1 | chr4:72511616-72513668 |
| 2884 | Aldoart2 | NM_001277340.1 | chr12:56666191-56667883 |
| 2885 | Aldob | NM_144903.2 | chr4:49548866-49562355 |
| 2886 | Aldoc | NM_009657.4 | chr11:78137699-78140262 |
| 2887 | Alg1 | NM_145362.2 | chr16:5239714-5245001 |
| 2888 | Alg10b | NM_001033441.3 | chr15:90054742-90060985 |
| 2889 | Alg13 | NM_001243161.1 | chr8:23171192-23182099 |
| 2890 | Alg13 | NM_183142.4 | chr8:23171192-23182099 |
| 2891 | Alg13 | NR_040650.1 | chr8:23171192-23182099 |
| 2892 | Alg12 | NM_001142357.1 | chr15:88635672-88649748 |
| 2893 | Alg12 | NM_145477.2 | chr15:88635672-88649748 |
| 2894 | Alg13 | NM_026247.3 | chrX:140752508-140808991 |
| 2895 | Alg13 | NR_037145.1 | chrX:140752508-140808991 |
| 2896 | Alg14 | NM_024178.2 | chr3:120994734-121064929 |
| 2897 | Alg2 | NM_019998.3 | chr4:47482704-47487239 |
| 2898 | Alg3 | NM_145939.2 | chr16:20605530-20610822 |
| 2899 | Alg5 | NM_025442.3 | chr3:54539460-54553717 |
| 2900 | Alg6 | NM_001081264.1 | chr4:99382320-99430151 |
| 2901 | Alg8 | NM_199035.2 | chr7:104520126-104540668 |
| 2902 | Alg9 | NM_133981.2 | chr9:50583329-50651744 |
| 2903 | Alg9 | NR_045601.1 | chr9:50583329-50651744 |
| 2904 | Alk | NM_007439.2 | chr17:72218327-72953647 |
| 2905 | Alkbh1 | NM_001102565.1 | chr12:88769028-88784789 |
| 2906 | Alkbh2 | NM_175016.2 | chr5:114573942-114578185 |
| 2907 | Alkbh3 | NM_026944.1 | chr2:93820791-93850887 |
| 2908 | Alkbh4 | NM_028070.1 | chr5:136614650-136617484 |
| 2909 | Alkbh5 | NM_172943.4 | chr11:60351184-60372014 |
| 2910 | Alkbh6 | NM_198027.2 | chr7:31093771-31099322 |
| 2911 | Alkbh7 | NM_025538.3 | chr17:57136761-57138759 |
| 2912 | Alkbh7 | NM_027372.1 | chr17:57136761-57138759 |
| 2913 | Alkbh8 | NM_026303.1 | chr9:3335230-3385846 |
| 2914 | Allc | NM_053156.2 | chr12:29238619-29267348 |
| 2915 | Alms1 | NM_145223.2 | chr6:85537524-85652745 |
| 2916 | Alms1-ps2 | NR_040440.2 | chr6:85742110-85754051 |
| 2917 | Alox12 | NM_007440.4 | chr11:70054956-70068843 |
| 2918 | Alox12b | NM_009659.2 | chr11:69076573-69083293 |
| 2919 | Alox12e | NM_145684.1 | chr11:70129114-70136020 |
| 2920 | Alox15 | NM_009660.3 | chr11:70157648-70165533 |
| 2921 | Alox5 | NM_009662.2 | chr6:116360088-116411196 |
| 2922 | Alox5ap | NM_009663.2 | chr5:150076633-150099623 |
| 2923 | Alox8 | NM_009661.4 | chr11:69097386-69011345 |
| 2924 | Aloxe3 | NM_011786.2 | chr11:68939878-68962617 |
| 2925 | Alpi | NM_001081082.2 | chr1:88994576-88998181 |
| 2926 | Alpk1 | NM_027808.3 | chr3:127373227-127483445 |
| 2927 | Alpk2 | NM_001037294.1 | chr18:65425185-65553542 |
| 2928 | Alpk3 | NM_054085.2 | chr7:88202485-88250498 |
| 2929 | Alpl | NM_001287172.1 | chr4:137297645-137352299 |
| 2930 | Alpl | NM_001287176.1 | chr4:137297645-137352299 |
| 2931 | Alpl | NM_007431.3 | chr4:137297645-137352299 |
| 2932 | Alppl2 | NM_007433.2 | chr1:88983265-88986503 |
| 2933 | Als2 | NM_001159948.2 | chr1:59177778-59294075 |
| 2934 | Als2 | NM_028717.6 | chr1:59177778-59294075 |
| 2935 | Als2 | NM_146109.3 | chr1:59177778-59294075 |
| 2936 | Als2cl | NM_001146059.1 | chr9:110782677-110803034 |
| 2937 | Als2cl | NM_001146060.1 | chr9:110782677-110803034 |
| 2938 | Als2cl | NM_146228.2 | chr9:110782677-110803034 |
| 2939 | Als2cr11 | NM_175200.4 | chr1:59107349-59151744 |
| 2940 | Als2cr12 | NM_175370.4 | chr1:58714963-58752833 |
| 2941 | Alx1 | NM_172553.4 | chr10:102470480-102491411 |
| 2942 | Alx3 | NM_007441.3 | chr3:107397948-107408793 |
| 2943 | Alx4 | NM_007442.3 | chr2:93482590-93521496 |
| 2944 | Alyref | NM_011568.1 | chr11:120455829-120459679 |
| 2945 | Alyref2 | NM_019484.4 | chr1:173433608-173434881 |
| 2946 | Amacr | NM_008537.4 | chr15:10911510-10926379 |
| 2947 | Ambn | NM_009664.2 | chr5:88885035-88897554 |
| 2948 | Ambp | NM_007443.3 | chr4:62804312-62815176 |
| 2949 | Ambra1 | NM_001080754.1 | chr2:91570294-91759006 |
| 2950 | Ambra1 | NM_172669.3 | chr2:91570294-91759006 |
| 2951 | Amd1 | NM_009665.5 | chr10:40007264-40021994 |
| 2952 | Amd2 | NM_007444.3 | chr10:40007271-40021992 |
| 2953 | Amdhd1 | NM_027908.1 | chr10:92986082-93002778 |
| 2954 | Amdhd2 | NM_172935.4 | chr17:24292799-24300700 |
| 2955 | Amelx | NM_001081978.2 | chrX:165233030-165742372 |
| 2956 | Amelx | NM_001290371.1 | chrX:165233030-165742372 |
| 2957 | Amelx | NM_009666.4 | chrX:165233030-165742372 |
| 2958 | Amer1 | NM_175179.4 | chrX:92615652-92640179 |
| 2959 | Amer2 | NM_001164705.1 | chr14:60997122-60999840 |
| 2960 | Amer2 | NM_028113.3 | chr14:60997122-60999840 |
| 2961 | Amer3 | NM_213727.2 | chr1:34636537-34647789 |
| 2962 | Amfr | NM_011787.2 | chr8:96495487-96536540 |
| 2963 | Amh | NM_007445.2 | chr10:80267992-80270393 |
| 2964 | Amhr2 | NM_144547.2 | chr15:102275797-102285070 |
| 2965 | Amical | NM_001005421.4 | chr9:44887266-44916614 |
| 2966 | Amigo1 | NM_001004293.2 | chr3:107989206-107995204 |
| 2967 | Amigo1 | NM_001287093.1 | chr3:107989206-107995204 |
| 2968 | Amigo1 | NM_146137.3 | chr3:107989206-107995204 |
| 2969 | Amigo2 | NM_001164563.1 | chr15:97074504-97216122 |
| 2970 | Amigo2 | NM_001164602.1 | chr15:97074504-97216122 |
| 2971 | Amigo2 | NM_178114.4 | chr15:97074504-97216122 |
| 2972 | Amigo3 | NM_177275.4 | chr9:107955490-107958032 |
| 2973 | Ammecr1 | NM_019496.3 | chrX:139288016-139401271 |
| 2974 | Ammecr1l | NM_001242430.1 | chr18:31919477-31943737 |
| 2975 | Ammecr1l | NM_153515.4 | chr18:31919477-31943737 |
| 2976 | Amn | NM_033603.2 | chr12:112509321-112514637 |
| 2977 | Amn1 | NM_001113424.1 | chr6:149106098-149137234 |
| 2978 | Amot | NM_001290274.1 | chrX:141880966-141922182 |
| 2979 | Amot | NM_153319.3 | chrX:141880966-141922182 |
| 2980 | Amotl1 | NM_001081395.1 | chr9:14346410-14419444 |
| 2981 | Amotl2 | NM_019764.2 | chr9:102620133-102635747 |
| 2982 | Ampd1 | NM_001033303.2 | chr3:102877936-102903643 |
| 2983 | Ampd2 | NM_001289719.1 | chr3:107876979-107889584 |
| 2984 | Ampd2 | NM_001289720.1 | chr3:107876979-107889584 |
| 2985 | Ampd2 | NM_028779.5 | chr3:107876979-107889584 |
| 2986 | Ampd3 | NM_001276301.3 | chr7:117911719-117955922 |
| 2987 | Ampd3 | NM_009667.3 | chr7:117911719-117955922 |
| 2988 | Amph | NM_001289546.1 | chr13:19040219-19242788 |
| 2989 | Amph | NM_175007.2 | chr13:19040219-19242788 |
| 2990 | Amt | NM_001013814.1 | chr9:108199252-108203928 |
| 2991 | Amtn | NM_027793.1 | chr5:88805132-88814941 |
| 2992 | Amy1 | NM_001110505.1 | chr3:113258869-113280668 |
| 2993 | Amy1 | NM_007446.2 | chr3:113258869-113280668 |
| 2994 | Amy2a2 | NM_001160152.1 | chr3:113,147,967-113,159,576 |
| 2995 | Amy2a4 | NM_001160150.1 | chr3:113147966-113159576 |
| 2996 | Amy2a4 | NM_001160150.1 | chr3:113082754-113094367 |
| 2997 | Amy2a5 | NM_001042711.2 | chr3:113052095-113061617 |
| 2998 | Amy2a5 | NM_001042711.2 | chr3:113115366-113126970 |
| 2999 | Amy2a5 | NM_001042711.2 | chr3:113147966-113159576 |
| 3000 | Amy2a5 | NM_001042711.2 | chr3:113082754-113094367 |
| 3001 | Amy2b | NM_001190403.1 | chr3:112950573-112959645 |
| 3002 | Amy2b | NM_001190404.1 | chr3:112950573-112959645 |
| 3003 | Amz1 | NM_173405.2 | chr5:141200080-141229266 |
| 3004 | Amz2 | NM_001252193.1 | chr11:109287259-109299462 |
| 3005 | Amz2 | NM_025275.4 | chr11:109287259-109299462 |
| 3006 | Anapc1 | NM_008569.2 | chr2:128435818-128513131 |
| 3007 | Anapc10 | NM_026904.2 | chr8:82235718-82301220 |
| 3008 | Anapc11 | NM_001038230.2 | chr11:120459734-120469512 |
| 3009 | Anapc11 | NM_025389.4 | chr11:120459734-120469512 |
| 3010 | Anapc13 | NM_181394.3 | chr9:102578625-102584574 |
| 3011 | Anapc15 | NM_001291348.1 | chr7:109029838-109048059 |
| 3012 | Anapc15 | NM_001291349.1 | chr7:109029838-109048059 |
| 3013 | Anapc15 | NM_001291352.1 | chr7:109029838-109048059 |
| 3014 | Anapc15 | NM_001291353.1 | chr7:109029838-109048059 |
| 3015 | Anapc15 | NM_027532.4 | chr7:109029838-109048059 |
| 3016 | Anapc16 | NM_025514.2 | chr10:59450657-59465860 |
| 3017 | Anapc2 | NM_175300.4 | chr2:25127985-25141436 |
| 3018 | Anapc4 | NM_024213.2 | chr5:53225373-53257973 |
| 3019 | Anapc5 | NM_001042491.2 | chr5:123237469-123271351 |
| 3020 | Anapc5 | NM_001289517.1 | chr5:123237469-123271351 |
| 3021 | Anapc5 | NM_001289518.1 | chr5:123237469-123271351 |
| 3022 | Anapc5 | NM_001289519.1 | chr5:123237469-123271351 |
| 3023 | Anapc5 | NM_001289520.1 | chr5:123237469-123271351 |
| 3024 | Anapc5 | NM_021505.3 | chr5:123237469-123271351 |
| 3025 | Anapc7 | NM_019805.4 | chr5:122872452-122894920 |
| 3026 | Ang | NM_001161731.2 | chr14:51710751-51725826 |
| 3027 | Ang | NM_007447.3 | chr14:51710751-51725826 |
| 3028 | Ang2 | NM_007449.2 | chr14:51815160-51815598 |
| 3029 | Ang3 | NM_001123394.2 | chr14:44534734-44540745 |
| 3030 | Ang4 | NM_177544.4 | chr14:52383566-52393265 |
| 3031 | Ang5 | NM_007448.2 | chr14:44534734-44540745 |

Fig. 25 - 17

| | | | | | | | |
|---|---|---|---|---|---|---|---|
| 3032 | Ang6 | NM_001011876.2 | chr14:44579328-44584083 | 3127 | Ankrd39 | NM_026241.3 | chr1:36595017-36604046 |
| 3033 | Angel1 | NM_144524.2 | chr12:88041451-88067410 | 3128 | Ankrd40 | NM_027799.2 | chr11:94189314-94203161 |
| 3034 | Angel2 | NM_001199020.1 | chr1:192748986-192770370 | 3129 | Ankrd40 | NM_146024.1 | chr11:94189314-94203161 |
| 3035 | Angel2 | NM_021421.4 | chr1:192748986-192770370 | 3130 | Ankrd42 | NM_028665.4 | chr7:99732692-99785652 |
| 3036 | Angel2 | NR_037578.1 | chr1:192748986-192770370 | 3131 | Ankrd44 | NM_001081433.3 | chr1:54702183-54983231 |
| 3037 | Angel2 | NR_037579.1 | chr1:192748986-192770370 | 3132 | Ankrd45 | NM_028664.1 | chr1:163072843-163100638 |
| 3038 | Angpt1 | NM_001286062.1 | chr15:42256212-42508523 | 3133 | Ankrd46 | NM_175134.4 | chr15:36407422-36426546 |
| 3039 | Angpt1 | NM_009640.4 | chr15:42256212-42508523 | 3134 | Ankrd49 | NM_019683.3 | chr9:14584641-14587408 |
| 3040 | Angpt2 | NM_007426.4 | chr8:18690263-18741562 | 3135 | Ankrd50 | NM_001167883.1 | chr3:38348182-38383738 |
| 3041 | Angpt4 | NM_009641.1 | chr2:151737067-151770390 | 3136 | Ankrd52 | NM_172790.2 | chr10:127814180-127831062 |
| 3042 | Angptl1 | NM_028333.2 | chr1:158769154-158791209 | 3137 | Ankrd53 | NM_029245.3 | chr6:83712639-83718320 |
| 3043 | Angptl2 | NM_011923.4 | chr2:33071481-33103234 | 3138 | Ankrd54 | NM_144849.1 | chr15:78885523-78893289 |
| 3044 | Angptl3 | NM_013913.3 | chr4:98697646-98704879 | 3139 | Ankrd55 | NM_001168403.1 | chr13:113078658-113174210 |
| 3045 | Angptl4 | NM_020581.2 | chr17:33911844-33918520 | 3140 | Ankrd55 | NM_001168404.1 | chr13:113078658-113174210 |
| 3046 | Angptl6 | NM_145154.2 | chr9:20678253-20684184 | 3141 | Ankrd55 | NM_001168405.1 | chr13:113078658-113174210 |
| 3047 | Angptl7 | NM_001039554.3 | chr4:147869389-147874571 | 3142 | Ankrd55 | NM_029898.3 | chr13:113078658-113174210 |
| 3048 | Ank | NM_020332.4 | chr15:27396432-27524662 | 3143 | Ankrd6 | NM_001012450.1 | chr4:32891009-33037801 |
| 3049 | Ank1 | NM_001110783.3 | chr8:24085307-24260969 | 3144 | Ankrd6 | NM_001012451.1 | chr4:32891009-33037801 |
| 3050 | Ank1 | NM_001277280.2 | chr8:24085307-24260969 | 3145 | Ankrd6 | NM_080471.3 | chr4:32891009-33037801 |
| 3051 | Ank1 | NM_001277281.2 | chr8:24085307-24260969 | 3146 | Ankrd60 | NM_001199955.1 | chr2:173394161-173403842 |
| 3052 | Ank1 | NM_001277284.2 | chr8:24085307-24260969 | 3147 | Ankrd60 | NM_027303.1 | chr2:173394161-173403842 |
| 3053 | Ank1 | NM_001277286.2 | chr8:24085307-24260969 | 3148 | Ankrd61 | NM_025732.3 | chr5:144651612-144655936 |
| 3054 | Ank1 | NM_001277289.1 | chr8:24085307-24260969 | 3149 | Ankrd63 | NM_001081971.1 | chr2:118524838-118529699 |
| 3055 | Ank1 | NM_031158.4 | chr8:24085307-24260969 | 3150 | Ankrd66 | NM_001254953.1 | chr17:43671122-43680588 |
| 3056 | Ank1 | NR_102385.1 | chr8:24085307-24260969 | 3151 | Ankrd7 | NM_001167757.1 | chr6:18816317-18829584 |
| 3057 | Ank1 | NR_102386.2 | chr8:24085307-24260969 | 3152 | Ankrd7 | NM_029202.2 | chr6:18816317-18829584 |
| 3058 | Ank2 | NM_001034168.1 | chr3:126624524-126701370 | 3153 | Ankrd9 | NM_175207.4 | chr12:112213562-112217231 |
| 3059 | Ank2 | NM_178655.3 | chr3:126624524-126701370 | 3154 | Anks1 | NM_001286040.1 | chr17:28046250-28199724 |
| 3060 | Ank3 | NM_009670.4 | chr10:68996455-69490184 | 3155 | Anks1 | NM_001286041.1 | chr17:28046250-28199724 |
| 3061 | Ank3 | NM_146005.3 | chr10:68996455-69490184 | 3156 | Anks1 | NM_181413.4 | chr17:28046250-28199724 |
| 3062 | Ank3 | NM_170687.3 | chr10:68996455-69490184 | 3157 | Anks1b | NM_001128086.2 | chr10:89336253-90435729 |
| 3063 | Ank3 | NM_170688.2 | chr10:68996455-69490184 | 3158 | Anks1b | NM_001177396.1 | chr10:89336253-90435729 |
| 3064 | Ank3 | NM_170689.2 | chr10:68996455-69490184 | 3159 | Anks1b | NM_001177397.1 | chr10:89336253-90435729 |
| 3065 | Ank3 | NM_170690.2 | chr10:68996455-69490184 | 3160 | Anks1b | NM_001177398.1 | chr10:89336253-90435729 |
| 3066 | Ank3 | NM_170728.2 | chr10:68996455-69490184 | 3161 | Anks1b | NM_181398.3 | chr10:89336253-90435729 |
| 3067 | Ank3 | NM_170729.2 | chr10:68996455-69490184 | 3162 | Anks3 | NM_028301.4 | chr16:4941419-4964330 |
| 3068 | Ank3 | NM_170730.2 | chr10:68996455-69490184 | 3163 | Anks4b | NM_028085.2 | chr7:127317371-127327230 |
| 3069 | Ankar | NM_176980.4 | chr1:72689553-72747138 | 3164 | Anks6 | NM_001024136.1 | chr4:47028560-47070178 |
| 3070 | Ankdd1b | NM_001047714.1 | chr13:97186088-97241115 | 3165 | Ankub1 | NM_001033349.2 | chr3:57471343-57496459 |
| 3071 | Ankef1 | NM_175667.4 | chr2:136358056-136381590 | 3166 | Ankzf1 | NM_001267620.1 | chr1:75188733-75207353 |
| 3072 | Ankfn1 | NM_001080933.1 | chr1:89282399-89399869 | 3167 | Ankzf1 | NM_026187.5 | chr1:75188733-75207353 |
| 3073 | Ankfy1 | NM_009671.5 | chr11:72503503-72585648 | 3168 | Ankzf1 | NR_051998.1 | chr1:75188733-75207353 |
| 3074 | Ankhd1 | NM_175375.3 | chr18:36720256-36818562 | 3169 | Ankzf1 | NR_051999.1 | chr1:75188733-75207353 |
| 3075 | Ankib1 | NM_001003909.4 | chr5:3689998-3803124 | 3170 | Anln | NM_028390.3 | chr9:22135657-22193650 |
| 3076 | Ankib1 | NM_001289527.1 | chr5:3689998-3803124 | 3171 | Ano1 | NM_001242349.1 | chr7:151774453-151924497 |
| 3077 | Ankib1 | NM_001289528.1 | chr5:3689998-3803124 | 3172 | Ano1 | NM_178642.5 | chr7:151774453-151924497 |
| 3078 | Ankib1 | NM_001289529.1 | chr5:3689998-3803124 | 3173 | Ano10 | NM_001271873.1 | chr9:122084991-122203541 |
| 3079 | Ankk1 | NM_172922.3 | chr9:49223326-49235126 | 3174 | Ano10 | NM_133979.3 | chr9:122084991-122203541 |
| 3080 | Ankle1 | NM_172756.2 | chr8:73929910-73934803 | 3175 | Ano2 | NM_153589.2 | chr6:125640436-125990146 |
| 3081 | Ankle2 | NM_001253814.1 | chr5:110660022-110685670 | 3176 | Ano3 | NM_001128103.2 | chr2:110495358-110790401 |
| 3082 | Ankle2 | NM_027922.2 | chr5:110660022-110685670 | 3177 | Ano4 | NM_001277188.1 | chr10:88411738-88720535 |
| 3083 | Ankmy1 | NM_172850.3 | chr1:94766705-94799483 | 3178 | Ano4 | NR_102339.1 | chr10:88411738-88720535 |
| 3084 | Ankmy2 | NM_148033.3 | chr12:36883710-36923878 | 3179 | Ano5 | NM_001271879.1 | chr7:58766398-58854077 |
| 3085 | Ankra2 | NM_001271388.1 | chr13:99033030-99044709 | 3180 | Ano5 | NM_177694.6 | chr7:58766398-58854077 |
| 3086 | Ankra2 | NM_001271389.1 | chr13:99033030-99044709 | 3181 | Ano5 | NR_073508.1 | chr7:58766398-58854077 |
| 3087 | Ankra2 | NM_001271390.1 | chr13:99033030-99044709 | 3182 | Ano6 | NM_001253813.1 | chr15:95621273-95805903 |
| 3088 | Ankra2 | NM_001271391.1 | chr13:99033030-99044709 | 3183 | Ano6 | NM_175344.4 | chr15:95621273-95805903 |
| 3089 | Ankra2 | NM_001271392.1 | chr13:99033030-99044709 | 3184 | Ano7 | NM_001271884.1 | chr1:95270472-95300881 |
| 3090 | Ankra2 | NM_023472.2 | chr13:99033030-99044709 | 3185 | Ano7 | NM_207031.2 | chr1:95270472-95300881 |
| 3091 | Ankrd1 | NM_013468.3 | chr19:36186454-36194334 | 3186 | Ano8 | NM_001164679.1 | chr8:73999918-74009966 |
| 3092 | Ankrd10 | NM_001167967.2 | chr8:11611580-11635757 | 3187 | Ano9 | NM_178381.3 | chr7:148287117-148303705 |
| 3093 | Ankrd10 | NM_001281974.1 | chr8:11611580-11635757 | 3188 | Anp32a | NM_009672.1 | chr9:62189148-62226609 |
| 3094 | Ankrd10 | NM_001281975.1 | chr8:11611580-11635757 | 3189 | Anp32b | NM_130889.2 | chr4:46463988-46485395 |
| 3095 | Ankrd10 | NM_133971.3 | chr8:11611580-11635757 | 3190 | Anp32e | NM_001253757.1 | chr3:95733179-95751310 |
| 3096 | Ankrd10 | NR_030781.2 | chr8:11611580-11635757 | 3191 | Anp32e | NM_001253758.1 | chr3:95733179-95751310 |
| 3097 | Ankrd11 | NM_001081379.2 | chr8:125407721-125566184 | 3192 | Anp32e | NM_023210.4 | chr3:95733179-95751310 |
| 3098 | Ankrd11 | NR_037865.1 | chr8:125407721-125566184 | 3193 | Anpep | NM_008486.2 | chr7:86966688-86987238 |
| 3099 | Ankrd12 | NM_001025572.1 | chr17:66316840-66426386 | 3194 | Antxr1 | NM_054041.2 | chr6:87083846-87285769 |
| 3100 | Ankrd13a | NM_026718.2 | chr5:115225148-115255829 | 3195 | Antxr2 | NM_133738.1 | chr5:98313706-98459981 |
| 3101 | Ankrd13b | NM_172783.2 | chr11:77283988-77303180 | 3196 | Antxrl | NM_172808.2 | chr14:34866656-34889185 |
| 3102 | Ankrd13c | NM_001013806.1 | chr3:157610429-157669801 | 3197 | Anxa1 | NM_010730.2 | chr19:20447923-20465161 |
| 3103 | Ankrd13d | NM_026720.2 | chr3:4270179-4283137 | 3198 | Anxa10 | NM_001136089.2 | chr8:64535838-64601990 |
| 3104 | Ankrd16 | NM_177268.4 | chr2:11699379-11711950 | 3199 | Anxa10 | NM_011923.3 | chr8:64535838-64601990 |
| 3105 | Ankrd17 | NM_030886.2 | chr5:90656190-90795211 | 3200 | Anxa11 | NM_013469.2 | chr14:26661640-26706290 |
| 3106 | Ankrd17 | NM_198010.2 | chr5:90656190-90795211 | 3201 | Anxa13 | NM_027211.2 | chr15:58173018-58220829 |
| 3107 | Ankrd2 | NM_020383.1 | chr19:42110527-42119600 | 3202 | Anxa2 | NM_007585.3 | chr9:69801490-69839592 |
| 3108 | Ankrd22 | NM_024204.6 | chr19:34197039-34240531 | 3203 | Anxa3 | NM_013470.2 | chr5:97222403-97274987 |
| 3109 | Ankrd23 | NM_153502.3 | chr1:36587378-36592574 | 3204 | Anxa4 | NM_013471.2 | chr6:86686833-86743578 |
| 3110 | Ankrd24 | NM_027480.3 | chr10:81091284-81110357 | 3205 | Anxa5 | NM_009673.2 | chr3:36347846-36374809 |
| 3111 | Ankrd26 | NM_001081112.1 | chr6:118452581-118512274 | 3206 | Anxa6 | NM_001110211.1 | chr11:54792463-54846973 |
| 3112 | Ankrd27 | NM_145633.3 | chr7:36371265-36424256 | 3207 | Anxa6 | NM_013472.4 | chr11:54792463-54846973 |
| 3113 | Ankrd27 | NM_178263.3 | chr7:36371265-36424256 | 3208 | Anxa7 | NM_001110794.1 | chr14:21274482-21299355 |
| 3114 | Ankrd28 | NM_001024604.2 | chr14:32513200-32643601 | 3209 | Anxa7 | NM_009674.3 | chr14:21274482-21299355 |
| 3115 | Ankrd29 | NM_001190371.1 | chr18:12410865-12464229 | 3210 | Anxa8 | NM_001281845.1 | chr14:34864315-34915940 |
| 3116 | Ankrd32 | NM_134071.3 | chr13:77182348-77274729 | 3211 | Anxa8 | NM_013473.4 | chr14:34864315-34915940 |
| 3117 | Ankrd33 | NM_144790.1 | chr15:100946185-100950455 | 3212 | Anxa9 | NM_001085383.1 | chr3:95086856-95111098 |
| 3118 | Ankrd33b | NM_001164441.1 | chr15:31221234-31297514 | 3213 | Anxa9 | NM_023628.2 | chr3:95086856-95111098 |
| 3119 | Ankrd33b | NM_026153.3 | chr15:31221234-31297514 | 3214 | Aoah | NM_001181854.1 | chr13:20885981-21116123 |
| 3120 | Ankrd33b | NM_027496.3 | chr15:31221234-31297514 | 3215 | Aoah | NM_012054.4 | chr13:20885981-21116123 |
| 3121 | Ankrd34a | NM_001024851.3 | chr3:96400558-96403701 | 3216 | Aoc1 | NM_001161621.1 | chr6:48845253-48859186 |
| 3122 | Ankrd34b | NM_175455.4 | chr3:93195923-93211613 | 3217 | Aoc1 | NM_001161622.1 | chr6:48845253-48859186 |
| 3123 | Ankrd34c | NM_207260.2 | chr9:89623086-89633313 | 3218 | Aoc1 | NM_029638.2 | chr6:48845253-48859186 |
| 3124 | Ankrd35 | NM_001081139.1 | chr3:96474053-96494957 | 3219 | Aoc2 | NM_178932.1 | chr11:101186376-101191008 |
| 3125 | Ankrd36 | NM_028816.2 | chr11:5469686-5589340 | 3220 | Aoc3 | NM_009675.3 | chr11:101191919-101200744 |
| 3126 | Ankrd37 | NM_001039562.1 | chr8:47082262-47085204 | 3221 | Aox1 | NM_009676.2 | chr1:58086812-58163254 |

Fig. 25 - 18

| | | | |
|---|---|---|---|
| 3222 | Aox2 | NM_001008419.2 | chr1:58335169-58436108 |
| 3223 | Aox3 | NM_023617.2 | chr1:58169979-58257296 |
| 3224 | Aox4 | NM_023631.2 | chr1:58267240-58325440 |
| 3225 | Ap1ar | NM_145964.2 | chr3:127510182-127540410 |
| 3226 | Ap1b1 | NM_001243043.1 | chr11:4838758-4942797 |
| 3227 | Ap1b1 | NM_001243044.1 | chr11:4838758-4942797 |
| 3228 | Ap1b1 | NM_007454.3 | chr11:4838758-4942797 |
| 3229 | Ap1g1 | NM_009677.6 | chr8:112302483-112388109 |
| 3230 | Ap1g2 | NM_007455.5 | chr14:55717672-55725430 |
| 3231 | Ap1m1 | NM_007456.4 | chr8:74764030-74781278 |
| 3232 | Ap1m2 | NM_001110300.1 | chr9:21099900-21116777 |
| 3233 | Ap1m2 | NM_009678.2 | chr9:21099900-21116777 |
| 3234 | Ap1s1 | NM_007457.1 | chr5:137510863-137521930 |
| 3235 | Ap1s2 | NM_001290378.1 | chrX:160346948-160371598 |
| 3236 | Ap1s2 | NM_001290379.1 | chrX:160346948-160371598 |
| 3237 | Ap1s2 | NM_026887.3 | chrX:160346948-160371598 |
| 3238 | Ap1s3 | NM_183027.2 | chr1:79603450-79668547 |
| 3239 | Ap2a1 | NM_001077264.1 | chr7:52151448-52184860 |
| 3240 | Ap2a1 | NM_007458.2 | chr7:52151448-52184860 |
| 3241 | Ap2a2 | NM_007459.3 | chr7:148748079-148818910 |
| 3242 | Ap2b1 | NM_001035854.2 | chr11:83116198-83218535 |
| 3243 | Ap2b1 | NM_027915.3 | chr11:83116198-83218535 |
| 3244 | Ap2m1 | NM_009679.3 | chr16:20535576-20544126 |
| 3245 | Ap2s1 | NM_198613.2 | chr7:17323792-17334639 |
| 3246 | Ap3b1 | NM_009680.3 | chr13:95128914-95336271 |
| 3247 | Ap3b2 | NM_021492.3 | chr7:88605284-88638811 |
| 3248 | Ap3d1 | NM_007460.1 | chr10:80169722-80204956 |
| 3249 | Ap3m1 | NM_018829.4 | chr14:21852963-21871664 |
| 3250 | Ap3m2 | NM_001122820.1 | chr8:23897825-23916126 |
| 3251 | Ap3m2 | NM_029505.3 | chr8:23897825-23916126 |
| 3252 | Ap3s1 | NM_009681.5 | chr18:46901570-46950480 |
| 3253 | Ap3s2 | NM_009682.3 | chr7:87020210-87065526 |
| 3254 | Ap4b1 | NM_001163552.1 | chr3:103613439-103625948 |
| 3255 | Ap4b1 | NM_001163553.1 | chr3:103613439-103625948 |
| 3256 | Ap4b1 | NM_026193.2 | chr3:103613439-103625948 |
| 3257 | Ap4e1 | NM_175550.3 | chr2:126834446-126895550 |
| 3258 | Ap4m1 | NM_021392.4 | chr5:138613249-138619913 |
| 3259 | Ap4s1 | NM_021710.3 | chr12:52791953-52839926 |
| 3260 | Ap5b1 | NM_001033448.2 | chr19:5568073-5571261 |
| 3261 | Ap5m1 | NM_144535.4 | chr14:49686170-49707398 |
| 3262 | Ap5s1 | NM_001291031.1 | chr2:131036095-131039250 |
| 3263 | Ap5s1 | NM_001291032.1 | chr2:131036095-131039250 |
| 3264 | Ap5s1 | NM_027129.3 | chr2:131036095-131039250 |
| 3265 | Ap5s1 | NR_110992.1 | chr2:131036095-131039250 |
| 3266 | Ap5z1 | NM_172725.2 | chr5:142949884-142954669 |
| 3267 | Apaf1 | NM_001042558.1 | chr10:90452055-90545488 |
| 3268 | Apaf1 | NM_001282947.1 | chr10:90452055-90545488 |
| 3269 | Apaf1 | NM_009684.2 | chr10:90452055-90545488 |
| 3270 | Apba1 | NM_177034.3 | chr19:23833365-24024087 |
| 3271 | Apba2 | NM_001291166.1 | chr7:71646591-71898762 |
| 3272 | Apba2 | NM_001291167.1 | chr7:71646591-71898762 |
| 3273 | Apba2 | NM_007461.2 | chr7:71646591-71898762 |
| 3274 | Apba3 | NM_018758.2 | chr10:80730917-80735992 |
| 3275 | Apbb1 | NM_001253885.1 | chr7:112706978-112730167 |
| 3276 | Apbb1 | NM_001253886.1 | chr7:112706978-112730167 |
| 3277 | Apbb1 | NM_001253887.1 | chr7:112706978-112730167 |
| 3278 | Apbb1 | NM_009685.3 | chr7:112706978-112730167 |
| 3279 | Apbb1ip | NM_019456.2 | chr2:22629846-22731173 |
| 3280 | Apbb2 | NM_001201413.1 | chr5:66689963-67010056 |
| 3281 | Apbb2 | NM_001201414.1 | chr5:66689963-67010056 |
| 3282 | Apbb2 | NM_001201415.1 | chr5:66689963-67010056 |
| 3283 | Apbb2 | NM_001201416.1 | chr5:66689963-67010056 |
| 3284 | Apbb2 | NM_009686.2 | chr5:66689963-67010056 |
| 3285 | Apbb3 | NM_146085.1 | chr18:36830813-36883020 |
| 3286 | Apc | NM_007462.3 | chr18:34380838-34481844 |
| 3287 | Apc2 | NM_011789.2 | chr10:79764565-79781001 |
| 3288 | Apcdd1 | NM_133237.3 | chr18:63081980-63112849 |
| 3289 | Apcs | NM_011318.2 | chr1:174824091-174825185 |
| 3290 | Apeh | NM_146226.2 | chr9:107987744-107996811 |
| 3291 | Apela | NR_040692.1 | chr8:67552315-67561235 |
| 3292 | Apex1 | NM_009687.2 | chr14:51544624-51546863 |
| 3293 | Apex2 | NM_029943.1 | chrX:147006049-147022692 |
| 3294 | Aph1a | NM_146104.3 | chr3:95697843-95708562 |
| 3295 | Aph1a | NM_146134.2 | chr3:95697843-95708562 |
| 3296 | Aph1b | NM_177583.4 | chr9:66623293-66643230 |
| 3297 | Aph1c | NM_026674.3 | chr9:66626800-66682513 |
| 3298 | Api5 | NM_007466.3 | chr2:94251883-94278304 |
| 3299 | Apip | NM_019735.4 | chr2:102913831-102932806 |
| 3300 | Apitd1 | NM_027283.2 | chr4:148502457-148511709 |
| 3301 | Aplf | NM_001170489.1 | chr6:87578422-87622162 |
| 3302 | Aplf | NM_024251.4 | chr6:87578422-87622162 |
| 3303 | Apln | NM_013912.3 | chrX:45378432-45388029 |
| 3304 | Aplnr | NM_011784.3 | chr2:84976516-84980080 |
| 3305 | Aplp1 | NM_007467.3 | chr7:31219998-31230601 |
| 3306 | Aplp2 | NM_001102455.1 | chr9:30942991-31066970 |
| 3307 | Aplp2 | NM_001102456.1 | chr9:30942991-31066970 |
| 3308 | Aplp2 | NM_009691.4 | chr9:30942991-31066970 |
| 3309 | Apmap | NM_027977.2 | chr2:150408816-150434259 |
| 3310 | Apoa1 | NM_009692.4 | chr9:46036712-46038552 |
| 3311 | Apoa1bp | NM_144897.3 | chr3:87860444-87862417 |
| 3312 | Apoa2 | NM_013474.2 | chr1:173155184-173156510 |
| 3313 | Apoa4 | NM_007468.2 | chr9:46048926-46051541 |
| 3314 | Apoa5 | NM_080434.3 | chr9:46076690-46080002 |
| 3315 | Apob | NM_009693.2 | chr12:7984482-8023645 |
| 3316 | Apobec1 | NM_001134391.1 | chr6:122527809-122552462 |
| 3317 | Apobec1 | NM_031159.2 | chr6:122527809-122552462 |
| 3318 | Apobec2 | NM_009694.3 | chr17:48558555-48572053 |
| 3319 | Apobec3 | NM_001160415.1 | chr15:79719961-79738859 |
| 3320 | Apobec3 | NM_030255.3 | chr15:79719961-79738859 |
| 3321 | Apobec4 | NM_001081197.1 | chr1:154597680-154604674 |
| 3322 | Apobr | NM_138310.1 | chr7:133728521-133732606 |
| 3323 | Apoc1 | NM_001110009.2 | chr7:20274828-20278008 |
| 3324 | Apoc1 | NM_007469.5 | chr7:20274828-20278008 |
| 3325 | Apoc2 | NM_001277944.1 | chr7:20256927-20263290 |
| 3326 | Apoc3 | NM_001289755.1 | chr9:46041132-46043719 |
| 3327 | Apoc3 | NM_001289756.1 | chr9:46041132-46043719 |
| 3328 | Apoc3 | NM_001289833.1 | chr9:46041132-46043719 |
| 3329 | Apoc3 | NM_023114.4 | chr9:46041132-46043719 |
| 3330 | Apoc4 | NM_007385.3 | chr7:20263432-20266809 |
| 3331 | Apod | NM_007470.3 | chr16:31296277-31314682 |
| 3332 | Apoe | NM_009696.4 | chr7:20281592-20284515 |
| 3333 | Apof | NM_133997.2 | chr10:127705052-127707207 |
| 3334 | Apoh | NM_013475.4 | chr11:108256610-108275710 |
| 3335 | Apol10a | NM_177744.4 | chr15:77307476-77321499 |
| 3336 | Apol10b | NM_177820.4 | chr15:77414587-77426555 |
| 3337 | Apol11a | NM_001177533.1 | chr15:77338700-77347749 |
| 3338 | Apol11b | NM_001143686.1 | chr15:77464380-77473716 |
| 3339 | Apol6 | NM_001163621.1 | chr15:76845916-76887538 |
| 3340 | Apol6 | NM_028010.1 | chr15:76845916-76887538 |
| 3341 | Apol7a | NM_001164640.1 | chr15:77218646-77229540 |
| 3342 | Apol7a | NM_029419.2 | chr15:77218646-77229540 |
| 3343 | Apol7b | NM_001024842.2 | chr15:77252638-77277890 |
| 3344 | Apol7b | NM_001024848.2 | chr15:77529318-77549718 |
| 3345 | Apol7c | NM_175391.4 | chr15:77355296-77363745 |
| 3346 | Apol7d | NR_040308.1 | chr1:71699908-71709417 |
| 3347 | Apol8 | NM_001081970.1 | chr15:77579042-77585659 |
| 3348 | Apol9a | NM_001162883.1 | chr15:77234218-77241510 |
| 3349 | Apol9a | NM_173786.1 | chr15:77234218-77241510 |
| 3350 | Apol9b | NM_001168660.1 | chr15:77559501-77566812 |
| 3351 | Apol9b | NM_173743.4 | chr15:77559501-77566812 |
| 3352 | Apold1 | NM_001109914.1 | chr6:134932018-134936854 |
| 3353 | Apom | NM_018816.1 | chr17:35265941-35268697 |
| 3354 | Apon | NM_133996.3 | chr10:127691186-127692957 |
| 3355 | Apoo | NM_001199337.1 | chrX:91612448-91662431 |
| 3356 | Apoo | NM_001199338.1 | chrX:91612448-91662431 |
| 3357 | Apoo | NM_001199339.1 | chrX:91612448-91662431 |
| 3358 | Apoo | NM_026673.4 | chrX:91612448-91662431 |
| 3359 | Apoot | NM_026565.2 | chrX:109425016-109486039 |
| 3360 | Apoo-ps | NR_004438.1 | chrX:91612463-91643541 |
| 3361 | Apopt1 | NM_001163388.1 | chr12:112951479-112993266 |
| 3362 | Apopt1 | NM_026511.2 | chr12:112951479-112993266 |
| 3363 | App | NM_001198823.1 | chr16:84954680-85173952 |
| 3364 | App | NM_001198824.1 | chr16:84954680-85173952 |
| 3365 | App | NM_001198825.1 | chr16:84954680-85173952 |
| 3366 | App | NM_001198826.1 | chr16:84954680-85173952 |
| 3367 | App | NM_007471.3 | chr16:84954680-85173952 |
| 3368 | Appbp2 | NM_025825.3 | chr11:85004811-85048622 |
| 3369 | Appl1 | NM_145221.2 | chr14:27732173-27783737 |
| 3370 | Appl2 | NM_145220.2 | chr10:83062778-83111409 |
| 3371 | Aprt | NM_009698.2 | chr8:125098536-125100807 |
| 3372 | Aptx | NM_001025444.3 | chr4:40629110-40650227 |
| 3373 | Aptx | NM_001025445.2 | chr4:40629110-40650227 |
| 3374 | Aptx | NM_025545.4 | chr4:40629110-40650227 |
| 3375 | Aqp1 | NM_007472.2 | chr6:55286292-55298549 |
| 3376 | Aqp11 | NM_175105.3 | chr7:104874888-104886757 |
| 3377 | Aqp12 | NM_001159658.1 | chr1:94902910-94908846 |
| 3378 | Aqp12 | NM_177587.2 | chr1:94902910-94908846 |
| 3379 | Aqp2 | NM_009699.3 | chr15:99409486-99414976 |
| 3380 | Aqp3 | NM_016689.2 | chr4:41039756-41045216 |
| 3381 | Aqp4 | NM_009700.2 | chr18:15547902-15562193 |
| 3382 | Aqp5 | NM_009701.4 | chr15:99431830-99425260 |
| 3383 | Aqp6 | NM_175087.4 | chr15:99431830-99435908 |
| 3384 | Aqp7 | NM_007473.4 | chr4:40980106-40995169 |
| 3385 | Aqp8 | NM_001109045.1 | chr7:130605807-130611517 |
| 3386 | Aqp8 | NM_007474.2 | chr7:130605807-130611517 |
| 3387 | Aqp9 | NM_001271843.1 | chr9:70958465-71011096 |
| 3388 | Aqp9 | NM_022026.3 | chr9:70958465-71011096 |
| 3389 | Aqp9 | NR_073483.1 | chr9:70958465-71011096 |
| 3390 | Aqr | NM_001290788.1 | chr2:113926896-114001075 |
| 3391 | Aqr | NM_009702.3 | chr2:113926896-114001075 |
| 3392 | Ar | NM_013476.4 | chrX:95345088-95512486 |
| 3393 | Araf | NM_001159645.1 | chrX:20425668-20498044 |
| 3394 | Araf | NM_009703.2 | chrX:20425668-20498044 |
| 3395 | Arap1 | NM_001040111.1 | chr7:108496582-108561100 |
| 3396 | Arap1 | NM_001040112.1 | chr7:108496582-108561100 |
| 3397 | Arap1 | NM_027180.2 | chr7:108496582-108561100 |
| 3398 | Arap1 | NM_198096.1 | chr7:108496582-108561100 |
| 3399 | Arap2 | NM_178407.3 | chr5:62993684-63157416 |
| 3400 | Arap3 | NM_001205336.1 | chr18:38132276-38158623 |
| 3401 | Arap3 | NM_139206.2 | chr18:38132276-38158623 |
| 3402 | Arc | NM_012776684.3 | chr15:74499510-74503000 |
| 3403 | Arc | NM_018790.1 | chr15:74499510-74503000 |
| 3404 | Arcn1 | NM_145985.4 | chr9:44550227-44575891 |
| 3405 | Areg | NM_009704.3 | chr5:91568640-91577458 |
| 3406 | Arel1 | NM_178065.4 | chr12:86259098-86311836 |
| 3407 | Arf1 | NM_001130408.1 | chr11:59024913-59041769 |
| 3408 | Arf1 | NM_007476.3 | chr11:59024913-59041769 |
| 3409 | Arf2 | NM_007477.5 | chr11:103828184-103846650 |
| 3410 | Arf3 | NM_007478.3 | chr15:98568056-98593549 |
| 3411 | Arf4 | NM_007479.3 | chr14:27457682-27476744 |

Fig. 25 - 19

| | | | |
|---|---|---|---|
| 3412 | Arf5 | NM_007480.1 | chr6:28373639-28376499 |
| 3413 | Arf6 | NM_007481.3 | chr12:70473136-70476967 |
| 3414 | Arfgap1 | NM_001177706.1 | chr2:180701929-180717229 |
| 3415 | Arfgap1 | NM_001177707.1 | chr2:180701929-180717229 |
| 3416 | Arfgap1 | NM_001177708.1 | chr2:180701929-180717229 |
| 3417 | Arfgap1 | NM_001177709.1 | chr2:180701929-180717229 |
| 3418 | Arfgap1 | NM_001177710.1 | chr2:180701929-180717229 |
| 3419 | Arfgap1 | NM_145760.3 | chr2:180701929-180717229 |
| 3420 | Arfgap2 | NM_001166024.1 | chr2:91105271-91117528 |
| 3421 | Arfgap2 | NM_023854.2 | chr2:91105271-91117528 |
| 3422 | Arfgap3 | NM_025445.4 | chr15:83130169-83180677 |
| 3423 | Arfgef1 | NM_001102430.1 | chr1:10127587-10222751 |
| 3424 | Arfgef2 | NM_001085495.2 | chr2:166631080-166723551 |
| 3425 | Arfip1 | NM_001081093.2 | chr3:84299985-84386547 |
| 3426 | Arfip2 | NM_029802.3 | chr7:112782714-112788930 |
| 3427 | Arfrp1 | NM_001165991.1 | chr2:181092394-181115498 |
| 3428 | Arfrp1 | NM_001165992.1 | chr2:181092394-181115498 |
| 3429 | Arfrp1 | NM_001165995.1 | chr2:181092394-181115498 |
| 3430 | Arfrp1 | NM_029702.4 | chr2:181092394-181115498 |
| 3431 | Arfrp1 | NR_028585.1 | chr2:181092394-181115498 |
| 3432 | Arg1 | NM_007482.3 | chr10:24635012-24647276 |
| 3433 | Arg2 | NM_009705.3 | chr12:80231775-80257288 |
| 3434 | Arglu1 | NM_176849.3 | chr8:8666576-8690537 |
| 3435 | Arhgap1 | NM_001145902.1 | chr2:91490274-91512477 |
| 3436 | Arhgap1 | NM_146114.3 | chr2:91490274-91512477 |
| 3437 | Arhgap1 | NR_027371.1 | chr2:91490274-91512477 |
| 3438 | Arhgap1 | NR_027372.1 | chr2:91490274-91512477 |
| 3439 | Arhgap1 | NR_027373.1 | chr2:91490274-91512477 |
| 3440 | Arhgap10 | NM_030113.2 | chr8:79774265-80041806 |
| 3441 | Arhgap11a | NM_181416.3 | chr2:113671849-113688818 |
| 3442 | Arhgap12 | NM_001039692.1 | chr18:6024447-6136096 |
| 3443 | Arhgap12 | NM_029277.1 | chr18:6024447-6136096 |
| 3444 | Arhgap15 | NM_001025377.1 | chr2:43604343-44243143 |
| 3445 | Arhgap15 | NM_153820.3 | chr2:43604343-44243143 |
| 3446 | Arhgap15os | NR_040622.1 | chr2:43914758-43920844 |
| 3447 | Arhgap17 | NM_001122640.1 | chr7:130422662-130513429 |
| 3448 | Arhgap17 | NM_001122641.1 | chr7:130422662-130513429 |
| 3449 | Arhgap17 | NM_001122642.1 | chr7:130422662-130513429 |
| 3450 | Arhgap17 | NM_001122643.1 | chr7:130422662-130513429 |
| 3451 | Arhgap17 | NM_144529.2 | chr7:130422662-130513429 |
| 3452 | Arhgap18 | NM_176837.2 | chr10:26492317-26638454 |
| 3453 | Arhgap19 | NM_001163496.1 | chr19:41841077-41876574 |
| 3454 | Arhgap19 | NM_027667.3 | chr19:41841077-41876574 |
| 3455 | Arhgap20 | NM_175535.3 | chr9:51573457-51661164 |
| 3456 | Arhgap20os | NR_033560.1 | chr9:51647598-51683990 |
| 3457 | Arhgap21 | NM_001081364.3 | chr2:20769545-20889348 |
| 3458 | Arhgap21 | NM_001128084.2 | chr2:20769545-20889348 |
| 3459 | Arhgap22 | NM_153800.4 | chr14:34030008-34183122 |
| 3460 | Arhgap23 | NM_021493.2 | chr11:97311474-97363714 |
| 3461 | Arhgap24 | NM_001286468.1 | chr5:102910409-103326956 |
| 3462 | Arhgap24 | NM_029270.2 | chr5:102910409-103326956 |
| 3463 | Arhgap24 | NM_146161.3 | chr5:102910409-103326956 |
| 3464 | Arhgap25 | NM_001037727.2 | chr6:87408538-87483253 |
| 3465 | Arhgap25 | NM_001286610.1 | chr6:87408538-87483253 |
| 3466 | Arhgap25 | NM_175476.4 | chr6:87408538-87483253 |
| 3467 | Arhgap25 | NR_104483.1 | chr6:87408538-87483253 |
| 3468 | Arhgap26 | NM_175164.4 | chr18:39151798-39535939 |
| 3469 | Arhgap27 | NM_001205236.1 | chr11:103192797-103225006 |
| 3470 | Arhgap27 | NM_133715.5 | chr11:103192797-103225006 |
| 3471 | Arhgap27 | NM_183288.3 | chr11:103192797-103225006 |
| 3472 | Arhgap27os3 | NR_045346.1 | chr11:103206067-103211440 |
| 3473 | Arhgap28 | NM_172964.4 | chr17:68192047-68353448 |
| 3474 | Arhgap29 | NM_172525.2 | chr3:121656243-121719071 |
| 3475 | Arhgap30 | NM_001005508.2 | chr1:173319090-173340370 |
| 3476 | Arhgap31 | NM_020260.2 | chr16:38598455-38713148 |
| 3477 | Arhgap32 | NM_001195632.1 | chr9:31923720-32073096 |
| 3478 | Arhgap32 | NM_177379.4 | chr9:31923720-32073096 |
| 3479 | Arhgap33 | NM_001289670.1 | chr7:31307244-31320079 |
| 3480 | Arhgap33 | NM_001289682.1 | chr7:31307244-31320079 |
| 3481 | Arhgap33 | NM_178252.3 | chr7:31307244-31320079 |
| 3482 | Arhgap33os | NR_036630.1 | chr7:31300140-31307212 |
| 3483 | Arhgap35 | NM_172739.4 | chr7:17079821-17200342 |
| 3484 | Arhgap36 | NM_001163123.1 | chrX:46823626-46853427 |
| 3485 | Arhgap39 | NM_001168288.1 | chr15:76554414-76648600 |
| 3486 | Arhgap39 | NM_198420.2 | chr15:76554414-76648600 |
| 3487 | Arhgap4 | NM_001162623.1 | chrX:71137440-71156637 |
| 3488 | Arhgap4 | NM_001162424.1 | chrX:71137440-71156637 |
| 3489 | Arhgap4 | NM_138630.2 | chrX:71137440-71156637 |
| 3490 | Arhgap40 | NM_001145016.1 | chr2:158338531-158376364 |
| 3491 | Arhgap42 | NM_027823.1 | chr9:8994953-9239013 |
| 3492 | Arhgap44 | NM_001099288.1 | chr11:64792536-64976463 |
| 3493 | Arhgap44 | NM_175003.3 | chr11:64792536-64976463 |
| 3494 | Arhgap5 | NM_009706.2 | chr12:53617063-53668838 |
| 3495 | Arhgap6 | NM_001287530.1 | chrX:165233030-165742372 |
| 3496 | Arhgap6 | NM_009707.4 | chrX:165233030-165742372 |
| 3497 | Arhgap6 | NM_178754.3 | chrX:165233030-165742372 |
| 3498 | Arhgap6 | NR_109847.1 | chrX:165233030-165742372 |
| 3499 | Arhgap8 | NM_001164627.1 | chr15:84545058-84602637 |
| 3500 | Arhgap8 | NM_001164628.1 | chr15:84545058-84602637 |
| 3501 | Arhgap8 | NM_001205334.1 | chr15:84545058-84602637 |
| 3502 | Arhgap8 | NM_028455.4 | chr15:84545058-84602637 |
| 3503 | Arhgap9 | NM_001285785.1 | chr10:126759019-126778635 |
| 3504 | Arhgap9 | NM_146011.2 | chr10:126759019-126778635 |
| 3505 | Arhgdia | NM_133796.7 | chr11:120438548-120442934 |
| 3506 | Arhgdib | NM_007486.5 | chr6:136872229-136890238 |
| 3507 | Arhgdig | NM_008113.3 | chr17:26336127-26338295 |
| 3508 | Arhgef1 | NM_001130150.1 | chr7:25688004-25711610 |
| 3509 | Arhgef1 | NM_001130151.1 | chr7:25688004-25711610 |
| 3510 | Arhgef1 | NM_001130152.1 | chr7:25688004-25711610 |
| 3511 | Arhgef1 | NM_001130153.1 | chr7:25688004-25711610 |
| 3512 | Arhgef1 | NM_008488.2 | chr7:25688004-25711610 |
| 3513 | Arhgef10 | NM_001037736.2 | chr8:14911662-15001085 |
| 3514 | Arhgef10 | NM_172751.3 | chr8:14911662-15001085 |
| 3515 | Arhgef10l | NM_001112722.1 | chr4:140070399-140221820 |
| 3516 | Arhgef10l | NM_001112723.1 | chr4:140070399-140221820 |
| 3517 | Arhgef10l | NM_001290803.1 | chr4:140070399-140221820 |
| 3518 | Arhgef10l | NM_172415.3 | chr4:140070399-140221820 |
| 3519 | Arhgef11 | NM_001003912.1 | chr3:87422673-87541955 |
| 3520 | Arhgef12 | NM_027144.2 | chr9:42771924-42913801 |
| 3521 | Arhgef15 | NM_177566.3 | chr11:68756655-68770360 |
| 3522 | Arhgef16 | NM_001112744.1 | chr4:153652578-153674004 |
| 3523 | Arhgef17 | NM_001081116.1 | chr7:108018260-108080675 |
| 3524 | Arhgef18 | NM_133962.3 | chr8:3393007-3456600 |
| 3525 | Arhgef19 | NM_172520.2 | chr4:140798798-140813477 |
| 3526 | Arhgef2 | NM_001198911.1 | chr3:88420128-88451974 |
| 3527 | Arhgef2 | NM_001198912.1 | chr3:88420128-88451974 |
| 3528 | Arhgef2 | NM_001198913.1 | chr3:88420128-88451974 |
| 3529 | Arhgef2 | NM_008487.3 | chr3:88420128-88451974 |
| 3530 | Arhgef25 | NM_001166413.1 | chr10:126619576-126627110 |
| 3531 | Arhgef25 | NM_028027.3 | chr10:126619576-126627110 |
| 3532 | Arhgef26 | NM_001081295.1 | chr3:62142698-62266143 |
| 3533 | Arhgef28 | NM_012026.2 | chr13:98668549-98976320 |
| 3534 | Arhgef3 | NM_001289686.1 | chr14:27957178-28217097 |
| 3535 | Arhgef3 | NM_001289687.1 | chr14:27957178-28217097 |
| 3536 | Arhgef3 | NM_001289688.1 | chr14:27957178-28217097 |
| 3537 | Arhgef3 | NM_027871.2 | chr14:27957178-28217097 |
| 3538 | Arhgef33 | NM_001145452.1 | chr17:80706747-80788029 |
| 3539 | Arhgef37 | NM_177828.3 | chr18:61653447-61696190 |
| 3540 | Arhgef38 | NM_029953.1 | chr3:132822494-132897853 |
| 3541 | Arhgef39 | NM_001033772.2 | chr4:43509015-43512532 |
| 3542 | Arhgef4 | NM_183019.2 | chr1:34858566-34869599 |
| 3543 | Arhgef40 | NM_001145921.1 | chr14:52604507-52640408 |
| 3544 | Arhgef40 | NM_001145922.1 | chr14:52604507-52640408 |
| 3545 | Arhgef40 | NM_198249.4 | chr14:52604507-52640408 |
| 3546 | Arhgef5 | NM_133674.1 | chr6:43215642-43239319 |
| 3547 | Arhgef6 | NM_152801.2 | chrX:54484661-54591906 |
| 3548 | Arhgef7 | NM_001113517.1 | chr8:11728104-11835217 |
| 3549 | Arhgef7 | NM_001113518.1 | chr8:11728104-11835217 |
| 3550 | Arhgef7 | NM_017402.4 | chr8:11728104-11835217 |
| 3551 | Arhgef9 | NM_001033329.3 | chrX:92244273-92361878 |
| 3552 | Arhgef9 | NM_001290384.1 | chrX:92244273-92361878 |
| 3553 | Arhgef9 | NM_001290385.1 | chrX:92244273-92361878 |
| 3554 | Arid1a | NM_001080819.1 | chr4:133234923-133309526 |
| 3555 | Arid1b | NM_001085355.3 | chr17:4995073-5347656 |
| 3556 | Arid2 | NM_175251.4 | chr15:96117952-96235894 |
| 3557 | Arid3a | NM_001288625.1 | chr10:79389787-79417763 |
| 3558 | Arid3a | NM_001288626.1 | chr10:79389787-79417763 |
| 3559 | Arid3a | NM_007880.4 | chr10:79389787-79417763 |
| 3560 | Arid3b | NM_019689.2 | chr9:57638315-57682041 |
| 3561 | Arid3c | NM_001017362.2 | chr4:41676867-41678174 |
| 3562 | Arid3c | NM_001252622.1 | chr4:41676867-41678174 |
| 3563 | Arid4a | NM_001081195.1 | chr12:71116953-72200338 |
| 3564 | Arid4b | NM_194262.2 | chr13:14156050-14291870 |
| 3565 | Arid4b | NM_198122.2 | chr13:14156050-14291870 |
| 3566 | Arid5a | NM_001172205.1 | chr1:36364577-36380874 |
| 3567 | Arid5a | NM_001172206.1 | chr1:36364577-36380874 |
| 3568 | Arid5a | NM_001290726.1 | chr1:36364577-36380874 |
| 3569 | Arid5a | NM_001290727.1 | chr1:36364577-36380874 |
| 3570 | Arid5a | NM_145996.4 | chr1:36364577-36380874 |
| 3571 | Arid5a | NR_033310.1 | chr1:36364577-36380874 |
| 3572 | Arid5b | NM_023598.2 | chr10:67558340-67741474 |
| 3573 | Arih1 | NM_019927.2 | chr9:59236361-59334181 |
| 3574 | Arih2 | NM_011790.2 | chr9:108505273-108551711 |
| 3575 | Arl1 | NM_025859.3 | chr10:88194158-88205947 |
| 3576 | Arl10 | NM_019968.1 | chr13:54676373-54682489 |
| 3577 | Arl11 | NM_177337.3 | chr14:61928589-61930773 |
| 3578 | Arl13a | NM_028947.1 | chrX:130722039-130742569 |
| 3579 | Arl13b | NM_026577.3 | chr16:62793515-62846866 |
| 3580 | Arl14 | NM_027843.1 | chr3:69026340-69027540 |
| 3581 | Arl14ep | NM_001025102.1 | chr2:106802685-106814554 |
| 3582 | Arl14ep | NM_173750.2 | chr2:106802685-106814554 |
| 3583 | Arl14epl | NM_001033446.2 | chr18:47081468-47093876 |
| 3584 | Arl15 | NM_172595.3 | chr13:114584716-114947669 |
| 3585 | Arl16 | NM_197995.2 | chr11:120325640-120328914 |
| 3586 | Arl2 | NM_019722.3 | chr19:6134388-6141137 |
| 3587 | Arl2bp | NM_024191.2 | chr8:97190499-97198357 |
| 3588 | Arl2bp | NM_024269.4 | chr8:97190499-97198357 |
| 3589 | Arl3 | NM_019718.2 | chr19:46605598-46647575 |
| 3590 | Arl4a | NM_001039515.1 | chr12:40759877-40764574 |
| 3591 | Arl4a | NM_007487.3 | chr12:40759877-40764574 |
| 3592 | Arl4c | NM_177305.4 | chr1:90594800-90598766 |
| 3593 | Arl4d | NM_025404.3 | chr11:101526854-101529146 |
| 3594 | Arl5a | NM_182994.2 | chr2:52253470-52280394 |
| 3595 | Arl5b | NM_029466.2 | chr2:14976988-15006818 |
| 3596 | Arl5c | NM_207231.1 | chr11:97850893-97857487 |
| 3597 | Arl6 | NM_019665.3 | chr16:59613147-59639165 |
| 3598 | Arl6ip1 | NM_019419.2 | chr7:125262403-125273139 |
| 3599 | Arl6ip4 | NM_144509.2 | chr5:124566116-124568204 |
| 3600 | Arl6ip5 | NM_022992.2 | chr6:97160785-97183309 |
| 3601 | Arl6ip6 | NM_022989.4 | chr2:53051117-53078255 |

Fig. 25 - 20

| | | | | | | | | |
|---|---|---|---|---|---|---|---|---|
| 3602 | Arl8a | NM_026823.2 | chr1:137043416-137052845 | | 3697 | Arv1 | NM_026855.4 | chr8:127246038-127258023 |
| 3603 | Arl8b | NM_026011.3 | chr6:108733052-108773717 | | 3698 | Arvcf | NM_001272028.1 | chr16:18348274-18479166 |
| 3604 | Arl9 | NM_208935.1 | chr5:77433080-77438502 | | 3699 | Arvcf | NM_001272029.1 | chr16:18348274-18479166 |
| 3605 | Armc1 | NM_028840.2 | chr3:19032143-19063065 | | 3700 | Arvcf | NM_001272030.1 | chr16:18348274-18479166 |
| 3606 | Armc10 | NM_026034.4 | chr5:21151801-21168410 | | 3701 | Arvcf | NM_001272031.1 | chr16:18348274-18479166 |
| 3607 | Armc12 | NM_026790.3 | chr17:28667805-28675920 | | 3702 | Arvcf | NM_001272032.1 | chr16:18348274-18479166 |
| 3608 | Armc2 | NM_001034858.3 | chr10:41634796-41738188 | | 3703 | Arvcf | NM_033474.3 | chr16:18348274-18479166 |
| 3609 | Armc3 | NM_001081083.2 | chr2:19120744-19231870 | | 3704 | Arx | NM_007492.4 | chrX:90531984-90543694 |
| 3610 | Armc3 | NM_001271563.1 | chr2:19120744-19231870 | | 3705 | Arxes1 | NM_029541.3 | chrX:132567905-132569485 |
| 3611 | Armc3 | NM_001271564.1 | chr2:19120744-19231870 | | 3706 | Arxes2 | NM_029823.2 | chrX:132528358-132529898 |
| 3612 | Armc3 | NM_001271565.1 | chr2:19120744-19231870 | | 3707 | As3mt | NM_020577.2 | chr19:46781932-46815585 |
| 3613 | Armc4 | NM_001081393.1 | chr18:7088230-7297899 | | 3708 | Asah1 | NM_019734.2 | chr8:42425996-42460051 |
| 3614 | Armc5 | NM_146205.2 | chr7:135380871-135388614 | | 3709 | Asah2 | NM_018830.1 | chr19:32059140-32177630 |
| 3615 | Armc6 | NM_133972.2 | chr8:72744092-72758321 | | 3710 | Asap1 | NM_001276461.1 | chr15:63918401-64214481 |
| 3616 | Armc7 | NM_177778.4 | chr11:115336991-115351780 | | 3711 | Asap1 | NM_001276462.1 | chr15:63918401-64214481 |
| 3617 | Armc8 | NM_001166138.1 | chr9:99356661-99469318 | | 3712 | Asap1 | NM_001276463.1 | chr15:63918401-64214481 |
| 3618 | Armc8 | NM_028768.3 | chr9:99356661-99469318 | | 3713 | Asap1 | NM_001276467.1 | chr15:63918401-64214481 |
| 3619 | Armc9 | NM_027456.1 | chr1:88051354-88174859 | | 3714 | Asap1 | NM_010026.3 | chr15:63918401-64214481 |
| 3620 | Armc9 | NM_030184.2 | chr1:88051354-88174859 | | 3715 | Asap2 | NM_001004364.2 | chr12:21117616-21292098 |
| 3621 | Armcx1 | NM_001166377.1 | chrX:131252476-131256451 | | 3716 | Asap2 | NM_001098168.1 | chr12:21117616-21292098 |
| 3622 | Armcx1 | NM_001166378.1 | chrX:131252476-131256451 | | 3717 | Asap2 | NM_001135192.1 | chr12:21117616-21292098 |
| 3623 | Armcx1 | NM_001166379.1 | chrX:131252476-131256451 | | 3718 | Asap3 | NM_001008232.2 | chr4:135762279-135802488 |
| 3624 | Armcx1 | NM_001166380.1 | chrX:131252476-131256451 | | 3719 | Asb1 | NM_001039126.2 | chr1:93437141-93456167 |
| 3625 | Armcx1 | NM_030066.3 | chrX:131252476-131256451 | | 3720 | Asb1 | NM_023046.4 | chr1:93437141-93456167 |
| 3626 | Armcx2 | NM_001166397.1 | chrX:131338680-131343760 | | 3721 | Asb10 | NM_080444.4 | chr5:24038514-24046266 |
| 3627 | Armcx2 | NM_001166398.1 | chrX:131338680-131343760 | | 3722 | Asb11 | NM_026853.1 | chrX:160876032-160897032 |
| 3628 | Armcx2 | NM_026139.2 | chrX:131338680-131343760 | | 3723 | Asb12 | NM_080858.3 | chrX:92665537-92673468 |
| 3629 | Armcx3 | NM_027870.3 | chrX:131291107-131295995 | | 3724 | Asb13 | NM_001267724.1 | chr13:3633277-3651025 |
| 3630 | Armcx4 | NM_001202500.3 | chrX:131221057-131232311 | | 3725 | Asb13 | NM_178283.4 | chr13:3633277-3651025 |
| 3631 | Armcx5 | NM_001009575.5 | chrX:132277231-132281865 | | 3726 | Asb14 | NM_001170748.1 | chr14:27707789-27728443 |
| 3632 | Armcx6 | NM_001007578.2 | chrX:131282993-131285958 | | 3727 | Asb14 | NM_080856.4 | chr14:27707789-27728443 |
| 3633 | Arnt | NM_001037737.2 | chr3:95238311-95301161 | | 3728 | Asb15 | NM_080847.3 | chr6:24478143-24523164 |
| 3634 | Arnt | NM_009709.4 | chr3:95238311-95301161 | | 3729 | Asb16 | NM_148953.2 | chr11:102130136-102139375 |
| 3635 | Arnt2 | NM_007488.3 | chr7:91394784-91558548 | | 3730 | Asb17 | NM_025758.4 | chr3:153507211-153516579 |
| 3636 | Arntl | NM_001243048.1 | chr7:120350978-120457640 | | 3731 | Asb17os | NR_040373.1 | chr3:153513338-153515388 |
| 3637 | Arntl | NM_007489.4 | chr7:120350978-120457640 | | 3732 | Asb18 | NM_139152.1 | chr1:91849252-91911152 |
| 3638 | Arntl2 | NM_001289679.1 | chr6:146754051-146782051 | | 3733 | Asb2 | NM_023049.1 | chr12:104559351-104594211 |
| 3639 | Arntl2 | NM_001289680.1 | chr6:146754051-146782051 | | 3734 | Asb3 | NM_023906.3 | chr11:30854398-31002704 |
| 3640 | Arntl2 | NM_001289681.1 | chr6:146754051-146782051 | | 3735 | Asb4 | NM_023048.5 | chr6:5333385-5383021 |
| 3641 | Arntl2 | NM_172309.2 | chr6:146754051-146782051 | | 3736 | Asb5 | NM_029569.3 | chr8:55635683-55673189 |
| 3642 | Arpc1a | NM_019767.2 | chr5:145844737-145869625 | | 3737 | Asb6 | NM_133346.2 | chr2:30678617-30683820 |
| 3643 | Arpc1b | NM_023142.1 | chr5:145875124-145889055 | | 3738 | Asb7 | NM_080443.2 | chr7:73789456-73834447 |
| 3644 | Arpc2 | NM_029711.1 | chr1:74283123-74314787 | | 3739 | Asb7 | NR_003961.1 | chr7:73789456-73834447 |
| 3645 | Arpc3 | NM_019824.3 | chr5:122841936-122856187 | | 3740 | Asb8 | NM_001170710.1 | chr15:97965070-97996009 |
| 3646 | Arpc4 | NM_001170485.1 | chr6:113328106-113364565 | | 3741 | Asb8 | NM_001170711.1 | chr15:97965070-97996009 |
| 3647 | Arpc4 | NM_001170486.1 | chr6:113328106-113364565 | | 3742 | Asb8 | NM_030121.4 | chr15:97965070-97996009 |
| 3648 | Arpc4 | NM_026552.3 | chr6:113328106-113364565 | | 3743 | Asb9 | NM_027027.2 | chrX:160935834-160977684 |
| 3649 | Arpc5 | NM_026369.2 | chr1:154613671-154622710 | | 3744 | Ascc1 | NM_001199187.2 | chr10:59450656-59562738 |
| 3650 | Arpc5l | NM_028809.1 | chr2:38863658-38871392 | | 3745 | Ascc1 | NM_026937.3 | chr10:59450656-59562738 |
| 3651 | Arpp19 | NM_001142655.1 | chr9:74885420-74908120 | | 3746 | Ascc2 | NM_029291.1 | chr11:4537795-4583388 |
| 3652 | Arpp19 | NM_021548.1 | chr9:74885420-74908120 | | 3747 | Ascc3 | NM_198007.2 | chr10:50312474-50571008 |
| 3653 | Arpp21 | NM_001177615.1 | chr9:111967594-112251429 | | 3748 | Ascl1 | NM_008553.4 | chr10:86953785-86956405 |
| 3654 | Arpp21 | NM_001177616.1 | chr9:111967594-112251429 | | 3749 | Ascl2 | NM_008554.3 | chr7:150152726-150155169 |
| 3655 | Arpp21 | NM_001177617.1 | chr9:111967594-112251429 | | 3750 | Ascl3 | NM_020051.1 | chr7:116870978-116875246 |
| 3656 | Arpp21 | NM_001177618.1 | chr9:111967594-112251429 | | 3751 | Ascl4 | NM_001163614.1 | chr10:85391235-85392392 |
| 3657 | Arpp21 | NM_001177619.1 | chr9:111967594-112251429 | | 3752 | Ascl5 | NM_001270609.1 | chr1:137947380-137947947 |
| 3658 | Arpp21 | NM_001177620.1 | chr9:111967594-112251429 | | 3753 | Asf1a | NM_025541.3 | chr10:53316767-53329021 |
| 3659 | Arpp21 | NM_001177623.1 | chr9:111967594-112251429 | | 3754 | Asf1b | NM_024184.2 | chr8:86479592-86494094 |
| 3660 | Arpp21 | NM_028755.3 | chr9:111967594-112251429 | | 3755 | Asgr1 | NM_001291131.1 | chr11:69867625-69871397 |
| 3661 | Arpp21 | NM_033264.2 | chr9:111967594-112251429 | | 3756 | Asgr1 | NM_001291132.1 | chr11:69867625-69871397 |
| 3662 | Arr3 | NM_133205.3 | chrX:97800835-97813832 | | 3757 | Asgr1 | NM_009714.3 | chr11:69867625-69871397 |
| 3663 | Arrb1 | NM_177231.2 | chr7:106683995-106755281 | | 3758 | Asgr2 | NM_007493.3 | chr11:69906145-69919688 |
| 3664 | Arrb1 | NM_178220.3 | chr7:106683995-106755281 | | 3759 | Ash1l | NM_138679.5 | chr3:88768733-88883297 |
| 3665 | Arrb2 | NM_001271358.1 | chr11:70246081-70254330 | | 3760 | Ash2l | NM_001080793.2 | chr8:26928472-26958166 |
| 3666 | Arrb2 | NM_001271359.1 | chr11:70246081-70254330 | | 3761 | Ash2l | NM_001286207.1 | chr8:26928472-26958166 |
| 3667 | Arrb2 | NM_001271360.1 | chr11:70246081-70254330 | | 3762 | Ash2l | NM_011791.3 | chr8:26928472-26958166 |
| 3668 | Arrb2 | NM_145429.5 | chr11:70246081-70254330 | | 3763 | Asic1 | NM_001289791.1 | chr15:99501148-99551561 |
| 3669 | Arrdc1 | NM_001162485.1 | chr2:24780871-24790801 | | 3764 | Asic1 | NM_009597.1 | chr15:99501148-99551561 |
| 3670 | Arrdc1 | NM_178408.3 | chr2:24780871-24790801 | | 3765 | Asic2 | NM_001034013.2 | chr11:80693664-81781898 |
| 3671 | Arrdc1 | NR_027876.1 | chr2:24780871-24790801 | | 3766 | Asic2 | NM_007384.3 | chr11:80693664-81781898 |
| 3672 | Arrdc2 | NM_027560.1 | chr8:73359036-73363619 | | 3767 | Asic3 | NM_183000.2 | chr5:23919268-23923652 |
| 3673 | Arrdc3 | NM_001042591.1 | chr13:81022682-81035303 | | 3768 | Asic4 | NM_183022.3 | chr1:75447084-75470915 |
| 3674 | Arrdc4 | NM_001042592.1 | chr7:75881879-75894124 | | 3769 | Asic5 | NM_021370.2 | chr3:81800843-81825155 |
| 3675 | Arrdc4 | NM_025549.3 | chr7:75881879-75894124 | | 3770 | Asl | NM_133768.4 | chr5:130487372-130500201 |
| 3676 | Arrdc5 | NM_029799.1 | chr17:56433533-56439709 | | 3771 | Asna1 | NM_019652.1 | chr8:87541829-87549177 |
| 3677 | Arsa | NM_009713.4 | chr15:89302907-89307855 | | 3772 | Asns | NM_012055.3 | chr6:7625176-7643182 |
| 3678 | Arsb | NM_009712.3 | chr13:94541634-94712971 | | 3773 | Asnsd1 | NM_001290984.1 | chr1:53401460-53409596 |
| 3679 | Arsg | NM_001166177.1 | chr11:109301391-109434643 | | 3774 | Asnsd1 | NM_133728.3 | chr1:53401460-53409596 |
| 3680 | Arsg | NM_028710.3 | chr11:109301391-109434643 | | 3775 | Aspa | NM_023113.5 | chr11:73118489-73138139 |
| 3681 | Arsi | NM_001038499.1 | chr18:61071893-61077422 | | 3776 | Aspdh | NM_026690.1 | chr7:51720804-51723121 |
| 3682 | Arsj | NM_173451.3 | chr3:126066769-126143292 | | 3777 | Aspg | NM_001081169.1 | chr12:113344894-113365784 |
| 3683 | Arsk | NM_029847.4 | chr13:76197869-76236108 | | 3778 | Asph | NM_001177849.1 | chr4:9196463-9596491 |
| 3684 | Art1 | NM_009710.4 | chr7:109250256-109259662 | | 3779 | Asph | NM_001177850.1 | chr4:9196463-9596491 |
| 3685 | Art2a-ps | NM_007490.1 | chr7:108700966-108709379 | | 3780 | Asph | NM_001177851.1 | chr4:9196463-9596491 |
| 3686 | Art2a-ps | NR_033804.1 | chr7:108700966-108709379 | | 3781 | Asph | NM_001177852.1 | chr4:9196463-9596491 |
| 3687 | Art2b | NM_019915.2 | chr7:108727373-108729675 | | 3782 | Asph | NM_001177853.1 | chr4:9196463-9596491 |
| 3688 | Art3 | NM_181728.2 | chr5:92760867-92843653 | | 3783 | Asph | NM_001177855.1 | chr4:9196463-9596491 |
| 3689 | Art4 | NM_026639.1 | chr6:136796971-136806121 | | 3784 | Asph | NM_001177856.1 | chr4:9196463-9596491 |
| 3690 | Art5 | NM_001291354.1 | chr7:109245392-109248743 | | 3785 | Asph | NM_001290367.1 | chr4:9196463-9596491 |
| 3691 | Art5 | NM_007491.2 | chr7:109245392-109248743 | | 3786 | Asph | NM_023066.3 | chr4:9196463-9596491 |
| 3692 | Art5 | NR_111935.1 | chr7:109245392-109248743 | | 3787 | Asph | NM_133723.2 | chr4:9196463-9596491 |
| 3693 | Artn | NM_001284191.1 | chr4:117598764-117602368 | | 3788 | Asphd1 | NM_001039645.1 | chr7:134089521-134093095 |
| 3694 | Artn | NM_001284192.1 | chr4:117598764-117602368 | | 3789 | Asphd2 | NM_028386.1 | chr5:112814465-112821233 |
| 3695 | Artn | NM_001284193.1 | chr4:117598764-117602368 | | 3790 | Aspm | NM_009791.4 | chr1:141351349-141390665 |
| 3696 | Artn | NM_009711.4 | chr4:117598764-117602368 | | | | | |

Fig. 25 - 21

| | | | |
|---|---|---|---|
| 3792 | Aspn | NM_001172481.1 | chr13:49559427-49748100 |
| 3793 | Aspn | NM_025711.3 | chr13:49559427-49748100 |
| 3794 | Asprv1 | NM_026414.2 | chr6:86578167-86579698 |
| 3795 | Aspscr1 | NM_001164224.1 | chr11:120534286-120570760 |
| 3796 | Aspscr1 | NM_026877.2 | chr11:120534286-120570760 |
| 3797 | Aspscr1 | NM_198223.2 | chr11:120534286-120570760 |
| 3798 | Asrgl1 | NM_025610.3 | chr9:9186208-9210056 |
| 3799 | Ass1 | NM_007494.3 | chr2:31325789-31376190 |
| 3800 | Aste1 | NM_001164828.1 | chr9:105297721-105308086 |
| 3801 | Aste1 | NM_025651.4 | chr9:105297721-105308086 |
| 3802 | Astl | NM_001291003.1 | chr2:127164374-127183391 |
| 3803 | Astl | NM_172539.3 | chr2:127164374-127183391 |
| 3804 | Astn1 | NM_001205204.1 | chr1:160292434-160621917 |
| 3805 | Astn1 | NM_007495.4 | chr1:160292434-160621917 |
| 3806 | Astn2 | NM_019514.3 | chr4:65041836-66065517 |
| 3807 | Astn2 | NM_207109.2 | chr4:65041836-66065517 |
| 3808 | Asun | NM_138757.2 | chr6:146498153-146526357 |
| 3809 | Asxl1 | NM_001039939.1 | chr2:153171874-153229743 |
| 3810 | Asxl2 | NM_001270988.1 | chr12:3426856-3506849 |
| 3811 | Asxl2 | NM_172421.5 | chr12:3426856-3506849 |
| 3812 | Asxl3 | NM_001167777.1 | chr18:22503589-22688728 |
| 3813 | Asz1 | NM_023729.3 | chr6:18000963-18059061 |
| 3814 | Atad1 | NM_026487.3 | chr19:32747052-32786788 |
| 3815 | Atad2 | NM_027435.2 | chr15:57925601-57966637 |
| 3816 | Atad2b | NM_001099628.1 | chr12:4924158-5054216 |
| 3817 | Atad3a | NM_179203.3 | chr4:155114748-155135207 |
| 3818 | Atad3aos | NR_027971.1 | chr4:155135300-155137669 |
| 3819 | Atad3aos | NR_027927.1 | chr4:155135300-155137669 |
| 3820 | Atad5 | NM_001029856.2 | chr11:79902901-79949293 |
| 3821 | Atat1 | NM_001142744.1 | chr17:36034540-36047013 |
| 3822 | Atat1 | NM_001142745.1 | chr17:36034540-36047013 |
| 3823 | Atat1 | NM_028476.4 | chr17:36034540-36047013 |
| 3824 | Atcay | NM_178662.3 | chr10:80667258-80693524 |
| 3825 | Atcayos | NR_015477.1 | chr10:80657436-80671115 |
| 3826 | Ate1 | NM_001029895.3 | chr7:137535007-137663883 |
| 3827 | Ate1 | NM_001130054.2 | chr7:137535007-137663883 |
| 3828 | Ate1 | NM_001271343.1 | chr7:137535007-137663883 |
| 3829 | Ate1 | NM_013799.3 | chr7:137535007-137663883 |
| 3830 | Atf1 | NM_007497.3 | chr15:100058289-100091679 |
| 3831 | Atf2 | NM_001025093.2 | chr2:73654565-73730696 |
| 3832 | Atf2 | NM_001284369.1 | chr2:73654565-73730696 |
| 3833 | Atf2 | NM_001284370.1 | chr2:73654565-73730696 |
| 3834 | Atf2 | NM_001284371.1 | chr2:73654565-73730696 |
| 3835 | Atf2 | NM_001284372.1 | chr2:73654565-73730696 |
| 3836 | Atf2 | NM_001284373.1 | chr2:73654565-73730696 |
| 3837 | Atf2 | NM_001284374.1 | chr2:73654565-73730696 |
| 3838 | Atf2 | NM_001284376.1 | chr2:73654565-73730696 |
| 3839 | Atf2 | NM_009715.3 | chr2:73654565-73730696 |
| 3840 | Atf3 | NM_007498.3 | chr1:192994175-193007212 |
| 3841 | Atf4 | NM_001287180.1 | chr15:80085613-80087975 |
| 3842 | Atf4 | NM_009716.3 | chr15:80085613-80087975 |
| 3843 | Atf5 | NM_030693.2 | chr7:52067625-52104449 |
| 3844 | Atf5 | NR_033136.1 | chr7:52067625-52104449 |
| 3845 | Atf6 | NM_001081304.1 | chr1:172634587-172797902 |
| 3846 | Atf6b | NM_017406.4 | chr17:34784090-34792019 |
| 3847 | Atf7 | NM_146065.1 | chr15:102367074-102455852 |
| 3848 | Atf7ip | NM_019426.2 | chr6:136467371-136555900 |
| 3849 | Atf7ip2 | NM_029253.1 | chr16:10192998-10243144 |
| 3850 | Atf7ip2 | NM_153123.2 | chr16:10192998-10243144 |
| 3851 | Atg10 | NM_025770.3 | chr13:91074953-91363592 |
| 3852 | Atg101 | NM_026566.2 | chr15:101114731-101121365 |
| 3853 | Atg12 | NM_026217.3 | chr18:46892070-46901223 |
| 3854 | Atg13 | NM_145528.3 | chr2:91514768-91550749 |
| 3855 | Atg14 | NM_172599.4 | chr14:48160567-48188109 |
| 3856 | Atg16l1 | NM_001205391.1 | chr1:89652585-89689003 |
| 3857 | Atg16l1 | NM_001205392.1 | chr1:89652585-89689003 |
| 3858 | Atg16l1 | NM_029846.4 | chr1:89652585-89689003 |
| 3859 | Atg16l2 | NM_001111111.1 | chr7:108438129-108450602 |
| 3860 | Atg2a | NM_194348.3 | chr19:6241667-6262304 |
| 3861 | Atg2b | NM_029654.4 | chr12:106851748-106923451 |
| 3862 | Atg3 | NM_026402.3 | chr16:45158941-45188651 |
| 3863 | Atg4a | NM_174875.3 | chrX:137491455-137598813 |
| 3864 | Atg4b | NM_174744.3 | chr1:95651609-95686106 |
| 3865 | Atg4c | NM_001145967.1 | chr4:98860624-98926478 |
| 3866 | Atg4c | NM_175029.3 | chr4:98860624-98926478 |
| 3867 | Atg4d | NM_153528.5 | chr9:21060729-21079281 |
| 3868 | Atg5 | NM_053069.5 | chr10:43988164-44084097 |
| 3869 | Atg7 | NM_001253717.1 | chr6:114593118-114810632 |
| 3870 | Atg7 | NM_001253718.1 | chr6:114593118-114810632 |
| 3871 | Atg7 | NM_028835.4 | chr6:114593118-114810632 |
| 3872 | Atg9a | NM_001003917.3 | chr1:75177434-75188584 |
| 3873 | Atg9a | NM_001288612.1 | chr1:75177434-75188584 |
| 3874 | Atg9a | NM_001288613.1 | chr1:75177434-75188584 |
| 3875 | Atg9a | NR_109938.1 | chr1:75177434-75188584 |
| 3876 | Atg9b | NM_001002897.3 | chr5:23889999-23897961 |
| 3877 | Ath1l | NM_145387.4 | chr7:148127479-148133557 |
| 3878 | Atic | NM_026025.3 | chr1:71603729-71625977 |
| 3879 | Atl1 | NM_178628.5 | chr12:70994092-71065072 |
| 3880 | Atl2 | NM_001286647.1 | chr17:80247729-80295463 |
| 3881 | Atl2 | NM_019717.3 | chr17:80247729-80295463 |
| 3882 | Atl2 | NM_178050.4 | chr17:80247729-80295463 |
| 3883 | Atl3 | NM_001163505.1 | chr19:7568529-7613099 |
| 3884 | Atl3 | NM_146091.4 | chr19:7568529-7613099 |
| 3885 | Atm | NM_007499.2 | chr9:53245226-53344776 |
| 3886 | Atmin | NM_177700.4 | chr8:119467292-119484345 |
| 3887 | Atn1 | NM_007881.4 | chr6:124692561-124706505 |
| 3888 | Atoh1 | NM_007500.4 | chr6:64679139-64681229 |
| 3889 | Atoh7 | NM_016864.1 | chr10:62562903-62563353 |
| 3890 | Atoh8 | NM_153778.3 | chr6:72156171-72185571 |
| 3891 | Atox1 | NM_009720.2 | chr11:55260144-55274640 |
| 3892 | Atp10a | NM_009728.2 | chr7:65913571-66084796 |
| 3893 | Atp10b | NM_176999.3 | chr11:42963378-43075787 |
| 3894 | Atp10d | NM_153389.1 | chr5:72594567-72690010 |
| 3895 | Atp10d | NR_003966.1 | chr5:72594567-72690010 |
| 3896 | Atp11a | NM_015804.3 | chr8:12757016-12868728 |
| 3897 | Atp11b | NM_029570.3 | chr3:35653059-35755198 |
| 3898 | Atp11c | NM_001001798.2 | chrX:57476466-57657156 |
| 3899 | Atp11c | NM_001037863.1 | chrX:57476466-57657156 |
| 3900 | Atp12a | NM_138652.2 | chr14:56983984-57007388 |
| 3901 | Atp13a1 | NM_133224.2 | chr8:72315061-72331647 |
| 3902 | Atp13a2 | NM_001146366.1 | chr4:140542787-140563616 |
| 3903 | Atp13a2 | NM_029097.2 | chr4:140542787-140563616 |
| 3904 | Atp13a3 | NM_001128094.1 | chr16:30312509-30388616 |
| 3905 | Atp13a3 | NM_001128096.1 | chr16:30312509-30388616 |
| 3906 | Atp13a4 | NM_001164612.1 | chr16:29396123-29544950 |
| 3907 | Atp13a4 | NM_001164613.1 | chr16:29396123-29544950 |
| 3908 | Atp13a4 | NM_172613.4 | chr16:29396123-29544950 |
| 3909 | Atp13a5 | NM_001284375.1 | chr16:29231999-29378818 |
| 3910 | Atp13a5 | NM_175650.4 | chr16:29231999-29378818 |
| 3911 | Atp1a1 | NM_144900.2 | chr3:101380141-101408630 |
| 3912 | Atp1a2 | NM_178405.3 | chr1:174201839-174228195 |
| 3913 | Atp1a3 | NM_001290469.1 | chr7:25763185-25790956 |
| 3914 | Atp1a3 | NM_144921.1 | chr7:25763185-25790956 |
| 3915 | Atp1a4 | NM_013734.1 | chr1:174153638-174188555 |
| 3916 | Atp1b1 | NM_009721.6 | chr1:166367230-166388486 |
| 3917 | Atp1b2 | NM_013415.5 | chr11:69413251-69419462 |
| 3918 | Atp1b3 | NM_007502.4 | chr9:96233094-96264718 |
| 3919 | Atp1b4 | NM_001290389.1 | chrX:35669298-35689961 |
| 3920 | Atp1b4 | NM_133690.3 | chrX:35669298-35689961 |
| 3921 | Atp2a1 | NM_007504.2 | chr7:133589374-133606587 |
| 3922 | Atp2a2 | NM_001110140.3 | chr5:122903521-122952234 |
| 3923 | Atp2a2 | NM_009722.3 | chr5:122903521-122952234 |
| 3924 | Atp2a2 | NR_027838.1 | chr5:122903521-122952234 |
| 3925 | Atp2a3 | NM_001163336.1 | chr11:72774670-72806545 |
| 3926 | Atp2a3 | NM_001163337.1 | chr11:72774670-72806545 |
| 3927 | Atp2a3 | NM_016745.3 | chr11:72774670-72806545 |
| 3928 | Atp2b1 | NM_026482.2 | chr10:98377785-98488777 |
| 3929 | Atp2b2 | NM_001036684.2 | chr6:113695661-113992074 |
| 3930 | Atp2b2 | NM_009723.5 | chr6:113695661-113992074 |
| 3931 | Atp2b3 | NM_177236.4 | chrX:70748424-70818609 |
| 3932 | Atp2b4 | NM_001167949.2 | chr1:135599250-135650324 |
| 3933 | Atp2b4 | NM_213616.4 | chr1:135599250-135650324 |
| 3934 | Atp2c1 | NM_001253831.1 | chr9:105313691-105423587 |
| 3935 | Atp2c1 | NM_001253834.1 | chr9:105313691-105423587 |
| 3936 | Atp2c1 | NM_001253836.1 | chr9:105313691-105423587 |
| 3937 | Atp2c1 | NM_175025.4 | chr9:105313691-105423587 |
| 3938 | Atp2c2 | NM_026922.1 | chr8:122223908-122281618 |
| 3939 | Atp4a | NM_001290627.1 | chr7:31497227-31510553 |
| 3940 | Atp4a | NM_018731.3 | chr7:31497227-31510553 |
| 3941 | Atp4b | NM_009724.2 | chr8:13396208-13396778 |
| 3942 | Atp5a1 | NM_007505.2 | chr18:78012506-78021607 |
| 3943 | Atp5b | NM_016774.3 | chr10:127520363-127527444 |
| 3944 | Atp5c1 | NM_001112738.1 | chr2:9977658-10002137 |
| 3945 | Atp5c1 | NM_020615.4 | chr2:9977658-10002137 |
| 3946 | Atp5d | NM_025313.2 | chr10:79605059-79608563 |
| 3947 | Atp5e | NM_025983.3 | chr2:174286575-174289602 |
| 3948 | Atp5f1 | NM_009725.4 | chr3:105745596-105763166 |
| 3949 | Atp5g1 | NM_001161419.1 | chr11:95934106-95937008 |
| 3950 | Atp5g1 | NM_007506.6 | chr11:95934106-95937008 |
| 3951 | Atp5g2 | NM_026468.2 | chr15:102493298-102501478 |
| 3952 | Atp5g3 | NM_175015.3 | chr2:73748506-73749351 |
| 3953 | Atp5h | NM_027862.1 | chr11:115277010-115281233 |
| 3954 | Atp5j | NM_016755.3 | chr16:84828116-84835870 |
| 3955 | Atp5j2 | NM_020582.2 | chr5:145944574-145952461 |
| 3956 | Atp5k | NM_007507.2 | chr5:108862271-108863397 |
| 3957 | Atp5l | NM_013795.5 | chr9:44721330-44728825 |
| 3958 | Atp5o | NM_138597.2 | chr16:91925467-91931875 |
| 3959 | Atp5s | NM_026536.1 | chr12:70825948-70845645 |
| 3960 | Atp5sl | NM_001290487.1 | chr7:26404432-26410569 |
| 3961 | Atp5sl | NM_025504.4 | chr7:26404432-26410569 |
| 3962 | Atp6ap1 | NM_018794.4 | chrX:71542435-71550060 |
| 3963 | Atp6ap1l | NM_001145879.1 | chr13:91023053-91044960 |
| 3964 | Atp6ap2 | NM_027439.4 | chrX:12164884-12194177 |
| 3965 | Atp6v0a1 | NM_001243049.1 | chr11:100870765-100925031 |
| 3966 | Atp6v0a1 | NM_001243050.1 | chr11:100870765-100925031 |
| 3967 | Atp6v0a1 | NM_001243051.1 | chr11:100870765-100925031 |
| 3968 | Atp6v0a1 | NM_016920.3 | chr11:100870765-100925031 |
| 3969 | Atp6v0a2 | NM_011596.5 | chr5:125079632-125204825 |
| 3970 | Atp6v0a4 | NM_080467.3 | chr6:37998483-38074586 |
| 3971 | Atp6v0b | NM_033617.3 | chr4:117556934-117559934 |
| 3972 | Atp6v0c | NM_009729.3 | chr17:24300833-24306374 |
| 3973 | Atp6v0c-ps2 | NR_037854.1 | chr17:24300832-24306364 |
| 3974 | Atp6v0d1 | NM_013477.3 | chr8:108048369-108089940 |
| 3975 | Atp6v0d2 | NM_175406.3 | chr4:19803984-19849713 |
| 3976 | Atp6v0e | NM_025272.2 | chr17:26813340-26836591 |
| 3977 | Atp6v0e2 | NM_133764.3 | chr6:48487567-48491799 |
| 3978 | Atp6v1a | NM_007508.5 | chr16:44085516-44139132 |
| 3979 | Atp6v1b1 | NM_134157.2 | chr6:83693010-83708804 |
| 3980 | Atp6v1b2 | NM_007509.3 | chr8:71612635-71637616 |
| 3981 | Atp6v1c1 | NM_025494.3 | chr15:38591658-38622199 |

Fig. 25 - 22

| | | | | | | | |
|---|---|---|---|---|---|---|---|
| 3982 | Atp6v1c2 | NM_001159632.1 | chr12:17273400-17331536 | 4075 | AV039307 | NR_038350.1 | chr2:120676391-120796451 |
| 3983 | Atp6v1c2 | NM_133699.2 | chr12:17273400-17331536 | 4076 | AV051173 | NR_040442.1 | chr4:116357570-116358627 |
| 3984 | Atp6v1d | NM_023721.1 | chr12:79943968-79962625 | 4077 | AV320801 | NM_177918.1 | chrX:132029126-132039133 |
| 3985 | Atp6v1e1 | NM_007510.2 | chr6:120745261-120772703 | 4078 | AV320801 | NM_177918.1 | chrX:131702162-131712171 |
| 3986 | Atp6v1e2 | NM_029121.3 | chr17:87343448-87347227 | 4079 | Aven | NM_001165935.1 | chr2:112333120-112471410 |
| 3987 | Atp6v1f | NM_025381.2 | chr6:29417782-29420509 | 4080 | Aven | NM_028844.3 | chr2:112333120-112471410 |
| 3988 | Atp6v1g1 | NM_024173.2 | chr4:63205798-63211735 | 4081 | Avil | NM_009635.3 | chr10:126437764-126458050 |
| 3989 | Atp6v1g2 | NM_023179.3 | chr17:35373540-35375712 | 4082 | Avil9 | NM_030235.1 | chr6:56664898-56711905 |
| 3990 | Atp6v1g3 | NM_177397.3 | chr1:140170314-140186039 | 4083 | Avp | NM_009732.1 | chr2:130406412-130408277 |
| 3991 | Atp6v1h | NM_133826.4 | chr1:5073253-5152630 | 4084 | Avpi1 | NM_027106.4 | chr19:42197764-42203483 |
| 3992 | Atp7a | NM_001109757.2 | chrX:103222562-103323499 | 4085 | Avpr1a | NM_016847.2 | chr10:121885554-121890509 |
| 3993 | Atp7a | NM_009726.5 | chrX:103222562-103323499 | 4086 | Avpr1b | NM_011924.2 | chr1:133495690-133508577 |
| 3994 | Atp7b | NM_007511.2 | chr8:23104819-23170546 | 4087 | Avpr2 | NM_001276298.1 | chrX:71137440-71156637 |
| 3995 | Atp8a1 | NM_001038999.2 | chr5:68009377-68238670 | 4088 | Avpr2 | NM_001276299.1 | chrX:71137440-71156637 |
| 3996 | Atp8a1 | NM_001284345.1 | chr5:68009377-68238670 | 4089 | Avpr2 | NM_019404.2 | chrX:71137440-71156637 |
| 3997 | Atp8a1 | NM_009727.3 | chr5:68009377-68238670 | 4090 | AW011738 | NR_030671.1 | chr4:155577392-155580137 |
| 3998 | Atp8a2 | NM_015803.2 | chr14:60266577-60705671 | 4091 | AW046200 | NR_040698.1 | chr8:60130550-60142227 |
| 3999 | Atp8b1 | NM_001001488.3 | chr18:64688632-64820654 | 4092 | AW112010 | NR_102366.1 | chr19:11122101-11125056 |
| 4000 | Atp8b2 | NM_001081182.2 | chr3:89743402-89767254 | 4093 | AW146154 | NM_001033530.3 | chr7:48734243-48755260 |
| 4001 | Atp8b3 | NM_026094.3 | chr10:79982329-80001869 | 4094 | AW209491 | NM_001104646.1 | chr13:14722511-14730469 |
| 4002 | Atp8b4 | NM_001080944.3 | chr2:126146708-126317289 | 4095 | AW209491 | NM_134067.4 | chr13:14722511-14730469 |
| 4003 | Atp8b5 | NM_177195.3 | chr4:43280036-43386703 | 4096 | AW495222 | NR_045086.1 | chr13:94476055-94489130 |
| 4004 | Atp9a | NM_001289445.1 | chr2:168459937-168567636 | 4097 | AW549542 | NR_045702.1 | chr5:120020137-120030367 |
| 4005 | Atp9a | NM_001289446.1 | chr2:168459937-168567636 | 4098 | AW549877 | NM_145930.1 | chr15:3932034-3945752 |
| 4006 | Atp9a | NM_015731.3 | chr2:168459937-168567636 | 4099 | AW551984 | NM_001199556.1 | chr9:39394980-39411709 |
| 4007 | Atp9b | NM_001291569.1 | chr18:80930879-81130797 | 4100 | AW551984 | NM_178737.5 | chr9:39394980-39411709 |
| 4008 | Atp9b | NM_015805.3 | chr18:80930879-81130797 | 4101 | AW554918 | NM_001033532.3 | chr18:25327520-25625822 |
| 4009 | Atpaf1 | NM_181040.4 | chr4:115457418-115484919 | 4102 | AW822252 | NR_110489.1 | chr5:51000098-51019755 |
| 4010 | Atpaf2 | NM_145427.2 | chr11:60214126-60230601 | 4103 | Awat1 | NM_001081136.1 | chrX:97767585-97773545 |
| 4011 | Atpif1 | NM_007512.4 | chr4:132086469-132089574 | 4104 | Awat2 | NM_001290395.1 | chrX:97597560-97638056 |
| 4012 | Atr | NM_019864.1 | chr9:95758016-95852063 | 4105 | Awat2 | NM_177746.4 | chrX:97597560-97638056 |
| 4013 | Atraid | NM_027855.4 | chr5:31235515-31651218 | 4106 | Axin1 | NM_001159598.1 | chr17:26275630-26332756 |
| 4014 | Atraid | NM_212470.3 | chr5:31235515-31651218 | 4107 | Axin1 | NM_009733.2 | chr17:26275630-26332756 |
| 4015 | Atrip | NM_172774.3 | chr9:108962260-108976638 | 4108 | Axin2 | NM_015732.4 | chr11:108781662-108812095 |
| 4016 | Atrn | NM_009730.2 | chr2:130732231-130856062 | 4109 | Axl | NM_001190974.1 | chr7:26541518-26573752 |
| 4017 | Atrnl1 | NM_181415.1 | chr19:57685524-58207830 | 4110 | Axl | NM_001190975.1 | chr7:26541518-26573752 |
| 4018 | Atrx | NM_009530.2 | chrX:102992955-103124711 | 4111 | Axl | NM_009465.4 | chr7:26541518-26573752 |
| 4019 | Atxn1 | NM_001199304.1 | chr13:45645124-46060360 | 4112 | AY074887 | NM_145229.2 | chr9:54798064-54798761 |
| 4020 | Atxn1 | NM_001199305.1 | chr13:45645124-46060360 | 4113 | AY358078 | NM_194347.1 | chr14:52419720-52446034 |
| 4021 | Atxn1 | NM_009124.2 | chr13:45645124-46060360 | 4114 | AY512915 | NR_033559.1 | chr6:95240567-95283987 |
| 4022 | Atxn10 | NM_016843.3 | chr15:85166810-85294266 | 4115 | AY512931 | NR_033588.1 | chr8:46146055-46150772 |
| 4023 | Atxn1l | NM_001080930.1 | chr8:112250350-112261639 | 4116 | AY761184 | NM_001007582.3 | chr8:22812995-22814119 |
| 4024 | Atxn2 | NM_009125.2 | chr5:122161617-122264959 | 4117 | AY761185 | NM_001012640.2 | chr8:22083372-22084427 |
| 4025 | Atxn2l | NM_183020.1 | chr7:133635221-133646816 | 4118 | AY761185 | NM_001012640.2 | chr8_random:264606-265659 |
| 4026 | Atxn3 | NM_001167814.1 | chr12:106751642-106753458 | 4119 | Aym1 | NM_001012726.2 | chr5:113786313-113786841 |
| 4027 | Atxn3 | NM_029705.3 | chr12:103157110-103196453 | 4120 | Azgp1 | NM_013478.2 | chr5:138422748-138431460 |
| 4028 | Atxn7 | NM_139227.1 | chr14:14845004-14939815 | 4121 | Azi2 | NM_001048146.2 | chr9:117949639-118059314 |
| 4029 | Atxn7l1 | NM_001033436.3 | chr12:33987379-34053142 | 4122 | Azi2 | NM_001286507.1 | chr9:117949639-118059314 |
| 4030 | Atxn7l1 | NM_028139.5 | chr12:33832550-33936022 | 4123 | Azi2 | NM_001286508.1 | chr9:117949639-118059314 |
| 4031 | Atxn7l2 | NM_001289545.1 | chr3:108005145-108013445 | 4124 | Azi2 | NM_013727.4 | chr9:117949639-118059314 |
| 4032 | Atxn7l2 | NM_175183.5 | chr3:108005145-108013445 | 4125 | Azin1 | NM_001102458.1 | chr15:38417184-38449021 |
| 4033 | Atxn7l3 | NM_001098836.1 | chr11:102146274-102157943 | 4126 | Azin1 | NM_018745.5 | chr15:38417184-38449021 |
| 4034 | Atxn7l3 | NM_001098837.1 | chr11:102146274-102157943 | 4127 | B020004C17Rik | NM_001256060.1 | chr14:57633970-57637819 |
| 4035 | Atxn7l3b | NM_001033474.2 | chr10:112362483-112366082 | 4128 | B020004J07Rik | NM_001033790.3 | chr4:101507573-101516627 |
| 4036 | AU015228 | NM_001033197.2 | chr2:129926129-129929111 | 4129 | B020014A21Rik | NR_045946.1 | chr10:7213347-7221452 |
| 4037 | AU015791 | NR_102381.1 | chr12:106751642-106753458 | 4130 | B020018J22Rik | NR_045950.1 | chr2:113666494-113673549 |
| 4038 | AU015836 | NR_028320.1 | chrX:91213994-91220809 | 4131 | B020031M17Rik | NM_001033769.2 | chrUn_random:2889606-2891056 |
| 4039 | AU016765 | NR_045899.1 | chr17:64863428-64904930 | 4132 | B130006D01Rik | NR_028263.1 | chr11:95584899-95588087 |
| 4040 | AU018091 | NM_001004153.2 | chr7:3154659-3169204 | 4133 | B130024G19Rik | NR_045850.1 | chr7:77510269-77556032 |
| 4041 | AU018829 | NM_001200055.1 | chrUn_random:1383589-1396311 | 4134 | B130034C11Rik | NR_040375.1 | chr16:87496317-87504243 |
| 4042 | AU018829 | NM_001200055.1 | chr5_random:308680-321393 | 4135 | B230112J18Rik | NR_110475.1 | chr5:116762368-136768283 |
| 4043 | AU018829 | NM_001200055.1 | chrUn_random:838715-851429 | 4136 | B230118H07Rik | NM_026592.3 | chr2:101400938-101469143 |
| 4044 | AU018829 | NM_001200055.1 | chr5:95294540-95307276 | 4137 | B230119M05Rik | NR_045454.1 | chrX:131219160-131221001 |
| 4045 | AU018829 | NM_001200055.1 | chr5:95611642-95624361 | 4138 | B230206H07Rik | NR_033532.1 | chr7:148545077-148551009 |
| 4046 | AU018829 | NM_001200055.1 | chrUn_random:2204168-2216886 | 4139 | B230208H11Rik | NR_038027.1 | chr10:12636443-12642925 |
| 4047 | AU019823 | NM_001134902.1 | chr9:50412005-50433105 | 4140 | B230208H11Rik | NR_038028.1 | chr10:12636443-12642925 |
| 4048 | AU019823 | NM_212449.2 | chr9:50412005-50433105 | 4141 | B230209E15Rik | NR_045727.1 | chr7:68674295-68760213 |
| 4049 | AU019990 | NR_033468.1 | chr2:132423931-132478800 | 4142 | B230214G05Rik | NR_045281.1 | chr15:88145303-88203081 |
| 4050 | AU019990 | NR_033469.1 | chr2:132423931-132478800 | 4143 | B230216G23Rik | NM_001242345.1 | chr6:142361950-142368260 |
| 4051 | AU021063 | NR_045996.1 | chr15:101051678-101052586 | 4144 | B230216N24Rik | NR_037993.1 | chr1:99927700-99944370 |
| 4052 | AU021092 | NM_001033203.3 | chr16:5211911-5222392 | 4145 | B230217C12Rik | NM_001080935.1 | chr11:97702093-97704357 |
| 4053 | AU022252 | NM_001012400.2 | chr4:118897742-118905329 | 4146 | B230217O12Rik | NM_040316.1 | chr9:57397686-57435389 |
| 4054 | AU022751 | NM_001033213.3 | chrX:5658335-5660538 | 4147 | B230219D22Rik | NM_181278.2 | chr13:57794484-55804861 |
| 4055 | AU022751 | NM_001166433.1 | chrX:5658335-5660538 | 4148 | B230312C02Rik | NR_040745.1 | chr2:180105563-180120590 |
| 4056 | AU022754 | NR_040433.1 | chr15:85411572-85424138 | 4149 | B230319C09Rik | NM_028382.1 | chr6:83391748-83398316 |
| 4057 | AU022793 | NR_045719.1 | chr15:39794194-39799061 | 4150 | B230323A14Rik | NR_040765.1 | chr9:69608952-69678006 |
| 4058 | AU023762 | NR_040760.1 | chr9:113405863-113496270 | 4151 | B2m | NM_009735.3 | chr2:121973423-121978818 |
| 4059 | AU040320 | NM_001035525.1 | chr4:126430798-126645167 | 4152 | B330016D10Rik | NR_030695.1 | chr4:141102076-141104228 |
| 4060 | AU040320 | NM_001035526.1 | chr4:126430798-126645167 | 4153 | B3galnt1 | NM_020026.4 | chr3:69377840-69402882 |
| 4061 | AU040320 | NM_133886.2 | chr4:126430798-126645167 | 4154 | B3galnt2 | NM_178640.2 | chr13:14046941-14091335 |
| 4062 | AU040972 | NR_045305.1 | chr11:79295225-79297533 | 4155 | B3galt1 | NM_020283.4 | chr2:67942728-67960939 |
| 4063 | AU041133 | NM_001163064.1 | chr10:81590757-81615810 | 4156 | B3galt2 | NM_020025.4 | chr1:145487827-145497067 |
| 4064 | Auh | NM_016709.2 | chr13:52930478-53025046 | 4157 | B3galt4 | NM_019420.2 | chr17:34086856-34088433 |
| 4065 | Aup1 | NM_007517.4 | chr6:83004646-83007676 | 4158 | B3galt5 | NM_001122993.1 | chr16:96457407-96541465 |
| 4066 | Aurka | NM_001291185.1 | chr2:172181689-172196070 | 4159 | B3galt5 | NM_033149.3 | chr16:96457407-96541465 |
| 4067 | Aurka | NM_011497.4 | chr2:172181689-172196070 | 4160 | B3galt6 | NM_080445.4 | chr4:155363574-155366787 |
| 4068 | Aurkaip1 | NM_025338.4 | chr4:155205377-155207207 | 4161 | B3gat1 | NM_029792.1 | chr9:26559146-26568923 |
| 4069 | Aurkb | NM_011496.1 | chr11:68859144-68865164 | 4162 | B3gat2 | NM_172124.2 | chr1:23768765-23854697 |
| 4070 | Aurkc | NM_001080965.1 | chr7:6948095-6955802 | 4163 | B3gat3 | NM_024256.2 | chr19:8994882-9001726 |
| 4071 | Aurkc | NM_001080966.1 | chr7:6948095-6955802 | 4164 | B3gct | NM_001081204.1 | chr5:150480831-150565174 |
| 4072 | Aurkc | NM_020572.2 | chr7:6948095-6955802 | 4165 | B3gnt1 | NM_175383.2 | chr19:5038825-5041134 |
| 4073 | Auts2 | NM_177047.3 | chr5:131913552-133018213 | 4166 | B3gnt2 | NM_001169114.1 | chr11:22734738-22760336 |
| 4074 | AV039307 | NR_038349.1 | chr2:120676391-120796451 | 4167 | B3gnt2 | NM_016888.5 | chr11:22734738-22760336 |
| | | | | 4168 | B3gnt3 | NM_028189.3 | chr8:74215617-74225699 |

Fig. 25 - 23

| | | | |
|---|---|---|---|
| 4169 | B3gnt4 | NM_198611.2 | chr5:123960469-123961891 |
| 4170 | B3gnt5 | NM_001159407.1 | chr16:19760326-19772846 |
| 4171 | B3gnt5 | NM_001159408.1 | chr16:19760326-19772846 |
| 4172 | B3gnt5 | NM_054052.3 | chr16:19760326-19772846 |
| 4173 | B3gnt6 | NM_001081167.1 | chr7:105340924-105347985 |
| 4174 | B3gnt7 | NM_145222.2 | chr1:88199795-88203880 |
| 4175 | B3gnt8 | NM_001036740.2 | chr7:26412642-26414509 |
| 4176 | B3gnt8 | NM_146184.4 | chr7:26412642-26414509 |
| 4177 | B3gnt9 | NM_001271915.1 | chr8:107749087-107779053 |
| 4178 | B3gnt9 | NM_178879.4 | chr8:107749087-107779053 |
| 4179 | B3gnt1 | NM_178664.5 | chr11:121477522-121534465 |
| 4180 | B430010I23Rik | NR_015457.1 | chr8:42102822-42109570 |
| 4181 | B430212C06Rik | NR_033214.1 | chr18:67480863-67503757 |
| 4182 | B430306N03Rik | NM_177083.4 | chr17:48455486-48465836 |
| 4183 | B430319G15Rik | NR_029474.1 | chr9:92433639-92437707 |
| 4184 | B4galnt1 | NM_001244617.1 | chr10:126602211-126609396 |
| 4185 | B4galnt1 | NM_001244618.1 | chr10:126602211-126609396 |
| 4186 | B4galnt1 | NM_008080.5 | chr10:126602211-126609396 |
| 4187 | B4galnt1 | NM_027529.2 | chr10:126602211-126609396 |
| 4188 | B4galnt1 | NR_045166.1 | chr10:126602211-126609396 |
| 4189 | B4galnt2 | NM_008081.3 | chr11:95724872-95776185 |
| 4190 | B4galnt3 | NM_198884.1 | chr6:120153827-120244577 |
| 4191 | B4galnt4 | NM_177897.3 | chr7:148247172-148258018 |
| 4192 | B4galt1 | NM_022305.4 | chr4:40751615-40801570 |
| 4193 | B4galt2 | NM_001253381.1 | chr4:117545604-117556081 |
| 4194 | B4galt2 | NM_017377.5 | chr4:117545604-117556081 |
| 4195 | B4galt2 | NR_045570.1 | chr4:117545604-117556081 |
| 4196 | B4galt3 | NM_020579.2 | chr1:173200458-173207026 |
| 4197 | B4galt4 | NM_001285793.1 | chr16:38742371-38769167 |
| 4198 | B4galt4 | NM_019804.4 | chr16:38742371-38769167 |
| 4199 | B4galt5 | NM_019835.2 | chr2:167123944-167174678 |
| 4200 | B4galt6 | NM_019737.2 | chr18:20843099-20904905 |
| 4201 | B4galt7 | NM_146045.1 | chr13:55701471-55711315 |
| 4202 | B630005N14Rik | NM_175314.4 | chr6:13575674-13627966 |
| 4203 | B630019K06Rik | NR_045448.1 | chrX:8469478-8472090 |
| 4204 | B830017H08Rik | NM_027959.1 | chr16:17833211-17835112 |
| 4205 | B930003M22Rik | NR_037588.1 | chr17:10512783-10514006 |
| 4206 | B930018H19Rik | NR_040706.1 | chr8:35652473-35703370 |
| 4207 | B930025P03Rik | NR_040705.1 | chr8:10870421-10882454 |
| 4208 | B930041F14Rik | NM_178699.4 | chr4:155068450-155070592 |
| 4209 | B930059L03Rik | NR_033340.1 | chr12:111829583-111830889 |
| 4210 | B930092H01Rik | NR_045334.1 | chr9:61107033-61141616 |
| 4211 | B9d1 | NM_013717.2 | chr11:61318673-61326429 |
| 4212 | B9d2 | NM_172148.1 | chr7:26466176-26471577 |
| 4213 | Baalc | NM_080640.5 | chr15:38765454-38784462 |
| 4214 | Baat | NM_007519.3 | chr4:49502289-49519430 |
| 4215 | Babam1 | NM_026636.2 | chr8:73920753-73928671 |
| 4216 | Bace1 | NM_001145947.1 | chr9:45646611-45670567 |
| 4217 | Bace1 | NM_011792.5 | chr9:45646611-45670567 |
| 4218 | Bace2 | NM_019517.4 | chr16:97578334-97660619 |
| 4219 | Bach1 | NM_007520.2 | chr16:87699198-87733591 |
| 4220 | Bach2 | NM_001109661.1 | chr4:32504410-32673083 |
| 4221 | Bach2os | NR_026843.1 | chr4:32646655-32658637 |
| 4222 | Bad | NM_001285453.1 | chr19:7012559-7026395 |
| 4223 | Bad | NM_007522.3 | chr19:7012559-7026395 |
| 4224 | Bag1 | NM_009716.3 | chr4:40883430-40895327 |
| 4225 | Bag2 | NM_145392.1 | chr1:33802328-33814595 |
| 4226 | Bag3 | NM_013863.5 | chr7:135667096-135690493 |
| 4227 | Bag4 | NM_026121.3 | chr8:26875010-26895681 |
| 4228 | Bag5 | NM_027404.2 | chr12:112947703-112951467 |
| 4229 | Bag6 | NM_001252468.1 | chr17:35272122-35284267 |
| 4230 | Bag6 | NM_001252469.1 | chr17:35272122-35284267 |
| 4231 | Bag6 | NM_057171.2 | chr17:35272122-35284267 |
| 4232 | Bahcc1 | NM_198423.3 | chr11:120094260-120153611 |
| 4233 | Bahd1 | NM_001045523.1 | chr2:118727350-118750260 |
| 4234 | Bai1 | NM_174991.3 | chr15:74346625-74419894 |
| 4235 | Bai2 | NM_001199696.1 | chr4:129662113-129699877 |
| 4236 | Bai2 | NM_001290714.1 | chr4:129662113-129699877 |
| 4237 | Bai2 | NM_001290715.1 | chr4:129662113-129699877 |
| 4238 | Bai2 | NM_173071.3 | chr4:129662113-129699877 |
| 4239 | Bai3 | NM_175642.4 | chr1:25124321-25886552 |
| 4240 | Baiap2 | NM_001037754.3 | chr11:119804405-119868096 |
| 4241 | Baiap2 | NM_001037755.3 | chr11:119804405-119868096 |
| 4242 | Baiap2 | NM_130862.4 | chr11:119804405-119868096 |
| 4243 | Baiap2l1 | NM_025833.3 | chr5:145025394-145118981 |
| 4244 | Baiap2l2 | NM_027920.2 | chr15:79088624-79115939 |
| 4245 | Baiap3 | NM_001163270.1 | chr17:25379604-25393309 |
| 4246 | Bak1 | NM_007523.2 | chr17:27156757-27165571 |
| 4247 | Bambi | NM_026505.2 | chr18:3507954-3516402 |
| 4248 | Bambi-ps1 | NR_027919.1 | chr2:122292318-122293533 |
| 4249 | Banf1 | NM_001038231.2 | chr19:5364632-5371511 |
| 4250 | Banf1 | NM_001286608.1 | chr19:5364632-5371511 |
| 4251 | Banf1 | NM_011793.3 | chr19:5364632-5371511 |
| 4252 | Banf1 | NR_104482.1 | chr19:5364632-5371511 |
| 4253 | Banf2 | NM_001044750.1 | chr2:143858837-143899715 |
| 4254 | Banf2 | NM_207275.1 | chr2:143858837-143899715 |
| 4255 | Bank1 | NM_001033350.2 | chr3:135716327-135989010 |
| 4256 | Banp | NM_001110100.2 | chr8:124474391-124553160 |
| 4257 | Banp | NM_001285981.1 | chr8:124474391-124553160 |
| 4258 | Banp | NM_001285983.1 | chr8:124474391-124553160 |
| 4259 | Banp | NM_016812.4 | chr8:124474391-124553160 |
| 4260 | Bap1 | NM_027088.2 | chr14:32064674-32073115 |
| 4261 | Bard1 | NM_007525.3 | chr1:71074108-71149546 |
| 4262 | Barhl1 | NM_001164186.1 | chr2:28763199-28771960 |
| 4263 | Barhl1 | NM_019446.4 | chr2:28763199-28771960 |
| 4264 | Barhl2 | NM_001005477.1 | chr5:106881541-106887185 |
| 4265 | Barx1 | NM_007526.4 | chr13:48758404-48761876 |
| 4266 | Barx2 | NM_013800.2 | chr9:31663628-31720870 |
| 4267 | Basp1 | NM_027395.2 | chr15:25293031-25343519 |
| 4268 | Batf | NM_016767.2 | chr12:87027669-87050037 |
| 4269 | Batf2 | NM_028967.1 | chr19:6164457-6172475 |
| 4270 | Batf3 | NM_030060.2 | chr1:192922292-192932822 |
| 4271 | Bax | NM_007527.3 | chr7:52717064-52722658 |
| 4272 | Baz1a | NM_013815.2 | chr12:55993975-56087323 |
| 4273 | Baz1b | NM_011714.2 | chr5:135663192-135721999 |
| 4274 | Baz2a | NM_054078.2 | chr10:127525838-127566359 |
| 4275 | Baz2b | NM_001001182.3 | chr2:59737419-59963797 |
| 4276 | Bb014433 | NR_037972.1 | chr8:15041445-15046078 |
| 4277 | Bb019430 | NR_033565.1 | chr10:58159492-58167025 |
| 4278 | Bb031773 | NR_028391.1 | chr4:102676711-102684570 |
| 4279 | Bb123696 | NR_027893.1 | chr13:52824738-52852574 |
| 4280 | Bb283400 | NR_038124.1 | chr6:30126622-30128040 |
| 4281 | Bb287469 | NM_001177573.1 | chr12:89055024-89059124 |
| 4282 | Bb287469 | NM_001177573.1 | chr12:88959817-88963905 |
| 4283 | Bb557941 | NR_040356.1 | chr2:56979887-57034165 |
| 4284 | Bbc3 | NM_133234.2 | chr7:16894931-16903683 |
| 4285 | Bbip1 | NM_001195338.1 | chr19:53966720-54107768 |
| 4286 | Bbip1 | NM_001195348.1 | chr19:53966720-54107768 |
| 4287 | Bbox1 | NM_130452.1 | chr2:110105239-110145882 |
| 4288 | Bbs1 | NM_001033128.3 | chr19:4886881-4906627 |
| 4289 | Bbs10 | NM_027914.2 | chr10:110735734-110738792 |
| 4290 | Bbs12 | NM_001008502.2 | chr3:37211475-37220373 |
| 4291 | Bbs12 | NM_001255992.1 | chr3:37211475-37220373 |
| 4292 | Bbs2 | NM_026116.2 | chr8:96591853-96622711 |
| 4293 | Bbs4 | NM_175325.3 | chr9:59169772-59201315 |
| 4294 | Bbs5 | NM_028284.2 | chr2:69485311-69505626 |
| 4295 | Bbs7 | NM_027810.3 | chr3:36472064-36512311 |
| 4296 | Bbs9 | NM_178415.1 | chr9:22280158-22692724 |
| 4297 | Bbs9 | NM_181316.4 | chr9:22280158-22692724 |
| 4298 | Bbx | NM_024444.3 | chr16:50191956-50432502 |
| 4299 | BC002163 | NR_002445.2 | chr16:42884482-43619236 |
| 4300 | BC002163 | NR_002445.2 | chr4:123389952-123395429 |
| 4301 | BC003331 | NM_001077237.1 | chr1:152208440-152313295 |
| 4302 | BC003331 | NM_145511.2 | chr1:152208440-152313295 |
| 4303 | BC003965 | NM_183150.2 | chr17:25321505-25324607 |
| 4304 | BC004004 | NM_030561.3 | chr17:29405732-29439832 |
| 4305 | BC005537 | NM_024473.3 | chr13:24893525-24904768 |
| 4306 | BC005561 | NM_001166581.1 | chr5:104937370-104951402 |
| 4307 | BC005624 | NM_144885.2 | chr2:30828352-30837461 |
| 4308 | BC005764 | NM_001170935.1 | chr10:79314121-79337379 |
| 4309 | BC005764 | NM_181681.2 | chr10:79314121-79337379 |
| 4310 | BC005764 | NR_033210.1 | chr10:79314121-79337379 |
| 4311 | BC006965 | NR_024085.1 | chr11:112525240-112572670 |
| 4312 | BC016579 | NM_145389.2 | chr16:45626960-45654231 |
| 4313 | BC017158 | NM_145590.2 | chr7:135414893-135441645 |
| 4314 | BC017643 | NM_001252548.1 | chr11:121038906-121090623 |
| 4315 | BC017643 | NM_001252549.1 | chr11:121038906-121090623 |
| 4316 | BC017643 | NM_001252550.1 | chr11:121038906-121090623 |
| 4317 | BC017643 | NM_001254735.1 | chr11:121038906-121090623 |
| 4318 | BC017643 | NM_144832.2 | chr11:121038906-121090623 |
| 4319 | BC018242 | NM_001290299.1 | chr9:21741453-21753351 |
| 4320 | BC018242 | NM_144935.1 | chr9:21741453-21753351 |
| 4321 | BC018473 | NR_003364.1 | chr11:116613480-116619197 |
| 4322 | BC018507 | NM_144837.3 | chr13:70727566-70776512 |
| 4323 | BC020402 | NR_033219.1 | chr10:7398768-7400956 |
| 4324 | BC021614 | NM_144869.2 | chr19:4057486-4059294 |
| 4325 | BC021767 | NR_033629.1 | chr3:94464510-94471074 |
| 4326 | BC021785 | NM_001001489.3 | chr10:39666717-39706452 |
| 4327 | BC021785 | NM_001113385.1 | chr10:39666717-39706452 |
| 4328 | BC021785 | NM_001113388.2 | chr10:39666717-39706452 |
| 4329 | BC021891 | NM_145608.2 | chr8:128434349-128471339 |
| 4330 | BC022687 | NM_145450.3 | chr12:114047185-114054456 |
| 4331 | BC023829 | NM_001033328.2 | chrX:67713230-67730218 |
| 4332 | BC024139 | NM_001142968.1 | chr15:75949948-75956986 |
| 4333 | BC024386 | NR_015583.1 | chr7:148091962-148093866 |
| 4334 | BC024978 | NM_001243888.1 | chr7:27972024-27990405 |
| 4335 | BC024978 | NM_001290511.1 | chr7:27972024-27990405 |
| 4336 | BC024978 | NM_001290513.1 | chr7:27972024-27990405 |
| 4337 | BC025920 | NR_030677.1 | chr10:81069052-81072581 |
| 4338 | BC026585 | NM_001033284.1 | chr1:159388712-159418864 |
| 4339 | BC027072 | NM_146082.3 | chr17:72092894-72102225 |
| 4340 | BC027231 | NM_145972.4 | chr16:44724413-44737397 |
| 4341 | BC028528 | NM_153513.2 | chr3:95688896-95695853 |
| 4342 | BC029214 | NM_153557.1 | chr2:25315007-25316614 |
| 4343 | BC029722 | NR_015528.1 | chr2:155643468-155644939 |
| 4344 | BC030307 | NM_001003910.2 | chr10:86168555-86239588 |
| 4345 | BC030307 | NM_001003939.2 | chr10:86168555-86239588 |
| 4346 | BC030307 | NM_153595.3 | chr10:86168555-86239588 |
| 4347 | BC030336 | NM_001164580.1 | chr7:127821133-127878368 |
| 4348 | BC030499 | NM_001287206.1 | chr11:78104342-78110307 |
| 4349 | BC030500 | NM_173411.2 | chr6:61390551-61393095 |
| 4350 | BC030867 | NM_153544.3 | chr11:102110195-102126497 |
| 4351 | BC030870 | NR_033217.1 | chr8:67609512-67653436 |
| 4352 | BC031181 | NM_001001181.1 | chr18:75165553-75169587 |
| 4353 | BC031361 | NR_033221.1 | chr16:38085150-38089346 |
| 4354 | BC033916 | NR_040470.1 | chr17:34042079-34043620 |
| 4355 | BC035044 | NM_001254946.1 | chr6:128798061-128848185 |
| 4356 | BC035044 | NM_001254947.1 | chr6:128798061-128848185 |
| 4357 | BC037032 | NR_028266.1 | chr15:3970511-3977406 |
| 4358 | BC037034 | NM_153161.3 | chr5:138700886-138705280 |

Fig. 25 - 24

| | | | |
|---|---|---|---|
| 4359 | BC037704 | NR_045645.1 | chr19:43749667-43751660 |
| 4360 | BC039771 | NR_033220.1 | chr2:145526930-145579408 |
| 4361 | BC039966 | NR_040670.1 | chr4:153322563-153324585 |
| 4362 | BC048403 | NM_173022.2 | chr10:121176892-121189915 |
| 4363 | BC048502 | NM_177631.3 | chr15:103269390-103278890 |
| 4364 | BC048507 | NM_001001185.3 | chr13:67964262-67964860 |
| 4365 | BC048546 | NM_001001179.3 | chr6:128489839-128531624 |
| 4366 | BC048562 | NM_001004192.1 | chr9:108338812-108348414 |
| 4367 | BC048602 | NR_045280.1 | chr15:35236764-35258290 |
| 4368 | BC048609 | NM_001111317.1 | chr19:6080038-6080785 |
| 4369 | BC048644 | NM_001033485.2 | chr8:124431733-124442328 |
| 4370 | BC048671 | NM_177738.2 | chr6:90251263-90255442 |
| 4371 | BC048679 | NM_001193274.1 | chr7:88639159-88643216 |
| 4372 | BC048679 | NM_183143.3 | chr7:88639159-88643216 |
| 4373 | BC049352 | NM_001198971.1 | chr9:45003849-45058068 |
| 4374 | BC049635 | NM_177585.4 | chr4:42880874-42887075 |
| 4375 | BC049715 | NM_178776.3 | chr6:136777364-136789075 |
| 4376 | BC049730 | NM_199150.1 | chr7:25494277-25499554 |
| 4377 | BC049762 | NM_177567.3 | chr11:51067152-51076453 |
| 4378 | BC051019 | NM_001040700.2 | chr7:116855695-116867285 |
| 4379 | BC051142 | NM_001001177.2 | chr17:34535764-34597679 |
| 4380 | BC051142 | NM_001163855.1 | chr17:34535764-34597679 |
| 4381 | BC051226 | NR_045146.1 | chr17:34045126-34046123 |
| 4382 | BC051537 | NR_046183.1 | chr17:34220788-34232254 |
| 4383 | BC051628 | NM_199312.3 | chr2:180954720-180957556 |
| 4384 | BC051665 | NM_199148.2 | chr13:60883247-60887725 |
| 4385 | BC052040 | NM_001145898.1 | chr2:115407451-115604504 |
| 4386 | BC052040 | NM_207264.4 | chr2:115407451-115604504 |
| 4387 | BC052688 | NR_028430.1 | chr13:61872939-61888642 |
| 4388 | BC053393 | NM_001025435.1 | chr11:46385014-46402734 |
| 4389 | BC053749 | NM_183321.1 | chr7:31324152-31337291 |
| 4390 | BC055111 | NM_183182.3 | chr4:106263513-106289843 |
| 4391 | BC055324 | NM_201364.1 | chr1:165884139-165924912 |
| 4392 | BC055402 | NR_037990.1 | chr1:57257488-57271840 |
| 4393 | BC061194 | NM_001001334.2 | chr2:18620648-18671232 |
| 4394 | BC061195 | NR_105038.1 | chrX:90401492-90402210 |
| 4395 | BC061195 | NR_105038.1 | chrX:90428565-90429283 |
| 4396 | BC061212 | NM_198667.1 | chr5:96161110-96165192 |
| 4397 | BC061237 | NM_198677.1 | chr14:45119792-45126016 |
| 4398 | BC064078 | NR_015455.1 | chr6:128943037-128956667 |
| 4399 | BC065397 | NR_033324.1 | chrX:133277496-133337900 |
| 4400 | BC068157 | NM_207203.2 | chr8:4209542-4217312 |
| 4401 | BC068281 | NM_001170858.1 | chr12:4850108-4863773 |
| 4402 | BC068281 | NM_173416.3 | chr12:4850108-4863773 |
| 4403 | BC080695 | NM_001007579.3 | chr4:143157369-143163701 |
| 4404 | BC089491 | NM_175033.2 | chr7:29069670-29076153 |
| 4405 | BC089597 | NM_145424.2 | chr10:127303531-127314375 |
| 4406 | BC094916 | NM_001024721.2 | chr1:175451441-175466088 |
| 4407 | Bc1 | NR_038088.1 | chr12:92439829-92786285 |
| 4408 | BC100451 | NM_021440.2 | chr11:118193674-118203848 |
| 4409 | BC100530 | NM_001082546.1 | chr16:36359467-36367656 |
| 4410 | BC107364 | NM_001256180.1 | chr3:96237710-96256229 |
| 4411 | BC107364 | NM_001256181.1 | chr3:96237710-96256229 |
| 4412 | BC117090 | NM_001001332.2 | chr16:36321750-36334418 |
| 4413 | BC147527 | NM_001037925.2 | chrUn_random:12474-21008 |
| 4414 | Bcam | NM_020486.2 | chr7:20341486-20355881 |
| 4415 | Bcan | NM_001109758.1 | chr3:87791452-87804278 |
| 4416 | Bcan | NM_007529.2 | chr3:87791452-87804278 |
| 4417 | Bcap29 | NM_001164090.1 | chr12:32280218-32319523 |
| 4418 | Bcap29 | NM_007530.3 | chr12:32280218-32319523 |
| 4419 | Bcap31 | NM_012060.4 | chrX:70931521-70961514 |
| 4420 | Bcar1 | NM_001198839.1 | chr8:114234374-114267749 |
| 4421 | Bcar1 | NM_009954.3 | chr8:114234374-114267749 |
| 4422 | Bcar3 | NM_013867.2 | chr3:122122697-122233100 |
| 4423 | Bcas1 | NM_001164369.1 | chr2:170172490-170253345 |
| 4424 | Bcas1 | NM_029815.2 | chr2:170172490-170253345 |
| 4425 | Bcas1os2 | NR_040610.1 | chr2:170181861-170205935 |
| 4426 | Bcas2 | NM_026602.3 | chr3:103275633-103283077 |
| 4427 | Bcas3 | NM_001166642.1 | chr11:85166665-85645890 |
| 4428 | Bcas3 | NM_001166643.1 | chr11:85166665-85645890 |
| 4429 | Bcas3 | NM_138681.4 | chr11:85166665-85645890 |
| 4430 | Bcas3os1 | NR_045875.1 | chr11:85515702-85533246 |
| 4431 | Bcas3os2 | NR_046194.1 | chr11:85580335-85589182 |
| 4432 | Bcat1 | NM_001024468.3 | chr6:144942354-145024677 |
| 4433 | Bcat1 | NM_007532.5 | chr6:144942354-145024677 |
| 4434 | Bcat2 | NM_001243052.1 | chr7:52823164-52845080 |
| 4435 | Bcat2 | NM_001243053.1 | chr7:52823164-52845080 |
| 4436 | Bcat2 | NM_009737.3 | chr7:52823164-52845080 |
| 4437 | Bccip | NM_025392.2 | chr7:140149016-140912828 |
| 4438 | Bcdin3d | NM_029236.2 | chr15:99300514-99305161 |
| 4439 | Bche | NM_009738.3 | chr3:73439730-73512337 |
| 4440 | Bckdha | NM_007533.5 | chr7:26414870-26443780 |
| 4441 | Bckdhb | NM_199195.1 | chr9:83842387-84017847 |
| 4442 | Bckdk | NM_009739.3 | chr7:135047586-135053178 |
| 4443 | Bcl10 | NM_009740.2 | chr3:145587225-145597328 |
| 4444 | Bcl11a | NM_001159289.1 | chr11:23978055-24073558 |
| 4445 | Bcl11a | NM_001159290.1 | chr11:23978055-24073558 |
| 4446 | Bcl11a | NM_001242934.1 | chr11:23978055-24073558 |
| 4447 | Bcl11a | NM_016707.3 | chr11:23978055-24073558 |
| 4448 | Bcl11b | NM_001079883.1 | chr12:109148612-109241624 |
| 4449 | Bcl11b | NM_001286343.1 | chr12:109148612-109241624 |
| 4450 | Bcl11b | NM_021399.2 | chr12:109148612-109241624 |
| 4451 | Bcl2 | NM_009741.4 | chr1:108434754-108610867 |
| 4452 | Bcl2 | NM_177410.2 | chr1:108434754-108610867 |
| 4453 | Bcl2a1a | NM_009742.3 | chr9:88851757-88857254 |
| 4454 | Bcl2a1b | NM_007534.3 | chr9:89094110-89102676 |
| 4455 | Bcl2a1c | NM_007535.2 | chr9:114239252-114239696 |
| 4456 | Bcl2a1d | NM_007536.2 | chr9:88618125-88626688 |
| 4457 | Bcl2l1 | NM_001289716.1 | chr2:152579908-152657464 |
| 4458 | Bcl2l1 | NM_001289717.1 | chr2:152579908-152657464 |
| 4459 | Bcl2l1 | NM_001289739.1 | chr2:152579908-152657464 |
| 4460 | Bcl2l1 | NM_009743.5 | chr2:152579908-152657464 |
| 4461 | Bcl2l10 | NM_013479.2 | chr9:75195564-75199447 |
| 4462 | Bcl2l11 | NM_001284410.2 | chr2:127951773-127988283 |
| 4463 | Bcl2l11 | NM_001291016.1 | chr2:127951773-127988283 |
| 4464 | Bcl2l11 | NM_009754.3 | chr2:127951773-127988283 |
| 4465 | Bcl2l11 | NM_207680.2 | chr2:127951773-127988283 |
| 4466 | Bcl2l11 | NM_207681.2 | chr2:127951773-127988283 |
| 4467 | Bcl2l12 | NM_029410.3 | chr7:52246592-52252949 |
| 4468 | Bcl2l13 | NM_153516.2 | chr6:120786247-120842860 |
| 4469 | Bcl2l14 | NM_025778.3 | chr6:134346346-134388742 |
| 4470 | Bcl2l15 | NM_001142959.1 | chr3:103636618-103656541 |
| 4471 | Bcl2l15 | NM_001142960.1 | chr3:103636618-103656541 |
| 4472 | Bcl2l2 | NM_007537.1 | chr14:55502261-55507071 |
| 4473 | Bcl3 | NM_033601.3 | chr7:20393810-20408104 |
| 4474 | Bcl6 | NM_009744.3 | chr16:23965137-23988698 |
| 4475 | Bcl6b | NM_007528.3 | chr11:70037628-70043300 |
| 4476 | Bcl7a | NM_029850.3 | chr5:123794456-123824092 |
| 4477 | Bcl7b | NM_009745.2 | chr5:135644241-135657722 |
| 4478 | Bcl7c | NM_009746.2 | chr7:134848492-134852280 |
| 4479 | Bcl9 | NM_029933.4 | chr3:97007564-97031287 |
| 4480 | Bcl9l | NM_030256.2 | chr9:44307218-44318495 |
| 4481 | Bclaf1 | NM_001025392.1 | chr10:20032274-20062307 |
| 4482 | Bclaf1 | NM_001025393.1 | chr10:20032274-20062307 |
| 4483 | Bclaf1 | NM_153787.2 | chr10:20032274-20062307 |
| 4484 | Bcmo1 | NM_001163028.1 | chr8:119619764-119657620 |
| 4485 | Bcmo1 | NM_021486.3 | chr8:119619764-119657620 |
| 4486 | Bco2 | NM_133217.3 | chr9:50341191-50363243 |
| 4487 | Bcor | NM_001168321.1 | chrX:11613863-11737481 |
| 4488 | Bcor | NM_029510.3 | chrX:11613863-11737481 |
| 4489 | Bcor | NM_175044.3 | chrX:11613863-11737481 |
| 4490 | Bcor | NM_175045.3 | chrX:11613863-11737481 |
| 4491 | Bcor | NM_175046.3 | chrX:11613863-11737481 |
| 4492 | Bcorl1 | NM_178782.1 | chrX:45694534-45759905 |
| 4493 | Bcr | NM_001081412.2 | chr10:74523640-74647668 |
| 4494 | Bcs1l | NM_025784.5 | chr1:74634934-74639017 |
| 4495 | Bdh1 | NM_001122683.1 | chr16:31422382-31458987 |
| 4496 | Bdh1 | NM_175177.4 | chr16:31422382-31458987 |
| 4497 | Bdh2 | NM_001172055.1 | chr3:134944184-134967389 |
| 4498 | Bdh2 | NM_027208.2 | chr3:134944184-134967389 |
| 4499 | Bdkrb1 | NM_007539.2 | chr12:106842300-106843638 |
| 4500 | Bdkrb2 | NM_009747.2 | chr12:106801381-106831281 |
| 4501 | Bdnf | NM_001048139.1 | chr2:109514856-109567200 |
| 4502 | Bdnf | NM_001048141.1 | chr2:109514856-109567200 |
| 4503 | Bdnf | NM_001048142.1 | chr2:109514856-109567200 |
| 4504 | Bdnf | NM_001285416.1 | chr2:109514856-109567200 |
| 4505 | Bdnf | NM_001285417.1 | chr2:109514856-109567200 |
| 4506 | Bdnf | NM_001285418.1 | chr2:109514856-109567200 |
| 4507 | Bdnf | NM_001285419.1 | chr2:109514856-109567200 |
| 4508 | Bdnf | NM_001285420.1 | chr2:109514856-109567200 |
| 4509 | Bdnf | NM_001285421.1 | chr2:109514856-109567200 |
| 4510 | Bdnf | NM_001285422.1 | chr2:109514856-109567200 |
| 4511 | Bdnf | NM_007540.4 | chr2:109514856-109567200 |
| 4512 | Bdp1 | NM_001081061.1 | chr13:100787948-100874025 |
| 4513 | Bean1 | NM_001141922.1 | chr8:106694412-106742997 |
| 4514 | Bean1 | NM_001141924.1 | chr8:106694412-106742997 |
| 4515 | Bean1 | NM_001141925.1 | chr8:106694412-106742997 |
| 4516 | Becn1 | NM_019584.3 | chr11:101149581-101163581 |
| 4517 | Becn2 | NM_001290692.1 | chr1:177850459-177852356 |
| 4518 | Begain | NM_001163175.1 | chr12:110270391-110306427 |
| 4519 | Bend3 | NM_199028.2 | chr10:43198945-43235223 |
| 4520 | Bend4 | NM_001164806.1 | chr5:67783385-67819038 |
| 4521 | Bend5 | NM_026279.3 | chr4:100070302-111335629 |
| 4522 | Bend5 | NR_033793.1 | chr4:100070302-111335629 |
| 4523 | Bend6 | NM_177235.3 | chr1:33908896-33964466 |
| 4524 | Bend7 | NM_001190400.1 | chr2:4638876-4723192 |
| 4525 | Bend7 | NM_178663.4 | chr2:4638876-4723192 |
| 4526 | Best1 | NM_011913.2 | chr19:10059661-10076123 |
| 4527 | Best2 | NM_001130194.1 | chr8:87531100-87538430 |
| 4528 | Best2 | NR_052011.1 | chr8:87531100-87538430 |
| 4529 | Best3 | NM_001007583.1 | chr10:116423369-116462096 |
| 4530 | Bet1 | NM_009748.2 | chr6:4026903-4036927 |
| 4531 | Bet1l | NM_018742.5 | chr7:148039282-148042242 |
| 4532 | Bex1 | NM_009052.2 | chrX:132748510-132750052 |
| 4533 | Bex2 | NM_009749.2 | chrX:132601103-132602775 |
| 4534 | Bex4 | NM_212457.2 | chrX:132673583-132674976 |
| 4535 | Bex6 | NM_001033539.2 | chr16:32179885-32187030 |
| 4536 | Bfar | NM_001175752.1 | chr16:13671950-13703705 |
| 4537 | Bfar | NM_025976.5 | chr16:13671950-13703705 |
| 4538 | Bfsp1 | NM_001291061.1 | chr2:143652263-143688909 |
| 4539 | Bfsp1 | NM_009751.2 | chr2:143652263-143688909 |
| 4540 | Bfsp2 | NM_001002896.2 | chr3:103327254-103382658 |
| 4541 | Bglap | NM_001037939.2 | chr3:88187416-88188388 |
| 4542 | Bglap | NM_007541.3 | chr3:88187416-88188388 |
| 4543 | Bglap2 | NM_001032298.2 | chr3:88181657-88182621 |
| 4544 | Bglap3 | NM_031368.5 | chr3:88172538-88173642 |
| 4545 | Bgn | NM_007542.4 | chrX:70728973-70741275 |
| 4546 | Bhlha15 | NM_010800.4 | chr5:144951154-144955310 |
| 4547 | Bhlha9 | NM_177182.4 | chr11:76485971-76487178 |
| 4548 | Bhlhb9 | NM_001098222.1 | chrX:132420389-132425620 |

Fig. 25 - 25

| # | Gene | Accession | Location |
|---|---|---|---|
| 4549 | Bhlhb9 | NM_198161.2 | chrX:132420389-132425620 |
| 4550 | Bhlhe22 | NM_021560.4 | chr3:17954324-17957514 |
| 4551 | Bhlhe23 | NM_080641.5 | chr2:180509085-180511605 |
| 4552 | Bhlhe40 | NM_011498.4 | chr6:108610623-108616919 |
| 4553 | Bhlhe41 | NM_001271768.1 | chr6:145806762-145813940 |
| 4554 | Bhlhe41 | NM_024469.2 | chr6:145806762-145813940 |
| 4555 | Bhmt | NM_016668.3 | chr13:94386845-94407713 |
| 4556 | Bhmt2 | NM_022884.2 | chr13:94426051-94444257 |
| 4557 | Bicc1 | NM_031397.2 | chr10:70387847-70622382 |
| 4558 | Bicd1 | NM_001112796.2 | chr6:149357505-149511848 |
| 4559 | Bicd1 | NM_009753.4 | chr6:149357505-149511848 |
| 4560 | Bicd2 | NM_001039179.2 | chr13:49436917-49482395 |
| 4561 | Bicd2 | NM_001039180.2 | chr13:49436917-49482395 |
| 4562 | Bicd2 | NM_029791.4 | chr13:49436917-49482395 |
| 4563 | Bid | NM_007544.3 | chr6:120843136-120866838 |
| 4564 | Bik | NM_007546.2 | chr15:83357291-83375065 |
| 4565 | Bin1 | NM_001083334.1 | chr18:32518710-32595394 |
| 4566 | Bin1 | NM_009668.2 | chr18:32518710-32595394 |
| 4567 | Bin2 | NM_001270537.1 | chr15:100471513-100499931 |
| 4568 | Bin3 | NM_021328.1 | chr14:70499952-70538013 |
| 4569 | Birc2 | NM_007465.2 | chr9:7818225-7835255 |
| 4570 | Birc3 | NM_007464.3 | chr9:7848700-7873170 |
| 4571 | Birc5 | NM_001012273.1 | chr11:117710550-117717057 |
| 4572 | Birc5 | NM_009689.2 | chr11:117710550-117717057 |
| 4573 | Birc6 | NM_007566.3 | chr17:74927634-75102696 |
| 4574 | Birc7 | NM_001163247.1 | chr2:180663727-180668715 |
| 4575 | Bivm | NM_144558.4 | chr1:44176812-44201616 |
| 4576 | Blcap | NM_016916.3 | chr2:157382098-157392097 |
| 4577 | Blk | NM_007549.2 | chr14:63991673-64036024 |
| 4578 | Blm | NM_001042527.2 | chr7:87599878-87680005 |
| 4579 | Blm | NM_007550.4 | chr7:87599878-87680005 |
| 4580 | Blnk | NM_178645.4 | chr1:76759157-76800891 |
| 4581 | Blnk | NM_008528.4 | chr19:41003416-41069025 |
| 4582 | Bloc1s1 | NM_015740.3 | chr10:128356969-128360580 |
| 4583 | Bloc1s2 | NM_028607.1 | chr19:44213736-44220936 |
| 4584 | Bloc1s3 | NM_177692.3 | chr7:20091152-20093680 |
| 4585 | Bloc1s4 | NM_133724.3 | chr5:37138612-37139918 |
| 4586 | Bloc1s5 | NM_139063.1 | chr13:38694574-38728678 |
| 4587 | Bloc1s6 | NM_019788.3 | chr2:122564240-122575223 |
| 4588 | Blvra | NM_026678.4 | chr2:126896392-126922820 |
| 4589 | Blvrb | NM_001290525.1 | chr7:28232996-28251000 |
| 4590 | Blvrb | NM_144923.3 | chr7:28232996-28251000 |
| 4591 | Blzf1 | NM_001160208.1 | chr1:166219930-166237615 |
| 4592 | Blzf1 | NM_001160209.1 | chr1:166219930-166237615 |
| 4593 | Blzf1 | NM_025505.4 | chr1:166219930-166237615 |
| 4594 | Bmf | NM_138313.3 | chr2:118354492-118375414 |
| 4595 | Bmi1 | NM_007552.4 | chr2:18598644-18608256 |
| 4596 | Bmp1 | NM_009755.3 | chr14:70874361-70920067 |
| 4597 | Bmp1 | NR_033241.1 | chr14:70874361-70920067 |
| 4598 | Bmp10 | NM_009756.2 | chr6:87378995-87384506 |
| 4599 | Bmp15 | NM_009757.4 | chrX:5891223-5897841 |
| 4600 | Bmp2 | NM_007553.3 | chr2:133377894-133388632 |
| 4601 | Bmp2k | NM_080708.1 | chr5:97426708-97520067 |
| 4602 | Bmp3 | NM_173404.3 | chr5:99283457-99309979 |
| 4603 | Bmp4 | NM_007554.2 | chr14:47003196-47010274 |
| 4604 | Bmp5 | NM_007555.3 | chr9:75623171-75746824 |
| 4605 | Bmp6 | NM_007556.2 | chr13:38437584-38591597 |
| 4606 | Bmp7 | NM_007557.3 | chr2:172693512-172765822 |
| 4607 | Bmp8a | NM_001256019.1 | chr4:122989890-123020495 |
| 4608 | Bmp8a | NM_007558.3 | chr4:122989890-123020495 |
| 4609 | Bmp8b | NM_007559.4 | chr4:122782408-122803334 |
| 4610 | Bmper | NM_028472.2 | chr9:23027519-23289659 |
| 4611 | Bmpr1a | NM_009758.4 | chr14:35224253-35315732 |
| 4612 | Bmpr1b | NM_001277216.1 | chr3:141500099-141832192 |
| 4613 | Bmpr1b | NM_001277217.1 | chr3:141500099-141832192 |
| 4614 | Bmpr1b | NM_001277218.1 | chr3:141500099-141832192 |
| 4615 | Bmpr1b | NM_001277220.1 | chr3:141500099-141832192 |
| 4616 | Bmpr1b | NM_007560.4 | chr3:141500099-141832192 |
| 4617 | Bmpr2 | NM_007561.4 | chr1:59821122-59934925 |
| 4618 | Bms1 | NM_194339.1 | chr6:118333398-118369435 |
| 4619 | Bmx | NM_009759.4 | chrX:160630773-160696125 |
| 4620 | Bmyc | NM_023326.2 | chr2:25562398-25563239 |
| 4621 | Bnc1 | NM_007562.1 | chr7:89111547-89137185 |
| 4622 | Bnc2 | NM_172870.4 | chr4:83918445-84320990 |
| 4623 | Bnip1 | NM_172149.5 | chr17:26918023-26929466 |
| 4624 | Bnip2 | NM_001038133.1 | chr9:69837272-69859466 |
| 4625 | Bnip2 | NM_016787.4 | chr9:69837272-69859466 |
| 4626 | Bnip3 | NM_009760.4 | chr7:146082518-146101189 |
| 4627 | Bnip3l | NM_009763.1 | chr14:67604076-67627714 |
| 4628 | Bnipl | NM_001168356.1 | chr3:95045214-95055115 |
| 4629 | Bnipl | NM_134253.2 | chr3:95045214-95055115 |
| 4630 | Boc | NM_172506.2 | chr16:44485158-44558983 |
| 4631 | Bod1 | NM_001024919.1 | chr13:31565149-31571862 |
| 4632 | Bod1l | NM_001081422.2 | chr5:42178777-42235554 |
| 4633 | Bok | NM_016778.3 | chr1:95582270-95592339 |
| 4634 | Bola1 | NM_026975.2 | chr3:96000510-96001509 |
| 4635 | Bola2 | NM_175103.2 | chr7:133839513-133840207 |
| 4636 | Bola3 | NM_175277.4 | chr6:83299477-83308386 |
| 4637 | Boll | NM_001113367.1 | chr1:55356912-55420313 |
| 4638 | Boll | NM_029267.3 | chr1:55356912-55420313 |
| 4639 | Bop1 | NM_013481.1 | chr15:76283426-76307699 |
| 4640 | Bora | NM_175265.4 | chr14:99445595-99473326 |
| 4641 | Bpgm | NM_007563.4 | chr6:34426355-34455610 |
| 4642 | Bphl | NM_026512.1 | chr13:34129509-34165943 |
| 4643 | Bpi | NM_177850.3 | chr2:158083976-158110267 |
| 4644 | Bpifa1 | NM_011126.3 | chr2:153968615-153974953 |
| 4645 | Bpifa2 | NM_008953.2 | chr2:153834011-153841809 |
| 4646 | Bpifa3 | NM_001291079.1 | chr2:153956071-153964095 |
| 4647 | Bpifa3 | NM_028528.3 | chr2:153956071-153964095 |
| 4648 | Bpifa5 | NM_025990.4 | chr2:153988342-153994182 |
| 4649 | Bpifa6 | NM_001080811.1 | chr2:153800680-153826231 |
| 4650 | Bpifb1 | NM_001012392.1 | chr2:154016553-154046079 |
| 4651 | Bpifb1 | NM_153418.2 | chr2:154016553-154046079 |
| 4652 | Bpifb2 | NM_025631.3 | chr2:153700780-153721006 |
| 4653 | Bpifb3 | NM_194357.1 | chr2:153743965-153758732 |
| 4654 | Bpifb4 | NM_001034875.3 | chr2:153766597-153789588 |
| 4655 | Bpifb5 | NM_144890.2 | chr2:154049477-154066638 |
| 4656 | Bpifb6 | NM_199303.2 | chr2:153726123-153738529 |
| 4657 | Bpifb9a | NM_175167.3 | chr2:154083614-154096982 |
| 4658 | Bpifb9b | NM_001025574.1 | chr2:154132979-154146378 |
| 4659 | Bpifc | NM_177772.4 | chr10:85422435-85474605 |
| 4660 | Bpnt1 | NM_011794.3 | chr1:187156037-187181648 |
| 4661 | Bptf | NM_176850.2 | chr11:106894394-106993236 |
| 4662 | Braf | NM_139294.5 | chr6:39553236-39675462 |
| 4663 | Brap | NM_001289543.1 | chr5:122110571-122137258 |
| 4664 | Brap | NM_001289544.1 | chr5:122110571-122137258 |
| 4665 | Brap | NM_028227.3 | chr5:122110571-122137258 |
| 4666 | Brat1 | NM_001276287.1 | chr5:141180964-141195332 |
| 4667 | Brat1 | NM_181066.3 | chr5:141180964-141195332 |
| 4668 | Brat1 | NR_074085.1 | chr5:141180964-141195332 |
| 4669 | Brca1 | NM_009764.3 | chr11:101356077-101413269 |
| 4670 | Brca2 | NM_001081001.2 | chr5:151325195-151372721 |
| 4671 | Brca2 | NM_009765.3 | chr5:151325195-151372721 |
| 4672 | Brcc3 | NM_001166457.1 | chrX:72661966-72701040 |
| 4673 | Brcc3 | NM_001166459.1 | chrX:72661966-72701040 |
| 4674 | Brcc3 | NM_145956.4 | chrX:72661966-72701040 |
| 4675 | Brd1 | NM_001033274.3 | chr15:88517464-88564649 |
| 4676 | Brd2 | NM_001204973.1 | chr17:34248963-34259552 |
| 4677 | Brd2 | NM_010238.3 | chr17:34248963-34259552 |
| 4678 | Brd2 | NR_037970.1 | chr17:34248963-34259552 |
| 4679 | Brd3 | NM_001113573.1 | chr2:27301100-27331193 |
| 4680 | Brd3 | NM_001113574.1 | chr2:27301100-27331193 |
| 4681 | Brd3 | NM_023336.4 | chr2:27301100-27331193 |
| 4682 | Brd4 | NM_001286680.1 | chr17:32333216-32421078 |
| 4683 | Brd4 | NM_020508.4 | chr17:32333216-32421078 |
| 4684 | Brd4 | NM_198094.2 | chr17:32333216-32421078 |
| 4685 | Brd7 | NM_012047.2 | chr8:90856209-90886090 |
| 4686 | Brd8 | NM_001289606.1 | chr18:34758268-34811390 |
| 4687 | Brd8 | NM_001289607.1 | chr18:34758268-34811390 |
| 4688 | Brd8 | NM_030147.3 | chr18:34758268-34811390 |
| 4689 | Brd9 | NM_001024508.3 | chr13:74075285-74098343 |
| 4690 | Brdt | NM_001079873.1 | chr5:107760212-107816077 |
| 4691 | Brdt | NM_054054.2 | chr5:107760212-107816077 |
| 4692 | Bre | NM_144541.1 | chr5:32000422-32387112 |
| 4693 | Bre | NM_181279.1 | chr5:32000422-32387112 |
| 4694 | Bre | NM_181280.1 | chr5:32000422-32387112 |
| 4695 | Bre | NM_181281.1 | chr5:32000422-32387112 |
| 4696 | Bre | NM_181282.1 | chr5:32000422-32387112 |
| 4697 | Brf1 | NM_028193.3 | chr12:114198073-114238832 |
| 4698 | Brf2 | NM_025686.2 | chr8:28234303-28239104 |
| 4699 | Bri3 | NM_001163709.1 | chr5:145005305-145121874 |
| 4700 | Bri3 | NM_018772.4 | chr5:145005305-145121874 |
| 4701 | Bri3bp | NM_029752.2 | chr5:125921937-125941255 |
| 4702 | Bricd5 | NM_175682.3 | chr17:24610829-24612414 |
| 4703 | Brinp1 | NM_019967.2 | chr4:68422405-68615431 |
| 4704 | Brinp2 | NM_267583.2 | chr1:160175399-160286391 |
| 4705 | Brinp3 | NM_001145807.1 | chr1:148342795-148749602 |
| 4706 | Brinp3 | NM_153539.3 | chr1:148342795-148749602 |
| 4707 | Brip1 | NM_178309.2 | chr11:85871637-86014695 |
| 4708 | Brix1 | NM_026396.3 | chr15:10404533-10415692 |
| 4709 | Brk1 | NM_133937.1 | chr6:113554755-113566945 |
| 4710 | Brms1 | NM_134155.1 | chr19:5041403-5049917 |
| 4711 | Brms1l | NM_001037756.2 | chr12:56937352-56970722 |
| 4712 | Brox | NM_027861.2 | chr1_random:249689-270356 |
| 4713 | Brpf1 | NM_001282126.1 | chr6:113257130-113274856 |
| 4714 | Brpf1 | NM_001282127.1 | chr6:113257130-113274856 |
| 4715 | Brpf1 | NM_001282128.1 | chr6:113257130-113274856 |
| 4716 | Brpf1 | NM_030178.2 | chr6:113257130-113274856 |
| 4717 | Brpf3 | NM_001081315.1 | chr17:28938070-28975734 |
| 4718 | Brs3 | NM_009766.1 | chrX:54296250-54301935 |
| 4719 | Brsk1 | NM_001003920.1 | chr7:4642529-4676853 |
| 4720 | Brsk1 | NM_001168572.1 | chr7:4642529-4676853 |
| 4721 | Brsk2 | NM_001009929.3 | chr7:149135655-149190148 |
| 4722 | Brsk2 | NM_001009930.3 | chr7:149135655-149190148 |
| 4723 | Brsk2 | NM_001276763.1 | chr7:149135655-149190148 |
| 4724 | Brsk2 | NM_029426.2 | chr7:149135655-149190148 |
| 4725 | Brwd1 | NM_001103179.1 | chr16:96213698-96304035 |
| 4726 | Brwd1 | NM_145125.3 | chr16:96213698-96304035 |
| 4727 | Brwd1 | NM_176928.1 | chr16:96213698-96304035 |
| 4728 | Brwd3 | NM_001081477.1 | chrX:105937546-106029694 |
| 4729 | Bscl2 | NM_001136064.3 | chr19:8911418-8923173 |
| 4730 | Bscl2 | NM_001290823.1 | chr19:8911418-8923173 |
| 4731 | Bscl2 | NM_008144.5 | chr19:8911418-8923173 |
| 4732 | Bsdc1 | NM_133889.2 | chr4:129138922-129165676 |
| 4733 | Bsg | NM_001077184.1 | chr10:79167102-79174724 |
| 4734 | Bsg | NM_009768.2 | chr10:79167102-79174724 |
| 4735 | Bsn | NM_007567.2 | chr9:107998352-108092714 |
| 4736 | Bsnd | NM_080458.2 | chr4:106156062-106164848 |
| 4737 | Bsph1 | NM_001033418.4 | chr7:14036189-14058798 |
| 4738 | Bsph2 | NM_001080942.2 | chr7:14140214-14156416 |

Fig. 25 - 26

| | | | |
|---|---|---|---|
| 4739 | Bspry | NM_138653.1 | chr4:62141100-62158332 |
| 4740 | Bst1 | NM_009763.3 | chr5:44210131-44234707 |
| 4741 | Bst2 | NM_198095.2 | chr8:74058160-74061336 |
| 4742 | Bsx | NM_178245.3 | chr9:40682209-40686055 |
| 4743 | Btaf1 | NM_001080706.1 | chr19:37000568-37088547 |
| 4744 | Btbd1 | NM_146193.2 | chr7:88936959-88974317 |
| 4745 | Btbd10 | NM_133700.2 | chr7:120459157-120512853 |
| 4746 | Btbd11 | NM_001017525.1 | chr10:84849558-85123037 |
| 4747 | Btbd11 | NM_028709.2 | chr10:84849558-85123037 |
| 4748 | Btbd16 | NM_001081038.2 | chr7:137917582-137969413 |
| 4749 | Btbd17 | NM_028055.4 | chr11:114651982-114657206 |
| 4750 | Btbd18 | NM_001145100.1 | chr2:84499235-84508938 |
| 4751 | Btbd19 | NR_024078.1 | chr4:116791822-116798330 |
| 4752 | Btbd2 | NM_145361.2 | chr10:80105361-80119816 |
| 4753 | Btbd3 | NM_001025431.1 | chr2:138082319-138113158 |
| 4754 | Btbd3 | NM_145534.2 | chr2:138082319-138113158 |
| 4755 | Btbd6 | NM_001145900.1 | chr12:114198072-114238832 |
| 4756 | Btbd6 | NM_201646.2 | chr12:114198072-114238832 |
| 4757 | Btbd7 | NM_172806.2 | chr12:104022857-104116616 |
| 4758 | Btbd8 | NM_001255991.1 | chr5:107867015-107920615 |
| 4759 | Btbd9 | NM_027060.1 | chr17:30352468-30713232 |
| 4760 | Btbd9 | NM_172618.2 | chr17:30352468-30713232 |
| 4761 | Btc | NM_007568.5 | chr5:91786286-91832020 |
| 4762 | Btd | NM_025295.4 | chr14:32454242-32481383 |
| 4763 | Btf3 | NM_001170540.1 | chr13:99079851-99086961 |
| 4764 | Btf3 | NM_145455.3 | chr13:99079851-99086961 |
| 4765 | Btf3l4 | NM_027453.2 | chr4:108486899-108506189 |
| 4766 | Btg1 | NM_007569.2 | chr10:96079634-96085445 |
| 4767 | Btg2 | NM_007570.2 | chr1:135971441-135975732 |
| 4768 | Btg3 | NM_009770.3 | chr16:78360105-78377055 |
| 4769 | Btg4 | NM_019493.3 | chr9:50924105-50927805 |
| 4770 | Btk | NM_013482.2 | chrX:131076879-131117679 |
| 4771 | Btla | NM_001037719.2 | chr16:45224449-45253008 |
| 4772 | Btla | NM_175584.3 | chr16:45224449-45253008 |
| 4773 | Btnl1a1 | NM_013483.2 | chr13:23548861-23557770 |
| 4774 | Btn2a2 | NM_001289614.1 | chr13:23568931-23580726 |
| 4775 | Btn2a2 | NM_001289615.1 | chr13:23568931-23580726 |
| 4776 | Btn2a2 | NM_175938.3 | chr13:23568931-23580726 |
| 4777 | Btnl1 | NM_001111094.1 | chr17:34514076-34522973 |
| 4778 | Btnl10 | NM_138678.2 | chr1:58731558-58740467 |
| 4779 | Btnl2 | NM_079835.2 | chr17:34491766-34506437 |
| 4780 | Btnl4 | NM_030746.1 | chr17:34605986-34612882 |
| 4781 | Btnl5-ps | NR_004051.1 | chr17:34624350-34634374 |
| 4782 | Btnl6 | NM_030747.1 | chr17:34644879-34654297 |
| 4783 | Btnl9 | NM_172793.2 | chr11:48981826-49000591 |
| 4784 | Btrc | NM_001037758.2 | chr19:45438223-45607833 |
| 4785 | Btrc | NM_001286465.1 | chr19:45438223-45607833 |
| 4786 | Btrc | NM_001286466.1 | chr19:45438223-45607833 |
| 4787 | Btrc | NM_009771.3 | chr19:45438223-45607833 |
| 4788 | Bub1 | NM_001113179.1 | chr2:127625935-127657595 |
| 4789 | Bub1 | NM_009772.2 | chr2:127625935-127657595 |
| 4790 | Bub1b | NM_009773.3 | chr2:118423946-118467328 |
| 4791 | Bub3 | NM_009774.3 | chr7:138703904-138715412 |
| 4792 | Bud13 | NM_146000.2 | chr9:46091094-46106866 |
| 4793 | Bud31 | NM_001008705.1 | chr5:145901266-145908943 |
| 4794 | Bves | NM_024265.2 | chr10:45055567-45089514 |
| 4795 | Bysl | NM_016859.3 | chr17:47736280-47748441 |
| 4796 | Bzrap1 | NM_172449.2 | chr11:87574042-87599430 |
| 4797 | Bzw1 | NM_025854.3 | chr1:58449979-58463392 |
| 4798 | Bzw2 | NM_025840.1 | chr12:36818421-36883412 |
| 4799 | C030006K11Rik | NM_145472.2 | chr15:76545705-76554275 |
| 4800 | C030006K11Rik | NM_178828.4 | chr15:76545705-76554275 |
| 4801 | C030007H22Rik | NR_040482.1 | chr1:91256916-91302708 |
| 4802 | C030013G03Rik | NR_077216.1 | chr17:12612839-12700570 |
| 4803 | C030013G03Rik | NR_077217.1 | chr17:12612839-12700570 |
| 4804 | C030016D13Rik | NR_027987.1 | chr19:27504526-27507121 |
| 4805 | C030018K13Rik | NR_045411.1 | chr5:64868246-64875205 |
| 4806 | C030018K13Rik | NR_045412.1 | chr5:64868246-64875205 |
| 4807 | C030018K13Rik | NR_045413.1 | chr5:64868246-64875205 |
| 4808 | C030023E24Rik | NR_033502.1 | chrX:58444467-58447339 |
| 4809 | C030029H02Rik | NR_102277.1 | chr7:143460006-143510194 |
| 4810 | C030034I22Rik | NR_028481.1 | chr17:69765786-69768532 |
| 4811 | C030034L19Rik | NR_015490.2 | chr3:9403077-9413903 |
| 4812 | C030037D09Rik | NR_038058.1 | chr1:88579956-88589886 |
| 4813 | C030039L03Rik | NM_001112731.1 | chr7:28459679-28491501 |
| 4814 | C030039L03Rik | NM_198417.2 | chr7:28459679-28491501 |
| 4815 | C030046E11Rik | NM_001081319.1 | chr19:29596771-29680411 |
| 4816 | C130021I20Rik | NR_046275.1 | chr2:33496712-33501183 |
| 4817 | C130026I21Rik | NM_001170979.1 | chr1:85242918-85267141 |
| 4818 | C130026L21Rik | NM_175219.3 | chr1:85242918-85267141 |
| 4819 | C130026L21Rik | NR_015546.2 | chr5:112010580-112016173 |
| 4820 | C130030K03Rik | NR_046212.1 | chr10:48813486-48815649 |
| 4821 | C130036L24Rik | NR_015507.2 | chr1:88256148-88264539 |
| 4822 | C130046K22Rik | NR_102388.1 | chr11:103559037-103586887 |
| 4823 | C130046K22Rik | NR_102389.1 | chr11:103559037-103586887 |
| 4824 | C130046K22Rik | NR_102396.1 | chr11:103559037-103586887 |
| 4825 | C130050O18Rik | NM_177000.3 | chr5:139882341-139892046 |
| 4826 | C130060C02Rik | NR_045355.1 | chr19:16059564-16085402 |
| 4827 | C130060K24Rik | NM_175524.4 | chr6:65331287-65408144 |
| 4828 | C130071C03Rik | NR_015561.2 | chr13:83867710-83875274 |
| 4829 | C130074J19Rik | NM_178892.3 | chr1:186695804-186706915 |
| 4830 | C130079G13Rik | NM_177661.3 | chr3:59729135-59741871 |
| 4831 | C130080G10Rik | NM_028422.1 | chr13:113880131-113887238 |
| 4832 | C130083M11Rik | NR_040717.1 | chr5:52591222-52607672 |
| 4833 | C1d | NM_020558.3 | chr11:17157620-17169179 |
| 4834 | C1galt1 | NM_052993.3 | chr6:7795223-7822042 |
| 4835 | C1galt1c1 | NM_023550.3 | chrX:35983959-35988320 |
| 4836 | C1qa | NM_007572.2 | chr4:136451830-136454759 |
| 4837 | C1qb | NM_009777.2 | chr4:136436060-136442092 |
| 4838 | C1qbp | NM_007573.2 | chr11:70791348-70796528 |
| 4839 | C1qc | NM_007574.2 | chr4:136445716-136448829 |
| 4840 | C1ql1 | NM_011795.2 | chr11:102800577-102807775 |
| 4841 | C1ql2 | NM_207233.1 | chr1:122237158-122239751 |
| 4842 | C1ql3 | NM_153155.2 | chr2:12923514-12932491 |
| 4843 | C1ql4 | NM_001024702.1 | chr15:98915184-98918159 |
| 4844 | C1qtnf1 | NM_001204129.1 | chr11:118289770-118316309 |
| 4845 | C1qtnf1 | NM_001204130.1 | chr11:118289770-118316309 |
| 4846 | C1qtnf1 | NM_019959.3 | chr11:118289770-118316309 |
| 4847 | C1qtnf2 | NM_026979.5 | chr11:43287807-43305027 |
| 4848 | C1qtnf3 | NM_001204134.1 | chr15:10882086-10909917 |
| 4849 | C1qtnf3 | NM_030888.4 | chr15:10882086-10909917 |
| 4850 | C1qtnf4 | NM_026161.3 | chr2:90725942-90730683 |
| 4851 | C1qtnf5 | NM_001040631.2 | chr9:43909852-43917270 |
| 4852 | C1qtnf5 | NM_001040632.2 | chr9:43909852-43917270 |
| 4853 | C1qtnf5 | NM_001190319.1 | chr9:43909852-43917270 |
| 4854 | C1qtnf5 | NM_145613.4 | chr9:43909852-43917270 |
| 4855 | C1qtnf6 | NM_001204152.1 | chr15:78353775-78360081 |
| 4856 | C1qtnf6 | NM_001204153.1 | chr15:78353775-78360081 |
| 4857 | C1qtnf6 | NM_028331.2 | chr15:78353775-78360081 |
| 4858 | C1qtnf7 | NM_001135172.1 | chr5:43906807-44007825 |
| 4859 | C1qtnf7 | NM_175425.4 | chr5:43906807-44007825 |
| 4860 | C1qtnf9 | NM_183175.4 | chr14:61386970-61399706 |
| 4861 | C1ra | NM_023143.3 | chr6:124462638-124473458 |
| 4862 | C1rb | NM_001113356.1 | chr6:124520447-124531062 |
| 4863 | C1rl | NM_181344.5 | chr6:124443130-124460661 |
| 4864 | C1s1 | NM_001097617.1 | chr6:124480361-124492377 |
| 4865 | C1s1 | NM_144938.2 | chr6:124480361-124492377 |
| 4866 | C1s2 | NM_173864.1 | chr6:124574642-124586103 |
| 4867 | C2 | NM_013484.2 | chr17:34999546-35019045 |
| 4868 | C230004F18Rik | NR_030706.1 | chrX:58369552-58392635 |
| 4869 | C230024C17Rik | NR_046371.1 | chr1:155568369-155584959 |
| 4870 | C230029M16 | NR_110482.1 | chr10:118357436-118364199 |
| 4871 | C230035H16Rik | NR_015492.1 | chr13:23519844-23522886 |
| 4872 | C230037L18Rik | NR_077233.1 | chr15:89306683-89315281 |
| 4873 | C230052I12Rik | NM_178643.5 | chr7:36177171-36181786 |
| 4874 | C230079O03Rik | NR_040459.1 | chr7:143523898-143541098 |
| 4875 | C230091D08Rik | NR_015479.1 | chr7:66563293-66579519 |
| 4876 | C2cd2 | NM_174847.2 | chr16:98076816-98144243 |
| 4877 | C2cd2l | NM_027909.2 | chr9:44117319-44128365 |
| 4878 | C2cd3 | NM_001017985.2 | chr7:107520742-107618668 |
| 4879 | C2cd4a | NM_001163143.1 | chr9:67678338-67680137 |
| 4880 | C2cd4b | NM_001081314.2 | chr9:67607243-67608740 |
| 4881 | C2cd4c | NM_001168624.1 | chr10:79069598-79076770 |
| 4882 | C2cd4c | NM_198614.3 | chr10:79069598-79076770 |
| 4883 | C2cd4d | NM_001136117.1 | chr3:94166365-94168489 |
| 4884 | C2cd5 | NM_001109688.2 | chr6:142959439-143048672 |
| 4885 | C2cd5 | NM_001286578.1 | chr6:142959439-143048672 |
| 4886 | C2cd5 | NM_029081.3 | chr6:142959439-143048672 |
| 4887 | C2cd5 | NM_029897.2 | chr6:142959439-143048672 |
| 4888 | C3 | NM_009778.3 | chr17:57343390-57367559 |
| 4889 | C330006A16Rik | NM_001256521.1 | chr2:25992326-25996026 |
| 4890 | C330006A16Rik | NM_001256522.1 | chr2:25992326-25996026 |
| 4891 | C330007P06Rik | NM_029951.1 | chrX:34388538-34404241 |
| 4892 | C330011F03Rik | NR_046166.1 | chr17:51564533-51587594 |
| 4893 | C330013E15Rik | NR_045701.1 | chr15:100444570-100445541 |
| 4894 | C330013F16Rik | NR_045455.1 | chrX:135774764-135892277 |
| 4895 | C330013F16Rik | NR_045456.1 | chrX:135774764-135892277 |
| 4896 | C330018D20Rik | NM_029909.1 | chr18:57115484-57135033 |
| 4897 | C330021F23Rik | NM_001024728.2 | chr8:3567997-3584776 |
| 4898 | C330022C24Rik | NR_045717.1 | chr7:148023120-148031588 |
| 4899 | C330024C12Rik | NR_046016.1 | chr17:87591555-87594282 |
| 4900 | C330024D21Rik | NR_015582.2 | chr5:67855136-67869138 |
| 4901 | C330024D21Rik | NM_110363.1 | chr5:67855136-67869138 |
| 4902 | C330027C09Rik | NM_172616.2 | chr16:48994300-49019818 |
| 4903 | C330046G13Rik | NR_040658.1 | chr10:84010161-84016083 |
| 4904 | C3ar1 | NM_009779.2 | chr6:122797157-122806175 |
| 4905 | C430002E04Rik | NR_040385.1 | chr3:41291602-41297121 |
| 4906 | C430002N11Rik | NR_102293.1 | chr9:96665980-96674816 |
| 4907 | C430002N11Rik | NR_102294.1 | chr9:96665980-96674816 |
| 4908 | C430002N11Rik | NR_102295.1 | chr9:96665980-96674816 |
| 4909 | C430002N11Rik | NR_102296.1 | chr9:96665980-96674816 |
| 4910 | C430049B03Rik | NR_038184.1 | chrX:50406288-50410367 |
| 4911 | C430049B03Rik | NR_038185.1 | chrX:50406288-50410367 |
| 4912 | C4a | NM_014134.2 | chr17:34946036-34960399 |
| 4913 | C4b | NM_009780.2 | chr17:34865325-34880842 |
| 4914 | C4bp | NM_007576.3 | chr1:132532497-132558195 |
| 4915 | C4bp-ps1 | NR_028304.1 | chr1:132566778-132578148 |
| 4916 | C530005A16Rik | NM_029450.1 | chr4:116626338-116670235 |
| 4917 | C530008M17Rik | NM_001163793.1 | chr5:77269623-77302579 |
| 4918 | C530044C16Rik | NR_045984.1 | chr6:50726113-50764893 |
| 4919 | C5ar1 | NM_001173550.1 | chr7:16832091-16844889 |
| 4920 | C5ar1 | NM_007577.4 | chr7:16832091-16844889 |
| 4921 | C5ar2 | NM_001146005.1 | chr7:16819933-16829503 |
| 4922 | C5ar2 | NM_176912.4 | chr7:16819933-16829503 |
| 4923 | C6 | NM_016704.2 | chr15:4677209-4754045 |
| 4924 | C630028M04Rik | NR_040668.1 | chr4:51980965-52063982 |
| 4925 | C630031E19Rik | NR_046080.1 | chr12:30360495-30371310 |
| 4926 | C630043F03Rik | NR_027923.1 | chr4:71862277-71864964 |
| 4927 | C7 | NM_001243837.1 | chr15:4938761-5013773 |
| 4928 | C730002L08Rik | NR_045778.1 | chr19:20609017-20626820 |

Fig. 25 - 27

| | | | |
|---|---|---|---|
| 4929 | C730027H18Rik | NR_038040.1 | chr10:70631484-70644788 |
| 4930 | C730036E19Rik | NR_038011.1 | chr5:152985163-152991225 |
| 4931 | C77080 | NM_001033189.3 | chr4:128867038-128938648 |
| 4932 | C77080 | NM_001285865.1 | chr4:128867038-128938648 |
| 4933 | C77080 | NM_001285866.1 | chr4:128867038-128938648 |
| 4934 | C77080 | NM_001285867.1 | chr4:128867038-128938648 |
| 4935 | C77370 | NM_001077354.2 | chrX:101271775-101396456 |
| 4936 | C78339 | NM_001033192.2 | chr13:46764890-46771142 |
| 4937 | C86187 | NR_015609.1 | chr7:54223116-54231281 |
| 4938 | C86695 | NM_001081662.1 | chr8:23069185-23074775 |
| 4939 | C87198 | NR_046002.1 | chr12:57692045-57695541 |
| 4940 | C87198 | NR_046003.1 | chr12:57692045-57695541 |
| 4941 | C87414 | NM_001164284.1 | chr5:94064210-94100489 |
| 4942 | C87414 | NM_001164285.1 | chr5:94064210-94100489 |
| 4943 | C87436 | NM_001243741.1 | chr6:86388391-86420381 |
| 4944 | C87436 | NM_001243742.1 | chr6:86388391-86420381 |
| 4945 | C87436 | NM_146170.4 | chr6:86388391-86420381 |
| 4946 | C87499 | NM_198663.3 | chr4:88273223-88280090 |
| 4947 | C87499 | NR_027385.1 | chr4:88273223-88280090 |
| 4948 | C87977 | NM_001177542.1 | chr4:143796664-143802920 |
| 4949 | C8a | NM_001290645.1 | chr4:104488284-104549003 |
| 4950 | C8a | NM_146148.2 | chr4:104488284-104549003 |
| 4951 | C8b | NM_133882.2 | chr4:104438921-104477153 |
| 4952 | C8g | NM_001271777.1 | chr2:25354169-25360990 |
| 4953 | C8g | NM_027062.2 | chr2:25354169-25360990 |
| 4954 | C9 | NM_013485.1 | chr15:6395332-6446476 |
| 4955 | C920006O11Rik | NR_040401.1 | chr9:78023720-78026689 |
| 4956 | C920009B18Rik | NR_015465.2 | chr10:22026526-22032748 |
| 4957 | C920021L13Rik | NR_040446.1 | chr3:95675445-95693016 |
| 4958 | C920025E04Rik | NM_001271005.1 | chr17:36245974-36248621 |
| 4959 | Caap1 | NM_026368.2 | chr4:94166769-94223487 |
| 4960 | Cab39 | NM_133781.4 | chr1:87690021-87748152 |
| 4961 | Cab39l | NM_026908.3 | chr14:60059817-60167740 |
| 4962 | Cabin1 | NM_172549.3 | chr10:75108854-75227102 |
| 4963 | Cables1 | NM_001146287.1 | chr18:11979596-12104136 |
| 4964 | Cables1 | NM_022021.2 | chr18:11979596-12104136 |
| 4965 | Cables2 | NM_145851.2 | chr2:179993243-180008170 |
| 4966 | Cabp1 | NM_013879.2 | chr5:115618699-115636130 |
| 4967 | Cabp2 | NM_001160252.1 | chr19:4082487-4087339 |
| 4968 | Cabp2 | NM_001160253.1 | chr19:4082487-4087339 |
| 4969 | Cabp2 | NM_013878.2 | chr19:4082487-4087339 |
| 4970 | Cabp4 | NM_144532.2 | chr19:4135422-4139609 |
| 4971 | Cabp5 | NM_013877.3 | chr7:13983503-13994227 |
| 4972 | Cabp7 | NM_138948.3 | chr11:4638823-4646781 |
| 4973 | Cabs1 | NM_027631.2 | chr5:88408475-88410566 |
| 4974 | Cabyr | NM_001042418.1 | chr18:12899863-12913651 |
| 4975 | Cabyr | NM_001042419.1 | chr18:12899863-12913651 |
| 4976 | Cabyr | NM_001042420.1 | chr18:12899863-12913651 |
| 4977 | Cabyr | NM_027687.2 | chr18:12899863-12913651 |
| 4978 | Cabyr | NM_181731.1 | chr18:12899863-12913651 |
| 4979 | Cacfd1 | NM_001243239.1 | chr2:26865445-26876609 |
| 4980 | Cacfd1 | NM_001243240.1 | chr2:26865445-26876609 |
| 4981 | Cacfd1 | NM_029862.4 | chr2:26865445-26876609 |
| 4982 | Cachd1 | NM_198037.1 | chr4:100449283-100676353 |
| 4983 | Cacna1a | NM_001252059.1 | chr8:86939262-87164148 |
| 4984 | Cacna1a | NM_001252060.1 | chr8:86939262-87164148 |
| 4985 | Cacna1a | NM_001252061.1 | chr8:86939262-87164148 |
| 4986 | Cacna1a | NM_007578.3 | chr8:86939262-87164148 |
| 4987 | Cacna1b | NM_001042528.2 | chr2:24459408-24618672 |
| 4988 | Cacna1b | NM_007579.3 | chr2:24459408-24618672 |
| 4989 | Cacna1c | NM_001159533.2 | chr6:118537257-119171632 |
| 4990 | Cacna1c | NM_001159534.2 | chr6:118537257-119171632 |
| 4991 | Cacna1c | NM_001159535.2 | chr6:118537257-119171632 |
| 4992 | Cacna1c | NM_001255997.2 | chr6:118537257-119171632 |
| 4993 | Cacna1c | NM_001255998.2 | chr6:118537257-119171632 |
| 4994 | Cacna1c | NM_001255999.2 | chr6:118537257-119171632 |
| 4995 | Cacna1c | NM_001256000.2 | chr6:118537257-119171632 |
| 4996 | Cacna1c | NM_001256001.2 | chr6:118537257-119171632 |
| 4997 | Cacna1c | NM_001256002.2 | chr6:118537257-119171632 |
| 4998 | Cacna1c | NM_001256005.1 | chr6:118537257-119171632 |
| 4999 | Cacna1c | NM_009781.4 | chr6:118537257-119171632 |
| 5000 | Cacna1d | NM_001083616.2 | chr14:30822185-31340242 |
| 5001 | Cacna1d | NM_028981.3 | chr14:30822185-31340242 |
| 5002 | Cacna1e | NM_009782.3 | chr1:156239648-156573050 |
| 5003 | Cacna1f | NM_019582.2 | chrX:7184228-7212322 |
| 5004 | Cacna1g | NM_001112813.1 | chr11:94269704-94335512 |
| 5005 | Cacna1g | NM_001177888.1 | chr11:94269704-94335512 |
| 5006 | Cacna1g | NM_001177890.1 | chr11:94269704-94335512 |
| 5007 | Cacna1g | NM_009783.3 | chr11:94269704-94335512 |
| 5008 | Cacna1h | NM_001163691.1 | chr17:25507497-25570728 |
| 5009 | Cacna1h | NM_021415.4 | chr17:25507497-25570728 |
| 5010 | Cacna1i | NM_001044308.2 | chr15:80117667-80228722 |
| 5011 | Cacna1s | NM_001081023.1 | chr1:137949477-138016399 |
| 5012 | Cacna1s | NM_014193.2 | chr1:137949477-138016399 |
| 5013 | Cacna2d1 | NM_001110843.1 | chr5:15440508-15880329 |
| 5014 | Cacna2d1 | NM_001110844.1 | chr5:15440508-15880329 |
| 5015 | Cacna2d1 | NM_001110846.1 | chr5:15440508-15880329 |
| 5016 | Cacna2d1 | NM_001110846.1 | chr5:15440508-15880329 |
| 5017 | Cacna2d1 | NM_009784.2 | chr5:15440508-15880329 |
| 5018 | Cacna2d2 | NM_001174047.1 | chr9:107302210-107431674 |
| 5019 | Cacna2d2 | NM_001174048.1 | chr9:107302210-107431674 |
| 5020 | Cacna2d2 | NM_001174049.1 | chr9:107302210-107431674 |
| 5021 | Cacna2d2 | NM_001174050.1 | chr9:107302210-107431674 |
| 5022 | Cacna2d2 | NM_020263.3 | chr9:107302210-107431674 |
| 5023 | Cacna2d3 | NM_009785.1 | chr14:29718129-30535050 |
| 5024 | Cacna2d4 | NM_001033382.2 | chr6:119186544-119302425 |
| 5025 | Cacnb1 | NM_001159319.2 | chr11:97862821-97883941 |
| 5026 | Cacnb1 | NM_001159320.2 | chr11:97862821-97883941 |
| 5027 | Cacnb1 | NM_001282977.1 | chr11:97862821-97883941 |
| 5028 | Cacnb1 | NM_001282978.1 | chr11:97862821-97883941 |
| 5029 | Cacnb1 | NM_031173.4 | chr11:97862821-97883941 |
| 5030 | Cacnb1 | NM_145121.3 | chr11:97862821-97883941 |
| 5031 | Cacnb2 | NM_001252533.1 | chr2:14525932-14909535 |
| 5032 | Cacnb2 | NM_023116.4 | chr2:14525932-14909535 |
| 5033 | Cacnb2 | NR_045533.1 | chr2:14525932-14909535 |
| 5034 | Cacnb3 | NM_001044741.2 | chr15:98462758-98474967 |
| 5035 | Cacnb3 | NM_001286226.1 | chr15:98462758-98474967 |
| 5036 | Cacnb3 | NM_007581.2 | chr15:98462758-98474967 |
| 5037 | Cacnb4 | NM_001037099.2 | chr2:52283839-52532128 |
| 5038 | Cacnb4 | NM_001285426.1 | chr2:52283839-52532128 |
| 5039 | Cacnb4 | NM_001285427.1 | chr2:52283839-52532128 |
| 5040 | Cacnb4 | NM_001285428.1 | chr2:52283839-52532128 |
| 5041 | Cacnb4 | NM_146123.3 | chr2:52283839-52532128 |
| 5042 | Cacng1 | NM_007582.2 | chr11:107564531-107577790 |
| 5043 | Cacng2 | NM_007583.2 | chr15:77824052-77949710 |
| 5044 | Cacng3 | NM_019430.2 | chr7:129815257-129912907 |
| 5045 | Cacng4 | NM_019431.2 | chr11:107596093-107655778 |
| 5046 | Cacng5 | NM_001199301.1 | chr11:107735918-107776369 |
| 5047 | Cacng5 | NM_080644.3 | chr11:107735918-107776369 |
| 5048 | Cacng6 | NM_133183.1 | chr7:3425422-3435658 |
| 5049 | Cacng7 | NM_133189.3 | chr7:3336684-3366537 |
| 5050 | Cacng8 | NM_133190.1 | chr7:3394458-3415366 |
| 5051 | Cactin | NM_027381.2 | chr10:80783847-80788996 |
| 5052 | Cacul1 | NM_001172096.1 | chr19:60600598-60656926 |
| 5053 | Cacul1 | NM_001172097.1 | chr19:60600598-60656926 |
| 5054 | Cacul1 | NM_030197.2 | chr19:60600598-60656926 |
| 5055 | Cacybp | NM_009786.2 | chr1:162132497-162143023 |
| 5056 | Cad | NM_001289522.1 | chr5:31235515-31651218 |
| 5057 | Cad | NM_001289523.1 | chr5:31235515-31651218 |
| 5058 | Cad | NM_023525.2 | chr5:31235515-31651218 |
| 5059 | Cadm1 | NM_001025600.1 | chr9:47338434-47661468 |
| 5060 | Cadm1 | NM_018770.3 | chr9:47338434-47661468 |
| 5061 | Cadm1 | NM_207675.2 | chr9:47338434-47661468 |
| 5062 | Cadm1 | NM_207676.2 | chr9:47338434-47661468 |
| 5063 | Cadm2 | NM_001145977.1 | chr16:66655665-67621153 |
| 5064 | Cadm2 | NM_178721.4 | chr16:66655665-67621153 |
| 5065 | Cadm3 | NM_053199.3 | chr1:175264384-175297826 |
| 5066 | Cadm4 | NM_153112.3 | chr7:25267041-25289552 |
| 5067 | Cadps | NM_001042617.1 | chr14:13205076-13655593 |
| 5068 | Cadps | NM_012061.3 | chr14:13205076-13655593 |
| 5069 | Cadps2 | NM_001252105.1 | chr6:23212773-23789421 |
| 5070 | Cadps2 | NM_001252106.1 | chr6:23212773-23789421 |
| 5071 | Cadps2 | NM_001252107.1 | chr6:23212773-23789421 |
| 5072 | Cadps2 | NM_001252108.1 | chr6:23212773-23789421 |
| 5073 | Cadps2 | NM_001252109.1 | chr6:23212773-23789421 |
| 5074 | Cadps2 | NM_001252110.1 | chr6:23212773-23789421 |
| 5075 | Cadps2 | NM_153163.4 | chr6:23212773-23789421 |
| 5076 | Cage1 | NM_027724.2 | chr13:38097920-38128806 |
| 5077 | Calb1 | NM_009788.4 | chr4:15808410-15833856 |
| 5078 | Calb2 | NM_007586.1 | chr8:112666437-112692106 |
| 5079 | Calca | NM_001033954.3 | chr7:121774991-121779871 |
| 5080 | Calca | NM_001289444.1 | chr7:121774991-121779871 |
| 5081 | Calca | NM_007587.2 | chr7:121774991-121779871 |
| 5082 | Calcb | NM_054084.2 | chr7:121862156-121866879 |
| 5083 | Calcoco1 | NM_026192.3 | chr15:102537207-102552609 |
| 5084 | Calcoco2 | NM_001271018.1 | chr11:95960229-95973276 |
| 5085 | Calcr | NM_001042725.1 | chr6:3635719-3714713 |
| 5086 | Calcr | NM_007588.2 | chr6:3635719-3714713 |
| 5087 | Calcrl | NM_018782.2 | chr2:84170782-84265423 |
| 5088 | Cald1 | NM_145575.3 | chr6:34659443-34725469 |
| 5089 | Calhm1 | NM_001081271.1 | chr19:47215524-47218664 |
| 5090 | Calhm2 | NM_133746.5 | chr19:47206721-47212784 |
| 5091 | Calm1 | NM_009790.4 | chr12:101437750-101448016 |
| 5092 | Calm2 | NM_007589.5 | chr17:87832740-87846275 |
| 5093 | Calm3 | NM_007590.3 | chr7:17500727-17509381 |
| 5094 | Calm4 | NM_020036.4 | chr13:3837002-3837917 |
| 5095 | Calm5 | NM_001008706.1 | chr13:3853418-3854007 |
| 5096 | Calml3 | NM_027416.3 | chr13:3802138-3803564 |
| 5097 | Calml4 | NM_001102468.1 | chr9:62686593-62723724 |
| 5098 | Calml4 | NM_138304.2 | chr9:62686593-62723724 |
| 5099 | Caln1 | NM_021371.2 | chr5:130845327-131316515 |
| 5100 | Caln1 | NM_181045.1 | chr5:130845327-131316515 |
| 5101 | Calr | NM_007591.3 | chr8:87365986-87370830 |
| 5102 | Calr3 | NM_028500.3 | chr8:74948081-74967677 |
| 5103 | Calr3 | NM_029782.3 | chr8:74948081-74967677 |
| 5104 | Calr4 | NM_001033226.4 | chr4:108891017-108927182 |
| 5105 | Calr4 | NM_001285895.1 | chr4:108891017-108927182 |
| 5106 | Calr4 | NM_001285896.1 | chr4:108891017-108927182 |
| 5107 | Calr4 | NM_001285897.1 | chr4:108891017-108927182 |
| 5108 | Calr4 | NM_001285898.1 | chr4:108891017-108927182 |
| 5109 | Calu | NM_001285412.1 | chr6:29298105-29330513 |
| 5110 | Calu | NM_007594.4 | chr6:29298105-29330513 |
| 5111 | Calu | NM_184053.3 | chr6:29298105-29330513 |
| 5112 | Caly | NM_001190385.1 | chr7:147255778-147268447 |
| 5113 | Caly | NM_001190386.1 | chr7:147255778-147268447 |
| 5114 | Caly | NM_026769.2 | chr7:147255778-147268447 |
| 5115 | Camk1 | NM_133926.2 | chr6:113284118-113293916 |
| 5116 | Camk1d | NM_001290374.1 | chr2:5214502-5635808 |
| 5117 | Camk1d | NM_001290375.1 | chr2:5214502-5635808 |
| 5118 | Camk1d | NM_001290376.1 | chr2:5214502-5635808 |

Fig. 25 - 28

| | | | | | | | | |
|---|---|---|---|---|---|---|---|---|
| 5119 | Camk1d | NM_177343.4 | chr2:5214502-5635808 | | 5214 | Car3 | NM_007606.3 | chr3:14863537-14872373 |
| 5120 | Camk1g | NM_144817.2 | chr1:195172539-195196476 | | 5215 | Car4 | NM_007607.2 | chr11:84771255-84779556 |
| 5121 | Camk2a | NM_001286809.1 | chr18:61085285-61147806 | | 5216 | Car5a | NM_007608.2 | chr8:124440044-124468812 |
| 5122 | Camk2a | NM_009792.3 | chr18:61085285-61147806 | | 5217 | Car5b | NM_181315.4 | chrX:160414753-160465942 |
| 5123 | Camk2a | NM_177407.4 | chr18:61085285-61147806 | | 5218 | Car6 | NM_009802.2 | chr4:149561124-149575244 |
| 5124 | Camk2b | NM_001174053.1 | chr11:5869668-5965751 | | 5219 | Car7 | NM_053070.3 | chr8:107064706-107074243 |
| 5125 | Camk2b | NM_001174054.1 | chr11:5869668-5965751 | | 5220 | Car8 | NM_007592.3 | chr4:8068639-8166188 |
| 5126 | Camk2b | NM_007595.5 | chr11:5869668-5965751 | | 5221 | Car9 | NM_139305.2 | chr4:43519897-43526597 |
| 5127 | Camk2d | NM_001025438.2 | chr3:126299890-126547972 | | 5222 | Card10 | NM_130859.2 | chr15:78605565-78633472 |
| 5128 | Camk2d | NM_001025439.2 | chr3:126299890-126547972 | | 5223 | Card11 | NM_175362.2 | chr5:141348952-141476550 |
| 5129 | Camk2d | NM_023813.4 | chr3:126299890-126547972 | | 5224 | Card14 | NM_130886.3 | chr11:119176101-119206689 |
| 5130 | Camk2g | NM_001039138.2 | chr14:21554094-21613310 | | 5225 | Card6 | NM_001163138.1 | chr15:5047438-5058533 |
| 5131 | Camk2g | NM_001039139.2 | chr14:21554094-21613310 | | 5226 | Card9 | NM_001037747.1 | chr2:26207831-26215067 |
| 5132 | Camk2g | NM_178597.5 | chr14:21554094-21613310 | | 5227 | Carf | NM_001285463.1 | chr1:60133711-60210797 |
| 5133 | Camk2n1 | NM_025451.2 | chr4:138011062-138016041 | | 5228 | Carf | NM_001285473.1 | chr1:60133711-60210797 |
| 5134 | Camk2n2 | NM_028420.2 | chr16:20619288-20621351 | | 5229 | Carf | NM_139150.5 | chr1:60133711-60210797 |
| 5135 | Camk4 | NM_009793.3 | chr18:33098694-33355421 | | 5230 | Carf | NR_104344.1 | chr1:60133711-60210797 |
| 5136 | Camkk1 | NM_018883.2 | chr11:72832509-72855567 | | 5231 | Carhsp1 | NM_025821.2 | chr16:8658679-8672246 |
| 5137 | Camkk2 | NM_001199676.1 | chr5:123181179-123229419 | | 5232 | Carkd | NM_001190357.1 | chr8:11497505-11513286 |
| 5138 | Camkk2 | NM_145358.2 | chr5:123181179-123229419 | | 5233 | Carkd | NM_026995.4 | chr8:11497505-11513286 |
| 5139 | Camkmt | NM_028576.3 | chr17:85490039-85857920 | | 5234 | Carm1 | NM_021531.5 | chr9:21351337-21400414 |
| 5140 | Camkv | NM_145621.2 | chr9:107838250-107852022 | | 5235 | Carm1 | NM_153141.1 | chr9:21351337-21400414 |
| 5141 | Caml | NM_007596.2 | chr3:55724365-55733777 | | 5236 | Carns1 | NM_134148.2 | chr19:4164323-4175479 |
| 5142 | Camp | NM_009921.2 | chr9:109749890-109751970 | | 5237 | Cars | NM_001252593.1 | chr7:150743134-150785995 |
| 5143 | Camsap1 | NM_001276359.1 | chr2:25782357-25838802 | | 5238 | Cars | NM_013742.5 | chr7:150743134-150785995 |
| 5144 | Camsap1 | NM_001276360.1 | chr2:25782357-25838802 | | 5239 | Cars2 | NM_024248.1 | chr8:11514016-11550771 |
| 5145 | Camsap1 | NM_001276361.1 | chr2:25782357-25838802 | | 5240 | Cartpt | NM_001081493.2 | chr13:100668437-100670638 |
| 5146 | Camsap2 | NM_001081360.1 | chr1:138164699-138242681 | | 5241 | Cartpt | NM_013732.7 | chr13:100668437-100670638 |
| 5147 | Camsap3 | NM_001183749.1 | chr8:3587449-3609075 | | 5242 | Casc1 | NM_177222.4 | chr6:145123392-145159490 |
| 5148 | Camsap3 | NM_027171.3 | chr8:3587449-3609075 | | 5243 | Casc3 | NM_138660.2 | chr11:98671122-98695121 |
| 5149 | Camta1 | NM_001018557.3 | chr4:150433631-151235877 | | 5244 | Casc4 | NM_001205369.1 | chr2:121692705-121761943 |
| 5150 | Camta1 | NM_001195565.1 | chr4:150433631-151235877 | | 5245 | Casc4 | NM_001205370.1 | chr2:121692705-121761943 |
| 5151 | Camta2 | NM_001190376.1 | chr11:70482964-70501607 | | 5246 | Casc4 | NM_001205371.1 | chr2:121692705-121761943 |
| 5152 | Camta2 | NM_001190378.1 | chr11:70482964-70501607 | | 5247 | Casc4 | NM_177054.4 | chr2:121692705-121761943 |
| 5153 | Camta2 | NM_001190379.1 | chr11:70482964-70501607 | | 5248 | Casc4 | NM_199038.3 | chr2:121692705-121761943 |
| 5154 | Camta2 | NM_178136.4 | chr11:70482964-70501607 | | 5249 | Casc5 | NM_029617.2 | chr2:118872854-118929857 |
| 5155 | Cand1 | NM_027994.1 | chr10:118635867-118677111 | | 5250 | Casd1 | NM_145398.2 | chr6:4551065-4593383 |
| 5156 | Cand2 | NM_025958.2 | chr6:115724575-115755573 | | 5251 | Cask | NM_001284503.1 | chrX:13094207-13423682 |
| 5157 | Cant1 | NM_001025617.2 | chr11:118267602-118280432 | | 5252 | Cask | NM_001284504.1 | chrX:13094207-13423682 |
| 5158 | Cant1 | NM_001025618.2 | chr11:118267602-118280432 | | 5253 | Cask | NM_001284505.1 | chrX:13094207-13423682 |
| 5159 | Cant1 | NM_001267591.1 | chr11:118267602-118280432 | | 5254 | Cask | NM_009806.3 | chrX:13094207-13423682 |
| 5160 | Cant1 | NM_001267592.1 | chr11:118267602-118280432 | | 5255 | Caskin1 | NM_027937.2 | chr17:24625728-24645852 |
| 5161 | Cant1 | NM_029502.3 | chr11:118267602-118280432 | | 5256 | Caskin2 | NM_080643.2 | chr11:115660665-115674906 |
| 5162 | Canx | NM_001110499.1 | chr11:50107458-50139175 | | 5257 | Casp1 | NM_009807.2 | chr9:5298516-5307281 |
| 5163 | Canx | NM_001110500.1 | chr11:50107458-50139175 | | 5258 | Casp12 | NM_009808.4 | chr9:5345475-5373034 |
| 5164 | Canx | NM_007597.3 | chr11:50107458-50139175 | | 5259 | Casp14 | NM_009809.5 | chr10:78174739-78181038 |
| 5165 | Cap1 | NM_007598.4 | chr4:122536470-122563124 | | 5260 | Casp2 | NM_007610.2 | chr6:42215037-42232495 |
| 5166 | Cap2 | NM_026056.4 | chr13:46597271-46745650 | | 5261 | Casp3 | NM_001284409.1 | chr8:47702644-47725052 |
| 5167 | Capg | NM_001042534.3 | chr6:72494384-72512977 | | 5262 | Casp3 | NM_009810.3 | chr8:47702644-47725052 |
| 5168 | Capg | NM_001271395.1 | chr6:72494384-72512977 | | 5263 | Casp4 | NM_007609.3 | chr9:5308859-5336791 |
| 5169 | Capg | NM_001271415.1 | chr6:72494384-72512977 | | 5264 | Casp6 | NM_009811.4 | chr3:129604342-129617020 |
| 5170 | Capg | NM_007599.3 | chr6:72494384-72512977 | | 5265 | Casp7 | NM_007611.2 | chr19:56471618-56516833 |
| 5171 | Capn1 | NM_001110504.1 | chr19:5988544-6018459 | | 5266 | Casp8 | NM_001080126.1 | chr1:58852217-58904347 |
| 5172 | Capn1 | NM_007600.3 | chr19:5988544-6018459 | | 5267 | Casp8 | NM_001277926.1 | chr1:58852217-58904347 |
| 5173 | Capn10 | NM_011796.2 | chr1:94830985-94844525 | | 5268 | Casp8 | NM_009812.2 | chr1:58852217-58904347 |
| 5174 | Capn11 | NM_001013767.1 | chr17:457767152-45796258 | | 5269 | Casp8ap2 | NM_001122978.1 | chr4:32702447-32740240 |
| 5175 | Capn12 | NM_001110807.1 | chr7:29666675-29678604 | | 5270 | Casp8ap2 | NM_011997.2 | chr4:32702447-32740240 |
| 5176 | Capn13 | NM_001033444.2 | chr17:73655803-73748636 | | 5271 | Casp9 | NM_001277932.1 | chr4:141349526-141381918 |
| 5177 | Capn15 | NM_015830.1 | chr17:26096500-26102450 | | 5272 | Casp9 | NM_015733.5 | chr4:141349526-141381918 |
| 5178 | Capn2 | NM_009794.3 | chr1:184397389-184447614 | | 5273 | Casq1 | NM_009813.2 | chr1:174140024-174150026 |
| 5179 | Capn3 | NM_001109761.2 | chr2:120181044-120330655 | | 5274 | Casq2 | NM_009814.3 | chr3:101890377-101950435 |
| 5180 | Capn3 | NM_001177799.1 | chr2:120181044-120330655 | | 5275 | Casr | NM_013803.2 | chr16:36493781-36562220 |
| 5181 | Capn3 | NM_007601.3 | chr2:120181044-120330655 | | 5276 | Cass4 | NM_001080820.2 | chr2:172219293-172259257 |
| 5182 | Capn5 | NM_007602.4 | chr7:105270069-105326784 | | 5277 | Cass4 | NM_001276422.1 | chr2:172219293-172259257 |
| 5183 | Capn6 | NM_007603.3 | chrX:140236779-140261955 | | 5278 | Cass4 | NM_001276423.1 | chr2:172219293-172259257 |
| 5184 | Capn7 | NM_009796.2 | chr14:32149909-32185169 | | 5279 | Cast | NM_009817.4 | chr13:74831733-74945369 |
| 5185 | Capn8 | NM_001145806.1 | chr1:184495137-184562483 | | 5280 | Casz1 | NM_001159344.1 | chr4:148178500-148329001 |
| 5186 | Capn8 | NM_130890.2 | chr1:184495137-184562483 | | 5281 | Casz1 | NM_027195.2 | chr4:148178500-148329001 |
| 5187 | Capn9 | NM_023709.4 | chr8:127100010-127142631 | | 5282 | Cat | NM_009804.2 | chr2:103294060-103325310 |
| 5188 | Capns1 | NM_009795.3 | chr7:30971960-30980067 | | 5283 | Catip | NM_001033345.2 | chr1:74408681-74415895 |
| 5189 | Capns2 | NM_027112.1 | chr8:95425294-95426308 | | 5284 | Catsper1 | NM_139301.2 | chr19:5335740-5344153 |
| 5190 | Caprin1 | NM_001111289.1 | chr2:103603101-103637797 | | 5285 | Catsper2 | NM_153075.3 | chr2:121220090-121239528 |
| 5191 | Caprin1 | NM_001111290.1 | chr2:103603101-103637797 | | 5286 | Catsper3 | NM_001252487.1 | chr13:55885939-55910361 |
| 5192 | Caprin1 | NM_001111291.1 | chr2:103603101-103637797 | | 5287 | Catsper3 | NM_001252488.1 | chr13:55885939-55910361 |
| 5193 | Caprin1 | NM_001111292.1 | chr2:103603101-103637797 | | 5288 | Catsper3 | NM_029772.4 | chr13:55885939-55910361 |
| 5194 | Caprin1 | NM_016739.3 | chr2:103603101-103637797 | | 5289 | Catsper4 | NM_001130030.1 | chr4:133767882-133783298 |
| 5195 | Caprin2 | NM_181541.4 | chr6:148791033-148844648 | | 5290 | Catsper4 | NM_177866.4 | chr4:133767882-133783298 |
| 5196 | Caps2 | NM_178278.4 | chr10:111602731-111653611 | | 5291 | Catsperb | NM_173023.2 | chr12:102642882-102864219 |
| 5197 | Capsl | NM_029341.1 | chr15:9365782-9395790 | | 5292 | Catsperd | NM_175350.3 | chr17:56767565-56803879 |
| 5198 | Capza1 | NM_009797.2 | chr3:104625702-104667423 | | 5293 | Catsperg1 | NM_001164658.1 | chr7:29966550-29959052 |
| 5199 | Capza2 | NM_007604.2 | chr6:17587097-17616536 | | 5294 | Catsperg2 | NM_029714.3 | chr7:30482237-30512034 |
| 5200 | Capza3 | NM_007605.4 | chr6:139990045-139991307 | | 5295 | Cav1 | NM_001243064.1 | chr6:17256334-17291328 |
| 5201 | Capzb | NM_001037761.2 | chr4:138748813-138847735 | | 5296 | Cav1 | NM_007616.4 | chr6:17256334-17291328 |
| 5202 | Capzb | NM_001271405.1 | chr4:138748813-138847735 | | 5297 | Cav2 | NM_001277756.1 | chr6:17231184-17239130 |
| 5203 | Capzb | NM_001271406.1 | chr4:138748813-138847735 | | 5298 | Cav2 | NM_016900.4 | chr6:17231184-17239130 |
| 5204 | Capzb | NM_009798.4 | chr4:138748813-138847735 | | 5299 | Cav3 | NM_007617.3 | chr6:112409498-112422866 |
| 5205 | Car1 | NM_001083957.1 | chr3:14766213-14808365 | | 5300 | Cbfa2t2 | NM_001285446.1 | chr2:154262219-154365092 |
| 5206 | Car1 | NM_009799.3 | chr3:14766213-14808365 | | 5301 | Cbfa2t2 | NM_009823.1 | chr2:154262219-154365092 |
| 5207 | Car10 | NM_028296.3 | chr11:92960603-93463065 | | 5302 | Cbfa2t2 | NM_172860.2 | chr2:154262219-154365092 |
| 5208 | Car11 | NM_009800.4 | chr7:52955336-52960031 | | 5303 | Cbfa2t3 | NM_001109873.1 | chr8:125149035-125223009 |
| 5209 | Car12 | NM_178396.5 | chr9:66561492-66614652 | | 5304 | Cbfa2t3 | NM_009824.2 | chr8:125149035-125223009 |
| 5210 | Car13 | NM_024495.5 | chr3:14641726-14663002 | | 5305 | Cbfa2t3 | NM_177289.1 | chr8:125149035-125223009 |
| 5211 | Car14 | NM_011797.2 | chr3:95701723-95708562 | | 5306 | Cbfb | NM_001161456.1 | chr8:107694573-107741888 |
| 5212 | Car15 | NM_030558.2 | chr17:17835368-17838279 | | 5307 | Cbfb | NM_001161457.1 | chr8:107694573-107741888 |
| 5213 | Car2 | NM_009801.4 | chr3:14886425-14900770 | | 5308 | Cbfb | NM_001161458.1 | chr8:107694573-107741888 |

Fig. 25 - 29

| | | | |
|---|---|---|---|
| 5309 | Cbfb | NM_022309.4 | chr8:107694573-107741888 |
| 5310 | Cbl | NM_007619.2 | chr9:43957344-44042129 |
| 5311 | Cblb | NM_001033238.1 | chr16:52031681-52208159 |
| 5312 | Cblc | NM_001161844.1 | chr7:20365066-20382158 |
| 5313 | Cblc | NM_023224.5 | chr7:20365066-20382158 |
| 5314 | Cbll1 | NM_001253847.1 | chr12:32169693-32184481 |
| 5315 | Cbll1 | NM_001253848.1 | chr12:32169693-32184481 |
| 5316 | Cbll1 | NM_134048.2 | chr12:32169693-32184481 |
| 5317 | Cbln1 | NM_019626.3 | chr8:89992751-89996491 |
| 5318 | Cbln2 | NM_172633.4 | chr18:86882439-86887675 |
| 5319 | Cbln3 | NM_019820.3 | chr14:56497756-56503093 |
| 5320 | Cbln4 | NM_175631.3 | chr2:171861835-171868966 |
| 5321 | Cbr1 | NM_007620.2 | chr16:93608081-93610594 |
| 5322 | Cbr2 | NM_007621.2 | chr11:120590798-120593335 |
| 5323 | Cbr3 | NM_173047.3 | chr16:93683463-93691236 |
| 5324 | Cbr4 | NM_145595.1 | chr8:63966530-63982297 |
| 5325 | Cbs | NM_001271353.1 | chr17:31749567-31774150 |
| 5326 | Cbs | NM_144855.3 | chr17:31749567-31774150 |
| 5327 | Cbs | NM_178224.3 | chr17:31749567-31774150 |
| 5328 | Cbwd1 | NM_146097.3 | chr19:24994405-25036106 |
| 5329 | Cbwd1 | NR_033744.1 | chr19:24994405-25036106 |
| 5330 | Cbx1 | NM_007622.3 | chr11:96650450-96669954 |
| 5331 | Cbx2 | NM_007623.2 | chr11:118884342-118892584 |
| 5332 | Cbx3 | NM_007624.3 | chr6:51420614-51433703 |
| 5333 | Cbx4 | NM_007625.2 | chr11:118938884-118947551 |
| 5334 | Cbx5 | NM_001076789.1 | chr15:103021976-103070247 |
| 5335 | Cbx5 | NM_001110216.1 | chr15:103021976-103070247 |
| 5336 | Cbx5 | NM_007626.3 | chr15:103021976-103070247 |
| 5337 | Cbx6 | NM_028763.2 | chr15:79654328-79664763 |
| 5338 | Cbx7 | NM_144811.3 | chr15:79746236-79763076 |
| 5339 | Cbx8 | NM_019590.1 | chr11:118899749-118902227 |
| 5340 | Cby1 | NM_028634.3 | chr15:79489656-79498090 |
| 5341 | Cc2d1a | NM_145970.1 | chr8:86656726-86671652 |
| 5342 | Cc2d1b | NM_177045.3 | chr4:108292560-108306727 |
| 5343 | Cc2d2a | NM_172274.2 | chr5:44053617-44132209 |
| 5344 | Ccar1 | NM_026201.3 | chr10:62206675-62255116 |
| 5345 | Ccar2 | NM_146055.3 | chr14:70537976-70553598 |
| 5346 | Ccbe1 | NM_178793.4 | chr18:66216510-66451492 |
| 5347 | Ccbl1 | NM_172404.2 | chr2:30040650-30061219 |
| 5348 | Ccbl2 | NM_173763.4 | chr3:142364043-142407874 |
| 5349 | Ccdc101 | NM_029339.3 | chr7:133792822-133816293 |
| 5350 | Ccdc102a | NM_001033533.3 | chr8:97426768-97441998 |
| 5351 | Ccdc103 | NM_028492.2 | chr11:102742558-102746529 |
| 5352 | Ccdc104 | NM_025740.1 | chr11:29121535-29147272 |
| 5353 | Ccdc105 | NM_027630.1 | chr10:78209668-78215812 |
| 5354 | Ccdc106 | NM_001290429.1 | chr7:5007753-5012386 |
| 5355 | Ccdc106 | NM_001290432.1 | chr7:5007753-5012386 |
| 5356 | Ccdc106 | NM_146178.2 | chr7:5007753-5012386 |
| 5357 | Ccdc107 | NM_001037913.2 | chr4:43506236-43508793 |
| 5358 | Ccdc108 | NM_001039495.1 | chr1:74948653-74982173 |
| 5359 | Ccdc109b | NM_025779.3 | chr3:129617877-129673124 |
| 5360 | Ccdc11 | NM_028948.2 | chr18:74442753-74519638 |
| 5361 | Ccdc11 | NR_029424.1 | chr18:74442753-74519638 |
| 5362 | Ccdc110 | NM_001033246.2 | chr8:47020002-47029499 |
| 5363 | Ccdc112 | NM_001160399.1 | chr18:46441804-46471582 |
| 5364 | Ccdc113 | NM_172914.2 | chr8:98057999-98082788 |
| 5365 | Ccdc114 | NM_001033243.2 | chr7:53183767-53204326 |
| 5366 | Ccdc115 | NM_027159.2 | chr1:34493514-34496517 |
| 5367 | Ccdc116 | NM_001164606.1 | chr16:17139156-17144516 |
| 5368 | Ccdc116 | NM_029779.2 | chr16:17139156-17144516 |
| 5369 | Ccdc117 | NM_134033.2 | chr11:5428890-5442220 |
| 5370 | Ccdc12 | NM_028312.3 | chr9:110559006-110614097 |
| 5371 | Ccdc120 | NM_207202.2 | chrX:7308839-7318450 |
| 5372 | Ccdc121 | NM_207280.3 | chr1:183439763-183441582 |
| 5373 | Ccdc122 | NM_175363.3 | chr14:77436578-77512011 |
| 5374 | Ccdc124 | NM_026964.3 | chr8:73392125-73397389 |
| 5375 | Ccdc125 | NM_001168386.2 | chr13:101439435-101500897 |
| 5376 | Ccdc125 | NM_183115.5 | chr13:101439435-101500897 |
| 5377 | Ccdc126 | NM_175098.5 | chr6:49269351-49291580 |
| 5378 | Ccdc127 | NM_001168658.1 | chr13:74487764-74503231 |
| 5379 | Ccdc127 | NM_001168659.1 | chr13:74487764-74503231 |
| 5380 | Ccdc127 | NM_024201.3 | chr13:74487764-74503231 |
| 5381 | Ccdc129 | NM_001168611.1 | chr6:55787011-55928592 |
| 5382 | Ccdc13 | NM_028384.1 | chr9:121706744-121748579 |
| 5383 | Ccdc130 | NM_026850.3 | chr8:86781693-86794259 |
| 5384 | Ccdc132 | NM_001167750.1 | chr6:3448392-3553531 |
| 5385 | Ccdc132 | NM_001167751.1 | chr6:3448392-3553531 |
| 5386 | Ccdc132 | NM_024260.5 | chr6:3448392-3553531 |
| 5387 | Ccdc134 | NM_172428.2 | chr15:81958351-81972632 |
| 5388 | Ccdc135 | NM_001042715.3 | chr8:97579002-97602041 |
| 5389 | Ccdc136 | NM_001201378.1 | chr6:29348925-29376995 |
| 5390 | Ccdc136 | NM_145574.3 | chr6:29348925-29376995 |
| 5391 | Ccdc137 | NM_152807.3 | chr11:120319443-120325667 |
| 5392 | Ccdc138 | NM_001162956.1 | chr10:57960684-58038992 |
| 5393 | Ccdc14 | NM_172824.3 | chr16:34690701-34725280 |
| 5394 | Ccdc141 | NM_001025576.3 | chr2:76847962-77008692 |
| 5395 | Ccdc142 | NM_001081266.1 | chr6:83051510-83059315 |
| 5396 | Ccdc144b | NM_178418.4 | chr3:35906169-35952469 |
| 5397 | Ccdc146 | NM_029195.1 | chr5:20798779-20930495 |
| 5398 | Ccdc147 | NM_001081267.1 | chr19:48012201-48109869 |
| 5399 | Ccdc148 | NM_001031178.1 | chr2:58674108-58998684 |
| 5400 | Ccdc149 | NM_001256059.1 | chr5:52765889-52862782 |
| 5401 | Ccdc15 | NM_001081429.1 | chr9:37083419-37159577 |
| 5402 | Ccdc150 | NM_030025.2 | chr1:54307526-54425571 |
| 5403 | Ccdc151 | NM_001163787.1 | chr9:21794314-21807078 |
| 5404 | Ccdc151 | NM_029939.3 | chr9:21794314-21807078 |
| 5405 | Ccdc152 | NM_001166063.2 | chr15:3230626-3253526 |
| 5406 | Ccdc153 | NM_001081369.2 | chr9:44048759-44055389 |
| 5407 | Ccdc154 | NM_001079929.2 | chr17:25299406-25308858 |
| 5408 | Ccdc155 | NM_201374.2 | chr7:52439045-52460262 |
| 5409 | Ccdc157 | NM_001164620.1 | chr11:4035162-4060296 |
| 5410 | Ccdc157 | NM_177616.3 | chr11:4035162-4060296 |
| 5411 | Ccdc158 | NM_177230.3 | chr5:93037320-93104153 |
| 5412 | Ccdc159 | NM_001164614.1 | chr9:21725452-21740316 |
| 5413 | Ccdc159 | NM_025977.3 | chr9:21725452-21740316 |
| 5414 | Ccdc160 | NM_001034059.1 | chrX:50144376-50152645 |
| 5415 | Ccdc162 | NM_001177571.1 | chr10:41,258,655-41,307,559 |
| 5416 | Ccdc163 | NM_026714.2 | chr4:116381534-116387709 |
| 5417 | Ccdc166 | NM_001163518.1 | chr15:75810301-75812715 |
| 5418 | Ccdc166 | NM_146059.2 | chr15:75810301-75812715 |
| 5419 | Ccdc167 | NM_001163741.2 | chr17:29797545-29853962 |
| 5420 | Ccdc167 | NM_026782.2 | chr17:29797545-29853962 |
| 5421 | Ccdc169 | NM_001290138.1 | chr3:54941260-54976858 |
| 5422 | Ccdc169 | NM_001290141.1 | chr3:54941260-54976858 |
| 5423 | Ccdc169 | NM_177203.3 | chr3:54941260-54976858 |
| 5424 | Ccdc169 | NR_110776.1 | chr3:54941260-54976858 |
| 5425 | Ccdc169 | NR_110780.1 | chr3:54941260-54976858 |
| 5426 | Ccdc169 | NR_110781.1 | chr3:54941260-54976858 |
| 5427 | Ccdc17 | NM_001037916.3 | chr4:116269335-116272871 |
| 5428 | Ccdc170 | NM_001195672.1 | chr10:5785429-5836669 |
| 5429 | Ccdc171 | NM_001081012.1 | chr4:83171448-83510574 |
| 5430 | Ccdc172 | NM_029372.2 | chr19:58586491-58627575 |
| 5431 | Ccdc173 | NM_001077684.1 | chr2:69696113-69627543 |
| 5432 | Ccdc174 | NM_172730.2 | chr6:91828046-91849842 |
| 5433 | Ccdc175 | NM_028687.1 | chr12:73202279-73286016 |
| 5434 | Ccdc176 | NM_028377.3 | chr12:85750018-85774730 |
| 5435 | Ccdc177 | NM_001008423.2 | chr12:81856433-81861702 |
| 5436 | Ccdc178 | NM_027616.3 | chr18:21969397-22329897 |
| 5437 | Ccdc18 | NM_028481.1 | chr5:108561932-108661968 |
| 5438 | Ccdc181 | NM_029115.3 | chr1:166205728-166217978 |
| 5439 | Ccdc183 | NM_029859.1 | chr2:25464148-25473198 |
| 5440 | Ccdc184 | NM_177716.3 | chr15:97998236-98000565 |
| 5441 | Ccdc185 | NM_001033547.2 | chr1:184677256-184679311 |
| 5442 | Ccdc19 | NM_027972.2 | chr1:174451261-174476001 |
| 5443 | Ccdc22 | NM_138603.3 | chrX:7170935-7182546 |
| 5444 | Ccdc23 | NM_001038998.2 | chr4:118867914-118873903 |
| 5445 | Ccdc23 | NM_024462.2 | chr4:118867914-118873903 |
| 5446 | Ccdc24 | NM_001034876.1 | chr4:117541867-117545075 |
| 5447 | Ccdc25 | NM_145944.4 | chr14:66456138-66485441 |
| 5448 | Ccdc27 | NM_001033455.2 | chr4:153400752-153416786 |
| 5449 | Ccdc28a | NM_144820.3 | chr10:17933490-17954787 |
| 5450 | Ccdc28b | NM_025455.2 | chr4:129296517-129301152 |
| 5451 | Ccdc3 | NM_028804.1 | chr2:5058821-5151912 |
| 5452 | Ccdc30 | NM_001270435.1 | chr4:118995497-119088126 |
| 5453 | Ccdc30 | NM_001270446.1 | chr4:118995497-119088126 |
| 5454 | Ccdc30 | NM_028506.1 | chr4:118995497-119088126 |
| 5455 | Ccdc30 | NM_028698.1 | chr4:118995497-119088126 |
| 5456 | Ccdc30 | NM_028857.1 | chr4:118995497-119088126 |
| 5457 | Ccdc30 | NM_029286.2 | chr4:118995497-119088126 |
| 5458 | Ccdc32 | NM_199310.2 | chr2:118843514-118855129 |
| 5459 | Ccdc33 | NM_001166282.1 | chr9:57876488-57966630 |
| 5460 | Ccdc33 | NM_029212.3 | chr9:57876488-57966630 |
| 5461 | Ccdc34 | NM_026613.4 | chr2:109857974-109885482 |
| 5462 | Ccdc34os | NR_040508.1 | chr2:109871407-109890636 |
| 5463 | Ccdc36 | NM_001135198.1 | chr9:108305963-108330813 |
| 5464 | Ccdc37 | NM_173775.3 | chr9:90353729-90378474 |
| 5465 | Ccdc38 | NM_175488.6 | chr10:93003377-93047071 |
| 5466 | Ccdc39 | NM_026222.2 | chr3:33711283-33749232 |
| 5467 | Ccdc40 | NM_175430.4 | chr11:119089885-119126526 |
| 5468 | Ccdc42 | NM_177779.3 | chr11:68400538-68411453 |
| 5469 | Ccdc42b | NM_001195094.1 | chr5:121078344-121084244 |
| 5470 | Ccdc43 | NM_025918.3 | chr11:102546001-102559039 |
| 5471 | Ccdc47 | NM_026009.2 | chr11:106060669-106077681 |
| 5472 | Ccdc50 | NM_001025615.3 | chr16:27389041-27452304 |
| 5473 | Ccdc50 | NM_001289436.1 | chr16:27389041-27452304 |
| 5474 | Ccdc50 | NM_026202.3 | chr16:27389041-27452304 |
| 5475 | Ccdc51 | NM_025689.4 | chr9:108985309-108995877 |
| 5476 | Ccdc53 | NM_001122960.1 | chr10:87663841-87708903 |
| 5477 | Ccdc53 | NM_026070.1 | chr10:87663841-87708903 |
| 5478 | Ccdc53 | NM_027487.1 | chr10:87663841-87708903 |
| 5479 | Ccdc54 | NM_027046.3 | chr16:50589972-50591267 |
| 5480 | Ccdc55 | NM_001012309.2 | chr11:76857794-76891939 |
| 5481 | Ccdc57 | NM_027745.1 | chr11:120687855-120794186 |
| 5482 | Ccdc58 | NM_001159421.1 | chr16:36071745-36092204 |
| 5483 | Ccdc58 | NM_001159422.1 | chr16:36071745-36092204 |
| 5484 | Ccdc58 | NM_198645.2 | chr16:36071745-36092204 |
| 5485 | Ccdc59 | NM_025602.3 | chr10:105278534-105284566 |
| 5486 | Ccdc6 | NM_001111121.1 | chr10:69559868-69655948 |
| 5487 | Ccdc60 | NM_177759.3 | chr5:116575589-116738994 |
| 5488 | Ccdc61 | NM_001033314.3 | chr7:19476232-19495753 |
| 5489 | Ccdc62 | NM_001134767.1 | chr5:124380697-124419904 |
| 5490 | Ccdc63 | NM_001289809.1 | chr5:122558060-122588071 |
| 5491 | Ccdc63 | NM_001289811.1 | chr5:122558060-122588071 |
| 5492 | Ccdc63 | NM_183307.4 | chr5:122558060-122588071 |
| 5493 | Ccdc64 | NM_001080808.1 | chr5:116099294-116181568 |
| 5494 | Ccdc64b | NM_153784.2 | chr17:23797490-23805586 |
| 5495 | Ccdc65 | NM_153518.1 | chr15:98538657-98553764 |
| 5496 | Ccdc66 | NM_177111.3 | chr14:28295596-28321646 |
| 5497 | Ccdc67 | NM_181816.2 | chr9:15364308-15432377 |
| 5498 | Ccdc68 | NM_201362.2 | chr18:70085212-70139138 |

Fig. 25 - 30

| | | | |
|---|---|---|---|
| 5499 | Ccdc69 | NM_174471.4 | chr11:54863239-54891633 |
| 5500 | Ccdc7 | NM_001197041.1 | chr8:131503918-131589392 |
| 5501 | Ccdc7 | NM_029061.3 | chr8:131503918-131589392 |
| 5502 | Ccdc70 | NM_026459.3 | chr8:23081067-23084513 |
| 5503 | Ccdc71 | NM_133744.4 | chr9:108362849-108368276 |
| 5504 | Ccdc71l | NM_001162903.1 | chr12:33063653-33067808 |
| 5505 | Ccdc73 | NM_177600.4 | chr2:104726481-104839894 |
| 5506 | Ccdc74a | NM_001166164.1 | chr16:17646562-17650831 |
| 5507 | Ccdc77 | NM_026028.5 | chr6:120274339-120394592 |
| 5508 | Ccdc77 | NR_045558.1 | chr6:120274339-120394592 |
| 5509 | Ccdc78 | NM_001165929.1 | chr7:25923525-25927458 |
| 5510 | Ccdc79 | NM_180958.3 | chr8:106970618-107033787 |
| 5511 | Ccdc8 | NM_001101535.1 | chr7:17579936-17581994 |
| 5512 | Ccdc80 | NM_026439.2 | chr16:45094165-45128037 |
| 5513 | Ccdc81 | NM_001162979.1 | chr7:97014657-97052139 |
| 5514 | Ccdc82 | NM_025534.2 | chr9_random:372078-417453 |
| 5515 | Ccdc83 | NM_029256.3 | chr7:97372387-97413942 |
| 5516 | Ccdc83 | NM_183293.1 | chr7:97372387-97413942 |
| 5517 | Ccdc83 | NR_111924.1 | chr7:97372387-97413942 |
| 5518 | Ccdc84 | NM_201372.3 | chr9:44218247-44226090 |
| 5519 | Ccdc85a | NM_001166661.2 | chr11:28285683-28484324 |
| 5520 | Ccdc85a | NM_001166662.1 | chr11:28285683-28484324 |
| 5521 | Ccdc85a | NM_181577.5 | chr11:28285683-28484324 |
| 5522 | Ccdc85b | NM_001243307.1 | chr19:5447697-5457563 |
| 5523 | Ccdc85b | NM_198616.4 | chr19:5447697-5457563 |
| 5524 | Ccdc85c | NM_001159910.1 | chr12:109444554-109513627 |
| 5525 | Ccdc86 | NM_023731.3 | chr19:11015971-11023756 |
| 5526 | Ccdc87 | NM_207268.3 | chr19:4839365-4842528 |
| 5527 | Ccdc88a | NM_176841.4 | chr11:29274171-29410808 |
| 5528 | Ccdc88b | NM_001081291.1 | chr19:6919112-6932701 |
| 5529 | Ccdc88c | NM_026681.4 | chr12:102150910-102267193 |
| 5530 | Ccdc89 | NM_027298.1 | chr7:97574821-97577174 |
| 5531 | Ccdc9 | NM_001136471.1 | chr7:16859390-16872144 |
| 5532 | Ccdc9 | NM_172297.1 | chr7:16859390-16872144 |
| 5533 | Ccdc90b | NM_001162918.1 | chr7:99709658-99730804 |
| 5534 | Ccdc90b | NM_025515.3 | chr7:99709658-99730804 |
| 5535 | Ccdc91 | NM_025911.2 | chr6:147424392-147581134 |
| 5536 | Ccdc92 | NM_144819.2 | chr5:125314801-125342591 |
| 5537 | Ccdc93 | NM_001025156.2 | chr1:123327643-123403037 |
| 5538 | Ccdc93 | NM_029955.3 | chr1:123327643-123403037 |
| 5539 | Ccdc94 | NM_028381.3 | chr17:56098610-56107374 |
| 5540 | Ccdc96 | NM_025725.2 | chr5:36827236-36830820 |
| 5541 | Ccdc97 | NM_028771.2 | chr7:26496135-26504072 |
| 5542 | Ccer1 | NM_025724.2 | chr10:97155693-97157960 |
| 5543 | Cchcr1 | NM_146248.2 | chr17:35654060-35667960 |
| 5544 | Ccin | NM_001002787.2 | chr4:43996375-43998405 |
| 5545 | Cck | NM_001284508.1 | chr9:121398941-121404812 |
| 5546 | Cck | NM_031161.4 | chr9:121398941-121404812 |
| 5547 | Cckar | NM_009827.2 | chr5:54089723-54098943 |
| 5548 | Cckbr | NM_007627.5 | chr7:112574333-112584852 |
| 5549 | Ccl1 | NM_011329.3 | chr11:81990167-81993314 |
| 5550 | Ccl11 | NM_011330.3 | chr11:81871333-81876457 |
| 5551 | Ccl12 | NM_011331.2 | chr11:81915346-81916901 |
| 5552 | Ccl17 | NM_011332.3 | chr8:97334352-97335936 |
| 5553 | Ccl19 | NM_011888.2 | chr4:42248503-42250497 |
| 5554 | Ccl19 | NM_011888.2 | chr4:42768056-42770050 |
| 5555 | Ccl2 | NM_011333.3 | chr11:81849078-81850954 |
| 5556 | Ccl20 | NM_001159738.1 | chr1:83113340-83115742 |
| 5557 | Ccl20 | NM_016960.2 | chr1:83113340-83115742 |
| 5558 | Ccl21a | NM_011124.4 | chr4:42231042-42232176 |
| 5559 | Ccl21a | NM_011124.4 | chr4:42786391-42787525 |
| 5560 | Ccl21b | NM_011335.2 | chr4:42104293-42104673 |
| 5561 | Ccl21b | NM_011335.2 | chr4:41763293-42104673 |
| 5562 | Ccl21b | NM_011335.2 | chr4:42391949-42393080 |
| 5563 | Ccl21b | NM_011335.2 | chr4:42625654-42626785 |
| 5564 | Ccl21b | NM_011335.2 | chrUn_random:527838-528969 |
| 5565 | Ccl21b | NM_011335.2 | chrUn_random:739162-740293 |
| 5566 | Ccl21c | NM_023052.2 | chr4:42,391,950-42,393,080 |
| 5567 | Ccl22 | NM_009137.2 | chr8:97269583-97275288 |
| 5568 | Ccl24 | NM_019577.4 | chr5:136045806-136048913 |
| 5569 | Ccl25 | NM_009138.3 | chr8:4325209-4360020 |
| 5570 | Ccl25 | NR_033527.1 | chr8:4325209-4360020 |
| 5571 | Ccl26 | NM_001013412.2 | chr5:136036317-136039439 |
| 5572 | Ccl27a | NM_001048179.1 | chr4:41707315-41721049 |
| 5573 | Ccl27a | NM_001164044.1 | chr4:41707315-41721049 |
| 5574 | Ccl27a | NM_001164045.1 | chr4:41707315-41721049 |
| 5575 | Ccl27a | NM_011336.1 | chr4:41707315-41721049 |
| 5576 | Ccl27b | NM_001199961.1 | chr4:41763293-42104673 |
| 5577 | Ccl27b | NM_001199961.1 | chr4:41763293-42104673 |
| 5578 | Ccl27b | NM_001199961.1 | chr4:42664135-42679295 |
| 5579 | Ccl28 | NM_020279.3 | chr13_random:362538-39397 8 |
| 5580 | Ccl3 | NM_011337.2 | chr11:83461344-83462880 |
| 5581 | Ccl4 | NM_013652.2 | chr11:83476085-83478185 |
| 5582 | Ccl5 | NM_013653.3 | chr11:83339280-83344020 |
| 5583 | Ccl6 | NM_009139.3 | chr11:83401388-83406589 |
| 5584 | Ccl7 | NM_013654.3 | chr11:81859213-81861025 |
| 5585 | Ccl8 | NM_021443.3 | chr11:81928686-81930301 |
| 5586 | Ccl9 | NM_011338.2 | chr11:83386418-83392138 |
| 5587 | Ccm2 | NM_001190343.1 | chr11:6446889-6496764 |
| 5588 | Ccm2 | NM_001190344.1 | chr11:6446889-6496764 |
| 5589 | Ccm2 | NM_146014.3 | chr11:6446889-6496764 |
| 5590 | Ccm2l | NM_145536.3 | chr2:152891690-152907471 |
| 5591 | Ccna1 | NM_007628.3 | chr3:54849390-54858977 |

| | | | |
|---|---|---|---|
| 5592 | Ccna2 | NM_009828.2 | chr3:36463787-36470918 |
| 5593 | Ccnb1 | NM_172301.3 | chr13:101548893-101556441 |
| 5594 | Ccnb1ip1 | NM_001111119.1 | chr14:51408923-51415403 |
| 5595 | Ccnb1ip2 | NM_007630.2 | chr9:70255495-70269361 |
| 5596 | Ccnb3 | NM_183015.3 | chrX:6556777-6618745 |
| 5597 | Ccnc | NM_011229822 | chr4:21654847-21694358 |
| 5598 | Ccnc | NM_001290420.1 | chr4:21654847-21694358 |
| 5599 | Ccnc | NM_001290422.1 | chr4:21654847-21694358 |
| 5600 | Ccnc | NM_016746.4 | chr4:21654847-21694358 |
| 5601 | Ccnd1 | NM_007631.2 | chr7:152115835-152125830 |
| 5602 | Ccnd2 | NM_009829.3 | chr6:127075727-127101066 |
| 5603 | Ccnd3 | NM_001081635.1 | chr17:47641999-47748441 |
| 5604 | Ccnd3 | NM_001081636.1 | chr17:47641999-47748441 |
| 5605 | Ccnd3 | NM_007632.2 | chr17:47641999-47748441 |
| 5606 | Ccndbp1 | NM_010761.2 | chr2:120834143-120842648 |
| 5607 | Ccne1 | NM_007633.2 | chr7:38883002-38892509 |
| 5608 | Ccne2 | NM_001037134.2 | chr4:11118497-11181406 |
| 5609 | Ccne2 | NM_001282943.1 | chr4:11118497-11181406 |
| 5610 | Ccne2 | NM_009830.3 | chr4:11118497-11181406 |
| 5611 | Ccnf | NM_007634.4 | chr17:24360177-24388354 |
| 5612 | Ccng1 | NM_009831.2 | chr11:40562053-40568788 |
| 5613 | Ccng2 | NM_007635.4 | chr5:93696598-93705257 |
| 5614 | Ccnh | NM_023243.5 | chr13:85329081-85353328 |
| 5615 | Ccni | NM_017367.3 | chr5:93610958-93635521 |
| 5616 | Ccnj | NM_172839.4 | chr19:40905768-40923060 |
| 5617 | Ccnjl | NM_001045530.2 | chr11:43342250-43400501 |
| 5618 | Ccnk | NM_009832.2 | chr12:109417947-109441569 |
| 5619 | Ccnl1 | NM_019937.3 | chr3:65750072-65762147 |
| 5620 | Ccnl2 | NM_207678.1 | chr4:155186597-155198652 |
| 5621 | Ccno | NM_001081062.1 | chr13:113778009-113780986 |
| 5622 | Ccnt1 | NM_009833.1 | chr15:98373642-98398067 |
| 5623 | Ccnt2 | NM_028399.1 | chr1:129670740-129701414 |
| 5624 | Ccny | NM_026484.3 | chr18:9314041-9450148 |
| 5625 | Ccnyl1 | NM_001097644.1 | chr1:64737918-64772216 |
| 5626 | Ccp110 | NM_182995.3 | chr7:125856124-125880532 |
| 5627 | Ccpg1 | NM_001114328.2 | chr9:72833310-72887506 |
| 5628 | Ccpg1 | NM_001286544.1 | chr9:72833310-72887506 |
| 5629 | Ccpg1 | NM_001286545.1 | chr9:72833310-72887506 |
| 5630 | Ccpg1 | NM_001286546.1 | chr9:72833310-72887506 |
| 5631 | Ccpg1 | NM_028181.5 | chr9:72833310-72887506 |
| 5632 | Ccpg1os | NM_001198789.1 | chr9:72827532-72833183 |
| 5633 | Ccr1 | NM_009912.4 | chr9:123876958-123883525 |
| 5634 | Ccr10 | NM_007721.4 | chr11:101034311-101036757 |
| 5635 | Ccr1l1 | NM_007718.3 | chr9:123891781-123893241 |
| 5636 | Ccr2 | NM_009915.2 | chr9:124016921-124023879 |
| 5637 | Ccr3 | NM_009914.4 | chr9:123936702-123946421 |
| 5638 | Ccr4 | NM_009916.2 | chr9:114399433-114405662 |
| 5639 | Ccr5 | NM_009917.5 | chr9:124036281-124041922 |
| 5640 | Ccr6 | NM_001190333.1 | chr17:8428907-8449994 |
| 5641 | Ccr6 | NM_001190334.1 | chr17:8428907-8449994 |
| 5642 | Ccr6 | NM_001190335.1 | chr17:8428907-8449994 |
| 5643 | Ccr6 | NM_001190336.1 | chr17:8428907-8449994 |
| 5644 | Ccr6 | NM_001190337.1 | chr17:8428907-8449994 |
| 5645 | Ccr6 | NM_001190338.1 | chr17:8428907-8449994 |
| 5646 | Ccr6 | NM_009835.4 | chr17:8428907-8449994 |
| 5647 | Ccr7 | NM_007719.2 | chr11:99005512-99016391 |
| 5648 | Ccr8 | NM_007720.2 | chr9:120001250-120004024 |
| 5649 | Ccr9 | NM_001166625.1 | chr9:123676328-123692575 |
| 5650 | Ccr9 | NM_009913.6 | chr9:123676328-123692575 |
| 5651 | Ccrl2 | NM_017466.5 | chr9:110957338-110959774 |
| 5652 | Ccrn4l | NM_009834.2 | chr3:51028368-51055576 |
| 5653 | Ccs | NM_016892.3 | chr19:4825365-4839322 |
| 5654 | Ccsap | NM_028536.1 | chr8:126364743-126384109 |
| 5655 | Ccser1 | NM_001164316.1 | chr6:61125597-62332857 |
| 5656 | Ccser1 | NM_183310.2 | chr6:61125597-62332857 |
| 5657 | Ccser2 | NM_027045.1 | chr14:37688121-37781950 |
| 5658 | Ccser2 | NM_028407.3 | chr14:37688121-37781950 |
| 5659 | Cct2 | NM_007636.2 | chr10:116488053-116500870 |
| 5660 | Cct3 | NM_009836.1 | chr3:88101056-88125688 |
| 5661 | Cct4 | NM_009837.1 | chr11:22890592-22903336 |
| 5662 | Cct5 | NM_007637.2 | chr15:31520638-31531559 |
| 5663 | Cct6a | NM_009838.2 | chr5:130293232-130322319 |
| 5664 | Cct6b | NM_001291242.1 | chr11:82532749-82577823 |
| 5665 | Cct6b | NM_009839.3 | chr11:82532749-82577823 |
| 5666 | Cct7 | NM_007638.4 | chr6:85401499-85418471 |
| 5667 | Cct8 | NM_009840.3 | chr16:87483570-87496114 |
| 5668 | Cct8l1 | NM_198621.2 | chr5:25021884-25023845 |
| 5669 | Ccz1 | NM_177682.3 | chr5:144748777-144775722 |
| 5670 | Cd101 | NM_001099932.2 | chr3:100797451-100833418 |
| 5671 | Cd101 | NM_001167906.1 | chr3:100797451-100833418 |
| 5672 | Cd109 | NM_153098.3 | chr9:78463352-78564067 |
| 5673 | Cd14 | NM_009841.2 | chr18:36884720-36886308 |
| 5674 | Cd151 | NM_001111049.1 | chr7:148653260-148657380 |
| 5675 | Cd151 | NM_001111050.1 | chr7:148653260-148657380 |
| 5676 | Cd151 | NM_009842.3 | chr7:148653260-148657380 |
| 5677 | Cd160 | NM_001163496.1 | chr3:96602685-96633274 |
| 5678 | Cd160 | NM_001163497.1 | chr3:96602685-96633274 |
| 5679 | Cd160 | NM_018767.3 | chr3:96602685-96633274 |
| 5680 | Cd163 | NM_001170395.1 | chr6:124254668-124280545 |
| 5681 | Cd163 | NM_053094.2 | chr6:124254668-124280545 |
| 5682 | Cd163l1 | NM_172909.4 | chr7:147404165-147417044 |
| 5683 | Cd164 | NM_016898.2 | chr10:41239305-41250848 |
| 5684 | Cd164l2 | NM_027152.1 | chr4:132776723-132780469 |
| 5685 | Cd177 | NM_026862.3 | chr7:25529001-25545330 |
| 5686 | Cd180 | NM_008533.2 | chr13:103483637-103496711 |

Fig. 25 - 31

| | | | |
|---|---|---|---|
| 5687 | Cd19 | NM_009844.1 | chr7:133551961-133558384 |
| 5688 | Cd1d1 | NM_007639.3 | chr3:86799757-86803262 |
| 5689 | Cd1d2 | NM_001289449.1 | chr3:86790507-86793454 |
| 5690 | Cd1d2 | NR_038188.1 | chr3:86790507-86793454 |
| 5691 | Cd2 | NM_013486.2 | chr3:101079830-101091862 |
| 5692 | Cd200 | NM_010818.3 | chr16:45382247-45409166 |
| 5693 | Cd200r1 | NM_021325.3 | chr16:44765848-44795090 |
| 5694 | Cd200r2 | NM_206535.1 | chr16:44867209-44915953 |
| 5695 | Cd200r3 | NM_001128132.1 | chr16:44943790-44981493 |
| 5696 | Cd200r3 | NM_001128133.1 | chr16:44943790-44981493 |
| 5697 | Cd200r3 | NM_027578.1 | chr16:44943790-44981493 |
| 5698 | Cd200r3 | NM_029018.4 | chr16:44943790-44981493 |
| 5699 | Cd200r4 | NM_207244.2 | chr16:44820840-44839263 |
| 5700 | Cd207 | NM_144943.3 | chr6:83621200-83627851 |
| 5701 | Cd209a | NM_133238.5 | chr8:3743394-3748984 |
| 5702 | Cd209b | NM_001037800.3 | chr8:3917654-3926841 |
| 5703 | Cd209b | NM_001287211.1 | chr8:3917654-3926841 |
| 5704 | Cd209b | NM_026972.5 | chr8:3917654-3926841 |
| 5705 | Cd209b | NR_104430.2 | chr8:3917654-3926841 |
| 5706 | Cd209c | NM_130903.3 | chr8:3940221-3946863 |
| 5707 | Cd209d | NM_130904.2 | chr8:3871823-3878499 |
| 5708 | Cd209e | NM_130905.2 | chr8:3847972-3854286 |
| 5709 | Cd209f | NM_026956.2 | chr8:4102792-4105764 |
| 5710 | Cd209g | NM_027343.3 | chr8:4134735-4137707 |
| 5711 | Cd22 | NM_001043317.2 | chr7:31650422-31665361 |
| 5712 | Cd22 | NM_009845.3 | chr7:31650422-31665361 |
| 5713 | Cd22 | NR_102722.1 | chr7:31650422-31665361 |
| 5714 | Cd22 | NR_102723.1 | chr7:31650422-31665361 |
| 5715 | Cd226 | NM_001039149.1 | chr18:89366818-89439719 |
| 5716 | Cd226 | NM_178687.2 | chr18:89366818-89439719 |
| 5717 | Cd244 | NM_018729.2 | chr1:173489323-173515447 |
| 5718 | Cd247 | NM_001113391.2 | chr1:167718811-167932765 |
| 5719 | Cd247 | NM_001113392.2 | chr1:167718811-167932765 |
| 5720 | Cd247 | NM_001113393.2 | chr1:167718811-167932765 |
| 5721 | Cd247 | NM_031162.4 | chr1:167718811-167932765 |
| 5722 | Cd247 | NR_103716.1 | chr1:167718811-167932765 |
| 5723 | Cd248 | NM_054042.2 | chr19:5068077-5070639 |
| 5724 | Cd24a | NM_009846.2 | chr10:43298974-43304071 |
| 5725 | Cd27 | NM_001033126.2 | chr6:125174229-125189952 |
| 5726 | Cd27 | NM_001042564.1 | chr6:125174229-125189952 |
| 5727 | Cd27 | NM_001286753.1 | chr6:125174229-125189952 |
| 5728 | Cd274 | NM_021893.3 | chr19:29441927-29462584 |
| 5729 | Cd276 | NM_133983.4 | chr9:58372106-58388747 |
| 5730 | Cd28 | NM_007642.4 | chr1:60803231-60830203 |
| 5731 | Cd2ap | NM_009847.3 | chr17:42929899-43013373 |
| 5732 | Cd2bp2 | NM_001285905.1 | chr7:134335173-134339591 |
| 5733 | Cd2bp2 | NM_001285906.1 | chr7:134335173-134339591 |
| 5734 | Cd2bp2 | NM_001285907.1 | chr7:134335173-134339591 |
| 5735 | Cd2bp2 | NM_027353.4 | chr7:134335173-134339591 |
| 5736 | Cd300a | NM_170758.3 | chr11:114751354-114765965 |
| 5737 | Cd300c | NM_199225.1 | chr11:114817591-114821731 |
| 5738 | Cd300e | NM_172050.2 | chr11:114913230-114923352 |
| 5739 | Cd300lb | NM_199221.2 | chr11:114784094-114795700 |
| 5740 | Cd300ld | NM_145437.2 | chr11:114843760-114851200 |
| 5741 | Cd300lf | NM_001169153.1 | chr11:114952744-115023554 |
| 5742 | Cd300lf | NM_145463.2 | chr11:114952744-115023554 |
| 5743 | Cd300lg | NM_001160711.1 | chr11:101902824-101916931 |
| 5744 | Cd300lg | NM_001160712.1 | chr11:101902824-101916931 |
| 5745 | Cd300lg | NM_001160713.1 | chr11:101902824-101916931 |
| 5746 | Cd300lg | NM_027987.3 | chr11:101902824-101916931 |
| 5747 | Cd300lh | NM_199201.1 | chr11:114903444-114909609 |
| 5748 | Cd302 | NM_001290660.1 | chr2:60090049-60122541 |
| 5749 | Cd302 | NM_025422.4 | chr2:60090049-60122541 |
| 5750 | Cd320 | NM_019421.3 | chr17:33980035-33986719 |
| 5751 | Cd33 | NM_001080818.2 | chr7:50782825-50788541 |
| 5752 | Cd33 | NM_021293.3 | chr7:50782825-50788541 |
| 5753 | Cd34 | NM_001111059.1 | chr1:196765014-196803153 |
| 5754 | Cd34 | NM_133654.3 | chr1:196765014-196803153 |
| 5755 | Cd36 | NM_001159555.1 | chr5:17287507-17394777 |
| 5756 | Cd36 | NM_001159557.1 | chr5:17287507-17394777 |
| 5757 | Cd36 | NM_001159558.1 | chr5:17287507-17394777 |
| 5758 | Cd36 | NM_001159558.1 | chr5:17287507-17394777 |
| 5759 | Cd36 | NM_007643.4 | chr5:17287507-17394777 |
| 5760 | Cd37 | NM_001290802.1 | chr7:52489001-52494485 |
| 5761 | Cd37 | NM_001290804.1 | chr7:52489001-52494485 |
| 5762 | Cd37 | NM_007645.4 | chr7:52489001-52494485 |
| 5763 | Cd38 | NM_007646.4 | chr5:44260065-44303613 |
| 5764 | Cd3d | NM_013487.3 | chr9:44789868-44795135 |
| 5765 | Cd3e | NM_007648.2 | chr9:44806825-44817673 |
| 5766 | Cd3eap | NM_145822.1 | chr7:19941358-19944832 |
| 5767 | Cd3g | NM_009850.2 | chr9:44777654-44788514 |
| 5768 | Cd4 | NM_013488.2 | chr6:124814710-124838227 |
| 5769 | Cd40 | NM_011611.2 | chr2:164881135-164897154 |
| 5770 | Cd40 | NM_170702.2 | chr2:164881135-164897154 |
| 5771 | Cd40 | NM_170703.1 | chr2:164881135-164897154 |
| 5772 | Cd40 | NM_170704.2 | chr2:164881135-164897154 |
| 5773 | Cd40 | NR_027852.1 | chr2:164881135-164897154 |
| 5774 | Cd40lg | NM_011616.2 | chrX:54465319-54477219 |
| 5775 | Cd44 | NM_001039150.1 | chr2:102651299-102741822 |
| 5776 | Cd44 | NM_001177785.1 | chr2:102651299-102741822 |
| 5777 | Cd44 | NM_001177785.1 | chr2:102651299-102741822 |
| 5778 | Cd44 | NM_001177786.1 | chr2:102651299-102741822 |
| 5779 | Cd44 | NM_001177787.1 | chr2:102651299-102741822 |
| 5780 | Cd44 | NM_009851.2 | chr2:102651299-102741822 |
| 5781 | Cd46 | NM_010778.3 | chr1:196868093-196918442 |

| | | | |
|---|---|---|---|
| 5782 | Cd47 | NM_010581.3 | chr16:49855766-49911796 |
| 5783 | Cd48 | NM_007649.4 | chr1:173612185-173635388 |
| 5784 | Cd5 | NM_007650.3 | chr19:10792632-10813464 |
| 5785 | Cd52 | NM_013706.2 | chr4:133649452-133650988 |
| 5786 | Cd53 | NM_007651.2 | chr3:106561778-106593067 |
| 5787 | Cd55 | NM_010016.2 | chr1:132335606-132359317 |
| 5788 | Cd59a | NM_001111060.2 | chr2:103935957-103955567 |
| 5789 | Cd59a | NM_007652.5 | chr2:103935957-103955567 |
| 5790 | Cd59b | NM_181858.1 | chr2:103911166-103925114 |
| 5791 | Cd5l | NM_009690.2 | chr3:87161802-87174996 |
| 5792 | Cd6 | NM_001037801.2 | chr19:10863828-10904548 |
| 5793 | Cd6 | NM_009852.3 | chr19:10863828-10904548 |
| 5794 | Cd63 | NM_001042580.1 | chr10:128345974-128349874 |
| 5795 | Cd63 | NM_001282966.1 | chr10:128345974-128349874 |
| 5796 | Cd63 | NM_007653.3 | chr10:128345974-128349874 |
| 5797 | Cd68 | NM_001291058.1 | chr11:69477714-69479672 |
| 5798 | Cd68 | NM_009853.1 | chr11:69477714-69479672 |
| 5799 | Cd68 | NR_110993.1 | chr11:69477714-69479672 |
| 5800 | Cd69 | NM_001033122.3 | chr6:129217342-129225387 |
| 5801 | Cd7 | NM_009854.2 | chr11:120898062-120900792 |
| 5802 | Cd70 | NM_011617.2 | chr17:57285419-57289200 |
| 5803 | Cd72 | NM_001110320.1 | chr4:43455148-43467498 |
| 5804 | Cd72 | NM_001110321.1 | chr4:43455148-43467498 |
| 5805 | Cd72 | NM_001110322.1 | chr4:43455148-43467498 |
| 5806 | Cd72 | NM_007654.2 | chr4:43455148-43467498 |
| 5807 | Cd74 | NM_001042605.1 | chr18:60963502-60972306 |
| 5808 | Cd74 | NM_010545.3 | chr18:60963502-60972306 |
| 5809 | Cd79a | NM_007655.3 | chr7:25682529-25687216 |
| 5810 | Cd79b | NM_008339.2 | chr11:106172654-106175843 |
| 5811 | Cd80 | NM_009855.2 | chr16:38459012-38487014 |
| 5812 | Cd81 | NM_133655.2 | chr7:150238655-150253835 |
| 5813 | Cd82 | NM_001136055.2 | chr2:93259258-93310031 |
| 5814 | Cd82 | NM_001271430.1 | chr2:93259258-93310031 |
| 5815 | Cd82 | NM_001271431.1 | chr2:93259258-93310031 |
| 5816 | Cd82 | NM_001271432.1 | chr2:93259258-93310031 |
| 5817 | Cd82 | NM_001271461.1 | chr2:93259258-93310031 |
| 5818 | Cd82 | NM_001271462.1 | chr2:93259258-93310031 |
| 5819 | Cd82 | NM_007656.5 | chr2:93259258-93310031 |
| 5820 | Cd83 | NM_001289915.1 | chr13:43880480-43898502 |
| 5821 | Cd83 | NM_009856.3 | chr13:43880480-43898502 |
| 5822 | Cd84 | NM_001252472.1 | chr1:173769827-173820849 |
| 5823 | Cd84 | NM_001289470.1 | chr1:173769827-173820849 |
| 5824 | Cd84 | NM_013489.3 | chr1:173769827-173820849 |
| 5825 | Cd86 | NM_019388.3 | chr16:36603954-36666163 |
| 5826 | Cd8a | NM_001081110.2 | chr6:71323420-71329165 |
| 5827 | Cd8a | NM_009857.1 | chr6:71323420-71329165 |
| 5828 | Cd8b1 | NM_009858.2 | chr6:71272805-71287445 |
| 5829 | Cd9 | NM_007657.3 | chr6:125410283-125444773 |
| 5830 | Cd93 | NM_010740.3 | chr2:148262386-148269271 |
| 5831 | Cd96 | NM_032465.2 | chr16:46035769-46120361 |
| 5832 | Cd97 | NM_001163029.1 | chr8:86239075-86265210 |
| 5833 | Cd97 | NM_001163030.1 | chr8:86239075-86265210 |
| 5834 | Cd97 | NM_001163031.1 | chr8:86239075-86265210 |
| 5835 | Cd97 | NM_011925.2 | chr8:86239075-86265210 |
| 5836 | Cd99l2 | NM_001199349.1 | chrX:68673234-68746024 |
| 5837 | Cd99l2 | NM_138309.3 | chrX:68673234-68746024 |
| 5838 | Cda | NM_028176.1 | chr4:137894442-137923870 |
| 5839 | Cdadc1 | NM_001168535.1 | chr14:60178224-60216796 |
| 5840 | Cdadc1 | NM_001168536.1 | chr14:60178224-60216796 |
| 5841 | Cdadc1 | NM_001168537.1 | chr14:60178224-60216796 |
| 5842 | Cdadc1 | NM_001168538.1 | chr14:60178224-60216796 |
| 5843 | Cdadc1 | NM_027986.3 | chr14:60178224-60216796 |
| 5844 | Cdan1 | NM_026891.2 | chr2:120541889-120557253 |
| 5845 | Cdc123 | NM_133837.4 | chr2:5715339-5766006 |
| 5846 | Cdc14a | NM_001080818.2 | chr3:115975470-116126950 |
| 5847 | Cdc14a | NM_001173553.1 | chr3:115975470-116126950 |
| 5848 | Cdc14b | NM_001122989.1 | chr13:64293852-64376296 |
| 5849 | Cdc14b | NM_172587.3 | chr13:64293852-64376296 |
| 5850 | Cdc16 | NM_027276.2 | chr8:13757689-13781882 |
| 5851 | Cdc20 | NM_023223.2 | chr4:118105506-118109948 |
| 5852 | Cdc20b | NM_001281487.1 | chr13:113825587-113881343 |
| 5853 | Cdc23 | NM_178347.4 | chr18:34791337-34811390 |
| 5854 | Cdc25a | NM_007658.3 | chr9:109778083-109796394 |
| 5855 | Cdc25b | NM_001111075.4 | chr2:131012683-131024247 |
| 5856 | Cdc25b | NM_023117.4 | chr2:131012683-131024247 |
| 5857 | Cdc25c | NM_009860.3 | chr18:34892650-34911187 |
| 5858 | Cdc26 | NM_139291.3 | chr4:62055622-62069657 |
| 5859 | Cdc27 | NM_001285988.1 | chr11:104363840-104411934 |
| 5860 | Cdc27 | NM_001285989.1 | chr11:104363840-104411934 |
| 5861 | Cdc27 | NM_001285990.1 | chr11:104363840-104411934 |
| 5862 | Cdc27 | NM_145436.2 | chr11:104363840-104411934 |
| 5863 | Cdc34 | NM_177613.2 | chr10:79144939-79151143 |
| 5864 | Cdc37 | NM_016742.4 | chr9:20942984-20954350 |
| 5865 | Cdc37l1 | NM_025950.3 | chr19:29064983-29092059 |
| 5866 | Cdc40 | NM_027879.2 | chr10:40551426-40602949 |
| 5867 | Cdc42 | NM_001243769.1 | chr4:136875610-136913674 |
| 5868 | Cdc42 | NM_009861.3 | chr4:136875610-136913674 |
| 5869 | Cdc42bpa | NM_001033285.1 | chr1:181891220-182095733 |
| 5870 | Cdc42bpb | NM_183016.2 | chr12:112531182-112615929 |
| 5871 | Cdc42bpg | NM_001033342.1 | chr19:6306456-6325652 |
| 5872 | Cdc42ep1 | NM_027219.3 | chr15:78673077-78681332 |
| 5873 | Cdc42ep2 | NM_026772.2 | chr19:5917555-5924816 |
| 5874 | Cdc42ep3 | NM_026514.2 | chr17:79733364-79754431 |
| 5875 | Cdc42ep4 | NM_001163346.1 | chr11:113588163-113613129 |
| 5876 | Cdc42ep4 | NM_020006.2 | chr11:113588163-113613129 |

Fig. 25 - 32

| | | | |
|---|---|---|---|
| 5877 | Cdc42ep5 | NM_021454.3 | chr7:4102861-4116301 |
| 5878 | Cdc42se1 | NM_001038708.3 | chr3:94985689-95040346 |
| 5879 | Cdc42se1 | NM_172395.3 | chr3:94985689-95040346 |
| 5880 | Cdc42se2 | NM_178626.3 | chr1:54530916-54601205 |
| 5881 | Cdc45 | NM_001161623.1 | chr16:18780539-18812065 |
| 5882 | Cdc45 | NM_009862.1 | chr16:18780539-18812065 |
| 5883 | Cdc5l | NM_152810.2 | chr17:45528838-45570656 |
| 5884 | Cdc6 | NM_001025779.1 | chr11:98769202-98785256 |
| 5885 | Cdc6 | NM_011799.2 | chr11:98769202-98785256 |
| 5886 | Cdc7 | NM_001271566.1 | chr5:107393340-107413458 |
| 5887 | Cdc7 | NM_001271567.1 | chr5:107393340-107413458 |
| 5888 | Cdc7 | NM_001271568.1 | chr5:107393340-107413458 |
| 5889 | Cdc7 | NM_009863.3 | chr5:107393340-107413458 |
| 5890 | Cdc73 | NM_145991.3 | chr1:145454629-145549814 |
| 5891 | Cdca2 | NM_001110162.1 | chr14:68294410-68333898 |
| 5892 | Cdca2 | NM_175384.4 | chr14:68294410-68333898 |
| 5893 | Cdca3 | NM_013538.3 | chr6:124780193-124783719 |
| 5894 | Cdca4 | NM_028023.3 | chr12:114058445-114067600 |
| 5895 | Cdca5 | NM_026410.3 | chr19:6085096-6091773 |
| 5896 | Cdca7 | NM_025866.2 | chr2:72314275-72324947 |
| 5897 | Cdca7l | NM_146040.1 | chr12:119082334-119117179 |
| 5898 | Cdca8 | NM_026560.4 | chr4:124595708-124614161 |
| 5899 | Cdcp1 | NM_133974.3 | chr9:123081402-123125156 |
| 5900 | Cdcp2 | NM_172873.3 | chr4:106769495-106780353 |
| 5901 | Cdh1 | NM_009864.2 | chr8:109127267-109194146 |
| 5902 | Cdh10 | NM_009865.2 | chr15:18750083-18943989 |
| 5903 | Cdh11 | NM_009866.4 | chr8:105156894-105309011 |
| 5904 | Cdh12 | NM_001008420.2 | chr15:21041206-21519288 |
| 5905 | Cdh13 | NM_019707.4 | chr8:120807654-121847348 |
| 5906 | Cdh15 | NM_007662.2 | chr8:125372273-125391297 |
| 5907 | Cdh16 | NM_001252627.1 | chr8:107125814-107148296 |
| 5908 | Cdh16 | NM_001252628.1 | chr8:107125814-107148296 |
| 5909 | Cdh16 | NM_007663.3 | chr8:107125814-107148296 |
| 5910 | Cdh17 | NM_019753.4 | chr4:11685303-11745052 |
| 5911 | Cdh18 | NM_001081299.1 | chr15:22966217-23404173 |
| 5912 | Cdh19 | NM_001081386.1 | chr1:112785771-112873949 |
| 5913 | Cdh2 | NM_007664.4 | chr18:16747385-16967558 |
| 5914 | Cdh20 | NM_011800.4 | chr1:106665395-106892058 |
| 5915 | Cdh22 | NM_174988.3 | chr2:164937006-165060237 |
| 5916 | Cdh23 | NM_001252635.1 | chr10:59765497-60159238 |
| 5917 | Cdh23 | NM_023370.3 | chr10:59765497-60159238 |
| 5918 | Cdh23 | NR_045556.1 | chr10:59765497-60159238 |
| 5919 | Cdh24 | NM_199470.2 | chr14:55250828-55260201 |
| 5920 | Cdh26 | NM_001291189.1 | chr2:178165219-178222071 |
| 5921 | Cdh26 | NM_198656.2 | chr2:178165219-178222071 |
| 5922 | Cdh3 | NM_001037809.5 | chr8:109034751-109080811 |
| 5923 | Cdh3 | NM_007665.3 | chr8:109034751-109080811 |
| 5924 | Cdh4 | NM_009867.2 | chr2:179177182-179634080 |
| 5925 | Cdh5 | NM_009868.4 | chr8:106625524-106668402 |
| 5926 | Cdh6 | NM_007666.3 | chr15:12963954-13103394 |
| 5927 | Cdh7 | NM_172853.2 | chr1:111880313-112035578 |
| 5928 | Cdh8 | NM_001039154.2 | chr8:101535786-101940371 |
| 5929 | Cdh8 | NM_001285913.1 | chr8:101535786-101940371 |
| 5930 | Cdh8 | NM_001285914.1 | chr8:101535786-101940371 |
| 5931 | Cdh8 | NM_007667.3 | chr8:101535786-101940371 |
| 5932 | Cdh9 | NM_009869.1 | chr15:16707855-16786532 |
| 5933 | Cdhr1 | NM_130878.2 | chr14:37891034-37911497 |
| 5934 | Cdhr2 | NM_001033364.3 | chr13:54802823-54854023 |
| 5935 | Cdhr3 | NM_001024478.1 | chr2:33718660-33777740 |
| 5936 | Cdhr5 | NM_001114322.1 | chr7:148454983-148462685 |
| 5937 | Cdhr5 | NM_028069.3 | chr7:148454983-148462685 |
| 5938 | Cdip1 | NM_025670.4 | chr16:4765461-4789935 |
| 5939 | Cdipt | NM_026638.3 | chr7:134119427-134124015 |
| 5940 | Cdk1 | NM_007659.3 | chr10:68799382-68815660 |
| 5941 | Cdk10 | NM_194444.2 | chr8:125748740-125756156 |
| 5942 | Cdk10 | NM_194446.2 | chr8:125748740-125756156 |
| 5943 | Cdk11b | NM_007661.3 | chr4:154998977-155024041 |
| 5944 | Cdk12 | NM_001109626.1 | chr11:98064618-98114854 |
| 5945 | Cdk12 | NM_001109628.1 | chr11:98064618-98114854 |
| 5946 | Cdk12 | NM_026952.2 | chr11:98064618-98114854 |
| 5947 | Cdk13 | NM_001081058.2 | chr13:17807795-17896931 |
| 5948 | Cdk13 | NM_027118.1 | chr13:17807795-17896931 |
| 5949 | Cdk14 | NM_011074.2 | chr5:4803384-5380251 |
| 5950 | Cdk15 | NM_001033373.2 | chr1:59313750-59409213 |
| 5951 | Cdk16 | NM_011049.4 | chrX:20265618-20277003 |
| 5952 | Cdk17 | NM_146239.2 | chr10:92623621-92704087 |
| 5953 | Cdk18 | NM_008795.2 | chr1:134010123-134036262 |
| 5954 | Cdk19 | NM_001168304.1 | chr10:40069113-40203624 |
| 5955 | Cdk19 | NM_001291816.1 | chr10:40069113-40203624 |
| 5956 | Cdk19 | NM_001291817.1 | chr10:40069113-40203624 |
| 5957 | Cdk19 | NM_198164.3 | chr10:40069113-40203624 |
| 5958 | Cdk2 | NM_016756.4 | chr10:128134994-128142107 |
| 5959 | Cdk2 | NM_183417.3 | chr10:128134994-128142107 |
| 5960 | Cdk20 | NM_053180.2 | chr13:64533860-64541029 |
| 5961 | Cdk2ap1 | NM_172879.2 | chr5:124195447-124804637 |
| 5962 | Cdk2ap2 | NM_026373.4 | chr19:4097350-4099017 |
| 5963 | Cdk3-ps | NR_004853.1 | chr11:116077315-116081601 |
| 5964 | Cdk4 | NM_009870.3 | chr10:126500658-126504338 |
| 5965 | Cdk5 | NM_007668.3 | chr5:23924059-23929348 |
| 5966 | Cdk5r1 | NM_009871.2 | chr11:80290547-80294681 |
| 5967 | Cdk5r2 | NM_009872.3 | chr1:74901602-74904306 |
| 5968 | Cdk5rap1 | NM_025876.2 | chr2:154161121-154198455 |
| 5969 | Cdk5rap2 | NM_145990.1 | chr4:69884057-70071401 |
| 5970 | Cdk5rap3 | NM_030248.2 | chr11:96769099-96777795 |
| 5971 | Cdk6 | NM_009873.2 | chr5:3344311-3522225 |
| 5972 | Cdk7 | NM_009874.1 | chr13:101466980-101500897 |
| 5973 | Cdk8 | NM_153599.3 | chr5:147043250-147114450 |
| 5974 | Cdk9 | NM_130860.3 | chr2:32561301-32568304 |
| 5975 | Cdkal1 | NM_144536.3 | chr13:29417174-29947457 |
| 5976 | Cdkl1 | NM_183294.2 | chr12:70847835-70891694 |
| 5977 | Cdkl2 | NM_001276315.1 | chr5:92435099-92472068 |
| 5978 | Cdkl2 | NM_016912.2 | chr5:92435099-92472068 |
| 5979 | Cdkl2 | NM_177270.4 | chr5:92435099-92472068 |
| 5980 | Cdkl3 | NM_001166653.1 | chr11:51817722-51898169 |
| 5981 | Cdkl3 | NM_001166654.1 | chr11:51817722-51898169 |
| 5982 | Cdkl3 | NM_001166655.1 | chr11:51817722-51898169 |
| 5983 | Cdkl3 | NM_001166656.1 | chr11:51817722-51898169 |
| 5984 | Cdkl3 | NM_001166657.1 | chr11:51817722-51898169 |
| 5985 | Cdkl3 | NM_153785.4 | chr11:51817722-51898169 |
| 5986 | Cdk4 | NM_001033443.4 | chr17:80922889-80963174 |
| 5987 | Cdkl5 | NM_001024624.2 | chrX:157222240-157432613 |
| 5988 | Cdkn1a | NM_001111099.1 | chr17:29227930-29237667 |
| 5989 | Cdkn1a | NM_007669.4 | chr17:29227930-29237667 |
| 5990 | Cdkn1b | NM_009875.4 | chr6:134870418-134875543 |
| 5991 | Cdkn1c | NM_001161624.1 | chr7:150644243-150646955 |
| 5992 | Cdkn1c | NM_009876.4 | chr7:150644243-150646955 |
| 5993 | Cdkn2a | NM_001040654.1 | chr4:88920376-88940523 |
| 5994 | Cdkn2a | NM_009877.2 | chr4:88920376-88940523 |
| 5995 | Cdkn2aip | NM_172407.3 | chr8:48794697-48799285 |
| 5996 | Cdkn2aipnl | NM_029976.3 | chr11:51781132-51790838 |
| 5997 | Cdkn2b | NM_007670.4 | chr4:88952197-88956941 |
| 5998 | Cdkn2c | NM_007671.3 | chr4:109333480-109372977 |
| 5999 | Cdkn2d | NM_009878.3 | chr9:123836859-123839607 |
| 6000 | Cdkn2d | NM_009878.3 | chr9:21092907-21095653 |
| 6001 | Cdkn3 | NM_028222.1 | chr14:47380215-47391200 |
| 6002 | Cdnf | NM_176647.4 | chr2:3430336-3443648 |
| 6003 | Cdo1 | NM_033037.3 | chr18:46872858-46887996 |
| 6004 | Cdon | NM_021339.2 | chr9:35259660-35315237 |
| 6005 | Cdpf1 | NM_001164625.1 | chr15:85637401-85642127 |
| 6006 | Cdpf1 | NM_001164626.1 | chr15:85637401-85642127 |
| 6007 | Cdpf1 | NM_197998.2 | chr15:85637401-85642127 |
| 6008 | Cdr1 | NM_001166658.1 | chrX:58436420-58438733 |
| 6009 | Cdr2 | NM_007672.2 | chr7:128100549-128125826 |
| 6010 | Cdr2l | NM_001080929.1 | chr11:115243229-115257446 |
| 6011 | Cdt1 | NM_025496.1 | chr11:62764694-62806597 |
| 6012 | Cds1 | NM_173370.3 | chr5:102194148-102252871 |
| 6013 | Cds2 | NM_001291039.1 | chr2:132088883-132137786 |
| 6014 | Cds2 | NM_001291040.1 | chr2:132088883-132137786 |
| 6015 | Cds2 | NM_138651.7 | chr2:132088883-132137786 |
| 6016 | Cdsn | NM_001008424.1 | chr17:35689072-35694125 |
| 6017 | Cdt1 | NM_026014.3 | chr8:125091914-125097030 |
| 6018 | Cdv3 | NM_001134426.1 | chr9:103255431-103268110 |
| 6019 | Cdv3 | NM_001134427.1 | chr9:103255431-103268110 |
| 6020 | Cdv3 | NM_175565.3 | chr9:103255431-103268110 |
| 6021 | Cdv3 | NM_175833.2 | chr9:103255431-103268110 |
| 6022 | Cdx1 | NM_009880.3 | chr18:61178515-61195853 |
| 6023 | Cdx2 | NM_007673.3 | chr5:148112475-148118825 |
| 6024 | Cdx4 | NM_007674.3 | chrX:100516736-100525563 |
| 6025 | Cdyl | NM_001123386.1 | chr13:35751730-35965933 |
| 6026 | Cdyl | NM_009881.3 | chr13:35751730-35965933 |
| 6027 | Cdyl2 | NM_029441.3 | chr8:119092623-119256891 |
| 6028 | Ceacam1 | NM_001039185.1 | chr7:26161837-26351436 |
| 6029 | Ceacam1 | NM_001039186.1 | chr7:26161837-26351436 |
| 6030 | Ceacam1 | NM_001039187.1 | chr7:26161837-26351436 |
| 6031 | Ceacam1 | NM_011926.2 | chr7:26161837-26351436 |
| 6032 | Ceacam10 | NM_007675.4 | chr7:25562222-25569674 |
| 6033 | Ceacam11 | NM_183289.2 | chr7:18557515-18563905 |
| 6034 | Ceacam12 | NM_001162523.1 | chr7:18651277-18663335 |
| 6035 | Ceacam12 | NM_001162524.1 | chr7:18651277-18663335 |
| 6036 | Ceacam12 | NM_026087.3 | chr7:18651277-18663335 |
| 6037 | Ceacam13 | NM_027210.1 | chr7:18595237-18604569 |
| 6038 | Ceacam13 | NM_028171.2 | chr7:18595237-18604569 |
| 6039 | Ceacam14 | NM_025957.4 | chr7:18398030-18400976 |
| 6040 | Ceacam15 | NM_175315.1 | chr7:17256679-17261054 |
| 6041 | Ceacam18 | NM_001033419.2 | chr7:20437446-20446648 |
| 6042 | Ceacam18 | NM_028236.1 | chr7:50890108-50904664 |
| 6043 | Ceacam19 | NM_177036.5 | chr7:20461090-20473314 |
| 6044 | Ceacam2 | NM_001113368.1 | chr7:26161837-26351436 |
| 6045 | Ceacam2 | NM_001113369.1 | chr7:26161837-26351436 |
| 6046 | Ceacam2 | NM_007543.4 | chr7:26161837-26351436 |
| 6047 | Ceacam20 | NM_027839.2 | chr7:20550760-20576460 |
| 6048 | Ceacam3 | NM_054059.1 | chr7:17735748-17748580 |
| 6049 | Ceacam5 | NM_028480.2 | chr7:18298600-18346470 |
| 6050 | Ceacam9 | NM_011927.4 | chr7:17307277-17311459 |
| 6051 | Ceacam-ps1 | NR_003247.2 | chr7:17234378-17242827 |
| 6052 | Cebpa | NM_001287514.1 | chr7:35904311-35906951 |
| 6053 | Cebpa | NM_007678.3 | chr7:35904311-35906951 |
| 6054 | Cebpb | NM_001287738.1 | chr2:167514414-167515932 |
| 6055 | Cebpd | NM_007679.4 | chr16:15887379-15889638 |
| 6056 | Cebpe | NM_207131.1 | chr14:55329199-55331011 |
| 6057 | Cebpg | NM_009884.3 | chr7:35831440-35841585 |
| 6058 | Cebpz | NM_001024806.2 | chr17:79318343-79336410 |
| 6059 | Cebpzos | NM_001177402.1 | chr17:79315838-79336410 |
| 6060 | Cebpzos | NM_001177403.1 | chr17:79315838-79336410 |
| 6061 | Cecr2 | NM_001128151.1 | chr6:120616438-120721209 |
| 6062 | Cecr5 | NM_144815.2 | chr6:120459511-120481317 |
| 6063 | Cecr6 | NM_033567.1 | chr6:120438956-120448825 |
| 6064 | Cel | NM_009885.1 | chr2:28411339-28418882 |
| 6065 | Cela1 | NM_033612.2 | chr15:100504852-100518351 |
| 6066 | Cela2a | NM_007919.2 | chr4:141370878-141381918 |

Fig. 25 - 33

| | | | |
|---|---|---|---|
| 6067 | Cela3b | NM_026419.2 | chr4:136976922-136986435 |
| 6068 | Celf1 | NM_001244891.1 | chr2:90780553-90859654 |
| 6069 | Celf1 | NM_001244903.1 | chr2:90780553-90859654 |
| 6070 | Celf1 | NM_017368.3 | chr2:90780553-90859654 |
| 6071 | Celf1 | NM_198683.2 | chr2:90780553-90859654 |
| 6072 | Celf2 | NM_001110228.1 | chr2:6460743-7317825 |
| 6073 | Celf2 | NM_001110229.1 | chr2:6460743-7317825 |
| 6074 | Celf2 | NM_001110230.1 | chr2:6460743-7317825 |
| 6075 | Celf2 | NM_001110231.1 | chr2:6460743-7317825 |
| 6076 | Celf2 | NM_001110232.1 | chr2:6460743-7317825 |
| 6077 | Celf2 | NM_001160292.1 | chr2:6460743-7317825 |
| 6078 | Celf2 | NM_001160293.1 | chr2:6460743-7317825 |
| 6079 | Celf2 | NM_010160.2 | chr2:6460743-7317825 |
| 6080 | Celf3 | NM_001289613.1 | chr3:94282216-94296120 |
| 6081 | Celf3 | NM_001289616.1 | chr3:94282216-94296120 |
| 6082 | Celf3 | NM_001289620.1 | chr3:94282216-94296120 |
| 6083 | Celf3 | NM_172434.3 | chr3:94282216-94296120 |
| 6084 | Celf3 | NR_110353.1 | chr3:94282216-94296120 |
| 6085 | Celf4 | NM_001146292.1 | chr18:25636120-25912484 |
| 6086 | Celf4 | NM_001146293.1 | chr18:25636120-25912484 |
| 6087 | Celf4 | NM_001146294.1 | chr18:25636120-25912484 |
| 6088 | Celf4 | NM_001146295.1 | chr18:25636120-25912484 |
| 6089 | Celf4 | NM_001174074.1 | chr18:25636120-25912484 |
| 6090 | Celf4 | NM_133195.3 | chr18:25636120-25912484 |
| 6091 | Celf5 | NM_176954.3 | chr10:80921972-80945454 |
| 6092 | Celf6 | NM_175235.3 | chr9:59426143-59455099 |
| 6093 | Celrr | NR_038008.1 | chr1:122983981-123017552 |
| 6094 | Celrr | NR_110450.1 | chr1:122983981-123017552 |
| 6095 | Celsr1 | NM_009886.2 | chr15:85729187-85864207 |
| 6096 | Celsr2 | NM_001004177.2 | chr3:108193765-108218412 |
| 6097 | Celsr2 | NM_017392.3 | chr3:108193765-108218412 |
| 6098 | Celsr3 | NM_080437.1 | chr9:108728650-108755300 |
| 6099 | Cemip | NM_030728.4 | chr7:91081366-91235015 |
| 6100 | Cend1 | NM_021316.4 | chr7:148612349-148615319 |
| 6101 | Cenpa | NM_007681.3 | chr5:30969274-30977199 |
| 6102 | Cenpb | NM_007682.2 | chr2:131003024-131005748 |
| 6103 | Cenpc1 | NM_007683.3 | chr5:86441049-86494608 |
| 6104 | Cenpe | NM_173762.4 | chr3:134875526-134936504 |
| 6105 | Cenpf | NM_001081363.1 | chr1:191464492-191511965 |
| 6106 | Cenph | NM_021886.1 | chr13:101529640-101545854 |
| 6107 | Cenpi | NM_145924.3 | chrX:130842701-130897178 |
| 6108 | Cenpj | NM_010149962 | chr14:57145597-57190683 |
| 6109 | Cenpk | NM_021790.2 | chr13:104995201-105039702 |
| 6110 | Cenpk | NM_181061.5 | chr13:104995201-105039702 |
| 6111 | Cenpk | NR_075088.1 | chr13:104995201-105039702 |
| 6112 | Cenpl | NM_001159930.2 | chr1:163001022-163016474 |
| 6113 | Cenpl | NM_027429.3 | chr1:163001022-163016474 |
| 6114 | Cenpm | NM_001080154.1 | chr15:82064205-82075177 |
| 6115 | Cenpm | NM_025639.4 | chr15:82064205-82075177 |
| 6116 | Cenpm | NM_178269.3 | chr15:82064205-82075177 |
| 6117 | Cenpo | NM_028131.3 | chr8:119445639-119465403 |
| 6118 | Cenpo | NM_134046.5 | chr12:4211672-4234294 |
| 6119 | Cenpp | NM_025495.3 | chr13:49559428-49748100 |
| 6120 | Cenpq | NM_031863.3 | chr17:41060003-41071500 |
| 6121 | Cenpt | NM_177150.2 | chr8:108368577-108375908 |
| 6122 | Cenpu | NM_027973.3 | chr8:47637423-47664938 |
| 6123 | Cenpv | NM_028448.1 | chr11:62338445-62352763 |
| 6124 | Cenpw | NM_001109747.1 | chr10:29915814-29920346 |
| 6125 | Cep104 | NM_177673.2 | chr4:153849669-153881334 |
| 6126 | Cep112 | NM_029586.2 | chr11:108286579-108721929 |
| 6127 | Cep112 | NM_029606.3 | chr11:108286579-108721929 |
| 6128 | Cep112 | NM_145688.2 | chr11:108286579-108721929 |
| 6129 | Cep120 | NM_178686.3 | chr18:53841377-53904201 |
| 6130 | Cep128 | NM_181815.3 | chr12:92236932-92622849 |
| 6131 | Cep131 | NM_009734.3 | chr11:119925743-119948141 |
| 6132 | Cep135 | NM_199032.2 | chr5:77020738-77075491 |
| 6133 | Cep152 | NM_001081091.1 | chr2:125388823-125450849 |
| 6134 | Cep162 | NM_199036.3 | chr9:87086797-87150367 |
| 6135 | Cep164 | NM_001081373.2 | chr9:45575028-45636721 |
| 6136 | Cep170 | NM_001085783.1 | chr1:178663784-178737255 |
| 6137 | Cep170b | NM_001024603.3 | chr12:113960385-113984802 |
| 6138 | Cep19 | NM_025892.2 | chr16:32099887-32108140 |
| 6139 | Cep192 | NM_027554.3 | chr18:67959760-68044824 |
| 6140 | Cep250 | NM_001129999.1 | chr2:155782293-155824636 |
| 6141 | Cep250 | NM_001130000.1 | chr2:155782293-155824636 |
| 6142 | Cep250 | NM_008383.3 | chr2:155782293-155824636 |
| 6143 | Cep250 | NM_177217.3 | chr2:155782293-155824636 |
| 6144 | Cep290 | NM_146009.2 | chr10:99950923-100036289 |
| 6145 | Cep350 | NM_001039184.1 | chr1:157692093-157820385 |
| 6146 | Cep41 | NM_031598.3 | chr6:30630456-30643682 |
| 6147 | Cep44 | NM_001009951.1 | chr8:59010318-59029363 |
| 6148 | Cep55 | NM_001164254.1 | chr19:38129514-38148915 |
| 6149 | Cep55 | NM_028293.1 | chr19:38129514-38148915 |
| 6150 | Cep55 | NM_028760.2 | chr19:38129514-38148915 |
| 6151 | Cep57 | NM_026665.4 | chr9:13612231-13631551 |
| 6152 | Cep57 | NR_037622.1 | chr9:13612231-13631551 |
| 6153 | Cep57l1 | NM_001243074.1 | chr10:41438645-41529674 |
| 6154 | Cep57l1 | NM_001243075.1 | chr10:41438645-41529674 |
| 6155 | Cep57l1 | NM_026643.5 | chr10:41438645-41529674 |
| 6156 | Cep57l1 | NM_029132.2 | chr10:41438645-41529674 |
| 6157 | Cep63 | NM_001081122.1 | chr9:102488907-102528454 |
| 6158 | Cep68 | NM_172260.3 | chr11:20127039-20149427 |
| 6159 | Cep70 | NM_099143886.2 | chr9:99143886-99200822 |
| 6160 | Cep72 | NM_028959.3 | chr13:74173942-74199733 |
| 6161 | Cep76 | NM_001081073.1 | chr18:67777050-67800990 |
| 6162 | Cep78 | NM_198019.2 | chr19:16030262-16059479 |
| 6163 | Cep83 | NM_029852.2 | chr10:94151534-94263081 |
| 6164 | Cep83os | NR_015524.1 | chr10:94136237-94151358 |
| 6165 | Cep85 | NM_144527.3 | chr4:133685772-133743000 |
| 6166 | Cep85l | NM_001204983.1 | chr10:52997887-53099657 |
| 6167 | Cep89 | NM_028120.2 | chr7:36182111-36223703 |
| 6168 | Cep95 | NM_001166685.1 | chr11:106650565-106680175 |
| 6169 | Cep95 | NM_177088.3 | chr11:106650565-106680175 |
| 6170 | Cep97 | NM_001159364.1 | chr16:55900000-55934961 |
| 6171 | Cep97 | NM_001159365.1 | chr16:55900000-55934961 |
| 6172 | Cep97 | NM_001159366.1 | chr16:55900000-55934961 |
| 6173 | Cep97 | NM_028815.4 | chr16:55900000-55934961 |
| 6174 | Cept1 | NM_133869.4 | chr3:106305178-106350720 |
| 6175 | Cer1 | NM_009887.2 | chr4:82527654-82531055 |
| 6176 | Cercam | NM_207298.2 | chr2:29725013-29738360 |
| 6177 | Cerk | NM_145475.4 | chr15:85969530-86016571 |
| 6178 | Cerkl | NM_001048176.1 | chr2:79172648-79269145 |
| 6179 | Cers1 | NM_138647.3 | chr8:72839674-72855487 |
| 6180 | Cers2 | NM_029789.1 | chr3:95119174-95127490 |
| 6181 | Cers3 | NM_001164201.1 | chr7:73888389-73968578 |
| 6182 | Cers4 | NM_026058.4 | chr8:4493404-4526079 |
| 6183 | Cers5 | NM_028015.2 | chr15:99566022-99602946 |
| 6184 | Cers6 | NM_172856.3 | chr2:68699613-68949347 |
| 6185 | Ces1a | NM_001013764.2 | chr8:95544113-95572091 |
| 6186 | Ces1b | NM_001081372.1 | chr8:95580625-95603916 |
| 6187 | Ces1c | NM_007954.4 | chr8:95622914-95655182 |
| 6188 | Ces1d | NM_053200.2 | chr8:95689970-95721703 |
| 6189 | Ces1e | NM_133660.3 | chr8:95725116-95753518 |
| 6190 | Ces1f | NM_144930.2 | chr8:95780134-95803635 |
| 6191 | Ces1g | NM_021456.4 | chr8:95826267-95861108 |
| 6192 | Ces2a | NM_001190330.1 | chr8:107257902-107265534 |
| 6193 | Ces2a | NM_133960.5 | chr8:107257902-107265534 |
| 6194 | Ces2b | NM_198171.2 | chr8:107355543-107362552 |
| 6195 | Ces2c | NM_145603.2 | chr8:107370967-107378382 |
| 6196 | Ces2d-ps | NR_033726.1 | chr8:107393323-107397982 |
| 6197 | Ces2e | NM_001163756.1 | chr8:107450159-107458572 |
| 6198 | Ces2e | NM_172759.3 | chr8:107450159-107458572 |
| 6199 | Ces2f | NM_001079865.2 | chr8:107471255-107479862 |
| 6200 | Ces2g | NM_197999.2 | chr8:107485617-107493437 |
| 6201 | Ces2h | NM_001272045.1 | chr8:107524752-107544310 |
| 6202 | Ces3a | NM_001164681.1 | chr8:107572498-107582314 |
| 6203 | Ces3a | NM_198672.1 | chr8:107572498-107582314 |
| 6204 | Ces3b | NM_001159415.1 | chr8:107607654-107617491 |
| 6205 | Ces3b | NM_145511.2 | chr8:107607654-107617491 |
| 6206 | Ces4a | NM_146213.2 | chr8:107655699-107674009 |
| 6207 | Ces5a | NM_001003951.2 | chr8:96038094-96059607 |
| 6208 | Cetn1 | NM_007593.5 | chr18:9618416-9619467 |
| 6209 | Cetn2 | NM_019405.2 | chrX:70158903-70163683 |
| 6210 | Cetn3 | NM_007684.3 | chr13:81922290-81936156 |
| 6211 | Cetn4 | NM_145825.2 | chr3:37207548-37211368 |
| 6212 | Cfb | NM_001142706.1 | chr17:34993318-34999459 |
| 6213 | Cfb | NM_008198.2 | chr17:34993318-34999459 |
| 6214 | Cfc1 | NM_007685.2 | chr1:34592492-34601156 |
| 6215 | Cfd | NM_001291915.1 | chr10:79353597-79355405 |
| 6216 | Cfd | NM_013459.3 | chr10:79353597-79355405 |
| 6217 | Cfdp1 | NM_011801.1 | chr8:114292372-114378210 |
| 6218 | Cfh | NM_009888.3 | chr1:141982431-142079988 |
| 6219 | Cfhr1 | NM_015780.2 | chr1:141443640-141456799 |
| 6220 | Cfhr2 | NM_001025575.2 | chr1:141706868-141755276 |
| 6221 | Cfi | NM_007686.2 | chr3:129539656-129578246 |
| 6222 | Cfl1 | NM_007687.5 | chr19:5490454-5494031 |
| 6223 | Cfl2 | NM_007688.2 | chr12:55959805-55963864 |
| 6224 | Cflar | NM_001289704.2 | chr1:58768351-58816047 |
| 6225 | Cflar | NM_009805.4 | chr1:58768351-58816047 |
| 6226 | Cflar | NM_207653.5 | chr1:58768351-58816047 |
| 6227 | Cflar | NR_110361.1 | chr1:58768351-58816047 |
| 6228 | Cfp | NM_008823.3 | chrX:20502660-20508650 |
| 6229 | Cftr | NM_021050.2 | chr6:18120686-18272769 |
| 6230 | Cga | NM_009839.2 | chr4:34841027-34854623 |
| 6231 | Cggbp1 | NM_178647.2 | chr16:64859910-64859317 |
| 6232 | Cgn | NM_001037711.2 | chr3:94563991-94590437 |
| 6233 | Cgnl1 | NM_026599.5 | chr9:71474315-71619409 |
| 6234 | Cgref1 | NM_001160149.1 | chr5:31235515-31651218 |
| 6235 | Cgref1 | NM_026770.1 | chr5:31235515-31651218 |
| 6236 | Cgrrf1 | NM_026832.3 | chr14:47451918-47473865 |
| 6237 | Ch25h | NM_009890.1 | chr19:34548273-34549625 |
| 6238 | Chac1 | NM_026929.4 | chr2:119176977-119180062 |
| 6239 | Chac2 | NM_001290667.1 | chr11:30854397-31002704 |
| 6240 | Chac2 | NM_026527.3 | chr11:30854397-31002704 |
| 6241 | Chad | NM_007689.4 | chr11:94426388-94430441 |
| 6242 | Chadl | NM_001164320.1 | chr15:81516597-81527717 |
| 6243 | Chaf1a | NM_013733.3 | chr17:56179838-56207449 |
| 6244 | Chaf1b | NM_028083.4 | chr16:93884145-93906351 |
| 6245 | Champ1 | NM_181854.2 | chr8:13869640-13881639 |
| 6246 | Chat | NM_009891.2 | chr14:33221389-33279095 |
| 6247 | Chchd1 | NM_025366.3 | chr14:21522249-21523647 |
| 6248 | Chchd10 | NM_175329.3 | chr10:75398318-75400439 |
| 6249 | Chchd2 | NM_024166.6 | chr5:130357031-130363340 |
| 6250 | Chchd3 | NM_025336.1 | chr6:32742226-33010152 |
| 6251 | Chchd4 | NM_133928.2 | chr6:91414269-91423417 |
| 6252 | Chchd5 | NM_025395.3 | chr2:128955435-128959847 |
| 6253 | Chchd6 | NM_001167736.1 | chr6:89333139-89545646 |
| 6254 | Chchd6 | NM_025351.3 | chr6:89333139-89545646 |
| 6255 | Chchd7 | NM_001190322.2 | chr4:3866034-3878529 |
| 6256 | Chchd7 | NM_001190323.2 | chr4:3866034-3878529 |

Fig. 25 - 34

| | | | | | | | | |
|---|---|---|---|---|---|---|---|---|
| 6257 | Chchd7 | NM_001190324.2 | chr4:3866034-3878529 | | 6352 | Chrna1 | NM_007389.5 | chr2:73401337-73418395 |
| 6258 | Chchd7 | NM_001285804.1 | chr4:3866034-3878529 | | 6353 | Chrna10 | NM_001081424.1 | chr7:109259779-109265227 |
| 6259 | Chchd7 | NM_181391.4 | chr4:3866034-3878529 | | 6354 | Chrna2 | NM_144803.2 | chr14:66759796-66771785 |
| 6260 | Chchd7 | NR_104354.1 | chr4:3866034-3878529 | | 6355 | Chrna3 | NM_145129.2 | chr9:54859149-54874366 |
| 6261 | Chchd7 | NR_104355.1 | chr4:3866034-3878529 | | 6356 | Chrna4 | NM_015730.5 | chr2:180757015-180773882 |
| 6262 | Chchd7 | NR_104356.1 | chr4:3866034-3878529 | | 6357 | Chrna5 | NM_176844.4 | chr9:54828686-54855586 |
| 6263 | Chchd7 | NR_104357.1 | chr4:3866034-3878529 | | 6358 | Chrna6 | NM_021369.2 | chr8:28513683-28524416 |
| 6264 | Chd1 | NM_007690.3 | chr17:15841930-15909576 | | 6359 | Chrna7 | NM_007390.3 | chr7:70243577-70357412 |
| 6265 | Chd1l | NM_026539.2 | chr3:97364670-97414113 | | 6360 | Chrna9 | NM_001081104.1 | chr5:66358362-66368725 |
| 6266 | Chd2 | NM_001081345.2 | chr7:80571538-80686632 | | 6361 | Chrnb1 | NM_009601.4 | chr11:69597537-69609439 |
| 6267 | Chd3 | NM_146019.4 | chr11:69156774-69182928 | | 6362 | Chrnb2 | NM_009602.4 | chr3:89557370-89568554 |
| 6268 | Chd3os | NR_027827.1 | chr11:69154270-69156149 | | 6363 | Chrnb3 | NM_027454.4 | chr8:28479182-28510202 |
| 6269 | Chd4 | NM_145979.2 | chr6:125046181-125080519 | | 6364 | Chrnb3 | NM_173212.4 | chr8:28479182-28510202 |
| 6270 | Chd5 | NM_001081376.1 | chr4:151712759-151764303 | | 6365 | Chrnb4 | NM_148944.4 | chr9:54875962-54896351 |
| 6271 | Chd5 | NM_029216.2 | chr4:151712759-151764303 | | 6366 | Chrnd | NM_021600.3 | chr1:89087171-89096645 |
| 6272 | Chd6 | NM_173368.3 | chr2:160772713-160934792 | | 6367 | Chrne | NM_009603.1 | chr11:70428385-70434696 |
| 6273 | Chd7 | NM_001277149.1 | chr4:8617552-8795596 | | 6368 | Chrng | NM_009604.3 | chr1:89102385-89108410 |
| 6274 | Chd8 | NM_201637.2 | chr14:52817826-52857247 | | 6369 | Chst1 | NM_023850.1 | chr2:92459863-92455409 |
| 6275 | Chd9 | NM_177224.2 | chr8:93352733-93578407 | | 6370 | Chst10 | NM_145142.2 | chr1:38920717-38955005 |
| 6276 | Chdh | NM_001136240.1 | chr14:30822185-31340242 | | 6371 | Chst11 | NM_021439.2 | chr10:82448241-82658636 |
| 6277 | Chdh | NM_172264.2 | chr14:30822185-31340242 | | 6372 | Chst12 | NM_021528.3 | chr5:140981562-141001192 |
| 6278 | Chdh | NM_175343.5 | chr14:30822185-31340242 | | 6373 | Chst13 | NM_027928.1 | chr6:90258344-90275179 |
| 6279 | Chek1 | NM_007691.5 | chr9:36516066-36534243 | | 6374 | Chst14 | NM_028117.3 | chr2:118752232-118754319 |
| 6280 | Chek2 | NM_016681.3 | chr5:111269035-111303152 | | 6375 | Chst15 | NM_029935.5 | chr7:139427938-139508838 |
| 6281 | Cherp | NM_138585.3 | chr8:74984382-74999132 | | 6376 | Chst2 | NM_018763.2 | chr9:95301344-95307689 |
| 6282 | Chfr | NM_001289577.1 | chr5:110564848-110605523 | | 6377 | Chst3 | NM_016803.3 | chr10:59644275-59682008 |
| 6283 | Chfr | NM_001289578.1 | chr5:110564848-110605523 | | 6378 | Chst4 | NM_011998.3 | chr8:112552974-112563234 |
| 6284 | Chfr | NM_001289579.1 | chr5:110564848-110605523 | | 6379 | Chst5 | NM_019950.2 | chr8:114413034-114434099 |
| 6285 | Chfr | NM_001289580.1 | chr5:110564848-110605523 | | 6380 | Chst7 | NM_021715.1 | chrX:19636695-19674646 |
| 6286 | Chfr | NM_172717.4 | chr5:110564848-110605523 | | 6381 | Chst8 | NM_175140.4 | chr7:35459486-35597730 |
| 6287 | Chga | NM_007693.1 | chr12:103793178-103803237 | | 6382 | Chst9 | NM_199055.2 | chr18:15610683-15876555 |
| 6288 | Chgb | NM_007694.4 | chr2:132607013-132620808 | | 6383 | Chsy1 | NM_001081163.1 | chr7:73254400-73318684 |
| 6289 | Chia1 | NM_023186.3 | chr3:105916299-105935034 | | 6384 | Chsy3 | NM_001081328.1 | chr18:59334993-59570990 |
| 6290 | Chic1 | NM_009767.2 | chrX:100551814-100591457 | | 6385 | Chtf18 | NM_145409.2 | chr17:25855975-25864360 |
| 6291 | Chic2 | NM_028850.5 | chr5:75402448-75440651 | | 6386 | Chtf8 | NM_145412.3 | chr8:109407762-109417493 |
| 6292 | Chid1 | NM_001142681.1 | chr7:148661134-148725756 | | 6387 | Chtop | NM_023215.6 | chr3:90302879-90313365 |
| 6293 | Chid1 | NM_026522.5 | chr7:148661134-148725756 | | 6388 | Chuk | NM_001162410.1 | chr19:44147823-44181967 |
| 6294 | Chil3 | NM_007695.3 | chr3:136078980-136086608 | | 6389 | Chuk | NM_007700.2 | chr19:44147823-44181967 |
| 6295 | Chil3 | NM_009892.2 | chr3:105950471-105970482 | | 6390 | Churc1 | NM_206534.1 | chr12:77866559-77884165 |
| 6296 | Chil4 | NM_145126.2 | chr3:106004408-106022397 | | 6391 | Ciao1 | NM_025296.4 | chr2:127066673-127073552 |
| 6297 | Chil6 | NM_178412.2 | chr3:106190301-106209100 | | 6392 | Ciapin1 | NM_134141.4 | chr8:97343718-97362240 |
| 6298 | Chit1 | NM_001284524.1 | chr1:136607818-136048117 | | 6393 | Ciart | NM_001033302.2 | chr3:95682428-95686151 |
| 6299 | Chit1 | NM_001284525.1 | chr1:136007818-136048117 | | 6394 | Cib1 | NM_001291275.1 | chr7:87372041-87377691 |
| 6300 | Chit1 | NM_027979.2 | chr1:136007818-136048117 | | 6395 | Cib1 | NM_001291276.1 | chr7:87372041-87377691 |
| 6301 | Chka | NM_001271496.1 | chr19:3851772-3894369 | | 6396 | Cib1 | NM_011870.2 | chr7:87372041-87377691 |
| 6302 | Chka | NM_013490.4 | chr19:3851772-3894369 | | 6397 | Cib2 | NM_019686.5 | chr9:54393158-54407886 |
| 6303 | Chka | NR_073190.1 | chr19:3851772-3894369 | | 6398 | Cib3 | NM_001080812.1 | chr8:74728233-74736736 |
| 6304 | Chkb | NM_007692.6 | chr15:89246835-89260358 | | 6399 | Cib4 | NM_028483.1 | chr5:30787956-30848209 |
| 6305 | Chkb | NR_037153.1 | chr15:89246835-89260358 | | 6400 | Cic | NM_001110131.1 | chr7:26067197-26079167 |
| 6306 | Chkb | NR_037154.1 | chr15:89246835-89260358 | | 6401 | Cic | NM_001110132.1 | chr7:26067197-26079167 |
| 6307 | ChkbCpt1b | NR_004843.2 | chr15:89246836-89260358 | | 6402 | Cic | NM_027882.4 | chr7:26067197-26079167 |
| 6308 | Chl1 | NM_007697.2 | chr6:103460869-103683029 | | 6403 | Cidea | NM_007702.2 | chr18:67503218-67527448 |
| 6309 | Chm | NM_148818.2 | chrX:110154200-110299124 | | 6404 | Cideb | NM_009894.3 | chr14:56372892-56377261 |
| 6310 | Chml | NM_021350.2 | chr1:177612369-177618484 | | 6405 | Cidec | NM_178373.3 | chr6:113374629-113385749 |
| 6311 | Chmp1a | NM_145606.3 | chr8:125728160-125736668 | | 6406 | Ciita | NM_001243760.2 | chr16:10480164-10527657 |
| 6312 | Chmp1b | NM_024190.2 | chr18:67365013-67367541 | | 6407 | Ciita | NM_001243761.1 | chr16:10480164-10527657 |
| 6313 | Chmp2a | NM_026885.3 | chr7:13617354-13620126 | | 6408 | Ciita | NM_007575.4 | chr16:10480164-10527657 |
| 6314 | Chmp2b | NM_026879.2 | chr16:65539377-65562942 | | 6409 | Cilp | NM_173385.2 | chr9:65112986-65128412 |
| 6315 | Chmp3 | NM_025783.3 | chr6:71493847-71531568 | | 6410 | Cilp2 | NM_026818.1 | chr8:72404264-72411291 |
| 6316 | Chmp4b | NM_029362.3 | chr2:154482761-154520519 | | 6411 | Cinp | NM_026048.4 | chr12:112110819-112127355 |
| 6317 | Chmp4c | NM_025519.2 | chr3:10366972-10391005 | | 6412 | Cinp | NM_027223.1 | chr12:112110819-112127355 |
| 6318 | Chmp5 | NM_029814.1 | chr4:40895585-40912335 | | 6413 | Cipc | NM_001289429.1 | chr12:88287990-88306316 |
| 6319 | Chmp6 | NM_001085498.2 | chr11:119775123-119780866 | | 6414 | Cipc | NM_001289430.1 | chr12:88287990-88306316 |
| 6320 | Chmp7 | NM_134078.4 | chr14:70116785-70132377 | | 6415 | Cipc | NM_001289431.1 | chr12:88287990-88306316 |
| 6321 | Chn1 | NM_001113246.2 | chr2:73434582-73613403 | | 6416 | Cipc | NM_001289432.1 | chr12:88287990-88306316 |
| 6322 | Chn1 | NM_001166603.1 | chr2:73434582-73613403 | | 6417 | Cipc | NM_173735.3 | chr12:88287990-88306316 |
| 6323 | Chn1 | NM_001166604.1 | chr2:73434582-73613403 | | 6418 | Cir1 | NM_025854.3 | chr2:73121928-73150649 |
| 6324 | Chn1 | NM_009716.3 | chr2:73434582-73613403 | | 6419 | Cirbp | NM_007705.2 | chr10:79630585-79634398 |
| 6325 | Chn1 | NM_175752.3 | chr2:73434582-73613403 | | 6420 | Cirh1a | NM_011574.2 | chr9:109417559-109446994 |
| 6326 | Chn1os3 | NR_040623.1 | chr2:73434583-73454069 | | 6421 | Cisd1 | NM_134007.4 | chr10:70793241-70807597 |
| 6327 | Chn2 | NM_001163640.1 | chr6:53989925-54380215 | | 6422 | Cisd2 | NM_025902.3 | chr3:135069375-135086397 |
| 6328 | Chn2 | NM_023543.2 | chr6:53989925-54380215 | | 6423 | Cisd3 | NM_001085500.2 | chr11:97547265-97549939 |
| 6329 | Chodl | NM_139134.3 | chr16:78931192-78951973 | | 6424 | Cish | NM_009895.3 | chr9:107199019-107204292 |
| 6330 | Chordc1 | NM_025844.2 | chr9:18096710-18118444 | | 6425 | Cistr-act | NR_104334.1 | chr15:102576871-102577340 |
| 6331 | Chp1 | NM_019769.3 | chr2:119373442-119412758 | | 6426 | Cit | NM_007708.3 | chr5:116295664-116456350 |
| 6332 | Chp2 | NM_027363.2 | chr7:129363089-129366053 | | 6427 | Cited1 | NM_001276466.1 | chrX:99442716-99447520 |
| 6333 | Chpf | NM_001001565.2 | chr1:75471143-75476046 | | 6428 | Cited1 | NM_001276473.1 | chrX:99442716-99447520 |
| 6334 | Chpf | NM_001001566.3 | chr1:75471143-75476046 | | 6429 | Cited1 | NM_001276474.1 | chrX:99442716-99447520 |
| 6335 | Chpf2 | NM_133913.2 | chr5:24092566-24098304 | | 6430 | Cited1 | NM_007709.4 | chrX:99442716-99447520 |
| 6336 | Chpt1 | NM_001146690.1 | chr10:87922331-87966715 | | 6431 | Cited2 | NM_010828.3 | chr10:17443033-17445480 |
| 6337 | Chpt1 | NM_144807.3 | chr10:87922331-87966715 | | 6432 | Cited4 | NM_019563.2 | chr4:120339167-120340425 |
| 6338 | Chpt1 | NR_027477.1 | chr10:87922331-87966715 | | 6433 | Ciz1 | NM_001252534.1 | chr2:32218529-32233833 |
| 6339 | Chrac1 | NM_053068.2 | chr15:72920841-72924505 | | 6434 | Ciz1 | NM_001252536.1 | chr2:32218529-32233833 |
| 6340 | Chrd | NM_001278041.1 | chr16:20724526-20742457 | | 6435 | Ciz1 | NM_001252537.1 | chr2:32218529-32233833 |
| 6341 | Chrd | NM_009893.2 | chr16:20724526-20742457 | | 6436 | Ciz1 | NM_001252538.1 | chr2:32218529-32233833 |
| 6342 | Chrdl1 | NM_001114385.1 | chrX:139720216-139828805 | | 6437 | Ciz1 | NM_028412.2 | chr2:32218529-32233833 |
| 6343 | Chrdl1 | NM_031258.3 | chrX:139720216-139828805 | | 6438 | CK137956 | NM_001134733.1 | chr4:127604835-127648085 |
| 6344 | Chrdl1 | NM_001291320.1 | chr7:107154913-107183236 | | 6439 | Ckap2 | NM_001004140.2 | chr8:23278623-23296291 |
| 6345 | Chrdl2 | NM_133709.3 | chr7:107154913-107183236 | | 6440 | Ckap2l | NM_181589.3 | chr2:129093945-129122948 |
| 6346 | Chrm1 | NM_001112697.1 | chr19:8738494-8758092 | | 6441 | Ckap4 | NM_175451.1 | chr10:83989049-83996633 |
| 6347 | Chrm1 | NM_007698.3 | chr19:8738494-8758092 | | 6442 | Ckap5 | NM_001165989.1 | chr2:91386478-91460822 |
| 6348 | Chrm2 | NM_203491.3 | chr6:36338684-36474774 | | 6443 | Ckap5 | NM_029437.2 | chr2:91386478-91460822 |
| 6349 | Chrm3 | NM_033269.4 | chr13:9875858-10360049 | | 6444 | Ckb | NM_021273.4 | chr12:112907565-112910549 |
| 6350 | Chrm4 | NM_007699.2 | chr2:91762346-91769986 | | 6445 | Cklf | NM_001037841.3 | chr8:106774760-106788836 |
| 6351 | Chrm5 | NM_205783.2 | chr2:112319228-112320974 | | 6446 | Cklf | NM_001286383.1 | chr8:106774760-106788836 |

Fig. 25 - 35

| | | | | | | | | |
|---|---|---|---|---|---|---|---|---|
| 6447 | Ckif | NM_029295.3 | chr8:106774760-106788836 | | 6542 | Clec14a | NM_025809.5 | chr12:59365706-59370245 |
| 6448 | Ckif | NR_104433.1 | chr8:106774760-106788836 | | 6543 | Clec16a | NM_001204229.1 | chr16:10545431-10744971 |
| 6449 | Ckm | NM_007710.2 | chr7:19996443-20006932 | | 6544 | Clec16a | NM_177562.5 | chr16:10545431-10744971 |
| 6450 | Ckmt1 | NM_009897.2 | chr2:121184377-121189473 | | 6545 | Clec18a | NM_181549.3 | chr8:113593396-113605608 |
| 6451 | Ckmt2 | NM_198415.2 | chr13:91992991-92016490 | | 6546 | Clec1a | NM_175526.3 | chr6:129376701-129402018 |
| 6452 | Cks1b | NM_016904.1 | chr3:89219393-89222213 | | 6547 | Clec1b | NM_001204239.1 | chr6:129347314-129355431 |
| 6453 | Cks1brt | NM_001037922.3 | chr8:87675822-87697521 | | 6548 | Clec1b | NM_001204253.1 | chr6:129347314-129355431 |
| 6454 | Cks2 | NM_025415.3 | chr13:51740600-51746031 | | 6549 | Clec1b | NM_019985.3 | chr6:129347314-129355431 |
| 6455 | Clasp1 | NM_001081276.1 | chr1:120285634-120506039 | | 6550 | Clec2d | NM_053109.3 | chr6:129130632-129136653 |
| 6456 | Clasp1 | NM_029709.2 | chr1:120285634-120506039 | | 6551 | Clec2e | NM_153506.4 | chr6:129041833-129050921 |
| 6457 | Clasp1 | NM_177548.2 | chr1:120285634-120506039 | | 6552 | Clec2f | NM_001277202.1 | chr6:128964129-128970545 |
| 6458 | Clasp2 | NM_001081960.1 | chr9:113650590-113828815 | | 6553 | Clec2g | NM_001168223.1 | chr6:128884398-128934725 |
| 6459 | Clasp2 | NM_001114347.1 | chr9:113650590-113828815 | | 6554 | Clec2g | NM_001168224.1 | chr6:128884398-128934725 |
| 6460 | Clasp2 | NM_001286599.1 | chr9:113650590-113828815 | | 6555 | Clec2g | NM_027562.4 | chr6:128884398-128934725 |
| 6461 | Clasp2 | NM_001286600.1 | chr9:113650590-113828815 | | 6556 | Clec2h | NM_053165.5 | chr6:128612402-128627392 |
| 6462 | Clasp2 | NM_001286601.1 | chr9:113650590-113828815 | | 6557 | Clec2i | NM_001289706.1 | chr6:128798061-128848185 |
| 6463 | Clasp2 | NM_001286602.1 | chr9:113650590-113828815 | | 6558 | Clec2i | NM_001289707.1 | chr6:128798061-128848185 |
| 6464 | Clasp2 | NM_001286603.1 | chr9:113650590-113828815 | | 6559 | Clec2i | NM_001289708.1 | chr6:128798061-128848185 |
| 6465 | Clasp2 | NM_029633.2 | chr9:113650590-113828815 | | 6560 | Clec2i | NM_020257.2 | chr6:128798061-128848185 |
| 6466 | Clasrp | NM_016680.5 | chr7:20166391-20189817 | | 6561 | Clec2l | NM_001101507.1 | chr6:38613068-38630864 |
| 6467 | Clca1 | NM_009899.4 | chr3:144393279-144423703 | | 6562 | Clec3a | NM_001007223.3 | chr8:116941933-116952033 |
| 6468 | Clca2 | NM_030601.3 | chr3:144459522-144482458 | | 6563 | Clec3b | NM_011606.2 | chr9:123060063-123066550 |
| 6469 | Clca3 | NM_017474.2 | chr3:144667500-144695740 | | 6564 | Clec4a1 | NM_199311.2 | chr6:122871865-122884637 |
| 6470 | Clca4 | NM_139148.2 | chr3:144485586-144512266 | | 6565 | Clec4a2 | NM_001170332.1 | chr6:123072707-123094017 |
| 6471 | Clca5 | NM_178693.4 | chr3:144373228-144762005 | | 6566 | Clec4a2 | NM_001170333.1 | chr6:123072707-123094017 |
| 6472 | Clca6 | NM_207208.3 | chr3:144615449-144638009 | | 6567 | Clec4a2 | NM_011999.4 | chr6:123072707-123094017 |
| 6473 | Clcc1 | NM_001177770.1 | chr3:108456830-108525217 | | 6568 | Clec4a3 | NM_001204241.1 | chr6:122902532-122919896 |
| 6474 | Clcc1 | NM_001177771.1 | chr3:108456830-108525217 | | 6569 | Clec4a3 | NM_153197.4 | chr6:122902532-122919896 |
| 6475 | Clcc1 | NM_145543.2 | chr3:108456830-108525217 | | 6570 | Clec4a4 | NM_001005860.2 | chr6:122940384-122974439 |
| 6476 | Clcf1 | NM_019952.3 | chr19:4214391-4222615 | | 6571 | Clec4b1 | NM_001190310.1 | chr6:122999979-123021573 |
| 6477 | Clcn1 | NM_013491.2 | chr6:42236683-42264655 | | 6572 | Clec4b1 | NM_027218.3 | chr6:122999979-123021573 |
| 6478 | Clcn2 | NM_009900.2 | chr16:20703039-20716709 | | 6573 | Clec4b2 | NM_001004159.2 | chr6:123123040-123154689 |
| 6479 | Clcn3 | NM_007711.3 | chr8:63389185-63462108 | | 6574 | Clec4d | NM_001163161.1 | chr6:123212124-123225286 |
| 6480 | Clcn3 | NM_173873.1 | chr8:63389185-63462108 | | 6575 | Clec4d | NM_010819.4 | chr6:123212124-123225286 |
| 6481 | Clcn3 | NM_173874.1 | chr8:63389185-63462108 | | 6576 | Clec4e | NM_019948.2 | chr6:123231806-123239889 |
| 6482 | Clcn3 | NM_173876.3 | chr8:63389185-63462108 | | 6577 | Clec4f | NM_016751.3 | chr6:83594535-83606110 |
| 6483 | Clcn4-2 | NM_011334.4 | chr7:7235020-7252268 | | 6578 | Clec4g | NM_029465.3 | chr8:3716070-3720663 |
| 6484 | Clcn5 | NM_001243762.1 | chrX:6735537-6896484 | | 6579 | Clec4n | NM_001190320.1 | chr6:123179860-123197042 |
| 6485 | Clcn5 | NM_016691.4 | chrX:6735537-6896484 | | 6580 | Clec4n | NM_001190321.1 | chr6:123179860-123197042 |
| 6486 | Clcn6 | NM_011929.2 | chr4:147380592-147412876 | | 6581 | Clec4n | NM_020001.2 | chr6:123179860-123197042 |
| 6487 | Clcn7 | NM_011930.3 | chr17:25270338-25299044 | | 6582 | Clec5a | NM_001038604.1 | chr6:40524896-40535804 |
| 6488 | Clcnka | NM_001146301.1 | chr4:140940525-140954621 | | 6583 | Clec5a | NM_021364.2 | chr6:40524896-40535804 |
| 6489 | Clcnka | NM_024412.1 | chr4:140940525-140954621 | | 6584 | Clec7a | NM_020008.2 | chr6:129411608-129422795 |
| 6490 | Clcnkb | NM_019701.2 | chr4:140960271-140971903 | | 6585 | Clec9a | NM_001205363.1 | chr6:129358879-129374782 |
| 6491 | Cldn1 | NM_016674.4 | chr16:26356731-26371925 | | 6586 | Clec9a | NM_001205364.1 | chr6:129358879-129374782 |
| 6492 | Cldn10 | NM_001160096.1 | chr14:119187092-119273747 | | 6587 | Clec9a | NM_001205365.1 | chr6:129358879-129374782 |
| 6493 | Cldn10 | NM_001160097.1 | chr14:119187092-119273747 | | 6588 | Clec9a | NM_172732.3 | chr6:129358879-129374782 |
| 6494 | Cldn10 | NM_001160098.1 | chr14:119187092-119273747 | | 6589 | Clgn | NM_009904.2 | chr8:85913789-85950728 |
| 6495 | Cldn10 | NM_001160099.1 | chr14:119187092-119273747 | | 6590 | Clhc1 | NM_001081099.1 | chr4:134066913-134079837 |
| 6496 | Cldn10 | NM_021386.4 | chr14:119187092-119273747 | | 6591 | Clic1 | NM_033444.2 | chr17:35187187-35195664 |
| 6497 | Cldn10 | NM_023878.2 | chr14:119187092-119273747 | | 6592 | Clic3 | NM_027085.3 | chr2:25313362-25314292 |
| 6498 | Cldn11 | NM_008770.3 | chr3:31048841-31063248 | | 6593 | Clic4 | NM_013885.2 | chr4:134769884-134828675 |
| 6499 | Cldn12 | NM_001193659.1 | chr17:44325520-44417117 | | 6594 | Clic5 | NM_172621.2 | chr17:44325520-44417117 |
| 6500 | Cldn12 | NM_001193660.1 | chr5:5505014-5514976 | | 6595 | Clic6 | NM_172469.3 | chr16:92498391-92541486 |
| 6501 | Cldn12 | NM_001193661.1 | chr5:5505014-5514976 | | 6596 | Clint1 | NM_001045520.1 | chr11:45665465-45724127 |
| 6502 | Cldn12 | NM_022890.2 | chr5:5505014-5514976 | | 6597 | Clip1 | NM_001291229.1 | chr5:124027802-124134370 |
| 6503 | Cldn13 | NM_020504.4 | chr5:135390119-135391400 | | 6598 | Clip1 | NM_019765.5 | chr5:124027802-124134370 |
| 6504 | Cldn14 | NM_001165925.1 | chr16:93919275-94009082 | | 6599 | Clip2 | NM_001039162.2 | chr5:134965252-135028304 |
| 6505 | Cldn14 | NM_001165926.1 | chr16:93919275-94009082 | | 6600 | Clip2 | NM_009990.3 | chr5:134965252-135028304 |
| 6506 | Cldn14 | NM_019500.4 | chr16:93919275-94009082 | | 6601 | Clip3 | NM_001081114.1 | chr7:31076771-31093386 |
| 6507 | Cldn15 | NM_021719.4 | chr5:137443738-137451715 | | 6602 | Clip4 | NM_001271483.1 | chr17:72119030-72213550 |
| 6508 | Cldn16 | NM_053241.5 | chr16:26463220-26482850 | | 6603 | Clip4 | NM_001271484.1 | chr17:72119030-72213550 |
| 6509 | Cldn17 | NM_181490.3 | chr16:88506051-88507223 | | 6604 | Clip4 | NM_030179.3 | chr17:72119030-72213550 |
| 6510 | Cldn18 | NM_001194921.1 | chr9:99591215-99617686 | | 6605 | Clip4 | NM_175378.1 | chr17:72119030-72213550 |
| 6511 | Cldn18 | NM_001194922.1 | chr9:99591215-99617686 | | 6606 | Clip4 | NR_073185.1 | chr17:72119030-72213550 |
| 6512 | Cldn18 | NM_001194923.1 | chr9:99591215-99617686 | | 6607 | Clk1 | NM_001042634.2 | chr1:58468831-58480932 |
| 6513 | Cldn18 | NM_019815.3 | chr9:99591215-99617686 | | 6608 | Clk1 | NR_027853.1 | chr1:58468831-58480932 |
| 6514 | Cldn19 | NM_001038590.1 | chr4:118928045-118935043 | | 6609 | Clk1 | NR_027854.1 | chr1:58468831-58480932 |
| 6515 | Cldn19 | NM_153105.7 | chr4:118928045-118935043 | | 6610 | Clk2 | NM_001163432.1 | chr3:88968726-88981009 |
| 6516 | Cldn2 | NM_016675.4 | chrX:136335346-136345927 | | 6611 | Clk2 | NM_007712.3 | chr3:88968726-88981009 |
| 6517 | Cldn20 | NM_001101560.1 | chr17:3532554-3533213 | | 6612 | Clk3 | NM_007713.4 | chr9:57598517-57613667 |
| 6518 | Cldn22 | NM_029383.1 | chr8:48909835-48910829 | | 6613 | Clk4 | NM_007714.6 | chr11:51076672-51095266 |
| 6519 | Cldn23 | NM_027998.4 | chr8:36887762-36889613 | | 6614 | Clmn | NM_001040682.1 | chr12:106001323-106103286 |
| 6520 | Cldn24 | NM_001111318.1 | chr8:48907496-48908159 | | 6615 | Clmn | NM_053155.2 | chr12:106001323-106103286 |
| 6521 | Cldn25 | NM_001252450.1 | chr16:58728022-58734360 | | 6616 | Clmn | NR_104435.1 | chr12:106001323-106103286 |
| 6522 | Cldn25 | NM_001252451.1 | chr16:58728022-58734360 | | 6617 | Clmn | NR_104436.1 | chr12:106001323-106103286 |
| 6523 | Cldn25 | NM_171826.3 | chr16:58728022-58734360 | | 6618 | Clmn | NR_104437.1 | chr12:106001323-106103286 |
| 6524 | Cldn25 | NR_045517.1 | chr16:58728022-58734360 | | 6619 | Clmn | NR_104438.1 | chr12:106001323-106103286 |
| 6525 | Cldn25 | NR_045518.1 | chr16:58728022-58734360 | | 6620 | Clmn | NR_104439.1 | chr12:106001323-106103286 |
| 6526 | Cldn26 | NM_029070.2 | chr16:8409368-8425229 | | 6621 | Clmp | NM_133733.4 | chr9:40494046-40592129 |
| 6527 | Cldn3 | NM_009902.4 | chr5:135462084-135463346 | | 6622 | Cln3 | NM_001146311.1 | chr7:133714913-133727794 |
| 6528 | Cldn4 | NM_009903.2 | chr5:135420992-135422804 | | 6623 | Cln3 | NM_009907.3 | chr7:133714913-133727794 |
| 6529 | Cldn5 | NM_013805.4 | chr16:18776939-18778355 | | 6624 | Cln5 | NM_001033242.1 | chr14:103469432-103476847 |
| 6530 | Cldn6 | NM_018777.4 | chr17:23816331-23819414 | | 6625 | Cln6 | NM_001033175.2 | chr9:62686594-62699809 |
| 6531 | Cldn7 | NM_001193619.1 | chr11:69778280-69781388 | | 6626 | Cln8 | NM_012000.3 | chr8:14888535-14901719 |
| 6532 | Cldn7 | NM_016887.6 | chr11:69778280-69781388 | | 6627 | Clnk | NM_013748.3 | chr5:39097698-39267932 |
| 6533 | Cldn8 | NM_018778.3 | chr16:88561070-88563428 | | 6628 | Clns1a | NM_023671.2 | chr7:104845166-104869303 |
| 6534 | Cldn9 | NM_020293.3 | chr17:23819550-23820993 | | 6629 | Clock | NM_001289826.1 | chr5:76638892-76733817 |
| 6535 | Cldnd2 | NM_028849.1 | chr7:50696185-50698690 | | 6630 | Clock | NM_007715.6 | chr5:76638892-76733817 |
| 6536 | Clec10a | NM_001204252.1 | chr11:69980124-69984338 | | 6631 | Clp1 | NM_133840.2 | chr2:84563278-84567425 |
| 6537 | Clec10a | NM_010796.3 | chr11:69980124-69984338 | | 6632 | Clpb | NM_009191.3 | chr7:108812281-108938682 |
| 6538 | Clec11a | NM_009131.1 | chr7:51559135-51562329 | | 6633 | Clpp | NM_017393.2 | chr17:57129686-57135794 |
| 6539 | Clec12a | NM_177686.4 | chr6:129300261-129315321 | | 6634 | Clps | NM_025469.2 | chr17:28695159-28697659 |
| 6540 | Clec12b | NM_001204223.1 | chr6:129325530-129335892 | | 6635 | Clpsl2 | NM_001034871.2 | chr17:28686431-28689563 |
| 6541 | Clec12b | NM_027709.2 | chr6:129325530-129335892 | | 6636 | Clptm1 | NM_019649.2 | chr7:20216928-20250379 |

Fig. 25 - 36

| | | | | | | | | |
|---|---|---|---|---|---|---|---|---|
| 6637 | Clptm1l | NM_146047.2 | chr13:73741449-73758087 | | 6732 | Cnnm3 | NM_053186.2 | chr1:36568720-36585082 |
| 6638 | Clpx | NM_001044389.2 | chr9:65142066-65178465 | | 6733 | Cnnm4 | NM_033570.2 | chr1:36528441-38566621 |
| 6639 | Clpx | NM_011802.3 | chr9:65142066-65178465 | | 6734 | Cnot1 | NM_001205226.1 | chr8:98243350-98345628 |
| 6640 | Clrn1 | NM_153384.3 | chr3:58647949-58689134 | | 6735 | Cnot1 | NM_153164.3 | chr8:98243350-98345628 |
| 6641 | Clrn1 | NM_153385.3 | chr3:58647949-58689134 | | 6736 | Cnot1 | NM_178078.2 | chr8:98243350-98345628 |
| 6642 | Clrn1 | NM_153386.3 | chr3:58647949-58689134 | | 6737 | Cnot10 | NM_153585.5 | chr9:114494991-114549318 |
| 6643 | Clrn2 | NM_001163317.1 | chr5:45844989-45855388 | | 6738 | Cnot11 | NM_028043.2 | chr1:39592646-39603722 |
| 6644 | Clrn3 | NM_178669.5 | chr7:142703138-142720337 | | 6739 | Cnot2 | NM_001037846.3 | chr10:115922216-116018567 |
| 6645 | Clspn | NM_175554.4 | chr4:126234224-126271147 | | 6740 | Cnot2 | NM_001037847.2 | chr10:115922216-116018567 |
| 6646 | Clstn1 | NM_001290989.1 | chr4:148960576-149023008 | | 6741 | Cnot2 | NM_001037848.3 | chr10:115922216-116018567 |
| 6647 | Clstn1 | NM_023051.5 | chr4:148960576-149023008 | | 6742 | Cnot2 | NM_028082.2 | chr10:115922216-116018567 |
| 6648 | Clstn2 | NM_022319.2 | chr9:97344814-97933586 | | 6743 | Cnot2 | NR_024327.1 | chr10:115922216-116018567 |
| 6649 | Clstn3 | NM_153508.4 | chr6:124380773-124414802 | | 6744 | Cnot3 | NM_146176.3 | chr7:3596871-3612711 |
| 6650 | Cita | NM_001080384.1 | chr4:44025514-44045720 | | 6745 | Cnot4 | NM_001164411.1 | chr6:34972064-35083737 |
| 6651 | Cita | NM_001080385.1 | chr4:44025514-44045720 | | 6746 | Cnot4 | NM_001164412.1 | chr6:34972064-35083737 |
| 6652 | Cita | NM_001080386.1 | chr4:44025514-44045720 | | 6747 | Cnot4 | NM_001164413.1 | chr6:34972064-35083737 |
| 6653 | Cita | NM_001290470.1 | chr4:44025514-44045720 | | 6748 | Cnot4 | NM_001164414.1 | chr6:34972064-35083737 |
| 6654 | Cita | NM_016780.2 | chr4:44025514-44045720 | | 6749 | Cnot4 | NM_016877.4 | chr6:34972064-35083737 |
| 6655 | Cltb | NM_028870.3 | chr13:54694299-54712633 | | 6750 | Cnot6 | NM_001290741.1 | chr11:49484998-49526224 |
| 6656 | Cltc | NM_001003908.1 | chr11:86508154-86570994 | | 6751 | Cnot6 | NM_212484.2 | chr11:49484998-49526224 |
| 6657 | Clu | NM_013492.2 | chr14:66587319-66600382 | | 6752 | Cnot6l | NM_001285511.1 | chr5:96499351-96591009 |
| 6658 | Cluap1 | NM_029738.2 | chr16:3909008-3941147 | | 6753 | Cnot6l | NM_001285514.1 | chr5:96499351-96591009 |
| 6659 | Cluh | NM_001081158.2 | chr11:74462996-74484349 | | 6754 | Cnot6l | NM_144910.2 | chr5:96499351-96591009 |
| 6660 | Clvs1 | NM_028940.2 | chr4:9196464-9378838 | | 6755 | Cnot6l | NM_178854.4 | chr5:96499351-96591009 |
| 6661 | Clvs2 | NM_175448.3 | chr10:33232139-33344406 | | 6756 | Cnot7 | NM_001271542.1 | chr8:41577891-41720146 |
| 6662 | Clybl | NM_029556.3 | chr14:122580916-122801456 | | 6757 | Cnot7 | NM_001271543.1 | chr8:41577891-41720146 |
| 6663 | Cma1 | NM_010780.2 | chr14:56560287-56563498 | | 6758 | Cnot7 | NM_011135.5 | chr8:41577891-41720146 |
| 6664 | Cma2 | NM_001024714.2 | chr14:56590264-56592832 | | 6759 | Cnot8 | NM_026949.3 | chr11:57917654-57932096 |
| 6665 | Cmah | NM_001111110.2 | chr13:24419272-24569158 | | 6760 | Cnp | NM_001146318.1 | chr11:100436252-100443053 |
| 6666 | Cmah | NM_001284519.1 | chr13:24419272-24569158 | | 6761 | Cnp | NM_009923.2 | chr11:100436252-100443053 |
| 6667 | Cmah | NM_001284520.1 | chr13:24419272-24569158 | | 6762 | Cnppd1 | NM_026977.2 | chr1:75131788-75138942 |
| 6668 | Cmah | NM_007717.5 | chr13:24419272-24569158 | | 6763 | Cnpy1 | NM_175651.4 | chr5:28532002-28564413 |
| 6669 | Cmas | NM_009908.2 | chr6:142705205-142724234 | | 6764 | Cnpy2 | NM_019953.1 | chr10:127759514-127764243 |
| 6670 | Cmbl | NM_181588.3 | chr15:31498866-31519874 | | 6765 | Cnpy3 | NM_028065.4 | chr17:46872661-46889161 |
| 6671 | Cmc1 | NM_026442.3 | chr9:117973645-118059314 | | 6766 | Cnpy4 | NM_178612.4 | chr5:138628762-138635122 |
| 6672 | Cmc2 | NM_026844.3 | chr8:119412584-119445336 | | 6767 | Cnr1 | NM_007726.3 | chr4:34011606-34035806 |
| 6673 | Cmip | NM_001163262.1 | chr8:119780918-119985405 | | 6768 | Cnr2 | NM_009924.4 | chr4:135451318-135476125 |
| 6674 | Cmip | NM_028941.1 | chr8:119780918-119985405 | | 6769 | Cnrip1 | NM_029861.2 | chr11:16951936-16979375 |
| 6675 | Cmklr1 | NM_008153.3 | chr5:114062363-114160399 | | 6770 | Cnst | NM_146105.3 | chr1:181476659-181557604 |
| 6676 | Cml1 | NM_023160.2 | chr6:85860147-85865671 | | 6771 | Cntd1 | NM_026562.2 | chr11:101140517-101150015 |
| 6677 | Cml2 | NM_053096.3 | chr6:85815415-85819131 | | 6772 | Cntf | NM_170786.2 | chr19:12838018-12840122 |
| 6678 | Cml3 | NM_001037842.3 | chr6:85710624-85715738 | | 6773 | Cntfr | NM_001136056.2 | chr4:41604528-41644123 |
| 6679 | Cml5 | NM_023493.2 | chr6:85767211-85770966 | | 6774 | Cntfr | NM_001146080.1 | chr4:41604528-41644123 |
| 6680 | Cmpk1 | NM_025647.3 | chr4:114633217-114659833 | | 6775 | Cntfr | NM_016673.2 | chr4:41604528-41644123 |
| 6681 | Cmpk2 | NM_020557.4 | chr12:27154079-27164702 | | 6776 | Cntln | NM_175275.4 | chr4:84530212-84777825 |
| 6682 | Cmss1 | NM_025599.3 | chr16:57302113-57606980 | | 6777 | Cntln | NM_177385.4 | chr4:84530212-84777825 |
| 6683 | Cmtm1 | NM_181990.2 | chr8:106817441-106834045 | | 6778 | Cntn1 | NM_001159647.1 | chr15:91881595-92172398 |
| 6684 | Cmtm2a | NM_027022.4 | chr8:106804941-106817081 | | 6779 | Cntn1 | NM_001159648.1 | chr15:91881595-92172398 |
| 6685 | Cmtm2b | NM_028524.3 | chr8:106846126-106854664 | | 6780 | Cntn1 | NM_007727.2 | chr15:91881595-92172398 |
| 6686 | Cmtm3 | NM_024217.3 | chr8:106864493-106871572 | | 6781 | Cntn2 | NM_177129.5 | chr1:134406001-134439517 |
| 6687 | Cmtm4 | NM_153582.5 | chr8:106872092-106919707 | | 6782 | Cntn3 | NM_008779.2 | chr6:102113299-102414661 |
| 6688 | Cmtm5 | NM_026066.2 | chr14:55555306-55558114 | | 6783 | Cntn4 | NM_001109749.1 | chr6:105627738-106649299 |
| 6689 | Cmtm5 | NM_029390.1 | chr14:55555306-55558114 | | 6784 | Cntn4 | NM_001109751.1 | chr6:105627738-106649299 |
| 6690 | Cmtm6 | NM_026036.3 | chr9:114640320-114658461 | | 6785 | Cntn4 | NM_173004.3 | chr6:105627738-106649299 |
| 6691 | Cmtm7 | NM_001252479.1 | chr9:114665953-114691111 | | 6786 | Cntn5 | NM_001033359.2 | chr9:9660890-10904775 |
| 6692 | Cmtm7 | NM_133978.2 | chr9:114665953-114691111 | | 6787 | Cntn5 | NM_001170787.1 | chr9:9660890-10904775 |
| 6693 | Cmtm8 | NM_027294.2 | chr9:114698462-114753270 | | 6788 | Cntn6 | NM_017383.3 | chr6:104443037-104813399 |
| 6694 | Cmtr1 | NM_028791.1 | chr17:29779546-29840304 | | 6789 | Cntnap1 | NM_016782.2 | chr11:101037430-101052034 |
| 6695 | Cntr2 | NM_146215.4 | chr8:112741859-112748389 | | 6790 | Cntnap2 | NM_001004357.2 | chr6:45010059-47251370 |
| 6696 | Cmya5 | NM_023821.3 | chr13:93810670-93914679 | | 6791 | Cntnap2 | NM_025771.3 | chr6:45010059-47251370 |
| 6697 | Cnbd2 | NM_027585.2 | chr2:156138209-156201374 | | 6792 | Cntnap3 | NM_001081129.1 | chr13:64838898-65005196 |
| 6698 | Cnbp | NM_001109745.1 | chr6:87792608-87801100 | | 6793 | Cntnap4 | NM_130457.2 | chr8:115093942-115406607 |
| 6699 | Cnbp | NM_001109746.1 | chr6:87792608-87801100 | | 6794 | Cntnap5a | NM_001077425.1 | chr1:117581713-118477251 |
| 6700 | Cnbp | NM_013493.2 | chr6:87792608-87801100 | | 6795 | Cntnap5b | NM_172851.2 | chr1:101169341-102382519 |
| 6701 | Cndp1 | NM_177450.4 | chr18:84779900-84819487 | | 6796 | Cntnap5c | NM_001081653.1 | chr17:57908992-58549765 |
| 6702 | Cndp2 | NM_001289531.1 | chr18:84836856-84855094 | | 6797 | Cntrl | NM_001290635.1 | chr2:34965011-35034342 |
| 6703 | Cndp2 | NM_023149.3 | chr18:84836856-84855094 | | 6798 | Cntrl | NM_012018.2 | chr2:34965011-35034342 |
| 6704 | Cnep1r1 | NM_029074.3 | chr8:90642657-90659096 | | 6799 | Cntrl | NM_030000.2 | chr2:34965011-35034342 |
| 6705 | Cnfn | NM_001081375.1 | chr7:26152634-26154743 | | 6800 | Cntrob | NM_172560.3 | chr11:69112997-69137375 |
| 6706 | Cnfn | NM_007723.2 | chr7:26152634-26154743 | | 6801 | Coa3 | NM_026618.2 | chr10:101139283-101140262 |
| 6707 | Cnga1 | NM_007723.2 | chr5:72994935-73033991 | | 6802 | Coa4 | NM_183270.2 | chr7:107685613-107688326 |
| 6708 | Cnga2 | NM_007724.3 | chrX:69237213-69255557 | | 6803 | Coa5 | NM_198006.4 | chr1:37473929-37486948 |
| 6709 | Cnga3 | NM_001282010.1 | chr1:37275122-37320229 | | 6804 | Coa6 | NM_174987.4 | chr11:128946400-128949335 |
| 6710 | Cnga3 | NM_009918.2 | chr1:37275122-37320229 | | 6805 | Coa7 | NM_027250.4 | chr4:108000756-108013323 |
| 6711 | Cnga4 | NM_001033317.3 | chr7:112553081-112557252 | | 6806 | Coasy | NM_027896.2 | chr11:100943938-100947933 |
| 6712 | Cngb1 | NM_001954013.1 | chr8:97762942-97830485 | | 6807 | Cobl | NM_001282993.1 | chr11:12136678-12364963 |
| 6713 | Cngb1 | NM_145601.1 | chr8:97762942-97830485 | | 6808 | Cobl | NM_001282994.1 | chr11:12136678-12364963 |
| 6714 | Cngb1 | NM_145601.1 | chr5:143200557-143579066 | | 6809 | Cobl | NM_172496.3 | chr11:12136678-12364963 |
| 6715 | Cngb3 | NM_013927.2 | chr4:19207996-19437770 | | 6810 | Cobll1 | NM_027225.3 | chr2:64926395-65076683 |
| 6716 | Cnih1 | NM_009919.2 | chr14:47395241-47408032 | | 6811 | Cobll1 | NM_177025.5 | chr2:64926395-65076683 |
| 6717 | Cnih2 | NM_009920.4 | chr19:5092868-5098521 | | 6812 | Coch | NM_001198835.1 | chr12:52694327-52706760 |
| 6718 | Cnih3 | NM_001160211.1 | chr1:183282758-183390772 | | 6813 | Coch | NM_007728.5 | chr12:52694327-52706760 |
| 6719 | Cnih3 | NM_001160212.1 | chr1:183282758-183390772 | | 6814 | Cog1 | NM_013581.3 | chr11:113510843-113523715 |
| 6720 | Cnih3 | NM_028408.3 | chr1:183282758-183390772 | | 6815 | Cog2 | NM_029746.3 | chr8:127044666-127075907 |
| 6721 | Cnih4 | NM_030131.3 | chr1:183081061-183099125 | | 6816 | Cog3 | NM_177381.3 | chr14:76102157-76154300 |
| 6722 | Cnksr1 | NM_001081047.1 | chr4:133783956-133794314 | | 6817 | Cog4 | NM_133973.2 | chr8:113370923-113406134 |
| 6723 | Cnksr2 | NM_007757.3 | chrX:154259504-154481042 | | 6818 | Cog5 | NM_001163126.1 | chr12:32339734-32622495 |
| 6724 | Cnksr3 | NM_172546.2 | chr10:3134303-3227479 | | 6819 | Cog6 | NM_026225.3 | chr3:52786044-52821145 |
| 6725 | Cnn1 | NM_009922.4 | chr9:21903696-21913665 | | 6820 | Cog7 | NM_001033318.3 | chr7:129066352-129125207 |
| 6726 | Cnn2 | NM_007725.4 | chr10:79451344-79458145 | | 6821 | Cog8 | NM_139229.4 | chr8:109572608-109580637 |
| 6727 | Cnn3 | NM_028044.2 | chr3:121129458-121161123 | | 6822 | Coil | NM_016706.2 | chr11:88835248-88852927 |
| 6728 | Cnnm1 | NM_031396.2 | chr19:43514925-43571703 | | 6823 | Col10a1 | NM_009925.4 | chr10:34109787-34116891 |
| 6729 | Cnnm2 | NM_033102471.1 | chr19:46836098-46953070 | | 6824 | Col11a1 | NM_007729.2 | chr3:113733457-113923244 |
| 6730 | Cnnm2 | NM_033569.3 | chr19:46836098-46953070 | | 6825 | Col11a2 | NM_009926.1 | chr17:34176381-34203187 |
| 6731 | Cnnm3 | NM_001039551.1 | chr1:36568720-36585082 | | 6826 | Col12a1 | NM_001290308.1 | chr9:79446793-79566529 |

Fig. 25 - 37

| | | | |
|---|---|---|---|
| 6827 | Col13a1 | NM_007731.3 | chr10:61301245-61441856 |
| 6828 | Col14a1 | NM_181277.3 | chr15:55139304-55352358 |
| 6829 | Col15a1 | NM_009928.3 | chr4:47220883-47326037 |
| 6830 | Col16a1 | NM_028266.5 | chr4:129725083-129776521 |
| 6831 | Col17a1 | NM_001290825.1 | chr19:47720830-47766532 |
| 6832 | Col17a1 | NM_007732.2 | chr19:47720830-47766532 |
| 6833 | Col18a1 | NM_001109991.1 | chr10:76514923-76629275 |
| 6834 | Col18a1 | NM_009929.3 | chr10:76514923-76629275 |
| 6835 | Col19a1 | NM_007733.2 | chr1:24264521-24594276 |
| 6836 | Col1a1 | NM_007742.3 | chr11:94797583-94813170 |
| 6837 | Col1a2 | NM_007743.2 | chr6:4455696-4491543 |
| 6838 | Col20a1 | NM_028518.1 | chr2:180721239-180752245 |
| 6839 | Col22a1 | NM_027174.1 | chr15:71628909-71864657 |
| 6840 | Col23a1 | NM_153393.2 | chr11:51103421-51397427 |
| 6841 | Col24a1 | NM_027770.2 | chr3:144955435-145214969 |
| 6842 | Col25a1 | NM_001244952.1 | chr3:129883762-130302801 |
| 6843 | Col25a1 | NM_029838.4 | chr3:129883762-130302801 |
| 6844 | Col25a1 | NM_198711.3 | chr3:129883762-130302801 |
| 6845 | Col26a1 | NM_024474.2 | chr5:137217633-137368977 |
| 6846 | Col27a1 | NM_025685.3 | chr4:62876446-62996024 |
| 6847 | Col28a1 | NM_001037865.1 | chr6:7947807-8142617 |
| 6848 | Col2a1 | NM_001113515.2 | chr15:97806032-97835155 |
| 6849 | Col2a1 | NM_031163.3 | chr15:97806032-97835155 |
| 6850 | Col3a1 | NM_009930.2 | chr1:45368382-45406551 |
| 6851 | Col4a1 | NM_009931.2 | chr8:11198422-11312826 |
| 6852 | Col4a2 | NM_009932.3 | chr8:11312828-11449287 |
| 6853 | Col4a3 | NM_007734.2 | chr1:82583495-82718634 |
| 6854 | Col4a3bp | NM_001164222.1 | chr13:97312689-97410122 |
| 6855 | Col4a3bp | NM_023420.2 | chr13:97312689-97410122 |
| 6856 | Col4a4 | NM_007735.2 | chr1:82447297-82583424 |
| 6857 | Col4a5 | NM_001163155.1 | chrX:137909961-138123778 |
| 6858 | Col4a5 | NM_007736.4 | chrX:137909961-138123778 |
| 6859 | Col4a6 | NM_053185.2 | chrX:137599945-137908619 |
| 6860 | Col5a1 | NM_015734.2 | chr2:27741944-27895030 |
| 6861 | Col5a2 | NM_007737.2 | chr1:45431175-45560127 |
| 6862 | Col5a3 | NM_016919.2 | chr9:20574493-20619478 |
| 6863 | Col6a3 | NM_009933.4 | chr10:76171536-76188789 |
| 6864 | Col6a2 | NM_146007.2 | chr10:76058500-76086149 |
| 6865 | Col6a3 | NM_001243258.1 | chr1:92663434-92740548 |
| 6866 | Col6a3 | NM_001243009.1 | chr1:92663434-92740548 |
| 6867 | Col6a4 | NM_026763.2 | chr9:105892648-105989022 |
| 6868 | Col6a5 | NM_001167953.1 | chr9:105758399-105862974 |
| 6869 | Col6a6 | NM_001102607.1 | chr9:105591746-105730415 |
| 6870 | Col6a6 | NM_172927.3 | chr9:105591746-105730415 |
| 6871 | Col7a1 | NM_007738.3 | chr9:108855790-108886920 |
| 6872 | Col8a1 | NM_007739.1 | chr16:57624368-57754850 |
| 6873 | Col8a2 | NM_199473.2 | chr4:125964037-125991574 |
| 6874 | Col9a1 | NM_001290691.1 | chr1:24184448-24259577 |
| 6875 | Col9a1 | NM_007740.3 | chr1:24184448-24259577 |
| 6876 | Col9a2 | NM_007741.2 | chr4:120712170-120727930 |
| 6877 | Col9a3 | NM_009936.2 | chr2:180332927-180356890 |
| 6878 | Colec10 | NM_173422.3 | chr15:54242328-54297913 |
| 6879 | Colec11 | NM_027866.1 | chr12:29279037-29308155 |
| 6880 | Colec12 | NM_130449.2 | chr18:9707645-9877993 |
| 6881 | Colgalt2 | NM_177756.4 | chr1:154246996-154357825 |
| 6882 | Colq | NM_009937.2 | chr14:32336269-32390569 |
| 6883 | Commd1 | NM_144514.2 | chr11:22799728-22882284 |
| 6884 | Commd10 | NM_178377.4 | chr18:47118529-47247648 |
| 6885 | Commd2 | NM_175095.4 | chr3:57448270-57455606 |
| 6886 | Commd3 | NM_147778.1 | chr2:18594088-18597843 |
| 6887 | Commd4 | NM_025417.2 | chr9:57002847-57006106 |
| 6888 | Commd5 | NM_025536.2 | chr15:76730370-76731727 |
| 6889 | Commd6 | NM_001033132.3 | chr14:102032982-102039688 |
| 6890 | Commd6 | NM_001168592.1 | chr14:102032982-102039688 |
| 6891 | Commd7 | NM_001195396.1 | chr2:153442665-153458517 |
| 6892 | Commd7 | NM_133850.2 | chr2:153442665-153458517 |
| 6893 | Commd9 | NM_178599.4 | chr2:72548298-72559422 |
| 6894 | Commd9 | NM_029635.3 | chr2:101726418-101741796 |
| 6895 | Comp | NM_016685.2 | chr8:72897446-72905965 |
| 6896 | Comt | NM_001111062.1 | chr16:18348274-18479166 |
| 6897 | Comt | NM_001111063.1 | chr16:18348274-18479166 |
| 6898 | Comt | NM_007744.3 | chr16:18348274-18479166 |
| 6899 | Comtd1 | NM_026965.2 | chr14:22665083-22668132 |
| 6900 | Copa | NM_009938.4 | chr1:174012660-174052463 |
| 6901 | Copb1 | NM_033370.3 | chr7:121359072-121398194 |
| 6902 | Copb2 | NM_015823.2 | chr9:98464149-98488794 |
| 6903 | Cope | NM_021538.1 | chr8:72826683-72836889 |
| 6904 | Copg1 | NM_017477.2 | chr6:87837933-87863588 |
| 6905 | Copg1 | NM_201244.1 | chr6:87837933-87863588 |
| 6906 | Copg2 | NM_017478.3 | chr6:30697554-30846794 |
| 6907 | Cops2 | NM_025556.3 | chr8:13884787-13890271 |
| 6908 | Cops2 | NM_001285507.1 | chr2:125656037-125684818 |
| 6909 | Cops2 | NM_001285512.1 | chr2:125656037-125684818 |
| 6910 | Cops2 | NM_001285513.1 | chr2:125656037-125684818 |
| 6911 | Cops2 | NM_009939.3 | chr2:125656037-125684818 |
| 6912 | Cops3 | NM_011991.1 | chr11:59631306-59653269 |
| 6913 | Cops4 | NM_012001.2 | chr5:100947327-100976821 |
| 6914 | Cops5 | NM_001277101.1 | chr1:10014680-10028240 |
| 6915 | Cops5 | NM_013715.2 | chr1:10014680-10028240 |
| 6916 | Cops5 | NR_102282.1 | chr1:10014680-10028240 |
| 6917 | Cops6 | NM_012002.3 | chr5:138602329-138605212 |
| 6918 | Cops7a | NM_001164089.1 | chr6:124908428-124915547 |
| 6919 | Cops7a | NM_012003.2 | chr6:124908428-124915547 |
| 6920 | Cops7b | NM_172974.2 | chr1:88483674-88503075 |
| 6921 | Cops8 | NM_133805.3 | chr1:92499999-92509916 |

| | | | |
|---|---|---|---|
| 6922 | Copz1 | NM_019817.1 | chr15:103103349-103130295 |
| 6923 | Copz2 | NM_019877.2 | chr11:96711190-96722516 |
| 6924 | Coq10a | NM_001081040.1 | chr10:127800152-127807093 |
| 6925 | Coq10b | NM_001039710.1 | chr1:55109613-55129546 |
| 6926 | Coq10b | NM_026424.3 | chr1:55109613-55129546 |
| 6927 | Coq2 | NM_027978.2 | chr5:101083744-101103275 |
| 6928 | Coq3 | NM_172687.1 | chr4:21806821-21839273 |
| 6929 | Coq4 | NM_178693.4 | chr2:29643782-29653263 |
| 6930 | Coq5 | NM_026504.2 | chr5:115729710-115746981 |
| 6931 | Coq6 | NM_172582.3 | chr12:85702917-85714746 |
| 6932 | Coq7 | NM_009940.3 | chr7:125668575-125676827 |
| 6933 | Coq9 | NM_026452.2 | chr8:97362316-97378795 |
| 6934 | Corin | NM_001122756.1 | chr5:72691263-72895779 |
| 6935 | Corin | NM_016869.3 | chr5:72691263-72895779 |
| 6936 | Coro1a | NM_009898.3 | chr7:133843287-133848268 |
| 6937 | Coro1b | NM_011778.2 | chr19:4148662-4154035 |
| 6938 | Coro1c | NM_011779.3 | chr5:114292447-114358715 |
| 6939 | Coro2a | NM_001164804.1 | chr4:46549808-46614801 |
| 6940 | Coro2a | NM_178893.4 | chr4:46549808-46614801 |
| 6941 | Coro2b | NM_175484.3 | chr9:62267298-62384851 |
| 6942 | Coro6 | NM_139128.1 | chr11:77277414-77283003 |
| 6943 | Coro6 | NM_139129.1 | chr11:77277414-77283003 |
| 6944 | Coro6 | NM_139130.2 | chr11:77277414-77283003 |
| 6945 | Coro7 | NM_030205.4 | chr16:4626884-4679720 |
| 6946 | Cort | NM_007745.3 | chr4:148499299-148500850 |
| 6947 | Cotl1 | NM_028071.2 | chr8:122333113-122364479 |
| 6948 | Cox10 | NM_178379.3 | chr11:63776128-63892974 |
| 6949 | Cox11 | NM_199008.2 | chr11:90499498-90507291 |
| 6950 | Cox14 | NM_183256.3 | chr15:99596048-99598567 |
| 6951 | Cox15 | NM_144874.4 | chr19:43807744-43827490 |
| 6952 | Cox16 | NM_025461.5 | chr12:82571690-82586097 |
| 6953 | Cox17 | NM_001017429.2 | chr16:38347084-38352849 |
| 6954 | Cox18 | NM_001033310.3 | chr5:90643749-90653021 |
| 6955 | Cox18 | NM_001163456.1 | chr5:90643749-90653021 |
| 6956 | Cox18 | NR_028088.1 | chr5:90643749-90653021 |
| 6957 | Cox19 | NM_197980.1 | chr15:139813775-139821120 |
| 6958 | Cox20 | NM_025511.1 | chr1:180249283-180252824 |
| 6959 | Cox4i1 | NM_009941.3 | chr8:123192189-123198109 |
| 6960 | Cox4i2 | NM_053091.2 | chr2:152579909-152590773 |
| 6961 | Cox5a | NM_007747.2 | chr9:57369038-57380233 |
| 6962 | Cox5b | NM_009942.2 | chr1:36748331-36750233 |
| 6963 | Cox6a1 | NM_007748.3 | chr5:115795662-115798964 |
| 6964 | Cox6a2 | NM_009943.2 | chr7:135348949-135349880 |
| 6965 | Cox6b1 | NM_025628.2 | chr7:31401992-31411170 |
| 6966 | Cox6b2 | NM_001289848.1 | chr7:4703393-4704696 |
| 6967 | Cox6b2 | NM_001289849.1 | chr7:4703393-4704696 |
| 6968 | Cox6b2 | NM_001289850.1 | chr7:4703393-4704696 |
| 6969 | Cox6b2 | NM_183405.2 | chr7:4703393-4704696 |
| 6970 | Cox6b2 | NM_183406.3 | chr7:4703393-4704696 |
| 6971 | Cox6b2 | NR_110411.1 | chr7:4703393-4704696 |
| 6972 | Cox6c | NM_053071.2 | chr15:35861730-35868001 |
| 6973 | Cox7a1 | NM_009944.3 | chr7:30969189-30971049 |
| 6974 | Cox7a2 | NM_009945.3 | chr9:79603047-79607660 |
| 6975 | Cox7a2l | NM_001159529.1 | chr17:83901256-83913673 |
| 6976 | Cox7a2l | NM_009187.3 | chr17:83901256-83913673 |
| 6977 | Cox7b | NM_025379.2 | chrX:103211038-103217789 |
| 6978 | Cox7b2 | NM_030052.3 | chr5:71834061-71939444 |
| 6979 | Cox7c | NM_007749.3 | chr13:86184402-86186400 |
| 6980 | Cox8a | NM_007750.2 | chr19:7289647-7292106 |
| 6981 | Cox8b | NM_007751.3 | chr7:148084840-148086345 |
| 6982 | Cox8c | NM_001039049.1 | chr12:104137515-104138744 |
| 6983 | Cp | NM_001276248.1 | chr3:19857053-19935310 |
| 6984 | Cp | NM_001276250.1 | chr3:19857053-19935310 |
| 6985 | Cp | NM_007752.3 | chr3:19857053-19935310 |
| 6986 | Cpa1 | NM_025350.3 | chr6:30589220-30595361 |
| 6987 | Cpa2 | NM_001024698.2 | chr6:30491641-30514473 |
| 6988 | Cpa3 | NM_007753.2 | chr3:20115515-20142080 |
| 6989 | Cpa4 | NM_027926.2 | chr6:30518375-30541747 |
| 6990 | Cpa5 | NM_144537.3 | chr6:30561009-30581521 |
| 6991 | Cpa6 | NM_001289497.1 | chr1:10314799-10710026 |
| 6992 | Cpa6 | NM_177834.4 | chr1:10314799-10710026 |
| 6993 | Cpb1 | NM_029706.1 | chr3:20149382-20174651 |
| 6994 | Cpb2 | NM_019775.3 | chr14:75642093-75683360 |
| 6995 | Cpd | NM_007754.2 | chr11:76580709-76660510 |
| 6996 | Cpe | NM_013494.3 | chr8:67071348-67171837 |
| 6997 | Cpeb1 | NM_001252525.1 | chr7:88491911-88599644 |
| 6998 | Cpeb1 | NM_001252526.1 | chr7:88491911-88599644 |
| 6999 | Cpeb1 | NM_007755.5 | chr7:88491911-88599644 |
| 7000 | Cpeb2 | NM_001177379.1 | chr5:43542924-43680963 |
| 7001 | Cpeb2 | NM_175937.3 | chr5:43542924-43680963 |
| 7002 | Cpeb3 | NM_001290826.1 | chr19:37095780-37281961 |
| 7003 | Cpeb3 | NM_001290827.1 | chr19:37095780-37281961 |
| 7004 | Cpeb3 | NM_001290828.1 | chr19:37095780-37281961 |
| 7005 | Cpeb3 | NM_001290829.1 | chr19:37095780-37281961 |
| 7006 | Cpeb3 | NM_198300.3 | chr19:37095780-37281961 |
| 7007 | Cpeb4 | NM_001290676.1 | chr11:31770939-31835635 |
| 7008 | Cpeb4 | NM_001290678.1 | chr11:31770939-31835635 |
| 7009 | Cpeb4 | NM_026252.4 | chr11:31770939-31835635 |
| 7010 | Cped1 | NM_001081351.1 | chr6:21935909-22205606 |
| 7011 | Cphx1 | NM_175342.3 | chr14:27041389-27055226 |
| 7012 | Cphx1 | NM_175342.3 | chr14:26762025-26775856 |
| 7013 | Cphx1 | NM_175342.3 | chr14:26901778-26915613 |
| 7014 | Cphx2 | NM_001270506.1 | chr14:26901778-26915613 |
| 7015 | Cphx2 | NM_001270506.1 | chr14:26762025-26775856 |
| 7016 | Cphx2 | NM_001270506.1 | chr14:27041389-27055226 |

Fig. 25 - 38

| ID | Gene | Accession | Location |
|---|---|---|---|
| 7017 | Cplx1 | NM_007756.3 | chr5:108947572-108979046 |
| 7018 | Cplx2 | NM_009946.3 | chr13:54472712-54485278 |
| 7019 | Cplx3 | NM_146223.3 | chr9:57447798-57454088 |
| 7020 | Cplx4 | NM_145493.1 | chr18:66115375-66129832 |
| 7021 | Cpm | NM_027468.1 | chr10:117066555-117124408 |
| 7022 | Cpn1 | NM_030703.2 | chr19:44030797-44061010 |
| 7023 | Cpn2 | NM_027904.2 | chr16:30256464-30267618 |
| 7024 | Cpne1 | NM_170588.3 | chr2:155897576-155937701 |
| 7025 | Cpne1 | NM_170590.3 | chr2:155897576-155937701 |
| 7026 | Cpne2 | NM_153507.2 | chr8:97056927-97094429 |
| 7027 | Cpne3 | NM_027769.2 | chr4:19446398-19497251 |
| 7028 | Cpne4 | NM_028719.1 | chr9:104472117-104936874 |
| 7029 | Cpne5 | NM_153166.2 | chr17:29293465-29374735 |
| 7030 | Cpne6 | NM_001136057.2 | chr14:56129284-56136268 |
| 7031 | Cpne6 | NM_001146183.1 | chr14:56129284-56136268 |
| 7032 | Cpne6 | NM_009947.3 | chr14:56129284-56136268 |
| 7033 | Cpne7 | NM_170684.2 | chr8:125641274-125659085 |
| 7034 | Cpne8 | NM_001033851.1 | chr15:90317911-90509819 |
| 7035 | Cpne8 | NM_025815.2 | chr15:90317911-90509819 |
| 7036 | Cpne9 | NM_170673.3 | chr6:113232300-113255565 |
| 7037 | Cpox | NM_007757.2 | chr16:58670320-58680502 |
| 7038 | Cpped1 | NM_146067.3 | chr16:11803814-11909516 |
| 7039 | Cpq | NM_018755.2 | chr15:33012883-33583191 |
| 7040 | Cpq | NM_176073.4 | chr15:33012883-33583191 |
| 7041 | Cps1 | NM_001080809.2 | chr1:67169600-67277843 |
| 7042 | Cpsf1 | NM_001164173.1 | chr15:76406788-76438021 |
| 7043 | Cpsf1 | NM_053193.2 | chr15:76406788-76438021 |
| 7044 | Cpsf2 | NM_026856.3 | chr12:103214183-103244203 |
| 7045 | Cpsf3 | NM_018813.3 | chr12:21292157-21320917 |
| 7046 | Cpsf3l | NM_028020.3 | chr4:155243676-155263212 |
| 7047 | Cpsf4 | NM_001291248.1 | chr5:145928081-145942910 |
| 7048 | Cpsf4 | NM_001291249.1 | chr5:145928081-145942910 |
| 7049 | Cpsf4 | NM_178576.3 | chr5:145928081-145942910 |
| 7050 | Cpsf4l | NM_001164532.1 | chr11:113559484-113571331 |
| 7051 | Cpsf4l | NM_026682.2 | chr11:113559484-113571331 |
| 7052 | Cpsf4l | NM_029794.2 | chr11:113559484-113571331 |
| 7053 | Cpsf6 | NM_001013391.2 | chr10:116781723-116814029 |
| 7054 | Cpsf7 | NM_001164272.1 | chr19:10599733-10622225 |
| 7055 | Cpsf7 | NM_172302.3 | chr19:10599733-10622225 |
| 7056 | Cpt1a | NM_013495.1 | chr19:3323300-3385733 |
| 7057 | Cpt1b | NM_009948.2 | chr15:89246836-89256293 |
| 7058 | Cpt1c | NM_001252470.1 | chr7:52214741-52230221 |
| 7059 | Cpt1c | NM_153679.2 | chr7:52214741-52230221 |
| 7060 | Cpt2 | NM_009949.2 | chr4:107576586-107596194 |
| 7061 | Cpvl | NM_001289713.1 | chr6:53823272-53928667 |
| 7062 | Cpvl | NM_001289714.1 | chr6:53823272-53928667 |
| 7063 | Cpvl | NM_027749.2 | chr6:53823272-53928667 |
| 7064 | Cpxcr1 | NM_001033471.3 | chrX:113562552-113592392 |
| 7065 | Cpxm1 | NM_019696.3 | chr2:130216510-130223365 |
| 7066 | Cpxm2 | NM_018867.4 | chr7:139234492-139346424 |
| 7067 | Cpz | NM_153107.2 | chr5:35844866-35868275 |
| 7068 | Cr1l | NM_013499.2 | chr1:196959981-196957764 |
| 7069 | Cr2 | NM_007758.2 | chr1:196963004-197002909 |
| 7070 | Crabp1 | NM_001284507.1 | chr9:54612554-54620917 |
| 7071 | Crabp1 | NM_013496.3 | chr9:54612554-54620917 |
| 7072 | Crabp2 | NM_007759.2 | chr3:87752614-87757294 |
| 7073 | Cradd | NM_009950.2 | chr10:94637379-94786731 |
| 7074 | Cramp1l | NM_020608.3 | chr17:25098170-25125175 |
| 7075 | Crat | NM_007760.3 | chr2:30255996-30271268 |
| 7076 | Crb1 | NM_133239.2 | chr1:141094830-141273653 |
| 7077 | Crb2 | NM_001163566.1 | chr2:37631769-37654623 |
| 7078 | Crb3 | NM_177638.4 | chr17:57201699-57205337 |
| 7079 | Crbn | NM_021449.1 | chr6:106719131-106750081 |
| 7080 | Crbn | NM_175357.3 | chr6:106719131-106750081 |
| 7081 | Crcp | NM_007761.2 | chr5:130505175-130536653 |
| 7082 | Crct1 | NM_028798.3 | chr3:92818126-92819608 |
| 7083 | Creb1 | NM_001037726.1 | chr1:64579377-64651122 |
| 7084 | Creb1 | NM_009952.2 | chr1:64579377-64651122 |
| 7085 | Creb1 | NM_133828.2 | chr1:64579377-64651122 |
| 7086 | Creb3 | NM_013497.3 | chr4:43575506-43579932 |
| 7087 | Creb3l1 | NM_011957.2 | chr2:91822484-91864327 |
| 7088 | Creb3l2 | NM_178661.4 | chr6:37281020-37392148 |
| 7089 | Creb3l3 | NM_145365.3 | chr10:80547077-80561617 |
| 7090 | Creb3l4 | NM_030080.3 | chr3:90041421-90047434 |
| 7091 | Creb5 | NM_172728.2 | chr6:53523367-53645826 |
| 7092 | Crebbp | NM_001025432.1 | chr16:4084047-4213404 |
| 7093 | Crebl2 | NM_177687.3 | chr6:134780216-134807901 |
| 7094 | Crebrf | NM_029870.2 | chr17:26852594-26913571 |
| 7095 | Crebzf | NM_145151.3 | chr7:97591290-97596553 |
| 7096 | Crebzf | NR_073436.1 | chr7:97591290-97596553 |
| 7097 | Crebzf | NR_073437.1 | chr7:97591290-97596553 |
| 7098 | Crebzf | NR_073438.1 | chr7:97591290-97596553 |
| 7099 | Creg1 | NM_011804.2 | chr1:167693910-167705435 |
| 7100 | Creg2 | NM_170597.4 | chr1:39675250-39708027 |
| 7101 | Creld1 | NM_133930.1 | chr6:113433562-113443332 |
| 7102 | Creld2 | NM_029720.2 | chr15:88650075-88657111 |
| 7103 | Crem | NM_001110850.2 | chr18:3266351-3366861 |
| 7104 | Crem | NM_001110851.1 | chr18:3266351-3366861 |
| 7105 | Crem | NM_001110852.1 | chr18:3266351-3366861 |
| 7106 | Crem | NM_001110853.1 | chr18:3266351-3366861 |
| 7107 | Crem | NM_001110854.1 | chr18:3266351-3366861 |
| 7108 | Crem | NM_001110855.1 | chr18:3266351-3366861 |
| 7109 | Crem | NM_001110856.2 | chr18:3266351-3366861 |
| 7110 | Crem | NM_001110857.2 | chr18:3266351-3366861 |
| 7111 | Crem | NM_001110858.2 | chr18:3266351-3366861 |
| 7112 | Crem | NM_001110859.2 | chr18:3266351-3366861 |
| 7113 | Crem | NM_001271504.1 | chr18:3266351-3366861 |
| 7114 | Crem | NM_001271505.1 | chr18:3266351-3366861 |
| 7115 | Crem | NM_001271506.1 | chr18:3266351-3366861 |
| 7116 | Crem | NM_013498.3 | chr18:3266351-3366861 |
| 7117 | Crem | NR_073193.1 | chr18:3266351-3366861 |
| 7118 | Crh | NM_205769.2 | chr3:19593400-19595396 |
| 7119 | Crhbp | NM_198408.3 | chr13:96261330-96214786 |
| 7120 | Crhr1 | NM_007762.4 | chr11:103994195-104036832 |
| 7121 | Crhr2 | NM_001288618.1 | chr6:55040042-55083010 |
| 7122 | Crhr2 | NM_001288619.1 | chr6:55040042-55083010 |
| 7123 | Crhr2 | NM_001288620.1 | chr6:55040042-55083010 |
| 7124 | Crhr2 | NM_009953.4 | chr6:55040042-55083010 |
| 7125 | Crim1 | NM_015800.3 | chr17:78595588-78775932 |
| 7126 | Crip1 | NM_007763.3 | chr12:114390222-114392090 |
| 7127 | Crip2 | NM_024223.2 | chr12:114378446-114383717 |
| 7128 | Crip3 | NM_053250.2 | chr17:46565890-46568720 |
| 7129 | Crip3 | NM_181664.2 | chr17:46565890-46568720 |
| 7130 | Cript | NM_019936.3 | chr17:87424900-87435148 |
| 7131 | Crisp1 | NM_009638.3 | chr17:40430706-40456156 |
| 7132 | Crisp2 | NM_001204071.1 | chr17:40901682-40931095 |
| 7133 | Crisp2 | NM_009420.2 | chr17:40901682-40931095 |
| 7134 | Crisp3 | NM_009639.2 | chr17:40358725-40379207 |
| 7135 | Crisp4 | NM_030033.1 | chr1:18105271-18127132 |
| 7136 | Crispld1 | NM_031402.2 | chr1:17717497-17756288 |
| 7137 | Crispld2 | NM_030209.3 | chr8:122516369-122576693 |
| 7138 | Crk | NM_001277219.1 | chr11:75492760-75521930 |
| 7139 | Crk | NM_001277221.1 | chr11:75492760-75521930 |
| 7140 | Crk | NM_133656.5 | chr11:75492760-75521930 |
| 7141 | Crkl | NM_001277231.1 | chr16:17452077-17487533 |
| 7142 | Crkl | NM_007764.5 | chr16:17452077-17487533 |
| 7143 | Crlf1 | NM_018827.2 | chr8:73017054-73027980 |
| 7144 | Crlf2 | NM_001164735.1 | chr5:109983727-109988012 |
| 7145 | Crlf2 | NM_016715.4 | chr5:109983727-109988012 |
| 7146 | Crlf3 | NM_001277106.1 | chr11:79859994-79894493 |
| 7147 | Crlf3 | NM_018776.2 | chr11:79859994-79894493 |
| 7148 | Crls1 | NM_001024385.1 | chr2:132672401-132692504 |
| 7149 | Crls1 | NM_025646.3 | chr2:132672401-132692504 |
| 7150 | Crmp1 | NM_001136058.2 | chr5:37633296-37683402 |
| 7151 | Crmp1 | NM_007765.2 | chr5:37633296-37683402 |
| 7152 | Crnde | NR_033641.3 | chr8:94849929-94880019 |
| 7153 | Crnde | NR_110452.1 | chr8:94849929-94880019 |
| 7154 | Crnkl1 | NM_025820.3 | chr2:145743217-145760436 |
| 7155 | Crnn | NM_001081200.1 | chr3:92948708-92953393 |
| 7156 | Crocc | NM_001145958.1 | chr4:140572551-140616460 |
| 7157 | Crocc | NM_172122.2 | chr4:140572551-140616460 |
| 7158 | Crot | NM_023733.3 | chr5:8966047-8997146 |
| 7159 | Crp | NM_007768.4 | chr1:174628186-174630097 |
| 7160 | Crtac1 | NM_145123.4 | chr19:42357526-42506273 |
| 7161 | Crtam | NM_001281954.1 | chr9:40780880-40812711 |
| 7162 | Crtam | NM_019465.4 | chr9:40780880-40812711 |
| 7163 | Crtap | NM_019922.2 | chr9:114284249-114299830 |
| 7164 | Crtc1 | NM_001004062.2 | chr8:72906256-72963472 |
| 7165 | Crtc2 | NM_028881.2 | chr3:90058202-90068047 |
| 7166 | Crtc3 | NM_173863.2 | chr7:87731518-87833763 |
| 7167 | Crx | NM_001113330.1 | chr7:16451295-16465304 |
| 7168 | Crx | NM_007770.4 | chr7:16451295-16465304 |
| 7169 | Crxos | NM_001033638.2 | chr7:16467965-16489379 |
| 7170 | Crxos | NM_001145190.2 | chr7:16467965-16489379 |
| 7171 | Crxos | NM_001205274.1 | chr7:16467965-16489379 |
| 7172 | Crxos | NR_038092.1 | chr7:16467965-16489379 |
| 7173 | Cry1 | NM_007771.1 | chr10:84594444-84647799 |
| 7174 | Cry2 | NM_009963.4 | chr2:92243804-92274226 |
| 7175 | Cryaa | NM_001278569.1 | chr17:31814875-31818675 |
| 7176 | Cryaa | NM_001278570.1 | chr17:31814875-31818675 |
| 7177 | Cryaa | NM_013501.3 | chr17:31814875-31818675 |
| 7178 | Cryab | NM_001289782.1 | chr9:50559176-50564740 |
| 7179 | Cryab | NM_001289784.1 | chr9:50559176-50564740 |
| 7180 | Cryab | NM_001289785.1 | chr9:50559176-50564740 |
| 7181 | Cryab | NM_009964.3 | chr9:50559176-50564740 |
| 7182 | Cryba1 | NM_009965.2 | chr11:77532233-77538795 |
| 7183 | Cryba2 | NM_021541.3 | chr1:74936507-74939717 |
| 7184 | Cryba4 | NM_021351.1 | chr5:112675552-112681522 |
| 7185 | Crybb1 | NM_023695.2 | chr5:112684840-112698602 |
| 7186 | Crybb2 | NM_007774.4 | chr5:113487284-113497786 |
| 7187 | Crybb3 | NM_001159650.1 | chr5:113504858-113510604 |
| 7188 | Crybb3 | NM_021352.3 | chr5:113504858-113510604 |
| 7189 | Crybg3 | NM_174848.3 | chr16:59490601-59555578 |
| 7190 | Cryga | NM_007774.3 | chr1:65146962-65149937 |
| 7191 | Crygb | NM_144761.2 | chr1:65126795-65128864 |
| 7192 | Crygc | NM_001082573.2 | chr1:65118098-65120106 |
| 7193 | Crygc | NM_007775.2 | chr1:65118098-65120106 |
| 7194 | Crygd | NM_007776.2 | chr1:65108411-65110014 |
| 7195 | Cryge | NM_007777.3 | chr1:65095130-65097737 |
| 7196 | Crygf | NM_027010.2 | chr1:65973895-65974878 |
| 7197 | Crygn | NM_153076.2 | chr5:24256819-24263661 |
| 7198 | Crygs | NM_009967.2 | chr16:22805275-22811483 |
| 7199 | Cryl1 | NM_030004.3 | chr14:57893876-58017320 |
| 7200 | Crym | NM_016669.1 | chr7:127329897-127345502 |
| 7201 | Cryz | NM_009968.3 | chr3:154259675-154286146 |
| 7202 | Cryzl1 | NM_026994.1 | chr16:91689142-91729047 |
| 7203 | Cryzl1 | NM_133679.2 | chr16:91689142-91729047 |
| 7204 | Cs | NM_026444.3 | chr10:127774887-127799535 |
| 7205 | Csad | NM_144942.4 | chr15:102007428-102019474 |

Fig. 25 - 39

| | | | |
|---|---|---|---|
| 7207 | Csdc2 | NM_145473.3 | chr15:81767188-81781371 |
| 7208 | Csde1 | NM_001161854.1 | chr3:102824468-102862112 |
| 7209 | Csde1 | NM_144901.3 | chr3:102824468-102862112 |
| 7210 | Cse1l | NM_023565.3 | chr2:166731595-166771889 |
| 7211 | Csf1 | NM_001113529.1 | chr3:107543965-107563387 |
| 7212 | Csf1 | NM_001113530.1 | chr3:107543965-107563387 |
| 7213 | Csf1 | NM_007778.4 | chr3:107543965-107563387 |
| 7214 | Csf1r | NM_001037859.2 | chr18:61265226-61290793 |
| 7215 | Csf2 | NM_009969.4 | chr11:54060771-54063401 |
| 7216 | Csf2ra | NM_009970.2 | chr19:61300304-61304321 |
| 7217 | Csf2rb | NM_007780.4 | chr15:78156420-78181431 |
| 7218 | Csf2rb2 | NM_001287389.1 | chr15:78112937-78136151 |
| 7219 | Csf2rb2 | NM_007781.3 | chr15:78112937-78136151 |
| 7220 | Csf3 | NM_009971.2 | chr11:98562626-98564943 |
| 7221 | Csf3r | NM_001252651.1 | chr4:125701902-125722219 |
| 7222 | Csf3r | NM_007782.3 | chr4:125701902-125722219 |
| 7223 | Csf3r | NR_045561.1 | chr4:125701902-125722219 |
| 7224 | Csgalnact1 | NM_001252623.1 | chr8:70880679-71259045 |
| 7225 | Csgalnact1 | NM_172753.5 | chr8:70880679-71259045 |
| 7226 | Csgalnact2 | NM_030165.3 | chr6:118057470-118089158 |
| 7227 | Csk | NM_007783.3 | chr9:57474452-57492987 |
| 7228 | Csl | NM_027945.3 | chr10:99220338-99222292 |
| 7229 | Csmd1 | NM_053171.2 | chr8:15892545-17535385 |
| 7230 | Csmd2 | NM_001281955.1 | chr4:127665288-128244900 |
| 7231 | Csmd2os | NM_029137.1 | chr4:127810767-127844211 |
| 7232 | Csmd3 | NM_001081391.2 | chr15:47412183-48623535 |
| 7233 | Csn1s1 | NM_001286015.1 | chr5:88095232-88111602 |
| 7234 | Csn1s1 | NM_001286016.1 | chr5:88095232-88111602 |
| 7235 | Csn1s1 | NM_007784.3 | chr5:88095232-88111602 |
| 7236 | Csn1s2a | NM_007785.2 | chr5:88203591-88217822 |
| 7237 | Csn1s2b | NM_009973.3 | chr5:88237146-88253446 |
| 7238 | Csn2 | NM_001286020.1 | chr5:88121643-88128450 |
| 7239 | Csn2 | NM_001286021.1 | chr5:88121643-88128450 |
| 7240 | Csn2 | NM_001286022.1 | chr5:88121643-88128450 |
| 7241 | Csn2 | NM_001286023.1 | chr5:88121643-88128450 |
| 7242 | Csn2 | NM_001286024.1 | chr5:88121643-88128450 |
| 7243 | Csn2 | NM_009972.2 | chr5:88121643-88128450 |
| 7244 | Csn3 | NM_007786.4 | chr5:88354658-88361289 |
| 7245 | Csnk1a1 | NM_146087.2 | chr18:61715235-61747953 |
| 7246 | Csnk1d | NM_027874.2 | chr11:120823054-120852647 |
| 7247 | Csnk1d | NM_139059.2 | chr11:120823054-120852647 |
| 7248 | Csnk1e | NM_001289898.1 | chr15:79248281-79272487 |
| 7249 | Csnk1e | NM_001289899.1 | chr15:79248281-79272487 |
| 7250 | Csnk1e | NM_013767.2 | chr15:79248281-79272487 |
| 7251 | Csnk1g1 | NM_173185.2 | chr9:65756816-65892821 |
| 7252 | Csnk1g2 | NM_001159591.1 | chr10:80085524-80103516 |
| 7253 | Csnk1g2 | NM_134002.2 | chr10:80085524-80103516 |
| 7254 | Csnk1g3 | NM_152809.2 | chr18:54021766-54115338 |
| 7255 | Csnk2a1 | NM_007788.3 | chr2:152085275-152107587 |
| 7256 | Csnk2a2 | NM_009974.3 | chr8:97969995-98012720 |
| 7257 | Csnk2b | NM_009975.3 | chr17:35253139-35258392 |
| 7258 | Csnka2ip | NM_173861.2 | chr16:64477636-64478960 |
| 7259 | Cspg4 | NM_139001.2 | chr9:56712910-56747677 |
| 7260 | Cspg5 | NM_001166273.1 | chr9:110146286-110165080 |
| 7261 | Cspg5 | NM_013884.3 | chr9:110146286-110165080 |
| 7262 | Cspp1 | NM_026493.3 | chr1:10028298-10126849 |
| 7263 | Csprs | NM_033616.3 | chr8_random:111571-163011 |
| 7264 | Csrnp1 | NM_153287.3 | chr9:119880283-119893776 |
| 7265 | Csrnp2 | NM_153407.2 | chr15:100310000-100325670 |
| 7266 | Csrnp3 | NM_001290665.1 | chr2:65683823-65869603 |
| 7267 | Csrnp3 | NM_001290666.1 | chr2:65683823-65869603 |
| 7268 | Csrnp3 | NM_153409.5 | chr2:65683823-65869603 |
| 7269 | Csrnp3 | NM_178634.2 | chr2:65683823-65869603 |
| 7270 | Csrp1 | NM_007791.5 | chr1:137625773-137648806 |
| 7271 | Csrp2 | NM_007792.4 | chr10:110357231-110376570 |
| 7272 | Csrp2bp | NM_001166640.1 | chr2:144194718-144233411 |
| 7273 | Csrp2bp | NM_181417.3 | chr2:144194718-144233411 |
| 7274 | Csrp3 | NM_001198841.1 | chr7:56085767-56103421 |
| 7275 | Csrp3 | NM_013808.4 | chr7:56085767-56103421 |
| 7276 | Cst10 | NM_149230984-149236014 | chr2:149230984-149236014 |
| 7277 | Cst11 | NM_030059.2 | chr2:148594353-148597233 |
| 7278 | Cst12 | NM_027054.1 | chr2:148615096-148619173 |
| 7279 | Cst13 | NM_027024.3 | chr2:148645834-148656146 |
| 7280 | Cst3 | NM_009976.3 | chr2:148697467-148701204 |
| 7281 | Cst6 | NM_028623.5 | chr19:5344704-5349574 |
| 7282 | Cst7 | NM_009977.3 | chr2:150396150-150404680 |
| 7283 | Cst8 | NM_009978.2 | chr2:148624574-148631320 |
| 7284 | Cst9 | NM_009979.1 | chr2:148660882-148664473 |
| 7285 | Csta1 | NM_001033239.3 | chr16:36120031-36131275 |
| 7286 | Cstad | NM_030137.2 | chr2:30450563-30464465 |
| 7287 | Cstb | NM_007793.3 | chr10:77888414-77890367 |
| 7288 | Cstf1 | NM_024199.2 | chr2:172196502-172206586 |
| 7289 | Cstf2 | NM_001290398.1 | chrX:130593714-130646393 |
| 7290 | Cstf2 | NM_001290399.1 | chrX:130593714-130646393 |
| 7291 | Cstf2 | NM_133196.3 | chrX:130593714-130646393 |
| 7292 | Cstf2t | NM_031249.2 | chr19:31157331-31161082 |
| 7293 | Cstf3 | NM_001037326.2 | chr2:104430640-104505582 |
| 7294 | Cstf3 | NM_145529.3 | chr2:104430640-104505582 |
| 7295 | Cstf3 | NM_177253.4 | chr2:104430640-104505582 |
| 7296 | Cstl1 | NM_177555.4 | chr2:148576096-148581114 |
| 7297 | Ctag2 | NM_027302.2 | chrX:62300818-62302192 |
| 7298 | Ctage5 | NM_001165253.1 | chr12:60230732-60291207 |
| 7299 | Ctage5 | NM_001165254.1 | chr12:60230732-60291207 |
| 7300 | Ctage5 | NM_146034.3 | chr12:60230732-60291207 |
| 7301 | Ctbp1 | NM_001198859.1 | chr5:33590371-33617653 |
| 7302 | Ctbp1 | NM_001198860.1 | chr5:33590371-33617653 |
| 7303 | Ctbp1 | NM_001198861.1 | chr5:33590371-33617653 |
| 7304 | Ctbp1 | NM_013502.3 | chr5:33590371-33617653 |
| 7305 | Ctbp2 | NM_001170744.1 | chr7:140178693-140315166 |
| 7306 | Ctbp2 | NM_009980.4 | chr7:140178693-140315166 |
| 7307 | Ctbs | NM_028836.4 | chr3:146113431-146128812 |
| 7308 | Ctc1 | NM_001013256.2 | chr11:68829412-68849975 |
| 7309 | Ctc1 | NM_001143790.1 | chr11:68829412-68849975 |
| 7310 | Ctc1 | NM_001281464.1 | chr11:68829412-68849975 |
| 7311 | Ctc1 | NM_001281465.1 | chr11:68829412-68849975 |
| 7312 | Ctcf | NM_181322.3 | chr8:108160437-108206822 |
| 7313 | Ctcfl | NM_001081387.2 | chr2:172919109-172945026 |
| 7314 | Ctcflos | NR_040321.1 | chr2:172950249-172958705 |
| 7315 | Ctdnep1 | NM_026017.2 | chr11:69794670-69804102 |
| 7316 | Ctdp1 | NM_026295.2 | chr18:80604697-80666406 |
| 7317 | Ctdsp1 | NM_153088.2 | chr1:74438183-74443859 |
| 7318 | Ctdsp2 | NM_001113470.1 | chr10:126415772-126437031 |
| 7319 | Ctdsp2 | NM_146012.2 | chr10:126415772-126437031 |
| 7320 | Ctdspl | NM_133710.3 | chr9:118835654-118953237 |
| 7321 | Ctdspl2 | NM_001290991.1 | chr2:121779506-121841062 |
| 7322 | Ctdspl2 | NM_001290992.1 | chr2:121779506-121841062 |
| 7323 | Ctdspl2 | NM_212450.4 | chr2:121779506-121841062 |
| 7324 | Ctf1 | NM_007795.1 | chr7:134856249-134861699 |
| 7325 | Ctf2 | NM_198858.1 | chr7:134862473-134869130 |
| 7326 | Ctgf | NM_010217.2 | chr10:24315247-24318488 |
| 7327 | Cth | NM_145953.2 | chr3:157557211-157588027 |
| 7328 | Cthrc1 | NM_026778.2 | chr15:38908477-38918665 |
| 7329 | Ctif | NM_201354.2 | chr18:75590871-75857350 |
| 7330 | Ctla2a | NM_001145799.1 | chr13:61035515-61037986 |
| 7331 | Ctla2a | NM_007796.2 | chr13:61035515-61037986 |
| 7332 | Ctla2b | NM_001145801.1 | chr13:60996711-60998808 |
| 7333 | Ctla2b | NM_007797.1 | chr13:60996711-60998808 |
| 7334 | Ctla4 | NM_001281976.1 | chr1:60965868-60972676 |
| 7335 | Ctla4 | NM_009843.4 | chr1:60965868-60972676 |
| 7336 | Ctnna1 | NM_009818.3 | chr18:35278566-35414429 |
| 7337 | Ctnna2 | NM_001109764.1 | chr6:76831630-77929661 |
| 7338 | Ctnna2 | NM_009819.2 | chr6:76831630-77929661 |
| 7339 | Ctnna2 | NM_145732.2 | chr6:76831630-77929661 |
| 7340 | Ctnna3 | NM_001164563.1 | chr10:62892845-64466415 |
| 7341 | Ctnna3 | NM_001164519.1 | chr10:62892845-64466415 |
| 7342 | Ctnna3 | NM_177612.3 | chr10:62892845-64466415 |
| 7343 | Ctnnal1 | NM_018761.3 | chr4:56823806-56878083 |
| 7344 | Ctnnb1 | NM_001165902.1 | chr9:120842517-120869625 |
| 7345 | Ctnnb1 | NM_007614.3 | chr9:120842517-120869625 |
| 7346 | Ctnnbip1 | NM_001141930.1 | chr4:148892349-148940546 |
| 7347 | Ctnnbip1 | NM_023465.4 | chr4:148892349-148940546 |
| 7348 | Ctnnbl1 | NM_025680.4 | chr2:157563136-157717639 |
| 7349 | Ctnnd1 | NM_001085448.1 | chr2:84440937-84490897 |
| 7350 | Ctnnd1 | NM_001085449.1 | chr2:84440937-84490897 |
| 7351 | Ctnnd1 | NM_001085450.1 | chr2:84440937-84490897 |
| 7352 | Ctnnd1 | NM_001085453.1 | chr2:84440937-84490897 |
| 7353 | Ctnnd1 | NM_007615.4 | chr2:84440937-84490897 |
| 7354 | Ctnnd2 | NM_008729.2 | chr15:30102347-30959098 |
| 7355 | Ctns | NM_031251.4 | chr11:72996634-73012521 |
| 7356 | Ctps | NM_016748.2 | chr4:120212472-120242881 |
| 7357 | Ctps2 | NM_001168568.1 | chrX:159339491-159472473 |
| 7358 | Ctps2 | NM_001168569.1 | chrX:159339491-159472473 |
| 7359 | Ctps2 | NM_001168571.1 | chrX:159339491-159472473 |
| 7360 | Ctps2 | NM_018737.5 | chrX:159339491-159472473 |
| 7361 | Ctps2 | NR_033143.1 | chrX:159339491-159472473 |
| 7362 | Ctr9 | NM_009431.2 | chr7:118172464-118199891 |
| 7363 | Ctrb1 | NM_025583.2 | chr8:114210410-114214910 |
| 7364 | Ctrc | NM_001038875.2 | chr4:141394155-141402274 |
| 7365 | Ctrcos | NR_040641.1 | chr4:141400236-141402905 |
| 7366 | Ctrl | NM_023182.2 | chr8:108455893-108457762 |
| 7367 | Cts3 | NM_026906.3 | chr13:61665989-61671487 |
| 7368 | Cts3 | NM_054092.1 | chr13:61665989-61671487 |
| 7369 | Cts6 | NM_021445.1 | chr13:61296507-61304753 |
| 7370 | Cts7 | NM_019539.3 | chr13:61453821-61459531 |
| 7371 | Cts8 | NM_019541.3 | chr13:61348107-61356709 |
| 7372 | Cts8-ps | NR_027871.2 | chr13:61382740-61390211 |
| 7373 | Ctsa | NM_001038492.2 | chr2:164656229-164683208 |
| 7374 | Ctsa | NM_008906.4 | chr2:164656229-164683208 |
| 7375 | Ctsb | NM_007798.3 | chr14:63741299-63764760 |
| 7376 | Ctsc | NM_009982.4 | chr7:95426602-95459385 |
| 7377 | Ctsd | NM_009983.2 | chr7:149561520-149573775 |
| 7378 | Ctse | NM_007799.3 | chr1:133534890-133572084 |
| 7379 | Ctsf | NM_019861.1 | chr19:4855128-4860912 |
| 7380 | Ctsg | NM_007800.4 | chr14:56718717-56721411 |
| 7381 | Ctsh | NM_007801.2 | chr9:89949104-89970933 |
| 7382 | Ctsj | NM_012007.1 | chr13:61101638-61107272 |
| 7383 | Ctsk | NM_007802.4 | chr3:95303131-95313309 |
| 7384 | Ctsl | NM_009984.3 | chr13:64464521-64471614 |
| 7385 | Ctsll3 | NM_027344.3 | chr13:60899610-60904205 |
| 7386 | Ctsm | NM_022326.3 | chr13:61637803-61643199 |
| 7387 | Ctso | NM_177662.2 | chr8:17386537-17760647 |
| 7388 | Ctsq | NM_029636.3 | chr13:61136402-61143958 |
| 7389 | Ctsr | NM_020284.1 | chr13:61260575-61265549 |
| 7390 | Ctss | NM_001267695.2 | chr3:95330707-95360327 |
| 7391 | Ctss | NM_021281.3 | chr3:95330707-95360327 |
| 7392 | Ctsw | NM_009985.1 | chr19:5465239-5468498 |
| 7393 | Ctsz | NM_022325.4 | chr2:174252995-174264493 |
| 7394 | Cttn | NM_001252572.1 | chr7:151621628-151656840 |
| 7395 | Cttn | NM_007803.5 | chr7:151621628-151656840 |
| 7396 | Cttnbp2 | NM_080285.1 | chr6:18316476-18464825 |

Fig. 25 - 40

| | | | |
|---|---|---|---|
| 7397 | Ctnnbp2nl | NM_001163332.1 | chr3:104804832-104856064 |
| 7398 | Ctnnbp2nl | NM_001163333.1 | chr3:104804832-104856064 |
| 7399 | Ctnnbp2nl | NM_030249.4 | chr3:104804832-104856064 |
| 7400 | Ctu1 | NM_145582.1 | chr7:50927400-50933667 |
| 7401 | Ctu2 | NM_153775.2 | chr8:125000043-125006992 |
| 7402 | Ctxn1 | NM_183315.2 | chr8:4257645-4259274 |
| 7403 | Ctxn2 | NM_001162934.1 | chr2:124962427-124973577 |
| 7404 | Ctxn3 | NM_001134697.1 | chr18:57628139-57637788 |
| 7405 | Cubn | NM_001081084.2 | chr2:13197964-13413503 |
| 7406 | Cuedc1 | NM_001172099.1 | chr11:87911559-88025009 |
| 7407 | Cuedc1 | NM_198013.3 | chr11:87911559-88025009 |
| 7408 | Cuedc2 | NM_001164290.1 | chr19:46402673-46413150 |
| 7409 | Cuedc2 | NM_001164291.1 | chr19:46402673-46413150 |
| 7410 | Cuedc2 | NM_001164292.1 | chr19:46402673-46413150 |
| 7411 | Cuedc2 | NM_001164293.1 | chr19:46402673-46413150 |
| 7412 | Cuedc2 | NM_001164294.1 | chr19:46402673-46413150 |
| 7413 | Cuedc2 | NM_001164295.1 | chr19:46402673-46413150 |
| 7414 | Cuedc2 | NM_024192.2 | chr19:46402673-46413150 |
| 7415 | Cul1 | NM_012042.3 | chr6:47404322-47476138 |
| 7416 | Cul2 | NM_029402.3 | chr18:3383222-3436998 |
| 7417 | Cul3 | NM_016716.4 | chr1:80263392-80337005 |
| 7418 | Cul4a | NM_146207.2 | chr8:13105721-13147939 |
| 7419 | Cul4b | NM_001110142.1 | chrX:35884797-35929373 |
| 7420 | Cul4b | NM_028288.5 | chrX:35884797-35929373 |
| 7421 | Cul5 | NM_001161618.1 | chr9:53422686-53475612 |
| 7422 | Cul5 | NM_027807.3 | chr9:53422686-53475612 |
| 7423 | Cul7 | NM_025611.5 | chr17:46787286-46801313 |
| 7424 | Cul9 | NM_001081335.2 | chr17:46637557-46683337 |
| 7425 | Cuta | NM_026307.3 | chr17:27074916-27076483 |
| 7426 | Cuta | NM_026948.1 | chr17:27074916-27076483 |
| 7427 | Cuta | NR_104458.1 | chr17:27074916-27076483 |
| 7428 | Cutal | NM_030021.3 | chr2:34729955-34747653 |
| 7429 | Cutc | NM_001113562.1 | chr19:43827512-43843128 |
| 7430 | Cutc | NM_025530.3 | chr19:43827512-43843128 |
| 7431 | Cux1 | NM_001291233.1 | chr5:136724004-137043360 |
| 7432 | Cux1 | NM_001291234.1 | chr5:136724004-137043360 |
| 7433 | Cux1 | NM_001291238.1 | chr5:136724004-137043360 |
| 7434 | Cux1 | NM_001291239.1 | chr5:136724004-137043360 |
| 7435 | Cux1 | NM_001291240.1 | chr5:136724004-137043360 |
| 7436 | Cux1 | NM_009986.4 | chr5:136724004-137043360 |
| 7437 | Cux1 | NM_198602.3 | chr5:136724004-137043360 |
| 7438 | Cux2 | NM_007804.2 | chr5:122310224-122497834 |
| 7439 | Cuzd1 | NM_008411.3 | chr7:138452067-138465806 |
| 7440 | Cwc15 | NM_023153.3 | chr9:14305062-14315064 |
| 7441 | Cwc22 | NM_001290240.1 | chr2:77733709-77784413 |
| 7442 | Cwc22 | NM_030560.5 | chr2:77733709-77784413 |
| 7443 | Cwc22 | NM_172667.2 | chr2:77733709-77784413 |
| 7444 | Cwc25 | NM_001186.4 | chr11:97606783-97627927 |
| 7445 | Cwc27 | NM_026072.1 | chr13:105421406-105607033 |
| 7446 | Cwf19l1 | NM_001081077.1 | chr19:44183126-44210366 |
| 7447 | Cwf19l2 | NM_027545.2 | chr9:3404084-3479236 |
| 7448 | Cwh43 | NM_181323.2 | chr5:73797316-73844664 |
| 7449 | Cx3cl1 | NM_009142.3 | chr8:97296079-97306326 |
| 7450 | Cx3cr1 | NM_009987.4 | chr9:119957800-119977414 |
| 7451 | Cxadr | NM_001025192.3 | chr16:78301915-78360030 |
| 7452 | Cxadr | NM_001276263.1 | chr16:78301915-78360030 |
| 7453 | Cxadr | NM_009988.4 | chr16:78301915-78360030 |
| 7454 | Cxcl1 | NM_008176.3 | chr5:91320270-91322141 |
| 7455 | Cxcl10 | NM_021274.2 | chr5:92775665-92777915 |
| 7456 | Cxcl11 | NM_019494.1 | chr5:92760866-92843653 |
| 7457 | Cxcl11 | NR_038116.1 | chr5:92760866-92843653 |
| 7458 | Cxcl12 | NM_001012477.2 | chr6:117118552-117131386 |
| 7459 | Cxcl12 | NM_013655.4 | chr6:117118552-117131386 |
| 7460 | Cxcl12 | NM_021704.3 | chr6:117118552-117131386 |
| 7461 | Cxcl13 | NM_018866.2 | chr5:96385957-96390087 |
| 7462 | Cxcl14 | NM_019568.2 | chr13:56390005-56397912 |
| 7463 | Cxcl15 | NM_011339.2 | chr5:91223559-91232093 |
| 7464 | Cxcl16 | NM_023158.6 | chr11:70267736-70273486 |
| 7465 | Cxcl17 | NM_153576.2 | chr7:26185072-26197905 |
| 7466 | Cxcl2 | NM_009140.2 | chr5:91332924-91334964 |
| 7467 | Cxcl3 | NM_203320.3 | chr5:91215126-91217119 |
| 7468 | Cxcl5 | NM_009141.3 | chr5:91188323-91190651 |
| 7469 | Cxcl9 | NM_008599.4 | chr5:92750356-92757105 |
| 7470 | Cxcr1 | NM_178241.4 | chr1:74238359-74241205 |
| 7471 | Cxcr2 | NM_009909.3 | chr1:74200567-74207820 |
| 7472 | Cxcr3 | NM_009910.3 | chrX:98926874-98929486 |
| 7473 | Cxcr4 | NM_009911.3 | chr1:130484775-130488876 |
| 7474 | Cxcr5 | NM_007551.2 | chr9:44319869-44334504 |
| 7475 | Cxcr6 | NM_030712.4 | chr9:123715595-123720872 |
| 7476 | Cxx1a | NM_024170.2 | chrX:50945665-50946940 |
| 7477 | Cxx1b | NM_001018063.1 | chrX:50972353-50973585 |
| 7478 | Cxx1c | NM_028375.3 | chrX:50911098-50912311 |
| 7479 | Cxxc1 | NM_028868.3 | chr18:74375865-74381145 |
| 7480 | Cxxc4 | NM_001004367.4 | chr3:133899459-133925053 |
| 7481 | Cxxc5 | NM_133863.1 | chr18:35989471-36021342 |
| 7482 | Cyb5 | NM_025797.3 | chr18:85020805-85049255 |
| 7483 | Cyb561 | NM_008061.3 | chr11:105795017-105805461 |
| 7484 | Cyb561a3 | NM_001282064.1 | chr19:10651646-10664531 |
| 7485 | Cyb561a3 | NM_001282065.1 | chr19:10651646-10664531 |
| 7486 | Cyb561a3 | NM_001282067.1 | chr19:10651646-10664531 |
| 7487 | Cyb561a3 | NM_201351.2 | chr19:10651646-10664531 |
| 7488 | Cyb561d1 | NM_001081320.2 | chr3:107998688-108003752 |
| 7489 | Cyb561d1 | NM_028061.1 | chr3:107998688-108003752 |
| 7490 | Cyb561d2 | NM_019720.4 | chr9:107441341-107444196 |
| 7491 | Cyb5b | NM_025558.5 | chr8:109674560-109711370 |
| 7492 | Cyb5d1 | NM_001045525.1 | chr11:69207113-69208848 |
| 7493 | Cyb5d2 | NM_001024926.3 | chr11:72590733-72609341 |
| 7494 | Cyb5r1 | NM_028057.2 | chr1:136302566-136308315 |
| 7495 | Cyb5r2 | NM_001205227.1 | chr7:114738564-114901546 |
| 7496 | Cyb5r2 | NM_177216.4 | chr7:114738564-114901546 |
| 7497 | Cyb5r3 | NM_029787.2 | chr15:82983931-83002638 |
| 7498 | Cyb5r4 | NM_024195.2 | chr9:86916863-86972609 |
| 7499 | Cyb5rl | NM_175471.2 | chr4:106742772-106757410 |
| 7500 | Cyba | NM_007806.3 | chr8:124948670-124956840 |
| 7501 | Cybb | NM_007807.5 | chrX:9012379-9046450 |
| 7502 | Cybrd1 | NM_028593.2 | chr2:70956110-70980983 |
| 7503 | Cyc1 | NM_025567.2 | chr15:76173952-76176364 |
| 7504 | Cycs | NM_007808.4 | chr6:50512561-50516473 |
| 7505 | Cyct | NM_009989.3 | chr2:76191999-76198505 |
| 7506 | Cyfip1 | NM_001164661.1 | chr7:63097440-63217863 |
| 7507 | Cyfip1 | NM_001164662.1 | chr7:63097440-63217863 |
| 7508 | Cyfip1 | NM_011370.3 | chr7:63097440-63217863 |
| 7509 | Cyfip2 | NM_001252459.1 | chr11:46007350-46126361 |
| 7510 | Cyfip2 | NM_001252460.1 | chr11:46007350-46126361 |
| 7511 | Cyfip2 | NM_133769.3 | chr11:46007350-46126361 |
| 7512 | Cygb | NM_030206.4 | chr11:116506908-116515627 |
| 7513 | Cyhr1 | NM_001276321.1 | chr15:76473824-76490638 |
| 7514 | Cyhr1 | NM_001276322.1 | chr15:76473824-76490638 |
| 7515 | Cyhr1 | NM_001276333.1 | chr15:76473824-76490638 |
| 7516 | Cyhr1 | NM_001276334.1 | chr15:76473824-76490638 |
| 7517 | Cyhr1 | NM_001276335.1 | chr15:76473824-76490638 |
| 7518 | Cyhr1 | NM_019396.3 | chr15:76473824-76490638 |
| 7519 | Cyhr1 | NM_180962.2 | chr15:76473824-76490638 |
| 7520 | Cylc1 | NM_026134.2 | chrX:108305756-108319213 |
| 7521 | Cylc2 | NM_001162865.1 | chr4:51229549-51242800 |
| 7522 | Cyld | NM_001128170.2 | chr8:91220926-91275845 |
| 7523 | Cyld | NM_001128171.2 | chr8:91220926-91275845 |
| 7524 | Cyld | NM_001276279.1 | chr8:91220926-91275845 |
| 7525 | Cyld | NM_173369.3 | chr8:91220926-91275845 |
| 7526 | Cyln | NM_001111143.1 | chr3:107014212-107024650 |
| 7527 | Cyp11a1 | NM_019779.3 | chr9:57862823-57874830 |
| 7528 | Cyp11b1 | NM_001033229.3 | chr15:74665321-74672073 |
| 7529 | Cyp11b2 | NM_009991.3 | chr15:74681449-74686748 |
| 7530 | Cyp17a1 | NM_007809.3 | chr19:46741654-46747490 |
| 7531 | Cyp19a1 | NM_007810.3 | chr9:54013743-54041249 |
| 7532 | Cyp1a1 | NM_001136059.2 | chr9:57535734-57551631 |
| 7533 | Cyp1a1 | NM_009992.4 | chr9:57535734-57551631 |
| 7534 | Cyp1a2 | NM_009993.3 | chr9:57524743-57531462 |
| 7535 | Cyp1b1 | NM_009994.1 | chr17:80106292-80114381 |
| 7536 | Cyp20a1 | NM_030013.2 | chr1:60400215-60444231 |
| 7537 | Cyp21a1 | NM_009995.2 | chr17:34938292-34941371 |
| 7538 | Cyp24a1 | NM_009996.3 | chr2:170308465-170322638 |
| 7539 | Cyp26a1 | NM_007811.2 | chr19:37772297-37776026 |
| 7540 | Cyp26b1 | NM_001177713.1 | chr6:84521407-84543902 |
| 7541 | Cyp26b1 | NM_175475.3 | chr6:84521407-84543902 |
| 7542 | Cyp26c1 | NM_001105201.1 | chr19:37760169-37767797 |
| 7543 | Cyp27a1 | NM_024264.4 | chr1:74760147-74784464 |
| 7544 | Cyp27b1 | NM_010009.2 | chr10:126485301-126490062 |
| 7545 | Cyp2a12 | NM_133657.1 | chr7:27814108-27821834 |
| 7546 | Cyp2a22 | NM_001101467.1 | chr7:27716649-27724405 |
| 7547 | Cyp2a4 | NM_009997.2 | chr7:27092210-27100107 |
| 7548 | Cyp2a5 | NM_007812.4 | chr7:27620357-27628283 |
| 7549 | Cyp2ab1 | NM_183158.3 | chr16:20308459-20325477 |
| 7550 | Cyp2b10 | NM_009999.4 | chr7:26682676-26711643 |
| 7551 | Cyp2b13 | NM_007813.2 | chr7:26846513-26881215 |
| 7552 | Cyp2b19 | NM_007814.2 | chr7:27542205-27557649 |
| 7553 | Cyp2b23 | NM_001081148.1 | chr7:27450245-27471449 |
| 7554 | Cyp2b9 | NM_010000.2 | chr7:26958427-26995679 |
| 7555 | Cyp2c29 | NM_007815.3 | chr19:39361574-39405203 |
| 7556 | Cyp2c37 | NM_010001.2 | chr19:40066913-40086733 |
| 7557 | Cyp2c38 | NM_010002.3 | chr19:39484045-39537565 |
| 7558 | Cyp2c39 | NM_010003.2 | chr19:39585311-39643019 |
| 7559 | Cyp2c40 | NM_010004.2 | chr19:39841562-39887304 |
| 7560 | Cyp2c44 | NM_001001446.3 | chr19:44079511-44103737 |
| 7561 | Cyp2c44 | NM_001167905.1 | chr19:44079511-44103737 |
| 7562 | Cyp2c50 | NM_001167875.1 | chr19:40164168-40188445 |
| 7563 | Cyp2c50 | NM_001167877.1 | chr19:40164168-40188445 |
| 7564 | Cyp2c50 | NM_134144.2 | chr19:40164168-40188445 |
| 7565 | Cyp2c53-ps | NR_033614.1 | chr19:39303743-39349227 |
| 7566 | Cyp2c54 | NM_206537.2 | chr19:40112429-40148303 |
| 7567 | Cyp2c55 | NM_028089.3 | chr19:39081508-39117177 |
| 7568 | Cyp2c65 | NM_028191.2 | chr19:39135495-39168438 |
| 7569 | Cyp2c66 | NM_001017707.1 | chr19:39188387-39261246 |
| 7570 | Cyp2c67 | NM_001024719.2 | chr19:39683348-39723532 |
| 7571 | Cyp2c68 | NM_001039555.2 | chr19:39763325-39815591 |
| 7572 | Cyp2c69 | NM_001104525.1 | chr19:39917149-39961259 |
| 7573 | Cyp2c70 | NM_145499.2 | chr19:40227850-40261776 |
| 7574 | Cyp2d10 | NM_010005.3 | chr15:82233275-82237624 |
| 7575 | Cyp2d11 | NM_001104531.1 | chr15:82,219,584-82,224,452 |
| 7576 | Cyp2d12 | NM_201360.1 | chr15:82385527-82389843 |
| 7577 | Cyp2d13 | NR_003552.1 | chr15:82467179-82472475 |
| 7578 | Cyp2d22 | NM_001163472.1 | chr15:82200956-82210690 |
| 7579 | Cyp2d22 | NM_019823.4 | chr15:82200956-82210690 |
| 7580 | Cyp2d26 | NM_029562.2 | chr15:82620536-82624675 |
| 7581 | Cyp2d34 | NM_145474.2 | chr15:82446394-82451337 |
| 7582 | Cyp2d37-ps | NR_033515.1 | chr15:82519179-82520488 |
| 7583 | Cyp2d40 | NM_026323.2 | chr15:82590622-82594552 |
| 7584 | Cyp2d9 | NM_010006.2 | chr15:82282806-82287257 |
| 7585 | Cyp2e1 | NM_021282.2 | chr7:149749730-149760876 |
| 7586 | Cyp2f2 | NM_007817.2 | chr7:27904973-27918679 |

Fig. 25 - 41

| | | | |
|---|---|---|---|
| 7587 | Cyp2g1 | NM_013809.1 | chr7:27593945-27606216 |
| 7588 | Cyp2j11 | NM_001004141.2 | chr4:95961198-96015371 |
| 7589 | Cyp2j12 | NM_001100182.2 | chr4:95766008-95807843 |
| 7590 | Cyp2j13 | NM_145548.4 | chr4:95709350-95744231 |
| 7591 | Cyp2j5 | NM_010007.2 | chr4:96294122-96330810 |
| 7592 | Cyp2j6 | NM_010008.4 | chr4:96182828-96220342 |
| 7593 | Cyp2j8 | NM_001104927.1 | chr4:96111278-96174077 |
| 7594 | Cyp2j9 | NM_028979.2 | chr4:96235119-96258176 |
| 7595 | Cyp2r1 | NM_177382.4 | chr7:121693676-121706486 |
| 7596 | Cyp2r1 | NR_110407.1 | chr7:121693676-121706486 |
| 7597 | Cyp2r1 | NR_110408.1 | chr7:121693676-121706486 |
| 7598 | Cyp2s1 | NM_028775.3 | chr7:26587494-26601549 |
| 7599 | Cyp2t4 | NM_001100184.1 | chr7:27938732-27943583 |
| 7600 | Cyp2u1 | NM_027816.3 | chr3:130993408-131006145 |
| 7601 | Cyp2w1 | NM_001160265.1 | chr5:139828570-139832987 |
| 7602 | Cyp39a1 | NM_001285947.1 | chr17:43804320-43888380 |
| 7603 | Cyp39a1 | NM_001285948.1 | chr17:43804320-43888380 |
| 7604 | Cyp39a1 | NM_018887.3 | chr17:43804320-43888380 |
| 7605 | Cyp3a11 | NM_007818.3 | chr5:146666182-146691430 |
| 7606 | Cyp3a13 | NM_007819.4 | chr5:138334160-138362847 |
| 7607 | Cyp3a16 | NM_007820.2 | chr5:146197177-146230592 |
| 7608 | Cyp3a25 | NM_019792.2 | chr5:146788769-146821194 |
| 7609 | Cyp3a25 | NR_030782.1 | chr5:146788769-146821194 |
| 7610 | Cyp3a41a | NM_017396.3 | chr5:146505623-146531712 |
| 7611 | Cyp3a41b | NM_001105159.1 | chr5:146313528-146345599 |
| 7612 | Cyp3a44 | NM_177380.3 | chr5:146585558-146617450 |
| 7613 | Cyp3a57 | NM_001100180.1 | chr5:146106138-146151381 |
| 7614 | Cyp3a59 | NM_001105160.1 | chr5:146890833-146924859 |
| 7615 | Cyp46a1 | NM_010010.1 | chr12:109572590-109600444 |
| 7616 | Cyp4a10 | NM_010011.3 | chr4:115190891-115206254 |
| 7617 | Cyp4a12a | NM_177406.3 | chr4:114971650-115005420 |
| 7618 | Cyp4a12b | NM_172306.2 | chr4:115084228-115111639 |
| 7619 | Cyp4a14 | NM_007822.2 | chr4:115158804-115168746 |
| 7620 | Cyp4a29 | NM_001100183.1 | chr4:114914688-114927162 |
| 7621 | Cyp4a30b | NM_001100185.1 | chr4:115125208-115143667 |
| 7622 | Cyp4a31 | NM_001252539.1 | chr4:115236253-115251620 |
| 7623 | Cyp4a31 | NM_201640.1 | chr4:115236253-115251620 |
| 7624 | Cyp4a32 | NM_001100181.1 | chr4:115273542-115294971 |
| 7625 | Cyp4b1 | NM_007823.2 | chr4:115297332-115320310 |
| 7626 | Cyp4b1-ps2 | NR_033575.1 | chr4:115254642-115255732 |
| 7627 | Cyp4f13 | NM_130882.1 | chr17:33061632-33084306 |
| 7628 | Cyp4f14 | NM_001204233.1 | chr17:33042014-33054287 |
| 7629 | Cyp4f14 | NM_001204334.1 | chr17:33042014-33054287 |
| 7630 | Cyp4f14 | NM_001204335.1 | chr17:33042014-33054287 |
| 7631 | Cyp4f14 | NM_001204336.1 | chr17:33042014-33054287 |
| 7632 | Cyp4f14 | NM_022434.2 | chr17:33042014-33054287 |
| 7633 | Cyp4f15 | NM_134127.1 | chr17:32822603-32840294 |
| 7634 | Cyp4f16 | NM_024442.1 | chr17:32673573-32688742 |
| 7635 | Cyp4f17 | NM_001101445.1 | chr17:32643406-32865839 |
| 7636 | Cyp4f18 | NM_024444.2 | chr8:74512380-74533525 |
| 7637 | Cyp4f37 | NM_001100187.1 | chr17:32758263-32773129 |
| 7638 | Cyp4f39 | NM_177307.3 | chr17:32589667-32630265 |
| 7639 | Cyp4f40 | NM_001100186.1 | chr17:32796427-32813425 |
| 7640 | Cyp4f41-ps | NR_033585.1 | chr17:33087905-33102661 |
| 7641 | Cyp4v3 | NM_133969.2 | chr8:46391155-46418550 |
| 7642 | Cyp4x1 | NM_001003947.1 | chr4:114781286-114806582 |
| 7643 | Cyp51 | NM_020010.2 | chr5:4080673-4104697 |
| 7644 | Cyp7a1 | NM_007824.2 | chr4:6192758-6202778 |
| 7645 | Cyp7b1 | NM_007825.4 | chr3:17971949-18143338 |
| 7646 | Cyp8b1 | NM_010012.3 | chr9:121823473-121825423 |
| 7647 | Cypt1 | NM_025738.2 | chrX:16099998-16100815 |
| 7648 | Cypt10 | NM_001039944.2 | chr9:24429648-24430181 |
| 7649 | Cypt12 | NM_029289.1 | chr3:17848443-17848952 |
| 7650 | Cypt14 | NM_001191032.1 | chrX:37216095-37216781 |
| 7651 | Cypt15 | NM_001177380.1 | chrX:36699442-36700138 |
| 7652 | Cypt2 | NM_173436.2 | chrX:102695110-102695976 |
| 7653 | Cypt3 | NM_173367.2 | chrX:149993135-149993972 |
| 7654 | Cypt4 | NM_173412.2 | chr9:24429629-24430272 |
| 7655 | Cypt7 | NM_001039943.2 | chrX:16,100,007-16,100,815 |
| 7656 | Cypt8 | NM_001039941.2 | chrX:16,099,998-16,100,815 |
| 7657 | Cyr61 | NM_010516.2 | chr3:145309934-145312949 |
| 7658 | Cys1 | NM_001004455.2 | chr12:25350702-25366660 |
| 7659 | Cys1 | NM_001181807.1 | chr12:25350702-25366660 |
| 7660 | Cys1 | NM_138686.3 | chr12:25350702-25366660 |
| 7661 | Cysltr1 | NM_001281859.1 | chrX:103771847-103905896 |
| 7662 | Cysltr1 | NM_001281862.1 | chrX:103771847-103905896 |
| 7663 | Cysltr1 | NM_021476.5 | chrX:103771847-103905896 |
| 7664 | Cysltr2 | NM_001162412.1 | chr14:73428934-73448921 |
| 7665 | Cysltr2 | NM_133720.3 | chr14:73428934-73448921 |
| 7666 | Cystm1 | NM_001081365.1 | chr18:36508277-36553024 |
| 7667 | Cyth1 | NM_001112699.1 | chr11:118025479-118109906 |
| 7668 | Cyth1 | NM_001112700.1 | chr11:118025479-118109906 |
| 7669 | Cyth1 | NM_011180.3 | chr11:118025479-118109906 |
| 7670 | Cyth2 | NM_001112701.1 | chr7:53062006-53069686 |
| 7671 | Cyth2 | NM_011181.3 | chr7:53062006-53069686 |
| 7672 | Cyth3 | NM_001163548.1 | chr5:144383315-144471117 |
| 7673 | Cyth3 | NM_181642.4 | chr5:144383315-144471117 |
| 7674 | Cyth4 | NM_028195.3 | chr15:78427476-78452449 |
| 7675 | Cytip | NM_139200.4 | chr2:57981549-58012533 |
| 7676 | Cytl1 | NM_001081106.1 | chr5:38126757-38131059 |
| 7677 | Cyyr1 | NM_144853.3 | chr16:85456489-85550618 |
| 7678 | D030018L15Rik | NR_003627.1 | chr15:95903767-95909983 |
| 7679 | D030024E09Rik | NR_040350.1 | chr5:61530838-61606006 |
| 7680 | D030025E07Rik | NR_045704.1 | chr9:127819932-127934523 |
| 7681 | D030025P21Rik | NR_028577.1 | chr12:86216752-86220705 |
| 7682 | D030028A08Rik | NR_003293.3 | chr11:96805460-96826374 |
| 7683 | D030040B21Rik | NR_037998.1 | chr1:16647632-16652359 |
| 7684 | D030045P18Rik | NR_040624.1 | chr10:45527509-45571824 |
| 7685 | D030047H15Rik | NR_033548.1 | chr7:4077942-4088528 |
| 7686 | D030056L22Rik | NM_177640.4 | chr19:18787725-18792918 |
| 7687 | D10Bwg1379e | NM_001033258.4 | chr10:18307816-18463564 |
| 7688 | D10Jhu81e | NM_138601.2 | chr10:77624811-77632513 |
| 7689 | D10Wsu102e | NM_026579.3 | chr10:82822965-82831580 |
| 7690 | D11Wsu47e | NM_177777.5 | chr11:113545725-113555961 |
| 7691 | D130009I18Rik | NR_015593.2 | chr14:105038363-105366000 |
| 7692 | D130017N08Rik | NR_015486.2 | chr5:144519222-144525811 |
| 7693 | D130020L05Rik | NR_038047.1 | chr12:102277618-102327137 |
| 7694 | D130020L05Rik | NR_038048.1 | chr12:102277618-102327137 |
| 7695 | D130020L05Rik | NR_038049.1 | chr12:102277618-102327137 |
| 7696 | D130020L05Rik | NR_038050.1 | chr12:102277618-102327137 |
| 7697 | D130040H23Rik | NM_172491.2 | chr8:71794978-71827274 |
| 7698 | D130043K22Rik | NM_001081051.2 | chr13:24936999-24993159 |
| 7699 | D130058E03 | NR_073373.1 | chr6:127246203-127257985 |
| 7700 | D14Ertd670e | NR_105025.1 | chr14:20658146-20663899 |
| 7701 | D15Ertd621e | NM_145959.3 | chr15:58247022-58289356 |
| 7702 | D16Ertd472e | NM_001252438.1 | chr16:78540580-78576933 |
| 7703 | D16Ertd472e | NM_001252439.1 | chr16:78540580-78576933 |
| 7704 | D16Ertd472e | NM_001252440.1 | chr16:78540580-78576933 |
| 7705 | D16Ertd472e | NM_025967.4 | chr16:78540580-78576933 |
| 7706 | D16Ertd519e | NM_040474.1 | chr16:70616669-70625067 |
| 7707 | D17Ertd648e | NR_045808.1 | chr17:12055936-12076055 |
| 7708 | D17H6S53E | NM_033477.2 | chr17:35263346-35265800 |
| 7709 | D17Wsu104e | NM_080837.2 | chr17:56315963-56323343 |
| 7710 | D17Wsu92e | NM_001033279.3 | chr17:27888176-27957487 |
| 7711 | D17Wsu92e | NM_001044719.2 | chr17:27888176-27957487 |
| 7712 | D17Wsu92e | NM_001271511.1 | chr17:27888176-27957487 |
| 7713 | D19Bwg1357e | NM_177474.5 | chr19:27463191-27504310 |
| 7714 | D1Ertd622e | NM_133825.3 | chr1:99540478-99558595 |
| 7715 | D1Pas1 | NM_033077.3 | chr1:188791294-188794506 |
| 7716 | D230025D16Rik | NM_145604.2 | chr8:107749088-107776951 |
| 7717 | D230030E09Rik | NR_045947.1 | chr12:119756769-119768666 |
| 7718 | D2hgdh | NM_178882.3 | chr1:95721816-95748751 |
| 7719 | D2Wsu81e | NM_172660.4 | chr2:30028967-30033979 |
| 7720 | D330032K18Rik | NR_040334.1 | chr2:31006568-31007811 |
| 7721 | D330041H03Rik | NR_033554.1 | chr17:24546426-24551458 |
| 7722 | D330045A20Rik | NM_175326.5 | chrX:136014905-136069119 |
| 7723 | D330050G23Rik | NR_040335.1 | chr2:116725887-116738527 |
| 7724 | D330050G23Rik | NR_040336.1 | chr2:116725887-116738527 |
| 7725 | D330050J16Rik | NR_033224.1 | chr19:5388336-5390069 |
| 7726 | D3Bwg0562e | NM_177664.5 | chr3:117022062-117063794 |
| 7727 | D3Ertd254e | NM_001101478.1 | chr3:36050001-36069263 |
| 7728 | D3Ertd751e | NM_001099785.1 | chr3:41546536-41562863 |
| 7729 | D3Ertd751e | NM_001291048.1 | chr3:41546536-41562863 |
| 7730 | D3Ertd751e | NM_027271.1 | chr3:41546536-41562863 |
| 7731 | D3Ertd751e | NM_028667.3 | chr3:41546536-41562863 |
| 7732 | D430020J02Rik | NM_001252508.1 | chr12:106692065-106731305 |
| 7733 | D430020J02Rik | NR_028421.1 | chr12:117640419-117643634 |
| 7734 | D430036J16Rik | NR_040393.1 | chr9:81524998-81538763 |
| 7735 | D430036J16Rik | NR_040394.1 | chr9:81524998-81538763 |
| 7736 | D430036J16Rik | NR_040395.1 | chr9:81524998-81538763 |
| 7737 | D430036J16Rik | NR_040396.1 | chr9:81524998-81538763 |
| 7738 | D430036J16Rik | NR_040397.1 | chr9:81524998-81538763 |
| 7739 | D430041D05Rik | NM_001033347.2 | chr2:103983231-104250491 |
| 7740 | D430042O09Rik | NM_001081022.1 | chr7:132851389-133018311 |
| 7741 | D4Ertd617e | NR_029469.1 | chr4:118299009-118304520 |
| 7742 | D530049I02Rik | NR_040605.1 | chr2:73445542-73477353 |
| 7743 | D5Ertd577e | NM_177187.4 | chr5:95885825-95914608 |
| 7744 | D5Ertd579e | NM_001081232.3 | chr5:36943137-37087260 |
| 7745 | D5Ertd605e | NR_033625.1 | chr5:148230195-148234620 |
| 7746 | D630003M21Rik | NM_001131021.2 | chr2:158008268-158054960 |
| 7747 | D630003M21Rik | NM_177657.5 | chr2:158008268-158054960 |
| 7748 | D630010B17Rik | NR_045629.1 | chr15:94077632-94086037 |
| 7749 | D630013N20Rik | NR_045291.1 | chr10:70063796-70118711 |
| 7750 | D630013N20Rik | NR_045292.1 | chr10:70063796-70118711 |
| 7751 | D630023F18Rik | NM_001285881.1 | chr1:65151858-65169788 |
| 7752 | D630023F18Rik | NM_001285882.1 | chr1:65151858-65169788 |
| 7753 | D630023F18Rik | NM_175293.4 | chr1:65151858-65169788 |
| 7754 | D630024L09Rik | NR_102310.1 | chr11:31700687-31724547 |
| 7755 | D630024D03Rik | NR_102311.1 | chr11:31700687-31724547 |
| 7756 | D630024D03Rik | NR_102312.1 | chr11:31700687-31724547 |
| 7757 | D630024D03Rik | NR_102314.1 | chr11:31700687-31724547 |
| 7758 | D630029K05Rik | NR_027846.1 | chr10:116401795-116406163 |
| 7759 | D630029K05Rik | NR_027847.1 | chr10:116401795-116406163 |
| 7760 | D630032G03Rik | NR_028329.1 | chr11:85046867-85051806 |
| 7761 | D630033O11Rik | NM_001243261.1 | chr9:43067961-43088158 |
| 7762 | D630039A03Rik | NM_178727.2 | chr4:57921255-57929136 |
| 7763 | D630041G03Rik | NR_028416.1 | chr7:4418847-4422486 |
| 7764 | D630045J12Rik | NM_194061.2 | chr6:38073174-38204009 |
| 7765 | D630045M09Rik | NR_045293.1 | chr13:73482112-73484832 |
| 7766 | D6Ertd474e | NR_027803.1 | chr6:143194407-143246399 |
| 7767 | D6Ertd527e | NM_001167937.1 | chr6:87054739-87062997 |
| 7768 | D6Ertd527e | NM_001167938.1 | chr6:87054739-87062997 |
| 7769 | D6Wsu163e | NM_138594.3 | chr6:126889983-126925722 |
| 7770 | D730001G18Rik | NR_027836.1 | chr15:74601337-74609289 |
| 7771 | D730001G18Rik | NR_027837.1 | chr15:74601337-74609289 |
| 7772 | D730005E14Rik | NR_030675.1 | chr15:79719962-79723568 |
| 7773 | D730045A05Rik | NR_045390.1 | chr18:74177561-74179742 |
| 7774 | D730048I06Rik | NR_026593.3 | chr9:35595634-35597697 |
| 7775 | D730050B12Rik | NR_046196.1 | chr13:72947048-72954211 |
| 7776 | D7Ertd143e | NR_028425.1 | chr7:3218785-3221016 |

Fig. 25 - 42

| | | | |
|---|---|---|---|
| 7777 | D7Ertd443e | NM_001081331.1 | chr7:141457944-141568511 |
| 7778 | D7Ertd443e | NM_001199941.1 | chr7:141457944-141568511 |
| 7779 | D7Ertd715e | NR_015456.1 | chr7:67114462-67119317 |
| 7780 | D830005E20Rik | NR_040657.1 | chr10:32942151-32976163 |
| 7781 | D830013O20Rik | NR_046013.1 | chr12:74465061-74510550 |
| 7782 | D830015G02Rik | NR_033497.1 | chr14:55587624-55593186 |
| 7783 | D830026I12Rik | NR_102304.1 | chr6:17147750-17155695 |
| 7784 | D830026I12Rik | NR_102305.1 | chr6:17147750-17155695 |
| 7785 | D830030K20Rik | NM_177335.4 | chr14:3224445-3234357 |
| 7786 | D830031N03Rik | NM_001167918.1 | chr4:123080844-123089154 |
| 7787 | D830032E09Rik | NR_102306.1 | chr1:109813835-109847524 |
| 7788 | D830032E09Rik | NR_102307.1 | chr1:109813835-109847524 |
| 7789 | D830046C22Rik | NR_033147.1 | chr5:139853651-139856007 |
| 7790 | D8Ertd738e | NM_001007571.2 | chr8:86770133-86773660 |
| 7791 | D8Ertd82e | NM_172911.3 | chr8:37157881-37210841 |
| 7792 | D930007P13Rik | NR_045743.1 | chr15:102953500-102977259 |
| 7793 | D930015E06Rik | NM_172681.4 | chr3:83702208-83844083 |
| 7794 | D930015M05Rik | NR_040621.1 | chr2:92249049-92272465 |
| 7795 | D930016O06Rik | NR_030673.1 | chr5:104964753-104983230 |
| 7796 | D930020B18Rik | NM_177335.4 | chr10:121078756-121130970 |
| 7797 | D930028M14Rik | NR_045847.1 | chr7:25937475-25941649 |
| 7798 | D930028M14Rik | NR_045848.1 | chr7:25937475-25941649 |
| 7799 | D930032P07Rik | NR_045330.1 | chr19:28752714-28794517 |
| 7800 | D930048N14Rik | NR_027958.1 | chr1:51464456-51471183 |
| 7801 | Daam1 | NM_001286452.1 | chr12:72932054-73093363 |
| 7802 | Daam1 | NM_026102.3 | chr12:72932054-73093363 |
| 7803 | Daam1 | NM_172464.3 | chr12:72932054-73093363 |
| 7804 | Daam2 | NM_001008231.2 | chr17:49595346-49703662 |
| 7805 | Dab1 | NM_010014.3 | chr4:104040142-104417449 |
| 7806 | Dab1 | NM_177259.4 | chr4:104040142-104417449 |
| 7807 | Dab1 | NR_104385.1 | chr4:104040142-104417449 |
| 7808 | Dab2 | NM_001008702.2 | chr15:6249788-6390709 |
| 7809 | Dab2 | NM_001037905.3 | chr15:6249788-6390709 |
| 7810 | Dab2 | NM_001102400.1 | chr15:6249788-6390709 |
| 7811 | Dab2 | NM_023118.5 | chr15:6249788-6390709 |
| 7812 | Dab2ip | NM_001001602.2 | chr2:35405053-35586514 |
| 7813 | Dab2ip | NM_001114124.1 | chr2:35405053-35586514 |
| 7814 | Dab2ip | NM_001114125.1 | chr2:35405053-35586514 |
| 7815 | Dab2ip | NM_001290639.1 | chr2:35405053-35586514 |
| 7816 | Dab2ip | NM_001290640.1 | chr2:35405053-35586514 |
| 7817 | Dab2ip | NM_001290641.1 | chr2:35405053-35586514 |
| 7818 | Dab2ip | NM_001290641.1 | chr2:35405053-35586514 |
| 7819 | Dach1 | NM_001038610.2 | chr14:98186064-98568984 |
| 7820 | Dach1 | NM_007826.3 | chr14:98186064-98568984 |
| 7821 | Dach2 | NM_001142570.1 | chrX:110411118-110949995 |
| 7822 | Dach2 | NM_001289732.1 | chrX:110411118-110949995 |
| 7823 | Dach2 | NM_001289733.1 | chrX:110411118-110949995 |
| 7824 | Dach2 | NM_001289734.1 | chrX:110411118-110949995 |
| 7825 | Dach2 | NM_033605.2 | chrX:110411118-110949995 |
| 7826 | Dact1 | NM_001190466.1 | chr12:72410870-72421094 |
| 7827 | Dact1 | NM_021532.4 | chr12:72410870-72421094 |
| 7828 | Dact2 | NM_172826.3 | chr17:14332236-14340838 |
| 7829 | Dact3 | NM_001081655.1 | chr7:17460665-17472650 |
| 7830 | Dad1 | NM_001113358.1 | chr14:54855159-54873604 |
| 7831 | Dad1 | NM_010015.4 | chr14:54855159-54873604 |
| 7832 | Daf2 | NM_007827.2 | chr1:132285104-132319576 |
| 7833 | Dag1 | NM_001276481.1 | chr9:108107191-108166289 |
| 7834 | Dag1 | NM_001276482.1 | chr9:108107191-108166289 |
| 7835 | Dag1 | NM_001276485.1 | chr9:108107191-108166289 |
| 7836 | Dag1 | NM_001276486.1 | chr9:108107191-108166289 |
| 7837 | Dag1 | NM_001276492.1 | chr9:108107191-108166289 |
| 7838 | Dag1 | NM_001276493.1 | chr9:108107191-108166289 |
| 7839 | Dag1 | NM_001276494.1 | chr9:108107191-108166289 |
| 7840 | Dag1 | NM_010017.4 | chr9:108107191-108166289 |
| 7841 | Dagla | NM_198114.2 | chr19:10319754-10379367 |
| 7842 | Daglb | NM_144915.3 | chr5:144225360-144265310 |
| 7843 | Dak | NM_145496.1 | chr19:10666686-10678748 |
| 7844 | Dalrd3 | NM_026378.2 | chr9:108472223-108475102 |
| 7845 | Dancr | NR_015531.1 | chr5:74489108-74490361 |
| 7846 | Dand5 | NM_201367.2 | chr8:87339303-87356164 |
| 7847 | Dand5 | NR_033145.1 | chr8:87339303-87356164 |
| 7848 | Dao | NM_001286396.1 | chr5:114453743-114475684 |
| 7849 | Dao | NM_001286397.1 | chr5:114453743-114475684 |
| 7850 | Dao | NM_010018.3 | chr5:114453743-114475684 |
| 7851 | Dap | NM_146057.3 | chr15:31154139-31204093 |
| 7852 | Dap3 | NM_001164533.1 | chr3:88724724-88754204 |
| 7853 | Dap3 | NM_022994.3 | chr3:88724724-88754204 |
| 7854 | Dapk1 | NM_001285917.1 | chr13:60703307-60864552 |
| 7855 | Dapk1 | NM_029563.3 | chr13:60703307-60864552 |
| 7856 | Dapk1 | NM_134062.2 | chr13:60703307-60864552 |
| 7857 | Dapk2 | NM_010019.3 | chr9:66006032-66120049 |
| 7858 | Dapk3 | NM_001190473.1 | chr10:80645751-80655942 |
| 7859 | Dapk3 | NM_001190474.1 | chr10:80645751-80655942 |
| 7860 | Dapk3 | NM_007828.2 | chr10:80645751-80655942 |
| 7861 | Dapl1 | NM_029723.3 | chr2:59322709-59343078 |
| 7862 | Dapp1 | NM_011932.2 | chr3:137593969-137644513 |
| 7863 | Dars | NM_145752.1 | chr1:130260283-130313993 |
| 7864 | Dars | NM_177445.5 | chr1:130260283-130313993 |
| 7865 | Dars2 | NM_172644.3 | chr1:162970743-163060763 |
| 7866 | Daw1 | NM_027725.3 | chr1:83156336-83207147 |
| 7867 | Daw1 | NR_027636.1 | chr1:83156336-83207147 |
| 7868 | Daxx | NM_001199733.1 | chr17:34046389-34052535 |
| 7869 | Daxx | NM_007829.4 | chr17:34046389-34052535 |
| 7870 | Dazap1 | NM_001122604.1 | chr10:79727735-79751158 |
| 7871 | Dazap1 | NM_001122605.1 | chr10:79727735-79751158 |
| 7872 | Dazap1 | NM_133188.2 | chr10:79727735-79751158 |
| 7873 | Dazap2 | NM_011873.2 | chr15:100446092-100451192 |
| 7874 | Dazl | NM_001277863.1 | chr17:50418717-50432945 |
| 7875 | Dazl | NM_010021.5 | chr17:50418717-50432945 |
| 7876 | Dbf4 | NM_001190717.1 | chr5:8396968-8422716 |
| 7877 | Dbf4 | NM_013726.3 | chr5:8396968-8422716 |
| 7878 | Dbh | NM_138942.3 | chr2:27021026-27038724 |
| 7879 | Dbhos | NR_040524.1 | chr2:27000417-27018223 |
| 7880 | Dbi | NM_001037999.2 | chr1:122009856-122017673 |
| 7881 | Dbi | NM_007830.4 | chr1:122009856-122017673 |
| 7882 | Dbil5 | NM_021294.2 | chr11:76031114-76032167 |
| 7883 | Dbn1 | NM_001177371.1 | chr13:55574788-55589437 |
| 7884 | Dbn1 | NM_001177372.1 | chr13:55574788-55589437 |
| 7885 | Dbn1 | NM_019813.4 | chr13:55574788-55589437 |
| 7886 | Dbndd1 | NM_001170975.2 | chr8:126028617-126039355 |
| 7887 | Dbndd1 | NM_001170976.1 | chr8:126028617-126039355 |
| 7888 | Dbndd1 | NM_028146.4 | chr8:126028617-126039355 |
| 7889 | Dbndd2 | NM_001048227.1 | chr2:164311639-164318823 |
| 7890 | Dbndd2 | NM_001048228.1 | chr2:164311639-164318823 |
| 7891 | Dbndd2 | NM_001048229.1 | chr2:164311639-164318823 |
| 7892 | Dbndd2 | NM_026797.2 | chr2:164311639-164318823 |
| 7893 | Dbnl | NM_001146308.1 | chr11:5688485-5700983 |
| 7894 | Dbnl | NM_001146309.1 | chr11:5688485-5700983 |
| 7895 | Dbnl | NM_013810.3 | chr11:5688485-5700983 |
| 7896 | Dbp | NM_016974.3 | chr7:52960617-52965573 |
| 7897 | Dbphtr2 | NM_198866.2 | chr12:75398460-75401455 |
| 7898 | Dbr1 | NM_031403.3 | chr9:99476217-99484762 |
| 7899 | Dbt | NM_010022.3 | chr3:116215996-116252899 |
| 7900 | Dbx1 | NM_001005232.1 | chr7:56886868-56892205 |
| 7901 | Dbx2 | NM_207533.2 | chr15:95453993-95485202 |
| 7902 | Dcaf10 | NM_153167.2 | chr4:45354972-45392594 |
| 7903 | Dcaf11 | NM_001199009.1 | chr14:56178865-56188902 |
| 7904 | Dcaf11 | NM_133734.3 | chr14:56178865-56188902 |
| 7905 | Dcaf11 | NR_037572.1 | chr14:56178865-56188902 |
| 7906 | Dcaf12 | NM_026893.3 | chr4:41238332-41261934 |
| 7907 | Dcaf12l1 | NM_001190718.1 | chrX:42139743-42143374 |
| 7908 | Dcaf12l1 | NM_178739.6 | chrX:42139743-42143374 |
| 7909 | Dcaf12l2 | NM_175539.3 | chrX:41718633-41721514 |
| 7910 | Dcaf13 | NM_198606.2 | chr15:38944419-38978401 |
| 7911 | Dcaf15 | NM_172502.3 | chr8:86620970-86628661 |
| 7912 | Dcaf17 | NM_001165980.1 | chr2:70893800-70937199 |
| 7913 | Dcaf17 | NM_001165981.1 | chr2:70893800-70937199 |
| 7914 | Dcaf17 | NM_001165982.1 | chr2:70893800-70937199 |
| 7915 | Dcaf17 | NM_198005.2 | chr2:70893800-70937199 |
| 7916 | Dcaf4 | NM_001165256.1 | chr12:84861415-84882942 |
| 7917 | Dcaf4 | NM_030246.2 | chr12:84861415-84882942 |
| 7918 | Dcaf5 | NM_177267.3 | chr12:81436834-81537588 |
| 7919 | Dcaf6 | NM_028759.1 | chr1:167259631-167390594 |
| 7920 | Dcaf7 | NM_027946.3 | chr11:105898185-105920637 |
| 7921 | Dcaf8 | NM_153555.2 | chr1:174078145-174126524 |
| 7922 | Dcakd | NM_026551.3 | chr11:102855376-102878461 |
| 7923 | Dcbld1 | NM_025705.3 | chr10:51953424-52041183 |
| 7924 | Dcbld2 | NM_028523.3 | chr16:58408647-58469858 |
| 7925 | Dcc | NM_007831.3 | chr18:71413285-72510723 |
| 7926 | Dcdc2a | NM_001195617.1 | chr13:25147872-25302575 |
| 7927 | Dcdc2a | NM_177577.3 | chr13:25147872-25302575 |
| 7928 | Dcdc2b | NM_001195730.1 | chr4:129285574-129291501 |
| 7929 | Dcdc2c | NM_001177964.2 | chr12:29122669-29233202 |
| 7930 | Dchs1 | NM_001162943.1 | chr7:112901502-112936064 |
| 7931 | Dck | NM_007832.4 | chr5:89194037-89212302 |
| 7932 | Dclk1 | NM_001111051.1 | chr3:55046447-55342990 |
| 7933 | Dclk1 | NM_001111052.1 | chr3:55046447-55342990 |
| 7934 | Dclk1 | NM_001110053.1 | chr3:55046447-55342990 |
| 7935 | Dclk1 | NM_001195538.1 | chr3:55046447-55342990 |
| 7936 | Dclk1 | NM_001195539.1 | chr3:55046447-55342990 |
| 7937 | Dclk1 | NM_001195540.1 | chr3:55046447-55342990 |
| 7938 | Dclk1 | NM_019978.3 | chr3:55046447-55342990 |
| 7939 | Dclk2 | NM_001195496.1 | chr3:86590071-86724806 |
| 7940 | Dclk2 | NM_001195497.1 | chr3:86590071-86724806 |
| 7941 | Dclk2 | NM_001195498.1 | chr3:86590071-86724806 |
| 7942 | Dclk2 | NM_001195499.1 | chr3:86590071-86724806 |
| 7943 | Dclk2 | NM_001195500.1 | chr3:86590071-86724806 |
| 7944 | Dclk2 | NM_027539.5 | chr3:86590071-86724806 |
| 7945 | Dclk3 | NM_172928.5 | chr9:111341584-111392115 |
| 7946 | Dclre1b | NM_019831.4 | chr19:56603650-56622712 |
| 7947 | Dclre1b | NM_001025312.1 | chr3:103604527-103613310 |
| 7948 | Dclre1b | NM_133865.2 | chr3:103604527-103613310 |
| 7949 | Dclre1c | NM_001110214.1 | chr2:3341402-3392258 |
| 7950 | Dclre1c | NM_146114.3 | chr2:3341402-3392258 |
| 7951 | Dclre1c | NM_175683.4 | chr2:3341402-3392258 |
| 7952 | Dcn | NM_001190451.1 | chr10:96942133-96980796 |
| 7953 | Dcn | NM_007833.5 | chr10:96942133-96980796 |
| 7954 | Dcp1a | NM_133761.3 | chr14:31292751-31340242 |
| 7955 | Dcp1b | NM_001033379.3 | chr6:119125271-119171632 |
| 7956 | Dcp2 | NM_027490.1 | chr18:44540159-44584623 |
| 7957 | Dcpp1 | NM_199910.2 | chr17:24017842-24019820 |
| 7958 | Dcpp2 | NM_001039238.2 | chr17:24035688-24037754 |
| 7959 | Dcpp3 | NM_001077633.1 | chr17:24054424-24056408 |
| 7960 | Dcps | NM_027030.2 | chr9:34931999-34983572 |
| 7961 | Dcst1 | NM_029974.2 | chr3:89154156-89169161 |
| 7962 | Dcstamp | NM_001289506.1 | chr15:39577475-39592484 |
| 7963 | Dcstamp | NM_001289508.1 | chr15:39577475-39592484 |
| 7964 | Dcstamp | NM_001289512.1 | chr15:39577475-39592484 |
| 7965 | Dcstamp | NM_001289513.1 | chr15:39577475-39592484 |
| 7966 | Dcstamp | NM_029422.3 | chr15:39577475-39592484 |

Fig. 25 - 43

| | | | |
|---|---|---|---|
| 7967 | Dct | NM_010024.3 | chr14:118412011-118451468 |
| 7968 | Dctd | NM_001161515.1 | chr8:49184445-49227021 |
| 7969 | Dctd | NM_001161516.1 | chr8:49184445-49227021 |
| 7970 | Dctd | NM_178788.4 | chr8:49184445-49227021 |
| 7971 | Dctd | NR_027759.1 | chr8:49184445-49227021 |
| 7972 | Dctn1 | NM_001198866.1 | chr6:83115917-83150112 |
| 7973 | Dctn1 | NM_001198867.1 | chr6:83115917-83150112 |
| 7974 | Dctn1 | NM_007835.2 | chr6:83115917-83150112 |
| 7975 | Dctn2 | NM_001190453.1 | chr10:126703317-126725827 |
| 7976 | Dctn2 | NM_001190454.1 | chr10:126703317-126725827 |
| 7977 | Dctn2 | NM_027151.2 | chr10:126703317-126725827 |
| 7978 | Dctn3 | NM_001159565.1 | chr4:41661829-41670195 |
| 7979 | Dctn3 | NM_016890.4 | chr4:41661829-41670195 |
| 7980 | Dctn4 | NM_026302.3 | chr18:60685874-60718416 |
| 7981 | Dctn5 | NM_021608.3 | chr7:129276554-129292558 |
| 7982 | Dctn6 | NM_011722.2 | chr8:35153476-35171565 |
| 7983 | Dctpp1 | NM_023203.1 | chr7:134400475-134404181 |
| 7984 | Dcun1d1 | NM_001205361.1 | chr3:35791026-35831888 |
| 7985 | Dcun1d1 | NM_001205362.1 | chr3:35791026-35831888 |
| 7986 | Dcun1d1 | NM_033623.6 | chr3:35791026-35831888 |
| 7987 | Dcun1d2 | NM_001024504.2 | chr8:13255962-13322924 |
| 7988 | Dcun1d2 | NM_001042649.1 | chr8:13255962-13322924 |
| 7989 | Dcun1d2 | NM_001042650.1 | chr8:13255962-13322924 |
| 7990 | Dcun1d2 | NM_001042651.1 | chr8:13255962-13322924 |
| 7991 | Dcun1d3 | NM_001163703.1 | chr7:126996676-127039259 |
| 7992 | Dcun1d3 | NM_173408.3 | chr7:126996676-127039259 |
| 7993 | Dcun1d4 | NM_001190733.1 | chr5:73872293-73952033 |
| 7994 | Dcun1d4 | NM_001190734.1 | chr5:73872293-73952033 |
| 7995 | Dcun1d4 | NM_178896.5 | chr5:73872293-73952033 |
| 7996 | Dcun1d5 | NM_029775.2 | chr9:7184565-7207031 |
| 7997 | Dcx | NM_001110222.1 | chrX:140290384-140367762 |
| 7998 | Dcx | NM_001110223.1 | chrX:140290384-140367762 |
| 7999 | Dcx | NM_001110224.1 | chrX:140290384-140367762 |
| 8000 | Dcx | NM_010025.2 | chrX:140290384-140367762 |
| 8001 | Dcxr | NM_026428.2 | chr11:120586686-120588595 |
| 8002 | Dda1 | NM_025600.2 | chr8:73993093-73999996 |
| 8003 | Ddah1 | NM_026993.3 | chr3:145421655-145557241 |
| 8004 | Ddah2 | NM_001190449.1 | chr17:35195979-35199044 |
| 8005 | Ddah2 | NM_016765.3 | chr17:35195979-35199044 |
| 8006 | Ddb1 | NM_015735.1 | chr19:10680114-10704311 |
| 8007 | Ddb2 | NM_028119.5 | chr2:91051739-91077223 |
| 8008 | Ddc | NM_001190448.1 | chr11:11714103-11798147 |
| 8009 | Ddc | NM_016672.4 | chr11:11714103-11798147 |
| 8010 | Ddhd1 | NM_001039106.3 | chr14:46212845-46277818 |
| 8011 | Ddhd1 | NM_001042719.2 | chr14:46212845-46277818 |
| 8012 | Ddhd1 | NM_001284399.1 | chr14:46212845-46277818 |
| 8013 | Ddhd1 | NM_176845.5 | chr14:46212845-46277818 |
| 8014 | Ddhd2 | NM_022863.2 | chr8:26835795-26864752 |
| 8015 | Ddi1 | NM_027942.1 | chr9:6265028-6266947 |
| 8016 | Ddi2 | NM_001017966.2 | chr4:141239478-141279334 |
| 8017 | Ddit3 | NM_001290183.1 | chr10:126727848-126748842 |
| 8018 | Ddit3 | NM_007837.4 | chr10:126727848-126748842 |
| 8019 | Ddit4 | NM_029083.2 | chr10:59412422-59414518 |
| 8020 | Ddit4l | NM_030143.4 | chr3:137286635-137291296 |
| 8021 | Ddn | NM_001013741.1 | chr15:98634212-98638356 |
| 8022 | Ddo | NM_027442.5 | chr10:40349816-40369737 |
| 8023 | Ddost | NM_007838.2 | chr4:137860652-137868526 |
| 8024 | Ddr1 | NM_001198831.1 | chr17:35818511-35841084 |
| 8025 | Ddr1 | NM_001198833.1 | chr17:35818511-35841084 |
| 8026 | Ddr1 | NM_007584.2 | chr17:35818511-35841084 |
| 8027 | Ddr1 | NM_172962.1 | chr17:35818511-35841084 |
| 8028 | Ddr2 | NM_022563.2 | chr1:171902438-172019075 |
| 8029 | Ddrgk1 | NM_029832.2 | chr2:130479818-130490381 |
| 8030 | Ddt | NM_010027.1 | chr10:75233977-75236119 |
| 8031 | Ddx1 | NM_134040.1 | chr12:13226112-13255980 |
| 8032 | Ddx10 | NM_029936.1 | chr9:52906558-53056217 |
| 8033 | Ddx11 | NM_001003919.1 | chr17:66472859-66501508 |
| 8034 | Ddx17 | NM_001040187.1 | chr15:79346837-79377171 |
| 8035 | Ddx17 | NM_152806.3 | chr15:79346837-79377171 |
| 8036 | Ddx17 | NM_199079.2 | chr15:79346837-79377171 |
| 8037 | Ddx17 | NM_199080.2 | chr15:79346837-79377171 |
| 8038 | Ddx18 | NM_025860.3 | chr1:123450411-123464557 |
| 8039 | Ddx19a | NM_007916.2 | chr8:113498890-113521723 |
| 8040 | Ddx19b | NM_001190786.1 | chr8:113527085-113555651 |
| 8041 | Ddx19b | NM_001190800.1 | chr8:113527085-113555651 |
| 8042 | Ddx19b | NM_172843.3 | chr8:113527085-113555651 |
| 8043 | Ddx20 | NM_017397.3 | chr3:105481379-105490489 |
| 8044 | Ddx21 | NM_019553.2 | chr10:62042994-62065046 |
| 8045 | Ddx23 | NM_001080981.1 | chr15:98475937-98493320 |
| 8046 | Ddx24 | NM_001159502.1 | chr12:104646185-104664077 |
| 8047 | Ddx24 | NM_020494.3 | chr12:104646185-104664077 |
| 8048 | Ddx25 | NM_013932.4 | chr9:35349432-35366055 |
| 8049 | Ddx26b | NM_172779.4 | chrX:53708015-53761020 |
| 8050 | Ddx27 | NM_153065.3 | chr2:166840812-166860445 |
| 8051 | Ddx28 | NM_028038.3 | chr8:108535515-108535386 |
| 8052 | Ddx31 | NM_001033294.3 | chr2:28695925-28761095 |
| 8053 | Ddx39 | NM_197982.3 | chr8:86239076-86247250 |
| 8054 | Ddx39b | NM_001252457.1 | chr17:35378690-35390652 |
| 8055 | Ddx39b | NM_019693.3 | chr17:35378690-35390652 |
| 8056 | Ddx3x | NM_010028.3 | chrX:12858147-12871109 |
| 8057 | Ddx3y | NM_012008.2 | chrY:597157-623056 |
| 8058 | Ddx4 | NM_001145885.1 | chr13:113388540-113442518 |
| 8059 | Ddx4 | NM_010029.2 | chr13:113388540-113442518 |
| 8060 | Ddx41 | NM_134059.2 | chr13:55631770-55638019 |
| 8061 | Ddx42 | NM_028074.4 | chr11:106078239-106110454 |
| 8062 | Ddx43 | NM_001191044.1 | chr9:78243583-78271396 |
| 8063 | Ddx46 | NM_001282055.1 | chr13:55736359-55782628 |
| 8064 | Ddx47 | NM_026360.3 | chr6:134961629-134973794 |
| 8065 | Ddx49 | NM_001024922.2 | chr8:72816765-72826351 |
| 8066 | Ddx5 | NM_007840.3 | chr11:106641670-106649808 |
| 8067 | Ddx50 | NM_053183.2 | chr10:62078770-62113946 |
| 8068 | Ddx51 | NM_027156.3 | chr5:111082469-111089515 |
| 8069 | Ddx52 | NM_030096.2 | chr11:83755591-83776588 |
| 8070 | Ddx54 | NM_028041.2 | chr5:121063139-121078601 |
| 8071 | Ddx55 | NM_001190795.1 | chr5:125002872-125019669 |
| 8072 | Ddx55 | NM_026409.4 | chr5:125002872-125019669 |
| 8073 | Ddx56 | NM_026538.3 | chr11:6157547-6167732 |
| 8074 | Ddx58 | NM_172689.3 | chr4:40150869-40186858 |
| 8075 | Ddx59 | NM_026500.3 | chr1:138311848-138336797 |
| 8076 | Ddx6 | NM_001110826.1 | chr9:44412974-44448814 |
| 8077 | Ddx6 | NM_007841.4 | chr9:44412974-44448814 |
| 8078 | Ddx6 | NM_181324.3 | chr9:44412974-44448814 |
| 8079 | Ddx60 | NM_001081215.1 | chr8:64406885-64516492 |
| 8080 | Deaf1 | NM_001282072.1 | chr7:148483074-148524682 |
| 8081 | Deaf1 | NM_001282073.1 | chr7:148483074-148524682 |
| 8082 | Deaf1 | NM_001282076.1 | chr7:148483074-148524682 |
| 8083 | Deaf1 | NM_016874.3 | chr7:148483074-148524682 |
| 8084 | Dear1 | NM_001040461.2 | chr3:84768978-84769502 |
| 8085 | Deb1 | NM_026794.2 | chr9:121619506-121622039 |
| 8086 | Decr1 | NM_026172.3 | chr4:15844387-15872654 |
| 8087 | Decr2 | NM_011933.2 | chr17:26218155-26227109 |
| 8088 | Dedd | NM_001128609.1 | chr1:173259275-173275776 |
| 8089 | Dedd | NM_011615.3 | chr1:173259275-173275776 |
| 8090 | Dedd2 | NM_207677.3 | chr7:25987859-26004878 |
| 8091 | Def6 | NM_027185.3 | chr17:28344722-28365553 |
| 8092 | Def8 | NM_001253783.1 | chr8:125966855-125987799 |
| 8093 | Def8 | NM_001253784.1 | chr8:125966855-125987799 |
| 8094 | Def8 | NM_001281803.1 | chr8:125966855-125987799 |
| 8095 | Def8 | NM_054046.5 | chr8:125966855-125987799 |
| 8096 | Defa17 | NM_001167790.1 | chr8:22766238-22767208 |
| 8097 | Defa2 | NM_001195634.2 | chr8:22619730-22620708 |
| 8098 | Defa20 | NM_183268.1 | chr8:22619730-22620709 |
| 8099 | Defa21 | NM_183253.2 | chr8:22165223-22166196 |
| 8100 | Defa22 | NM_207658.4 | chr8:22301955-22302928 |
| 8101 | Defa23 | NM_001012307.2 | chr8:22194718-22195696 |
| 8102 | Defa23 | NM_001012307.2 | chr8:22331251-22332229 |
| 8103 | Defa24 | NM_001024225.2 | chr8:22844966-22845943 |
| 8104 | Defa25 | NM_007849.1 | chr8:22224120-22224964 |
| 8105 | Defa26 | NM_001079933.2 | chr8:22728639-22729444 |
| 8106 | Defa3 | NM_007850.2 | chr8:22427087-22428056 |
| 8107 | Defa4 | NM_010039.2 | chr8:22371749-22371912 |
| 8108 | Defa5 | NM_007851.2 | chr8:22437072-22438054 |
| 8109 | Defa6 | NM_007852.1 | chr8:22845009-22845849 |
| 8110 | Defa-ps1 | NR_003146.1 | chr8:22805483-22806325 |
| 8111 | Defa-ps12 | NR_002878.2 | chr8:19210461-19212760 |
| 8112 | Defa-ps13 | NR_002881.2 | chr8:19300676-19304794 |
| 8113 | Defa-rs1 | NM_007844.2 | chr8:22465566-22466699 |
| 8114 | Defa-rs7 | NM_007848.2 | chr8:22194718-22195696 |
| 8115 | Defa-rs7 | NM_007848.2 | chr8:22331251-22332229 |
| 8116 | Defb1 | NM_007843.3 | chr8:22887026-22905657 |
| 8117 | Defb10 | NM_139225.2 | chr8:22969372-22972482 |
| 8118 | Defb11 | NM_139221.2 | chr8:23015845-23016904 |
| 8119 | Defb12 | NM_152802.3 | chr8:19113930-19114833 |
| 8120 | Defb13 | NM_139223.3 | chr8:23057233-23059094 |
| 8121 | Defb14 | NM_183026.2 | chr8:19194327-19195309 |
| 8122 | Defb15 | NM_139222.3 | chr8:23040264-23043182 |
| 8123 | Defb18 | NM_001039123.1 | chr1:18226553-18227524 |
| 8124 | Defb19 | NM_145157.3 | chr2:152401821-152406048 |
| 8125 | Defb2 | NM_010030.1 | chr8:22950397-22953953 |
| 8126 | Defb20 | NM_176950.3 | chr2:152302798-152305670 |
| 8127 | Defb21 | NM_207276.2 | chr2:152398479-152400679 |
| 8128 | Defb22 | NM_001002791.2 | chr2:152311401-152315874 |
| 8129 | Defb23 | NM_001037933.2 | chr2:152284790-152290356 |
| 8130 | Defb25 | NM_001039122.1 | chr2:152448091-152448789 |
| 8131 | Defb26 | NM_001039120.2 | chr2:152333491-152337472 |
| 8132 | Defb28 | NM_001037502.2 | chr2:152343990-152347183 |
| 8133 | Defb29 | NM_001001444.2 | chr2:152366449-152365777 |
| 8134 | Defb3 | NM_013756.2 | chr8:19293360-19295339 |
| 8135 | Defb30 | NM_001039566.2 | chr14:63652923-63656683 |
| 8136 | Defb33 | NM_001039119.2 | chr_random:311631-316688 |
| 8137 | Defb34 | NM_139035.1 | chr8:19123751-19126540 |
| 8138 | Defb35 | NM_139224.1 | chr8:23048823-23051350 |
| 8139 | Defb36 | NM_001037247.4 | chr2:152430062-152438465 |
| 8140 | Defb37 | NM_181683.2 | chr8:18986232-18991055 |
| 8141 | Defb38 | NM_183036.1 | chr8:19023463-19026529 |
| 8142 | Defb39 | NM_183038.2 | chr8:19052825-19064810 |
| 8143 | Defb4 | NM_019728.4 | chr8:19198703-19201547 |
| 8144 | Defb40 | NM_183039.3 | chr8:18974939-18978116 |
| 8145 | Defb41 | NM_183124.3 | chr1:18241059-18255219 |
| 8146 | Defb42 | NM_001034910.3 | chr14:63665827-63667443 |
| 8147 | Defb43 | NM_001039121.3 | chr14:63630607-63636925 |
| 8148 | Defb44-ps | NR_002879.2 | chr1:18200133-18213645 |
| 8149 | Defb45 | NM_001037752.1 | chr2:152418926-152422221 |
| 8150 | Defb46 | NM_001025351.1 | chr8:19239915-19242143 |
| 8151 | Defb47 | NM_001039125.2 | chr14:63616913-63619997 |
| 8152 | Defb48 | NM_001037751.3 | chr14:63596360-63603347 |
| 8153 | Defb5 | NM_030734.2 | chr8:19247591-19250828 |
| 8154 | Defb50 | NM_199067.1 | chr8:22934010-22941768 |
| 8155 | Defb6 | NM_054074.1 | chr8:19225477-19228209 |
| 8156 | Defb7 | NM_139220.1 | chr8:19495096-19497775 |

Fig. 25 - 44

| | | | |
|---|---|---|---|
| 8157 | Defb8 | NM_153108.4 | chr8:19445769-19447606 |
| 8158 | Defb9 | NM_139219.2 | chr8:22992184-22995906 |
| 8159 | Degs1 | NM_007853.4 | chr1:184205900-184212890 |
| 8160 | Degs2 | NM_001171002.1 | chr12:109609362-109940516 |
| 8161 | Degs2 | NM_027299.5 | chr12:109609362-109940516 |
| 8162 | Dek | NM_025900.2 | chr13:47180136-47201589 |
| 8163 | Dennd1a | NM_146122.3 | chr2:37654510-38142904 |
| 8164 | Dennd1b | NM_001166501.1 | chr1:140860285-141072619 |
| 8165 | Dennd1b | NM_181347.3 | chr1:140860285-141072619 |
| 8166 | Dennd1c | NM_153551.1 | chr17:57205477-57217933 |
| 8167 | Dennd2a | NM_172477.4 | chr6:39412376-39507833 |
| 8168 | Dennd2c | NM_177857.1 | chr3:102931478-102973656 |
| 8169 | Dennd2d | NM_001093754.2 | chr3:106284903-106350679 |
| 8170 | Dennd2d | NM_001278941.1 | chr3:106284903-106350679 |
| 8171 | Dennd2d | NM_028110.2 | chr3:106284903-106350679 |
| 8172 | Dennd3 | NM_001081066.1 | chr15:73342989-73402672 |
| 8173 | Dennd4a | NM_001134465.2 | chr9:64658817-64767474 |
| 8174 | Dennd4b | NM_201407.4 | chr3:90070436-90084587 |
| 8175 | Dennd4c | NM_184088.1 | chr4:86394458-86496506 |
| 8176 | Dennd5a | NM_021494.1 | chr7:117037294-117103936 |
| 8177 | Dennd5b | NM_177192.3 | chr6:148936590-149050202 |
| 8178 | Dennd6a | NM_001134465.2 | chr14:27393343-27453808 |
| 8179 | Dennd6a | NM_001285466.1 | chr14:27393343-27453808 |
| 8180 | Dennd6a | NM_001285467.1 | chr14:27393343-27453808 |
| 8181 | Dennd6a | NM_145969.4 | chr14:27393343-27453808 |
| 8182 | Dennd6b | NM_027081.3 | chr15:89012643-89026905 |
| 8183 | Denr | NM_026603.4 | chr5:124357283-124378841 |
| 8184 | Depdc1a | NM_001172092.1 | chr3:159158396-159192919 |
| 8185 | Depdc1a | NM_001172093.1 | chr3:159158396-159192919 |
| 8186 | Depdc1a | NM_029523.3 | chr3:159158396-159192919 |
| 8187 | Depdc1b | NM_178683.4 | chr3:109106530-109179751 |
| 8188 | Depdc5 | NM_001025426.2 | chr5:33206369-33336882 |
| 8189 | Depdc5 | NM_001170567.1 | chr5:33206369-33336882 |
| 8190 | Depdc5 | NM_177786.4 | chr5:33206369-33336882 |
| 8191 | Depdc7 | NM_144804.1 | chr2:104561943-104582958 |
| 8192 | Deptor | NM_001037937.3 | chr15:54931471-55090828 |
| 8193 | Deptor | NM_145470.3 | chr15:54931471-55090828 |
| 8194 | Dera | NM_172733.1 | chr6:137703097-137786393 |
| 8195 | Derl1 | NM_024207.4 | chr15:57701056-57723973 |
| 8196 | Derl2 | NM_001291146.1 | chr11:70820941-70840636 |
| 8197 | Derl2 | NM_001291147.1 | chr11:70820941-70840636 |
| 8198 | Derl2 | NM_001291148.1 | chr11:70820941-70840636 |
| 8199 | Derl2 | NM_033562.4 | chr11:70820941-70840636 |
| 8200 | Derl3 | NM_024440.2 | chr10:75356142-75358686 |
| 8201 | Des | NM_010043.2 | chr1:75356867-75365154 |
| 8202 | Desi1 | NM_134095.2 | chr15:81822952-81846570 |
| 8203 | Desi2 | NM_024282.3 | chr1:180117547-180182728 |
| 8204 | Det1 | NM_029585.3 | chr7:85972359-85992097 |
| 8205 | Dexi | NM_021428.4 | chr16:10530299-10543147 |
| 8206 | Dffa | NM_001025296.2 | chr4:148478250-148494762 |
| 8207 | Dffa | NM_010044.3 | chr4:148478250-148494762 |
| 8208 | Dffa | NR_104263.1 | chr4:148478250-148494762 |
| 8209 | Dffb | NM_007859.3 | chr4:153338557-153349190 |
| 8210 | Dfna5 | NM_018769.3 | chr6:50157401-50211768 |
| 8211 | Dfnb59 | NM_001080711.2 | chr2:76488329-76496611 |
| 8212 | Dgat1 | NM_010046.2 | chr15:76332444-76342248 |
| 8213 | Dgat2 | NM_026384.3 | chr7:106301172-106331223 |
| 8214 | Dgat2l6 | NM_001114084.1 | chrX:97720176-97741447 |
| 8215 | Dgcr14 | NM_001081633.1 | chr16:17900801-17911441 |
| 8216 | Dgcr14 | NM_022408.2 | chr16:17900801-17911441 |
| 8217 | Dgcr2 | NM_001109750.1 | chr16:17840450-17891823 |
| 8218 | Dgcr2 | NM_010048.3 | chr16:17840450-17891823 |
| 8219 | Dgcr6 | NM_001289813.1 | chr16:18052952-18071725 |
| 8220 | Dgcr6 | NM_001289814.1 | chr16:18052952-18071725 |
| 8221 | Dgcr6 | NM_010047.4 | chr16:18052952-18071725 |
| 8222 | Dgcr6 | NR_110380.1 | chr16:18052952-18071725 |
| 8223 | Dgcr8 | NM_033324.2 | chr16:18254058-18289261 |
| 8224 | Dgka | NM_016811.2 | chr10:128157192-128181112 |
| 8225 | Dgkb | NM_178681.4 | chr12:38607292-39359997 |
| 8226 | Dgkd | NM_177646.3 | chr1:89749861-89841064 |
| 8227 | Dgke | NM_019505.3 | chr11:88898895-88922062 |
| 8228 | Dgkeos | NR_110336.1 | chr11:88922064-88929198 |
| 8229 | Dgkg | NM_138650.2 | chr16:22466642-22657304 |
| 8230 | Dgkh | NM_001081336.1 | chr14:78969415-79124896 |
| 8231 | Dgkh | NM_001253766.1 | chr14:78969415-79124896 |
| 8232 | Dgkh | NM_001281794.1 | chr14:78969415-79124896 |
| 8233 | Dgkh | NR_104044.1 | chr14:78969415-79124896 |
| 8234 | Dgki | NM_001081206.1 | chr6:36796021-37249976 |
| 8235 | Dgkk | NM_177914.3 | chrX:6356431-6525489 |
| 8236 | Dgkq | NM_199011.1 | chr5:109076063-109089788 |
| 8237 | Dgkz | NM_001166597.1 | chr2:91772978-91803720 |
| 8238 | Dgkz | NM_138306.2 | chr2:91772978-91803720 |
| 8239 | Dguok | NM_001162521.1 | chr6:83430207-83456963 |
| 8240 | Dguok | NM_013764.2 | chr6:83430207-83456963 |
| 8241 | Dhcr24 | NM_053272.2 | chr4:106233642-106261718 |
| 8242 | Dhcr7 | NM_007856.2 | chr7:151009071-151034315 |
| 8243 | Dhdds | NM_026144.4 | chr4:133524971-133556779 |
| 8244 | Dhdh | NM_027903.3 | chr7:52728933-52744166 |
| 8245 | Dhfr | NM_010049.3 | chr13:93124738-93159008 |
| 8246 | Dhh | NM_007829.3 | chr15:98723457-98728971 |
| 8247 | Dhodh | NM_020046.3 | chr8:112117147-112132573 |
| 8248 | Dhps | NM_001039514.1 | chr8:87595656-87599060 |
| 8249 | Dhrs1 | NM_026819.3 | chr14:56357856-56364521 |
| 8250 | Dhrs11 | NM_177564.5 | chr11:84634229-84642505 |
| 8251 | Dhrs13 | NM_183286.2 | chr11:77851814-77851366 |
| 8252 | Dhrs2 | NM_027790.2 | chr14:55840843-55860277 |
| 8253 | Dhrs3 | NM_001172424.1 | chr4:144482729-144517548 |
| 8254 | Dhrs3 | NM_011303.6 | chr4:144482729-144517548 |
| 8255 | Dhrs4 | NM_001037938.2 | chr14:56097594-56109177 |
| 8256 | Dhrs4 | NM_030686.2 | chr14:56097594-56109177 |
| 8257 | Dhrs7 | NM_025522.5 | chr12:73751339-73765815 |
| 8258 | Dhrs7b | NM_001172112.1 | chr11:60644132-60671925 |
| 8259 | Dhrs7b | NM_145428.2 | chr11:60644132-60671925 |
| 8260 | Dhrs7c | NM_001013013.2 | chr11:67611772-67629504 |
| 8261 | Dhrs9 | NM_175512.2 | chr2:69218518-69241143 |
| 8262 | Dhrsx | NM_001033326.2 | chr4_random:109801-130134 |
| 8263 | Dhtkd1 | NM_001081131.2 | chr2:5819105-5863838 |
| 8264 | Dhx15 | NM_001042620.2 | chr5:52541441-52581785 |
| 8265 | Dhx15 | NM_007839.3 | chr5:52541441-52581785 |
| 8266 | Dhx15 | NR_104311.1 | chr5:52541441-52581785 |
| 8267 | Dhx16 | NM_026987.2 | chr17:36016722-36029613 |
| 8268 | Dhx29 | NM_172594.2 | chr13:113718000-113759395 |
| 8269 | Dhx30 | NM_001252682.1 | chr9:109986822-110020120 |
| 8270 | Dhx30 | NM_001252683.1 | chr9:109986822-110020120 |
| 8271 | Dhx30 | NM_133347.2 | chr9:109986822-110020120 |
| 8272 | Dhx32 | NM_001286030.1 | chr7:140901015-141073215 |
| 8273 | Dhx32 | NM_001286031.1 | chr7:140901015-141073215 |
| 8274 | Dhx32 | NM_001286032.1 | chr7:140901015-141073215 |
| 8275 | Dhx32 | NM_133941.2 | chr7:140901015-141073215 |
| 8276 | Dhx33 | NM_178367.4 | chr11:70797592-70817934 |
| 8277 | Dhx34 | NM_001285931.1 | chr7:16782569-16807381 |
| 8278 | Dhx34 | NM_001285932.1 | chr7:16782569-16807381 |
| 8279 | Dhx34 | NM_027883.3 | chr7:16782569-16807381 |
| 8280 | Dhx35 | NM_001291144.1 | chr2:158620542-158683956 |
| 8281 | Dhx35 | NM_145742.2 | chr2:158620542-158683956 |
| 8282 | Dhx36 | NM_028136.2 | chr3:62272563-62310910 |
| 8283 | Dhx37 | NM_203319.1 | chr5:125894773-125914418 |
| 8284 | Dhx38 | NM_178380.1 | chr8:112071923-112089501 |
| 8285 | Dhx40 | NM_026191.2 | chr11:86582350-86621162 |
| 8286 | Dhx57 | NM_001163759.1 | chr17:80637643-80696816 |
| 8287 | Dhx57 | NM_198942.2 | chr17:80637643-80696816 |
| 8288 | Dhx58 | NM_030150.2 | chr11:100556197-100565585 |
| 8289 | Dhx8 | NM_144831.2 | chr11:101594269-101628671 |
| 8290 | Dhx9 | NM_007842.2 | chr1:155302887-155334790 |
| 8291 | Diablo | NM_023232.3 | chr5:123961339-123974173 |
| 8292 | Diap1 | NM_007858.3 | chr18:38003255-38095077 |
| 8293 | Diap2 | NM_172493.2 | chrX:126284277-127000369 |
| 8294 | Diap3 | NM_019670.1 | chr14:87056129-87540921 |
| 8295 | Dicer1 | NM_148948.2 | chr12:105925951-105990162 |
| 8296 | Dido1 | NM_001291432.1 | chr2:180392667-180444704 |
| 8297 | Dido1 | NM_001291433.1 | chr2:180392667-180444704 |
| 8298 | Dido1 | NM_011805.3 | chr2:180392667-180444704 |
| 8299 | Dido1 | NM_175551.4 | chr2:180392667-180444704 |
| 8300 | Dido1 | NM_177852.1 | chr2:180392667-180444704 |
| 8301 | Dido1 | NR_111965.1 | chr2:180392667-180444704 |
| 8302 | Diexf | NM_145415.2 | chr1:194930596-194956445 |
| 8303 | Dimt1 | NM_025447.4 | chr13:107737208-107750304 |
| 8304 | Dio1 | NM_007860.3 | chr4:106964069-106979748 |
| 8305 | Dio2 | NM_010050.2 | chr12:91962991-91976878 |
| 8306 | Dio3 | NM_172119.2 | chr12:111517439-111519307 |
| 8307 | Dio3os | NR_002866.2 | chr12:111513595-111516278 |
| 8308 | Dip2a | NM_001081419.2 | chr10:75725793-75808036 |
| 8309 | Dip2b | NM_001159361.1 | chr15:99869094-100049904 |
| 8310 | Dip2b | NM_172819.3 | chr15:99869094-100049904 |
| 8311 | Dip2c | NM_001081426.2 | chr13:9275770-9668172 |
| 8312 | Diras1 | NM_145217.2 | chr10:80482334-80488122 |
| 8313 | Diras2 | NM_001024474.2 | chr13:52599743-52626205 |
| 8314 | Dirc2 | NM_153550.3 | chr16:35694988-35769442 |
| 8315 | Dis3 | NM_028315.2 | chr14:99478593-99498989 |
| 8316 | Dis3l | NM_001001295.2 | chr9:64154562-64189064 |
| 8317 | Dis3l | NM_001177784.1 | chr9:64154562-64189064 |
| 8318 | Dis3l | NM_172519.3 | chr9:64154562-64189064 |
| 8319 | Dis3l2 | NM_001172157.1 | chr1:88600378-88946672 |
| 8320 | Dis3l2 | NM_153530.2 | chr1:88600378-88946672 |
| 8321 | Disc1 | NM_174853.2 | chr8:127578094-127785051 |
| 8322 | Disc1 | NM_174854.2 | chr8:127578094-127785051 |
| 8323 | Disp1 | NM_001278218.1 | chr1_random:48173-185338 |
| 8324 | Disp1 | NM_001278219.1 | chr1_random:48173-185338 |
| 8325 | Disp1 | NM_001278220.1 | chr1_random:48173-185338 |
| 8326 | Disp1 | NM_026866.3 | chr1_random:48173-185338 |
| 8327 | Disp2 | NM_170593.3 | chr2:118605454-118620911 |
| 8328 | Dixdc1 | NM_178118.2 | chr9:50470857-50536089 |
| 8329 | Dkc1 | NM_001030307.2 | chrX:72341193-72355115 |
| 8330 | Dkk1 | NM_010051.3 | chr19:30620373-30623986 |
| 8331 | Dkk2 | NM_020265.4 | chr3:131748255-131843268 |
| 8332 | Dkk3 | NM_015814.2 | chr7:119259532-119302571 |
| 8333 | Dkk4 | NM_145592.2 | chr8:23734514-23738018 |
| 8334 | Dkkl1 | NM_015789.3 | chr7:52462894-52467253 |
| 8335 | Dlat | NM_145614.4 | chr9:50442737-50467485 |
| 8336 | Dlc1 | NM_001194940.2 | chr8:37630792-38015496 |
| 8337 | Dlc1 | NM_001194941.1 | chr8:37630792-38015496 |
| 8338 | Dlc1 | NM_015802.3 | chr8:37630792-38015496 |
| 8339 | Dld | NM_007861.5 | chr12:32016426-32036336 |
| 8340 | Dlec1 | NM_177117.3 | chr9:119011595-119056812 |
| 8341 | Dleu2 | NR_028264.1 | chr14:62221673-62301210 |
| 8342 | Dleu7 | NM_173419.2 | chr14:62895065-62911816 |
| 8343 | Dlg1 | NM_001252433.1 | chr16:31663528-31873442 |
| 8344 | Dlg1 | NM_001252434.1 | chr16:31663528-31873442 |
| 8345 | Dlg1 | NM_001252435.1 | chr16:31663528-31873442 |
| 8346 | Dlg1 | NM_001252436.1 | chr16:31663528-31873442 |

Fig. 25 - 45

| | | | | | | | | |
|---|---|---|---|---|---|---|---|---|
| 8347 | Dlg1 | NM_007862.3 | chr16:31663528-31873442 | | 8442 | Dnaaf3 | NM_001033548.2 | chr7:4474558-4484044 |
| 8348 | Dlg1 | NR_045516.1 | chr16:31663528-31873442 | | 8443 | Dnah1 | NM_001033668.1 | chr14:32073560-32137082 |
| 8349 | Dlg2 | NM_001243046.1 | chr7:98239295-99597756 | | 8444 | Dnah10 | NM_019536.1 | chr5:125205454-125314678 |
| 8350 | Dlg2 | NM_001243047.1 | chr7:98239295-99597756 | | 8445 | Dnah11 | NM_010060.3 | chr12:119116455-119437516 |
| 8351 | Dlg2 | NM_011807.3 | chr7:98239295-99597756 | | 8446 | Dnah17 | NM_001167746.1 | chr11:117883037-117990533 |
| 8352 | Dlg3 | NM_001177778.1 | chrX:97963060-98013749 | | 8447 | Dnah2 | NM_001081330.1 | chr11:69234310-69362610 |
| 8353 | Dlg3 | NM_001177779.1 | chrX:97963060-98013749 | | 8448 | Dnah5 | NM_133365.3 | chr15:28133520-28401800 |
| 8354 | Dlg3 | NM_001177780.1 | chrX:97963060-98013749 | | 8449 | Dnah6 | NM_001164669.1 | chr6:72967600-73171625 |
| 8355 | Dlg3 | NM_001290402.1 | chrX:97963060-98013749 | | 8450 | Dnah7a | NM_001252070.1 | chr1:53453845-53763628 |
| 8356 | Dlg3 | NM_016747.4 | chrX:97963060-98013749 | | 8451 | Dnah7b | NM_001160386.1 | chr1:46123582-46430395 |
| 8357 | Dlg4 | NM_001109752.1 | chr11:69832106-69859033 | | 8452 | Dnah8 | NM_013811.3 | chr17:30763880-31012209 |
| 8358 | Dlg4 | NM_007864.3 | chr11:69832106-69859033 | | 8453 | Dnah9 | NM_001099633.1 | chr11:65644825-65982053 |
| 8359 | Dlg5 | NM_001163513.1 | chr14:24953174-25065142 | | 8454 | Dnaic1 | NM_175138.4 | chr4:41516827-41585191 |
| 8360 | Dlg5 | NM_027726.3 | chr14:24953174-25065142 | | 8455 | Dnaic2 | NM_001034878.2 | chr11:114548725-114619200 |
| 8361 | Dlgap1 | NM_001128180.1 | chr17:70774131-71170753 | | 8456 | Dnaja1 | NM_001164671.1 | chr4:40667186-40704918 |
| 8362 | Dlgap1 | NM_001128181.1 | chr17:70774131-71170753 | | 8457 | Dnaja1 | NM_001164672.1 | chr4:40667186-40704918 |
| 8363 | Dlgap1 | NM_027712.3 | chr17:70774131-71170753 | | 8458 | Dnaja1 | NM_008298.5 | chr4:40667186-40704918 |
| 8364 | Dlgap1 | NM_177539.6 | chr17:70774131-71170753 | | 8459 | Dnaja2 | NM_019794.3 | chr8:88061538-88079170 |
| 8365 | Dlgap2 | NM_001145065.1 | chr8:14095874-14847686 | | 8460 | Dnaja3 | NM_001135112.1 | chr16:4684069-4707693 |
| 8366 | Dlgap2 | NM_172910.3 | chr8:14095874-14847686 | | 8461 | Dnaja3 | NM_023646.4 | chr16:4684069-4707693 |
| 8367 | Dlgap3 | NM_198618.5 | chr4:126846514-126914266 | | 8462 | Dnaja4 | NM_021422.3 | chr9:54547366-54564124 |
| 8368 | Dlgap4 | NM_001042487.1 | chr2:156439432-156590099 | | 8463 | Dnajb1 | NM_018808.3 | chr8:86132073-86135802 |
| 8369 | Dlgap4 | NM_001042488.2 | chr2:156439432-156590099 | | 8464 | Dnajb11 | NM_001190804.1 | chr16:22857917-22899524 |
| 8370 | Dlgap4 | NM_001277186.1 | chr2:156439432-156590099 | | 8465 | Dnajb11 | NM_001190805.1 | chr16:22857917-22899524 |
| 8371 | Dlgap4 | NM_001277187.1 | chr2:156439432-156590099 | | 8466 | Dnajb11 | NM_026400.5 | chr16:22857917-22899524 |
| 8372 | Dlgap4 | NM_146128.6 | chr2:156439432-156590099 | | 8467 | Dnajb12 | NM_019965.2 | chr10:59342338-59360764 |
| 8373 | Dlgap5 | NM_144553.2 | chr14:48007453-48038082 | | 8468 | Dnajb13 | NM_153527.2 | chr7:107651528-107663324 |
| 8374 | Dlk1 | NM_001190703.1 | chr12:110691032-110701546 | | 8469 | Dnajb14 | NM_001033155.1 | chr3:137530638-137571895 |
| 8375 | Dlk1 | NM_001190704.1 | chr12:110691032-110701546 | | 8470 | Dnajb2 | NM_001159883.1 | chr1:75232997-75242267 |
| 8376 | Dlk1 | NM_001190705.1 | chr12:110691032-110701546 | | 8471 | Dnajb2 | NM_001159884.1 | chr1:75232997-75242267 |
| 8377 | Dlk1 | NM_010052.5 | chr12:110691032-110701546 | | 8472 | Dnajb2 | NM_001159885.1 | chr1:75232997-75242267 |
| 8378 | Dlk1 | NR_033813.1 | chr12:110691032-110701546 | | 8473 | Dnajb2 | NM_020266.2 | chr1:75232997-75242267 |
| 8379 | Dlk2 | NM_001286013.1 | chr17:46434431-46464972 | | 8474 | Dnajb2 | NM_178055.4 | chr1:75232997-75242267 |
| 8380 | Dlk2 | NM_001286028.1 | chr17:46434431-46464972 | | 8475 | Dnajb3 | NM_008299.3 | chr1:90101807-90102323 |
| 8381 | Dll1 | NM_007865.3 | chr17:15504317-15512787 | | 8476 | Dnajb4 | NM_025926.4 | chr3:151846834-151873047 |
| 8382 | Dll3 | NM_007866.2 | chr7:29078573-29086804 | | 8477 | Dnajb4 | NM_027287.4 | chr3:151846834-151873047 |
| 8383 | Dll4 | NM_019454.3 | chr2:119151520-119161402 | | 8478 | Dnajb5 | NM_019874.3 | chr4:42965965-42971604 |
| 8384 | Dlst | NM_030225.4 | chr12:86451782-86475041 | | 8479 | Dnajb6 | NM_001037940.4 | chr5:30061873-30113018 |
| 8385 | Dlx1 | NM_010053.1 | chr2:71367502-71372037 | | 8480 | Dnajb6 | NM_001037941.3 | chr5:30061873-30113018 |
| 8386 | Dlx1as | NR_002854.2 | chr2:71368695-71375948 | | 8481 | Dnajb6 | NM_001127367.1 | chr5:30061873-30113018 |
| 8387 | Dlx2 | NM_010054.2 | chr2:71381464-71384811 | | 8482 | Dnajb6 | NM_011847.4 | chr5:30061873-30113018 |
| 8388 | Dlx3 | NM_010055.3 | chr11:94981430-94986605 | | 8483 | Dnajb7 | NM_021317.2 | chr15:81237518-81238703 |
| 8389 | Dlx4 | NM_007867.4 | chr11:95001761-95007115 | | 8484 | Dnajb8 | NM_019964.1 | chr6:88172261-88173250 |
| 8390 | Dlx5 | NM_010056.3 | chr6:6827800-6832068 | | 8485 | Dnajb9 | NM_013760.4 | chr12:45306883-45311055 |
| 8391 | Dlx5 | NM_198654.2 | chr6:6827800-6832068 | | 8486 | Dnajc1 | NM_001190817.1 | chr2:17976863-18314457 |
| 8392 | Dlx6 | NM_010057.2 | chr6:6813334-6817970 | | 8487 | Dnajc1 | NM_007869.3 | chr2:17976863-18314457 |
| 8393 | Dlx6as2 | NR_002839.2 | chr6:6813797-6815150 | | 8488 | Dnajc10 | NM_024181.2 | chr2:80155622-80194212 |
| 8394 | Dlx6os1 | NR_015388.1 | chr6:6770546-6819533 | | 8489 | Dnajc11 | NM_172704.3 | chr4:151307828-151356068 |
| 8395 | Dmap1 | NM_023178.2 | chr4:117347290-117354830 | | 8490 | Dnajc12 | NM_001253685.1 | chr10:62845190-62871588 |
| 8396 | Dmbt1 | NM_007769.2 | chr7:138175589-138265142 | | 8491 | Dnajc12 | NM_013888.3 | chr10:62845190-62871588 |
| 8397 | Dmbx1 | NM_001025567.1 | chr4:115587723-115612531 | | 8492 | Dnajc13 | NM_001163026.1 | chr9:104053926-104165260 |
| 8398 | Dmbx1 | NM_130865.2 | chr4:115587723-115612531 | | 8493 | Dnajc14 | NM_028873.4 | chr10:128242732-128256502 |
| 8399 | Dmc1 | NM_010057.2 | chr15:79391927-79435539 | | 8494 | Dnajc15 | NM_025384.3 | chr14:78226023-78274724 |
| 8400 | Dmc1 | NM_010059.3 | chr15:79391927-79435539 | | 8495 | Dnajc16 | NM_172338.2 | chr4:141317912-141346559 |
| 8401 | Dmc1 | NR_103477.1 | chr15:79391927-79435539 | | 8496 | Dnajc17 | NM_139139.2 | chr2:118998236-119034531 |
| 8402 | Dmd | NM_007868.5 | chrX:80194209-82450389 | | 8497 | Dnajc18 | NM_029669.4 | chr18:35830758-35862798 |
| 8403 | Dmgdh | NM_028772.3 | chr13:94444391-94522778 | | 8498 | Dnajc19 | NM_001026211.2 | chr3:33919000-33980276 |
| 8404 | Dmkn | NM_001166173.1 | chr7:31548774-31566085 | | 8499 | Dnajc19 | NM_001286972.1 | chr3:33919000-33980276 |
| 8405 | Dmkn | NM_001166174.1 | chr7:31548774-31566085 | | 8500 | Dnajc19 | NM_001286973.1 | chr3:33919000-33980276 |
| 8406 | Dmkn | NM_028618.2 | chr7:31548774-31566085 | | 8501 | Dnajc19 | NM_026332.4 | chr3:33919000-33980276 |
| 8407 | Dmkn | NM_172899.4 | chr7:31548774-31566085 | | 8502 | Dnajc2 | NM_009584.4 | chr5:21263094-21290983 |
| 8408 | Dmp1 | NM_016779.2 | chr5:104631635-104643121 | | 8503 | Dnajc21 | NM_030046.2 | chr15:10376517-10400271 |
| 8409 | Dmpk | NM_001190490.1 | chr7:19669197-19679169 | | 8504 | Dnajc22 | NM_178835.2 | chr15:98929914-98935138 |
| 8410 | Dmpk | NM_001190491.1 | chr7:19669197-19679169 | | 8505 | Dnajc24 | NM_026992.3 | chr2:105806864-105843706 |
| 8411 | Dmpk | NM_032418.2 | chr7:19669197-19679169 | | 8506 | Dnajc24 | NR_033993.1 | chr2:105806864-105843706 |
| 8412 | Dmr | NR_102372.1 | chr5:145005305-145121874 | | 8507 | Dnajc25 | NM_001033165.3 | chr4:59018064-59036270 |
| 8413 | Dmr | NR_102373.1 | chr5:145005305-145121874 | | 8508 | Dnajc27 | NM_153082.4 | chr12:4082573-4110612 |
| 8414 | Dmr | NR_102374.1 | chr5:145005305-145121874 | | 8509 | Dnajc28 | NM_001099738.1 | chr16:91614501-91619244 |
| 8415 | Dmrt1 | NM_015826.5 | chr19:25580195-25678818 | | 8510 | Dnajc28 | NM_138664.2 | chr16:91614501-91619244 |
| 8416 | Dmrt2 | NM_145831.3 | chr19:25746900-25753481 | | 8511 | Dnajc3 | NM_008929.2 | chr14:119337153-119380924 |
| 8417 | Dmrt3 | NM_177360.3 | chr19:25685026-25698411 | | 8512 | Dnajc30 | NM_025362.3 | chr5:135540076-135541235 |
| 8418 | Dmrta1 | NM_175647.3 | chr4:89354888-89361457 | | 8513 | Dnajc4 | NM_020566.1 | chr19:7062400-7066762 |
| 8419 | Dmrta2 | NM_172296.2 | chr4:109650629-109656289 | | 8514 | Dnajc5 | NM_001271584.1 | chr2:181255189-181287585 |
| 8420 | Dmrtb1 | NM_019872.1 | chr4:107348894-107356767 | | 8515 | Dnajc5 | NM_001271585.1 | chr2:181255189-181287585 |
| 8421 | Dmrtc1a | NM_001038616.2 | chrX:100098859-100104026 | | 8516 | Dnajc5 | NM_016775.3 | chr2:181255189-181287585 |
| 8422 | Dmrtc1a | NM_027591.3 | chrX:100098859-100104026 | | 8517 | Dnajc5 | NR_073369.1 | chr2:181255189-181287585 |
| 8423 | Dmrtc1a | NM_029378.2 | chrX:100098859-100104026 | | 8518 | Dnajc5b | NM_001163536.1 | chr3:19408594-19510862 |
| 8424 | Dmrtc1b | NM_001039116.2 | chrX:99903219-99910548 | | 8519 | Dnajc5b | NM_001163537.1 | chr3:19408594-19510862 |
| 8425 | Dmrtc1c1 | NM_001142691.1 | chrX:100041977-100049955 | | 8520 | Dnajc5b | NM_025489.3 | chr3:19408594-19510862 |
| 8426 | Dmrtc1c2 | NM_001142690.1 | chrX:99998301-100005281 | | 8521 | Dnajc5g | NM_177677.3 | chr5:31410692-31414897 |
| 8427 | Dmrtc2 | NM_027732.2 | chr7:25655075-25662670 | | 8522 | Dnajc6 | NM_001164583.1 | chr4:101169252-101315404 |
| 8428 | Dmtf1 | NM_001110327.1 | chr5:9100736-9161776 | | 8523 | Dnajc6 | NM_001164584.1 | chr4:101169252-101315404 |
| 8429 | Dmtf1 | NM_011806.3 | chr5:9100736-9161776 | | 8524 | Dnajc6 | NM_001164585.1 | chr4:101169252-101315404 |
| 8430 | Dmtn | NM_001252662.1 | chr14:71001990-71035855 | | 8525 | Dnajc6 | NM_198412.2 | chr4:101169252-101315404 |
| 8431 | Dmtn | NM_001252663.1 | chr14:71001990-71035855 | | 8526 | Dnajc7 | NM_019795.4 | chr11:100444149-100481482 |
| 8432 | Dmtn | NM_001252664.1 | chr14:71001990-71035855 | | 8527 | Dnajc8 | NM_172400.3 | chr4:132091473-132109657 |
| 8433 | Dmtn | NM_001252665.1 | chr14:71001990-71035855 | | 8528 | Dnajc9 | NM_134081.5 | chr14:21203859-21208132 |
| 8434 | Dmtn | NM_001252666.1 | chr14:71001990-71035855 | | 8529 | Dnal1 | NM_028821.3 | chr12:85455277-85484460 |
| 8435 | Dmtn | NM_013514.4 | chr14:71001990-71035855 | | 8530 | Dnal4 | NM_017470.2 | chr15:79591878-79604897 |
| 8436 | Dmwd | NM_010058.2 | chr7:19661548-19668124 | | 8531 | Dnali1 | NM_175223.4 | chr4:124732583-124742901 |
| 8437 | Dmxl1 | NM_001081371.2 | chr18:49992650-50125127 | | 8532 | Dnase1 | NM_010061.5 | chr16:4037145-4040024 |
| 8438 | Dmxl2 | NM_172771.2 | chr9:54212964-54349433 | | 8533 | Dnase1l1 | NM_001172154.1 | chrX:71518555-71527672 |
| 8439 | Dna2 | NM_177372.3 | chr10:62409776-62436936 | | 8534 | Dnase1l1 | NM_027109.2 | chrX:71518555-71527672 |
| 8440 | Dnaaf1 | NM_026648.4 | chr8:122099135-122122354 | | 8535 | Dnase1l2 | NM_025718.3 | chr17:24577712-24580046 |
| 8441 | Dnaaf2 | NM_027269.3 | chr12:70290825-70299416 | | 8536 | Dnase1l3 | NM_007870.3 | chr14:8797703-8826696 |

Fig. 25 - 46

| | | | | | | | | |
|---|---|---|---|---|---|---|---|---|
| 8537 | Dnase2a | NM_010062.3 | chr8:87432522-87435360 | | 8632 | Dpcr1 | NM_001033366.3 | chr17:35772699-35780640 |
| 8538 | Dnase2b | NM_019957.4 | chr3:146244337-146278562 | | 8633 | Dpep1 | NM_007876.2 | chr8:125710134-125725713 |
| 8539 | Dnd1 | NM_173383.2 | chr18:36923325-36925868 | | 8634 | Dpep2 | NM_176913.4 | chr8:108508956-108520323 |
| 8540 | Dner | NM_152915.1 | chr1:84366414-84692796 | | 8635 | Dpep3 | NM_027960.2 | chr8:108497419-108503319 |
| 8541 | Dnlz | NM_001139503.1 | chr2:26171052-26207630 | | 8636 | Dpf1 | NM_013874.2 | chr7:30089023-30102605 |
| 8542 | Dnlz | NM_001139504.1 | chr2:26171052-26207630 | | 8637 | Dpf2 | NM_001291078.1 | chr19:5896515-5912871 |
| 8543 | Dnlz | NM_026828.3 | chr2:26171052-26207630 | | 8638 | Dpf2 | NM_011262.5 | chr19:5896515-5912871 |
| 8544 | Dnm1 | NM_010065.3 | chr2:32163991-32208849 | | 8639 | Dpf3 | NM_001267625.1 | chr12:84314737-84828686 |
| 8545 | Dnm1l | NM_001025947.2 | chr16:16312320-16359124 | | 8640 | Dpf3 | NM_001267626.1 | chr12:84314737-84828686 |
| 8546 | Dnm1l | NM_001276340.1 | chr16:16312320-16359124 | | 8641 | Dpf3 | NM_058212.2 | chr12:84314737-84828686 |
| 8547 | Dnm1l | NM_001276341.1 | chr16:16312320-16359124 | | 8642 | Dph1 | NM_144491.2 | chr11:74991145-75003985 |
| 8548 | Dnm1l | NM_152816.3 | chr16:16312320-16359124 | | 8643 | Dph2 | NM_026344.3 | chr4:117561247-117564608 |
| 8549 | Dnm1l | NR_075074.1 | chr16:16312320-16359124 | | 8644 | Dph3 | NM_001047433.2 | chr14:32893702-32898878 |
| 8550 | Dnm2 | NM_001039520.2 | chr9:21229351-21314630 | | 8645 | Dph3 | NM_001284346.1 | chr14:32893702-32898878 |
| 8551 | Dnm2 | NM_001253893.1 | chr9:21229351-21314630 | | 8646 | Dph3 | NM_172254.4 | chr14:32893702-32898878 |
| 8552 | Dnm2 | NM_001253894.1 | chr9:21229351-21314630 | | 8647 | Dph3 | NR_104303.1 | chr14:32893702-32898878 |
| 8553 | Dnm2 | NM_007871.2 | chr9:21229351-21314630 | | 8648 | Dph3 | NR_104304.1 | chr14:32893702-32898878 |
| 8554 | Dnm3 | NM_001038619.1 | chr1:163917432-164408165 | | 8649 | Dph3 | NR_104305.1 | chr14:32893702-32898878 |
| 8555 | Dnm3 | NM_172646.2 | chr1:163917432-164408165 | | 8650 | Dph5 | NM_027193.2 | chr3:115591100-115632241 |
| 8556 | Dnm3os | NR_002870.2 | chr1:164147754-164155681 | | 8651 | Dph6 | NM_025675.4 | chr2:114342153-114480664 |
| 8557 | Dnmbp | NM_028029.4 | chr19:43921308-44014688 | | 8652 | Dph7 | NM_026044.3 | chr2:24817942-24828991 |
| 8558 | Dnmt1 | NM_001199431.1 | chr9:20711649-20764332 | | 8653 | Dpm1 | NM_010072.3 | chr2:168034547-168055879 |
| 8559 | Dnmt1 | NM_001199432.1 | chr9:20711649-20764332 | | 8654 | Dpm2 | NM_010073.2 | chr2:32426377-32429091 |
| 8560 | Dnmt1 | NM_001199433.1 | chr9:20711649-20764332 | | 8655 | Dpm3 | NM_026767.4 | chr3:89070382-89071001 |
| 8561 | Dnmt1 | NM_010066.4 | chr9:20711649-20764332 | | 8656 | Dpp10 | NM_199021.3 | chr1:125228714-125942136 |
| 8562 | Dnmt3a | NM_001271753.1 | chr12:3806979-3914443 | | 8657 | Dpp3 | NM_133803.2 | chr19:4907228-4928287 |
| 8563 | Dnmt3a | NM_007872.4 | chr12:3806979-3914443 | | 8658 | Dpp4 | NM_001159543.1 | chr2:62168129-62250288 |
| 8564 | Dnmt3a | NM_153743.4 | chr12:3806979-3914443 | | 8659 | Dpp4 | NM_010074.3 | chr2:62168129-62250288 |
| 8565 | Dnmt3aos | NR_045884.1 | chr12:3859293-3862244 | | 8660 | Dpp6 | NM_001136060.2 | chr5:27143896-28054040 |
| 8566 | Dnmt3b | NM_001003960.4 | chr2:153475184-153513466 | | 8661 | Dpp6 | NM_001198886.1 | chr5:27143896-28054040 |
| 8567 | Dnmt3b | NM_001003961.4 | chr2:153475184-153513466 | | 8662 | Dpp6 | NM_010075.2 | chr5:27143896-28054040 |
| 8568 | Dnmt3b | NM_001003963.4 | chr2:153475184-153513466 | | 8663 | Dpp6 | NM_207282.3 | chr5:27143896-28054040 |
| 8569 | Dnmt3b | NM_001122997.2 | chr2:153475184-153513466 | | 8664 | Dpp7 | NM_031843.2 | chr2:25207809-25211852 |
| 8570 | Dnmt3b | NM_001271744.1 | chr2:153475184-153513466 | | 8665 | Dpp8 | NM_028906.2 | chr9:64880264-64930458 |
| 8571 | Dnmt3b | NM_001271745.1 | chr2:153475184-153513466 | | 8666 | Dpp9 | NM_172624.3 | chr17:56326104-56358312 |
| 8572 | Dnmt3b | NM_001271746.1 | chr2:153475184-153513466 | | 8667 | Dppa1 | NM_001163358.1 | chr11:46420511-46442776 |
| 8573 | Dnmt3b | NM_001271747.1 | chr2:153475184-153513466 | | 8668 | Dppa1 | NM_178247.3 | chr11:46420511-46442776 |
| 8574 | Dnmt3b | NM_010068.5 | chr2:153475184-153513466 | | 8669 | Dppa2 | NM_028615.1 | chr16:48310386-48319626 |
| 8575 | Dnmt3l | NM_001081695.2 | chr10:77492766-77526367 | | 8670 | Dppa3 | NM_139218.1 | chr6:122576441-122580289 |
| 8576 | Dnmt3l | NM_001284197.1 | chr10:77492766-77526367 | | 8671 | Dppa4 | NM_001018002.1 | chr16:48283847-48294405 |
| 8577 | Dnmt3l | NM_001284198.1 | chr10:77492766-77526367 | | 8672 | Dppa4 | NM_028610.2 | chr16:48283847-48294405 |
| 8578 | Dnmt3l | NM_001284199.1 | chr10:77492766-77526367 | | 8673 | Dppa5a | NM_025274.3 | chr9:78214860-78216006 |
| 8579 | Dnmt3l | NM_001284200.1 | chr10:77492766-77526367 | | 8674 | Dpt | NM_019759.1 | chr1:166726862-166754397 |
| 8580 | Dnmt3l | NM_019448.4 | chr10:77492766-77526367 | | 8675 | Dpy19l1 | NM_172920.4 | chr9:24216224-24307584 |
| 8581 | Dnpep | NM_001110831.1 | chr1:75305139-75314212 | | 8676 | Dpy19l2 | NM_001166207.1 | chr9:24361492-24500737 |
| 8582 | Dnpep | NM_016878.4 | chr1:75305139-75314212 | | 8677 | Dpy19l3 | NM_178704.3 | chr7:36470518-36539473 |
| 8583 | Dnph1 | NM_207161.3 | chr17:46633737-46636567 | | 8678 | Dpy19l4 | NM_001081201.1 | chr4:11192225-11249278 |
| 8584 | Dntt | NM_001043228.1 | chr19:41103764-41134015 | | 8679 | Dpy30 | NM_001146222.1 | chr7:74698813-74723284 |
| 8585 | Dntt | NM_009345.2 | chr19:41103764-41134015 | | 8680 | Dpy30 | NM_001146223.1 | chr17:74698813-74723284 |
| 8586 | Dnttip1 | NM_133763.1 | chr2:164571514-164593719 | | 8681 | Dpy30 | NM_001146224.1 | chr17:74698813-74723284 |
| 8587 | Dnttip2 | NM_153806.1 | chr3:121977331-121988189 | | 8682 | Dpy30 | NM_024428.4 | chr17:74698813-74723284 |
| 8588 | Doc2a | NM_010069.1 | chr7:133991067-133996219 | | 8683 | Dpyd | NM_170778.2 | chr3:118265095-119135836 |
| 8589 | Doc2b | NM_007873.2 | chr11:75328591-75605559 | | 8684 | Dpys | NM_001164466.1 | chr15:39600030-39689016 |
| 8590 | Doc2g | NM_021791.3 | chr19:4003384-4007005 | | 8685 | Dpys | NM_022722.3 | chr15:39600030-39689016 |
| 8591 | Dock1 | NM_001033420.2 | chr7:141861370-142365330 | | 8686 | Dpysl2 | NM_009955.3 | chr14:67421700-67487437 |
| 8592 | Dock10 | NM_001285927.1 | chr1:80497642-80755128 | | 8687 | Dpysl3 | NM_001136086.2 | chr18:43480632-43597940 |
| 8593 | Dock10 | NM_175291.4 | chr1:80497642-80755128 | | 8688 | Dpysl3 | NM_001291455.1 | chr18:43480632-43597940 |
| 8594 | Dock11 | NM_001009947.3 | chrX:33428826-33616557 | | 8689 | Dpysl3 | NM_009468.5 | chr18:43480632-43597940 |
| 8595 | Dock2 | NM_033374.3 | chr11:34126821-34597407 | | 8690 | Dpysl4 | NM_011993.4 | chr7:146271899-146287690 |
| 8596 | Dock3 | NM_153413.2 | chr9:106795156-107134240 | | 8691 | Dpysl5 | NM_023047.2 | chr5:31014267-31101742 |
| 8597 | Dock4 | NM_172803.2 | chr12:41172839-41573075 | | 8692 | DQ267100 | NR_046304.1 | chr12:110887827-110887897 |
| 8598 | Dock5 | NM_177030.3 | chr14:68369985-68551629 | | 8693 | DQ267101 | NR_046305.1 | chr12:110889634-110889705 |
| 8599 | Dock6 | NM_177030.3 | chr9:21604624-21857079 | | 8694 | DQ267102 | NR_046306.1 | chr12:110894555-110894625 |
| 8600 | Dock7 | NM_001290636.1 | chr4:98603349-98787606 | | 8695 | Dqx1 | NM_033606.3 | chr5:83007837-83017213 |
| 8601 | Dock7 | NM_026062.5 | chr4:98603349-98787606 | | 8696 | Dr1 | NM_026106.4 | chr5:108697915-108709540 |
| 8602 | Dock8 | NM_028785.3 | chr19:25074018-25276922 | | 8697 | Dram1 | NM_027878.2 | chr10:87785548-87819820 |
| 8603 | Dock9 | NM_001081039.1 | chr14:121941260-122196956 | | 8698 | Dram2 | NM_001025582.2 | chr3:106350715-106378259 |
| 8604 | Dock9 | NM_001128307.1 | chr14:121941260-122196956 | | 8699 | Dram2 | NM_001286986.1 | chr3:106350715-106378259 |
| 8605 | Dock9 | NM_001128308.1 | chr14:121941260-122196956 | | 8700 | Dram2 | NM_001286987.1 | chr3:106350715-106378259 |
| 8606 | Dock9 | NM_134074.2 | chr14:121941260-122196956 | | 8701 | Dram2 | NM_026013.3 | chr3:106350715-106378259 |
| 8607 | Dohh | NM_133964.2 | chr10:80847173-80851097 | | 8702 | Drap1 | NM_001291080.1 | chr19:5406814-5424979 |
| 8608 | Dok1 | NM_001291799.1 | chr6:82980929-82983465 | | 8703 | Drap1 | NM_024176.2 | chr19:5406814-5424979 |
| 8609 | Dok1 | NM_010070.4 | chr6:82980929-82983465 | | 8704 | Draxin | NM_027428.3 | chr4:147472545-147504807 |
| 8610 | Dok2 | NM_010071.2 | chr14:71174187-71178301 | | 8705 | Drc1 | NM_001033460.3 | chr5:30607913-30668993 |
| 8611 | Dok3 | NM_013739.2 | chr13:55624595-55629899 | | 8706 | Drd1a | NM_001291801.1 | chr13:54146552-54151027 |
| 8612 | Dok4 | NM_053246.4 | chr8:97387728-97400212 | | 8707 | Drd1a | NM_010076.3 | chr13:54146552-54151027 |
| 8613 | Dok5 | NM_001163686.1 | chr2:170557306-170705275 | | 8708 | Drd2 | NM_010077.2 | chr9:49148766-49215319 |
| 8614 | Dok5 | NM_029761.4 | chr2:170557306-170705275 | | 8709 | Drd3 | NM_007877.1 | chr16:43762354-43822952 |
| 8615 | Dok6 | NM_001039173.1 | chr18:89470526-89938528 | | 8710 | Drd4 | NM_007878.2 | chr7:148477904-148480900 |
| 8616 | Dok7 | NM_172708.3 | chr5:35399732-35430480 | | 8711 | Drd5 | NM_013503.5 | chr5:38710747-38713549 |
| 8617 | Dolk | NM_177648.3 | chr2:30139748-30141874 | | 8712 | Dreh | NR_105051.1 | chr17:65116450-65117271 |
| 8618 | Dolpp1 | NM_001290508.1 | chr2:30247773-30271268 | | 8713 | Drg1 | NM_007879.1 | chr11:3149924-3166389 |
| 8619 | Dolpp1 | NM_001290509.1 | chr2:30247773-30271268 | | 8714 | Drg2 | NM_021354.1 | chr11:60268118-60282207 |
| 8620 | Dolpp1 | NM_020329.4 | chr2:30247773-30271268 | | 8715 | Drosha | NM_001130149.1 | chr15:12754569-12865046 |
| 8621 | Dolpp1 | NR_110963.1 | chr2:30247773-30271268 | | 8716 | Drosha | NM_026799.3 | chr15:12754569-12865046 |
| 8622 | Donson | NM_021720.1 | chr16:91679509-91688973 | | 8717 | Drp2 | NM_010078.3 | chrX:130939318-130991112 |
| 8623 | Dopey1 | NM_177028.3 | chr9:86360761-86494413 | | 8718 | Dsc1 | NM_001291804.1 | chr18:20241972-20273274 |
| 8624 | Dopey2 | NM_026700.2 | chr16:93712151-93810833 | | 8719 | Dsc1 | NM_013504.5 | chr18:20241972-20273274 |
| 8625 | Dopey2 | NM_027293.1 | chr16:93712151-93810833 | | 8720 | Dsc2 | NM_013505.3 | chr18:20189298-20218006 |
| 8626 | Dos | NM_001195268.1 | chr10:79579280-79602112 | | 8721 | Dsc3 | NM_001291809.1 | chr18:20119430-20160598 |
| 8627 | Dos | NR_036582.1 | chr10:79579280-79602112 | | 8722 | Dsc3 | NM_007882.3 | chr18:20119430-20160598 |
| 8628 | Dot1l | NM_199322.1 | chr10:80217950-80257092 | | 8723 | Dscam | NM_031174.4 | chr16:96813686-97392342 |
| 8629 | Doxl2 | NM_001029987.1 | chr6:48925141-48928744 | | 8724 | Dscaml1 | NM_001081270.1 | chr9:45238376-45561796 |
| 8630 | Dpagt1 | NM_007875.2 | chr9:44134927-44141683 | | 8725 | Dscc1 | NM_183089.2 | chr15:54907655-54922033 |
| 8631 | Dpcd | NM_172639.2 | chr19:45635105-45652777 | | 8726 | Dscr3 | NM_007834.3 | chr16:94719330-94748236 |

Fig. 25 - 47

| | | | |
|---|---|---|---|
| 8727 | Dse | NM_172508.2 | chr10:33871198-33927357 |
| 8728 | Dsel | NM_001081316.1 | chr1:113755278-113761495 |
| 8729 | Dsg1a | NM_010079.2 | chr18:20469373-20501854 |
| 8730 | Dsg1b | NM_181682.1 | chr18:20535335-20568242 |
| 8731 | Dsg1c | NM_181680.1 | chr18:20405840-20442424 |
| 8732 | Dsg2 | NM_007883.2 | chr18:20716616-20763027 |
| 8733 | Dsg3 | NM_030596.3 | chr18:20668804-20699811 |
| 8734 | Dsg4 | NM_181564.2 | chr18:20594675-20630322 |
| 8735 | Dsn1 | NM_025853.3 | chr2:156820797-156832811 |
| 8736 | Dsp | NM_023842.2 | chr13:38243162-38290446 |
| 8737 | Dspp | NM_010080.2 | chr5:104599730-104609146 |
| 8738 | Dst | NM_001276764.1 | chr1:33965069-34365507 |
| 8739 | Dst | NM_010081.2 | chr1:33965069-34365507 |
| 8740 | Dst | NM_133833.3 | chr1:33965069-34365507 |
| 8741 | Dst | NM_134448.3 | chr1:33965069-34365507 |
| 8742 | Dstn | NM_019771.2 | chr2:143741066-143769060 |
| 8743 | Dstyk | NM_172516.4 | chr1:134314029-134363536 |
| 8744 | Dtd1 | NM_025314.3 | chr2:144425688-144594483 |
| 8745 | Dtd2 | NM_029545.2 | chr12:53098493-53107488 |
| 8746 | Dthd1 | NM_001170705.1 | chr5:63205061-63279557 |
| 8747 | Dtl | NM_029766.3 | chr1:193361243-193399413 |
| 8748 | Dtna | NM_001285807.1 | chr18:23468520-23818220 |
| 8749 | Dtna | NM_001285808.1 | chr18:23468520-23818220 |
| 8750 | Dtna | NM_001285810.1 | chr18:23468520-23818220 |
| 8751 | Dtna | NM_001285811.1 | chr18:23468520-23818220 |
| 8752 | Dtna | NM_001285813.1 | chr18:23468520-23818220 |
| 8753 | Dtna | NM_001285817.1 | chr18:23468520-23818220 |
| 8754 | Dtna | NM_207650.4 | chr18:23468520-23818220 |
| 8755 | Dtna | NM_001162465.1 | chr18:23468520-23818220 |
| 8756 | Dtnb | NM_007886.2 | chr12:3572390-3781398 |
| 8757 | Dtnb | NR_027869.1 | chr12:3572390-3781398 |
| 8758 | Dtnb | NR_027870.1 | chr12:3572390-3781398 |
| 8759 | Dtnb | NM_025772.4 | chr12:3572390-3781398 |
| 8760 | Dtnbp1 | NM_026981.2 | chr13:45017448-45097465 |
| 8761 | Dtwd1 | NM_001170960.1 | chr2:125977876-125991013 |
| 8762 | Dtwd2 | NM_026854.3 | chr18:49855798-49915255 |
| 8763 | Dtwd2 | NM_008052.3 | chr18:49855798-49915255 |
| 8764 | Dtx1 | NM_001256097.1 | chr5:121130272-121161678 |
| 8765 | Dtx2 | NM_001256098.1 | chr5:136470669-136508751 |
| 8766 | Dtx2 | NM_023842.2 | chr5:136470669-136508751 |
| 8767 | Dtx2 | NM_030714.2 | chr5:136470669-136508751 |
| 8768 | Dtx2 | NM_001013371.2 | chr5:136470669-136508751 |
| 8769 | Dtx3 | NM_172442.3 | chr10:126627434-126632765 |
| 8770 | Dtx3l | NM_001105667.1 | chr16:35926601-35939113 |
| 8771 | Dtx4 | NM_023136.2 | chr19:12540825-12576406 |
| 8772 | Dtymk | NM_001099297.1 | chr1:95689152-95698511 |
| 8773 | Dtymk | NM_177610.2 | chr1:95689152-95698511 |
| 8774 | Duox1 | NM_145395.2 | chr2:122114407-122173708 |
| 8775 | Duox2 | NM_001013826.2 | chr2:122106172-122123901 |
| 8776 | Duoxa1 | NM_026824.3 | chr2:122129284-122139466 |
| 8777 | Duoxa2 | NM_025518.4 | chr2:122124635-122128621 |
| 8778 | Dupd1 | NM_144858.2 | chr14:22495793-22533798 |
| 8779 | Dus1l | NM_028002.2 | chr11:120650515-120657709 |
| 8780 | Dus2 | NM_013642.3 | chr8:108535406-108577719 |
| 8781 | Dus3l | NM_022019.5 | chr7:56904173-56909516 |
| 8782 | Dus4l | NM_028099.4 | chr12:32324919-32339691 |
| 8783 | Dusp1 | NM_023173.2 | chr17:26641535-26645417 |
| 8784 | Dusp10 | NM_001007268.1 | chr1:185858339-185899515 |
| 8785 | Dusp11 | NM_013849.3 | chr6:85892262-85911661 |
| 8786 | Dusp12 | NM_001159376.1 | chr1:172804318-172815671 |
| 8787 | Dusp13 | NM_145744.2 | chr14:22552617-22567844 |
| 8788 | Dusp13 | NM_019819.3 | chr14:22552617-22567844 |
| 8789 | Dusp14 | NM_001048054.1 | chr11:83861546-83881859 |
| 8790 | Dusp15 | NM_130447.3 | chr2:152766730-152777318 |
| 8791 | Dusp15 | NM_173745.5 | chr2:152766730-152777318 |
| 8792 | Dusp16 | NM_024438.4 | chr6:134665485-134742646 |
| 8793 | Dusp16 | NM_010090.4 | chr6:134665485-134742646 |
| 8794 | Dusp18 | NM_028568.1 | chr17:3795242-3801299 |
| 8795 | Dusp19 | NM_001037955.4 | chr2:80457371-80471818 |
| 8796 | Dusp2 | NM_026268.3 | chr2:127161894-127164113 |
| 8797 | Dusp21 | NM_134833.3 | chrX:17722995-17723818 |
| 8798 | Dusp22 | NM_026725.2 | chr13:30751927-30803101 |
| 8799 | Dusp22 | NM_025869.3 | chr13:30751927-30803101 |
| 8800 | Dusp23 | NM_001033344.3 | chr1:174560899-174563105 |
| 8801 | Dusp26 | NM_001160049.1 | chr8:32200133-32207519 |
| 8802 | Dusp27 | NM_175118.3 | chr1:168028278-168058029 |
| 8803 | Dusp27 | NM_028207.3 | chr1:168028278-168058029 |
| 8804 | Dusp28 | NM_176933.4 | chr1:94803565-94805197 |
| 8805 | Dusp3 | NM_010085390.1 | chr11:101832457-101846105 |
| 8806 | Dusp4 | NM_026268.3 | chr8:35870663-35882948 |
| 8807 | Dusp5 | NM_026268.3 | chr19:53603807-53615812 |
| 8808 | Dusp6 | NM_153459.4 | chr10:98725864-98730123 |
| 8809 | Dusp7 | NM_008748.3 | chr9:106270962-106278054 |
| 8810 | Dusp8 | NM_029352.3 | chr7:149265391-149281189 |
| 8811 | Dusp9 | NM_001159646.1 | chrX:70884779-70888853 |
| 8812 | Dut | NM_023595.6 | chr2:125072983-125084785 |
| 8813 | Dut | NM_001081954.1 | chr2:125072983-125084785 |
| 8814 | Dux | NM_183389.1 | chr10:57693398-57695423 |
| 8815 | Duxbl1 | NM_183389.1 | chr14:26802490-26809652 |
| 8816 | Duxbl2 | NM_001177538.1 | chr14:27081743-27088920 |
| 8817 | Duxbl2 | NM_001177539.1 | chr14:26942094-26949271 |
| 8818 | Duxbl3 | NM_010091.4 | chr14:26802490-26809652 |
| 8819 | Duxbl3 | NM_007888.3 | chr4:155221426-155233412 |
| 8820 | Dvl1 | NM_007888.3 | chr4:155221426-155233412 |
| 8821 | Dvl2 | NM_007888.3 | chr11:69814127-69824611 |
| 8822 | Dvl3 | NM_007889.2 | chr16:20517136-20532260 |
| 8823 | DXBay18 | NM_001025384.3 | chrX:70382973-70374599 |
| 8824 | DXBay18 | NM_001025384.3 | chrX:70382570-70403738 |
| 8825 | Dxo | NM_001163770.1 | chr17:34973963-34976131 |
| 8826 | Dxo | NM_033613.2 | chr17:34973963-34976131 |
| 8827 | Dydc1 | NM_027094.1 | chr14:41886199-41905486 |
| 8828 | Dydc2 | NM_027717.1 | chr14:41862497-41882363 |
| 8829 | Dym | NM_027727.2 | chr18:75178425-75446620 |
| 8830 | Dynap | NM_029346.1 | chr18:70400082-70404238 |
| 8831 | Dync1h1 | NM_030238.2 | chr12:111839604-111905154 |
| 8832 | Dync1i1 | NM_001191023.1 | chr6:5675638-5978039 |
| 8833 | Dync1i1 | NM_001191025.1 | chr6:5675638-5978039 |
| 8834 | Dync1i1 | NM_001191026.1 | chr6:5675638-5978039 |
| 8835 | Dync1i1 | NM_001191027.1 | chr6:5675638-5978039 |
| 8836 | Dync1i1 | NM_010063.4 | chr6:5675638-5978039 |
| 8837 | Dync1i2 | NM_001198872.1 | chr2:71049762-71101359 |
| 8838 | Dync1i2 | NM_001198873.1 | chr2:71049762-71101359 |
| 8839 | Dync1i2 | NM_001198874.1 | chr2:71049762-71101359 |
| 8840 | Dync1i2 | NM_001198875.1 | chr2:71049762-71101359 |
| 8841 | Dync1i2 | NM_001198876.1 | chr2:71049762-71101359 |
| 8842 | Dync1i2 | NM_001198877.1 | chr2:71049762-71101359 |
| 8843 | Dync1i2 | NM_001198878.1 | chr2:71049762-71101359 |
| 8844 | Dync1i2 | NM_010064.4 | chr2:71049762-71101359 |
| 8845 | Dync1li1 | NM_146229.2 | chr9:114597948-114632895 |
| 8846 | Dync1li2 | NM_001013380.2 | chr8:106941573-106966947 |
| 8847 | Dync2h1 | NM_029851.2 | chr9:6928502-7177046 |
| 8848 | Dync2li1 | NM_172256.1 | chr17:85025838-85054904 |
| 8849 | Dynlt1 | NM_019682.4 | chr5:115747118-115750999 |
| 8850 | Dynll2 | NM_001168471.1 | chr11:87793026-87811800 |
| 8851 | Dynll2 | NM_001168472.1 | chr11:87793026-87811800 |
| 8852 | Dynll2 | NM_026556.4 | chr11:87793026-87811800 |
| 8853 | Dynlrb1 | NM_001291108.1 | chr2:155062268-155076013 |
| 8854 | Dynlrb1 | NM_025947.3 | chr2:155062268-155076013 |
| 8855 | Dynlrb1 | NR_111890.1 | chr2:155062268-155076013 |
| 8856 | Dynlrb1 | NR_111891.1 | chr2:155062268-155076013 |
| 8857 | Dynlrb2 | NM_029297.1 | chr8:119028914-119039815 |
| 8858 | Dynlt1a | NM_001166629.2 | chr17:6306344-6317474 |
| 8859 | Dynlt1b | NM_009342.2 | chr17:6429259-6435443 |
| 8860 | Dynlt1c | NM_001166630.1 | chr17:6600795-6610127 |
| 8861 | Dynlt1c | NM_001166630.1 | chr17:6851323-6860656 |
| 8862 | Dynlt1c | NM_001166630.1 | chr17:6648832-6655064 |
| 8863 | Dynlt1c | NM_001166630.1 | chr17:6806387-6812617 |
| 8864 | Dynlt1f | NM_001166627.1 | chr17:6851323-6860656 |
| 8865 | Dynlt1f | NM_001166627.1 | chr17:6806387-6812617 |
| 8866 | Dynlt1f | NM_001166627.1 | chr17:6600795-6610127 |
| 8867 | Dynlt1f | NM_001166627.1 | chr17:6648832-6655064 |
| 8868 | Dynlt1f | NM_001199948.1 | chr17:6600795-6610127 |
| 8869 | Dynlt1f | NM_001199948.1 | chr17:6851323-6860656 |
| 8870 | Dynlt3 | NM_025975.5 | chrX:9231395-9240109 |
| 8871 | Dyrk1a | NM_001113389.1 | chr16:94791812-94917126 |
| 8872 | Dyrk1a | NM_007890.2 | chr16:94791812-94917126 |
| 8873 | Dyrk1b | NM_001037957.3 | chr7:28964501-28972317 |
| 8874 | Dyrk1b | NM_001271370.1 | chr7:28964501-28972317 |
| 8875 | Dyrk1b | NM_010092.2 | chr7:28964501-28972317 |
| 8876 | Dyrk2 | NM_001014390.2 | chr10:118296404-118305959 |
| 8877 | Dyrk3 | NM_145508.2 | chr1:133025017-133034811 |
| 8878 | Dyrk4 | NM_207210.2 | chr6:126826216-126871857 |
| 8879 | Dysf | NM_001077694.2 | chr6:83958591-84161053 |
| 8880 | Dysf | NM_021469.3 | chr6:83958591-84161053 |
| 8881 | Dytn | NM_001081658.1 | chr1:63669424-63733501 |
| 8882 | Dyx1c1 | NM_001163725.1 | chr9:72806591-72820874 |
| 8883 | Dyx1c1 | NM_026314.3 | chr9:72806591-72820874 |
| 8884 | Dzank1 | NM_172859.2 | chr2:144296292-144353134 |
| 8885 | Dzip1 | NM_025943.3 | chr14:119274741-119322389 |
| 8886 | Dzip1l | NM_028258.3 | chr9:99530013-99569675 |
| 8887 | Dzip3 | NM_001110017.1 | chr16:48924340-48994225 |
| 8888 | Dzip3 | NM_027341.2 | chr16:48924340-48994225 |
| 8889 | E030002O03Rik | NM_172905.2 | chr7:111301526-111313330 |
| 8890 | E030003E18Rik | NR_015502.1 | chr19:20567205-20630900 |
| 8891 | E030011O05Rik | NR_015511.2 | chr9:96631994-96653250 |
| 8892 | E030013I19Rik | NR_040353.1 | chr2:12222873-12233942 |
| 8893 | E030018B13Rik | NM_001256311.1 | chr7:71061743-71065425 |
| 8894 | E030019B06Rik | NM_001243018.1 | chr7:146786849-146802228 |
| 8895 | E030019B13Rik | NR_045082.1 | chr12:57591414-57630407 |
| 8896 | E030024N20Rik | NR_033228.1 | chr19:16238588-16244948 |
| 8897 | E030025P04Rik | NR_037978.1 | chr11:109006604-109005683 |
| 8898 | E030030I06Rik | NM_001254744.1 | chr10:21832855-21869076 |
| 8899 | E030030I06Rik | NM_001254745.1 | chr10:21832855-21869076 |
| 8900 | E030044B06Rik | NR_045343.1 | chr9:40942805-40957129 |
| 8901 | E130006D01Rik | NR_045832.1 | chr5:112163303-112190748 |
| 8902 | E130006D01Rik | NR_045833.1 | chr5:112163303-112190748 |
| 8903 | E130006D01Rik | NR_045834.1 | chr5:112163303-112190748 |
| 8904 | E130008D07Rik | NR_045153.1 | chr17:43282989-43295240 |
| 8905 | E130008D07Rik | NR_045154.1 | chr17:43282989-43295240 |
| 8906 | E130008D07Rik | NR_045155.1 | chr17:43282989-43295240 |
| 8907 | E130012A19Rik | NR_175332.3 | chr11:97488700-97491030 |
| 8908 | E130018N17Rik | NR_040327.1 | chr16:167978102-167980013 |
| 8909 | E130102H24Rik | NR_040708.1 | chr4:101019129-101028853 |
| 8910 | E130112N10Rik | NR_015604.2 | chr6:125181294-125189952 |
| 8911 | E130114P18Rik | NR_015513.2 | chr4:97234566-97251282 |
| 8912 | E130201H02Rik | NR_024324.1 | chr7:127741138-127741989 |
| 8913 | E130215H24Rik | NR_040331.1 | chr3:150493230-150494668 |
| 8914 | E130218I03Rik | NR_040435.1 | chr4:133799220-133801788 |
| 8915 | E130218I03Rik | NR_040436.1 | chr4:133799220-133801788 |
| 8916 | E130304I02Rik | NR_033567.1 | chr7:36587611-36623093 |

Fig. 25 - 48

| | | | | | | | |
|---|---|---|---|---|---|---|---|
| 8917 | E130307A14Rik | NR_038037.1 | chr10:39341217-39451813 | 9011 | Eci2 | NM_001110331.1 | chr13:35069616-35086013 |
| 8918 | E130308A19Rik | NM_001015681.2 | chr4:59639082-59767175 | 9012 | Eci2 | NM_011868.3 | chr13:35069616-35086013 |
| 8919 | E130308A19Rik | NM_153158.5 | chr4:59639082-59767175 | 9013 | Eci2 | NR_073427.1 | chr13:35069616-35086013 |
| 8920 | E130309D02Rik | NM_172726.4 | chr5:144062750-144077039 | 9014 | Eci3 | NM_026947.2 | chr13:35038483-35055678 |
| 8921 | E130309D14Rik | NM_001013784.1 | chr11:74433106-74455018 | 9015 | Ecm1 | NM_001252653.1 | chr3:95538070-95543492 |
| 8922 | E130309F12Rik | NM_178756.4 | chr4:49072333-49353133 | 9016 | Ecm1 | NM_007899.2 | chr3:95538070-95543492 |
| 8923 | E130310I04Rik | NR_045722.1 | chr16:34785035-35002520 | 9017 | Ecm2 | NM_001012324.2 | chr13:49600179-49628158 |
| 8924 | E130310I04Rik | NR_045723.1 | chr16:34785035-35002520 | 9018 | Ecscr | NM_001033141.1 | chr18:35872742-35881145 |
| 8925 | E130311K13Rik | NM_177856.4 | chr3:63718617-63733307 | 9019 | Ecsit | NM_001253897.1 | chr9:21859903-21890575 |
| 8926 | E130317F20Rik | NR_029447.1 | chr10:79314122-79317716 | 9020 | Ecsit | NM_001253898.1 | chr9:21859903-21890575 |
| 8927 | E230008N13Rik | NM_198660.2 | chr4:45903174-45963646 | 9021 | Ecsit | NM_012029.2 | chr9:21859903-21890575 |
| 8928 | E230016K23Rik | NR_036452.1 | chr11:83395562-83437195 | 9022 | Ect2 | NM_001177625.1 | chr3:26996143-27052800 |
| 8929 | E230016K23Rik | NR_036453.1 | chr11:83395562-83437195 | 9023 | Ect2 | NM_001177626.1 | chr3:26996143-27052800 |
| 8930 | E230016M11Rik | NM_040278.1 | chr6:66986593-67030646 | 9024 | Ect2 | NM_007900.3 | chr3:26996143-27052800 |
| 8931 | E230019M04Rik | NM_177921.1 | chrX:136597417-136641336 | 9025 | Ect2l | NM_001195036.1 | chr10:17848827-17930696 |
| 8932 | E230025N22Rik | NM_172834.2 | chr18:36844576-36855579 | 9026 | Eda | NM_001177937.1 | chrX:97170944-97596099 |
| 8933 | E230029C05Rik | NR_110364.1 | chr7:97177668-97197581 | 9027 | Eda | NM_001177938.1 | chrX:97170944-97596099 |
| 8934 | E230029C05Rik | NR_110365.1 | chr7:97177668-97197581 | 9028 | Eda | NM_001177939.1 | chrX:97170944-97596099 |
| 8935 | E2f1 | NM_001291105.1 | chr2:154385135-154395628 | 9029 | Eda | NM_001177940.1 | chrX:97170944-97596099 |
| 8936 | E2f1 | NM_007891.5 | chr2:154385135-154395628 | 9030 | Eda | NM_001177941.1 | chrX:97170944-97596099 |
| 8937 | E2f2 | NM_177733.7 | chr4:135728308-135751971 | 9031 | Eda | NM_001177942.1 | chrX:97170944-97596099 |
| 8938 | E2f3 | NM_001289920.1 | chr13:29998443-30077932 | 9032 | Eda | NM_001177943.1 | chrX:97170944-97596099 |
| 8939 | E2f3 | NM_010093.3 | chr13:29998443-30077932 | 9033 | Eda | NM_001177944.1 | chrX:97170944-97596099 |
| 8940 | E2f4 | NM_148952.1 | chr8:107821562-107829270 | 9034 | Eda | NM_010099.2 | chrX:97170944-97596099 |
| 8941 | E2f5 | NM_007892.2 | chr3:14578671-14606309 | 9035 | Eda2r | NM_001161432.1 | chrX:94529179-94572548 |
| 8942 | E2f6 | NM_033270.2 | chr12:16817770-16833558 | 9036 | Eda2r | NM_001161433.1 | chrX:94529179-94572548 |
| 8943 | E2f6 | NR_027677.1 | chr12:16817770-16833558 | 9037 | Eda2r | NM_175540.5 | chrX:94529179-94572548 |
| 8944 | E2f7 | NM_178609.4 | chr10:110182520-110224440 | 9038 | Edar | NM_010100.3 | chr10:58063535-58138444 |
| 8945 | E2f8 | NM_001013368.5 | chr7:56121798-56136411 | 9039 | Edaradd | NM_133643.1 | chr13:12563475-12612717 |
| 8946 | E330009J07Rik | NM_175528.4 | chr6:40357496-40386132 | 9040 | Edc3 | NM_153799.3 | chr9:57556375-57597969 |
| 8947 | E330011O21Rik | NR_045698.1 | chr16:78251107-78255699 | 9041 | Edc4 | NM_181594.3 | chr8:108404850-108417107 |
| 8948 | E330012B07Rik | NR_033640.1 | chr6:147128762-147156816 | 9042 | Eddm3b | NM_203508.1 | chr14:51736227-51737466 |
| 8949 | E330013P04Rik | NR_026942.1 | chr19:60220577-60238494 | 9043 | Edem1 | NM_138677.2 | chr6:108778634-108809350 |
| 8950 | E330014E10Rik | NM_001122668.1 | chr5:96204888-96233254 | 9044 | Edem2 | NM_145537.2 | chr2:155527408-155555211 |
| 8951 | E330014E10Rik | NM_001122668.1 | chrUn_random:1663024-1691372 | 9045 | Edem3 | NM_001039644.2 | chr1:153602503-153669458 |
| 8952 | E330017A01Rik | NM_175011.2 | chr16:58635374-58838516 | 9046 | Edf1 | NM_021519.1 | chr2:25413419-25417602 |
| 8953 | E330017L17Rik | NR_045190.2 | chr4:129583469-129586240 | 9047 | Edil3 | NM_001037987.3 | chr13:88961076-89462830 |
| 8954 | E330020D12Rik | NR_033736.1 | chr1:155251315-155261363 | 9048 | Edil3 | NM_010103.4 | chr13:88961076-89462830 |
| 8955 | E330021D16Rik | NM_001201390.1 | chr6:136350340-136364090 | 9049 | Edn1 | NM_010104.3 | chr13:42396638-42403358 |
| 8956 | E330023G01Rik | NR_045332.1 | chr9:98649017-98720506 | 9050 | Edn2 | NM_007902.2 | chr4:119834028-119839965 |
| 8957 | E330033B04Rik | NR_030690.1 | chr15:96098994-96105706 | 9051 | Edn3 | NM_007903.4 | chr2:174586258-174609543 |
| 8958 | E330034G19Rik | NM_001033214.2 | chr14:25112585-25129181 | 9052 | Ednra | NM_010332.2 | chr8:80186927-80248351 |
| 8959 | E430016F16Rik | NR_015542.1 | chr7:85725951-85863106 | 9053 | Ednrb | NM_001136061.1 | chr14:104213831-104243693 |
| 8960 | E430018J23Rik | NM_198011.2 | chr7:134534349-134537135 | 9054 | Ednrb | NM_001276296.1 | chr14:104213831-104243693 |
| 8961 | E430025E21Rik | NM_153548.2 | chr15:59163551-59205707 | 9055 | Ednrb | NM_007904.4 | chr14:104213831-104243693 |
| 8962 | E4f1 | NM_007893.4 | chr17:24580723-24592256 | 9056 | Edrf1 | NM_178115.4 | chr7:140829357-140864700 |
| 8963 | E530001F21Rik | NR_002167.2 | chrX:102359716-102360844 | 9057 | Eea1 | NM_001001932.2 | chr10:95403296-95508152 |
| 8964 | E530011L22Rik | NR_033503.1 | chr9:121665758-121669061 | 9058 | Eed | NM_021876.3 | chr7:97103163-97129486 |
| 8965 | Eaf1 | NM_028932.4 | chr14:32308264-32323044 | 9059 | Eef1a1 | NM_010106.2 | chr9:78326260-78329531 |
| 8966 | Eaf2 | NM_001113401.1 | chr16:36792969-36874912 | 9060 | Eef1a2 | NM_007906.2 | chr2:180882396-180891720 |
| 8967 | Eaf2 | NM_001113405.1 | chr16:36792969-36874912 | 9061 | Eef1b2 | NM_018796.3 | chr1:63223405-63227060 |
| 8968 | Eaf2 | NM_134111.2 | chr16:36792969-36874912 | 9062 | Eef1d | NM_001285429.1 | chr15:75725225-75739986 |
| 8969 | Eapp | NM_025456.3 | chr12:55774453-55796852 | 9063 | Eef1d | NM_001285430.1 | chr15:75725225-75739986 |
| 8970 | Ear1 | NM_007894.2 | chr14:44396430-44397304 | 9064 | Eef1d | NM_001285431.1 | chr15:75725225-75739986 |
| 8971 | Ear10 | NM_053112.1 | chr14:44500562-44501033 | 9065 | Eef1d | NM_001285432.1 | chr15:75725225-75739986 |
| 8972 | Ear14 | NM_017389.2 | chr14:51823370-51823831 | 9066 | Eef1d | NM_001285433.1 | chr15:75725225-75739986 |
| 8973 | Ear2 | NM_007895.2 | chr14:44680319-44681196 | 9067 | Eef1d | NM_001285434.1 | chr15:75725225-75739986 |
| 8974 | Ear3 | NM_017388.1 | chr14:44680552-44681022 | 9068 | Eef1d | NM_023240.3 | chr15:75725225-75739986 |
| 8975 | Ear4 | NM_001017422.1 | chr14:51823365-51823831 | 9069 | Eef1d | NM_029663.2 | chr15:75725225-75739986 |
| 8976 | Ear6 | NM_053111.2 | chr14:52473443-52474317 | 9070 | Eef1e1 | NM_025380.2 | chr13:38737559-38750897 |
| 8977 | Ear7 | NM_017385.1 | chr14:52473673-52474140 | 9071 | Eef1g | NM_026007.4 | chr19:9041530-9052670 |
| 8978 | Ears2 | NM_026140.3 | chr7:129182334-129210577 | 9072 | Eef2 | NM_007907.2 | chr10:80639376-80645254 |
| 8979 | Ebag9 | NM_019480.4 | chr15:44451186-44472572 | 9073 | Eef2k | NM_001267710.1 | chr7:127986344-128050733 |
| 8980 | Ebf1 | NM_001290709.1 | chr11:44431601-44821598 | 9074 | Eef2k | NM_001267711.1 | chr7:127986344-128050733 |
| 8981 | Ebf1 | NM_001290710.1 | chr11:44431601-44821598 | 9075 | Eef2k | NM_007908.4 | chr7:127986344-128050733 |
| 8982 | Ebf1 | NM_001290711.1 | chr11:44431601-44821598 | 9076 | Eefsec | NM_023060.3 | chr6:88207327-88396633 |
| 8983 | Ebf1 | NM_007897.3 | chr11:44431601-44821598 | 9077 | Eepd1 | NM_026189.3 | chr9:25289181-25411695 |
| 8984 | Ebf2 | NM_001276387.1 | chr14:67852128-68049789 | 9078 | Efcab1 | NM_025769.3 | chr16:14906738-14924615 |
| 8985 | Ebf2 | NM_010095.6 | chr14:67852128-68049789 | 9079 | Efcab10 | NM_029152.1 | chr12:34079718-34086134 |
| 8986 | Ebf3 | NM_001113414.1 | chr7:144385353-144506128 | 9080 | Efcab11 | NM_030172.2 | chr12:100955740-101121652 |
| 8987 | Ebf3 | NM_001113415.1 | chr7:144385353-144506128 | 9081 | Efcab12 | NM_001110506.1 | chr6:115760746-115788430 |
| 8988 | Ebf3 | NM_010096.3 | chr7:144385353-144506128 | 9082 | Efcab14 | NM_172698.2 | chr4:115410677-115449932 |
| 8989 | Ebf4 | NM_001110513.1 | chr2:130121674-130196217 | 9083 | Efcab2 | NM_026626.2 | chr1:180336011-180413380 |
| 8990 | Ebi3 | NM_015766.2 | chr17:56092046-56096445 | 9084 | Efcab3 | NM_001081046.1 | chr11:104953532-104978851 |
| 8991 | Ebna1bp2 | NM_026932.4 | chr4:118293404-118300381 | 9085 | Efcab4a | NM_001025103.2 | chr7:148646992-148652501 |
| 8992 | Ebp | NM_007898.3 | chrX:7762456-7770638 | 9086 | Efcab4b | NM_001033464.3 | chr6:127527992-127579956 |
| 8993 | Ebpl | NM_026598.3 | chr14:61958599-61979282 | 9087 | Efcab5 | NM_176965.3 | chr11:76903416-77002470 |
| 8994 | Ecd | NM_027475.3 | chr14:21139080-21167343 | 9088 | Efcab6 | NM_001161628.1 | chr15:83697141-83895779 |
| 8995 | Ece1 | NM_199307.2 | chr4:137418151-137521144 | 9089 | Efcab6 | NM_001161629.1 | chr15:83697141-83895779 |
| 8996 | Ece2 | NM_025462.2 | chr16:20611673-20645988 | 9090 | Efcab6 | NM_029946.4 | chr15:83697141-83895779 |
| 8997 | Ece2 | NM_139293.2 | chr16:20611673-20645988 | 9091 | Efcab7 | NM_145549.1 | chr4:99496190-99585388 |
| 8998 | Ece2 | NM_177940.1 | chr16:20611673-20645988 | 9092 | Efcab8 | NR_036629.1 | chr2:153606614-153620918 |
| 8999 | Ece2 | NM_177941.1 | chr16:20611673-20645988 | 9093 | Efcab9 | NM_027031.3 | chr11:32422732-32427574 |
| 9000 | Ece2 | NM_177942.1 | chr16:20611673-20645988 | 9094 | Efcc1 | NM_001159697.1 | chr6:87680862-87705905 |
| 9001 | Ecel1 | NM_001277925.1 | chr1:89044229-89052931 | 9095 | Efemp1 | NM_146015.2 | chr11:28753204-28826743 |
| 9002 | Ecel1 | NM_021306.2 | chr1:89044229-89052931 | 9096 | Efemp2 | NM_001164352.1 | chr19:5474689-5481854 |
| 9003 | Ech1 | NM_016772.1 | chr7:29610356-29617258 | 9097 | Efemp2 | NM_021474.3 | chr19:5474689-5481854 |
| 9004 | Echdc1 | NM_001110195.1 | chr10:29032971-29082248 | 9098 | Efhb | NM_172497.3 | chr17:53538213-53602646 |
| 9005 | Echdc1 | NM_025855.4 | chr10:29032971-29082248 | 9099 | Efhc1 | NM_027974.1 | chr1:20941706-20980922 |
| 9006 | Echdc2 | NM_001254754.1 | chr4:107838041-107851913 | 9100 | Efhc2 | NM_028916.4 | chrX:16709174-16896494 |
| 9007 | Echdc2 | NM_026728.4 | chr4:107838041-107851913 | 9101 | Efhd1 | NM_028889.2 | chr1:89160938-89207366 |
| 9008 | Echdc3 | NM_024208.4 | chr2:6109511-6134040 | 9102 | Efhd2 | NM_025994.3 | chr4:141414056-141430835 |
| 9009 | Echs1 | NM_053119.2 | chr7:147291621-147302322 | 9103 | Efna1 | NM_001162425.1 | chr3:89075651-89084873 |
| 9010 | Eci1 | NM_010023.4 | chr17:24563627-24576261 | 9104 | Efna1 | NM_010107.4 | chr3:89075651-89084873 |
| | | | | 9105 | Efna2 | NM_007909.3 | chr10:79642226-79652755 |

Fig. 25 - 49

| | | | |
|---|---|---|---|
| 9106 | Efna3 | NM_010108.1 | chr3:89118872-89126801 |
| 9107 | Efna4 | NM_007910.2 | chr3:89137314-89141950 |
| 9108 | Efna5 | NM_010109.3 | chr17:62952305-63230666 |
| 9109 | Efna5 | NM_207854.2 | chr17:62952305-63230666 |
| 9110 | Efnb1 | NM_010110.5 | chrX:96331468-96344330 |
| 9111 | Efnb2 | NM_010111.5 | chr8:8617438-8660773 |
| 9112 | Efnb3 | NM_007911.5 | chr11:69367593-69373739 |
| 9113 | Efr3a | NM_133766.3 | chr15:65618602-65705374 |
| 9114 | Efr3b | NM_001082483.1 | chr12:3962553-4038915 |
| 9115 | Efs | NM_010112.4 | chr14:55535379-55545625 |
| 9116 | Eftud1 | NM_001159672.1 | chr7:89797123-89926362 |
| 9117 | Eftud1 | NM_175317.3 | chr7:89797123-89926362 |
| 9118 | Eftud2 | NM_001109995.1 | chr11:102699785-102742289 |
| 9119 | Eftud2 | NM_011431.3 | chr11:102699785-102742289 |
| 9120 | Egf | NM_010113.3 | chr3:129380493-129458240 |
| 9121 | Egfbp2 | NM_010115.6 | chr7:51268081-51272338 |
| 9122 | Egfem1 | NM_001167748.1 | chr3:28981498-29589978 |
| 9123 | Egfem1 | NM_029412.1 | chr3:28981498-29589978 |
| 9124 | Egfl6 | NM_019397.3 | chrX:162960938-163023648 |
| 9125 | Egfl7 | NM_001164564.1 | chr2:26436575-26448202 |
| 9126 | Egfl7 | NM_178444.4 | chr2:26436575-26448202 |
| 9127 | Egfl7 | NM_198724.2 | chr2:26436575-26448202 |
| 9128 | Egfl7 | NM_198725.2 | chr2:26436575-26448202 |
| 9129 | Egfl8 | NM_152922.3 | chr17:34750295-34752916 |
| 9130 | Egflam | NM_001289496.1 | chr15:7156119-7348395 |
| 9131 | Egflam | NM_001289498.1 | chr15:7156119-7348395 |
| 9132 | Egflam | NM_178748.6 | chr15:7156119-7348395 |
| 9133 | Egfr | NM_010119.5 | chr11:16652205-16813910 |
| 9134 | Egfr | NM_207655.2 | chr11:16652205-16813910 |
| 9135 | Egln1 | NM_053207.2 | chr8:127432486-127473154 |
| 9136 | Egln2 | NM_053426.3 | chr7:27943676-27951821 |
| 9137 | Egln3 | NM_028133.2 | chr12:55279967-55304861 |
| 9138 | Egr1 | NM_007913.5 | chr18:35020860-35024610 |
| 9139 | Egr2 | NM_010118.3 | chr10:67000616-67004936 |
| 9140 | Egr3 | NM_001289925.1 | chr14:70477251-70482420 |
| 9141 | Egr3 | NM_001289927.1 | chr14:70477251-70482420 |
| 9142 | Egr3 | NM_018781.3 | chr14:70477251-70482420 |
| 9143 | Egr4 | NM_020596.2 | chr6:85461115-85463536 |
| 9144 | Ehbp1 | NM_001252515.1 | chr11:21905828-22186798 |
| 9145 | Ehbp1 | NM_153078.4 | chr11:21905828-22186798 |
| 9146 | Ehbp1l1 | NM_001114595.1 | chr19:5707373-5726317 |
| 9147 | Ehbp1l1 | NM_001112518.3 | chr19:5707373-5726317 |
| 9148 | Ehbp1l1 | NM_001114597.1 | chr19:5707373-5726317 |
| 9149 | Ehbp1l1 | NM_053252.3 | chr19:5707373-5726317 |
| 9150 | Ehd1 | NM_010119.5 | chr19:6276895-6300096 |
| 9151 | Ehd2 | NM_153068.3 | chr7:16534335-16552884 |
| 9152 | Ehd3 | NM_020578.1 | chr17:74154180-74181433 |
| 9153 | Ehd4 | NM_133838.4 | chr2:119915222-119980311 |
| 9154 | Ehf | NM_007914.3 | chr2:103103589-103143353 |
| 9155 | Ehhadh | NM_023737.3 | chr16:21761357-21787907 |
| 9156 | Ehmt1 | NM_001012518.3 | chr2:24646288-24775129 |
| 9157 | Ehmt1 | NM_001109686.2 | chr2:24646288-24775129 |
| 9158 | Ehmt1 | NM_001109687.2 | chr2:24646288-24775129 |
| 9159 | Ehmt1 | NM_172545.4 | chr2:24646288-24775129 |
| 9160 | Ehmt2 | NM_001286573.1 | chr17:35035436-35050995 |
| 9161 | Ehmt2 | NM_001286575.1 | chr17:35035436-35050995 |
| 9162 | Ehmt2 | NM_145830.2 | chr17:35035436-35050995 |
| 9163 | Ehmt2 | NM_147151.2 | chr17:35035436-35050995 |
| 9164 | Ei24 | NM_001199494.1 | chr9:36586737-36604978 |
| 9165 | Ei24 | NM_007915.5 | chr9:36586737-36604978 |
| 9166 | Eid1 | NM_025613.3 | chr2:125498836-125501378 |
| 9167 | Eid2 | NM_198425.2 | chr7:29052899-29054187 |
| 9168 | Eid2b | NM_001177427.1 | chr7:29062724-29065148 |
| 9169 | Eid3 | NM_025499.2 | chr10:82329371-82330674 |
| 9170 | Eif1 | NM_011508.1 | chr11:100181309-100183410 |
| 9171 | Eif1a | NM_010120.5 | chr18:46757357-46769879 |
| 9172 | Eif1ad | NM_027236.2 | chr19:5366813-5371511 |
| 9173 | Eif1ax | NM_025437.4 | chrX:155810126-155823631 |
| 9174 | Eif1b | NM_026892.3 | chr9:120401723-120404445 |
| 9175 | Eif2a | NM_001005509.2 | chr3:58329743-58361423 |
| 9176 | Eif2ak1 | NM_013557.2 | chr5:144578661-144663586 |
| 9177 | Eif2ak2 | NM_011163.4 | chr17:79251889-79281912 |
| 9178 | Eif2ak3 | NM_010121.2 | chr6:70794520-70855234 |
| 9179 | Eif2ak4 | NM_001177806.1 | chr2:118214352-118300970 |
| 9180 | Eif2ak4 | NM_013719.3 | chr2:118214352-118300970 |
| 9181 | Eif2b1 | NM_145371.3 | chr5:125020222-125029066 |
| 9182 | Eif2b2 | NM_145445.3 | chr12:86560462-86567578 |
| 9183 | Eif2b3 | NM_001111277.1 | chr4:116692012-116759457 |
| 9184 | Eif2b3 | NM_175435.4 | chr4:116692012-116759457 |
| 9185 | Eif2b4 | NM_001127355.1 | chr5:31235515-31651218 |
| 9186 | Eif2b4 | NM_001127356.1 | chr5:31235515-31651218 |
| 9187 | Eif2b4 | NM_010122.2 | chr5:31235515-31651218 |
| 9188 | Eif2b5 | NM_172265.2 | chr16:20498889-20509398 |
| 9189 | Eif2d | NM_001136070.1 | chr1:133049783-133070048 |
| 9190 | Eif2d | NM_010709.3 | chr1:133049783-133070048 |
| 9191 | Eif2s1 | NM_026114.3 | chr12:79963058-79987997 |
| 9192 | Eif2s2 | NM_026030.2 | chr2:154697145-154718642 |
| 9193 | Eif2s3x | NM_012010.3 | chrX:91434047-91457990 |
| 9194 | Eif2s3y | NM_012011.1 | chrY:347054-365037 |
| 9195 | Eif3a | NM_010123.3 | chr19:60837019-60866596 |
| 9196 | Eif3b | NM_133916.2 | chr5:140895259-140919312 |
| 9197 | Eif3c | NM_146200.1 | chr7:133690424-133709880 |
| 9198 | Eif3d | NM_018749.2 | chr15:77789427-77801254 |
| 9199 | Eif3e | NM_008388.2 | chr15:43081585-43114282 |
| 9200 | Eif3f | NM_025344.2 | chr7:116077928-116085456 |
| 9201 | Eif3g | NM_016876.3 | chr9:20698792-20703034 |
| 9202 | Eif3h | NM_080635.1 | chr15:51618108-51697007 |
| 9203 | Eif3i | NM_018799.2 | chr4:129269217-129277892 |
| 9204 | Eif3j1 | NM_144545.4 | chr2:121854316-121879368 |
| 9205 | Eif3j2 | NM_001256055.1 | chr2:121854319-121879367 |
| 9206 | Eif3k | NM_001285942.1 | chr7:29756390-29766907 |
| 9207 | Eif3k | NM_001285943.1 | chr7:29756390-29766907 |
| 9208 | Eif3k | NM_028659.3 | chr7:29756390-29766907 |
| 9209 | Eif3l | NM_145139.2 | chr15:78905652-78924830 |
| 9210 | Eif3m | NM_145380.2 | chr2:104839814-104857184 |
| 9211 | Eif4a1 | NM_001159375.1 | chr11:69480437-69485925 |
| 9212 | Eif4a1 | NM_144958.4 | chr11:69480437-69485925 |
| 9213 | Eif4a2 | NM_001123037.2 | chr16:23107540-23127803 |
| 9214 | Eif4a2 | NM_001123038.2 | chr16:23107540-23127803 |
| 9215 | Eif4a2 | NM_013506.3 | chr16:23107540-23127803 |
| 9216 | Eif4a2 | NR_110335.1 | chr16:23107540-23127803 |
| 9217 | Eif4a3 | NM_138669.1 | chr11:119149676-119161357 |
| 9218 | Eif4b | NM_145625.3 | chr15:101904203-101927604 |
| 9219 | Eif4e | NM_007917.3 | chr3:138189155-138220563 |
| 9220 | Eif4e1b | NM_001033269.3 | chr13:54885358-54889819 |
| 9221 | Eif4e1b | NM_001039683.2 | chr13:54885358-54889819 |
| 9222 | Eif4e1b | NM_001286178.1 | chr13:54885358-54889819 |
| 9223 | Eif4e1b | NM_001286179.1 | chr13:54885358-54889819 |
| 9224 | Eif4e1b | NM_001286180.1 | chr13:54885358-54889819 |
| 9225 | Eif4e1b | NR_104406.1 | chr13:54885358-54889819 |
| 9226 | Eif4e1b | NR_104407.1 | chr13:54885358-54889819 |
| 9227 | Eif4e2 | NM_001039169.1 | chr1:89110488-89137063 |
| 9228 | Eif4e2 | NM_001039170.1 | chr1:89110488-89137063 |
| 9229 | Eif4e2 | NM_023314.3 | chr1:89110488-89137063 |
| 9230 | Eif4e3 | NM_025829.2 | chr6:99575130-99616765 |
| 9231 | Eif4ebp1 | NM_007918.3 | chr8:28370798-28386128 |
| 9232 | Eif4ebp2 | NM_010124.2 | chr10:60895244-60915417 |
| 9233 | Eif4ebp3 | NM_201256.4 | chr18:36823713-36825978 |
| 9234 | Eif4enif1 | NM_001166547.1 | chr11:3102355-3144591 |
| 9235 | Eif4enif1 | NM_001166548.1 | chr11:3102355-3144591 |
| 9236 | Eif4enif1 | NM_001166549.1 | chr11:3102355-3144591 |
| 9237 | Eif4enif1 | NM_023743.2 | chr11:3102355-3144591 |
| 9238 | Eif4g1 | NM_001005331.1 | chr16:20672821-20692956 |
| 9239 | Eif4g1 | NM_145941.3 | chr16:20672821-20692956 |
| 9240 | Eif4g2 | NM_001040131.2 | chr7:118211498-118226544 |
| 9241 | Eif4g2 | NM_013507.3 | chr7:118211498-118226544 |
| 9242 | Eif4g3 | NM_001256195.1 | chr4:137549370-137762994 |
| 9243 | Eif4g3 | NM_001256198.1 | chr4:137549370-137762994 |
| 9244 | Eif4g3 | NM_172703.3 | chr4:137549370-137762994 |
| 9245 | Eif4h | NM_033561.1 | chr5:135095745-135115198 |
| 9246 | Eif5 | NM_173363.5 | chr12:112776311-112784964 |
| 9247 | Eif5 | NM_178041.2 | chr12:112776311-112784964 |
| 9248 | Eif5a | NM_001166589.1 | chr11:69730213-69735460 |
| 9249 | Eif5a | NM_001166590.1 | chr11:69730213-69735460 |
| 9250 | Eif5a | NM_001166591.1 | chr11:69730213-69735460 |
| 9251 | Eif5a | NM_001166592.1 | chr11:69730213-69735460 |
| 9252 | Eif5a | NM_001166593.1 | chr11:69730213-69735460 |
| 9253 | Eif5a | NM_001166594.1 | chr11:69730213-69735460 |
| 9254 | Eif5a | NM_001166595.1 | chr11:69730213-69735460 |
| 9255 | Eif5a | NM_001166596.1 | chr11:69730213-69735460 |
| 9256 | Eif5a | NM_181582.4 | chr11:69730213-69735460 |
| 9257 | Eif5a2 | NM_177586.5 | chr3:28680232-28697768 |
| 9258 | Eif5b | NM_198303.2 | chr1:38054855-38112424 |
| 9259 | Eif6 | NM_010579.2 | chr2:155645572-155652661 |
| 9260 | Elac1 | NM_053255.3 | chr18:73894691-73914133 |
| 9261 | Elac2 | NM_023479.2 | chr11:64792557-64815578 |
| 9262 | Elane | NM_015779.2 | chr10:79349056-79350961 |
| 9263 | Elavl1 | NM_010485.3 | chr8:4284781-4325100 |
| 9264 | Elavl2 | NM_001177883.1 | chr4:90917456-91066675 |
| 9265 | Elavl2 | NM_010486.2 | chr4:90917456-91066675 |
| 9266 | Elavl2 | NM_207685.1 | chr4:90917456-91066675 |
| 9267 | Elavl2 | NM_207686.1 | chr4:90917456-91066675 |
| 9268 | Elavl3 | NM_010487.2 | chr9:21819448-21856467 |
| 9269 | Elavl4 | NM_001038698.1 | chr4:109876341-110024516 |
| 9270 | Elavl4 | NM_001163397.1 | chr4:109876341-110024516 |
| 9271 | Elavl4 | NM_001163399.1 | chr4:109876341-110024516 |
| 9272 | Elavl4 | NM_010488.4 | chr4:109876341-110024516 |
| 9273 | Elf1 | NM_001286411.1 | chr14:79859743-79982298 |
| 9274 | Elf1 | NM_001286412.1 | chr14:79859743-79982298 |
| 9275 | Elf1 | NM_007920.4 | chr14:79859743-79982298 |
| 9276 | Elf2 | NM_001291059.1 | chr3:51056641-51144566 |
| 9277 | Elf2 | NM_001291062.1 | chr3:51056641-51144566 |
| 9278 | Elf2 | NM_001291063.1 | chr3:51056641-51144566 |
| 9279 | Elf2 | NM_023502.2 | chr3:51056641-51144566 |
| 9280 | Elf3 | NM_001163131.1 | chr1:137150150-137155049 |
| 9281 | Elf3 | NM_007921.3 | chr1:137150150-137155049 |
| 9282 | Elf4 | NM_019680.2 | chrX:45764225-45816309 |
| 9283 | Elf5 | NM_001145813.1 | chr2:103252254-103291145 |
| 9284 | Elf5 | NM_010125.3 | chr2:103252254-103291145 |
| 9285 | Elfn1 | NM_175522.3 | chr5:140383896-140450678 |
| 9286 | Elfn2 | NM_183141.2 | chr15:78500436-78548543 |
| 9287 | Elk1 | NM_007922.5 | chrX:20510520-20527734 |
| 9288 | Elk3 | NM_001282967.1 | chr10:92710160-92773904 |
| 9289 | Elk3 | NM_013508.2 | chr10:92710160-92773904 |
| 9290 | Elk4 | NM_007923.2 | chr1:133904181-133922261 |
| 9291 | Ell | NM_007924.2 | chr8:73063573-73116757 |
| 9292 | Ell2 | NM_139953.2 | chr13:75844931-75909806 |
| 9293 | Ell3 | NM_145973.2 | chr2:121264762-121268337 |
| 9294 | Elmo1 | NM_080288.2 | chr13:20182375-20700222 |
| 9295 | Elmo1 | NM_198093.3 | chr13:20182375-20700222 |

Fig. 25 - 50

| | | | |
|---|---|---|---|
| 9296 | Elmo2 | NM_080287.2 | chr2:165113530-165151979 |
| 9297 | Elmo2 | NM_207705.1 | chr2:165113530-165151979 |
| 9298 | Elmo2 | NM_207706.1 | chr2:165113530-165151979 |
| 9299 | Elmo3 | NM_172760.3 | chr8:107829501-107834523 |
| 9300 | Elmo1 | NM_177769.4 | chr9:53759266-53823108 |
| 9301 | Elmod2 | NM_001170691.1 | chr8:85836530-85856385 |
| 9302 | Elmod2 | NM_178736.5 | chr8:85836530-85856385 |
| 9303 | Elmod3 | NM_001253692.1 | chr6:72515915-72548407 |
| 9304 | Elmod3 | NM_144917.5 | chr6:72515915-72548407 |
| 9305 | Elmsan1 | NM_001163501.1 | chr12:85490122-85559831 |
| 9306 | Elmsan1 | NM_001163502.1 | chr12:85490122-85559831 |
| 9307 | Eln | NM_007925.3 | chr5:135178465-135223124 |
| 9308 | Elof1 | NM_170777.3 | chr9:21917433-21918613 |
| 9309 | Elovl1 | NM_001039175.2 | chr4:118100697-118109948 |
| 9310 | Elovl1 | NM_001039176.2 | chr4:118100697-118109948 |
| 9311 | Elovl1 | NM_019422.3 | chr4:118100697-118109948 |
| 9312 | Elovl2 | NM_019423.2 | chr13:41277750-41315772 |
| 9313 | Elovl3 | NM_007703.2 | chr19:46206389-46210184 |
| 9314 | Elovl4 | NM_148941.2 | chr9:83672298-83699912 |
| 9315 | Elovl5 | NM_134255.3 | chr9:77765171-77832326 |
| 9316 | Elovl6 | NM_130450.2 | chr3:129235303-129341411 |
| 9317 | Elovl7 | NM_029001.5 | chr13:109004597-109077301 |
| 9318 | Elp2 | NM_021448.2 | chr18:24762461-24797331 |
| 9319 | Elp3 | NM_001253812.1 | chr14:66149282-66211949 |
| 9320 | Elp3 | NM_028811.3 | chr14:66149282-66211949 |
| 9321 | Elp3 | NR_045599.1 | chr14:66149282-66211949 |
| 9322 | Elp4 | NM_023876.3 | chr2:105540265-105744657 |
| 9323 | Elp5 | NM_001253700.1 | chr11:69781726-69804102 |
| 9324 | Elp5 | NM_018740.2 | chr11:69781726-69804102 |
| 9325 | Elp6 | NM_001081381.1 | chr9:110207695-110224606 |
| 9326 | Eltd1 | NM_133222.3 | chr3:151100845-151208045 |
| 9327 | Emb | NM_010330.4 | chr13:118009379-118063222 |
| 9328 | Emc1 | NM_001039200.2 | chr4:138908501-138934650 |
| 9329 | Emc1 | NM_146157.4 | chr4:138908501-138934650 |
| 9330 | Emc10 | NM_197991.2 | chr7:51745307-51751883 |
| 9331 | Emc2 | NM_025736.2 | chr15:43308774-43359323 |
| 9332 | Emc3 | NM_175101.2 | chr6:113464880-113481632 |
| 9333 | Emc4 | NM_026519.3 | chr2:112203176-112208184 |
| 9334 | Emc6 | NM_001146870.1 | chr11:72989004-72990544 |
| 9335 | Emc6 | NM_025318.3 | chr11:72989004-72990544 |
| 9336 | Emc7 | NM_133749.2 | chr2:112295181-112307593 |
| 9337 | Emc8 | NM_010926.5 | chr8:123177813-123192012 |
| 9338 | Emc9 | NM_033146.1 | chr14:56200361-56204091 |
| 9339 | Emcn | NM_001163522.1 | chr3:137004041-137094033 |
| 9340 | Emcn | NM_016885.2 | chr3:137004041-137094033 |
| 9341 | Emd | NM_007927.3 | chrX:71500025-71503232 |
| 9342 | Eme1 | NM_177752.4 | chr11:94506316-94515068 |
| 9343 | Eme2 | NM_001163102.1 | chr17:25029096-25032032 |
| 9344 | Emg1 | NM_013536.2 | chr6:124654388-124662196 |
| 9345 | Emid1 | NM_080595.2 | chr11:5006268-5052225 |
| 9346 | Emilin1 | NM_133918.2 | chr5:31216158-31223646 |
| 9347 | Emilin2 | NM_145158.3 | chr17:71601515-71660305 |
| 9348 | Emilin3 | NM_001291145.1 | chr2:160732173-160738075 |
| 9349 | Emilin3 | NM_182840.2 | chr2:160732173-160738075 |
| 9350 | Eml1 | NM_001043335.1 | chr12:109609362-109940516 |
| 9351 | Eml1 | NM_001043336.1 | chr12:109609362-109940516 |
| 9352 | Eml1 | NM_001286346.1 | chr12:109609362-109940516 |
| 9353 | Eml1 | NM_001286347.1 | chr12:109609362-109940516 |
| 9354 | Eml2 | NM_001162996.1 | chr7:19766518-19791831 |
| 9355 | Eml2 | NM_028153.1 | chr7:19766518-19791831 |
| 9356 | Eml3 | NM_144872.1 | chr19:9004183-9016072 |
| 9357 | Eml4 | NM_001114361.1 | chr17:83750270-83879699 |
| 9358 | Eml4 | NM_001114362.1 | chr17:83750270-83879699 |
| 9359 | Eml4 | NM_001286567.1 | chr17:83750270-83879699 |
| 9360 | Eml4 | NM_199466.3 | chr17:83750270-83879699 |
| 9361 | Eml5 | NM_001081191.1 | chr12:100024814-100139694 |
| 9362 | Eml6 | NM_146016.2 | chr11:29643051-29926033 |
| 9363 | Emp1 | NM_001288627.1 | chr6:135312948-135333191 |
| 9364 | Emp1 | NM_001288628.1 | chr6:135312948-135333191 |
| 9365 | Emp1 | NM_010128.4 | chr6:135312948-135333191 |
| 9366 | Emp2 | NM_007929.2 | chr16:10281841-10314061 |
| 9367 | Emp3 | NM_001146346.1 | chr7:53173392-53176796 |
| 9368 | Emp3 | NM_010128.2 | chr7:53173392-53176796 |
| 9369 | Emr1 | NM_010130.4 | chr17:57498108-57622952 |
| 9370 | Emr4 | NM_139138.3 | chr17:55889248-55992927 |
| 9371 | Emx1 | NM_010131.2 | chr6:85173924-85154457 |
| 9372 | Emx2 | NM_010132.2 | chr19:59533179-59539847 |
| 9373 | Emx2os | NR_002863.2 | chr19:59499593-59533125 |
| 9374 | En1 | NM_010133.2 | chr1:122499063-122504568 |
| 9375 | En2 | NM_010134.3 | chr5:28492235-28498706 |
| 9376 | Enah | NM_001083120.2 | chr1:183826515-183950111 |
| 9377 | Enah | NM_001083121.2 | chr1:183826515-183950111 |
| 9378 | Enah | NM_008680.3 | chr1:183826515-183950111 |
| 9379 | Enah | NM_010135.3 | chr1:183826515-183950111 |
| 9380 | Enam | NM_017468.3 | chr5:88916999-88935074 |
| 9381 | Enc1 | NM_007930.4 | chr13:98011059-98022995 |
| 9382 | Endod1 | NM_028013.3 | chr9:14158433-14185686 |
| 9383 | Endog | NM_007931.1 | chr2:30027044-30029589 |
| 9384 | Endou | NM_001168693.1 | chr15:97541449-97561836 |
| 9385 | Endou | NM_008902.3 | chr15:97541449-97561836 |
| 9386 | Endov | NM_001164636.1 | chr11:119352660-119372779 |
| 9387 | Endov | NM_177394.3 | chr11:119352660-119372779 |
| 9388 | Eng | NM_001146348.1 | chr2:32502114-32549695 |
| 9389 | Eng | NM_001146350.1 | chr2:32502114-32549695 |
| 9390 | Eng | NM_007932.2 | chr2:32502114-32549695 |
| 9391 | Engase | NM_172573.2 | chr11:118338273-118350512 |
| 9392 | Enho | NM_027147.1 | chr4:41585177-41587335 |
| 9393 | Enkd1 | NM_198299.1 | chr8:108227551-108232068 |
| 9394 | Enkur | NM_027728.2 | chr2:21102357-21126992 |
| 9395 | Eno1 | NM_023119.2 | chr4:149611306-149622982 |
| 9396 | Eno1b | NM_001025388.1 | chr18:48082494-48267634 |
| 9397 | Eno1b | NM_001025388.1 | chr4:149611305-149622982 |
| 9398 | Eno2 | NM_013509.3 | chr6:124710072-124719527 |
| 9399 | Eno3 | NM_001136062.2 | chr11:70470677-70476015 |
| 9400 | Eno3 | NM_001276285.1 | chr11:70470677-70476015 |
| 9401 | Eno3 | NM_007933.3 | chr11:70470677-70476015 |
| 9402 | Eno4 | NM_178689.4 | chr19:59017914-59045911 |
| 9403 | Enoph1 | NM_001163035.1 | chr5:100469012-100497784 |
| 9404 | Enoph1 | NM_026421.3 | chr5:100469012-100497784 |
| 9405 | Enoph1 | NR_027990.1 | chr5:100469012-100497784 |
| 9406 | Enox1 | NM_001253759.1 | chr14:77556569-78121570 |
| 9407 | Enox1 | NM_172813.3 | chr14:77556569-78121570 |
| 9408 | Enox2 | NM_001271447.1 | chrX:46362883-46641419 |
| 9409 | Enox2 | NM_001271448.1 | chrX:46362883-46641419 |
| 9410 | Enox2 | NM_001271449.1 | chrX:46362883-46641419 |
| 9411 | Enox2 | NM_001271450.1 | chrX:46362883-46641419 |
| 9412 | Enox2 | NM_001271451.1 | chrX:46362883-46641419 |
| 9413 | Enox2 | NM_145951.5 | chrX:46362883-46641419 |
| 9414 | Enpep | NM_007934.3 | chr3:128972094-129035667 |
| 9415 | Enpp1 | NM_008813.4 | chr10:24361216-24431908 |
| 9416 | Enpp2 | NM_001136077.2 | chr15:54670233-54751701 |
| 9417 | Enpp2 | NM_001285994.1 | chr15:54670233-54751701 |
| 9418 | Enpp2 | NM_001285995.1 | chr15:54670233-54751701 |
| 9419 | Enpp2 | NM_015744.3 | chr15:54670233-54751701 |
| 9420 | Enpp3 | NM_134005.2 | chr10:24493619-24556001 |
| 9421 | Enpp4 | NM_199016.2 | chr17:44233258-44242757 |
| 9422 | Enpp5 | NM_001168620.1 | chr17:44215794-44223510 |
| 9423 | Enpp5 | NM_032003.2 | chr17:44215794-44223510 |
| 9424 | Enpp6 | NM_177304.3 | chr8:48072278-48180249 |
| 9425 | Enpp7 | NM_001030291.1 | chr11:118849501-118854155 |
| 9426 | Ensa | NM_001026212.1 | chr3:95428901-95436039 |
| 9427 | Ensa | NM_019561.2 | chr3:95428901-95436039 |
| 9428 | Enthd1 | NM_001163189.1 | chr15:80282669-80390900 |
| 9429 | Enthd2 | NM_183137.2 | chr11:119951835-119960045 |
| 9430 | Entpd1 | NM_009848.4 | chr19:40734283-40816092 |
| 9431 | Entpd2 | NM_009849.2 | chr2:25251393-25256843 |
| 9432 | Entpd3 | NM_178676.4 | chr9:120448935-120477443 |
| 9433 | Entpd4 | NM_026174.1 | chr14:69955207-69984799 |
| 9434 | Entpd5 | NM_001026214.2 | chr12:85714825-85749979 |
| 9435 | Entpd5 | NM_001286049.1 | chr12:85714825-85749979 |
| 9436 | Entpd5 | NM_001286058.1 | chr12:85714825-85749979 |
| 9437 | Entpd5 | NM_007647.3 | chr12:85714825-85749979 |
| 9438 | Entpd6 | NM_172117.5 | chr2:150574816-150597410 |
| 9439 | Entpd7 | NM_053103.5 | chr19:43784179-43808343 |
| 9440 | Entpd8 | NM_028093.1 | chr2:24935843-24941239 |
| 9441 | Eny2 | NM_175009.3 | chr15:44259657-44269231 |
| 9442 | Eogt | NM_175313.4 | chr6:97060937-97098877 |
| 9443 | Eomes | NM_001164789.1 | chr9:118387306-118395250 |
| 9444 | Eomes | NM_010136.2 | chr9:118387306-118395250 |
| 9445 | Ep300 | NM_177821.6 | chr15:81416643-81482507 |
| 9446 | Ep400 | NM_029337.2 | chr5:111093391-111199736 |
| 9447 | Ep400 | NM_173066.1 | chr5:111093391-111199736 |
| 9448 | Epas1 | NM_010137.3 | chr17:87153203-87232750 |
| 9449 | Epb4.1 | NM_001128606.1 | chr4:131479340-131631228 |
| 9450 | Epb4.1 | NM_001128607.1 | chr4:131479340-131631228 |
| 9451 | Epb4.1 | NM_183428.3 | chr4:131479340-131631228 |
| 9452 | Epb4.1l1 | NM_001003815.2 | chr2:156246644-156368950 |
| 9453 | Epb4.1l1 | NM_001006664.3 | chr2:156246644-156368950 |
| 9454 | Epb4.1l1 | NM_001291120.1 | chr2:156246644-156368950 |
| 9455 | Epb4.1l1 | NM_001291121.1 | chr2:156246644-156368950 |
| 9456 | Epb4.1l1 | NM_001291122.1 | chr2:156246644-156368950 |
| 9457 | Epb4.1l1 | NM_001291123.1 | chr2:156246644-156368950 |
| 9458 | Epb4.1l1 | NM_013510.4 | chr2:156246644-156368950 |
| 9459 | Epb4.1l2 | NM_001199265.1 | chr10:25079603-25243324 |
| 9460 | Epb4.1l2 | NM_013511.3 | chr10:25079603-25243324 |
| 9461 | Epb4.1l3 | NM_033813.1 | chr17:69506150-69639327 |
| 9462 | Epb4.1l4a | NM_013512.2 | chr18:33955980-34166860 |
| 9463 | Epb4.1l4b | NM_019427.2 | chr4:57074597-57156028 |
| 9464 | Epb4.1l5 | NM_001113416.1 | chr1:121441609-121545577 |
| 9465 | Epb4.1l5 | NM_145506.4 | chr1:121441609-121545577 |
| 9466 | Epb4.2 | NM_013513.2 | chr2:120843952-120862491 |
| 9467 | Epc1 | NM_001276350.1 | chr18:6435948-6516106 |
| 9468 | Epc1 | NM_007935.2 | chr18:6435948-6516106 |
| 9469 | Epc1 | NM_027497.3 | chr18:6435948-6516106 |
| 9470 | Epc2 | NM_172663.1 | chr2:49307005-49407129 |
| 9471 | Epcam | NM_008532.2 | chr17:88035318-88050467 |
| 9472 | Epdr1 | NM_134065.4 | chr13:19683576-19711699 |
| 9473 | Epg5 | NM_001195633.1 | chr18:78135205-78231766 |
| 9474 | Epgn | NM_053087.2 | chr5:91456542-91464238 |
| 9475 | Epha1 | NM_023580.4 | chr6:42308486-42323267 |
| 9476 | Epha10 | NM_001256432.3 | chr4:124559028-124595044 |
| 9477 | Epha10 | NM_177671.5 | chr4:124559028-124595044 |
| 9478 | Epha2 | NM_010139.3 | chr4:140857135-140885299 |
| 9479 | Epha3 | NM_010140.1 | chr16:63545043-63863983 |
| 9480 | Epha4 | NM_007936.3 | chr1:77363760-77511663 |
| 9481 | Epha5 | NM_007937.3 | chr5:84483787-84846407 |
| 9482 | Epha6 | NM_007938.3 | chr16:59653309-60605357 |
| 9483 | Epha7 | NM_001122889.1 | chr4:28740280-28894653 |
| 9484 | Epha7 | NM_001290434.1 | chr4:28740280-28894653 |
| 9485 | Epha7 | NM_010141.4 | chr4:28740280-28894653 |

Fig. 25 - 51

| | | | |
|---|---|---|---|
| 9486 | Epha8 | NM_007939.2 | chr4:136485333-136512731 |
| 9487 | Ephb1 | NM_001168296.1 | chr9:101824457-102257023 |
| 9488 | Ephb1 | NM_173447.3 | chr9:101824457-102257023 |
| 9489 | Ephb2 | NM_001290753.1 | chr4:136209524-136391926 |
| 9490 | Ephb2 | NM_010142.3 | chr4:136209524-136391926 |
| 9491 | Ephb3 | NM_010143.1 | chr16:21204867-21223377 |
| 9492 | Ephb4 | NM_001159971.1 | chr5:137791336-137815750 |
| 9493 | Ephb4 | NM_010144.6 | chr5:137791336-137815750 |
| 9494 | Ephb6 | NM_001146351.1 | chr6:41555480-41570506 |
| 9495 | Ephb6 | NM_007680.4 | chr6:41555480-41570506 |
| 9496 | Ephx1 | NM_010145.2 | chr1:182919686-182947626 |
| 9497 | Ephx2 | NM_001271402.1 | chr14:66703208-66743359 |
| 9498 | Ephx2 | NM_001271403.1 | chr14:66703208-66743359 |
| 9499 | Ephx2 | NM_001271421.1 | chr14:66703208-66743359 |
| 9500 | Ephx2 | NM_007940.4 | chr14:66703208-66743359 |
| 9501 | Ephx3 | NM_001033163.3 | chr17:32320714-32326408 |
| 9502 | Ephx4 | NM_001001804.2 | chr5:107832531-107859050 |
| 9503 | Epm2a | NM_010146.2 | chr10:11063242-11177275 |
| 9504 | Epm2aip1 | NM_175266.4 | chr9:111174348-111181595 |
| 9505 | Epn1 | NM_001252454.1 | chr7:5031836-5049780 |
| 9506 | Epn1 | NM_010147.3 | chr7:5031836-5049780 |
| 9507 | Epn2 | NM_001252188.1 | chr11:61330750-61393189 |
| 9508 | Epn2 | NM_001252189.1 | chr11:61330750-61393189 |
| 9509 | Epn2 | NM_010148.3 | chr11:61330750-61393189 |
| 9510 | Epn3 | NM_027984.3 | chr11:94350912-94361288 |
| 9511 | Epo | NM_007942.2 | chr5:137924247-137927044 |
| 9512 | Epor | NM_010149.3 | chr9:21763342-21768020 |
| 9513 | Eppin | NM_029325.2 | chr2:164413842-164419071 |
| 9514 | Eppk1 | NM_144848.2 | chr15:75931918-75950625 |
| 9515 | Eprs | NM_029735.1 | chr1:187186973-187252234 |
| 9516 | Eps15 | NM_001159964.1 | chr4:108952879-109060421 |
| 9517 | Eps15 | NM_007943.3 | chr4:108952879-109060421 |
| 9518 | Eps15l1 | NM_001122832.1 | chr8:74864895-74945373 |
| 9519 | Eps15l1 | NM_001289859.1 | chr8:74864895-74945373 |
| 9520 | Eps15l1 | NM_007944.3 | chr8:74864895-74945373 |
| 9521 | Eps8 | NM_001271587.1 | chr6:137425765-137597806 |
| 9522 | Eps8 | NM_001271588.1 | chr6:137425765-137597806 |
| 9523 | Eps8 | NM_001271589.1 | chr6:137425765-137597806 |
| 9524 | Eps8 | NM_001271595.1 | chr6:137425765-137597806 |
| 9525 | Eps8 | NM_007945.3 | chr6:137425765-137597806 |
| 9526 | Eps8l1 | NM_001290416.1 | chr7:4416336-4432089 |
| 9527 | Eps8l1 | NM_026146.4 | chr7:4416336-4432089 |
| 9528 | Eps8l2 | NM_133191.2 | chr7:148524901-148548915 |
| 9529 | Eps8l3 | NM_133867.2 | chr3:107680148-107695818 |
| 9530 | Epsti1 | NM_029495.2 | chr14:78304045-78402463 |
| 9531 | Epsti1 | NM_178825.4 | chr14:78304045-78402463 |
| 9532 | Ept1 | NM_027652.2 | chr5:30559157-30598976 |
| 9533 | Epx | NM_007946.2 | chr11:87677499-87689038 |
| 9534 | Epyc | NM_007884.2 | chr10:97106702-97144534 |
| 9535 | Eqtn | NM_001290623.1 | chr4:94573957-94595534 |
| 9536 | Eqtn | NM_027089.4 | chr4:94573957-94595534 |
| 9537 | Eral1 | NM_022313.2 | chr11:77886877-77893885 |
| 9538 | Erap1 | NM_030711.4 | chr13:74777319-74829323 |
| 9539 | Eras | NM_181548.2 | chrX:7501402-7505733 |
| 9540 | Erbb2 | NM_001003817.1 | chr11:98273798-98299030 |
| 9541 | Erbb2ip | NM_001005868.2 | chr13:104608865-104710666 |
| 9542 | Erbb2ip | NM_001289473.1 | chr13:104608865-104710666 |
| 9543 | Erbb2ip | NM_001289474.1 | chr13:104608865-104710666 |
| 9544 | Erbb2ip | NM_001289475.1 | chr13:104608865-104710666 |
| 9545 | Erbb3 | NM_010153.1 | chr10:128006424-128026557 |
| 9546 | Erbb4 | NM_010154.1 | chr1:68086539-69154633 |
| 9547 | Erc1 | NM_053204.2 | chr6:119520813-119798168 |
| 9548 | Erc1 | NM_178085.3 | chr6:119520813-119798168 |
| 9549 | Erc1 | NR_104484.1 | chr6:119520813-119798168 |
| 9550 | Erc2 | NM_177814.4 | chr14:28435627-29291723 |
| 9551 | Ercc1 | NM_001127324.1 | chr7:19930419-19944832 |
| 9552 | Ercc1 | NM_007948.2 | chr7:19930419-19944832 |
| 9553 | Ercc2 | NM_007949.4 | chr7:19967388-19981041 |
| 9554 | Ercc3 | NM_133658.1 | chr18:32399984-32429801 |
| 9555 | Ercc4 | NM_015769.2 | chr16:13109828-13152102 |
| 9556 | Ercc5 | NM_011729.2 | chr1:44204588-44238105 |
| 9557 | Ercc6 | NM_001081221.1 | chr14:33326706-33394175 |
| 9558 | Ercc6l | NM_146235.3 | chrX:99338158-99352430 |
| 9559 | Ercc6l2 | NM_001013608.2 | chr13:63916627-64001609 |
| 9560 | Ercc6l2 | NM_023507.3 | chr13:63916627-64001609 |
| 9561 | Ercc8 | NM_028042.3 | chr13:108948931-108985175 |
| 9562 | Ereg | NM_007950.2 | chr5:91503642-91522675 |
| 9563 | Erf | NM_010155.3 | chr7:26027578-26035777 |
| 9564 | Erg | NM_133659.3 | chr16:95581810-95751972 |
| 9565 | Ergic1 | NM_026170.3 | chr17:26698456-26793878 |
| 9566 | Ergic2 | NM_001286560.1 | chr6:147995937-148392874 |
| 9567 | Ergic2 | NM_026168.4 | chr6:147995937-148392874 |
| 9568 | Ergic2 | NM_026355.3 | chr6:147995937-148392874 |
| 9569 | Ergic3 | NM_025516.4 | chr2:155833860-155844015 |
| 9570 | Erh | NM_007951.3 | chr12:81735009-81744848 |
| 9571 | Eri1 | NM_026067.3 | chr8:36528318-36558587 |
| 9572 | Eri2 | NM_027672.2 | chr7:126927340-126937572 |
| 9573 | Eri3 | NM_001285899.1 | chr4:117222928-117346902 |
| 9574 | Eri3 | NM_001285901.1 | chr4:117222928-117346902 |
| 9575 | Eri3 | NM_001285902.1 | chr4:117222928-117346902 |
| 9576 | Eri3 | NM_080469.4 | chr4:117222928-117346902 |
| 9577 | Erich1 | NM_001034862.2 | chr8:14027564-14090327 |
| 9578 | Erich2 | NM_025744.2 | chr2:70346876-70378941 |
| 9579 | Erich3 | NM_175176.3 | chr3:154374096-154411976 |
| 9580 | Erich4 | NM_001039243.3 | chr7:26399639-26400911 |
| 9581 | Erich5 | NM_173421.2 | chr15:34383066-34403647 |
| 9582 | Erich6 | NM_001081262.1 | chr3:58420221-58441129 |
| 9583 | Erec1 | NM_025745.3 | chr11:30829783-30854131 |
| 9584 | Erlin1 | NM_001164359.1 | chr19:44109432-44144275 |
| 9585 | Erlin1 | NM_001164360.1 | chr19:44109432-44144275 |
| 9586 | Erlin1 | NM_145502.3 | chr19:44109432-44144275 |
| 9587 | Erlin2 | NM_153592.2 | chr8:28134270-28149907 |
| 9588 | Ermap | NM_013848.2 | chr4:118848061-118862616 |
| 9589 | Ermard | NM_001034891.3 | chr17:15178575-15201196 |
| 9590 | Ermard | NM_001039552.2 | chr17:15178575-15201196 |
| 9591 | Ermn | NM_029972.3 | chr2:57897525-57905163 |
| 9592 | Ermp1 | NM_001081213.1 | chr19:29684372-29722910 |
| 9593 | Ern1 | NM_023913.2 | chr11:106258933-106349110 |
| 9594 | Ern2 | NM_012016.2 | chr7:129313406-129329730 |
| 9595 | Ero1l | NM_015774.2 | chr14:45902761-45938247 |
| 9596 | Ero1lb | NM_026184.2 | chr13:12658149-12701795 |
| 9597 | Erp27 | NM_026983.2 | chr6:136855907-136870701 |
| 9598 | Erp29 | NM_026129.2 | chr5:121894761-121902483 |
| 9599 | Erp44 | NM_029572.2 | chr4:48206202-48292461 |
| 9600 | Errfi1 | NM_133753.1 | chr4:150229199-150242989 |
| 9601 | Ervl3 | NM_001166206.1 | chr2:131679413-131685483 |
| 9602 | Esam | NM_027102.3 | chr9:37335673-37345904 |
| 9603 | Esco1 | NM_001081222.1 | chr18:10566509-10610350 |
| 9604 | Esco2 | NM_028039.2 | chr14:66437863-66452806 |
| 9605 | Esd | NM_001285423.1 | chr14:75132103-75150572 |
| 9606 | Esd | NM_016903.5 | chr14:75132103-75150572 |
| 9607 | Esf1 | NM_001081090.1 | chr2:139945616-139996294 |
| 9608 | Esm1 | NM_023612.3 | chr13:113999866-114008312 |
| 9609 | Esp1 | NM_001038500.2 | chr17:40864068-40868731 |
| 9610 | Esp15 | NM_001244651.1 | chr17:39777901-39782612 |
| 9611 | Esp16 | NM_001255977.1 | chr17:39673086-39677792 |
| 9612 | Esp18 | NM_001244763.1 | chr17:39543303-39547937 |
| 9613 | Esp23 | NM_001177582.1 | chr17:39210635-39213982 |
| 9614 | Esp24 | NM_001256050.1 | chr17:39173639-39177172 |
| 9615 | Esp3 | NM_001251916.1 | chr17:40769023-40774009 |
| 9616 | Esp33 | NM_001177586.1 | chr17:38776391-38782598 |
| 9617 | Esp34 | NM_001177585.1 | chr17:38691136-38697566 |
| 9618 | Esp36 | NM_001177587.1 | chr17:38553418-38557130 |
| 9619 | Esp38 | NM_001256051.1 | chr17:40087464-40092232 |
| 9620 | Esp4 | NM_001177583.1 | chr17:40735542-40739566 |
| 9621 | Esp5 | NM_001287194.1 | chr17:40711660-40716498 |
| 9622 | Esp6 | NM_001177529.1 | chr17:40698456-40702573 |
| 9623 | Esp6-esp5 | NM_001287195.1 | chr17:40698456-40716498 |
| 9624 | Esp8 | NM_001177584.1 | chr17:40656970-40667651 |
| 9625 | Espl1 | NM_001014976.2 | chr15:102126723-102154787 |
| 9626 | Espn | NM_019585.3 | chr4:151494984-151526316 |
| 9627 | Espn | NM_207687.2 | chr4:151494984-151526316 |
| 9628 | Espn | NM_207688.2 | chr4:151494984-151526316 |
| 9629 | Espn | NM_207689.2 | chr4:151494984-151526316 |
| 9630 | Espn | NM_207690.2 | chr4:151494984-151526316 |
| 9631 | Espn | NM_207691.2 | chr4:151494984-151526316 |
| 9632 | Espnl | NM_001033292.3 | chr1:93218651-93244880 |
| 9633 | Esr1 | NM_007956.5 | chr10:5342779-5734495 |
| 9634 | Esr2 | NM_010157.3 | chr12:77221405-77278246 |
| 9635 | Esr2 | NM_207707.1 | chr12:77221405-77278246 |
| 9636 | Esr2 | NR_104386.1 | chr12:77221405-77278246 |
| 9637 | Esrp1 | NM_001290383.1 | chr4:11259079-11313930 |
| 9638 | Esrp1 | NM_194055.3 | chr4:11259079-11313930 |
| 9639 | Esrp2 | NM_176838.2 | chr8:108655083-108660874 |
| 9640 | Esrra | NM_007953.2 | chr19:6985467-6996298 |
| 9641 | Esrrb | NM_001159500.1 | chr12:87702666-87862578 |
| 9642 | Esrrb | NM_011934.4 | chr12:87702666-87862578 |
| 9643 | Esrrg | NM_001243792.1 | chr1:189432884-190038763 |
| 9644 | Esrrg | NM_011935.3 | chr1:189432884-190038763 |
| 9645 | Esx1 | NM_007957.2 | chrX:133649935-133654865 |
| 9646 | Esyt1 | NM_011843.2 | chr10:127947306-127962915 |
| 9647 | Esyt2 | NM_028731.5 | chr12:117519694-117611571 |
| 9648 | Esyt3 | NM_177775.3 | chr9:99210385-99258949 |
| 9649 | Etaa1 | NM_026576.2 | chr11:17838751-17853878 |
| 9650 | Etd | NR_034074.1 | chrX:50788094-50796753 |
| 9651 | Etf1 | NM_144866.3 | chr18:35062438-35091657 |
| 9652 | Etfa | NM_145615.4 | chr9:55302242-55360050 |
| 9653 | Etfb | NM_026695.3 | chr7:50699441-50713170 |
| 9654 | Etfb | NR_075104.1 | chr7:50699441-50713170 |
| 9655 | Etfdh | NM_025794.2 | chr3:79407709-79432689 |
| 9656 | Ethe1 | NM_023154.3 | chr7:25372562-25393944 |
| 9657 | Etl4 | NM_001081006.1 | chr2:20211539-20732162 |
| 9658 | Etl4 | NM_001177630.2 | chr2:20211539-20732162 |
| 9659 | Etl4 | NM_001177631.1 | chr2:20211539-20732162 |
| 9660 | Etl4 | NM_029895.4 | chr2:20211539-20732162 |
| 9661 | Etl4 | NM_178059.5 | chr2:20211539-20732162 |
| 9662 | Etnk1 | NM_029250.2 | chr6:143157066-143157066 |
| 9663 | Etnk2 | NM_175443.5 | chr1:135260148-135276895 |
| 9664 | Etnppl | NM_001163587.1 | chr3:130320365-130338668 |
| 9665 | Etnppl | NM_027907.3 | chr3:130320365-130338668 |
| 9666 | Etohd2 | NR_015349.2 | chr13:59871327-59875041 |
| 9667 | Etohi1 | NM_001177399.1 | chr2:177757988-177770564 |
| 9668 | Etohi1 | NM_001177400.1 | chr2:177757988-177770564 |
| 9669 | Ets1 | NM_001038642.1 | chr9:32503826-32565405 |
| 9670 | Ets1 | NM_011808.2 | chr9:32503826-32565405 |
| 9671 | Ets2 | NM_011809.1 | chr16:95924013-95942656 |
| 9672 | Etv1 | NM_001163154.1 | chr12:39506844-39594802 |
| 9673 | Etv1 | NM_007960.4 | chr12:39506844-39594802 |
| 9674 | Etv2 | NM_007959.2 | chr7:31418634-31420871 |
| 9675 | Etv3 | NM_001083318.2 | chr3:87329499-87344080 |

Fig. 25 - 52

| | | | |
|---|---|---|---|
| 9676 | Etv3 | NM_001286844.1 | chr3:87329499-87344080 |
| 9677 | Etv3 | NM_012051.4 | chr3:87329499-87344080 |
| 9678 | Etv4 | NM_008815.2 | chr11:101631055-101646624 |
| 9679 | Etv5 | NM_023794.2 | chr16:22381385-22439643 |
| 9680 | Etv6 | NM_007961.4 | chr6:133985724-134220165 |
| 9681 | EU599041 | NM_001177525.1 | chr7:50469408-50482212 |
| 9682 | Eva1a | NM_145570.2 | chr6:81991621-82043093 |
| 9683 | Eva1b | NM_172145.3 | chr4:125825246-125827118 |
| 9684 | Eva1c | NM_001199210.1 | chr16:90831103-90905130 |
| 9685 | Eva1c | NM_027627.2 | chr16:90831103-90905130 |
| 9686 | Evc | NM_021292.2 | chr5:37690409-37728120 |
| 9687 | Evc2 | NM_145920.3 | chr5:37729716-37816293 |
| 9688 | Evi2a | NM_001033711.1 | chr11:79153393-79395111 |
| 9689 | Evi2a | NM_010161.3 | chr11:79153393-79395111 |
| 9690 | Evi2a-evi2b | NM_146023.4 | chr11:79326887-79344111 |
| 9691 | Evi2b | NM_001077496.1 | chr11:79326887-79337264 |
| 9692 | Evi5 | NM_007964.2 | chr5:108173814-108304126 |
| 9693 | Evi5l | NM_001039578.3 | chr8:4166566-4193701 |
| 9694 | Evl | NM_001163394.1 | chr12:109609362-109940516 |
| 9695 | Evl | NM_001163395.1 | chr12:109609362-109940516 |
| 9696 | Evl | NM_001163396.2 | chr12:109609362-109940516 |
| 9697 | Evl | NM_007965.3 | chr12:109609362-109940516 |
| 9698 | Evpl | NM_025276.3 | chr11:116081872-116099405 |
| 9699 | Evx1 | NM_007966.4 | chr6:52263492-52268372 |
| 9700 | Evx2 | NM_007967.2 | chr2:74493672-74497476 |
| 9701 | Ewsr1 | NM_001283061.1 | chr11:4969689-4999091 |
| 9702 | Ewsr1 | NM_001283062.1 | chr11:4969689-4999091 |
| 9703 | Ewsr1 | NM_001283063.1 | chr11:4969689-4999091 |
| 9704 | Ewsr1 | NM_007968.3 | chr11:4969689-4999091 |
| 9705 | Exd1 | NM_172857.2 | chr2:119345139-119373363 |
| 9706 | Exd2 | NM_133798.3 | chr12:81564081-81599122 |
| 9707 | Exo1 | NM_012012.4 | chr1:177810908-177841527 |
| 9708 | Exo5 | NM_001160043.1 | chr4:120593806-120597610 |
| 9709 | Exo5 | NM_028457.2 | chr4:120593806-120597610 |
| 9710 | Exoc1 | NM_001289770.1 | chr5:76958335-76999323 |
| 9711 | Exoc1 | NM_001289771.1 | chr5:76958335-76999323 |
| 9712 | Exoc1 | NM_027270.2 | chr5:76958335-76999323 |
| 9713 | Exoc2 | NM_025588.2 | chr13:30905787-31065916 |
| 9714 | Exoc3 | NM_177333.3 | chr13:74307252-74346148 |
| 9715 | Exoc3l | NM_177788.4 | chr8:107813823-107819998 |
| 9716 | Exoc3l4 | NM_001289487.1 | chr12:112655640-112669891 |
| 9717 | Exoc3l4 | NM_001289488.1 | chr12:112655640-112669891 |
| 9718 | Exoc3l4 | NM_001289489.1 | chr12:112655640-112669891 |
| 9719 | Exoc3l4 | NM_028807.1 | chr12:112655640-112669891 |
| 9720 | Exoc4 | NM_009148.3 | chr6:33199149-33922930 |
| 9721 | Exoc5 | NM_207214.3 | chr14:49631819-49686342 |
| 9722 | Exoc6 | NM_175353.2 | chr19:37624907-37757739 |
| 9723 | Exoc6b | NM_177077.2 | chr6:84568479-85019507 |
| 9724 | Exoc7 | NM_001162872.1 | chr11:116149311-116168052 |
| 9725 | Exoc7 | NM_016857.2 | chr11:116149311-116168052 |
| 9726 | Exoc8 | NM_198103.2 | chr8:127414198-127421605 |
| 9727 | Exog | NM_001172136.1 | chr9:119354040-119374636 |
| 9728 | Exog | NM_172762.3 | chr9:119354040-119374636 |
| 9729 | Exosc1 | NM_001164561.1 | chr19:41997469-42007804 |
| 9730 | Exosc1 | NM_025644.4 | chr19:41997469-42007804 |
| 9731 | Exosc10 | NM_016699.2 | chr4:147932535-147956509 |
| 9732 | Exosc2 | NM_144886.2 | chr2:31526256-31536827 |
| 9733 | Exosc3 | NM_025513.3 | chr4:45329501-45333475 |
| 9734 | Exosc4 | NM_175399.4 | chr15:76157826-76161100 |
| 9735 | Exosc5 | NM_138586.3 | chr7:26444171-26453051 |
| 9736 | Exosc5 | NR_104358.1 | chr7:26444171-26453051 |
| 9737 | Exosc6 | NM_028274.4 | chr8:113580238-113581564 |
| 9738 | Exosc7 | NM_001081188.1 | chr9:123022348-123045247 |
| 9739 | Exosc8 | NM_001163570.1 | chr3:54532600-54539286 |
| 9740 | Exosc8 | NM_027148.3 | chr3:54532600-54539286 |
| 9741 | Exosc9 | NM_019393.2 | chr3:36451528-36464649 |
| 9742 | Exph5 | NM_176846.3 | chr9:53109774-53189263 |
| 9743 | Ext1 | NM_010164.2 | chr15:52899817-53177738 |
| 9744 | Ext2 | NM_010163.3 | chr2:93535787-93662725 |
| 9745 | Extl1 | NM_019578.2 | chr4:133912287-133928462 |
| 9746 | Extl2 | NM_001163514.1 | chr3:115710366-115731934 |
| 9747 | Extl2 | NM_001163515.1 | chr3:115710366-115731934 |
| 9748 | Extl2 | NM_023388.4 | chr3:115710366-115731934 |
| 9749 | Extl3 | NM_018788.3 | chr14:65670895-65716943 |
| 9750 | Eya1 | NM_001252192.1 | chr1:14159038-14300280 |
| 9751 | Eya1 | NM_010164.2 | chr1:14159038-14300280 |
| 9752 | Eya2 | NM_001271962.1 | chr2:165420527-165597227 |
| 9753 | Eya2 | NM_001271963.1 | chr2:165420527-165597227 |
| 9754 | Eya2 | NM_010165.3 | chr2:165420527-165597227 |
| 9755 | Eya3 | NM_010166.3 | chr4:132194960-132280680 |
| 9756 | Eya3 | NM_210071.2 | chr4:132194960-132280680 |
| 9757 | Eya3 | NM_211573.2 | chr4:132194960-132280680 |
| 9758 | Eya4 | NM_010167.4 | chr10:22823973-23069709 |
| 9759 | Ezh1 | NM_007970.3 | chr11:101052428-101087764 |
| 9760 | Ezh2 | NM_001146689.1 | chr6:47480272-47545029 |
| 9761 | Ezh2 | NM_007971.2 | chr6:47480272-47545029 |
| 9762 | Ezr | NM_009510.2 | chr17:6942479-6987129 |
| 9763 | F10 | NM_001242368.1 | chr8:13037307-13056676 |
| 9764 | F10 | NM_007972.4 | chr8:13037307-13056676 |
| 9765 | F11 | NM_028066.2 | chr8:46326523-46347385 |
| 9766 | F11r | NM_172647.2 | chr1:173367691-173394724 |
| 9767 | F12 | NM_021489.3 | chr13:55519326-55528163 |
| 9768 | F13a1 | NM_001166391.1 | chr13:36959046-37142113 |
| 9769 | F13a1 | NM_028784.3 | chr13:36959046-37142113 |
| 9770 | F13b | NM_031164.2 | chr1:141398283-141420333 |
| 9771 | F2 | NM_010168.2 | chr2:91465476-91476571 |
| 9772 | F2r | NM_010169.3 | chr13:96371743-96388388 |
| 9773 | F2rl1 | NM_007974.4 | chr13:96281683-96295195 |
| 9774 | F2rl2 | NM_010170.4 | chr13:96468875-96472723 |
| 9775 | F2rl3 | NM_007975.3 | chr8:75285778-75287784 |
| 9776 | F3 | NM_010171.3 | chr3:121426454-121437970 |
| 9777 | F420014N23Rik | NR_045715.1 | chr10:126627433-126648678 |
| 9778 | F420014N23Rik | NR_045715.1 | chr10:126627433-126648678 |
| 9779 | F5 | NM_007976.3 | chr1:166081966-166150408 |
| 9780 | F630028O10Rik | NR_030718.1 | chrX:93435265-93438981 |
| 9781 | F630042J09Rik | NR_033540.1 | chr13:67379529-67384297 |
| 9782 | F630111L10Rik | NR_045641.1 | chr3:58950218-58957550 |
| 9783 | F630206G17Rik | NR_045876.1 | chr11:45621584-45656380 |
| 9784 | F7 | NM_010172.4 | chr8:13026033-13035809 |
| 9785 | F730035M05Rik | NR_045174.1 | chr12:71328827-71335152 |
| 9786 | F730043M19Rik | NR_015602.2 | chr12:33796575-33832451 |
| 9787 | F8 | NM_001161373.1 | chrX:72418055-72625380 |
| 9788 | F8 | NM_001161374.1 | chrX:72418055-72625380 |
| 9789 | F8 | NM_007977.2 | chrX:72418055-72625380 |
| 9790 | F830002L21Rik | NR_033558.1 | chr10:43313232-43350719 |
| 9791 | F830016B08Rik | NM_001101475.2 | chr18:60453033-60462670 |
| 9792 | F830045P16Rik | NM_177653.3 | chr2:129284094-129362338 |
| 9793 | F8a | NM_007978.3 | chrX:70473644-70476134 |
| 9794 | F9 | NM_007979.2 | chrX:57252640-57281935 |
| 9795 | F930015N05Rik | NR_028445.1 | chr11:64246637-64250176 |
| 9796 | Fa2h | NM_178086.3 | chr8:113869037-113917721 |
| 9797 | Faah | NM_010173.4 | chr4:115669260-115690507 |
| 9798 | Fabp1 | NM_017399.4 | chr6:71149881-71155017 |
| 9799 | Fabp12 | NM_029310.1 | chr3:10244208-10301183 |
| 9800 | Fabp2 | NM_007980.3 | chr3:122597990-122602424 |
| 9801 | Fabp3 | NM_010174.1 | chr4:129986021-129992707 |
| 9802 | Fabp4 | NM_024406.2 | chr3:10204342-10208576 |
| 9803 | Fabp5 | NM_001272097.1 | chr3:10012584-10016610 |
| 9804 | Fabp5 | NM_001272098.1 | chr3:10012584-10016610 |
| 9805 | Fabp5 | NM_010634.3 | chr3:10012584-10016610 |
| 9806 | Fabp6 | NM_008375.2 | chr11:43409541-43415064 |
| 9807 | Fabp7 | NM_021272.3 | chr10:57504728-57508256 |
| 9808 | Fabp9 | NM_011598.3 | chr3:10193623-10197283 |
| 9809 | Fadd | NM_010175.5 | chr7:151764227-151768341 |
| 9810 | Fads1 | NM_146094.2 | chr19:10257378-10271362 |
| 9811 | Fads2 | NM_019699.1 | chr19:10158653-10175993 |
| 9812 | Fads3 | NM_021890.3 | chr19:10116037-10134161 |
| 9813 | Fads6 | NM_178035.4 | chr11:115144679-115158860 |
| 9814 | Faf1 | NM_007983.2 | chr4:109349231-109636565 |
| 9815 | Faf2 | NM_178397.3 | chr13:54723144-54765424 |
| 9816 | Fah | NM_010176.4 | chr7:91733669-91754452 |
| 9817 | Fahd1 | NM_023480.2 | chr17:24985840-24987247 |
| 9818 | Fahd2a | NM_029629.2 | chr1:127261950-127270301 |
| 9819 | Faim | NM_001122851.1 | chr9:98886791-98902438 |
| 9820 | Faim | NM_011810.3 | chr9:98886791-98902438 |
| 9821 | Faim2 | NM_001038658.2 | chr15:99327435-99358596 |
| 9822 | Faim2 | NM_028224.4 | chr15:99327435-99358596 |
| 9823 | Faim3 | NM_026976.2 | chr1:132762353-132777367 |
| 9824 | Fam101a | NM_028443.2 | chr5:125483844-125492917 |
| 9825 | Fam101b | NM_029658.1 | chr11:75832696-75841284 |
| 9826 | Fam102a | NM_153560.4 | chr2:32390878-32425270 |
| 9827 | Fam102b | NM_001163567.1 | chr3:108773914-108830525 |
| 9828 | Fam103a1 | NM_025997.2 | chr7:88907838-88914376 |
| 9829 | Fam104a | NM_138598.5 | chr11:113522633-113545465 |
| 9830 | Fam105a | NM_001242423.1 | chr15:27584825-27611297 |
| 9831 | Fam105a | NM_001242424.1 | chr15:27584825-27611297 |
| 9832 | Fam105a | NM_198301.2 | chr15:27584825-27611297 |
| 9833 | Fam107a | NM_183187.3 | chr14:9128791-9142290 |
| 9834 | Fam107b | NM_025626.4 | chr2:3630729-3699406 |
| 9835 | Fam109a | NM_175474.3 | chr5:122299036-122304608 |
| 9836 | Fam109b | NM_177391.4 | chr15:82171608-82176140 |
| 9837 | Fam110a | NM_001289150.1 | chr2:151795131-151805955 |
| 9838 | Fam110a | NM_001289151.1 | chr2:151795131-151805955 |
| 9839 | Fam110a | NM_028666.2 | chr2:151795131-151805955 |
| 9840 | Fam110a | NM_146127.3 | chr2:151795131-151805955 |
| 9841 | Fam110b | NM_173426.2 | chr4:5571325-5727091 |
| 9842 | Fam110c | NM_027828.2 | chr12:31758832-31764805 |
| 9843 | Fam111a | NM_026640.2 | chr19:12648015-12664186 |
| 9844 | Fam114a1 | NM_026667.3 | chr5:65361314-65433140 |
| 9845 | Fam114a2 | NM_001168667.1 | chr11:57296491-57332146 |
| 9846 | Fam114a2 | NM_001168668.1 | chr11:57296491-57332146 |
| 9847 | Fam114a2 | NM_026342.3 | chr11:57296491-57332146 |
| 9848 | Fam115a | NM_029930.2 | chr4:42622545-42643058 |
| 9849 | Fam115c | NM_146174.1 | chr6:42573041-42595040 |
| 9850 | Fam115e | NM_203396.1 | chr4:42537211-42547371 |
| 9851 | Fam117a | NM_172543.4 | chr11:95198331-95243186 |
| 9852 | Fam117b | NM_001037725.3 | chr1:59969849-60042192 |
| 9853 | Fam118a | NM_133750.4 | chr15:84867491-84893260 |
| 9854 | Fam118b | NM_001286604.1 | chr9:35018787-35075390 |
| 9855 | Fam118b | NM_175411.5 | chr9:35018787-35075390 |
| 9856 | Fam118b | NM_194257.2 | chr9:35018787-35075390 |
| 9857 | Fam120a | NM_001033268.2 | chr13:48974585-49063197 |
| 9858 | Fam120aos | NR_015601.1 | chr13:49063480-49065274 |
| 9859 | Fam120b | NM_024203.3 | chr17:15533165-15570545 |
| 9860 | Fam120b | NR_033586.1 | chr17:15533165-15570545 |
| 9861 | Fam120c | NM_198105.2 | chrX:147778785-147908677 |
| 9862 | Fam122a | NM_026520.2 | chr19:24550269-24551964 |
| 9863 | Fam122b | NM_001166365.2 | chrX:50596591-50622982 |
| 9864 | Fam122b | NM_001166583.1 | chrX:50596591-50622982 |
| 9865 | Fam122b | NM_030167.4 | chrX:50596591-50622982 |

Fig. 25 - 53

| | | | | | | | | |
|---|---|---|---|---|---|---|---|---|
| 9866 | Fam122c | NM_028671.2 | chrX:50626609-50654678 | | 9961 | Fam181b | NM_021427.2 | chr7:100228388-100230231 |
| 9867 | Fam124a | NM_001243857.1 | chr14:63174573-63227322 | | 9962 | Fam183b | NM_001162878.1 | chr11:58606303-58615462 |
| 9868 | Fam124b | NM_173425.3 | chr1:80195273-80210519 | | 9963 | Fam183b | NM_029283.1 | chr11:58606303-58615462 |
| 9869 | Fam126a | NM_053090.2 | chr5:23466753-23536501 | | 9964 | Fam184a | NM_001081428.1 | chr10:53352951-53470715 |
| 9870 | Fam126b | NM_172513.3 | chr1:58579649-58643177 | | 9965 | Fam184b | NM_021416.3 | chrX:45920944-46030740 |
| 9871 | Fam129a | NM_022018.3 | chr1:153418502-153566477 | | 9966 | Fam185a | NM_177869.4 | chr5:20930720-20987942 |
| 9872 | Fam129b | NM_146119.2 | chr2:32731654-32780773 | | 9967 | Fam186b | NM_001081254.1 | chr15:99101448-99117611 |
| 9873 | Fam129c | NM_001166213.1 | chr8:74121544-74132048 | | 9968 | Fam187a | NM_025766.2 | chr11:102746483-102748045 |
| 9874 | Fam131a | NM_133778.2 | chr16:20695130-20703109 | | 9969 | Fam187b | NM_001242647.1 | chr7:31758822-31774744 |
| 9875 | Fam131b | NM_001113327.2 | chr6:42265303-42274639 | | 9970 | Fam187b | NM_175240.4 | chr7:31758822-31774744 |
| 9876 | Fam131b | NM_001286584.1 | chr6:42265303-42274639 | | 9971 | Fam187b | NR_038860.1 | chr7:31758822-31774744 |
| 9877 | Fam131b | NM_029528.5 | chr6:42265303-42274639 | | 9972 | Fam188a | NM_024185.4 | chr2:12268890-12341087 |
| 9878 | Fam131c | NM_001085513.2 | chr4:140924106-140940089 | | 9973 | Fam188b | NM_001142781.1 | chr6:55153376-55270216 |
| 9879 | Fam132a | NM_026125.3 | chr4:155336420-155346738 | | 9974 | Fam188b | NM_177883.4 | chr6:55153376-55270216 |
| 9880 | Fam132b | NM_173395.2 | chr1:93263006-93270794 | | 9975 | Fam189a1 | NM_183087.4 | chr7:71900982-72301414 |
| 9881 | Fam133b | NM_001042501.1 | chr5:3543832-3570546 | | 9976 | Fam189a2 | NM_001114174.1 | chr19:24047239-24105509 |
| 9882 | Fam134a | NM_170755.2 | chr1:75139359-75144483 | | 9977 | Fam189b | NM_001014995.1 | chr3:88987146-88993211 |
| 9883 | Fam134b | NM_001034851.2 | chr15:25773052-25903451 | | 9978 | Fam192a | NM_028221.4 | chr8:97098840-97125626 |
| 9884 | Fam134b | NM_001277315.1 | chr15:25773052-25903451 | | 9979 | Fam193a | NM_001243123.1 | chr5:34712581-34829107 |
| 9885 | Fam134b | NM_001277316.1 | chr15:25773052-25903451 | | 9980 | Fam193b | NM_145382.4 | chr13:55640676-55672481 |
| 9886 | Fam134b | NM_001277317.1 | chr15:25773052-25903451 | | 9981 | Fam195a | NM_026633.3 | chr17:26000642-26005683 |
| 9887 | Fam134b | NM_001277318.1 | chr15:25773052-25903451 | | 9982 | Fam195b | NM_001033231.2 | chr11:120404201-120411041 |
| 9888 | Fam134b | NM_025459.3 | chr15:25773052-25903451 | | 9983 | Fam196a | NM_001143802.1 | chr7:142073591-142130113 |
| 9889 | Fam134c | NM_026501.2 | chr1:100957635-100981157 | | 9984 | Fam196b | NM_001025382.2 | chr11:34214822-34322640 |
| 9890 | Fam134c | NM_028933.3 | chr1:100957635-100981157 | | 9985 | Fam198a | NM_001199927.1 | chr9:121860105-121889326 |
| 9891 | Fam135a | NM_026604.4 | chr1:24017596-24107180 | | 9986 | Fam198a | NM_177743.5 | chr9:121860105-121889326 |
| 9892 | Fam135b | NM_177819.3 | chr15:71276107-71558268 | | 9987 | Fam198b | NM_133187.3 | chr3:79689851-79750200 |
| 9893 | Fam136a | NM_025593.2 | chr6:86315676-86320052 | | 9988 | Fam19x | NM_146261.2 | chrX:133584132-133617040 |
| 9894 | Fam13a | NM_153574.2 | chr6:58883529-58974496 | | 9989 | Fam19a1 | NM_182808.3 | chr6:96063148-96607192 |
| 9895 | Fam13b | NM_146084.1 | chr18:34602005-34666477 | | 9990 | Fam19a2 | NM_001252387.1 | chr10:122701131-123178260 |
| 9896 | Fam13c | NM_001143776.1 | chr10:69903415-70062039 | | 9991 | Fam19a2 | NM_182807.3 | chr10:122701131-123178260 |
| 9897 | Fam13c | NM_001143777.1 | chr10:69903415-70062039 | | 9992 | Fam19a2 | NR_045514.1 | chr10:122701131-123178260 |
| 9898 | Fam13c | NM_024244.4 | chr10:69903415-70062039 | | 9993 | Fam19a3 | NM_183224.3 | chr3:104570322-104580465 |
| 9899 | Fam149a | NM_153635.3 | chr8:46422068-46467645 | | 9994 | Fam19a4 | NM_177233.5 | chr6:96781202-97010405 |
| 9900 | Fam149b | NM_001024512.2 | chr14:21167383-21202713 | | 9995 | Fam19a5 | NM_001252310.1 | chr15:87374728-87589794 |
| 9901 | Fam149b | NM_001177633.1 | chr14:21167383-21202713 | | 9996 | Fam19a5 | NM_134096.2 | chr15:87374728-87589794 |
| 9902 | Fam149b | NM_172379.3 | chr14:21167383-21202713 | | 9997 | Fam19a5 | NR_045510.1 | chr15:87374728-87589794 |
| 9903 | Fam150a | NM_001195732.1 | chr1:6349411-6384812 | | 9998 | Fam203a | NM_021555.2 | chr15:76199327-76201841 |
| 9904 | Fam150b | NM_001159743.1 | chr12:31569189-31578719 | | 9999 | Fam204a | NM_029648.6 | chr19:60274488-60302600 |
| 9905 | Fam151a | NM_146149.1 | chr4:106406520-106420897 | | 10000 | Fam206a | NM_001081420.1 | chr4:56815201-56822477 |
| 9906 | Fam151b | NM_001163627.1 | chr13:93219574-93253986 | | 10001 | Fam207a | NM_133998.3 | chr10:76949399-76978558 |
| 9907 | Fam154a | NM_001081096.1 | chr4:86090601-86204207 | | 10002 | Fam208a | NM_001114879.1 | chr14:28242032-28321646 |
| 9908 | Fam154b | NM_177894.4 | chr7:89781469-89797038 | | 10003 | Fam208a | NM_028945.2 | chr14:28242032-28321646 |
| 9909 | Fam155a | NM_173446.2 | chr8:9206009-9771023 | | 10004 | Fam208b | NM_134063.3 | chr13:3565281-3610354 |
| 9910 | Fam159a | NM_001099303.2 | chr4:108040381-108056260 | | 10005 | Fam20a | NM_029608.1 | chr2:172298053-172299816 |
| 9911 | Fam159b | NM_029984.1 | chr13:105635362-105653973 | | 10006 | Fam20a | NM_153782.1 | chr11:109534239-109583570 |
| 9912 | Fam160a1 | NM_172682.3 | chr3:85463984-85550131 | | 10007 | Fam20b | NM_145413.4 | chr1:158608701-158649041 |
| 9913 | Fam160a2 | NM_001242363.2 | chr7:112519724-112548568 | | 10008 | Fam20c | NM_030565.6 | chr5:139231034-139286017 |
| 9914 | Fam160a2 | NM_001242364.2 | chr7:112519724-112548568 | | 10009 | Fam21 | NM_026585.3 | chr6:116158050-116212689 |
| 9915 | Fam160a2 | NM_001242365.2 | chr7:112519724-112548568 | | 10010 | Fam210a | NM_153794.4 | chr18:68419839-68459987 |
| 9916 | Fam160a2 | NM_199209.3 | chr7:112519724-112548568 | | 10011 | Fam210b | NM_025912.4 | chr2:172171076-172181249 |
| 9917 | Fam160b1 | NM_145505.4 | chr19:57435498-57464084 | | 10012 | Fam212a | NM_026597.3 | chr9:107886654-107888247 |
| 9918 | Fam160b2 | NM_194345.1 | chr14:70983101-70999642 | | 10013 | Fam212b | NM_001163356.1 | chr3:105507516-105523760 |
| 9919 | Fam161a | NM_028672.2 | chr11:22913386-22923741 | | 10014 | Fam212b | NM_175398.4 | chr3:105507516-105523760 |
| 9920 | Fam161b | NM_172581.2 | chr12:85686266-85702771 | | 10015 | Fam213a | NM_027464.3 | chr14:41807028-41827064 |
| 9921 | Fam162a | NM_027342.1 | chr16:36043929-36071601 | | 10016 | Fam213b | NM_025582.3 | chr4:154270538-154273152 |
| 9922 | Fam162b | NM_029894.1 | chr10:51305255-51310266 | | 10017 | Fam214a | NM_001113283.1 | chr9:74800859-74880275 |
| 9923 | Fam163a | NM_177838.3 | chr1:157923085-158135156 | | 10018 | Fam214a | NM_153584.2 | chr9:74800859-74880275 |
| 9924 | Fam163b | NM_175427.4 | chr2:26965898-26997997 | | 10019 | Fam214b | NM_001253353.1 | chr4:43045285-43059092 |
| 9925 | Fam166a | NM_026624.3 | chr2:25074265-25077801 | | 10020 | Fam214b | NM_001253354.1 | chr4:43045285-43059092 |
| 9926 | Fam166b | NM_001162381.1 | chr4:43394853-43442006 | | 10021 | Fam214b | NM_172691.2 | chr4:43045285-43059092 |
| 9927 | Fam166b | NM_177377.5 | chr4:43394853-43442006 | | 10022 | Fam214b | NR_045567.1 | chr4:43045285-43059092 |
| 9928 | Fam167a | NM_177628.4 | chr14:64055230-64084339 | | 10023 | Fam216a | NM_026883.3 | chr5:122814592-122821972 |
| 9929 | Fam167b | NM_182783.2 | chr4:129254058-129255824 | | 10024 | Fam216b | NM_177629.4 | chr14:78480830-78488814 |
| 9930 | Fam168a | NM_178755.2 | chr7:107855215-107990144 | | 10025 | Fam217a | NM_027967.2 | chr13:35001832-35011861 |
| 9931 | Fam168b | NM_001160235.1 | chr1:34870062-34899895 | | 10026 | Fam217b | NM_001081289.1 | chr2:178149238-178156866 |
| 9932 | Fam168b | NM_001160236.1 | chr1:34870062-34899895 | | 10027 | Fam219a | NM_001159583.1 | chr4:41464469-41516560 |
| 9933 | Fam168b | NM_174997.2 | chr1:34870062-34899895 | | 10028 | Fam219a | NM_027993.3 | chr4:41464469-41516560 |
| 9934 | Fam169a | NM_001100458.1 | chr13:97837241-97907881 | | 10029 | Fam219aos | NR_045726.1 | chr4:41464470-41465962 |
| 9935 | Fam169a | NM_001146045.1 | chr13:97837241-97907881 | | 10030 | Fam219b | NM_001166364.1 | chr9:57385334-57390994 |
| 9936 | Fam169b | NM_001013811.2 | chr7:75418725-75507976 | | 10031 | Fam219b | NM_175273.4 | chr9:57385334-57390994 |
| 9937 | Fam170a | NM_001004061.1 | chr18:50438022-50442673 | | 10032 | Fam220a | NM_026050.2 | chr5:144309573-144325393 |
| 9938 | Fam170b | NM_001146345.1 | chr14:33647147-33649974 | | 10033 | Fam220a | NM_133703.4 | chr5:144309573-144325393 |
| 9939 | Fam171a1 | NM_001081161.1 | chr2:3035659-3145681 | | 10034 | Fam221a | NM_001172216.1 | chr6:49317737-49339903 |
| 9940 | Fam171a2 | NM_199200.2 | chr11:102298295-102308977 | | 10035 | Fam221a | NM_172727.3 | chr6:49317737-49339903 |
| 9941 | Fam171b | NM_175514.2 | chr2:83652884-83721515 | | 10036 | Fam221b | NM_175517.3 | chr4:43672493-43681731 |
| 9942 | Fam172a | NM_001163419.1 | chr13:77847950-78305501 | | 10037 | Fam222a | NM_001004180.1 | chr5:115018259-115063227 |
| 9943 | Fam172a | NM_001163420.1 | chr13:77847950-78305501 | | 10038 | Fam222b | NM_145430.2 | chr11:77908174-77970841 |
| 9944 | Fam172a | NM_138312.1 | chr13:77847950-78305501 | | 10039 | Fam227a | NM_029407.2 | chr15:79440005-79489386 |
| 9945 | Fam172a | NR_028109.1 | chr13:77847950-78305501 | | 10040 | Fam227b | NM_029455.3 | chr2:125809219-125977740 |
| 9946 | Fam173a | NM_001285982.1 | chr17:25923524-25929339 | | 10041 | Fam228a | NM_029107.2 | chr12:4720611-4745189 |
| 9947 | Fam173a | NM_145410.4 | chr17:25923524-25929339 | | 10042 | Fam228b | NM_175431.4 | chr12:4753021-4776073 |
| 9948 | Fam173b | NM_026546.3 | chr15:31531870-31547290 | | 10043 | Fam229a | NM_001085491.2 | chr4:129168433-129169200 |
| 9949 | Fam174a | NM_026321.4 | chr1:97210204-97231861 | | 10044 | Fam229b | NM_183254.1 | chr10:38838613-38853701 |
| 9950 | Fam174b | NM_001162532.1 | chr7:80885192-80921805 | | 10045 | Fam24a | NM_183272.2 | chr7:138478135-138480230 |
| 9951 | Fam175a | NM_172405.3 | chr5:101233820-101249954 | | 10046 | Fam25c | NM_183278.2 | chr14:35165067-35168579 |
| 9952 | Fam175b | NM_198013.2 | chr7:140050907-140076797 | | 10047 | Fam26d | NM_001081165.1 | chr10:33758590-33764119 |
| 9953 | Fam178a | NM_001081225.1 | chr19:45005609-45058277 | | 10048 | Fam26e | NM_178908.3 | chr10:33811158-33816325 |
| 9954 | Fam178b | NM_001126046.1 | chr1:36619540-36740028 | | 10049 | Fam26f | NM_175449.4 | chr10:33845872-33847778 |
| 9955 | Fam178b | NM_027957.1 | chr1:36619540-36740028 | | 10050 | Fam32a | NM_026455.4 | chr8:74743628-74747674 |
| 9956 | Fam178b | NM_201365.2 | chr1:36619540-36740028 | | 10051 | Fam35a | NM_029389.2 | chr14:35050220-35123689 |
| 9957 | Fam179a | NM_177087.4 | chr17:72022600-72079009 | | 10052 | Fam3a | NM_025473.3 | chrX:71630058-71638478 |
| 9958 | Fam179b | NM_001166728.1 | chr12:66066728-66123560 | | 10053 | Fam3b | NM_020622.2 | chr16:97692692-97726543 |
| 9959 | Fam180a | NM_173375.1 | chr6:35262745-35276141 | | 10054 | Fam3c | NM_138587.4 | chr6:22256521-22306081 |
| 9960 | Fam181a | NM_001195726.1 | chr12:104553168-104555275 | | 10055 | Fam43a | NM_177632.3 | chr16:30599808-30602883 |

Fig. 25 - 54

| | | | |
|---|---|---|---|
| 10056 | Fam43b | NM_001081672.2 | chr4:137950006-137952373 |
| 10057 | Fam45a | NM_001167829.1 | chr19:60887472-60912132 |
| 10058 | Fam45a | NM_026437.3 | chr19:60887472-60912132 |
| 10059 | Fam46a | NM_001160378.1 | chr9:85214045-85220757 |
| 10060 | Fam46a | NM_001160379.1 | chr9:85214045-85220757 |
| 10061 | Fam46b | NM_175307.6 | chr4:133036047-133043855 |
| 10062 | Fam46c | NM_001142952.1 | chr3:100275458-100293115 |
| 10063 | Fam46d | NM_001163104.2 | chrX:104978090-105068250 |
| 10064 | Fam46d | NM_001271008.1 | chrX:104978090-105068250 |
| 10065 | Fam47c | NM_001164739.1 | chrX:75983101-75984749 |
| 10066 | Fam47e | NM_001033478.2 | chr5:93000562-93020310 |
| 10067 | Fam47e | NM_001170571.1 | chr5:93000562-93020310 |
| 10068 | Fam49a | NM_001146119.1 | chr12:12268944-12399281 |
| 10069 | Fam49a | NM_029758.4 | chr12:12268944-12399281 |
| 10070 | Fam49b | NM_144846.5 | chr15:63760648-63892010 |
| 10071 | Fam50a | NM_138607.3 | chrX:71558372-71565488 |
| 10072 | Fam50b | NM_138746.2 | chr13:34831510-34839491 |
| 10073 | Fam53a | NM_178390.3 | chr5:33943001-33972284 |
| 10074 | Fam53b | NM_175268.4 | chr7:139903766-140004879 |
| 10075 | Fam53b | NM_212473.1 | chr7:139903766-140004879 |
| 10076 | Fam53c | NM_175104.4 | chr18:34918559-34933414 |
| 10077 | Fam57a | NM_027773.3 | chr11:76015557-76021759 |
| 10078 | Fam57b | NM_001146347.1 | chr7:133960398-133973733 |
| 10079 | Fam57b | NM_026884.1 | chr7:133960398-133973733 |
| 10080 | Fam57b | NM_029978.1 | chr7:133960398-133973733 |
| 10081 | Fam58b | NM_197989.1 | chr11:78564007-78565231 |
| 10082 | Fam60a | NM_019643.3 | chr6:148869580-148894954 |
| 10083 | Fam63a | NM_133858.4 | chr3:95086856-95111098 |
| 10084 | Fam63a | NM_199475.1 | chr3:95086856-95111098 |
| 10085 | Fam63b | NM_172772.2 | chr9:70446820-70504981 |
| 10086 | Fam64a | NM_144526.3 | chr11:71856003-71860872 |
| 10087 | Fam65a | NM_001081241.1 | chr8:108129129-108146118 |
| 10088 | Fam65b | NM_001080381.1 | chr13:24674057-24825675 |
| 10089 | Fam65b | NM_001286100.1 | chr13:24674057-24825675 |
| 10090 | Fam65b | NM_001286101.1 | chr13:24674057-24825675 |
| 10091 | Fam65b | NM_029679.2 | chr13:24674057-24825675 |
| 10092 | Fam65b | NM_178658.5 | chr13:24674057-24825675 |
| 10093 | Fam65c | NM_001080708.2 | chr2:167806285-167836093 |
| 10094 | Fam69a | NM_026062.4 | chr5:108337061-108416096 |
| 10095 | Fam69b | NM_019833.3 | chr2:26483976-26492017 |
| 10096 | Fam69c | NM_173770.4 | chr18:84889633-84909828 |
| 10097 | Fam71a | NM_001109759.1 | chr1:192986462-192988696 |
| 10098 | Fam71b | NM_001013783.1 | chr11:46218229-46221487 |
| 10099 | Fam71d | NM_027597.4 | chr12:79792521-79835506 |
| 10100 | Fam71d | NM_029069.1 | chr12:79792521-79835506 |
| 10101 | Fam71e1 | NM_028169.1 | chr7:51751957-51756504 |
| 10102 | Fam71e2 | NM_172895.3 | chr7:4704828-4722872 |
| 10103 | Fam71f1 | NM_001289663.1 | chr6:29269139-29286022 |
| 10104 | Fam71f1 | NM_001289664.1 | chr6:29269139-29286022 |
| 10105 | Fam71f1 | NM_001289665.1 | chr6:29269139-29286022 |
| 10106 | Fam71f1 | NM_207253.3 | chr6:29269139-29286022 |
| 10107 | Fam71f2 | NM_001101486.1 | chr6:29231140-29240676 |
| 10108 | Fam72a | NM_175382.3 | chr1:134424565-134436449 |
| 10109 | Fam73a | NM_001162375.1 | chr3:151936423-152003371 |
| 10110 | Fam73a | NM_174868.4 | chr3:151936423-152003371 |
| 10111 | Fam73b | NM_001242407.1 | chr2:30219752-30241039 |
| 10112 | Fam73b | NM_175392.3 | chr2:30219752-30241039 |
| 10113 | Fam76a | NM_001163792.1 | chr4:132455127-132478466 |
| 10114 | Fam76a | NM_145553.2 | chr4:132455127-132478466 |
| 10115 | Fam76b | NM_176836.3 | chr9:13632170-13650966 |
| 10116 | Fam78a | NM_175511.4 | chr2:31922404-31939225 |
| 10117 | Fam78b | NM_001168026.1 | chr1:168931547-169021433 |
| 10118 | Fam78b | NM_001160262.1 | chr1:168931547-169021433 |
| 10119 | Fam78b | NM_175461.4 | chr1:168931547-169021433 |
| 10120 | Fam81a | NM_029784.2 | chr9:69937116-69989364 |
| 10121 | Fam83a | NM_173862.2 | chr15:57817457-57842257 |
| 10122 | Fam83b | NM_001045518.1 | chr9:76338511-76393611 |
| 10123 | Fam83c | NM_027788.2 | chr2:155654918-155660590 |
| 10124 | Fam83d | NM_027975.2 | chr2:158593834-158612373 |
| 10125 | Fam83e | NM_001033170.4 | chr7:52976590-52984862 |
| 10126 | Fam83f | NM_145986.2 | chr15:80502277-80530855 |
| 10127 | Fam83g | NM_178618.3 | chr1:61497912-61523452 |
| 10128 | Fam83h | NM_001168523.1 | chr15:75831521-75844766 |
| 10129 | Fam83h | NM_134087.2 | chr15:75831521-75844766 |
| 10130 | Fam84a | NM_029007.2 | chr12:14154403-14158844 |
| 10131 | Fam84b | NM_001162926.1 | chr15:60650551-60656635 |
| 10132 | Fam86 | NM_027446.1 | chr5:5244248-5256049 |
| 10133 | Fam89a | NM_001081120.1 | chr8:127264156-127275709 |
| 10134 | Fam89b | NM_023186.2 | chr19:5728086-5729666 |
| 10135 | Fam89b | NM_181452.2 | chr19:5728086-5729666 |
| 10136 | Fam92a | NM_026558.4 | chr4:12080868-12099162 |
| 10137 | Fam92b | NM_001033980.2 | chr8:122690296-122701369 |
| 10138 | Fam96a | NM_026635.3 | chr9:65974417-65986775 |
| 10139 | Fam96b | NM_026753.2 | chr8:107163738-107165628 |
| 10140 | Fam98a | NM_133747.2 | chr17:75936425-75951286 |
| 10141 | Fam98b | NM_026620.3 | chr2:117075474-117097276 |
| 10142 | Fam98c | NM_001146023.1 | chr7:29937529-29941229 |
| 10143 | Fan1 | NM_177893.3 | chr7:71491643-71518981 |
| 10144 | Fanca | NM_016925.3 | chr8:125792144-125842476 |
| 10145 | Fancb | NM_001146081.1 | chrX:161418523-161435204 |
| 10146 | Fancb | NM_175027.4 | chrX:161418523-161435204 |
| 10147 | Fancc | NM_001042673.2 | chr13:63066252-63533053 |
| 10148 | Fancc | NM_001282942.1 | chr13:63066252-63533053 |
| 10149 | Fancc | NM_007985.3 | chr13:63066252-63533053 |
| 10150 | Fancd2 | NM_001033244.3 | chr6:113481675-113546279 |
| 10151 | Fancd2os | NM_026633.3 | chr6:113546755-113550709 |
| 10152 | Fance | NM_001163819.1 | chr17:28450474-28463519 |
| 10153 | Fance | NM_001163820.1 | chr17:28450474-28463519 |
| 10154 | Fance | NR_028296.1 | chr17:28450474-28463519 |
| 10155 | Fance | NR_028297.1 | chr17:28450474-28463519 |
| 10156 | Fancf | NM_001115087.1 | chr7:59115948-59117637 |
| 10157 | Fancg | NM_001163233.1 | chr4:43015208-43023173 |
| 10158 | Fancg | NM_053081.2 | chr4:43015208-43023173 |
| 10159 | Fanci | NM_145946.2 | chr7:86537224-86595150 |
| 10160 | Fancl | NM_001277273.1 | chr11:26287083-26493920 |
| 10161 | Fancl | NM_025923.3 | chr11:26287083-26493920 |
| 10162 | Fancl | NR_102382.1 | chr11:26287083-26493920 |
| 10163 | Fancm | NM_178912.3 | chr12:66176592-66233045 |
| 10164 | Fank1 | NM_025850.2 | chr7:140968574-141073215 |
| 10165 | Fap | NM_007986.3 | chr2:62338992-62412078 |
| 10166 | Far1 | NM_001285831.1 | chr7:120657347-120714402 |
| 10167 | Far1 | NM_027379.3 | chr7:120657347-120714402 |
| 10168 | Far2 | NM_178797.3 | chr6:147995938-148131282 |
| 10169 | Farp1 | NM_134082.3 | chr14:121434795-121682948 |
| 10170 | Farp2 | NM_145519.2 | chr1:95408681-95518553 |
| 10171 | Fars2 | NM_001039189.2 | chr13:36209511-36629464 |
| 10172 | Fars2 | NM_024274.3 | chr13:36209511-36629464 |
| 10173 | Farsa | NM_025648.3 | chr8:87380885-87393156 |
| 10174 | Farsb | NM_001278075.1 | chr1:78306920-78485472 |
| 10175 | Farsb | NM_011811.4 | chr1:78306920-78485472 |
| 10176 | Farsb | NR_102757.1 | chr1:78306920-78485472 |
| 10177 | Farsb | NR_102758.1 | chr1:78306920-78485472 |
| 10178 | Fas | NM_001146708.1 | chr19:34365148-34402260 |
| 10179 | Fas | NM_007987.2 | chr19:34365148-34402260 |
| 10180 | Fasl | NM_001205243.1 | chr1:163710822-163718626 |
| 10181 | Fasl | NM_010177.4 | chr1:163710822-163718626 |
| 10182 | Fasn | NM_007988.3 | chr11:120667271-120685861 |
| 10183 | Fastk | NM_023229.2 | chr5:23946857-23951053 |
| 10184 | Fastkd1 | NM_177244.3 | chr2:69524880-69550663 |
| 10185 | Fastkd2 | NM_172422.3 | chr1:63777198-63799959 |
| 10186 | Fastkd3 | NM_027123.4 | chr13:68721124-68731156 |
| 10187 | Fastkd5 | NM_001146084.1 | chr2:130415731-130455774 |
| 10188 | Fastkd5 | NM_198176.2 | chr2:130415731-130455774 |
| 10189 | Fat1 | NM_001081286.2 | chr8:46035561-46137611 |
| 10190 | Fat2 | NM_001029988.2 | chr11:55064111-55125759 |
| 10191 | Fat3 | NM_001080814.1 | chr9:15714636-16182675 |
| 10192 | Fat4 | NM_183221.3 | chr3:38785861-38910905 |
| 10193 | Fate1 | NR_003243.2 | chrX:69218324-69234385 |
| 10194 | Fau | NM_001160239.2 | chr19:6057887-6059524 |
| 10195 | Fau | NM_001190436.1 | chr19:6057887-6059524 |
| 10196 | Fau | NM_007990.3 | chr19:6057887-6059524 |
| 10197 | Faxc | NM_175234.4 | chr4:21858472-21928608 |
| 10198 | Fbf1 | NM_172571.3 | chr11:116003598-116029492 |
| 10199 | Fbl | NM_007991.3 | chr7:28954766-28964288 |
| 10200 | Fblim1 | NM_001163256.1 | chr4:141131976-141161967 |
| 10201 | Fblim1 | NM_133754.5 | chr4:141131976-141161967 |
| 10202 | Fbll1 | NM_001004147.3 | chr11:35610881-35612386 |
| 10203 | Fbln1 | NM_010180.2 | chr15:85036437-85116724 |
| 10204 | Fbln2 | NM_001081437.1 | chr6:91162757-91222534 |
| 10205 | Fbln2 | NM_007992.2 | chr6:91162757-91222534 |
| 10206 | Fbln5 | NM_011812.1 | chr12:102984774-103057329 |
| 10207 | Fbln7 | NM_024237.4 | chr2:128689667-128722770 |
| 10208 | Fbn1 | NM_007993.2 | chr2:125126329-125332174 |
| 10209 | Fbn2 | NM_010181.2 | chr18:58168276-58369580 |
| 10210 | Fbp1 | NM_019395.3 | chr13:62966112-62989642 |
| 10211 | Fbp2 | NM_007994.3 | chr13:62938244-62959730 |
| 10212 | Fbrs | NM_009183.1 | chr7:134628735-134635027 |
| 10213 | Fbrsl1 | NM_001126642.1 | chr5:110790770-110877522 |
| 10214 | Fbrsl1 | NM_028596.2 | chr5:110790770-110877522 |
| 10215 | Fbxl12 | NM_001002846.2 | chr9:20442192-20451233 |
| 10216 | Fbxl12 | NM_001286529.1 | chr9:20442192-20451233 |
| 10217 | Fbxl12 | NM_001286530.1 | chr9:20442192-20451233 |
| 10218 | Fbxl12 | NM_139113 | chr9:20442192-20451233 |
| 10219 | Fbxl12os | NR_033729.1 | chr9:20415918-20421715 |
| 10220 | Fbxl13 | NM_001199632.1 | chr5:20989664-21151423 |
| 10221 | Fbxl13 | NM_177076.3 | chr5:20989664-21151423 |
| 10222 | Fbxl14 | NM_133940.3 | chr6:119429686-119431904 |
| 10223 | Fbxl15 | NM_133634.2 | chr19:46402674-46404936 |
| 10224 | Fbxl16 | NM_001164225.1 | chr17:25946029-25958210 |
| 10225 | Fbxl17 | NM_015794.1 | chr17:63395300-63849929 |
| 10226 | Fbxl18 | NM_001033312.3 | chr5:143633467-143656917 |
| 10227 | Fbxl19 | NM_172748.2 | chr7:134890288-134912442 |
| 10228 | Fbxl2 | NM_178624.6 | chr9:113886076-113935869 |
| 10229 | Fbxl20 | NM_028149.1 | chr11:97943867-98010930 |
| 10230 | Fbxl21 | NM_178674.4 | chr13:56623868-56639147 |
| 10231 | Fbxl22 | NM_175206.4 | chr9:66356266-66362400 |
| 10232 | Fbxl3 | NM_155822.2 | chr14:103479455-103498726 |
| 10233 | Fbxl4 | NM_172988.4 | chr4:22284689-22361238 |
| 10234 | Fbxl4 | NR_104378.1 | chr4:22284689-22361238 |
| 10235 | Fbxl4 | NR_104379.1 | chr4:22284689-22361238 |
| 10236 | Fbxl4 | NR_104380.1 | chr4:22284689-22361238 |
| 10237 | Fbxl5 | NM_001159963.1 | chr5:44135856-44173388 |
| 10238 | Fbxl5 | NM_178729.4 | chr5:44135856-44173388 |
| 10239 | Fbxl6 | NM_013909.2 | chr15:76366157-76369176 |
| 10240 | Fbxl7 | NM_176959.3 | chr15:26470213-26825319 |
| 10241 | Fbxl8 | NM_015821.2 | chr8:107788547-107793226 |
| 10242 | Fbxo10 | NM_001024142.1 | chr4:45047120-45097476 |
| 10243 | Fbxo11 | NM_001081034.1 | chr17:88390199-88464625 |
| 10244 | Fbxo15 | NM_015798.3 | chr18:85104417-85150784 |
| 10245 | Fbxo16 | NM_015795.1 | chr14:65885537-65940339 |

Fig. 25 - 55

| | | | |
|---|---|---|---|
| 10246 | Fbxo17 | NM_015796.2 | chr7:29501808-29523159 |
| 10247 | Fbxo18 | NM_015792.1 | chr2:11664199-11699154 |
| 10248 | Fbxo2 | NM_176848.1 | chr4:147534776-147540526 |
| 10249 | Fbxo21 | NM_145564.3 | chr5:118426778-118460200 |
| 10250 | Fbxo22 | NM_028049.2 | chr9:55056742-55072240 |
| 10251 | Fbxo24 | NM_027708.1 | chr5:138053732-138066306 |
| 10252 | Fbxo25 | NM_025785.2 | chr8:13907805-13940521 |
| 10253 | Fbxo27 | NM_001163702.1 | chr7:29477867-29484356 |
| 10254 | Fbxo27 | NM_207238.3 | chr7:29477867-29484356 |
| 10255 | Fbxo28 | NM_175127.2 | chr1:184243232-184271737 |
| 10256 | Fbxo3 | NM_020593.2 | chr2:103867955-103903394 |
| 10257 | Fbxo3 | NM_212433.1 | chr2:103867955-103903394 |
| 10258 | Fbxo30 | NM_001168297.1 | chr10:11001127-11017767 |
| 10259 | Fbxo30 | NM_027968.3 | chr10:11001127-11017767 |
| 10260 | Fbxo31 | NM_133765.4 | chr8:124073342-124102706 |
| 10261 | Fbxo32 | NM_026346.3 | chr15:58007433-58046447 |
| 10262 | Fbxo33 | NM_001033156.4 | chr12:60301641-60320470 |
| 10263 | Fbxo34 | NM_001146085.1 | chr14:48092235-48151637 |
| 10264 | Fbxo34 | NM_001146086.1 | chr14:48092235-48151637 |
| 10265 | Fbxo34 | NM_030236.3 | chr14:48092235-48151637 |
| 10266 | Fbxo34 | NR_027414.1 | chr14:48092235-48151637 |
| 10267 | Fbxo36 | NM_025386.3 | chr1:84836415-84897061 |
| 10268 | Fbxo38 | NM_134136.3 | chr18:62663712-62708397 |
| 10269 | Fbxo39 | NM_001099688.2 | chr11:72127945-72132923 |
| 10270 | Fbxo4 | NM_134099.2 | chr15:3913563-3929573 |
| 10271 | Fbxo40 | NM_001037321.1 | chr16:36966158-36979222 |
| 10272 | Fbxo41 | NM_001001160.3 | chr6:85419569-85452988 |
| 10273 | Fbxo41 | NM_001289674.1 | chr6:85419569-85452988 |
| 10274 | Fbxo41 | NM_001289675.1 | chr6:85419569-85452988 |
| 10275 | Fbxo42 | NM_172518.3 | chr4:140703836-140759977 |
| 10276 | Fbxo43 | NM_001081253.1 | chr15:36079814-36094639 |
| 10277 | Fbxo44 | NM_001161851.2 | chr4:147526907-147534203 |
| 10278 | Fbxo44 | NM_001161852.2 | chr4:147526907-147534203 |
| 10279 | Fbxo44 | NM_173401.1 | chr4:147526907-147534203 |
| 10280 | Fbxo44 | NR_104374.1 | chr4:147526907-147534203 |
| 10281 | Fbxo44 | NR_104375.1 | chr4:147526907-147534203 |
| 10282 | Fbxo45 | NM_173439.2 | chr16:32230197-32247111 |
| 10283 | Fbxo46 | NM_175530.3 | chr7:19705207-19723610 |
| 10284 | Fbxo47 | NM_001081435.1 | chr11:97715620-97745468 |
| 10285 | Fbxo48 | NM_176982.2 | chr11:16851412-16854775 |
| 10286 | Fbxo5 | NM_025995.2 | chr10:4541075-4547383 |
| 10287 | Fbxo6 | NM_001163669.2 | chr4:147519824-147526244 |
| 10288 | Fbxo6 | NM_001163705.1 | chr4:147519824-147526244 |
| 10289 | Fbxo6 | NM_001163706.1 | chr4:147519824-147526244 |
| 10290 | Fbxo6 | NM_001163707.1 | chr4:147519824-147526244 |
| 10291 | Fbxo6 | NM_015797.4 | chr4:147519824-147526244 |
| 10292 | Fbxo7 | NM_153195.2 | chr10:85484673-85511073 |
| 10293 | Fbxo8 | NM_015791.3 | chr8:59029930-59072736 |
| 10294 | Fbxo9 | NM_001081490.2 | chr9:77929305-77956872 |
| 10295 | Fbxo9 | NM_023605.2 | chr9:77929305-77956872 |
| 10296 | Fbxw10 | NM_001033669.2 | chr11:62660624-62690964 |
| 10297 | Fbxw10 | NM_001291441.1 | chr11:62660624-62690964 |
| 10298 | Fbxw11 | NM_001271347.1 | chr11:32542554-32646814 |
| 10299 | Fbxw11 | NM_001271348.1 | chr11:32542554-32646814 |
| 10300 | Fbxw11 | NM_001271349.1 | chr11:32542554-32646814 |
| 10301 | Fbxw11 | NM_134015.3 | chr11:32542554-32646814 |
| 10302 | Fbxw13 | NM_177598.3 | chr9:109081740-109098489 |
| 10303 | Fbxw14 | NM_015793.2 | chr9:109173638-109190190 |
| 10304 | Fbxw15 | NM_199036.2 | chr9:109465515-109470776 |
| 10305 | Fbxw16 | NM_177070.3 | chr9:109334831-109351654 |
| 10306 | Fbxw17 | NM_175401.3 | chr13:50513245-50529138 |
| 10307 | Fbxw18 | NM_001033794.3 | chr9:109579247-109605214 |
| 10308 | Fbxw19 | NM_177703.3 | chr9:109381088-109398368 |
| 10309 | Fbxw2 | NM_001164768.1 | chr2:34659883-34681755 |
| 10310 | Fbxw2 | NM_001164769.1 | chr2:34659883-34681755 |
| 10311 | Fbxw2 | NM_001164770.1 | chr2:34659883-34681755 |
| 10312 | Fbxw2 | NM_001164772.1 | chr2:34659883-34681755 |
| 10313 | Fbxw2 | NM_013890.4 | chr2:34659883-34681755 |
| 10314 | Fbxw20 | NM_001008428.3 | chr9:109119945-109137268 |
| 10315 | Fbxw21 | NM_177069.3 | chr9:109041967-109064556 |
| 10316 | Fbxw22 | NM_001014395.2 | chr9:109280922-109306808 |
| 10317 | Fbxw24 | NM_001013776.4 | chr9:109503629-109528573 |
| 10318 | Fbxw26 | NM_198674.2 | chr9:109620079-109648603 |
| 10319 | Fbxw28 | NM_001177419.1 | chr9:109225399-109242173 |
| 10320 | Fbxw28 | NM_001177420.1 | chr9:109225399-109242173 |
| 10321 | Fbxw4 | NM_013907.2 | chr19:45652747-45734683 |
| 10322 | Fbxw5 | NM_013908.4 | chr2:25356298-25360990 |
| 10323 | Fbxw7 | NM_001177773.1 | chr3:84619498-84783120 |
| 10324 | Fbxw7 | NM_001177774.1 | chr3:84619498-84783120 |
| 10325 | Fbxw7 | NM_080428.3 | chr3:84619498-84783120 |
| 10326 | Fbxw8 | NM_172721.2 | chr5:118514989-118605467 |
| 10327 | Fbxw9 | NM_026791.2 | chr8:87584018-87591019 |
| 10328 | Fcamr | NM_001170632.1 | chr1:132697478-132711317 |
| 10329 | Fcamr | NM_144960.2 | chr1:132697478-132711317 |
| 10330 | Fcer1a | NM_001284.4 | chr1:175151401-175157360 |
| 10331 | Fcer1g | NM_010185.4 | chr1:173159702-173164480 |
| 10332 | Fcer2a | NM_001253737.1 | chr8:3681736-3694174 |
| 10333 | Fcer2a | NM_001253739.1 | chr8:3681736-3694174 |
| 10334 | Fcer2a | NM_001253743.1 | chr8:3681736-3694174 |
| 10335 | Fcer2a | NM_001253745.1 | chr8:3681736-3694174 |
| 10336 | Fcer2a | NM_001253746.1 | chr8:3681736-3694174 |
| 10337 | Fcer2a | NM_001253747.1 | chr8:3681736-3694174 |
| 10338 | Fcer2a | NM_013517.3 | chr8:3681736-3694174 |
| 10339 | Fcf1 | NM_028632.2 | chr2:86311879-86324253 |
| 10340 | Fcgbp | NM_001122603.1 | chr7:28856254-28905883 |
| 10341 | Fcgr1 | NM_010186.5 | chr3:96086831-96097892 |
| 10342 | Fcgr2b | NM_001077189.1 | chr1:172890688-172906202 |
| 10343 | Fcgr2b | NM_010187.2 | chr1:172890688-172906202 |
| 10344 | Fcgr3 | NM_010188.5 | chr1:172981299-172989534 |
| 10345 | Fcgr4 | NM_144559.2 | chr1:172949056-172959892 |
| 10346 | Fcgrt | NM_010189.3 | chr7:52348362-52359192 |
| 10347 | Fcho1 | NM_028715.3 | chr8:74232285-74249580 |
| 10348 | Fcho1 | NR_028267.1 | chr8:74232285-74249580 |
| 10349 | Fcho2 | NM_172591.3 | chr13:99493360-99585404 |
| 10350 | Fchsd1 | NM_175684.4 | chr18:38117088-38129385 |
| 10351 | Fchsd2 | NM_001146010.1 | chr7:108257288-108432919 |
| 10352 | Fchsd2 | NM_199012.2 | chr7:108257288-108432919 |
| 10353 | Fcna | NM_007995.3 | chr2:25480186-25483494 |
| 10354 | Fcnb | NM_010190.1 | chr2:27931998-27940398 |
| 10355 | Fcrl1 | NM_001136236.1 | chr3:87180308-87196055 |
| 10356 | Fcrl1 | NM_153090.2 | chr3:87180308-87196055 |
| 10357 | Fcrl1 | NM_178165.4 | chr3:87180308-87196055 |
| 10358 | Fcrl5 | NM_001113238.1 | chr3:87239703-87304600 |
| 10359 | Fcrl5 | NM_183222.3 | chr3:87239703-87304600 |
| 10360 | Fcrl6 | NM_001164725.1 | chr1:174526770-174532682 |
| 10361 | Fcrla | NM_001160215.1 | chr1:172847724-172857714 |
| 10362 | Fcrla | NM_145141.2 | chr1:172847724-172857714 |
| 10363 | Fcrla | NR_027666.1 | chr1:172847724-172857714 |
| 10364 | Fcrlb | NM_001029984.2 | chr1:172837403-172843072 |
| 10365 | Fcrls | NM_030707.3 | chr3:87054886-87067446 |
| 10366 | Fdft1 | NM_010191.1 | chr14:63763988-63798415 |
| 10367 | Fdps | NM_001253751.1 | chr3:88897509-88905889 |
| 10368 | Fdps | NM_134469.4 | chr3:88897509-88905889 |
| 10369 | Fdx1 | NM_007996.2 | chr9:51751411-51771638 |
| 10370 | Fdx1l | NM_001039824.2 | chr9:20871964-20877958 |
| 10371 | Fdxacb1 | NM_198675.2 | chr9:50576342-50580775 |
| 10372 | Fdxr | NM_007997.1 | chr11:115129338-115138283 |
| 10373 | Fech | NM_007998.6 | chr18:64616203-64648720 |
| 10374 | Fem1a | NM_010192.4 | chr17:56396215-56403031 |
| 10375 | Fem1b | NM_010193.4 | chr9:62639635-62659455 |
| 10376 | Fem1c | NM_173423.4 | chr18:46664259-46685625 |
| 10377 | Fen1 | NM_001271614.1 | chr19:10273621-10278433 |
| 10378 | Fen1 | NM_001271615.1 | chr19:10273621-10278433 |
| 10379 | Fen1 | NM_007999.4 | chr19:10273621-10278433 |
| 10380 | Fendrr | NR_045471.2 | chr8:123578781-123606932 |
| 10381 | Fer1l4 | NM_001136556.1 | chr2:155844875-155878683 |
| 10382 | Fer1l5 | NM_001277076.1 | chr1:36429135-36478955 |
| 10383 | Ferd3l | NM_033522.2 | chr12:34613289-34614174 |
| 10384 | Fermt1 | NM_198029.2 | chr2:132729914-132771772 |
| 10385 | Fermt2 | NM_146054.2 | chr14:46078466-46149740 |
| 10386 | Fermt3 | NM_153795.2 | chr19:7073448-7093959 |
| 10387 | Fert2 | NM_001037997.3 | chr17:64213329-64488846 |
| 10388 | Fert2 | NM_001286415.1 | chr17:64213329-64488846 |
| 10389 | Fert2 | NM_008000.2 | chr17:64213329-64488846 |
| 10390 | Fes | NM_010194.2 | chr7:87522643-87532832 |
| 10391 | Fetub | NM_001083904.1 | chr16:22918454-22939841 |
| 10392 | Fetub | NM_001083905.1 | chr16:22918454-22939841 |
| 10393 | Fetub | NM_021564.2 | chr16:22918454-22939841 |
| 10394 | Fev | NM_153111.2 | chr1:74928082-74931982 |
| 10395 | Fez1 | NM_183171.4 | chr9:36651243-36686225 |
| 10396 | Fez2 | NM_001285940.1 | chr17:78599587-78817492 |
| 10397 | Fez2 | NM_001285946.1 | chr17:78599587-78817492 |
| 10398 | Fez2 | NM_001285949.1 | chr17:78599587-78817492 |
| 10399 | Fez2 | NM_199448.3 | chr17:78599587-78817492 |
| 10400 | Fezf1 | NM_028462.1 | chr6:23195046-23198264 |
| 10401 | Fezf2 | NM_080433.3 | chr14:13174405-13178379 |
| 10402 | Ffar1 | NM_194057.2 | chr7:31646586-31646489 |
| 10403 | Ffar2 | NM_001168509.1 | chr7:31603375-31608794 |
| 10404 | Ffar2 | NM_001168510.1 | chr7:31603375-31608794 |
| 10405 | Ffar2 | NM_001168511.1 | chr7:31603375-31608794 |
| 10406 | Ffar2 | NM_001168512.1 | chr7:31603375-31608794 |
| 10407 | Ffar2 | NM_146187.4 | chr7:31603375-31608794 |
| 10408 | Ffar3 | NM_001033316.2 | chr7:31639348-31641197 |
| 10409 | Ffar4 | NM_181748.2 | chr19:38171568-38188753 |
| 10410 | Fga | NM_001111048.2 | chr3:82830074-82837539 |
| 10411 | Fga | NM_010196.4 | chr3:82830074-82837539 |
| 10412 | Fgb | NM_181849.2 | chr3:82846226-82853712 |
| 10413 | Fgd1 | NM_008001.4 | chrX:147481713-147524229 |
| 10414 | Fgd2 | NM_001159538.1 | chr17:29497858-29516480 |
| 10415 | Fgd2 | NM_013710.4 | chr17:29497858-29516480 |
| 10416 | Fgd3 | NM_015759.2 | chr13:49358478-49404577 |
| 10417 | Fgd4 | NM_139232.3 | chr16:16422070-16560289 |
| 10418 | Fgd4 | NM_139233.2 | chr16:16422070-16560289 |
| 10419 | Fgd4 | NM_139234.2 | chr16:16422070-16560289 |
| 10420 | Fgd5 | NM_172731.2 | chr6:91937103-92025999 |
| 10421 | Fgd6 | NM_053072.3 | chr10:93498745-93608084 |
| 10422 | Fgf1 | NM_010197.3 | chr18:38998327-39078353 |
| 10423 | Fgf10 | NM_008002.4 | chr13:119503505-119581380 |
| 10424 | Fgf11 | NM_001291104.1 | chr11:69609569-69615218 |
| 10425 | Fgf11 | NM_010198.2 | chr11:69609569-69615218 |
| 10426 | Fgf12 | NM_001276419.2 | chr16:28158669-28753329 |
| 10427 | Fgf12 | NM_001276420.1 | chr16:28158669-28753329 |
| 10428 | Fgf12 | NM_010199.4 | chr16:28158669-28753329 |
| 10429 | Fgf12 | NM_183064.5 | chr16:28158669-28753329 |
| 10430 | Fgf13 | NM_001290414.1 | chrX:56315323-56838749 |
| 10431 | Fgf13 | NM_001290415.1 | chrX:56315323-56838749 |
| 10432 | Fgf13 | NM_010200.3 | chrX:56315323-56838749 |
| 10433 | Fgf14 | NM_010201.4 | chr14:124377512-125076349 |
| 10434 | Fgf14 | NM_207667.3 | chr14:124377512-125076349 |
| 10435 | Fgf15 | NM_008003.2 | chr7:152082436-152086856 |

Fig. 25 - 56

| ID | Gene | Accession | Location |
|---|---|---|---|
| 10436 | Fgf16 | NM_030614.2 | chrX:102959815-102971871 |
| 10437 | Fgf17 | NM_008004.4 | chr14:71036011-71042075 |
| 10438 | Fgf18 | NM_008005.2 | chr11:33016977-33047400 |
| 10439 | Fgf18 | NR_102395.1 | chr11:33016977-33047400 |
| 10440 | Fgf2 | NM_008006.2 | chr3:37247554-37303752 |
| 10441 | Fgf20 | NM_030610.2 | chr8:41364519-41372307 |
| 10442 | Fgf21 | NM_020013.4 | chr7:52869259-52870860 |
| 10443 | Fgf22 | NM_023304.1 | chr10:79217863-79219706 |
| 10444 | Fgf23 | NM_022657.4 | chr6:127022919-127032314 |
| 10445 | Fgf3 | NM_008007.2 | chr7:152024516-152029253 |
| 10446 | Fgf4 | NM_010202.5 | chr7:152047290-152051148 |
| 10447 | Fgf5 | NM_001277268.1 | chr5:98683202-98706052 |
| 10448 | Fgf5 | NM_010203.5 | chr5:98683202-98706052 |
| 10449 | Fgf6 | NM_010204.1 | chr6:126965559-126974736 |
| 10450 | Fgf7 | NM_008008.4 | chr2:125860394-125916921 |
| 10451 | Fgf8 | NM_001166361.1 | chr19:45811287-45817374 |
| 10452 | Fgf8 | NM_001166362.1 | chr19:45811287-45817374 |
| 10453 | Fgf8 | NM_001166363.1 | chr19:45811287-45817374 |
| 10454 | Fgf8 | NM_010205.2 | chr19:45811287-45817374 |
| 10455 | Fgf9 | NM_013518.2 | chr14:58691522-58731557 |
| 10456 | Fgfbp1 | NM_001271616.1 | chr5:44370096-44373038 |
| 10457 | Fgfbp1 | NM_008009.4 | chr5:44370096-44373038 |
| 10458 | Fgfbp3 | NM_028263.1 | chr19:36992039-36994089 |
| 10459 | Fgfr1 | NM_001079908.2 | chr8:26629230-26686190 |
| 10460 | Fgfr1 | NM_001079909.2 | chr8:26629230-26686190 |
| 10461 | Fgfr1 | NM_010206.3 | chr8:26629230-26686190 |
| 10462 | Fgfr1op | NM_001197046.1 | chr17:8358382-8389335 |
| 10463 | Fgfr1op | NM_201230.5 | chr17:8358382-8389335 |
| 10464 | Fgfr1op2 | NM_026218.2 | chr6:146526432-146547720 |
| 10465 | Fgfr2 | NM_010207.2 | chr7:137305964-137410322 |
| 10466 | Fgfr2 | NM_201601.2 | chr7:137305964-137410322 |
| 10467 | Fgfr3 | NM_001163215.2 | chr5:34064372-34079717 |
| 10468 | Fgfr3 | NM_001163216.2 | chr5:34064372-34079717 |
| 10469 | Fgfr3 | NM_001163217.2 | chr5:34064372-34079717 |
| 10470 | Fgfr3 | NM_001205270.1 | chr5:34064372-34079717 |
| 10471 | Fgfr3 | NM_008010.3 | chr5:34064372-34079717 |
| 10472 | Fgfr4 | NM_008011.2 | chr13:55254178-55270120 |
| 10473 | Fgfrl1 | NM_001164259.1 | chr5:109123247-109135969 |
| 10474 | Fgfrl1 | NM_054071.2 | chr5:109123247-109135969 |
| 10475 | Fgg | NM_133862.1 | chr3:82811817-82818971 |
| 10476 | Fggy | NM_001113412.1 | chr4:95224197-95593630 |
| 10477 | Fggy | NM_029347.2 | chr4:95224197-95593630 |
| 10478 | Fgl1 | NM_145594.2 | chr8:42276787-42300510 |
| 10479 | Fgl2 | NM_008013.4 | chr5:20878491-20884204 |
| 10480 | Fgr | NM_010208.4 | chr4:132530009-132557797 |
| 10481 | Fh1 | NM_010209.2 | chr1:177531508-177555766 |
| 10482 | Fhad1 | NM_177868.4 | chr4:141446538-141567566 |
| 10483 | Fhadlos1 | NR_040672.1 | chr4:141538907-141542712 |
| 10484 | Fhdc1 | NM_001333301.4 | chr3:84246117-84284361 |
| 10485 | Fhdc1 | NM_001205355.1 | chr3:84246117-84284361 |
| 10486 | Fhit | NM_010210.3 | chr14:10382608-11994549 |
| 10487 | Fhl1 | NM_001077361.1 | chrX:53984937-54046523 |
| 10488 | Fhl1 | NM_001077362.2 | chrX:53984937-54046523 |
| 10489 | Fhl1 | NM_001287800.1 | chrX:53984937-54046523 |
| 10490 | Fhl1 | NM_010211.3 | chrX:53984937-54046523 |
| 10491 | Fhl2 | NM_001289533.1 | chr1:43179915-43253606 |
| 10492 | Fhl2 | NM_010212.4 | chr1:43179915-43253606 |
| 10493 | Fhl3 | NM_010213.1 | chr4:124377942-124385855 |
| 10494 | Fhl4 | NM_010214.4 | chr10:84559763-84565240 |
| 10495 | Fhl5 | NM_021318.3 | chr4:25127055-25170023 |
| 10496 | Fhod1 | NM_177699.4 | chr8:107853059-107871870 |
| 10497 | Fhod3 | NM_001289654.1 | chr18:24867123-25327378 |
| 10498 | Fhod3 | NM_001289655.1 | chr18:24867123-25327378 |
| 10499 | Fhod3 | NM_175276.4 | chr18:24867123-25327378 |
| 10500 | Fibcd1 | NM_178887.4 | chr2:31668809-31701525 |
| 10501 | Fibin | NM_026271.1 | chr2:110201081-110203150 |
| 10502 | Fibp | NM_001253832.1 | chr19:5460606-5465052 |
| 10503 | Fibp | NM_021438.4 | chr19:5460606-5465052 |
| 10504 | Ficd | NM_001010825.3 | chr5:114185790-114190616 |
| 10505 | Fig4 | NM_133999.1 | chr10:40907977-41023047 |
| 10506 | Figf | NM_010216.2 | chrX:160811479-160840579 |
| 10507 | Figla | NM_012013.1 | chr6:85967184-85970990 |
| 10508 | Fign | NM_001267846.1 | chr2:63809564-63936095 |
| 10509 | Fign | NM_001267847.1 | chr2:63809564-63936095 |
| 10510 | Fign | NM_021716.5 | chr2:63809564-63936095 |
| 10511 | Fignl1 | NM_001163585.1 | chr11:11700290-11708965 |
| 10512 | Fignl1 | NM_001163360.1 | chr11:11700290-11708965 |
| 10513 | Fignl1 | NM_021891.3 | chr11:11700290-11708965 |
| 10514 | Fignl2 | NM_001214911.2 | chr15:100880622-100884830 |
| 10515 | Filip1 | NM_001081243.1 | chr9:79663368-79825689 |
| 10516 | Filip1l | NM_001040397.4 | chr16:57302112-57606980 |
| 10517 | Filip1l | NM_001177871.1 | chr16:57302112-57606980 |
| 10518 | Fip1l1 | NM_001159573.1 | chr5:74931506-75098928 |
| 10519 | Fip1l1 | NM_001159574.1 | chr5:74931506-75098928 |
| 10520 | Fip1l1 | NM_024183.5 | chr5:74931506-75098928 |
| 10521 | Firre | NR_015505.2 | chrX:47908920-47988435 |
| 10522 | Firre | NR_026976.1 | chrX:47908920-47988435 |
| 10523 | Fis1 | NM_001163243.1 | chr5:137429144-137442104 |
| 10524 | Fis1 | NM_025562.3 | chr5:137429144-137442104 |
| 10525 | Fitm1 | NM_026808.1 | chr14:56194510-56195789 |
| 10526 | Fitm2 | NM_173397.4 | chr2:163294439-163298365 |
| 10527 | Fiz1 | NM_001110328.1 | chr7:4958657-4966330 |
| 10528 | Fiz1 | NM_001110329.1 | chr7:4958657-4966330 |
| 10529 | Fiz1 | NM_001110330.1 | chr7:4958657-4966330 |
| 10530 | Fiz1 | NM_011813.3 | chr7:4958657-4966330 |
| 10531 | Fjx1 | NM_010218.2 | chr2:102289522-102291949 |
| 10532 | Fkbp10 | NM_001163481.1 | chr11:100277007-100302403 |
| 10533 | Fkbp10 | NM_010221.2 | chr11:100277007-100302403 |
| 10534 | Fkbp11 | NM_024169.3 | chr15:98554798-98558629 |
| 10535 | Fkbp14 | NM_153573.1 | chr6:54527598-54543122 |
| 10536 | Fkbp15 | NM_001045528.1 | chr4:61961375-62021582 |
| 10537 | Fkbp1a | NM_008019.3 | chr2:151368234-151387427 |
| 10538 | Fkbp1b | NM_016863.3 | chr12:4839979-4848401 |
| 10539 | Fkbp2 | NM_001166368.1 | chr19:7052228-7054951 |
| 10540 | Fkbp2 | NM_008020.3 | chr19:7052228-7054951 |
| 10541 | Fkbp3 | NM_013902.4 | chr12:66163419-66174925 |
| 10542 | Fkbp4 | NM_010219.3 | chr6:128380124-128388649 |
| 10543 | Fkbp5 | NM_010220.4 | chr17:28535697-28623094 |
| 10544 | Fkbp6 | NM_001277891.1 | chr5:135767573-135825914 |
| 10545 | Fkbp6 | NM_001277892.1 | chr5:135767573-135825914 |
| 10546 | Fkbp6 | NM_001277893.1 | chr5:135767573-135825914 |
| 10547 | Fkbp6 | NM_033571.3 | chr5:135767573-135825914 |
| 10548 | Fkbp7 | NM_010222.2 | chr2:76501090-76511155 |
| 10549 | Fkbp8 | NM_001111066.1 | chr8:73051641-73059227 |
| 10550 | Fkbp8 | NM_001199631.1 | chr8:73051641-73059227 |
| 10551 | Fkbp8 | NM_010223.2 | chr8:73051641-73059227 |
| 10552 | Fkbp9 | NM_012056.2 | chr6:56782052-56829354 |
| 10553 | Fkbpl | NM_019873.2 | chr17:34781827-34783272 |
| 10554 | Fkrp | NM_173430.2 | chr7:17394616-17402081 |
| 10555 | Fktn | NM_139309.4 | chr4:53727053-53776143 |
| 10556 | Flad1 | NM_177041.3 | chr3:89206594-89215785 |
| 10557 | Flcn | NM_001271356.1 | chr11:59604909-59623541 |
| 10558 | Flcn | NM_001271357.1 | chr11:59604909-59623541 |
| 10559 | Flcn | NM_146018.2 | chr11:59604909-59623541 |
| 10560 | Flcn | NR_073164.1 | chr11:59604909-59623541 |
| 10561 | Flg2 | NM_001013804.1 | chr3:93001194-93025298 |
| 10562 | Fli1 | NM_008026.5 | chr9:32229792-32348953 |
| 10563 | Flii | NM_022009.2 | chr11:60527649-60540765 |
| 10564 | Flna | NM_001290421.1 | chrX:71468799-71491873 |
| 10565 | Flna | NM_010227.3 | chrX:71468799-71491873 |
| 10566 | Flnb | NM_001081427.1 | chr14:8650470-8784101 |
| 10567 | Flnb | NM_134080.1 | chr14:8650470-8784101 |
| 10568 | Flnc | NM_001081185.1 | chr6:29383152-29411888 |
| 10569 | Flot1 | NM_008027.2 | chr17:35960301-35969752 |
| 10570 | Flot2 | NM_001040403.1 | chr11:77851442-77873934 |
| 10571 | Flot2 | NM_001284227.1 | chr11:77851442-77873934 |
| 10572 | Flot2 | NM_001284228.1 | chr11:77851442-77873934 |
| 10573 | Flot2 | NM_008028.2 | chr11:77851442-77873934 |
| 10574 | Flrt1 | NM_201411.2 | chr19:7166502-7180219 |
| 10575 | Flrt2 | NM_201518.4 | chr12:96930435-97023423 |
| 10576 | Flrt3 | NM_001172160.1 | chr2:140221165-142215786 |
| 10577 | Flrt3 | NM_178382.4 | chr2:140221165-142215786 |
| 10578 | Flt1 | NM_010228.3 | chr5:148373771-148537564 |
| 10579 | Flt3 | NM_010229.2 | chr5:148142316-148212065 |
| 10580 | Flt3l | NM_013520.3 | chr7:52386558-52391802 |
| 10581 | Flt3l | NR_102725.1 | chr7:52386558-52391802 |
| 10582 | Flt4 | NM_008029.3 | chr11:49423180-49466241 |
| 10583 | Flywch1 | NM_153791.2 | chr17:23892389-23908558 |
| 10584 | Flywch2 | NM_029798.3 | chr17:23913884-23923044 |
| 10585 | Fmn1 | NM_001285458.1 | chr2:113167892-113556924 |
| 10586 | Fmn1 | NM_001285459.1 | chr2:113167892-113556924 |
| 10587 | Fmn1 | NM_001287817.1 | chr2:113167892-113556924 |
| 10588 | Fmn1 | NM_001287818.1 | chr2:113167892-113556924 |
| 10589 | Fmn1 | NM_010230.2 | chr2:113167892-113556924 |
| 10590 | Fmn2 | NM_019445.2 | chr1:176431955-176752860 |
| 10591 | Fmnl1 | NM_001077698.1 | chr11:103032451-103060214 |
| 10592 | Fmnl1 | NM_019679.2 | chr11:103032451-103060214 |
| 10593 | Fmnl2 | NM_172409.2 | chr2:52716901-52993236 |
| 10594 | Fmnl3 | NM_011711.1 | chr15:99147653-99200897 |
| 10595 | Fmo1 | NM_010231.2 | chr1:164759691-164796679 |
| 10596 | Fmo2 | NM_018881.3 | chr1:164805177-164828843 |
| 10597 | Fmo3 | NM_008030.1 | chr1:164883930-164914622 |
| 10598 | Fmo4 | NM_144878.1 | chr1:164724013-164742680 |
| 10599 | Fmo5 | NM_001161763.1 | chr3:97432726-97459210 |
| 10600 | Fmo5 | NM_001161765.1 | chr3:97432726-97459210 |
| 10601 | Fmo5 | NM_010232.4 | chr3:97432726-97459210 |
| 10602 | Fmo6 | NM_001178038.1 | chr1:164846681-164867356 |
| 10603 | Fmo9 | NM_172844.2 | chr1:168592185-168611976 |
| 10604 | Fmod | NM_021355.3 | chr1:135934091-135944854 |
| 10605 | Fmr1 | NM_001290424.1 | chrX:65931715-65971136 |
| 10606 | Fmr1 | NM_008031.3 | chrX:65931715-65971136 |
| 10607 | Fmr1nb | NM_001166619.1 | chrX:66015013-66057735 |
| 10608 | Fmr1nb | NM_001166620.1 | chrX:66015013-66057735 |
| 10609 | Fmr1nb | NM_174993.2 | chrX:66015013-66057735 |
| 10610 | Fn1 | NM_001276408.1 | chr1:71632046-71699808 |
| 10611 | Fn1 | NM_001276409.1 | chr1:71632046-71699808 |
| 10612 | Fn1 | NM_001276410.1 | chr1:71632046-71699808 |
| 10613 | Fn1 | NM_001276411.1 | chr1:71632046-71699808 |
| 10614 | Fn1 | NM_001276412.1 | chr1:71632046-71699808 |
| 10615 | Fn1 | NM_001276413.1 | chr1:71632046-71699808 |
| 10616 | Fn1 | NM_010233.2 | chr1:71632046-71699808 |
| 10617 | Fn3k | NM_001038699.2 | chr11:121296266-121311804 |
| 10618 | Fn3k | NM_022014.4 | chr11:121296266-121311804 |
| 10619 | Fn3krp | NM_181420.3 | chr11:121282686-121292082 |
| 10620 | Fnbp1 | NM_001038700.2 | chr2:30881725-30997528 |
| 10621 | Fnbp1 | NM_001177648.1 | chr2:30881725-30997528 |
| 10622 | Fnbp1 | NM_001177649.1 | chr2:30881725-30997528 |
| 10623 | Fnbp1 | NM_001177650.1 | chr2:30881725-30997528 |
| 10624 | Fnbp1 | NM_019406.3 | chr2:30881725-30997528 |
| 10625 | Fnbp1l | NM_001114665.2 | chr3:122241636-122322632 |

Fig. 25 - 57

| | | | |
|---|---|---|---|
| 10626 | Fnbp1l | NM_153118.3 | chr3:122241636-122322632 |
| 10627 | Fnbp4 | NM_018828.2 | chr2:90585526-90621177 |
| 10628 | Fnd3c2 | NM_001033424.3 | chrX:103430584-103450711 |
| 10629 | Fndc1 | NM_001081416.1 | chr17:7931432-7997839 |
| 10630 | Fndc3a | NM_207636.2 | chr14:72937759-73109810 |
| 10631 | Fndc3b | NM_173182.2 | chr3:27315084-27609361 |
| 10632 | Fndc3c1 | NM_001007580.1 | chrX:103615381-103680568 |
| 10633 | Fndc4 | NM_022424.5 | chr5:31594619-31598250 |
| 10634 | Fndc5 | NM_027402.3 | chr4:128814303-128821837 |
| 10635 | Fndc7 | NM_001165965.1 | chr3:108656595-108692926 |
| 10636 | Fndc7 | NM_177091.5 | chr3:108656595-108692926 |
| 10637 | Fndc8 | NM_030224.1 | chr11:82705646-82714239 |
| 10638 | Fndc9 | NM_177075.4 | chr11:46049059-46053373 |
| 10639 | Fnip1 | NM_173753.4 | chr11:54251680-54331743 |
| 10640 | Fnip2 | NM_001162999.2 | chr3:79259893-79371601 |
| 10641 | Fnta | NM_008033.3 | chr8:27109193-27126073 |
| 10642 | Fntb | NM_145927.2 | chr12:77938453-78022399 |
| 10643 | Focad | NM_001081184.1 | chr4:87740534-88056915 |
| 10644 | Folh1 | NM_001159706.1 | chr7:93867485-93924374 |
| 10645 | Folh1 | NM_016770.3 | chr7:93867485-93924374 |
| 10646 | Folr1 | NM_001252552.1 | chr7:109006844-109019302 |
| 10647 | Folr1 | NM_001252553.1 | chr7:109006844-109019302 |
| 10648 | Folr1 | NM_001252554.1 | chr7:109006844-109019302 |
| 10649 | Folr1 | NM_008034.3 | chr7:109006844-109019302 |
| 10650 | Folr2 | NM_008035.2 | chr7:108988501-108993845 |
| 10651 | Folr4 | NM_022858.2 | chr9:14690257-14708395 |
| 10652 | Folr4 | NM_178807.4 | chr9:14690257-14708395 |
| 10653 | Fopnl | NM_025345.2 | chr16:14299336-14317425 |
| 10654 | Fos | NM_010234.2 | chr12:86814850-86818219 |
| 10655 | Fosb | NM_008036.2 | chr7:19888044-19895394 |
| 10656 | Fosl1 | NM_010235.2 | chr19:5447698-5455938 |
| 10657 | Fosl2 | NM_008037.4 | chr5:32438844-32460212 |
| 10658 | Foxa1 | NM_008259.3 | chr12:58641618-58647108 |
| 10659 | Foxa2 | NM_001291065.1 | chr2:147868612-147872705 |
| 10660 | Foxa2 | NM_001291067.1 | chr2:147868612-147872705 |
| 10661 | Foxa2 | NM_010446.3 | chr2:147868612-147872705 |
| 10662 | Foxa3 | NM_008260.2 | chr7:19598631-19608888 |
| 10663 | Foxb1 | NM_022378.3 | chr9:69605516-69608747 |
| 10664 | Foxb2 | NM_008083.2.1 | chr19:16946805-16948320 |
| 10665 | Foxc1 | NM_008592.2 | chr13:31898514-31902504 |
| 10666 | Foxc2 | NM_013519.2 | chr8:123640070-123642794 |
| 10667 | Foxd1 | NM_008242.2 | chr13:99124199-99126660 |
| 10668 | Foxd2 | NM_008593.3 | chr4:114578884-114581503 |
| 10669 | Foxd2os | NR_030721.1 | chr4:114581893-114593723 |
| 10670 | Foxd3 | NM_010425.3 | chr4:99322989-99325362 |
| 10671 | Foxd4 | NM_008022.2 | chr19:24973454-24975799 |
| 10672 | Foxe1 | NM_183298.1 | chr4:46357065-46358181 |
| 10673 | Foxe3 | NM_015758.2 | chr4:114697751-114598618 |
| 10674 | Foxf1 | NM_010426.2 | chr8:123608285-123612054 |
| 10675 | Foxf2 | NM_010225.2 | chr13:31717684-31723275 |
| 10676 | Foxg1 | NM_001160112.1 | chr12:50483869-50487854 |
| 10677 | Foxg1 | NM_008241.2 | chr12:50483869-50487854 |
| 10678 | Foxh1 | NM_007989.4 | chr15:76498653-76500378 |
| 10679 | Foxi1 | NM_023907.4 | chr11:34104340-34108029 |
| 10680 | Foxi2 | NM_183193.2 | chr7:142602049-142605298 |
| 10681 | Foxi3 | NM_001101464.1 | chr6:70906599-70911060 |
| 10682 | Foxj1 | NM_008240.3 | chr11:116192017-116196668 |
| 10683 | Foxj2 | NM_023899.3 | chr6:122770202-122795384 |
| 10684 | Foxj3 | NM_001290696.1 | chr4:119212265-119301724 |
| 10685 | Foxj3 | NM_172699.3 | chr4:119212265-119301724 |
| 10686 | Foxk1 | NM_199068.2 | chr5:142877450-142937969 |
| 10687 | Foxk2 | NM_001080932.2 | chr11:121121300-121171210 |
| 10688 | Foxl1 | NM_008024.2 | chr8:123651584-123654544 |
| 10689 | Foxl2 | NM_012020.2 | chr9:98856025-98858545 |
| 10690 | Foxl2os | NR_024248.3 | chr9:98849573-98855729 |
| 10691 | Foxm1 | NM_008021.4 | chr6:128313012-128325904 |
| 10692 | Foxn1 | NM_001277290.1 | chr11:78171078-78200110 |
| 10693 | Foxn1 | NM_008238.2 | chr11:78171078-78200110 |
| 10694 | Foxn2 | NM_180974.4 | chr17:88840051-88889873 |
| 10695 | Foxn3 | NM_183186.2 | chr12:100433303-100688284 |
| 10696 | Foxn4 | NM_148935.2 | chr5:114704172-114723770 |
| 10697 | Foxo1 | NM_019739.3 | chr3:52072258-52154031 |
| 10698 | Foxo3 | NM_019740.2 | chr10:41905591-41996548 |
| 10699 | Foxo4 | NM_018789.2 | chrX:98449866-98456212 |
| 10700 | Foxo6 | NM_194060.1 | chr4:119939682-119959866 |
| 10701 | Foxp1 | NM_001197321.1 | chr6:98875335-99385339 |
| 10702 | Foxp1 | NM_001197322.1 | chr6:98875335-99385339 |
| 10703 | Foxp1 | NM_053202.2 | chr6:98875335-99385339 |
| 10704 | Foxp2 | NM_001286607.1 | chr6:14851348-15391677 |
| 10705 | Foxp2 | NM_053242.4 | chr6:14851348-15391677 |
| 10706 | Foxp2 | NM_212435.1 | chr6:14851348-15391677 |
| 10707 | Foxp3 | NM_001199347.1 | chrX:7135687-7182546 |
| 10708 | Foxp3 | NM_001199348.1 | chrX:7135687-7182546 |
| 10709 | Foxp3 | NM_054039.2 | chrX:7135687-7182546 |
| 10710 | Foxp4 | NM_001110824.1 | chr17:48004081-48061581 |
| 10711 | Foxp4 | NM_001110825.1 | chr17:48004081-48061581 |
| 10712 | Foxp4 | NM_172697.2 | chr17:48004081-48061581 |
| 10713 | Foxq1 | NM_008239.4 | chr13:31650038-31652843 |
| 10714 | Foxr1 | NM_001033469.2 | chr9:44242316-44248951 |
| 10715 | Foxr2 | NM_001034894.3 | chrX:149553330-149567404 |
| 10716 | Foxred1 | NM_001291448.1 | chr9:35011805-35018640 |
| 10717 | Foxred1 | NM_001291449.1 | chr9:35011805-35018640 |
| 10718 | Foxred1 | NM_172291.2 | chr9:35011805-35018640 |
| 10719 | Foxred2 | NM_001017983.2 | chr15:77770951-77787152 |
| 10720 | Foxred2 | NM_001168260.1 | chr15:77770951-77787152 |
| 10721 | Foxs1 | NM_010226.2 | chr2:152757633-152758944 |
| 10722 | Fpgs | NM_010236.2 | chr2:32538129-32549695 |
| 10723 | Fpgt | NM_029330.2 | chr3:154747882-154756342 |
| 10724 | Fpr1 | NM_013521.2 | chr17:18013434-18020903 |
| 10725 | Fpr2 | NM_008039.2 | chr17:18024787-18030916 |
| 10726 | Fpr3 | NM_008042.2 | chr17:18107421-18108641 |
| 10727 | Fpr-rs3 | NM_008040.2 | chr17:20760809-20761841 |
| 10728 | Fpr-rs4 | NM_008041.2 | chr17:18158696-18159668 |
| 10729 | Fpr-rs6 | NM_177316.2 | chr17:20319041-20320061 |
| 10730 | Fra10ac1 | NM_001081075.1 | chr19:38262968-38298622 |
| 10731 | Fras1 | NM_175473.3 | chr5:96802973-97213747 |
| 10732 | Frat1 | NM_008043.3 | chr19:41904459-41907073 |
| 10733 | Frat2 | NM_177603.3 | chr19:41920464-41922622 |
| 10734 | Frem1 | NM_001198811.1 | chr4:82543823-82698071 |
| 10735 | Frem1 | NM_177863.4 | chr4:82543823-82698071 |
| 10736 | Frem2 | NM_172862.3 | chr3:53317859-53461277 |
| 10737 | Frem3 | NM_001167898.1 | chr8:83134937-83219456 |
| 10738 | Frg1 | NM_013522.3 | chr8:42487807-42502472 |
| 10739 | Frk | NM_001159544.1 | chr10:34203205-34331036 |
| 10740 | Frk | NM_010237.3 | chr10:34203205-34331036 |
| 10741 | Frmd3 | NM_001163732.1 | chr4:73659506-73848118 |
| 10742 | Frmd3 | NM_172869.4 | chr4:73659506-73848118 |
| 10743 | Frmd4a | NM_001177843.1 | chr2:4073908-4535089 |
| 10744 | Frmd4a | NM_001177844.1 | chr2:4073908-4535089 |
| 10745 | Frmd4a | NM_172475.3 | chr2:4073908-4535089 |
| 10746 | Frmd4b | NM_145148.2 | chr6:97236860-97567651 |
| 10747 | Frmd5 | NM_172673.3 | chr2:121371264-121632793 |
| 10748 | Frmd6 | NM_028127.3 | chr12:71926500-72003221 |
| 10749 | Frmd7 | NM_001190332.1 | chrX:48245821-48295887 |
| 10750 | Frmd8 | NM_026169.4 | chr19:5850973-5875208 |
| 10751 | Frmpd1 | NM_001081172.2 | chr4:45197778-45298808 |
| 10752 | Frmpd1os | NR_040666.1 | chr4:45247595-45256862 |
| 10753 | Frmpd3 | NM_177750.2 | chrX:136909032-136929059 |
| 10754 | Frmpd4 | NM_001033330.3 | chrX:163909237-165015165 |
| 10755 | Frmpd4 | NM_001290427.1 | chrX:163909237-165015165 |
| 10756 | Frmpd4 | NM_001290428.1 | chrX:163909237-165015165 |
| 10757 | Frrs1 | NM_001113478.1 | chr3:116562484-116606668 |
| 10758 | Frrs1 | NM_009146.3 | chr3:116562484-116606668 |
| 10759 | Frrs1l | NM_001142965.1 | chr4:56973007-57003263 |
| 10760 | Frs2 | NM_177798.3 | chr10:116507182-116585530 |
| 10761 | Frs3 | NM_144939.2 | chr17:47832156-47841235 |
| 10762 | Frs3os | NR_045912.1 | chr17:47832155-47841235 |
| 10763 | Frs3os | NR_045913.1 | chr17:47832155-47841235 |
| 10764 | Fry | NM_172887.2 | chr5:151062504-151300328 |
| 10765 | Fryl | NM_028194.2 | chr5:73411429-73647857 |
| 10766 | Frzb | NM_011356.4 | chr2:80252126-80287553 |
| 10767 | Fsbp | NM_001256142.1 | chr4:11506809-11514949 |
| 10768 | Fscb | NM_001163271.1 | chr12:65572319-65575885 |
| 10769 | Fscn1 | NM_007984.2 | chr5:143722033-143734868 |
| 10770 | Fscn2 | NM_172802.4 | chr11:120222847-120229487 |
| 10771 | Fscn3 | NM_019569.2 | chr6:28377900-28388622 |
| 10772 | Fsd1 | NM_183178.2 | chr17:56125933-56136304 |
| 10773 | Fsd1l | NM_001195284.1 | chr4:53644342-53719881 |
| 10774 | Fsd1l | NM_178966.4 | chr4:53644342-53719881 |
| 10775 | Fsd2 | NM_172904.2 | chr7:88679239-88711867 |
| 10776 | Fshb | NM_008045.2 | chr2:106896297-106899808 |
| 10777 | Fshr | NM_013523.3 | chr17:89384291-89600015 |
| 10778 | Fsip1 | NM_027759.3 | chr2:118030623-118082702 |
| 10779 | Fst | NM_008046.3 | chr13:115242469-115248938 |
| 10780 | Fstl1 | NM_008047.5 | chr16:37777140-37836602 |
| 10781 | Fstl3 | NM_031380.2 | chr10:79240019-79245375 |
| 10782 | Fstl4 | NM_177059.3 | chr11:52578208-53000849 |
| 10783 | Fstl5 | NM_001253719.1 | chr3:75878482-76513927 |
| 10784 | Fstl5 | NM_178673.4 | chr3:75878482-76513927 |
| 10785 | Ftcd | NM_080845.2 | chr10:76038392-76053083 |
| 10786 | Fth1 | NM_010239.2 | chr19:10055089-10059601 |
| 10787 | Fth1 | NR_073181.1 | chr19:10055089-10059601 |
| 10788 | Fthl17 | NM_031261.2 | chrX:8610611-8611459 |
| 10789 | Ftl1 | NM_010240.2 | chr7:52713313-52715256 |
| 10790 | Ftmt | NM_026286.3 | chr18:52491189-52492650 |
| 10791 | Fto | NM_011936.2 | chr8:93837423-94192332 |
| 10792 | Ftsj1 | NM_001290430.1 | chrX:7815793-7829532 |
| 10793 | Ftsj1 | NM_133991.2 | chrX:7815793-7829532 |
| 10794 | Ftsj2 | NM_026510.1 | chr5:140803627-140807852 |
| 10795 | Ftsj3 | NM_025310.2 | chr11:106110457-106117116 |
| 10796 | Ftx | NR_028380.1 | chrX:100756248-100819093 |
| 10797 | Ftx | NR_028381.1 | chrX:100756248-100819093 |
| 10798 | Fubp1 | NM_057172.1 | chr3:151873421-151899794 |
| 10799 | Fubp3 | NM_001033389.4 | chr2:31428170-31473046 |
| 10800 | Fubp3 | NM_001290548.1 | chr2:31428170-31473046 |
| 10801 | Fuca1 | NM_024243.4 | chr4:135476640-135496215 |
| 10802 | Fuca2 | NM_025799.4 | chr10:13220833-13237081 |
| 10803 | Fuk | NM_172283.3 | chr8:113406355-113426388 |
| 10804 | Fuk | NR_052009.1 | chr8:113406355-113426388 |
| 10805 | Fundc1 | NM_028058.3 | chrX:17133694-17149423 |
| 10806 | Fundc2 | NM_026126.4 | chrX:72627737-72642497 |
| 10807 | Fuom | NM_001286217.1 | chr7:147283713-147288340 |
| 10808 | Fuom | NM_001286218.1 | chr7:147283713-147288340 |
| 10809 | Fuom | NM_026928.3 | chr7:147283713-147288340 |
| 10810 | Fuom | NR_104415.1 | chr7:147283713-147288340 |
| 10811 | Furin | NM_001081454.1 | chr7:87534079-87550317 |
| 10812 | Furin | NM_011046.2 | chr7:87534079-87550317 |
| 10813 | Fus | NM_139149.2 | chr7:135110992-135125545 |
| 10814 | Fut1 | NM_001271981.1 | chr7:52872975-52876429 |
| 10815 | Fut1 | NM_008051.6 | chr7:52872975-52876429 |

Fig. 25 - 58

| | | | |
|---|---|---|---|
| 10816 | Fut10 | NM_001012517.5 | chr8:32297802-32372396 |
| 10817 | Fut10 | NM_001286422.1 | chr8:32297802-32372396 |
| 10818 | Fut10 | NM_001286424.1 | chr8:32297802-32372396 |
| 10819 | Fut10 | NM_001286425.1 | chr8:32297802-32372396 |
| 10820 | Fut10 | NM_134161.3 | chr8:32297802-32372396 |
| 10821 | Fut11 | NM_028428.2 | chr14:21514189-21519419 |
| 10822 | Fut2 | NM_001271993.1 | chr7:52903960-52921764 |
| 10823 | Fut2 | NM_018876.4 | chr7:52903960-52921764 |
| 10824 | Fut4 | NM_010242.3 | chr9:14552902-14556566 |
| 10825 | Fut4-ps1 | NR_033644.1 | chr17:56873650-56878715 |
| 10826 | Fut7 | NM_001177366.1 | chr2:25278761-25281893 |
| 10827 | Fut7 | NM_001177367.1 | chr2:25278761-25281893 |
| 10828 | Fut7 | NM_001289453.1 | chr2:25278761-25281893 |
| 10829 | Fut7 | NM_001289454.1 | chr2:25278761-25281893 |
| 10830 | Fut7 | NM_001289455.1 | chr2:25278761-25281893 |
| 10831 | Fut7 | NM_001289456.1 | chr2:25278761-25281893 |
| 10832 | Fut7 | NM_013524.3 | chr2:25278761-25281893 |
| 10833 | Fut8 | NM_001252614.1 | chr12:78339090-78576983 |
| 10834 | Fut8 | NM_001252615.1 | chr12:78339090-78576983 |
| 10835 | Fut8 | NM_001252616.1 | chr12:78339090-78576983 |
| 10836 | Fut8 | NM_016893.5 | chr12:78339090-78576983 |
| 10837 | Fut8 | NR_045554.1 | chr12:78339090-78576983 |
| 10838 | Fut9 | NM_010243.3 | chr4:25536479-25727150 |
| 10839 | Fuz | NM_027376.3 | chr7:52151449-52155994 |
| 10840 | Fv1 | NM_010424.3 | chr4:147243087-147244467 |
| 10841 | Fxn | NM_008044.2 | chr19:24335942-24355076 |
| 10842 | Fxr1 | NM_001113188.1 | chr3:33919000-33980276 |
| 10843 | Fxr1 | NM_001113189.1 | chr3:33919000-33980276 |
| 10844 | Fxr1 | NM_008053.2 | chr3:33919000-33980276 |
| 10845 | Fxr2 | NM_011814.2 | chr11:69446473-69466799 |
| 10846 | Fxyd1 | NM_019503.4 | chr7:31836696-31840675 |
| 10847 | Fxyd1 | NM_052991.4 | chr7:31836696-31840675 |
| 10848 | Fxyd1 | NM_052992.3 | chr7:31836696-31840675 |
| 10849 | Fxyd1 | NM_194321.2 | chr7:31836696-31840675 |
| 10850 | Fxyd2 | NM_007503.3 | chr9:45207791-45218361 |
| 10851 | Fxyd2 | NM_052823.2 | chr9:45207791-45218361 |
| 10852 | Fxyd2 | NR_028499.1 | chr9:45207791-45218361 |
| 10853 | Fxyd3 | NM_008557.2 | chr7:31855554-31861716 |
| 10854 | Fxyd4 | NM_001173571.1 | chr6:117883576-117887353 |
| 10855 | Fxyd4 | NM_033648.1 | chr6:117883576-117887353 |
| 10856 | Fxyd5 | NM_001111073.2 | chr7:31817741-31827350 |
| 10857 | Fxyd5 | NM_001287216.1 | chr7:31817741-31827350 |
| 10858 | Fxyd5 | NM_001287217.1 | chr7:31817741-31827350 |
| 10859 | Fxyd5 | NM_008761.4 | chr7:31817741-31827350 |
| 10860 | Fxyd6 | NM_022004.2 | chr9:45178267-45204242 |
| 10861 | Fxyd7 | NM_022007.1 | chr7:31827533-31836473 |
| 10862 | Fyb | NM_001278269.1 | chr15:6529846-6615608 |
| 10863 | Fyb | NM_011815.5 | chr15:6529846-6615608 |
| 10864 | Fyco1 | NM_001110253.2 | chr9:123698617-123761020 |
| 10865 | Fyco1 | NM_148925.3 | chr9:123698617-123761020 |
| 10866 | Fyn | NM_001122892.1 | chr10:39089604-39285180 |
| 10867 | Fyn | NM_001122893.1 | chr10:39089604-39285180 |
| 10868 | Fyn | NM_008054.2 | chr10:39089604-39285180 |
| 10869 | Fyttd1 | NM_001159349.1 | chr16:32877869-32909049 |
| 10870 | Fyttd1 | NM_027226.4 | chr16:32877869-32909049 |
| 10871 | Fzd1 | NM_021457.3 | chr5:4753838-4758216 |
| 10872 | Fzd10 | NM_175284.3 | chr5:129106980-129109968 |
| 10873 | Fzd2 | NM_020510.2 | chr11:102465744-102469372 |
| 10874 | Fzd3 | NM_021458.2 | chr14:65811277-65881300 |
| 10875 | Fzd4 | NM_008055.4 | chr7:96552875-96558620 |
| 10876 | Fzd5 | NM_001042659.1 | chr1:64777131-64784324 |
| 10877 | Fzd5 | NM_022721.3 | chr1:64777131-64784324 |
| 10878 | Fzd6 | NM_001162494.1 | chr15:38837825-38869736 |
| 10879 | Fzd6 | NM_008056.3 | chr15:38837825-38869736 |
| 10880 | Fzd7 | NM_095338990-59543799 | chr1:59538990-59543799 |
| 10881 | Fzd8 | NM_008058.2 | chr18:9212853-9216199 |
| 10882 | Fzd9 | NM_010246.1 | chr5:135724807-135726917 |
| 10883 | Fzr1 | NM_019757.1 | chr10:80829623-80841115 |
| 10884 | G0s2 | NM_008059.3 | chr1:195098853-195099382 |
| 10885 | G2e3 | NM_001015099.2 | chr12:52449216-52477973 |
| 10886 | G2e3 | NM_001167963.1 | chr12:52449216-52477973 |
| 10887 | G2e3 | NM_001167964.1 | chr12:52449216-52477973 |
| 10888 | G3bp1 | NM_013716.2 | chr11:55283254-55314389 |
| 10889 | G3bp2 | NM_001080794.2 | chr5:92481171-92512761 |
| 10890 | G3bp2 | NM_001080795.2 | chr5:92481171-92512761 |
| 10891 | G3bp2 | NM_001080796.2 | chr5:92481171-92512761 |
| 10892 | G3bp2 | NM_001080797.2 | chr5:92481171-92512761 |
| 10893 | G3bp2 | NM_011816.4 | chr5:92481171-92512761 |
| 10894 | G530011O06Rik | NM_029457.1 | chrX:166412975-166416849 |
| 10895 | G630025P09Rik | NR_027913.1 | chr11:69617171-69619540 |
| 10896 | G630055G22Rik | NR_045404.1 | chr18:48082495-48267634 |
| 10897 | G630071F17Rik | NM_045401.1 | chr18:60823063-60831278 |
| 10898 | G630090E17Rik | NM_001173500.2 | chr10:39666718-39679959 |
| 10899 | G630093K05Rik | NR_045156.1 | chr13:48005803-48029670 |
| 10900 | G6b | NM_001033221.3 | chr17:35199637-35203129 |
| 10901 | G6b | NM_001191012.1 | chr17:35199637-35203129 |
| 10902 | G6bos | NR_046462.1 | chr17:35201382-35202541 |
| 10903 | G6pc | NM_008061.3 | chr11:101229043-101239217 |
| 10904 | G6pc2 | NM_001289856.1 | chr2:69049129-69066050 |
| 10905 | G6pc2 | NM_001289857.1 | chr2:69049129-69066050 |
| 10906 | G6pc2 | NM_021331.4 | chr2:69049129-69066050 |
| 10907 | G6pc3 | NM_175935.3 | chr11:102051012-102055396 |
| 10908 | G6pd2 | NM_019468.2 | chr5:62200081-62201716 |
| 10909 | G6pdx | NM_008062.2 | chrX:71654825-71674500 |
| 10910 | G730013B05Rik | NR_040379.1 | chr16:50526357-50559572 |
| 10911 | G730013B05Rik | NR_040380.1 | chr16:50526357-50559572 |
| 10912 | Gaa | NM_001159324.1 | chr11:119129280-119147012 |
| 10913 | Gaa | NM_008064.3 | chr11:119129280-119147012 |
| 10914 | Gab1 | NM_021356.2 | chr8:83288332-83404378 |
| 10915 | Gab2 | NM_001162477.1 | chr7:104230260-104457461 |
| 10916 | Gab2 | NM_010248.2 | chr7:104230260-104457461 |
| 10917 | Gab3 | NM_181584.4 | chrX:72233886-72330244 |
| 10918 | Gabarap | NM_019749.4 | chr11:69804871-69808451 |
| 10919 | Gabarapl1 | NM_020590.4 | chr6:129483210-129492349 |
| 10920 | Gabarapl2 | NM_026693.5 | chr8:114464602-114476815 |
| 10921 | Gabbr1 | NM_019439.3 | chr17:37182910-37211250 |
| 10922 | Gabbr2 | NM_001081141.1 | chr4:46676769-47004586 |
| 10923 | Gabpa | NM_008065.2 | chr16:84835369-84864023 |
| 10924 | Gabpb1 | NM_001271467.1 | chr2:126454642-126502073 |
| 10925 | Gabpb1 | NM_001271468.1 | chr2:126454642-126502073 |
| 10926 | Gabpb1 | NM_001271469.1 | chr2:126454642-126502073 |
| 10927 | Gabpb1 | NM_001271470.1 | chr2:126454642-126502073 |
| 10928 | Gabpb1 | NM_001271492.1 | chr2:126454642-126502073 |
| 10929 | Gabpb1 | NM_010249.2 | chr2:126454642-126502073 |
| 10930 | Gabpb1 | NM_207669.2 | chr2:126454642-126502073 |
| 10931 | Gabpb1 | NR_073183.1 | chr2:126454642-126502073 |
| 10932 | Gabpb2 | NM_029885.1 | chr3:94985689-95040346 |
| 10933 | Gabpb2 | NM_172512.1 | chr3:94985689-95040346 |
| 10934 | Gabra1 | NM_010250.5 | chr11:41944440-41996432 |
| 10935 | Gabra2 | NM_008066.3 | chr5:71352295-71487088 |
| 10936 | Gabra3 | NM_008067.4 | chrX:69678015-69801585 |
| 10937 | Gabra4 | NM_010251.2 | chr5:71960972-72049547 |
| 10938 | Gabra5 | NM_176942.4 | chr7:64663039-64765379 |
| 10939 | Gabra6 | NM_001099641.2 | chr11:42119938-42134574 |
| 10940 | Gabra6 | NM_008068.3 | chr11:42119938-42134574 |
| 10941 | Gabrb2 | NM_008069.4 | chr5:72091254-72528483 |
| 10942 | Gabrb2 | NM_008070.3 | chr11:42233258-42446093 |
| 10943 | Gabrb3 | NM_001038701.2 | chr7:64845887-65084171 |
| 10944 | Gabrb3 | NM_008071.3 | chr7:64845887-65084171 |
| 10945 | Gabrd | NM_008072.2 | chr4:154759087-154772178 |
| 10946 | Gabre | NM_017369.2 | chrX:69502771-69520060 |
| 10947 | Gabrg1 | NM_010252.4 | chr5:71142285-71233856 |
| 10948 | Gabrg2 | NM_008073.3 | chr11:41723691-41814216 |
| 10949 | Gabrg2 | NM_177408.6 | chr11:41723691-41814216 |
| 10950 | Gabrg3 | NM_008074.2 | chr7:63979611-64642241 |
| 10951 | Gabrp | NM_146017.3 | chr11:33450780-33478957 |
| 10952 | Gabrq | NM_001290435.1 | chrX:70070516-70087941 |
| 10953 | Gabrq | NM_020488.2 | chrX:70070516-70087941 |
| 10954 | Gabrr1 | NM_008075.2 | chr4:33219530-33250563 |
| 10955 | Gabrr2 | NM_008076.3 | chr4:33150086-33182840 |
| 10956 | Gabrr3 | NM_001081190.1 | chr16:59407207-59461565 |
| 10957 | Gad1 | NM_008077.4 | chr2:70400221-70440069 |
| 10958 | Gad1os | NR_040496.1 | chr2:70327997-70401414 |
| 10959 | Gad2 | NM_008078.2 | chr2:22477847-22549397 |
| 10960 | Gadd45a | NM_007836.1 | chr6:66985090-66987401 |
| 10961 | Gadd45b | NM_008655.1 | chr10:80392835-80394949 |
| 10962 | Gadd45g | NM_011817.2 | chr13:51942043-51943843 |
| 10963 | Gadd45gip1 | NM_183358.4 | chr8:87356181-87359381 |
| 10964 | Gadl1 | NM_028638.1 | chr9:115818572-115985294 |
| 10965 | Gak | NM_001282051.1 | chr5:108998125-109058796 |
| 10966 | Gak | NM_001282052.1 | chr5:108998125-109058796 |
| 10967 | Gak | NM_153569.2 | chr5:108998125-109058796 |
| 10968 | Gal | NM_010253.3 | chr19:3409916-3414457 |
| 10969 | Gal3st1 | NM_001177691.1 | chr11:3883638-3899331 |
| 10970 | Gal3st1 | NM_001177703.1 | chr11:3883638-3899331 |
| 10971 | Gal3st1 | NM_016922.3 | chr11:3883638-3899331 |
| 10972 | Gal3st2 | NM_199366.4 | chr1:95757920-95773071 |
| 10973 | Gal3st3 | NM_001024717.2 | chr19:5298330-5308739 |
| 10974 | Gal3st4 | NM_001033416.1 | chr5:138706193-138713982 |
| 10975 | Galc | NM_008079.4 | chr12:99440509-99497547 |
| 10976 | Gale | NM_178389.3 | chr4:135521079-135524093 |
| 10977 | Galk1 | NM_016905.2 | chr11:115869671-115874033 |
| 10978 | Galk2 | NM_001291002.1 | chr2:125684844-125977740 |
| 10979 | Galk2 | NM_175154.3 | chr2:125684844-125977740 |
| 10980 | Galm | NM_176963.4 | chr17:80526810-80584372 |
| 10981 | Galns | NM_001193645.1 | chr8:125102136-125135387 |
| 10982 | Galns | NM_016722.4 | chr8:125102136-125135387 |
| 10983 | Galnt1 | NM_001160404.1 | chr18:24363844-24445317 |
| 10984 | Galnt1 | NM_013814.3 | chr18:24363844-24445317 |
| 10985 | Galnt10 | NM_134189.2 | chr11:57458943-57601002 |
| 10986 | Galnt11 | NM_144908.3 | chr5:24728710-24771736 |
| 10987 | Galnt12 | NM_172693.3 | chr4:47104824-47135914 |
| 10988 | Galnt13 | NM_173030.2 | chr2:54288797-54970155 |
| 10989 | Galnt14 | NM_027864.2 | chr17:73843090-74059791 |
| 10990 | Galnt15 | NM_030166.1 | chr14:32842288-32871512 |
| 10991 | Galnt16 | NM_001081421.1 | chr12:81619976-81704883 |
| 10992 | Galnt17 | NM_173739.3 | chr7:118615174-118923491 |
| 10993 | Galnt2 | NM_139272.2 | chr8:126755293-126869622 |
| 10994 | Galnt3 | NM_015736.2 | chr2:65920822-65962850 |
| 10995 | Galnt4 | NM_015737.4 | chr10:98570769-98575881 |
| 10996 | Galnt5 | NM_172855.3 | chr5:57850565-57891582 |
| 10997 | Galnt6 | NM_001161767.1 | chr15:100520345-100559807 |
| 10998 | Galnt6 | NM_001161768.1 | chr15:100520345-100559807 |
| 10999 | Galnt6 | NM_172451.3 | chr15:100520345-100559807 |
| 11000 | Galnt7 | NM_001167981.1 | chr8:60002621-60142227 |
| 11001 | Galnt7 | NM_144731.4 | chr8:60002621-60142227 |
| 11002 | Galnt9 | NM_001122639.1 | chr5:110973373-111050402 |
| 11003 | Galnt9 | NM_198306.2 | chr5:110973373-111050402 |
| 11004 | Galnt9 | NR_104449.1 | chr5:110973373-111050402 |
| 11005 | Galnt15 | NM_026449.3 | chr5:24687297-24726107 |

Fig. 25 - 59

| | | | | | | | |
|---|---|---|---|---|---|---|---|
| 11006 | Galnt6 | NM_175032.3 | chr8:60252849-61390424 | 11101 | Gck | NM_010292.5 | chr11:5800823-5850084 |
| 11007 | Galp | NM_178028.2 | chr7:6148691-6167739 | 11102 | Gckr | NM_144909.1 | chr5:31599954-31629675 |
| 11008 | Galr1 | NM_008082.2 | chr18:82561887-82576169 | 11103 | Gclc | NM_010295.2 | chr9:77602341-77642296 |
| 11009 | Galr2 | NM_010254.4 | chr11:116142252-116145252 | 11104 | Gclm | NM_008129.4 | chr3:121948474-121970133 |
| 11010 | Galr3 | NM_015738.2 | chr15:78872315-78873988 | 11105 | Gcm1 | NM_008103.3 | chr9:77899764-77913431 |
| 11011 | Galt | NM_016658.3 | chr4:41702125-41705998 | 11106 | Gcm2 | NM_008104.2 | chr13:41196795-41205357 |
| 11012 | Gamt | NM_010255.3 | chr10:79720895-79723713 | 11107 | Gcn1l1 | NM_172719.2 | chr5:116015272-116072663 |
| 11013 | Gan | NM_001081151.1 | chr8:119682034-119729086 | 11108 | Gcnt1 | NM_001136484.3 | chr19:17400630-17447334 |
| 11014 | Ganab | NM_008060.2 | chr19:8972600-8991155 | 11109 | Gcnt1 | NM_010265.5 | chr19:17400630-17447334 |
| 11015 | Ganc | NM_172672.2 | chr2:120229632-120286588 | 11110 | Gcnt3 | NM_173442.5 | chr19:17400630-17447334 |
| 11016 | Gap43 | NM_008083.2 | chr16:42248674-42340764 | 11111 | Gcnt2 | NM_008105.1 | chr13:40955136-41056261 |
| 11017 | Gapdh | NM_001289726.1 | chr6:125111869-125116485 | 11112 | Gcnt2 | NM_023887.4 | chr13:40955136-41056261 |
| 11018 | Gapdh | NM_008084.3 | chr6:125111869-125116485 | 11113 | Gcnt2 | NM_133219.1 | chr13:40955136-41056261 |
| 11019 | Gapdhs | NM_001290631.1 | chr7:31514797-31528700 | 11114 | Gcnt3 | NM_028087.2 | chr9:69879302-69885895 |
| 11020 | Gapdhs | NM_008085.2 | chr7:31514797-31528700 | 11115 | Gcnt4 | NM_001166065.1 | chr13:97694643-97720869 |
| 11021 | Gapt | NM_177713.3 | chr13:111142822-111147380 | 11116 | Gcnt7 | NM_001039560.3 | chr2:172275813-172284096 |
| 11022 | Gapvd1 | NM_025709.2 | chr2:34532501-34610752 | 11117 | Gcsam | NM_001159297.1 | chr16:45610552-45622980 |
| 11023 | Gar1 | NM_026578.3 | chr3:129527829-129534314 | 11118 | Gcsam | NM_008099.4 | chr16:45610552-45622980 |
| 11024 | Garem | NM_001033445.2 | chr18:21285842-21458640 | 11119 | Gcsh | NM_026572.3 | chr8:119505727-119517349 |
| 11025 | Gareml | NM_001167879.1 | chr5:30431736-30444920 | 11120 | Gda | NM_010266.2 | chr19:21465796-21547151 |
| 11026 | Garnl3 | NM_178888.4 | chr2:32841885-32942724 | 11121 | Gdap1 | NM_010267.2 | chr1:17135453-17154351 |
| 11027 | Gars | NM_180678.3 | chr6:54987994-55029498 | 11122 | Gdap10 | NR_045032.1 | chr12:33508981-33511773 |
| 11028 | Gart | NM_010256.2 | chr16:91621641-91647217 | 11123 | Gdap1l1 | NM_144891.2 | chr2:163264202-163281060 |
| 11029 | Gas1 | NM_008086.2 | chr13:60275765-60278896 | 11124 | Gdap2 | NM_010269.3 | chr3:99966385-100010912 |
| 11030 | Gas2 | NM_008087.2 | chr7:59134514-59249828 | 11125 | Gdap2 | NR_104341.1 | chr3:99966385-100010912 |
| 11031 | Gas2l1 | NM_001190406.1 | chr11:4954133-4965330 | 11126 | Gde1 | NM_019580.4 | chr7:125832071-125849252 |
| 11032 | Gas2l1 | NM_001190408.1 | chr11:4954133-4965330 | 11127 | Gdf1 | NM_001163282.2 | chr8:72839673-72877172 |
| 11033 | Gas2l1 | NM_030228.3 | chr11:4954133-4965330 | 11128 | Gdf1 | NM_008107.4 | chr8:72839673-72877172 |
| 11034 | Gas2l1 | NM_144560.3 | chr11:4954133-4965330 | 11129 | Gdf10 | NM_145741.2 | chr14:34736772-34748468 |
| 11035 | Gas2l2 | NM_001013759.2 | chr11:83235136-83243023 | 11130 | Gdf11 | NM_010272.1 | chr10:128321601-128328774 |
| 11036 | Gas2l3 | NM_001033331.2 | chr10:88871567-88906712 | 11131 | Gdf15 | NM_011819.2 | chr8:73153292-73155534 |
| 11037 | Gas2l3 | NM_001079876.1 | chr10:88871567-88906712 | 11132 | Gdf2 | NM_019506.4 | chr14:34754224-34760384 |
| 11038 | Gas2l3 | NM_001284344.1 | chr10:88871567-88906712 | 11133 | Gdf3 | NM_008108.4 | chr6:122555420-122560089 |
| 11039 | Gas5 | NR_002840.2 | chr1:162965297-162968668 | 11134 | Gdf5 | NM_008109.2 | chr2:155766760-155771100 |
| 11040 | Gas6 | NM_019521.2 | chr8:13465373-13494535 | 11135 | Gdf6 | NM_013526.3 | chr4:9771518-9780492 |
| 11041 | Gas7 | NM_001109657.3 | chr11:67346499-67502494 | 11136 | Gdf7 | NM_013527.1 | chr12:8304723-8308760 |
| 11042 | Gas7 | NM_001277079.1 | chr11:67346499-67502494 | 11137 | Gdf9 | NM_008110.2 | chr11:53246787-53251404 |
| 11043 | Gas7 | NM_001277080.1 | chr11:67346499-67502494 | 11138 | Gdi1 | NM_010273.4 | chrX:71550355-71557206 |
| 11044 | Gas7 | NM_008088.5 | chr11:67346499-67502494 | 11139 | Gdi2 | NM_008112.4 | chr13:3537321-3565507 |
| 11045 | Gas8 | NM_018855.2 | chr8:126042734-126060550 | 11140 | Gdnf | NM_010275.3 | chr15:7761010-7787575 |
| 11046 | Gast | NM_010257.3 | chr11:100195725-100198310 | 11141 | Gdpd1 | NM_025638.2 | chr11:86847295-86887639 |
| 11047 | Gata1 | NM_008089.2 | chrX:7536385-7545036 | 11142 | Gdpd2 | NM_023608.4 | chrX:97925185-97934238 |
| 11048 | Gata2 | NM_008090.5 | chr6:88148657-88157026 | 11143 | Gdpd3 | NM_024228.2 | chr7:133909927-133919159 |
| 11049 | Gata3 | NM_008091.3 | chr2:9778704-9800227 | 11144 | Gdpd4 | NM_176696.3 | chr7:105068467-105198173 |
| 11050 | Gata4 | NM_008092.3 | chr14:63817751-63864097 | 11145 | Gdpd5 | NM_201352.2 | chr7:106530058-106609494 |
| 11051 | Gata5 | NM_008093.2 | chr2:180059793-180069384 | 11146 | Gdpgp1 | NM_178752.3 | chr7:87377778-87386306 |
| 11052 | Gata5os | NR_045877.1 | chr2:180067562-180075437 | 11147 | Gem | NM_010276.4 | chr4:11631593-11642140 |
| 11053 | Gata6 | NM_010258.3 | chr18:11052508-11085633 | 11148 | Gemin2 | NM_025656.2 | chr12:60114379-60128975 |
| 11054 | Gatad1 | NM_026033.2 | chr5:3639960-3647936 | 11149 | Gemin4 | NM_177367.3 | chr11:76024072-76031074 |
| 11055 | Gatad2a | NM_001113346.1 | chr8:72430967-72520283 | 11150 | Gemin5 | NM_001166669.1 | chr11:57933502-57982041 |
| 11056 | Gatad2a | NM_001286450.1 | chr8:72430967-72520283 | 11151 | Gemin5 | NM_001166670.1 | chr11:57933502-57982041 |
| 11057 | Gatad2a | NM_145596.4 | chr8:72430967-72520283 | 11152 | Gemin5 | NM_001166671.1 | chr11:57933502-57982041 |
| 11058 | Gatad2b | NM_139304.1 | chr3:90148575-90162042 | 11153 | Gemin5 | NM_172558.3 | chr11:57933502-57982041 |
| 11059 | Gatc | NM_029645.3 | chr5:115783250-115791170 | 11154 | Gemin6 | NM_026053.3 | chr17:80623828-80627837 |
| 11060 | Gatm | NM_025961.5 | chr2:122420208-122437013 | 11155 | Gemin7 | NM_027189.2 | chr7:20150297-20158692 |
| 11061 | Gatsl2 | NM_030739.3 | chr5:134575617-134617628 | 11156 | Gemin8 | NM_146238.3 | chrX:162608411-162628444 |
| 11062 | Gatsl3 | NM_028022.1 | chr11:4118253-4122412 | 11157 | Gen1 | NM_177331.4 | chr12:11247731-11272593 |
| 11063 | Gba | NM_001077411.2 | chr3:89006849-89012603 | 11158 | Get4 | NM_001163316.1 | chr5:139728277-139746004 |
| 11064 | Gba | NM_008094.5 | chr3:89006849-89012603 | 11159 | Get4 | NM_026269.2 | chr5:139728277-139746004 |
| 11065 | Gba2 | NM_172692.3 | chr4:43579800-43591736 | 11160 | Gfap | NM_001131020.1 | chr11:102748649-102758514 |
| 11066 | Gbas | NM_008095.4 | chr5:130230949-130264201 | 11161 | Gfap | NM_010277.3 | chr11:102748649-102758514 |
| 11067 | Gbe1 | NM_028803.4 | chr16:70314193-70569965 | 11162 | Gfer | NM_023040.3 | chr17:24830135-24833101 |
| 11068 | Gbf1 | NM_178930.3 | chr19:46227047-46361000 | 11163 | Gfi1 | NM_001267621.1 | chr5:108145673-108154825 |
| 11069 | Gbgt1 | NM_139197.2 | chr2:28352410-28360935 | 11164 | Gfi1 | NM_010278.2 | chr5:108145673-108154825 |
| 11070 | Gbp10 | NM_001039646.2 | chr5:105644717-105668552 | 11165 | Gfi1b | NM_001160406.1 | chr2:28464969-28477502 |
| 11071 | Gbp11 | NM_001039647.2 | chr5:105752044-105775491 | 11166 | Gfi1b | NM_008114.3 | chr2:28464969-28477502 |
| 11072 | Gbp2 | NM_010260.1 | chr3:142283627-142300972 | 11167 | Gfm1 | NM_138591.2 | chr3:67234037-67278990 |
| 11073 | Gbp2b | NM_010259.2 | chr3:142257810-142282140 | 11168 | Gfm2 | NM_001146043.2 | chr13:97907891-97968312 |
| 11074 | Gbp3 | NM_001289492.1 | chr3:142223015-142236176 | 11169 | Gfm2 | NM_001271463.1 | chr13:97907891-97968312 |
| 11075 | Gbp3 | NM_001289493.1 | chr3:142223015-142236176 | 11170 | Gfm2 | NM_001271464.1 | chr13:97907891-97968312 |
| 11076 | Gbp3 | NM_018734.3 | chr3:142223015-142236176 | 11171 | Gfm2 | NM_001271465.1 | chr13:97907891-97968312 |
| 11077 | Gbp4 | NM_001256005.1 | chr5:105544785-105568605 | 11172 | Gfm2 | NM_177266.5 | chr13:97907891-97968312 |
| 11078 | Gbp4 | NM_008620.3 | chr5:105544785-105568605 | 11173 | Gfod1 | NM_001033399.4 | chr13:43290887-43399541 |
| 11079 | Gbp5 | NM_153564.2 | chr3:142159897-142185308 | 11174 | Gfod2 | NM_027469.4 | chr8:108240012-108282507 |
| 11080 | Gbp6 | NM_194336.2 | chr5:105699720-105722718 | 11175 | Gfpt1 | NM_013528.3 | chr6:86992839-87042201 |
| 11081 | Gbp7 | NM_001083312.2 | chr3:142193299-142213115 | 11176 | Gfpt2 | NM_013529.3 | chr11:49607656-49652122 |
| 11082 | Gbp7 | NM_145545.4 | chr3:142193299-142213115 | 11177 | Gfra1 | NM_001285457.1 | chr19:58310070-58529888 |
| 11083 | Gbp8 | NM_029509.4 | chr5:105443171-105482580 | 11178 | Gfra1 | NM_010279.3 | chr19:58310070-58529888 |
| 11084 | Gbp9 | NM_172777.3 | chr5:105507412-105539311 | 11179 | Gfra1 | NR_104342.1 | chr19:58310070-58529888 |
| 11085 | Gbx1 | NM_015739.2 | chr5:24010243-24032666 | 11180 | Gfra2 | NM_008115.3 | chr14:71289936-71379645 |
| 11086 | Gbx2 | NM_010262.3 | chr1:91824536-91827751 | 11181 | Gfra3 | NM_010280.3 | chr18:34849556-34880041 |
| 11087 | Gc | NM_008096.2 | chr5:89846535-89886923 | 11182 | Gfra4 | NM_001136063.2 | chr2:130865367-130868824 |
| 11088 | Gca | NM_145523.3 | chr2:62502383-62532166 | 11183 | Gfra4 | NM_001271001.1 | chr2:130865367-130868824 |
| 11089 | Gcat | NM_001161712.1 | chr15:78861303-78873988 | 11184 | Gfra4 | NM_001271002.1 | chr2:130865367-130868824 |
| 11090 | Gcat | NM_013847.3 | chr15:78861303-78873988 | 11185 | Gfra4 | NM_020014.2 | chr2:130865367-130868824 |
| 11091 | Gcc1 | NM_028900.4 | chr6:28366602-28371724 | 11186 | Gfral | NM_205844.3 | chr9:76011908-76061464 |
| 11092 | Gcc2 | NM_027375.2 | chr10:57718273-57768340 | 11187 | Gfy | NM_001195255.1 | chr7:52431718-52434967 |
| 11093 | Gcdh | NM_001044744.1 | chr8:87396009-87417820 | 11188 | Gga1 | NM_145929.2 | chr15:78707620-78725015 |
| 11094 | Gcdh | NM_008097.2 | chr8:87396009-87417820 | 11189 | Gga2 | NM_028758.2 | chr7:129130235-129164712 |
| 11095 | Gcfc2 | NM_177884.3 | chr6:81873663-81909092 | 11190 | Gga3 | NM_001252067.1 | chr11:115445568-115465230 |
| 11096 | Gcg | NM_008100.4 | chr2:62312586-62321710 | 11191 | Gga3 | NM_173048.3 | chr11:115445568-115465230 |
| 11097 | Gcgr | NM_008101.2 | chr11:120392040-120400298 | 11192 | Ggact | NM_145466.2 | chr14:123290081-123312387 |
| 11098 | Gch1 | NM_008102.3 | chr14:47773569-47809077 | 11193 | Ggct | NM_026637.3 | chr6:54935088-54942861 |
| 11099 | Gchfr | NM_177157.4 | chr2:118993523-118998125 | 11194 | Ggcx | NM_019802.5 | chr6:72364301-72381100 |
| 11100 | Gck | NM_001287386.1 | chr11:5800823-5850084 | 11195 | Ggh | NM_010281.2 | chr4:19969198-19993258 |

Fig. 25 - 60

| | | | |
|---|---|---|---|
| 11196 | Ggn | NM_182694.2 | chr7:29955228-29958952 |
| 11197 | Ggn | NM_182696.2 | chr7:29955228-29958952 |
| 11198 | Ggnbp1 | NM_001251881.1 | chr17:27154979-27173323 |
| 11199 | Ggnbp1 | NM_027544.2 | chr17:27154979-27173323 |
| 11200 | Ggnbp2 | NM_153144.2 | chr11:84645862-84684240 |
| 11201 | Ggps1 | NM_010282.2 | chr13:14144713-14155668 |
| 11202 | Ggt1 | NM_008116.3 | chr10:75036337-75048927 |
| 11203 | Ggt5 | NM_011820.4 | chr10:75052125-75079713 |
| 11204 | Ggt6 | NM_027819.2 | chr11:72249027-72251906 |
| 11205 | Ggt7 | NM_144786.2 | chr2:155316115-155340582 |
| 11206 | Ggta1 | NM_001145821.2 | chr2:35255698-35316945 |
| 11207 | Ggta1 | NM_010283.4 | chr2:35255698-35316945 |
| 11208 | Gh | NM_008117.3 | chr11:106161574-106163210 |
| 11209 | Ghdc | NM_031871.3 | chr11:100627645-100632271 |
| 11210 | Ghitm | NM_001199122.1 | chr14:37933631-37948508 |
| 11211 | Ghitm | NM_078478.5 | chr14:37933631-37948508 |
| 11212 | Ghr | NM_001048178.2 | chr15:3267754-3533352 |
| 11213 | Ghr | NM_001286370.1 | chr15:3267754-3533352 |
| 11214 | Ghr | NM_010284.3 | chr15:3267754-3533352 |
| 11215 | Ghrh | NM_010285.2 | chr2:157155231-157172391 |
| 11216 | Ghrhr | NM_001003685.3 | chr6:55326288-55338524 |
| 11217 | Ghrl | NM_001286404.1 | chr6:113666112-113669905 |
| 11218 | Ghrl | NM_001286405.1 | chr6:113666112-113669905 |
| 11219 | Ghrl | NM_001286406.1 | chr6:113666112-113669905 |
| 11220 | Ghrl | NM_021488.5 | chr6:113666112-113669905 |
| 11221 | Ghsr | NM_177330.4 | chr3:27270272-27276932 |
| 11222 | Gid4 | NM_025757.4 | chr11:60230646-60258779 |
| 11223 | Gid8 | NM_001289651.1 | chr2:180444930-180456304 |
| 11224 | Gid8 | NM_001289652.1 | chr2:180444930-180456304 |
| 11225 | Gid8 | NM_029607.2 | chr2:180444930-180456304 |
| 11226 | Gif | NM_008118.3 | chr19:11822048-11837937 |
| 11227 | Gigyf1 | NM_031408.2 | chr5:137960107-137969163 |
| 11228 | Gigyf2 | NM_001110212.2 | chr1:89223572-89347385 |
| 11229 | Gigyf2 | NM_146112.4 | chr1:89223572-89347385 |
| 11230 | Gimap1 | NM_008376.3 | chr6:48689045-48693794 |
| 11231 | Gimap1 | NM_175035.5 | chr6:48689045-48693794 |
| 11232 | Gimap3 | NM_031247.3 | chr6:48714462-48720850 |
| 11233 | Gimap4 | NM_001243199.1 | chr6:48634576-48642061 |
| 11234 | Gimap4 | NM_001243200.1 | chr6:48634576-48642061 |
| 11235 | Gimap4 | NM_001243201.1 | chr6:48634576-48642061 |
| 11236 | Gimap4 | NM_174990.4 | chr6:48634576-48642061 |
| 11237 | Gimap4 | NM_175048.3 | chr6:48634576-48642061 |
| 11238 | Gimap5 | NM_175035.5 | chr6:48696195-48704199 |
| 11239 | Gimap6 | NM_153175.3 | chr6:48651581-48658243 |
| 11240 | Gimap7 | NM_146167.3 | chr6:48668619-48674635 |
| 11241 | Gimap8 | NM_001077410.1 | chr6:48597232-48610874 |
| 11242 | Gimap8 | NM_001286629.1 | chr6:48597232-48610874 |
| 11243 | Gimap8 | NM_212486.2 | chr6:48597232-48610874 |
| 11244 | Gimap9 | NM_174960.2 | chr6:48626133-48628703 |
| 11245 | Gin1 | NM_026250.2 | chr1:99666755-99689548 |
| 11246 | Ginm1 | NM_145418.4 | chr10:7487744-7500715 |
| 11247 | Gins1 | NM_001163476.1 | chr2:150735329-150757016 |
| 11248 | Gins1 | NM_027014.1 | chr2:150735329-150757016 |
| 11249 | Gins2 | NM_178856.1 | chr8:123105166-123112975 |
| 11250 | Gins3 | NM_030198.3 | chr8:98157458-98168959 |
| 11251 | Gins4 | NM_024240.6 | chr8:24337081-24348140 |
| 11252 | Gip | NM_008119.2 | chr11:95885858-95892142 |
| 11253 | Gipc1 | NM_018771.3 | chr8:86176576-86188688 |
| 11254 | Gipc2 | NM_016867.1 | chr3:151756804-151828864 |
| 11255 | Gipc3 | NM_148951.1 | chr10:80800506-80806011 |
| 11256 | Gipr | NM_001080815.1 | chr7:19742473-19751476 |
| 11257 | Git1 | NM_001004144.1 | chr11:77306913-77321276 |
| 11258 | Git2 | NM_001077359.1 | chr5:115177416-115223501 |
| 11259 | Git2 | NM_001077360.1 | chr5:115177416-115223501 |
| 11260 | Git2 | NM_019834.3 | chr5:115177416-115223501 |
| 11261 | Gja1 | NM_010288.3 | chr10:56097105-56110225 |
| 11262 | Gja10 | NM_010289.2 | chr4:32687839-32689357 |
| 11263 | Gja3 | NM_001271623.1 | chr14:57653296-57676867 |
| 11264 | Gja3 | NM_016975.3 | chr14:57653296-57676867 |
| 11265 | Gja4 | NM_008120.3 | chr4:126988663-126991283 |
| 11266 | Gja5 | NM_001271628.1 | chr3:96836324-96857557 |
| 11267 | Gja5 | NM_008121.3 | chr3:96836324-96857557 |
| 11268 | Gja6 | NM_001014196.2 | chrX:157340048-157344984 |
| 11269 | Gja8 | NM_008123.3 | chr3:96717488-96729974 |
| 11270 | Gjb1 | NM_008124.3 | chrX:98572675-98580963 |
| 11271 | Gjb2 | NM_008125.3 | chr14:57717438-57721539 |
| 11272 | Gjb3 | NM_001160012.1 | chr4:127002478-127008080 |
| 11273 | Gjb3 | NM_008126.2 | chr4:127002478-127008080 |
| 11274 | Gjb4 | NM_008127.2 | chr4:127018329-127031325 |
| 11275 | Gjb5 | NM_010291.3 | chr4:127032652-127035408 |
| 11276 | Gjb6 | NM_001010937.2 | chr14:57742137-57752448 |
| 11277 | Gjb6 | NM_001271663.1 | chr14:57742137-57752448 |
| 11278 | Gjc1 | NM_001159382.1 | chr11:102660791-102681000 |
| 11279 | Gjc1 | NM_001159383.1 | chr11:102660791-102681000 |
| 11280 | Gjc1 | NM_008122.3 | chr11:102660791-102681000 |
| 11281 | Gjc2 | NM_080454.4 | chr11:58989065-58996715 |
| 11282 | Gjc2 | NM_175452.4 | chr11:58989065-58996715 |
| 11283 | Gjc3 | NM_080450.4 | chr5:138395036-138404187 |
| 11284 | Gjd2 | NM_010290.2 | chr2:113835337-113839355 |
| 11285 | Gjd3 | NM_178596.2 | chr11:98843493-98844330 |
| 11286 | Gjd4 | NM_153086.5 | chr18:9278604-9282807 |
| 11287 | Gje1 | NM_029722.1 | chr10:14435432-14438020 |
| 11288 | Gk2 | NM_010294.1 | chr5:97884180-97886027 |
| 11289 | Gk5 | NM_177352.4 | chr9:96019847-96083372 |
| 11290 | Gkap1 | NM_019832.3 | chr13:58334711-58375549 |

| | | | |
|---|---|---|---|
| 11291 | Gkn1 | NM_025466.1 | chr6:87295646-87300909 |
| 11292 | Gkn2 | NM_025467.1 | chr6:87323358-87329488 |
| 11293 | Gkn3 | NM_026860.1 | chr6:87333312-87338929 |
| 11294 | Gla | NM_013463.2 | chrX:131122707-131135544 |
| 11295 | Glb1 | NM_009752.2 | chr9:114310195-114383497 |
| 11296 | Glb1 | NR_108101.1 | chr9:114310195-114383497 |
| 11297 | Glb1 | NR_108102.1 | chr9:114310195-114383497 |
| 11298 | Glb1l | NM_029010.1 | chr1:75194810-75207353 |
| 11299 | Glb1l2 | NM_153803.1 | chr9:26570628-26614002 |
| 11300 | Glb1l3 | NM_001113323.1 | chr9:26625537-26668408 |
| 11301 | Glcci1 | NM_001286728.1 | chr6:8459599-8547549 |
| 11302 | Glcci1 | NM_001286729.1 | chr6:8459599-8547549 |
| 11303 | Glcci1 | NM_133236.3 | chr6:8459599-8547549 |
| 11304 | Glce | NM_033320.4 | chr9:61905055-61918413 |
| 11305 | Gldc | NM_138595.2 | chr19:30172930-30249931 |
| 11306 | Gldn | NM_177350.5 | chr9:54134293-54189584 |
| 11307 | Gldnos | NR_045805.1 | chr9:54116387-54149377 |
| 11308 | Gle1 | NM_028923.3 | chr2:29790928-29814952 |
| 11309 | Glg1 | NM_009149.2 | chr8:113681457-113783102 |
| 11310 | Gli1 | NM_010296.2 | chr10:126766938-126778635 |
| 11311 | Gli2 | NM_001081125.1 | chr1:120730637-120950196 |
| 11312 | Gli3 | NM_008130.2 | chr13:15555555-15821858 |
| 11313 | Glipr1 | NM_028608.3 | chr10:111422504-111434320 |
| 11314 | Glipr1l1 | NM_027018.1 | chr10:111497244-111515566 |
| 11315 | Glipr1l2 | NM_026223.2 | chr10:111520409-111545154 |
| 11316 | Glipr2 | NM_027450.3 | chr4:43970573-43991990 |
| 11317 | Glis1 | NM_147221.2 | chr4:107107323-107307664 |
| 11318 | Glis2 | NM_031184.3 | chr16:4594712-4615957 |
| 11319 | Glis3 | NM_175459.4 | chr19:28333341-28754567 |
| 11320 | Glmn | NM_001161738.1 | chr5:107963729-108090872 |
| 11321 | Glmn | NM_001161739.1 | chr5:107963729-108090872 |
| 11322 | Glmn | NM_133248.2 | chr5:107963729-108090872 |
| 11323 | Glo1 | NM_001113560.1 | chr17:30729806-30749604 |
| 11324 | Glo1 | NM_025374.3 | chr17:30729806-30749604 |
| 11325 | Glod4 | NM_026029.3 | chr11:76033896-76057201 |
| 11326 | Glod5 | NM_027227.2 | chr5:7581326-7595618 |
| 11327 | Glp1r | NM_021332.2 | chr17:31038811-31073455 |
| 11328 | Glp2r | NM_175681.3 | chr11:67519931-67584655 |
| 11329 | Gira1 | NM_001290821.1 | chr11:55327740-55421700 |
| 11330 | Gira1 | NM_020492.4 | chr11:55327740-55421700 |
| 11331 | Gira2 | NM_183427.4 | chrX:161566948-161764913 |
| 11332 | Gira3 | NM_080438.2 | chr8:58419621-58604149 |
| 11333 | Gira4 | NM_010297.2 | chrX:133292213-133314260 |
| 11334 | Girb | NM_001281969.1 | chr3:80647520-80717582 |
| 11335 | Girb | NM_010298.6 | chr3:80647520-80717582 |
| 11336 | Girp1 | NM_008132.2 | chr1:90396445-90406641 |
| 11337 | Girx | NM_053108.4 | chr13:75997333-75987599 |
| 11338 | Girx2 | NM_001038592.1 | chr1:145586478-145596808 |
| 11339 | Girx2 | NM_001038593.1 | chr1:145586478-145596808 |
| 11340 | Girx2 | NM_001038594.1 | chr1:145586478-145596808 |
| 11341 | Girx2 | NM_023505.2 | chr1:145586478-145596808 |
| 11342 | Girx3 | NM_023140.4 | chr7:144629331-144660277 |
| 11343 | Girx5 | NM_028419.2 | chr12:106270898-106279120 |
| 11344 | Gls | NM_001081081.2 | chr1:52220293-52290076 |
| 11345 | Gls | NM_001113383.1 | chr1:52220293-52290076 |
| 11346 | Gls2 | NM_001033264.2 | chr10:127631690-127648850 |
| 11347 | Gls2 | NM_001285777.1 | chr10:127631690-127648850 |
| 11348 | Gls2 | NM_001285779.1 | chr10:127631690-127648850 |
| 11349 | Git1d1 | NM_177005.4 | chr5:128112631-128187890 |
| 11350 | Git25d1 | NM_146211.3 | chr8:74134922-74148810 |
| 11351 | Git28d2 | NM_177130.3 | chr3:85673767-85691440 |
| 11352 | Git8d1 | NM_001039095.1 | chr2:25649486-25671356 |
| 11353 | Git8d1 | NM_001165930.1 | chr14:31813011-31832317 |
| 11354 | Git8d1 | NM_029626.2 | chr14:31813011-31832317 |
| 11355 | Git8d2 | NM_029102.3 | chr82:113178-82153395 |
| 11356 | Gitp | NM_019821.2 | chr5:115119510-115140944 |
| 11357 | Gitpd1 | NM_024472.4 | chr4:155238831-155243549 |
| 11358 | Gitpd2 | NM_146020.1 | chr11:70332710-70334238 |
| 11359 | Gitscr1 | NM_001081418.1 | chr7:16556610-16584844 |
| 11360 | Gitscr1l | NM_001100452.1 | chr17:46935064-46968362 |
| 11361 | Gitscr2 | NM_133831.3 | chr7:16523185-16531457 |
| 11362 | Glud1 | NM_008133.2 | chr14:35123912-35158219 |
| 11363 | Glul | NM_008131.4 | chr1:155747059-155756853 |
| 11364 | Glyat | NM_145935.3 | chr19:12707797-12726227 |
| 11365 | Glyatl3 | NM_001145060.1 | chr17:41041689-41051299 |
| 11366 | Glycam1 | NM_001285987.1 | chr15:103393190-103395512 |
| 11367 | Glycam1 | NM_008134.3 | chr15:103393190-103395512 |
| 11368 | Glyctk | NM_001039586.1 | chr9:106055190-106060469 |
| 11369 | Glyctk | NM_174846.4 | chr9:106055190-106060469 |
| 11370 | Glyr1 | NM_001079814.1 | chr16:5013994-5050003 |
| 11371 | Glyr1 | NM_028720.2 | chr16:5013994-5050003 |
| 11372 | Gm10007 | NR_040449.1 | chr19:58370694-58374838 |
| 11373 | Gm10012 | NR_028042.1 | chr17:26038801-26039172 |
| 11374 | Gm10024 | NM_001081452.2 | chr10:77174191-77174754 |
| 11375 | Gm10033 | NR_038043.1 | chr8:71894923-71919443 |
| 11376 | Gm10033 | NR_038044.1 | chr8:71894923-71919443 |
| 11377 | Gm10046 | NR_033484.1 | chr7:28550691-28555991 |
| 11378 | Gm10052 | NR_002885.3 | chr15:103070863-103075015 |
| 11379 | Gm10057 | NM_001243016.1 | chrX:150436132-150447185 |
| 11380 | Gm10057 | NM_001243016.1 | chrX:150457322-150468372 |
| 11381 | Gm10057 | NM_001243016.1 | chrX:150478528-150489584 |
| 11382 | Gm10058 | NM_001109969.2 | chrX:24475577-24498514 |
| 11383 | Gm10058 | NM_001109969.2 | chrX:27574931-27597871 |
| 11384 | Gm10058 | NM_001109969.2 | chrX:28236042-28258941 |
| 11385 | Gm10058 | NM_001109969.2 | chrX:32607378-32630311 |

Fig. 25 - 61

| | | | | | | | | |
|---|---|---|---|---|---|---|---|---|
| 11386 | Gm10058 | NM_001109969.2 | chrX:32944181-32967088 | | 11481 | Gm10486 | NM_001109970.1 | chrX:26881314-26904251 |
| 11387 | Gm10058 | NM_001109969.2 | chrX:27889230-27912141 | | 11482 | Gm10486 | NM_001109970.1 | chrX:27228255-27251155 |
| 11388 | Gm10058 | NM_001109969.2 | chrX:26881314-26904251 | | 11483 | Gm10486 | NM_001109970.1 | chrX:32607378-32630311 |
| 11389 | Gm10058 | NM_001109969.2 | chrX:29924763-29947708 | | 11484 | Gm10486 | NM_001109970.1 | chrX:29483950-29506884 |
| 11390 | Gm10058 | NM_001109969.2 | chrX:26799159-26822068 | | 11485 | Gm10486 | NM_001109970.1 | chrX:29924763-29947708 |
| 11391 | Gm10058 | NM_001109969.2 | chrX:29483950-29506884 | | 11486 | Gm10486 | NM_001109970.1 | chrX:27574931-27597871 |
| 11392 | Gm10058 | NM_001109969.2 | chrX:27228255-27251155 | | 11487 | Gm10486 | NM_001109970.1 | chrX:27889230-27912141 |
| 11393 | Gm10058 | NM_001109969.2 | chrX:29130521-29153420 | | 11488 | Gm10486 | NM_001100609.1 | chrX:26799159-26822068 |
| 11394 | Gm10069 | NR_028592.1 | chr6:128388774-128476738 | | 11489 | Gm10487 | NM_001100609.1 | chrX:27228255-27251155 |
| 11395 | Gm10069 | NR_028593.1 | chr6:128388774-128476738 | | 11490 | Gm10487 | NM_001100609.1 | chrX:27574931-27597871 |
| 11396 | Gm10081 | NM_001162940.1 | chr7:114249425-114250373 | | 11491 | Gm10487 | NM_001100609.1 | chrX:32607378-32630311 |
| 11397 | Gm10094 | NM_001142441.1 | chr14:58417055-58421167 | | 11492 | Gm10487 | NM_001100609.1 | chrX:27889230-27912141 |
| 11398 | Gm10096 | NM_001102678.2 | chrX:26799159-26822068 | | 11493 | Gm10487 | NM_001100609.1 | chrX:28236042-28258941 |
| 11399 | Gm10096 | NM_001102678.2 | chrX:26881314-26904251 | | 11494 | Gm10488 | NM_001099325.2 | chrX:29483950-29506884 |
| 11400 | Gm10096 | NM_001102678.2 | chrX:32607378-32630311 | | 11495 | Gm10488 | NM_001099325.2 | chrX:27228255-27251155 |
| 11401 | Gm10096 | NM_001102678.2 | chrX:32944181-32967088 | | 11496 | Gm10488 | NM_001099325.2 | chrX:26799159-26822068 |
| 11402 | Gm10096 | NM_001102678.2 | chrX:27228255-27251155 | | 11497 | Gm10488 | NM_001099325.2 | chrX:32607378-32630311 |
| 11403 | Gm10096 | NM_001102678.2 | chrX:27574931-27597871 | | 11498 | Gm10488 | NM_001099325.2 | chrX:32944181-32967088 |
| 11404 | Gm10096 | NM_001102678.2 | chrX:27889230-27912141 | | 11499 | Gm10488 | NM_001099325.2 | chrX:27889230-27912141 |
| 11405 | Gm10096 | NM_001102678.2 | chrX:28236042-28258941 | | 11500 | Gm10488 | NM_001099325.2 | chrX:28236042-28258941 |
| 11406 | Gm10096 | NM_001102678.2 | chrX:24475577-24498514 | | 11501 | Gm10488 | NM_001099325.2 | chrX:29130521-29153420 |
| 11407 | Gm10096 | NM_001102678.2 | chrX:29130521-29153420 | | 11502 | Gm10494 | NR_033462.1 | chr17:79905388-79909826 |
| 11408 | Gm10096 | NM_001102678.2 | chrX:29483950-29506884 | | 11503 | Gm10509 | NR_045766.1 | chr17:21827178-21829180 |
| 11409 | Gm10096 | NM_001102678.2 | chrX:29924763-29947708 | | 11504 | Gm10510 | NR_033511.1 | chr17:15487776-15491425 |
| 11410 | Gm101 | NM_001153074.1 | chr1:121820095-121891787 | | 11505 | Gm10512 | NR_033458.1 | chr17:13897907-13399077 |
| 11411 | Gm10100 | NM_001205033.1 | chr10:77189231-77189593 | | 11506 | Gm10516 | NR_033536.1 | chr1:193960780-193974907 |
| 11412 | Gm10104 | NM_001177481.1 | chr8:22204716-22205680 | | 11507 | Gm10532 | NR_045879.1 | chr18:75674299-75682460 |
| 11413 | Gm10125 | NR_033552.1 | chr18:5491499-5592435 | | 11508 | Gm10536 | NR_033455.1 | chr18:57095913-57100172 |
| 11414 | Gm10142 | NM_001205035.1 | chr10:77178552-77178914 | | 11509 | Gm10538 | NR_045892.1 | chr1:134625930-134629403 |
| 11415 | Gm10147 | NM_001099919.2 | chrX:24475577-24498514 | | 11510 | Gm10548 | NR_040534.1 | chr18:34367429-34381426 |
| 11416 | Gm10147 | NM_001099919.2 | chrX:26799159-26822068 | | 11511 | Gm10549 | NR_045415.1 | chr18:33623816-33634364 |
| 11417 | Gm10147 | NM_001099919.2 | chrX:32944181-32967088 | | 11512 | Gm10556 | NR_045881.1 | chr18:4812483-4850957 |
| 11418 | Gm10147 | NM_001099919.2 | chrX:26881314-26904251 | | 11513 | Gm10560 | NR_040563.1 | chr4:155395753-155397933 |
| 11419 | Gm10147 | NM_001099919.2 | chrX:27228255-27251155 | | 11514 | Gm10578 | NR_045885.1 | chr7:144426366-144434292 |
| 11420 | Gm10147 | NM_001099919.2 | chrX:27574931-27597871 | | 11515 | Gm10584 | NR_028578.1 | chr7:139507347-139509974 |
| 11421 | Gm10147 | NM_001099919.2 | chrX:27889230-27912141 | | 11516 | Gm10591 | NM_001193668.1 | chr4:41763293-42104673 |
| 11422 | Gm10147 | NM_001099919.2 | chrX:28236042-28258941 | | 11517 | Gm10591 | NM_001193668.1 | chr4:41763293-42104673 |
| 11423 | Gm10147 | NM_001099919.2 | chrX:29130521-29153420 | | 11518 | Gm10591 | NM_001193668.1 | chrUn_random:527838-528569 |
| 11424 | Gm10147 | NM_001099919.2 | chrX:29483950-29506884 | | | | | |
| 11425 | Gm10147 | NM_001099919.2 | chrX:29924763-29947708 | | 11519 | Gm10619 | NR_077222.1 | chr7:80953107-80961389 |
| 11426 | Gm10147 | NM_001099919.2 | chrX:32607378-32630311 | | 11520 | Gm10635 | NR_045336.1 | chr9:79291843-79367109 |
| 11427 | Gm10190 | NR_028385.1 | chr17:80771197-80772882 | | 11521 | Gm10636 | NR_033542.1 | chr3:146030116-146041908 |
| 11428 | Gm10220 | NM_001134299.1 | chr5:26441303-26447965 | | 11522 | Gm10637 | NR_040697.1 | chr8:89693645-89723749 |
| 11429 | Gm10228 | NM_001270487.1 | chr16:89041167-89041717 | | 11523 | Gm10638 | NR_027829.1 | chr8:89269598-89270959 |
| 11430 | Gm10229 | NM_001199334.2 | chr16:89015521-89016091 | | 11524 | Gm10639 | NM_001122660.2 | chr9:78137734-78153332 |
| 11431 | Gm10230 | NM_001099347.2 | chrX:27574931-27597871 | | 11525 | Gm10640 | NR_046062.1 | chr3:31947376-31955660 |
| 11432 | Gm10230 | NM_001099347.2 | chrX:26799159-26822068 | | 11526 | Gm10649 | NR_028579.1 | chr8:79272985-79424072 |
| 11433 | Gm10230 | NM_001099347.2 | chrX:26881314-26904251 | | 11527 | Gm10653 | NR_003965.2 | chr9:62689284-62709831 |
| 11434 | Gm10248 | NR_033550.1 | chr14:23857417-23913793 | | 11528 | Gm10658 | NR_045886.1 | chr9:56904704-56919773 |
| 11435 | Gm10267 | NM_001281470.1 | chr18:44316056-44319539 | | 11529 | Gm10662 | NM_001201364.1 | chr7:23917641-23929499 |
| 11436 | Gm10272 | NR_026831.1 | chr10:77169332-77169731 | | 11530 | Gm10662 | NM_001201364.1 | chr7:22694452-22706310 |
| 11437 | Gm10280 | NR_033584.1 | chr8:115591161-115617233 | | 11531 | Gm10665 | NM_001167160.1 | chr7:23248128-23249094 |
| 11438 | Gm10318 | NM_001162944.1 | chr10:77315604-77316533 | | 11532 | Gm10667 | NM_001167161.1 | chr7:21059308-21060274 |
| 11439 | Gm10319 | NR_003624.2 | chr6:122086645-122100976 | | 11533 | Gm10677 | NR_046048.1 | chr9:47607243-47626291 |
| 11440 | Gm10324 | NM_001177832.1 | chr3:66214388-66223772 | | 11534 | Gm10681 | NM_001270429.1 | chr3:98302995-98314490 |
| 11441 | Gm10334 | NM_001103153.1 | chr6:41392212-41396096 | | 11535 | Gm10681 | NM_001270429.1 | chr3:98356465-98367961 |
| 11442 | Gm10336 | NR_045170.1 | chr3:12274983-12278755 | | 11536 | Gm10684 | NR_033547.1 | chr9:44915259-44943689 |
| 11443 | Gm10354 | NM_001281514.1 | chr5:14974497-14978899 | | 11537 | Gm10696 | NM_001146107.1 | chr3:93978333-93982115 |
| 11444 | Gm10364 | NR_073535.1 | chr14:55657298-55661813 | | 11538 | Gm10697 | NM_001163731.1 | chr3:93764213-93765236 |
| 11445 | Gm10373 | NR_046064.1 | chr15:43262488-43308582 | | 11539 | Gm10714 | NR_040530.1 | chr1:173950538-174009419 |
| 11446 | Gm10375 | NM_001098269.2 | chr14:44180291-44185678 | | 11540 | Gm10731 | NR_045392.1 | chr3:40657398-40659207 |
| 11447 | Gm10377 | NM_001244671.1 | chr14:43371374-43376742 | | 11541 | Gm10745 | NR_040751.1 | chr3:11823228-11844359 |
| 11448 | Gm10377 | NM_001244671.1 | chr14:43688720-43694109 | | 11542 | Gm10754 | NR_033537.1 | chr10:97144048-97429724 |
| 11449 | Gm10389 | NR_033541.1 | chr15:10530048-10541406 | | 11543 | Gm10767 | NM_001177750.1 | chr13:67006350-67010102 |
| 11450 | Gm10390 | NR_045793.1 | chr5:120571105-120589272 | | 11544 | Gm10768 | NR_033472.1 | chr19:43913292-43915335 |
| 11451 | Gm10400 | NR_033555.1 | chr6:141289074-141292908 | | 11545 | Gm10778 | NM_001142963.1 | chr10:81111813-81130106 |
| 11452 | Gm10406 | NM_001164727.1 | chr14:7838628-7859963 | | 11546 | Gm10778 | NM_001142963.1 | chr10:81274930-81289235 |
| 11453 | Gm10408 | NM_001256501.1 | chr14:3500819-3668655 | | 11547 | Gm10782 | NR_046061.1 | chr13:56464260-56470218 |
| 11454 | Gm10408 | NM_001256501.1 | chr14:3740222-3906698 | | 11548 | Gm10785 | NR_040389.1 | chr16:91689143-91716000 |
| 11455 | Gm10408 | NM_001256501.1 | chr14:6653690-7119724 | | 11549 | Gm10787 | NR_045882.1 | chr10:76474739-76484959 |
| 11456 | Gm10409 | NR_033121.1 | chr14:3740222-3906698 | | 11550 | Gm10789 | NR_033476.1 | chr16:90142481-90147072 |
| 11457 | Gm10409 | NR_033121.1 | chr14:6653690-7119724 | | 11551 | Gm10790 | NR_033545.1 | chr13:41961283-42008461 |
| 11458 | Gm10409 | NR_033121.1 | chr14:3500819-3668655 | | 11552 | Gm10791 | NR_045889.1 | chr16:84972456-84979696 |
| 11459 | Gm10413 | NM_029288.3 | chr14:3500819-3668655 | | 11553 | Gm10804 | NR_040532.1 | chr2:93259258-93310031 |
| 11460 | Gm10413 | NM_029288.3 | chr14:3740222-3906698 | | 11554 | Gm10804 | NR_040533.1 | chr2:93259258-93310031 |
| 11461 | Gm10413 | NM_029288.3 | chr14:6653690-7119724 | | 11555 | Gm10814 | NR_045783.1 | chr19:6012620-6018459 |
| 11462 | Gm10415 | NR_045480.1 | chr6:126236666-126278704 | | 11556 | Gm10823 | NR_033475.1 | chr16:27850015-27926214 |
| 11463 | Gm10416 | NR_027964.1 | chr5:110262519-110263161 | | 11557 | Gm10825 | NR_028580.1 | chr10:22122618-22127276 |
| 11464 | Gm10421 | NR_033538.1 | chr12:118382996-118389742 | | 11558 | Gm10845 | NR_033535.1 | chr14:80260327-80268983 |
| 11465 | Gm10432 | NR_045741.1 | chr12:101514819-101539118 | | 11559 | Gm10857 | NR_033470.1 | chr2:6053914-6061616 |
| 11466 | Gm10433 | NR_045282.1 | chr12:101426177-101431748 | | 11560 | Gm10857 | NR_033471.1 | chr2:6053914-6061616 |
| 11467 | Gm10434 | NM_001105254.1 | chr12:89414033-89420338 | | 11561 | Gm10863 | NR_029470.1 | chr15:78996495-79046831 |
| 11468 | Gm10439 | NM_001037716.2 | chrX:146029143-146071164 | | 11562 | Gm10865 | NR_045746.1 | chr15:78825385-78841471 |
| 11469 | Gm10440 | NR_038045.1 | chr5:54741230-54749781 | | 11563 | Gm10872 | NR_045747.1 | chr15:76097217-76100269 |
| 11470 | Gm10445 | NR_046063.1 | chr6:84362935-84373832 | | 11564 | Gm10921 | NM_001085553.1 | chr4:4074963-4076923 |
| 11471 | Gm1045 | NM_001177577.1 | chr5:92416498-92424343 | | 11565 | Gm10921 | NM_001085553.1 | chr30245481-30247441 |
| 11472 | Gm10451 | NR_028520.1 | chr12:77545483-77549685 | | 11566 | Gm10922 | NM_001085554.1 | chr3:3993613-3995573 |
| 11473 | Gm10466 | NR_033491.1 | chr11:24621005-24630722 | | 11567 | Gm10943 | NR_026944.1 | chr10:76720517-76721968 |
| 11474 | Gm10471 | NM_001177579.1 | chr5:26408712-26415804 | | 11568 | Gm1110 | NM_001281475.1 | chr9:26687151-26730666 |
| 11475 | Gm10474 | NR_028431.1 | chrX:65920688-65931574 | | 11569 | Gm1110 | NR_033508.1 | chr17:57231446-57245365 |
| 11476 | Gm10486 | NM_001109970.1 | chrX:32944181-32967088 | | 11570 | Gm11127 | NM_001199967.1 | chr17:36192761-36195316 |
| 11477 | Gm10486 | NM_001109970.1 | chrX:24475577-24498514 | | 11571 | Gm11128 | NM_001201389.1 | chr6:85758044-85759871 |
| 11478 | Gm10486 | NM_001109970.1 | chrX:28236042-28258941 | | 11572 | Gm11149 | NR_029465.1 | chr9:49326393-49376130 |
| 11479 | Gm10486 | NM_001109970.1 | chrX:29130521-29153420 | | 11573 | Gm11166 | NR_024558.1 | chr17:13289525-13291338 |
| 11480 | Gm10486 | NM_001109970.1 | chrX:26799159-26822068 | | 11574 | Gm11186 | NR_046047.1 | chr11:52924953-52933558 |

Fig. 25 - 62

| | | | | | | | | |
|---|---|---|---|---|---|---|---|---|
| 11575 | Gm11190 | NR_033549.1 | chr11:77725628-77742790 | | 11670 | Gm12709 | NR_040444.1 | chr4:102639871-102662360 |
| 11576 | Gm11201 | NR_045873.1 | chr11:78837099-78848507 | | 11671 | Gm12718 | NR_040673.1 | chr4:103055104-103164793 |
| 11577 | Gm11213 | NR_028583.1 | chr4:63257934-63266295 | | 11672 | Gm12789 | NM_001085520.2 | chr4:101659444-101662836 |
| 11578 | Gm11213 | NR_028584.1 | chr4:63257934-63266295 | | 11673 | Gm12794 | NM_001085516.1 | chr4:101613011-101615788 |
| 11579 | Gm1123 | NM_001080776.1 | chr9:98907383-98936109 | | 11674 | Gm128 | NM_001024841.3 | chr9:95040841-95045031 |
| 11580 | Gm11237 | NM_001256481.2 | chr4:73281698-73288077 | | 11675 | Gm12830 | NR_033617.1 | chr4:114494324-114528771 |
| 11581 | Gm11237 | NM_001256481.2 | chr4:73311921-73318302 | | 11676 | Gm12886 | NM_001144948.1 | chr4:121087339-121095704 |
| 11582 | Gm11237 | NM_001256481.2 | chr4:73296797-73303179 | | 11677 | Gm12887 | NM_001099309.1 | chr4:121286608-121294730 |
| 11583 | Gm11240 | NR_046041.1 | chr4:73437147-73444282 | | 11678 | Gm12888 | NM_001033791.3 | chr4:120988920-120997522 |
| 11584 | Gm11240 | NR_046042.1 | chr4:73437147-73444282 | | 11679 | Gm12942 | NM_001099319.2 | chr4:126803286-126806904 |
| 11585 | Gm11346 | NR_024599.1 | chr13:24689994-24696636 | | 11680 | Gm12992 | NR_102393.1 | chr4:131429553-131475944 |
| 11586 | Gm11351 | NR_045062.1 | chr13:26012902-26058185 | | 11681 | Gm12992 | NR_102394.1 | chr4:131429553-131475944 |
| 11587 | Gm1140 | NM_001126317.1 | chrX:64936074-64946737 | | 11682 | Gm13003 | NR_040443.1 | chr4:136714996-136720981 |
| 11588 | Gm1140 | NM_001126317.1 | chrX:64948872-64959525 | | 11683 | Gm13011 | NM_001126318.1 | chr4:136957468-136965706 |
| 11589 | Gm1141 | NR_027801.1 | chrX:69177776-69186210 | | 11684 | Gm13023 | NM_001007077.2 | chr4:143379236-143385488 |
| 11590 | Gm11413 | NR_045463.1 | chr4:83024220-83036572 | | 11685 | Gm13031 | NR_045911.1 | chr4:140503581-140513817 |
| 11591 | Gm11426 | NR_033582.1 | chr1:82446854-82449811 | | 11686 | Gm13032 | NR_045944.1 | chr4:140366908-140373426 |
| 11592 | Gm11437 | NM_001037932.2 | chr1:83961864-83980978 | | 11687 | Gm13034 | NR_030771.1 | chr4:146034924-146036119 |
| 11593 | Gm11468 | NR_033467.1 | chr2:166099407-166120331 | | 11688 | Gm13040 | NM_001113736.1 | chr4:143125856-143132374 |
| 11594 | Gm11487 | NM_001013393.1 | chr4:73062065-73066106 | | 11689 | Gm13043 | NM_001039595.2 | chr4:143101246-143107734 |
| 11595 | Gm11517 | NR_033523.1 | chr1:96656646-96659470 | | 11690 | Gm13051 | NM_001037926.2 | chr4:146064712-146094024 |
| 11596 | Gm11529 | NR_033524.1 | chr1:96308212-96325861 | | 11691 | Gm13057 | NM_001113735.1 | chr4:143141602-143148139 |
| 11597 | Gm11538 | NR_108029.1 | chr1:96064767-96066794 | | 11692 | Gm13057 | NM_001113735.1 | chr4:143101214-143107736 |
| 11598 | Gm11541 | NM_001007584.2 | chr1:94555811-94565813 | | 11693 | Gm13078 | NM_001085412.2 | chr4:143309353-143319061 |
| 11599 | Gm11544 | NM_001205037.1 | chr1:94706144-94710907 | | 11694 | Gm13083 | NM_001126324.1 | chr4:143204905-143208498 |
| 11600 | Gm11545 | NM_001105561.1 | chr1:94616449-94622496 | | 11695 | Gm13084 | NM_001005371.3 | chr4:143399893-143405996 |
| 11601 | Gm11548 | NR_040590.1 | chr3:36398725-36405731 | | 11696 | Gm13088 | NM_001126325.1 | chr4:143243662-143247149 |
| 11602 | Gm11549 | NR_040411.1 | chr3:36413978-36420367 | | 11697 | Gm13102 | NM_001085419.1 | chr4:143689782-143700004 |
| 11603 | Gm11554 | NM_001099313.2 | chr1:99659386-99671210 | | 11698 | Gm13103 | NM_177571.3 | chr4:143436399-143443540 |
| 11604 | Gm11554 | NM_001099313.2 | chr1:99659386-99671210 | | 11699 | Gm13119 | NM_001034101.2 | chr4:143947866-143954322 |
| 11605 | Gm11559 | NM_001177484.2 | chr1:99725789-99726885 | | 11700 | Gm13124 | NM_001085542.1 | chr4:144144902-144155037 |
| 11606 | Gm11562 | NM_001177537.2 | chr1:99480911-99481718 | | 11701 | Gm13125 | NM_001115077.1 | chr4:143962662-143967836 |
| 11607 | Gm11563 | NM_001126320.2 | chr1:99519255-99520273 | | 11702 | Gm13128 | NM_001085541.1 | chr4:143920151-143923368 |
| 11608 | Gm11564 | NM_001100614.1 | chr1:99676289-99676980 | | 11703 | Gm13139 | NM_001083918.1 | chr4:146506202-146554688 |
| 11609 | Gm11565 | NM_001126323.1 | chr1:99776064-99776985 | | 11704 | Gm13152 | NM_001039209.2 | chr4:146549975-146887529 |
| 11610 | Gm11567 | NM_001101613.1 | chr1:99740550-99741543 | | 11705 | Gm13156 | NM_001014397.4 | chr4:146927385-146959310 |
| 11611 | Gm11568 | NM_001205030.1 | chr1:99719230-99720374 | | 11706 | Gm13157 | NM_001127189.3 | chr4:147128082-147183897 |
| 11612 | Gm11569 | NM_001099312.1 | chr1:99664862-99665760 | | 11707 | Gm13177 | NM_001081248.1 | chr4:144203609-144213301 |
| 11613 | Gm11570 | NM_001256057.1 | chr1:99846016-99847907 | | 11708 | Gm13180 | NM_001085536.1 | chr4:144293093-144311307 |
| 11614 | Gm11595 | NM_001126322.1 | chr1:99633027-99634227 | | 11709 | Gm13212 | NM_001205101.1 | chr4:145207048-145214297 |
| 11615 | Gm11596 | NM_001099311.2 | chr1:99653988-99654606 | | 11710 | Gm1322 | NM_001033477.3 | chr2:67011890-67024269 |
| 11616 | Gm11627 | NR_040286.1 | chr1:102437712-102440433 | | 11711 | Gm13238 | NR_033612.1 | chr4:145427121-145427895 |
| 11617 | Gm11651 | NR_104047.1 | chr1:105826921-105847008 | | 11712 | Gm13242 | NM_001103158.2 | chr4:145260509-145294340 |
| 11618 | Gm11696 | NR_038097.1 | chr1:109216092-109224968 | | 11713 | Gm13247 | NM_001243138.1 | chr4:145651165-145696039 |
| 11619 | Gm11710 | NM_001101656.2 | chr1:114892760-114899004 | | 11714 | Gm13247 | NM_001243139.1 | chr4:145651165-145696039 |
| 11620 | Gm11711 | NM_001101657.2 | chr1:114882002-114888247 | | 11715 | Gm13251 | NM_001085522.2 | chr4:145728598-145749009 |
| 11621 | Gm11744 | NM_001163318.1 | chr1:116518421-116529703 | | 11716 | Gm13265 | NM_001085528.1 | chr4:88400771-88401320 |
| 11622 | Gm11747 | NR_045902.1 | chr1:118305514-118316309 | | 11717 | Gm13272 | NM_001161608.1 | chr4:88425754-88426564 |
| 11623 | Gm11757 | NM_001085538.2 | chr4:73547809-73551857 | | 11718 | Gm13275 | NM_001085533.2 | chr4:88439645-88441201 |
| 11624 | Gm11757 | NM_001085538.2 | chr4:73532968-73537016 | | 11719 | Gm13275 | NM_001085533.2 | chr4:88445478-88447034 |
| 11625 | Gm11757 | NM_001085538.2 | chr4:73518122-73522170 | | 11720 | Gm13276 | NM_001085532.3 | chr4:88430957-88432419 |
| 11626 | Gm11758 | NM_001097978.2 | chr4:73518122-73522170 | | 11721 | Gm13277 | NM_001098840.3 | chr4:88433881-88435342 |
| 11627 | Gm11758 | NM_001097978.2 | chr4:73532968-73537016 | | 11722 | Gm13278 | NM_001098841.3 | chr4:88442645-88444108 |
| 11628 | Gm11758 | NM_001097978.2 | chr4:73547809-73551857 | | 11723 | Gm13278 | NM_001098841.3 | chr4:88436798-88438261 |
| 11629 | Gm11762 | NR_045099.1 | chr1:119409943-119430360 | | 11724 | Gm13279 | NM_001243166.1 | chr4:88436798-88438261 |
| 11630 | Gm11780 | NM_001277919.1 | chr4:4454920-4456605 | | 11725 | Gm13279 | NM_001243166.1 | chr4:88442645-88444108 |
| 11631 | Gm11837 | NM_001243100.1 | chr4:14857788-14880177 | | 11726 | Gm13283 | NM_001085531.2 | chr4:88406677-88407488 |
| 11632 | Gm11937 | NM_001099346.1 | chr1:99471107-99471503 | | 11727 | Gm13285 | NM_001161609.1 | chr4:88449157-88449706 |
| 11633 | Gm11938 | NM_001127354.1 | chr1:99463959-99464622 | | 11728 | Gm13285 | NM_001161609.1 | chr4:88451434-88454284 |
| 11634 | Gm11944 | NR_045708.1 | chr1:3209003-3220725 | | 11729 | Gm13285 | NM_001161609.1 | chr4:88445478-88447034 |
| 11635 | Gm11961 | NR_027797.1 | chr1:4520277-4530014 | | 11730 | Gm13285 | NM_001161609.1 | chr4:88419737-88420705 |
| 11636 | Gm11961 | NR_027798.2 | chr1:4520277-4530014 | | 11731 | Gm13285 | NM_001161609.1 | chr4:88442645-88444108 |
| 11637 | Gm11974 | NR_045893.1 | chr1:6425593-6428763 | | 11732 | Gm13285 | NM_001161609.1 | chr4:88436798-88438261 |
| 11638 | Gm11978 | NR_028586.1 | chr1:6550151-6560239 | | 11733 | Gm13285 | NM_001161609.1 | chr4:88422665-88423633 |
| 11639 | Gm11981 | NR_046025.1 | chr1:6616003-6620040 | | 11734 | Gm13285 | NM_001161609.1 | chr4:88425753-88426564 |
| 11640 | Gm11985 | NR_045101.1 | chr1:7083159-7088572 | | 11735 | Gm13285 | NM_001161609.1 | chr4:88433880-88435342 |
| 11641 | Gm11992 | NM_001037928.3 | chr1:8948595-8969357 | | 11736 | Gm13288 | NM_001243150.1 | chr4:88403747-88404296 |
| 11642 | Gm12 | NM_001195544.1 | chr1:98459604-98460900 | | 11737 | Gm13288 | NM_001243167.1 | chr4:88451435-88454284 |
| 11643 | Gm12060 | NR_004857.1 | chr1:23458059-23458842 | | 11738 | Gm13290 | NM_001243155.1 | chr4:88419737-88420705 |
| 11644 | Gm12070 | NR_002890.1 | chr1:26685107-26687859 | | 11739 | Gm13290 | NM_001243155.1 | chr4:88422665-88423633 |
| 11645 | Gm12130 | NR_040295.1 | chr1:38305049-38333547 | | 11740 | Gm13290 | NM_001243155.1 | chr4:88451434-88454284 |
| 11646 | Gm12159 | NR_045100.1 | chr1:44916367-44930430 | | 11741 | Gm13293 | NR_040369.1 | chr2:11261116-11265733 |
| 11647 | Gm12169 | NM_001163571.1 | chr1:46337752-46351658 | | 11742 | Gm13298 | NM_001085530.1 | chr4:42535970-42541769 |
| 11648 | Gm12171 | NM_001163353.1 | chr1:46361914-46369570 | | 11743 | Gm13298 | NM_001085530.1 | chrUn_random:671916-677715 |
| 11649 | Gm12185 | NM_001045540.2 | chr1:48718157-48740684 | | 11744 | Gm13298 | NM_001085530.1 | chr4:41763293-42104673 |
| 11650 | Gm12191 | NR_028101.1 | chr15:34370261-34372988 | | 11745 | Gm13304 | NM_001193666.1 | chr4:42391949-42393080 |
| 11651 | Gm12216 | NR_033332.1 | chr1:53598990-53672758 | | 11746 | Gm13304 | NM_001193666.1 | chr4:42625654-42626785 |
| 11652 | Gm12238 | NR_028480.1 | chr1:55296208-55296331 | | 11747 | Gm13305 | NM_001099348.1 | chr4:42664135-42679295 |
| 11653 | Gm12250 | NM_001135115.1 | chr1:57997344-58003700 | | 11748 | Gm13305 | NM_001099348.1 | chr4:41763293-42104673 |
| 11654 | Gm12253 | NM_001045542.1 | chr1:58246060-58255124 | | 11749 | Gm13305 | NM_001099348.1 | chr4:42339258-42354418 |
| 11655 | Gm12295 | NR_040669.1 | chr1:65091155-65101335 | | 11750 | Gm13308 | NM_001177580.1 | chr4:41763293-42104673 |
| 11656 | Gm12298 | NR_033539.1 | chr1:66719134-66760588 | | 11751 | Gm13308 | NM_001177580.1 | chrUn_random:701089-702124 |
| 11657 | Gm12338 | NR_110477.1 | chr1:75413146-75413733 | | 11752 | Gm13315 | NR_028497.1 | chr2:14642269-14644249 |
| 11658 | Gm12359 | NR_033551.1 | chr1:98659623-98671403 | | 11753 | Gm13363 | NR_002688.1 | chr1:30998487-31006555 |
| 11659 | Gm12409 | NR_046068.1 | chr4:45775248-45777095 | | 11754 | Gm13375 | NR_033225.1 | chr2:20890500-20891975 |
| 11660 | Gm12429 | NM_001277167.1 | chr4:42860943-42866760 | | 11755 | Gm13446 | NR_045894.1 | chr2:35405054-35414222 |
| 11661 | Gm12504 | NR_040414.1 | chr4:44314764-44316995 | | 11756 | Gm13483 | NR_040361.1 | chr2:50152329-50289487 |
| 11662 | Gm12505 | NR_040674.1 | chr4:55423314-55431714 | | 11757 | Gm13483 | NR_040362.1 | chr2:50152329-50289487 |
| 11663 | Gm12522 | NR_040560.1 | chr3:108182195-108186659 | | 11758 | Gm13490 | NR_040639.1 | chr2:51512485-51587529 |
| 11664 | Gm12530 | NR_040669.1 | chr4:57184942-57189426 | | 11759 | Gm13497 | NR_040636.1 | chr2:51097350-51151465 |
| 11665 | Gm12603 | NR_033533.1 | chr4:88696210-88730514 | | 11760 | Gm13498 | NR_033595.1 | chr2:50765203-50767366 |
| 11666 | Gm12633 | NR_033610.1 | chr4:90026315-90028005 | | 11761 | Gm13539 | NR_045340.1 | chr2:25640136-25642542 |
| 11667 | Gm12657 | NM_001081019.1 | chr4:94267010 | | 11762 | Gm13544 | NR_040365.1 | chr2:58129190-58139313 |
| 11668 | Gm12669 | NR_033611.1 | chr7:144629357-144659663 | | 11763 | Gm13546 | NR_045895.1 | chr2:58016384-58029474 |
| 11669 | Gm12695 | NM_001081284.1 | chr4:96390577-96451851 | | | | | |

Fig. 25 - 63

| | | | |
|---|---|---|---|
| 11764 | Gm13546 | NR_045896.1 | chr2:58016384-58029474 |
| 11765 | Gm13547 | NM_001177392.1 | chr2:29617047-29619609 |
| 11766 | Gm13580 | NR_046065.1 | chr2:60249581-60250631 |
| 11767 | Gm13582 | NR_045335.1 | chr2:60802432-60813208 |
| 11768 | Gm136 | NM_001033255.2 | chr4:34691036-34703508 |
| 11769 | Gm13629 | NR_033495.1 | chr2:66278937-66385529 |
| 11770 | Gm13710 | NR_046046.1 | chr2:84340904-84347030 |
| 11771 | Gm13749 | NR_027824.1 | chr1:64011300-64015573 |
| 11772 | Gm13752 | NR_040370.1 | chr2:80231520-80238373 |
| 11773 | Gm13769 | NM_001270423.1 | chr2:90061723-90064628 |
| 11774 | Gm13769 | NM_001270423.1 | chr2:90162378-90165283 |
| 11775 | Gm13807 | NR_040529.1 | chr2:93243703-93257987 |
| 11776 | Gm13826 | NM_001271590.1 | chr5:115552930-115560277 |
| 11777 | Gm13826 | NM_001271591.1 | chr5:115552930-115560277 |
| 11778 | Gm13871 | NM_001175782.2 | chr4:73532968-73537016 |
| 11779 | Gm13871 | NM_001175782.2 | chr4:73518122-73522170 |
| 11780 | Gm13871 | NM_001175782.2 | chr4:73547809-73551857 |
| 11781 | Gm13889 | NM_001145034.1 | chr2:93795966-93797257 |
| 11782 | Gm13939 | NR_033473.1 | chr2:109742552-109753476 |
| 11783 | Gm13944 | NR_040368.1 | chr2:77300701-77318995 |
| 11784 | Gm14005 | NR_028589.1 | chr2:128124398-128255087 |
| 11785 | Gm14005 | NR_028590.1 | chr2:128124398-128255087 |
| 11786 | Gm14005 | NR_028591.1 | chr2:128124398-128255087 |
| 11787 | Gm14015 | NR_040637.1 | chr2:106303979-106363260 |
| 11788 | Gm14023 | NR_040371.1 | chr2:129123106-129133562 |
| 11789 | Gm14057 | NR_024097.1 | chr2:130627702-130629837 |
| 11790 | Gm14085 | NM_001085518.1 | chr2:122310676-122353776 |
| 11791 | Gm14092 | NM_001037929.2 | chr2:145375191-145380718 |
| 11792 | Gm14124 | NM_001142410.1 | chr2:150083252-150096036 |
| 11793 | Gm14137 | NM_001039223.3 | chr2:119000245-119003311 |
| 11794 | Gm14139 | NM_001145863.1 | chr2:150007490-150019015 |
| 11795 | Gm14151 | NM_001097977.1 | chr2:150923980-150929545 |
| 11796 | Gm14151 | NM_001097977.1 | chr2:150912521-150918086 |
| 11797 | Gm14164 | NR_033505.1 | chr2:152171406-152201058 |
| 11798 | Gm14169 | NR_040372.1 | chr2:156434933-156439158 |
| 11799 | Gm14204 | NR_040358.1 | chr2:158421207-158436459 |
| 11800 | Gm14204 | NR_040359.1 | chr2:158421207-158436459 |
| 11801 | Gm14207 | NR_030683.1 | chr2:119146935-119151933 |
| 11802 | Gm14288 | NM_001033123.3 | chr2:175594788-176850107 |
| 11803 | Gm14288 | NM_001033123.3 | chr2:174952492-175261278 |
| 11804 | Gm14288 | NM_001033123.3 | chr2:176583305-176693409 |
| 11805 | Gm14295 | NM_001205057.2 | chr2:176583305-176693409 |
| 11806 | Gm14305 | NM_001099327.1 | chr2:175594788-176850107 |
| 11807 | Gm14305 | NM_001099327.1 | chr2:175594788-176850107 |
| 11808 | Gm14306 | NM_001242944.1 | chr2:175594788-176850107 |
| 11809 | Gm14306 | NM_001242944.1 | chr2:175295525-175308823 |
| 11810 | Gm14308 | NM_001099349.2 | chr2:175594788-176850107 |
| 11811 | Gm14308 | NM_001099349.2 | chr2:175594788-176850107 |
| 11812 | Gm14308 | NM_001099349.2 | chr2:175594788-176850107 |
| 11813 | Gm14322 | NM_001243903.1 | chr2:177493992-177507980 |
| 11814 | Gm14325 | NM_001204829.2 | chr2:177563695-177575023 |
| 11815 | Gm14326 | NM_001190302.2 | chr2:177670697-177691993 |
| 11816 | Gm14326 | NM_001282028.1 | chr2:177670697-177691993 |
| 11817 | Gm14327 | NR_038101.2 | chr2:177631867-177662555 |
| 11818 | Gm14345 | NM_001085545.1 | chrX:3,461,361-3,463,320 |
| 11819 | Gm14346 | NM_001085551.1 | chrX:30291071-30293031 |
| 11820 | Gm14346 | NM_001085551.1 | chrX:3665477-3667437 |
| 11821 | Gm14346 | NM_001085551.1 | chrX:3410667-3412627 |
| 11822 | Gm14347 | NM_001085543.1 | chrX:3907011-3908970 |
| 11823 | Gm14351 | NM_001085552.2 | chrX:3410667-3412627 |
| 11824 | Gm14351 | NM_001085552.2 | chrX:3461360-3463320 |
| 11825 | Gm14351 | NM_001085552.2 | chrX:3665477-3667437 |
| 11826 | Gm14351 | NM_001085552.2 | chrX:30291071-30293031 |
| 11827 | Gm14351 | NM_001085552.2 | chrX:31750506-31752466 |
| 11828 | Gm14374 | NM_001085553.1 | chrX:5246184-5248144 |
| 11829 | Gm14378 | NM_001195258.1 | chr8:4248213-4251423 |
| 11830 | Gm14379 | NR_026741.1 | chrX:6953050-6955168 |
| 11831 | Gm14391 | NM_001099308.2 | chr2:175594788-176850107 |
| 11832 | Gm14391 | NM_001099308.2 | chr2:174952492-175261278 |
| 11833 | Gm14391 | NM_001177480.1 | chr2:175594788-176850107 |
| 11834 | Gm14391 | NM_001177480.1 | chr2:174952492-175261278 |
| 11835 | Gm14393 | NM_001085546.2 | chr2:174887049-174893270 |
| 11836 | Gm14403 | NR_036450.1 | chr2:177282930-177297016 |
| 11837 | Gm14405 | NR_040256.1 | chr2:175393150-175404796 |
| 11838 | Gm14405 | NR_040256.1 | chr2:175594788-176850107 |
| 11839 | Gm14405 | NR_040256.1 | chr2:175594788-176850107 |
| 11840 | Gm14420 | NM_001177568.1 | chr2:177249446-177263899 |
| 11841 | Gm14430 | NM_001100415.1 | chr2:175,147,335-176,421,028 |
| 11842 | Gm14431 | NM_001177404.1 | chr2:175594788-176850107 |
| 11843 | Gm14431 | NM_001177404.1 | chr2:175594788-176850107 |
| 11844 | Gm14431 | NM_001177406.1 | chr2:175594788-176850107 |
| 11845 | Gm14434 | NM_001101804.1 | chr2:174952492-175261278 |
| 11846 | Gm14434 | NM_001101804.1 | chr2:174952492-175261278 |
| 11847 | Gm14436 | NM_001242943.1 | chr2:175295525-175308823 |
| 11848 | Gm14436 | NM_001242943.1 | chr2:175594788-176850107 |
| 11849 | Gm14440 | NM_001199308.1 | chr2:175594788-176850107 |
| 11850 | Gm14440 | NM_001199308.1 | chr2:175594788-176850107 |
| 11851 | Gm14440 | NM_001199308.1 | chr2:174952492-175261278 |
| 11852 | Gm14446 | NM_001101605.1 | chr19:34667377-34676458 |
| 11853 | Gm14446 | NM_001110517.1 | chr19:34667377-34676458 |
| 11854 | Gm14458 | NM_001099326.2 | chrX:8563065-8563798 |
| 11855 | Gm14459 | NM_001126491.1 | chrX:8091177-8102080 |
| 11856 | Gm14461 | NM_177843.3 | chr2:78077703-78142387 |
| 11857 | Gm14474 | NM_001242947.1 | chrX:10879557-10880047 |
| 11858 | Gm14475 | NM_001242954.1 | chrX:10882780-10883098 |
| 11859 | Gm14475 | NM_001242954.1 | chrX:10895381-10895890 |
| 11860 | Gm14475 | NM_001242954.1 | chrX:10876382-10876883 |
| 11861 | Gm14477 | NM_001242949.1 | chrX:10901784-10902102 |
| 11862 | Gm14477 | NM_001242949.1 | chrX:10892214-10892723 |
| 11863 | Gm14478 | NM_001242953.1 | chrX:10895381-10895890 |
| 11864 | Gm14478 | NM_001242953.1 | chrX:10898548-10899057 |
| 11865 | Gm14479 | NM_001242951.1 | chrX:10885880-10886389 |
| 11866 | Gm14479 | NM_001242951.1 | chrX:10898548-10899057 |
| 11867 | Gm14482 | NM_001242952.1 | chrX:10885880-10886389 |
| 11868 | Gm14482 | NM_001242952.1 | chrX:10892214-10892723 |
| 11869 | Gm14482 | NM_001242952.1 | chrX:10895381-10895890 |
| 11870 | Gm14482 | NM_001242952.1 | chrX:10898548-10899057 |
| 11871 | Gm14483 | NM_001111037.1 | chrX:10876382-10876883 |
| 11872 | Gm14483 | NM_001111037.1 | chrX:10885880-10886389 |
| 11873 | Gm14484 | NM_001025260.2 | chrX:10889059-10889553 |
| 11874 | Gm14496 | NM_001205282.1 | chr2:181725930-181735792 |
| 11875 | Gm14499 | NM_001277184.1 | chrX:8620676-8621536 |
| 11876 | Gm14499 | NM_001277184.1 | chrX:8552843-8553715 |
| 11877 | Gm14501 | NM_001085537.2 | chrX:8927724-8928263 |
| 11878 | Gm14511 | NM_001085525.2 | chrX:8552844-8553685 |
| 11879 | Gm14525 | NM_001162364.2 | chrX:26099906-26129764 |
| 11880 | Gm14548 | NM_001166672.1 | chr7:3835814-3849694 |
| 11881 | Gm14625 | NM_001204498.1 | chrX:52683411-52700069 |
| 11882 | Gm14632 | NM_001100610.2 | chrX:24475577-24498514 |
| 11883 | Gm14632 | NM_001100610.2 | chrX:29130521-29154420 |
| 11884 | Gm14632 | NM_001100610.2 | chrX:29483950-29506884 |
| 11885 | Gm14632 | NM_001100610.2 | chrX:27889230-27912141 |
| 11886 | Gm14634 | NR_045852.1 | chrX:12339403-12398618 |
| 11887 | Gm14635 | NR_045321.1 | chrX:11916904-11932122 |
| 11888 | Gm14685 | NM_001025383.2 | chrX:70352973-70374599 |
| 11889 | Gm14685 | NM_001025383.2 | chrX:70382570-70403738 |
| 11890 | Gm14692 | NM_001163195.1 | chrX:64936074-64946737 |
| 11891 | Gm14692 | NM_001163195.1 | chrX:64948872-64959525 |
| 11892 | Gm14718 | NR_038463.1 | chrX:54453813-54457553 |
| 11893 | Gm14725 | NM_001081476.1 | chrX:67798732-67799560 |
| 11894 | Gm14743 | NM_001126321.2 | chrX:75485800-75491260 |
| 11895 | Gm14744 | NM_001085544.1 | chrX:75110096-75115372 |
| 11896 | Gm14812 | NM_001205268.1 | chrX:88877532-88881010 |
| 11897 | Gm14812 | NR_033544.2 | chrX:96600669-96639136 |
| 11898 | Gm14819 | NM_001110250.2 | chrX:28236042-28258941 |
| 11899 | Gm14819 | NM_001110250.2 | chrX:27228255-27251155 |
| 11900 | Gm14819 | NM_001110250.2 | chrX:32944181-32967088 |
| 11901 | Gm14819 | NM_001110250.2 | chrX:29924763-29947708 |
| 11902 | Gm14819 | NM_001110250.2 | chrX:32607378-32630311 |
| 11903 | Gm14827 | NR_045323.1 | chrX:91688070-91693066 |
| 11904 | Gm14850 | NM_001177522.1 | chr8:22675858-22676822 |
| 11905 | Gm14857 | NM_001177482.1 | chr8:22234649-22235729 |
| 11906 | Gm14858 | NR_040285.1 | chr5:99447989-99453028 |
| 11907 | Gm14920 | NM_001102665.1 | chrX:114128365-114128713 |
| 11908 | Gm14920 | NR_045917.1 | chrX:34450829-34451980 |
| 11909 | Gm15023 | NM_001099321.2 | chr1:131702162-131712171 |
| 11910 | Gm15023 | NM_001099321.2 | chr1:132029126-132039133 |
| 11911 | Gm15055 | NR_110440.1 | chr6:52052947-52063683 |
| 11912 | Gm15056 | NM_001177471.1 | chr8:22040296-22041664 |
| 11913 | Gm15056 | NM_001177471.1 | chr8_random:307381-308749 |
| 11914 | Gm15085 | NM_001122734.1 | chrX:144615266-144955989 |
| 11915 | Gm15085 | NM_001122734.1 | chrX:145522857-145739546 |
| 11916 | Gm15085 | NM_001122734.1 | chrX:144427535-144467717 |
| 11917 | Gm15085 | NM_001122734.1 | chrX:144615266-144955989 |
| 11918 | Gm15085 | NM_001122734.1 | chrX:145882159-145922327 |
| 11919 | Gm15091 | NM_001122735.1 | chrX:146376198-146419525 |
| 11920 | Gm15093 | NM_001099920.1 | chrX_random:395346-427969 |
| 11921 | Gm15093 | NM_001099920.1 | chrX:144615266-144955989 |
| 11922 | Gm15093 | NM_001099920.1 | chrX:145522857-145739546 |
| 11923 | Gm15093 | NM_001099920.1 | chrX_random:562213-602417 |
| 11924 | Gm15093 | NM_001099920.1 | chrX:144427535-144467717 |
| 11925 | Gm15093 | NM_001099920.1 | chrX:145882159-145922327 |
| 11926 | Gm15093 | NM_001099920.1 | chrX:145522857-145739546 |
| 11927 | Gm15097 | NM_001198987.2 | chrX:146219047-146261237 |
| 11928 | Gm15104 | NM_001101501.1 | chrX:146747493-146747907 |
| 11929 | Gm15107 | NM_001081648.1 | chrX:144615267-144669253 |
| 11930 | Gm15114 | NM_001082966.1 | chrX:144923492-144955989 |
| 11931 | Gm15127 | NM_001114400.2 | chrX:145098146-145138392 |
| 11932 | Gm15127 | NM_001114400.2 | chrX:146219021-146419525 |
| 11933 | Gm15133 | NR_040749.1 | chr7:111463545-111473352 |
| 11934 | Gm15179 | NR_037976.1 | chr1:75364785-75371590 |
| 11935 | Gm15217 | NR_037981.1 | chr14:46999199-47003281 |
| 11936 | Gm1527 | NM_001033479.4 | chr3:28791538-28825646 |
| 11937 | Gm15284 | NM_001177485.1 | chr8:22274328-22275277 |
| 11938 | Gm15292 | NM_001177487.1 | chr8:22389440-22390140 |
| 11939 | Gm15293 | NM_001177486.1 | chr8:22341282-22342125 |
| 11940 | Gm15299 | NM_001170955.1 | chr8:22455224-22456066 |
| 11941 | Gm15315 | NM_001177528.1 | chr8:22776269-22777205 |
| 11942 | Gm15319 | NM_001177408.1 | chr8:19933241-19958780 |
| 11943 | Gm15328 | NR_045399.1 | chr18:16974915-16981292 |
| 11944 | Gm15348 | NR_033546.1 | chr8:12706943-12719127 |
| 11945 | Gm15350 | NR_045775.1 | chr8:12828338-12831919 |
| 11946 | Gm15386 | NM_001040027.2 | chr18:18250605-18255219 |
| 11947 | Gm15401 | NR_040421.1 | chr6:72576364-72739039 |
| 11948 | Gm15401 | NR_040422.1 | chr6:72576364-72739039 |
| 11949 | Gm15408 | NR_040429.1 | chr2:149818537-149824352 |
| 11950 | Gm15412 | NR_046043.1 | chr7:103487993-103490474 |
| 11951 | Gm15413 | NR_045874.1 | chr7:103939943-103950059 |
| 11952 | Gm15417 | NR_040403.1 | chr3:89181567-89202701 |

Fig. 25 - 64

| | | | | | | | | |
|---|---|---|---|---|---|---|---|---|
| 11953 | Gm15417 | NR_040404.1 | chr3:89181567-89202701 | | 12045 | Gm16712 | NR_108021.1 | chr17:56094194-56098824 |
| 11954 | Gm15421 | NR_004442.1 | chr5:22034039-22034848 | | 12046 | Gm1673 | NM_001033458.1 | chr5:34326122-34327655 |
| 11955 | Gm15441 | NR_040409.1 | chr3:96359691-96370724 | | 12047 | Gm16740 | NR_108026.1 | chr3:95021379-95030580 |
| 11956 | Gm15446 | NR_040366.1 | chr5:110362581-110370729 | | 12048 | Gm16793 | NR_040376.1 | chr8:36645557-36652074 |
| 11957 | Gm15455 | NM_001161816.1 | chr1:33892743-33895759 | | 12049 | Gm16796 | NR_040367.1 | chr2:170324857-170337427 |
| 11958 | Gm15471 | NR_040412.1 | chr3:103607052-103612363 | | 12050 | Gm16833 | NR_045754.1 | chr9:9236288-9260885 |
| 11959 | Gm1553 | NM_001255990.1 | chr10:81949277-81955363 | | 12051 | Gm16845 | NR_040406.1 | chr9:21859903-21890575 |
| 11960 | Gm15545 | NR_045266.1 | chr7:52242270-52248971 | | 12052 | Gm16845 | NR_040407.1 | chr9:21859903-21890575 |
| 11961 | Gm156 | NM_001014997.1 | chr6:129716664-129725867 | | 12053 | Gm16853 | NR_045742.1 | chr9:21209686-21216164 |
| 11962 | Gm15612 | NR_045880.1 | chr6:88792848-88797268 | | 12054 | Gm16861 | NR_037666.1 | chr16:4935164-4939585 |
| 11963 | Gm1564 | NM_001127576.2 | chr11:102526898-102543552 | | 12055 | Gm16863 | NR_046162.1 | chr16:21247572-21296945 |
| 11964 | Gm15645 | NR_033578.1 | chr7:113010294-113011841 | | 12056 | Gm16880 | NR_037986.1 | chr1:138592787-138622305 |
| 11965 | Gm15663 | NR_038032.1 | chr10:105011606-105020926 | | 12057 | Gm16894 | NR_037980.1 | chr1:40133057-40142696 |
| 11966 | Gm15679 | NR_110579.1 | chr8:101535787-101556641 | | 12058 | Gm16897 | NR_033564.1 | chr1:196781953-196803153 |
| 11967 | Gm15698 | NR_003564.1 | chr11:88825980-88828231 | | 12059 | Gm16907 | NR_045794.1 | chr13:63390462-63398455 |
| 11968 | Gm15706 | NR_045598.1 | chr6:145199071-145200376 | | 12060 | Gm16938 | NR_045969.1 | chr7:105270074-105333309 |
| 11969 | Gm15708 | NR_040432.1 | chr5:145037930-145041383 | | 12061 | Gm16938 | NR_045970.1 | chr7:105270074-105333309 |
| 11970 | Gm15713 | NR_046026.1 | chr16:43410631-43420309 | | 12062 | Gm16938 | NR_045971.1 | chr7:105270074-105333309 |
| 11971 | Gm15760 | NR_030670.1 | chr16.20545184-20548629 | | 12063 | Gm16938 | NR_045972.1 | chr7:105270074-105333309 |
| 11972 | Gm15772 | NR_003373.1 | chr11:68715091-68718036 | | 12064 | Gm16973 | NR_046209.1 | chr14:57287084-57319837 |
| 11973 | Gm15787 | NR_040430.1 | chr5:110564848-110605523 | | 12065 | Gm16973 | NR_046210.1 | chr14:57287084-57319837 |
| 11974 | Gm15787 | NR_040431.1 | chr5:110564848-110605523 | | 12066 | Gm16982 | NR_040337.1 | chr7:148795965-148799646 |
| 11975 | Gm15800 | NM_181421.4 | chr5:121670227-121818586 | | 12067 | Gm16998 | NR_038016.1 | chr10:53795727-53800887 |
| 11976 | Gm15816 | NM_001282148.1 | chr8:24249257-24260057 | | 12068 | Gm17019 | NM_182957.1 | chr5:15028949-15033007 |
| 11977 | Gm15850 | NR_046167.1 | chr1:138024295-138027760 | | 12069 | Gm17066 | NR_040628.1 | chr14:105505945-105513893 |
| 11978 | Gm15850 | NR_046168.1 | chr1:138024295-138027760 | | 12070 | Gm1715 | NR_045333.1 | chr9:52487967-52606877 |
| 11979 | Gm15850 | NR_046169.1 | chr1:138024295-138027760 | | 12071 | Gm1720 | NR_046015.1 | chrX:163099956-163127744 |
| 11980 | Gm15850 | NR_046170.1 | chr1:138024295-138027760 | | 12072 | Gm17252 | NM_001199953.1 | chr9:35492663-35494956 |
| 11981 | Gm1587 | NM_001033446.2 | chr14:78193751-78198775 | | 12073 | Gm17296 | NM_001159907.1 | chr8:128950551-128998965 |
| 11982 | Gm15880 | NR_040343.1 | chr7:87780903-87789270 | | 12074 | Gm17359 | NM_001142953.1 | chr3:79149298-79268050 |
| 11983 | Gm15881 | NM_001177534.2 | chr8:61177646-61179593 | | 12075 | Gm17365 | NM_001167592.2 | chr9:35452697-35455787 |
| 11984 | Gm15910 | NR_038023.1 | chr10:120294685-120300384 | | 12076 | Gm17455 | NM_001164374.1 | chr10:59862474-59866306 |
| 11985 | Gm15915 | NR_038017.1 | chr10:93136963-93146067 | | 12077 | Gm17644 | NR_045297.1 | chr1:12657643-12663171 |
| 11986 | Gm15941 | NR_045283.1 | chr15:37350888-37362419 | | 12078 | Gm17660 | NM_001163772.1 | chr5:104499079-104506627 |
| 11987 | Gm15987 | NR_045009.2 | chr6:128902371-128925047 | | 12079 | Gm17677 | NM_001167588.1 | chr9:35548633-35549837 |
| 11988 | Gm15997 | NR_045423.1 | chr5:150291631-150340605 | | 12080 | Gm17689 | NM_001167584.1 | chr9:36388862-36390220 |
| 11989 | Gm16023 | NR_040441.1 | chr5:154982406-154998864 | | 12081 | Gm17727 | NM_001167673.1 | chr9:35584108-35585694 |
| 11990 | Gm16039 | NR_033518.1 | chr6:8209287-8378765 | | 12082 | Gm17745 | NR_038014.1 | chr10:92798976-92811624 |
| 11991 | Gm16046 | NM_001033442.3 | chr17:7229891-7291946 | | 12083 | Gm17745 | NR_045844.1 | chr12:25814038-25817139 |
| 11992 | Gm16046 | NM_001033442.3 | chr17:8231374-8294093 | | 12084 | Gm17751 | NR_038012.1 | chr1:76485707-76498603 |
| 11993 | Gm16062 | NR_045686.1 | chr11:59623582-59631864 | | 12085 | Gm17751 | NR_038013.1 | chr1:76485707-76498603 |
| 11994 | Gm16063 | NR_046178.1 | chr5:120075950-120084471 | | 12086 | Gm17757 | NR_040453.1 | chr7:113043632-113102484 |
| 11995 | Gm16130 | NM_001243265.1 | chr9:57880081-57896804 | | 12087 | Gm17757 | NR_040453.1 | chr7:113300049-113358854 |
| 11996 | Gm16157 | NR_040340.1 | chr7:75411224-75507976 | | 12088 | Gm17762 | NR_028378.1 | chr2:17948876-17952204 |
| 11997 | Gm16157 | NR_040343.1 | chr7:75411224-75507976 | | 12089 | Gm17765 | NR_027377.1 | chr10:76881120-76883684 |
| 11998 | Gm16287 | NR_033543.1 | chr4:138731321-138736570 | | 12090 | Gm17801 | NR_027452.1 | chr17:25411069-25412473 |
| 11999 | Gm16291 | NR_045788.1 | chr15:39628591-39643923 | | 12091 | Gm17821 | NR_033146.1 | chr12:68757728-68770258 |
| 12000 | Gm16294 | NR_046185.1 | chr15:40342867-40358823 | | 12092 | Gm17830 | NR_033486.1 | chr17:49443803-49452285 |
| 12001 | Gm1631 | NR_037979.1 | chr2:71557473-71569023 | | 12093 | Gm1821 | NR_002875.2 | chr14:46703701-46704632 |
| 12002 | Gm16325 | NR_045949.1 | chr3:146304896-146314679 | | 12094 | Gm18409 | NR_038018.1 | chr10:99101365-99104554 |
| 12003 | Gm16336 | NR_045267.1 | chr7:118048499-118049365 | | 12095 | Gm18853 | NR_040456.1 | chr7:113043632-113102484 |
| 12004 | Gm16367 | NM_001031622.2 | chr5_random:340702-352536 | | 12096 | Gm18853 | NR_040456.1 | chr7:113300049-113358854 |
| 12005 | Gm16367 | NM_001031622.2 | chr5_random:122203-134052 | | 12097 | Gm19276 | NR_040357.1 | chr15:10758805-10762468 |
| 12006 | Gm16367 | NM_001031622.2 | chrUn_random:870738-88257 2 | | 12098 | Gm19277 | NR_040360.1 | chr15:84979683-84986562 |
| 12007 | Gm16367 | NM_001031622.2 | chrUn_random:838715-85142 9 | | 12099 | Gm19299 | NR_045748.1 | chr9:66981367-67011595 |
| 12008 | Gm16367 | NM_001031622.2 | chr5_random:308680-321393 | | 12100 | Gm19303 | NR_045092.1 | chr15:51063185-51227356 |
| 12009 | Gm16367 | NM_001031622.2 | chrUn_random:1383589-139 6311 | | 12101 | Gm19395 | NM_001270489.1 | chr7:20437352-20443704 |
| 12010 | Gm16367 | NM_001031622.2 | chrUn_random:2204168-221 6886 | | 12102 | Gm19395 | NR_038015.1 | chr10:53000076-53003493 |
| 12011 | Gm16367 | NM_001031622.2 | chr5:95294540-95307276 | | 12103 | Gm19402 | NM_001205032.1 | chr10:77152702-77153502 |
| 12012 | Gm16367 | NM_001031622.2 | chr5:95611642-95624361 | | 12104 | Gm19424 | NR_040320.1 | chr19:41821450-41824587 |
| 12013 | Gm16381 | NM_001166062.2 | chr12:89080291-89085164 | | 12105 | Gm1943 | NR_002928.2 | chr8:111863699-111864808 |
| 12014 | Gm16381 | NM_001166062.2 | chr12:88985074-88989933 | | 12106 | Gm19434 | NR_040296.1 | chr6:135138497-135144977 |
| 12015 | Gm16386 | NR_030709.2 | chr17:22913196-22954714 | | 12107 | Gm19461 | NR_037984.1 | chr1:135146429-135166385 |
| 12016 | Gm16390 | NM_001097980.1 | chrX:151321345-151324810 | | 12108 | Gm19466 | NR_040349.1 | chr18:53807805-53865072 |
| 12017 | Gm16404 | NM_001220497.1 | chrX:52804772-52821634 | | 12109 | Gm19510 | NR_045076.1 | chr15:59619971-59626514 |
| 12018 | Gm16430 | NM_001166601.1 | chrX:51925387-51942193 | | 12110 | Gm19522 | NR_040402.1 | chr16:42884483-42912183 |
| 12019 | Gm16430 | NM_001166601.1 | chrX:51834384-51851190 | | 12111 | Gm19557 | NR_045322.1 | chr19:47587472-47591068 |
| 12020 | Gm16432 | NM_001034899.3 | chr1:179921565-179978422 | | 12112 | Gm19583 | NR_045792.1 | chr5:75506345-75543132 |
| 12021 | Gm16445 | NM_001243032.1 | chrX:150587113-150591430 | | 12113 | Gm19589 | NR_037971.1 | chr1:90448091-90458741 |
| 12022 | Gm16451 | NM_001167149.1 | chr7:22902340-22903264 | | 12114 | Gm19619 | NR_040428.1 | chr5:91686596-91712102 |
| 12023 | Gm16451 | NM_001167149.1 | chr7:20707004-20707928 | | 12115 | Gm1965 | NM_001033491.2 | chr6:89090998-89096010 |
| 12024 | Gm1647 | NM_001243000.1 | chr3:68935154-68961099 | | 12116 | Gm1966 | NM_001277179.1 | chr7:113739062-113788159 |
| 12025 | Gm16497 | NR_045003.1 | chr12:14268339-14292490 | | 12117 | Gm1966 | NM_001277180.1 | chr7:113739062-113788159 |
| 12026 | Gm16501 | NM_001113395.1 | chrY:1976248-1976584 | | 12118 | Gm1966 | NM_001277181.1 | chr7:113739062-113788159 |
| 12027 | Gm16515 | NM_025294.5 | chr11:60715747-60727294 | | 12119 | Gm1966 | NM_001277182.1 | chr7:113739062-113788159 |
| 12028 | Gm16523 | NR_033526.1 | chr2:39013006-39017755 | | 12120 | Gm1966 | NM_001277183.1 | chr7:113739062-113788159 |
| 12029 | Gm1653 | NR_040591.3 | chr3:148937700-148942944 | | 12121 | Gm19668 | NM_001205034.1 | chr10:77261332-77261878 |
| 12030 | Gm16532 | NM_001134752.1 | chr7:6367885-6383797 | | 12122 | Gm1968 | NR_037689.1 | chr16:29958012-29979210 |
| 12031 | Gm16548 | NR_037987.1 | chr1:166078707-166082348 | | 12123 | Gm19705 | NR_045094.1 | chr17:83432931-83477565 |
| 12032 | Gm16551 | NR_045284.1 | chr9:74696243-74700679 | | 12124 | Gm19705 | NR_045324.1 | chr1:138579972-138587382 |
| 12033 | Gm16576 | NR_045069.1 | chr15:79573127-79587824 | | 12125 | Gm19705 | NR_045325.1 | chr1:138579972-138587382 |
| 12034 | Gm16596 | NR_045751.1 | chr12:109609362-109940516 | | 12126 | Gm19710 | NR_045749.1 | chr3:89802682-89805247 |
| 12035 | Gm16596 | NR_045752.1 | chr12:109609362-109940516 | | 12127 | Gm19757 | NR_040297.1 | chr6:105431259-105442662 |
| 12036 | Gm16596 | NR_045753.1 | chr12:109609362-109940516 | | 12128 | Gm1976 | NR_045963.1 | chr17:95149439-95234160 |
| 12037 | Gm166 | NM_001033040.3 | chr7:134725897-134732109 | | 12129 | Gm1976 | NR_045964.1 | chr17:95149439-95234160 |
| 12038 | Gm1661 | NM_001033774.2 | chr4:116885937-116924522 | | 12130 | Gm19782 | NR_045071.1 | chr15:69754662-69908634 |
| 12039 | Gm1661 | NM_001145637.1 | chr4:116885937-116924522 | | 12131 | Gm19784 | NR_040461.1 | chr18:67084415-67109615 |
| 12040 | Gm16617 | NR_045728.1 | chr14:52606064-52608504 | | 12132 | Gm1979 | NM_001281519.1 | chr5:26326711-26331267 |
| 12041 | Gm16675 | NR_045750.1 | chr8:47816323-47824869 | | 12133 | Gm1987 | NM_001193667.1 | chr4:42231042-42232176 |
| 12042 | Gm16677 | NR_045091.1 | chr14:69947763-69955194 | | 12134 | Gm1987 | NM_001193667.1 | chr4:42786391-42787525 |
| 12043 | Gm16701 | NR_037988.1 | chr1:168649153-168929861 | | 12135 | Gm19897 | NR_040339.1 | chr7:29559918-29566533 |
| 12044 | Gm16702 | NR_045795.1 | chr17:8571910-8582333 | | 12136 | Gm1993 | NM_001102677.2 | chrX_random:1375835-13977 84 |
| | | | | | 12137 | Gm1993 | NM_001102677.2 | chrX:24975626-24997575 |
| | | | | | 12138 | Gm1995 | NR_033562.1 | chr12:89099797-89104138 |

Fig. 25 - 65

| | | | |
|---|---|---|---|
| 12139 | Gm19990 | NR_045048.1 | chr12:57354229-57367368 |
| 12140 | Gm2002 | NM_001100596.1 | chr4:42664135-42679295 |
| 12141 | Gm2002 | NM_001100596.1 | chr4:42339258-42354418 |
| 12142 | Gm2002 | NM_001100596.1 | chr4:41763293-42104673 |
| 12143 | Gm20063 | NR_045049.1 | chr12:62600646-62622807 |
| 12144 | Gm20098 | NR_045095.1 | chr17:52022051-52104582 |
| 12145 | Gm2011 | NR_038067.1 | chr3:40650921-40679931 |
| 12146 | Gm20110 | NR_038019.1 | chr10:99071805-99120768 |
| 12147 | Gm2012 | NM_001104946.2 | chrX:25628009-26362795 |
| 12148 | Gm20125 | NR_038020.1 | chr10:16670899-16815588 |
| 12149 | Gm20139 | NR_038021.1 | chr10:18861554-18927753 |
| 12150 | Gm20139 | NR_038022.1 | chr10:18861554-18927753 |
| 12151 | Gm2016 | NM_001122662.1 | chr12:89112519-89116307 |
| 12152 | Gm20172 | NM_001204913.1 | chr1:25333249-25334799 |
| 12153 | Gm20187 | NR_045052.1 | chr12:27775101-27799860 |
| 12154 | Gm20199 | NR_045640.1 | chr9:59325552-59329548 |
| 12155 | Gm2022 | NM_001177574.1 | chr12:89133277-89135166 |
| 12156 | Gm20257 | NR_045007.1 | chr1:58709484-58712675 |
| 12157 | Gm20268 | NR_037989.1 | chr1:103052344-103071779 |
| 12158 | Gm2027 | NR_045113.1 | chr12:45322342-45325367 |
| 12159 | Gm2030 | NM_001100445.2 | chrX:25714325-25737170 |
| 12160 | Gm20300 | NR_045008.1 | chr10:30323000-30326440 |
| 12161 | Gm20319 | NR_105063.1 | chr16:26714768-26755588 |
| 12162 | Gm20324 | NR_045068.1 | chr15:82729510-82736246 |
| 12163 | Gm20337 | NR_045057.1 | chr12:82043638-82046386 |
| 12164 | Gm20356 | NR_040450.1 | chr3:73813140-73821199 |
| 12165 | Gm20362 | NR_040301.1 | chr6:78982035-78985863 |
| 12166 | Gm20362 | NR_040302.1 | chr6:78982035-78985863 |
| 12167 | Gm2042 | NM_001270792.1 | chr12:89192923-89199126 |
| 12168 | Gm2042 | NM_001270793.1 | chr12:89192923-89199126 |
| 12169 | Gm20554 | NR_030701.1 | chr13:72760913-72766012 |
| 12170 | Gm20556 | NR_040347.1 | chr15:84545059-84550696 |
| 12171 | Gm20594 | NM_001190732.1 | chr6:79768024-79768358 |
| 12172 | Gm20597 | NR_037973.1 | chr10:53218248-53238795 |
| 12173 | Gm20604 | NM_001142939.1 | chr12:103978040-103996020 |
| 12174 | Gm20605 | NR_033148.1 | chr5:138070351-138084124 |
| 12175 | Gm2061 | NR_040305.1 | chr1:187270995-187279447 |
| 12176 | Gm20611 | NR_040638.1 | chr10:60494050-60500828 |
| 12177 | Gm20735 | NR_015497.2 | chr8:124956168-124975222 |
| 12178 | Gm20736 | NM_001037748.1 | chrY_random:3373245-3399402 |
| 12179 | Gm20736 | NM_001037748.1 | chrY_random:13907848-13934075 |
| 12180 | Gm20736 | NM_001037748.1 | chrY_random:52063164-52089373 |
| 12181 | Gm20736 | NM_001037748.1 | chrY_random:20391963-20418154 |
| 12182 | Gm20736 | NM_001037748.1 | chrY_random:28642180-28668330 |
| 12183 | Gm20736 | NM_001037748.1 | chrY_random:37572379-37598536 |
| 12184 | Gm20736 | NM_001037748.1 | chrY_random:15940900-15967135 |
| 12185 | Gm20736 | NM_001037748.1 | chrY_random:46209687-46235866 |
| 12186 | Gm20736 | NM_001037748.1 | chrY_random:50987249-51013472 |
| 12187 | Gm20738 | NM_207162.2 | chrY_random:15824126-15826459 |
| 12188 | Gm20738 | NM_207162.2 | chrY_random:29870815-29873147 |
| 12189 | Gm20738 | NM_207162.2 | chrY_random:50814753-50817087 |
| 12190 | Gm20740 | NR_045279.1 | chr15:63245951-63311163 |
| 12191 | Gm20741 | NR_045150.1 | chr16:88811684-88812465 |
| 12192 | Gm20743 | NR_040303.1 | chr1:166793251-166801569 |
| 12193 | Gm20744 | NR_045744.1 | chr7:89215272-89226644 |
| 12194 | Gm20745 | NR_045745.1 | chr9:67865770-67873521 |
| 12195 | Gm20747 | NM_001025241.3 | chrY_random:52515005-52517353 |
| 12196 | Gm20747 | NM_001025241.3 | chrY_random:4246222-4248568 |
| 12197 | Gm20747 | NM_001025241.3 | chrY_random:48319177-48321522 |
| 12198 | Gm20748 | NR_045420.2 | chr18:61,799,307-61,807,139 |
| 12199 | Gm20750 | NR_040555.1 | chr3:52710677-52731588 |
| 12200 | Gm20751 | NR_046022.1 | chr13:43812159-43814407 |
| 12201 | Gm20752 | NR_040750.1 | chr3:158739327-158971044 |
| 12202 | Gm20753 | NR_040630.1 | chr1:108049201-108068101 |
| 12203 | Gm20754 | NR_040557.1 | chr3:72790273-73398752 |
| 12204 | Gm20755 | NR_040559.1 | chr3:37797734-37891650 |
| 12205 | Gm20756 | NR_040771.1 | chr6:25881425-25927227 |
| 12206 | Gm20757 | NR_046027.1 | chr10:91634045-91838118 |
| 12207 | Gm20758 | NR_046029.1 | chr10:111291576-111311432 |
| 12208 | Gm20759 | NR_046030.1 | chr11:85816159-85837852 |
| 12209 | Gm20765 | NM_001270644.1 | chr10:103605568-103625055 |
| 12210 | Gm20765 | NM_001270644.1 | chr10:103631096-103633576 |
| 12211 | Gm20806 | NM_001160135.2 | chrY_random:32818620-32813619 |
| 12212 | Gm20806 | NM_001160135.2 | chrY_random:53819454-53820453 |
| 12213 | Gm20809 | NM_001160137.1 | chrY_random:43342347-43343335 |
| 12214 | Gm20809 | NM_001160137.1 | chrY_random:45614366-45615358 |
| 12215 | Gm20809 | NM_001160137.1 | chrY_random:52881631-52882623 |
| 12216 | Gm20809 | NM_001160137.1 | chrY_random:58501954-58502946 |
| 12217 | Gm20809 | NM_001160137.1 | chrY_random:14172529-14173524 |
| 12218 | Gm20809 | NM_001160137.1 | chrY_random:27290996-27291988 |
| 12219 | Gm20809 | NM_001160137.1 | chrY_random:36699243-36700235 |
| 12220 | Gm20815 | NM_001017394.2 | chrY_random:54420148-54423069 |
| 12221 | Gm20816 | NM_001160144.1 | chrY_random:3559697-3562029 |
| 12222 | Gm20816 | NM_001160144.1 | chrY_random:4951014-4953345 |
| 12223 | Gm20816 | NM_001160144.1 | chrY_random:39019757-39022085 |
| 12224 | Gm20822 | NM_001199331.1 | chrY_random:7875234-7875921 |
| 12225 | Gm20822 | NM_001199331.1 | chrY_random:6428618-6429305 |
| 12226 | Gm20823 | NM_001160143.1 | chrY_random:13735461-13737796 |
| 12227 | Gm20823 | NM_001160143.1 | chrY_random:23673854-23676187 |
| 12228 | Gm20823 | NM_001160143.1 | chrY_random:15824126-15826459 |
| 12229 | Gm20823 | NM_001160143.1 | chrY_random:29870815-29873147 |
| 12230 | Gm20823 | NM_001160143.1 | chrY_random:50814753-50817087 |
| 12231 | Gm20826 | NM_001101623.1 | chrY_random:16925232-16925990 |
| 12232 | Gm2083 | NM_001134644.1 | chr4:60591133-60675237 |
| 12233 | Gm20831 | NM_001103152.1 | chrY_random:9452829-9455268 |
| 12234 | Gm20854 | NM_001160131.1 | chrY_random:18518132-18520125 |
| 12235 | Gm20857 | NR_038297.1 | chrY_random:29419582-29445584 |
| 12236 | Gm20857 | NR_038297.1 | chrY_random:37863737-37889770 |
| 12237 | Gm20857 | NR_038297.1 | chrY_random:38065066-38091071 |
| 12238 | Gm20865 | NM_001160141.1 | chrY_random:19988052-19988910 |
| 12239 | Gm20865 | NM_001160141.1 | chrY_random:48242250-48243108 |
| 12240 | Gm20865 | NM_001160141.1 | chrY_random:52590932-52591790 |
| 12241 | Gm20867 | NM_001160142.1 | chrY_random:2860158-2862495 |
| 12242 | Gm20867 | NM_001160142.1 | chrY_random:44066622-44068949 |
| 12243 | Gm20867 | NM_001160142.1 | chrY_random:3559697-3562029 |
| 12244 | Gm20867 | NM_001160142.1 | chrY_random:4951014-4953345 |
| 12245 | Gm20867 | NM_001160142.1 | chrY_random:39019757-39022085 |
| 12246 | Gm2087 | NR_102437.1 | chr9:83325154-83348181 |
| 12247 | Gm20871 | NR_038299.1 | chrY_random:25657822-25982665 |
| 12248 | Gm20871 | NR_038299.1 | chrY_random:40360135-40386184 |
| 12249 | Gm20877 | NM_001199332.1 | chrY_random:41874313-41876322 |
| 12250 | Gm20877 | NM_001199332.1 | chrY_random:8781434-8783443 |
| 12251 | Gm20878 | NM_001270431.1 | chr4:41763293-42104673 |
| 12252 | Gm20878 | NM_001270431.1 | chrUn_random:701089-702124 |
| 12253 | Gm20917 | NM_001160136.1 | chrY_random:28838095-28839087 |
| 12254 | Gm21002 | NM_001270555.1 | chr8:22639501-22640484 |
| 12255 | Gm21057 | NR_045695.1 | chr7:87207596-87220143 |
| 12256 | Gm2109 | NR_046066.1 | chr9:83585081-83586854 |
| 12257 | Gm21119 | NM_001270553.1 | chr8_random:689551-717784 |
| 12258 | Gm21119 | NM_001270553.1 | chr8:19729575-19753602 |
| 12259 | Gm2115 | NR_045098.1 | chr7:91677463-91726849 |
| 12260 | Gm21221 | NR_077242.1 | chr1:150604564-150614326 |
| 12261 | Gm21221 | NR_102737.1 | chr7:80970809-80981435 |
| 12262 | Gm21276 | NR_073038.1 | chr7:46511993-46519904 |
| 12263 | Gm21283 | NR_105058.1 | chr8:113019266-113026256 |
| 12264 | Gm21284 | NR_078345.1 | chr6:83518033-83538120 |
| 12265 | Gm21293 | NM_001270898.1 | chr10:103631096-103633576 |
| 12266 | Gm21293 | NM_001270898.1 | chr10:103605568-103625055 |
| 12267 | Gm21304 | NM_001270901.1 | chr10:103631096-103633547 |
| 12268 | Gm21312 | NM_001270642.1 | chr10:103605568-103625055 |
| 12269 | Gm21312 | NM_001270642.1 | chr10:103605568-103625055 |
| 12270 | Gm21319 | NM_001270722.1 | chr12:89320165-89569046 |
| 12271 | Gm21498 | NM_001270613.1 | chr8:22675858-22676816 |
| 12272 | Gm21637 | NM_001270685.1 | chrX:3546313-3547091 |
| 12273 | Gm21637 | NM_001270685.1 | chrX:30823249-30824027 |
| 12274 | Gm21637 | NM_001270685.1 | chrX:31428919-31429697 |
| 12275 | Gm21671 | NM_001281516.1 | chr5:26344961-26431831 |
| 12276 | Gm21704 | NM_001270515.1 | chrY:2156898-2168120 |
| 12277 | Gm21704 | NM_001270515.1 | chrY:2188491-2398856 |
| 12278 | Gm2176 | NR_028424.1 | chr18:80738630-80741285 |
| 12279 | Gm21943 | NM_001017393.3 | chrY_random:27836148-27838458 |
| 12280 | Gm21943 | NM_001017393.3 | chrY_random:46075784-46078095 |
| 12281 | Gm21944 | NR_002880.1 | chr8_random:320241-332856 |
| 12282 | Gm21949 | NM_001113419.2 | chr8:67696142-68430404 |
| 12283 | Gm21950 | NM_001270667.1 | chrX:32129796-32131700 |
| 12284 | Gm21950 | NM_001270667.1 | chrX:3241669-3243629 |
| 12285 | Gm21950 | NM_001270667.1 | chrX:3461360-3463320 |
| 12286 | Gm21950 | NM_001270667.1 | chrX:3907010-3908970 |
| 12287 | Gm21950 | NM_001270667.1 | chrX:30291071-30293031 |
| 12288 | Gm21950 | NM_001270667.1 | chrX:30732633-30734588 |
| 12289 | Gm21950 | NM_001270667.1 | chrX:30977792-30979742 |
| 12290 | Gm21951 | NM_001270669.1 | chrX:3461360-3463320 |
| 12291 | Gm21951 | NM_001270669.1 | chrX:30977792-30979742 |

Fig. 25 - 66

| | | | |
|---|---|---|---|
| 12292 | Gm21951 | NM_001270669.1 | chrX:3241669-3243629 |
| 12293 | Gm21951 | NM_001270669.1 | chrX:3907010-3908970 |
| 12294 | Gm21951 | NM_001270669.1 | chrX:30291871-30293031 |
| 12295 | Gm21951 | NM_001270669.1 | chrX:30732633-30734588 |
| 12296 | Gm2373 | NR_110430.1 | chr13:98204924-98267619 |
| 12297 | Gm2373 | NR_110431.1 | chr13:98204924-98267619 |
| 12298 | Gm2373 | NR_110432.1 | chr13:98204924-98267619 |
| 12299 | Gm2381 | NR_046214.1 | chr7:50072196-50122604 |
| 12300 | Gm2382 | NM_001128601.1 | chr9:88583442-88614636 |
| 12301 | Gm2447 | NR_038079.1 | chr3:52543645-52580576 |
| 12302 | Gm2516 | NR_046067.1 | chr8:51453465-51501443 |
| 12303 | Gm2518 | NR_015538.1 | chr19:8848975-8851452 |
| 12304 | Gm266 | NM_001033248.3 | chr12:112722819-112724034 |
| 12305 | Gm2663 | NM_001102660.1 | chr6:40945820-40949478 |
| 12306 | Gm2694 | NR_033430.1 | chr8:89996710-90049453 |
| 12307 | Gm2696 | NM_001025009.1 | chr10:77277427-77278149 |
| 12308 | Gm2721 | NR_045085.1 | chr12:106633065-106641970 |
| 12309 | Gm2762 | NR_037991.1 | chr13:53489057-53550999 |
| 12310 | Gm2799 | NM_001168334.1 | chrX:30598310-30600259 |
| 12311 | Gm2799 | NM_001168334.1 | chrX:30732633-30734588 |
| 12312 | Gm2825 | NM_001168337.1 | chrX:30977793-30979742 |
| 12313 | Gm2837 | NR_040388.1 | chrX:31060181-31060959 |
| 12314 | Gm2848 | NR_046069.1 | chr13:52665248-52668594 |
| 12315 | Gm2863 | NM_001099333.3 | chrX:31349046-31350997 |
| 12316 | Gm2897 | NM_001177715.2 | chr14:3049285-3076838 |
| 12317 | Gm2913 | NM_001243015.1 | chrX:3461360-3463320 |
| 12318 | Gm2913 | NM_001243015.1 | chrX:31750506-31752466 |
| 12319 | Gm2927 | NM_001282034.1 | chrX:31832259-31834202 |
| 12320 | Gm2933 | NM_001145038.1 | chrX:31875768-31877469 |
| 12321 | Gm2933 | NM_001145038.1 | chrX:31750506-31752466 |
| 12322 | Gm2a | NM_010299.3 | chr11:54911486-54926530 |
| 12323 | Gm3002 | NR_033388.1 | chr14:3920623-3936392 |
| 12324 | Gm3020 | NR_033117.1 | chr14:3500819-3668655 |
| 12325 | Gm3020 | NR_033117.1 | chr14:3740222-3906698 |
| 12326 | Gm3020 | NR_033117.1 | chr14:6653690-7119724 |
| 12327 | Gm3086 | NR_036607.1 | chr2:71064396-71070731 |
| 12328 | Gm3139 | NM_001243937.1 | chr5:94955308-94967392 |
| 12329 | Gm3139 | NM_001243938.1 | chr5:94955308-94967392 |
| 12330 | Gm3143 | NR_038347.1 | chr3:34598561-34615584 |
| 12331 | Gm3143 | NR_038348.1 | chr3:34598561-34615584 |
| 12332 | Gm3219 | NR_027380.1 | chr14:35158240-35158844 |
| 12333 | Gm3230 | NR_033642.1 | chr2:19577432-19579524 |
| 12334 | Gm3238 | NM_001101630.1 | chr10:77233378-77234070 |
| 12335 | Gm3258 | NM_011509.1 | chr10:31133532-31134241 |
| 12336 | Gm3259 | NM_001270456.1 | chr5:95734941-95772594 |
| 12337 | Gm3264 | NM_001242945.1 | chr14:4974180-4978876 |
| 12338 | Gm3264 | NM_001242945.1 | chr14:4534030-4622491 |
| 12339 | Gm3279 | NR_046071.1 | chr6:55634564-55644568 |
| 12340 | Gm3285 | NM_001101631.1 | chr10:77324720-77325383 |
| 12341 | Gm3286 | NM_001122678.2 | chr5:96204888-96233254 |
| 12342 | Gm3286 | NM_001122678.2 | chr5:95885824-95914608 |
| 12343 | Gm3286 | NM_001122678.2 | chr5:95939760-95951421 |
| 12344 | Gm3286 | NM_001122678.2 | chrUn_random:1663024-1691372 |
| 12345 | Gm3286 | NM_001167792.1 | chr5:95939760-95951421 |
| 12346 | Gm3286 | NM_001167792.1 | chr5:95885824-95914608 |
| 12347 | Gm3286 | NM_001167793.1 | chr5:95885824-95914608 |
| 12348 | Gm3286 | NM_001167793.1 | chr5:96204888-96233254 |
| 12349 | Gm3286 | NM_001167793.1 | chrUn_random:1663024-1691372 |
| 12350 | Gm3286 | NM_001167793.1 | chr5:95939760-95951421 |
| 12351 | Gm3317 | NM_001242941.2 | chr14:6451733-6458384 |
| 12352 | Gm3317 | NM_001242941.2 | chr14:5266666-5273317 |
| 12353 | Gm3317 | NM_001242941.2 | chr14:6653690-7119724 |
| 12354 | Gm3336 | NM_001195253.1 | chr8:73242441-73246534 |
| 12355 | Gm3376 | NM_001270512.1 | chrY:2387258-2398856 |
| 12356 | Gm3383 | NM_001205306.1 | chr14:5468459-6240637 |
| 12357 | Gm3383 | NM_001205306.1 | chr14:5468459-6240637 |
| 12358 | Gm3383 | NM_001205306.1 | chr14:6653690-7119724 |
| 12359 | Gm3383 | NM_001205306.1 | chr14:5468459-6240637 |
| 12360 | Gm3383 | NM_001291093.1 | chr14:6653690-7119724 |
| 12361 | Gm3383 | NM_001291093.1 | chr14:5468459-6240637 |
| 12362 | Gm3383 | NM_001291093.1 | chr14:5468459-6240637 |
| 12363 | Gm3383 | NM_001291093.1 | chr14:5468459-6240637 |
| 12364 | Gm3383 | NM_001291094.1 | chr14:5468459-6240637 |
| 12365 | Gm3383 | NM_001291094.1 | chr14:6653690-7119724 |
| 12366 | Gm3383 | NM_001291094.1 | chr14:5468459-6240637 |
| 12367 | Gm3383 | NM_001291094.1 | chr14:5468459-6240637 |
| 12368 | Gm3402 | NM_001243111.1 | chr5:147313952-147328478 |
| 12369 | Gm3402 | NM_001243111.1 | chr5:147367688-147370491 |
| 12370 | Gm3404 | NM_001243109.1 | chr5:147337376-147340129 |
| 12371 | Gm3409 | NM_001243113.1 | chr5:147349223-147352003 |
| 12372 | Gm3414 | NR_027993.1 | chr5:46110906-46118817 |
| 12373 | Gm3415 | NM_001243114.1 | chr5:147313952-147328478 |
| 12374 | Gm3415 | NM_001243114.1 | chr5:147367688-147370491 |
| 12375 | Gm3417 | NM_001123368.1 | chr17:15164114-15178523 |
| 12376 | Gm3417 | NM_001123368.1 | chr17:15132746-15159413 |
| 12377 | Gm3428 | NR_030729.1 | chr9:35656129-35657465 |
| 12378 | Gm3434 | NR_030729.1 | chr17:35941871-35943215 |
| 12379 | Gm3435 | NM_001123372.1 | chr17:15146804-15159413 |
| 12380 | Gm3448 | NM_001123367.1 | chr15:101152-15115776 |
| 12381 | Gm3458 | NR_110518.1 | chr9:71059719-71063193 |
| 12382 | Gm3458 | NR_110519.1 | chr9:71059719-71063193 |
| 12383 | Gm3500 | NM_001256886.1 | chr14:5468459-6240637 |
| 12384 | Gm3500 | NM_001256886.1 | chr14:5468459-6240637 |
| 12385 | Gm3500 | NM_001256886.1 | chr14:6653690-7119724 |
| 12386 | Gm3558 | NM_001270842.1 | chr14:8377664-8401080 |
| 12387 | Gm3604 | NM_001162910.1 | chr13:62469075-62484534 |
| 12388 | Gm362 | NM_001195271.1 | chrX:40944165-40946707 |
| 12389 | Gm364 | NM_001128625.2 | chrX:54662325-54741948 |
| 12390 | Gm3646 | NM_001177348.1 | chr1:39860985-39862177 |
| 12391 | Gm3696 | NM_001024712.2 | chr14:7915539-7937971 |
| 12392 | Gm3706 | NM_001243001.1 | chrX:3748108-3750057 |
| 12393 | Gm3706 | NM_001243001.1 | chrX:4446441-4448390 |
| 12394 | Gm3706 | NM_001243001.1 | chr3:3241669-3243629 |
| 12395 | Gm3716 | NR_045078.1 | chr5:64985101-65001938 |
| 12396 | Gm3763 | NM_001243024.1 | chrX:4598165-4600108 |
| 12397 | Gm3776 | NM_001243092.1 | chr9:78104935-78116973 |
| 12398 | Gm382 | NM_001033241.3 | chrX:123574503-123598518 |
| 12399 | Gm3893 | NR_033506.1 | chr4:41763294-42104673 |
| 12400 | Gm3985 | NM_001177589.1 | chr8:33998976-34060498 |
| 12401 | Gm4013 | NR_033452.1 | chr18:42434033-42434851 |
| 12402 | Gm4027 | NM_001177564.1 | chr12:88959859-88963093 |
| 12403 | Gm4070 | NM_001243039.1 | chr7:113043632-113102484 |
| 12404 | Gm4070 | NM_001243039.1 | chr7:113300049-113358854 |
| 12405 | Gm4070 | NM_001243040.1 | chr7:113300049-113358854 |
| 12406 | Gm4070 | NM_001243040.1 | chr7:113043632-113102484 |
| 12407 | Gm41 | NR_036689.1 | chrX:83590813-83600333 |
| 12408 | Gm4133 | NM_001167158.1 | chr7:20918490-20919414 |
| 12409 | Gm4133 | NM_001167158.1 | chr7:23113812-23114736 |
| 12410 | Gm4141 | NM_001167163.1 | chr7:21160669-21161590 |
| 12411 | Gm4175 | NM_001167165.1 | chr7:22085545-23769692 |
| 12412 | Gm4177 | NM_001167167.1 | chr7:22580829-22581747 |
| 12413 | Gm4201 | NM_001167162.1 | chr7:23349441-23350362 |
| 12414 | Gm4214 | NM_001167164.1 | chr7:22545549-22546494 |
| 12415 | Gm4214 | NM_001167164.1 | chr7:23768747-23769692 |
| 12416 | Gm4216 | NM_001167166.1 | chr7:23804024-23804942 |
| 12417 | Gm4224 | NR_046074.1 | chr7:12806664-12811156 |
| 12418 | Gm4251 | NR_046075.1 | chr14:71651079-71670866 |
| 12419 | Gm4251 | NR_046076.1 | chr14:71651079-71670866 |
| 12420 | Gm4262 | NR_040518.1 | chr16:11008990-11015277 |
| 12421 | Gm4265 | NR_046077.1 | chr7:137105678-137122183 |
| 12422 | Gm4278 | NR_046078.1 | chr14:75374892-75386911 |
| 12423 | Gm428 | NM_001081644.1 | chr4:73329418-73333463 |
| 12424 | Gm4285 | NM_045294.1 | chr14:76242724-76244771 |
| 12425 | Gm4297 | NM_001100446.2 | chrX:24129375-24150431 |
| 12426 | Gm4302 | NM_001166634.1 | chr10:99808603-99824881 |
| 12427 | Gm4302 | NM_001166634.1 | chr10:99808603-99824881 |
| 12428 | Gm4303 | NM_001166638.1 | chr10:99803471-99804396 |
| 12429 | Gm4303 | NM_001166638.1 | chr10:99808603-99824881 |
| 12430 | Gm4303 | NM_001166638.1 | chr10:99808603-99824881 |
| 12431 | Gm4305 | NM_001166639.1 | chr10:99,803,472-99,824,881 |
| 12432 | Gm4312 | NM_001166636.1 | chr10:99829132-99830046 |
| 12433 | Gm4312 | NM_001166636.1 | chr10:99798309-99799223 |
| 12434 | Gm4312 | NM_001166636.1 | chr10:99844280-99845194 |
| 12435 | Gm4340 | NM_001177535.1 | chr10:103605568-103625055 |
| 12436 | Gm4340 | NM_001177535.1 | chr10:103605568-103625055 |
| 12437 | Gm4349 | NR_033637.1 | chr3:95231270-95235007 |
| 12438 | Gm436 | NM_001085564.1 | chr4:144259839-144276271 |
| 12439 | Gm4371 | NR_028311.1 | chr15:96013231-96033901 |
| 12440 | Gm438 | NM_001126316.1 | chrX:144367106-144376486 |
| 12441 | Gm44 | NM_001101450.1 | chrX:88137480-88138473 |
| 12442 | Gm4432 | NR_102329.1 | chr17:32378865-32379800 |
| 12443 | Gm4461 | NM_001199062.1 | chr17:33352205-33353296 |
| 12444 | Gm4477 | NM_001253910.2 | chr6:85656700-85658555 |
| 12445 | Gm4489 | NR_027637.1 | chr10:121556752-121567614 |
| 12446 | Gm4498 | NM_001167151.1 | chr7:23013582-23014503 |
| 12447 | Gm4498 | NM_001167151.1 | chr7:21696445-21697366 |
| 12448 | Gm4532 | NR_030674.1 | chr7:134375931-134376644 |
| 12449 | Gm4541 | NR_033693.1 | chr7:21196232-21215690 |
| 12450 | Gm4541 | NR_033693.1 | chr7:22230791-22250942 |
| 12451 | Gm4541 | NR_033693.1 | chr7:22713597-22733746 |
| 12452 | Gm4541 | NR_033693.1 | chr7:23385002-23404469 |
| 12453 | Gm4541 | NR_033693.1 | chr7:23936779-23963780 |
| 12454 | Gm4559 | NM_001199309.1 | chr7:149459668-149460268 |
| 12455 | Gm4566 | NR_028023.1 | chr17:71682540-71691144 |
| 12456 | Gm4567 | NM_001037248.3 | chr7:21309847-21315960 |
| 12457 | Gm4567 | NM_001037248.3 | chr7:21509530-21515643 |
| 12458 | Gm4567 | NM_001037248.3 | chr7:23498616-23685774 |
| 12459 | Gm4598 | NR_030681.1 | chr7:25446312-25448128 |
| 12460 | Gm4710 | NR_033456.1 | chr17:76260362-76288379 |
| 12461 | Gm4719 | NR_045852.1 | chr17:89778580-89784333 |
| 12462 | Gm4736 | NM_053251.1 | chr6:132064239-132314153 |
| 12463 | Gm4745 | NM_001038676.1 | chr7:15245056-15251345 |
| 12464 | Gm4759 | NR_003967.1 | chr7:113565063-113584587 |
| 12465 | Gm4763 | NM_177593.1 | chr7:25507512-25509309 |
| 12466 | Gm4776 | NR_037690.1 | chr1:46077259-46087282 |
| 12467 | Gm4776 | NR_037691.1 | chr1:46077259-46087282 |
| 12468 | Gm4787 | NM_001038995.2 | chr12:82477977-82480473 |
| 12469 | Gm4788 | NM_001029977.3 | chr1:141594495-141677816 |
| 12470 | Gm4788 | NM_001160303.1 | chr1:141594495-141677816 |
| 12471 | Gm4788 | NM_001160304.1 | chr1:141594495-141677816 |
| 12472 | Gm4791 | NM_001243258.1 | chr9:46806823-46811943 |
| 12473 | Gm4792 | NR_033209.1 | chr10:93756407-93761448 |
| 12474 | Gm4794 | NM_001101452.1 | chr10:33486229-33501921 |
| 12475 | Gm4814 | NR_036451.1 | chr13:93843259-93844710 |
| 12476 | Gm4827 | NR_045935.1 | chr16:50019770-50072965 |
| 12477 | Gm4832 | NM_001190356.1 | chr17:88524851-88530456 |
| 12478 | Gm4836 | NM_009529.3 | chrX:29483950-29506884 |
| 12479 | Gm4836 | NM_009529.3 | chrX:29924763-29947708 |
| 12480 | Gm4836 | NM_009529.3 | chrX:32944181-32967088 |

Fig. 25 - 67

| | | | | | | | |
|---|---|---|---|---|---|---|---|
| 12481 | Gm4841 | NM_001034859.3 | chr18:60427954-60432921 | 12576 | Gm5476 | NR_002868.1 | chr15:101417748-101419003 |
| 12482 | Gm4846 | NM_001164306.1 | chr1:168413743-168427719 | 12577 | Gm5477 | NR_002869.1 | chr15:101439305-101440910 |
| 12483 | Gm4847 | NM_001164312.1 | chr1:168559101-168577824 | 12578 | Gm5478 | NR_003960.1 | chr15:101473451-101477811 |
| 12484 | Gm4850 | NR_015347.1 | chr1:31321691-31324906 | 12579 | Gm5483 | NM_001082547.1 | chr16:36184297-36188196 |
| 12485 | Gm4858 | NM_001034860.2 | chr3:92872744-92879427 | 12580 | Gm5485 | NR_015373.1 | chr16:48399565-48412529 |
| 12486 | Gm4858 | NM_001177694.1 | chr3:92872744-92879427 | 12581 | Gm5512 | NR_002891.1 | chr19:12979720-12981475 |
| 12487 | Gm4861 | NM_177665.3 | chr3:137213008-137215586 | 12582 | Gm5512 | NR_002891.1 | chr10:5914188-5943372 |
| 12488 | Gm4871 | NM_001101463.1 | chr5:145790468-145793633 | 12583 | Gm5523 | NR_004447.1 | chr1:13775765-13777010 |
| 12489 | Gm4872 | NR_073371.1 | chr6:53171157-53176593 | 12584 | Gm5531 | NM_001008426.3 | chr1:155721474-155724001 |
| 12490 | Gm4872 | NR_073372.1 | chr6:53171157-53176593 | 12585 | Gm5535 | NM_001033778.1 | chr2:143998885-144015026 |
| 12491 | Gm4884 | NM_183166.2 | chr7:48288088-48300672 | 12586 | Gm5538 | NM_001101531.1 | chr3:59533707-59556319 |
| 12492 | Gm4890 | NM_001034864.1 | chr8:81818976-81831673 | 12587 | Gm5544 | NM_001033779.2 | chr3:97734095-97770941 |
| 12493 | Gm4890 | NR_045823.1 | chr8:81818976-81831673 | 12588 | Gm5547 | NR_045845.1 | chr3:105618484-105620277 |
| 12494 | Gm4894 | NM_177701.3 | chr9:49058635-49088699 | 12589 | Gm5549 | NM_001270430.1 | chr3:132293154-132307613 |
| 12495 | Gm4906 | NM_001114529.1 | chrX:10904947-10905277 | 12590 | Gm5577 | NR_026990.1 | chr6:87931676-87934174 |
| 12496 | Gm4907 | NM_001034864.3 | chrX:23469888-23484676 | 12591 | Gm5591 | NM_001013810.2 | chr7:39303157-39313212 |
| 12497 | Gm4922 | NM_177706.4 | chr10:18499532-18506599 | 12592 | Gm5592 | NM_001033782.3 | chr7:48539696-48545553 |
| 12498 | Gm4925 | NM_001037166.2 | chr10:88192285-88193846 | 12593 | Gm5595 | NM_001008427.1 | chr7:49915477-49948088 |
| 12499 | Gm4926 | NR_028066.1 | chr1:146450007-46458508 | 12594 | Gm5607 | NR_027975.2 | chr8:12385771-12436732 |
| 12500 | Gm4937 | NM_001013760.2 | chrX:73509644-73513012 | 12595 | Gm561 | NM_001033297.2 | chr2:144419800-144421101 |
| 12501 | Gm4944 | NM_001205095.1 | chr17:22334231-22362581 | 12596 | Gm5615 | NM_001033783.2 | chr9:36339987-36349548 |
| 12502 | Gm4951 | NM_001033767.3 | chr18:60317730-60407474 | 12597 | Gm5617 | NM_001004191.3 | chr9:48303447-48304080 |
| 12503 | Gm4952 | NM_001013762.2 | chr19:12674473-12702106 | 12598 | Gm5622 | NM_001013816.1 | chr14:52172464-52282628 |
| 12504 | Gm4952 | NM_001167907.1 | chr19:12674473-12702106 | 12599 | Gm5627 | NR_033301.1 | chr9:102641977-102659015 |
| 12505 | Gm4956 | NR_028658.1 | chr1:21275326-21288393 | 12600 | Gm5634 | NM_001085524.1 | chrX:8539259-8540101 |
| 12506 | Gm4961 | NR_045694.2 | chr5:30419479-30424226 | 12601 | Gm5635 | NM_001038697.2 | chrX:8640215-8640948 |
| 12507 | Gm4971 | NR_033604.1 | chr7:80830377-80831449 | 12602 | Gm5640 | NM_001099302.1 | chrX:71884457-71890974 |
| 12508 | Gm4975 | NM_001085687.1 | chr8:66403490-66430967 | 12603 | Gm5643 | NR_002883.1 | chr8:138732047-138733780 |
| 12509 | Gm4980 | NM_001195529.1 | chr7:106772576-106775613 | 12604 | Gm5643 | NR_002883.1 | chr15:103070827-103077129 |
| 12510 | Gm4981 | NM_001034869.2 | chr10:57697595-57699408 | 12605 | Gm5662 | NM_001013824.3 | chr12:89509080-89512941 |
| 12511 | Gm4984 | NM_001101484.1 | chrX:12229008-12229946 | 12606 | Gm5712 | NR_033594.1 | chr3:129136590-129137630 |
| 12512 | Gm5 | NR_024513.1 | chr5:151302321-151304794 | 12607 | Gm572 | NM_001085505.1 | chr4:148017425-148045681 |
| 12513 | Gm5039 | NR_003647.2 | chr12:89558566-89560206 | 12608 | Gm5725 | NM_001166711.1 | chr7:22628362-22629286 |
| 12514 | Gm5065 | NR_003622.2 | chr7:5302244-5312284 | 12609 | Gm5725 | NM_001167146.1 | chr7:23318982-23319906 |
| 12515 | Gm5069 | NR_003623.1 | chr1:182257100-182260680 | 12610 | Gm5728 | NM_001166713.1 | chr7:20959841-20960759 |
| 12516 | Gm5071 | NM_001256004.1 | chr5:89177284-89178319 | 12611 | Gm5728 | NM_001166713.1 | chr7:23155140-23156058 |
| 12517 | Gm5072 | NM_001114678.1 | chrX:88637838-88638873 | 12612 | Gm5741 | NM_001195531.1 | chr8:87591466-87591881 |
| 12518 | Gm5072 | NM_001114678.1 | chrX:88725464-88726499 | 12613 | Gm5766 | NR_003628.1 | chr16:4229228-4231205 |
| 12519 | Gm5082 | NM_001145878.1 | chr13:41744811-41752146 | 12614 | Gm5771 | NM_001038997.2 | chr6:41342354-41347255 |
| 12520 | Gm5082 | NM_177808.4 | chr13:41744811-41752146 | 12615 | Gm5779 | NR_033602.1 | chr10:74814799-74815706 |
| 12521 | Gm5083 | NR_045285.1 | chr13:44216535-44220548 | 12616 | Gm5795 | NM_001270806.1 | chr14:3188283-3196683 |
| 12522 | Gm5084 | NR_036449.1 | chr13:60306831-60317379 | 12617 | Gm5795 | NM_001270806.1 | chr14:3500819-3668655 |
| 12523 | Gm5086 | NR_046157.1 | chr13:98329954-98353949 | 12618 | Gm5795 | NM_001270806.1 | chr14:3740222-3906698 |
| 12524 | Gm5087 | NM_177813.3 | chr14:13989901-14117152 | 12619 | Gm5796 | NM_001029930.2 | chr14:4126976-4144402 |
| 12525 | Gm5088 | NR_002862.3 | chr14:90296030-90299254 | 12620 | Gm5797 | NM_001025085.2 | chr14:8156501-8164909 |
| 12526 | Gm5089 | NR_033325.1 | chr14:122580915-122850368 | 12621 | Gm5800 | NM_001034102.2 | chr14:52333318-52336807 |
| 12527 | Gm5089 | NR_033326.1 | chr14:122580915-122850368 | 12622 | Gm5801 | NR_002889.2 | chr14:56629128-56630317 |
| 12528 | Gm5091 | NR_046164.1 | chr17:15368548-15377747 | 12623 | Gm5801 | NR_002889.2 | chr4:155317921-155333713 |
| 12529 | Gm5095 | NR_033454.1 | chr18:47697388-47878290 | 12624 | Gm5803 | NM_001165971.3 | chr15:22643574-22644739 |
| 12530 | Gm5105 | NR_037975.1 | chr3:137711724-137730352 | 12625 | Gm5820 | NM_001033789.2 | chr18:39052110-39130928 |
| 12531 | Gm5108 | NM_001256184.1 | chr5:68332908-68368309 | 12626 | Gm5833 | NR_040304.1 | chr1:140536671-140578652 |
| 12532 | Gm5111 | NM_183309.3 | chr6:48539443-48540583 | 12627 | Gm5860 | NR_040659.1 | chr4:81711283-81748711 |
| 12533 | Gm5113 | NM_001054940-30965228 | chr7:30954940-30965228 | 12628 | Gm5862 | NM_001281525.1 | chr5:26344861-26349431 |
| 12534 | Gm5114 | NM_177890.3 | chr7:46662663-46668530 | 12629 | Gm5868 | NM_001024147.2 | chr5:72972877-72978789 |
| 12535 | Gm5122 | NR_040767.1 | chr9:60864875-60867604 | 12630 | Gm5878 | NM_001034902.2 | chr6:85061409-85076088 |
| 12536 | Gm5124 | NR_045868.1 | chrX:29037990-29041750 | 12631 | Gm5885 | NM_001185040.1 | chr6:133479206-133482780 |
| 12537 | Gm5126 | NR_026596.1 | chrX:100127385-100129562 | 12632 | Gm5886 | NM_001177652.2 | chr6:133714016-133717421 |
| 12538 | Gm5127 | NM_001033541.2 | chrX:103778525-103905896 | 12633 | Gm5891 | NM_001034904.2 | chr7:23917641-23929499 |
| 12539 | Gm5128 | NM_183320.3 | chrX:131907822-131917932 | 12634 | Gm5891 | NM_001034904.2 | chr7:22694452-22706310 |
| 12540 | Gm5128 | NM_183320.3 | chrX:131968373-131978536 | 12635 | Gm5893 | NR_045096.1 | chr7:25603813-25625294 |
| 12541 | Gm5129 | NR_028426.1 | chr5:30061874-30062476 | 12636 | Gm590 | NM_001195437.1 | chr9:110817242-110819365 |
| 12542 | Gm5132 | NM_001085517.1 | chrX:9149085-9149517 | 12637 | Gm5901 | NM_001195727.1 | chr7:112523612-112526801 |
| 12543 | Gm5134 | NM_198635.3 | chr10:75417259-75472334 | 12638 | Gm5916 | NM_001167587.1 | chr9:35927518-35936364 |
| 12544 | Gm5136 | NM_203660.2 | chr10:108136100-108137216 | 12639 | Gm5925 | NR_040410.1 | chrX:4219982-4221937 |
| 12545 | Gm5141 | NM_001256065.1 | chr13:62873559-62887168 | 12640 | Gm5934 | NM_001100444.2 | chrX:24051433-24076289 |
| 12546 | Gm5142 | NM_001004158.2 | chr14:59777339-59797586 | 12641 | Gm5935 | NM_001081657.1 | chrX:24330287-24352290 |
| 12547 | Gm5148 | NM_198657.2 | chr3:37613111-37623282 | 12642 | Gm5936 | NM_001081670.2 | chrX:72082534-72088708 |
| 12548 | Gm5150 | NM_001081687.1 | chr3:15848069-15906332 | 12643 | Gm5938 | NM_001085534.2 | chrX:75370805-75375742 |
| 12549 | Gm5166 | NR_027707.1 | chrX:99986534-99993728 | 12644 | Gm5941 | NM_001034103.1 | chrX:89735288-89736018 |
| 12550 | Gm5168 | NM_001085439.1 | chrX:25455339-25478167 | 12645 | Gm595 | NM_001085499.1 | chrX:46194642-46230890 |
| 12551 | Gm5169 | NM_001040669.1 | chrX:24704608-24728581 | 12646 | Gm597 | NM_001013750.1 | chr1:28832966-28837097 |
| 12552 | Gm5176 | NR_033603.1 | chr10:110937843-110938401 | 12647 | Gm6026 | NM_001177569.1 | chr1:1855008-1855344 |
| 12553 | Gm5177 | NR_033630.1 | chr10:10325742-10336111 | 12648 | Gm6034 | NM_001034909.3 | chr17:36179906-36195590 |
| 12554 | Gm525 | NM_001033266.2 | chr11:88935154-88954378 | 12649 | Gm6040 | NM_001025353.2 | chr8:22056168-22061750 |
| 12555 | Gm527 | NM_001025605.1 | chr12:66018897-66025578 | 12650 | Gm6040 | NM_001025353.2 | chr8_random:287283-292865 |
| 12556 | Gm5294 | NM_001195128.1 | chr5:139296033-139297573 | 12651 | Gm6042 | NR_002872.1 | chr15:101334246-101336744 |
| 12557 | Gm53 | NR_037977.1 | chr1:96112973-96125798 | 12652 | Gm608 | NM_001029889.2 | chr16:44173509-44227578 |
| 12558 | Gm5334 | NR_003648.2 | chr7:75763341-75764895 | 12653 | Gm6083 | NR_102704.1 | chr5:29864488-29865164 |
| 12559 | Gm5346 | NM_001025240.1 | chr8:44710328-44712539 | 12654 | Gm6086 | NM_001039219.2 | chr1:95887085-95908116 |
| 12560 | Gm5347 | NM_001079931.2 | chr8:44759011-44784845 | 12655 | Gm609 | NM_001005854.2 | chr16:45416867-45493082 |
| 12561 | Gm5382 | NM_001034100.1 | chrX:13788273-13788783 | 12656 | Gm6116 | NR_045866.1 | chr5:75345218-75362393 |
| 12562 | Gm5409 | NM_001036305-41369692 | chr6:41365305-41369692 | 12657 | Gm6121 | NM_001114754.1 | chrX:26339870-26362795 |
| 12563 | Gm5414 | NM_001003670.1 | chr15:101454459-101458619 | 12658 | Gm614 | NM_001033362.2 | chrX:98456715-98459331 |
| 12564 | Gm5415 | NM_001164286.1 | chr1:32600391-32604138 | 12659 | Gm6150 | NR_038036.1 | chr10:9404519-9411707 |
| 12565 | Gm5416 | NM_001082542.1 | chr6:36210488-36217874 | 12660 | Gm6164 | NM_001167153.1 | chr7:20790032-20790956 |
| 12566 | Gm5420 | NR_045843.1 | chr10:21410656-21413784 | 12661 | Gm6164 | NM_001167153.1 | chr7:22985359-22986283 |
| 12567 | Gm5424 | NR_033512.1 | chr10:61533769-61535319 | 12662 | Gm6194 | NR_033512.1 | chr3:8461386-8463098 |
| 12568 | Gm5431 | NM_001024230.2 | chr11:48700923-48715654 | 12663 | Gm6213 | NR_044988.1 | chr8:40383333-40453622 |
| 12569 | Gm5434 | NR_003649.1 | chr12:36816965-36818416 | 12664 | Gm6225 | NR_033457.1 | chr18:3336414-3366861 |
| 12570 | Gm5441 | NR_044987.1 | chr12:118472994-118575485 | 12665 | Gm6249 | NR_046021.1 | chr7:143859637-143902287 |
| 12571 | Gm5458 | NM_001024706.2 | chr14:20413359-20421809 | 12666 | Gm6251 | NM_001101561.2 | chr10:19928245-19928836 |
| 12572 | Gm5460 | NM_001034880.2 | chr14:34854263-34860167 | 12667 | Gm6260 | NR_040405.1 | chr3:143333855-143375107 |
| 12573 | Gm5464 | NM_001034881.3 | chr14:67487686-67489842 | 12668 | Gm6268 | NR_044989.1 | chrX:33943471-33944649 |
| 12574 | Gm5468 | NR_027376.1 | chr15:25343946-25382173 | 12669 | Gm6277 | NR_045421.1 | chr18:11979597-11997886 |
| 12575 | Gm5475 | NR_040351.1 | chr15:100253623-100258581 | 12670 | Gm6289 | NM_001039222.1 | chr3:144542288-144558975 |

Fig. 25 - 68

| | | | |
|---|---|---|---|
| 12671 | Gm6297 | NR_077221.1 | chr4:40667186-40704918 |
| 12672 | Gm6297 | NR_077226.1 | chr4:40667186-40704918 |
| 12673 | Gm6300 | NR_033591.2 | chr3:14363116-14374239 |
| 12674 | Gm6307 | NR_045331.1 | chr2:180120309-180136507 |
| 12675 | Gm6313 | NR_045867.1 | chr6:148555307-148562831 |
| 12676 | Gm6329 | NR_040690.1 | chr8:46245847-46250499 |
| 12677 | Gm6367 | NR_044992.1 | chr5:95417718-95455565 |
| 12678 | Gm6367 | NR_044992.1 | chrUn_random:1919827-1957720 |
| 12679 | Gm6370 | NM_001243110.1 | chr5:147302938-147305708 |
| 12680 | Gm6377 | NM_001037917.2 | chrX:106392094-106395784 |
| 12681 | Gm6402 | NR_030688.1 | chr17:30531770-30533125 |
| 12682 | Gm6406 | NM_001134661.1 | chr9:98757009-98757771 |
| 12683 | Gm6408 | NM_001243104.1 | chr5:147293518-147296278 |
| 12684 | Gm6416 | NR_046023.1 | chr13:117918831-117924691 |
| 12685 | Gm6432 | NM_001244762.1 | chr9:99129794-99137658 |
| 12686 | Gm6455 | NR_003596.2 | chr5:10865028-10870808 |
| 12687 | Gm6460 | NM_001037919.2 | chr5:11594955-11599480 |
| 12688 | Gm648 | NM_001033372.2 | chrX:53797050-53802783 |
| 12689 | Gm6484 | NM_001080940.1 | chr9:21639954-21641791 |
| 12690 | Gm6498 | NR_003630.2 | chr14:48818391-48848088 |
| 12691 | Gm6524 | NR_028307.1 | chr8:11692981-11694514 |
| 12692 | Gm6525 | NR_036654.1 | chr3:83978560-83979115 |
| 12693 | Gm6537 | NM_001195091.1 | chr7:29541193-29543983 |
| 12694 | Gm6548 | NR_003363.1 | chr17:79249844-79251884 |
| 12695 | Gm6559 | NR_110455.1 | chr6:51329708-51342790 |
| 12696 | Gm6567 | NR_046024.1 | chr7:80242637-80246954 |
| 12697 | Gm6568 | NR_040420.2 | chrX:153978735-153979682 |
| 12698 | Gm6578 | NR_003631.2 | chr6:12049522-12059580 |
| 12699 | Gm6583 | NM_001039228.4 | chr5:112782793-112785053 |
| 12700 | Gm6588 | NM_001177504.1 | chr5:112878446-112880758 |
| 12701 | Gm6592 | NM_001081564.1 | chrX:8421119-8426733 |
| 12702 | Gm6602 | NR_045362.1 | chr3:111684820-111884919 |
| 12703 | Gm6607 | NR_033622.2 | chr9:22134585-22135134 |
| 12704 | Gm6614 | NM_001081318.1 | chr6:141920716-141957266 |
| 12705 | Gm6623 | NR_033619.1 | chr17:36315721-36318309 |
| 12706 | Gm6634 | NR_040556.1 | chr3:70576300-70611213 |
| 12707 | Gm6639 | NR_040748.1 | chr3:35496073-35565085 |
| 12708 | Gm6642 | NR_033643.2 | chr19:31004876-31005452 |
| 12709 | Gm6644 | NR_037965.1 | chr6:34253934-34267443 |
| 12710 | Gm6654 | NR_038089.1 | chr6:146595699-146596324 |
| 12711 | Gm6682 | NR_033599.1 | chr12:4788975-4790318 |
| 12712 | Gm6696 | NM_001177523.1 | chr8:22693498-22694339 |
| 12713 | Gm6710 | NM_001164689.1 | chr2:174952492-175261278 |
| 12714 | Gm6710 | NM_001164689.1 | chr2:175594788-176850107 |
| 12715 | Gm6756 | NR_076393.1 | chr18:37079958-37081861 |
| 12716 | Gm6760 | NM_001177377.1 | chrX:61404580-61405373 |
| 12717 | Gm6763 | NM_001270899.1 | chr10:103,605,569-103,633,547 |
| 12718 | Gm6787 | NR_003632.2 | chrX:7674212-7683827 |
| 12719 | Gm6792 | NM_001177416.1 | chr7:6204311-6233463 |
| 12720 | Gm6792 | NM_001177417.1 | chr7:6204311-6233463 |
| 12721 | Gm6793 | NR_033513.1 | chr2:75497347-75503813 |
| 12722 | Gm6812 | NM_001098842.2 | chrX:66145547-66146228 |
| 12723 | Gm6815 | NR_102685.1 | chr16:36194565-36197972 |
| 12724 | Gm684 | NM_001195681.1 | chr9:51078362-51086659 |
| 12725 | Gm6878 | NM_001037931.3 | chr14:67923725-67935548 |
| 12726 | Gm6880 | NM_001099305.1 | chrX:71725625-71726738 |
| 12727 | Gm6890 | NM_001099306.1 | chr7:71986265-71987527 |
| 12728 | Gm6902 | NM_001270494.1 | chr7:24057806-24060262 |
| 12729 | Gm6902 | NM_001270494.1 | chr7:21509530-21515643 |
| 12730 | Gm6902 | NM_001270494.1 | chr7:23498616-23685774 |
| 12731 | Gm6904 | NM_001164329.1 | chr14:59863277-59879053 |
| 12732 | Gm6927 | NM_001101585.1 | chrX:74920152-74920791 |
| 12733 | Gm6936 | NR_045001.1 | chr16:49980572-49997588 |
| 12734 | Gm6938 | NR_033482.1 | chrX:20889035-20911853 |
| 12735 | Gm694 | NM_001033374.3 | chr4:140988586-140992020 |
| 12736 | Gm6981 | NR_023357.1 | chr9:51810166-51856810 |
| 12737 | Gm6994 | NR_033141.1 | chr14:77879290-77906675 |
| 12738 | Gm7008 | NR_045157.1 | chr12:40949950-40955770 |
| 12739 | Gm7030 | NM_001177467.1 | chr17:36264553-36266370 |
| 12740 | Gm7056 | NR_037571.1 | chr5:90045450-90051636 |
| 12741 | Gm7073 | NM_001039240.3 | chrX:57689226-57709370 |
| 12742 | Gm7102 | NM_001177513.1 | chr19:61250588-61252212 |
| 12743 | Gm7104 | NR_033570.1 | chr12:89521311-89525514 |
| 12744 | Gm711 | NM_198628.2 | chr2:26789588-26809016 |
| 12745 | Gm7120 | NM_001099244.3 | chr13:120276063-120284312 |
| 12746 | Gm7120 | NM_001177666.1 | chr13:120276063-120284312 |
| 12747 | Gm7134 | NR_033597.1 | chrX:107568091-107570495 |
| 12748 | Gm715 | NM_001217548.1 | chrX:57801182-57802391 |
| 12749 | Gm7157 | NM_001199311.1 | chrX:148997876-148998512 |
| 12750 | Gm7168 | NM_001122977.1 | chr17:14085379-14087685 |
| 12751 | Gm7173 | NM_001099307.1 | chrX:76727906-76762624 |
| 12752 | Gm7244 | NM_001101597.2 | chr9:31078985-31082970 |
| 12753 | Gm7257 | NM_001167586.1 | chr9:36239468-36242523 |
| 12754 | Gm7271 | NR_033501.1 | chr6:76913101-76945653 |
| 12755 | Gm732 | NM_001033252.2 | chrX:105141073-105143775 |
| 12756 | Gm7325 | NM_001177468.1 | chr17:45737915-45739051 |
| 12757 | Gm7325 | NM_001177469.1 | chr17:45737915-45739051 |
| 12758 | Gm7325 | NM_001177470.1 | chr17:45737915-45739051 |
| 12759 | Gm7334 | NR_002700.1 | chr16:78360108-78377002 |
| 12760 | Gm7337 | NR_003652.2 | chr5:88279383-88282037 |
| 12761 | Gm7361 | NM_001281527.1 | chr5:26584301-26588728 |
| 12762 | Gm7367 | NR_003376.2 | chr11:116295527-116300345 |
| 12763 | Gm7444 | NR_033529.1 | chr9:55875442-55879380 |
| 12764 | Gm7457 | NR_045707.1 | chr6:142762751-142782014 |
| 12765 | Gm7534 | NM_001080712.1 | chr4:133746718-133758919 |
| 12766 | Gm7538 | NR_046033.1 | chr5:119644321-119650027 |
| 12767 | Gm7550 | NR_033689.1 | chr12:55488719-55492305 |
| 12768 | Gm7609 | NM_001081746.1 | chr1:85196185-85210337 |
| 12769 | Gm7616 | NM_001101600.1 | chr9:59799100-59806851 |
| 12770 | Gm765 | NM_001128092.1 | chr6:98188007-98292748 |
| 12771 | Gm766 | NM_001145390.1 | chr6:142734300-142752986 |
| 12772 | Gm7694 | NM_001198955.1 | chr1:172228323-172236463 |
| 12773 | Gm7714 | NM_001110779.1 | chr5:88697943-88711860 |
| 12774 | Gm773 | NM_001033423.2 | chrX:53443003-53466058 |
| 12775 | Gm7788 | NR_110491.1 | chr18:23376096-23376319 |
| 12776 | Gm7849 | NM_001177518.1 | chr8:22565898-22566989 |
| 12777 | Gm7849 | NM_001177518.1 | chr8:22703846-22704937 |
| 12778 | Gm7854 | NR_028417.1 | chr5:43542925-43626593 |
| 12779 | Gm7861 | NM_001177526.1 | chr8:22565898-22566989 |
| 12780 | Gm7861 | NM_001177526.1 | chr8:22703846-22704937 |
| 12781 | Gm7904 | NR_003372.1 | chr9:21411530-21412773 |
| 12782 | Gm7977 | NR_040408.1 | chr3:47829933-47830681 |
| 12783 | Gm7978 | NM_001270457.1 | chr5:94495479-94499571 |
| 12784 | Gm7978 | NM_001270457.1 | chrUn_random:1737772-1741852 |
| 12785 | Gm805 | NR_046081.1 | chr12:87510290-87536052 |
| 12786 | Gm806 | NM_001033400.2 | chr13:50562675-50570724 |
| 12787 | Gm8096 | NR_033590.1 | chr8:29193665-29195325 |
| 12788 | Gm813 | NM_001033404.2 | chr16:58613798-58617091 |
| 12789 | Gm815 | NM_001033407.2 | chr19:26960414-26963137 |
| 12790 | Gm8179 | NR_046039.1 | chr8:33262366-33292319 |
| 12791 | Gm8221 | NR_033577.1 | chr15:77449397-77457828 |
| 12792 | Gm8234 | NR_004433.3 | chr3:58455963-58457963 |
| 12793 | Gm826 | NM_001033411.3 | chr2:160137136-160153230 |
| 12794 | Gm8267 | NM_001162954.1 | chr14:45336841-45344662 |
| 12795 | Gm829 | NM_001033412.2 | chr4:45696460-45736578 |
| 12796 | Gm8298 | NM_001243003.1 | chr3:59664972-59681235 |
| 12797 | Gm8300 | NM_001177565.1 | chr12:88855265-88859215 |
| 12798 | Gm833 | NR_033138.1 | chr4:152071648-152075031 |
| 12799 | Gm8363 | NR_073378.1 | chr17:5480988-5483069 |
| 12800 | Gm8369 | NM_001164202.1 | chr19:11566527-11587067 |
| 12801 | Gm8390 | NR_033190.1 | chr6:89362190-89166173 |
| 12802 | Gm8439 | NM_001101603.1 | chr4:120261349-120282277 |
| 12803 | Gm853 | NM_001034872.2 | chr4:129886352-129899539 |
| 12804 | Gm8579 | NR_036696.1 | chr6:32385818-3267019 |
| 12805 | Gm8580 | NR_027478.1 | chr10:93127989-93128599 |
| 12806 | Gm8615 | NR_028061.1 | chr5:149965704-149967768 |
| 12807 | Gm8633 | NR_045179.1 | chr10:97762560-97814501 |
| 12808 | Gm867 | NM_001277132.1 | chr10:75400468-75403417 |
| 12809 | Gm8677 | NM_001167147.1 | chr7:21130182-21131106 |
| 12810 | Gm8693 | NM_001167154.1 | chr7:23476415-23477336 |
| 12811 | Gm8693 | NM_001167154.1 | chr7:21287647-21288568 |
| 12812 | Gm8709 | NR_033633.1 | chr10:26393251-26394457 |
| 12813 | Gm8720 | NM_001166756.1 | chr7:23851551-23852475 |
| 12814 | Gm8765 | NM_001244649.1 | chr13:50793697-50798778 |
| 12815 | Gm8773 | NR_033499.1 | chr5:5573798-5576203 |
| 12816 | Gm8787 | NM_001099310.1 | chrX:76575851-76603407 |
| 12817 | Gm8801 | NR_028278.1 | chr17:36084098-36090262 |
| 12818 | Gm8817 | NM_001101606.1 | chrX:163501380-163508302 |
| 12819 | Gm884 | NM_001033434.2 | chr11:103395890-103476053 |
| 12820 | Gm8882 | NM_001177588.1 | chr6:132311123-132314152 |
| 12821 | Gm8883 | NR_027658.1 | chr1:71934685-71937778 |
| 12822 | Gm8883 | NR_027659.1 | chr1:71934685-71937778 |
| 12823 | Gm8884 | NR_026561.1 | chr9:48262444-48262828 |
| 12824 | Gm8898 | NM_001177405.1 | chr2:174952492-175261278 |
| 12825 | Gm8898 | NM_001177407.1 | chr2:174952492-175261278 |
| 12826 | Gm8898 | NM_001177407.1 | chr2:175594788-176850107 |
| 12827 | Gm8909 | NM_001081032.2 | chr17:36303388-36305482 |
| 12828 | Gm8979 | NR_030719.1 | chr7:113219245-113222662 |
| 12829 | Gm8989 | NR_030720.1 | chr7:113465909-113468042 |
| 12830 | Gm8989 | NR_030720.1 | chr7:113219245-113222662 |
| 12831 | Gm8994 | NM_001142734.1 | chr6:136277556-136280001 |
| 12832 | Gm9 | NM_001033234.2 | chrX:34748496-34751036 |
| 12833 | Gm904 | NM_001033770.1 | chr13:50738596-50741207 |
| 12834 | Gm9047 | NM_001145360.1 | chr6:29421436-29423429 |
| 12835 | Gm9054 | NR_045872.1 | chr3:95789432-95790890 |
| 12836 | Gm906 | NM_001033438.2 | chr13:50340549-50345677 |
| 12837 | Gm9079 | NR_004652.1 | chr10:121515167-121516935 |
| 12838 | Gm9112 | NM_001177365.1 | chrX:99902226-99903009 |
| 12839 | Gm9125 | NM_001163730.2 | chr3:93740554-93747465 |
| 12840 | Gm9125 | NM_001163730.2 | chr3:93851902-93858807 |
| 12841 | Gm9159 | NR_033398.1 | chrX:100740838-100743038 |
| 12842 | Gm9199 | NR_027860.1 | chr14:73425409-73426697 |
| 12843 | Gm9268 | NM_001106061.1 | chr7:50274167-50303476 |
| 12844 | Gm933 | NM_001256309.1 | chr16:32804973-32810532 |
| 12845 | Gm9376 | NM_001101609.1 | chr14:118666379-118666992 |
| 12846 | Gm94 | NM_001033280.2 | chr18:43936849-43952532 |
| 12847 | Gm9513 | NM_001128510.1 | chr9:36283222-36284765 |
| 12848 | Gm9573 | NM_001244654.1 | chr17:35754867-35763582 |
| 12849 | Gm960 | NM_001033447.3 | chr19:4625840-4698668 |
| 12850 | Gm9696 | NR_037189.1 | chr3:59756230-59777516 |
| 12851 | Gm973 | NM_001013771.2 | chr1:59573107-59691353 |
| 12852 | Gm9731 | NR_003107.1 | chr8:28406516-28407672 |
| 12853 | Gm9733 | NM_001076679.2 | chr3:15296550-15332302 |
| 12854 | Gm9758 | NM_198666.3 | chr5:14910123-14914889 |
| 12855 | Gm9767 | NR_028030.2 | chr10:25798061-25799253 |
| 12856 | Gm9776 | NR_045619.1 | chr13:95126703-95128878 |
| 12857 | Gm9833 | NR_045710.1 | chr3:10088276-10092562 |
| 12858 | Gm9839 | NM_001199956.1 | chr1:32576408-32577844 |

Fig. 25 - 69

| | | | |
|---|---|---|---|
| 12859 | Gm9855 | NR_037190.1 | chr10:82092587-82113022 |
| 12860 | Gm9866 | NR_045868.1 | chr12:27825660-27845381 |
| 12861 | Gm9866 | NR_045869.1 | chr12:27825660-27845381 |
| 12862 | Gm9866 | NR_045870.1 | chr12:27825660-27845381 |
| 12863 | Gm9871 | NR_027989.1 | chr6:101724242-101751976 |
| 12864 | Gm9895 | NR_045687.1 | chr19:29141790-29143993 |
| 12865 | Gm9899 | NR_040427.1 | chr5:30876360-30890992 |
| 12866 | Gm9920 | NR_045093.1 | chr15:54931472-54945137 |
| 12867 | Gm9926 | NR_040528.1 | chr8:66663831-66671391 |
| 12868 | Gm9958 | NR_045618.1 | chr5:90796022-90797514 |
| 12869 | Gm996 | NM_001005424.2 | chr2:25430935-25435619 |
| 12870 | Gm9961 | NR_033509.1 | chr16:11901457-11930687 |
| 12871 | Gm9962 | NR_033504.1 | chr7:64642642-64665311 |
| 12872 | Gm9992 | NM_001142539.1 | chr17:7568060-7589654 |
| 12873 | Gm9994 | NM_001205249.1 | chr1:95815013-95837816 |
| 12874 | Gm9999 | NR_033461.1 | chr7:54232001-54243173 |
| 12875 | Gmcl1 | NM_011818.3 | chr6:86641761-86683372 |
| 12876 | Gmcl1l | NM_027955.3 | chrX:30732634-30734588 |
| 12877 | Gmds | NM_146041.2 | chr13:31911454-32430413 |
| 12878 | Gmeb1 | NM_001122992.1 | chr4:131776939-131817464 |
| 12879 | Gmeb1 | NM_020273.2 | chr4:131776939-131817464 |
| 12880 | Gmeb2 | NM_198169.2 | chr2:180986155-181022671 |
| 12881 | Gmfb | NM_022023.2 | chr14:47427823-47441917 |
| 12882 | Gmfg | NM_001039192.1 | chr7:29222465-29231914 |
| 12883 | Gmfg | NM_001290550.1 | chr7:29222465-29231914 |
| 12884 | Gmfg | NM_022024.2 | chr7:29222465-29231914 |
| 12885 | Gmip | NM_198101.1 | chr8:72332585-72345769 |
| 12886 | Gml | NM_177524.1 | chr15:74643884-74649245 |
| 12887 | Gmnc | NM_001013761.1 | chr16:26957320-26991738 |
| 12888 | Gmnc | NM_001285916.1 | chr16:26957320-26991738 |
| 12889 | Gmnc | NM_001285918.1 | chr16:26957320-26991738 |
| 12890 | Gmnn | NM_020567.2 | chr13:24843713-24853806 |
| 12891 | Gmppa | NM_133708.1 | chr1:75432517-75439751 |
| 12892 | Gmppb | NM_177910.3 | chr9:107951621-107954267 |
| 12893 | Gmpr | NM_025508.5 | chr13:45602837-45641750 |
| 12894 | Gmpr2 | NM_177992.2 | chr14:56291071-56297588 |
| 12895 | Gmps | NM_001033300.2 | chr3:63780064-63823000 |
| 12896 | Gna11 | NM_010301.3 | chr10:80991476-81007791 |
| 12897 | Gna12 | NM_010302.3 | chr5:141235897-141306385 |
| 12898 | Gna13 | NM_010303.3 | chr11:109224108-109262683 |
| 12899 | Gna14 | NM_008137.4 | chr19:16510156-16685308 |
| 12900 | Gna15 | NM_010304.3 | chr10:80965058-80986970 |
| 12901 | Gnai1 | NM_010305.1 | chr5:17770952-17866231 |
| 12902 | Gnai2 | NM_008138.4 | chr9:107516468-107537673 |
| 12903 | Gnai3 | NM_010306.3 | chr3:107910192-107949070 |
| 12904 | Gnal | NM_010307.3 | chr18:67247951-67405484 |
| 12905 | Gnal | NM_177137.5 | chr18:67247951-67405484 |
| 12906 | Gnao1 | NM_001113384.1 | chr8:96334737-96493288 |
| 12907 | Gnao1 | NM_010308.3 | chr8:96334737-96493288 |
| 12908 | Gnaq | NM_008139.5 | chr19:16207321-16461943 |
| 12909 | Gnas | NM_001077507.3 | chr2:174174637-174172243 |
| 12910 | Gnas | NM_001077510.2 | chr2:174106737-174172243 |
| 12911 | Gnas | NM_019690.2 | chr2:174106737-174172243 |
| 12912 | Gnas | NM_022000.2 | chr2:174106737-174172243 |
| 12913 | Gnas | NM_201616.1 | chr2:174106737-174172243 |
| 12914 | Gnas | NM_201617.1 | chr2:174106737-174172243 |
| 12915 | Gnas | NM_201618.1 | chr2:174106737-174172243 |
| 12916 | Gnas | NR_003258.1 | chr2:174106737-174172243 |
| 12917 | Gnat1 | NM_008140.2 | chr9:107576804-107581923 |
| 12918 | Gnat2 | NM_008141.3 | chr3:107895983-107904348 |
| 12919 | Gnat3 | NM_001081143.1 | chr5:17468387-17525486 |
| 12920 | Gnaz | NM_010311.3 | chr10:74429976-74478022 |
| 12921 | Gnb1 | NM_001160016.1 | chr4:154865469-154933378 |
| 12922 | Gnb1 | NM_001160017.1 | chr4:154865469-154933378 |
| 12923 | Gnb1 | NM_008142.4 | chr4:154865469-154933378 |
| 12924 | Gnb1l | NM_001081682.2 | chr16:18498805-18566773 |
| 12925 | Gnb1l | NM_001285491.1 | chr16:18498805-18566773 |
| 12926 | Gnb1l | NM_001285493.1 | chr16:18498805-18566773 |
| 12927 | Gnb1l | NM_001285494.1 | chr16:18498805-18566773 |
| 12928 | Gnb1l | NM_001038637.1 | chr16:18498805-18566773 |
| 12929 | Gnb1l | NR_104347.1 | chr16:18498805-18566773 |
| 12930 | Gnb2 | NM_010312.4 | chr5:137969357-137974457 |
| 12931 | Gnb2l1 | NM_008143.3 | chr11:48613862-48619743 |
| 12932 | Gnb3 | NM_013530.1 | chr6:124784257-124790293 |
| 12933 | Gnb4 | NM_013531.4 | chr3:32482449-32515457 |
| 12934 | Gnb5 | NM_010313.3 | chr9:75154094-75193730 |
| 12935 | Gnb5 | NM_138719.5 | chr9:75154094-75193730 |
| 12936 | Gnb5 | NR_073186.1 | chr9:75154094-75193730 |
| 12937 | Gne | NM_015190414.1 | chr4:44046946-44097049 |
| 12938 | Gne | NM_015828.3 | chr4:44046946-44097049 |
| 12939 | Gng10 | NM_025277.3 | chr4:59048027-59054771 |
| 12940 | Gng11 | NM_025321.2 | chr6:3953986-3958446 |
| 12941 | Gng12 | NM_001177556.1 | chr6:66846390-66971355 |
| 12942 | Gng12 | NM_001177557.1 | chr6:66846390-66971355 |
| 12943 | Gng12 | NM_001177558.1 | chr6:66846390-66971355 |
| 12944 | Gng12 | NM_001177559.1 | chr6:66846390-66971355 |
| 12945 | Gng12 | NM_001177560.1 | chr6:66846390-66971355 |
| 12946 | Gng12 | NM_025278.3 | chr6:66846390-66971355 |
| 12947 | Gng13 | NM_022422.5 | chr17:25854117-25856047 |
| 12948 | Gng2 | NM_001285908.1 | chr14:20691780-20796471 |
| 12949 | Gng2 | NM_001285909.1 | chr14:20691780-20796471 |
| 12950 | Gng2 | NM_001285910.1 | chr14:20691780-20796471 |
| 12951 | Gng2 | NM_001285911.1 | chr14:20691780-20796471 |
| 12952 | Gng2 | NM_001285911.1 | chr14:20691780-20796471 |
| 12953 | Gng2 | NM_010315.4 | chr14:20691780-20796471 |
| 12954 | Gng3 | NM_010316.3 | chr19:8911419-8913736 |
| 12955 | Gng4 | NM_010317.3 | chr13:13876805-13920162 |
| 12956 | Gng5 | NM_010318.2 | chr3:146162799-146168507 |
| 12957 | Gng7 | NM_001038655.1 | chr10:80411368-80477670 |
| 12958 | Gng7 | NM_010319.3 | chr10:80411368-80477670 |
| 12959 | Gng8 | NM_010320.3 | chr7:17477134-17480784 |
| 12960 | Gngt1 | NM_010314.2 | chr6:3944011-3947436 |
| 12961 | Gngt2 | NM_001038664.2 | chr11:95685813-95707045 |
| 12962 | Gngt2 | NM_001284393.1 | chr11:95685813-95707045 |
| 12963 | Gngt2 | NM_001284397.1 | chr11:95685813-95707045 |
| 12964 | Gngt2 | NM_023121.2 | chr11:95685813-95707045 |
| 12965 | Gni1 | NM_008136.2 | chr17:36116899-36126407 |
| 12966 | Gni2 | NM_145552.2 | chr4:124707258-124732626 |
| 12967 | Gni3 | NM_153547.6 | chr14:31813011-31832317 |
| 12968 | Gni3 | NR_104298.1 | chr14:31813011-31832317 |
| 12969 | Gni3l | NM_001168600.1 | chrX:147417675-147451865 |
| 12970 | Gni3l | NM_198110.2 | chrX:147417675-147451865 |
| 12971 | Gnmt | NM_010321.1 | chr17:46862612-46866114 |
| 12972 | Gnpat | NM_010322.3 | chr8:127386932-127413957 |
| 12973 | Gnpda1 | NM_011937.2 | chr18:38487190-38498647 |
| 12974 | Gnpda2 | NM_001038015.1 | chr5:69966240-69983524 |
| 12975 | Gnpnat1 | NM_019425.2 | chr14:45996096-46008471 |
| 12976 | Gnptab | NM_001004164.2 | chr10:87842156-87910074 |
| 12977 | Gnptg | NM_172529.3 | chr17:25371262-25377061 |
| 12978 | Gnrh1 | NM_008145.2 | chr14:68363285-68367493 |
| 12979 | Gnrhr | NM_010323.1 | chr5:86611022-86626895 |
| 12980 | Gns | NM_029364.3 | chr10:120802145-120834301 |
| 12981 | Golga1 | NM_001290649.1 | chr2:38871675-38921061 |
| 12982 | Golga1 | NM_029793.2 | chr2:38871675-38921061 |
| 12983 | Golga1 | NR_110968.1 | chr2:38871675-38921061 |
| 12984 | Golga2 | NM_001080968.1 | chr2:32143772-32163441 |
| 12985 | Golga2 | NM_133852.2 | chr2:32143772-32163441 |
| 12986 | Golga3 | NM_008146.3 | chr5:110605719-110652174 |
| 12987 | Golga4 | NM_018748.3 | chr9:118415435-118491637 |
| 12988 | Golga5 | NM_001199004.1 | chr12:103707343-103736117 |
| 12989 | Golga5 | NM_013747.4 | chr12:103707343-103736117 |
| 12990 | Golga7 | NM_001042484.1 | chr8:24351797-24367552 |
| 12991 | Golga7 | NM_020585.2 | chr8:24351797-24367552 |
| 12992 | Golga7b | NM_001141983.1 | chr19:42322067-42344838 |
| 12993 | Golga7b | NM_027694.2 | chr19:42322067-42344838 |
| 12994 | Golgb1 | NM_030035.1 | chr16:36885097-36933171 |
| 12995 | Golim4 | NM_001291069.1 | chr3:75680104-75760871 |
| 12996 | Golim4 | NM_175193.6 | chr3:75680104-75760871 |
| 12997 | Golm1 | NM_001035122.2 | chr13:59736356-59777145 |
| 12998 | Golm1 | NM_027307.4 | chr13:59736356-59777145 |
| 12999 | Golph3 | NM_025673.2 | chr15:12251250-12281022 |
| 13000 | Golph3l | NM_001177669.1 | chr3:95392855-95423169 |
| 13001 | Golph3l | NM_001177670.1 | chr3:95392855-95423169 |
| 13002 | Golph3l | NM_146133.3 | chr3:95392855-95423169 |
| 13003 | Golt1a | NM_026680.4 | chr1:135206399-135219603 |
| 13004 | Golt1b | NM_025872.4 | chr6:142335762-142352378 |
| 13005 | Gon4l | NM_001242372.1 | chr3:88639152-88717872 |
| 13006 | Gon4l | NM_027389.3 | chr3:88639152-88717872 |
| 13007 | Gopc | NM_001199272.1 | chr10:52056829-52101930 |
| 13008 | Gopc | NM_053187.3 | chr10:52056829-52101930 |
| 13009 | Gorab | NM_178883.5 | chr1:165315039-165333772 |
| 13010 | Gorasp1 | NM_028976.2 | chr9:119834791-119866676 |
| 13011 | Gorasp2 | NM_027352.4 | chr2:70499565-70529782 |
| 13012 | Gorasp2 | NR_027343.1 | chr2:70499565-70529782 |
| 13013 | Gosr1 | NM_016810.3 | chr11:76540103-76577057 |
| 13014 | Gosr2 | NM_019650.3 | chr11:103538162-103559024 |
| 13015 | Got1 | NM_010324.2 | chr19:43574242-43599095 |
| 13016 | Got1l1 | NM_029674.1 | chr8:28307930-28313019 |
| 13017 | Got2 | NM_010325.2 | chr8:98388036-98412265 |
| 13018 | Gp1ba | NM_010326.2 | chr11:70452623-70455557 |
| 13019 | Gp1bb | NM_001001999.1 | chr16:18620411-18630031 |
| 13020 | Gp1bb | NM_010327.2 | chr16:18620411-18630031 |
| 13021 | Gp2 | NM_025989.3 | chr7:126586057-126602786 |
| 13022 | Gp49a | NM_001291892.1 | chr10:51200417-51206135 |
| 13023 | Gp49a | NM_001291893.1 | chr10:51200417-51206135 |
| 13024 | Gp49a | NM_008147.2 | chr10:51200417-51206135 |
| 13025 | Gp5 | NM_008148.4 | chr16:30307770-30310867 |
| 13026 | Gp6 | NM_001163014.1 | chr7:4320314-4349346 |
| 13027 | Gp9 | NM_018762.1 | chr6:87728129-87729756 |
| 13028 | Gpa33 | NM_021610.1 | chr1:168060590-168096641 |
| 13029 | Gpaa1 | NM_010331.2 | chr15:76161723-76165329 |
| 13030 | Gpalpp1 | NM_026177.3 | chr14:76486078-76510622 |
| 13031 | Gpam | NM_008149.3 | chr19:55144223-55173937 |
| 13032 | Gpank1 | NM_001128597.1 | chr17:35258440-35261760 |
| 13033 | Gpank1 | NM_032460.2 | chr17:35258440-35261760 |
| 13034 | Gpat2 | NM_001081089.2 | chr2:127250934-127261828 |
| 13035 | Gpatch1 | NM_026181.1 | chr7:36061562-36103459 |
| 13036 | Gpatch11 | NM_181649.1 | chr17:79234855-79247648 |
| 13037 | Gpatch2 | NM_026367.4 | chr1:189039389-189175308 |
| 13038 | Gpatch2l | NM_027405.2 | chr12:87582827-87632318 |
| 13039 | Gpatch3 | NM_172876.2 | chr4:133130859-133140157 |
| 13040 | Gpatch4 | NM_001110809.2 | chr3:87847027-87859916 |
| 13041 | Gpatch4 | NM_001286857.1 | chr3:87847027-87859916 |
| 13042 | Gpatch4 | NM_025663.4 | chr3:87847027-87859916 |
| 13043 | Gpatch8 | NM_001159492.1 | chr11:102337229-102417472 |
| 13044 | Gpbar1 | NM_174985.1 | chr1:74325173-74326163 |
| 13045 | Gpbp1 | NM_001122963.1 | chr13:112215887-112280249 |
| 13046 | Gpbp1 | NM_028487.4 | chr13:112215887-112280249 |
| 13047 | Gpbp1l1 | NM_029868.2 | chr4:116230332-116266487 |
| 13048 | Gpc1 | NM_016696.4 | chr1:94728263-94756773 |

Fig. 25 - 70

| | | | |
|---|---|---|---|
| 13049 | Gpc2 | NM_172412.2 | chr5:138714887-138721165 |
| 13050 | Gpc3 | NM_016697.3 | chrX:49625604-49967151 |
| 13051 | Gpc4 | NM_008150.2 | chrX:49406194-49518100 |
| 13052 | Gpc5 | NM_175500.4 | chr14:115491437-116924414 |
| 13053 | Gpc6 | NM_001079844.2 | chr14:117324518-118378751 |
| 13054 | Gpc6 | NM_011821.3 | chr14:117324518-118378751 |
| 13055 | Gpcpd1 | NM_001042671.1 | chr2:132354817-132403984 |
| 13056 | Gpcpd1 | NM_001042672.1 | chr2:132354817-132403984 |
| 13057 | Gpcpd1 | NM_001291050.1 | chr2:132354817-132403984 |
| 13058 | Gpcpd1 | NM_001291051.1 | chr2:132354817-132403984 |
| 13059 | Gpcpd1 | NM_001291052.1 | chr2:132354817-132403984 |
| 13060 | Gpcpd1 | NM_027096.2 | chr2:132354817-132403984 |
| 13061 | Gpcpd1 | NM_028802.3 | chr2:132354817-132403984 |
| 13062 | Gpd1 | NM_010271.2 | chr15:99548023-99555438 |
| 13063 | Gpd1l | NM_175380.5 | chr9:114808456-114843105 |
| 13064 | Gpd2 | NM_001145820.1 | chr2:57090088-57223130 |
| 13065 | Gpd2 | NM_010274.3 | chr2:57090088-57223130 |
| 13066 | Gper1 | NM_029771.3 | chr5:139899133-139903754 |
| 13067 | Gpha2 | NM_130453.3 | chr19:6226401-6227768 |
| 13068 | Ghhb5 | NM_175644.3 | chr12:76512706-76517768 |
| 13069 | Gphn | NM_145965.2 | chr12:79326641-79785756 |
| 13070 | Gphn | NM_172952.3 | chr12:79327641-79785756 |
| 13071 | Gpi1 | NM_008155.3 | chr7:34986345-35015355 |
| 13072 | Gpihbp1 | NM_026730.1 | chr15:75427087-75428643 |
| 13073 | Gpkow | NM_173747.3 | chrX:7274259-7287385 |
| 13074 | Gpld1 | NM_008156.2 | chr13:25035020-25083805 |
| 13075 | Gpm6a | NM_001253754.1 | chr8:55864786-56146231 |
| 13076 | Gpm6a | NM_001253756.1 | chr8:55864786-56146231 |
| 13077 | Gpm6a | NM_153581.6 | chr8:55864786-56146231 |
| 13078 | Gpm6b | NM_001177955.1 | chrX:162676874-162826965 |
| 13079 | Gpm6b | NM_001177956.1 | chrX:162676874-162826965 |
| 13080 | Gpm6b | NM_001177957.1 | chrX:162676874-162826965 |
| 13081 | Gpm6b | NM_001177958.1 | chrX:162676874-162826965 |
| 13082 | Gpm6b | NM_001177959.1 | chrX:162676874-162826965 |
| 13083 | Gpm6b | NM_001177960.1 | chrX:162676874-162826965 |
| 13084 | Gpm6b | NM_001177961.1 | chrX:162676874-162826965 |
| 13085 | Gpm6b | NM_001177962.1 | chrX:162676874-162826965 |
| 13086 | Gpm6b | NM_023122.3 | chrX:162676874-162826965 |
| 13087 | Gpn1 | NM_133756.4 | chr5:31797133-31814600 |
| 13088 | Gpn2 | NM_001290742.1 | chr4:133140287-133147650 |
| 13089 | Gpn2 | NM_133884.2 | chr4:133140287-133147650 |
| 13090 | Gpn3 | NM_024216.1 | chr5:122822516-122832778 |
| 13091 | Gpnmb | NM_053110.4 | chr6:48986516-49008181 |
| 13092 | Gpr1 | NM_146250.2 | chr1:63229145-63260855 |
| 13093 | Gpr101 | NM_001033360.3 | chrX:54749844-54756934 |
| 13094 | Gpr107 | NM_178760.4 | chr2:31007835-31072087 |
| 13095 | Gpr108 | NM_030084.4 | chr17:57374337-57387064 |
| 13096 | Gpr110 | NM_133776.2 | chr17:43407295-43461355 |
| 13097 | Gpr111 | NM_001033493.2 | chr17:42845885-42879128 |
| 13098 | Gpr113 | NM_001014394.2 | chr5:30519970-30532262 |
| 13099 | Gpr114 | NM_001033468.3 | chr8:97447593-97467190 |
| 13100 | Gpr114 | NM_001145972.1 | chr8:97447593-97467190 |
| 13101 | Gpr115 | NM_001289499.1 | chr17:42793835-42829233 |
| 13102 | Gpr115 | NM_001289500.1 | chr17:42793835-42829233 |
| 13103 | Gpr115 | NM_001289501.1 | chr17:42793835-42829233 |
| 13104 | Gpr115 | NM_030067.2 | chr17:42793835-42829233 |
| 13105 | Gpr116 | NM_001081178.1 | chr17:43526414-43596506 |
| 13106 | Gpr119 | NM_181751.2 | chrX:46021155-46027655 |
| 13107 | Gpr12 | NM_001010941.2 | chr5:147393725-147396815 |
| 13108 | Gpr12 | NM_008151.3 | chr5:147393725-147396815 |
| 13109 | Gpr123 | NM_177469.3 | chr7:147020072-147063987 |
| 13110 | Gpr124 | NM_054044.2 | chr8:28196312-28233908 |
| 13111 | Gpr125 | NM_133911.1 | chr5:50351189-50450235 |
| 13112 | Gpr126 | NM_001002268.3 | chr10:14122390-14264842 |
| 13113 | Gpr128 | NM_172825.3 | chr6:56724721-56795971 |
| 13114 | Gpr132 | NM_019925.4 | chr12:114089086-114099127 |
| 13115 | Gpr133 | NM_001081342.1 | chr5:129602624-129710474 |
| 13116 | Gpr135 | NM_181752.1 | chr12:73170604-73171978 |
| 13117 | Gpr137 | NM_001177360.1 | chr19:7012559-7026395 |
| 13118 | Gpr137 | NM_001177361.1 | chr19:7012559-7026395 |
| 13119 | Gpr137 | NM_001177362.1 | chr19:7012559-7026395 |
| 13120 | Gpr137 | NM_207220.2 | chr19:7012559-7026395 |
| 13121 | Gpr137b | NM_031999.2 | chr13:13449887-13485891 |
| 13122 | Gpr137b-ps | NR_003568.1 | chr12:12706332-12742662 |
| 13123 | Gpr137c | NM_027518.2 | chr14:45589991-45900651 |
| 13124 | Gpr139 | NM_001024138.1 | chr7:126287836-126327888 |
| 13125 | Gpr141 | NM_181784.4 | chr13:19841550-19916126 |
| 13126 | Gpr142 | NM_181749.1 | chr11:114660237-114668059 |
| 13127 | Gpr143 | NM_010951.3 | chrX:149216463-149243189 |
| 13128 | Gpr146 | NM_001038703.2 | chr5:139835692-139936488 |
| 13129 | Gpr146 | NM_030258.4 | chr5:139835692-139936488 |
| 13130 | Gpr149 | NM_177346.4 | chr3:62333884-62409062 |
| 13131 | Gpr15 | NM_001162955.1 | chr16:58717547-58718837 |
| 13132 | Gpr150 | NM_175495.2 | chr13:76192298-76194444 |
| 13133 | Gpr151 | NM_181815.1 | chr18:42737673-42739306 |
| 13134 | Gpr152 | NM_206973.2 | chr19:4139798-4145740 |
| 13135 | Gpr153 | NM_178456.4 | chr4:151648470-151659446 |
| 13136 | Gpr155 | NM_001190297.2 | chr2:73179562-73224537 |
| 13137 | Gpr155 | NM_001276443.1 | chr2:73179562-73224537 |
| 13138 | Gpr155 | NM_001276444.1 | chr2:73179562-73224537 |
| 13139 | Gpr156 | NM_153394.2 | chr16:37916581-38007615 |
| 13140 | Gpr157 | NM_177366.3 | chr4:149461611-149480036 |
| 13141 | Gpr158 | NM_001004761.1 | chr2:21289193-21752169 |
| 13142 | Gpr160 | NM_001134385.2 | chr3:30754871-30796116 |
| 13143 | Gpr160 | NM_001134386.2 | chr3:30754871-30796116 |
| 13144 | Gpr160 | NM_001286994.1 | chr3:30754871-30796116 |
| 13145 | Gpr160 | NM_001286995.1 | chr3:30754871-30796116 |
| 13146 | Gpr160 | NM_001286996.1 | chr3:30754871-30796116 |
| 13147 | Gpr160 | NM_027965.2 | chr3:30754871-30796116 |
| 13148 | Gpr161 | NM_001081126.1 | chr1:167225896-167251982 |
| 13149 | Gpr162 | NM_013533.3 | chr6:124808462-124813935 |
| 13150 | Gpr165 | NM_029536.3 | chrX:93908806-93914727 |
| 13151 | Gpr17 | NM_001025381.1 | chr18:32102653-32109290 |
| 13152 | Gpr171 | NM_173398.3 | chr3:58900370-58905743 |
| 13153 | Gpr173 | NM_027543.3 | chrX:148779188-148802654 |
| 13154 | Gpr174 | NM_001033251.4 | chrX:104451216-104492108 |
| 13155 | Gpr174 | NM_001177781.1 | chrX:104451216-104492108 |
| 13156 | Gpr174 | NM_001177782.1 | chrX:104451216-104492108 |
| 13157 | Gpr176 | NM_201367.3 | chr2:118102834-118199155 |
| 13158 | Gpr179 | NM_001081220.1 | chr11:97193422-97213387 |
| 13159 | Gpr18 | NM_182806.1 | chr14:122310656-122314996 |
| 13160 | Gpr180 | NM_021434.5 | chr14:118536348-118563454 |
| 13161 | Gpr182 | NM_007412.2 | chr10:127186657-127188854 |
| 13162 | Gpr183 | NM_183031.2 | chr14:122351553-122364415 |
| 13163 | Gpr19 | NM_001167694.1 | chr6:134819109-134847943 |
| 13164 | Gpr19 | NM_001167695.1 | chr6:134819109-134847943 |
| 13165 | Gpr19 | NM_001167696.2 | chr6:134819109-134847943 |
| 13166 | Gpr19 | NM_001167697.2 | chr6:134819109-134847943 |
| 13167 | Gpr19 | NM_001167699.2 | chr6:134819109-134847943 |
| 13168 | Gpr19 | NM_001167700.2 | chr6:134819109-134847943 |
| 13169 | Gpr19 | NM_008157.3 | chr6:134819109-134847943 |
| 13170 | Gpr19 | NR_072990.2 | chr6:134819109-134847943 |
| 13171 | Gpr19 | NR_074084.1 | chr6:134819109-134847943 |
| 13172 | Gpr20 | NM_173365.2 | chr15:73525036-73537935 |
| 13173 | Gpr21 | NM_177383.4 | chr2:37372146-37374801 |
| 13174 | Gpr22 | NM_175191.1 | chr12:32391732-32398791 |
| 13175 | Gpr25 | NM_001101516.1 | chr1:138155490-138157450 |
| 13176 | Gpr26 | NM_173410.3 | chr7:139158142-139177316 |
| 13177 | Gpr27 | NM_008158.1 | chr6:99642672-99643812 |
| 13178 | Gpr3 | NM_008154.3 | chr4:132765254-132768451 |
| 13179 | Gpr31b | NM_001013832.2 | chr17:13244186-13245146 |
| 13180 | Gpr33 | NM_008159.2 | chr12:53123990-53129050 |
| 13181 | Gpr34 | NM_011823.4 | chrX:13209895-13217984 |
| 13182 | Gpr35 | NM_001104529.1 | chr1:94869695-94882968 |
| 13183 | Gpr35 | NM_001271766.1 | chr1:94869695-94882968 |
| 13184 | Gpr35 | NM_022320.4 | chr1:94869695-94882968 |
| 13185 | Gpr37 | NM_010338.2 | chr6:25618522-25639980 |
| 13186 | Gpr37l1 | NM_134438.3 | chr1:137056826-137064258 |
| 13187 | Gpr39 | NM_027677.2 | chr1:127573573-127770438 |
| 13188 | Gpr4 | NM_175668.4 | chr7:19797886-19809525 |
| 13189 | Gpr45 | NM_053107.4 | chr1:43009716-43092294 |
| 13190 | Gpr50 | NM_010340.2 | chrX:68916941-68921264 |
| 13191 | Gpr52 | NM_001146330.1 | chr1:162506799-162507884 |
| 13192 | Gpr55 | NM_001033290.2 | chr1:87836111-87857630 |
| 13193 | Gpr56 | NM_001198894.1 | chr8:97501008-97538108 |
| 13194 | Gpr56 | NM_188882.3 | chr8:97501008-97538108 |
| 13195 | Gpr6 | NM_199058.1 | chr10:40790298-40791390 |
| 13196 | Gpr61 | NM_175470.4 | chr3:107951238-107957800 |
| 13197 | Gpr62 | NM_001159652.1 | chr9:106366291-106368271 |
| 13198 | Gpr63 | NM_030733.3 | chr4:24900565-24936380 |
| 13199 | Gpr64 | NM_001079847.2 | chrX:156828621-156936008 |
| 13200 | Gpr64 | NM_001079848.2 | chrX:156828621-156936008 |
| 13201 | Gpr64 | NM_001079857.2 | chrX:156828621-156936008 |
| 13202 | Gpr64 | NM_001290445.1 | chrX:156828621-156936008 |
| 13203 | Gpr64 | NM_001290446.1 | chrX:156828621-156936008 |
| 13204 | Gpr64 | NM_178712.4 | chrX:156828621-156936008 |
| 13205 | Gpr65 | NM_008152.3 | chr12:99506844-99514932 |
| 13206 | Gpr68 | NM_001177673.1 | chr12:102114891-102146408 |
| 13207 | Gpr68 | NM_001177674.1 | chr12:102114891-102146408 |
| 13208 | Gpr68 | NM_175493.4 | chr12:102114891-102146408 |
| 13209 | Gpr75 | NM_175490.4 | chr11:30785357-30793725 |
| 13210 | Gpr82 | NM_175669.3 | chrX:13238489-13244559 |
| 13211 | Gpr83 | NM_010287.2 | chr9:14664697-14673943 |
| 13212 | Gpr84 | NM_030720.1 | chr15:103138665-103140869 |
| 13213 | Gpr85 | NM_145066.4 | chr6:13785073-13789848 |
| 13214 | Gpr87 | NM_032399.1 | chr3:58,982,845-58,984,007 |
| 13215 | Gpr88 | NM_022427.2 | chr3:115952571-115956402 |
| 13216 | Gpr89 | NM_026229.4 | chr3:96674988-96709221 |
| 13217 | Gpr97 | NM_173036.3 | chr8:97541591-97569149 |
| 13218 | Gpr98 | NM_054053.4 | chr13:81234066-81772143 |
| 13219 | Gprasp1 | NM_001004359.2 | chrX:132277230-132338007 |
| 13220 | Gprasp1 | NM_001005385.1 | chrX:132277230-132338007 |
| 13221 | Gprasp1 | NM_026081.5 | chrX:132277230-132338007 |
| 13222 | Gprasp2 | NM_001163015.1 | chrX:132373572-132379269 |
| 13223 | Gprasp2 | NM_001163016.1 | chrX:132373572-132379269 |
| 13224 | Gprasp2 | NM_001163017.1 | chrX:132373572-132379269 |
| 13225 | Gprc5a | NM_181444.2 | chr6:135015679-135034726 |
| 13226 | Gprc5b | NM_001195774.1 | chr7:125985731-126138725 |
| 13227 | Gprc5b | NM_022420.2 | chr7:125985731-126138725 |
| 13228 | Gprc5c | NM_001110337.1 | chr11:114712845-114733931 |
| 13229 | Gprc5c | NM_001110338.1 | chr11:114712845-114733931 |
| 13230 | Gprc5c | NM_147217.3 | chr11:114712845-114733931 |
| 13231 | Gprc5d | NM_001205396.1 | chr6:135056008-135068301 |
| 13232 | Gprc5d | NM_053118.1 | chr6:135056008-135068301 |
| 13233 | Gprc6a | NM_153071.1 | chr10:51334628-51351264 |
| 13234 | Gprin1 | NM_012014.3 | chr13:54838503-54851030 |
| 13235 | Gprin2 | NM_183209.2 | chr14:35007626-35014819 |
| 13236 | Gprin3 | NM_183183.2 | chr6:59302454-59376284 |
| 13237 | Gps1 | NM_001177874.1 | chr11:120645585-120650416 |
| 13238 | Gps1 | NM_145370.2 | chr11:120645585-120650416 |

Fig. 25 - 71

| | | | |
|---|---|---|---|
| 13239 | Gps2 | NM_019726.3 | chr11:69727693-69730093 |
| 13240 | Gpsm1 | NM_001199146.1 | chr2:26171052-26207630 |
| 13241 | Gpsm1 | NM_001199147.1 | chr2:26171052-26207630 |
| 13242 | Gpsm1 | NM_153410.5 | chr2:26171052-26207630 |
| 13243 | Gpsm2 | NM_029522.2 | chr3:108481556-108525217 |
| 13244 | Gpsm3 | NM_134116.5 | chr17:34726756-34728699 |
| 13245 | Gpt | NM_182805.2 | chr15:76527193-76530105 |
| 13246 | Gpt2 | NM_173866.3 | chr8:88016515-88051457 |
| 13247 | Gpx1 | NM_008160.3 | chr9:108241410-108242673 |
| 13248 | Gpx2 | NM_030677.2 | chr12:77893321-77896541 |
| 13249 | Gpx2-ps1 | NR_033563.1 | chr7:107410054-107414071 |
| 13250 | Gpx3 | NM_008161.3 | chr11:54716355-54723884 |
| 13251 | Gpx4 | NM_001037741.3 | chr10:79509910-79519184 |
| 13252 | Gpx4 | NM_008162.3 | chr10:79509910-79519184 |
| 13253 | Gpx4 | NR_110342.1 | chr10:79509910-79519184 |
| 13254 | Gpx5 | NM_010343.2 | chr13:21378297-21384555 |
| 13255 | Gpx6 | NM_145451.3 | chr13:21404071-21411493 |
| 13256 | Gpx7 | NM_024198.3 | chr4:108072821-108079318 |
| 13257 | Gpx8 | NM_027127.2 | chr13:113832971-113836596 |
| 13258 | Gramd1a | NM_027898.1 | chr7:31915145-31936069 |
| 13259 | Gramd1b | NM_172768.1 | chr9:40105492-40263349 |
| 13260 | Gramd1c | NM_001172107.1 | chr16:43980462-44028058 |
| 13261 | Gramd1c | NM_153528.2 | chr16:43980462-44028058 |
| 13262 | Gramd2 | NM_001033498.1 | chr9:59555570-59564231 |
| 13263 | Gramd3 | NM_026240.2 | chr18:56591785-56663446 |
| 13264 | Gramd4 | NM_001205353.1 | chr15:85888124-85968066 |
| 13265 | Gramd4 | NM_172611.4 | chr15:85888124-85968066 |
| 13266 | Grap | NM_027817.3 | chr11:61466822-61486279 |
| 13267 | Grap2 | NM_001289442.1 | chr15:80403026-80483284 |
| 13268 | Grap2 | NM_010815.3 | chr15:80403026-80483284 |
| 13269 | Grasp | NM_019518.3 | chr15:101054638-101063187 |
| 13270 | Grb10 | NM_001177629.1 | chr11:11830501-11937423 |
| 13271 | Grb10 | NM_010345.4 | chr11:11830501-11937423 |
| 13272 | Grb14 | NM_016719.1 | chr2:64750059-64860823 |
| 13273 | Grb2 | NM_008163.3 | chr11:115505457-115569911 |
| 13274 | Grb7 | NM_010346.2 | chr11:98308147-98316687 |
| 13275 | Grcc10 | NM_013535.1 | chr6:124689201-124691097 |
| 13276 | Greb1 | NM_001252071.1 | chr12:16677420-16807692 |
| 13277 | Greb1 | NM_015764.4 | chr12:16677420-16807692 |
| 13278 | Greb1l | NM_001083628.1 | chr18:10325176-10562939 |
| 13279 | Grem1 | NM_011824.4 | chr2:113588831-113598805 |
| 13280 | Grem2 | NM_011825.1 | chr1:176763915-176851950 |
| 13281 | Grhl1 | NM_001161406.1 | chr12:25257151-25302256 |
| 13282 | Grhl1 | NM_145890.2 | chr12:25257151-25302256 |
| 13283 | Grhl2 | NM_026496.4 | chr15:37162790-37293323 |
| 13284 | Grhl3 | NM_001013756.1 | chr4:135097802-135129535 |
| 13285 | Grhpr | NM_080289.1 | chr4:44994282-45003568 |
| 13286 | Gria1 | NM_001113325.1 | chr11:56825119-57143746 |
| 13287 | Gria1 | NM_001252403.1 | chr11:56825119-57143746 |
| 13288 | Gria1 | NM_008165.4 | chr11:56825119-57143746 |
| 13289 | Gria2 | NM_001039195.1 | chr3:80488857-80606713 |
| 13290 | Gria2 | NM_001083806.1 | chr3:80488857-80606713 |
| 13291 | Gria2 | NM_013540.2 | chr3:80488857-80606713 |
| 13292 | Gria3 | NM_001281929.1 | chrX:38754477-39031778 |
| 13293 | Gria3 | NM_001290451.1 | chrX:38754477-39031778 |
| 13294 | Gria3 | NM_016886.4 | chrX:38754477-39031778 |
| 13295 | Gria3 | NR_104053.1 | chrX:38754477-39031778 |
| 13296 | Gria4 | NM_001113180.1 | chr9:4417892-4796234 |
| 13297 | Gria4 | NM_001113181.1 | chr9:4417892-4796234 |
| 13298 | Gria4 | NM_019691.4 | chr9:4417892-4796234 |
| 13299 | Grid1 | NM_008166.2 | chr14:35633322-36394301 |
| 13300 | Grid2 | NM_008167.2 | chr6:63206850-64616273 |
| 13301 | Grid2ip | NM_001159321.1 | chr5:144119016-144153477 |
| 13302 | Grid2ip | NM_133355.1 | chr5:144119016-144153477 |
| 13303 | Grifin | NM_030022.1 | chr5:141039142-141041021 |
| 13304 | Grik1 | NM_010348.3 | chr16:87896141-88290503 |
| 13305 | Grik1 | NM_146072.4 | chr16:87896141-88290503 |
| 13306 | Grik2 | NM_001111268.1 | chr10:48819268-49508560 |
| 13307 | Grik2 | NM_010349.2 | chr10:48819268-49508560 |
| 13308 | Grik3 | NM_001051097.2 | chr4:125168075-125391417 |
| 13309 | Grik4 | NM_175481.5 | chr9:42328494-42752454 |
| 13310 | Grik5 | NM_008168.2 | chr7:25794869-25857388 |
| 13311 | Grin1 | NM_001177656.1 | chr2:25145430-25174707 |
| 13312 | Grin1 | NM_001177657.2 | chr2:25145430-25174707 |
| 13313 | Grin1 | NM_008169.3 | chr2:25145430-25174707 |
| 13314 | Grin1os | NM_001242940.1 | chr2:25146748-25154448 |
| 13315 | Grin2a | NM_008170.2 | chr16:9577802-9992626 |
| 13316 | Grin2b | NM_008171.3 | chr6:135679822-136123529 |
| 13317 | Grin2c | NM_010350.3 | chr11:15110482-15128557 |
| 13318 | Grin2d | NM_008172.2 | chr7:53087852-53122051 |
| 13319 | Grin3a | NM_001033351.2 | chr4:49674482-49858641 |
| 13320 | Grin3a | NM_001276355.1 | chr4:49674482-49858641 |
| 13321 | Grin3b | NM_130455.2 | chr10:79433469-79439935 |
| 13322 | Grina | NM_023168.3 | chr15:76077237-76080334 |
| 13323 | Grip1 | NM_001277292.1 | chr10:118891089-119550021 |
| 13324 | Grip1 | NM_001277293.1 | chr10:118891089-119550021 |
| 13325 | Grip1 | NM_001277294.1 | chr10:118891089-119550021 |
| 13326 | Grip1 | NM_001277295.1 | chr10:118891089-119550021 |
| 13327 | Grip1 | NM_028736.2 | chr10:118891089-119550021 |
| 13328 | Grip1 | NM_130150.2 | chr10:118891089-119550021 |
| 13329 | Grip1 | NM_133442.2 | chr10:118891089-119550021 |
| 13330 | Grip1os | NR_102387.1 | chr10:118891089-119550021 |
| 13331 | Grip1os2 | NR_045359.1 | chr10:119183118-119198755 |
| 13332 | Grip2 | NM_001159507.1 | chr6:91715502-91757387 |
| 13333 | Gripap1 | NM_001290455.1 | chrX:7367118-7397693 |
| 13334 | Gripap1 | NM_207670.2 | chrX:7367118-7397693 |
| 13335 | Grk1 | NM_013881.3 | chr8:13405080-13421949 |
| 13336 | Grk4 | NM_001080743.1 | chr5:35003027-35097952 |
| 13337 | Grk4 | NM_019497.2 | chr5:35003027-35097952 |
| 13338 | Grk5 | NM_018869.3 | chr19:60865651-61168458 |
| 13339 | Grk6 | NM_001038018.4 | chr13:55546432-55562288 |
| 13340 | Grk6 | NM_001112711.2 | chr13:55546432-55562288 |
| 13341 | Grk6 | NM_001286063.1 | chr13:55546432-55562288 |
| 13342 | Grk6 | NM_001286064.1 | chr13:55546432-55562288 |
| 13343 | Grk6 | NM_001286065.1 | chr13:55546432-55562288 |
| 13344 | Grk6 | NM_001286066.1 | chr13:55546432-55562288 |
| 13345 | Grk6 | NM_011938.4 | chr13:55546432-55562288 |
| 13346 | Grm1 | NM_001114333.2 | chr10:10405856-10802129 |
| 13347 | Grm1 | NM_016976.3 | chr10:10405856-10802129 |
| 13348 | Grm2 | NM_001160353.1 | chr9:106546865-106558440 |
| 13349 | Grm3 | NM_181850.2 | chr5:9485235-9725352 |
| 13350 | Grm4 | NM_001013385.2 | chr17:27559332-27640478 |
| 13351 | Grm4 | NM_001291045.1 | chr17:27559332-27640478 |
| 13352 | Grm5 | NM_001081414.2 | chr7:94732677-95283573 |
| 13353 | Grm5 | NM_001143834.1 | chr7:94732677-95283573 |
| 13354 | Grm6 | NM_173372.2 | chr11:50664186-50679710 |
| 13355 | Grm7 | NM_177328.3 | chr6:110595591-111517224 |
| 13356 | Grm8 | NM_008174.2 | chr6:27225121-28084369 |
| 13357 | Grn | NM_008175.4 | chr11:102291635-102298123 |
| 13358 | Grp | NM_175012.3 | chr18:66033132-66046250 |
| 13359 | Grpel1 | NM_024478.2 | chr5:36807834-36816726 |
| 13360 | Grpel2 | NM_021296.2 | chr18:61872077-61885985 |
| 13361 | Grpr | NM_008177.3 | chrX:159951835-159987579 |
| 13362 | Grrp1 | NM_001099296.2 | chr4:133807024-133810021 |
| 13363 | Grsf1 | NM_001098476.2 | chr5:89088257-89105196 |
| 13364 | Grsf1 | NM_178700.5 | chr5:89088257-89105196 |
| 13365 | Grtp1 | NM_025768.2 | chr8:13176869-13200624 |
| 13366 | Grwd1 | NM_153419.2 | chr7:53080592-53086159 |
| 13367 | Grxcr1 | NM_001018019.2 | chr5:68423073-68557637 |
| 13368 | Grxcr2 | NM_001033426.2 | chr18:42145854-42158703 |
| 13369 | Gsap | NM_175437.3 | chr5:20692084-20797519 |
| 13370 | Gsc | NM_010351.1 | chr12:105709418-105711446 |
| 13371 | Gsc2 | NM_029469.1 | chr16:17913646-17915152 |
| 13372 | Gsdma | NM_021347.4 | chr11:98525664-98539022 |
| 13373 | Gsdma2 | NM_029727.2 | chr11:98508072-98519271 |
| 13374 | Gsdma3 | NM_001007461.1 | chr11:98487673-98499403 |
| 13375 | Gsdmc | NM_031378.3 | chr15:63607525-63640294 |
| 13376 | Gsdmc2 | NM_001168274.1 | chr15:63655900-63676731 |
| 13377 | Gsdmc2 | NM_177912.4 | chr15:63655900-63676731 |
| 13378 | Gsdmc3 | NM_183194.3 | chr15:63689279-63710113 |
| 13379 | Gsdmc4 | NM_028992.1 | chr15:63722819-63743852 |
| 13380 | Gsdmcl1 | NR_108051.1 | chr15:63678863-63682497 |
| 13381 | Gsdmcl2 | NR_108053.1 | chr15:68712261-63720628 |
| 13382 | Gsdmcl-ps | NR_029414.1 | chr15:63746015-63757008 |
| 13383 | Gsdmd | NM_026960.4 | chr15:75692768-75697834 |
| 13384 | Gse1 | NM_001145896.1 | chr8:123012765-123112975 |
| 13385 | Gse1 | NM_001145897.1 | chr8:123012765-123112975 |
| 13386 | Gse1 | NM_198671.2 | chr8:123012765-123112975 |
| 13387 | Gsg1 | NM_001080552.1 | chr6:135187347-135204354 |
| 13388 | Gsg1 | NM_001080553.1 | chr6:135187347-135204354 |
| 13389 | Gsg1 | NM_010352.2 | chr6:135187347-135204354 |
| 13390 | Gsg1l | NM_001101488.1 | chr7:133021932-133225925 |
| 13391 | Gsg2 | NM_010353.2 | chr11:72948986-72951796 |
| 13392 | Gsk3a | NM_001031667.1 | chr7:26013278-26022870 |
| 13393 | Gsk3b | NM_019827.3 | chr16:38089087-38246165 |
| 13394 | Gskip | NM_178613.3 | chr12:106923561-106941267 |
| 13395 | Gsn | NM_001206367.1 | chr2:35111878-35163422 |
| 13396 | Gsn | NM_001206368.1 | chr2:35111878-35163422 |
| 13397 | Gsn | NM_001206369.1 | chr2:35111878-35163422 |
| 13398 | Gsn | NM_146120.4 | chr2:35111878-35163422 |
| 13399 | Gspt1 | NM_001130008.1 | chr16:11203475-11254418 |
| 13400 | Gspt1 | NM_146066.2 | chr16:11203475-11254418 |
| 13401 | Gspt2 | NM_008179.2 | chrX:91881407-91883900 |
| 13402 | Gsr | NM_010344.4 | chr8:34763709-34808634 |
| 13403 | Gss | NM_001291111.1 | chr2:155388916-155418546 |
| 13404 | Gss | NM_008180.2 | chr2:155388916-155418546 |
| 13405 | Gsta1 | NM_008181.3 | chr9:78078475-78090490 |
| 13406 | Gsta2 | NM_008182.3 | chr9:78178826-78194952 |
| 13407 | Gsta3 | NM_001077353.2 | chr1:21230665-21255656 |
| 13408 | Gsta3 | NM_001288617.1 | chr1:21230665-21255656 |
| 13409 | Gsta3 | NM_010356.4 | chr1:21230665-21255656 |
| 13410 | Gsta4 | NM_010357.3 | chr9:78039772-78057156 |
| 13411 | Gstcd | NM_026231.2 | chr3:132645514-132754704 |
| 13412 | Gstk1 | NM_029555.2 | chr6:42195933-42200440 |
| 13413 | Gstm1 | NM_010358.5 | chr3:107815167-107820891 |
| 13414 | Gstm2 | NM_008183.3 | chr3:107784619-107789354 |
| 13415 | Gstm3 | NM_010359.2 | chr3:107766613-107772092 |
| 13416 | Gstm4 | NM_001160411.1 | chr3:107843325-107847777 |
| 13417 | Gstm4 | NM_026764.3 | chr3:107843325-107847777 |
| 13418 | Gstm5 | NM_010360.2 | chr3:107698772-107701603 |
| 13419 | Gstm6 | NM_008184.3 | chr3:107741765-107746667 |
| 13420 | Gstm7 | NM_026672.2 | chr3:107729251-107734663 |
| 13421 | Gsto1 | NM_010362.2 | chr19:47929478-47939278 |
| 13422 | Gsto2 | NM_026619.2 | chr19:47940034-47960795 |
| 13423 | Gsto2 | NM_030051.1 | chr19:47940034-47960795 |
| 13424 | Gstp1 | NM_013541.1 | chr19:4035410-4037912 |
| 13425 | Gstp2 | NM_181796.2 | chr19:4040287-4042221 |
| 13426 | Gstt1 | NM_008185.3 | chr10:75246557-75261329 |
| 13427 | Gstt2 | NM_010361.2 | chr10:75294589-75297626 |
| 13428 | Gstt3 | NM_133994.3 | chr10:75236866-75244159 |

Fig. 25 - 72

| | | | |
|---|---|---|---|
| 13429 | Gstt4 | NM_029472.3 | chr10:75277688-75285288 |
| 13430 | Gstz1 | NM_001252555.1 | chr12:88447815-88505673 |
| 13431 | Gstz1 | NM_001252556.1 | chr12:88447815-88505673 |
| 13432 | Gstz1 | NM_010363.4 | chr12:88447815-88505673 |
| 13433 | Gsx1 | NM_008178.2 | chr5:148000271-148002522 |
| 13434 | Gsx2 | NM_133256.2 | chr5:75471625-75473918 |
| 13435 | Gt(ROSA)26Sor | NR_027008.1 | chr6:112996320-113027238 |
| 13436 | Gt(ROSA)26Sor | NR_027009.1 | chr6:112996320-113027238 |
| 13437 | Gt(ROSA)26Sor | NR_027010.1 | chr6:112996320-113027238 |
| 13438 | Gtdc1 | NM_172662.3 | chr2:44419931-44717142 |
| 13439 | Gtf2a1 | NM_031391.2 | chr12:92793701-92828927 |
| 13440 | Gtf2a1 | NM_175335.3 | chr12:92793701-92828927 |
| 13441 | Gtf2a1l | NM_023630.2 | chr17:89067999-89114490 |
| 13442 | Gtf2a2 | NM_001039519.2 | chr9:69860354-69870673 |
| 13443 | Gtf2a2 | NM_001282083.1 | chr9:69860354-69870673 |
| 13444 | Gtf2a2 | NM_001282084.1 | chr9:69860354-69870673 |
| 13445 | Gtf2a2 | NR_104093.1 | chr9:69860354-69870673 |
| 13446 | Gtf2b | NM_145546.1 | chr3:142428210-142446569 |
| 13447 | Gtf2e1 | NM_028812.3 | chr16:37509881-37539855 |
| 13448 | Gtf2e2 | NM_001167921.1 | chr8:34842385-34887645 |
| 13449 | Gtf2e2 | NM_001167922.1 | chr8:34842385-34887645 |
| 13450 | Gtf2e2 | NM_026584.3 | chr8:34842385-34887645 |
| 13451 | Gtf2f1 | NM_133801.2 | chr17:57142824-57150711 |
| 13452 | Gtf2f2 | NM_026816.3 | chr14:76296744-76410672 |
| 13453 | Gtf2h1 | NM_001291075.1 | chr7:54051463-54079170 |
| 13454 | Gtf2h1 | NM_008186.4 | chr7:54051463-54079170 |
| 13455 | Gtf2h2 | NM_022011.4 | chr13:101238531-101262564 |
| 13456 | Gtf2h3 | NM_181410.3 | chr5:125029156-125047689 |
| 13457 | Gtf2h4 | NM_010364.4 | chr17:35804683-35810627 |
| 13458 | Gtf2h5 | NM_181392.3 | chr17:6079827-6085485 |
| 13459 | Gtf2i | NM_001080746.2 | chr5:134713701-134790630 |
| 13460 | Gtf2i | NM_001080747.2 | chr5:134713701-134790630 |
| 13461 | Gtf2i | NM_001080748.2 | chr5:134713701-134790630 |
| 13462 | Gtf2i | NM_001080749.2 | chr5:134713701-134790630 |
| 13463 | Gtf2i | NM_010365.1 | chr5:134713701-134790630 |
| 13464 | Gtf2ird1 | NM_001081462.2 | chr5:134833530-134932586 |
| 13465 | Gtf2ird1 | NM_001081463.2 | chr5:134833530-134932586 |
| 13466 | Gtf2ird1 | NM_001081464.2 | chr5:134833530-134932586 |
| 13467 | Gtf2ird1 | NM_001081465.1 | chr5:134833530-134932586 |
| 13468 | Gtf2ird1 | NM_001081466.2 | chr5:134833530-134932586 |
| 13469 | Gtf2ird1 | NM_001081467.2 | chr5:134833530-134932586 |
| 13470 | Gtf2ird1 | NM_001081468.2 | chr5:134833530-134932586 |
| 13471 | Gtf2ird1 | NM_001081469.2 | chr5:134833530-134932586 |
| 13472 | Gtf2ird1 | NM_001081470.2 | chr5:134833530-134932586 |
| 13473 | Gtf2ird1 | NM_001249436.1 | chr5:134833530-134932586 |
| 13474 | Gtf2ird1 | NM_020331.2 | chr5:134833530-134932586 |
| 13475 | Gtf2ird2 | NM_053266.1 | chr5:134659907-134694013 |
| 13476 | Gtf3a | NM_025652.3 | chr5:147760233-147767190 |
| 13477 | Gtf3c1 | NM_207239.1 | chr7:132784467-132851202 |
| 13478 | Gtf3c2 | NM_027901.2 | chr5:31458379-31482517 |
| 13479 | Gtf3c3 | NM_001033194.2 | chr1:54454424-54495815 |
| 13480 | Gtf3c4 | NM_001166033.1 | chr2:28677819-28695880 |
| 13481 | Gtf3c4 | NM_172977.3 | chr2:28677819-28695880 |
| 13482 | Gtf3c5 | NM_001290484.1 | chr2:28421764-28438799 |
| 13483 | Gtf3c5 | NM_148928.2 | chr2:28421764-28438799 |
| 13484 | Gtf3c6 | NM_026113.4 | chr10:39969008-39977471 |
| 13485 | Gtl3 | NM_008187.2 | chr8:97944149-97958769 |
| 13486 | Gtpbp1 | NM_013818.2 | chr15:79521325-79551909 |
| 13487 | Gtpbp10 | NM_153116.1 | chr5:5537456-5559501 |
| 13488 | Gtpbp2 | NM_001145979.1 | chr17:46297980-46306319 |
| 13489 | Gtpbp2 | NM_019581.3 | chr17:46297980-46306319 |
| 13490 | Gtpbp3 | NM_032544.3 | chr8:74012001-74017299 |
| 13491 | Gtpbp4 | NM_027000.4 | chr13:8971723-8995258 |
| 13492 | Gtpbp6 | NM_145147.5 | chr5:110532996-110537216 |
| 13493 | Gtpbp8 | NM_001159329.1 | chr16:44738991-44746476 |
| 13494 | Gtpbp8 | NM_025332.3 | chr16:44738991-44746476 |
| 13495 | Gtse1 | NM_001168672.1 | chr15:85690136-85707003 |
| 13496 | Gtse1 | NM_013882.2 | chr15:85690136-85707003 |
| 13497 | Gtsf1 | NM_028797.1 | chr15:103232889-103260858 |
| 13498 | Gtsf1l | NM_026630.2 | chr2:162912766-162915337 |
| 13499 | Guca1a | NM_008189.2 | chr17:47531506-47537533 |
| 13500 | Guca1b | NM_146079.1 | chr17:47522341-47529916 |
| 13501 | Guca2a | NM_008190.1 | chr4:119310336-119312070 |
| 13502 | Guca2b | NM_008191.2 | chr4:119329207-119331550 |
| 13503 | Gucd1 | NM_175133.1 | chr10:74969558-74980067 |
| 13504 | Gucy1a2 | NM_001033322.2 | chr9:3532348-3905787 |
| 13505 | Gucy1a3 | NM_021896.5 | chr3:81896349-81949799 |
| 13506 | Gucy1b2 | NM_001204340.1 | chr14:63011506-63075126 |
| 13507 | Gucy1b2 | NM_172810.3 | chr14:63011506-63075126 |
| 13508 | Gucy1b3 | NM_001161796.1 | chr3:81835925-81878633 |
| 13509 | Gucy1b3 | NM_017469.4 | chr3:81835925-81878633 |
| 13510 | Gucy2c | NM_001127318.1 | chr6:136645804-136730263 |
| 13511 | Gucy2c | NM_145067.3 | chr6:136645804-136730263 |
| 13512 | Gucy2d | NM_001130693.3 | chr7:105588925-105625988 |
| 13513 | Gucy2e | NM_008192.2 | chr11:69031618-69050524 |
| 13514 | Gucy2f | NM_001607576.2 | chrX:138513831-138631479 |
| 13515 | Gucy2g | NM_001081076.2 | chr19:55272587-55315726 |
| 13516 | Guf1 | NM_172711.2 | chr5:69948180-69964869 |
| 13517 | Guk1 | NM_001159410.1 | chr11:58997356-59005454 |
| 13518 | Guk1 | NM_008193.3 | chr11:58997356-59005454 |
| 13519 | Gulo | NM_178747.3 | chr14:66605623-66628047 |
| 13520 | Gulp1 | NM_028450.3 | chr1:44608516-44853681 |
| 13521 | Gusb | NM_010368.1 | chr5:130464890-130478698 |
| 13522 | Gvin1 | NM_001039160.2 | chr7:113300049-113358854 |
| 13523 | Gvin1 | NM_001039160.2 | chr7:113043632-113102484 |
| 13524 | Gvin1 | NM_029000.3 | chr7:113043632-113102484 |
| 13525 | Gvin1 | NM_029000.3 | chr7:113300049-113358854 |
| 13526 | Gxylt1 | NM_001033275.4 | chr15:93070172-93105515 |
| 13527 | Gxylt2 | NM_198612.2 | chr6:100654727-100755075 |
| 13528 | Gyg | NM_013755.2 | chr3:20021969-20055015 |
| 13529 | Gyk | NM_008194.3 | chrX:82947275-83022158 |
| 13530 | Gyk | NM_212444.2 | chrX:82947275-83022158 |
| 13531 | Gykl1 | NM_010293.3 | chr18:52853332-52855247 |
| 13532 | Gyltl1b | NM_001166633.2 | chr2:92205202-92211214 |
| 13533 | Gyltl1b | NM_001290773.1 | chr2:92205202-92211214 |
| 13534 | Gyltl1b | NM_001290774.1 | chr2:92205202-92211214 |
| 13535 | Gyltl1b | NM_001290775.1 | chr2:92205202-92211214 |
| 13536 | Gyltl1b | NM_172670.3 | chr2:92205202-92211214 |
| 13537 | Gypa | NM_010369.3 | chr8:80317943-80034684 |
| 13538 | Gypc | NM_001048207.1 | chr18:32687973-32719688 |
| 13539 | Gys1 | NM_030678.3 | chr7:52690208-52711987 |
| 13540 | Gys2 | NM_145572.2 | chr6:142371132-142421629 |
| 13541 | Gzf1 | NM_028986.3 | chr2:148506855-148518685 |
| 13542 | Gzma | NM_010370.2 | chr13:113884034-113891189 |
| 13543 | Gzmb | NM_013542.2 | chr14:56877694-56881097 |
| 13544 | Gzmc | NM_010371.2 | chr14:56850237-56853493 |
| 13545 | Gzmd | NM_010372.2 | chr14:56748404-56751430 |
| 13546 | Gzme | NM_010373.3 | chr14:56736455-56739462 |
| 13547 | Gzmf | NM_010374.3 | chr14:56824099-56830244 |
| 13548 | Gzmg | NM_010375.2 | chr14:56775417-56778416 |
| 13549 | Gzmk | NM_008196.1 | chr13:113962081-113971105 |
| 13550 | Gzmm | NM_008504.3 | chr10:79151764-79158005 |
| 13551 | Gzmn | NM_153052.2 | chr14:56784632-56793433 |
| 13552 | H13 | NM_001159551.1 | chr2:152495196-152534404 |
| 13553 | H13 | NM_001159552.1 | chr2:152495196-152534404 |
| 13554 | H13 | NM_001159553.1 | chr2:152495196-152534404 |
| 13555 | H13 | NM_010376.4 | chr2:152495196-152534404 |
| 13556 | H19 | NR_001592.1 | chr7:149,761,437-149,764,051 |
| 13557 | H1f0 | NM_008197.3 | chr15:78858641-78860930 |
| 13558 | H1fnt | NM_027304.2 | chr15:98086412-98087738 |
| 13559 | H1foo | NM_138311.2 | chr6:115894956-115900251 |
| 13560 | H1fx | NM_198622.1 | chr6:87930414-87931476 |
| 13561 | H2-Aa | NM_010378.2 | chr17:34419695-34424716 |
| 13562 | H2-Ab1 | NM_207105.3 | chr17:34400171-34406363 |
| 13563 | H2afb1 | NM_026627.1 | chr2:17918048-17918573 |
| 13564 | H2afb2 | NM_001281530.1 | chrX:113794786-113795134 |
| 13565 | H2afb3 | NM_001281531.1 | chrX:117426357-117426704 |
| 13566 | H2afj | NM_177688.4 | chr6:136756768-136758595 |
| 13567 | H2afv | NM_029938.1 | chr11:6327228-6344446 |
| 13568 | H2afx | NM_010436.2 | chr9:44142797-44144156 |
| 13569 | H2afy | NM_001159513.1 | chr13:56174982-56236911 |
| 13570 | H2afy | NM_001159514.1 | chr13:56174982-56236911 |
| 13571 | H2afy | NM_001159515.1 | chr13:56174982-56236911 |
| 13572 | H2afy | NM_012015.2 | chr13:56174982-56236911 |
| 13573 | H2afy2 | NM_207000.2 | chr10:61201395-61246612 |
| 13574 | H2afy3 | NR_003523.1 | chr15:62049096-62051006 |
| 13575 | H2afz | NM_016750.3 | chr3:137527450-137529886 |
| 13576 | H2bfm | NM_027067.2 | chrX:133461863-133462912 |
| 13577 | H2-Bl | NM_008199.2 | chr17:36217133-36221194 |
| 13578 | H2-D1 | NM_010380.3 | chr17:35400039-35404442 |
| 13579 | H2-DMa | NM_010386.4 | chr17:34259776-34276046 |
| 13580 | H2-DMb1 | NM_010387.3 | chr17:34290135-34297174 |
| 13581 | H2-DMb2 | NM_010388.4 | chr17:34282360-34288040 |
| 13582 | H2-Ea-ps | NM_010381.2 | chr17:34479156-34481590 |
| 13583 | H2-Eb1 | NM_010382.1 | chr17:34442811-34453619 |
| 13584 | H2-Eb2 | NM_001039978.3 | chr17:34462619-34478355 |
| 13585 | H2-K1 | NM_001001892.2 | chr17:34132956-34137278 |
| 13586 | H2-K2 | NR_004446.1 | chr17:34111603-34115736 |
| 13587 | H2-Ke2 | NM_001185182.1 | chr17:34075853-34077288 |
| 13588 | H2-Ke2 | NM_010385.2 | chr17:34075853-34077288 |
| 13589 | H2-Ke6 | NM_013543.2 | chr17:34168977-34165000 |
| 13590 | H2-L | NM_001267808.1 | chr17:35400068-35403675 |
| 13591 | H2-M1 | NM_177636.2 | chr17:36808952-36809142 |
| 13592 | H2-M10.1 | NM_013544.3 | chr17:36458804-36463095 |
| 13593 | H2-M10.2 | NM_177923.1 | chr17:36421225-36423366 |
| 13594 | H2-M10.3 | NM_201608.2 | chr17:36501948-36505362 |
| 13595 | H2-M10.4 | NM_177634.1 | chr17:36597108-36599274 |
| 13596 | H2-M10.5 | NM_177637.3 | chr17:36909854-36913180 |
| 13597 | H2-M10.6 | NM_201611.2 | chr17:36949119-36952511 |
| 13598 | H2-M11 | NM_177635.1 | chr17:36684019-36686197 |
| 13599 | H2-M2 | NM_008204.2 | chr17:37617795-37620474 |
| 13600 | H2-M3 | NM_013819.2 | chr17:37407178-37411430 |
| 13601 | H2-M5 | NM_001115075.1 | chr17:37123799-37126449 |
| 13602 | H2-M9 | NM_008205.1 | chr17:36777369-36779589 |
| 13603 | H2-Oa | NM_008206.2 | chr17:34229324-34232179 |
| 13604 | H2-Ob | NM_010389.3 | chr17:34375849-34382853 |
| 13605 | H2-Q1 | NM_010390.3 | chr17:35457503-35462044 |
| 13606 | H2-Q10 | NM_010391.4 | chr17:35607033-35611508 |
| 13607 | H2-Q2 | NM_010392.2 | chr17:35479277-35482667 |
| 13608 | H2-Q4 | NM_001143689.1 | chr17:35516561-35521619 |
| 13609 | H2-Q5 | NR_051981.1 | chr17:35531043-35532575 |
| 13610 | H2-Q6 | NM_207648.2 | chr17:35561822-35565306 |
| 13611 | H2-Q7 | NM_001198560.1 | chr17:35576099-35580718 |
| 13612 | H2-Q7 | NM_001198561.1 | chr17:35576099-35580718 |
| 13613 | H2-Q7 | NM_010394.4 | chr17:35576099-35580718 |
| 13614 | H2-Q8 | NM_023124.5 | chr17:35561792-35565306 |
| 13615 | H2-Q9 | NM_001201460.1 | chr17:35576112-35580715 |
| 13616 | H2-T10 | NM_010395.7 | chr17:36252815-36258389 |
| 13617 | H2-T10 | NR_046286.1 | chr17:36252815-36258389 |

Fig. 25 - 73

| | | | | | | | | |
|---|---|---|---|---|---|---|---|---|
| 13618 | H2-T22 | NM_010397.4 | chr17:36175354-36179647 | | 13713 | Hcls1 | NM_008225.2 | chr16:36935068-36963300 |
| 13619 | H2-T23 | NM_010398.3 | chr17:36166922-36169646 | | 13714 | Hcn1 | NM_010408.3 | chr13:118391127-118769835 |
| 13620 | H2-T24 | NM_008207.3 | chr17:36142640-36157505 | | 13715 | Hcn2 | NM_008226.2 | chr10:79179378-79198853 |
| 13621 | H2-T3 | NM_008208.4 | chr17:36322515-36327096 | | 13716 | Hcn3 | NM_008227.1 | chr3:88950696-88964079 |
| 13622 | H2-T9 | NM_010399.2 | chr17:36175354-36179637 | | 13717 | Hcn4 | NM_001081192.1 | chr9:58671318-58708762 |
| 13623 | H3f3a | NM_008210.4 | chr1:182732698-182743734 | | 13718 | Hcrt | NM_010410.2 | chr11:100623006-100624245 |
| 13624 | H3f3b | NM_008211.3 | chr11:115883274-115885818 | | 13719 | Hcrtr1 | NM_001163027.1 | chr4:129807460-129816406 |
| 13625 | H60b | NM_001177775.1 | chr10:21993280-22008654 | | 13720 | Hcrtr1 | NM_198959.2 | chr4:129807460-129816406 |
| 13626 | H60c | NM_001204916.2 | chr10:7078769-7090333 | | 13721 | Hcrtr2 | NM_198962.3 | chr9:76073686-76171385 |
| 13627 | H6pd | NM_001291004.1 | chr4:149353582-149383132 | | 13722 | Hcst | NM_011827.3 | chr7:31202730-31204873 |
| 13628 | H6pd | NM_173371.4 | chr4:149353582-149383132 | | 13723 | Hdac1 | NM_008228.2 | chr4:129193347-129219890 |
| 13629 | Haao | NM_025325.2 | chr17:84230693-84246130 | | 13724 | Hdac10 | NM_199198.2 | chr15:88953732-88959130 |
| 13630 | Habp2 | NM_146101.1 | chr19:56362428-56394579 | | 13725 | Hdac10 | NR_028447.1 | chr15:88953732-88959130 |
| 13631 | Habp4 | NM_019986.3 | chr13:64263173-64287845 | | 13726 | Hdac10 | NR_028448.1 | chr15:88953732-88959130 |
| 13632 | Hace1 | NM_172473.3 | chr10:45297634-45432151 | | 13727 | Hdac10 | NR_028449.1 | chr15:88953732-88959130 |
| 13633 | Hacl1 | NM_019975.3 | chr14:32420411-32454151 | | 13728 | Hdac11 | NM_144919.2 | chr6:91106808-91124677 |
| 13634 | Hadh | NM_008212.4 | chr3:130936337-130975019 | | 13729 | Hdac2 | NM_008229.2 | chr10:36694349-36721694 |
| 13635 | Hadha | NM_178878.2 | chr5:30444844-30481520 | | 13730 | Hdac3 | NM_010411.2 | chr18:38096624-38114642 |
| 13636 | Hadhb | NM_001289798.1 | chr5:30481792-30511133 | | 13731 | Hdac4 | NM_207225.1 | chr1:93829931-94044970 |
| 13637 | Hadhb | NM_001289799.1 | chr5:30481792-30511133 | | 13732 | Hdac5 | NM_001077696.1 | chr11:102057060-102091486 |
| 13638 | Hadhb | NM_145558.2 | chr5:30481792-30511133 | | 13733 | Hdac5 | NM_001284248.1 | chr11:102057060-102091486 |
| 13639 | Hagh | NM_001159626.1 | chr17:24987434-25001395 | | 13734 | Hdac5 | NM_001284249.1 | chr11:102057060-102091486 |
| 13640 | Hagh | NM_024284.2 | chr17:24987434-25001395 | | 13735 | Hdac5 | NM_001284250.1 | chr11:102057060-102091486 |
| 13641 | Haghl | NM_001271433.1 | chr17:25910720-25922531 | | 13736 | Hdac5 | NM_010412.3 | chr11:102057060-102091486 |
| 13642 | Haghl | NM_001271434.1 | chr17:25910720-25922531 | | 13737 | Hdac6 | NM_001130416.1 | chrX:7507247-7525015 |
| 13643 | Haghl | NM_001271435.1 | chr17:25910720-25922531 | | 13738 | Hdac6 | NM_010413.3 | chrX:7507247-7525015 |
| 13644 | Haghl | NM_001271436.1 | chr17:25910720-25922531 | | 13739 | Hdac7 | NM_001204275.1 | chr15:97614795-97674933 |
| 13645 | Haghl | NM_001271437.1 | chr17:25910720-25922531 | | 13740 | Hdac7 | NM_001204276.1 | chr15:97614795-97674933 |
| 13646 | Haghl | NM_026897.3 | chr17:25910720-25922531 | | 13741 | Hdac7 | NM_001204277.1 | chr15:97614795-97674933 |
| 13647 | Hal | NM_010401.3 | chr10:92951512-92979488 | | 13742 | Hdac7 | NM_001204278.1 | chr15:97614795-97674933 |
| 13648 | Hamp | NM_032541.1 | chr7:31727387-31729036 | | 13743 | Hdac7 | NM_001204279.1 | chr15:97614795-97674933 |
| 13649 | Hamp2 | NM_183257.3 | chr7:31707390-31709200 | | 13744 | Hdac7 | NM_001204280.1 | chr15:97614795-97674933 |
| 13650 | Hand1 | NM_008213.2 | chr11:57642214-57645649 | | 13745 | Hdac7 | NM_001204281.1 | chr15:97614795-97674933 |
| 13651 | Hand2 | NM_010402.4 | chr8:59799779-59803314 | | 13746 | Hdac7 | NM_019572.3 | chr15:97614795-97674933 |
| 13652 | Hao1 | NM_010403.2 | chr2:134323096-134380088 | | 13747 | Hdac8 | NM_027382.3 | chrX:99479978-99700487 |
| 13653 | Hao2 | NM_019545.4 | chr3:98678441-98697153 | | 13748 | Hdac9 | NM_001271386.1 | chr12:34732446-35601767 |
| 13654 | Hap1 | NM_010404.3 | chr11:100208640-100217455 | | 13749 | Hdac9 | NM_024174.3 | chr12:34732446-35601767 |
| 13655 | Hap1 | NM_177981.2 | chr11:100208640-100217455 | | 13750 | Hdc | NM_008230.6 | chr2:126419395-126444414 |
| 13656 | Hapln1 | NM_013500.4 | chr13:89680240-89751437 | | 13751 | Hddc2 | NM_027168.2 | chr10:31033216-31047892 |
| 13657 | Hapln2 | NM_022031.2 | chr3:87825671-87831433 | | 13752 | Hddc3 | NM_026812.2 | chr7:87488022-87490983 |
| 13658 | Hapln3 | NM_178255.3 | chr7:86261912-86275904 | | 13753 | Hdgf | NM_008231.4 | chr3:87710242-87720054 |
| 13659 | Hapln4 | NM_177904.2 | chr8:72607427-72614761 | | 13754 | Hdgfl1 | NM_008232.3 | chr13:26860040-26862034 |
| 13660 | Harbi1 | NM_178724.4 | chr2:91551106-91561723 | | 13755 | Hdgfrp2 | NM_008233.3 | chr17:56219054-56240027 |
| 13661 | Hars | NM_008214.4 | chr18:36926181-36942859 | | 13756 | Hdgfrp3 | NM_013886.3 | chr7:89026142-89079345 |
| 13662 | Hars2 | NM_080636.2 | chr18:36942933-36952214 | | 13757 | Hdhd1a | NM_026108.3 | chr18:50727309-50728353 |
| 13663 | Has1 | NM_008215.2 | chr17:17980289-17992152 | | 13758 | Hdhd2 | NM_001039201.1 | chr18:77182853-77210910 |
| 13664 | Has2 | NM_008216.3 | chr15:56497182-56526101 | | 13759 | Hdhd2 | NM_001039202.1 | chr18:77182853-77210910 |
| 13665 | Has2os | NR_002874.2 | chr15:56521499-56526015 | | 13760 | Hdhd2 | NM_029826.2 | chr18:77182853-77210910 |
| 13666 | Has3 | NM_008217.4 | chr8:109394141-109406802 | | 13761 | Hdhd3 | NM_024257.1 | chr4:62160087-62163234 |
| 13667 | Hat1 | NM_026115.4 | chr2:71227316-71279679 | | 13762 | Hdlbp | NM_133808.5 | chr1:95302516-95375385 |
| 13668 | Haus1 | NM_146089.2 | chr18:77996305-78006519 | | 13763 | Hdx | NM_001080549.2 | chrX:108688812-108810688 |
| 13669 | Haus2 | NM_001290807.1 | chr2:120429973-120447295 | | 13764 | Hdx | NM_001290459.1 | chrX:108688812-108810688 |
| 13670 | Haus2 | NM_001290808.1 | chr2:120429973-120447295 | | 13765 | Heatr1 | NM_144835.4 | chr13:12487641-12531160 |
| 13671 | Haus2 | NM_025475.3 | chr2:120429973-120447295 | | 13766 | Heatr2 | NM_001081265.1 | chr5:139626176-139662459 |
| 13672 | Haus3 | NM_146159.1 | chr5:34496548-34512073 | | 13767 | Heatr3 | NM_172757.3 | chr8:90661784-90695842 |
| 13673 | Haus4 | NM_145462.2 | chr14:55160621-55173198 | | 13768 | Heatr5a | NM_177171.4 | chr12:52976859-53072308 |
| 13674 | Haus5 | NM_027999.1 | chr7:31438726-31450013 | | 13769 | Heatr5b | NM_001081179.1 | chr17:79152245-79234721 |
| 13675 | Haus6 | NM_173400.2 | chr4:86227189-86257926 | | 13770 | Heatr6 | NM_145432.3 | chr11:83567138-83597256 |
| 13676 | Haus7 | NM_028633.3 | chrX:70682653-70704368 | | 13771 | Heatr9 | NM_001045543.2 | chr11:83325180-83335601 |
| 13677 | Haus7 | NM_207104.1 | chrX:70682653-70704368 | | 13772 | Hebp1 | NM_013546.2 | chr6:135087536-135118233 |
| 13678 | Haus8 | NM_001163042.1 | chr8:73775022-73796489 | | 13773 | Hebp2 | NM_019487.3 | chr10:18259928-18265882 |
| 13679 | Haus8 | NM_029621.3 | chr8:73775022-73796489 | | 13774 | Heca | NM_001034432.3 | chr10:17620271-17667873 |
| 13680 | Havcr1 | NM_001166631.1 | chr11:46553724-46593080 | | 13775 | Hectd1 | NM_144788.2 | chr12:52844708-52930523 |
| 13681 | Havcr1 | NM_001166632.1 | chr11:46553724-46593080 | | 13776 | Hectd2 | NM_001163471.1 | chr19:36629128-36763969 |
| 13682 | Havcr1 | NM_134184.2 | chr11:46553724-46593080 | | 13777 | Hectd2 | NM_172637.3 | chr19:36629128-36763969 |
| 13683 | Havcr2 | NM_134250.1 | chr11:46268432-46294756 | | 13778 | Hectd3 | NM_175244.2 | chr4:116687952-116677882 |
| 13684 | Hax1 | NM_001282032.1 | chr3:89799367-89802638 | | 13779 | Hecw1 | NM_001081348.3 | chr13:14318704-14615493 |
| 13685 | Hax1 | NM_011826.4 | chr3:89799367-89802638 | | 13780 | Hecw2 | NM_001001883.3 | chr1:53863717-54251878 |
| 13686 | Hba-a1 | NM_008218.2 | chr11:32183671-32184493 | | 13781 | Hecw2 | NM_172655.3 | chr1:53863717-54251878 |
| 13687 | Hba-a1 | NM_008218.2 | chr11:32196488-32197310 | | 13782 | Heg1 | NM_175256.5 | chr16:33684551-33768281 |
| 13688 | Hba-a2 | NM_001083955.1 | chr11:32183671-32184493 | | 13783 | Heh | NM_080446.2 | chr10:119520664-119550021 |
| 13689 | Hba-a2 | NM_001083955.1 | chr11:32196488-32197310 | | 13784 | Hells | NM_008234.3 | chr19:39005479-39042767 |
| 13690 | Hba-x | NM_010405.4 | chr11:32176599-32178115 | | 13785 | Helq | NM_001081107.1 | chr5:101191166-101227619 |
| 13691 | Hbb-b1 | NM_001278161.1 | chr7:110975046-110976443 | | 13786 | Helt | NM_173789.4 | chr8:47377401-47380025 |
| 13692 | Hbb-bh1 | NM_008219.3 | chr7:110990151-110991676 | | 13787 | Helz | NM_198298.1 | chr11:107409274-107548257 |
| 13693 | Hbb-bh2 | NM_001127686.1 | chr7:110987637-110989035 | | 13788 | Helz2 | NM_183162.2 | chr2:180962319-180976732 |
| 13694 | Hbb-bs | NM_001201391.1 | chr7:110975037-110976442 | | 13789 | Hemgn | NM_053149.2 | chr4:46406860-46417055 |
| 13695 | Hbb-bt | NM_008220.5 | chr7:110961037-110962437 | | 13790 | Hemk1 | NM_133984.2 | chr9:107229412-107240681 |
| 13696 | Hbb-y | NM_008221.4 | chr7:111000267-111001721 | | 13791 | Hemt1 | NM_010416.3 | chr15:74649505-74654866 |
| 13697 | Hbegf | NM_010415.2 | chr18:36644580-36675459 | | 13792 | Henmt1 | NM_001078646.1 | chr3:108743001-108763694 |
| 13698 | Hbp1 | NM_153198.2 | chr12:32339733-32635400 | | 13793 | Henmt1 | NM_025723.2 | chr3:108743001-108763694 |
| 13699 | Hbp1 | NM_177993.3 | chr12:32339733-32635400 | | 13794 | Hepacam | NM_175189.2 | chr9:37175190-37194156 |
| 13700 | Hbq1a | NM_175000.2 | chr11:32200068-32200873 | | 13795 | Hepacam2 | NM_178899.5 | chr6:3407088-3444498 |
| 13701 | Hbq1b | NM_001033981.3 | chr11:32186963-32187912 | | 13796 | Heph | NM_001159627.1 | chrX:93650774-93769823 |
| 13702 | Hbs1l | NM_001042593.1 | chr10:21015784-21088695 | | 13797 | Heph | NM_001159628.1 | chrX:93650774-93769823 |
| 13703 | Hbs1l | NM_001145209.1 | chr10:21015784-21088695 | | 13798 | Heph | NM_010417.2 | chrX:93650774-93769823 |
| 13704 | Hbs1l | NM_019702.2 | chr10:21015784-21088695 | | 13799 | Heph | NM_181273.4 | chrX:93650774-93769823 |
| 13705 | Hc | NM_010406.2 | chr2:34838850-34916961 | | 13800 | Hephl1 | NM_001164797.1 | chr9:14856284-14916552 |
| 13706 | Hcar1 | NM_175520.3 | chr5:124826744-124830029 | | 13801 | Herc1 | NM_145617.3 | chr9:66198257-66356582 |
| 13707 | Hcar2 | NM_030701.3 | chr5:124313578-124315525 | | 13802 | Herc2 | NM_010418.2 | chr7:63305524-63487168 |
| 13708 | Hccs | NM_008222.4 | chrX:165749462-165758275 | | 13803 | Herc3 | NM_028705.3 | chr6:58783694-58870390 |
| 13709 | Hcfc1 | NM_008224.4 | chrX:71188130-71211696 | | 13804 | Herc4 | NM_026101.4 | chr10:62706544-62780629 |
| 13710 | Hcfc1r1 | NM_181821.1 | chr17:23810575-23812491 | | 13805 | Herc4 | NM_030114.2 | chr10:62706544-62780629 |
| 13711 | Hcfc2 | NM_001081218.1 | chr10:82161751-82204137 | | 13806 | Herc6 | NM_025992.2 | chr6:57530985-57615130 |
| 13712 | Hck | NM_001172117.1 | chr2:152934203-152977177 | | 13807 | Herpud1 | NM_022331.1 | chr8:96910399-96919258 |

Fig. 25 - 74

| | | | |
|---|---|---|---|
| 13808 | Herpud2 | NM_020586.2 | chr9:24912573-24956280 |
| 13809 | Hes1 | NM_008235.2 | chr16:30065442-30067882 |
| 13810 | Hes2 | NM_008236.4 | chr4:151532975-151536578 |
| 13811 | Hes3 | NM_008237.4 | chr4:151660080-151665771 |
| 13812 | Hes5 | NM_010419.4 | chr4:154335031-154336480 |
| 13813 | Hes6 | NM_019479.3 | chr1:93308059-93309799 |
| 13814 | Hes7 | NM_033041.4 | chr11:68933954-68936761 |
| 13815 | Hesx1 | NM_010420.2 | chr14:27813547-27815511 |
| 13816 | Hexa | NM_010421.4 | chr9:59387473-59412912 |
| 13817 | Hexb | NM_010422.2 | chr13:97946286-97968312 |
| 13818 | Hexdc | NM_001001333.2 | chr11:121038906-121090623 |
| 13819 | Hexdc | NM_001146073.1 | chr11:121038906-121090623 |
| 13820 | Hexim1 | NM_138753.2 | chr11:102977638-102981038 |
| 13821 | Hexim2 | NM_001130515.1 | chr11:102994652-103001222 |
| 13822 | Hexim2 | NM_001130516.1 | chr11:102994652-103001222 |
| 13823 | Hexim2 | NM_027658.2 | chr11:102994652-103001222 |
| 13824 | Hey1 | NM_010423.2 | chr3:8663358-8667038 |
| 13825 | Hey2 | NM_013904.1 | chr10:30552164-30562589 |
| 13826 | Heyl | NM_013905.3 | chr4:122910798-122927113 |
| 13827 | Hfe | NM_010424.4 | chr13:23795709-23802680 |
| 13828 | Hfe2 | NM_027126.4 | chr3:96329107-96333139 |
| 13829 | Hfm1 | NM_001252516.1 | chr5:107269215-107354909 |
| 13830 | Hfm1 | NM_177873.3 | chr5:107269215-107354909 |
| 13831 | Hgd | NM_013547.3 | chr16:37580238-37632112 |
| 13832 | Hgd | NR_027778.1 | chr16:37580238-37632112 |
| 13833 | Hgf | NM_001289458.1 | chr5:16059312-16125257 |
| 13834 | Hgf | NM_001289459.1 | chr5:16059312-16125257 |
| 13835 | Hgf | NM_001289460.1 | chr5:16059312-16125257 |
| 13836 | Hgf | NM_001289461.1 | chr5:16059312-16125257 |
| 13837 | Hgf | NM_010427.5 | chr5:16059312-16125257 |
| 13838 | Hgfac | NM_019447.2 | chr5:35384201-35391085 |
| 13839 | Hgs | NM_001159328.1 | chr11:120328948-120345298 |
| 13840 | Hgs | NM_008244.3 | chr11:120328948-120345298 |
| 13841 | Hgsnat | NM_029884.1 | chr8:27054930-27087216 |
| 13842 | Hhat | NM_144881.4 | chr1:194336709-194597413 |
| 13843 | Hhatl | NM_029095.2 | chr9:121693133-121701625 |
| 13844 | Hhatl | NR_027967.1 | chr9:121693133-121701625 |
| 13845 | Hhex | NM_008245.3 | chr19:37509330-37515221 |
| 13846 | Hhip | NM_020259.4 | chr8:82489749-82581907 |
| 13847 | Hhip1 | NM_001044380.1 | chr12:109544479-109566510 |
| 13848 | Hhipl2 | NM_030175.5 | chr1_random:391850-410401 |
| 13849 | Hhla1 | NM_001145096.1 | chr15:65754004-65808366 |
| 13850 | Hiat1 | NM_008246.2 | chr3:116334084-116365595 |
| 13851 | Hiatl1 | NM_001083901.1 | chr13:65166337-65214290 |
| 13852 | Hiatl1 | NM_133880.3 | chr13:65166337-65214290 |
| 13853 | Hibadh | NM_145567.1 | chr6:52496223-52590294 |
| 13854 | Hibch | NM_146108.1 | chr1:52901889-52977704 |
| 13855 | Hic1 | NM_001098203.1 | chr11:74978066-74983757 |
| 13856 | Hic1 | NM_010430.2 | chr11:74978066-74983757 |
| 13857 | Hic2 | NM_178922.3 | chr16:17233679-17263523 |
| 13858 | Hid1 | NM_175454.2 | chr11:115209022-115229033 |
| 13859 | Hif1a | NM_010431.2 | chr12:75008853-75048517 |
| 13860 | Hif1an | NM_176958.3 | chr19:44637343-44650764 |
| 13861 | Hif3a | NM_001162950.1 | chr7:17616341-17647776 |
| 13862 | Hif3a | NM_016868.3 | chr7:17616341-17647776 |
| 13863 | Higd1a | NM_019814.4 | chr9:121757677-121767118 |
| 13864 | Higd1b | NM_080846.1 | chr11:102697609-102699353 |
| 13865 | Higd1c | NM_001002900.1 | chr15:100195016-100214386 |
| 13866 | Higd2a | NM_025933.3 | chr11:54691591-54692508 |
| 13867 | Hilpda | NM_001190461.1 | chr6:29222487-29225449 |
| 13868 | Hilpda | NM_023516.5 | chr6:29222487-29225449 |
| 13869 | Hils1 | NM_010178.1 | chr11:94828975-94829770 |
| 13870 | Hinfp | NM_172162.3 | chr9:44103755-44113754 |
| 13871 | Hint1 | NM_008248.2 | chr11:54679939-54683998 |
| 13872 | Hint2 | NM_026871.1 | chr4:43667098-43669317 |
| 13873 | Hint3 | NM_025738.3 | chr10:30328012-30338172 |
| 13874 | Hip1 | NM_146001.2 | chr5:135882887-136020992 |
| 13875 | Hip1r | NM_145070.3 | chr5:124423637-124453224 |
| 13876 | Hipk1 | NM_010432.2 | chr3:103543737-103595198 |
| 13877 | Hipk2 | NM_001136065.2 | chr6:38647838-38826189 |
| 13878 | Hipk2 | NM_010433.2 | chr6:38647838-38826189 |
| 13879 | Hipk3 | NM_001145824.1 | chr2:104266638-104334646 |
| 13880 | Hipk3 | NM_010434.2 | chr2:104266638-104334646 |
| 13881 | Hipk4 | NM_001033315.2 | chr7:28308279-28316193 |
| 13882 | Hira | NM_010435.2 | chr16:18876842-18970401 |
| 13883 | Hirip3 | NM_172746.3 | chr7:134005485-134008636 |
| 13884 | Hist1h1a | NM_030609.3 | chr13:23855536-23856281 |
| 13885 | Hist1h1b | NM_020034.2 | chr13:21871700-21872494 |
| 13886 | Hist1h1c | NM_015786.1 | chr13:23830675-23831400 |
| 13887 | Hist1h1d | NM_145713.3 | chr13:23646900-23647676 |
| 13888 | Hist1h1e | NM_015787.4 | chr13:23713645-23714427 |
| 13889 | Hist1h1t | NM_010377.3 | chr13:23787679-23788414 |
| 13890 | Hist1h2aa | NM_175658.2 | chr13:24026330-24026782 |
| 13891 | Hist1h2ab | NM_175660.3 | chr13:23842956-23843461 |
| 13892 | Hist1h2ac | NM_178159.3 | chr13:23775341-23775828 |
| 13893 | Hist1h2ad | NM_178188.4 | chr13:23666249-23666784 |
| 13894 | Hist1h2ae | NM_178187.3 | chr13:23662531-23663089 |
| 13895 | Hist1h2af | NM_175661.2 | chr13:23625779-23626247 |
| 13896 | Hist1h2ag | NM_178186.3 | chr13:22134346-22134818 |
| 13897 | Hist1h2ah | NM_175659.2 | chr13:22126990-22127512 |
| 13898 | Hist1h2ai | NM_178182.2 | chr13:21808280-21808728 |
| 13899 | Hist1h2ak | NM_178183.2 | chr13:21845245-21845781 |
| 13900 | Hist1h2an | NM_178184.2 | chr13:21878640-21879087 |
| 13901 | Hist1h2ao | NM_001177544.2 | chr13:21902235-21902787 |
| 13902 | Hist1h2ao | NM_001177544.2 | chr13:21924892-21925444 |
| 13903 | Hist1h2ap | NM_178185.2 | chr13:21902235-21902787 |
| 13904 | Hist1h2ap | NM_178185.2 | chr13:21924892-21925444 |
| 13905 | Hist1h2ba | NM_175663.2 | chr13:24025593-24026025 |
| 13906 | Hist1h2bb | NM_175664.3 | chr13:23838602-23839092 |
| 13907 | Hist1h2bc | NM_001290380.1 | chr13:23776067-23784349 |
| 13908 | Hist1h2bc | NM_023422.3 | chr13:23776067-23784349 |
| 13909 | Hist1h2be | NM_001177653.1 | chr13:23675538-23712993 |
| 13910 | Hist1h2be | NM_001290530.1 | chr13:23675538-23712993 |
| 13911 | Hist1h2be | NM_178194.2 | chr13:23675538-23712993 |
| 13912 | Hist1h2bf | NM_178195.2 | chr13:23665628-23666059 |
| 13913 | Hist1h2bg | NM_178196.4 | chr13:23663268-23663732 |
| 13914 | Hist1h2bh | NM_178197.2 | chr13:23634791-23635313 |
| 13915 | Hist1h2bj | NM_178198.2 | chr13:22135098-22135527 |
| 13916 | Hist1h2bk | NM_175665.2 | chr13:22127689-22128189 |
| 13917 | Hist1h2bl | NM_178199.2 | chr13:21807581-21808012 |
| 13918 | Hist1h2bm | NM_178200.2 | chr13:21813912-21814395 |
| 13919 | Hist1h2bn | NM_178201.2 | chr13:21845991-21846422 |
| 13920 | Hist1h2bp | NM_001290466.1 | chr13:21879356-21881082 |
| 13921 | Hist1h2bp | NM_178202.2 | chr13:21879356-21881082 |
| 13922 | Hist1h2bq | NM_001097979.2 | chr13:21898280-21902068 |
| 13923 | Hist1h2bq | NM_001097979.2 | chr13:21925611-21929399 |
| 13924 | Hist1h3a | NM_013550.5 | chr13:23853753-23854255 |
| 13925 | Hist1h3b | NM_178203.2 | chr13:23844248-23844709 |
| 13926 | Hist1h3c | NM_175653.1 | chr13:23836910-23837390 |
| 13927 | Hist1h3d | NM_178204.2 | chr13:23667631-23668135 |
| 13928 | Hist1h3e | NM_178205.2 | chr13:23653764-23654234 |
| 13929 | Hist1h3f | NM_013548.4 | chr13:23635920-23636823 |
| 13930 | Hist1h3g | NM_145073.2 | chr13:23627286-23627778 |
| 13931 | Hist1h3h | NM_178206.2 | chr13:21809496-21809984 |
| 13932 | Hist1h3i | NM_178207.2 | chr13:21874783-21875266 |
| 13933 | Hist1h4a | NM_178192.1 | chr13:23852663-23853118 |
| 13934 | Hist1h4b | NM_178193.2 | chr13:23848805-23849255 |
| 13935 | Hist1h4c | NM_178208.2 | chr13:23789952-23790327 |
| 13936 | Hist1h4d | NM_175654.2 | chr13:23673470-23673838 |
| 13937 | Hist1h4f | NM_175655.2 | chr13:23643154-23643512 |
| 13938 | Hist1h4h | NM_153173.4 | chr13:23622912-23623347 |
| 13939 | Hist1h4i | NM_175656.3 | chr13:22132828-22133231 |
| 13940 | Hist1h4j | NM_178210.1 | chr13:21826964-21827276 |
| 13941 | Hist1h4k | NM_178211.2 | chr13:21842013-21842422 |
| 13942 | Hist1h4m | NM_001195421.1 | chr13:21903615-21904019 |
| 13943 | Hist1h4n | NM_175657.2 | chr13:21923661-21924027 |
| 13944 | Hist1h4n | NM_175657.2 | chr13:21903614-21904019 |
| 13945 | Hist2h2aa1 | NM_013549.2 | chr3:96043701-96044297 |
| 13946 | Hist2h2aa1 | NM_013549.2 | chr3:96049379-96049975 |
| 13947 | Hist2h2aa2 | NM_178212.3 | chr3:96043701-96044297 |
| 13948 | Hist2h2aa2 | NM_178212.3 | chr3:96049379-96049975 |
| 13949 | Hist2h2ab | NM_178213.4 | chr3:96023838-96024276 |
| 13950 | Hist2h2ac | NM_175662.2 | chr3:96024335-96024803 |
| 13951 | Hist2h2bb | NM_175666.2 | chr3:96073622-96074115 |
| 13952 | Hist2h2be | NM_178214.3 | chr3:96025043-96027661 |
| 13953 | Hist2h3b | NM_178215.2 | chr3:96072576-96073078 |
| 13954 | Hist2h3c1 | NM_178216.3 | chr3:96042401-96043065 |
| 13955 | Hist2h3c1 | NM_178216.3 | chr3:96050607-96051271 |
| 13956 | Hist2h3c2 | NM_054045.4 | chr3:96042401-96043065 |
| 13957 | Hist2h3c2 | NM_054045.4 | chr3:96050607-96051271 |
| 13958 | Hist2h4 | NM_033596.3 | chr3:96066856-98067240 |
| 13959 | Hist3h2a | NM_178218.4 | chr11:58768186-58768694 |
| 13960 | Hist3h2ba | NM_030082.4 | chr11:58762412-58762874 |
| 13961 | Hist3h2bb-ps | NM_206882.1 | chr11:58767549-58768014 |
| 13962 | Hist4h4 | NM_175652.3 | chr6:136752513-136752952 |
| 13963 | Hivep1 | NM_007772.2 | chr13:42147389-42280395 |
| 13964 | Hivep2 | NM_010437.2 | chr10:13686184-13871184 |
| 13965 | Hivep3 | NM_010657.3 | chr4:119487282-119808016 |
| 13966 | Hjurp | NM_198652.2 | chr1:90155431-90174154 |
| 13967 | Hk1 | NM_001146100.1 | chr10:61731602-61842656 |
| 13968 | Hk1 | NM_010438.3 | chr10:61731602-61842656 |
| 13969 | Hk1os | NR_038038.1 | chr10:61803355-61812614 |
| 13970 | Hk2 | NM_013820.3 | chr6:82675020-82724448 |
| 13971 | Hk3 | NM_001033245.4 | chr13:55050792-55122746 |
| 13972 | Hk3 | NM_001206390.1 | chr13:55050792-55122746 |
| 13973 | Hk3 | NM_001206391.1 | chr13:55050792-55122746 |
| 13974 | Hk3 | NM_001206392.1 | chr13:55050792-55122746 |
| 13975 | Hkdc1 | NM_145419.1 | chr10:61845884-61885205 |
| 13976 | Hlcs | NM_199145.4 | chr16:94350911-94509463 |
| 13977 | Hlf | NM_172563.3 | chr11:90197848-90252231 |
| 13978 | Hltf | NM_009210.3 | chr3:19957810-20018377 |
| 13979 | Hltf | NR_105046.1 | chr3:19957810-20018377 |
| 13980 | Hltf | NR_105047.1 | chr3:19957810-20018377 |
| 13981 | Hlx | NM_008250.2 | chr1:186551023-186556372 |
| 13982 | Hmbox1 | NM_177338.5 | chr14:65441054-65568684 |
| 13983 | Hmbs | NM_001110251.1 | chr9:44144430-44152311 |
| 13984 | Hmbs | NM_013551.2 | chr9:44144430-44152311 |
| 13985 | Hmces | NM_173737.2 | chr6:87863969-87886607 |
| 13986 | Hmcn1 | NM_001024720.3 | chr1:152409631-152840565 |
| 13987 | Hmg20a | NM_025812.2 | chr9:56266652-56344743 |
| 13988 | Hmg20b | NM_001163165.1 | chr10:80808790-80813202 |
| 13989 | Hmg20b | NM_001163166.1 | chr10:80808790-80813202 |
| 13990 | Hmg20b | NM_010440.3 | chr10:80808790-80813202 |
| 13991 | Hmga1 | NM_001025427.3 | chr17:27693518-27700617 |
| 13992 | Hmga1 | NM_001039356.2 | chr17:27693518-27700617 |
| 13993 | Hmga1 | NM_001166535.1 | chr17:27693518-27700617 |
| 13994 | Hmga1 | NM_001166536.1 | chr17:27693518-27700617 |
| 13995 | Hmga1 | NM_001166537.1 | chr17:27693518-27700617 |
| 13996 | Hmga1 | NM_001166539.1 | chr17:27693518-27700617 |
| 13997 | Hmga1 | NM_001166540.1 | chr17:27693518-27700617 |

Fig. 25 - 75

| | | | |
|---|---|---|---|
| 13998 | Hmga1 | NM_001166541.1 | chr17:27693518-27700617 |
| 13999 | Hmga1 | NM_001166542.1 | chr17:27693518-27700617 |
| 14000 | Hmga1 | NM_001166543.1 | chr17:27693518-27700617 |
| 14001 | Hmga1 | NM_001166544.1 | chr17:27693518-27700617 |
| 14002 | Hmga1 | NM_001166545.1 | chr17:27693518-27700617 |
| 14003 | Hmga1 | NM_001166546.1 | chr17:27693518-27700617 |
| 14004 | Hmga1 | NM_016660.3 | chr17:27693518-27700617 |
| 14005 | Hmga1-rs1 | NM_001166476.1 | chr17:27693518-27700617 |
| 14006 | Hmga1-rs1 | NM_001166477.1 | chr17:27693518-27700617 |
| 14007 | Hmga2 | NM_010441.2 | chr10:119798331-119913991 |
| 14008 | Hmga2-ps1 | NR_037996.1 | chr1:178764755-178766264 |
| 14009 | Hmgb1 | NM_010439.3 | chr5:149858803-149864613 |
| 14010 | Hmgb1-rs17 | NR_033589.1 | chr8:34594782-34596229 |
| 14011 | Hmgb2 | NM_008252.3 | chr8:59990639-59994796 |
| 14012 | Hmgb3 | NM_008253.4 | chrX:68809167-68813829 |
| 14013 | Hmgb4 | NM_027036.3 | chr4:127937456-127938139 |
| 14014 | Hmgcl | NM_008254.2 | chr4:135502367-135518532 |
| 14015 | Hmgcll1 | NM_173731.2 | chr9:75862783-75984157 |
| 14016 | Hmgcr | NM_008255.2 | chr13:97418918-97440891 |
| 14017 | Hmgcs1 | NM_001291439.1 | chr13_random:114526-132436 |
| 14018 | Hmgcs1 | NM_001291439.1 | chr13_random:308436-326346 |
| 14019 | Hmgcs1 | NM_145942.5 | chr13_random:308436-326346 |
| 14020 | Hmgcs1 | NM_145942.5 | chr13_random:114526-132436 |
| 14021 | Hmgcs2 | NM_008256.4 | chr3:98084353-98114661 |
| 14022 | Hmgn1 | NM_008251.3 | chr16:96343194-96349332 |
| 14023 | Hmgn2 | NM_016957.3 | chr4:133520653-133523906 |
| 14024 | Hmgn3 | NM_026122.4 | chr9:83003548-83040214 |
| 14025 | Hmgn3 | NM_175074.2 | chr9:83003548-83040214 |
| 14026 | Hmgn5 | NM_016710.2 | chrX:106199875-106208719 |
| 14027 | Hmgxb3 | NM_134134.2 | chr18:61290930-61336704 |
| 14028 | Hmgxb3 | NM_178277.1 | chr18:61290930-61336704 |
| 14029 | Hmgxb4 | NM_178017.1 | chr8:77517601-77555871 |
| 14030 | Hmha1 | NM_001142701.1 | chr10:79479416-79494216 |
| 14031 | Hmha1 | NM_027521.3 | chr10:79479416-79494216 |
| 14032 | Hmmr | NM_013552.2 | chr11:40514889-40546939 |
| 14033 | Hmox1 | NM_010442.2 | chr8:77617516-77624492 |
| 14034 | Hmox2 | NM_001136066.2 | chr16:4726360-4789935 |
| 14035 | Hmox2 | NM_010443.2 | chr16:4726360-4789935 |
| 14036 | Hmx1 | NM_010445.2 | chr5:35731765-35735521 |
| 14037 | Hmx2 | NM_145998.3 | chr7:138697575-138700096 |
| 14038 | Hmx3 | NM_008257.3 | chr7:138686476-138688445 |
| 14039 | Hn1 | NM_008258.1 | chr11:115358666-115375684 |
| 14040 | Hn1l | NM_198937.2 | chr17:25079414-25097568 |
| 14041 | Hnf1a | NM_009327.3 | chr5:115398988-115421071 |
| 14042 | Hnf1b | NM_001291268.1 | chr11:83664370-83719419 |
| 14043 | Hnf1b | NM_001291269.1 | chr11:83664370-83719419 |
| 14044 | Hnf1b | NM_009330.3 | chr11:83664370-83719419 |
| 14045 | Hnf4a | NM_008261.2 | chr2:163372923-163398643 |
| 14046 | Hnf4aos | NR_027970.1 | chr2:163319540-163367457 |
| 14047 | Hnf4g | NM_013920.2 | chr3:3508029-3659800 |
| 14048 | Hnrnpt | NM_080462.2 | chr2:23858431-23904899 |
| 14049 | Hnrnpa0 | NM_029872.1 | chr13:58227239-58229317 |
| 14050 | Hnrnpa1 | NM_001039129.4 | chr15:103070827-103077129 |
| 14051 | Hnrnpa1 | NM_010447.5 | chr15:103070827-103077129 |
| 14052 | Hnrnpa1 | NR_104427.1 | chr15:103070827-103077129 |
| 14053 | Hnrnpa2b1 | NM_016806.3 | chr6:51410433-51419893 |
| 14054 | Hnrnpa2b1 | NM_182650.4 | chr6:51410433-51419893 |
| 14055 | Hnrnpa2b1 | NR_104468.1 | chr6:51410433-51419893 |
| 14056 | Hnrnpa3 | NM_053263.1 | chr2:75497315-75507464 |
| 14057 | Hnrnpa3 | NM_146130.3 | chr2:75497315-75507464 |
| 14058 | Hnrnpa3 | NM_198090.2 | chr2:75497315-75507464 |
| 14059 | Hnrnpab | NM_001048061.1 | chr11:51398258-51420383 |
| 14060 | Hnrnpab | NM_010448.3 | chr11:51398258-51420383 |
| 14061 | Hnrnpc | NM_001170981.1 | chr14:52693054-52723703 |
| 14062 | Hnrnpc | NM_001170982.1 | chr14:52693054-52723703 |
| 14063 | Hnrnpc | NM_001170983.1 | chr14:52693054-52723703 |
| 14064 | Hnrnpc | NM_001170984.1 | chr14:52693054-52723703 |
| 14065 | Hnrnpc | NM_016884.1 | chr14:52693054-52723703 |
| 14066 | Hnrnpd | NM_001077265.2 | chr5:100384953-100407957 |
| 14067 | Hnrnpd | NM_001077266.2 | chr5:100384953-100407957 |
| 14068 | Hnrnpd | NM_001077267.2 | chr5:100384953-100407957 |
| 14069 | Hnrnpd | NM_007516.3 | chr5:100384953-100407957 |
| 14070 | Hnrnpdl | NM_016690.4 | chr5:100462597-100468241 |
| 14071 | Hnrnpf | NM_001166427.1 | chr6:117850357-117875640 |
| 14072 | Hnrnpf | NM_001166428.1 | chr6:117850357-117875640 |
| 14073 | Hnrnpf | NM_001166429.1 | chr6:117850357-117875640 |
| 14074 | Hnrnpf | NM_001166430.1 | chr6:117850357-117875640 |
| 14075 | Hnrnpf | NM_001166431.1 | chr6:117850357-117875640 |
| 14076 | Hnrnpf | NM_001166432.1 | chr6:117850357-117875640 |
| 14077 | Hnrnpf | NM_133834.2 | chr6:117850357-117875640 |
| 14078 | Hnrnph1 | NM_021510.2 | chr11:50191220-50200030 |
| 14079 | Hnrnph2 | NM_019868.3 | chrX:131135824-131141593 |
| 14080 | Hnrnph3 | NM_001079824.1 | chr10:62477412-62496597 |
| 14081 | Hnrnpk | NM_025279.3 | chr13:58492493-58503873 |
| 14082 | Hnrnpl | NM_177301.4 | chr7:29595908-29607285 |
| 14083 | Hnrnpll | NM_144802.4 | chr17:80428826-80461608 |
| 14084 | Hnrnpm | NM_001109913.1 | chr17:33783177-33822403 |
| 14085 | Hnrnpm | NM_029804.3 | chr17:33783177-33822403 |
| 14086 | Hnrnpr | NM_001277121.1 | chr4:135866856-135901894 |
| 14087 | Hnrnpr | NM_001277122.1 | chr4:135866856-135901894 |
| 14088 | Hnrnpr | NM_001277123.1 | chr4:135866856-135901894 |
| 14089 | Hnrnpr | NM_028871.2 | chr4:135866856-135901894 |
| 14090 | Hnrnpu | NM_016805.2 | chr1:180258430-180267915 |
| 14091 | Hnrnpul1 | NM_144922.2 | chr7:26507057-26539739 |
| 14092 | Hnrnpul1 | NM_178089.2 | chr7:26507057-26539739 |
| 14093 | Hnrnpul2 | NM_001081196.1 | chr19:8893890-8908632 |
| 14094 | Hoga1 | NM_026152.1 | chr19:42120341-42145429 |
| 14095 | Homer1 | NM_001284189.1 | chr13:94074449-94175084 |
| 14096 | Homer1 | NM_011982.3 | chr13:94074449-94175084 |
| 14097 | Homer1 | NM_147176.3 | chr13:94074449-94175084 |
| 14098 | Homer1 | NM_152134.3 | chr13:94074449-94175084 |
| 14099 | Homer2 | NM_001164086.1 | chr7:88745366-88851811 |
| 14100 | Homer2 | NM_001164087.1 | chr7:88745366-88851811 |
| 14101 | Homer2 | NM_011983.2 | chr7:88745366-88851811 |
| 14102 | Homer3 | NM_001146153.1 | chr8:72806897-72826351 |
| 14103 | Homer3 | NM_011984.2 | chr8:72806897-72826351 |
| 14104 | Homez | NM_001177705.1 | chr14:55471573-55482995 |
| 14105 | Homez | NM_183174.3 | chr14:55471573-55482995 |
| 14106 | Hook1 | NM_030014.2 | chr4:95634070-95690965 |
| 14107 | Hook2 | NM_001167991.1 | chr8:87514493-87527263 |
| 14108 | Hook2 | NM_133255.2 | chr8:87514493-87527263 |
| 14109 | Hook3 | NM_207659.3 | chr8:27131893-27229696 |
| 14110 | Hopx | NM_001159900.1 | chr5:77516010-77544148 |
| 14111 | Hopx | NM_001159901.1 | chr5:77516010-77544148 |
| 14112 | Hopx | NM_175606.3 | chr5:77516010-77544148 |
| 14113 | Hormad1 | NM_001289532.1 | chr3:95363598-95391782 |
| 14114 | Hormad1 | NM_001289534.1 | chr3:95363598-95391782 |
| 14115 | Hormad1 | NM_001289537.1 | chr3:95363598-95391782 |
| 14116 | Hormad1 | NM_026489.3 | chr3:95363598-95391782 |
| 14117 | Hormad2 | NM_029458.1 | chr11:4246385-4341085 |
| 14118 | Hotair | NR_047528.1 | chr15:102774492-102778377 |
| 14119 | Hottip | NR_110441.1 | chr6:52212768-52217597 |
| 14120 | Hottip | NR_110442.1 | chr6:52212768-52217597 |
| 14121 | Hoxa1 | NM_010449.4 | chr6:52105365-52108316 |
| 14122 | Hoxa10 | NM_001122950.2 | chr6:52181195-52190853 |
| 14123 | Hoxa10 | NM_008263.3 | chr6:52181195-52190853 |
| 14124 | Hoxa11 | NM_010450.3 | chr6:52192104-52195809 |
| 14125 | Hoxa11os | NR_015348.1 | chr6:52195242-52199768 |
| 14126 | Hoxa13 | NM_008264.1 | chr6:52208851-52210874 |
| 14127 | Hoxa2 | NM_010451.2 | chr6:52112415-52114830 |
| 14128 | Hoxa3 | NM_010452.3 | chr6:52119061-52163066 |
| 14129 | Hoxa4 | NM_008265.3 | chr6:52139686-52141702 |
| 14130 | Hoxa5 | NM_010453.5 | chr6:52151753-52154586 |
| 14131 | Hoxa6 | NM_010454.1 | chr6:52156364-52158623 |
| 14132 | Hoxa7 | NM_010455.2 | chr6:52165622-52168572 |
| 14133 | Hoxa9 | NM_001277238.1 | chr6:52173095-52177369 |
| 14134 | Hoxa9 | NM_010456.3 | chr6:52173095-52177369 |
| 14135 | Hoxb1 | NM_008266.5 | chr11:96227071-96229567 |
| 14136 | Hoxb13 | NM_008267.2 | chr11:96055674-96057913 |
| 14137 | Hoxb2 | NM_134032.2 | chr11:96212945-96215328 |
| 14138 | Hoxb3 | NM_001079869.1 | chr11:96184439-96209244 |
| 14139 | Hoxb3 | NM_010458.2 | chr11:96184439-96209244 |
| 14140 | Hoxb4 | NM_010459.1 | chr11:96179580-96182952 |
| 14141 | Hoxb5 | NM_008268.2 | chr11:96164825-96167435 |
| 14142 | Hoxb6 | NM_008269.1 | chr11:96160484-96162883 |
| 14143 | Hoxb7 | NM_010460.2 | chr11:96147959-96151477 |
| 14144 | Hoxb8 | NM_010461.2 | chr11:96143218-96146639 |
| 14145 | Hoxb9 | NM_008270.2 | chr11:96132643-96137907 |
| 14146 | Hoxc10 | NM_010462.5 | chr15:102797226-102803328 |
| 14147 | Hoxc11 | NM_001024842.1 | chr15:102784956-102787132 |
| 14148 | Hoxc12 | NM_010463.1 | chr15:102767283-102768948 |
| 14149 | Hoxc13 | NM_010464.1 | chr15:102751561-102759245 |
| 14150 | Hoxc4 | NM_013553.2 | chr15:102864825-102867283 |
| 14151 | Hoxc5 | NM_175730.5 | chr15:102844439-102847860 |
| 14152 | Hoxc6 | NM_010465.2 | chr15:102839992-102842312 |
| 14153 | Hoxc8 | NM_010466.2 | chr15:102820969-102824685 |
| 14154 | Hoxc9 | NM_008272.3 | chr15:102807462-102814875 |
| 14155 | Hoxd1 | NM_010467.2 | chr2:74601036-74603199 |
| 14156 | Hoxd10 | NM_013554.5 | chr2:74529947-74533163 |
| 14157 | Hoxd11 | NM_008273.2 | chr2:74517614-74525073 |
| 14158 | Hoxd11 | NR_073086.1 | chr2:74517614-74525073 |
| 14159 | Hoxd12 | NM_008274.3 | chr2:74513069-74515762 |
| 14160 | Hoxd13 | NM_008275.3 | chr2:74506366-74509656 |
| 14161 | Hoxd3 | NM_010468.2 | chr2:74550050-74586328 |
| 14162 | Hoxd3os1 | NR_027899.1 | chr2:74548101-74554187 |
| 14163 | Hoxd4 | NM_010469.2 | chr2:74560035-74567216 |
| 14164 | Hoxd8 | NM_001290730.1 | chr2:74542671-74545989 |
| 14165 | Hoxd8 | NM_001290731.1 | chr2:74542671-74545989 |
| 14166 | Hoxd8 | NM_008276.3 | chr2:74542671-74545989 |
| 14167 | Hoxd9 | NM_013555.4 | chr2:74535819-74538265 |
| 14168 | Hp | NM_017370.2 | chr8:112099027-112103072 |
| 14169 | Hp1bp3 | NM_001122896.2 | chr4:137772526-137800597 |
| 14170 | Hp1bp3 | NM_001122897.2 | chr4:137772526-137800597 |
| 14171 | Hp1bp3 | NM_001285478.1 | chr4:137772526-137800597 |
| 14172 | Hp1bp3 | NM_001285479.1 | chr4:137772526-137800597 |
| 14173 | Hp1bp3 | NM_001285480.1 | chr4:137772526-137800597 |
| 14174 | Hp1bp3 | NM_001285481.1 | chr4:137772526-137800597 |
| 14175 | Hp1bp3 | NM_010470.3 | chr4:137772526-137800597 |
| 14176 | Hpca | NM_001130419.2 | chr4:128782773-128799169 |
| 14177 | Hpca | NM_001286081.1 | chr4:128782773-128799169 |
| 14178 | Hpca | NM_001286083.1 | chr4:128782773-128799169 |
| 14179 | Hpca | NM_010471.4 | chr4:128782773-128799169 |
| 14180 | Hpcal1 | NM_016677.4 | chr12:17697619-17798732 |
| 14181 | Hpcal4 | NM_174998.4 | chr4:122860746-122871942 |
| 14182 | Hpd | NM_008277.2 | chr5:123621815-123632695 |
| 14183 | Hpdl | NM_146256.3 | chr4:116492551-116494113 |
| 14184 | Hpgd | NM_008278.2 | chr8:58773348-58799843 |

Fig. 25 - 76

| | | | |
|---|---|---|---|
| 14185 | Hpgds | NM_019455.4 | chr6:65067286-65094724 |
| 14186 | Hpn | NM_001110252.2 | chr7:31883743-31900345 |
| 14187 | Hpn | NM_001276269.1 | chr7:31883743-31900345 |
| 14188 | Hpn | NM_008281.4 | chr7:31883743-31900345 |
| 14189 | Hprt | NM_013556.2 | chrX:50341254-50374837 |
| 14190 | Hps1 | NM_019424.2 | chr19:42829685-42854466 |
| 14191 | Hps3 | NM_001146323.1 | chr3:19857053-19935310 |
| 14192 | Hps3 | NM_001146324.1 | chr3:19857053-19935310 |
| 14193 | Hps3 | NM_080634.4 | chr3:19857053-19935310 |
| 14194 | Hps4 | NM_138646.3 | chr5:112772115-112807444 |
| 14195 | Hps5 | NM_001005247.2 | chr7:54015835-54051251 |
| 14196 | Hps5 | NM_001005248.2 | chr7:54015835-54051251 |
| 14197 | Hps5 | NM_001167864.1 | chr7:54015835-54051251 |
| 14198 | Hps6 | NM_176785.3 | chr19:46077967-46080663 |
| 14199 | Hpse | NM_152803.4 | chr5:101108504-101148702 |
| 14200 | Hpse2 | NM_001081257.2 | chr19:42863084-43462845 |
| 14201 | Hpx | NM_017371.2 | chr7:112740124-112748630 |
| 14202 | Hr | NM_021877.3 | chr14:70953862-70973355 |
| 14203 | Hras | NM_001130443.1 | chr7:148375832-148379903 |
| 14204 | Hras | NM_001130444.1 | chr7:148375832-148379903 |
| 14205 | Hras | NM_008284.2 | chr7:148375832-148379903 |
| 14206 | Hrasls | NM_019751.5 | chr16:29209780-29230616 |
| 14207 | Hrasls5 | NM_025731.2 | chr19:7687058-7713728 |
| 14208 | Hrc | NM_010473.2 | chr7:52590638-52594342 |
| 14209 | Hrct1 | NM_027511.1 | chr4:43740069-43740982 |
| 14210 | Hrg | NM_053176.2 | chr16:22951144-22961732 |
| 14211 | Hrh1 | NM_001252642.1 | chr6:114347929-114433290 |
| 14212 | Hrh1 | NM_001252643.1 | chr6:114347929-114433290 |
| 14213 | Hrh1 | NM_008285.3 | chr6:114347929-114433290 |
| 14214 | Hrh2 | NM_001010973.2 | chr13:54287497-54317801 |
| 14215 | Hrh2 | NM_008286.2 | chr13:54287497-54317801 |
| 14216 | Hrh3 | NM_133849.3 | chr2:179834169-179839112 |
| 14217 | Hrh3 | NR_102309.1 | chr2:179834169-179839112 |
| 14218 | Hrh4 | NM_153087.2 | chr18:13165498-13181391 |
| 14219 | Hrk | NM_007545.2 | chr5:118619772-118639487 |
| 14220 | Hrnr | NM_133698.2 | chr3:93123670-93137494 |
| 14221 | Hrsp12 | NM_008287.3 | chr15:34413776-34425001 |
| 14222 | Hs1bp3 | NM_021429.3 | chr12:8320238-8350630 |
| 14223 | Hs2st1 | NM_011828.3 | chr3:144094070-144233180 |
| 14224 | Hs3st1 | NM_010474.2 | chr5:40005173-40035870 |
| 14225 | Hs3st2 | NM_001081327.1 | chr7:128535809-128645282 |
| 14226 | Hs3st3a1 | NM_178870.5 | chr11:64248834-64336337 |
| 14227 | Hs3st3b1 | NM_018805.2 | chr11:63698194-63735786 |
| 14228 | Hs3st4 | NM_001252072.1 | chr7:131126694-131542503 |
| 14229 | Hs3st5 | NM_001081208.2 | chr10:36226612-36554200 |
| 14230 | Hs3st5 | NM_001253355.1 | chr10:36226612-36554200 |
| 14231 | Hs3st6 | NM_001253356.1 | chr10:36226612-36554200 |
| 14232 | Hs3st6 | NM_001012402.1 | chr17:24889947-24895629 |
| 14233 | Hs6st1 | NM_015818.2 | chr1:36125244-36163291 |
| 14234 | Hs6st2 | NM_001077202.2 | chrX:48739813-49034779 |
| 14235 | Hs6st2 | NM_001290467.1 | chrX:48739813-49034779 |
| 14236 | Hs6st2 | NM_001290468.1 | chrX:48739813-49034779 |
| 14237 | Hs6st2 | NM_015819.4 | chrX:48739813-49034779 |
| 14238 | Hs6st3 | NM_015820.3 | chr14:119537487-120269037 |
| 14239 | Hsbp1 | NM_024219.1 | chr8:121868437-121872829 |
| 14240 | Hsbp1l1 | NM_001136161.1 | chr18:80426494-80443841 |
| 14241 | Hscb | NM_153571.2 | chr5:111258088-111268796 |
| 14242 | Hsd11b1 | NM_001044751.1 | chr1:195047834-195090239 |
| 14243 | Hsd11b1 | NM_008288.2 | chr1:195047834-195090239 |
| 14244 | Hsd11b2 | NM_008289.2 | chr8:108042645-108047888 |
| 14245 | Hsd17b1 | NM_010475.1 | chr11:100939724-100941819 |
| 14246 | Hsd17b10 | NM_016763.2 | chrX:148436438-148438985 |
| 14247 | Hsd17b11 | NM_053262.3 | chr5:104418783-104450815 |
| 14248 | Hsd17b12 | NM_019657.4 | chr2:93872853-93998066 |
| 14249 | Hsd17b13 | NM_001163486.1 | chr5:104384460-104406407 |
| 14250 | Hsd17b13 | NM_198030.2 | chr5:104384460-104406407 |
| 14251 | Hsd17b14 | NM_025330.3 | chr7:52810297-52822691 |
| 14252 | Hsd17b2 | NM_008292.2 | chr8:120225845-120282929 |
| 14253 | Hsd17b3 | NM_008291.3 | chr13:64159581-64190509 |
| 14254 | Hsd17b4 | NM_008292.4 | chr18:50287854-50355924 |
| 14255 | Hsd17b6 | NM_013786.2 | chr10:127427991-127444564 |
| 14256 | Hsd17b7 | NM_010476.3 | chr1:171879667-171899336 |
| 14257 | Hsd3b1 | NM_008293.3 | chr3:98656119-98663717 |
| 14258 | Hsd3b2 | NM_153193.3 | chr3:98515029-98528466 |
| 14259 | Hsd3b3 | NM_001012306.2 | chr3:98545398-98567051 |
| 14260 | Hsd3b3 | NM_001042489.1 | chr3:98545398-98567051 |
| 14261 | Hsd3b3 | NM_001161743.1 | chr3:98545398-98567051 |
| 14262 | Hsd3b3 | NM_001161744.1 | chr3:98545398-98567051 |
| 14263 | Hsd3b3 | NM_001161745.1 | chr3:98545398-98567051 |
| 14264 | Hsd3b4 | NM_001111336.1 | chr3:98302995-98314490 |
| 14265 | Hsd3b4 | NM_001111336.1 | chr3:98356450-98367961 |
| 14266 | Hsd3b4 | NM_008294.2 | chr3:98302995-98314490 |
| 14267 | Hsd3b4 | NM_008294.2 | chr3:98356450-98367961 |
| 14268 | Hsd3b5 | NM_008295.2 | chr3:98422558-98449457 |
| 14269 | Hsd3b6 | NM_013821.3 | chr3:98609426-98618366 |
| 14270 | Hsd3b7 | NM_001040684.1 | chr7:134944122-134947316 |
| 14271 | Hsd3b7 | NM_133943.2 | chr7:134944122-134947316 |
| 14272 | Hsdl1 | NM_175185.4 | chr12:122085877-122099100 |
| 14273 | Hsdl2 | NM_024255.3 | chr4:59594434-59631566 |
| 14274 | Hsf1 | NM_008296.2 | chr15:76307874-76331402 |
| 14275 | Hsf2 | NM_008297.3 | chr10:57206190-57232949 |
| 14276 | Hsf2bp | NM_028902.1 | chr17:32081713-32171453 |
| 14277 | Hsf3 | NM_172931.3 | chrX:93502205-93552579 |
| 14278 | Hsf4 | NM_001256042.1 | chr8:107793700-107799745 |
| 14279 | Hsf4 | NM_001256044.1 | chr8:107793700-107799745 |

| | | | |
|---|---|---|---|
| 14280 | Hsf4 | NM_011939.3 | chr8:107793700-107799745 |
| 14281 | Hsf4 | NR_045689.1 | chr8:107793700-107799745 |
| 14282 | Hsf5 | NM_001045527.1 | chr11:87430665-87473044 |
| 14283 | Hsfy2 | NM_027661.2 | chr1:56692892-56694295 |
| 14284 | Hsh2d | NM_197944.1 | chr8:74713566-74724857 |
| 14285 | Hsp90aa1 | NM_010480.5 | chr12:111929245-111934605 |
| 14286 | Hsp90ab1 | NM_008302.3 | chr17:45704726-45710210 |
| 14287 | Hsp90b1 | NM_011631.1 | chr10:86153585-86168189 |
| 14288 | Hspa12a | NM_175199.3 | chr19:58870240-58935474 |
| 14289 | Hspa12b | NM_028306.3 | chr2:130953147-130971719 |
| 14290 | Hspa13 | NM_030201.3 | chr16:75755435-75767063 |
| 14291 | Hspa13 | NR_027492.1 | chr16:75755435-75767063 |
| 14292 | Hspa14 | NM_015765.2 | chr2:3406125-3430086 |
| 14293 | Hspa14 | NR_103465.1 | chr2:3406125-3430086 |
| 14294 | Hspa1a | NM_010479.2 | chr17:35106303-35109101 |
| 14295 | Hspa1b | NM_010478.2 | chr17:35093373-35096183 |
| 14296 | Hspa1l | NM_013558.2 | chr17:35109647-35116173 |
| 14297 | Hspa2 | NM_001002012.1 | chr12:77505162-77507923 |
| 14298 | Hspa2 | NM_008301.4 | chr12:77505162-77507923 |
| 14299 | Hspa4 | NM_008300.3 | chr11:53073315-53113981 |
| 14300 | Hspa4l | NM_011020.3 | chr3:40549534-40594287 |
| 14301 | Hspa5 | NM_001163434.1 | chr2:34627609-34632049 |
| 14302 | Hspa5 | NM_022310.3 | chr2:34627609-34632049 |
| 14303 | Hspa8 | NM_031165.4 | chr9:40609355-40613282 |
| 14304 | Hspa9 | NM_010481.2 | chr18:35097068-35114005 |
| 14305 | Hspb1 | NM_013560.2 | chr5:136363788-136365433 |
| 14306 | Hspb11 | NM_028394.2 | chr4:106926538-106952493 |
| 14307 | Hspb2 | NM_001164708.1 | chr9:50559176-50564740 |
| 14308 | Hspb2 | NM_024441.3 | chr9:50559176-50564740 |
| 14309 | Hspb3 | NM_019960.2 | chr13:114453103-114453884 |
| 14310 | Hspb6 | NM_001012401.2 | chr7:31338320-31340458 |
| 14311 | Hspb7 | NM_013868.4 | chr4:140976693-140981225 |
| 14312 | Hspb8 | NM_030704.3 | chr5:116858503-116872873 |
| 14313 | Hspb9 | NM_029307.1 | chr11:100575163-100575889 |
| 14314 | Hspbap1 | NM_175111.3 | chr16:35770471-35828548 |
| 14315 | Hspbp1 | NM_024172.3 | chr7:4612122-4636565 |
| 14316 | Hspd1 | NM_010477.4 | chr1:55134677-55144776 |
| 14317 | Hspe1 | NM_008303.4 | chr1:55144991-55148161 |
| 14318 | Hspg2 | NM_008305.3 | chr4:137024718-137126545 |
| 14319 | Hsph1 | NM_013559.2 | chr5:150419419-150438890 |
| 14320 | Htatip2 | NM_001146049.1 | chr7:57014475-57029369 |
| 14321 | Htatip2 | NM_001146050.1 | chr7:57014475-57029369 |
| 14322 | Htatip2 | NM_001146052.1 | chr7:57014475-57029369 |
| 14323 | Htatip2 | NM_001146053.1 | chr7:57014475-57029369 |
| 14324 | Htatip2 | NM_016865.3 | chr7:57014475-57029369 |
| 14325 | Htatsf1 | NM_028242.2 | chrX:54306746-54320359 |
| 14326 | Htatsf1 | NM_029371.1 | chrX:54306746-54320359 |
| 14327 | Htr1a | NM_008308.4 | chr13:106233772-106238213 |
| 14328 | Htr1b | NM_010482.1 | chr9:81524999-81526159 |
| 14329 | Htr1d | NM_001285482.1 | chr4:135979438-136000316 |
| 14330 | Htr1d | NM_001285483.1 | chr4:135979438-136000316 |
| 14331 | Htr1d | NM_001285484.1 | chr4:135979438-136000316 |
| 14332 | Htr1d | NM_008309.5 | chr4:135979438-136000316 |
| 14333 | Htr1f | NM_008310.3 | chr16:64924554-65105610 |
| 14334 | Htr2a | NM_172812.2 | chr14:75040646-75106666 |
| 14335 | Htr2b | NM_008311.2 | chr1:87996612-88008545 |
| 14336 | Htr2c | NM_008312.4 | chrX:143397056-143631820 |
| 14337 | Htr3a | NM_001099644.1 | chr9:48707317-48719204 |
| 14338 | Htr3a | NM_013561.2 | chr9:48707317-48719204 |
| 14339 | Htr3b | NM_020274.4 | chr9:48743112-48773095 |
| 14340 | Htr4 | NM_008313.4 | chr18:62483857-62627456 |
| 14341 | Htr5a | NM_008314.2 | chr5:28168486-28181626 |
| 14342 | Htr5b | NM_010483.2 | chr1:123406349-123425042 |
| 14343 | Htr6 | NM_021358.2 | chr4:138617323-138630704 |
| 14344 | Htr7 | NM_008315.2 | chr19:36033218-36131856 |
| 14345 | Htra1 | NM_019564.3 | chr7:138079716-138129172 |
| 14346 | Htra2 | NM_019752.3 | chr6:83001262-83004565 |
| 14347 | Htra3 | NM_001042615.2 | chr5:35994674-36022429 |
| 14348 | Htra3 | NM_030127.3 | chr5:35994674-36022429 |
| 14349 | Htra4 | NM_001081187.3 | chr8:26135399-26149434 |
| 14350 | Htt | NM_010414.3 | chr5:35104388-35255183 |
| 14351 | Hunk | NM_015755.2 | chr16:90386641-90499798 |
| 14352 | Hus1 | NM_008316.5 | chr11:8893144-8911140 |
| 14353 | Hus1b | NM_153072.2 | chr13:31038445-31039630 |
| 14354 | Huwe1 | NM_021523.4 | chrX:148237825-148369961 |
| 14355 | Hvcn1 | NM_001042489.2 | chr5:122659737-122714469 |
| 14356 | Hvcn1 | NM_028752.3 | chr5:122659737-122714469 |
| 14357 | Hyal1 | NM_008317.4 | chr9:107479282-107482464 |
| 14358 | Hyal2 | NM_010489.2 | chr9:107471493-107475109 |
| 14359 | Hyal3 | NM_178020.3 | chr9:107483627-107489690 |
| 14360 | Hyal4 | NM_029848.1 | chr6:24698366-24716519 |
| 14361 | Hyal5 | NM_028957.2 | chr6:24807996-24841958 |
| 14362 | Hyal6 | NM_028920.2 | chr6:24683244-24695452 |
| 14363 | Hydin | NM_172916.2 | chr8:112790877-113134153 |
| 14364 | Hyi | NM_026601.1 | chr4:118032603-118081868 |
| 14365 | Hyi | NR_039946.2 | chr4:118032603-118081868 |
| 14366 | Hykk | NM_177351.4 | chr9:54765096-54797731 |
| 14367 | Hyls1 | NM_029762.1 | chr9:35368406-35377654 |
| 14368 | Hyou1 | NM_021395.4 | chr9:44187572-44200452 |
| 14369 | Hvpk | NM_026318.3 | chr2:121282823-121284176 |
| 14370 | I730028E13Rik | NR_045705.1 | chr9:60986321-60993066 |
| 14371 | I730030J21Rik | NR_045781.1 | chr15:100560935-100563168 |
| 14372 | I730030J21Rik | NR_045782.1 | chr15:100560935-100563168 |
| 14373 | I830012O16Rik | NM_001005858.3 | chr19:34682446-34687891 |
| 14374 | I830077J02Rik | NM_001033780.1 | chr3:105728808-105735582 |

Fig. 25 - 77

| | | | |
|---|---|---|---|
| 14375 | iah1 | NM_026347.3 | chr12:21322253-21329468 |
| 14376 | iapp | NM_010491.2 | chr6:142246945-142252339 |
| 14377 | iars | NM_172015.3 | chr13:49777498-49829636 |
| 14378 | iars2 | NM_198653.2 | chr1:187110541-187153280 |
| 14379 | iba57 | NM_001270791.1 | chr11:58968870-58977247 |
| 14380 | iba57 | NM_173785.6 | chr11:58968870-58977247 |
| 14381 | ibsp | NM_008318.3 | chr5:104728305-104740491 |
| 14382 | ibtk | NM_001081282.2 | chr9:85580966-85642941 |
| 14383 | ica1 | NM_001252266.1 | chr6:8580526-8728484 |
| 14384 | ica1 | NM_010492.3 | chr6:8580526-8728484 |
| 14385 | ical1 | NM_027407.3 | chr1:60045911-60099931 |
| 14386 | icam1 | NM_010493.2 | chr9:20820403-20833240 |
| 14387 | icam2 | NM_010494.1 | chr11:106238969-106243955 |
| 14388 | icam4 | NM_023892.2 | chr9:20833816-20834975 |
| 14389 | icam5 | NM_008319.2 | chr9:20836482-20843480 |
| 14390 | ick | NM_001163780.1 | chr9:77956998-78019916 |
| 14391 | ick | NM_019987.2 | chr9:77956998-78019916 |
| 14392 | icmt | NM_133788.2 | chr4:151671322-151692734 |
| 14393 | icmt | NR_037908.1 | chr4:151671322-151692734 |
| 14394 | icos | NM_017480.2 | chr1:61034757-61057164 |
| 14395 | icosl | NM_015790.3 | chr10:77532112-77542270 |
| 14396 | ict1 | NM_026729.1 | chr11:115265079-115272227 |
| 14397 | id1 | NM_010495.3 | chr2:152561986-152563146 |
| 14398 | id2 | NM_010496.3 | chr12:25778663-25780957 |
| 14399 | id3 | NM_008321.2 | chr4:136699736-135701307 |
| 14400 | id4 | NM_031166.2 | chr13:48356796-48359405 |
| 14401 | ide | NM_031156.3 | chr19:37343230-37405103 |
| 14402 | idh1 | NM_001111320.1 | chr1:65205189-65233053 |
| 14403 | idh1 | NM_010497.3 | chr1:65205189-65233053 |
| 14404 | idh2 | NM_173011.2 | chr7:87239733-87260236 |
| 14405 | idh3a | NM_029573.2 | chr9:54434317-54452469 |
| 14406 | idh3b | NM_130884.4 | chr2:130105045-130110187 |
| 14407 | idh3g | NM_008323.1 | chrX:71024301-71032236 |
| 14408 | idi1 | NM_145360.2 | chr13:8884851-8891642 |
| 14409 | idi2 | NM_177197.4 | chr13:8952108-8960181 |
| 14410 | idnk | NM_001048060.2 | chr13:58259009-58266054 |
| 14411 | idnk | NM_198004.3 | chr13:58259009-58266054 |
| 14412 | ido1 | NM_008324.2 | chr8:25694612-25707481 |
| 14413 | ido2 | NM_145949.2 | chr8:25642363-25686805 |
| 14414 | ids | NM_010498.3 | chrX:67596244-67618260 |
| 14415 | idua | NM_008325.4 | chr5:109058828-109114465 |
| 14416 | idua | NM_172997.1 | chr5:109058828-109114465 |
| 14417 | ier2 | NM_010499.4 | chr8:87185229-87186751 |
| 14418 | ier3 | NM_133662.2 | chr17:35958657-35959856 |
| 14419 | ier3ip1 | NM_025409.3 | chr18:77168765-77180353 |
| 14420 | ier5 | NM_010500.2 | chr1:156943496-156946766 |
| 14421 | ier5l | NM_030244.3 | chr2:30328160-30329719 |
| 14422 | iffo1 | NM_001039669.3 | chr6:125095258-125111800 |
| 14423 | iffo1 | NM_178787.6 | chr6:125095258-125111800 |
| 14424 | iffo2 | NM_001205173.1 | chr4:139086462-139176297 |
| 14425 | iffo2 | NM_183148.3 | chr4:139086462-139176297 |
| 14426 | ifi202b | NM_008327.2 | chr1:175892699-175912975 |
| 14427 | ifi202b | NM_011940.2 | chr1:175892699-175912975 |
| 14428 | ifi203 | NM_001045481.1 | chr1:175850533-175872623 |
| 14429 | ifi203 | NM_008328.2 | chr1:175850533-175872623 |
| 14430 | ifi204 | NM_008329.2 | chr1:175677424-175697050 |
| 14431 | ifi205 | NM_172648.3 | chr1:175941128-175961886 |
| 14432 | ifi27 | NM_026790.2 | chr12:104672082-104681890 |
| 14433 | ifi27 | NM_194066.2 | chr12:104672082-104681890 |
| 14434 | ifi27 | NM_194067.2 | chr12:104672082-104681890 |
| 14435 | ifi27 | NM_194068.1 | chr12:104672082-104681890 |
| 14436 | ifi27 | NM_194069.1 | chr12:104672082-104681890 |
| 14437 | ifi27l2a | NM_001281830.1 | chr12:104672082-104681890 |
| 14438 | ifi27l2a | NM_029803.3 | chr12:104672082-104681890 |
| 14439 | ifi27l2b | NM_145449.2 | chr12:104689107-104695433 |
| 14440 | ifi30 | NM_023065.3 | chr8:73286671-73290562 |
| 14441 | ifi35 | NM_027320.4 | chr11:101309725-101320015 |
| 14442 | ifi44 | NM_133871.2 | chr3:151393886-151412923 |
| 14443 | ifi44l | NM_031367.1 | chr3:151421700-151425855 |
| 14444 | ifi47 | NM_001270676.1 | chr11:48851161-48948889 |
| 14445 | ifi47 | NM_001271677.1 | chr11:48851161-48948889 |
| 14446 | ifi47 | NM_008330.2 | chr11:48851161-48948889 |
| 14447 | ifih1 | NM_001164771.1 | chr2:62433849-62484312 |
| 14448 | ifih1 | NM_027835.3 | chr2:62433849-62484312 |
| 14449 | ifit1 | NM_008331.3 | chr19:34715378-34724499 |
| 14450 | ifit2 | NM_008332.3 | chr19:34625183-34651024 |
| 14451 | ifit3 | NM_010501.2 | chr19:34658018-34663472 |
| 14452 | ifitm1 | NM_001112715.1 | chr7:148153327-148155726 |
| 14453 | ifitm1 | NM_026820.3 | chr7:148153327-148155726 |
| 14454 | ifitm10 | NM_177265.4 | chr7:149512014-149558164 |
| 14455 | ifitm2 | NM_030694.1 | chr7:148140737-148141860 |
| 14456 | ifitm3 | NM_025378.2 | chr7:148195488-148196643 |
| 14457 | ifitm5 | NM_053088.2 | chr7:148134860-148136138 |
| 14458 | ifitm6 | NM_001033632.1 | chr7:148201710-148202791 |
| 14459 | ifitm7 | NM_001270718.1 | chr13:13981795-13986960 |
| 14460 | ifitd1 | NM_028742.2 | chr6:145345754-145383445 |
| 14461 | ifna1 | NM_010502.2 | chr4:88495990-88496660 |
| 14462 | ifna11 | NM_008333.2 | chr4:88465822-88466469 |
| 14463 | ifna12 | NM_177361.2 | chr4:88248483-88249280 |
| 14464 | ifna13 | NM_177347.2 | chr4:88289544-88290363 |
| 14465 | ifna14 | NM_206975.1 | chr4:88217132-88217702 |
| 14466 | ifna15 | NM_206870.1 | chr4:88203576-88204149 |
| 14467 | ifna16 | NM_206867.1 | chr4:88322190-88322760 |
| 14468 | ifna2 | NM_010503.2 | chr4:88329110-88329683 |
| 14469 | ifna4 | NM_010504.2 | chr4:88487719-88488363 |

| | | | |
|---|---|---|---|
| 14470 | ifna5 | NM_010505.2 | chr4:88481428-88481998 |
| 14471 | ifna6 | NM_206871.1 | chr4:88473319-88473889 |
| 14472 | ifna7 | NM_008334.3 | chr4:88462128-88462704 |
| 14473 | ifna9 | NM_010507.1 | chr4:88237716-88238289 |
| 14474 | ifnab | NM_008336.2 | chr4:88336502-88337172 |
| 14475 | ifnar1 | NM_010508.2 | chr16:91485459-91510767 |
| 14476 | ifnar2 | NM_001110498.1 | chr16:91373027-91405832 |
| 14477 | ifnar2 | NM_010509.2 | chr16:91373027-91405832 |
| 14478 | ifnb1 | NM_010510.1 | chr4:88167928-88168698 |
| 14479 | ifne | NM_177348.2 | chr4:88525441-88526105 |
| 14480 | ifng | NM_008337.3 | chr10:117878102-117882948 |
| 14481 | ifngr1 | NM_010511.2 | chr10:19311763-19330031 |
| 14482 | ifngr2 | NM_008338.3 | chr16:91547338-91564252 |
| 14483 | ifnk | NM_199157.2 | chr4:35099804-35101268 |
| 14484 | ifnl2 | NM_001024673.2 | chr7:29293879-29295379 |
| 14485 | ifnl3 | NM_177396.1 | chr7:29307854-29309341 |
| 14486 | ifnlr1 | NM_174851.3 | chr4:135242371-135264095 |
| 14487 | ifnz | NM_197889.2 | chr4:88428034-88429496 |
| 14488 | ifrd1 | NM_013562.2 | chr12:40929716-40949776 |
| 14489 | ifrd2 | NM_025903.2 | chr9:107490048-107495369 |
| 14490 | ift122 | NM_001167763.1 | chr6:115803545-115876717 |
| 14491 | ift122 | NM_031177.4 | chr6:115803545-115876717 |
| 14492 | ift140 | NM_134126.3 | chr17:25153031-25236442 |
| 14493 | ift172 | NM_026298.5 | chr5:31555652-31593487 |
| 14494 | ift20 | NM_018854.4 | chr11:78349937-78354975 |
| 14495 | ift22 | NM_026073.2 | chr5:137384019-137389114 |
| 14496 | ift27 | NM_025931.2 | chr15:77989892-78004538 |
| 14497 | ift43 | NM_001198843.1 | chr12:87423510-87503409 |
| 14498 | ift43 | NM_029601.3 | chr12:87423510-87503409 |
| 14499 | ift46 | NM_023831.3 | chr9:44581091-44600797 |
| 14500 | ift52 | NM_172150.4 | chr2:162843207-162871871 |
| 14501 | ift57 | NM_028680.3 | chr16:49699406-49765239 |
| 14502 | ift74 | NM_001290568.1 | chr4:94281181-94359924 |
| 14503 | ift74 | NM_026319.3 | chr4:94281181-94359924 |
| 14504 | ift80 | NM_026641.2 | chr3:68696420-68808492 |
| 14505 | ift81 | NM_009879.3 | chr5:123000212-123064527 |
| 14506 | ift88 | NM_009376.2 | chr14:58042907-58136773 |
| 14507 | igbp1 | NM_008784.3 | chrX:97689629-97711464 |
| 14508 | igbp1b | NM_015777.2 | chr13:138605613-138606965 |
| 14509 | igdcc3 | NM_008988.2 | chr9:64988995-65033677 |
| 14510 | igdcc4 | NM_001290315.1 | chr9:64949292-64985754 |
| 14511 | igdcc4 | NM_020043.3 | chr9:64949292-64985754 |
| 14512 | igf1 | NM_001111274.1 | chr10:87321800-87399792 |
| 14513 | igf1 | NM_001111275.1 | chr10:87321800-87399792 |
| 14514 | igf1 | NM_001111276.1 | chr10:87321800-87399792 |
| 14515 | igf1 | NM_010512.4 | chr10:87321800-87399792 |
| 14516 | igf1 | NM_184052.3 | chr10:87321800-87399792 |
| 14517 | igf1r | NM_010513.2 | chr7:75097142-75378553 |
| 14518 | igf2 | NM_001122736.3 | chr7:149836672-149856261 |
| 14519 | igf2 | NM_001122737.1 | chr7:149836672-149856261 |
| 14520 | igf2 | NM_010514.3 | chr7:149836672-149856261 |
| 14521 | igf2bp1 | NM_009951.4 | chr11:95818478-95867258 |
| 14522 | igf2bp2 | NM_183029.2 | chr16:22059081-22163372 |
| 14523 | igf2bp3 | NM_023670.3 | chr6:49035216-49164953 |
| 14524 | igf2os | NR_002855.2 | chr7:149845598-149856261 |
| 14525 | igf2r | NM_010515.2 | chr17:12875272-12962572 |
| 14526 | igfals | NM_008340.3 | chr17:25015714-25018953 |
| 14527 | igfbp1 | NM_008341.4 | chr11:7097789-7102549 |
| 14528 | igfbp2 | NM_008342.3 | chr1:72871053-72899045 |
| 14529 | igfbp3 | NM_008343.2 | chr11:7106095-7113926 |
| 14530 | igfbp4 | NM_010517.3 | chr11:98902573-98913957 |
| 14531 | igfbp5 | NM_010518.2 | chr1:72904638-72921439 |
| 14532 | igfbp6 | NM_008344.3 | chr15:101974616-101979943 |
| 14533 | igfbp7 | NM_001159518.1 | chr5:77739508-77837070 |
| 14534 | igfbp7 | NM_008048.2 | chr5:77739508-77837070 |
| 14535 | igfbpl1 | NM_018741.2 | chr4:45822378-45839699 |
| 14536 | igf3 | NM_001003393.1 | chr7:18761842-18767211 |
| 14537 | igflr1 | NM_145580.2 | chr7:31350445-31352981 |
| 14538 | igfn1 | NM_177642.3 | chr1:137850154-137902919 |
| 14539 | ighmbp2 | NM_009212.2 | chr19:3259075-3283010 |
| 14540 | igip | NM_001267796.1 | chr18:36459754-36461132 |
| 14541 | igj | NM_152839.3 | chr5:88948833-88956922 |
| 14542 | igll1 | NM_001190325.1 | chr16:16860763-16864078 |
| 14543 | iglon5 | NM_001164518.1 | chr7:50728276-50745393 |
| 14544 | igsf1 | NM_177591.4 | chrX:47135713-47150922 |
| 14545 | igsf1 | NM_177915.4 | chrX:47135713-47150922 |
| 14546 | igsf1 | NM_183335.2 | chrX:47135713-47150922 |
| 14547 | igsf1 | NM_183336.2 | chrX:47135713-47150922 |
| 14548 | igsf10 | NM_001162884.1 | chr3:59120657-59148178 |
| 14549 | igsf11 | NM_170599.2 | chr16:38902457-39027270 |
| 14550 | igsf21 | NM_198610.2 | chr4:139582766-139602726 |
| 14551 | igsf2 | NM_027308.2 | chr7:20522653-20536092 |
| 14552 | igsf3 | NM_207205.2 | chr3:101181047-101266983 |
| 14553 | igsf5 | NM_001177886.1 | chr16:96583363-96643728 |
| 14554 | igsf5 | NM_001177887.1 | chr16:96583363-96643728 |
| 14555 | igsf5 | NM_028078.3 | chr16:96583363-96643728 |
| 14556 | igsf6 | NM_030691.1 | chr7:128207581-128218044 |
| 14557 | igsf8 | NM_080419.1 | chr1:174242537-174249966 |
| 14558 | igsf9 | NM_001145800.1 | chr1:174412343-174429008 |
| 14559 | igsf9 | NM_033608.3 | chr1:174412343-174429008 |
| 14560 | igsf9b | NM_001033323.3 | chr9:27106812-27142348 |
| 14561 | igsf9b | NM_001129787.1 | chr9:27106812-27142348 |
| 14562 | igtp | NM_018738.4 | chr11:58013057-58021094 |
| 14563 | ihh | NM_010544.2 | chr1:74991891-74998225 |
| 14564 | iigp1 | NM_001146275.1 | chr18:60535682-60552283 |

Fig. 25 - 78

| | | | | | | | | |
|---|---|---|---|---|---|---|---|---|
| 14565 | igp1 | NM_021792.4 | chr18:60535682-60552283 | | 14660 | il20 | NM_021380.1 | chr1:132803768-132807873 |
| 14566 | ik | NM_011879.2 | chr18:36904309-36917293 | | 14661 | il20ra | NM_172786.2 | chr10:19432392-19479859 |
| 14567 | ikbip | NM_026166.2 | chr10:90545783-90565358 | | 14662 | il20rb | NM_001033543.3 | chr9:100358137-100386892 |
| 14568 | ikbip | NM_027078.2 | chr10:90545783-90565358 | | 14663 | il21 | NM_001291041.1 | chr3:37121680-37131558 |
| 14569 | ikbkap | NM_026079.3 | chr4:56762552-56815203 | | 14664 | il21 | NM_021782.3 | chr3:37121680-37131558 |
| 14570 | ikbkb | NM_001159774.1 | chr8:23769676-23817055 | | 14665 | il21r | NM_021887.2 | chr7:132746942-132777084 |
| 14571 | ikbkb | NM_010546.2 | chr8:23769676-23817055 | | 14666 | il22 | NM_016971.2 | chr10:117642019-117647102 |
| 14572 | ikbke | NM_019777.3 | chr1:133151178-133176140 | | 14667 | il22ra1 | NM_178257.2 | chr4:135284073-135311298 |
| 14573 | ikbkg | NM_001136067.2 | chrX:71638629-71699117 | | 14668 | il22ra2 | NM_178258.2 | chr10:19341833-19354487 |
| 14574 | ikbkg | NM_001161421.1 | chrX:71638629-71699117 | | 14669 | il23a | NM_031252.2 | chr10:127733195-127735140 |
| 14575 | ikbkg | NM_001161422.1 | chrX:71638629-71699117 | | 14670 | il23r | NM_144548.1 | chr6:67372925-67441849 |
| 14576 | ikbkg | NM_001161423.1 | chrX:71638629-71699117 | | 14671 | il24 | NM_053095.2 | chr1:132778650-132783988 |
| 14577 | ikbkg | NM_001161424.1 | chrX:71638629-71699117 | | 14672 | il25 | NM_080729.3 | chr14:55551531-55554673 |
| 14578 | ikbkg | NM_010547.2 | chrX:71638629-71699117 | | 14673 | il27 | NM_145636.1 | chr7:133732808-133738424 |
| 14579 | ikbkg | NM_178590.4 | chrX:71638629-71699117 | | 14674 | il27ra | NM_016671.3 | chr8:86554185-86566474 |
| 14580 | ikzf1 | NM_001025597.2 | chr11:11586215-11672929 | | 14675 | il2ra | NM_008367.3 | chr2:11564418-11614821 |
| 14581 | ikzf1 | NM_009578.3 | chr11:11586215-11672929 | | 14676 | il2rb | NM_008368.4 | chr15:78310978-78325496 |
| 14582 | ikzf2 | NM_011770.4 | chr1:69577783-69732534 | | 14677 | il2rg | NM_013563.4 | chrX:98459725-98463545 |
| 14583 | ikzf3 | NM_011771.1 | chr11:98326006-98407345 | | 14678 | il3 | NM_010556.4 | chr11:54078586-54080781 |
| 14584 | ikzf4 | NM_011772.2 | chr10:128069470-128083049 | | 14679 | il31 | NM_029594.1 | chr5:123930161-123932110 |
| 14585 | ikzf5 | NM_175115.4 | chr7:138532162-138553992 | | 14680 | il31ra | NM_139299.2 | chr13:113313015-113370870 |
| 14586 | il10 | NM_010548.2 | chr1:132916421-132921547 | | 14681 | il33 | NM_001164724.1 | chr19:29999603-30035205 |
| 14587 | il10ra | NM_008348.2 | chr9:45061922-45077229 | | 14682 | il33 | NM_133775.2 | chr19:29999603-30035205 |
| 14588 | il10rb | NM_008349.5 | chr16:91406479-91426079 | | 14683 | il34 | NM_001135100.2 | chr8:113265728-113329824 |
| 14589 | il11 | NM_001290423.1 | chr7:4723979-4734459 | | 14684 | il34 | NM_029646.3 | chr8:113265728-113329824 |
| 14590 | il11 | NM_008350.4 | chr7:4723979-4734459 | | 14685 | il3ra | NM_008369.1 | chr14:15179608-15188004 |
| 14591 | il11ra1 | NM_001163401.1 | chr4:41707315-41721049 | | 14686 | il4 | NM_021283.2 | chr11:53425962-53432167 |
| 14592 | il11ra1 | NM_001172054.1 | chr4:41707315-41721049 | | 14687 | il4 | NR_027491.1 | chr11:53425962-53432167 |
| 14593 | il11ra1 | NM_010549.3 | chr4:41707315-41721049 | | 14688 | il4i1 | NM_010215.3 | chr7:52091658-52096179 |
| 14594 | il12a | NM_001159424.2 | chr3:68494565-68502469 | | 14689 | il4ra | NM_001008700.3 | chr7:132695795-132722988 |
| 14595 | il12a | NM_008351.3 | chr3:68494565-68502469 | | 14690 | il5 | NM_010558.1 | chr11:53534295-53538605 |
| 14596 | il12b | NM_008352.2 | chr11:44213564-44227519 | | 14691 | il5ra | NM_008370.2 | chr6:106660372-106699031 |
| 14597 | il12rb1 | NM_008353.2 | chr8:73332347-73345322 | | 14692 | il6 | NM_031168.1 | chr5:30339700-30346508 |
| 14598 | il12rb2 | NM_008354.3 | chr6:67242011-67326131 | | 14693 | il6ra | NM_010559.2 | chr3:89673245-89717084 |
| 14599 | il13 | NM_008355.3 | chr11:53444824-53448204 | | 14694 | il6st | NM_010560.3 | chr13:113254277-113297068 |
| 14600 | il13ra1 | NM_133990.5 | chrX:63652133-63711256 | | 14695 | il7 | NM_008371.4 | chr3:7572076-7613427 |
| 14601 | il13ra2 | NM_008356.4 | chrX:143818020-143838375 | | 14696 | il7r | NM_008372.4 | chr15:9435913-9459631 |
| 14602 | il15 | NM_001254747.1 | chr8:84855522-84926485 | | 14697 | il9 | NM_008373.1 | chr13:56580637-56583607 |
| 14603 | il15 | NM_008357.2 | chr8:84855522-84926485 | | 14698 | il9r | NM_001134458.1 | chr11:32088996-32100279 |
| 14604 | il15ra | NM_001271497.1 | chr2:11626919-11655612 | | 14699 | il9r | NM_008374.2 | chr11:32088996-32100279 |
| 14605 | il15ra | NM_001271498.1 | chr2:11626919-11655612 | | 14700 | ildr1 | NM_001285788.1 | chr16:36694063-36726890 |
| 14606 | il15ra | NM_001271499.1 | chr2:11626919-11655612 | | 14701 | ildr1 | NM_001285791.1 | chr16:36694063-36726890 |
| 14607 | il15ra | NM_001271500.1 | chr2:11626919-11655612 | | 14702 | ildr1 | NM_134109.2 | chr16:36694063-36726890 |
| 14608 | il15ra | NM_001271501.1 | chr2:11626919-11655612 | | 14703 | ildr2 | NM_001164528.1 | chr1:168184269-168246963 |
| 14609 | il15ra | NM_008358.3 | chr2:11626919-11655612 | | 14704 | ilf2 | NM_026374.3 | chr3:90280123-90292301 |
| 14610 | il15ra | NM_133836.2 | chr2:11626919-11655612 | | 14705 | ilf3 | NM_001042707.2 | chr9:21172314-21216164 |
| 14611 | il15ra | NR_073191.1 | chr2:11626919-11655612 | | 14706 | ilf3 | NM_001042708.2 | chr9:21172314-21216164 |
| 14612 | il15ra | NR_073192.1 | chr2:11626919-11655612 | | 14707 | ilf3 | NM_001042709.2 | chr9:21172314-21216164 |
| 14613 | il6 | NM_010551.3 | chr7:90791572-90884000 | | 14708 | ilf3 | NM_001277321.1 | chr9:21172314-21216164 |
| 14614 | il17a | NM_010552.3 | chr1:20720985-20724577 | | 14709 | ilf3 | NM_001277322.1 | chr9:21172314-21216164 |
| 14615 | il17b | NM_019508.1 | chr18:61847588-61852191 | | 14710 | ilf3 | NM_010561.3 | chr9:21172314-21216164 |
| 14616 | il17c | NM_145834.3 | chr8:124945984-124947539 | | 14711 | ilk | NM_001161724.1 | chr7:112880243-112892852 |
| 14617 | il17d | NM_154837.3 | chr14:58143665-58162003 | | 14712 | ilk | NM_010562.2 | chr7:112880243-112892852 |
| 14618 | il17f | NM_145856.2 | chr1:20767229-20774351 | | 14713 | ilkap | NM_023343.2 | chr1:93272407-93295360 |
| 14619 | il17ra | NM_008359.2 | chr6:120413214-120433745 | | 14714 | iltifb | NM_054079.2 | chr10:117726685-117732094 |
| 14620 | il17rb | NM_019583.3 | chr14:30809353-30822082 | | 14715 | ilvbl | NM_173751.4 | chr10:78037244-78047247 |
| 14621 | il17rc | NM_134159.4 | chr6:113421448-113433157 | | 14716 | immp1l | NM_028260.2 | chr2:105744794-105805715 |
| 14622 | il17rc | NM_178942.1 | chr6:113421448-113433157 | | 14717 | immp2l | NM_053122.4 | chr12:41759677-43056575 |
| 14623 | il17rd | NM_134437.3 | chr14:27852186-27920472 | | 14718 | immt | NM_001253681.1 | chr6:71781313-71825260 |
| 14624 | il17re | NM_001034029.1 | chr6:113408477-113420745 | | 14719 | immt | NM_001253686.1 | chr6:71781313-71825260 |
| 14625 | il17re | NM_001034031.1 | chr6:113408477-113420745 | | 14720 | immt | NM_001253687.1 | chr6:71781313-71825260 |
| 14626 | il17re | NM_145826.5 | chr6:113408477-113420745 | | 14721 | immt | NM_001253688.1 | chr6:71781313-71825260 |
| 14627 | il18 | NM_008360.1 | chr9:50373472-50389942 | | 14722 | immt | NM_001253689.1 | chr6:71781313-71825260 |
| 14628 | il18bp | NM_010531.1 | chr7:109163590-109166669 | | 14723 | immt | NM_029673.3 | chr6:71781313-71825260 |
| 14629 | il18r1 | NM_001161842.1 | chr1:40522396-40557699 | | 14724 | imp3 | NM_133976.2 | chr9:56785306-56786205 |
| 14630 | il18r1 | NM_001161843.1 | chr1:40522396-40557699 | | 14725 | imp4 | NM_176601.3 | chr1:34496673-34502592 |
| 14631 | il18r1 | NM_008365.2 | chr1:40522396-40557699 | | 14726 | impa1 | NM_018864.5 | chr3:10313539-10331439 |
| 14632 | il18rap | NM_010553.2 | chr1:40572206-40608550 | | 14727 | impa2 | NM_053261.2 | chr18:67448876-67478495 |
| 14633 | il19 | NM_001009940.1 | chr1:132829232-132835818 | | 14728 | impact | NM_008378.2 | chr18:13130760-13151457 |
| 14634 | il1a | NM_010554.4 | chr2:129125346-129135708 | | 14729 | impad1 | NM_177730.3 | chr4:4691500-4720453 |
| 14635 | il1b | NM_008361.3 | chr2:129190316-129196856 | | 14730 | impdh1 | NM_011829.3 | chr6:29150439-29162271 |
| 14636 | il1bos | NR_015474.1 | chr2:129195638-129201469 | | 14731 | impdh2 | NM_011830.1 | chr9:108462831-108467897 |
| 14637 | il1f10 | NM_153077.2 | chr2:24146715-24149340 | | 14732 | impg1 | NM_022016.3 | chr9:80161136-80359045 |
| 14638 | il1f5 | NM_001146087.1 | chr2:24132473-24137952 | | 14733 | impg2 | NM_174876.3 | chr16:56204425-56273866 |
| 14639 | il1f5 | NM_001146088.1 | chr2:24132473-24137952 | | 14734 | ina | NM_146100.4 | chr19:47089188-47098836 |
| 14640 | il1f5 | NM_019451.2 | chr2:24132473-24137952 | | 14735 | inadl | NM_001005784.1 | chr4:98062516-98386294 |
| 14641 | il1f6 | NM_019450.3 | chr2:24070936-24081221 | | 14736 | inadl | NM_001005787.1 | chr4:98062516-98386294 |
| 14642 | il1f8 | NM_027163.1 | chr2:24008691-24015623 | | 14737 | inadl | NM_007704.2 | chr4:98062516-98386294 |
| 14643 | il1f9 | NM_153511.3 | chr2:24041995-24049087 | | 14738 | inadl | NM_172696.2 | chr4:98062516-98386294 |
| 14644 | il1r1 | NM_001123382.1 | chr1:40281924-40373022 | | 14739 | inca1 | NM_001252482.1 | chr11:70501862-70513657 |
| 14645 | il1r1 | NM_008362.2 | chr1:40281924-40373022 | | 14740 | inca1 | NM_001252483.1 | chr11:70501862-70513657 |
| 14646 | il1r2 | NM_010555.4 | chr1:40141613-40182070 | | 14741 | inca1 | NM_001252484.1 | chr11:70501862-70513657 |
| 14647 | il1rap | NM_001159317.1 | chr16:26581790-26755588 | | 14742 | inca1 | NM_001252485.1 | chr11:70501862-70513657 |
| 14648 | il1rap | NM_001159318.1 | chr16:26581790-26755588 | | 14743 | inca1 | NM_213729.1 | chr11:70501862-70513657 |
| 14649 | il1rap | NM_008364.2 | chr16:26581790-26755588 | | 14744 | incenp | NM_016692.3 | chr19:9946786-9974023 |
| 14650 | il1rap | NM_134103.2 | chr16:26581790-26755588 | | 14745 | inf2 | NM_198411.2 | chr12:113826994-113853768 |
| 14651 | il1rapl1 | NM_001160403.1 | chrX:83992580-85360962 | | 14746 | ing1 | NM_011919.5 | chr8:11556065-11563250 |
| 14652 | il1rapl2 | NM_030688.1 | chrX:134106088-135381494 | | 14747 | ing2 | NM_023503.3 | chr8:48752531-48760513 |
| 14653 | il1rl1 | NM_001025602.3 | chr1:40496493-40522259 | | 14748 | ing3 | NM_023626.4 | chr6:21899614-21926037 |
| 14654 | il1rl1 | NM_010743.3 | chr1:40496493-40522259 | | 14749 | ing4 | NM_133345.2 | chr6:124989865-124999282 |
| 14655 | il1rl2 | NM_133193.3 | chr1:40381471-40422316 | | 14750 | ing5 | NM_025454.2 | chr1:95700541-95718677 |
| 14656 | il1rn | NM_001039701.3 | chr2:24192379-24207011 | | 14751 | inha | NM_010564.4 | chr1:75503651-75506929 |
| 14657 | il1rn | NM_001159562.1 | chr2:24192379-24207011 | | 14752 | inhba | NM_008380.1 | chr13:16106307-16119044 |
| 14658 | il1rn | NM_031167.5 | chr2:24192379-24207011 | | 14753 | inhbb | NM_008381.3 | chr1:121312041-121318825 |
| 14659 | il2 | NM_008366.3 | chr3:37019641-37024876 | | 14754 | inhbc | NM_010565.3 | chr10:126793381-126807600 |

Fig. 25 - 79

| | | | |
|---|---|---|---|
| 14755 | Inhbe | NM_008382.2 | chr10:126786457-126788828 |
| 14756 | Inip | NM_001013577.1 | chr4:59782518-59796727 |
| 14757 | Inmt | NM_009349.3 | chr6:55120620-55124984 |
| 14758 | Ino80 | NM_026574.3 | chr2:119198778-119303365 |
| 14759 | Ino80b | NM_023547.1 | chr6:83071821-83075023 |
| 14760 | Ino80c | NM_172625.2 | chr18:24263261-24280320 |
| 14761 | Ino80d | NM_001081436.2 | chr1:63094374-63160841 |
| 14762 | Ino80d | NM_001114609.1 | chr1:63094374-63160841 |
| 14763 | Ino80dos | NR_045914.1 | chr1:63161044-63223396 |
| 14764 | Ino80dos | NR_045915.1 | chr1:63161044-63223396 |
| 14765 | Ino80e | NM_153580.1 | chr7:133995947-134004977 |
| 14766 | Inppl | NM_008384.2 | chr1:52846263-52874532 |
| 14767 | Inpp4a | NM_001290797.1 | chr1:37356682-37467585 |
| 14768 | Inpp4a | NM_001290798.1 | chr1:37356682-37467585 |
| 14769 | Inpp4a | NM_001290799.1 | chr1:37356682-37467585 |
| 14770 | Inpp4a | NM_030266.4 | chr1:37356682-37467585 |
| 14771 | Inpp4a | NM_172971.3 | chr1:37356682-37467585 |
| 14772 | Inpp4b | NM_001024617.3 | chr8:84239098-84646460 |
| 14773 | Inpp5a | NM_001127363.1 | chr7:146575007-146768696 |
| 14774 | Inpp5a | NM_183144.3 | chr7:146575007-146768696 |
| 14775 | Inpp5b | NM_008385.4 | chr4:124419094-124478755 |
| 14776 | Inpp5d | NM_001110192.2 | chr1:89516886-89617083 |
| 14777 | Inpp5d | NM_001110193.2 | chr1:89516886-89617083 |
| 14778 | Inpp5d | NM_010566.3 | chr1:89516886-89617083 |
| 14779 | Inpp5e | NM_001290437.1 | chr2:26244867-26264739 |
| 14780 | Inpp5e | NM_033134.3 | chr2:26244867-26264739 |
| 14781 | Inpp5e | NR_110957.1 | chr2:26244867-26264739 |
| 14782 | Inpp5f | NM_178641.5 | chr7:135754878-135839950 |
| 14783 | Inpp5j | NM_172439.3 | chr11:3394274-3404824 |
| 14784 | Inpp5k | NM_008916.2 | chr11:75444521-75462367 |
| 14785 | Inppl1 | NM_001122739.1 | chr7:108966826-108986740 |
| 14786 | Inppl1 | NM_010567.2 | chr7:108966826-108986740 |
| 14787 | Ins1 | NM_008386.3 | chr19:52338812-52339948 |
| 14788 | Ins2 | NM_001185083.1 | chr7:149864560-149865613 |
| 14789 | Ins2 | NM_001185084.1 | chr7:149864560-149865613 |
| 14790 | Ins2 | NM_008387.4 | chr7:149864560-149865613 |
| 14791 | Insc | NM_173767.3 | chr7:121889279-121993894 |
| 14792 | Insig1 | NM_153526.5 | chr5:28397951-28405202 |
| 14793 | Insig2 | NM_001271531.1 | chr1:123200929-123229166 |
| 14794 | Insig2 | NM_001271532.1 | chr1:123200929-123229166 |
| 14795 | Insig2 | NM_133748.2 | chr1:123200929-123229166 |
| 14796 | Insig2 | NM_178082.3 | chr1:123200929-123229166 |
| 14797 | Insl3 | NM_013564.7 | chr8:74213151-74214476 |
| 14798 | Insl5 | NM_001290648.1 | chr4:102690477-102699447 |
| 14799 | Insl5 | NM_011831.2 | chr4:102690477-102699447 |
| 14800 | Insl6 | NM_013754.1 | chr19:29395843-29399808 |
| 14801 | Insm1 | NM_016889.3 | chr2:146047732-146050754 |
| 14802 | Insm2 | NM_020287.2 | chr12:56699903-56703004 |
| 14803 | Insr | NM_010568.2 | chr8:3150921-3279617 |
| 14804 | Insrr | NM_011832.2 | chr3:87600872-87620023 |
| 14805 | Ints1 | NM_026748.2 | chr5:140227236-140251632 |
| 14806 | Ints10 | NM_027590.4 | chr8:71317852-71351543 |
| 14807 | Ints12 | NM_027927.3 | chr3:132754916-132773949 |
| 14808 | Ints2 | NM_027421.2 | chr11:86024184-86071070 |
| 14809 | Ints3 | NM_145540.3 | chr3:90195301-90237558 |
| 14810 | Ints3 | NM_178876.3 | chr3:90195301-90237558 |
| 14811 | Ints4 | NM_027256.2 | chr7:104629465-104689908 |
| 14812 | Ints5 | NM_176843.3 | chr19:8967476-8972380 |
| 14813 | Ints6 | NM_008715.1 | chr14:63295165-63379949 |
| 14814 | Ints8 | NM_178632.6 | chr11:193399612-193445570 |
| 14815 | Ints8 | NM_001159595.1 | chr4:11118497-11181406 |
| 14816 | Ints8 | NM_178112.5 | chr4:11118497-11181406 |
| 14817 | Ints9 | NM_001253731.1 | chr14:65568881-65658672 |
| 14818 | Ints9 | NM_153414.4 | chr14:65568881-65658672 |
| 14819 | Intu | NM_175515.5 | chr3:40439688-40508696 |
| 14820 | Invs | NM_001281977.1 | chr4:48292631-48486294 |
| 14821 | Invs | NM_001281978.1 | chr4:48292631-48486294 |
| 14822 | Invs | NM_010569.4 | chr4:48292631-48486294 |
| 14823 | Ip6k1 | NM_013785.2 | chr9:107904978-107951113 |
| 14824 | Ip6k2 | NM_029634.2 | chr9:108698324-108708664 |
| 14825 | Ip6k3 | NM_173027.2 | chr17:27280915-27304709 |
| 14826 | Ipcef1 | NM_001033391.2 | chr10:3308331-3557940 |
| 14827 | Ipcef1 | NM_001170800.1 | chr10:3308331-3557940 |
| 14828 | Ipcef1 | NM_001170801.1 | chr10:3308331-3557940 |
| 14829 | Ipcef1 | NM_001170802.1 | chr10:3308331-3557940 |
| 14830 | Ipmk | NM_027184.4 | chr10:70810540-70848633 |
| 14831 | Ipo11 | NM_029665.3 | chr13:107584518-107726995 |
| 14832 | Ipo13 | NM_146152.3 | chr4:117567097-117587604 |
| 14833 | Ipo4 | NM_024287.6 | chr14:56244465-56254515 |
| 14834 | Ipo5 | NM_023579.4 | chr14:121310415-121347266 |
| 14835 | Ipo7 | NM_181517.3 | chr7:117161939-117198628 |
| 14836 | Ipo8 | NM_001081113.1 | chr6:148719205-148779989 |
| 14837 | Ipo9 | NM_153774.1 | chr1:137278891-137327068 |
| 14838 | Ipp | NM_008389.3 | chr4:116180153-116210840 |
| 14839 | Ippk | NM_001276399.1 | chr13:49516591-49558429 |
| 14840 | Ippk | NM_199056.3 | chr13:49516591-49558429 |
| 14841 | Ippk | NR_075085.1 | chr13:49516591-49558429 |
| 14842 | Ipw | NR_015351.1 | chr7:66874528-66934248 |
| 14843 | Iqca | NM_029122.2 | chr1:91988706-92049976 |
| 14844 | Iqcb1 | NM_177128.1 | chr16:36828486-36872801 |
| 14845 | Iqcc | NM_198026.2 | chr4:129292860-129296337 |
| 14846 | Iqcd | NM_029408.2 | chr5:121039031-121057122 |
| 14847 | Iqce | NM_028833.3 | chr5:141139458-141178332 |
| 14848 | Iqcf1 | NM_001146701.1 | chr9:106402297-106404581 |
| 14849 | Iqcf1 | NM_028843.1 | chr9:106402297-106404581 |
| 14850 | Iqcf3 | NM_026645.3 | chr9:106445719-106463956 |
| 14851 | Iqcf4 | NM_026090.2 | chr9:106470649-106473298 |
| 14852 | Iqcf5 | NM_029300.1 | chr9:106416903-106418334 |
| 14853 | Iqcf6 | NM_001101628.1 | chr9:106528812-106529943 |
| 14854 | Iqcg | NM_178378.3 | chr16:33014356-33056272 |
| 14855 | Iqch | NM_030068.1 | chr9:63269427-63450255 |
| 14856 | Iqcj | NM_177585.3 | chr3:67696142-67860515 |
| 14857 | Iqck | NM_001081446.1 | chr7:125999289-126116166 |
| 14858 | Iqgap1 | NM_016721.2 | chr7:87856468-87948217 |
| 14859 | Iqgap2 | NM_027711.1 | chr13:96397132-96661877 |
| 14860 | Iqgap3 | NM_001033484.1 | chr3:87885972-87924970 |
| 14861 | Iqsec1 | NM_001134383.1 | chr6:90609591-90760117 |
| 14862 | Iqsec1 | NM_001134384.1 | chr6:90609591-90760117 |
| 14863 | Iqsec2 | NM_001005475.2 | chrX:148578810-148659780 |
| 14864 | Iqsec2 | NM_001114664.2 | chrX:148578810-148659780 |
| 14865 | Iqsec3 | NM_001033354.3 | chr6:121322945-121423696 |
| 14866 | Iqsec3 | NM_001289685.1 | chr6:121322945-121423696 |
| 14867 | Iqsec3 | NR_110358.1 | chr6:121322945-121423696 |
| 14868 | Iqub | NM_172535.3 | chr6:24394864-24465067 |
| 14869 | Irak1 | NM_001177973.1 | chrX:71259252-71269275 |
| 14870 | Irak1 | NM_001177974.1 | chrX:71259252-71269275 |
| 14871 | Irak1 | NM_001177975.1 | chrX:71259252-71269275 |
| 14872 | Irak1 | NM_001177976.1 | chrX:71259252-71269275 |
| 14873 | Irak1 | NM_008363.2 | chrX:71259252-71269275 |
| 14874 | Irak1bp1 | NM_001168240.1 | chr9:82723412-82741295 |
| 14875 | Irak1bp1 | NM_029986.4 | chr9:82723412-82741295 |
| 14876 | Irak2 | NM_001113553.1 | chr6:113588460-113645020 |
| 14877 | Irak2 | NM_172161.4 | chr6:113588460-113645020 |
| 14878 | Irak3 | NM_028679.3 | chr10:119578709-119638593 |
| 14879 | Irak4 | NM_029926.5 | chr15:94374090-94398747 |
| 14880 | Ireb2 | NM_022655.3 | chr9:54711561-54760341 |
| 14881 | Irf1 | NM_001159393.1 | chr11:53583515-53591876 |
| 14882 | Irf1 | NM_001159396.1 | chr11:53583515-53591876 |
| 14883 | Irf1 | NM_008390.2 | chr11:53583515-53591876 |
| 14884 | Irf2 | NM_008391.4 | chr8:47825098-47932812 |
| 14885 | Irf2bp1 | NM_178757.3 | chr7:19589413-19592112 |
| 14886 | Irf2bp2 | NM_001164598.1 | chr8:129112195-129117336 |
| 14887 | Irf2bpl | NM_145836.2 | chr12:88221652-88225764 |
| 14888 | Irf3 | NM_016849.4 | chr7:52253017-52258218 |
| 14889 | Irf3 | NR_045611.1 | chr7:52253017-52258218 |
| 14890 | Irf4 | NM_013674.1 | chr13:30841126-30858796 |
| 14891 | Irf5 | NM_001252382.1 | chr6:29476624-29487320 |
| 14892 | Irf5 | NM_012057.4 | chr6:29476624-29487320 |
| 14893 | Irf6 | NM_016851.2 | chr1:194979305-194998229 |
| 14894 | Irf7 | NM_001252600.1 | chr7:148449081-148452323 |
| 14895 | Irf7 | NM_001252601.1 | chr7:148449081-148452323 |
| 14896 | Irf7 | NM_016850.3 | chr7:148449081-148452323 |
| 14897 | Irf8 | NM_008320.4 | chr8:123260275-123280592 |
| 14898 | Irf9 | NM_001159417.1 | chr14:56222821-56228867 |
| 14899 | Irf9 | NM_001159418.1 | chr14:56222821-56228867 |
| 14900 | Irf9 | NM_008394.3 | chr14:56222821-56228867 |
| 14901 | Irg1 | NM_008392.1 | chr14:103446228-103455790 |
| 14902 | Irgc1 | NM_199013.2 | chr7:25216944-25230701 |
| 14903 | Irgm1 | NM_008326.1 | chr11:48678750-48684848 |
| 14904 | Irgm2 | NM_019440.3 | chr11:58028478-58036285 |
| 14905 | Irgq | NM_153134.3 | chr7:25315666-25323619 |
| 14906 | Irs1 | NM_010570.4 | chr1:82229679-82288014 |
| 14907 | Irs2 | NM_001081212.1 | chr8:10986964-11008430 |
| 14908 | Irs3 | NM_010571.3 | chr5:138084259-138086942 |
| 14909 | Irs4 | NM_010572.2 | chrX:138145540-138159760 |
| 14910 | Irx1 | NM_010573.2 | chr13:72095679-72101171 |
| 14911 | Irx2 | NM_010574.2 | chr13:72766425-72771642 |
| 14912 | Irx3 | NM_001253822.1 | chr8:94322409-94325553 |
| 14913 | Irx3 | NM_008393.3 | chr8:94322409-94325553 |
| 14914 | Irx4 | NM_018885.2 | chr13:73397944-73407068 |
| 14915 | Irx5 | NM_018826.2 | chr8:94881694-94885355 |
| 14916 | Irx6 | NM_022428.3 | chr8:95198300-95203979 |
| 14917 | Isca1 | NM_026921.4 | chr13:59856775-59871150 |
| 14918 | Isca2 | NM_028863.1 | chr12:86114219-86116039 |
| 14919 | Iscu | NM_025526.4 | chr5:114222820-114228291 |
| 14920 | Isg15 | NM_035783.3 | chr4:155573532-155574927 |
| 14921 | Isg20 | NM_001113527.1 | chr7:86058309-86065282 |
| 14922 | Isg20 | NM_001291220.1 | chr7:86058309-86065282 |
| 14923 | Isg20 | NM_001291221.1 | chr7:86058309-86065282 |
| 14924 | Isg20 | NM_020583.5 | chr7:86058309-86065282 |
| 14925 | Isg20l2 | NM_177663.4 | chr3:87734235-87744608 |
| 14926 | Isl1 | NM_021459.4 | chr13:117088477-117099896 |
| 14927 | Isl2 | NM_027397.3 | chr9:55388955-55393985 |
| 14928 | Islr | NM_001195431.1 | chr9:58004070-58007028 |
| 14929 | Islr | NM_012043.4 | chr9:58004070-58007028 |
| 14930 | Islr2 | NM_001161535.1 | chr9:58044103-58056615 |
| 14931 | Islr2 | NM_001161536.1 | chr9:58044103-58056615 |
| 14932 | Islr2 | NM_001161537.1 | chr9:58044103-58056615 |
| 14933 | Islr2 | NM_001161538.1 | chr9:58044103-58056615 |
| 14934 | Islr2 | NM_001161539.1 | chr9:58044103-58056615 |
| 14935 | Islr2 | NM_001161540.1 | chr9:58044103-58056615 |
| 14936 | Islr2 | NM_001161541.1 | chr9:58044103-58056615 |
| 14937 | Islr2 | NM_177193.5 | chr9:58044103-58056615 |
| 14938 | Ism1 | NM_001276489.1 | chr2:139503913-139584317 |
| 14939 | Ism2 | NM_001290302.1 | chr12:88619587-88640655 |
| 14940 | Isoc1 | NM_025478.3 | chr18:58819535-58839224 |
| 14941 | Isoc2a | NM_001101598.1 | chr7:4828654-4847318 |
| 14942 | Isoc2b | NM_026158.2 | chr7:4796561-4817781 |
| 14943 | Ispd | NM_001289502.1 | chr12:37108036-37416090 |
| 14944 | Ispd | NM_001289503.1 | chr12:37108036-37416090 |

Fig. 25 - 80

| | | | | | | | | |
|---|---|---|---|---|---|---|---|---|
| 14945 | Ispd | NM_001289504.1 | chr12:37108036-37416090 | | 15040 | Iyd | NM_027391.3 | chr10:6791663-6806262 |
| 14946 | Ispd | NM_178629.6 | chr12:37108036-37416090 | | 15041 | Izumo1 | NM_001018013.1 | chr7:52877180-52882612 |
| 14947 | Ist1 | NM_028018.2 | chr8:112195221-112217194 | | 15042 | Izumo2 | NM_029317.1 | chr7:51964112-51975212 |
| 14948 | Isx | NM_027837.3 | chr8:77397072-77417405 | | 15043 | Izumo3 | NM_027034.1 | chr4:91811008-91813912 |
| 14949 | Isy1 | NM_133934.4 | chr6:87768441-87788753 | | 15044 | Izumo4 | NM_027829.3 | chr10:80165437-80168127 |
| 14950 | Isyna1 | NM_023627.1 | chr8:73118379-73121189 | | 15045 | Jade1 | NM_001130184.1 | chr3:41359655-41420786 |
| 14951 | Itch | NM_001243712.1 | chr2:154959216-155052591 | | 15046 | Jade1 | NM_001130185.1 | chr3:41359655-41420786 |
| 14952 | Itch | NM_008395.3 | chr2:154959216-155052591 | | 15047 | Jade1 | NM_001130186.1 | chr3:41359655-41420786 |
| 14953 | Itfg1 | NM_028007.3 | chr8:88241455-88364848 | | 15048 | Jade1 | NM_172303.4 | chr3:41359655-41420786 |
| 14954 | Itfg2 | NM_133927.1 | chr6:128359461-128374928 | | 15049 | Jade2 | NM_199299.3 | chr11:51626957-51670983 |
| 14955 | Itfg3 | NM_001206335.1 | chr17:26349636-26381187 | | 15050 | Jade3 | NM_001289684.1 | chrX:20002813-20097065 |
| 14956 | Itfg3 | NM_207217.4 | chr17:26349636-26381187 | | 15051 | Jade3 | NM_199317.2 | chrX:20002813-20097065 |
| 14957 | Itga1 | NM_001033228.3 | chr13:115748289-115892172 | | 15052 | Jag1 | NM_013822.5 | chr2:136907186-136942256 |
| 14958 | Itga10 | NM_001081053.1 | chr3:96449506-96468442 | | 15053 | Jag2 | NM_010588.2 | chr12:114146801-114167706 |
| 14959 | Itga11 | NM_176922.5 | chr9:62525661-62631786 | | 15054 | Jagn1 | NM_001205025.1 | chr6:113392510-113398223 |
| 14960 | Itga2 | NM_008396.2 | chr13:115626119-115722249 | | 15055 | Jagn1 | NM_001243739.1 | chr6:113392510-113398223 |
| 14961 | Itga2b | NM_010575.2 | chr11:102314610-102331197 | | 15056 | Jagn1 | NM_026365.3 | chr6:113392510-113398223 |
| 14962 | Itga3 | NM_013565.3 | chr11:94905795-94938028 | | 15057 | Jak1 | NM_146145.2 | chr4:100824579-100937887 |
| 14963 | Itga4 | NM_010576.3 | chr2:79095583-79173271 | | 15058 | Jak2 | NM_001048177.2 | chr19:29326292-29387570 |
| 14964 | Itga5 | NM_010577.3 | chr15:103174718-103197179 | | 15059 | Jak2 | NM_008413.3 | chr19:29326292-29387570 |
| 14965 | Itga6 | NM_001277970.1 | chr2:71624995-71696484 | | 15060 | Jak3 | NM_001190830.1 | chr8:74200281-74214476 |
| 14966 | Itga6 | NM_008397.2 | chr2:71624995-71696484 | | 15061 | Jak3 | NM_010589.6 | chr8:74200281-74214476 |
| 14967 | Itga7 | NM_008398.2 | chr10:128370869-128395340 | | 15062 | Jakmip1 | NM_178394.1 | chr5:37442095-37516537 |
| 14968 | Itga8 | NM_001001309.2 | chr2:12028287-12223547 | | 15063 | Jakmip2 | NM_001163637.1 | chr18:43691961-43847427 |
| 14969 | Itga9 | NM_001113514.1 | chr9:118515826-118810121 | | 15064 | Jakmip3 | NM_028708.2 | chr7:146132412-146269875 |
| 14970 | Itga9 | NM_133721.2 | chr9:118515826-118810121 | | 15065 | Jam2 | NM_023844.5 | chr16:84774367-84826620 |
| 14971 | Itgad | NM_001029872.3 | chr7:135317460-135349017 | | 15066 | Jam3 | NM_023277.4 | chr9:26904968-26963006 |
| 14972 | Itgae | NM_008399.2 | chr11:72904096-72960951 | | 15067 | Jarid2 | NM_001205043.1 | chr13:44826142-45017012 |
| 14973 | Itgae | NM_172944.2 | chr11:72904096-72960951 | | 15068 | Jarid2 | NM_001205044.1 | chr13:44826142-45017012 |
| 14974 | Itgal | NM_001253872.1 | chr7:134439773-134478651 | | 15069 | Jarid2 | NM_021878.3 | chr13:44826142-45017012 |
| 14975 | Itgal | NM_001253873.1 | chr7:134439773-134478651 | | 15070 | Jazf1 | NM_001168277.1 | chr6:52718061-53018618 |
| 14976 | Itgal | NM_001253874.1 | chr7:134439773-134478651 | | 15071 | Jazf1 | NM_173406.3 | chr6:52718061-53018618 |
| 14977 | Itgal | NM_008400.3 | chr7:134439773-134478651 | | 15072 | Jdp2 | NM_001205052.1 | chr12:86940054-86980828 |
| 14978 | Itgam | NM_001082960.1 | chr7:135206153-135262005 | | 15073 | Jdp2 | NM_001205053.1 | chr12:86940054-86980828 |
| 14979 | Itgam | NM_008401.2 | chr7:135206153-135262005 | | 15074 | Jdp2 | NM_030887.2 | chr12:86940054-86980828 |
| 14980 | Itgav | NM_008402.3 | chr2:83564553-83647074 | | 15075 | Jkamp | NM_001205067.1 | chr12:73186825-73286016 |
| 14981 | Itgax | NM_021334.2 | chr7:135273081-135294171 | | 15076 | Jkamp | NM_024205.2 | chr12:73186825-73286016 |
| 14982 | Itgb1 | NM_010578.2 | chr8:131209553-131257479 | | 15077 | Jmjd1c | NM_001242396.1 | chr10:66590005-66719074 |
| 14983 | Itgb1bp1 | NM_008843.4 | chr12:21725667-21292098 | | 15078 | Jmjd1c | NM_207221.2 | chr10:66590005-66719074 |
| 14984 | Itgb1bp2 | NM_013712.2 | chrX:98644447-98648880 | | 15079 | Jmjd4 | NM_001205068.1 | chr11:59263546-59272069 |
| 14985 | Itgb2 | NM_008404.4 | chr10:76993092-77028419 | | 15080 | Jmjd4 | NM_178659.6 | chr11:59263546-59272069 |
| 14986 | Itgb2l | NM_008405.3 | chr16:96643904-96665221 | | 15081 | Jmjd4 | NR_037992.1 | chr11:59263546-59272069 |
| 14987 | Itgb3 | NM_016780.2 | chr11:104469313-104531785 | | 15082 | Jmjd6 | NM_033398.2 | chr11:116698745-116704763 |
| 14988 | Itgb3bp | NM_026348.3 | chr4:99432092-99495809 | | 15083 | Jmjd7 | NM_001114637.1 | chr2:119853219-119858340 |
| 14989 | Itgb4 | NM_001005608.2 | chr11:115836038-115874033 | | 15084 | Jmjd7-pla2g4b | NR_104353.1 | chr2:119853219-119868768 |
| 14990 | Itgb4 | NM_133663.2 | chr11:115836038-115874033 | | 15085 | Jmjd8 | NM_028101.4 | chr17:25965988-25968788 |
| 14991 | Itgb5 | NM_001145884.1 | chr16:33829750-33949424 | | 15086 | Jmy | NM_021310.3 | chr13:94200051-94269763 |
| 14992 | Itgb5 | NM_010580.2 | chr16:33829750-33949424 | | 15087 | Josd1 | NM_028792.3 | chr15:79504679-79518302 |
| 14993 | Itgb6 | NM_001159564.1 | chr2:60436348-60560660 | | 15088 | Josd2 | NM_001205070.1 | chr7:51723349-51727028 |
| 14994 | Itgb6 | NM_021359.3 | chr2:60436348-60560660 | | 15089 | Josd2 | NM_001205071.1 | chr7:51723349-51727028 |
| 14995 | Itgb7 | NM_013566.2 | chr15:102046425-102062366 | | 15090 | Josd2 | NM_001205072.1 | chr7:51723349-51727028 |
| 14996 | Itgb8 | NM_177290.3 | chr12:120401275-120476749 | | 15091 | Josd2 | NM_001205073.1 | chr7:51723349-51727028 |
| 14997 | Itgbl1 | NM_145467.2 | chr14:124050361-124373301 | | 15092 | Josd2 | NM_025368.4 | chr7:51723349-51727028 |
| 14998 | Itih1 | NM_008406.3 | chr14:31742365-31756475 | | 15093 | Jph1 | NM_020604.2 | chr1:16985020-17087970 |
| 14999 | Itih2 | NM_010582.3 | chr2:10016217-10052310 | | 15094 | Jph2 | NM_001205076.1 | chr2:163161977-163223729 |
| 15000 | Itih3 | NM_008407.2 | chr14:31721759-31736773 | | 15095 | Jph2 | NM_021566.2 | chr2:163161977-163223729 |
| 15001 | Itih4 | NM_001159299.2 | chr14:31699661-31715172 | | 15096 | Jph3 | NM_020605.3 | chr8:124254458-124314983 |
| 15002 | Itih4 | NM_001289632.1 | chr14:31699661-31715172 | | 15097 | Jph4 | NM_177049.5 | chr14:55725662-55735772 |
| 15003 | Itih4 | NM_001289633.1 | chr14:31699661-31715172 | | 15098 | Jpx | NR_015508.3 | chrX:100688914-100701764 |
| 15004 | Itih4 | NM_018746.4 | chr14:31699661-31715172 | | 15099 | Jrk | NM_008415.6 | chr15:74532842-74539752 |
| 15005 | Itih5 | NM_172471.2 | chr2:10075169-10178156 | | 15100 | Jrkl | NM_001033181.1 | chr9_random:367889-370843 |
| 15006 | Itk | NM_001281965.1 | chr11:46138649-46203017 | | 15101 | Jsrp1 | NM_028001.3 | chr10:80271240-80276243 |
| 15007 | Itk | NM_001281966.1 | chr11:46138649-46203017 | | 15102 | Jtb | NM_206924.2 | chr3:90035518-90039762 |
| 15008 | Itk | NM_001281967.1 | chr11:46138649-46203017 | | 15103 | Jun | NM_010591.2 | chr4:94715726-94718913 |
| 15009 | Itk | NM_001281968.1 | chr11:46138649-46203017 | | 15104 | Junb | NM_008416.3 | chr8:87500807-87502647 |
| 15010 | Itk | NM_010583.3 | chr11:46138649-46203017 | | 15105 | Jund | NM_001286944.1 | chr8:73221637-73224515 |
| 15011 | Itln1 | NM_010584.3 | chr1:173484254-173465425 | | 15106 | Jup | NM_010593.2 | chr11:100230169-100259104 |
| 15012 | Itm2a | NM_008409.2 | chrX:104592533-104598699 | | 15107 | Kairn | NM_001164268.1 | chr16:33969158-34514113 |
| 15013 | Itm2b | NM_008410.2 | chr14:73762038-73785078 | | 15108 | Kairn | NM_177357.3 | chr16:33969158-34514113 |
| 15014 | Itm2c | NM_022417.3 | chr1:87791084-87805273 | | 15109 | Kank1 | NM_181404.5 | chr19:25311691-25508986 |
| 15015 | Itpa | NM_025922.2 | chr2:130493576-130507350 | | 15110 | Kank2 | NM_145611.4 | chr9:21571216-21602990 |
| 15016 | Itpk1 | NM_172584.3 | chr12:103806793-103943079 | | 15111 | Kank3 | NM_030697.2 | chr17:33947467-33959859 |
| 15017 | Itpka | NM_146125.2 | chr2:119568072-119576989 | | 15112 | Kank4 | NM_172873.3 | chr4:98421583-98484228 |
| 15018 | Itpkb | NM_001081175.1 | chr1:182260607-182353790 | | 15113 | Kank4os | NR_040437.1 | chr4:98460459-98465728 |
| 15019 | Itpkc | NM_181593.2 | chr7:27992188-28013616 | | 15114 | Kansl1 | NM_001081045.1 | chr11:104194542-104303605 |
| 15020 | Itpr1 | NM_010585.5 | chr6:108163090-108501110 | | 15115 | Kansl1l | NM_001122738.1 | chr1:66747466-66864169 |
| 15021 | Itpr2 | NM_010586.2 | chr6:146056820-146450745 | | 15116 | Kansl1l | NM_177645.4 | chr1:66747466-66864169 |
| 15022 | Itpr2 | NM_019923.4 | chr6:146056820-146450745 | | 15117 | Kansl2 | NM_001289437.1 | chr15:98348088-98364700 |
| 15023 | Itpr3 | NM_080553.3 | chr17:27194249-27259168 | | 15118 | Kansl2 | NM_001289438.1 | chr15:98348088-98364700 |
| 15024 | Itprip | NM_001001738.2 | chr19:47969085-47993789 | | 15119 | Kansl2 | NM_001289439.1 | chr15:98348088-98364700 |
| 15025 | Itpripl1 | NM_001163527.1 | chr2:126964504-126969193 | | 15120 | Kansl2 | NM_001289440.1 | chr15:98348088-98364700 |
| 15026 | Itpripl1 | NM_001163528.1 | chr2:126964504-126969193 | | 15121 | Kansl2 | NM_133714.5 | chr15:98348088-98364700 |
| 15027 | Itpripl2 | NM_001033380.3 | chr7:125628625-125635489 | | 15122 | Kansl3 | NM_172652.3 | chr1:36392575-36426026 |
| 15028 | Itsn1 | NM_001110275.1 | chr16:91729615-91920824 | | 15123 | Kap | NM_010594.2 | chr6:133799872-133803685 |
| 15029 | Itsn1 | NM_001110276.1 | chr16:91729615-91920824 | | 15124 | Kars | NM_001130868.2 | chr8:114517338-114535254 |
| 15030 | Itsn1 | NM_010587.2 | chr16:91729615-91920824 | | 15125 | Kars | NM_001286384.1 | chr8:114517338-114535254 |
| 15031 | Itsn2 | NM_001198968.2 | chr12:4599813-4745189 | | 15126 | Kars | NM_053092.3 | chr8:114517338-114535254 |
| 15032 | Itsn2 | NM_001198969.2 | chr12:4599813-4745189 | | 15127 | Kat2a | NM_001038010.2 | chr11:100566059-100573781 |
| 15033 | Itsn2 | NM_011365.4 | chr12:4599813-4745189 | | 15128 | Kat2a | NM_020004.5 | chr11:100566059-100573781 |
| 15034 | Ivd | NM_019826.3 | chr2:118687735-118707093 | | 15129 | Kat2b | NM_001190846.1 | chr17:53706295-53812046 |
| 15035 | Ivl | NM_008412.3 | chr3:92374821-92377657 | | 15130 | Kat2b | NM_020005.4 | chr17:53706295-53812046 |
| 15036 | Ivns1abp | NM_001039511.1 | chr1:153191627-153211575 | | 15131 | Kat5 | NM_001199247.1 | chr19:5603013-5610094 |
| 15037 | Ivns1abp | NM_001289512.1 | chr1:153191627-153211575 | | 15132 | Kat5 | NM_001199248.1 | chr19:5603013-5610094 |
| 15038 | Ivns1abp | NM_054102.2 | chr1:153191627-153211575 | | 15133 | Kat5 | NM_001199249.1 | chr19:5603013-5610094 |
| 15039 | Iws1 | NM_173441.3 | chr18:32227387-32263985 | | 15134 | Kat5 | NM_178637.2 | chr19:5603013-5610094 |

Fig. 25 - 81

| | | | | | | | |
|---|---|---|---|---|---|---|---|
| 15135 | Kat5 | NR_037603.1 | chr19:5603013-5610094 | 15230 | Kcnip4 | NM_001199245.1 | chr5:48780741-49676898 |
| 15136 | Kat6a | NM_001081149.1 | chr8:23970010-24053734 | 15231 | Kcnip4 | NM_030265.3 | chr5:48780741-49676898 |
| 15137 | Kat6b | NM_001205241.1 | chr14:22318991-22491700 | 15232 | Kcnj1 | NM_001168354.1 | chr9:32180002-32206779 |
| 15138 | Kat6b | NM_017479.3 | chr14:22318991-22491700 | 15233 | Kcnj1 | NM_019659.3 | chr9:32180002-32206779 |
| 15139 | Kat7 | NM_001195003.1 | chr11:95133166-95171560 | 15234 | Kcnj10 | NM_001039484.1 | chr1:174271340-174304216 |
| 15140 | Kat7 | NM_001195004.1 | chr11:95133166-95171560 | 15235 | Kcnj11 | NM_001204411.1 | chr7:53352492-53356134 |
| 15141 | Kat7 | NM_177619.3 | chr11:95133166-95171560 | 15236 | Kcnj11 | NM_010602.3 | chr7:53352492-53356134 |
| 15142 | Kat8 | NM_026370.1 | chr7:135056031-135069276 | 15237 | Kcnj12 | NM_001267593.1 | chr11:60836065-60886769 |
| 15143 | Katna1 | NM_011835.2 | chr10:7445797-7482948 | 15238 | Kcnj12 | NM_010603.6 | chr11:60836065-60886769 |
| 15144 | Katnal1 | NM_153572.2 | chr5:149683159-149740223 | 15239 | Kcnj13 | NM_001110227.1 | chr1:89282859-89291304 |
| 15145 | Katnal2 | NM_027721.2 | chr18:77231938-77286035 | 15240 | Kcnj14 | NM_145963.2 | chr7:53071836-53080117 |
| 15146 | Katnb1 | NM_028805.2 | chr8:97605101-97623774 | 15241 | Kcnj15 | NM_001039056.2 | chr16:95479164-95521865 |
| 15147 | Katnbl1 | NM_024254.3 | chr2:112219367-112254394 | 15242 | Kcnj15 | NM_001039057.2 | chr16:95479164-95521865 |
| 15148 | Kazald1 | NM_178929.4 | chr19:45150628-45153779 | 15243 | Kcnj15 | NM_001271687.1 | chr16:95479164-95521865 |
| 15149 | Kazn | NM_001109684.1 | chr4:141658304-141795316 | 15244 | Kcnj15 | NM_001271689.1 | chr16:95479164-95521865 |
| 15150 | Kazn | NM_001109685.1 | chr4:141658304-141795316 | 15245 | Kcnj15 | NM_001271690.1 | chr16:95479164-95521865 |
| 15151 | Kazn | NM_144531.3 | chr4:141658304-141795316 | 15246 | Kcnj15 | NM_001271691.1 | chr16:95479164-95521865 |
| 15152 | Kbtbd11 | NM_029116.2 | chr8:15011024-15033332 | 15247 | Kcnj15 | NM_001271692.1 | chr16:95479164-95521865 |
| 15153 | Kbtbd12 | NM_001278671.1 | chr6:88497715-88577442 | 15248 | Kcnj15 | NM_001271693.1 | chr16:95479164-95521865 |
| 15154 | Kbtbd13 | NM_028974.1 | chr9:65236490-65239459 | 15249 | Kcnj15 | NM_001271694.1 | chr16:95479164-95521865 |
| 15155 | Kbtbd2 | NM_145958.2 | chr6:56727518-56747807 | 15250 | Kcnj15 | NM_001271695.1 | chr16:95479164-95521865 |
| 15156 | Kbtbd3 | NM_001164574.1 | chr9:4309742-4331732 | 15251 | Kcnj15 | NM_019664.5 | chr16:95479164-95521865 |
| 15157 | Kbtbd3 | NM_026962.3 | chr9:4309742-4331732 | 15252 | Kcnj15 | NR_073406.1 | chr16:95479164-95521865 |
| 15158 | Kbtbd4 | NM_025993.3 | chr2:90744942-90750717 | 15253 | Kcnj16 | NM_001252207.1 | chr11:110829346-110889281 |
| 15159 | Kbtbd7 | NM_001024135.2 | chr2:78626317-79830845 | 15254 | Kcnj16 | NM_001252208.1 | chr11:110829346-110889281 |
| 15160 | Kbtbd8 | NM_001008785.5 | chr6:95067873-95079787 | 15255 | Kcnj16 | NM_001252209.2 | chr11:110829346-110889281 |
| 15161 | Kbtbd8 | NM_001102670.2 | chr6:95067873-95079787 | 15256 | Kcnj16 | NM_001252210.2 | chr11:110829346-110889281 |
| 15162 | Kcmf1 | NM_019715.2 | chr6:72791107-72849973 | 15257 | Kcnj16 | NM_010604.3 | chr11:110829346-110889281 |
| 15163 | Kcna1 | NM_010595.3 | chr6:126586480-126595819 | 15258 | Kcnj2 | NM_008425.4 | chr11:110927477-110938139 |
| 15164 | Kcna10 | NM_001081140.1 | chr3:106986060-106998639 | 15259 | Kcnj3 | NM_008426.2 | chr2:55289566-55447936 |
| 15165 | Kcna2 | NM_008417.5 | chr3:106904484-106917923 | 15260 | Kcnj4 | NM_008427.4 | chr15:79314143-79335671 |
| 15166 | Kcna3 | NM_008418.2 | chr3:106839079-106841047 | 15261 | Kcnj5 | NM_010605.2 | chr9:32112367-32151822 |
| 15167 | Kcna4 | NM_021275.4 | chr2:107130745-107138661 | 15262 | Kcnj6 | NM_001025584.2 | chr16:94970289-95219303 |
| 15168 | Kcna5 | NM_145983.2 | chr6:126482568-126485573 | 15263 | Kcnj6 | NM_001025585.2 | chr16:94970289-95219303 |
| 15169 | Kcna6 | NM_013568.6 | chr6:126658346-126690692 | 15264 | Kcnj6 | NM_001025590.1 | chr16:94970289-95219303 |
| 15170 | Kcna7 | NM_010596.2 | chr7:52661329-52666752 | 15265 | Kcnj6 | NM_010606.2 | chr16:94970289-95219303 |
| 15171 | Kcnab1 | NM_001289450.1 | chr3:64913289-65182147 | 15266 | Kcnj8 | NM_008428.4 | chr6:142513458-142619876 |
| 15172 | Kcnab1 | NM_010597.4 | chr3:64913289-65182147 | 15267 | Kcnj9 | NM_008429.2 | chr1:174251163-174259394 |
| 15173 | Kcnab2 | NM_001252654.1 | chr4:151764848-151851658 | 15268 | Kcnk1 | NM_008430.2 | chr8:128519001-128554585 |
| 15174 | Kcnab2 | NM_001252655.1 | chr4:151764848-151851658 | 15269 | Kcnk10 | NM_029911.2 | chr12:99672203-99816150 |
| 15175 | Kcnab2 | NM_001252656.1 | chr4:151764848-151851658 | 15270 | Kcnk12 | NM_199251.1 | chr17:88145160-88197334 |
| 15176 | Kcnab2 | NM_010598.3 | chr4:151764848-151851658 | 15271 | Kcnk13 | NM_001164426.1 | chr12:101202708-101300892 |
| 15177 | Kcnab3 | NM_010599.4 | chr11:69139759-69146543 | 15272 | Kcnk13 | NM_001164427.1 | chr12:101202708-101300892 |
| 15178 | Kcnb1 | NM_008420.4 | chr2:166921468-167014318 | 15273 | Kcnk13 | NM_146037.2 | chr12:101202708-101300892 |
| 15179 | Kcnb2 | NM_001098528.2 | chr1:15302532-15704295 | 15274 | Kcnk15 | NM_001030292.1 | chr2:163679485-163684610 |
| 15180 | Kcnc1 | NM_001112739.2 | chr7:53651837-53694074 | 15275 | Kcnk16 | NM_029006.1 | chr14:21081977-21088384 |
| 15181 | Kcnc1 | NM_008421.3 | chr7:53651837-53694074 | 15276 | Kcnk18 | NM_207261.3 | chr19:59294137-59311860 |
| 15182 | Kcnc2 | NM_001025581.1 | chr10:111708178-111903360 | 15277 | Kcnk2 | NM_001159850.1 | chr1:191031808-191226152 |
| 15183 | Kcnc3 | NM_001290682.1 | chr7:51846255-51860121 | 15278 | Kcnk2 | NM_001281847.1 | chr1:191031808-191226152 |
| 15184 | Kcnc3 | NM_008422.2 | chr7:51846255-51860121 | 15279 | Kcnk2 | NM_001281848.1 | chr1:191031808-191226152 |
| 15185 | Kcnc4 | NM_145922.2 | chr3:107241220-107261816 | 15280 | Kcnk2 | NM_010607.3 | chr1:191031808-191226152 |
| 15186 | Kcnd1 | NM_008423.2 | chrX:7400968-7413629 | 15281 | Kcnk3 | NM_010608.2 | chr5:30890543-30927643 |
| 15187 | Kcnd2 | NM_019697.3 | chr6:21166108-21679805 | 15282 | Kcnk4 | NM_008431.2 | chr19:7000179-7009005 |
| 15188 | Kcnd3 | NM_001039347.1 | chr3:105251107-105476920 | 15283 | Kcnk5 | NM_021542.4 | chr14:20959279-21001004 |
| 15189 | Kcnd3 | NM_019931.1 | chr3:105251107-105476920 | 15284 | Kcnk6 | NM_001033525.3 | chr7:30006946-30017541 |
| 15190 | Kcnd3os | NR_040759.1 | chr3:105251108-105255873 | 15285 | Kcnk7 | NM_010609.2 | chr19:5704475-5707101 |
| 15191 | Kcne1 | NM_008424.3 | chr16:92346245-92359713 | 15286 | Kcnk9 | NM_001033876.1 | chr15:72342548-72376709 |
| 15192 | Kcne1l | NM_021487.1 | chrX:138739295-138740741 | 15287 | Kcnma1 | NM_001253358.1 | chr14:24117915-24823427 |
| 15193 | Kcne2 | NM_134110.3 | chr16:92292633-92298378 | 15288 | Kcnma1 | NM_001253359.1 | chr14:24117915-24823427 |
| 15194 | Kcne3 | NM_001190869.1 | chr7:107325179-107333379 | 15289 | Kcnma1 | NM_001253360.1 | chr14:24117915-24823427 |
| 15195 | Kcne3 | NM_001190870.1 | chr7:107325179-107333379 | 15290 | Kcnma1 | NM_001253361.1 | chr14:24117915-24823427 |
| 15196 | Kcne3 | NM_001190871.2 | chr7:107325179-107333379 | 15291 | Kcnma1 | NM_001253362.1 | chr14:24117915-24823427 |
| 15197 | Kcne3 | NM_001190950.1 | chr7:107325179-107333379 | 15292 | Kcnma1 | NM_001253363.1 | chr14:24117915-24823427 |
| 15198 | Kcne3 | NM_020574.5 | chr7:107325179-107333379 | 15293 | Kcnma1 | NM_001253364.1 | chr14:24117915-24823427 |
| 15199 | Kcne4 | NM_021342.1 | chr1:78813523-78816600 | 15294 | Kcnma1 | NM_001253365.1 | chr14:24117915-24823427 |
| 15200 | Kcnf1 | NM_201531.3 | chr12:17178906-17183694 | 15295 | Kcnma1 | NM_001253366.1 | chr14:24117915-24823427 |
| 15201 | Kcng1 | NM_001081134.1 | chr2:168087197-168094831 | 15296 | Kcnma1 | NM_001253367.1 | chr14:24117915-24823427 |
| 15202 | Kcng2 | NM_001190373.1 | chr18:80491282-80560993 | 15297 | Kcnma1 | NM_001253368.1 | chr14:24117915-24823427 |
| 15203 | Kcng3 | NM_153512.1 | chr17:83985296-84031235 | 15298 | Kcnma1 | NM_001253369.1 | chr14:24117915-24823427 |
| 15204 | Kcng4 | NM_025734.2 | chr8:122147753-122159580 | 15299 | Kcnma1 | NM_001253370.1 | chr14:24117915-24823427 |
| 15205 | Kcnh1 | NM_001038607.2 | chr1:194014753-194334040 | 15300 | Kcnma1 | NM_001253371.1 | chr14:24117915-24823427 |
| 15206 | Kcnh1 | NM_010600.3 | chr1:194014753-194334040 | 15301 | Kcnma1 | NM_001253372.1 | chr14:24117915-24823427 |
| 15207 | Kcnh2 | NM_013569.2 | chr5:23825406-23857422 | 15302 | Kcnma1 | NM_001253373.1 | chr14:24117915-24823427 |
| 15208 | Kcnh3 | NM_010601.3 | chr15:99055407-99073248 | 15303 | Kcnma1 | NM_001253374.1 | chr14:24117915-24823427 |
| 15209 | Kcnh4 | NM_001081194.2 | chr11:100601691-100621092 | 15304 | Kcnma1 | NM_001253375.1 | chr14:24117915-24823427 |
| 15210 | Kcnh5 | NM_172805.3 | chr12:75998203-76278319 | 15305 | Kcnma1 | NM_001253376.1 | chr14:24117915-24823427 |
| 15211 | Kcnh6 | NM_001037712.1 | chr11:105869516-105895378 | 15306 | Kcnma1 | NM_001253377.1 | chr14:24117915-24823427 |
| 15212 | Kcnh7 | NM_133207.2 | chr2:62541002-63022344 | 15307 | Kcnma1 | NM_001253378.1 | chr14:24117915-24823427 |
| 15213 | Kcnh8 | NM_001031811.2 | chr17:52742033-53044544 | 15308 | Kcnma1 | NM_010610.3 | chr14:24117915-24823427 |
| 15214 | Kcnh8 | NM_001031811.2 | chr17:53092465-53121330 | 15309 | Kcnmb1 | NM_031169.2 | chr11:33863013-33873638 |
| 15215 | Kcnip1 | NM_001190885.1 | chr11:33529340-33893193 | 15310 | Kcnmb2 | NM_028231.2 | chr3:31801624-32099102 |
| 15216 | Kcnip1 | NM_001190886.1 | chr11:33529340-33893193 | 15311 | Kcnmb3 | NM_001195074.1 | chr3:32371242-32380891 |
| 15217 | Kcnip1 | NM_001290690.1 | chr11:33529340-33893193 | 15312 | Kcnmb4 | NM_021452.1 | chr10:115854924-115910579 |
| 15218 | Kcnip1 | NM_027398.3 | chr11:33529340-33893193 | 15313 | Kcnmb4os1 | NR_028107.1 | chr10:115855177-115858291 |
| 15219 | Kcnip2 | NM_001276358.1 | chr19:45866835-45890553 | 15314 | Kcnn1 | NM_032397.2 | chr8:73365947-73380907 |
| 15220 | Kcnip2 | NM_030716.3 | chr19:45866835-45890553 | 15315 | Kcnn2 | NM_080465.2 | chr18:45719808-45845537 |
| 15221 | Kcnip2 | NM_145703.2 | chr19:45866835-45890553 | 15316 | Kcnn3 | NM_080466.3 | chr3:89324085-89476416 |
| 15222 | Kcnip2 | NM_145704.2 | chr19:45866835-45890553 | 15317 | Kcnn4 | NM_001163510.1 | chr7:25155281-25170231 |
| 15223 | Kcnip3 | NM_001111331.1 | chr2:127282233-127347830 | 15318 | Kcnn4 | NM_008433.4 | chr7:25155281-25170231 |
| 15224 | Kcnip3 | NM_001291005.1 | chr2:127282233-127347830 | 15319 | Kcnq1 | NM_008434.2 | chr7:150293159-150612947 |
| 15225 | Kcnip3 | NM_019789.4 | chr2:127282233-127347830 | 15320 | Kcnq1ot1 | NR_001461.5 | chr7:150399016-150482452 |
| 15226 | Kcnip3 | NR_110989.1 | chr2:127282233-127347830 | 15321 | Kcnq2 | NM_001003824.2 | chr2:180810283-180869930 |
| 15227 | Kcnip4 | NM_001199242.1 | chr5:48780741-49676898 | 15322 | Kcnq2 | NM_001003825.3 | chr2:180810283-180869930 |
| 15228 | Kcnip4 | NM_001199243.1 | chr5:48780741-49676898 | 15323 | Kcnq2 | NM_001006668.2 | chr2:180810283-180869930 |
| 15229 | Kcnip4 | NM_001199244.1 | chr5:48780741-49676898 | 15324 | Kcnq2 | NM_001006669.2 | chr2:180810283-180869930 |

Fig. 25 - 82

| | | | |
|---|---|---|---|
| 15325 | Kcnq2 | NM_001006674.2 | chr2:180810283-180869930 |
| 15326 | Kcnq2 | NM_001006675.1 | chr2:180810283-180869930 |
| 15327 | Kcnq2 | NM_001006676.1 | chr2:180810283-180869930 |
| 15328 | Kcnq2 | NM_001006677.1 | chr2:180810283-180869930 |
| 15329 | Kcnq2 | NM_001006678.1 | chr2:180810283-180869930 |
| 15330 | Kcnq2 | NM_001006679.1 | chr2:180810283-180869930 |
| 15331 | Kcnq2 | NM_001006680.1 | chr2:180810283-180869930 |
| 15332 | Kcnq2 | NM_010611.3 | chr2:180810283-180869930 |
| 15333 | Kcnq3 | NM_152923.2 | chr15:65826476-66117786 |
| 15334 | Kcnq4 | NM_001081142.1 | chr4:120370077-120419781 |
| 15335 | Kcnq5 | NM_001160139.1 | chr1:21388483-21952023 |
| 15336 | Kcnq5 | NM_023872.3 | chr1:21388483-21952023 |
| 15337 | Kcnrg | NM_001039105.3 | chr14:62217062-62301210 |
| 15338 | Kcnrg | NM_206974.1 | chr14:62217062-62301210 |
| 15339 | Kcns1 | NM_008435.2 | chr2:163989354-163996849 |
| 15340 | Kcns2 | NM_001271704.1 | chr15:34767109-34773162 |
| 15341 | Kcns2 | NM_181317.4 | chr15:34767109-34773162 |
| 15342 | Kcns3 | NM_001168564.1 | chr12:11097007-11157648 |
| 15343 | Kcns3 | NM_173443.7 | chr12:11097007-11157648 |
| 15344 | Kcnt1 | NM_001145403.2 | chr2:25719373-25773793 |
| 15345 | Kcnt1 | NM_175462.4 | chr2:25719373-25773793 |
| 15346 | Kcnt2 | NM_001081027.2 | chr1:142142834-142506838 |
| 15347 | Kcnu1 | NM_008432.2 | chr8:26960094-27048406 |
| 15348 | Kcnv1 | NM_026200.3 | chr15:44937829-44946480 |
| 15349 | Kcnv2 | NM_183179.1 | chr19:27397108-27411669 |
| 15350 | Kcp | NM_001029985.4 | chr6:29432035-29457952 |
| 15351 | Kctd1 | NM_001142731.1 | chr18:15127193-15309955 |
| 15352 | Kctd1 | NM_134112.5 | chr18:15127193-15309955 |
| 15353 | Kctd10 | NM_001159941.1 | chr5:114764949-114830514 |
| 15354 | Kctd10 | NM_026145.4 | chr5:114764949-114830514 |
| 15355 | Kctd11 | NM_153143.4 | chr11:69691765-69694487 |
| 15356 | Kctd12 | NM_177715.4 | chr14:103375798-103381854 |
| 15357 | Kctd12b | NM_175429.3 | chrX:150119696-150130823 |
| 15358 | Kctd13 | NM_172747.2 | chr7:134072392-134089123 |
| 15359 | Kctd14 | NM_001010826.3 | chr7:104599843-104608067 |
| 15360 | Kctd14 | NM_001012434.3 | chr7:104599843-104608067 |
| 15361 | Kctd14 | NM_001136235.1 | chr7:104599843-104608067 |
| 15362 | Kctd15 | NM_146188.1 | chr7:35424035-35437860 |
| 15363 | Kctd16 | NM_026135.1 | chr18:40418014-40690838 |
| 15364 | Kctd17 | NM_001289671.1 | chr15:78258993-78269733 |
| 15365 | Kctd17 | NM_001289672.1 | chr15:78258993-78269733 |
| 15366 | Kctd17 | NM_001289673.1 | chr15:78258993-78269733 |
| 15367 | Kctd17 | NR_110357.1 | chr15:78258993-78269733 |
| 15368 | Kctd18 | NM_001159864.1 | chr1:58011944-58026928 |
| 15369 | Kctd18 | NM_001159865.1 | chr1:58011944-58026928 |
| 15370 | Kctd18 | NR_027630.1 | chr1:58011944-58026928 |
| 15371 | Kctd19 | NM_177791.3 | chr8:107906707-107937402 |
| 15372 | Kctd2 | NM_183285.3 | chr11:115281439-115292588 |
| 15373 | Kctd20 | NM_025888.5 | chr17:29090160-29104882 |
| 15374 | Kctd21 | NM_001039039.3 | chr7:104480832-104498726 |
| 15375 | Kctd3 | NM_172650.2 | chr1:190794976-190831719 |
| 15376 | Kctd4 | NM_026214.3 | chr14:76354810-76365024 |
| 15377 | Kctd5 | NM_027008.2 | chr17:24184686-24210452 |
| 15378 | Kctd6 | NM_027782.3 | chr14:9046661-9056083 |
| 15379 | Kctd7 | NM_172509.3 | chr5:130620757-130631678 |
| 15380 | Kctd8 | NM_175519.5 | chr5:69500523-69732948 |
| 15381 | Kctd9 | NM_001111028.1 | chr14:68334154-68360367 |
| 15382 | Kctd9 | NM_001285933.1 | chr14:68334154-68360367 |
| 15383 | Kctd9 | NM_134073.2 | chr14:68334154-68360367 |
| 15384 | Kdelc1 | NM_023645.3 | chr1:44163390-44175618 |
| 15385 | Kdelc2 | NM_212445.2 | chr9:53192128-53209972 |
| 15386 | Kdelr1 | NM_133950.2 | chr7:53128209-53139096 |
| 15387 | Kdelr2 | NM_025841.4 | chr5:144165498-144182955 |
| 15388 | Kdelr3 | NM_134090.2 | chr15:79346838-79358169 |
| 15389 | Kdf1 | NM_001083916.1 | chr4:133074877-133086705 |
| 15390 | Kdf1 | NM_133707.2 | chr4:133074877-133086705 |
| 15391 | Kdm1a | NM_133872.2 | chr4:136106447-136158638 |
| 15392 | Kdm1b | NM_172262.3 | chr13:47138868-47180648 |
| 15393 | Kdm2a | NM_001001984.2 | chr19:4316146-4397077 |
| 15394 | Kdm2b | NM_001003953.2 | chr5:123320684-123439101 |
| 15395 | Kdm2b | NM_001005866.1 | chr5:123320684-123439101 |
| 15396 | Kdm2b | NM_013910.2 | chr5:123320684-123439101 |
| 15397 | Kdm3a | NM_001038695.3 | chr6:71538963-71582911 |
| 15398 | Kdm3a | NM_173001.3 | chr6:71538963-71582911 |
| 15399 | Kdm3b | NM_001081256.1 | chr18:34986661-34999024 |
| 15400 | Kdm4a | NM_001161823.1 | chr4:117809608-117852648 |
| 15401 | Kdm4a | NM_172382.2 | chr4:117809608-117852648 |
| 15402 | Kdm4b | NM_172132.2 | chr17:56465472-56542296 |
| 15403 | Kdm4c | NM_001166095.1 | chr4:73888400-74051768 |
| 15404 | Kdm4c | NM_144787.2 | chr4:73888400-74051768 |
| 15405 | Kdm4d | NM_173433.2 | chr9:14267024-14304926 |
| 15406 | Kdm5a | NM_145997.3 | chr6:120314117-120394592 |
| 15407 | Kdm5b | NM_152895.2 | chr1:136456754-136529455 |
| 15408 | Kdm5c | NM_013668.4 | chrX:148667769-148713642 |
| 15409 | Kdm5d | NM_011419.3 | chrY:234230-280254 |
| 15410 | Kdm6a | NM_009483.1 | chrX:17739792-17856484 |
| 15411 | Kdm6b | NM_001017426.1 | chr11:69212019-69227177 |
| 15412 | Kdm7a | NM_001033430.4 | chr6:39086619-39156772 |
| 15413 | Kdm8 | NM_029842.5 | chr7:132588133-132605782 |
| 15414 | Kdr | NM_010612.2 | chr5:76329298-76374453 |
| 15415 | Kdsr | NM_027534.2 | chr1:108616986-108656319 |
| 15416 | Keap1 | NM_001110305.1 | chr9:21034173-21043776 |
| 15417 | Keap1 | NM_001110306.1 | chr9:21034173-21043776 |
| 15418 | Keap1 | NM_001110307.1 | chr9:21034173-21043776 |
| 15419 | Keap1 | NM_016679.4 | chr9:21034173-21043776 |
| 15420 | Keg1 | NM_029550.4 | chr19:12770279-12794386 |
| 15421 | Kel | NM_032540.3 | chr6:41636328-41654324 |
| 15422 | Kera | NM_008438.3 | chr10:97069838-97076322 |
| 15423 | Khdc1a | NM_183322.2 | chr1:21339757-21342280 |
| 15424 | Khdc1b | NM_001113187.1 | chr1:21373636-21376465 |
| 15425 | Khdc1c | NM_001033904.1 | chr1:21358411-21359824 |
| 15426 | Khdc3 | NM_025890.3 | chr9:72950204-72952250 |
| 15427 | Khdrbs1 | NM_011317.4 | chr4:129380412-129419547 |
| 15428 | Khdrbs1 | NR_045036.1 | chr4:129380412-129419547 |
| 15429 | Khdrbs2 | NM_133235.2 | chr1:32229651-32714583 |
| 15430 | Khdrbs3 | NM_010158.2 | chr15:68758849-68923948 |
| 15431 | Khk | NM_008439.3 | chr5:31224267-31233619 |
| 15432 | Khnyn | NM_027143.2 | chr14:56503805-56515618 |
| 15433 | Khsrp | NM_010613.3 | chr17:57160471-57170930 |
| 15434 | Kidins220 | NM_001081378.1 | chr12:25659796-25744562 |
| 15435 | Kif11 | NM_010615.1 | chr19:37450892-37496349 |
| 15436 | Kif12 | NM_010616.2 | chr4:62826670-62833165 |
| 15437 | Kif13a | NM_010617.2 | chr13:46844456-47025087 |
| 15438 | Kif13b | NM_001081177.1 | chr14:65271367-65425133 |
| 15439 | Kif14 | NM_001287179.2 | chr1:138364511-138428088 |
| 15440 | Kif15 | NM_010620.3 | chr9:122860198-122927851 |
| 15441 | Kif16b | NM_001081133.2 | chr2:142444080-142727200 |
| 15442 | Kif17 | NM_001190978.1 | chr4:137818165-137857888 |
| 15443 | Kif17 | NM_010623.4 | chr4:137818165-137857888 |
| 15444 | Kif18a | NM_139303.1 | chr2:109120894-109181903 |
| 15445 | Kif18b | NM_197959.2 | chr11:102766832-102786438 |
| 15446 | Kif19a | NM_001102615.1 | chr11:114626702-114651889 |
| 15447 | Kif1a | NM_001110315.2 | chr1:94912032-94998442 |
| 15448 | Kif1a | NM_008440.4 | chr1:94912032-94998442 |
| 15449 | Kif1b | NM_001290995.1 | chr4:148550427-148681842 |
| 15450 | Kif1b | NM_008441.2 | chr4:148550427-148681842 |
| 15451 | Kif1b | NM_207682.2 | chr4:148550427-148681842 |
| 15452 | Kif1c | NM_153103.2 | chr11:70514050-70545472 |
| 15453 | Kif20a | NM_001166406.1 | chr18:34758268-34811390 |
| 15454 | Kif20a | NM_001166407.1 | chr18:34758268-34811390 |
| 15455 | Kif20a | NM_009004.4 | chr18:34758268-34811390 |
| 15456 | Kif20b | NM_183046.1 | chr19:34996847-35050221 |
| 15457 | Kif21a | NM_001109040.2 | chr15:90763705-90880382 |
| 15458 | Kif21a | NM_001109041.2 | chr15:90763705-90880382 |
| 15459 | Kif21a | NM_001109042.1 | chr15:90763705-90880382 |
| 15460 | Kif21a | NM_016705.3 | chr15:90763705-90880382 |
| 15461 | Kif21b | NM_001039472.1 | chr1:138072977-138074591 |
| 15462 | Kif22 | NM_145588.1 | chr7:134171244-134185934 |
| 15463 | Kif23 | NM_024245.1 | chr9:61765084-61794606 |
| 15464 | Kif24 | NM_024241.2 | chr4:41337780-41411881 |
| 15465 | Kif26a | NM_001097621.1 | chr12:113384418-113419958 |
| 15466 | Kif26b | NM_001161665.1 | chr1:180459255-180862988 |
| 15467 | Kif27 | NM_175214.3 | chr13:58388877-58456223 |
| 15468 | Kif2a | NM_001145779.1 | chr13:107750664-107812194 |
| 15469 | Kif2a | NM_008442.2 | chr13:107750664-107812194 |
| 15470 | Kif2b | NM_028547.2 | chr11:91436599-91438869 |
| 15471 | Kif2c | NM_001290662.1 | chr4:116832237-116855229 |
| 15472 | Kif2c | NM_134471.4 | chr4:116832237-116855229 |
| 15473 | Kif3a | NM_001290805.1 | chr11:53380870-53417748 |
| 15474 | Kif3a | NM_001290806.1 | chr11:53380870-53417748 |
| 15475 | Kif3a | NM_008443.2 | chr11:53380870-53417748 |
| 15476 | Kif3b | NM_008444.4 | chr2:153117151-153159125 |
| 15477 | Kif3c | NM_008445.2 | chr12:3365132-3406494 |
| 15478 | Kif4 | NM_008446.2 | chrX:97821403-97922610 |
| 15479 | Kif4-ps | NR_033653.1 | chr12:102383818-102387483 |
| 15480 | Kif5a | NM_001039000.4 | chr10:126662750-126700419 |
| 15481 | Kif5a | NM_008447.4 | chr10:126662750-126700419 |
| 15482 | Kif5b | NM_008448.3 | chr18:6201002-6241522 |
| 15483 | Kif5c | NM_008449.2 | chr2:49474833-49630298 |
| 15484 | Kif6 | NM_177052.3 | chr17:49754496-50049172 |
| 15485 | Kif7 | NM_001291227.1 | chr7:86805081-86859072 |
| 15486 | Kif7 | NM_010626.3 | chr7:86805081-86859072 |
| 15487 | Kif9 | NM_001163569.1 | chr9:110379461-110427678 |
| 15488 | Kif9 | NM_010628.3 | chr9:110379461-110427678 |
| 15489 | Kifap3 | NM_010629.3 | chr1:165709809-165847231 |
| 15490 | Kifc1 | NM_001195298.1 | chr17:34012610-34027578 |
| 15491 | Kifc2 | NM_010630.2 | chr15:76491070-76498626 |
| 15492 | Kifc3 | NM_001145831.1 | chr8:97605100-97666440 |
| 15493 | Kifc3 | NM_001145832.1 | chr8:97605100-97666440 |
| 15494 | Kifc3 | NM_010631.2 | chr8:97605100-97666440 |
| 15495 | Kifc5b | NM_053173.2 | chr17:27054035-27069524 |
| 15496 | Kin | NM_025280.2 | chr2:10002238-10014328 |
| 15497 | Kir3dl1 | NM_177749.3 | chrX:133052537-133068847 |
| 15498 | Kir3dl2 | NM_177748.2 | chrX:132982645-133003580 |
| 15499 | Kirrel | NM_001170985.1 | chr3:86882513-86978669 |
| 15500 | Kirrel | NM_130867.3 | chr3:86882513-86978669 |
| 15501 | Kirrel2 | NM_172898.3 | chr7:31232784-31242534 |
| 15502 | Kirrel3 | NM_001190911.1 | chr9:34296315-34843892 |
| 15503 | Kirrel3 | NM_001190912.1 | chr9:34296315-34843892 |
| 15504 | Kirrel3 | NM_001190913.1 | chr9:34296315-34843892 |
| 15505 | Kirrel3 | NM_001190914.1 | chr9:34296315-34843892 |
| 15506 | Kirrel3 | NM_026324.3 | chr9:34296315-34843892 |
| 15507 | Kiss1 | NR_003188.1 | chrX:50095740-50097770 |
| 15508 | Kiss1 | NM_178260.3 | chr1:135223788-135226299 |
| 15509 | Kiss1r | NM_053244.5 | chr10:79379715-79385017 |
| 15510 | Kit | NM_001122733.1 | chr5:75971011-76052746 |
| 15511 | Kit | NM_021099.3 | chr5:75971011-76052746 |
| 15512 | Kitl | NM_013598.2 | chr10:99478457-99563046 |
| 15513 | Kiz | NM_001033298.3 | chr2:146681624-146795825 |
| 15514 | Kl | NM_013823.2 | chr5:151755181-151796392 |

Fig. 25 - 83

| | | | |
|---|---|---|---|
| 15515 | Kl6 | NM_031180.2 | chr5:65739649-65775242 |
| 15516 | Klc1 | NM_001025358.2 | chr12:112997059-113052052 |
| 15517 | Klc1 | NM_001025359.2 | chr12:112997059-113052052 |
| 15518 | Klc1 | NM_001025360.2 | chr12:112997059-113052052 |
| 15519 | Klc1 | NM_001025361.2 | chr12:112997059-113052052 |
| 15520 | Klc1 | NM_001025362.2 | chr12:112997059-113052052 |
| 15521 | Klc1 | NM_001025363.2 | chr12:112997059-113052052 |
| 15522 | Klc1 | NM_001081959.1 | chr12:112997059-113052052 |
| 15523 | Klc1 | NM_008450.2 | chr12:112997059-113052052 |
| 15524 | Klc2 | NM_008451.2 | chr19:5107745-5118408 |
| 15525 | Klc2 | NR_045528.1 | chr19:5107745-5118408 |
| 15526 | Klc3 | NM_001286038.1 | chr7:19967387-19989453 |
| 15527 | Klc3 | NM_001286039.1 | chr7:19967387-19989453 |
| 15528 | Klc3 | NM_146182.4 | chr7:19967387-19989453 |
| 15529 | Klc4 | NM_029091.2 | chr17:46767579-46782093 |
| 15530 | Klf1 | NM_010635.2 | chr8:87425826-87429194 |
| 15531 | Klf10 | NM_001289471.1 | chr15:38221218-38230466 |
| 15532 | Klf10 | NM_013692.3 | chr15:38221218-38230466 |
| 15533 | Klf11 | NM_178357.3 | chr12:25336235-25347647 |
| 15534 | Klf12 | NM_010636.3 | chr14:100269861-100549015 |
| 15535 | Klf13 | NM_021366.3 | chr7:71031237-71083801 |
| 15536 | Klf14 | NM_001135093.1 | chr6:30906020-30908890 |
| 15537 | Klf15 | NM_023184.3 | chr6:90412619-90425203 |
| 15538 | Klf16 | NM_078477.2 | chr10:80029865-80040041 |
| 15539 | Klf17 | NM_029416.2 | chr4:117429263-117438271 |
| 15540 | Klf2 | NM_008452.2 | chr8:74842960-74845553 |
| 15541 | Klf3 | NM_008453.5 | chr5:65194761-65221368 |
| 15542 | Klf4 | NM_010637.3 | chr4:55540008-55545347 |
| 15543 | Klf5 | NM_009769.4 | chr14:99697909-99712628 |
| 15544 | Klf6 | NM_011803.2 | chr13:5860734-5869639 |
| 15545 | Klf7 | NM_033563.3 | chr1:64082247-64167963 |
| 15546 | Klf8 | NM_173780.3 | chrX:149672587-149830677 |
| 15547 | Klf9 | NM_010638.4 | chr19:23215716-23241401 |
| 15548 | Klhdc1 | NM_178253.5 | chr12:70342818-70384948 |
| 15549 | Klhdc10 | NM_029742.2 | chr6:30351908-30405174 |
| 15550 | Klhdc2 | NM_027137.3 | chr12:70397667-70411674 |
| 15551 | Klhdc3 | NM_001163729.2 | chr17:46811499-46841951 |
| 15552 | Klhdc3 | NM_027910.3 | chr17:46811499-46841951 |
| 15553 | Klhdc4 | NM_145605.2 | chr8:124320207-124353469 |
| 15554 | Klhdc7a | NM_173427.2 | chr4:139518088-139523941 |
| 15555 | Klhdc7b | NM_001160178.1 | chr15:89217321-89219139 |
| 15556 | Klhdc8a | NM_144810.5 | chr1:134195202-134203934 |
| 15557 | Klhdc8b | NM_030075.2 | chr9:108349970-108363912 |
| 15558 | Klhdc9 | NM_001033039.2 | chr1:173288579-173290929 |
| 15559 | Klhl1 | NM_053105.2 | chr14:96504483-96918253 |
| 15560 | Klhl10 | NM_025727.3 | chr11:100303237-100318338 |
| 15561 | Klhl11 | NM_172565.2 | chr11:100323925-100334096 |
| 15562 | Klhl12 | NM_153128.2 | chr1:136352131-136387450 |
| 15563 | Klhl13 | NM_001290476.1 | chrX:22796396-22942208 |
| 15564 | Klhl13 | NM_026167.4 | chrX:22796396-22942208 |
| 15565 | Klhl14 | NM_001081403.1 | chr18:21708878-21810869 |
| 15566 | Klhl15 | NM_001039059.1 | chrX:91480268-91518854 |
| 15567 | Klhl15 | NM_001039060.1 | chrX:91480268-91518854 |
| 15568 | Klhl15 | NM_001039061.1 | chrX:91480268-91518854 |
| 15569 | Klhl15 | NM_153165.2 | chrX:91480268-91518854 |
| 15570 | Klhl17 | NM_198305.2 | chr4:155603153-155608966 |
| 15571 | Klhl18 | NM_177771.5 | chr9:110328429-110379198 |
| 15572 | Klhl2 | NM_178633.3 | chr8:67218471-67373822 |
| 15573 | Klhl20 | NM_001039482.1 | chr1:163018508-163061610 |
| 15574 | Klhl21 | NM_001033352.3 | chr4:151382999-151391786 |
| 15575 | Klhl22 | NM_145479.4 | chr16:17759713-17793475 |
| 15576 | Klhl23 | NM_177784.4 | chr2:69660426-69674708 |
| 15577 | Klhl24 | NM_029436.3 | chr16:20097626-20127817 |
| 15578 | Klhl25 | NM_001122780.1 | chr7:82993223-83019016 |
| 15579 | Klhl25 | NM_029652.1 | chr7:82993223-83019016 |
| 15580 | Klhl25 | NM_182782.2 | chr7:82993223-83019016 |
| 15581 | Klhl26 | NM_001122830.1 | chr8:72974126-73000842 |
| 15582 | Klhl26 | NM_178771.3 | chr8:72974126-73000842 |
| 15583 | Klhl28 | NM_025707.3 | chr12:66043426-66066523 |
| 15584 | Klhl29 | NM_001164493.1 | chr12:5084273-5382488 |
| 15585 | Klhl3 | NM_001195075.1 | chr13:58106318-58203789 |
| 15586 | Klhl30 | NM_027551.2 | chr1:93247649-93258981 |
| 15587 | Klhl31 | NM_172925.2 | chr9:77484538-77507929 |
| 15588 | Klhl32 | NM_001033531.3 | chr4:24544419-24778233 |
| 15589 | Klhl32 | NM_001163020.1 | chr4:24544419-24778233 |
| 15590 | Klhl33 | NM_001166651.1 | chr14:51511063-51512930 |
| 15591 | Klhl34 | NM_001081667.2 | chrX:154256366-154258992 |
| 15592 | Klhl35 | NM_028145.1 | chr7:106614513-106622530 |
| 15593 | Klhl36 | NM_146219.1 | chr8:122386204-122400889 |
| 15594 | Klhl38 | NM_177755.3 | chr15:58146127-58155724 |
| 15595 | Klhl4 | NM_001290477.1 | chrX:111587941-111674738 |
| 15596 | Klhl4 | NM_001290478.1 | chrX:111587941-111674738 |
| 15597 | Klhl4 | NM_172781.2 | chrX:111587941-111674738 |
| 15598 | Klhl40 | NM_028202.3 | chr9:121686724-121692937 |
| 15599 | Klhl41 | NM_001081087.1 | chr2:69508176-69522296 |
| 15600 | Klhl42 | NM_001081237.1 | chr6:147039596-147061300 |
| 15601 | Klhl5 | NM_175174.4 | chr5:65522469-65559381 |
| 15602 | Klhl6 | NM_183890.3 | chr16:19946585-19983122 |
| 15603 | Klhl7 | NM_001161800.1 | chr5:23606407-23667049 |
| 15604 | Klhl7 | NM_026448.3 | chr5:23606407-23667049 |
| 15605 | Klhl8 | NM_178741.2 | chr5:104291068-104340248 |
| 15606 | Klhl9 | NM_172871.2 | chr4:88364195-88368412 |
| 15607 | Klk1 | NM_010639.7 | chr7:51480806-51484987 |
| 15608 | Klk10 | NM_133712.2 | chr7:51036423-51040780 |
| 15609 | Klk11 | NM_001177373.1 | chr7:51029986-51034632 |

| | | | |
|---|---|---|---|
| 15610 | Klk11 | NM_019974.2 | chr7:51029986-51034632 |
| 15611 | Klk12 | NM_027097.1 | chr7:51024469-51028851 |
| 15612 | Klk13 | NM_001039042.2 | chr7:50967936-50982128 |
| 15613 | Klk14 | NM_174866.2 | chr7:50945787-50950905 |
| 15614 | Klk15 | NM_174865.1 | chr7:51189140-51194960 |
| 15615 | Klk1b1 | NM_010645.2 | chr7:51222137-51226685 |
| 15616 | Klk1b11 | NM_010640.1 | chr7:51251248-51255245 |
| 15617 | Klk1b16 | NM_008454.2 | chr7:51392136-51396974 |
| 15618 | Klk1b21 | NM_010642.2 | chr7:51357661-51361949 |
| 15619 | Klk1b22 | NM_010114.1 | chr7:51368052-51372246 |
| 15620 | Klk1b24 | NM_010643.1 | chr7:51443632-51447821 |
| 15621 | Klk1b26 | NM_010644.2 | chr7:51268048-51272335 |
| 15622 | Klk1b27 | NM_020268.3 | chr7:51307659-51312081 |
| 15623 | Klk1b3 | NM_008693.2 | chr7:51453560-51457721 |
| 15624 | Klk1b4 | NM_010915.3 | chr7:51462804-51467124 |
| 15625 | Klk1b5 | NM_008456.3 | chr7:51471844-51476073 |
| 15626 | Klk1b7-ps | NR_033120.1 | chr7:51200381-51201297 |
| 15627 | Klk1b8 | NM_008457.2 | chr7:51206041-51210308 |
| 15628 | Klk1b9 | NM_010116.1 | chr7:51231430-51235746 |
| 15629 | Klk4 | NM_019928.1 | chr7:51136541-51141174 |
| 15630 | Klk5 | NM_026806.2 | chr7:51097638-51106551 |
| 15631 | Klk6 | NM_001164696.1 | chr7:51079913-51087397 |
| 15632 | Klk6 | NM_001164697.1 | chr7:51079913-51087397 |
| 15633 | Klk6 | NM_001164698.1 | chr7:51079913-51087397 |
| 15634 | Klk6 | NM_011177.2 | chr7:51079913-51087397 |
| 15635 | Klk7 | NM_011872.1 | chr7:51066813-51071729 |
| 15636 | Klk8 | NM_008940.2 | chr7:51052946-51059192 |
| 15637 | Klk9 | NM_028660.3 | chr7:51047260-51052126 |
| 15638 | Klkb1 | NM_008455.2 | chr8:46354806-46380189 |
| 15639 | Klra1 | NM_016659.3 | chr6:130313936-130336892 |
| 15640 | Klra10 | NM_008459.2 | chr6:130219212-130231946 |
| 15641 | Klra12 | NM_010646.1 | chr6:129994042-130256499 |
| 15642 | Klra13-ps | NR_033451.1 | chr6:130241179-130256450 |
| 15643 | Klra14-ps | NR_104105.1 | chr6:129922099-130336892 |
| 15644 | Klra14-ps | NR_104106.1 | chr6:129922111-130330680 |
| 15645 | Klra15 | NM_013793.2 | chr6:129922099-130336892 |
| 15646 | Klra17 | NM_133203.5 | chr6:129781171-129826690 |
| 15647 | Klra18 | NM_053153.2 | chr6:129993750-130017276 |
| 15648 | Klra19 | NM_053154.2 | chr6:129963052-129976978 |
| 15649 | Klra2 | NM_001170851.1 | chr6:131169252-131197380 |
| 15650 | Klra2 | NM_008462.5 | chr6:131169252-131197380 |
| 15651 | Klra21 | NM_053151.1 | chr6:130032616-130079897 |
| 15652 | Klra22 | NM_053152.2 | chr6:129922100-130330826 |
| 15653 | Klra23 | NM_024470.1 | chr6:130241179-130258379 |
| 15654 | Klra3 | NM_001289604.1 | chr6:129922099-130336892 |
| 15655 | Klra3 | NM_001289605.1 | chr6:129922099-130336892 |
| 15656 | Klra3 | NM_010648.3 | chr6:129922099-130336892 |
| 15657 | Klra33 | NM_001039118.1 | chr6:129,994,057-130,015,320 |
| 15658 | Klra4 | NM_001252577.1 | chr6:129922099-130336892 |
| 15659 | Klra4 | NM_010649.3 | chr6:129922099-130336892 |
| 15660 | Klra5 | NM_008463.2 | chr6:129849008-129863242 |
| 15661 | Klra6 | NM_008464.2 | chr6:129963051-129976972 |
| 15662 | Klra7 | NM_001110323.1 | chr6:129922099-130336892 |
| 15663 | Klra7 | NM_014194.5 | chr6:129922099-130336892 |
| 15664 | Klra8 | NM_001101620.1 | chr6:129922099-130336892 |
| 15665 | Klra8 | NM_010650.3 | chr6:129922099-130336892 |
| 15666 | Klra9 | NM_010651.3 | chr6:130128700-130143130 |
| 15667 | Klrb1 | NM_001099918.1 | chr6:128656525-128673064 |
| 15668 | Klrb1a | NM_001159902.1 | chr6:128559244-128572952 |
| 15669 | Klrb1a | NM_010737.3 | chr6:128559244-128572952 |
| 15670 | Klrb1b | NM_030599.4 | chr6:128763723-128776333 |
| 15671 | Klrb1c | NM_001159904.1 | chr6:128728502-128738659 |
| 15672 | Klrb1c | NM_008527.2 | chr6:128728502-128738659 |
| 15673 | Klrb1f | NM_153094.2 | chr6:128995918-129007489 |
| 15674 | Klrb1f | NR_024262.1 | chr6:128995918-129007489 |
| 15675 | Klrb1f | NR_024263.1 | chr6:128995918-129007489 |
| 15676 | Klrb1-ps1 | NR_073569.1 | chr6:129066535-129079464 |
| 15677 | Klrc1 | NM_001136068.2 | chr6:129616034-129628991 |
| 15678 | Klrc1 | NM_001288664.1 | chr6:129616034-129628991 |
| 15679 | Klrc1 | NM_010652.2 | chr6:129616034-129628991 |
| 15680 | Klrc2 | NM_001098669.1 | chr6:129606363-129610614 |
| 15681 | Klrc2 | NM_010653.4 | chr6:129606363-129610614 |
| 15682 | Klrc3 | NM_021378.1 | chr6:129589102-129593306 |
| 15683 | Klrd1 | NM_010654.3 | chr6:129541828-129548793 |
| 15684 | Klre1 | NM_153590.3 | chr6:129528303-129535845 |
| 15685 | Klrg1 | NM_016970.1 | chr6:122220618-122232851 |
| 15686 | Klrg2 | NM_001033171.2 | chr6:38576659-38587239 |
| 15687 | Klri1 | NM_001012520.2 | chr6:129647235-129667150 |
| 15688 | Klri2 | NM_177155.4 | chr6:129679058-129690502 |
| 15689 | Klrk1 | NM_001083322.2 | chr6:129560340-129573882 |
| 15690 | Klrk1 | NM_001286018.1 | chr6:129560340-129573882 |
| 15691 | Klrk1 | NM_033078.4 | chr6:129560340-129573882 |
| 15692 | Kmo | NM_133809.1 | chr1:177562323-177590984 |
| 15693 | Kmt2a | NM_001081049.1 | chr9:44611437-44689357 |
| 15694 | Kmt2b | NM_001290573.1 | chr7:31353873-31373745 |
| 15695 | Kmt2b | NM_029274.2 | chr7:31353873-31373745 |
| 15696 | Kmt2c | NM_001081383.1 | chr5:24777611-25004601 |
| 15697 | Kmt2d | NM_001033276.3 | chr15:98662099-98701636 |
| 15698 | Kmt2e | NM_026984.1 | chr5:22940247-23010047 |
| 15699 | Kncn | NM_001039124.3 | chr4:115557004-115560569 |
| 15700 | Kndc1 | NM_177261.4 | chr7:147080594-147127439 |
| 15701 | Kng1 | NM_001102411.1 | chr16:23058372-23082151 |
| 15702 | Kng1 | NM_001102412.1 | chr16:23058372-23082151 |
| 15703 | Kng1 | NM_023125.3 | chr16:23058372-23082151 |

Fig. 25 - 84

| | | | | | | | | |
|---|---|---|---|---|---|---|---|---|
| 15704 | Kng2 | NM_001102409.1 | chr16:22985924-23029174 | | 15799 | Krtap19-3 | NM_130857.2 | chr16:88877757-88878283 |
| 15705 | Kng2 | NM_001102410.1 | chr16:22985924-23029174 | | 15800 | Krtap19-4 | NM_130873.1 | chr16:88885030-88885334 |
| 15706 | Kng2 | NM_201375.2 | chr16:22985924-23029174 | | 15801 | Krtap19-5 | NM_010676.2 | chr16:88896212-88896694 |
| 15707 | Knop1 | NM_001168218.1 | chr7:125985731-126138725 | | 15802 | Krtap19-9b | NM_133359.1 | chr16:88932048-88932509 |
| 15708 | Knop1 | NM_001168219.1 | chr7:125985731-126138725 | | 15803 | Krtap20-2 | NM_001163615.1 | chr16:89206105-89206639 |
| 15709 | Knop1 | NM_001168220.1 | chr7:125985731-126138725 | | 15804 | Krtap21-1 | NM_028621.3 | chr16:89403271-89404019 |
| 15710 | Knop1 | NM_023197.3 | chr7:125985731-126138725 | | 15805 | Krtap22-2 | NM_001191018.1 | chr16:89010624-89011004 |
| 15711 | Knstrn | NM_026412.3 | chr2:118639738-118661948 | | 15806 | Krtap2-4 | NM_027800.1 | chr11:99475330-99476160 |
| 15712 | Kntc1 | NM_001042421.1 | chr5:124199734-124271602 | | 15807 | Krtap24-1 | NM_001163141.1 | chr16:88610953-88612524 |
| 15713 | Kpna1 | NM_008465.5 | chr16:35983448-36036248 | | 15808 | Krtap26-1 | NM_027105.2 | chr16:88647068-88648041 |
| 15714 | Kpna2 | NM_010655.3 | chr11:106849942-106860839 | | 15809 | Krtap27-1 | NM_001163105.1 | chr16:88671290-88671899 |
| 15715 | Kpna3 | NM_008466.3 | chr14:61984022-62058784 | | 15810 | Krtap3-1 | NM_023511.1 | chr11:99427340-99427944 |
| 15716 | Kpna4 | NM_008467.4 | chr3:68876142-68931014 | | 15811 | Krtap31-1 | NM_027568.2 | chr11:99769233-99770204 |
| 15717 | Kpna6 | NM_008468.4 | chr4:129321222-129356011 | | 15812 | Krtap31-2 | NM_001025244.3 | chr11:99797604-99798539 |
| 15718 | Kpna7 | NM_001013774.2 | chr5:145744612-145770505 | | 15813 | Krtap3-2 | NM_025720.3 | chr11:99417136-99418167 |
| 15719 | Kpnb1 | NM_008379.3 | chr11:97021023-97049206 | | 15814 | Krtap3-3 | NM_025524.2 | chr11:99411445-99412177 |
| 15720 | Kptn | NM_028629.1 | chr3:92626995-92631169 | | 15815 | Krtap4-1 | NM_001048196.1 | chr11:99488542-99489553 |
| 15721 | Kptn | NM_133727.2 | chr7:16705224-16712865 | | 15816 | Krtap4-13 | NM_027087.3 | chr11:99659386-99671210 |
| 15722 | Kras | NM_021284.6 | chr6:145165218-145198751 | | 15817 | Krtap4-13 | NM_027087.3 | chr11:99659386-99671210 |
| 15723 | Krba1 | NM_133922.3 | chr6:48345584-48369854 | | 15818 | Krtap4-16 | NM_001013823.1 | chr11:99711968-99712919 |
| 15724 | Krcc1 | NM_145568.3 | chr6:71222012-71235313 | | 15819 | Krtap4-2 | NM_026807.2 | chr11:99495427-99496398 |
| 15725 | Kremen1 | NM_032396.3 | chr11:5091555-5161613 | | 15820 | Krtap4-6 | NM_026834.2 | chr11:99526356-99527274 |
| 15726 | Kremen2 | NM_028416.2 | chr17:23878165-23882796 | | 15821 | Krtap4-7 | NM_029613.1 | chr11:99504425-99505403 |
| 15727 | Krit1 | NM_145416.3 | chr9:21077901-21092413 | | 15822 | Krtap4-8 | NM_001085547.2 | chr11:99641327-99641957 |
| 15728 | Krit1 | NM_001170552.1 | chr5:3803164-3844515 | | 15823 | Krtap4-9 | NM_001085548.2 | chr11:99646513-99647571 |
| 15729 | Krit1 | NM_030675.3 | chr5:3803164-3844515 | | 15824 | Krtap5-1 | NM_015808.1 | chr7:149482181-149482974 |
| 15730 | Krit1 | NR_033173.1 | chr5:3803164-3844515 | | 15825 | Krtap5-2 | NM_027844.4 | chr7:149360436-149361910 |
| 15731 | Krr1 | NM_178610.4 | chr10:111409751-111425486 | | 15826 | Krtap5-3 | NM_023860.1 | chr7:149387268-149388920 |
| 15732 | Krt1 | NM_008473.2 | chr11:101675856-101681217 | | 15827 | Krtap5-4 | NM_015809.2 | chr7:149489406-149490408 |
| 15733 | Krt10 | NM_010660.2 | chr11:99246568-99250678 | | 15828 | Krtap5-5 | NM_001037822.1 | chr7:149414699-149415876 |
| 15734 | Krt12 | NM_010661.2 | chr11:99276977-99283573 | | 15829 | Krtap6-1 | NM_010672.3 | chr16:89031943-89032537 |
| 15735 | Krt13 | NM_010662.1 | chr11:99978909-99982809 | | 15830 | Krtap6-2 | NM_010673.1 | chr16:89419567-89420356 |
| 15736 | Krt14 | NM_016958.1 | chr11:100064475-100068824 | | 15831 | Krtap6-5 | NM_130856.2 | chr16:89047533-89048144 |
| 15737 | Krt15 | NM_008469.2 | chr11:99993072-99997263 | | 15832 | Krtap7-1 | NM_027771.1 | chr16:89507947-89508568 |
| 15738 | Krt16 | NM_008470.1 | chr11:100107405-100110216 | | 15833 | Krtap8-1 | NM_010675.3 | chr16:89487618-89488197 |
| 15739 | Krt17 | NM_010663.2 | chr11:100117530-100122303 | | 15834 | Krtap9-1 | NM_015741.2 | chr11:99734702-99735314 |
| 15740 | Krt18 | NM_010664.2 | chr15:101858646-101862457 | | 15835 | Krtap9-3 | NM_029351.2 | chr11:99458661-99459420 |
| 15741 | Krt19 | NM_008471.2 | chr11:100002125-100007233 | | 15836 | Krtap9-5 | NM_001085527.1 | chr11:99809788-99810865 |
| 15742 | Krt2 | NM_010662.2 | chr15:101641119-101648600 | | 15837 | Krtcap2 | NM_025327.2 | chr3:89050359-89053644 |
| 15743 | Krt20 | NM_023256.1 | chr11:99289716-99299467 | | 15838 | Krtcap3 | NM_027221.3 | chr5:31554079-31555570 |
| 15744 | Krt222 | NM_172946.2 | chr11:99094411-99105381 | | 15839 | Krtdap | NM_001033131.3 | chr7:31572923-31576102 |
| 15745 | Krt23 | NM_033373.1 | chr11:99339286-99354424 | | 15840 | Ksr1 | NM_013571.2 | chr11:78828303-78959856 |
| 15746 | Krt24 | NM_029393.1 | chr11:99141406-99146552 | | 15841 | Ksr2 | NM_001114545.2 | chr5:117864010-118217997 |
| 15747 | Krt25 | NM_133730.1 | chr11:99177157-99184255 | | 15842 | Kti12 | NM_029571.2 | chr4:108520462-108522017 |
| 15748 | Krt26 | NM_001033397.5 | chr11:99189797-99199279 | | 15843 | Ktn1 | NM_008477.2 | chr14:48283430-48356239 |
| 15749 | Krt27 | NM_010666.1 | chr11:99206879-99212408 | | 15844 | Kxd1 | NM_029366.2 | chr8:73037294-73047079 |
| 15750 | Krt28 | NM_027574.1 | chr11:99226320-99236217 | | 15845 | Ky | NM_024291.3 | chr9:102408467-102448569 |
| 15751 | Krt31 | NM_010659.2 | chr11:99907959-99911865 | | 15846 | Kynu | NM_001289593.1 | chr2:43410844-43538568 |
| 15752 | Krt32 | NM_001159374.2 | chr11:99942161-99949540 | | 15847 | Kynu | NM_001289594.1 | chr2:43410844-43538568 |
| 15753 | Krt33a | NM_027983.3 | chr11:99872512-99877526 | | 15848 | Kynu | NM_027552.2 | chr2:43410844-43538568 |
| 15754 | Krt33b | NM_013570.1 | chr11:99884947-99891182 | | 15849 | L1cam | NM_008478.3 | chrX:71099118-71126173 |
| 15755 | Krt34 | NM_027563.3 | chr11:99898664-99902868 | | 15850 | L1td1 | NM_001081202.1 | chr4:98393444-98405177 |
| 15756 | Krt35 | NM_008488.2 | chr11:99953505-99957538 | | 15851 | L2hgdh | NM_145443.2 | chr12:70791422-70825861 |
| 15757 | Krt36 | NM_001174099.1 | chr11:99963326-99966940 | | 15852 | L3hypdh | NM_026038.2 | chr12:73174414-73186300 |
| 15758 | Krt39 | NM_213730.2 | chr11:99375937-99382572 | | 15853 | L3mbtl1 | NM_001081338.1 | chr2:162769200-162800258 |
| 15759 | Krt4 | NM_008475.2 | chr15:101748965-101755166 | | 15854 | L3mbtl2 | NM_001289711.1 | chr15:81494318-81527717 |
| 15760 | Krt40 | NM_001039666.1 | chr11:99398798-99404472 | | 15855 | L3mbtl2 | NM_001289712.1 | chr15:81494318-81527717 |
| 15761 | Krt42 | NM_212483.2 | chr11:100124195-100131185 | | 15856 | L3mbtl2 | NM_145993.5 | chr15:81494318-81527717 |
| 15762 | Krt5 | NM_027011.2 | chr15:101537500-101543322 | | 15857 | L3mbtl2 | NR_110362.1 | chr15:81494318-81527717 |
| 15763 | Krt6a | NM_008476.3 | chr15:101520359-101524736 | | 15858 | L3mbtl3 | NM_172787.2 | chr10:25995257-26094991 |
| 15764 | Krt6b | NM_010669.2 | chr15:101506454-101510720 | | 15859 | L3mbtl4 | NM_177278.5 | chr17:68623136-69129426 |
| 15765 | Krt7 | NM_033073.3 | chr15:101242833-101258237 | | 15860 | l7Rn6 | NM_001291286.1 | chr7:97067194-97089714 |
| 15766 | Krt71 | NM_019956.1 | chr15:101564379-101573528 | | 15861 | l7Rn6 | NM_001291287.1 | chr7:97067194-97089714 |
| 15767 | Krt72 | NM_213728.1 | chr15:101606990-101616889 | | 15862 | l7Rn6 | NM_001291288.1 | chr7:97067194-97089714 |
| 15768 | Krt73 | NM_212485.2 | chr15:101623738-101632763 | | 15863 | l7Rn6 | NM_001291289.1 | chr7:97067194-97089714 |
| 15769 | Krt74 | NR_033444.1 | chr15:101584689-101593935 | | 15864 | l7Rn6 | NM_026304.3 | chr7:97067194-97089714 |
| 15770 | Krt75 | NM_133357.3 | chr15:101393774-101404335 | | 15865 | l7Rn6 | NR_111916.1 | chr7:97067194-97089714 |
| 15771 | Krt76 | NM_001033177.2 | chr15:101714781-101723351 | | 15866 | lacc1 | NM_172488.2 | chr14:77424007-77436424 |
| 15772 | Krt77 | NM_001003667.1 | chr15:101690286-101700049 | | 15867 | lace1 | NM_145743.2 | chr10:42032390-42198371 |
| 15773 | Krt78 | NM_212487.4 | chr15:101776434-101784718 | | 15868 | lactb | NM_030717.1 | chr9:66803199-66823291 |
| 15774 | Krt79 | NM_146063.1 | chr15:101759762-101770755 | | 15869 | lactb2 | NM_145381.2 | chr1:13615979-13650590 |
| 15775 | Krt8 | NM_031170.2 | chr15:101827141-101834773 | | 15870 | lactbl1 | NM_001243262.1 | chr4:136178535-136194025 |
| 15776 | Krt80 | NM_028770.2 | chr15:101180002-101200556 | | 15871 | lad1 | NM_133664.3 | chr1:137715174-137729918 |
| 15777 | Krt81 | NM_001166157.1 | chr15:101289491-101294196 | | 15872 | lag3 | NM_008479.2 | chr6:124854376-124861723 |
| 15778 | Krt82 | NM_053249.3 | chr15:101371656-101381090 | | 15873 | lage3 | NM_025410.2 | chrX:71597500-71598957 |
| 15779 | Krt83 | NM_001003668.2 | chr15:101261920-101269235 | | 15874 | lair1 | NM_001113474.1 | chr7:3958674-4014806 |
| 15780 | Krt84 | NM_008474.2 | chr15:101355457-101363251 | | 15875 | lair1 | NM_178611.6 | chr7:3958674-4014806 |
| 15781 | Krt85 | NM_016879.2 | chr15:101346119-101521940 | | 15876 | lalba | NM_010679.1 | chr15:98310830-98313114 |
| 15782 | Krt86 | NM_201255.2 | chr15:101303908-101310414 | | 15877 | lama1 | NM_008480.2 | chr17:68046604-68171985 |
| 15783 | Krt9 | NM_201255.2 | chr11:100048094-100054560 | | 15878 | lama2 | NM_008481.2 | chr10:26701091-27336748 |
| 15784 | Krtap10-10 | NM_001024709.3 | chr10:77298692-77299996 | | 15879 | lama3 | NM_010680.1 | chr18:12492532-12741521 |
| 15785 | Krtap10-4 | NM_001135991.1 | chr10:77288914-77289815 | | 15880 | lama4 | NM_010814.1 | chr10:38685320-38829994 |
| 15786 | Krtap11-1 | NM_001113406.1 | chr16:89570420-89571428 | | 15881 | lama5 | NM_001081171.2 | chr2:179911078-179960564 |
| 15787 | Krtap12-1 | NM_010670.1 | chr11:77183331-77184001 | | 15882 | lamb1 | NM_008482.2 | chr12:31956158-32014504 |
| 15788 | Krtap13 | NM_010671.1 | chr16:88750989-88751873 | | 15883 | lamb2 | NM_008483.3 | chr9:108382192-108392861 |
| 15789 | Krtap1-3 | NM_001085526.2 | chr11:99451775-99452691 | | 15884 | lamb3 | NM_001277928.1 | chr1:195128187-195170072 |
| 15790 | Krtap13-1 | NM_183196.1 | chr16:88729106-88729806 | | 15885 | lamb3 | NM_008484.2 | chr1:195128187-195170072 |
| 15791 | Krtap14 | NM_013707.2 | chr16:88825535-88826390 | | 15886 | lamc1 | NM_010683.2 | chr1:155066051-155179916 |
| 15792 | Krtap1-4 | NM_001039502.2 | chr11:99443862-99444991 | | 15887 | lamc2 | NM_008485.3 | chr1:154969685-155033577 |
| 15793 | Krtap15 | NM_013713.1 | chr16:88829253-88830089 | | 15888 | lamc3 | NM_010836.1 | chr2:31742800-31802055 |
| 15794 | Krtap1-5 | NM_027157.3 | chr11:99441290-99442330 | | 15889 | lamp1 | NM_010684.2 | chr8:13159134-13175338 |
| 15795 | Krtap16-1 | NM_130870.1 | chr16:88873909-88874514 | | 15890 | lamp2 | NM_001017959.2 | chrX:35754533-35809637 |
| 15796 | Krtap16-3 | NM_183296.1 | chr16:88962548-88963118 | | 15891 | lamp2 | NM_001290485.1 | chrX:35754533-35809637 |
| 15797 | Krtap17-1 | NM_001099774.2 | chr11:99854545-99855308 | | 15892 | lamp2 | NM_010685.4 | chrX:35754533-35809637 |
| 15798 | Krtap19-1 | NM_130876.3 | chr16:88869162-88869655 | | 15893 | lamp3 | NM_177356.3 | chr16:19653473-19706458 |

Fig. 25 - 85

| | | | | | | | | |
|---|---|---|---|---|---|---|---|---|
| 15894 | Lamp5 | NM_029530.2 | chr2:135883662-135895653 | | 15989 | Lcp1 | NM_001247984.1 | chr14:75530929-75630649 |
| 15895 | Lamtor1 | NM_025605.3 | chr7:109054351-109060417 | | 15990 | Lcp1 | NM_008879.4 | chr14:75530929-75630649 |
| 15896 | Lamtor2 | NM_031248.2 | chr3:88353740-88356849 | | 15991 | Lcp2 | NM_010696.3 | chr11:33947200-33992280 |
| 15897 | Lamtor3 | NM_019920.2 | chr3:137581518-137591726 | | 15992 | Lct | NM_001081078.1 | chr1:130181340-130224895 |
| 15898 | Lamtor4 | NM_001081108.2 | chr5:138696709-138700623 | | 15993 | Lctl | NM_145835.2 | chr9:63964954-63985925 |
| 15899 | Lamtor5 | NM_026774.2 | chr3:107081775-107086999 | | 15994 | Ldb1 | NM_001113408.1 | chr19:46107090-46119701 |
| 15900 | Lancl1 | NM_001190984.1 | chr1:67047090-67085446 | | 15995 | Ldb1 | NM_010697.1 | chr19:46107090-46119701 |
| 15901 | Lancl1 | NM_001190985.1 | chr1:67047090-67085446 | | 15996 | Ldb2 | NM_001077398.2 | chr5:44863371-45190985 |
| 15902 | Lancl1 | NM_021295.3 | chr1:67047090-67085446 | | 15997 | Ldb2 | NM_001286348.1 | chr5:44863371-45190985 |
| 15903 | Lancl2 | NM_133737.2 | chr6:57652448-57689443 | | 15998 | Ldb2 | NM_010698.4 | chr5:44863371-45190985 |
| 15904 | Lancl3 | NM_173414.3 | chrX:8777098-8845211 | | 15999 | Ldb3 | NM_001039071.2 | chr14:35339884-35401867 |
| 15905 | Lao1 | NM_133892.4 | chr4:118634571-118641515 | | 16000 | Ldb3 | NM_001039072.2 | chr14:35339884-35401867 |
| 15906 | Lap3 | NM_024434.6 | chr5:45884612-45903930 | | 16001 | Ldb3 | NM_001039073.2 | chr14:35339884-35401867 |
| 15907 | Laptm4a | NM_008640.2 | chr12:8928112-8945547 | | 16002 | Ldb3 | NM_001039074.2 | chr14:35339884-35401867 |
| 15908 | Laptm4b | NM_033521.3 | chr15:34167780-34214050 | | 16003 | Ldb3 | NM_001039075.2 | chr14:35339884-35401867 |
| 15909 | Laptm5 | NM_010686.3 | chr4:130469248-130492063 | | 16004 | Ldb3 | NM_001039076.2 | chr14:35339884-35401867 |
| 15910 | Large | NM_010687.1 | chr8:75338498-75876455 | | 16005 | Ldb3 | NM_011918.4 | chr14:35339884-35401867 |
| 15911 | Larp1 | NM_028451.1 | chr11:57822565-57875534 | | 16006 | Ldha | NM_001136069.2 | chr7:54101173-54110997 |
| 15912 | Larp1b | NM_001040399.1 | chr3:40754552-40781715 | | 16007 | Ldha | NM_010699.2 | chr7:54101173-54110997 |
| 15913 | Larp4 | NM_001024526.2 | chr15:99800495-99846789 | | 16008 | Ldha | NR_102727.1 | chr7:54101173-54110997 |
| 15914 | Larp4 | NM_001080948.2 | chr15:99800495-99846789 | | 16009 | Ldhal6b | NM_175349.2 | chr17:5417323-5418767 |
| 15915 | Larp4 | NM_001284521.1 | chr15:99800495-99846789 | | 16010 | Ldhb | NM_008492.3 | chr6:142438768-142456463 |
| 15916 | Larp4 | NM_001284522.1 | chr15:99800495-99846789 | | 16011 | Ldhc | NM_013580.4 | chr7:54116632-54133512 |
| 15917 | Larp4 | NM_001284523.1 | chr15:99800495-99846789 | | 16012 | Ldhd | NM_027570.3 | chr8:114150170-114154222 |
| 15918 | Larp4b | NM_172585.2 | chr13:9093150-9172336 | | 16013 | Ldlr | NM_001252658.1 | chr9:21528019-21554362 |
| 15919 | Larp6 | NM_026235.4 | chr9:60560927-60586608 | | 16014 | Ldlr | NM_001252659.1 | chr9:21528019-21554362 |
| 15920 | Larp7 | NM_138593.2 | chr3:127239632-127256267 | | 16015 | Ldlr | NM_010700.3 | chr9:21528019-21554362 |
| 15921 | Lars | NM_134137.2 | chr18:42362002-42421725 | | 16016 | Ldlrad1 | NM_001081272.1 | chr4:106881784-106890519 |
| 15922 | Lars2 | NM_153168.2 | chr9:123276057-123371782 | | 16017 | Ldlrad2 | NM_001033979.1 | chr4:137126790-137131095 |
| 15923 | Lasp1 | NM_152822.3 | chrX:93130651-93152313 | | 16018 | Ldlrad3 | NM_001290784.1 | chr2:101790357-102026617 |
| 15924 | Lasp1 | NM_010688.4 | chr11:97660985-97700078 | | 16019 | Ldlrad3 | NM_178886.3 | chr2:101790357-102026617 |
| 15925 | Lat | NM_010689.2 | chr7:133507342-133513048 | | 16020 | Ldlrad4 | NM_172631.3 | chr18:68092910-68415203 |
| 15926 | Lat2 | NM_020044.3 | chr5:135075972-135090895 | | 16021 | Ldlrap1 | NM_145554.2 | chr4:134301326-134323919 |
| 15927 | Lat2 | NM_022964.4 | chr5:135075972-135090895 | | 16022 | Ldoc1 | NM_001018087.1 | chrX:58962790-58964125 |
| 15928 | Lats1 | NM_010690.1 | chr10:7401006-7436259 | | 16023 | Ldoc1l | NM_177630.3 | chr15:84383627-84388253 |
| 15929 | Lats2 | NM_015771.2 | chr14:58308498-58364960 | | 16024 | Leap2 | NM_153069.3 | chr11:53235682-53236638 |
| 15930 | Lats2 | NM_153382.1 | chr14:58308498-58364960 | | 16025 | Lect1 | NM_010701.2 | chr14:80037496-80061977 |
| 15931 | Lax1 | NM_001159649.1 | chr1:135575605-135586685 | | 16026 | Lect2 | NM_010702.2 | chr13:56648820-56649899 |
| 15932 | Lax1 | NM_172842.3 | chr1:135575605-135586685 | | 16027 | Lef1 | NM_001276402.1 | chr3:130813214-130927275 |
| 15933 | Layn | NM_001033534.1 | chr9:50864884-50885199 | | 16028 | Lef1 | NM_001276403.2 | chr3:130813214-130927275 |
| 15934 | Lbh | NM_029999.4 | chr17:73267644-73291286 | | 16029 | Lef1 | NM_010703.4 | chr3:130813214-130927275 |
| 15935 | Lbp | NM_008489.2 | chr2:158132228-158158588 | | 16030 | Lefty1 | NM_010094.3 | chr1:182865169-182868532 |
| 15936 | Lbr | NM_133815.2 | chr1:183745445-183772532 | | 16031 | Lefty2 | NM_177099.3 | chr1:182823249-182829233 |
| 15937 | Lbx1 | NM_010691.5 | chr19:45308217-45309726 | | 16032 | Lekr1 | NM_001037923.4 | chr3:65470149-65635084 |
| 15938 | Lbx2 | NM_010692.3 | chr6:83036358-83038235 | | 16033 | Lekr1 | NM_001166659.1 | chr3:65470149-65635084 |
| 15939 | Lca5 | NM_027448.2 | chr9:83284961-83348181 | | 16034 | Lelp1 | NM_027042.1 | chr3:91938915-91946676 |
| 15940 | Lca5 | NM_029434.3 | chr9:83284961-83348181 | | 16035 | Lemd1 | NM_001033250.4 | chr1:134088013-134153959 |
| 15941 | Lca5l | NM_001001492.2 | chr16:96380012-96413864 | | 16036 | Lemd2 | NM_146075.2 | chr17:27326544-27341383 |
| 15942 | Lcat | NM_008490.2 | chr8:108463450-108467302 | | 16037 | Lemd3 | NM_001081193.2 | chr10:120360466-120416386 |
| 15943 | Lce1a1 | NM_025984.2 | chr3:92450453-92452229 | | 16038 | Lenep | NM_020517.4 | chr3:89205817-89206572 |
| 15944 | Lce1a2 | NM_028625.2 | chr3:92472534-92474237 | | 16039 | Leng1 | NM_027203.3 | chr7:3611709-3617442 |
| 15945 | Lce1b | NM_026822.1 | chr3:92459571-92460848 | | 16040 | Leng8 | NM_172736.3 | chr7:4088657-4099775 |
| 15946 | Lce1c | NM_028622.2 | chr3:92483168-92484840 | | 16041 | Leng9 | NM_175529.3 | chr7:4099784-4101474 |
| 15947 | Lce1d | NM_027137.2 | chr3:92489420-92491132 | | 16042 | Leo1 | NM_001039522.1 | chr9:75289330-75314239 |
| 15948 | Lce1e | NM_026811.2 | chr3:92511321-92512996 | | 16043 | Lep | NM_008493.3 | chr6:29010220-29023876 |
| 15949 | Lce1f | NM_026394.3 | chr3:92522617-92524272 | | 16044 | Lepr | NM_001122899.1 | chr4:101390011-101487959 |
| 15950 | Lce1g | NM_025413.2 | chr3:92554072-92556260 | | 16045 | Lepr | NM_010704.2 | chr4:101390011-101487959 |
| 15951 | Lce1h | NM_026335.2 | chr3:92567136-92568987 | | 16046 | Lepr | NM_146146.2 | chr4:101390011-101487959 |
| 15952 | Lce1i | NM_029667.2 | chr3:92581131-92582821 | | 16047 | Lepre1 | NM_001042411.1 | chr4:118905519-118921582 |
| 15953 | Lce1j | NM_001081499.1 | chr3:92592765-92594436 | | 16048 | Lepre1 | NM_001286148.1 | chr4:118905519-118921582 |
| 15954 | Lce1k | NM_001254760.1 | chr3:92610212-92611813 | | 16049 | Lepre1 | NM_019782.3 | chr4:118905519-118921582 |
| 15955 | Lce1l | NM_028628.2 | chr3:92653870-92655208 | | 16050 | Lepre1 | NM_019783.2 | chr4:118905519-118921582 |
| 15956 | Lce1m | NM_025420.2 | chr3:92821728-92822982 | | 16051 | Leprel1 | NM_173379.2 | chr16:25960408-26105870 |
| 15957 | Lce3a | NM_001039594.1 | chr3:92729208-92730152 | | 16052 | Leprel2 | NM_013534.4 | chr6:124791112-124807705 |
| 15958 | Lce3b | NM_025365.3 | chr3:92736900-92738018 | | 16053 | Leprel4 | NM_176830.2 | chr11:100270063-100276133 |
| 15959 | Lce3c | NM_033175.3 | chr3:92748407-92749652 | | 16054 | Leprot | NM_175036.4 | chr4:101320387-101331963 |
| 15960 | Lce3d | NM_001270426.1 | chr3:92761311-92762496 | | 16055 | Leprotl1 | NM_026609.2 | chr8:35198625-35209793 |
| 15961 | Lce3e | NM_001054257.1 | chr3:92770982-92772203 | | 16056 | Letm1 | NM_019694.1 | chr5:34084000-34125353 |
| 15962 | Lce3f | NM_001018079.1 | chr3:92796147-92797348 | | 16057 | Letm2 | NM_173012.3 | chr8:26688961-26707959 |
| 15963 | Lce6a | NM_001046172.1 | chr3:92424006-92425582 | | 16058 | Letmd1 | NM_134093.2 | chr15:100299464-100309683 |
| 15964 | Lck | NM_001162432.1 | chr4:129225587-129250885 | | 16059 | Lfng | NM_008494.3 | chr5:141083294-141091499 |
| 15965 | Lck | NM_001162433.1 | chr4:129225587-129250885 | | 16060 | Lgals1 | NM_008495.2 | chr15:78757154-78760895 |
| 15966 | Lck | NM_010693.3 | chr4:129225587-129250885 | | 16061 | Lgals12 | NM_019516.1 | chr19:7671150-7681666 |
| 15967 | Lclat1 | NM_001081071.2 | chr17:73457324-73592706 | | 16062 | Lgals2 | NM_025622.3 | chr15:78681290-78685959 |
| 15968 | Lclat1 | NM_001177967.1 | chr17:73457324-73592706 | | 16063 | Lgals3 | NM_001145953.1 | chr14:47993534-48005842 |
| 15969 | Lclat1 | NM_001177968.1 | chr17:73457324-73592706 | | 16064 | Lgals3 | NM_010705.3 | chr14:47993534-48005842 |
| 15970 | Lcmt1 | NM_025304.3 | chr7:130521495-130573872 | | 16065 | Lgals3bp | NM_011150.2 | chr11:118254065-118263245 |
| 15971 | Lcmt2 | NM_177846.3 | chr2:120963028-120966434 | | 16066 | Lgals4 | NM_010706.2 | chr7:29618813-29626722 |
| 15972 | Lcn10 | NM_178036.4 | chr2:25538245-25541601 | | 16067 | Lgals6 | NM_010707.2 | chr7:29619201-29626652 |
| 15973 | Lcn11 | NM_001100455.2 | chr2:25632536-25635799 | | 16068 | Lgals7 | NM_008496.4 | chr7:29649404-29651303 |
| 15974 | Lcn12 | NM_029958.1 | chr2:25346364-25349431 | | 16069 | Lgals8 | NM_001199043.1 | chr13:12531668-12554005 |
| 15975 | Lcn2 | NM_008491.1 | chr2:32240156-32243259 | | 16070 | Lgals8 | NM_001291055.1 | chr13:12531668-12554005 |
| 15976 | Lcn3 | NM_010694.1 | chr2:25621088-25623619 | | 16071 | Lgals8 | NM_001291057.1 | chr13:12531668-12554005 |
| 15977 | Lcn4 | NM_010695.1 | chr2:25623193-25626802 | | 16072 | Lgals8 | NM_001291060.1 | chr13:12531668-12554005 |
| 15978 | Lcn5 | NM_001042630.2 | chr2:25513471-25517750 | | 16073 | Lgals8 | NM_018886.5 | chr13:12531668-12554005 |
| 15979 | Lcn5 | NM_001276257.1 | chr2:25513471-25517750 | | 16074 | Lgals9 | NM_001159301.1 | chr11:78776480-78798426 |
| 15980 | Lcn5 | NM_007947.3 | chr2:25513471-25517750 | | 16075 | Lgals9 | NM_010708.2 | chr11:78776480-78798426 |
| 15981 | Lcn6 | NM_001076448.1 | chr2:25532305-25537127 | | 16076 | Lgalsl | NM_173752.4 | chr11:20723357-20731111 |
| 15982 | Lcn6 | NM_177840.4 | chr2:25532305-25537127 | | 16077 | Lgi1 | NM_020278.2 | chr19:38383271-38383429 |
| 15983 | Lcn8 | NM_033145.1 | chr2:25508637-25511736 | | 16078 | Lgi2 | NM_144945.2 | chr5:52929102-52957519 |
| 15984 | Lcn9 | NM_029959.2 | chr2:25678672-25681057 | | 16079 | Lgi3 | NM_145219.4 | chr14:70930627-70938131 |
| 15985 | Lcor | NM_172154.4 | chr19:41624128-41634271 | | 16080 | Lgi4 | NM_144556.2 | chr7:31844954-31855954 |
| 15986 | Lcorl | NM_001036073.1 | chr5:46061163-46248779 | | 16081 | Lgmn | NM_011175.2 | chr12:103632307-103677907 |
| 15987 | Lcorl | NM_172153.3 | chr5:46061163-46248779 | | 16082 | Lgr4 | NM_172671.2 | chr2:109757803-109854414 |
| 15988 | Lcorl | NM_178142.5 | chr5:46061163-46248779 | | 16083 | Lgr5 | NM_010195.2 | chr10:114887370-115024836 |

Fig. 25 - 86

| | | | |
|---|---|---|---|
| 16084 | Lgr6 | NM_001033409.3 | chr1:136882929-137001853 |
| 16085 | Lgsn | NM_153601.1 | chr1:31233280-31261570 |
| 16086 | Lhb | NM_008497.2 | chr7:52676315-52677224 |
| 16087 | Lhcgr | NM_013582.2 | chr17:89140888-89191316 |
| 16088 | Lhfp | NM_175386.3 | chr3:52845468-53085601 |
| 16089 | Lhfpl1 | NM_178358.3 | chrX:141724901-141783437 |
| 16090 | Lhfpl2 | NM_172589.2 | chr13:94827750-94965364 |
| 16091 | Lhfpl3 | NM_001081231.2 | chr5:22244728-22781415 |
| 16092 | Lhfpl3 | NM_029990.1 | chr5:22244728-22781415 |
| 16093 | Lhfpl4 | NM_177763.1 | chr6:113118086-113145378 |
| 16094 | Lhfpl5 | NM_026571.2 | chr17:28712663-28720538 |
| 16095 | Lhpp | NM_029609.1 | chr7:139802325-139898102 |
| 16096 | Lhx1 | NM_008498.2 | chr11:84332880-84349036 |
| 16097 | Lhx1os | NR_038057.1 | chr11:84339161-84349333 |
| 16098 | Lhx2 | NM_001290646.1 | chr2:38194800-38225257 |
| 16099 | Lhx2 | NM_010710.4 | chr2:38194800-38225257 |
| 16100 | Lhx3 | NM_001039653.2 | chr2:26055731-26063769 |
| 16101 | Lhx3 | NM_010711.2 | chr2:26055731-26063769 |
| 16102 | Lhx4 | NM_010712.2 | chr1:157548823-157589157 |
| 16103 | Lhx5 | NM_008499.5 | chr5:120881894-120891466 |
| 16104 | Lhx6 | NM_001083125.1 | chr2:35937472-35960928 |
| 16105 | Lhx6 | NM_010711.2 | chr2:35937472-35960928 |
| 16106 | Lhx6 | NM_001083127.1 | chr2:35937472-35960928 |
| 16107 | Lhx6 | NM_008500.2 | chr2:35937472-35960928 |
| 16108 | Lhx8 | NM_010713.2 | chr3:153969257-153993524 |
| 16109 | Lhx9 | NM_001025565.2 | chr1:140721762-140744156 |
| 16110 | Lhx9 | NM_001042577.1 | chr1:140721762-140744156 |
| 16111 | Lhx9 | NM_010713.2 | chr1:140721762-140744156 |
| 16112 | Lias | NM_024471.4 | chr5:65782735-65800446 |
| 16113 | Lif | NM_001039537.2 | chr11:4157570-4172517 |
| 16114 | Lif | NM_008501.2 | chr11:4157570-4172517 |
| 16115 | Lifr | NM_001113386.1 | chr15:7079571-7147489 |
| 16116 | Lifr | NM_013584.2 | chr15:7079571-7147489 |
| 16117 | Lig1 | NM_001083188.1 | chr7:13844315-13896776 |
| 16118 | Lig1 | NM_001199310.1 | chr7:13844315-13896776 |
| 16119 | Lig1 | NM_010715.2 | chr7:13844315-13896776 |
| 16120 | Lig3 | NM_001291245.1 | chr11:82594610-82684712 |
| 16121 | Lig3 | NM_001291246.1 | chr11:82594610-82684712 |
| 16122 | Lig3 | NM_001291247.1 | chr11:82594610-82684712 |
| 16123 | Lig3 | NM_010716.3 | chr11:82594610-82684712 |
| 16124 | Lig4 | NM_176953.3 | chr8:9970019-9976323 |
| 16125 | Lilra5 | NM_001081239.2 | chr7:4189355-4195065 |
| 16126 | Lilra6 | NM_013090.2 | chr7:3683234-3867103 |
| 16127 | Lilra6 | NR_028115.1 | chr7:3683234-3867103 |
| 16128 | Lilrb4 | NM_001291894.1 | chr10:51210703-51216417 |
| 16129 | Lilrb4 | NM_013532.3 | chr10:51210703-51216417 |
| 16130 | Lim2 | NM_177693.3 | chr7:50685470-50691361 |
| 16131 | Lima1 | NM_001113545.1 | chr15:99608898-99705887 |
| 16132 | Lima1 | NM_023063.4 | chr15:99608898-99705887 |
| 16133 | Limch1 | NM_001001980.2 | chr5:67137078-67448398 |
| 16134 | Limch1 | NM_001256122.1 | chr5:67137078-67448398 |
| 16135 | Limd1 | NM_013860.2 | chr9:123387818-123430670 |
| 16136 | Limd2 | NM_172977.3 | chr11:106017569-106021456 |
| 16137 | Lime1 | NM_023684.2 | chr2:181115939-181118333 |
| 16138 | Limk1 | NM_010717.3 | chr5:135131908-135164460 |
| 16139 | Limk2 | NM_001034030.2 | chr11:3243299-3309241 |
| 16140 | Limk2 | NM_010718.1 | chr11:3243299-3309241 |
| 16141 | Limk2 | NM_173053.1 | chr11:3243299-3309241 |
| 16142 | Lims1 | NM_144862.3 | chr18:32091161-32118273 |
| 16143 | Lims1 | NM_026148.3 | chr10:57786213-57887439 |
| 16144 | Lims1 | NM_201242.1 | chr10:57786213-57887439 |
| 16145 | Lims2 | NM_144862.3 | chr18:32091161-32118273 |
| 16146 | Lin28a | NM_145833.1 | chr4:133559244-133574731 |
| 16147 | Lin28b | NM_001031772.2 | chr10:45096424-45190007 |
| 16148 | Lin37 | NM_001290569.1 | chr7:31340459-31344665 |
| 16149 | Lin37 | NM_029377.2 | chr7:31340459-31344665 |
| 16150 | Lin52 | NM_173756.4 | chr12:85792457-85872483 |
| 16151 | Lin54 | NM_001115010.1 | chr5:100871057-100929658 |
| 16152 | Lin54 | NM_172714.4 | chr5:100871057-100929658 |
| 16153 | Lin7a | NM_001033233.2 | chr10:106708886-106862199 |
| 16154 | Lin7a | NM_001039354.1 | chr10:106708886-106862199 |
| 16155 | Lin7a | NM_001284329.1 | chr10:106708886-106862199 |
| 16156 | Lin7b | NM_011698.3 | chr7:52623261-52625934 |
| 16157 | Lin7c | NM_011699.3 | chr2:109731034-109741093 |
| 16158 | Lin9 | NM_001103182.2 | chr1:182571464-182620818 |
| 16159 | Lin9 | NM_175186.4 | chr1:182571464-182620818 |
| 16160 | Lincrna-cox2 | NR_110420.1 | chr1:152006172-152012078 |
| 16161 | Lingo1 | NM_181074.4 | chr9:56466281-56533060 |
| 16162 | Lingo2 | NM_001185999.1 | chr4:35653896-36898777 |
| 16163 | Lingo2 | NM_001166000.1 | chr4:35653896-36898777 |
| 16164 | Lingo2 | NM_001166001.1 | chr4:35653896-36898777 |
| 16165 | Lingo2 | NM_175516.4 | chr4:35653896-36898777 |
| 16166 | Lingo3 | NM_001013758.2 | chr10:80295547-80306784 |
| 16167 | Lingo4 | NM_177250.2 | chr3:94203140-94208423 |
| 16168 | Lins | NM_001191001.1 | chr7:73834774-73862142 |
| 16169 | Lins | NM_152815.1 | chr7:73834774-73862142 |
| 16170 | Lins | NR_034030.1 | chr7:73834774-73862142 |
| 16171 | Lipa | NM_001111100.1 | chr19:34566805-34601964 |
| 16172 | Lipa | NM_021460.3 | chr19:34566805-34601964 |
| 16173 | Lipc | NM_008280.2 | chr9:70645934-70782615 |
| 16174 | Lipe | NM_001039507.2 | chr7:26161837-26351436 |
| 16175 | Lipe | NM_010719.5 | chr7:26161837-26351436 |
| 16176 | Lipf | NM_026334.1 | chr19:34035737-34051303 |
| 16177 | Lipg | NM_010720.3 | chr18:75098975-75120917 |
| 16178 | Liph | NM_001083894.1 | chr16:21953890-21995615 |
| 16179 | Liph | NM_001289581.1 | chr16:21953890-21995615 |
| 16180 | Liph | NM_001289582.1 | chr16:21953890-21995615 |
| 16181 | Liph | NM_153404.3 | chr16:21953890-21995615 |
| 16182 | Lipi | NM_001252513.1 | chr16:75540758-75586306 |
| 16183 | Lipk | NM_001205349.1 | chr19:34082743-34122393 |
| 16184 | Lipk | NM_172837.4 | chr19:34082743-34122393 |
| 16185 | Lipm | NM_023903.1 | chr19:34175433-34197177 |
| 16186 | Lipn | NM_027340.2 | chr19:34141847-34159408 |
| 16187 | Lipo1 | NM_001013770.3 | chr19:33629770-33664801 |
| 16188 | Lipt1 | NM_001037918.3 | chr1:37929050-37933143 |
| 16189 | Lipt2 | NM_026010.2 | chr7:107307786-107309441 |
| 16190 | Litaf | NM_019980.2 | chr16:10969365-10993214 |
| 16191 | Lix1 | NM_025681.2 | chr17:17539649-17596351 |
| 16192 | Lix1l | NM_001163170.1 | chr3:96405056-96429275 |
| 16193 | Lkaaear1 | NM_199023.3 | chr2:181431499-181433147 |
| 16194 | Llgl1 | NM_001159404.1 | chr11:60513191-60540723 |
| 16195 | Llgl1 | NM_001159405.1 | chr11:60513191-60540723 |
| 16196 | Llgl1 | NM_008502.2 | chr11:60513191-60540723 |
| 16197 | Llgl2 | NM_001252532.1 | chr11:115685371-115717094 |
| 16198 | Llgl2 | NM_145438.2 | chr11:115685371-115717094 |
| 16199 | Llph | NM_025431.1 | chr10:119664115-119669126 |
| 16200 | Lman1 | NM_001172062.1 | chr18:66140392-66162289 |
| 16201 | Lman1 | NM_027400.3 | chr18:66140392-66162289 |
| 16202 | Lman1l | NM_199222.3 | chr9:57454839-57468581 |
| 16203 | Lman2 | NM_025828.3 | chr13:55445193-55464144 |
| 16204 | Lman2l | NM_001013374.1 | chr1:36480030-36502084 |
| 16205 | Lmbr1 | NM_020295.3 | chr5:29556341-29794930 |
| 16206 | Lmbrd | NM_029098.3 | chr15:98734351-98748529 |
| 16207 | Lmbrd1 | NM_026719.2 | chr1:24685382-24823146 |
| 16208 | Lmbrd2 | NM_177178.3 | chr15:9070326-9127206 |
| 16209 | Lmcd1 | NM_144799.2 | chr6:112223752-112280417 |
| 16210 | Lmf1 | NM_029624.4 | chr17:25716118-25799771 |
| 16211 | Lmf1 | NR_045520.1 | chr17:25716118-25799771 |
| 16212 | Lmf2 | NM_178919.4 | chr15:89181434-89186090 |
| 16213 | Lmln | NM_172823.2 | chr16:33062607-33125745 |
| 16214 | Lmna | NM_001002011.3 | chr3:88285069-88307274 |
| 16215 | Lmna | NM_001111102.2 | chr3:88285069-88307274 |
| 16216 | Lmna | NM_019390.3 | chr3:88285069-88307274 |
| 16217 | Lmnb1 | NM_010721.2 | chr18:56867466-56913079 |
| 16218 | Lmnb2 | NM_010722.5 | chr10:80364107-80380990 |
| 16219 | Lmo1 | NM_057173.3 | chr7:116282085-116313822 |
| 16220 | Lmo2 | NM_001142335.1 | chr2:103798151-103822035 |
| 16221 | Lmo2 | NM_001142336.1 | chr2:103798151-103822035 |
| 16222 | Lmo2 | NM_001142337.1 | chr2:103798151-103822035 |
| 16223 | Lmo2 | NM_008505.4 | chr2:103798151-103822035 |
| 16224 | Lmo3 | NM_207222.1 | chr6:138313001-138530489 |
| 16225 | Lmo4 | NM_001161769.1 | chr3:143851493-143868219 |
| 16226 | Lmo4 | NM_001161770.1 | chr3:143851493-143868219 |
| 16227 | Lmo4 | NM_010723.3 | chr3:143851493-143868219 |
| 16228 | Lmo7 | NM_201529.2 | chr14:102129144-102333910 |
| 16229 | Lmod1 | NM_053106.2 | chr1:137221389-137264642 |
| 16230 | Lmod2 | NM_053098.2 | chr6:24547770-24555414 |
| 16231 | Lmod3 | NM_001081157.1 | chr6:97188521-97202774 |
| 16232 | Lmtk2 | NM_001081109.1 | chr5:144861304-144949073 |
| 16233 | Lmtk3 | NM_001005513.3 | chr7:53039316-53059512 |
| 16234 | Lmtk3 | NM_001290990.1 | chr7:53039316-53059512 |
| 16235 | Lmtk3 | NR_110987.1 | chr7:53039316-53059512 |
| 16236 | Lmx1a | NM_033652.5 | chr1:169619688-169798864 |
| 16237 | Lmx1b | NM_010725.2 | chr2:33420055-33496031 |
| 16238 | Lnp | NM_001110209.1 | chr2:74352893-74417005 |
| 16239 | Lnp | NM_027133.3 | chr2:74352893-74417005 |
| 16240 | Lnpep | NM_172827.3 | chr17:17664686-17761453 |
| 16241 | Lnx1 | NM_001159577.1 | chr5:74931506-75098928 |
| 16242 | Lnx1 | NM_001159578.1 | chr5:74931506-75098928 |
| 16243 | Lnx1 | NM_001159579.1 | chr5:74931506-75098928 |
| 16244 | Lnx1 | NM_001159580.1 | chr5:74931506-75098928 |
| 16245 | Lnx1 | NM_010727.4 | chr5:74931506-75098928 |
| 16246 | Lnx2 | NM_080795.4 | chr5:147828230-147888148 |
| 16247 | LOC100038947 | NM_001173459.2 | chr3:15695146-15748487 |
| 16248 | LOC100040786 | NM_001160129.1 | chrY_random:17981233-17983607 |
| 16249 | LOC100043315 | NR_015482.1 | chr15:94928052-94979749 |
| 16250 | LOC100048884 | NM_001199333.1 | chr4:61331211-61335128 |
| 16251 | LOC100502896 | NM_001277512.1 | chr4:73268577-73272959 |
| 16252 | LOC100503280 | NM_001251890.1 | chrX:72212182-72214464 |
| 16253 | LOC100503496 | NR_040680.1 | chr11:109301392-109314673 |
| 16254 | LOC100503676 | NR_103491.1 | chr8:87437234-87446814 |
| 16255 | LOC100504039 | NR_102724.1 | chrX:50989704-50994502 |
| 16256 | LOC100504608 | NM_001205036.1 | chr10:126469960-126478450 |
| 16257 | LOC100504703 | NR_040660.1 | chr10:126507536-126508157 |
| 16258 | LOC100505025 | NR_105062.1 | chr7:80455266-80460079 |
| 16259 | LOC100861615 | NM_001270812.1 | chr14:3049284-3077025 |
| 16260 | LOC100861615 | NM_001270812.1 | chr14:5468459-6240637 |
| 16261 | LOC100861615 | NM_001270812.1 | chr14:6653690-7119724 |
| 16262 | LOC100861615 | NM_001270812.1 | chr14:7915538-8007047 |
| 16263 | LOC100861978 | NM_001267702.1 | chr4:42339258-42354418 |
| 16264 | LOC100861978 | NM_001267703.1 | chr4:42664135-42679295 |
| 16265 | LOC100861978 | NM_001267703.1 | chr4:42339258-42354418 |
| 16266 | LOC100861978 | NM_001267704.1 | chr4:42664135-42679295 |
| 16267 | LOC100861978 | NM_001267704.1 | chr4:41763293-42104673 |
| 16268 | LOC100861978 | NM_001267704.1 | chr4:42339258-42354418 |
| 16269 | LOC100861978 | NM_001277531.1 | chr4:73,281,699-73,318,302 |
| 16270 | LOC100862268 | NR_105029.1 | chr3:126864222-126871208 |
| 16271 | LOC100862268 | NR_105030.1 | chr3:126864222-126871208 |
| 16272 | LOC101055769 | NR_105031.1 | chr4:59272922-59282016 |

Fig. 25 - 87

| | | | |
|---|---|---|---|
| 16273 | LOC101055863 | NM_001277487.1 | chr4:73281698-73288077 |
| 16274 | LOC101055863 | NM_001277487.1 | chr4:73311921-73318302 |
| 16275 | LOC101055863 | NM_001277487.1 | chr4:73327081-73333464 |
| 16276 | LOC101056043 | NR_106032.1 | chr5:110858894-110860974 |
| 16277 | LOC101056136 | NR_105055.1 | chr14:42833465-42838855 |
| 16278 | LOC101056149 | NR_105041.1 | chr13:34744791-34758643 |
| 16279 | LOC101056236 | NR_105054.1 | chr16:92377315-92382928 |
| 16280 | LOC101243624 | NR_102297.1 | chr3:132505165-132541560 |
| 16281 | LOC101243624 | NR_102298.1 | chr3:132505165-132541560 |
| 16282 | LOC101669761 | NR_103513.1 | chr16:31986917-31987877 |
| 16283 | LOC102308570 | NM_001286103.1 | chr9:8958368-8965249 |
| 16284 | LOC102631757 | NR_110502.1 | chr5:143200557-143579066 |
| 16285 | LOC102631757 | NR_110502.1 | chr17:31289696-31301998 |
| 16286 | LOC102631757 | NR_110503.1 | chr17:31289696-31301998 |
| 16287 | LOC102631757 | NR_110503.1 | chr5:143200557-143579066 |
| 16288 | LOC102632423 | NR_110507.1 | chr6:118250184-118258737 |
| 16289 | LOC102632430 | NR_110508.1 | chr16:22875056-22894459 |
| 16290 | LOC102633035 | NR_110509.1 | chr9:101244523-101250347 |
| 16291 | LOC102633315 | NR_110510.1 | chr8:26659145-26666655 |
| 16292 | LOC102634101 | NR_110511.1 | chr10:66467823-66504074 |
| 16293 | LOC102634403 | NR_110447.1 | chr2:74590741-74591799 |
| 16294 | LOC102634431 | NR_110513.1 | chr9:8644078-8740988 |
| 16295 | LOC102634753 | NR_110516.1 | chr3:98853744-98857665 |
| 16296 | LOC102635087 | NR_110517.1 | chr9:71016582-71055929 |
| 16297 | LOC102636514 | NR_110474.1 | chr7:106408990-106415728 |
| 16298 | LOC106740 | NR_027905.1 | chr17:15084741-15085828 |
| 16299 | LOC171588 | NR_038065.1 | chr2:144290912-144292468 |
| 16300 | LOC381967 | NR_103487.1 | chr7:106408990-106415728 |
| 16301 | LOC547349 | NM_001025208.1 | chr17:35402724-35462354 |
| 16302 | LOC666331 | NM_001256318.1 | chr11:101472013-101477270 |
| 16303 | Loh12cr1 | NM_001170479.1 | chr6:134589529-134661202 |
| 16304 | Loh12cr1 | NM_026371.3 | chr6:134589529-134661202 |
| 16305 | Lonp1 | NM_028782.2 | chr17:56753721-56766326 |
| 16306 | Lonp2 | NM_001168591.1 | chr8:89147941-89240535 |
| 16307 | Lonp2 | NM_025827.3 | chr8:89147941-89240535 |
| 16308 | Lonrf1 | NM_001081150.1 | chr8:37279117-37312570 |
| 16309 | Lonrf2 | NM_001029878.1 | chr1:38851353-38878060 |
| 16310 | Lonrf3 | NM_028894.1 | chrX:33868403-33906851 |
| 16311 | Lor | NM_008508.2 | chr3:91884192-91887064 |
| 16312 | Lox | NM_001286181.1 | chr18:52675713-52689521 |
| 16313 | Lox | NM_001286182.1 | chr18:52675713-52689521 |
| 16314 | Lox | NM_010728.3 | chr18:52675713-52689521 |
| 16315 | Loxhd1 | NM_172834.2 | chr18:77520696-77680996 |
| 16316 | Loxl1 | NM_010729.3 | chr9:58135529-58161019 |
| 16317 | Loxl2 | NM_033325.2 | chr14:70009283-70095641 |
| 16318 | Loxl3 | NM_013586.4 | chr6:82984218-83002558 |
| 16319 | Loxl4 | NM_001164311.1 | chr19:42666768-42687296 |
| 16320 | Loxl4 | NM_053083.3 | chr19:42666768-42687296 |
| 16321 | Lpar1 | NM_001290486.1 | chr4:58448123-58566363 |
| 16322 | Lpar1 | NM_010336.2 | chr4:58448123-58566363 |
| 16323 | Lpar1 | NM_172989.1 | chr4:58448123-58566363 |
| 16324 | Lpar2 | NM_020028.3 | chr8:72346463-72355001 |
| 16325 | Lpar3 | NM_022983.4 | chr3:145383924-145449178 |
| 16326 | Lpar4 | NM_175271.4 | chrX:104115963-104129238 |
| 16327 | Lpar4 | NM_001163268.1 | chr6:125017937-125032490 |
| 16328 | Lpar5 | NM_001163269.1 | chr6:125017937-125032490 |
| 16329 | Lpar6 | NM_175116.4 | chr14:73637698-73640165 |
| 16330 | Lpcat1 | NM_145376.5 | chr13:73604830-73651986 |
| 16331 | Lpcat2 | NM_173014.1 | chr8:95379249-95443178 |
| 16332 | Lpcat2b | NM_027599.3 | chr5:107860567-107864058 |
| 16333 | Lpcat3 | NM_145130.2 | chr6:124619122-124654734 |
| 16334 | Lpcat4 | NM_207206.2 | chr2:112079997-112087268 |
| 16335 | Lpgat1 | NM_001134829.1 | chr1:193541902-193608134 |
| 16336 | Lpgat1 | NM_172266.3 | chr1:193541902-193608134 |
| 16337 | Lphn1 | NM_181039.2 | chr8:86423996-86465853 |
| 16338 | Lphn2 | NM_001081298.1 | chr3:148478549-148617599 |
| 16339 | Lphn3 | NM_198702.2 | chr5:81450617-82224755 |
| 16340 | Lpin1 | NM_001130412.1 | chr12:16542474-16596576 |
| 16341 | Lpin1 | NM_015763.4 | chr12:16542474-16596576 |
| 16342 | Lpin1 | NM_172950.3 | chr12:16542474-16596576 |
| 16343 | Lpin2 | NM_001164885.1 | chr17:71533317-71599158 |
| 16344 | Lpin2 | NM_022882.4 | chr17:71533317-71599158 |
| 16345 | Lpin3 | NM_001199118.1 | chr2:160706405-160731736 |
| 16346 | Lpin3 | NM_022883.3 | chr2:160706405-160731736 |
| 16347 | Lpl | NM_008509.2 | chr8:71404853-71430831 |
| 16348 | Lpo | NM_080422.2 | chr11:87619929-87639616 |
| 16349 | Lpp | NM_001145952.1 | chr16:24392641-24992664 |
| 16350 | Lpp | NM_001145954.1 | chr16:24392641-24992664 |
| 16351 | Lpp | NM_178565.5 | chr16:24392641-24992664 |
| 16352 | Lpxn | NM_134152.3 | chr19:12873098-12908298 |
| 16353 | Lrat | NM_023624.4 | chr3:82696504-82707896 |
| 16354 | Lrba | NM_001077687.1 | chr3:86028611-86586616 |
| 16355 | Lrba | NM_001077688.1 | chr3:86028611-86586616 |
| 16356 | Lrba | NM_030695.2 | chr3:86028611-86586616 |
| 16357 | Lrch1 | NM_001033439.3 | chr14:75154479-75347684 |
| 16358 | Lrch1 | NM_001252132.1 | chr14:75154479-75347684 |
| 16359 | Lrch2 | NM_001081173.1 | chrX:149906236-149988624 |
| 16360 | Lrch3 | NM_001081255.1 | chr16:32914186-33016115 |
| 16361 | Lrch4 | NM_001168652.1 | chr5:138070350-138084130 |
| 16362 | Lrch4 | NM_146164.2 | chr5:138070350-138084130 |
| 16363 | Lrcol1 | NM_001033459.3 | chr5:110783114-110785106 |
| 16364 | Lrfn1 | NM_001141921.1 | chr7:29237003-29252567 |
| 16365 | Lrfn1 | NM_030562.2 | chr7:29237003-29252567 |
| 16366 | Lrfn2 | NM_027452.3 | chr7:49071906-49236915 |
| 16367 | Lrfn3 | NM_175478.2 | chr7:31140532-31147791 |

| | | | |
|---|---|---|---|
| 16368 | Lrfn4 | NM_153388.4 | chr19:4611784-4615667 |
| 16369 | Lrfn5 | NM_178714.4 | chr12:62625618-62946245 |
| 16370 | Lrg1 | NM_029796.2 | chr17:56259100-56261369 |
| 16371 | Lrguk | NM_028886.1 | chr6:33979447-34084034 |
| 16372 | Lrif1 | NM_001039478.1 | chr3:106487904-106539494 |
| 16373 | Lrif1 | NM_001039488.1 | chr3:106487904-106539494 |
| 16374 | Lrif1 | NM_001286685.1 | chr3:106487904-106539494 |
| 16375 | Lrif1 | NM_028081.2 | chr3:106487904-106539494 |
| 16376 | Lrig1 | NM_008377.2 | chr6:94554523-94650139 |
| 16377 | Lrig2 | NM_001025067.1 | chr3:104257905-104315779 |
| 16378 | Lrig3 | NM_177152.5 | chr10:125403274-125452415 |
| 16379 | Lrit1 | NM_146245.2 | chr14:37868015-37878124 |
| 16380 | Lrit2 | NM_173418.3 | chr14:37881234-37886921 |
| 16381 | Lrit3 | NM_001287224.1 | chr3:129491208-129506948 |
| 16382 | Lrmp | NM_001281980.1 | chr6:145064155-145159490 |
| 16383 | Lrmp | NM_001281981.1 | chr6:145064155-145159490 |
| 16384 | Lrmp | NM_008511.3 | chr6:145064155-145159490 |
| 16385 | Lrp1 | NM_008512.2 | chr10:126975213-127058204 |
| 16386 | Lrp10 | NM_022993.3 | chr14:55082983-55089128 |
| 16387 | Lrp11 | NM_172784.3 | chr10:7309597-7345275 |
| 16388 | Lrp12 | NM_172814.3 | chr15:39702148-39775303 |
| 16389 | Lrp1b | NM_053011.2 | chr2:40452293-42509918 |
| 16390 | Lrp2 | NM_001081088.1 | chr2:69262391-69424124 |
| 16391 | Lrp2bp | NM_026278.3 | chr8:47095955-47114830 |
| 16392 | Lrp3 | NM_001024707.2 | chr7:35985897-36000364 |
| 16393 | Lrp4 | NM_001145857.1 | chr2:91297687-91354058 |
| 16394 | Lrp4 | NM_172668.3 | chr2:91297687-91354058 |
| 16395 | Lrp5 | NM_008513.3 | chr19:3584824-3686564 |
| 16396 | Lrp6 | NM_008514.4 | chr6:134396495-134516931 |
| 16397 | Lrp8 | NM_001080926.1 | chr4:107474863-107549445 |
| 16398 | Lrp8 | NR_033496.1 | chr4:107474863-107549445 |
| 16399 | Lrpap1 | NM_013587.2 | chr5:35434154-35448346 |
| 16400 | Lrpprc | NM_028233.2 | chr17:85104586-85190126 |
| 16401 | Lrr1 | NM_001081406.1 | chr12:70269800-70279997 |
| 16402 | Lrrc1 | NM_001146048.1 | chr9:77278629-77392659 |
| 16403 | Lrrc1 | NM_172528.3 | chr9:77278629-77392659 |
| 16404 | Lrrc10 | NM_146242.2 | chr10:116482396-116483824 |
| 16405 | Lrrc10b | NM_001111140.2 | chr19:10529860-10531937 |
| 16406 | Lrrc14 | NM_145471.2 | chr15:76541169-76545521 |
| 16407 | Lrrc14b | NM_001033042.3 | chr13:74497030-74501448 |
| 16408 | Lrrc15 | NM_028973.2 | chr16:30269387-30283340 |
| 16409 | Lrrc16a | NM_026825.3 | chr13:24104352-24372659 |
| 16410 | Lrrc16b | NM_001024645.1 | chr14:56109929-56127101 |
| 16411 | Lrrc17 | NM_028977.1 | chr5:21049345-21081720 |
| 16412 | Lrrc18 | NM_001146021.1 | chr14:33772732-33998252 |
| 16413 | Lrrc18 | NM_026253.4 | chr14:33772732-33998252 |
| 16414 | Lrrc19 | NM_175305.4 | chr4:94303351-94316835 |
| 16415 | Lrrc2 | NM_028838.2 | chr9:110854048-110886568 |
| 16416 | Lrrc20 | NM_153542.5 | chr10:60938580-61044976 |
| 16417 | Lrrc23 | NM_013588.1 | chr6:124719880-124729736 |
| 16418 | Lrrc24 | NM_198119.2 | chr15:76545706-76552603 |
| 16419 | Lrrc25 | NM_153074.2 | chr8:73140742-73144749 |
| 16420 | Lrrc27 | NM_146117.2 | chr2:25145431-25146713 |
| 16421 | Lrrc27 | NM_001143755.1 | chr7:146289536-146428872 |
| 16422 | Lrrc27 | NM_027164.1 | chr7:146289536-146428872 |
| 16423 | Lrrc28 | NM_027413.1 | chr7:74658295-74790122 |
| 16424 | Lrrc28 | NM_175124.5 | chr7:74658295-74790122 |
| 16425 | Lrrc28 | NR_028143.1 | chr7:74658295-74790122 |
| 16426 | Lrrc28 | NR_028144.1 | chr7:74658295-74790122 |
| 16427 | Lrrc29 | NM_177449.3 | chr8:107836239-107850176 |
| 16428 | Lrrc3 | NM_145152.4 | chr10:77360319-77365281 |
| 16429 | Lrrc30 | NM_001033340.3 | chr17:67980304-67982063 |
| 16430 | Lrrc32 | NM_001133379.1 | chr7:105642731-105650340 |
| 16431 | Lrrc34 | NM_027941.1 | chr3:30523189-30546740 |
| 16432 | Lrrc36 | NM_001033371.3 | chr8:107937521-107987986 |
| 16433 | Lrrc36 | NM_001170788.1 | chr8:107937521-107987986 |
| 16434 | Lrrc36 | NM_001170789.1 | chr8:107937521-107987986 |
| 16435 | Lrrc38 | NM_001162983.1 | chr4:142939652-142960931 |
| 16436 | Lrrc39 | NM_027321.3 | chr3:116265890-116333904 |
| 16437 | Lrrc39 | NM_175413.3 | chr3:116265890-116333904 |
| 16438 | Lrrc3b | NM_146052.4 | chr14:16190030-16271501 |
| 16439 | Lrrc4 | NM_138682.2 | chr6:28778126-28781747 |
| 16440 | Lrrc40 | NM_001289524.1 | chr3:157699645-157730054 |
| 16441 | Lrrc40 | NM_001289525.1 | chr3:157699645-157730054 |
| 16442 | Lrrc40 | NM_024194.6 | chr3:157699645-157730054 |
| 16443 | Lrrc41 | NM_153521.2 | chr4:115747574-115769714 |
| 16444 | Lrrc42 | NM_029985.2 | chr4:106906118-106926138 |
| 16445 | Lrrc43 | NM_001033461.3 | chr5:123939333-123958214 |
| 16446 | Lrrc43 | NM_001289821.1 | chr5:123939333-123958214 |
| 16447 | Lrrc43 | NM_001289822.1 | chr5:123939333-123958214 |
| 16448 | Lrrc45 | NM_153545.2 | chr11:120575266-120582441 |
| 16449 | Lrrc46 | NM_027026.2 | chr11:96895915-96902683 |
| 16450 | Lrrc47 | NM_201226.1 | chr4:153385912-153395621 |
| 16451 | Lrrc48 | NM_029044.2 | chr11:60166881-60207835 |
| 16452 | Lrrc49 | NM_001146046.1 | chr9:60435043-60535941 |
| 16453 | Lrrc49 | NM_001146047.1 | chr9:60435043-60535941 |
| 16454 | Lrrc4b | NM_145616.2 | chr7:51697856-51718714 |
| 16455 | Lrrc4b | NM_198250.1 | chr7:51697856-51718714 |
| 16456 | Lrrc4c | NM_001289742.1 | chr2:96158325-97471821 |
| 16457 | Lrrc4c | NM_001289743.1 | chr2:96158325-97471821 |
| 16458 | Lrrc4c | NM_001289744.1 | chr2:96158325-97471821 |
| 16459 | Lrrc4c | NM_178725.5 | chr2:96158325-97471821 |
| 16460 | Lrrc51 | NM_001162973.1 | chr7:109061502-109082371 |
| 16461 | Lrrc51 | NM_001162974.1 | chr7:109061502-109082371 |
| 16462 | Lrrc51 | NM_027053.1 | chr7:109061502-109082371 |

Fig. 25 - 88

| | | | |
|---|---|---|---|
| 16463 | Lrrc52 | NM_001013382.2 | chr1:169375805-169396911 |
| 16464 | Lrrc55 | NM_001033346.2 | chr2:85028227-85036856 |
| 16465 | Lrrc56 | NM_001172064.1 | chr7:148380028-148399979 |
| 16466 | Lrrc56 | NM_001172065.1 | chr7:148380028-148399979 |
| 16467 | Lrrc56 | NM_153777.2 | chr7:148380028-148399979 |
| 16468 | Lrrc57 | NM_001159609.1 | chr2:120429973-120447295 |
| 16469 | Lrrc57 | NM_001159610.1 | chr2:120429973-120447295 |
| 16470 | Lrrc57 | NM_001159612.1 | chr2:120429973-120447295 |
| 16471 | Lrrc57 | NM_025657.3 | chr2:120429973-120447295 |
| 16472 | Lrrc57 | NR_027510.1 | chr2:120429973-120447295 |
| 16473 | Lrrc58 | NM_177093.3 | chr16:37868485-37888943 |
| 16474 | Lrrc59 | NM_133807.1 | chr1:94491138-94506530 |
| 16475 | Lrrc6 | NM_019457.2 | chr15:66211419-66332472 |
| 16476 | Lrrc61 | NM_001110160.1 | chr6:48504797-48522669 |
| 16477 | Lrrc61 | NM_177736.3 | chr6:48504797-48522669 |
| 16478 | Lrrc63 | NM_027581.1 | chr14:75484109-75530690 |
| 16479 | Lrrc66 | NM_153568.1 | chr5:73997880-74023660 |
| 16480 | Lrrc69 | NM_028499.2 | chr4:14592900-14723199 |
| 16481 | Lrrc7 | NM_001081358.2 | chr3:157745858-158225185 |
| 16482 | Lrrc7 | NM_001291452.1 | chr3:157745858-158225185 |
| 16483 | Lrrc7 | NM_001291453.1 | chr3:157745858-158225185 |
| 16484 | Lrrc71 | NM_028971.1 | chr3:87540845-87552545 |
| 16485 | Lrrc72 | NM_001177877.1 | chr12:36934931-36979985 |
| 16486 | Lrrc72 | NM_027699.2 | chr12:36934931-36979985 |
| 16487 | Lrrc73 | NM_001111142.1 | chr17:46391113-46394265 |
| 16488 | Lrrc74 | NM_001195767.1 | chr12:88075318-88104745 |
| 16489 | Lrrc75a | NM_198861.1 | chr11:62418385-62462025 |
| 16490 | Lrrc75b | NM_198860.2 | chr10:75012869-75023075 |
| 16491 | Lrrc8a | NM_177725.4 | chr2:30093288-30119310 |
| 16492 | Lrrc8b | NM_001033550.2 | chr5:105844793-105915208 |
| 16493 | Lrrc8c | NM_133897.2 | chr5:105948489-106037973 |
| 16494 | Lrrc8d | NM_001122768.1 | chr5:106128987-106244234 |
| 16495 | Lrrc8d | NM_178701.3 | chr5:106128987-106244234 |
| 16496 | Lrrc8e | NM_028175.2 | chr8:4226826-4237470 |
| 16497 | Lrrc9 | NM_001142728.1 | chr12:73542852-73611552 |
| 16498 | Lrrc9 | NM_001142729.1 | chr12:73542852-73611552 |
| 16499 | Lrrc9 | NM_030070.3 | chr12:73542852-73611552 |
| 16500 | Lrrcc1 | NM_001163579.1 | chr3:14533787-14572658 |
| 16501 | Lrrcc1 | NM_001163583.1 | chr3:14533787-14572658 |
| 16502 | Lrrcc1 | NM_028915.3 | chr3:14533787-14572658 |
| 16503 | Lrrd1 | NM_172879.1 | chr5:3845172-3866596 |
| 16504 | Lrrfip1 | NM_001111311.1 | chr1:92895303-93025521 |
| 16505 | Lrrfip1 | NM_001111312.1 | chr1:92895303-93025521 |
| 16506 | Lrrfip1 | NM_008515.4 | chr1:92895303-93025521 |
| 16507 | Lrrfip2 | NM_146483.1 | chr9:111020614-111128172 |
| 16508 | Lrrfip2 | NM_027742.3 | chr9:111020614-111128172 |
| 16509 | Lrriq1 | NM_001163559.1 | chr10:102525831-102698956 |
| 16510 | Lrriq1 | NM_029134.2 | chr10:102525831-102698956 |
| 16511 | Lrriq3 | NM_028938.2 | chr3:154756397-154857242 |
| 16512 | Lrriq4 | NM_001290510.1 | chr3:30523188-30571353 |
| 16513 | Lrriq4 | NM_026668.2 | chr3:30523188-30571353 |
| 16514 | Lrrk1 | NM_146191.2 | chr7:73403633-73533227 |
| 16515 | Lrrk2 | NM_025730.3 | chr15:91503654-91646555 |
| 16516 | Lrrn1 | NM_008516.4 | chr6:107479719-107520222 |
| 16517 | Lrrn2 | NM_010732.4 | chr1:134776931-134836582 |
| 16518 | Lrrn3 | NM_001271708.1 | chr12:41750676-43056575 |
| 16519 | Lrrn3 | NM_001271709.1 | chr12:41750676-43056575 |
| 16520 | Lrrn3 | NM_010733.3 | chr12:41750676-43056575 |
| 16521 | Lrrn4 | NM_177303.4 | chr2:132694251-132706598 |
| 16522 | Lrrn4cl | NM_001013019.2 | chr19:8925274-8928399 |
| 16523 | Lrrtm1 | NM_028880.3 | chr6:77192711-77195511 |
| 16524 | Lrrtm2 | NM_178005.4 | chr18:35368663-35374678 |
| 16525 | Lrrtm3 | NM_178678.4 | chr10:63391245-63553003 |
| 16526 | Lrrtm4 | NM_001134743.1 | chr6:79968870-80760137 |
| 16527 | Lrrtm4 | NM_001204122.1 | chr6:79968870-80760137 |
| 16528 | Lrrtm4 | NM_178731.5 | chr6:79968870-80760137 |
| 16529 | Lrsam1 | NM_199302.2 | chr2:32780735-32816775 |
| 16530 | Lrtm1 | NM_176920.4 | chr14:29831394-29846828 |
| 16531 | Lrtm2 | NM_001172207.1 | chr6:119186543-119302425 |
| 16532 | Lrtm2 | NM_172492.3 | chr6:119186543-119302425 |
| 16533 | Lrwd1 | NM_027891.4 | chr5:136598935-136611944 |
| 16534 | Lsamp | NM_175548.3 | chr16:41533454-42146826 |
| 16535 | Lsg1 | NM_178069.5 | chr16:30561454-30587675 |
| 16536 | Lsm1 | NM_026032.1 | chr8:26896062-26914447 |
| 16537 | Lsm10 | NM_001163266.1 | chr4:125773896-125775828 |
| 16538 | Lsm10 | NM_138721.2 | chr4:125773896-125775828 |
| 16539 | Lsm11 | NM_028185.2 | chr11:45741770-45758437 |
| 16540 | Lsm12 | NM_172947.3 | chr11:102024802-102046570 |
| 16541 | Lsm14a | NM_025948.2 | chr7:35129738-35174559 |
| 16542 | Lsm14b | NM_177727.4 | chr2:179759691-179770166 |
| 16543 | Lsm2 | NM_001110101.2 | chr17:35118798-35122838 |
| 16544 | Lsm2 | NM_001204273.1 | chr17:35118798-35122838 |
| 16545 | Lsm2 | NM_001204274.1 | chr17:35118798-35122838 |
| 16546 | Lsm2 | NM_030597.3 | chr17:35118798-35122838 |
| 16547 | Lsm3 | NM_026309.2 | chr6:91466028-91472614 |
| 16548 | Lsm4 | NM_015816.4 | chr8:73197129-73202651 |
| 16549 | Lsm5 | NM_025520.3 | chr6:56651056-56654693 |
| 16550 | Lsm6 | NM_001191004.1 | chr8:81328766-81345051 |
| 16551 | Lsm6 | NM_030145.3 | chr8:81328766-81345051 |
| 16552 | Lsm7 | NM_025349.2 | chr10:80315569-80317954 |
| 16553 | Lsm8 | NM_133939.1 | chr6:18798634-18804052 |
| 16554 | Lsmem1 | NM_001033437.2 | chr12:40902972-40925902 |
| 16555 | Lsp1 | NM_001136071.2 | chr7:149646716-149701914 |
| 16556 | Lsp1 | NM_001271508.1 | chr7:149646716-149701914 |
| 16557 | Lsp1 | NM_001271509.1 | chr7:149646716-149701914 |
| 16558 | Lsp1 | NM_001271510.1 | chr7:149646716-149701914 |
| 16559 | Lsp1 | NM_001271523.1 | chr7:149646716-149701914 |
| 16560 | Lsp1 | NM_019391.3 | chr7:149646716-149701914 |
| 16561 | Lsr | NM_001164184.1 | chr7:31742788-31758488 |
| 16562 | Lsr | NM_001164185.1 | chr7:31742788-31758488 |
| 16563 | Lsr | NM_017405.2 | chr7:31742788-31758488 |
| 16564 | Lss | NM_146006.2 | chr10:75994350-76019884 |
| 16565 | Lst1 | NM_010734.2 | chr17:35322039-35325385 |
| 16566 | Lta | NM_010735.2 | chr17:35340110-35342296 |
| 16567 | Lta4h | NM_008517.2 | chr10:92916140-92947641 |
| 16568 | Ltb | NM_008518.2 | chr17:35331452-35333250 |
| 16569 | Ltb4r1 | NM_008519.2 | chr14:56384798-56387329 |
| 16570 | Ltb4r2 | NM_020490.2 | chr14:56380264-56382066 |
| 16571 | Ltbp1 | NM_019919.1 | chr17:75404868-75792307 |
| 16572 | Ltbp1 | NM_206958.2 | chr17:75404868-75792307 |
| 16573 | Ltbp2 | NM_013589.3 | chr12:86124162-86217445 |
| 16574 | Ltbp3 | NM_008520.2 | chr19:5740904-5758552 |
| 16575 | Ltbp4 | NM_001113549.1 | chr7:28090159-28122631 |
| 16576 | Ltbp4 | NM_175641.2 | chr7:28090159-28122631 |
| 16577 | Ltbr | NM_010736.3 | chr6:125256588-125263888 |
| 16578 | Ltc4s | NM_008521.1 | chr11:50049973-50051973 |
| 16579 | Ltf | NM_008522.3 | chr9:110921795-110945270 |
| 16580 | Ltk | NM_008523.2 | chr2:119577061-119586167 |
| 16581 | Ltk | NM_203345.2 | chr2:119577061-119586167 |
| 16582 | Ltk | NM_206941.1 | chr2:119577061-119586167 |
| 16583 | Ltk | NM_206942.1 | chr2:119577061-119586167 |
| 16584 | Ltn1 | NM_001081068.1 | chr16:87376895-87432851 |
| 16585 | Ltv1 | NM_181470.4 | chr10:12898443-12912943 |
| 16586 | Luc7l | NM_025881.3 | chr17:26389854-26422451 |
| 16587 | Luc7l | NM_028190.3 | chr17:26389854-26422451 |
| 16588 | Luc7l | NR_037905.1 | chr17:26389854-26422451 |
| 16589 | Luc7l | NR_037906.1 | chr17:26389854-26422451 |
| 16590 | Luc7l2 | NM_001170848.1 | chr6:38501443-38559470 |
| 16591 | Luc7l2 | NM_001170849.1 | chr6:38501443-38559470 |
| 16592 | Luc7l2 | NM_138680.2 | chr6:38501443-38559470 |
| 16593 | Luc7l3 | NM_026313.1 | chr11:94152452-94183225 |
| 16594 | Lum | NM_008524.2 | chr10:97028134-97035337 |
| 16595 | Lurap1 | NM_026547.1 | chr4:115809332-115817221 |
| 16596 | Lurap1l | NM_026821.5 | chr4:80556589-80600205 |
| 16597 | Luzp1 | NM_024452.2 | chr4:136025675-136105233 |
| 16598 | Luzp2 | NM_178705.5 | chr7:62090614-62524258 |
| 16599 | Luzp4 | NM_001114383.1 | chrX:145317118-145358682 |
| 16600 | Lxn | NM_016753.4 | chr3:67261921-67267829 |
| 16601 | Ly6a | NM_001271416.1 | chr15:74825306-74828461 |
| 16602 | Ly6a | NM_001271417.1 | chr15:74825306-74828461 |
| 16603 | Ly6a | NM_001271418.1 | chr15:74825306-74828461 |
| 16604 | Ly6a | NM_001271419.1 | chr15:74825306-74828461 |
| 16605 | Ly6a | NM_001271446.1 | chr15:74825306-74828461 |
| 16606 | Ly6a | NM_010738.3 | chr15:74825306-74828461 |
| 16607 | Ly6c1 | NM_001252055.1 | chr15:74874447-74879267 |
| 16608 | Ly6c1 | NM_001252056.1 | chr15:74874447-74879267 |
| 16609 | Ly6c1 | NM_001252057.1 | chr15:74874447-74879267 |
| 16610 | Ly6c1 | NM_001252058.1 | chr15:74874447-74879267 |
| 16611 | Ly6c1 | NM_010741.3 | chr15:74874447-74879267 |
| 16612 | Ly6c2 | NM_001099217.1 | chr15:74938590-74942379 |
| 16613 | Ly6d | NM_010742.1 | chr15:74592485-74593997 |
| 16614 | Ly6e | NM_001164036.1 | chr15:74785480-74790335 |
| 16615 | Ly6e | NM_001164037.1 | chr15:74785480-74790335 |
| 16616 | Ly6e | NM_001164038.1 | chr15:74785480-74790335 |
| 16617 | Ly6e | NM_001164039.1 | chr15:74785480-74790335 |
| 16618 | Ly6e | NM_001164040.1 | chr15:74785480-74790335 |
| 16619 | Ly6e | NM_008529.3 | chr15:74785480-74790335 |
| 16620 | Ly6f | NM_008530.2 | chr15:75098850-75102664 |
| 16621 | Ly6g5b | NM_148939.2 | chr17:35250889-35252345 |
| 16622 | Ly6g5c | NM_148947.1 | chr17:35245244-35248898 |
| 16623 | Ly6g6c | NM_023463.3 | chr17:35204269-35206993 |
| 16624 | Ly6g6d | NM_033478.2 | chr17:35208292-35211409 |
| 16625 | Ly6g6e | NM_027366.1 | chr17:35213886-35215749 |
| 16626 | Ly6g6f | NM_001163192.1 | chr17:35217482-35222540 |
| 16627 | Ly6h | NM_001135688.1 | chr15:75395174-75397612 |
| 16628 | Ly6h | NM_001135689.1 | chr15:75395174-75397612 |
| 16629 | Ly6h | NM_013837.3 | chr15:75395174-75397612 |
| 16630 | Ly6i | NM_020498.2 | chr15:74810241-74813860 |
| 16631 | Ly6k | NM_029627.1 | chr15:74627303-74630398 |
| 16632 | Ly75 | NM_013825.3 | chr2:60131816-60221288 |
| 16633 | Ly86 | NM_010745.2 | chr13:37437213-37510905 |
| 16634 | Ly9 | NM_001277968.1 | chr1:173518743-173537541 |
| 16635 | Ly9 | NM_008534.3 | chr1:173518743-173537541 |
| 16636 | Ly9 | NR_102726.1 | chr1:173518743-173537541 |
| 16637 | Ly96 | NM_001159711.1 | chr1:16678536-16699686 |
| 16638 | Ly96 | NM_016923.2 | chr1:16678536-16699686 |
| 16639 | Lyar | NM_025281.3 | chr5:38611720-38625545 |
| 16640 | Lyg1 | NM_027111.3 | chr1:38003582-38014604 |
| 16641 | Lyg2 | NM_001033427.3 | chr1:37962767-37973338 |
| 16642 | Lyl1 | NM_008535.2 | chr8:87225356-87228615 |
| 16643 | Lyn | NM_001111096.1 | chr4:3605267-3718759 |
| 16644 | Lyn | NM_010747.2 | chr4:3605267-3718759 |
| 16645 | Lynx1 | NM_011838.6 | chr15:74578285-74583409 |
| 16646 | Lypd1 | NM_145100.3 | chr1:127768619-127808791 |
| 16647 | Lypd2 | NM_026671.1 | chr15:74562681-74564743 |
| 16648 | Lypd3 | NM_133743.3 | chr7:25421588-25426137 |
| 16649 | Lypd4 | NM_182785.3 | chr7:25649638-25654710 |
| 16650 | Lypd5 | NM_029806.1 | chr7:25134242-25138852 |
| 16651 | Lypd6 | NM_177139.5 | chr2:49921948-50049089 |
| 16652 | Lypd6 | NR_033304.2 | chr2:49921948-50049089 |

Fig. 25 - 89

| | | | |
|---|---|---|---|
| 16653 | Lypd6b | NM_027990.3 | chr2:49643205-49804366 |
| 16654 | Lypd8 | NM_001083884.1 | chr11:58192533-58204043 |
| 16655 | Lypd8 | NM_027339.2 | chr11:58192533-58204043 |
| 16656 | Lypla1 | NM_008866.2 | chr1:4797973-4836816 |
| 16657 | Lypla2 | NM_011942.1 | chr4:135524139-135528509 |
| 16658 | Lyplal1 | NM_146106.2 | chr1:187911610-187941189 |
| 16659 | Lyrm1 | NM_001285959.1 | chr7:127039374-127060270 |
| 16660 | Lyrm1 | NM_001285960.1 | chr7:127039374-127060270 |
| 16661 | Lyrm1 | NM_001285961.2 | chr7:127039374-127060270 |
| 16662 | Lyrm1 | NM_029610.3 | chr7:127039374-127060270 |
| 16663 | Lyrm1 | NR_104377.1 | chr7:127039374-127060270 |
| 16664 | Lyrm2 | NM_175364.3 | chr4:32887233-32889229 |
| 16665 | Lyrm4 | NM_201358.2 | chr13:36070665-36209226 |
| 16666 | Lyrm5 | NM_001163628.1 | chr6:145159653-145165062 |
| 16667 | Lyrm5 | NM_133688.3 | chr6:145159653-145165062 |
| 16668 | Lyrm7 | NM_029327.3 | chr11:54652790-54674093 |
| 16669 | Lyrm7os | NR_040284.1 | chr11:54633420-54638469 |
| 16670 | Lyrm9 | NM_001076681.2 | chr11:78640096-78657401 |
| 16671 | Lysmd1 | NM_153121.2 | chr3:94938010-94943447 |
| 16672 | Lysmd2 | NM_027309.2 | chr9:75473538-75485580 |
| 16673 | Lysmd3 | NM_030257.1 | chr13:81796804-81810889 |
| 16674 | Lysmd4 | NM_001151051.1 | chr7:74367429-74373354 |
| 16675 | Lysmd4 | NM_175215.4 | chr7:74367429-74373354 |
| 16676 | Lyst | NM_010748.2 | chr13:13682675-13869707 |
| 16677 | Lyve1 | NM_053247.4 | chr7:117994120-118006467 |
| 16678 | Lyz1 | NM_013590.4 | chr10:116724850-116729924 |
| 16679 | Lyz2 | NM_017372.3 | chr10:116714596-116719328 |
| 16680 | Lyzl1 | NM_026092.3 | chr18:4165829-4182234 |
| 16681 | Lyzl4 | NM_026915.2 | chr9:121486961-121550684 |
| 16682 | Lyzl4os | NR_040740.1 | chr9:121496138-121523373 |
| 16683 | Lyzl6 | NM_027083.1 | chr11:103492388-103500188 |
| 16684 | Lzic | NM_026963.1 | chr4:148859441-148870776 |
| 16685 | Lztfl1 | NM_033322.2 | chr9:123606710-123626675 |
| 16686 | Lztr1 | NM_025808.3 | chr16:17509063-17526423 |
| 16687 | Lzts1 | NM_199364.2 | chr8:71659401-71664852 |
| 16688 | Lzts2 | NM_001163136.1 | chr12:120681882-120705405 |
| 16689 | Lzts2 | NM_001130526.1 | chr19:45089665-45120262 |
| 16690 | Lzts2 | NM_145503.2 | chr19:45089665-45120262 |
| 16691 | Lzts3 | NM_001291027.1 | chr2:130458500-130468580 |
| 16692 | Lzts3 | NM_001291028.1 | chr2:130458500-130468580 |
| 16693 | Lzts3 | NM_197945.4 | chr2:130458500-130468580 |
| 16694 | M1ap | NM_033079.3 | chr6:82896915-82980303 |
| 16695 | M6pr | NM_010749.6 | chr6:122259027-122267695 |
| 16696 | Maats1 | NM_001081025.1 | chr16:38297839-38341946 |
| 16697 | Mab21l1 | NM_010750.3 | chr3:55586432-55589209 |
| 16698 | Mab21l2 | NM_011839.3 | chr3:86349503-86352205 |
| 16699 | Mab21l3 | NM_172295.4 | chr3:101616998-101640146 |
| 16700 | Macc1 | NM_001163136.1 | chr12:120681882-120705405 |
| 16701 | Macf1 | NM_001199136.1 | chr4:123026875-123361603 |
| 16702 | Macf1 | NM_001199137.1 | chr4:123026875-123361603 |
| 16703 | Macrod1 | NM_134147.4 | chr19:7131258-7272552 |
| 16704 | Macrod2 | NM_001013802.3 | chr2:140221165-142215786 |
| 16705 | Macrod2 | NM_028584.1 | chr2:140221165-142215786 |
| 16706 | Mad1l1 | NM_010752.3 | chr5:140484642-140797506 |
| 16707 | Mad2l1 | NM_019499.4 | chr6:66485461-66490985 |
| 16708 | Mad2l1bp | NM_025649.3 | chr17:46284333-46290500 |
| 16709 | Mad2l2 | NM_027985.3 | chr4:147514598-147519805 |
| 16710 | Madcam1 | NM_013591.2 | chr10:79127318-79131281 |
| 16711 | Madd | NM_001177719.1 | chr2:90977516-91023204 |
| 16712 | Madd | NM_001177720.1 | chr2:90977516-91023204 |
| 16713 | Madd | NM_145527.4 | chr2:90977516-91023204 |
| 16714 | Maea | NM_021502.2 | chr5:33678220-33715943 |
| 16715 | Mael | NM_175296.4 | chr1:168131515-168168875 |
| 16716 | Maf | NM_001025577.2 | chr8:118227152-118230794 |
| 16717 | Maf1 | NM_001164601.1 | chr15:76181723-76184808 |
| 16718 | Maf1 | NM_001164608.1 | chr15:76181723-76184808 |
| 16719 | Maf1 | NM_026859.3 | chr15:76181723-76184808 |
| 16720 | Mafa | NM_194350.1 | chr15:75577272-75578352 |
| 16721 | Mafb | NM_010658.3 | chr2:160189412-160192801 |
| 16722 | Maff | NM_010755.4 | chr15:79178197-79189506 |
| 16723 | Mafg | NM_010756.3 | chr11:120489666-120494861 |
| 16724 | Mafk | NM_010757.2 | chr5:140267489-140278606 |
| 16725 | Mag | NM_010758.2 | chr7:31684201-31699851 |
| 16726 | Magea1 | NM_020015.2 | chrX:151523061-151524333 |
| 16727 | Magea10 | NM_001085506.1 | chrX:69627208-69632197 |
| 16728 | Magea2 | NM_020016.1 | chrX:151461743-151467835 |
| 16729 | Magea3 | NM_020017.2 | chrX:151383005-151384112 |
| 16730 | Magea4 | NM_020280.2 | chrX:69467355-69468303 |
| 16731 | Magea5 | NM_020018.1 | chrX:151487603-151496096 |
| 16732 | Magea6 | NM_020019.3 | chrX:151358554-151360658 |
| 16733 | Magea8 | NM_020020.4 | chrX:151420317-151430393 |
| 16734 | Mageb1 | NM_001057093.1 | chrX:88577093-88578236 |
| 16735 | Mageb1 | NM_010759.1 | chrX:89260529-89261672 |
| 16736 | Mageb16 | NM_001113734.1 | chrX:76868569-76916774 |
| 16737 | Mageb16 | NM_028025.1 | chrX:76868569-76916774 |
| 16738 | Mageb16-ps1 | NR_033647.1 | chrX:140987301-140990782 |
| 16739 | Mageb18 | NM_173783.3 | chrX:89364218-89844911 |
| 16740 | Mageb2 | NM_031171.1 | chrX:89260529-89261672 |
| 16741 | Mageb2 | NM_031171.1 | chrX:88577093-88578236 |
| 16742 | Mageb3 | NM_008545.2 | chr1:121779507-121781828 |
| 16743 | Mageb4 | NM_001033492.2 | chrX:83495594-83501558 |
| 16744 | Mageb5 | NM_028847.1 | chrX:89024946-89028315 |
| 16745 | Maged1 | NM_019791.2 | chrX:91780812-91787413 |
| 16746 | Maged2 | NM_001199246.1 | chrX:147240963-147248882 |
| 16747 | Maged2 | NM_030700.2 | chrX:147240963-147248882 |
| 16748 | Magee1 | NM_053201.3 | chrX:102315734-102319250 |
| 16749 | Magee2 | NM_053206.2 | chrX:102050290-102052606 |
| 16750 | Mageh1 | NM_023788.3 | chrX:149470708-149472106 |
| 16751 | Magel2 | NM_013779.2 | chr7:69521864-69526526 |
| 16752 | Magi1 | NM_001029850.4 | chr6:93625446-94233911 |
| 16753 | Magi1 | NM_001083320.2 | chr6:93625446-94233911 |
| 16754 | Magi1 | NM_001083321.2 | chr6:93625446-94233911 |
| 16755 | Magi1 | NM_001286784.1 | chr6:93625446-94233911 |
| 16756 | Magi1 | NM_001286785.1 | chr6:93625446-94233911 |
| 16757 | Magi1 | NM_001286786.1 | chr6:93625446-94233911 |
| 16758 | Magi1 | NM_001286788.1 | chr6:93625446-94233911 |
| 16759 | Magi1 | NM_010367.3 | chr6:93625446-94233911 |
| 16760 | Magi1 | NR_104594.1 | chr6:93625446-94233911 |
| 16761 | Magi2 | NM_001170745.1 | chr5:18732863-20210610 |
| 16762 | Magi2 | NM_001170746.1 | chr5:18732863-20210610 |
| 16763 | Magi2 | NM_015823.3 | chr5:18732863-20210610 |
| 16764 | Magi3 | NM_001159354.1 | chr3:103817187-104024329 |
| 16765 | Magi3 | NM_133853.3 | chr3:103817187-104024329 |
| 16766 | Magix | NM_018832.2 | chrX:7250291-7258377 |
| 16767 | Magix | NR_037581.1 | chrX:7250291-7258377 |
| 16768 | Magoh | NM_001282737.1 | chr4:107552359-107560029 |
| 16769 | Magoh | NM_010760.1 | chr4:107552359-107560029 |
| 16770 | Magohb | NM_025564.2 | chr6:131234406-131243262 |
| 16771 | Magt1 | NM_001190409.1 | chrX:103163423-103207238 |
| 16772 | Magt1 | NM_025952.4 | chrX:103163423-103207238 |
| 16773 | Mak | NM_001145802.1 | chr13:41120488-41175075 |
| 16774 | Mak | NM_001145803.1 | chr13:41120488-41175075 |
| 16775 | Mak | NM_008547.2 | chr13:41120488-41175075 |
| 16776 | Mak16 | NM_026453.3 | chr8:32269940-32279196 |
| 16777 | Mal | NM_001171187.1 | chr2:127458961-127482431 |
| 16778 | Mal | NM_010762.5 | chr2:127458961-127482431 |
| 16779 | Mal2 | NM_178920.4 | chr15:54402920-54434401 |
| 16780 | Malat1 | NR_002847.2 | chr19:5795689-5802671 |
| 16781 | Mall | NM_145532.3 | chr2:127530125-127555633 |
| 16782 | Malsu1 | NM_029353.1 | chr6:49023793-49034716 |
| 16783 | Malt1 | NM_172833.2 | chr18:65590650-65638446 |
| 16784 | Mamdc2 | NM_174857.3 | chr19:23377098-23522812 |
| 16785 | Mamdc4 | NM_001081199.1 | chr2:25418634-25426836 |
| 16786 | Maml1 | NM_175334.3 | chr11:50069136-50105838 |
| 16787 | Maml2 | NM_001013813.3 | chr9:13424432-13513977 |
| 16788 | Maml2 | NM_173776.3 | chr9:13424432-13513977 |
| 16789 | Maml3 | NM_001004176.2 | chr3:51491534-51908928 |
| 16790 | Mamld1 | NM_001081354.2 | chrX:68303430-68407892 |
| 16791 | Mamld1 | NM_001256048.1 | chrX:68303430-68407892 |
| 16792 | Mamstr | NM_172418.2 | chr7:52895346-52901138 |
| 16793 | Man1a | NM_008548.4 | chr10:53625838-53795602 |
| 16794 | Man1a2 | NM_010763.2 | chr3:100366126-100489396 |
| 16795 | Man1b1 | NM_001029985.3 | chr2:25188262-25207733 |
| 16796 | Man1c1 | NM_207237.3 | chr4:134117605-134260205 |
| 16797 | Man2a1 | NM_008549.2 | chr17:64950988-65104450 |
| 16798 | Man2a2 | NM_172903.4 | chr7:87493982-87516261 |
| 16799 | Man2b1 | NM_010764.2 | chr8:87607167-87622638 |
| 16800 | Man2b2 | NM_008550.2 | chr5:37198051-37221888 |
| 16801 | Man2c1 | NM_028636.2 | chr9:56978584-56990017 |
| 16802 | Man2c1os | NR_102289.1 | chr9:56977789-56979097 |
| 16803 | Manba | NM_027288.2 | chr3:135148574-135234367 |
| 16804 | Manbal | NM_026968.3 | chr2:157193329-157222499 |
| 16805 | Manea | NM_172865.2 | chr4:26251652-26273799 |
| 16806 | Maneal | NM_001007573.2 | chr4:124532483-124539415 |
| 16807 | Manf | NM_029103.3 | chr9:106789745-106794269 |
| 16808 | Manr | NR_110437.1 | chr3:29789938-29823113 |
| 16809 | Mansc1 | NM_026345.4 | chr6:134659224-134582506 |
| 16810 | Mansc4 | NM_001034903.3 | chr6:147023583-147035554 |
| 16811 | Maoa | NM_173740.1 | chrX:16196823-16264938 |
| 16812 | Maob | NM_172778.2 | chrX:16286406-16394492 |
| 16813 | Map10 | NM_028908.3 | chr1:128193717-128197265 |
| 16814 | Map1a | NM_001173506.1 | chr2:121115337-121176749 |
| 16815 | Map1a | NM_032393.2 | chr2:121115337-121176749 |
| 16816 | Map1b | NM_008634.2 | chr13:100191418-100286557 |
| 16817 | Map1lc3a | NM_025735.3 | chr2:155102099-155103809 |
| 16818 | Map1lc3a | NR_046364.1 | chr2:155102099-155103809 |
| 16819 | Map1lc3b | NM_026160.4 | chr8:124114367-124121947 |
| 16820 | Map1s | NM_173013.3 | chr8:73429872-73441428 |
| 16821 | Map2 | NM_001039934.1 | chr1:66221902-66489157 |
| 16822 | Map2 | NM_008632.2 | chr1:66221902-66489157 |
| 16823 | Map2k1 | NM_008927.3 | chr9:64036600-64101412 |
| 16824 | Map2k2 | NM_023138.4 | chr10:80568691-80587442 |
| 16825 | Map2k3 | NM_008928.4 | chr11:60745558-60766305 |
| 16826 | Map2k3os | NR_027800.1 | chr11:60734442-60745369 |
| 16827 | Map2k4 | NM_009157.4 | chr11:65501746-65601799 |
| 16828 | Map2k5 | NM_011840.2 | chr9:63011576-63225659 |
| 16829 | Map2k6 | NM_011943.2 | chr11:110260435-110374951 |
| 16830 | Map2k7 | NM_001042557.2 | chr8:4238739-4247897 |
| 16831 | Map2k7 | NM_001164172.1 | chr8:4238739-4247897 |
| 16832 | Map2k7 | NM_001291777.1 | chr8:4238739-4247897 |
| 16833 | Map2k7 | NM_001291778.1 | chr8:4238739-4247897 |
| 16834 | Map2k7 | NM_001291783.1 | chr8:4238739-4247897 |
| 16835 | Map2k7 | NM_011944.3 | chr8:4238739-4247897 |
| 16836 | Map3k1 | NM_011945.2 | chr13:112536642-112599191 |
| 16837 | Map3k10 | NM_001081292.1 | chr7:28441393-28459617 |
| 16838 | Map3k10 | NM_001290528.1 | chr7:28441393-28459617 |
| 16839 | Map3k11 | NM_022012.3 | chr19:5689130-5702864 |
| 16840 | Map3k12 | NM_001163643.1 | chr15:102301062-102347435 |
| 16841 | Map3k12 | NM_009582.4 | chr15:102301062-102347435 |
| 16842 | Map3k13 | NM_172821.3 | chr16:21892041-21931950 |

Fig. 25 - 90

| | | | | | | | | |
|---|---|---|---|---|---|---|---|---|
| 16843 | Map3k14 | NM_016896.3 | chr11:103081077-103128715 | 16938 | Mapt | NM_010838.4 | chr11:104092749-104193403 |
| 16844 | Map3k15 | NM_001163085.2 | chrX:156426365-156561283 | 16939 | Marc1 | NM_001290273.1 | chr1:186610645-186635179 |
| 16845 | Map3k19 | NM_011737.1 | chr1:129711847-129736867 | 16940 | Marc2 | NM_133684.3 | chr1:186636946-186669726 |
| 16846 | Map3k2 | NM_011946.3 | chr18:32322742-32396405 | 16941 | March1 | NM_001166372.1 | chr8:68141938-68995536 |
| 16847 | Map3k3 | NM_011947.3 | chr11:105946215-106016748 | 16942 | March1 | NM_001166375.1 | chr8:68141938-68995536 |
| 16848 | Map3k4 | NM_011948.2 | chr17:12420486-12511526 | 16943 | March1 | NM_175188.4 | chr8:68141938-68995536 |
| 16849 | Map3k5 | NM_008580.4 | chr10:19654331-19862556 | 16944 | March10 | NM_001039242.2 | chr11:105222111-105318049 |
| 16850 | Map3k6 | NM_016693.5 | chr4:132796732-132808843 | 16945 | March10 | NM_172568.2 | chr11:105222111-105318049 |
| 16851 | Map3k7 | NM_009316.1 | chr4:32051081-32110441 | 16946 | March11 | NM_177597.5 | chr15:26238826-26339328 |
| 16852 | Map3k7 | NM_172688.3 | chr4:32051081-32110441 | 16947 | March2 | NM_001252480.1 | chr17:33822636-33855622 |
| 16853 | Map3k7cl | NM_144854.2 | chr16:87553574-87595581 | 16948 | March2 | NM_145486.5 | chr17:33822636-33855622 |
| 16854 | Map3k8 | NM_007746.2 | chr18:4331324-4352951 | 16949 | March2 | NR_045522.1 | chr17:33822636-33855622 |
| 16855 | Map3k9 | NM_001174107.1 | chr12:82815936-82882157 | 16950 | March2 | NR_045523.1 | chr17:33822636-33855622 |
| 16856 | Map3k9 | NM_177395.5 | chr12:82815936-82882157 | 16951 | March3 | NM_177115.2 | chr18:56921369-57085202 |
| 16857 | Map4 | NM_001205330.1 | chr9:109834277-109986458 | 16952 | March4 | NM_001045533.1 | chr1:72473685-72583138 |
| 16858 | Map4 | NM_001205331.1 | chr9:109834277-109986458 | 16953 | March5 | NM_001164336.1 | chr19:37282034-37298947 |
| 16859 | Map4 | NM_001205332.1 | chr9:109834277-109986458 | 16954 | March5 | NM_001164337.1 | chr19:37282034-37298947 |
| 16860 | Map4 | NM_008633.4 | chr9:109834277-109986458 | 16955 | March5 | NM_027314.3 | chr19:37282034-37298947 |
| 16861 | Map4k1 | NM_008279.2 | chr7:29767872-29788297 | 16956 | March6 | NM_172606.2 | chr15:31385653-31460792 |
| 16862 | Map4k2 | NM_001291787.1 | chr19:6341159-6355619 | 16957 | March7 | NM_020575.2 | chr2:60047992-60086442 |
| 16863 | Map4k2 | NM_009006.3 | chr19:6341159-6355619 | 16958 | March8 | NM_027920.5 | chr6:116288140-116359558 |
| 16864 | Map4k2 | NR_117093.1 | chr19:6341159-6355619 | 16959 | March9 | NM_001033262.2 | chr10:126493105-126497240 |
| 16865 | Map4k3 | NM_001290345.1 | chr17:80979852-81127365 | 16960 | Marcks | NM_008538.2 | chr10:36853048-36858732 |
| 16866 | Map4k4 | NM_001252200.1 | chr1:39957757-40083155 | 16961 | Marcksl1 | NM_010807.4 | chr4:129190824-129193225 |
| 16867 | Map4k4 | NM_001252201.1 | chr1:39957757-40083155 | 16962 | Marcksl1-ps4 | NR_028405.1 | chr13:4247980-4249023 |
| 16868 | Map4k4 | NM_001252202.1 | chr1:39957757-40083155 | 16963 | Marco | NM_010766.2 | chr1:122371114-122401661 |
| 16869 | Map4k4 | NM_008696.2 | chr1:39957757-40083155 | 16964 | Marf1 | NM_001081154.2 | chr16:14109258-14159367 |
| 16870 | Map4k5 | NM_201519.2 | chr2:70904744-70994150 | 16965 | Mark1 | NM_145515.2 | chr1:186823428 |
| 16871 | Map6 | NM_001043355.2 | chr7:106415956-106485647 | 16966 | Mark2 | NM_001080388.2 | chr19:7349885-7416350 |
| 16872 | Map6 | NM_001048167.1 | chr7:106415956-106485647 | 16967 | Mark2 | NM_001080389.1 | chr19:7349885-7416350 |
| 16873 | Map6 | NM_010873.3 | chr7:106415956-106485647 | 16968 | Mark2 | NM_001080390.1 | chr19:7349885-7416350 |
| 16874 | Map6d1 | NM_198599.2 | chr16:20233381-20241431 | 16969 | Mark2 | NM_007928.3 | chr19:7349885-7416350 |
| 16875 | Map7 | NM_001198635.1 | chr10:19868725-20001396 | 16970 | Mark3 | NM_021516.4 | chr12:112812720-112894438 |
| 16876 | Map7 | NM_008635.2 | chr10:19868725-20001396 | 16971 | Mark3 | NM_022801.4 | chr12:112812720-112894438 |
| 16877 | Map7d1 | NM_001145970.1 | chr4:125909411-125933563 | 16972 | Mark4 | NM_172279.3 | chr7:20011423-20043843 |
| 16878 | Map7d1 | NM_144941.3 | chr4:125909411-125933563 | 16973 | Mars | NM_001003913.2 | chr10:126727848-126748842 |
| 16879 | Map7d2 | NM_001081124.1 | chrX:155852509-155936879 | 16974 | Mars | NM_001171582.1 | chr10:126727848-126748842 |
| 16880 | Map9 | NM_001081230.1 | chr3:82161993-82199190 | 16975 | Mars2 | NM_175439.3 | chr1:55294020-55296902 |
| 16881 | Mapk1 | NM_001038663.1 | chr16:16983474-17047546 | 16976 | Marveld1 | NM_183195.2 | chr19:42221878-42226193 |
| 16882 | Mapk1 | NM_011949.3 | chr16:16983474-17047546 | 16977 | Marveld2 | NM_001038602.3 | chr13:101365911-101386926 |
| 16883 | Mapk10 | NM_001081567.1 | chr5:103336966-103640353 | 16978 | Marveld2 | NM_178410.3 | chr13:101365911-101386926 |
| 16884 | Mapk10 | NM_009158.2 | chr5:103336966-103640353 | 16979 | Marveld3 | NM_028584.3 | chr8:112471808-112486105 |
| 16885 | Mapk11 | NM_011161.5 | chr15:88972913-88980036 | 16980 | Marveld3 | NM_212447.2 | chr8:112471808-112486105 |
| 16886 | Mapk12 | NM_013871.3 | chr15:88961013-88971133 | 16981 | Mas1 | NM_008552.4 | chr17:13033871-13061009 |
| 16887 | Mapk13 | NM_011950.2 | chr17:28906261-28915649 | 16982 | Masp1 | NM_008555.1 | chr16:23451857-23520663 |
| 16888 | Mapk14 | NM_001168508.1 | chr17:28828286-28885350 | 16983 | Masp2 | NM_001003893.2 | chr4:147976652-148001105 |
| 16889 | Mapk14 | NM_001168513.1 | chr17:28828286-28885350 | 16984 | Masp2 | NM_010767.3 | chr4:147976652-148001105 |
| 16890 | Mapk14 | NM_001168514.1 | chr17:28828286-28885350 | 16985 | Mast1 | NM_019945.2 | chr8:87435752-87461252 |
| 16891 | Mapk14 | NM_011951.1 | chr17:28828286-28885350 | 16986 | Mast2 | NM_001042743.2 | chr4:115979364-116136786 |
| 16892 | Mapk15 | NM_177922.2 | chr15:75824198-75829583 | 16987 | Mast2 | NM_008641.3 | chr4:115979364-116136786 |
| 16893 | Mapk1ip1 | NM_001045443.1 | chr7:146027500-146037950 | 16988 | Mast3 | NM_199308.2 | chr8:73302015-73316332 |
| 16894 | Mapk1ip1 | NM_027115.2 | chr7:146027500-146037950 | 16989 | Mast4 | NM_175171.3 | chr13:103522568-104124572 |
| 16895 | Mapk1ip1l | NM_178684.5 | chr14:47917988-47942766 | 16990 | Mastl | NM_025979.4 | chr2:22972063-23011544 |
| 16896 | Mapk3 | NM_011952.2 | chr7:133903139-133909330 | 16991 | Mat1a | NM_133653.3 | chr14:41918321-41937717 |
| 16897 | Mapk4 | NM_172632.2 | chr18:74088141-74224603 | 16992 | Mat2a | NM_145569.4 | chr6:72382793-72389552 |
| 16898 | Mapk6 | NM_015806.5 | chr9:75234588-75257823 | 16993 | Mat2b | NM_001199274.1 | chr11:40492815-40508705 |
| 16899 | Mapk6 | NM_027418.2 | chr9:75234588-75257823 | 16994 | Mat2b | NM_134017.2 | chr11:40492815-40508705 |
| 16900 | Mapk7 | NM_001291033.1 | chr11:61302313-61307768 | 16995 | Matk | NM_001285853.1 | chr10:80715679-80725726 |
| 16901 | Mapk7 | NM_001291034.1 | chr11:61302313-61307768 | 16996 | Matk | NM_001285854.1 | chr10:80715679-80725726 |
| 16902 | Mapk7 | NM_001291035.1 | chr11:61302313-61307768 | 16997 | Matk | NM_001285855.1 | chr10:80715679-80725726 |
| 16903 | Mapk7 | NM_001291036.1 | chr11:61302313-61307768 | 16998 | Matk | NM_010768.2 | chr10:80715679-80725726 |
| 16904 | Mapk7 | NM_001291037.1 | chr11:61302313-61307768 | 16999 | Matn1 | NM_010769.2 | chr4:130500299-130513391 |
| 16905 | Mapk7 | NM_011841.2 | chr11:61302313-61307768 | 17000 | Matn2 | NM_016762.2 | chr15:34236436-34365995 |
| 16906 | Mapk8 | NM_016700.4 | chr14:34191083-34260344 | 17001 | Matn3 | NM_010770.4 | chr12:8954734-8978834 |
| 16907 | Mapk8ip1 | NM_001202445.1 | chr2:92223832-92241420 | 17002 | Matn4 | NM_001252563.1 | chr2:164215128-164240948 |
| 16908 | Mapk8ip1 | NM_001202446.1 | chr2:92223832-92241420 | 17003 | Matn4 | NM_013592.4 | chr2:164215128-164240948 |
| 16909 | Mapk8ip1 | NM_011162.5 | chr2:92223832-92241420 | 17004 | Matr3 | NM_010771.6 | chr18:35721811-35751699 |
| 16910 | Mapk8ip2 | NM_021921.3 | chr15:89284341-89292878 | 17005 | Mau2 | NM_001167939.1 | chr8:72540021-72566633 |
| 16911 | Mapk8ip3 | NM_001163447.1 | chr17:25033444-25073922 | 17006 | Mau2 | NM_028993.4 | chr8:72540021-72566633 |
| 16912 | Mapk8ip3 | NM_001163448.1 | chr17:25033444-25073922 | 17007 | Mavs | NM_001206382.1 | chr2:131059798-131073760 |
| 16913 | Mapk8ip3 | NM_001163449.1 | chr17:25033444-25073922 | 17008 | Mavs | NM_001206383.1 | chr2:131059798-131073760 |
| 16914 | Mapk8ip3 | NM_001163450.1 | chr17:25033444-25073922 | 17009 | Mavs | NM_001206385.1 | chr2:131059798-131073760 |
| 16915 | Mapk8ip3 | NM_001163451.1 | chr17:25033444-25073922 | 17010 | Mavs | NM_144888.2 | chr2:131059798-131073760 |
| 16916 | Mapk8ip3 | NM_001163453.1 | chr17:25033444-25073922 | 17011 | Max | NM_001146176.1 | chr12:78038255-78063235 |
| 16917 | Mapk8ip3 | NM_013931.4 | chr17:25033444-25073922 | 17012 | Max | NM_008558.2 | chr12:78038255-78063235 |
| 16918 | Mapk9 | NM_001163671.1 | chr11:49660252-49699923 | 17013 | Maz | NM_010772.1 | chr7:134165650-134169993 |
| 16919 | Mapk9 | NM_001163672.1 | chr11:49660252-49699923 | 17014 | Mb | NM_001164047.1 | chr15:76845916-76887538 |
| 16920 | Mapk9 | NM_016961.3 | chr11:49660252-49699923 | 17015 | Mb | NM_001164048.1 | chr15:76845916-76887538 |
| 16921 | Mapk9 | NM_207692.2 | chr11:49660252-49699923 | 17016 | Mb | NM_013593.3 | chr15:76845916-76887538 |
| 16922 | Mapkap1 | NM_001290625.1 | chr2:34262290-34480478 | 17017 | Mb21d1 | NM_173386.5 | chr9:78278324-78290954 |
| 16923 | Mapkap1 | NM_001290626.1 | chr2:34262290-34480478 | 17018 | Mb21d2 | NM_177718.3 | chr16:28826261-28929784 |
| 16924 | Mapkap1 | NM_177345.4 | chr2:34262290-34480478 | 17019 | Mbd1 | NM_013594.2 | chr18:74427941-74442338 |
| 16925 | Mapkapk2 | NM_008551.1 | chr1:132950280-132994120 | 17020 | Mbd2 | NM_010773.2 | chr18:70727945-70785785 |
| 16926 | Mapkapk3 | NM_178907.3 | chr9:107157257-107192208 | 17021 | Mbd3 | NM_013595.3 | chr10:79855285-79862224 |
| 16927 | Mapkapk5 | NM_010765.2 | chr5:121975059-121995901 | 17022 | Mbd3l1 | NM_028557.2 | chr9:18282838-18289736 |
| 16928 | Mapkbp1 | NM_011941.3 | chr2:119798435-119853139 | 17023 | Mbd3l2 | NM_144934.3 | chr9:18235058-18250760 |
| 16929 | Mapre1 | NM_007896.3 | chr2:153567022-153599050 | 17024 | Mbd4 | NM_010774.2 | chr6:115790714-115803359 |
| 16930 | Mapre2 | NM_001162941.1 | chr18:23910833-24052362 | 17025 | Mbd5 | NM_001290656.1 | chr2:48805027-49172589 |
| 16931 | Mapre2 | NM_001162942.1 | chr18:23910833-24052362 | 17026 | Mbd5 | NM_029924.2 | chr2:48805027-49172589 |
| 16932 | Mapre3 | NM_153058.4 | chr18:23910833-24052362 | 17027 | Mbd6 | NM_033072.2 | chr10:126719012-126725827 |
| 16933 | Mapre3 | NM_133350.1 | chr5:31117128-31166479 | 17028 | Mbip | NM_145442.5 | chr12:57429293-57446881 |
| 16934 | Mapt | NM_001038609.2 | chr11:104092749-104193403 | 17029 | Mbl1 | NM_010775.2 | chr14:41964744-41972248 |
| 16935 | Mapt | NM_001285454.1 | chr11:104092749-104193403 | 17030 | Mbl2 | NM_010776.1 | chr19:30307446-30314172 |
| 16936 | Mapt | NM_001285455.1 | chr11:104092749-104193403 | 17031 | Mblac1 | NM_177878.3 | chr5:138635541-138636849 |
| 16937 | Mapt | NM_001285456.1 | chr11:104092749-104193403 | 17032 | Mblac2 | NM_028372.1 | chr13:81850415-81892274 |

Fig. 25 - 91

| | | | | | | | | |
|---|---|---|---|---|---|---|---|---|
| 17033 | Mbnl1 | NM_001253708.1 | chr3:60276751-60433670 | | 17128 | Mdh1b | NM_029696.4 | chr1:63745400-63776892 |
| 17034 | Mbnl1 | NM_001253709.1 | chr3:60276751-60433670 | | 17129 | Mdh2 | NM_008617.2 | chr5:136254518-136266256 |
| 17035 | Mbnl1 | NM_001253710.1 | chr3:60276751-60433670 | | 17130 | Mdk | NM_001012335.2 | chr2:91762345-91772454 |
| 17036 | Mbnl1 | NM_001253711.1 | chr3:60276751-60433670 | | 17131 | Mdk | NM_001012336.2 | chr2:91762345-91772454 |
| 17037 | Mbnl1 | NM_001253713.1 | chr3:60276751-60433670 | | 17132 | Mdk | NM_001291481.1 | chr2:91762345-91772454 |
| 17038 | Mbnl1 | NM_020007.3 | chr3:60276751-60433670 | | 17133 | Mdk | NM_001291482.1 | chr2:91762345-91772454 |
| 17039 | Mbnl2 | NM_175341.4 | chr14:120674890-120830920 | | 17134 | Mdk | NM_001291483.1 | chr2:91762345-91772454 |
| 17040 | Mbnl2 | NM_207515.2 | chr14:120674890-120830920 | | 17135 | Mdk | NM_010784.5 | chr2:91762345-91772454 |
| 17041 | Mbnl3 | NM_134163.4 | chrX:48466670-48559009 | | 17136 | Mdm1 | NM_001162904.1 | chr10:117578842-117606055 |
| 17042 | Mboat1 | NM_153546.4 | chr13:30228358-30338563 | | 17137 | Mdm1 | NM_001162905.1 | chr10:117578842-117606055 |
| 17043 | Mboat2 | NM_001083341.1 | chr12:25516463-25645164 | | 17138 | Mdm1 | NM_010785.2 | chr10:117578842-117606055 |
| 17044 | Mboat2 | NM_026037.3 | chr12:25516463-25645164 | | 17139 | Mdm1 | NM_148922.3 | chr10:117578842-117606055 |
| 17045 | Mboat4 | NM_001126314.2 | chr8:35178089-35188239 | | 17140 | Mdm2 | NM_001288586.1 | chr10:117125930-117147814 |
| 17046 | Mboat7 | NM_029934.3 | chr7:3629390-3645127 | | 17141 | Mdm2 | NM_010786.4 | chr10:117125930-117147814 |
| 17047 | Mbp | NM_001025245.1 | chr18:82644514-82755029 | | 17142 | Mdm4 | NM_008575.4 | chr1:134886421-134921925 |
| 17048 | Mbp | NM_001025251.2 | chr18:82644514-82755029 | | 17143 | Mdn1 | NM_001081392.1 | chr4:32744093-32862192 |
| 17049 | Mbp | NM_001025254.2 | chr18:82644514-82755029 | | 17144 | Mdp1 | NM_023397.4 | chr14:56276715-56279345 |
| 17050 | Mbp | NM_001025255.2 | chr18:82644514-82755029 | | 17145 | Mdp1 | NR_028316.1 | chr14:56276715-56279345 |
| 17051 | Mbp | NM_001025256.2 | chr18:82644514-82755029 | | 17146 | Me1 | NM_001198933.1 | chr9:86474969-86595286 |
| 17052 | Mbp | NM_001025258.2 | chr18:82644514-82755029 | | 17147 | Me1 | NM_008615.2 | chr9:86474969-86595286 |
| 17053 | Mbp | NM_001025259.2 | chr18:82644514-82755029 | | 17148 | Me2 | NM_145494.2 | chr18:73929693-73975046 |
| 17054 | Mbp | NM_010777.3 | chr18:82644514-82755029 | | 17149 | Me3 | NM_181407.4 | chr7:96781327-97002869 |
| 17055 | Mbtd1 | NM_134012.3 | chr11:93747532-93808298 | | 17150 | Mea1 | NM_001277309.1 | chr17:46811499-46841951 |
| 17056 | Mbtps1 | NM_001167910.1 | chr8:122032051-122082661 | | 17151 | Mea1 | NM_001277310.1 | chr17:46811499-46841951 |
| 17057 | Mbtps1 | NM_019709.4 | chr8:122032051-122082661 | | 17152 | Mea1 | NM_001277311.1 | chr17:46811499-46841951 |
| 17058 | Mbtps2 | NM_172307.3 | chrX:153985754-154036647 | | 17153 | Mea1 | NM_001277312.1 | chr17:46811499-46841951 |
| 17059 | Mc1r | NM_008559.2 | chr8:125930981-125934647 | | 17154 | Mea1 | NM_010787.2 | chr17:46811499-46841951 |
| 17060 | Mc2r | NM_001271716.1 | chr18:68566552-68588974 | | 17155 | Mea1 | NR_102392.1 | chr17:46811499-46841951 |
| 17061 | Mc2r | NM_001271717.1 | chr18:68566552-68588974 | | 17156 | Meaf6 | NM_001290701.1 | chr4:124762377-124787314 |
| 17062 | Mc2r | NM_008560.3 | chr18:68566552-68588974 | | 17157 | Meaf6 | NM_027310.4 | chr4:124762377-124787314 |
| 17063 | Mc3r | NM_008561.3 | chr2:172073991-172076614 | | 17158 | Mecom | NM_007963.2 | chr3:29850217-29912126 |
| 17064 | Mc4r | NM_016977.4 | chr18:67017358-67020141 | | 17159 | Mecom | NM_021442.2 | chr3:30135490-30408409 |
| 17065 | Mc5r | NM_013596.2 | chr18:68497256-68499365 | | 17160 | Mecp2 | NM_001081979.2 | chrX:71272160-71330975 |
| 17066 | Mcam | NM_023061.2 | chr9:43942740-43950809 | | 17161 | Mecp2 | NM_010788.4 | chrX:71272160-71330975 |
| 17067 | Mcat | NM_001030014.2 | chr15:83377226-83386141 | | 17162 | Mecr | NM_025297.2 | chr4:131399385-131423702 |
| 17068 | Mcc | NM_001085373.1 | chr18:44584713-44971836 | | 17163 | Med1 | NM_001080118.1 | chr11:98013468-98054607 |
| 17069 | Mcc | NM_001085374.1 | chr18:44584713-44971836 | | 17164 | Med1 | NM_013634.4 | chr11:98013468-98054607 |
| 17070 | Mccc1 | NM_023644.4 | chr3:35858231-35899600 | | 17165 | Med1 | NM_134027.2 | chr11:98013468-98054607 |
| 17071 | Mccc1os | NR_029464.1 | chr3:35898835-35907750 | | 17166 | Med10 | NM_138563.2 | chr13:69948759-69954972 |
| 17072 | Mccc2 | NM_030026.2 | chr13:100718486-100785594 | | 17167 | Med11 | NM_025397.2 | chr11:70265432-70267228 |
| 17073 | Mcee | NM_028626.1 | chr7:71537656-71557005 | | 17168 | Med12 | NM_021521.2 | chrX:98469429-98494273 |
| 17074 | Mcemp1 | NM_026985.1 | chr8:3665761-3668905 | | 17169 | Med12l | NM_177855.3 | chr3:58810900-59122334 |
| 17075 | Mcf2 | NM_001289730.1 | chrX:57309132-57432266 | | 17170 | Med13 | NM_001080931.1 | chr11:86079216-86171027 |
| 17076 | Mcf2 | NM_001289731.1 | chrX:57309132-57432266 | | 17171 | Med13l | NM_172424.4 | chr5:119010727-119215446 |
| 17077 | Mcf2 | NM_133197.4 | chrX:57309132-57432266 | | 17172 | Med14 | NM_001048208.1 | chrX:12252496-12339099 |
| 17078 | Mcf2l | NM_001159485.1 | chr8:12915892-13020509 | | 17173 | Med14 | NM_012005.3 | chrX:12252496-12339099 |
| 17079 | Mcf2l | NM_001159486.1 | chr8:12915892-13020509 | | 17174 | Med15 | NM_001040683.2 | chr16:17651300-17723040 |
| 17080 | Mcf2l | NM_178076.3 | chr8:12915892-13020509 | | 17175 | Med15 | NM_001285884.1 | chr16:17651300-17723040 |
| 17081 | Mcfd2 | NM_139295.3 | chr17:87653782-87665287 | | 17176 | Med15 | NM_001285886.1 | chr16:17651300-17723040 |
| 17082 | Mcfd2 | NM_176808.5 | chr17:87653782-87665287 | | 17177 | Med15 | NM_033609.3 | chr16:17651300-17723040 |
| 17083 | Mchr1 | NM_145132.2 | chr15:81065928-81069394 | | 17178 | Med16 | NM_001163276.1 | chr10:79357451-79371683 |
| 17084 | Mcidas | NM_001037914.3 | chr13:113784075-113790602 | | 17179 | Med16 | NM_198107.2 | chr10:79357451-79371683 |
| 17085 | Mcl1 | NM_008562.3 | chr3:95462642-95467101 | | 17180 | Med17 | NM_144933.1 | chr14:56079216-56094311 |
| 17086 | Mcm10 | NM_027290.3 | chr2:4911769-4933837 | | 17181 | Med18 | NM_026039.3 | chr4:132014643-132019836 |
| 17087 | Mcm2 | NM_008564.2 | chr6:88833467-88848774 | | 17182 | Med19 | NM_025885.2 | chr2:84518559-84528372 |
| 17088 | Mcm3 | NM_008563.2 | chr1:20793094-20810294 | | 17183 | Med20 | NM_020048.3 | chr17:47748544-47761367 |
| 17089 | Mcm3ap | NM_019434.2 | chr10:75931716-75978602 | | 17184 | Med21 | NM_025315.3 | chr6:146591101-146599122 |
| 17090 | Mcm4 | NM_008565.3 | chr16:15623989-15637493 | | 17185 | Med22 | NM_001033908.1 | chr2:26760786-26766162 |
| 17091 | Mcm5 | NM_008566.3 | chr8:77633426-77652938 | | 17186 | Med22 | NM_011513.2 | chr2:26760786-26766162 |
| 17092 | Mcm6 | NM_008567.1 | chr1:130228167-130256233 | | 17187 | Med23 | NM_001166416.1 | chr10:24589791-24633335 |
| 17093 | Mcm7 | NM_008568.2 | chr5:138605817-138613090 | | 17188 | Med23 | NM_027347.3 | chr10:24589791-24633335 |
| 17094 | Mcm8 | NM_001291054.1 | chr2:132641876-132669924 | | 17189 | Med24 | NM_011869.2 | chr11:98565904-98590749 |
| 17095 | Mcm8 | NM_025676.4 | chr2:132641876-132669924 | | 17190 | Med25 | NM_029365.2 | chr7:52134755-52147736 |
| 17096 | Mcm9 | NM_027830.2 | chr10:53257130-53350245 | | 17191 | Med26 | NM_027485.4 | chr8:75018457-75072209 |
| 17097 | Mcmbp | NM_145955.3 | chr7:135839972-135883943 | | 17192 | Med27 | NM_001290489.1 | chr2:29202329-29380310 |
| 17098 | Mcmdc2 | NM_177722.3 | chr1:9898718-9931035 | | 17193 | Med27 | NM_026896.5 | chr2:29202329-29380310 |
| 17099 | Mcoln1 | NM_053177.1 | chr8:3500518-3515231 | | 17194 | Med27 | NM_029615.1 | chr2:29202329-29380310 |
| 17100 | Mcoln2 | NM_001005846.2 | chr3:145812796-145858476 | | 17195 | Med28 | NM_025895.4 | chr5:45911467-45920523 |
| 17101 | Mcoln2 | NM_026656.4 | chr3:145812796-145858476 | | 17196 | Med29 | NM_026042.3 | chr7:29170265-29177709 |
| 17102 | Mcoln3 | NM_134140.3 | chr3:145784754-145803610 | | 17197 | Med30 | NM_027212.2 | chr15:52543999-52561986 |
| 17103 | Mcph1 | NM_173189.2 | chr8:18595173-18803188 | | 17198 | Med31 | NM_026068.2 | chr11:72025226-72029094 |
| 17104 | Mcpt1 | NM_008570.1 | chr14:56636800-56639228 | | 17199 | Med4 | NM_026119.3 | chr14:73909855-73918352 |
| 17105 | Mcpt2 | NM_008571.1 | chr14:56660969-56663471 | | 17200 | Med6 | NM_027213.2 | chr12:82674550-82695945 |
| 17106 | Mcpt4 | NM_010779.2 | chr14:56678580-56681147 | | 17201 | Med7 | NM_001104530.1 | chr11:46250448-46256223 |
| 17107 | Mcpt8 | NM_008572.1 | chr14:56701000-56704034 | | 17202 | Med7 | NM_001104556.1 | chr11:46250448-46256223 |
| 17108 | Mcpt9 | NM_010782.3 | chr14:56645780-56649332 | | 17203 | Med7 | NM_001104557.1 | chr11:46250448-46256223 |
| 17109 | Mcpt-ps1 | NR_028284.1 | chr14:56568645-56571208 | | 17204 | Med7 | NM_025426.3 | chr11:46250448-46256223 |
| 17110 | Mcrs1 | NM_001164156.1 | chr15:99055406-99092472 | | 17205 | Med8 | NM_001290688.1 | chr4:118081941-118088429 |
| 17111 | Mcrs1 | NM_016786.3 | chr15:99055406-99092472 | | 17206 | Med8 | NM_020000.3 | chr4:118081941-118088429 |
| 17112 | Mctp1 | NM_030174.2 | chr13:76522408-77171071 | | 17207 | Med8 | NM_173719.3 | chr4:118081941-118088429 |
| 17113 | Mctp2 | NM_001024703.1 | chr7:79222715-79451481 | | 17208 | Med9 | NM_026119.3 | chr11:59761716-59776808 |
| 17114 | Mcts1 | NM_026902.3 | chrX:35953894-35966699 | | 17209 | Med9os | NR_045273.1 | chr11:59760393-59761649 |
| 17115 | Mcts2 | NM_025543.2 | chr2:152512884-152513678 | | 17210 | Medag | NM_027519.3 | chr5:150214380-150234278 |
| 17116 | Mcu | NM_001033259.4 | chr10:58909731-59079440 | | 17211 | Mef2a | NM_001033713.2 | chr7:74376048-74517744 |
| 17117 | Mcur1 | NM_001001059.3 | chr13:43633774-43659560 | | 17212 | Mef2a | NM_001291191.1 | chr7:74376048-74517744 |
| 17118 | Mdc1 | NM_001010833.2 | chr17:35978442-35996615 | | 17213 | Mef2a | NM_001291195.1 | chr7:74376048-74517744 |
| 17119 | Mdfi | NM_001199973.2 | chr17:47952276-47971640 | | 17214 | Mef2a | NM_001291196.1 | chr7:74376048-74517744 |
| 17120 | Mdfi | NM_001276390.1 | chr17:47952276-47971640 | | 17215 | Mef2b | NM_001045484.1 | chr8:72676676-72691387 |
| 17121 | Mdfi | NM_001276391.1 | chr17:47952276-47971640 | | 17216 | Mef2b | NM_008578.2 | chr8:72676676-72691387 |
| 17122 | Mdfi | NM_010783.3 | chr17:47952276-47971640 | | 17217 | Mef2c | NM_001170537.1 | chr13:83643032-83806684 |
| 17123 | Mdfic | NM_175088.5 | chr6:15670660-15752169 | | 17218 | Mef2c | NM_025282.3 | chr13:83643032-83806684 |
| 17124 | Mdga1 | NM_001081160.1 | chr17:29964902-30024827 | | 17219 | Mef2d | NM_133665.3 | chr3:87946316-87973089 |
| 17125 | Mdga2 | NM_001193266.1 | chr12:67567045-68323536 | | 17220 | Mefv | NM_001161790.1 | chr16:3707214-3718124 |
| 17126 | Mdga2 | NM_207010.2 | chr12:67567045-68323536 | | 17221 | Mefv | NM_001161791.1 | chr16:3707214-3718124 |
| 17127 | Mdh1 | NM_008618.3 | chr11:21456694-21471937 | | 17222 | Mefv | NM_019453.2 | chr16:3707214-3718124 |

Fig. 25 - 92

| | | | |
|---|---|---|---|
| 17223 | Meg3 | NR_003633.3 | chr12:110779205-110809939 |
| 17224 | Meg3 | NR_027651.2 | chr12:110779205-110809939 |
| 17225 | Meg3 | NR_027652.1 | chr12:110779205-110809939 |
| 17226 | Megf10 | NM_001001979.2 | chr18:57292743-57457121 |
| 17227 | Megf11 | NM_001134399.1 | chr9:64233432-64557012 |
| 17228 | Megf11 | NM_172522.4 | chr9:64233432-64557012 |
| 17229 | Megf6 | NM_001162977.1 | chr4:153544821-153649830 |
| 17230 | Megf8 | NM_001160400.1 | chr7:26102182-26150936 |
| 17231 | Megf9 | NM_172694.2 | chr4:70092960-70195962 |
| 17232 | Mei1 | NM_028897.3 | chr15:81900546-81957244 |
| 17233 | Mei4 | NM_175213.3 | chr9:81757350-81921098 |
| 17234 | Meig1 | NM_008579.4 | chr2:3326314-3339920 |
| 17235 | Meiob | NM_029197.1 | chr17:24941326-24976732 |
| 17236 | Meis1 | NM_001193271.1 | chr11:18780430-18918972 |
| 17237 | Meis1 | NM_010789.3 | chr11:18780430-18918972 |
| 17238 | Meis2 | NM_001136072.2 | chr2:115686999-115890794 |
| 17239 | Meis2 | NM_001159567.1 | chr2:115686999-115890794 |
| 17240 | Meis2 | NM_001159568.1 | chr2:115686999-115890794 |
| 17241 | Meis2 | NM_001159569.1 | chr2:115686999-115890794 |
| 17242 | Meis2 | NM_001159570.1 | chr2:115686999-115890794 |
| 17243 | Meis2 | NM_010825.3 | chr2:115686999-115890794 |
| 17244 | Meis3 | NM_001277988.2 | chr7:16760673-16771852 |
| 17245 | Meis3 | NM_001277989.2 | chr7:16760673-16771852 |
| 17246 | Meis3 | NM_008627.4 | chr7:16760673-16771852 |
| 17247 | Meis3 | NR_102730.2 | chr7:16760673-16771852 |
| 17248 | Melk | NM_010790.2 | chr4:44313788-44377547 |
| 17249 | Memo1 | NM_133771.2 | chr17:74600039-74694203 |
| 17250 | Men1 | NM_001168488.1 | chr19:6334978-6340894 |
| 17251 | Men1 | NM_001168489.1 | chr19:6334978-6340894 |
| 17252 | Men1 | NM_001168490.1 | chr19:6334978-6340894 |
| 17253 | Men1 | NM_008583.2 | chr19:6334978-6340894 |
| 17254 | Meox1 | NM_010791.3 | chr11:101738823-101755668 |
| 17255 | Meox2 | NM_008584.3 | chr12:37835132-37906115 |
| 17256 | Mep1a | NM_008585.2 | chr17:43611277-43639722 |
| 17257 | Mep1b | NM_008586.2 | chr18:21230844-21258700 |
| 17258 | Mepce | NM_144913.3 | chr5:138223133-138227929 |
| 17259 | Mepe | NM_053172.2 | chr5:104754347-104767630 |
| 17260 | Mertk | NM_008587.1 | chr2:128524732-128627924 |
| 17261 | Mesdc1 | NM_030705.4 | chr7:91029004-91032851 |
| 17262 | Mesdc2 | NM_023403.3 | chr7:91040509-91050042 |
| 17263 | Mesp1 | NM_008588.2 | chr7:86937126-86938476 |
| 17264 | Mesp2 | NM_008589.2 | chr7:86955612-86958317 |
| 17265 | Mest | NM_001252292.1 | chr6:30683505-30846794 |
| 17266 | Mest | NM_001252293.1 | chr6:30683505-30846794 |
| 17267 | Mest | NM_008590.2 | chr6:30683505-30846794 |
| 17268 | Met | NM_008591.2 | chr6:17413956-17523980 |
| 17269 | Metap1 | NM_175224.4 | chr3:138121923-138152346 |
| 17270 | Metap1d | NM_025633.3 | chr2:71291394-71363248 |
| 17271 | Metap2 | NM_019648.3 | chr10:93321234-93353947 |
| 17272 | Metrn | NM_133719.2 | chr17:25931515-25933990 |
| 17273 | Metrnl | NM_144797.3 | chr11:121563740-121578703 |
| 17274 | Mettl1 | NM_010792.1 | chr10:126478987-126482517 |
| 17275 | Mettl10 | NM_028095.1 | chr7:140019143-140044330 |
| 17276 | Mettl11b | NM_001143956.1 | chr1:165633123-165655363 |
| 17277 | Mettl13 | NM_144877.1 | chr1:164463802-164478476 |
| 17278 | Mettl14 | NM_201638.2 | chr3:123071212-123088908 |
| 17279 | Mettl15 | NM_029790.3 | chr2:108932456-109118447 |
| 17280 | Mettl16 | NM_026197.3 | chr11:74584364-74632194 |
| 17281 | Mettl17 | NM_001029990.1 | chr14:52504516-52511643 |
| 17282 | Mettl18 | NM_027279.2 | chr1:165925075-165927374 |
| 17283 | Mettl2 | NM_172567.3 | chr11:104987738-105002460 |
| 17284 | Mettl20 | NM_001252094.1 | chr6:149090034-149099692 |
| 17285 | Mettl20 | NM_001252095.1 | chr6:149090034-149099692 |
| 17286 | Mettl20 | NM_001252096.1 | chr6:149090034-149099692 |
| 17287 | Mettl20 | NM_001252097.1 | chr6:149090034-149099692 |
| 17288 | Mettl20 | NM_177101.5 | chr6:149090034-149099692 |
| 17289 | Mettl21a | NM_025964.3 | chr1:64653053-64663742 |
| 17290 | Mettl21c | NM_001013799.1 | chr14:44066252-44076851 |
| 17291 | Mettl21e | NM_207281.3 | chr1:44260914-44275776 |
| 17292 | Mettl22 | NM_146124.1 | chr16:8470905-8490290 |
| 17293 | Mettl23 | NM_028865.3 | chr11:116704828-116711054 |
| 17294 | Mettl24 | NM_177793.3 | chr10:40403087-40530889 |
| 17295 | Mettl25 | NM_207522.2 | chr10:105200240-105278436 |
| 17296 | Mettl3 | NM_019721.1 | chr14:52914517-52924799 |
| 17297 | Mettl4 | NM_176917.4 | chr17:95126419-95149232 |
| 17298 | Mettl5 | NM_027334.3 | chr2:69699618-69723672 |
| 17299 | Mettl5 | NR_110977.1 | chr2:69699618-69723672 |
| 17300 | Mettl6 | NM_025907.3 | chr14:32291983-32306138 |
| 17301 | Mettl7a1 | NM_027334.3 | chr15:100135247-100144779 |
| 17302 | Mettl7a2 | NM_199477.2 | chr15:100183631-100192250 |
| 17303 | Mettl7a2Higd1c | NM_001024672.3 | chr15:100183631-100214866 |
| 17304 | Mettl7a3 | NM_001081471.1 | chr15:100165359-100170600 |
| 17305 | Mettl7b | NM_027853.2 | chr10:128395333-128398044 |
| 17306 | Mettl8 | NM_001110512.1 | chr2:70802619-70893663 |
| 17307 | Mettl8 | NM_145524.3 | chr2:70802619-70893663 |
| 17308 | Mettl9 | NM_021554.2 | chr7:128177959-128220349 |
| 17309 | Mex3a | NM_001009379.2 | chr3:88336317-88345316 |
| 17310 | Mex3b | NM_175366.3 | chr7:90015842-90020086 |
| 17311 | Mex3c | NM_001039214.4 | chr18:73732358-73752232 |
| 17312 | Mex3d | NM_198515.2 | chr10:79843099-79850396 |
| 17313 | Mfap1a | NM_026220.4 | chr2:121318416-121332392 |
| 17314 | Mfap1b | NM_001081975.3 | chr2:121287401-121299759 |
| 17315 | Mfap2 | NM_001161799.1 | chr4:140566338-140571899 |
| 17316 | Mfap2 | NM_008546.3 | chr4:140566338-140571899 |
| 17317 | Mfap3 | NM_145426.2 | chr11:57332166-57347319 |

| | | | |
|---|---|---|---|
| 17318 | Mfap3 | NM_180599.1 | chr11:57332166-57347319 |
| 17319 | Mfap3l | NM_001177881.1 | chr8:63111656-63155528 |
| 17320 | Mfap3l | NM_001177882.1 | chr8:63111656-63155528 |
| 17321 | Mfap3l | NM_027756.3 | chr8:63111656-63155528 |
| 17322 | Mfap4 | NM_029568.2 | chr11:61298945-61302206 |
| 17323 | Mfap5 | NM_015776.2 | chr6:122463693-122479305 |
| 17324 | Mff | NM_029409.2 | chr1:82721492-82748964 |
| 17325 | Mfge8 | NM_001045489.1 | chr7:86278653-86293946 |
| 17326 | Mfge8 | NM_008594.2 | chr7:86278653-86293946 |
| 17327 | Mfhas1 | NM_001081279.1 | chr8:36650852-36742503 |
| 17328 | Mfi2 | NM_013900.2 | chr16:31878895-31899105 |
| 17329 | Mfn1 | NM_024200.4 | chr3:32428403-32478147 |
| 17330 | Mfn2 | NM_001285920.1 | chr4:147247694-147279018 |
| 17331 | Mfn2 | NM_001285921.1 | chr4:147247694-147279018 |
| 17332 | Mfn2 | NM_001285922.1 | chr4:147247694-147279018 |
| 17333 | Mfn2 | NM_001285923.1 | chr4:147247694-147279018 |
| 17334 | Mfn2 | NM_133201.3 | chr4:147247694-147279018 |
| 17335 | Mfng | NM_008595.2 | chr15:78586312-78603875 |
| 17336 | Mfrp | NM_001190314.1 | chr9:43909853-43917270 |
| 17337 | Mfsd1 | NM_025813.1 | chr3:67386689-67408153 |
| 17338 | Mfsd10 | NM_026660.2 | chr5:34976295-34979763 |
| 17339 | Mfsd11 | NM_178620.3 | chr11:116715328-116736951 |
| 17340 | Mfsd12 | NM_028657.3 | chr10:80826315-80826780 |
| 17341 | Mfsd2a | NM_029662.1 | chr4:122624093-122638431 |
| 17342 | Mfsd2b | NM_001033488.2 | chr12:4869243-4881165 |
| 17343 | Mfsd3 | NM_027122.3 | chr15:76531972-76534669 |
| 17344 | Mfsd4 | NM_001114662.1 | chr1:133923197-133964639 |
| 17345 | Mfsd4 | NM_172510.4 | chr1:133923197-133964639 |
| 17346 | Mfsd5 | NM_134100.4 | chr15:102109886-102112175 |
| 17347 | Mfsd6 | NM_133829.2 | chr1:52713147-52784162 |
| 17348 | Mfsd6 | NM_178081.4 | chr1:52713147-52784162 |
| 17349 | Mfsd6l | NM_146004.1 | chr11:68369687-68371747 |
| 17350 | Mfsd7a | NM_172883.2 | chr5:108870072-108877910 |
| 17351 | Mfsd7b | NM_001081259.1 | chr1:192829711-192850069 |
| 17352 | Mfsd7c | NM_145447.2 | chr12:87087488-87154535 |
| 17353 | Mfsd8 | NM_028140.4 | chr3:40622093-40650776 |
| 17354 | Mfsd9 | NM_172499.2 | chr1:40828884-40847502 |
| 17355 | Mga | NM_001164274.1 | chr2:119722963-119795317 |
| 17356 | Mga | NM_013720.2 | chr2:119722963-119795317 |
| 17357 | Mgam | NM_001171003.1 | chr6:40578829-40719122 |
| 17358 | Mgarp | NM_026358.3 | chr3:51192334-51200469 |
| 17359 | Mgarp | NR_028121.1 | chr3:51192334-51200469 |
| 17360 | Mgat1 | NM_001110148.1 | chr11:49057692-49076526 |
| 17361 | Mgat1 | NM_001110149.1 | chr11:49057692-49076526 |
| 17362 | Mgat1 | NM_001110150.1 | chr11:49057692-49076526 |
| 17363 | Mgat1 | NM_010794.3 | chr11:49057692-49076526 |
| 17364 | Mgat2 | NM_146035.2 | chr12:70285144-70287760 |
| 17365 | Mgat3 | NM_010795.4 | chr15:80004150-80045949 |
| 17366 | Mgat4a | NM_001290801.1 | chr1:37496184-37597861 |
| 17367 | Mgat4a | NM_173870.3 | chr1:37496184-37597861 |
| 17368 | Mgat4b | NM_145926.3 | chr11:50038837-50048605 |
| 17369 | Mgat4c | NM_001162368.1 | chr10:101144120-101854102 |
| 17370 | Mgat4c | NM_001162369.1 | chr10:101144120-101854102 |
| 17371 | Mgat4c | NM_001205098.1 | chr10:101144120-101854102 |
| 17372 | Mgat4c | NM_026243.4 | chr10:101144120-101854102 |
| 17373 | Mgat5 | NM_145128.3 | chr1:129101562-129379549 |
| 17374 | Mgat5b | NM_172948.3 | chr11:116780176-116848258 |
| 17375 | Mgea5 | NM_023799.3 | chr19:45824748-45857781 |
| 17376 | Mgl2 | NM_145137.2 | chr11:69943858-69951044 |
| 17377 | Mgll | NM_001166249.1 | chr6:88674405-88778354 |
| 17378 | Mgll | NM_001166250.1 | chr6:88674405-88778354 |
| 17379 | Mgll | NM_001166251.1 | chr6:88674405-88778354 |
| 17380 | Mgll | NM_011844.4 | chr6:88674405-88778354 |
| 17381 | Mgme1 | NM_001289630.1 | chr2:144096639-144106963 |
| 17382 | Mgme1 | NM_001289631.1 | chr2:144096639-144106963 |
| 17383 | Mgme1 | NM_028984.5 | chr2:144096639-144106963 |
| 17384 | Mgmt | NM_008598.2 | chr7:144086293-144319871 |
| 17385 | Mgp | NM_008597.3 | chr6:136820955-136824326 |
| 17386 | Mgrn1 | NM_001252437.1 | chr16:4886099-4941025 |
| 17387 | Mgrn1 | NM_029657.4 | chr16:4886099-4941025 |
| 17388 | Mgst1 | NM_019946.4 | chr6:138089057-138105273 |
| 17389 | Mgst2 | NM_174995.2 | chr3:51465114-51486597 |
| 17390 | Mgst3 | NM_025569.1 | chr1:169302514-169323928 |
| 17391 | Mia | NM_019394.3 | chr7:27964759-27966168 |
| 17392 | Mia2 | NM_177321.2 | chr12:60196786-60210117 |
| 17393 | Mia3 | NM_177389.1 | chr1_random:299583-342913 |
| 17394 | Miat | NR_003718.2 | chr5:112642247-112657968 |
| 17395 | Miat | NR_033657.1 | chr5:112642247-112657968 |
| 17396 | Mib1 | NM_144860.2 | chr18:10726623-10812215 |
| 17397 | Mib2 | NM_001256107.1 | chr4:155028580-155043363 |
| 17398 | Mib2 | NM_001256108.2 | chr4:155028580-155043363 |
| 17399 | Mib2 | NM_145124.3 | chr4:155028580-155043363 |
| 17400 | Mical1 | NM_001164433.1 | chr10:41196119-41206836 |
| 17401 | Mical1 | NM_138315.2 | chr10:41196119-41206836 |
| 17402 | Mical2 | NM_001193305.1 | chr7:119369349-119498708 |
| 17403 | Mical2 | NM_177282.5 | chr7:119369349-119498708 |
| 17404 | Mical3 | NM_001270475.1 | chr6:120881563-121081040 |
| 17405 | Mical3 | NM_153396.3 | chr6:120881563-121081040 |
| 17406 | Micald | NM_027587.2 | chr7:119511821-119556618 |
| 17407 | Micall1 | NM_177461.1 | chr15:78939413-78967331 |
| 17408 | Micall2 | NM_174850.3 | chr5:140182646-140212287 |
| 17409 | Micu1 | NM_001291442.1 | chr10:59165310-59326882 |
| 17410 | Micu1 | NM_001291443.1 | chr10:59165310-59326882 |
| 17411 | Micu1 | NM_144822.3 | chr10:59165310-59326882 |
| 17412 | Micu2 | NM_028643.3 | chr14:58535116-58618099 |

Fig. 25 - 93

| | | | | | | | | |
|---|---|---|---|---|---|---|---|---|
| 17413 | Micu3 | NM_030110.1 | chr8:41393404-41471658 | | 17508 | Mir1306 | NR_035467.2 | chr16:18284332-18284410 |
| 17414 | Mid1 | NM_001290504.1 | chrX:166123130-166428729 | | 17509 | Mir130a | NR_029544.1 | chr2:84581271-84581335 |
| 17415 | Mid1 | NM_001290505.1 | chrX:166123130-166428729 | | 17510 | Mir130b | NR_029659.1 | chr16:17124154-17124235 |
| 17416 | Mid1 | NM_001290506.1 | chrX:166123130-166428729 | | 17511 | Mir130c | NR_105807.1 | chr9:53208910-53208991 |
| 17417 | Mid1 | NM_001290512.1 | chrX:166123130-166428729 | | 17512 | Mir132 | NR_029546.1 | chr11:74987183-74987249 |
| 17418 | Mid1 | NM_010797.3 | chrX:166123130-166428729 | | 17513 | Mir133a-1 | NR_029547.1 | chr18:10782907-10782974 |
| 17419 | Mid1 | NM_183151.1 | chrX:166123130-166428729 | | 17514 | Mir133a-2 | NR_029901.1 | chr2:180133084-180133187 |
| 17420 | Mid1ip1 | NM_001166635.1 | chrX:10294490-10296828 | | 17515 | Mir133b | NR_029902.1 | chr1:20672849-20672968 |
| 17421 | Mid1ip1 | NM_026524.4 | chrX:10294490-10296828 | | 17516 | Mir133c | NR_105753.1 | chr2:29330735-29330814 |
| 17422 | Mid2 | NM_011845.2 | chrX:137212566-137302254 | | 17517 | Mir134 | NR_029548.1 | chr12:110972348-110972419 |
| 17423 | Midn | NM_021565.5 | chr10:79611034-79621112 | | 17518 | Mir135a-1 | NR_029549.1 | chr9:106056455-106056544 |
| 17424 | Mief1 | NM_178719.5 | chr15:80064509-80083801 | | 17519 | Mir135a-2 | NR_029812.1 | chr10:91534830-91534930 |
| 17425 | Mief2 | NM_001009927.2 | chr11:60541900-60546453 | | 17520 | Mir135b | NR_029777.1 | chr1:134094665-134094761 |
| 17426 | Mien1 | NM_025559.2 | chr11:98299022-98300302 | | 17521 | Mir136 | NR_029550.1 | chr12:110833537-110833598 |
| 17427 | Mier1 | NM_001039081.2 | chr4:102786994-102838359 | | 17522 | Mir137 | NR_029551.1 | chr3:118136774-118136847 |
| 17428 | Mier1 | NM_001286221.1 | chr4:102786994-102838359 | | 17523 | Mir138-1 | NR_029819.1 | chr9:122591993-122592092 |
| 17429 | Mier1 | NM_001286222.1 | chr4:102786994-102838359 | | 17524 | Mir138-2 | NR_029552.1 | chrX_random:11265261-11265297 |
| 17430 | Mier1 | NM_001286223.1 | chr4:102786994-102838359 | | 17525 | Mir138-2 | NR_029552.1 | chr8:96848210-96848281 |
| 17431 | Mier1 | NM_027696.3 | chr4:102786994-102838359 | | 17526 | Mir139 | NR_029791.1 | chr7:108623890-108623957 |
| 17432 | Mier2 | NM_027422.2 | chr10:79002989-79017836 | | 17527 | Mir140 | NR_029553.1 | chr8:100075144-100075213 |
| 17433 | Mier3 | NM_172593.3 | chr13:112476385-112508802 | | 17528 | Mir141 | NR_029554.1 | chr6:124667931-124668003 |
| 17434 | Mif | NM_010798.2 | chr10:75322097-75322995 | | 17529 | Mir142 | NR_029555.1 | chr11:87570366-87570429 |
| 17435 | Mif4gd | NM_001243584.1 | chr11:115469232-115474283 | | 17530 | Mir142b | NR_106176.1 | chr11:87570343-87570457 |
| 17436 | Mif4gd | NM_001243586.1 | chr11:115469232-115474283 | | 17531 | Mir143 | NR_029601.1 | chr18:61808850-61808912 |
| 17437 | Mif4gd | NM_001243587.1 | chr11:115469232-115474283 | | 17532 | Mir143hg | NR_045402.1 | chr18:61805532-61825192 |
| 17438 | Mif4gd | NM_027162.4 | chr11:115469232-115474283 | | 17533 | Mir144 | NR_029556.1 | chr11:77886506-77886572 |
| 17439 | Miip | NM_001025365.2 | chr4:147234886-147242828 | | 17534 | Mir145 | NR_029557.1 | chr18:61,807,479-61,807,548 |
| 17440 | Mill1 | NM_153749.4 | chr7:18830695-18851441 | | 17535 | Mir145b | NR_105780.1 | chr18:69181852-69181927 |
| 17441 | Mill2 | NM_153760.2 | chr7:19425314-19444002 | | 17536 | Mir146 | NR_029558.1 | chr11:43187898-43187963 |
| 17442 | Mill2 | NM_153761.3 | chr7:19425314-19444002 | | 17537 | Mir146b | NR_030468.1 | chr19:46417251-46417360 |
| 17443 | Milr1 | NM_001033435.3 | chr11:106612539-106640851 | | 17538 | Mir147 | NR_030547.1 | chr2:122466539-122466617 |
| 17444 | Milr1 | NM_001271372.1 | chr11:106612539-106640851 | | 17539 | Mir148a | NR_029719.1 | chr6:51219810-51219909 |
| 17445 | Milr1 | NM_001271373.1 | chr11:106612539-106640851 | | 17540 | Mir148b | NR_029766.1 | chr15:103115556-103115652 |
| 17446 | Milr1 | NM_001271374.1 | chr11:106612539-106640851 | | 17541 | Mir149 | NR_029559.1 | chr1:94746955-94747020 |
| 17447 | Milr1 | NM_001271375.1 | chr11:106612539-106640851 | | 17542 | Mir150 | NR_029560.1 | chr7:52377126-52377191 |
| 17448 | Milr1 | NR_073165.1 | chr11:106612539-106640851 | | 17543 | Mir152 | NR_029562.1 | chr11:96711707-96711779 |
| 17449 | Mina | NM_025910.3 | chr16:59471601-59492277 | | 17544 | Mir153 | NR_029563.1 | chr12:118489290-118489358 |
| 17450 | Mink1 | NM_001045959.1 | chr11:70376382-70427984 | | 17545 | Mir154 | NR_029564.1 | chr12:110976643-110976708 |
| 17451 | Mink1 | NM_001045964.1 | chr11:70376382-70427984 | | 17546 | Mir155 | NR_029565.1 | chr16:84714384-84714449 |
| 17452 | Mink1 | NM_016713.2 | chr11:70376382-70427984 | | 17547 | Mir15a | NR_029733.1 | chr14:62250864-62250947 |
| 17453 | Mink1 | NM_176893.2 | chr11:70376382-70427984 | | 17548 | Mir15b | NR_029529.1 | chr3:68813694-68813757 |
| 17454 | Minos1 | NM_001163006.2 | chr4:138657728-138687028 | | 17549 | Mir16-1 | NR_029734.1 | chr14:62250717-62250809 |
| 17455 | Minos1 | NR_033745.1 | chr4:138657728-138687028 | | 17550 | Mir16-2 | NR_029735.1 | chr3:68813824-68813918 |
| 17456 | Minpp1 | NM_010799.2 | chr19:32560258-32589860 | | 17551 | Mir1668 | NR_106188.1 | chr8:86247777-86247883 |
| 17457 | Mios | NM_145334.2 | chr6:8159226-8186273 | | 17552 | Mir17 | NR_029785.1 | chr14:115442892-115442976 |
| 17458 | Miox | NM_019977.2 | chr15:89164903-89167438 | | 17553 | Mir17hg | NR_029382.1 | chr14:115443612-115445950 |
| 17459 | Mip | NM_008600.4 | chr10:127662893-127668867 | | 17554 | Mir18 | NR_029736.1 | chr14:115443072-115443168 |
| 17460 | Mipep | NM_027436.3 | chr14:61403402-61524317 | | 17555 | Mir181a-1 | NR_029795.1 | chr1:139863031-139863118 |
| 17461 | Mipep | NR_040642.1 | chr14:61403402-61524317 | | 17556 | Mir181a-2 | NR_029568.1 | chr2:38708255-38708330 |
| 17462 | Mipol1 | NM_001164370.1 | chr12:58331412-58558228 | | 17557 | Mir181b-1 | NR_029820.1 | chr1:139863215-139863295 |
| 17463 | Mir100 | NR_029790.1 | chr9:41339507-41339587 | | 17558 | Mir181b-2 | NR_029904.1 | chr2:38709350-38709435 |
| 17464 | Mir101a | NR_029537.1 | chr4:101019550-101019632 | | 17559 | Mir181c | NR_029821.1 | chr8:86702771-86702860 |
| 17465 | Mir101b | NR_029778.1 | chr19:29209769-29209865 | | 17560 | Mir181d | NR_030534.1 | chr8:86702614-86702686 |
| 17466 | Mir101c | NR_039546.1 | chr9:3038668-3038743 | | 17561 | Mir182 | NR_029569.1 | chr6:30115917-30115992 |
| 17467 | Mir103-1 | NR_029754.1 | chr1:35595898-35595983 | | 17562 | Mir183 | NR_030713.1 | chr6:30119667-30119737 |
| 17468 | Mir103-2 | NR_029755.1 | chr2:131113788-131113873 | | 17563 | Mir1839 | NR_035501.1 | chr7:88674802-88674874 |
| 17469 | Mir105 | NR_030546.1 | chrX:69836839-69836918 | | 17564 | Mir184 | NR_029570.1 | chr9:89697097-89697166 |
| 17470 | Mir106a | NR_029657.1 | chrX:50095680-50095744 | | 17565 | Mir1843 | NR_037207.1 | chr12:81492600-81492664 |
| 17471 | Mir106b | NR_029658.1 | chr5:138606965-138607046 | | 17566 | Mir1843b | NR_039543.1 | chr1:161270489-161270554 |
| 17472 | Mir107 | NR_029783.1 | chr19:34895177-34895263 | | 17567 | Mir185 | NR_029571.1 | chr16:18327494-18327558 |
| 17473 | Mir10a | NR_029784.1 | chr11:96178478-96178588 | | 17568 | Mir186 | NR_029572.1 | chr3:157207243-157207313 |
| 17474 | Mir10b | NR_029566.1 | chr2:74564127-74564194 | | 17569 | Mir187 | NR_029573.1 | chr18:24587610-24587671 |
| 17475 | Mir1187 | NR_035415.1 | chr5:83227968-83228090 | | 17570 | Mir188 | NR_029574.1 | chrX:6825115-6825182 |
| 17476 | Mir1188 | NR_035419.1 | chr12:110850032-110850151 | | 17571 | Mir1892 | NR_035439.1 | chr12:55746920-55746999 |
| 17477 | Mir1190 | NR_035421.2 | chr12:102259883-102259978 | | 17572 | Mir1893 | NR_035446.1 | chr18:6490562-6490644 |
| 17478 | Mir1191b | NR_106141.1 | chr10:80878985-80879042 | | 17573 | Mir1894 | NR_035445.1 | chr17:36054834-36054914 |
| 17479 | Mir1192 | NR_035423.1 | chr19:23223921-23224041 | | 17574 | Mir1895 | NR_035435.1 | chr3:133903469-133903547 |
| 17480 | Mir1193 | NR_035424.1 | chr12:110953880-110954001 | | 17575 | Mir1896 | NR_035441.1 | chr13:21537029-21537109 |
| 17481 | Mir1195 | NR_035427.2 | chr16:30920640-31275783 | | 17576 | Mir1897 | NR_035433.1 | chr3:34537386-34537464 |
| 17482 | Mir1197 | NR_035429.1 | chr12:110950526-110950646 | | 17577 | Mir1898 | NR_035443.1 | chr15:12101247-12101329 |
| 17483 | Mir1199 | NR_035431.1 | chr8:86535414-86535532 | | 17578 | Mir1899 | NR_035437.1 | chr9:8246785-8246881 |
| 17484 | Mir1224 | NR_035407.1 | chr16:20604525-20604609 | | 17579 | Mir18b | NR_030548.1 | chrX:50095507-50095590 |
| 17485 | Mir122a | NR_029600.1 | chr18:65408514-65408580 | | 17580 | Mir190 | NR_029576.1 | chr9:67084467-67084533 |
| 17486 | Mir1231 | NR_049188.1 | chr1:137351180-137351260 | | 17581 | Mir1900 | NR_035438.1 | chr9:20836695-20836772 |
| 17487 | Mir1247 | NR_037204.1 | chr12:111516258-111516339 | | 17582 | Mir1901 | NR_035447.1 | chr18:11998870-11998947 |
| 17488 | Mir1249 | NR_037206.1 | chr15:84781956-84782053 | | 17583 | Mir1902 | NR_035432.1 | chr2:104269018-104269097 |
| 17489 | Mir124a-1 | NR_029813.1 | chr14:65209494-65209578 | | 17584 | Mir1903 | NR_035436.1 | chr8:130883141-130883220 |
| 17490 | Mir124a-2 | NR_029814.1 | chr3:17695662-17695770 | | 17585 | Mir1904 | NR_035442.1 | chr13:110694017-110694096 |
| 17491 | Mir124a-3 | NR_029538.1 | chr2:180628744-180628812 | | 17586 | Mir1905 | NR_035434.1 | chr3:88340223-88340304 |
| 17492 | Mir125 | NR_037219.1 | chr10:91599885-91599968 | | 17587 | Mir1906-1 | NR_035440.1 | chrX:86,004,813-86,004,892; chr12:110,782,751-110,782,830 |
| 17493 | Mir125a | NR_106160.1 | chr18:56697793-56697852 | | | | | |
| 17494 | Mir125a | NR_029539.1 | chr17:17967775-17967843 | | | | | |
| 17495 | Mir125b-1 | NR_029822.1 | chr9:41390009-41390085 | | 17588 | Mir1906-2 | NR_037313.1 | chrX:86004812-86004892 |
| 17496 | Mir125b-2 | NR_029540.1 | chr16:77646517-77646588 | | 17589 | Mir1907 | NR_035444.1 | chr15:50720571-50720660 |
| 17497 | Mir126 | NR_029541.1 | chr2:26446877-26446949 | | 17590 | Mir190b | NR_030543.1 | chr3:89873941-89874021 |
| 17498 | Mir1264 | NR_037205.1 | chrX:143445144-143445229 | | 17591 | Mir191 | NR_029577.1 | chr9:108470649-108470723 |
| 17499 | Mir126b | NR_106155.1 | chr2:26446883-26446940 | | 17592 | Mir1912 | NR_037300.1 | chrX:143443984-143444070 |
| 17500 | Mir127 | NR_029542.1 | chr12:110831056-110831125 | | 17593 | Mir192 | NR_029720.1 | chr19:6264843-6264932 |
| 17501 | Mir128-1 | NR_029543.1 | chr1:130098938-130099007 | | 17594 | Mir1929 | NR_035450.1 | chr10:44079482-44079574 |
| 17502 | Mir128-2 | NR_029823.1 | chr9:112021140-112021215 | | 17595 | Mir193 | NR_029579.1 | chr11:79525470-79525536 |
| 17503 | Mir1291 | NR_106171.1 | chr15:98350193-98350309 | | 17596 | Mir1930 | NR_035451.1 | chr10:77103968-77104052 |
| 17504 | Mir129-1 | NR_029567.1 | chr6:28972618-28972691 | | 17597 | Mir1931 | NR_035452.1 | chr10:92625530-92625648 |
| 17505 | Mir129-2 | NR_029752.1 | chr2:94081521-94081610 | | 17598 | Mir1932 | NR_035453.1 | chr11:119251785-119251875 |
| 17506 | Mir1298 | NR_037210.1 | chrX:143499448-143499545 | | 17599 | Mir1933 | NR_035454.1 | chr11:21244591-21244678 |
| 17507 | Mir129b | NR_106139.1 | chr2:94081535-94081599 | | 17600 | Mir1934 | NR_035455.1 | chr11:69476544-69476627 |

Fig. 25 - 94

| | | | | | | | | |
|---|---|---|---|---|---|---|---|---|
| 17601 | Mir1936 | NR_035457.1 | chr12:103923138-103923230 | | 17696 | Mir26b | NR_029743.1 | chr1:74440884-74440968 |
| 17602 | Mir1938 | NR_035459.1 | chr12:40949299-40949398 | | 17697 | Mir27a | NR_029746.1 | chr8:86732570-86732657 |
| 17603 | Mir193b | NR_030549.1 | chr16:13449615-13449694 | | 17698 | Mir27b | NR_029531.1 | chr13:63402020-63402092 |
| 17604 | Mir1940 | NR_035461.1 | chr13:96,100,535-96,100,638 | | 17699 | Mir2861 | NR_037217.1 | chr2:32568326-32568408 |
| 17605 | Mir1941 | NR_035462.1 | chr15:101199783-101199865 | | 17700 | Mir28 | NR_039551.1 | chr8:75540411-75540490 |
| 17606 | Mir194-1 | NR_029580.1 | chr1:187137198-187137264 | | 17701 | Mir290 | NR_029640.1 | chr7:3218627-3218709 |
| 17607 | Mir1942 | NR_035463.1 | chr1:76046041-76046103 | | 17702 | Mir290b | NR_106158.1 | chr7:3218639-3218696 |
| 17608 | Mir194-2 | NR_029830.1 | chr19:6264642-6264728 | | 17703 | Mir291a | NR_029641.1 | chr7:3218920-3219001 |
| 17609 | Mir1943 | NR_035464.1 | chr15:79205658-79205730 | | 17704 | Mir291b | NR_030276.1 | chr7:3219483-3219561 |
| 17610 | Mir1945 | NR_035466.1 | chr16:11254460-11254538 | | 17705 | Mir292 | NR_029642.1 | chr7:3219190-3219271 |
| 17611 | Mir1946a | NR_035468.1 | chr16:32267535-32267669 | | 17706 | Mir292b | NR_106140.1 | chr7:3219199-3219260 |
| 17612 | Mir1947 | NR_035469.1 | chr16:33105447-33105531 | | 17707 | Mir293 | NR_029643.1 | chr7:3220344-3220423 |
| 17613 | Mir1948 | NR_035471.1 | chr18:12873320-12873404 | | 17708 | Mir294 | NR_029644.1 | chr7:3220642-3220725 |
| 17614 | Mir1949 | NR_035472.1 | chr18:35714221-35714290 | | 17709 | Mir295 | NR_029645.1 | chr7:3220774-3220842 |
| 17615 | Mir195 | NR_029581.1 | chr11:70048543-70048637 | | 17710 | Mir296 | NR_029646.1 | chr2:174092547-174092626 |
| 17616 | Mir1951 | NR_035476.1 | chr2:115464461-115464549 | | 17711 | Mir297-1 | NR_029647.1 | chr15:27175876-27246498 |
| 17617 | Mir1952 | NR_035477.1 | chr2:138645664-138645743 | | 17712 | Mir297a-3 | NR_030551.1 | chr2:10437447-10437548 |
| 17618 | Mir1953 | NR_035478.1 | chr2:151793264-151793353 | | 17713 | Mir297b | NR_030474.1 | chr2:10433294-10433402 |
| 17619 | Mir1955 | NR_035480.1 | chr2:92032134-92032231 | | 17714 | Mir297c | NR_030555.1 | chr2:10437447-10437543 |
| 17620 | Mir1956 | NR_035481.1 | chr3:138189385-138189449 | | 17715 | Mir298 | NR_029649.1 | chr2:174093004-174093086 |
| 17621 | Mir1957b | NR_105819.1 | chr3:113974100-113974222 | | 17716 | Mir299 | NR_029650.1 | chr12:110948848-110948910 |
| 17622 | Mir195b | NR_105751.1 | chr2:56638221-56638318 | | 17717 | Mir299b | NR_049185.1 | chr12:110948855-110948903 |
| 17623 | Mir1960 | NR_035486.1 | chr5:30497279-30497356 | | 17718 | Mir29a | NR_029744.1 | chr6:31012659-31012747 |
| 17624 | Mir1961 | NR_035487.1 | chr5:93217477-93217588 | | 17719 | Mir29b-1 | NR_029532.1 | chr6:31013022-31013093 |
| 17625 | Mir1962 | NR_035488.1 | chr7:142757845-142757965 | | 17720 | Mir29b-2 | NR_029809.1 | chr1:196863234-196863314 |
| 17626 | Mir1963 | NR_035489.1 | chr7:29868655-29868713 | | 17721 | Mir29c | NR_029745.1 | chr1:196863741-196863828 |
| 17627 | Mir1964 | NR_035490.1 | chr7:30558313-30558395 | | 17722 | Mir300 | NR_029651.1 | chr12:110962522-110962601 |
| 17628 | Mir1966 | NR_035492.1 | chr8:108139366-108139473 | | 17723 | Mir301 | NR_029652.1 | chr11:86926506-86926591 |
| 17629 | Mir1967 | NR_035493.1 | chr8:126546540-126546622 | | 17724 | Mir301b | NR_030415.1 | chr16:17124493-17124589 |
| 17630 | Mir1968 | NR_035494.1 | chr8:13189031-13189098 | | 17725 | Mir302a | NR_029653.1 | chr3:127248414-127248482 |
| 17631 | Mir1969 | NR_035495.1 | chr8:73449423-73449517 | | 17726 | Mir302b | NR_030403.1 | chr3:127248146-127248219 |
| 17632 | Mir196a-1 | NR_029721.1 | chr11:96126477-96126579 | | 17727 | Mir302c | NR_030404.1 | chr3:127248281-127248348 |
| 17633 | Mir196a-2 | NR_029722.1 | chr15:102803780-102803865 | | 17728 | Mir302d | NR_030405.1 | chr3:127248542-127248607 |
| 17634 | Mir196b | NR_029812.1 | chr6:52180079-52180164 | | 17729 | Mir3057 | NR_037218.1 | chr10:80734342-80734432 |
| 17635 | Mir1971 | NR_035499.1 | chr14:78591179-78591285 | | 17730 | Mir3058 | NR_037212.1 | chr10:95021865-95021955 |
| 17636 | Mir1981 | NR_035502.1 | chr1:186646286-186646367 | | 17731 | Mir3059 | NR_037211.1 | chr10:101235326-101235406 |
| 17637 | Mir1982 | NR_035503.1 | chr10:80291542-80291615 | | 17732 | Mir3060 | NR_037220.1 | chr11:4039367-4039449 |
| 17638 | Mir1983 | NR_035500.1 | chr13:21988786-21988918 | | 17733 | Mir3061 | NR_037221.1 | chr11:51940247-51940338 |
| 17639 | Mir199a-1 | NR_029585.1 | chr9:21300939-21301008 | | 17734 | Mir3062 | NR_037222.1 | chr11:68804076-68804180 |
| 17640 | Mir199a-2 | NR_029810.1 | chr1:164147945-164148054 | | 17735 | Mir3063 | NR_037223.1 | chr11:95824606-95824697 |
| 17641 | Mir199b | NR_029811.1 | chr2:32173980-32174089 | | 17736 | Mir3064 | NR_037224.1 | chr11:106644007-106644073 |
| 17642 | Mir19a | NR_029786.1 | chr14:115443221-115443303 | | 17737 | Mir3065 | NR_037225.1 | chr11:119876081-119876167 |
| 17643 | Mir19b-1 | NR_029815.1 | chr14:115443527-115443613 | | 17738 | Mir3066 | NR_037226.1 | chr12:17362198-17362280 |
| 17644 | Mir19b-2 | NR_029715.1 | chrX:50095159-50095243 | | 17739 | Mir3067 | NR_037227.1 | chr12:82267138-82267221 |
| 17645 | Mir1a-1 | NR_029528.1 | chr2:180123753-180123829 | | 17740 | Mir3068 | NR_037228.1 | chr12:88778629-88778707 |
| 17646 | Mir1a-2 | NR_029781.1 | chr18:10785479-10785550 | | 17741 | Mir3069 | NR_037229.1 | chr12:106269287-106269351 |
| 17647 | Mir1b | NR_035413.1 | chr18:10785444-10785565 | | 17742 | Mir3070a | NR_037230.1 | chr12:110826152-110826241 |
| 17648 | Mir200a | NR_029723.1 | chr4:155429004-155429094 | | 17743 | Mir3070b | NR_037231.1 | chr12:110826801-110826890 |
| 17649 | Mir200b | NR_029587.1 | chr4:155429789-155429859 | | 17744 | Mir3071 | NR_037232.1 | chr12:110833528-110833607 |
| 17650 | Mir200c | NR_029792.1 | chr6:124668339-124668408 | | 17745 | Mir3072 | NR_037233.1 | chr12:110986088-110986170 |
| 17651 | Mir201 | NR_029588.1 | chrX:65241270-65241336 | | 17746 | Mir3073 | NR_037234.1 | chr12:113347449-113347533 |
| 17652 | Mir202 | NR_029589.1 | chr7:147143587-147143659 | | 17747 | Mir3073b | NR_049197.1 | chr12:113347461-113347520 |
| 17653 | Mir203 | NR_029590.1 | chr12:113369090-113369166 | | 17748 | Mir3074-1 | NR_037235.1 | chr13:63402507-63402591 |
| 17654 | Mir204 | NR_029591.1 | chr19:22825095-22825162 | | 17749 | Mir3074-2 | NR_037294.1 | chr8:86732724-86732806 |
| 17655 | Mir205 | NR_029592.1 | chr1:195333656-195333724 | | 17750 | Mir3075 | NR_037236.1 | chr14:26353925-26354009 |
| 17656 | Mir206 | NR_029593.1 | chr1:20669090-20669163 | | 17751 | Mir3076 | NR_037237.1 | chr14:31385335-31385394 |
| 17657 | Mir207 | NR_029594.1 | chr4:40669950-40670028 | | 17752 | Mir3077 | NR_037238.1 | chr14:58417261-58417324 |
| 17658 | Mir208a | NR_029724.1 | chr14:55567897-55567979 | | 17753 | Mir3078 | NR_037239.1 | chr14:65210022-65210108 |
| 17659 | Mir208b | NR_030607.1 | chr14:55594537-55594613 | | 17754 | Mir3081 | NR_037242.1 | chr16:44558159-44558242 |
| 17660 | Mir20a | NR_029737.1 | chr14:115443378-115443485 | | 17755 | Mir3082 | NR_037243.1 | chr17:25968310-25968373 |
| 17661 | Mir20b | NR_030273.1 | chrX:50095289-50095369 | | 17756 | Mir3083 | NR_037244.1 | chr17:27085001-27085064 |
| 17662 | Mir21 | NR_029738.1 | chr11:86397589-86397660 | | 17757 | Mir3084 | NR_037245.1 | chr19:24994405-25036106 |
| 17663 | Mir210 | NR_029793.1 | chr7:148407282-148407392 | | 17758 | Mir3085 | NR_037246.1 | chr19:60837018-60866596 |
| 17664 | Mir211 | NR_029805.1 | chr7:71350692-71350797 | | 17759 | Mir3086 | NR_037246.1 | chr19:42354571-42354660 |
| 17665 | Mir212 | NR_029794.1 | chr11:74986889-74986980 | | 17760 | Mir3086 | NR_037247.1 | chr19:58986162-58986249 |
| 17666 | Mir2136 | NR_035516.1 | chr9:104328442-104328517 | | 17761 | Mir3087 | NR_037270.1 | chr2:25298299-25298354 |
| 17667 | Mir2137 | NR_035517.1 | chrX:70237418-70237483 | | 17762 | Mir3088 | NR_037271.1 | chr2:28588798-28588871 |
| 17668 | Mir2139 | NR_035519.1 | chr4:139523441-139523535 | | 17763 | Mir3089 | NR_037272.1 | chr2:30576729-30576813 |
| 17669 | Mir214 | NR_029796.1 | chr1:164153499-164153608 | | 17764 | Mir3091 | NR_037274.1 | chr2:179992241-179992316 |
| 17670 | Mir215 | NR_029588.1 | chr1:187137460-187137570 | | 17765 | Mir3092 | NR_037275.1 | chr3:27483822-27483917 |
| 17671 | Mir216a | NR_029797.1 | chr11:28657011-28657083 | | 17766 | Mir3093 | NR_037276.1 | chr3:88019092-88019179 |
| 17672 | Mir216b | NR_030419.1 | chr11:28646191-28646276 | | 17767 | Mir3094 | NR_037277.1 | chr4:40940728-40940791 |
| 17673 | Mir216c | NR_106152.1 | chr11:28646198-28646266 | | 17768 | Mir3095 | NR_037278.1 | chr4:58453884-58453970 |
| 17674 | Mir217 | NR_029828.1 | chr11:28663727-28663835 | | 17769 | Mir3097 | NR_037280.1 | chr5:35363698-35363764 |
| 17675 | Mir218-1 | NR_029798.1 | chr5:48615181-48615290 | | 17770 | Mir3099 | NR_037213.1 | chr7:6756298-6756381 |
| 17676 | Mir218-2 | NR_029759.1 | chr11:35430318-35430427 | | 17771 | Mir30a | NR_029533.1 | chr1:23279167-23279178 |
| 17677 | Mir219-1 | NR_029800.1 | chr17:34161928-34162037 | | 17772 | Mir30b | NR_029534.1 | chr15:68168976-68169072 |
| 17678 | Mir219-2 | NR_029838.1 | chr2:29701151-29701247 | | 17773 | Mir30c-1 | NR_029716.1 | chr4:120442139-120442227 |
| 17679 | Mir219b | NR_106101.1 | chr12:29701167-29701231 | | 17774 | Mir30c-2 | NR_029717.1 | chr1:23298539-23298623 |
| 17680 | Mir219c | NR_106154.1 | chr17:34161957-34162016 | | 17775 | Mir30d | NR_029718.1 | chr15:68172769-68172851 |
| 17681 | Mir21b | NR_105796.1 | chr3:29535666-29535773 | | 17776 | Mir30f | NR_105851.1 | chr4:120445211-120445302 |
| 17682 | Mir21c | NR_105822.1 | chr8:130802047-130802125 | | 17777 | Mir31 | NR_029747.1 | chr4:88556460-88556566 |
| 17683 | Mir22 | NR_029739.1 | chr11:75277218-75277312 | | 17778 | Mir3100 | NR_037282.1 | chr7:19672177-19672241 |
| 17684 | Mir221 | NR_029806.1 | chrX:18723419-18723514 | | 17779 | Mir3101 | NR_037283.1 | chr7:27961025-27961112 |
| 17685 | Mir222 | NR_029807.1 | chrX:18724018-18724097 | | 17780 | Mir3102 | NR_037289.1 | chr7:108030820-108030923 |
| 17686 | Mir223 | NR_029801.1 | chrX:93438156-93438265 | | 17781 | Mir3103 | NR_037290.1 | chr7:135431883-135431949 |
| 17687 | Mir224 | NR_029808.1 | chrX:69506370-69506451 | | 17782 | Mir3104 | NR_037291.1 | chr7:149178084-149178146 |
| 17688 | Mir22hg | NR_030711.1 | chr11:75275041-75280192 | | 17783 | Mir3106 | NR_037214.1 | chr8:16168757-16168838 |
| 17689 | Mir23a | NR_029740.1 | chr8:86732416-86732491 | | 17784 | Mir3107 | NR_037293.1 | chr8:24253045-24253134 |
| 17690 | Mir23b | NR_029530.1 | chr13:63401792-63401865 | | 17785 | Mir3108 | NR_037295.1 | chr8:111460760-111460838 |
| 17691 | Mir24-1 | NR_029575.1 | chr8:63402516-63402583 | | 17786 | Mir3109 | NR_037296.1 | chr9:69304751-69304838 |
| 17692 | Mir24-2 | NR_029741.1 | chr8:86732714-86732820 | | 17787 | Mir3110 | NR_037297.1 | chrX:35563618-35563697 |
| 17693 | Mir25 | NR_029787.1 | chr5:138606549-138606632 | | 17788 | Mir3112 | NR_037299.1 | chrX:130609855-130609936 |
| 17694 | Mir26a-1 | NR_029742.1 | chr9:118940914-118941003 | | 17789 | Mir32 | NR_029789.1 | chr4:56908101-56908170 |
| 17695 | Mir26a-2 | NR_029803.1 | chr10:126432586-126432669 | | 17790 | Mir320 | NR_029802.1 | chr14:70843316-70843398 |

Fig. 25 - 95

| | | | | | | | | |
|---|---|---|---|---|---|---|---|---|
| 17791 | Mir322 | NR_029756.1 | chrX:50407432-50407526 | | 17886 | Mir450-2 | NR_030274.1 | chrX:50401475-50401544 |
| 17792 | Mir323 | NR_029757.1 | chr12:110950717-110950803 | | 17887 | Mir450b | NR_030498.1 | chrX:50401173-50401255 |
| 17793 | Mir324 | NR_029758.1 | chr11:69825545-69825633 | | 17888 | Mir451 | NR_029971.1 | chr11:77886671-77886743 |
| 17794 | Mir326 | NR_029760.1 | chr7:106700779-106700873 | | 17889 | Mir452 | NR_029974.1 | chrX:69507563-69507647 |
| 17795 | Mir328 | NR_029761.1 | chr8:107832264-107832360 | | 17890 | Mir453 | NR_030559.1 | chr12:110973829-110973910 |
| 17796 | Mir329 | NR_029762.1 | chr12:110951690-110951787 | | 17891 | Mir455 | NR_030477.1 | chr4:62917885-62917966 |
| 17797 | Mir33 | NR_029804.1 | chr15:82028552-82028620 | | 17892 | Mir463 | NR_030147.1 | chrX:64052397-64052472 |
| 17798 | Mir330 | NR_029763.1 | chr7:19766814-19766911 | | 17893 | Mir465 | NR_030149.1 | chrX:64092228-64092300 |
| 17799 | Mir331 | NR_029764.1 | chr10:93426512-93426608 | | 17894 | Mir465b-1 | NR_030561.1 | chrX:64082376-64082455 |
| 17800 | Mir335 | NR_029900.1 | chr6:30691299-30691396 | | 17895 | Mir465b-2 | NR_030561.1 | chrX:64088938-64089017 |
| 17801 | Mir337 | NR_029765.1 | chr12:110823999-110824095 | | 17896 | Mir465c-1 | NR_030562.1 | chrX:64079129-64079210 |
| 17802 | Mir338 | NR_029767.1 | chr11:119876079-119876176 | | 17897 | Mir465c-2 | NR_030563.1 | chrX:64085691-64085772 |
| 17803 | Mir339 | NR_029768.1 | chr5:139845604-139845699 | | 17898 | Mir465d | NR_106148.1 | chrX:64075830-64075888 |
| 17804 | Mir340 | NR_029769.1 | chr11:49883204-49883301 | | 17899 | Mir466 | NR_030150.1 | chr2:10429545-10429617 |
| 17805 | Mir341 | NR_029770.1 | chr12:110849710-110849805 | | 17900 | Mir4660 | NR_037248.1 | chr2:10394167-10394250 |
| 17806 | Mir343 | NR_030759.1 | chr7:19971992-19972066 | | 17901 | Mir466g | NR_030569.1 | chr2:10436222-10436301 |
| 17807 | Mir344 | NR_029772.1 | chr7:69022656-69022750 | | 17902 | Mir466i | NR_035412.1 | chr13:17839307-17839427 |
| 17808 | Mir344-2 | NR_030557.1 | chr7:69084912-69084992 | | 17903 | Mir466p | NR_105742.1 | chr2:10427633-10427721 |
| 17809 | Mir344b | NR_037285.1 | chr7:68935405-68935467 | | 17904 | Mir467a-1 | NR_035406.1 | chr2:10292077-10516880 |
| 17810 | Mir344c | NR_037286.1 | chr7:68982197-68982288 | | 17905 | Mir467a-1 | NR_035406.1 | chr2:10292077-10516880 |
| 17811 | Mir344d-1 | NR_037215.1 | chr7:68828009-68828078 | | 17906 | Mir467a-1 | NR_035406.1 | chr2:10292077-10516880 |
| 17812 | Mir344d-2 | NR_037216.1 | chr7:68830157-68830237 | | 17907 | Mir467a-1 | NR_035406.1 | chr2:10292077-10516880 |
| 17813 | Mir344d-3 | NR_037209.1 | chr7:68871135-68871214 | | 17908 | Mir467a-1 | NR_035406.1 | chr2:10292077-10516880 |
| 17814 | Mir344e | NR_037284.1 | chr7:68880423-68880488 | | 17909 | Mir467a-1 | NR_035406.1 | chr2:10292077-10516880 |
| 17815 | Mir344f | NR_037288.1 | chr7:69191066-69191134 | | 17910 | Mir467a-1 | NR_035406.1 | chr2:10292077-10516880 |
| 17816 | Mir344g | NR_037287.1 | chr7:69127175-69127245 | | 17911 | Mir467a-1 | NR_035406.1 | chr2:10292077-10516880 |
| 17817 | Mir344h-2 | NR_049202.1 | chr7:68850735-69072460 | | 17912 | Mir467a-1 | NR_035406.1 | chr2:10292077-10516880 |
| 17818 | Mir344h-2 | NR_049202.1 | chr7:68850735-69072460 | | 17913 | Mir467a-1 | NR_035406.1 | chr2:10292077-10516880 |
| 17819 | Mir344i | NR_049204.1 | chr7:69230108-69230196 | | 17914 | Mir467a-10 | NR_037267.1 | chr2:10,405,305-10,424,982 |
| 17820 | Mir345 | NR_029773.1 | chr12:110075182-110075278 | | 17915 | Mir467a-2 | NR_037249.1 | chr2:10397969-10422531 |
| 17821 | Mir346 | NR_029774.1 | chr14:35707795-35707892 | | 17916 | Mir467a-3 | NR_037252.1 | chr2:10292077-10516880 |
| 17822 | Mir3471-1 | NR_037304.1 | chr9:30942992-31066970 | | 17917 | Mir467a-3 | NR_037252.1 | chr2:10292077-10516880 |
| 17823 | Mir3473 | NR_037311.1 | chrX:159312850-159312927 | | 17918 | Mir467a-4 | NNR_037254.1 | chr2:10292077-10516880 |
| 17824 | Mir3473c | NR_039566.1 | chr1:193822435-193822515 | | 17919 | Mir467a-4 | NR_037254.1 | chr2:10292077-10516880 |
| 17825 | Mir3473d | NR_039583.1 | chr8:113540350-113540430 | | 17920 | Mir467a-4 | NNR_037254.1 | chr2:10292077-10516880 |
| 17826 | Mir3473e | NR_105859.1 | chr5:31969604-31969713 | | 17921 | Mir467a-5 | NR_037256.1 | chr2:10,397,969-10,422,531 |
| 17827 | Mir3473f | NR_106164.1 | chr1:108443073-108443208 | | 17922 | Mir467a-8 | NR_037263.1 | chr2:10292077-10516880 |
| 17828 | Mir3473g | NR_106202.1 | chr2:126727986-126728121 | | 17923 | Mir467a-8 | NR_037263.1 | chr2:10292077-10516880 |
| 17829 | Mir3474 | NR_037312.1 | chr2:158464319-158464376 | | 17924 | Mir467a-9 | NR_037265.1 | chr2:10,397,969-10,422,531 |
| 17830 | Mir3475 | NR_037208.1 | chrX:136845486-136845551 | | 17925 | Mir467b | NR_030472.1 | chr2:10402875-10402947 |
| 17831 | Mir34a | NR_029751.1 | chr4:149442562-149442664 | | 17926 | Mir467d | NR_030572.1 | chr2:10429257-10429341 |
| 17832 | Mir34b | NR_029655.1 | chr9:50911666-50911750 | | 17927 | Mir467f | NR_035420.1 | chr11:69448902-69449021 |
| 17833 | Mir34c | NR_029854.1 | chr9:50911138-50911215 | | 17928 | Mir468 | NR_030151.1 | chr8:81846592-81846670 |
| 17834 | Mir350 | NR_029775.1 | chr1:178702456-178702554 | | 17929 | Mir470 | NR_030153.1 | chrX:64067125-64067200 |
| 17835 | Mir351 | NR_029776.1 | chrX:50406432-50406530 | | 17930 | Mir471 | NR_030154.1 | chrX:64045769-64045836 |
| 17836 | Mir3535 | NR_106184.1 | chr1:88248556-88248702 | | 17931 | Mir483 | NR_030251.1 | chr7:149840829-149840901 |
| 17837 | Mir3544 | NR_049184.1 | chr12:110824023-110824083 | | 17932 | Mir484 | NR_030252.1 | chr16:14159718-14159785 |
| 17838 | Mir3547 | NR_105913.1 | chr17:25382496-25382583 | | 17933 | Mir485 | NR_030253.1 | chr12:110973111-110973184 |
| 17839 | Mir3569 | NR_106134.1 | chr7:31374398-31374456 | | 17934 | Mir486 | NR_030254.1 | chr8:24253027-24253154 |
| 17840 | Mir3572 | NR_039587.1 | chr7:3607564-3607649 | | 17935 | Mir487b | NR_030271.1 | chr12:110965542-110965624 |
| 17841 | Mir362 | NR_029851.1 | chrX:6819109-6819172 | | 17936 | Mir488 | NR_030441.1 | chr1:160435756-160435864 |
| 17842 | Mir3620 | NR_106147.1 | chr2:146981928-146981988 | | 17937 | Mir489 | NR_030250.1 | chr6:3671897-3672003 |
| 17843 | Mir363 | NR_029853.1 | chrX:50094869-50094944 | | 17938 | Mir490 | NR_030524.1 | chr6:36371742-36371825 |
| 17844 | Mir365-1 | NR_029855.1 | chr16:13453932-13454019 | | 17939 | Mir491 | NR_030478.1 | chr4:87767944-87768029 |
| 17845 | Mir365-2 | NR_029959.1 | chr11:79539901-79540013 | | 17940 | Mir493 | NR_030573.1 | chr12:110818442-110818525 |
| 17846 | Mir367 | NR_030268.1 | chr3:127248651-127248725 | | 17941 | Mir494 | NR_030269.1 | chr12:110953527-110953612 |
| 17847 | Mir369 | NR_030272.1 | chr12:110981628-110981706 | | 17942 | Mir495 | NR_030446.1 | chr12:110956963-110957026 |
| 17848 | Mir370 | NR_029918.1 | chr12:110856468-110856546 | | 17943 | Mir496 | NR_030437.1 | chr12:110977329-110977407 |
| 17849 | Mir374 | NR_030418.1 | chrX:100768399-100768493 | | 17944 | Mir496b | NR_105832.1 | chr19:16389382-16389494 |
| 17850 | Mir374c | NR_037298.1 | chrX:100768424-100768472 | | 17945 | Mir497 | NR_030444.1 | chr11:70048219-70048302 |
| 17851 | Mir375 | NR_029876.1 | chr1:74947231-74947295 | | 17946 | Mir497b | NR_106178.1 | chr11:70048194-70048318 |
| 17852 | Mir376a | NR_029877.1 | chr12:110961990-110962058 | | 17947 | Mir499 | NR_030757.1 | chr2:155448616-155448694 |
| 17853 | Mir376b | NR_029915.1 | chr12:110961667-110961749 | | 17948 | Mir500 | NR_030495.1 | chrX:6814809-6814960 |
| 17854 | Mir376c | NR_030270.1 | chr12:110960927-110961012 | | 17949 | Mir501 | NR_030496.1 | chrX:6818369-6818477 |
| 17855 | Mir377 | NR_029878.1 | chr12:110978720-110978787 | | 17950 | Mir503 | NR_030275.1 | chrX:50407161-50407231 |
| 17856 | Mir378b | NR_039545.1 | chr11:88166275-88166366 | | 17951 | Mir504 | NR_030574.1 | chr1:56350835-56350913 |
| 17857 | Mir379 | NR_029880.1 | chr12:110947269-110947335 | | 17952 | Mir5046 | NR_039555.1 | chr19:6904376-6904434 |
| 17858 | Mir380 | NR_029881.1 | chr12:110950012-110950073 | | 17953 | Mir505 | NR_030499.1 | chrX:57647578-57647667 |
| 17859 | Mir381 | NR_029882.1 | chr12:110965031-110965106 | | 17954 | Mir509 | NR_030575.1 | chrX:65263279-65263354 |
| 17860 | Mir382 | NR_029883.1 | chr12:110971980-110972056 | | 17955 | Mir5098 | NR_039557.1 | chr5:77,701,782-77,701,863; chr8:109,780,064-109,983,274; chr11:119,743,603-119,790,231; chr17:28,264,296-28,410,567 |
| 17861 | Mir383 | NR_029884.1 | chr8:39315187-39315256 | | | | | |
| 17862 | Mir384 | NR_029910.1 | chrX:102539620-102539708 | | | | | |
| 17863 | Mir3960 | NR_039536.1 | chr2:32568419-32568492 | | | | | |
| 17864 | Mir3966 | NR_039547.1 | chr10:96886111-96886196 | | 17956 | Mir5100 | NR_039559.1 | chr11:60542165-60542228 |
| 17865 | Mir3967 | NR_039548.1 | chr2:22509803-22509870 | | 17957 | Mir5101 | NR_039560.1 | chr12:77010090-77010172 |
| 17866 | Mir3968 | NR_039549.1 | chr15:115309275-115309374 | | 17958 | Mir5103 | NR_039562.1 | chr1:34489965-34490044 |
| 17867 | Mir3969 | NR_039550.1 | chr5:88024926-88025018 | | 17959 | Mir5104 | NR_039563.1 | chr10:7556179-7556272 |
| 17868 | Mir3971 | NR_039553.1 | chr11:75364931-75365013 | | 17960 | Mir5106 | NR_039565.1 | chr4:44234066-44234139 |
| 17869 | Mir409 | NR_029913.1 | chr12:110981368-110981446 | | 17961 | Mir5107 | NR_039567.1 | chr18:60971730-60971817 |
| 17870 | Mir410 | NR_029914.1 | chr12:110981925-110982005 | | 17962 | Mir5108 | NR_039568.1 | chr10:61237485-61237569 |
| 17871 | Mir411 | NR_029916.1 | chr12:110948384-110948466 | | 17963 | Mir511 | NR_030609.1 | chr2:14182630-14182708 |
| 17872 | Mir412 | NR_029917.1 | chr12:110981499-110981578 | | 17964 | Mir5112 | NR_039572.1 | chr18:82886672-82886932 |
| 17873 | Mir421 | NR_030558.1 | chrX:100768260-100768335 | | 17965 | Mir5113 | NR_039573.1 | chr15:80770469-80770550 |
| 17874 | Mir423 | NR_030756.1 | chr11:76891566-76891674 | | 17966 | Mir5114 | NR_039574.1 | chr19:44377661-44377721 |
| 17875 | Mir425 | NR_029947.1 | chr9:108471107-108471192 | | 17967 | Mir5116 | NR_039576.1 | chrX:53841029-53841091 |
| 17876 | Mir429 | NR_029958.1 | chr4:155428013-155428096 | | 17968 | Mir5119 | NR_039579.1 | chr11:98123919-98123976 |
| 17877 | Mir431 | NR_029952.1 | chr12:110828657-110828747 | | 17969 | Mir5121 | NR_039581.1 | chr7:52382288-52382361 |
| 17878 | Mir432 | NR_035526.1 | chr12:110833166-110833240 | | 17970 | Mir5122 | NR_039582.1 | chr4:132925691-132925779 |
| 17879 | Mir433 | NR_029952.1 | chr12:110829925-110830048 | | 17971 | Mir5123 | NR_039584.1 | chr4:40797089-40797171 |
| 17880 | Mir434 | NR_029953.1 | chr12:110832716-110832809 | | 17972 | Mir5124b | NR_105811.1 | chr6:41680062-41735061 |
| 17881 | Mir448 | NR_029956.1 | chrX:143592753-143592864 | | 17973 | Mir5126 | NR_039588.1 | chr1:84692414-84692490 |
| 17882 | Mir449a | NR_029961.1 | chr13:113827742-113827832 | | 17974 | Mir5127 | NR_039589.1 | chr18:82188748-82188819 |
| 17883 | Mir449b | NR_030602.1 | chr13:113827627-113827706 | | 17975 | Mir5128 | NR_039590.1 | chr2:37543720-37543804 |
| 17884 | Mir449c | NR_030452.1 | chr13:113826191-113826299 | | 17976 | Mir5129 | NR_039591.1 | chr2:44878620-44878697 |
| 17885 | Mir450-1 | NR_029963.1 | chrX:50401330-50401421 | | | | | |

Fig. 25 - 96

| | | | | | | | | |
|---|---|---|---|---|---|---|---|---|
| 17977 | Mir5130 | NR_039592.1 | chr14:103381766-103381849 | 18072 | Mir6389 | NR_105812.1 | chr7:64836430-64836532 |
| 17978 | Mir5131 | NR_039593.1 | chr14:46277636-46277728 | 18073 | Mir6390 | NR_105814.1 | chr14:106022858-106022987 |
| 17979 | Mir5132 | NR_039594.1 | chrX:71268867-71268937 | 18074 | Mir6391 | NR_105815.1 | chr14:118991591-118991694 |
| 17980 | Mir5133 | NR_039595.1 | chr9:61970324-61970401 | 18075 | Mir6392 | NR_105816.1 | chr15:83998700-83998807 |
| 17981 | Mir5134 | NR_039596.1 | chr17:24371472-24371549 | 18076 | Mir6393 | NR_105817.1 | chr15:87626279-87626373 |
| 17982 | Mir5135 | NR_039597.1 | chr12:77634120-77634199 | 18077 | Mir6394 | NR_105818.1 | chr7:103454177-103454275 |
| 17983 | Mir5136 | NR_039598.1 | chr19:8963189-8963264 | 18078 | Mir6395 | NR_105820.1 | chr8:35229676-35229766 |
| 17984 | Mir532 | NR_030242.1 | chrX:6825528-6825623 | 18079 | Mir6396 | NR_105821.1 | chr8:125146165-125146275 |
| 17985 | Mir539 | NR_030262.1 | chr12:110966338-110966412 | 18080 | Mir6397 | NR_105823.1 | chr4:107759962-107760054 |
| 17986 | Mir540 | NR_030260.1 | chr12:110824289-110824356 | 18081 | Mir6398 | NR_105824.1 | chr4:123293663-123293764 |
| 17987 | Mir541 | NR_030263.1 | chr12:110980619-110980708 | 18082 | Mir6399 | NR_105825.1 | chr4:137719124-137719207 |
| 17988 | Mir542 | NR_030264.1 | chrX:50402579-50402664 | 18083 | Mir6400 | NR_105826.1 | chr4:15870047-15870138 |
| 17989 | Mir543 | NR_030261.1 | chr12:110955467-110955543 | 18084 | Mir6401 | NR_105827.1 | chr7:146964916-146965025 |
| 17990 | Mir546 | NR_030259.1 | chr5:126435496-126435616 | 18085 | Mir6402 | NR_105828.1 | chr4:91039975-91040054 |
| 17991 | Mir547 | NR_030265.1 | chrX:65241548-65241626 | 18086 | Mir6403 | NR_105829.1 | chr4:134123638-134123766 |
| 17992 | Mir551b | NR_030422.1 | chr3:29315745-29315842 | 18087 | Mir6404 | NR_105830.1 | chr7:151119019-151119113 |
| 17993 | Mir5615-1 | NR_049186.1 | chr10:80567359-80567418 | 18088 | Mir6405 | NR_105831.1 | chr19:44882896-44883019 |
| 17994 | Mir5615-2 | NR_049187.1 | chr10:80567361-80567420 | 18089 | Mir6406 | NR_105833.1 | chr11:68034394-68034513 |
| 17995 | Mir5616 | NR_049189.1 | chr4:148911972-148912031 | 18090 | Mir6407 | NR_105834.1 | chr19:53085146-53085246 |
| 17996 | Mir5617 | NR_049190.1 | chrX:20440252-20440308 | 18091 | Mir6408 | NR_105835.1 | chr10:60385770-60385861 |
| 17997 | Mir5618 | NR_049191.1 | chr9:7784390-7784440 | 18092 | Mir6409 | NR_105836.1 | chr10:75471671-75471762 |
| 17998 | Mir5619 | NR_049192.1 | chr5:104477022-104477082 | 18093 | Mir6410 | NR_105837.1 | chr10:77897543-77897647 |
| 17999 | Mir5620 | NR_049193.1 | chr7:7251602-7251657 | 18094 | Mir6411 | NR_105838.1 | chr10:103724322-103724430 |
| 18000 | Mir5621 | NR_049194.1 | chr1:115657138-115657200 | 18095 | Mir6412 | NR_105839.1 | chr17:30393402-30393480 |
| 18001 | Mir5622 | NR_049195.1 | chr2:152690803-152690862 | 18096 | Mir6413 | NR_105840.1 | chr10:20017386-20017494 |
| 18002 | Mir5623 | NR_049196.1 | chr19:58125657-58125726 | 18097 | Mir6414 | NR_105842.1 | chr5:42282580-42282662 |
| 18003 | Mir5624 | NR_049198.1 | chr13:94560732-94560792 | 18098 | Mir6415 | NR_105843.1 | chr5:92887583-92887682 |
| 18004 | Mir5625 | NR_049199.1 | chr5:30960309-30960388 | 18099 | Mir6416 | NR_105844.1 | chr7:71394869-71394985 |
| 18005 | Mir5626 | NR_049200.1 | chr9:70253500-70253560 | 18100 | Mir6417 | NR_105845.1 | chr5:52527140-52527256 |
| 18006 | Mir5627 | NR_049203.1 | chr12:45311299-45311360 | 18101 | Mir6418 | NR_105846.1 | chr5:137970708-137970822 |
| 18007 | Mir568 | NR_030576.1 | chr16:43640767-43640850 | 18102 | Mir6419 | NR_105847.1 | chr2:17485141-17485253 |
| 18008 | Mir5709 | NR_049205.1 | chr17:67375487-67375575 | 18103 | Mir6420 | NR_105848.1 | chr17:64790145-64790247 |
| 18009 | Mir5710 | NR_049206.1 | chr9:54556120-54556188 | 18104 | Mir6481 | NR_105852.1 | chr3:99003268-99003376 |
| 18010 | Mir574 | NR_030577.1 | chr5:65361557-65361634 | 18105 | Mir6516 | NR_105853.1 | chr11:116938662-116938771 |
| 18011 | Mir582 | NR_030644.1 | chr13:110114938-110115017 | 18106 | Mir6537 | NR_105855.1 | chr6:3671301-3671385 |
| 18012 | Mir592 | NR_030420.1 | chr6:27886655-27886750 | 18107 | Mir6538 | NR_105856.1 | chr7:25882085-25882194 |
| 18013 | Mir598 | NR_030611.1 | chr14:64846026-64846104 | 18108 | Mir6538 | NR_105856.1 | chr12:27099766-27099875 |
| 18014 | Mir599 | NR_035527.1 | chr15:35590586-35590673 | 18109 | Mir6539 | NR_105857.1 | chr14:68477693-68477802 |
| 18015 | Mir615 | NR_030526.1 | chr15:102845341-102845432 | 18110 | Mir654 | NR_030578.1 | chr12:110981427-110961511 |
| 18016 | Mir6236 | NR_105744.1 | chr9:110183790-110183913 | 18111 | Mir6540 | NR_105858.1 | chr16:42303475-42303582 |
| 18017 | Mir6237 | NR_105745.1 | chr9:9894431-9894521 | 18112 | Mir6541 | NR_105860.1 | chr14:63484379-63484488 |
| 18018 | Mir6238 | NR_105746.1 | chr7:61147130-61147259 | 18113 | Mir6546 | NR_106103.1 | chr1:172994721-172994783 |
| 18019 | Mir6239 | NR_105747.1 | chr14:118352965-118353069 | 18114 | Mir664 | NR_035529.1 | chr1:187066854-187066922 |
| 18020 | Mir6240 | NR_105748.1 | chr2:145076789-145209256 | 18115 | Mir665 | NR_030425.1 | chr12:110824523-110824617 |
| 18021 | Mir6241 | NR_105749.1 | chr14:118657855-118657958 | 18116 | Mir666 | NR_030435.1 | chr12:110955294-110955393 |
| 18022 | Mir6244 | NR_105750.1 | chr9:51923728-51923844 | 18117 | Mir667 | NR_030426.1 | chr12:110958215-110958307 |
| 18023 | Mir6335 | NR_105752.1 | chr2:67619099-67619197 | 18118 | Mir668 | NR_030424.1 | chr12:110972941-110973007 |
| 18024 | Mir6336 | NR_105754.1 | chr2:42302959-42303088 | 18119 | Mir669a-1 | NR_035408.1 | chr2:10292077-10516880 |
| 18025 | Mir6337 | NR_105755.1 | chr2:65202352-65202457 | 18120 | Mir669a-1 | NR_035408.1 | chr2:10292077-10516880 |
| 18026 | Mir6338 | NR_105756.1 | chr11:72202257-72202366 | 18121 | Mir669a-1 | NR_035408.1 | chr2:10292077-10516880 |
| 18027 | Mir6339 | NR_105757.1 | chr2:129842028-129842144 | 18122 | Mir669a-1 | NR_035408.1 | chr2:10292077-10516880 |
| 18028 | Mir6340 | NR_105758.1 | chr2:173526531-173526649 | 18123 | Mir669a-1 | NR_035408.1 | chr2:10292077-10516880 |
| 18029 | Mir6341 | NR_105759.1 | chr1:12416066-12416187 | 18124 | Mir669a-1 | NR_035408.1 | chr2:10292077-10516880 |
| 18030 | Mir6342 | NR_105760.1 | chr1:29478332-29478457 | 18125 | Mir669a-1 | NR_035408.1 | chr2:10292077-10516880 |
| 18031 | Mir6343 | NR_105761.1 | chr1:76506134-76506218 | 18126 | Mir669a-1 | NR_035408.1 | chr2:10292077-10516880 |
| 18032 | Mir6344 | NR_105762.1 | chr1:82128490-82128594 | 18127 | Mir669a-1 | NR_035408.1 | chr2:10292077-10516880 |
| 18033 | Mir6345 | NR_105763.1 | chr1:95248735-95248862 | 18128 | Mir669a-1 | NR_035408.1 | chr2:10292077-10516880 |
| 18034 | Mir6348 | NR_105766.1 | chr1:170420773-170420893 | 18129 | Mir669a-11 | NR_037266.1 | chr2:10,398,484-10,425,504 |
| 18035 | Mir6349 | NR_105767.1 | chr1:39243740-39243837 | 18130 | Mir669a-12 | NR_037268.1 | chr2:10292077-10516880 |
| 18036 | Mir6350 | NR_105768.1 | chr1:47523864-47523969 | 18131 | Mir669a-12 | NR_037268.1 | chr2:10292077-10516880 |
| 18037 | Mir6351 | NR_105769.1 | chr1:73902051-73902149 | 18132 | Mir669a-2 | NR_030470.1 | chr2:10292077-10516880 |
| 18038 | Mir6352 | NR_105770.1 | chr1:77493228-77493343 | 18133 | Mir669a-2 | NR_030470.1 | chr2:10292077-10516880 |
| 18039 | Mir6353 | NR_105771.1 | chr1:84215424-84215536 | 18134 | Mir669a-2 | NR_030470.1 | chr2:10292077-10516880 |
| 18040 | Mir6355 | NR_105773.1 | chr18:59739283-59739389 | 18135 | Mir669a-2 | NR_030470.1 | chr2:10292077-10516880 |
| 18041 | Mir6356 | NR_105774.1 | chr18:68899053-68899155 | 18136 | Mir669a-2 | NR_030470.1 | chr2:10292077-10516880 |
| 18042 | Mir6357 | NR_105775.1 | chr18:70676440-70676543 | 18137 | Mir669a-2 | NR_030470.1 | chr2:10292077-10516880 |
| 18043 | Mir6358 | NR_105776.1 | chr18:76330205-76330306 | 18138 | Mir669a-2 | NR_030470.1 | chr2:10292077-10516880 |
| 18044 | Mir6359 | NR_105777.1 | chr18:89141422-89141502 | 18139 | Mir669a-2 | NR_030470.1 | chr2:10292077-10516880 |
| 18045 | Mir6360 | NR_105778.1 | chr18:23933365-23933490 | 18140 | Mir669a-2 | NR_030470.1 | chr2:10292077-10516880 |
| 18046 | Mir6361 | NR_105779.1 | chr18:33040226-33040327 | 18141 | Mir669a-2 | NR_030470.1 | chr2:10292077-10516880 |
| 18047 | Mir6362 | NR_105781.1 | chr5:30115550-30297028 | 18142 | Mir669a-3 | NR_030471.1 | chr2:10396060-10396168 |
| 18048 | Mir6363 | NR_105782.1 | chr16:50727245-50727358 | 18143 | Mir669a-4 | NR_037250.1 | chr2:10292077-10516880 |
| 18049 | Mir6364 | NR_105783.1 | chr2:166498218-166547652 | 18144 | Mir669a-4 | NR_037250.1 | chr2:10292077-10516880 |
| 18050 | Mir6365 | NR_105784.1 | chr16:13471172-13471273 | 18145 | Mir669a-4 | NR_037250.1 | chr2:10292077-10516880 |
| 18051 | Mir6366 | NR_105785.1 | chr16:18165181-18165263 | 18146 | Mir669a-4 | NR_037250.1 | chr2:10292077-10516880 |
| 18052 | Mir6367 | NR_105786.1 | chr16:91527687-91527789 | 18147 | Mir669a-5 | NR_037251.1 | chr2:10,398,484-10,425,504 |
| 18053 | Mir6368 | NR_105787.1 | chr13:28802650-28802742 | 18148 | Mir669a-9 | NNR_037260.1 | chr2:10292077-10516880 |
| 18054 | Mir6369 | NR_105788.1 | chr13:58388876-58456223 | 18149 | Mir669a-9 | NNR_037260.1 | chr2:10292077-10516880 |
| 18055 | Mir6369 | NR_105788.1 | chr5:31235515-31651218 | 18150 | Mir669b | NR_030469.1 | chr2:10389417-10389513 |
| 18056 | Mir6370 | NR_105789.1 | chr6:19505341-19505461 | 18151 | Mir669c | NR_030473.1 | chr2:10430923-10431031 |
| 18057 | Mir6372 | NR_105791.1 | chr11:26102240-26102348 | 18152 | Mir669e | NR_035426.1 | chr2:10389122-10389240 |
| 18058 | Mir6373 | NR_105792.1 | chr6:102744377-102744479 | 18153 | Mir669g | NR_035411.1 | chr2:10398777-10398899 |
| 18059 | Mir6374 | NR_105793.1 | chr6:83350990-83351096 | 18154 | Mir669h | NR_035418.1 | chr2:10439782-10439906 |
| 18060 | Mir6375 | NR_105794.1 | chr6:85740133-85740228 | 18155 | Mir669i | NR_035417.1 | chr2:10439231-10439357 |
| 18061 | Mir6376 | NR_105795.1 | chr6:88054122-88054252 | 18156 | Mir669j | NR_035416.1 | chr2:10399537-10399657 |
| 18062 | Mir6378 | NR_105799.1 | chr3:34821466-34821573 | 18157 | Mir669k | NR_035410.1 | chr2:10396927-10397053 |
| 18063 | Mir6380 | NR_105801.1 | chr12:61837949-61837970 | 18158 | Mir669l-1 | NR_035474.1 | chr2:10435062-10435155 |
| 18064 | Mir6381 | NR_105802.1 | chr3:142286824-142286910 | 18159 | Mir669m-1 | NR_035475.1 | chr2:10435061-10435158 |
| 18065 | Mir6382 | NR_105803.1 | chrX:103505164-103505274 | 18160 | Mir669p-1 | NR_037257.1 | chr2:10410743-10418210 |
| 18066 | Mir6383 | NR_105804.1 | chrX:132717783-132717899 | 18161 | Mir669p-2 | NR_037262.1 | chr2:10,410,743-10,418,210 |
| 18067 | Mir6384 | NR_105805.1 | chrX:49731298-49731358 | 18162 | Mir670 | NR_030431.1 | chr2:94101456-94101556 |
| 18068 | Mir6385 | NR_105806.1 | chr9:58068957-58069061 | 18163 | Mir671 | NR_030423.1 | chr5:24097932-24098029 |
| 18069 | Mir6386 | NR_105808.1 | chr9:92162096-92162199 | 18164 | Mir6715 | NR_106146.1 | chr19:55267168-55267224 |
| 18070 | Mir6387 | NR_105809.1 | chr12:158078000-158079075 | 18165 | Mir672 | NR_030430.1 | chrX:101311514-101311613 |
| 18071 | Mir6388 | NR_105810.1 | chr12:116933930-116934005 | 18166 | Mir673 | NR_030438.1 | chr12:110810199-110810290 |

Fig. 25 - 97

| | | | | | | | | |
|---|---|---|---|---|---|---|---|---|
| 18167 | Mir674 | NR_030440.1 | chr2:117010862-117010962 | | 18262 | Mir6956 | NR_105921.1 | chr15:78832653-78832714 |
| 18168 | Mir675 | NR_030416.1 | chr7:149762969-149763052 | | 18263 | Mir6957 | NR_105922.1 | chr15:80476503-80476566 |
| 18169 | Mir676 | NR_030525.1 | chrX:97576436-97576524 | | 18264 | Mir6958 | NR_105923.1 | chr15:89015895-89015967 |
| 18170 | Mir6769b | NR_106035.1 | chr8:74154946-74155005 | | 18265 | Mir6959 | NR_105924.1 | chr15:89136089-89136163 |
| 18171 | Mir677 | NR_030442.2 | chr10:127522342-127522419 | | 18266 | Mir6960 | NR_105925.1 | chr15:98911236-98911296 |
| 18172 | Mir678 | NR_030443.1 | chr10:75670071-75670154 | | 18267 | Mir6961 | NR_105926.1 | chr15:100479594-100479660 |
| 18173 | Mir679 | NR_030445.1 | chr12:110953786-110953860 | | 18268 | Mir6962 | NR_105927.1 | chr15:101024300-101024362 |
| 18174 | Mir680-1 | NR_030447.1 | chr6:129641552-129641661 | | 18269 | Mir6963 | NR_105928.1 | chr15:103180886-103180956 |
| 18175 | Mir680-2 | NR_030448.1 | chrX:140732332-140732442 | | 18270 | Mir6964 | NR_105929.1 | chr16:98098840-98098898 |
| 18176 | Mir680-3 | NR_030449.1 | chr12:35879482-35879569 | | 18271 | Mir6965 | NR_105930.1 | chr17:24377829-24377892 |
| 18177 | Mir681 | NR_030450.1 | chr12:70864822-70864931 | | 18272 | Mir6966 | NR_105932.1 | chr17:25917753-25917824 |
| 18178 | Mir682 | NR_030451.1 | chr13:75782493-75782589 | | 18273 | Mir6968 | NR_105934.1 | chr17:27072417-27072484 |
| 18179 | Mir683-1 | NR_030453.1 | chr13:50639994-50640103 | | 18274 | Mir6969 | NR_105935.1 | chr17:28695386-28695446 |
| 18180 | Mir683-1 | NR_030453.1 | chr13:50696346-50696449 | | 18275 | Mir697 | NR_030479.1 | chr4:124408938-124409046 |
| 18181 | Mir684-1 | NR_030454.1 | chr2:36245430-36245515 | | 18276 | Mir6970 | NR_105936.1 | chr17:34982046-34982112 |
| 18182 | Mir684-1 | NR_030454.1 | chr10:129102810-129102895 | | 18277 | Mir6971 | NR_105937.1 | chr17:34978754-34978816 |
| 18183 | Mir684-1 | NR_030454.1 | chr7:134542429-134542514 | | 18278 | Mir6972 | NR_105938.1 | chr17:34994514-34994577 |
| 18184 | Mir684-1 | NR_030454.1 | chrX:7330214-7330299 | | 18279 | Mir6973a | NR_105939.1 | chr17:35331917-35331994 |
| 18185 | Mir684-1 | NR_030454.1 | chr5:23763345-23763430 | | 18280 | Mir6973b | NR_105969.1 | chr2:130866055-130866134 |
| 18186 | Mir684-1 | NR_030454.1 | chr11:115384422-115397544 | | 18281 | Mir6974 | NR_105940.1 | chr17:35341420-35341502 |
| 18187 | Mir684-1 | NR_030454.1 | chr16:20141135-20232646 | | 18282 | Mir6975 | NR_105941.1 | chr17:35381020-35381080 |
| 18188 | Mir684-1 | NR_030454.1 | chr11:74739373-74977950 | | 18283 | Mir6976 | NR_105942.1 | chr17:46690776-46690838 |
| 18189 | Mir684-1 | NR_030454.1 | chr2:80457370-80471818 | | 18284 | Mir6977 | NR_105943.1 | chr17:56558269-56558332 |
| 18190 | Mir684-2 | NR_030455.1 | chr4:11061243-11061329 | | 18285 | Mir6978 | NR_105944.1 | chr17:57356595-57356651 |
| 18191 | Mir686 | NR_030457.1 | chr14:55235514-55235622 | | 18286 | Mir6979 | NR_105945.1 | chr18:38014259-38014314 |
| 18192 | Mir687 | NR_030459.1 | chr14:73606570-73606658 | | 18287 | Mir698 | NR_030480.1 | chr4:124421025-124421133 |
| 18193 | Mir688 | NR_030460.1 | chr15:102502222-102502297 | | 18288 | Mir6980 | NR_105946.1 | chr18:38150541-38150599 |
| 18194 | Mir6896 | NR_105861.1 | chr1:34174204-34174276 | | 18289 | Mir6981 | NR_105947.1 | chr18:38134157-38134271 |
| 18195 | Mir6897 | NR_105862.1 | chr1:36201097-36201158 | | 18290 | Mir6982 | NR_105948.1 | chr18:61117727-61117794 |
| 18196 | Mir6898 | NR_105863.1 | chr1:36405527-36405603 | | 18291 | Mir6983 | NR_105949.1 | chr18:61277122-61277185 |
| 18197 | Mir6899 | NR_105864.1 | chr1:64089012-64089075 | | 18292 | Mir6984 | NR_105950.1 | chr19:3288920-3288983 |
| 18198 | Mir690 | NR_030463.1 | chr16:28600021-28600129 | | 18293 | Mir6985 | NR_105951.1 | chr19:4263818-4263878 |
| 18199 | Mir6900 | NR_105865.1 | chr1:94361060-94361119 | | 18294 | Mir6986 | NR_105952.1 | chr19:4623898-4623955 |
| 18200 | Mir6901 | NR_105866.1 | chr1:95171126-95171187 | | 18295 | Mir6987 | NR_105953.1 | chr19:5679004-5679076 |
| 18201 | Mir6902 | NR_105867.1 | chr1:95242669-95242732 | | 18296 | Mir6988 | NR_105954.1 | chr19:6051334-6051392 |
| 18202 | Mir6903 | NR_105868.1 | chr1:135623135-135623222 | | 18297 | Mir6989 | NR_105955.1 | chr19:6346480-6346544 |
| 18203 | Mir6904 | NR_105869.1 | chr1:182517332-182517398 | | 18298 | Mir6990 | NR_105956.1 | chr19:6988686-6988776 |
| 18204 | Mir6905 | NR_105870.1 | chr10:24630470-24630539 | | 18299 | Mir6991 | NR_105957.1 | chr19:7497063-7497132 |
| 18205 | Mir6906 | NR_105871.1 | chr10:59589524-59589581 | | 18300 | Mir6992 | NR_105958.1 | chr19:8817461-8817569 |
| 18206 | Mir6907 | NR_105872.1 | chr10:77871220-77871290 | | 18301 | Mir6993 | NR_105959.1 | chr19:10265865-10265929 |
| 18207 | Mir6908 | NR_105873.1 | chr10:77907840-77907902 | | 18302 | Mir6994 | NR_105960.1 | chr19:11998218-11998290 |
| 18208 | Mir6909 | NR_105874.1 | chr10:78993774-78993835 | | 18303 | Mir6995 | NR_105961.1 | chr19:47348009-47348079 |
| 18209 | Mir691 | NR_030464.1 | chr16:74342235-74342312 | | 18304 | Mir6996 | NR_105962.1 | chr2:26325579-26325639 |
| 18210 | Mir6910 | NR_105875.1 | chr10:79325332-79325397 | | 18305 | Mir6997 | NR_105963.1 | chr2:29851470-29851540 |
| 18211 | Mir6911 | NR_105876.1 | chr10:79740909-79740977 | | 18306 | Mir6998 | NR_105964.1 | chr2:31467941-31468004 |
| 18212 | Mir6912 | NR_105877.1 | chr10:80072005-80072074 | | 18307 | Mir6999 | NR_105965.1 | chr2:91785027-91785087 |
| 18213 | Mir6913 | NR_105878.1 | chr10:80849092-80849157 | | 18308 | Mir700 | NR_030481.1 | chr4:134972470-134972548 |
| 18214 | Mir6914 | NR_105879.1 | chr10:127819894-127819962 | | 18309 | Mir7000 | NR_105966.1 | chr2:92227541-92227603 |
| 18215 | Mir6915 | NR_105880.1 | chr10:127825888-127825956 | | 18310 | Mir7001 | NR_105967.1 | chr2:93262086-93262164 |
| 18216 | Mir6916 | NR_105881.1 | chr10:127949024-127949086 | | 18311 | Mir7002 | NR_105968.1 | chr2:113976252-113976306 |
| 18217 | Mir6917 | NR_105882.1 | chr10:128021493-128021553 | | 18312 | Mir7003 | NR_105970.1 | chr2:162893826-162893891 |
| 18218 | Mir6918 | NR_105883.1 | chr11:4791348-4791405 | | 18313 | Mir7004 | NR_105971.1 | chr2:168466196-168466259 |
| 18219 | Mir6919 | NR_105884.1 | chr11:50045747-50045808 | | 18314 | Mir7005 | NR_105972.1 | chr2:179914460-179914528 |
| 18220 | Mir6920 | NR_105885.1 | chr11:53222699-53222769 | | 18315 | Mir7006 | NR_105973.1 | chr2:181322605-181322673 |
| 18221 | Mir6921 | NR_105886.1 | chr11:60014040-60014119 | | 18316 | Mir7007 | NR_105974.1 | chr3:20122189-20122258 |
| 18222 | Mir692-1 | NR_030465.1 | chr17:7099577-7099686 | | 18317 | Mir7008 | NR_105975.1 | chr3:30937888-30937950 |
| 18223 | Mir6922 | NR_105887.1 | chr11:60015764-60015829 | | 18318 | Mir7009 | NR_105976.1 | chr3:36374383-36374446 |
| 18224 | Mir692-2a | NR_109835.1 | chr4:74544513-125182101 | | 18319 | Mir701 | NR_030482.1 | chr5:111433163-111433271 |
| 18225 | Mir692-2b | NR_035409.1 | chr3:74544512-74544621 | | 18320 | Mir7010 | NR_105977.1 | chr3:81910169-81910231 |
| 18226 | Mir6923 | NR_105888.1 | chr11:66913306-66913377 | | 18321 | Mir7011 | NR_105978.1 | chr3:88244801-88244873 |
| 18227 | Mir6924 | NR_105889.1 | chr11:69695534-69695596 | | 18322 | Mir7012 | NR_105979.1 | chr3:90074071-90074134 |
| 18228 | Mir6925 | NR_105890.1 | chr11:70519492-70519561 | | 18323 | Mir7013 | NR_105980.1 | chr3:94808090-94808161 |
| 18229 | Mir6926 | NR_105891.1 | chr11:74681629-74681696 | | 18324 | Mir7014 | NR_105981.1 | chr3:95538834-95538896 |
| 18230 | Mir6927 | NR_105892.1 | chr11:97538374-97538444 | | 18325 | Mir7015 | NR_105982.1 | chr4:120645864-120645927 |
| 18231 | Mir6928 | NR_105893.1 | chr11:100891654-100891723 | | 18326 | Mir7016 | NR_105983.1 | chr4:129361744-129361815 |
| 18232 | Mir6929 | NR_105894.1 | chr11:101280501-101280567 | | 18327 | Mir7017 | NR_105984.1 | chr4:132751570-132751631 |
| 18233 | Mir693 | NR_030466.1 | chr17:46368480-46368568 | | 18328 | Mir7018 | NR_105985.1 | chr4:137094201-137094285 |
| 18234 | Mir6930 | NR_105895.1 | chr11:102266234-102266301 | | 18329 | Mir7019 | NR_105986.1 | chr4:137872047-137872115 |
| 18235 | Mir6931 | NR_105896.1 | chr11:102861162-102861235 | | 18330 | Mir702 | NR_030483.1 | chr4:137467303-137467411 |
| 18236 | Mir6932 | NR_105897.1 | chr11:107499036-107499093 | | 18331 | Mir7020 | NR_105987.1 | chr4:139199957-139200026 |
| 18237 | Mir6933 | NR_105898.1 | chr11:117863584-117863664 | | 18332 | Mir7021 | NR_105988.1 | chr4:142726003-142726065 |
| 18238 | Mir6934 | NR_105899.1 | chr11:119015390-119015451 | | 18333 | Mir7022 | NR_105989.1 | chr4:147521045-147521105 |
| 18239 | Mir6935 | NR_105900.1 | chr11:120208664-120208727 | | 18334 | Mir7023 | NR_105990.1 | chr4:149029613-149029676 |
| 18240 | Mir6936 | NR_105901.1 | chr11:120486137-120486190 | | 18335 | Mir7024 | NR_105991.1 | chr5:34241559-34241620 |
| 18241 | Mir6937 | NR_105902.1 | chr12:29364190-29364254 | | 18336 | Mir7025 | NR_105992.1 | chr5:75572856-75572929 |
| 18242 | Mir6938 | NR_105903.1 | chr12:86586873-86586935 | | 18337 | Mir7026 | NR_105993.1 | chr5:111095094-111095160 |
| 18243 | Mir6939 | NR_105904.1 | chr12:113897488-113897562 | | 18338 | Mir7027 | NR_105994.1 | chr5:114854477-114854548 |
| 18244 | Mir694 | NR_030467.1 | chr18:66378918-66378987 | | 18339 | Mir7028 | NR_105995.1 | chr5:115169524-115169587 |
| 18245 | Mir6940 | NR_105905.1 | chr12:113971533-113971602 | | 18340 | Mir7029 | NR_105996.1 | chr5:116030958-116031018 |
| 18246 | Mir6941 | NR_105906.1 | chr12:114158694-114158752 | | 18341 | Mir703 | NR_030484.1 | chr5:98904575-98904683 |
| 18247 | Mir6942 | NR_105907.1 | chr13:21488447-21488507 | | 18342 | Mir7030 | NR_105997.1 | chr5:116095582-116095641 |
| 18248 | Mir6943 | NR_105908.1 | chr13:55554467-55554532 | | 18343 | Mir7031 | NR_105998.1 | chr5:122269218-122269282 |
| 18249 | Mir6944 | NR_105909.1 | chr13:55579042-55579137 | | 18344 | Mir7032 | NR_105999.1 | chr5:124446861-124446939 |
| 18250 | Mir6945 | NR_105910.1 | chr13:55608986-55609053 | | 18345 | Mir7033 | NR_106000.1 | chr5:135859600-135859680 |
| 18251 | Mir6946 | NR_105911.1 | chr14:21509857-21509925 | | 18346 | Mir7034 | NR_106001.1 | chr5:136211676-136211759 |
| 18252 | Mir6947 | NR_105912.1 | chr14:30802074-30802138 | | 18347 | Mir7035 | NR_106002.1 | chr5:136581392-136581473 |
| 18253 | Mir6948 | NR_105913.1 | chr14:55261886-55261947 | | 18348 | Mir7036 | NR_106003.1 | chr5:137737852-137737916 |
| 18254 | Mir6949 | NR_105914.1 | chr14:56701238-56701305 | | 18349 | Mir7036b | NR_106111.1 | chr5:34916800-34916862 |
| 18255 | Mir695 | NR_030475.1 | chr2:155182553-155182661 | | 18350 | Mir7037 | NR_106004.1 | chr5:140243833-140243897 |
| 18256 | Mir6950 | NR_105915.1 | chr14:70092055-70092127 | | 18351 | Mir7038 | NR_106005.1 | chr5:140903293-140903363 |
| 18257 | Mir6951 | NR_105916.1 | chr15:38420228-38420302 | | 18352 | Mir7039 | NR_106006.1 | chr5:145657601-145657685 |
| 18258 | Mir6952 | NR_105917.1 | chr15:75895258-75895318 | | 18353 | Mir704 | NR_030485.1 | chr6:47753575-47753651 |
| 18259 | Mir6953 | NR_105918.1 | chr15:76078621-76078688 | | 18354 | Mir7040 | NR_106007.1 | chr6:82999705-82999767 |
| 18260 | Mir6954 | NR_105919.1 | chr15:76263644-76263703 | | 18355 | Mir7041 | NR_106008.1 | chr6:94556358-94556409 |
| 18261 | Mir6955 | NR_105920.1 | chr15:78722270-78722343 | | 18356 | Mir7042 | NR_106009.1 | chr6:113657202-113657259 |

Fig. 25 - 98

| | | | | | | | | |
|---|---|---|---|---|---|---|---|---|
| 18357 | Mir7043 | NR_106010.1 | chr6:116595996-116596065 | | 18452 | Mir7234 | NR_106093.1 | chr7:80964475-80964527 |
| 18358 | Mir7044 | NR_106011.1 | chr6:118035210-118035281 | | 18453 | Mir7235 | NR_106094.1 | chr11:97007678-97007733 |
| 18359 | Mir7045 | NR_106012.1 | chr6:125047042-125047104 | | 18454 | Mir7236 | NR_106095.1 | chr11:121248459-121248518 |
| 18360 | Mir7046 | NR_106013.1 | chr7:25755029-25755094 | | 18455 | Mir7237 | NR_106096.1 | chr8:124501924-124501986 |
| 18361 | Mir7047 | NR_106014.1 | chr7:25772623-25772686 | | 18456 | Mir7238 | NR_106097.1 | chr8:11635694-11635736 |
| 18362 | Mir7048 | NR_106015.1 | chr7:26002687-26002744 | | 18457 | Mir7239 | NR_106098.1 | chr11:45983588-45983645 |
| 18363 | Mir7049 | NR_106016.1 | chr7:29345944-29346003 | | 18458 | Mir7240 | NR_106099.1 | chr8:73322033-73322091 |
| 18364 | Mir705 | NR_030486.1 | chr6:85286286-85286367 | | 18459 | Mir7241 | NR_106100.1 | chr9:67575523-67575587 |
| 18365 | Mir7050 | NR_106017.1 | chr7:31825277-31825336 | | 18460 | Mir7242 | NR_106101.1 | chr9:67577305-67577384 |
| 18366 | Mir7051 | NR_106018.1 | chr7:50712867-50712939 | | 18461 | Mir7243 | NR_106163.1 | chr9:102207254-102207305 |
| 18367 | Mir7052 | NR_106019.1 | chr7:51725717-51725781 | | 18462 | Mir741 | NR_030530.1 | chrX:64049979-64050050 |
| 18368 | Mir7053 | NR_106020.1 | chr7:51793476-51793548 | | 18463 | Mir742 | NR_030531.1 | chrX:64033547-64033612 |
| 18369 | Mir7054 | NR_106021.1 | chr7:52267796-52267857 | | 18464 | Mir743 | NR_030532.1 | chrX:64029931-64029993 |
| 18370 | Mir7055 | NR_106022.1 | chr7:52428673-52428731 | | 18465 | Mir743b | NR_030535.1 | chrX:64030430-64030507 |
| 18371 | Mir7056 | NR_106023.1 | chr7:54338536-54338594 | | 18466 | Mir744 | NR_030417.1 | chr11:65548235-65548334 |
| 18372 | Mir7057 | NR_106024.1 | chr7:73526553-73526610 | | 18467 | Mir7578 | NR_106102.1 | chr2:27306089-27306150 |
| 18373 | Mir7058 | NR_106025.1 | chr7:133511485-133511559 | | 18468 | Mir758 | NR_030421.1 | chr12:110951019-110951100 |
| 18374 | Mir7059 | NR_106026.1 | chr7:133722988-133723046 | | 18469 | Mir759 | NR_030436.1 | chr14:80138237-80138335 |
| 18375 | Mir706 | NR_030487.1 | chr6:119984246-119984329 | | 18470 | Mir760 | NR_030439.1 | chr3:121996502-121996621 |
| 18376 | Mir7060 | NR_106027.1 | chr7:134632765-134632901 | | 18471 | Mir761 | NR_030432.1 | chr4:108690260-108690335 |
| 18377 | Mir7061 | NR_106028.1 | chr7:138051782-138051849 | | 18472 | Mir762 | NR_030428.1 | chr7:134852001-134852076 |
| 18378 | Mir7062 | NR_106029.1 | chr7:147172708-147172773 | | 18473 | Mir763 | NR_030434.1 | chr10:119885047-119885166 |
| 18379 | Mir7063 | NR_106030.1 | chr7:148806600-148806690 | | 18474 | Mir764 | NR_030433.1 | chrX:143436802-143436909 |
| 18380 | Mir7064 | NR_106031.1 | chr7:150756576-150756664 | | 18475 | Mir7646 | NR_106104.1 | chrX:132281255-132281308 |
| 18381 | Mir7065 | NR_106032.1 | chr8:13136072-13136132 | | 18476 | Mir7647 | NR_106105.1 | chr5:123972646-123972704 |
| 18382 | Mir7066 | NR_106033.1 | chr8:72626423-72626485 | | 18477 | Mir7648 | NR_106106.1 | chr15:90054791-90054843 |
| 18383 | Mir7067 | NR_106034.1 | chr8:73419407-73419469 | | 18478 | Mir7649 | NR_106107.1 | chr6:128881810-128881863 |
| 18384 | Mir7068 | NR_106036.1 | chr8:74993915-74993988 | | 18479 | Mir7649 | NR_106107.1 | chr6:128884398-128934725 |
| 18385 | Mir7069 | NR_106037.1 | chr8:87391846-87391907 | | 18480 | Mir7650 | NR_106108.1 | chr9:15117055-15117113 |
| 18386 | Mir707 | NR_030488.1 | chr7:52105069-52105141 | | 18481 | Mir7652 | NR_106112.1 | chr1:151871390-151899332 |
| 18387 | Mir7070 | NR_106038.1 | chr8:87585985-87586070 | | 18482 | Mir7653 | NR_106113.1 | chr11:77992329-77992389 |
| 18388 | Mir7071 | NR_106039.1 | chr8:90662105-90662173 | | 18483 | Mir7654 | NR_106114.1 | chr8:8690093-8690162 |
| 18389 | Mir7072 | NR_106040.1 | chr8:97028946-97029005 | | 18484 | Mir7655 | NR_106115.1 | chr2:17979473-17979530 |
| 18390 | Mir7073 | NR_106041.1 | chr8:98277051-98277114 | | 18485 | Mir7656 | NR_106116.1 | chr9:94652248-94652309 |
| 18391 | Mir7074 | NR_106042.1 | chr8:108475537-108475599 | | 18486 | Mir7657 | NR_106117.1 | chr3:122244543-122244599 |
| 18392 | Mir7075 | NR_106043.1 | chr8:109619925-109620006 | | 18487 | Mir7658 | NR_106118.1 | chr4:155604168-155604224 |
| 18393 | Mir7076 | NR_106044.1 | chr8:114213501-114213574 | | 18488 | Mir7659 | NR_106119.1 | chr10:77802895-77802952 |
| 18394 | Mir7077 | NR_106045.1 | chr8:119976923-119976979 | | 18489 | Mir7661 | NR_106121.1 | chr6:108439737-108439797 |
| 18395 | Mir7078 | NR_106046.1 | chr8:119983165-119983228 | | 18490 | Mir7662 | NR_106122.1 | chr10:61656915-61656975 |
| 18396 | Mir7079 | NR_106047.1 | chr8:125628875-125628943 | | 18491 | Mir7663 | NR_106123.1 | chr10:22449178-22449238 |
| 18397 | Mir708 | NR_030489.1 | chr7:103397934-103398042 | | 18492 | Mir7665 | NR_106125.1 | chr2:119843253-119843315 |
| 18398 | Mir7080 | NR_106048.1 | chr8:125654006-125654072 | | 18493 | Mir7666 | NR_106126.1 | chr8:41393228-41393283 |
| 18399 | Mir7081 | NR_106049.1 | chr9:20718534-20718608 | | 18494 | Mir7667 | NR_106127.1 | chr17:29732483-29732545 |
| 18400 | Mir7082 | NR_106050.1 | chr9:20879941-20880032 | | 18495 | Mir7668 | NR_106128.1 | chr7:30691528-30691586 |
| 18401 | Mir7083 | NR_106051.1 | chr9:21614385-21614444 | | 18496 | Mir7669 | NR_106129.1 | chr1:35579458-35579478 |
| 18402 | Mir7084 | NR_106052.1 | chr9:21918388-21918457 | | 18497 | Mir7669 | NR_106129.1 | chr1:91090107-91090127 |
| 18403 | Mir7085 | NR_106053.1 | chr9:44208506-44208571 | | 18498 | Mir7669 | NR_106129.1 | chr10:79210453-79210473 |
| 18404 | Mir7086 | NR_106054.1 | chr9:45074726-45074790 | | 18499 | Mir7669 | NR_106129.1 | chr10:14375138-14425295 |
| 18405 | Mir7087 | NR_106055.1 | chr9:45747604-45747673 | | 18500 | Mir7669 | NR_106129.1 | chrX:162676874-162826965 |
| 18406 | Mir7088 | NR_106056.1 | chr9:107983829-107983914 | | 18501 | Mir767 | NR_035528.1 | chrX:69835327-69835433 |
| 18407 | Mir7089 | NR_106057.1 | chr9:109792147-109792214 | | 18502 | Mir7670 | NR_106130.1 | chr6:38457325-38457393 |
| 18408 | Mir709 | NR_030490.1 | chr8:86609998-86610085 | | 18503 | Mir7671 | NR_106131.1 | chr11:53577098-53577156 |
| 18409 | Mir7090 | NR_106058.1 | chr9:120864204-120864265 | | 18504 | Mir7672 | NR_106132.1 | chr14:27489033-27489094 |
| 18410 | Mir7091 | NR_106059.1 | chrX:71519366-71519444 | | 18505 | Mir7673 | NR_106133.1 | chrX:91519912-91519976 |
| 18411 | Mir7092 | NR_106060.1 | chrX:71562701-71562768 | | 18506 | Mir7674 | NR_106135.1 | chr2:31906466-31906528 |
| 18412 | Mir7093 | NR_106061.1 | chrX:131292170-131292270 | | 18507 | Mir7675 | NR_106136.1 | chr12:11306693-11306750 |
| 18413 | Mir7094-1 | NR_106062.1 | chr12:115707617-115707677 | | 18508 | Mir7676-1 | NR_106137.1 | chr15:78,179,029-78,179,090 ; chr15:78115218-78115279 |
| 18414 | Mir7094-2 | NR_106063.1 | chr12:115751845-115751905 | | 18509 | Mir7676-2 | NR_106138.1 | chr15:78115218-78179090 |
| 18415 | Mir7-1 | NR_029825.1 | chr13:58494140-58494247 | | 18510 | Mir7677 | NR_106142.1 | chr17:27228190-27228256 |
| 18416 | Mir710 | NR_030491.1 | chr8:66993128-66993238 | | 18511 | Mir7678 | NR_106143.1 | chr2:164180049-164180119 |
| 18417 | Mir711 | NR_030492.1 | chr9:108871967-108872048 | | 18512 | Mir7679 | NR_106144.1 | chr11:82798505-82798567 |
| 18418 | Mir7115 | NR_106064.1 | chr1:70251757-70251820 | | 18513 | Mir7680 | NR_106145.1 | chr16:21256086-21256139 |
| 18419 | Mir7117 | NR_106065.1 | chr15:27501249-27501313 | | 18514 | Mir7681 | NR_106149.1 | chr1:53906268-53906399 |
| 18420 | Mir7118 | NR_106066.1 | chr15:88993278-88993338 | | 18515 | Mir7682 | NR_106150.1 | chr1:153289523-153289580 |
| 18421 | Mir7119 | NR_106067.1 | chr4:126237104-126237162 | | 18516 | Mir7683 | NR_106151.1 | chr1:173571971-173572031 |
| 18422 | Mir713 | NR_030493.1 | chr13:62862098-62862206 | | 18517 | Mir7684 | NR_106153.1 | chr15:82224349-82224408 |
| 18423 | Mir717 | NR_030497.1 | chrX:49775684-49775692 | | 18518 | Mir7685 | NR_106156.1 | chr2:158069239-158069301 |
| 18424 | Mir718 | NR_030758.1 | chrX:71269188-71269275 | | 18519 | Mir7686 | NR_106157.1 | chr7:147143464-147143521 |
| 18425 | Mir719 | NR_030458.1 | chr14:60847643-60847752 | | 18520 | Mir7687 | NR_106159.1 | chr8:123062586-123062654 |
| 18426 | Mir7-2 | NR_029826.1 | chr7:86033162-86033259 | | 18521 | Mir770 | NR_030427.1 | chr12:110801902-110801995 |
| 18427 | Mir7210 | NR_030500.1 | chr5:136851586-136851673 | | 18522 | Mir7b | NR_029827.1 | chr17:56382410-56382521 |
| 18428 | Mir7210 | NR_106069.1 | chr14:24908098-24908152 | | 18523 | Mir802 | NR_030429.1 | chr16:93369964-93370061 |
| 18429 | Mir7211 | NR_106070.1 | chr10:94048882-94048944 | | 18524 | Mir804 | NR_030529.1 | chr11:50171286-50171381 |
| 18430 | Mir7212 | NR_106071.1 | chr15:25877982-25878042 | | 18525 | Mir8091 | NR_106166.1 | chr19:41663140-41663279 |
| 18431 | Mir7213 | NR_106072.1 | chr15:79829400-79829456 | | 18526 | Mir8092 | NR_106167.1 | chr19:40969193-40969279 |
| 18432 | Mir7214 | NR_106073.1 | chr17:27453979-27454040 | | 18527 | Mir8093 | NR_106168.1 | chr2:32543150-32543286 |
| 18433 | Mir7215 | NR_106074.1 | chr10:62145256-62145306 | | 18528 | Mir8094 | NR_106169.1 | chr17:35388234-35388350 |
| 18434 | Mir7216 | NR_106075.1 | chr17:27465329-27465405 | | 18529 | Mir8095 | NR_106170.1 | chr16:22532129-22532257 |
| 18435 | Mir7217 | NR_106076.1 | chr17:27492682-27492744 | | 18530 | Mir8096 | NR_106172.1 | chr1:87648522-87648649 |
| 18436 | Mir7218 | NR_106077.1 | chr17:27495041-27495100 | | 18531 | Mir8097 | NR_106173.1 | chr15:36169801-36169919 |
| 18437 | Mir7219 | NR_106078.1 | chr18:68420574-68420627 | | 18532 | Mir8098 | NR_106174.1 | chr14:63456558-63456694 |
| 18438 | Mir7220 | NR_106079.1 | chr18:61113527-61113586 | | 18533 | Mir8099-2 | NR_106201.1 | chr12:95165497-95165624 |
| 18439 | Mir7221 | NR_106080.1 | chr2:92432362-92432434 | | 18534 | Mir8099-2 | NR_106201.1 | chr3:94938009-94846282 |
| 18440 | Mir7222 | NR_106081.1 | chr2:92434758-92434833 | | 18535 | Mir8100 | NR_106177.1 | chr11:45915772-45915892 |
| 18441 | Mir7223 | NR_106082.1 | chr11:107858162-107858230 | | 18536 | Mir8101 | NR_106179.1 | chr11:102091354-102091464 |
| 18442 | Mir7224 | NR_106083.1 | chr2:67513513-67513573 | | 18537 | Mir8102 | NR_106180.1 | chr11:97606210-97606349 |
| 18443 | Mir7225 | NR_106084.1 | chr3:97494432-97494485 | | 18538 | Mir8103 | NR_106181.1 | chr11:96925082-96925188 |
| 18444 | Mir7226 | NR_106085.1 | chr4:117883110-117883169 | | 18539 | Mir8104 | NR_106182.1 | chr10:122116371-122116471 |
| 18445 | Mir7227 | NR_106086.1 | chr4:133272965-133273023 | | 18540 | Mir8105 | NR_106183.1 | chr10:127895735-127895824 |
| 18446 | Mir7228 | NR_106087.1 | chr5:135047945-135047984 | | 18541 | Mir8106 | NR_106185.1 | chr9:122183008-122183146 |
| 18447 | Mir7229 | NR_106088.1 | chr5:113753512-113753565 | | 18542 | Mir8107 | NR_106186.1 | chr9:110538503-110538619 |
| 18448 | Mir7230 | NR_106089.1 | chr5:113766609-113766665 | | 18543 | Mir8108 | NR_106187.1 | chr8:26269597-26269705 |
| 18449 | Mir7231 | NR_106090.1 | chr6:122781495-122781455 | | 18544 | Mir8109 | NR_106189.1 | chr8:88224803-88224920 |
| 18450 | Mir7232 | NR_106091.1 | chr6:81845583-81845657 | | 18545 | Mir8110 | NR_106190.1 | chr8:91548633-91548730 |
| 18451 | Mir7233 | NR_106092.1 | chr6:127738101-127738161 | | | | | |

Fig. 25 - 99

| | | | |
|---|---|---|---|
| 18546 | Mir8111 | NR_106191.1 | chr8:86529526-86529663 |
| 18547 | Mir8112 | NR_106192.1 | chr6:71221664-71221795 |
| 18548 | Mir8113 | NR_106193.1 | chr6:125184702-125184830 |
| 18549 | Mir8114 | NR_106194.1 | chr1:155747056-155747166 |
| 18550 | Mir8115 | NR_106195.1 | chr15:41209536-41423539 |
| 18551 | Mir8116 | NR_106196.1 | chr5:137735008-137735104 |
| 18552 | Mir8118 | NR_106198.1 | chr4:33525056-33525184 |
| 18553 | Mir8119 | NR_106199.1 | chr4:129234927-129235055 |
| 18554 | Mir8120 | NR_106200.1 | chr3:65463209-65463348 |
| 18555 | Mir871 | NR_030536.1 | chrX:64063602-64063679 |
| 18556 | Mir872 | NR_030604.1 | chr4:94331848-94331928 |
| 18557 | Mir873 | NR_030605.1 | chr4:36615543-36615619 |
| 18558 | Mir874 | NR_030544.1 | chr13:58124486-58124561 |
| 18559 | Mir875 | NR_030606.1 | chr15:35590725-35590802 |
| 18560 | Mir876 | NR_030545.1 | chr4:36592406-36592486 |
| 18561 | Mir877 | NR_030608.1 | chr17:36097675-36097759 |
| 18562 | Mir878 | NR_030603.1 | chrX:64054682-64054760 |
| 18563 | Mir879 | NR_030537.1 | chr5:9375704-9375779 |
| 18564 | Mir880 | NR_030538.1 | chrX:64053704-64053782 |
| 18565 | Mir881 | NR_030539.1 | chrX:64055118-64055196 |
| 18566 | Mir882 | NR_030540.1 | chr12:110920406-110920483 |
| 18567 | Mir883a | NR_030541.1 | chrX:64033932-64034008 |
| 18568 | Mir883b | NR_030542.1 | chrX:64043064-64043142 |
| 18569 | Mir9-1 | NR_029817.1 | chr3:88019519-88019608 |
| 18570 | Mir9-2 | NR_029545.1 | chr13:83878418-83878490 |
| 18571 | Mir92-1 | NR_029816.1 | chr14:115443649-115443728 |
| 18572 | Mir92-2 | NR_029748.1 | chrX:50095014-50095105 |
| 18573 | Mir92b | NR_030579.1 | chr3:89031037-89031120 |
| 18574 | Mir93 | NR_029749.1 | chr5:138606751-138606838 |
| 18575 | Mir9-3 | NR_029818.1 | chr7:86650150-86650239 |
| 18576 | Mir96 | NR_029750.1 | chr6:30119445-30119551 |
| 18577 | Mir98 | NR_029753.1 | chrX:148347757-148347864 |
| 18578 | Mir99a | NR_029535.1 | chr16:77599180-77599245 |
| 18579 | Mir99b | NR_029536.1 | chr17:17967151-17967221 |
| 18580 | Mira | NR_045199.1 | chr6:52164489-52165287 |
| 18581 | Mirg | NM_028265.1 | chr12:110973191-110987667 |
| 18582 | Mirlet7a-1 | NR_029725.1 | chr13:48633547-48633641 |
| 18583 | Mirlet7a-2 | NR_029726.1 | chr9:41344798-41344894 |
| 18584 | Mirlet7b | NR_029727.1 | chr15:85537749-85537833 |
| 18585 | Mirlet7bhg | NR_110483.1 | chr15:85534203-85537954 |
| 18586 | Mirlet7c-1 | NR_029728.1 | chr16:77599901-77599995 |
| 18587 | Mirlet7c-2 | NR_029729.1 | chr15:85537033-85537127 |
| 18588 | Mirlet7d | NR_029656.1 | chr13:48631380-48631483 |
| 18589 | Mirlet7e | NR_029730.1 | chr17:17967315-17967408 |
| 18590 | Mirlet7f-1 | NR_029731.1 | chr13:48633197-48633286 |
| 18591 | Mirlet7f-2 | NR_029732.1 | chrX:148346889-148346971 |
| 18592 | Mirlet7g | NR_029526.1 | chr9:106081171-106081258 |
| 18593 | Mirlet7i | NR_029527.1 | chr10:122422695-122422780 |
| 18594 | Mirlet7j | NR_105798.1 | chr3:139691212-139691334 |
| 18595 | Mirlet7k | NR_105854.1 | chr5:148094764-148094874 |
| 18596 | Mis12 | NM_025993.2 | chr11:70833113-70840636 |
| 18597 | Mis18a | NM_025642.1 | chr16:90719556-90727616 |
| 18598 | Mis18bp1 | NM_172578.2 | chr12:66233720-66273567 |
| 18599 | Misp | NM_030218.2 | chr10:79283765-79293197 |
| 18600 | Mitd1 | NM_026913.2 | chr1:37935734-37947256 |
| 18601 | Mitf | NM_001113198.1 | chr6:97757051-97971352 |
| 18602 | Mitf | NM_001178049.1 | chr6:97757051-97971352 |
| 18603 | Mitf | NM_008601.3 | chr6:97757051-97971352 |
| 18604 | Mix | NM_013729.3 | chr1:182623178-182627165 |
| 18605 | Mki67 | NM_001081117.2 | chr7:142881470-142908062 |
| 18606 | Mkks | NM_001141946.1 | chr2:136899515-136895514 |
| 18607 | Mkks | NM_001286981.1 | chr2:136899515-136895514 |
| 18608 | Mkks | NM_001286983.1 | chr2:136899515-136895514 |
| 18609 | Mkks | NM_021527.2 | chr2:136899515-136895514 |
| 18610 | Mkl1 | NM_001082536.1 | chr15:80808194-81021187 |
| 18611 | Mkl1 | NM_153049.3 | chr15:80808194-81021187 |
| 18612 | Mkl2 | NM_001122667.2 | chr16:13256573-13417622 |
| 18613 | Mkl2 | NM_153588.3 | chr16:13256573-13417622 |
| 18614 | Mkl2 | NM_181860.1 | chr16:13256573-13417622 |
| 18615 | Mkln1 | NM_013791.2 | chr6:31348827-31459477 |
| 18616 | Mkln1os | NR_040300.1 | chr6:31316884-31348773 |
| 18617 | Mknk1 | NM_001285487.1 | chr4:115511802-115551861 |
| 18618 | Mknk1 | NM_001285488.1 | chr4:115511802-115551861 |
| 18619 | Mknk1 | NM_021461.5 | chr4:115511802-115551861 |
| 18620 | Mknk2 | NM_021462.4 | chr10:80128073-80134721 |
| 18621 | Mkrn1 | NM_018810.2 | chr6:39347819-39370368 |
| 18622 | Mkrn2 | NM_023290.2 | chr6:115551956-115568688 |
| 18623 | Mkrn3 | NM_011746.2 | chr7:69562478-69565025 |
| 18624 | Mks1 | NM_010390684.2 | chr11:87666726-87677181 |
| 18625 | Mkx | NM_177595.4 | chr18:6934963-7004777 |
| 18626 | Mlana | NM_029993.1 | chr19:29772430-29782796 |
| 18627 | Mlc1 | NM_133241.2 | chr15:88786313-88808883 |
| 18628 | Mlec | NM_175403.3 | chr5:115592989-115608185 |
| 18629 | Mlf1 | NM_001039543.2 | chr3:67178018-67203922 |
| 18630 | Mlf1 | NM_010801.3 | chr3:67178018-67203922 |
| 18631 | Mlf2 | NM_001170341.1 | chr6:124881405-124886167 |
| 18632 | Mlf2 | NM_145385.2 | chr6:124881405-124886167 |
| 18633 | Mlh1 | NM_026810.2 | chr9:111130731-111174112 |
| 18634 | Mlh3 | NM_175337.2 | chr12:86575416-86611549 |
| 18635 | Mlip | NM_001177569.2 | chr9:76949890-77195677 |
| 18636 | Mlkl | NM_029005.2 | chr8:113835699-113861803 |
| 18637 | Mlt1 | NM_022328.2 | chr17:57032033-57074811 |
| 18638 | Mllt10 | NM_001252560.1 | chr2:17976863-18314457 |
| 18639 | Mllt10 | NM_001252561.1 | chr2:17976863-18314457 |
| 18640 | Mllt10 | NM_010804.4 | chr2:17976863-18314457 |
| 18641 | Mllt10 | NR_045538.1 | chr2:17976863-18314457 |
| 18642 | Mllt10 | NR_045539.1 | chr2:17976863-18314457 |
| 18643 | Mllt11 | NM_019914.4 | chr3:95022466-95032599 |
| 18644 | Mllt3 | NM_001286158.1 | chr4:87415828-87679311 |
| 18645 | Mllt3 | NM_027326.3 | chr4:87415828-87679311 |
| 18646 | Mllt3 | NM_029931.3 | chr4:87415828-87679311 |
| 18647 | Mllt4 | NM_010806.1 | chr17:13897548-14042801 |
| 18648 | Mllt6 | NM_139311.2 | chr11:97524726-97546772 |
| 18649 | Mlph | NM_053015.3 | chr1:92811678-92847719 |
| 18650 | Mlst8 | NM_001252463.1 | chr17:24610494-24616023 |
| 18651 | Mlst8 | NM_001252464.1 | chr17:24610494-24616023 |
| 18652 | Mlst8 | NM_001252465.1 | chr17:24610494-24616023 |
| 18653 | Mlst8 | NM_019988.5 | chr17:24610494-24616023 |
| 18654 | Mix | NM_001159384.1 | chr11:100948603-100956749 |
| 18655 | Mix | NM_001159385.1 | chr11:100948603-100956749 |
| 18656 | Mix | NM_011550.3 | chr11:100948603-100956749 |
| 18657 | Mixip | NM_133917.3 | chr5:123844806-123907940 |
| 18658 | Mixip | NM_177582.3 | chr5:123844806-123907940 |
| 18659 | Mixipl | NM_021455.4 | chr5:135582760-135614252 |
| 18660 | Mlycd | NM_019966.2 | chr8:121918791-121934988 |
| 18661 | Mmaa | NM_133823.4 | chr8:81790322-81818855 |
| 18662 | Mmab | NM_029956.3 | chr5:114881042-114894036 |
| 18663 | Mmachc | NM_025962.3 | chr4:116375038-116380990 |
| 18664 | Mmadhc | NM_133839.2 | chr2:50135400-50152197 |
| 18665 | Mmd | NM_026178.2 | chr11:90110789-90139887 |
| 18666 | Mmd2 | NM_175217.6 | chr5:143039434-143084706 |
| 18667 | Mme | NM_001289462.1 | chr3:63099356-63187635 |
| 18668 | Mme | NM_001289463.1 | chr3:63099356-63187635 |
| 18669 | Mme | NM_008604.4 | chr3:63099356-63187635 |
| 18670 | Mmel1 | NM_013783.2 | chr4:154243693-154269639 |
| 18671 | Mmgt1 | NM_146234.3 | chrX:53838689-53851096 |
| 18672 | Mmgt2 | NM_175002.2 | chr11:62462165-62479861 |
| 18673 | Mmp10 | NM_019471.3 | chr9:7502341-7510242 |
| 18674 | Mmp11 | NM_008606.3 | chr10:75385968-75395208 |
| 18675 | Mmp12 | NM_008605.3 | chr9:7347373-7360463 |
| 18676 | Mmp13 | NM_008607.2 | chr9:7272513-7283333 |
| 18677 | Mmp14 | NM_008608.3 | chr14:55050440-55060095 |
| 18678 | Mmp15 | NM_008609.3 | chr8:97876236-97898193 |
| 18679 | Mmp16 | NM_019724.3 | chr4:17780628-18045881 |
| 18680 | Mmp17 | NM_011846.4 | chr5:130090088-130114086 |
| 18681 | Mmp19 | NM_001164197.1 | chr10:128227965-128241426 |
| 18682 | Mmp19 | NM_021412.2 | chr10:128227965-128241426 |
| 18683 | Mmp1a | NM_032006.3 | chr9:7464140-7476869 |
| 18684 | Mmp1b | NM_032007.3 | chr9:7367869-7388026 |
| 18685 | Mmp2 | NM_008610.2 | chr8:95351226-95377319 |
| 18686 | Mmp20 | NM_013903.2 | chr9:7628230-7674968 |
| 18687 | Mmp21 | NM_152944.1 | chr7:140865952-140871744 |
| 18688 | Mmp23 | NM_011985.2 | chr4:155024763-155027493 |
| 18689 | Mmp24 | NM_010808.3 | chr2:155601080-155644102 |
| 18690 | Mmp25 | NM_001033339.3 | chr17:23766424-23782236 |
| 18691 | Mmp27 | NM_001030289.1 | chr9:7571457-7581393 |
| 18692 | Mmp28 | NM_080453.2 | chr11:83255377-83276463 |
| 18693 | Mmp28 | NM_172797.2 | chr11:83255377-83276463 |
| 18694 | Mmp3 | NM_010809.1 | chr9:7445821-7455974 |
| 18695 | Mmp7 | NM_010810.4 | chr9:7692110-7699416 |
| 18696 | Mmp8 | NM_008611.4 | chr9:7558428-7568486 |
| 18697 | Mmp9 | NM_013599.3 | chr2:164773718-164781349 |
| 18698 | Mmrn1 | NM_001163507.1 | chr6:60894310-60939372 |
| 18699 | Mmrn1 | NM_027613.1 | chr6:60894310-60939372 |
| 18700 | Mmrn2 | NM_153127.3 | chr14:35188689-35217472 |
| 18701 | Mms19 | NM_028152.3 | chr19:42018197-42055626 |
| 18702 | Mms22l | NM_199467.2 | chr4:24423608-24530095 |
| 18703 | Mn1 | NM_001081235.1 | chr5:111847185-111886045 |
| 18704 | Mnat1 | NM_008612.2 | chr12:74224703-74374975 |
| 18705 | Mnd1 | NM_029797.3 | chr3:83891855-83959708 |
| 18706 | Mnd1-ps | NR_030680.1 | chr14:10716609-10719382 |
| 18707 | Mnda | NM_001033450.4 | chr1:175826485-175843053 |
| 18708 | Mndal | NM_001170853.1 | chr1:175787350-175810318 |
| 18709 | Mns1 | NM_008613.3 | chr9:72286336-72306383 |
| 18710 | Mnt | NM_010813.3 | chr11:74644425-74659227 |
| 18711 | Mnx1 | NM_019944.2 | chr5:29800362-29805010 |
| 18712 | Moap1 | NM_001142937.2 | chr12:103978039-103996020 |
| 18713 | Moap1 | NM_022323.7 | chr12:103978039-103996020 |
| 18714 | Mob1a | NM_145571.2 | chr6:83276032-83290943 |
| 18715 | Mob1b | NM_026735.2 | chr5:89149895-89187480 |
| 18716 | Mob2 | NM_028308.2 | chr7:149194457-149246939 |
| 18717 | Mob3a | NM_172457.2 | chr10:80147997-80164565 |
| 18718 | Mob3b | NM_178061.5 | chr4:34896323-35104733 |
| 18719 | Mob3c | NM_175308.4 | chr4:115508696-115508788 |
| 18720 | Mob4 | NM_025283.3 | chr1:55188088-55211743 |
| 18721 | Mobp | NM_001039364.2 | chr9:120058859-120085209 |
| 18722 | Mobp | NM_001039365.2 | chr9:120058859-120085209 |
| 18723 | Mobp | NM_008614.2 | chr9:120058859-120085209 |
| 18724 | Mocos | NM_026779.1 | chr18:24812191-24860057 |
| 18725 | Mocs1 | NM_020042.2 | chr17:49567688-49594755 |
| 18726 | Mocs1 | NM_028464.1 | chr17:49567688-49594755 |
| 18727 | Mocs2 | NM_001113374.1 | chr13:115608444-115619628 |
| 18728 | Mocs2 | NM_001113375.1 | chr13:115608444-115619628 |
| 18729 | Mocs2 | NM_013826.3 | chr13:115608444-115619628 |
| 18730 | Mocs3 | NM_001160330.1 | chr2:168056121-168057803 |
| 18731 | Mog | NM_010814.2 | chr17:37147684-37160343 |
| 18732 | Mogat1 | NM_026713.3 | chr1:78507634-78534748 |
| 18733 | Mogat2 | NM_177448.4 | chr7:106367593-106387121 |
| 18734 | Mogs | NM_020619.2 | chr6:83065499-83068892 |
| 18735 | Mok | NM_011973.2 | chr12:112046007-112079149 |

Fig. 25 - 100

| | | | | | | | | |
|---|---|---|---|---|---|---|---|---|
| 18736 | Mon1a | NM_028369.3 | chr9:107790459-107805470 | 18831 | Mpzl1 | NM_001083897.1 | chr1:167522311-167564672 |
| 18737 | Mon1b | NM_001048143.2 | chr8:116159485-116179433 | 18832 | Mpzl2 | NM_007962.4 | chr9:44850426-44862126 |
| 18738 | Mon1b | NM_173015.3 | chr8:116159485-116179433 | 18833 | Mpzl3 | NM_001093749.2 | chr9:44863263-44883125 |
| 18739 | Mon2 | NM_001163024.1 | chr10:122429116-122513561 | 18834 | Mr1 | NM_008209.4 | chr1:156975007-156993910 |
| 18740 | Mon2 | NM_001163026.1 | chr10:122429116-122513561 | 18835 | Mrap | NM_029844.3 | chr16:90738568-90750021 |
| 18741 | Mon2 | NM_153395.2 | chr10:122429116-122513561 | 18836 | Mrap2 | NM_001101482.2 | chr9:87039140-87078880 |
| 18742 | Morc1 | NM_010816.1 | chr16:48431349-48631018 | 18837 | Mrap2 | NM_001177731.1 | chr9:87039140-87078880 |
| 18743 | Morc2a | NM_001159288.1 | chr11:3549496-3590375 | 18838 | Mras | NM_008624.3 | chr9:99285838-99337131 |
| 18744 | Morc2a | NM_198162.1 | chr11:3549496-3590375 | 18839 | Mrc1 | NM_008625.2 | chr2:14151041-14253650 |
| 18745 | Morc2b | NM_177719.4 | chr17:33272534-33276628 | 18840 | Mrc2 | NM_008626.3 | chr11:105153959-105212459 |
| 18746 | Morc3 | NM_001045529.3 | chr16:93832365-93876318 | 18841 | Mre11a | NM_018736.2 | chr9:14589150-14638861 |
| 18747 | Morc4 | NM_001193309.1 | chrX:136356173-136406193 | 18842 | Mreg | NM_001005423.2 | chr1:72205806-72258881 |
| 18748 | Morc4 | NM_029413.4 | chrX:136356173-136406193 | 18843 | Mrfap1 | NM_026242.3 | chr5:37186105-37187993 |
| 18749 | Morf4l1 | NM_001039147.2 | chr9:89986506-90009658 | 18844 | Mrgbp | NM_028479.1 | chr2:180316008-180320339 |
| 18750 | Morf4l1 | NM_024431.3 | chr9:89986506-90009658 | 18845 | Mrgpra1 | NM_153095.2 | chr7:54590244-54609610 |
| 18751 | Morf4l2 | NM_001168225.1 | chrX:133267489-133337900 | 18846 | Mrgpra2a | NM_001172588.1 | chr7:54681698-54707509 |
| 18752 | Morf4l2 | NM_001168226.1 | chrX:133267489-133337900 | 18847 | Mrgpra2b | NM_153101.3 | chr7:54719176-54744952 |
| 18753 | Morf4l2 | NM_001168227.1 | chrX:133267489-133337900 | 18848 | Mrgpra3 | NM_153067.2 | chr7:54844319-54856742 |
| 18754 | Morf4l2 | NM_001168228.1 | chrX:133267489-133337900 | 18849 | Mrgpra4 | NM_153524.2 | chr7:55236613-55237666 |
| 18755 | Morf4l2 | NM_001168229.1 | chrX:133267489-133337900 | 18850 | Mrgpra6 | NM_205821.2 | chr7:54441135-54444725 |
| 18756 | Morf4l2 | NM_001168230.1 | chrX:133267489-133337900 | 18851 | Mrgpra9 | NM_001288801.1 | chr7:54490288-54508218 |
| 18757 | Morf4l2 | NM_019768.4 | chrX:133267489-133337900 | 18852 | Mrgprb1 | NM_205810.4 | chr7:55699482-55711712 |
| 18758 | Morn1 | NM_001081100.1 | chr4:154460685-154519616 | 18853 | Mrgprb2 | NM_175531.4 | chr7:55806335-55813456 |
| 18759 | Morn2 | NM_194269.2 | chr17:80689552-80696816 | 18854 | Mrgprb3 | NM_207537.1 | chr7:55898232-55899171 |
| 18760 | Morn3 | NM_029112.1 | chr5:123487135-123496829 | 18855 | Mrgprb4 | NM_205795.1 | chr7:55453582-55454548 |
| 18761 | Morn4 | NM_198108.2 | chr19:42149428-42160860 | 18856 | Mrgprb5 | NM_207538.1 | chr7:55423386-55424355 |
| 18762 | Morn5 | NM_029309.2 | chr2:35904992-35935229 | 18857 | Mrgprb8 | NM_207539.2 | chr7:55643895-55645018 |
| 18763 | Mos | NM_020212.2 | chr4:3797804-3799252 | 18858 | Mrgprd | NM_203490.3 | chr7:152500739-152509964 |
| 18764 | Mospd1 | NM_001290514.1 | chrX:50697770-50723736 | 18859 | Mrgpre | NM_175534.3 | chr7:150964267-150970405 |
| 18765 | Mospd1 | NM_027409.5 | chrX:50697770-50723736 | 18860 | Mrgprf | NM_145379.2 | chr7:152486813-152495462 |
| 18766 | Mospd1 | NR_110964.1 | chrX:50697770-50723736 | 18861 | Mrgprg | NM_203492.2 | chr7:150949614-150952898 |
| 18767 | Mospd2 | NM_001290523.1 | chrX:161374105-161418307 | 18862 | Mrgprh | NM_030726.1 | chr17:13068899-13070708 |
| 18768 | Mospd2 | NM_001290524.1 | chrX:161374105-161418307 | 18863 | Mrgprx1 | NM_207540.3 | chr7:55276340-55282967 |
| 18769 | Mospd2 | NM_029730.4 | chrX:161374105-161418307 | 18864 | Mrgprx2 | NM_001034868.3 | chr7:55783988-55754640 |
| 18770 | Mospd3 | NM_001254762.1 | chr5:138037874-138042287 | 18865 | Mri1 | NM_026423.4 | chr8:86774474-86781223 |
| 18771 | Mospd3 | NM_030037.2 | chr5:138037874-138042287 | 18866 | Mrm1 | NM_145433.1 | chr11:84626562-84633017 |
| 18772 | Mospd4 | NR_045438.1 | chr18:46624587-46625470 | 18867 | Mro | NM_027741.1 | chr18:74019040-74038788 |
| 18773 | Mov10 | NM_001163440.1 | chr3:104597749-104621481 | 18868 | Mroh1 | NM_001162489.1 | chr15:76210942-76307699 |
| 18774 | Mov10 | NM_001163441.1 | chr3:104597749-104621481 | 18869 | Mroh1 | NM_175457.4 | chr15:76210942-76307699 |
| 18775 | Mov10 | NM_008619.2 | chr3:104597749-104621481 | 18870 | Mroh2a | NM_001281466.1 | chr1:90123595-90158864 |
| 18776 | Mov10l1 | NM_031260.2 | chr15:88813423-88885582 | 18871 | Mroh2b | NM_001166066.1 | chr15:4848736-4912201 |
| 18777 | Moxd1 | NM_021509.5 | chr10:23943322-24022589 | 18872 | Mroh4 | NM_001177437.1 | chr15:74436457-74466748 |
| 18778 | Moxd2 | NM_139296.2 | chr6:40828792-40837493 | 18873 | Mroh5 | NM_001033365.2 | chr15:73617365-73670101 |
| 18779 | Mpc1 | NM_018819.4 | chr17:8476678-8490526 | 18874 | Mroh6 | NM_001282443.1 | chr15:75713363-75719153 |
| 18780 | Mpc2 | NM_027430.2 | chr1:167391338-167411345 | 18875 | Mroh7 | NM_001126487.1 | chr4:106353021-106400535 |
| 18781 | Mpdu1 | NM_013900.4 | chr11:69470201-69476151 | 18876 | Mroh8 | NM_001039957.4 | chr2:157034284-157105285 |
| 18782 | Mpdz | NM_010820.3 | chr4:80924403-81088709 | 18877 | Mroh9 | NM_030071.1 | chr1:164954432-165015801 |
| 18783 | Mpeg1 | NM_010821.1 | chr19:12535268-12539775 | 18878 | Mrpl1 | NM_001039084.1 | chr5:96639133-96695746 |
| 18784 | Mpg | NM_010822.3 | chr11:32126505-32132702 | 18879 | Mrpl1 | NM_053158.3 | chr5:96639133-96695746 |
| 18785 | Mphosph10 | NM_026483.2 | chr7:71521426-71537122 | 18880 | Mrpl10 | NM_026154.1 | chr11:96902899-96910527 |
| 18786 | Mphosph6 | NM_026758.3 | chr8:120315544-120325829 | 18881 | Mrpl11 | NM_025553.4 | chr19:4962305-4966995 |
| 18787 | Mphosph8 | NM_023773.2 | chr14:57287085-57316266 | 18882 | Mrpl12 | NM_027204.2 | chr11:120345982-120350068 |
| 18788 | Mphosph9 | NM_001081323.2 | chr5:124700967-124777981 | 18883 | Mrpl13 | NM_026759.3 | chr15:55365649-55388867 |
| 18789 | Mphosph9 | NM_001277867.1 | chr5:124700967-124777981 | 18884 | Mrpl14 | NM_026732.2 | chr17:45823320-45835444 |
| 18790 | Mphosph9 | NR_102690.1 | chr5:124700967-124777981 | 18885 | Mrpl15 | NM_001177658.1 | chr1:4763278-4775807 |
| 18791 | Mpi | NM_025837.2 | chr9:57392074-57400659 | 18886 | Mrpl15 | NM_025300.4 | chr1:4763278-4775807 |
| 18792 | Mpi | NM_001122949.2 | chr4:118115019-118130118 | 18887 | Mrpl15 | NR_033530.1 | chr1:4763278-4775807 |
| 18793 | Mpi | NM_001285496.1 | chr4:118115019-118130118 | 18888 | Mrpl16 | NM_025606.3 | chr19:11844904-11849436 |
| 18794 | Mpi | NM_001285497.1 | chr4:118115019-118130118 | 18889 | Mrpl17 | NM_025301.2 | chr7:112952295-112959601 |
| 18795 | Mpi | NM_010823.3 | chr4:118115019-118130118 | 18890 | Mrpl18 | NM_026310.3 | chr17:13104220-13108957 |
| 18796 | Mpikip | NM_025479.5 | chr13:17787246-17790939 | 18891 | Mrpl19 | NM_026490.2 | chr6:81907840-81915943 |
| 18797 | Mpnd | NM_026530.5 | chr17:56148624-56156206 | 18892 | Mrpl2 | NM_025302.3 | chr17:46783196-46787081 |
| 18798 | Mpo | NM_010824.2 | chr11:87607285-87617914 | 18893 | Mrpl20 | NM_025570.2 | chr4:155177726-155182938 |
| 18799 | Mpp1 | NM_008621.3 | chrX:72355072-72376355 | 18894 | Mrpl21 | NM_172252.3 | chr19:3283047-3292837 |
| 18800 | Mpp2 | NM_016695.3 | chr11:101918330-101949829 | 18895 | Mrpl22 | NM_175001.3 | chr11:57985155-57993082 |
| 18801 | Mpp3 | NM_007863.2 | chr11:101860966-101888269 | 18896 | Mrpl23 | NM_011288.1 | chr7:149719021-149726647 |
| 18802 | Mpp4 | NM_001164682.1 | chr1:59177778-59294075 | 18897 | Mrpl24 | NM_026591.3 | chr3:87723466-87727355 |
| 18803 | Mpp4 | NM_145143.3 | chr1:59177778-59294075 | 18898 | Mrpl27 | NM_053161.2 | chr11:94515104-94521401 |
| 18804 | Mpp5 | NM_019579.3 | chr12:79849933-79941700 | 18899 | Mrpl28 | NM_024227.3 | chr17:26260447-26263558 |
| 18805 | Mpp6 | NM_001164733.1 | chr6:50060239-50148597 | 18900 | Mrpl3 | NM_053159.3 | chr9:104955597-104979806 |
| 18806 | Mpp6 | NM_001164734.1 | chr6:50060239-50148597 | 18901 | Mrpl30 | NM_027098.2 | chr1:37947397-37955178 |
| 18807 | Mpp6 | NM_019939.2 | chr6:50060239-50148597 | 18902 | Mrpl32 | NM_029271.2 | chr13:14702567-14705304 |
| 18808 | Mpp7 | NM_001081287.2 | chr18:7347959-7626861 | 18903 | Mrpl33 | NM_025796.3 | chr5:31916323-31925017 |
| 18809 | Mpp7 | NM_001161620.1 | chr18:7347959-7626861 | 18904 | Mrpl34 | NM_053162.2 | chr8:73988824-73989652 |
| 18810 | Mppe1 | NM_172630.2 | chr18:67385184-67405484 | 18905 | Mrpl35 | NM_025430.3 | chr6:71762990-71773778 |
| 18811 | Mpped1 | NM_173768.3 | chr18:63610452-83688904 | 18906 | Mrpl36 | NM_053163.1 | chr13:73468456-73469626 |
| 18812 | Mpped2 | NM_001143683.1 | chr2:106533615-106708517 | 18907 | Mrpl37 | NM_025500.2 | chr4:106728478-106739471 |
| 18813 | Mpped2 | NM_029837.1 | chr2:106533615-106708517 | 18908 | Mrpl38 | NM_024177.1 | chr11:115993130-116000182 |
| 18814 | Mprip | NM_010727.2 | chr11:59475996-59594362 | 18909 | Mrpl39 | NM_017404.4 | chr16:84717824-84735547 |
| 18815 | Mprip | NM_201245.3 | chr11:59475996-59594362 | 18910 | Mrpl4 | NM_023167.2 | chr9:20807180-20813281 |
| 18816 | Mpst | NM_001162492.1 | chr15:78237141-78244445 | 18911 | Mrpl40 | NM_010922.2 | chr16:18872110-18876730 |
| 18817 | Mpst | NM_001162494.1 | chr15:78237141-78244445 | 18912 | Mrpl41 | NM_001031808.2 | chr2:24827990-24830618 |
| 18818 | Mpst | NM_138670.3 | chr15:78237141-78244445 | 18913 | Mrpl42 | NM_026065.3 | chr10:94943439-94964561 |
| 18819 | Mptx1 | NM_025470.3 | chr1:176260648-176263008 | 18914 | Mrpl43 | NM_053164.3 | chr19:45079503-45080932 |
| 18820 | Mptx2 | NM_001205011.2 | chr1:175204591-175207887 | 18915 | Mrpl44 | NM_001081210.1 | chr7:79772592-79778020 |
| 18821 | Mpv17 | NM_008622.6 | chr5:31443036-31456624 | 18916 | Mrpl45 | NM_025927.4 | chr11:97177029-97191234 |
| 18822 | Mpv17l | NM_001289553.1 | chr16:13903253-13949712 | 18917 | Mrpl46 | NM_023331.2 | chr7:85920226-85927975 |
| 18823 | Mpv17l | NM_001289562.1 | chr16:13903253-13949712 | 18918 | Mrpl47 | NM_029017.2 | chr3:32626418-32635677 |
| 18824 | Mpv17l | NM_001289563.1 | chr16:13903253-13949712 | 18919 | Mrpl48 | NM_198831.2 | chr7:107697630-107789782 |
| 18825 | Mpv17l | NM_001289565.1 | chr16:13903253-13949712 | 18920 | Mrpl48 | NR_003559.1 | chr7:107697630-107789782 |
| 18826 | Mpv17l | NM_001289567.1 | chr16:13903253-13949712 | 18921 | Mrpl49 | NM_026246.3 | chr19:6053630-6057751 |
| 18827 | Mpv17l | NM_033564.3 | chr16:13903253-13949712 | 18922 | Mrpl50 | NM_178603.4 | chr4:49525468-49533955 |
| 18828 | Mpv17l2 | NM_183170.2 | chr8:73282548-73284820 | 18923 | Mrpl51 | NM_025595.3 | chr6:125142217-125144410 |
| 18829 | Mpz | NM_008623.4 | chr1:173080843-173091254 | 18924 | Mrpl52 | NM_026851.2 | chr14:55045745-55048587 |
| 18830 | Mpzl1 | NM_001001880.2 | chr1:167522311-167564672 | 18925 | Mrpl53 | NM_026744.3 | chr6:83059102-83059926 |

Fig. 25 - 101

| | | | |
|---|---|---|---|
| 18926 | Mrpl54 | NM_025317.2 | chr10:80727466-80729671 |
| 18927 | Mrpl55 | NM_026035.3 | chr11:59016018-59019504 |
| 18928 | Mrpl57 | NM_026401.2 | chr14:58445075-58447582 |
| 18929 | Mrpl9 | NM_030116.2 | chr3:94247257-94262630 |
| 18930 | Mrps10 | NM_001146211.1 | chr17:47505835-47515628 |
| 18931 | Mrps10 | NM_001146212.1 | chr17:47505835-47515628 |
| 18932 | Mrps10 | NM_183086.2 | chr17:47505835-47515628 |
| 18933 | Mrps11 | NM_026498.2 | chr7:85928016-85937874 |
| 18934 | Mrps12 | NM_011885.4 | chr7:29524659-29526800 |
| 18935 | Mrps14 | NM_025474.3 | chr1:162125396-162131317 |
| 18936 | Mrps15 | NM_025544.2 | chr4:125724171-125732780 |
| 18937 | Mrps16 | NM_025440.2 | chr14:21210452-21212777 |
| 18938 | Mrps17 | NM_025450.4 | chr5:130221402-130224566 |
| 18939 | Mrps18a | NM_026768.3 | chr17:46247952-46265857 |
| 18940 | Mrps18b | NM_025878.1 | chr17:36047329-36053314 |
| 18941 | Mrps18c | NM_026826.1 | chr5:101227777-101233486 |
| 18942 | Mrps2 | NM_001166031.1 | chr2:28323585-28326697 |
| 18943 | Mrps2 | NM_080452.3 | chr2:28323585-28326697 |
| 18944 | Mrps21 | NM_078479.3 | chr3:95666574-95674542 |
| 18945 | Mrps22 | NM_025485.3 | chr9:98489149-98502098 |
| 18946 | Mrps23 | NM_001291270.1 | chr11:87911559-88025009 |
| 18947 | Mrps23 | NM_001291271.1 | chr11:87911559-88025009 |
| 18948 | Mrps23 | NM_001291272.1 | chr11:87911559-88025009 |
| 18949 | Mrps23 | NM_001291273.1 | chr11:87911559-88025009 |
| 18950 | Mrps23 | NM_024174.6 | chr11:87911559-88025009 |
| 18951 | Mrps23 | NR_111902.1 | chr11:87911559-88025009 |
| 18952 | Mrps24 | NM_026080.2 | chr11:5603985-5607702 |
| 18953 | Mrps25 | NM_025578.4 | chr6:92119517-92134017 |
| 18954 | Mrps26 | NM_207207.1 | chr2:130389492-130391130 |
| 18955 | Mrps27 | NM_173757.3 | chr13:100114741-100185516 |
| 18956 | Mrps28 | NM_025434.3 | chr3:8802145-8923857 |
| 18957 | Mrps30 | NM_021556.3 | chr13:119168916-119176059 |
| 18958 | Mrps31 | NM_020560.2 | chr8:23521811-23540137 |
| 18959 | Mrps33 | NM_001010930.1 | chr6:39751806-39760935 |
| 18960 | Mrps33 | NM_010270.2 | chr6:39751806-39760935 |
| 18961 | Mrps34 | NM_023260.1 | chr17:25032064-25033218 |
| 18962 | Mrps35 | NM_145573.2 | chr6:146991291-147019424 |
| 18963 | Mrps36 | NM_001190264.1 | chr13:101505894-101514614 |
| 18964 | Mrps36 | NM_025369.3 | chr13:101505894-101514614 |
| 18965 | Mrps5 | NM_029963.2 | chr2:127413161-127429722 |
| 18966 | Mrps6 | NM_080456.1 | chr16:92058581-92124472 |
| 18967 | Mrps7 | NM_025535.2 | chr11:115465464-115468938 |
| 18968 | Mrps9 | NM_023514.4 | chr1:42908077-42962528 |
| 18969 | Mrrf | NM_026422.2 | chr2:35991918-36045803 |
| 18970 | Mrs2 | NM_001013389.2 | chr13:25084163-25112186 |
| 18971 | Mrto4 | NM_001290810.1 | chr4:138903354-138908491 |
| 18972 | Mrto4 | NM_023536.3 | chr4:138903354-138908491 |
| 18973 | Mrvi1 | NM_010826.5 | chr7:118011771-118126975 |
| 18974 | Mrvi1 | NM_194464.3 | chr7:118011771-118126975 |
| 18975 | Ms4a1 | NM_007641.5 | chr19:11325093-11340641 |
| 18976 | Ms4a10 | NM_023529.2 | chr19:11036784-11049160 |
| 18977 | Ms4a13 | NM_198224.1 | chr19:11243907-11271213 |
| 18978 | Ms4a15 | NM_001034898.2 | chr19:11052796-11067740 |
| 18979 | Ms4a18 | NM_001251849.1 | chr19:11071514-11092453 |
| 18980 | Ms4a2 | NM_001276328.1 | chr19:11690010-11698209 |
| 18981 | Ms4a2 | NM_001276329.1 | chr19:11690010-11698209 |
| 18982 | Ms4a2 | NM_001276330.1 | chr19:11690010-11698209 |
| 18983 | Ms4a2 | NM_013516.2 | chr19:11690010-11698209 |
| 18984 | Ms4a3 | NM_133246.5 | chr19:11703986-11715324 |
| 18985 | Ms4a4b | NM_021718.2 | chr19:11518047-11538038 |
| 18986 | Ms4a4c | NM_029499.3 | chr19:11482150-11501736 |
| 18987 | Ms4a4d | NM_025658.4 | chr19:11611338-11632956 |
| 18988 | Ms4a5 | NM_183190.2 | chr19:11348356-11358303 |
| 18989 | Ms4a6b | NM_027209.3 | chr19:11593048-11604893 |
| 18990 | Ms4a6c | NM_001166376.1 | chr19:11543857-11556686 |
| 18991 | Ms4a6c | NM_028595.4 | chr19:11543857-11556686 |
| 18992 | Ms4a6d | NM_026835.2 | chr19:11661095-11679294 |
| 18993 | Ms4a7 | NM_001025610.4 | chr19:11395528-11410636 |
| 18994 | Ms4a7 | NM_001276398.1 | chr19:11395528-11410636 |
| 18995 | Ms4a7 | NM_027920.2 | chr19:11395528-11410636 |
| 18996 | Ms4a8a | NM_022430.1 | chr19:11141960-11155593 |
| 18997 | Msantd1 | NM_207277.1 | chr5:35258563-35266488 |
| 18998 | Msantd2 | NM_146222.2 | chr9:37296905-37331735 |
| 18999 | Msantd3 | NM_001145924.1 | chr4:48552817-48574792 |
| 19000 | Msantd3 | NM_001145925.1 | chr4:48552817-48574792 |
| 19001 | Msantd3 | NM_028137.3 | chr4:48552817-48574792 |
| 19002 | Msantd4 | NM_145609.1 | chr9:4383536-4386869 |
| 19003 | Msc | NM_010827.2 | chr1:14743428-14746047 |
| 19004 | Msgn1 | NM_019544.1 | chr12:11215187-11215754 |
| 19005 | Msh2 | NM_008628.2 | chr17:88071896-88113053 |
| 19006 | Msh3 | NM_010829.1 | chr13:92981836-93124958 |
| 19007 | Msh4 | NM_001282054.1 | chr3:153520104-153569102 |
| 19008 | Msh4 | NM_031870.3 | chr3:153520104-153569102 |
| 19009 | Msh5 | NM_001146215.2 | chr17:35165549-35183668 |
| 19010 | Msh5 | NM_013600.3 | chr17:35165549-35183668 |
| 19011 | Msh6 | NM_010830.2 | chr17:88374396-88390232 |
| 19012 | Msi1 | NM_008629.1 | chr5:115879693-115904211 |
| 19013 | Msi2 | NM_001201341.1 | chr11:88152883-88579581 |
| 19014 | Msi2 | NM_054043.3 | chr11:88152883-88579581 |
| 19015 | Msl1 | NM_028722.2 | chr11:98657083-98669173 |
| 19016 | Msl2 | NM_001100451.2 | chr9:100978485-101007129 |
| 19017 | Msl3 | NM_010832.5 | chrX:165091030-165111834 |
| 19018 | Msl3l2 | NM_001163833.1 | chr10:55826723-55836686 |
| 19019 | Msln | NM_018857.1 | chr17:25885557-25891272 |
| 19020 | Mslnl | NM_177822.3 | chr17:25872984-25885275 |
| 19021 | Msmb | NM_020597.3 | chr14:32955208-32971512 |
| 19022 | Msmo1 | NM_025436.2 | chr8:67196941-67212375 |
| 19023 | Msmp | NM_001099314.1 | chr4:43596088-43597366 |
| 19024 | Msn | NM_010833.2 | chrX:93291383-93363892 |
| 19025 | Msr1 | NM_001113326.1 | chr8:40667053-40728032 |
| 19026 | Msr1 | NM_031195.2 | chr8:40667053-40728032 |
| 19027 | Msra | NM_001253712.1 | chr14:64741457-65074740 |
| 19028 | Msra | NM_001253714.1 | chr14:64741457-65074740 |
| 19029 | Msra | NM_001253715.1 | chr14:64741457-65074740 |
| 19030 | Msra | NM_001253716.1 | chr14:64741457-65074740 |
| 19031 | Msra | NM_026322.4 | chr14:64741457-65074740 |
| 19032 | Msrb1 | NM_013759.2 | chr17:24873586-24879723 |
| 19033 | Msrb2 | NM_029619.2 | chr2:19293262-19316597 |
| 19034 | Msrb3 | NM_177092.4 | chr10:120218157-120336027 |
| 19035 | Mss51 | NM_029104.1 | chr14:21302085-21316123 |
| 19036 | Mst1 | NM_008243.3 | chr9:107982767-107987358 |
| 19037 | Mst1r | NM_001287261.1 | chr9:107809219-107822714 |
| 19038 | Mst1r | NM_009074.2 | chr9:107809219-107822714 |
| 19039 | Mst1r | NR_109782.1 | chr9:107809219-107822714 |
| 19040 | Mstn | NM_010834.2 | chr1:53118506-53124923 |
| 19041 | Msto1 | NM_144898.2 | chr3:88713538-88717872 |
| 19042 | Msx1 | NM_010835.2 | chr5:38211730-38215824 |
| 19043 | Msx1os | NR_027920.1 | chr5:38211803-38213990 |
| 19044 | Msx2 | NM_013601.2 | chr13:53562249-53568149 |
| 19045 | Msx3 | NM_010836.3 | chr7:147232055-147234987 |
| 19046 | Mt1 | NM_013602.3 | chr8:96702988-96704227 |
| 19047 | Mt2 | NM_008630.2 | chr8:96696517-96697467 |
| 19048 | Mt3 | NM_013603.2 | chr8:96676506-96678048 |
| 19049 | Mt4 | NM_008631.2 | chr8:96661103-96662931 |
| 19050 | Mta1 | NM_054081.2 | chr12:114336488-114375417 |
| 19051 | Mta2 | NM_011842.3 | chr19:9016409-9026790 |
| 19052 | Mta3 | NM_001171052.1 | chr17:84105502-84214245 |
| 19053 | Mta3 | NM_001171053.1 | chr17:84105502-84214245 |
| 19054 | Mta3 | NM_001171054.1 | chr17:84105502-84214245 |
| 19055 | Mta3 | NM_054082.2 | chr17:84105502-84214245 |
| 19056 | Mtag2 | NR_015480.1 | chr7:52594495-52625934 |
| 19057 | Mtag2 | NR_027802.1 | chr7:52594495-52625934 |
| 19058 | Mtap | NM_024433.2 | chr4:88783273-88826994 |
| 19059 | Mtap7d3 | NM_177293.3 | chrX:54051129-54075502 |
| 19060 | Mtbp | NM_001168250.1 | chr15:55388962-55457978 |
| 19061 | Mtbp | NM_134092.2 | chr15:55388962-55457978 |
| 19062 | Mtch1 | NM_019880.3 | chr17:29469020-29484849 |
| 19063 | Mtch2 | NM_019758.2 | chr2:90687311-90706791 |
| 19064 | Mtcl1 | NM_001114098.1 | chr17:66686321-66799090 |
| 19065 | Mtcl1 | NM_172963.4 | chr17:66686321-66799090 |
| 19066 | Mtcp1 | NM_001039373.5 | chrX:72650185-72661882 |
| 19067 | Mtcp1 | NM_010839.6 | chrX:72650185-72661882 |
| 19068 | Mtdh | NM_026002.4 | chr15:34012473-34072140 |
| 19069 | Mterf1a | NM_001013023.2 | chr5:3890580-3893933 |
| 19070 | Mterf1a | NM_172135.2 | chr5:3890580-3893933 |
| 19071 | Mterf1b | NM_001042670.1 | chr5:4192366-4197651 |
| 19072 | Mterfd1 | NM_025547.3 | chr13:67013034-67034008 |
| 19073 | Mterfd2 | NM_178051.3 | chr11:95195787-95202447 |
| 19074 | Mterfd3 | NM_028832.3 | chr10:84582177-84590772 |
| 19075 | Mtf1 | NM_008636.4 | chr4:124479793-124527044 |
| 19076 | Mtf2 | NM_001253877.1 | chr5:108494692-108538238 |
| 19077 | Mtf2 | NM_001253878.1 | chr5:108494692-108538238 |
| 19078 | Mtf2 | NM_001253879.1 | chr5:108494692-108538238 |
| 19079 | Mtf2 | NM_001253880.1 | chr5:108494692-108538238 |
| 19080 | Mtf2 | NM_013827.3 | chr5:108494692-108538238 |
| 19081 | Mtf2 | NR_045608.1 | chr5:108494692-108538238 |
| 19082 | Mtfmt | NM_027134.3 | chr9:65283588-65300861 |
| 19083 | Mtfp1 | NM_026443.4 | chr11:3991483-3995434 |
| 19084 | Mtfr1 | NM_001253390.1 | chr3:19087328-19120817 |
| 19085 | Mtfr1 | NM_001253391.1 | chr3:19087328-19120817 |
| 19086 | Mtfr1 | NM_026182.5 | chr3:19087328-19120817 |
| 19087 | Mtfr1 | NR_045575.1 | chr3:19087328-19120817 |
| 19088 | Mtfr1l | NM_001256112.1 | chr4:134081469-134091302 |
| 19089 | Mtfr1l | NM_029759.4 | chr4:134081469-134091302 |
| 19090 | Mtfr2 | NM_027930.3 | chr10:20067624-20081475 |
| 19091 | Mtg1 | NM_199301.2 | chr7:147323463-147336685 |
| 19092 | Mtg2 | NM_001083328.1 | chr2:179805297-179820607 |
| 19093 | Mtg2 | NM_001083329.1 | chr2:179805297-179820607 |
| 19094 | Mtg2 | NM_028422.1 | chr2:179805297-179820607 |
| 19095 | Mtg2 | NM_181424.3 | chr2:179805297-179820607 |
| 19096 | Mthfd1 | NM_138745.2 | chr12:77356218-77420807 |
| 19097 | Mthfd1l | NM_001170785.1 | chr10:6179459-6373466 |
| 19098 | Mthfd1l | NM_001170786.1 | chr10:6179459-6373466 |
| 19099 | Mthfd1l | NM_172308.4 | chr10:6179459-6373466 |
| 19100 | Mthfd2 | NM_008638.2 | chr6:83255697-83267598 |
| 19101 | Mthfd2l | NM_026788.1 | chr5:91360221-91450395 |
| 19102 | Mthfr | NM_001161798.1 | chr4:147413185-147433671 |
| 19103 | Mthfr | NM_010840.3 | chr4:147413185-147433671 |
| 19104 | Mthfr | NR_027809.1 | chr4:147413185-147433671 |
| 19105 | Mthfs | NM_026829.2 | chr9:89106027-89135063 |
| 19106 | Mthfsd | NM_001166482.1 | chr8:123621456-123632279 |
| 19107 | Mthfsd | NM_172761.3 | chr8:123621456-123632279 |
| 19108 | Mtif2 | NM_001282118.1 | chr11:29426396-29445447 |
| 19109 | Mtif2 | NM_001282119.1 | chr11:29426396-29445447 |
| 19110 | Mtif2 | NM_001282120.1 | chr11:29426396-29445447 |
| 19111 | Mtif2 | NM_133767.3 | chr11:29426396-29445447 |
| 19112 | Mtif3 | NM_001256100.1 | chr5:147760232-147775373 |
| 19113 | Mtif3 | NM_001256101.1 | chr5:147760232-147775373 |
| 19114 | Mtif3 | NM_001256102.1 | chr5:147760232-147775373 |
| 19115 | Mtif3 | NM_029581.4 | chr5:147760232-147775373 |

Fig. 25 - 102

| | | | |
|---|---|---|---|
| 19116 | Mt15 | NM_001039657.2 | chr19:3388856-3407823 |
| 19117 | Mt15 | NM_001039658.2 | chr19:3388856-3407823 |
| 19118 | Mt15 | NM_001286557.1 | chr19:3388856-3407823 |
| 19119 | Mt15 | NM_001286558.1 | chr19:3388856-3407823 |
| 19120 | Mtm1 | NM_001164190.1 | chrX:68463941-68568470 |
| 19121 | Mtm1 | NM_001164191.1 | chrX:68463941-68568470 |
| 19122 | Mtm1 | NM_001164192.1 | chrX:68463941-68568470 |
| 19123 | Mtm1 | NM_001164193.1 | chrX:68463941-68568470 |
| 19124 | Mtm1 | NM_019926.3 | chrX:68463941-68568470 |
| 19125 | Mtmr1 | NM_016985.2 | chrX:68617934-68672371 |
| 19126 | Mtmr10 | NM_172742.2 | chr7:71432555-71485692 |
| 19127 | Mtmr11 | NM_181409.3 | chr3:95965892-95975641 |
| 19128 | Mtmr12 | NM_172958.3 | chr15:12134848-12201995 |
| 19129 | Mtmr14 | NM_026849.2 | chr6:113187836-113231386 |
| 19130 | Mtmr2 | NM_023858.3 | chr9:13553624-13610925 |
| 19131 | Mtmr2 | NR_024025.1 | chr9:13553624-13610925 |
| 19132 | Mtmr3 | NM_028860.2 | chr11:4380870-4494818 |
| 19133 | Mtmr4 | NM_133215.1 | chr11:87405718-87429798 |
| 19134 | Mtmr6 | NM_144843.4 | chr14:60846041-60921208 |
| 19135 | Mtmr7 | NM_001040699.1 | chr8:41635513-41720146 |
| 19136 | Mtmr9 | NM_177594.1 | chr14:64142446-64162790 |
| 19137 | Mtnr1a | NM_008639.2 | chr8:46154563-46173860 |
| 19138 | Mtnr1b | NM_145712.2 | chr9:15667057-15679000 |
| 19139 | Mto1 | NM_026658.2 | chr9:78296016-78321959 |
| 19140 | Mtor | NM_020009.2 | chr4:147822691-147931794 |
| 19141 | Mtpap | NM_026157.2 | chr18:4375589-4397328 |
| 19142 | Mtpn | NM_008098.4 | chr6:35458823-35489888 |
| 19143 | Mtr | NM_001081128.3 | chr13:12278806-12350380 |
| 19144 | Mtrf1 | NM_145960.4 | chr14:79797578-79823457 |
| 19145 | Mtrf1l | NM_175374.3 | chr10:4522597-4534664 |
| 19146 | Mtrr | NM_172480.3 | chr13:68699656-68720998 |
| 19147 | Mtss1 | NM_001146180.1 | chr15:58772788-58913581 |
| 19148 | Mtss1 | NM_144800.2 | chr15:58772788-58913581 |
| 19149 | Mtss1l | NM_198625.1 | chr8:113245383-113265300 |
| 19150 | Mttp | NM_001163457.1 | chr3:137752818-137806352 |
| 19151 | Mttp | NM_008642.2 | chr3:137752818-137806352 |
| 19152 | Mturn | NM_001289740.1 | chr6:54631617-54653849 |
| 19153 | Mturn | NM_001289741.1 | chr6:54631617-54653849 |
| 19154 | Mtus1 | NM_001005863.2 | chr8:42076265-42219080 |
| 19155 | Mtus1 | NM_001005864.3 | chr8:42076265-42219080 |
| 19156 | Mtus1 | NM_001005865.3 | chr8:42076265-42219080 |
| 19157 | Mtus1 | NM_001286413.1 | chr8:42076265-42219080 |
| 19158 | Mtus2 | NM_029920.7 | chr5:148768895-149127641 |
| 19159 | Mtx1 | NM_001161824.1 | chr3:89013002-89018257 |
| 19160 | Mtx1 | NM_013605.4 | chr3:89013002-89018257 |
| 19161 | Mtx2 | NM_016804.4 | chr2:74663868-74714805 |
| 19162 | Mtx3 | NM_001162945.1 | chr13:93614741-93628185 |
| 19163 | Muc1 | NM_013605.1 | chr3:89032977-89037303 |
| 19164 | Muc13 | NM_010739.2 | chr16:33794122-33820013 |
| 19165 | Muc15 | NM_001290786.1 | chr2:110495357-110790401 |
| 19166 | Muc15 | NM_172979.3 | chr2:110495357-110790401 |
| 19167 | Muc19 | NM_207243.2 | chr15:91668757-91764986 |
| 19168 | Muc2 | NM_023566.3 | chr7:148876238-148940599 |
| 19169 | Muc20 | NM_001145874.1 | chr16:32735971-32797521 |
| 19170 | Muc20 | NM_146071.2 | chr16:32735971-32797521 |
| 19171 | Muc4 | NM_080457.3 | chr16:32735972-32782476 |
| 19172 | Muc5ac | NM_010844.1 | chr7:148974915-149005040 |
| 19173 | Muc5b | NM_028801.2 | chr7:149024976-149058990 |
| 19174 | Muc6 | NM_181729.2 | chr7:148841947-148841200 |
| 19175 | Mucl1 | NM_009268.1 | chrUn_random:4834599-4838176 |
| 19176 | Mug1 | NM_008645.3 | chr6:121788558-121839075 |
| 19177 | Mug2 | NM_008646.3 | chr6:121956815-122035985 |
| 19178 | Mug-ps1 | NR_027619.1 | chr6:122126070-122198584 |
| 19179 | Mul1 | NM_026689.3 | chr4:137990586-137998180 |
| 19180 | Mum1 | NM_023431.5 | chr10:79689342-79707889 |
| 19181 | Mum1l1 | NM_001164630.1 | chrX:135744582-135772874 |
| 19182 | Mum1l1 | NM_001164631.1 | chrX:135744582-135772874 |
| 19183 | Mum1l1 | NM_001164632.1 | chrX:135744582-135772874 |
| 19184 | Mum1l1 | NM_001164633.1 | chrX:135744582-135772874 |
| 19185 | Mum1l1 | NM_175541.3 | chrX:135744582-135772874 |
| 19186 | Mup1 | NM_001163010.1 | chr4:60510884-60514832 |
| 19187 | Mup1 | NM_001163011.1 | chr4:60510884-60514832 |
| 19188 | Mup1 | NM_031188.2 | chr4:60510884-60514832 |
| 19189 | Mup10 | NM_001226147.1 | chr4:60591133-60595027 |
| 19190 | Mup11 | NM_001164526.1 | chr4:60671339-60675267 |
| 19191 | Mup12 | NM_001199995.1 | chr4:60732253-60736153 |
| 19192 | Mup13 | NM_001134674.1 | chr4:60885338-60889318 |
| 19193 | Mup14 | NM_001199999.1 | chr4:60961069-60965030 |
| 19194 | Mup15 | NM_001200004.1 | chr4:60079340-60152730 |
| 19195 | Mup15 | NM_001200004.1 | chr4:60961050-61100736 |
| 19196 | Mup16 | NM_001199936.1 | chr4:61176624-61180518 |
| 19197 | Mup17 | NM_001200006.1 | chr4:61252962-61256864 |
| 19198 | Mup19 | NM_001135127.2 | chr4:61439361-61443258 |
| 19199 | Mup2 | NM_001045550.2 | chr4:60591112-60675267 |
| 19200 | Mup2 | NM_001045550.2 | chr4:60079340-60152730 |
| 19201 | Mup2 | NM_001045550.2 | chr4:60961050-61100736 |
| 19202 | Mup2 | NM_001286096.1 | chr4:60079340-60152730 |
| 19203 | Mup2 | NM_001286096.1 | chr4:60591112-60675267 |
| 19204 | Mup2 | NM_001286096.1 | chr4:60961050-61100736 |
| 19205 | Mup2 | NM_008647.4 | chr4:60591112-60675267 |
| 19206 | Mup2 | NM_008647.4 | chr4:60079340-60152730 |
| 19207 | Mup2 | NM_008647.4 | chr4:60961050-61100736 |
| 19208 | Mup20 | NM_001012323.1 | chr4:61711268-61715151 |
| 19209 | Mup21 | NM_001009550.2 | chr4:61808865-61811875 |
| 19210 | Mup3 | NM_001039544.1 | chr4:61744510-61748346 |
| 19211 | Mup4 | NM_008648.1 | chr4:59969677-59973537 |
| 19212 | Mup5 | NM_008649.2 | chr4:61492352-61496214 |
| 19213 | Mup6 | NM_001081285.1 | chr4:60016420-60019086 |
| 19214 | Mup7 | NM_001134675.1 | chr4:60079341-60083347 |
| 19215 | Mup8 | NM_001134676.1 | chr4:60231492-60235471 |
| 19216 | Mup9 | NM_001281979.1 | chr4:60430918-60434824 |
| 19217 | Murc | NM_026509.3 | chr4:48676385-48686364 |
| 19218 | Mus81 | NM_027877.3 | chr19:5482839-5488336 |
| 19219 | Musk | NM_001037127.2 | chr4:58298833-58387175 |
| 19220 | Musk | NM_001037128.1 | chr4:58298833-58387175 |
| 19221 | Musk | NM_001037129.1 | chr4:58298833-58387175 |
| 19222 | Musk | NM_001037130.1 | chr4:58298833-58387175 |
| 19223 | Musk | NM_001165996.1 | chr4:58298833-58387175 |
| 19224 | Musk | NM_010944.2 | chr4:58298833-58387175 |
| 19225 | Mustn1 | NM_181390.3 | chr14:31692442-31694796 |
| 19226 | Mut | NM_008650.3 | chr17:41071633-41098938 |
| 19227 | Mutyh | NM_001159581.1 | chr4:116480338-116492036 |
| 19228 | Mutyh | NM_133250.2 | chr4:116480338-116492036 |
| 19229 | Mvb12a | NM_028617.2 | chr8:74066828-74071925 |
| 19230 | Mvb12b | NM_175184.4 | chr2:33585476-33743466 |
| 19231 | Mvd | NM_138656.2 | chr8:124957495-124967322 |
| 19232 | Mvd | NR_028354.1 | chr8:124957495-124967322 |
| 19233 | Mvk | NM_023556.3 | chr5:114849314-114910599 |
| 19234 | Mvp | NM_080638.3 | chr7:134130373-134158108 |
| 19235 | Mx1 | NM_010846.1 | chr16:97668641-97684513 |
| 19236 | Mx1 | NR_003520.1 | chr16:97668641-97684513 |
| 19237 | Mx2 | NM_013606.1 | chr16:97757687-97782508 |
| 19238 | Mx2 | NR_003508.1 | chr16:97757687-97782508 |
| 19239 | Mxd1 | NM_010751.3 | chr6:86597038-86619153 |
| 19240 | Mxd3 | NM_016662.4 | chr13:55426529-55431091 |
| 19241 | Mxd4 | NM_010753.2 | chr5:34519228-34530359 |
| 19242 | Mxi1 | NM_001008542.2 | chr19:53384995-53450300 |
| 19243 | Mxi1 | NM_001008543.2 | chr19:53384995-53450300 |
| 19244 | Mxi1 | NM_010847.3 | chr19:53384995-53450300 |
| 19245 | Mxra7 | NM_026280.3 | chr11:116664713-116689360 |
| 19246 | Mxra8 | NM_024263.4 | chr4:155213788-155218211 |
| 19247 | Myadm | NM_001093764.1 | chr7:3289038-3299350 |
| 19248 | Myadm | NM_001093765.1 | chr7:3289038-3299350 |
| 19249 | Myadm | NM_001093766.1 | chr7:3289038-3299350 |
| 19250 | Myadm | NM_016969.2 | chr7:3289038-3299350 |
| 19251 | Myadml2 | NM_001204820.1 | chr11:120507344-120509651 |
| 19252 | Myadml2 | NM_026751.1 | chr11:120507344-120509651 |
| 19253 | Myb | NM_001198914.1 | chr10:20844735-20880790 |
| 19254 | Myb | NM_010848.3 | chr10:20844735-20880790 |
| 19255 | Mybbp1a | NM_016776.2 | chr11:72254879-72265052 |
| 19256 | Mybl1 | NM_001290397.1 | chr1:9657491-9690290 |
| 19257 | Mybl1 | NM_008651.3 | chr1:9657491-9690290 |
| 19258 | Mybl2 | NM_008652.3 | chr2:162880371-162910423 |
| 19259 | Mybpc1 | NM_001252372.1 | chr10:87981023-88067897 |
| 19260 | Mybpc1 | NM_175418.5 | chr10:87981023-88067897 |
| 19261 | Mybpc2 | NM_146189.3 | chr7:51757068-51780039 |
| 19262 | Mybpc3 | NM_008653.2 | chr2:90958300-90976673 |
| 19263 | Mybph | NM_016749.2 | chr1:136090025-136097809 |
| 19264 | Mybphl | NM_026831.1 | chr3:108167829-108182975 |
| 19265 | Myc | NM_001177352.1 | chr15:61816895-61821916 |
| 19266 | Myc | NM_001177353.1 | chr15:61816895-61821916 |
| 19267 | Mycbp | NM_019660.3 | chr4:123582255-123589493 |
| 19268 | Mycbp2 | NM_207215.2 | chr14:103512627-103746017 |
| 19269 | Mycbpap | NM_170671.2 | chr11:94362660-94382816 |
| 19270 | Mycl | NM_008506.3 | chr4:122673341-122679723 |
| 19271 | Mycn | NM_008709.3 | chr12:12942898-12948642 |
| 19272 | Mycs | NM_010850.2 | chrX:5044021-5046383 |
| 19273 | Myct1 | NM_026793.2 | chr10:4739751-4752813 |
| 19274 | Myd88 | NM_010851.2 | chr9:119245105-119249158 |
| 19275 | Myef2 | NM_001162417.1 | chr2:124893862-124949396 |
| 19276 | Myef2 | NM_001162418.1 | chr2:124893862-124949396 |
| 19277 | Myef2 | NM_010852.2 | chr2:124893862-124949396 |
| 19278 | Myeov2 | NM_001163425.1 | chr1:94533721-94538562 |
| 19279 | Myeov2 | NR_028108.1 | chr1:94533721-94538562 |
| 19280 | Myf5 | NM_008656.5 | chr10:106919963-106923190 |
| 19281 | Myf6 | NM_008657.2 | chr10:106929915-106931785 |
| 19282 | Myg1 | NM_021713.2 | chr15:102162139-102168569 |
| 19283 | Myh1 | NM_030679.1 | chr11:67013615-67038077 |
| 19284 | Myh10 | NM_175260.2 | chr11:68505416-68630126 |
| 19285 | Myh11 | NM_001161775.1 | chr16:14194619-14291501 |
| 19286 | Myh11 | NM_013607.2 | chr16:14194619-14291501 |
| 19287 | Myh13 | NM_001081250.1 | chr11:67140604-67185004 |
| 19288 | Myh14 | NM_001271538.1 | chr7:51861172-51926213 |
| 19289 | Myh14 | NM_001271540.1 | chr7:51861172-51926213 |
| 19290 | Myh14 | NM_028021.3 | chr7:51861172-51926213 |
| 19291 | Myh15 | NM_001166210.1 | chr16:49057598-49199217 |
| 19292 | Myh2 | NM_001039545.2 | chr11:66984528-67011019 |
| 19293 | Myh3 | NM_001099635.1 | chr11:67051313-67073949 |
| 19294 | Myh4 | NM_010855.3 | chr11:67051313-67073949 |
| 19295 | Myh6 | NM_001164171.1 | chr14:55560757-55585444 |
| 19296 | Myh6 | NM_010856.4 | chr14:55560757-55585444 |
| 19297 | Myh7 | NM_080728.2 | chr14:55589525-55613386 |
| 19298 | Myh7b | NM_001085378.2 | chr2:155436979-155460043 |
| 19299 | Myh8 | NM_177369.3 | chr11:67090625-67122135 |
| 19300 | Myh9 | NM_022410.3 | chr15:77591014-77672605 |
| 19301 | Myl1 | NM_001113387.1 | chr1:66970869-66991630 |
| 19302 | Myl1 | NM_021285.3 | chr1:66970869-66991630 |
| 19303 | Myl10 | NM_001085387.2 | chr5:137169015-137176964 |
| 19304 | Myl10 | NM_021611.3 | chr5:137169015-137176964 |

Fig. 25 - 103

| | | | | | | | |
|---|---|---|---|---|---|---|---|
| 19305 | Myl12a | NM_026064.2 | chr17:71343132-71351873 | 19400 | N4bp2 | NM_001024917.1 | chr5:66154759-66218023 |
| 19306 | Myl12b | NM_023402.2 | chr17:71323302-71339856 | 19401 | N4bp2l1 | NM_133898.4 | chr5:151374217-151397100 |
| 19307 | Myl2 | NM_010861.3 | chr5:122550988-122556863 | 19402 | N4bp2l2 | NM_201369.3 | chr5:151438547-151468187 |
| 19308 | Myl3 | NM_010859.2 | chr9:110666184-110672298 | 19403 | N4bp3 | NM_145974.3 | chr11:51456591-51464575 |
| 19309 | Myl4 | NM_010858.4 | chr11:104411976-104448533 | 19404 | N6amt1 | NM_001159331.1 | chr16:87354429-87368894 |
| 19310 | Myl6 | NM_010860.3 | chr10:127927916-127930881 | 19405 | N6amt1 | NM_026366.2 | chr16:87354429-87368894 |
| 19311 | Myl6b | NM_172259.1 | chr10:127931212-127935741 | 19406 | N6amt2 | NM_026526.2 | chr14:58168434-58190406 |
| 19312 | Myl7 | NM_022879.2 | chr11:5796639-5798785 | 19407 | Naa10 | NM_001177965.1 | chrX:71162208-71167283 |
| 19313 | Myl9 | NM_172118.1 | chr2:156601199-156607393 | 19408 | Naa10 | NM_019870.3 | chrX:71162208-71167283 |
| 19314 | Mylip | NM_153789.3 | chr13:45485116-45507309 | 19409 | Naa11 | NM_001033191.2 | chr5:97811227-97821349 |
| 19315 | Mylk | NM_139300.3 | chr16:34785036-35002520 | 19410 | Naa15 | NM_053089.3 | chr3:51219937-51279907 |
| 19316 | Mylk2 | NM_001081044.2 | chr2:152737087-152748801 | 19411 | Naa16 | NM_025832.2 | chr14:79734313-79790475 |
| 19317 | Mylk3 | NM_175441.5 | chr8:87848827-87889223 | 19412 | Naa20 | NM_001141965.1 | chr2:145728976-145742161 |
| 19318 | Mylk4 | NM_001166030.1 | chr13:32792695-32873648 | 19413 | Naa20 | NM_026425.3 | chr2:145728976-145742161 |
| 19319 | Mylpf | NM_016754.5 | chr7:134355121-134357801 | 19414 | Naa25 | NM_172722.3 | chr5:121847990-121890122 |
| 19320 | Mynn | NM_001289621.1 | chr3:30501008-30518795 | 19415 | Naa30 | NM_001081430.1 | chr14:49791901-49810706 |
| 19321 | Mynn | NM_001289622.1 | chr3:30501008-30518795 | 19416 | Naa35 | NM_030153.2 | chr13:59686693-59736142 |
| 19322 | Mynn | NM_001289623.1 | chr3:30501008-30518795 | 19417 | Naa38 | NM_030083.2 | chr11:69209293-69210173 |
| 19323 | Mynn | NM_030557.3 | chr3:30501008-30518795 | 19418 | Naa40 | NM_027643.1 | chr19:7300157-7315712 |
| 19324 | Myo10 | NM_019472.2 | chr15:25552304-25743426 | 19419 | Naa50 | NM_028108.3 | chr16:44139921-44163477 |
| 19325 | Myo15 | NM_001103171.1 | chr11:60282840-60341870 | 19420 | Naa60 | NM_001290689.1 | chr16:3884618-3904781 |
| 19326 | Myo15 | NM_010862.2 | chr11:60282840-60341870 | 19421 | Naa60 | NM_029090.3 | chr16:3884618-3904781 |
| 19327 | Myo15 | NM_182698.2 | chr11:60282840-60341870 | 19422 | Naaa | NM_001163687.1 | chr5:92686685-92707207 |
| 19328 | Myo16 | NM_001081397.1 | chr8:10153922-10633950 | 19423 | Naaa | NM_025972.4 | chr5:92686685-92707207 |
| 19329 | Myo18a | NM_001291212.1 | chr11:77590736-77679490 | 19424 | Naaladl2 | NM_028279.3 | chr9:18127464-18190372 |
| 19330 | Myo18a | NM_001291213.1 | chr11:77590736-77679490 | 19425 | Naaladl1 | NM_001009546.1 | chr19:6105797-6115555 |
| 19331 | Myo18a | NM_001291214.1 | chr11:77590736-77679490 | 19426 | Nab1 | NM_008667.3 | chr1:52512692-52557292 |
| 19332 | Myo18a | NM_001291215.1 | chr11:77590736-77679490 | 19427 | Nab2 | NM_001122895.1 | chr10:127080041-127103759 |
| 19333 | Myo18a | NM_011586.3 | chr11:77590736-77679490 | 19428 | Nab2 | NM_008668.2 | chr10:127080041-127103759 |
| 19334 | Myo18b | NM_028901.2 | chr5:113117896-113325382 | 19429 | Nabp1 | NM_028696.3 | chr1:51526331-51535243 |
| 19335 | Myo19 | NM_025414.3 | chr11:84693722-84724633 | 19430 | Nabp2 | NM_027257.1 | chr10:127838450-127846852 |
| 19336 | Myo1a | NM_001081219.2 | chr10:127142311-127157996 | 19431 | Naca | NM_001113199.1 | chr10:127472401-127485693 |
| 19337 | Myo1b | NM_001161817.2 | chr1:51806601-51972822 | 19432 | Naca | NM_001282976.1 | chr10:127472401-127485693 |
| 19338 | Myo1b | NM_001290982.1 | chr1:51806601-51972822 | 19433 | Naca | NM_013608.3 | chr10:127472401-127485693 |
| 19339 | Myo1b | NM_010863.4 | chr1:51806601-51972822 | 19434 | Nacad | NM_001081652.1 | chr11:6497825-6506057 |
| 19340 | Myo1c | NM_001080774.1 | chr11:75465010-75488136 | 19435 | Naccl | NM_025788.3 | chr8:87194377-87211761 |
| 19341 | Myo1c | NM_001080775.1 | chr11:75465010-75488136 | 19436 | Nacc2 | NM_001037098.1 | chr2:25911055-25978331 |
| 19342 | Myo1c | NM_008659.3 | chr11:75465010-75488136 | 19437 | Nacc2 | NM_026495.3 | chr2:25911055-25978331 |
| 19343 | Myo1d | NM_177390.3 | chr11:80295628-80593527 | 19438 | Nadk | NM_001159637.1 | chr4:154936500-154965110 |
| 19344 | Myo1e | NM_181072.3 | chr9:70055156-70247874 | 19439 | Nadk | NM_138671.2 | chr4:154936500-154965110 |
| 19345 | Myo1f | NM_053214.2 | chr17:33692651-33744709 | 19440 | Nadk2 | NM_001040395.4 | chr15:9001008-9040253 |
| 19346 | Myo1g | NM_178440.4 | chr11:6406550-6420961 | 19441 | Nadk2 | NM_001085410.2 | chr15:9001008-9040253 |
| 19347 | Myo1h | NM_001164573.1 | chr5:114764950-114814585 | 19442 | Nadk2 | NM_001286253.1 | chr15:9001008-9040253 |
| 19348 | Myo3a | NM_148413.3 | chr2:22149129-22473772 | 19443 | Nadk2 | NM_001286255.1 | chr15:9001008-9040253 |
| 19349 | Myo3b | NM_177376.2 | chr2:69877182-70267252 | 19444 | Nadsyn1 | NM_030221.2 | chr7:150981498-151008746 |
| 19350 | Myo5a | NM_010864.2 | chr9:74919012-75071494 | 19445 | Nae1 | NM_144931.3 | chr8:107034927-107058537 |
| 19351 | Myo5b | NM_201600.2 | chr18:74602273-74931131 | 19446 | Naf1 | NM_001163564.1 | chr8:69384115-69414463 |
| 19352 | Myo5c | NM_001081322.1 | chr9:75079820-75153257 | 19447 | Naga | NM_008669.4 | chr15:82159961-82169256 |
| 19353 | Myo6 | NM_001039546.2 | chr9:80012840-80159536 | 19448 | Nagk | NM_001164187.1 | chr6:83745050-83752550 |
| 19354 | Myo7a | NM_001256081.1 | chr7:105199563-105268003 | 19449 | Nagk | NM_019542.2 | chr6:83745050-83752550 |
| 19355 | Myo7a | NM_001256082.1 | chr7:105199563-105268003 | 19450 | Naglu | NM_013792.2 | chr11:100931407-100938985 |
| 19356 | Myo7a | NM_001256083.1 | chr7:105199563-105268003 | 19451 | Nagpa | NM_013796.3 | chr16:5195372-5204105 |
| 19357 | Myo7a | NM_008663.2 | chr7:105199563-105268003 | 19452 | Nagpa | NR_027804.1 | chr16:5195372-5204105 |
| 19358 | Myo7b | NM_032394.3 | chr18:32118887-32196585 | 19453 | Nags | NM_145829.2 | chr11:102006826-102010842 |
| 19359 | Myo9a | NM_173018.2 | chr9:59598980-59776673 | 19454 | Naif1 | NM_194335.2 | chr2:32305977-32310996 |
| 19360 | Myo9b | NM_001142322.1 | chr8:73796612-73884611 | 19455 | Naip1 | NM_008670.2 | chr13:101177724-101222819 |
| 19361 | Myo9b | NM_001142323.1 | chr8:73796612-73884611 | 19456 | Naip2 | NM_001126182.2 | chr13:100914017-100972077 |
| 19362 | Myo9b | NM_015742.2 | chr8:73796612-73884611 | 19457 | Naip2 | NM_010872.3 | chr13:100914017-100972077 |
| 19363 | Myoc | NM_164569281.1 | chr1:164569281-164579825 | 19458 | Naip5 | NM_010870.2 | chr13:100981694-101017291 |
| 19364 | Myocd | NM_145136.4 | chr11:64990071-65083491 | 19459 | Naip6 | NM_010871.2 | chr13:101051076-101086571 |
| 19365 | Myocd | NM_146386.3 | chr11:64990071-65083491 | 19460 | Naip7 | NM_021545.1 | chr13:101053070-101087643 |
| 19366 | Myod1 | NM_010866.2 | chr7:53631843-53634462 | 19461 | Nalcn | NM_177393.4 | chr14:123675862-124026366 |
| 19367 | Myof | NM_001099634.1 | chr19:37973525-38118067 | 19462 | Nampt | NM_021524.2 | chr12:33505200-33538234 |
| 19368 | Myog | NM_031189.2 | chr1:136186580-136189125 | 19463 | Nanog | NM_001289828.1 | chr6:122657506-122664651 |
| 19369 | Myom1 | NM_001083934.1 | chr17:71368896-71476196 | 19464 | Nanog | NM_001289830.1 | chr6:122657506-122664651 |
| 19370 | Myom1 | NM_010867.2 | chr17:71368896-71476196 | 19465 | Nanog | NM_001289831.1 | chr6:122657506-122664651 |
| 19371 | Myom2 | NM_008664.2 | chr8:15057652-15133419 | 19466 | Nanog | NM_028016.3 | chr6:122657506-122664651 |
| 19372 | Myom3 | NM_001085509.2 | chr4:135315629-135371482 | 19467 | Nanos1 | NM_178421.3 | chr19:60831889-60835817 |
| 19373 | Myot | NM_001033621.3 | chr18:44493727-44515376 | 19468 | Nanos2 | NM_194064.2 | chr7:19572872-19574311 |
| 19374 | Myoz1 | NM_021508.3 | chr4:21468323-21475762 | 19469 | Nanos3 | NM_194059.2 | chr8:86697631-86700451 |
| 19375 | Myoz2 | NM_021503.2 | chr3:122709123-122737905 | 19470 | Nanp | NM_026086.2 | chr2:150855420-150865115 |
| 19376 | Myoz3 | NM_133363.3 | chr18:60733370-60751370 | 19471 | Nars | NM_053179.3 | chr4:46502200-46516310 |
| 19377 | Mypn | NM_182927.2 | chr10:62578542-62666700 | 19472 | Napl1l | NM_001146707.1 | chr10:110910247-110935206 |
| 19378 | Mypop | NM_145579.3 | chr7:19576593-19587115 | 19473 | Nap1l1 | NM_015781.4 | chr10:110910247-110935206 |
| 19379 | Myrf | NM_001033481.1 | chr19:10282760-10315238 | 19474 | Nap1l2 | NM_008671.2 | chrX:100379397-100382003 |
| 19380 | Myrfl | NM_001033333.2 | chr10:116213600-116333935 | 19475 | Nap1l3 | NM_138742.1 | chrX:119508169-119510994 |
| 19381 | Myrip | NM_144557.5 | chr9:120213190-120383952 | 19476 | Nap1l4 | NM_001285489.1 | chr7:150699483-150735025 |
| 19382 | Mysm1 | NM_177239.2 | chr4:94608731-94645791 | 19477 | Nap1l4 | NM_001285490.1 | chr7:150699483-150735025 |
| 19383 | Myt1 | NM_001171615.1 | chr2:181498036-181562480 | 19478 | Nap1l4 | NM_008672.3 | chr7:150699483-150735025 |
| 19384 | Myt1 | NM_001171616.1 | chr2:181498036-181562480 | 19479 | Nap1l5 | NM_021432.2 | chr6:58855227-58857120 |
| 19385 | Myt1 | NM_001171680.1 | chr2:181498036-181562480 | 19480 | Napa | NM_025898.3 | chr7:16683991-16703324 |
| 19386 | Myt1 | NM_008665.4 | chr2:181498036-181562480 | 19481 | Napb | NM_019632.3 | chr2:148520392-148558156 |
| 19387 | Myt1l | NM_001093775.1 | chr12:30213248-30608074 | 19482 | Napepld | NM_178728.5 | chr5:21168720-21207163 |
| 19388 | Myt1l | NM_001093776.1 | chr12:30213248-30608074 | 19483 | Napg | NM_028017.1 | chr18:63137569-63159104 |
| 19389 | Myt1l | NM_001093778.1 | chr12:30213248-30608074 | 19484 | Naprt1 | NM_172607.3 | chr15:75723193-75724911 |
| 19390 | Myt1l | NM_008666.3 | chr12:30213248-30608074 | 19485 | Napsa | NM_008437.1 | chr7:51827814-51842216 |
| 19391 | Myzap | NM_001033208.4 | chr9:71352153-71440167 | 19486 | Narf | NM_026272.3 | chr11:121098549-121117170 |
| 19392 | Mzb1 | NM_027222.3 | chr18:35806918-35809021 | 19487 | Narfl | NM_026238.4 | chr17:25910721-25920277 |
| 19393 | Mzf1 | NM_001290452.1 | chr7:13627651-13640113 | 19488 | Narg2 | NM_145618.3 | chr9:69245804-69280881 |
| 19394 | Mzf1 | NM_001290453.1 | chr7:13627651-13640113 | 19489 | Nars | NM_001142950.1 | chr18:64659300-64676211 |
| 19395 | Mzf1 | NM_145819.2 | chr7:13627651-13640113 | 19490 | Nars | NM_027350.3 | chr18:64659300-64676211 |
| 19396 | Mzt1 | NM_175245.4 | chr14:99433762-99445355 | 19491 | Nars2 | NM_153591.4 | chr7:104100036-104213267 |
| 19397 | Mzt2 | NM_029354.2 | chr16:15488533-15863415 | 19492 | Nasp | NM_001081475.1 | chr4:116273656-116300556 |
| 19398 | N28178 | NM_172690.2 | chr4:42930122-42954479 | 19493 | Nasp | NM_001284229.1 | chr4:116273656-116300556 |
| 19399 | N4bp1 | NM_030563.2 | chr8:89365037-89409157 | 19494 | Nasp | NM_016777.3 | chr4:116273656-116300556 |

Fig. 25 - 104

| | | | | | | | | |
|---|---|---|---|---|---|---|---|---|
| 19495 | Nat1 | NM_008673.1 | chr8:70014656-70016002 | | 19590 | Nde1 | NM_001114085.1 | chr16:14163367-14193016 |
| 19496 | Nat10 | NM_153126.2 | chr2:103661415-103691407 | | 19591 | Nde1 | NM_001285503.1 | chr16:14163367-14193016 |
| 19497 | Nat14 | NM_201355.3 | chr7:4873852-4876608 | | 19592 | Nde1 | NM_001285504.1 | chr16:14163367-14193016 |
| 19498 | Nat2 | NM_001168577.1 | chr8:70018773-70026477 | | 19593 | Nde1 | NM_023317.2 | chr16:14163367-14193016 |
| 19499 | Nat2 | NM_008674.3 | chr8:70018773-70026477 | | 19594 | Ndel1 | NM_023668.2 | chr11:68634948-68666633 |
| 19500 | Nat3 | NM_008674.2 | chr8:70047752-70072526 | | 19595 | Ndfip1 | NM_022996.1 | chr18:38578628-38624060 |
| 19501 | Nat6 | NM_019750.3 | chr9:107482501-107486379 | | 19596 | Ndfip2 | NM_001190989.1 | chr14:105657889-105708515 |
| 19502 | Nat8 | NM_023455.3 | chr6:85780380-85781884 | | 19597 | Ndfip2 | NM_029561.4 | chr14:105657889-105708515 |
| 19503 | Nat8l | NM_001001985.3 | chr5:34338632-34348565 | | 19598 | Ndn | NM_010882.3 | chr7:69493162-69494813 |
| 19504 | Nat9 | NM_025400.3 | chr11:115044145-115048630 | | 19599 | Ndnf | NM_172399.3 | chr6:65621604-65656924 |
| 19505 | Nav1 | NM_173437.2 | chr1:137831157-137481932 | | 19600 | Ndni2 | NM_023239.4 | chr7:72016536-72017926 |
| 19506 | Nav2 | NM_001111016.1 | chr7:56214442-56865458 | | 19601 | Ndor1 | NM_001082476.2 | chr2:25100332-25110934 |
| 19507 | Nav2 | NM_175272.3 | chr7:56214442-56865458 | | 19602 | Ndor1 | NM_001252541.1 | chr2:25100332-25110934 |
| 19508 | Nav3 | NM_001081035.1 | chr10:109120494-109437275 | | 19603 | Ndor1 | NM_001252542.1 | chr2:25100332-25110934 |
| 19509 | Nbas | NM_027706.1 | chr12:13275932-13590617 | | 19604 | Ndp | NM_010883.3 | chrX:16462647-16488890 |
| 19510 | Nbea | NM_030595.1 | chr3:55429120-55987623 | | 19605 | Ndrg1 | NM_008681.2 | chr15:66760879-66801203 |
| 19511 | Nbeal1 | NM_173444.2 | chr1:60237442-60391549 | | 19606 | Ndrg2 | NM_001145959.1 | chr14:52524945-52533163 |
| 19512 | Nbeal2 | NM_183276.2 | chr9:110527293-110556665 | | 19607 | Ndrg2 | NM_013864.2 | chr14:52524945-52533163 |
| 19513 | Nbl1 | NM_008675.2 | chr4:138638206-138648885 | | 19608 | Ndrg3 | NM_013865.2 | chr2:156753077-156817847 |
| 19514 | Nbn | NM_013752.3 | chr4:15885113-15919736 | | 19609 | Ndrg3 | NM_180956.1 | chr2:156753077-156817847 |
| 19515 | Nbr1 | NM_001252220.1 | chr11:101413420-101443265 | | 19610 | Ndrg4 | NM_001195006.1 | chr8:98226936-98239019 |
| 19516 | Nbr1 | NM_001252222.1 | chr11:101413420-101443265 | | 19611 | Ndrg4 | NM_145602.3 | chr8:98226936-98239019 |
| 19517 | Nbr1 | NM_001252223.1 | chr11:101413420-101443265 | | 19612 | Ndst1 | NM_008306.4 | chr18:60845629-60873043 |
| 19518 | Nbr1 | NM_008676.3 | chr11:101413420-101443265 | | 19613 | Ndst2 | NM_010811.2 | chr14:21542951-21553784 |
| 19519 | Ncald | NM_001170866.1 | chr15:37295929-37722183 | | 19614 | Ndst3 | NM_031186.3 | chr3:123229083-123375310 |
| 19520 | Ncald | NM_001170867.1 | chr15:37295929-37722183 | | 19615 | Ndst4 | NM_022565.2 | chr3:125107608-125427904 |
| 19521 | Ncald | NM_001170868.1 | chr15:37295929-37722183 | | 19616 | Ndufa1 | NM_019443.2 | chrX:34727583-34731233 |
| 19522 | Ncald | NM_134894.3 | chr15:37295929-37722183 | | 19617 | Ndufa10 | NM_024197.1 | chr1:94836296-94370335 |
| 19523 | Ncam1 | NM_001081445.1 | chr9:49310250-49607174 | | 19618 | Ndufa11 | NM_027244.1 | chr17:56857184-56866671 |
| 19524 | Ncam1 | NM_001113204.1 | chr9:49310250-49607174 | | 19619 | Ndufa12 | NM_025551.3 | chr10:93661753-93683693 |
| 19525 | Ncam1 | NM_010875.3 | chr9:49310250-49607174 | | 19620 | Ndufa13 | NM_023312.2 | chr8:72418081-72426457 |
| 19526 | Ncam2 | NM_001113208.1 | chr16:81200941-81624532 | | 19621 | Ndufa2 | NM_010885.5 | chr18:36901986-36904241 |
| 19527 | Ncam2 | NM_010954.4 | chr16:81200941-81624532 | | 19622 | Ndufa3 | NM_025348.2 | chr7:3568974-3571763 |
| 19528 | Ncan | NM_007789.3 | chr8:72616984-72644743 | | 19623 | Ndufa4 | NM_010886.2 | chr6:11850372-11857446 |
| 19529 | Ncapd2 | NM_146171.1 | chr6:125118025-125141604 | | 19624 | Ndufa4l2 | NM_001098789.1 | chr10:126951995-126954210 |
| 19530 | Ncapd3 | NM_178113.3 | chr9:26837759-26902900 | | 19625 | Ndufa5 | NM_026614.2 | chr6:24468665-24477687 |
| 19531 | Ncapg | NM_019438.1 | chr5:46061164-46091786 | | 19626 | Ndufa6 | NM_025987.3 | chr15:82180568-82184721 |
| 19532 | Ncapg2 | NM_133762.3 | chr12:117643874-117702004 | | 19627 | Ndufa7 | NM_023202.4 | chr17:33961516-33975261 |
| 19533 | Ncaph | NM_144818.3 | chr2:126929545-126959690 | | 19628 | Ndufa7 | NR_103514.1 | chr17:33961516-33975261 |
| 19534 | Ncaph2 | NM_001115132.2 | chr15:89186149-89207468 | | 19629 | Ndufa7 | NR_103515.1 | chr17:33961516-33975261 |
| 19535 | Ncaph2 | NM_001271600.1 | chr15:89186149-89207468 | | 19630 | Ndufa7 | NR_103516.1 | chr17:33961516-33975261 |
| 19536 | Ncaph2 | NM_001271601.1 | chr15:89186149-89207468 | | 19631 | Ndufa8 | NM_026703.2 | chr2:35891853-35904812 |
| 19537 | Ncaph2 | NR_073376.1 | chr15:89186149-89207468 | | 19632 | Ndufa9 | NM_025358.3 | chr6:126771880-126799162 |
| 19538 | Ncbp1 | NM_001033201.3 | chr4:46151382-46185274 | | 19633 | Ndufab1 | NM_028177.3 | chr7:129231557-129245362 |
| 19539 | Ncbp2 | NM_026554.4 | chr16:31948631-31958558 | | 19634 | Ndufaf1 | NM_027175.3 | chr2:119481186-119488534 |
| 19540 | Nccrp1 | NM_001081115.1 | chr7:29328615-29332273 | | 19635 | Ndufaf2 | NM_001127346.1 | chr13:108842782-108948819 |
| 19541 | Ncdn | NM_011986.4 | chr4:126420993-126430673 | | 19636 | Ndufaf3 | NM_023247.1 | chr9:108468195-108469673 |
| 19542 | Nceh1 | NM_178772.3 | chr3:27081925-27143833 | | 19637 | Ndufaf4 | NM_026742.4 | chr4:24825229-24832148 |
| 19543 | Ncf1 | NM_001286037.1 | chr5:134695922-134705495 | | 19638 | Ndufaf5 | NM_027093.4 | chr2:139996381-140030988 |
| 19544 | Ncf1 | NM_010876.4 | chr5:134695922-134705495 | | 19639 | Ndufaf6 | NM_001085493.2 | chr4:10978194-11003352 |
| 19545 | Ncf1 | NR_104383.1 | chr5:134695922-134705495 | | 19640 | Ndufaf7 | NM_028611.3 | chr17:79336474-79347392 |
| 19546 | Ncf2 | NM_010877.4 | chr1:154655019-154684120 | | 19641 | Ndufb10 | NM_026684.2 | chr17:24859011-24861333 |
| 19547 | Ncf4 | NM_008700.2 | chr15:78075240-78093010 | | 19642 | Ndufb11 | NM_019435.4 | chrX:20192452-20194690 |
| 19548 | Nck1 | NM_010878.2 | chr9:100395421-100446472 | | 19643 | Ndufb2 | NM_026612.3 | chr6:39542581-39549470 |
| 19549 | Nck2 | NM_010879.3 | chr1:43502595-43627363 | | 19644 | Ndufb3 | NM_025597.2 | chr1:58643442-58652792 |
| 19550 | Nckap1 | NM_001001884.1 | chr2:80340668-80421339 | | 19645 | Ndufb4 | NM_026610.1 | chr16:37647687-37654454 |
| 19551 | Nckap1 | NM_016965.3 | chr2:80340668-80421339 | | 19646 | Ndufb5 | NM_025316.2 | chr3:32635984-32650481 |
| 19552 | Nckap1l | NM_153505.4 | chr15:103284255-103329231 | | 19647 | Ndufb6 | NM_001033305.2 | chr4:40217695-40226401 |
| 19553 | Nckap5 | NM_001081795.1 | chr1:127810212-128727209 | | 19648 | Ndufb7 | NM_025843.3 | chr8:86090656-86095522 |
| 19554 | Nckap5 | NM_172484.3 | chr1:127810212-128727209 | | 19649 | Ndufb8 | NM_026061.2 | chr19:44624743-44629905 |
| 19555 | Nckap5 | NM_176957.1 | chr1:127810212-128727209 | | 19650 | Ndufb9 | NM_023172.3 | chr15:58765364-58771044 |
| 19556 | Nckap5l | NM_001001884.1 | chr15:99252464-99288179 | | 19651 | Ndufc1 | NM_025523.1 | chr3:51209400-51212877 |
| 19557 | Nckipsd | NM_030729.4 | chr9:108710710-108720697 | | 19652 | Ndufc2 | NM_024220.2 | chr7:104548512-104556310 |
| 19558 | Ncl | NM_010880.3 | chr1:88241294-88256030 | | 19653 | Ndufs1 | NM_001160038.1 | chr1:63161044-63223396 |
| 19559 | Ncln | NM_134009.3 | chr10:80949203-80959108 | | 19654 | Ndufs1 | NM_001160039.1 | chr1:63161044-63223396 |
| 19560 | Ncmap | NM_001168498.1 | chr4:134925491-134954142 | | 19655 | Ndufs1 | NM_001160040.1 | chr1:63161044-63223396 |
| 19561 | Ncmap | NM_001168500.1 | chr4:134925491-134954142 | | 19656 | Ndufs2 | NM_145518.2 | chr1:63161044-63223396 |
| 19562 | Ncmap | NM_001243305.1 | chr4:134925491-134954142 | | 19657 | Ndufs2 | NM_153064.4 | chr1:173164990-173177243 |
| 19563 | Ncmap | NM_001243306.1 | chr4:134925491-134954142 | | 19658 | Ndufs3 | NM_026688.2 | chr2:90734792-90744878 |
| 19564 | Ncmap | NM_145543.2 | chr4:134925491-134954142 | | 19659 | Ndufs4 | NM_010887.2 | chr13:115078002-115178302 |
| 19565 | Ncmap | NM_181047.1 | chr4:134925491-134954142 | | 19660 | Ndufs5 | NM_001030274.1 | chr4:123389953-123395429 |
| 19566 | Ncoa1 | NM_010881.2 | chr12:4247361-4484060 | | 19661 | Ndufs6 | NM_010888.2 | chr13:73457323-73465930 |
| 19567 | Ncoa2 | NM_001001795.1 | chr1:13129239-13364164 | | 19662 | Ndufs6 | NR_033306.1 | chr13:73457323-73465930 |
| 19568 | Ncoa2 | NM_008678.3 | chr1:13129239-13364164 | | 19663 | Ndufs7 | NM_029272.3 | chr10:79712196-79719537 |
| 19569 | Ncoa3 | NM_008679.3 | chr2:165818136-165898742 | | 19664 | Ndufs8 | NM_001271443.1 | chr19:3908862-3912774 |
| 19570 | Ncoa4 | NM_001033988.2 | chr14:32973072-32993041 | | 19665 | Ndufs8 | NM_001271444.1 | chr19:3908862-3912774 |
| 19571 | Ncoa4 | NM_001284319.1 | chr14:32973072-32993041 | | 19666 | Ndufs8 | NM_144870.5 | chr19:3908862-3912774 |
| 19572 | Ncoa4 | NM_019744.4 | chr14:32973072-32993041 | | 19667 | Ndufv1 | NM_133666.3 | chr19:4007498-4012755 |
| 19573 | Ncoa5 | NM_144892.1 | chr2:164825856-164860279 | | 19668 | Ndufv2 | NM_001278415.1 | chr17:66428134-66450899 |
| 19574 | Ncoa6 | NM_001242558.1 | chr2:155216391-155266519 | | 19669 | Ndufv2 | NM_028388.3 | chr17:66428134-66450899 |
| 19575 | Ncoa6 | NM_019825.3 | chr2:155216391-155266519 | | 19670 | Ndufv3 | NM_001083891.1 | chr17:31657059-31668270 |
| 19576 | Ncoa7 | NM_001112672.2 | chr10:30365387-30522913 | | 19671 | Ndufv3 | NM_030087.2 | chr17:31657059-31668270 |
| 19577 | Ncoa7 | NM_172495.5 | chr10:30365387-30522913 | | 19672 | Neat1 | NR_003513.3 | chr19:5842301-5845478 |
| 19578 | Ncor1 | NM_001252313.1 | chr11:62094974-62270834 | | 19673 | Neb | NM_010889.1 | chr2:51992167-52194318 |
| 19579 | Ncor1 | NM_011308.3 | chr11:62094974-62270834 | | 19674 | Neb1 | NM_028757.2 | chr17:17268361-17652695 |
| 19580 | Ncor1 | NM_177229.3 | chr11:62094974-62270834 | | 19675 | Necab1 | NM_178617.4 | chr4:14879392-15076278 |
| 19581 | Ncor2 | NM_001253904.1 | chr5:125497522-125659584 | | 19676 | Necab2 | NM_054095.2 | chr8:121970618-121996535 |
| 19582 | Ncor2 | NM_001253905.1 | chr5:125497522-125659584 | | 19677 | Necab3 | NM_021546.3 | chr2:154370141-154384589 |
| 19583 | Ncor2 | NM_011424.3 | chr5:125497522-125659584 | | 19678 | Necap1 | NM_026267.2 | chr6:122824574-122838959 |
| 19584 | Ncr1 | NM_010746.3 | chr7:4289325-4296766 | | 19679 | Necap2 | NM_025383.3 | chr4:140622426-140634260 |
| 19585 | Ncs1 | NM_019681.3 | chr2:31101442-31150991 | | 19680 | Nedd1 | NM_008682.2 | chr10:92147489-92185163 |
| 19586 | Ncstn | NM_021607.3 | chr1:173996144-174012880 | | 19681 | Nedd4 | NM_010890.3 | chr9:72510153-72597655 |
| 19587 | Nctc1 | NR_002452.2 | chr7:149730513-149744503 | | 19682 | Nedd4l | NM_001114386.1 | chr18:65047409-65377480 |
| 19588 | Ndc1 | NM_028355.3 | chr4:107040388-107086943 | | 19683 | Nedd4l | NM_031881.2 | chr18:65047409-65377480 |
| 19589 | Ndc80 | NM_023294.2 | chr17:71845439-71876197 | | 19684 | Nedd8 | NM_008683.3 | chr14:56281103-56290743 |

Fig. 25 - 105

| | | | |
|---|---|---|---|
| 19685 | Nedd9 | NM_001111324.2 | chr13:41405284-41582729 |
| 19686 | Nedd9 | NM_017464.5 | chr13:41405284-41582729 |
| 19687 | Nefh | NM_010904.3 | chr11:4838759-4848067 |
| 19688 | Nefl | NM_010910.1 | chr14:68701940-68705794 |
| 19689 | Nefm | NM_008691.2 | chr14:68737602-68743061 |
| 19690 | Negr1 | NM_001039094.3 | chr3:156224757-156979428 |
| 19691 | Negr1 | NM_177274.4 | chr3:156224757-156979428 |
| 19692 | Neil1 | NM_028347.2 | chr9:56991062-56994841 |
| 19693 | Neil2 | NM_201610.2 | chr14:63801281-63812362 |
| 19694 | Neil3 | NM_146208.2 | chr8:54672220-54724419 |
| 19695 | Nek1 | NM_175089.4 | chr8:63472016-63609031 |
| 19696 | Nek10 | NM_001195229.1 | chr14:15653328-15839207 |
| 19697 | Nek11 | NM_172461.3 | chr9:105064796-105297617 |
| 19698 | Nek2 | NM_010892.3 | chr1:193645351-193656928 |
| 19699 | Nek3 | NM_001162947.1 | chr8:23238754-23276907 |
| 19700 | Nek3 | NM_011848.4 | chr8:23238754-23276907 |
| 19701 | Nek4 | NM_011849.3 | chr14:31764673-31800587 |
| 19702 | Nek5 | NM_177898.4 | chr8:23184087-23235525 |
| 19703 | Nek6 | NM_001159631.1 | chr2:38367216-38443010 |
| 19704 | Nek6 | NM_021606.3 | chr2:38367216-38443010 |
| 19705 | Nek7 | NM_021605.3 | chr1:140381290-140516273 |
| 19706 | Nek8 | NM_080849.3 | chr11:77979607-77990168 |
| 19707 | Nek9 | NM_145138.2 | chr12:86640463-86680312 |
| 19708 | Nelfa | NM_011914.2 | chr5:34240829-34278907 |
| 19709 | Nelfb | NM_021393.2 | chr2:25055231-25067009 |
| 19710 | Nelfcd | NM_020580.3 | chr2:174241305-174253003 |
| 19711 | Nelfe | NM_001045863.1 | chr17:34987335-34993317 |
| 19712 | Nelfe | NM_001045864.1 | chr17:34987335-34993317 |
| 19713 | Nelfe | NM_138580.2 | chr17:34987335-34993317 |
| 19714 | Nell1 | NM_001037906.2 | chr7:57230720-58118659 |
| 19715 | Nell1os | NR_045928.1 | chr7:57772679-57831254 |
| 19716 | Nell2 | NM_001289653.1 | chr15:95049870-95358683 |
| 19717 | Nemf | NM_025441.3 | chr12:70412529-70458163 |
| 19718 | Nenf | NM_025424.2 | chr1:193130675-193141997 |
| 19719 | Neo1 | NM_001042752.1 | chr9:58722486-58884248 |
| 19720 | Neo1 | NM_008684.2 | chr9:58722486-58884248 |
| 19721 | Nepn | NM_025684.2 | chr10:52111413-52124410 |
| 19722 | Nes | NM_016701.3 | chr3:87775014-87784373 |
| 19723 | Nespas | NR_002846.2 | chr2:174106738-174120937 |
| 19724 | Net1 | NM_001047159.2 | chr13:3881263-3917466 |
| 19725 | Net1 | NM_019671.3 | chr13:3881263-3917466 |
| 19726 | Neto1 | NM_144946.4 | chr18:86564343-86671289 |
| 19727 | Neto2 | NM_001081324.1 | chr8:88160486-88214908 |
| 19728 | Neu1 | NM_010893.3 | chr17:35068197-35074242 |
| 19729 | Neu2 | NM_001160163.1 | chr1:89470601-89494415 |
| 19730 | Neu2 | NM_001160164.1 | chr1:89470601-89494415 |
| 19731 | Neu2 | NM_001160165.1 | chr1:89470601-89494415 |
| 19732 | Neu2 | NM_015750.3 | chr1:89470601-89494415 |
| 19733 | Neu3 | NM_016720.2 | chr7:106959948-106976927 |
| 19734 | Neu4 | NM_173772.3 | chr1:95917069-95924907 |
| 19735 | Neurl1a | NM_001163480.1 | chr19:47253309-47333931 |
| 19736 | Neurl1a | NM_021360.4 | chr19:47253309-47333931 |
| 19737 | Neurl1b | NM_001081656.2 | chr17:26551909-26583287 |
| 19738 | Neurl2 | NM_001082974.2 | chr2:164656230-164659096 |
| 19739 | Neurl3 | NM_153408.2 | chr1:36321446-36330270 |
| 19740 | Neurl4 | NM_001013414.3 | chr11:69715317-69727326 |
| 19741 | Neurl4 | NM_001291118.1 | chr11:69715317-69727326 |
| 19742 | Neurl4 | NM_001291119.1 | chr11:69715317-69727326 |
| 19743 | Neurod1 | NM_010894.1 | chr2:79292797-79296793 |
| 19744 | Neurod2 | NM_010895.3 | chr11:98186730-98190959 |
| 19745 | Neurod4 | NM_007501.4 | chr10:129705207-129717296 |
| 19746 | Neurod6 | NM_009717.2 | chr6:55627812-55631257 |
| 19747 | Neurog1 | NM_010896.2 | chr13:56351859-56353524 |
| 19748 | Neurog2 | NM_009718.2 | chr3:127336062-127338549 |
| 19749 | Neurog3 | NM_009719.6 | chr10:61595837-61597511 |
| 19750 | Nexn | NM_199465.2 | chr3:151899947-151929284 |
| 19751 | Nf1 | NM_010897.2 | chr11:79153394-79395111 |
| 19752 | Nf2 | NM_001252250.1 | chr11:4665847-4749547 |
| 19753 | Nf2 | NM_001252251.1 | chr11:4665847-4749547 |
| 19754 | Nf2 | NM_001252252.1 | chr11:4665847-4749547 |
| 19755 | Nf2 | NM_001252253.1 | chr11:4665847-4749547 |
| 19756 | Nf2 | NM_010898.4 | chr11:4665847-4749547 |
| 19757 | Nfam1 | NM_001271411.1 | chr15:82827165-82863827 |
| 19758 | Nfam1 | NM_001271412.1 | chr15:82827165-82863827 |
| 19759 | Nfam1 | NM_001271413.1 | chr15:82827165-82863827 |
| 19760 | Nfam1 | NM_001271414.1 | chr15:82827165-82863827 |
| 19761 | Nfam1 | NM_028728.3 | chr15:82827165-82863827 |
| 19762 | Nfasc | NM_001160316.1 | chr1:134461266-134638374 |
| 19763 | Nfasc | NM_001160317.1 | chr1:134461266-134638374 |
| 19764 | Nfasc | NM_001160318.1 | chr1:134461266-134638374 |
| 19765 | Nfasc | NM_182716.4 | chr1:134461266-134638374 |
| 19766 | Nfat5 | NM_001286260.1 | chr8:109817369-109903417 |
| 19767 | Nfat5 | NM_018823.2 | chr8:109817369-109903417 |
| 19768 | Nfat5 | NM_133957.3 | chr8:109817369-109903417 |
| 19769 | Nfatc1 | NM_001164109.1 | chr18:80802943-80909810 |
| 19770 | Nfatc1 | NM_001164110.1 | chr18:80802943-80909810 |
| 19771 | Nfatc1 | NM_001164111.1 | chr18:80802943-80909810 |
| 19772 | Nfatc1 | NM_001164112.1 | chr18:80802943-80909810 |
| 19773 | Nfatc1 | NM_016791.4 | chr18:80802943-80909810 |
| 19774 | Nfatc1 | NM_198429.2 | chr18:80802943-80909810 |
| 19775 | Nfatc2 | NM_001037177.2 | chr2:168301909-168427157 |
| 19776 | Nfatc2 | NM_001037178.2 | chr2:168301909-168427157 |
| 19777 | Nfatc2 | NM_001136073.2 | chr2:168301909-168427157 |
| 19778 | Nfatc2 | NM_001291168.1 | chr2:168301909-168427157 |
| 19779 | Nfatc2 | NM_001291169.1 | chr2:168301909-168427157 |
| 19780 | Nfatc2 | NM_001291170.1 | chr2:168301909-168427157 |
| 19781 | Nfatc2 | NM_001291171.1 | chr2:168301909-168427157 |
| 19782 | Nfatc2 | NM_001291172.1 | chr2:168301909-168427157 |
| 19783 | Nfatc2 | NM_001291173.1 | chr2:168301909-168427157 |
| 19784 | Nfatc2 | NM_001291174.1 | chr2:168301909-168427157 |
| 19785 | Nfatc2 | NM_001291175.1 | chr2:168301909-168427157 |
| 19786 | Nfatc2 | NM_001291176.1 | chr2:168301909-168427157 |
| 19787 | Nfatc2 | NM_001291177.1 | chr2:168301909-168427157 |
| 19788 | Nfatc2 | NM_001291178.1 | chr2:168301909-168427157 |
| 19789 | Nfatc2 | NM_001291179.1 | chr2:168301909-168427157 |
| 19790 | Nfatc2 | NM_010899.3 | chr2:168301909-168427157 |
| 19791 | Nfatc2 | NR_111897.1 | chr2:168301909-168427157 |
| 19792 | Nfatc2 | NR_111898.1 | chr2:168301909-168427157 |
| 19793 | Nfatc2ip | NM_010900.3 | chr7:133526367-133540251 |
| 19794 | Nfatc3 | NM_010901.2 | chr8:108583502-108654437 |
| 19795 | Nfatc4 | NM_001168346.1 | chr14:56443631-56452780 |
| 19796 | Nfatc4 | NM_023699.3 | chr14:56443631-56452780 |
| 19797 | Nfe2 | NM_008685.3 | chr15:103078648-103085847 |
| 19798 | Nfe2l1 | NM_001130450.1 | chr11:96678727-96691282 |
| 19799 | Nfe2l1 | NM_001130451.1 | chr11:96678727-96691282 |
| 19800 | Nfe2l1 | NM_001130452.1 | chr11:96678727-96691282 |
| 19801 | Nfe2l1 | NM_001130453.1 | chr11:96678727-96691282 |
| 19802 | Nfe2l1 | NM_001130454.1 | chr11:96678727-96691282 |
| 19803 | Nfe2l1 | NM_008686.3 | chr11:96678727-96691282 |
| 19804 | Nfe2l2 | NM_010902.3 | chr2:75513575-75542698 |
| 19805 | Nfe2l3 | NM_010903.1 | chr6:51382668-51408767 |
| 19806 | Nfia | NM_001122952.1 | chr4:97234565-97785567 |
| 19807 | Nfia | NM_001122953.1 | chr4:97234565-97785567 |
| 19808 | Nfia | NM_010905.3 | chr4:97234565-97785567 |
| 19809 | Nfib | NM_001113209.2 | chr4:81936076-82151683 |
| 19810 | Nfib | NM_001113210.2 | chr4:81936076-82151683 |
| 19811 | Nfib | NM_001286127.1 | chr4:81936076-82151683 |
| 19812 | Nfib | NM_001286131.1 | chr4:81936076-82151683 |
| 19813 | Nfib | NM_008687.6 | chr4:81936076-82151683 |
| 19814 | Nfic | NM_008688.3 | chr10:80858935-80889918 |
| 19815 | Nfic | NM_026756.2 | chr10:80858935-80889918 |
| 19816 | Nfil3 | NM_017373.2 | chr13:53062577-53076408 |
| 19817 | Nfix | NM_001081981.2 | chr8:87225355-87324237 |
| 19818 | Nfix | NM_001081982.2 | chr8:87225355-87324237 |
| 19819 | Nfix | NM_010906.3 | chr8:87225355-87324237 |
| 19820 | Nfkb1 | NM_008689.2 | chr3:135247618-135354511 |
| 19821 | Nfkb2 | NM_001177369.1 | chr19:46379226-46401646 |
| 19822 | Nfkb2 | NM_001177370.1 | chr19:46379226-46401646 |
| 19823 | Nfkb2 | NM_019408.3 | chr19:46379226-46401646 |
| 19824 | Nfkbia | NM_010907.2 | chr12:56590395-56593634 |
| 19825 | Nfkbib | NM_010908.5 | chr7:29543270-29551663 |
| 19826 | Nfkbid | NM_172142.3 | chr7:31208322-31213765 |
| 19827 | Nfkbie | NM_008690.2 | chr17:45692664-45700117 |
| 19828 | Nfkbil1 | NM_010909.4 | chr17:35357119-35372760 |
| 19829 | Nfkbiz | NM_001159394.1 | chr16:55811489-55838754 |
| 19830 | Nfkbiz | NM_001159395.1 | chr16:55811489-55838754 |
| 19831 | Nfkbiz | NM_030612.3 | chr16:55811489-55838754 |
| 19832 | Nfrcb | NM_172766.3 | chr9:31193776-31228918 |
| 19833 | Nfs1 | NM_010911.2 | chr2:155949373-155969922 |
| 19834 | Nfu1 | NM_001170591.1 | chr6:86959829-86978455 |
| 19835 | Nfu1 | NM_020045.3 | chr6:86959829-86978455 |
| 19836 | Nfx1 | NM_001290448.1 | chr4:40917938-40973025 |
| 19837 | Nfx1 | NM_001290449.1 | chr4:40917938-40973025 |
| 19838 | Nfx1 | NM_023739.3 | chr4:40917938-40973025 |
| 19839 | Nfxl1 | NM_133921.2 | chr5:72904542-72950884 |
| 19840 | Nfya | NM_001110832.1 | chr17:48526209-48549145 |
| 19841 | Nfya | NM_010913.2 | chr17:48526209-48549145 |
| 19842 | Nfyb | NM_010914.2 | chr10:82211444-82226886 |
| 19843 | Nfyc | NM_001048168.2 | chr4:120430039-120504184 |
| 19844 | Nfyc | NM_001277095.1 | chr4:120430039-120504184 |
| 19845 | Nfyc | NM_008692.4 | chr4:120430039-120504184 |
| 19846 | Ngb | NM_022414.2 | chr12:88438480-88443489 |
| 19847 | Ngdn | NM_026890.2 | chr14:55634290-55642974 |
| 19848 | Ngef | NM_001111314.1 | chr1:89373403-89470445 |
| 19849 | Ngef | NM_019867.2 | chr1:89373403-89470445 |
| 19850 | Ngf | NM_001112698.2 | chr3:102273841-102324936 |
| 19851 | Ngf | NM_013609.3 | chr3:102273841-102324936 |
| 19852 | Ngfr | NM_033217.3 | chr11:95436139-95449012 |
| 19853 | Ngfrap1 | NM_001110233.1 | chrX:132804791-132806517 |
| 19854 | Ngfrap1 | NM_001110234.1 | chrX:132804791-132806517 |
| 19855 | Ngfrap1 | NM_009750.2 | chrX:132804791-132806517 |
| 19856 | Ngly1 | NM_021504.3 | chr14:17081828-17144440 |
| 19857 | Ngp | NM_008694.2 | chr9:110322311-110325516 |
| 19858 | Ngrn | NM_031375.3 | chr7:87406100-87410264 |
| 19859 | Ngrn | NR_028053.1 | chr7:87406100-87410264 |
| 19860 | Nhej1 | NM_029342.4 | chr1:75013919-75121800 |
| 19861 | Nhlh1 | NM_010916.2 | chr1:173982422-173987727 |
| 19862 | Nhlh2 | NM_178777.3 | chr3:101814067-101819415 |
| 19863 | Nhlrc1 | NM_175340.3 | chr13:47107925-47110219 |
| 19864 | Nhlrc2 | NM_025811.3 | chr19:56622750-56673336 |
| 19865 | Nhlrc3 | NM_172501.2 | chr3:53255917-53267180 |
| 19866 | Nhlrc4 | NM_001039038.2 | chr17:26079177-26081876 |
| 19867 | Nhp2 | NM_026631.3 | chr11:51433275-51437216 |
| 19868 | Nhp2l1 | NM_011482.4 | chr15:81871774-81878028 |
| 19869 | Nhs | NM_001081052.1 | chrX:158274361-158597373 |
| 19870 | Nhs | NM_001290526.1 | chrX:158274361-158597373 |
| 19871 | Nhsl1 | NM_001163592.1 | chr10:18127480-18253697 |
| 19872 | Nhsl1 | NM_173390.3 | chr10:18127480-18253697 |
| 19873 | Nhsl2 | NM_001163610.1 | chrX:99044724-99287394 |
| 19874 | Nicn1 | NM_025449.3 | chr9:108192787-108198827 |

Fig. 25 - 106

| | | | |
|---|---|---|---|
| 19875 | Nid1 | NM_010917.2 | chr13:13529868-13604542 |
| 19876 | Nid2 | NM_008695.2 | chr14:20570479-20631009 |
| 19877 | Nif3l1 | NM_022988.2 | chr1:58504476-58519120 |
| 19878 | Nifk | NM_026472.4 | chr1:120218419-120230408 |
| 19879 | Nim1k | NM_175538.3 | chr13_random:66904-112693 |
| 19880 | Nim1k | NM_175538.3 | chr13_random:260753-306603 |
| 19881 | Nin | NM_001081453.1 | chr12:71112421-71213022 |
| 19882 | Nin | NM_001286079.2 | chr12:71112421-71213022 |
| 19883 | Nin | NM_001286080.2 | chr12:71112421-71213022 |
| 19884 | Nin | NM_008697.4 | chr12:71112421-71213022 |
| 19885 | Nin | NR_104397.2 | chr12:71112421-71213022 |
| 19886 | Nin | NR_104398.2 | chr12:71112421-71213022 |
| 19887 | Ninj1 | NM_013610.2 | chr13:49282915-49291620 |
| 19888 | Ninj2 | NM_016718.2 | chr6:120043397-120150356 |
| 19889 | Ninl | NM_207204.2 | chr2:150760254-150835134 |
| 19890 | Nip7 | NM_001164472.1 | chr8:109580776-109584828 |
| 19891 | Nip7 | NM_025391.2 | chr8:109580776-109584828 |
| 19892 | Nip7 | NR_028367.1 | chr8:109580776-109584828 |
| 19893 | Nipa1 | NM_153578.2 | chr7:63233854-63274943 |
| 19894 | Nipa2 | NM_001256130.1 | chr7:63097440-63217863 |
| 19895 | Nipa2 | NM_001256131.1 | chr7:63097440-63217863 |
| 19896 | Nipa2 | NM_001256132.1 | chr7:63097440-63217863 |
| 19897 | Nipa2 | NM_001256133.1 | chr7:63097440-63217863 |
| 19898 | Nipa2 | NM_023647.5 | chr7:63097440-63217863 |
| 19899 | Nipal1 | NM_001081205.1 | chr5:73039034-73062317 |
| 19900 | Nipal2 | NM_145469.5 | chr15:34502554-34608461 |
| 19901 | Nipal3 | NM_028995.3 | chr4:135004815-135050419 |
| 19902 | Nipal4 | NM_172524.3 | chr4:145961656-45979861 |
| 19903 | Nipbl | NM_027707.3 | chr15:8239823-8394463 |
| 19904 | Nipbl | NM_201232.2 | chr15:8239823-8394463 |
| 19905 | Nipsnap1 | NM_008698.2 | chr11:4774006-4794263 |
| 19906 | Nipsnap3a | NM_028529.1 | chr4:53002155-53013726 |
| 19907 | Nipsnap3b | NM_025623.2 | chr4:53024795-53034931 |
| 19908 | Nisch | NM_022656.2 | chr14:31984113-32020012 |
| 19909 | Nit1 | NM_001242580.1 | chr1:173259275-173275776 |
| 19910 | Nit1 | NM_012049.2 | chr1:173259275-173275776 |
| 19911 | Nit2 | NM_023175.1 | chr16:57156777-57167445 |
| 19912 | Nkain1 | NM_130125704-130169623 | chr4:130125704-130169623 |
| 19913 | Nkain2 | NM_001013411.2 | chr10:31409124-32609721 |
| 19914 | Nkain2 | NM_001025286.2 | chr10:31409124-32609721 |
| 19915 | Nkain3 | NM_001290410.1 | chr4:20046020-20705815 |
| 19916 | Nkain3 | NM_172987.2 | chr4:20046020-20705815 |
| 19917 | Nkain4 | NM_001141933.1 | chr2:180669476-180689404 |
| 19918 | Nkain4 | NM_021426.4 | chr2:180669476-180689404 |
| 19919 | Nkap | NM_025937.4 | chrX:34666758-34690741 |
| 19920 | Nkapl | NM_025719.3 | chr13:21558915-21560370 |
| 19921 | Nkd1 | NM_001163660.1 | chr8:91045242-91118786 |
| 19922 | Nkd1 | NM_027780.3 | chr8:91045242-91118786 |
| 19923 | Nkd2 | NM_028186.4 | chr13:73956775-73985079 |
| 19924 | Nkg7 | NM_024253.4 | chr7:50692507-50693616 |
| 19925 | Nkiras1 | NM_023526.3 | chr14:19103656-19116514 |
| 19926 | Nkiras2 | NM_028624.2 | chr11:100484269-100488916 |
| 19927 | Nkpd1 | NM_027116.1 | chr7:20104079-20110399 |
| 19928 | Nkrf | NM_029891.2 | chrX:34427536-34442894 |
| 19929 | Nktr | NM_010918.2 | chr9:121628299-121665959 |
| 19930 | Nkx1-1 | NM_011320.1 | chr5:33773382-33776739 |
| 19931 | Nkx1-2 | NM_009123.2 | chr7:139787921-139791320 |
| 19932 | Nkx2-1 | NM_001146198.1 | chr12:57632923-57637895 |
| 19933 | Nkx2-1 | NM_009385.3 | chr12:57632923-57637895 |
| 19934 | Nkx2-2 | NM_001077632.1 | chr2:147003281-147157417 |
| 19935 | Nkx2-2 | NM_010919.2 | chr2:147003281-147157417 |
| 19936 | Nkx2-2os | NR_030769.2 | chr2:147009819-147157417 |
| 19937 | Nkx2-3 | NM_008699.2 | chr19:43686814-43690382 |
| 19938 | Nkx2-4 | NM_023504.1 | chr2:146909611-146911081 |
| 19939 | Nkx2-5 | NM_008700.2 | chr17:26975609-26978510 |
| 19940 | Nkx2-6 | NM_010920.2 | chr14:69789859-69793597 |
| 19941 | Nkx2-9 | NM_008701.2 | chr12:57712383-57714271 |
| 19942 | Nkx3-1 | NM_010921.3 | chr14:69808748-69812715 |
| 19943 | Nkx3-2 | NM_007524.3 | chr5:42152721-42155459 |
| 19944 | Nkx6-1 | NM_144955.1 | chr5:102088215-102093730 |
| 19945 | Nkx6-2 | NM_183248.3 | chr7:146575007-146768696 |
| 19946 | Nkx6-2 | NR_027857.1 | chr7:146575007-146768696 |
| 19947 | Nkx6-3 | NM_029002.2 | chr8:24263742-24269420 |
| 19948 | Nle1 | NM_145412.2 | chr11:82714269-82721897 |
| 19949 | Nlgn1 | NM_001163387.1 | chr3:25330762-26230831 |
| 19950 | Nlgn1 | NM_138666.3 | chr3:25330762-26230831 |
| 19951 | Nlgn2 | NM_198862.2 | chr11:69636624-69648351 |
| 19952 | Nlgn3 | NM_172932.4 | chrX:98494517-98516689 |
| 19953 | Nlk | NM_008702.3 | chr11:78380869-78510927 |
| 19954 | Nln | NM_029447.2 | chr13:104813518-104899694 |
| 19955 | Nlrc3 | NM_001081280.1 | chr16:3946932-3976632 |
| 19956 | Nlrc3 | NM_175547.3 | chr16:3946932-3976632 |
| 19957 | Nlrc4 | NM_001033667.3 | chr17:74825634-74858448 |
| 19958 | Nlrc5 | NM_001033207.3 | chr8:96996663-97051172 |
| 19959 | Nlrp10 | NM_175532.3 | chr7:116065366-116073672 |
| 19960 | Nlrp12 | NM_001033431.1 | chr7:3221510-3249741 |
| 19961 | Nlrp14 | NM_001002894.2 | chr7:114310503-114341617 |
| 19962 | Nlrp1a | NM_001004142.2 | chr11:70904698-70968206 |
| 19963 | Nlrp1b | NM_001040696.1 | chr11:70966603-71044235 |
| 19964 | Nlrp1b | NM_001162414.1 | chr11:70966603-71044235 |
| 19965 | Nlrp1c-ps | NR_027858.1 | chr11:71055931-71098734 |
| 19966 | Nlrp3 | NM_177690.3 | chr7:5250149-5302637 |
| 19967 | Nlrp3 | NM_145827.3 | chr11:59356187-59380458 |
| 19968 | Nlrp4a | NM_172896.2 | chr7:27220131-27260477 |
| 19969 | Nlrp4b | NM_172481.2 | chr7:11273141-11315507 |
| 19970 | Nlrp4c | NM_031389.2 | chr7:5996782-6056751 |
| 19971 | Nlrp4e | NM_001004194.2 | chr7:24086210-24147296 |
| 19972 | Nlrp4f | NM_175290.4 | chr13:65278418-65307024 |
| 19973 | Nlrp4g | NM_001004145.2 | chr9_random:113043-134706 |
| 19974 | Nlrp5 | NM_001039143.2 | chr7:24170915-24226940 |
| 19975 | Nlrp5 | NM_011860.3 | chr7:24170915-24226940 |
| 19976 | Nlrp5-ps | NR_045119.1 | chr7:15116002-15208415 |
| 19977 | Nlrp5-ps | NR_045120.1 | chr7:15116002-15208415 |
| 19978 | Nlrp6 | NM_133946.2 | chr7:148106800-148115091 |
| 19979 | Nlrp9a | NM_001048219.2 | chr7:27320083-27359165 |
| 19980 | Nlrp9a | NM_001048220.2 | chr7:27320083-27359165 |
| 19981 | Nlrp9b | NM_194058.2 | chr7:20593371-20648287 |
| 19982 | Nlrp9c | NM_001042612.1 | chr7:27149905-27179262 |
| 19983 | Nlrx1 | NM_001163742.1 | chr9:44060795-44076682 |
| 19984 | Nlrx1 | NM_001163743.1 | chr9:44060795-44076682 |
| 19985 | Nlrx1 | NM_178420.3 | chr9:44060795-44076682 |
| 19986 | Nmb | NM_001291280.1 | chr7:88047112-88049948 |
| 19987 | Nmb | NM_026523.4 | chr7:88047112-88049948 |
| 19988 | Nmbr | NM_008703.2 | chr10:14480094-14490362 |
| 19989 | Nmd3 | NM_133787.2 | chr3:69525976-69552968 |
| 19990 | Nme1 | NM_008704.2 | chr11:93820238-93829835 |
| 19991 | Nme2 | NM_001077529.2 | chr11:93811127-93817570 |
| 19992 | Nme2 | NM_008705.5 | chr11:93811127-93817570 |
| 19993 | Nme3 | NM_019730.2 | chr17:25033445-25034474 |
| 19994 | Nme4 | NM_019731.1 | chr17:26228689-26232415 |
| 19995 | Nme5 | NM_080637.3 | chr18:34722294-34738760 |
| 19996 | Nme6 | NM_018757.1 | chr9:109735307-109745475 |
| 19997 | Nme7 | NM_138314.4 | chr1:166237805-166388486 |
| 19998 | Nme7 | NM_178071.6 | chr1:166237805-166388486 |
| 19999 | Nme8 | NM_001167909.1 | chr13:19736947-19789629 |
| 20000 | Nme8 | NM_181591.3 | chr13:19736947-19789629 |
| 20001 | Nme9 | NM_001165957.1 | chr9:99356662-99380318 |
| 20002 | Nmi | NM_001141948.1 | chr2:51804018-51828728 |
| 20003 | Nmi | NM_001141949.1 | chr2:51804018-51828728 |
| 20004 | Nmi | NM_019401.2 | chr2:51804018-51828728 |
| 20005 | Nmnat1 | NM_133435.1 | chr4:148842895-148859251 |
| 20006 | Nmnat2 | NM_175460.3 | chr1:154802230-154966391 |
| 20007 | Nmnat3 | NM_144533.2 | chr9:98197001-98311847 |
| 20008 | Nmral1 | NM_001290761.1 | chr16:4711317-4719356 |
| 20009 | Nmral1 | NM_001290762.1 | chr16:4711317-4719356 |
| 20010 | Nmral1 | NM_001290763.1 | chr16:4711317-4719356 |
| 20011 | Nmral1 | NM_026393.2 | chr16:4711317-4719356 |
| 20012 | Nmrk1 | NM_145497.2 | chr19:18706505-18726674 |
| 20013 | Nmrk2 | NM_027120.2 | chr10:80660915-80664782 |
| 20014 | Nms | NM_001011684.2 | chr1:38995993-39007121 |
| 20015 | Nmt1 | NM_008707.3 | chr11:102889875-102927419 |
| 20016 | Nmt2 | NM_001290368.1 | chr2:3201483-3246149 |
| 20017 | Nmt2 | NM_001290369.1 | chr2:3201483-3246149 |
| 20018 | Nmt2 | NM_001290370.1 | chr2:3201483-3246149 |
| 20019 | Nmt2 | NM_008708.2 | chr2:3201483-3246149 |
| 20020 | Nmu | NM_019515.1 | chr5:76762519-76792802 |
| 20021 | Nmur1 | NM_010341.1 | chr1:88282898-88284716 |
| 20022 | Nmur2 | NM_153079.4 | chr11:55838491-55854489 |
| 20023 | Nnat | NM_001291128.1 | chr2:157382097-157392097 |
| 20024 | Nnat | NM_001291129.1 | chr2:157382097-157392097 |
| 20025 | Nnat | NM_001291130.1 | chr2:157382097-157392097 |
| 20026 | Nnat | NM_010923.3 | chr2:157382097-157392097 |
| 20027 | Nnat | NM_180960.3 | chr2:157382097-157392097 |
| 20028 | Nnmt | NM_010924.2 | chr9:48399994-48413182 |
| 20029 | Nnt | NM_008710.3 | chr13:120123123-120197945 |
| 20030 | Nnt | NR_003544.1 | chr13:120123123-120197945 |
| 20031 | Noa1 | NM_019836.3 | chr5:77723193-77739111 |
| 20032 | Nob1 | NM_026277.3 | chr8:109936388-109948938 |
| 20033 | Nobox | NM_130869.3 | chr6:43253672-43259553 |
| 20034 | Noc3l | NM_021315.2 | chr19:38862617-38893727 |
| 20035 | Noc4l | NM_153570.2 | chr5:111077437-111082401 |
| 20036 | Nod1 | NM_001171007.1 | chr6:54873935-54922606 |
| 20037 | Nod1 | NM_172729.3 | chr6:54873935-54922606 |
| 20038 | Nod2 | NM_145857.2 | chr8:91171245-91212373 |
| 20039 | Nodal | NM_013611.4 | chr10:60880719-60888085 |
| 20040 | Nog | NM_008711.2 | chr11:89161951-89163873 |
| 20041 | Noi10 | NM_001008421.1 | chr12:17355299-17436901 |
| 20042 | Nol11 | NM_001161329.1 | chr11:107027974-107050695 |
| 20043 | Nol11 | NM_133702.2 | chr11:107027974-107050695 |
| 20044 | Nol12 | NM_133800.3 | chr15:78765362-78772340 |
| 20045 | Nol3 | NM_030152.4 | chr8:107800347-107805839 |
| 20046 | Nol4 | NM_001161483.1 | chr18:22851655-23200154 |
| 20047 | Nol4 | NM_199024.2 | chr18:22851655-23200154 |
| 20048 | Nol6 | NM_139236.3 | chr4:41061459-41071372 |
| 20049 | Nol7 | NM_023554.2 | chr13:43493745-43498227 |
| 20050 | Nol8 | NM_001271397.1 | chr13:49748446-49774385 |
| 20051 | Nol8 | NR_073167.1 | chr13:49748446-49774385 |
| 20052 | Nol8 | NR_073168.1 | chr13:49748446-49774385 |
| 20053 | Nol9 | NM_001159599.2 | chr4:151413435-151435603 |
| 20054 | Nol9 | NM_028727.3 | chr4:151413435-151435603 |
| 20055 | Nolc1 | NM_001039351.1 | chr19:46150336-46160033 |
| 20056 | Nolc1 | NM_001039352.2 | chr19:46150336-46160033 |
| 20057 | Nolc1 | NM_001039353.1 | chr19:46150336-46160033 |
| 20058 | Nolc1 | NM_053086.3 | chr19:46150336-46160033 |
| 20059 | Nom1 | NM_001033457.2 | chr5:29761206-29778709 |
| 20060 | Nomo1 | NM_153057.4 | chr7:53289065-53339582 |
| 20061 | Nono | NM_001252518.1 | chrX:98624989-98643932 |
| 20062 | Nono | NM_023144.2 | chrX:98624989-98643932 |
| 20063 | Nop10 | NM_025403.4 | chr2:112102082-112103055 |

Fig. 25 - 107

| | | | | | | | |
|---|---|---|---|---|---|---|---|
| 20064 | Nop14 | NM_029278.2 | chr5:34981184-35002797 | 20159 | Npw | NM_001099664.1 | chr17:24794274-24795370 |
| 20065 | Nop16 | NM_178605.4 | chr13:54685551-54691435 | 20160 | Npy | NM_023456.2 | chr6:49772727-49779504 |
| 20066 | Nop2 | NM_138747.2 | chr6:125081900-125094771 | 20161 | Npy1r | NM_010934.4 | chr8:69221320-69230697 |
| 20067 | Nop56 | NM_024193.2 | chr2:130100148-130105049 | 20162 | Npy2r | NM_001205099.1 | chr3:82342304-82352007 |
| 20068 | Nop58 | NM_018868.2 | chr1:59741850-59768354 | 20163 | Npy2r | NM_008731.3 | chr3:82342304-82352007 |
| 20069 | Nop9 | NM_026403.3 | chr14:56364536-56374471 | 20164 | Npy4r | NM_008919.4 | chr14:34958831-34965605 |
| 20070 | Nos1 | NM_008712.3 | chr5:118317127-118403820 | 20165 | Npy5r | NM_016708.3 | chr8:69203863-69211993 |
| 20071 | Nos1ap | NM_001109985.1 | chr1:172247626-172519980 | 20166 | Npy6r | NM_010935.3 | chr18:44429780-44437354 |
| 20072 | Nos1ap | NM_027528.2 | chr1:172247626-172519980 | 20167 | Nqo1 | NM_008706.5 | chr8:109912124-109927105 |
| 20073 | Nos2 | NM_010927.3 | chr11:78734360-78773626 | 20168 | Nqo2 | NM_001163239.1 | chr13:34009786-34094663 |
| 20074 | Nos3 | NM_008713.4 | chr5:23870637-23890292 | 20169 | Nqo2 | NM_001163241.1 | chr13:34009786-34094663 |
| 20075 | Nosip | NM_001163684.1 | chr7:52317798-52333873 | 20170 | Nqo2 | NM_001163242.1 | chr13:34009786-34094663 |
| 20076 | Nosip | NM_025533.3 | chr7:52317798-52333873 | 20171 | Nqo2 | NM_020282.3 | chr13:34009786-34094663 |
| 20077 | Nostrin | NM_181547.3 | chr2:68973856-69027386 | 20172 | Nr0b1 | NM_007430.5 | chrX:83437113-83441283 |
| 20078 | Notch1 | NM_008714.3 | chr2:26313422-26359342 | 20173 | Nr0b2 | NM_011850.2 | chr4:133109304-133112451 |
| 20079 | Notch2 | NM_010928.2 | chr3:97817460-97954290 | 20174 | Nr1d1 | NM_145434.4 | chr11:98629245-98636691 |
| 20080 | Notch3 | NM_008716.2 | chr17:32257837-32303797 | 20175 | Nr1d2 | NM_011584.4 | chr14:19036569-19071620 |
| 20081 | Notch4 | NM_010929.2 | chr17:34701239-34725488 | 20176 | Nr1h2 | NM_001285517.1 | chr7:51804985-51809335 |
| 20082 | Noto | NM_001007472.2 | chr6:85373879-85378871 | 20177 | Nr1h2 | NM_001285518.1 | chr7:51804985-51809335 |
| 20083 | Notum | NM_175263.4 | chr11:120515102-120522151 | 20178 | Nr1h2 | NM_001285519.1 | chr7:51804985-51809335 |
| 20084 | Nov | NM_010930.4 | chr15:54577482-54585316 | 20179 | Nr1h2 | NM_009473.3 | chr7:51804985-51809335 |
| 20085 | Nova1 | NM_021361.1 | chr12:47795503-47919762 | 20180 | Nr1h3 | NM_001177730.1 | chr2:91024217-91035273 |
| 20086 | Nova2 | NM_001029877.3 | chr7:19511236-19550668 | 20181 | Nr1h3 | NM_013839.4 | chr2:91024217-91035273 |
| 20087 | Nox1 | NM_172203.2 | chrX:130620960-130646393 | 20182 | Nr1h4 | NM_001163504.1 | chr10:88916978-88996367 |
| 20088 | Nox3 | NM_198958.4 | chr17:3635239-3696261 | 20183 | Nr1h4 | NM_001163700.3 | chr10:88916978-88996367 |
| 20089 | Nox4 | NM_001285833.1 | chr7:94395158-94547218 | 20184 | Nr1h4 | NM_009108.2 | chr10:88916978-88996367 |
| 20090 | Nox4 | NM_001285835.1 | chr7:94395158-94547218 | 20185 | Nr1h5 | NM_198658.2 | chr3:102743580-102768056 |
| 20091 | Nox4 | NM_015760.5 | chr7:94395158-94547218 | 20186 | Nr1h5 | NM_201619.2 | chr3:102743580-102768056 |
| 20092 | Noxa1 | NM_001163626.1 | chr2:24935842-24950725 | 20187 | Nr1h5 | NM_201622.2 | chr3:102743580-102768056 |
| 20093 | Noxa1 | NM_172204.4 | chr2:24935842-24950725 | 20188 | Nr1i2 | NM_001098404.1 | chr16:38248434-38294910 |
| 20094 | Noxo1 | NM_027988.4 | chr17:24833178-24837474 | 20189 | Nr1i2 | NM_010936.3 | chr16:38248434-38294910 |
| 20095 | Noxred1 | NM_027744.1 | chr12:88562072-88579551 | 20190 | Nr1i3 | NM_001243062.1 | chr1:173144100-173152645 |
| 20096 | Npas1 | NM_008718.2 | chr7:17041069-17062129 | 20191 | Nr1i3 | NM_001243063.1 | chr1:173144100-173152645 |
| 20097 | Npas2 | NM_008719.2 | chr1:39251116-39420085 | 20192 | Nr1i3 | NM_009803.5 | chr1:173144100-173152645 |
| 20098 | Npas3 | NM_013780.2 | chr12:54349663-55173162 | 20193 | Nr2c1 | NM_011629.3 | chr10:93610675-93659959 |
| 20099 | Npas4 | NM_153553.4 | chr19:4984354-4989971 | 20194 | Nr2c2 | NM_011630.3 | chr6:92041412-92123052 |
| 20100 | Npat | NM_001081152.1 | chr9:53345151-53383732 | 20195 | Nr2c2ap | NM_001025586.2 | chr8:72654704-72663096 |
| 20101 | Npb | NM_153288.3 | chr11:120469790-120470414 | 20196 | Nr2c2ap | NM_001025587.2 | chr8:72654704-72663096 |
| 20102 | Npbwr1 | NM_010342.1 | chr1:5903787-5907479 | 20197 | Nr2c2ap | NR_104434.1 | chr8:72654704-72663096 |
| 20103 | Npc1 | NM_008720.2 | chr18:12348203-12394895 | 20198 | Nr2e1 | NM_152229.2 | chr10:42281776-42303394 |
| 20104 | Npc1l1 | NM_207242.2 | chr11:6111013-6130248 | 20199 | Nr2e3 | NM_013708.4 | chr9:59790577-59797886 |
| 20105 | Npc2 | NM_023409.4 | chr12:86095508-86114062 | 20200 | Nr2f1 | NM_010151.2 | chr13:78328236-78338243 |
| 20106 | Npcd | NM_001013360.2 | chr15:79616780-79664763 | 20201 | Nr2f2 | NM_009697.3 | chr7:77496835-77556032 |
| 20107 | Npcd | NM_001013362.2 | chr15:79616780-79664763 | 20202 | Nr2f2 | NM_183261.3 | chr7:77496835-77556032 |
| 20108 | Npdc1 | NM_008721.4 | chr2:25258569-25265014 | 20203 | Nr2f6 | NM_010150.2 | chr8:73898017-73905851 |
| 20109 | Npepl1 | NM_213733.2 | chr2:173935851-173948203 | 20204 | Nr3c1 | NM_008173.3 | chr18:39570198-39646899 |
| 20110 | Npepps | NM_008942.2 | chr11:97067170-97141890 | 20205 | Nr3c2 | NM_001083906.1 | chr8:79426406-79767538 |
| 20111 | Npff | NM_018787.1 | chr15:102354269-102355373 | 20206 | Nr4a1 | NM_010444.2 | chr15:101097276-101105225 |
| 20112 | Npff | NR_033409.1 | chr15:102354269-102355373 | 20207 | Nr4a2 | NM_001139509.1 | chr2:56959636-56976414 |
| 20113 | Npffr1 | NM_001177511.1 | chr10:61058231-61089133 | 20208 | Nr4a2 | NM_013613.2 | chr2:56959636-56976414 |
| 20114 | Npffr2 | NM_133192.3 | chr5:89956453-90012765 | 20209 | Nr4a3 | NM_015743.3 | chr4:48064119-48096224 |
| 20115 | Nphp1 | NM_001291012.1 | chr2:127566467-127614627 | 20210 | Nr5a1 | NM_139051.3 | chr2:38548179-38570062 |
| 20116 | Nphp1 | NM_001291013.1 | chr2:127566467-127614627 | 20211 | Nr5a2 | NM_001159769.2 | chr1:138740160-138857025 |
| 20117 | Nphp1 | NM_016902.4 | chr2:127566467-127614627 | 20212 | Nr5a2 | NM_030676.3 | chr1:138740160-138857025 |
| 20118 | Nphp3 | NM_028721.3 | chr9:103904873-103946141 | 20213 | Nr6a1 | NM_001159548.1 | chr2:38578893-38781981 |
| 20119 | Nphp3 | NM_172460.3 | chr9:103904873-103946141 | 20214 | Nr6a1 | NM_001159549.1 | chr2:38578893-38781981 |
| 20120 | Nphp4 | NM_153424.2 | chr4:151851250-151937293 | 20215 | Nr6a1 | NM_010264.4 | chr2:38578893-38781981 |
| 20121 | Nphs1 | NM_019459.2 | chr7:31245077-31273628 | 20216 | Nradd | NM_026012.2 | chr9:110523638-110526897 |
| 20122 | Nphs1os | NR_004443.1 | chr7:31247183-31250610 | 20217 | Nrap | NM_001286552.1 | chr19:56362427-56464528 |
| 20123 | Nphs2 | NM_130456.3 | chr1:158240865-158258166 | 20218 | Nrap | NM_008733.4 | chr19:56362427-56464528 |
| 20124 | Npl | NM_028749.1 | chr1:155350145-155396844 | 20219 | Nrap | NM_198059.3 | chr19:56362427-56464528 |
| 20125 | Nploc4 | NM_001195023.1 | chr11:120241111-120299014 | 20220 | Nrarp | NM_025980.2 | chr2:25036277-25038852 |
| 20126 | Nploc4 | NM_199469.2 | chr11:120241111-120299014 | 20221 | Nras | NM_010937.2 | chr3:102862207-102871837 |
| 20127 | Npm1 | NM_001252260.1 | chr11:33052497-33063206 | 20222 | Nrbf2 | NM_001036293.2 | chr10:66729436-66748029 |
| 20128 | Npm1 | NM_001252261.1 | chr11:33052497-33063206 | 20223 | Nrbp1 | NM_147201.2 | chr5:31543291-31553935 |
| 20129 | Npm1 | NM_008722.3 | chr11:33052497-33063206 | 20224 | Nrbp2 | NM_144847.1 | chr15:75916023-75920443 |
| 20130 | Npm2 | NM_181345.3 | chr14:71047108-71052891 | 20225 | Nrcam | NM_001146031.1 | chr12:45429871-45702833 |
| 20131 | Npm3 | NM_008723.3 | chr19:45822223-45824053 | 20226 | Nrcam | NM_176930.4 | chr12:45429871-45702833 |
| 20132 | Npm3-ps1 | NR_002702.1 | chr6:85026134-85027120 | 20227 | Nrd1 | NM_146150.2 | chr4:108673410-108734376 |
| 20133 | Npnt | NM_001287100.1 | chr3:132544708-132613255 | 20228 | Nrde2 | NM_001290303.1 | chr12:101363659-101397863 |
| 20134 | Npnt | NM_001287101.1 | chr3:132544708-132613255 | 20229 | Nrde2 | NM_183155.3 | chr12:101363659-101397863 |
| 20135 | Npnt | NM_001287102.1 | chr3:132544708-132613255 | 20230 | Nrep | NM_001109988.1 | chr18:33596672-33623683 |
| 20136 | Npnt | NM_001287103.1 | chr3:132544708-132613255 | 20231 | Nrep | NM_001109989.2 | chr18:33596672-33623683 |
| 20137 | Npnt | NM_033525.3 | chr3:132544708-132613255 | 20232 | Nrep | NM_001267717.1 | chr18:33596672-33623683 |
| 20138 | Nppa | NM_008725.2 | chr4:147374854-147376176 | 20233 | Nrep | NM_053078.4 | chr18:33596672-33623683 |
| 20139 | Nppb | NM_001287348.1 | chr4:147359896-147361314 | 20234 | Nrf1 | NM_001164226.1 | chr6:29997987-30103458 |
| 20140 | Nppb | NM_008726.5 | chr4:147359896-147361314 | 20235 | Nrf1 | NM_001164227.1 | chr6:29997987-30103458 |
| 20141 | Nppc | NM_010933.5 | chr1:88562867-88567148 | 20236 | Nrf1 | NM_001164228.1 | chr6:29997987-30103458 |
| 20142 | Npr1 | NM_008727.5 | chr3:90254513-90269788 | 20237 | Nrf1 | NM_001164229.1 | chr6:29997987-30103458 |
| 20143 | Npr2 | NM_173788.3 | chr4:43644806-43664112 | 20238 | Nrf1 | NM_001164230.1 | chr6:29997987-30103458 |
| 20144 | Npr3 | NM_001039181.1 | chr15:11769650-11837126 | 20239 | Nrf1 | NM_010938.1 | chr6:29997987-30103458 |
| 20145 | Npr3 | NM_001286395.1 | chr15:11769650-11837126 | 20240 | Nrg1 | NM_178591.2 | chr8:32918499-33028675 |
| 20146 | Npr3 | NM_008728.2 | chr15:11769650-11837126 | 20241 | Nrg2 | NM_001167891.1 | chr18:36177312-36356814 |
| 20147 | Nprl2 | NM_018879.2 | chr9:107444539-107448037 | 20242 | Nrg3 | NM_001190187.1 | chr14:39182136-40286376 |
| 20148 | Nprl3 | NM_001284359.1 | chr11:32126504-32167707 | 20243 | Nrg3 | NM_001190188.1 | chr14:39182136-40286376 |
| 20149 | Nprl3 | NM_001284360.1 | chr11:32126504-32167707 | 20244 | Nrg3 | NM_008734.3 | chr14:39182136-40286376 |
| 20150 | Nprl3 | NM_175678.3 | chr11:32126504-32167707 | 20245 | Nrg3os | NR_045713.1 | chr14:39711590-39772082 |
| 20151 | Nprl3 | NR_104306.1 | chr11:32126504-32167707 | 20246 | Nrg4 | NM_032002.2 | chr9:55068029-55131432 |
| 20152 | Nps | NM_001163611.1 | chr7:142460301-142464625 | 20247 | Nrgn | NM_022029.1 | chr9:37352077-37360330 |
| 20153 | Npsr1 | NM_175678.2 | chr9:23902461-24120842 | 20248 | Nrip1 | NM_173440.2 | chr16:76291106-76373294 |
| 20154 | Npte | NM_009145.2 | chr9:58430047-58500686 | 20249 | Nrip2 | NM_001162858.1 | chr6:128349783-128358953 |
| 20155 | Nptx1 | NM_008730.2 | chr11:119400032-119409134 | 20250 | Nrip2 | NM_021717.2 | chr6:128349783-128358953 |
| 20156 | Nptx2 | NM_016789.3 | chr5:145306755-145318347 | 20251 | Nrip3 | NM_020610.1 | chr7:116901569-116925059 |
| 20157 | Nptxr | NM_030689.4 | chr15:79616781-79635139 | 20252 | Nrk | NM_013724.2 | chrX:135448968-135543629 |
| 20158 | Npvf | NM_021892.1 | chr6:50600869-50604392 | 20253 | Nrl | NM_001136074.2 | chr14:56137814-56143818 |

Fig. 25 - 108

| | | | |
|---|---|---|---|
| 20254 | Nrl | NM_001271916.1 | chr14:56137814-56143818 |
| 20255 | Nrl | NM_001271917.1 | chr14:56137814-56143818 |
| 20256 | Nrl | NM_008736.3 | chr14:56137814-56143818 |
| 20257 | Nrn | NM_134122.2 | chr17:35998262-36002345 |
| 20258 | Nrn1 | NM_153529.2 | chr13:36817490-36826846 |
| 20259 | Nrn1l | NM_175024.2 | chr8:108417469-108418915 |
| 20260 | Nron | NR_045729.1 | chr2:33661336-33669111 |
| 20261 | Nrp | NM_001013372.2 | chr12:88783798-88784967 |
| 20262 | Nrp1 | NM_008737.2 | chr8:130882973-131029375 |
| 20263 | Nrp2 | NM_001077403.1 | chr1:62749890-62865266 |
| 20264 | Nrp2 | NM_001077404.1 | chr1:62749890-62865266 |
| 20265 | Nrp2 | NM_001077405.1 | chr1:62749890-62865266 |
| 20266 | Nrp2 | NM_001077406.1 | chr1:62749890-62865266 |
| 20267 | Nrp2 | NM_001077407.1 | chr1:62749890-62865266 |
| 20268 | Nrp2 | NM_010939.2 | chr1:62749890-62865266 |
| 20269 | Nrros | NM_148608.4 | chr16:32142910-32165562 |
| 20270 | Nrsn1 | NM_009513.2 | chr13:25343907-25361865 |
| 20271 | Nrsn2 | NM_001009948.1 | chr2:152194494-152202302 |
| 20272 | Nrtn | NM_008738.2 | chr17:56890747-56896953 |
| 20273 | Nrxn1 | NM_020252.3 | chr17:90432983-91492142 |
| 20274 | Nrxn1 | NM_177284.2 | chr17:90432983-91492142 |
| 20275 | Nrxn2 | NM_001205234.1 | chr19:6418737-6533217 |
| 20276 | Nrxn2 | NM_001205235.1 | chr19:6418737-6533217 |
| 20277 | Nrxn2 | NM_020253.3 | chr19:6418737-6533217 |
| 20278 | Nrxn3 | NM_001198587.3 | chr12:90032947-91573373 |
| 20279 | Nrxn3 | NM_001252074.2 | chr12:90032947-91573373 |
| 20280 | Nrxn3 | NM_172544.3 | chr12:90032947-91573373 |
| 20281 | Nsa2 | NM_021552.5 | chr13:97899382-97907881 |
| 20282 | Nsd1 | NM_008739.3 | chr13:55311142-55419686 |
| 20283 | Nsdhl | NM_010941.3 | chrX:70163859-70203867 |
| 20284 | Nsf | NM_008740.4 | chr11:103683096-103815370 |
| 20285 | Nsfl1c | NM_001291074.1 | chr2:151319917-151337046 |
| 20286 | Nsfl1c | NM_198326.3 | chr2:151319917-151337046 |
| 20287 | Nsg1 | NM_010942.3 | chr5:38528432-38550706 |
| 20288 | Nsg2 | NM_001290680.1 | chr11:31900418-31959211 |
| 20289 | Nsg2 | NM_001290681.1 | chr11:31900418-31959211 |
| 20290 | Nsg2 | NM_008741.2 | chr11:31900418-31959211 |
| 20291 | Nsl1 | NM_198654.3 | chr1:192886899-192908437 |
| 20292 | Nsmaf | NM_010779.2 | chr4:6323353-6381418 |
| 20293 | Nsmce1 | NM_026330.3 | chr7:132611153-132635056 |
| 20294 | Nsmce2 | NM_001164604.1 | chr15:59205752-59433239 |
| 20295 | Nsmce2 | NM_026746.3 | chr15:59205752-59433239 |
| 20296 | Nsmce4a | NM_001162855.1 | chr7:137676039-137690895 |
| 20297 | Nsmf | NM_001039386.1 | chr2:24909898-24918401 |
| 20298 | Nsmf | NM_001039387.1 | chr2:24909898-24918401 |
| 20299 | Nsmf | NM_001177654.1 | chr2:24909898-24918401 |
| 20300 | Nsmf | NM_001177655.1 | chr2:24909898-24918401 |
| 20301 | Nsmf | NM_020276.3 | chr2:24909898-24918401 |
| 20302 | Nsun2 | NM_145354.5 | chr13:69750893-69774657 |
| 20303 | Nsun3 | NM_178925.3 | chr16:62734677-62786542 |
| 20304 | Nsun4 | NM_028142.4 | chr4:115704374-115726481 |
| 20305 | Nsun5 | NM_145414.2 | chr5:135845823-135852667 |
| 20306 | Nsun6 | NM_001165941.1 | chr2:14916757-14976499 |
| 20307 | Nsun6 | NM_001165942.1 | chr2:14916757-14976499 |
| 20308 | Nsun6 | NM_001165943.1 | chr2:14916757-14976499 |
| 20309 | Nsun6 | NM_025549.2 | chr2:14916757-14976499 |
| 20310 | Nsun7 | NM_027602.2 | chr5:66651363-66689255 |
| 20311 | Nt5c | NM_015807.3 | chr11:115351740-115353128 |
| 20312 | Nt5c1a | NM_001085502.1 | chr4:122878795-122893450 |
| 20313 | Nt5c1b | NM_027588.3 | chr12:10376776-10396980 |
| 20314 | Nt5c2 | NM_001164363.1 | chr19:46961320-47098836 |
| 20315 | Nt5c2 | NM_001164365.1 | chr19:46961320-47098836 |
| 20316 | Nt5c2 | NM_029810.4 | chr19:46961320-47098836 |
| 20317 | Nt5c2 | NR_028353.1 | chr19:46961320-47098836 |
| 20318 | Nt5c3 | NM_001252374.1 | chr6:56832394-56873926 |
| 20319 | Nt5c3 | NM_026004.3 | chr6:56832394-56873926 |
| 20320 | Nt5c3b | NM_001102650.1 | chr11:100277007-100302403 |
| 20321 | Nt5c3b | NM_026561.4 | chr11:100277007-100302403 |
| 20322 | Nt5dc1 | NM_176968.4 | chr10:34023418-34138334 |
| 20323 | Nt5dc2 | NM_027804.2 | chr14:31948039-31952310 |
| 20324 | Nt5dc3 | NM_175331.3 | chr10:86241749-86301134 |
| 20325 | Nt5e | NM_011851.4 | chr9:88222446-88266927 |
| 20326 | Nt5m | NM_134429.2 | chr11:59661574-59690035 |
| 20327 | Ntan1 | NM_010946.3 | chr16:13819370-13835543 |
| 20328 | Ntf3 | NM_001164034.1 | chr6:126051429-126116762 |
| 20329 | Ntf3 | NM_001164035.1 | chr6:126051429-126116762 |
| 20330 | Ntf3 | NM_008742.3 | chr6:126051429-126116762 |
| 20331 | Ntf5 | NM_198190.1 | chr7:52669064-52672549 |
| 20332 | Nthl1 | NM_008743.2 | chr17:24769626-24775783 |
| 20333 | Ntm | NM_172290.3 | chr9:28803548-29770714 |
| 20334 | Ntmt1 | NM_170592.2 | chr2:30663496-30678534 |
| 20335 | Ntn1 | NM_008744.2 | chr11:68022866-68200328 |
| 20336 | Ntn3 | NM_010947.3 | chr17:24340791-24346332 |
| 20337 | Ntn4 | NM_021320.3 | chr10:93103794-93208717 |
| 20338 | Ntn5 | NM_001033356.3 | chr7:52933056-52949926 |
| 20339 | Ntn5 | NM_001289692.1 | chr7:52933056-52949926 |
| 20340 | Ntn5 | NM_001289692.1 | chr7:52933056-52949926 |
| 20341 | Ntng1 | NM_001163348.1 | chr3:109582967-109946390 |
| 20342 | Ntng1 | NM_001163349.1 | chr3:109582967-109946390 |
| 20343 | Ntng1 | NM_001163350.1 | chr3:109582967-109946390 |
| 20344 | Ntng1 | NM_001163351.1 | chr3:109582967-109946390 |
| 20345 | Ntng1 | NM_030699.2 | chr3:109582967-109946390 |
| 20346 | Ntng1 | NM_133488.1 | chr3:109582967-109946390 |
| 20347 | Ntng2 | NM_133500.2 | chr2:29050340-29108513 |
| 20348 | Ntng2 | NM_133501.2 | chr2:29050340-29108513 |
| 20349 | Ntpcr | NM_025636.5 | chr8:128258102-128272135 |
| 20350 | Ntrk1 | NM_001033124.1 | chr3:87582165-87599084 |
| 20351 | Ntrk2 | NM_001025074.2 | chr13:58907929-59235331 |
| 20352 | Ntrk2 | NM_001282961.1 | chr13:58907929-59235331 |
| 20353 | Ntrk2 | NM_008745.3 | chr13:58907929-59235331 |
| 20354 | Ntrk3 | NM_008746.5 | chr7:85336999-85722724 |
| 20355 | Ntrk3 | NM_182809.2 | chr7:85336999-85722724 |
| 20356 | Nts | NM_024435.2 | chr10:101944389-101953052 |
| 20357 | Ntsr1 | NM_018766.2 | chr2:180234680-180279684 |
| 20358 | Ntsr2 | NM_008747.2 | chr12:16660275-16667042 |
| 20359 | Nuak1 | NM_001004363.1 | chr10:83834063-83903216 |
| 20360 | Nuak2 | NM_001195025.1 | chr1:134212701-134230065 |
| 20361 | Nuak2 | NM_028778.4 | chr1:134212701-134230065 |
| 20362 | Nubl | NM_016736.3 | chr5:24191632-24216373 |
| 20363 | Nubp1 | NM_019955.2 | chr16:10412031-10424518 |
| 20364 | Nubp2 | NM_011956.3 | chr17:25019555-25023295 |
| 20365 | Nubpl | NM_029760.2 | chr12:53198732-53411946 |
| 20366 | Nucb1 | NM_001163662.1 | chr7:52728932-52777973 |
| 20367 | Nucb1 | NM_008749.2 | chr7:52728932-52777973 |
| 20368 | Nucb2 | NM_001130479.2 | chr7:123647882-123684102 |
| 20369 | Nucks1 | NM_001145804.1 | chr1:133807034-133832898 |
| 20370 | Nucks1 | NM_175294.3 | chr1:133807034-133832898 |
| 20371 | Nudc | NM_010948.3 | chr4:133088456-133101942 |
| 20372 | Nudcd1 | NM_001135554.1 | chr15:44206772-44269231 |
| 20373 | Nudcd1 | NM_026149.2 | chr15:44206772-44269231 |
| 20374 | Nudcd2 | NM_001290697.1 | chr11:40547162-40553548 |
| 20375 | Nudcd2 | NM_026023.5 | chr11:40547162-40553548 |
| 20376 | Nudcd3 | NM_173748.4 | chr11:6005695-6100454 |
| 20377 | Nudt1 | NM_008637.1 | chr5:140807875-140814089 |
| 20378 | Nudt10 | NM_001031664.1 | chrX:5745814-5750109 |
| 20379 | Nudt11 | NM_021431.2 | chrX:5624624-5631869 |
| 20380 | Nudt12 | NM_026497.2 | chr17:59140823-59152745 |
| 20381 | Nudt13 | NM_026341.2 | chr14:21113911-21136797 |
| 20382 | Nudt14 | NM_025399.3 | chr12:114172943-114180329 |
| 20383 | Nudt15 | NM_172527.2 | chr14:73919679-73948049 |
| 20384 | Nudt16 | NM_029385.2 | chr9:105031667-105034135 |
| 20385 | Nudt16l1 | NM_025839.3 | chr16:4939111-4941025 |
| 20386 | Nudt17 | NM_001162925.1 | chr3:96500297-96512483 |
| 20387 | Nudt17 | NM_030094.1 | chr3:96500297-96512483 |
| 20388 | Nudt18 | NM_153136.4 | chr14:70977653-70982378 |
| 20389 | Nudt19 | NM_033080.2 | chr7:36332203-36340947 |
| 20390 | Nudt2 | NM_025539.2 | chr4:41412180-41427959 |
| 20391 | Nudt21 | NM_026623.3 | chr8:96543302-96560939 |
| 20392 | Nudt22 | NM_026675.2 | chr19:7067508-7070527 |
| 20393 | Nudt3 | NM_001291046.1 | chr17:27716326-27760397 |
| 20394 | Nudt3 | NM_019837.2 | chr17:27716326-27760397 |
| 20395 | Nudt4 | NM_027722.4 | chr10:95009641-95026801 |
| 20396 | Nudt5 | NM_016918.3 | chr2:5766079-5789782 |
| 20397 | Nudt6 | NM_001291044.1 | chr3:37303903-37318518 |
| 20398 | Nudt6 | NM_153561.3 | chr3:37303903-37318518 |
| 20399 | Nudt7 | NM_001290180.1 | chr8:116657473-116676212 |
| 20400 | Nudt7 | NM_001290181.1 | chr8:116657473-116676212 |
| 20401 | Nudt7 | NM_001290182.1 | chr8:116657473-116676212 |
| 20402 | Nudt7 | NM_024437.4 | chr8:116657473-116676212 |
| 20403 | Nudt7 | NM_024446.5 | chr8:116657473-116676212 |
| 20404 | Nudt8 | NM_025529.3 | chr19:4000579-4002102 |
| 20405 | Nudt9 | NM_028794.4 | chr5:104475883-104494397 |
| 20406 | Nuf2 | NM_023284.3 | chr1:171428064-171461595 |
| 20407 | Nufip1 | NM_013745.5 | chr14:76510697-76537186 |
| 20408 | Nufip2 | NM_001024205.2 | chr11:77499640-77531468 |
| 20409 | Nuggc | NM_001195674.2 | chr14:66224103-66267280 |
| 20410 | Numa1 | NM_133947.3 | chr7:109118356-109163473 |
| 20411 | Numb | NM_001136075.2 | chr12:85134983-85262884 |
| 20412 | Numb | NM_001272055.1 | chr12:85134983-85262884 |
| 20413 | Numb | NM_001272056.1 | chr12:85134983-85262884 |
| 20414 | Numb | NM_010949.2 | chr12:85134983-85262884 |
| 20415 | Numb | NR_073563.1 | chr12:85134983-85262884 |
| 20416 | Numb | NR_073564.1 | chr12:85134983-85262884 |
| 20417 | Numbl | NM_010950.2 | chr7:28043779-28067169 |
| 20418 | Nup107 | NM_134010.2 | chr10:117187698-117229761 |
| 20419 | Nup133 | NM_172288.2 | chr8:126421022-126473165 |
| 20420 | Nup153 | NM_175749.2 | chr13:46775270-46823218 |
| 20421 | Nup155 | NM_133227.3 | chr15:8059312-8109859 |
| 20422 | Nup160 | NM_021512.2 | chr2:90517371-90576485 |
| 20423 | Nup188 | NM_198304.2 | chr2:30141952-30199782 |
| 20424 | Nup205 | NM_027513.1 | chr6:35127615-35197598 |
| 20425 | Nup210 | NM_018815.2 | chr6:90963060-91066820 |
| 20426 | Nup210l | NM_029937.1 | chr3:89908053-90015939 |
| 20427 | Nup214 | NM_172268.2 | chr2:31829970-31909495 |
| 20428 | Nup35 | NM_001190179.1 | chr2:80478968-80500228 |
| 20429 | Nup35 | NM_027091.4 | chr2:80478968-80500228 |
| 20430 | Nup37 | NM_027191.2 | chr10:87609736-87641140 |
| 20431 | Nup37 | NM_028334.4 | chr10:87609736-87641140 |
| 20432 | Nup43 | NM_145706.2 | chr10:7387301-7398684 |
| 20433 | Nup50 | NM_016714.2 | chr15:84753857-84773393 |
| 20434 | Nup54 | NM_183392.2 | chr5:92844565-92864225 |
| 20435 | Nup62 | NM_053074.1 | chr7:52071790-52086176 |
| 20436 | Nup62cl | NM_001081668.1 | chrX:136542211-136597107 |
| 20437 | Nup62-il4i1 | NM_001171024.1 | chr7:52071740-52096173 |
| 20438 | Nup85 | NM_001002929.4 | chr11:115425757-115445238 |
| 20439 | Nup88 | NM_001083331.2 | chr11:70658262-70783475 |
| 20440 | Nup88 | NM_001276406.1 | chr11:70658262-70783475 |
| 20441 | Nup88 | NM_172394.3 | chr11:70658262-70783475 |
| 20442 | Nup88 | NR_075087.1 | chr11:70658262-70783475 |
| 20443 | Nup93 | NM_172410.2 | chr8:96738500-96838966 |

Fig. 25 - 109

| | | | | | | | | |
|---|---|---|---|---|---|---|---|---|
| 20444 | Nup98 | NM_001287164.1 | chr7:109267913-109358680 | | 20539 | Odam | NM_027128.2 | chr5:88314719-88321767 |
| 20445 | Nup98 | NM_001287165.1 | chr7:109267913-109358680 | | 20540 | Odc1 | NM_013614.2 | chr12:17551678-17558308 |
| 20446 | Nup98 | NM_001287166.1 | chr7:109267913-109358680 | | 20541 | Odf1 | NM_008757.3 | chr15:38148957-38156490 |
| 20447 | Nup98 | NM_001287167.1 | chr7:109267913-109358680 | | 20542 | Odf2 | NM_001113213.1 | chr2:29745239-29787266 |
| 20448 | Nup98 | NM_022979.2 | chr7:109267913-109358680 | | 20543 | Odf2 | NM_001113214.1 | chr2:29745239-29787266 |
| 20449 | Nupl1 | NM_170591.1 | chr14:60838305-60870215 | | 20544 | Odf2 | NM_001177659.1 | chr2:29745239-29787266 |
| 20450 | Nupl2 | NM_153092.4 | chr5:23670780-23689826 | | 20545 | Odf2 | NM_001177661.1 | chr2:29745239-29787266 |
| 20451 | Nupr1 | NM_019738.1 | chr7:133766759-133768984 | | 20546 | Odf2 | NM_013615.3 | chr2:29745239-29787266 |
| 20452 | Nupr1l | NM_026916.3 | chr5:130384409-130387151 | | 20547 | Odf2l | NM_001162538.1 | chr3:144781552-144816879 |
| 20453 | Nus1 | NM_030250.2 | chr10:52137352-52159998 | | 20548 | Odf2l | NM_001162539.1 | chr3:144781552-144816879 |
| 20454 | Nusap1 | NM_001042652.1 | chr2:119435267-119475896 | | 20549 | Odf2l | NM_025714.4 | chr3:144781552-144816879 |
| 20455 | Nusap1 | NM_133851.3 | chr2:119435267-119475896 | | 20550 | Odf3 | NM_027019.3 | chr7:148033814-148036824 |
| 20456 | Nutf2 | NM_026532.3 | chr8:108384534-108404301 | | 20551 | Odf3b | NM_001013022.1 | chr15:89207879-89209685 |
| 20457 | Nutf2-ps1 | NR_033574.1 | chr8:108384560-108403237 | | 20552 | Odf3l1 | NM_198673.2 | chr9:56696465-56699770 |
| 20458 | Nutm1 | NM_172521.1 | chr2:112088104-112099448 | | 20553 | Odf3l2 | NM_001034473.2 | chr10:79102270-79108483 |
| 20459 | Nvl | NM_026171.1 | chr1:183023553-183074288 | | 20554 | Odf4 | NM_145746.2 | chr11:68735336-68740583 |
| 20460 | Nwd1 | NM_176940.5 | chr8:75170609-75238645 | | 20555 | Ofcc1 | NM_172143.2 | chr13:40097250-40383389 |
| 20461 | Nwd2 | NM_177006.3 | chr5:64040341-64201782 | | 20556 | Ofd1 | NM_177429.3 | chrX:162827964-162878636 |
| 20462 | Nxf1 | NM_001276704.1 | chr19:8831592-8845400 | | 20557 | Ogdh | NM_001252282.1 | chr11:6191599-6259097 |
| 20463 | Nxf1 | NM_016813.2 | chr19:8831592-8845400 | | 20558 | Ogdh | NM_001252283.1 | chr11:6191599-6259097 |
| 20464 | Nxf2 | NM_001289735.1 | chrX:131479064-131499293 | | 20559 | Ogdh | NM_001252287.1 | chr11:6191599-6259097 |
| 20465 | Nxf2 | NM_001289736.1 | chrX:131479064-131499293 | | 20560 | Ogdh | NM_001252288.1 | chr11:6191599-6259097 |
| 20466 | Nxf2 | NM_031259.1 | chrX:131479064-131499293 | | 20561 | Ogdh | NM_010956.4 | chr11:6191599-6259097 |
| 20467 | Nxf3 | NM_001024141.4 | chrX:132606637-132619794 | | 20562 | Ogdhl | NM_001081130.1 | chr14:33135204-33161006 |
| 20468 | Nxf7 | NM_130888.1 | chrX:132114325-132128394 | | 20563 | Ogfod1 | NM_001093757.1 | chr8:96561097-96591822 |
| 20469 | Nxn | NM_008750.5 | chr11:76070727-76212643 | | 20564 | Ogfod1 | NM_177767.4 | chr8:96561097-96591822 |
| 20470 | Nxnl1 | NM_145598.2 | chr8:74084453-74090548 | | 20565 | Ogfod2 | NM_025671.2 | chr5:124562346-124565485 |
| 20471 | Nxnl2 | NM_029173.4 | chr3:51266393-51270556 | | 20566 | Ogfod3 | NM_025402.2 | chr11:121038907-121065962 |
| 20472 | Nxpe2 | NM_030069.3 | chr9:48126086-48148981 | | 20567 | Ogfr | NM_031373.3 | chr2:180324111-180330452 |
| 20473 | Nxpe3 | NM_001134457.1 | chr16:55840065-55895392 | | 20568 | Ogfrl1 | NM_001081079.1 | chr1:23373262-23390014 |
| 20474 | Nxpe4 | NM_172921.3 | chr9:48170123-48208108 | | 20569 | Ogg1 | NM_010957.4 | chr6:113276970-113284180 |
| 20475 | Nxpe5 | NM_001013773.3 | chr5:138667131-138693103 | | 20570 | Ogn | NM_008760.4 | chr13:49703440-49719869 |
| 20476 | Nxph1 | NM_008751.5 | chr6:8900018-9198578 | | 20571 | Ogt | NM_001290535.1 | chrX:98835389-98879690 |
| 20477 | Nxph2 | NM_008752.2 | chr2:23176765-23257493 | | 20572 | Ogt | NM_139144.4 | chrX:98835389-98879690 |
| 20478 | Nxph3 | NM_130858.3 | chr11:95371159-95375879 | | 20573 | Oip5 | NM_001042653.1 | chr2:119435268-119444241 |
| 20479 | Nxph4 | NM_183297.2 | chr10:126962528-126971615 | | 20574 | Oit1 | NM_146050.2 | chr14:9181461-9211277 |
| 20480 | Nxt1 | NM_001110159.1 | chr2:148498350-148501762 | | 20575 | Oit3 | NM_010959.2 | chr10:58885707-58904527 |
| 20481 | Nxt1 | NM_019761.6 | chr2:148498350-148501762 | | 20576 | Ola1 | NM_025942.2 | chr2:72930857-73052504 |
| 20482 | Nxt2 | NM_001161430.2 | chrX:138661312-138674243 | | 20577 | Ola1 | NM_030091.1 | chr2:72930857-73052504 |
| 20483 | Nxt2 | NM_001290532.1 | chrX:138661312-138674243 | | 20578 | Olah | NM_145921.1 | chr2:3259259-3283841 |
| 20484 | Nxt2 | NM_001290533.1 | chrX:138661312-138674243 | | 20579 | Olfm1 | NM_001038612.1 | chr2:28048612-28086256 |
| 20485 | Nxt2 | NM_172782.4 | chrX:138661312-138674243 | | 20580 | Olfm1 | NM_001038613.1 | chr2:28048612-28086256 |
| 20486 | Nyap1 | NM_175521.3 | chr5:138172190-138181226 | | 20581 | Olfm1 | NM_001038614.1 | chr2:28048612-28086256 |
| 20487 | Nyap2 | NM_172849.3 | chr1:81073891-81268226 | | 20582 | Olfm1 | NM_019498.2 | chr2:28048612-28086256 |
| 20488 | Nynrin | NM_001040072.1 | chr14:56472951-56493573 | | 20583 | Olfm2 | NM_173777.3 | chr9:20472429-20532658 |
| 20489 | Nyx | NM_173415.4 | chrX:13044797-13066439 | | 20584 | Olfm3 | NM_001286750.1 | chr3:114606995-114828682 |
| 20490 | Oacyl | NM_177028.3 | chr18:65857921-65911191 | | 20585 | Olfm3 | NM_153157.3 | chr3:114606995-114828682 |
| 20491 | Oaf | NM_178644.3 | chr9:43029360-43047899 | | 20586 | Olfm3 | NM_153458.3 | chr3:114606995-114828682 |
| 20492 | Oard1 | NM_001289490.1 | chr17:48549324-48556595 | | 20587 | Olfm4 | NM_001030294.1 | chr14:80400108-80421737 |
| 20493 | Oard1 | NM_001289491.1 | chr17:48549324-48556595 | | 20588 | Olfml1 | NM_172907.3 | chr7:114710946-114734879 |
| 20494 | Oard1 | NM_207219.4 | chr17:48549324-48556595 | | 20589 | Olfml2a | NM_172854.2 | chr2:38787499-38816105 |
| 20495 | Oas1a | NM_145211.2 | chr5:121346265-121357534 | | 20590 | Olfml2b | NM_177068.4 | chr3:172574662-172612920 |
| 20496 | Oas1b | NM_001083925.1 | chr5:121262643-121274169 | | 20591 | Olfml3 | NM_133859.2 | chr3:103539316-103541924 |
| 20497 | Oas1b | NR_003507.1 | chr5:121262643-121274169 | | 20592 | Olfr1 | NM_146921.2 | chr11:73208577-73212997 |
| 20498 | Oas1c | NM_033541.4 | chr5:121250207-121262523 | | 20593 | Olfr10 | NM_206822.1 | chr11:49131049-49131985 |
| 20499 | Oas1d | NM_133893.3 | chr5:121364826-121371656 | | 20594 | Olfr100 | NM_207673.1 | chr17:37450401-37451327 |
| 20500 | Oas1e | NM_145210.2 | chr5:121236320-121245539 | | 20595 | Olfr1000 | NM_001011695.1 | chr2:85448120-85449065 |
| 20501 | Oas1f | NM_145153.1 | chr5:121297375-121307995 | | 20596 | Olfr1002 | NM_146573.2 | chr2:85487519-85488476 |
| 20502 | Oas1g | NM_011852.1 | chr5:121286150-121337607 | | 20597 | Olfr1006 | NM_146570.2 | chr2:85514367-85518898 |
| 20503 | Oas1h | NM_001159934.1 | chr5:121311430-121323514 | | 20598 | Olfr1008 | NM_146866.1 | chr2:85529587-85530529 |
| 20504 | Oas1h | NM_145228.2 | chr5:121311430-121323514 | | 20599 | Olfr1009 | NM_146572.2 | chr2:85561563-85562508 |
| 20505 | Oas2 | NM_145181.3 | chr5:121180341-121199857 | | 20600 | Olfr101 | NM_146834.1 | chr17:37436438-37437365 |
| 20506 | Oas3 | NM_145226.2 | chr5:121203106-121227668 | | 20601 | Olfr1010 | NM_207149.2 | chr2:85593519-85594463 |
| 20507 | Oasl1 | NM_145209.3 | chr5:115373248-115387920 | | 20602 | Olfr1012 | NM_146568.2 | chr2:85599595-85600531 |
| 20508 | Oasl2 | NM_011854.2 | chr5:115364942-115362254 | | 20603 | Olfr1013 | NM_146762.2 | chr2:85609959-85610877 |
| 20509 | Oat | NM_016978.2 | chr7:139749157-139768081 | | 20604 | Olfr1014 | NM_146569.2 | chr2:85616742-85617660 |
| 20510 | Oaz1 | NM_008753.4 | chr10:80289401-80292035 | | 20605 | Olfr1015 | NM_146571.2 | chr2:85625630-85626646 |
| 20511 | Oaz1-ps | NR_027656.1 | chr10:80289441-80291962 | | 20606 | Olfr1016 | NM_001011758.2 | chr2:85639495-85640425 |
| 20512 | Oaz2 | NM_010952.3 | chr9:65524354-65538107 | | 20607 | Olfr1018 | NM_146586.2 | chr2:85663129-85664065 |
| 20513 | Oaz3 | NM_016901.3 | chr3:94237087-94240538 | | 20608 | Olfr1019 | NM_147015.1 | chr2:85681013-85681946 |
| 20514 | Obfc1 | NM_175360.2 | chr19:47575538-47611510 | | 20609 | Olfr102 | NM_001011721.2 | chr17:37450356-37451382 |
| 20515 | Obox1 | NM_027802.2 | chr7:16132605-16142195 | | 20610 | Olfr1020 | NM_146580.2 | chr2:85689576-85690655 |
| 20516 | Obox2 | NM_145708.2 | chr7:15974199-15983892 | | 20611 | Olfr1022 | NM_146589.2 | chr2:85708750-85709698 |
| 20517 | Obox2 | NM_145708.2 | chr7_random:257108-266801 | | 20612 | Olfr1023 | NM_146587.2 | chr2:85726958-85727894 |
| 20518 | Obox3 | NM_145707.3 | chr7:16210654-16225126 | | 20613 | Olfr1024 | NM_001005230.2 | chr2:85744225-85745209 |
| 20519 | Obox5 | NM_145709.2 | chr7:16335718-16344623 | | 20614 | Olfr1026 | NM_146584.2 | chr2:85763426-85764350 |
| 20520 | Obox6 | NM_145710.2 | chr7:16418598-16425028 | | 20615 | Olfr1028 | NM_001011774.2 | chr2:85791221-85792196 |
| 20521 | Obp1a | NM_008754.2 | chrX:75330843-75336713 | | 20616 | Olfr1029 | NM_001011852.2 | chr2:85815369-85816430 |
| 20522 | Obp2a | NM_153558.1 | chr2:25555593-25558846 | | 20617 | Olfr103 | NM_146833.1 | chr17:37473233-37474175 |
| 20523 | Obp2b | NM_001099301.1 | chr2:25597528-25595617 | | 20618 | Olfr1030 | NM_146588.2 | chr2:85819468-85824955 |
| 20524 | Obscn | NM_001171512.2 | chr11:58807758-58949877 | | 20619 | Olfr1031 | NM_001011759.2 | chr2:85831975-85832986 |
| 20525 | Obscn | NM_199152.3 | chr11:58807758-58949877 | | 20620 | Olfr1032 | NM_146579.2 | chr2:85847934-85848867 |
| 20526 | Obsl1 | NM_178884.5 | chr1:75482399-75503027 | | 20621 | Olfr1033 | NM_146578.2 | chr2:85860796-85884965 |
| 20527 | Oc90 | NM_010953.2 | chr15:65707614-65743849 | | 20622 | Olfr1034 | NM_001011872.2 | chr2:85886600-85887623 |
| 20528 | Oca2 | NM_021429.4 | chr7:63495140-63791887 | | 20623 | Olfr1036 | NM_207142.2 | chr2:85914860-85915875 |
| 20529 | Ocel1 | NM_029865.2 | chr8:73895196-73897588 | | 20624 | Olfr1037 | NM_001015532.2 | chr2:85924886-85926011 |
| 20530 | Ociad1 | NM_001159887.1 | chr5:73684032-73705316 | | 20625 | Olfr1038-ps | NM_147013.2 | chr2:85960380-85963194 |
| 20531 | Ociad1 | NM_001159888.1 | chr5:73684032-73705316 | | 20626 | Olfr1039 | NM_001011784.2 | chr2:85970858-85971818 |
| 20532 | Ociad1 | NM_001159889.1 | chr5:73684032-73705316 | | 20627 | Olfr1040 | NM_207561.2 | chr2:85985947-85986889 |
| 20533 | Ociad1 | NM_023039.3 | chr5:73684032-73705316 | | 20628 | Olfr1042 | NM_001011777.2 | chr2:85999501-86000598 |
| 20534 | Ociad2 | NM_026950.3 | chr5:73713437-73729878 | | 20629 | Olfr1043 | NM_146577.2 | chr2:86002159-86003104 |
| 20535 | Ocln | NM_008756.2 | chr13:101267321-101322453 | | 20630 | Olfr1044 | NM_147011.1 | chr2:86011027-86011972 |
| 20536 | Ocm | NM_033039.3 | chr5:144780675-144811478 | | 20631 | Olfr1045 | NM_147017.2 | chr2:86037959-86038907 |
| 20537 | Ocrl | NM_177215.3 | chrX:45265632-45319043 | | 20632 | Olfr1046 | NM_146582.2 | chr2:86056914-86057865 |
| 20538 | Ocstamp | NM_029021.1 | chr2:165220949-165225894 | | 20633 | Olfr1047 | NM_147012.1 | chr2:86068166-86069126 |

Fig. 25 - 110

| | | | | | | | | |
|---|---|---|---|---|---|---|---|---|
| 20634 | Olfr1048 | NM_147014.1 | chr2:86076027-86076990 | | 20729 | Olfr117 | NM_207155.2 | chr17:37796322-37797276 |
| 20635 | Olfr1049 | NM_147016.2 | chr2:86094921-86095848 | | 20730 | Olfr1170 | NM_146532.1 | chr2:88064236-88065187 |
| 20636 | Olfr1051 | NM_207562.1 | chr2:86115715-86116642 | | 20731 | Olfr1173 | NM_207566.1 | chr2:88114265-88115204 |
| 20637 | Olfr1052 | NM_147010.2 | chr2:86137974-86138913 | | 20732 | Olfr1176 | NM_146771.1 | chr2:88179723-88180671 |
| 20638 | Olfr1053 | NM_001177857.1 | chr2:86154499-86155442 | | 20733 | Olfr1178 | NM_001011868.1 | chr2:88231405-88232377 |
| 20639 | Olfr1054 | NM_147019.1 | chr2:86172572-86173511 | | 20734 | Olfr1179 | NM_146917.2 | chr2:88242165-88243089 |
| 20640 | Olfr1055 | NM_147021.1 | chr2:86186982-86187921 | | 20735 | Olfr118 | NM_213721.2 | chr17:37808969-37809935 |
| 20641 | Olfr1056 | NM_147018.2 | chr2:86195515-86196594 | | 20736 | Olfr1180 | NM_146918.2 | chr2:88251783-88252846 |
| 20642 | Olfr1057 | NM_207563.2 | chr2:86214619-86215567 | | 20737 | Olfr1181 | NM_001011816.1 | chr2:88263244-88264180 |
| 20643 | Olfr1058 | NM_146391.2 | chr2:86225622-86226573 | | 20738 | Olfr1182 | NM_001011535.2 | chr2:88286175-88289278 |
| 20644 | Olfr1061 | NM_207134.1 | chr2:86253265-86254207 | | 20739 | Olfr1183 | NM_146529.2 | chr2:88301498-88302410 |
| 20645 | Olfr1062 | NM_147078.2 | chr2:86262875-86263831 | | 20740 | Olfr1184 | NM_146823.1 | chr2:88326890-88327826 |
| 20646 | Olfr1065 | NM_146408.2 | chr2:86285169-86286161 | | 20741 | Olfr1186 | NM_146530.2 | chr2:88365657-88366747 |
| 20647 | Olfr1066 | NM_001011735.2 | chr2:86295484-86296426 | | 20742 | Olfr1188 | NM_146919.2 | chr2:88399607-88400575 |
| 20648 | Olfr107 | NM_146511.2 | chr17:37542421-37543454 | | 20743 | Olfr1189 | NM_146772.2 | chr2:88431962-88432883 |
| 20649 | Olfr1076 | NM_146406.2 | chr2:86348617-86349559 | | 20744 | Olfr119 | NM_001011830.2 | chr17:37833629-37838582 |
| 20650 | Olfr1077-ps1 | NR_033507.1 | chr2:86365819-86368584 | | 20745 | Olfr1193 | NM_001011517.2 | chr2:88518013-88518970 |
| 20651 | Olfr1079 | NM_146407.1 | chr2:86378122-86379070 | | 20746 | Olfr1195 | NM_146753.2 | chr2:88522980-88523887 |
| 20652 | Olfr108 | NM_146465.2 | chr17:37582424-37583462 | | 20747 | Olfr1196 | NM_146464.2 | chr2:88540539-88541484 |
| 20653 | Olfr1080 | NM_146409.2 | chr2:86393337-86398295 | | 20748 | Olfr1197 | NM_001005225.1 | chr2:88568809-88569754 |
| 20654 | Olfr1082 | NM_207674.2 | chr2:86434041-86438966 | | 20749 | Olfr1198 | NM_207567.1 | chr2:88586116-88587043 |
| 20655 | Olfr1084 | NM_207135.2 | chr2:86478921-86479875 | | 20750 | Olfr1199 | NM_146458.1 | chr2:88595897-88596830 |
| 20656 | Olfr1085 | NM_146590.2 | chr2:86497671-86498613 | | 20751 | Olfr12 | NM_206896.2 | chr1:94516457-94517578 |
| 20657 | Olfr1086 | NM_146592.1 | chr2:86516555-86517488 | | 20752 | Olfr120 | NM_146631.1 | chr17:37862943-37863936 |
| 20658 | Olfr1087 | NM_146864.2 | chr2:86530188-86531130 | | 20753 | Olfr1200 | NM_001005227.2 | chr2:88607459-88608470 |
| 20659 | Olfr1089 | NM_001011771.2 | chr2:86572831-86573767 | | 20754 | Olfr1201 | NM_146895.1 | chr2:88634540-88635464 |
| 20660 | Olfr109 | NM_146835.1 | chr17:37603152-37604097 | | 20755 | Olfr1202 | NM_146462.1 | chr2:88657329-88658259 |
| 20661 | Olfr1090 | NM_146843.1 | chr2:86593951-86594893 | | 20756 | Olfr1204 | NM_146463.2 | chr2:88692108-88693038 |
| 20662 | Olfr1093 | NM_146366.1 | chr2:86625888-86626857 | | 20757 | Olfr1205 | NM_146896.3 | chr2:88669913-88672199 |
| 20663 | Olfr1094 | NM_146365.2 | chr2:86668832-86669979 | | 20758 | Olfr1206 | NM_001001810.2 | chr2:88704763-88705687 |
| 20664 | Olfr1095 | NM_146730.2 | chr2:86690926-86691853 | | 20759 | Olfr1208 | NM_146778.1 | chr2:88736825-88737752 |
| 20665 | Olfr1097 | NM_146843.2 | chr2:86730382-86732320 | | 20760 | Olfr1209 | NM_146461.2 | chr2:88749615-88750548 |
| 20666 | Olfr1098 | NM_146845.1 | chr2:86762739-86763687 | | 20761 | Olfr121 | NM_146629.2 | chr17:37888810-37889949 |
| 20667 | Olfr1099 | NM_146768.1 | chr2:86798674-86799613 | | 20762 | Olfr1211 | NM_001011804.1 | chr2:88769534-88770470 |
| 20668 | Olfr11 | NM_146542.2 | chr13:21730448-21731390 | | 20763 | Olfr1212 | NM_207140.3 | chr2:88798624-88799560 |
| 20669 | Olfr110 | NM_146328.2 | chr17:37629412-37636619 | | 20764 | Olfr1213 | NM_146898.2 | chr2:88813110-88820424 |
| 20670 | Olfr1100 | NM_146594.1 | chr2:86817985-86818951 | | 20765 | Olfr1214 | NM_146897.2 | chr2:88827421-88828357 |
| 20671 | Olfr1101 | NM_146591.2 | chr2:86828398-86829331 | | 20766 | Olfr1215 | NM_146459.2 | chr2:88841504-88842447 |
| 20672 | Olfr1102 | NM_207154.2 | chr2:86842088-86843151 | | 20767 | Olfr1216 | NM_146893.2 | chr2:88853283-88854219 |
| 20673 | Olfr1104 | NM_146767.2 | chr2:86861766-86862699 | | 20768 | Olfr1217 | NM_146901.2 | chr2:88863151-88864256 |
| 20674 | Olfr1105 | NM_001011825.1 | chr2:86873437-86874376 | | 20769 | Olfr1218 | NM_146818.2 | chr2:88894645-88895581 |
| 20675 | Olfr1106 | NM_146752.2 | chr2:86888452-86889391 | | 20770 | Olfr1219 | NM_146899.2 | chr2:88914310-88915246 |
| 20676 | Olfr1107 | NM_146844.2 | chr2:86911272-86912380 | | 20771 | Olfr122 | NM_146288.3 | chr17:37905586-37909565 |
| 20677 | Olfr1109 | NM_146766.2 | chr2:86932613-86933552 | | 20772 | Olfr1220 | NM_146900.2 | chr2:88937094-88938120 |
| 20678 | Olfr111 | NM_001005485.2 | chr17:37666901-37667942 | | 20773 | Olfr1221 | NM_146902.2 | chr2:88951731-88952667 |
| 20679 | Olfr1110 | NM_146769.1 | chr2:86975537-86976476 | | 20774 | Olfr1222 | NM_001011860.1 | chr2:88964950-88965886 |
| 20680 | Olfr1111 | NM_146593.2 | chr2:86989876-86990816 | | 20775 | Olfr1223 | NM_146892.2 | chr2:88984242-88991493 |
| 20681 | Olfr1112 | NM_146663.2 | chr2:87031845-87032802 | | 20776 | Olfr1225 | NM_146891.2 | chr2:89010375-89011402 |
| 20682 | Olfr1113 | NM_207565.1 | chr2:87053050-87054031 | | 20777 | Olfr1226 | NM_146967.1 | chr2:89033256-89034189 |
| 20683 | Olfr1115 | NM_146297.2 | chr2:87091996-87093098 | | 20778 | Olfr1228 | NM_146971.1 | chr2:89088877-89089849 |
| 20684 | Olfr1116-ps | NM_001011734.1 | chr2:87109002-87109926 | | 20779 | Olfr1229 | NM_001011761.1 | chr2:89122352-89123288 |
| 20685 | Olfr1118 | NM_207632.2 | chr2:87148920-87149916 | | 20780 | Olfr123 | NM_146630.1 | chr17:37932390-37933320 |
| 20686 | Olfr112 | NM_001013575.4 | chr17:37700183-37706396 | | 20781 | Olfr1230 | NM_146589.1 | chr2:89136507-89137425 |
| 20687 | Olfr1120 | NM_147029.1 | chr2:87197602-87198547 | | 20782 | Olfr1231 | NM_146454.2 | chr2:89142805-89143747 |
| 20688 | Olfr1121 | NM_146348.2 | chr2:87211690-87212635 | | 20783 | Olfr1232 | NM_146323.1 | chr2:89165399-89166835 |
| 20689 | Olfr1122 | NM_147031.1 | chr2:87227883-87228844 | | 20784 | Olfr1233 | NM_146972.2 | chr2:89179539-89180457 |
| 20690 | Olfr1123 | NM_146350.2 | chr2:87258206-87259178 | | 20785 | Olfr1234 | NM_146973.2 | chr2:89202639-89203584 |
| 20691 | Olfr1124 | NM_147028.2 | chr2:87274645-87275602 | | 20786 | Olfr1238 | NM_146790.1 | chr2:89246286-89247234 |
| 20692 | Olfr1126 | NM_146857.2 | chr2:87297323-87298268 | | 20787 | Olfr1239 | NM_146970.1 | chr2:89257650-89258568 |
| 20693 | Olfr1128 | NM_146349.2 | chr2:87384763-87385699 | | 20788 | Olfr124 | NM_147062.2 | chr17:37942013-37943135 |
| 20694 | Olfr1129 | NM_001011836.2 | chr2:87415242-87416187 | | 20789 | Olfr1240 | NM_146808.2 | chr2:89279426-89280500 |
| 20695 | Olfr113 | NM_146289.1 | chr17:37711427-37712366 | | 20790 | Olfr1241 | NM_146455.1 | chr2:89323290-89323290 |
| 20696 | Olfr1130 | NM_146838.2 | chr2:87446368-87448491 | | 20791 | Olfr1242 | NM_146968.2 | chr2:89333450-89334503 |
| 20697 | Olfr1131 | NM_146658.1 | chr2:87468621-87469551 | | 20792 | Olfr1243 | NM_146969.1 | chr2:89367647-89368565 |
| 20698 | Olfr1132 | NM_146836.1 | chr2:87474975-87475902 | | 20793 | Olfr1245 | NM_146788.2 | chr2:89414868-89415930 |
| 20699 | Olfr1133 | NM_146351.2 | chr2:87485336-87486278 | | 20794 | Olfr1246 | NM_146792.2 | chr2:89430225-89431303 |
| 20700 | Olfr1134 | NM_147030.2 | chr2:87496081-87498614 | | 20795 | Olfr1247 | NM_146966.2 | chr2:89449245-89450310 |
| 20701 | Olfr1135 | NM_146660.2 | chr2:87511589-87512522 | | 20796 | Olfr1248 | NM_146791.2 | chr2:89457324-89458402 |
| 20702 | Olfr1136 | NM_146659.3 | chr2:87533037-87534104 | | 20797 | Olfr1249 | NM_001011796.2 | chr2:89470096-89471053 |
| 20703 | Olfr1137 | NM_001011833.1 | chr2:87551128-87552061 | | 20798 | Olfr125 | NM_146290.2 | chr17:37971855-37972973 |
| 20704 | Olfr1138 | NM_146639.1 | chr2:87577543-87578479 | | 20799 | Olfr1250 | NM_146965.1 | chr2:89496651-89497596 |
| 20705 | Olfr114 | NM_146287.1 | chr17:37726357-37727296 | | 20800 | Olfr1251 | NM_001011529.1 | chr2:89507084-89508041 |
| 20706 | Olfr1140 | NM_146642.2 | chr2:87586317-87587337 | | 20801 | Olfr1252 | NM_207568.1 | chr2:89561321-89562266 |
| 20707 | Olfr1141 | NM_146637.1 | chr2:87593212-87594148 | | 20802 | Olfr1253 | NM_146373.1 | chr2:89592026-89592983 |
| 20708 | Olfr1143 | NM_146293.2 | chr2:87642547-87643492 | | 20803 | Olfr1254 | NM_146476.1 | chr2:89628562-89629507 |
| 20709 | Olfr1145 | NM_146320.2 | chr2:87649978-87650956 | | 20804 | Olfr1255 | NM_146977.2 | chr2:89656484-89657417 |
| 20710 | Olfr1148 | NM_001011519.1 | chr2:87673197-87674142 | | 20805 | Olfr1256 | NM_146983.1 | chr2:89675179-89676100 |
| 20711 | Olfr115 | NM_001011753.2 | chr17:37746729-37747724 | | 20806 | Olfr1257 | NM_146982.1 | chr2:89720984-89721914 |
| 20712 | Olfr1151 | NM_146638.1 | chr2:87697333-87698260 | | 20807 | Olfr1258 | NM_146978.1 | chr2:89769967-89770903 |
| 20713 | Olfr1152 | NM_001011834.1 | chr2:87708149-87709082 | | 20808 | Olfr1259 | NM_146341.1 | chr2:89783340-89784270 |
| 20714 | Olfr1153 | NM_146640.2 | chr2:87736333-87737290 | | 20809 | Olfr126 | NM_146890.2 | chr17:37987538-37988498 |
| 20715 | Olfr1154 | NM_146647.2 | chr2:87742898-87743831 | | 20810 | Olfr1260 | NM_146981.1 | chr2:89817936-89818869 |
| 20716 | Olfr1155 | NM_146643.2 | chr2:87782838-87783783 | | 20811 | Olfr1261 | NM_146474.1 | chr2:89833551-89834472 |
| 20717 | Olfr1156 | NM_146817.2 | chr2:87789346-87790422 | | 20812 | Olfr1262 | NM_146974.1 | chr2:89842564-89843479 |
| 20718 | Olfr1157 | NM_146849.2 | chr2:87802108-87808414 | | 20813 | Olfr1263 | NM_146794.1 | chr2:89855088-89856009 |
| 20719 | Olfr1158 | NM_146645.2 | chr2:87830269-87831211 | | 20814 | Olfr1264 | NM_021368.1 | chr2:89861294-89862221 |
| 20720 | Olfr116 | NM_146649.1 | chr17:37760612-37761578 | | 20815 | Olfr1265 | NM_146343.1 | chr2:89877077-89878002 |
| 20721 | Olfr1160 | NM_146649.2 | chr2:87845973-87846933 | | 20816 | Olfr1269 | NM_146342.1 | chr2:89958823-89959753 |
| 20722 | Olfr1161 | NM_146848.1 | chr2:87864858-87865870 | | 20817 | Olfr127 | NM_146377.1 | chr17:38040492-38041464 |
| 20723 | Olfr1162 | NM_001011835.1 | chr2:87889834-87890779 | | 20818 | Olfr1270 | NM_146985.2 | chr2:89989175-89990193 |
| 20724 | Olfr1163 | NM_146644.2 | chr2:87910521-87911564 | | 20819 | Olfr1271 | NM_146793.1 | chr2:90105667-90106585 |
| 20725 | Olfr1164 | NM_146641.2 | chr2:87933011-87934123 | | 20820 | Olfr1272 | NM_146980.1 | chr2:90121803-90122730 |
| 20726 | Olfr1166 | NM_146650.2 | chr2:87963516-87965150 | | 20821 | Olfr1273-ps | NM_146975.1 | chr2:90136092-90137016 |
| 20727 | Olfr1167 | NM_146294.2 | chr2:87989140-87990240 | | 20822 | Olfr1274-ps | NM_146263.2 | chr2:90240796-90241831 |
| 20728 | Olfr1168 | NM_146531.2 | chr2:88025035-88025974 | | 20823 | Olfr1275 | NM_001011795.1 | chr2:111071009-111071948 |

Fig. 25 - 111

| | | | | | | | | |
|---|---|---|---|---|---|---|---|---|
| 20824 | Olfr1276 | NM_146395.1 | chr2:111097273-111098212 | | 20919 | Olfr1378 | NM_146910.1 | chr11:50782521-50783469 |
| 20825 | Olfr1277 | NM_146396.1 | chr2:111109610-111110522 | | 20920 | Olfr138 | NM_130868.1 | chr17:38411717-38412656 |
| 20826 | Olfr1278 | NM_146394.1 | chr2:111132426-111133368 | | 20921 | Olfr1380 | NM_207573.1 | chr11:49377424-49378360 |
| 20827 | Olfr1279 | NM_146393.1 | chr2:111146357-111147299 | | 20922 | Olfr1381 | NM_146469.2 | chr11:49365250-49366186 |
| 20828 | Olfr128 | NM_206816.1 | chr17:38060512-38061439 | | 20923 | Olfr1382 | NM_001011790.1 | chr11:49348688-49349624 |
| 20829 | Olfr1280 | NM_146908.1 | chr2:111155637-111156555 | | 20924 | Olfr1383 | NM_207574.1 | chr11:49337226-49338162 |
| 20830 | Olfr1281 | NM_001005568.1 | chr2:111168577-111169495 | | 20925 | Olfr1384 | NM_146472.2 | chr11:49327119-49328153 |
| 20831 | Olfr1282 | NM_146907.2 | chr2:111175315-111176233 | | 20926 | Olfr1385 | NM_001011805.1 | chr11:49308036-49308966 |
| 20832 | Olfr1283 | NM_207236.1 | chr2:111208790-111209708 | | 20927 | Olfr1386 | NM_001011741.2 | chr11:49283555-49284683 |
| 20833 | Olfr1284 | NM_146381.1 | chr2:111219158-111220094 | | 20928 | Olfr1387 | NM_146473.1 | chr11:49273182-49274118 |
| 20834 | Olfr1286 | NM_207254.1 | chr2:111260188-111261106 | | 20929 | Olfr1388 | NM_146467.1 | chr11:49257354-49258290 |
| 20835 | Olfr1287 | NM_001011773.1 | chr2:111289298-111290216 | | 20930 | Olfr1389 | NM_147066.2 | chr11:49243928-49245001 |
| 20836 | Olfr1288 | NM_146400.2 | chr2:111318942-111319881 | | 20931 | Olfr139 | NM_147003.1 | chr11:73857826-73858774 |
| 20837 | Olfr1289 | NM_146404.1 | chr2:111323588-111324485 | | 20932 | Olfr1390 | NM_147065.1 | chr11:49154035-49154971 |
| 20838 | Olfr129 | NM_146327.2 | chr17:38191543-38196729 | | 20933 | Olfr1391 | NM_146468.1 | chr1:49140914-48141850 |
| 20839 | Olfr1290 | NM_001278787.1 | chr2:111329374-111333972 | | 20934 | Olfr1392 | NM_146470.2 | chr11:49106798-49107824 |
| 20840 | Olfr1290 | NM_001278788.1 | chr2:111329374-111333972 | | 20935 | Olfr1393 | NM_146471.1 | chr11:49093651-49094587 |
| 20841 | Olfr1290 | NM_146262.3 | chr2:111329374-111333972 | | 20936 | Olfr1394 | NM_146276.1 | chr11:48973517-48974456 |
| 20842 | Olfr1294 | NM_146885.1 | chr2:111375505-111378444 | | 20937 | Olfr1395 | NM_146877.1 | chr11:48961760-48962714 |
| 20843 | Olfr1295 | NM_146403.1 | chr2:111404660-111405599 | | 20938 | Olfr1396 | NM_146337.1 | chr11:48926279-48927259 |
| 20844 | Olfr1297 | NM_146888.1 | chr2:111461290-111462229 | | 20939 | Olfr140 | NM_020515.1 | chr2:89891570-89892479 |
| 20845 | Olfr1298 | NM_146886.1 | chr2:111485213-111486152 | | 20940 | Olfr1402 | NM_146275.1 | chr3:97214139-97215102 |
| 20846 | Olfr1299 | NM_146884.2 | chr2:111501609-111505323 | | 20941 | Olfr1404 | NM_146881.2 | chr1:175145737-175146771 |
| 20847 | Olfr13 | NM_146652.1 | chr6:43123986-43124919 | | 20942 | Olfr1406 | NM_146763.2 | chr1:175113572-175114635 |
| 20848 | Olfr130 | NM_146487.1 | chr17:38204117-38205071 | | 20943 | Olfr1408 | NM_146764.1 | chr1:175060413-175061346 |
| 20849 | Olfr1300-ps1 | NR_033534.1 | chr2:111507593-111533476 | | 20944 | Olfr141 | NM_181818.2 | chr2:86646177-86647154 |
| 20850 | Olfr1301 | NM_146887.1 | chr2:111594407-111595346 | | 20945 | Olfr1410 | NM_146491.1 | chr1:94504415-94505384 |
| 20851 | Olfr1302 | NM_146489.2 | chr2:111620469-111621417 | | 20946 | Olfr1411 | NM_146490.1 | chr1:94493097-94494069 |
| 20852 | Olfr1303 | NM_146402.2 | chr2:111653942-111654881 | | 20947 | Olfr1412 | NM_146277.1 | chr1:94484908-94485874 |
| 20853 | Olfr1305 | NM_146401.2 | chr2:111713071-111714010 | | 20948 | Olfr1413 | NM_147037.2 | chr1:94469701-94470783 |
| 20854 | Olfr1306 | NM_001011803.2 | chr2:111752146-111753085 | | 20949 | Olfr1414 | NM_147039.2 | chr1:94407624-94415092 |
| 20855 | Olfr1307 | NM_001011787.1 | chr2:111784672-111785611 | | 20950 | Olfr1415 | NM_001011525.1 | chr1:94387394-94388330 |
| 20856 | Olfr1308 | NM_207151.1 | chr2:111800265-111801228 | | 20951 | Olfr1416 | NM_147038.1 | chr1:94376257-94377196 |
| 20857 | Olfr1309 | NM_146447.1 | chr2:111823290-111824253 | | 20952 | Olfr1417 | NM_146936.1 | chr19:11902566-11903514 |
| 20858 | Olfr131 | NM_146867.1 | chr17:38218976-38219921 | | 20953 | Olfr1418 | NM_001011524.1 | chr19:11929484-11930441 |
| 20859 | Olfr1310 | NM_146449.1 | chr2:111848402-111849341 | | 20954 | Olfr1419 | NM_001011775.1 | chr19:11944672-11945704 |
| 20860 | Olfr1311 | NM_146274.1 | chr2:111861070-111862009 | | 20955 | Olfr142 | NM_146984.1 | chr2:90092225-90093148 |
| 20861 | Olfr1312 | NM_146362.1 | chr2:111882233-111883187 | | 20956 | Olfr1420 | NM_146410.1 | chr19:11970512-11971442 |
| 20862 | Olfr1313 | NM_207150.1 | chr2:111911802-111912738 | | 20957 | Olfr1423 | NM_146680.1 | chr12:12110297-12111230 |
| 20863 | Olfr1314 | NM_146450.2 | chr2:111931917-111932856 | | 20958 | Olfr1424 | NM_146681.1 | chr19:12133298-12134240 |
| 20864 | Olfr1316 | NM_146742.1 | chr2:111970027-111970972 | | 20959 | Olfr1425 | NM_001011853.1 | chr19:12148184-12149120 |
| 20865 | Olfr1317 | NM_146448.1 | chr2:111982103-111983054 | | 20960 | Olfr1426 | NM_146809.2 | chr19:12162099-12166337 |
| 20866 | Olfr1318 | NM_001011802.2 | chr2:111996054-111997164 | | 20961 | Olfr1427 | NM_146679.1 | chr19:12173191-12174127 |
| 20867 | Olfr132 | NM_001005481.1 | chr17:38267193-38268135 | | 20962 | Olfr1428 | NM_146678.2 | chr19:12183089-12184034 |
| 20868 | Olfr1320 | NM_207240.3 | chrX:47036680-47037640 | | 20963 | Olfr143 | NM_146806.2 | chr9:38061003-38061945 |
| 20869 | Olfr1321 | NM_207631.1 | chrX:47080149-47081109 | | 20964 | Olfr1431 | NM_146414.1 | chr19:12284057-12284996 |
| 20870 | Olfr1322 | NM_001011794.1 | chrX:47238645-47239578 | | 20965 | Olfr1433 | NM_146685.3 | chr19:12354344-12358478 |
| 20871 | Olfr1323 | NM_146390.1 | chrX:47362482-47363412 | | 20966 | Olfr1434 | NM_207626.1 | chr19:12,357,540-12,358,478 |
| 20872 | Olfr1324 | NM_146292.1 | chrX:47778672-47779671 | | 20967 | Olfr1436 | NM_146687.2 | chr19:12372672-12373620 |
| 20873 | Olfr1325 | NM_146398.1 | chrX:71839666-71840614 | | 20968 | Olfr1437 | NM_001011839.1 | chr19:12396376-12397315 |
| 20874 | Olfr1328 | NM_146399.2 | chr4:118606503-118607445 | | 20969 | Olfr1440 | NM_146684.1 | chr19:12468754-12469702 |
| 20875 | Olfr1329 | NM_001011870.2 | chr4:118589128-118590070 | | 20970 | Olfr1441 | NM_146683.1 | chr19:12496800-12497757 |
| 20876 | Olfr133 | NM_148831.1 | chr17:38285534-38286473 | | 20971 | Olfr1442 | NM_146697.2 | chr17:12748668-12749733 |
| 20877 | Olfr1330 | NM_146334.2 | chr4:118565689-118566637 | | 20972 | Olfr1443 | NM_146698.2 | chr19:12752655-12758335 |
| 20878 | Olfr1331 | NM_001011856.2 | chr4:118541387-118542341 | | 20973 | Olfr1444 | NM_146702.1 | chr19:12936266-12937226 |
| 20879 | Olfr1333 | NM_207157.2 | chr4:118502089-118503043 | | 20974 | Olfr1445 | NM_146699.1 | chr19:12958372-12959317 |
| 20880 | Olfr1335 | NM_207703.1 | chr4:118481459-118482467 | | 20975 | Olfr1446 | NM_146704.1 | chr19:12964138-12965065 |
| 20881 | Olfr1336 | NM_146915.1 | chr7:6413221-6414166 | | 20976 | Olfr1447 | NM_146703.1 | chr19:12975338-12976268 |
| 20882 | Olfr1337 | NM_146309.3 | chr4:118454240-118455191 | | 20977 | Olfr1448 | NM_146701.1 | chr19:12993852-12994797 |
| 20883 | Olfr1338 | NM_207152.1 | chr4:118426199-118427141 | | 20978 | Olfr1449 | NM_146303.1 | chr19:13009229-13010174 |
| 20884 | Olfr1339 | NM_146852.2 | chr4:118407135-118408083 | | 20979 | Olfr145 | NM_146313.1 | chr9:37704990-37705923 |
| 20885 | Olfr134 | NM_146832.1 | chr17:38312030-38312969 | | 20980 | Olfr1450 | NM_146371.1 | chr19:13028080-13029058 |
| 20886 | Olfr1340 | NM_146304.2 | chr4:118398853-118399801 | | 20981 | Olfr1451 | NM_146705.1 | chr19:13073477-13074410 |
| 20887 | Olfr1341 | NM_146853.2 | chr4:118382013-118382952 | | 20982 | Olfr1453 | NM_146700.1 | chr19:13101893-13102817 |
| 20888 | Olfr1342 | NM_146362107-118363055 | chr4:118362107-118363055 | | 20983 | Olfr1454 | NM_146692.1 | chr19:13137902-13138826 |
| 20889 | Olfr1344 | NM_177061.3 | chr7:6392612-6393578 | | 20984 | Olfr1457 | NM_146575.1 | chr19:13169182-13170136 |
| 20890 | Olfr1346 | NM_146916.1 | chr7:6426822-6427764 | | 20985 | Olfr1459 | NM_146689.1 | chr19:13220223-13221147 |
| 20891 | Olfr1347 | NM_146440623-6441583 | chr7:6440623-6441583 | | 20986 | Olfr146 | NM_146747.1 | chr9:38826203-38827124 |
| 20892 | Olfr1348 | NM_146913.1 | chr7:6453996-6454935 | | 20987 | Olfr1461 | NM_146302.1 | chr19:13239505-13240444 |
| 20893 | Olfr1349 | NM_146467184-6468138 | chr7:6467184-6468138 | | 20988 | Olfr1462 | NM_146693.1 | chr19:13265158-13266082 |
| 20894 | Olfr135 | NM_146332.1 | chr17:38345191-38346130 | | 20989 | Olfr1463 | NM_001011840.1 | chr19:13308741-13309674 |
| 20895 | Olfr1350 | NM_146389.1 | chr7:6522703-6523630 | | 20990 | Olfr1465 | NM_001011841.1 | chr19:13387849-13388773 |
| 20896 | Olfr1351 | NM_147040.1 | chr10:78480068-78481028 | | 20991 | Olfr1466 | NM_146694.1 | chr19:13416249-13417182 |
| 20897 | Olfr1352 | NM_147071.2 | chr10:78443794-78447466 | | 20992 | Olfr1467 | NM_146691.1 | chr19:13439119-13440046 |
| 20898 | Olfr1353 | NM_147042.2 | chr10:78426053-78433357 | | 20993 | Olfr1469 | NM_146695.1 | chr19:13485060-13485990 |
| 20899 | Olfr1354 | NM_001199840.1 | chr10:78379586-78380681 | | 20994 | Olfr147 | NM_146869.2 | chr9:38209295-38211414 |
| 20900 | Olfr1355 | NM_207571.1 | chr10:78338293-78342851 | | 20995 | Olfr1471 | NM_207132.1 | chr19:13519503-13520448 |
| 20901 | Olfr1356 | NM_146308.2 | chr10:78309695-78310658 | | 20996 | Olfr1472 | NM_146690.2 | chr19:13528060-13529005 |
| 20902 | Olfr1357 | NM_001011820.1 | chr10:78074413-78080819 | | 20997 | Olfr1474 | NM_001011842.1 | chr19:13545461-13546406 |
| 20903 | Olfr1359 | NM_001011820.1 | chr13:21794871-21795813 | | 20998 | Olfr1475 | NM_146301.1 | chr19:13553741-13554686 |
| 20904 | Olfr1359 | NM_001011820.1 | chr13:21765869-21766849 | | 20999 | Olfr1477 | NM_146696.2 | chr19:13575035-13577782 |
| 20905 | Olfr136 | NM_146807.1 | chr17:38472103-38473042 | | 21000 | Olfr148 | NM_146505.1 | chr9:39421153-39422086 |
| 20906 | Olfr1360 | NM_146543.2 | chr13:21765870-21766849 | | 21001 | Olfr1480 | NM_207575.1 | chr19:13604164-13605112 |
| 20907 | Olfr1361 | NM_146541.2 | chr13:21750236-21751190 | | 21002 | Olfr1484 | NM_146291.1 | chr19:13659795-13660743 |
| 20908 | Olfr1362 | NM_146744.2 | chr13:21702888-21703873 | | 21003 | Olfr1487 | NM_146636.1 | chr19:13693653-13694601 |
| 20909 | Olfr1364 | NM_146540.2 | chr13:21665378-21666323 | | 21004 | Olfr1489 | NM_146635.1 | chr19:13707602-13708544 |
| 20910 | Olfr1366 | NM_146263.2 | chr13:21628842-21629896 | | 21005 | Olfr149 | NM_207138.1 | chr9:39508416-39510352 |
| 20911 | Olfr1367 | NM_146533.1 | chr13:21438798-21439749 | | 21006 | Olfr1490 | NM_001011832.1 | chr19:13728935-13729886 |
| 20912 | Olfr1368 | NM_146534.1 | chr13:21233979-21234924 | | 21007 | Olfr1491 | NM_146345.1 | chr19:13779318-13780278 |
| 20913 | Olfr137 | NM_146488.1 | chr17:38441465-38442404 | | 21008 | Olfr1494 | NM_146990.1 | chr19:13823597-13824545 |
| 20914 | Olfr1370 | NM_146535.1 | chr13:21164217-21165168 | | 21009 | Olfr1495 | NM_146344.1 | chr19:13842833-13843793 |
| 20915 | Olfr1371 | NM_207253.1 | chr11:52026553-52027489 | | 21010 | Olfr1496 | NM_146989.2 | chr19:13855037-13856104 |
| 20916 | Olfr1372-ps1 | NR_034155.1 | chr11:51968377-51971409 | | 21011 | Olfr1497 | NM_146741.1 | chr19:13869154-13870099 |
| 20917 | Olfr1373 | NM_207227.1 | chr11:51958094-51959030 | | 21012 | Olfr1499 | NM_146796.1 | chr19:13889133-13890078 |
| 20918 | Olfr1377 | NM_146911.1 | chr11:50798204-50799128 | | 21013 | Olfr15 | NM_008762.2 | chr16:3838974-3839913 |

Fig. 25 - 112

| | | | | | | | | |
|---|---|---|---|---|---|---|---|---|
| 21014 | Olfr150 | NM_146609.2 | chr9:39544401-39545340 | | 21109 | Olfr251 | NM_207553.2 | chr9:38185467-38186418 |
| 21015 | Olfr1500 | NM_001011831.1 | chr19:13901948-13902884 | | 21110 | Olfr259 | NM_146770.2 | chr2:86947603-86948542 |
| 21016 | Olfr1501 | NM_146633.2 | chr19:13912713-13913661 | | 21111 | Olfr26 | NM_146783.2 | chr9:38662644-38663575 |
| 21017 | Olfr1502 | NM_146797.1 | chr19:13936284-13937235 | | 21112 | Olfr262 | NM_146688.1 | chr19:12315210-12316149 |
| 21018 | Olfr1504 | NM_146634.1 | chr19:13961750-13962698 | | 21113 | Olfr263 | NM_010984.1 | chr13:21224645-21225599 |
| 21019 | Olfr1505 | NM_001011850.1 | chr19:13993511-13994462 | | 21114 | Olfr266 | NM_146489.1 | chr3:106624524-106625475 |
| 21020 | Olfr1507 | NM_001170918.1 | chr14:53109609-53115370 | | 21115 | Olfr267 | NM_146920.2 | chr4:58797650-58798592 |
| 21021 | Olfr1507 | NM_020512.2 | chr14:53109609-53115370 | | 21116 | Olfr27 | NM_146829.2 | chr9:38935752-38952655 |
| 21022 | Olfr1508 | NM_020513.2 | chr14:53082395-53087136 | | 21117 | Olfr270 | NM_146607.1 | chr4:52983500-52984439 |
| 21023 | Olfr1509 | NM_020514.2 | chr14:53070067-53071077 | | 21118 | Olfr272 | NM_146839.1 | chr4:52923704-52924664 |
| 21024 | Olfr151 | NM_207664.2 | chr9:37537561-37538646 | | 21119 | Olfr273 | NM_146824.1 | chr4:52868429-52869383 |
| 21025 | Olfr1510 | NM_146431.2 | chr14:53029563-53030602 | | 21120 | Olfr275 | NM_146858.2 | chr4:52838271-52839230 |
| 21026 | Olfr1511 | NM_146271.2 | chr14:53009489-53010446 | | 21121 | Olfr279 | NM_001001807.1 | chr15:98327904-98328837 |
| 21027 | Olfr1512 | NM_146432.2 | chr14:52991784-52992726 | | 21122 | Olfr281 | NM_146280.1 | chr15:98286742-98287678 |
| 21028 | Olfr1513 | NM_001012269.2 | chr14:52968777-52969719 | | 21123 | Olfr282 | NM_146457.1 | chr15:98267900-98268828 |
| 21029 | Olfr152 | NM_146646.2 | chr2:87622692-87623643 | | 21124 | Olfr283 | NM_147036.1 | chr15:98208809-98209539 |
| 21030 | Olfr153 | NM_206823.1 | chr2:87372191-87373115 | | 21125 | Olfr284 | NM_146281.1 | chr15:98170452-98171370 |
| 21031 | Olfr1532-ps1 | NM_001011542.1 | chr7:114057713-114058637 | | 21126 | Olfr285 | NM_001011778.1 | chr15:98143019-98143979 |
| 21032 | Olfr1535 | NM_207572.1 | chr13:21646908-21647889 | | 21127 | Olfr286 | NM_001011779.1 | chr15:98057105-98064881 |
| 21033 | Olfr1537 | NM_207665.1 | chr9:39045071-39046016 | | 21128 | Olfr287 | NM_001011780.1 | chr15:98037401-98051487 |
| 21034 | Olfr154 | NM_013728.2 | chr2:85503533-85504612 | | 21129 | Olfr288 | NM_001011733.2 | chr15:98016443-98025973 |
| 21035 | Olfr155 | NM_146867.1 | chr4:43867163-43868335 | | 21130 | Olfr290 | NM_146416.2 | chr7:92064290-92065238 |
| 21036 | Olfr156 | NM_019474.2 | chr4:43833206-43834305 | | 21131 | Olfr291 | NM_146415.2 | chr7:92002080-92005828 |
| 21037 | Olfr157 | NM_019475.3 | chr4:43847623-43849389 | | 21132 | Olfr292 | NM_146620.2 | chr7:93836850-93843894 |
| 21038 | Olfr159 | NM_019476.1 | chr4:43782921-43783881 | | 21133 | Olfr293 | NM_001011752.1 | chr7:93812173-93813184 |
| 21039 | Olfr16 | NM_008763.2 | chr1:174886898-174887948 | | 21134 | Olfr294 | NM_001011750.2 | chr7:93764145-93765153 |
| 21040 | Olfr160 | NM_030553.2 | chr9:37518932-37519865 | | 21135 | Olfr295 | NM_146851.2 | chr7:93733786-93734716 |
| 21041 | Olfr161 | NM_146860.1 | chr16:3592397-3593339 | | 21136 | Olfr297 | NM_146618.2 | chr7:93675268-93676201 |
| 21042 | Olfr164 | NM_146451.1 | chr16:19285886-19286834 | | 21137 | Olfr298 | NM_001011751.1 | chr7:93637060-93638059 |
| 21043 | Olfr165 | NM_146466.1 | chr16:19407168-19408110 | | 21138 | Olfr299 | NM_001011767.1 | chr7:93613922-93614915 |
| 21044 | Olfr166 | NM_147068.1 | chr16:19486932-19487871 | | 21139 | Olfr29-ps1 | NR_033638.1 | chr4:43794236-43795199 |
| 21045 | Olfr167 | NM_146935.1 | chr16:19514788-19515727 | | 21140 | Olfr3 | NM_206903.1 | chr2:36667668-36668610 |
| 21046 | Olfr168 | NM_146357.1 | chr16:19530072-19531011 | | 21141 | Olfr30 | NM_146878.2 | chr11:58268416-58269482 |
| 21047 | Olfr169 | NM_001011855.1 | chr16:19566032-19566974 | | 21142 | Olfr301 | NM_212436.2 | chr7:93552358-93561809 |
| 21048 | Olfr17 | NM_020598.2 | chr7:114240980-114241928 | | 21143 | Olfr303 | NM_146619.1 | chr7:93543046-93544006 |
| 21049 | Olfr170 | NM_146957.1 | chr16:19605817-19606759 | | 21144 | Olfr304 | NM_001011828.1 | chr7:93534166-93535168 |
| 21050 | Olfr171 | NM_146958.2 | chr16:19624249-19625194 | | 21145 | Olfr305 | NM_146616.2 | chr7:93511885-93512845 |
| 21051 | Olfr172 | NM_147001.2 | chr16:58760265-58761353 | | 21146 | Olfr307 | NM_146617.1 | chr7:93483962-93484904 |
| 21052 | Olfr173 | NM_147000.2 | chr16:58796574-58797738 | | 21147 | Olfr308 | NM_146621.1 | chr7:93469533-93470460 |
| 21053 | Olfr175-ps1 | NM_147002.2 | chr16:58823606-58826587 | | 21148 | Olfr309 | NM_001011866.1 | chr7:93454694-93455621 |
| 21054 | Olfr176 | NM_146993.1 | chr16:58872041-58872974 | | 21149 | Olfr31 | NM_147027.2 | chr14:15160626-151161580 |
| 21055 | Olfr177 | NM_146996.2 | chr16:58872045-58872974 | | 21150 | Olfr310 | NM_001011520.2 | chr7:93417239-93418321 |
| 21056 | Olfr178 | NM_146997.2 | chr16:58889084-58890044 | | 21151 | Olfr311 | NM_146537.2 | chr11:58654617-58655544 |
| 21057 | Olfr18 | NM_146563.1 | chr9:20118335-20140538 | | 21152 | Olfr312 | NM_001011819.2 | chr11:58644657-58645584 |
| 21058 | Olfr180 | NM_001011662.1 | chr16:58915511-58918312 | | 21153 | Olfr313 | NM_146536.2 | chr11:58630429-58631503 |
| 21059 | Olfr181 | NM_146999.2 | chr16:58925382-58928470 | | 21154 | Olfr314 | NM_001011760.2 | chr11:58599640-58600771 |
| 21060 | Olfr183 | NM_146485.2 | chr16:58995229-59000442 | | 21155 | Olfr315 | NM_146538.2 | chr11:58591590-58592588 |
| 21061 | Olfr186 | NM_146321.1 | chr16:59026801-59027731 | | 21156 | Olfr316 | NM_001011818.2 | chr11:58571168-58572089 |
| 21062 | Olfr187 | NM_146322.2 | chr16:59035605-59039575 | | 21157 | Olfr317 | NM_001011769.2 | chr11:58545597-58546725 |
| 21063 | Olfr19 | NM_146335.1 | chr16:16673142-16674072 | | 21158 | Olfr318 | NM_146501.2 | chr11:58533570-58534596 |
| 21064 | Olfr190 | NM_146397.2 | chr16:59073980-59074904 | | 21159 | Olfr319 | NM_146500.2 | chr11:58515204-58516125 |
| 21065 | Olfr191 | NM_001011807.2 | chr16:59085377-59086307 | | 21160 | Olfr32 | NM_010980.2 | chr2:89978336-89982450 |
| 21066 | Olfr192 | NM_207991.1 | chr16:59087891-59088816 | | 21161 | Olfr320 | NM_207230.1 | chr11:58497376-58498297 |
| 21067 | Olfr193 | NM_001011791.1 | chr16:59109504-59110434 | | 21162 | Olfr322 | NM_207693.1 | chr11:58479062-58480046 |
| 21068 | Olfr194 | NM_001005524.2 | chr16:59118973-59119894 | | 21163 | Olfr323 | NM_146376.2 | chr11:58438574-58439546 |
| 21069 | Olfr195 | NM_146498.1 | chr16:59148677-59149604 | | 21164 | Olfr324 | NM_001011743.2 | chr11:58410846-58411968 |
| 21070 | Olfr196 | NM_146779.2 | chr16:59167037-59167967 | | 21165 | Olfr325 | NM_207153.2 | chr11:58394338-58395379 |
| 21071 | Olfr197 | NM_146484.1 | chr16:59185381-59186307 | | 21166 | Olfr328 | NM_146502.2 | chr11:58364806-58365739 |
| 21072 | Olfr198 | NM_001011808.1 | chr16:59201329-59202250 | | 21167 | Olfr329-ps | NM_001011531.2 | chr11:58355948-58358440 |
| 21073 | Olfr199 | NM_207550.2 | chr16:59215510-59216437 | | 21168 | Olfr33 | NM_147073.1 | chr7:109861968-109862925 |
| 21074 | Olfr2 | NM_010983.1 | chr7:114144388-114146119 | | 21169 | Olfr330 | NM_146879.2 | chr11:58342430-58348327 |
| 21075 | Olfr20 | NM_146923.2 | chr7:73164360-73168201 | | 21170 | Olfr331 | NM_001011861.2 | chr11:58315099-58316056 |
| 21076 | Olfr201 | NM_146994.2 | chr16:59268564-59269491 | | 21171 | Olfr332 | NM_001011770.2 | chr11:58303220-58306001 |
| 21077 | Olfr202 | NM_146995.1 | chr16:59283397-59284321 | | 21172 | Olfr338 | NM_146947.1 | chr2:36232297-36233218 |
| 21078 | Olfr203 | NM_146486.2 | chr16:59302980-59303901 | | 21173 | Olfr339 | NM_146949.1 | chr2:36276919-36277849 |
| 21079 | Olfr204 | NM_146932.2 | chr16:59314313-59315231 | | 21174 | Olfr340 | NM_146951.1 | chr2:36308106-36309045 |
| 21080 | Olfr205 | NM_001011736.1 | chr16:59328415-59329333 | | 21175 | Olfr341 | NM_146950.1 | chr2:36334706-36335648 |
| 21081 | Olfr206 | NM_146991.1 | chr16:59344604-59345525 | | 21176 | Olfr342 | NM_146948.1 | chr2:36382933-36383872 |
| 21082 | Olfr207 | NM_001011792.1 | chr16:59361124-59362042 | | 21177 | Olfr344 | NM_146628.1 | chr2:36424119-36425049 |
| 21083 | Olfr211 | NM_146912.1 | chr6:116443628-116444558 | | 21178 | Olfr345 | NM_146945.1 | chr2:36495560-36496496 |
| 21084 | Olfr212 | NM_001011800.2 | chr6:116456533-116467983 | | 21179 | Olfr346 | NM_146938.1 | chr2:36543523-36544453 |
| 21085 | Olfr213 | NM_001011801.1 | chr6:116490472-116491456 | | 21180 | Olfr347 | NM_146943.1 | chr2:36589842-36590781 |
| 21086 | Olfr214 | NM_146759.1 | chr6:116500644-116507407 | | 21181 | Olfr348 | NM_146944.1 | chr2:36642046-36642988 |
| 21087 | Olfr215 | NM_146446.1 | chr6:116532029-116532962 | | 21182 | Olfr350 | NM_146627.1 | chr2:36705567-36706506 |
| 21088 | Olfr218 | NM_001001809.2 | chr1:175133488-175134430 | | 21183 | Olfr351 | NM_146942.1 | chr2:36714933-36715866 |
| 21089 | Olfr220 | NM_207694.1 | chr17:176378755-176379733 | | 21184 | Olfr352 | NM_146940.1 | chr2:36725087-36726035 |
| 21090 | Olfr221 | NM_001011808.2 | chr14:52654848-52655784 | | 21185 | Olfr353 | NM_146941.1 | chr2:36745430-36746366 |
| 21091 | Olfr222 | NM_001011789.1 | chr11:59384283-59385240 | | 21186 | Olfr354 | NM_146939.1 | chr2:36762467-36763421 |
| 21092 | Olfr223 | NM_146429.1 | chr11:59402629-59403589 | | 21187 | Olfr355 | NM_146625.1 | chr2:36782699-36783632 |
| 21093 | Olfr224 | NM_207695.1 | chr11:58379900-58380845 | | 21188 | Olfr356 | NM_146624.1 | chr2:36792640-36793588 |
| 21094 | Olfr225 | NM_001011740.2 | chr11:59426467-59427727 | | 21189 | Olfr357 | NM_146623.1 | chr2:36852331-36853258 |
| 21095 | Olfr228 | NM_146405.2 | chr2:86322955-86323897 | | 21190 | Olfr358 | NM_207235.1 | chr2:36880139-36881132 |
| 21096 | Olfr229 | NM_146613.1 | chr9:39717389-39718313 | | 21191 | Olfr360 | NM_146622.1 | chr2:36923826-36924780 |
| 21097 | Olfr23 | NM_010970.1 | chr11:73753749-73754727 | | 21192 | Olfr361 | NM_146368.1 | chr2:36940297-36941266 |
| 21098 | Olfr231 | NM_001005520.2 | chr11:176047221-176048145 | | 21193 | Olfr362 | NM_147051.1 | chr2:36960214-36961168 |
| 21099 | Olfr235 | NM_146686.2 | chr19:12342721-12343660 | | 21194 | Olfr365 | NM_146662.1 | chr2:37056762-37057701 |
| 21100 | Olfr237-ps1 | NM_146654.1 | chr6:43103305-43104238 | | 21195 | Olfr366 | NM_001005569.1 | chr2:37075010-37075940 |
| 21101 | Olfr239 | NM_207175.2 | chr17:33336006-33336954 | | 21196 | Olfr367-ps | NM_001081010.2 | chr2:37122470-37126907 |
| 21102 | Olfr24 | NM_146806.1 | chr9:18559135-18560077 | | 21197 | Olfr368 | NM_146374.1 | chr2:37187268-37188252 |
| 21103 | Olfr242 | NM_010974.1 | chr9:38951687-38952603 | | 21198 | Olfr370 | NM_146270.2 | chr8:86064991-86066087 |
| 21104 | Olfr243 | NM_001025386.1 | chr7:110865109-110866060 | | 21199 | Olfr371 | NM_146859.2 | chr8:87754395-87755334 |
| 21105 | Olfr247 | NM_146269.2 | chr10:129411660-129412605 | | 21200 | Olfr372 | NM_207555.2 | chr8:74581558-74582574 |
| 21106 | Olfr247 | NM_146269.2 | chr10:129420535-129421480 | | 21201 | Olfr373 | NM_146539.2 | chr8:74623660-74624605 |
| 21107 | Olfr248 | NM_146714.2 | chr1:176321176-176322186 | | 21202 | Olfr374 | NM_146338.2 | chr8:74630938-74634408 |
| 21108 | Olfr25 | NM_146870.2 | chr9:38137076-38138144 | | 21203 | Olfr376 | NM_001172686.1 | chr11:73184747-73189206 |

Fig. 25 - 113

| | | | | | | | | |
|---|---|---|---|---|---|---|---|---|
| 21204 | Olfr376 | NM_146922.2 | chr11:73184747-73189206 | | 21299 | Olfr498 | NM_146307.2 | chr7:115608839-115609832 |
| 21205 | Olfr378 | NM_147024.2 | chr11:73238538-73241979 | | 21300 | Olfr5 | NM_146914.2 | chr7:6432926-6439524 |
| 21206 | Olfr38 | NM_148986.1 | chr6:42712052-42713006 | | 21301 | Olfr50 | NM_146946.1 | chr2:36648757-36649696 |
| 21207 | Olfr380 | NM_147025.1 | chr11:73266778-73267712 | | 21302 | Olfr502 | NM_146739.1 | chr7:115666517-115667462 |
| 21208 | Olfr381 | NM_147023.1 | chr11:73299388-73300324 | | 21303 | Olfr503 | NM_001011527.1 | chr7:115688040-115689012 |
| 21209 | Olfr382 | NM_146443.1 | chr11:73329760-73330699 | | 21304 | Olfr504 | NM_001011858.1 | chr7:115708350-115709307 |
| 21210 | Olfr384 | NM_207224.1 | chr11:73416083-73417022 | | 21305 | Olfr506 | NM_001011871.1 | chr7:115755822-115756767 |
| 21211 | Olfr385 | NM_147023.1 | chr11:73402299-73403238 | | 21306 | Olfr507 | NM_146743.1 | chr7:115765327-115766278 |
| 21212 | Olfr389 | NM_147009.3 | chr11:73589888-73594091 | | 21307 | Olfr508 | NM_146773.1 | chr7:115773507-115774440 |
| 21213 | Olfr39 | NM_146825.2 | chr9:20086794-20091092 | | 21308 | Olfr509 | NM_146372.1 | chr7:115789122-115790088 |
| 21214 | Olfr390 | NM_146347.1 | chr11:73600441-73601377 | | 21309 | Olfr51 | NM_146909.1 | chr11:50820475-50821399 |
| 21215 | Olfr391-ps | NM_001159775.1 | chr11:73612254-73616486 | | 21310 | Olfr510 | NM_146311.1 | chr7:115810931-115811876 |
| 21216 | Olfr392 | NM_147006.2 | chr11:73627643-73630379 | | 21311 | Olfr512 | NM_146724.1 | chr7:115856868-115857849 |
| 21217 | Olfr393 | NM_147008.2 | chr11:73660686-73661625 | | 21312 | Olfr513 | NM_146723.1 | chr7:115898371-115899301 |
| 21218 | Olfr394 | NM_147007.1 | chr11:73700939-73701872 | | 21313 | Olfr514 | NM_146726.1 | chr7:115968578-115969511 |
| 21219 | Olfr395 | NM_147005.1 | chr11:73720053-73720992 | | 21314 | Olfr516 | NM_146725.1 | chr7:115988577-115989522 |
| 21220 | Olfr397 | NM_146346.1 | chr11:73778111-73779059 | | 21315 | Olfr517 | NM_001011846.1 | chr7:116011721-116012666 |
| 21221 | Olfr398 | NM_146710.1 | chr11:73797163-73798108 | | 21316 | Olfr518 | NM_146306.1 | chr7:116024116-116025118 |
| 21222 | Olfr399 | NM_147004.2 | chr11:73867277-73868280 | | 21317 | Olfr519 | NM_207160.1 | chr7:116036974-116037919 |
| 21223 | Olfr401 | NM_146706.1 | chr11:73934792-73935740 | | 21318 | Olfr52 | NM_146583.1 | chr2:86021306-86022266 |
| 21224 | Olfr402 | NM_146708.1 | chr11:73968657-73969605 | | 21319 | Olfr520 | NM_147063.2 | chr7:106883654-106884605 |
| 21225 | Olfr403 | NM_207622.1 | chr11:74009006-74009948 | | 21320 | Olfr521 | NM_146356.2 | chr7:106915673-106916639 |
| 21226 | Olfr406 | NM_001011863.1 | chr11:74082892-74083864 | | 21321 | Olfr522 | NM_146952.1 | chr7:147347908-147348847 |
| 21227 | Olfr410 | NM_146707.1 | chr11:74147783-74148731 | | 21322 | Olfr523 | NM_146518.1 | chr7:147362002-147362956 |
| 21228 | Olfr411 | NM_146709.1 | chr11:74160125-74161174 | | 21323 | Olfr524 | NM_001011814.1 | chr7:147387710-147388667 |
| 21229 | Olfr412 | NM_001011851.1 | chr11:74178172-74179111 | | 21324 | Olfr525 | NM_146956.1 | chr7:147508599-147509529 |
| 21230 | Olfr414 | NM_146761.2 | chr1:176360560-176361515 | | 21325 | Olfr527 | NM_001011776.1 | chr7:147521762-147522680 |
| 21231 | Olfr417 | NM_207137.3 | chr1:176299049-176299979 | | 21326 | Olfr53 | NM_146960.2 | chr7:147832350-147838818 |
| 21232 | Olfr418-ps1 | NM_146651.1 | chr1:175200277-175201268 | | 21327 | Olfr530 | NM_146519.1 | chr7:147558583-147559507 |
| 21233 | Olfr419 | NM_146715.2 | chr1:176180019-176181107 | | 21328 | Olfr531 | NM_146953.1 | chr7:147586028-147586943 |
| 21234 | Olfr420 | NM_146305.2 | chr1:176088852-176089898 | | 21329 | Olfr532 | NM_147026.1 | chr7:147604740-147605670 |
| 21235 | Olfr421-ps1 | NR_046667.1 | chr1:176081611-176082661 | | 21330 | Olfr533 | NM_001011815.1 | chr7:147652101-147653064 |
| 21236 | Olfr424 | NM_146721.1 | chr1:176066876-176067824 | | 21331 | Olfr535 | NM_146954.1 | chr7:147678538-147679477 |
| 21237 | Olfr426 | NM_001206926.1 | chr1:176029591-176030541 | | 21332 | Olfr536 | NM_146520.2 | chr7:147686251-147693217 |
| 21238 | Olfr427 | NM_207158.1 | chr1:176029591-176030538 | | 21333 | Olfr538 | NM_001011867.1 | chr7:147760053-147760986 |
| 21239 | Olfr429 | NM_146722.2 | chr1:176019168-176020111 | | 21334 | Olfr539 | NM_146961.1 | chr7:147853187-147854147 |
| 21240 | Olfr43 | NM_146711.2 | chr11:74019699-74020791 | | 21335 | Olfr54 | NM_010997.1 | chr11:50840505-50841447 |
| 21241 | Olfr430 | NM_146718.2 | chr1:175999430-176000384 | | 21336 | Olfr541 | NM_146962.1 | chr7:147890151-147891090 |
| 21242 | Olfr432 | NM_146716.2 | chr1:175980505-175981444 | | 21337 | Olfr543 | NM_001011782.2 | chr7:109625286-109626416 |
| 21243 | Olfr433 | NM_146717.2 | chr1:175972063-175973067 | | 21338 | Olfr544 | NM_020289.2 | chr7:109632627-109636821 |
| 21244 | Olfr434 | NM_146369.1 | chr6:43166913-43167879 | | 21339 | Olfr545 | NM_146840.1 | chr7:109642336-109643287 |
| 21245 | Olfr435 | NM_146653.1 | chr6:43151644-43152586 | | 21340 | Olfr547 | NM_147079.2 | chr7:109683262-109684202 |
| 21246 | Olfr437 | NM_146296.1 | chr6:43117058-43117991 | | 21341 | Olfr549 | NM_147101.2 | chr7:109702799-109703750 |
| 21247 | Olfr44 | NM_146830.1 | chr9:39291788-39301573 | | 21342 | Olfr55 | NM_010998.2 | chr17:33313360-33314308 |
| 21248 | Olfr441 | NM_146655.1 | chr6:43065742-43066675 | | 21343 | Olfr550 | NM_147104.2 | chr7:109726982-109728020 |
| 21249 | Olfr444 | NM_146656.1 | chr6:42905498-42906431 | | 21344 | Olfr551 | NM_146755.2 | chr7:109736254-109737333 |
| 21250 | Olfr446 | NM_146295.1 | chr6:42877231-42878158 | | 21345 | Olfr552 | NM_147102.2 | chr7:109752869-109753823 |
| 21251 | Olfr447 | NM_146988.1 | chr6:42861523-42862456 | | 21346 | Olfr553 | NM_207621.1 | chr7:109762520-109763501 |
| 21252 | Olfr448 | NM_146273.1 | chr6:42846451-42847384 | | 21347 | Olfr554 | NM_146325.2 | chr7:109788761-109789715 |
| 21253 | Olfr449 | NM_147064.1 | chr6:42787881-42788817 | | 21348 | Olfr555 | NM_147103.2 | chr7:109807336-109808284 |
| 21254 | Olfr45 | NM_146963.1 | chr7:147876805-147877741 | | 21349 | Olfr556 | NM_146754.2 | chr7:109818414-109819437 |
| 21255 | Olfr450 | NM_146445.1 | chr6:42767471-42768404 | | 21350 | Olfr557 | NM_146361.2 | chr7:109846729-109847786 |
| 21256 | Olfr452 | NM_001011869.1 | chr6:42740039-42740993 | | 21351 | Olfr558 | NM_147093.3 | chr7:109858036-109860568 |
| 21257 | Olfr453 | NM_001011799.1 | chr6:42694037-42694991 | | 21352 | Olfr559 | NM_147112.2 | chr7:109872045-109873002 |
| 21258 | Olfr455 | NM_001081301.2 | chr6:42488065-42489019 | | 21353 | Olfr56 | NM_010999.2 | chr11:488864235-48948889 |
| 21259 | Olfr456 | NM_001011528.2 | chr6:42436161-42437213 | | 21354 | Olfr560 | NM_147113.2 | chr7:109901497-109902441 |
| 21260 | Olfr457 | NM_146987.1 | chr6:42421233-42422175 | | 21355 | Olfr561 | NM_147092.1 | chr7:109923039-109923984 |
| 21261 | Olfr458 | NM_146444.1 | chr6:42410074-42411016 | | 21356 | Olfr564 | NM_146359.2 | chr7:109951993-109952944 |
| 21262 | Olfr459 | NM_146576.1 | chr6:41721352-41722296 | | 21357 | Olfr568 | NM_001011536.1 | chr7:110004834-110005785 |
| 21263 | Olfr46 | NM_146934.2 | chr7:147787238-147797023 | | 21358 | Olfr568 | NM_147091.1 | chr7:110025635-110026577 |
| 21264 | Olfr460 | NM_146383.1 | chr6:40521386-40522331 | | 21359 | Olfr569 | NM_147088.1 | chr7:110035720-110036665 |
| 21265 | Olfr461 | NM_148382.1 | chr6:40494034-40494976 | | 21360 | Olfr57 | NM_147041.2 | chr10:78497467-78498547 |
| 21266 | Olfr462 | NM_146411.2 | chr11:87702460-87703396 | | 21361 | Olfr570 | NM_147110.1 | chr7:110048882-110049821 |
| 21267 | Olfr463 | NM_146413.2 | chr11:87706488-87707424 | | 21362 | Olfr571 | NM_147085.2 | chr7:110057382-110058351 |
| 21268 | Olfr464 | NM_146412.2 | chr11:87727421-87728505 | | 21363 | Olfr572 | NM_147089.2 | chr7:110076143-110077100 |
| 21269 | Olfr466 | NM_148819.2 | chr13:65253533-65254460 | | 21364 | Olfr574 | NM_146360.2 | chr7:110096980-110098021 |
| 21270 | Olfr467 | NM_001005488.1 | chr7:114958099-114959020 | | 21365 | Olfr575 | NM_147114.2 | chr7:110103177-110104134 |
| 21271 | Olfr469 | NM_146426.1 | chr7:114966036-114966981 | | 21366 | Olfr576 | NM_001001805.2 | chr7:110113615-110114554 |
| 21272 | Olfr47 | NM_146370.1 | chr6:43185608-43186574 | | 21367 | Olfr577 | NM_147109.1 | chr7:110121565-110122504 |
| 21273 | Olfr470 | NM_146425.1 | chr7:114988300-114989245 | | 21368 | Olfr578 | NM_147115.1 | chr7:110132734-110133676 |
| 21274 | Olfr472 | NM_146774.1 | chr7:115046232-115047165 | | 21369 | Olfr58 | NM_011001.2 | chr9:19584726-19588508 |
| 21275 | Olfr473 | NM_146775.1 | chr7:115077035-115077968 | | 21370 | Olfr582 | NM_147053.1 | chr7:110189994-110190954 |
| 21276 | Olfr474 | NM_146949.1 | chr7:115098156-115099089 | | 21371 | Olfr583 | NM_146757.1 | chr7:110199813-110200773 |
| 21277 | Olfr476 | NM_146924.1 | chr7:115110912-115111845 | | 21372 | Olfr584 | NM_147054.1 | chr7:110234033-110234993 |
| 21278 | Olfr477 | NM_146926.1 | chr7:115133880-115134813 | | 21373 | Olfr585 | NM_147087.2 | chr7:110246256-110247213 |
| 21279 | Olfr478 | NM_146734.1 | chr7:115174910-115175855 | | 21374 | Olfr586 | NM_147111.1 | chr7:110270342-110271296 |
| 21280 | Olfr479 | NM_001011742.1 | chr7:115198497-115199481 | | 21375 | Olfr589 | NM_147052.1 | chr7:110303305-110304259 |
| 21281 | Olfr48 | NM_010990.1 | chr2:89684222-89685128 | | 21376 | Olfr59 | NM_011002.2 | chr11:74097310-74103148 |
| 21282 | Olfr480 | NM_020029.1 | chr7:115209281-115210310 | | 21377 | Olfr591 | NM_001011847.1 | chr7:110321204-110322149 |
| 21283 | Olfr481 | NM_146925.1 | chr7:115224309-115225248 | | 21378 | Olfr592 | NM_207556.2 | chr7:110335116-110336055 |
| 21284 | Olfr482 | NM_146733.1 | chr7:115238110-115239082 | | 21379 | Olfr593 | NM_146380.1 | chr7:110360375-110361359 |
| 21285 | Olfr483 | NM_146735.1 | chr7:115246824-115247772 | | 21380 | Olfr594 | NM_207143.1 | chr7:110368233-110369169 |
| 21286 | Olfr484 | NM_146499.1 | chr7:115267809-115268775 | | 21381 | Olfr596 | NM_001190381.1 | chr7:110458236-110459175 |
| 21287 | Olfr485 | NM_001011810.2 | chr7:115302431-115303385 | | 21382 | Olfr597 | NM_001011845.2 | chr7:110468926-110469874 |
| 21288 | Olfr486 | NM_146496.1 | chr7:115315311-115316256 | | 21383 | Olfr598 | NM_001011793.1 | chr7:110477001-110477961 |
| 21289 | Olfr487 | NM_001011811.1 | chr7:115355096-115356041 | | 21384 | Olfr599 | NM_146731.1 | chr7:110486569-110487517 |
| 21290 | Olfr488 | NM_146732.1 | chr7:115398705-115399650 | | 21385 | Olfr6 | NM_206897.2 | chr7:114099497-114100448 |
| 21291 | Olfr49 | NM_010991.2 | chr14:54901570-54902600 | | 21386 | Olfr60 | NM_146955.1 | chr7:147530950-147531886 |
| 21292 | Olfr490 | NM_146498.1 | chr7:115429693-115430638 | | 21387 | Olfr600 | NM_147046.2 | chr7:110494495-110495440 |
| 21293 | Olfr491 | NM_146736.1 | chr7:115460409-115461342 | | 21388 | Olfr601 | NM_146314.2 | chr7:110506737-110507727 |
| 21294 | Olfr492 | NM_146497.1 | chr7:115466243-115467188 | | 21389 | Olfr603 | NM_147070.2 | chr7:110531575-110532514 |
| 21295 | Olfr493 | NM_146310.1 | chr7:115489548-115490493 | | 21390 | Olfr605 | NM_001011854.2 | chr7:110590653-110591664 |
| 21296 | Olfr494 | NM_146737.1 | chr7:115511905-115511950 | | 21391 | Olfr606 | NM_147094.1 | chr7:110599852-110600812 |
| 21297 | Olfr495 | NM_146364.1 | chr7:115538635-115539628 | | 21392 | Olfr608 | NM_146756.2 | chr7:110618554-110619505 |
| 21298 | Olfr497 | NM_146738.1 | chr7:115566086-115567031 | | 21393 | Olfr609 | NM_147082.2 | chr7:110640430-110641390 |

Fig. 25 - 114

| | | | | | | | | |
|---|---|---|---|---|---|---|---|---|
| 21394 | Olfr61 | NM_146964.1 | chr7:147823601-147824537 | | 21489 | Olfr715 | NM_146780.2 | chr7:114271865-114272996 |
| 21395 | Olfr610 | NM_147081.2 | chr7:110654510-110655458 | | 21490 | Olfr716 | NM_146604.1 | chr7:114290831-114291776 |
| 21396 | Olfr611 | NM_146727.2 | chr7:110665924-110666896 | | 21491 | Olfr720 | NM_146392.1 | chr14:15007643-15008594 |
| 21397 | Olfr612 | NM_001200027.1 | chr7:110686774-110687746 | | 21492 | Olfr722 | NM_146494.2 | chr14:50513932-50521616 |
| 21398 | Olfr613 | NM_147100.3 | chr7:110698881-110704018 | | 21493 | Olfr723 | NM_001011530.2 | chr14:50548237-50549243 |
| 21399 | Olfr615 | NM_147080.2 | chr7:110708992-110709934 | | 21494 | Olfr724 | NM_146492.2 | chr14:50579765-50580771 |
| 21400 | Olfr616 | NM_147099.2 | chr7:110711837-110713791 | | 21495 | Olfr725 | NM_146317.2 | chr14:50654065-50655175 |
| 21401 | Olfr617 | NM_146841.1 | chr7:110732537-110733494 | | 21496 | Olfr726 | NM_146316.2 | chr14:50703388-50704354 |
| 21402 | Olfr618 | NM_147047.2 | chr7:110745831-110746788 | | 21497 | Olfr727 | NM_146319.2 | chr14:50746227-50747262 |
| 21403 | Olfr619 | NM_147076.2 | chr7:110752102-110753225 | | 21498 | Olfr728 | NM_001011809.1 | chr14:50759376-50760312 |
| 21404 | Olfr62 | NM_146315.2 | chr4:118338123-118339071 | | 21499 | Olfr729 | NM_146278.1 | chr14:50767575-50768547 |
| 21405 | Olfr620 | NM_146812.2 | chr7:110759923-110760865 | | 21500 | Olfr73 | NM_054090.1 | chr2:87874352-87875294 |
| 21406 | Olfr622 | NM_147083.1 | chr7:110787698-110788652 | | 21501 | Olfr730 | NM_146493.2 | chr14:50805936-50806893 |
| 21407 | Olfr623 | NM_147122.2 | chr7:110808757-110809832 | | 21502 | Olfr731 | NM_146363.2 | chr14:50857577-50858558 |
| 21408 | Olfr624 | NM_001011865.2 | chr7:110818616-110819543 | | 21503 | Olfr732 | NM_146665.2 | chr14:50900902-50901946 |
| 21409 | Olfr628 | NM_147097.2 | chr7:110880441-110881392 | | 21504 | Olfr733 | NM_146663.1 | chr14:50918011-50919005 |
| 21410 | Olfr629 | NM_146821.2 | chr7:110888714-110889836 | | 21505 | Olfr734 | NM_146664.1 | chr14:50939566-50940508 |
| 21411 | Olfr63 | NM_146937.1 | chr17:33405670-33406621 | | 21506 | Olfr735 | NM_001011754.2 | chr14:50965050-50966115 |
| 21412 | Olfr630 | NM_147098.2 | chr7:110902663-110905864 | | 21507 | Olfr736 | NM_146666.1 | chr14:51012432-51013371 |
| 21413 | Olfr631 | NM_001271020.1 | chr7:111063575-111078425 | | 21508 | Olfr738 | NM_146420.2 | chr14:51033220-51034156 |
| 21414 | Olfr631 | NM_146959.2 | chr7:111063575-111078425 | | 21509 | Olfr739 | NM_146668.2 | chr14:51044195-51045125 |
| 21415 | Olfr632 | NM_147085.1 | chr7:111085895-111086849 | | 21510 | Olfr74 | NM_054091.2 | chr2:87813863-87814820 |
| 21416 | Olfr633 | NM_146354.1 | chr7:111095081-111096020 | | 21511 | Olfr740 | NM_146667.1 | chr14:51072728-51073664 |
| 21417 | Olfr635 | NM_147118.2 | chr7:111127689-111128655 | | 21512 | Olfr741 | NM_207133.2 | chr14:51092731-51106070 |
| 21418 | Olfr638 | NM_147120.1 | chr7:111151772-111152738 | | 21513 | Olfr742 | NM_146430.2 | chr14:51134796-51135915 |
| 21419 | Olfr639 | NM_147084.1 | chr7:111160263-111161214 | | 21514 | Olfr743 | NM_001177508.1 | chr14:51153088-51154024 |
| 21420 | Olfr64 | NM_013617.3 | chr7:111041323-111042985 | | 21515 | Olfr744 | NM_001011738.1 | chr14:51237898-51238870 |
| 21421 | Olfr640 | NM_146822.2 | chr7:111169885-111170830 | | 21516 | Olfr745 | NM_146299.2 | chr14:51261869-51263044 |
| 21422 | Olfr641 | NM_147072.1 | chr7:111188311-111189250 | | 21517 | Olfr746 | NM_146298.2 | chr14:51272913-51273858 |
| 21423 | Olfr642 | NM_146329.1 | chr7:111197921-111198866 | | 21518 | Olfr747 | NM_207156.2 | chr14:51300365-51301320 |
| 21424 | Olfr643 | NM_147077.1 | chr7:111207169-111208114 | | 21519 | Olfr748 | NM_001011837.2 | chr14:51330006-51330930 |
| 21425 | Olfr644 | NM_147121.1 | chr7:111216598-111217543 | | 21520 | Olfr749 | NM_020288.2 | chr14:51355893-51363999 |
| 21426 | Olfr645 | NM_207144.1 | chr7:111232644-111233592 | | 21521 | Olfr750 | NM_207558.2 | chr14:51689985-51691117 |
| 21427 | Olfr646 | NM_147056.1 | chr7:111254794-111255733 | | 21522 | Olfr75-ps1 | NR_002859.2 | chr11:73218951-73223360 |
| 21428 | Olfr648 | NM_146751.1 | chr7:111327969-111328920 | | 21523 | Olfr75-ps1 | NR_033528.1 | chr11:73218951-73223360 |
| 21429 | Olfr649 | NM_147055.1 | chr7:111337780-111338719 | | 21524 | Olfr76 | NM_146682.1 | chr19:12194210-12195164 |
| 21430 | Olfr65 | NM_013616.4 | chr7:111054855-111055961 | | 21525 | Olfr761 | NM_001011829.1 | chr17:38088995-38089967 |
| 21431 | Olfr651 | NM_146813.2 | chr7:111701397-111702466 | | 21526 | Olfr763 | NM_146862.1 | chr10:128448342-128449272 |
| 21432 | Olfr652 | NM_147049.2 | chr7:111712665-111713726 | | 21527 | Olfr765 | NM_001085477.1 | chr10:128483187-128484117 |
| 21433 | Olfr653 | NM_147074.2 | chr7:111728137-111729183 | | 21528 | Olfr767 | NM_146318.2 | chr10:128516087-128517017 |
| 21434 | Olfr654 | NM_146379.1 | chr7:111736268-111737294 | | 21529 | Olfr768 | NM_146864.1 | chr10:128530089-128531028 |
| 21435 | Olfr655 | NM_146820.2 | chr7:111744766-111745693 | | 21530 | Olfr769 | NM_146267.1 | chr10:128548540-128549479 |
| 21436 | Olfr656 | NM_147075.1 | chr7:111766170-111767160 | | 21531 | Olfr77 | NM_146339.3 | chr9:19721672-19726954 |
| 21437 | Olfr657 | NM_146312.2 | chr7:111784189-111785149 | | 21532 | Olfr770 | NM_146863.1 | chr10:128569886-128570822 |
| 21438 | Olfr658 | NM_147049.4 | chr7:111791393-111795819 | | 21533 | Olfr771 | NM_146547.1 | chr10:128597084-128598038 |
| 21439 | Olfr659 | NM_147050.1 | chr7:111819217-111820186 | | 21534 | Olfr772 | NM_146266.2 | chr10:128611106-128612110 |
| 21440 | Olfr66 | NM_013618.3 | chr7:111029819-111030755 | | 21535 | Olfr773 | NM_207008.2 | chr10:128623539-128624475 |
| 21441 | Olfr661 | NM_146748.1 | chr7:111836530-111837490 | | 21536 | Olfr774 | NM_207620.1 | chr10:128675206-128676145 |
| 21442 | Olfr663 | NM_001011757.1 | chr7:111852082-111853117 | | 21537 | Olfr775 | NM_146545.2 | chr10:128687591-128688530 |
| 21443 | Olfr665 | NM_146814.1 | chr7:112029222-112030173 | | 21538 | Olfr776 | NM_207559.1 | chr10:128698018-128698957 |
| 21444 | Olfr666 | NM_147096.1 | chr7:112041183-112042140 | | 21539 | Olfr777 | NM_146544.1 | chr10:128705441-128706377 |
| 21445 | Olfr667 | NM_147060.2 | chr7:112064827-112065808 | | 21540 | Olfr78 | NM_001168503.1 | chr7:109889234-109907985 |
| 21446 | Olfr668 | NM_147059.1 | chr7:112073319-112074276 | | 21541 | Olfr78 | NM_130866.4 | chr7:109889234-109907985 |
| 21447 | Olfr669 | NM_147043.1 | chr7:112087041-112087995 | | 21542 | Olfr780 | NM_146284.1 | chr10:128758680-128759619 |
| 21448 | Olfr67 | NM_013619.3 | chr7:110935725-110940344 | | 21543 | Olfr781 | NM_146728.1 | chr10:128769938-128770874 |
| 21449 | Olfr670 | NM_207146.1 | chr7:112109244 | | 21544 | Olfr782 | NM_001011797.1 | chr10:128787620-128788565 |
| 21450 | Olfr671 | NM_001011755.1 | chr7:112123555-112124497 | | 21545 | Olfr784 | NM_146729.1 | chr10:128824690-128825650 |
| 21451 | Olfr672 | NM_146760.1 | chr7:112144477-112145416 | | 21546 | Olfr786 | NM_146549.1 | chr10:128873869-128748808 |
| 21452 | Olfr675 | NM_001011848.1 | chr7:112172538-112173480 | | 21547 | Olfr787 | NM_001011822.1 | chr10:128899733-128900672 |
| 21453 | Olfr676 | NM_147095.1 | chr7:112183713-112184667 | | 21548 | Olfr788 | NM_146551.1 | chr10:128909749-128910685 |
| 21454 | Olfr677 | NM_146358.1 | chr7:112204761-112205700 | | 21549 | Olfr790 | NM_146933.1 | chr10:128937941-128938910 |
| 21455 | Olfr678 | NM_146758.1 | chr7:112217982-112218924 | | 21550 | Olfr791 | NM_146930.1 | chr10:128963284-128964223 |
| 21456 | Olfr679 | NM_147044.1 | chr7:112234231-112235179 | | 21551 | Olfr792 | NM_001011849.1 | chr10:128977594-128978530 |
| 21457 | Olfr68 | NM_013620.2 | chr7:110925909-110926857 | | 21552 | Olfr794 | NM_146378.1 | chr10:129007712-129008675 |
| 21458 | Olfr681 | NM_207557.2 | chr7:112269972-112270920 | | 21553 | Olfr796 | NM_146931.1 | chr10:129044602-129045555 |
| 21459 | Olfr683 | NM_147045.1 | chr7:112291863-112292823 | | 21554 | Olfr798 | NM_146556.2 | chr10:129062179-129063115 |
| 21460 | Olfr684 | NM_207249.1 | chr7:112305255-112306194 | | 21555 | Olfr799 | NM_146927.1 | chr10:129084185-129085121 |
| 21461 | Olfr685 | NM_001011857.1 | chr7:112328874-112329825 | | 21556 | Olfr8 | NM_207201.1 | chr10:78417951-78418884 |
| 21462 | Olfr686 | NM_147069.1 | chr7:112351901-112352855 | | 21557 | Olfr800 | NM_146548.1 | chr10:129096863-129097799 |
| 21463 | Olfr688 | NM_001011533.2 | chr7:112436608-112437574 | | 21558 | Olfr801 | NM_146285.1 | chr10:129106616-129107573 |
| 21464 | Olfr689 | NM_146750.1 | chr7:112462519-112463482 | | 21559 | Olfr802 | NM_146932.1 | chr10:129118854-129119793 |
| 21465 | Olfr69 | NM_013621.3 | chr7:110915790-110920108 | | 21560 | Olfr803 | NM_146554.1 | chr10:129128168-129129095 |
| 21466 | Olfr690 | NM_020290.2 | chr7:112477730-112478792 | | 21561 | Olfr804 | NM_001011821.1 | chr10:129141935-129142880 |
| 21467 | Olfr691 | NM_147061.1 | chr7:112485259-112486228 | | 21562 | Olfr805 | NM_146555.1 | chr10:129159638-129160598 |
| 21468 | Olfr692 | NM_146355.1 | chr7:112516841-112517831 | | 21563 | Olfr806 | NM_146553.1 | chr10:129175029-129175971 |
| 21469 | Olfr693 | NM_146453.2 | chr7:113821047-113821999 | | 21564 | Olfr807 | NM_146929.1 | chr10:129191568-129192504 |
| 21470 | Olfr694 | NM_146452.2 | chr7:113832295-113833243 | | 21565 | Olfr808 | NM_146928.1 | chr10:129204553-129205492 |
| 21471 | Olfr695 | NM_146598.2 | chr7:113857245-113859859 | | 21566 | Olfr809 | NM_146324.1 | chr10:129212926-129213913 |
| 21472 | Olfr697 | NM_146599.2 | chr7:113884421-113885470 | | 21567 | Olfr810 | NM_146550.1 | chr10:129227704-129228643 |
| 21473 | Olfr698 | NM_146602.2 | chr7:113895964-113896900 | | 21568 | Olfr811 | NM_146552.1 | chr10:129238619-129239579 |
| 21474 | Olfr699 | NM_001011862.1 | chr7:113933562-113934513 | | 21569 | Olfr812 | NM_146795.1 | chr10:129279163-129280096 |
| 21475 | Olfr70 | NM_019485.2 | chr4:43707871-43713679 | | 21570 | Olfr813 | NM_207147.1 | chr10:129293575-129294508 |
| 21476 | Olfr700 | NM_146600.1 | chr7:113949023-113949974 | | 21571 | Olfr814 | NM_207159.1 | chr10:129310878-129311811 |
| 21477 | Olfr701 | NM_028910.3 | chr7:113957697-113964223 | | 21572 | Olfr815 | NM_146670.1 | chr10:129338831-129339782 |
| 21478 | Olfr702 | NM_146597.2 | chr7:113967002-113970257 | | 21573 | Olfr816 | NM_146672.1 | chr10:129348393-129349332 |
| 21479 | Olfr703 | NM_146596.1 | chr7:113988126-113989086 | | 21574 | Olfr818 | NM_146777.1 | chr10:129382159-129383116 |
| 21480 | Olfr704 | NM_001011749.1 | chr7:114008495-114009443 | | 21575 | Olfr819 | NM_001165944.1 | chr10:129402791-129403759 |
| 21481 | Olfr705 | NM_147032.2 | chr7:114016806-114017757 | | 21576 | Olfr820 | NM_146675.1 | chr10:129454418-129455357 |
| 21482 | Olfr706 | NM_146353.2 | chr7:114029378-114030329 | | 21577 | Olfr821 | NM_146776.1 | chr10:129470683-129471616 |
| 21483 | Olfr707 | NM_001005570.2 | chr7:114034697-114035621 | | 21578 | Olfr822 | NM_146671.1 | chr10:129511467-129512406 |
| 21484 | Olfr71 | NM_019486.1 | chr4:43718499-43719438 | | 21579 | Olfr823 | NM_146673.2 | chr10:129548896-129549844 |
| 21485 | Olfr710 | NM_146601.1 | chr7:114087580-114091826 | | 21580 | Olfr824 | NM_146674.1 | chr10:129563163-129564111 |
| 21486 | Olfr711 | NM_146035.2 | chr7:114114881-114118965 | | 21581 | Olfr825 | NM_146677.1 | chr10:129599417-129600380 |
| 21487 | Olfr713 | NM_147034.1 | chr7:114179649-114180624 | | 21582 | Olfr826 | NM_146676.1 | chr10:129616992-129617934 |
| 21488 | Olfr714 | NM_147033.2 | chr7:114217343-114218297 | | 21583 | Olfr827 | NM_146300.1 | chr10:129647215-129648184 |

Fig. 25 - 115

| | | | |
|---|---|---|---|
| 21584 | Olfr828 | NM_146605.1 | chr9:18619797-18620736 |
| 21585 | Olfr829 | NM_147067.1 | chr9:18661070-18662036 |
| 21586 | Olfr830 | NM_146566.1 | chr9:18679772-18680720 |
| 21587 | Olfr832 | NM_001011824.1 | chr9:18749093-18750032 |
| 21588 | Olfr834 | NM_001011823.1 | chr9:18792433-18793372 |
| 21589 | Olfr835 | NM_001012266.1 | chr9:18839568-18840504 |
| 21590 | Olfr836 | NM_146564.2 | chr9:18925400-18926355 |
| 21591 | Olfr837 | NM_146565.2 | chr9:18941371-18942411 |
| 21592 | Olfr843 | NM_146567.1 | chr9:19052800-19053907 |
| 21593 | Olfr845 | NM_207145.2 | chr9:19142902-19143844 |
| 21594 | Olfr846 | NM_146282.2 | chr9:19164858-19165800 |
| 21595 | Olfr847 | NM_146525.1 | chr9:19179384-19180323 |
| 21596 | Olfr849 | NM_146527.1 | chr9:19245358-19246297 |
| 21597 | Olfr850 | NM_146523.1 | chr9:19281744-19282692 |
| 21598 | Olfr851 | NM_146905.2 | chr9:19301193-19302132 |
| 21599 | Olfr853 | NM_146906.1 | chr9:19341454-19342372 |
| 21600 | Olfr854 | NM_146522.1 | chr9:19370878-19371826 |
| 21601 | Olfr855 | NM_146524.2 | chr9:19388954-19389946 |
| 21602 | Olfr856-ps1 | NR_033621.1 | chr9:19461482-19463124 |
| 21603 | Olfr857 | NM_001012265.1 | chr9:19517272-19518202 |
| 21604 | Olfr859 | NM_146526.2 | chr9:19612763-19613693 |
| 21605 | Olfr860 | NM_146528.2 | chr9:19650066-19654191 |
| 21606 | Olfr862 | NM_146562.1 | chr9:19687826-19688747 |
| 21607 | Olfr866 | NM_146558.2 | chr9:19831402-19832479 |
| 21608 | Olfr867 | NM_001011748.1 | chr9:19858909-19859905 |
| 21609 | Olfr868 | NM_146559.2 | chr9:19903089-19906134 |
| 21610 | Olfr869 | NM_146557.2 | chr9:19933563-19942533 |
| 21611 | Olfr870 | NM_146904.1 | chr9:19975077-19976013 |
| 21612 | Olfr871 | NM_146903.2 | chr9:20016650-20017797 |
| 21613 | Olfr872 | NM_146560.2 | chr9:20041605-20065357 |
| 21614 | Olfr873 | NM_146561.1 | chr9:20104654-20105614 |
| 21615 | Olfr874 | NM_146882.2 | chr9:37553720-37554653 |
| 21616 | Olfr875 | NM_146749.2 | chr9:37580221-37581225 |
| 21617 | Olfr876 | NM_146883.2 | chr9:37611473-37612521 |
| 21618 | Olfr877 | NM_146417.1 | chr9:37662404-37663340 |
| 21619 | Olfr878 | NM_146798.2 | chr9:37726132-37727197 |
| 21620 | Olfr881 | NM_146418.2 | chr9:37800076-37801024 |
| 21621 | Olfr883 | NM_146419.2 | chr9:37833392-37834322 |
| 21622 | Olfr884 | NM_001011798.1 | chr9:37854808-37855738 |
| 21623 | Olfr885 | NM_001011739.1 | chr9:37868906-37869836 |
| 21624 | Olfr887 | NM_146423.1 | chr9:37892422-37893352 |
| 21625 | Olfr888 | NM_146424.1 | chr9:37916272-37917217 |
| 21626 | Olfr889 | NM_146482.1 | chr9:37923382-37924312 |
| 21627 | Olfr890 | NM_146481.2 | chr9:37950721-37951666 |
| 21628 | Olfr891 | NM_146478.2 | chr9:37987455-37988406 |
| 21629 | Olfr893 | NM_146336.2 | chr9:38016636-38017578 |
| 21630 | Olfr894 | NM_146868.2 | chr9:38026402-38027351 |
| 21631 | Olfr895 | NM_146876.2 | chr9:38076099-38077050 |
| 21632 | Olfr898 | NM_146871.2 | chr9:38156669-38157620 |
| 21633 | Olfr899 | NM_146479.1 | chr9:38175132-38176128 |
| 21634 | Olfr9 | NM_146861.1 | chr16:128426969-128427908 |
| 21635 | Olfr90 | NM_146477.2 | chr17:37222135-37223181 |
| 21636 | Olfr901 | NM_001011806.1 | chr9:38237868-38238804 |
| 21637 | Olfr902 | NM_146802.2 | chr9:38256376-38257432 |
| 21638 | Olfr904 | NM_146801.2 | chr9:38271627-38272560 |
| 21639 | Olfr905 | NM_146804.2 | chr9:38280333-38281266 |
| 21640 | Olfr906 | NM_146803.2 | chr9:38295615-38296551 |
| 21641 | Olfr907 | NM_146805.2 | chr9:38306255-38307188 |
| 21642 | Olfr908 | NM_146872.1 | chr9:38323618-38324550 |
| 21643 | Olfr91 | NM_182714.2 | chr17:37229878-37230817 |
| 21644 | Olfr910 | NM_146811.2 | chr9:38345466-38347414 |
| 21645 | Olfr911-ps1 | NM_146873.2 | chr9:38331314-38332254 |
| 21646 | Olfr912 | NM_146810.2 | chr9:38387828-38389796 |
| 21647 | Olfr913 | NM_001011523.2 | chr9:38400387-38402746 |
| 21648 | Olfr914 | NM_146786.2 | chr9:38414051-38415002 |
| 21649 | Olfr915 | NM_146785.2 | chr9:38454174-38455107 |
| 21650 | Olfr916 | NM_146784.1 | chr9:38465042-38465975 |
| 21651 | Olfr917 | NM_001011864.1 | chr9:38472497-38473427 |
| 21652 | Olfr918 | NM_146375.2 | chr9:38480088-38481066 |
| 21653 | Olfr919 | NM_146404.1 | chr9:38505013-38505961 |
| 21654 | Olfr92 | NM_146456.2 | chr17:37247986-37248925 |
| 21655 | Olfr920 | NM_146787.2 | chr9:38560380-38564448 |
| 21656 | Olfr921 | NM_146782.2 | chr9:38580672-38583939 |
| 21657 | Olfr922 | NM_146781.2 | chr9:38622992-38624124 |
| 21658 | Olfr923 | NM_146816.2 | chr9:38635199-38636267 |
| 21659 | Olfr924 | NM_207565.1 | chr9:38655708-38656627 |
| 21660 | Olfr926 | NM_146815.1 | chr9:38684762-38685689 |
| 21661 | Olfr93 | NM_001011813.1 | chr17:37287976-37288915 |
| 21662 | Olfr930 | NM_146272.1 | chr9:38737757-38738684 |
| 21663 | Olfr933 | NM_146441.1 | chr9:38783262-38784189 |
| 21664 | Olfr934 | NM_146442.1 | chr9:38789694-38790627 |
| 21665 | Olfr935 | NM_146746.1 | chr9:38802091-38803018 |
| 21666 | Olfr936 | NM_207139.1 | chr9:38854198-38855134 |
| 21667 | Olfr937 | NM_146439.1 | chr9:38867313-38868249 |
| 21668 | Olfr938 | NM_146438.1 | chr9:38885380-38886328 |
| 21669 | Olfr94 | NM_001011518.1 | chr17:37333756-37334911 |
| 21670 | Olfr943 | NM_146263.3 | chr9:38973894-38992709 |
| 21671 | Olfr944 | NM_146507.1 | chr9:39024943-39025879 |
| 21672 | Olfr945 | NM_146506.1 | chr9:39065304-39066264 |
| 21673 | Olfr947-ps1 | NR_033620.1 | chr9:39095510-39107066 |
| 21674 | Olfr948 | NM_001011756.1 | chr9:39126231-39127197 |
| 21675 | Olfr95 | NM_146513.1 | chr17:37347857-37348796 |
| 21676 | Olfr951 | NM_001011377.1 | chr9:39201377-39202322 |
| 21677 | Olfr952 | NM_146503.1 | chr9:39233709-39234654 |
| 21678 | Olfr954 | NM_146331.1 | chr9:39269017-39269962 |
| 21679 | Olfr955 | NM_207141.1 | chr9:39277364-39278309 |
| 21680 | Olfr957 | NM_146745.2 | chr9:39318367-39319303 |
| 21681 | Olfr958 | NM_146330.1 | chr9:39357515-39358454 |
| 21682 | Olfr959 | NM_146508.1 | chr9:39379906-39380842 |
| 21683 | Olfr96 | NM_146514.1 | chr17:37362071-37363013 |
| 21684 | Olfr960 | NM_146279.1 | chr9:39430709-39431660 |
| 21685 | Olfr961 | NM_146504.1 | chr9:39454312-39455257 |
| 21686 | Olfr963 | NM_001011827.1 | chr9:39476643-39477579 |
| 21687 | Olfr965 | NM_001011859.1 | chr9:39526813-39527752 |
| 21688 | Olfr967 | NM_001011826.1 | chr9:39557972-39558905 |
| 21689 | Olfr968 | NM_146612.2 | chr9:39579356-39580383 |
| 21690 | Olfr969 | NM_146826.1 | chr9:39602961-39603897 |
| 21691 | Olfr97 | NM_146512.1 | chr17:37368380-37369313 |
| 21692 | Olfr970 | NM_146611.1 | chr9:39627225-39628161 |
| 21693 | Olfr971 | NM_146614.1 | chr9:39647020-39647944 |
| 21694 | Olfr972 | NM_146610.1 | chr9:39680861-39681806 |
| 21695 | Olfr974 | NM_147107.1 | chr9:39749846-39750779 |
| 21696 | Olfr975 | NM_146828.1 | chr9:39757421-39758354 |
| 21697 | Olfr976 | NM_146367.2 | chr9:39761841-39764654 |
| 21698 | Olfr978 | NM_147105.2 | chr9:39801396-39802332 |
| 21699 | Olfr979 | NM_147108.2 | chr9:39807790-39808835 |
| 21700 | Olfr98 | NM_146510.1 | chr17:37399677-37400607 |
| 21701 | Olfr980 | NM_147106.2 | chr9:39813578-39814614 |
| 21702 | Olfr981 | NM_146286.1 | chr9:39829979-39830912 |
| 21703 | Olfr982 | NM_146854.1 | chr9:39881881-39882847 |
| 21704 | Olfr983 | NM_146827.2 | chr9:39899601-39901143 |
| 21705 | Olfr984 | NM_146608.1 | chr9:39908128-39909073 |
| 21706 | Olfr985 | NM_146855.2 | chr9:39934508-39935624 |
| 21707 | Olfr986 | NM_146615.2 | chr9:39994663-39995679 |
| 21708 | Olfr987 | NM_001011785.1 | chr2:85171123-85172053 |
| 21709 | Olfr988 | NM_001011534.1 | chr2:85193151-85194081 |
| 21710 | Olfr99 | NM_146515.2 | chr17:37416445-37417363 |
| 21711 | Olfr992 | NM_146865.1 | chr2:85239758-85240688 |
| 21712 | Olfr993 | NM_146435.1 | chr2:85254089-85255034 |
| 21713 | Olfr994 | NM_146433.1 | chr2:85270039-85270984 |
| 21714 | Olfr995 | NM_146434.1 | chr2:85278365-85279313 |
| 21715 | Olfr996 | NM_146437.2 | chr2:85419371-85420439 |
| 21716 | Olfr998 | NM_146436.2 | chr2:85430666-85431678 |
| 21717 | Olig1 | NM_016968.4 | chr16:91270013-91272184 |
| 21718 | Olig2 | NM_016967.2 | chr16:91225794-91228922 |
| 21719 | Olig3 | NM_053008.2 | chr10:19076344-19078410 |
| 21720 | Olr1 | NM_138648.2 | chr6:129485265-129457183 |
| 21721 | Oma1 | NM_025909.3 | chr4:102986450-103039033 |
| 21722 | Omd | NM_012050.2 | chr13:49678116-49687978 |
| 21723 | Omg | NM_019409.2 | chr11:79314484-79317584 |
| 21724 | Omp | NM_011010.2 | chr7:105291869-105293957 |
| 21725 | Omt2a | NM_001111286.2 | chr9:78159778-78162604 |
| 21726 | Omt2a | NM_001164523.1 | chr9:78159778-78162604 |
| 21727 | Omt2b | NM_205822.2 | chr9:78175836-78177427 |
| 21728 | Onecut1 | NM_008262.3 | chr9:74709727-74737454 |
| 21729 | Onecut2 | NM_194268.2 | chr18:64500017-64558142 |
| 21730 | Onecut3 | NM_139226.3 | chr10:79957650-79980005 |
| 21731 | Ooep | NM_026480.3 | chr9:78224709-78226395 |
| 21732 | Oog1 | NM_178657.5 | chr12:88943614-88949795 |
| 21733 | Oog1 | NM_178657.5 | chr12:89192923-89199126 |
| 21734 | Oog2 | NM_198661.3 | chr4:143780619-143786837 |
| 21735 | Oog3 | NM_201258.2 | chr4:143747458-143752554 |
| 21736 | Oog4 | NM_173773.1 | chr4:143027066-143040205 |
| 21737 | Oosp1 | NM_133353.3 | chr19:11741949-11765541 |
| 21738 | Oosp2 | NM_001037634.3 | chr19:11721773-11735049 |
| 21739 | Oosp3 | NM_001033283.2 | chr19:11771544-11786348 |
| 21740 | Opa1 | NM_001199177.1 | chr16:29579419-29654688 |
| 21741 | Opa1 | NM_133752.3 | chr16:29579419-29654688 |
| 21742 | Opa3 | NM_207525.3 | chr7:19813737-19832166 |
| 21743 | Opalin | NM_153520.1 | chr19:41137909-41151603 |
| 21744 | Opcml | NM_177906.4 | chr9:27598853-28732633 |
| 21745 | Ophn1 | NM_052976.3 | chrX:95752853-96086324 |
| 21746 | Oplah | NM_153122.2 | chr15:76127033-76137675 |
| 21747 | Opn1mw | NM_008106.2 | chrX:71372804-71396094 |
| 21748 | Opn1sw | NM_007538.3 | chr6:29326671-29330513 |
| 21749 | Opn3 | NM_010098.3 | chr1:177592553-177622763 |
| 21750 | Opn4 | NM_001128599.1 | chr14:35403803-35413328 |
| 21751 | Opn4 | NM_013887.2 | chr14:35403803-35413328 |
| 21752 | Opn5 | NM_181753.4 | chr17:42693731-42748262 |
| 21753 | Oprd1 | NM_013622.3 | chr4:131666640-131700401 |
| 21754 | Oprk1 | NM_001204371.1 | chr1:5578573-5596214 |
| 21755 | Oprk1 | NM_011011.2 | chr1:5578573-5596214 |
| 21756 | Oprl1 | NM_001252565.1 | chr2:181449720-181455690 |
| 21757 | Oprl1 | NM_011012.5 | chr2:181449720-181455690 |
| 21758 | Oprl1 | NR_045540.1 | chr2:181449720-181455690 |
| 21759 | Oprl1 | NR_045541.1 | chr2:181449720-181455690 |
| 21760 | Oprl1 | NR_045542.1 | chr2:181449720-181455690 |
| 21761 | Oprm1 | NM_001039652.2 | chr10:3308332-3557965 |
| 21762 | Optc | NM_001160420.2 | chr1:135793770-135804576 |
| 21763 | Optc | NM_001160421.2 | chr1:135793770-135804576 |
| 21764 | Optc | NM_001160422.1 | chr1:135793770-135804576 |
| 21765 | Optc | NM_054076.3 | chr1:135793770-135804576 |
| 21766 | Optn | NM_181848.4 | chr2:4941687-4984984 |
| 21767 | Orai1 | NM_175423.3 | chr5:123465082-123480461 |
| 21768 | Orai2 | NM_178751.3 | chr5:136623331-136646526 |
| 21769 | Orai3 | NM_198424.3 | chr7:134913328-134918664 |
| 21770 | Oraov1 | NM_028184.3 | chr7:152101098-152107042 |
| 21771 | Orc1 | NM_011015.2 | chr4:108252058-108287436 |
| 21772 | Orc2 | NM_001025378.2 | chr1:58519614-58561953 |
| 21773 | Orc2 | NM_001271526.1 | chr1:58519614-58561953 |

Fig. 25 - 116

| | | | |
|---|---|---|---|
| 21774 | Orc2 | NM_008765.3 | chr1:58519614-58561953 |
| 21775 | Orc3 | NM_001159563.1 | chr4:34497863-34562191 |
| 21776 | Orc3 | NM_015824.4 | chr4:34497863-34562191 |
| 21777 | Orc4 | NM_001177313.1 | chr2:48669628-48804787 |
| 21778 | Orc4 | NM_011958.3 | chr2:48669628-48804787 |
| 21779 | Orc4 | NR_033442.1 | chr2:48669628-48804787 |
| 21780 | Orc5 | NM_011959.2 | chr5:21992307-22056149 |
| 21781 | Orc6 | NM_001163791.1 | chr8:87823530-87832178 |
| 21782 | Orc6 | NM_019716.2 | chr8:87823530-87832178 |
| 21783 | Orc6 | NR_028268.1 | chr8:87823530-87832178 |
| 21784 | Orm1 | NM_008768.1 | chr4:63005599-63009196 |
| 21785 | Orm2 | NM_011016.2 | chr4:63023482-63026911 |
| 21786 | Orm3 | NM_013623.2 | chr4:63017195-63020545 |
| 21787 | Ormdl1 | NM_145517.4 | chr1:53353938-53367089 |
| 21788 | Ormdl2 | NM_024180.5 | chr10:128254513-128258687 |
| 21789 | Ormdl3 | NM_025661.4 | chr11:98442607-98448559 |
| 21790 | Os9 | NM_001171026.1 | chr10:126531314-126558216 |
| 21791 | Os9 | NM_177614.3 | chr10:126531314-126558216 |
| 21792 | Osbp | NM_001033174.1 | chr19:12040333-12068604 |
| 21793 | Osbp2 | NM_152818.2 | chr11:3603733-3763906 |
| 21794 | Osbpl10 | NM_148958.2 | chr9:114976396-115141341 |
| 21795 | Osbpl11 | NM_176840.3 | chr16:33185156-33243398 |
| 21796 | Osbpl1a | NM_001252489.1 | chr18:12913820-13100350 |
| 21797 | Osbpl1a | NM_001252490.1 | chr18:12913820-13100350 |
| 21798 | Osbpl1a | NM_001252491.1 | chr18:12913820-13100350 |
| 21799 | Osbpl1a | NM_001252492.1 | chr18:12913820-13100350 |
| 21800 | Osbpl1a | NM_001252493.1 | chr18:12913820-13100350 |
| 21801 | Osbpl1a | NM_207530.3 | chr18:12913820-13100350 |
| 21802 | Osbpl1a | NR_045524.1 | chr18:12913820-13100350 |
| 21803 | Osbpl2 | NM_144500.3 | chr2:179854070-179897385 |
| 21804 | Osbpl3 | NM_001163645.1 | chr6:50243325-50406169 |
| 21805 | Osbpl3 | NM_027881.3 | chr6:50243325-50406169 |
| 21806 | Osbpl5 | NM_001199227.1 | chr7:150874666-150927868 |
| 21807 | Osbpl5 | NM_024289.2 | chr7:150874666-150927868 |
| 21808 | Osbpl6 | NM_001290733.1 | chr2:76244564-76438704 |
| 21809 | Osbpl6 | NM_001290734.1 | chr2:76244564-76438704 |
| 21810 | Osbpl6 | NM_001290735.1 | chr2:76244564-76438704 |
| 21811 | Osbpl6 | NM_145525.3 | chr2:76244564-76438704 |
| 21812 | Osbpl7 | NM_001081434.1 | chr11:96912134-96930218 |
| 21813 | Osbpl8 | NM_001003717.1 | chr10:110601857-110734303 |
| 21814 | Osbpl8 | NM_175489.3 | chr10:110601857-110734303 |
| 21815 | Osbpl9 | NM_001134791.2 | chr4:108673409-108874877 |
| 21816 | Osbpl9 | NM_133885.4 | chr4:108673409-108874877 |
| 21817 | Osbpl9 | NM_173350.3 | chr4:108673409-108874877 |
| 21818 | Oscar | NM_001290771.1 | chr7:3561415-3567759 |
| 21819 | Oscar | NM_175632.3 | chr7:3561415-3567759 |
| 21820 | Oscp1 | NM_172701.2 | chr4:125735808-125766578 |
| 21821 | Oser1 | NM_025699.2 | chr2:163231557-163245206 |
| 21822 | Osgep | NM_133676.2 | chr14:51535048-51544568 |
| 21823 | Osgepl1 | NM_001285839.1 | chr1:53370467-53383186 |
| 21824 | Osgepl1 | NR_104360.1 | chr1:53370467-53383186 |
| 21825 | Osgepl1 | NR_104361.1 | chr1:53370467-53383186 |
| 21826 | Osgin1 | NM_027969.2 | chr8:121691061-121970156 |
| 21827 | Osgin2 | NM_145950.4 | chr4:15924267-15941024 |
| 21828 | Osm | NM_001013365.2 | chr11:4136787-4141029 |
| 21829 | Osmr | NM_011019.3 | chr15:6763576-6824313 |
| 21830 | Osr1 | NM_011859.3 | chr12:9581247-9588306 |
| 21831 | Osr2 | NM_054049.2 | chr15:35225866-35233060 |
| 21832 | Ost4 | NM_001134692.2 | chr5:31191224-31210161 |
| 21833 | Ost4 | NM_024460.4 | chr5:31191224-31210161 |
| 21834 | Ostc | NM_025509.3 | chr3:130398834-130412362 |
| 21835 | Ostf1 | NM_017375.3 | chr19:18654853-18706309 |
| 21836 | Ostm1 | NM_172416.3 | chr10:42398721-42422268 |
| 21837 | Ostn | NM_198211.2 | chr16:27307726-27351295 |
| 21838 | Otc | NM_008769.3 | chrX:9829484-9898150 |
| 21839 | Otoa | NM_139310.1 | chr7:128226951-128306603 |
| 21840 | Otof | NM_001100395.1 | chr5:30669350-30764305 |
| 21841 | Otof | NM_001286421.1 | chr5:30669350-30764305 |
| 21842 | Otof | NM_031875.2 | chr5:30669350-30764305 |
| 21843 | Otog | NM_013624.2 | chr7:53496356-53566804 |
| 21844 | Otogl | NM_001177567.1 | chr10:107199365-107349190 |
| 21845 | Otol1 | NM_001018031.2 | chr3:69811534-69832630 |
| 21846 | Otop1 | NM_172709.3 | chr5:38668642-38695456 |
| 21847 | Otop2 | NM_172801.2 | chr11:115168477-115193617 |
| 21848 | Otop3 | NM_027132.2 | chr11:115196047-115208240 |
| 21849 | Otor | NM_020595.2 | chr2:129042227-142907435 |
| 21850 | Otos | NM_153114.2 | chr1:94540794-94545418 |
| 21851 | Otp | NM_011021.3 | chr13:95645581-95653636 |
| 21852 | Ott | NM_011022.1 | chrX_random:562213-602417 |
| 21853 | Ott | NM_011022.1 | chrX:145522857-145739546 |
| 21854 | OTTMUSG00000016609 | NM_001100416.2 | chr2:175594788-176850107 |
| 21855 | OTTMUSG00000016609 | NM_001100416.2 | chr2:175594788-176850107 |
| 21856 | Otub1 | NM_134150.2 | chr19:7272695-7280774 |
| 21857 | Otub2 | NM_001177841.1 | chr12:104615103-104644560 |
| 21858 | Otub2 | NM_026580.4 | chr12:104615103-104644560 |
| 21859 | Otub2 | NR_033587.1 | chr12:104615103-104644560 |
| 21860 | Otud1 | NM_027715.3 | chr2:19579688-19582217 |
| 21861 | Otud3 | NM_028453.1 | chr4:138451293-138469862 |
| 21862 | Otud4 | NM_001081164.1 | chr8:82163574-82201654 |
| 21863 | Otud4 | NM_001256033.1 | chr8:82163574-82201654 |
| 21864 | Otud5 | NM_001290536.1 | chrX:7418956-7453752 |
| 21865 | Otud5 | NM_001290537.1 | chrX:7418956-7453752 |
| 21866 | Otud5 | NM_138604.3 | chrX:7418956-7453752 |
| 21867 | Otud6a | NM_001163191.1 | chrX:97624352-97625224 |
| 21868 | Otud6b | NM_152812.3 | chr4:14736651-14753734 |
| 21869 | Otud7a | NM_130880.1 | chr7:70589657-70903913 |
| 21870 | Otud7b | NM_001025613.1 | chr3:95908449-95965052 |
| 21871 | Otud7b | NM_001025614.1 | chr3:95908449-95965052 |
| 21872 | Otulin | NM_001013792.2 | chr15:27535675-27560448 |
| 21873 | Otx1 | NM_011023.3 | chr11:21894766-21901654 |
| 21874 | Otx2 | NM_001286481.1 | chr14:49277351-49287319 |
| 21875 | Otx2 | NM_001286482.1 | chr14:49277351-49287319 |
| 21876 | Otx2 | NM_001286483.1 | chr14:49277351-49287319 |
| 21877 | Otx2 | NM_144841.4 | chr14:49277351-49287319 |
| 21878 | Otx2os1 | NR_029384.1 | chr14:49288962-49413023 |
| 21879 | Ovca2 | NM_027136.3 | chr11:74989445-74992310 |
| 21880 | Ovch2 | NM_172908.3 | chr7:114925057-114944693 |
| 21881 | Ovgp1 | NM_007696.2 | chr3:105776719-105790341 |
| 21882 | Ovol1 | NM_019935.3 | chr19:5549136-5560575 |
| 21883 | Ovol2 | NM_026924.3 | chr2:144130911-144157816 |
| 21884 | Ovol2 | NM_152947.2 | chr2:144130911-144157816 |
| 21885 | Ovol3 | NM_001289817.1 | chr7:31018316-31021784 |
| 21886 | Oxa1l | NM_026936.3 | chr14:54980525-54989353 |
| 21887 | Oxct1 | NM_024188.6 | chr15:3976428-4105344 |
| 21888 | Oxct2a | NM_022033.4 | chr4:122999118-123000922 |
| 21889 | Oxct2b | NM_181859.2 | chr4:122793491-122795243 |
| 21890 | Oxgr1 | NM_001014490.3 | chr14:120418806-120441657 |
| 21891 | Oxld1 | NM_025560.2 | chr11:120317917-120319377 |
| 21892 | Oxnad1 | NM_145460.2 | chr14:32898913-32916389 |
| 21893 | Oxr1 | NM_001130163.1 | chr15:41209535-41692593 |
| 21894 | Oxr1 | NM_001130164.1 | chr15:41209535-41692593 |
| 21895 | Oxr1 | NM_001130165.1 | chr15:41209535-41692593 |
| 21896 | Oxr1 | NM_001130166.1 | chr15:41209535-41692593 |
| 21897 | Oxr1 | NM_130885.2 | chr15:41209535-41692593 |
| 21898 | Oxsm | NM_027695.3 | chr14:17071173-17082322 |
| 21899 | Oxsr1 | NM_133985.2 | chr9:119147550-119231545 |
| 21900 | Oxsr1 | NR_045693.1 | chr9:119147550-119231545 |
| 21901 | Oxt | NM_011025.4 | chr2:130401904-130402789 |
| 21902 | Oxtr | NM_001081147.1 | chr6:112423677-112439802 |
| 21903 | P2rx1 | NM_008771.3 | chr11:72812646-72828699 |
| 21904 | P2rx2 | NM_001164833.1 | chr5:110768830-110772054 |
| 21905 | P2rx2 | NM_001164834.1 | chr5:110768830-110772054 |
| 21906 | P2rx2 | NM_153400.4 | chr5:110768830-110772054 |
| 21907 | P2rx3 | NM_145526.2 | chr2:84836708-84875991 |
| 21908 | P2rx4 | NM_011026.2 | chr5:123157565-123179051 |
| 21909 | P2rx5 | NM_033321.3 | chr11:72974031-72986189 |
| 21910 | P2rx6 | NM_001159561.1 | chr16:17561977-17572105 |
| 21911 | P2rx6 | NM_011028.2 | chr16:17561977-17572105 |
| 21912 | P2rx7 | NM_001038839.2 | chr5:123093919-123141441 |
| 21913 | P2rx7 | NM_001038845.2 | chr5:123093919-123141441 |
| 21914 | P2rx7 | NM_001038887.1 | chr5:123093919-123141441 |
| 21915 | P2rx7 | NM_001284402.1 | chr5:123093919-123141441 |
| 21916 | P2rx7 | NM_011027.3 | chr5:123093919-123141441 |
| 21917 | P2ry1 | NM_001282016.1 | chr3:60806706-60812904 |
| 21918 | P2ry1 | NM_008772.5 | chr3:60806706-60812904 |
| 21919 | P2ry10 | NM_172435.3 | chrX:104284673-104300309 |
| 21920 | P2ry12 | NM_027571.3 | chr3:59020193-59066753 |
| 21921 | P2ry13 | NM_028808.3 | chr3:59011814-59014804 |
| 21922 | P2ry14 | NM_001008497.2 | chr3:58810899-59148178 |
| 21923 | P2ry14 | NM_001287119.1 | chr3:58810899-59148178 |
| 21924 | P2ry14 | NM_001287120.1 | chr3:58810899-59148178 |
| 21925 | P2ry14 | NM_001287121.1 | chr3:58810899-59148178 |
| 21926 | P2ry14 | NM_001287122.1 | chr3:58810899-59148178 |
| 21927 | P2ry14 | NM_001287123.1 | chr3:58810899-59148178 |
| 21928 | P2ry14 | NM_001287124.1 | chr3:58810899-59148178 |
| 21929 | P2ry14 | NM_133200.4 | chr3:58810899-59148178 |
| 21930 | P2ry2 | NM_008773.4 | chr7:108145085-108160505 |
| 21931 | P2ry4 | NM_020621.4 | chrX:97785492-97790208 |
| 21932 | P2ry6 | NM_183168.2 | chr7:108086147-108112880 |
| 21933 | P4ha1 | NM_011030.2 | chr10:58786043-58836052 |
| 21934 | P4ha2 | NM_001136076.2 | chr11:53914425-53945169 |
| 21935 | P4ha2 | NM_011031.2 | chr11:53914425-53945169 |
| 21936 | P4ha3 | NM_177161.4 | chr7:107434029-107468209 |
| 21937 | P4hb | NM_011032.2 | chr11:120421617-120434250 |
| 21938 | P4htm | NM_028944.3 | chr9:108481156-108499931 |
| 21939 | Pa2g4 | NM_011119.3 | chr10:127994821-128002990 |
| 21940 | Pabpc1 | NM_008774.3 | chr15:36525412-36538728 |
| 21941 | Pabpc1l | NM_001114079.2 | chr2:163850959-163876274 |
| 21942 | Pabpc2 | NM_011033.2 | chr18:39933150-39935736 |
| 21943 | Pabpc4 | NM_130881.2 | chr4:122960153-122976076 |
| 21944 | Pabpc4 | NM_148917.2 | chr4:122960153-122976076 |
| 21945 | Pabpc4l | NM_001101479.1 | chr3:46246118-46251863 |
| 21946 | Pabpc5 | NM_053114.2 | chrX:117040804-117043774 |
| 21947 | Pabpc6 | NM_001163836.1 | chr17:9859361-9862569 |
| 21948 | Pabpn1 | NM_019402.2 | chr14:55512979-55517764 |
| 21949 | Pabpn1l | NM_001007462.1 | chr8:125143371-125146635 |
| 21950 | Pacrg | NM_027032.2 | chr17:10595878-11033057 |
| 21951 | Pacrgl | NM_025755.3 | chr5:48763630-48779995 |
| 21952 | Pacs1 | NM_153129.2 | chr19:5133684-5273119 |
| 21953 | Pacs2 | NM_001081170.1 | chr12:114252718-114312612 |
| 21954 | Pacs2 | NM_001291444.1 | chr12:114252718-114312612 |
| 21955 | Pacs2 | NM_001291445.1 | chr12:114252718-114312612 |
| 21956 | Pacsin1 | NM_001286743.1 | chr17:27792535-27848062 |
| 21957 | Pacsin1 | NM_001286744.1 | chr17:27792535-27848062 |
| 21958 | Pacsin1 | NM_011861.3 | chr17:27792535-27848062 |
| 21959 | Pacsin1 | NM_178365.4 | chr17:27792535-27848062 |
| 21960 | Pacsin2 | NM_001159509.1 | chr15:83206036-83295036 |
| 21961 | Pacsin2 | NM_001159510.1 | chr15:83206036-83295036 |
| 21962 | Pacsin2 | NM_011862.3 | chr15:83206036-83295036 |

Fig. 25 - 117

| | | | |
|---|---|---|---|
| 21963 | Pacsin3 | NM_001289677.1 | chr2:91096321-91104837 |
| 21964 | Pacsin3 | NM_001289678.1 | chr2:91096321-91104837 |
| 21965 | Pacsin3 | NM_028733.4 | chr2:91096321-91104837 |
| 21966 | Pacsin3 | NM_030880.3 | chr2:91096321-91104837 |
| 21967 | Padi1 | NM_011059.2 | chr4:140368896-140401693 |
| 21968 | Padi2 | NM_008812.2 | chr4:140462275-140508501 |
| 21969 | Padi3 | NM_011060.2 | chr4:140341283-140366563 |
| 21970 | Padi4 | NM_011061.2 | chr4:140301422-140330118 |
| 21971 | Padi6 | NM_153106.2 | chr4:140283269-140298558 |
| 21972 | Paf1 | NM_019458.3 | chr7:29178014-29184402 |
| 21973 | Pafah1b1 | NM_013625.4 | chr11:74487450-74537886 |
| 21974 | Pafah1b1 | NR_037610.2 | chr11:74487450-74537886 |
| 21975 | Pafah1b2 | NM_008775.3 | chr9:45773393-45792954 |
| 21976 | Pafah1b3 | NM_008776.2 | chr7:26080067-26082974 |
| 21977 | Pafah2 | NM_001285872.1 | chr4:133952234-133983327 |
| 21978 | Pafah2 | NM_001285874.1 | chr4:133952234-133983327 |
| 21979 | Pafah2 | NM_001285875.1 | chr4:133952234-133983327 |
| 21980 | Pafah2 | NM_001285877.1 | chr4:133952234-133983327 |
| 21981 | Pafah2 | NM_133880.3 | chr4:133952234-133983327 |
| 21982 | Pag1 | NM_001195031.1 | chr3:9687481-9833679 |
| 21983 | Pag1 | NM_053182.5 | chr3:9687481-9833679 |
| 21984 | Pagr1a | NM_030240.1 | chr7:134158564-134160866 |
| 21985 | Pah | NM_008777.3 | chr10:86984539-87046882 |
| 21986 | Paics | NM_025939.2 | chr5:77380436-77396531 |
| 21987 | Paip1 | NM_001079849.1 | chr13:120217406-120249130 |
| 21988 | Paip1 | NM_145457.4 | chr13:120217406-120249130 |
| 21989 | Paip2 | NM_026420.2 | chr18:35758321-35776839 |
| 21990 | Paip2b | NM_146169.2 | chr6:83756052-83781735 |
| 21991 | Pak1 | NM_011035.2 | chr7:104991448-105060891 |
| 21992 | Pak1ip1 | NM_026550.3 | chr13:41096378-41108402 |
| 21993 | Pak2 | NM_177326.3 | chr16:32016375-32079428 |
| 21994 | Pak3 | NM_001195046.1 | chrX:139953133-140232339 |
| 21995 | Pak3 | NM_001195047.1 | chrX:139953133-140232339 |
| 21996 | Pak3 | NM_001195048.1 | chrX:139953133-140232339 |
| 21997 | Pak3 | NM_001195049.1 | chrX:139953133-140232339 |
| 21998 | Pak3 | NM_008778.3 | chrX:139953133-140232339 |
| 21999 | Pak4 | NM_027470.3 | chr7:29343838-29383203 |
| 22000 | Pak6 | NM_001033254.3 | chr2:118489312-118523756 |
| 22001 | Pak6 | NM_001145654.1 | chr2:118489312-118523756 |
| 22002 | Pak7 | NM_172858.2 | chr2:135906823-136213703 |
| 22003 | Palb2 | NM_001081238.2 | chr7:129250775-129276460 |
| 22004 | Palb2 | NM_001289842.1 | chr7:129250775-129276460 |
| 22005 | Palb2 | NM_001289843.1 | chr7:129250775-129276460 |
| 22006 | Palb2 | NM_001289844.1 | chr7:129250775-129276460 |
| 22007 | Palb2 | NM_001289845.1 | chr7:129250775-129276460 |
| 22008 | Pald1 | NM_013753.2 | chr10:60782404-60846271 |
| 22009 | Palld | NM_001081390.1 | chr8:63993819-64381487 |
| 22010 | Palm | NM_001161747.1 | chr10:79256316-79283641 |
| 22011 | Palm | NM_023128.4 | chr10:79256316-79283641 |
| 22012 | Palm2 | NM_172868.3 | chr4:57581119-57730000 |
| 22013 | Palm3 | NM_028877.1 | chr8:86545373-86554194 |
| 22014 | Palmd | NM_023245.3 | chr3:116621180-116671870 |
| 22015 | Pam | NM_013626.3 | chr1:99717671-99992209 |
| 22016 | Pam16 | NM_025571.1 | chr16:4616465-4624946 |
| 22017 | Pamr1 | NM_173749.4 | chr2:102390177-102483197 |
| 22018 | Pan2 | NM_001252326.1 | chr10:127740390-127758414 |
| 22019 | Pan2 | NM_001252327.1 | chr10:127740390-127758414 |
| 22020 | Pan2 | NM_133992.3 | chr10:127740390-127758414 |
| 22021 | Pan3 | NM_028291.4 | chr5:148242155-148360077 |
| 22022 | Pank1 | NM_001114339.2 | chr19:34881425-34953945 |
| 22023 | Pank1 | NM_023792.2 | chr19:34881425-34953945 |
| 22024 | Pank2 | NM_153501.2 | chr2:131088236-131124924 |
| 22025 | Pank3 | NM_145962.2 | chr11:35582997-35604787 |
| 22026 | Pank4 | NM_172990.2 | chr4:154338241-154355047 |
| 22027 | Panx1 | NM_019482.2 | chr9:14810228-14849922 |
| 22028 | Panx2 | NM_001002005.2 | chr15:88890155-88901337 |
| 22029 | Panx3 | NM_172454.2 | chr9:37467486-37476807 |
| 22030 | Paox | NM_153783.4 | chr7:147311583-147320233 |
| 22031 | Papd4 | NM_133905.1 | chr13:93917854-93962238 |
| 22032 | Papd5 | NM_001164497.1 | chr8:90723111-90783621 |
| 22033 | Papd5 | NM_001164498.1 | chr8:90723111-90783621 |
| 22034 | Papd5 | NM_001164499.1 | chr8:90723111-90783621 |
| 22035 | Papd7 | NM_001169131.1 | chr13:69636836-69672742 |
| 22036 | Papd7 | NM_198600.2 | chr13:69636836-69672742 |
| 22037 | Papl | NM_175319.4 | chr7:29392655-29416034 |
| 22038 | Papln | NM_001253343.1 | chr12:85104583-85133334 |
| 22039 | Papln | NM_130887.3 | chr12:85104583-85133334 |
| 22040 | Papola | NM_011112.3 | chr12:107022911-107077153 |
| 22041 | Papolb | NM_019943.2 | chr5:14803694-143006030 |
| 22042 | Papolg | NM_172555.1 | chr11:23762645-23795270 |
| 22043 | Pappa | NM_021362.1 | chr4:64785207-65018543 |
| 22044 | Pappa2 | NM_001085376.2 | chr1:160641861-160887569 |
| 22045 | Papss1 | NM_001289477.1 | chr3:131227731-131306635 |
| 22046 | Papss1 | NM_001289478.1 | chr3:131227731-131306635 |
| 22047 | Papss1 | NM_001289479.1 | chr3:131227731-131306635 |
| 22048 | Papss1 | NM_011863.2 | chr3:131227731-131306635 |
| 22049 | Papss2 | NM_001201470.1 | chr19:32670204-32741677 |
| 22050 | Papss2 | NM_011864.3 | chr19:32670204-32741677 |
| 22051 | Paqr3 | NM_198422.2 | chr5:97511348-97540615 |
| 22052 | Paqr4 | NM_023824.3 | chr17:23873153-23877297 |
| 22053 | Paqr5 | NM_028748.2 | chr9:61801544-61874597 |
| 22054 | Paqr6 | NM_198410.3 | chr3:88168510-88172463 |
| 22055 | Paqr7 | NM_001285845.1 | chr4:134052675-134066152 |
| 22056 | Paqr7 | NM_001285846.1 | chr4:134052675-134066152 |
| 22057 | Paqr7 | NM_001285847.1 | chr4:134052675-134066152 |

| | | | |
|---|---|---|---|
| 22058 | Paqr7 | NM_001285849.1 | chr4:134052675-134066152 |
| 22059 | Paqr7 | NM_027995.3 | chr4:134052675-134066152 |
| 22060 | Paqr8 | NM_028829.3 | chr1:20880702-20928837 |
| 22061 | Paqr9 | NM_198414.2 | chr9:95460235-95462540 |
| 22062 | Pard3 | NM_001013580.3 | chr8:129587955-130136186 |
| 22063 | Pard3 | NM_001013581.2 | chr8:129587955-130136186 |
| 22064 | Pard3 | NM_001122850.1 | chr8:129587955-130136186 |
| 22065 | Pard3 | NM_033620.2 | chr8:129587955-130136186 |
| 22066 | Pard3b | NM_001081050.2 | chr1:61685397-62688858 |
| 22067 | Pard6a | NM_001047435.2 | chr8:108225047-108227394 |
| 22068 | Pard6a | NM_001047436.2 | chr8:108225047-108227394 |
| 22069 | Pard6a | NM_001286344.1 | chr8:108225047-108227394 |
| 22070 | Pard6a | NM_001286345.1 | chr8:108225047-108227394 |
| 22071 | Pard6a | NM_019695.3 | chr8:108225047-108227394 |
| 22072 | Pard6b | NM_021409.2 | chr2:167906503-167926703 |
| 22073 | Pard6g | NM_053117.3 | chr18:80243633-80316379 |
| 22074 | Parg | NM_011960.2 | chr14:33015156-33110735 |
| 22075 | Park2 | NM_016694.1 | chr17:11033250-12256226 |
| 22076 | Park7 | NM_020569.3 | chr4:150271241-150284030 |
| 22077 | Parl | NM_001005767.4 | chr16:20279893-20302435 |
| 22078 | Parm1 | NM_145562.2 | chr5:91946725-92053022 |
| 22079 | Parn | NM_028761.3 | chr16:13538056-13668263 |
| 22080 | Parp1 | NM_007415.2 | chr1:182499106-182531385 |
| 22081 | Parp10 | NM_001163575.1 | chr15:76063424-76073870 |
| 22082 | Parp10 | NM_001163576.1 | chr15:76063424-76073870 |
| 22083 | Parp11 | NM_181402.3 | chr6:127403740-127444257 |
| 22084 | Parp12 | NM_172893.1 | chr6:39036410-39068348 |
| 22085 | Parp14 | NM_001039530.3 | chr16:35832963-35871468 |
| 22086 | Parp16 | NM_177460.4 | chr9:65062496-65087026 |
| 22087 | Parp2 | NM_009632.2 | chr14:51427620-51440975 |
| 22088 | Parp3 | NM_145619.2 | chr9:106372683-106378982 |
| 22089 | Parp4 | NM_001145978.2 | chr14:57194455-57278635 |
| 22090 | Parp6 | NM_001205239.1 | chr9:59465090-59498097 |
| 22091 | Parp6 | NM_029922.3 | chr9:59465090-59498097 |
| 22092 | Parp6 | NR_038074.1 | chr9:59465090-59498097 |
| 22093 | Parp6 | NR_038075.1 | chr9:59465090-59498097 |
| 22094 | Parp8 | NM_001081009.1 | chr13:117643630-117814323 |
| 22095 | Parp9 | NM_030253.3 | chr16:35938556-35972707 |
| 22096 | Parpbp | NM_029249.2 | chr10:87554143-87609686 |
| 22097 | Pars2 | NM_001083887.2 | chr4:106323673-106327887 |
| 22098 | Pars2 | NM_001285783.1 | chr4:106323673-106327887 |
| 22099 | Pars2 | NM_001285784.1 | chr4:106323673-106327887 |
| 22100 | Pars2 | NM_172272.2 | chr4:106323673-106327887 |
| 22101 | Parva | NM_020606.5 | chr7:119571219-119735202 |
| 22102 | Parvb | NM_133167.3 | chr15:84062472-84146039 |
| 22103 | Parvg | NM_001162500.1 | chr15:84155149-84173408 |
| 22104 | Parvg | NM_022321.4 | chr15:84155149-84173408 |
| 22105 | Pask | NM_080850.2 | chr1:95206013-95239365 |
| 22106 | Pate2 | NM_001033421.3 | chr9:35477223-35480474 |
| 22107 | Pate4 | NM_020264.4 | chr9:35414677-35419470 |
| 22108 | Patl1 | NM_172635.3 | chr19:11986889-12019586 |
| 22109 | Patl2 | NM_026251.2 | chr2:121945844-122011925 |
| 22110 | Patz1 | NM_001253690.1 | chr11:3189133-3220725 |
| 22111 | Patz1 | NM_001253691.1 | chr11:3189133-3220725 |
| 22112 | Patz1 | NM_019574.3 | chr11:3189133-3220725 |
| 22113 | Patz1 | NR_045108.2 | chr11:3189133-3220725 |
| 22114 | Patz1 | NR_045109.2 | chr11:3189133-3220725 |
| 22115 | Paupar | NR_117095.1 | chr2:105498019-105501500 |
| 22116 | Pawr | NM_054056.2 | chr10:107769244-107851447 |
| 22117 | Pax1 | NM_008780.2 | chr2:147190729-147200784 |
| 22118 | Pax2 | NM_011037.4 | chr19:44831884-44912359 |
| 22119 | Pax3 | NM_001159520.1 | chr1:78097841-78193711 |
| 22120 | Pax3 | NM_008781.4 | chr1:78097841-78193711 |
| 22121 | Pax4 | NM_001159925.1 | chr6:28392333-28399340 |
| 22122 | Pax4 | NM_001159926.1 | chr6:28392333-28399340 |
| 22123 | Pax4 | NM_011038.2 | chr6:28392333-28399340 |
| 22124 | Pax5 | NM_008782.2 | chr4:44544378-44723312 |
| 22125 | Pax6 | NM_001244198.1 | chr2:105376236-105537521 |
| 22126 | Pax6 | NM_001244200.1 | chr2:105376236-105537521 |
| 22127 | Pax6 | NM_001244201.1 | chr2:105376236-105537521 |
| 22128 | Pax6 | NM_001244202.1 | chr2:105376236-105537521 |
| 22129 | Pax6 | NM_013627.5 | chr2:105376236-105537521 |
| 22130 | Pax6os1 | NR_002867.2 | chr2:105376237-105510487 |
| 22131 | Pax7 | NM_011039.2 | chr4:139293995-139388883 |
| 22132 | Pax8 | NM_011040.4 | chr2:24276070-24331119 |
| 22133 | Pax9 | NM_011041.2 | chr12:57796625-57812217 |
| 22134 | Paxbp1 | NM_026110.2 | chr16:91014282-91044624 |
| 22135 | Paxip1 | NM_018878.3 | chr5:28066620-28118090 |
| 22136 | Pbdc1 | NM_001281871.1 | chrX:102275094-102312429 |
| 22137 | Pbdc1 | NM_026312.3 | chrX:102275094-102312429 |
| 22138 | Pbk | NM_023209.2 | chr14:66424747-66436659 |
| 22139 | Pbld1 | NM_026701.2 | chr10:62524364-62540284 |
| 22140 | Pbld2 | NM_026085.2 | chr10:62487259-62521560 |
| 22141 | Pbp2 | NM_029595.3 | chr6:135259146-135260402 |
| 22142 | Pbrm1 | NM_001081251.1 | chr14:31832323-31934778 |
| 22143 | Pbsn | NM_017471.2 | chrX:75083236-75098839 |
| 22144 | Pbx1 | NM_001291508.1 | chr1:170049494-170362300 |
| 22145 | Pbx1 | NM_001291509.1 | chr1:170049494-170362300 |
| 22146 | Pbx1 | NM_008783.3 | chr1:170049494-170362300 |
| 22147 | Pbx1 | NM_183355.3 | chr1:170049494-170362300 |
| 22148 | Pbx2 | NM_017463.2 | chr17:34729415-34734286 |
| 22149 | Pbx3 | NM_001290576.1 | chr2:34026976-34227565 |
| 22150 | Pbx3 | NM_016768.2 | chr2:34026976-34227565 |
| 22151 | Pbx4 | NM_001024954.1 | chr8:72356602-72396191 |
| 22152 | Pbxip1 | NM_146131.2 | chr3:89240625-89254874 |

Fig. 25 - 118

| | | | |
|---|---|---|---|
| 22153 | Pcbd1 | NM_025273.4 | chr10:60552078-60557077 |
| 22154 | Pcbd2 | NM_028281.1 | chr13:55828728-55878191 |
| 22155 | Pcbp1 | NM_011865.3 | chr6:86474490-86476159 |
| 22156 | Pcbp2 | NM_001103165.1 | chr15:102301062-102347435 |
| 22157 | Pcbp2 | NM_001103166.1 | chr15:102301062-102347435 |
| 22158 | Pcbp2 | NM_001174073.1 | chr15:102301062-102347435 |
| 22159 | Pcbp2 | NM_011042.2 | chr15:102301062-102347435 |
| 22160 | Pcbp3 | NM_021568.2 | chr10:76224598-76424692 |
| 22161 | Pcbp4 | NM_021567.5 | chr9:106356169-106366342 |
| 22162 | Pcca | NM_144844.2 | chr14:122933549-123289166 |
| 22163 | Pccb | NM_025835.2 | chr9:100882456-100935294 |
| 22164 | Pcdh1 | NM_029357.3 | chr18:38356347-38369416 |
| 22165 | Pcdh10 | NM_001098170.1 | chr3:45182319-45243231 |
| 22166 | Pcdh10 | NM_001098171.1 | chr3:45182319-45243231 |
| 22167 | Pcdh10 | NM_001098172.1 | chr3:45182319-45243231 |
| 22168 | Pcdh10 | NM_011043.3 | chr3:45182319-45243231 |
| 22169 | Pcdh11x | NM_001271809.1 | chrX:117403935-118024227 |
| 22170 | Pcdh11x | NM_001271810.1 | chrX:117403935-118024227 |
| 22171 | Pcdh11x | NR_073451.1 | chrX:117403935-118024227 |
| 22172 | Pcdh11x | NR_073452.1 | chrX:117403935-118024227 |
| 22173 | Pcdh12 | NM_017378.2 | chr18:38426745-38444055 |
| 22174 | Pcdh15 | NM_001142735.1 | chr10:73284614-74112477 |
| 22175 | Pcdh15 | NM_001142736.1 | chr10:73284614-74112477 |
| 22176 | Pcdh15 | NM_001142737.1 | chr10:73284614-74112477 |
| 22177 | Pcdh15 | NM_001142738.1 | chr10:73284614-74112477 |
| 22178 | Pcdh15 | NM_001142739.1 | chr10:73284614-74112477 |
| 22179 | Pcdh15 | NM_001142740.1 | chr10:73284614-74112477 |
| 22180 | Pcdh15 | NM_001142741.1 | chr10:73284614-74112477 |
| 22181 | Pcdh15 | NM_001142742.1 | chr10:73284614-74112477 |
| 22182 | Pcdh15 | NM_001142743.1 | chr10:73284614-74112477 |
| 22183 | Pcdh15 | NM_001142747.1 | chr10:73284614-74112477 |
| 22184 | Pcdh15 | NM_001142747.1 | chr10:73284614-74112477 |
| 22185 | Pcdh15 | NM_001142748.1 | chr10:73284614-74112477 |
| 22186 | Pcdh15 | NM_001142760.1 | chr10:73284614-74112477 |
| 22187 | Pcdh15 | NM_023115.3 | chr10:73284614-74112477 |
| 22188 | Pcdh17 | NM_001033753.2 | chr14:84843370-84936867 |
| 22189 | Pcdh18 | NM_130448.3 | chr3:49547217-49561238 |
| 22190 | Pcdh19 | NM_001105245.1 | chrX:130117399-130223532 |
| 22191 | Pcdh19 | NM_001105245.1 | chrX:130117399-130223532 |
| 22192 | Pcdh20 | NM_178685.5 | chr14:88864553-88871203 |
| 22193 | Pcdh7 | NM_001122758.1 | chr5:58109259-58523479 |
| 22194 | Pcdh7 | NM_018764.2 | chr5:58109259-58523479 |
| 22195 | Pcdh8 | NM_001042726.3 | chr14:80166578-80171119 |
| 22196 | Pcdh8 | NM_021543.4 | chr14:80166578-80171119 |
| 22197 | Pcdh9 | NM_001081377.2 | chr14:93412918-94289888 |
| 22198 | Pcdh9 | NM_001271798.1 | chr14:93412918-94289888 |
| 22199 | Pcdh9 | NM_001271799.1 | chr14:93412918-94289888 |
| 22200 | Pcdh9 | NM_001271800.1 | chr14:93412918-94289888 |
| 22201 | Pcdha1 | NM_054072.1 | chr18:37089939-37347311 |
| 22202 | Pcdha10 | NM_009961.1 | chr18:37164974-37347311 |
| 22203 | Pcdha11 | NM_009090.1 | chr18:37170512-37347311 |
| 22204 | Pcdha12 | NM_138663.2 | chr18:37179884-37347311 |
| 22205 | Pcdha2 | NM_198117.2 | chr18:37098859-37347314 |
| 22206 | Pcdha3 | NM_138662.1 | chr18:37105861-37347311 |
| 22207 | Pcdha4 | NM_007766.2 | chr18:37112343-37347311 |
| 22208 | Pcdha4-g | NM_001174154.2 | chr18:37112302-38001526 |
| 22209 | Pcdha5 | NM_009959.1 | chr18:37120094-37347311 |
| 22210 | Pcdha6 | NM_007767.3 | chr18:37127410-37347311 |
| 22211 | Pcdha7 | NM_009957.1 | chr18:37135578-37347311 |
| 22212 | Pcdha8 | NM_201243.1 | chr18:37152121-37347311 |
| 22213 | Pcdha9 | NM_138661.1 | chr18:37157534-37347311 |
| 22214 | Pcdhac1 | NM_001003671.1 | chr18:37249790-37347311 |
| 22215 | Pcdhac2 | NM_001003672.1 | chr18:37303623-37347311 |
| 22216 | Pcdhb1 | NM_053126.1 | chr18:37424652-37427108 |
| 22217 | Pcdhb10 | NM_053135.2 | chr18:37571328-37574168 |
| 22218 | Pcdhb11 | NM_053136.3 | chr18:37581072-37584686 |
| 22219 | Pcdhb12 | NM_053137.2 | chr18:37595275-37598308 |
| 22220 | Pcdhb13 | NM_053138.3 | chr18:37602171-37605863 |
| 22221 | Pcdhb14 | NM_053139.3 | chr18:37607311-37610748 |
| 22222 | Pcdhb15 | NM_053140.3 | chr18:377-376 |
| 22223 | Pcdhb16 | NM_053141.3 | chr18:37637422-37642691 |
| 22224 | Pcdhb17 | NM_053142.3 | chr18:37644675-37647944 |
| 22225 | Pcdhb18 | NM_053143.2 | chr18:37649139-37654157 |
| 22226 | Pcdhb19 | NM_053144.2 | chr18:37656652-37661365 |
| 22227 | Pcdhb2 | NM_053127.2 | chr18:37454494-37457268 |
| 22228 | Pcdhb20 | NM_053145.2 | chr18:37663918-37667314 |
| 22229 | Pcdhb21 | NM_053146.2 | chr18:37673306-37676017 |
| 22230 | Pcdhb22 | NM_053147.3 | chr18:37678007-37681073 |
| 22231 | Pcdhb3 | NM_053128.2 | chr18:37460453-37464239 |
| 22232 | Pcdhb4 | NM_053129.3 | chr18:37467109-37470827 |
| 22233 | Pcdhb5 | NM_053130.3 | chr18:37480095-37483567 |
| 22234 | Pcdhb6 | NM_053131.1 | chr18:37493682-37496000 |
| 22235 | Pcdhb7 | NM_053132.3 | chr18:37501356-37504861 |
| 22236 | Pcdhb8 | NM_053133.1 | chr18:37514925-37517264 |
| 22237 | Pcdhb9 | NM_053134.3 | chr18:37560509-37563563 |
| 22238 | Pcdhga1 | NM_033584.1 | chr18:37821599-38001524 |
| 22239 | Pcdhga10 | NM_033593.3 | chr18:37906842-38001526 |
| 22240 | Pcdhga11 | NM_033594.2 | chr18:37915427-38001526 |
| 22241 | Pcdhga12 | NM_033595.4 | chr18:37925234-38001526 |
| 22242 | Pcdhga2 | NM_033585.1 | chr18:37828759-38001526 |
| 22243 | Pcdhga3 | NM_033586.2 | chr18:37833989-38001526 |
| 22244 | Pcdhga4 | NM_033587.3 | chr18:37845054-38001524 |
| 22245 | Pcdhga5 | NM_033588.4 | chr18:37854155-38001524 |
| 22246 | Pcdhga6 | NM_033589.1 | chr18:37866883-38001524 |
| 22247 | Pcdhga7 | NM_033590.3 | chr18:37874488-38001526 |

| | | | |
|---|---|---|---|
| 22248 | Pcdhga8 | NM_033591.3 | chr18:37885360-38001526 |
| 22249 | Pcdhga9 | NM_033592.3 | chr18:37896590-38001517 |
| 22250 | Pcdhgb1 | NM_033574.3 | chr18:37840112-38001524 |
| 22251 | Pcdhgb2 | NM_033575.3 | chr18:37849513-38001526 |
| 22252 | Pcdhgb4 | NM_033576.1 | chr18:37880208-38001524 |
| 22253 | Pcdhgb5 | NM_033577.1 | chr18:37890808-38001524 |
| 22254 | Pcdhgb6 | NM_033578.3 | chr18:37901748-38001526 |
| 22255 | Pcdhgb7 | NM_033579.1 | chr18:37911433-38001524 |
| 22256 | Pcdhgb8 | NM_033580.2 | chr18:37921455-38001526 |
| 22257 | Pcdhgc3 | NM_033581.3 | chr18:37966064-38001526 |
| 22258 | Pcdhgc4 | NM_033582.2 | chr18:37974733-38001526 |
| 22259 | Pcdhgc5 | NM_033583.3 | chr18:37979200-38001526 |
| 22260 | Pced1a | NM_001114541.1 | chr2:130243419-130270005 |
| 22261 | Pced1a | NM_178762.4 | chr2:130243419-130270005 |
| 22262 | Pced1b | NM_172293.4 | chr15:97077538-97216122 |
| 22263 | Pcf11 | NM_029078.3 | chr7:99792221-99818422 |
| 22264 | Pcgf1 | NM_197992.1 | chr6:83028383-83030849 |
| 22265 | Pcgf2 | NM_001163307.1 | chr11:97550136-97561811 |
| 22266 | Pcgf2 | NM_001163308.1 | chr11:97550136-97561811 |
| 22267 | Pcgf2 | NM_009545.2 | chr11:97550136-97561811 |
| 22268 | Pcgf3 | NM_172716.4 | chr5:108890350-108932118 |
| 22269 | Pcgf5 | NM_029508.3 | chr19:36453556-36530694 |
| 22270 | Pcgf6 | NM_027654.2 | chr19:47108108-47125335 |
| 22271 | Pcid2 | NM_178708.2 | chr8:13077524-13105343 |
| 22272 | Pcif1 | NM_146129.3 | chr2:164704867-164716937 |
| 22273 | Pck1 | NM_011044.2 | chr2:172978573-172984754 |
| 22274 | Pck2 | NM_028994.1 | chr14:56159102-56168854 |
| 22275 | Pclo | NM_001110796.2 | chr5:14514917-14863459 |
| 22276 | Pclo | NM_011995.4 | chr5:14514917-14863459 |
| 22277 | Pcm1 | NM_023662.3 | chr8:42325112-42419441 |
| 22278 | Pcmt1 | NM_008786.2 | chr10:7350034-7383382 |
| 22279 | Pcmtd1 | NM_183028.3 | chr1:7079000-7163709 |
| 22280 | Pcmtd2 | NM_001291211.1 | chr2:181572558-181592165 |
| 22281 | Pcmtd2 | NM_153594.3 | chr2:181572558-181592165 |
| 22282 | Pcna | NM_011045.2 | chr2:132075021-132078916 |
| 22283 | Pcnp | NM_001024622.2 | chr16:56015620-56029830 |
| 22284 | Pcnt | NM_001282992.1 | chr10:75813998-75905657 |
| 22285 | Pcnt | NM_008787.3 | chr10:75813998-75905657 |
| 22286 | Pcnt | NM_018814.3 | chr12:82961016-83101911 |
| 22287 | Pcnxl2 | NM_175561.4 | chr8:128275407-128422217 |
| 22288 | Pcnxl3 | NM_144868.3 | chr19:5664635-5688908 |
| 22289 | Pcnxl4 | NM_026327.3 | chr12:73637343-73681200 |
| 22290 | Pcolce | NM_008788.2 | chr5:138046334-138052632 |
| 22291 | Pcolce2 | NM_029620.2 | chr9:95538046-95595970 |
| 22292 | Pcp2 | NM_001129803.1 | chr8:3621550-3625545 |
| 22293 | Pcp2 | NM_001129804.1 | chr8:3621550-3625545 |
| 22294 | Pcp2 | NM_008790.2 | chr8:3621550-3625545 |
| 22295 | Pcp4 | NM_008791.2 | chr16:96689212-96747400 |
| 22296 | Pcp4l1 | NM_025557.1 | chr1:173103394-173126399 |
| 22297 | Pcsk1 | NM_013628.2 | chr13:75227434-75269946 |
| 22298 | Pcsk1n | NM_013892.3 | chrX:7496948-7501536 |
| 22299 | Pcsk2 | NM_008792.4 | chr2:143371869-143642018 |
| 22300 | Pcsk2os1 | NR_040354.1 | chr2:143361212-143373573 |
| 22301 | Pcsk2os2 | NR_040625.1 | chr2:143573319-143614922 |
| 22302 | Pcsk4 | NM_008793.2 | chr10:79784027-79792218 |
| 22303 | Pcsk5 | NM_001163144.1 | chr19:17507321-17912122 |
| 22304 | Pcsk5 | NM_001190483.1 | chr19:17507321-17912122 |
| 22305 | Pcsk6 | NM_001291184.1 | chr7:73007021-73195272 |
| 22306 | Pcsk6 | NM_011048.1 | chr7:73007021-73195272 |
| 22307 | Pcsk7 | NM_001281934.1 | chr9:45671773-45744141 |
| 22308 | Pcsk7 | NM_008794.2 | chr9:45671773-45744141 |
| 22309 | Pcsk7 | NR_104055.1 | chr9:45671773-45744141 |
| 22310 | Pcsk9 | NM_153565.2 | chr4:106114938-106136930 |
| 22311 | Pctp | NM_008796.2 | chr11:89844730-89864208 |
| 22312 | Pcx | NM_001162946.1 | chr19:4510471-4621752 |
| 22313 | Pcx | NM_008797.3 | chr19:4510471-4621752 |
| 22314 | Pcyox1 | NM_025823.4 | chr6:86335999-86347144 |
| 22315 | Pcyox1l | NM_172832.4 | chr18:61856490-61867289 |
| 22316 | Pcyt1a | NM_001163159.1 | chr16:32431006-32475151 |
| 22317 | Pcyt1a | NM_001163160.1 | chr16:32431006-32475151 |
| 22318 | Pcyt1a | NM_009981.4 | chr16:32431006-32475151 |
| 22319 | Pcyt1b | NM_177546.2 | chrX:90900201-90995287 |
| 22320 | Pcyt1b | NM_211138.1 | chrX:90900201-90995287 |
| 22321 | Pcyt2 | NM_024229.2 | chr11:120471400-120479204 |
| 22322 | Pdap1 | NM_001033313.3 | chr5:145889638-145900958 |
| 22323 | Pdc | NM_001159730.1 | chr1:152166546-152193901 |
| 22324 | Pdc | NM_024458.2 | chr1:152166546-152193901 |
| 22325 | Pdcd1 | NM_008798.2 | chr1:95934881-95949130 |
| 22326 | Pdcd10 | NM_019745.4 | chr3:75320411-75360774 |
| 22327 | Pdcd11 | NM_011053.2 | chr19:47165255-47205635 |
| 22328 | Pdcd1lg2 | NM_021396.2 | chr19:29485408-29547417 |
| 22329 | Pdcd2 | NM_008799.2 | chr17:15658538-15664265 |
| 22330 | Pdcd2l | NM_026549.3 | chr7:34969515-34981666 |
| 22331 | Pdcd4 | NM_001168491.1 | chr19:53966720-54107768 |
| 22332 | Pdcd4 | NM_001168492.1 | chr19:53966720-54107768 |
| 22333 | Pdcd4 | NM_011050.4 | chr19:53966720-54107768 |
| 22334 | Pdcd5 | NM_019746.4 | chr7:36427003-36432501 |
| 22335 | Pdcd6 | NM_011051.3 | chr13:74440568-74454774 |
| 22336 | Pdcd6ip | NM_001164677.1 | chr9:113560861-113617377 |
| 22337 | Pdcd6ip | NM_001164678.1 | chr9:113560861-113617377 |
| 22338 | Pdcd6ip | NM_011052.2 | chr9:113560861-113617377 |
| 22339 | Pdcd7 | NM_016688.2 | chr9:65193874-65207450 |
| 22340 | Pdcl | NM_026176.3 | chr7:37205593-37214852 |
| 22341 | Pdcl2 | NM_023508.6 | chr5:76741170-76760136 |
| 22342 | Pdcl3 | NM_026850.4 | chr1:39044658-39054081 |

Fig. 25 - 119

| | | | |
|---|---|---|---|
| 22343 | Pddc1 | NM_172116.4 | chr7:148594082-148600024 |
| 22344 | Pde10a | NM_001290707.1 | chr17:8719665-9179513 |
| 22345 | Pde10a | NM_011866.2 | chr17:8719665-9179513 |
| 22346 | Pde11a | NM_001081033.1 | chr2:75829188-76176710 |
| 22347 | Pde12 | NM_178668.3 | chr14:27483603-27489332 |
| 22348 | Pde1a | NM_001009978.1 | chr2:79674609-79969569 |
| 22349 | Pde1a | NM_001009979.1 | chr2:79674609-79969569 |
| 22350 | Pde1a | NM_001159582.1 | chr2:79674609-79969569 |
| 22351 | Pde1a | NM_016744.4 | chr2:79674609-79969569 |
| 22352 | Pde1b | NM_001285890.1 | chr15:103333464-103360487 |
| 22353 | Pde1b | NM_008800.2 | chr15:103333464-103360487 |
| 22354 | Pde1c | NM_001025568.2 | chr6:56019797-56319628 |
| 22355 | Pde1c | NM_001159952.1 | chr6:56019797-56319628 |
| 22356 | Pde1c | NM_001159953.1 | chr6:56019797-56319628 |
| 22357 | Pde1c | NM_001159955.1 | chr6:56019797-56319628 |
| 22358 | Pde1c | NM_001159956.1 | chr6:56019797-56319628 |
| 22359 | Pde1c | NM_001159959.1 | chr6:56019797-56319628 |
| 22360 | Pde1c | NM_001159960.1 | chr6:56019797-56319628 |
| 22361 | Pde1c | NM_011054.4 | chr6:56019797-56319628 |
| 22362 | Pde2a | NM_001008548.4 | chr7:108570204-108661343 |
| 22363 | Pde2a | NM_001143848.2 | chr7:108570204-108661343 |
| 22364 | Pde2a | NM_001143849.2 | chr7:108570204-108661343 |
| 22365 | Pde2a | NM_001243757.1 | chr7:108570204-108661343 |
| 22366 | Pde2a | NM_001243758.1 | chr7:108570204-108661343 |
| 22367 | Pde3a | NM_018779.1 | chr6:141197790-141447872 |
| 22368 | Pde3b | NM_011055.2 | chr7:121558767-121681451 |
| 22369 | Pde4a | NM_019798.5 | chr9:20970157-21017692 |
| 22370 | Pde4a | NM_183408.3 | chr9:20970157-21017692 |
| 22371 | Pde4b | NM_001177980.1 | chr4:101927346-102279867 |
| 22372 | Pde4b | NM_001177981.1 | chr4:101927346-102279867 |
| 22373 | Pde4b | NM_001177982.1 | chr4:101927346-102279867 |
| 22374 | Pde4b | NM_001177983.1 | chr4:101927346-102279867 |
| 22375 | Pde4b | NM_019840.1 | chr4:101927346-102279867 |
| 22376 | Pde4c | NM_201607.2 | chr8:73247962-73275075 |
| 22377 | Pde4d | NM_011056.3 | chr13:109444371-110746177 |
| 22378 | Pde4dip | NM_001039535.2 | chr3:97493750-97692630 |
| 22379 | Pde4dip | NM_001289701.1 | chr3:97493750-97692630 |
| 22380 | Pde4dip | NM_001289702.1 | chr3:97493750-97692630 |
| 22381 | Pde4dip | NM_178080.4 | chr3:97493750-97692630 |
| 22382 | Pde4dip | NR_110360.1 | chr3:97493750-97692630 |
| 22383 | Pde5a | NM_153422.2 | chr3:122432076-122562292 |
| 22384 | Pde6a | NM_146804.2 | chr18:61380152-61449372 |
| 22385 | Pde6b | NM_008806.2 | chr5:108817391-108860761 |
| 22386 | Pde6c | NM_001170959.1 | chr19:38207270-38258441 |
| 22387 | Pde6c | NM_033614.2 | chr19:38207270-38258441 |
| 22388 | Pde6d | NM_008801.2 | chr1:88439589-88479076 |
| 22389 | Pde6g | NM_012065.3 | chr11:120308923-120314797 |
| 22390 | Pde6h | NM_023898.4 | chr6:136908043-136912004 |
| 22391 | Pde7a | NM_001222759.2 | chr3:19123108-19211322 |
| 22392 | Pde7a | NM_008802.3 | chr3:19123108-19211322 |
| 22393 | Pde7b | NM_013875.5 | chr10:20117809-20444874 |
| 22394 | Pde8a | NM_008803.2 | chr7:88358689-88478508 |
| 22395 | Pde8b | NM_001170669.1 | chr13:95794059-96020259 |
| 22396 | Pde8b | NM_172263.2 | chr13:95794059-96020259 |
| 22397 | Pde9a | NM_001163748.1 | chr17:31523178-31613254 |
| 22398 | Pde9a | NM_008804.4 | chr17:31523178-31613254 |
| 22399 | Pdf | NM_026513.2 | chr8:109570189-109572514 |
| 22400 | Pdgfa | NM_008808.3 | chr5:139452928-139470907 |
| 22401 | Pdgfb | NM_011057.3 | chr15:79826306-79845238 |
| 22402 | Pdgfc | NM_019971.2 | chr3:80840337-81017953 |
| 22403 | Pdgfd | NM_027924.2 | chr9:6168612-6377519 |
| 22404 | Pdgfra | NM_001083316.1 | chr5:75548315-75594229 |
| 22405 | Pdgfra | NM_011058.2 | chr5:75548315-75594229 |
| 22406 | Pdgfrb | NM_001146268.1 | chr18:61204803-61244721 |
| 22407 | Pdgfrb | NM_008809.2 | chr18:61204803-61244721 |
| 22408 | Pdgfrl | NM_026840.3 | chr8:42015586-42076124 |
| 22409 | Pdha1 | NM_008810.2 | chrX:156560151-156576268 |
| 22410 | Pdha2 | NM_008811.3 | chr3:140872967-140875319 |
| 22411 | Pdhb | NM_024221.3 | chr14:8998504-9005506 |
| 22412 | Pdhx | NM_175094.4 | chr2:102861212-102913670 |
| 22413 | Pdia2 | NM_001081070.1 | chr17:26332943-26336032 |
| 22414 | Pdia3 | NM_007952.2 | chr2:121239637-121264422 |
| 22415 | Pdia4 | NM_009787.2 | chr6:47746140-47776511 |
| 22416 | Pdia5 | NM_028295.1 | chr16:35397397-35490959 |
| 22417 | Pdia6 | NM_027959.3 | chr12:17273401-17291576 |
| 22418 | Pdik1l | NM_001163764.1 | chr4:133830920-133843761 |
| 22419 | Pdik1l | NM_146156.3 | chr4:133830920-133843761 |
| 22420 | Pdilt | NM_027943.1 | chr7:126630100-126666996 |
| 22421 | Pdk1 | NM_172665.5 | chr2:71711280-71741915 |
| 22422 | Pdk2 | NM_133667.2 | chr11:94887571-94902685 |
| 22423 | Pdk3 | NM_145630.2 | chrX:91009954-91077434 |
| 22424 | Pdk4 | NM_013743.2 | chr6:5433450-5446278 |
| 22425 | Pdlim1 | NM_016861.4 | chr19:40296728-40346106 |
| 22426 | Pdlim2 | NM_001253736.1 | chr14:70564024-70577479 |
| 22427 | Pdlim2 | NM_145978.2 | chr14:70564024-70577479 |
| 22428 | Pdlim3 | NM_016798.3 | chr8:46970838-47004900 |
| 22429 | Pdlim4 | NM_019417.3 | chr11:53868429-53882519 |
| 22430 | Pdlim5 | NM_001190852.1 | chr3:141902548-142058660 |
| 22431 | Pdlim5 | NM_001190853.1 | chr3:141902548-142058660 |
| 22432 | Pdlim5 | NM_001190854.1 | chr3:141902548-142058660 |
| 22433 | Pdlim5 | NM_001190855.1 | chr3:141902548-142058660 |
| 22434 | Pdlim5 | NM_001190856.1 | chr3:141902548-142058660 |
| 22435 | Pdlim5 | NM_001190857.1 | chr3:141902548-142058660 |
| 22436 | Pdlim5 | NM_019808.3 | chr3:141902548-142058660 |
| 22437 | Pdlim5 | NM_019809.3 | chr3:141902548-142058660 |
| 22438 | Pdlim5 | NM_022554.3 | chr3:141902548-142058660 |
| 22439 | Pdlim7 | NM_001114087.2 | chr13:55598847-55614807 |
| 22440 | Pdlim7 | NM_001114088.2 | chr13:55598847-55614807 |
| 22441 | Pdlim7 | NM_026131.4 | chr13:55598847-55614807 |
| 22442 | Pdlim7 | NR_104287.1 | chr13:55598847-55614807 |
| 22443 | Pdp1 | NM_001033453.3 | chr4:11885329-11893597 |
| 22444 | Pdp1 | NM_001098230.1 | chr4:11885329-11893597 |
| 22445 | Pdp1 | NM_001098231.1 | chr4:11885329-11893597 |
| 22446 | Pdp1 | NM_001290387.1 | chr4:11885329-11893597 |
| 22447 | Pdp1 | NM_001290391.1 | chr4:11885329-11893597 |
| 22448 | Pdp2 | NM_001024606.1 | chr8:107115367-107120749 |
| 22449 | Pdpk1 | NM_001080773.2 | chr17:24210646-24287889 |
| 22450 | Pdpk1 | NM_001286662.1 | chr17:24210646-24287889 |
| 22451 | Pdpk1 | NM_011062.4 | chr17:24210646-24287889 |
| 22452 | Pdpn | NM_001290822.1 | chr4:142857311-142889467 |
| 22453 | Pdpn | NM_010329.3 | chr4:142857311-142889467 |
| 22454 | Pdpr | NM_198308.1 | chr8:113618645-113659044 |
| 22455 | Pdrg1 | NM_178939.2 | chr2:152834625-152841119 |
| 22456 | Pds5a | NM_001081321.1 | chr5:66006498-66089095 |
| 22457 | Pds5b | NM_175310.6 | chr5:151476401-151613245 |
| 22458 | Pdss1 | NM_019501.3 | chr2:22751042-22795779 |
| 22459 | Pdss2 | NM_001168289.1 | chr10:42941291-43184688 |
| 22460 | Pdss2 | NM_027772.2 | chr10:42941291-43184688 |
| 22461 | Pdx1 | NM_008814.3 | chr5:148081707-148086725 |
| 22462 | Pdxdc1 | NM_001039533.2 | chr16:13819369-13903238 |
| 22463 | Pdxdc1 | NM_001291017.1 | chr16:13819369-13903238 |
| 22464 | Pdxdc1 | NM_053181.3 | chr16:13819369-13903238 |
| 22465 | Pdxk | NM_172134.2 | chr10:77899492-77927693 |
| 22466 | Pdxk-ps | NR_027316.1 | chr17:32213027-32228368 |
| 22467 | Pdxp | NM_020271.3 | chr15:78744348-78749947 |
| 22468 | Pdyn | NM_001286502.1 | chr2:129512284-129525674 |
| 22469 | Pdyn | NM_018863.4 | chr2:129512284-129525674 |
| 22470 | Pdzd11 | NM_028303.3 | chrX:97818244-97821246 |
| 22471 | Pdzd2 | NM_001081064.1 | chr15:12286808-12522311 |
| 22472 | Pdzd3 | NM_133226.2 | chr9:44055394-44059547 |
| 22473 | Pdzd4 | NM_001029868.2 | chrX:71038695-71070308 |
| 22474 | Pdzd4 | NM_001290540.1 | chrX:71038695-71070308 |
| 22475 | Pdzd7 | NM_001195265.1 | chr19:45101397-45120262 |
| 22476 | Pdzd8 | NM_001033222.3 | chr19:59370573-59420270 |
| 22477 | Pdzd9 | NM_001040136.2 | chr7:127778702-127813857 |
| 22478 | Pdzd9 | NM_001040137.2 | chr7:127778702-127813857 |
| 22479 | Pdzk1 | NM_001146001.1 | chr3:96663748-96674849 |
| 22480 | Pdzk1 | NM_021517.2 | chr3:96663748-96674849 |
| 22481 | Pdzk1ip1 | NM_001164557.1 | chr4:114761312-114766499 |
| 22482 | Pdzk1ip1 | NM_001164558.1 | chr4:114761312-114766499 |
| 22483 | Pdzk1ip1 | NM_026018.3 | chr4:114761312-114766499 |
| 22484 | Pdzrn3 | NM_018884.2 | chr6:101099600-101327891 |
| 22485 | Pdzrn4 | NM_001164593.1 | chr15:92227240-92602250 |
| 22486 | Pdzrn4 | NM_001164594.1 | chr15:92227240-92602250 |
| 22487 | Pea15a | NM_011063.2 | chr1:174126859-174136912 |
| 22488 | Pea15b | NR_027806.1 | chr5:77940219-77940773 |
| 22489 | Peak1 | NM_172924.3 | chr9:56048935-56265857 |
| 22490 | Pear1 | NM_001032413.1 | chr3:87553018-87572875 |
| 22491 | Pear1 | NM_001032414.1 | chr3:87553018-87572875 |
| 22492 | Pear1 | NM_001289600.1 | chr3:87553018-87572875 |
| 22493 | Pear1 | NM_001289601.1 | chr3:87553018-87572875 |
| 22494 | Pear1 | NM_028460.2 | chr3:87553018-87572875 |
| 22495 | Pear1 | NM_152799.2 | chr3:87553018-87572875 |
| 22496 | Pebp1 | NM_018858.2 | chr5:117732659-117737573 |
| 22497 | Pebp4 | NM_028526.4 | chr14:70240213-70459725 |
| 22498 | Pebp4 | NM_028560.4 | chr14:70240213-70459725 |
| 22499 | Pecam1 | NM_001032378.2 | chr11:106515531-106576595 |
| 22500 | Pecam1 | NM_008816.3 | chr11:106515531-106576595 |
| 22501 | Pecr | NM_023523.5 | chr1:72305746-72330888 |
| 22502 | Pef1 | NM_026441.4 | chr4:129784799-129805378 |
| 22503 | Peg10 | NM_001040611.1 | chr6:4697305-4710516 |
| 22504 | Peg12 | NM_013788.2 | chr7:69606756-69609396 |
| 22505 | Peg13 | NR_002864.1 | chr15:72636030-72640754 |
| 22506 | Peg3 | NM_008817.2 | chr7:6658671-6683130 |
| 22507 | Peg3os | NR_023846.1 | chr7:6659471-6660335 |
| 22508 | Peli1 | NM_023324.2 | chr11:20991326-21050330 |
| 22509 | Peli2 | NM_033602.2 | chr14:48740544-48880558 |
| 22510 | Peli3 | NM_172835.3 | chr19:4931854-4943092 |
| 22511 | Pelo | NM_134058.3 | chr13:115878563-115880366 |
| 22512 | Pelp1 | NM_029231.4 | chr11:70206382-70223533 |
| 22513 | Pemt | NM_001290011.1 | chr11:59784115-59859991 |
| 22514 | Pemt | NM_001290012.1 | chr11:59784115-59859991 |
| 22515 | Pemt | NM_001290013.1 | chr11:59784115-59859991 |
| 22516 | Pemt | NM_001290014.1 | chr11:59784115-59859991 |
| 22517 | Pemt | NM_008819.3 | chr11:59784115-59859991 |
| 22518 | Penk | NM_001002927.2 | chr4:4060682-4065592 |
| 22519 | Peo1 | NM_153796.3 | chr19:45081047-45087252 |
| 22520 | Pepd | NM_008820.2 | chr7:35697425-35829727 |
| 22521 | Per1 | NM_001159367.1 | chr11:68912457-68923459 |
| 22522 | Per1 | NM_011065.4 | chr11:68912457-68923459 |
| 22523 | Per2 | NM_011066.2 | chr1:93312558-93355905 |
| 22524 | Per3 | NM_001289877.1 | chr4:150377763-150418774 |
| 22525 | Per3 | NM_001289878.1 | chr4:150377763-150418774 |
| 22526 | Per3 | NM_011067.3 | chr4:150377763-150418774 |
| 22527 | Peril | NR_110488.1 | chr3:34670996-34681268 |
| 22528 | Perm1 | NM_172417.3 | chr4:155590035-155595416 |
| 22529 | Perp | NM_022032.4 | chr10:18564876-18576878 |
| 22530 | Pes1 | NM_022889.3 | chr11:3863977-3880007 |
| 22531 | Pet100 | NM_001195244.1 | chr8:3621551-3624235 |
| 22532 | Pet112 | NM_144896.1 | chr3:85378050-85458392 |

Fig. 25 - 120

| | | | |
|---|---|---|---|
| 22533 | Pet117 | NM_001164813.1 | chr2:144194719-144199073 |
| 22534 | Pet2 | NM_008821.2 | chrX:86649186-86655028 |
| 22535 | Pex1 | NM_027777.2 | chr5:3596066-3637230 |
| 22536 | Pex10 | NM_001042407.1 | chr4:154441138-154446515 |
| 22537 | Pex11a | NM_011068.1 | chr7:86882149-86887911 |
| 22538 | Pex11b | NM_001162387.1 | chr3:96439279-96449304 |
| 22539 | Pex11b | NM_001162388.1 | chr3:96439279-96449304 |
| 22540 | Pex11b | NM_011069.3 | chr3:96439279-96449304 |
| 22541 | Pex11b | NR_027844.1 | chr3:96439279-96449304 |
| 22542 | Pex11b | NR_027845.1 | chr3:96439279-96449304 |
| 22543 | Pex11g | NM_026951.2 | chr8:3458816-3467648 |
| 22544 | Pex12 | NM_134025.3 | chr11:83108147-83112479 |
| 22545 | Pex13 | NM_023651.4 | chr11:23546479-23565935 |
| 22546 | Pex14 | NM_019781.2 | chr4:148334643-148473921 |
| 22547 | Pex16 | NM_145122.2 | chr2:92214832-92221377 |
| 22548 | Pex16 | NR_028114.1 | chr2:92214832-92221377 |
| 22549 | Pex19 | NM_001159525.1 | chr1:174056885-174066628 |
| 22550 | Pex19 | NM_023041.3 | chr1:174056885-174066628 |
| 22551 | Pex2 | NM_001163301.2 | chr3:5560187-5576248 |
| 22552 | Pex2 | NM_001163302.2 | chr3:5560187-5576248 |
| 22553 | Pex2 | NM_001163305.2 | chr3:5560187-5576248 |
| 22554 | Pex2 | NM_001163306.2 | chr3:5560187-5576248 |
| 22555 | Pex2 | NM_001267714.1 | chr3:5560187-5576248 |
| 22556 | Pex2 | NM_001267715.1 | chr3:5560187-5576248 |
| 22557 | Pex2 | NM_008994.4 | chr3:5560187-5576248 |
| 22558 | Pex26 | NM_028730.6 | chr6:121138684-121146203 |
| 22559 | Pex3 | NM_001164195.1 | chr10:13243647-13283182 |
| 22560 | Pex3 | NM_019961.3 | chr10:13243647-13283182 |
| 22561 | Pex5 | NM_001277330.1 | chr6:124346833-124365085 |
| 22562 | Pex5 | NM_001277805.1 | chr6:124346833-124365085 |
| 22563 | Pex5 | NM_008995.3 | chr6:124346833-124365085 |
| 22564 | Pex5 | NM_175933.2 | chr6:124346833-124365085 |
| 22565 | Pex5l | NM_001163516.2 | chr3:32848555-33042113 |
| 22566 | Pex5l | NM_001163517.2 | chr3:32848555-33042113 |
| 22567 | Pex5l | NM_001289505.1 | chr3:32848555-33042113 |
| 22568 | Pex5l | NM_021483.4 | chr3:32848555-33042113 |
| 22569 | Pex6 | NM_145488.1 | chr17:46848411-46862490 |
| 22570 | Pex7 | NM_001161825.1 | chr10:19579895-19627480 |
| 22571 | Pex7 | NM_008822.2 | chr10:19579895-19627480 |
| 22572 | Pf4 | NM_019932.4 | chr5:91201460-91202409 |
| 22573 | Pfas | NM_001159519.1 | chr11:68799203-68821962 |
| 22574 | Pfdn1 | NM_026027.3 | chr18:36563332-36614449 |
| 22575 | Pfdn2 | NM_011070.3 | chr1:173275829-173288301 |
| 22576 | Pfdn4 | NM_001013369.1 | chr2:170308464-170344570 |
| 22577 | Pfdn4 | NM_001110152.2 | chr2:170308464-170344570 |
| 22578 | Pfdn4 | NM_001199902.1 | chr2:170308464-170344570 |
| 22579 | Pfdn5 | NM_027044.3 | chr15:102156546-102161920 |
| 22580 | Pfkfb1 | NM_008824.4 | chrX:147024463-147078421 |
| 22581 | Pfkfb2 | NM_001162415.1 | chr1:132585619-132625830 |
| 22582 | Pfkfb2 | NM_001162416.1 | chr1:132585619-132625830 |
| 22583 | Pfkfb2 | NM_008825.4 | chr1:132585619-132625830 |
| 22584 | Pfkfb2 | NR_027859.1 | chr1:132585619-132625830 |
| 22585 | Pfkfb3 | NM_001177752.1 | chr2:11393057-11475556 |
| 22586 | Pfkfb3 | NM_001177753.1 | chr2:11393057-11475556 |
| 22587 | Pfkfb3 | NM_001177754.1 | chr2:11393057-11475556 |
| 22588 | Pfkfb3 | NM_001177755.1 | chr2:11393057-11475556 |
| 22589 | Pfkfb3 | NM_001177756.1 | chr2:11393057-11475556 |
| 22590 | Pfkfb3 | NM_001177757.1 | chr2:11393057-11475556 |
| 22591 | Pfkfb3 | NM_001177758.1 | chr2:11393057-11475556 |
| 22592 | Pfkfb3 | NM_133232.3 | chr2:11393057-11475556 |
| 22593 | Pfkfb4 | NM_173019.5 | chr9:108893946-108934739 |
| 22594 | Pfkl | NM_008826.4 | chr10:77449693-77472541 |
| 22595 | Pfkm | NM_001163487.1 | chr15:97869174-97962878 |
| 22596 | Pfkm | NM_001163488.1 | chr15:97869174-97962878 |
| 22597 | Pfkm | NM_021514.4 | chr15:97869174-97962878 |
| 22598 | Pfkp | NM_001291071.1 | chr13:6547402-6648017 |
| 22599 | Pfkp | NM_019703.4 | chr13:6547402-6648017 |
| 22600 | Pfn1 | NM_011072.4 | chr11:70465348-70468152 |
| 22601 | Pfn2 | NM_019410.3 | chr3:57645816-57651679 |
| 22602 | Pfn3 | NM_029303.2 | chr13:55516049-55516593 |
| 22603 | Pfn4 | NM_028376.2 | chr12:4776100-4785072 |
| 22604 | Pfpl | NM_019540.1 | chr19:12502394-12506600 |
| 22605 | Pga5 | NM_021584.4 | chr19:10743446-10752541 |
| 22606 | Pgam1 | NM_023418.2 | chr19:41986360-41993155 |
| 22607 | Pgam2 | NM_018870.3 | chr11:5701639-5703799 |
| 22608 | Pgam5 | NM_001163538.1 | chr5:110688153-110698918 |
| 22609 | Pgam5 | NM_028273.3 | chr5:110688153-110698918 |
| 22610 | Pgap1 | NM_001163314.2 | chr1:54529843-54614528 |
| 22611 | Pgap2 | NM_001291358.1 | chr7:109358848-109387078 |
| 22612 | Pgap2 | NM_145583.3 | chr7:109358848-109387078 |
| 22613 | Pgap2 | NR_111937.1 | chr7:109358848-109387078 |
| 22614 | Pgap2 | NR_111938.1 | chr7:109358848-109387078 |
| 22615 | Pgap3 | NM_001033537.2 | chr11:98249985-98261804 |
| 22616 | Pgbd1 | NM_001012311.2 | chr13:21513143-21532922 |
| 22617 | Pgbd1 | NM_001162919.1 | chr13:21513143-21532922 |
| 22618 | Pgbd1 | NM_001162920.1 | chr13:21513143-21532922 |
| 22619 | Pgbd5 | NM_171824.2 | chr8:126892948-126957836 |
| 22620 | Pgc | NM_025973.3 | chr17:47863790-47871427 |
| 22621 | Pgd | NM_001081274.1 | chr4:148524093-148540816 |
| 22622 | Pgf | NM_001271705.1 | chr12:86507588-86518263 |
| 22623 | Pgf | NM_008827.3 | chr12:86507588-86518263 |
| 22624 | Pggt1b | NM_172627.3 | chr18:46399602-46440504 |
| 22625 | Pgk1 | NM_008828.3 | chrX:103382438-103399038 |
| 22626 | Pgk2 | NM_031190.2 | chr17:40343962-40345554 |
| 22627 | Pgls | NM_025396.3 | chr8:74116082-74120166 |
| 22628 | Pglyrp1 | NM_009402.2 | chr7:19470038-19475787 |
| 22629 | Pglyrp2 | NM_001271476.1 | chr17:32549405-32561112 |
| 22630 | Pglyrp2 | NM_001271477.1 | chr17:32549405-32561112 |
| 22631 | Pglyrp2 | NM_001271478.1 | chr17:32549405-32561112 |
| 22632 | Pglyrp2 | NM_001271479.1 | chr17:32549405-32561112 |
| 22633 | Pglyrp2 | NM_021319.5 | chr17:32549405-32561112 |
| 22634 | Pglyrp2 | NR_073184.1 | chr17:32549405-32561112 |
| 22635 | Pglyrp3 | NM_207247.4 | chr3:91818504-91835506 |
| 22636 | Pglyrp4 | NM_001165968.1 | chr3:90530827-90545439 |
| 22637 | Pglyrp4 | NM_207263.2 | chr3:90530827-90545439 |
| 22638 | Pgm1 | NM_025700.2 | chr5:64484188-64519397 |
| 22639 | Pgm2 | NM_028132.3 | chr4:99602055-99659899 |
| 22640 | Pgm2l1 | NM_027629.3 | chr7:107376117-107427382 |
| 22641 | Pgm3 | NM_001163746.1 | chr9:86360760-86465449 |
| 22642 | Pgm3 | NM_028352.4 | chr9:86360760-86465449 |
| 22643 | Pgm5 | NM_175013.2 | chr19:24752751-24936332 |
| 22644 | Pgp | NM_025954.3 | chr17:24607417-24608541 |
| 22645 | Pgpep1 | NM_023217.4 | chr8:73170334-73183637 |
| 22646 | Pgpep1l | NM_030101.1 | chr7:75381493-75409119 |
| 22647 | Pgr | NM_008829.2 | chr9:8899832-8968611 |
| 22648 | Pgr15l | NM_001033361.3 | chrX:94267934-94277443 |
| 22649 | Pgrmc1 | NM_016783.3 | chrX:34138219-34146074 |
| 22650 | Pgrmc2 | NM_027558.1 | chr3:40870247-40886968 |
| 22651 | Pgs1 | NM_133757.2 | chr11:117848171-117885325 |
| 22652 | Phactr1 | NM_001005740.1 | chr13:42775991-43233881 |
| 22653 | Phactr1 | NM_001005748.2 | chr13:42775991-43233881 |
| 22654 | Phactr1 | NM_198419.3 | chr13:42775991-43233881 |
| 22655 | Phactr2 | NM_001033257.4 | chr10:12927522-13194202 |
| 22656 | Phactr2 | NM_001195065.1 | chr10:12927522-13194202 |
| 22657 | Phactr2 | NM_001195066.1 | chr10:12927522-13194202 |
| 22658 | Phactr2 | NM_001195096.1 | chr10:12927522-13194202 |
| 22659 | Phactr3 | NM_001007154.2 | chr2:177853679-178073197 |
| 22660 | Phactr3 | NM_001177789.1 | chr2:177853679-178073197 |
| 22661 | Phactr3 | NM_001177790.1 | chr2:177853679-178073197 |
| 22662 | Phactr3 | NM_001177791.1 | chr2:177853679-178073197 |
| 22663 | Phactr3 | NM_028806.2 | chr2:177853679-178073197 |
| 22664 | Phactr4 | NM_001161797.1 | chr4:131911838-131978361 |
| 22665 | Phactr4 | NM_175306.4 | chr4:131911838-131978361 |
| 22666 | Phax | NM_001162989.1 | chr18:56685389-56747366 |
| 22667 | Phax | NM_019996.4 | chr18:56685389-56747366 |
| 22668 | Phb | NM_008831.4 | chr11:95528270-95542087 |
| 22669 | Phb2 | NM_007531.2 | chr6:124662306-124666963 |
| 22670 | Phc1 | NM_001042623.2 | chr6:122267748-122290245 |
| 22671 | Phc1 | NM_001271579.1 | chr6:122267748-122290245 |
| 22672 | Phc1 | NM_007905.3 | chr6:122267748-122290245 |
| 22673 | Phc1 | NR_073364.1 | chr6:122267748-122290245 |
| 22674 | Phc2 | NM_001195083.1 | chr4:128331945-128430125 |
| 22675 | Phc2 | NM_001195130.1 | chr4:128331945-128430125 |
| 22676 | Phc2 | NM_018774.4 | chr4:128331945-128430125 |
| 22677 | Phc3 | NM_001165954.1 | chr3:30798216-30868337 |
| 22678 | Phc3 | NM_001165955.1 | chr3:30798216-30868337 |
| 22679 | Phc3 | NM_001165956.1 | chr3:30798216-30868337 |
| 22680 | Phc3 | NM_153421.2 | chr3:30798216-30868337 |
| 22681 | Phex | NM_011077.2 | chrX:153596617-153853218 |
| 22682 | Phf1 | NM_009343.3 | chr17:27070072-27074853 |
| 22683 | Phf10 | NM_024250.4 | chr17:15082000-15098237 |
| 22684 | Phf11a | NM_172603.3 | chr14:59895749-59916359 |
| 22685 | Phf11b | NM_001164327.1 | chr14:59939800-59960167 |
| 22686 | Phf11c | NM_001164289.1 | chr14:59999669-60012349 |
| 22687 | Phf11d | NM_199015.4 | chr14:59966243-59984327 |
| 22688 | Phf12 | NM_174852.3 | chr11:77796317-77844037 |
| 22689 | Phf13 | NM_172705.2 | chr4:151363739-151370288 |
| 22690 | Phf14 | NM_001168382.1 | chr6:11875880-12031198 |
| 22691 | Phf14 | NM_029404.3 | chr6:11875880-12031198 |
| 22692 | Phf19 | NM_028716.4 | chr2:34749274-34769496 |
| 22693 | Phf2 | NM_011078.3 | chr13:48897118-48966254 |
| 22694 | Phf2l | NM_172674.2 | chr2:156022382-156135689 |
| 22695 | Phf20l1 | NM_001081409.1 | chr15:66409133-66476817 |
| 22696 | Phf21a | NM_001109690.1 | chr2:92024338-92204823 |
| 22697 | Phf21a | NM_001109691.1 | chr2:92024338-92204823 |
| 22698 | Phf21a | NM_138755.2 | chr2:92024338-92204823 |
| 22699 | Phf21b | NM_001081166.2 | chr15:84615805-84686559 |
| 22700 | Phf21b | NR_030731.1 | chr15:84615805-84686559 |
| 22701 | Phf23 | NM_001291125.1 | chr11:69809267-69813513 |
| 22702 | Phf23 | NM_001291126.1 | chr11:69809267-69813513 |
| 22703 | Phf23 | NM_001291127.1 | chr11:69809267-69813513 |
| 22704 | Phf23 | NM_030064.4 | chr11:69809267-69813513 |
| 22705 | Phf3 | NM_001081080.1 | chr1:30859186-30920101 |
| 22706 | Phf5a | NM_026737.3 | chr15:81694945-81702322 |
| 22707 | Phf6 | NM_001290546.1 | chrX:50265390-50310138 |
| 22708 | Phf6 | NM_027642.2 | chrX:50265390-50310138 |
| 22709 | Phf7 | NM_027949.1 | chr14:32050881-32064404 |
| 22710 | Phf8 | NM_001133954.1 | chrX:147955214-148068400 |
| 22711 | Phf8 | NM_177201.1 | chrX:147955214-148068400 |
| 22712 | Phgdh | NM_016966.3 | chr3:98117093-98143892 |
| 22713 | Phgr1 | NM_001145644.1 | chr1:118598504-118603900 |
| 22714 | Phip | NM_001081216.1 | chr9:82759765-82869096 |
| 22715 | Phka1 | NM_008832.3 | chrX:99709313-99839585 |
| 22716 | Phka1 | NM_173021.3 | chrX:99709313-99839585 |
| 22717 | Phka2 | NM_001177878.1 | chrX:156940097-157036810 |
| 22718 | Phka2 | NM_001177879.1 | chrX:156940097-157036810 |
| 22719 | Phka2 | NM_172783.3 | chrX:156940097-157036810 |
| 22720 | Phkb | NM_199446.1 | chr8:88364900-88584541 |
| 22721 | Phkg1 | NM_011079.2 | chr5:130339311-130354954 |
| 22722 | Phkg2 | NM_026888.3 | chr7:134716862-134726821 |

Fig. 25 - 121

| | | | | | | | |
|---|---|---|---|---|---|---|---|
| 22723 | Phlda1 | NM_009344.3 | chr10:110943341-110945705 | 22818 | Pigv | NM_178698.5 | chr4:133217339-133228562 |
| 22724 | Phlda2 | NM_009434.2 | chr7:150687452-150688429 | 22819 | Pigw | NM_001077636.1 | chr11:84689814-84729858 |
| 22725 | Phlda3 | NM_013750.2 | chr1:137662681-137665711 | 22820 | Pigw | NM_027388.2 | chr11:84689814-84729858 |
| 22726 | Phldb1 | NM_153537.4 | chr9:44494390-44543281 | 22821 | Pigx | NM_001111025.1 | chr16:32084501-32099813 |
| 22727 | Phldb2 | NM_001252442.1 | chr16:45746343-45844491 | 22822 | Pigx | NM_024464.3 | chr16:32084501-32099813 |
| 22728 | Phldb2 | NM_153412.4 | chr16:45746343-45844491 | 22823 | Pigyl | NM_001082532.1 | chr9:21961289-21962798 |
| 22729 | Phldb3 | NM_001102613.1 | chr7:25396346-25414316 | 22824 | Pigz | NM_172822.3 | chr16:31933936-31946132 |
| 22730 | Phpp1 | NM_133821.3 | chr1:108068445-108290822 | 22825 | Pih1d1 | NM_001278207.1 | chr7:52397209-52415434 |
| 22731 | Phpp2 | NM_001122594.2 | chr8:112392502-112468571 | 22826 | Pih1d1 | NM_001285904.1 | chr7:52397209-52415434 |
| 22732 | Phospho1 | NM_153104.3 | chr11:95685814-95693454 | 22827 | Pih1d1 | NM_029406.4 | chr7:52397209-52415434 |
| 22733 | Phospho2 | NM_028521.2 | chr2:69627793-69635225 | 22828 | Pih1d2 | NM_028300.2 | chr9:50425426-50433105 |
| 22734 | Phox2a | NM_008887.2 | chr7:108966827-108971240 | 22829 | Pih1d3 | NM_029062.2 | chr1:31279683-31281132 |
| 22735 | Phox2b | NM_008888.3 | chr5:67485635-67490365 | 22830 | Pik3ap1 | NM_031376.3 | chr19:41348707-41459560 |
| 22736 | Phpt1 | NM_029293.2 | chr2:25428950-25430391 | 22831 | Pik3c2a | NM_011083.2 | chr7:123480789-123586972 |
| 22737 | Phrf1 | NM_001081118.1 | chr7:148414686-148448650 | 22832 | Pik3c2b | NM_001099276.2 | chr1:134942588-135005265 |
| 22738 | Phtf1 | NM_001163467.1 | chr3:103718042-103811414 | 22833 | Pik3c2g | NM_011164.2 | chr6:139535771-139917804 |
| 22739 | Phtf1 | NM_001163468.1 | chr3:103718042-103811414 | 22834 | Pik3c2g | NM_207683.2 | chr6:139535771-139917804 |
| 22740 | Phtf1 | NM_001163469.1 | chr3:103718042-103811414 | 22835 | Pik3c3 | NM_181414.5 | chr18:30432549-30507774 |
| 22741 | Phtf1 | NM_013629.2 | chr3:103718042-103811414 | 22836 | Pik3ca | NM_008839.2 | chr3:32335072-32367408 |
| 22742 | Phtf1os | NR_030676.1 | chr3:103768459-103772239 | 22837 | Pik3cb | NM_029094.3 | chr9:98938820-99040630 |
| 22743 | Phtf2 | NM_172992.3 | chr5:20264481-20387942 | 22838 | Pik3cd | NM_001029837.2 | chr4:149023276-149075738 |
| 22744 | Phxr4 | NR_028271.1 | chr9:13234580-13235960 | 22839 | Pik3cd | NM_001164049.1 | chr4:149023276-149075738 |
| 22745 | Phyh | NM_010726.2 | chr2:4840041-4859789 | 22840 | Pik3cd | NM_001164050.1 | chr4:149023276-149075738 |
| 22746 | Phyhd1 | NM_001252568.2 | chr2:30121722-30137669 | 22841 | Pik3cd | NM_001164051.1 | chr4:149023276-149075738 |
| 22747 | Phyhd1 | NM_001252570.1 | chr2:30121722-30137669 | 22842 | Pik3cd | NM_001164052.1 | chr4:149023276-149075738 |
| 22748 | Phyhd1 | NM_001252571.1 | chr2:30121722-30137669 | 22843 | Pik3cd | NM_008840.3 | chr4:149023276-149075738 |
| 22749 | Phyhd1 | NM_001281829.1 | chr2:30121722-30137669 | 22844 | Pik3cg | NM_001146200.1 | chr12:32858261-32893514 |
| 22750 | Phyhd1 | NM_172267.4 | chr2:30121722-30137669 | 22845 | Pik3cg | NM_001146201.1 | chr12:32858261-32893514 |
| 22751 | Phyhip | NM_145981.3 | chr14:70857323-70868631 | 22846 | Pik3cg | NM_020272.1 | chr12:32858261-32893514 |
| 22752 | Phyhipl | NM_001162846.1 | chr10:69903415-70062039 | 22847 | Pik3ip1 | NM_178149.4 | chr11:3230733-3242974 |
| 22753 | Phyhipl | NM_178621.4 | chr10:69903415-70062039 | 22848 | Pik3r1 | NM_001024955.2 | chr13:102450715-102538172 |
| 22754 | Phykpl | NM_028398.2 | chr11:51398259-51416771 | 22849 | Pik3r1 | NM_001077495.2 | chr13:102450715-102538172 |
| 22755 | Pi15 | NM_053191.2 | chr1:17591981-17621020 | 22850 | Pik3r2 | NM_008841.1 | chr8:73292079-73300611 |
| 22756 | Pi16 | NM_023734.3 | chr17:29455826-29465847 | 22851 | Pik3r3 | NM_181585.3 | chr4:115894518-115975661 |
| 22757 | Pi4k2a | NM_145501.2 | chr19:42164924-42196708 | 22852 | Pik3r4 | NM_001081309.1 | chr9:105545324-105589985 |
| 22758 | Pi4k2b | NM_025951.3 | chr5:53132812-53160583 | 22853 | Pik3r5 | NM_177320.2 | chr11:68245626-68311348 |
| 22759 | Pi4k2b | NM_028744.3 | chr5:53132812-53160583 | 22854 | Pik3r6 | NM_001004435.2 | chr11:68316520-68366200 |
| 22760 | Pi4ka | NM_001001983.2 | chr16:17280444-17406407 | 22855 | Pik3r6 | NM_001081566.1 | chr11:68316520-68366200 |
| 22761 | Pi4kb | NM_175356.3 | chr3:94778653-94810859 | 22856 | Pikfyve | NM_011086.2 | chr1:65233258-65325270 |
| 22762 | Pianp | NM_001145926.1 | chr6:124946737-124953117 | 22857 | Pilra | NM_153510.3 | chr5:138263180-138277506 |
| 22763 | Pianp | NM_001145927.1 | chr6:124946737-124953117 | 22858 | Pilrb1 | NM_133209.2 | chr5:138293374-138299277 |
| 22764 | Pianp | NM_175696.4 | chr6:124946737-124953117 | 22859 | Pilrb2 | NM_001024932.2 | chr5:138307056-138312986 |
| 22765 | Pias1 | NM_019663.3 | chr9:62727883-62828686 | 22860 | Pim1 | NM_008842.2 | chr17:29627989-29632404 |
| 22766 | Pias2 | NM_001164167.1 | chr18:77303946-77394447 | 22861 | Pim2 | NM_138606.2 | chrX:7455431-7460558 |
| 22767 | Pias2 | NM_001164168.1 | chr18:77303946-77394447 | 22862 | Pim3 | NM_145478.2 | chr15:88692623-88696156 |
| 22768 | Pias2 | NM_001164169.1 | chr18:77303946-77394447 | 22863 | Pin1 | NM_023371.3 | chr9:20456573-20471028 |
| 22769 | Pias2 | NM_001164170.1 | chr18:77303946-77394447 | 22864 | Pin1rt1 | NM_001033768.2 | chr2:104554082-104556447 |
| 22770 | Pias2 | NM_008602.4 | chr18:77303946-77394447 | 22865 | Pin4 | NM_027181.1 | chrX:99814803-99323012 |
| 22771 | Pias3 | NM_001165949.1 | chr3:96500297-96512483 | 22866 | Pinc | NR_003202.1 | chr3:73437959-73454143 |
| 22772 | Pias3 | NM_018812.2 | chr3:96500297-96512483 | 22867 | Pink1 | NM_026880.2 | chr4:137869325-137882211 |
| 22773 | Pias3 | NM_146135.2 | chr3:96500297-96512483 | 22868 | Pinlyp | NM_001037143.2 | chr7:25326676-25331024 |
| 22774 | Pias4 | NM_021501.4 | chr10:80616715-80630465 | 22869 | Pinx1 | NM_028228.3 | chr14:64479148-64538696 |
| 22775 | Pitbf1 | NM_029320.3 | chr14:94498643-99653713 | 22870 | Pip | NM_008843.3 | chr6:41797547-41802061 |
| 22776 | Picalm | NM_001252520.1 | chr7:97278741-97357957 | 22871 | Pip4k2a | NM_008845.4 | chr2:18763882-18919748 |
| 22777 | Picalm | NM_001252521.1 | chr7:97278741-97357957 | 22872 | Pip4k2b | NM_054051.1 | chr11:97576470-97606018 |
| 22778 | Picalm | NM_001252522.1 | chr7:97278741-97357957 | 22873 | Pip4k2c | NM_054097.3 | chr10:126634123-126648678 |
| 22779 | Picalm | NM_001252523.1 | chr7:97278741-97357957 | 22874 | Pip5k1a | NM_008847.3 | chr3:94863519-94910780 |
| 22780 | Picalm | NM_001252524.1 | chr7:97278741-97357957 | 22875 | Pip5k1b | NM_008846.2 | chr19:24369286-24630317 |
| 22781 | Picalm | NM_146194.4 | chr7:97278741-97357957 | 22876 | Pip5k1c | NM_001146687.2 | chr10:80755716-80782719 |
| 22782 | Pick1 | NM_001045558.1 | chr15:79059602-79079896 | 22877 | Pip5k1c | NM_008844.3 | chr10:80755716-80782719 |
| 22783 | Pick1 | NM_008837.3 | chr15:79059602-79079896 | 22878 | Pip5kl1 | NM_198191.2 | chr2:32431338-32439299 |
| 22784 | Pid1 | NM_001039948.2 | chr1:84032868-84281220 | 22879 | Pipox | NM_008952.2 | chr11:77694116-77707374 |
| 22785 | Pidd1 | NM_022654.1 | chr7:148624413-148629254 | 22880 | Pir | NM_027153.2 | chrX:160707362-160810945 |
| 22786 | Piezo1 | NM_001037298.1 | chr8:125005598-125075229 | 22881 | Pira1 | NM_011087.1 | chr7:3788417-3867086 |
| 22787 | Piezo2 | NM_001039485.4 | chr18:63169866-63546837 | 22882 | Pira11 | NM_011088.1 | chr7:3789756-3849695 |
| 22788 | Pif1 | NM_172453.3 | chr9:65435011-65443769 | 22883 | Pira2 | NM_011089.2 | chr7:3788412-3796653 |
| 22789 | Pifo | NM_001200028.1 | chr3:105799874-105817564 | 22884 | Pira4 | NM_011091.1 | chr7:3789729-3849694 |
| 22790 | Pifo | NM_029604.3 | chr3:105799874-105817564 | 22885 | Pira6 | NM_001289428.1 | chr7:3683234-3867103 |
| 22791 | Piga | NM_011081.2 | chrX:160857718-160871847 | 22886 | Pira6 | NM_008848.1 | chr7:4225744-4234530 |
| 22792 | Pigb | NM_018859.3 | chr9:72863503-72887506 | 22887 | Pira6 | NM_011093.1 | chr7:4225744-4234530 |
| 22793 | Pigc | NM_001039045.1 | chr1:163872219-163909767 | 22888 | Pira7 | NM_011094.1 | chr7:3789724-3849722 |
| 22794 | Pigc | NM_026078.2 | chr1:163872219-163909767 | 22889 | Pirb | NM_011095.2 | chr7:3664106-3671984 |
| 22795 | Pigf | NM_008838.1 | chr7:87396599-87424741 | 22890 | Pirt | NM_178656.3 | chr11:66725493-66742202 |
| 22796 | Pigg | NM_001081234.1 | chr5:108741943-108777798 | 22891 | Pisd | NM_177298.3 | chr5:33078961-33128275 |
| 22797 | Pigh | NM_029988.2 | chr12:80181658-80190657 | 22892 | Pisd-ps1 | NR_003517.1 | chr11:3024024-3031947 |
| 22798 | Pigk | NM_026232.5 | chr3:152377063-152451977 | 22893 | Pisd-ps2 | NR_003519.3 | chr17:3064317-3084183 |
| 22799 | Pigk | NM_178016.3 | chr3:152377063-152451977 | 22894 | Pisd-ps3 | NR_003518.2 | chr11:3024030-3031945 |
| 22800 | Pigl | NM_001039536.2 | chr11:62271961-62327402 | 22895 | Pithd1 | NM_025411.4 | chr4:135531516-135543159 |
| 22801 | Pigm | NM_026234.4 | chr1:174306661-174314230 | 22896 | Pitpna | NM_008850.1 | chr11:75401610-75442280 |
| 22802 | Pign | NM_013784.3 | chr1:107414998-107560253 | 22897 | Pitpnb | NM_019640.5 | chr5:111759782-111817379 |
| 22803 | Pigo | NM_020035.2 | chr4:43030509-43038628 | 22898 | Pitpnc1 | NM_145823.2 | chr11:107069205-107332034 |
| 22804 | Pigp | NM_001159616.1 | chr16:94580369-94690828 | 22899 | Pitpnm1 | NM_008851.4 | chr19:4099997-4125858 |
| 22805 | Pigp | NM_001159617.1 | chr16:94580369-94690828 | 22900 | Pitpnm1 | NR_075078.1 | chr19:4099997-4125858 |
| 22806 | Pigp | NM_001159618.1 | chr16:94580369-94690828 | 22901 | Pitpnm2 | NM_001289472.1 | chr5:124568697-124699769 |
| 22807 | Pigp | NM_001159619.1 | chr16:94580369-94690828 | 22902 | Pitpnm2 | NM_011256.3 | chr5:124568697-124699769 |
| 22808 | Pigp | NM_001159620.1 | chr16:94580369-94690828 | 22903 | Pitpnm2os1 | NR_045369.1 | chr5:124679734-124687146 |
| 22809 | Pigq | NM_001159623.1 | chr16:94580369-94690828 | 22904 | Pitpnm3 | NM_001024927.2 | chr11:71861029-71949391 |
| 22810 | Pigq | NM_001291025.1 | chr17:26063364-26078934 | 22905 | Pitpnm3 | NM_001081641.1 | chr11:71861029-71949391 |
| 22811 | Pigq | NM_011822.4 | chr17:26063364-26078934 | 22906 | Pitrm1 | NM_145131.1 | chr13:6547403-6579395 |
| 22812 | Pigr | NM_011082.2 | chr1:132723260-132748826 | 22907 | Pitx1 | NM_011097.2 | chr13:55926414-55932786 |
| 22813 | Pigs | NM_201406.1 | chr11:78141923-78156278 | 22908 | Pitx2 | NM_001042504.2 | chr3:128902795-128922512 |
| 22814 | Pigt | NM_133779.2 | chr2:164323024-164333801 | 22909 | Pitx2 | NM_001286942.1 | chr3:128902795-128922512 |
| 22815 | Pigu | NM_001103988.1 | chr2:155103988-155183160 | 22910 | Pitx2 | NM_001287048.1 | chr3:128902795-128922512 |
| 22816 | Pigv | NM_001145955.1 | chr4:133217339-133228562 | 22911 | Pitx2 | NM_011098.4 | chr3:128902795-128922512 |
| 22817 | Pigv | NM_001145956.1 | chr4:133217339-133228562 | 22912 | Pitx3 | NM_008852.4 | chr19:46210176-46222815 |

Fig. 25 - 122

| | | | |
|---|---|---|---|
| 22913 | Piwil1 | NM_021311.3 | chr5:129242126-129261349 |
| 22914 | Piwil2 | NM_021308.1 | chr14:70772286-70828901 |
| 22915 | Piwil4 | NM_177905.3 | chr9:14506801-14545177 |
| 22916 | Pja1 | NM_001083110.2 | chrX:96661072-96666074 |
| 22917 | Pja1 | NM_001290555.1 | chrX:96661072-96666074 |
| 22918 | Pja1 | NM_001290556.1 | chrX:96661072-96666074 |
| 22919 | Pja1 | NM_008853.3 | chrX:96661072-96666074 |
| 22920 | Pja2 | NM_001025309.1 | chr17:64630354-64681223 |
| 22921 | Pja2 | NM_144859.2 | chr17:64630354-64681223 |
| 22922 | Pkd1 | NM_013630.2 | chr17:24686895-24733459 |
| 22923 | Pkd1l2 | NM_029686.4 | chr8:119519578-119606349 |
| 22924 | Pkd1l3 | NM_001039700.2 | chr8:112138416-112217194 |
| 22925 | Pkd1l3 | NM_001286454.1 | chr8:112138416-112217194 |
| 22926 | Pkd1l3 | NM_181544.2 | chr8:112138416-112217194 |
| 22927 | Pkd2 | NM_008861.3 | chr5:104888475-104934838 |
| 22928 | Pkd2l1 | NM_181422.3 | chr19:44222126-44266932 |
| 22929 | Pkd2l2 | NM_001163004.1 | chr18:34569076-34666477 |
| 22930 | Pkd2l2 | NM_016927.3 | chr18:34569076-34666477 |
| 22931 | Pkdcc | NM_134117.2 | chr17:83614622-83624409 |
| 22932 | Pkdrej | NM_011105.2 | chr15:85645105-85652163 |
| 22933 | Pkhd1 | NM_153179.3 | chr1:20047860-20608138 |
| 22934 | Pkhd1l1 | NM_138674.2 | chr15:44289098-44428681 |
| 22935 | Pkia | NM_008862.3 | chr3:7366603-7445365 |
| 22936 | Pkib | NM_001039050.1 | chr10:57351786-57460918 |
| 22937 | Pkib | NM_001039051.2 | chr10:57351786-57460918 |
| 22938 | Pkib | NM_001039052.1 | chr10:57351786-57460918 |
| 22939 | Pkib | NM_001039053.2 | chr10:57351786-57460918 |
| 22940 | Pkib | NM_001039402.1 | chr10:57351786-57460918 |
| 22941 | Pkib | NM_008863.4 | chr10:57351786-57460918 |
| 22942 | Pkig | NM_001039390.2 | chr2:163484121-163551894 |
| 22943 | Pkig | NM_001039391.2 | chr2:163484121-163551894 |
| 22944 | Pkig | NM_001164053.1 | chr2:163484121-163551894 |
| 22945 | Pkig | NM_001164055.1 | chr2:163484121-163551894 |
| 22946 | Pkig | NM_001072096.1 | chr2:163484121-163551894 |
| 22947 | Pkig | NM_011106.2 | chr2:163484121-163551894 |
| 22948 | Pklr | NM_001099779.1 | chr3:88940063-88950516 |
| 22949 | Pklr | NM_013631.2 | chr3:88940063-88950516 |
| 22950 | Pkm | NM_001253883.1 | chr9:59504174-59527182 |
| 22951 | Pkm | NM_011009.3 | chr9:59504174-59527182 |
| 22952 | Pkmyt1 | NM_023058.1 | chr17:23863303-23873696 |
| 22953 | Pkn1 | NM_001199593.1 | chr8:86190538-86223078 |
| 22954 | Pkn1 | NM_177262.4 | chr8:86190538-86223078 |
| 22955 | Pkn2 | NM_178654.4 | chr3:142453865-142544968 |
| 22956 | Pkn3 | NM_153805.1 | chr2:29934286-29946539 |
| 22957 | Pknox1 | NM_016670.3 | chr17:31701717-31744638 |
| 22958 | Pknox1 | NR_027493.1 | chr17:31701717-31744638 |
| 22959 | Pknox2 | NM_001029838.2 | chr9:36698563-36954907 |
| 22960 | Pknox2 | NM_148950.3 | chr9:36698563-36954907 |
| 22961 | Pkp1 | NM_019645.2 | chr1:137767971-137815601 |
| 22962 | Pkp2 | NM_026163.2 | chr16:16213437-16272805 |
| 22963 | Pkp3 | NM_001162924.1 | chr7:148264127-148276409 |
| 22964 | Pkp3 | NM_019762.2 | chr7:148264127-148276409 |
| 22965 | Pkp4 | NM_026361.2 | chr2:58998906-59193262 |
| 22966 | Pkp4 | NM_175464.2 | chr2:58998906-59193262 |
| 22967 | Pla1a | NM_134102.4 | chr16:38396202-38433225 |
| 22968 | Pla2g10 | NM_001291009.1 | chr16:13715149-13739564 |
| 22969 | Pla2g10 | NM_011987.3 | chr16:13715149-13739564 |
| 22970 | Pla2g10 | NR_110990.1 | chr16:13715149-13739564 |
| 22971 | Pla2g10os | NR_040574.1 | chr16:13729929-13739564 |
| 22972 | Pla2g12a | NM_001286948.1 | chr3:129581523-129598743 |
| 22973 | Pla2g12a | NM_023196.4 | chr3:129581523-129598743 |
| 22974 | Pla2g12a | NM_183423.3 | chr3:129581523-129598743 |
| 22975 | Pla2g12a | NR_104611.1 | chr3:129581523-129598743 |
| 22976 | Pla2g12b | NM_023530.2 | chr10:58866432-58884724 |
| 22977 | Pla2g15 | NM_133792.2 | chr8:108674298-108686615 |
| 22978 | Pla2g16 | NM_139269.2 | chr19:7631948-7663035 |
| 22979 | Pla2g1b | NM_011107.1 | chr5:115916274-115924726 |
| 22980 | Pla2g2a | NM_001082531.1 | chr4:138355161-138419384 |
| 22981 | Pla2g2a | NR_002926.3 | chr4:138355161-138419384 |
| 22982 | Pla2g2c | NM_008868.3 | chr4:138281240-138300490 |
| 22983 | Pla2g2d | NM_011109.2 | chr4:138331649-138338058 |
| 22984 | Pla2g2e | NM_012044.2 | chr4:138433856-138438729 |
| 22985 | Pla2g2f | NM_012045.4 | chr4:138306447-138313513 |
| 22986 | Pla2g3 | NM_172791.2 | chr11:3388229-3394169 |
| 22987 | Pla2g4a | NM_008869.2 | chr1:151676751-151808414 |
| 22988 | Pla2g4b | NM_145934.2 | chr2:119859169-119868768 |
| 22989 | Pla2g4c | NM_001004762.3 | chr7:13911015-13946017 |
| 22990 | Pla2g4c | NM_001168504.1 | chr7:13911015-13946017 |
| 22991 | Pla2g4d | NM_001024137.1 | chr2:120091604-120114805 |
| 22992 | Pla2g4e | NM_177845.4 | chr2:119992147-120071071 |
| 22993 | Pla2g4f | NM_001024145.2 | chr2:120125692-120139901 |
| 22994 | Pla2g5 | NM_001122954.1 | chr4:138355161-138419384 |
| 22995 | Pla2g5 | NM_011110.4 | chr4:138355161-138419384 |
| 22996 | Pla2g6 | NM_001199023.1 | chr15:79116657-79158801 |
| 22997 | Pla2g6 | NM_001199024.1 | chr15:79116657-79158801 |
| 22998 | Pla2g6 | NM_001199025.1 | chr15:79116657-79158801 |
| 22999 | Pla2g6 | NM_016915.4 | chr15:79116657-79158801 |
| 23000 | Pla2g7 | NM_013737.5 | chr17:43705400-43749150 |
| 23001 | Pla2r1 | NM_008867.2 | chr2:60255599-60391365 |
| 23002 | Plaa | NM_172695.2 | chr4:94231830-94269938 |
| 23003 | Plac1 | NM_019538.4 | chrX:50423178-50467582 |
| 23004 | Plac8 | NM_139198.2 | chr5:100982751-101001224 |
| 23005 | Plac8l1 | NM_027072.1 | chr18:42338328-42356363 |
| 23006 | Plac9a | NM_207229.1 | chr14:26707419-26722457 |
| 23007 | Plac9a | NM_207229.1 | chr14:26847189-26862223 |

| | | | |
|---|---|---|---|
| 23008 | Plac9a | NM_207229.1 | chr14:26986803-27001837 |
| 23009 | Plac9b | NM_001270503.1 | chr14:26986803-27001837 |
| 23010 | Plac9b | NM_001270503.1 | chr14:26847189-26862223 |
| 23011 | Plac9b | NM_001270503.1 | chr14:26707419-26722457 |
| 23012 | Plag1 | NM_019969.3 | chr4:3828304-3865552 |
| 23013 | Plagl1 | NM_009538.2 | chr10:12810593-12851501 |
| 23014 | Plagl2 | NM_018807.5 | chr2:153053504-153067094 |
| 23015 | Plat | NM_008872.2 | chr8:23868215-23893320 |
| 23016 | Plau | NM_008873.3 | chr14:21655883-21662610 |
| 23017 | Plaur | NM_011113.3 | chr7:25247518-25260892 |
| 23018 | Plb1 | NM_001081407.1 | chr5:32535080-32666729 |
| 23019 | Plb1 | NM_030072.1 | chr5:32535080-32666729 |
| 23020 | Plb1 | NM_172147.2 | chr5:32535080-32666729 |
| 23021 | Plbd1 | NM_025806.2 | chr6:136560591-136610414 |
| 23022 | Plbd2 | NM_023625.1 | chr5:120933902-120953632 |
| 23023 | Plcb1 | NM_001145830.1 | chr2:134611899-135300994 |
| 23024 | Plcb1 | NM_019677.2 | chr2:134611899-135300994 |
| 23025 | Plcb2 | NM_001290790.1 | chr2:118533252-118554174 |
| 23026 | Plcb2 | NM_177568.2 | chr2:118533252-118554174 |
| 23027 | Plcb3 | NM_001290349.1 | chr19:7028202-7044304 |
| 23028 | Plcb3 | NM_008874.4 | chr19:7028202-7044304 |
| 23029 | Plcb4 | NM_013829.2 | chr2:135567565-135838804 |
| 23030 | Plcd1 | NM_019676.1 | chr9:118980645-119002614 |
| 23031 | Plcd3 | NM_152813.3 | chr11:102931609-102962972 |
| 23032 | Plcd4 | NM_001081456.1 | chr1:74455957-74634602 |
| 23033 | Plcd4 | NM_148937.2 | chr1:74455957-74634602 |
| 23034 | Plce1 | NM_019588.2 | chr19:38598686-38859590 |
| 23035 | Plcg1 | NM_021280.3 | chr2:160557046-160601496 |
| 23036 | Plcg2 | NM_172285.1 | chr8:120022190-120159042 |
| 23037 | Plch1 | NM_001177732.1 | chr3:63500155-63654913 |
| 23038 | Plch1 | NM_001177733.1 | chr3:63500155-63654913 |
| 23039 | Plch1 | NM_183191.3 | chr3:63500155-63654913 |
| 23040 | Plch2 | NM_001113360.2 | chr4:154357223-154385093 |
| 23041 | Plch2 | NM_175556.3 | chr4:154357223-154385093 |
| 23042 | Plcl1 | NM_001114663.1 | chr1:55462789-55811129 |
| 23043 | Plcl2 | NM_013880.1 | chr17:50648871-50827819 |
| 23044 | Plcxd1 | NM_001281812.1 | chr5:110528987-110537216 |
| 23045 | Plcxd1 | NM_207279.2 | chr5:110528987-110537216 |
| 23046 | Plcxd2 | NM_001134480.1 | chr16:45959373-46010526 |
| 23047 | Plcxd3 | NM_177355.3 | chr15:4325490-4525579 |
| 23048 | Plcz1 | NM_054066.4 | chr6:139938242-139999938 |
| 23049 | Pld1 | NM_001164056.1 | chr3:27837601-28032284 |
| 23050 | Pld1 | NM_008875.4 | chr3:27837601-28032284 |
| 23051 | Pld2 | NM_008876.3 | chr11:70353665-70371612 |
| 23052 | Pld3 | NM_011116.1 | chr7:28317036-28338131 |
| 23053 | Pld4 | NM_178911.4 | chr12:113998865-114007197 |
| 23054 | Pld5 | NM_001195816.1 | chr1:177892436-178205443 |
| 23055 | Pld5 | NM_176916.2 | chr1:177892436-178205443 |
| 23056 | Pld6 | NM_001290283.2 | chr11:59597394-59601159 |
| 23057 | Pld6 | NM_183139.2 | chr11:59597394-59601159 |
| 23058 | Pld6 | NR_110894.1 | chr11:59597394-59601159 |
| 23059 | Pldi | NR_033616.1 | chr10:60390973-60400880 |
| 23060 | Plec | NM_001163540.1 | chr15:76001403-76061808 |
| 23061 | Plec | NM_001163542.1 | chr15:76001403-76061808 |
| 23062 | Plec | NM_001163549.1 | chr15:76001403-76061808 |
| 23063 | Plec | NM_001164063.1 | chr15:76001403-76061808 |
| 23064 | Plec | NM_011117.2 | chr15:76001403-76061808 |
| 23065 | Plec | NM_201385.2 | chr15:76001403-76061808 |
| 23066 | Plec | NM_201386.2 | chr15:76001403-76061808 |
| 23067 | Plec | NM_201387.3 | chr15:76001403-76061808 |
| 23068 | Plec | NM_201388.2 | chr15:76001403-76061808 |
| 23069 | Plec | NM_201389.2 | chr15:76001403-76061808 |
| 23070 | Plec | NM_201390.2 | chr15:76001403-76061808 |
| 23071 | Plec | NM_201391.2 | chr15:76001403-76061808 |
| 23072 | Plec | NM_201392.2 | chr15:76001403-76061808 |
| 23073 | Plec | NM_201393.2 | chr15:76001403-76061808 |
| 23074 | Plec | NM_201394.2 | chr15:76001403-76061808 |
| 23075 | Plek | NM_019549.2 | chr11:16871208-16908721 |
| 23076 | Plek2 | NM_013738.3 | chr12:79989683-80007925 |
| 23077 | Plekha1 | NM_133942.2 | chr7:138009424-138056816 |
| 23078 | Plekha2 | NM_031257.3 | chr8:26149616-26212283 |
| 23079 | Plekha3 | NM_031256.1 | chr2:76513371-76535392 |
| 23080 | Plekha4 | NM_148927.2 | chr7:52781699-52809599 |
| 23081 | Plekha5 | NM_144920.3 | chr6:140372619-140543427 |
| 23082 | Plekha6 | NM_001160268.1 | chr1:135142673-135200012 |
| 23083 | Plekha6 | NM_182930.2 | chr1:135142673-135200012 |
| 23084 | Plekha7 | NM_172743.3 | chr7:123267631-123333355 |
| 23085 | Plekha8 | NM_001001335.2 | chr6:54545104-54595816 |
| 23086 | Plekha8 | NM_001164361.1 | chr6:54545104-54595816 |
| 23087 | Plekhb1 | NM_001163182.1 | chr7:107792409-107810908 |
| 23088 | Plekhb1 | NM_001163183.1 | chr7:107792409-107810908 |
| 23089 | Plekhb1 | NM_001163184.1 | chr7:107792409-107810908 |
| 23090 | Plekhb1 | NM_001163185.1 | chr7:107792409-107810908 |
| 23091 | Plekhb1 | NM_001163186.1 | chr7:107792409-107810908 |
| 23092 | Plekhb1 | NM_001163187.1 | chr7:107792409-107810908 |
| 23093 | Plekhb1 | NM_001291336.1 | chr7:107792409-107810908 |
| 23094 | Plekhb1 | NM_013746.3 | chr7:107792409-107810908 |
| 23095 | Plekhb2 | NM_145516.2 | chr1:34906803-34936430 |
| 23096 | Plekhb2 | NM_175421.1 | chr1:34906803-34936430 |
| 23097 | Plekhd1 | NM_001177503.1 | chr12:81793587-81825203 |
| 23098 | Plekhd1os | NR_037995.1 | chr12:81787361-81793453 |
| 23099 | Plekhf1 | NM_024413.2 | chr7:39005672-39013013 |
| 23100 | Plekhf2 | NM_175175.4 | chr4:10915808-10934766 |
| 23101 | Plekhg1 | NM_001033253.3 | chr10:6379238-6606164 |
| 23102 | Plekhg1 | NM_001159942.1 | chr10:6379238-6606164 |

Fig. 25 - 123

| | | | | | | | | |
|---|---|---|---|---|---|---|---|---|
| 23103 | Plekhg2 | NM_001083912.1 | chr7:29144622-29157681 | | 23198 | Pmp2 | NM_001030305.2 | chr3:10179850-10183885 |
| 23104 | Plekhg2 | NM_001290542.1 | chr7:29144622-29157681 | | 23199 | Pmp22 | NM_008885.3 | chr11:62945011-62973048 |
| 23105 | Plekhg2 | NM_138752.2 | chr7:29144622-29157681 | | 23200 | Pmpca | NM_173180.3 | chr2:26244868-26252641 |
| 23106 | Plekhg3 | NM_153804.4 | chr12:77634547-77680026 | | 23201 | Pmpcb | NM_028431.2 | chr5:21242977-21262970 |
| 23107 | Plekhg4 | NM_001081333.1 | chr8:107899281-107906762 | | 23202 | Pms1 | NM_153556.1 | chr1:53246031-53353840 |
| 23108 | Plekhg5 | NM_001285999.1 | chr4:151460971-151489513 | | 23203 | Pms2 | NM_008886.2 | chr5:144670869-144692625 |
| 23109 | Plekhg5 | NR_104381.1 | chr4:151460971-151489513 | | 23204 | Pmvk | NM_026784.3 | chr3:89263039-89272931 |
| 23110 | Plekhg6 | NM_198604.2 | chr6:125312668-125330522 | | 23205 | Pmvk | NM_027348.1 | chr3:89263039-89272931 |
| 23111 | Plekhh1 | NM_181073.3 | chr12:80130150-80182642 | | 23206 | Pnck | NM_001199351.1 | chrX:70901330-70905409 |
| 23112 | Plekhh2 | NM_177606.4 | chr17:84911234-85021482 | | 23207 | Pnck | NM_001199352.1 | chrX:70901330-70905409 |
| 23113 | Plekhh3 | NM_146030.2 | chr11:101023992-101032616 | | 23208 | Pnck | NM_012040.3 | chrX:70901330-70905409 |
| 23114 | Plekhj1 | NM_023900.2 | chr10:80258843-80261371 | | 23209 | Pnisr | NM_025669.1 | chr4:21774730-21803622 |
| 23115 | Plekhm1 | NM_183034.1 | chr11:103226405-103273978 | | 23210 | Pnkd | NM_001039509.1 | chr1:74331607-74400266 |
| 23116 | Plekhm2 | NM_001033150.1 | chr4:141181648-141220030 | | 23211 | Pnkd | NM_019999.2 | chr1:74331607-74400266 |
| 23117 | Plekhm3 | NM_001039493.1 | chr1:64835694-65003398 | | 23212 | Pnkd | NM_025580.2 | chr1:74331607-74400266 |
| 23118 | Plekhn1 | NM_001002833.3 | chr4:155595564-155602651 | | 23213 | Pnkp | NM_001290764.1 | chr7:52112515-52118299 |
| 23119 | Plekho1 | NM_023320.2 | chr3:95792762-95799762 | | 23214 | Pnkp | NM_001290766.1 | chr7:52112515-52118299 |
| 23120 | Plekho2 | NM_153119.3 | chr9:65400383-65427894 | | 23215 | Pnkp | NM_001290767.1 | chr7:52112515-52118299 |
| 23121 | Plekhs1 | NM_001164263.1 | chr19:56536126-56561219 | | 23216 | Pnkp | NM_021549.3 | chr7:52112515-52118299 |
| 23122 | Plekhs1 | NM_172641.3 | chr19:56536126-56561219 | | 23217 | Pnldc1 | NM_001034866.1 | chr17:13081767-13102866 |
| 23123 | Plet1 | NM_029639.2 | chr9:50302630-50313744 | | 23218 | Pnlip | NM_026925.3 | chr19:58744854-58756278 |
| 23124 | Plet1os | NR_040714.1 | chr9:50296904-50312910 | | 23219 | Pnliprp1 | NM_018874.2 | chr19:58803376-58818659 |
| 23125 | Plg | NM_008877.3 | chr17:12571474-12612250 | | 23220 | Pnliprp2 | NM_011128.2 | chr19:58834212-58852024 |
| 23126 | Plgrkt | NM_026362.2 | chr19:29423166-29436361 | | 23221 | Pnma1 | NM_027438.3 | chr12:85487080-85489439 |
| 23127 | Plin1 | NM_001113471.1 | chr7:86866049-86877662 | | 23222 | Pnma2 | NM_175498.2 | chr14:67530044-67538898 |
| 23128 | Plin1 | NM_175640.2 | chr7:86866049-86877662 | | 23223 | Pnma3 | NM_153169.2 | chrX:70310125-70313530 |
| 23129 | Plin2 | NM_007408.3 | chr4:86302468-86315963 | | 23224 | Pnma5 | NM_001100461.3 | chrX:70279319-70282442 |
| 23130 | Plin3 | NM_025436.3 | chr17:56418384-56429934 | | 23225 | Pnmal1 | NM_001007569.1 | chr7:17545143-17547669 |
| 23131 | Plin4 | NM_020568.3 | chr17:56240014-56249225 | | 23226 | Pnmal2 | NM_001099636.2 | chr7:17530030-17534177 |
| 23132 | Plin5 | NM_001077348.1 | chr17:56251023-56256971 | | 23227 | Pnmt | NM_008890.1 | chr11:98247945-98249411 |
| 23133 | Plin5 | NM_025874.3 | chr17:56251023-56256971 | | 23228 | Pnn | NM_008891.2 | chr12:60167905-60175004 |
| 23134 | Plk1 | NM_011121.3 | chr7:129302950-129313389 | | 23229 | Pno1 | NM_025443.2 | chr11:17103202-17111592 |
| 23135 | Plk2 | NM_152804.2 | chr13:111185251-111191051 | | 23230 | Pnoc | NM_001205075.1 | chr14:66019509-66044309 |
| 23136 | Plk3 | NM_013807.2 | chr4:116801260-116806557 | | 23231 | Pnoc | NM_010932.2 | chr14:66019509-66044309 |
| 23137 | Plk4 | NM_011495.2 | chr3:40603872-40620805 | | 23232 | Pnp | NM_013632.4 | chr14:51563975-51573087 |
| 23138 | Plk4 | NM_173169.2 | chr3:40603872-40620805 | | 23233 | Pnp | NM_001123371.2 | chr14:51575815-51584424 |
| 23139 | Plk4 | NR_045576.1 | chr3:40603872-40620805 | | 23234 | Pnpla1 | NM_001034885.3 | chr17:28995355-29027253 |
| 23140 | Plk5 | NM_183152.3 | chr10:79819203-79828234 | | 23235 | Pnpla2 | NM_001163689.1 | chr7:148641086-148646642 |
| 23141 | Plp | NM_026385.4 | chr8:97198794-97220142 | | 23236 | Pnpla2 | NM_025802.3 | chr7:148641086-148646642 |
| 23142 | Pln | NM_001141927.1 | chr10:52997886-53099657 | | 23237 | Pnpla2 | NR_028142.1 | chr7:148641086-148646642 |
| 23143 | Pln | NM_023129.5 | chr10:52997886-53099657 | | 23238 | Pnpla3 | NM_054088.3 | chr15:83998246-84019951 |
| 23144 | Plod1 | NM_011272.3 | chr4:147283861-147310885 | | 23239 | Pnpla5 | NM_029427.1 | chr15:83943050-83953605 |
| 23145 | Plod2 | NM_001142916.1 | chr9:92433638-92503265 | | 23240 | Pnpla6 | NM_001128818.2 | chr8:3515383-3544267 |
| 23146 | Plod2 | NM_011961.3 | chr9:92433638-92503265 | | 23241 | Pnpla6 | NM_015801.2 | chr8:3515383-3544267 |
| 23147 | Plod3 | NM_011962.3 | chr5:137462889-137472516 | | 23242 | Pnpla7 | NM_146251.4 | chr2:24831552-24909592 |
| 23148 | Plp1 | NM_001290561.1 | chrX:133357284-133373121 | | 23243 | Pnpla8 | NM_026164.2 | chr12:45370140-45414422 |
| 23149 | Plp1 | NM_001290562.1 | chrX:133357284-133373121 | | 23244 | Pnpo | NM_134021.2 | chr11:96799129-96805333 |
| 23150 | Plp1 | NM_011123.3 | chrX:133357284-133373121 | | 23245 | Pnpt1 | NM_027869.1 | chr11:29030750-29061828 |
| 23151 | Plp2 | NM_019755.4 | chrX:7245242-7248404 | | 23246 | Pnrc1 | NM_001033225.2 | chr4:33332397-33335762 |
| 23152 | Plrg1 | NM_016784.3 | chr3:82859459-82876213 | | 23247 | Pnrc2 | NM_026383.3 | chr4:135426840-135429761 |
| 23153 | Pls1 | NM_001033210.3 | chr9:95653060-95745698 | | 23248 | Poc1a | NM_027354.2 | chr9:106183391-106252222 |
| 23154 | Pls3 | NM_001166453.1 | chrX:73030992-73120509 | | 23249 | Poc1b | NM_027740.4 | chr10:98569805-98660622 |
| 23155 | Pls3 | NM_001166454.2 | chrX:73030992-73120509 | | 23250 | Poc5 | NM_026173.3 | chr13:97158248-97185542 |
| 23156 | Pls3 | NM_145629.2 | chrX:73030992-73120509 | | 23251 | Podn | NM_001285956.1 | chr4:107687397-107704695 |
| 23157 | Plscr1 | NM_011636.2 | chr9:92145032-92167399 | | 23252 | Podn | NM_001285958.1 | chr4:107687397-107704695 |
| 23158 | Plscr2 | NM_001195084.1 | chr9:92170439-92192590 | | 23253 | Podn | NM_172874.3 | chr4:107687397-107704695 |
| 23159 | Plscr2 | NM_008880.1 | chr9:92170439-92192590 | | 23254 | Podnl1 | NM_001013384.2 | chr8:86649887-86656416 |
| 23160 | Plscr3 | NM_001168497.1 | chr11:69659873-69672232 | | 23255 | Podxl | NM_013723.1 | chr6:31469492-31513937 |
| 23161 | Plscr3 | NM_025566.4 | chr11:69659873-69672232 | | 23256 | Podxl2 | NM_176973.4 | chr6:88792552-88824038 |
| 23162 | Plscr3 | NR_033133.1 | chr11:69659873-69672232 | | 23257 | Pof1b | NM_181579.1 | chrX:109752035-109812260 |
| 23163 | Plscr4 | NM_178711.3 | chr9:92352215-92387354 | | 23258 | Pofut1 | NM_080463.3 | chr2:153067267-153095985 |
| 23164 | Plscr5 | NM_001195693.1 | chr9:92087773-92104536 | | 23259 | Pofut2 | NM_030262.3 | chr10:76722044-76732331 |
| 23165 | Pltp | NM_011125.2 | chr2:164665018-164683208 | | 23260 | Pogk | NM_001142948.1 | chr1:168309297-168339959 |
| 23166 | Plvap | NM_032398.2 | chr8:74021651-74035668 | | 23261 | Pogk | NM_175170.4 | chr1:168309297-168339959 |
| 23167 | Plxdc1 | NM_001016530.1 | chr11:97784550-97847760 | | 23262 | Pogtul1 | NM_172380.4 | chr16:38525263-38550266 |
| 23168 | Plxdc1 | NM_028199.1 | chr11:97784550-97847760 | | 23263 | Pogz | NM_001165948.1 | chr3:94641488-94687489 |
| 23169 | Plxdc2 | NM_026162.5 | chr2:16277930-16677466 | | 23264 | Pogz | NM_172683.3 | chr3:94641488-94687489 |
| 23170 | Plxna1 | NM_008881.2 | chr6:89266307-89312607 | | 23265 | Pola1 | NM_008892.2 | chrX:90550304-90877494 |
| 23171 | Plxna2 | NM_008882.2 | chr1:196446022-196643062 | | 23266 | Pola2 | NM_001164057.1 | chr19:5940542-5964206 |
| 23172 | Plxna3 | NM_008883.3 | chrX:71574404-71590028 | | 23267 | Pola2 | NM_008893.3 | chr19:5940542-5964206 |
| 23173 | Plxna4 | NM_175750.3 | chr6:32094559-32538192 | | 23268 | Polb | NM_011130.2 | chr8:23738591-23763909 |
| 23174 | Plxna4os1 | NR_040277.1 | chr6:32461141-32465576 | | 23269 | Pold1 | NM_011131.3 | chr7:51788114-51804185 |
| 23175 | Plxnb1 | NM_172775.2 | chr9:108997949-109022429 | | 23270 | Pold2 | NM_008894.2 | chr11:5772183-5778259 |
| 23176 | Plxnb2 | NM_001159521.2 | chr15:88985975-89011218 | | 23271 | Pold3 | NM_183692.2 | chr7:107230622-107270010 |
| 23177 | Plxnb2 | NM_001284506.1 | chr15:88985975-89011218 | | 23272 | Pold4 | NM_027196.3 | chr19:4231898-4233634 |
| 23178 | Plxnb2 | NM_138749.3 | chr15:88985975-89011218 | | 23273 | Poldip2 | NM_026389.3 | chr11:78325797-78336238 |
| 23179 | Plxnb3 | NM_019587.2 | chrX:71002441-71017849 | | 23274 | Poldip3 | NM_178627.3 | chr15:82956407-82979766 |
| 23180 | Plxnc1 | NM_018797.2 | chr10:94253611-94407212 | | 23275 | Pole | NM_011132.2 | chr5:110715337-110766472 |
| 23181 | Plxnd1 | NM_026376.3 | chr6:115904828-115945023 | | 23276 | Pole2 | NM_011133.2 | chr12:70302765-70329177 |
| 23182 | Pm20d1 | NM_178079.3 | chr1:133693971-133714692 | | 23277 | Pole3 | NM_021498.2 | chr4:62184834-62186048 |
| 23183 | Pm20d2 | NM_001034867.2 | chr4:33257381-33276712 | | 23278 | Pole4 | NM_025882.3 | chr6:82596705-82602859 |
| 23184 | Pmaip1 | NM_021451.2 | chr18:66618257-66625212 | | 23279 | Polg | NM_017462.2 | chr7:86594269-86611159 |
| 23185 | Pmch | NM_029971.2 | chr10:87553817-87555119 | | 23280 | Polg2 | NM_015810.2 | chr11:106612539-106640851 |
| 23186 | Pmel | NM_021882.4 | chr10:128143314-128157294 | | 23281 | Polg2 | NR_027785.1 | chr11:106612539-106640851 |
| 23187 | Pmepa1 | NM_022995.3 | chr2:173049965-173102034 | | 23282 | Polh | NM_030715.3 | chr17:46308941-46339574 |
| 23188 | Pmf1 | NM_025928.3 | chr3:88198064-88214238 | | 23283 | Poli | NM_001136090.2 | chr18:70668333-70689975 |
| 23189 | Pmfbp1 | NM_019938.3 | chr8:112017926-112066542 | | 23284 | Poli | NM_001289515.1 | chr18:70668333-70689975 |
| 23190 | Pmis2 | NR_027848.1 | chr7:31455740-31456624 | | 23285 | Poli | NM_001289516.1 | chr18:70668333-70689975 |
| 23191 | Pmis2 | NR_027849.1 | chr7:31455740-31456624 | | 23286 | Poli | NM_013972.1 | chr18:70668333-70689975 |
| 23192 | Pml | NM_008884.5 | chr9:58064986-58097593 | | 23287 | Polk | NM_012048.2 | chr13:97250643-97312440 |
| 23193 | Pml | NM_178087.4 | chr9:58064986-58097593 | | 23288 | Poll | NM_020032.1 | chr19:45626765-45635033 |
| 23194 | Pmm1 | NM_001282040.1 | chr15:81781535-81791360 | | 23289 | Polm | NM_017401.2 | chr11:5727862-5738019 |
| 23195 | Pmm1 | NM_001113471.1 | chr15:81781535-81791360 | | 23290 | Poln | NM_001289803.1 | chr5:34349827-34512175 |
| 23196 | Pmm1 | NM_013872.4 | chr15:81781535-81791360 | | 23291 | Poln | NM_001289804.1 | chr5:34349827-34512175 |
| 23197 | Pmm2 | NM_016881.2 | chr16:8637799-8657617 | | 23292 | Poln | NM_181857.4 | chr5:34349827-34512175 |

Fig. 25 - 124

| | | | |
|---|---|---|---|
| 23293 | Polq | NM_001159369.1 | chr16:37011871-37095503 |
| 23294 | Polq | NM_029977.2 | chr16:37011871-37095503 |
| 23295 | Polr1a | NM_009088.3 | chr6:71859046-71929355 |
| 23296 | Polr1b | NM_009086.2 | chr2:128926731-128952331 |
| 23297 | Polr1c | NM_009085.2 | chr17:46380868-46384994 |
| 23298 | Polr1d | NM_009087.2 | chr5:147888921-147922937 |
| 23299 | Polr1d | NM_181730.4 | chr5:147888921-147922937 |
| 23300 | Polr1e | NM_001285800.1 | chr4:45031480-45097476 |
| 23301 | Polr1e | NM_022811.3 | chr4:45031480-45097476 |
| 23302 | Polr2a | NM_001291068.1 | chr11:69547500-69572135 |
| 23303 | Polr2a | NM_009089.2 | chr11:69547500-69572135 |
| 23304 | Polr2b | NM_153798.2 | chr5:77739509-77778353 |
| 23305 | Polr2c | NM_009090.5 | chr8:97381350-97388140 |
| 23306 | Polr2d | NM_027602.3 | chr18:31948812-31956355 |
| 23307 | Polr2d | NM_027101.2 | chr18:31948812-31956355 |
| 23308 | Polr2e | NM_025554.2 | chr10:79498697-79502404 |
| 23309 | Polr2f | NM_027231.1 | chr15:78971796-78982197 |
| 23310 | Polr2g | NM_026329.2 | chr19:8867618-8873047 |
| 23311 | Polr2h | NM_145632.2 | chr16:20717898-20722338 |
| 23312 | Polr2i | NM_027259.1 | chr7:31017093-31018406 |
| 23313 | Polr2j | NM_011293.2 | chr5:136592560-136598817 |
| 23314 | Polr2k | NM_001039638.2 | chr15:36103764-36106767 |
| 23315 | Polr2k | NM_023127.3 | chr15:36103764-36106767 |
| 23316 | Polr2l | NM_025593.1 | chr7:148657758-148661052 |
| 23317 | Polr2m | NM_001164793.1 | chr9:71326243-71333790 |
| 23318 | Polr2m | NM_178602.3 | chr9:71326243-71333790 |
| 23319 | Polr3a | NM_001081247.1 | chr14:25267915-25306268 |
| 23320 | Polr3b | NM_027423.1 | chr10:84085181-84189923 |
| 23321 | Polr3c | NM_028925.1 | chr3:96515817-96531362 |
| 23322 | Polr3d | NM_001164082.1 | chr14:70838554-70843278 |
| 23323 | Polr3d | NM_025945.3 | chr14:70838554-70843278 |
| 23324 | Polr3e | NM_001164096.1 | chr7:128061257-128090946 |
| 23325 | Polr3e | NM_025298.3 | chr7:128061257-128090946 |
| 23326 | Polr3f | NM_029763.3 | chr2:144353480-144367515 |
| 23327 | Polr3g | NM_001081176.1 | chr13:81812835-81850012 |
| 23328 | Polr3gl | NM_027241.4 | chr3:96381796-96398081 |
| 23329 | Polr3h | NM_030229.1 | chr15:81745460-81756643 |
| 23330 | Polr3k | NM_025901.2 | chr2:181599064-181605531 |
| 23331 | Polrmt | NM_172551.3 | chr10:79198869-79209326 |
| 23332 | Pom121 | NM_148932.2 | chr5:135852010-135870416 |
| 23333 | Pom121l2 | NM_001164166.1 | chr13:144992421-45000319 |
| 23334 | Pom121l2 | NM_001162928.1 | chr13:22073049-22080603 |
| 23335 | Pom121l2 | NM_001162929.1 | chr13:22073049-22080603 |
| 23336 | Pomc | NM_001278581.1 | chr12:3954944-3960643 |
| 23337 | Pomc | NM_001278583.1 | chr12:3954944-3960643 |
| 23338 | Pomc | NM_001278583.1 | chr12:3954944-3960643 |
| 23339 | Pomc | NM_001278584.1 | chr12:3954944-3960643 |
| 23340 | Pomc | NM_008895.4 | chr12:3954944-3960643 |
| 23341 | Pomgnt1 | NM_001290658.1 | chr4:115823122-115832449 |
| 23342 | Pomgnt1 | NM_026651.2 | chr4:115823122-115832449 |
| 23343 | Pomgnt1 | NM_029786.2 | chr4:115823122-115832449 |
| 23344 | Pomgnt2 | NM_001289558.1 | chr9:121890723-121905144 |
| 23345 | Pomgnt2 | NM_001289559.1 | chr9:121890723-121905144 |
| 23346 | Pomgnt2 | NM_001289560.1 | chr9:121890723-121905144 |
| 23347 | Pomgnt2 | NM_153540.4 | chr9:121890723-121905144 |
| 23348 | Pomk | NM_029037.2 | chr8:27091075-27104593 |
| 23349 | Pomp | NM_025624.2 | chr5:148671203-148687354 |
| 23350 | Pomt1 | NM_145145.1 | chr2:32092203-32110525 |
| 23351 | Pomt2 | NM_153415.3 | chr12:88447816-88488852 |
| 23352 | Pon1 | NM_011134.3 | chr6:5118089-5143946 |
| 23353 | Pon2 | NM_183308.2 | chr6:5214623-5248373 |
| 23354 | Pon3 | NM_173006.1 | chr6:5170851-5206203 |
| 23355 | Pop1 | NM_026340.3 | chr15:34425065-34460408 |
| 23356 | Pop1 | NM_152894.2 | chr15:34425065-34460408 |
| 23357 | Pop4 | NM_025390.4 | chr7:39047838-39056367 |
| 23358 | Pop5 | NM_026338.4 | chr5:115685859-115690979 |
| 23359 | Pop7 | NM_028753.2 | chr5:137942666-137943657 |
| 23360 | Popdc2 | NM_001081984.2 | chr16:38362258-38378302 |
| 23361 | Popdc2 | NM_022318.3 | chr16:38362258-38378302 |
| 23362 | Popdc3 | NM_024286.1 | chr10:45009110-45038256 |
| 23363 | Por | NM_008898.2 | chr5:136165083-136211195 |
| 23364 | Porcn | NM_016913.4 | chrX:7770975-7783651 |
| 23365 | Porcn | NM_023638.4 | chrX:7770975-7783651 |
| 23366 | Porcn | NM_145907.4 | chrX:7770975-7783651 |
| 23367 | Porcn | NM_145908.2 | chrX:7770975-7783651 |
| 23368 | Postn | NM_001198765.1 | chr3:54165028-54194963 |
| 23369 | Postn | NM_001198766.1 | chr3:54165028-54194963 |
| 23370 | Postn | NM_015784.3 | chr3:54165028-54194963 |
| 23371 | Pot1a | NM_133931.4 | chr6:25693734-25759026 |
| 23372 | Pot1b | NM_028370.1 | chr17:55791322-55851926 |
| 23373 | Poteg | NM_026256.2 | chr8:28558141-28605644 |
| 23374 | Poteg | NM_027618.1 | chr8:28558141-28605644 |
| 23375 | Pou1f1 | NM_008849.4 | chr16:65520963-65534316 |
| 23376 | Pou2af1 | NM_011136.2 | chr9:51021794-51048184 |
| 23377 | Pou2f1 | NM_011137.3 | chr1:167718811-167932765 |
| 23378 | Pou2f1 | NM_198932.3 | chr1:167718811-167932765 |
| 23379 | Pou2f1 | NM_198933.1 | chr1:167718811-167932765 |
| 23380 | Pou2f1 | NM_198934.3 | chr1:167718811-167932765 |
| 23381 | Pou2f2 | NM_001163554.1 | chr7:25876133-25917479 |
| 23382 | Pou2f2 | NM_001163555.1 | chr7:25876133-25917479 |
| 23383 | Pou2f2 | NM_001163556.1 | chr7:25876133-25917479 |
| 23384 | Pou2f2 | NM_011138.2 | chr7:25876133-25917479 |
| 23385 | Pou2f3 | NM_042932021-43013838 | chr9:42932021-43013838 |
| 23386 | Pou3f1 | NM_011141.2 | chr4:124334888-124337899 |
| 23387 | Pou3f2 | NM_008899.2 | chr4:22409241-22415513 |

| | | | |
|---|---|---|---|
| 23388 | Pou3f3 | NM_008900.2 | chr1:42753990-42757054 |
| 23389 | Pou3f3os | NR_027826.1 | chr1:42755044-42751670 |
| 23390 | Pou3f4 | NM_008901.1 | chrX:108009803-108010889 |
| 23391 | Pou4f1 | NM_011143.4 | chr14:104861540-104867216 |
| 23392 | Pou4f2 | NM_138944.2 | chr8:80956907-80960551 |
| 23393 | Pou4f3 | NM_138945.2 | chr18:42554250-42555747 |
| 23394 | Pou5f1 | NM_001252452.1 | chr17:35642976-35647722 |
| 23395 | Pou5f1 | NM_013633.3 | chr17:35642976-35647722 |
| 23396 | Pou5f2 | NM_029315.1 | chr13:78164163-78165557 |
| 23397 | Pou6f1 | NM_010127.3 | chr15:100405748-100416796 |
| 23398 | Pou6f2 | NM_175006.2 | chr13:18216793-18473873 |
| 23399 | Pp2d1 | NM_173449.3 | chr17:53646785-53678776 |
| 23400 | Ppa1 | NM_026438.4 | chr10:61111368-61136913 |
| 23401 | Ppa2 | NM_146141.2 | chr3:132973079-133041033 |
| 23402 | Ppan | NM_145610.2 | chr9:20692618-20696623 |
| 23403 | Ppap2a | NM_008247.3 | chr13:113590984-113717588 |
| 23404 | Ppap2a | NM_008903.2 | chr13:113590984-113717588 |
| 23405 | Ppap2b | NM_080555.2 | chr4:104829951-104905372 |
| 23406 | Ppap2c | NM_015817.3 | chr10:78989169-78996532 |
| 23407 | Ppapdc1a | NM_001080963.1 | chr7:136400607-136534821 |
| 23408 | Ppapdc1b | NM_028000.1 | chr8:26830519-26835359 |
| 23409 | Ppapdc2 | NM_028922.3 | chr19:29038410-29041291 |
| 23410 | Ppapdc3 | NM_145521.3 | chr2:31951170-31966340 |
| 23411 | Ppara | NM_001113418.1 | chr15:85565993-85637281 |
| 23412 | Ppara | NM_011144.6 | chr15:85565993-85637281 |
| 23413 | Ppard | NM_011145.3 | chr17:28369699-28438414 |
| 23414 | Pparg | NM_001127330.2 | chr6:115311238-115440419 |
| 23415 | Pparg | NM_011146.3 | chr6:115311238-115440419 |
| 23416 | Ppargc1a | NM_008904.2 | chr5:51845487-51945160 |
| 23417 | Ppargc1a | NR_027710.1 | chr5:51845487-51945160 |
| 23418 | Ppargc1b | NM_133249.2 | chr18:61457789-61560085 |
| 23419 | Ppat | NM_172146.2 | chr5:77342274-77380603 |
| 23420 | Ppbp | NM_023785.2 | chr5:91197543-91199086 |
| 23421 | Ppcdc | NM_176831.2 | chr9:57260470-57287921 |
| 23422 | Ppcs | NM_026494.3 | chr4:119091137-119095025 |
| 23423 | Ppdpf | NM_025598.2 | chr2:180922047-180923209 |
| 23424 | Ppef1 | NM_011147.1 | chrX:157061026-157157904 |
| 23425 | Ppef2 | NM_011148.3 | chr5:92655999-92682185 |
| 23426 | Ppfia1 | NM_001033319.2 | chr7:151662659-151739634 |
| 23427 | Ppfia1 | NM_001195086.1 | chr7:151662659-151739634 |
| 23428 | Ppfia2 | NM_001205341.1 | chr10:105907365-106370524 |
| 23429 | Ppfia2 | NM_177373.4 | chr10:105907365-106370524 |
| 23430 | Ppfia3 | NM_029741.2 | chr7:52594496-52622389 |
| 23431 | Ppfia4 | NM_001144855.1 | chr1:136193359-136229505 |
| 23432 | Ppfibp1 | NM_001170433.1 | chr6:146837015-146980545 |
| 23433 | Ppfibp1 | NM_026221.2 | chr6:146837015-146980545 |
| 23434 | Ppfibp2 | NM_001163557.1 | chr7:114738564-114901546 |
| 23435 | Ppfibp2 | NM_008905.2 | chr7:114738564-114901546 |
| 23436 | Pphln1 | NM_001083114.1 | chr15:93228780-93322343 |
| 23437 | Pphln1 | NM_001285863.1 | chr15:93228780-93322343 |
| 23438 | Pphln1 | NM_001285864.1 | chr15:93228780-93322343 |
| 23439 | Pphln1 | NM_146062.3 | chr15:93228780-93322343 |
| 23440 | Pphln1 | NM_175363.4 | chr15:93228780-93322343 |
| 23441 | Ppia | NM_008907.1 | chr11:6315872-6319813 |
| 23442 | Ppib | NM_011149.2 | chr9:65907976-65914436 |
| 23443 | Ppic | NM_008908.4 | chr18:53565994-53577661 |
| 23444 | Ppid | NM_026352.3 | chr3:79395310-79407572 |
| 23445 | Ppie | NM_019489.5 | chr4:122804367-122817184 |
| 23446 | Ppif | NM_134084.1 | chr14:26513656-26519952 |
| 23447 | Ppifos | NR_028021.1 | chr14:26515842-26520768 |
| 23448 | Ppig | NM_001081086.1 | chr2:69561144-69592116 |
| 23449 | Ppih | NM_001110129.1 | chr4:118972614-118993128 |
| 23450 | Ppih | NM_001110130.1 | chr4:118972614-118993128 |
| 23451 | Ppih | NM_028677.4 | chr4:118972614-118993128 |
| 23452 | Ppil1 | NM_026845.4 | chr17:29387779-29400916 |
| 23453 | Ppil2 | NM_001252444.1 | chr16:17070231-17111345 |
| 23454 | Ppil2 | NM_001252445.1 | chr16:17070231-17111345 |
| 23455 | Ppil2 | NM_144954.3 | chr16:17070231-17111345 |
| 23456 | Ppil3 | NM_001285826.1 | chr1:58487836-58502330 |
| 23457 | Ppil3 | NM_001285827.1 | chr1:58487836-58502330 |
| 23458 | Ppil3 | NM_027351.3 | chr1:58487836-58502330 |
| 23459 | Ppil3 | NM_027374.3 | chr1:58487836-58502330 |
| 23460 | Ppil4 | NM_026141.3 | chr10:7512691-7542361 |
| 23461 | Ppil6 | NM_028430.1 | chr10:41210244-41234094 |
| 23462 | Ppip5k1 | NM_178795.4 | chr2:121136297-121176749 |
| 23463 | Ppip5k2 | NM_173760.5 | chr1:99602619-99666669 |
| 23464 | Ppl | NM_008909.2 | chr16:5086383-5132574 |
| 23465 | Ppm1a | NM_008910.3 | chr12:73862197-73895927 |
| 23466 | Ppm1b | NM_001159496.1 | chr17:85316521-85423332 |
| 23467 | Ppm1b | NM_001159497.1 | chr17:85316521-85423332 |
| 23468 | Ppm1b | NM_001159498.1 | chr17:85316521-85423332 |
| 23469 | Ppm1b | NM_011151.2 | chr17:85316521-85423332 |
| 23470 | Ppm1d | NM_016910.3 | chr11:85124755-85160573 |
| 23471 | Ppm1e | NM_177167.4 | chr11:87040407-87172496 |
| 23472 | Ppm1f | NM_176833.4 | chr16:16896561-16927468 |
| 23473 | Ppm1g | NM_008014.3 | chr5:31505041-31522918 |
| 23474 | Ppm1h | NM_001110218.1 | chr10:122115817-122382849 |
| 23475 | Ppm1h | NM_176919.4 | chr10:122115817-122382849 |
| 23476 | Ppm1j | NM_027982.2 | chr3:104583973-104588935 |
| 23477 | Ppm1k | NM_175523.2 | chr6:57456495-57485420 |
| 23478 | Ppm1l | NM_178726.3 | chr3:69120839-69359318 |
| 23479 | Ppm1m | NM_026447.4 | chr9:106097283-106101564 |
| 23480 | Ppm1m | NM_198931.3 | chr9:106097283-106101564 |
| 23481 | Ppm1n | NM_177691.3 | chr7:19862155-19865398 |
| 23482 | Ppme1 | NM_028292.2 | chr7:107475246-107520406 |

Fig. 25 - 125

| | | | | | | | | |
|---|---|---|---|---|---|---|---|---|
| 23483 | Ppox | NM_008911.1 | chr1:173207122-173211317 | | 23578 | Ppp4r1 | NM_001114131.1 | chr17:66132694-66191266 |
| 23484 | Ppp1ca | NM_031868.2 | chr9:4192174-4195419 | | 23579 | Ppp4r1 | NM_146081.2 | chr17:66132694-66191266 |
| 23485 | Ppp1cb | NM_172707.3 | chr5:32761342-32796085 | | 23580 | Ppp4r1 | NR_104465.1 | chr17:66132694-66191266 |
| 23486 | Ppp1cc | NM_013636.3 | chr5:122608287-122625278 | | 23581 | Ppp4rl-ps | NR_027957.1 | chr2:173404820-173485040 |
| 23487 | Ppp1r10 | NM_001163818.1 | chr17:36054141-36069228 | | 23582 | Ppp4r2 | NM_182939.4 | chr5:100783631-100818711 |
| 23488 | Ppp1r11 | NM_029632.3 | chr17:37085299-37088737 | | 23583 | Ppp4r4 | NM_028980.3 | chr12:104770774-104852042 |
| 23489 | Ppp1r12a | NM_027892.2 | chr10:107599455-107714631 | | 23584 | Ppp5c | NM_011155.2 | chr7:17589989-17613263 |
| 23490 | Ppp1r12b | NM_001081307.1 | chr1:136662519-136852517 | | 23585 | Ppp6c | NM_024209.2 | chr2:39052317-39081858 |
| 23491 | Ppp1r12b | NR_035606.3 | chr1:136662519-136852517 | | 23586 | Ppp6r1 | NM_172894.2 | chr7:4583096-4610552 |
| 23492 | Ppp1r12c | NM_029834.3 | chr7:4433122-4453282 | | 23587 | Ppp6r2 | NM_026813.1 | chr15:89041989-89116692 |
| 23493 | Ppp1r13b | NM_011625.1 | chr12:113066668-113146266 | | 23588 | Ppp6r2 | NM_027805.2 | chr15:89041989-89116692 |
| 23494 | Ppp1r13l | NM_001010836.3 | chr7:19946564-19963882 | | 23589 | Ppp6r3 | NM_001164159.1 | chr19:3454927-3575749 |
| 23495 | Ppp1r14a | NM_026731.3 | chr7:30074338-30078409 | | 23590 | Ppp6r3 | NM_028999.1 | chr19:3454927-3575749 |
| 23496 | Ppp1r14b | NM_008889.2 | chr19:7049537-7051814 | | 23591 | Ppp6r3 | NM_029456.2 | chr19:3454927-3575749 |
| 23497 | Ppp1r14c | NM_133485.2 | chr10:6881565-6980391 | | 23592 | Pprc1 | NM_001081214.1 | chr19:46131028-46147399 |
| 23498 | Pppr14d | NM_001290796.1 | chr2:119043854-119055601 | | 23593 | Ppt1 | NM_008917.3 | chr4:122513469-122536418 |
| 23499 | Ppp1r14d | NM_028104.4 | chr2:119043854-119055601 | | 23594 | Ppt2 | NM_019441.5 | chr17:34753606-34764042 |
| 23500 | Ppp1r15a | NM_008654.2 | chr7:52778287-52781638 | | 23595 | Pptc7 | NM_177242.4 | chr5:122734406-122774290 |
| 23501 | Ppp1r15b | NM_133819.3 | chr1:135027742-135036377 | | 23596 | Ppwd1 | NM_172807.4 | chr13:104995202-105018924 |
| 23502 | Ppp1r16a | NM_033371.2 | chr15:76502109-76525345 | | 23597 | Ppy | NM_008918.1 | chr11:101961244-101962614 |
| 23503 | Ppp1r16b | NM_001159662.1 | chr2:158492468-158592070 | | 23598 | Pqbp1 | NM_001252528.1 | chrX:7471644-7476395 |
| 23504 | Ppp1r16b | NM_153089.4 | chr2:158492468-158592070 | | 23599 | Pqbp1 | NM_001252529.1 | chrX:7471644-7476395 |
| 23505 | Ppp1r17 | NM_011153.3 | chr6:55967508-55982682 | | 23600 | Pqbp1 | NM_019478.4 | chrX:7471644-7476395 |
| 23506 | Ppp1r18 | NM_001146710.1 | chr17:36002539-36012541 | | 23601 | Pqlc1 | NM_001164420.1 | chr18:80451983-80489463 |
| 23507 | Ppp1r18 | NM_001146711.1 | chr17:36002539-36012541 | | 23602 | Pqlc1 | NM_001164421.1 | chr18:80451983-80489463 |
| 23508 | Ppp1r18 | NM_175242.1 | chr17:36002539-36012541 | | 23603 | Pqlc1 | NM_001164422.1 | chr18:80451983-80489463 |
| 23509 | Ppp1r1a | NM_021391.1 | chr15:103360709-103368423 | | 23604 | Pqlc1 | NM_001164423.1 | chr18:80451983-80489463 |
| 23510 | Ppp1r1b | NM_144828.1 | chr11:98210052-98219109 | | 23605 | Pqlc1 | NM_001164424.1 | chr18:80451983-80489463 |
| 23511 | Ppp1r1c | NM_001290743.1 | chr2:79547936-79658703 | | 23606 | Pqlc1 | NM_025861.1 | chr18:80451983-80489463 |
| 23512 | Ppp1r1c | NM_172420.4 | chr2:79547936-79658703 | | 23607 | Pqlc2 | NM_145384.2 | chr4:138853919-138866615 |
| 23513 | Ppp1r1c | NR_110979.1 | chr2:79547936-79658703 | | 23608 | Pqlc3 | NM_001161111.1 | chr12:16995453-17006924 |
| 23514 | Ppp1r1c | NR_110980.1 | chr2:79547936-79658703 | | 23609 | Pqlc3 | NM_172574.2 | chr12:16995453-17006924 |
| 23515 | Ppp1r2 | NM_025800.3 | chr16:31251627-31275363 | | 23610 | Pradc1 | NM_001163427.1 | chr6:85396778-85418471 |
| 23516 | Ppp1r21 | NM_028258.4 | chr17:88929463-88987707 | | 23611 | Pradc1 | NM_028505.2 | chr6:85396778-85418471 |
| 23517 | Ppp1r26 | NM_001005420.1 | chr2:28303460-28311028 | | 23612 | Pradc1 | NR_028081.1 | chr6:85396778-85418471 |
| 23518 | Ppp1r27 | NM_026814.3 | chr11:120411288-120412446 | | 23613 | Praf2 | NM_138602.4 | chrX:7305696-7308189 |
| 23519 | Ppp1r2-ps3 | NR_003650.1 | chr19:30613365-30614169 | | 23614 | Pram1 | NM_001002842.2 | chr17:33775000-33782651 |
| 23520 | Ppp1r2-ps7 | NR_033731.1 | chrX:22038721-22040669 | | 23615 | Pram1 | NR_028279.1 | chr17:33775000-33782651 |
| 23521 | Ppp1r2-ps9 | NR_033171.1 | chrX:14687711-14688615 | | 23616 | Prame | NM_029459.2 | chrX:132147540-132162244 |
| 23522 | Ppp1r32 | NM_133689.1 | chr19:10548746-10557387 | | 23617 | Pramef12 | NM_029948.2 | chr4:143981576-143998367 |
| 23523 | Ppp1r35 | NM_027242.4 | chr5:138220145-138221335 | | 23618 | Pramef17 | NM_001085540.2 | chr4:143581029-143584272 |
| 23524 | Ppp1r36 | NM_001165286.1 | chr12:77518585-77540478 | | 23619 | Pramef25 | NM_001126315.2 | chr4:143538085-143540919 |
| 23525 | Ppp1r37 | NM_199149.3 | chr7:20116315-20147747 | | 23620 | Pramef6 | NM_001085414.2 | chr4:143484139-143490283 |
| 23526 | Ppp1r3a | NM_080464.2 | chr6:14663821-14705274 | | 23621 | Pramef8 | NM_172877.2 | chr4:143002328-143010990 |
| 23527 | Ppp1r3b | NM_177741.4 | chr8:36438794-36451191 | | 23622 | Prameli | NM_031377.2 | chr4:142984343-142989722 |
| 23528 | Ppp1r3c | NM_016854.2 | chr19:36806220-36811094 | | 23623 | Prameli3 | NM_031390.2 | chrX:131836854-131847175 |
| 23529 | Ppp1r3d | NM_001085501.2 | chr2:178145910-178149168 | | 23624 | Pramel4 | NM_001001319.3 | chr4:143649028-143659221 |
| 23530 | Ppp1r3e | NM_001167908.1 | chr14:55494483-55496375 | | 23625 | Pramel5 | NM_001085418.2 | chr4:143860535-143870369 |
| 23531 | Ppp1r3f | NM_001290574.1 | chrX:7135687-7182546 | | 23626 | Pramel6 | NM_178249.1 | chr2:87348614-87351022 |
| 23532 | Ppp1r3f | NM_138605.3 | chrX:7135687-7182546 | | 23627 | Pramel7 | NM_178250.2 | chr2:87329244-87332575 |
| 23533 | Ppp1r3fos | NR_029473.1 | chrX:7150726-7158142 | | 23628 | Prap1 | NM_009475.2 | chr7:147279294-147283102 |
| 23534 | Ppp1r3g | NM_029628.1 | chr13:36059774-36062257 | | 23629 | Prb1 | NM_198669.1 | chr6:132156813-132160539 |
| 23535 | Ppp1r42 | NM_027033.4 | chr1:9958702-9999217 | | 23630 | Prc1 | NM_001285997.1 | chr7:87439336-87461145 |
| 23536 | Ppp1r42 | NM_145692.2 | chr1:9958702-9999217 | | 23631 | Prc1 | NM_001285998.1 | chr7:87439336-87461145 |
| 23537 | Ppp1r42 | NR_110971.1 | chr1:9958702-9999217 | | 23632 | Prc1 | NM_145150.3 | chr7:87439336-87461145 |
| 23538 | Ppp1r7 | NM_023200.2 | chr1:95240222-95264195 | | 23633 | Prcc | NM_033573.2 | chr3:87662824-87689484 |
| 23539 | Ppp1r8 | NM_001290725.1 | chr4:132382838-132399084 | | 23634 | Prcp | NM_028243.3 | chr7:100023762-100083091 |
| 23540 | Ppp1r8 | NM_146154.3 | chr4:132382838-132399084 | | 23635 | Prdm1 | NM_007548.4 | chr10:44156980-44178493 |
| 23541 | Ppp1r9a | NM_181595.3 | chr6:4853319-5115661 | | 23636 | Prdm10 | NM_001080817.1 | chr9:31122691-31186128 |
| 23542 | Ppp1r9b | NM_172261.3 | chr11:94852525-94868212 | | 23637 | Prdm11 | NM_001177536.1 | chr2:92815063-92886301 |
| 23543 | Ppp2ca | NM_019411.4 | chr11:51912325-51936251 | | 23638 | Prdm12 | NM_001123362.1 | chr2:31495556-31511315 |
| 23544 | Ppp2ch | NM_017374.3 | chr8:34710093-34730276 | | 23639 | Prdm13 | NM_001080771.1 | chr4:21604626-21613110 |
| 23545 | Ppp2r1a | NM_016891.3 | chr17:21082417-21102869 | | 23640 | Prdm14 | NM_001081209.2 | chr1:13103508-13117244 |
| 23546 | Ppp2r1b | NM_001034085.2 | chr9:50665028-50817178 | | 23641 | Prdm15 | NM_144789.2 | chr16:98013073-98072834 |
| 23547 | Ppp2r1b | NM_001266553.1 | chr9:50665028-50817178 | | 23642 | Prdm16 | NM_001177995.1 | chr4:153690233-154010982 |
| 23548 | Ppp2r1b | NM_028614.3 | chr9:50665028-50817178 | | 23643 | Prdm16 | NM_001291026.1 | chr4:153690233-154010982 |
| 23549 | Ppp2r2a | NM_001205188.1 | chr14:67632892-67691308 | | 23644 | Prdm16 | NM_001291029.1 | chr4:153690233-154010982 |
| 23550 | Ppp2r2a | NM_028032.3 | chr14:67632892-67691308 | | 23645 | Prdm16 | NM_027504.3 | chr4:153690233-154010982 |
| 23551 | Ppp2r2b | NM_028392.3 | chr18:42804874-43219125 | | 23646 | Prdm2 | NM_001081355.3 | chr4:142697293-142802612 |
| 23552 | Ppp2r2b | NR_073583.1 | chr18:42804874-43219125 | | 23647 | Prdm2 | NM_001256380.1 | chr4:142697293-142802612 |
| 23553 | Ppp2r2c | NM_172994.2 | chr5:37259809-37346317 | | 23648 | Prdm4 | NM_181650.3 | chr10:85354712-85379690 |
| 23554 | Ppp2r2cos | NR_045505.1 | chr5:37264834-37268118 | | 23649 | Prdm5 | NM_027547.2 | chr6:65728955-65886371 |
| 23555 | Ppp2r2d | NM_026391.2 | chr7:146038068-146074739 | | 23650 | Prdm6 | NM_001033281.3 | chr18:53624199-53735511 |
| 23556 | Ppp2r3a | NM_001161362.3 | chr9:101007319-101154162 | | 23651 | Prdm8 | NM_029947.2 | chr5:98609887-98616467 |
| 23557 | Ppp2r3a | NM_172144.3 | chr9:101007319-101154162 | | 23652 | Prdm9 | NM_144809.2 | chr17:15680042-15700287 |
| 23558 | Ppp2r3c | NM_021534.2 | chr12:56381801-56403987 | | 23653 | Prdx1 | NM_011034.4 | chr4:116358204-116372605 |
| 23559 | Ppp2r3d | NM_001163415.1 | chr9_random:46928-56293 | | 23654 | Prdx2 | NM_011563.5 | chr8:87493546-87498212 |
| 23560 | Ppp2r3d | NM_011154.2 | chr9_random:46928-56293 | | 23655 | Prdx3 | NM_007452.2 | chr19:60939968-60950441 |
| 23561 | Ppp2r3d | NR_028110.2 | chr9_random:46928-56293 | | 23656 | Prdx4 | NM_016764.4 | chrX:151758462-151772997 |
| 23562 | Ppp2r3d | NR_102716.1 | chr9_random:46928-56293 | | 23657 | Prdx5 | NM_012021.2 | chr19:6981308-6984135 |
| 23563 | Ppp2r4 | NM_138748.5 | chr2:30271569-30303327 | | 23658 | Prdx6 | NM_007453.2 | chr1:163170242-163181297 |
| 23564 | Ppp2r5a | NM_144880.4 | chr1:193175860-193220920 | | 23659 | Prdx6b | NM_172256.5 | chr2:80132626-80135515 |
| 23565 | Ppp2r5b | NM_198168.3 | chr19:6227767-6235840 | | 23660 | Preb | NM_016703.3 | chr5:31254040-31262700 |
| 23566 | Ppp2r5c | NM_001081457.2 | chr12:111685388-111821284 | | 23661 | Prelid1 | NM_025596.5 | chr13:55423416-55426633 |
| 23567 | Ppp2r5c | NM_001081458.2 | chr12:111685388-111821284 | | 23662 | Prelid2 | NM_029942.1 | chr18:42035349-42110848 |
| 23568 | Ppp2r5c | NM_001135001.1 | chr12:111685388-111821284 | | 23663 | Prelp | NM_054077.4 | chr1:135806881-135817978 |
| 23569 | Ppp2r5c | NM_012023.9 | chr12:111685388-111821284 | | 23664 | Prep | NM_011156.2 | chr10:44787019-44878801 |
| 23570 | Ppp2r5d | NM_009358.3 | chr17:46819940-46841951 | | 23665 | Prepl | NM_001163622.1 | chr17:85427686-85489614 |
| 23571 | Ppp2r5e | NM_012024.2 | chr12:76551867-76697187 | | 23666 | Prepl | NM_001163623.1 | chr17:85427686-85489614 |
| 23572 | Ppp3ca | NM_008913.5 | chr3:136333733-136598743 | | 23667 | Prepl | NM_001163624.1 | chr17:85427686-85489614 |
| 23573 | Ppp3cb | NM_008914.2 | chr14:21318536-21365795 | | 23668 | Prepl | NM_145984.3 | chr17:85427686-85489614 |
| 23574 | Ppp3cc | NM_008915.3 | chr14:70617704-70689256 | | 23669 | Prex1 | NM_177782.3 | chr2:166391845-166559332 |
| 23575 | Ppp3r1 | NM_024459.2 | chr11:17059300-17100383 | | 23670 | Prex2 | NM_001033636.4 | chr1:10983545-11293763 |
| 23576 | Ppp3r2 | NM_001004025.4 | chr4:49691619-49694855 | | 23671 | Prex2 | NM_029525.1 | chr1:10983545-11293763 |
| 23577 | Ppp4c | NM_019674.3 | chr7:133929381-133935985 | | 23672 | Prf1 | NM_011073.3 | chr10:60760583-60767011 |

Fig. 25 - 126

| | | | |
|---|---|---|---|
| 23673 | Prg2 | NM_008920.4 | chr2:84820617-84823789 |
| 23674 | Prg3 | NM_016914.2 | chr2:84828371-84834643 |
| 23675 | Prg4 | NM_001110146.1 | chr1:152208440-152313295 |
| 23676 | Prg4 | NM_021400.3 | chr1:152208440-152313295 |
| 23677 | Prh1 | NM_011174.4 | chr6:132519859-132522419 |
| 23678 | Prickle1 | NM_001033217.4 | chr15:93329544-93426322 |
| 23679 | Prickle2 | NM_001081146.2 | chr6:92320885-92656178 |
| 23680 | Prickle2 | NM_001134459.1 | chr6:92320885-92656178 |
| 23681 | Prickle2 | NM_001134460.1 | chr6:92320885-92656178 |
| 23682 | Prickle2 | NM_001134461.1 | chr6:92320885-92656178 |
| 23683 | Prickle3 | NM_001290624.1 | chrX:7234504-7248404 |
| 23684 | Prickle3 | NM_175097.3 | chrX:7234504-7248404 |
| 23685 | Prickle4 | NM_001290337.1 | chr17:47825423-47831685 |
| 23686 | Prim1 | NM_008921.2 | chr10:127452270-127467086 |
| 23687 | Prim2 | NM_008922.2 | chr1:33510652-33726639 |
| 23688 | Prima1 | NM_133364.2 | chr12:104435117-104480356 |
| 23689 | Primpol | NM_001001184.1 | chr8:47660948-47702554 |
| 23690 | Prkaa1 | NM_001013367.3 | chr5:5093860-5131899 |
| 23691 | Prkaa2 | NM_178143.2 | chr4:104702254-104782503 |
| 23692 | Prkab1 | NM_031869.2 | chr5:116463598-116474437 |
| 23693 | Prkab2 | NM_182997.2 | chr3:97462134-97476980 |
| 23694 | Prkaca | NM_001277898.1 | chr8:86496876-86520341 |
| 23695 | Prkaca | NM_008854.5 | chr8:86496876-86520341 |
| 23696 | Prkacb | NM_001164198.1 | chr3:146392542-146475910 |
| 23697 | Prkacb | NM_001164199.1 | chr3:146392542-146475910 |
| 23698 | Prkacb | NM_001164200.1 | chr3:146392542-146475910 |
| 23699 | Prkacb | NM_011100.4 | chr3:146392542-146475910 |
| 23700 | Prkag1 | NM_016781.2 | chr15:98643227-98661939 |
| 23701 | Prkag2 | NM_001170555.1 | chr5:24368552-24606460 |
| 23702 | Prkag2 | NM_001170556.1 | chr5:24368552-24606460 |
| 23703 | Prkag2 | NM_145401.2 | chr5:24368552-24606460 |
| 23704 | Prkag2os1 | NR_040684.1 | chr5:24408387-24412667 |
| 23705 | Prkag3 | NM_153744.3 | chr1:74785495-74795529 |
| 23706 | Prkar1a | NM_021880.2 | chr11:109512262-109530962 |
| 23707 | Prkar1b | NM_001253890.1 | chr5:139493257-139606340 |
| 23708 | Prkar1b | NM_008923.3 | chr5:139493257-139606340 |
| 23709 | Prkar2a | NM_008924.2 | chr9:108594473-108651842 |
| 23710 | Prkar2b | NM_011158.3 | chr12:32643343-32746144 |
| 23711 | Prkca | NM_011101.3 | chr11:107794701-108205202 |
| 23712 | Prkcb | NM_008855.1 | chr7:129432638-129777915 |
| 23713 | Prkcd | NM_011103.3 | chr14:31408539-31439394 |
| 23714 | Prkcdbp | NM_028444.1 | chr7:112629129-112630711 |
| 23715 | Prkce | NM_011104.3 | chr17:86567125-87057259 |
| 23716 | Prkcg | NM_001291434.1 | chr7:3303657-3331154 |
| 23717 | Prkcg | NM_011104.2 | chr7:3303657-3331154 |
| 23718 | Prkch | NM_008856.3 | chr12:74686027-74879171 |
| 23719 | Prkci | NM_008857.3 | chr3:30894693-30951662 |
| 23720 | Prkcq | NM_008859.2 | chr2:11094008-11222853 |
| 23721 | Prkcsh | NM_008925.2 | chr9:21807478-21818666 |
| 23722 | Prkcz | NM_001039079.2 | chr4:154634226-154735537 |
| 23723 | Prkcz | NM_008860.3 | chr4:154634226-154735537 |
| 23724 | Prkd1 | NM_008858.3 | chr12:51442218-51750210 |
| 23725 | Prkd2 | NM_001254458.1 | chr7:17428250-17455810 |
| 23726 | Prkd2 | NM_178900.4 | chr7:17428250-17455810 |
| 23727 | Prkd3 | NM_001171004.1 | chr17:79348744-79420156 |
| 23728 | Prkd3 | NM_001171005.1 | chr17:79348744-79420156 |
| 23729 | Prkd3 | NM_029239.3 | chr17:79348744-79420156 |
| 23730 | Prkdc | NM_011159.2 | chr16:15637958-15842332 |
| 23731 | Prkg1 | NM_001013833.3 | chr19:30638976-31839523 |
| 23732 | Prkg1 | NM_011160.3 | chr19:30638976-31839523 |
| 23733 | Prkg2 | NM_008926.4 | chr5:99358791-99466098 |
| 23734 | Prkra | NM_011871.2 | chr2:76467993-76486051 |
| 23735 | Prkrip1 | NM_025774.3 | chr5:136656226-136674824 |
| 23736 | Prkrir | NM_028410.1 | chr7:105851872-105866571 |
| 23737 | Prkx | NM_016914.2 | chrX:75007373-75041299 |
| 23738 | Prl | NM_001163530.1 | chr13:27149438-27157072 |
| 23739 | Prl | NM_011164.1 | chr13:27149438-27157072 |
| 23740 | Prl2a1 | NM_019991.1 | chr13:27893523-27900065 |
| 23741 | Prl2b1 | NM_025532.3 | chr13:27475233-27482715 |
| 23742 | Prl2c1 | NM_001165522.2 | chr13:27941210-27949577 |
| 23743 | Prl2c2 | NM_031191.1 | chr13:13088390-13097597 |
| 23744 | Prl2c3 | NM_011118.2 | chr13:12883088-12892346 |
| 23745 | Prl2c4 | NM_011954.2 | chr13:12883083-12892325 |
| 23746 | Prl2c5 | NM_181852.1 | chr13:13275048-13284107 |
| 23747 | Prl3a1 | NM_025896.2 | chr13:27351357-27368529 |
| 23748 | Prl3b1 | NM_008865.3 | chr13:27334298-27341609 |
| 23749 | Prl3c1 | NM_001163218.1 | chr13:27288528-27295618 |
| 23750 | Prl3c1 | NM_013766.2 | chr13:27288528-27295618 |
| 23751 | Prl3d1 | NM_001163222.1 | chr13:27186057-27192129 |
| 23752 | Prl3d1 | NM_008864.3 | chr13:27186057-27192129 |
| 23753 | Prl3d2 | NM_172155.1 | chr13:27213572-27219351 |
| 23754 | Prl3d3 | NM_172156.2 | chr13:27248667-27254389 |
| 23755 | Prl4a1 | NM_011165.3 | chr13:28108091-28115415 |
| 23756 | Prl5a1 | NM_023746.4 | chr13:28234352-28243464 |
| 23757 | Prl6a1 | NM_011166.2 | chr13:27404495-27411121 |
| 23758 | Prl7a1 | NM_001164058.1 | chr13:27725232-27734362 |
| 23759 | Prl7a1 | NM_008930.2 | chr13:27725232-27734362 |
| 23760 | Prl7a2 | NM_011168.4 | chr13:27750452-27759905 |
| 23761 | Prl7b1 | NM_029355.2 | chr13:27693687-27702451 |
| 23762 | Prl7c1 | NM_026206.2 | chr13:27656363-27872673 |
| 23763 | Prl7d1 | NM_011120.2 | chr13:27800866-27808606 |
| 23764 | Prl8a1 | NM_028477.2 | chr13:27665790-27674040 |
| 23765 | Prl8a2 | NM_001289919.1 | chr13:27437541-27446084 |
| 23766 | Prl8a2 | NM_010088.2 | chr13:27437541-27446084 |
| 23767 | Prl8a6 | NM_001271378.1 | chr13:27524549-27530557 |
| 23768 | Prl8a6 | NM_001271379.1 | chr13:27524549-27530557 |
| 23769 | Prl8a6 | NM_011167.3 | chr13:27524549-27530557 |
| 23770 | Prl8a6 | NR_073166.1 | chr13:27524549-27530557 |
| 23771 | Prl8a8 | NM_023741.2 | chr13:27598940-27605082 |
| 23772 | Prl8a9 | NM_023332.3 | chr13:27649869-27656473 |
| 23773 | Prlh | NM_001101647.1 | chr1:92849684-92850589 |
| 23774 | Prlhr | NM_201615.2 | chr19:60542635-60544207 |
| 23775 | Prlr | NM_001253781.1 | chr15:10106992-10278935 |
| 23776 | Prlr | NM_001253782.2 | chr15:10106992-10278935 |
| 23777 | Prlr | NM_011169.2 | chr15:10106992-10278935 |
| 23778 | Prm1 | NM_013637.4 | chr16:10796424-10796916 |
| 23779 | Prm2 | NM_008933.1 | chr16:10791473-10792190 |
| 23780 | Prm3 | NM_013638.1 | chr16:10790600-10791007 |
| 23781 | Prmt1 | NM_001252476.1 | chr7:52232124-52241790 |
| 23782 | Prmt1 | NM_001252477.1 | chr7:52232124-52241790 |
| 23783 | Prmt1 | NM_019830.3 | chr7:52232124-52241790 |
| 23784 | Prmt1 | NR_045521.1 | chr7:52232124-52241790 |
| 23785 | Prmt10 | NM_001081240.3 | chr8:80073295-80105237 |
| 23786 | Prmt2 | NM_001077638.2 | chr10:75669966-75700610 |
| 23787 | Prmt2 | NM_133182.3 | chr10:75669966-75700610 |
| 23788 | Prmt3 | NM_133740.2 | chr7:57033727-57113635 |
| 23789 | Prmt5 | NM_013768.3 | chr14:55126018-55136307 |
| 23790 | Prmt6 | NM_178891.5 | chr3:110049021-110053917 |
| 23791 | Prmt6 | NR_024139.2 | chr3:110049021-110053917 |
| 23792 | Prmt7 | NM_145404.1 | chr8:108734953-108775594 |
| 23793 | Prmt8 | NM_201371.2 | chr6:127639626-127719177 |
| 23794 | Prn | NM_001278258.1 | chr2:131735663-131781867 |
| 23795 | Prn | NM_001278259.1 | chr2:131735663-131781867 |
| 23796 | Prnd | NM_001126338.2 | chr2:131735663-131781867 |
| 23797 | Prnd | NM_001278257.1 | chr2:131735663-131781867 |
| 23798 | Prnd | NM_001278520.1 | chr2:131735663-131781867 |
| 23799 | Prnd | NM_023043.3 | chr2:131735663-131781867 |
| 23800 | Prnp | NM_001278256.1 | chr2:131735663-131781867 |
| 23801 | Prnp | NM_011170.3 | chr2:131735663-131781867 |
| 23802 | Prob1 | NM_001270646.1 | chr18:35810004-35814853 |
| 23803 | Proc | NM_001042767.2 | chr18:32282779-32299224 |
| 23804 | Proc | NM_001042768.2 | chr18:32282779-32299224 |
| 23805 | Proc | NM_008934.3 | chr18:32282779-32299224 |
| 23806 | Proc | NR_045173.1 | chr18:32282779-32299224 |
| 23807 | Proca1 | NM_001045516.2 | chr11:78006893-78019265 |
| 23808 | Procr | NM_011171.2 | chr2:155576952-155581214 |
| 23809 | Prodh | NM_011172.1 | chr16:18071818-18089283 |
| 23810 | Prodh2 | NM_019546.5 | chr7:31278676-31298421 |
| 23811 | Prok1 | NM_001044382.1 | chr3:107038448-107042625 |
| 23812 | Prok2 | NM_001037539.2 | chr6:99661292-99676386 |
| 23813 | Prok2 | NM_001170419.1 | chr6:99661292-99676386 |
| 23814 | Prok2 | NM_015768.2 | chr6:99661292-99676386 |
| 23815 | Prokr1 | NM_021381.3 | chr6:87528585-87540695 |
| 23816 | Prokr2 | NM_144944.3 | chr2:132196064-132211183 |
| 23817 | Prol1 | NM_008644.2 | chr5:88746336-88757842 |
| 23818 | Prom1 | NM_001163577.1 | chr5:44384860-44492975 |
| 23819 | Prom1 | NM_001163578.1 | chr5:44384860-44492975 |
| 23820 | Prom1 | NM_001163581.1 | chr5:44384860-44492975 |
| 23821 | Prom1 | NM_001163582.1 | chr5:44384860-44492975 |
| 23822 | Prom1 | NM_001163583.1 | chr5:44384860-44492975 |
| 23823 | Prom1 | NM_001163584.1 | chr5:44384860-44492975 |
| 23824 | Prom1 | NM_001163585.1 | chr5:44384860-44492975 |
| 23825 | Prom1 | NM_008935.2 | chr5:44384860-44492975 |
| 23826 | Prom2 | NM_138750.2 | chr2:127352688-127367153 |
| 23827 | Prom2 | NM_178047.4 | chr2:127352688-127367153 |
| 23828 | Prop1 | NM_008936.1 | chr11:50764307-50767134 |
| 23829 | Prorsd1 | NM_001163454.2 | chr11:29411756-29415033 |
| 23830 | Prorsd1 | NM_026465.3 | chr11:29411756-29415033 |
| 23831 | Pros1 | NM_011173.2 | chr16:62854199-62929166 |
| 23832 | Prosc | NM_001039077.2 | chr8:28153026-28166604 |
| 23833 | Prosc | NM_001039078.2 | chr8:28153026-28166604 |
| 23834 | Prosc | NM_054057.4 | chr8:28153026-28166604 |
| 23835 | Proser1 | NM_173382.1 | chr3:53267738-53285677 |
| 23836 | Proser2 | NM_001159657.1 | chr2:6019545-6051231 |
| 23837 | Proser2 | NM_144883.4 | chr2:6019545-6051231 |
| 23838 | Prox1 | NM_008937.1 | chr1:191945657-191994559 |
| 23839 | Prox2 | NM_175198.4 | chr12:86427765-86447381 |
| 23840 | Proz | NM_025834.3 | chr8:13060907-13075006 |
| 23841 | Prp2 | NM_031499.2 | chr6:132545963-132550720 |
| 23842 | Prpf18 | NM_026045.3 | chr2:4543212-4573132 |
| 23843 | Prpf19 | NM_001253843.1 | chr19:10969720-10984049 |
| 23844 | Prpf19 | NM_001253844.1 | chr19:10969720-10984049 |
| 23845 | Prpf19 | NM_134129.4 | chr19:10969720-10984049 |
| 23846 | Prpf3 | NM_027541.4 | chr3:95634544-95659676 |
| 23847 | Prpf31 | NM_001159714.1 | chr7:3581586-3594086 |
| 23848 | Prpf31 | NM_027328.4 | chr7:3581586-3594086 |
| 23849 | Prpf38a | NM_172697.3 | chr4:108137471-108251941 |
| 23850 | Prpf38b | NM_025845.2 | chr3:108705724-108714622 |
| 23851 | Prpf39 | NM_177806.3 | chr12:66137321-66164373 |
| 23852 | Prpf4 | NM_027297.3 | chr4:62069816-62088024 |
| 23853 | Prpf40a | NM_018785.2 | chr2:52997508-53050221 |
| 23854 | Prpf40b | NM_018786.2 | chr15:99125839-99147438 |
| 23855 | Prpf4b | NM_013830.3 | chr13:34967362-34994747 |
| 23856 | Prpf6 | NM_133701.2 | chr2:181336023-181390366 |
| 23857 | Prpf8 | NM_138659.2 | chr11:75300278-75322949 |
| 23858 | Prph | NM_001163588.1 | chr15:98885604-98889409 |
| 23859 | Prph | NM_001163589.1 | chr15:98885604-98889409 |
| 23860 | Prph | NM_013639.2 | chr15:98885604-98889409 |
| 23861 | Prph2 | NM_008938.1 | chr17:47047433-47061875 |
| 23862 | Prpmp5 | NM_001024705.2 | chr6:132261608-132264761 |

Fig. 25 - 127

| | | | | | | | | |
|---|---|---|---|---|---|---|---|---|
| 23863 | Prps1 | NM_021463.4 | chrX:136991141-137010679 | | 23958 | Prss53 | NM_001081268.1 | chr7:135028958-135034484 |
| 23864 | Prps1l1 | NM_029294.2 | chr12:35669432-35671108 | | 23959 | Prss54 | NM_027640.1 | chr8:98083191-98099097 |
| 23865 | Prps1l3 | NM_001037746.3 | chr12:58331399-58343155 | | 23960 | Prss55 | NM_001081063.1 | chr14:64694279-64704226 |
| 23866 | Prps2 | NM_026862.4 | chrX:163784264-163820631 | | 23961 | Prss56 | NM_027084.1 | chr1:89080067-89084979 |
| 23867 | Prpsap1 | NM_026364.1 | chr11:116332129-116351660 | | 23962 | Prss57 | NM_001042710.1 | chr10:79244219-79251730 |
| 23868 | Prpsap2 | NM_001164242.1 | chr11:61543151-61575590 | | 23963 | Prss58 | NM_175020.3 | chr6:40845260-40850386 |
| 23869 | Prpsap2 | NM_001164243.1 | chr11:61543151-61575590 | | 23964 | Prss8 | NM_133351.3 | chr7:135069231-135073627 |
| 23870 | Prpsap2 | NM_001164244.1 | chr11:61543151-61575590 | | 23965 | Prtg | NM_175485.4 | chr9:72655080-72765114 |
| 23871 | Prpsap2 | NM_144806.2 | chr11:61543151-61575590 | | 23966 | Prtn3 | NM_011178.2 | chr10:79342411-79345917 |
| 23872 | Prr11 | NM_175563.5 | chr11:86902657-86922216 | | 23967 | Prune | NM_173347.2 | chr3:95057595-95085998 |
| 23873 | Prr12 | NM_175022.2 | chr7:52283076-52308251 | | 23968 | Prune2 | NM_181348.3 | chr19:17030607-17298422 |
| 23874 | Prr13 | NM_001170911.1 | chr15:102289600-102293237 | | 23969 | Prx | NM_019412.2 | chr7:28284342-28305060 |
| 23875 | Prr13 | NM_025385.3 | chr15:102289600-102293237 | | 23970 | Prx | NM_198048.2 | chr7:28284342-28305060 |
| 23876 | Prr14 | NM_145589.2 | chr7:134615127-134620272 | | 23971 | Psap | NM_001146120.1 | chr10:59740375-59765348 |
| 23877 | Prr14l | NM_194340.2 | chr5:33131855-33196879 | | 23972 | Psap | NM_001146121.1 | chr10:59740375-59765348 |
| 23878 | Prr15 | NM_030024.2 | chr6:54277006-54280194 | | 23973 | Psap | NM_001146122.1 | chr10:59740375-59765348 |
| 23879 | Prr15l | NM_146026.1 | chr11:96790637-96796961 | | 23974 | Psap | NM_001146123.1 | chr10:59740375-59765348 |
| 23880 | Prr16 | NM_001081224.2 | chr18:51277551-51464295 | | 23975 | Psap | NM_001146124.1 | chr10:59740375-59765348 |
| 23881 | Prr18 | NM_178774.4 | chr17:8533270-8536978 | | 23976 | Psap | NM_011179.3 | chr10:59740375-59765348 |
| 23882 | Prr18 | NR_028280.1 | chr17:8533270-8536978 | | 23977 | Psapl1 | NM_175249.3 | chr5:36546670-36549216 |
| 23883 | Prr19 | NM_001081294.1 | chr7:26086377-26089152 | | 23978 | Psat1 | NM_001205339.1 | chr19:15979612-15999549 |
| 23884 | Prr22 | NM_001195673.1 | chr17:56909698-56911557 | | 23979 | Psat1 | NM_177420.2 | chr19:15979612-15999549 |
| 23885 | Prr23a | NM_001134660.1 | chr9:98743005-98744064 | | 23980 | Psca | NM_028216.2 | chr15:74545268-74547495 |
| 23886 | Prr24 | NM_001136270.1 | chr7:16857361-16859041 | | 23981 | Psd | NM_028627.2 | chr19:46386577-46403646 |
| 23887 | Prr27 | NM_001163551.1 | chr5:88254721-88275411 | | 23982 | Psd2 | NM_001289602.1 | chr18:36124483-36174369 |
| 23888 | Prr27 | NM_028648.3 | chr5:88254721-88275411 | | 23983 | Psd2 | NM_028707.2 | chr18:36124483-36174369 |
| 23889 | Prr3 | NM_001165892.1 | chr17:36109483-36116770 | | 23984 | Psd2 | NR_110349.1 | chr18:36124483-36174369 |
| 23890 | Prr3 | NM_001282012.1 | chr17:36109483-36116770 | | 23985 | Psd3 | NM_027626.1 | chr8:70212980-70498473 |
| 23891 | Prr3 | NM_001282013.1 | chr17:36109483-36116770 | | 23986 | Psd3 | NM_030263.5 | chr8:70212980-70498473 |
| 23892 | Prr3 | NM_001282024.1 | chr17:36109483-36116770 | | 23987 | Psd3 | NM_177698.4 | chr8:70212980-70498473 |
| 23893 | Prr3 | NM_001282025.1 | chr17:36109483-36116770 | | 23988 | Psd4 | NM_177611.3 | chr2:24240916-24264249 |
| 23894 | Prr3 | NM_145487.3 | chr17:36109483-36116770 | | 23989 | Psen1 | NM_008943.2 | chr12:85029512-85076149 |
| 23895 | Prr30 | NM_029680.1 | chr14:101596906-101599286 | | 23990 | Psen2 | NM_001128605.1 | chr1:182157134-182186431 |
| 23896 | Prr32 | NM_026841.1 | chrX:42444080-42445967 | | 23991 | Psen2 | NM_011183.3 | chr1:182157134-182186431 |
| 23897 | Prr33 | NR_033261.1 | chr7:149676985-149692676 | | 23992 | Psenen | NM_025498.2 | chr7:31346884-31348203 |
| 23898 | Prr5 | NM_146061.2 | chr15:84511427-84534103 | | 23993 | Psg16 | NM_007676.4 | chr7:17659388-17684320 |
| 23899 | Prr5l | NM_001083810.2 | chr2:101554441-101679137 | | 23994 | Psg17 | NM_007677.2 | chr7:19399285-19406940 |
| 23900 | Prr5l | NM_001110849.1 | chr2:101554441-101679137 | | 23995 | Psg18 | NM_001163685.1 | chr7:18931156-18940356 |
| 23901 | Prr5l | NM_175181.5 | chr2:101554441-101679137 | | 23996 | Psg18 | NM_011963.2 | chr7:18931156-18940356 |
| 23902 | Prr7 | NM_001030296.4 | chr13:55565627-55574516 | | 23997 | Psg19 | NM_011964.2 | chr7:19374474-19383859 |
| 23903 | Prr9 | NM_175424.3 | chr3:91926125-91927869 | | 23998 | Psg20 | NM_054058.1 | chr7:19259714-19271341 |
| 23904 | Prrc1 | NM_028447.3 | chr18:57514386-57552373 | | 23999 | Psg21 | NM_027403.4 | chr7:19232002-19242074 |
| 23905 | Prrc2a | NM_001199044.1 | chr17:35286030-35301822 | | 24000 | Psg22 | NM_001004152.2 | chr7:19303438-19312597 |
| 23906 | Prrc2a | NM_020027.3 | chr17:35286030-35301822 | | 24001 | Psg23 | NM_020261.4 | chr7:19191691-19201850 |
| 23907 | Prrc2b | NM_001159634.1 | chr2:32006667-32090057 | | 24002 | Psg25 | NM_054060.1 | chr7:19105050-19117576 |
| 23908 | Prrc2b | NM_172661.2 | chr2:32006667-32090057 | | 24003 | Psg26 | NM_001029893.1 | chr7:19059930-19069498 |
| 23909 | Prrc2c | NM_001081290.1 | chr1:164601915-164670687 | | 24004 | Psg27 | NM_001037168.1 | chr7:19141862-19152654 |
| 23910 | Prrg1 | NM_001164275.2 | chrX:75694948-75829236 | | 24005 | Psg28 | NM_054063.4 | chr7:19007884-19017404 |
| 23911 | Prrg1 | NM_001289683.1 | chrX:75694948-75829236 | | 24006 | Psg29 | NM_054064.3 | chr7:17788825-17801105 |
| 23912 | Prrg1 | NM_027322.2 | chrX:75694948-75829236 | | 24007 | Psg-ps1 | NR_002857.1 | chr7:18257661-18267409 |
| 23913 | Prrg2 | NM_022999.1 | chr7:52308976-52317022 | | 24008 | Psip1 | NM_001290527.1 | chr4:83101584-83132352 |
| 23914 | Prrg3 | NM_001081135.2 | chrX:69208359-69218067 | | 24009 | Psip1 | NM_133948.1 | chr4:83101584-83132352 |
| 23915 | Prrg4 | NM_178665.5 | chr2:104670897-104690007 | | 24010 | Pskh1 | NM_173432.2 | chr8:108424373-108455702 |
| 23916 | Prrt1 | NM_030890.1 | chr17:34766630-34769205 | | 24011 | Psma1 | NM_011965.2 | chr7:121408063-121419630 |
| 23917 | Prrt2 | NM_001102563.1 | chr7:134161055-134164725 | | 24012 | Psma2 | NM_008944.2 | chr13:14705508-14717940 |
| 23918 | Prrt3 | NM_001289699.1 | chr6:113443632-113451925 | | 24013 | Psma3 | NM_011184.2 | chr12:72075610-72095910 |
| 23919 | Prrt3 | NM_001289700.1 | chr6:113443632-113451925 | | 24014 | Psma4 | NM_011966.3 | chr9:54798666-54805837 |
| 23920 | Prrt3 | NM_172487.4 | chr6:113443632-113451925 | | 24015 | Psma5 | NM_011967.3 | chr3:108059843-108082870 |
| 23921 | Prrt4 | NM_001101443.1 | chr6:29119229-29129584 | | 24016 | Psma6 | NM_011968.3 | chr12:56499811-56519446 |
| 23922 | Prrx1 | NM_001025570.1 | chr1:165175249-165243781 | | 24017 | Psma7 | NM_001289476.1 | chr2:179771071-179777169 |
| 23923 | Prrx1 | NM_011127.2 | chr1:165175249-165243781 | | 24018 | Psma7 | NM_011969.2 | chr2:179771071-179777169 |
| 23924 | Prrx1 | NM_175686.3 | chr1:165175249-165243781 | | 24019 | Psma8 | NM_001163609.1 | chr18:14864659-14920808 |
| 23925 | Prrx2 | NM_009116.2 | chr2:30700886-30736767 | | 24020 | Psmb1 | NM_011185.3 | chr17:15612684-15635240 |
| 23926 | Prrxl1 | NM_001001796.4 | chr14:33413112-33462432 | | 24021 | Psmb10 | NM_013640.3 | chr8:108459627-108462292 |
| 23927 | Prss1 | NM_053243.2 | chr6:41408928-41413785 | | 24022 | Psmb11 | NM_175204.4 | chr14:55244146-55248393 |
| 23928 | Prss12 | NM_008939.2 | chr3:123149830-123209520 | | 24023 | Psmb2 | NM_011970.4 | chr4:126354886-126386959 |
| 23929 | Prss16 | NM_019429.2 | chr13:22094044-22101610 | | 24024 | Psmb3 | NM_011971.4 | chr11:97564747-97574814 |
| 23930 | Prss2 | NM_009430.2 | chr6:41471774-41475078 | | 24025 | Psmb4 | NM_008945.3 | chr3:94688245-94690880 |
| 23931 | Prss21 | NM_020487.4 | chr17:24005038-24010080 | | 24026 | Psmb5 | NM_011186.1 | chr14:55232957-55236832 |
| 23932 | Prss22 | NM_133731.2 | chr17:24130500-24135067 | | 24027 | Psmb6 | NM_008946.4 | chr11:70338858-70341360 |
| 23933 | Prss23 | NM_029614.1 | chr7:96656294-96666096 | | 24028 | Psmb7 | NM_011187.1 | chr2:38443565-38499426 |
| 23934 | Prss27 | NM_175440.4 | chr17:24175209-24182916 | | 24029 | Psmb8 | NM_010724.2 | chr17:34385139-34388399 |
| 23935 | Prss28 | NM_053243.2 | chr17:25445590-25448821 | | 24030 | Psmb9 | NM_013585.2 | chr17:34319043-34324275 |
| 23936 | Prss29 | NM_053260.3 | chr17:25455598-25459629 | | 24031 | Psmc1 | NM_008947.3 | chr12:101350540-101361574 |
| 23937 | Prss3 | NM_011645.2 | chr6:41323757-41327612 | | 24032 | Psmc2 | NM_011188.1 | chr5:21291100-21309602 |
| 23938 | Prss30 | NM_001289093.1 | chr17:24109093-24112197 | | 24033 | Psmc3 | NM_008948.2 | chr2:90894172-90899595 |
| 23939 | Prss32 | NM_027220.2 | chr17:23990738-23996743 | | 24034 | Psmc3ip | NM_008949.3 | chr11:100953455-100956749 |
| 23940 | Prss33 | NM_001081399.2 | chr17:23970327-23972734 | | 24035 | Psmc4 | NM_011874.2 | chr7:28826720-28835111 |
| 23941 | Prss34 | NM_178172.2 | chr17:25435338-25437106 | | 24036 | Psmc5 | NM_008950.1 | chr11:106117498-106124426 |
| 23942 | Prss35 | NM_178738.1 | chr9:86636433-86650678 | | 24037 | Psmc6 | NM_025959.3 | chr14:45949498-45968746 |
| 23943 | Prss36 | NM_001081374.1 | chr7:135076151-135090239 | | 24038 | Psmd1 | NM_027357.2 | chr1:87961194-88035870 |
| 23944 | Prss37 | NM_026317.2 | chr6:40464822-40469507 | | 24039 | Psmd10 | NM_001164177.1 | chrX:137482963-137491250 |
| 23945 | Prss38 | NM_001045521.1 | chr1:59186170-59189155 | | 24040 | Psmd10 | NM_016883.2 | chrX:137482963-137491250 |
| 23946 | Prss39 | NM_009355.2 | chr1:34555274-34559907 | | 24041 | Psmd11 | NM_178616.3 | chr11:80242116-80285635 |
| 23947 | Prss40 | NM_009626.2 | chr1:34609176-34617788 | | 24042 | Psmd12 | NM_025894.2 | chr11:107340841-107359350 |
| 23948 | Prss41 | NM_027644.1 | chr17:23973751-23981123 | | 24043 | Psmd13 | NM_011875.4 | chr7:148068292-148084541 |
| 23949 | Prss42 | NM_153099.1 | chr9:110700688-110706248 | | 24044 | Psmd14 | NM_021526.2 | chr2:61549750-61638433 |
| 23950 | Prss43 | NM_199471.1 | chr9:110729193-110734008 | | 24045 | Psmd2 | NM_134101.2 | chr16:20651724-20663487 |
| 23951 | Prss44 | NM_148940.3 | chr9:110716497-110720503 | | 24046 | Psmd2 | NR_027485.1 | chr16:20651724-20663487 |
| 23952 | Prss45 | NM_153172.1 | chr9:110737091-110743814 | | 24047 | Psmd3 | NM_009439.1 | chr11:98543867-98557292 |
| 23953 | Prss46 | NM_183103.2 | chr9:110747009-110759026 | | 24048 | Psmd4 | NM_001282017.1 | chr3:94836612-94846536 |
| 23954 | Prss48 | NM_001001650.1 | chr3:85797731-85806413 | | 24049 | Psmd4 | NM_008951.2 | chr3:94836612-94846536 |
| 23955 | Prss50 | NM_146227.4 | chr9:110760470-110767132 | | 24050 | Psmd5 | NM_080554.2 | chr2:34707608-34726482 |
| 23956 | Prss51 | NM_001193631.1 | chr14:64712532-64716509 | | 24051 | Psmd6 | NM_025550.5 | chr14:14946698-14953418 |
| 23957 | Prss52 | NM_028525.2 | chr14:64723159-64732588 | | 24052 | Psmd7 | NM_010817.2 | chr8:110104279-110112382 |

Fig. 25 - 128

| | | | |
|---|---|---|---|
| 24053 | Psmd8 | NM_026545.3 | chr7:29959205-29965692 |
| 24054 | Psmd9 | NM_026000.2 | chr5:123678198-123700134 |
| 24055 | Psme1 | NM_011189.1 | chr14:56197331-56200364 |
| 24056 | Psme2 | NM_001029855.1 | chr14:56206278-56209938 |
| 24057 | Psme2 | NM_011190.3 | chr14:56206276-56209938 |
| 24058 | Psme2b | NM_001281472.1 | chr11:48758851-48759912 |
| 24059 | Psme3 | NM_011192.3 | chr11:101177564-101184844 |
| 24060 | Psme4 | NM_134013.3 | chr11:30671774-30780361 |
| 24061 | Psmf1 | NM_212446.2 | chr2:151541797-151567029 |
| 24062 | Psmg1 | NM_019537.2 | chr16:96201541-96212510 |
| 24063 | Psmg2 | NM_134138.1 | chr18:67801252-67813816 |
| 24064 | Psmg3 | NM_025604.3 | chr5:140299547-140302797 |
| 24065 | Psmg4 | NM_001101430.2 | chr13:34254832-34270041 |
| 24066 | Psmg4 | NM_001110515.2 | chr13:34254832-34270041 |
| 24067 | Psorsic2 | NM_020576.2 | chr17:35670145-35671592 |
| 24068 | Pspc1 | NM_025682.3 | chr14:57341285-57397153 |
| 24069 | Psph | NM_133900.4 | chr5:130271433-130293129 |
| 24070 | Pspn | NM_008954.2 | chr17:57138879-57139441 |
| 24071 | Psrc1 | NM_001190161.1 | chr3:108186721-108191149 |
| 24072 | Psrc1 | NM_019976.3 | chr3:108186721-108191149 |
| 24073 | Pstk | NM_001039534.1 | chr7:138514659-138531352 |
| 24074 | Pstpip1 | NM_011193.2 | chr9:55937782-55976697 |
| 24075 | Pstpip2 | NM_013831.1 | chr18:78033288-78121618 |
| 24076 | Ptafr | NM_001081211.1 | chr4:132119981-132136781 |
| 24077 | Ptar1 | NM_028208.1 | chr14:57341889-23795619 |
| 24078 | Ptbp1 | NM_001077363.2 | chr10:79314121-79337379 |
| 24079 | Ptbp1 | NM_001283013.1 | chr10:79314121-79337379 |
| 24080 | Ptbp1 | NM_008956.3 | chr10:79314121-79337379 |
| 24081 | Ptbp2 | NM_019550.2 | chr3:119421659-119486306 |
| 24082 | Ptbp3 | NM_144904.2 | chr4:59484739-59562236 |
| 24083 | Ptbp3 | NM_178164.3 | chr4:59484739-59562236 |
| 24084 | Ptcd1 | NM_133735.2 | chr5:145908247-145927973 |
| 24085 | Ptcd2 | NM_026873.2 | chr13:100089603-100114633 |
| 24086 | Ptcd3 | NM_027275.3 | chr6:71830631-71858756 |
| 24087 | Ptch1 | NM_008957.2 | chr13:63612840-63666828 |
| 24088 | Ptch2 | NM_008958.2 | chr4:116768960-116787436 |
| 24089 | Ptchd1 | NM_001093750.1 | chrX:152004278-152057870 |
| 24090 | Ptchd2 | NM_001083342.1 | chr4:147610965-147662074 |
| 24091 | Ptchd3 | NM_029049.1 | chr11:121691531-121704750 |
| 24092 | Ptchd4 | NM_028474.1 | chr17:42452895-42644690 |
| 24093 | Pcbra | NM_011195.2 | chr7:46892611-46900661 |
| 24094 | Ptdss1 | NM_008959.3 | chr13:67033766-67099337 |
| 24095 | Ptdss2 | NM_013782.4 | chr7:148317184-148342053 |
| 24096 | Pten | NM_008960.2 | chr19:32832066-32900650 |
| 24097 | Pter | NM_008961.3 | chr2:12845668-12925081 |
| 24098 | Ptf1a | NM_018809.2 | chr2:19367289-19369128 |
| 24099 | Ptgdr | NM_008962.4 | chr14:45470909-45479050 |
| 24100 | Ptgdr2 | NM_009962.3 | chr19:11011650-11017001 |
| 24101 | Ptgds | NM_008963.2 | chr2:25322231-25325269 |
| 24102 | Ptger1 | NM_013641.2 | chr8:86190539-86194002 |
| 24103 | Ptger2 | NM_008964.4 | chr14:45607785-45623495 |
| 24104 | Ptger3 | NM_011196.2 | chr3:157229855-157307722 |
| 24105 | Ptger4 | NM_001136079.2 | chr15:5183398-5194187 |
| 24106 | Ptger4 | NM_008965.2 | chr15:5183398-5194187 |
| 24107 | Ptges | NM_022415.3 | chr2:30744990-30758817 |
| 24108 | Ptges2 | NM_133783.2 | chr2:32251409-32258260 |
| 24109 | Ptges3 | NM_019766.4 | chr10:127496037-127514310 |
| 24110 | Ptges3l | NM_026865.2 | chr11:101280128-101286647 |
| 24111 | Ptgfr | NM_008966.3 | chr3:151461573-151500492 |
| 24112 | Ptgfrn | NM_011197.3 | chr3:100844158-100914089 |
| 24113 | Ptgir | NM_008967.3 | chr7:17491838-17496254 |
| 24114 | Ptgis | NM_008968.3 | chr2:167028695-167066037 |
| 24115 | Ptgr1 | NM_025968.3 | chr4:58978461-58999950 |
| 24116 | Ptgr2 | NM_001252625.1 | chr12:85626245-85656782 |
| 24117 | Ptgr2 | NM_001252626.1 | chr12:85626245-85656782 |
| 24118 | Ptgr2 | NM_029880.3 | chr12:85626245-85656782 |
| 24119 | Ptgs1 | NM_008969.4 | chr2:36085945-36107791 |
| 24120 | Ptgs2 | NM_011198.3 | chr1:151947253-151955142 |
| 24121 | Ptgs2os | NR_015466.3 | chr1:151923790-151946896 |
| 24122 | Pth | NM_020629.2 | chr7:120529089-120532087 |
| 24123 | Pth1r | NM_001083935.1 | chr9:110624588-110649649 |
| 24124 | Pth1r | NM_001083936.1 | chr9:110624588-110649649 |
| 24125 | Pth1r | NM_011199.2 | chr9:110624588-110649649 |
| 24126 | Pth2 | NM_053256.2 | chr7:52436364-52437208 |
| 24127 | Pth2r | NM_139270.2 | chr1:65357830-65435818 |
| 24128 | Pthlh | NM_008970.3 | chr6:147200631-147212607 |
| 24129 | Ptk2 | NM_001130409.1 | chr15:73035534-73253621 |
| 24130 | Ptk2 | NM_007982.2 | chr15:73035534-73253621 |
| 24131 | Ptk2b | NM_001162365.1 | chr14:66772093-66899889 |
| 24132 | Ptk2b | NM_001162366.1 | chr14:66772093-66899889 |
| 24133 | Ptk2b | NM_172498.3 | chr14:66772093-66899889 |
| 24134 | Ptk6 | NM_009184.2 | chr2:180929828-180937494 |
| 24135 | Ptk7 | NM_175168.4 | chr17:46701399-46766453 |
| 24136 | Ptma | NM_008972.2 | chr1:88423310-88427273 |
| 24137 | Ptms | NM_026988.1 | chr6:124863692-124867964 |
| 24138 | Ptn | NM_008973.1 | chr6:36665662-36761361 |
| 24139 | Ptov1 | NM_133813.1 | chr7:52118437-52125158 |
| 24140 | Ptp4a1 | NM_011200.2 | chr1:30997148-31006600 |
| 24141 | Ptp4a2 | NM_001164745.1 | chr4:129497722-129527247 |
| 24142 | Ptp4a2 | NM_008974.4 | chr4:129497722-129527247 |
| 24143 | Ptp4a3 | NM_001166388.1 | chr15:73553574-73589196 |
| 24144 | Ptp4a3 | NM_001166389.1 | chr15:73553574-73589196 |
| 24145 | Ptp4a3 | NM_001166390.1 | chr15:73553574-73589196 |
| 24146 | Ptp4a3 | NM_008975.3 | chr15:73553574-73589196 |
| 24147 | Ptpdc1 | NM_207232.2 | chr13:48673240-48720942 |

| | | | |
|---|---|---|---|
| 24148 | Ptpla | NM_001012396.2 | chr2:13948457-13977662 |
| 24149 | Ptpla | NM_013935.3 | chr2:13948457-13977662 |
| 24150 | Ptplad1 | NM_021345.2 | chr9:64834789-64869524 |
| 24151 | Ptplad2 | NM_025760.4 | chr4:88058833-88084830 |
| 24152 | Ptplb | NM_023587.2 | chr16:35022506-35109261 |
| 24153 | Ptpmt1 | NM_025576.2 | chr2:90750869-90758207 |
| 24154 | Ptpn1 | NM_011201.3 | chr2:167757826-167804885 |
| 24155 | Ptpn11 | NM_001109992.1 | chr5:121580541-121641406 |
| 24156 | Ptpn11 | NM_011202.3 | chr5:121580541-121641406 |
| 24157 | Ptpn12 | NM_011203.2 | chr5:20492462-20561615 |
| 24158 | Ptpn13 | NM_011204.2 | chr5:103854210-104027380 |
| 24159 | Ptpn14 | NM_008976.2 | chr1:191552146-191700572 |
| 24160 | Ptpn18 | NM_011206.2 | chr1:34516590-34530624 |
| 24161 | Ptpn2 | NM_001127177.1 | chr18:67825154-67884275 |
| 24162 | Ptpn2 | NM_008977.3 | chr18:67825154-67884275 |
| 24163 | Ptpn20 | NM_008978.2 | chr14:34402455-34453940 |
| 24164 | Ptpn21 | NM_001146199.1 | chr12:99914950-99975615 |
| 24165 | Ptpn21 | NM_011877.2 | chr12:99914950-99975615 |
| 24166 | Ptpn22 | NM_008979.2 | chr3:103663717-103716175 |
| 24167 | Ptpn22 | NR_104070.1 | chr3:103663717-103716175 |
| 24168 | Ptpn23 | NM_001081043.1 | chr9:110287592-110310714 |
| 24169 | Ptpn3 | NM_011207.2 | chr4:57203712-57314709 |
| 24170 | Ptpn4 | NM_019933.2 | chr1:121554669-121733648 |
| 24171 | Ptpn5 | NM_001163565.1 | chr7:54333169-54389054 |
| 24172 | Ptpn5 | NM_013643.2 | chr7:54333169-54389054 |
| 24173 | Ptpn6 | NM_001077705.2 | chr6:124670724-124688727 |
| 24174 | Ptpn6 | NM_013545.3 | chr6:124670724-124688727 |
| 24175 | Ptpn7 | NM_177081.3 | chr1:137029301-137041897 |
| 24176 | Ptpn9 | NM_019651.2 | chr9:56842775-56910614 |
| 24177 | Ptpra | NM_001163688.1 | chr2:130276013-130389485 |
| 24178 | Ptpra | NM_008980.2 | chr2:130276013-130389485 |
| 24179 | Ptprb | NM_029928.2 | chr10:115738429-115826594 |
| 24180 | Ptprc | NM_001111316.2 | chr1:139959435-140071882 |
| 24181 | Ptprc | NM_001268286.1 | chr1:139959435-140071882 |
| 24182 | Ptprc | NM_011210.4 | chr1:139959435-140071882 |
| 24183 | Ptprcap | NM_016933.3 | chr19:4154645-4156710 |
| 24184 | Ptprd | NM_011211.3 | chr4:75587140-77857799 |
| 24185 | Ptpre | NM_011212.3 | chr7:142729507-142877977 |
| 24186 | Ptprf | NM_011213.2 | chr4:117880818-117964002 |
| 24187 | Ptprg | NM_008981.3 | chr14:12386066-13074553 |
| 24188 | Ptprh | NM_207270.2 | chr7:4500215-4555643 |
| 24189 | Ptprj | NM_001135657.1 | chr2:90269912-90420804 |
| 24190 | Ptprj | NM_008982.5 | chr2:90269912-90420804 |
| 24191 | Ptprk | NM_008983.2 | chr10:27794625-28317203 |
| 24192 | Ptprm | NM_008984.2 | chr17:67016188-67703799 |
| 24193 | Ptprn | NM_008985.2 | chr1:75243615-75260783 |
| 24194 | Ptprn2 | NM_011215.2 | chr12:117724193-118516640 |
| 24195 | Ptpro | NM_001164401.1 | chr6:137200819-137413154 |
| 24196 | Ptpro | NM_001164402.3 | chr6:137200819-137413154 |
| 24197 | Ptpro | NM_001164403.1 | chr6:137200819-137413154 |
| 24198 | Ptpro | NM_011216.3 | chr6:137200819-137413154 |
| 24199 | Ptprq | NM_001081432.1 | chr10:106954415-107157083 |
| 24200 | Ptprr | NM_001161837.1 | chr10:115455418-115711985 |
| 24201 | Ptprr | NM_001161838.1 | chr10:115455418-115711985 |
| 24202 | Ptprr | NM_001161839.1 | chr10:115455418-115711985 |
| 24203 | Ptprr | NM_001161840.1 | chr10:115455418-115711985 |
| 24204 | Ptprr | NM_011217.2 | chr10:115455418-115711985 |
| 24205 | Ptprs | NM_001252453.1 | chr17:56551848-56615903 |
| 24206 | Ptprs | NM_001252455.1 | chr17:56551848-56615903 |
| 24207 | Ptprs | NM_001252456.1 | chr17:56551848-56615903 |
| 24208 | Ptprs | NM_011218.2 | chr17:56551848-56615903 |
| 24209 | Ptprt | NM_001291149.1 | chr2:161347723-162486883 |
| 24210 | Ptprt | NM_001291150.1 | chr2:161347723-162486883 |
| 24211 | Ptprt | NM_001291151.1 | chr2:161347723-162486883 |
| 24212 | Ptprt | NM_021464.1 | chr2:161347723-162486883 |
| 24213 | Ptprtos | NR_040617.1 | chr2:162216549-162219682 |
| 24214 | Ptpru | NM_001083119.2 | chr4:131324371-131394193 |
| 24215 | Ptpru | NM_011214.2 | chr4:131324371-131394193 |
| 24216 | Ptprv | NM_007955.3 | chr1:137005074-137029152 |
| 24217 | Ptprz1 | NM_001081306.1 | chr6:22825501-23002916 |
| 24218 | Ptrf | NM_008986.2 | chr11:100818050-100831931 |
| 24219 | Ptrh1 | NM_178595.3 | chr2:32631341-32633113 |
| 24220 | Ptrh2 | NM_001098810.2 | chr11:86497484-86505959 |
| 24221 | Ptrh2 | NM_175004.2 | chr11:86497484-86505959 |
| 24222 | Ptrhd1 | NM_001204912.1 | chr12:4234027-4240123 |
| 24223 | Pts | NM_011220.2 | chr9:50329721-50336746 |
| 24224 | Pttg1 | NM_001131054.1 | chr11:43233749-43239750 |
| 24225 | Pttg1 | NM_013917.2 | chr11:43233749-43239750 |
| 24226 | Pttg1ip | NM_145925.2 | chr10:77044511-77061477 |
| 24227 | Ptx3 | NM_008987.3 | chr3:66023809-66029728 |
| 24228 | Ptx4 | NM_001163416.1 | chr17:25257704-25262213 |
| 24229 | Ptx4 | NM_026747.1 | chr17:25257704-25262213 |
| 24230 | Puf60 | NM_001164600.1 | chr15:75900611-75911376 |
| 24231 | Puf60 | NM_028364.2 | chr15:75900611-75911376 |
| 24232 | Puf60 | NM_133691.5 | chr15:75900611-75911376 |
| 24233 | Pum1 | NM_001159603.1 | chr4:130219273-130337479 |
| 24234 | Pum1 | NM_001159604.1 | chr4:130219273-130337479 |
| 24235 | Pum1 | NM_001159605.1 | chr4:130219273-130337479 |
| 24236 | Pum1 | NM_001159606.1 | chr4:130219273-130337479 |
| 24237 | Pum1 | NM_030722.2 | chr4:130219273-130337479 |
| 24238 | Pum2 | NM_001160219.1 | chr12:8680939-8759389 |
| 24239 | Pum2 | NM_001160220.1 | chr12:8680939-8759389 |
| 24240 | Pum2 | NM_001160221.1 | chr12:8680939-8759389 |
| 24241 | Pum2 | NM_001160222.1 | chr12:8680939-8759389 |
| 24242 | Pum2 | NM_030723.2 | chr12:8680939-8759389 |

Fig. 25 - 129

| | | | |
|---|---|---|---|
| 24243 | Pum2 | NR_027670.1 | chr12:8680939-8759389 |
| 24244 | Pura | NM_008989.3 | chr18:36440815-36447898 |
| 24245 | Purb | NM_011221.3 | chr11:6367601-6376079 |
| 24246 | Purg | NM_001098233.1 | chr8:34496796-34527941 |
| 24247 | Purg | NM_152821.2 | chr8:34496796-34527941 |
| 24248 | Pus1 | NM_001025561.3 | chr5:111202685-111209634 |
| 24249 | Pus1 | NM_001025562.2 | chr5:111202685-111209634 |
| 24250 | Pus1 | NM_019700.4 | chr5:111202685-111209634 |
| 24251 | Pus10 | NM_001033654.2 | chr11:23546478-23632876 |
| 24252 | Pus10 | NM_028304.2 | chr11:23546478-23632876 |
| 24253 | Pus10 | NM_028956.4 | chr11:23546478-23632876 |
| 24254 | Pus3 | NM_023292.4 | chr9:35367051-35374985 |
| 24255 | Pus7 | NM_001289780.1 | chr5:23245982-23289529 |
| 24256 | Pus7 | NM_001289781.1 | chr5:23245982-23289529 |
| 24257 | Pus7 | NM_178403.1 | chr5:23245982-23289529 |
| 24258 | Pus7l | NM_172437.3 | chr15:94353070-94373938 |
| 24259 | Pusl1 | NM_001033490.1 | chr4:155262969-155265871 |
| 24260 | Pvalb | NM_013645.3 | chr15:78021547-78034586 |
| 24261 | Pvr | NM_027514.2 | chr7:20488926-20506492 |
| 24262 | Pvrl1 | NM_021424.2 | chr9:43552658-43615544 |
| 24263 | Pvrl2 | NM_001159724.1 | chr7:20301992-20334922 |
| 24264 | Pvrl2 | NM_008990.3 | chr7:20301992-20334922 |
| 24265 | Pvrl3 | NM_021495.4 | chr16:46394970-46497080 |
| 24266 | Pvrl3 | NM_021496.3 | chr16:46394970-46497080 |
| 24267 | Pvrl3 | NM_021497.2 | chr16:46394970-46497080 |
| 24268 | Pvrl4 | NM_001122680.1 | chr1:173300303-173318418 |
| 24269 | Pvrl4 | NM_027893.3 | chr1:173300303-173318418 |
| 24270 | Pvt1 | NR_003368.1 | chr15:61869542-62082530 |
| 24271 | Pwp1 | NM_133993.3 | chr10:85334575-85351848 |
| 24272 | Pwp2 | NM_029546.2 | chr10:77633654-77647894 |
| 24273 | Pwwp2a | NM_001164231.1 | chr11:43495499-43536135 |
| 24274 | Pwwp2a | NM_027557.1 | chr11:43495499-43536135 |
| 24275 | Pwwp2b | NM_001033206.2 | chr7:146434380-146453152 |
| 24276 | Pwwp2b | NM_001098636.1 | chr7:146434380-146453152 |
| 24277 | Pxdc1 | NM_025831.3 | chr13:34719709-34744550 |
| 24278 | Pxdn | NM_181350.2 | chr12:30622900-30702523 |
| 24279 | Pxk | NM_145458.3 | chr14:8930726-8997625 |
| 24280 | Pxk | NM_178279.2 | chr14:8930726-8997625 |
| 24281 | Pxmp2 | NM_008993.2 | chr5:110703304-110715187 |
| 24282 | Pxmp4 | NM_021534.3 | chr2:154412779-154429409 |
| 24283 | Pxn | NM_011223.3 | chr5:115956684-116005996 |
| 24284 | Pxn | NM_133915.3 | chr5:115956684-116005996 |
| 24285 | Pxt1 | NM_153390.1 | chr17:29070930-29079207 |
| 24286 | Pxylp1 | NM_001289645.1 | chr9:96723761-96789893 |
| 24287 | Pxylp1 | NM_001289646.1 | chr9:96723761-96789893 |
| 24288 | Pxylp1 | NM_001289647.1 | chr9:96723761-96789893 |
| 24289 | Pxylp1 | NM_153420.3 | chr9:96723761-96789893 |
| 24290 | Pycard | NM_023258.4 | chr7:135134886-135137381 |
| 24291 | Pycr1 | NM_144795.3 | chr11:120497025-120504984 |
| 24292 | Pycr2 | NM_133705.2 | chr1:182834404-182838219 |
| 24293 | Pycrl | NM_025412.2 | chr15:75746892-75751990 |
| 24294 | Pydc3 | NM_001162938.1 | chr1:175603810-175628523 |
| 24295 | Pydc4 | NM_001177349.1 | chr1:175522087-175529405 |
| 24296 | Pydc4 | NM_001177350.1 | chr1:175522087-175529405 |
| 24297 | Pygb | NM_153781.1 | chr2:150612531-150657484 |
| 24298 | Pygl | NM_133198.2 | chr12:71291801-71328670 |
| 24299 | Pygm | NM_011224.1 | chr19:6384428-6398459 |
| 24300 | Pygo1 | NM_028116.2 | chr9:72773456-72793822 |
| 24301 | Pygo2 | NM_026869.1 | chr3:89234758-89239050 |
| 24302 | Pyhin1 | NM_175026.3 | chr1:175560989-175578059 |
| 24303 | Pyroxd1 | NM_183165.3 | chr6:142294217-142311144 |
| 24304 | Pyroxd2 | NM_029011.2 | chr19:42800347-42827265 |
| 24305 | Pyurf | NM_025574.3 | chr6:57634732-57842072 |
| 24306 | Pyy | NM_145435.1 | chr11:101967990-101969090 |
| 24307 | Pzp | NM_007376.4 | chr6:128433585-128476738 |
| 24308 | Qars | NM_001168270.1 | chr9:108410335-108418272 |
| 24309 | Qars | NM_133794.2 | chr9:108410335-108418272 |
| 24310 | Qdpr | NM_024236.2 | chr5:45825270-45841468 |
| 24311 | Qk | NM_001159516.1 | chr17:10399335-10512226 |
| 24312 | Qk | NM_001159517.1 | chr17:10399335-10512226 |
| 24313 | Qk | NM_021881.2 | chr17:10399335-10512226 |
| 24314 | Qpct | NM_027455.2 | chr17:79451245-79489583 |
| 24315 | Qpctl | NM_026111.3 | chr7:19725565-19734545 |
| 24316 | Qprt | NM_133686.1 | chr7:134251283-134265543 |
| 24317 | Qrfp | NM_183424.3 | chr2:31661687-31666038 |
| 24318 | Qrfpr | NM_198192.2 | chr3:36078347-36121197 |
| 24319 | Qrich1 | NM_001114119.1 | chr9:108419417-108462498 |
| 24320 | Qrich1 | NM_175143.5 | chr9:108419417-108462498 |
| 24321 | Qrich2 | NM_001033267.2 | chr11:116302638-116315661 |
| 24322 | Qrsl1 | NM_001081054.2 | chr10:43593995-43621542 |
| 24323 | Qser1 | NM_001123327.2 | chr2:104594949-104656853 |
| 24324 | Qsox1 | NM_001024945.1 | chr1:157625284-157660029 |
| 24325 | Qsox1 | NM_023268.2 | chr1:157625284-157660029 |
| 24326 | Qsox2 | NM_153559.3 | chr2:26064649-26092940 |
| 24327 | Qtrt1 | NM_021168.2 | chr9:21216280-21224723 |
| 24328 | Qtrtd1 | NM_029128.2 | chr16:43861525-43889789 |
| 24329 | R3hcc1 | NM_001146012.2 | chr14:70097110-70107387 |
| 24330 | R3hcc1l | NM_177464.4 | chr19:42593294-42666746 |
| 24331 | R3hdm1 | NM_181750.2 | chr1:129999883-130134312 |
| 24332 | R3hdm2 | NM_001168292.1 | chr10:126827366-126936440 |
| 24333 | R3hdm2 | NM_001168293.1 | chr10:126827366-126936440 |
| 24334 | R3hdm2 | NM_027900.4 | chr10:126827366-126936440 |
| 24335 | R3hdm4 | NM_177994.4 | chr10:79372797-79379675 |
| 24336 | R3hdml | NM_001099331.2 | chr2:163318054-163328348 |
| 24337 | R74862 | NR_015529.2 | chr7:150207688-150253835 |
| 24338 | R74862 | NR_110354.1 | chr7:150207688-150253835 |
| 24339 | R74862 | NR_110355.1 | chr7:150207688-150253835 |
| 24340 | Rab1 | NM_008996.3 | chr11:20101604-20126859 |
| 24341 | Rab10 | NM_016676.5 | chr12:3247428-3309969 |
| 24342 | Rab10os | NR_015551.1 | chr12:3235791-3250374 |
| 24343 | Rab11a | NM_017382.3 | chr9:64563106-64585563 |
| 24344 | Rab11b | NM_008997.3 | chr17:33879428-33897431 |
| 24345 | Rab11fip1 | NM_001080813.2 | chr8:28249244-28285118 |
| 24346 | Rab11fip1 | NM_029423.2 | chr8:28249244-28285118 |
| 24347 | Rab11fip2 | NM_001033172.3 | chr19:59978786-60019557 |
| 24348 | Rab11fip2 | NM_001164367.1 | chr19:59978786-60019557 |
| 24349 | Rab11fip3 | NM_001162868.1 | chr17:26125980-26206122 |
| 24350 | Rab11fip3 | NM_001162869.1 | chr17:26125980-26206122 |
| 24351 | Rab11fip3 | NM_153140.2 | chr17:26125980-26206122 |
| 24352 | Rab11fip4 | NM_175543.3 | chr11:79404719-79507514 |
| 24353 | Rab11fip4os1 | NR_003283.1 | chr11:79420581-79436665 |
| 24354 | Rab11fip4os2 | NR_045898.2 | chr11:79483875-79488588 |
| 24355 | Rab11fip5 | NM_001003955.2 | chr6:85284955-85324628 |
| 24356 | Rab11fip5 | NM_177466.4 | chr6:85284955-85324628 |
| 24357 | Rab12 | NM_024448.2 | chr17:66843851-66869010 |
| 24358 | Rab13 | NM_026677.1 | chr3:90024738-90029885 |
| 24359 | Rab14 | NM_026697.3 | chr2:35035724-35056640 |
| 24360 | Rab15 | NM_134050.4 | chr12:77898949-77923511 |
| 24361 | Rab17 | NM_001159725.2 | chr1:92854709-92866197 |
| 24362 | Rab17 | NM_008998.4 | chr1:92854709-92866197 |
| 24363 | Rab18 | NM_001278447.1 | chr18:6765164-6791604 |
| 24364 | Rab18 | NM_181070.6 | chr18:6765164-6791604 |
| 24365 | Rab19 | NM_011226.1 | chr6:39331426-39340378 |
| 24366 | Rab1b | NM_029576.3 | chr19:5099206-5106996 |
| 24367 | Rab20 | NM_011227.1 | chr8:11453976-11478499 |
| 24368 | Rab21 | NM_024454.2 | chr10:114726917-114752647 |
| 24369 | Rab22a | NM_024436.3 | chr2:173485346-173527683 |
| 24370 | Rab23 | NM_001159729.1 | chr1:33776740-33799409 |
| 24371 | Rab23 | NM_008999.4 | chr1:33776740-33799409 |
| 24372 | Rab24 | NM_009000.3 | chr13:55420583-55423341 |
| 24373 | Rab25 | NM_016899.4 | chr3:88345950-88352201 |
| 24374 | Rab26 | NM_177375.1 | chr17:24665998-24670692 |
| 24375 | Rab26os | NR_045289.1 | chr17:24665195-24665689 |
| 24376 | Rab27a | NM_023635.6 | chr9:72892671-72945399 |
| 24377 | Rab27b | NM_001082553.2 | chr18:70138784-70301244 |
| 24378 | Rab27b | NM_030554.4 | chr18:70138784-70301244 |
| 24379 | Rab28 | NM_027295.2 | chr5:42016214-42099394 |
| 24380 | Rab2a | NM_021518.3 | chr4:8462790-8534849 |
| 24381 | Rab2b | NM_172601.3 | chr14:52881434-52899070 |
| 24382 | Rab30 | NM_029494.2 | chr7:99890223-99985627 |
| 24383 | Rab31 | NM_133685.2 | chr17:66001065-66122092 |
| 24384 | Rab32 | NM_026405.3 | chr10:10264836-10278005 |
| 24385 | Rab33a | NM_011228.2 | chrX:45872461-45883417 |
| 24386 | Rab33b | NM_016858.2 | chr3:51287887-51300134 |
| 24387 | Rab34 | NM_001159482.1 | chr11:78001928-78005695 |
| 24388 | Rab34 | NM_033475.3 | chr11:78001928-78005695 |
| 24389 | Rab35 | NM_198163.1 | chr5:116081996-116097167 |
| 24390 | Rab36 | NM_029781.3 | chr10:74499833-74516845 |
| 24391 | Rab37 | NM_001163753.1 | chr11:114952744-115023554 |
| 24392 | Rab37 | NM_021411.4 | chr11:114952744-115023554 |
| 24393 | Rab38 | NM_028238.7 | chr7:95578782-95640082 |
| 24394 | Rab39 | NM_175562.3 | chr9:53492214-53514337 |
| 24395 | Rab39b | NM_175122.6 | chrX:72817383-72823570 |
| 24396 | Rab3a | NM_001166399.2 | chr8:73278577-73284820 |
| 24397 | Rab3a | NM_009001.6 | chr8:73278577-73284820 |
| 24398 | Rab3b | NM_023537.5 | chr4:108551675-108615929 |
| 24399 | Rab3c | NM_023852.5 | chr13:110844395-113070414 |
| 24400 | Rab3d | NM_031874.4 | chr9:21711954-21722565 |
| 24401 | Rab3gap1 | NM_178690.4 | chr1:129765349-129840453 |
| 24402 | Rab3gap2 | NM_001163754.1 | chr1:187028047-187110625 |
| 24403 | Rab3il1 | NM_144538.2 | chr19:10092717-10110076 |
| 24404 | Rab3ip | NM_001003950.2 | chr10:116342839-116387436 |
| 24405 | Rab40b | NM_139147.3 | chr11:121217435-121249565 |
| 24406 | Rab40c | NM_139154.2 | chr17:26019059-26056659 |
| 24407 | Rab42 | NM_001081651.1 | chr4:131858108-131859271 |
| 24408 | Rab43 | NM_001039394.1 | chr6:87738846-87762158 |
| 24409 | Rab43 | NM_133717.3 | chr6:87738846-87762158 |
| 24410 | Rab43 | NR_104477.1 | chr6:87738846-87762158 |
| 24411 | Rab43 | NR_104478.1 | chr6:87738846-87762158 |
| 24412 | Rab44 | NM_001002786.2 | chr17:29272000-29285921 |
| 24413 | Rab4a | NM_009003.3 | chr8:126329895-126336191 |
| 24414 | Rab4b | NM_029391.2 | chr7:27953452-27963902 |
| 24415 | Rab5a | NM_025887.4 | chr17:53618559-53647003 |
| 24416 | Rab5b | NM_177411.4 | chr10:128114238-128133324 |
| 24417 | Rab5c | NM_024456.5 | chr11:100576579-100599444 |
| 24418 | Rab6a | NM_001163663.1 | chr7:107697630-107789782 |
| 24419 | Rab6a | NM_024287.4 | chr7:107697630-107789782 |
| 24420 | Rab6b | NM_173781.4 | chr9:103014403-103087600 |
| 24421 | Rab7 | NM_009005.3 | chr6:87950428-87963684 |
| 24422 | Rab7l1 | NM_144875.2 | chr1:133763853-133769464 |
| 24423 | Rab8a | NM_023126.2 | chr8:74685698-74705265 |
| 24424 | Rab8b | NM_173413.3 | chr9:66691470-66767512 |
| 24425 | Rab9 | NM_019773.2 | chrX:162895183-162917799 |
| 24426 | Rab9b | NM_176971.2 | chrX:133392689-133403079 |
| 24427 | Rabac1 | NM_010261.2 | chr7:25754769-25757747 |
| 24428 | Rabep1 | NM_001291141.1 | chr11:70658262-70783475 |
| 24429 | Rabep1 | NM_001291142.1 | chr11:70658262-70783475 |
| 24430 | Rabep1 | NM_001291143.1 | chr11:70658262-70783475 |
| 24431 | Rabep1 | NM_019400.3 | chr11:70658262-70783475 |
| 24432 | Rabep2 | NM_030566.2 | chr7:133572281-133589421 |

Fig. 25 - 130

| | | | |
|---|---|---|---|
| 24433 | Rabepk | NM_145522.4 | chr2:34634185-34655432 |
| 24434 | Rabgap1 | NM_001033960.1 | chr2:37298804-37421957 |
| 24435 | Rabgap1 | NM_146121.2 | chr2:37298804-37421957 |
| 24436 | Rabgap1l | NM_001038621.2 | chr1:162149304-162723069 |
| 24437 | Rabgap1l | NM_013862.5 | chr1:162149304-162723069 |
| 24438 | Rabgef1 | NM_001199059.1 | chr5:130647688-130690207 |
| 24439 | Rabgef1 | NM_019983.2 | chr5:130647688-130690207 |
| 24440 | Rabggta | NM_019519.2 | chr14:56334713-56341013 |
| 24441 | Rabggtb | NM_001163478.1 | chr3:153570252-153575930 |
| 24442 | Rabggtb | NM_001163479.1 | chr3:153570252-153575930 |
| 24443 | Rabggtb | NM_011231.2 | chr3:153570252-153575930 |
| 24444 | Rabggtb | NR_028094.1 | chr3:153570252-153575930 |
| 24445 | Rabggtb | NR_028095.1 | chr3:153570252-153575930 |
| 24446 | Rabggtb | NR_028096.1 | chr3:153570252-153575930 |
| 24447 | Rabggtb | NR_028097.1 | chr3:153570252-153575930 |
| 24448 | Rabggtb | NR_028098.1 | chr3:153570252-153575930 |
| 24449 | Rabif | NM_145510.1 | chr1:136391236-136404461 |
| 24450 | Rabl2 | NM_026817.3 | chr15:89412957-89422354 |
| 24451 | Rabl3 | NM_001042499.1 | chr16:37539979-37572471 |
| 24452 | Rabl6 | NM_001024616.1 | chr2:25438537-25463966 |
| 24453 | Rac1 | NM_009007.2 | chr5:144266348-144288861 |
| 24454 | Rac2 | NM_009008.3 | chr15:78389598-78403213 |
| 24455 | Rac3 | NM_133223.4 | chr11:120582781-120585283 |
| 24456 | Racgap1 | NM_001253808.1 | chr15:99450927-99482087 |
| 24457 | Racgap1 | NM_001253809.1 | chr15:99450927-99482087 |
| 24458 | Racgap1 | NM_012025.2 | chr15:99450927-99482087 |
| 24459 | Rad1 | NM_001289447.1 | chr15:10415772-10428818 |
| 24460 | Rad1 | NM_001289448.1 | chr15:10415772-10428818 |
| 24461 | Rad1 | NM_011232.3 | chr15:10415772-10428818 |
| 24462 | Rad17 | NM_001044371.2 | chr13:101387118-101421016 |
| 24463 | Rad17 | NM_001283011.1 | chr13:101387118-101421016 |
| 24464 | Rad17 | NM_011233.3 | chr13:101387118-101421016 |
| 24465 | Rad18 | NM_001167730.1 | chr6:112569844-112646664 |
| 24466 | Rad18 | NM_021385.2 | chr6:112569844-112646664 |
| 24467 | Rad21 | NM_009009.4 | chr15:51794149-51823306 |
| 24468 | Rad21l | NM_001276400.1 | chr2:151471139-151494269 |
| 24469 | Rad23a | NM_009010.5 | chr8:87358551-87364564 |
| 24470 | Rad23b | NM_009011.4 | chr4:55362913-55405109 |
| 24471 | Rad50 | NM_009012.2 | chr11:53463020-53520821 |
| 24472 | Rad51 | NM_011234.4 | chr2:118938552-118961806 |
| 24473 | Rad51ap1 | NM_009013.3 | chr6:126873436-126889573 |
| 24474 | Rad51ap2 | NM_001111118.1 | chr12:11462884-11469734 |
| 24475 | Rad51b | NM_001252562.1 | chr12:80398268-80915677 |
| 24476 | Rad51b | NM_009014.3 | chr12:80398268-80915677 |
| 24477 | Rad51c | NM_001291440.1 | chr11:87191108-87218456 |
| 24478 | Rad51c | NM_053269.3 | chr11:87191108-87218456 |
| 24479 | Rad51d | NM_001277938.1 | chr11:82685463-82704126 |
| 24480 | Rad51d | NM_001277939.1 | chr11:82685463-82704126 |
| 24481 | Rad51d | NM_001277941.1 | chr11:82685463-82704126 |
| 24482 | Rad51d | NM_001277942.1 | chr11:82685463-82704126 |
| 24483 | Rad51d | NM_011235.2 | chr11:82685463-82704126 |
| 24484 | Rad51d | NR_102717.1 | chr11:82685463-82704126 |
| 24485 | Rad51d | NR_102718.1 | chr11:82685463-82704126 |
| 24486 | Rad51d | NR_102719.1 | chr11:82685463-82704126 |
| 24487 | Rad51d | NR_102720.1 | chr11:82685463-82704126 |
| 24488 | Rad52 | NM_001166381.1 | chr6:119852715-119872841 |
| 24489 | Rad52 | NM_001166382.1 | chr6:119852715-119872841 |
| 24490 | Rad52 | NM_001166383.1 | chr6:119852715-119872841 |
| 24491 | Rad52 | NM_011236.2 | chr6:119852715-119872841 |
| 24492 | Rad54b | NM_001039556.3 | chr4:11486066-11542955 |
| 24493 | Rad54b | NM_001256145.1 | chr4:11486066-11542955 |
| 24494 | Rad54l | NM_001122958.1 | chr4:115748069-115796295 |
| 24495 | Rad54l | NM_001122959.1 | chr4:115748069-115796295 |
| 24496 | Rad54l | NM_009015.3 | chr4:115748069-115796295 |
| 24497 | Rad54l2 | NM_030730.2 | chr9:106590410-106691544 |
| 24498 | Rad9a | NM_011237.2 | chr19:4195198-4201603 |
| 24499 | Rad9b | NM_144912.3 | chr5:122775516-122804204 |
| 24500 | Radil | NM_001289588.1 | chr5:142960792-143027052 |
| 24501 | Radil | NM_178702.1 | chr5:142960792-143027052 |
| 24502 | Rae1 | NM_175112.5 | chr2:172822617-172841240 |
| 24503 | Raet1a | NM_009016.1 | chr10:21878415-22093945 |
| 24504 | Raet1b | NM_009017.1 | chr10:21893681-22093919 |
| 24505 | Raet1c | NM_009018.3 | chr10:21893708-22093945 |
| 24506 | Raet1d | NM_020030.2 | chr10:22081700-22093945 |
| 24507 | Raet1e | NM_198193.2 | chr10:21893327-21903720 |
| 24508 | Raf1 | NM_029780.3 | chr6:115568591-115626653 |
| 24509 | Rag1 | NM_009019.2 | chr2:101478410-101489689 |
| 24510 | Rag2 | NM_009020.3 | chr2:101464905-101472685 |
| 24511 | Rai1 | NM_001077764.1 | chr11:59918514-60034106 |
| 24512 | Rai1 | NM_009021.2 | chr11:59918514-60034106 |
| 24513 | Rai14 | NM_001166408.1 | chr15:10498732-10644386 |
| 24514 | Rai14 | NM_030690.3 | chr15:10498732-10644386 |
| 24515 | Rai2 | NM_001103367.1 | chrX:158154967-158217426 |
| 24516 | Rai2 | NM_198409.3 | chrX:158154967-158217426 |
| 24517 | Rala | NM_019491.2 | chr13:17972408-18036051 |
| 24518 | Ralb | NM_022327.5 | chr1:121366881-121401359 |
| 24519 | Ralbp1 | NM_001198949.1 | chr17:66197768-66235095 |
| 24520 | Ralbp1 | NM_009067.3 | chr17:66197768-66235095 |
| 24521 | Ralgapa1 | NM_001103719.2 | chr12:56703876-56922503 |
| 24522 | Ralgapa1 | NM_001112714.2 | chr12:56703876-56922503 |
| 24523 | Ralgapa1 | NM_001286263.1 | chr12:56703876-56922503 |
| 24524 | Ralgapa1 | NM_019994.5 | chr12:56703876-56922503 |
| 24525 | Ralgapa2 | NM_001033348.1 | chr2:146067035-146337740 |
| 24526 | Ralgapb | NM_001291137.1 | chr2:158235588-158324989 |
| 24527 | Ralgapb | NM_001291138.1 | chr2:158235588-158324989 |
| 24528 | Ralgapb | NM_177658.3 | chr2:158235588-158324989 |
| 24529 | Ralgds | NM_001145834.1 | chr2:28368686-28408602 |
| 24530 | Ralgds | NM_001145835.1 | chr2:28368686-28408602 |
| 24531 | Ralgds | NM_001145836.1 | chr2:28368686-28408602 |
| 24532 | Ralgds | NM_009058.2 | chr2:28368686-28408602 |
| 24533 | Ralgps1 | NM_001290570.1 | chr2:32988938-33227014 |
| 24534 | Ralgps1 | NM_001290572.1 | chr2:32988938-33227014 |
| 24535 | Ralgps1 | NM_175211.5 | chr2:32988938-33227014 |
| 24536 | Ralgps2 | NM_001159965.1 | chr1:158734296-158869757 |
| 24537 | Ralgps2 | NM_001159966.1 | chr1:158734296-158869757 |
| 24538 | Ralgps2 | NM_001159967.1 | chr1:158734296-158869757 |
| 24539 | Ralgps2 | NM_001159968.1 | chr1:158734296-158869757 |
| 24540 | Ralgps2 | NM_023884.4 | chr1:158734296-158869757 |
| 24541 | Ralgps2 | NR_027640.1 | chr1:158734296-158869757 |
| 24542 | Raly | NM_001139511.1 | chr2:154616845-154692997 |
| 24543 | Raly | NM_001139512.1 | chr2:154616845-154692997 |
| 24544 | Raly | NM_001139513.1 | chr2:154616845-154692997 |
| 24545 | Raly | NM_023130.3 | chr2:154616845-154692997 |
| 24546 | Ralyl | NM_001163328.1 | chr3:13471654-14182287 |
| 24547 | Ralyl | NM_001163329.1 | chr3:13471654-14182287 |
| 24548 | Ralyl | NM_001163330.1 | chr3:13471654-14182287 |
| 24549 | Ralyl | NM_178631.4 | chr3:13471654-14182287 |
| 24550 | Ramp1 | NM_001168392.1 | chr1:93076398-93121773 |
| 24551 | Ramp1 | NM_016894.3 | chr1:93076398-93121773 |
| 24552 | Ramp1 | NM_178401.3 | chr1:93076398-93121773 |
| 24553 | Ramp2 | NM_019444.2 | chr11:101107647-101109564 |
| 24554 | Ramp3 | NM_019511.1 | chr11:6558536-6577478 |
| 24555 | Ran | NM_009391.3 | chr5:129526030-129530196 |
| 24556 | Ranbp1 | NM_011239.2 | chr16:18240071-18248787 |
| 24557 | Ranbp10 | NM_145824.4 | chr8:108292207-108351250 |
| 24558 | Ranbp17 | NM_023146.2 | chr11:33111793-33413746 |
| 24559 | Ranbp17 | NR_110973.1 | chr11:33111793-33413746 |
| 24560 | Ranbp2 | NM_011240.3 | chr10:57909599-57956902 |
| 24561 | Ranbp3 | NM_001252466.1 | chr17:56812647-56851192 |
| 24562 | Ranbp3 | NM_001252467.1 | chr17:56812647-56851192 |
| 24563 | Ranbp3 | NM_027933.3 | chr17:56812647-56851192 |
| 24564 | Ranbp3 | NR_045519.1 | chr17:56812647-56851192 |
| 24565 | Ranbp3l | NM_198024.2 | chr15:8917948-8997082 |
| 24566 | Ranbp6 | NM_177721.2 | chr19:29882597-29887464 |
| 24567 | Ranbp9 | NM_019930.2 | chr13:43498042-43576342 |
| 24568 | Rangap1 | NM_001146174.1 | chr15:81534677-81560349 |
| 24569 | Rangap1 | NM_011241.4 | chr15:81534677-81560349 |
| 24570 | Rangrf | NM_001285441.1 | chr11:68781632-68788687 |
| 24571 | Rangrf | NM_001285442.1 | chr11:68781632-68788687 |
| 24572 | Rangrf | NM_001285443.1 | chr11:68781632-68788687 |
| 24573 | Rangrf | NM_021329.3 | chr11:68781632-68788687 |
| 24574 | Rap1a | NM_145541.5 | chr3:105530177-105604299 |
| 24575 | Rap1b | NM_024457.2 | chr10:117251652-117283030 |
| 24576 | Rap1gap | NM_001081155.2 | chr4:137220640-137285776 |
| 24577 | Rap1gap | NM_001256218.1 | chr4:137220640-137285776 |
| 24578 | Rap1gap | NM_029563.1 | chr4:137220640-137285776 |
| 24579 | Rap1gap2 | NM_001015046.2 | chr11:74196984-74403660 |
| 24580 | Rap1gds1 | NM_001040690.2 | chr3:138588860-138738165 |
| 24581 | Rap1gds1 | NM_001286759.1 | chr3:138588860-138738165 |
| 24582 | Rap1gds1 | NM_145544.3 | chr3:138588860-138738165 |
| 24583 | Rap2a | NM_029519.3 | chr14:120877682-120906414 |
| 24584 | Rap2b | NM_028712.2 | chr3:61168428-61172625 |
| 24585 | Rap2c | NM_172413.2 | chrX:48357090-48371195 |
| 24586 | Rapgef1 | NM_001039086.1 | chr2:29475239-29595883 |
| 24587 | Rapgef1 | NM_001039087.1 | chr2:29475239-29595883 |
| 24588 | Rapgef1 | NM_054050.2 | chr2:29475239-29595883 |
| 24589 | Rapgef2 | NM_001099624.2 | chr3:78846456-78949797 |
| 24590 | Rapgef3 | NM_001177810.1 | chr15:97575200-97598097 |
| 24591 | Rapgef3 | NM_001177811.1 | chr15:97575200-97598097 |
| 24592 | Rapgef3 | NM_144850.2 | chr15:97575200-97598097 |
| 24593 | Rapgef4 | NM_001204165.1 | chr2:71819271-72095531 |
| 24594 | Rapgef4 | NM_001204166.1 | chr2:71819271-72095531 |
| 24595 | Rapgef4 | NM_001204167.1 | chr2:71819271-72095531 |
| 24596 | Rapgef4 | NM_019688.2 | chr2:71819271-72095531 |
| 24597 | Rapgef5 | NM_175930.5 | chr12:118754951-118995451 |
| 24598 | Rapgef6 | NM_001252494.1 | chr11:54336346-54512788 |
| 24599 | Rapgef6 | NM_001252496.1 | chr11:54336346-54512788 |
| 24600 | Rapgef6 | NM_001252497.1 | chr11:54336346-54512788 |
| 24601 | Rapgef6 | NM_001252498.1 | chr11:54336346-54512788 |
| 24602 | Rapgef6 | NM_175258.4 | chr11:54336346-54512788 |
| 24603 | Rapgefl1 | NM_001080925.1 | chr11:98698098-98714319 |
| 24604 | Raph1 | NM_001045513.3 | chr1:60540028-60623609 |
| 24605 | Rapsn | NM_009023.3 | chr2:90875783-90885886 |
| 24606 | Rara | NM_001176528.1 | chr11:98799009-98836256 |
| 24607 | Rara | NM_001177302.1 | chr11:98799009-98836256 |
| 24608 | Rara | NM_001177303.1 | chr11:98799009-98836256 |
| 24609 | Rara | NM_009024.2 | chr11:98799009-98836256 |
| 24610 | Rarb | NM_001289760.1 | chr14:17263353-17914845 |
| 24611 | Rarb | NM_001289761.1 | chr14:17263353-17914845 |
| 24612 | Rarb | NM_001289762.1 | chr14:17263353-17914845 |
| 24613 | Rarb | NM_011243.2 | chr14:17263353-17914845 |
| 24614 | Rarg | NM_001042727.2 | chr15:102065368-102087953 |
| 24615 | Rarg | NM_011244.1 | chr15:102065368-102087953 |
| 24616 | Rarres1 | NM_001164763.1 | chr3:67282807-67319445 |
| 24617 | Rarres2 | NM_027852.2 | chr6:48519697-48522669 |
| 24618 | Rars | NM_025936.3 | chr11:35621882-35648030 |
| 24619 | Rars2 | NM_181406.3 | chr4:34562206-34607416 |
| 24620 | Rasa1 | NM_145452.2 | chr13:85354303-85429091 |
| 24621 | Rasa2 | NM_053268.2 | chr9:96439718-96531922 |
| 24622 | Rasa3 | NM_009025.2 | chr8:13567217-13677587 |

Fig. 25 - 131

| | | | |
|---|---|---|---|
| 24623 | Rasa4 | NM_001039103.3 | chr5:136559785-136587731 |
| 24624 | Rasa4 | NM_133914.3 | chr5:136559785-136587731 |
| 24625 | Rasal1 | NM_001281999.1 | chr5:121098820-121129619 |
| 24626 | Rasal1 | NM_013832.4 | chr5:121098820-121129619 |
| 24627 | Rasa2 | NM_177644.2 | chr1:159065314-159342726 |
| 24628 | Rasa3 | NM_178785.3 | chr17:32527606-32540526 |
| 24629 | Rasd1 | NM_009026.4 | chr11:59776685-59778444 |
| 24630 | Rasd2 | NM_029182.1 | chr7:77737842-77748012 |
| 24631 | Rasef | NM_001017427.1 | chr4:73360482-73436506 |
| 24632 | Rasgef1a | NM_027526.1 | chr5:118016403-118041564 |
| 24633 | Rasgef1b | NM_145839.2 | chr5:99646438-99681946 |
| 24634 | Rasgef1b | NM_181318.4 | chr5:99646438-99681946 |
| 24635 | Rasgef1c | NM_029004.1 | chr11:49715336-49793725 |
| 24636 | Rasgrf1 | NM_001039655.1 | chr9:89804612-89921817 |
| 24637 | Rasgrf1 | NM_011245.2 | chr9:89804612-89921817 |
| 24638 | Rasgrf2 | NM_009027.3 | chr13:92020011-92901449 |
| 24639 | Rasgrp1 | NM_011246.2 | chr2:117105728-117168613 |
| 24640 | Rasgrp2 | NM_011242.2 | chr19:6400582-6415216 |
| 24641 | Rasgrp3 | NM_001166403.1 | chr17:75835244-75928393 |
| 24642 | Rasgrp3 | NM_207246.4 | chr17:75835244-75928393 |
| 24643 | Rasgrp4 | NM_001174155.1 | chr7:29919951-29941229 |
| 24644 | Rasgrp4 | NM_145149.4 | chr7:29919951-29941229 |
| 24645 | Rasgrp4 | NR_045676.1 | chr7:29919951-29941229 |
| 24646 | Rasip1 | NM_028544.1 | chr7:52882906-52894462 |
| 24647 | Rasl10a | NM_145236.3 | chr11:4958131-4960386 |
| 24648 | Rasl10b | NM_001013386.2 | chr11:83223573-83234540 |
| 24649 | Rasl11a | NM_026864.1 | chr5:147656646-147659302 |
| 24650 | Rasl11b | NM_026878.1 | chr5:74591350-74595502 |
| 24651 | Rasl12 | NM_001033158.2 | chr9:65246294-65270580 |
| 24652 | Rasl12 | NM_001162923.1 | chr9:65246294-65270580 |
| 24653 | Rasl2-9 | NM_009028.2 | chr7:5076543-5077552 |
| 24654 | Rassf1 | NM_001243748.1 | chr9:107453885-107464598 |
| 24655 | Rassf1 | NM_019713.4 | chr9:107453885-107464598 |
| 24656 | Rassf10 | NM_175279.3 | chr7:120097475-120100972 |
| 24657 | Rassf2 | NM_175445.4 | chr2:131818585-131855724 |
| 24658 | Rassf3 | NM_138956.3 | chr10:120847406-120913306 |
| 24659 | Rassf4 | NM_178045.4 | chr6:116583026-116623854 |
| 24660 | Rassf5 | NM_018750.3 | chr1:133072986-133141755 |
| 24661 | Rassf6 | NM_028478.2 | chr5:91032101-91069513 |
| 24662 | Rassf7 | NM_025886.3 | chr7:148401758-148404557 |
| 24663 | Rassf8 | NM_027760.2 | chr6:145756902-145766104 |
| 24664 | Rassf9 | NM_146240.4 | chr10:101974855-102009194 |
| 24665 | Raver1 | NM_027911.3 | chr9:20878609-20896432 |
| 24666 | Raver1-fdx1l | NR_038081.2 | chr9:20871958-20896452 |
| 24667 | Raver2 | NM_183024.1 | chr4:100741643-100824975 |
| 24668 | Rax | NM_013833.2 | chr18:66094292-66098743 |
| 24669 | Rb1 | NM_009029.2 | chr14:73595309-73725598 |
| 24670 | Rb1cc1 | NM_009826.4 | chr1:6204742-6266185 |
| 24671 | Rbak | NM_001045482.2 | chr5:143933864-143942454 |
| 24672 | Rbak | NM_021326.3 | chr5:143933864-143942454 |
| 24673 | Rbakdn | NR_040424.1 | chr5:143926457-143927430 |
| 24674 | Rbakdn | NR_040425.1 | chr5:143926457-143927430 |
| 24675 | Rbakdn | NR_040426.1 | chr5:143926457-143927430 |
| 24676 | Rbbp4 | NM_009030.3 | chr4:128984344-129012614 |
| 24677 | Rbbp5 | NM_172517.2 | chr1:134373943-134402242 |
| 24678 | Rbbp6 | NM_011247.2 | chr7:130114077-130146086 |
| 24679 | Rbbp6 | NM_175023.3 | chr7:130114077-130146086 |
| 24680 | Rbbp7 | NM_009031.3 | chrX:159198304-159217022 |
| 24681 | Rbbp8 | NM_001081223.2 | chr18:11791784-11901716 |
| 24682 | Rbbp8 | NM_001252495.1 | chr18:11791784-11901716 |
| 24683 | Rbbp8 | NR_045526.1 | chr18:11791784-11901716 |
| 24684 | Rbbp8 | NR_045527.1 | chr18:11791784-11901716 |
| 24685 | Rbbp8nl | NM_173031.3 | chr2:180012350-180024584 |
| 24686 | Rbbp9 | NM_015754.2 | chr2:144368000-144376595 |
| 24687 | Rbck1 | NM_001083921.1 | chr2:152142069-152158375 |
| 24688 | Rbck1 | NM_019705.3 | chr2:152142069-152158375 |
| 24689 | Rbfa | NM_199197.1 | chr18:80389002-80397358 |
| 24690 | Rbfox1 | NM_021477.5 | chr16:5884885-7412573 |
| 24691 | Rbfox1 | NM_183188.2 | chr16:5884885-7412573 |
| 24692 | Rbfox2 | NM_001110827.2 | chr15:76909419-77137483 |
| 24693 | Rbfox2 | NM_001110828.2 | chr15:76909419-77137483 |
| 24694 | Rbfox2 | NM_001110829.1 | chr15:76909419-77137483 |
| 24695 | Rbfox2 | NM_001110830.2 | chr15:76909419-77137483 |
| 24696 | Rbfox2 | NM_001286417.1 | chr15:76909419-77137483 |
| 24697 | Rbfox2 | NM_001286418.1 | chr15:76909419-77137483 |
| 24698 | Rbfox2 | NM_001286419.1 | chr15:76909419-77137483 |
| 24699 | Rbfox2 | NM_053104.6 | chr15:76909419-77137483 |
| 24700 | Rbfox2 | NM_175387.3 | chr15:76909419-77137483 |
| 24701 | Rbfox3 | NM_001024931.2 | chr11:118351073-118772911 |
| 24702 | Rbfox3 | NM_001039167.1 | chr11:118351073-118772911 |
| 24703 | Rbfox3 | NM_001039168.1 | chr11:118351073-118772911 |
| 24704 | Rbfox3 | NM_001285436.1 | chr11:118351073-118772911 |
| 24705 | Rbfox3 | NM_001285437.1 | chr11:118351073-118772911 |
| 24706 | Rbfox3 | NM_001285438.1 | chr11:118351073-118772911 |
| 24707 | Rbks | NM_153196.1 | chr5:31926812-31999983 |
| 24708 | Rbl1 | NM_001139516.1 | chr2:156971629-157030270 |
| 24709 | Rbl1 | NM_011250.2 | chr2:156971629-157030270 |
| 24710 | Rbl2 | NM_001282000.1 | chr8:93593955-93659395 |
| 24711 | Rbl2 | NM_001282001.1 | chr8:93593955-93659395 |
| 24712 | Rbl2 | NM_011250.4 | chr8:93593955-93659395 |
| 24713 | Rbm10 | NM_001167775.1 | chrX:20192451-20228031 |
| 24714 | Rbm10 | NM_001167776.1 | chrX:20192451-20228031 |
| 24715 | Rbm10 | NM_145627.2 | chrX:20192451-20228031 |
| 24716 | Rbm11 | NM_198302.1 | chr16:75593135-75603070 |
| 24717 | Rbm12 | NM_029397.3 | chr2:155897576-155937701 |
| 24718 | Rbm12 | NM_170598.2 | chr2:155897576-155937701 |
| 24719 | Rbm12b1 | NM_028226.2 | chr4:12067263-12073892 |
| 24720 | Rbm12b2 | NM_198957.2 | chr4:12016516-12023418 |
| 24721 | Rbm14 | NM_019869.3 | chr19:4800566-4811634 |
| 24722 | Rbm14-rbm4 | NM_001290127.1 | chr19:4784292-4811634 |
| 24723 | Rbm14-rbm4 | NM_001290128.1 | chr19:4784292-4811634 |
| 24724 | Rbm15 | NM_001045807.1 | chr3:107129027-107136207 |
| 24725 | Rbm15b | NM_175402.4 | chr9:106786315-106789331 |
| 24726 | Rbm17 | NM_152824.1 | chr2:11507065-11524826 |
| 24727 | Rbm18 | NM_001159635.1 | chr2:35971598-36045803 |
| 24728 | Rbm18 | NM_026434.4 | chr2:35971598-36045803 |
| 24729 | Rbm18 | NR_027515.1 | chr2:35971598-36045803 |
| 24730 | Rbm19 | NM_028762.1 | chr5:120566522-120648980 |
| 24731 | Rbm20 | NM_001170847.1 | chr19:53751795-53941570 |
| 24732 | Rbm22 | NM_025776.2 | chr18:60720439-60732383 |
| 24733 | Rbm24 | NM_001081425.1 | chr13:46513868-46526468 |
| 24734 | Rbm25 | NM_027349.3 | chr12:84973183-85024073 |
| 24735 | Rbm26 | NM_134077.4 | chr14:105513736-105576544 |
| 24736 | Rbm27 | NM_172626.2 | chr18:42435006-42501194 |
| 24737 | Rbm28 | NM_133925.2 | chr6:29073572-29114724 |
| 24738 | Rbm3 | NM_001166409.2 | chrX:7716100-7725089 |
| 24739 | Rbm3 | NM_001166410.2 | chrX:7716100-7725089 |
| 24740 | Rbm3 | NM_001166411.2 | chrX:7716100-7725089 |
| 24741 | Rbm3 | NM_016809.6 | chrX:7716100-7725089 |
| 24742 | Rbm31y | NM_028970.1 | chrY_random:8474586-8476544 |
| 24743 | Rbm33 | NM_028234.1 | chr5:28643728-28745782 |
| 24744 | Rbm34 | NM_172762.2 | chr8:129471072-129494979 |
| 24745 | Rbm38 | NM_019547.2 | chr2:172847402-172860232 |
| 24746 | Rbm39 | NM_001291114.1 | chr2:155972975-156005974 |
| 24747 | Rbm39 | NM_001291115.1 | chr2:155972975-156005974 |
| 24748 | Rbm39 | NM_133242.3 | chr2:155972975-156005974 |
| 24749 | Rbm3os | NR_033561.1 | chrX:7722553-7725089 |
| 24750 | Rbm4 | NM_001290122.1 | chr19:4784292-4811634 |
| 24751 | Rbm4 | NM_001290123.1 | chr19:4784292-4811634 |
| 24752 | Rbm4 | NM_001290124.1 | chr19:4784292-4811634 |
| 24753 | Rbm4 | NM_001290125.1 | chr19:4784292-4811634 |
| 24754 | Rbm4 | NM_009032.3 | chr19:4784292-4811634 |
| 24755 | Rbm41 | NM_001172147.1 | chrX:136424049-136533134 |
| 24756 | Rbm41 | NM_001172148.1 | chrX:136424049-136533134 |
| 24757 | Rbm41 | NM_001290630.1 | chrX:136424049-136533134 |
| 24758 | Rbm41 | NM_153586.2 | chrX:136424049-136533134 |
| 24759 | Rbm42 | NM_133693.2 | chr7:31426013-31435247 |
| 24760 | Rbm43 | NM_001141981.1 | chr2:51779968-51790529 |
| 24761 | Rbm43 | NM_001141982.1 | chr2:51779968-51790529 |
| 24762 | Rbm43 | NM_030243.4 | chr2:51779968-51790529 |
| 24763 | Rbm44 | NM_001033408.4 | chr1:93041679-93067372 |
| 24764 | Rbm45 | NM_153405.2 | chr2:76208040-76221824 |
| 24765 | Rbm46 | NM_001277170.1 | chr3:82640444-82680405 |
| 24766 | Rbm46os | NR_040381.1 | chr3:82680626-82747560 |
| 24767 | Rbm46os | NR_040382.1 | chr3:82680626-82747560 |
| 24768 | Rbm47 | NM_001127382.2 | chr5:66407787-66543193 |
| 24769 | Rbm47 | NM_001291226.1 | chr5:66407787-66543193 |
| 24770 | Rbm47 | NM_139065.3 | chr5:66407787-66543193 |
| 24771 | Rbm47 | NM_178446.4 | chr5:66407787-66543193 |
| 24772 | Rbm48 | NM_172991.4 | chr5:3583978-3596547 |
| 24773 | Rbm4b | NM_025717.3 | chr19:4756524-4765940 |
| 24774 | Rbm5 | NM_148930.3 | chr9:107642825-107673333 |
| 24775 | Rbm6 | NM_011251.3 | chr9:107675890-107775150 |
| 24776 | Rbm6 | NM_029169.3 | chr9:107675890-107775150 |
| 24777 | Rbm7 | NM_144948.2 | chr9:48296801-48303435 |
| 24778 | Rbm7 | NR_037589.1 | chr9:48296801-48303435 |
| 24779 | Rbm8a | NM_001102407.1 | chr3:96433850-96437714 |
| 24780 | Rbm8a | NM_025875.2 | chr3:96433850-96437714 |
| 24781 | Rbms1 | NM_001141931.1 | chr2:60590009-60801261 |
| 24782 | Rbms1 | NM_001141932.1 | chr2:60590009-60801261 |
| 24783 | Rbms1 | NM_020296.2 | chr2:60590009-60801261 |
| 24784 | Rbms2 | NM_001039080.3 | chr10:127566525-127617353 |
| 24785 | Rbms2 | NM_019711.2 | chr10:127566525-127617353 |
| 24786 | Rbms3 | NM_001172121.1 | chr9:116481863-117539031 |
| 24787 | Rbms3 | NM_001172122.1 | chr9:116481863-117539031 |
| 24788 | Rbms3 | NM_001172123.1 | chr9:116481863-117539031 |
| 24789 | Rbms3 | NM_001172124.1 | chr9:116481863-117539031 |
| 24790 | Rbms3 | NM_001172126.1 | chr9:116481863-117539031 |
| 24791 | Rbms3 | NM_178660.4 | chr9:116481863-117539031 |
| 24792 | Rbmx | NM_001166623.1 | chrX:54636524-54646213 |
| 24793 | Rbmx | NM_011252.4 | chrX:54636524-54646213 |
| 24794 | Rbmx | NR_029425.1 | chrX:54636524-54646213 |
| 24795 | Rbmx2 | NM_173376.3 | chrX:46048186-46063896 |
| 24796 | Rbmxl1 | NM_001252089.1 | chr8:81029167-81032827 |
| 24797 | Rbmxl1 | NM_009033.2 | chr8:81029167-81032827 |
| 24798 | Rbmxl2 | NM_029660.2 | chr7:114352958-114354430 |
| 24799 | Rbmy | NM_001166384.1 | chrY:2188491-2398856 |
| 24800 | Rbmy | NM_011253.2 | chrY:2156898-2168120 |
| 24801 | Rbmy | NM_011253.2 | chrY:2188491-2398856 |
| 24802 | Rbp1 | NM_011254.5 | chr9:98323379-98346969 |
| 24803 | Rbp2 | NM_009034.4 | chr9:98390955-98410190 |
| 24804 | Rbp3 | NM_015745.2 | chr14:34767207-34777402 |
| 24805 | Rbp4 | NM_001159487.1 | chr19:38191109-38199811 |
| 24806 | Rbp4 | NM_011255.3 | chr19:38191109-38199811 |
| 24807 | Rbp7 | NM_022020.2 | chr4:148823810-148829077 |
| 24808 | Rbpj | NM_001080927.2 | chr5:53947017-54048684 |
| 24809 | Rbpj | NM_001080928.1 | chr5:53947017-54048684 |
| 24810 | Rbpj | NM_001277116.1 | chr5:53947017-54048684 |
| 24811 | Rbpj | NM_009035.5 | chr5:53947017-54048684 |

Fig. 25 - 132

| | | | |
|---|---|---|---|
| 24812 | Rbpjl | NM_009036.1 | chr2:164228694-164240948 |
| 24813 | Rbpms | NM_001042674.2 | chr8:34893115-35040335 |
| 24814 | Rbpms | NM_001042675.2 | chr8:34893115-35040335 |
| 24815 | Rbpms | NM_001286168.1 | chr8:34893115-35040335 |
| 24816 | Rbpms | NM_019733.3 | chr8:34893115-35040335 |
| 24817 | Rbpms2 | NM_028030.3 | chr9:65478388-65508325 |
| 24818 | Rbx1 | NM_019712.3 | chr15:81296745-81306799 |
| 24819 | Rc3h1 | NM_001024952.2 | chr1:162836541-162905107 |
| 24820 | Rc3h2 | NM_001100591.1 | chr2:37225590-37278423 |
| 24821 | Rc3h2 | NM_001290642.1 | chr2:37225590-37278423 |
| 24822 | Rcan1 | NM_001081549.2 | chr16:92392195-92466414 |
| 24823 | Rcan1 | NM_019466.4 | chr16:92392195-92466414 |
| 24824 | Rcan2 | NM_001286653.1 | chr17:43938799-44176465 |
| 24825 | Rcan2 | NM_001286654.1 | chr17:43938799-44176465 |
| 24826 | Rcan2 | NM_030598.2 | chr17:43938799-44176465 |
| 24827 | Rcan2 | NM_207649.1 | chr17:43938799-44176465 |
| 24828 | Rcan3 | NM_022980.4 | chr4:134968224-134989720 |
| 24829 | Rcbtb1 | NM_027784.2 | chr14:59820064-59856102 |
| 24830 | Rcbtb2 | NM_001170694.1 | chr14:73542316-73583861 |
| 24831 | Rcbtb2 | NM_134083.4 | chr14:73542316-73583861 |
| 24832 | Rcbtb2 | NR_033185.1 | chr14:73542316-73583861 |
| 24833 | Rcc1 | NM_001197082.1 | chr4:131887833-131901665 |
| 24834 | Rcc1 | NM_133878.3 | chr4:131887833-131901665 |
| 24835 | Rcc2 | NM_173867.5 | chr4:140257387-140279135 |
| 24836 | Rccd1 | NM_173445.4 | chr7:87461501-87469340 |
| 24837 | Rce1 | NM_023131.1 | chr19:4622551-4625617 |
| 24838 | Rchy1 | NM_001271797.1 | chr5:92377867-92401163 |
| 24839 | Rchy1 | NM_026557.4 | chr5:92377867-92401163 |
| 24840 | Rchy1 | NR_073442.1 | chr5:92377867-92401163 |
| 24841 | Rcl1 | NM_021525.2 | chr19:29175865-29218333 |
| 24842 | Rcn1 | NM_009037.2 | chr2:105226104-105239476 |
| 24843 | Rcn2 | NM_001278274.1 | chr9:55889651-55906890 |
| 24844 | Rcn2 | NM_011992.2 | chr9:55889651-55906890 |
| 24845 | Rcn3 | NM_026555.1 | chr7:52338283-52347583 |
| 24846 | Rcor1 | NM_198023.2 | chr12:112278008-112351597 |
| 24847 | Rcor2 | NM_054048.3 | chr19:7344253-7349715 |
| 24848 | Rcor3 | NM_001290278.1 | chr1:193922428-193974907 |
| 24849 | Rcor3 | NM_001290279.1 | chr1:193922428-193974907 |
| 24850 | Rcor3 | NM_001290280.1 | chr1:193922428-193974907 |
| 24851 | Rcor3 | NM_001290282.1 | chr1:193922428-193974907 |
| 24852 | Rcor3 | NM_144814.3 | chr1:193922428-193974907 |
| 24853 | Rcsd1 | NM_001038846.1 | chr1:167579075-167638225 |
| 24854 | Rcsd1 | NM_178593.3 | chr1:167579075-167638225 |
| 24855 | Rcvrn | NM_009038.2 | chr11:67508827-67516857 |
| 24856 | Rd3 | NM_001179000.2 | chr1:193801253-193812163 |
| 24857 | Rd3 | NM_023727.4 | chr1:193801253-193812163 |
| 24858 | Rd3l | NM_001127685.1 | chr12:113217534-113218962 |
| 24859 | Rdh1 | NM_080436.3 | chr10:127196818-127205355 |
| 24860 | Rdh10 | NM_133832.3 | chr1:16095962-16122631 |
| 24861 | Rdh11 | NM_021557.3 | chr12:80276537-80292806 |
| 24862 | Rdh12 | NM_030017.3 | chr12:80309900-80323648 |
| 24863 | Rdh13 | NM_001290409.1 | chr7:4377266-4397259 |
| 24864 | Rdh13 | NM_001290411.1 | chr7:4377266-4397259 |
| 24865 | Rdh13 | NM_175372.4 | chr7:4377266-4397259 |
| 24866 | Rdh14 | NM_023697.2 | chr12:10397585-10402368 |
| 24867 | Rdh16 | NM_009040.3 | chr10:127238208-127252895 |
| 24868 | Rdh18-ps | NR_037604.1 | chr10:127261271-127283621 |
| 24869 | Rdh19 | NM_147222.2 | chr10:127286983-127298232 |
| 24870 | Rdh5 | NM_134006.4 | chr10:128350646-128356353 |
| 24871 | Rdh7 | NM_001150749.1 | chr10:127321082-127325789 |
| 24872 | Rdh7 | NM_017473.4 | chr10:127321082-127325789 |
| 24873 | Rdh8 | NM_001030290.1 | chr9:20622947-20630607 |
| 24874 | Rdh9 | NM_153133.2 | chr10:127213460-127229753 |
| 24875 | Rdm1 | NM_025654.2 | chr11:101489262-101497395 |
| 24876 | Rdx | NM_001046616.1 | chr9:51810165-51896843 |
| 24877 | Rdx | NM_001104617.1 | chr9:51810165-51896843 |
| 24878 | Rdx | NM_009041.1 | chr9:51810165-51896843 |
| 24879 | Rec8 | NM_020002.3 | chr14:56237002-56244232 |
| 24880 | Reck | NM_016678.2 | chr4:43888401-43957678 |
| 24881 | Recql | NM_001204906.1 | chr6:142294216-142335607 |
| 24882 | Recql | NM_001204907.1 | chr6:142294216-142335607 |
| 24883 | Recql | NM_023042.3 | chr6:142294216-142335607 |
| 24884 | Recql4 | NM_058214.3 | chr15:76533983-76540989 |
| 24885 | Recql5 | NM_130454.2 | chr11:115753909-115794806 |
| 24886 | Redrum | NR_040338.1 | chr18:54581948-54612948 |
| 24887 | Reep1 | NM_178608.4 | chr6:71657674-71760699 |
| 24888 | Reep2 | NM_001204914.1 | chr18:35000242-35007117 |
| 24889 | Reep2 | NM_144865.2 | chr18:35000242-35007117 |
| 24890 | Reep3 | NM_001204915.1 | chr10:66467822-66559736 |
| 24891 | Reep3 | NM_178606.5 | chr10:66467822-66559736 |
| 24892 | Reep4 | NM_180588.1 | chr14:70945057-70948742 |
| 24893 | Reep5 | NM_007874.3 | chr18:34505439-34533069 |
| 24894 | Reep6 | NM_001204931.1 | chr10:79792889-79799186 |
| 24895 | Reep6 | NM_139292.2 | chr10:79792889-79799186 |
| 24896 | Reg1 | NM_009042.2 | chr6:78355976-78378660 |
| 24897 | Reg2 | NM_009043.1 | chr6:78355148-78358091 |
| 24898 | Reg3a | NM_011259.4 | chr6:78330702-78333833 |
| 24899 | Reg3b | NM_011036.1 | chr6:78320878-78323460 |
| 24900 | Reg3d | NM_001161741.1 | chr6:78325867-78328859 |
| 24901 | Reg3d | NM_013893.2 | chr6:78325867-78328859 |
| 24902 | Reg3g | NM_011260.1 | chr6:78416261-78418868 |
| 24903 | Reg4 | NM_026328.2 | chr3:98026078-98040671 |
| 24904 | Rel | NM_009044.2 | chr11:23641728-23670970 |
| 24905 | Rela | NM_009045.4 | chr19:5637489-5648130 |
| 24906 | Relb | NM_001290457.1 | chr7:20191570-20214787 |
| 24907 | Relb | NM_009046.2 | chr7:20191570-20214787 |
| 24908 | Rell1 | NM_145923.4 | chr5:64300136-64360136 |
| 24909 | Rell2 | NM_153793.2 | chr18:38115213-38118833 |
| 24910 | Reln | NM_011261.2 | chr5:21390271-21850523 |
| 24911 | Relt | NM_177073.6 | chr7:107994361-108011927 |
| 24912 | Rem1 | NM_009047.5 | chr2:152452743-152460927 |
| 24913 | Rem2 | NM_080726.3 | chr14:55094936-55099271 |
| 24914 | Ren1 | NM_031192.3 | chr1:135247251-135256896 |
| 24915 | Ren2 | NM_031193.2 | chr1:135247143-135256900 |
| 24916 | Renbp | NM_001164704.1 | chrX:71167459-71176189 |
| 24917 | Renbp | NM_023132.3 | chrX:71167459-71176189 |
| 24918 | Rep15 | NM_025620.2 | chr6:146981058-146982040 |
| 24919 | Repin1 | NM_001079901.1 | chr6:48543881-48549081 |
| 24920 | Repin1 | NM_001079902.1 | chr6:48543881-48549081 |
| 24921 | Repin1 | NM_001079903.1 | chr6:48543881-48549081 |
| 24922 | Repin1 | NM_001079904.1 | chr6:48543881-48549081 |
| 24923 | Repin1 | NM_001079905.1 | chr6:48543881-48549081 |
| 24924 | Repin1 | NM_175099.3 | chr6:48543881-48549081 |
| 24925 | Reps1 | NM_001111065.1 | chr10:17775745-17844961 |
| 24926 | Reps1 | NM_009048.2 | chr10:17775745-17844961 |
| 24927 | Reps2 | NM_001290633.1 | chrX:158849883-159081590 |
| 24928 | Reps2 | NM_178256.4 | chrX:158849883-159081590 |
| 24929 | Rer1 | NM_026395.1 | chr4:154448220-154460406 |
| 24930 | Rere | NM_001085492.1 | chr4:149656024-149996075 |
| 24931 | Rerg | NM_001164212.1 | chr6:137003345-137119017 |
| 24932 | Rerg | NM_001164214.1 | chr6:137003345-137119017 |
| 24933 | Rerg | NM_181988.2 | chr6:137003345-137119017 |
| 24934 | Rergl | NM_001128090.1 | chr6:139441702-139450430 |
| 24935 | Respl8 | NM_009049.1 | chr7:75268776-75274955 |
| 24936 | Rest | NM_011263.2 | chr5:77694519-77712722 |
| 24937 | Ret | NM_001080780.1 | chr6:118101765-118147762 |
| 24938 | Ret | NM_009050.2 | chr6:118101765-118147762 |
| 24939 | Retn | NM_001204959.1 | chr8:3655769-3659818 |
| 24940 | Retn | NM_022984.2 | chr8:3655769-3659818 |
| 24941 | Retnla | NM_020509.3 | chr16:48842664-48844574 |
| 24942 | Retnlb | NM_023881.4 | chr16:48816968-48819005 |
| 24943 | Retnlg | NM_181596.4 | chr16:48872720-48874611 |
| 24944 | Retsat | NM_026159.4 | chr6:72548621-72557482 |
| 24945 | Rev1 | NM_019570.3 | chr1:38109631-38186507 |
| 24946 | Rev3l | NM_011264.3 | chr10:39451965-39595011 |
| 24947 | Rex2 | NM_001177767.1 | chr4:145850602-145889553 |
| 24948 | Rex2 | NM_001177767.1 | chr4:146395958-146434908 |
| 24949 | Rexo1 | NM_025852.3 | chr10:80003670-80024305 |
| 24950 | Rexo2 | NM_024233.3 | chr9:48276618-48288716 |
| 24951 | Rexo4 | NM_207234.2 | chr2:26809082-26819906 |
| 24952 | Rfc1 | NM_011258.2 | chr5:65653090-65726878 |
| 24953 | Rfc2 | NM_020022.2 | chr5:135058559-135074198 |
| 24954 | Rfc3 | NM_027009.2 | chr5:152445398-152453783 |
| 24955 | Rfc4 | NM_145480.1 | chr16:23114021-23127803 |
| 24956 | Rfc5 | NM_028128.1 | chr5:117829153-117839032 |
| 24957 | Rfesd | NM_001131068.1 | chr13:76138982-76156160 |
| 24958 | Rfesd | NM_001131069.1 | chr13:76138982-76156160 |
| 24959 | Rfesd | NM_178916.5 | chr13:76138982-76156160 |
| 24960 | Rffl | NM_001007465.3 | chr11:82594610-82684712 |
| 24961 | Rffl | NM_001164569.1 | chr11:82594610-82684712 |
| 24962 | Rffl | NM_001164570.1 | chr11:82594610-82684712 |
| 24963 | Rffl | NM_001164571.1 | chr11:82594610-82684712 |
| 24964 | Rffl | NM_026097.3 | chr11:82594610-82684712 |
| 24965 | Rfk | NM_019437.3 | chr19:17468532-17475839 |
| 24966 | Rfng | NM_009053.2 | chr11:120642058-120645518 |
| 24967 | Rfpl3s | NM_183111.2 | chr9:55810395-55828739 |
| 24968 | Rfpl4 | NM_001145013.1 | chr7:5061388-5068513 |
| 24969 | Rfpl4 | NM_138954.3 | chr7:5061388-5068513 |
| 24970 | Rfpl4b | NM_001177783.1 | chr10:38540346-38541585 |
| 24971 | Rft1 | NM_177815.3 | chr14:31467560-31504499 |
| 24972 | Rftn1 | NM_181397.2 | chr17:50132631-50329822 |
| 24973 | Rftn1 | NM_028713.1 | chr1:55227003-55283626 |
| 24974 | Rfwd2 | NM_019931.3 | chr1:161162457-161277711 |
| 24975 | Rfwd3 | NM_146218.4 | chr8:113794843-113824122 |
| 24976 | Rfx1 | NM_009055.4 | chr8:86590735-86620891 |
| 24977 | Rfx2 | NM_009056.2 | chr17:56915319-56970431 |
| 24978 | Rfx2 | NM_027787.1 | chr17:56915319-56970431 |
| 24979 | Rfx3 | NM_001166414.1 | chr19:27836210-28085656 |
| 24980 | Rfx3 | NM_011265.3 | chr19:27836210-28085656 |
| 24981 | Rfx4 | NM_001024918.1 | chr10:84218792-84369283 |
| 24982 | Rfx4 | NM_178693.3 | chr10:84218792-84369283 |
| 24983 | Rfx5 | NM_017395.2 | chr3:94758936-94765483 |
| 24984 | Rfx6 | NM_001159389.1 | chr10:51397565-51450235 |
| 24985 | Rfx6 | NM_177306.3 | chr10:51397565-51450235 |
| 24986 | Rfx7 | NM_001033536.1 | chr9:72380046-72470756 |
| 24987 | Rfx8 | NM_001145660.1 | chr1:39722145-39777834 |
| 24988 | Rfxank | NM_001025589.1 | chr8:72654704-72663096 |
| 24989 | Rfxank | NM_011266.2 | chr8:72654704-72663096 |
| 24990 | Rfxap | NM_133231.2 | chr3:54607036-54611713 |
| 24991 | Rgag1 | NM_001040434.2 | chrX:139534136-139538878 |
| 24992 | Rgag4 | NM_001278534.1 | chrX:99261881-99266646 |
| 24993 | Rgcc | NM_025427.2 | chr14:79688556-79703442 |
| 24994 | Rgl1 | NM_016846.2 | chr1:154364659-154472241 |
| 24995 | Rgl2 | NM_009059.2 | chr17:34066838-34074632 |
| 24996 | Rgl3 | NM_023622.4 | chr9:21775970-21793897 |
| 24997 | Rgma | NM_177740.5 | chr7:80520406-80564785 |
| 24998 | Rgmb | NM_178615.3 | chr17:15943216-15963550 |
| 24999 | Rgn | NM_009060.2 | chrX:20126943-20139213 |
| 25000 | Rgs1 | NM_172866.3 | chr1:43591607-43600359 |
| 25001 | Rgr | NM_021340.4 | chr14:37850675-37862150 |

Fig. 25 - 133

| | | | |
|---|---|---|---|
| 25002 | Rgs1 | NM_015811.2 | chr1:146091798-146096234 |
| 25003 | Rgs10 | NM_026418.2 | chr7:135517138-135561686 |
| 25004 | Rgs11 | NM_001081069.1 | chr17:26339906-26348269 |
| 25005 | Rgs12 | NM_001163512.1 | chr5:35292096-35376242 |
| 25006 | Rgs12 | NM_173402.2 | chr5:35292096-35376242 |
| 25007 | Rgs13 | NM_153171.4 | chr1:145985796-146024502 |
| 25008 | Rgs14 | NM_016758.3 | chr13:55471092-55486048 |
| 25009 | Rgs16 | NM_011267.3 | chr1:155587482-155592598 |
| 25010 | Rgs17 | NM_001161822.1 | chr10:4424140-4520877 |
| 25011 | Rgs17 | NM_019958.4 | chr10:4424140-4520877 |
| 25012 | Rgs18 | NM_022851.4 | chr1:146599970-146622551 |
| 25013 | Rgs19 | NM_001291205.1 | chr2:181423123-181428682 |
| 25014 | Rgs19 | NM_001291206.1 | chr2:181423123-181428682 |
| 25015 | Rgs19 | NM_001291207.1 | chr2:181423123-181428682 |
| 25016 | Rgs19 | NM_001291208.1 | chr2:181423123-181428682 |
| 25017 | Rgs19 | NM_001291209.1 | chr2:181423123-181428682 |
| 25018 | Rgs19 | NM_001291210.1 | chr2:181423123-181428682 |
| 25019 | Rgs19 | NM_026446.4 | chr2:181423123-181428682 |
| 25020 | Rgs2 | NM_009061.4 | chr1:145846467-145851279 |
| 25021 | Rgs20 | NM_001177795.1 | chr1:4899656-5060366 |
| 25022 | Rgs20 | NM_001290372.1 | chr1:4899656-5060366 |
| 25023 | Rgs20 | NM_021374.5 | chr1:4899656-5060366 |
| 25024 | Rgs21 | NM_001290269.1 | chr1:146366819-146414797 |
| 25025 | Rgs21 | NR_110891.1 | chr1:146366819-146414797 |
| 25026 | Rgs22 | NM_001195748.1 | chr15:35939231-36070155 |
| 25027 | Rgs3 | NM_001081650.2 | chr4:62220880-62364053 |
| 25028 | Rgs3 | NM_019492.3 | chr4:62220880-62364053 |
| 25029 | Rgs3 | NM_134257.3 | chr4:62220880-62364053 |
| 25030 | Rgs4 | NM_009062.3 | chr1:171671607-171677773 |
| 25031 | Rgs5 | NM_009063.3 | chr1:171585631-171623657 |
| 25032 | Rgs6 | NM_001122061.1 | chr12:83718024-84259800 |
| 25033 | Rgs6 | NM_015812.3 | chr12:83718024-84259800 |
| 25034 | Rgs7 | NM_001199003.1 | chr1:176989206-177422676 |
| 25035 | Rgs7 | NM_011880.3 | chr1:176989206-177422676 |
| 25036 | Rgs7bp | NM_029879.2 | chr13:105737232-105845010 |
| 25037 | Rgs8 | NM_026380.3 | chr1:155500166-155544795 |
| 25038 | Rgs9 | NM_001165934.1 | chr11:109086668-109159495 |
| 25039 | Rgs9 | NM_011268.2 | chr11:109086668-109159495 |
| 25040 | Rgs9bp | NM_145840.3 | chr7:36364012-36370601 |
| 25041 | Rgsl1 | NM_001243223.1 | chr1:155626516-155691271 |
| 25042 | Rhag | NM_011269.2 | chr17:40948097-40977703 |
| 25043 | Rhbdd1 | NM_001122685.1 | chr1:82313153-82441941 |
| 25044 | Rhbdd1 | NM_029777.3 | chr1:82313153-82441941 |
| 25045 | Rhbdd2 | NM_146002.2 | chr5:136108523-136122246 |
| 25046 | Rhbdd3 | NM_001290491.1 | chr11:4999275-5006103 |
| 25047 | Rhbdd3 | NM_001290492.1 | chr11:4999275-5006103 |
| 25048 | Rhbdd3 | NM_001290493.1 | chr11:4999275-5006103 |
| 25049 | Rhbdd3 | NM_177370.4 | chr11:4999275-5006103 |
| 25050 | Rhbdd3 | NR_110961.1 | chr11:4999275-5006103 |
| 25051 | Rhbdf1 | NM_001291818.1 | chr11:32109584-32122293 |
| 25052 | Rhbdf1 | NM_011117.2 | chr11:32109584-32122293 |
| 25053 | Rhbdf2 | NM_001167680.1 | chr11:116459478-116488333 |
| 25054 | Rhbdf2 | NM_172572.1 | chr11:116459478-116488333 |
| 25055 | Rhbdl1 | NM_144816.1 | chr17:25971409-25974072 |
| 25056 | Rhbdl2 | NM_183163.2 | chr4:123465117-123507147 |
| 25057 | Rhbdl3 | NM_139228.3 | chr11:80114413-80169488 |
| 25058 | Rhbg | NM_021375.3 | chr3:88046795-88058606 |
| 25059 | Rhcg | NM_019799.3 | chr7:86738248-86762543 |
| 25060 | Rhd | NM_011270.3 | chr4:134420450-134452087 |
| 25061 | Rheb | NM_053075.3 | chr5:24308640-24348179 |
| 25062 | Rhebl1 | NM_026967.4 | chr15:98708190-98711845 |
| 25063 | Rhno1 | NR_027334.1 | chr6:128307017-128312915 |
| 25064 | Rhno1 | NR_027360.1 | chr6:128307017-128312915 |
| 25065 | Rho | NM_145383.1 | chr6:115881944-115888848 |
| 25066 | Rhoa | NM_016802.4 | chr9:108208535-108240270 |
| 25067 | Rhob | NM_007483.2 | chr12:8504564-8506791 |
| 25068 | Rhobtb1 | NM_001081347.1 | chr10:68671299-68754532 |
| 25069 | Rhobtb1 | NM_001252636.1 | chr10:68671299-68754532 |
| 25070 | Rhobtb1 | NM_001252637.1 | chr10:68671299-68754532 |
| 25071 | Rhobtb1 | NM_001252638.1 | chr10:68671299-68754532 |
| 25072 | Rhobtb2 | NM_153514.5 | chr14:70184796-70205352 |
| 25073 | Rhobtb3 | NM_028493.2 | chr13:76006984-76081272 |
| 25074 | Rhoc | NM_001191951.1 | chr3:104591951-104597377 |
| 25075 | Rhoc | NM_007484.2 | chr3:104591951-104597377 |
| 25076 | Rhod | NM_007485.4 | chr19:4425457-4439424 |
| 25077 | Rhof | NM_175092.3 | chr5:123568188-123582638 |
| 25078 | Rhog | NM_019566.3 | chr7:109387636-109398632 |
| 25079 | Rhoh | NM_001081105.1 | chr5:66254807-66287939 |
| 25080 | Rhoj | NM_023275.2 | chr12:76409299-76502442 |
| 25081 | Rhoq | NM_145491.2 | chr17:87362451-87399409 |
| 25082 | Rhot1 | NM_001163354.1 | chr11:80022556-80081409 |
| 25083 | Rhot1 | NM_001163355.1 | chr11:80022556-80081409 |
| 25084 | Rhot1 | NM_021536.7 | chr11:80022556-80081409 |
| 25085 | Rhot2 | NM_145999.2 | chr17:25975783-25981796 |
| 25086 | Rhou | NM_133955.4 | chr8:126177828-126187780 |
| 25087 | Rhov | NM_145530.2 | chr2:119094936-119096962 |
| 25088 | Rhox1 | NM_001033799.4 | chrX:34753799-34762253 |
| 25089 | Rhox10 | NM_001024850.2 | chrX:35419651-35424865 |
| 25090 | Rhox11 | NM_198598.2 | chrX:35429774-35438316 |
| 25091 | Rhox12 | NM_001025083.2 | chrX:35457238-35464084 |
| 25092 | Rhox13 | NM_001185002.1 | chrX:35474016-35483143 |
| 25093 | Rhox2a | NM_029203.2 | chrX:34784987-34789685 |
| 25094 | Rhox2b | NM_001099316.1 | chrX:34826612-34831313 |
| 25095 | Rhox2c | NM_001099318.1 | chrX:34868165-34872882 |
| 25096 | Rhox2d | NM_001081669.2 | chrX:34907916-34912222 |
| 25097 | Rhox2e | NM_001085348.1 | chrX:34944974-34956316 |
| 25098 | Rhox2e | NM_001085348.1 | chrX:34784986-34831313 |
| 25099 | Rhox2f | NM_001085356.1 | chrX:34985927-34990666 |
| 25100 | Rhox2g | NM_001114153.1 | chrX:35053618-35057977 |
| 25101 | Rhox2h | NM_001100465.1 | chrX:35083503-35087784 |
| 25102 | Rhox3a | NM_194063.3 | chrX:34789914-34798973 |
| 25103 | Rhox3c | NM_001102457.1 | chrX:34884374-34888468 |
| 25104 | Rhox3e | NM_001184969.1 | chrX:34961481-34965404 |
| 25105 | Rhox3e | NM_001184969.1 | chrX:34784986-34831313 |
| 25106 | Rhox3f | NM_001040089.1 | chrX:34995858-35000003 |
| 25107 | Rhox3g | NM_001145406.3 | chrX:35037938-35042646 |
| 25108 | Rhox3h | NM_001114157.1 | chrX:35072194-35083271 |
| 25109 | Rhox4a | NM_001039688.3 | chrX:34805370-34810130 |
| 25110 | Rhox4b | NM_021300.2 | chrX:34847000-34851785 |
| 25111 | Rhox4c | NM_001039689.1 | chrX:34894843-34899631 |
| 25112 | Rhox4d | NM_001039695.1 | chrX:34929041-34933682 |
| 25113 | Rhox4e | NM_201236.3 | chrX:34971918-34976789 |
| 25114 | Rhox4f | NM_001039696.1 | chrX:35017401-35022193 |
| 25115 | Rhox4g | NM_001039698.1 | chrX:35061007-35065834 |
| 25116 | Rhox6 | NM_008955.1 | chrX:35180231-35183034 |
| 25117 | Rhox7 | NM_001025086.2 | chrX:35184862-35194348 |
| 25118 | Rhox8 | NM_001004193.2 | chrX:35227952-35232121 |
| 25119 | Rhox9 | NM_023894.1 | chrX:35252273-35254947 |
| 25120 | Rhpn1 | NM_001163465.1 | chr15:75534717-75544849 |
| 25121 | Rhpn1 | NM_008164.2 | chr15:75534717-75544849 |
| 25122 | Rhpn2 | NM_027897.4 | chr7:36119256-36177306 |
| 25123 | Rian | NR_028261.1 | chr12:110842155-110899921 |
| 25124 | Ribc1 | NM_025660.2 | chrX:148439126-148450838 |
| 25125 | Ribc2 | NM_026357.2 | chr15:84962528-84974999 |
| 25126 | Ric3 | NM_001038624.1 | chr7:116154393-116226838 |
| 25127 | Ric3 | NM_178780.3 | chr7:116154393-116226838 |
| 25128 | Ric8 | NM_053194.4 | chr7:148043296-148049630 |
| 25129 | Ric8b | NM_001013441.2 | chr10:84380357-84481082 |
| 25130 | Ric8b | NM_183172.2 | chr10:84380357-84481082 |
| 25131 | Rictor | NM_030168.3 | chr15:6658380-6750400 |
| 25132 | Rif1 | NM_175238.5 | chr2:51928356-51977901 |
| 25133 | Riiad1 | NM_025506.2 | chr3:94268966-94277513 |
| 25134 | Rilp | NM_001029938.2 | chr11:75323595-75326668 |
| 25135 | Rilpl1 | NM_021430.2 | chr5:124943088-124981400 |
| 25136 | Rilpl2 | NM_030259.1 | chr5:124913273-124928244 |
| 25137 | Rimbp2 | NM_001081388.1 | chr5:129266275-129459237 |
| 25138 | Rimbp3 | NM_001033338.3 | chr16:17208227-17214075 |
| 25139 | Rimkla | NM_177572.4 | chr4:119137890-119165203 |
| 25140 | Rimklb | NM_027664.1 | chr6:122403626-122436323 |
| 25141 | Rims1 | NM_001012623.1 | chr1:22278502-22812563 |
| 25142 | Rims1 | NM_001012624.1 | chr1:22278502-22812563 |
| 25143 | Rims1 | NM_001012625.1 | chr1:22278502-22812563 |
| 25144 | Rims1 | NM_053270.1 | chr1:22278502-22812563 |
| 25145 | Rims1 | NM_183018.2 | chr1:22278502-22812563 |
| 25146 | Rims2 | NM_001256382.1 | chr15:39029831-39515918 |
| 25147 | Rims2 | NM_001256383.1 | chr15:39029831-39515918 |
| 25148 | Rims2 | NM_001256384.1 | chr15:39029831-39515918 |
| 25149 | Rims2 | NM_053271.2 | chr15:39029831-39515918 |
| 25150 | Rims3 | NM_182929.2 | chr4:120550473-120564165 |
| 25151 | Rims4 | NM_183023.1 | chr2:163689616-163744419 |
| 25152 | Rin1 | NM_145495.2 | chr19:5050807-5057071 |
| 25153 | Rin2 | NM_028724.2 | chr2:145611851-145713352 |
| 25154 | Rin3 | NM_001161365.1 | chr12:103521283-103629064 |
| 25155 | Rin3 | NM_177620.4 | chr12:103521283-103629064 |
| 25156 | Ring1 | NM_009066.3 | chr17:34157736-34161625 |
| 25157 | Rinl | NM_177158.5 | chr7:29573987-29583984 |
| 25158 | Rint1 | NM_177323.3 | chr5:23293561-23326187 |
| 25159 | Riok1 | NM_024242.3 | chr13:38128857-38153302 |
| 25160 | Riok2 | NM_025934.2 | chr17:17511295-17531863 |
| 25161 | Riok3 | NM_024182.4 | chr18:12287358-12315876 |
| 25162 | Ripk1 | NM_009068.3 | chr13:34094742-34127039 |
| 25163 | Ripk2 | NM_138952.3 | chr4:16050521-16090645 |
| 25164 | Ripk3 | NM_001164107.1 | chr14:56403831-56407694 |
| 25165 | Ripk3 | NM_001164108.1 | chr14:56403831-56407694 |
| 25166 | Ripk3 | NM_019955.2 | chr14:56403831-56407694 |
| 25167 | Ripk4 | NM_023663.6 | chr16:97963548-97985362 |
| 25168 | Ripply1 | NM_001037915.2 | chrX:136314219-136316892 |
| 25169 | Ripply2 | NM_001037907.1 | chr9:86910371-86914751 |
| 25170 | Ripply3 | NM_183229.2 | chr16:94550028-94558542 |
| 25171 | Rit1 | NM_001163310.1 | chr3:88520775-88534970 |
| 25172 | Rit1 | NM_009069.4 | chr3:88520775-88534970 |
| 25173 | Rit1 | NR_028056.1 | chr3:88520775-88534970 |
| 25174 | Rit2 | NM_009065.2 | chr18:31133967-31476782 |
| 25175 | Rita1 | NM_029096.3 | chr5:121059068-121062598 |
| 25176 | Rita1 | NM_133908.1 | chr5:121059068-121062598 |
| 25177 | Rlbp1 | NM_001173483.1 | chr7:86519755-86531913 |
| 25178 | Rlbp1 | NM_020599.2 | chr7:86519755-86531913 |
| 25179 | Rlf | NM_001081013.1 | chr4:120817977-120861139 |
| 25180 | Rlim | NM_011276.3 | chrX:101152505-101176623 |
| 25181 | Rln1 | NM_011272.2 | chr19:29406244-29409160 |
| 25182 | Rln3 | NM_173184.1 | chr8:86566965-86568878 |
| 25183 | Rltpr | NM_001033320.2 | chr16:23943122082065 |
| 25184 | Rmdn1 | NM_025476.6 | chr4:19502212-19534079 |
| 25185 | Rmdn2 | NM_201361.2 | chr17:80014239-80081492 |
| 25186 | Rmdn3 | NM_001033136.3 | chr2:118962733-118982770 |
| 25187 | Rmi1 | NM_001168248.1 | chr13:58493311-58512510 |
| 25188 | Rmi1 | NM_028904.3 | chr13:58493311-58512510 |
| 25189 | Rmi1 | NR_031761.1 | chr13:58493311-58512510 |
| 25190 | Rmi2 | NM_001162932.1 | chr16:10835151-10843328 |
| 25191 | Rmnd1 | NM_025343.5 | chr10:5914189-5943372 |

Fig. 25 - 134

| | | | |
|---|---|---|---|
| 25192 | Rmnd5a | NM_024288.2 | chr6:71338627-71390631 |
| 25193 | Rmnd5b | NM_025346.1 | chr11:51437175-51449898 |
| 25194 | Rmrp | NR_001460.1 | chr4:43505656-43505931 |
| 25195 | Rmst | NR_028262.1 | chr10:91544491-91627923 |
| 25196 | Rn4.5s | NR_002841.1 | chr6:47635201-47635375 |
| 25197 | Rn4.5s | NR_002841.1 | chr6:47702750-47702924 |
| 25198 | Rn4.5s | NR_002841.1 | chr6:47617916-47618090 |
| 25199 | Rn4.5s | NR_002841.1 | chr6:47694056-47694230 |
| 25200 | Rn4.5s | NR_002841.1 | chr6:47630883-47631057 |
| 25201 | Rn4.5s | NR_002841.1 | chr6:47604919-47605093 |
| 25202 | Rn4.5s | NR_002841.1 | chr6:47622224-47622398 |
| 25203 | Rn4.5s | NR_002841.1 | chr6:47609240-47609414 |
| 25204 | Rn4.5s | NR_002841.1 | chr6:47613580-47613754 |
| 25205 | Rn4.5s | NR_002841.1 | chr6:47626562-47626736 |
| 25206 | Rn45s | NR_046233.2 | chr17:39979941-39985774 |
| 25207 | Rnase1 | NM_011271.2 | chr14:51764676-51766442 |
| 25208 | Rnase10 | NM_001162863.1 | chr14:51627425-51630433 |
| 25209 | Rnase10 | NM_029145.3 | chr14:51627425-51630433 |
| 25210 | Rnase11 | NM_001011877.2 | chr14:51669125-51669838 |
| 25211 | Rnase12 | NM_001011875.2 | chr14:51676372-51676917 |
| 25212 | Rnase13 | NM_001011687.2 | chr14:52541834-52542448 |
| 25213 | Rnase2a | NM_053113.2 | chr14:51874936-51875787 |
| 25214 | Rnase2b | NM_019398.2 | chr14:51781934-51782693 |
| 25215 | Rnase4 | NM_021472.4 | chr14:51710751-51725826 |
| 25216 | Rnase4 | NM_201239.3 | chr14:51710751-51725826 |
| 25217 | Rnase6 | NM_030098.2 | chr14:51748742-51750796 |
| 25218 | Rnase9 | NM_183032.2 | chr14:51658133-51661542 |
| 25219 | Rnaseh1 | NM_011275.3 | chr12:29334466-29344456 |
| 25220 | Rnaseh1 | NR_104608.1 | chr12:29334466-29344456 |
| 25221 | Rnaseh2a | NM_027187.3 | chr8:87480508-87489910 |
| 25222 | Rnaseh2b | NM_026001.2 | chr14:62950941-62991829 |
| 25223 | Rnaseh2c | NM_026616.2 | chr19:5601872-5602959 |
| 25224 | Rnasek | NM_173742.3 | chr11:70051624-70053354 |
| 25225 | Rnasel | NM_011882.2 | chr1:155596555-155611351 |
| 25226 | Rnaset2a | NM_001083988.2 | chr17:8321463-8340653 |
| 25227 | Rnaset2b | NM_026611.2 | chr17:7183208-7202542 |
| 25228 | Rnaset2b | NM_026611.2 | chr17:8321455-8340697 |
| 25229 | Rnd1 | NM_172612.3 | chr15:98499635-98507892 |
| 25230 | Rnd2 | NM_009708.1 | chr11:101329651-101332620 |
| 25231 | Rnd3 | NM_028810.2 | chr2:50985958-51004631 |
| 25232 | Rnf10 | NM_016698.2 | chr5:115691778-115722904 |
| 25233 | Rnf103 | NM_009543.3 | chr6:71443887-71460875 |
| 25234 | Rnf11 | NM_013876.2 | chr4:109125461-109149110 |
| 25235 | Rnf111 | NM_033604.2 | chr9:70273235-70351532 |
| 25236 | Rnf112 | NM_001291024.1 | chr11:61261918-61267494 |
| 25237 | Rnf112 | NM_009548.3 | chr11:61261918-61267494 |
| 25238 | Rnf113a1 | NM_153503.1 | chrX:34731337-34732460 |
| 25239 | Rnf113a2 | NM_025525.2 | chr2:85758150-85759528 |
| 25240 | Rnf114 | NM_030743.1 | chr2:167318145-167341666 |
| 25241 | Rnf115 | NM_026406.3 | chr3:96531533-96595078 |
| 25242 | Rnf121 | NM_029211.2 | chr7:109168385-109213646 |
| 25243 | Rnf122 | NM_175136.2 | chr8:32222317-32241945 |
| 25244 | Rnf123 | NM_032543.2 | chr9:107954003-107981706 |
| 25245 | Rnf125 | NM_026301.2 | chr18:21103125-21142349 |
| 25246 | Rnf126 | NM_144528.3 | chr10:79221259-79229697 |
| 25247 | Rnf126 | NR_027505.2 | chr10:79221259-79229697 |
| 25248 | Rnf128 | NM_001254761.1 | chrX:136097878-136207684 |
| 25249 | Rnf128 | NM_023270.5 | chrX:136097878-136207684 |
| 25250 | Rnf13 | NM_001113413.2 | chr3:57539987-57639155 |
| 25251 | Rnf13 | NM_011883.4 | chr3:57539987-57639155 |
| 25252 | Rnf130 | NM_001290749.1 | chr11:49838832-49939221 |
| 25253 | Rnf130 | NM_001290750.1 | chr11:49838832-49939221 |
| 25254 | Rnf130 | NM_021540.4 | chr11:49838832-49939221 |
| 25255 | Rnf133 | NM_198251.2 | chr6:23598869-23600305 |
| 25256 | Rnf135 | NM_028019.3 | chr11:79997373-80013255 |
| 25257 | Rnf138 | NM_019706.1 | chr18:21159841-21186724 |
| 25258 | Rnf138 | NM_207623.2 | chr18:21159841-21186724 |
| 25259 | Rnf138rt1 | NM_028842.3 | chrX:160198070-160199264 |
| 25260 | Rnf139 | NM_175226.4 | chr15:58720784-58733945 |
| 25261 | Rnf14 | NM_001164620.1 | chr18:38456288-38477503 |
| 25262 | Rnf14 | NM_001164622.1 | chr18:38456288-38477503 |
| 25263 | Rnf14 | NM_020012.2 | chr18:38456288-38477503 |
| 25264 | Rnf141 | NM_025959.3 | chr7:117960048-117987895 |
| 25265 | Rnf144a | NM_001081977.2 | chr12:26991658-27100127 |
| 25266 | Rnf144a | NM_080563.4 | chr12:26991658-27100127 |
| 25267 | Rnf144b | NM_001170643.1 | chr13:47218088-47343360 |
| 25268 | Rnf144b | NM_146042.4 | chr13:47218088-47343360 |
| 25269 | Rnf145 | NM_001166553.1 | chr11:44332465-44379022 |
| 25270 | Rnf145 | NM_028862.3 | chr11:44332465-44379022 |
| 25271 | Rnf146 | NM_001110196.1 | chr10:29032971-29082248 |
| 25272 | Rnf146 | NM_001110197.1 | chr10:29032971-29082248 |
| 25273 | Rnf146 | NM_001110198.1 | chr10:29032971-29082248 |
| 25274 | Rnf146 | NM_001284279.1 | chr10:29032971-29082248 |
| 25275 | Rnf146 | NM_026518.4 | chr10:29032971-29082248 |
| 25276 | Rnf148 | NM_027754.1 | chr6:23603895-23605136 |
| 25277 | Rnf149 | NM_001033135.3 | chr1:39608143-39634192 |
| 25278 | Rnf150 | NM_177378.4 | chr8:85387254-85615519 |
| 25279 | Rnf151 | NM_026205.3 | chr17:24852784-24855002 |
| 25280 | Rnf152 | NM_001160368.1 | chr1:107173493-107253287 |
| 25281 | Rnf152 | NM_178779.4 | chr1:107173493-107253287 |
| 25282 | Rnf157 | NM_027258.1 | chr11:116197658-116274346 |
| 25283 | Rnf165 | NM_001164504.1 | chr18:77694848-77803875 |
| 25284 | Rnf166 | NM_001033142.2 | chr8:124990046-124999964 |
| 25285 | Rnf167 | NM_027445.1 | chr11:70461090-70464916 |
| 25286 | Rnf168 | NM_027355.2 | chr16:32277546-32301525 |
| 25287 | Rnf169 | NM_175388.3 | chr7:107068764-107128968 |
| 25288 | Rnf17 | NM_001033043.1 | chr14:57021533-57143868 |
| 25289 | Rnf170 | NM_029965.2 | chr8:27229851-27254341 |
| 25290 | Rnf180 | NM_027934.2 | chr13:105937573-106083094 |
| 25291 | Rnf181 | NM_025607.3 | chr6:72309708-72312375 |
| 25292 | Rnf182 | NM_183204.4 | chr13:43711165-43766313 |
| 25293 | Rnf183 | NM_153504.3 | chr4:62088575-62095760 |
| 25294 | Rnf185 | NM_001290472.1 | chr11:3315975-3379834 |
| 25295 | Rnf185 | NM_001290473.1 | chr11:3315975-3379834 |
| 25296 | Rnf185 | NM_145355.5 | chr11:3315975-3379834 |
| 25297 | Rnf185 | NR_110959.1 | chr11:3315975-3379834 |
| 25298 | Rnf186 | NM_025786.3 | chr4:138523026-138524281 |
| 25299 | Rnf187 | NM_022423.2 | chr11:58745789-58752408 |
| 25300 | Rnf19a | NM_013923.2 | chr15:36169689-36212902 |
| 25301 | Rnf19b | NM_029219.1 | chr4:128735514-128761770 |
| 25302 | Rnf2 | NM_011277.2 | chr1:153316535-153347953 |
| 25303 | Rnf20 | NM_001163263.1 | chr4:49644931-49669758 |
| 25304 | Rnf20 | NM_182999.2 | chr4:49644931-49669758 |
| 25305 | Rnf207 | NM_001033489.2 | chr4:151681132-151692734 |
| 25306 | Rnf208 | NM_176834.2 | chr2:25098448-25099781 |
| 25307 | Rnf214 | NM_178709.4 | chr9:45671774-45714960 |
| 25308 | Rnf215 | NM_027859.2 | chr11:4035163-4041195 |
| 25309 | Rnf216 | NM_080561.4 | chr5:143752571-143874699 |
| 25310 | Rnf216 | NM_207110.1 | chr5:143752571-143874699 |
| 25311 | Rnf217 | NM_001146349.1 | chr10:31221692-31329531 |
| 25312 | Rnf219 | NM_026047.4 | chr14:104876750-104921883 |
| 25313 | Rnf220 | NM_025739.2 | chr4:116944068-117169520 |
| 25314 | Rnf222 | NM_177060.3 | chr11:68702054-68708517 |
| 25315 | Rnf223 | NM_001220499.1 | chr4:155506278-155507528 |
| 25316 | Rnf224 | NM_001033410.2 | chr2:25089995-25092307 |
| 25317 | Rnf24 | NM_178607.4 | chr2:131124224-131178628 |
| 25318 | Rnf25 | NM_021313.3 | chr1:74640325-74647971 |
| 25319 | Rnf26 | NM_153762.3 | chr9:43918863-43921134 |
| 25320 | Rnf31 | NM_194346.2 | chr14:56210626-56222508 |
| 25321 | Rnf32 | NM_001289757.1 | chr5:29522532-29552064 |
| 25322 | Rnf32 | NM_021470.6 | chr5:29522532-29552064 |
| 25323 | Rnf32 | NR_110371.1 | chr5:29522532-29552064 |
| 25324 | Rnf34 | NM_030564.1 | chr5:123300196-123318954 |
| 25325 | Rnf38 | NM_001038993.3 | chr4:44139083-44181155 |
| 25326 | Rnf38 | NM_175201.5 | chr4:44139083-44181155 |
| 25327 | Rnf39 | NM_001096321.1 | chr17:37079995-37084931 |
| 25328 | Rnf4 | NM_011278.5 | chr5:34679038-34696079 |
| 25329 | Rnf40 | NM_172281.2 | chr7:134732211-134747119 |
| 25330 | Rnf41 | NM_001164237.1 | chr10:127848671-127878497 |
| 25331 | Rnf41 | NM_026259.3 | chr10:127848671-127878497 |
| 25332 | Rnf41 | NR_104288.1 | chr10:127848671-127878497 |
| 25333 | Rnf41 | NR_104289.1 | chr10:127848671-127878497 |
| 25334 | Rnf41 | NR_104290.1 | chr10:127848671-127878497 |
| 25335 | Rnf43 | NM_172448.3 | chr11:87476589-87549041 |
| 25336 | Rnf44 | NM_001146025.1 | chr13:54780759-54795321 |
| 25337 | Rnf44 | NM_001146026.1 | chr13:54780759-54795321 |
| 25338 | Rnf44 | NM_001146027.1 | chr13:54780759-54795321 |
| 25339 | Rnf44 | NM_134064.2 | chr13:54780759-54795321 |
| 25340 | Rnf44 | NR_027395.1 | chr13:54780759-54795321 |
| 25341 | Rnf44 | NR_027396.1 | chr13:54780759-54795321 |
| 25342 | Rnf5 | NM_019403.3 | chr17:34738043-34740506 |
| 25343 | Rnf6 | NM_001256085.1 | chr5:147020769-147033033 |
| 25344 | Rnf6 | NM_001256086.1 | chr5:147020769-147033033 |
| 25345 | Rnf6 | NM_001256087.1 | chr5:147020769-147033033 |
| 25346 | Rnf6 | NM_028774.3 | chr5:147020769-147033033 |
| 25347 | Rnf7 | NM_011279.2 | chr9:96371375-96379014 |
| 25348 | Rnf8 | NM_021419.1 | chr17:29751775-29778604 |
| 25349 | Rnft1 | NM_029788.5 | chr11:86298158-86312509 |
| 25350 | Rnft2 | NM_001109902.1 | chr5:118640744-118695034 |
| 25351 | Rnft2 | NM_172998.3 | chr5:118640744-118695034 |
| 25352 | Rngtt | NM_011884.3 | chr4:33397286-33589589 |
| 25353 | Rnh1 | NM_001172100.1 | chr7:148346224-148358750 |
| 25354 | Rnh1 | NM_001172101.1 | chr7:148346224-148358750 |
| 25355 | Rnh1 | NM_145135.3 | chr7:148346224-148358750 |
| 25356 | Rnls | NM_001146342.2 | chr19:33212234-33466785 |
| 25357 | Rnls | NM_001167818.1 | chr19:33212234-33466785 |
| 25358 | Rnmt | NM_001170953.1 | chr18:68460008-68484506 |
| 25359 | Rnmt | NM_026440.4 | chr18:68460008-68484506 |
| 25360 | Rnmtl1 | NM_183263.5 | chr11:76057237-76064124 |
| 25361 | Rnpc3 | NM_001038696.1 | chr3:113307984-113333067 |
| 25362 | Rnpc3 | NM_001287015.1 | chr3:113307984-113333067 |
| 25363 | Rnpc3 | NM_026043.3 | chr3:113307984-113333067 |
| 25364 | Rnpep | NM_001159624.1 | chr1:137159275-137180661 |
| 25365 | Rnpep | NM_145417.3 | chr1:137159275-137180661 |
| 25366 | Rnpepl1 | NM_181405.4 | chr1:94807401-94817162 |
| 25367 | Rnps1 | NM_001080127.1 | chr17:24551619-24562842 |
| 25368 | Rnps1 | NM_001080128.1 | chr17:24551619-24562842 |
| 25369 | Rnps1 | NM_009070.2 | chr17:24551619-24562842 |
| 25370 | Rnu11 | NR_002865.2 | chr4:131825993-131826101 |
| 25371 | Rnu12 | NR_004432.2 | chr15:82980074-82980224 |
| 25372 | Rnu73b | NR_004418.1 | chr8:85944539-85944609 |
| 25373 | Robo1 | NM_019413.2 | chr16:72663393-73046345 |
| 25374 | Robo2 | NM_175549.4 | chr16:73892551-74411157 |
| 25375 | Robo3 | NM_001164767.1 | chr9:37223629-37240760 |
| 25376 | Robo4 | NM_028783.3 | chr9:37209630-37221607 |
| 25377 | Rock1 | NM_009071.2 | chr18:10064398-10181790 |
| 25378 | Rock2 | NM_009072.2 | chr12:16901783-16950080 |
| 25379 | Rogdi | NM_133185.2 | chr16:5008821-5013646 |
| 25380 | Rom1 | NM_009073.4 | chr19:9001871-9003846 |
| 25381 | Romo1 | NM_001164216.1 | chr2:155949372-155971530 |

Fig. 25 - 135

| | | | |
|---|---|---|---|
| 25382 | Romo1 | NM_001164217.2 | chr2:155949372-155971530 |
| 25383 | Romo1 | NM_025946.6 | chr2:155949372-155971530 |
| 25384 | Ropn1 | NM_030744.2 | chr16:34651296-34678696 |
| 25385 | Ropn1l | NM_145852.1 | chr15:31370964-31383444 |
| 25386 | Ror1 | NM_013845.4 | chr4:99768395-100115150 |
| 25387 | Ror2 | NM_013846.3 | chr13:53204685-53381478 |
| 25388 | Rora | NM_001289916.1 | chr9:68501592-69236053 |
| 25389 | Rora | NM_001289917.1 | chr9:68501592-69236053 |
| 25390 | Rora | NM_013646.2 | chr9:68501592-69236053 |
| 25391 | Rorb | NM_001043354.2 | chr19:19005098-19185686 |
| 25392 | Rorb | NM_001289921.1 | chr19:19005098-19185686 |
| 25393 | Rorb | NM_146095.4 | chr19:19005098-19185686 |
| 25394 | Rorc | NM_011281.3 | chr3:94176747-94202161 |
| 25395 | Ros1 | NM_011282.2 | chr10:51765731-51915650 |
| 25396 | Rp1 | NM_001195662.1 | chr1:4280926-4399322 |
| 25397 | Rp1 | NM_011283.2 | chr1:4280926-4399322 |
| 25398 | Rp1l1 | NM_146246.3 | chr14:64611267-64652343 |
| 25399 | Rp2h | NM_001290643.1 | chrX:19941606-19982779 |
| 25400 | Rp2h | NM_001290644.1 | chrX:19941606-19982779 |
| 25401 | Rp2h | NM_133669.5 | chrX:19941606-19982779 |
| 25402 | Rp2h | NR_110466.1 | chrX:19941606-19982779 |
| 25403 | Rp2h | NR_110967.1 | chrX:19941606-19982779 |
| 25404 | Rp9 | NM_018739.2 | chr9:22252755-22272800 |
| 25405 | Rpa1 | NM_001164223.1 | chr11:75113760-75161885 |
| 25406 | Rpa1 | NM_026653.2 | chr11:75113760-75161885 |
| 25407 | Rpa2 | NM_011284.3 | chr4:132324274-132334661 |
| 25408 | Rpa3 | NM_026632.4 | chr6:8205935-8209141 |
| 25409 | Rpain | NM_001252413.1 | chr11:70783701-70796528 |
| 25410 | Rpain | NM_001252414.1 | chr11:70783701-70796528 |
| 25411 | Rpain | NM_001252415.1 | chr11:70783701-70796528 |
| 25412 | Rpain | NM_027186.2 | chr11:70783701-70796528 |
| 25413 | Rpap1 | NM_001163701.1 | chr2:119589694-119613273 |
| 25414 | Rpap1 | NM_177294.5 | chr2:119589694-119613273 |
| 25415 | Rpap2 | NM_001163461.2 | chr5:107963729-108090872 |
| 25416 | Rpap2 | NM_001163462.2 | chr5:107963729-108090872 |
| 25417 | Rpap2 | NM_001289569.1 | chr5:107963729-108090872 |
| 25418 | Rpap2 | NM_001289570.1 | chr5:107963729-108090872 |
| 25419 | Rpap2 | NM_144911.3 | chr5:107963729-108090872 |
| 25420 | Rpap3 | NM_028003.2 | chr15:97505535-97536253 |
| 25421 | Rpe | NM_025683.2 | chr1:66747467-66766379 |
| 25422 | Rpe65 | NM_029987.2 | chr3:159262144-159288271 |
| 25423 | Rpf1 | NM_027332.5 | chr3:146169309-146184387 |
| 25424 | Rpf1 | NM_027371.3 | chr3:146169309-146184387 |
| 25425 | Rpf2 | NM_001042556.1 | chr10:39943051-39966845 |
| 25426 | Rpf2 | NM_023323.3 | chr10:39943051-39966845 |
| 25427 | Rpgr | NM_001177950.1 | chrX:9735341-9793921 |
| 25428 | Rpgr | NM_001177951.1 | chrX:9735341-9793921 |
| 25429 | Rpgr | NM_001177952.1 | chrX:9735341-9793921 |
| 25430 | Rpgr | NM_001177953.1 | chrX:9735341-9793921 |
| 25431 | Rpgr | NM_001177954.1 | chrX:9735341-9793921 |
| 25432 | Rpgr | NM_011285.2 | chrX:9735341-9793921 |
| 25433 | Rpgrip1 | NM_001168515.1 | chr14:52730577-52816914 |
| 25434 | Rpgrip1 | NM_023879.3 | chr14:52730577-52816914 |
| 25435 | Rpgrip1l | NM_173431.2 | chr8:93740928-93837121 |
| 25436 | Rph3a | NM_011286.3 | chr5:121390508-121459527 |
| 25437 | Rph3al | NM_001291159.1 | chr11:75644493-75739393 |
| 25438 | Rph3al | NM_029548.4 | chr11:75644493-75739393 |
| 25439 | Rpia | NM_009075.2 | chr6:70715713-70742169 |
| 25440 | Rpl10 | NM_052835.3 | chrX:71516155-71518474 |
| 25441 | Rpl10a | NM_011287.2 | chr17:28465415-28467978 |
| 25442 | Rpl10l | NM_001162933.1 | chr12:67384365-67385388 |
| 25443 | Rpl11 | NM_025919.2 | chr4:135605862-135609286 |
| 25444 | Rpl12 | NM_009076.3 | chr2:32817232-32819565 |
| 25445 | Rpl13 | NM_016738.5 | chr8:125626250-125629142 |
| 25446 | Rpl13a | NM_009438.3 | chr7:52380933-52384115 |
| 25447 | Rpl14 | NM_025974.2 | chr9:120480633-120483770 |
| 25448 | Rpl14-ps1 | NR_110499.1 | chr7:52580328-52581021 |
| 25449 | Rpl15 | NM_025586.3 | chr14:19100336-19103500 |
| 25450 | Rpl17 | NM_001002239.1 | chr18:75160131-75163035 |
| 25451 | Rpl18 | NM_009077.2 | chr7:52973440-52976205 |
| 25452 | Rpl18a | NM_029751.4 | chr8:73418621-73421342 |
| 25453 | Rpl19 | NM_001159483.1 | chr11:97888023-97891807 |
| 25454 | Rpl19 | NM_009078.2 | chr11:97888023-97891807 |
| 25455 | Rpl21 | NM_019647.6 | chr5:147644465-147648608 |
| 25456 | Rpl22 | NM_001277113.1 | chr4:151698544-151708191 |
| 25457 | Rpl22 | NM_001277114.1 | chr4:151698544-151708191 |
| 25458 | Rpl22 | NM_009079.3 | chr4:151698544-151708191 |
| 25459 | Rpl22 | NR_102291.1 | chr4:151698544-151708191 |
| 25460 | Rpl22 | NR_102292.1 | chr4:151698544-151708191 |
| 25461 | Rpl22l1 | NM_026517.2 | chr3:28704432-28706337 |
| 25462 | Rpl23 | NM_022891.3 | chr11:97638840-97643753 |
| 25463 | Rpl23a | NM_207523.3 | chr11:77994437-77997086 |
| 25464 | Rpl24 | NM_024218.4 | chr16:55966387-55971550 |
| 25465 | Rpl26 | NM_009080.2 | chr11:68715068-68718036 |
| 25466 | Rpl27 | NM_011289.3 | chr11:101303558-101306910 |
| 25467 | Rpl27a | NM_011975.3 | chr7:116662709-116665883 |
| 25468 | Rpl28 | NM_009081.2 | chr7:4744566-4746149 |
| 25469 | Rpl29 | NM_009082.2 | chr9:106331869-106333898 |
| 25470 | Rpl3 | NM_013762.2 | chr15:79908211-79913836 |
| 25471 | Rpl30 | NM_001163485.1 | chr15:34370260-34373031 |
| 25472 | Rpl30 | NM_009083.4 | chr15:34370260-34373031 |
| 25473 | Rpl31 | NM_001252218.1 | chr1:39424695-39535592 |
| 25474 | Rpl31 | NM_053257.3 | chr1:39424695-39535592 |
| 25475 | Rpl31 | NM_053257.3 | chr1:39424695-39535592 |
| 25476 | Rpl31-ps12 | NM_001258458.1 | chr16:16819806-16820289 |
| 25477 | Rpl32 | NM_172086.2 | chr6:115755532-115758761 |
| 25478 | Rpl34 | NM_001005859.3 | chr3:130429744-130433316 |
| 25479 | Rpl34 | NM_001287581.1 | chr3:130429744-130433316 |
| 25480 | Rpl34 | NM_026724.2 | chr3:130429744-130433316 |
| 25481 | Rpl34-ps1 | NM_001199350.1 | chr3:130429755-130433247 |
| 25482 | Rpl35 | NM_025992.3 | chr2:38857101-38860651 |
| 25483 | Rpl35a | NM_001130484.1 | chr16:33056538-33060274 |
| 25484 | Rpl35a | NM_001130485.1 | chr16:33056538-33060274 |
| 25485 | Rpl35a | NM_021338.3 | chr16:33056538-33060274 |
| 25486 | Rpl36 | NM_018730.3 | chr17:56752817-56753669 |
| 25487 | Rpl36a | NM_019865.5 | chrX:131120192-131122601 |
| 25488 | Rpl36al | NM_025589.4 | chr12:70283720-70285054 |
| 25489 | Rpl37 | NM_026069.3 | chr15:5066613-5069140 |
| 25490 | Rpl37a | NM_009084.4 | chr1:72757833-72760387 |
| 25491 | Rpl38 | NM_001048057.1 | chr11:114529856-114533645 |
| 25492 | Rpl38 | NM_001048058.1 | chr11:114529856-114533645 |
| 25493 | Rpl38 | NM_023372.2 | chr11:114529856-114533645 |
| 25494 | Rpl39 | NM_026055.1 | chrX:34622515-34625179 |
| 25495 | Rpl39l | NM_026594.2 | chr16:10176320-10175004 |
| 25496 | Rpl3l | NM_001163945.1 | chr17:24864773-24873094 |
| 25497 | Rpl3l | NM_025425.4 | chr17:24864773-24873094 |
| 25498 | Rpl4 | NM_024212.4 | chr9:64021194-64026369 |
| 25499 | Rpl41 | NM_018860.1 | chr10:127985165-127986224 |
| 25500 | Rpl5 | NM_016980.2 | chr5:108329547-108338024 |
| 25501 | Rpl6 | NM_011290.2 | chr5:121654509-121659250 |
| 25502 | Rpl7 | NM_011291.5 | chr1:16091375-16094514 |
| 25503 | Rpl7a | NM_013721.3 | chr2:26766326-26768831 |
| 25504 | Rpl7l1 | NM_025433.3 | chr17:46910855-46919605 |
| 25505 | Rpl8 | NM_012053.2 | chr15:76734500-76736748 |
| 25506 | Rpl9 | NM_011292.2 | chr5:65779602-65782670 |
| 25507 | Rplp0 | NM_007475.5 | chr5:116049475-116013738 |
| 25508 | Rplp1 | NM_018853.3 | chr9:61761089-61762317 |
| 25509 | Rplp2 | NM_026020.6 | chr7:148633549-148637241 |
| 25510 | Rplp2-ps1 | NR_038063.1 | chr12:76731912-76732736 |
| 25511 | Rpn1 | NM_133933.4 | chr6:88034467-88055298 |
| 25512 | Rpn2 | NM_019642.4 | chr2:157104834-157152054 |
| 25513 | Rpp14 | NM_025938.4 | chr14:8912826-8924360 |
| 25514 | Rpp21 | NM_026308.2 | chr17:36392617-36394791 |
| 25515 | Rpp25 | NM_133982.1 | chr9:57351908-57353254 |
| 25516 | Rpp25l | NM_027278.3 | chr4:41659064-41660549 |
| 25517 | Rpp30 | NM_019428.3 | chr19:36158205-36179263 |
| 25518 | Rpp38 | NM_001013376.2 | chr2:3246220-3249900 |
| 25519 | Rpp40 | NM_145938.4 | chr13:35986972-35998216 |
| 25520 | Rpph1 | NR_002142.2 | chr14:51427121-51427446 |
| 25521 | Rprd1a | NM_144861.2 | chr18:24643462-24688705 |
| 25522 | Rprd1b | NM_001291134.1 | chr2:157854232-157917533 |
| 25523 | Rprd1b | NM_001291135.1 | chr2:157854232-157917533 |
| 25524 | Rprd1b | NM_001291136.1 | chr2:157854232-157917533 |
| 25525 | Rprd1b | NM_027434.3 | chr2:157854232-157917533 |
| 25526 | Rprd2 | NM_001081293.1 | chr3:95563795-95622876 |
| 25527 | Rprl1 | NR_004434.3 | chr5:69276930-69277168 |
| 25528 | Rprl2 | NR_004439.2 | chr3:22150291-22150529 |
| 25529 | Rprl3 | NM_024198.2 | chr8:3803124-3803361 |
| 25530 | Rprm | NM_023396.5 | chr2:53936503-53937963 |
| 25531 | Rprml | NM_001033212.2 | chr11:103510822-103511894 |
| 25532 | Rps10 | NM_025963.3 | chr17:27767373-27772187 |
| 25533 | Rps11 | NM_013725.4 | chr7:52377758-52379759 |
| 25534 | Rps12 | NM_011295.6 | chr10:23504989-23507015 |
| 25535 | Rps13 | NM_026533.3 | chr7:123475020-123477704 |
| 25536 | Rps14 | NM_020600.4 | chr18:60934249-60938200 |
| 25537 | Rps15 | NM_009091.2 | chr10:79755175-79756859 |
| 25538 | Rps15a | NM_170669.2 | chr7:125247889-125259661 |
| 25539 | Rps15a-ps4 | NR_036572.1 | chr4:131775807-131776504 |
| 25540 | Rps15a-ps6 | NR_029471.2 | chr11:6072511-6073334 |
| 25541 | Rps16 | NM_013647.2 | chr7:29135708-29137717 |
| 25542 | Rps17 | NM_009092.3 | chr7:88487618-88490120 |
| 25543 | Rps18 | NM_011296.2 | chr17:34088943-34092586 |
| 25544 | Rps19 | NM_023133.1 | chr7:25669732-25674821 |
| 25545 | Rps19bp1 | NM_175109.3 | chr15:80091043-80094736 |
| 25546 | Rps19-ps3 | NR_033639.1 | chr4:147195885-147196311 |
| 25547 | Rps2 | NM_008503.1 | chr17:24857008-24858872 |
| 25548 | Rps20 | NM_026147.5 | chr4:3761619-3762747 |
| 25549 | Rps21 | NM_025587.2 | chr2:179992084-179993149 |
| 25550 | Rps23 | NM_024175.3 | chr13:91062726-91064337 |
| 25551 | Rps24 | NM_011297.2 | chr14:25309902-25315368 |
| 25552 | Rps24 | NM_207634.2 | chr14:25309902-25315368 |
| 25553 | Rps24 | NM_207635.1 | chr14:25309902-25315368 |
| 25554 | Rps25 | NM_024266.3 | chr9:44215797-44218489 |
| 25555 | Rps26 | NM_013765.2 | chr10:128061584-128063562 |
| 25556 | Rps27 | NM_027015.4 | chr3:90016588-90017570 |
| 25557 | Rps27 | NR_033727.1 | chr3:90016588-90017570 |
| 25558 | Rps27a | NM_001033865.1 | chr11:29445841-29478352 |
| 25559 | Rps27a | NM_024277.2 | chr11:29445841-29478352 |
| 25560 | Rps27l | NM_026467.3 | chr9:66793924-66797316 |
| 25561 | Rps27rt | NM_001190258.1 | chr3:90016589-90017569 |
| 25562 | Rps28 | NM_016844.2 | chr17:33959981-33961443 |
| 25563 | Rps29 | NM_009093.2 | chr12:70258708-70260173 |
| 25564 | Rps3 | NM_012052.2 | chr7:106626407-106632219 |
| 25565 | Rps3a1 | NM_016959.2 | chr8:85941862-85946590 |
| 25566 | Rps4l | NR_003634.2 | chr5:148303178-148304118 |
| 25567 | Rps4x | NM_009094.1 | chrX:99380281-99383710 |
| 25568 | Rps5 | NM_009095.2 | chr7:13507659-13512035 |
| 25569 | Rps6 | NM_009096.3 | chr4:86500802-86503271 |
| 25570 | Rps6ka1 | NM_001285505.1 | chr4:133403205-133443712 |
| 25571 | Rps6ka1 | NM_001285506.1 | chr4:133403205-133443712 |

Fig. 25 - 136

| | | | | | | |
|---|---|---|---|---|---|---|
| 25572 | Rps6ka1 | NM_009097.5 | chr4:133403205-133443712 | 25667 | Rtel1 | NM_001166668.1 | chr2:181054428-181091321 |
| 25573 | Rps6ka2 | NM_011299.1 | chr17:7374463-7507664 | 25668 | Rtel1 | NR_030710.1 | chr2:181054428-181091321 |
| 25574 | Rps6ka3 | NM_148945.2 | chrX:155693713-155806176 | 25669 | Rtf1 | NM_030112.2 | chr2:119500803-119561143 |
| 25575 | Rps6ka4 | NM_019924.2 | chr19:6903574-6915117 | 25670 | Rtfdc1 | NM_025542.2 | chr2:172266078-172295399 |
| 25576 | Rps6ka5 | NM_153587.2 | chr12:101787987-101963238 | 25671 | Rtkn | NM_001136227.1 | chr6:83085801-83102573 |
| 25577 | Rps6ka6 | NM_025949.3 | chrX:108501445-108651568 | 25672 | Rtkn | NM_009106.2 | chr6:83085801-83102573 |
| 25578 | Rps6kb1 | NM_001114334.1 | chr11:86312512-86358309 | 25673 | Rtkn | NM_133641.2 | chr6:83085801-83102573 |
| 25579 | Rps6kb1 | NM_028259.4 | chr11:86312512-86358309 | 25674 | Rtkn2 | NM_001081346.1 | chr10:67442345-67506612 |
| 25580 | Rps6kb2 | NM_021485.2 | chr19:4156976-4163245 | 25675 | Rtl1 | NM_184109.1 | chr12:110828379-110833613 |
| 25581 | Rps6kc1 | NM_178775.4 | chr1:192596757-192735649 | 25676 | Rtn1 | NM_001007596.2 | chr12:73312735-73510041 |
| 25582 | Rps6kl1 | NM_146244.4 | chr12:86476545-86492214 | 25677 | Rtn1 | NM_001286448.1 | chr12:73312735-73510041 |
| 25583 | Rps7 | NM_011300.3 | chr12:29315711-29320818 | 25678 | Rtn1 | NM_153457.2 | chr12:73312735-73510041 |
| 25584 | Rps8 | NM_009098.2 | chr4:116826441-116828737 | 25679 | Rtn1 | NR_104446.1 | chr12:73312735-73510041 |
| 25585 | Rps9 | NM_029767.2 | chr7:3655642-3658499 | 25680 | Rtn2 | NM_001025364.3 | chr7:19867972-19881513 |
| 25586 | Rpsa | NM_011029.4 | chr9:120036884-120041487 | 25681 | Rtn2 | NM_013648.6 | chr7:19867972-19881513 |
| 25587 | Rptn | NM_009100.2 | chr3:93197620-93203364 | 25682 | Rtn3 | NM_001003933.2 | chr19:7492114-7557781 |
| 25588 | Rptor | NM_028898.3 | chr11:119464219-119760905 | 25683 | Rtn3 | NM_001003934.2 | chr19:7492114-7557781 |
| 25589 | Rptoros | NR_045312.1 | chr11:119464308-119760905 | 25684 | Rtn3 | NM_001271486.1 | chr19:7492114-7557781 |
| 25590 | Rptoros | NR_045313.1 | chr11:119464308-119760905 | 25685 | Rtn3 | NM_001271487.1 | chr19:7492114-7557781 |
| 25591 | Rpusd1 | NM_028009.3 | chr17:25864695-25868401 | 25686 | Rtn3 | NM_053076.3 | chr19:7492114-7557781 |
| 25592 | Rpusd2 | NM_173450.3 | chr2:118860525-118867933 | 25687 | Rtn4 | NM_024226.4 | chr11:29592897-29926033 |
| 25593 | Rpusd3 | NM_001033204.1 | chr6:113365312-113369334 | 25688 | Rtn4 | NM_194051.3 | chr11:29592897-29926033 |
| 25594 | Rpusd4 | NM_028040.2 | chr9:35075465-35083542 | 25689 | Rtn4 | NM_194052.3 | chr11:29592897-29926033 |
| 25595 | Rqcd1 | NM_021383.5 | chr1:74552634-74577416 | 25690 | Rtn4 | NM_194053.3 | chr11:29592897-29926033 |
| 25596 | Rrad | NM_019662.2 | chr8:107151965-107155221 | 25691 | Rtn4 | NM_194054.3 | chr11:29592897-29926033 |
| 25597 | Rraga | NM_178376.3 | chr4:86221576-86223187 | 25692 | Rtn4ip1 | NM_130892.4 | chr10:43621612-43667668 |
| 25598 | Rragb | NM_001004154.2 | chrX:149574500-149606486 | 25693 | Rtn4r | NM_022982.2 | chr16:18127798-18152501 |
| 25599 | Rragc | NM_017475.2 | chr4:123594675-123614240 | 25694 | Rtn4rl1 | NM_177708.5 | chr11:75007494-75081264 |
| 25600 | Rragd | NM_027491.2 | chr4:33069972-33109155 | 25695 | Rtn4rl2 | NM_199223.1 | chr2:84712102-84726849 |
| 25601 | Rras | NM_009101.2 | chr7:52273376-52277014 | 25696 | Rtp1 | NM_001004151.2 | chr16:23429205-23434033 |
| 25602 | Rras2 | NM_025846.2 | chr7:121190295-121261295 | 25697 | Rtp2 | NM_001008230.3 | chr16:23915633-23930880 |
| 25603 | Rrbp1 | NM_024281.2 | chr2:143773130-143836999 | 25698 | Rtp3 | NM_153100.2 | chr9:110887446-110892217 |
| 25604 | Rrbp1 | NM_133626.2 | chr2:143773130-143836999 | 25699 | Rtp4 | NM_023386.5 | chr16:23610004-23614308 |
| 25605 | Rreb1 | NM_001039188.1 | chr13:37917906-38043874 | 25700 | Rttn | NM_175542.3 | chr18:89141182-89300406 |
| 25606 | Rreb1 | NM_001177868.1 | chr13:37917906-38043874 | 25701 | Rubie | NR_046459.1 | chr14:47188005-47195526 |
| 25607 | Rreb1 | NM_001177869.1 | chr13:37917906-38043874 | 25702 | Rufy1 | NM_172557.2 | chr11:50202804-50244613 |
| 25608 | Rreb1 | NM_026830.2 | chr13:37917906-38043874 | 25703 | Rufy2 | NM_027425.3 | chr10:62442971-62481490 |
| 25609 | Rreb1 | NR_033218.1 | chr13:37917906-38043874 | 25704 | Rufy3 | NM_001289774.1 | chr5:88994064-89080442 |
| 25610 | Rreb1 | NR_033615.1 | chr13:37917906-38043874 | 25705 | Rufy3 | NM_001289775.1 | chr5:88994064-89080442 |
| 25611 | Rrh | NM_009102.3 | chr3:129511492-129525423 | 25706 | Rufy3 | NM_001289776.1 | chr5:88994064-89080442 |
| 25612 | Rrm1 | NM_009103.3 | chr7:109590208-109618285 | 25707 | Rufy3 | NM_001289777.1 | chr5:88994064-89080442 |
| 25613 | Rrm2 | NM_009104.2 | chr12:25393118-25399011 | 25708 | Rufy3 | NM_027530.3 | chr5:88994064-89080442 |
| 25614 | Rrm2b | NM_199476.1 | chr15:37853707-37890810 | 25709 | Rufy4 | NM_001034060.3 | chr1:74172114-74194804 |
| 25615 | Rrn3 | NM_001039521.1 | chr16:13780791-13814934 | 25710 | Rufy4 | NM_001170641.1 | chr1:74172114-74194804 |
| 25616 | Rrnad1 | NM_153562.1 | chr3:87726523-87734117 | 25711 | Rundc1 | NM_172566.4 | chr11:101286399-101296979 |
| 25617 | Rrp1 | NM_010925.2 | chr10:77863107-77875788 | 25712 | Rundc3a | NM_001252347.1 | chr11:102254716-102264253 |
| 25618 | Rrp12 | NM_199447.2 | chr19:41937340-41970643 | 25713 | Rundc3a | NM_016759.4 | chr11:102254716-102264253 |
| 25619 | Rrp15 | NM_026041.2 | chr1:186544964-186573237 | 25714 | Rundc3b | NM_198620.1 | chr5:8490935-8622952 |
| 25620 | Rrp1b | NM_001163734.1 | chr17:32173106-32199807 | 25715 | Runx1 | NM_001111021.2 | chr16:92601710-92826319 |
| 25621 | Rrp1b | NM_028244.2 | chr17:32173106-32199807 | 25716 | Runx1 | NM_001111022.2 | chr16:92601710-92826319 |
| 25622 | Rrp36 | NM_144857.1 | chr17:46804404-46811204 | 25717 | Runx1 | NM_001111023.2 | chr16:92601710-92826319 |
| 25623 | Rrp7a | NM_029101.4 | chr15:82946277-82953231 | 25718 | Runx1 | NM_009821.3 | chr16:92601710-92826319 |
| 25624 | Rrp8 | NM_025897.2 | chr7:112880243-112892852 | 25719 | Runx1t1 | NM_001111026.2 | chr4:13670448-13822202 |
| 25625 | Rrp8 | NM_133951.1 | chr7:112880243-112892852 | 25720 | Runx1t1 | NM_001111027.2 | chr4:13670448-13822202 |
| 25626 | Rrp9 | NM_145620.4 | chr9:106379639-106387746 | 25721 | Runx1t1 | NM_009822.3 | chr4:13670448-13822202 |
| 25627 | Rrs1 | NM_021511.2 | chr1:9535488-9537536 | 25722 | Runx2 | NM_001145920.2 | chr17:44632935-45256233 |
| 25628 | Rs1 | NM_011302.3 | chrX:157205945-157237595 | 25723 | Runx2 | NM_001146038.2 | chr17:44632935-45256233 |
| 25629 | Rsad1 | NM_001013381.2 | chr11:94401111-94410521 | 25724 | Runx2 | NM_001271627.1 | chr17:44632935-45256233 |
| 25630 | Rsad2 | NM_021384.4 | chr12:27127607-27141317 | 25725 | Runx2 | NM_001271630.1 | chr17:44632935-45256233 |
| 25631 | Rsbn1 | NM_172884.2 | chr3:103718043-103770543 | 25726 | Runx2 | NM_001271631.1 | chr17:44632935-45256233 |
| 25632 | Rsbn1l | NM_001080977.1 | chr5:20398842-20457640 | 25727 | Runx2 | NM_009820.5 | chr17:44632935-45256233 |
| 25633 | Rsc1a1 | NM_023544.5 | chr4:141239478-141241631 | 25728 | Runx2 | NR_073392.1 | chr17:44632935-45256233 |
| 25634 | Rsf1 | NM_001081267.2 | chr7:104728405-104841292 | 25729 | Runx2 | NR_073425.1 | chr17:44632935-45256233 |
| 25635 | Rsg1 | NM_001081174.2 | chr4:140769870-140776029 | 25730 | Runx3 | NM_019732.2 | chr4:134676559-134733905 |
| 25636 | Rsl1 | NM_001013769.1 | chr13:67274117-67284434 | 25731 | Rusc1 | NM_001083807.1 | chr3:88887900-88897285 |
| 25637 | Rslid1 | NM_025546.2 | chr16:11193129-11203385 | 25732 | Rusc1 | NM_001083808.1 | chr3:88887900-88897285 |
| 25638 | Rsl24d1 | NM_198609.2 | chr9:72961275-72971140 | 25733 | Rusc1 | NM_028188.2 | chr3:88887900-88897285 |
| 25639 | Rslcan18 | NM_001256052.1 | chr3:67197549-67214964 | 25734 | Rusc2 | NM_001037709.2 | chr4:43394853-43442006 |
| 25640 | Rsph1 | NM_025290.3 | chr17:31391964-31414301 | 25735 | Rusc2 | NM_199057.3 | chr4:43394853-43442006 |
| 25641 | Rsph3a | NM_025875.3 | chr17:8138478-8172421 | 25736 | Ruvbl1 | NM_019685.2 | chr6:88415416-88447560 |
| 25642 | Rsph3b | NM_001083945.1 | chr17:7109064-7152705 | 25737 | Ruvbl2 | NM_011304.3 | chr7:52677267-52689834 |
| 25643 | Rsph4a | NM_001162957.1 | chr10:33624916-33635827 | 25738 | Rwdd1 | NM_025614.3 | chr10:33716360-33739422 |
| 25644 | Rsph6a | NM_001165671.1 | chr7:19640035-19659796 | 25739 | Rwdd2a | NM_001145968.1 | chr9:86465594-86468506 |
| 25645 | Rsph6a | NM_031255.2 | chr7:19640035-19659796 | 25740 | Rwdd2a | NM_001145969.1 | chr9:86465594-86468506 |
| 25646 | Rsph9 | NM_029338.3 | chr17:46266225-46281147 | 25741 | Rwdd2a | NM_027100.2 | chr9:86465594-86468506 |
| 25647 | Rspo1 | NM_138683.2 | chr4:124663673-124686343 | 25742 | Rwdd2b | NM_016924.2 | chr16:87433575-87440837 |
| 25648 | Rspo2 | NM_172815.3 | chr15:42852340-43002364 | 25743 | Rwdd3 | NM_025637.3 | chr3:120858319-120874613 |
| 25649 | Rspo3 | NM_028351.3 | chr10:29172912-29255673 | 25744 | Rwdd3 | NM_028456.3 | chr3:120858319-120874613 |
| 25650 | Rspo4 | NM_001040689.1 | chr2:151668662-151700404 | 25745 | Rwdd4a | NM_203507.3 | chr8:48618998-48638191 |
| 25651 | Rspry1 | NM_026274.4 | chr8:97125840-97184176 | 25746 | Rxfp1 | NM_212452.1 | chr3:79448637-79541716 |
| 25652 | Rsrc1 | NM_025822.3 | chr3:66789593-67162325 | 25747 | Rxfp2 | NM_001289564.1 | chr5:150821249-150884761 |
| 25653 | Rsrc2 | NM_001005525.2 | chr5:124178434-124199423 | 25748 | Rxfp2 | NM_001289566.1 | chr5:150821249-150884761 |
| 25654 | Rsrp1 | NM_023665.3 | chr4:134479539-134483285 | 25749 | Rxfp2 | NM_080468.2 | chr5:150821249-150884761 |
| 25655 | Rsu1 | NM_009105.4 | chr2:12998593-13193042 | 25750 | Rxfp3 | NM_178717.3 | chr15:10963471-10967723 |
| 25656 | Rtbdn | NM_144929.2 | chr7:87470889-87480502 | 25751 | Rxfp4 | NM_181817.1 | chr3:88455819-88457064 |
| 25657 | Rtca | NM_025517.3 | chr3:116191881-116211093 | 25752 | Rxra | NM_001290481.1 | chr2:27532720-27618839 |
| 25658 | Rtcb | NM_145422.4 | chr10:85401381-85420538 | 25753 | Rxra | NM_001290482.1 | chr2:27532720-27618839 |
| 25659 | Rtdr1 | NM_001163533.1 | chr10:74420221-74495331 | 25754 | Rxra | NM_011305.3 | chr2:27532720-27618839 |
| 25660 | Rtdr1 | NM_001163534.1 | chr10:74420221-74495331 | 25755 | Rxrb | NM_001205214.1 | chr17:34168756-34175348 |
| 25661 | Rtdr1 | NM_001163535.1 | chr10:74420221-74495331 | 25756 | Rxrb | NM_001205215.1 | chr17:34168756-34175348 |
| 25662 | Rtdr1 | NM_027730.1 | chr10:74420221-74495331 | 25757 | Rxrb | NM_001205216.1 | chr17:34168756-34175348 |
| 25663 | Rtel1 | NM_001001882.3 | chr2:181054428-181091321 | 25758 | Rxrb | NM_011306.4 | chr17:34168756-34175348 |
| 25664 | Rtel1 | NM_001166665.1 | chr2:181054428-181091321 | 25759 | Rxrg | NM_001159731.1 | chr1:169528492-169569754 |
| 25665 | Rtel1 | NM_001166666.1 | chr2:181054428-181091321 | 25760 | Rxrg | NM_009107.3 | chr1:169528492-169569754 |
| 25666 | Rtel1 | NM_001166667.1 | chr2:181054428-181091321 | 25761 | Rybp | NM_019743.3 | chr6:100178558-100237352 |

Fig. 25 - 137

| | | | |
|---|---|---|---|
| 25762 | Ryk | NM_001042607.1 | chr9:102737249-102810637 |
| 25763 | Ryk | NM_001284258.1 | chr9:102737249-102810637 |
| 25764 | Ryk | NM_013649.3 | chr9:102737249-102810637 |
| 25765 | Ryr1 | NM_009109.2 | chr7:29788359-29910170 |
| 25766 | Ryr2 | NM_023868.2 | chr13:11645369-12199212 |
| 25767 | Ryr3 | NM_177652.2 | chr2:112471538-112870488 |
| 25768 | S100a1 | NM_011309.3 | chr3:90314955-90318252 |
| 25769 | S100a10 | NM_009112.2 | chr3:93359038-93368567 |
| 25770 | S100a11 | NM_016740.3 | chr3:93324417-93330210 |
| 25771 | S100a13 | NM_009113.4 | chr3:90318356-90328503 |
| 25772 | S100a14 | NM_001163525.2 | chr3:90330770-90332757 |
| 25773 | S100a14 | NM_001163526.2 | chr3:90330770-90332757 |
| 25774 | S100a14 | NM_025393.4 | chr3:90330770-90332757 |
| 25775 | S100a16 | NM_026416.2 | chr3:90345144-90347073 |
| 25776 | S100a2 | NM_001195760.1 | chr3:90394168-90395430 |
| 25777 | S100a3 | NM_011310.2 | chr3:90404136-90406624 |
| 25778 | S100a4 | NM_011311.2 | chr3:90407691-90409967 |
| 25779 | S100a5 | NM_011312.2 | chr3:90412443-90415702 |
| 25780 | S100a6 | NM_011313.2 | chr3:90416815-90418336 |
| 25781 | S100a7a | NM_199422.1 | chr3:90458223-90462052 |
| 25782 | S100a8 | NM_013650.2 | chr3:90472992-90473956 |
| 25783 | S100a9 | NM_001281852.1 | chr3:90496551-90499643 |
| 25784 | S100a9 | NM_009114.3 | chr3:90496551-90499643 |
| 25785 | S100b | NM_009115.3 | chr10:75716580-75724064 |
| 25786 | S100g | NM_009789.2 | chrX:159309924-159402533 |
| 25787 | S100pbp | NM_029036.2 | chr4:128828068-128866726 |
| 25788 | SJ00z | NM_001081159.1 | chr13:96247255-96248610 |
| 25789 | S1pr1 | NM_007901.2 | chr3:115413350-115417973 |
| 25790 | S1pr2 | NM_010333.4 | chr9:20770395-20781237 |
| 25791 | S1pr3 | NM_010101.4 | chr13:51503986-51518166 |
| 25792 | S1pr4 | NM_010102.2 | chr10:80960489-80962882 |
| 25793 | S1pr5 | NM_053190.2 | chr9:21047360-21052887 |
| 25794 | Saa1 | NM_009117.3 | chr7:53995868-53998350 |
| 25795 | Saa2 | NM_011314.2 | chr7:54007202-54009684 |
| 25796 | Saa3 | NM_011315.3 | chr7:53967367-53971046 |
| 25797 | Saa4 | NM_011316.3 | chr7:53983368-53987913 |
| 25798 | Saal1 | NM_030233.1 | chr7:53941477-53966021 |
| 25799 | Sac3d1 | NM_133678.3 | chr19:6116003-6118586 |
| 25800 | Sacm1l | NM_030692.4 | chr9:123438999-123501716 |
| 25801 | Sacs | NM_172809.3 | chr14:61757294-61859530 |
| 25802 | Sae1 | NM_001285891.1 | chr7:16905584-16973245 |
| 25803 | Sae1 | NM_001285892.1 | chr7:16905584-16973245 |
| 25804 | Sae1 | NM_019748.3 | chr7:16905584-16973245 |
| 25805 | Safb | NM_001163300.1 | chr17:56724404-56745717 |
| 25806 | Safb2 | NM_001029979.1 | chr17:56702364-56724006 |
| 25807 | Sag | NM_009118.2 | chr1:89700254-89741732 |
| 25808 | Sall1 | NM_021390.3 | chr8:91551142-91568061 |
| 25809 | Sall2 | NM_001244916.1 | chr14:52930851-52948345 |
| 25810 | Sall2 | NM_015772.3 | chr14:52930851-52948345 |
| 25811 | Sall3 | NM_178280.3 | chr18:81163112-81183317 |
| 25812 | Sall4 | NM_175303.4 | chr2:168573831-168592701 |
| 25813 | Sall4 | NM_201395.3 | chr2:168573831-168592701 |
| 25814 | Sall4 | NM_201396.3 | chr2:168573831-168592701 |
| 25815 | Samd1 | NM_001081415.1 | chr8:86521570-86524285 |
| 25816 | Samd10 | NM_172676.2 | chr2:181329923-181333852 |
| 25817 | Samd12 | NM_177225.4 | chr15:53293355-53733991 |
| 25818 | Samd14 | NM_146025.2 | chr11:94871192-94887401 |
| 25819 | Samd15 | NM_001290288.1 | chr12:88541492-88554488 |
| 25820 | Samd3 | NM_001163766.2 | chr10:25949512-25991978 |
| 25821 | Samd3 | NM_001115154.1 | chr10:25949512-25991978 |
| 25822 | Samd4 | NM_001037221.2 | chr14:47502639-47725492 |
| 25823 | Samd4 | NM_001163443.1 | chr14:47502639-47725492 |
| 25824 | Samd4 | NM_028966.3 | chr14:47502639-47725492 |
| 25825 | Samd4b | NM_175021.3 | chr7:29184540-29221210 |
| 25826 | Samd5 | NM_177271.3 | chr10:9347056-9395006 |
| 25827 | Samd7 | NM_029489.3 | chr3:30645214-30666096 |
| 25828 | Samd7 | NR_028060.1 | chr3:30645214-30666096 |
| 25829 | Samd8 | NM_026183.2 | chr14:22569752-22617947 |
| 25830 | Samd9l | NM_010156.3 | chr6:3322256-3349571 |
| 25831 | Samhd1 | NM_001139253.1 | chr2:156923264-156960958 |
| 25832 | Samhd1 | NM_018851.3 | chr2:156923264-156960958 |
| 25833 | Samm50 | NM_178614.4 | chr15:84022662-84044733 |
| 25834 | Samsn1 | NM_023380.2 | chr16:75859038-75909511 |
| 25835 | Samt1 | NM_030036.1 | chrX:150544175-150555228 |
| 25836 | Samt1 | NM_030036.1 | chrX:150436132-150447185 |
| 25837 | Samt1 | NM_030036.1 | chrX:150457322-150468372 |
| 25838 | Samt1 | NM_030036.1 | chrX:150478528-150489584 |
| 25839 | Samt2 | NM_001037167.1 | chrX:151009770-151013873 |
| 25840 | Samt3 | NM_028554.3 | chrX:83289537-83292852 |
| 25841 | Samt4 | NM_029199.2 | chrX:150916544-150919225 |
| 25842 | Sap130 | NM_172965.2 | chr18:31794036-31838715 |
| 25843 | Sap18 | NM_009119.3 | chr14:58417026-58423817 |
| 25844 | Sap25 | NM_001081962.2 | chr5:138082701-138084130 |
| 25845 | Sap30 | NM_021788.2 | chr8:59961498-59966657 |
| 25846 | Sap30bp | NM_020483.3 | chr11:115794972-115826848 |
| 25847 | Sap30l | NM_001081168.1 | chr11:57615138-57624117 |
| 25848 | Sapcd1 | NM_021483.3 | chr17:35153523-35164961 |
| 25849 | Sapcd1 | NR_028258.1 | chr17:35153523-35164961 |
| 25850 | Sapcd2 | NM_001081085.2 | chr2:25227554-25233733 |
| 25851 | Sapcd2 | NM_001290407.1 | chr2:25227554-25233733 |
| 25852 | Sar1a | NM_009120.2 | chr10:61143068-61156045 |
| 25853 | Sar1b | NM_025535.2 | chr11:51577164-51605455 |
| 25854 | Sardh | NM_138665.2 | chr2:27043912-27102823 |
| 25855 | Sarm1 | NM_001168521.1 | chr11:78285831-78311256 |
| 25856 | Sarm1 | NM_172795.3 | chr11:78285831-78311256 |
| 25857 | Sarnp | NM_025364.2 | chr10:128258826-128314694 |
| 25858 | Sars | NM_001204979.1 | chr3:108227781-108248177 |
| 25859 | Sars | NM_011319.1 | chr3:108227781-108248177 |
| 25860 | Sars2 | NM_026637.3 | chr7:29526986-29538898 |
| 25861 | Sart1 | NM_016882.3 | chr19:5377523-5388703 |
| 25862 | Sart3 | NM_016926.1 | chr5:114192454-114221658 |
| 25863 | Sash1 | NM_175155.4 | chr10:8442016-8605868 |
| 25864 | Sash3 | NM_028773.3 | chrX:45499703-45514740 |
| 25865 | Sass6 | NM_001289568.1 | chr3:116265890-116333904 |
| 25866 | Sass6 | NM_001289571.1 | chr3:116265890-116333904 |
| 25867 | Sass6 | NM_028349.3 | chr3:116265890-116333904 |
| 25868 | Sat1 | NM_001291865.1 | chrX:151647668-151650992 |
| 25869 | Sat1 | NM_009121.4 | chrX:151647668-151650992 |
| 25870 | Sat2 | NM_026991.2 | chr11:69435610-69437371 |
| 25871 | Satb1 | NM_001163630.1 | chr17:51875511-51972615 |
| 25872 | Satb1 | NM_001163631.1 | chr17:51875511-51972615 |
| 25873 | Satb1 | NM_001163632.1 | chr17:51875511-51972615 |
| 25874 | Satb1 | NM_009122.2 | chr17:51875511-51972615 |
| 25875 | Satb2 | NM_139146.2 | chr1:56850824-57028178 |
| 25876 | Satl1 | NM_028655.1 | chrX:109497913-109520388 |
| 25877 | Sav1 | NM_022028.2 | chr12:71065999-71087989 |
| 25878 | Saysd1 | NM_026209.1 | chr14:20894857-20902394 |
| 25879 | Sbds | NM_023248.1 | chr5:130721601-130731332 |
| 25880 | Sbf1 | NM_001081030.2 | chr15:89118666-89145742 |
| 25881 | Sbf1 | NM_001170561.1 | chr15:89118666-89145742 |
| 25882 | Sbf2 | NM_177324.2 | chr7:117451526-117758434 |
| 25883 | Sbk1 | NM_145587.2 | chr7:133416132-133438513 |
| 25884 | Sbk2 | NM_001146329.1 | chr7:4908682-4915950 |
| 25885 | Sbk3 | NM_001200041.1 | chr7:4916861-4922563 |
| 25886 | Sbno1 | NM_001081203.1 | chr5:124818710-124875923 |
| 25887 | Sbno2 | NM_183426.1 | chr10:79519758-79565447 |
| 25888 | Sbp | NM_013321.3 | chr17:24078962-24082574 |
| 25889 | Sbpl | NM_001077421.1 | chr17:24090051-24092240 |
| 25890 | Sbsn | NM_001083903.1 | chr7:31536489-31541153 |
| 25891 | Sbsn | NM_172205.3 | chr7:31536489-31541153 |
| 25892 | Sbspon | NM_001033288.3 | chr1:15843942-15882803 |
| 25893 | Sc5d | NM_172769.2 | chr9:42062259-42072383 |
| 25894 | Scaf1 | NM_001008422.1 | chr7:52258320-52271619 |
| 25895 | Scaf11 | NM_028148.2 | chr15:96242128-96291274 |
| 25896 | Scaf4 | NM_178923.3 | chr16:90229384-90284670 |
| 25897 | Scaf8 | NM_134123.3 | chr17:3114971-3188859 |
| 25898 | Scai | NM_178778.3 | chr2:38921735-39046250 |
| 25899 | Scamp1 | NM_029153.1 | chr13:94971387-95055236 |
| 25900 | Scamp2 | NM_022813.3 | chr9:57408750-57436605 |
| 25901 | Scamp3 | NM_011886.2 | chr3:88981406-88986692 |
| 25902 | Scamp4 | NM_019575.4 | chr10:80065627-80078528 |
| 25903 | Scamp5 | NM_020270.3 | chr9:57289133-57315831 |
| 25904 | Scand1 | NM_020255.3 | chr2:156137582-156138440 |
| 25905 | Scap | NM_001001144.3 | chr9:110235791-110287453 |
| 25906 | Scap | NM_001103162.2 | chr9:110235791-110287453 |
| 25907 | Scaper | NM_001081341.1 | chr9:55397689-55785922 |
| 25908 | Scara3 | NM_172604.3 | chr14:66538231-66572581 |
| 25909 | Scara5 | NM_001168318.1 | chr14:66285239-66383663 |
| 25910 | Scara5 | NM_028903.2 | chr14:66285239-66383663 |
| 25911 | Scarb1 | NM_001205082.1 | chr5:125757456-125821464 |
| 25912 | Scarb1 | NM_001205083.1 | chr5:125757456-125821464 |
| 25913 | Scarb1 | NM_016741.2 | chr5:125757456-125821464 |
| 25914 | Scarb2 | NM_007644.3 | chr5:92872899-92934634 |
| 25915 | Scarf1 | NM_001004157.2 | chr11:75327042-75340082 |
| 25916 | Scarf2 | NM_153790.2 | chr16:17797374-17808380 |
| 25917 | Scarletltr | NR_040743.1 | chr9:63928567-63935852 |
| 25918 | Scarna10 | NR_028517.2 | chr6:125136379-125136449 |
| 25919 | Scarna13 | NR_028576.1 | chr12:106269287-106269559 |
| 25920 | Scarna17 | NR_028560.1 | chr18:74938047-74938109 |
| 25921 | Scarna2 | NR_028538.1 | chr3:108357259-108357320 |
| 25922 | Scarna3a | NR_028518.1 | chr1:161270438-161270555 |
| 25923 | Scarna3b | NR_028544.1 | chr12:81492601-81492724 |
| 25924 | Scarna6 | NR_028519.2 | chr18:89681146-89681393 |
| 25925 | Scarna8 | NR_028545.1 | chr4:86232357-86232474 |
| 25926 | Scarna9 | NR_028568.2 | chr9:15130733-15130774 |
| 25927 | Sccpdh | NM_178653.3 | chr1:181598361-181617315 |
| 25928 | Scd1 | NM_009127.4 | chr19:44468939-44482199 |
| 25929 | Scd2 | NM_009128.2 | chr19:44368166-44381352 |
| 25930 | Scd3 | NM_024450.2 | chr19:44277777-44318506 |
| 25931 | Scd4 | NM_183216.3 | chr19:44407815-44421233 |
| 25932 | Scel | NM_022886.2 | chr14:103912557-104012563 |
| 25933 | Scfd1 | NM_029825.3 | chr12:52478566-52551083 |
| 25934 | Scfd2 | NM_001114660.2 | chr5:74600840-74927767 |
| 25935 | Scfd2 | NM_001286437.1 | chr5:74600840-74927767 |
| 25936 | Scfd2 | NM_178672.7 | chr5:74600840-74927767 |
| 25937 | Scg2 | NM_009129.2 | chr1:79431243-79436665 |
| 25938 | Scg3 | NM_001164790.1 | chr9:75491172-75531863 |
| 25939 | Scg3 | NM_009130.3 | chr9:75491172-75531863 |
| 25940 | Scg5 | NM_009162.3 | chr2:113616469-113669248 |
| 25941 | Scgb1a1 | NM_011681.2 | chr19:9158131-9162446 |
| 25942 | Scgb1b19 | NM_001281526.1 | chr7:34072325-34073510 |
| 25943 | Scgb1b2 | NM_020563.3 | chr7:32075537-32076835 |
| 25944 | Scgb1b20 | NM_001270543.1 | chr7:34158252-34159577 |
| 25945 | Scgb1b24 | NM_001099329.2 | chr7:34528817-34530122 |
| 25946 | Scgb1b27 | NM_009596.1 | chr7:34806685-34807900 |
| 25947 | Scgb1b29 | NM_001256066.1 | chr7:33226559-33227863 |
| 25948 | Scgb1b3 | NM_001256073.1 | chr7:32160610-32161935 |
| 25949 | Scgb1b30 | NM_001099330.2 | chr7:34880449-34885856 |
| 25950 | Scgb1b7 | NM_001270542.1 | chr7:32497683-32498999 |
| 25951 | Scgb1c1 | NM_001099742.1 | chr7:148031464-148032668 |

Fig. 25 - 138

| | | | | | | | | |
|---|---|---|---|---|---|---|---|---|
| 25952 | Scgb2b12 | NM_001281508.1 | chr7:33110304-33112264 | | 26047 | Sdc2 | NM_008304.2 | chr15:32850477-32964476 |
| 25953 | Scgb2b15 | NM_001281523.1 | chr7:33839600-33841571 | | 26048 | Sdc3 | NM_013520.3 | chr4:130348451-130382233 |
| 25954 | Scgb2b17 | NM_001281524.1 | chr7:33612701-33614672 | | 26049 | Sdc4 | NM_011521.2 | chr2:164249746-164268688 |
| 25955 | Scgb2b19 | NM_001193336.1 | chr7:34063384-34065360 | | 26050 | Sdcbp | NM_001098227.1 | chr4:6292826-6323269 |
| 25956 | Scgb2b2 | NM_207262.2 | chr7:32087787-32089996 | | 26051 | Sdcbp | NM_016807.2 | chr4:6292826-6323269 |
| 25957 | Scgb2b20 | NM_001009952.2 | chr7:34149361-34151338 | | 26052 | Sdcbp2 | NM_145535.2 | chr2:151398358-151415741 |
| 25958 | Scgb2b23-ps | NR_045685.1 | chr7:34410163-34438300 | | 26053 | Sdccag3 | NM_001085407.1 | chr2:26238319-26244836 |
| 25959 | Scgb2b24 | NM_177446.2 | chr7:34522211-34524314 | | 26054 | Sdccag3 | NM_001085408.1 | chr2:26238319-26244836 |
| 25960 | Scgb2b26 | NM_178308.2 | chr7:34728015-34730004 | | 26055 | Sdccag3 | NM_026563.3 | chr2:26238319-26244836 |
| 25961 | Scgb2b27 | NM_001100464.2 | chr7:34796937-34798961 | | 26056 | Sdccag8 | NM_029756.3 | chr1:178744791-178950563 |
| 25962 | Scgb2b27 | NM_001276475.1 | chr7:34796937-34798961 | | 26057 | Sde2 | NM_145943.1 | chr1:182781281-182798245 |
| 25963 | Scgb2b3 | NM_001270541.1 | chr7:32144056-32147091 | | 26058 | Sdf2 | NM_009143.3 | chr11:78059247-78068998 |
| 25964 | Scgb2h7 | NM_001198871.1 | chr7:32488797-32490773 | | 26059 | Sdf2l1 | NM_022324.3 | chr16:17130230-17132476 |
| 25965 | Scgb3a1 | NM_054037.2 | chr11:49477096-49478620 | | 26060 | Sdf4 | NM_011341.5 | chr4:155367022-155387719 |
| 25966 | Scgb3a1 | NM_170727.2 | chr11:49477096-49478620 | | 26061 | Sdha | NM_023281.1 | chr13:74459702-74487688 |
| 25967 | Scgb3a2 | NM_001289643.1 | chr18:43923954-43927053 | | 26062 | Sdhaf1 | NM_001033140.3 | chr7:31106427-31107394 |
| 25968 | Scgb3a2 | NM_001289644.1 | chr18:43923954-43927053 | | 26063 | Sdhaf2 | NM_025333.4 | chr19:10575001-10599699 |
| 25969 | Scgn | NM_145399.1 | chr13:24045325-24083083 | | 26064 | Sdhb | NM_023374.3 | chr4:140517185-140535107 |
| 25970 | Schip1 | NM_001113420.1 | chr3:67696141-68430404 | | 26065 | Sdhc | NM_025321.3 | chr1:173059287-173080734 |
| 25971 | Schip1 | NM_001113421.1 | chr3:67696141-68430404 | | 26066 | Sdhd | NM_025848.3 | chr9:50404444-50411954 |
| 25972 | Schip1 | NM_001282044.1 | chr3:67696141-68430404 | | 26067 | Sdk1 | NM_177879.5 | chr5:141717487-142689745 |
| 25973 | Schip1 | NM_001282045.1 | chr3:67696141-68430404 | | 26068 | Sdk2 | NM_172800.2 | chr11:113642103-113927265 |
| 25974 | Schip1 | NM_013928.5 | chr3:67696141-68430404 | | 26069 | Sdpr | NM_138741.1 | chr1:51345970-51359804 |
| 25975 | Scimp | NM_001045526.2 | chr11:70604433-70626063 | | 26070 | Sdr16c5 | NM_181989.1 | chr4:3923088-3946810 |
| 25976 | Scin | NM_001146196.1 | chr12:40786357-40860815 | | 26071 | Sdr16c6 | NM_001080710.2 | chr4:3983812-4004661 |
| 25977 | Scin | NM_009132.2 | chr12:40786357-40860815 | | 26072 | Sdr39u1 | NM_001082975.1 | chr14:56516121-56519069 |
| 25978 | Scit1 | NM_001081411.1 | chr3:41430626-41546436 | | 26073 | Sdr42e1 | NM_028725.3 | chr8:120185298-120195415 |
| 25979 | Scly | NM_016717.3 | chr1:93194914-93217657 | | 26074 | Sdr9c7 | NM_027301.3 | chr10:127335590-127348815 |
| 25980 | Scmh1 | NM_001159630.1 | chr4:120077885-120202804 | | 26075 | Sds | NM_145565.1 | chr5:120926556-120933914 |
| 25981 | Scmh1 | NM_013883.2 | chr4:120077885-120202804 | | 26076 | Sdsl | NM_133902.2 | chr5:120908210-120922772 |
| 25982 | Scml2 | NM_001290651.1 | chrX:157600681-157696145 | | 26077 | Sebox | NM_008759.2 | chr11:78317014-78318584 |
| 25983 | Scml2 | NM_001290652.1 | chrX:157600681-157696145 | | 26078 | Sec1 | NM_001271578.1 | chr7:52933057-52949772 |
| 25984 | Scml2 | NM_133194.3 | chrX:157600681-157696145 | | 26079 | Sec11a | NM_019951.1 | chr7:88060264-88092436 |
| 25985 | Scml4 | NM_172938.3 | chr10:42580317-42680588 | | 26080 | Sec11c | NM_025468.2 | chr18:65960231-65977311 |
| 25986 | Scn10a | NM_001205321.1 | chr9:119517573-119628150 | | 26081 | Sec13 | NM_024206.4 | chr6:113678045-113690675 |
| 25987 | Scn10a | NM_009134.3 | chr9:119517573-119628150 | | 26082 | Sec14l1 | NM_001166506.1 | chr11:116976485-117020582 |
| 25988 | Scn11a | NM_011887.3 | chr9:119662882-119734574 | | 26083 | Sec14l1 | NM_001166507.1 | chr11:116976485-117020582 |
| 25989 | Scn1a | NM_018733.2 | chr2:66108838-66278894 | | 26084 | Sec14l1 | NM_028777.3 | chr11:116976485-117020582 |
| 25990 | Scn1b | NM_011322.1 | chr7:31901542-31911964 | | 26085 | Sec14l1 | NR_029459.1 | chr11:116976485-117020582 |
| 25991 | Scn2a1 | NM_001099298.2 | chr2:65508501-65605504 | | 26086 | Sec14l2 | NM_144520.2 | chr11:3997042-4018732 |
| 25992 | Scn2b | NM_001014761.2 | chr9:44925959-44938153 | | 26087 | Sec14l3 | NM_001029937.2 | chr11:3964855-3978993 |
| 25993 | Scn3a | NM_018732.3 | chr2:65295174-65405549 | | 26088 | Sec14l4 | NM_146013.1 | chr11:3931784-3948012 |
| 25994 | Scn3b | NM_001083917.1 | chr9:40076800-40099203 | | 26089 | Sec14l5 | NM_001127725.1 | chr16:5147201-5184027 |
| 25995 | Scn3b | NM_001286614.1 | chr9:40076800-40099203 | | 26090 | Sec16a | NM_153125.2 | chr2:26264950-26300736 |
| 25996 | Scn3b | NM_178227.4 | chr9:40076800-40099203 | | 26091 | Sec16b | NM_001159986.1 | chr1:159436926-159498555 |
| 25997 | Scn4a | NM_133199.2 | chr11:106179906-106210704 | | 26092 | Sec16b | NM_033354.3 | chr1:159436926-159498555 |
| 25998 | Scn4b | NM_001013390.1 | chr9:44947124-44962144 | | 26093 | Sec16b | NR_027641.1 | chr1:159436926-159498555 |
| 25999 | Scn5a | NM_001253860.1 | chr9:119392525-119488134 | | 26094 | Sec22a | NM_133704.4 | chr16:35311216-35364004 |
| 26000 | Scn5a | NM_021544.4 | chr9:119392525-119488134 | | 26095 | Sec22b | NM_011342.4 | chr3:97705149-97726241 |
| 26001 | Scn7a | NM_009135.2 | chr2:66511482-66622967 | | 26096 | Sec22c | NM_001164562.1 | chr9:121589182-121614147 |
| 26002 | Scn8a | NM_001077499.2 | chr15:100701075-100876369 | | 26097 | Sec22c | NM_178677.1 | chr9:121589162-121614147 |
| 26003 | Scn8a | NM_011323.3 | chr15:100701075-100876369 | | 26098 | Sec23a | NM_009147.2 | chr12:60059370-60113004 |
| 26004 | Scn9a | NM_001290674.1 | chr2:66278936-66473019 | | 26099 | Sec23b | NM_001252543.1 | chr2:144381964-144416489 |
| 26005 | Scn9a | NM_001290675.1 | chr2:66278936-66473019 | | 26100 | Sec23b | NM_001252544.1 | chr2:144381964-144416489 |
| 26006 | Scn9a | NM_018852.2 | chr2:66278936-66473019 | | 26101 | Sec23b | NM_001252545.1 | chr2:144381964-144416489 |
| 26007 | Scnm1 | NM_001163573.1 | chr3:94933640-94937934 | | 26102 | Sec23b | NM_001281816.1 | chr2:144381964-144416489 |
| 26008 | Scnm1 | NM_027013.2 | chr3:94933640-94937934 | | 26103 | Sec23b | NM_019787.4 | chr2:144381964-144416489 |
| 26009 | Scnn1a | NM_011324.2 | chr6:125271357-125294960 | | 26104 | Sec23ip | NM_001029982.2 | chr7:135888383-135928349 |
| 26010 | Scnn1b | NM_001272023.1 | chr7:129008551-129062242 | | 26105 | Sec24a | NM_001290785.1 | chr11:51505764-51570336 |
| 26011 | Scnn1b | NM_011325.2 | chr7:129008551-129062242 | | 26106 | Sec24a | NM_175255.3 | chr11:51505764-51570336 |
| 26012 | Scnn1b | NR_073548.1 | chr7:129008551-129062242 | | 26107 | Sec24b | NM_267209.2 | chr3:129686102-129763825 |
| 26013 | Scnn1g | NM_011326.2 | chr7:128878020-128911991 | | 26108 | Sec24c | NM_001168273.1 | chr14:21493542-21514072 |
| 26014 | Sco1 | NM_001040026.1 | chr11:66866171-66880942 | | 26109 | Sec24c | NM_172596.2 | chr14:21493542-21514072 |
| 26015 | Sco2 | NM_001111288.1 | chr15:89202068-89204249 | | 26110 | Sec24d | NM_027135.2 | chr3:122970413-123068554 |
| 26016 | Scoc | NM_001039137.3 | chr8:85958390-85982295 | | 26111 | Sec31a | NM_026969.1 | chr5:100790667-100845253 |
| 26017 | Scoc | NM_001285992.1 | chr8:85958390-85982295 | | 26112 | Sec31b | NM_001033343.1 | chr19:44591446-44620338 |
| 26018 | Scoc | NM_019708.4 | chr8:85958390-85982295 | | 26113 | Sec61a1 | NM_016906.1 | chr6:88453600-88468794 |
| 26019 | Scp2 | NM_011327.4 | chr4:107716435-107791152 | | 26114 | Sec61a2 | NM_021305.3 | chr2:5792032-5816399 |
| 26020 | Scp2d1 | NM_025490.2 | chr2:144649401-144650151 | | 26115 | Sec61b | NM_024171.2 | chr4:47487532-47496105 |
| 26021 | Scpep1 | NM_029023.3 | chr11:88785334-88816756 | | 26116 | Sec61g | NM_001109971.1 | chr11:16401640-16408487 |
| 26022 | Scpep1os | NR_045955.1 | chr11:88767242-88797375 | | 26117 | Sec61g | NM_001109972.1 | chr11:16401640-16408487 |
| 26023 | Scrg1 | NM_009136.3 | chr8:59934719-59956382 | | 26118 | Sec61g | NM_011343.3 | chr11:16401640-16408487 |
| 26024 | Scrib | NM_134089.1 | chr15:75877616-75900160 | | 26119 | Sec62 | NM_027016.2 | chr3:30691797-30720185 |
| 26025 | Scrn1 | NM_027268.2 | chr6:54458809-54516376 | | 26120 | Sec63 | NM_153055.3 | chr10:42481301-42552320 |
| 26026 | Scrn2 | NM_146027.2 | chr11:96891265-96895274 | | 26121 | Secisbp2 | NM_029279.2 | chr13:51747082-51779015 |
| 26027 | Scrn3 | NM_029629.2 | chr2:73150708-73175864 | | 26122 | Secisbp2l | NM_177608.3 | chr2:125562721-125608606 |
| 26028 | Scrt1 | NM_130893.3 | chr15:76346632-76352559 | | 26123 | Sectm1a | NM_145373.2 | chr11:120928716-120942453 |
| 26029 | Scrt2 | NM_001160410.1 | chr2:151907264-151921538 | | 26124 | Sectm1b | NM_026907.3 | chr11:120914736-120924883 |
| 26030 | Sct | NM_001287171.1 | chr7:148464227-148465032 | | 26125 | Seh1l | NM_001039088.1 | chr18:67934529-67959597 |
| 26031 | Sct | NM_011328.3 | chr7:148464227-148465032 | | 26126 | Seh1l | NM_028112.2 | chr18:67934529-67959597 |
| 26032 | Sct | NR_105048.1 | chr7:148464227-148465032 | | 26127 | Sel1l | NM_001039089.1 | chr12:93044482-93087597 |
| 26033 | Sctr | NM_001012122.2 | chr1:121903556-121960109 | | 26128 | Sel1l | NM_011344.2 | chr12:93044482-93087597 |
| 26034 | Scube1 | NM_001271472.1 | chr15:83433012-83555469 | | 26129 | Sel1l2 | NM_001033296.2 | chr2:140055593-140215446 |
| 26035 | Scube1 | NM_001271473.1 | chr15:83433012-83555469 | | 26130 | Sel1l3 | NM_172710.3 | chr5:53498321-53604691 |
| 26036 | Scube1 | NM_022723.3 | chr15:83433012-83555469 | | 26131 | Sele | NM_011345.2 | chr1:165978364-165987808 |
| 26037 | Scube2 | NM_020052.2 | chr7:116942204-117009193 | | 26132 | Selenbp1 | NM_009150.3 | chr3:94737004-94748680 |
| 26038 | Scube3 | NM_001004366.1 | chr17:28279470-28308290 | | 26133 | Selenbp2 | NM_019414.2 | chr3:94497494-94508328 |
| 26039 | Scx | NM_198885.3 | chr15:76287868-76289898 | | 26134 | Selk | NM_019979.2 | chr14:30781565-30788260 |
| 26040 | Scyl1 | NM_023912.5 | chr19:5758427-5771461 | | 26135 | Sell | NM_001164059.1 | chr1:165992206-166010916 |
| 26041 | Scyl2 | NM_198021.2 | chr10:89102851-89149030 | | 26136 | Sell | NM_011346.2 | chr1:165992206-166010916 |
| 26042 | Scyl3 | NM_001286002.1 | chr1:165859230-165924912 | | 26137 | Selm | NM_053267.2 | chr11:3414704-3417354 |
| 26043 | Scyl3 | NM_001286003.1 | chr1:165859230-165924912 | | 26138 | Selo | NM_027905.2 | chr15:88919537-88930770 |
| 26044 | Scyl3 | NM_028776.5 | chr1:165859230-165924912 | | 26139 | Selp | NM_011347.2 | chr1:166045395-166080157 |
| 26045 | Sdad1 | NM_172713.2 | chr5:92713035-92739050 | | 26140 | Selplg | NM_009151.3 | chr5:114267806-114280510 |
| 26046 | Sdc1 | NM_011519.2 | chr12:8778201-8800493 | | 26141 | Selt | NM_001040396.2 | chr3:58380579-58397466 |

Fig. 25 - 139

| | | | |
|---|---|---|---|
| 26142 | Sema3a | NM_001243072.1 | chr5:13396783-13603485 |
| 26143 | Sema3a | NM_001243073.1 | chr5:13396783-13603485 |
| 26144 | Sema3a | NM_009152.4 | chr5:13396783-13603485 |
| 26145 | Sema3b | NM_001042779.2 | chr9:107500004-107511572 |
| 26146 | Sema3b | NM_001291537.1 | chr9:107500004-107511572 |
| 26147 | Sema3b | NM_001291538.1 | chr9:107500004-107511572 |
| 26148 | Sema3b | NM_001291539.1 | chr9:107500004-107511572 |
| 26149 | Sema3b | NM_009153.3 | chr9:107500004-107511572 |
| 26150 | Sema3b | NR_111986.1 | chr9:107500004-107511572 |
| 26151 | Sema3c | NM_013657.5 | chr5:17080633-17236085 |
| 26152 | Sema3d | NM_028852.4 | chr5:12383165-12588943 |
| 26153 | Sema3e | NM_011348.2 | chr5:14025275-14256689 |
| 26154 | Sema3f | NM_011349.3 | chr9:107583832-107612806 |
| 26155 | Sema3g | NM_001025379.1 | chr14:32031058-32042697 |
| 26156 | Sema4a | NM_001163489.1 | chr3:88239883-88265104 |
| 26157 | Sema4a | NM_001163490.1 | chr3:88239883-88265104 |
| 26158 | Sema4a | NM_001163491.1 | chr3:88239883-88265104 |
| 26159 | Sema4a | NM_013658.3 | chr3:88239883-88265104 |
| 26160 | Sema4b | NM_013659.4 | chr7:87331726-87371410 |
| 26161 | Sema4c | NM_001126047.3 | chr1:36605484-36615226 |
| 26162 | Sema4d | NM_001281880.1 | chr13:51796616-51889116 |
| 26163 | Sema4d | NM_013660.3 | chr13:51796616-51889116 |
| 26164 | Sema4f | NM_001113481.1 | chr6:82861878-82889744 |
| 26165 | Sema4f | NM_011350.4 | chr6:82861878-82889744 |
| 26166 | Sema4g | NM_011976.1 | chr19:45063833-45077885 |
| 26167 | Sema5a | NM_009154.2 | chr15:32174567-32626096 |
| 26168 | Sema5b | NM_013661.2 | chr16:35541447-35664344 |
| 26169 | Sema6a | NM_018744.2 | chr18:47404907-47528522 |
| 26170 | Sema6b | NM_001130456.1 | chr17:56262507-56279766 |
| 26171 | Sema6b | NM_013662.2 | chr17:56262507-56279766 |
| 26172 | Sema6c | NM_001272024.1 | chr3:94964341-94977972 |
| 26173 | Sema6c | NM_011351.2 | chr3:94964341-94977972 |
| 26174 | Sema6c | NR_073549.1 | chr3:94964341-94977972 |
| 26175 | Sema6c | NR_073550.1 | chr3:94964341-94977972 |
| 26176 | Sema6c | NR_073551.1 | chr3:94964341-94977972 |
| 26177 | Sema6d | NM_001290997.1 | chr2:123915704-124493525 |
| 26178 | Sema6d | NM_001291000.1 | chr2:123915704-124493525 |
| 26179 | Sema6d | NM_172537.4 | chr2:123915704-124493525 |
| 26180 | Sema6d | NM_199238.3 | chr2:123915704-124493525 |
| 26181 | Sema6d | NM_199239.3 | chr2:123915704-124493525 |
| 26182 | Sema6d | NM_199240.3 | chr2:123915704-124493525 |
| 26183 | Sema6d | NM_199241.3 | chr2:123915704-124493525 |
| 26184 | Sema7a | NM_011352.2 | chr9:57787941-57810672 |
| 26185 | Senp1 | NM_144851.5 | chr15:97869175-97924000 |
| 26186 | Senp2 | NM_029457.3 | chr16:22009556-22049342 |
| 26187 | Senp2 | NR_027488.1 | chr16:22009556-22049342 |
| 26188 | Senp3 | NM_001163571.1 | chr11:69486611-69495586 |
| 26189 | Senp3 | NM_030702.4 | chr11:69486611-69495586 |
| 26190 | Senp5 | NM_177103.4 | chr16:31959756-32003373 |
| 26191 | Senp6 | NM_146003.2 | chr9:79914709-79992587 |
| 26192 | Senp7 | NM_001003971.2 | chr16:56075521-56190124 |
| 26193 | Senp7 | NM_001003972.2 | chr16:56075521-56190124 |
| 26194 | Senp7 | NM_001003973.2 | chr16:56075521-56190124 |
| 26195 | Senp7 | NM_025483.4 | chr16:56075521-56190124 |
| 26196 | Senp8 | NM_001172068.1 | chr9:59582065-59598456 |
| 26197 | Senp8 | NM_001172069.1 | chr9:59582065-59598456 |
| 26198 | Senp8 | NM_001172070.1 | chr9:59582065-59598456 |
| 26199 | Senp8 | NM_001172071.1 | chr9:59582065-59598456 |
| 26200 | Senp8 | NM_027838.3 | chr9:59582065-59598456 |
| 26201 | Sephs1 | NM_175400.6 | chr2:4802609-4831602 |
| 26202 | Sephs2 | NM_009266.3 | chr7:134415394-134417573 |
| 26203 | Sepn1 | NM_029100.2 | chr4:134093806-134108081 |
| 26204 | Sepp1 | NM_001042613.1 | chr15:3220766-3230508 |
| 26205 | Sepp1 | NM_001042614.1 | chr15:3220766-3230508 |
| 26206 | Sepp1 | NM_009155.3 | chr15:3220766-3230508 |
| 26207 | Sepsecs | NM_172430.3 | chr5:53034645-53080940 |
| 26208 | Sept1 | NM_017461.2 | chr7:134357955-134361959 |
| 26209 | Sept10 | NM_001024910.3 | chr10:58604374-58684595 |
| 26210 | Sept10 | NM_001024911.2 | chr10:58604374-58684595 |
| 26211 | Sept11 | NM_001009818.1 | chr5:93522482-93603984 |
| 26212 | Sept12 | NM_027669.3 | chr16:4986950-4997945 |
| 26213 | Sept12 | NM_029374.1 | chr16:4986950-4997945 |
| 26214 | Sept14 | NM_028826.1 | chr5:130189265-130214386 |
| 26215 | Sep15 | NM_053102.2 | chr3:144233390-144260640 |
| 26216 | Sept2 | NM_001159717.1 | chr1:95375569-95406309 |
| 26217 | Sept2 | NM_001159718.1 | chr1:95375569-95406309 |
| 26218 | Sept2 | NM_001159719.1 | chr1:95375569-95406309 |
| 26219 | Sept2 | NM_010891.2 | chr1:95375569-95406309 |
| 26220 | Sept3 | NM_011889.2 | chr15:82105364-82124872 |
| 26221 | Sept4 | NM_001284392.1 | chr11:87391890-87404041 |
| 26222 | Sept4 | NM_001284394.1 | chr11:87391890-87404041 |
| 26223 | Sept4 | NM_001284398.1 | chr11:87391890-87404041 |
| 26224 | Sept4 | NM_011129.2 | chr11:87391890-87404041 |
| 26225 | Sept5 | NM_213614.2 | chr16:18621904-18630031 |
| 26226 | Sept6 | NM_001177323.2 | chrX:34450828-34529690 |
| 26227 | Sept6 | NM_001177324.1 | chrX:34450828-34529690 |
| 26228 | Sept6 | NM_001253706.1 | chrX:34450828-34529690 |
| 26229 | Sept6 | NM_019942.5 | chrX:34450828-34529690 |
| 26230 | Sept7 | NM_001205367.1 | chr9:25060039-25116156 |
| 26231 | Sept7 | NM_009859.4 | chr9:25060039-25116156 |
| 26232 | Sept8 | NM_001252332.1 | chr11:53333237-53357598 |
| 26233 | Sept8 | NM_001252333.1 | chr11:53333237-53357598 |
| 26234 | Sept8 | NM_033144.2 | chr11:53333237-53357598 |
| 26235 | Sept9 | NM_001113486.1 | chr11:117060974-117223639 |
| 26236 | Sept9 | NM_001113487.1 | chr11:117060974-117223639 |
| 26237 | Sept9 | NM_001113488.1 | chr11:117060974-117223639 |
| 26238 | Sept9 | NM_017380.2 | chr11:117060974-117223639 |
| 26239 | Sepw1 | NM_009156.2 | chr7:16502556-16507720 |
| 26240 | Serac1 | NM_001111017.1 | chr17:5941279-6079739 |
| 26241 | Serac1 | NM_177311.4 | chr17:5941279-6079739 |
| 26242 | Serbp1 | NM_001113564.1 | chr6:67216972-67239296 |
| 26243 | Serbp1 | NM_001113565.1 | chr6:67216972-67239296 |
| 26244 | Serbp1 | NM_001113566.1 | chr6:67216972-67239296 |
| 26245 | Serbp1 | NM_025814.2 | chr6:67216972-67239296 |
| 26246 | Serf1 | NM_011353.2 | chr13:100877973-100884188 |
| 26247 | Serf2 | NM_001290837.1 | chr2:121274933-121282500 |
| 26248 | Serf2 | NM_011354.3 | chr2:121274933-121282500 |
| 26249 | Serf2 | NR_110986.1 | chr2:121274933-121282500 |
| 26250 | Sergef | NM_013789.2 | chr7:53698528-53895177 |
| 26251 | Serhl | NM_023475.3 | chr15:82930635-82947101 |
| 26252 | Serinc1 | NM_019760.3 | chr10:57235581-57252335 |
| 26253 | Serinc2 | NM_001253386.1 | chr4:129930740-129952830 |
| 26254 | Serinc2 | NM_172702.3 | chr4:129930740-129952830 |
| 26255 | Serinc3 | NM_012032.4 | chr2:163449009-163470879 |
| 26256 | Serinc4 | NM_001025371.2 | chr2:121276913-121282500 |
| 26257 | Serinc5 | NM_172588.2 | chr13:93381092-93481901 |
| 26258 | Serp1 | NM_030685.3 | chr3:58325893-58329806 |
| 26259 | Serp2 | NM_001160326.1 | chr14:76932618-76956696 |
| 26260 | Serp2 | NR_027699.1 | chr14:76932618-76956696 |
| 26261 | Serpina10 | NM_144834.4 | chr12:104854884-104869615 |
| 26262 | Serpina11 | NM_001166350.1 | chr12:105218452-105228167 |
| 26263 | Serpina11 | NM_199314.2 | chr12:105218452-105228167 |
| 26264 | Serpina12 | NM_026535.2 | chr12:105266978-105282653 |
| 26265 | Serpina1a | NM_001252569.1 | chr12:105091504-105101829 |
| 26266 | Serpina1a | NM_009243.4 | chr12:105091504-105101829 |
| 26267 | Serpina1b | NM_009244.4 | chr12:104966365-104976399 |
| 26268 | Serpina1c | NM_009245.2 | chr12:105133135-105143160 |
| 26269 | Serpina1d | NM_009246.3 | chr12:105001796-105011843 |
| 26270 | Serpina1e | NM_009247.2 | chr12:105185141-105195107 |
| 26271 | Serpina1f | NM_001164742.1 | chr12:104926253-104933739 |
| 26272 | Serpina1f | NM_026687.2 | chr12:104926253-104933739 |
| 26273 | Serpina3a | NM_001167705.1 | chr12:105350933-105360106 |
| 26274 | Serpina3a | NM_028740.2 | chr12:105350933-105360106 |
| 26275 | Serpina3b | NM_173024.3 | chr12:105386205-105377755 |
| 26276 | Serpina3c | NM_008458.2 | chr12:105385116-105392082 |
| 26277 | Serpina3f | NM_001033335.3 | chr12:105452753-105480144 |
| 26278 | Serpina3f | NM_001168294.1 | chr12:105452753-105480144 |
| 26279 | Serpina3f | NM_001168295.1 | chr12:105452753-105480144 |
| 26280 | Serpina3g | NM_009251.1 | chr12:105452754-105480144 |
| 26281 | Serpina3h | NR_033450.1 | chr12:105486105-105492615 |
| 26282 | Serpina3i | NM_001199940.1 | chr12:105501331-105507575 |
| 26283 | Serpina3j | NM_001101472.2 | chr12:105552779-105558796 |
| 26284 | Serpina3k | NM_011458.2 | chr12:105576695-105583949 |
| 26285 | Serpina3m | NM_009253.2 | chr12:105625373-105632467 |
| 26286 | Serpina3n | NM_009252.2 | chr12:105644917-105652539 |
| 26287 | Serpina4-ps1 | NR_002861.2 | chr12:105316168-105325130 |
| 26288 | Serpina5 | NM_172953.3 | chr12:105339322-105344347 |
| 26289 | Serpina6 | NM_007618.2 | chr12:104884841-104895281 |
| 26290 | Serpina7 | NM_177920.5 | chrX:135613788-135619775 |
| 26291 | Serpina9 | NM_027997.2 | chr12:105234829-105251862 |
| 26292 | Serpinb10 | NM_001160307.1 | chr1:109425579-109445848 |
| 26293 | Serpinb10 | NM_198028.3 | chr1:109425579-109445848 |
| 26294 | Serpinb11 | NM_025867.2 | chr1:109258890-109277052 |
| 26295 | Serpinb12 | NM_001199213.1 | chr1:108831025-108853657 |
| 26296 | Serpinb12 | NM_027971.2 | chr1:108831025-108853657 |
| 26297 | Serpinb13 | NM_172852.3 | chr1:108877560-108897772 |
| 26298 | Serpinb1a | NM_025429.2 | chr13:32933960-32943054 |
| 26299 | Serpinb1b | NM_173052.2 | chr13:33175971-33186249 |
| 26300 | Serpinb1c | NM_173051.2 | chr13:32973265-32990009 |
| 26301 | Serpinb2 | NM_001174170.1 | chr1:109407999-109422177 |
| 26302 | Serpinb2 | NM_011111.4 | chr1:109407999-109422177 |
| 26303 | Serpinb3a | NM_009126.3 | chr1:108942163-108948880 |
| 26304 | Serpinb3b | NM_198680.2 | chr1:109050537-109057691 |
| 26305 | Serpinb3c | NM_201363.2 | chr1:109167777-109174948 |
| 26306 | Serpinb3d | NM_201376.1 | chr1:108974769-108980057 |
| 26307 | Serpinb5 | NM_009257.3 | chr1:108757756-108779925 |
| 26308 | Serpinb6a | NM_001164117.1 | chr13:34009786-34094663 |
| 26309 | Serpinb6a | NM_001164118.1 | chr13:34009786-34094663 |
| 26310 | Serpinb6a | NM_001243192.1 | chr13:34009786-34094663 |
| 26311 | Serpinb6a | NM_009254.3 | chr13:34009786-34094663 |
| 26312 | Serpinb6b | NM_011454.1 | chr13:33057381-33070906 |
| 26313 | Serpinb6c | NM_148942.2 | chr13:33971684-33997577 |
| 26314 | Serpinb6d | NM_001076790.2 | chr13:33753273-33763454 |
| 26315 | Serpinb6e | NM_001045535.2 | chr13:33924213-33935277 |
| 26316 | Serpinb7 | NM_027548.3 | chr1:109319265-109349266 |
| 26317 | Serpinb8 | NM_001159748.1 | chr1:109486582-109505555 |
| 26318 | Serpinb8 | NM_011459.4 | chr1:109486582-109505555 |
| 26319 | Serpinb9 | NM_009256.3 | chr13:33096409-33109824 |
| 26320 | Serpinb9b | NM_011452.2 | chr13:33119282-33132427 |
| 26321 | Serpinb9c | NM_001164524.1 | chr13:33241143-33251623 |
| 26322 | Serpinb9c | NM_011453.6 | chr13:33241143-33251623 |
| 26323 | Serpinb9d | NM_011460.1 | chr13:33284827-33295849 |
| 26324 | Serpinb9e | NM_011456.2 | chr13:33341478-33352715 |
| 26325 | Serpinb9f | NM_183197.1 | chr13:33415945-33427235 |
| 26326 | Serpinb9g | NM_011455.3 | chr13:33576658-33587869 |
| 26327 | Serpinc1 | NM_080844.4 | chr1:162908736-162933145 |
| 26328 | Serpind1 | NM_008223.3 | chr16:17331464-17343665 |
| 26329 | Serpine1 | NM_008871.2 | chr5:137537375-137548142 |
| 26330 | Serpine2 | NM_009255.2 | chr1:79790895-79855240 |
| 26331 | Serpine3 | NM_001199945.1 | chr14:63282504-63311080 |

Fig. 25 - 140

| | | | | | | | |
|---|---|---|---|---|---|---|---|
| 26332 | Serpinf1 | NM_011340.3 | chr11:75223530-75236125 | 26427 | Sgce | NM_001130189.1 | chr6:4624349-4697204 |
| 26333 | Serpinf2 | NM_008878.2 | chr11:75245237-75253003 | 26428 | Sgce | NM_001130190.1 | chr6:4624349-4697204 |
| 26334 | Serping1 | NM_009776.3 | chr2:84605516-84615586 | 26429 | Sgce | NM_001130191.1 | chr6:4624349-4697204 |
| 26335 | Serpinh1 | NM_001111043.1 | chr7:106493884-106501749 | 26430 | Sgce | NM_011360.3 | chr6:4624349-4697204 |
| 26336 | Serpinh1 | NM_001111044.1 | chr7:106493884-106501749 | 26431 | Sgcg | NM_011892.3 | chr14:61837952-61877327 |
| 26337 | Serpinh1 | NM_001285776.1 | chr7:106493884-106501749 | 26432 | Sgcz | NM_145841.2 | chr8:38585608-39724562 |
| 26338 | Serpinh1 | NM_009825.2 | chr7:106493884-106501749 | 26433 | Sgip1 | NM_001285852.1 | chr4:102432739-102684570 |
| 26339 | Serpini1 | NM_009250.2 | chr3:75361454-75446445 | 26434 | Sgip1 | NM_001285859.1 | chr4:102432739-102684570 |
| 26340 | Serpini2 | NM_026460.3 | chr3:75046278-75074000 | 26435 | Sgip1 | NM_001285860.1 | chr4:102432739-102684570 |
| 26341 | Sertad1 | NM_018820.3 | chr7:28271971-28275333 | 26436 | Sgip1 | NM_001285862.1 | chr4:102432739-102684570 |
| 26342 | Sertad2 | NM_001038625.1 | chr11:20443255-20553026 | 26437 | Sgip1 | NM_144906.2 | chr4:102432739-102684570 |
| 26343 | Sertad2 | NM_021372.2 | chr11:20443255-20553026 | 26438 | Sgk1 | NM_001161845.2 | chr10:21601989-21719708 |
| 26344 | Sertad3 | NM_133210.2 | chr7:28258858-28262383 | 26439 | Sgk1 | NM_001161847.2 | chr10:21601989-21719708 |
| 26345 | Sertad4 | NM_001177794.1 | chr1:194670681-194681946 | 26440 | Sgk1 | NM_001161848.2 | chr10:21601989-21719708 |
| 26346 | Sertad4 | NM_198247.2 | chr1:194670681-194681946 | 26441 | Sgk1 | NM_001161849.2 | chr10:21601989-21719708 |
| 26347 | Sertm1 | NM_177854.4 | chr9:54700990-54719809 | 26442 | Sgk1 | NM_001161850.2 | chr10:21601989-21719708 |
| 26348 | Sesn1 | NM_001013370.2 | chr10:41530379-41628242 | 26443 | Sgk1 | NM_011361.3 | chr10:21601989-21719708 |
| 26349 | Sesn1 | NM_001162908.1 | chr10:41530379-41628242 | 26444 | Sgk2 | NM_001291152.1 | chr2:162813216-162839875 |
| 26350 | Sesn2 | NM_144907.1 | chr4:132048721-132066371 | 26445 | Sgk2 | NM_001291154.1 | chr2:162813216-162839875 |
| 26351 | Sesn3 | NM_030261.4 | chr9:14080744-14130578 | 26446 | Sgk2 | NM_013731.3 | chr2:162813216-162839875 |
| 26352 | Sestd1 | NM_175465.6 | chr2:77018396-77118649 | 26447 | Sgk3 | NM_001037759.1 | chr1:9788210-9892649 |
| 26353 | Set | NM_001204875.1 | chr2:29917515-29928097 | 26448 | Sgk3 | NM_133220.2 | chr1:9788210-9892649 |
| 26354 | Set | NM_023871.4 | chr2:29917515-29928097 | 26449 | Sgk3 | NM_175547.3 | chr1:9788210-9892649 |
| 26355 | Setbp1 | NM_053099.2 | chr18:78947116-79306130 | 26450 | Sgms1 | NM_001168525.1 | chr19:32197216-32462944 |
| 26356 | Setd1a | NM_178029.3 | chr7:134920902-134943633 | 26451 | Sgms1 | NM_001168526.1 | chr19:32197216-32462944 |
| 26357 | Setd1b | NM_001040398.2 | chr5:123592201-123618639 | 26452 | Sgms1 | NM_144792.4 | chr19:32197216-32462944 |
| 26358 | Setd2 | NM_001081340.2 | chr9:110485100-110521137 | 26453 | Sgms2 | NM_028943.5 | chr3:131021903-131047841 |
| 26359 | Setd3 | NM_028262.3 | chr12:109344640-109417494 | 26454 | Sgol1 | NM_028232.2 | chr17:53814111-53828640 |
| 26360 | Setd4 | NM_145482.3 | chr16:93583705-93604060 | 26455 | Sgol2 | NM_001177867.1 | chr1:58042183-58083121 |
| 26361 | Setd5 | NM_028385.1 | chr6:113027632-113103418 | 26456 | Sgol2 | NM_199007.2 | chr1:58042183-58083121 |
| 26362 | Setd6 | NM_001035123.3 | chr8:98239812-98242904 | 26457 | Sgpl1 | NM_009163.3 | chr10:60561389-60610413 |
| 26363 | Setd7 | NM_080793.5 | chr3:51319240-51364745 | 26458 | Sgpp1 | NM_030750.3 | chr12:76815234-76836716 |
| 26364 | Setd8 | NM_030241.2 | chr5:124889938-124912316 | 26459 | Sgpp2 | NM_001004173.2 | chr1:78306921-78416861 |
| 26365 | Setdb1 | NM_001163641.1 | chr3:95119173-95161124 | 26460 | Sgsh | NM_018822.3 | chr11:119204803-119216824 |
| 26366 | Setdb1 | NM_001163642.1 | chr3:95119173-95161124 | 26461 | Sgsm1 | NM_001162965.1 | chr5:113672239-113739806 |
| 26367 | Setdb1 | NM_018877.3 | chr3:95119173-95161124 | 26462 | Sgsm1 | NM_001254731.1 | chr5:113672239-113739806 |
| 26368 | Setdb2 | NM_001081024.1 | chr14:60020847-60059714 | 26463 | Sgsm1 | NM_172718.3 | chr5:113672239-113739806 |
| 26369 | Setmar | NM_001276356.1 | chr6:108015038-108027121 | 26464 | Sgsm1 | NR_027934.1 | chr5:113672239-113739806 |
| 26370 | Setmar | NM_178391.1 | chr6:108015038-108027121 | 26465 | Sgsm1 | NR_027936.1 | chr5:113672239-113739806 |
| 26371 | Setx | NM_198033.2 | chr2:28980511-29037991 | 26466 | Sgsm2 | NM_197943.2 | chr11:74662766-74710582 |
| 26372 | Sez6 | NM_001291225.1 | chr11:77744340-77792554 | 26467 | Sgsm3 | NM_134091.2 | chr15:80808195-80842720 |
| 26373 | Sez6 | NM_021286.4 | chr11:77744340-77792554 | 26468 | Sgta | NM_024499.1 | chr10:80506817-80522899 |
| 26374 | Sez6l | NM_001253916.1 | chr5:112848170-113006218 | 26469 | Sgtb | NM_144838.1 | chr13:104899869-104931521 |
| 26375 | Sez6l | NM_001253917.1 | chr5:112848170-113006218 | 26470 | Sh2b1 | NM_001081459.2 | chr7:133610506-133618644 |
| 26376 | Sez6l | NM_019982.3 | chr5:112848170-113006218 | 26471 | Sh2b1 | NM_001289538.1 | chr7:133610506-133618644 |
| 26377 | Sez6l2 | NM_001252566.1 | chr7:134094048-134114120 | 26472 | Sh2b1 | NM_001289539.1 | chr7:133610506-133618644 |
| 26378 | Sez6l2 | NM_001252567.1 | chr7:134094048-134114120 | 26473 | Sh2b1 | NM_001289540.1 | chr7:133610506-133618644 |
| 26379 | Sez6l2 | NM_144926.3 | chr7:134094048-134114120 | 26474 | Sh2b1 | NM_001289541.1 | chr7:133610506-133618644 |
| 26380 | Sf1 | NM_001110791.1 | chr19:6363689-6378038 | 26475 | Sh2b1 | NM_001289542.1 | chr7:133610506-133618644 |
| 26381 | Sf1 | NM_011750.2 | chr19:6363689-6378038 | 26476 | Sh2b1 | NM_011363.3 | chr7:133610506-133618644 |
| 26382 | Sf3a1 | NM_026175.5 | chr11:4060356-4082544 | 26477 | Sh2b1 | NR_110346.1 | chr7:133610506-133618644 |
| 26383 | Sf3a2 | NM_013651.4 | chr10:80261479-80267667 | 26478 | Sh2b2 | NM_018825.4 | chr5:136694018-136720773 |
| 26384 | Sf3a3 | NM_029757.3 | chr4:124392105-124400666 | 26479 | Sh2b3 | NM_008507.4 | chr5:122265480-122286868 |
| 26385 | Sf3b1 | NM_031179.2 | chr1:55042012-55084322 | 26480 | Sh2d1a | NM_011364.3 | chrX:39855784-39875252 |
| 26386 | Sf3b2 | NM_030109.2 | chr19:5273920-5295455 | 26481 | Sh2d1b1 | NM_012009.4 | chr1:172207454-172215793 |
| 26387 | Sf3b3 | NM_133953.3 | chr8:113334392-113370703 | 26482 | Sh2d1b2 | NM_001033499.1 | chr1:172163001-172181718 |
| 26388 | Sf3b4 | NM_153053.4 | chr3:95976472-95981487 | 26483 | Sh2d2a | NM_001025571.2 | chr3:87650676-87659644 |
| 26389 | Sf3b5 | NM_175102.4 | chr10:12728255-12728989 | 26484 | Sh2d2a | NM_021309.3 | chr3:87650676-87659644 |
| 26390 | Sf3b6 | NM_025323.2 | chr12:4824413-4834465 | 26485 | Sh2d3c | NM_001252547.1 | chr2:32576574-32610527 |
| 26391 | Sfi1 | NM_030207.2 | chr11:3031853-3093466 | 26486 | Sh2d3c | NM_013781.3 | chr2:32576574-32610527 |
| 26392 | Sfmbt1 | NM_001166531.1 | chr14:31528034-31635907 | 26487 | Sh2d3c | NR_045535.1 | chr2:32576574-32610527 |
| 26393 | Sfmbt1 | NM_001166532.1 | chr14:31528034-31635907 | 26488 | Sh2d4a | NM_028182.1 | chr8:70800426-70871603 |
| 26394 | Sfmbt1 | NM_019460.2 | chr14:31528034-31635907 | 26489 | Sh2d4b | NM_177816.3 | chr14:41629156-41706254 |
| 26395 | Sfmbt2 | NM_001198808.1 | chr2:10292077-10516880 | 26490 | Sh2d5 | NM_001099631.1 | chr4:137806325-137816883 |
| 26396 | Sfmbt2 | NM_001198809.1 | chr2:10292077-10516880 | 26491 | Sh2d7 | NM_173778.3 | chr9:54386790-54392827 |
| 26397 | Sfmbt2 | NM_177386.5 | chr2:10292077-10516880 | 26492 | Sh3bgr | NM_015825.2 | chr16:96422076-96450540 |
| 26398 | Sfn | NM_018754.2 | chr4:133156470-133158003 | 26493 | Sh3bgrl | NM_019989.2 | chrX:106290745-106357806 |
| 26399 | Sfpq | NM_023603.3 | chr4:126698544-126714258 | 26494 | Sh3bgrl2 | NM_172507.5 | chr9:83441944-83493898 |
| 26400 | Sfpq | NR_045010.1 | chr4:126698544-126714258 | 26495 | Sh3bgrl3 | NM_080559.1 | chr4:133683320-133684668 |
| 26401 | Sfr1 | NM_134514.2 | chr19:47806245-47810078 | 26496 | Sh3bp1 | NM_009164.2 | chr15:78730215-78742482 |
| 26402 | Sfrp1 | NM_013834.3 | chr8:24521973-24560104 | 26497 | Sh3bp2 | NM_001145858.1 | chr5:34868432-34906288 |
| 26403 | Sfrp2 | NM_009144.2 | chr3:83570242-83578236 | 26498 | Sh3bp2 | NM_001145859.1 | chr5:34868432-34906288 |
| 26404 | Sfrp4 | NM_016687.3 | chr13:19715043-19724692 | 26499 | Sh3bp2 | NM_011893.3 | chr5:34868432-34906288 |
| 26405 | Sfrp5 | NM_018780.3 | chr19:42272460-42276742 | 26500 | Sh3bp4 | NM_133816.2 | chr1:90967036-91050368 |
| 26406 | Sfswap | NM_172276.3 | chr5:130077105-130077259 | 26501 | Sh3bp5 | NM_011894.2 | chr14:32187149-32249219 |
| 26407 | Sft2d1 | NM_134514.2 | chr17:78503968-78520307 | 26502 | Sh3bp5l | NM_001161338.2 | chr11:58144219-58161230 |
| 26408 | Sft2d2 | NM_145512.4 | chr1:167104471-167124564 | 26503 | Sh3bp5l | NM_024480.5 | chr11:58144219-58161230 |
| 26409 | Sft2d3 | NM_026006.1 | chr18:32068747-32071557 | 26504 | Sh3d19 | NM_001082414.2 | chr3:85888355-85934443 |
| 26410 | Sfta2 | NM_001185194.1 | chr17:35786652-35787514 | 26505 | Sh3d21 | NM_001162533.1 | chr4:125827845-125840585 |
| 26411 | Sftpa1 | NM_023134.4 | chr14:41945076-41949662 | 26506 | Sh3d21 | NM_025856.3 | chr4:125827845-125840585 |
| 26412 | Sftpb | NM_001282071.2 | chr6:72254603-72264367 | 26507 | Sh3gl1 | NM_001252471.1 | chr17:56148623-56176060 |
| 26413 | Sftpb | NM_147779.2 | chr6:72254603-72264367 | 26508 | Sh3gl1 | NM_013664.3 | chr17:56148623-56176060 |
| 26414 | Sftpc | NM_011359.2 | chr14:70920748-70923888 | 26509 | Sh3gl2 | NM_019535.2 | chr4:84851359-85035283 |
| 26415 | Sftpd | NM_009160.2 | chr14:41985506-41998487 | 26510 | Sh3gl3 | NM_001277954.1 | chr7:89408417-89455930 |
| 26416 | Sfxn1 | NM_027324.5 | chr13:54167213-54203714 | 26511 | Sh3gl3 | NM_001277955.1 | chr7:89408417-89455930 |
| 26417 | Sfxn2 | NM_053196.3 | chr19:46647854-46671390 | 26512 | Sh3gl3 | NM_017400.6 | chr7:89408417-89455930 |
| 26418 | Sfxn3 | NM_001178012.1 | chr19:45122065-45130873 | 26513 | Sh3glb1 | NM_001282037.1 | chr3:144346641-144383299 |
| 26419 | Sfxn3 | NM_001178013.1 | chr19:45122065-45130873 | 26514 | Sh3glb1 | NM_001282042.1 | chr3:144346641-144383299 |
| 26420 | Sfxn3 | NM_053197.4 | chr19:45122065-45130873 | 26515 | Sh3glb1 | NM_019464.3 | chr3:144346641-144383299 |
| 26421 | Sfxn4 | NM_053198.3 | chr19:60913179-60937333 | 26516 | Sh3glb2 | NM_001289709.1 | chr2:30200296-30214836 |
| 26422 | Sfxn5 | NM_178639.4 | chr6:85163044-85283416 | 26517 | Sh3glb2 | NM_001289710.1 | chr2:30200296-30214836 |
| 26423 | Sgca | NM_009161.4 | chr11:94824091-94837641 | 26518 | Sh3glb2 | NM_139302.2 | chr2:30200296-30214836 |
| 26424 | Sgcb | NM_011890.4 | chr5:74025987-74038970 | 26519 | Sh3kbp1 | NM_001135727.2 | chrX:156065203-156413852 |
| 26425 | Sgcd | NM_011891.4 | chr11:46792284-47192804 | 26520 | Sh3kbp1 | NM_001135728.2 | chrX:156065203-156413852 |
| 26426 | Sgce | NM_001130188.1 | chr6:4624349-4697204 | 26521 | Sh3kbp1 | NM_001290661.1 | chrX:156065203-156413852 |

Fig. 25 - 141

| | | | |
|---|---|---|---|
| 26522 | Sh3kbp1 | NM_001290664.1 | chrX:156065203-156413852 |
| 26523 | Sh3kbp1 | NM_021389.6 | chrX:156065203-156413852 |
| 26524 | Sh3kbp1 | NR_110969.1 | chrX:156065203-156413852 |
| 26525 | Sh3kbp1 | NR_110970.1 | chrX:156065203-156413852 |
| 26526 | Sh3pxd2a | NM_001164717.1 | chr19:47334663-47538901 |
| 26527 | Sh3pxd2a | NM_008018.4 | chr19:47334663-47538901 |
| 26528 | Sh3pxd2b | NM_177364.3 | chr11:32247810-32328183 |
| 26529 | Sh3rf1 | NM_021506.2 | chr8:63702968-63874869 |
| 26530 | Sh3rf2 | NM_001146299.1 | chr18:42213363-42318349 |
| 26531 | Sh3rf2 | NM_172966.3 | chr18:42213363-42318349 |
| 26532 | Sh3rf3 | NM_172788.3 | chr10:58276106-58601664 |
| 26533 | Sh3tc1 | NM_194344.2 | chr5:36039828-36071925 |
| 26534 | Sh3tc2 | NM_172628.2 | chr18:62112728-62175373 |
| 26535 | Sh3yl1 | NM_001289480.1 | chr12:31596533-31645025 |
| 26536 | Sh3yl1 | NM_013709.5 | chr12:31596533-31645025 |
| 26537 | Sh3yl1 | NR_110343.1 | chr12:31596533-31645025 |
| 26538 | Shank1 | NM_001034115.1 | chr7:51565633-51613723 |
| 26539 | Shank2 | NM_001081370.2 | chr7:151361424-151608580 |
| 26540 | Shank2 | NM_001133373.2 | chr7:151361424-151608580 |
| 26541 | Shank3 | NM_021423.3 | chr15:89330287-89390691 |
| 26542 | Sharpin | NM_025340.2 | chr15:76177469-76181540 |
| 26543 | Shb | NM_001033306.1 | chr4:45436147-45543700 |
| 26544 | Shbg | NM_011367.2 | chr11:69428317-69431407 |
| 26545 | Shc1 | NM_001113331.2 | chr3:89222472-89233951 |
| 26546 | Shc1 | NM_011368.5 | chr3:89222472-89233951 |
| 26547 | Shc2 | NM_001024539.1 | chr10:79080682-79100663 |
| 26548 | Shc3 | NM_009167.3 | chr13:51526410-51662453 |
| 26549 | Shc4 | NM_199022.2 | chr2:125453183-125549884 |
| 26550 | Shcbp1 | NM_011369.2 | chr8:4735979-4779534 |
| 26551 | Shcbp1l | NM_001033162.2 | chr1:155272338-155299704 |
| 26552 | Shd | NM_001159523.1 | chr7:56109904-56116042 |
| 26553 | Shd | NM_009168.2 | chr17:56109904-56116042 |
| 26554 | She | NM_172530.3 | chr3:89635291-89662768 |
| 26555 | Shf | NM_001013829.2 | chr2:122174627-122194654 |
| 26556 | Shfm1 | NM_009169.2 | chr6:6508274-6528658 |
| 26557 | Shh | NM_009170.3 | chr5:28783380-28793641 |
| 26558 | Shisa2 | NM_145463.5 | chr14:60244117-60250497 |
| 26559 | Shisa3 | NM_001033415.3 | chr5:67999121-68005226 |
| 26560 | Shisa4 | NM_175259.4 | chr1:137268032-137271640 |
| 26561 | Shisa5 | NM_001284332.1 | chr9:108941080-108960306 |
| 26562 | Shisa5 | NM_025858.3 | chr9:108941080-108960306 |
| 26563 | Shisa5 | NM_026381.5 | chr9:108941080-108960306 |
| 26564 | Shisa6 | NM_001034874.3 | chr11:66025226-66339628 |
| 26565 | Shisa7 | NM_001290291.1 | chr7:4777153-4796298 |
| 26566 | Shisa7 | NM_172737.4 | chr7:4777153-4796298 |
| 26567 | Shisa9 | NM_001174086.1 | chr16:11984205-12270997 |
| 26568 | Shisa9 | NM_028277.2 | chr16:11984205-12270997 |
| 26569 | Shkbp1 | NM_138676.2 | chr7:28127151-28141027 |
| 26570 | Shmt1 | NM_009171.2 | chr11:60602398-60624767 |
| 26571 | Shmt2 | NM_001252316.1 | chr10:126951994-126959500 |
| 26572 | Shmt2 | NM_028230.4 | chr10:126951994-126959500 |
| 26573 | Shoc2 | NM_001168505.1 | chr19:53966720-54107768 |
| 26574 | Shoc2 | NM_013566.6 | chr19:53966720-54107768 |
| 26575 | Shox2 | NM_013665.1 | chr3:66777190-66785693 |
| 26576 | Shpk | NM_029031.3 | chr11:73012983-73038008 |
| 26577 | Shprh | NM_001177707.1 | chr10:10869227-10935071 |
| 26578 | Shprh | NM_001284354.1 | chr10:10869227-10935071 |
| 26579 | Shprh | NM_172937.3 | chr10:10869227-10935071 |
| 26580 | Shq1 | NM_181590.5 | chr6:100523075-100621151 |
| 26581 | Shroom1 | NM_001290789.1 | chr11:53270706-53281268 |
| 26582 | Shroom1 | NM_027917.3 | chr11:53270706-53281268 |
| 26583 | Shroom2 | NM_001290694.1 | chrX:149044051-149204029 |
| 26584 | Shroom2 | NM_001290685.1 | chrX:149044051-149204029 |
| 26585 | Shroom2 | NM_001290686.1 | chrX:149044051-149204029 |
| 26586 | Shroom2 | NM_001290687.1 | chrX:149044051-149204029 |
| 26587 | Shroom2 | NM_172441.3 | chrX:149044051-149204029 |
| 26588 | Shroom3 | NM_001077595.2 | chr5:93112460-93394785 |
| 26589 | Shroom3 | NM_001077596.2 | chr5:93112460-93394785 |
| 26590 | Shroom3 | NM_015756.2 | chr5:93112460-93394785 |
| 26591 | Shroom4 | NM_001040459.1 | chrX:5977263-6210835 |
| 26592 | Siae | NM_013734.3 | chr9:37421431-37455903 |
| 26593 | Siah1a | NM_009172.2 | chr8:89247837-89269905 |
| 26594 | Siah1b | NM_009173.2 | chrX:160508634-160513981 |
| 26595 | Siah2 | NM_009174.3 | chr3:58478870-58496310 |
| 26596 | Siah3 | NM_001128093.1 | chr14:75855788-75925948 |
| 26597 | Sidt1 | NM_001159419.1 | chr16:44240292-44332951 |
| 26598 | Sidt1 | NM_198034.3 | chr16:44240292-44332951 |
| 26599 | Sidt2 | NM_001289668.1 | chr9:45745939-45763332 |
| 26600 | Sidt2 | NM_172257.4 | chr9:45745939-45763332 |
| 26601 | Sigirr | NM_023059.3 | chr7:148277073-148286445 |
| 26602 | Siglec1 | NM_011426.3 | chr2:130894955-130912501 |
| 26603 | Siglec15 | NM_001101038.1 | chr18:78240352-78254007 |
| 26604 | Siglec5 | NM_001271019.1 | chr7:50606710-50614840 |
| 26605 | Siglec5 | NM_145581.2 | chr7:50606710-50614840 |
| 26606 | Siglece | NM_031181.2 | chr7:50906439-50915931 |
| 26607 | Siglecg | NM_172900.3 | chr7:50663649-50673219 |
| 26608 | Siglech | NM_178706.4 | chr7:50823547-63034203 |
| 26609 | Sigmar1 | NM_001286538.1 | chr4:41685365-41688232 |
| 26610 | Sigmar1 | NM_001286539.1 | chr4:41685365-41688232 |
| 26611 | Sigmar1 | NM_001286540.1 | chr4:41685365-41688232 |
| 26612 | Sigmar1 | NM_001286541.1 | chr4:41685365-41688232 |
| 26613 | Sigmar1 | NM_001286542.1 | chr4:41685365-41688232 |
| 26614 | Sigmar1 | NM_001286551.1 | chr4:41685365-41688232 |
| 26615 | Sigmar1 | NM_001286605.1 | chr4:41685365-41688232 |
| 26616 | Sigmar1 | NM_011014.3 | chr4:41685365-41688232 |
| 26617 | Sik1 | NM_010831.2 | chr17:31981194-31992737 |
| 26618 | Sik2 | NM_178710.3 | chr9:50700906-50817178 |
| 26619 | Sik3 | NM_027498.3 | chr9:45820902-46032277 |
| 26620 | Sike1 | NM_025679.3 | chr3:102799662-102807837 |
| 26621 | Sil1 | NM_030749.2 | chr18:35426049-35658579 |
| 26622 | Sim1 | NM_011376.1 | chr10:50615456-50708958 |
| 26623 | Sim2 | NM_011377.2 | chr16:94085504-94348638 |
| 26624 | Simc1 | NM_178947.4 | chr13:54605166-54652651 |
| 26625 | Sin3a | NM_001110350.1 | chr9:56919846-56976175 |
| 26626 | Sin3a | NM_001110351.1 | chr9:56919846-56976175 |
| 26627 | Sin3a | NM_011378.2 | chr9:56919846-56976175 |
| 26628 | Sin3b | NM_001113248.2 | chr8:75247168-75282102 |
| 26629 | Sin3b | NM_009188.4 | chr8:75247168-75282102 |
| 26630 | Sipa1 | NM_001164480.1 | chr19:5651184-5663707 |
| 26631 | Sipa1 | NM_001164481.1 | chr19:5651184-5663707 |
| 26632 | Sipa1 | NM_001164482.1 | chr19:5651184-5663707 |
| 26633 | Sipa1 | NM_001164568.1 | chr19:5651184-5663707 |
| 26634 | Sipa1 | NM_011379.4 | chr19:5651184-5663707 |
| 26635 | Sipa1l1 | NM_001167963.1 | chr12:83271002-83552771 |
| 26636 | Sipa1l1 | NM_172579.3 | chr12:83271002-83552771 |
| 26637 | Sipa1l2 | NM_001081337.1 | chr8:127941962-128016610 |
| 26638 | Sipa1l3 | NM_001081028.1 | chr7:30105396-30290479 |
| 26639 | Sirpa | NM_001177646.1 | chr2:129418574-129457964 |
| 26640 | Sirpa | NM_001177647.2 | chr2:129418574-129457964 |
| 26641 | Sirpa | NM_001291019.1 | chr2:129418574-129457964 |
| 26642 | Sirpa | NM_001291020.1 | chr2:129418574-129457964 |
| 26643 | Sirpa | NM_001291021.1 | chr2:129418574-129457964 |
| 26644 | Sirpa | NM_001291022.1 | chr2:129418574-129457964 |
| 26645 | Sirpa | NM_007547.2 | chr2:129418574-129457964 |
| 26646 | Sirpb1a | NM_001002898.1 | chr3:15371826-15426427 |
| 26647 | Sirpb1b | NM_001173460.1 | chr3:15495753-15575065 |
| 26648 | Sirt1 | NM_001159589.1 | chr10:62781752-62801783 |
| 26649 | Sirt1 | NM_019812.2 | chr10:62781752-62801783 |
| 26650 | Sirt2 | NM_001122765.1 | chr7:29551770-29573684 |
| 26651 | Sirt2 | NM_001122766.1 | chr7:29551770-29573684 |
| 26652 | Sirt2 | NM_022432.4 | chr7:29551770-29573684 |
| 26653 | Sirt3 | NM_001127351.1 | chr7:148043295-148068208 |
| 26654 | Sirt3 | NM_001177804.1 | chr7:148043295-148068208 |
| 26655 | Sirt3 | NM_022433.2 | chr7:148043295-148068208 |
| 26656 | Sirt4 | NM_001167691.1 | chr5:115928018-115934493 |
| 26657 | Sirt4 | NM_133760.1 | chr5:115928018-115934493 |
| 26658 | Sirt5 | NM_178848.3 | chr13:43466084-43490572 |
| 26659 | Sirt6 | NM_001163430.1 | chr10:81084530-81090353 |
| 26660 | Sirt6 | NM_181586.3 | chr10:81084530-81090353 |
| 26661 | Sirt7 | NM_153056.2 | chr11:120479686-120486316 |
| 26662 | Sis | NM_001081137.1 | chr3:72692481-72770788 |
| 26663 | Sit1 | NM_019436.3 | chr4:43494954-43496581 |
| 26664 | Siva1 | NM_001161737.1 | chr12:113883038-113887363 |
| 26665 | Siva1 | NM_013929.2 | chr12:113883038-113887363 |
| 26666 | Six1 | NM_009189.3 | chr12:74142813-74147699 |
| 26667 | Six2 | NM_011380.2 | chr17:86083607-86087594 |
| 26668 | Six3 | NM_011381.4 | chr17:86020173-86025531 |
| 26669 | Six3os1 | NR_015385.2 | chr17:86001271-86017736 |
| 26670 | Six3os1 | NR_015386.2 | chr17:86001271-86017736 |
| 26671 | Six3os1 | NR_015387.2 | chr17:86001271-86017736 |
| 26672 | Six3os1 | NR_038082.1 | chr17:86001271-86017736 |
| 26673 | Six3os1 | NR_038083.1 | chr17:86001271-86017736 |
| 26674 | Six3os1 | NR_038084.1 | chr17:86001271-86017736 |
| 26675 | Six3os1 | NR_038085.1 | chr17:86001271-86017736 |
| 26676 | Six3os1 | NR_038086.1 | chr17:86001271-86017736 |
| 26677 | Six4 | NM_011382.2 | chr12:74201245-74214232 |
| 26678 | Six5 | NM_011383.1 | chr7:19679892-19683694 |
| 26679 | Six6 | NM_011384.4 | chr12:74040931-74045886 |
| 26680 | Ska1 | NM_001164355.1 | chr18:74354952-74367472 |
| 26681 | Ska1 | NM_025581.4 | chr18:74354952-74367472 |
| 26682 | Ska2 | NM_025377.3 | chr11:86922763-86936476 |
| 26683 | Ska3 | NM_198605.3 | chr14:58425397-58445000 |
| 26684 | Skap1 | NM_001033186.3 | chr11:96325904-96620936 |
| 26685 | Skap1 | NM_001177898.1 | chr11:96325904-96620936 |
| 26686 | Skap1 | NM_001177899.1 | chr11:96325904-96620936 |
| 26687 | Skap2 | NM_018773.2 | chr6:51809163-51962548 |
| 26688 | Ski | NM_011385.2 | chr4:154528183-154596644 |
| 26689 | Skida1 | NM_028317.2 | chr2:17965713-17970076 |
| 26690 | Skil | NM_001039090.2 | chr3:30993979-31021845 |
| 26691 | Skil | NM_001271772.1 | chr3:30993979-31021845 |
| 26692 | Skil | NM_011386.3 | chr3:30993979-31021845 |
| 26693 | Skint1 | NM_001102662.1 | chr4:111678873-111702143 |
| 26694 | Skint10 | NM_177668.2 | chr4:112383434-112447466 |
| 26695 | Skint11 | NM_001166027.1 | chr4:113835988-113917633 |
| 26696 | Skint11 | NM_177669.4 | chr4:113835988-113917633 |
| 26697 | Skint2 | NM_001285963.1 | chr4:112286344-112324853 |
| 26698 | Skint2 | NM_001285965.1 | chr4:112286344-112324853 |
| 26699 | Skint3 | NM_001102474.1 | chr4:111904849-111973073 |
| 26700 | Skint3 | NM_177578.4 | chr4:111904849-111973073 |
| 26701 | Skint5 | NM_178786.4 | chr4:111754074-111840681 |
| 26702 | Skint5 | NM_001167876.1 | chr4:113150495-113672108 |
| 26703 | Skint5 | NM_001167878.1 | chr4:113150495-113672108 |
| 26704 | Skint6 | NM_001103199.1 | chr4:112477220-112599578 |
| 26705 | Skint7 | NM_001142775.1 | chr4:111645531-111660826 |
| 26706 | Skint7 | NM_177818.3 | chr4:111645531-111660826 |
| 26707 | Skint8 | NM_001100466.1 | chr4:111592159-111622961 |
| 26708 | Skint9 | NM_177864.2 | chr4:112058573-112106590 |
| 26709 | Skiv2l | NM_021337.2 | chr17:34976171-34987149 |
| 26710 | Skiv2l2 | NM_028151.2 | chr13:113657988-113717588 |
| 26711 | Skor1 | NM_001163755.1 | chr9:62985970-62996768 |

Fig. 25 - 142

| | | | |
|---|---|---|---|
| 26712 | Skor1 | NM_001163757.1 | chr9:62985970-62996768 |
| 26713 | Skor1 | NM_001163758.1 | chr9:62985970-62996768 |
| 26714 | Skor1 | NM_172446.3 | chr9:62985970-62996768 |
| 26715 | Skor2 | NM_001109743.1 | chr18:77095143-77139081 |
| 26716 | Skp1a | NM_011543.4 | chr11:52045496-52060360 |
| 26717 | Skp2 | NM_001285980.1 | chr15:9041738-9127206 |
| 26718 | Skp2 | NM_013787.3 | chr15:9041738-9127206 |
| 26719 | Sla | NM_001029841.4 | chr15:66502331-66682282 |
| 26720 | Sla | NM_009192.3 | chr15:66502331-66682282 |
| 26721 | Sla2 | NM_029983.5 | chr2:156698658-156712814 |
| 26722 | Slain1 | NM_198014.2 | chr14:104049460-104104016 |
| 26723 | Slain1os | NR_045148.1 | chr14:104092200-104098649 |
| 26724 | Slain2 | NM_001113423.2 | chr5:73305600-73370080 |
| 26725 | Slain2 | NM_153567.3 | chr5:73305600-73370080 |
| 26726 | Slamf1 | NM_013730.4 | chr1:173697262-173731315 |
| 26727 | Slamf6 | NM_030710.2 | chr1:173847667-173873999 |
| 26728 | Slamf7 | NM_144539.5 | chr1:173562534-173583168 |
| 26729 | Slamf8 | NM_029084.3 | chr1:174511507-174520699 |
| 26730 | Slamf9 | NM_029612.4 | chr1:174405490-174408540 |
| 26731 | Slbp | NM_001289724.1 | chr5:33982703-33995223 |
| 26732 | Slbp | NM_001289725.1 | chr5:33982703-33995223 |
| 26733 | Slbp | NM_009193.2 | chr5:33982703-33995223 |
| 26734 | Slc10a1 | NM_001177561.1 | chr12:82054171-82069066 |
| 26735 | Slc10a1 | NM_011387.2 | chr12:82054171-82069066 |
| 26736 | Slc10a2 | NM_011388.2 | chr8:5085622-5105232 |
| 26737 | Slc10a3 | NM_001256104.1 | chrX:71611056-71618688 |
| 26738 | Slc10a3 | NM_145406.2 | chrX:71611056-71618688 |
| 26739 | Slc10a3-ubl4 | NM_001278271.1 | chrX:71611056-71618688 |
| 26740 | Slc10a3-ubl4 | NM_001278272.1 | chrX:71611056-71618688 |
| 26741 | Slc10a3-ubl4 | NR_103489.1 | chrX:71611056-71618688 |
| 26742 | Slc10a4 | NM_173403.2 | chr5:73398142-73404194 |
| 26743 | Slc10a5 | NM_001010834.2 | chr3:10331733-10335656 |
| 26744 | Slc10a6 | NM_029415.2 | chr5:104034729-104058422 |
| 26745 | Slc10a7 | NM_001009981.2 | chr8:81033226-81257911 |
| 26746 | Slc10a7 | NM_001282108.1 | chr8:81033226-81257911 |
| 26747 | Slc10a7 | NM_001282109.1 | chr8:81033226-81257911 |
| 26748 | Slc10a7 | NM_029736.2 | chr8:81033226-81257911 |
| 26749 | Slc10a7 | NR_104094.1 | chr8:81033226-81257911 |
| 26750 | Slc11a1 | NM_013642.2 | chr1:74421776-74432625 |
| 26751 | Slc11a2 | NM_001146161.1 | chr15:100218330-100253486 |
| 26752 | Slc11a2 | NM_008732.2 | chr15:100218330-100253486 |
| 26753 | Slc12a1 | NM_001079690.1 | chr2:124978335-125055737 |
| 26754 | Slc12a1 | NM_183354.2 | chr2:124978335-125055737 |
| 26755 | Slc12a2 | NM_009194.3 | chr18:58038331-58106475 |
| 26756 | Slc12a3 | NM_001205311.1 | chr8:96853107-96890121 |
| 26757 | Slc12a3 | NM_019415.2 | chr8:96853107-96890121 |
| 26758 | Slc12a4 | NM_001253804.1 | chr8:108467489-108490015 |
| 26759 | Slc12a4 | NM_009195.3 | chr8:108467489-108490015 |
| 26760 | Slc12a4 | NR_045594.1 | chr8:108467489-108490015 |
| 26761 | Slc12a5 | NM_020333.2 | chr2:164793487-164825231 |
| 26762 | Slc12a6 | NM_133649.2 | chr2:112106470-112208184 |
| 26763 | Slc12a6 | NM_133649.2 | chr2:112106470-112208184 |
| 26764 | Slc12a7 | NM_011390.2 | chr13:73901144-73954190 |
| 26765 | Slc12a8 | NM_001083902.1 | chr16:33518414-33664221 |
| 26766 | Slc12a8 | NM_134251.2 | chr16:33518414-33664221 |
| 26767 | Slc12a9 | NM_031406.3 | chr5:137755785-137774810 |
| 26768 | Slc13a1 | NM_019481.2 | chr6:24038182-24118092 |
| 26769 | Slc13a2 | NM_022411.3 | chr11:78210778-78235687 |
| 26770 | Slc13a2os | NR_003282.2 | chr11:78207987-78219159 |
| 26771 | Slc13a3 | NM_054055.2 | chr2:165230794-165298697 |
| 26772 | Slc13a4 | NM_172892.3 | chr6:35217952-35258126 |
| 26773 | Slc13a5 | NM_001004148.4 | chr11:72055495-72080106 |
| 26774 | Slc14a1 | NM_001171010.1 | chr18:78296829-78338858 |
| 26775 | Slc14a1 | NM_001171011.1 | chr18:78296829-78338858 |
| 26776 | Slc14a1 | NM_028122.4 | chr18:78296829-78338858 |
| 26777 | Slc14a2 | NM_001110273.1 | chr18:78342882-78793689 |
| 26778 | Slc14a2 | NM_001110274.1 | chr18:78342882-78793689 |
| 26779 | Slc14a2 | NM_030683.3 | chr18:78342882-78793689 |
| 26780 | Slc14a2 | NM_207651.3 | chr18:78342882-78793689 |
| 26781 | Slc15a1 | NM_053079.1 | chr14:121858842-121904476 |
| 26782 | Slc15a2 | NM_001145899.1 | chr16:36750249-36785048 |
| 26783 | Slc15a2 | NM_021301.3 | chr16:36750249-36785048 |
| 26784 | Slc15a3 | NM_023044.2 | chr19:10917034-10932405 |
| 26785 | Slc15a4 | NM_133895.1 | chr5:128076035-128097762 |
| 26786 | Slc15a5 | NM_177787.4 | chr6:137982110-138028437 |
| 26787 | Slc16a1 | NM_009196.4 | chr3:104442586-104462385 |
| 26788 | Slc16a10 | NM_001114332.1 | chr10:39753340-39862060 |
| 26789 | Slc16a10 | NM_028247.4 | chr10:39753340-39862060 |
| 26790 | Slc16a11 | NM_153081.3 | chr11:70027411-70029916 |
| 26791 | Slc16a12 | NM_172838.3 | chr19:34742895-34821601 |
| 26792 | Slc16a13 | NM_172371.3 | chr11:70030293-70034496 |
| 26793 | Slc16a14 | NM_027921.3 | chr1:84903279-84931658 |
| 26794 | Slc16a2 | NM_009197.2 | chrX:100892752-101017327 |
| 26795 | Slc16a3 | NM_001038653.1 | chr11:120809797-120820314 |
| 26796 | Slc16a3 | NM_001038654.1 | chr11:120809797-120820314 |
| 26797 | Slc16a3 | NM_030696.3 | chr11:120809797-120820314 |
| 26798 | Slc16a4 | NM_146136.1 | chr3:107094209-107115033 |
| 26799 | Slc16a5 | NM_001080934.1 | chr11:115323786-115335712 |
| 26800 | Slc16a6 | NM_001029842.1 | chr11:109301391-109434643 |
| 26801 | Slc16a6 | NM_134038.2 | chr11:109301391-109434643 |
| 26802 | Slc16a7 | NM_011391.1 | chr10:124664540-124765591 |
| 26803 | Slc16a8 | NM_020516.2 | chr15:79081446-79095178 |
| 26804 | Slc16a9 | NM_025807.3 | chr10:69708023-69748699 |
| 26805 | Slc17a1 | NM_001170638.1 | chr13:23962141-23987599 |
| 26806 | Slc17a1 | NM_009198.3 | chr13:23962141-23987599 |
| 26807 | Slc17a2 | NM_144836.2 | chr13:23898895-23915394 |
| 26808 | Slc17a3 | NM_001164743.1 | chr13:23931302-23952583 |
| 26809 | Slc17a3 | NM_134069.3 | chr13:23931302-23952583 |
| 26810 | Slc17a4 | NM_177016.3 | chr13:23989757-24006876 |
| 26811 | Slc17a5 | NM_001276452.1 | chr9:78384293-78435852 |
| 26812 | Slc17a5 | NM_172773.3 | chr9:78384293-78435852 |
| 26813 | Slc17a6 | NM_080853.1 | chr7:58877199-58926496 |
| 26814 | Slc17a7 | NM_182993.2 | chr7:52419291-52431509 |
| 26815 | Slc17a8 | NM_182959.3 | chr10:89036764-89083994 |
| 26816 | Slc17a9 | NM_183161.3 | chr2:180460043-180476983 |
| 26817 | Slc18a1 | NM_153054.2 | chr8:71561607-71613121 |
| 26818 | Slc18a2 | NM_172523.3 | chr19:59335367-59370502 |
| 26819 | Slc18a3 | NM_021712.2 | chr14:33275623-33278036 |
| 26820 | Slc18b1 | NM_183116.2 | chr10:23516791-23547774 |
| 26821 | Slc19a1 | NM_001199271.1 | chr10:76495483-76513177 |
| 26822 | Slc19a1 | NM_031196.3 | chr10:76495483-76513177 |
| 26823 | Slc19a2 | NM_001276455.1 | chr1:166179176-166195516 |
| 26824 | Slc19a2 | NM_054087.3 | chr1:166179176-166195516 |
| 26825 | Slc19a3 | NM_030556.2 | chr1:83009097-83035023 |
| 26826 | Slc1a1 | NM_009199.2 | chr19:28909655-28988450 |
| 26827 | Slc1a2 | NM_001077514.3 | chr2:102498839-102630941 |
| 26828 | Slc1a2 | NM_001077515.2 | chr2:102498839-102630941 |
| 26829 | Slc1a2 | NM_011393.2 | chr2:102498839-102630941 |
| 26830 | Slc1a3 | NM_148938.3 | chr15:8584123-8660807 |
| 26831 | Slc1a4 | NM_018861.3 | chr11:20202182-20232716 |
| 26832 | Slc1a5 | NM_009201.2 | chr7:17366694-17383623 |
| 26833 | Slc1a6 | NM_009200.3 | chr10:78243240-78277570 |
| 26834 | Slc1a7 | NM_146255.2 | chr4:107640938-107686137 |
| 26835 | Slc20a1 | NM_001159593.1 | chr2:129024508-129037348 |
| 26836 | Slc20a1 | NM_015747.2 | chr2:129024508-129037348 |
| 26837 | Slc20a2 | NM_011394.3 | chr8:23587172-23680088 |
| 26838 | Slc22a1 | NM_009202.5 | chr17:12841740-12868704 |
| 26839 | Slc22a12 | NM_009203.3 | chr19:6535855-6543070 |
| 26840 | Slc22a13 | NM_133980.3 | chr9:119102095-119118223 |
| 26841 | Slc22a13b-ps | NR_033303.1 | chr9:119129608-119140810 |
| 26842 | Slc22a14 | NM_001037749.2 | chr9:119078573-119099511 |
| 26843 | Slc22a15 | NM_001039371.2 | chr3:101659693-101728376 |
| 26844 | Slc22a16 | NM_027572.1 | chr10:40290167-40323938 |
| 26845 | Slc22a17 | NM_021551.4 | chr14:55525563-55531969 |
| 26846 | Slc22a18 | NM_001042760.1 | chr7:150659659-150685237 |
| 26847 | Slc22a18 | NM_008767.2 | chr7:150659659-150685237 |
| 26848 | Slc22a19 | NM_144856.2 | chr19:7747565-7785800 |
| 26849 | Slc22a2 | NM_013667.2 | chr17:12777054-12821354 |
| 26850 | Slc22a20 | NM_198650.2 | chr19:5970233-5986143 |
| 26851 | Slc22a21 | NM_019723.2 | chr11:53764325-53793529 |
| 26852 | Slc22a22 | NM_172378.2 | chr15:57075325-57309180 |
| 26853 | Slc22a23 | NM_001033167.3 | chr13:34271026-34437051 |
| 26854 | Slc22a26 | NM_146232.1 | chr19:7856472-7877157 |
| 26855 | Slc22a27 | NM_134256.1 | chr19:7938878-8040517 |
| 26856 | Slc22a28 | NM_001013820.3 | chr19:8136698-8206472 |
| 26857 | Slc22a29 | NM_172776.2 | chr19:8234657-8293329 |
| 26858 | Slc22a3 | NM_011395.2 | chr17:12612840-12700570 |
| 26859 | Slc22a30 | NM_177002.3 | chr19:8410112-8479595 |
| 26860 | Slc22a4 | NM_019687.3 | chr11:53796627-53841592 |
| 26861 | Slc22a5 | NM_011396.3 | chr11:53678043-53705205 |
| 26862 | Slc22a6 | NM_008766.3 | chr19:8692485-8702789 |
| 26863 | Slc22a7 | NM_144856.2 | chr17:46569133-46575426 |
| 26864 | Slc22a8 | NM_001164634.1 | chr19:8665743-8686325 |
| 26865 | Slc22a8 | NM_001164635.1 | chr19:8665743-8686325 |
| 26866 | Slc22a8 | NM_031194.5 | chr19:8665743-8686325 |
| 26867 | Slc23a1 | NM_011397.4 | chr18:35774258-35786881 |
| 26868 | Slc23a2 | NM_018824.2 | chr2:131878231-131970844 |
| 26869 | Slc23a3 | NM_194333.3 | chr1:75122115-75130464 |
| 26870 | Slc24a1 | NM_144813.1 | chr9:64770667-64799414 |
| 26871 | Slc24a2 | NM_001110240.1 | chr4:86629029-86876444 |
| 26872 | Slc24a2 | NM_172426.2 | chr4:86629029-86876444 |
| 26873 | Slc24a3 | NM_053195.2 | chr2:145068347-145467675 |
| 26874 | Slc24a4 | NM_172152.2 | chr12:103367628-103504959 |
| 26875 | Slc24a5 | NM_175034.3 | chr2:124893863-124914413 |
| 26876 | Slc25a1 | NM_153150.2 | chr16:17925303-17928312 |
| 26877 | Slc25a10 | NM_013770.2 | chr11:120353150-120362475 |
| 26878 | Slc25a11 | NM_024211.3 | chr11:70457528-70460541 |
| 26879 | Slc25a12 | NM_172436.3 | chr2:71112351-71205611 |
| 26880 | Slc25a13 | NM_001177572.1 | chr6:5991217-6167173 |
| 26881 | Slc25a13 | NM_015829.3 | chr6:5991217-6167173 |
| 26882 | Slc25a14 | NM_001166450.2 | chrX:45976754-46015475 |
| 26883 | Slc25a14 | NM_001290703.1 | chrX:45976754-46015475 |
| 26884 | Slc25a14 | NM_001290704.1 | chrX:45976754-46015475 |
| 26885 | Slc25a14 | NM_001290705.1 | chrX:45976754-46015475 |
| 26886 | Slc25a14 | NM_011398.2 | chrX:45976754-46015475 |
| 26887 | Slc25a15 | NM_181325.4 | chr8:23486021-23509093 |
| 26888 | Slc25a16 | NM_175194.2 | chr10:62383380-62409242 |
| 26889 | Slc25a17 | NM_013399.3 | chr15:81149350-81191195 |
| 26890 | Slc25a18 | NM_001081048.2 | chr6:120723785-120744000 |
| 26891 | Slc25a19 | NM_001252884.1 | chr11:115475494-115489609 |
| 26892 | Slc25a19 | NM_001252394.1 | chr11:115475494-115489609 |
| 26893 | Slc25a19 | NM_001252395.1 | chr11:115475494-115489609 |
| 26894 | Slc25a19 | NM_001252396.1 | chr11:115475494-115489609 |
| 26895 | Slc25a19 | NM_026071.3 | chr11:115475494-115489609 |
| 26896 | Slc25a2 | NM_001159275.1 | chr18:37797032-37798377 |
| 26897 | Slc25a20 | NM_020520.4 | chr9:108564428-108586972 |
| 26898 | Slc25a21 | NM_001167976.1 | chr12:57813620-58298459 |
| 26899 | Slc25a21 | NM_172577.3 | chr12:57813620-58298459 |
| 26900 | Slc25a22 | NM_001177576.1 | chr7:148615647-148623773 |
| 26901 | Slc25a22 | NM_026646.3 | chr7:148615647-148623773 |

Fig. 25 - 143

| | | | | | | | | |
|---|---|---|---|---|---|---|---|---|
| 26902 | Slc25a23 | NM_025877.4 | chr17:57183133-57199286 | | 26997 | Slc30a4 | NM_011774.3 | chr2:122506968-122528399 |
| 26903 | Slc25a24 | NM_172685.1 | chr3:108926066-108971327 | | 26998 | Slc30a5 | NM_022885.2 | chr13:101572602-101603382 |
| 26904 | Slc25a25 | NM_001164357.1 | chr2:32270006-32310996 | | 26999 | Slc30a6 | NM_001252478.1 | chr17:74794947-74823569 |
| 26905 | Slc25a25 | NM_001164358.1 | chr2:32270006-32310996 | | 27000 | Slc30a6 | NM_144798.6 | chr17:74794947-74823569 |
| 26906 | Slc25a25 | NM_001290558.1 | chr2:32270006-32310996 | | 27001 | Slc30a7 | NM_023214.7 | chr3:115641890-115710324 |
| 26907 | Slc25a25 | NM_146118.3 | chr2:32270006-32310996 | | 27002 | Slc30a8 | NM_172816.3 | chr15:52127107-52167288 |
| 26908 | Slc25a26 | NM_026255.5 | chr6:94450308-94554646 | | 27003 | Slc30a9 | NM_178651.3 | chr5:67698195-67747384 |
| 26909 | Slc25a27 | NM_028711.3 | chr17:43778848-43803964 | | 27004 | Slc31a1 | NM_175090.4 | chr4:62021734-62052803 |
| 26910 | Slc25a28 | NM_145156.1 | chr19:43738291-43749371 | | 27005 | Slc31a2 | NM_001290518.1 | chr4:61947462-61959446 |
| 26911 | Slc25a29 | NM_181328.3 | chr12:110064087-110074086 | | 27006 | Slc31a2 | NM_025286.3 | chr4:61947462-61959446 |
| 26912 | Slc25a3 | NM_133668.3 | chr10:90579322-90586708 | | 27007 | Slc32a1 | NM_009508.2 | chr2:158436493-158441483 |
| 26913 | Slc25a30 | NM_026232.3 | chr14:76161805-76186844 | | 27008 | Slc33a1 | NM_001272035.1 | chr3:63746245-63768655 |
| 26914 | Slc25a31 | NM_178386.3 | chr3:40512792-40530016 | | 27009 | Slc33a1 | NM_015728.5 | chr3:63746245-63768655 |
| 26915 | Slc25a32 | NM_172402.3 | chr15:38925736-38944262 | | 27010 | Slc34a1 | NM_011392.2 | chr13:55501009-55516056 |
| 26916 | Slc25a33 | NM_027460.2 | chr4:149118144-149148376 | | 27011 | Slc34a2 | NM_011402.3 | chr5:53440591-53462902 |
| 26917 | Slc25a34 | NM_001013780.1 | chr4:141174739-141179749 | | 27012 | Slc34a3 | NM_080854.3 | chr2:25084416-25089754 |
| 26918 | Slc25a35 | NM_028048.2 | chr11:68781633-68786017 | | 27013 | Slc35a1 | NM_011895.3 | chr4:34610505-34634687 |
| 26919 | Slc25a36 | NM_138756.4 | chr9:96977429-97011460 | | 27014 | Slc35a2 | NM_001083937.1 | chrX:7461369-7471618 |
| 26920 | Slc25a37 | NM_026331.3 | chr14:69859907-69903160 | | 27015 | Slc35a2 | NM_078484.2 | chrX:7461369-7471618 |
| 26921 | Slc25a38 | NM_144793.1 | chr9:120019516-120033437 | | 27016 | Slc35a3 | NM_144902.3 | chr3:116373715-116415198 |
| 26922 | Slc25a39 | NM_026542.3 | chr11:102264295-102268831 | | 27017 | Slc35a4 | NM_001083317.1 | chr18:36830812-36843516 |
| 26923 | Slc25a4 | NM_007450.1 | chr8:47292697-47296363 | | 27018 | Slc35a4 | NM_026404.2 | chr18:36830812-36843516 |
| 26924 | Slc25a40 | NM_001289595.1 | chr5:8422837-8454839 | | 27019 | Slc35a5 | NM_028756.4 | chr16:45139685-45158786 |
| 26925 | Slc25a40 | NM_001289596.1 | chr5:8422837-8454839 | | 27020 | Slc35b1 | NM_016752.1 | chr11:95246235-95252966 |
| 26926 | Slc25a40 | NM_178746.5 | chr5:8422837-8454839 | | 27021 | Slc35b2 | NM_028662.2 | chr17:45701100-45704618 |
| 26927 | Slc25a41 | NM_175333.3 | chr17:57172194-57181077 | | 27022 | Slc35b3 | NM_001170430.1 | chr13:39024008-39052744 |
| 26928 | Slc25a42 | NM_001007570.2 | chr8:72708238-72736180 | | 27023 | Slc35b3 | NM_001170431.1 | chr13:39024008-39052744 |
| 26929 | Slc25a43 | NM_001085497.2 | chrX:34283626-34317302 | | 27024 | Slc35b3 | NM_134060.4 | chr13:39024008-39052744 |
| 26930 | Slc25a43 | NR_075096.1 | chrX:34283626-34317302 | | 27025 | Slc35b4 | NM_021435.3 | chr6:34105878-34127054 |
| 26931 | Slc25a43 | NR_075097.1 | chrX:34283626-34317302 | | 27026 | Slc35c1 | NM_145832.3 | chr2:92292921-92300675 |
| 26932 | Slc25a44 | NM_001145876.2 | chr3:88214415-88229063 | | 27027 | Slc35c1 | NM_211358.2 | chr2:92292921-92300675 |
| 26933 | Slc25a44 | NM_001145877.2 | chr3:88214415-88229063 | | 27028 | Slc35c2 | NM_001252573.1 | chr2:165102021-165113338 |
| 26934 | Slc25a44 | NM_001281795.1 | chr3:88214415-88229063 | | 27029 | Slc35c2 | NM_001252574.1 | chr2:165102021-165113338 |
| 26935 | Slc25a44 | NM_178696.5 | chr3:88214415-88229063 | | 27030 | Slc35c2 | NM_001252575.1 | chr2:165102021-165113338 |
| 26936 | Slc25a45 | NM_134154.3 | chr19:5878465-5885768 | | 27031 | Slc35c2 | NM_144893.2 | chr2:165102021-165113338 |
| 26937 | Slc25a46 | NM_026165.3 | chr18:31739821-31769556 | | 27032 | Slc35c2 | NR_045544.1 | chr2:165102021-165113338 |
| 26938 | Slc25a47 | NM_001012310.2 | chr12:110089338-110095025 | | 27033 | Slc35d1 | NM_177732.4 | chr4:102844322-102887489 |
| 26939 | Slc25a48 | NM_177809.4 | chr13:56539715-56573724 | | 27034 | Slc35d2 | NM_001001321.3 | chr13:64197617-64230638 |
| 26940 | Slc25a5 | NM_007453.4 | chrX:34335646-34338801 | | 27035 | Slc35d3 | NM_029529.3 | chr10:19567722-19571265 |
| 26941 | Slc25a51 | NM_001009949.3 | chr4:45408795-45421638 | | 27036 | Slc35e1 | NM_177766.3 | chr8:75001893-75016513 |
| 26942 | Slc25a53 | NM_001082412.2 | chrX:133515654-133572841 | | 27037 | Slc35e2 | NM_177186.4 | chr4:154975525-154997450 |
| 26943 | Slc25a53 | NM_001114176.1 | chrX:133515654-133572841 | | 27038 | Slc35e3 | NM_029875.2 | chr10:117170733-117183414 |
| 26944 | Slc25a54 | NM_029054.1 | chr3:108883416-108919500 | | 27039 | Slc35e4 | NM_153142.3 | chr11:3807024-3814667 |
| 26945 | Slc26a1 | NM_174870.3 | chr5:109099566-109104668 | | 27040 | Slc35f1 | NM_178675.4 | chr10:52410306-52831428 |
| 26946 | Slc26a10 | NM_177615.2 | chr10:126609481-126617701 | | 27041 | Slc35f2 | NM_028060.2 | chr9:53619341-53665968 |
| 26947 | Slc26a11 | NM_178743.3 | chr11:119216870-119242390 | | 27042 | Slc35f3 | NM_175434.3 | chr8:128822478-128919877 |
| 26948 | Slc26a2 | NM_007885.2 | chr18:61356507-61371250 | | 27043 | Slc35f4 | NM_029238.2 | chr14:49918194-50145512 |
| 26949 | Slc26a3 | NM_021353.1 | chr12:32123083-32158784 | | 27044 | Slc35f5 | NM_028787.4 | chr1:127457592-127492261 |
| 26950 | Slc26a4 | NM_011867.3 | chr12:32204683-32244834 | | 27045 | Slc35f6 | NM_175675.3 | chr5:30950312-30962102 |
| 26951 | Slc26a5 | NM_001289787.1 | chr5:21314818-21371422 | | 27046 | Slc35g1 | NM_175507.3 | chr19:38470469-38480097 |
| 26952 | Slc26a5 | NM_001289788.1 | chr5:21314818-21371422 | | 27047 | Slc35g2 | NM_001101483.1 | chr9:100452606-100471504 |
| 26953 | Slc26a5 | NM_030727.1 | chr5:21314818-21371422 | | 27048 | Slc35g3 | NM_019871.2 | chr11:69573386-69575346 |
| 26954 | Slc26a6 | NM_134204.4 | chr9:108756373-108815380 | | 27049 | Slc36a1 | NM_153139.4 | chr11:55017841-55049832 |
| 26955 | Slc26a7 | NM_145947.2 | chr4:14432343-14548925 | | 27050 | Slc36a1os | NR_046034.1 | chr11:55005220-55011184 |
| 26956 | Slc26a8 | NM_001290320.1 | chr17:28774723-28826932 | | 27051 | Slc36a2 | NM_153170.3 | chr11:54971969-54998579 |
| 26957 | Slc26a9 | NM_177243.4 | chr1:133640598-133666982 | | 27052 | Slc36a3 | NM_172258.3 | chr11:54938324-54965208 |
| 26958 | Slc27a1 | NM_011977.3 | chr8:74092825-74110607 | | 27053 | Slc36a4 | NM_172289.4 | chr9:15514212-15543233 |
| 26959 | Slc27a2 | NM_011978.2 | chr2:126378759-126413979 | | 27054 | Slc37a1 | NM_001242427.1 | chr17:31432427-31487643 |
| 26960 | Slc27a3 | NM_011988.2 | chr3:90189154-90193849 | | 27055 | Slc37a1 | NM_153062.2 | chr17:31432427-31487643 |
| 26961 | Slc27a4 | NM_011989.4 | chr2:29658199-29673042 | | 27056 | Slc37a2 | NM_001145960.1 | chr9:37036733-37063323 |
| 26962 | Slc27a5 | NM_009512.2 | chr7:13573695-13583541 | | 27057 | Slc37a2 | NM_020258.1 | chr9:37036733-37063323 |
| 26963 | Slc27a6 | NM_001081072.1 | chr18:58715893-58772523 | | 27058 | Slc37a3 | NM_028123.3 | chr6:39284769-39327706 |
| 26964 | Slc28a1 | NM_001004184.3 | chr7:88259684-88315302 | | 27059 | Slc37a4 | NM_008063.2 | chr9:44206259-44211048 |
| 26965 | Slc28a2 | NM_172980.2 | chr2:122252212-122286866 | | 27060 | Slc38a1 | NM_001166456.1 | chr15:96401848-96473344 |
| 26966 | Slc28a3 | NM_022317.3 | chr13:58654668-58712238 | | 27061 | Slc38a1 | NM_001166458.1 | chr15:96401848-96473344 |
| 26967 | Slc29a1 | NM_001199113.1 | chr17:45722148-45736552 | | 27062 | Slc38a1 | NM_134086.4 | chr15:96401848-96473344 |
| 26968 | Slc29a1 | NM_001199114.1 | chr17:45722148-45736552 | | 27063 | Slc38a10 | NM_001164798.1 | chr11:119965264-120012665 |
| 26969 | Slc29a1 | NM_001199115.1 | chr17:45722148-45736552 | | 27064 | Slc38a10 | NM_001164799.1 | chr11:119965264-120012665 |
| 26970 | Slc29a1 | NM_001199116.1 | chr17:45722148-45736552 | | 27065 | Slc38a10 | NM_001164800.1 | chr11:119965264-120012665 |
| 26971 | Slc29a1 | NM_022880.3 | chr17:45722148-45736552 | | 27066 | Slc38a10 | NM_001164801.1 | chr11:119965264-120012665 |
| 26972 | Slc29a2 | NM_007854.3 | chr19:5024005-5031972 | | 27067 | Slc38a10 | NM_001164802.1 | chr11:119965264-120012665 |
| 26973 | Slc29a3 | NM_023596.3 | chr10:60174819-60215530 | | 27068 | Slc38a10 | NM_024249.5 | chr11:119965264-120012665 |
| 26974 | Slc29a4 | NM_146257.2 | chr5:143178054-143198443 | | 27069 | Slc38a11 | NM_177074.2 | chr2:65154689-65202083 |
| 26975 | Slc2a1 | NM_011400.3 | chr4:118781349-118809934 | | 27070 | Slc38a2 | NM_175121.3 | chr15:96517822-96530129 |
| 26976 | Slc2a10 | NM_130451.3 | chr2:165329896-165345417 | | 27071 | Slc38a3 | NM_001199217.1 | chr9:107553485-107571299 |
| 26977 | Slc2a12 | NM_178934.4 | chr10:22364817-22423686 | | 27072 | Slc38a3 | NM_001199218.1 | chr9:107553485-107571299 |
| 26978 | Slc2a13 | NM_001083633.3 | chr15:91098121-91403692 | | 27073 | Slc38a3 | NM_023805.3 | chr9:107553485-107571299 |
| 26979 | Slc2a2 | NM_031197.2 | chr3:28596824-28627282 | | 27074 | Slc38a4 | NM_027052.3 | chr15:96825253-96886387 |
| 26980 | Slc2a3 | NM_011401.4 | chr6:122677826-122692763 | | 27075 | Slc38a5 | NM_172479.3 | chrX:7848506-7857302 |
| 26981 | Slc2a4 | NM_009204.2 | chr11:69755787-69761692 | | 27076 | Slc38a6 | NM_001037717.3 | chr12:74387834-74455032 |
| 26982 | Slc2a4rg-ps | NR_045164.1 | chr2:181118954-181122301 | | 27077 | Slc38a7 | NM_172758.4 | chr8:98359822-98377391 |
| 26983 | Slc2a5 | NM_019741.3 | chr4:149493452-149518277 | | 27078 | Slc38a8 | NM_001009950.1 | chr8:122003502-122025598 |
| 26984 | Slc2a6 | NM_001177627.1 | chr2:26876884-26883518 | | 27079 | Slc38a9 | NM_178746.9 | chr13:113450973-113528960 |
| 26985 | Slc2a6 | NM_172659.2 | chr2:26876884-26883518 | | 27080 | Slc39a1 | NM_013901.2 | chr3:90052113-90057534 |
| 26986 | Slc2a7 | NM_001085529.1 | chr4:149523080-149542591 | | 27081 | Slc39a10 | NM_172653.2 | chr1:46864388-46910354 |
| 26987 | Slc2a8 | NM_019488.4 | chr2:32828508-32837576 | | 27082 | Slc39a11 | NM_001166503.1 | chr11:113106168-113427129 |
| 26988 | Slc2a9 | NM_001012363.2 | chr5:38740511-38893391 | | 27083 | Slc39a11 | NM_027216.5 | chr11:113106168-113427129 |
| 26989 | Slc2a9 | NM_001102414.1 | chr5:38740511-38893391 | | 27084 | Slc39a12 | NM_001012305.2 | chr2:14310024-14416604 |
| 26990 | Slc2a9 | NM_001102415.1 | chr5:38740511-38893391 | | 27085 | Slc39a13 | NM_001290765.1 | chr2:90901937-90910472 |
| 26991 | Slc2a9 | NM_145559.2 | chr5:38740511-38893391 | | 27086 | Slc39a13 | NM_026721.3 | chr2:90901937-90910472 |
| 26992 | Slc30a1 | NM_009579.3 | chr1:193730660-193737126 | | 27087 | Slc39a13 | NR_110981.1 | chr2:90901937-90910472 |
| 26993 | Slc30a10 | NM_001033286.2 | chr1:187728727-187292640 | | 27088 | Slc39a14 | NM_001135151.1 | chr14:70703273-70751231 |
| 26994 | Slc30a2 | NM_001039677.2 | chr4:133898960-133910399 | | 27089 | Slc39a14 | NM_001135152.1 | chr14:70703273-70751231 |
| 26995 | Slc30a3 | NM_011773.2 | chr5:31388479-31395900 | | 27090 | Slc39a14 | NM_144808.4 | chr14:70703273-70751231 |
| 26996 | Slc30a4 | NM_001290993.1 | chr2:122506968-122528399 | | 27091 | Slc39a2 | NM_001039676.2 | chr14:52513284-52516420 |

Fig. 25 - 144

| | | | | | | | | |
|---|---|---|---|---|---|---|---|---|
| 27092 | Slc39a3 | NM_134135.1 | chr10:80491284-80496657 | | 27187 | Slc6a12 | NM_133661.3 | chr6:121296714-121315791 |
| 27093 | Slc39a4 | NM_028064.2 | chr15:76442812-76447282 | | 27188 | Slc6a13 | NM_144512.2 | chr6:121250313-121287736 |
| 27094 | Slc39a5 | NM_001136237.1 | chr10:127832987-127838280 | | 27189 | Slc6a14 | NM_020049.4 | chrX:21292025-21319483 |
| 27095 | Slc39a5 | NM_028051.3 | chr10:127832987-127838280 | | 27190 | Slc6a15 | NM_001252330.1 | chr10:102830441-102882013 |
| 27096 | Slc39a5 | NM_028092.3 | chr10:127832987-127838280 | | 27191 | Slc6a15 | NM_175328.3 | chr10:102830441-102882013 |
| 27097 | Slc39a6 | NM_139143.3 | chr18:24738381-24762318 | | 27192 | Slc6a17 | NM_172271.1 | chr3:107270465-107320936 |
| 27098 | Slc39a7 | NM_001077709.1 | chr17:34165210-34168635 | | 27193 | Slc6a18 | NM_001040692.3 | chr13:73799197-73815471 |
| 27099 | Slc39a7 | NM_008202.2 | chr17:34165210-34168635 | | 27194 | Slc6a18 | NM_001136087.2 | chr13:73799197-73815471 |
| 27100 | Slc39a8 | NM_001135149.1 | chr3:135488242-135551536 | | 27195 | Slc6a18 | NM_001168643.1 | chr13:73799197-73815471 |
| 27101 | Slc39a8 | NM_001135150.1 | chr3:135488242-135551536 | | 27196 | Slc6a18 | NM_001168644.1 | chr13:73799197-73815471 |
| 27102 | Slc39a8 | NM_026228.5 | chr3:135488242-135551536 | | 27197 | Slc6a18 | NM_001168645.1 | chr13:73799197-73815471 |
| 27103 | Slc39a9 | NM_026244.2 | chr12:81745201-81784329 | | 27198 | Slc6a18 | NM_001168646.1 | chr13:73799197-73815471 |
| 27104 | Slc3a1 | NM_009205.2 | chr17:85427687-85463581 | | 27199 | Slc6a19 | NM_028878.3 | chr13:73818605-73838143 |
| 27105 | Slc3a2 | NM_001161413.1 | chr19:8781371-8797859 | | 27200 | Slc6a19os | NM_027780.1 | chr13:73837274-73847304 |
| 27106 | Slc3a2 | NM_008577.4 | chr19:8781371-8797859 | | 27201 | Slc6a2 | NM_009209.3 | chr8:95484945-95525566 |
| 27107 | Slc40a1 | NM_016917.2 | chr1:45964914-45982439 | | 27202 | Slc6a20a | NM_139142.2 | chr9:123546024-123587950 |
| 27108 | Slc41a1 | NM_173865.3 | chr1:133724588-133745440 | | 27203 | Slc6a20b | NM_011731.3 | chr9:123502937-123541683 |
| 27109 | Slc41a2 | NM_177388.3 | chr10:82693883-82800562 | | 27204 | Slc6a3 | NM_010020.3 | chr13:73674194-73716120 |
| 27110 | Slc41a3 | NM_001037493.2 | chr6:90554873-90596406 | | 27205 | Slc6a4 | NM_010484.2 | chr11:76812098-76845845 |
| 27111 | Slc41a3 | NM_027868.2 | chr6:90554873-90596406 | | 27206 | Slc6a5 | NM_001146013.1 | chr7:57165668-57214863 |
| 27112 | Slc43a1 | NM_001081349.2 | chr2:84679564-84703743 | | 27207 | Slc6a5 | NM_148931.2 | chr7:57165668-57214863 |
| 27113 | Slc43a1 | NM_001083809.1 | chr2:84679564-84703743 | | 27208 | Slc6a6 | NM_009320.4 | chr6:91634060-91709057 |
| 27114 | Slc43a1 | NM_024497.1 | chr2:84679564-84703743 | | 27209 | Slc6a7 | NM_201353.1 | chr18:61155033-61173853 |
| 27115 | Slc43a2 | NM_001199283.1 | chr11:75345195-75391074 | | 27210 | Slc6a8 | NM_001142809.1 | chrX:70918471-70927839 |
| 27116 | Slc43a2 | NM_001199284.1 | chr11:75345195-75391074 | | 27211 | Slc6a8 | NM_001142810.1 | chrX:70918471-70927839 |
| 27117 | Slc43a2 | NM_173388.2 | chr11:75345195-75391074 | | 27212 | Slc6a8 | NM_133987.2 | chrX:70918471-70927839 |
| 27118 | Slc43a3 | NM_021398.3 | chr2:84776802-84798666 | | 27213 | Slc6a9 | NM_008135.4 | chr4:117507863-117541910 |
| 27119 | Slc44a1 | NM_001159633.1 | chr4:53453284-53635350 | | 27214 | Slc7a1 | NM_007513.4 | chr5:149138985-149211480 |
| 27120 | Slc44a1 | NM_133891.3 | chr4:53453284-53635350 | | 27215 | Slc7a10 | NM_017394.4 | chr7:35971404-35986130 |
| 27121 | Slc44a2 | NM_001199186.1 | chr9:21125162-21159472 | | 27216 | Slc7a11 | NM_011990.2 | chr3:50168857-50247535 |
| 27122 | Slc44a2 | NM_152808.3 | chr9:21125162-21159472 | | 27217 | Slc7a12 | NM_080852.2 | chr3:14480698-14505818 |
| 27123 | Slc44a3 | NM_145394.3 | chr3:121162445-121235262 | | 27218 | Slc7a13 | NM_028746.3 | chr4:19745873-19769360 |
| 27124 | Slc44a4 | NM_023557.3 | chr17:35051410-35067381 | | 27219 | Slc7a14 | NM_172861.3 | chr3:31101777-31209241 |
| 27125 | Slc44a5 | NM_001081263.1 | chr3:153636399-153934684 | | 27220 | Slc7a15 | NM_001038660.2 | chr12:8535288-8605872 |
| 27126 | Slc45a1 | NM_173774.3 | chr4:150003564-150026283 | | 27221 | Slc7a15 | NM_001286385.1 | chr12:8535288-8605872 |
| 27127 | Slc45a2 | NM_053077.3 | chr15:10930475-10958988 | | 27222 | Slc7a15 | NM_177802.3 | chr12:8535288-8605872 |
| 27128 | Slc45a3 | NM_001177628.2 | chr1:133859491-133879549 | | 27223 | Slc7a2 | NM_001044740.2 | chr8:41947720-42007424 |
| 27129 | Slc45a3 | NM_145977.2 | chr1:133859491-133879549 | | 27224 | Slc7a2 | NM_007514.3 | chr8:41947720-42007424 |
| 27130 | Slc45a4 | NM_001033219.3 | chr15:73410720-73455174 | | 27225 | Slc7a3 | NM_007515.3 | chrX:98274559-98280691 |
| 27131 | Slc45a4 | NM_001168255.1 | chr15:73410720-73455174 | | 27226 | Slc7a4 | NM_144852.3 | chr16:17572110-17576764 |
| 27132 | Slc46a1 | NM_026740.2 | chr11:78279202-78285447 | | 27227 | Slc7a5 | NM_011404.3 | chr8:124405045-124431586 |
| 27133 | Slc46a2 | NM_021053.4 | chr4:59918770-59927928 | | 27228 | Slc7a6 | NM_178798.3 | chr8:106692774-108722604 |
| 27134 | Slc46a3 | NM_027872.3 | chr5:148690016-148706378 | | 27229 | Slc7a6os | NM_001007567.2 | chr8:108724337-108734833 |
| 27135 | Slc47a1 | NM_026183.5 | chr11:61156901-61191577 | | 27230 | Slc7a7 | NM_001253679.1 | chr14:54980524-55036539 |
| 27136 | Slc47a2 | NM_001033542.2 | chr11:61115132-61156362 | | 27231 | Slc7a7 | NM_001253680.1 | chr14:54980524-55036539 |
| 27137 | Slc48a1 | NM_026353.4 | chr15:97614796-97623123 | | 27232 | Slc7a7 | NM_011405.4 | chr14:54980524-55036539 |
| 27138 | Slc4a1 | NM_011403.2 | chr11:102210133-102226595 | | 27233 | Slc7a8 | NM_016972.2 | chr14:55341051-55400723 |
| 27139 | Slc4a10 | NM_001242378.1 | chr2:61884571-62164800 | | 27234 | Slc7a9 | NM_001199015.1 | chr7:36234110-36251053 |
| 27140 | Slc4a10 | NM_001242379.1 | chr2:61884571-62164800 | | 27235 | Slc7a9 | NM_001199016.1 | chr7:36234110-36251053 |
| 27141 | Slc4a10 | NM_001242380.1 | chr2:61884571-62164800 | | 27236 | Slc7a9 | NM_023291.3 | chr7:36234110-36251053 |
| 27142 | Slc4a10 | NM_001242381.1 | chr2:61884571-62164800 | | 27237 | Slc8a1 | NM_001112798.2 | chr17:81772444-82137727 |
| 27143 | Slc4a10 | NM_001242382.1 | chr2:61884571-62164800 | | 27238 | Slc8a1 | NM_001286684.1 | chr17:81772444-82137727 |
| 27144 | Slc4a10 | NM_001242383.1 | chr2:61884571-62164800 | | 27239 | Slc8a1 | NM_011406.3 | chr17:81772444-82137727 |
| 27145 | Slc4a10 | NM_033552.3 | chr2:61884571-62164800 | | 27240 | Slc8a1 | NR_104580.1 | chr17:81772444-82137727 |
| 27146 | Slc4a11 | NM_001081162.1 | chr2:130509843-130523255 | | 27241 | Slc8a2 | NM_148946.2 | chr7:16715648-16745860 |
| 27147 | Slc4a1ap | NM_009062.2 | chr5:31829367-31856411 | | 27242 | Slc8a3 | NM_001167920.1 | chr12:82298901-82434167 |
| 27148 | Slc4a2 | NM_001253892.1 | chr5:23931049-23946765 | | 27243 | Slc8a3 | NM_080440.3 | chr12:82298901-82434167 |
| 27149 | Slc4a2 | NM_009207.3 | chr5:23931049-23946765 | | 27244 | Slc8b1 | NM_001177594.1 | chr5:120961200-120984033 |
| 27150 | Slc4a3 | NM_009208.3 | chr1:75542840-75556006 | | 27245 | Slc8b1 | NM_001177595.1 | chr5:120961200-120984033 |
| 27151 | Slc4a4 | NM_001136260.1 | chr5:89316284-89668681 | | 27246 | Slc8b1 | NM_133221.2 | chr5:120961200-120984033 |
| 27152 | Slc4a4 | NM_001197147.1 | chr5:89316284-89668681 | | 27247 | Slc9a1 | NM_016981.2 | chr4:132925687-132979613 |
| 27153 | Slc4a4 | NM_018760.2 | chr5:89316284-89668681 | | 27248 | Slc9a2 | NM_001033289.1 | chr1:40738556-40825730 |
| 27154 | Slc4a5 | NM_001166067.1 | chr6:83187368-83254939 | | 27249 | Slc9a3 | NM_001081060.1 | chr13:74258962-74303512 |
| 27155 | Slc4a7 | NM_001033270.2 | chr14:15535538-15632457 | | 27250 | Slc9a3r1 | NM_012030.2 | chr11:115024654-115042492 |
| 27156 | Slc4a8 | NM_001592177-100654402 | chr15:100592177-100654402 | | 27251 | Slc9a3r2 | NM_023055.2 | chr17:24776226-24787250 |
| 27157 | Slc4a9 | NM_001271544.1 | chr18:36687805-36715926 | | 27252 | Slc9a3r2 | NM_023449.3 | chr17:24776226-24787250 |
| 27158 | Slc4a9 | NM_001271545.1 | chr18:36687805-36715926 | | 27253 | Slc9a4 | NM_177084.3 | chr1:40637071-40687576 |
| 27159 | Slc4a9 | NM_001271546.1 | chr18:36687805-36715926 | | 27254 | Slc9a5 | NM_001081332.1 | chr8:107872157-107893781 |
| 27160 | Slc4a9 | NM_001271547.1 | chr18:36687805-36715926 | | 27255 | Slc9a6 | NM_172780.3 | chrX:53863011-53917407 |
| 27161 | Slc4a9 | NM_172783.2 | chr18:36687805-36715926 | | 27256 | Slc9a7 | NM_177353.3 | chrX:19682880-19868890 |
| 27162 | Slc50a1 | NM_009057.3 | chr3:89072167-89074492 | | 27257 | Slc9a8 | NM_148929.3 | chr2:167247220-167302498 |
| 27163 | Slc51a | NM_145932.3 | chr16:32475663-32487965 | | 27258 | Slc9a8 | NM_178371.3 | chr2:167247220-167302498 |
| 27164 | Slc51b | NM_178933.3 | chr9:65260560-65270680 | | 27259 | Slc9a9 | NM_177909.5 | chr9:94570311-95130671 |
| 27165 | Slc52a2 | NM_029643.3 | chr15:76369372-76372560 | | 27260 | Slc9b1 | NM_028946.3 | chr3:135011900-135060791 |
| 27166 | Slc52a3 | NM_001164819.1 | chr2:151822246-151834994 | | 27261 | Slc9b2 | NM_178877.6 | chr3:134970663-135005731 |
| 27167 | Slc52a3 | NM_001164820.1 | chr2:151822246-151834994 | | 27262 | Slc9c1 | NM_198106.4 | chr16:45535378-45607114 |
| 27168 | Slc52a3 | NM_027172.3 | chr2:151822246-151834994 | | 27263 | Slco1a1 | NM_013797.5 | chr6:141855801-141895483 |
| 27169 | Slc5a1 | NM_019810.4 | chr5:33446867-33505348 | | 27264 | Slco1a4 | NM_030687.1 | chr6:141715960-141804692 |
| 27170 | Slc5a10 | NM_001161486284-61534301 | chr11:61486284-61534301 | | 27265 | Slco1a5 | NM_001267707.1 | chr6:142182747-142271501 |
| 27171 | Slc5a11 | NM_146198.2 | chr7:130358379-130416765 | | 27266 | Slco1a5 | NM_130861.3 | chr6:142182747-142271501 |
| 27172 | Slc5a12 | NM_001003915.2 | chr2:110437455-110489502 | | 27267 | Slco1a6 | NM_023718.3 | chr6:142034288-142134670 |
| 27173 | Slc5a12 | NM_001177624.1 | chr2:110437455-110489502 | | 27268 | Slco1b2 | NM_020495.1 | chr6:141578038-141635156 |
| 27174 | Slc5a2 | NM_133254.3 | chr7:135409211-135415947 | | 27269 | Slco1c1 | NM_001177772.1 | chr6:141472906-141518698 |
| 27175 | Slc5a3 | NM_017391.3 | chr16:92058567-92087718 | | 27270 | Slco1c1 | NM_021471.2 | chr6:141472906-141518698 |
| 27176 | Slc5a4a | NM_133184.2 | chr10:75610195-75652010 | | 27271 | Slco2a1 | NM_033314.3 | chr9:102910818-102990179 |
| 27177 | Slc5a4b | NM_023219.2 | chr10:75521365-75573763 | | 27272 | Slco2b1 | NM_001252530.1 | chr7:106806313-106859850 |
| 27178 | Slc5a5 | NM_053248.2 | chr8:73406787-73416656 | | 27273 | Slco2b1 | NM_001252531.1 | chr7:106806313-106859850 |
| 27179 | Slc5a6 | NM_001177621.1 | chr5:31235515-31651218 | | 27274 | Slco2b1 | NM_175316.3 | chr7:106806313-106859850 |
| 27180 | Slc5a6 | NM_001177622.1 | chr5:31235515-31651218 | | 27275 | Slco3a1 | NM_001038643.1 | chr7:81420303-81699666 |
| 27181 | Slc5a6 | NM_177870.5 | chr5:31235515-31651218 | | 27276 | Slco3a1 | NM_023908.2 | chr7:81420303-81699666 |
| 27182 | Slc5a7 | NM_022025.4 | chr17:54412914-54438359 | | 27277 | Slco4a1 | NM_148933.2 | chr2:180195682-180209557 |
| 27183 | Slc5a8 | NM_145423.2 | chr10:88348736-88392260 | | 27278 | Slco4c1 | NM_172658.3 | chr1:98715360-98768748 |
| 27184 | Slc5a9 | NM_145551.4 | chr4:111547981-111575401 | | 27279 | Slco5a1 | NM_172841.2 | chr1:12856630-12981216 |
| 27185 | Slc6a1 | NM_178703.4 | chr6:114232628-114267519 | | 27280 | Slco6b1 | NM_001039475.1 | chr1:98802752-98894137 |
| 27186 | Slc6a11 | NM_172890.3 | chr6:114081234-114199880 | | 27281 | Slco6c1 | NM_028942.4 | chr1:98956025-99024880 |

Fig. 25 - 145

| | | | |
|---|---|---|---|
| 27282 | Slco6d1 | NM_001164233.1 | chr1:100317700-100405957 |
| 27283 | Slco6d1 | NM_027584.1 | chr1:100317700-100405957 |
| 27284 | Slfn1 | NM_011407.1 | chr11:82930346-82936161 |
| 27285 | Slfn10-ps | NR_073523.1 | chr11:82841629-82854035 |
| 27286 | Slfn10-ps | NR_073524.1 | chr11:82841629-82854035 |
| 27287 | Slfn14 | NM_001166028.1 | chr11:83088613-83100228 |
| 27288 | Slfn2 | NM_011408.1 | chr11:82878613-82884180 |
| 27289 | Slfn3 | NM_011409.1 | chr11:83004831-83028656 |
| 27290 | Slfn4 | NM_011410.3 | chr11:82988687-83003718 |
| 27291 | Slfn5 | NM_183201.4 | chr11:82765604-82778352 |
| 27292 | Slfn5os | NR_045932.1 | chr11:82755843-82774183 |
| 27293 | Slfn8 | NM_001167743.1 | chr11:82815659-82834312 |
| 27294 | Slfn8 | NM_181545.4 | chr11:82815659-82834312 |
| 27295 | Slfn9 | NM_172796.2 | chr11:82793805-82805332 |
| 27296 | Slfnl1 | NM_177570.3 | chr4:120204835-120209266 |
| 27297 | Slirp | NM_026908.3 | chr12:88784846-88790874 |
| 27298 | Slit1 | NM_015748.3 | chr19:41674746-41818346 |
| 27299 | Slit2 | NM_001291227.1 | chr5:48374393-48697521 |
| 27300 | Slit2 | NM_001291228.1 | chr5:48374393-48697521 |
| 27301 | Slit2 | NM_178804.4 | chr5:48374393-48697521 |
| 27302 | Slit2 | NR_111900.1 | chr5:48374393-48697521 |
| 27303 | Slit3 | NM_011412.3 | chr11:34934958-35522009 |
| 27304 | Slitrk1 | NM_199065.2 | chr14:109309205-109313456 |
| 27305 | Slitrk2 | NM_001161431.1 | chrX:63902492-63914577 |
| 27306 | Slitrk2 | NM_198633.2 | chrX:63902492-63914577 |
| 27307 | Slitrk3 | NM_198864.2 | chr3:72852046-72860865 |
| 27308 | Slitrk4 | NM_178740.4 | chrX:61522618-61530171 |
| 27309 | Slitrk5 | NM_198866.1 | chr14:112074336-112082357 |
| 27310 | Slitrk6 | NM_175499.4 | chr14:111147799-111154371 |
| 27311 | Slk | NM_001164639.1 | chr19:47654508-47719736 |
| 27312 | Slk | NM_009289.3 | chr19:47654508-47719736 |
| 27313 | Slmap | NM_032008.3 | chr14:27232660-27353226 |
| 27314 | Slmo1 | NM_144867.2 | chr18:67624502-67640235 |
| 27315 | Slmo2 | NM_025531.2 | chr2:174290591-174298442 |
| 27316 | Sln | NM_025540.2 | chr9:53698057-53701656 |
| 27317 | Slpi | NM_011414.3 | chr2:164179806-164182243 |
| 27318 | Sltm | NM_025690.3 | chr9:70390584-70440039 |
| 27319 | Sltm | NM_026337.1 | chr9:70390584-70440039 |
| 27320 | Slu7 | NM_148673.3 | chr11:43247232-43261483 |
| 27321 | Slu7 | NM_198936.1 | chr11:43247232-43261483 |
| 27322 | Slurp1 | NM_020519.1 | chr15:74557073-74558456 |
| 27323 | Slx | NM_001136475.1 | chrX:25949783-25972691 |
| 27324 | Slx1b | NM_029420.4 | chr7:133832440-133839297 |
| 27325 | Slx1b | NR_033446.1 | chr7:133832440-133839297 |
| 27326 | Slx4 | NM_177472.5 | chr16:3979105-4001678 |
| 27327 | Slx4ip | NM_001038641.1 | chr2:136699515-136895514 |
| 27328 | Slx4ip | NM_028201.2 | chr2:136699515-136895514 |
| 27329 | Slx4ip | NM_028834.2 | chr2:136699515-136895514 |
| 27330 | Slxl1 | NM_029181.1 | chrX:52480052-52496913 |
| 27331 | Sly | NM_201530.2 | chrY_random:30931020-3095 7169 |
| 27332 | Sly | NM_201530.2 | chrY_random:28156517-2818 2665 |
| 27333 | Sly | NM_201530.2 | chrY_random:1294311-13205 09 |
| 27334 | Smad1 | NM_008539.3 | chr8:81862297-81923367 |
| 27335 | Smad2 | NM_001252481.1 | chr18:76401354-76471401 |
| 27336 | Smad2 | NM_010754.5 | chr18:76401354-76471401 |
| 27337 | Smad3 | NM_016769.4 | chr9:63494573-63605801 |
| 27338 | Smad4 | NM_008540.2 | chr18:73798666-73863395 |
| 27339 | Smad5 | NM_001164041.1 | chr13:56804370-56843739 |
| 27340 | Smad5 | NM_001164042.1 | chr13:56804370-56843739 |
| 27341 | Smad5 | NM_008541.3 | chr13:56804370-56843739 |
| 27342 | Smad6 | NM_008542.3 | chr9:63800882-63869866 |
| 27343 | Smad7 | NM_001042660.1 | chr18:75527018-75555588 |
| 27344 | Smad9 | NM_019483.5 | chr3:54559503-54605191 |
| 27345 | Smagp | NM_001033872.2 | chr15:100451770-100467371 |
| 27346 | Smagp | NM_001285413.1 | chr15:100451770-100467371 |
| 27347 | Smagp | NM_001285414.1 | chr15:100451770-100467371 |
| 27348 | Smagp | NM_174992.4 | chr15:100451770-100467371 |
| 27349 | Smagp | NR_104337.1 | chr15:100451770-100467371 |
| 27350 | Smagp | NR_104338.1 | chr15:100451770-100467371 |
| 27351 | Smap1 | NM_001290683.1 | chr1:23768764-23929220 |
| 27352 | Smap1 | NM_028534.3 | chr1:23768764-23929220 |
| 27353 | Smap1 | NR_110972.1 | chr1:23768764-23929220 |
| 27354 | Smap2 | NM_133716.3 | chr4:120640922-120689852 |
| 27355 | Smarca1 | NM_001290708.1 | chrX:45162546-45245729 |
| 27356 | Smarca1 | NM_053123.4 | chrX:45162546-45245729 |
| 27357 | Smarca2 | NM_011416.2 | chr19:26679649-26898397 |
| 27358 | Smarca2 | NM_026003.2 | chr19:26679649-26898397 |
| 27359 | Smarca4 | NM_001174078.1 | chr9:21420612-21508674 |
| 27360 | Smarca4 | NM_001174079.1 | chr9:21420612-21508674 |
| 27361 | Smarca4 | NM_011417.3 | chr9:21420612-21508674 |
| 27362 | Smarca5 | NM_053124.2 | chr8:83223842-83263358 |
| 27363 | Smarca5-ps | NR_002888.2 | chr4:145054112-145057864 |
| 27364 | Smarcad1 | NM_001253392.1 | chr6:64992660-65066043 |
| 27365 | Smarcad1 | NM_007958.1 | chr6:64992660-65066043 |
| 27366 | Smarcal1 | NM_018817.2 | chr1:72629824-72683364 |
| 27367 | Smarcb1 | NM_001161853.1 | chr10:75359513-75384359 |
| 27368 | Smarcb1 | NM_011418.2 | chr10:75359513-75384359 |
| 27369 | Smarcc2 | NM_009211.2 | chr10:110034527-110142682 |
| 27370 | Smarcc2 | NM_001114096.1 | chr10:127896291-127927230 |
| 27371 | Smarcc2 | NM_001114097.1 | chr10:127896291-127927230 |
| 27372 | Smarcc2 | NM_198160.2 | chr10:127896291-127927230 |
| 27373 | Smarcd1 | NM_031842.2 | chr15:99537717-99544426 |
| 27374 | Smarcd2 | NM_001130187.1 | chr11:106124484-106134286 |
| 27375 | Smarcd2 | NM_031878.2 | chr11:106124484-106134286 |
| 27376 | Smarcd3 | NM_025891.3 | chr5:24098439-24107820 |
| 27377 | Smarce1 | NM_020618.4 | chr11:99070361-99092331 |
| 27378 | Smc1a | NM_019710.2 | chrX:148450970-148496516 |
| 27379 | Smc1b | NM_080470.1 | chr15:84895118-84962387 |
| 27380 | Smc2 | NM_008017.4 | chr4:52452120-52501131 |
| 27381 | Smc2os | NR_045175.1 | chr4:52443155-52451836 |
| 27382 | Smc3 | NM_007790.3 | chr19:53674885-53720321 |
| 27383 | Smc4 | NM_133786.3 | chr3:68808894-68838545 |
| 27384 | Smc5 | NM_001252684.1 | chr19:23280930-23348387 |
| 27385 | Smc5 | NM_001252685.1 | chr19:23280930-23348387 |
| 27386 | Smc5 | NM_153808.2 | chr19:23280930-23348387 |
| 27387 | Smc6 | NM_025695.4 | chr12:11272692-11326591 |
| 27388 | Smchd1 | NM_028887.3 | chr17:71693833-71824683 |
| 27389 | Smco1 | NM_183283.2 | chr16:32271694-32274865 |
| 27390 | Smco2 | NM_027059.1 | chr6:146798631-146819926 |
| 27391 | Smco3 | NM_001039558.2 | chr6:136778452-136783971 |
| 27392 | Smco4 | NM_133214.2 | chr9:15309938-15349703 |
| 27393 | Smcp | NM_008574.3 | chr3:92387787-92392946 |
| 27394 | Smcr8 | NM_001085440.1 | chr11:60591026-60601789 |
| 27395 | Smcr8 | NM_175491.4 | chr11:60591026-60601789 |
| 27396 | Smdt1 | NM_026914.1 | chr15:82176475-82179492 |
| 27397 | Smek1 | NM_001160214.1 | chr12:102277618-102327137 |
| 27398 | Smek1 | NM_211355.2 | chr12:102277618-102327137 |
| 27399 | Smek2 | NM_134034.2 | chr11:29072906-29120797 |
| 27400 | Smg1 | NM_001031814.1 | chr7:125274625-125387151 |
| 27401 | Smg5 | NM_178246.3 | chr3:88140181-88166259 |
| 27402 | Smg6 | NM_001002764.1 | chr11:74739374-74977950 |
| 27403 | Smg7 | NM_001005507.2 | chr1:154684124-154749776 |
| 27404 | Smg7 | NM_001160256.1 | chr1:154684124-154749776 |
| 27405 | Smg7 | NM_001160257.1 | chr1:154684124-154749776 |
| 27406 | Smg8 | NM_024262.1 | chr11:86891233-86900279 |
| 27407 | Smg9 | NM_028047.2 | chr7:25184646-25207796 |
| 27408 | Smgc | NM_198927.3 | chr15:91668759-91691866 |
| 27409 | Smim1 | NM_001163721.1 | chr4:153385911-153400153 |
| 27410 | Smim1 | NM_001163722.1 | chr4:153385911-153400153 |
| 27411 | Smim11 | NM_138743.2 | chr16:92301548-92313286 |
| 27412 | Smim12 | NM_030252.1 | chr4:126921027-126925053 |
| 27413 | Smim13 | NM_001155577.2 | chr13:41345212-41371946 |
| 27414 | Smim14 | NM_133697.3 | chr5:65839993-65884074 |
| 27415 | Smim15 | NM_001048250.2 | chr13:108834667-108839340 |
| 27416 | Smim18 | NM_001206849.1 | chr8:34852584-34858242 |
| 27417 | Smim19 | NM_001012667.2 | chr8:23573085-23680088 |
| 27418 | Smim19 | NM_001146117.1 | chr8:23573085-23680088 |
| 27419 | Smim20 | NM_001145433.1 | chr5:53658344-53669779 |
| 27420 | Smim22 | NM_001253796.1 | chr16:5007380-5008401 |
| 27421 | Smim22 | NM_001253797.1 | chr16:5007380-5008401 |
| 27422 | Smim22 | NM_001253802.1 | chr16:5007380-5008401 |
| 27423 | Smim22 | NM_001253803.1 | chr16:5007380-5008401 |
| 27424 | Smim22 | NR_045595.1 | chr16:5007380-5008401 |
| 27425 | Smim22 | NR_045596.1 | chr16:5007380-5008401 |
| 27426 | Smim23 | NM_027050.1 | chr11:32720375-32724594 |
| 27427 | Smim24 | NM_001099917.1 | chr10:80855808-80857824 |
| 27428 | Smim3 | NM_134133.2 | chr18:60633844-60661637 |
| 27429 | Smim4 | NR_024069.2 | chr14:31937690-31942116 |
| 27430 | Smim5 | NM_183259.3 | chr11:115761453-115767583 |
| 27431 | Smim6 | NM_001162998.1 | chr11:115773331-115775231 |
| 27432 | Smim7 | NM_172396.3 | chr8:75089096-75094947 |
| 27433 | Smim8 | NM_025471.2 | chr4:34715920-34725586 |
| 27434 | Smim9 | NM_001033786.2 | chrX:72391395-72409090 |
| 27435 | Smlr1 | NM_001195596.1 | chr16:25247748-25256078 |
| 27436 | Smn1 | NM_001252629.1 | chr13:100893159-100907653 |
| 27437 | Smn1 | NM_011420.2 | chr13:100893159-100907653 |
| 27438 | Smndc1 | NM_172429.2 | chr19:53453703-53465063 |
| 27439 | Smo | NM_176996.4 | chr6:29685496-29711366 |
| 27440 | Smoc1 | NM_001146217.1 | chr12:81127794-82287401 |
| 27441 | Smoc1 | NM_022316.2 | chr12:81127794-82287401 |
| 27442 | Smoc2 | NM_022315.2 | chr17:14416513-14541797 |
| 27443 | Smok2a | NM_013741.1 | chr17:13414053-13420524 |
| 27444 | Smok2b | NM_001167913.2 | chr17:13423128-13430055 |
| 27445 | Smok3a | NM_001126045.1 | chr5:138462503-138475893 |
| 27446 | Smok3a | NM_001168602.1 | chr5:138462503-138475893 |
| 27447 | Smok3b | NM_001039889.3 | chr5:138478451-138491861 |
| 27448 | Smok4a | NR_030763.1 | chr17:13714322-13721300 |
| 27449 | Smox | NM_001177833.1 | chr2:131317597-131350919 |
| 27450 | Smox | NM_001177834.1 | chr2:131317597-131350919 |
| 27451 | Smox | NM_001177835.1 | chr2:131317597-131350919 |
| 27452 | Smox | NM_001177836.1 | chr2:131317597-131350919 |
| 27453 | Smox | NM_001177837.1 | chr2:131317597-131350919 |
| 27454 | Smox | NM_001177838.1 | chr2:131317597-131350919 |
| 27455 | Smox | NM_001177839.1 | chr2:131317597-131350919 |
| 27456 | Smox | NM_001177840.1 | chr2:131317597-131350919 |
| 27457 | Smox | NM_145533.2 | chr2:131317597-131350919 |
| 27458 | Smpd1 | NM_011421.2 | chr7:112702873-112706903 |
| 27459 | Smpd2 | NM_009213.2 | chr10:41206977-41210146 |
| 27460 | Smpd3 | NM_021491.3 | chr8:108776447-108861888 |
| 27461 | Smpd4 | NM_001164609.1 | chr16:17619446-17644923 |
| 27462 | Smpd4 | NM_001164610.1 | chr16:17619446-17644923 |
| 27463 | Smpd4 | NM_001164611.1 | chr16:17619446-17644923 |
| 27464 | Smpd4 | NM_029945.3 | chr16:17619446-17644923 |
| 27465 | Smpd5 | NM_001195537.1 | chr15:76124964-76127326 |
| 27466 | Smpdl3a | NM_020561.2 | chr10:57514349-57531636 |
| 27467 | Smpdl3b | NM_133888.2 | chr4:132288880-132313086 |
| 27468 | Smpx | NM_001252591.2 | chrX:154136904-154190523 |
| 27469 | Smpx | NR_045569.1 | chrX:154136904-154190523 |

Fig. 25 - 146

| | | | | | | | | |
|---|---|---|---|---|---|---|---|---|
| 27470 | Smpx | NR_103722.1 | chrX:154136904-154190523 | | 27565 | Snora47 | NR_034043.1 | chr13:96100566-96100691 |
| 27471 | Smr2 | NM_001252679.1 | chr5:88515580-88538078 | | 27566 | Snora52 | NR_034049.2 | chr7:148634702-148634835 |
| 27472 | Smr2 | NM_001252680.1 | chr5:88515580-88538078 | | 27567 | Snora5c | NR_034042.1 | chr11:6520322-6520422 |
| 27473 | Smr2 | NM_001252681.1 | chr5:88515580-88538078 | | 27568 | Snora61 | NR_034046.1 | chr4:131866222-131866283 |
| 27474 | Smr2 | NM_021289.2 | chr5:88515580-88538078 | | 27569 | Snora62 | NR_002902.2 | chr9:120039552-120039679 |
| 27475 | Smr3a | NM_011422.3 | chr5:88431549-88437559 | | 27570 | Snora64 | NR_002897.1 | chr17:24857734-24857850 |
| 27476 | Sms | NM_009214.3 | chrX:153881885-153929978 | | 27571 | Snora65 | NR_002898.2 | chr2:32818821-32818938 |
| 27477 | Smtn | NM_001159284.1 | chr11:3417524-3439295 | | 27572 | Snora68 | NR_002901.1 | chr8:73419658-73419755 |
| 27478 | Smtn | NM_001284427.1 | chr11:3417524-3439295 | | 27573 | Snora69 | NR_002900.1 | chrX:34622907-34623028 |
| 27479 | Smtn | NM_001284428.1 | chr11:3417524-3439295 | | 27574 | Snora70 | NR_002899.1 | chrX:71517831-71517959 |
| 27480 | Smtn | NM_001284429.1 | chr11:3417524-3439295 | | 27575 | Snora74a | NR_002905.3 | chr18:35716684-35716881 |
| 27481 | Smtn | NM_013870.3 | chr11:3417524-3439295 | | 27576 | Snora75 | NR_028478.1 | chr1:88247745-88247860 |
| 27482 | Smtnl1 | NM_024230.2 | chr2:84651332-84662809 | | 27577 | Snora78 | NR_028515.1 | chr17:24856621-24856777 |
| 27483 | Smtnl2 | NM_177776.3 | chr11:72203615-72225215 | | 27578 | Snora7a | NR_028546.1 | chr6:115757993-115758121 |
| 27484 | Smu1 | NM_021535.4 | chr4:40682682-40704918 | | 27579 | Snora81 | NR_034048.1 | chr16:23110843-23111006 |
| 27485 | Smug1 | NM_027885.3 | chr15:102983720-102993715 | | 27580 | Snord100 | NR_037681.1 | chr10:23505560-23505627 |
| 27486 | Smurf1 | NM_001038627.1 | chr5:145637363-145726699 | | 27581 | Snord104 | NR_030703.1 | chr11:106362304-106362377 |
| 27487 | Smurf1 | NM_029438.3 | chr5:145637363-145726699 | | 27582 | Snord11 | NR_028521.1 | chr1:59761652-59761714 |
| 27488 | Smurf2 | NM_025481.2 | chr11:106681377-106782029 | | 27583 | Snord110 | NR_028547.1 | chr2:130101251-130101309 |
| 27489 | Smyd1 | NM_001160127.1 | chr6:71163933-71212275 | | 27584 | Snord111 | NR_028559.1 | chr8:113362435-113362498 |
| 27490 | Smyd1 | NM_009762.2 | chr6:71163933-71212275 | | 27585 | Snord116 | NR_002895.2 | chr7:67006618-67006708 |
| 27491 | Smyd2 | NM_026796.1 | chr1:191704370-191746167 | | 27586 | Snord116 | NR_002895.2 | chr7:66938957-66939047 |
| 27492 | Smyd3 | NM_027188.3 | chr1:180885169-181448134 | | 27587 | Snord116 | NR_002895.2 | chr7:66951115-66951205 |
| 27493 | Smyd4 | NM_001102611.1 | chr11:75161934-75219207 | | 27588 | Snord116 | NR_002895.2 | chr7:67021820-67021910 |
| 27494 | Smyd5 | NM_144918.2 | chr6:85381969-85396423 | | 27589 | Snord116 | NR_002895.2 | chr7:67004101-67004191 |
| 27495 | Snai1 | NM_011427.2 | chr2:167363726-167368311 | | 27590 | Snord116 | NR_002895.2 | chr7:66874527-66934248 |
| 27496 | Snai2 | NM_011415.2 | chr16:14705951-14709475 | | 27591 | Snord116l1 | NR_033778.1 | chr7:67014217-67014307 |
| 27497 | Snai3 | NM_013914.2 | chr8:124978105-124984592 | | 27592 | Snord116l2 | NR_033779.1 | chr7:67011675-67011765 |
| 27498 | Snap23 | NM_001177792.1 | chr2:120393406-120426458 | | 27593 | Snord116l2 | NR_033779.1 | chr7:67019267-67019357 |
| 27499 | Snap23 | NM_001177793.1 | chr2:120393406-120426458 | | 27594 | Snord116l2 | NR_033779.1 | chr7:66874527-66934248 |
| 27500 | Snap23 | NM_009222.3 | chr2:120393406-120426458 | | 27595 | Snord12 | NR_028540.1 | chr2:166890793-166890858 |
| 27501 | Snap25 | NM_001291056.1 | chr2:136539185-136608164 | | 27596 | Snord123 | NR_028575.2 | chr15:32171600-32171687 |
| 27502 | Snap25 | NM_011428.3 | chr2:136539185-136608164 | | 27597 | Snord15a | NR_002172.1 | chr7:106631295-106631442 |
| 27503 | Snap29 | NM_023348.4 | chr16:17406093-17430919 | | 27598 | Snord15b | NR_002173.1 | chr7:106628073-106628217 |
| 27504 | Snap47 | NM_144521.2 | chr11:59220651-59263458 | | 27599 | Snord16a | NR_028548.1 | chr9:64023239-64023329 |
| 27505 | Snap91 | NM_001277982.1 | chr9:86659229-86775284 | | 27600 | Snord17 | NR_030762.1 | chr2:144091718-144091938 |
| 27506 | Snap91 | NM_001277983.1 | chr9:86659229-86775284 | | 27601 | Snord19 | NR_028523.1 | chr14:31829405-31829458 |
| 27507 | Snap91 | NM_001277985.1 | chr9:86659229-86775284 | | 27602 | Snord1a | NR_028570.1 | chr11:116535911-116535986 |
| 27508 | Snap91 | NM_001277986.1 | chr9:86659229-86775284 | | 27603 | Snord1b | NR_028567.1 | chr11:116535461-116535537 |
| 27509 | Snap91 | NM_013669.2 | chr9:86659229-86775284 | | 27604 | Snord1c | NR_028569.1 | chr11:116533819-116533896 |
| 27510 | Snap91 | NR_102729.1 | chr9:86659229-86775284 | | 27605 | Snord2 | NR_030705.1 | chr16:23109026-23109093 |
| 27511 | Snapc1 | NM_178392.4 | chr12:75065516-75085807 | | 27606 | Snord22 | NR_004445.1 | chr19:8800356-8800481 |
| 27512 | Snapc2 | NM_133968.1 | chr8:4253101-4256220 | | 27607 | Snord23 | NR_028539.1 | chr16:16524111-16524209 |
| 27513 | Snapc3 | NM_029949.3 | chr4:83063647-83099244 | | 27608 | Snord32a | NR_000002.8 | chr7:52382753-52382833 |
| 27514 | Snapc4 | NM_172394.4 | chr2:26218284-26236173 | | 27609 | Snord33 | NR_001277.2 | chr7:52382234-52382315 |
| 27515 | Snapc4 | NR_033572.1 | chr2:26218284-26236173 | | 27610 | Snord34 | NR_002455.1 | chr7:52381973-52382038 |
| 27516 | Snapc5 | NM_183316.2 | chr9:64027103-64030495 | | 27611 | Snord35a | NR_000003.8 | chr7:52381717-52381805 |
| 27517 | Snapin | NM_133854.3 | chr3:90291948-90294935 | | 27612 | Snord35b | NR_000004.8 | chr7:52378396-52378481 |
| 27518 | Snca | NM_001042451.2 | chr6:60681566-60779849 | | 27613 | Snord37 | NR_028549.1 | chr10:80641706-80641758 |
| 27519 | Snca | NM_009221.2 | chr6:60681566-60779849 | | 27614 | Snord38a | NR_028524.1 | chr4:116827121-116827179 |
| 27520 | Sncaip | NM_001199151.1 | chr18:52927464-53075585 | | 27615 | Snord42a | NR_037682.1 | chr11:77994804-77994848 |
| 27521 | Sncaip | NM_001199153.1 | chr18:52927464-53075585 | | 27616 | Snord42b | NR_037683.1 | chr11:77996561-77996615 |
| 27522 | Sncaip | NM_001199154.1 | chr18:52927464-53075585 | | 27617 | Snord43 | NR_028281.1 | chr15:79913289-79913336 |
| 27523 | Sncaip | NM_026408.4 | chr18:52927464-53075585 | | 27618 | Snord45b | NR_028561.1 | chr3:153573531-153573575 |
| 27524 | Sncb | NM_033610.2 | chr13:54860220-54867801 | | 27619 | Snord45c | NR_028525.1 | chr3:153575093-153575153 |
| 27525 | Sncg | NM_011430.3 | chr14:35183459-35187855 | | 27620 | Snord47 | NR_028543.1 | chr1:162968223-162968287 |
| 27526 | Snd1 | NM_019776.2 | chr6:28430348-28838832 | | 27621 | Snord49a | NR_028550.1 | chr11:62416962-62417023 |
| 27527 | Sned1 | NM_172463.4 | chr1:95132474-95193025 | | 27622 | Snord49b | NR_028526.1 | chr11:62416588-62416650 |
| 27528 | Snf8 | NM_033568.2 | chr11:95896230-95908719 | | 27623 | Snord4a | NR_030702.1 | chr11:77995189-77995258 |
| 27529 | Snhg1 | NR_002896.3 | chr19:8797977-8800816 | | 27624 | Snord52 | NR_028527.1 | chr17:35087895-35087953 |
| 27530 | Snhg10 | NR_003145.3 | chr12:106268827-106270489 | | 27625 | Snord53 | NR_028551.1 | chr17:71990229-71990296 |
| 27531 | Snhg11 | NM_175692.3 | chr2:158201373-158211881 | | 27626 | Snord55 | NR_030704.1 | chr4:116828376-116828453 |
| 27532 | Snhg12 | NR_029468.1 | chr4:131864593-131866939 | | 27627 | Snord57 | NR_028528.1 | chr2:130103762-130103824 |
| 27533 | Snhg18 | NR_038186.1 | chr15:32170323-32174417 | | 27628 | Snord58b | NR_028552.1 | chr14:52688989-52689043 |
| 27534 | Snhg3 | NR_003270.2 | chr4:131907847-131909601 | | 27629 | Snord58b | NR_028552.1 | chr18:75160130-75163035 |
| 27535 | Snhg4 | NR_038073.1 | chr18:35713084-35717970 | | 27630 | Snord61 | NR_002903.2 | chrX:54644625-54644686 |
| 27536 | Snhg5 | NR_040721.1 | chr9:88415890-88417735 | | 27631 | Snord64 | NR_028529.1 | chr7:67123696-67123742 |
| 27537 | Snhg6 | NR_024067.2 | chr1:9932106-9934199 | | 27632 | Snord65 | NR_028541.1 | chr11:62418032-62418088 |
| 27538 | Snhg7 | NR_024068.2 | chr2:26492696-26495764 | | 27633 | Snord66 | NR_028530.1 | chr16:20684329-20684386 |
| 27539 | Snhg8 | NR_028516.1 | chr3:123210470-123211254 | | 27634 | Snord67 | NR_028553.1 | chr2:91436238-91436335 |
| 27540 | Snhg9 | NR_027900.2 | chr17:24856476-24856910 | | 27635 | Snord68 | NR_028128.1 | chr8:125626958-125627005 |
| 27541 | Snip1 | NM_175246.1 | chr4:124743936-124751287 | | 27636 | Snord69 | NR_028531.1 | chr14:31827479-31827537 |
| 27542 | Snn | NM_009223.3 | chr16:11066391-11075078 | | 27637 | Snord7 | NR_028362.1 | chr11:83107806-83107901 |
| 27543 | Snora15 | NR_003681.1 | chr5:130300437-130300552 | | 27638 | Snord70 | NR_028554.1 | chr1:59748802-59748854 |
| 27544 | Snora16a | NR_029412.1 | chr4:131865380-131865515 | | 27639 | Snord71 | NR_028532.1 | chr8:112363212-112363275 |
| 27545 | Snora17 | NR_028571.1 | chr2:26494710-26494841 | | 27640 | Snord72 | NR_028091.1 | chr15:5068421-5068480 |
| 27546 | Snora19 | NR_034047.1 | chr19:24994405-25036106 | | 27641 | Snord73a | NR_004417.1 | chr3:85942713-85942780 |
| 27547 | Snora19 | NR_034047.1 | chr19:60837018-60866596 | | 27642 | Snord8 | NR_028542.1 | chr14:52829461-52829559 |
| 27548 | Snora20 | NR_028479.1 | chr17:13115723-13115783 | | 27643 | Snord82 | NR_002851.1 | chr1:88252835-88252902 |
| 27549 | Snora21 | NR_028078.1 | chr11:97642953-97643080 | | 27644 | Snord83b | NR_028282.1 | chr15:79908933-79909009 |
| 27550 | Snora23 | NR_033336.1 | chr7:117189878-117190061 | | 27645 | Snord85 | NR_028565.1 | chr4:130305553-130305617 |
| 27551 | Snora24 | NR_028523.1 | chr3:123210855-123210984 | | 27646 | Snord87 | NR_004410.1 | chr1:9932551-9932624 |
| 27552 | Snora26 | NR_031758.1 | chr5:74489555-74489675 | | 27647 | Snord88a | NR_028533.1 | chr7:51505520-51505591 |
| 27553 | Snora28 | NR_033168.1 | chr12:112779157-112779277 | | 27648 | Snord88c | NR_028534.1 | chr7:51505225-51505308 |
| 27554 | Snora2b | NR_034052.1 | chr15:98356779-98356890 | | 27649 | Snord89 | NR_028555.1 | chr13:39605695-39605685 |
| 27555 | Snora3 | NR_028079.1 | chr7:116663646-116663765 | | 27650 | Snord90 | NR_028535.1 | chr2:37255581-37255648 |
| 27556 | Snora30 | NR_034045.1 | chr7:134671410-134671517 | | 27651 | Snord91a | NR_028562.1 | chr11:74718948-74719007 |
| 27557 | Snora31 | NR_028481.1 | chr14:76247730-76247841 | | 27652 | Snord92 | NR_028556.1 | chr17:71980619-71980701 |
| 27558 | Snora33 | NR_037680.1 | chr10:23505153-23505257 | | 27653 | Snord93 | NR_028536.1 | chr5:23358051-23358095 |
| 27559 | Snora34 | NR_034051.1 | chr15:98350148-98350265 | | 27654 | Snord94 | NR_028564.1 | chr11:48616641-48616708 |
| 27560 | Snora35 | NR_028446.1 | chrX:143428933-143429051 | | 27655 | Snord96a | NR_028563.1 | chr11:48615535-48615611 |
| 27561 | Snora36b | NR_034044.1 | chr1:187066805-187066917 | | 27656 | Snord99 | NR_028537.1 | chr4:131866618-131866673 |
| 27562 | Snora41 | NR_028558.1 | chr1:63225597-63225709 | | 27657 | Snph | NM_001291076.1 | chr2:151416284-151458329 |
| 27563 | Snora43 | NR_028572.1 | chr2:26493367-26493505 | | 27658 | Snph | NM_001291077.1 | chr2:151416284-151458329 |
| 27564 | Snora44 | NR_034050.1 | chr4:131865868-131865984 | | 27659 | Snph | NM_198214.3 | chr2:151416284-151458329 |

Fig. 25 - 147

| | | | |
|---|---|---|---|
| 27660 | Snrk | NM_001164572.1 | chr9:122026383-122078820 |
| 27661 | Snrk | NM_133741.2 | chr9:122026383-122078820 |
| 27662 | Snrnp200 | NM_177214.4 | chr2:127034139-127066187 |
| 27663 | Snrnp25 | NM_030093.3 | chr11:32105414-32108995 |
| 27664 | Snrnp27 | NM_025665.2 | chr6:86625162-86634485 |
| 27665 | Snrnp35 | NM_029532.2 | chr5:124933163-124941131 |
| 27666 | Snrnp40 | NM_025645.2 | chr4:130037378-130067278 |
| 27667 | Snrnp48 | NM_026382.2 | chr13:38296807-38319532 |
| 27668 | Snrnp70 | NM_009224.5 | chr7:52631823-52651017 |
| 27669 | Snrpa | NM_001046637.1 | chr7:27972024-27990405 |
| 27670 | Snrpa | NM_001285825.1 | chr7:27972024-27990405 |
| 27671 | Snrpa | NM_015782.3 | chr7:27972024-27990405 |
| 27672 | Snrpa1 | NM_021336.4 | chr7:73205221-73219473 |
| 27673 | Snrpb | NM_009225.2 | chr2:129997371-130005100 |
| 27674 | Snrpb2 | NM_021335.3 | chr2:142888804-142897788 |
| 27675 | Snrpc | NM_011432.2 | chr17:27977031-27988912 |
| 27676 | Snrpd1 | NM_009226.4 | chr18:10617793-10628228 |
| 27677 | Snrpd2 | NM_026943.1 | chr7:19735186-19738075 |
| 27678 | Snrpd3 | NM_026095.4 | chr10:74980786-74998185 |
| 27679 | Snrpe | NM_009227.3 | chr1:135500447-135506857 |
| 27680 | Snrpf | NM_027246.1 | chr10:93045774-93052403 |
| 27681 | Snrpg | NM_026506.2 | chr6:86321533-86328896 |
| 27682 | Snrpn | NM_001082961.1 | chr7:67127386-67285105 |
| 27683 | Snrpn | NM_001082962.1 | chr7:67127386-67285105 |
| 27684 | Snrpn | NM_013670.3 | chr7:67127386-67285105 |
| 27685 | Snta1 | NM_009228.2 | chr2:154202049-154233820 |
| 27686 | Sntb1 | NM_016667.3 | chr15:55470708-55738504 |
| 27687 | Sntb2 | NM_009229.4 | chr8:109459649-109538092 |
| 27688 | Sntg1 | NM_001290390.1 | chr1:8349819-9289958 |
| 27689 | Sntg1 | NM_001290392.1 | chr1:8349819-9289958 |
| 27690 | Sntg1 | NM_001290393.1 | chr1:8349819-9289958 |
| 27691 | Sntg1 | NM_027671.5 | chr1:8349819-9289958 |
| 27692 | Sntg2 | NM_172951.3 | chr12:30859421-31058240 |
| 27693 | Sntn | NM_177624.3 | chr14:14503389-14515662 |
| 27694 | Snupn | NM_178374.3 | chr9:56798730-56831006 |
| 27695 | Snurf | NM_033174.3 | chr7:67127387-67150042 |
| 27696 | Snw1 | NM_025507.2 | chr12:88790860-88813249 |
| 27697 | Snx1 | NM_019727.2 | chr9:65935933-65972693 |
| 27698 | Snx10 | NM_001127348.1 | chr6:51473901-51540669 |
| 27699 | Snx10 | NM_001127349.1 | chr6:51473901-51540669 |
| 27700 | Snx10 | NM_028035.4 | chr6:51473901-51540669 |
| 27701 | Snx11 | NM_001163389.1 | chr11:96628862-96638869 |
| 27702 | Snx11 | NM_028965.4 | chr11:96628862-96638869 |
| 27703 | Snx12 | NM_001110310.1 | chrX:98293124-98417902 |
| 27704 | Snx12 | NM_001110311.1 | chrX:98293124-98417902 |
| 27705 | Snx12 | NM_018875.2 | chrX:98293124-98417902 |
| 27706 | Snx13 | NM_001014973.2 | chr12:35731860-35832149 |
| 27707 | Snx14 | NM_172926.3 | chr9:88271584-88333789 |
| 27708 | Snx15 | NM_026912.1 | chr19:6119403-6128215 |
| 27709 | Snx16 | NM_001127191.2 | chr3:10417816-10440130 |
| 27710 | Snx16 | NM_029068.4 | chr3:10417816-10440130 |
| 27711 | Snx17 | NM_153680.1 | chr5:31495677-31501273 |
| 27712 | Snx18 | NM_130796.4 | chr13:113382386-114408772 |
| 27713 | Snx19 | NM_028874.2 | chr9:30234913-30274311 |
| 27714 | Snx2 | NM_026386.1 | chr18:53336018-53380514 |
| 27715 | Snx20 | NM_027840.3 | chr8:91150726-91160027 |
| 27716 | Snx21 | NM_133924.3 | chr2:164611521-164618270 |
| 27717 | Snx22 | NM_001025612.2 | chr9:65912983-65917538 |
| 27718 | Snx24 | NM_029394.3 | chr18:53405315-53550479 |
| 27719 | Snx25 | NM_207213.2 | chr8:47118614-47209500 |
| 27720 | Snx27 | NM_001082484.2 | chr3:94301463-94386638 |
| 27721 | Snx27 | NM_029721.2 | chr3:94301463-94386638 |
| 27722 | Snx29 | NM_001290148.1 | chr16:11322996-11755566 |
| 27723 | Snx29 | NM_028964.4 | chr16:11322996-11755566 |
| 27724 | Snx3 | NM_017472.4 | chr10:42221859-42255175 |
| 27725 | Snx30 | NM_172468.2 | chr4:59818521-59917612 |
| 27726 | Snx31 | NM_025712.4 | chr15:36433816-36485327 |
| 27727 | Snx32 | NM_001024560.2 | chr19:5495278-5510489 |
| 27728 | Snx33 | NM_175483.5 | chr9:56765006-56776178 |
| 27729 | Snx4 | NM_080572.2 | chr16:33251541-33299648 |
| 27730 | Snx5 | NM_001199188.1 | chr2:144075858-144096638 |
| 27731 | Snx5 | NM_024225.5 | chr2:144075858-144096638 |
| 27732 | Snx6 | NM_026998.3 | chr12:55847343-55896649 |
| 27733 | Snx7 | NM_001190156.1 | chr3:117484414-117571854 |
| 27734 | Snx7 | NM_029655.3 | chr3:117484414-117571854 |
| 27735 | Snx8 | NM_172277.2 | chr5:140816256-140865201 |
| 27736 | Snx9 | NM_025664.5 | chr17:5841379-5930711 |
| 27737 | Soat1 | NM_009230.3 | chr1:158358238-158404459 |
| 27738 | Soat2 | NM_146064.1 | chr15:101981005-101993867 |
| 27739 | Sobp | NM_175407.3 | chr10:42722305-42894336 |
| 27740 | Socs1 | NM_001271603.1 | chr16:10783901-10785629 |
| 27741 | Socs1 | NM_009896.2 | chr16:10783901-10785629 |
| 27742 | Socs2 | NM_001168655.1 | chr10:94874123-94879491 |
| 27743 | Socs2 | NM_001168656.1 | chr10:94874123-94879491 |
| 27744 | Socs2 | NM_001168657.1 | chr10:94874123-94879491 |
| 27745 | Socs2 | NM_007706.4 | chr10:94874123-94879491 |
| 27746 | Socs3 | NM_007707.2 | chr11:117827400-117830680 |
| 27747 | Socs4 | NM_080843.2 | chr14:47896817-47911266 |
| 27748 | Socs5 | NM_019654.2 | chr17:87507018-87536925 |
| 27749 | Socs6 | NM_018821.4 | chr18:89037271-89063599 |
| 27750 | Socs7 | NM_138657.3 | chr11:97223864-97259856 |
| 27751 | Sod1 | NM_011434.1 | chr16:90220986-90226569 |
| 27752 | Sod2 | NM_013671.3 | chr17:13200704-13210985 |
| 27753 | Sod3 | NM_011435.3 | chr5:52755042-52760977 |
| 27754 | Soga1 | NM_001164663.1 | chr2:156836177-156905001 |

| | | | |
|---|---|---|---|
| 27755 | Soga3 | NM_026138.2 | chr10:28863801-28919434 |
| 27756 | Sohlh1 | NM_001001714.1 | chr2:25698516-25702768 |
| 27757 | Sohlh2 | NM_028937.3 | chr3:54985965-55013879 |
| 27758 | Son | NM_019973.2 | chr16:91648068-91679437 |
| 27759 | Son | NM_178880.4 | chr16:91648068-91679437 |
| 27760 | Sorbs1 | NM_001034962.1 | chr19:40366529-40588302 |
| 27761 | Sorbs1 | NM_001034963.1 | chr19:40366529-40588302 |
| 27762 | Sorbs1 | NM_001034964.1 | chr19:40366529-40588302 |
| 27763 | Sorbs1 | NM_009166.3 | chr19:40366529-40588302 |
| 27764 | Sorbs1 | NM_178362.1 | chr19:40366529-40588302 |
| 27765 | Sorbs2 | NM_001205219.1 | chr8:46593141-46913260 |
| 27766 | Sorbs2 | NM_172752.4 | chr8:46593141-46913260 |
| 27767 | Sorbs2os | NR_045739.1 | chr8:46808679-46804651 |
| 27768 | Sorbs3 | NM_001271407.1 | chr14:70580274-70607478 |
| 27769 | Sorbs3 | NM_001271408.1 | chr14:70580274-70607478 |
| 27770 | Sorbs3 | NM_001271409.1 | chr14:70580274-70607478 |
| 27771 | Sorbs3 | NM_011366.3 | chr14:70580274-70607478 |
| 27772 | Sorcs1 | NM_001252501.1 | chr19:50217790-50753136 |
| 27773 | Sorcs1 | NM_001290356.1 | chr19:50217790-50753136 |
| 27774 | Sorcs1 | NM_021377.3 | chr19:50217790-50753136 |
| 27775 | Sorcs2 | NM_030889.2 | chr5:36359830-36740788 |
| 27776 | Sorcs3 | NM_025696.3 | chr19:48280514-48879995 |
| 27777 | Sord | NM_146126.4 | chr2:122065574-122091073 |
| 27778 | Sorl1 | NM_011436.3 | chr9:41776571-41932372 |
| 27779 | Sort1 | NM_001271599.1 | chr3:108086981-108164437 |
| 27780 | Sort1 | NM_019972.3 | chr3:108086981-108164437 |
| 27781 | Sos1 | NM_009231.2 | chr17:80793091-80879793 |
| 27782 | Sos2 | NM_001135559.1 | chr12:70684747-70782839 |
| 27783 | Sost | NM_024449.6 | chr11:101823771-101828329 |
| 27784 | Sostdc1 | NM_025312.3 | chr12:37040755-37045039 |
| 27785 | Sowaha | NM_183173.2 | chr11:53290079-53293697 |
| 27786 | Sowahb | NM_175270.4 | chr5:93470148-93474048 |
| 27787 | Sowahc | NM_172939.3 | chr10:58684669-58689181 |
| 27788 | Sowahd | NM_173779.3 | chrX:34588839-34590413 |
| 27789 | Sox1 | NM_009233.3 | chr8:12395519-12399555 |
| 27790 | Sox10 | NM_011437.1 | chr15:78985342-78994920 |
| 27791 | Sox11 | NM_009234.6 | chr12:28019132-28027583 |
| 27792 | Sox12 | NM_011438.2 | chr2:152219347-152223782 |
| 27793 | Sox13 | NM_011439.2 | chr1:135278876-135320789 |
| 27794 | Sox14 | NM_011440.1 | chr9:99774524-99776589 |
| 27795 | Sox15 | NM_009235.2 | chr11:69468539-69470229 |
| 27796 | Sox17 | NM_001289464.1 | chr1:4481008-4487435 |
| 27797 | Sox17 | NM_001289465.1 | chr1:4481008-4487435 |
| 27798 | Sox17 | NM_001289466.1 | chr1:4481008-4487435 |
| 27799 | Sox17 | NM_001289467.1 | chr1:4481008-4487435 |
| 27800 | Sox17 | NM_011441.5 | chr1:4481008-4487435 |
| 27801 | Sox18 | NM_009236.2 | chr2:181404541-181406345 |
| 27802 | Sox2 | NM_011443.3 | chr3:34548927-34551382 |
| 27803 | Sox21 | NM_177753.3 | chr14:118632455-118636252 |
| 27804 | Sox2ot | NR_015580.2 | chr3:34459303-34576915 |
| 27805 | Sox3 | NM_009237.2 | chrX:58144540-58146605 |
| 27806 | Sox30 | NM_173384.2 | chr11:45793811-45831494 |
| 27807 | Sox4 | NM_009238.3 | chr13:29042588-29045551 |
| 27808 | Sox5 | NM_001113559.2 | chr6:143776944-144158088 |
| 27809 | Sox5 | NM_001243163.1 | chr6:143776944-144158088 |
| 27810 | Sox5 | NM_011444.3 | chr6:143776944-144158088 |
| 27811 | Sox5os3 | NR_040519.1 | chr6:144621387-144642352 |
| 27812 | Sox6 | NM_001025559.3 | chr7:122614385-123182258 |
| 27813 | Sox6 | NM_001025560.2 | chr7:122614385-123182258 |
| 27814 | Sox6 | NM_001277326.1 | chr7:122614385-123182258 |
| 27815 | Sox6 | NM_001277327.1 | chr7:122614385-123182258 |
| 27816 | Sox6 | NM_001277328.1 | chr7:122614385-123182258 |
| 27817 | Sox6 | NM_011445.4 | chr7:122614385-123182258 |
| 27818 | Sox7 | NM_011446.1 | chr14:64562542-64569569 |
| 27819 | Sox8 | NM_011447.3 | chr17:25702837-25707631 |
| 27820 | Sox9 | NM_011448.4 | chr11:112843523-112649071 |
| 27821 | Sp1 | NM_013672.2 | chr15:102236746-102266835 |
| 27822 | Sp100 | NM_013673.3 | chr1:87546624-87606023 |
| 27823 | Sp110 | NM_030194.1 | chr1:87473474-87541611 |
| 27824 | Sp110 | NM_175397.4 | chr1:87473474-87541611 |
| 27825 | Sp140 | NM_001013817.2 | chr1:87497278-87541611 |
| 27826 | Sp2 | NM_001080964.1 | chr11:96805459-96839002 |
| 27827 | Sp2 | NM_030220.3 | chr11:96805459-96839002 |
| 27828 | Sp3 | NM_001018042.3 | chr2:72774489-72827306 |
| 27829 | Sp3 | NM_001098425.3 | chr2:72774489-72827306 |
| 27830 | Sp3os | NR_045269.2 | chr2:72817489-72827306 |
| 27831 | Sp4 | NM_001166385.2 | chr12:119470158-119539913 |
| 27832 | Sp4 | NM_009239.4 | chr12:119470158-119539913 |
| 27833 | Sp5 | NM_022435.2 | chr2:70312979-70315783 |
| 27834 | Sp6 | NM_031183.2 | chr11:96874882-96886052 |
| 27835 | Sp7 | NM_130458.3 | chr15:102187607-102196702 |
| 27836 | Sp8 | NM_177082.4 | chr12:120084801-120091051 |
| 27837 | Sp9 | NM_001005343.2 | chr2:73109982-73113828 |
| 27838 | Spa17 | NM_011449.2 | chr9:37410878-37421305 |
| 27839 | Spaca1 | NM_001290443.1 | chr4:34111846-34137042 |
| 27840 | Spaca1 | NM_026293.3 | chr4:34111846-34137042 |
| 27841 | Spaca3 | NM_029367.1 | chr11:80671890-80683316 |
| 27842 | Spaca4 | NM_027055.3 | chr7:52980477-52981186 |
| 27843 | Spaca5 | NM_001085393.2 | chrX:20645613-20655085 |
| 27844 | Spaca6 | NM_001162909.1 | chr17:17967938-17976035 |
| 27845 | Spaca7 | NM_024279.2 | chr8:12573048-12600738 |
| 27846 | Spag1 | NM_012031.3 | chr15:36109284-36164932 |
| 27847 | Spag11a | NM_153115.1 | chr8:19157886-19159578 |
| 27848 | Spag11b | NM_001034905.2 | chr8:19140758-19143010 |
| 27849 | Spag11b | NM_001039563.3 | chr8:19140758-19143010 |

Fig. 25 - 148

| | | | |
|---|---|---|---|
| 27850 | Spag11b | NM_001286493.1 | chr8:19140758-19143010 |
| 27851 | Spag16 | NM_001271533.1 | chr1:69873543-70771706 |
| 27852 | Spag16 | NM_025728.4 | chr1:69873543-70771706 |
| 27853 | Spag16 | NM_029160.3 | chr1:69873543-70771706 |
| 27854 | Spag17 | NM_028892.4 | chr3:99689340-99947245 |
| 27855 | Spag4 | NM_139151.4 | chr2:155890948-155895235 |
| 27856 | Spag5 | NM_017407.2 | chr11:78115092-78135956 |
| 27857 | Spag6 | NM_015773.2 | chr16:16753109-16829456 |
| 27858 | Spag7 | NM_001167669.1 | chr11:70477270-70482918 |
| 27859 | Spag7 | NM_172561.3 | chr11:70477270-70482918 |
| 27860 | Spag8 | NM_001007463.1 | chr4:43664201-43666424 |
| 27861 | Spag8 | NM_001290462.1 | chr4:43664201-43666424 |
| 27862 | Spag9 | NM_001025428.1 | chr11:93857404-93987396 |
| 27863 | Spag9 | NM_001025429.1 | chr11:93857404-93987396 |
| 27864 | Spag9 | NM_001025430.1 | chr11:93857404-93987396 |
| 27865 | Spag9 | NM_001199203.1 | chr11:93857404-93987396 |
| 27866 | Spag9 | NM_001199204.1 | chr11:93857404-93987396 |
| 27867 | Spag9 | NM_001199205.1 | chr11:93857404-93987396 |
| 27868 | Spag9 | NM_027569.2 | chr11:93857404-93987396 |
| 27869 | Spam1 | NM_001079875.2 | chr6:24741187-24751048 |
| 27870 | Spam1 | NM_009241.3 | chr6:24741187-24751048 |
| 27871 | Sparc | NM_001290817.1 | chr11:55207660-55233582 |
| 27872 | Sparc | NM_009242.5 | chr11:55207660-55233582 |
| 27873 | Sparcl1 | NM_010097.4 | chr5:104508127-104543107 |
| 27874 | Spast | NM_001162870.1 | chr17:74738326-74790453 |
| 27875 | Spast | NM_016962.2 | chr17:74738326-74790453 |
| 27876 | Spata1 | NM_027617.3 | chr3:146120167-146162717 |
| 27877 | Spata13 | NM_001033272.1 | chr14:61253565-61383393 |
| 27878 | Spata16 | NM_027583.3 | chr3:26536552-26882134 |
| 27879 | Spata16 | NM_029150.4 | chr3:26536552-26882134 |
| 27880 | Spata17 | NM_028848.3 | chr1:188872285-189039325 |
| 27881 | Spata17 | NM_029067.1 | chr1:188872285-189039325 |
| 27882 | Spata18 | NM_178387.3 | chr5:74042618-74070723 |
| 27883 | Spata19 | NM_029299.3 | chr9:27204405-27209295 |
| 27884 | Spata2 | NM_170756.2 | chr2:167306636-167318374 |
| 27885 | Spata20 | NM_144827.4 | chr11:94340217-94346624 |
| 27886 | Spata21 | NM_177867.3 | chr4:140644259-140668674 |
| 27887 | Spata22 | NM_001045531.1 | chr1:73143242-73159546 |
| 27888 | Spata24 | NM_027733.5 | chr18:35816342-35821840 |
| 27889 | Spata24 | NM_029485.2 | chr18:35816342-35821840 |
| 27890 | Spata25 | NM_029370.1 | chr2:164652881-164654034 |
| 27891 | Spata2L | NM_030176.2 | chr8:125756158-125760109 |
| 27892 | Spata3 | NM_001122732.1 | chr1:87918516-87926533 |
| 27893 | Spata3 | NM_027029.2 | chr1:87918516-87926533 |
| 27894 | Spata3 | NM_027300.3 | chr1:87918516-87926533 |
| 27895 | Spata3 | NM_028647.4 | chr1:87918516-87926533 |
| 27896 | Spata31 | NM_030047.2 | chr13:65018713-65024503 |
| 27897 | Spata31d1a | NM_028157.2 | chr13:59801443-59807558 |
| 27898 | Spata31d1b | NM_001167593.1 | chr13:59813644-59820650 |
| 27899 | Spata31d1c | NM_001083890.2 | chr13:65134365-65139312 |
| 27900 | Spata31d1d | NM_177711.3 | chr13:59827285-59833113 |
| 27901 | Spata32 | NM_177801.3 | chr11:103069441-103079746 |
| 27902 | Spata33 | NM_177279.4 | chr8:125736757-125745945 |
| 27903 | Spata4 | NM_133711.3 | chr8:55686133-55695451 |
| 27904 | Spata45 | NM_029336.1 | chr1:192860700-192866820 |
| 27905 | Spata5 | NM_001163510.1 | chr3:37319201-37478017 |
| 27906 | Spata5 | NM_021343.2 | chr3:37319201-37478017 |
| 27907 | Spata5l1 | NM_001033256.3 | chr2:122456360-122458440 |
| 27908 | Spata6 | NM_026470.3 | chr4:111392614-111501745 |
| 27909 | Spata7 | NM_001289572.1 | chr12:99866351-99908029 |
| 27910 | Spata7 | NM_001289573.1 | chr12:99866351-99908029 |
| 27911 | Spata7 | NM_001289574.1 | chr12:99866351-99908029 |
| 27912 | Spata7 | NM_178914.4 | chr12:99866351-99908029 |
| 27913 | Spata9 | NM_029343.3 | chr13:76105186-76136416 |
| 27914 | Spatc1 | NM_028852.1 | chr15:76098519-76123002 |
| 27915 | Spatc1l | NM_029661.1 | chr10:76025016-76032945 |
| 27916 | Spats1 | NM_027649.3 | chr17:45585885-45611887 |
| 27917 | Spats2 | NM_139140.1 | chr15:98957275-99042897 |
| 27918 | Spats2l | NM_001164566.1 | chr1:57831704-58005241 |
| 27919 | Spats2l | NM_144852.4 | chr1:57831704-58005241 |
| 27920 | Spc24 | NM_026282.5 | chr9:21559885-21564730 |
| 27921 | Spc25 | NM_001199123.2 | chr2:69031951-69044247 |
| 27922 | Spc25 | NM_001199124.2 | chr2:69031951-69044247 |
| 27923 | Spc25 | NM_025565.4 | chr2:69031951-69044247 |
| 27924 | Spcs1 | NM_026911.3 | chr14:31813012-31814852 |
| 27925 | Spcs2 | NM_026568.3 | chr7:106986078-107007393 |
| 27926 | Spcs3 | NM_029701.1 | chr8:55605786-55615351 |
| 27927 | Spdef | NM_013891.4 | chr17:27851391-27865896 |
| 27928 | Spdl1 | NM_027411.2 | chr11:34622686-34647103 |
| 27929 | Spdya | NM_001142631.1 | chr17:71901400-71948101 |
| 27930 | Spdya | NM_029254.1 | chr17:71901400-71948101 |
| 27931 | Spdyb | NM_029048.3 | chr5:143977994-143987561 |
| 27932 | Specc1 | NM_001029936.3 | chr11:61770264-62036515 |
| 27933 | Specc1 | NM_001281818.1 | chr11:61770264-62036515 |
| 27934 | Specc1l | NM_001145826.1 | chr10:74674817-74775145 |
| 27935 | Specc1l | NM_153406.3 | chr10:74674817-74775145 |
| 27936 | Speer1-ps1 | NR_130340.7-1134627.3 | chr5:11340407-11346273 |
| 27937 | Speer2 | NM_173069.2 | chr16:69857118-69863989 |
| 27938 | Speer3 | NM_027850.3 | chr5:13791618-13796819 |
| 27939 | Speer4a | NM_029376.2 | chr5:26360810-26366045 |
| 27940 | Speer4b | NM_028561.2 | chr5:27822349-27827932 |
| 27941 | Speer4c | NM_001281511.1 | chr5:15215323-15220089 |
| 27942 | Speer4d | NM_001275789.3 | chr5:15124916-15129682 |
| 27943 | Speer4e | NM_001122661.1 | chr5:14933630-14938475 |
| 27944 | Speer4f | NM_027609.2 | chr5:16981939-16986754 |
| 27945 | Speer5-ps1 | NR_001582.2 | chr10:43890252-43939391 |
| 27946 | Speer5-ps1 | NR_027506.1 | chr10:43890252-43939391 |
| 27947 | Speer6-ps1 | NR_001581.2 | chr13:3148720-3188924 |
| 27948 | Speer7-ps1 | NR_001585.3 | chr5:15186528-15220414 |
| 27949 | Speer8-ps1 | NR_001584.2 | chr5:14945294-14978541 |
| 27950 | Speer9-ps1 | NR_001583.3 | chr7:3128145-3144993 |
| 27951 | Spef1 | NM_027641.2 | chr2:130995996-131000546 |
| 27952 | Spef2 | NM_177123.4 | chr15:9592490-9678561 |
| 27953 | Speg | NM_001085370.1 | chr1:75371871-75428881 |
| 27954 | Speg | NM_001085371.1 | chr1:75371871-75428881 |
| 27955 | Speg | NM_001173477.1 | chr1:75371871-75428881 |
| 27956 | Speg | NM_007463.4 | chr1:75371871-75428881 |
| 27957 | Spem1 | NM_028855.1 | chr11:69634372-69635667 |
| 27958 | Spen | NM_019763.2 | chr4:141023805-141094512 |
| 27959 | Spert | NM_001164139.1 | chr14:75982640-75992923 |
| 27960 | Spert | NM_001164140.1 | chr14:75982640-75992923 |
| 27961 | Spert | NM_001164141.1 | chr14:75982640-75992923 |
| 27962 | Spert | NM_026457.2 | chr14:75982640-75992923 |
| 27963 | Spesp1 | NM_025721.2 | chr9:62118535-62129986 |
| 27964 | Spg11 | NM_145531.2 | chr2:121879262-121944122 |
| 27965 | Spg20 | NM_001144987.1 | chr3:54916029-54941254 |
| 27966 | Spg20 | NM_001144988.1 | chr3:54916029-54941254 |
| 27967 | Spg20 | NM_144895.2 | chr3:54916029-54941254 |
| 27968 | Spg21 | NM_138584.2 | chr9:65308743-65336277 |
| 27969 | Spg7 | NM_153176.4 | chr8:125589407-125621651 |
| 27970 | Sphk1 | NM_001172472.1 | chr11:116393224-116397989 |
| 27971 | Sphk1 | NM_001172473.1 | chr11:116393224-116397989 |
| 27972 | Sphk1 | NM_001172475.1 | chr11:116393224-116397989 |
| 27973 | Sphk1 | NM_011451.1 | chr11:116393224-116397989 |
| 27974 | Sphk1 | NM_025367.6 | chr11:116393224-116397989 |
| 27975 | Sphk2 | NM_001172561.1 | chr7:52960616-52973372 |
| 27976 | Sphk2 | NM_020011.5 | chr7:52960616-52973372 |
| 27977 | Sphk2 | NM_203280.3 | chr7:52960616-52973372 |
| 27978 | Sphkap | NM_172430.3 | chr1:83252355-83404775 |
| 27979 | Spi1 | NM_011355.1 | chr2:90936953-90955913 |
| 27980 | Spib | NM_019866.1 | chr7:51781364-51787441 |
| 27981 | Spic | NM_011461.3 | chr10:88138014-88145768 |
| 27982 | Spice1 | NM_144550.4 | chr16:44347513-44388605 |
| 27983 | Spidr | NM_146068.4 | chr16:15889318-16146944 |
| 27984 | Spin1 | NM_001283028.1 | chr13:51196248-51247931 |
| 27985 | Spin1 | NM_001283029.1 | chr13:51196248-51247931 |
| 27986 | Spin1 | NM_001283030.1 | chr13:51196248-51247931 |
| 27987 | Spin1 | NM_011462.3 | chr13:51196248-51247931 |
| 27988 | Spin1 | NM_146043.4 | chr13:51196248-51247931 |
| 27989 | Spin2c | NM_001005370.1 | chrX:150266835-150268783 |
| 27990 | Spin2d | NM_001243002.1 | chrX:70420640-70422328 |
| 27991 | Spin4 | NM_178753.4 | chrX:92217845-92222021 |
| 27992 | Spink10 | NM_177829.3 | chr18:62708565-62821042 |
| 27993 | Spink11 | NM_001048217.3 | chr18:44349698-44355831 |
| 27994 | Spink12 | NM_030061.3 | chr18:44264176-44268197 |
| 27995 | Spink13 | NM_001168423.2 | chr18:62767194-62901041 |
| 27996 | Spink14 | NM_001039218.2 | chr18:44187522-44191862 |
| 27997 | Spink2 | NM_001289764.1 | chr5:77634130-77640496 |
| 27998 | Spink2 | NM_001289767.1 | chr5:77634130-77640496 |
| 27999 | Spink2 | NM_001289768.1 | chr5:77634130-77640496 |
| 28000 | Spink2 | NM_183284.3 | chr5:77634130-77640496 |
| 28001 | Spink3 | NM_009258.5 | chr18:43887722-43896891 |
| 28002 | Spink4 | NM_011463.2 | chr4:40867088-40878428 |
| 28003 | Spink5 | NM_001081180.1 | chr18:44122894-44182141 |
| 28004 | Spink6 | NM_001013797.1 | chr18:44231046-44243264 |
| 28005 | Spink7 | NM_001001803.2 | chr18:62752667-62755918 |
| 28006 | Spink8 | NM_183136.2 | chr9:109719140-109729141 |
| 28007 | Spinki | NM_183123.2 | chr18:44326011-44334727 |
| 28008 | Spint1 | NM_016907.3 | chr2:119063095-119075249 |
| 28009 | Spint2 | NM_001082548.1 | chr7:30041348-30066996 |
| 28010 | Spint2 | NM_011464.2 | chr7:30041348-30066996 |
| 28011 | Spint3 | NM_001177401.1 | chr2:164395194-164438956 |
| 28012 | Spint4 | NM_030058.2 | chr2:164524000-164527948 |
| 28013 | Spint5 | NM_001040055.1 | chr2:164540804-164543568 |
| 28014 | Spire1 | NM_176832.2 | chr18:67647862-67712375 |
| 28015 | Spire1 | NM_194355.2 | chr18:67647862-67712375 |
| 28016 | Spire2 | NM_172287.2 | chr8:125856612-125893418 |
| 28017 | Spn | NM_001037810.2 | chr7:134275745-134281337 |
| 28018 | Spn | NM_009259.5 | chr7:134275745-134281337 |
| 28019 | Spn | NR_110337.1 | chr7:134275745-134281337 |
| 28020 | Spn-ps | NR_033583.1 | chr15:90721826-90728907 |
| 28021 | Spns1 | NM_023712.2 | chr7:133513573-133521448 |
| 28022 | Spns1 | NR_045537.1 | chr7:133513573-133521448 |
| 28023 | Spns2 | NM_001276383.1 | chr11:72265139-72303422 |
| 28024 | Spns2 | NM_153060.3 | chr11:72265139-72303422 |
| 28025 | Spns3 | NM_029932.3 | chr11:72311657-72363748 |
| 28026 | Spo11 | NM_001083959.1 | chr2:172805342-172819077 |
| 28027 | Spo11 | NM_001083960.1 | chr2:172805342-172819077 |
| 28028 | Spo11 | NM_012046.2 | chr2:172805342-172819077 |
| 28029 | Spock1 | NM_001166463.1 | chr13:57522555-58009693 |
| 28030 | Spock1 | NM_001166464.1 | chr13:57522555-58009693 |
| 28031 | Spock1 | NM_001166465.1 | chr13:57522555-58009693 |
| 28032 | Spock1 | NM_001166466.1 | chr13:57522555-58009693 |
| 28033 | Spock1 | NM_009262.3 | chr13:57522555-58009693 |
| 28034 | Spock2 | NM_052994.2 | chr10:59569005-59596661 |
| 28035 | Spock3 | NM_001252620.1 | chr8:65430028-65835893 |
| 28036 | Spock3 | NM_001252621.1 | chr8:65430028-65835893 |
| 28037 | Spock3 | NM_023689.3 | chr8:65430028-65835893 |
| 28038 | Spon1 | NM_145584.2 | chr7:120909511-121186889 |
| 28039 | Spon2 | NM_133903.3 | chr5:33556166-33560887 |

Fig. 25 - 149

| | | | |
|---|---|---|---|
| 28040 | Spop | NM_025287.2 | chr11:95275396-95354724 |
| 28041 | Spopl | NM_001165997.1 | chr2:23365573-23427624 |
| 28042 | Spopl | NM_001165998.1 | chr2:23365573-23427624 |
| 28043 | Spopl | NM_029773.2 | chr2:23365573-23427624 |
| 28044 | Spp1 | NM_001204201.1 | chr5:104864129-104870072 |
| 28045 | Spp1 | NM_001204202.1 | chr5:104864129-104870072 |
| 28046 | Spp1 | NM_001204203.1 | chr5:104864129-104870072 |
| 28047 | Spp1 | NM_001204233.1 | chr5:104864129-104870072 |
| 28048 | Spp1 | NM_009263.3 | chr5:104864129-104870072 |
| 28049 | Spp2 | NM_029269.2 | chr1:90303593-90323013 |
| 28050 | Sppl2a | NM_023220.2 | chr2:126716131-126758971 |
| 28051 | Sppl2b | NM_175195.3 | chr10:80318019-80331453 |
| 28052 | Sppl2c | NM_001082535.1 | chr11:104047640-104052480 |
| 28053 | Sppl2c | NM_199019.2 | chr11:104047640-104052480 |
| 28054 | Sppl3 | NM_029012.2 | chr5:115461532-115548799 |
| 28055 | Spr | NM_011467.2 | chr6:85083673-85087758 |
| 28056 | Spred1 | NM_001277256.1 | chr2:116946806-117008013 |
| 28057 | Spred1 | NM_033524.3 | chr2:116946806-117008013 |
| 28058 | Spred2 | NM_033523.4 | chr11:19824444-19922600 |
| 28059 | Spred3 | NM_182927.3 | chr7:29943847-29953666 |
| 28060 | Sprn | NM_183147.2 | chr7:147336527-147340558 |
| 28061 | Sprr1a | NM_009264.2 | chr3:92287875-92289803 |
| 28062 | Sprr1b | NM_009265.3 | chr3:92240730-92242701 |
| 28063 | Sprr2a2 | NM_001164787.1 | chr3:92019756-92026413 |
| 28064 | Sprr2a2 | NM_001164781.1 | chr3:92054568-92061226 |
| 28065 | Sprr2b | NM_011469.3 | chr3:92120626-92122007 |
| 28066 | Sprr2d | NM_011470.2 | chr3:92143061-92144795 |
| 28067 | Sprr2e | NM_011471.2 | chr3:92156064-92157371 |
| 28068 | Sprr2f | NM_011472.2 | chr3:92169108-92170364 |
| 28069 | Sprr2g | NR_003548.1 | chr3:92177836-92179151 |
| 28070 | Sprr2h | NM_011474.3 | chr3:92189606-92191241 |
| 28071 | Sprr2i | NM_011475.3 | chr3:92211912-92213193 |
| 28072 | Sprr2j-ps | NR_003185.1 | chr3:92222008-92223318 |
| 28073 | Sprr2k | NM_011477.3 | chr3:92236503-92237849 |
| 28074 | Sprr3 | NM_001204427.1 | chr3:92260423-92262642 |
| 28075 | Sprr3 | NM_011478.2 | chr3:92260423-92262642 |
| 28076 | Sprr4 | NM_173070.1 | chr3:92304184-92304415 |
| 28077 | Sprtn | NM_001111141.1 | chr8:127421785-127427713 |
| 28078 | Spry1 | NM_011896.3 | chr3:37538871-37543521 |
| 28079 | Spry2 | NM_011897.3 | chr14:106291163-106296036 |
| 28080 | Spry3 | NM_001030293.2 | chrx_random:101351-106392 |
| 28081 | Spry4 | NM_011898.2 | chr18:38745918-38760922 |
| 28082 | Spryd3 | NM_001033277.3 | chr15:101946958-101966646 |
| 28083 | Spryd4 | NM_025716.2 | chr10:127646966-127648850 |
| 28084 | Spryd7 | NM_025697.3 | chr14:62153141-62175723 |
| 28085 | Spsb1 | NM_029035.2 | chr4:149270392-149329135 |
| 28086 | Spsb2 | NM_013539.1 | chr6:124758936-124760634 |
| 28087 | Spsb3 | NM_001163756.1 | chr17:25023618-25029092 |
| 28088 | Spsb3 | NM_001163751.1 | chr17:25023618-25029092 |
| 28089 | Spsb3 | NM_027141.2 | chr17:25023618-25029092 |
| 28090 | Spsb4 | NM_145134.3 | chr9:96843900-96918774 |
| 28091 | Spt1 | NM_009267.2 | chrUn_random:2674944-2678407 |
| 28092 | Spta1 | NM_011465.4 | chr1:176102906-176178580 |
| 28093 | Sptan1 | NM_001076554.2 | chr2:29821079-29886970 |
| 28094 | Sptan1 | NM_001177667.1 | chr2:29821079-29886970 |
| 28095 | Sptan1 | NM_001177668.1 | chr2:29821079-29886970 |
| 28096 | Sptb | NM_013675.3 | chr12:77681474-77811534 |
| 28097 | Sptbn1 | NM_009260.2 | chr11:29999394-30119772 |
| 28098 | Sptbn1 | NM_175836.2 | chr11:29999394-30119772 |
| 28099 | Sptbn2 | NM_021287.1 | chr19:4711222-4752352 |
| 28100 | Sptbn4 | NM_001199234.1 | chr7:28141401-28231608 |
| 28101 | Sptbn4 | NM_001199235.1 | chr7:28141401-28231608 |
| 28102 | Sptbn4 | NM_001199236.1 | chr7:28141401-28231608 |
| 28103 | Sptbn4 | NM_032610.2 | chr7:28141401-28231608 |
| 28104 | Sptlc1 | NM_009269.2 | chr13:53428118-53472730 |
| 28105 | Sptlc2 | NM_011479.3 | chr12:88648838-88729188 |
| 28106 | Sptlc3 | NM_175467.3 | chr2:139319655-139463410 |
| 28107 | Sptssa | NM_134054.2 | chr12:55746361-55757559 |
| 28108 | Sptssb | NM_001164210.2 | chr3:69623460-69683816 |
| 28109 | Sptssb | NM_001286959.1 | chr3:69623460-69683816 |
| 28110 | Sptssb | NM_133675.3 | chr3:69623460-69683816 |
| 28111 | Sptv2d1 | NM_175318.4 | chr7:54245765-54263784 |
| 28112 | Spz1 | NM_030237.3 | chr13:93344586-93346187 |
| 28113 | Sqle | NM_009270.3 | chr15:59146646-59162748 |
| 28114 | Sqrdl | NM_001162503.1 | chr2:122591094-122635287 |
| 28115 | Sqrdl | NM_021507.3 | chr2:122591094-122635287 |
| 28116 | Sqrdl | NR_027888.1 | chr2:122591094-122635287 |
| 28117 | Sqstm1 | NM_001290769.1 | chr11:50013653-50024322 |
| 28118 | Sqstm1 | NM_011018.2 | chr11:50013653-50024322 |
| 28119 | Sra1 | NM_001164406.1 | chr18:36826840-36829965 |
| 28120 | Sra1 | NM_025291.3 | chr18:36826840-36829965 |
| 28121 | Sra1 | NR_028355.1 | chr18:36826840-36829965 |
| 28122 | Srbd1 | NM_033323.3 | chr17:86384004-86544515 |
| 28123 | Src | NM_001025395.2 | chr2:157250028-157297574 |
| 28124 | Src | NM_009271.3 | chr2:157250028-157297574 |
| 28125 | Srcin1 | NM_018873.1 | chr11:97370653-97436440 |
| 28126 | Srcrb4d | NM_001160366.1 | chr5:136436092-136450346 |
| 28127 | Srd5a1 | NM_175283.3 | chr13:69712326-69750341 |
| 28128 | Srd5a2 | NM_053188.2 | chr17:74367045-74397256 |
| 28129 | Srd5a3 | NM_020611.4 | chr5:76569297-76584528 |
| 28130 | Srebf1 | NM_011480.3 | chr11:60012591-60034106 |
| 28131 | Srebf2 | NM_033218.1 | chr15:81977699-82035390 |
| 28132 | Srek1 | NM_172592.2 | chr13:104531894-104554662 |
| 28133 | Srek1ip1 | NM_026075.2 | chr13:105607318-105628739 |
| 28134 | Srf | NM_020493.2 | chr17:46683788-46693111 |
| 28135 | Srfbp1 | NM_026040.3 | chr18:52625346-52650392 |
| 28136 | Srgap1 | NM_001081037.2 | chr10:121218046-121484371 |
| 28137 | Srgap1 | NM_001242411.1 | chr10:121218046-121484371 |
| 28138 | Srgap2 | NM_001081011.2 | chr1:133181827-133423938 |
| 28139 | Srgap3 | NM_080448.4 | chr6:112667965-112897260 |
| 28140 | Srgn | NM_011157.2 | chr10:61957175-61970503 |
| 28141 | Sri | NM_001080974.1 | chr5:8046077-8069314 |
| 28142 | Sri | NM_025618.3 | chr5:8046077-8069314 |
| 28143 | Sri | NM_175347.4 | chr16:4480227-4523053 |
| 28144 | Srm | NM_009272.4 | chr4:147965621-147968728 |
| 28145 | Srms | NM_011481.3 | chr2:180940267-180947876 |
| 28146 | Srp14 | NM_009273.4 | chr2:118301578-118305432 |
| 28147 | Srp19 | NM_025527.3 | chr18:34490798-34496253 |
| 28148 | Srp54a | NM_011899.4 | chr12:56181482-56216354 |
| 28149 | Srp54a | NM_011899.4 | chr12:56256090-56365681 |
| 28150 | Srp54b | NM_001100109.1 | chr12:56256091-56290200 |
| 28151 | Srp54c | NM_001100110.1 | chr12:56331465-56364007 |
| 28152 | Srp68 | NM_146032.3 | chr11:116186479-116135531 |
| 28153 | Srp72 | NM_025691.1 | chr5:77403725-77428960 |
| 28154 | Srp9 | NM_012058.3 | chr1:184054867-184062546 |
| 28155 | Srpk1 | NM_016795.3 | chr17:28726536-28759399 |
| 28156 | Srpk2 | NM_009274.2 | chr5:23009174-23122389 |
| 28157 | Srpk3 | NM_019684.1 | chrX:71019760-71024263 |
| 28158 | Srpr | NM_026130.1 | chr9:35018788-35024588 |
| 28159 | Srprb | NM_009275.4 | chr9:103090362-103104395 |
| 28160 | Srpx | NM_016911.4 | chrX:9615102-9694787 |
| 28161 | Srpx2 | NM_001083895.3 | chrX:130442963-130466985 |
| 28162 | Srpx2 | NM_026838.4 | chrX:130442963-130466985 |
| 28163 | Srr | NM_001163311.1 | chr11:74711581-74739300 |
| 28164 | Srr | NM_013761.4 | chr11:74711581-74739300 |
| 28165 | Srrd | NM_027323.2 | chr5:112766411-112772060 |
| 28166 | Srrm1 | NM_001130477.1 | chr4:134876398-134909129 |
| 28167 | Srrm1 | NM_016799.3 | chr4:134876398-134909129 |
| 28168 | Srrm2 | NM_175229.3 | chr17:23940154-23961710 |
| 28169 | Srrm3 | NM_021403.3 | chr5:136293975-136350642 |
| 28170 | Srrm4 | NM_026886.3 | chr5:116889282-117041826 |
| 28171 | Srrm4os | NR_015595.2 | chr5:116888731-116915496 |
| 28172 | Srrt | NM_001109909.1 | chr5:137736931-137748902 |
| 28173 | Srrt | NM_001109910.1 | chr5:137736931-137748902 |
| 28174 | Srrt | NM_031405.2 | chr5:137736931-137748902 |
| 28175 | Srsf1 | NM_001078167.2 | chr11:87860874-87867259 |
| 28176 | Srsf1 | NM_173374.4 | chr11:87860874-87867259 |
| 28177 | Srsf10 | NM_001080387.2 | chr4:135411985-135425814 |
| 28178 | Srsf10 | NM_001284195.1 | chr4:135411985-135425814 |
| 28179 | Srsf10 | NM_001284196.1 | chr4:135411985-135425814 |
| 28180 | Srsf10 | NM_010178.3 | chr4:135411985-135425814 |
| 28181 | Srsf11 | NM_001093752.1 | chr3:157673456-157699603 |
| 28182 | Srsf11 | NM_001093753.1 | chr3:157673456-157699603 |
| 28183 | Srsf11 | NM_026989.3 | chr3:157673456-157699603 |
| 28184 | Srsf12 | NM_177774.4 | chr4:33295965-33320315 |
| 28185 | Srsf2 | NM_011358.2 | chr11:116711210-116714408 |
| 28186 | Srsf3 | NM_013663.5 | chr17:29169604-29180317 |
| 28187 | Srsf3 | NR_036613.1 | chr17:29169604-29180317 |
| 28188 | Srsf4 | NM_020587.2 | chr4:131429554-131457640 |
| 28189 | Srsf5 | NM_001079694.1 | chr12:82046490-82051494 |
| 28190 | Srsf5 | NM_001079695.1 | chr12:82046490-82051494 |
| 28191 | Srsf5 | NM_009159.2 | chr12:82046490-82051494 |
| 28192 | Srsf6 | NM_026499.4 | chr2:162757243-162762856 |
| 28193 | Srsf7 | NM_001195485.1 | chr17:80599419-80606645 |
| 28194 | Srsf7 | NM_001195486.1 | chr17:80599419-80606645 |
| 28195 | Srsf7 | NM_001195487.1 | chr17:80599419-80606645 |
| 28196 | Srsf7 | NM_146083.2 | chr17:80599419-80606645 |
| 28197 | Srsf7 | NR_036615.1 | chr17:80599419-80606645 |
| 28198 | Srsf9 | NM_025573.3 | chr5:115777185-115783089 |
| 28199 | Srsf9 | NR_036616.1 | chr5:115777185-115783089 |
| 28200 | Srxn1 | NM_029688.5 | chr2:151931259-151937112 |
| 28201 | Sry | NM_011564.1 | chrY:1918380-1919568 |
| 28202 | Ss18 | NM_001161369.1 | chr18:14784137-14841423 |
| 28203 | Ss18 | NM_001161370.1 | chr18:14784137-14841423 |
| 28204 | Ss18 | NM_001161371.1 | chr18:14784137-14841423 |
| 28205 | Ss18 | NM_009280.2 | chr18:14784137-14841423 |
| 28206 | Ss18l1 | NM_178750.5 | chr2:179777187-179804906 |
| 28207 | Ssb | NM_001110145.1 | chr2:69699618-69723672 |
| 28208 | Ssb | NM_009278.4 | chr2:69699618-69723672 |
| 28209 | Ssbp1 | NM_001286663.1 | chr6:40421413-40431822 |
| 28210 | Ssbp1 | NM_028358.2 | chr6:40421413-40431822 |
| 28211 | Ssbp1 | NM_212468.3 | chr6:40421413-40431822 |
| 28212 | Ssbp2 | NM_024186.5 | chr13:91600701-91925753 |
| 28213 | Ssbp2 | NM_024272.4 | chr13:91600701-91925753 |
| 28214 | Ssbp3 | NM_023672.2 | chr4:106584074-106722299 |
| 28215 | Ssbp3 | NM_198438.3 | chr4:106584074-106722299 |
| 28216 | Ssbp4 | NM_133772.2 | chr8:73121388-73132213 |
| 28217 | Ssc5d | NM_173008.2 | chr7:4877445-4896399 |
| 28218 | Ssfa2 | NM_080558.4 | chr2:79475581-79513121 |
| 28219 | Ssh1 | NM_198109.4 | chr5:114392227-114443766 |
| 28220 | Ssh2 | NM_001291190.1 | chr11:77029926-77273721 |
| 28221 | Ssh2 | NM_177710.4 | chr11:77029926-77273721 |
| 28222 | Ssh3 | NM_198113.2 | chr19:4261668-4269172 |
| 28223 | Ssmem1 | NM_027073.1 | chr6:30459848-30470253 |
| 28224 | Ssmem1 | NM_029373.4 | chr6:30459848-30470253 |
| 28225 | Ssna1 | NM_023464.2 | chr2:25126558-25127938 |
| 28226 | Sspn | NM_010656.2 | chr6:145882666-145913745 |
| 28227 | Sspo | NM_173428.3 | chr6:48398227-48451249 |
| 28228 | Ssr1 | NM_025965.3 | chr13:38063269-38086059 |

Fig. 25 - 150

| | | | |
|---|---|---|---|
| 28229 | Ssr2 | NM_025448.3 | chr3:88383592-88392335 |
| 28230 | Ssr3 | NM_026155.3 | chr3:65183578-65196475 |
| 28231 | Ssr4 | NM_001166480.1 | chrX:71032366-71036167 |
| 28232 | Ssr4 | NM_009279.3 | chrX:71032366-71036167 |
| 28233 | Ssrp1 | NM_001136081.2 | chr2:84877276-84887271 |
| 28234 | Ssrp1 | NM_182990.4 | chr2:84877276-84887271 |
| 28235 | Ssscal | NM_020491.5 | chr19:5730305-5731732 |
| 28236 | Sst | NM_009215.1 | chr16:23889666-23890930 |
| 28237 | Sstr1 | NM_009216.3 | chr12:59312790-59317023 |
| 28238 | Sstr2 | NM_001042606.2 | chr11:113480794-113487209 |
| 28239 | Sstr2 | NM_009217.4 | chr11:113480794-113487209 |
| 28240 | Sstr3 | NM_009218.3 | chr15:78367444-78374775 |
| 28241 | Sstr4 | NM_009219.3 | chr2:148221112-148222500 |
| 28242 | Sstr5 | NM_001191008.1 | chr17:25626819-25634233 |
| 28243 | Sstr5 | NM_011425.3 | chr17:25626819-25634233 |
| 28244 | Ssty1 | NM_009220.1 | chrY_random:9328876-9331261 |
| 28245 | Ssty1 | NM_009220.1 | chrY_random:48388360-48390745 |
| 28246 | Ssty2 | NM_023546.3 | chrY_random:18284670-18287000 |
| 28247 | Ssu2 | NM_175525.3 | chr6:112309317-112338017 |
| 28248 | Ssu72 | NM_026899.3 | chr4:155078923-155107982 |
| 28249 | Ssx2ip | NM_001253768.1 | chr3:146067605-146103101 |
| 28250 | Ssx2ip | NM_001253769.1 | chr3:146067605-146103101 |
| 28251 | Ssx2ip | NM_001253770.1 | chr3:146067605-146103101 |
| 28252 | Ssx2ip | NM_138744.3 | chr3:146067605-146103101 |
| 28253 | Ssx9 | NM_199063.2 | chrX:8325555-8331713 |
| 28254 | Ssxb1 | NM_026492.3 | chrX:7990430-7999283 |
| 28255 | Ssxb10 | NM_199064.1 | chrX:7904549-7913361 |
| 28256 | Ssxb2 | NM_001001450.4 | chrX:8031468-8038852 |
| 28257 | Ssxb2 | NM_001134226.1 | chrX:8031468-8038852 |
| 28258 | Ssxb3 | NM_198898.2 | chrX:8160669-8166372 |
| 28259 | Ssxb5 | NM_199319.3 | chrX:8380816-8386512 |
| 28260 | Ssxb6 | NM_001205108.1 | chrX:8119729-8125381 |
| 28261 | Ssxb8 | NM_001081565.1 | chrX:8262456-8267970 |
| 28262 | Ssxb9 | NM_199066.2 | chrX:7944103-7952514 |
| 28263 | St13 | NM_133726.2 | chr15:81195473-81230124 |
| 28264 | St14 | NM_011176.4 | chr9:30896174-30939384 |
| 28265 | St18 | NM_001244692.1 | chr1:6477311-6851021 |
| 28266 | St18 | NM_001244693.1 | chr1:6477311-6851021 |
| 28267 | St18 | NM_173868.2 | chr1:6477311-6851021 |
| 28268 | St18 | NR_045188.1 | chr1:6477311-6851021 |
| 28269 | St18 | NR_045189.1 | chr1:6477311-6851021 |
| 28270 | St3gal1 | NM_009177.2 | chr15:66934436-67008444 |
| 28271 | St3gal2 | NM_009179.3 | chr8:113443764-113496397 |
| 28272 | St3gal3 | NM_001161774.2 | chr4:117604757-117807551 |
| 28273 | St3gal3 | NM_001285520.1 | chr4:117604757-117807551 |
| 28274 | St3gal3 | NM_001285521.1 | chr4:117604757-117807551 |
| 28275 | St3gal3 | NM_009176.5 | chr4:117604757-117807551 |
| 28276 | St3gal4 | NM_009178.3 | chr9:34854164-34924395 |
| 28277 | St3gal5 | NM_001035228.2 | chr6:72047601-72104564 |
| 28278 | St3gal5 | NM_011375.3 | chr6:72047601-72104564 |
| 28279 | St3gal6 | NM_018784.2 | chr16:58470654-58523425 |
| 28280 | St5 | NM_001001326.1 | chr7:116667424-116760661 |
| 28281 | St5 | NM_029811.2 | chr7:116667424-116760661 |
| 28282 | St5 | NR_037617.1 | chr7:116667424-116760661 |
| 28283 | St6gal1 | NM_001252505.1 | chr16:23224812-23360423 |
| 28284 | St6gal1 | NM_001252506.1 | chr16:23224812-23360423 |
| 28285 | St6gal1 | NM_145933.4 | chr16:23224812-23360423 |
| 28286 | St6gal2 | NM_172829.2 | chr17:55585014-55638524 |
| 28287 | St6galnac1 | NM_011371.2 | chr11:116626338-116636821 |
| 28288 | St6galnac2 | NM_009180.3 | chr11:116538018-116555974 |
| 28289 | St6galnac3 | NM_011372.2 | chr3:152865472-153388097 |
| 28290 | St6galnac4 | NM_001276425.1 | chr2:32442597-32455216 |
| 28291 | St6galnac4 | NM_011373.3 | chr2:32442597-32455216 |
| 28292 | St6galnac5 | NM_012028.4 | chr3:152483673-152645171 |
| 28293 | St6galnac6 | NM_025310.2 | chr2:32455228-32476329 |
| 28294 | St6galnac6 | NM_001025311.2 | chr2:32455228-32476329 |
| 28295 | St6galnac6 | NM_001289547.1 | chr2:32455228-32476329 |
| 28296 | St6galnac6 | NM_001289548.1 | chr2:32455228-32476329 |
| 28297 | St6galnac6 | NM_001289549.1 | chr2:32455228-32476329 |
| 28298 | St6galnac6 | NM_016973.3 | chr2:32455228-32476329 |
| 28299 | St6galnac6 | NR_045152.1 | chr2:32455228-32476329 |
| 28300 | St7 | NM_001083315.2 | chr6:17643993-17893023 |
| 28301 | St7 | NM_001289624.1 | chr6:17643993-17893023 |
| 28302 | St7 | NM_001289625.1 | chr6:17643993-17893023 |
| 28303 | St7 | NM_001289626.1 | chr6:17643993-17893023 |
| 28304 | St7 | NM_001289627.1 | chr6:17643993-17893023 |
| 28305 | St7 | NM_001289629.1 | chr6:17643993-17893023 |
| 28306 | St7 | NM_022332.3 | chr6:17643993-17893023 |
| 28307 | St7l | NM_001253702.1 | chr3:104667423-104732981 |
| 28308 | St7l | NM_001253703.1 | chr3:104667423-104732981 |
| 28309 | St7l | NM_153091.3 | chr3:104667423-104732981 |
| 28310 | St7l | NR_045188.1 | chr3:104667423-104732981 |
| 28311 | St8sia1 | NM_011374.2 | chr6:142770061-142912972 |
| 28312 | St8sia2 | NM_009181.2 | chr7:81084005-81158568 |
| 28313 | St8sia3 | NM_009183.2 | chr18:64314013-64435798 |
| 28314 | St8sia3os | NR_045366.1 | chr18:64317378-64436834 |
| 28315 | St8sia4 | NM_001159745.1 | chr1:97484258-97564171 |
| 28316 | St8sia4 | NM_009183.2 | chr1:97484258-97564171 |
| 28317 | St8sia5 | NM_013666.2 | chr18:77424585-77494189 |
| 28318 | St8sia5 | NM_153124.2 | chr18:77424585-77494189 |
| 28319 | St8sia6 | NM_145838.1 | chr2:13576564-13715147 |
| 28320 | Stab1 | NM_138672.2 | chr14:31952203-31981827 |
| 28321 | Stab2 | NM_138673.2 | chr10:86303954-86470687 |

| | | | |
|---|---|---|---|
| 28322 | Stac | NM_016853.2 | chr9:111463937-111592720 |
| 28323 | Stac2 | NM_146028.4 | chr11:97897937-97914776 |
| 28324 | Stac3 | NM_177707.2 | chr10:126938772-126945871 |
| 28325 | Stag1 | NM_009282.3 | chr9:100544041-100858963 |
| 28326 | Stag2 | NM_001077712.2 | chrX:39502588-39630363 |
| 28327 | Stag2 | NM_001290713.1 | chrX:39502588-39630363 |
| 28328 | Stag2 | NM_021465.4 | chrX:39502588-39630363 |
| 28329 | Stag3 | NM_016964.2 | chr5:138721736-138753621 |
| 28330 | Stam | NM_011484.2 | chr2:13995738-14069957 |
| 28331 | Stam2 | NM_019667.2 | chr2:52547724-52601183 |
| 28332 | Stambp | NM_024239.2 | chr6:83493200-83522498 |
| 28333 | Stambpl1 | NM_029682.4 | chr19:34266759-34314818 |
| 28334 | Stamos | NR_038162.1 | chr2:13991959-13995561 |
| 28335 | Stap1 | NM_019992.3 | chr5:86500852-86533018 |
| 28336 | Stap2 | NM_145934.2 | chr17:56136498-56145029 |
| 28337 | Stap2 | NR_102313.1 | chr17:56136498-56145029 |
| 28338 | Star | NM_011485.4 | chr8:26918984-26926454 |
| 28339 | Stard10 | NM_019990.4 | chr7:108469832-108494826 |
| 28340 | Stard13 | NM_001163493.1 | chr5:151840089-151992768 |
| 28341 | Stard13 | NM_146258.2 | chr5:151840089-151992768 |
| 28342 | Stard3 | NM_021547.3 | chr11:98219681-98242426 |
| 28343 | Stard3nl | NM_024270.3 | chr13:19449544-19487621 |
| 28344 | Stard4 | NM_133774.4 | chr18:33361074-33373470 |
| 28345 | Stard5 | NM_023377.4 | chr7:90780526-90790838 |
| 28346 | Stard6 | NM_001289648.1 | chr18:70612793-70660719 |
| 28347 | Stard6 | NM_001289649.1 | chr18:70612793-70660719 |
| 28348 | Stard6 | NM_001289650.1 | chr18:70612793-70660719 |
| 28349 | Stard6 | NM_029019.4 | chr18:70612793-70660719 |
| 28350 | Stard7 | NM_139308.2 | chr2:127095964-127124670 |
| 28351 | Stard8 | NM_199018.2 | chrX:96237919-96270067 |
| 28352 | Stat1 | NM_001205313.1 | chr1:52176281-52218709 |
| 28353 | Stat1 | NM_001205314.1 | chr1:52176281-52218709 |
| 28354 | Stat1 | NM_009283.1 | chr1:52176281-52218709 |
| 28355 | Stat2 | NM_019963.1 | chr10:127707631-127729905 |
| 28356 | Stat3 | NM_011486.3 | chr11:100748123-100800825 |
| 28357 | Stat3 | NM_213659.2 | chr11:100748123-100800825 |
| 28358 | Stat3 | NM_213660.2 | chr11:100748123-100800825 |
| 28359 | Stat4 | NM_011487.5 | chr1:52065087-52164028 |
| 28360 | Stat5a | NM_001164062.1 | chr11:100720664-100746483 |
| 28361 | Stat5a | NM_011488.3 | chr11:100720664-100746483 |
| 28362 | Stat5b | NM_001113563.1 | chr11:100642044-100711899 |
| 28363 | Stat5b | NM_011489.3 | chr11:100642044-100711899 |
| 28364 | Stat6 | NM_009284.2 | chr10:127080042-127098043 |
| 28365 | Stau1 | NM_001109905.2 | chr2:166773048-166821799 |
| 28366 | Stau1 | NM_001109906.2 | chr2:166773048-166821799 |
| 28367 | Stau1 | NM_001291160.1 | chr2:166773048-166821799 |
| 28368 | Stau1 | NM_011490.4 | chr2:166773048-166821799 |
| 28369 | Stau1 | NR_111895.1 | chr2:166773048-166821799 |
| 28370 | Stau2 | NM_001111272.1 | chr1:16218890-16509383 |
| 28371 | Stau2 | NM_025303.3 | chr1:16218890-16509383 |
| 28372 | Stbd1 | NM_175096.3 | chr5:93032076-93035605 |
| 28373 | Stc1 | NM_009285.3 | chr14:69647345-69659458 |
| 28374 | Stc2 | NM_011491.3 | chr11:31259440-31270061 |
| 28375 | Steap1 | NM_027399.3 | chr5:5736321-5749317 |
| 28376 | Steap2 | NM_001103156.2 | chr5:5664828-5694568 |
| 28377 | Steap2 | NM_001103157.2 | chr5:5664828-5694568 |
| 28378 | Steap2 | NM_001285469.1 | chr5:5664828-5694568 |
| 28379 | Steap2 | NM_001285470.1 | chr5:5664828-5694568 |
| 28380 | Steap2 | NM_001285471.1 | chr5:5664828-5694568 |
| 28381 | Steap2 | NM_028734.5 | chr5:5664828-5694568 |
| 28382 | Steap3 | NM_001085409.1 | chr1:122122992-122167659 |
| 28383 | Steap3 | NM_133186.3 | chr1:122122992-122167659 |
| 28384 | Steap4 | NM_054098.3 | chr5:7960471-7982213 |
| 28385 | Stfa1 | NM_001082543.1 | chr16:36277233-36285457 |
| 28386 | Stfa2 | NM_001082545.1 | chr16:36404031-36408449 |
| 28387 | Stfa2l1 | NM_173869.3 | chr16:36156896-36162034 |
| 28388 | Stfa3 | NM_025288.2 | chr16:36456622-36455478 |
| 28389 | Sti | NM_009185.3 | chr4:114672722-114715803 |
| 28390 | Stim1 | NM_009287.4 | chr7:109416357-109585369 |
| 28391 | Stim2 | NM_001081103.2 | chr5:54389761-54512296 |
| 28392 | Stip1 | NM_016737.2 | chr19:7095185-7114516 |
| 28393 | Stk10 | NM_009288.2 | chr11:32433265-32524595 |
| 28394 | Stk11 | NM_011492.4 | chr10:79578548-79593430 |
| 28395 | Stk11ip | NM_027886.3 | chr1:75518103-75533910 |
| 28396 | Stk16 | NM_001277992.1 | chr1:75207403-75215828 |
| 28397 | Stk16 | NM_011494.5 | chr1:75207403-75215828 |
| 28398 | Stk16 | NR_102731.1 | chr1:75207403-75215828 |
| 28399 | Stk17b | NM_133810.3 | chr1:53812355-53842059 |
| 28400 | Stk19 | NM_019442.3 | chr17:34960937-34973848 |
| 28401 | Stk24 | NM_145465.2 | chr14:121685562-121778452 |
| 28402 | Stk25 | NM_021537.3 | chr1:95517328-95532304 |
| 28403 | Stk3 | NM_019635.3 | chr15:34805253-35085561 |
| 28404 | Stk31 | NM_029916.2 | chr6:49345602-49419501 |
| 28405 | Stk32a | NM_178749.3 | chr18:43367350-43477135 |
| 28406 | Stk32b | NM_022416.2 | chr5:37838063-38108392 |
| 28407 | Stk32c | NM_001162540.1 | chr7:146289536-146428872 |
| 28408 | Stk32c | NM_021302.3 | chr7:146289536-146428872 |
| 28409 | Stk33 | NM_054103.1 | chr7:116422729-116582567 |
| 28410 | Stk35 | NM_001038635.2 | chr2:129624104-129658021 |
| 28411 | Stk35 | NM_183262.3 | chr2:129624104-129658021 |
| 28412 | Stk36 | NM_175031.3 | chr1:74648028-74683467 |
| 28413 | Stk38 | NM_134115.2 | chr17:29107829-29144882 |
| 28414 | Stk38l | NM_172734.3 | chr6:146673451-146727336 |
| 28415 | Stk39 | NM_016866.2 | chr2:68048503-68310038 |
| 28416 | Stk4 | NM_021420.3 | chr2:163899913-163981257 |

Fig. 25 - 151

| | | | |
|---|---|---|---|
| 28417 | Stk40 | NM_001145827.1 | chr4:125781200-125818273 |
| 28418 | Stk40 | NM_028800.3 | chr4:125781200-125818273 |
| 28419 | Stmn1 | NM_019641.4 | chr4:134024234-134029758 |
| 28420 | Stmn1-rs1 | NR_029430.1 | chr9:115190210-115191188 |
| 28421 | Stmn2 | NM_025285.2 | chr3:8509526-8561604 |
| 28422 | Stmn3 | NM_009133.3 | chr2:181041163-181049205 |
| 28423 | Stmn4 | NM_019675.2 | chr14:66963211-66980517 |
| 28424 | Stmnd1 | NM_001005422.1 | chr13:46369089-46395484 |
| 28425 | Stom | NM_013515.2 | chr2:35169509-35192529 |
| 28426 | Stoml1 | NM_026942.3 | chr9:58100970-58110331 |
| 28427 | Stoml1 | NR_028146.1 | chr9:58100970-58110331 |
| 28428 | Stoml2 | NM_023231.2 | chr4:43040561-43044256 |
| 28429 | Stoml3 | NM_153156.1 | chr3:53292714-53311574 |
| 28430 | Ston1 | NM_029858.2 | chr17:89025894-89045064 |
| 28431 | Ston2 | NM_175367.6 | chr12:92871448-93024876 |
| 28432 | Stox1 | NM_001033260.1 | chr10:62122170-62188847 |
| 28433 | Stox2 | NM_001114311.1 | chr8:48265401-48437702 |
| 28434 | Stox2 | NM_001286376.1 | chr8:48265401-48437702 |
| 28435 | Stox2 | NM_175162.2 | chr8:48265401-48437702 |
| 28436 | Stpg1 | NM_030189.3 | chr4:135051901-135093718 |
| 28437 | Stpg2 | NM_198659.2 | chr3:138868856-139373263 |
| 28438 | Stra13 | NM_016665.2 | chr11:120572254-120575081 |
| 28439 | Stra6 | NM_001162475.1 | chr9:57976894-58001804 |
| 28440 | Stra6 | NM_001162476.1 | chr9:57976894-58001804 |
| 28441 | Stra6 | NM_001162479.1 | chr9:57976894-58001804 |
| 28442 | Stra6 | NM_009291.2 | chr9:57976894-58001804 |
| 28443 | Stra8 | NM_009292.1 | chr6:34870959-34889342 |
| 28444 | Strada | NM_001252448.1 | chr11:106024287-106054917 |
| 28445 | Strada | NM_001252449.1 | chr11:106024287-106054917 |
| 28446 | Strada | NM_028126.3 | chr11:106024287-106054917 |
| 28447 | Stradb | NM_172656.5 | chr1:59030414-59051965 |
| 28448 | Strap | NM_011499.3 | chr6:137683602-137700451 |
| 28449 | Strbp | NM_009261.3 | chr2:37425387-37502805 |
| 28450 | Strc | NM_080459.2 | chr2:121189463-121206676 |
| 28451 | Strip1 | NM_153563.2 | chr3:107415449-107434628 |
| 28452 | Strip2 | NM_001037740.1 | chr6:29867012-29909680 |
| 28453 | Strip2 | NM_177204.3 | chr6:29867012-29909680 |
| 28454 | Strip2 | NR_104576.1 | chr6:29867012-29909680 |
| 28455 | Strn | NM_011550.2 | chr17:79053303-79135900 |
| 28456 | Strn3 | NM_001172098.1 | chr12:52709527-52839926 |
| 28457 | Strn3 | NM_052973.2 | chr12:52709527-52839926 |
| 28458 | Strn4 | NM_001039878.2 | chr7:17394615-17426280 |
| 28459 | Strn4 | NM_133789.3 | chr7:17394615-17426280 |
| 28460 | Stt3a | NM_008408.4 | chr9:36539997-36575163 |
| 28461 | Stt3b | NM_024222.2 | chr9:115151700-115219539 |
| 28462 | Stub1 | NM_019719.3 | chr17:25967581-25970306 |
| 28463 | Stx11 | NM_001163590.1 | chr10:12659786-12684065 |
| 28464 | Stx11 | NM_001163591.1 | chr10:12659786-12684065 |
| 28465 | Stx11 | NM_029075.1 | chr10:12659786-12684065 |
| 28466 | Stx12 | NM_133887.4 | chr4:132409978-132440373 |
| 28467 | Stx16 | NM_001102423.1 | chr2:173902551-173925272 |
| 28468 | Stx16 | NM_001102424.1 | chr2:173902551-173925272 |
| 28469 | Stx16 | NM_001102425.1 | chr2:173902551-173925272 |
| 28470 | Stx16 | NM_172675.4 | chr2:173902551-173925272 |
| 28471 | Stx17 | NM_026343.2 | chr4:48137790-48199378 |
| 28472 | Stx18 | NM_001289535.1 | chr5:38430468-38550706 |
| 28473 | Stx18 | NM_001289536.1 | chr5:38430468-38550706 |
| 28474 | Stx18 | NM_026959.3 | chr5:38430468-38550706 |
| 28475 | Stx19 | NM_026588.1 | chr16:62814502-62822548 |
| 28476 | Stx1a | NM_016801.3 | chr5:135499441-135526969 |
| 28477 | Stx1b | NM_024414.2 | chr7:134950357-134968045 |
| 28478 | Stx2 | NM_001286033.1 | chr5:129490432-129514447 |
| 28479 | Stx2 | NM_001286034.1 | chr5:129490432-129514447 |
| 28480 | Stx2 | NM_007941.3 | chr5:129490432-129514447 |
| 28481 | Stx3 | NM_001025307.1 | chr19:11849607-11893893 |
| 28482 | Stx3 | NM_001286543.1 | chr19:11849607-11893893 |
| 28483 | Stx3 | NM_011502.3 | chr19:11849607-11893893 |
| 28484 | Stx3 | NM_152220.2 | chr19:11849607-11893893 |
| 28485 | Stx4a | NM_009294.3 | chr7:134985321-134992479 |
| 28486 | Stx5a | NM_001167799.1 | chr19:8815913-8830132 |
| 28487 | Stx5a | NM_019829.4 | chr19:8815913-8830132 |
| 28488 | Stx6 | NM_021433.3 | chr1:157005832-157050647 |
| 28489 | Stx7 | NM_016797.4 | chr10:23896122-23908765 |
| 28490 | Stx8 | NM_018768.2 | chr11:67779984-68020650 |
| 28491 | Stxbp1 | NM_001113569.1 | chr2:32643126-32702757 |
| 28492 | Stxbp1 | NM_009295.2 | chr2:32643126-32702757 |
| 28493 | Stxbp2 | NM_011503.4 | chr8:3631159-3643644 |
| 28494 | Stxbp3a | NM_011504.1 | chr3:108596097-108643420 |
| 28495 | Stxbp3b | NR_073559.1 | chr19:9632095-9633738 |
| 28496 | Stxbp4 | NM_011505.2 | chr11:90337806-90499422 |
| 28497 | Stxbp5 | NM_001081344.2 | chr10:9475344-9620838 |
| 28498 | Stxbp5l | NM_001114611.1 | chr16:37107395-37385044 |
| 28499 | Stxbp5l | NM_001114612.1 | chr16:37107395-37385044 |
| 28500 | Stxbp5l | NM_001114613.1 | chr16:37107395-37385044 |
| 28501 | Stxbp5l | NM_172440.3 | chr16:37107395-37385044 |
| 28502 | Stxbp6 | NM_144552.3 | chr12:45953472-46175470 |
| 28503 | Styk1 | NM_172891.2 | chr6:131249161-131263845 |
| 28504 | Styx | NM_019637.3 | chr14:45970861-45996559 |
| 28505 | Styxl1 | NM_001289554.1 | chr5:136223089-136254255 |
| 28506 | Styxl1 | NM_001289555.1 | chr5:136223089-136254255 |
| 28507 | Styxl1 | NM_001289556.1 | chr5:136223089-136254255 |
| 28508 | Styxl1 | NM_001289557.1 | chr5:136223089-136254255 |
| 28509 | Styxl1 | NM_029659.4 | chr5:136223089-136254255 |
| 28510 | Sub1 | NM_011294.3 | chr15:11911093-11925762 |
| 28511 | Sucla2 | NM_011506.3 | chr14:73952592-73995949 |
| 28512 | Suclg1 | NM_019879.3 | chr6:73198498-73226901 |
| 28513 | Suclg2 | NM_011507.3 | chr6:95423002-95668840 |
| 28514 | Sucnr1 | NM_032400.2 | chr3:59885790-59891488 |
| 28515 | Suco | NM_172645.2 | chr1:163746242-163769792 |
| 28516 | Suds3 | NM_001122666.2 | chr5:117541686-117566002 |
| 28517 | Suds3 | NM_178622.5 | chr5:117541686-117566002 |
| 28518 | Sufu | NM_001025912.2 | chr19:46471385-46563294 |
| 28519 | Sufu | NM_015752.3 | chr19:46471385-46563294 |
| 28520 | Sugct | NM_138654.3 | chr13:16949309-17786599 |
| 28521 | Sugp1 | NM_027481.2 | chr8:72566711-72595852 |
| 28522 | Sugp2 | NM_001168290.1 | chr8:72744091-72787004 |
| 28523 | Sugp2 | NM_172755.3 | chr8:72744091-72787004 |
| 28524 | Sugt1 | NM_026474.5 | chr14:79987497-80029562 |
| 28525 | Sulf1 | NM_001198565.1 | chr1:12682510-12850453 |
| 28526 | Sulf1 | NM_001198566.1 | chr1:12682510-12850453 |
| 28527 | Sulf1 | NM_172294.1 | chr1:12682510-12850453 |
| 28528 | Sulf2 | NM_001252578.1 | chr2:165899398-165981183 |
| 28529 | Sulf2 | NM_001252579.1 | chr2:165899398-165981183 |
| 28530 | Sulf2 | NM_028072.5 | chr2:165899398-165981183 |
| 28531 | Sult1a1 | NM_133670.1 | chr7:133816383-133819871 |
| 28532 | Sult1b1 | NM_019878.4 | chr5:87942363-87967220 |
| 28533 | Sult1c1 | NM_018751.2 | chr17:54100939-54129956 |
| 28534 | Sult1c1 | NM_018751.2 | chr17_random:581194-612733 |
| 28535 | Sult1c2 | NM_026935.4 | chr17:53968961-53985283 |
| 28536 | Sult1d1 | NM_016771.3 | chr5:87983674-87998031 |
| 28537 | Sult1e1 | NM_023135.2 | chr5:88004992-88020636 |
| 28538 | Sult2a1 | NM_001111296.2 | chr7:14381594-14422759 |
| 28539 | Sult2a2 | NM_009286.2 | chr7:14318854-14364986 |
| 28540 | Sult2a3 | NM_001101586.2 | chr7:14652903-14708342 |
| 28541 | Sult2a4 | NM_001101534.1 | chr7:14495025-14574937 |
| 28542 | Sult2a5 | NM_001184980.1 | chr7:14209315-14256156 |
| 28543 | Sult2a6 | NM_001081325.2 | chr7:14807751-14840219 |
| 28544 | Sult2a7 | NM_001184981.1 | chr7:15050507-15078275 |
| 28545 | Sult2b1 | NM_017465.2 | chr7:52985352-53014925 |
| 28546 | Sult3a1 | NM_020565.2 | chr10:33577527-33599281 |
| 28547 | Sult4a1 | NM_013873.3 | chr15:83906526-83936184 |
| 28548 | Sult5a1 | NM_020564.3 | chr8:125666746-125682180 |
| 28549 | Sult6b1 | NM_001163625.1 | chr17:79283277-79306332 |
| 28550 | Sumf1 | NM_145937.3 | chr6:108057014-108135577 |
| 28551 | Sumf2 | NM_026445.2 | chr5:130322866-130339827 |
| 28552 | Sumo1 | NM_009460.2 | chr1:59696277-59727678 |
| 28553 | Sumo2 | NM_133354.2 | chr11:115384423-115397544 |
| 28554 | Sumo3 | NM_019929.4 | chr10:77068978-77081076 |
| 28555 | Sun1 | NM_001256115.1 | chr5:139676590-139725793 |
| 28556 | Sun1 | NM_001256116.1 | chr5:139676590-139725793 |
| 28557 | Sun1 | NM_001256117.1 | chr5:139676590-139725793 |
| 28558 | Sun1 | NM_001256118.1 | chr5:139676590-139725793 |
| 28559 | Sun1 | NM_024451.2 | chr5:139676590-139725793 |
| 28560 | Sun2 | NM_001205345.1 | chr15:79554497-79572966 |
| 28561 | Sun2 | NM_001205346.1 | chr15:79554497-79572966 |
| 28562 | Sun2 | NM_194342.3 | chr15:79554497-79572966 |
| 28563 | Sun3 | NM_001290519.1 | chr11:8916056-8969357 |
| 28564 | Sun3 | NM_001290520.1 | chr11:8916056-8969357 |
| 28565 | Sun3 | NM_175576.3 | chr11:8916056-8969357 |
| 28566 | Sun5 | NM_029599.1 | chr2:153681925-153696820 |
| 28567 | Suox | NM_173733.3 | chr10:128106942-128110974 |
| 28568 | Supt16 | NM_033618.3 | chr14:52780094-52816914 |
| 28569 | Supt20 | NM_019995.3 | chr3:54497026-54520759 |
| 28570 | Supt3 | NM_178652.2 | chr17:44914120-45256233 |
| 28571 | Supt4a | NM_009296.1 | chr11:87551066-87557119 |
| 28572 | Supt5 | NM_013676.1 | chr7:29099914-29123738 |
| 28573 | Supt6 | NM_009297.1 | chr11:78020250-78059205 |
| 28574 | Supt7l | NM_028150.2 | chr5:31816941-31829135 |
| 28575 | Supv3l1 | NM_181423.2 | chr10:61892126-61912441 |
| 28576 | Surf1 | NM_001271724.1 | chr2:26768897-26789031 |
| 28577 | Surf1 | NM_013677.2 | chr2:26768897-26789031 |
| 28578 | Surf1 | NR_073420.1 | chr2:26768897-26789031 |
| 28579 | Surf2 | NM_013678.2 | chr2:26771941-26775690 |
| 28580 | Surf4 | NM_011512.3 | chr2:26775561-26789031 |
| 28581 | Surf6 | NM_009298.3 | chr2:26746291-26758333 |
| 28582 | Susd1 | NM_001163288.2 | chr4:59327554-59451505 |
| 28583 | Susd2 | NM_001162913.1 | chr10:75099363-75106753 |
| 28584 | Susd2 | NM_027890.5 | chr10:75099363-75106753 |
| 28585 | Susd3 | NM_025491.3 | chr13:49326199-49344075 |
| 28586 | Susd3 | NM_028340.1 | chr13:49326199-49344075 |
| 28587 | Susd4 | NM_144796.4 | chr1:184895036-184825785 |
| 28588 | Susd5 | NM_001101510.1 | chr9:113966471-114007851 |
| 28589 | Suv39h1 | NM_001290716.1 | chrX:7638296-7651886 |
| 28590 | Suv39h1 | NM_011514.2 | chrX:7638296-7651886 |
| 28591 | Suv39h2 | NM_022724.4 | chr2:3341402-3392258 |
| 28592 | Suv39h2 | NR_027509.1 | chr2:3341402-3392258 |
| 28593 | Suv420h1 | NM_001167884.1 | chr19:3767420-3818303 |
| 28594 | Suv420h1 | NM_001167885.1 | chr19:3767420-3818303 |
| 28595 | Suv420h1 | NM_001167886.1 | chr19:3767420-3818303 |
| 28596 | Suv420h1 | NM_001167887.1 | chr19:3767420-3818303 |
| 28597 | Suv420h1 | NM_001167888.1 | chr19:3767420-3818303 |
| 28598 | Suv420h1 | NM_001167889.1 | chr19:3767420-3818303 |
| 28599 | Suv420h1 | NM_144871.4 | chr19:3767420-3818303 |
| 28600 | Suv420h2 | NM_001115018.1 | chr7:4691728-4699116 |
| 28601 | Suv420h2 | NM_146177.2 | chr7:4691728-4699116 |
| 28602 | Suz12 | NM_001163018.1 | chr11:79806607-79847625 |
| 28603 | Suz12 | NM_199196.2 | chr11:79806607-79847625 |
| 28604 | Sv2a | NM_022030.3 | chr3:95985149-95999103 |
| 28605 | Sv2b | NM_001109753.1 | chr7:82259780-82476305 |

Fig. 25 - 152

| | | | |
|---|---|---|---|
| 28606 | Sv2b | NM_153579.4 | chr7:82259780-82476305 |
| 28607 | Sv2c | NM_029210.1 | chr13:96729397-96902532 |
| 28608 | Sva | NM_009299.2 | chr6:41988392-41992850 |
| 28609 | Svs1 | NM_027832.3 | chr6:41901626-41906097 |
| 28610 | Svs2 | NM_032542.1 | chr6:41810337-41814321 |
| 28611 | Svs3 | NM_001003952.1 | chr6:41918138-41923089 |
| 28612 | Svep1 | NM_022814.2 | chr4:58055667-58219468 |
| 28613 | Svil | NM_153153.3 | chr18:5046586-5119291 |
| 28614 | Svip | NM_001160345.1 | chr7:59252530-59261388 |
| 28615 | Svip | NR_027704.1 | chr7:59252530-59261388 |
| 28616 | Svop | NM_026805.1 | chr5:114476921-114541389 |
| 28617 | Svopl | NM_177200.4 | chr6:37933738-37996996 |
| 28618 | Svs1 | NM_172888.3 | chr6:48936859-48941723 |
| 28619 | Svs2 | NM_017890.4 | chr2:164061664-164064077 |
| 28620 | Svs3a | NM_021363.2 | chr2:164115003-164117236 |
| 28621 | Svs3b | NM_173377.2 | chr2:164080098-164082379 |
| 28622 | Svs4 | NM_009300.3 | chr2:164101691-164104043 |
| 28623 | Svs5 | NM_009301.2 | chr2:164158500-164160130 |
| 28624 | Svs6 | NM_013679.2 | chr2:164142486-164144186 |
| 28625 | Swap70 | NM_009302.3 | chr7:117365216-117427020 |
| 28626 | Swi5 | NM_001290552.1 | chr2:32134324-32143589 |
| 28627 | Swi5 | NM_175190.5 | chr2:32134324-32143589 |
| 28628 | Swi5 | NR_110965.1 | chr2:32134324-32143589 |
| 28629 | Swsap1 | NM_025870.1 | chr9:21760196-21762714 |
| 28630 | Swt1 | NM_025819.4 | chr1:153214828-153275565 |
| 28631 | Syap1 | NM_025932.2 | chrX:159294775-159326394 |
| 28632 | Sybu | NM_001032727.1 | chr15:44503402-44637375 |
| 28633 | Sybu | NM_001285840.1 | chr15:44503402-44637375 |
| 28634 | Sybu | NM_001285841.1 | chr15:44503402-44637375 |
| 28635 | Sybu | NM_001285842.1 | chr15:44503402-44637375 |
| 28636 | Sybu | NM_001285843.1 | chr15:44503402-44637375 |
| 28637 | Sybu | NM_001285844.1 | chr15:44503402-44637375 |
| 28638 | Sybu | NM_176998.4 | chr15:44503402-44637375 |
| 28639 | Sybu | NM_178765.3 | chr15:44503402-44637375 |
| 28640 | Syce1 | NM_001143765.1 | chr7:147963127-147973753 |
| 28641 | Syce1l | NM_001048145.1 | chr8:116159485-116179433 |
| 28642 | Syce1l | NM_001286494.1 | chr8:116159485-116179433 |
| 28643 | Syce1l | NM_029139.1 | chr8:116159485-116179433 |
| 28644 | Syce2 | NM_001168244.1 | chr8:87396009-87417820 |
| 28645 | Syce2 | NM_001168246.1 | chr8:87396009-87417820 |
| 28646 | Syce2 | NM_027954.3 | chr8:87396009-87417820 |
| 28647 | Syce2 | NR_031759.1 | chr8:87396009-87417820 |
| 28648 | Syce3 | NM_001162880.1 | chr15:89220604-89240934 |
| 28649 | Syce3 | NM_001162882.1 | chr15:89220604-89240934 |
| 28650 | Sycn | NM_026716.3 | chr7:29325903-29327229 |
| 28651 | Sycp1 | NM_011516.2 | chr3:102622421-102740023 |
| 28652 | Sycp1-ps1 | NR_024208.1 | chr7:19371651-19374763 |
| 28653 | Sycp2 | NM_177191.3 | chr2:178080000-178142363 |
| 28654 | Sycp3 | NM_011517.2 | chr10:87922332-87935981 |
| 28655 | Syde1 | NM_027875.1 | chr10:78047247-78054709 |
| 28656 | Syde2 | NM_001166064.1 | chr3:145650833-145684684 |
| 28657 | Syf2 | NM_026780.3 | chr4:134486894-134493452 |
| 28658 | Syk | NM_001198977.1 | chr13:52678805-52744161 |
| 28659 | Syk | NM_011518.2 | chr13:52678805-52744161 |
| 28660 | Sympk | NM_026605.2 | chr7:19609725-19639971 |
| 28661 | Syn1 | NM_001110780.1 | chrX:20425668-20498044 |
| 28662 | Syn1 | NM_013680.4 | chrX:20425668-20498044 |
| 28663 | Syn2 | NM_001111015.1 | chr6:115084919-115232644 |
| 28664 | Syn2 | NM_013681.3 | chr6:115084919-115232644 |
| 28665 | Syn3 | NM_001164495.1 | chr10:85511490-85961641 |
| 28666 | Syn3 | NM_013722.3 | chr10:85511490-85961641 |
| 28667 | Syna | NM_001013751.2 | chr5:135033123-135036041 |
| 28668 | Synb | NM_173420.3 | chr14:69908454-69911236 |
| 28669 | Sync | NM_023485.3 | chr4:128964865-128985803 |
| 28670 | Syncrip | NM_001284328.1 | chr9:88344201-88377235 |
| 28671 | Syncrip | NM_019666.2 | chr9:88344201-88377235 |
| 28672 | Syncrip | NM_019796.5 | chr9:88344201-88377235 |
| 28673 | Syndig1 | NM_001085521.2 | chr2:149656518-149830128 |
| 28674 | Syndig1l | NM_001033334.2 | chr12:86018227-86039757 |
| 28675 | Syne1 | NM_001079686.1 | chr10:4795848-5009592 |
| 28676 | Syne1 | NM_022027.2 | chr10:5151833-5326342 |
| 28677 | Syne1 | NM_153399.1 | chr10:5151833-5326342 |
| 28678 | Syne2 | NM_001005510.2 | chr12:76919305-77211915 |
| 28679 | Syne3 | NM_001042699.2 | chr12:106168142-106248019 |
| 28680 | Syne3 | NM_172500.3 | chr12:106168142-106248019 |
| 28681 | Syne4 | NM_029065.1 | chr7:31099834-31104064 |
| 28682 | Syne4 | NM_153577.2 | chr7:31099834-31104064 |
| 28683 | Syngap1 | NM_001281491.1 | chr17:27078397-27117590 |
| 28684 | Syngr1 | NM_009303.2 | chr15:79921763-79949931 |
| 28685 | Syngr1 | NM_207708.1 | chr15:79921763-79949931 |
| 28686 | Syngr2 | NM_009304.2 | chr11:117670980-117675600 |
| 28687 | Syngr3 | NM_011525.2 | chr17:24822036-24826894 |
| 28688 | Syngr4 | NM_001291064.1 | chr7:53142214-53152081 |
| 28689 | Syngr4 | NM_021482.2 | chr7:53142214-53152081 |
| 28690 | Synj1 | NM_001045515.1 | chr16:90936341-91044624 |
| 28691 | Synj1 | NM_001164483.1 | chr16:90936341-91044624 |
| 28692 | Synj2 | NM_001113351.1 | chr17:5941279-6079739 |
| 28693 | Synj2 | NM_001113352.2 | chr17:5941279-6079739 |
| 28694 | Synj2 | NM_001113353.2 | chr17:5941279-6079739 |
| 28695 | Synj2 | NM_001290698.1 | chr17:5941279-6079739 |
| 28696 | Synj2 | NM_011523.2 | chr17:5941279-6079739 |
| 28697 | Synj2bp | NM_025292.6 | chr12:82593180-82628934 |
| 28698 | Synm | NM_183312.3 | chr7:74875046-74904628 |
| 28699 | Synm | NM_201639.2 | chr7:74875046-74904628 |
| 28700 | Synm | NM_207663.3 | chr7:74875046-74904628 |

| | | | |
|---|---|---|---|
| 28701 | Synpo | NM_001109975.1 | chr18:60753643-60783959 |
| 28702 | Synpo | NM_177340.2 | chr18:60753643-60783959 |
| 28703 | Synpo2 | NM_080451.2 | chr3:122779436-122939067 |
| 28704 | Synpo2l | NM_175132.3 | chr14:21478639-21487528 |
| 28705 | Synpr | NM_001163032.1 | chr14:14117293-14447983 |
| 28706 | Synpr | NM_028052.4 | chr14:14117293-14447983 |
| 28707 | Synrg | NM_194341.2 | chr11:83777932-83858078 |
| 28708 | Syp | NM_009305.2 | chrX:7215705-7230382 |
| 28709 | Sypl | NM_013635.3 | chr12:33638809-33664367 |
| 28710 | Sypl | NM_198710.3 | chr12:33638809-33664367 |
| 28711 | Sypl2 | NM_008596.1 | chr3:108015183-108029517 |
| 28712 | Sys1 | NM_025575.3 | chr2:164286470-164291010 |
| 28713 | Syt1 | NM_001252341.1 | chr10:107934705-108448031 |
| 28714 | Syt1 | NM_001252342.1 | chr10:107934705-108448031 |
| 28715 | Syt1 | NM_009306.3 | chr10:107934705-108448031 |
| 28716 | Syt10 | NM_018803.2 | chr15:89612823-89672291 |
| 28717 | Syt11 | NM_018804.3 | chr3:88548622-88576521 |
| 28718 | Syt12 | NM_134164.5 | chr19:4445908-4477143 |
| 28719 | Syt13 | NM_030725.4 | chr2:92755257-92796208 |
| 28720 | Syt14 | NM_181546.3 | chr1:194723500-194861892 |
| 28721 | Syt15 | NM_169931.2 | chr14:35033231-35043607 |
| 28722 | Syt15 | NM_181529.4 | chr14:35033231-35043607 |
| 28723 | Syt16 | NM_172804.2 | chr12:75098747-75368903 |
| 28724 | Syt17 | NM_138649.1 | chr7:125525369-125587066 |
| 28725 | Syt2 | NM_009307.3 | chr1:136543257-136645994 |
| 28726 | Syt3 | NM_001114116.1 | chr7:51639495-51655400 |
| 28727 | Syt3 | NM_016663.3 | chr7:51639495-51655400 |
| 28728 | Syt4 | NM_009308.3 | chr18:31597461-31607069 |
| 28729 | Syt5 | NM_016908.2 | chr7:4491366-4498169 |
| 28730 | Syt6 | NM_001276676.1 | chr3:103379204-103449490 |
| 28731 | Syt6 | NM_001276677.1 | chr3:103379204-103449490 |
| 28732 | Syt6 | NM_001276679.1 | chr3:103379204-103449490 |
| 28733 | Syt6 | NM_001276680.1 | chr3:103379204-103449490 |
| 28734 | Syt6 | NM_001276681.1 | chr3:103379204-103449490 |
| 28735 | Syt6 | NM_018800.4 | chr3:103379204-103449490 |
| 28736 | Syt7 | NM_018801.3 | chr19:10463579-10527671 |
| 28737 | Syt7 | NM_173067.3 | chr19:10463579-10527671 |
| 28738 | Syt7 | NM_173068.2 | chr19:10463579-10527671 |
| 28739 | Syt8 | NM_001285857.1 | chr7:149620881-149626301 |
| 28740 | Syt8 | NM_001285858.1 | chr7:149620881-149626301 |
| 28741 | Syt8 | NM_001285861.1 | chr7:149620881-149626301 |
| 28742 | Syt8 | NM_018802.5 | chr7:149620881-149626301 |
| 28743 | Syt9 | NM_021889.4 | chr7:114514303-114692169 |
| 28744 | Sytl1 | NM_031393.2 | chr4:132809004-132819002 |
| 28745 | Sytl2 | NM_001040085.2 | chr7:97450864-97559229 |
| 28746 | Sytl2 | NM_001040087.2 | chr7:97450864-97559229 |
| 28747 | Sytl2 | NM_001040088.2 | chr7:97450864-97559229 |
| 28748 | Sytl2 | NM_001289583.1 | chr7:97450864-97559229 |
| 28749 | Sytl2 | NM_001289584.1 | chr7:97450864-97559229 |
| 28750 | Sytl2 | NM_001289585.1 | chr7:97450864-97559229 |
| 28751 | Sytl2 | NM_001289586.1 | chr7:97450864-97559229 |
| 28752 | Sytl2 | NM_031394.3 | chr7:97450864-97559229 |
| 28753 | Sytl2 | NR_110348.1 | chr7:97450864-97559229 |
| 28754 | Sytl3 | NM_031395.2 | chr17:6877959-6942393 |
| 28755 | Sytl3 | NM_183368.2 | chr17:6877959-6942393 |
| 28756 | Sytl3 | NM_183370.2 | chr17:6877959-6942393 |
| 28757 | Sytl4 | NM_001290717.1 | chrX:130470923-130516351 |
| 28758 | Sytl4 | NM_001290718.1 | chrX:130470923-130516351 |
| 28759 | Sytl4 | NM_001290719.1 | chrX:130470923-130516351 |
| 28760 | Sytl4 | NM_013757.2 | chrX:130470923-130516351 |
| 28761 | Sytl5 | NM_001290728.1 | chrX:9462746-9575990 |
| 28762 | Sytl5 | NM_177704.3 | chrX:9462746-9575990 |
| 28763 | Syvn1 | NM_001164709.1 | chr19:6046575-6057751 |
| 28764 | Syvn1 | NM_028769.5 | chr19:6046575-6057751 |
| 28765 | Szrd1 | NM_001025608.2 | chr4:140668892-140695711 |
| 28766 | Szrd1 | NM_001277195.1 | chr4:140668892-140695711 |
| 28767 | Szrd1 | NR_102343.1 | chr4:140668892-140695711 |
| 28768 | Szrd1 | NR_102344.1 | chr4:140668892-140695711 |
| 28769 | Szt2 | NM_198170.4 | chr4:118035345-118081868 |
| 28770 | T | NM_009309.2 | chr17:8627287-8635361 |
| 28771 | T2 | NM_001161832.1 | chr17:8565261-8615591 |
| 28772 | Taar1 | NM_053205.1 | chr10:23640211-23643210 |
| 28773 | Taar2 | NM_001007266.1 | chr10:23658377-23661389 |
| 28774 | Taar3 | NM_001008429.1 | chr10:23669363-23670395 |
| 28775 | Taar4 | NM_001008499.1 | chr10:23680299-23681343 |
| 28776 | Taar5 | NM_001009574.1 | chr10:23690511-23691525 |
| 28777 | Taar6 | NM_001010828.1 | chr10:23704414-23705452 |
| 28778 | Taar7a | NM_001010829.1 | chr10:23712210-23713287 |
| 28779 | Taar7b | NM_001010827.1 | chr10:23719744-23720821 |
| 28780 | Taar7d | NM_001010838.1 | chr10:23747027-23748104 |
| 28781 | Taar7e | NM_001010835.1 | chr10:23757419-23758496 |
| 28782 | Taar7f | NM_001010839.1 | chr10:23769315-23770392 |
| 28783 | Taar8a | NM_001010830.1 | chr10:23796305-23797340 |
| 28784 | Taar8b | NM_001010837.1 | chr10:23811065-23812100 |
| 28785 | Taar8c | NM_001010840.1 | chr10:23820648-23821757 |
| 28786 | Taar9 | NM_001010831.1 | chr10:23828293-23829340 |
| 28787 | Tab1 | NM_025609.2 | chr15:79963583-79992132 |
| 28788 | Tab2 | NM_138667.3 | chr10:7625445-7675921 |
| 28789 | Tab3 | NM_025729.4 | chrX:82819360-82879808 |
| 28790 | Tac1 | NM_009311.2 | chr6:7505070-7512973 |
| 28791 | Tac2 | NM_001199971.1 | chr10:127161533-127168824 |
| 28792 | Tac2 | NM_009312.2 | chr10:127161533-127168824 |
| 28793 | Tac4 | NM_053093.1 | chr11:95122842-95130575 |
| 28794 | Tacc1 | NM_177089.5 | chr8:26265023-26312014 |
| 28795 | Tacc1 | NM_199323.3 | chr8:26265023-26312014 |

Fig. 25 - 153

| | | | | | | | | |
|---|---|---|---|---|---|---|---|---|
| 28796 | Tacc2 | NM_001004468.2 | chr7:137720997-137908298 | | 28891 | Tas1r3 | NM_031872.2 | chr4:155233379-155237462 |
| 28797 | Tacc2 | NM_021314.4 | chr7:137720997-137908298 | | 28892 | Tas2r102 | NM_199153.2 | chr6:132712148-132713192 |
| 28798 | Tacc2 | NM_206856.2 | chr7:137720997-137908298 | | 28893 | Tas2r103 | NM_053211.1 | chr6:132986180-132987119 |
| 28799 | Tacc3 | NM_001040435.2 | chr5:34000795-34014846 | | 28894 | Tas2r104 | NM_207011.1 | chr6:131634853-131635762 |
| 28800 | Taco1 | NM_027346.1 | chr11:105927420-105934926 | | 28895 | Tas2r105 | NM_020501.1 | chr6:131636578-131637481 |
| 28801 | Tacr1 | NM_009313.5 | chr6:82352468-82510098 | | 28896 | Tas2r106 | NM_207016.1 | chr6:131627977-131628904 |
| 28802 | Tacr2 | NM_009314.4 | chr10:61715185-61728738 | | 28897 | Tas2r107 | NM_199154.1 | chr6:131609175-131610102 |
| 28803 | Tacr3 | NM_021382.6 | chr3:134491970-134597545 | | 28898 | Tas2r108 | NM_020502.1 | chr6:40443590-40444484 |
| 28804 | Tacstd2 | NM_020047.3 | chr6:67484052-67485816 | | 28899 | Tas2r109 | NM_207017.1 | chr6:132930032-132930983 |
| 28805 | Tada1 | NM_030245.3 | chr1:168309298-168323751 | | 28900 | Tas2r110 | NM_199155.2 | chr6:132818025-132819027 |
| 28806 | Tada2a | NM_172562.3 | chr6:183892421-83943070 | | 28901 | Tas2r113 | NM_207018.1 | chr6:132843028-132843958 |
| 28807 | Tada2b | NM_001170454.1 | chr5:36816319-36826934 | | 28902 | Tas2r114 | NM_207019.1 | chr6:131639151-131640081 |
| 28808 | Tada3 | NM_133932.2 | chr6:113316654-113327514 | | 28903 | Tas2r115 | NM_207020.1 | chr6:132687071-132688004 |
| 28809 | Taf1 | NM_001081008.1 | chrX:98728073-98797128 | | 28904 | Tas2r116 | NM_053212.1 | chr6:132805455-132806373 |
| 28810 | Taf1 | NM_001290729.1 | chrX:98728073-98797128 | | 28905 | Tas2r117 | NM_207021.1 | chr6:132752918-132753911 |
| 28811 | Taf10 | NM_020024.3 | chr7:112891408-112892852 | | 28906 | Tas2r118 | NM_207022.1 | chr6:23919180-23920060 |
| 28812 | Taf11 | NM_026836.2 | chr17:28038072-28044669 | | 28907 | Tas2r119 | NM_020503.2 | chr15:32107043-32108049 |
| 28813 | Taf12 | NM_025579.3 | chr4:131830289-131849244 | | 28908 | Tas2r120 | NM_207023.1 | chr6:132606974-132607862 |
| 28814 | Taf13 | NM_025444.2 | chr3:108374616-108384986 | | 28909 | Tas2r121 | NM_207024.1 | chr6:132650107-132651025 |
| 28815 | Taf15 | NM_027427.2 | chr11:83286609-83320242 | | 28910 | Tas2r122 | NM_001039128.1 | chr6:132661016-132661946 |
| 28816 | Taf1a | NM_001277957.1 | chr1_random:362232-383551 | | 28911 | Tas2r123 | NM_207025.1 | chr6:132797159-132798161 |
| 28817 | Taf1a | NM_001277958.1 | chr1_random:362232-383551 | | 28912 | Tas2r124 | NM_207026.1 | chr6:132704747-132705677 |
| 28818 | Taf1a | NM_001277959.1 | chr1_random:362232-383551 | | 28913 | Tas2r125 | NM_207027.1 | chr6:132859668-132860604 |
| 28819 | Taf1a | NM_021466.3 | chr1_random:362232-383551 | | 28914 | Tas2r126 | NM_207028.1 | chr6:42384533-42385460 |
| 28820 | Taf1b | NM_020614.2 | chr12:25183445-25243436 | | 28915 | Tas2r129 | NM_207029.1 | chr6:132901119-132902082 |
| 28821 | Taf1b | NR_028341.1 | chr12:25183445-25243436 | | 28916 | Tas2r130 | NM_199156.1 | chr6:131579909-131580848 |
| 28822 | Taf1c | NM_021441.2 | chr8:122121874-122129140 | | 28917 | Tas2r131 | NM_207030.1 | chr6:132906929-132907862 |
| 28823 | Taf1d | NM_027261.3 | chr9:15087780-15162232 | | 28918 | Tas2r134 | NM_199158.1 | chr2:51483030-51483927 |
| 28824 | Taf1d | NM_029248.2 | chr9:15087780-15162232 | | 28919 | Tas2r135 | NM_199159.1 | chr6:42355527-42356493 |
| 28825 | Taf1d | NR_028401.1 | chr9:15087780-15162232 | | 28920 | Tas2r136 | NM_181276.1 | chr6:132727196-132728180 |
| 28826 | Taf2 | NM_001081288.1 | chr15:54846683-54903707 | | 28921 | Tas2r137 | NM_001025385.1 | chr6:40441236-40442238 |
| 28827 | Taf3 | NM_027748.3 | chr2:9836178-9970236 | | 28922 | Tas2r138 | NM_001001451.1 | chr6:40562313-40563309 |
| 28828 | Taf4a | NM_001081092.1 | chr2:179646850-179711351 | | 28923 | Tas2r139 | NM_181275.1 | chr6:42090934-42091894 |
| 28829 | Taf4b | NM_001100449.1 | chr18:14941753-15058868 | | 28924 | Tas2r140 | NM_021562.1 | chr6:133004872-133005811 |
| 28830 | Taf5 | NM_177342.3 | chr19:47142238-47157969 | | 28925 | Tas2r143 | NM_001001452.1 | chr6:42350236-42351118 |
| 28831 | Taf5l | NM_133966.2 | chr8:126520215-126545209 | | 28926 | Tas2r144 | NM_001001453.1 | chr6:42165326-42166286 |
| 28832 | Taf6 | NM_009315.3 | chr5:138619845-138628414 | | 28927 | Tasp1 | NM_001159640.2 | chr2:139659214-139892541 |
| 28833 | Taf6l | NM_001177798.1 | chr19:8847011-8860907 | | 28928 | Tasp1 | NM_001159641.2 | chr2:139659214-139892541 |
| 28834 | Taf6l | NM_146092.2 | chr19:8847011-8860907 | | 28929 | Tasp1 | NM_001289611.1 | chr2:139659214-139892541 |
| 28835 | Taf7 | NM_175770.4 | chr18:37800145-37803858 | | 28930 | Tasp1 | NM_175225.5 | chr2:139659214-139892541 |
| 28836 | Taf7l | NM_028958.4 | chrX:130994654-131011029 | | 28931 | Tasp1 | NR_110350.1 | chr2:139659214-139892541 |
| 28837 | Taf8 | NM_022015.3 | chr17:47624998-47639236 | | 28932 | Tasp1 | NR_110351.1 | chr2:139659214-139892541 |
| 28838 | Taf9 | NM_001015889.2 | chr13:101421297-101436370 | | 28933 | Tasp1 | NR_110352.1 | chr2:139659214-139892541 |
| 28839 | Taf9 | NM_027139.5 | chr13:101421297-101436370 | | 28934 | Tat | NM_146214.3 | chr8:112514335-112523704 |
| 28840 | Taf9b | NM_001001176.1 | chrX:103402212-103416497 | | 28935 | Tatdn1 | NM_175151.4 | chr15:58721708-58765285 |
| 28841 | Taf9b | NM_001167988.1 | chrX:103402212-103416497 | | 28936 | Tatdn2 | NM_001033463.3 | chr13:647493-113661062 |
| 28842 | Tagap | NM_145968.2 | chr17_random:39676-48574 | | 28937 | Tatdn3 | NM_001163421.1 | chr1:192869708-192886811 |
| 28843 | Tagap | NM_145968.2 | chr17:8118864-8127762 | | 28938 | Tatdn3 | NM_001163422.1 | chr1:192869708-192886811 |
| 28844 | Tagap1 | NM_147155.2 | chr17:7159313-7165505 | | 28939 | Tatdn3 | NM_026895.1 | chr1:192869708-192886811 |
| 28845 | Tagln | NM_011526.5 | chr9:45737711-45744141 | | 28940 | Tax1bp1 | NM_025816.3 | chr6:52663722-52716773 |
| 28846 | Tagln2 | NM_178586.2 | chr1:174430376-174437506 | | 28941 | Tax1bp3 | NM_029564.2 | chr11:72990584-72995548 |
| 28847 | Tagln3 | NM_019754.3 | chr16:45711342-45724644 | | 28942 | Taz | NM_001173547.2 | chrX:71528056-71535490 |
| 28848 | Tal1 | NM_001287388.1 | chr4:114729030-114744360 | | 28943 | Taz | NM_001242615.2 | chrX:71528056-71535490 |
| 28849 | Tal1 | NM_011527.3 | chr4:114729030-114744360 | | 28944 | Taz | NM_001242616.2 | chrX:71528056-71535490 |
| 28850 | Tal2 | NM_009317.1 | chr4:53792576-53799757 | | 28945 | Taz | NM_001290738.1 | chrX:71528056-71535490 |
| 28851 | Taldo1 | NM_011528.4 | chr7:148578058-148588875 | | 28946 | Taz | NM_181516.6 | chrX:71528056-71535490 |
| 28852 | Tamm41 | NM_026894.1 | chr6:114954398-114987892 | | 28947 | Tbata | NM_001017407.1 | chr10:60634711-60651589 |
| 28853 | Tanc1 | NM_001290659.1 | chr2:59450098-59684270 | | 28948 | Tbata | NM_001017409.1 | chr10:60634711-60651589 |
| 28854 | Tanc1 | NM_198294.2 | chr2:59450098-59684270 | | 28949 | Tbata | NM_001017419.2 | chr10:60634711-60651589 |
| 28855 | Tanc2 | NM_181071.3 | chr11:105451299-105790617 | | 28950 | Tbata | NM_001017433.2 | chr10:60634711-60651589 |
| 28856 | Tango2 | NM_138583.2 | chr16:18300918-18344025 | | 28951 | Tbata | NM_001017441.2 | chr10:60634711-60651589 |
| 28857 | Tango6 | NM_173037.1 | chr8:109206967-109375339 | | 28952 | Tbata | NM_023064.3 | chr10:60634711-60651589 |
| 28858 | Tank | NM_001164071.1 | chr2:61416642-61492226 | | 28953 | Tbc1d1 | NM_001289514.1 | chr5:64551498-64742725 |
| 28859 | Tank | NM_001164072.1 | chr2:61416642-61492226 | | 28954 | Tbc1d1 | NM_019636.3 | chr5:64551498-64742725 |
| 28860 | Tank | NM_011529.2 | chr2:61416642-61492226 | | 28955 | Tbc1d10a | NM_134023.1 | chr11:4086835-4115508 |
| 28861 | Taok1 | NM_144825.2 | chr11:77342663-77421317 | | 28956 | Tbc1d10b | NM_144522.5 | chr7:134340973-134351982 |
| 28862 | Taok2 | NM_001163774.1 | chr7:134009190-134028481 | | 28957 | Tbc1d10c | NM_178650.3 | chr19:4184356-4191047 |
| 28863 | Taok2 | NM_001163775.1 | chr7:134009190-134028481 | | 28958 | Tbc1d12 | NM_145952.3 | chr19:38911068-38994413 |
| 28864 | Taok3 | NM_001081308.2 | chr5:117570137-117725107 | | 28959 | Tbc1d13 | NM_146252.2 | chr2:29989390-30007533 |
| 28865 | Taok3 | NM_001199685.1 | chr5:117570137-117725107 | | 28960 | Tbc1d14 | NM_001113362.1 | chr5:36833252-36928875 |
| 28866 | Taok3 | NM_183306.2 | chr5:117570137-117725107 | | 28961 | Tbc1d14 | NM_001113364.1 | chr5:36833252-36928875 |
| 28867 | Tap1 | NM_001161730.1 | chr17:34324500-34334170 | | 28962 | Tbc1d14 | NM_133910.3 | chr5:36833252-36928875 |
| 28868 | Tap1 | NM_013683.2 | chr17:34324500-34334170 | | 28963 | Tbc1d15 | NM_025706.3 | chr10:114634926-114688549 |
| 28869 | Tap2 | NM_011530.3 | chr17:34341423-34353266 | | 28964 | Tbc1d16 | NM_172443.3 | chr11:119004357-119089813 |
| 28870 | Tapbp | NM_001025313.1 | chr17:34056422-34066235 | | 28965 | Tbc1d17 | NM_001042655.1 | chr7:52096146-52104449 |
| 28871 | Tapbp | NM_009318.2 | chr17:34056422-34066235 | | 28966 | Tbc1d19 | NM_144517.4 | chr5:54200865-54295619 |
| 28872 | Tapbpl | NM_145391.2 | chr6:125174230-125181878 | | 28967 | Tbc1d2 | NM_198664.5 | chr4:46617261-46663071 |
| 28873 | Tapt1 | NM_173764.3 | chr5:44566400-44617845 | | 28968 | Tbc1d20 | NM_024196.3 | chr2:152119607-152138326 |
| 28874 | Tarbp2 | NM_001253795.1 | chr15:102348622-102354107 | | 28969 | Tbc1d21 | NM_028854.3 | chr9:58207610-58218176 |
| 28875 | Tarbp2 | NM_009319.3 | chr15:102348622-102354107 | | 28970 | Tbc1d22a | NM_145476.2 | chr15:86044888-86328933 |
| 28876 | Tardbp | NM_001003898.3 | chr4:147976652-148001105 | | 28971 | Tbc1d22b | NM_198647.1 | chr17:29686747-29743753 |
| 28877 | Tardbp | NM_001003899.2 | chr4:147976652-148001105 | | 28972 | Tbc1d22bos | NR_045447.1 | chr17:29715761-29733250 |
| 28878 | Tardbp | NM_001008545.2 | chr4:147976652-148001105 | | 28973 | Tbc1d23 | NM_026254.2 | chr16:57168676-57231579 |
| 28879 | Tardbp | NM_001008546.2 | chr4:147976652-148001105 | | 28974 | Tbc1d24 | NM_001163847.1 | chr17:24312375-24346332 |
| 28880 | Tardbp | NM_145556.4 | chr4:147976652-148001105 | | 28975 | Tbc1d24 | NM_001163848.1 | chr17:24312375-24346332 |
| 28881 | Tardbp | NR_028864.1 | chr4:147976652-148001105 | | 28976 | Tbc1d24 | NM_001163849.1 | chr17:24312375-24346332 |
| 28882 | Tarm1 | NM_177363.3 | chr7:3489696-3503433 | | 28977 | Tbc1d24 | NM_001163850.1 | chr17:24312375-24346332 |
| 28883 | Tars | NM_033074.3 | chr15:11313417-11329413 | | 28978 | Tbc1d24 | NM_001163851.1 | chr17:24312375-24346332 |
| 28884 | Tars2 | NM_001163617.1 | chr3:95543896-95558900 | | 28979 | Tbc1d24 | NM_001163852.1 | chr17:24312375-24346332 |
| 28885 | Tars2 | NM_001163618.1 | chr3:95543896-95558900 | | 28980 | Tbc1d24 | NM_001163853.1 | chr17:24312375-24346332 |
| 28886 | Tars2 | NM_001163619.1 | chr3:95543896-95558900 | | 28981 | Tbc1d24 | NM_173186.4 | chr17:24312375-24346332 |
| 28887 | Tars2 | NM_027931.3 | chr3:95543896-95558900 | | 28982 | Tbc1d25 | NM_001166437.1 | chrX:7731597-7753307 |
| 28888 | Tarsl2 | NM_172310.2 | chr7:72789783-72836979 | | 28983 | Tbc1d25 | NM_172478.3 | chrX:7731597-7753307 |
| 28889 | Tas1r1 | NM_031867.2 | chr4:151402022-151412599 | | 28984 | Tbc1d2b | NM_194334.2 | chr9:90096886-90165607 |
| 28890 | Tas1r2 | NM_031873.1 | chr4:139209452-139226194 | | 28985 | Tbc1d30 | NM_029057.1 | chr10:120700875-120748245 |

Fig. 25 - 154

| | | | |
|---|---|---|---|
| 28986 | Tbc1d31 | NM_001081396.2 | chr15:57743753-57801623 |
| 28987 | Tbc1d31 | NM_001167679.1 | chr15:57743753-57801623 |
| 28988 | Tbc1d32 | NM_001033385.3 | chr10:55734100-55948495 |
| 28989 | Tbc1d4 | NM_001081278.2 | chr14:101841576-102008408 |
| 28990 | Tbc1d5 | NM_001285991.1 | chr17:50872451-51318677 |
| 28991 | Tbc1d5 | NM_001285993.1 | chr17:50872451-51318677 |
| 28992 | Tbc1d5 | NM_028162.4 | chr17:50872451-51318677 |
| 28993 | Tbc1d7 | NM_001252639.1 | chr13:43247108-43266870 |
| 28994 | Tbc1d7 | NM_001252640.1 | chr13:43247108-43266870 |
| 28995 | Tbc1d7 | NM_025935.3 | chr13:43247108-43266870 |
| 28996 | Tbc1d8 | NM_018775.4 | chr1:39428342-39535592 |
| 28997 | Tbc1d8b | NM_001081499.2 | chrX:136219534-136288757 |
| 28998 | Tbc1d9 | NM_001111304.1 | chr8:85689250-85796839 |
| 28999 | Tbc1d9 | NM_027758.4 | chr8:85689250-85796839 |
| 29000 | Tbc1d9b | NM_001290759.1 | chr11:49944861-49986287 |
| 29001 | Tbc1d9b | NM_001290760.1 | chr11:49944861-49986287 |
| 29002 | Tbc1d9b | NM_029745.2 | chr11:49944861-49986287 |
| 29003 | Tbca | NM_009321.2 | chr13:95558897-95612854 |
| 29004 | Tbcb | NM_025548.3 | chr7:31009149-31017048 |
| 29005 | Tbcc | NM_178385.3 | chr17:47027569-47029412 |
| 29006 | Tbccd1 | NM_001081368.1 | chr16:22813287-22857642 |
| 29007 | Tbcd | NM_029878.3 | chr11:121313263-121478484 |
| 29008 | Tbce | NM_178337.3 | chr13:14090218-14131905 |
| 29009 | Tbcel | NM_178038.3 | chr9:42220399-42280309 |
| 29010 | Tbck | NM_001163455.2 | chr3:132347107-132501470 |
| 29011 | Tbck | NM_178032.3 | chr3:132347107-132501470 |
| 29012 | Tbkl | NM_019786.4 | chr10:120983512-121023850 |
| 29013 | Tbkbp1 | NM_198100.2 | chr11:96997485-97011026 |
| 29014 | Tbl1x | NM_020601.2 | chrX:74756565-74905604 |
| 29015 | Tbl1xr1 | NM_030732.1 | chr3:21975573-22115516 |
| 29016 | Tbl2 | NM_011763.2 | chr5:135625580-135638532 |
| 29017 | Tbl3 | NM_145396.4 | chr17:24837597-24844598 |
| 29018 | Tbp | NM_013684.3 | chr17:15636851-15654391 |
| 29019 | Tbpl1 | NM_011603.5 | chr10:22423683-22451253 |
| 29020 | Tbpl2 | NM_001289689.1 | chr2:23926885-23952115 |
| 29021 | Tbpl2 | NM_199059.2 | chr2:23926885-23952115 |
| 29022 | Tbpl2 | NR_110359.1 | chr2:23926885-23952115 |
| 29023 | Tbr1 | NM_009322.3 | chr2:61642509-61652170 |
| 29024 | Tbrg1 | NM_025289.3 | chr9:37456766-37464897 |
| 29025 | Tbrg3 | NR_027799.1 | chr15:82720913-82728891 |
| 29026 | Tbrg4 | NM_001130457.1 | chr1:6515600-6526070 |
| 29027 | Tbrg4 | NM_134011.2 | chr1:6515600-6526070 |
| 29028 | Tbx1 | NM_001285472.1 | chr16:18581796-18590764 |
| 29029 | Tbx1 | NM_001285476.1 | chr16:18581796-18590764 |
| 29030 | Tbx1 | NM_011532.2 | chr16:18581796-18590764 |
| 29031 | Tbx10 | NM_001001320.1 | chr19:3992751-3999512 |
| 29032 | Tbx10 | NM_011533.2 | chr19:3992751-3999512 |
| 29033 | Tbx15 | NM_009323.2 | chr3:99057682-99158183 |
| 29034 | Tbx18 | NM_023814.4 | chr9:87597634-87626095 |
| 29035 | Tbx19 | NM_032005.4 | chr1:167067983-167090904 |
| 29036 | Tbx2 | NM_009324.2 | chr11:85646116-85655450 |
| 29037 | Tbx20 | NM_001205085.1 | chr9:24525255-24578747 |
| 29038 | Tbx20 | NM_020496.3 | chr9:24525255-24578747 |
| 29039 | Tbx20 | NM_194263.2 | chr9:24525255-24578747 |
| 29040 | Tbx21 | NM_019507.2 | chr11:96959320-96976645 |
| 29041 | Tbx22 | NM_001290747.1 | chrX:104863302-104884319 |
| 29042 | Tbx22 | NM_145224.3 | chrX:104863302-104884319 |
| 29043 | Tbx22 | NM_181319.5 | chrX:104863302-104884319 |
| 29044 | Tbx3 | NM_011535.3 | chr5:120120870-120134733 |
| 29045 | Tbx3 | NM_198052.2 | chr5:120120870-120134733 |
| 29046 | Tbx3os2 | NR_040416.1 | chr5:120135096-120141227 |
| 29047 | Tbx4 | NM_011536.2 | chr11:85703564-85729599 |
| 29048 | Tbx4 | NM_172798.1 | chr11:85703564-85729599 |
| 29049 | Tbx5 | NM_011537.3 | chr5:120284671-120335227 |
| 29050 | Tbx6 | NM_011538.2 | chr7:133924996-133929662 |
| 29051 | Tbxa2r | NM_001277265.1 | chr10:80791447-80797919 |
| 29052 | Tbxa2r | NM_009325.4 | chr10:80791447-80797919 |
| 29053 | Tbxas1 | NM_011539.3 | chr6:38868985-39034578 |
| 29054 | Tc2n | NM_001082976.2 | chr12:102883655-102956733 |
| 29055 | Tc2n | NM_001286364.1 | chr12:102883655-102956733 |
| 29056 | Tc2n | NM_028924.3 | chr12:102883655-102956733 |
| 29057 | Tcaim | NM_001013405.2 | chr9:122714664-122745450 |
| 29058 | Tcam1 | NM_029467.3 | chr11:106137985-106149457 |
| 29059 | Tcap | NM_011540.2 | chr11:98245124-98246267 |
| 29060 | Tcea1 | NM_001159750.1 | chr1:4847774-4887990 |
| 29061 | Tcea1 | NM_001159751.1 | chr1:4847774-4887990 |
| 29062 | Tcea1 | NM_011541.4 | chr1:4847774-4887990 |
| 29063 | Tcea2 | NM_009326.2 | chr2:181415014-181427756 |
| 29064 | Tcea3 | NM_011543.2 | chr4:135803871-135830814 |
| 29065 | Tceal1 | NM_146236.1 | chrX:133242603-133244405 |
| 29066 | Tceal3 | NM_001029978.2 | chrX:133200913-133202916 |
| 29067 | Tceal5 | NM_177519.1 | chrX:132735489-132738390 |
| 29068 | Tceal6 | NM_025355.4 | chrX:131743224-131745226 |
| 29069 | Tceal7 | NM_001127169.1 | chrX:132758579-132760639 |
| 29070 | Tceal8 | NM_001168578.1 | chrX:132703522-132706790 |
| 29071 | Tceal8 | NM_025703.1 | chrX:132703522-132706790 |
| 29072 | Tceanc | NM_001007577.2 | chrX:162937746-162948410 |
| 29073 | Tceanc2 | NM_025617.2 | chr4:106806766-106850971 |
| 29074 | Tceb1 | NM_026456.2 | chr1:16632845-16646946 |
| 29075 | Tceb2 | NM_026305.2 | chr17:23961707-23966076 |
| 29076 | Tceb3 | NM_013736.4 | chr4:135559284-135577564 |
| 29077 | Tcerg1 | NM_001039474.1 | chr18:42671140-42735439 |
| 29078 | Tcerg1 | NM_001289526.1 | chr18:42671140-42735439 |
| 29079 | Tcerg1 | NR_110344.1 | chr18:42671140-42735439 |
| 29080 | Tcerg1l | NM_183289.3 | chr7:145400654-145589413 |
| 29081 | Tcf12 | NM_001253862.1 | chr9:71692058-71959626 |
| 29082 | Tcf12 | NM_001253863.1 | chr9:71692058-71959626 |
| 29083 | Tcf12 | NM_001253864.1 | chr9:71692058-71959626 |
| 29084 | Tcf12 | NM_001253865.1 | chr9:71692058-71959626 |
| 29085 | Tcf12 | NM_011544.3 | chr9:71692058-71959626 |
| 29086 | Tcf15 | NM_009328.2 | chr2:151969344-151974832 |
| 29087 | Tcf19 | NM_001163763.1 | chr17:35649679-35653769 |
| 29088 | Tcf19 | NM_001163764.1 | chr17:35649679-35653769 |
| 29089 | Tcf19 | NM_025674.2 | chr17:35649679-35653769 |
| 29090 | Tcf20 | NM_001114140.1 | chr15:82639054-82742564 |
| 29091 | Tcf20 | NM_013836.3 | chr15:82639054-82742564 |
| 29092 | Tcf21 | NM_011545.1 | chr10:22537078-22539934 |
| 29093 | Tcf23 | NM_053085.2 | chr5:31271050-31279391 |
| 29094 | Tcf24 | NM_001285425.1 | chr1:9950243-9957566 |
| 29095 | Tcf25 | NM_001037877.3 | chr8:125897610-125928074 |
| 29096 | Tcf25 | NM_001037878.3 | chr8:125897610-125928074 |
| 29097 | Tcf25 | NM_001286362.1 | chr8:125897610-125928074 |
| 29098 | Tcf25 | NM_001286363.1 | chr8:125897610-125928074 |
| 29099 | Tcf25 | NM_025804.3 | chr8:125897610-125928074 |
| 29100 | Tcf3 | NM_001164147.1 | chr10:79871909-79896398 |
| 29101 | Tcf3 | NM_001164148.1 | chr10:79871909-79896398 |
| 29102 | Tcf3 | NM_001164149.1 | chr10:79871909-79896398 |
| 29103 | Tcf3 | NM_001164150.1 | chr10:79871909-79896398 |
| 29104 | Tcf3 | NM_001164151.1 | chr10:79871909-79896398 |
| 29105 | Tcf3 | NM_001164152.1 | chr10:79871909-79896398 |
| 29106 | Tcf3 | NM_001164153.1 | chr10:79871909-79896398 |
| 29107 | Tcf3 | NM_011548.4 | chr10:79871909-79896398 |
| 29108 | Tcf4 | NM_001083967.1 | chr18:69504145-69847621 |
| 29109 | Tcf4 | NM_013685.2 | chr18:69504145-69847621 |
| 29110 | Tcf7 | NM_009331.3 | chr11:52066105-52095752 |
| 29111 | Tcf7l1 | NM_001079822.2 | chr6:72576364-72739039 |
| 29112 | Tcf7l1 | NM_009332.3 | chr6:72576364-72739039 |
| 29113 | Tcf7l2 | NM_001142918.1 | chr19:55816299-56008145 |
| 29114 | Tcf7l2 | NM_001142919.1 | chr19:55816299-56008145 |
| 29115 | Tcf7l2 | NM_001142920.1 | chr19:55816299-56008145 |
| 29116 | Tcf7l2 | NM_001142921.1 | chr19:55816299-56008145 |
| 29117 | Tcf7l2 | NM_001142922.1 | chr19:55816299-56008145 |
| 29118 | Tcf7l2 | NM_001142923.1 | chr19:55816299-56008145 |
| 29119 | Tcf7l2 | NM_001142924.1 | chr19:55816299-56008145 |
| 29120 | Tcf7l2 | NM_009333.3 | chr19:55816299-56008145 |
| 29121 | Tcfl5 | NM_178254.2 | chr2:180356662-180377396 |
| 29122 | Tchh | NM_001163098.1 | chr3:93246251-93252999 |
| 29123 | Tchhl1 | NM_027762.3 | chr3:93272675-93275902 |
| 29124 | Tchp | NM_029992.2 | chr5:115157788-115172336 |
| 29125 | Tcirg1 | NM_001136091.2 | chr19:3896049-3907133 |
| 29126 | Tcirg1 | NM_001167784.1 | chr19:3896049-3907133 |
| 29127 | Tcirg1 | NM_016921.3 | chr19:3896049-3907133 |
| 29128 | Tcl1 | NM_001289468.1 | chr12:106454964-106460947 |
| 29129 | Tcl1 | NM_009337.3 | chr12:106454964-106460947 |
| 29130 | Tcl1 | NR_110339.1 | chr12:106454964-106460947 |
| 29131 | Tcl1 | NR_110340.1 | chr12:106454964-106460947 |
| 29132 | Tcl1 | NR_110341.1 | chr12:106454964-106460947 |
| 29133 | Tcl1b1 | NM_013773.1 | chr12:106397913-106404835 |
| 29134 | Tcl1b2 | NM_013775.1 | chr12:106385242-106393435 |
| 29135 | Tcl1b3 | NM_013772.2 | chr12:106429254-106433609 |
| 29136 | Tcl1b4 | NM_013774.2 | chr12:106440631-106445203 |
| 29137 | Tcl1b5 | NM_013776.1 | chr12:106414567-106419355 |
| 29138 | Tcn2 | NM_001130458.1 | chr11:3817080-3832081 |
| 29139 | Tcn2 | NM_001130459.1 | chr11:3817080-3832081 |
| 29140 | Tcn2 | NM_015749.3 | chr11:3817080-3832081 |
| 29141 | Tcof1 | NM_001198984.1 | chr18:60973409-61008618 |
| 29142 | Tcof1 | NM_011552.3 | chr18:60973409-61008618 |
| 29143 | Tcp1 | NM_001290712.1 | chr17:13109194-13133262 |
| 29144 | Tcp1 | NM_013686.4 | chr17:13109194-13133262 |
| 29145 | Tcp10a | NM_011553.4 | chr17:7529008-7550209 |
| 29146 | Tcp10a | NR_046291.1 | chr17:7529008-7550209 |
| 29147 | Tcp10b | NM_009341.2 | chr17:13253976-13275092 |
| 29148 | Tcp10c | NM_001167578.1 | chr17:13547437-13570089 |
| 29149 | Tcp11 | NM_001085555.1 | chr17:28203691-28217584 |
| 29150 | Tcp11 | NM_013687.3 | chr17:28203691-28217584 |
| 29151 | Tcp11l1 | NM_177190.5 | chr2:104520136-104552319 |
| 29152 | Tcp11l2 | NM_146008.2 | chr10:84039691-84077100 |
| 29153 | Tcstv1 | NM_018756.3 | chrUn_random:37342-38736 |
| 29154 | Tcstv3 | NM_153523.3 | chrUn_random:3052-4452 |
| 29155 | Tcta | NM_139986.1 | chr9:108205288-108208282 |
| 29156 | Tctel | NM_013688.2 | chr17:45660383-45679626 |
| 29157 | Tcte2 | NM_022311.2 | chr17:13853443-13898401 |
| 29158 | Tcte3 | NM_011560.3 | chr17:15164114-15178523 |
| 29159 | Tcte3 | NM_198104.2 | chr17:15164114-15178523 |
| 29160 | Tctex1d1 | NM_001163767.1 | chr4:102432739-102684570 |
| 29161 | Tctex1d1 | NM_001163768.1 | chr4:102432739-102684570 |
| 29162 | Tctex1d1 | NM_026100.3 | chr4:102432739-102684570 |
| 29163 | Tctex1d2 | NM_025329.3 | chr16:32419787-32428978 |
| 29164 | Tctex1d4 | NM_175030.2 | chr4:116799418-116801335 |
| 29165 | Tctn1 | NM_001039153.3 | chr5:122659737-122714469 |
| 29166 | Tctn1 | NR_104441.1 | chr5:122659737-122714469 |
| 29167 | Tctn2 | NM_026486.3 | chr5:125048757-125077658 |
| 29168 | Tctn3 | NM_026260.2 | chr19:40670935-40686705 |
| 29169 | Tdg | NM_011561.2 | chr10:82092582-82153395 |
| 29170 | Tdg | NM_172552.3 | chr10:82092582-82153395 |
| 29171 | Tdgf1 | NM_011562.1 | chr9:110842111-110848662 |
| 29172 | Tdh | NM_021480.5 | chr14:64111183-64177929 |
| 29173 | Tdo2 | NM_019911.2 | chr3:81762335-81779650 |
| 29174 | Tdp1 | NM_028354.4 | chr12:101122724-101193426 |
| 29175 | Tdp2 | NM_019551.2 | chr13:24923527-24934022 |

Fig. 25 - 155

| | | | | | | | | |
|---|---|---|---|---|---|---|---|---|
| 29176 | Tdpoz1 | NM_148949.2 | chr3:93473254-93480205 | | 29271 | Tex11 | NM_001167997.1 | chrX:98033986-98254978 |
| 29177 | Tdpoz2 | NM_001007222.3 | chr3:93455463-93456608 | | 29272 | Tex11 | NM_031384.2 | chrX:98033986-98254978 |
| 29178 | Tdpoz3 | NM_207271.2 | chr3:93629941-93631039 | | 29273 | Tex12 | NM_025687.3 | chr9:50365252-50369373 |
| 29179 | Tdpoz4 | NM_207272.2 | chr3:93600319-93601432 | | 29274 | Tex13 | NM_031381.2 | chrX:137342845-137347972 |
| 29180 | Tdpoz5 | NM_207273.2 | chr3:93875543-93876566 | | 29275 | Tex13a | NM_026469.2 | chrX:134742704-134744119 |
| 29181 | Tdrd1 | NM_001002238.2 | chr19:56900698-56944502 | | 29276 | Tex14 | NM_001199293.1 | chr11:87218566-87369325 |
| 29182 | Tdrd1 | NM_001002240.2 | chr19:56900698-56944502 | | 29277 | Tex14 | NM_031386.2 | chr11:87218566-87369325 |
| 29183 | Tdrd1 | NM_001002241.2 | chr19:56900698-56944502 | | 29278 | Tex15 | NM_031374.2 | chr8:34681015-34696057 |
| 29184 | Tdrd1 | NM_031387.3 | chr19:56900698-56944502 | | 29279 | Tex16 | NM_031382.2 | chrX:109267128-109240935 |
| 29185 | Tdrd12 | NM_028034.2 | chr7:36278628-36322763 | | 29280 | Tex19.1 | NM_028602.2 | chr11:121007456-121009627 |
| 29186 | Tdrd3 | NM_001253755.1 | chr14:87816389-87945315 | | 29281 | Tex19.2 | NM_027622.3 | chr11:120977528-120979991 |
| 29187 | Tdrd3 | NM_172605.3 | chr14:87816389-87945315 | | 29282 | Tex2 | NM_198292.3 | chr11:106363452-106474244 |
| 29188 | Tdrd5 | NM_001134741.1 | chr1:158185425-158233737 | | 29283 | Tex21 | NM_001159532.1 | chr12:77299676-77347733 |
| 29189 | Tdrd5 | NM_001277730.1 | chr1:158185425-158233737 | | 29284 | Tex23 | NM_019784.5 | chr12:77299676-77347733 |
| 29190 | Tdrd6 | NM_001161366.1 | chr17:43752283-43767248 | | 29285 | Tex22 | NM_029381.1 | chr12:114312712-114327125 |
| 29191 | Tdrd6 | NM_001161367.1 | chr17:43752283-43767248 | | 29286 | Tex24 | NM_001013609.2 | chr8:28454865-28459660 |
| 29192 | Tdrd6 | NM_198418.2 | chr17:43752283-43767248 | | 29287 | Tex26 | NM_029464.1 | chr5:150242280-150273195 |
| 29193 | Tdrd7 | NM_001290475.1 | chr4:45978206-46047637 | | 29288 | Tex261 | NM_009357.2 | chr6:83720407-83725806 |
| 29194 | Tdrd7 | NM_146142.2 | chr4:45978206-46047637 | | 29289 | Tex264 | NM_001081654.2 | chr9:106561076-106588283 |
| 29195 | Tdrd9 | NM_029056.1 | chr12:113209770-113307065 | | 29290 | Tex264 | NM_001286498.1 | chr9:106561076-106588283 |
| 29196 | Tdrkh | NM_028307.1 | chr3:94217239-94235421 | | 29291 | Tex264 | NM_015733.3 | chr9:106561076-106588283 |
| 29197 | Tdrp | NM_178744.4 | chr8:13952007-13974777 | | 29292 | Tex264 | NR_104459.1 | chr9:106561076-106588283 |
| 29198 | Tead1 | NM_001166584.1 | chr7:119822833-120050319 | | 29293 | Tex28 | NM_001126488.2 | chrX:71396282-71413177 |
| 29199 | Tead1 | NM_001166585.1 | chr7:119822833-120050319 | | 29294 | Tex29 | NM_029326.1 | chr8:11840520-11855761 |
| 29200 | Tead1 | NM_009346.3 | chr7:119822833-120050319 | | 29295 | Tex30 | NM_029368.1 | chr1:44143461-44159233 |
| 29201 | Tead2 | NM_001285498.1 | chr7:52471122-52488989 | | 29296 | Tex33 | NM_001163612.2 | chr15:78208829-78226342 |
| 29202 | Tead2 | NM_001285500.1 | chr7:52471122-52488989 | | 29297 | Tex33 | NM_001163613.1 | chr15:78208829-78226342 |
| 29203 | Tead2 | NM_011565.2 | chr7:52471122-52488989 | | 29298 | Tex33 | NM_028522.1 | chr15:78208829-78226342 |
| 29204 | Tead3 | NM_001098226.3 | chr17:28468617-28487750 | | 29299 | Tex35 | NM_028540.3 | chr1:159029278-159038776 |
| 29205 | Tead3 | NM_001204156.1 | chr17:28468617-28487750 | | 29300 | Tex36 | NM_028654.1 | chr7:140778706-140793798 |
| 29206 | Tead3 | NM_011565.4 | chr17:28468617-28487750 | | 29301 | Tex37 | NM_028825.1 | chr6:70863082-70868916 |
| 29207 | Tead4 | NM_001080979.1 | chr6:128177160-128250831 | | 29302 | Tex38 | NM_029196.1 | chr4:115452438-115453639 |
| 29208 | Tead4 | NM_011567.2 | chr6:128177160-128250831 | | 29303 | Tex40 | NM_001039494.2 | chr19:6996915-6999870 |
| 29209 | Tec | NM_001113460.2 | chr5:73146956-73259687 | | 29304 | Tex43 | NM_026099.3 | chr18:56748001-56754433 |
| 29210 | Tec | NM_001113461.2 | chr5:73146956-73259687 | | 29305 | Tex9 | NM_009359.4 | chr9:72305862-72339766 |
| 29211 | Tec | NM_001113464.2 | chr5:73146956-73259687 | | 29306 | Tfam | NM_009360.4 | chr10:70688224-70700792 |
| 29212 | Tec | NM_013689.5 | chr5:73146956-73259687 | | 29307 | Tfap2a | NM_001122948.1 | chr13:40811043-40829192 |
| 29213 | Tecpr1 | NM_027410.1 | chr5:144956217-144984447 | | 29308 | Tfap2a | NM_011547.4 | chr13:40811043-40829192 |
| 29214 | Tecpr2 | NM_001081057.2 | chr12:112127473-112210606 | | 29309 | Tfap2b | NM_001025305.2 | chr1:19198994-19228926 |
| 29215 | Tecpr2 | NM_001289510.1 | chr12:112127473-112210606 | | 29310 | Tfap2b | NM_001286340.1 | chr1:19198994-19228926 |
| 29216 | Tecpr2 | NM_175336.3 | chr12:112127473-112210606 | | 29311 | Tfap2b | NM_009334.3 | chr1:19198994-19228926 |
| 29217 | Tecr | NM_027410.1 | chr8:86095596-86118390 | | 29312 | Tfap2c | NM_001159696.1 | chr2:172375092-172384121 |
| 29218 | Tecr | NM_134118.5 | chr8:86095596-86118390 | | 29313 | Tfap2c | NM_009335.2 | chr2:172375092-172384121 |
| 29219 | Tecrl | NM_153801.3 | chr5:83707146-83784220 | | 29314 | Tfap2d | NM_153154.2 | chr1:19093102-19156413 |
| 29220 | Tecta | NM_009347.2 | chr9:42137704-42208012 | | 29315 | Tfap2e | NM_198960.2 | chr4:126393246-126413513 |
| 29221 | Tectb | NM_009348.3 | chr19:55255375-55270803 | | 29316 | Tfap4 | NM_031182.2 | chr16:4544660-4559720 |
| 29222 | Teddm1 | NM_178244.3 | chr1:155738775-155740190 | | 29317 | Tfb1m | NM_146074.1 | chr17:3519256-3557713 |
| 29223 | Tef | NM_017376.3 | chr15:81633102-81657293 | | 29318 | Tfb2m | NM_008249.4 | chr1:181458186-181476398 |
| 29224 | Tef | NM_153484.3 | chr15:81633102-81657293 | | 29319 | Tfcp2 | NM_001289603.1 | chr15:100333178-100382439 |
| 29225 | Tefm | NM_183275.2 | chr11:79950179-79955655 | | 29320 | Tfcp2 | NM_033476.3 | chr15:100333178-100382439 |
| 29226 | Tek | NM_001290549.1 | chr4:94405979-94541667 | | 29321 | Tfcp2l1 | NM_023755.2 | chr1:120524521-120581745 |
| 29227 | Tek | NM_001290551.1 | chr4:94405979-94541667 | | 29322 | Tfdp1 | NM_001291765.1 | chr8:13338750-13378448 |
| 29228 | Tek | NM_013690.3 | chr4:94405979-94541667 | | 29323 | Tfdp1 | NM_001291766.1 | chr8:13338750-13378448 |
| 29229 | Tekt1 | NM_001282006.1 | chr11:72158218-72175944 | | 29324 | Tfdp1 | NM_001291768.1 | chr8:13338750-13378448 |
| 29230 | Tekt1 | NM_001282007.1 | chr11:72158218-72175944 | | 29325 | Tfdp1 | NM_009361.3 | chr8:13338750-13378448 |
| 29231 | Tekt1 | NM_011569.3 | chr11:72158218-72175944 | | 29326 | Tfdp2 | NM_001184706.1 | chr9:96096893-96224065 |
| 29232 | Tekt2 | NM_011902.2 | chr4:125999364-126002443 | | 29327 | Tfdp2 | NM_001184708.1 | chr9:96096893-96224065 |
| 29233 | Tekt3 | NM_027660.1 | chr11:62875160-62908462 | | 29328 | Tfdp2 | NM_001184709.1 | chr9:96096893-96224065 |
| 29234 | Tekt4 | NM_027951.1 | chr17:25608854-25613539 | | 29329 | Tfdp2 | NM_001184710.1 | chr9:96096893-96224065 |
| 29235 | Tekt5 | NM_001099275.1 | chr16:10358044-10395558 | | 29330 | Tfdp2 | NM_001184711.1 | chr9:96096893-96224065 |
| 29236 | Tekt5 | NM_001291001.1 | chr16:10358044-10395558 | | 29331 | Tfdp2 | NM_178667.4 | chr9:96096893-96224065 |
| 29237 | Telo2 | NM_001163661.1 | chr17:25236513-25252912 | | 29332 | Tfe3 | NM_001105196.1 | chrX:7339786-7352328 |
| 29238 | Telo2 | NM_027880.2 | chr17:25236513-25252912 | | 29333 | Tfe3 | NM_001105197.1 | chrX:7339786-7352328 |
| 29239 | Ten1 | NM_027107.1 | chr11:116060169-116076632 | | 29334 | Tfe3 | NM_001271489.1 | chrX:7339786-7352328 |
| 29240 | Tenc1 | NM_153533.2 | chr15:101933418-101946832 | | 29335 | Tfe3 | NM_001271490.1 | chrX:7339786-7352328 |
| 29241 | Tenm1 | NM_011855.4 | chrX:39885569-40627961 | | 29336 | Tfe3 | NM_001271491.1 | chrX:7339786-7352328 |
| 29242 | Tenm2 | NM_001290702.1 | chr11:35820157-36757743 | | 29337 | Tfe3 | NM_172472.3 | chrX:7339786-7352328 |
| 29243 | Tenm2 | NM_011856.4 | chr11:35820157-36757743 | | 29338 | Tfeb | NM_001161722.1 | chr17:47873985-47929365 |
| 29244 | Tenm3 | NM_001145937.1 | chr8:49311018-49760044 | | 29339 | Tfeb | NM_001161723.1 | chr17:47873985-47929365 |
| 29245 | Tenm3 | NM_011873.3 | chr8:49311018-49760044 | | 29340 | Tfeb | NM_011549.3 | chr17:47873985-47929365 |
| 29246 | Tenm4 | NM_011858.3 | chr7:103359147-104057064 | | 29341 | Tfec | NM_031198.3 | chr6:16783380-16848441 |
| 29247 | Tep1 | NM_009351.2 | chr14:51443735-51490229 | | 29342 | Tff1 | NM_009362.2 | chr17:31289696-31303998 |
| 29248 | Tepp | NM_028532.3 | chr8:97835497-97845229 | | 29343 | Tff1 | NM_009362.2 | chr15:143200557-143579066 |
| 29249 | Tepp | NM_199455.2 | chr8:97835497-97845229 | | 29344 | Tff2 | NM_009363.3 | chr17:31278006-31281227 |
| 29250 | Terc | NR_001579.1 | chr3:96218359-96218756 | | 29345 | Tff3 | NM_011575.2 | chr17:31262250-31266556 |
| 29251 | Terf1 | NM_001286628.1 | chr1:15795726-15834133 | | 29346 | Tfg | NM_001252443.1 | chr16:56690441-56717563 |
| 29252 | Terf1 | NM_009352.3 | chr1:15795726-15834133 | | 29347 | Tfg | NM_019678.3 | chr16:56690441-56717563 |
| 29253 | Terf2 | NM_001083118.2 | chr8:109593301-109620445 | | 29348 | Tfip11 | NM_018783.4 | chr5:112755389-112767093 |
| 29254 | Terf2 | NM_001286200.1 | chr8:109593301-109620445 | | 29349 | Tfpi | NM_001177319.1 | chr2:84273016-84316932 |
| 29255 | Terf2 | NM_009353.2 | chr8:109593301-109620445 | | 29350 | Tfpi | NM_001177320.1 | chr2:84273016-84316932 |
| 29256 | Terf2 | NR_104410.1 | chr8:109593301-109620445 | | 29351 | Tfpi | NM_011576.1 | chr2:84273016-84316932 |
| 29257 | Terf2ip | NM_020584.2 | chr8:114535258-114544428 | | 29352 | Tfpi2 | NM_009364.3 | chr6:3912594-3918354 |
| 29258 | Tert | NM_009354.1 | chr13:73764448-73786489 | | 29353 | Tfpt | NM_001290381.1 | chr7:3571925-3581531 |
| 29259 | Tes | NM_207176.3 | chr6:17015148-17055825 | | 29354 | Tfpt | NM_023524.2 | chr7:3571925-3581531 |
| 29260 | Tesc | NM_021344.3 | chr5:118477832-118511879 | | 29355 | Tfr2 | NM_001289507.1 | chr5:138011067-138029309 |
| 29261 | Tesc1 | NM_001163810.1 | chr7:25118098-25118984 | | 29356 | Tfr2 | NM_001289509.1 | chr5:138011067-138029309 |
| 29262 | Tesk1 | NM_011573.3 | chr4:43455149-43460947 | | 29357 | Tfr2 | NM_001289511.1 | chr5:138011067-138029309 |
| 29263 | Tesk2 | NM_146151.4 | chr4:116393560-116476853 | | 29358 | Tfr2 | NM_015799.4 | chr5:138011067-138029309 |
| 29264 | Tespa1 | NM_183264.4 | chr10:129759907-129799698 | | 29359 | Tfrc | NM_011638.4 | chr16:32608981-32632880 |
| 29265 | Tet1 | NM_001253857.1 | chr10:62267317-62342762 | | 29360 | Tg | NM_009375.2 | chr15:66502332-66682232 |
| 29266 | Tet1 | NM_027384.1 | chr10:62267317-62342762 | | 29361 | Tgds | NM_029578.3 | chr14:118511132-118531987 |
| 29267 | Tet2 | NM_001040400.1 | chr3:133126640-133207354 | | 29362 | Tgfa | NM_031199.2 | chr6:86145244-86225443 |
| 29268 | Tet3 | NM_183138.2 | chr6:83312368-83391672 | | 29363 | Tgfb1 | NM_011577.1 | chr7:26472020-26490015 |
| 29269 | Tex10 | NM_172304.3 | chr4:48443828-48486294 | | 29364 | Tgfb1i1 | NM_001289550.1 | chr7:135390325-135399213 |
| 29270 | Tex101 | NM_019981.2 | chr7:25453030-25457069 | | 29365 | Tgfb1i1 | NM_001289551.1 | chr7:135390325-135399213 |

Fig. 25 - 156

| | | | | | | | |
|---|---|---|---|---|---|---|---|
| 29366 | Tgfb1i1 | NM_001289552.1 | chr7:135390325-135399213 | 29461 | Thumpd1 | NM_145585.2 | chr7:126858607-126864312 |
| 29367 | Tgfb1i1 | NM_001289553.1 | chr7:135390325-135399213 | 29462 | Thumpd2 | NM_028138.1 | chr17:81425666-81464425 |
| 29368 | Tgfb2 | NM_009367.3 | chr1:188447064-188529871 | 29463 | Thumpd3 | NM_008188.2 | chr6:112996321-113018267 |
| 29369 | Tgfb3 | NM_009368.3 | chr12:87397692-87419991 | 29464 | Thy1 | NM_009382.3 | chr9:43851466-43856662 |
| 29370 | Tgfbi | NM_009369.4 | chr13:56710963-56740700 | 29465 | Thyn1 | NM_144543.2 | chr9:26807262-26814919 |
| 29371 | Tgfbr1 | NM_009370.2 | chr4:47366176-47427796 | 29466 | Tia1 | NM_001164078.1 | chr6:86354212-86383399 |
| 29372 | Tgfbr2 | NM_009371.3 | chr9:115996812-116084481 | 29467 | Tia1 | NM_001164079.1 | chr6:86354212-86383399 |
| 29373 | Tgfbr2 | NM_029575.3 | chr9:115996812-116084481 | 29468 | Tia1 | NM_011585.4 | chr6:86354212-86383399 |
| 29374 | Tgfbr3 | NM_011578.3 | chr5:107535588-107718614 | 29469 | Tial1 | NM_009383.2 | chr7:135583290-135605027 |
| 29375 | Tgfbrap1 | NM_001013025.2 | chr1:43104113-43155467 | 29470 | Tiam1 | NM_001145886.1 | chr16:89787355-89974944 |
| 29376 | Tgif1 | NM_001164074.1 | chr17:71193544-71202872 | 29471 | Tiam1 | NM_001145887.1 | chr16:89787355-89974944 |
| 29377 | Tgif1 | NM_001164075.1 | chr17:71193544-71202872 | 29472 | Tiam1 | NM_009384.3 | chr16:89787355-89974944 |
| 29378 | Tgif1 | NM_001164076.1 | chr17:71193544-71202872 | 29473 | Tiam2 | NM_001122998.1 | chr17:3326572-3557713 |
| 29379 | Tgif1 | NM_001164077.1 | chr17:71193544-71202872 | 29474 | Tiam2 | NM_001286757.1 | chr17:3326572-3557713 |
| 29380 | Tgif1 | NM_009372.3 | chr17:71193544-71202872 | 29475 | Tiam2 | NM_001286758.1 | chr17:3326572-3557713 |
| 29381 | Tgif2 | NM_001291124.1 | chr2:156665742-156688681 | 29476 | Tiam2 | NM_011878.2 | chr17:3326572-3557713 |
| 29382 | Tgif2 | NM_173396.3 | chr2:156665742-156688681 | 29477 | Ticam1 | NM_174989.4 | chr17:56408884-56416190 |
| 29383 | Tgif2lx1 | NM_153109.1 | chrX:115540835-115541867 | 29478 | Ticam2 | NM_173394.3 | chr18:46717884-46734187 |
| 29384 | Tgif2lx1 | NM_153109.1 | chrX:115593314-115594346 | 29479 | Ticrr | NM_029835.1 | chr7:86805082-86843031 |
| 29385 | Tgif2lx2 | NM_001142750.1 | chrX:115593314-115594346 | 29480 | Tie1 | NM_011587.2 | chr4:118143795-118162454 |
| 29386 | Tgif2lx2 | NM_001142750.1 | chrX:115540835-115541867 | 29481 | Tifa | NM_145133.3 | chr3:127492830-127501307 |
| 29387 | Tgm1 | NM_001161714.1 | chr14:56318845-56332329 | 29482 | Tifab | NM_001168615.1 | chr13:56275063-56280246 |
| 29388 | Tgm1 | NM_001161715.1 | chr14:56318845-56332329 | 29483 | Tifab | NM_145976.4 | chr13:56275063-56280246 |
| 29389 | Tgm1 | NM_019984.3 | chr14:56318845-56332329 | 29484 | Tigd2 | NM_001081145.1 | chr6:59158863-59162027 |
| 29390 | Tgm2 | NM_009373.3 | chr2:157942140-157972128 | 29485 | Tigd3 | NM_198634.1 | chr19:5891137-5894107 |
| 29391 | Tgm3 | NM_009374.3 | chr2:129838076-129876135 | 29486 | Tigd4 | NM_207278.2 | chr3:84397495-84400954 |
| 29392 | Tgm4 | NM_177911.4 | chr9:122943858-122976676 | 29487 | Tigd5 | NM_178646.4 | chr15:75740164-75744965 |
| 29393 | Tgm5 | NM_028799.2 | chr2:120871846-120911495 | 29488 | Tigit | NM_001146325.1 | chr16:43648973-43664297 |
| 29394 | Tgm6 | NM_001289747.1 | chr2:129938151-129979968 | 29489 | Timd2 | NM_001161355.1 | chr11:46482461-46520606 |
| 29395 | Tgm6 | NM_001289748.1 | chr2:129938151-129979968 | 29490 | Timd2 | NM_001161356.1 | chr11:46482461-46520606 |
| 29396 | Tgm6 | NM_001289749.1 | chr2:129938151-129979968 | 29491 | Timd2 | NM_134249.5 | chr11:46482461-46520606 |
| 29397 | Tgm6 | NM_177726.4 | chr2:129938151-129979968 | 29492 | Timd4 | NM_178759.4 | chr11:46624300-46657835 |
| 29398 | Tgm7 | NM_001160424.1 | chr2:120919324-120935527 | 29493 | Timeless | NM_001136082.2 | chr10:127669118-127689997 |
| 29399 | Tgoln1 | NM_009443.3 | chr6:72558415-72566994 | 29494 | Timeless | NM_001164080.1 | chr10:127669118-127689997 |
| 29400 | Tgoln2 | NM_009444.1 | chr6:72560951-72566742 | 29495 | Timeless | NM_001164081.1 | chr10:127669118-127689997 |
| 29401 | Tgs1 | NM_054089.4 | chr4:3502025-3543770 | 29496 | Timeless | NM_011589.2 | chr10:127669118-127689997 |
| 29402 | Tgtp1 | NM_011579.3 | chr11:48798831-48805748 | 29497 | Timm10 | NM_013899.2 | chr2:84667177-84670370 |
| 29403 | Tgtp2 | NM_001145164.1 | chr11:48798830-48805756 | 29498 | Timm10b | NM_019502.2 | chr7:112789053-112790359 |
| 29404 | Tgtp2 | NM_001145164.1 | chr11:48851161-48948889 | 29499 | Timm13 | NM_013895.4 | chr10:80362195-80363714 |
| 29405 | Th | NM_009377.1 | chr7:150078680-150085871 | 29500 | Timm17a | NM_011590.2 | chr1:137198111-137210314 |
| 29406 | Tha1 | NM_027919.4 | chr11:117729262-117734840 | 29501 | Timm17b | NM_011591.4 | chrX:7476523-7484778 |
| 29407 | Thada | NM_183021.3 | chr17:84589395-84865548 | 29502 | Timm21 | NM_025969.4 | chr18:85116686-85120916 |
| 29408 | Thap1 | NM_199042.2 | chr8:27268640-27274623 | 29503 | Timm22 | NM_001291161.1 | chr11:76220426-76229815 |
| 29409 | Thap11 | NM_021513.2 | chr8:108379002-108380850 | 29504 | Timm22 | NM_019818.5 | chr11:76220426-76229815 |
| 29410 | Thap2 | NM_025780.3 | chr10:114807021-114821491 | 29505 | Timm22 | NM_023355.2 | chr11:76220426-76229815 |
| 29411 | Thap3 | NM_001145929.1 | chr4:151356746-151363095 | 29506 | Timm22 | NR_111896.1 | chr11:76220426-76229815 |
| 29412 | Thap3 | NM_175152.4 | chr4:151356746-151363095 | 29507 | Timm23 | NM_016897.3 | chr14:32993351-33015077 |
| 29413 | Thap4 | NM_025920.3 | chr1:95601967-95651415 | 29508 | Timm44 | NM_011592.2 | chr8:4259736-4275905 |
| 29414 | Thap6 | NR_028429.1 | chr5:92391908-92401163 | 29509 | Timm50 | NM_025616.3 | chr7:29080844-29097065 |
| 29415 | Thap7 | NM_026909.2 | chr16:17528074-17531145 | 29510 | Timm8a1 | NM_013898.2 | chrX:131071796-131076168 |
| 29416 | Thbd | NM_009378.3 | chr2:148230206-148233924 | 29511 | Timm8a2 | NM_001037744.1 | chr14:122433895-122437644 |
| 29417 | Thbs1 | NM_011580.3 | chr2:117937657-117952869 | 29512 | Timm8b | NM_013897.2 | chr9:50412006-50413425 |
| 29418 | Thbs2 | NM_011581.3 | chr17:14802506-14831269 | 29513 | Timm9 | NM_001024853.1 | chr12:72212414-72237662 |
| 29419 | Thbs3 | NM_013691.2 | chr3:89019108-89030759 | 29514 | Timm9 | NM_001024854.1 | chr12:72212414-72237662 |
| 29420 | Thbs4 | NM_011582.3 | chr13:93521540-93564773 | 29515 | Timm9 | NM_001286203.2 | chr12:72212414-72237662 |
| 29421 | Theg | NM_011583.3 | chr10:79039221-79049881 | 29516 | Timm9 | NM_013896.3 | chr12:72212414-72237662 |
| 29422 | Theg | NM_199226.1 | chr10:79039221-79049881 | 29517 | Timmdc1 | NM_024273.2 | chr16:38497924-38522747 |
| 29423 | Them4 | NM_029431.3 | chr3:94114053-94136454 | 29518 | Timp1 | NM_001044384.1 | chrX:20425668-20498044 |
| 29424 | Them5 | NM_025416.3 | chr3:94146020-94151274 | 29519 | Timp1 | NM_011593.2 | chrX:20425668-20498044 |
| 29425 | Them6 | NM_198607.1 | chr15:74551663-74554803 | 29520 | Timp2 | NM_011594.3 | chr11:118162375-118216725 |
| 29426 | Them7 | NM_001159638.1 | chr2:105064498-105220017 | 29521 | Timp3 | NM_011595.2 | chr10:85763157-85812250 |
| 29427 | Them7 | NM_028747.2 | chr2:105064498-105220017 | 29522 | Timp4 | NM_080639.3 | chr6:115195634-115201867 |
| 29428 | Themis | NM_178666.6 | chr10:28388200-28602555 | 29523 | Tinag | NM_012033.3 | chr9:76799504-76893588 |
| 29429 | Themis2 | NM_001033308.2 | chr4:132338271-132352279 | 29524 | Tinagl1 | NM_001168333.1 | chr4:129842843-129852366 |
| 29430 | Themis3 | NM_028998.1 | chr17:66904591-66943962 | 29525 | Tinagl1 | NM_023476.3 | chr4:129842843-129852366 |
| 29431 | Thg1l | NM_001080969.3 | chr11:45758808-45769005 | 29526 | Tinf2 | NM_145705.3 | chr14:56297917-56300654 |
| 29432 | Thg1l | NM_001290737.1 | chr11:45758808-45769005 | 29527 | Tiparp | NM_178892.5 | chr3:65332369-65359440 |
| 29433 | Thnsl1 | NM_001001297.2 | chr2:21127350-21136636 | 29528 | Tipin | NM_025372.3 | chr9:64129413-64152599 |
| 29434 | Thnsl1 | NM_177588.2 | chr2:21127350-21136636 | 29529 | Tipr1 | NM_145513.4 | chr1:167142416-167167089 |
| 29435 | Thnsl2 | NM_001033929.2 | chr6:71078159-71094374 | 29530 | Tirap | NM_001177845.1 | chr9:34991975-35007876 |
| 29436 | Thnsl2 | NM_178413.5 | chr6:71078159-71094374 | 29531 | Tirap | NM_001177846.1 | chr9:34991975-35007876 |
| 29437 | Thoc1 | NM_153552.3 | chr18:9958178-9995482 | 29532 | Tirap | NM_001177847.1 | chr9:34991975-35007876 |
| 29438 | Thoc2 | NM_001033422.1 | chrX:39148170-39265078 | 29533 | Tirap | NM_054096.2 | chr9:34991975-35007876 |
| 29439 | Thoc3 | NM_028597.3 | chr13:54560197-54570201 | 29534 | Tjap1 | NM_001252473.1 | chr17:46394799-46419975 |
| 29440 | Thoc5 | NM_172438.3 | chr11:4795346-4828868 | 29535 | Tjap1 | NM_001252474.1 | chr17:46394799-46419975 |
| 29441 | Thoc6 | NM_001008425.1 | chr17:23805586-23810737 | 29536 | Tjap1 | NM_001252475.1 | chr17:46394799-46419975 |
| 29442 | Thoc7 | NM_001285780.1 | chr14:14781525-14793827 | 29537 | Tjap1 | NM_028751.3 | chr17:46394799-46419975 |
| 29443 | Thoc7 | NM_025435.3 | chr14:14781525-14793827 | 29538 | Tjp1 | NM_001163574.1 | chr7:72441050-72516130 |
| 29444 | Thop1 | NM_022654.3 | chr10:80532827-80545105 | 29539 | Tjp1 | NM_009386.2 | chr7:72441050-72516130 |
| 29445 | Thpo | NM_001173505.1 | chr16:20724526-20742457 | 29540 | Tjp2 | NM_001198985.1 | chr19:24168991-24299516 |
| 29446 | Thpo | NM_001289894.1 | chr16:20724526-20742457 | 29541 | Tjp2 | NM_011597.4 | chr19:24168991-24299516 |
| 29447 | Thpo | NM_001289896.1 | chr16:20724526-20742457 | 29542 | Tjp3 | NM_001282095.1 | chr10:80730916-80754326 |
| 29448 | Thpo | NM_009379.3 | chr16:20724526-20742457 | 29543 | Tjp3 | NM_001282096.1 | chr10:80730916-80754326 |
| 29449 | Thra | NM_178060.3 | chr11:98603186-98626425 | 29544 | Tjp3 | NM_013769.3 | chr10:80730916-80754326 |
| 29450 | Thrap3 | NM_146153.3 | chr4:126841326-125879954 | 29545 | Tk1 | NM_001177729.1 | chr11:117676832-117701222 |
| 29451 | Thrb | NM_001113417.1 | chr14:18493473-18870602 | 29546 | Tk1 | NM_009387.2 | chr11:117676832-117701222 |
| 29452 | Thrb | NM_009380.3 | chr14:18493473-18870602 | 29547 | Tk2 | NM_021028.3 | chr8:106750590-106772458 |
| 29453 | Thrsp | NM_009381.2 | chr7:104561466-104566020 | 29548 | Tk2 | NR_045642.1 | chr8:106750590-106772458 |
| 29454 | Thsd1 | NM_001205253.1 | chr8:23337774-23371804 | 29549 | Tkt | NM_009388.6 | chr14:31362317-31387911 |
| 29455 | Thsd1 | NM_019576.2 | chr8:23337774-23371804 | 29550 | Tktl1 | NM_031379.2 | chrX:71422597-71453837 |
| 29456 | Thsd4 | NM_001040426.3 | chr9:59814737-60358842 | 29551 | Tktl2 | NM_001271574.1 | chr8:69035638-69043098 |
| 29457 | Thsd4 | NM_172444.4 | chr9:59814737-60358842 | 29552 | Tktl2 | NM_028927.3 | chr8:69035638-69043098 |
| 29458 | Thsd7a | NM_001164805.1 | chr6:12261607-12699253 | 29553 | Tlcd1 | NM_001291235.1 | chr11:77991650-77994321 |
| 29459 | Thsd7b | NM_172485.3 | chr1:131169880-132115855 | 29554 | Tlcd1 | NM_001291236.1 | chr11:77991650-77994321 |
| 29460 | Thtpa | NM_153083.5 | chr14:55713621-55717832 | 29555 | Tlcd1 | NM_001291237.1 | chr11:77991650-77994321 |

Fig. 25 - 157

| | | | | | | | | |
|---|---|---|---|---|---|---|---|---|
| 29556 | Ticd1 | NM_026708.2 | chr11:77991650-77994321 | 29651 | Tmco5 | NM_026104.4 | chr2:116704426-116718236 |
| 29557 | Ticd2 | NM_001291156.1 | chr11:75281551-75284401 | 29652 | Tmco5b | NM_029232.2 | chr2:113125888-113137347 |
| 29558 | Ticd2 | NM_027249.3 | chr11:75281551-75284401 | 29653 | Tmco6 | NM_028036.3 | chr18:36894724-36902045 |
| 29559 | Tidc1 | NM_028883.2 | chr8:122284486-122302316 | 29654 | Tmed1 | NM_010744.3 | chr9:21311824-21314630 |
| 29560 | Tidc2 | NM_001177439.1 | chr2:156912790-156922217 | 29655 | Tmed10 | NM_026775.4 | chr12:86681563-86715667 |
| 29561 | Tie1 | NM_001285529.1 | chr4:71770978-71861927 | 29656 | Tmed11 | NM_026109.2 | chr5:109206253-109224382 |
| 29562 | Tie1 | NM_001285530.1 | chr4:71770978-71861927 | 29657 | Tmed2 | NM_019770.2 | chr5:124990799-125000512 |
| 29563 | Tie1 | NM_001285531.1 | chr4:71770978-71861927 | 29658 | Tmed3 | NM_025360.2 | chr9:89594040-89599881 |
| 29564 | Tie1 | NM_001285532.1 | chr4:71770978-71861927 | 29659 | Tmed4 | NM_134020.1 | chr11:6170716-6174840 |
| 29565 | Tie1 | NM_011599.5 | chr4:71770978-71861927 | 29660 | Tmed5 | NM_028876.2 | chr5:108550665-108561610 |
| 29566 | Tie2 | NM_001252401.1 | chr10:81038031-81053590 | 29661 | Tmed6 | NM_025458.2 | chr8:109585383-109589544 |
| 29567 | Tie2 | NM_019725.2 | chr10:81038031-81053590 | 29662 | Tmed7 | NM_025698.1 | chr18:46745581-46757189 |
| 29568 | Tie3 | NM_001083927.1 | chr9:61220172-61266304 | 29663 | Tmed8 | NM_001033475.3 | chr12:88507191-88541179 |
| 29569 | Tie3 | NM_001083928.1 | chr9:61220172-61266304 | 29664 | Tmed9 | NM_026211.3 | chr13:55694495-55699055 |
| 29570 | Tie3 | NM_009389.2 | chr9:61220172-61266304 | 29665 | Tmeff1 | NM_021436.2 | chr4:48598064-48676003 |
| 29571 | Tie4 | NM_001600.3 | chr19:14522561-14672473 | 29666 | Tmeff2 | NM_019790.4 | chr1:50984386-51244114 |
| 29572 | Tie6 | NM_053254.2 | chr10:81053649-81063645 | 29667 | Tmem100 | NM_026433.2 | chr11:89891661-89897819 |
| 29573 | Tik1 | NM_172664.3 | chr2:70550464-70663537 | 29668 | Tmem101 | NM_029649.2 | chr11:102013860-102017721 |
| 29574 | Tik2 | NM_001112705.2 | chr11:105042843-105145270 | 29669 | Tmem102 | NM_001034433.1 | chr7:69617097-69619126 |
| 29575 | Tik2 | NM_011903.3 | chr11:105042843-105145270 | 29670 | Tmem104 | NM_001033393.2 | chr11:115048800-115108339 |
| 29576 | Tk1 | NM_009390.2 | chr8:66493566-66684790 | 29671 | Tmem106a | NM_144830.3 | chr11:101443555-101453099 |
| 29577 | Tk2 | NM_011904.3 | chr19:41158470-41281264 | 29672 | Tmem106b | NM_027992.3 | chr6:13019758-13039269 |
| 29578 | Tln1 | NM_011602.5 | chr4:43544384-43575455 | 29673 | Tmem106c | NM_001252153.1 | chr15:97794659-97800717 |
| 29579 | Tln2 | NM_001081242.2 | chr9:67064892-67407510 | 29674 | Tmem106c | NM_201359.2 | chr15:97794659-97800717 |
| 29580 | Tlr1 | NM_001276445.1 | chr5:65315918-65324797 | 29675 | Tmem107 | NM_025838.2 | chr11:68884310-68886795 |
| 29581 | Tlr1 | NM_030682.1 | chr5:65315918-65324797 | 29676 | Tmem107 | NM_028336.3 | chr11:68884310-68886795 |
| 29582 | Tlr11 | NM_205819.3 | chr14:50977588-50983338 | 29677 | Tmem108 | NM_178638.4 | chr9:103385266-103664167 |
| 29583 | Tlr12 | NM_205823.2 | chr4:128292689-128295863 | 29678 | Tmem109 | NM_134142.1 | chr19:10945151-10956233 |
| 29584 | Tlr13 | NM_205820.1 | chrX:103338613-103355832 | 29679 | Tmem11 | NM_001168507.1 | chr11:60677953-60692540 |
| 29585 | Tlr2 | NM_011905.3 | chr3:83640193-83645530 | 29680 | Tmem11 | NM_173453.3 | chr11:60677953-60692540 |
| 29586 | Tlr3 | NM_126166.4 | chr8:46481018-46495893 | 29681 | Tmem110 | NM_028839.4 | chr14:31638779-31690396 |
| 29587 | Tlr4 | NM_021297.2 | chr4:66488844-66503830 | 29682 | Tmem115 | NM_019704.2 | chr9:107436275-107440987 |
| 29588 | Tlr5 | NM_016928.2 | chr1:184884918-184906175 | 29683 | Tmem116 | NM_001161626.1 | chr5:121902717-121945430 |
| 29589 | Tlr6 | NM_011604.3 | chr5:65344333-65351273 | 29684 | Tmem116 | NM_001161627.1 | chr5:121902717-121945430 |
| 29590 | Tlr7 | NM_001290755.1 | chrX:163742857-163768503 | 29685 | Tmem116 | NM_029912.2 | chr5:121902717-121945430 |
| 29591 | Tlr7 | NM_001290756.1 | chrX:163742857-163768503 | 29686 | Tmem117 | NM_178789.4 | chr15:94459615-94926528 |
| 29592 | Tlr7 | NM_001290757.1 | chrX:163742857-163768503 | 29687 | Tmem119 | NM_146162.2 | chr5:114243737-114250361 |
| 29593 | Tlr7 | NM_001290758.1 | chrX:163742857-163768503 | 29688 | Tmem120a | NM_172541.2 | chr5:136211360-136220042 |
| 29594 | Tlr7 | NM_133211.4 | chrX:163742857-163768503 | 29689 | Tmem120b | NM_001039723.2 | chr5:123528283-123567454 |
| 29595 | Tlr8 | NM_133212.2 | chrX:163680663-163701720 | 29690 | Tmem121 | NM_153776.2 | chr12:114424113-114427733 |
| 29596 | Tlr9 | NM_031178.2 | chr9:106124928-106129207 | 29691 | Tmem123 | NM_133739.2 | chr9:7764077-7794332 |
| 29597 | Tlx1 | NM_021901.3 | chr19:45225204-45231433 | 29692 | Tmem125 | NM_172383.3 | chr4:118213545-118216331 |
| 29598 | Tlx2 | NM_009392.2 | chr6:83018318-83020219 | 29693 | Tmem126a | NM_025460.2 | chr7:97599221-97605718 |
| 29599 | Tlx3 | NM_019916.2 | chr11:33100751-33103588 | 29694 | Tmem126b | NM_026734.1 | chr7:97617338-97624505 |
| 29600 | Tm2d1 | NM_053157.2 | chr4:98022060-98049956 | 29695 | Tmem127 | NM_175145.3 | chr2:127073710-127086500 |
| 29601 | Tm2d2 | NM_027194.3 | chr8:26127682-26133732 | 29696 | Tmem128 | NM_025480.3 | chr5:38651613-38660857 |
| 29602 | Tm2d3 | NM_026795.3 | chr7:72838302-72846799 | 29697 | Tmem129 | NM_026698.2 | chr5:33995864-34000481 |
| 29603 | Tm2d3 | NM_178056.3 | chr7:72838302-72846799 | 29698 | Tmem130 | NM_177735.4 | chr5:145496783-145522447 |
| 29604 | Tm4sf1 | NM_008536.3 | chr3:57090985-57105841 | 29699 | Tmem131 | NM_018872.2 | chr1:36849033-36996372 |
| 29605 | Tm4sf19 | NM_001160402.1 | chr16:32400591-32408313 | 29700 | Tmem132a | NM_133804.2 | chr19:10932319-10944269 |
| 29606 | Tm4sf20 | NM_025453.3 | chr1:82753223-82765031 | 29701 | Tmem132b | NM_001190352.1 | chr5:126012787-126272953 |
| 29607 | Tm4sf4 | NM_145539.2 | chr3:57229331-57245597 | 29702 | Tmem132c | NM_175432.3 | chr5:127722196-128046160 |
| 29608 | Tm4sf5 | NM_029360.3 | chr11:70318775-70324686 | 29703 | Tmem132cos | NR_038127.1 | chr5:127722195-128046160 |
| 29609 | Tm6sf1 | NM_001291282.1 | chr7:89003886-89079345 | 29704 | Tmem132cos | NR_038128.1 | chr5:127722195-128046160 |
| 29610 | Tm6sf1 | NM_145375.4 | chr7:89003886-89079345 | 29705 | Tmem132cos | NR_038129.1 | chr5:127722195-128046160 |
| 29611 | Tm6sf1 | NR_111910.1 | chr7:89003886-89079345 | 29706 | Tmem132d | NM_172885.2 | chr5:128263860-128938937 |
| 29612 | Tm6sf2 | NM_181540.4 | chr8:72596830-72603951 | 29707 | Tmem132e | NM_023438.2 | chr11:82202401-82259829 |
| 29613 | Tm7sf2 | NM_028454.2 | chr19:6062821-6067850 | 29708 | Tmem134 | NM_001078649.1 | chr19:4125959-4132307 |
| 29614 | Tm7sf3 | NM_026281.2 | chr6:146550797-146583114 | 29709 | Tmem134 | NM_025889.2 | chr19:4125959-4132307 |
| 29615 | Tm9sf1 | NM_028780.3 | chr14:56254802-56262643 | 29710 | Tmem135 | NM_028343.4 | chr7:96288230-96487297 |
| 29616 | Tm9sf2 | NM_080556.3 | chr14:122506303-122558825 | 29711 | Tmem136 | NM_001034863.3 | chr9:42916735-42924653 |
| 29617 | Tm9sf3 | NM_133352.2 | chr19:41285331-41338494 | 29712 | Tmem138 | NM_028411.4 | chr19:10645374-10651587 |
| 29618 | Tm9sf4 | NM_133847.3 | chr2:152987036-153036199 | 29713 | Tmem139 | NM_175408.4 | chr6:42211968-42214554 |
| 29619 | Tma16 | NM_025485.2 | chr8:69000244-69010406 | 29714 | Tmem140 | NM_197986.2 | chr6:34813146-34824946 |
| 29620 | Tma7 | NM_183250.2 | chr9:108980501-108984895 | 29715 | Tmem141 | NM_001040130.3 | chr2:25475585-25477525 |
| 29621 | Tmbim1 | NM_027154.5 | chr1:74334821-74350910 | 29716 | Tmem141 | NM_001109993.1 | chr2:25475585-25477525 |
| 29622 | Tmbim4 | NM_026617.3 | chr10:119645881-119661953 | 29717 | Tmem143 | NM_144801.2 | chr7:53152438-53172783 |
| 29623 | Tmbim6 | NM_001171034.1 | chr15:99223377-99240480 | 29718 | Tmem144 | NM_027495.4 | chr3:79617074-79646584 |
| 29624 | Tmbim6 | NM_001171035.1 | chr15:99223377-99240480 | 29719 | Tmem145 | NM_183311.2 | chr7:26091126-26101214 |
| 29625 | Tmbim6 | NM_001171036.1 | chr15:99223377-99240480 | 29720 | Tmem147 | NM_027215.2 | chr7:31512719-31514553 |
| 29626 | Tmbim6 | NM_026669.4 | chr15:99223377-99240480 | 29721 | Tmem14a | NM_001290679.1 | chr1:21208655-21220248 |
| 29627 | Tmbim7 | NM_029141.4 | chr5:3657003-3679544 | 29722 | Tmem14a | NM_029398.3 | chr1:21208655-21220248 |
| 29628 | Tmbim7 | NM_139101.1 | chr5:3657003-3679544 | 29723 | Tmem14c | NM_025387.3 | chr13:41111618-41117951 |
| 29629 | Tmc1 | NM_028953.2 | chr19:20857947-21028692 | 29724 | Tmem150a | NM_144916.3 | chr6:72305477-72309756 |
| 29630 | Tmc2 | NM_138655.1 | chr2:130020929-130090181 | 29725 | Tmem150b | NM_001142792.1 | chr7:4642529-4676853 |
| 29631 | Tmc3 | NM_177045.2 | chr7:90733440-90772219 | 29726 | Tmem150b | NM_177887.4 | chr7:4642529-4676853 |
| 29632 | Tmc4 | NM_181820.2 | chr7:3617356-3629155 | 29727 | Tmem150c | NM_182841.1 | chr5:100506892-100588827 |
| 29633 | Tmc5 | NM_001105252.1 | chr7:125740810-125818599 | 29728 | Tmem150cos | NR_045993.1 | chr5:100506981-100524292 |
| 29634 | Tmc5 | NM_028930.3 | chr7:125740810-125818599 | 29729 | Tmem151a | NM_001001885.1 | chr19:5079336-5085477 |
| 29635 | Tmc6 | NM_145439.2 | chr11:117627298-117641997 | 29730 | Tmem151b | NM_001013749.2 | chr17:45678889-45686626 |
| 29636 | Tmc6 | NM_181321.3 | chr11:117627298-117641997 | 29731 | Tmem154 | NM_177260.2 | chr3:84470113-84508497 |
| 29637 | Tmc7 | NM_172476.4 | chr7:125679357-125728200 | 29732 | Tmem158 | NM_001002267.2 | chr9:123168174-123169907 |
| 29638 | Tmc8 | NM_001195088.1 | chr11:117643610-117654451 | 29733 | Tmem159 | NM_145586.3 | chr7:127245939-127264500 |
| 29639 | Tmc8 | NM_001195089.1 | chr11:117643610-117654451 | 29734 | Tmem160 | NM_026938.1 | chr7:17038127-17040839 |
| 29640 | Tmc8 | NM_001195090.1 | chr11:117643610-117654451 | 29735 | Tmem161a | NM_145597.4 | chr8:72696309-72707562 |
| 29641 | Tmc8 | NM_181856.2 | chr11:117643610-117654451 | 29736 | Tmem161b | NM_175187.5 | chr13:84361900-84435571 |
| 29642 | Tmcc1 | NM_177412.1 | chr6:115968635-116143392 | 29737 | Tmem161b | NR_029418.1 | chr13:84361900-84435571 |
| 29643 | Tmcc2 | NM_178874.2 | chr1:134252891-134287858 | 29738 | Tmem161b | NR_029419.1 | chr13:84361900-84435571 |
| 29644 | Tmcc3 | NM_001168684.1 | chr10:93977601-94053699 | 29739 | Tmem163 | NM_028135.2 | chr1:129386918-129574598 |
| 29645 | Tmcc3 | NM_177453.3 | chr10:93977601-94053699 | 29740 | Tmem164 | NM_001199357.1 | chrX:139115942-139278037 |
| 29646 | Tmcc3 | NM_177026.1 | chr10:93977601-94053699 | 29741 | Tmem164 | NM_001199360.1 | chrX:139115942-139278037 |
| 29647 | Tmco1 | NM_001039483.1 | chr1:169238800-169264109 | 29742 | Tmem164 | NM_175592.4 | chrX:139115942-139278037 |
| 29648 | Tmco2 | NM_001081312.1 | chr4:120778255-120781831 | 29743 | Tmem165 | NM_011626.2 | chr5:76612904-76638269 |
| 29649 | Tmco3 | NM_172282.2 | chr8:13288013-13322924 | 29744 | Tmem167 | NM_025335.3 | chr13:90229271-90254526 |
| 29650 | Tmco4 | NM_029857.3 | chr4:138528819-138615086 | 29745 | Tmem167b | NM_026198.2 | chr3:108359342-108365384 |

Fig. 25 - 158

| | | | | | | | | |
|---|---|---|---|---|---|---|---|---|
| 29746 | Tmem168 | NM_028990.4 | chr6:13530688-13558063 | | 29841 | Tmem219 | NM_026827.1 | chr7:134029732-134041792 |
| 29747 | Tmem169 | NM_175564.4 | chr3:72330946-72349569 | | 29842 | Tmem219 | NM_028389.1 | chr7:134029732-134041792 |
| 29748 | Tmem17 | NM_153596.3 | chr11:22412285-22419234 | | 29843 | Tmem220 | NM_001291042.1 | chr11:66838655-66848814 |
| 29749 | Tmem170 | NM_025781.2 | chr8:114388797-114400575 | | 29844 | Tmem220 | NM_001291043.1 | chr11:66838655-66848814 |
| 29750 | Tmem170b | NM_001163572.1 | chr13:41701584-41736726 | | 29845 | Tmem220 | NM_177392.3 | chr11:66838655-66848814 |
| 29751 | Tmem171 | NM_001025606.1 | chr13:99456192-99464786 | | 29846 | Tmem221 | NM_001100462.1 | chr8:74078201-74082770 |
| 29752 | Tmem173 | NM_001289591.1 | chr18:35893331-35900208 | | 29847 | Tmem222 | NM_025667.3 | chr4:132821959-132833705 |
| 29753 | Tmem173 | NM_001289592.1 | chr18:35893331-35900208 | | 29848 | Tmem222 | NR_110978.1 | chr4:132821959-132833705 |
| 29754 | Tmem173 | NM_028261.1 | chr18:35893331-35900208 | | 29849 | Tmem223 | NM_025791.1 | chr19:8845485-8846965 |
| 29755 | Tmem174 | NM_026685.2 | chr13:99404932-99407365 | | 29850 | Tmem225 | NM_029379.1 | chr9:39955706-39958463 |
| 29756 | Tmem175 | NM_001163531.1 | chr5:109058828-109114465 | | 29851 | Tmem229a | NM_177013.1 | chr6:24901140-24906125 |
| 29757 | Tmem175 | NM_001163532.1 | chr5:109058828-109114465 | | 29852 | Tmem229b | NM_001170401.1 | chr12:80062781-80108264 |
| 29758 | Tmem175 | NM_028223.3 | chr5:109058828-109114465 | | 29853 | Tmem229b | NM_178745.4 | chr12:80062781-80108264 |
| 29759 | Tmem176a | NM_001098271.1 | chr6:48791481-48795363 | | 29854 | Tmem230 | NM_001141971.1 | chr2:132065227-132073524 |
| 29760 | Tmem176a | NM_025326.4 | chr6:48791481-48795363 | | 29855 | Tmem230 | NM_027478.3 | chr2:132065227-132073524 |
| 29761 | Tmem176b | NM_001164207.1 | chr6:48783810-48791373 | | 29856 | Tmem231 | NM_001033321.1 | chr8:114435917-114457691 |
| 29762 | Tmem176b | NM_001164208.1 | chr6:48783810-48791373 | | 29857 | Tmem232 | NM_001008973.2 | chr17:65605344-65890122 |
| 29763 | Tmem176b | NM_001164209.2 | chr6:48783810-48791373 | | 29858 | Tmem232 | NM_001289485.1 | chr17:65605344-65890122 |
| 29764 | Tmem176b | NM_001286651.1 | chr6:48783810-48791373 | | 29859 | Tmem232 | NM_001289486.1 | chr17:65605344-65890122 |
| 29765 | Tmem176b | NM_001286652.1 | chr6:48783810-48791373 | | 29860 | Tmem233 | NM_001101546.1 | chr5:116490542-116533255 |
| 29766 | Tmem176b | NM_023056.4 | chr6:48783810-48791373 | | 29861 | Tmem234 | NM_029748.2 | chr4:129277950-129285123 |
| 29767 | Tmem176b | NR_104575.1 | chr6:48783810-48791373 | | 29862 | Tmem235 | NM_001085535.1 | chr11:117722065-117726857 |
| 29768 | Tmem177 | NM_175106.3 | chr1:121804477-121809745 | | 29863 | Tmem236 | NM_001081310.2 | chr2:14096150-14143620 |
| 29769 | Tmem178 | NM_026516.2 | chr17:81343971-81401156 | | 29864 | Tmem237 | NM_001033449.1 | chr1:59157436-59176940 |
| 29770 | Tmem178b | NM_001004182.3 | chr6:40060251-40198352 | | 29865 | Tmem237 | NM_001037812.2 | chr1:59157436-59176940 |
| 29771 | Tmem179 | NM_178915.3 | chr12:113738394-113749371 | | 29866 | Tmem238 | NM_029384.1 | chr7:4736386-4741162 |
| 29772 | Tmem179b | NM_026325.3 | chr19:8847011-8860907 | | 29867 | Tmem239 | NM_025753.3 | chr2:130232257-130233530 |
| 29773 | Tmem179b | NR_028418.1 | chr19:8847011-8860907 | | 29868 | Tmem240 | NM_001101506.1 | chr4:155108912-155114673 |
| 29774 | Tmem179b | NR_028419.1 | chr19:8847011-8860907 | | 29869 | Tmem241 | NM_001289666.1 | chr18:12139811-12280046 |
| 29775 | Tmem18 | NM_172049.2 | chr12:31269307-31276084 | | 29870 | Tmem241 | NM_001289667.1 | chr18:12139811-12280046 |
| 29776 | Tmem180 | NM_029136.4 | chr19:46431369-46449744 | | 29871 | Tmem241 | NM_178801.5 | chr18:12139811-12280046 |
| 29777 | Tmem181a | NM_001033178.2 | chr17:6270470-6308314 | | 29872 | Tmem241 | NR_110356.1 | chr18:12139811-12280046 |
| 29778 | Tmem181b-ps | NR_033520.1 | chr17:6438149-6450142 | | 29873 | Tmem242 | NM_027457.4 | chr17:5410864-5440260 |
| 29779 | Tmem181c-ps | NR_028305.2 | chr17:6635807-6646630 | | 29874 | Tmem243 | NM_001081029.1 | chr5:9100737-9118983 |
| 29780 | Tmem181c-ps | NR_028305.2 | chr17:6814820-6825643 | | 29875 | Tmem245 | NM_175518.5 | chr4:56888885-56960301 |
| 29781 | Tmem182 | NM_001081198.1 | chr1:40862445-40912112 | | 29876 | Tmem246 | NM_025944.3 | chr4:49597377-49610742 |
| 29782 | Tmem183a | NM_001042485.1 | chr1:136242673-136258576 | | 29877 | Tmem247 | NM_001277980.1 | chr17:87316687-87321707 |
| 29783 | Tmem183a | NM_020588.2 | chr1:136242673-136258576 | | 29878 | Tmem247 | NM_030104.1 | chr17:87316687-87321707 |
| 29784 | Tmem184a | NM_001161543.1 | chr5:140280905-140290237 | | 29879 | Tmem248 | NM_001081394.1 | chr5:130695613-130719635 |
| 29785 | Tmem184a | NM_144914.3 | chr5:140280905-140290237 | | 29880 | Tmem248 | NM_027854.1 | chr5:130695613-130719635 |
| 29786 | Tmem184b | NM_001253817.1 | chr15:79191113-79233733 | | 29881 | Tmem25 | NM_027865.2 | chr9:44601861-44607299 |
| 29787 | Tmem184b | NM_001253819.1 | chr15:79191113-79233733 | | 29882 | Tmem251 | NM_177140.3 | chr12:103981970-103983607 |
| 29788 | Tmem184b | NM_001253820.1 | chr15:79191113-79233733 | | 29883 | Tmem252 | NM_183160.3 | chr19:24748498-24754151 |
| 29789 | Tmem184b | NM_172608.1 | chr15:79191113-79233733 | | 29884 | Tmem253 | NM_001033805.2 | chr14:52636540-52639462 |
| 29790 | Tmem184c | NM_145599.4 | chr8:80119878-80134652 | | 29885 | Tmem254a | NM_025311.3 | chr14:26742783-26747158 |
| 29791 | Tmem185b | NM_146103.2 | chr1:121422730-121425560 | | 29886 | Tmem254a | NM_025311.3 | chr14:26882536-26886911 |
| 29792 | Tmem186 | NM_025708.4 | chr16:8633823-8637794 | | 29887 | Tmem254a | NM_025311.3 | chr14:27022152-27026527 |
| 29793 | Tmem189 | NM_145558.2 | chr2:167468724-167487044 | | 29888 | Tmem254a | NM_026679.2 | chr14:26742783-26747158 |
| 29794 | Tmem19 | NM_133683.3 | chr10:114777795-114799318 | | 29889 | Tmem254a | NM_026679.2 | chr14:27022152-27026527 |
| 29795 | Tmem190 | NM_030028.1 | chr7:4734541-4735942 | | 29890 | Tmem254a | NM_026679.2 | chr14:26882536-26886911 |
| 29796 | Tmem191c | NM_177473.3 | chr16:17276392-17278754 | | 29891 | Tmem254b | NM_001270495.1 | chr14:27022152-27026527 |
| 29797 | Tmem192 | NM_001163747.1 | chr8:67471083-67492935 | | 29892 | Tmem254b | NM_001270495.1 | chr14:26882536-26886911 |
| 29798 | Tmem192 | NM_028427.3 | chr8:67471083-67492935 | | 29893 | Tmem254b | NM_001270495.1 | chr14:26742783-26747158 |
| 29799 | Tmem194 | NM_001113211.1 | chr10:127114120-127138103 | | 29894 | Tmem254b | NM_001270496.1 | chr14:26882536-26886911 |
| 29800 | Tmem194 | NM_173732.3 | chr10:127114120-127138103 | | 29895 | Tmem254b | NM_001270496.1 | chr14:26742783-26747158 |
| 29801 | Tmem194b | NM_001142647.1 | chr1:52687548-52708763 | | 29896 | Tmem254c | NM_001270496.1 | chr14:27022152-27026527 |
| 29802 | Tmem194b | NR_024590.1 | chr1:52687548-52708763 | | 29897 | Tmem254c | NM_001270498.1 | chr14:27022152-27026527 |
| 29803 | Tmem196 | NM_001160385.2 | chr12:121184434-121257179 | | 29898 | Tmem254c | NM_001270498.1 | chr14:26882536-26886911 |
| 29804 | Tmem198 | NM_177056.4 | chr1:75476106-75482268 | | 29899 | Tmem254c | NM_001270498.1 | chr14:26742783-26747158 |
| 29805 | Tmem198b | NM_178066.2 | chr10:128237092-128241426 | | 29900 | Tmem254c | NM_001270499.1 | chr14:26742783-26747158 |
| 29806 | Tmem199 | NM_199199.3 | chr11:78320556-78325670 | | 29901 | Tmem254c | NM_001270499.1 | chr14:27022152-27026527 |
| 29807 | Tmem2 | NM_001033759.2 | chr19:21852829-21932850 | | 29902 | Tmem254c | NM_001270499.1 | chr14:26882536-26886911 |
| 29808 | Tmem2 | NM_031997.4 | chr19:21852829-21932850 | | 29903 | Tmem255a | NM_001289727.1 | chrX:35542969-35605658 |
| 29809 | Tmem200a | NM_029881.3 | chr10:25710992-25798858 | | 29904 | Tmem255a | NM_001289728.1 | chrX:35542969-35605658 |
| 29810 | Tmem200b | NM_001201367.1 | chr4:131477685-131479055 | | 29905 | Tmem255a | NM_172930.4 | chrX:35542969-35605658 |
| 29811 | Tmem200c | NM_001206661.1 | chr17:69186475-69192478 | | 29906 | Tmem255b | NM_001143671.1 | chr8:13435458-13461451 |
| 29812 | Tmem201 | NM_001284270.1 | chr4:149089483-149112177 | | 29907 | Tmem255b | NM_001143672.1 | chr8:13435458-13461451 |
| 29813 | Tmem201 | NM_001284273.1 | chr4:149089483-149112177 | | 29908 | Tmem256 | NM_026982.1 | chr11:69652026-69653060 |
| 29814 | Tmem201 | NM_177672.4 | chr4:149089483-149112177 | | 29909 | Tmem258 | NM_001163431.1 | chr19:10278691-10282314 |
| 29815 | Tmem202 | NM_178358.3 | chr9:59366491-59373308 | | 29910 | Tmem258 | NM_026919.1 | chr19:10278691-10282314 |
| 29816 | Tmem203 | NM_177344.2 | chr2:25110958-25111872 | | 29911 | Tmem259 | NM_001003949.3 | chr10:79439865-79447075 |
| 29817 | Tmem204 | NM_001001183.1 | chr17:25194647-25218059 | | 29912 | Tmem26 | NM_177794.3 | chr10:68186493-68245402 |
| 29818 | Tmem205 | NM_001253867.1 | chr9:21725452-21740316 | | 29913 | Tmem260 | NM_172600.3 | chr14:49066026-49134834 |
| 29819 | Tmem205 | NM_001253868.1 | chr9:21725452-21740316 | | 29914 | Tmem261 | NM_025849.3 | chr4:74923257-74924190 |
| 29820 | Tmem205 | NM_001253869.1 | chr9:21725452-21740316 | | 29915 | Tmem263 | NM_001013028.2 | chr10:84565371-84580492 |
| 29821 | Tmem205 | NM_001253870.1 | chr9:21725452-21740316 | | 29916 | Tmem27 | NM_020626.2 | chrX:160528118-160556791 |
| 29822 | Tmem205 | NM_178577.5 | chr9:21725452-21740316 | | 29917 | Tmem28 | NM_001081283.1 | chrX:97016407-97041684 |
| 29823 | Tmem205 | NR_045606.1 | chr9:21725452-21740316 | | 29918 | Tmem29 | NM_001164683.1 | chrX:146832315-146893693 |
| 29824 | Tmem206 | NM_025864.3 | chr1:193149844-193176804 | | 29919 | Tmem29 | NM_001164684.1 | chrX:146832315-146893693 |
| 29825 | Tmem207 | NM_001101640.1 | chr16:26503878-26526857 | | 29920 | Tmem29 | NM_001164686.1 | chrX:146832315-146893693 |
| 29826 | Tmem208 | NM_025486.2 | chr8:107850263-107852957 | | 29921 | Tmem30a | NM_133718.4 | chr9:79616747-79641237 |
| 29827 | Tmem209 | NM_178625.3 | chr6:30431232-30459706 | | 29922 | Tmem30b | NM_178715.3 | chr12:74644100-74647382 |
| 29828 | Tmem210 | NM_030055.1 | chr2:25143664-25144707 | | 29923 | Tmem30c | NM_027651.1 | chr16:57266251-57292964 |
| 29829 | Tmem211 | NM_001033428.2 | chr5:113665928-113668283 | | 29924 | Tmem33 | NM_001285452.1 | chr5:67651803-67682700 |
| 29830 | Tmem212 | NM_001064437.1 | chr3:27764986-27795290 | | 29925 | Tmem33 | NM_028975.4 | chr5:67651803-67682700 |
| 29831 | Tmem213 | NM_029921.1 | chr6:38059353-38065806 | | 29926 | Tmem33 | NM_030108.2 | chr5:67651803-67682700 |
| 29832 | Tmem214 | NM_144705.3 | chr5:31172019-31179840 | | 29927 | Tmem35 | NM_026239.2 | chrX:130829763-130840508 |
| 29833 | Tmem215 | NM_001166009.1 | chr4:40419212-40422686 | | 29928 | Tmem37 | NM_019432.2 | chr1:121963953-121970357 |
| 29834 | Tmem215 | NM_177175.4 | chr4:40419212-40422686 | | 29929 | Tmem38a | NM_144534.1 | chr8:75096001-75111183 |
| 29835 | Tmem216 | NM_001277860.1 | chr19:10624950-10630728 | | 29930 | Tmem38b | NM_028053.2 | chr4:53838916-53874890 |
| 29836 | Tmem216 | NM_001277861.1 | chr19:10624950-10630728 | | 29931 | Tmem39a | NM_001205286.1 | chr16:38558810-38592275 |
| 29837 | Tmem216 | NM_026798.3 | chr19:10624950-10630728 | | 29932 | Tmem39a | NM_001205287.1 | chr16:38558810-38592275 |
| 29838 | Tmem217 | NM_001162901.1 | chr17:29662962-29686538 | | 29933 | Tmem39a | NM_026407.3 | chr16:38558810-38592275 |
| 29839 | Tmem217 | NM_001162902.1 | chr17:29662962-29686538 | | 29934 | Tmem39b | NM_199305.1 | chr4:129353599-129374082 |
| 29840 | Tmem218 | NM_025464.2 | chr9:37015917-37030796 | | 29935 | Tmem40 | NM_001168256.1 | chr6:115679156-115712484 |

Fig. 25 - 159

| | | | |
|---|---|---|---|
| 29936 | Tmem40 | NM_001168257.1 | chr6:115679156-115712484 |
| 29937 | Tmem40 | NM_001168258.1 | chr6:115679156-115712484 |
| 29938 | Tmem40 | NM_001168259.1 | chr6:115679156-115712484 |
| 29939 | Tmem40 | NM_144805.2 | chr6:115679156-115712484 |
| 29940 | Tmem41a | NM_025693.4 | chr16:21934399-21947625 |
| 29941 | Tmem41a | NR_037773.1 | chr16:21934399-21947625 |
| 29942 | Tmem41b | NM_153525.5 | chr7:117115700-117129744 |
| 29943 | Tmem42 | NM_001164823.1 | chr9:122930443-122932609 |
| 29944 | Tmem42 | NM_025339.3 | chr9:122930443-122932609 |
| 29945 | Tmem43 | NM_028766.2 | chr6:91423744-91438452 |
| 29946 | Tmem44 | NM_172614.3 | chr16:30511940-30550664 |
| 29947 | Tmem45a | NM_019631.3 | chr16:56805273-56886276 |
| 29948 | Tmem45b | NM_144936.1 | chr9:31233780-31271823 |
| 29949 | Tmem47 | NM_138751.2 | chrX:78315982-78343214 |
| 29950 | Tmem5 | NM_153059.1 | chr10:121518315-121534158 |
| 29951 | Tmem50a | NM_027935.2 | chr4:134453763-134470831 |
| 29952 | Tmem50b | NM_030018.3 | chr16:91574752-91597925 |
| 29953 | Tmem51 | NM_145402.3 | chr4:141586908-141640219 |
| 29954 | Tmem51os1 | NR_027137.1 | chr4:141640213-141644016 |
| 29955 | Tmem52 | NM_001253856.1 | chr4:154843222-154844967 |
| 29956 | Tmem52 | NM_001253858.1 | chr4:154843222-154844967 |
| 29957 | Tmem52 | NM_025382.3 | chr4:154843222-154844967 |
| 29958 | Tmem52b | NM_001081186.1 | chr6:129462574-129469245 |
| 29959 | Tmem53 | NM_001285812.1 | chr4:116924555-116941193 |
| 29960 | Tmem53 | NM_001285814.1 | chr4:116924555-116941193 |
| 29961 | Tmem53 | NM_001285815.1 | chr4:116924555-116941193 |
| 29962 | Tmem53 | NM_001285816.1 | chr4:116924555-116941193 |
| 29963 | Tmem53 | NM_026433.3 | chr4:116924555-116941193 |
| 29964 | Tmem53 | NM_029589.1 | chr4:116924555-116941193 |
| 29965 | Tmem54 | NM_001290706.1 | chr4:128782773-128799169 |
| 29966 | Tmem54 | NM_025452.4 | chr4:128782773-128799169 |
| 29967 | Tmem54 | NM_133881.1 | chr4:128782773-128799169 |
| 29968 | Tmem55a | NM_028264.4 | chr4:14791365-14842407 |
| 29969 | Tmem55b | NM_001033271.4 | chr14:51545745-51550524 |
| 29970 | Tmem56 | NM_178936.3 | chr3:120904927-120966234 |
| 29971 | Tmem57 | NM_025382.6 | chr4:134358675-134409260 |
| 29972 | Tmem59 | NM_029565.3 | chr4:106851234-106873601 |
| 29973 | Tmem59l | NM_182991.2 | chr8:73007769-73011257 |
| 29974 | Tmem60 | NM_177601.3 | chr5:20388270-20392688 |
| 29975 | Tmem62 | NM_175285.3 | chr2:120802797-120833578 |
| 29976 | Tmem63a | NM_144794.2 | chr1:182872648-182905235 |
| 29977 | Tmem63b | NM_198161.7 | chr17:45797125-45823167 |
| 29978 | Tmem63c | NM_172583.2 | chr12:88367513-88430989 |
| 29979 | Tmem64 | NM_181401.3 | chr4:15192966-15213900 |
| 29980 | Tmem65 | NM_175212.4 | chr15:58613823-58654982 |
| 29981 | Tmem66 | NM_026432.3 | chr8:35217617-35233901 |
| 29982 | Tmem67 | NM_177861.4 | chr4:11966503-12015154 |
| 29983 | Tmem67 | NR_110955.1 | chr4:11966503-12015154 |
| 29984 | Tmem68 | NM_028097.3 | chr4:3476187-3501915 |
| 29985 | Tmem69 | NM_177670.4 | chr4:116224132-116228548 |
| 29986 | Tmem70 | NM_026392.1 | chr1:16655271-16668356 |
| 29987 | Tmem70 | NM_027415.2 | chr1:16655271-16668356 |
| 29988 | Tmem71 | NM_172514.3 | chr15:66357773-66392608 |
| 29989 | Tmem72 | NM_178768.4 | chr6:116642742-116666776 |
| 29990 | Tmem74 | NM_175502.3 | chr15:43698240-43701575 |
| 29991 | Tmem74b | NM_001160363.1 | chr2:151527743-151533046 |
| 29992 | Tmem79 | NM_024246.1 | chr3:88132574-88138355 |
| 29993 | Tmem8 | NM_021793.2 | chr17:26250260-26260198 |
| 29994 | Tmem80 | NM_001141950.1 | chr7:148483074-148524682 |
| 29995 | Tmem80 | NM_027797.3 | chr7:148483074-148524682 |
| 29996 | Tmem80 | NR_024509.1 | chr7:148483074-148524682 |
| 29997 | Tmem81 | NM_029025.3 | chr1:134402806-134405216 |
| 29998 | Tmem82 | NM_145987.2 | chr4:141170148-141174548 |
| 29999 | Tmem86a | NM_026436.3 | chr7:54306009-54310146 |
| 30000 | Tmem86b | NM_023440.2 | chr7:4579641-4582084 |
| 30001 | Tmem87a | NM_001110496.1 | chr2:120181044-120330655 |
| 30002 | Tmem87a | NM_001110497.1 | chr2:120181044-120330655 |
| 30003 | Tmem87a | NM_173734.3 | chr2:120181044-120330655 |
| 30004 | Tmem87b | NM_028248.2 | chr2:128644038-128679997 |
| 30005 | Tmem88 | NM_025915.4 | chr11:69210018-69211736 |
| 30006 | Tmem88b | NM_001083394.3 | chr4:155155699-155159983 |
| 30007 | Tmem89 | NM_027066.1 | chr9:108816949-108817894 |
| 30008 | Tmem8b | NM_001085823.1 | chr4:43681842-43705539 |
| 30009 | Tmem8c | NM_001159602.1 | chr2:26917155-26927681 |
| 30010 | Tmem8c | NM_025376.3 | chr2:26917155-26927681 |
| 30011 | Tmem9 | NM_001160145.1 | chr1:137904795-137931607 |
| 30012 | Tmem9 | NM_001160146.1 | chr1:137904795-137931607 |
| 30013 | Tmem9 | NM_025439.3 | chr1:137904795-137931607 |
| 30014 | Tmem91 | NM_001034896.2 | chr7:26454158-26460185 |
| 30015 | Tmem91 | NM_001290498.1 | chr7:26454158-26460185 |
| 30016 | Tmem91 | NM_177102.4 | chr7:26454158-26460185 |
| 30017 | Tmem92 | NM_001034895.2 | chr11:94638530-94693316 |
| 30018 | Tmem92 | NM_001163172.1 | chr11:94638530-94693316 |
| 30019 | Tmem95 | NM_001195710.1 | chr11:69690185-69691520 |
| 30020 | Tmem97 | NM_133706.2 | chr11:78355318-78364237 |
| 30021 | Tmem98 | NM_029537.1 | chr11:80623916-80635535 |
| 30022 | Tmem9b | NM_020050.1 | chr7:116879349-116895777 |
| 30023 | Tmevpg1 | NR_104123.1 | chr10:117939090-117993581 |
| 30024 | Tmf1 | NM_001081111.2 | chr6:97101943-97129118 |
| 30025 | Tmie | NM_146260.2 | chr9:110768549-110782587 |
| 30026 | Tmigd1 | NM_025655.2 | chr11:76718046-76730088 |
| 30027 | Tmlhe | NM_138758.1 | chrX_random:159647-334187 |
| 30028 | Tmod1 | NM_021883.2 | chr4:46052094-46128904 |
| 30029 | Tmod2 | NM_001038710.1 | chr9:75413428-75459132 |
| 30030 | Tmod2 | NM_016711.3 | chr9:75413428-75459132 |
| 30031 | Tmod3 | NM_016963.2 | chr9:75345590-75407464 |
| 30032 | Tmod4 | NM_016712.3 | chr3:94928435-94933130 |
| 30033 | Tmpo | NM_001080129.2 | chr10:90610315-90634364 |
| 30034 | Tmpo | NM_001080130.2 | chr10:90610315-90634364 |
| 30035 | Tmpo | NM_001080131.2 | chr10:90610315-90634364 |
| 30036 | Tmpo | NM_001080132.2 | chr10:90610315-90634364 |
| 30037 | Tmpo | NM_001283048.1 | chr10:90610315-90634364 |
| 30038 | Tmpo | NM_011605.3 | chr10:90610315-90634364 |
| 30039 | Tmppe | NM_001200002.1 | chr9:114310213-114320319 |
| 30040 | Tmprss11a | NM_001033233.2 | chr5:86839434-86898015 |
| 30041 | Tmprss11bnl | NM_177024.4 | chr5:87088546-87105323 |
| 30042 | Tmprss11c | NM_001030297.2 | chr5:86660505-86718333 |
| 30043 | Tmprss11d | NM_145561.2 | chr5:86731878-86802412 |
| 30044 | Tmprss11e | NM_172880.2 | chr5:87134210-87174832 |
| 30045 | Tmprss11f | NM_178730.3 | chr5:86950250-87061449 |
| 30046 | Tmprss11g | NM_177162.4 | chr5:86914981-86947625 |
| 30047 | Tmprss12 | NM_183109.3 | chr15:100111267-100123484 |
| 30048 | Tmprss13 | NM_001013373.2 | chr9:45127183-45155663 |
| 30049 | Tmprss15 | NM_008941.3 | chr16:78953252-79091342 |
| 30050 | Tmprss15 | NM_178855.4 | chr16:78953252-79091342 |
| 30051 | Tmprss2 | NM_015775.2 | chr16:77786288-97832802 |
| 30052 | Tmprss3 | NM_001163776.1 | chr17:31316211-31335919 |
| 30053 | Tmprss3 | NM_080727.2 | chr17:31316211-31335919 |
| 30054 | Tmprss4 | NM_145403.2 | chr9:44980809-45012158 |
| 30055 | Tmprss5 | NM_030709.1 | chr9:48910883-48925693 |
| 30056 | Tmprss6 | NM_027902.2 | chr15:78270096-78299064 |
| 30057 | Tmprss7 | NM_172455.3 | chr16:45656429-45693771 |
| 30058 | Tmprss9 | NM_001081688.2 | chr10:80342561-80362239 |
| 30059 | Tmsb10 | NM_001039392.2 | chr6:72907340-72908742 |
| 30060 | Tmsb10 | NM_001190327.1 | chr6:72907340-72908742 |
| 30061 | Tmsb10 | NM_025284.4 | chr6:72907340-72908742 |
| 30062 | Tmsb15a | NM_030106.2 | chrX:132253205-132255212 |
| 30063 | Tmsb15b1 | NM_001081983.1 | chrX:133508561-133511413 |
| 30064 | Tmsb15b2 | NM_001080962.1 | chrX:133489529-133492518 |
| 30065 | Tmsb15l | NM_207267.4 | chrX:133489529-133511413 |
| 30066 | Tmsb4x | NM_021278.2 | chrX:163645025-163647150 |
| 30067 | Tmtc1 | NM_198967.5 | chr6:148180952-148392874 |
| 30068 | Tmtc2 | NM_177368.4 | chr10:104624719-105011535 |
| 30069 | Tmtc3 | NM_001033332.2 | chr10:99906535-99949981 |
| 30070 | Tmtc3 | NM_001110013.1 | chr10:99906535-99949981 |
| 30071 | Tmtc4 | NM_028651.2 | chr14:123318196-123382483 |
| 30072 | Tmub1 | NM_024418.3 | chr5:23951280-23953664 |
| 30073 | Tmub2 | NM_028076.3 | chr11:102146253-102150741 |
| 30074 | Tmx1 | NM_028339.1 | chr12:71554140-71568611 |
| 30075 | Tmx2 | NM_001290751.1 | chr2:84511467-84555321 |
| 30076 | Tmx2 | NM_025868.4 | chr2:84511467-84555321 |
| 30077 | Tmx3 | NM_198295.2 | chr18:90679545-90712659 |
| 30078 | Tmx4 | NM_029148.1 | chr2:134420241-134469857 |
| 30079 | Tnc | NM_011607.3 | chr4:63620818-63708049 |
| 30080 | Tnf | NM_001278601.1 | chr17:35336311-35338952 |
| 30081 | Tnf | NM_013693.3 | chr17:35336311-35338952 |
| 30082 | Tnfaip1 | NM_001159392.1 | chr11:78336351-78349762 |
| 30083 | Tnfaip1 | NM_009395.4 | chr11:78336351-78349762 |
| 30084 | Tnfaip2 | NM_009396.2 | chr12:112680871-112693229 |
| 30085 | Tnfaip3 | NM_001166402.1 | chr10:18720716-18735216 |
| 30086 | Tnfaip3 | NM_009397.3 | chr10:18720716-18735216 |
| 30087 | Tnfaip6 | NM_009398.2 | chr2:51893632-51912201 |
| 30088 | Tnfaip8 | NM_001177759.1 | chr18:50139080-50252883 |
| 30089 | Tnfaip8 | NM_001177760.1 | chr18:50139080-50252883 |
| 30090 | Tnfaip8 | NM_134131.2 | chr18:50139080-50252883 |
| 30091 | Tnfaip8l1 | NM_025566.3 | chr17:56301913-56313378 |
| 30092 | Tnfaip8l2 | NM_027206.2 | chr3:94943443-94946282 |
| 30093 | Tnfaip8l3 | NM_001033535.3 | chr9:53873412-53916218 |
| 30094 | Tnfrsf10b | NM_020275.4 | chr14:70169778-70184218 |
| 30095 | Tnfrsf11a | NM_009399.3 | chr1:107677299-107744558 |
| 30096 | Tnfrsf11b | NM_008764.3 | chr15:54082173-54110039 |
| 30097 | Tnfrsf12a | NM_001161746.1 | chr17:23797489-23814416 |
| 30098 | Tnfrsf12a | NM_013749.2 | chr17:23797489-23814416 |
| 30099 | Tnfrsf13b | NM_021349.1 | chr11:60954336-60961144 |
| 30100 | Tnfrsf13c | NM_028075.2 | chr15:82052173-82054766 |
| 30101 | Tnfrsf14 | NM_178931.2 | chr4:154296318-154302186 |
| 30102 | Tnfrsf17 | NM_011608.1 | chr16:11313901-11320161 |
| 30103 | Tnfrsf18 | NM_009400.2 | chr4:155400450-155403000 |
| 30104 | Tnfrsf18 | NM_021985.2 | chr4:155400450-155403000 |
| 30105 | Tnfrsf19 | NM_001164155.1 | chr14:61582670-61665692 |
| 30106 | Tnfrsf19 | NM_013869.5 | chr14:61582670-61665692 |
| 30107 | Tnfrsf1a | NM_011609.4 | chr6:125299740-125312501 |
| 30108 | Tnfrsf1b | NM_011610.3 | chr4:144802270-144836773 |
| 30109 | Tnfrsf21 | NM_178589.3 | chr17:43153503-43226137 |
| 30110 | Tnfrsf22 | NM_023680.3 | chr7:150822629-150835543 |
| 30111 | Tnfrsf23 | NM_024290.4 | chr7:150851711-150871777 |
| 30112 | Tnfrsf25 | NM_001291010.1 | chr4:151490042-151494228 |
| 30113 | Tnfrsf25 | NM_033042.4 | chr4:151490042-151494228 |
| 30114 | Tnfrsf26 | NM_175649.5 | chr7:150793589-150813750 |
| 30115 | Tnfrsf4 | NM_011659.2 | chr4:155387873-155390698 |
| 30116 | Tnfrsf8 | NM_009401.2 | chr4:144858878-144905050 |
| 30117 | Tnfrsf9 | NM_001077508.1 | chr4:150294263-150320211 |
| 30118 | Tnfrsf9 | NM_001077509.1 | chr4:150294263-150320211 |
| 30119 | Tnfrsf9 | NM_011612.2 | chr4:150294263-150320211 |
| 30120 | Tnfsf10 | NM_009425.2 | chr3:27215998-27238587 |
| 30121 | Tnfsf11 | NM_011613.3 | chr14:78677252-78707850 |
| 30122 | Tnfsf12 | NM_011614.3 | chr11:69499742-69509600 |
| 30123 | Tnfsf12Tnfsf13 | NM_001034097.2 | chr11:69496078-69509600 |
| 30124 | Tnfsf12Tnfsf13 | NM_001159503.2 | chr11:69496078-69509600 |
| 30125 | Tnfsf13 | NM_001159505.1 | chr11:69496078-69509600 |

Fig. 25 - 160

| | | | |
|---|---|---|---|
| 30126 | Tnfsf13 | NM_023517.2 | chr11:69496078-69509600 |
| 30127 | Tnfsf13b | NM_033622.1 | chr8:10006632-10035999 |
| 30128 | Tnfsf14 | NM_019418.3 | chr17:57328896-57333604 |
| 30129 | Tnfsf15 | NM_177371.3 | chr4:63385636-63406147 |
| 30130 | Tnfsf18 | NM_183391.3 | chr1:163424787-163435421 |
| 30131 | Tnfsf4 | NM_009452.2 | chr1:163325568-163348337 |
| 30132 | Tnfsf8 | NM_009403.3 | chr4:63493857-63522318 |
| 30133 | Tnfsf9 | NM_009404.3 | chr17:57244808-57247180 |
| 30134 | Tnik | NM_001163007.1 | chr3:28162135-28569507 |
| 30135 | Tnik | NM_001163008.1 | chr3:28162135-28569507 |
| 30136 | Tnik | NM_001163009.1 | chr3:28162135-28569507 |
| 30137 | Tnik | NM_026910.1 | chr3:28162135-28569507 |
| 30138 | Tnip1 | NM_001199275.2 | chr11:54724288-54776442 |
| 30139 | Tnip1 | NM_001199276.2 | chr11:54724288-54776442 |
| 30140 | Tnip1 | NM_001271455.1 | chr11:54724288-54776442 |
| 30141 | Tnip1 | NM_001271456.1 | chr11:54724288-54776442 |
| 30142 | Tnip1 | NM_021327.4 | chr11:54724288-54776442 |
| 30143 | Tnip2 | NM_139064.2 | chr5:34838744-34856628 |
| 30144 | Tnip3 | NM_001001495.1 | chr6:65540391-65584034 |
| 30145 | Tnk1 | NM_031880.3 | chr11:69664065-69672232 |
| 30146 | Tnk2 | NM_001110147.1 | chr16:32644728-32683579 |
| 30147 | Tnk2 | NM_001289443.1 | chr16:32644728-32683579 |
| 30148 | Tnk2 | NM_016788.3 | chr16:32644728-32683579 |
| 30149 | Tnk2os | NR_033493.1 | chr16:32665309-32668283 |
| 30150 | Tnks | NM_175091.3 | chr8:35892232-36028744 |
| 30151 | Tnks1bp1 | NM_001081260.2 | chr2:84890616-84913205 |
| 30152 | Tnks2 | NM_001163635.1 | chr19:36908721-36967967 |
| 30153 | Tnmd | NM_022322.2 | chrX:130385546-130400116 |
| 30154 | Tnn | NM_177839.3 | chr1:162015162-162083706 |
| 30155 | Tnnc1 | NM_009393.2 | chr14:32021497-32024897 |
| 30156 | Tnnc2 | NM_009394.2 | chr2:164602661-164606234 |
| 30157 | Tnni1 | NM_001112702.1 | chr1:137695997-137707566 |
| 30158 | Tnni1 | NM_021467.5 | chr1:137695997-137707566 |
| 30159 | Tnni2 | NM_009405.2 | chr7:149628372-149630310 |
| 30160 | Tnni3 | NM_009406.3 | chr7:4469909-4474045 |
| 30161 | Tnni3k | NM_177066.5 | chr3:154449254-154718371 |
| 30162 | Tnnt1 | NM_001277903.1 | chr7:4456171-4467577 |
| 30163 | Tnnt1 | NM_001277904.1 | chr7:4456171-4467577 |
| 30164 | Tnnt1 | NM_011618.2 | chr7:4456171-4467577 |
| 30165 | Tnnt2 | NM_001130174.2 | chr1:137732910-137748845 |
| 30166 | Tnnt2 | NM_001130175.2 | chr1:137732910-137748845 |
| 30167 | Tnnt2 | NM_001130176.1 | chr1:137732910-137748845 |
| 30168 | Tnnt2 | NM_001130177.2 | chr1:137732910-137748845 |
| 30169 | Tnnt2 | NM_001130178.2 | chr1:137732910-137748845 |
| 30170 | Tnnt2 | NM_001130179.1 | chr1:137732910-137748845 |
| 30171 | Tnnt2 | NM_001130180.2 | chr1:137732910-137748845 |
| 30172 | Tnnt2 | NM_001130181.2 | chr1:137732910-137748845 |
| 30173 | Tnnt2 | NM_011619.3 | chr1:137732910-137748845 |
| 30174 | Tnnt3 | NM_001163664.1 | chr7:149646716-149701914 |
| 30175 | Tnnt3 | NM_001163665.1 | chr7:149646716-149701914 |
| 30176 | Tnnt3 | NM_001163666.1 | chr7:149646716-149701914 |
| 30177 | Tnnt3 | NM_001163667.1 | chr7:149646716-149701914 |
| 30178 | Tnnt3 | NM_001163668.1 | chr7:149646716-149701914 |
| 30179 | Tnnt3 | NM_001163669.1 | chr7:149646716-149701914 |
| 30180 | Tnnt3 | NM_001163670.1 | chr7:149646716-149701914 |
| 30181 | Tnnt3 | NM_011620.3 | chr7:149646716-149701914 |
| 30182 | Tnp1 | NM_009407.2 | chr1:73061648-73062473 |
| 30183 | Tnp2 | NM_013694.4 | chr16:10788027-10788748 |
| 30184 | Tnpo1 | NM_001048267.1 | chr13:99612035-99696339 |
| 30185 | Tnpo1 | NM_178716.3 | chr13:99612035-99696339 |
| 30186 | Tnpo2 | NM_001122843.1 | chr8:87560813-87591019 |
| 30187 | Tnpo2 | NM_145390.2 | chr8:87560813-87591019 |
| 30188 | Tnpo3 | NM_177296.4 | chr6:29490826-29559607 |
| 30189 | Tnr | NM_023312.3 | chr1:161453899-161855053 |
| 30190 | Tnrc18 | NM_001122730.2 | chr5:143200557-143579066 |
| 30191 | Tnrc18 | NM_178242.2 | chr5:143200557-143579066 |
| 30192 | Tnrc6a | NM_144925.3 | chr7:123567398-130338810 |
| 30193 | Tnrc6b | NM_144812.2 | chr15:80541742-80771516 |
| 30194 | Tnrc6b | NM_177124.4 | chr15:80541742-80771516 |
| 30195 | Tnrc6c | NM_198022.2 | chr11:117515602-117624753 |
| 30196 | Tns1 | NM_001289895.1 | chr1:73956804-74171023 |
| 30197 | Tns1 | NM_027884.3 | chr1:73956804-74171023 |
| 30198 | Tns3 | NM_001083587.1 | chr11:8331654-8564538 |
| 30199 | Tns4 | NM_172564.3 | chr11:98826991-98950620 |
| 30200 | Tnxb | NM_031176.2 | chr17:34807479-34856760 |
| 30201 | Tob1 | NM_009427.2 | chr11:94072767-94076806 |
| 30202 | Tob2 | NM_020507.3 | chr15:81678699-81688756 |
| 30203 | Toe1 | NM_026654.2 | chr4:116476608-116480164 |
| 30204 | Tollip | NM_023784.3 | chr7:149067489-149088311 |
| 30205 | Tom1 | NM_001136259.1 | chr8:77557584-77594020 |
| 30206 | Tom1 | NM_011622.3 | chr8:77557584-77594020 |
| 30207 | Tom1l1 | NM_028011.2 | chr11:90507005-90548915 |
| 30208 | Tom1l2 | NM_001039092.3 | chr11:60040215-60166407 |
| 30209 | Tom1l2 | NM_001039093.1 | chr11:60040215-60166407 |
| 30210 | Tom1l2 | NM_153080.2 | chr11:60040215-60166407 |
| 30211 | Tomm20 | NM_024214.2 | chr8:129454563-129469821 |
| 30212 | Tomm20l | NM_029227.1 | chr12:72212415-72224209 |
| 30213 | Tomm22 | NM_172609.3 | chr15:79501297-79503292 |
| 30214 | Tomm34 | NM_001291155.1 | chr2:163879275-163896905 |
| 30215 | Tomm34 | NM_025996.5 | chr2:163879275-163896905 |
| 30216 | Tomm40 | NM_001109748.1 | chr7:20286661-20300778 |
| 30217 | Tomm40 | NM_016871.2 | chr7:20286661-20300778 |
| 30218 | Tomm40l | NM_001037170.2 | chr1:173147934-173152645 |
| 30219 | Tomm5 | NM_001099675.1 | chr4:45118081-45120985 |
| 30220 | Tomm5 | NM_001134646.1 | chr4:45118081-45120985 |
| 30221 | Tomm6 | NM_001164729.1 | chr17:47823593-47831685 |
| 30222 | Tomm6 | NM_025365.3 | chr17:47823593-47831685 |
| 30223 | Tomm6os | NR_045945.1 | chr17:47824559-47828041 |
| 30224 | Tomm7 | NM_025394.3 | chr5:23344761-23349963 |
| 30225 | Tomm70a | NM_138599.5 | chr16:57121826-57154643 |
| 30226 | Tomt | NM_001081679.1 | chr7:109048321-109060417 |
| 30227 | Tomt | NM_001282088.1 | chr7:109048321-109060417 |
| 30228 | Tonsl | NM_183091.3 | chr15:76456666-76470359 |
| 30229 | Top1 | NM_009408.2 | chr2:160471632-160548499 |
| 30230 | Top1mt | NM_028404.2 | chr15:75487462-75509220 |
| 30231 | Top2a | NM_011623.2 | chr11:98854260-98885503 |
| 30232 | Top2b | NM_009409.2 | chr14:17197719-17263301 |
| 30233 | Top3a | NM_009410.2 | chr11:60553560-60590867 |
| 30234 | Top3b | NM_011624.2 | chr16:16870983-16893079 |
| 30235 | Topaz1 | NM_001199736.1 | chr9:122656463-122711192 |
| 30236 | Topbp1 | NM_176979.5 | chr9:103207856-103252757 |
| 30237 | Topors | NM_134097.3 | chr4:40206639-40216874 |
| 30238 | Toporsl | NM_026652.2 | chr4:52609145-52625035 |
| 30239 | Toporsos | NR_045265.1 | chr4:40216612-40217254 |
| 30240 | Tor1a | NM_144884.2 | chr2:30816080-30823438 |
| 30241 | Tor1aip1 | NM_001160018.1 | chr1:157851728-157915989 |
| 30242 | Tor1aip1 | NM_001160019.1 | chr1:157851728-157915989 |
| 30243 | Tor1aip1 | NM_144791.2 | chr1:157851728-157915989 |
| 30244 | Tor1aip2 | NM_001160180.1 | chr1:157851728-157915989 |
| 30245 | Tor1aip2 | NM_001160181.1 | chr1:157851728-157915989 |
| 30246 | Tor1aip2 | NM_001160182.1 | chr1:157851728-157915989 |
| 30247 | Tor1aip2 | NM_022329.4 | chr1:157851728-157915989 |
| 30248 | Tor1aip2 | NM_172843.4 | chr1:157851728-157915989 |
| 30249 | Tor1b | NM_138673.3 | chr2:30808520-30814535 |
| 30250 | Tor2a | NM_152800.3 | chr2:32612545-32631153 |
| 30251 | Tor2a | NR_045485.1 | chr2:32612545-32631153 |
| 30252 | Tor3a | NM_023141.2 | chr1:158583747-158604470 |
| 30253 | Tor4a | NM_146115.4 | chr2:25048239-25052333 |
| 30254 | Tox | NM_145711.4 | chr4:6614532-6917870 |
| 30255 | Tox2 | NM_001098799.1 | chr2:163051189-163148838 |
| 30256 | Tox3 | NM_172913.3 | chr8:92771010-92872151 |
| 30257 | Tox4 | NM_023434.3 | chr14:52898821-52915184 |
| 30258 | Tpbg | NM_001164792.1 | chr9:85735986-85740662 |
| 30259 | Tpbg | NM_011627.4 | chr9:85735986-85740662 |
| 30260 | Tpbpa | NM_009411.4 | chr13:61040052-61043296 |
| 30261 | Tpbpb | NM_026429.4 | chr13:61002655-61066208 |
| 30262 | Tpcn1 | NM_145853.2 | chr5:120984165-121038622 |
| 30263 | Tpcn2 | NM_146206.4 | chr7:152439827-152469832 |
| 30264 | Tpd52 | NM_001025261.1 | chr3:8929435-9004515 |
| 30265 | Tpd52 | NM_001025262.1 | chr3:8929435-9004515 |
| 30266 | Tpd52 | NM_001025263.1 | chr3:8929435-9004515 |
| 30267 | Tpd52 | NM_001025264.1 | chr3:8929435-9004515 |
| 30268 | Tpd52 | NM_009412.2 | chr3:8929435-9004515 |
| 30269 | Tpd52l1 | NM_009413.1 | chr10:31052186-31165727 |
| 30270 | Tpd52l2 | NM_001291197.1 | chr2:181231846-181252667 |
| 30271 | Tpd52l2 | NM_001291200.1 | chr2:181231846-181252667 |
| 30272 | Tpd52l2 | NM_001291201.1 | chr2:181231846-181252667 |
| 30273 | Tpd52l2 | NM_001291202.1 | chr2:181231846-181252667 |
| 30274 | Tpd52l2 | NM_001291203.1 | chr2:181231846-181252667 |
| 30275 | Tpd52l2 | NM_001291204.1 | chr2:181231846-181252667 |
| 30276 | Tpd52l2 | NM_025482.3 | chr2:181231846-181252667 |
| 30277 | Tpd52l2 | NR_111899.1 | chr2:181231846-181252667 |
| 30278 | Tpgs1 | NM_148934.2 | chr10:79132154-79138871 |
| 30279 | Tpgs2 | NM_001004361.2 | chr18:24867123-25327378 |
| 30280 | Tpgs2 | NM_001142697.1 | chr18:24867123-25327378 |
| 30281 | Tpgs2 | NM_001142698.1 | chr18:24867123-25327378 |
| 30282 | Tph1 | NM_001136084.2 | chr7:53900010-53927907 |
| 30283 | Tph1 | NM_001276372.1 | chr7:53900010-53927907 |
| 30284 | Tph1 | NM_009414.3 | chr7:53900010-53927907 |
| 30285 | Tph2 | NM_173391.3 | chr10:114515696-114622078 |
| 30286 | Tpi1 | NM_009415.2 | chr6:124760610-124764314 |
| 30287 | Tpk1 | NM_013861.3 | chr6:43295006-43616174 |
| 30288 | Tpm1 | NM_001164248.1 | chr9:66870399-66897020 |
| 30289 | Tpm1 | NM_001164249.1 | chr9:66870399-66897020 |
| 30290 | Tpm1 | NM_001164250.1 | chr9:66870399-66897020 |
| 30291 | Tpm1 | NM_001164251.1 | chr9:66870399-66897020 |
| 30292 | Tpm1 | NM_001164252.1 | chr9:66870399-66897020 |
| 30293 | Tpm1 | NM_001164253.1 | chr9:66870399-66897020 |
| 30294 | Tpm1 | NM_001164254.1 | chr9:66870399-66897020 |
| 30295 | Tpm1 | NM_001164255.1 | chr9:66870399-66897020 |
| 30296 | Tpm1 | NM_001164256.1 | chr9:66870399-66897020 |
| 30297 | Tpm1 | NM_024427.4 | chr9:66870399-66897020 |
| 30298 | Tpm2 | NM_001277875.1 | chr4:43526597-43536426 |
| 30299 | Tpm2 | NM_001277876.1 | chr4:43526597-43536426 |
| 30300 | Tpm2 | NM_009416.4 | chr4:43526597-43536426 |
| 30301 | Tpm3 | NM_001253738.1 | chr3:89876572-89904824 |
| 30302 | Tpm3 | NM_001253740.1 | chr3:89876572-89904824 |
| 30303 | Tpm3 | NM_001271764.1 | chr3:89876572-89904824 |
| 30304 | Tpm3 | NM_022314.3 | chr3:89876572-89904824 |
| 30305 | Tpm4 | NM_001001491.1 | chr8:74659190-74677028 |
| 30306 | Tpmt | NM_016785.2 | chr13:47118911-47138586 |
| 30307 | Tpo | NM_009417.2 | chr12:30739525-30817474 |
| 30308 | Tpp1 | NM_009906.5 | chr7:112893360-112900721 |
| 30309 | Tpp2 | NM_009418.2 | chr1:43990851-44059816 |
| 30310 | Tppp | NM_182839.2 | chr13:74146866-74173201 |
| 30311 | Tppp2 | NM_001128634.1 | chr14:52538435-52540375 |
| 30312 | Tppp3 | NM_026481.3 | chr8:107991391-107995322 |
| 30313 | Tpr | NM_133780.3 | chr1:152239968-152297065 |
| 30314 | Tpra1 | NM_011906.2 | chr6:88852244-88862234 |
| 30315 | Tprg | NM_175165.3 | chr16:25286902-25422430 |

Fig. 25 - 161

| | | | |
|---|---|---|---|
| 30316 | Tprg1 | NM_026388.2 | chr4:153531594-153534793 |
| 30317 | Tprkb | NM_001170488.1 | chr6:85865712-85880278 |
| 30318 | Tprkb | NM_176842.3 | chr6:85865712-85880278 |
| 30319 | Tprn | NM_175286.4 | chr2:25118117-25125406 |
| 30320 | Tpsab1 | NM_031187.4 | chr17:25480189-25482507 |
| 30321 | Tpsab1 | NR_033521.1 | chr17:25480189-25482507 |
| 30322 | Tpsb2 | NM_010781.3 | chr17:25503277-25505037 |
| 30323 | Tpsg1 | NM_012034.3 | chr17:25507498-25511387 |
| 30324 | Tpst1 | NM_001130476.2 | chr5:130549195-130611603 |
| 30325 | Tpst1 | NM_013837.2 | chr5:130549195-130611603 |
| 30326 | Tpst2 | NM_009419.3 | chr5:112705726-112744376 |
| 30327 | Tpt1 | NM_009429.3 | chr14:76245063-76248110 |
| 30328 | Tpre | NM_199257.2 | chr8:23393912-23481890 |
| 30329 | Tpx2 | NM_001141975.1 | chr2:152673699-152721057 |
| 30330 | Tpx2 | NM_001141976.1 | chr2:152673699-152721057 |
| 30331 | Tpx2 | NM_001141977.1 | chr2:152673699-152721057 |
| 30332 | Tpx2 | NM_001141978.1 | chr2:152673699-152721057 |
| 30333 | Tpx2 | NM_028109.4 | chr2:152673699-152721057 |
| 30334 | Tra2a | NM_198102.2 | chr6:49193919-49214051 |
| 30335 | Tra2b | NM_009186.4 | chr16:22245813-22266002 |
| 30336 | Trabd | NM_026485.2 | chr15:88906493-88917505 |
| 30337 | Trabd2b | NM_001085549.1 | chr4:114079328-114287703 |
| 30338 | Tradd | NM_001033161.2 | chr8:107782474-107788494 |
| 30339 | Traf1 | NM_009421.3 | chr2:34798777-34817292 |
| 30340 | Traf2 | NM_001290421.1 | chr2:25373501-25402460 |
| 30341 | Traf2 | NM_009422.3 | chr2:25373501-25402460 |
| 30342 | Traf3 | NM_001286122.1 | chr12:112404580-112505366 |
| 30343 | Traf3 | NM_011632.3 | chr12:112404580-112505366 |
| 30344 | Traf3ip1 | NM_028718.2 | chr1:93391244-93425884 |
| 30345 | Traf3ip2 | NM_134000.3 | chr10:39332740-39375113 |
| 30346 | Traf3ip3 | NM_153137.4 | chr1:195001698-195027740 |
| 30347 | Traf4 | NM_009423.4 | chr11:77971924-77979052 |
| 30348 | Traf5 | NM_011633.2 | chr1:193821084-193916480 |
| 30349 | Traf6 | NM_009424.3 | chr2:101518596-101541131 |
| 30350 | Traf7 | NM_001172113.1 | chr17:24625727-24664883 |
| 30351 | Traf7 | NM_001172114.1 | chr17:24625727-24664883 |
| 30352 | Traf7 | NM_153792.2 | chr17:24625727-24664883 |
| 30353 | Trafd1 | NM_001163470.1 | chr5:121821733-121835624 |
| 30354 | Trafd1 | NM_172275.2 | chr5:121821733-121835624 |
| 30355 | Traip | NM_011634.3 | chr9:107853293-107874599 |
| 30356 | Trak1 | NM_175114.3 | chr9:121276075-121384036 |
| 30357 | Trak2 | NM_172406.3 | chr1:58957293-59030326 |
| 30358 | Tram1 | NM_028173.5 | chr1:13554782-13579945 |
| 30359 | Tram1l1 | NM_146140.3 | chr3:124023954-124026178 |
| 30360 | Tram2 | NM_177439.3 | chr1:20991477-21069306 |
| 30361 | Trank1 | NM_001164659.1 | chr9:111214242-111298279 |
| 30362 | Trap1 | NM_026508.2 | chr16:4039977-4077810 |
| 30363 | Trap1a | NM_011635.1 | chrX:135868222-135872704 |
| 30364 | Trappc1 | NM_001024206.2 | chr11:69137487-69139295 |
| 30365 | Trappc10 | NM_001081055.1 | chr10:77649470-77707387 |
| 30366 | Trappc11 | NM_177240.3 | chr8:48575481-48618824 |
| 30367 | Trappc12 | NM_001161410.1 | chr12:29375492-29435318 |
| 30368 | Trappc12 | NM_001161411.1 | chr12:29375492-29435318 |
| 30369 | Trappc12 | NM_178811.4 | chr12:29375492-29435318 |
| 30370 | Trappc13 | NM_001093759.1 | chr13:104932232-104968546 |
| 30371 | Trappc13 | NM_001093760.1 | chr13:104932232-104968546 |
| 30372 | Trappc13 | NM_025879.2 | chr13:104932232-104968546 |
| 30373 | Trappc13 | NR_003546.1 | chr13:104932232-104968546 |
| 30374 | Trappc2 | NM_025432.3 | chrX:162878756-162890475 |
| 30375 | Trappc2l | NM_021502.2 | chr8:125135525-125139491 |
| 30376 | Trappc3 | NM_013718.2 | chr4:125939648-125953127 |
| 30377 | Trappc3l | NM_001162937.1 | chr10:33757403-33829621 |
| 30378 | Trappc4 | NM_021789.2 | chr9:44211841-44215631 |
| 30379 | Trappc5 | NM_025701.4 | chr8:3676479-3680921 |
| 30380 | Trappc6a | NM_025960.3 | chr7:20094077-20101494 |
| 30381 | Trappc6b | NM_030057.3 | chr12:60144078-60162448 |
| 30382 | Trappc8 | NM_029491.2 | chr18:20975724-21054579 |
| 30383 | Trappc8 | NM_177038.3 | chr18:20975724-21054579 |
| 30384 | Trappc9 | NM_001164641.1 | chr15:72420049-72891634 |
| 30385 | Trappc9 | NM_001164642.1 | chr15:72420049-72891634 |
| 30386 | Trappc9 | NM_001164643.1 | chr15:72420049-72891634 |
| 30387 | Trappc9 | NM_029640.2 | chr15:72420049-72891634 |
| 30388 | Trappc9 | NM_180662.2 | chr15:72420049-72891634 |
| 30389 | Trat1 | NM_198297.3 | chr16:48734802-48772069 |
| 30390 | Trcg1 | NM_001014398.2 | chr9:57084362-57097671 |
| 30391 | Trdmt1 | NM_010067.4 | chr2:13431787-13466291 |
| 30392 | Trdn | NM_029726.2 | chr10:32803289-33196515 |
| 30393 | Treh | NM_001277847.1 | chr9:44481315-44494388 |
| 30394 | Treh | NM_001277851.1 | chr9:44481315-44494388 |
| 30395 | Treh | NM_021481.3 | chr9:44481315-44494388 |
| 30396 | Trem1 | NM_021406.5 | chr17:48371902-48386091 |
| 30397 | Trem2 | NM_001272078.1 | chr17:48485725-48491601 |
| 30398 | Trem2 | NM_031254.3 | chr17:48485725-48491601 |
| 30399 | Trem3 | NM_021407.3 | chr17:48386895-48398213 |
| 30400 | Treml1 | NM_001289451.1 | chr17:48499240-48506501 |
| 30401 | Treml1 | NM_001289457.1 | chr17:48499240-48506501 |
| 30402 | Treml1 | NM_027963.4 | chr17:48499240-48506501 |
| 30403 | Treml1 | NR_110338.1 | chr17:48499240-48506501 |
| 30404 | Treml2 | NM_001033405.2 | chr17:48439362-48451859 |
| 30405 | Treml4 | NM_001033922.2 | chr17:48403660-48414724 |
| 30406 | Treml4 | NM_001163795.1 | chr17:48403660-48414724 |
| 30407 | Treml4 | NM_001163796.1 | chr17:48403660-48414724 |
| 30408 | Treml4 | NM_172623.2 | chr17:48403660-48414724 |
| 30409 | Trerf1 | NM_001097623.1 | chr17:47277890-47496407 |
| 30410 | Trerf1 | NM_172622.2 | chr17:47277890-47496407 |

| | | | |
|---|---|---|---|
| 30411 | Trex1 | NM_001012236.1 | chr9:108960445-108962237 |
| 30412 | Trex1 | NM_011637.6 | chr9:108960445-108962237 |
| 30413 | Trex2 | NM_011907.4 | chrX:70679043-70680682 |
| 30414 | Trf | NM_133977.2 | chr9:103111205-103132616 |
| 30415 | Trh | NM_009426.3 | chr6:92192054-92194644 |
| 30416 | Trhde | NM_146241.2 | chr10:113835876-114238426 |
| 30417 | Trhr | NM_013696.1 | chr15:44027680-44067458 |
| 30418 | Trhr2 | NM_133202.2 | chr8:124880866-124884646 |
| 30419 | Triap1 | NM_026333.2 | chr5:115791255-115793561 |
| 30420 | Trib1 | NM_144549.4 | chr15:59480208-59488654 |
| 30421 | Trib2 | NM_144551.5 | chr12:15798533-15823591 |
| 30422 | Trib3 | NM_175093.2 | chr2:152163160-152169796 |
| 30423 | Tril | NM_025817.4 | chr6:53765461-53770819 |
| 30424 | Trim10 | NM_011280.2 | chr17:37006518-37014778 |
| 30425 | Trim11 | NM_001290988.1 | chr11:58791594-58804964 |
| 30426 | Trim11 | NM_053168.2 | chr11:58791594-58804964 |
| 30427 | Trim12a | NM_023835.2 | chr7:111448411-111464009 |
| 30428 | Trim12c | NM_001146007.1 | chr7:111487267-111501872 |
| 30429 | Trim12c | NM_175677.4 | chr7:111487267-111501872 |
| 30430 | Trim13 | NM_001164220.1 | chr14:62217062-62301210 |
| 30431 | Trim13 | NM_023233.3 | chr14:62217062-62301210 |
| 30432 | Trim14 | NM_029077.4 | chr4:46517943-46549013 |
| 30433 | Trim15 | NM_001024134.2 | chr17:36997635-37004155 |
| 30434 | Trim15 | NM_001177872.1 | chr17:36997635-37004155 |
| 30435 | Trim16 | NM_053169.2 | chr11:62633754-62656450 |
| 30436 | Trim17 | NM_031172.2 | chr11:58777282-58785231 |
| 30437 | Trim2 | NM_001271725.1 | chr3:83964360-84108697 |
| 30438 | Trim2 | NM_001271726.1 | chr3:83964360-84108697 |
| 30439 | Trim2 | NM_001271727.1 | chr3:83964360-84108697 |
| 30440 | Trim2 | NM_001271728.1 | chr3:83964360-84108697 |
| 30441 | Trim2 | NM_030706.3 | chr3:83964360-84108697 |
| 30442 | Trim21 | NM_001082552.2 | chr7:109706433-109713996 |
| 30443 | Trim21 | NM_009277.4 | chr7:109706433-109713996 |
| 30444 | Trim23 | NM_030731.3 | chr13:104969177-104992128 |
| 30445 | Trim24 | NM_001272064.1 | chr6:37820810-37918445 |
| 30446 | Trim24 | NM_001272076.1 | chr6:37820810-37918445 |
| 30447 | Trim24 | NM_145076.4 | chr6:37820810-37918445 |
| 30448 | Trim25 | NM_009546.2 | chr11:88860716-88881607 |
| 30449 | Trim26 | NM_001025599.3 | chr17:36974090-36996343 |
| 30450 | Trim26 | NM_001286726.1 | chr17:36974090-36996343 |
| 30451 | Trim26 | NM_001286727.1 | chr17:36974090-36996343 |
| 30452 | Trim27 | NM_009054.3 | chr13:21271799-21286592 |
| 30453 | Trim28 | NM_011588.3 | chr7:13609500-13616381 |
| 30454 | Trim29 | NM_023655.2 | chr9:43118845-43144208 |
| 30455 | Trim3 | NM_001285870.1 | chr7:112752976-112782085 |
| 30456 | Trim3 | NM_001285871.1 | chr7:112752976-112782085 |
| 30457 | Trim3 | NM_001285873.1 | chr7:112752976-112782085 |
| 30458 | Trim3 | NM_018880.3 | chr7:112752976-112782085 |
| 30459 | Trim30a | NM_009099.2 | chr7:111557539-111613707 |
| 30460 | Trim30b | NM_175648.2 | chr7:111503911-111507160 |
| 30461 | Trim30d | NM_001167828.1 | chr7:111618528-111656363 |
| 30462 | Trim30d | NM_199146.2 | chr7:111618528-111656363 |
| 30463 | Trim30e-ps1 | NR_033673.1 | chr7:111503492-111683875 |
| 30464 | Trim31 | NM_146077.2 | chr17:37035074-37047162 |
| 30465 | Trim32 | NM_001161782.1 | chr4:65041836-66065517 |
| 30466 | Trim32 | NM_053084.2 | chr4:65041836-66065517 |
| 30467 | Trim33 | NM_001079830.2 | chr3:103083215-103162693 |
| 30468 | Trim33 | NM_053170.3 | chr3:103083215-103162693 |
| 30469 | Trim34a | NM_030684.3 | chr7:111392970-111410750 |
| 30470 | Trim34b | NM_001243916.1 | chr7:111477984-111485131 |
| 30471 | Trim35 | NM_029979.3 | chr14:66915862-66930261 |
| 30472 | Trim36 | NM_001170855.1 | chr18:46324953-46372261 |
| 30473 | Trim36 | NM_178872.4 | chr18:46324953-46372261 |
| 30474 | Trim37 | NM_197987.2 | chr11:86940576-87034188 |
| 30475 | Trim38 | NM_001029935.2 | chr13:23874409-23883397 |
| 30476 | Trim39 | NM_024468.2 | chr17:36395817-36408949 |
| 30477 | Trim39 | NM_178281.1 | chr17:36395817-36408949 |
| 30478 | Trim40 | NM_001033235.3 | chr17:37018542-37027070 |
| 30479 | Trim40 | NM_001172168.1 | chr17:37018542-37027070 |
| 30480 | Trim41 | NM_145377.2 | chr11:48619905-48630893 |
| 30481 | Trim42 | NM_030219.2 | chr9:97249980-97270377 |
| 30482 | Trim43a | NM_001034906.2 | chr9:88475873-88483657 |
| 30483 | Trim43b | NM_001170884.1 | chr9:88979461-88987673 |
| 30484 | Trim43c | NM_001177858.1 | chr9:88734002-88743028 |
| 30485 | Trim44 | NM_020267.2 | chr2:102140275-102241057 |
| 30486 | Trim45 | NM_001165952.1 | chr3:100726415-100740848 |
| 30487 | Trim45 | NM_001165953.1 | chr3:100726415-100740848 |
| 30488 | Trim45 | NM_194343.2 | chr3:100726415-100740848 |
| 30489 | Trim46 | NM_001039466.1 | chr3:89038098-89049819 |
| 30490 | Trim46 | NM_183037.2 | chr3:89038098-89049819 |
| 30491 | Trim47 | NM_001205081.1 | chr11:115967063-115971549 |
| 30492 | Trim47 | NM_172570.5 | chr11:115967063-115971549 |
| 30493 | Trim50 | NM_178240.2 | chr5:135829165-135843524 |
| 30494 | Trim52 | NM_198601.1 | chr14:106505414-106535079 |
| 30495 | Trim52 | NR_073203.1 | chr14:106505414-106535079 |
| 30496 | Trim54 | NM_021447.2 | chr5:31418985-31439999 |
| 30497 | Trim55 | NM_001081281.1 | chr3:19544459-19591599 |
| 30498 | Trim56 | NM_201373.4 | chr5:137587155-137592077 |
| 30499 | Trim58 | NM_001039047.1 | chr11:58453966-58465906 |
| 30500 | Trim59 | NM_025863.3 | chr3:68839215-68848664 |
| 30501 | Trim6 | NM_001013616.2 | chr7:111367308-111383666 |
| 30502 | Trim60 | NM_153097.2 | chr8:67522347-67542587 |
| 30503 | Trim61 | NM_001177551.1 | chr8:67522346-67542587 |
| 30504 | Trim61 | NM_153110.4 | chr8:67522346-67542587 |
| 30505 | Trim62 | NM_178110.2 | chr4:128561383-128588570 |

Fig. 25 - 162

| | | | |
|---|---|---|---|
| 30506 | Trim63 | NM_001039048.2 | chr4:133871034-133885544 |
| 30507 | Trim65 | NM_178802.4 | chr11:115986021-115992442 |
| 30508 | Trim66 | NM_001170912.1 | chr7:116592514-116651648 |
| 30509 | Trim66 | NM_001170913.1 | chr7:116592514-116651648 |
| 30510 | Trim66 | NM_181853.4 | chr7:116592514-116651648 |
| 30511 | Trim67 | NM_198632.2 | chr8:127316918-127358604 |
| 30512 | Trim68 | NM_198012.3 | chr7:109826093-109835840 |
| 30513 | Trim69 | NM_080510.2 | chr2:121986436-122004763 |
| 30514 | Trim7 | NM_053166.2 | chr11:48639639-48663697 |
| 30515 | Trim71 | NM_001042503.2 | chr9:114420398-114475487 |
| 30516 | Trim72 | NM_001079932.3 | chr7:135147891-135154907 |
| 30517 | Trim75 | NM_001033429.2 | chr8:67505549-67511543 |
| 30518 | Trim8 | NM_053100.2 | chr19:46576137-46590945 |
| 30519 | Trim9 | NM_001110202.1 | chr12:71345520-71448601 |
| 30520 | Trim9 | NM_001110203.1 | chr12:71345520-71448601 |
| 30521 | Trim9 | NM_001286386.1 | chr12:71345520-71448601 |
| 30522 | Trim9 | NM_001286387.1 | chr12:71345520-71448601 |
| 30523 | Trim9 | NM_001286388.1 | chr12:71345520-71448601 |
| 30524 | Trim9 | NM_053167.3 | chr12:71345520-71448601 |
| 30525 | Trimi1 | NM_177742.4 | chr8:44215160-44226840 |
| 30526 | Trimi2 | NM_001160412.1 | chr8:44268475-44279238 |
| 30527 | Trio | NM_001081302.1 | chr15:27660403-27955603 |
| 30528 | Triobp | NM_001024716.1 | chr15:78778153-78841471 |
| 30529 | Triobp | NM_001039155.1 | chr15:78778153-78841471 |
| 30530 | Triobp | NM_001039156.1 | chr15:78778153-78841471 |
| 30531 | Triobp | NM_138579.4 | chr15:78778153-78841471 |
| 30532 | Trip10 | NM_001242389.1 | chr17:57388873-57403120 |
| 30533 | Trip10 | NM_001242390.1 | chr17:57388873-57403120 |
| 30534 | Trip10 | NM_001242391.1 | chr17:57388873-57403120 |
| 30535 | Trip10 | NM_134125.4 | chr17:57388873-57403120 |
| 30536 | Trip11 | NM_028446.1 | chr12:103075581-103151381 |
| 30537 | Trip12 | NM_133975.4 | chr1:84717763-84835879 |
| 30538 | Trip13 | NM_027182.2 | chr13:74049909-74075215 |
| 30539 | Trip4 | NM_001170907.1 | chr9:65676732-65756601 |
| 30540 | Trip4 | NM_019797.4 | chr9:65676732-65756601 |
| 30541 | Trip6 | NM_011639.3 | chr5:137751126-137755469 |
| 30542 | Triqk | NM_001171801.1 | chr4:12833983-12908632 |
| 30543 | Triqk | NM_173746.3 | chr4:12833983-12908632 |
| 30544 | Trit1 | NM_025873.2 | chr4:122693839-122732177 |
| 30545 | Trmt1 | NM_001164559.1 | chr8:87213145-87223707 |
| 30546 | Trmt1 | NM_001164560.1 | chr8:87213145-87223707 |
| 30547 | Trmt1 | NM_198012.2 | chr8:87213145-87223707 |
| 30548 | Trmt10a | NM_175389.4 | chr3:137806501-137822784 |
| 30549 | Trmt10b | NM_027286.4 | chr4:45310039-45329003 |
| 30550 | Trmt10c | NM_029092.3 | chr16:56033832-56037887 |
| 30551 | Trmt11 | NM_028604.2 | chr10:30254030-30320555 |
| 30552 | Trmt112 | NM_001166370.1 | chr19:6984187-6996298 |
| 30553 | Trmt112 | NM_026306.3 | chr19:6984187-6996298 |
| 30554 | Trmt12 | NM_026642.2 | chr15:58704203-58708336 |
| 30555 | Trmt13 | NM_030016.1 | chr3:116284254-116317505 |
| 30556 | Trmt1l | NM_026876.3 | chr1:153275778-153305313 |
| 30557 | Trmt2a | NM_001080999.2 | chr16:18248975-18289261 |
| 30558 | Trmt2a | NM_001081000.2 | chr16:18248975-18289261 |
| 30559 | Trmt2a | NM_001195205.1 | chr16:18248975-18289261 |
| 30560 | Trmt2b | NM_001167994.1 | chrX:130757493-130811523 |
| 30561 | Trmt2b | NM_001167995.1 | chrX:130757493-130811523 |
| 30562 | Trmt2b | NM_172540.2 | chrX:130757493-130811523 |
| 30563 | Trmt44 | NM_030208.3 | chr5:35898857-35917719 |
| 30564 | Trmt5 | NM_029580.3 | chr12:74381396-74387698 |
| 30565 | Trmt6 | NM_175113.3 | chr2:132629950-132641790 |
| 30566 | Trmt61a | NM_001099792.1 | chr12:112916315-112922113 |
| 30567 | Trmt61a | NM_001099793.1 | chr12:112916315-112922113 |
| 30568 | Trmt61a | NM_177374.4 | chr12:112916315-112922113 |
| 30569 | Trmt61b | NR_015649.1 | chr17:71901400-71948101 |
| 30570 | Trmt61b | NR_027952.1 | chr17:71901400-71948101 |
| 30571 | Trmt61b | NR_027953.1 | chr17:71901400-71948101 |
| 30572 | Trmu | NM_028063.2 | chr15:85709756-85727823 |
| 30573 | Trnaulap | NM_027925.3 | chr4:131867577-131885453 |
| 30574 | Trnp1 | NM_001081156.2 | chr4:133047014-133054465 |
| 30575 | Trnt1 | NM_001242358.1 | chr6:106719131-106750081 |
| 30576 | Trnt1 | NM_001242360.1 | chr6:106719131-106750081 |
| 30577 | Trnt1 | NM_027296.3 | chr6:106719131-106750081 |
| 30578 | Tro | NM_001002272.3 | chrX:147079252-147092126 |
| 30579 | Tro | NM_001290770.1 | chrX:147079252-147092126 |
| 30580 | Tro | NM_001290771.1 | chrX:147079252-147092126 |
| 30581 | Tro | NM_001290772.1 | chrX:147079252-147092126 |
| 30582 | Tro | NM_019548.4 | chrX:147079252-147092126 |
| 30583 | Troap | NM_001162506.1 | chr15:98905403-98913840 |
| 30584 | Troap | NM_030139.1 | chr15:98905403-98913840 |
| 30585 | Trove2 | NM_013835.2 | chr1:145597920-145624181 |
| 30586 | Trp53 | NM_001127233.1 | chr11:69393860-69405375 |
| 30587 | Trp53 | NM_011640.3 | chr11:69393860-69405375 |
| 30588 | Trp53bp1 | NM_001290830.1 | chr2:120996903-121097143 |
| 30589 | Trp53bp1 | NM_013735.4 | chr2:120996903-121097143 |
| 30590 | Trp53bp2 | NM_173378.2 | chr1:184339297-184392567 |
| 30591 | Trp53cor1 | NR_036469.2 | chr17:29194418-29216071 |
| 30592 | Trp53i11 | NM_001024919.2 | chr2:93027740-93041914 |
| 30593 | Trp53i13 | NM_001024920.1 | chr11:77321600-77326775 |
| 30594 | Trp53inp1 | NM_001199105.1 | chr4:11083587-11101524 |
| 30595 | Trp53inp1 | NM_021897.3 | chr4:11083587-11101524 |
| 30596 | Trp53inp2 | NM_178111.3 | chr2:155207591-155215583 |
| 30597 | Trp53rk | NM_023815.4 | chr2:166619266-166624992 |
| 30598 | Trp53tg5 | NM_001271575.1 | chr2:164295803-164299224 |
| 30599 | Trp63 | NM_001127259.1 | chr16:25683850-25892174 |
| 30600 | Trp63 | NM_001127260.1 | chr16:25683850-25892174 |
| 30601 | Trp63 | NM_001127261.1 | chr16:25683850-25892174 |
| 30602 | Trp63 | NM_001127262.1 | chr16:25683850-25892174 |
| 30603 | Trp63 | NM_001127263.1 | chr16:25683850-25892174 |
| 30604 | Trp63 | NM_001127264.1 | chr16:25683850-25892174 |
| 30605 | Trp63 | NM_001127265.1 | chr16:25683850-25892174 |
| 30606 | Trp63 | NM_011641.2 | chr16:25683850-25892174 |
| 30607 | Trp73 | NM_001126330.1 | chr4:153430357-153514317 |
| 30608 | Trp73 | NM_001126331.1 | chr4:153430357-153514317 |
| 30609 | Trp73 | NM_011642.3 | chr4:153430357-153514317 |
| 30610 | Trpa1 | NM_177781.4 | chr1:14862728-14908943 |
| 30611 | Trpc1 | NM_011643.2 | chr9:95607047-95650777 |
| 30612 | Trpc2 | NM_001109897.2 | chr7:109231630-109245378 |
| 30613 | Trpc3 | NM_019510.2 | chr3:36519403-36589089 |
| 30614 | Trpc4 | NM_001253682.1 | chr3:53959978-54122393 |
| 30615 | Trpc4 | NM_001253683.1 | chr3:53959978-54122393 |
| 30616 | Trpc4 | NM_016984.3 | chr3:53959978-54122393 |
| 30617 | Trpc4 | NR_046161.1 | chr3:53959978-54122393 |
| 30618 | Trpc4ap | NM_001163452.1 | chr2:155436978-155518120 |
| 30619 | Trpc4ap | NM_019828.2 | chr2:155436978-155518120 |
| 30620 | Trpc5 | NM_009428.2 | chrX:140816214-141122723 |
| 30621 | Trpc5os | NM_001195579.1 | chrX:140891125-140911606 |
| 30622 | Trpc6 | NM_001282086.1 | chr9:8544141-8740988 |
| 30623 | Trpc6 | NM_001282087.1 | chr9:8544141-8740988 |
| 30624 | Trpc6 | NM_013838.2 | chr9:8544141-8740988 |
| 30625 | Trpc7 | NM_012035.3 | chr13:56874468-56996949 |
| 30626 | Trpd52l3 | NM_025741.2 | chr19:30078279-30080510 |
| 30627 | Trpm1 | NM_001039104.2 | chr7:71298720-71414645 |
| 30628 | Trpm1 | NM_018752.3 | chr7:71298720-71414645 |
| 30629 | Trpm2 | NM_138301.2 | chr10:77370466-77432617 |
| 30630 | Trpm3 | NM_001035239.2 | chr19:22213606-23064374 |
| 30631 | Trpm3 | NM_001035240.2 | chr19:22213606-23064374 |
| 30632 | Trpm3 | NM_001035241.2 | chr19:22213606-23064374 |
| 30633 | Trpm3 | NM_001035242.1 | chr19:22213606-23064374 |
| 30634 | Trpm3 | NM_001035243.2 | chr19:22213606-23064374 |
| 30635 | Trpm3 | NM_001035244.1 | chr19:22213606-23064374 |
| 30636 | Trpm3 | NM_001035245.1 | chr19:22213606-23064374 |
| 30637 | Trpm3 | NM_001035246.1 | chr19:22213606-23064374 |
| 30638 | Trpm3 | NM_177341.4 | chr19:22213606-23064374 |
| 30639 | Trpm4 | NM_175130.4 | chr7:52558525-52589150 |
| 30640 | Trpm5 | NM_020277.2 | chr7:150257433-150280547 |
| 30641 | Trpm6 | NM_153417.1 | chr19:18824472-18967001 |
| 30642 | Trpm7 | NM_001164215.1 | chr2:126617293-126701997 |
| 30643 | Trpm7 | NM_021450.2 | chr2:126617293-126701997 |
| 30644 | Trpm8 | NM_134252.3 | chr1:90203286-90285426 |
| 30645 | Trps1 | NM_032000.2 | chr15:50486305-50721587 |
| 30646 | Trpt1 | NM_153597.2 | chr19:7070620-7093959 |
| 30647 | Trpt1 | NR_027351.1 | chr19:7070620-7093959 |
| 30648 | Trpv1 | NM_001001445.2 | chr11:73051760-73074009 |
| 30649 | Trpv2 | NM_011706.2 | chr11:62387987-62413807 |
| 30650 | Trpv3 | NM_145099.2 | chr11:73081121-73110702 |
| 30651 | Trpv4 | NM_022017.3 | chr5:115072162-115108430 |
| 30652 | Trpv5 | NM_001007572.2 | chr6:41602768-41630722 |
| 30653 | Trpv6 | NM_022413.4 | chr6:41570617-41586404 |
| 30654 | Trrap | NM_001081362.1 | chr5:145529660-145620642 |
| 30655 | Trub1 | NM_028115.1 | chr19:57527395-57565495 |
| 30656 | Trub1 | NM_029839.3 | chr19:57527395-57565495 |
| 30657 | Trub2 | NM_001290495.1 | chr2:29630203-29643191 |
| 30658 | Trub2 | NM_001290496.1 | chr2:29630203-29643191 |
| 30659 | Trub2 | NM_145520.5 | chr2:29630203-29643191 |
| 30660 | Trub2 | NR_027344.1 | chr2:29630203-29643191 |
| 30661 | Trub2 | NR_110962.1 | chr2:29630203-29643191 |
| 30662 | Try10 | NM_001038996.2 | chr6:41304103-41307943 |
| 30663 | Try4 | NM_011646.5 | chr6:41252270-41255532 |
| 30664 | Try5 | NM_001003405.4 | chr6:41261230-41264709 |
| 30665 | Tsacc | NM_029801.2 | chr3:88086681-88100760 |
| 30666 | Tsc1 | NM_001289575.1 | chr2:28496752-28546692 |
| 30667 | Tsc1 | NM_001289576.1 | chr2:28496752-28546692 |
| 30668 | Tsc1 | NM_022887.4 | chr2:28496752-28546692 |
| 30669 | Tsc2 | NM_001039363.2 | chr17:24686894-24769572 |
| 30670 | Tsc2 | NM_001286713.1 | chr17:24686894-24769572 |
| 30671 | Tsc2 | NM_001286714.1 | chr17:24686894-24769572 |
| 30672 | Tsc2 | NM_001286716.1 | chr17:24686894-24769572 |
| 30673 | Tsc2 | NM_001286718.1 | chr17:24686894-24769572 |
| 30674 | Tsc2 | NM_001286720.1 | chr17:24686894-24769572 |
| 30675 | Tsc2 | NM_011647.3 | chr17:24686894-24769572 |
| 30676 | Tsc22d1 | NM_001177751.1 | chr14:76815627-76907573 |
| 30677 | Tsc22d1 | NM_009366.2 | chr14:76815627-76907573 |
| 30678 | Tsc22d1 | NM_207652.2 | chr14:76815627-76907573 |
| 30679 | Tsc22d2 | NM_001081229.1 | chr3:58219610-58270709 |
| 30680 | Tsc22d3 | NM_001077364.1 | chrX:137074067-137135061 |
| 30681 | Tsc22d3 | NM_010286.4 | chrX:137074067-137135061 |
| 30682 | Tsc22d4 | NM_023910.6 | chr5:138187196-138209681 |
| 30683 | Tsc22d4 | NM_029805.1 | chr5:138187196-138209681 |
| 30684 | Tsen15 | NM_025677.2 | chr1:154217865-154233812 |
| 30685 | Tsen2 | NM_199033.1 | chr6:115494721-115528354 |
| 30686 | Tsen34 | NM_001164204.1 | chr7:3645211-3652637 |
| 30687 | Tsen34 | NM_001164205.1 | chr7:3645211-3652637 |
| 30688 | Tsen34 | NM_024168.2 | chr7:3645211-3652637 |
| 30689 | Tsen54 | NM_029557.1 | chr11:115676052-115684416 |
| 30690 | Tsfm | NM_025537.3 | chr10:126459387-126467870 |
| 30691 | Tsg101 | NM_021884.3 | chr7:54144396-54175300 |
| 30692 | Tsga10 | NM_001290720.1 | chr1:37811416-37922143 |
| 30693 | Tsga10 | NM_001290721.1 | chr1:37811416-37922143 |
| 30694 | Tsga10 | NM_207228.3 | chr1:37811416-37922143 |
| 30695 | Tsga10 | NR_110976.1 | chr1:37811416-37922143 |

Fig. 25 - 163

| | | | |
|---|---|---|---|
| 30696 | Tsga13 | NM_054073.2 | chr6:30846980-30865573 |
| 30697 | Tsga8 | NM_021898.2 | chrX:80732015-80733263 |
| 30698 | Tshb | NM_001165939.1 | chr3:102581320-102586637 |
| 30699 | Tshb | NM_001165940.1 | chr3:102581320-102586637 |
| 30700 | Tshb | NM_009432.2 | chr3:102581320-102586637 |
| 30701 | Tshr | NM_001113404.1 | chr12:92236931-92786285 |
| 30702 | Tshr | NM_011648.5 | chr12:92236931-92786285 |
| 30703 | Tshz1 | NM_001081300.1 | chr18:84181018-84255954 |
| 30704 | Tshz2 | NM_080455.2 | chr2:169459145-169714004 |
| 30705 | Tshz3 | NM_172298.2 | chr7:37483136-37558476 |
| 30706 | Tsix | NR_002844.2 | chrX:100626856-100680296 |
| 30707 | Tsks | NM_001077591.1 | chr7:52198609-52213405 |
| 30708 | Tsks | NM_011651.2 | chr7:52198609-52213405 |
| 30709 | Tsku | NM_001024619.3 | chr7:105499177-105509838 |
| 30710 | Tsku | NM_001168539.1 | chr7:105499177-105509838 |
| 30711 | Tsku | NM_001168540.1 | chr7:105499177-105509838 |
| 30712 | Tsku | NM_001168541.1 | chr7:105499177-105509838 |
| 30713 | Tslp | NM_021367.2 | chr18:32823295-33026074 |
| 30714 | Tslp | NR_033206.1 | chr18:32823295-33026074 |
| 30715 | Tsn | NM_011650.3 | chr1:120195094-120207709 |
| 30716 | Tsnax | NM_016909.2 | chr8_random:580369-601515 |
| 30717 | Tsnax | NM_016909.2 | chr8:127536896-127558092 |
| 30718 | Tsnaxip1 | NM_024445.4 | chr8:108351643-108368576 |
| 30719 | Tspan1 | NM_133681.4 | chr4:115834485-115840203 |
| 30720 | Tspan10 | NM_145363.2 | chr11:120303944-120308635 |
| 30721 | Tspan11 | NM_026743.3 | chr6:127837839-127903049 |
| 30722 | Tspan12 | NM_173007.3 | chr6:21721394-21802515 |
| 30723 | Tspan13 | NM_025359.3 | chr12:36741141-36769065 |
| 30724 | Tspan14 | NM_145928.1 | chr14:41719732-41780096 |
| 30725 | Tspan15 | NM_197996.2 | chr10:61648144-61693966 |
| 30726 | Tspan17 | NM_028841.3 | chr13:54890765-54898136 |
| 30727 | Tspan18 | NM_183180.2 | chr2:93041916-93174644 |
| 30728 | Tspan2 | NM_001243132.1 | chr3:102524153-102576233 |
| 30729 | Tspan2 | NM_027533.3 | chr3:102524153-102576233 |
| 30730 | Tspan2os | NR_040588.1 | chr3:102524154-102539340 |
| 30731 | Tspan3 | NM_019793.3 | chr9:55983690-56008877 |
| 30732 | Tspan31 | NM_025982.4 | chr10:126504345-126507317 |
| 30733 | Tspan32 | NM_001128080.2 | chr7:150190950-150205390 |
| 30734 | Tspan32 | NM_001128081.1 | chr7:150190950-150205390 |
| 30735 | Tspan32 | NM_001128082.1 | chr7:150190950-150205390 |
| 30736 | Tspan32 | NM_020286.3 | chr7:150190950-150205390 |
| 30737 | Tspan33 | NM_146173.3 | chr6:29644255-29668558 |
| 30738 | Tspan4 | NM_001252588.1 | chr7:148661134-148725756 |
| 30739 | Tspan4 | NM_053082.3 | chr7:148661134-148725756 |
| 30740 | Tspan5 | NM_019571.5 | chr3:138405158-138567388 |
| 30741 | Tspan6 | NM_019656.3 | chrX:130425608-130432968 |
| 30742 | Tspan7 | NM_019634.2 | chrX:10062241-10173730 |
| 30743 | Tspan8 | NM_001168679.1 | chr10:115254339-115286949 |
| 30744 | Tspan8 | NM_001168680.1 | chr10:115254339-115286949 |
| 30745 | Tspan8 | NM_146010.2 | chr10:115254339-115286949 |
| 30746 | Tspan9 | NM_175414.4 | chr6:127911417-128093596 |
| 30747 | Tspear | NM_001287074.1 | chr10:77149314-77349514 |
| 30748 | Tspo | NM_009775.4 | chr15:83394002-83404633 |
| 30749 | Tspo2 | NM_027292.2 | chr17:48587759-48590826 |
| 30750 | Tspyl1 | NM_009433.3 | chr10:34001995-34004691 |
| 30751 | Tspyl2 | NM_029836.3 | chrX:148771394-148777027 |
| 30752 | Tspyl3 | NM_198617.2 | chr2:153048105-153051177 |
| 30753 | Tspyl4 | NM_030203.2 | chr10:34017226-34021126 |
| 30754 | Tspyl5 | NM_001085421.1 | chr15:33613629-33617638 |
| 30755 | Tspy-ps | NR_027507.1 | chrY:392206-395311 |
| 30756 | Tsr1 | NM_177325.3 | chr11:74711582-74722842 |
| 30757 | Tsr2 | NM_001164578.1 | chrX:147481712-147531086 |
| 30758 | Tsr2 | NM_175146.4 | chrX:147481712-147531086 |
| 30759 | Tsr2 | NR_028392.1 | chrX:147481712-147531086 |
| 30760 | Tsr3 | NM_001163718.1 | chr17:25377114-25393309 |
| 30761 | Tsr3 | NM_026676.3 | chr17:25377114-25393309 |
| 30762 | Tssc1 | NM_201357.2 | chr12:29436692-29552356 |
| 30763 | Tssc4 | NM_001115085.1 | chr7:150255272-150256992 |
| 30764 | Tssc4 | NM_020285.2 | chr7:150255272-150256992 |
| 30765 | Tssc4 | NM_138631.1 | chr7:150255272-150256992 |
| 30766 | Tssk1 | NM_009435.2 | chr16:17894295-17895746 |
| 30767 | Tssk2 | NM_009436.2 | chr16:17898729-17900117 |
| 30768 | Tssk3 | NM_080442.2 | chr4:129166251-129168014 |
| 30769 | Tssk4 | NM_001253888.1 | chr14:56269020-56271376 |
| 30770 | Tssk4 | NM_001253889.1 | chr14:56269020-56271376 |
| 30771 | Tssk4 | NM_027673.3 | chr14:56269020-56271376 |
| 30772 | Tssk5 | NM_183099.2 | chr15:76202387-76205368 |
| 30773 | Tssk6 | NM_032004.1 | chr8:72426114-72427417 |
| 30774 | Tst | NM_009437.4 | chr15:78229985-78236289 |
| 30775 | Tsta3 | NM_031201.1 | chr15:75755112-75760160 |
| 30776 | Tstd1 | NM_001164525.1 | chr1:173349163-173350483 |
| 30777 | Tstd2 | NM_173033.3 | chr4:46127619-46151347 |
| 30778 | Tstd3 | NM_029840.1 | chr4:21684529-21694358 |
| 30779 | Tsx | NM_009440.2 | chrX:100609805-100619922 |
| 30780 | Ttbk1 | NM_001162864.1 | chr17:46579396-46624624 |
| 30781 | Ttbk2 | NM_001024856.2 | chr2:120558551-120676320 |
| 30782 | Ttbk2 | NM_001024857.2 | chr2:120558551-120676320 |
| 30783 | Ttbk2 | NM_080788.3 | chr2:120558551-120676320 |
| 30784 | Ttc1 | NM_133795.1 | chr11:43543507-43561475 |
| 30785 | Ttc12 | NM_172770.3 | chr9:49245065-49294330 |
| 30786 | Ttc13 | NM_145607.3 | chr8:127195226-127245875 |
| 30787 | Ttc14 | NM_001290500.1 | chr3:33699104-33743232 |
| 30788 | Ttc14 | NM_001290502.1 | chr3:33699104-33743232 |
| 30789 | Ttc14 | NM_025978.4 | chr3:33699104-33743232 |
| 30790 | Ttc14 | NM_027619.4 | chr3:33699104-33743232 |
| 30791 | Ttc16 | NM_001290563.1 | chr2:32612545-32631153 |
| 30792 | Ttc16 | NM_001290564.1 | chr2:32612545-32631153 |
| 30793 | Ttc16 | NM_001290566.1 | chr2:32612545-32631153 |
| 30794 | Ttc16 | NM_001290567.1 | chr2:32612545-32631153 |
| 30795 | Ttc16 | NM_177384.3 | chr2:32612545-32631153 |
| 30796 | Ttc17 | NM_183106.2 | chr2:94140922-94246846 |
| 30797 | Ttc18 | NM_001163638.1 | chr14:21213411-21271447 |
| 30798 | Ttc18 | NM_001163639.1 | chr14:21213411-21271447 |
| 30799 | Ttc18 | NM_029698.1 | chr14:21213411-21271447 |
| 30800 | Ttc19 | NM_028360.2 | chr11:62094974-62270834 |
| 30801 | Ttc19 | NM_029704.2 | chr11:62094974-62270834 |
| 30802 | Ttc21a | NM_028735.3 | chr9:119846723-119876911 |
| 30803 | Ttc21b | NM_001047604.2 | chr2:66022383-66094674 |
| 30804 | Ttc21b | NM_001290669.1 | chr2:66022383-66094674 |
| 30805 | Ttc22 | NM_177667.4 | chr4:106295053-106312792 |
| 30806 | Ttc23 | NM_001168475.1 | chr7:74792295-74871462 |
| 30807 | Ttc23 | NM_001168476.1 | chr7:74792295-74871462 |
| 30808 | Ttc23 | NM_001168477.1 | chr7:74792295-74871462 |
| 30809 | Ttc23 | NM_025905.3 | chr7:74792295-74871462 |
| 30810 | Ttc23l | NM_029430.1 | chr15:10433701-10488423 |
| 30811 | Ttc24 | NM_172526.3 | chr3:87873331-87882226 |
| 30812 | Ttc25 | NM_028918.2 | chr11:100406945-100433880 |
| 30813 | Ttc26 | NM_153600.2 | chr6:38331523-38377647 |
| 30814 | Ttc27 | NM_152817.4 | chr17:75117089-75262910 |
| 30815 | Ttc28 | NM_001267622.1 | chr5:111308822-111718799 |
| 30816 | Ttc29 | NM_183096.3 | chr8:80737240-80918225 |
| 30817 | Ttc3 | NM_009441.1 | chr16:94592346-94690828 |
| 30818 | Ttc30a1 | NM_030188.3 | chr2:75817162-75820024 |
| 30819 | Ttc30a2 | NM_001081228.1 | chr2:75814228-75816236 |
| 30820 | Ttc30b | NM_028235.1 | chr2:75773906-75776519 |
| 30821 | Ttc32 | NM_029321.2 | chr12:9036802-9043200 |
| 30822 | Ttc33 | NM_026213.3 | chr15:5135559-5168332 |
| 30823 | Ttc34 | NM_172878.3 | chr4:154230308-154241236 |
| 30824 | Ttc36 | NM_138951.1 | chr9:44607482-44611034 |
| 30825 | Ttc37 | NM_001081352.1 | chr13:76236181-76325431 |
| 30826 | Ttc38 | NM_001033337.4 | chr15:85662733-85689252 |
| 30827 | Ttc39a | NM_001145948.1 | chr4:109079704-109117350 |
| 30828 | Ttc39a | NM_153392.2 | chr4:109079704-109117350 |
| 30829 | Ttc39b | NM_027238.2 | chr4:82866204-82970093 |
| 30830 | Ttc39c | NM_028341.4 | chr18:12802042-12895561 |
| 30831 | Ttc39d | NM_026351.2 | chr17:80615253-80617276 |
| 30832 | Ttc4 | NM_001172073.1 | chr4:106334412-106351549 |
| 30833 | Ttc4 | NM_028209.2 | chr4:106334412-106351549 |
| 30834 | Ttc5 | NM_001080949.2 | chr14:51385083-51405195 |
| 30835 | Ttc5 | NM_177625.4 | chr14:51385083-51405195 |
| 30836 | Ttc7 | NM_028639.3 | chr17:87682225-87781110 |
| 30837 | Ttc7b | NM_001033213.1 | chr12:101538980-101759032 |
| 30838 | Ttc8 | NM_029553.3 | chr12:100158783-100221448 |
| 30839 | Ttc8 | NM_198311.1 | chr12:100158783-100221448 |
| 30840 | Ttc9 | NM_001033149.2 | chr12:82732355-82765928 |
| 30841 | Ttc9b | NM_028417.1 | chr7:28438942-28441226 |
| 30842 | Ttc9c | NM_027412.3 | chr19:8883564-8893784 |
| 30843 | Ttf1 | NM_009442.2 | chr2:28915782-28943170 |
| 30844 | Ttf2 | NM_001013026.2 | chr3:100742782-100773586 |
| 30845 | Tth1 | NM_029282.1 | chr2:157807538-157835096 |
| 30846 | Tti1 | NM_001199988.1 | chr8:32260787-32279196 |
| 30847 | Tti2 | NM_144927.3 | chr8:32260787-32279196 |
| 30848 | Tti2 | NR_103719.1 | chr8:32260787-32279196 |
| 30849 | Ttk | NM_001110265.1 | chr9:83728295-83765997 |
| 30850 | Ttk | NM_001284272.1 | chr9:83728295-83765997 |
| 30851 | Ttk | NM_009445.2 | chr9:83728295-83765997 |
| 30852 | Ttl | NM_027192.2 | chr2:128891682-128922019 |
| 30853 | Ttll1 | NM_178869.4 | chr15:83314198-83341337 |
| 30854 | Ttll10 | NM_029264.2 | chr4:155408945-155424926 |
| 30855 | Ttll11 | NM_029774.2 | chr2:35606746-35835144 |
| 30856 | Ttll12 | NM_183017.2 | chr15:83405523-83425587 |
| 30857 | Ttll13 | NM_177765.3 | chr7:87391261-87405707 |
| 30858 | Ttll2 | NM_001098267.1 | chr17:7555252-7557045 |
| 30859 | Ttll3 | NM_001142732.1 | chr6:113328106-113364565 |
| 30860 | Ttll3 | NM_133923.6 | chr6:113328106-113364565 |
| 30861 | Ttll4 | NM_001014974.1 | chr1:74708327-74744547 |
| 30862 | Ttll5 | NM_001081423.2 | chr12:87165899-87394710 |
| 30863 | Ttll6 | NM_172799.4 | chr11:95995099-96026766 |
| 30864 | Ttll7 | NM_027594.1 | chr3:146515330-146645714 |
| 30865 | Ttll8 | NM_172818.3 | chr15:88744327-88784848 |
| 30866 | Ttll9 | NM_001083618.1 | chr2:152788220-152834218 |
| 30867 | Ttll9 | NM_029064.2 | chr2:152788220-152834218 |
| 30868 | Ttn | NM_011652.3 | chr2:76542040-76820604 |
| 30869 | Ttn | NM_028004.2 | chr2:76542040-76820604 |
| 30870 | Ttpa | NM_015767.3 | chr4:19935574-19957932 |
| 30871 | Ttpal | NM_029512.2 | chr2:163428049-163444749 |
| 30872 | Ttpal | NM_181734.3 | chr2:163428049-163444749 |
| 30873 | Ttr | NM_013697.5 | chr18:20823750-20832827 |
| 30874 | Ttyh1 | NM_001001454.4 | chr7:4025726-4088528 |
| 30875 | Ttyh1 | NM_001109765.2 | chr7:4025726-4088528 |
| 30876 | Ttyh1 | NM_021324.6 | chr7:4025726-4088528 |
| 30877 | Ttyh2 | NM_053273.2 | chr11:114536781-114582298 |
| 30878 | Ttyh3 | NM_175274.5 | chr5:141096531-141124985 |
| 30879 | Tub | NM_021885.4 | chr7:116154394-116177973 |
| 30880 | Tuba1a | NM_011653.2 | chr15:98780277-98783932 |
| 30881 | Tuba1b | NM_011654.2 | chr15:98761861-98764821 |
| 30882 | Tuba1c | NM_009448.4 | chr15:98860321-98868536 |
| 30883 | Tuba3a | NM_009446.2 | chr6:125228291-125236060 |
| 30884 | Tuba3b | NM_009449.2 | chr6:145564482-145569997 |
| 30885 | Tuba4a | NM_009447.3 | chr1:75211549-75215828 |

Fig. 25 - 164

| | | | | | | |
|---|---|---|---|---|---|---|
| 30886 | Tuba8 | NM_017379.1 | chr6:121160787-121176115 | 30981 | Txnrd1 | NM_015762.2 | chr10:82296695-82360469 |
| 30887 | Tubal3 | NM_001033879.3 | chr13:3923940-3934523 | 30982 | Txnrd2 | NM_013711.3 | chr16:18426510-18479166 |
| 30888 | Tubb1 | NM_001080971.2 | chr2:174276095-174283881 | 30983 | Txnrd3 | NM_001178058.1 | chr6:89593981-89625523 |
| 30889 | Tubb2a | NM_009450.2 | chr13:34166146-34169877 | 30984 | Txnrd3 | NM_001178060.1 | chr6:89593981-89625523 |
| 30890 | Tubb2a-ps2 | NR_003964.2 | chr12:11889001-11889705 | 30985 | Tyk2 | NM_001205312.1 | chr9:20908511-20935719 |
| 30891 | Tubb2b | NM_023716.2 | chr13:34218876-34222223 | 30986 | Tyk2 | NM_018793.2 | chr9:20908511-20935719 |
| 30892 | Tubb3 | NM_023279.2 | chr8:125935463-125945910 | 30987 | Tymp | NM_138302.1 | chr15:89202362-89207468 |
| 30893 | Tubb4a | NM_009451.3 | chr17:57219488-57227205 | 30988 | Tyms | NM_021288.4 | chr5:30384739-30400165 |
| 30894 | Tubb4b | NM_146116.2 | chr2:25077678-25080222 | 30989 | Tyms | NR_033402.1 | chr5:30384739-30400165 |
| 30895 | Tubb5 | NM_011655.5 | chr17:35970864-35975246 | 30990 | Tyms-ps | NR_000040.1 | chr10:87429415-87430762 |
| 30896 | Tubb6 | NM_026473.2 | chr18:67550384-67562403 | 30991 | Tyr | NM_011661.4 | chr7:94575914-94641921 |
| 30897 | Tubd1 | NM_001199045.1 | chr11:86358492-86380862 | 30992 | Tyro3 | NM_001290800.1 | chr2:119623475-119643839 |
| 30898 | Tubd1 | NM_001199046.1 | chr11:86358492-86380862 | 30993 | Tyro3 | NM_019392.2 | chr2:119623475-119643839 |
| 30899 | Tubd1 | NM_001199047.1 | chr11:86358492-86380862 | 30994 | Tyrobp | NM_011662.2 | chr7:31198806-31202598 |
| 30900 | Tubd1 | NM_019756.3 | chr11:86358492-86380862 | 30995 | Tyrp1 | NM_001282014.1 | chr4:80480116-80497640 |
| 30901 | Tube1 | NM_028006.2 | chr10:38853829-38870864 | 30996 | Tyrp1 | NM_001282015.1 | chr4:80480116-80497640 |
| 30902 | Tubg1 | NM_134024.2 | chr11:100981444-100987733 | 30997 | Tyrp1 | NM_031202.3 | chr4:80480116-80497640 |
| 30903 | Tubg2 | NM_134028.2 | chr11:101017197-101023101 | 30998 | Tysnd1 | NM_001272090.1 | chr10:61158261-61165521 |
| 30904 | Tubgcp2 | NM_001286007.1 | chr7:147181853-147226504 | 30999 | Tysnd1 | NM_001272091.1 | chr10:61158261-61165521 |
| 30905 | Tubgcp2 | NM_001286009.1 | chr7:147181853-147226504 | 31000 | Tysnd1 | NM_001272092.1 | chr10:61158261-61165521 |
| 30906 | Tubgcp2 | NM_001286011.1 | chr7:147181853-147226504 | 31001 | Tysnd1 | NM_027912.1 | chr10:61158261-61165521 |
| 30907 | Tubgcp2 | NM_133755.2 | chr7:147181853-147226504 | 31002 | Tysnd1 | NR_073587.1 | chr10:61158261-61165521 |
| 30908 | Tubgcp3 | NM_198031.1 | chr8:12614276-12672100 | 31003 | Tyw1 | NM_001015876.2 | chr5:130731488-130817437 |
| 30909 | Tubgcp4 | NM_001290824.1 | chr2:120996903-121097143 | 31004 | Tyw1 | NM_178897.4 | chr5:130731488-130817437 |
| 30910 | Tubgcp4 | NM_153387.3 | chr2:120996903-121097143 | 31005 | Tyw3 | NM_001168358.1 | chr3:154239483-154286146 |
| 30911 | Tubgcp4 | NR_077245.2 | chr2:120996903-121097143 | 31006 | Tyw3 | NM_172474.5 | chr3:154239483-154286146 |
| 30912 | Tubgcp4 | NR_110985.1 | chr2:120996903-121097143 | 31007 | Tyw5 | NM_001037742.2 | chr1:57445087-57472802 |
| 30913 | Tubgcp5 | NM_146190.2 | chr7:63049517-63086817 | 31008 | Tyw5 | NM_001114102.1 | chr1:57445087-57472802 |
| 30914 | Tubgcp6 | NM_001183319.1 | chr15:88929528-88953580 | 31009 | Tyw5 | NR_004860.1 | chr1:57445087-57472802 |
| 30915 | Tufm | NM_001163713.1 | chr7:133630868-133634245 | 31010 | U2af1 | NM_001163769.1 | chr17:31784026-31795699 |
| 30916 | Tufm | NM_172475.3 | chr7:133630868-133634245 | 31011 | U2af1 | NM_024187.4 | chr17:31784026-31795699 |
| 30917 | Tuft1 | NM_011656.3 | chr3:94416680-94462728 | 31012 | U2af1l4 | NM_170760.3 | chr7:31348358-31350383 |
| 30918 | Tug1 | NR_002321.2 | chr11:3539787-3548817 | 31013 | U2af2 | NM_001205231.1 | chr7:5013744-5031547 |
| 30919 | Tug1 | NR_002322.2 | chr11:3539787-3548817 | 31014 | U2af2 | NM_133671.2 | chr7:5013744-5031547 |
| 30920 | Tug1 | NR_110480.1 | chr11:3539787-3548817 | 31015 | U2surp | NM_001114977.1 | chr9:95357312-95412415 |
| 30921 | Tulp1 | NM_021478.1 | chr17:28488463-28502088 | 31016 | U2surp | NM_026476.2 | chr9:95357312-95412415 |
| 30922 | Tulp2 | NM_001045555.2 | chr7:52728932-52777973 | 31017 | U90926 | NR_033483.1 | chr5:92638920-92644434 |
| 30923 | Tulp2 | NM_001290996.2 | chr7:52728932-52777973 | 31018 | Uaca | NM_028283.2 | chr9:60642354-60728177 |
| 30924 | Tulp2 | NM_001290998.2 | chr7:52728932-52777973 | 31019 | Uap1 | NM_133806.5 | chr1:172072133-172105077 |
| 30925 | Tulp2 | NM_001290999.2 | chr7:52728932-52777973 | 31020 | Uap1l1 | NM_001033293.2 | chr2:25217011-25221146 |
| 30926 | Tulp2 | NM_008807.3 | chr7:52728932-52777973 | 31021 | Uba1 | NM_001136085.2 | chrX:20235427-20260305 |
| 30927 | Tulp3 | NM_011657.2 | chr6:128271178-128305869 | 31022 | Uba1 | NM_001276316.1 | chrX:20235427-20260305 |
| 30928 | Tulp4 | NM_001103181.1 | chr17:6106829-6240637 | 31023 | Uba1 | NM_001276317.1 | chrX:20235427-20260305 |
| 30929 | Tulp4 | NM_054040.3 | chr17:6106829-6240637 | 31024 | Uba1 | NM_009457.4 | chrX:20235427-20260305 |
| 30930 | Tunar | NR_045047.1 | chr12:106574803-106622142 | 31025 | Uba1y | NM_011667.2 | chrY_random:43172477-4319 7989 |
| 30931 | Tusc1 | NM_026954.1 | chr4:93000838-93002202 | 31026 | Uba1y | NM_011667.2 | chrY:155155-180667 |
| 30932 | Tusc2 | NM_019742.4 | chr9:107465585-107468439 | 31027 | Uba2 | NM_016682.2 | chr7:34925715-34953548 |
| 30933 | Tusc3 | NM_030254.3 | chr8:40068920-40250468 | 31028 | Uba3 | NM_001111106.2 | chr6:97133809-97155636 |
| 30934 | Tusc5 | NM_177709.3 | chr11:76493374-76512166 | 31029 | Uba3 | NM_011666.3 | chr6:97133809-97155636 |
| 30935 | Tut1 | NM_197993.2 | chr19:9028339-9040700 | 31030 | Uba5 | NM_025692.3 | chr9:103948917-103965451 |
| 30936 | Tvp23a | NM_001013778.1 | chr16:10420652-10447443 | 31031 | Uba52 | NM_019883.3 | chr8:73032164-73034266 |
| 30937 | Tvp23b | NM_026210.4 | chr11:62692991-62708686 | 31032 | Uba6 | NM_172712.2 | chr5:86539753-86601768 |
| 30938 | Twf1 | NM_008971.4 | chr15:94408378-94420255 | 31033 | Uba7 | NM_023738.4 | chr9:107877897-107886387 |
| 30939 | Twf2 | NM_011876.3 | chr9:106105438-106117718 | 31034 | Ubac1 | NM_133835.2 | chr2:25852477-25877280 |
| 30940 | Twist1 | NM_011658.2 | chr12:34642535-34644696 | 31035 | Ubac2 | NM_026861.2 | chr14:122277828-122420257 |
| 30941 | Twist2 | NM_007855.2 | chr1:93698053-93744604 | 31036 | Ubald1 | NM_145359.2 | chr16:4874778-4879851 |
| 30942 | Twistnb | NM_172253.2 | chr12:34114488-34124245 | 31037 | Ubald2 | NM_176902.3 | chr11:116295408-116300391 |
| 30943 | Twsg1 | NM_023053.3 | chr17:66272404-66300527 | 31038 | Ubap1 | NM_001290454.1 | chr4:41296028-41336799 |
| 30944 | Txk | NM_001227754.2 | chr5:73087216-73144016 | 31039 | Ubap1 | NM_023305.3 | chr4:41296028-41336799 |
| 30945 | Txk | NM_001289494.1 | chr5:73087216-73144016 | 31040 | Ubap1l | NM_001111145.1 | chr9:65208866-65228184 |
| 30946 | Txk | NM_001289495.1 | chr5:73087216-73144016 | 31041 | Ubap2 | NM_026872.1 | chr4:41141347-41222168 |
| 30947 | Txk | NM_013698.3 | chr5:73087216-73144016 | 31042 | Ubap2l | NM_001165983.1 | chr3:89802681-89872269 |
| 30948 | Txlna | NM_001005506.3 | chr4:129303320-129318309 | 31043 | Ubap2l | NM_001165984.1 | chr3:89802681-89872269 |
| 30949 | Txlna | NM_001199695.1 | chr4:129303320-129318309 | 31044 | Ubap2l | NM_001165985.1 | chr3:89802681-89872269 |
| 30950 | Txlnb | NM_138628.3 | chr10:17516024-17565469 | 31045 | Ubap2l | NM_001165986.1 | chr3:89802681-89872269 |
| 30951 | Txlng | NM_001290776.1 | chrX:159198303-159267386 | 31046 | Ubap2l | NM_001165987.1 | chr3:89802681-89872269 |
| 30952 | Txlng | NM_001290777.1 | chrX:159198303-159267386 | 31047 | Ubap2l | NM_001165988.1 | chr3:89802681-89872269 |
| 30953 | Txlng | NM_001290778.1 | chrX:159198303-159267386 | 31048 | Ubap2l | NM_028475.2 | chr3:89802681-89872269 |
| 30954 | Txlng | NM_178935.5 | chrX:159198303-159267386 | 31049 | Ubap2l | NM_153489.2 | chr3:89802681-89872269 |
| 30955 | Txn1 | NM_011660.3 | chr4:57956244-57969283 | 31050 | Ubash3a | NM_177823.4 | chr17:31345010-31379348 |
| 30956 | Txn2 | NM_019913.5 | chr15:77745486-77759424 | 31051 | Ubash3b | NM_176860.1 | chr9:40821723-40965577 |
| 30957 | Txndc11 | NM_029582.2 | chr16:11066390-11134625 | 31052 | Ubb | NM_011664.3 | chr11:62365005-62366714 |
| 30958 | Txndc11 | NM_134105.2 | chr16:11066390-11134625 | 31053 | Ubc | NM_019639.4 | chr5:125866334-125870387 |
| 30959 | Txndc12 | NM_025334.3 | chr4:108507283-108534724 | 31054 | Ubd | NM_023137.3 | chr17:37330836-37333046 |
| 30960 | Txndc15 | NM_175150.3 | chr13:55816010-55827588 | 31055 | Ube2a | NM_019668.3 | chrX:34414360-34424215 |
| 30961 | Txndc16 | NM_172567.2 | chr14:45754122-45839609 | 31056 | Ube2b | NM_009458.4 | chr11:51798647-51813968 |
| 30962 | Txndc17 | NM_026559.3 | chr11:72021055-72023989 | 31057 | Ube2c | NM_026785.2 | chr2:164595428-164598402 |
| 30963 | Txndc2 | NM_001146002.1 | chr17:65986844-65991544 | 31058 | Ube2cbp | NM_027394.2 | chr9:86200840-86358523 |
| 30964 | Txndc2 | NM_153519.2 | chr17:65986844-65991544 | 31059 | Ube2d1 | NM_145420.1 | chr10:70717727-70748010 |
| 30965 | Txndc5 | NM_001289598.1 | chr13:38592139-38620693 | 31060 | Ube2d2a | NM_019912.2 | chr18:35931212-35966826 |
| 30966 | Txndc5 | NM_001289599.1 | chr13:38592139-38620693 | 31061 | Ube2d2b | NM_001276397.1 | chr5:108259181-108260796 |
| 30967 | Txndc5 | NM_145453.4 | chr13:38592139-38620693 | 31062 | Ube2d3 | NM_025356.4 | chr3:135101722-135130142 |
| 30968 | Txndc8 | NM_026132.2 | chr4:57996900-58021996 | 31063 | Ube2dnl1 | NM_001276396.1 | chrX:112018620-112019550 |
| 30969 | Txndc9 | NM_172054.4 | chr1:38040711-38054053 | 31064 | Ube2dnl2 | NM_001081661.1 | chrX:112021190-112022119 |
| 30970 | Txnip | NM_001009935.2 | chr3:96359690-96370724 | 31065 | Ube2e1 | NM_009455.3 | chr14:19115243-19164358 |
| 30971 | Txnip | NM_023719.2 | chr3:96359690-96370724 | 31066 | Ube2e2 | NM_144839.1 | chr14:19406080-19726141 |
| 30972 | Txnl1 | NM_016792.2 | chr18:63822454-63852013 | 31067 | Ube2e3 | NM_009454.2 | chr2:78709203-78760740 |
| 30973 | Txnl4a | NM_001038608.2 | chr18:80403536-80422590 | 31068 | Ube2f | NM_026454.3 | chr1:93146896-93182602 |
| 30974 | Txnl4a | NM_001042408.1 | chr18:80403536-80422590 | 31069 | Ube2g1 | NM_025985.2 | chr11:72420762-72499983 |
| 30975 | Txnl4a | NM_025299.3 | chr18:80403536-80422590 | 31070 | Ube2g2 | NM_019803.3 | chr10:77085066-77108735 |
| 30976 | Txnl4a | NM_178804.3 | chr18:80403536-80422590 | 31071 | Ube2h | NM_001169576.1 | chr6:30161288-30254539 |
| 30977 | Txnl4b | NM_175646.3 | chr8:112089885-112097951 | 31072 | Ube2h | NM_001169577.1 | chr6:30161288-30254539 |
| 30978 | Txnrd1 | NM_001042513.1 | chr10:82296695-82360469 | 31073 | Ube2h | NM_009459.3 | chr6:30161288-30254539 |
| 30979 | Txnrd1 | NM_001042514.1 | chr10:82296695-82360469 | 31074 | Ube2i | NM_001177609.1 | chr17:25397455-25412473 |
| 30980 | Txnrd1 | NM_001042523.1 | chr10:82296695-82360469 | | | | |

Fig. 25 - 165

| | | | |
|---|---|---|---|
| 31075 | Ube2i | NM_001177610.1 | chr17:25397455-25412473 |
| 31076 | Ube2i | NM_011665.4 | chr17:25397455-25412473 |
| 31077 | Ube2j1 | NM_019586.3 | chr4:33118399-33139339 |
| 31078 | Ube2j2 | NM_001039157.2 | chr4:155317921-155333713 |
| 31079 | Ube2j2 | NM_001039158.2 | chr4:155317921-155333713 |
| 31080 | Ube2j2 | NM_001039159.2 | chr4:155317921-155333713 |
| 31081 | Ube2j2 | NM_001284312.1 | chr4:155317921-155333713 |
| 31082 | Ube2j2 | NM_001284314.1 | chr4:155317921-155333713 |
| 31083 | Ube2j2 | NM_021402.6 | chr4:155317921-155333713 |
| 31084 | Ube2k | NM_016786.3 | chr5:65928499-65990228 |
| 31085 | Ube2l3 | NM_009456.2 | chr16:17152197-17201585 |
| 31086 | Ube2l6 | NM_019949.2 | chr2:84638984-84650160 |
| 31087 | Ube2m | NM_001168469.2 | chr7:13620468-13623624 |
| 31088 | Ube2m | NM_001243968.1 | chr7:13620468-13623624 |
| 31089 | Ube2m | NM_145578.3 | chr7:13620468-13623624 |
| 31090 | Ube2n | NM_080560.3 | chr10:94977795-95008292 |
| 31091 | Ube2o | NM_173755.3 | chr11:116399066-116442761 |
| 31092 | Ube2q1 | NM_027315.4 | chr3:89577530-89587919 |
| 31093 | Ube2q2 | NM_180600.3 | chr9:54997175-55055336 |
| 31094 | Ube2ql1 | NM_001145162.1 | chr13:69841709-69878775 |
| 31095 | Ube2r2 | NM_026275.4 | chr4:41083053-41140403 |
| 31096 | Ube2s | NM_133777.2 | chr7:4759615-4763996 |
| 31097 | Ube2t | NM_001278115.1 | chr1:136859141-136870756 |
| 31098 | Ube2t | NM_026024.3 | chr1:136859141-136870756 |
| 31099 | Ube2u | NM_001033773.4 | chr4:100151471-100222750 |
| 31100 | Ube2v1 | NM_023230.2 | chr2:167433138-167457505 |
| 31101 | Ube2v2 | NM_001159351.1 | chr16:15551078-15594611 |
| 31102 | Ube2v2 | NM_023585.4 | chr16:15551078-15594611 |
| 31103 | Ube2w | NM_001271016.1 | chr1:16530868-16609419 |
| 31104 | Ube2w | NM_001271017.1 | chr1:16530868-16609419 |
| 31105 | Ube2w | NM_025773.4 | chr1:16530868-16609419 |
| 31106 | Ube2w | NR_073122.1 | chr1:16530868-16609419 |
| 31107 | Ube2z | NM_172300.3 | chr11:95908749-95926678 |
| 31108 | Ube3a | NM_001033962.1 | chr7:66484119-66562097 |
| 31109 | Ube3a | NM_011668.2 | chr7:66484119-66562097 |
| 31110 | Ube3a | NM_173010.3 | chr7:66484119-66562097 |
| 31111 | Ube3b | NM_054093.2 | chr5:114830616-114871175 |
| 31112 | Ube3c | NM_133907.3 | chr5:29895781-30002617 |
| 31113 | Ube4a | NM_145400.2 | chr9:44731209-44773683 |
| 31114 | Ube4b | NM_022022.3 | chr4:148702524-148800740 |
| 31115 | Ubfd1 | NM_138589.2 | chr7:129210711-129225713 |
| 31116 | Ubiad1 | NM_027273.2 | chr4:147808605-147818860 |
| 31117 | Ubl3 | NM_011908.2 | chr5:149316206-149364364 |
| 31118 | Ubl4 | NM_145405.2 | chrX:71611056-71618688 |
| 31119 | Ubl4 | NR_045779.1 | chrX:71611056-71618688 |
| 31120 | Ubl4b | NM_026261.2 | chr3:107356615-107357991 |
| 31121 | Ubl5 | NM_025401.3 | chr9:20447762-20451233 |
| 31122 | Ubl7 | NM_001122873.1 | chr9:57758792-57777775 |
| 31123 | Ubl7 | NM_027086.3 | chr9:57758792-57777775 |
| 31124 | Ublcp1 | NM_024475.5 | chr11:44268072-44284050 |
| 31125 | Ubn1 | NM_026066.3 | chr16:5050160-5086378 |
| 31126 | Ubn2 | NM_177185.4 | chr6:38383925-38462763 |
| 31127 | Ubox5 | NM_001255993.1 | chr2:130415731-130455774 |
| 31128 | Ubox5 | NM_001255994.1 | chr2:130415731-130455774 |
| 31129 | Ubox5 | NM_080562.5 | chr2:130415731-130455774 |
| 31130 | Ubp1 | NM_001083319.1 | chr9:113840051-113935869 |
| 31131 | Ubp1 | NM_013699.2 | chr9:113840051-113935869 |
| 31132 | Ubqln1 | NM_026842.4 | chr13:58277516-58317014 |
| 31133 | Ubqln1 | NM_152234.2 | chr13:58277516-58317014 |
| 31134 | Ubqln2 | NM_018798.2 | chrX:149932774-149936101 |
| 31135 | Ubqln3 | NM_198623.2 | chr7:111289136-111291786 |
| 31136 | Ubqln4 | NM_033526.2 | chr3:88357637-88373647 |
| 31137 | Ubqlnl | NM_198624.3 | chr7:111296772-111299070 |
| 31138 | Ubr1 | NM_009461.2 | chr2:120686012-120796461 |
| 31139 | Ubr2 | NM_001177374.1 | chr17:47065239-47147481 |
| 31140 | Ubr2 | NM_146078.3 | chr17:47065239-47147481 |
| 31141 | Ubr3 | NM_001081548.2 | chr2:69735302-69862070 |
| 31142 | Ubr3 | NM_177786.6 | chr2:69735302-69862070 |
| 31143 | Ubr4 | NM_001160319.1 | chr4:138936573-139045447 |
| 31144 | Ubr5 | NM_001081359.2 | chr15:37897082-38008609 |
| 31145 | Ubr5 | NM_001112721.2 | chr15:37897082-38008609 |
| 31146 | Ubr7 | NM_025666.2 | chr12:103996184-104015911 |
| 31147 | Ubtd1 | NM_145500.3 | chr19:42056252-42109131 |
| 31148 | Ubtd2 | NM_173784.3 | chr11:32355371-32418709 |
| 31149 | Ubtf | NM_001044383.2 | chr11:102165873-102180410 |
| 31150 | Ubtf | NM_011551.6 | chr11:102165873-102180410 |
| 31151 | Ubtf1 | NM_001033793.3 | chr9:18208861-18215946 |
| 31152 | Ubxn1 | NM_146093.1 | chr19:8946048-8950146 |
| 31153 | Ubxn10 | NM_001285928.1 | chr4:138265751-138300490 |
| 31154 | Ubxn10 | NM_001285929.1 | chr4:138265751-138300490 |
| 31155 | Ubxn10 | NM_001285930.1 | chr4:138265751-138300490 |
| 31156 | Ubxn10 | NM_178671.5 | chr4:138265751-138300490 |
| 31157 | Ubxn10 | NR_104373.1 | chr4:138265751-138300490 |
| 31158 | Ubxn11 | NM_026257.3 | chr4:133658497-133682695 |
| 31159 | Ubxn11 | NR_045571.1 | chr4:133658497-133682695 |
| 31160 | Ubxn2a | NM_145441.3 | chr12:4885837-4914326 |
| 31161 | Ubxn2b | NM_026566.3 | chr4:6118251-6146935 |
| 31162 | Ubxn4 | NM_026390.2 | chr1:130140757-130175954 |
| 31163 | Ubxn6 | NM_024832.2 | chr17:56207676-56224412 |
| 31164 | Ubxn7 | NM_177633.4 | chr16:32332337-32393833 |
| 31165 | Ubxn8 | NM_178648.2 | chr8:34730058-34752448 |
| 31166 | Uchl1 | NM_011670.2 | chr5:67067360-67078473 |
| 31167 | Uchl1os | NR_102714.1 | chr5:67017734-67067736 |
| 31168 | Uchl3 | NM_016723.2 | chr14:102053183-102095342 |
| 31169 | Uchl4 | NM_033607.1 | chr9:64083008-64084169 |

| | | | |
|---|---|---|---|
| 31170 | Uchl5 | NM_001159866.1 | chr1:145624407-145654596 |
| 31171 | Uchl5 | NM_019562.2 | chr1:145624407-145654596 |
| 31172 | Uck1 | NM_011675.2 | chr2:32110522-32115625 |
| 31173 | Uck2 | NM_030724.3 | chr1:169156216-169215258 |
| 31174 | Uckl1 | NM_026765.3 | chr2:181303859-181316678 |
| 31175 | Uckl1os | NR_027289.1 | chr2:181303858-181327166 |
| 31176 | Uckl1os | NR_027290.1 | chr2:181303858-181327166 |
| 31177 | Ucma | NM_001113558.2 | chr2:4897167-4906794 |
| 31178 | Ucma | NM_001165932.1 | chr2:4897167-4906794 |
| 31179 | Ucma | NM_026754.3 | chr2:4897167-4906794 |
| 31180 | Ucn | NM_021290.2 | chr5:31440362-31441268 |
| 31181 | Ucn2 | NM_145077.1 | chr9:108888207-108889209 |
| 31182 | Ucn3 | NM_031250.2 | chr13:3939933-3944595 |
| 31183 | Ucp1 | NM_009463.3 | chr8:85814246-85822355 |
| 31184 | Ucp2 | NM_011671.5 | chr7:107641853-107650682 |
| 31185 | Ucp3 | NM_009464.3 | chr7:107621499-107634941 |
| 31186 | Uevld | NM_001040695.1 | chr7:54178585-54213888 |
| 31187 | Ufc1 | NM_025388.2 | chr1:173218694-173225113 |
| 31188 | Ufd1l | NM_011687.4 | chr16:18812386-18835354 |
| 31189 | Ufd1l | NR_028403.1 | chr16:18812386-18835354 |
| 31190 | Ufl1 | NM_026194.4 | chr4:25175732-25208968 |
| 31191 | Ufm1 | NM_026435.5 | chr3:53657297-53667729 |
| 31192 | Ufsp1 | NM_027356.2 | chr5:137735896-137736892 |
| 31193 | Ufsp2 | NM_198668.2 | chr8:47060882-47082310 |
| 31194 | Ugcg | NM_011673.3 | chr4:59202421-59235705 |
| 31195 | Ugdh | NM_009466.2 | chr5:65804460-65827081 |
| 31196 | Uggt1 | NM_198899.2 | chr1:36196873-36301147 |
| 31197 | Uggt2 | NM_001081252.2 | chr14:119384206-119498656 |
| 31198 | Ugp2 | NM_001290634.1 | chr11:21139034-21271270 |
| 31199 | Ugp2 | NM_139297.5 | chr11:21139034-21271270 |
| 31200 | Ugt1a1 | NM_201645.2 | chr1:90108534-90116577 |
| 31201 | Ugt1a10 | NM_201641.1 | chr1:89951986-90116577 |
| 31202 | Ugt1a2 | NM_013701.3 | chr1:90097186-90116577 |
| 31203 | Ugt1a5 | NM_201643.2 | chr1:90062587-90116577 |
| 31204 | Ugt1a6a | NM_145079.3 | chr1:90031384-90116577 |
| 31205 | Ugt1a6b | NM_201410.3 | chr1:89999832-90115573 |
| 31206 | Ugt1a7c | NM_201642.4 | chr1:89991576-90116577 |
| 31207 | Ugt1a9 | NM_201644.2 | chr1:89967354-90116577 |
| 31208 | Ugt2a1 | NM_053184.2 | chr5:87888515-87919896 |
| 31209 | Ugt2a2 | NM_001024148.1 | chr5:87888518-87911283 |
| 31210 | Ugt2a3 | NM_028094.3 | chr5:87753996-87766220 |
| 31211 | Ugt2b1 | NM_152811.1 | chr5:87345663-87355528 |
| 31212 | Ugt2b34 | NM_153598.2 | chr5:87318794-87335962 |
| 31213 | Ugt2b35 | NM_172881.3 | chr5:87429884-87442299 |
| 31214 | Ugt2b36 | NM_001029867.1 | chr5:87494951-87521580 |
| 31215 | Ugt2b37 | NM_053215.3 | chr5:87669516-87683813 |
| 31216 | Ugt2b38 | NM_133894.2 | chr5:87838964-87853228 |
| 31217 | Ugt2b5 | NM_009467.3 | chr5:87553971-87569365 |
| 31218 | Ugt3a1 | NM_207216.2 | chr15:9209583-9244791 |
| 31219 | Ugt3a2 | NM_144845.3 | chr15:9265352-9300625 |
| 31220 | Ugt8a | NM_011674.2 | chr3:125568260-125641468 |
| 31221 | Uhmk1 | NM_010633.3 | chr1:172129386-172145524 |
| 31222 | Uhrf1 | NM_001111078.1 | chr17:56442759-56462909 |
| 31223 | Uhrf1 | NM_001111079.1 | chr17:56442759-56462909 |
| 31224 | Uhrf1 | NM_001111080.1 | chr17:56442759-56462909 |
| 31225 | Uhrf1 | NM_010931.2 | chr17:56442759-56462909 |
| 31226 | Uhrf1bp1 | NM_001080769.1 | chr17:27993451-28036985 |
| 31227 | Uhrf1bp1l | NM_029166.2 | chr10:89207735-89282614 |
| 31228 | Uhrf2 | NM_144873.2 | chr19:30105002-30168214 |
| 31229 | Uimc1 | NM_011307.2 | chr13:55129240-55201656 |
| 31230 | Uimc1 | NM_029975.2 | chrUn_random:3058602-3072666 |
| 31231 | Ulk1 | NM_009469.3 | chr5:111213507-111239100 |
| 31232 | Ulk2 | NM_013881.4 | chr11:61589099-61668594 |
| 31233 | Ulk3 | NM_027895.1 | chr9:57437258-57444040 |
| 31234 | Ulk4 | NM_177589.3 | chr9:120873571-121186290 |
| 31235 | Umod | NM_001278605.1 | chr7:126606221-126622776 |
| 31236 | Umod | NM_009470.5 | chr7:126606221-126622776 |
| 31237 | Umodl1 | NM_177465.4 | chr17:31091627-31147655 |
| 31238 | Umps | NM_009471.2 | chr16:33955097-33967089 |
| 31239 | Unc119 | NM_011676.2 | chr11:78157023-78162658 |
| 31240 | Unc119b | NM_175352.4 | chr5:115572574-115584984 |
| 31241 | Unc13a | NM_001029873.2 | chr8:74150612-74195656 |
| 31242 | Unc13b | NM_001081413.1 | chr4:43071855-43277759 |
| 31243 | Unc13b | NM_021468.2 | chr4:43071855-43277759 |
| 31244 | Unc13c | NM_001081153.1 | chr9:73327230-73781374 |
| 31245 | Unc13d | NM_001009573.2 | chr11:115923409-115939275 |
| 31246 | Unc45a | NM_133952.2 | chr7:87470178-87485305 |
| 31247 | Unc45b | NM_178680.4 | chr11:82724755-82756908 |
| 31248 | Unc50 | NM_026123.3 | chr1:37487016-37495969 |
| 31249 | Unc5a | NM_153131.3 | chr13:55050793-55107379 |
| 31250 | Unc5b | NM_029770.2 | chr10:60225342-60294329 |
| 31251 | Unc5c | NM_009472.4 | chr3:141128527-141497886 |
| 31252 | Unc5cl | NM_152823.4 | chr17:48594225-48608009 |
| 31253 | Unc5d | NM_153135.2 | chr8:29757188-30330108 |
| 31254 | Unc79 | NM_001081017.2 | chr12:104187068-104422207 |
| 31255 | Unc80 | NM_175510.3 | chr1:66515020-66745722 |
| 31256 | Unc93a | NM_199252.2 | chr17:13301482-13324657 |
| 31257 | Unc93b1 | NM_001161428.1 | chr19:3935185-3949340 |
| 31258 | Unc93b1 | NM_019449.2 | chr19:3935185-3949340 |
| 31259 | Uncx | NM_013702.3 | chr5:140019851-140024132 |
| 31260 | Ung | NM_001040690.1 | chr5:114580443-114589330 |
| 31261 | Ung | NM_011677.2 | chr5:114580443-114589330 |
| 31262 | Unk | NM_001286006.1 | chr11:115891629-115922528 |
| 31263 | Unk | NM_172569.4 | chr11:115891629-115922528 |

Fig. 25 - 166

| | | | |
|---|---|---|---|
| 31264 | Unkl | NM_001197024.1 | chr17:25325344-25377061 |
| 31265 | Unkl | NM_001290736.1 | chr17:25325344-25377061 |
| 31266 | Unkl | NM_028789.3 | chr17:25325344-25377061 |
| 31267 | Uox | NM_009474.5 | chr3:146260113-146294447 |
| 31268 | Upb1 | NM_133995.4 | chr10:74869655-74904424 |
| 31269 | Upf1 | NM_001122829.1 | chr8:72839673-72877172 |
| 31270 | Upf1 | NM_030680.2 | chr8:72839673-72877172 |
| 31271 | Upf2 | NM_001081132.1 | chr2:5872514-5977749 |
| 31272 | Upf3a | NM_025924.1 | chr8:13785614-13798537 |
| 31273 | Upf3b | NM_026573.2 | chrX:34631828-34650317 |
| 31274 | Upk1a | NM_026815.2 | chr7:31388110-31397493 |
| 31275 | Upk1b | NM_178924.4 | chr16:38773296-38800316 |
| 31276 | Upk2 | NM_009476.2 | chr9:44260797-44262850 |
| 31277 | Upk3a | NM_023478.2 | chr15:84847576-84852990 |
| 31278 | Upk3b | NM_175309.3 | chr5:136514365-136520863 |
| 31279 | Upk3bl | NM_027158.1 | chr5:136533135-136540194 |
| 31280 | Upp1 | NM_001159401.1 | chr11:9018010-9036173 |
| 31281 | Upp1 | NM_001159402.1 | chr11:9018010-9036173 |
| 31282 | Upp1 | NM_009477.3 | chr11:9018010-9036173 |
| 31283 | Upp2 | NM_001289659.1 | chr2:58419744-58645382 |
| 31284 | Upp2 | NM_001289660.1 | chr2:58419744-58645382 |
| 31285 | Upp2 | NM_029692.3 | chr2:58419744-58645382 |
| 31286 | Uprt | NM_001081189.1 | chrX:101678120-101701601 |
| 31287 | Uqcc1 | NM_018888.4 | chr2:155672621-155756046 |
| 31288 | Uqcc1 | NR_024487.2 | chr2:155672621-155756046 |
| 31289 | Uqcc2 | NM_026063.2 | chr17:27259609-27270836 |
| 31290 | Uqcr10 | NM_197979.2 | chr11:4601970-4604347 |
| 31291 | Uqcr11 | NM_025650.2 | chr10:79865741-79869566 |
| 31292 | Uqcrb | NM_026219.1 | chr13:67001556-67006286 |
| 31293 | Uqcrc1 | NM_025407.2 | chr9:108838660-108851686 |
| 31294 | Uqcrc2 | NM_025899.2 | chr7:127778703-127803037 |
| 31295 | Uqcrfs1 | NM_025710.2 | chr13:30632180-30637185 |
| 31296 | Uqcrh | NM_025641.3 | chr4:115739569-115747675 |
| 31297 | Uqcrq | NM_025352.2 | chr11:53242449-53244333 |
| 31298 | Urad | NM_001039678.2 | chr5:148126559-148134016 |
| 31299 | Urah | NM_029821.2 | chr7:148021395-148023867 |
| 31300 | Urb1 | NM_029497.1 | chr16:90751771-90810658 |
| 31301 | Urb2 | NM_001029876.1 | chr8:126547372-126572404 |
| 31302 | Urgcp | NM_001077661.1 | chr11:5613419-5684713 |
| 31303 | Urgcp | NM_178623.3 | chr11:5613419-5684713 |
| 31304 | Uri1 | NM_011274.5 | chr7:38745010-38804571 |
| 31305 | Urm1 | NM_026615.4 | chr2:29682908-29700516 |
| 31306 | Uroc1 | NM_144940.2 | chr6:90283282-90314542 |
| 31307 | Urod | NM_009478.3 | chr4:116662821-116666980 |
| 31308 | Uros | NM_009479.3 | chr7:140878012-140900978 |
| 31309 | Usb1 | NM_139954.2 | chr8:97856183-97871413 |
| 31310 | Use1 | NM_001145780.1 | chr8:73890746-73893631 |
| 31311 | Use1 | NM_025917.4 | chr8:73890746-73893631 |
| 31312 | Usf1 | NM_009480.3 | chr1:173341811-173348873 |
| 31313 | Usf2 | NM_011680.2 | chr7:31730266-31741822 |
| 31314 | Ush1c | NM_001163733.1 | chr7:53450720-53493860 |
| 31315 | Ush1c | NM_001291182.1 | chr7:53450720-53493860 |
| 31316 | Ush1c | NM_023649.2 | chr7:53450720-53493860 |
| 31317 | Ush1c | NM_153677.2 | chr7:53450720-53493860 |
| 31318 | Ush1g | NM_176847.3 | chr11:115176506-115183232 |
| 31319 | Ush2a | NM_021408.3 | chr1:190086716-190788918 |
| 31320 | Ushbp1 | NM_181418.3 | chr8:73903172-73919700 |
| 31321 | Usmg5 | NM_023211.4 | chr19:47159961-47165115 |
| 31322 | Uso1 | NM_019401.1 | chr5:92566963-92631821 |
| 31323 | Usp1 | NM_146144.4 | chr4:98590500-98602224 |
| 31324 | Usp10 | NM_009462.1 | chr8:122434751-122481457 |
| 31325 | Usp11 | NM_145628.4 | chrX:20281034-20297865 |
| 31326 | Usp12 | NM_011669.3 | chr5:147546387-147606532 |
| 31327 | Usp13 | NM_001013024.2 | chr3:32716547-32834179 |
| 31328 | Usp14 | NM_001038586.2 | chr18:9958177-10030147 |
| 31329 | Usp14 | NM_021522.4 | chr18:9958177-10030147 |
| 31330 | Usp15 | NM_027604.4 | chr10:122550299-122633979 |
| 31331 | Usp16 | NM_024258.2 | chr16:87455230-87483758 |
| 31332 | Usp17la | NM_007887.2 | chr7:112005529-112011181 |
| 31333 | Usp17lb | NM_201406.2 | chr7:111988825-111991018 |
| 31334 | Usp17lc | NM_010089.3 | chr7:110565209-110567688 |
| 31335 | Usp17ld | NM_001001559.2 | chr7:110398599-110401019 |
| 31336 | Usp17le | NM_001256973.1 | chr7:110916562-110925984 |
| 31337 | Usp18 | NM_011909.2 | chr6:121195923-121220935 |
| 31338 | Usp19 | NM_001168371.2 | chr9:108393006-108404668 |
| 31339 | Usp19 | NM_001168372.2 | chr9:108393006-108404668 |
| 31340 | Usp19 | NM_001168373.2 | chr9:108393006-108404668 |
| 31341 | Usp19 | NM_027804.4 | chr9:108393006-108404668 |
| 31342 | Usp19 | NM_145407.3 | chr9:108393006-108404668 |
| 31343 | Usp2 | NM_016808.2 | chr9:43875103-43903710 |
| 31344 | Usp2 | NM_198091.2 | chr9:43875103-43903710 |
| 31345 | Usp2 | NM_198092.3 | chr9:43875103-43903710 |
| 31346 | Usp20 | NM_028846.5 | chr2:30837798-30878175 |
| 31347 | Usp21 | NM_013919.4 | chr1:173212083-173218092 |
| 31348 | Usp22 | NM_0001044143.4 | chr11:60965282-60988561 |
| 31349 | Usp24 | NM_183225.2 | chr4:105988817-106113932 |
| 31350 | Usp25 | NM_014314.3 | chr16:77014313-77117025 |
| 31351 | Usp26 | NM_031388.2 | chrX:49107135-49154410 |
| 31352 | Usp27x | NM_019461.4 | chrX:6949716-6952956 |
| 31353 | Usp28 | NM_175482.3 | chr9:48793489-48850622 |
| 31354 | Usp29 | NM_001290994.1 | chr7:6683293-6929373 |
| 31355 | Usp29 | NM_021323.3 | chr7:6683293-6929373 |
| 31356 | Usp3 | NM_144937.4 | chr9:66365687-66440787 |
| 31357 | Usp30 | NM_001033202.3 | chr5:114550341-114572933 |
| 31358 | Usp31 | NM_001033173.1 | chr7:128785534-128850767 |
| 31359 | Usp32 | NM_001029934.1 | chr11:84797989-84953457 |
| 31360 | Usp33 | NM_001076676.2 | chr3:152009441-152056578 |
| 31361 | Usp33 | NM_001252486.1 | chr3:152009441-152056578 |
| 31362 | Usp33 | NM_133247.3 | chr3:152009441-152056578 |
| 31363 | Usp34 | NM_001190401.2 | chr11:23206895-23390560 |
| 31364 | Usp35 | NM_001177412.1 | chr7:104457889-104474474 |
| 31365 | Usp36 | NM_001033528.1 | chr11:118120966-118151558 |
| 31366 | Usp37 | NM_178972.4 | chr1:74482084-74590860 |
| 31367 | Usp38 | NM_027554.2 | chr8:83504631-83538805 |
| 31368 | Usp39 | NM_138592.4 | chr6:72268669-72295169 |
| 31369 | Usp4 | NM_011678.2 | chr9:108250161-108294860 |
| 31370 | Usp40 | NM_001033291.2 | chr1:89841695-89905126 |
| 31371 | Usp40 | NM_001198573.1 | chr1:89841695-89905126 |
| 31372 | Usp42 | NM_029749.2 | chr5:144471194-144493149 |
| 31373 | Usp43 | NM_001291049.1 | chr11:67668024-67735655 |
| 31374 | Usp43 | NM_173754.4 | chr11:67668024-67735655 |
| 31375 | Usp44 | NM_001206851.1 | chr10:93294299-93320832 |
| 31376 | Usp44 | NM_183199.3 | chr10:93294299-93320832 |
| 31377 | Usp45 | NM_001290425.1 | chr4:21703416-21765019 |
| 31378 | Usp45 | NM_152825.2 | chr4:21703416-21765019 |
| 31379 | Usp46 | NM_177561.2 | chr5:74396061-74464436 |
| 31380 | Usp47 | NM_133758.3 | chr7:119167019-119254900 |
| 31381 | Usp47 | NM_177249.1 | chr7:119167019-119254900 |
| 31382 | Usp48 | NM_130879.2 | chr4:137150103-137214452 |
| 31383 | Usp49 | NM_198421.1 | chr17:47767638-47821016 |
| 31384 | Usp5 | NM_013700.1 | chr6:124765036-124779465 |
| 31385 | Usp50 | NM_029163.3 | chr2:126586785-126609196 |
| 31386 | Usp51 | NM_001137547.1 | chrX:149441011-149444002 |
| 31387 | Usp53 | NM_133857.3 | chr3:122636518-122687365 |
| 31388 | Usp54 | NM_030180.2 | chr14:21368134-21437576 |
| 31389 | Usp6nl | NM_001080548.1 | chr2:6243802-6364866 |
| 31390 | Usp6nl | NM_181399.3 | chr2:6243802-6364866 |
| 31391 | Usp7 | NM_001003918.2 | chr16:8688814-8738435 |
| 31392 | Usp8 | NM_001252580.1 | chr2:126533063-126585050 |
| 31393 | Usp8 | NM_019729.3 | chr2:126533063-126585050 |
| 31394 | Usp9x | NM_009481.2 | chrX:12648623-12750453 |
| 31395 | Usp9y | NM_148943.2 | chrY:635403-796225 |
| 31396 | Uspl1 | NM_001013378.2 | chr5:149996135-150027010 |
| 31397 | Uspl1 | NM_001115149.1 | chr5:149996135-150027010 |
| 31398 | Uspl1 | NM_001115150.1 | chr5:149996135-150027010 |
| 31399 | Uspl1 | NM_001115151.1 | chr5:149996135-150027010 |
| 31400 | Uspl1 | NM_001115153.1 | chr5:149996135-150027010 |
| 31401 | Uspl1 | NM_001286824.1 | chr5:149996135-150027010 |
| 31402 | Uspl1 | NM_001286825.1 | chr5:149996135-150027010 |
| 31403 | Ust | NM_177387.3 | chr10:7924550-8238623 |
| 31404 | Utf1 | NM_009482.2 | chr7:147129754-147131011 |
| 31405 | Utp11l | NM_026031.3 | chr4:124356007-124370798 |
| 31406 | Utp14a | NM_028276.1 | chrX:45610111-45635626 |
| 31407 | Utp14b | NM_001001981.3 | chr1:78654399-78704318 |
| 31408 | Utp14b | NM_001136226.1 | chr1:78654399-78704318 |
| 31409 | Utp15 | NM_178918.3 | chr13:99016799-99032947 |
| 31410 | Utp18 | NM_001013375.1 | chr11:93720556-93747080 |
| 31411 | Utp20 | NM_175158.3 | chr10:88209351-88289559 |
| 31412 | Utp23 | NM_030132.5 | chr15:51708986-51716168 |
| 31413 | Utp3 | NM_023054.1 | chr5:88983507-88985108 |
| 31414 | Utp6 | NM_144826.3 | chr11:79747457-79775889 |
| 31415 | Utrn | NM_011682.4 | chr10:12101985-12581533 |
| 31416 | Uts2 | NM_011910.2 | chr4:150371205-150375919 |
| 31417 | Uts2b | NM_198166.3 | chr16:27353407-27370325 |
| 31418 | Uts2r | NM_145440.1 | chr11:121021584-121023287 |
| 31419 | Uty | NM_009484.2 | chrY:433586-582181 |
| 31420 | Uvrag | NM_178635.3 | chr7:106035252-106289654 |
| 31421 | Uvssa | NM_001081101.2 | chr5:33721344-33762403 |
| 31422 | Uxs1 | NM_026430.3 | chr1:43807075-43884553 |
| 31423 | Uxt | NM_013840.3 | chrX:20528791-20539164 |
| 31424 | V1ra8 | NM_053223.1 | chr6:90152810-90153650 |
| 31425 | V1rd18 | NM_207618.2 | chr7:24788110-24789266 |
| 31426 | V1rd19 | NM_207619.2 | chr7:24788130-24789047 |
| 31427 | Vac14 | NM_146216.2 | chr8:113142537-113244299 |
| 31428 | Vamp1 | NM_001080557.1 | chr6:125165598-125172324 |
| 31429 | Vamp1 | NM_009496.3 | chr6:125165598-125172324 |
| 31430 | Vamp2 | NM_009497.3 | chr11:68902029-68905883 |
| 31431 | Vamp3 | NM_009498.4 | chr4:150421413-150432062 |
| 31432 | Vamp4 | NM_016796.3 | chr1:164500958-164529209 |
| 31433 | Vamp5 | NM_001080742.2 | chr6:72318042-72330462 |
| 31434 | Vamp5 | NM_016872.4 | chr6:72318042-72330462 |
| 31435 | Vamp7 | NM_011515.5 | chrX_random:10737-39148 |
| 31436 | Vamp8 | NM_016794.3 | chr6:72335214-72340661 |
| 31437 | Vangl1 | NM_001165951.2 | chr3:101959822-102008616 |
| 31438 | Vangl1 | NM_177545.5 | chr3:101959822-102008616 |
| 31439 | Vangl2 | NM_033509.3 | chr1:173943501-173957399 |
| 31440 | Vapa | NM_013933.3 | chr17:65929392-65962895 |
| 31441 | Vapb | NM_019806.5 | chr2:173563071-173609837 |
| 31442 | Vars | NM_011690.3 | chr17:35137851-35153274 |
| 31443 | Vars2 | NM_175137.4 | chr17:35792579-35804537 |
| 31444 | Vash1 | NM_177354.4 | chr12:88019649-88036631 |
| 31445 | Vash2 | NM_144879.2 | chr1:192771524-192803175 |
| 31446 | Vash2 | NR_027352.1 | chr1:192771524-192803175 |
| 31447 | Vasn | NM_139307.3 | chr16:4639945-4651166 |
| 31448 | Vasp | NM_001282021.1 | chr7:19842278-19857203 |
| 31449 | Vasp | NM_001282022.1 | chr7:19842278-19857203 |
| 31450 | Vasp | NM_009499.3 | chr7:19842278-19857203 |
| 31451 | Vasp | NR_104069.1 | chr7:19842278-19857203 |
| 31452 | Vat1 | NM_012037.2 | chr11:101320061-101327513 |
| 31453 | Vat1l | NM_173016.3 | chr8:116729540-116897970 |

Fig. 25 - 167

| | | | |
|---|---|---|---|
| 31454 | Vaultrc5 | NR_027885.1 | chr18:36961416-36961761 |
| 31455 | Vav1 | NM_001163815.1 | chr17:57418522-57468659 |
| 31456 | Vav1 | NM_001163816.1 | chr17:57418522-57468659 |
| 31457 | Vav1 | NM_011691.4 | chr17:57418522-57468659 |
| 31458 | Vav2 | NM_009500.1 | chr2:27119154-27282345 |
| 31459 | Vav3 | NM_020505.2 | chr3:109143600-109488612 |
| 31460 | Vav3 | NM_146139.2 | chr3:109143600-109488612 |
| 31461 | Vax1 | NM_009501.1 | chr19:59240676-59244519 |
| 31462 | Vax2 | NM_011912.3 | chr6:83661258-83688298 |
| 31463 | Vax2os | NR_002871.1 | chr6:83642799-83688298 |
| 31464 | Vax2os | NR_002873.2 | chr6:83642799-83688298 |
| 31465 | Vax2os | NR_075094.1 | chr6:83642799-83688298 |
| 31466 | Vax2os | NR_075095.1 | chr6:83642799-83688298 |
| 31467 | Vbp1 | NM_011692.2 | chrX:72759635-72780285 |
| 31468 | Vcam1 | NM_011693.3 | chr3:115812937-115832606 |
| 31469 | Vcan | NM_001081249.1 | chr13:89794914-89882117 |
| 31470 | Vcan | NM_001134474.1 | chr13:89794914-89882117 |
| 31471 | Vcan | NM_001134475.1 | chr13:89794914-89882117 |
| 31472 | Vcan | NM_019389.2 | chr13:89794914-89882117 |
| 31473 | Vcan | NM_172955.1 | chr13:89794914-89882117 |
| 31474 | Vcl | NM_009502.4 | chr14:21748654-21852895 |
| 31475 | Vcp | NM_009503.4 | chr4:42992835-43013379 |
| 31476 | Vcpip1 | NM_173443.3 | chr1:9708703-9738463 |
| 31477 | Vcpkmt | NM_001033236.2 | chr12:70678614-70684015 |
| 31478 | Vdac1 | NM_011694.3 | chr11:52174616-52202898 |
| 31479 | Vdac2 | NM_011695.2 | chr14:22650783-22665101 |
| 31480 | Vdac3 | NM_001198998.1 | chr8:23687546-23704285 |
| 31481 | Vdac3 | NM_011696.2 | chr8:23687546-23704285 |
| 31482 | Vdr | NM_009504.4 | chr15:97684857-97738727 |
| 31483 | Vegfa | NM_001110266.1 | chr17:46153942-46169326 |
| 31484 | Vegfa | NM_001110267.1 | chr17:46153942-46169326 |
| 31485 | Vegfa | NM_001110268.1 | chr17:46153942-46169326 |
| 31486 | Vegfa | NM_001287056.1 | chr17:46153942-46169326 |
| 31487 | Vegfa | NM_001287058.1 | chr17:46153942-46169326 |
| 31488 | Vegfa | NM_009505.4 | chr17:46153942-46169326 |
| 31489 | Vegfb | NM_001185164.1 | chr19:7056961-7062141 |
| 31490 | Vegfb | NM_011697.3 | chr19:7056961-7062141 |
| 31491 | Vegfc | NM_009506.2 | chr8:55162885-55271808 |
| 31492 | Veph1 | NM_145820.3 | chr3:65857480-66100759 |
| 31493 | Vezf1 | NM_016686.4 | chr11:87881780-87898231 |
| 31494 | Vezt | NM_172538.5 | chr10:93430844-93498493 |
| 31495 | Vgf | NM_001039385.1 | chr5:137506164-137509221 |
| 31496 | Vgll1 | NM_133251.1 | chrX:54341282-54358623 |
| 31497 | Vgll2 | NM_153786.2 | chr10:51742491-51748277 |
| 31498 | Vgll3 | NM_028572.1 | chr16:65815877-65863311 |
| 31499 | Vgll4 | NM_177683.2 | chr6:114812107-114871770 |
| 31500 | Vhl | NM_009507.3 | chr6:113574014-113581627 |
| 31501 | Vill | NM_009509.2 | chr1:74455958-74482134 |
| 31502 | Vil1 | NM_001164567.1 | chr9:118961895-118980643 |
| 31503 | Vil1 | NM_011700.2 | chr9:118961895-118980643 |
| 31504 | Vim | NM_011701.4 | chr2:13495937-13504453 |
| 31505 | Vmp | NM_024439.3 | chr7:73224534-73234291 |
| 31506 | Vip | NM_011702.2 | chr10:4698926-4707323 |
| 31507 | Vipas39 | NM_001142580.1 | chr12:88579824-88607236 |
| 31508 | Vipas39 | NM_001142581.1 | chr12:88579824-88607236 |
| 31509 | Vipas39 | NM_134044.3 | chr12:88579824-88607236 |
| 31510 | Vipr1 | NM_011703.4 | chr9:121551833-121582072 |
| 31511 | Vipr2 | NM_009511.2 | chr12:117316195-117384734 |
| 31512 | Vit | NM_197028.1 | chr17:78907402-79026749 |
| 31513 | Vit | NM_028813.2 | chr17:78907402-79026749 |
| 31514 | Vkorc1 | NM_178600.2 | chr7:135036576-135039131 |
| 31515 | Vkorc1l1 | NM_001001327.2 | chr5:130417978-130462562 |
| 31516 | Vkorc1l1 | NM_001286382.1 | chr5:130417978-130462562 |
| 31517 | Vkorc1l1 | NM_027121.4 | chr5:130417978-130462562 |
| 31518 | Vldlr | NM_001161420.1 | chr19:27291509-27328721 |
| 31519 | Vldlr | NM_013703.2 | chr19:27291509-27328721 |
| 31520 | Vma21 | NM_001081356.3 | chrX:69061418-69070045 |
| 31521 | Vma21 | NM_001290780.1 | chrX:69061418-69070045 |
| 31522 | Vma21 | NM_001290781.1 | chrX:69061418-69070045 |
| 31523 | Vmac | NM_001166728.1 | chr17:56853354-56857122 |
| 31524 | Vmac | NM_178926.3 | chr17:56853354-56857122 |
| 31525 | Vmn1r1 | NM_001166728.1 | chr1:184087308-184088229 |
| 31526 | Vmn1r10 | NM_053231.2 | chr6:57063418-57064354 |
| 31527 | Vmn1r100 | NM_001166844.1 | chr7:21003290-21004214 |
| 31528 | Vmn1r100 | NM_001166844.1 | chr7:23197249-23199687 |
| 31529 | Vmn1r101 | NM_001166836.1 | chr7:21027018-21027942 |
| 31530 | Vmn1r101 | NM_001166836.1 | chr7:23222324-23223248 |
| 31531 | Vmn1r103 | NM_001166737.1 | chr7:21094965-21095883 |
| 31532 | Vmn1r104 | NM_001166738.1 | chr7:21119185-21120109 |
| 31533 | Vmn1r11 | NM_053233.2 | chr6:57087346-57088246 |
| 31534 | Vmn1r111 | NM_001166746.1 | chr7:22812995-22813916 |
| 31535 | Vmn1r112 | NM_001166739.1 | chr7:21556203-21557097 |
| 31536 | Vmn1r113 | NM_001166716.1 | chr7:21572303-21573227 |
| 31537 | Vmn1r114 | NM_001166837.1 | chr7:21596239-21597205 |
| 31538 | Vmn1r115 | NM_001166745.1 | chr7:21629116-21630004 |
| 31539 | Vmn1r116 | NM_001166744.1 | chr7:21657274-21658198 |
| 31540 | Vmn1r117 | NM_001166743.1 | chr7:21668216-21669140 |
| 31541 | Vmn1r118 | NM_001166742.1 | chr7:20818256-20819177 |
| 31542 | Vmn1r119 | NM_001166708.1 | chr7:21796550-21797474 |
| 31543 | Vmn1r12 | NM_001101579.1 | chr6:57109813-57109837 |
| 31544 | Vmn1r120 | NM_001166715.1 | chr7:21837885-21838803 |
| 31545 | Vmn1r121 | NM_001166741.1 | chr7:21882587-21883532 |
| 31546 | Vmn1r122 | NM_001166714.1 | chr7:21918229-21919147 |
| 31547 | Vmn1r123 | NM_001166707.1 | chr7:21947203-21948127 |
| 31548 | Vmn1r124 | NM_001166757.1 | chr7:22044712-22045636 |
| 31549 | Vmn1r125 | NM_001166740.1 | chr7:22057197-22058121 |
| 31550 | Vmn1r126 | NM_001166838.1 | chr7:22085521-22086486 |
| 31551 | Vmn1r127 | NM_001166726.1 | chr7:22103962-22104880 |
| 31552 | Vmn1r128 | NM_001166739.1 | chr7:22134391-22135315 |
| 31553 | Vmn1r129 | NM_001166725.1 | chr7:22145386-22146310 |
| 31554 | Vmn1r13 | NM_053235.2 | chr6:57159851-57160754 |
| 31555 | Vmn1r130 | NM_001166848.1 | chr7:21254266-21255190 |
| 31556 | Vmn1r131 | NM_001166839.1 | chr7:21487314-21488235 |
| 31557 | Vmn1r132 | NM_001122682.1 | chr7:22397763-22400165 |
| 31558 | Vmn1r132 | NM_001122682.1 | chr7:22880538-22882940 |
| 31559 | Vmn1r135 | NM_001166747.1 | chr7:23840558-23841482 |
| 31560 | Vmn1r138 | NM_001167169.1 | chr7:24035780-24036701 |
| 31561 | Vmn1r139 | NM_001166748.1 | chr7:22880538-22882940 |
| 31562 | Vmn1r139 | NM_001166748.1 | chr7:22397763-22400165 |
| 31563 | Vmn1r14 | NM_053237.2 | chr6:57183432-57184344 |
| 31564 | Vmn1r142 | NM_001166749.1 | chr7:22948136-22949054 |
| 31565 | Vmn1r143 | NM_001166750.1 | chr7:20779058-20779982 |
| 31566 | Vmn1r143 | NM_001166750.1 | chr7:22974395-22975319 |
| 31567 | Vmn1r144 | NM_030736.2 | chr7:23197250-23199687 |
| 31568 | Vmn1r15 | NM_053236.2 | chr6:57208142-57209042 |
| 31569 | Vmn1r151 | NM_001166712.1 | chr7:23283779-23284697 |
| 31570 | Vmn1r152 | NM_001166712.1 | chr7:23307985-23308909 |
| 31571 | Vmn1r155 | NM_001166753.1 | chr7:21453935-21454859 |
| 31572 | Vmn1r157 | NM_001166754.1 | chr7:21357946-21358840 |
| 31573 | Vmn1r157 | NM_001166754.1 | chr7:23498616-23685774 |
| 31574 | Vmn1r158 | NM_001166841.1 | chr7:23574878-23575801 |
| 31575 | Vmn1r159 | NM_001166758.1 | chr7:23627707-23628624 |
| 31576 | Vmn1r16 | NM_134184.2 | chr6:57272717-57273629 |
| 31577 | Vmn1r160 | NM_001166724.1 | chr7:23656243-23657166 |
| 31578 | Vmn1r163 | NM_001166755.1 | chr7:22617369-22618293 |
| 31579 | Vmn1r165 | NM_001166850.1 | chr7:22779605-22780529 |
| 31580 | Vmn1r165 | NM_001166850.1 | chr7:22296798-22297722 |
| 31581 | Vmn1r165 | NM_001166850.1 | chr7:23443036-23443960 |
| 31582 | Vmn1r165 | NM_001166850.1 | chr7:24002350-24003274 |
| 31583 | Vmn1r166 | NM_001167168.1 | chr7:22330188-22331109 |
| 31584 | Vmn1r167 | NM_001101562.1 | chr7:24289660-24290608 |
| 31585 | Vmn1r168 | NM_001166842.1 | chr7:24325738-24326668 |
| 31586 | Vmn1r169 | NM_001166843.1 | chr7:24362203-24363118 |
| 31587 | Vmn1r17 | NM_134171.1 | chr6:57310460-57311372 |
| 31588 | Vmn1r170 | NM_001166722.1 | chr7:24391193-24392108 |
| 31589 | Vmn1r171 | NM_030737.2 | chr7:24417006-24418587 |
| 31590 | Vmn1r172 | NM_030735.1 | chr7:24443334-24445682 |
| 31591 | Vmn1r173 | NM_001166718.1 | chr7:24487360-24488302 |
| 31592 | Vmn1r174 | NM_207548.2 | chr7:24538929-24539871 |
| 31593 | Vmn1r175 | NM_001166727.1 | chr7:24593304-24594219 |
| 31594 | Vmn1r176 | NM_001166721.1 | chr7:24619830-24620745 |
| 31595 | Vmn1r177 | NM_206872.2 | chr7:24650538-24651468 |
| 31596 | Vmn1r178 | NM_206868.1 | chr7:24678547-24679462 |
| 31597 | Vmn1r179 | NM_207545.1 | chr7:24713404-24714376 |
| 31598 | Vmn1r18 | NM_134181.1 | chr6:57339661-57340561 |
| 31599 | Vmn1r180 | NM_206869.2 | chr7:24737405-24738375 |
| 31600 | Vmn1r181 | NM_207546.2 | chr7:24768979-24770067 |
| 31601 | Vmn1r183 | NM_203489.1 | chr7:24839792-24840710 |
| 31602 | Vmn1r184 | NM_001167540.1 | chr7:27051849-27052794 |
| 31603 | Vmn1r185 | NM_134231.1 | chr7:27396137-27397097 |
| 31604 | Vmn1r186 | NM_001167567.1 | chr7:5626205-5628199 |
| 31605 | Vmn1r186 | NM_001167567.1 | chr7_random:93812-95806 |
| 31606 | Vmn1r187 | NM_001167568.1 | chr7:5753949-5757047 |
| 31607 | Vmn1r187 | NM_001167568.1 | chr7_random:148881-151977 |
| 31608 | Vmn1r188 | NM_145850.1 | chr13:22179746-22180673 |
| 31609 | Vmn1r189 | NM_145844.1 | chr13:22193595-22194534 |
| 31610 | Vmn1r19 | NM_134182.1 | chr6:57354457-57355384 |
| 31611 | Vmn1r191 | NM_145849.1 | chr13:22270554-22271451 |
| 31612 | Vmn1r192 | NM_145845.1 | chr13:22279014-22279917 |
| 31613 | Vmn1r193 | NM_134225.1 | chr13:22310729-22311689 |
| 31614 | Vmn1r194 | NM_001080972.1 | chr13:22336083-22336974 |
| 31615 | Vmn1r195 | NM_134223.2 | chr13:22370185-22371273 |
| 31616 | Vmn1r196 | NM_001167541.1 | chr13:22385061-22385967 |
| 31617 | Vmn1r197 | NM_134244.1 | chr13:22419779-22420676 |
| 31618 | Vmn1r198 | NM_134220.1 | chr13:22446214-22447117 |
| 31619 | Vmn1r199 | NM_134213.1 | chr13:22474406-22475510 |
| 31620 | Vmn1r2 | NM_001167534.1 | chr4:3099229-3100150 |
| 31621 | Vmn1r20 | NM_001101533.1 | chr6:57381684-57382596 |
| 31622 | Vmn1r200 | NM_134212.1 | chr13:22486897-22487836 |
| 31623 | Vmn1r201 | NM_134221.1 | chr13:22566486-22567389 |
| 31624 | Vmn1r202 | NM_134224.1 | chr13:22593205-22594114 |
| 31625 | Vmn1r203 | NM_134236.1 | chr13:22615919-22616855 |
| 31626 | Vmn1r204 | NM_001045544.1 | chr13:22648069-22648978 |
| 31627 | Vmn1r205 | NM_134217.1 | chr13:22683848-22684799 |
| 31628 | Vmn1r206 | NM_134216.1 | chr13:22711965-22712904 |
| 31629 | Vmn1r207-ps | NM_001166709.1 | chr13:22817552-22818491 |
| 31630 | Vmn1r208 | NM_134218.1 | chr13:22864267-22865194 |
| 31631 | Vmn1r209 | NM_001013787.1 | chr13:22897448-22898387 |
| 31632 | Vmn1r21 | NM_134183.1 | chr6:57793557-57794451 |
| 31633 | Vmn1r210 | NM_134235.1 | chr13:22919062-22919983 |
| 31634 | Vmn1r211 | NM_134243.1 | chr13:22943467-22944364 |
| 31635 | Vmn1r212 | NM_134241.1 | chr13:22974956-22976030 |
| 31636 | Vmn1r213 | NM_134215.1 | chr13:23103117-23104272 |
| 31637 | Vmn1r214 | NM_134214.1 | chr13:23126206-23127310 |
| 31638 | Vmn1r215 | NM_134219.1 | chr13:23167660-23168563 |
| 31639 | Vmn1r216 | NM_134245.1 | chr13:23191017-23191914 |
| 31640 | Vmn1r217 | NM_134239.1 | chr13:23205702-23206599 |
| 31641 | Vmn1r218 | NM_134222.1 | chr13:23228353-23229250 |
| 31642 | Vmn1r219 | NM_134238.1 | chr13:23254511-23255450 |
| 31643 | Vmn1r22 | NM_134178.1 | chr6:57850075-57850984 |

Fig. 25 - 168

| | | | |
|---|---|---|---|
| 31644 | Vmn1r220 | NM_134237.1 | chr13:23275496-23276393 |
| 31645 | Vmn1r221 | NM_001167542.1 | chr13:23309241-23310180 |
| 31646 | Vmn1r222 | NM_134240.1 | chr13:23323983-23324910 |
| 31647 | Vmn1r223 | NM_001083311.1 | chr13:23341108-23342192 |
| 31648 | Vmn1r224 | NM_001166735.1 | chr17:20556126-20557023 |
| 31649 | Vmn1r225 | NM_134194.1 | chr17:20639262-20640159 |
| 31650 | Vmn1r226 | NM_134191.1 | chr17:20824471-20825368 |
| 31651 | Vmn1r227 | NM_134195.2 | chr17:20872063-20873090 |
| 31652 | Vmn1r228 | NM_134192.3 | chr17:20913022-20914465 |
| 31653 | Vmn1r229 | NM_134190.1 | chr17:20951458-20952379 |
| 31654 | Vmn1r23 | NM_134179.1 | chr6:57875876-57876785 |
| 31655 | Vmn1r230 | NM_134197.1 | chr17:20983514-20984465 |
| 31656 | Vmn1r231 | NM_134196.1 | chr17:21026679-21027615 |
| 31657 | Vmn1r232 | NM_134193.2 | chr17:21050168-21051327 |
| 31658 | Vmn1r233 | NM_134202.1 | chr17:21130690-21131650 |
| 31659 | Vmn1r234 | NM_134198.1 | chr17:21365789-21366779 |
| 31660 | Vmn1r235 | NM_134199.3 | chr17:21397390-21399827 |
| 31661 | Vmn1r236 | NM_134201.2 | chr17:21423496-21424617 |
| 31662 | Vmn1r237 | NM_134200.1 | chr17:20599336-20618200 |
| 31663 | Vmn1r238 | NM_001167539.1 | chr18:3112491-3123412 |
| 31664 | Vmn1r24 | NM_134173.2 | chr6:57905634-57906525 |
| 31665 | Vmn1r25 | NM_053238.2 | chr6:57928387-57929296 |
| 31666 | Vmn1r26 | NM_134172.1 | chr6:57958176-57959196 |
| 31667 | Vmn1r27 | NM_134186.2 | chr6:58165099-58166011 |
| 31668 | Vmn1r28 | NM_134180.1 | chr6:58215167-58216076 |
| 31669 | Vmn1r29 | NM_053232.1 | chr6:58257290-58258202 |
| 31670 | Vmn1r3 | NM_001167535.1 | chr4:3111531-3112452 |
| 31671 | Vmn1r30 | NM_134177.1 | chr6:58384930-58385839 |
| 31672 | Vmn1r31 | NM_001166729.1 | chr6:58421960-58422872 |
| 31673 | Vmn1r32 | NM_134170.3 | chr6:66502176-66509702 |
| 31674 | Vmn1r33 | NM_134169.1 | chr6:66561644-66562562 |
| 31675 | Vmn1r34 | NM_001166719.1 | chr6:66586816-66587746 |
| 31676 | Vmn1r35 | NM_134167.1 | chr6:66628787-66629678 |
| 31677 | Vmn1r36 | NM_134166.1 | chr6:66665965-66666883 |
| 31678 | Vmn1r37 | NM_134165.1 | chr6:66681385-66682294 |
| 31679 | Vmn1r38 | NM_134177.1 | chr6:66726215-66727124 |
| 31680 | Vmn1r39 | NM_001166720.1 | chr6:66754408-66755326 |
| 31681 | Vmn1r4 | NM_134176.1 | chr6:56906506-56907400 |
| 31682 | Vmn1r40 | NM_053226.1 | chr6:89664196-89665129 |
| 31683 | Vmn1r41 | NM_053230.2 | chr6:89690881-89697408 |
| 31684 | Vmn1r42 | NM_053221.2 | chr6:89794511-89795609 |
| 31685 | Vmn1r43 | NM_053220.2 | chr6:89819454-89820523 |
| 31686 | Vmn1r44 | NM_053227.2 | chr6:89843267-89844200 |
| 31687 | Vmn1r45 | NM_011684.2 | chr6:89881643-89890501 |
| 31688 | Vmn1r46 | NM_053229.1 | chr6:89926164-89927094 |
| 31689 | Vmn1r47 | NM_053219.2 | chr6:89971881-89972814 |
| 31690 | Vmn1r48 | NM_053218.1 | chr6:89985926-89986835 |
| 31691 | Vmn1r49 | NM_011911.1 | chr6:90022079-90023012 |
| 31692 | Vmn1r5 | NM_134174.2 | chr6:56935335-56936283 |
| 31693 | Vmn1r50 | NM_053225.1 | chr6:90057268-90058201 |
| 31694 | Vmn1r51 | NM_011683.2 | chr6:90072636-90080639 |
| 31695 | Vmn1r52 | NM_053222.1 | chr6:90128709-90129639 |
| 31696 | Vmn1r53 | NM_053223.2 | chr6:90173310-90174432 |
| 31697 | Vmn1r54 | NM_053224.1 | chr6:90219099-90220047 |
| 31698 | Vmn1r55 | NM_001166706.1 | chr7:5098091-5099024 |
| 31699 | Vmn1r56 | NM_030740.1 | chr7:5146517-5148349 |
| 31700 | Vmn1r57 | NM_001166734.1 | chr7:5172079-5173012 |
| 31701 | Vmn1r58 | NM_030739.2 | chr7:5360491-5364747 |
| 31702 | Vmn1r59 | NM_207543.1 | chr7:5405428-5406361 |
| 31703 | Vmn1r6 | NM_134175.1 | chr6:56952348-56953260 |
| 31704 | Vmn1r60 | NM_001166732.1 | chr7:5495798-5496701 |
| 31705 | Vmn1r61 | NM_001166733.1 | chr7:5562012-5562915 |
| 31706 | Vmn1r62 | NM_030741.2 | chr7:5626205-5628199 |
| 31707 | Vmn1r62 | NM_030741.2 | chr7_random:93812-95806 |
| 31708 | Vmn1r63 | NM_030742.1 | chr7:5753949-5757047 |
| 31709 | Vmn1r63 | NM_030742.1 | chr7_random:148881-151977 |
| 31710 | Vmn1r64 | NM_207544.1 | chr7:5835181-5836144 |
| 31711 | Vmn1r65 | NM_030738.1 | chr7:5959351-5962612 |
| 31712 | Vmn1r66 | NM_134230.3 | chr7:10859176-10860700 |
| 31713 | Vmn1r67 | NM_134229.2 | chr7:11032137-11033136 |
| 31714 | Vmn1r68 | NM_001172071.1 | chr7:11112558-11113518 |
| 31715 | Vmn1r69 | NM_145842.3 | chr7:11165104-11166836 |
| 31716 | Vmn1r7 | NM_001166710.1 | chr7:56974331-56975267 |
| 31717 | Vmn1r70 | NM_134228.1 | chr7:11218935-11219832 |
| 31718 | Vmn1r71 | NM_145848.3 | chr7:11332850-11334887 |
| 31719 | Vmn1r72 | NM_145843.1 | chr7:12254947-12255868 |
| 31720 | Vmn1r73 | NM_134203.1 | chr7:12341605-12342517 |
| 31721 | Vmn1r74 | NM_134206.1 | chr7:12432123-12433038 |
| 31722 | Vmn1r75 | NM_134207.1 | chr7:12465691-12466609 |
| 31723 | Vmn1r76 | NM_134205.2 | chr7:12515659-12516634 |
| 31724 | Vmn1r77 | NM_001166731.1 | chr7:12626647-12627568 |
| 31725 | Vmn1r78 | NM_134208.2 | chr7:12737812-12738754 |
| 31726 | Vmn1r79 | NM_001166835.1 | chr7:12761541-12762462 |
| 31727 | Vmn1r8 | NM_134187.3 | chr6:56985906-56987119 |
| 31728 | Vmn1r80 | NM_134204.2 | chr7:12778313-12779240 |
| 31729 | Vmn1r81 | NM_134210.1 | chr7:12845107-12846028 |
| 31730 | Vmn1r82 | NM_134234.1 | chr7:12890153-12891068 |
| 31731 | Vmn1r83 | NM_134209.1 | chr7:12906556-12907477 |
| 31732 | Vmn1r84 | NM_134233.1 | chr7:12947156-12948113 |
| 31733 | Vmn1r85 | NM_145847.1 | chr7:13669637-13670564 |
| 31734 | Vmn1r86 | NM_001167536.1 | chr7:13687345-13688296 |
| 31735 | Vmn1r87 | NM_134227.1 | chr7:13716819-13717707 |
| 31736 | Vmn1r88 | NM_001167537.1 | chr7:13763067-13764018 |
| 31737 | Vmn1r89 | NM_134226.1 | chr7:13804687-13805638 |
| 31738 | Vmn1r9 | NM_134185.2 | chr6:57020888-57021939 |
| 31739 | Vmn1r90 | NM_001244031.1 | chr7:15146591-15147520 |
| 31740 | Vmn1r91 | NM_001166736.1 | chr7:20686506-20687430 |
| 31741 | Vmn1r93 | NM_207547.2 | chr7:20723471-20724437 |
| 31742 | Vmn1r93 | NM_207547.2 | chr7:22918794-22919760 |
| 31743 | Vmn1r94 | NM_001166723.1 | chr7:20752808-20753726 |
| 31744 | Vmn1r-ps103 | NM_134211.2 | chr13:22533140-22534112 |
| 31745 | Vmn1r-ps79 | NR_030707.1 | chr7:20941974-20944267 |
| 31746 | Vmn1r-ps79 | NR_030707.1 | chr7:23137281-23139574 |
| 31747 | Vmn2r1 | NM_019918.2 | chr3:63885563-63909380 |
| 31748 | Vmn2r10 | NM_009491.3 | chr5:109424557-109435455 |
| 31749 | Vmn2r100 | NM_001104562.1 | chr17:19641774-19669024 |
| 31750 | Vmn2r101 | NM_001104563.1 | chr17:19714194-19749281 |
| 31751 | Vmn2r102 | NM_001104564.1 | chr17:19797362-19831712 |
| 31752 | Vmn2r103 | NM_001104565.1 | chr17:19910326-19949500 |
| 31753 | Vmn2r104 | NM_001104566.1 | chr17:20166388-20185169 |
| 31754 | Vmn2r105 | NM_001104567.1 | chr17:20345193-20371836 |
| 31755 | Vmn2r106 | NM_001104568.1 | chr17:20404510-20422394 |
| 31756 | Vmn2r107 | NM_001104569.1 | chr17:20482388-20512736 |
| 31757 | Vmn2r108 | NM_001104570.1 | chr17:20599336-20618200 |
| 31758 | Vmn2r109 | NM_001104571.1 | chr17:20677480-20701720 |
| 31759 | Vmn2r11 | NM_001104622.1 | chr5:109475891-109488471 |
| 31760 | Vmn2r110 | NM_001104572.1 | chr17:20710792-20733223 |
| 31761 | Vmn2r111 | NM_001104573.1 | chr17:22684907-22710240 |
| 31762 | Vmn2r112 | NM_001104575.1 | chr17:22738114-22756100 |
| 31763 | Vmn2r113 | NM_001104578.1 | chr17:23080150-23095781 |
| 31764 | Vmn2r114 | NM_001102584.1 | chr17:23427900-23449280 |
| 31765 | Vmn2r115 | NM_001104579.1 | chr17:23480943-23497095 |
| 31766 | Vmn2r116 | NM_001104580.1 | chr17:23521769-23538831 |
| 31767 | Vmn2r117 | NM_001104581.1 | chr17:23596641-23616564 |
| 31768 | Vmn2r118 | NM_001104582.1 | chr17:55731638-55763970 |
| 31769 | Vmn2r12 | NM_001104623.1 | chr5:109514867-109526883 |
| 31770 | Vmn2r120 | NM_001104591.1 | chr17:57648205-57684737 |
| 31771 | Vmn2r121 | NM_001100616.1 | chrX:121240947-121249519 |
| 31772 | Vmn2r123 | NM_009485.1 | chrUn_random:2735833-2743962 |
| 31773 | Vmn2r124 | NM_001271883.1 | chr17:18186447-18211184 |
| 31774 | Vmn2r13 | NM_001104624.1 | chr5:109585086-109621126 |
| 31775 | Vmn2r14 | NM_001104625.1 | chr5:109644520-109653641 |
| 31776 | Vmn2r15 | NM_001104626.1 | chr5:109715287-109726575 |
| 31777 | Vmn2r16 | NM_001104627.1 | chr5:109759399-109793500 |
| 31778 | Vmn2r17 | NM_001104628.1 | chr5:109849031-109882406 |
| 31779 | Vmn2r18 | NM_001102582.1 | chr5:152364235-152389499 |
| 31780 | Vmn2r19 | NM_001104632.1 | chr6:123258350-123286555 |
| 31781 | Vmn2r2 | NM_001104592.1 | chr3:63920353-63941402 |
| 31782 | Vmn2r20 | NM_001104634.1 | chr6:123335279-123368079 |
| 31783 | Vmn2r21 | NM_001104635.1 | chr6:123442525-123488424 |
| 31784 | Vmn2r22 | NM_001104637.1 | chr6:123559775-123600653 |
| 31785 | Vmn2r23 | NM_001104638.1 | chr6:123652838-123692257 |
| 31786 | Vmn2r24 | NM_001104639.1 | chr6:123728988-123766298 |
| 31787 | Vmn2r25 | NM_001104641.1 | chr6:123772831-123803208 |
| 31788 | Vmn2r26 | NM_019917.2 | chr6:123974775-124012053 |
| 31789 | Vmn2r27 | NM_001104642.1 | chr6:124141613-124181802 |
| 31790 | Vmn2r28 | NM_001081405.1 | chr7:5432057-5445453 |
| 31791 | Vmn2r29 | NM_001113468.1 | chr7:7165706-7231000 |
| 31792 | Vmn2r29 | NR_003555.1 | chr7:7165706-7231000 |
| 31793 | Vmn2r3 | NM_001104614.1 | chr3:64062852-64091339 |
| 31794 | Vmn2r30 | NM_009490.3 | chr7:7264984-7290204 |
| 31795 | Vmn2r31 | NM_001105062.1 | chr7:7336695-7352338 |
| 31796 | Vmn2r32 | NM_001105063.1 | chr7:7416679-7432684 |
| 31797 | Vmn2r33 | NM_001105065.2 | chr7:7503677-7519497 |
| 31798 | Vmn2r34 | NM_001105066.1 | chr7:7624539-7642109 |
| 31799 | Vmn2r35 | NM_001105067.1 | chr7:7738861-7772578 |
| 31800 | Vmn2r35 | NM_001105067.1 | chr8:8639867-8851885 |
| 31801 | Vmn2r36 | NM_001105068.1 | chr7:7829363-7855173 |
| 31802 | Vmn2r36 | NM_001105068.1 | chr8:8557271-8583083 |
| 31803 | Vmn2r37 | NM_009489.2 | chr8:8954256-8972357 |
| 31804 | Vmn2r38 | NM_001105070.1 | chr7:9080031-9103000 |
| 31805 | Vmn2r39 | NM_001105071.1 | chr7:9147158-9163091 |
| 31806 | Vmn2r4 | NM_001104615.1 | chr3:64192542-64213979 |
| 31807 | Vmn2r40 | NM_001105072.1 | chr7:9246438-9270107 |
| 31808 | Vmn2r41 | NM_001105073.1 | chr7:9965778-9989425 |
| 31809 | Vmn2r42 | NM_009493.2 | chr7:9927008-9944061 |
| 31810 | Vmn2r43 | NM_198961.2 | chr7:9866726-9882971 |
| 31811 | Vmn2r44 | NM_001105074.1 | chr7:9744079-9759858 |
| 31812 | Vmn2r45 | NM_001105075.1 | chr7:9638310-9655801 |
| 31813 | Vmn2r46 | NM_001105076.1 | chr7:10339984-10355920 |
| 31814 | Vmn2r46 | NM_001105076.1 | chr8:8317008-8332944 |
| 31815 | Vmn2r47 | NM_001105151.1 | chr7:9352155-9376703 |
| 31816 | Vmn2r47 | NM_001105151.1 | chr8:8246254-8270798 |
| 31817 | Vmn2r47 | NM_001105151.1 | chr7:10092186-10116991 |
| 31818 | Vmn2r47 | NM_001105151.1 | chr7:10402130-10426674 |
| 31819 | Vmn2r48 | NM_001105152.1 | chr7:10512972-10538934 |
| 31820 | Vmn2r49 | NM_001105156.1 | chr7:10561593-10577483 |
| 31821 | Vmn2r5 | NM_001104618.1 | chr3:64294742-64311607 |
| 31822 | Vmn2r50 | NM_001105178.1 | chr7:10622583-10638527 |
| 31823 | Vmn2r51 | NM_001105179.1 | chr7:10672546-10691008 |
| 31824 | Vmn2r52 | NM_001105191.1 | chr7:10744080-10761635 |
| 31825 | Vmn2r53 | NM_001104644.1 | chr7:13166818-13191893 |
| 31826 | Vmn2r54 | NM_001081449.2 | chr7:13209581-13221483 |
| 31827 | Vmn2r55 | NM_001104645.1 | chr7:13237054-13270340 |
| 31828 | Vmn2r56 | NM_001104648.1 | chr7:13279346-13318454 |
| 31829 | Vmn2r57 | NM_177764.4 | chr7:48655101-48704011 |
| 31830 | Vmn2r58 | NM_001105055.1 | chr7:49092250-49128040 |
| 31831 | Vmn2r59 | NM_001105056.1 | chr7:49267161-49314351 |
| 31832 | Vmn2r6 | NM_001104619.1 | chr3:64341482-64363740 |

Fig. 25 - 169

| | | | |
|---|---|---|---|
| 31833 | Vmn2r60 | NM_001105057.1 | chr7:49371840-49451146 |
| 31834 | Vmn2r61 | NM_001105058.1 | chr7:49515422-49556125 |
| 31835 | Vmn2r62 | NM_001105059.1 | chr7:50019807-50048866 |
| 31836 | Vmn2r63 | NM_001105060.1 | chr7:50158620-50189159 |
| 31837 | Vmn2r65 | NM_001105180.1 | chr7:92088678-92112519 |
| 31838 | Vmn2r66 | NM_001033878.3 | chr7:92143154-92160530 |
| 31839 | Vmn2r67 | NM_001102579.1 | chr7:92284749-92304412 |
| 31840 | Vmn2r68 | NM_001105181.1 | chr7:92370027-92386214 |
| 31841 | Vmn2r69 | NM_001105182.1 | chr7:92554885-92564186 |
| 31842 | Vmn2r7 | NM_175674.3 | chr3:64494582-64523524 |
| 31843 | Vmn2r70 | NM_001105183.1 | chr7:92707212-92717598 |
| 31844 | Vmn2r71 | NM_001105184.1 | chr7:92763971-92773057 |
| 31845 | Vmn2r72 | NM_001105185.1 | chr7:92886293-92903491 |
| 31846 | Vmn2r73 | NM_001105186.1 | chr7:93000056-93024448 |
| 31847 | Vmn2r74 | NM_001105187.1 | chr7:93100376-93109992 |
| 31848 | Vmn2r75 | NM_001102578.1 | chr7:93296551-93320234 |
| 31849 | Vmn2r76 | NM_001105280.1 | chr7:93373715-93394711 |
| 31850 | Vmn2r77 | NM_001105188.1 | chr7:93943650-93960542 |
| 31851 | Vmn2r78 | NM_001105189.1 | chr7:94063858-94103687 |
| 31852 | Vmn2r79 | NM_001105190.1 | chr7:94144974-94186478 |
| 31853 | Vmn2r8 | NM_001104620.1 | chr5:109226211-109237773 |
| 31854 | Vmn2r80 | NM_001103368.1 | chr10:78611560-78657678 |
| 31855 | Vmn2r81 | NM_175936.1 | chr10:78710521-78757280 |
| 31856 | Vmn2r82 | NM_001101572.1 | chr10:78819335-78859511 |
| 31857 | Vmn2r83 | NM_001104537.1 | chr10:78931702-78954899 |
| 31858 | Vmn2r84 | NM_001081448.1 | chr10:129822855-129831297 |
| 31859 | Vmn2r85 | NM_001102602.1 | chr10:129855316-129866668 |
| 31860 | Vmn2r86 | NM_001103365.1 | chr10:129883254-129892950 |
| 31861 | Vmn2r87 | NM_001103366.1 | chr10:129908876-129934435 |
| 31862 | Vmn2r88 | NM_011686.1 | chr14:52030675-52038557 |
| 31863 | Vmn2r89 | NM_009486.3 | chr14:52071636-52080968 |
| 31864 | Vmn2r89 | NM_009487.1 | chr14:52071636-52080968 |
| 31865 | Vmn2r89 | NR_104384.1 | chr14:52071636-52080968 |
| 31866 | Vmn2r9 | NM_001104539.1 | chr5:109271965-109281529 |
| 31867 | Vmn2r90 | NM_001104539.1 | chr17:17840904-17871131 |
| 31868 | Vmn2r91 | NM_001104540.1 | chr17:18222020-18273607 |
| 31869 | Vmn2r92 | NM_001104541.1 | chr17:18288893-18322142 |
| 31870 | Vmn2r93 | NM_001104542.1 | chr17:18435244-18463405 |
| 31871 | Vmn2r94 | NM_001104543.1 | chr17:18380533-18414530 |
| 31872 | Vmn2r95 | NM_001102581.1 | chr17:18561067-18589288 |
| 31873 | Vmn2r96 | NM_001104547.1 | chr17:18718690-18735121 |
| 31874 | Vmn2r97 | NM_001104549.1 | chr17:19051285-19085035 |
| 31875 | Vmn2r98 | NM_001104550.1 | chr17:19190456-19218275 |
| 31876 | Vmn2r99 | NM_001104551.2 | chr17:19499098-19531554 |
| 31877 | Vmn2r-ps11 | NR_003962.1 | chr3:64436785-64648665 |
| 31878 | Vmn2r-ps129 | NR_033648.1 | chr17:23141937-23143626 |
| 31879 | Vmn2r-ps159 | NR_038052.1 | chrUn_random:2735805-2743961 |
| 31880 | Vmn2r-ps54 | NR_004441.1 | chr7:48923383-48982563 |
| 31881 | Vmn2r-ps60 | NR_028441.1 | chr7:49685474-49685739 |
| 31882 | Vmo1 | NM_001013607.1 | chr10:70327017-70328118 |
| 31883 | Vmp1 | NM_029478.3 | chr11:86397367-86497324 |
| 31884 | Vnn1 | NM_011704.3 | chr10:23614493-23625149 |
| 31885 | Vnn3 | NM_011979.2 | chr10:23571267-23589649 |
| 31886 | Vopp1 | NM_146168.1 | chr6:57702257-57775119 |
| 31887 | Vprbp | NM_001015507.2 | chr9:106724306-106783323 |
| 31888 | Vpreb1 | NM_016982.2 | chr16:16868493-16869348 |
| 31889 | Vpreb2 | NM_016983.1 | chr16:17980657-17981173 |
| 31890 | Vpreb3 | NM_009514.4 | chr10:75411056-75412391 |
| 31891 | Vps11 | NM_027889.1 | chr9:44156187-44169753 |
| 31892 | Vps13a | NM_173028.4 | chr19:16689856-16895423 |
| 31893 | Vps13b | NM_177151.3 | chr15:35301301-35860984 |
| 31894 | Vps13c | NM_177164.3 | chr9:67688202-67843441 |
| 31895 | Vps13d | NM_001276465.1 | chr4:144562524-144784908 |
| 31896 | Vps13d | NM_001276502.1 | chr4:144562524-144784908 |
| 31897 | Vps16 | NM_030559.3 | chr2:130250056-130270005 |
| 31898 | Vps18 | NM_172269.3 | chr2:119114477-119124189 |
| 31899 | Vps25 | NM_001284411.1 | chr11:101115020-101120861 |
| 31900 | Vps25 | NM_001284412.1 | chr11:101115020-101120861 |
| 31901 | Vps25 | NM_001284414.1 | chr11:101115020-101120861 |
| 31902 | Vps25 | NM_026776.4 | chr11:101115020-101120861 |
| 31903 | Vps26a | NM_001113355.1 | chr10:61917590-61949553 |
| 31904 | Vps26a | NM_133672.3 | chr10:61917590-61949553 |
| 31905 | Vps26b | NM_178027.4 | chr9:26812087-26837679 |
| 31906 | Vps28 | NM_025842.4 | chr15:76452517-76456457 |
| 31907 | Vps29 | NM_019780.1 | chr5:122804421-122813296 |
| 31908 | Vps33a | NM_029929.3 | chr5:129978768-124023024 |
| 31909 | Vps33b | NM_178070.4 | chr7:87414540-87436465 |
| 31910 | Vps35 | NM_022997.4 | chr8:87784290-87823396 |
| 31911 | Vps36 | NM_027338.1 | chr8:23303331-23329069 |
| 31912 | Vps37a | NM_033560.3 | chr8:41597137-41636488 |
| 31913 | Vps37b | NM_177876.4 | chr5:124454649-124482269 |
| 31914 | Vps37c | NM_181403.2 | chr19:10763304-10788909 |
| 31915 | Vps37d | NM_001199671.1 | chr5:135548769-135554136 |
| 31916 | Vps37d | NM_175574.4 | chr5:135548769-135554136 |
| 31917 | Vps39 | NM_147153.3 | chr2:120142196-120178869 |
| 31918 | Vps39 | NM_178851.3 | chr2:120142196-120178869 |
| 31919 | Vps39 | NR_027618.1 | chr2:120142196-120178869 |
| 31920 | Vps41 | NM_172120.4 | chr13:18809160-18968680 |
| 31921 | Vps45 | NM_013841.3 | chr3:95803754-95862378 |
| 31922 | Vps4a | NM_126165.1 | chr8:109555225-109569656 |
| 31923 | Vps4b | NM_009190.2 | chr1:108667364-108693302 |
| 31924 | Vps51 | NM_001081041.1 | chr19:6067842-6077187 |
| 31925 | Vps52 | NM_172620.3 | chr17:34092826-34103433 |
| 31926 | Vps53 | NM_026664.3 | chr11:75859727-75893132 |
| 31927 | Vps54 | NM_001290628.1 | chr11:21139034-21271270 |
| 31928 | Vps54 | NM_139061.5 | chr11:21139034-21271270 |
| 31929 | Vps72 | NM_009336.2 | chr3:94914963-94926973 |
| 31930 | Vps8 | NM_001285893.1 | chr16:21423190-21644754 |
| 31931 | Vps8 | NM_001285894.1 | chr16:21423190-21644754 |
| 31932 | Vps9d1 | NM_028200.1 | chr8:125766256-125778075 |
| 31933 | Vrk1 | NM_001029843.1 | chr12:107248472-107315620 |
| 31934 | Vrk1 | NM_001029844.1 | chr12:107248472-107315620 |
| 31935 | Vrk1 | NM_011705.3 | chr12:107248472-107315620 |
| 31936 | Vrk2 | NM_001252447.1 | chr11:26287083-26493920 |
| 31937 | Vrk2 | NM_027260.3 | chr11:26287083-26493920 |
| 31938 | Vrk3 | NM_133945.1 | chr7:52003998-52032884 |
| 31939 | Vrtn | NM_001033776.2 | chr12:85981968-85992405 |
| 31940 | Vrtn | NM_001168588.1 | chr12:85981968-85992405 |
| 31941 | Vrtn | NM_001168589.2 | chr12:85981968-85992405 |
| 31942 | Vsig1 | NM_026103.1 | chrX:137442146-137474011 |
| 31943 | Vsig1 | NM_030181.3 | chrX:137442146-137474011 |
| 31944 | Vsig10 | NM_001033112.2 | chr5:117769274-117805015 |
| 31945 | Vsig10l | NM_001290316.1 | chr7:50718602-50727384 |
| 31946 | Vsig2 | NM_020518.2 | chr9:37346839-37351790 |
| 31947 | Vsig4 | NM_177789.4 | chrX:93442541-93488777 |
| 31948 | Vsig8 | NM_177723.4 | chr1:174486068-174493848 |
| 31949 | Vsig8 | NR_027644.1 | chr1:174486068-174493848 |
| 31950 | Vsnl1 | NM_012038.4 | chr12:11332050-11443455 |
| 31951 | Vstm2a | NM_001290539.1 | chr11:16157726-16184554 |
| 31952 | Vstm2a | NM_145967.2 | chr11:16157726-16184554 |
| 31953 | Vstm2b | NM_021387.3 | chr7:48154647-48185338 |
| 31954 | Vstm2l | NM_198627.2 | chr2:157740388-157770455 |
| 31955 | Vstm4 | NM_178791.4 | chr14:33669941-33752675 |
| 31956 | Vstm5 | NM_026955.2 | chr9:15043488-15063857 |
| 31957 | Vsx1 | NM_054068.2 | chr2:150506439-150514873 |
| 31958 | Vsx2 | NM_007701.3 | chr12:85910801-85936407 |
| 31959 | Vta1 | NM_025418.3 | chr10:14375139-14425295 |
| 31960 | Vtcn1 | NM_178594.3 | chr3:100629381-100700845 |
| 31961 | Vti1a | NM_016862.1 | chr19:55390840-55701051 |
| 31962 | Vti1b | NM_016800.3 | chr12:80257004-80273445 |
| 31963 | Vtn | NM_011707.2 | chr11:78312621-78315827 |
| 31964 | Vwa1 | NM_147776.4 | chr4:155142603-155148670 |
| 31965 | Vwa2 | NM_172840.2 | chr19:56948905-56986568 |
| 31966 | Vwa3a | NM_177697.3 | chr7:127883070-127949054 |
| 31967 | Vwa5a | NM_001145957.1 | chr9:38525852-38550922 |
| 31968 | Vwa5a | NM_172767.3 | chr9:38525852-38550922 |
| 31969 | Vwa5b1 | NM_029401.1 | chr4:138124883-138179907 |
| 31970 | Vwa5b2 | NM_001144953.1 | chr16:20589654-20605450 |
| 31971 | Vwa5b2 | NM_182636.4 | chr16:20589654-20605450 |
| 31972 | Vwa7 | NM_138582.1 | chr17:35153524-35163686 |
| 31973 | Vwa8 | NM_027906.1 | chr14:79248984-79602117 |
| 31974 | Vwa8 | NM_173758.3 | chr14:79248984-79602117 |
| 31975 | Vwa9 | NM_001077631.2 | chr9:64808638-64834788 |
| 31976 | Vwa9 | NM_175153.4 | chr9:64808638-64834788 |
| 31977 | Vwc2 | NM_177033.3 | chr11:11014018-11163529 |
| 31978 | Vwc2l | NM_177164.3 | chr1:70772288-70931971 |
| 31979 | Vwce | NM_027913.1 | chr19:10708723-10739700 |
| 31980 | Vwde | NM_001013757.2 | chr6:13135609-13174965 |
| 31981 | Vwf | NM_011708.4 | chr6:125502965-125636697 |
| 31982 | Wac | NM_001146298.2 | chr18:7868829-7929026 |
| 31983 | Wac | NM_001282093.1 | chr18:7868829-7929026 |
| 31984 | Wac | NM_153085.4 | chr18:7868829-7929026 |
| 31985 | Wap | NM_011709.5 | chr11:6535485-6538652 |
| 31986 | Wapal | NM_001004436.4 | chr14:35487113-35559403 |
| 31987 | Wars | NM_001164314.1 | chr12:110098239-110132384 |
| 31988 | Wars | NM_001164488.1 | chr12:110098239-110132384 |
| 31989 | Wars | NM_011710.3 | chr12:110098239-110132384 |
| 31990 | Wars2 | NM_027462.4 | chr3:98945013-99024126 |
| 31991 | Was | NM_009515.2 | chrX:7658591-7667617 |
| 31992 | Wasf1 | NM_031877.3 | chr10:40603339-40658375 |
| 31993 | Wasf2 | NM_153423.6 | chr4:132686548-132754245 |
| 31994 | Wasf3 | NM_145155.3 | chr5:147196581-147282701 |
| 31995 | Wash | NM_001037757.1 | chr17:66460885-66469843 |
| 31996 | Wash | NM_026833.1 | chr17:66460885-66469843 |
| 31997 | Wasl | NM_001167745.1 | chr6:24563809-24614995 |
| 31998 | Wasl | NM_028459.2 | chr6:24563809-24614995 |
| 31999 | Wbp1 | NM_001083922.1 | chr6:83069037-83071455 |
| 32000 | Wbp1 | NM_001083923.1 | chr6:83069037-83071455 |
| 32001 | Wbp1 | NM_016757.2 | chr6:83069037-83071455 |
| 32002 | Wbp11 | NM_021714.4 | chr6:136762174-136776737 |
| 32003 | Wbp1l | NM_001177812.1 | chr19:46673595-46731879 |
| 32004 | Wbp1l | NM_001177813.1 | chr19:46673595-46731879 |
| 32005 | Wbp1l | NM_146099.3 | chr19:46673595-46731879 |
| 32006 | Wbp2 | NM_016852.2 | chr11:115939886-115948278 |
| 32007 | Wbp2nl | NM_029066.1 | chr15:82129413-82144988 |
| 32008 | Wbp4 | NM_018765.3 | chr14:79859744-79881075 |
| 32009 | Wbp5 | NM_011712.2 | chrX:132779618-132781678 |
| 32010 | Wbscr16 | NM_033572.2 | chr5:134623927-134652637 |
| 32011 | Wbscr17 | NM_145218.3 | chr5:131350820-131783392 |
| 32012 | Wbscr22 | NM_025375.3 | chr5:135528827-135540536 |
| 32013 | Wbscr25 | NR_026907.1 | chr5:135463303-135477220 |
| 32014 | Wbscr27 | NM_024479.2 | chr5:135408242-135418507 |
| 32015 | Wbscr28 | NM_029681.3 | chr5:135377462-135382603 |
| 32016 | Wbscr28 | NM_194065.3 | chr5:135377462-135382603 |
| 32017 | Wdfy1 | NM_001111279.1 | chr1:79698836-79758344 |
| 32018 | Wdfy1 | NM_027057.3 | chr1:79698836-79758344 |
| 32019 | Wdfy2 | NM_175546.4 | chr14:63456527-63575723 |
| 32020 | Wdfy3 | NM_172882.3 | chr5:102263971-102498940 |
| 32021 | Wdfy4 | NM_001146022.2 | chr14:33772733-33998252 |

Fig. 25 - 170

| | | | | | | | |
|---|---|---|---|---|---|---|---|
| 32022 | Wdhd1 | NM_172598.3 | chr14:47860618-47896532 | 32117 | Wdr96 | NM_027559.2 | chr19:47811346-47911851 |
| 32023 | Wdpcp | NM_145425.3 | chr11:21472283-21798689 | 32118 | Wdsub1 | NM_001159636.1 | chr2:59690421-59720663 |
| 32024 | Wdr1 | NM_011715.2 | chr5:38918051-38952834 | 32119 | Wdsub1 | NM_028118.2 | chr2:59690421-59720663 |
| 32025 | Wdr11 | NM_172255.3 | chr7:136735376-136779252 | 32120 | Wdtc1 | NM_199306.4 | chr4:132848380-132895230 |
| 32026 | Wdr12 | NM_001199060.1 | chr1:60133711-60210797 | 32121 | Wdyhv1 | NM_029734.1 | chr15:57972990-57990209 |
| 32027 | Wdr12 | NM_001199061.1 | chr1:60133711-60210797 | 32122 | Wee1 | NM_009516.3 | chr7:117265572-117286813 |
| 32028 | Wdr12 | NM_021312.5 | chr1:60133711-60210797 | 32123 | Wee2 | NM_201370.2 | chr6:40392861-40416814 |
| 32029 | Wdr13 | NM_001290783.1 | chrX:7700426-7709984 | 32124 | Wfdc1 | NM_023395.2 | chr8:122190264-122211920 |
| 32030 | Wdr13 | NM_026137.5 | chrX:7700426-7709984 | 32125 | Wfdc10 | NM_001039501.2 | chr2:164481545-164482868 |
| 32031 | Wdr13 | NM_028542.1 | chrX:7700426-7709984 | 32126 | Wfdc11 | NM_001161806.1 | chr2:164488393-164499587 |
| 32032 | Wdr13 | NR_029428.1 | chrX:7700426-7709984 | 32127 | Wfdc12 | NM_138684.2 | chr2:164014966-164016294 |
| 32033 | Wdr16 | NM_027963.2 | chr11:67738307-67779144 | 32128 | Wfdc13 | NM_001012704.1 | chr2:164510606-164513206 |
| 32034 | Wdr17 | NM_001172152.1 | chr8:55714968-55809721 | 32129 | Wfdc15a | NM_183271.2 | chr2:164024607-164025853 |
| 32035 | Wdr17 | NM_028220.3 | chr8:55714968-55809721 | 32130 | Wfdc15b | NM_001045554.1 | chr2:164040189-164047399 |
| 32036 | Wdr18 | NM_175450.4 | chr10:79422886-79431991 | 32131 | Wfdc15b | NM_138685.2 | chr2:164040189-164047399 |
| 32037 | Wdr19 | NM_153173.2 | chr5:65590934-65651654 | 32132 | Wfdc16 | NM_001012723.2 | chr2:164460207-164464302 |
| 32038 | Wdr20 | NM_027149.2 | chr12:111976158-112033238 | 32133 | Wfdc17 | NM_001081957.1 | chr2:83517557-83519771 |
| 32039 | Wdr20rt | NM_027614.1 | chr12:66326503-66329441 | 32134 | Wfdc18 | NM_007969.3 | chr11:83522505-83524862 |
| 32040 | Wdr24 | NM_173741.3 | chr17:25960571-25965675 | 32135 | Wfdc2 | NM_026323.2 | chr2:164388215-164394006 |
| 32041 | Wdr25 | NM_177602.3 | chr12:110132481-110266662 | 32136 | Wfdc3 | NM_027961.1 | chr2:164556725-164568767 |
| 32042 | Wdr26 | NM_145514.5 | chr1:183103356-183142109 | 32137 | Wfdc5 | NM_145369.3 | chr2:164002060-164008478 |
| 32043 | Wdr27 | NM_175173.3 | chr17:14955678-15080129 | 32138 | Wfdc6a | NM_001033240.4 | chr2:164405018-164410947 |
| 32044 | Wdr3 | NM_175552.4 | chr3:99942103-99966326 | 32139 | Wfdc6a | NM_001177848.1 | chr2:164405018-164410947 |
| 32045 | Wdr31 | NM_001290521.1 | chr4:62113665-62131929 | 32140 | Wfdc6b | NM_001012725.2 | chr2:164439199-164443713 |
| 32046 | Wdr31 | NM_001290522.1 | chr4:62113665-62131929 | 32141 | Wfdc8 | NM_001080550.2 | chr2:164421957-164439126 |
| 32047 | Wdr31 | NM_023597.2 | chr4:62113665-62131929 | 32142 | Wfdc8 | NM_001276431.1 | chr2:164421957-164439126 |
| 32048 | Wdr33 | NM_001170966.1 | chr18:31963710-32068641 | 32143 | Wfdc8 | NM_001276432.1 | chr2:164421957-164439126 |
| 32049 | Wdr33 | NM_001170967.1 | chr18:31963710-32068641 | 32144 | Wfdc9 | NM_001160414.1 | chr2:164475124-164480466 |
| 32050 | Wdr33 | NM_001170970.1 | chr18:31963710-32068641 | 32145 | Wfikkn1 | NM_001100454.1 | chr17:26014572-26017803 |
| 32051 | Wdr33 | NM_028866.3 | chr18:31963710-32068641 | 32146 | Wfikkn2 | NM_181819.2 | chr11:94097265-94103893 |
| 32052 | Wdr34 | NM_001004498.2 | chr2:29887077-29904399 | 32147 | Wfs1 | NM_011716.2 | chr5:37357342-37380221 |
| 32053 | Wdr35 | NM_001159527.1 | chr12:8980806-9035653 | 32148 | Whamm | NM_001004185.3 | chr7:88716177-88741722 |
| 32054 | Wdr35 | NM_172470.3 | chr12:8980806-9035653 | 32149 | Whrn | NM_001008791.2 | chr4:63075943-63157025 |
| 32055 | Wdr36 | NM_001110015.1 | chr18:32832295-33026074 | 32150 | Whrn | NM_001008792.2 | chr4:63075943-63157025 |
| 32056 | Wdr36 | NM_001110016.1 | chr18:32832295-33026074 | 32151 | Whrn | NM_001008793.2 | chr4:63075943-63157025 |
| 32057 | Wdr36 | NM_144863.2 | chr18:32832295-33026074 | 32152 | Whrn | NM_001276371.1 | chr4:63075943-63157025 |
| 32058 | Wdr37 | NM_001039388.2 | chr13:8802211-8870982 | 32153 | Whrn | NM_028640.2 | chr4:63075943-63157025 |
| 32059 | Wdr37 | NM_001039389.2 | chr13:8802211-8870982 | 32154 | Whsc1 | NM_001081102.2 | chr5:34185760-34240615 |
| 32060 | Wdr37 | NM_172485.3 | chr13:8802211-8870982 | 32155 | Whsc1 | NM_001177884.1 | chr5:34185760-34240615 |
| 32061 | Wdr38 | NM_029687.3 | chr2:38853829-38857104 | 32156 | Whsc1 | NM_175231.2 | chr5:34185760-34240615 |
| 32062 | Wdr4 | NM_021322.2 | chr17:31631266-31649432 | 32157 | Whsc1l1 | NM_001001735.2 | chr8:26712777-26830139 |
| 32063 | Wdr41 | NM_172759.3 | chr13:95746298-95793271 | 32158 | Whsc1l1 | NM_001081269.2 | chr8:26712777-26830139 |
| 32064 | Wdr43 | NM_175639.1 | chr17:71965555-72008371 | 32159 | Wibg | NM_001170869.2 | chr10:128184934-128203624 |
| 32065 | Wdr44 | NM_175180.3 | chrX:23270242-23383127 | 32160 | Wibg | NM_001253704.1 | chr10:128184934-128203624 |
| 32066 | Wdr45 | NM_001290793.1 | chrX:7299345-7305327 | 32161 | Wibg | NM_001253705.1 | chr10:128184934-128203624 |
| 32067 | Wdr45 | NM_001290794.1 | chrX:7299345-7305327 | 32162 | Wibg | NM_030100.4 | chr10:128184934-128203624 |
| 32068 | Wdr45 | NM_001290795.1 | chrX:7299345-7305327 | 32163 | Wif1 | NM_011915.2 | chr10:120471059-120537698 |
| 32069 | Wdr45 | NM_172372.2 | chrX:7299345-7305327 | 32164 | Wipf1 | NM_001289722.1 | chr2:73267666-73367544 |
| 32070 | Wdr45b | NM_025793.3 | chr11:121188518-121215761 | 32165 | Wipf1 | NM_001289723.1 | chr2:73267666-73367544 |
| 32071 | Wdr46 | NM_020603.2 | chr17:34077667-34086640 | 32166 | Wipf1 | NM_153138.4 | chr2:73267666-73367544 |
| 32072 | Wdr47 | NM_181400.3 | chr3:108394195-108448637 | 32167 | Wipf2 | NM_197940.2 | chr11:98724911-98766892 |
| 32073 | Wdr48 | NM_026236.3 | chr9:119804013-119835697 | 32168 | Wipf3 | NM_001167860.1 | chr6:54402876-54453762 |
| 32074 | Wdr5 | NM_080848.2 | chr2:27370666-27392055 | 32169 | Wipf3 | NM_001167861.1 | chr6:54402876-54453762 |
| 32075 | Wdr52 | NM_001033247.1 | chr16:44394911-44482541 | 32170 | Wipi1 | NM_145940.2 | chr11:109434834-109472703 |
| 32076 | Wdr53 | NM_001185162.1 | chr16:32247312-32257169 | 32171 | Wipi2 | NM_178398.4 | chr5:143105537-143145324 |
| 32077 | Wdr53 | NM_026898.2 | chr16:32247312-32257169 | 32172 | Wisp1 | NM_018865.2 | chr15:66722954-86754761 |
| 32078 | Wdr54 | NM_023790.2 | chr6:83102703-83106373 | 32173 | Wisp2 | NM_016873.2 | chr2:163646569-163658883 |
| 32079 | Wdr55 | NM_026464.2 | chr18:36919893-36923362 | 32174 | Wisp3 | NM_001127376.1 | chr10:38870777-38883600 |
| 32080 | Wdr59 | NM_001170742.1 | chr8:113972683-114046007 | 32175 | Wiz | NM_011717.4 | chr17:32490994-32526384 |
| 32081 | Wdr59 | NM_001170743.1 | chr8:113972683-114046007 | 32176 | Wiz | NM_212438.3 | chr17:32490994-32526384 |
| 32082 | Wdr59 | NM_176923.4 | chr8:113972683-114046007 | 32177 | Wiz | NR_033525.1 | chr17:32490994-32526384 |
| 32083 | Wdr5b | NM_027113.2 | chr16:36041275-36043060 | 32178 | Wls | NM_026582.1 | chr3:159502658-159598139 |
| 32084 | Wdr6 | NM_031392.2 | chr9:108474644-108481001 | 32179 | Wls | NR_037590.1 | chr3:159502658-159598139 |
| 32085 | Wdr60 | NM_146039.3 | chr12:117445522-117501498 | 32180 | Wnk1 | NM_001185020.1 | chr6:119873986-119988673 |
| 32086 | Wdr61 | NM_001025375.2 | chr9:54564959-54582356 | 32181 | Wnk1 | NM_001185021.1 | chr6:119873986-119988673 |
| 32087 | Wdr61 | NM_001025376.2 | chr9:54564959-54582356 | 32182 | Wnk1 | NM_001199083.1 | chr6:119873986-119988673 |
| 32088 | Wdr61 | NM_023191.3 | chr9:54564959-54582356 | 32183 | Wnk1 | NM_001199084.1 | chr6:119873986-119988673 |
| 32089 | Wdr62 | NM_146186.3 | chr7:31025156-31065440 | 32184 | Wnk1 | NM_198703.3 | chr6:119873986-119988673 |
| 32090 | Wdr63 | NM_172864.3 | chr3:145703489-145771000 | 32185 | Wnk2 | NM_001290311.1 | chr13:49131670-49243697 |
| 32091 | Wdr64 | NM_029453.2 | chr1:177628723-177745864 | 32186 | Wnk2 | NM_001290313.1 | chr13:49131670-49243697 |
| 32092 | Wdr65 | NM_026789.4 | chr4:118227155-118293010 | 32187 | Wnk2 | NM_029361.4 | chr13:49131670-49243697 |
| 32093 | Wdr7 | NM_001014981.1 | chr18:63868348-64149413 | 32188 | Wnk3 | NM_001271678.1 | chrX:147632620-147776422 |
| 32094 | Wdr70 | NM_001081402.1 | chr15:7823054-8049209 | 32189 | Wnk3 | NM_001271679.1 | chrX:147632620-147776422 |
| 32095 | Wdr72 | NM_001033500.3 | chr9:73958140-74131010 | 32190 | Wnk4 | NM_175638.3 | chr11:101121880-101138723 |
| 32096 | Wdr73 | NM_028026.2 | chr7:88035608-88046155 | 32191 | Wnt1 | NM_021279.4 | chr15:98620287-98624261 |
| 32097 | Wdr73 | NR_027976.1 | chr7:88035608-88046155 | 32192 | Wnt10a | NM_009518.2 | chr1:74838592-74850749 |
| 32098 | Wdr74 | NM_134139.1 | chr19:8810328-8815114 | 32193 | Wnt10b | NM_011718.1 | chr15:98602182-98608581 |
| 32099 | Wdr75 | NM_028599.2 | chr1:45852345-45880458 | 32194 | Wnt11 | NM_001285792.1 | chr7:105983621-106003257 |
| 32100 | Wdr76 | NM_001290986.1 | chr2:121332458-121370595 | 32195 | Wnt11 | NM_001285794.1 | chr7:105983621-106003257 |
| 32101 | Wdr76 | NM_001290987.1 | chr2:121332458-121370595 | 32196 | Wnt11 | NM_001285795.1 | chr7:105983621-106003257 |
| 32102 | Wdr76 | NM_030254.2 | chr2:121332458-121370595 | 32197 | Wnt11 | NM_009519.2 | chr7:105983621-106003257 |
| 32103 | Wdr77 | NM_027432.3 | chr3:105762416-105772678 | 32198 | Wnt16 | NM_053116.4 | chr6:22238226-22248522 |
| 32104 | Wdr78 | NM_146254.4 | chr4:102710669-102786904 | 32199 | Wnt2 | NM_023653.5 | chr6:17938939-17980445 |
| 32105 | Wdr8 | NM_021499.2 | chr4:153516480-153530927 | 32200 | Wnt2b | NM_009520.3 | chr3:104747722-104764627 |
| 32106 | Wdr81 | NM_138950.3 | chr11:75254444-75268219 | 32201 | Wnt3 | NM_009521.2 | chr11:103635488-103679335 |
| 32107 | Wdr82 | NM_029896.1 | chr9:106073286-106094037 | 32202 | Wnt3a | NM_009522.2 | chr11:59061543-59104253 |
| 32108 | Wdr83 | NM_026389.4 | chr8:87598934-87604645 | 32203 | Wnt4 | NM_009523.2 | chr4:136833549-136855416 |
| 32109 | Wdr83os | NM_001001493.2 | chr8:87604861-87606238 | 32204 | Wnt5a | NM_001256224.1 | chr14:29318658-29338701 |
| 32110 | Wdr86 | NM_001081441.1 | chr5:24218086-24236498 | 32205 | Wnt5a | NM_009524.3 | chr14:29318658-29338701 |
| 32111 | Wdr89 | NM_028203.1 | chr12:76731581-76770524 | 32206 | Wnt5b | NM_001271757.1 | chr6:119382548-119494365 |
| 32112 | Wdr90 | NM_001163766.1 | chr17:25981679-25998460 | 32207 | Wnt5b | NM_001271758.1 | chr6:119382548-119494365 |
| 32113 | Wdr91 | NM_001013366.1 | chr6:34830425-34860831 | 32208 | Wnt5b | NM_009525.3 | chr6:119382548-119494365 |
| 32114 | Wdr92 | NM_178909.4 | chr11:17111895-17135203 | 32209 | Wnt6 | NM_009526.3 | chr1:74818465-74831893 |
| 32115 | Wdr93 | NM_001037927.1 | chr7:86888048-86930836 | 32210 | Wnt7a | NM_009527.3 | chr6:91313976-91361363 |
| 32116 | Wdr95 | NM_029440.3 | chr5:150331254-150414469 | 32211 | Wnt7b | NM_001163633.1 | chr15:85365866-85424138 |

Fig. 25 - 171

| | | | |
|---|---|---|---|
| 32212 | Wnt7b | NM_001163634.1 | chr15:85365866-85424138 |
| 32213 | Wnt7b | NM_009528.3 | chr15:85365866-85424138 |
| 32214 | Wnt8a | NM_009290.2 | chr18:34701981-34707715 |
| 32215 | Wnt8b | NM_011720.3 | chr19:44567961-44588763 |
| 32216 | Wnt9a | NM_139298.2 | chr11:59120431-59147054 |
| 32217 | Wnt9b | NM_011719.4 | chr11:103588676-103611135 |
| 32218 | Wrap53 | NM_144824.2 | chr11:69375255-69392826 |
| 32219 | Wrb | NM_207301.2 | chr16:96367025-96379459 |
| 32220 | Wrn | NM_001122822.1 | chr8:34344844-34495999 |
| 32221 | Wrn | NM_011721.4 | chr8:34344844-34495999 |
| 32222 | Wrnip1 | NM_030215.3 | chr13:32893898-32914479 |
| 32223 | Wsb1 | NM_001042565.3 | chr11:79052883-79068197 |
| 32224 | Wsb1 | NM_019653.3 | chr11:79052883-79068197 |
| 32225 | Wsb2 | NM_021539.4 | chr5:117807313-117828568 |
| 32226 | Wscd1 | NM_177618.4 | chr11:71564204-71603148 |
| 32227 | Wscd2 | NM_177292.3 | chr5:113919466-114039679 |
| 32228 | Wt1 | NM_144783.2 | chr2:104966685-105013771 |
| 32229 | Wt1os | NR_015462.1 | chr2:104916694-104966667 |
| 32230 | Wtap | NM_001113530.1 | chr17:13159664-13185405 |
| 32231 | Wtap | NM_001113533.1 | chr17:13159664-13185405 |
| 32232 | Wtap | NM_175394.2 | chr17:13159664-13185405 |
| 32233 | Wtip | NM_207212.2 | chr7:34894566-34918287 |
| 32234 | Wwc1 | NM_170779.1 | chr11:35652679-35793591 |
| 32235 | Wwc2 | NM_133791.4 | chr8:48912963-49075905 |
| 32236 | Wwox | NM_019573.3 | chr8:116963551-117876612 |
| 32237 | Wwp1 | NM_001276292.1 | chr4:19535445-19636151 |
| 32238 | Wwp1 | NM_177327.5 | chr4:19535445-19636151 |
| 32239 | Wwp1 | NR_074089.1 | chr4:19535445-19636151 |
| 32240 | Wwp1 | NR_074090.1 | chr4:19535445-19636151 |
| 32241 | Wwp2 | NM_025830.3 | chr8:109960298-110082495 |
| 32242 | Wwtr1 | NM_001168281.1 | chr3:57259565-57379832 |
| 32243 | Wwtr1 | NM_133784.3 | chr3:57259565-57379832 |
| 32244 | Xab2 | NM_026156.2 | chr8:3610089-3621296 |
| 32245 | Xaf1 | NM_001037713.4 | chr11:72115130-72127235 |
| 32246 | Xaf1 | NM_001291153.1 | chr11:72115130-72127235 |
| 32247 | Xbp1 | NM_001271730.1 | chr11:5420643-5425996 |
| 32248 | Xbp1 | NM_013842.3 | chr11:5420643-5425996 |
| 32249 | Xcl1 | NM_008510.1 | chr1:166861778-166865641 |
| 32250 | Xcr1 | NM_011798.4 | chr9:123761435-123771246 |
| 32251 | Xdh | NM_011723.3 | chr17:74233234-74299536 |
| 32252 | Xiap | NM_009688.1 | chrX:39421012-39462841 |
| 32253 | Xirp1 | NM_011724.3 | chr9:119922872-119932716 |
| 32254 | Xirp2 | NM_001024618.2 | chr2:67284058-67364663 |
| 32255 | Xirp2 | NM_001083919.1 | chr2:67284058-67364663 |
| 32256 | Xist | NR_001463.3 | chrX:100626855-100680296 |
| 32257 | Xist | NR_001570.2 | chrX:100626855-100680296 |
| 32258 | Xk | NM_023500.2 | chrX:8849910-8890371 |
| 32259 | Xkr4 | NM_001011874.1 | chr1:3204562-3661579 |
| 32260 | Xkr5 | NM_001113350.2 | chr8:18932728-18950975 |
| 32261 | Xkr5 | NM_001286469.1 | chr8:18932728-18950975 |
| 32262 | Xkr5 | NM_176951.1 | chr8:18932728-18950975 |
| 32263 | Xkr6 | NM_173393.2 | chr14:64225367-64439247 |
| 32264 | Xkr7 | NM_001011732.1 | chr2:152857587-152881511 |
| 32265 | Xkr8 | NM_201368.1 | chr4:132280818-132288461 |
| 32266 | Xkr9 | NM_001011873.2 | chr1:13658851-13691804 |
| 32267 | Xkrx | NM_183519.3 | chrX:130683583-130696467 |
| 32268 | Xlr | NM_001291747.1 | chrX:51080294-51100883 |
| 32269 | Xlr | NM_001291748.1 | chrX:51080294-51100883 |
| 32270 | Xlr | NM_011725.2 | chrX:51080294-51100883 |
| 32271 | Xlr3a | NM_001110784.1 | chrX:70331631-70342434 |
| 32272 | Xlr3b | NM_001081643.1 | chrX:70437517-70448269 |
| 32273 | Xlr3c | NM_011727.2 | chrX:70499878-70510729 |
| 32274 | Xlr4a | NM_001081642.1 | chrX:70319683-70327846 |
| 32275 | Xlr4b | NM_021365.3 | chrX:70459703-70467792 |
| 32276 | Xlr4c | NM_183634.3 | chrX:70479414-70488469 |
| 32277 | Xlr5a | NM_001045539.2 | chrX:70352974-70363041 |
| 32278 | Xlr5b | NM_001111293.1 | chrX:70394180-70403738 |
| 32279 | Xlr5c | NM_031493.1 | chrX:70530535-70535854 |
| 32280 | Xndc1 | NM_001286689.1 | chr7:109214004-109245378 |
| 32281 | Xndc1 | NM_001286690.1 | chr7:109214004-109245378 |
| 32282 | Xntrpc | NM_011644.3 | chr7:109214004-109245378 |
| 32283 | Xntrpc | NR_104562.1 | chr7:109214004-109245378 |
| 32284 | Xpa | NM_011728.2 | chr4:46188093-46209183 |
| 32285 | Xpc | NM_009531.2 | chr6:91439301-91465882 |
| 32286 | Xpnpep1 | NM_133216.3 | chr19:53065670-53113144 |
| 32287 | Xpnpep2 | NM_001289729.1 | chrX:45461901-45490158 |
| 32288 | Xpnpep2 | NM_133213.2 | chrX:45461901-45490158 |
| 32289 | Xpnpep3 | NM_177310.2 | chr15:81230618-81285318 |
| 32290 | Xpo1 | NM_001035226.1 | chr11:23156040-23197597 |
| 32291 | Xpo1 | NM_134014.3 | chr11:23156040-23197597 |
| 32292 | Xpo4 | NM_020506.1 | chr14:58201107-58283793 |
| 32293 | Xpo5 | NM_024198.2 | chr17:46399804-46379248 |
| 32294 | Xpo6 | NM_028816.2 | chr7:133245232-133343922 |
| 32295 | Xpo7 | NM_023045.2 | chr14:71054052-71166435 |
| 32296 | Xpot | NM_001081056.1 | chr10:121024435-121063372 |
| 32297 | Xpr1 | NM_011273.2 | chr1:157122786-157264574 |
| 32298 | Xrcc1 | NM_009532.4 | chr7:25332168-25358457 |
| 32299 | Xrcc2 | NM_020570.2 | chr5:25195633-25211615 |
| 32300 | Xrcc3 | NM_028875.2 | chr12:113041404-113052052 |
| 32301 | Xrcc4 | NM_028012.4 | chr13:89988518-90229213 |
| 32302 | Xrcc5 | NM_009533.2 | chr1:72353994-72441527 |
| 32303 | Xrcc6 | NM_010247.2 | chr15:81846798-81870514 |
| 32304 | Xrcc6bp1 | NM_001159559.1 | chr10:126305483-126338427 |
| 32305 | Xrcc6bp1 | NM_026858.3 | chr10:126305483-126338427 |
| 32306 | Xrn1 | NM_011916.2 | chr9:95855178-95953448 |
| 32307 | Xrn2 | NM_011917.2 | chr2:146838795-146903723 |
| 32308 | Xrra1 | NM_001164258.1 | chr7:107007727-107066334 |
| 32309 | Xxylt1 | NM_198626.2 | chr16:30955589-31081518 |
| 32310 | Xylb | NM_001033209.3 | chr9:119266498-119302915 |
| 32311 | Xylb | NM_001199568.1 | chr9:119266498-119302915 |
| 32312 | Xylt1 | NM_175645.3 | chr7:124524492-124811144 |
| 32313 | Xylt2 | NM_145828.3 | chr11:94525160-94538807 |
| 32314 | Yae1d1 | NM_025904.3 | chr13:18078473-18085185 |
| 32315 | Yaf2 | NM_024189.2 | chr15:93114263-93167366 |
| 32316 | Yaf2 | NR_028315.1 | chr15:93114263-93167366 |
| 32317 | Yap1 | NM_001171147.1 | chr9:7932000-8004596 |
| 32318 | Yap1 | NM_009534.3 | chr9:7932000-8004596 |
| 32319 | Yars | NM_134151.4 | chr4:128867039-128896851 |
| 32320 | Yars2 | NM_198246.2 | chr16:16303057-16309733 |
| 32321 | Yars2 | NR_038046.1 | chr16:16303057-16309733 |
| 32322 | Ybey | NM_172550.4 | chr10:75922312-75931859 |
| 32323 | Ybx1 | NM_011732.2 | chr4:118945931-118967118 |
| 32324 | Ybx2 | NM_016875.2 | chr11:69749400-69755101 |
| 32325 | Ybx3 | NM_011733.2 | chr6:131314875-131338468 |
| 32326 | Ybx3 | NM_139117.2 | chr6:131314875-131338468 |
| 32327 | Ydjc | NM_026940.4 | chr16:17147059-17148950 |
| 32328 | Yeats2 | NM_001033237.2 | chr16:20141135-20232646 |
| 32329 | Yeats2 | NM_001145930.1 | chr16:20141135-20232646 |
| 32330 | Yeats2 | NM_001145931.1 | chr16:20141135-20232646 |
| 32331 | Yeats4 | NM_026570.2 | chr10:116652196-116661563 |
| 32332 | Yes1 | NM_001205132.1 | chr5:32913543-32989439 |
| 32333 | Yes1 | NM_001205133.1 | chr5:32913543-32989439 |
| 32334 | Yes1 | NM_009535.3 | chr5:32913543-32989439 |
| 32335 | Yif1a | NM_026553.4 | chr19:5088538-5092879 |
| 32336 | Yif1b | NM_001110201.1 | chr7:30023341-30033486 |
| 32337 | Yif1b | NM_029887.3 | chr7:30023341-30033486 |
| 32338 | Yipf1 | NM_001205156.1 | chr4:106986967-107032428 |
| 32339 | Yipf1 | NM_145550.3 | chr4:106986967-107032428 |
| 32340 | Yipf2 | NM_001205157.1 | chr9:21351337-21400414 |
| 32341 | Yipf2 | NM_001205158.1 | chr9:21351337-21400414 |
| 32342 | Yipf2 | NM_138303.2 | chr9:21351337-21400414 |
| 32343 | Yipf2 | NR_038062.1 | chr9:21351337-21400414 |
| 32344 | Yipf3 | NM_145353.2 | chr17:46385028-46389486 |
| 32345 | Yipf4 | NM_026417.4 | chr17:74888832-74899617 |
| 32346 | Yipf5 | NM_023311.3 | chr18:40364518-40379053 |
| 32347 | Yipf6 | NM_207633.2 | chrX:96133119-96144359 |
| 32348 | Yipf7 | NM_023784.5 | chr5:69907908-69933886 |
| 32349 | Ykt6 | NM_019661.4 | chr11:5855760-5867783 |
| 32350 | Ylpm1 | NM_178363.3 | chr12:86337270-86411465 |
| 32351 | Ymel1 | NM_013771.5 | chr2:23012024-23054780 |
| 32352 | Yod1 | NM_178691.4 | chr1:132613904-132618634 |
| 32353 | Ypel1 | NM_001291047.1 | chr16:17070231-17111345 |
| 32354 | Ypel1 | NM_001291053.1 | chr16:17070231-17111345 |
| 32355 | Ypel1 | NM_023249.6 | chr16:17070231-17111345 |
| 32356 | Ypel2 | NM_001005341.3 | chr11:86749926-86807264 |
| 32357 | Ypel3 | NM_025347.2 | chr7:133920488-133924028 |
| 32358 | Ypel3 | NM_026875.2 | chr7:133920488-133924028 |
| 32359 | Ypel4 | NM_001005342.2 | chr2:84574360-84578034 |
| 32360 | Ypel5 | NM_027166.5 | chr17:73186043-73200535 |
| 32361 | Yrdc | NM_153566.2 | chr4:124528003-124532486 |
| 32362 | Ythdc1 | NM_177680.3 | chr5:87233514-87265682 |
| 32363 | Ythdc2 | NM_001163013.1 | chr18:44988318-45049374 |
| 32364 | Ythdf1 | NM_173761.3 | chr2:180639081-180655641 |
| 32365 | Ythdf2 | NM_145393.4 | chr4:131740830-131763171 |
| 32366 | Ythdf3 | NM_001145919.1 | chr3:16083182-16117038 |
| 32367 | Ythdf3 | NM_172677.3 | chr3:16083182-16117038 |
| 32368 | Ythdf3 | NR_027375.1 | chr3:16083182-16117038 |
| 32369 | Ywhab | NM_018753.6 | chr2:163820932-163844323 |
| 32370 | Ywhae | NM_009536.4 | chr11:75546388-75579343 |
| 32371 | Ywhag | NM_018871.3 | chr5:136384248-136410511 |
| 32372 | Ywhah | NM_011738.2 | chr5:33361464-33370615 |
| 32373 | Ywhaq | NM_011739.3 | chr12:21396189-21423297 |
| 32374 | Ywhaz | NM_001253805.1 | chr15:36700015-36726684 |
| 32375 | Ywhaz | NM_001253806.1 | chr15:36700015-36726684 |
| 32376 | Ywhaz | NM_001253807.1 | chr15:36700015-36726684 |
| 32377 | Ywhaz | NM_011740.3 | chr15:36700015-36726684 |
| 32378 | Yy1 | NM_009537.3 | chr12:110031520-110054842 |
| 32379 | Yy2 | NM_001098723.1 | chrX:154004051-154006917 |
| 32380 | Zadh2 | NM_146090.5 | chr18:84257549-84266906 |
| 32381 | Zak | NM_001164791.1 | chr2:72123693-72280667 |
| 32382 | Zak | NM_023057.5 | chr2:72123693-72280667 |
| 32383 | Zak | NM_178084.4 | chr2:72123693-72280667 |
| 32384 | Zan | NM_011741.2 | chr5:137819864-137918292 |
| 32385 | Zap70 | NM_001289612.1 | chr1:36818642-36839665 |
| 32386 | Zap70 | NM_001289765.1 | chr1:36818642-36839665 |
| 32387 | Zap70 | NM_001289766.1 | chr1:36818642-36839665 |
| 32388 | Zap70 | NM_009539.3 | chr1:36818642-36839665 |
| 32389 | Zar1 | NM_174877.3 | chr5:72968352-72972323 |
| 32390 | Zar1l | NM_001159693.1 | chr5:151309643-151320734 |
| 32391 | Zbbx | NM_172515.2 | chr3:74841828-74947645 |
| 32392 | Zbed3 | NM_028106.3 | chr13:96094780-96107797 |
| 32393 | Zbed4 | NM_181412.3 | chr15:88582140-88614946 |
| 32394 | Zbed5 | NM_183088.2 | chr5:130371592-130379492 |
| 32395 | Zbed6 | NM_001166552.1 | chr1:135552456-135557462 |
| 32396 | Zbp1 | NM_001139519.1 | chr2:173032113-173044423 |
| 32397 | Zbp1 | NM_021394.2 | chr2:173032113-173044423 |
| 32398 | Zbtb1 | NM_178744.2 | chr12:77471252-77489734 |
| 32399 | Zbtb10 | NM_177660.3 | chr9:9250566-9285332 |
| 32400 | Zbtb11 | NM_173026.2 | chr16:55937917-56009025 |
| 32401 | Zbtb12 | NM_198886.3 | chr17:35031503-35033789 |

Fig. 25 - 172

| | | | |
|---|---|---|---|
| 32402 | Zbtb14 | NM_009547.2 | chr17:69733317-69739884 |
| 32403 | Zbtb16 | NM_001033324.2 | chr9:48462401-48644050 |
| 32404 | Zbtb17 | NM_009541.2 | chr4:141000588-141023852 |
| 32405 | Zbtb18 | NM_001012330.1 | chr1:179374791-179380897 |
| 32406 | Zbtb18 | NM_013915.3 | chr1:179374791-179380897 |
| 32407 | Zbtb2 | NM_001033466.3 | chr10:5958432-5979467 |
| 32408 | Zbtb20 | NM_001255805.1 | chr16:42884482-43619236 |
| 32409 | Zbtb20 | NM_019778.2 | chr16:42884482-43619236 |
| 32410 | Zbtb20 | NM_181058.1 | chr16:42884482-43619236 |
| 32411 | Zbtb21 | NM_001081684.1 | chr16:98168598-98183786 |
| 32412 | Zbtb21 | NM_001081685.1 | chr16:98168598-98183786 |
| 32413 | Zbtb21 | NM_175428.3 | chr16:98168598-98183786 |
| 32414 | Zbtb22 | NM_020625.3 | chr17:34053120-34096270 |
| 32415 | Zbtb24 | NM_001277229.1 | chr10:41170163-41185388 |
| 32416 | Zbtb24 | NM_001277230.1 | chr10:41170163-41185388 |
| 32417 | Zbtb24 | NM_153398.3 | chr10:41170163-41185388 |
| 32418 | Zbtb24 | NR_102360.1 | chr10:41170163-41185388 |
| 32419 | Zbtb25 | NM_001172104.1 | chr12:77449886-77470547 |
| 32420 | Zbtb25 | NM_028356.2 | chr12:77449886-77470547 |
| 32421 | Zbtb26 | NM_199025.2 | chr2:37287687-37298641 |
| 32422 | Zbtb3 | NM_001098237.1 | chr19:8876985-8879344 |
| 32423 | Zbtb3 | NM_133759.3 | chr19:8876985-8879344 |
| 32424 | Zbtb32 | NM_021397.2 | chr7:31374699-31377961 |
| 32425 | Zbtb33 | NM_001079513.1 | chrX:35542969-35605658 |
| 32426 | Zbtb33 | NM_020626.2 | chrX:35542969-35605658 |
| 32427 | Zbtb34 | NM_001085507.1 | chr2:33261627-33286844 |
| 32428 | Zbtb34 | NM_001276332.1 | chr2:33261627-33286844 |
| 32429 | Zbtb37 | NM_173404.3 | chr1:162947886-162964390 |
| 32430 | Zbtb38 | NM_175537.3 | chr9:96585842-96632094 |
| 32431 | Zbtb39 | NM_198035.1 | chr10:127176593-127184395 |
| 32432 | Zbtb4 | NM_029348.2 | chr11:69579413-69597528 |
| 32433 | Zbtb40 | NM_198248.1 | chr4:136535646-136604610 |
| 32434 | Zbtb41 | NM_172643.5 | chr1:141318959-141349584 |
| 32435 | Zbtb42 | NM_001100460.1 | chr12:113917050-113920958 |
| 32436 | Zbtb43 | NM_001025594.1 | chr2:33305807-33324052 |
| 32437 | Zbtb43 | NM_027947.2 | chr2:33305807-33324052 |
| 32438 | Zbtb44 | NM_001115130.1 | chr9:30838228-30883470 |
| 32439 | Zbtb44 | NM_172765.3 | chr9:30838228-30883470 |
| 32440 | Zbtb45 | NM_001024699.1 | chr7:13591014-13595149 |
| 32441 | Zbtb46 | NM_027656.2 | chr2:181125590-181194131 |
| 32442 | Zbtb46 | NM_028125.3 | chr2:181125590-181194131 |
| 32443 | Zbtb48 | NM_133879.2 | chr4:151393884-151401780 |
| 32444 | Zbtb49 | NM_029162.2 | chr5:38591282-38611667 |
| 32445 | Zbtb5 | NM_001163283.1 | chr4:45004114-45025284 |
| 32446 | Zbtb5 | NM_001163285.1 | chr4:45004114-45025284 |
| 32447 | Zbtb5 | NM_173399.3 | chr4:45004114-45025284 |
| 32448 | Zbtb6 | NM_146253.5 | chr2:37281019-37286439 |
| 32449 | Zbtb7a | NM_010731.3 | chr10:80599015-80614402 |
| 32450 | Zbtb7b | NM_009565.4 | chr3:89181568-89197125 |
| 32451 | Zbtb7c | NM_145356.3 | chr18:75979832-76308218 |
| 32452 | Zbtb8a | NM_028603.4 | chr4:129030875-129055272 |
| 32453 | Zbtb8b | NM_153541.3 | chr4:129103008-129118062 |
| 32454 | Zbtb8os | NM_025970.3 | chr4:129013269-129024273 |
| 32455 | Zbtb9 | NM_001005916.2 | chr17:27110123-27113148 |
| 32456 | Zbtbd6 | NM_001034882.3 | chr14:79851641-79854623 |
| 32457 | Zc2hc1a | NM_173181.3 | chr3:7503425-7553848 |
| 32458 | Zc2hc1b | NM_029172.1 | chr10:12869449-12897829 |
| 32459 | Zc2hc1c | NM_172414.4 | chr12:86629540-86640308 |
| 32460 | Zc3h10 | NM_134003.1 | chr10:127980620-127984800 |
| 32461 | Zc3h11a | NM_001276767.1 | chr1:135516447-135557976 |
| 32462 | Zc3h11a | NM_144530.6 | chr1:135516447-135557976 |
| 32463 | Zc3h12a | NM_153159.2 | chr4:124926657-124805125 |
| 32464 | Zc3h12b | NM_001034907.2 | chrX:92907017-93123309 |
| 32465 | Zc3h12c | NM_001162921.1 | chr9:51920090-51976216 |
| 32466 | Zc3h12d | NM_172783.3 | chr10:7552268-7590195 |
| 32467 | Zc3h13 | NM_026083.2 | chr14:75684179-75744233 |
| 32468 | Zc3h14 | NM_001008506.2 | chr12:99985177-100139694 |
| 32469 | Zc3h14 | NM_001160107.1 | chr12:99985177-100139694 |
| 32470 | Zc3h14 | NM_001160108.1 | chr12:99985177-100139694 |
| 32471 | Zc3h14 | NM_029034.2 | chr12:99985177-100139694 |
| 32472 | Zc3h14 | NR_027648.1 | chr12:99985177-100139694 |
| 32473 | Zc3h15 | NM_026934.3 | chr2:83484734-83504773 |
| 32474 | Zc3h18 | NM_001029905.1 | chr8:124900515-124941260 |
| 32475 | Zc3h18 | NM_001029994.1 | chr8:124900515-124941260 |
| 32476 | Zc3h3 | NM_172121.1 | chr15:75584876-75672338 |
| 32477 | Zc3h4 | NM_198631.2 | chr7:16286544-17023045 |
| 32478 | Zc3h6 | NM_178404.3 | chr2:128793137-128844299 |
| 32479 | Zc3h7a | NM_145931.2 | chr16:11136686-11176486 |
| 32480 | Zc3h7a | NR_027502.1 | chr16:11136686-11176486 |
| 32481 | Zc3h7b | NM_001081016.1 | chr15:81575277-81626699 |
| 32482 | Zc3h8 | NM_020594.2 | chr2:128752003-128769756 |
| 32483 | Zc3hav1 | NM_028411.1 | chr6:38260496-38304603 |
| 32484 | Zc3hav1 | NM_028864.2 | chr6:38260496-38304603 |
| 32485 | Zc3hav1l | NM_172467.3 | chr6:38237393-38249259 |
| 32486 | Zc3hc1 | NM_172793.2 | chr6:30316817-30341010 |
| 32487 | Zc4h2 | NM_001603916.2 | chrX:92834532-92853848 |
| 32488 | Zc4h2 | NM_026496.1 | chrX:92834532-92853848 |
| 32489 | Zc4h2 | NM_001289697.1 | chrX:92834532-92853848 |
| 32490 | Zcchc10 | NM_026479.4 | chr11:53138190-53146803 |
| 32491 | Zcchc11 | NM_175472.3 | chr4:108132030-108232020 |
| 32492 | Zcchc12 | NM_028325.3 | chrX:33735898-33739153 |
| 32493 | Zcchc13 | NM_029158.2 | chrX:100825924-100827003 |
| 32494 | Zcchc14 | NM_080855.2 | chr8:124126602-124175833 |
| 32495 | Zcchc16 | NM_001083795.4 | chrX:141123449-141156953 |
| 32496 | Zcchc17 | NM_153160.4 | chr4:129993328-130037190 |

| | | | |
|---|---|---|---|
| 32497 | Zcchc18 | NM_001035509.1 | chrX:133515654-133572841 |
| 32498 | Zcchc18 | NM_001035510.1 | chrX:133515654-133572841 |
| 32499 | Zcchc18 | NM_025893.2 | chrX:133515654-133572841 |
| 32500 | Zcchc2 | NM_001122675.1 | chr1:107886982-107930654 |
| 32501 | Zcchc2 | NM_001122676.1 | chr1:107886982-107930654 |
| 32502 | Zcchc24 | NM_001101433.1 | chr14:26531125-26588342 |
| 32503 | Zcchc3 | NM_175126.4 | chr2:152237691-152240780 |
| 32504 | Zcchc4 | NM_030185.3 | chr5:53174305-53211004 |
| 32505 | Zcchc5 | NM_199468.1 | chrX:104032420-104035982 |
| 32506 | Zcchc6 | NM_153538.3 | chr13:59873240-59924508 |
| 32507 | Zcchc7 | NM_138590.4 | chr4:44769430-44945086 |
| 32508 | Zcchc8 | NM_027494.3 | chr5:124148310-124171053 |
| 32509 | Zcchc9 | NM_145453.2 | chr13:91936137-91947301 |
| 32510 | Zcrb1 | NM_026025.2 | chr15:93216543-93228721 |
| 32511 | Zcwpw1 | NM_001005426.2 | chr5:138229030-138263849 |
| 32512 | Zdbf2 | NM_001267872.1 | chr1:63229144-63361149 |
| 32513 | Zdbf2 | NM_001285936.1 | chr1:63229144-63361149 |
| 32514 | Zdbf2 | NM_001285937.1 | chr1:63229144-63361149 |
| 32515 | Zdbf2 | NM_028673.1 | chr1:63229144-63361149 |
| 32516 | Zdhhc1 | NM_175160.3 | chr8:107996324-108020770 |
| 32517 | Zdhhc11 | NM_027704.2 | chr13:74101309-74130288 |
| 32518 | Zdhhc12 | NM_001037762.1 | chr2:29934285-29949155 |
| 32519 | Zdhhc12 | NM_025428.2 | chr2:29934285-29949155 |
| 32520 | Zdhhc13 | NM_028031.3 | chr7:56044372-56082807 |
| 32521 | Zdhhc14 | NM_146073.3 | chr17:5492599-5753891 |
| 32522 | Zdhhc15 | NM_175358.4 | chrX:101732306-101866403 |
| 32523 | Zdhhc16 | NM_023740.2 | chr19:42007962-42018593 |
| 32524 | Zdhhc17 | NM_172554.2 | chr10:110378835-110447122 |
| 32525 | Zdhhc18 | NM_001017968.2 | chr4:133182906-133189344 |
| 32526 | Zdhhc19 | NM_199309.2 | chr16:32496366-32507300 |
| 32527 | Zdhhc2 | NM_178395.3 | chr8:41509168-41570196 |
| 32528 | Zdhhc20 | NM_029492.4 | chr14:58451538-58509099 |
| 32529 | Zdhhc21 | NM_026647.3 | chr4:82444641-82505565 |
| 32530 | Zdhhc22 | NM_001080943.2 | chr12:88324330-88329626 |
| 32531 | Zdhhc23 | NM_001007460.1 | chr16:43969258-43979163 |
| 32532 | Zdhhc24 | NM_001168516.1 | chr19:4878667-4885397 |
| 32533 | Zdhhc24 | NM_001168517.1 | chr19:4878667-4885397 |
| 32534 | Zdhhc24 | NM_027476.3 | chr19:4878667-4885397 |
| 32535 | Zdhhc25 | NM_027306.1 | chr15:88430731-88432099 |
| 32536 | Zdhhc3 | NM_026917.4 | chr9:122981427-123022323 |
| 32537 | Zdhhc4 | NM_028379.5 | chr5:144078167-144090917 |
| 32538 | Zdhhc5 | NM_144887.4 | chr2:84528077-84555321 |
| 32539 | Zdhhc6 | NM_001035573.1 | chr19:55372788-55390522 |
| 32540 | Zdhhc6 | NM_025883.3 | chr19:55372788-55390522 |
| 32541 | Zdhhc7 | NM_133967.1 | chr8:122604994-122625372 |
| 32542 | Zdhhc8 | NM_172151.3 | chr16:18220845-18235229 |
| 32543 | Zdhhc9 | NM_172465.4 | chrX:45525147-45561879 |
| 32544 | Zeb1 | NM_011546.3 | chr18:5591858-5775466 |
| 32545 | Zeb2 | NM_001289521.1 | chr2:44839031-44969604 |
| 32546 | Zeb2 | NM_015753.4 | chr2:44839031-44969604 |
| 32547 | Zeb2os | NR_110571.1 | chr2:44839031-44969604 |
| 32548 | Zeb2os | NR_110572.1 | chr2:44839031-44969604 |
| 32549 | Zer1 | NM_001290503.1 | chr2:29952802-29980131 |
| 32550 | Zer1 | NM_178694.4 | chr2:29952802-29980131 |
| 32551 | Zf12 | NR_003547.2 | chrX_random:268799-270075 |
| 32552 | Zfand1 | NM_025512.2 | chr3:10339955-10351301 |
| 32553 | Zfand2a | NM_001159908.1 | chr5:139947169-139960445 |
| 32554 | Zfand2a | NM_133349.3 | chr5:139947169-139960445 |
| 32555 | Zfand2b | NM_001159905.1 | chr1:75165219-75168200 |
| 32556 | Zfand2b | NM_001159906.1 | chr1:75165219-75168200 |
| 32557 | Zfand2b | NM_026846.3 | chr1:75165219-75168200 |
| 32558 | Zfand3 | NM_148926.2 | chr17:30142031-30346965 |
| 32559 | Zfand4 | NM_001290338.1 | chr6:116214236-116280322 |
| 32560 | Zfand4 | NM_001290339.1 | chr6:116214236-116280322 |
| 32561 | Zfand5 | NM_009551.5 | chr19:21346767-21361330 |
| 32562 | Zfand6 | NM_029985.6 | chr7:91763563-91827861 |
| 32563 | Zfa-ps | NR_037920.1 | chr10:52262125-52265545 |
| 32564 | Zfat | NM_001145288.1 | chr15:67915299-68090418 |
| 32565 | Zfat | NM_198644.2 | chr15:67915299-68090418 |
| 32566 | Zfc3h1 | NM_001033261.2 | chr10:114822014-114869827 |
| 32567 | Zfhx2 | NM_001039198.1 | chr14:55680496-55710885 |
| 32568 | Zfhx2os | NR_004444.2 | chr14:55691928-55694711 |
| 32569 | Zfhx3 | NM_007496.2 | chr8:111238544-111485536 |
| 32570 | Zfhx4 | NM_030708.2 | chr3:5218554-5415855 |
| 32571 | Zfml | NM_001166371.1 | chr6:83864346-83936865 |
| 32572 | Zfml | NM_008717.3 | chr6:83864346-83936865 |
| 32573 | Zfp1 | NM_001037665.2 | chr8:114167342-114194911 |
| 32574 | Zfp1 | NM_011742.2 | chr8:114167342-114194911 |
| 32575 | Zfp101 | NM_009542.2 | chr17:33517123-33531582 |
| 32576 | Zfp105 | NM_009544.3 | chr9:122832195-122840146 |
| 32577 | Zfp106 | NM_011743.2 | chr2:120332565-120389567 |
| 32578 | Zfp108 | NM_018791.2 | chr7:25039812-25047463 |
| 32579 | Zfp109 | NM_020262.3 | chr7:25012813-25022617 |
| 32580 | Zfp11 | NM_172462.3 | chr5:130160469-130175963 |
| 32581 | Zfp110 | NM_022981.4 | chr7:13420158-13435933 |
| 32582 | Zfp111 | NM_019940.2 | chr7:24978233-24993168 |
| 32583 | Zfp112 | NM_021307.2 | chr7:24897338-24912971 |
| 32584 | Zfp113 | NM_019747.4 | chr5:138568929-138596972 |
| 32585 | Zfp114 | NM_001029933.2 | chr7:24960063-24967337 |
| 32586 | Zfp119a | NM_144546.6 | chr17:56004156-56018218 |
| 32587 | Zfp119b | NM_146249.4 | chr17:56077797-56084682 |
| 32588 | Zfp12 | NM_001289589.1 | chr5:143996841-144010513 |
| 32589 | Zfp12 | NM_001289590.1 | chr5:143996841-144010513 |
| 32590 | Zfp12 | NM_177681.4 | chr5:143996841-144010513 |
| 32591 | Zfp120 | NM_023266.4 | chr2:149940142-149962414 |

Fig. 25 - 173

| | | | | | | | | |
|---|---|---|---|---|---|---|---|---|
| 32592 | Zfp120 | NM_181266.2 | chr2:149940142-149962414 | | 32686 | Zfp319 | NM_024467.3 | chr8:97850035-97855850 |
| 32593 | Zfp128 | NM_153802.4 | chr7:13466526-13478771 | | 32687 | Zfp322a | NM_001111107.2 | chr13:23444971-23461077 |
| 32594 | Zfp13 | NM_011747.2 | chr17:23712818-23736454 | | 32688 | Zfp322a | NM_001286155.1 | chr13:23444971-23461077 |
| 32595 | Zfp131 | NM_028245.4 | chr13_random:31981-57600 | | 32689 | Zfp322a | NM_001286156.1 | chr13:23444971-23461077 |
| 32596 | Zfp131 | NM_028245.4 | chr13_random:225853-251473 | | 32690 | Zfp322a | NM_172586.4 | chr13:23444971-23461077 |
| 32597 | Zfp133-ps | NR_033459.1 | chr2:144285016-144293530 | | 32691 | Zfp324 | NM_178732.3 | chr7:13551212-13559171 |
| 32598 | Zfp14 | NM_011748.2 | chr7:30821377-30836415 | | 32692 | Zfp326 | NM_018759.2 | chr5:106305586-106344837 |
| 32599 | Zfp14 | NM_178733.5 | chr7:30821377-30836415 | | 32693 | Zfp326 | NR_030777.1 | chr5:106305586-106344837 |
| 32600 | Zfp142 | NM_029888.2 | chr1:74611702-74634602 | | 32694 | Zfp329 | NM_026046.3 | chr7:13389126-13404209 |
| 32601 | Zfp143 | NM_009281.3 | chr7:117205215-117238906 | | 32695 | Zfp330 | NM_145600.1 | chr8:85287518-85298025 |
| 32602 | Zfp146 | NM_011980.3 | chr7:30946286-30954746 | | 32696 | Zfp334 | NM_178411.3 | chr2:165202935-165213759 |
| 32603 | Zfp148 | NM_011749.4 | chr16:33380860-33503989 | | 32697 | Zfp335 | NM_199027.2 | chr2:164717391-164737250 |
| 32604 | Zfp157 | NM_028130.3 | chr5:138882703-138901922 | | 32698 | Zfp341 | NM_199304.1 | chr2:154439103-154472653 |
| 32605 | Zfp160 | NM_145483.2 | chr17:21145904-21165820 | | 32699 | Zfp345 | NM_001034900.3 | chr2:150296726-150310799 |
| 32606 | Zfp169 | NM_001164575.1 | chr13:48583028-48608805 | | 32700 | Zfp346 | NM_012017.2 | chr13:55206669-55236432 |
| 32607 | Zfp169 | NM_001164576.1 | chr13:48583028-48608805 | | 32701 | Zfp35 | NM_011755.2 | chr18:24148134-24163872 |
| 32608 | Zfp169 | NM_026450.3 | chr13:48583028-48608805 | | 32702 | Zfp352 | NM_153102.3 | chr4:89885510-89892378 |
| 32609 | Zfp174 | NM_001081217.1 | chr16:38847222-38858880 | | 32703 | Zfp354a | NM_009329.3 | chr11:50872758-50886301 |
| 32610 | Zfp180 | NM_001045486.2 | chr7:24866915-24892727 | | 32704 | Zfp354b | NM_013744.3 | chr11:50735287-50745137 |
| 32611 | Zfp180 | NM_001289634.1 | chr7:24866915-24892727 | | 32705 | Zfp354c | NM_013922.4 | chr11:50624586-50641233 |
| 32612 | Zfp180 | NM_001289637.1 | chr7:24866915-24892727 | | 32706 | Zfp358 | NM_080461.2 | chr8:3493337-3497208 |
| 32613 | Zfp180 | NM_001289640.1 | chr7:24866915-24892727 | | 32707 | Zfp36 | NM_011756.4 | chr7:29161802-29164247 |
| 32614 | Zfp180 | NM_001289641.1 | chr7:24866915-24892727 | | 32708 | Zfp362 | NM_001081098.1 | chr4:128456328-128483356 |
| 32615 | Zfp180 | NM_172483.2 | chr7:24866915-24892727 | | 32709 | Zfp365 | NM_178679.2 | chr10:67348352-67375410 |
| 32616 | Zfp182 | NM_001013387.2 | chrX:20603309-20639164 | | 32710 | Zfp366 | NM_001004149.1 | chr13:99954777-100016987 |
| 32617 | Zfp182 | NM_001111076.1 | chrX:20603309-20639164 | | 32711 | Zfp367 | NM_175494.4 | chr13:64234364-64254507 |
| 32618 | Zfp184 | NM_183014.1 | chr13:22036962-22052354 | | 32712 | Zfp369 | NM_178364.5 | chr13:65380161-65399103 |
| 32619 | Zfp185 | NM_001109043.1 | chrX:70232677-70276882 | | 32713 | Zfp36l1 | NM_007564.5 | chr12:81208746-81214000 |
| 32620 | Zfp185 | NM_009545.3 | chrX:70232677-70276882 | | 32714 | Zfp36l2 | NM_001001806.2 | chr17:84583268-84587287 |
| 32621 | Zfp189 | NM_001289901.1 | chr4:49534047-49544430 | | 32715 | Zfp36l3 | NM_001009549.2 | chrX:51075862-51079571 |
| 32622 | Zfp189 | NM_145547.3 | chr4:49534047-49544430 | | 32716 | Zfp37 | NM_001290350.1 | chr4:61850570-61869580 |
| 32623 | Zfp191 | NM_021559.2 | chr18:24170767-24179272 | | 32717 | Zfp37 | NM_001290351.1 | chr4:61850570-61869580 |
| 32624 | Zfp2 | NM_001044697.2 | chr11:50712213-50729663 | | 32718 | Zfp37 | NM_001290353.1 | chr4:61850570-61869580 |
| 32625 | Zfp2 | NM_001044698.2 | chr11:50712213-50729663 | | 32719 | Zfp37 | NM_009554.4 | chr4:61850570-61869580 |
| 32626 | Zfp2 | NM_001044699.1 | chr11:50712213-50729663 | | 32720 | Zfp382 | NM_001081007.1 | chr7:30906966-30920051 |
| 32627 | Zfp2 | NM_001044700.2 | chr11:50712213-50729663 | | 32721 | Zfp383 | NM_001243908.1 | chr7:30693535-30701832 |
| 32628 | Zfp202 | NM_030713.2 | chr9:39999900-40021189 | | 32722 | Zfp384 | NM_001252083.1 | chr6:124959255-124987888 |
| 32629 | Zfp207 | NM_001130169.1 | chr11:80196780-80219375 | | 32723 | Zfp384 | NM_175557.5 | chr6:124959255-124987888 |
| 32630 | Zfp207 | NM_001130170.1 | chr11:80196780-80219375 | | 32724 | Zfp385a | NM_013866.2 | chr15:103144325-103170517 |
| 32631 | Zfp207 | NM_001130171.1 | chr11:80196780-80219375 | | 32725 | Zfp385b | NM_001113399.1 | chr2:77248688-77654873 |
| 32632 | Zfp207 | NM_011751.3 | chr11:80196780-80219375 | | 32726 | Zfp385b | NM_001113400.1 | chr2:77248688-77654873 |
| 32633 | Zfp207 | NR_046038.1 | chr11:80196780-80219375 | | 32727 | Zfp385b | NM_178723.6 | chr2:77248688-77654873 |
| 32634 | Zfp212 | NM_001145881.1 | chr6:47870566-47882636 | | 32728 | Zfp385c | NM_177790.4 | chr11:100487533-100512007 |
| 32635 | Zfp212 | NM_145576.2 | chr6:47870566-47882636 | | 32729 | Zfp386 | NM_001004066.3 | chr12:117285934-117301675 |
| 32636 | Zfp213 | NM_001033496.3 | chr17:23693733-23701193 | | 32730 | Zfp386 | NM_001286214.1 | chr12:117285934-117301675 |
| 32637 | Zfp217 | NM_001033299.3 | chr2:169934142-169968175 | | 32731 | Zfp386 | NM_019565.4 | chr12:117285934-117301675 |
| 32638 | Zfp217 | NM_001159683.1 | chr2:169934142-169968175 | | 32732 | Zfp389 | NR_026798.1 | chr13:21596184-21598393 |
| 32639 | Zfp219 | NM_001253694.1 | chr14:52604507-52640408 | | 32733 | Zfp39 | NM_011758.2 | chr11:58701654-58717727 |
| 32640 | Zfp219 | NM_001253695.1 | chr14:52604507-52640408 | | 32734 | Zfp395 | NM_199029.2 | chr14:65977512-66017767 |
| 32641 | Zfp219 | NM_001253696.1 | chr14:52604507-52640408 | | 32735 | Zfp397 | NM_027007.2 | chr18:24113188-24123171 |
| 32642 | Zfp219 | NM_027248.2 | chr14:52604507-52640408 | | 32736 | Zfp398 | NM_027477.3 | chr6:47785659-47818256 |
| 32643 | Zfp229 | NM_001164676.1 | chr17:21870690-21885936 | | 32737 | Zfp398 | NM_173034.3 | chr6:47785659-47818256 |
| 32644 | Zfp235 | NM_019941.2 | chr7:24919181-24928260 | | 32738 | Zfp40 | NM_009555.2 | chr17:23310835-23330195 |
| 32645 | Zfp236 | NM_177832.3 | chr18:82762988-82862126 | | 32739 | Zfp407 | NM_001033341.2 | chr18:84377093-84758896 |
| 32646 | Zfp239 | NM_001001792.1 | chr6:117813094-117822784 | | 32740 | Zfp408 | NM_001033451.2 | chr2:91483844-91489948 |
| 32647 | Zfp239 | NM_008616.2 | chr6:117813094-117822784 | | 32741 | Zfp41 | NM_001044718.2 | chr15:75447113-75455730 |
| 32648 | Zfp248 | NM_028335.2 | chr6:118377336-118405524 | | 32742 | Zfp41 | NM_011759.3 | chr15:75447113-75455730 |
| 32649 | Zfp251 | NM_001007568.2 | chr15:76682573-76701865 | | 32743 | Zfp410 | NM_001252582.1 | chr12:85657808-85685389 |
| 32650 | Zfp26 | NM_011753.3 | chr9:20232761-20254604 | | 32744 | Zfp410 | NM_001252583.1 | chr12:85657808-85685389 |
| 32651 | Zfp260 | NM_011981.4 | chr7:30880094-30892633 | | 32745 | Zfp410 | NM_144833.3 | chr12:85657808-85685389 |
| 32652 | Zfp263 | NM_148924.3 | chr16:3744098-3750788 | | 32746 | Zfp410 | NR_045546.1 | chr12:85657808-85685389 |
| 32653 | Zfp266 | NM_001082485.1 | chr9:20299512-20325863 | | 32747 | Zfp410 | NR_045615.1 | chr12:85657808-85685389 |
| 32654 | Zfp266 | NM_001135019.1 | chr9:20299512-20325863 | | 32748 | Zfp414 | NM_026712.3 | chr17:33766036-33768659 |
| 32655 | Zfp27 | NM_001037707.1 | chr7:30678355-30691586 | | 32749 | Zfp414 | NR_034153.1 | chr17:33766036-33768659 |
| 32656 | Zfp27 | NM_001285797.1 | chr7:30678355-30691586 | | 32750 | Zfp418 | NM_146179.2 | chr7:7124063-7136271 |
| 32657 | Zfp27 | NM_001285798.1 | chr7:30678355-30691586 | | 32751 | Zfp42 | NM_009556.3 | chr8:44380420-44392363 |
| 32658 | Zfp27 | NM_011754.2 | chr7:30678355-30691586 | | 32752 | Zfp420 | NM_172740.2 | chr7:30644997-30662321 |
| 32659 | Zfp273 | NM_198322.3 | chr13:67914753-67927937 | | 32753 | Zfp422 | NM_026057.3 | chr6:116574033-116578995 |
| 32660 | Zfp275 | NM_001160229.1 | chrX:70587958-70604419 | | 32754 | Zfp423 | NM_033327.2 | chr8:90185708-90483494 |
| 32661 | Zfp275 | NM_031494.2 | chrX:70587958-70604419 | | 32755 | Zfp426 | NM_001110309.1 | chr9:20272992-20297190 |
| 32662 | Zfp276 | NM_020497.2 | chr8:125778095-125794451 | | 32756 | Zfp426 | NM_146221.4 | chr9:20272992-20297190 |
| 32663 | Zfp277 | NM_172575.3 | chr12:41041632-41172377 | | 32757 | Zfp428 | NM_001290461.1 | chr7:25292105-25300701 |
| 32664 | Zfp277 | NM_178845.3 | chr12:41041632-41172377 | | 32758 | Zfp428 | NM_146183.2 | chr7:25292105-25300701 |
| 32665 | Zfp28 | NM_175247.3 | chr7:6336027-6349347 | | 32759 | Zfp428 | NM_175142.1 | chr7:25292105-25300701 |
| 32666 | Zfp280b | NM_177475.3 | chr10:75495356-75505714 | | 32760 | Zfp428 | NR_110958.1 | chr7:25292105-25300701 |
| 32667 | Zfp280c | NM_001166648.1 | chrX:45894802-45947629 | | 32761 | Zfp429 | NM_001080941.1 | chr13:67490264-67500703 |
| 32668 | Zfp280c | NM_001166649.1 | chrX:45894802-45947629 | | 32762 | Zfp433 | NM_001243067.1 | chr10:81167569-81184721 |
| 32669 | Zfp280c | NM_001166650.1 | chrX:45894802-45947629 | | 32763 | Zfp433 | NM_001243067.1 | chr10:81326678-81343831 |
| 32670 | Zfp280c | NM_153532.3 | chrX:45894802-45947629 | | 32764 | Zfp438 | NM_178722.5 | chr18:5210028-5334437 |
| 32671 | Zfp280d | NM_146224.4 | chr9:72122705-72211578 | | 32765 | Zfp442 | NM_001177550.1 | chr2:150232872-150277230 |
| 32672 | Zfp281 | NM_001160251.1 | chr1:138521477-138526968 | | 32766 | Zfp444 | NM_001146024.1 | chr7:6124114-6144706 |
| 32673 | Zfp281 | NM_177643.4 | chr1:138521477-138526968 | | 32767 | Zfp444 | NM_028316.3 | chr7:6124114-6144706 |
| 32674 | Zfp282 | NM_013705.1 | chr6:47827553-47858483 | | 32768 | Zfp445 | NM_173364.5 | chr9:122758027-122775124 |
| 32675 | Zfp286 | NM_138949.3 | chr11:62591888-62602919 | | 32769 | Zfp446 | NM_001168561.1 | chr7:13563196-13571065 |
| 32676 | Zfp287 | NM_133208.2 | chr11:62524987-62542595 | | 32770 | Zfp446 | NM_001168562.1 | chr7:13563196-13571065 |
| 32677 | Zfp292 | NM_013889.2 | chr4:34750358-34830197 | | 32771 | Zfp446 | NM_175558.4 | chr7:13563196-13571065 |
| 32678 | Zfp296 | NM_022409.2 | chr7:20162635-20166005 | | 32772 | Zfp449 | NM_030139.4 | chrX:53599576-53618851 |
| 32679 | Zfp3 | NM_177565.3 | chr11:70577948-70586431 | | 32773 | Zfp451 | NM_001290699.1 | chr1:33818385-33871440 |
| 32680 | Zfp30 | NM_013705.1 | chr7:30569808-30579559 | | 32774 | Zfp451 | NM_001290700.1 | chr1:33818385-33871440 |
| 32681 | Zfp300 | NM_183185.3 | chrX:20656275-20666355 | | 32775 | Zfp451 | NM_133817.3 | chr1:33818385-33871440 |
| 32682 | Zfp316 | NM_017467.3 | chr5:144011373-144031701 | | 32776 | Zfp454 | NM_172794.2 | chr11:50686224-50700945 |
| 32683 | Zfp317 | NM_172918.4 | chr9:19426534-19454175 | | 32777 | Zfp455 | NM_001048204.1 | chr13:67295441-67310234 |
| 32684 | Zfp318 | NM_021346.2 | chr17:46520714-46557867 | | 32778 | Zfp456 | NM_001001186.3 | chr13:67464519-67476699 |
| 32685 | Zfp318 | NM_207671.4 | chr17:46520714-46557867 | | 32779 | Zfp457 | NM_001003666.2 | chr13:67393386-67407348 |
| | | | | | 32780 | Zfp458 | NM_001001152.2 | chr13:67355853-67370004 |

Fig. 25 - 174

| | | | |
|---|---|---|---|
| 32781 | Zfp459 | NM_177811.4 | chr13:67506649-67522354 |
| 32782 | Zfp46 | NM_009557.3 | chr4:135841983-135849857 |
| 32783 | Zfp462 | NM_172867.3 | chr4:54960816-55096435 |
| 32784 | Zfp467 | NM_001085415.1 | chr6:48377690-48395824 |
| 32785 | Zfp467 | NM_001085416.1 | chr6:48377690-48395824 |
| 32786 | Zfp467 | NM_001085417.1 | chr6:48377690-48395824 |
| 32787 | Zfp467 | NM_020589.2 | chr6:48377690-48395824 |
| 32788 | Zfp472 | NM_153063.3 | chr17:33102775-33116156 |
| 32789 | Zfp473 | NM_001289836.1 | chr7:51986851-52003987 |
| 32790 | Zfp473 | NM_001289837.1 | chr7:51986851-52003987 |
| 32791 | Zfp473 | NM_001289838.1 | chr7:51986851-52003987 |
| 32792 | Zfp473 | NM_001289839.1 | chr7:51986851-52003987 |
| 32793 | Zfp473 | NM_178734.4 | chr7:51986851-52003987 |
| 32794 | Zfp474 | NM_025749.3 | chr18:52775568-52799484 |
| 32795 | Zfp488 | NM_001013777.2 | chr14:34780255-34791950 |
| 32796 | Zfp493 | NM_028402.2 | chr13:67880629-67890017 |
| 32797 | Zfp503 | NM_145459.3 | chr14:22803183-22808823 |
| 32798 | Zfp507 | NM_177739.3 | chr7:36557369-36588008 |
| 32799 | Zfp51 | NM_009558.4 | chr17:21587315-21602553 |
| 32800 | Zfp511 | NM_027201.1 | chr7:147222290-147226504 |
| 32801 | Zfp512 | NM_172993.3 | chr5:31754808-31784126 |
| 32802 | Zfp513 | NM_001177901.1 | chr5:31235515-31651218 |
| 32803 | Zfp513 | NM_175311.4 | chr5:31235515-31651218 |
| 32804 | Zfp516 | NM_001177464.1 | chr18:83080270-83174706 |
| 32805 | Zfp516 | NM_183033.2 | chr18:83080270-83174706 |
| 32806 | Zfp518a | NM_028319.1 | chr19:40969195-40992437 |
| 32807 | Zfp518b | NM_001081144.2 | chr5:39059722-39076065 |
| 32808 | Zfp518b | NM_001177902.1 | chr5:39059722-39076065 |
| 32809 | Zfp52 | NM_144515.2 | chr17:21672502-21699565 |
| 32810 | Zfp521 | NM_145492.4 | chr18:13845522-14131242 |
| 32811 | Zfp523 | NM_172617.3 | chr17:28314362-28342831 |
| 32812 | Zfp524 | NM_025324.2 | chr7:4967109-4970090 |
| 32813 | Zfp526 | NM_175436.4 | chr7:26006469-26012524 |
| 32814 | Zfp53 | NM_013843.3 | chr17:21625951-21647441 |
| 32815 | Zfp532 | NM_207255.2 | chr18:65739883-65849090 |
| 32816 | Zfp534 | NM_001127188.2 | chr4:147048333-147076740 |
| 32817 | Zfp536 | NM_172385.2 | chr7:38264127-38554771 |
| 32818 | Zfp54 | NM_011760.2 | chr17:21560190-21572348 |
| 32819 | Zfp541 | NM_001099277.1 | chr7:16657290-16681677 |
| 32820 | Zfp551 | NM_001033820.3 | chr7:13000496-13007840 |
| 32821 | Zfp553 | NM_146201.1 | chr7:134376956-134381374 |
| 32822 | Zfp558 | NM_028935.1 | chr9:18258497-18278003 |
| 32823 | Zfp560 | NM_001004190.3 | chr9:20149579-20189602 |
| 32824 | Zfp563 | NM_001024950.2 | chr17:33226311-33247649 |
| 32825 | Zfp566 | NM_152814.2 | chr7:30862355-30875529 |
| 32826 | Zfp568 | NM_001033355.3 | chr7:30768973-30813301 |
| 32827 | Zfp568 | NM_001167872.1 | chr7:30768973-30813301 |
| 32828 | Zfp568 | NM_001167873.1 | chr7:30768973-30813301 |
| 32829 | Zfp57 | NM_001013745.2 | chr17:37138107-37147674 |
| 32830 | Zfp57 | NM_001168501.1 | chr17:37138107-37147674 |
| 32831 | Zfp57 | NM_001168502.1 | chr17:37138107-37147674 |
| 32832 | Zfp57 | NR_033137.1 | chr17:37138107-37147674 |
| 32833 | Zfp572 | NR_045613.1 | chr15:59138502-59143568 |
| 32834 | Zfp574 | NM_001168506.1 | chr7:25862223-25868511 |
| 32835 | Zfp574 | NM_175477.4 | chr7:25862223-25868511 |
| 32836 | Zfp575 | NM_001033205.3 | chr7:25368857-25372660 |
| 32837 | Zfp579 | NM_026741.2 | chr7:4944453-4947703 |
| 32838 | Zfp58 | NM_001007575.2 | chr13:67591102-67601458 |
| 32839 | Zfp580 | NM_026900.1 | chr7:5003133-5005325 |
| 32840 | Zfp583 | NM_001033249.3 | chr7:6267266-6282036 |
| 32841 | Zfp59 | NM_011762.3 | chr7:28623602-28641793 |
| 32842 | Zfp592 | NM_178707.4 | chr7:88138569-88190048 |
| 32843 | Zfp593 | NM_024215.2 | chr4:133799221-133801506 |
| 32844 | Zfp595 | NM_177622.3 | chr13:67413933-67433496 |
| 32845 | Zfp597 | NM_001033159.2 | chr16:3861543-3872374 |
| 32846 | Zfp598 | NM_183149.1 | chr17:24806696-24818961 |
| 32847 | Zfp599 | NM_181419.3 | chr9:22051873-22064339 |
| 32848 | Zfp60 | NM_009560.2 | chr7:28516427-28536708 |
| 32849 | Zfp60 | NM_029531.2 | chr7:28516427-28536708 |
| 32850 | Zfp600 | NM_001175545.2 | chr4:146124227-146166157 |
| 32851 | Zfp600 | NM_001177546.2 | chr4:146124227-146166157 |
| 32852 | Zfp605 | NM_001163996.1 | chr5:110539110-110558813 |
| 32853 | Zfp606 | NM_001039951.2 | chr7:13063653-13081584 |
| 32854 | Zfp606 | NM_026112.4 | chr7:13063653-13081584 |
| 32855 | Zfp607 | NM_001024726.2 | chr7:28645603-28665844 |
| 32856 | Zfp608 | NM_175751.4 | chr18:55047698-55149834 |
| 32857 | Zfp61 | NM_172536.3 | chr9:65539389-65675371 |
| 32858 | Zfp61 | NM_009561.2 | chr7:25076064-25084568 |
| 32859 | Zfp612 | NM_175480.4 | chr8:112603633-112616652 |
| 32860 | Zfp616 | NM_001177570.1 | chr11:73883671-73900803 |
| 32861 | Zfp617 | NM_139358.3 | chr8:74446723-74458529 |
| 32862 | Zfp618 | NM_028326.1 | chr4:62626607-62795064 |
| 32863 | Zfp619 | NM_001004139.2 | chr7:46773135-46795785 |
| 32864 | Zfp62 | NM_001024846.1 | chr11:49017001-49032318 |
| 32865 | Zfp62 | NM_009562.2 | chr11:49017001-49032318 |
| 32866 | Zfp622 | NM_144523.2 | chr15:25914126-25928237 |
| 32867 | Zfp623 | NM_030199.3 | chr15:75771381-75779830 |
| 32868 | Zfp628 | NM_170759.2 | chr7:4866818-4873605 |
| 32869 | Zfp629 | NM_177226.5 | chr7:134750548-134757947 |
| 32870 | Zfp637 | NM_177684.2 | chr6:117791259-117795974 |
| 32871 | Zfp639 | NM_001161818.1 | chr3:32409471-32419755 |
| 32872 | Zfp639 | NM_144519.4 | chr3:32409471-32419755 |
| 32873 | Zfp64 | NM_009564.2 | chr2:168750860-168781087 |
| 32874 | Zfp641 | NM_173769.3 | chr15:98116552-98126514 |
| 32875 | Zfp644 | NM_026856.2 | chr5:107045759-107125849 |
| 32876 | Zfp646 | NM_172749.4 | chr7:135021215-135029510 |
| 32877 | Zfp647 | NM_001168276.1 | chr15:76740799-76755878 |
| 32878 | Zfp647 | NM_172817.3 | chr15:76740799-76755878 |
| 32879 | Zfp648 | NM_001204908.1 | chr1:156048316-156052804 |
| 32880 | Zfp65 | NM_145622.2 | chr13:67806242-67830110 |
| 32881 | Zfp651 | NM_001166644.1 | chr9:121669150-121680860 |
| 32882 | Zfp652 | NM_201609.2 | chr11:95610380-95626027 |
| 32883 | Zfp652os | NR_045780.1 | chr11:95561419-95574068 |
| 32884 | Zfp653 | NM_177318.2 | chr9:21859904-21875789 |
| 32885 | Zfp654 | NM_028059.2 | chr16:64780172-64786147 |
| 32886 | Zfp655 | NM_001083958.1 | chr5:145992583-146008175 |
| 32887 | Zfp655 | NM_028298.3 | chr5:145992583-146008175 |
| 32888 | Zfp658 | NM_001008549.2 | chr7:50817739-50830831 |
| 32889 | Zfp661 | NM_001111029.1 | chr2:127401268-127410413 |
| 32890 | Zfp661 | NM_028141.3 | chr2:127401268-127410413 |
| 32891 | Zfp663 | NM_001005425.1 | chr2:165176796-165187619 |
| 32892 | Zfp664 | NM_001081750.1 | chr5:125343074-125369000 |
| 32893 | Zfp667 | NM_001024928.2 | chr7:6238181-6259485 |
| 32894 | Zfp668 | NM_146259.3 | chr7:135008872-135020337 |
| 32895 | Zfp672 | NM_001256516.1 | chr11:58128615-58143841 |
| 32896 | Zfp672 | NM_001256517.1 | chr11:58128615-58143841 |
| 32897 | Zfp672 | NM_001256518.1 | chr11:58128615-58143841 |
| 32898 | Zfp672 | NM_001256519.1 | chr11:58128615-58143841 |
| 32899 | Zfp672 | NM_001256520.1 | chr11:58128615-58143841 |
| 32900 | Zfp672 | NM_178761.5 | chr11:58128615-58143841 |
| 32901 | Zfp672 | NR_028331.2 | chr11:58128615-58143841 |
| 32902 | Zfp672 | NR_046280.1 | chr11:58128615-58143841 |
| 32903 | Zfp677 | NM_172486.2 | chr17:21520711-21536229 |
| 32904 | Zfp68 | NM_001044747.2 | chr5:139044879-139060971 |
| 32905 | Zfp68 | NM_001163797.1 | chr5:139044879-139060971 |
| 32906 | Zfp68 | NM_013844.2 | chr5:139044879-139060971 |
| 32907 | Zfp687 | NM_030074.2 | chr3:94810624-94819160 |
| 32908 | Zfp688 | NM_026999.4 | chr7:134562479-134565548 |
| 32909 | Zfp689 | NM_175163.3 | chr7:134585649-134592672 |
| 32910 | Zfp69 | NM_001005788.3 | chr4:120602741-120624306 |
| 32911 | Zfp691 | NM_001145935.1 | chr4:118842122-118846800 |
| 32912 | Zfp691 | NM_001145936.1 | chr4:118842122-118846800 |
| 32913 | Zfp691 | NM_183140.3 | chr4:118842122-118846800 |
| 32914 | Zfp692 | NM_001040686.1 | chr11:58120570-58128115 |
| 32915 | Zfp692 | NM_182996.3 | chr11:58120570-58128115 |
| 32916 | Zfp697 | NM_172863.4 | chr3:98186603-98235872 |
| 32917 | Zfp7 | NM_145916.2 | chr15:76709705-76722824 |
| 32918 | Zfp703 | NM_001101502.1 | chr8:28087807-28091934 |
| 32919 | Zfp703 | NM_001110508.1 | chr8:28087807-28091934 |
| 32920 | Zfp704 | NM_133218.2 | chr3:9427009-9610085 |
| 32921 | Zfp706 | NM_026521.4 | chr15:36926781-36937157 |
| 32922 | Zfp707 | NM_001081065.1 | chr15:75799614-75806295 |
| 32923 | Zfp708 | NM_001012325.2 | chr13:67170333-67214964 |
| 32924 | Zfp708 | NM_001012448.2 | chr13:67170333-67214964 |
| 32925 | Zfp708 | NM_001012449.2 | chr13:67170333-67214964 |
| 32926 | Zfp709 | NM_145624.4 | chr8:74405966-74416464 |
| 32927 | Zfp710 | NM_001145999.1 | chr7:87169699-87237637 |
| 32928 | Zfp710 | NM_001146000.1 | chr7:87169699-87237637 |
| 32929 | Zfp710 | NM_175433.5 | chr7:87169699-87237637 |
| 32930 | Zfp711 | NM_177747.3 | chrX:109714134-109748671 |
| 32931 | Zfp712 | NM_001166218.1 | chr13:67139529-67162106 |
| 32932 | Zfp715 | NM_027264.3 | chr7:50551892-50568631 |
| 32933 | Zfp719 | NM_172482.1 | chr7:50834955-50849080 |
| 32934 | Zfp72 | NM_001081680.1 | chr13:74508873-74514014 |
| 32935 | Zfp735 | NM_001126489.2 | chr11:73502279-73527310 |
| 32936 | Zfp738 | NM_001001187.3 | chr13:67768377-67784449 |
| 32937 | Zfp74 | NM_178384.3 | chr7:30717809-30736912 |
| 32938 | Zfp740 | NM_001289690.1 | chr15:102034075-102046041 |
| 32939 | Zfp740 | NM_001289691.1 | chr15:102034075-102046041 |
| 32940 | Zfp740 | NM_001289694.1 | chr15:102034075-102046041 |
| 32941 | Zfp740 | NM_001289695.1 | chr15:102034075-102046041 |
| 32942 | Zfp746 | NM_001163475.1 | chr6:48012393-48036592 |
| 32943 | Zfp747 | NM_175560.3 | chr7:134516050-134519564 |
| 32944 | Zfp748 | NM_001035231.3 | chr13:67639576-67654088 |
| 32945 | Zfp750 | NM_178763.4 | chr11:121372290-121380656 |
| 32946 | Zfp758 | NM_145484.2 | chr17:22498419-22514248 |
| 32947 | Zfp759 | NM_172392.3 | chr13:67229163-67242723 |
| 32948 | Zfp760 | NM_001008501.2 | chr17:21844707-21862603 |
| 32949 | Zfp763 | NM_028543.3 | chr17:33153808-33170326 |
| 32950 | Zfp764 | NM_001167832.1 | chr7:134547181-134550336 |
| 32951 | Zfp764 | NM_146203.4 | chr7:134547181-134550336 |
| 32952 | Zfp768 | NM_146202.1 | chr7:134486308-134488828 |
| 32953 | Zfp770 | NM_175466.4 | chr2:114019196-114027168 |
| 32954 | Zfp771 | NM_177362.3 | chr7:134388039-134398315 |
| 32955 | Zfp772 | NM_145577.2 | chr7:154832-7162709 |
| 32956 | Zfp773 | NM_029584.1 | chr7:7083388-7089466 |
| 32957 | Zfp775 | NM_173429.2 | chr6:48563178-48573226 |
| 32958 | Zfp777 | NM_001081382.1 | chr6:47974186-47998113 |
| 32959 | Zfp78 | NM_001025163.1 | chr7:6316014-6335315 |
| 32960 | Zfp78 | NM_001112805.1 | chr7:6316014-6335315 |
| 32961 | Zfp78 | NM_177888.4 | chr7:6316014-6335315 |
| 32962 | Zfp780b | NM_001081021.1 | chr7:28744818-28764176 |
| 32963 | Zfp781 | NM_199062.1 | chr10:81205565-81233887 |
| 32964 | Zfp781 | NM_199062.1 | chr10:81364655-81393225 |
| 32965 | Zfp783 | NR_027963.1 | chr6:47893174-47904548 |
| 32966 | Zfp784 | NM_001039532.2 | chr7:4986047-4990048 |
| 32967 | Zfp786 | NM_177882.4 | chr6:47769264-47780504 |
| 32968 | Zfp787 | NM_001013012.1 | chr7:6083090-6107573 |
| 32969 | Zfp788 | NM_023363.2 | chr7:48888900-48906902 |
| 32970 | Zfp790 | NM_001145880.1 | chr7:30601090-30617061 |

Fig. 25 - 175

| | | | |
|---|---|---|---|
| 32971 | Zfp790 | NM_146185.2 | chr7:30601090-30617061 |
| 32972 | Zfp791 | NM_001037745.1 | chr8:87633065-87646994 |
| 32973 | Zfp799 | NM_177359.5 | chr17:32954148-32967193 |
| 32974 | Zfp800 | NM_001081678.1 | chr7:28189930-28211601 |
| 32975 | Zfp804a | NM_175513.3 | chr2:81893814-82100035 |
| 32976 | Zfp804b | NM_001163223.1 | chr5:6769030-7344378 |
| 32977 | Zfp808 | NM_001039239.2 | chr13:62231249-62275296 |
| 32978 | Zfp809 | NM_001164624.1 | chr9:22030146-22047798 |
| 32979 | Zfp809 | NM_172763.3 | chr9:22030146-22047798 |
| 32980 | Zfp809 | NR_028420.1 | chr9:22030146-22047798 |
| 32981 | Zfp81 | NM_207541.1 | chr17:33470672-33495823 |
| 32982 | Zfp810 | NM_145612.2 | chr9:22081191-22112082 |
| 32983 | Zfp811 | NM_001267583.1 | chr17:32932620-32946876 |
| 32984 | Zfp811 | NM_183177.3 | chr17:32932620-32946876 |
| 32985 | Zfp819 | NM_028913.3 | chr7:50862538-50873649 |
| 32986 | Zfp82 | NM_001252519.1 | chr7:30841052-30857842 |
| 32987 | Zfp82 | NM_001253385.1 | chr7:30841052-30857842 |
| 32988 | Zfp82 | NM_177889.5 | chr7:30841052-30857842 |
| 32989 | Zfp820 | NM_029281.2 | chr17:21953842-21982726 |
| 32990 | Zfp821 | NM_001167946.2 | chr8:112229445-112248832 |
| 32991 | Zfp821 | NM_001286391.1 | chr8:112229445-112248832 |
| 32992 | Zfp821 | NM_001286393.1 | chr8:112229445-112248832 |
| 32993 | Zfp821 | NM_029468.3 | chr8:112229445-112248832 |
| 32994 | Zfp825 | NM_146231.1 | chr13:74617504-74631398 |
| 32995 | Zfp827 | NM_178267.3 | chr8:81552335-81717665 |
| 32996 | Zfp830 | NM_025854.4 | chr11:82577846-82581124 |
| 32997 | Zfp831 | NM_001099328.1 | chr2:174469034-174536331 |
| 32998 | Zfp839 | NM_001199785.1 | chr12:112088488-112108208 |
| 32999 | Zfp839 | NM_028365.2 | chr12:112088488-112108208 |
| 33000 | Zfp84 | NM_023750.2 | chr7:30555971-30566438 |
| 33001 | Zfp846 | NM_172919.2 | chr9:20385771-20399637 |
| 33002 | Zfp85 | NM_001001130.2 | chr13:67848737-67856071 |
| 33003 | Zfp850 | NM_001254951.1 | chr7:28769489-28799134 |
| 33004 | Zfp85os | NR_027969.1 | chr13:67830199-67857775 |
| 33005 | Zfp862-ps | NR_015597.1 | chr6:48454337-48484831 |
| 33006 | Zfp862-ps | NR_027808.1 | chr6:48454337-48484831 |
| 33007 | Zfp865 | NM_001033383.2 | chr7:4971977-4984825 |
| 33008 | Zfp865 | NM_001290426.1 | chr7:4971977-4984825 |
| 33009 | Zfp866 | NM_177899.3 | chr8:72285222-72298810 |
| 33010 | Zfp867 | NM_178417.3 | chr11:59274698-59285976 |
| 33011 | Zfp868 | NM_001045553.1 | chr8:72134552-72149447 |
| 33012 | Zfp868 | NM_177712.4 | chr8:72134552-72149447 |
| 33013 | Zfp869 | NM_001039965.1 | chr8:72229036-72240801 |
| 33014 | Zfp869 | NM_001039967.1 | chr8:72229036-72240801 |
| 33015 | Zfp869 | NM_181274.3 | chr8:72229036-72240801 |
| 33016 | Zfp87 | NM_133228.3 | chr13:67616717-67627167 |
| 33017 | Zfp870 | NM_207245.2 | chr17:33016165-33028548 |
| 33018 | Zfp871 | NM_172458.3 | chr17:32902441-32925232 |
| 33019 | Zfp872 | NM_001033813.4 | chr9:21992609-22006567 |
| 33020 | Zfp873 | NM_001024626.2 | chr10:81510871-81524331 |
| 33021 | Zfp874a | NM_177712.4 | chr13:67541366-67552560 |
| 33022 | Zfp874b | NM_001076791.2 | chr13:67572448-67585189 |
| 33023 | Zfp879 | NM_001290779.1 | chr11:50645533-50655054 |
| 33024 | Zfp879 | NM_173387.3 | chr11:50645533-50655054 |
| 33025 | Zfp882 | NM_001166645.1 | chr8:74432504-74442750 |
| 33026 | Zfp9 | NM_011763.2 | chr6:118411967-118429291 |
| 33027 | Zfp90 | NM_011764.3 | chr8:108939238-108949789 |
| 33028 | Zfp91 | NM_053009.3 | chr19:12841429-12870613 |
| 33029 | Zfp91cntf | NR_024093.1 | chr19:12838018-12870613 |
| 33030 | Zfp92 | NM_009566.4 | chrX:70656441-70672326 |
| 33031 | Zfp93 | NM_009567.4 | chr7:25055436-25062813 |
| 33032 | Zfp930 | NM_001013379.1 | chr8:71732944-71754438 |
| 33033 | Zfp931 | NM_001162922.1 | chr2:177801582-177813130 |
| 33034 | Zfp932 | NM_145863.2 | chr5:110425545-110439430 |
| 33035 | Zfp933 | NM_198199.1 | chr4:147197094-147222484 |
| 33036 | Zfp934 | NM_001162911.1 | chr13:62618156-62659959 |
| 33037 | Zfp934 | NM_175252.4 | chr13:62618156-62659959 |
| 33038 | Zfp935 | NM_001136496.1 | chr13:62554375-62568172 |
| 33039 | Zfp935 | NM_178875.4 | chr13:62554375-62568172 |
| 33040 | Zfp936 | NM_001032957.1 | chr7:50432957-50447479 |
| 33041 | Zfp937 | NM_001142411.2 | chr2:150043834-150070610 |
| 33042 | Zfp938 | NM_001105557.2 | chr10:81687601-81704020 |
| 33043 | Zfp939 | NM_001042021.1 | chr7:46704887-46732786 |
| 33044 | Zfp94 | NM_001199321.1 | chr7:25086722-25101685 |
| 33045 | Zfp94 | NM_009568.3 | chr7:25086722-25101685 |
| 33046 | Zfp940 | NM_177712.3 | chr7:30628954-30638667 |
| 33047 | Zfp941 | NM_001001180.2 | chr7:147995575-148008077 |
| 33048 | Zfp942 | NM_001199048.1 | chr17:22063929-22099431 |
| 33049 | Zfp943 | NM_001025373.2 | chr17:22099525-22131333 |
| 33050 | Zfp944 | NM_176962.4 | chr17:22474955-22498367 |
| 33051 | Zfp945 | NM_001110254.1 | chr17:22983663-23004101 |
| 33052 | Zfp945 | NM_177358.4 | chr17:22983663-23004101 |
| 33053 | Zfp946 | NM_198003.2 | chr17:22561234-22593656 |
| 33054 | Zfp947 | NM_177596.3 | chr17:22281325-22302944 |
| 33055 | Zfp948 | NM_001002008.1 | chr17:21704009-21725649 |
| 33056 | Zfp949 | NM_001142943.1 | chr9:88442857-88465924 |
| 33057 | Zfp949 | NM_163061.1 | chr9:88442857-88465924 |
| 33058 | Zfp951 | NM_001039231.1 | chr5:105242186-105289087 |
| 33059 | Zfp952 | NM_001045559.1 | chr17:33130083-33142402 |
| 33060 | Zfp953 | NM_001038651.3 | chr13:67440244-67461508 |
| 33061 | Zfp954 | NM_172738.3 | chr7:7067393-7074187 |
| 33062 | Zfp955a | NM_029952.3 | chr17:33376451-33392090 |
| 33063 | Zfp955b | NM_001142957.1 | chr17:33426488-33441634 |
| 33064 | Zfp956 | NM_178898.4 | chr6:47903389-47915298 |
| 33065 | Zfp957 | NM_001033215.3 | chr14:79612161-79647174 |
| 33066 | Zfp958 | NM_145591.4 | chr8:4613169-4630231 |
| 33067 | Zfp959 | NM_145490.4 | chr17:56031515-56038353 |
| 33068 | Zfp960 | NM_001005358.2 | chr17:17201066-17226595 |
| 33069 | Zfp960 | NM_001163919.1 | chr17:17201066-17226595 |
| 33070 | Zfp961 | NM_001164581.1 | chr8:74474964-74494232 |
| 33071 | Zfp963 | NM_001200023.1 | chr8:72265537-72273861 |
| 33072 | Zfp964 | NM_001177527.1 | chr8:72178454-72188352 |
| 33073 | Zfp97 | NM_011765.5 | chr17:17258346-17283842 |
| 33074 | Zfpl1 | NM_024231.2 | chr19:6086763-6084891 |
| 33075 | Zfpm1 | NM_009569.3 | chr8:124806040-124861147 |
| 33076 | Zfpm2 | NM_011766.5 | chr15:40486587-40936138 |
| 33077 | Zfr | NM_011767.2 | chr15:12047606-12115205 |
| 33078 | Zfr2 | NM_001034895.3 | chr10:80695907-80714868 |
| 33079 | Zfx | NM_001044386.1 | chrX:91319969-91368746 |
| 33080 | Zfx | NM_011768.2 | chrX:91319969-91368746 |
| 33081 | Zfy1 | NM_009570.4 | chrY:61649-133852 |
| 33082 | Zfy2 | NM_009571.2 | chrY:1362122-1426357 |
| 33083 | Zfyve1 | NM_183154.3 | chr12:84887890-84938097 |
| 33084 | Zfyve16 | NM_173392.4 | chr13:93257703-93300765 |
| 33085 | Zfyve19 | NM_001164827.1 | chr2:118998235-119042786 |
| 33086 | Zfyve19 | NM_028054.3 | chr2:118998235-119042786 |
| 33087 | Zfyve20 | NM_030081.2 | chr6:92136705-92164805 |
| 33088 | Zfyve21 | NM_026752.4 | chr12:113052380-113066599 |
| 33089 | Zfyve26 | NM_001008550.1 | chr12:80333333-80397269 |
| 33090 | Zfyve27 | NM_001164531.1 | chr19:42245056-42269082 |
| 33091 | Zfyve27 | NM_177319.3 | chr19:42245056-42269082 |
| 33092 | Zfyve28 | NM_001015039.1 | chr5:34537542-34630973 |
| 33093 | Zfyve9 | NM_183300.2 | chr4:108311864-108396481 |
| 33094 | Zg16 | NM_026918.2 | chr7:134193669-134195491 |
| 33095 | Zglp1 | NM_001103168.1 | chr9:20866836-20871537 |
| 33096 | Zgpat | NM_001048148.1 | chr2:181092394-181115498 |
| 33097 | Zgpat | NM_144894.3 | chr2:181092394-181115498 |
| 33098 | Zgrf1 | NM_197997.2 | chr3:127256406-127320941 |
| 33099 | Zhx1 | NM_001042438.2 | chr15:57878557-57908063 |
| 33100 | Zhx1 | NM_009572.4 | chr15:57878557-57908063 |
| 33101 | Zhx2 | NM_199449.2 | chr15:57526221-57671387 |
| 33102 | Zhx3 | NM_177263.3 | chr2:160596183-160698726 |
| 33103 | Zic1 | NM_009573.3 | chr9:91255182-91260637 |
| 33104 | Zic2 | NM_009574.3 | chr14:122874605-122879550 |
| 33105 | Zic3 | NM_009575.2 | chrX:55283804-55289807 |
| 33106 | Zic4 | NM_009576.2 | chr9:91263809-91284186 |
| 33107 | Zic5 | NM_022987.3 | chr14:122858881-122864880 |
| 33108 | Zik1 | NM_009577.3 | chr7:11072572-11080730 |
| 33109 | Zim1 | NM_011769.4 | chr7:6628153-6649143 |
| 33110 | Zim3 | NR_036631.2 | chr7:6908397-6929373 |
| 33111 | Zkscan1 | NM_029869.1 | chr5:138526311-138549050 |
| 33112 | Zkscan1 | NM_133906.4 | chr5:138526311-138549050 |
| 33113 | Zkscan14 | NM_023322.2 | chr5:145955814-145962751 |
| 33114 | Zkscan16 | NM_001099323.2 | chr4:58956499-58971227 |
| 33115 | Zkscan17 | NM_001130529.2 | chr11:59299022-59324569 |
| 33116 | Zkscan17 | NM_001291014.1 | chr11:59299022-59324569 |
| 33117 | Zkscan17 | NM_172941.4 | chr11:59299022-59324569 |
| 33118 | Zkscan2 | NM_001081329.1 | chr7:130622153-130643963 |
| 33119 | Zkscan3 | NM_001145778.1 | chr13:21478872-21494624 |
| 33120 | Zkscan3 | NM_023685.4 | chr13:21478872-21494624 |
| 33121 | Zkscan4 | NM_001309115.2 | chr13:21570717-21577374 |
| 33122 | Zkscan5 | NM_001167944.1 | chr5:145965427-145982619 |
| 33123 | Zkscan5 | NM_016683.2 | chr5:145965427-145982619 |
| 33124 | Zkscan6 | NM_026107.3 | chr11:65620745-65642741 |
| 33125 | Zkscan7 | NM_001177505.1 | chr9:122797588-122805242 |
| 33126 | Zkscan8 | NM_001251833.1 | chr13:21605089-21622983 |
| 33127 | Zkscan8 | NM_001251834.1 | chr13:21605089-21622983 |
| 33128 | Zkscan8 | NM_139141.4 | chr13:21605089-21622983 |
| 33129 | Zmat1 | NM_175446.3 | chrX:131509911-131543748 |
| 33130 | Zmat2 | NM_025594.3 | chr18:36953576-36959314 |
| 33131 | Zmat3 | NM_009517.2 | chr3:32233716-32264587 |
| 33132 | Zmat4 | NM_001277239.1 | chr8:24780132-25173588 |
| 33133 | Zmat4 | NM_177086.4 | chr8:24780132-25173588 |
| 33134 | Zmat5 | NM_026015.2 | chr11:4604680-4637669 |
| 33135 | Zmiz1 | NM_183208.3 | chr14:26278671-26486233 |
| 33136 | Zmiz2 | NM_001005867.1 | chr11:6295127-6306165 |
| 33137 | Zmiz2 | NM_028601.3 | chr11:6295127-6306165 |
| 33138 | Zmpste24 | NM_172700.2 | chr4:120731842-120770848 |
| 33139 | Zmym1 | NM_026670.4 | chr4:126724337-126738376 |
| 33140 | Zmym2 | NM_029498.3 | chr14:57506631-57581416 |
| 33141 | Zmym3 | NM_001177985.1 | chrX:98599722-98616024 |
| 33142 | Zmym3 | NM_001177986.1 | chrX:98599722-98616024 |
| 33143 | Zmym3 | NM_001177987.1 | chrX:98599722-98616024 |
| 33144 | Zmym3 | NM_001177988.1 | chrX:98599722-98616024 |
| 33145 | Zmym3 | NM_019831.3 | chrX:98599722-98616024 |
| 33146 | Zmym4 | NM_001114399.1 | chr4:126539065-126645167 |
| 33147 | Zmym5 | NM_001253752.1 | chr14:57409421-57430553 |
| 33148 | Zmym5 | NM_001253753.1 | chr14:57409421-57430553 |
| 33149 | Zmym5 | NM_144842.3 | chr14:57409421-57430553 |
| 33150 | Zmym6 | NM_001285885.1 | chr4:126754626-126801618 |
| 33151 | Zmym6 | NM_001285887.1 | chr4:126754626-126801618 |
| 33152 | Zmym6 | NM_001285888.1 | chr4:126754626-126801618 |
| 33153 | Zmym6 | NM_177462.5 | chr4:126754626-126801618 |
| 33154 | Zmym6 | NR_104366.1 | chr4:126754626-126801618 |
| 33155 | Zmynd10 | NM_053253.3 | chr9:107449640-107453650 |
| 33156 | Zmynd11 | NM_001199141.1 | chr13:9684081-9764560 |
| 33157 | Zmynd11 | NM_144516.3 | chr13:9684081-9764560 |
| 33158 | Zmynd12 | NM_001014900.2 | chr4:119095288-119126504 |
| 33159 | Zmynd15 | NM_001029929.2 | chr11:70273124-70279701 |
| 33160 | Zmynd19 | NM_026021.3 | chr2:24805321-24814933 |

Fig. 25 - 176

| | | | |
|---|---|---|---|
| 33161 | Zmynd8 | NM_001252584.2 | chr2:165609651-165710338 |
| 33162 | Zmynd8 | NM_001252585.2 | chr2:165609651-165710338 |
| 33163 | Zmynd8 | NM_001252587.2 | chr2:165609651-165710338 |
| 33164 | Zmynd8 | NM_001281926.1 | chr2:165609651-165710338 |
| 33165 | Zmynd8 | NM_001291158.1 | chr2:165609651-165710338 |
| 33166 | Zmynd8 | NM_027230.4 | chr2:165609651-165710338 |
| 33167 | Znf41-ps | NR_040355.1 | chr4:146514186-146556724 |
| 33168 | Znfs12b | NM_001164597.1 | chr2:181316808-181327166 |
| 33169 | Znfx1 | NM_001033196.2 | chr2:166861295-166891362 |
| 33170 | Znfx1 | NM_001291162.1 | chr2:166861295-166891362 |
| 33171 | Znhit1 | NM_027318.3 | chr5:137458071-137463752 |
| 33172 | Znhit2 | NM_013859.2 | chr19:6061206-6062468 |
| 33173 | Znhit3 | NM_001005223.2 | chr11:84724457-84729858 |
| 33174 | Znhit6 | NM_001081094.1 | chr3:145239171-145268209 |
| 33175 | Znrd1 | NM_023162.4 | chr17:37091302-37095373 |
| 33176 | Znrd1as | NM_029602.1 | chr17:37095536-37102568 |
| 33177 | Znrf1 | NM_001168621.1 | chr8:114060539-114149930 |
| 33178 | Znrf1 | NM_001168622.1 | chr8:114060539-114149930 |
| 33179 | Znrf1 | NM_001168623.1 | chr8:114060539-114149930 |
| 33180 | Znrf1 | NM_133206.3 | chr8:114060539-114149930 |
| 33181 | Znrf2 | NM_199143.2 | chr6:54766909-54840218 |
| 33182 | Znrf3 | NM_001080924.2 | chr11:5176331-5344850 |
| 33183 | Znrf3 | NM_001290501.1 | chr11:5176331-5344850 |
| 33184 | Znrf4 | NM_011483.2 | chr17:56650670-56651906 |
| 33185 | Zp1 | NM_009580.2 | chr19:10988786-10995091 |
| 33186 | Zp2 | NM_011775.6 | chr7:127275874-127288804 |
| 33187 | Zp3 | NM_011776.1 | chr5:136455974-136464494 |
| 33188 | Zp3r | NM_009581.2 | chr1:132473282-132526183 |
| 33189 | Zp4-ps | NR_027813.1 | chr13:11614318-11617949 |
| 33190 | Zpbp | NM_001185153.1 | chr11:11180042-11362422 |
| 33191 | Zpbp | NM_015785.2 | chr11:11180042-11362422 |
| 33192 | Zpbp2 | NM_001166494.1 | chr11:98412410-98419979 |
| 33193 | Zpbp2 | NM_001166495.1 | chr11:98412410-98419979 |
| 33194 | Zpbp2 | NM_027061.2 | chr11:98412410-98419979 |
| 33195 | Zpbp2 | NM_199419.3 | chr11:98412410-98419979 |
| 33196 | Zpld1 | NM_178720.4 | chr16:55225287-55283350 |
| 33197 | Zpr1 | NM_011752.2 | chr9:46081146-46090725 |
| 33198 | Zranb1 | NM_207302.1 | chr7:140141304-140175634 |
| 33199 | Zranb2 | NM_017381.2 | chr3:157197361-157211303 |
| 33200 | Zranb3 | NM_001285945.1 | chr1:129850755-129999624 |
| 33201 | Zranb3 | NM_027678.3 | chr1:129850755-129999624 |
| 33202 | Zrsr1 | NM_011663.3 | chr11:22872005-22876496 |
| 33203 | Zrsr2 | NM_009453.3 | chrX:160373374-160396598 |
| 33204 | Zrsr2 | NM_178794.4 | chrX:160373374-160396598 |
| 33205 | Zscan10 | NM_001033425.4 | chr17:23737792-23747986 |
| 33206 | Zscan10 | NM_001289481.1 | chr17:23737792-23747986 |
| 33207 | Zscan10 | NM_001289482.1 | chr17:23737792-23747986 |
| 33208 | Zscan10 | NM_001289483.1 | chr17:23737792-23747986 |
| 33209 | Zscan10 | NM_001289484.1 | chr17:23737792-23747986 |
| 33210 | Zscan12 | NM_016684.2 | chr13:21454688-21464171 |
| 33211 | Zscan18 | NM_001017955.2 | chr7:13353440-13361007 |
| 33212 | Zscan2 | NM_009553.2 | chr7:88006993-88021399 |
| 33213 | Zscan20 | NM_177758.4 | chr4:128260782-128287342 |
| 33214 | Zscan21 | NM_001044703.2 | chr5:138558132-138575493 |
| 33215 | Zscan21 | NM_001044704.2 | chr5:138558132-138575493 |
| 33216 | Zscan21 | NM_001044705.2 | chr5:138558132-138575493 |
| 33217 | Zscan21 | NM_011757.3 | chr5:138558132-138575493 |
| 33218 | Zscan22 | NM_001001447.3 | chr7:13483157-13494432 |
| 33219 | Zscan22 | NM_001290436.1 | chr7:13483157-13494432 |
| 33220 | Zscan22 | NM_001290438.1 | chr7:13483157-13494432 |
| 33221 | Zscan22 | NM_001290440.1 | chr7:13483157-13494432 |
| 33222 | Zscan22 | NM_001290441.1 | chr7:13483157-13494432 |
| 33223 | Zscan22 | NM_001290442.1 | chr7:13483157-13494432 |
| 33224 | Zscan25 | NM_001081431.1 | chr5:146044211-146052338 |
| 33225 | Zscan26 | NM_001013786.2 | chr13:21534044-21545596 |
| 33226 | Zscan29 | NM_001290819.1 | chr2:120983162-120996885 |
| 33227 | Zscan29 | NM_001290820.1 | chr2:120983162-120996885 |
| 33228 | Zscan29 | NM_178889.4 | chr2:120983162-120996885 |
| 33229 | Zscan4a | NR_033707.1 | chr7:11379589-11384414 |
| 33230 | Zscan4b | NM_001185173.1 | chr7:11486088-11490399 |
| 33231 | Zscan4c | NM_001013765.2 | chr7:11591093-11595896 |
| 33232 | Zscan4d | NM_001100186.1 | chr7:11746991-11751497 |
| 33233 | Zscan4e | NM_001161802.1 | chr7:11891726-11896031 |
| 33234 | Zscan4f | NM_001110316.2 | chr7:11983263-11987667 |
| 33235 | Zscan5b | NM_133204.2 | chr7:6173879-6191014 |
| 33236 | Zswim1 | NM_028028.2 | chr2:164648185-164652367 |
| 33237 | Zswim2 | NM_027964.2 | chr2:83755235-83781383 |
| 33238 | Zswim3 | NM_178375.2 | chr2:164630613-164647627 |
| 33239 | Zswim4 | NM_172503.3 | chr8:86734840-86780941 |
| 33240 | Zswim5 | NM_001029912.2 | chr4:116550006-116661710 |
| 33241 | Zswim6 | NM_145456.2 | chr13:108514696-108680258 |
| 33242 | Zswim7 | NM_027198.1 | chr11:62080725-62094897 |
| 33243 | Zswim8 | NM_001252081.1 | chr14:21526773-21542841 |
| 33244 | Zswim8 | NM_001252082.1 | chr14:21526773-21542841 |
| 33245 | Zswim8 | NM_027996.3 | chr14:21526773-21542841 |
| 33246 | Zufsp | NM_028287.2 | chr10:33646741-33671018 |
| 33247 | Zw10 | NM_012039.2 | chr9:48863685-48886878 |
| 33248 | Zwilch | NM_026507.4 | chr9:63984951-64020738 |
| 33249 | Zwint | NM_025635.4 | chr10:72117642-72132537 |
| 33250 | Zxda | NR_003292.1 | chrX:92036623-92043628 |
| 33251 | Zxdb | NM_001081473.1 | chrX:91969907-91975530 |
| 33252 | Zxdc | NM_030260.3 | chr6:90319487-90353480 |
| 33253 | Zxdc | NM_173002.3 | chr6:90319487-90353480 |
| 33254 | Zyg11a | NM_001167936.1 | chr4:107854538-107890527 |
| 33255 | Zyg11b | NM_001033634.3 | chr4:107900359-107973695 |
| 33256 | Zyx | NM_001289617.1 | chr6:42299826-42330557 |
| 33257 | Zyx | NM_001289618.1 | chr6:42299826-42330557 |
| 33258 | Zyx | NM_001289619.1 | chr6:42299826-42330557 |
| 33259 | Zyx | NM_011777.3 | chr6:42299826-42330557 |
| 33260 | Zzef1 | NM_001045536.2 | chr11:72609727-72740622 |
| 33261 | Zzz3 | NM_001080755.2 | chr3:152058966-152344396 |
| 33262 | Zzz3 | NM_001287139.1 | chr3:152058966-152344396 |

Fig. 26 - 1

| Line No. | Gene Name | Reference Seq. ID | Chromosome Location |
|---|---|---|---|
| 1 | 0610005C13Rik | NR_038165.1 | chr7:45567794-45575176 |
| 2 | 0610007P14Rik | NM_021446.2 | chr12:85815454-85824545 |
| 3 | 0610009B22Rik | NM_025319.2 | chr11:51685384-51688634 |
| 4 | 0610009L18Rik | NR_038126.1 | chr11:120348677-120351190 |
| 5 | 0610009O20Rik | NM_024179.5 | chr18:38250248-38262629 |
| 6 | 0610010B08Rik | NM_001177543.1 | chr2:175965355-175981734 |
| 7 | 0610010F05Rik | NM_027860.2 | chr11:23573775-23633631 |
| 8 | 0610010K14Rik | NM_001177601.1 | chr11:70235203-70237914 |
| 9 | 0610011F06Rik | NM_026686.2 | chr17:25875499-25877163 |
| 10 | 0610012G03Rik | NR_027897.1 | chr16:31947050-31948521 |
| 11 | 0610030E20Rik | NM_026696.1 | chr6:72347316-72353160 |
| 12 | 0610031J06Rik | NM_020003.1 | chr3:88325022-88328631 |
| 13 | 0610031O16Rik | NR_045760.1 | chr3:138210716-138239663 |
| 14 | 0610037L13Rik | NM_026754.2 | chr4:107889898-107897802 |
| 15 | 0610038B21Rik | NR_028125.1 | chr8:77517055-77518578 |
| 16 | 0610039K10Rik | NR_028113.1 | chr2:163644849-163645800 |
| 17 | 0610040B10Rik | NR_027874.1 | chr5:143329307-143332704 |
| 18 | 0610040F04Rik | NR_040757.1 | chr6:108610217-108623167 |
| 19 | 0610040J01Rik | NM_029554.4 | chr5:63812494-63899619 |
| 20 | 0610043K17Rik | NR_040640.1 | chr4:101353782-101399185 |
| 21 | 1010001N08Rik | NR_106022.1 | chr18:11049928-11052567 |
| 22 | 1100001G20Rik | NM_183249.2 | chr1:83746939-83752646 |
| 23 | 1100001J03Rik | NM_025363.3 | chr6:38534860-38539449 |
| 24 | 1110002L01Rik | NR_030694.1 | chr2:34403882-3426747 |
| 25 | 1110004E09Rik | NM_026502.2 | chr16:90925810-90934849 |
| 26 | 1110004F10Rik | NM_019772.2 | chr7:116093379-116105210 |
| 27 | 1110006O24Rik | NR_027810.1 | chr5:115631048-115631816 |
| 28 | 1110007C09Rik | NR_026738.2 | chr3:49202950-49216026 |
| 29 | 1110008F13Rik | NM_026124.3 | chr2:156863121-156873562 |
| 30 | 1110008L16Rik | NM_025373.1 | chr12:55302636-55382491 |
| 31 | 1110008P14Rik | NM_198001.2 | chr2:32379100-32381915 |
| 32 | 1110012L19Rik | NM_026787.2 | chrX:70385912-70389416 |
| 33 | 1110015O18Rik | NR_045272.1 | chr3:4798707-4814911 |
| 34 | 1110017D15Rik | NM_001048005.1 | chr4:41505008-41517333 |
| 35 | 1110019D14Rik | NR_045995.1 | chr6:13871568-13896421 |
| 36 | 1110020A21Rik | NR_027929.1 | chr17:84917181-84957423 |
| 37 | 1110025L11Rik | NM_001076278.1 | chr16:89063409-89064002 |
| 38 | 1110028F11Rik | NR_045139.1 | chr11:87699523-87705327 |
| 39 | 1110028F18Rik | NR_045470.1 | chr8:106587142-106594820 |
| 40 | 1110032A03Rik | NM_023483.3 | chr9:50762827-50768152 |
| 41 | 1110032F04Rik | NM_001167996.1 | chr3:68869585-68872163 |
| 42 | 1110034G24Rik | NM_028637.1 | chr2:132690282-132751055 |
| 43 | 1110036E04Rik | NR_040713.1 | chr9:64049828-64054100 |
| 44 | 1110037F02Rik | NM_001081183.1 | chr4:11485957-11551143 |
| 45 | 1110038B12Rik | NR_015536.1 | chr17:34950235-34952471 |
| 46 | 1110038F14Rik | NM_054099.2 | chr15:76948543-76950731 |
| 47 | 1110046J04Rik | NR_040707.1 | chr13:33936031-33960181 |
| 48 | 1110051M20Rik | NR_175123.4 | chr2:91277827-91444642 |
| 49 | 1110054M08Rik | NR_037954.1 | chr16:24392555-24393655 |
| 50 | 1110057K04Rik | NM_001167767.1 | chr12:8208126-8285759 |
| 51 | 1110058L19Rik | NM_026503.3 | chr1:23995938-24005640 |
| 52 | 1110059E24Rik | NM_025423.2 | chr19:21597312-21652791 |
| 53 | 1110059G10Rik | NM_025419.4 | chr9:122945088-122951000 |
| 54 | 1110065P20Rik | NM_001142727.1 | chr4:124849484-124850730 |
| 55 | 1190002F15Rik | NR_037955.1 | chr6:134929091-134951718 |
| 56 | 1190002N15Rik | NM_001033145.2 | chr9:94517863-94538081 |
| 57 | 1190003K10Rik | NM_001195435.1 | chr13:64481245-64497792 |
| 58 | 1190005I06Rik | NM_197988.1 | chr8:120608601-120634382 |
| 59 | 1190007J07Rik | NM_001135567.1 | chr10:82619850-82623228 |
| 60 | 1200014J11Rik | NM_025818.3 | chr11:73047866-73083579 |
| 61 | 1300002E11Rik | NR_037957.1 | chr16:21794346-21806125 |
| 62 | 1300002K09Rik | NM_028788.4 | chr4:45848946-45887010 |
| 63 | 1300017J02Rik | NM_027918.2 | chr9:103250529-103288297 |
| 64 | 1500004A13Rik | NR_015498.2 | chr3:88822009-88832487 |
| 65 | 1500009C09Rik | NR_073974.1 | chr15:82252396-82260751 |
| 66 | 1500009L16Rik | NM_001145198.1 | chr10:83722864-83762762 |
| 67 | 1500011B03Rik | NR_027817.1 | chr5:114808195-114813976 |
| 68 | 1500011K16Rik | NR_015476.1 | chr2:127791376-127792488 |
| 69 | 1500012F01Rik | NM_001081005.1 | chr2:167062933-167065862 |
| 70 | 1500012K07Rik | NR_045812.1 | chr7:75308695-75318485 |
| 71 | 1500015A07Rik | NM_029432.1 | chr18:61726389-61728253 |
| 72 | 1500015L24Rik | NR_045817.2 | chr19:20405287-20422785 |
| 73 | 1500015O10Rik | NM_024283.3 | chr1:43730601-43742564 |
| 74 | 1500017E21Rik | NR_033510.1 | chr19:36619417-36689479 |
| 75 | 1600002D24Rik | NR_040484.1 | chr16:95841885-95929077 |
| 76 | 1600002H07Rik | NM_028156.2 | chr17:24215055-24220769 |
| 77 | 1600002K03Rik | NM_027207.2 | chr10:80172943-80175119 |
| 78 | 1600010M07Rik | NR_037959.1 | chr7:109998376-110006646 |
| 79 | 1600012H06Rik | NM_001083880.1 | chr17:14943183-14945939 |
| 80 | 1600014C10Rik | NM_001085385.1 | chr7:38183216-38197565 |
| 81 | 1600014C23Rik | NM_028164.1 | chr17:45732863-45733844 |
| 82 | 1600014K23Rik | NM_028046.3 | chrX:85249676-85270291 |
| 83 | 1600015I10Rik | NM_001081273.2 | chr6:48929895-48933687 |
| 84 | 1600016N20Rik | NM_028050.2 | chr7:141210042-141214080 |
| 85 | 1600019A05Rik | NR_040481.1 | chr16:35503169-35509419 |
| 86 | 1600020E01Rik | NR_037960.1 | chr6:86527329-86564449 |
| 87 | 1600023N17Rik | NR_073433.1 | chr5:45668700-45669708 |
| 88 | 1600025I08Rik | NR_038168.1 | chrX:86317407-56320664 |
| 89 | 1600027J07Rik | NR_036588.1 | chr8:103343877-103347534 |
| 90 | 1600029I14Rik | NR_028123.1 | chr9:99476420-99474751 |
| 91 | 1600029O15Rik | NR_033522.1 | chr9:58202896-58208808 |
| 92 | 1700001C02Rik | NM_029285.1 | chr5:30466076-30484087 |
| 93 | 1700001C19Rik | NM_001172091.1 | chr17:47412733-47414711 |
| 94 | 1700001D01Rik | NR_045475.1 | chr8:61281521-61288872 |
| 95 | 1700001F09Rik | NM_027940.2 | chr14:43342383-43347811 |
| 96 | 1700001G11Rik | NR_038077.1 | chr14:66295328-66297129 |
| 97 | 1700001G17Rik | NR_033199.1 | chr1:33669823-33670712 |
| 98 | 1700001J03Rik | NM_001008547.1 | chr5:146182449-146185304 |
| 99 | 1700001J11Rik | NR_033613.1 | chr9:40050557-40053025 |
| 100 | 1700001K19Rik | NM_025488.2 | chr12:110667688-110682619 |
| 101 | 1700001K23Rik | NR_036590.1 | chr19:53248735-53255205 |
| 102 | 1700001L05Rik | NM_027980.1 | chr15:83353846-83367297 |
| 103 | 1700001L19Rik | NM_027035.1 | chr13:68597438-68614231 |
| 104 | 1700001O22Rik | NM_198000.3 | chr2:30795562-30801737 |
| 105 | 1700001P01Rik | NM_028156.2 | chr11:97771480-97775918 |
| 106 | 1700003C15Rik | NR_045478.1 | chr5:11749832-11769308 |
| 107 | 1700003D09Rik | NR_045477.1 | chr11:98350717-98358283 |
| 108 | 1700003E16Rik | NM_027948.1 | chr6:83156403-83162975 |
| 109 | 1700003E24Rik | NR_103799.1 | chrX:93156220-93183944 |
| 110 | 1700003F12Rik | NM_029305.2 | chr2:154548903-154550048 |
| 111 | 1700003G13Rik | NM_040720.1 | chr9:45318265-45322079 |
| 112 | 1700003G18Rik | NR_029433.1 | chr7:116081761-116093149 |
| 113 | 1700003H04Rik | NR_015460.1 | chr3:124565890-124581091 |
| 114 | 1700003L19Rik | NR_040507.1 | chr18:12811389-12848653 |
| 115 | 1700003M02Rik | NM_027041.4 | chr4:34711331-34730206 |
| 116 | 1700003M07Rik | NR_040647.1 | chr4:129966373-129965138 |
| 117 | 1700003P14Rik | NR_045982.1 | chr13:118556167-118588629 |
| 118 | 1700006A11Rik | NM_027939.1 | chr3:124401154-124426028 |
| 119 | 1700006E09Rik | NM_029287.1 | chr11:101987055-101992264 |
| 120 | 1700006F04Rik | NR_045621.1 | chr14:119749226-119751564 |
| 121 | 1700006H21Rik | NR_045900.2 | chr13:107687396-107692168 |
| 122 | 1700007B14Rik | NM_001164235.1 | chr8:75448693-75984507 |
| 123 | 1700007F19Rik | NR_040538.1 | chr3:58141706-58163807 |
| 124 | 1700007G11Rik | NM_001024614.1 | chr5:98829303-98802019 |
| 125 | 1700007I10Rik | NR_045476.1 | chr11:59725916-59740154 |
| 126 | 1700007K09Rik | NM_027037.2 | chr7:131325930-131329499 |
| 127 | 1700007K13Rik | NM_027040.1 | chr2:28462000-28466324 |
| 128 | 1700007L15Rik | NR_045709.1 | chr16:33379853-33380736 |
| 129 | 1700007P06Rik | NR_040654.1 | chr1:187125137-187127852 |
| 130 | 1700008F21Rik | NM_001168369.1 | chr8:129067133-129183732 |
| 131 | 1700008I05Rik | NM_027952.3 | chrX:135654697-135693790 |
| 132 | 1700008J07Rik | NR_024131.1 | chr7:127510437-127512869 |
| 133 | 1700008K24Rik | NR_038141.1 | chr17:49112263-49113533 |
| 134 | 1700008O03Rik | NM_027049.1 | chr7:44360044-44375030 |
| 135 | 1700008P02Rik | NM_027048.1 | chr3:6615412-6620443 |
| 136 | 1700009C05Rik | NR_046040.1 | chr6:81900464-81910800 |
| 137 | 1700009J07Rik | NR_015547.1 | chr10:77893419-77896111 |
| 138 | 1700009N14Rik | NM_001081095.1 | chr4:39450292-39451778 |
| 139 | 1700009P17Rik | NM_001081275.1 | chr1:171121660-171126967 |
| 140 | 1700010B08Rik | NM_029308.1 | chr2:173719414-173722086 |
| 141 | 1700010D01Rik | NM_029590.3 | chrX:95732589-95733265 |
| 142 | 1700010I02Rik | NR_040587.1 | chr3:7925302-7954487 |
| 143 | 1700010I14Rik | NM_025851.3 | chr17:8988332-9008319 |
| 144 | 1700010I16Rik | NR_040579.1 | chr10:112726925-112785599 |
| 145 | 1700010K23Rik | NR_040512.1 | chr16:66657117-66664626 |
| 146 | 1700011A15Rik | NM_025487.3 | chr15:101447744-101453909 |
| 147 | 1700011B04Rik | NR_045616.1 | chr13:35181622-35188014 |
| 148 | 1700011E24Rik | NM_029298.1 | chr17:87389570-87427741 |
| 149 | 1700011H14Rik | NM_025956.4 | chr14:49226358-49245428 |
| 150 | 1700011I03Rik | NM_029290.1 | chr18:57533825-57731065 |
| 151 | 1700011L22Rik | NM_026315.1 | chr8:79210429-79248583 |
| 152 | 1700011M02Rik | NR_073044.1 | chrX:102908904-102909651 |
| 153 | 1700012A03Rik | NM_029587.2 | chr6:32050287-32058915 |
| 154 | 1700012B07Rik | NM_001162428.1 | chr11:109788290-109828046 |
| 155 | 1700012B09Rik | NM_029306.3 | chr9:14758193-14771030 |
| 156 | 1700012D01Rik | NR_045171.2 | chr10:127567122-127668851 |
| 157 | 1700012D14Rik | NR_015573.2 | chr7:111117672-111122675 |
| 158 | 1700012I11Rik | NR_045140.1 | chr15:67226768-67377094 |
| 159 | 1700012L04Rik | NM_029588.3 | chrX:9283763-9284288 |
| 160 | 1700012P22Rik | NM_027056.1 | chr4:144418190-144438772 |
| 161 | 1700013D24Rik | NM_001177502.1 | chr6:124347593-124357086 |
| 162 | 1700013F07Rik | NM_029314.2 | chr3:108537583-108544697 |
| 163 | 1700013J07Rik | NM_027063.2 | chr4:137453295-137455461 |
| 164 | 1700013H16Rik | NM_001200013.1 | chrX:53742900-53757831 |
| 165 | 1700015E13Rik | NM_001039593.1 | chr1:170308860-170312125 |
| 166 | 1700015F17Rik | NM_001200025.1 | chr5:5437826-5479143 |
| 167 | 1700015G11Rik | NM_001195601.1 | chr7:52011679-52015716 |
| 168 | 1700016C15Rik | NM_027077.2 | chr1:177729813-177753305 |
| 169 | 1700016D06Rik | NM_024271.1 | chr8:11654923-11678750 |
| 170 | 1700016G22Rik | NR_045891.1 | chr13:5855508-5858092 |
| 171 | 1700016H13Rik | NM_001163550.1 | chr5:103648586-103655732 |
| 172 | 1700016K19Rik | NM_198637.2 | chr11:75999911-76003569 |
| 173 | 1700016L04Rik | NR_045824.1 | chr10:14705608-14759019 |
| 174 | 1700016L21Rik | NR_040460.1 | chr1:80445931-80475660 |
| 175 | 1700016P04Rik | NR_038149.1 | chr6:13413336-13415996 |
| 176 | 1700017B05Rik | NM_028820.2 | chr9:57252321-57262599 |
| 177 | 1700017D01Rik | NM_027058.1 | chr19:11096815-11130878 |
| 178 | 1700017G19Rik | NR_040445.1 | chr3:40504864-40522912 |
| 179 | 1700017J07Rik | NR_040326.1 | chr2:168978268-168978906 |
| 180 | 1700017N19Rik | NM_001081246.1 | chr10:100592385-100618391 |
| 181 | 1700018A04Rik | NM_029439.1 | chr13:31565491-31582513 |
| 182 | 1700018B08Rik | NM_029597.1 | chr8:121530783-121541954 |
| 183 | 1700018B24Rik | NR_003617.1 | chr3:48605730-48609100 |
| 184 | 1700018C11Rik | NM_029324.2 | chr4:63607090-63622429 |
| 185 | 1700018F24Rik | NM_027069.3 | chr5:145042989-145045678 |
| 186 | 1700018G05Rik | NR_045422.1 | chrX:102928371-102929107 |
| 187 | 1700018L02Rik | NM_028360.1 | chr19:29047482-29048729 |
| 188 | 1700019A02Rik | NM_027070.1 | chr1:53158576-53187617 |

Fig. 26 - 2

| 189 | 1700019B03Rik | NM_029598.1 | chr8:3470861-3487178 |
|---|---|---|---|
| 190 | 1700019B21Rik | NR_045442.1 | chrX:62510638-62527011 |
| 191 | 1700019D03Rik | NM_144953.2 | chr1:52925126-52952840 |
| 192 | 1700019E08Rik | NR_040497.1 | chr2:45696604-45698447 |
| 193 | 1700019G17Rik | NM_001145895.1 | chr6:85899050-85902533 |
| 194 | 1700019G24Rik | NR_040255.1 | chr6:5963896-5977393 |
| 195 | 1700019L03Rik | NM_025619.1 | chr2:32777412-32784405 |
| 196 | 1700019M22Rik | NR_103800.1 | chr12:96046620-96047222 |
| 197 | 1700019N19Rik | NM_026208.2 | chr19:58785802-58794414 |
| 198 | 1700019O17Rik | NM_027966.1 | chr1:86426328-86428049 |
| 199 | 1700020A23Rik | NM_001163483.1 | chr2:130405295-130406074 |
| 200 | 1700020D05Rik | NM_023781.5 | chr19:5502768-5503787 |
| 201 | 1700020G17Rik | NR_045979.1 | chr10:110801173-110896507 |
| 202 | 1700020I14Rik | NR_015473.1 | chr2:119594295-119600744 |
| 203 | 1700020L24Rik | NM_025492.3 | chr11:83477693-83441232 |
| 204 | 1700020M21Rik | NR_040742.1 | chr9:120913773-120915250 |
| 205 | 1700020N01Rik | NR_027968.1 | chr10:21593144-21622375 |
| 206 | 1700020N15Rik | NM_029316.1 | chrX:69945280-69945980 |
| 207 | 1700020N18Rik | NR_026924.1 | chr1:91404878-91406029 |
| 208 | 1700021F05Rik | NM_026411.1 | chr10:43525120-43540994 |
| 209 | 1700021F07Rik | NM_028158.1 | chr2:173522591-173528502 |
| 210 | 1700021K19Rik | NM_001200038.1 | chr16:32821701-32868366 |
| 211 | 1700021N21Rik | NR_045800.1 | chr4:134448764-134450171 |
| 212 | 1700022A21Rik | NR_003953.1 | chr5:24645452-24648860 |
| 213 | 1700022A22Rik | NR_045509.1 | chr5:46324584-46373899 |
| 214 | 1700022E09Rik | NR_040568.1 | chr6:59466871-59469238 |
| 215 | 1700022H16Rik | NR_045488.1 | chr12:9565235-9570585 |
| 216 | 1700022I11Rik | NM_026088.3 | chr4:42969945-42974325 |
| 217 | 1700023C21Rik | NR_045909.1 | chr11:109845877-109848476 |
| 218 | 1700023E05Rik | NM_027970.1 | chr5:77016022-77061522 |
| 219 | 1700023F02Rik | NR_038039.1 | chr10:66120608-66124064 |
| 220 | 1700023F06Rik | NM_001254724.2 | chr11:103198943-103208548 |
| 221 | 1700023L04Rik | NR_040263.1 | chr6:29985328-29993531 |
| 222 | 1700024B18Rik | NR_045479.1 | chr14:123987634-124015684 |
| 223 | 1700024F13Rik | NR_045363.1 | chr3:3498049-3501393 |
| 224 | 1700024G13Rik | NM_001034037.1 | chr14:32376501-32388373 |
| 225 | 1700024P04Rik | NM_027064.1 | chr13:98984089-98984565 |
| 226 | 1700024P16Rik | NM_001162980.1 | chr4:104913455-105016863 |
| 227 | 1700025B11Rik | NR_040301.1 | chr5:77558239-77561892 |
| 228 | 1700025C18Rik | NR_033448.1 | chr2:165078692-165090750 |
| 229 | 1700025F22Rik | NM_027074.3 | chr19:11139682-11165320 |
| 230 | 1700025F24Rik | NR_040578.1 | chr10:119413443-119426864 |
| 231 | 1700025G04Rik | NM_197990.3 | chr1:151884523-152090320 |
| 232 | 1700025K24Rik | NR_045825.1 | chr17:54352582-54370074 |
| 233 | 1700025M24Rik | NR_040687.1 | chr5:73268579-73284184 |
| 234 | 1700025N23Rik | NR_040523.1 | chr6:39063878-39067586 |
| 235 | 1700026D08Rik | NM_029335.3 | chr7:83775616-83794839 |
| 236 | 1700026D11Rik | NR_028286.1 | chr2:132490727-132524057 |
| 237 | 1700026F02Rik | NR_045487.1 | chr8:71006727-71026755 |
| 238 | 1700026L06Rik | NM_027283.1 | chr2:28692079-28699651 |
| 239 | 1700027A15Rik | NR_038001.1 | chr1:73016035-73025508 |
| 240 | 1700027F09Rik | NR_040681.1 | chr5:64454812-64467942 |
| 241 | 1700027H10Rik | NR_040594.1 | chr3:45416583-45439309 |
| 242 | 1700027I24Rik | NR_040741.1 | chr9:36668855-36693189 |
| 243 | 1700027J07Rik | NR_040581.2 | chr10:43746157-43765836 |
| 244 | 1700028B04Rik | NR_033605.1 | chr7:28496940-28497492 |
| 245 | 1700028D13Rik | NR_045377.1 | chr5:112206762-112210002 |
| 246 | 1700028E10Rik | NR_045699.1 | chr5:151368674-151396164 |
| 247 | 1700028I16Rik | NR_038042.1 | chr10:82812122-82824242 |
| 248 | 1700028J19Rik | NR_029436.1 | chr7:44229929-44236122 |
| 249 | 1700028K03Rik | NM_175241.1 | chr5:107534710-107551542 |
| 250 | 1700028M03Rik | NR_036591.1 | chr3:83555366-83574118 |
| 251 | 1700028P14Rik | NR_026188.2 | chr19:23558759-23652812 |
| 252 | 1700028P15Rik | NR_040509.1 | chr2:171956878-171962799 |
| 253 | 1700029B22Rik | NR_040531.1 | chr7:131146438-131150578 |
| 254 | 1700029F12Rik | NM_001080777.2 | chr13:97021863-97034362 |
| 255 | 1700029H14Rik | NM_001080781.2 | chr8:135050721-13562461 |
| 256 | 1700029I15Rik | NM_183112.3 | chr2:92382917-92383603 |
| 257 | 1700029J03Rik | NR_040494.1 | chr16:93396814-93458872 |
| 258 | 1700029J07Rik | NM_001033148.3 | chr8:45953605-45975252 |
| 259 | 1700029M20Rik | NR_015613.1 | chr4:135626654-135630198 |
| 260 | 1700029N11Rik | NR_045489.1 | chr13:44439726-44457567 |
| 261 | 1700029P11Rik | NM_025503.4 | chr15:81980539-81981563 |
| 262 | 1700030A11Rik | NR_045457.1 | chr17:28905264-28906771 |
| 263 | 1700030C10Rik | NR_015521.1 | chr12:20804891-20815779 |
| 264 | 1700030F04Rik | NR_045731.1 | chr5:117679286-117751769 |
| 265 | 1700030F18Rik | NM_028180.3 | chr15:99918347-99931658 |
| 266 | 1700030J22Rik | NM_027103.2 | chr8:116969598-116978943 |
| 267 | 1700030K09Rik | NM_028170.2 | chr8:72443879-72460541 |
| 268 | 1700030L20Rik | NR_040592.1 | chr3:136435269-136449349 |
| 269 | 1700030M09Rik | NR_045903.1 | chr8:121544387-121547652 |
| 270 | 1700030N03Rik | NR_045304.1 | chr19:3153798-3197703 |
| 271 | 1700030O20Rik | NR_045345.1 | chr10:116723066-116729177 |
| 272 | 1700031A10Rik | NR_045439.1 | chr17:36923791-36933432 |
| 273 | 1700031F05Rik | NM_028496.1 | chrX:102859186-102866353 |
| 274 | 1700031M16Rik | NR_015496.1 | chr5:98398444-98416135 |
| 275 | 1700031P21Rik | NR_045610.1 | chr12:52599983-52602322 |
| 276 | 1700034E13Rik | NM_030097.1 | chr18:52646219-52663731 |
| 277 | 1700034F02Rik | NM_001163521.1 | chr1:29547949-29576352 |
| 278 | 1700034G24Rik | NR_045396.1 | chr5:112582935-112589996 |
| 279 | 1700034H15Rik | NR_030669.1 | chr1:191894071-191907527 |
| 280 | 1700034I23Rik | NR_045380.1 | chr3:40900198-40902543 |
| 281 | 1700034J05Rik | NM_001164236.1 | chr6:146951300-146954421 |
| 282 | 1700034K08Rik | NR_040756.1 | chr9:92979915-93005733 |
| 283 | 1700034O15Rik | NM_029671.2 | chr6:41684430-41685717 |
| 284 | 1700034P13Rik | NR_040462.1 | chr1:9747647-9771256 |
| 285 | 1700036G14Rik | NR_040542.1 | chr3:85317518-85332027 |
| 286 | 1700037C18Rik | NM_028484.2 | chr16:3905797-3908689 |
| 287 | 1700037H04Rik | NM_026091.2 | chr2:131146324-131160020 |
| 288 | 1700039E15Rik | NM_001033176.1 | chr7:45282872-45288993 |
| 289 | 1700039E22Rik | NR_045315.1 | chr19:44828492-44835938 |
| 290 | 1700040L02Rik | NM_028491.1 | chr10:68430955-68541875 |
| 291 | 1700041C23Rik | NR_033784.1 | chr9:57175274-57186110 |
| 292 | 1700041M19Rik | NR_040573.1 | chr16:77004227-77010881 |
| 293 | 1700042B14Rik | NM_001081671.1 | chrX:155124980-155147849 |
| 294 | 1700042G07Rik | NM_001099295.2 | chr4:116173371-116174297 |
| 295 | 1700042G15Rik | NR_038178.1 | chr4:57359791-57364292 |
| 296 | 1700042O10Rik | NR_045178.1 | chr11:11868122-11885321 |
| 297 | 1700044C05Rik | NR_045624.1 | chr14:118365877-118398165 |
| 298 | 1700044K03Rik | NR_033785.1 | chr18:49523288-49524441 |
| 299 | 1700045H11Rik | NR_040649.1 | chr4:150828224-150854949 |
| 300 | 1700046C09Rik | NR_045918.1 | chr11:14560335-14599225 |
| 301 | 1700047A11Rik | NR_110583.1 | chr8:26082608-26096520 |
| 302 | 1700047E10Rik | NR_073363.1 | chr14:44191606-44213237 |
| 303 | 1700047G03Rik | NR_040447.1 | chr15:11967061-11970083 |
| 304 | 1700047H7Rik2 | NM_001100116.1 | chr12:55124527-55217146 |
| 305 | 1700047L14Rik | NR_040691.1 | chr5:108763841-108768917 |
| 306 | 1700047M11Rik | NR_015458.1 | chr1:182300833-182303289 |
| 307 | 1700048M11Rik | NR_045300.1 | chr16:92308715-92312466 |
| 308 | 1700048M20Rik | NR_033553.1 | chr9:121937274-121947016 |
| 309 | 1700049E15Rik | NR_033636.1 | chr6:147690240-147702374 |
| 310 | 1700049E22Rik | NR_040525.1 | chr6:100527399-100533426 |
| 311 | 1700049G17Rik | NM_028533.1 | chr7:27907391-27929430 |
| 312 | 1700049L16Rik | NR_003644.1 | chr10:71979884-71980690 |
| 313 | 1700051A21Rik | NR_045922.1 | chr11:72266843-72268556 |
| 314 | 1700052I22Rik | NR_033786.1 | chr12:80923431-80924447 |
| 315 | 1700052K11Rik | NR_027956.1 | chr11:105179020-105181433 |
| 316 | 1700052N19Rik | NM_024261.2 | chr10:4432604-4455140 |
| 317 | 1700054A03Rik | NR_045320.1 | chr19:53076251-53084392 |
| 318 | 1700054K19Rik | NR_027865.1 | chr6:112210707-112212518 |
| 319 | 1700054M17Rik | NR_045919.1 | chr2:118304913-118308166 |
| 320 | 1700054O13Rik | NR_026096.1 | chrX:9846946-9847500 |
| 321 | 1700055C04Rik | NR_040726.1 | chr9:64038464-64041465 |
| 322 | 1700055N04Rik | NM_028545.2 | chr19:3958807-3970438 |
| 323 | 1700056E22Rik | NR_028516.1 | chr1:184033031-184033998 |
| 324 | 1700057G04Rik | NM_001033184.3 | chr9:92309376-92357876 |
| 325 | 1700057H15Rik | NR_040774.1 | chr4:124449625-124485959 |
| 326 | 1700060C16Rik | NR_045732.1 | chr3:143593352-143651288 |
| 327 | 1700060C20Rik | NR_036606.2 | chr2:158192007-158195734 |
| 328 | 1700061F12Rik | NR_038180.1 | chr2:9189514-9197484 |
| 329 | 1700061G19Rik | NM_030141.1 | chr17:56875632-56888838 |
| 330 | 1700061I17Rik | NR_038029.1 | chr3:117060521-117077765 |
| 331 | 1700063A18Rik | NR_040467.1 | chr1:95990658-96021758 |
| 332 | 1700063D05Rik | NR_040392.1 | chr9:41206154-41217627 |
| 333 | 1700063O14Rik | NR_045383.1 | chr5:91766241-91767300 |
| 334 | 1700064I06Rik | NR_045348.1 | chr10:119092904-119103107 |
| 335 | 1700064M15Rik | NR_045288.1 | chr12:99626052-99627974 |
| 336 | 1700065C05Rik | NM_001171569.1 | chr9:95855417-95857882 |
| 337 | 1700065I16Rik | NR_040315.2 | chr15:63817187-63819540 |
| 338 | 1700065J11Rik | NR_040526.1 | chr6:35330845-35336829 |
| 339 | 1700065J18Rik | NR_040465.1 | chr1:192841704-192842739 |
| 340 | 1700065L07Rik | NR_108032.1 | chr6:73436964-73471021 |
| 341 | 1700065O20Rik | NR_045386.1 | chr18:49803331-49817956 |
| 342 | 1700066B17Rik | NR_040465.1 | chr1:39842427-39847330 |
| 343 | 1700066B19Rik | NM_001033168.2 | chr18:35726998-35730869 |
| 344 | 1700066M21Rik | NM_028546.1 | chr1:57377619-57385422 |
| 345 | 1700066N21Rik | NR_045694.1 | chr5:87908587-87979351 |
| 346 | 1700066O22Rik | NR_015541.2 | chr18:57504421-57533752 |
| 347 | 1700067G17Rik | NR_040471.1 | chr1:89016112-89022210 |
| 348 | 1700067K01Rik | NM_183097.2 | chr8:84001705-84004770 |
| 349 | 1700067P10Rik | NR_026625.2 | chr17:48089631-48090920 |
| 350 | 1700069L16Rik | NR_033216.1 | chr5:113692423-113724772 |
| 351 | 1700069P05Rik | NR_040527.1 | chr6:118246694-118248454 |
| 352 | 1700071K01Rik | NM_001033765.2 | chr11:81572501-81573539 |
| 353 | 1700071M16Rik | NR_045444.1 | chr17:43588339-43591509 |
| 354 | 1700072B07Rik | NR_040727.1 | chr9:58370503-58374183 |
| 355 | 1700072O05Rik | NR_045733.1 | chr6:120554795-120574204 |
| 356 | 1700073E17Rik | NR_003625.1 | chr8:145387624-145392223 |
| 357 | 1700074H08Rik | NR_045296.1 | chr13:119680041-119681582 |
| 358 | 1700074P13Rik | NM_028550.3 | chr6:40920459-40940557 |
| 359 | 1700080E17Rik | NM_028562.3 | chr9:105143343-105145082 |
| 360 | 1700080N15Rik | NR_040500.1 | chr2:4132064-4141141 |
| 361 | 1700080O16Rik | NM_028851.1 | chrX:51968694-51972772 |
| 362 | 1700081H04Rik | NM_028965.1 | chr5:119108235-119114543 |
| 363 | 1700084C01Rik | NM_001033185.2 | chr1:169928938-169934653 |
| 364 | 1700084E18Rik | NR_028299.1 | chr2:30237397-30237631 |
| 365 | 1700084G22Rik | NR_045965.1 | chr13:70004049-70028348 |
| 366 | 1700084J12Rik | NR_033608.1 | chr15:33405208-33405939 |
| 367 | 1700085C21Rik | NR_046045.1 | chr12:82932519-82939155 |
| 368 | 1700085L19Rik | NR_030733.1 | chr12:74284275-74295950 |
| 369 | 1700086G06Rik | NR_015475.1 | chr18:38238404-38250198 |
| 370 | 1700088E04Rik | NM_138581.2 | chr15:79134654-79141251 |
| 371 | 1700091H14Rik | NR_073362.1 | chr14:42089749-42095277 |
| 372 | 1700092C02Rik | NR_045467.1 | chr8:77624171-77628956 |
| 373 | 1700092C14Rik | NR_045931.1 | chr14:69164798-69171843 |
| 374 | 1700092E19Rik | NR_045933.1 | chr13:26283158-26312406 |
| 375 | 1700092K14Rik | NR_045930.1 | chr11:114198257-114199199 |
| 376 | 1700092M07Rik | NM_001177347.1 | chr19:8740717-8741225 |
| 377 | 1700093K21Rik | NM_001110133.1 | chr11:235162202-235199422 |
| 378 | 1700094D03Rik | NM_028567.1 | chr3:90062795-90068347 |

Fig. 26 - 3

| | | | |
|---|---|---|---|
| 379 | 1700094J05Rik | NR_040580.1 | chr10:76389014-76401507 |
| 380 | 1700094M24Rik | NR_046049.1 | chr6:52492450-52500085 |
| 381 | 1700095A21Rik | NR_045468.1 | chr4:146519038-146546873 |
| 382 | 1700095B10Rik | NR_040675.1 | chr5:112793291-112801701 |
| 383 | 1700096J18Rik | NR_027883.1 | chr11:109346856-109353651 |
| 384 | 1700096K18Rik | NR_027388.1 | chr5:25530017-25531466 |
| 385 | 1700097N02Rik | NR_045287.1 | chr7:30622440-30626905 |
| 386 | 1700100L14Rik | NR_045934.1 | chr13:70573240-70576104 |
| 387 | 1700101E01Rik | NM_001166705.1 | chr2:28955480-29055066 |
| 388 | 1700101I11Rik | NR_045270.1 | chr6:129532183-129533284 |
| 389 | 1700101O22Rik | NR_045045.1 | chr12:7372038-7380330 |
| 390 | 1700102H20Rik | NR_045302.1 | chr17:3557823-3559863 |
| 391 | 1700102P08Rik | NM_053216.2 | chr9:108392833-108397767 |
| 392 | 1700104L18Rik | NR_108033.1 | chr12:54233614-54242320 |
| 393 | 1700105P06Rik | NR_045703.1 | chr19:7383002-7383557 |
| 394 | 1700106I16Rik | NM_028859.1 | chr1:88294042-88295261 |
| 395 | 1700108F19Rik | NR_015485.1 | chr14:76677567-76687108 |
| 396 | 1700108J01Rik | NR_015532.1 | chr14:122229904-122233638 |
| 397 | 1700109G14Rik | NR_037883.1 | chr14:61292982-61305334 |
| 398 | 1700109G15Rik | NR_046197.1 | chr1:84716975-84720432 |
| 399 | 1700109H08Rik | NM_029843.2 | chr5:3571715-3584341 |
| 400 | 1700109I08Rik | NR_045936.1 | chr14:39655662-39685293 |
| 401 | 1700109K24Rik | NR_108037.1 | chr15:77084397-77096314 |
| 402 | 1700110C19Rik | NR_045461.1 | chr17:10324601-10329312 |
| 403 | 1700110I01Rik | NR_038059.1 | chr14:3262401-3783730 |
| 404 | 1700110K17Rik | NR_040728.1 | chr9:40333471-40343337 |
| 405 | 1700111N16Rik | NR_033213.2 | chrX:69929259-70143588 |
| 406 | 1700112E06Rik | NM_026775.1 | chr14:22019711-23056088 |
| 407 | 1700112H15Rik | NR_040472.1 | chr1:184527840-184557691 |
| 408 | 1700112J05Rik | NR_077218.1 | chr5:77006441-77018863 |
| 409 | 1700113A16Rik | NR_045997.1 | chr3:88171559-88177785 |
| 410 | 1700113H08Rik | NM_029685.1 | chr10:87058045-87230599 |
| 411 | 1700119H24Rik | NR_040536.1 | chr16:34935854-34939329 |
| 412 | 1700120C14Rik | NR_045622.2 | chr15:99251787-99262041 |
| 413 | 1700120E14Rik | NR_045368.1 | chr18:74495677-74531124 |
| 414 | 1700120G07Rik | NR_046050.1 | chr7:135191764-135196002 |
| 415 | 1700120K04Rik | NR_027915.1 | chr7:127603902-127604445 |
| 416 | 1700121L16Rik | NR_045453.1 | chrX:104816775-104842455 |
| 417 | 1700121N20Rik | NR_036593.1 | chr12:106442651-106447666 |
| 418 | 1700122O11Rik | NM_029689.1 | chr17:48036744-48038293 |
| 419 | 1700123J01Rik | NM_001165919.1 | chr19:6184409-6224219 |
| 420 | 1700123K08Rik | NM_029693.2 | chr5:138561839-138564694 |
| 421 | 1700123L14Rik | NR_003643.1 | chr6:96164502-96166205 |
| 422 | 1700123M08Rik | NR_040577.1 | chr4:11966573-11994295 |
| 423 | 1700123O12Rik | NR_045185.1 | chr4:10508030-10797802 |
| 424 | 1700123O20Rik | NM_021437.2 | chr14:54686170-54690742 |
| 425 | 1700123O21Rik | NR_045799.1 | chr16:5975586-5998496 |
| 426 | 1700124L16Rik | NR_105027.1 | chr6:83761758-83762508 |
| 427 | 1700125G02Rik | NR_040651.1 | chr4:124890887-124894782 |
| 428 | 1700125G22Rik | NR_040548.1 | chr3:27154025-27157019 |
| 429 | 1700125H03Rik | NR_038181.1 | chr8:68368458-68375710 |
| 430 | 1700125H20Rik | NM_028589.1 | chr11:85171095-85181154 |
| 431 | 1700126H14Rik | NR_040695.1 | chr5:66166606-66191335 |
| 432 | 1700128A07Rik | NR_045938.2 | chr14:106417186-106486520 |
| 433 | 1700128F08Rik | NR_033618.2 | chr9:8221888-8241987 |
| 434 | 1700129C05Rik | NM_026461.2 | chr14:59133039-59142893 |
| 435 | 1810006J02Rik | NR_040439.1 | chr1:98131466-98144655 |
| 436 | 1810007C17Rik | NR_045472.1 | chr12:49476992-49480862 |
| 437 | 1810007D17Rik | NR_038136.1 | chr19:58606328-58629753 |
| 438 | 1810008I18Rik | NR_045301.1 | chr7:65804051-65806223 |
| 439 | 1810009A15Rik | NM_025463.3 | chr19:8888882-8896759 |
| 440 | 1810009J06Rik | NM_027073 | chr6:40964771-40988427 |
| 441 | 1810010D01Rik | NR_033626.1 | chr7:145205817-145208119 |
| 442 | 1810010H24Rik | NM_001163473.1 | chr11:107028222-107030442 |
| 443 | 1810011H11Rik | NM_001163616.1 | chr14:32785962-32817968 |
| 444 | 1810011O10Rik | NR_026931.2 | chr8:24437815-24438946 |
| 445 | 1810012K16Rik | NR_045473.1 | chr8:22398720-22399591 |
| 446 | 1810013A23Rik | NR_045427.1 | chr7:28271707-28273163 |
| 447 | 1810013L24Rik | NM_001081400.3 | chr18:8830099-8858924 |
| 448 | 1810014J01Rik | NR_015572.2 | chr10:86685526-86689954 |
| 449 | 1810018F18Rik | NR_038140.1 | chr19:58698916-58701323 |
| 450 | 1810019D21Rik | NR_040344.1 | chr8:106135399-106138722 |
| 451 | 1810020O05Rik | NR_045482.1 | chr6:87675592-87690847 |
| 452 | 1810021B22Rik | NR_040417.1 | chr5:89071197-89075854 |
| 453 | 1810022K09Rik | NM_001099674.1 | chr3:14606288-14611256 |
| 454 | 1810024B03Rik | NM_198630.2 | chr12:127186354-127208280 |
| 455 | 1810026B05Rik | NR_037569.1 | chr7:73539797-73558395 |
| 456 | 1810026J23Rik | NR_178619.4 | chr9:21592721-21595870 |
| 457 | 1810030O07Rik | NM_175141.4 | chrX:12654880-12673639 |
| 458 | 1810032O08Rik | NR_027819.1 | chr11:116671659-116675798 |
| 459 | 1810034E14Rik | NR_045798.1 | chr13:64248699-64268145 |
| 460 | 1810037I17Rik | NM_024461.2 | chr3:122924496-122926194 |
| 461 | 1810041L15Rik | NM_001163145.1 | chr15:84379202-84447097 |
| 462 | 1810043G02Rik | NM_026431.2 | chr10:77978649-77985438 |
| 463 | 1810043H04Rik | NM_001110242.1 | chr11:120098933-120100424 |
| 464 | 1810044D09Rik | NR_038153.1 | chr6:91440986-91441755 |
| 465 | 1810046K07Rik | NM_027217.1 | chr9:51289685-51328917 |
| 466 | 1810053B23Rik | NR_040486.1 | chr6:93343723-93353189 |
| 467 | 1810055G02Rik | NR_028077.2 | chr19:3708832-3717881 |
| 468 | 1810058I24Rik | NR_015608.1 | chr6:35252698-35262059 |
| 469 | 1810062G17Rik | NM_028183.1 | chr3:36475936-36482299 |
| 470 | 1810062O18Rik | NR_033571.1 | chr14:20546292-20570680 |
| 471 | 1810064F22Rik | NR_027981.1 | chr9:22206785-22213860 |
| 472 | 1810065E05Rik | NM_027239.2 | chr1:58421110-58426023 |
| 473 | 2010001E11Rik | NM_001163503.1 | chr10:39920381-39926923 |
| 474 | 2010002M12Rik | NM_053217.2 | chr19:34617050-34640743 |
| 475 | 2010003K11Rik | NM_027237.1 | chr19:4496787-4498583 |
| 476 | 2010005H15Rik | NM_029733.3 | chr16:36221561-36257427 |
| 477 | 2010009K17Rik | NR_040609.1 | chr2:158070363-158091797 |
| 478 | 2010010A06Rik | NR_045393.1 | chr18:75295674-75297329 |
| 479 | 2010012O05Rik | NR_025563.3 | chr19:46689905-46703382 |
| 480 | 2010015L04Rik | NM_001166029.1 | chr4:155409189-155421996 |
| 481 | 2010016I18Rik | NR_033207.1 | chr3:106481985-106485913 |
| 482 | 2010106C02Rik | NR_045435.1 | chr17:86285166-86287178 |
| 483 | 2010106E10Rik | NM_001168590.1 | chrX:112495273-112558343 |
| 484 | 2010107E04Rik | NR_027360.2 | chr12:111961375-111966977 |
| 485 | 2010107G12Rik | NM_001025573.2 | chr6:34945294-34977999 |
| 486 | 2010107G23Rik | NM_027251.3 | chr10:62107655-62111013 |
| 487 | 2010109A21Rik | NM_029363.1 | chr5:93206517-93213474 |
| 488 | 2010109I03Rik | NM_025929.2 | chr15:74878335-74881704 |
| 489 | 2010111I01Rik | NM_001289924.1 | chr13:62964892-63302877 |
| 490 | 2010204K13Rik | NM_027924.1 | chrX:7411816-7422988 |
| 491 | 2010300C02Rik | NM_028096.1 | chr1:37611675-37719811 |
| 492 | 2010305F09Rik | NR_045449.1 | chrX:13234640-13247733 |
| 493 | 2010310C07Rik | NR_045169.1 | chr6:42370670-42380558 |
| 494 | 2010315B03Rik | NM_001243117.1 | chr9:124291803-124312694 |
| 495 | 2010320M18Rik | NR_029440.1 | chr8:70776861-70777606 |
| 496 | 2200002D01Rik | NM_028179.1 | chr7:29247520-29248467 |
| 497 | 2200002J24Rik | NM_026961.2 | chr7:30698925-30700534 |
| 498 | 2210010C04Rik | NM_023333.4 | chr6:41030267-41035509 |
| 499 | 2210011C24Rik | NM_001291292.1 | chr8:84010227-84011720 |
| 500 | 2210013O21Rik | NM_027327.1 | chrX:153723553-153741296 |
| 501 | 2210015D19Rik | NR_015577.1 | chr11:5762149-5784710 |
| 502 | 2210016F16Rik | NM_027335.1 | chr13:58380045-58385225 |
| 503 | 2210016L21Rik | NM_028211.1 | chr5:114942201-114948540 |
| 504 | 2210018M11Rik | NM_172280.2 | chr7:98590605-98656669 |
| 505 | 2210019H11Rik | NR_038157.1 | chr5:147228597-147271521 |
| 506 | 2210039B01Rik | NR_044985.1 | chr12:73548482-73551986 |
| 507 | 2210404O09Rik | NM_001256493.1 | chr17:21879569-21909926 |
| 508 | 2210407C18Rik | NM_144544.2 | chr11:58608205-58613492 |
| 509 | 2210408F21Rik | NR_040257.1 | chr6:31220350-31337394 |
| 510 | 2210408I21Rik | NM_001081353.1 | chr13:77135535-77193905 |
| 511 | 2210409D07Rik | NR_045360.1 | chr18:57632078-57638585 |
| 512 | 2210409E21Rik | NR_003842.2 | chr11:88972637-88973014 |
| 513 | 2210414B05Rik | NR_040643.1 | chr4:3656505-3663108 |
| 514 | 2210416O15Rik | NR_045499.1 | chr11:88098057-88100107 |
| 515 | 2210417A02Rik | NR_028285.1 | chr5:148741839-148743139 |
| 516 | 2210420H20Rik | NR_045389.1 | chr18:82754504-82759039 |
| 517 | 2300002M23Rik | NM_175148.3 | chr17:35567484-35568945 |
| 518 | 2300003K06Rik | NM_001195383.1 | chr11:99837147-99838066 |
| 519 | 2300005B03Rik | NM_001081961.1 | chr15:74742838-74746687 |
| 520 | 2300009A05Rik | NM_027090.1 | chr9:63394446-63399244 |
| 521 | 2310001H17Rik | NR_040265.1 | chr6:129232622-129238045 |
| 522 | 2310001K24Rik | NR_028122.1 | chr2:163472544-163473003 |
| 523 | 2310002D06Rik | NR_045490.1 | chr12:80507205-80517954 |
| 524 | 2310002F09Rik | NR_077063.1 | chr7:43745465-43755936 |
| 525 | 2310002J15Rik | NM_026415.3 | chr2:25238818-25239897 |
| 526 | 2310002L09Rik | NM_027104.3 | chr4:73939370-73950846 |
| 527 | 2310003H01Rik | NM_027980.1 | chr11:120369561-120378746 |
| 528 | 2310005A03Rik | NR_040634.1 | chr2:155097790-155100079 |
| 529 | 2310005E17Rik | NR_045435.1 | chr13:98424109-98435065 |
| 530 | 2310005G13Rik | NM_183281.2 | chr16:57036966-57071346 |
| 531 | 2310007B03Rik | NM_001159940.1 | chr1:93151354-93160870 |
| 532 | 2310007L24Rik | NM_029345.1 | chr11:106374825-106377114 |
| 533 | 2310008N11Rik | NR_045904.1 | chr8:26814596-26824423 |
| 534 | 2310009A05Rik | NM_001308425.1 | chr9:73039718-73042775 |
| 535 | 2310009B15Rik | NM_001081226.1 | chr1:138851978-138856854 |
| 536 | 2310010J17Rik | NR_046006.1 | chr7:90124835-90129474 |
| 537 | 2310011J03Rik | NM_025521.3 | chr10:80318254-80320548 |
| 538 | 2310014L17Rik | NM_029809.2 | chr7:12927415-12931072 |
| 539 | 2310015A10Rik | NR_033514.1 | chr12:80120545-80132844 |
| 540 | 2310015B20Rik | NM_001304739.1 | chr10:70204667-70219711 |
| 541 | 2310015D24Rik | NR_037997.1 | chr16:13514130-13520419 |
| 542 | 2310016D03Rik | NR_045491.1 | chr12:30410558-30467358 |
| 543 | 2310020H05Rik | NR_045495.1 | chr13:99076527-99087921 |
| 544 | 2310022A10Rik | NM_001122767.1 | chr7:27560475-27582098 |
| 545 | 2310022B05Rik | NM_175149.4 | chr8:124635755-124661369 |
| 546 | 2310030A07Rik | NR_040603.1 | chr1:150320680-150346771 |
| 547 | 2310030G06Rik | NM_025865.2 | chr9:50739690-50746521 |
| 548 | 2310033P09Rik | NM_024210.2 | chr11:59208360-59210734 |
| 549 | 2310034C09Rik | NM_054100.2 | chr18:88758646-88759789 |
| 550 | 2310034G01Rik | NR_040418.1 | chr19:46348290-46348988 |
| 551 | 2310034O05Rik | NR_040679.1 | chr5:100210691-100218049 |
| 552 | 2310035C23Rik | NM_029349.1 | chr1:105663860-105755131 |
| 553 | 2310036O22Rik | NM_026760.2 | chr8:85026832-85030286 |
| 554 | 2310039H08Rik | NM_025966.3 | chr17:46772634-46773407 |
| 555 | 2310039L15Rik | NR_045337.1 | chr10:95336275-95363216 |
| 556 | 2310040G24Rik | NR_040292.1 | chr6:86483375-86488227 |
| 557 | 2310042E22Rik | NM_025634.3 | chr16:21152658-21153944 |
| 558 | 2310043A19Rik | NR_037994.1 | chr1:177641541-177642943 |
| 559 | 2310043O21Rik | NR_045757.1 | chr15:38548943-38594934 |
| 560 | 2310045N01Rik | NM_001145552.2 | chr8:70134998-70148634 |
| 561 | 2310047M10Rik | NR_028005.3 | chr11:69059774-69061576 |
| 562 | 2310050C09Rik | NM_025621.2 | chr9:92868358-92870205 |
| 563 | 2310057J18Rik | NM_026636.3 | chr10:28972287-28986306 |
| 564 | 2310057M21Rik | NM_026655.3 | chr7:131342717-131362698 |
| 565 | 2310057N15Rik | NM_027170.1 | chr16:88773180-88774206 |
| 566 | 2310059E24Rik | NR_027981.1 | chr17:35892676-35897378 |
| 567 | 2310061J03Rik | NR_027965.1 | chr16:55973267-55974617 |
| 568 | 2310061N02Rik | NM_027155.1 | chr16:88707170-88707962 |

Fig. 26 - 4

| | | | |
|---|---|---|---|
| 569 | 2310065F04Rik | NR_038055.1 | chr11:67112460-67120080 |
| 570 | 2310067B10Rik | NM_028014.3 | chr11:115765432-115799033 |
| 571 | 2310068J16Rik | NR_028124.1 | chr15:99972166-99973287 |
| 572 | 2310069B03Rik | NR_040520.1 | chr6:82877865-82881853 |
| 573 | 2310069G16Rik | NR_040309.1 | chr15:44787762-44805829 |
| 574 | 2310079G19Rik | NM_027173.1 | chr16:88626787-88627666 |
| 575 | 2310081J21Rik | NR_045474.1 | chr3:50261814-50680224 |
| 576 | 2410002F23Rik | NM_025880.4 | chr7:44246721-44252319 |
| 577 | 2410003L11Rik | NR_045498.1 | chr1:97598510-97622893 |
| 578 | 2410004B18Rik | NM_025555.4 | chr3:145938031-145944275 |
| 579 | 2410004I01Rik | NR_037963.1 | chr11:102958299-102964154 |
| 580 | 2410004N09Rik | NR_038151.1 | chr18:33794891-33795989 |
| 581 | 2410004P03Rik | NM_001201332.1 | chr12:17004957-17011727 |
| 582 | 2410006H16Rik | NR_030738.1 | chr1:62602876-62604806 |
| 583 | 2410007B07Rik | NR_040539.1 | chr3:75647440-75655731 |
| 584 | 2410012E07Rik | NR_045939.1 | chr14:70852932-70873954 |
| 585 | 2410012M07Rik | NM_028033.1 | chr9:98864766-98866580 |
| 586 | 2410015M20Rik | NM_153152.3 | chr17:56607451-56609771 |
| 587 | 2410016O06Rik | NM_023633.3 | chr12:83950607-83952953 |
| 588 | 2410017I17Rik | NR_033517.1 | chr7:36145017-36162374 |
| 589 | 2410018L13Rik | NR_015504.1 | chr12:22953996-23010243 |
| 590 | 2410021H03Rik | NR_045428.1 | chr17:69275361-69277206 |
| 591 | 2410076I21Rik | NM_028598.1 | chr9:58652855-58741559 |
| 592 | 2410088K16Rik | NR_040493.1 | chr1:88754889-88755733 |
| 593 | 2410089E03Rik | NM_001162036.1 | chr15:8169105-8271158 |
| 594 | 2410114N07Rik | NR_040652.1 | chr4:34909788-34911481 |
| 595 | 2410124H12Rik | NM_029740.1 | chr16:92478741-92497365 |
| 596 | 2410127L17Rik | NM_026120.4 | chr19:18670779-18704792 |
| 597 | 2410131K14Rik | NM_001081236.1 | chr5:118245226-118263114 |
| 598 | 2410137M14Rik | NM_029747.3 | chr17:36977700-36981237 |
| 599 | 2410141K09Rik | NM_001290196.1 | chr13:66431027-66441118 |
| 600 | 2500004C02Rik | NR_040318.1 | chr2:153341156-153345810 |
| 601 | 2510002D24Rik | NM_001033164.2 | chr16:18836579-18840113 |
| 602 | 2510003E04Rik | NM_026197.2 | chr10:62558449-62578457 |
| 603 | 2510009E07Rik | NM_001001881.2 | chr16:21649044-21694665 |
| 604 | 2510039O18Rik | NM_029841.3 | chr4:147940894-147947314 |
| 605 | 2510049J12Rik | NM_001101431.1 | chr6:115583546-115592576 |
| 606 | 2610001J05Rik | NR_024619.1 | chr6:13869073-13871483 |
| 607 | 2610002J02Rik | NM_001190445.1 | chr4:155249965-155256687 |
| 608 | 2610002M06Rik | NR_025921.3 | chrX:107782751-107816334 |
| 609 | 2610005L07Rik | NR_028428.1 | chr8:20385781-20424814 |
| 610 | 2610008E11Rik | NM_001004362.2 | chr10:79064373-79097600 |
| 611 | 2610015P09Rik | NM_027801.1 | chr16:43889901-43964314 |
| 612 | 2610016A17Rik | NR_045347.1 | chr19:25671133-25672239 |
| 613 | 2610018G03Rik | NM_133729.2 | chrX:50841370-50893098 |
| 614 | 2610020C07Rik | NR_038156.1 | chr16:11203382-11225796 |
| 615 | 2610020H08Rik | NM_001004187.1 | chr7:119794186-119848941 |
| 616 | 2610027K06Rik | NR_077059.1 | chr11:85791659-85832388 |
| 617 | 2610028E06Rik | NR_015560.1 | chr4:125887850-125922310 |
| 618 | 2610028H24Rik | NM_029816.2 | chr10:76449080-76461218 |
| 619 | 2610034B18Rik | NM_027420.4 | chr7:79925358-79935264 |
| 620 | 2610034M16Rik | NM_027001.3 | chr7:58878807-58991375 |
| 621 | 2610035D17Rik | NR_015556.1 | chr11:113043905-113201838 |
| 622 | 2610035F20Rik | NR_045046.3 | chr14:122470376-122475199 |
| 623 | 2610037D02Rik | NR_040423.1 | chr15:96190473-96197974 |
| 624 | 2610044O15Rik8 | NM_153780.3 | chr8:129216353-129234046 |
| 625 | 2610100L16Rik | NR_033490.1 | chr3:177889920-17880071 |
| 626 | 2610203C20Rik | NR_015483.1 | chr9:41581252-41592829 |
| 627 | 2610203C22Rik | NR_015470.1 | chr1:9560832-9631092 |
| 628 | 2610206C17Rik | NR_038175.1 | chr7:84689639-84776549 |
| 629 | 2610207O16Rik | NR_110495.1 | chr1:42707062-42713454 |
| 630 | 2610301B20Rik | NM_026005.3 | chr4:108744497-108899423 |
| 631 | 2610305D13Rik | NM_145074.2 | chr4:147611935-147642508 |
| 632 | 2610306M01Rik | NM_028298.1 | chr6:86848406-86849440 |
| 633 | 2610307P16Rik | NR_045053.1 | chr13:28460033-28865422 |
| 634 | 2610316D01Rik | NR_045047.1 | chr3:45280438-45378260 |
| 635 | 2610318N02Rik | NM_183287.2 | chr16:17113397-17125106 |
| 636 | 2610507B11Rik | NM_001002004.2 | chr11:78261753-78290625 |
| 637 | 2610507I01Rik | NR_037964.1 | chr1:59197792-59202431 |
| 638 | 2610524H06Rik | NM_181075.3 | chr5:114821936-114823468 |
| 639 | 2610528A11Rik | NM_001206684.1 | chr14:37102139-37110101 |
| 640 | 2610528J11Rik | NR_025572.2 | chr4:118527274-118530217 |
| 641 | 2700029M09Rik | NM_028299.1 | chr8:60890450-60907572 |
| 642 | 2700038G22Rik | NR_045040.1 | chr5:23850596-23855033 |
| 643 | 2700046A07Rik | NR_037693.1 | chr18:62751673-62756347 |
| 644 | 2700046G09Rik | NR_033198.1 | chr19:32389215-32391184 |
| 645 | 2700049A03Rik | NM_001163375.1 | chr12:71136847-71243303 |
| 646 | 2700054A10Rik | NR_045436.1 | chr17:13487020-13554094 |
| 647 | 2700060E02Rik | NM_026528.3 | chr4:19811401-19823823 |
| 648 | 2700062C07Rik | NM_026529.4 | chr18:24470870-24477767 |
| 649 | 2700069J18Rik | NR_045909.1 | chr3:5177823-5220823 |
| 650 | 2700070H01Rik | NR_046019.1 | chr14:63055072-63058149 |
| 651 | 2700080I15Rik | NM_175381.6 | chr19:7417624-7425904 |
| 652 | 2700086A05Rik | NR_015611.1 | chr6:52201123-52213597 |
| 653 | 2700089E24Rik | NM_001163445.2 | chr6:133105238-133107750 |
| 654 | 2700089I24Rik | NR_045308.3 | chr19:59493135-59559391 |
| 655 | 2700094K13Rik | NM_001033166.2 | chr2:84669220-84670708 |
| 656 | 2700097O09Rik | NM_028314.2 | chr2:55045660-55080110 |
| 657 | 2700099C18Rik | NR_024720.1 | chr17:94750099-94775129 |
| 658 | 2810091G20Rik | NR_033780.1 | chr1:64079483-64083259 |
| 659 | 2810002D19Rik | NR_027831.1 | chr2:94406706-94411680 |
| 660 | 2810004N23Rik | NM_025615.2 | chr8:124839354-124863029 |
| 661 | 2810006K23Rik | NM_001134717.2 | chr5:124328088-124341852 |
| 662 | 2810007I24Rik | NM_001199306.1 | chr7:14410685-14438551 |
| 663 | 2810008D09Rik | NR_027059.1 | chr11:117076782-117078955 |
| 664 | 2810013P06Rik | NR_045268.1 | chr8:123042574-123044602 |
| 665 | 2810021U22Rik | NM_172403.2 | chr11:58867239-58884338 |
| 666 | 2810025M15Rik | NR_027984.1 | chr1:157412351-157420236 |
| 667 | 2810029C07Rik | NR_045295.1 | chr12:111572316-111574402 |
| 668 | 2810032G03Rik | NR_015579.1 | chr12:5376501-5416132 |
| 669 | 2810047C21Rik1 | NR_015598.1 | chr7:8086046-8093037 |
| 670 | 2810049E08Rik | NR_036594.1 | chr13:83891207-83928710 |
| 671 | 2810055G20Rik | NR_015543.2 | chr16:77329327-77558428 |
| 672 | 2810403A07Rik | NM_028814.3 | chr3:88685793-88712933 |
| 673 | 2810403D21Rik | NR_015493.2 | chrX:108834477-108886896 |
| 674 | 2810404M03Rik | NR_045497.1 | chr8:41827266-42046202 |
| 675 | 2810405F15Rik | NR_033447.1 | chr2:116074547-116076096 |
| 676 | 2810408A11Rik | NM_027419.3 | chr11:69897357-69900986 |
| 677 | 2810408I11Rik | NR_038009.1 | chr1:64679868-64690659 |
| 678 | 2810408M09Rik | NM_001007581.1 | chr2:165490111-165493314 |
| 679 | 2810410L24Rik | NR_030682.1 | chr11:120186649-120189856 |
| 680 | 2810417H13Rik | NM_026705.2 | chr9:65890322-65903551 |
| 681 | 2810428I15Rik | NM_025577.2 | chr8:70504295-70506739 |
| 682 | 2810429I04Rik | NR_015522.1 | chr13:3478302-3492398 |
| 683 | 2810433D01Rik | NR_033474.1 | chr1:102619506-102624416 |
| 684 | 2810442I21Rik | NR_110421.1 | chr11:16934708-16951282 |
| 685 | 2810442N19Rik | NR_040562.1 | chr1:162004968-162016485 |
| 686 | 2810454H06Rik | NR_029441.1 | chr6:134897960-134900785 |
| 687 | 2810459M11Rik | NM_001144992.1 | chr1:86045862-86055456 |
| 688 | 2810468N07Rik | NR_045176.1 | chr17:25570810-25575043 |
| 689 | 2810471M01Rik | NR_045906.1 | chr11:28681563-28693276 |
| 690 | 2810474O19Rik | NM_001289661.1 | chr6:149309413-149335663 |
| 691 | 2900005J15Rik | NR_027851.1 | chr5:25100974-25103007 |
| 692 | 2900008C10Rik | NR_045434.1 | chrX:12134453-12160346 |
| 693 | 2900009J06Rik | NR_045298.1 | chr1:127753616-127774054 |
| 694 | 2900011O08Rik | NM_144518.3 | chr16:139866636-14101494 |
| 695 | 2900026A02Rik | NM_172884.3 | chr5:113086322-113163313 |
| 696 | 2900041M22Rik | NR_015489.2 | chr11:117611246-117613417 |
| 697 | 2900052N01Rik | NR_015605.1 | chr9:46913602-46927366 |
| 698 | 2900055J20Rik | NR_045177.1 | chr18:40256961-40257687 |
| 699 | 2900056M20Rik | NR_040269.2 | chrX:152294823-152327493 |
| 700 | 2900057B20Rik | NR_045365.1 | chr18:76091556-76088471 |
| 701 | 2900060B14Rik | NR_027901.1 | chr1:118458668-118459265 |
| 702 | 2900076A07Rik | NR_045299.1 | chr7:81523549-81531498 |
| 703 | 2900079G21Rik | NR_015468.1 | chr9:112234380-112236018 |
| 704 | 2900092C05Rik | NM_028434.3 | chr7:12512550-12556323 |
| 705 | 2900092D14Rik | NR_027891.1 | chr1:42700335-42703176 |
| 706 | 2900097C17Rik | NR_024329.1 | chr2:156388062-156392979 |
| 707 | 3000002C10Rik | NR_033215.1 | chr9:109830153-109831431 |
| 708 | 3010001F23Rik | NR_045451.1 | chrX:152368571-152416702 |
| 709 | 3010026O09Rik | NM_026543.3 | chr11:501748850-50200135 |
| 710 | 3010033K07Rik | NM_077224.1 | chr8:108553251-108584677 |
| 711 | 3100003L05Rik | NR_045907.1 | chr7:124625669-124708935 |
| 712 | 3100001J22Rik | NM_025653.2 | chr16:13672019-13678385 |
| 713 | 3100002H16Rik | NM_029623.2 | chr18:12168729-12189969 |
| 714 | 3100007F17Rik | NM_028426.2 | chrX:123103522-123145654 |
| 715 | 3100009E18Rik | NM_001172074.1 | chr1:120121186-120188189 |
| 716 | 3100009F21Rik | NR_045466.1 | chr12:110151653-110158073 |
| 717 | 3100015C05Rik | NR_045908.1 | chr13:111211468-111229431 |
| 718 | 3100021A11Rik | NR_030776.1 | chr6:119848192-119849016 |
| 719 | 3100021N24Rik | NM_001254730.1 | chr4:108719648-108781904 |
| 720 | 3100035S14Rik | NM_178399.4 | chr1:9601266-9627142 |
| 721 | 3110039I08Rik | NR_040725.2 | chr9:41376525-41432079 |
| 722 | 3110039M20Rik | NR_026733.1 | chr12:49389651-49407346 |
| 723 | 3110040N11Rik | NM_026077.3 | chr7:81782186-81789453 |
| 724 | 3110043O21Rik | NM_001081343.1 | chr4:35191281-35225880 |
| 725 | 3110045C21Rik | NR_040438.1 | chr1:169969408-169972396 |
| 726 | 3110052M02Rik | NM_001166497.1 | chr17:21650610-21664966 |
| 727 | 3110056K07Rik | NR_045055.1 | chr12:70991614-71015823 |
| 728 | 3110057O12Rik | NM_026622.3 | chr3:40894276-40936307 |
| 729 | 3110062M04Rik | NM_001135611.1 | chr6:34871770-34878065 |
| 730 | 3110070M22Rik | NR_027974.1 | chr13:119487256-119488384 |
| 731 | 3110079O15Rik | NM_028473.1 | chr7:87470263-87475459 |
| 732 | 3110082I17Rik | NM_028469.3 | chr5:139359738-139460534 |
| 733 | 3110082J24Rik | NM_001256263.1 | chr5:30103583-30106086 |
| 734 | 3110099E03Rik | NR_030712.1 | chr2:115493512-115512201 |
| 735 | 3200001D21Rik | NR_045888.2 | chr12:88365313-88377323 |
| 736 | 3300002I08Rik | NM_027017.1 | chr2:150310936-150362765 |
| 737 | 3300005D19Rik | NM_207779.2 | chr17:5799489-5803242 |
| 738 | 3425401B19Rik | NM_001195097.1 | chr14:32659118-32685272 |
| 739 | 3632451O06Rik | NM_026142.4 | chr14:49682018-49783367 |
| 740 | 3632454L22Rik | NR_040283.1 | chr5:135022421-135036602 |
| 741 | 3830403N18Rik | NR_027510.2 | chr5:56136571-56153496 |
| 742 | 3830406C13Rik | NM_001284383.1 | chr14:12284202-12303231 |
| 743 | 3830408C21Rik | NR_015471.1 | chr13:107022569-107033518 |
| 744 | 3830417A13Rik | NR_027512.2 | chr6:64173547-64178778 |
| 745 | 3930402G23Rik | NR_030751.1 | chr8:10924426-10928457 |
| 746 | 4430402I18Rik | NM_198651.2 | chr19:28923063-28964154 |
| 747 | 4631405J19Rik | NR_110333.1 | chr2:93029347-93033445 |
| 748 | 4632415L05Rik | NR_027985.1 | chr3:19894870-19898984 |
| 749 | 4632427E13Rik | NR_015510.1 | chr7:92740705-92741459 |
| 750 | 4632428C04Rik | NR_036631.1 | chr16:30008666-30021430 |
| 751 | 4632428N05Rik | NM_001159572.1 | chr10:60346850-60372684 |
| 752 | 4632434I11Rik | NM_001080995.1 | chr7:92857526-92874232 |
| 753 | 4732416N19Rik | NR_015615.1 | chr6:148212287-148245663 |
| 754 | 4732456N10Rik | NM_177717.4 | chr15:101552355-101562950 |
| 755 | 4732471J01Rik | NR_015569.3 | chr7:25394712-25566417 |
| 756 | 4732490B19Rik | NR_040276.1 | chr11:113203314-113209669 |

Fig. 26 - 5

| | | | | | | |
|---|---|---|---|---|---|---|
| 757 | 4732491K20Rik | NR_045290.1 | chr17:12318852-12327250 | 852 | 4930429F24Rik | NR_040734.1 | chr9:79793640-79803235 |
| 758 | 4831440E17Rik | NR_030700.1 | chr5:25499796-25504473 | 853 | 4930430A15Rik | NM_026248.3 | chr2:111193253-111229600 |
| 759 | 4833403J15Rik | NM_029008.1 | chr18:46850038-46905446 | 854 | 4930430D24Rik | NM_001034856.2 | chrX:38038198-38043114 |
| 760 | 4833411C07Rik | NR_102285.1 | chr8:10899921-10902314 | 855 | 4930430F08Rik | NM_175128.2 | chr10:100572273-100589259 |
| 761 | 4833412C05Rik | NR_045954.1 | chr7:67784537-67803496 | 856 | 4930430F21Rik | NR_045186.1 | chr15:31039125-31043331 |
| 762 | 4833417C18Rik | NR_045187.1 | chr11:95858816-95861046 | 857 | 4930430J02Rik | NR_040729.1 | chr9:57391069-57400364 |
| 763 | 4833418N02Rik | NR_015506.2 | chr17:87274885-87282814 | 858 | 4930431F12Rik | NR_073013.1 | chr5:44966200-44978805 |
| 764 | 4833419F23Rik | NR_040328.1 | chr18:4353546-4368945 | 859 | 4930431P03Rik | NR_045059.1 | chr14:44954899-44961307 |
| 765 | 4833420G17Rik | NM_001113550.1 | chr13:119462758-119486117 | 860 | 4930432J09Rik | NR_045953.1 | chr14:103977827-104027142 |
| 766 | 4833422C13Rik | NR_015501.1 | chr13:91701664-91741872 | 861 | 4930432K21Rik | NM_001163752.1 | chr8:84148037-84172597 |
| 767 | 4833423E24Rik | NM_001081664.2 | chr2:85484091-85518935 | 862 | 4930432M17Rik | NM_001033814.1 | chr3:121670762-121682982 |
| 768 | 4833424O15Rik | NM_029425.3 | chr3:117575226-117689508 | 863 | 4930433B08Rik | NR_040544.1 | chr3:18468284-18480477 |
| 769 | 4833427F10Rik | NR_045459.1 | chr17:35772449-35780687 | 864 | 4930433I11Rik | NM_207248.3 | chr7:40987668-40994833 |
| 770 | 4833427G06Rik | NM_177702.3 | chr9:51081312-51102078 | 865 | 4930433N12Rik | NR_027988.1 | chr9:3190268-3199813 |
| 771 | 4833428I15Rik | NR_040732.1 | chr9:45416625-45431232 | 866 | 4930434J06Rik | NR_046274.1 | chr14:71856708-71920438 |
| 772 | 4833439L19Rik | NR_001252645.1 | chr13:54551217-54565382 | 867 | 4930435E12Rik | NM_029042.1 | chr16:38812204-38828749 |
| 773 | 4921501E09Rik | NM_001009544.2 | chr17:33064142-33068058 | 868 | 4930438E09Rik | NR_045961.1 | chr14:67332041-67397742 |
| 774 | 4921504A21Rik | NR_102341.1 | chr5:19202367-19226555 | 869 | 4930440C22Rik | NR_040473.1 | chr1:94797441-94802472 |
| 775 | 4921504E06Rik | NM_027600.4 | chr2:19462836-19553910 | 870 | 4930440O19Rik | NR_108098.1 | chr2:78051176-78194430 |
| 776 | 4921506M07Rik | NM_001312644.1 | chr12:57564415-57622105 | 871 | 4930441J16Rik | NR_040501.1 | chr2:74298939-74307717 |
| 777 | 4921507L20Rik | NR_045827.1 | chr2:93980033-93983575 | 872 | 4930442J19Rik | NR_040747.1 | chr2:151302038-151316003 |
| 778 | 4921507P07Rik | NM_027564.3 | chr6:50573303-50596590 | 873 | 4930442L01Rik | NR_015596.1 | chr3:96829825-96832070 |
| 779 | 4921508D12Rik | NR_045802.1 | chr2:132424740-132452499 | 874 | 4930443O20Rik | NR_040504.1 | chr2:85073613-85086461 |
| 780 | 4921509C19Rik | NM_198655.2 | chr2:151470541-151476151 | 875 | 4930444F02Rik | NR_038034.1 | chr10:18801085-18831930 |
| 781 | 4921509O07Rik | NR_045501.1 | chr3:113446287-113502844 | 876 | 4930444G20Rik | NM_053264.2 | chr10:22066308-22068079 |
| 782 | 4921511C10Rik | NR_045502.1 | chr3:79212918-79253913 | 877 | 4930444M15Rik | NR_045660.1 | chr14:76514557-76520855 |
| 783 | 4921511C20Rik | NR_003646.1 | chrX:127394292-127395898 | 878 | 4930444P10Rik | NM_001243238.2 | chr1:16065978-16093325 |
| 784 | 4921511H03Rik | NR_027603.2 | chr5:7304163-7311491 | 879 | 4930447A16Rik | NM_029113.1 | chr15:37425553-37440644 |
| 785 | 4921511J17Rik | NR_045829.1 | chr12:12351521-12392475 | 880 | 4930447C04Rik | NM_029484.2 | chr12:72881108-72917765 |
| 786 | 4921511M17Rik | NR_001201358.1 | chrX:154001589-154120685 | 881 | 4930447J18Rik | NR_045959.1 | chr14:47898863-47944189 |
| 787 | 4921513I08Rik | NR_038000.1 | chr10:120765731-120778886 | 882 | 4930447K03Rik | NR_046184.1 | chr13:34084154-34113272 |
| 788 | 4921515E04Rik | NR_045711.1 | chr15:18078136-18369627 | 883 | 4930447N0SRik | NR_045168.1 | chr3:122795090-122801980 |
| 789 | 4921517D22Rik | NR_183290.2 | chr13:59687401-59694101 | 884 | 4930448C13Rik | NR_045960.1 | chr12:14996388-15050389 |
| 790 | 4921524J17Rik | NM_025722.3 | chr8:85408758-85432841 | 885 | 4930448F21Rik | NR_046032.1 | chr13:18084946-18100202 |
| 791 | 4921524L21Rik | NM_027598.1 | chr18:6603632-6638966 | 886 | 4930448H16Rik | NR_040700.1 | chr5:143226991-143234748 |
| 792 | 4921525O09Rik | NR_045061.1 | chr3:52096740-52124160 | 887 | 4930448I06Rik | NR_040696.1 | chr1:41167559-41181252 |
| 793 | 4921529L05Rik | NR_110484.1 | chr6:53978690-54017383 | 888 | 4930448J18Rik | NR_040696.1 | chr5:50151332-50156092 |
| 794 | 4921530L21Rik | NM_025733.2 | chr14:95881265-95882775 | 889 | 4930448K20Rik | NR_004448.2 | chr4:9915964-9917397 |
| 795 | 4921531C22Rik | NR_033782.1 | chr2:179976852-179979013 | 890 | 4930449E01Rik | NR_045921.1 | chr14:105498787-105505628 |
| 796 | 4921531P14Rik | NR_045361.1 | chr18:83292791-83325884 | 891 | 4930449E18Rik | NR_045319.1 | chr19:57273959-57277052 |
| 797 | 4921533I20Rik | NR_033607.1 | chr18:17234482-17235482 | 892 | 4930449J24Rik | NM_026136.2 | chr5:146502398-146505183 |
| 798 | 4921534H16Rik | NR_110443.1 | chr9:98003419-98012175 | 893 | 4930451C15Rik | NM_001145435.1 | chr16:17544464-17561247 |
| 799 | 4921536K21Rik | NM_026150.3 | chr11:3886087-3895126 | 894 | 4930451G09Rik | NM_001271586.1 | chr16:4964287-4978054 |
| 800 | 4921539E11Rik | NM_001163494.1 | chr4:103230444-103290863 | 895 | 4930451I11Rik | NM_183131.2 | chr7:126830473-126831496 |
| 801 | 4922502D21Rik | NM_199034.3 | chr6:129322164-129331781 | 896 | 4930452A19Rik | NR_045433.1 | chr17:9750751-9775866 |
| 802 | 4922502H24Rik | NR_046187.1 | chr13:101391870-101397580 | 897 | 4930452B06Rik | NM_028934.3 | chr14:8431171-8666290 |
| 803 | 4922502N22Rik | NR_045149.1 | chr6:139315596-139322576 | 898 | 4930452G13Rik | NR_045060.1 | chr14:79702919-79712930 |
| 804 | 4930401C15Rik | NR_045349.1 | chr10:25779313-25837437 | 899 | 4930452N14Rik | NR_040629.1 | chr1:154241520-154256906 |
| 805 | 4930401O10Rik | NR_045942.1 | chr11:71928470-71940122 | 900 | 4930453H23Rik | NM_001252013.1 | chr2:21206579-21221665 |
| 806 | 4930401O12Rik | NR_045957.1 | chr13:31213409-31241086 | 901 | 4930453L07Rik | NR_073360.1 | chr8:9144668-9149050 |
| 807 | 4930402F06Rik | NM_001080709.2 | chr2:35375561-35397174 | 902 | 4930453N24Rik | NM_029723.2 | chr16:64766104-64770939 |
| 808 | 4930402F11Rik | NR_045940.1 | chr7:69496093-69499689 | 903 | 4930455J4Rik | NR_045968.1 | chr14:8666389-8673378 |
| 809 | 4930402H24Rik | NM_029432.2 | chr2:130706199-130840145 | 904 | 4930455S12Rik | NR_045352.1 | chr10:21319087-21342055 |
| 810 | 4930402J13Rik | NM_001270700.1 | chrX:9104561-9106342 | 905 | 4930455D15Rik | NR_045381.1 | chr18:32663641-32837287 |
| 811 | 4930404A05Rik | NR_040495.1 | chr6:52799507-52815744 | 906 | 4930455F16Rik | NR_040570.1 | chr16:4219911-4229116 |
| 812 | 4930404A10Rik | NM_029016.2 | chr11:54370651-54426790 | 907 | 4930455H04Rik | NR_040695.1 | chr3:116968266-116984406 |
| 813 | 4930404H11Rik | NR_045941.1 | chr12:71540606-71556133 | 908 | 4930455J16Rik | NR_045469.1 | chr13:58741073-58762311 |
| 814 | 4930404J05Rik | NR_028368.1 | chr16:91011248-91016503 | 909 | 4930456L15Rik | NR_045887.1 | chr4:103290958-103311832 |
| 815 | 4930404N11Rik | NM_001014836.3 | chr10:81364023-81365820 | 910 | 4930459O07Rik | NR_110443.1 | chr10:96226206-96248708 |
| 816 | 4930405A10Rik | NR_046307.1 | chr14:22507173-22542798 | 911 | 4930459L07Rik | NR_046190.1 | chr5:58443239-58452998 |
| 817 | 4930405A21Rik | NR_040505.1 | chr2:156714538-156720909 | 912 | 4930461G14Rik | NR_040736.1 | chr9:58455172-58469623 |
| 818 | 4930405D11Rik | NR_045956.1 | chr11:90804690-90895152 | 913 | 4930463O16Rik | NR_108059.1 | chr10:84488292-84497676 |
| 819 | 4930405I17Rik | NR_045350.1 | chr10:20199246-20201854 | 914 | 4930465K10Rik | NR_027978.1 | chr18:77714183-77715445 |
| 820 | 4930405L22Rik | NR_110478.1 | chr5:45926821-45932409 | 915 | 4930465M20Rik | NR_045973.1 | chr12:107723742-107735488 |
| 821 | 4930406D18Rik | NR_040543.1 | chr3:100426404-100437754 | 916 | 4930467D21Rik | NR_045972.1 | chr5:97392416-97588126 |
| 822 | 4930407I10Rik | NM_001166475.1 | chr15:82059150-82066538 | 917 | 4930467E23Rik | NM_001039553.2 | chr8:19729575-19753602 |
| 823 | 4930412B13Rik | NR_040631.1 | chr2:117821927-117909136 | 918 | 4930467K11Rik | NR_045353.1 | chr10:57478382-57486853 |
| 824 | 4930412C18Rik | NR_030693.1 | chr4:9770584-9823411 | 919 | 4930468A15Rik | NM_001201395.1 | chrX:76582609-76602924 |
| 825 | 4930412D23Rik | NM_001281537.1 | chrX:127721175-127736554 | 920 | 4930469G21Rik | NM_001195189.1 | chr1:161156842-161159314 |
| 826 | 4930412G13Rik | NR_024257.1 | chr2:9881245-9886767 | 921 | 4930470H14Rik | NR_045764.1 | chr17:4044657-4082995 |
| 827 | 4930413E15Rik | NR_040694.1 | chr5:118952338-118961261 | 922 | 4930470P17Rik | NR_027825.1 | chr2:170579417-170602017 |
| 828 | 4930413F20Rik | NR_045883.2 | chr15:34675072-34679204 | 923 | 4930471C04Rik | NR_046192.1 | chr14:64099294-64104235 |
| 829 | 4930413G21Rik | NR_045694.1 | chr7:122969057-122970459 | 924 | 4930471I10Rik | NR_045711.1 | chr18:36106202-36109954 |
| 830 | 4930413M19Rik | NR_045759.1 | chr14:50503768-50520943 | 925 | 4930471M09Rik | NR_045980.1 | chr9:91430459-91440854 |
| 831 | 4930414L22Rik | NR_046011.1 | chr6:72438682-72440615 | 926 | 4930473A02Rik | NR_040348.1 | chr2:130543790-130563749 |
| 832 | 4930414N06Rik | NR_046294.1 | chr19:44972116-44984550 | 927 | 4930473J02Rik | NR_045356.1 | chr16:97590983-97596931 |
| 833 | 4930415F15Rik | NM_028669.1 | chr1:11489265-11515190 | 928 | 4930474G06Rik | NR_045398.1 | chr18:28560163-28998176 |
| 834 | 4930415L06Rik | NR_001033880.3 | chrX:89930096-89932852 | 929 | 4930474H20Rik | NR_045712.1 | chr14:90126890-90269760 |
| 835 | 4930415O20Rik | NM_001201322.1 | chr15:98571003-98589588 | 930 | 4930474M22Rik | NR_027986.1 | chr17:14389106-14398942 |
| 836 | 4930417O13Rik | NR_015527.1 | chr6:125265524-125273777 | 931 | 4930474N05Rik | NM_175008.3 | chr14:36094964-36096855 |
| 837 | 4930417O22Rik | NR_045806.1 | chr11:101952420-101960574 | 932 | 4930474N09Rik | NR_038130.1 | chr12:99161276-99162808 |
| 838 | 4930419G24Rik | NR_040595.1 | chr3:33024776-33088607 | 933 | 4930478L05Rik | NR_046060.1 | chr16:78560315-78564869 |
| 839 | 4930423M02Rik | NR_038183.1 | chr4:5632327-5642284 | 934 | 4930478P22Rik | NR_046060.1 | chr5:35361552-35367677 |
| 840 | 4930425K10Rik | NR_038182.1 | chr5:67933611-67943081 | 935 | 4930479D17Rik | NR_046277.1 | chr6:146657217-146665403 |
| 841 | 4930425O10Rik | NR_040545.1 | chr3:138711534-138726984 | 936 | 4930480E11Rik | NM_001177966.2 | chrX:78369642-78371128 |
| 842 | 4930426D05Rik | NM_001271580.1 | chr18:21651564-21656107 | 937 | 4930480G23Rik | NR_040768.1 | chr4:19979444-20005739 |
| 843 | 4930426L09Rik | NR_024323.1 | chr2:18998318-18999804 | 938 | 4930480L05Rik | NR_045463.1 | chr17:90861168-90867102 |
| 844 | 4930427A07Rik | NM_134041.3 | chr12:113156420-113165458 | 939 | 4930480M12Rik | NR_046278.1 | chr12:26211266-26240707 |
| 845 | 4930428D18Rik | NM_001033799.2 | chrX:76393349-76397979 | 940 | 4930481A15Rik | NR_015545.2 | chr19:5406814-5422847 |
| 846 | 4930428E07Rik | NR_045943.1 | chr2:38552808-38614521 | 941 | 4930482G09Rik | NR_108043.1 | chr3:153147942-153152108 |
| 847 | 4930428G15Rik | NR_040730.1 | chr9:115336160-115341924 | 942 | 4930483J18Rik | NR_015603.1 | chr15:81190852-81192757 |
| 848 | 4930428O21Rik | NR_045871.1 | chr5:107698211-107703480 | 943 | 4930483K19Rik | NR_045354.1 | chr10:76545870-76562226 |
| 849 | 4930429B21Rik | NR_027966.1 | chr3:32365488-32367438 | 944 | 4930483O08Rik | NR_046273.1 | chr7:133128250-133142457 |
| 850 | 4930429D17Rik | NR_040699.1 | chr5:103230374-103299029 | 945 | 4930486F22Rik | NR_038024.1 | chr10:86095853-86113585 |
| 851 | 4930429F11Rik | NR_033463.1 | chr17:79475623-79477885 | 946 | 4930486I03Rik | NR_045734.1 | chr1:20356453-20392300 |

Fig. 26 - 6

| | | | |
|---|---|---|---|
| 947 | 4930486L24Rik | NM_178098.2 | chr13:60842611-60864416 |
| 948 | 4930487D11Rik | NR_046191.1 | chr5:38344388-38349197 |
| 949 | 4930487H11Rik | NR_040601.1 | chr1:62790917-62794732 |
| 950 | 4930488B22Rik | NR_040627.1 | chr1:184712496-184718989 |
| 951 | 4930488L21Rik | NR_026888.1 | chr8:93811693-93813555 |
| 952 | 4930500F04Rik | NR_045758.1 | chr5:149847746-149864280 |
| 953 | 4930500J02Rik | NR_040322.1 | chr2:104559183-104571429 |
| 954 | 4930500L23Rik | NR_040701.1 | chr5:139523750-139541339 |
| 955 | 4930502A04Rik | NR_040737.1 | chr9:68470901-68520200 |
| 956 | 4930502E09Rik | NR_046281.1 | chr11:84829177-84830868 |
| 957 | 4930502E18Rik | NM_029142.1 | chrX:53724830-53738222 |
| 958 | 4930503B20Rik | NM_029144.3 | chr3:146646258-146651317 |
| 959 | 4930503E14Rik | NM_029131.3 | chr14:44163166-44171371 |
| 960 | 4930503E24Rik | NR_028310.1 | chr6:124469073-124524488 |
| 961 | 4930503H13Rik | NR_033598.1 | chrX:156539482-156540117 |
| 962 | 4930503L19Rik | NM_172967.2 | chr18:70453139-70472480 |
| 963 | 4930503O07Rik | NR_040477.1 | chr1:194212186-194222759 |
| 964 | 4930504O13Rik | NM_207527.3 | chr11:58446142-58452966 |
| 965 | 4930505A04Rik | NM_001100394.1 | chr11:30426005-30471829 |
| 966 | 4930505G20Rik | NR_045761.1 | chr14:115396550-115409552 |
| 967 | 4930506C21Rik | NR_073374.1 | chr17:8293365-8311118 |
| 968 | 4930506M07Rik | NM_001114312.1 | chr19:58973357-59076069 |
| 969 | 4930507D05Rik | NR_027926.1 | chr10:62449159-62451353 |
| 970 | 4930507D10Rik | NR_110449.1 | chr11:80850380-80858300 |
| 971 | 4930509E16Rik | NR_045735.1 | chr9:72518249-72531858 |
| 972 | 4930509J09Rik | NR_040547.1 | chr3:73351205-73481651 |
| 973 | 4930509K18Rik | NR_040663.1 | chr4:40313231-40317719 |
| 974 | 4930511A02Rik | NR_045966.1 | chr12:11438232-11444812 |
| 975 | 4930511E03Rik | NR_040761.1 | chr6:94943833-94951545 |
| 976 | 4930511M06Rik | NR_015494.1 | chr18:57546013-57552397 |
| 977 | 4930512B01Rik | NR_033573.1 | chr12:69790343-69841880 |
| 978 | 4930513D17Rik | NR_045416.1 | chr5:39461748-39603574 |
| 979 | 4930513N10Rik | NR_015574.2 | chr8:95806829-95821728 |
| 980 | 4930513O06Rik | NM_029174.3 | chrX:139086242-139093403 |
| 981 | 4930515B02Rik | NR_040654.1 | chr4:140872692-140878057 |
| 982 | 4930515G01Rik | NR_027872.1 | chr5:114773732-114774983 |
| 983 | 4930515G16Rik | NR_003100.1 | chr6:67565233-67565699 |
| 984 | 4930515L03Rik | NR_040632.1 | chr2:16918677-17013726 |
| 985 | 4930515L19Rik | NR_045440.1 | chrX:46267558-46328911 |
| 986 | 4930517E11Rik | NR_040611.1 | chr2:124123635-124129956 |
| 987 | 4930518P08Rik | NR_045364.1 | chr13:50753392-50765248 |
| 988 | 4930519D14Rik | NR_045975.1 | chr13:30615042-30624258 |
| 989 | 4930519F09Rik | NR_033601.1 | chr10:28921962-28923507 |
| 990 | 4930519F16Rik | NM_029170.1 | chrX:103232280-103256606 |
| 991 | 4930519F24Rik | NR_040763.1 | chr9:100022299-100034670 |
| 992 | 4930519G04Rik | NM_026263.2 | chr5:114853713-114883879 |
| 993 | 4930519H02Rik | NR_045974.1 | chr5:15863927-15883766 |
| 994 | 4930520O04Rik | NR_040383.1 | chr9:114368323-114377238 |
| 995 | 4930520P13Rik | NR_036596.1 | chr13:70232821-70248122 |
| 996 | 4930521E06Rik | NR_040602.1 | chr1:44739674-44744949 |
| 997 | 4930522H14Rik | NM_001199090.1 | chr4:109505331-109531204 |
| 998 | 4930522O17Rik | NR_040665.1 | chr4:53246195-53251120 |
| 999 | 4930523C07Rik | NM_001162896.1 | chr1:160044379-160078586 |
| 1000 | 4930523O13Rik | NR_040451.1 | chr15:46435865-46496179 |
| 1001 | 4930524B15Rik | NM_026262.1 | chr1:31965632-31979651 |
| 1002 | 4930524C18Rik | NR_045661.1 | chr14:114831964-114861327 |
| 1003 | 4930524N10Rik | NM_001256259.1 | chrX:154339224-154343392 |
| 1004 | 4930524O05Rik | NR_045316.1 | chr19:10645693-10648053 |
| 1005 | 4930524O08Rik | NR_040735.1 | chr9:89826518-89864028 |
| 1006 | 4930525D18Rik | NR_040738.1 | chr9:114341110-114364627 |
| 1007 | 4930525G20Rik | NR_045194.1 | chr13:67796593-67830985 |
| 1008 | 4930525M21Rik | NM_001243943.1 | chrX:38013907-38018815 |
| 1009 | 4930526I15Rik | NR_015516.2 | chr9:124423786-124424856 |
| 1010 | 4930526L06Rik | NR_045317.1 | chr19:11196816-11299884 |
| 1011 | 4930527F14Rik | NR_045809.1 | chr14:45543709-45562876 |
| 1012 | 4930527G23Rik | NR_045395.1 | chr18:29442199-29466107 |
| 1013 | 4930528A17Rik | NR_028344.1 | chr4:21846326-21848448 |
| 1014 | 4930528D03Rik | NR_045977.1 | chr13:59733649-59737470 |
| 1015 | 4930528P14Rik | NR_040516.1 | chr2:115329265-115344280 |
| 1016 | 4930529C04Rik | NR_033593.1 | chr3:91071661-91075192 |
| 1017 | 4930529K09Rik | NR_040457.1 | chr14:86245969-86262042 |
| 1018 | 4930529L06Rik | NR_040537.1 | chr16:84679788-84685147 |
| 1019 | 4930529M08Rik | NM_175280.3 | chr2:145934783-145964226 |
| 1020 | 4930532M18Rik | NR_108050.1 | chr1:154255688-154270436 |
| 1021 | 4930533B01Rik | NR_040614.1 | chr2:113691052-113708550 |
| 1022 | 4930533P14Rik | NR_040478.1 | chr1:96612056-96662573 |
| 1023 | 4930538K18Rik | NM_029198.3 | chr4:119205054-119218217 |
| 1024 | 4930539C22Rik | NR_040600.1 | chr3:134404142-134423635 |
| 1025 | 4930539E08Rik | NM_172450.3 | chr17:28896394-28915324 |
| 1026 | 4930539J05Rik | NR_030689.1 | chr3:135436220-135438665 |
| 1027 | 4930539M17Rik | NR_040597.1 | chr3:9061963-9071076 |
| 1028 | 4930539N22Rik | NR_040598.1 | chr3:13597138-13652865 |
| 1029 | 4930540M03Rik | NR_040746.1 | chr9:15619856-15641220 |
| 1030 | 4930542C21Rik | NR_040565.1 | chr16:38017322-38054526 |
| 1031 | 4930542D17Rik | NR_040566.1 | chr16:50590502-50654166 |
| 1032 | 4930543E12Rik | NR_045978.1 | chr7:113100235-113142015 |
| 1033 | 4930544D05Rik | NM_001145537.1 | chr1:70615893-70616890 |
| 1034 | 4930544G11Rik | NM_001161773.1 | chr6:65952570-65954014 |
| 1035 | 4930544M13Rik | NR_045976.1 | chr2:114607227-114697822 |
| 1036 | 4930545E07Rik | NR_045374.1 | chr18:17568745-17580890 |
| 1037 | 4930545H06Rik | NR_045357.1 | chr10:68319064-68321142 |
| 1038 | 4930545L23Rik | NR_040517.1 | chr2:135169572-135215616 |
| 1039 | 4930546C10Rik | NR_038051.1 | chr18:68889486-68951528 |
| 1040 | 4930546K05Rik | NR_040754.1 | chr9:42182237-42209231 |
| 1041 | 4930547E08Rik | NR_040514.1 | chr2:103804451-103810622 |
| 1042 | 4930547E14Rik | NR_040564.1 | chr16:59636944-59672993 |
| 1043 | 4930548G14Rik | NR_045811.1 | chr15:46623304-46639858 |
| 1044 | 4930548H24Rik | NM_026296.3 | chr5:31485858-31488262 |
| 1045 | 4930548J01Rik | NR_045462.1 | chr17:4119445-4122102 |
| 1046 | 4930548K13Rik | NR_040656.1 | chr4:26635819-26705449 |
| 1047 | 4930549C01Rik | NM_026300.2 | chr4:136610436-136613213 |
| 1048 | 4930549G23Rik | NR_045376.1 | chr18:67776032-67799943 |
| 1049 | 4930550C14Rik | NM_029247.3 | chr9:53405285-53432803 |
| 1050 | 4930550L24Rik | NM_023774.3 | chrX:58911460-58920304 |
| 1051 | 4930552N02Rik | NR_040661.1 | chr4:52814603-52828269 |
| 1052 | 4930552P12Rik | NR_045318.1 | chr19:55640588-55702204 |
| 1053 | 4930553E22Rik | NR_040567.1 | chr16:84371142-84375505 |
| 1054 | 4930554C24Rik | NR_040739.1 | chr9:84774397-84784351 |
| 1055 | 4930555B11Rik | NR_040633.1 | chr2:57181830-57188257 |
| 1056 | 4930555G01Rik | NM_175393.4 | chr14:5050628-5059243 |
| 1057 | 4930556C24Rik | NR_040506.1 | chr16:85819210-85826772 |
| 1058 | 4930556G01Rik | NR_040655.1 | chr4:30664595-30855744 |
| 1059 | 4930556I02Rik | NR_045714.1 | chr14:61492687-61500382 |
| 1060 | 4930556M19Rik | NR_045063.1 | chr15:10714835-10790123 |
| 1061 | 4930556N09Rik | NR_045358.1 | chr10:97035767-97061059 |
| 1062 | 4930557A04Rik | NM_029229.1 | chrX:9849702-9850252 |
| 1063 | 4930557J02Rik | NR_040703.1 | chr5:34118739-34135339 |
| 1064 | 4930558C23Rik | NR_015490.1 | chr3:95386457-95402841 |
| 1065 | 4930558G05Rik | NR_045441.1 | chrX:129051523-129067146 |
| 1066 | 4930558J18Rik | NR_037999.1 | chr1:57359221-57377544 |
| 1067 | 4930558K02Rik | NM_001204904.1 | chr1:161942088-161979636 |
| 1068 | 4930562C15Rik | NM_030192.1 | chr16:4835415-4867691 |
| 1069 | 4930562F07Rik | NR_038030.1 | chr1:160074734-160077918 |
| 1070 | 4930563D23Rik | NR_029252.2 | chr16:92318762-92321441 |
| 1071 | 4930563E18Rik | NR_045379.1 | chr18:10706859-10711832 |
| 1072 | 4930563E22Rik | NM_001163728.1 | chr11:72215137-72218450 |
| 1073 | 4930563F08Rik | NR_040704.1 | chr5:131880268-131883768 |
| 1074 | 4930563M20Rik | NR_046193.1 | chr8:116783711-116801412 |
| 1075 | 4930564B18Rik | NM_029230.1 | chr14:75642258-75667137 |
| 1076 | 4930564C03Rik | NM_029257.3 | chr17:44879703-44880885 |
| 1077 | 4930564D02Rik | NM_029228.1 | chr3:105066843-105078806 |
| 1078 | 4930565D16Rik | NR_040752.1 | chr3:84349375-84379921 |
| 1079 | 4930565N06Rik | NR_040476.1 | chr16:36888051-38897189 |
| 1080 | 4930567H12Rik | NR_015535.2 | chr8:125584637-125616670 |
| 1081 | 4930567H17Rik | NM_001033807.2 | chrX:70393900-70394740 |
| 1082 | 4930567J20Rik | NR_040576.1 | chr16:71249803-71267176 |
| 1083 | 4930567K20Rik | NR_046010.1 | chr10:10751045-10758131 |
| 1084 | 4930568D16Rik | NM_029463.1 | chr2:35354217-35367729 |
| 1085 | 4930568E12Rik | NR_040755.1 | chr9:13091266-13105855 |
| 1086 | 4930568G15Rik | NR_040480.1 | chr1:165066616-165091930 |
| 1087 | 4930570G19Rik | NR_040398.1 | chr3:156548414-156561687 |
| 1088 | 4930571K23Rik | NM_001145759.1 | chr7:125368860-125371013 |
| 1089 | 4930571O06Rik | NR_110476.1 | chr8:113517281-113550808 |
| 1090 | 4930572K03Rik | NR_045371.1 | chr5:127170564-127184356 |
| 1091 | 4930572O03Rik | NR_073011.1 | chr5:15652287-15657059 |
| 1092 | 4930572O13Rik | NR_045718.1 | chr14:25139794-25143241 |
| 1093 | 4930573O16Rik | NR_040620.1 | chr2:52291001-52315240 |
| 1094 | 4930577N17Rik | NR_073429.1 | chr3:51628760-51278407 |
| 1095 | 4930578C19Rik | NM_175228.2 | chrX:18418426-18461397 |
| 1096 | 4930578E11Rik | NR_045391.1 | chr18:29396715-29496416 |
| 1097 | 4930578I06Rik | NM_026359.3 | chr14:63971121-63987780 |
| 1098 | 4930578M01Rik | NR_045991.1 | chr15:98985964-98989281 |
| 1099 | 4930578N18Rik | NR_040575.1 | chr16:76122612-76156086 |
| 1100 | 4930579P18Rik | NM_001163985.1 | chr3:138164134-138186713 |
| 1101 | 4930579G18Rik | NR_038053.1 | chr14:54655010-54655100 |
| 1102 | 4930579G24Rik | NM_029482.1 | chr3:79629078-79632819 |
| 1103 | 4930579K19Rik | NR_029444.1 | chr9:98562459-98563611 |
| 1104 | 4930581F22Rik | NR_029475.1 | chr9:35116727-35130922 |
| 1105 | 4930583K01Rik | NR_027879.1 | chr7:118243906-118245551 |
| 1106 | 4930583P06Rik | NR_040612.1 | chr2:124217678-124222358 |
| 1107 | 4930584F24Rik | NR_029445.1 | chr5:26460089-26493314 |
| 1108 | 4930590J08Rik | NM_198668.2 | chr6:91904232-91950725 |
| 1109 | 4930590L20Rik | NR_040604.1 | chr1:140570175-140656402 |
| 1110 | 4930591A17Rik | NM_026596.2 | chr2:179414935-179416880 |
| 1111 | 4930592A05Rik | NR_045070.1 | chr15:33593880-33653436 |
| 1112 | 4930592I03Rik | NR_033307.1 | chr18:82918404-82920560 |
| 1113 | 4930593A02Rik | NR_045167.1 | chr5:58692588-58788524 |
| 1114 | 4930593C15Rik | NR_040518.1 | chr9:120924454-120930802 |
| 1115 | 4930594C11Rik | NR_024017.1 | chr3:37485850-37488605 |
| 1116 | 4930595M18Rik | NM_173435.3 | chrX:81419574-81458122 |
| 1117 | 4930596D02Rik | NM_001033766.3 | chr14:35809485-35811978 |
| 1118 | 4930596I21Rik | NR_108103.1 | chr1:138977656-138979246 |
| 1119 | 4930597G03Rik | NR_045736.1 | chr14:51317334-51345489 |
| 1120 | 4930598F16Rik | NR_040479.1 | chr1:95701183-95716518 |
| 1121 | 4930599N23Rik | NR_045813.1 | chr6:39118472-39148312 |
| 1122 | 4931402G19Rik | NR_040608.1 | chr2:120455697-120469367 |
| 1123 | 4931403C20Rik | NR_045306.1 | chr19:26768800-26823907 |
| 1124 | 4931403G20Rik | NR_038172.1 | chr12:69843685-69853671 |
| 1125 | 4931406B18Rik | NM_028737.3 | chr7:43492043-43505938 |
| 1126 | 4931406C07Rik | NM_001199484.1 | chr9:15283336-15306448 |
| 1127 | 4931406H21Rik | NR_033492.1 | chr14:25586803-25590661 |
| 1128 | 4931406M04Rik | NM_172741.2 | chr7:34236713-34285609 |
| 1129 | 4931408C20Rik | NM_001033764.3 | chr1:26681800-26687460 |
| 1130 | 4931408D14Rik | NR_040298.1 | chr19:37258425-37264095 |
| 1131 | 4931409K22Rik | NM_177676.6 | chr5:24543433-24555469 |
| 1132 | 4931412M21 | NR_110487.1 | chr12:10446387-10531303 |
| 1133 | 4931414P19Rik | NM_028890.2 | chr14:54583662-54605908 |
| 1134 | 4931417E11Rik | NR_257737.3 | chr6:73468572-73469667 |
| 1135 | 4931419H13Rik | NR_040593.1 | chr3:55055241-55084002 |
| 1136 | 4931420L22Rik | NR_040561.1 | chr16:71131075-71139029 |

Fig. 26 - 7

| | | | | | | | |
|---|---|---|---|---|---|---|---|
| 1137 | 4931423N10Rik | NM_027635.1 | chr2:23207475-23267129 | 1232 | 4933417G07Rik | NR_033592.1 | chr3:55847104-55848065 |
| 1138 | 4931428F04Rik | NM_001166394.1 | chr8:105280408-105289528 | 1233 | 4933417O13Rik | NR_045842.1 | chr7:143322771-143330650 |
| 1139 | 4931428L18Rik | NR_033445.1 | chr1:31141077-31222656 | 1234 | 4933421I07Rik | NR_027702.2 | chr7:42445461-42448080 |
| 1140 | 4931429I11Rik | NM_001081121.1 | chr9:40894848-40964112 | 1235 | 4933421O10Rik | NR_036602.1 | chr4:33027138-33031323 |
| 1141 | 4931429I15Rik | NM_183104.2 | chr9:46303360-46319986 | 1236 | 4933422A05Rik | NR_040715.1 | chr9:35281104-35285423 |
| 1142 | 4931429P17Rik | NR_038004.1 | chr13:47960329-48018608 | 1237 | 4933422H20Rik | NM_001033775.3 | chr11:115440544-115448268 |
| 1143 | 4931430N09Rik | NR_046053.1 | chr6:118880157-118885543 | 1238 | 4933424G05Rik | NR_045372.1 | chr18:14988994-15047987 |
| 1144 | 4931431B13Rik | NR_045183.1 | chr7:128192049-128203328 | 1239 | 4933424G06Rik | NR_040290.1 | chr1:36714537-36757960 |
| 1145 | 4931431C16Rik | NR_045807.1 | chr5:35581226-35588763 | 1240 | 4933425B07Rik | NR_046460.1 | chr14:46602805-46637423 |
| 1146 | 4931431F19Rik | NM_027634.1 | chr7:104127912-104129823 | 1241 | 4933425L06Rik | NM_025751.3 | chr13:105082121-105121782 |
| 1147 | 4931440F15Rik | NM_176829.2 | chr11:29822394-29825668 | 1242 | 4933426M11Rik | NM_001242419.1 | chr12:80790531-80880833 |
| 1148 | 4931440I10Rik | NR_045503.1 | chr14:62760500-62830126 | 1243 | 4933427D06Rik | NM_175017.3 | chr6:89096114-89110037 |
| 1149 | 4931440L10Rik | NM_001145300.2 | chr1:134540940-134549682 | 1244 | 4933427D14Rik | NM_028963.2 | chr11:72154096-72203371 |
| 1150 | 4931440P22Rik | NR_027955.1 | chr3:65527484-65529414 | 1245 | 4933427F11Rik | NR_033197.1 | chr15:74709160-74710374 |
| 1151 | 4932411E22Rik | NM_172534.2 | chr1:89390222-89418948 | 1246 | 4933427E13Rik | NR_045853.1 | chr11:25326106-25367137 |
| 1152 | 4932411N23Rik | NM_177705.3 | chrX:126812461-126834004 | 1247 | 4933427G17Rik | NM_028955.1 | chr7:120982508-121014787 |
| 1153 | 4932412D23Rik | NR_040521.1 | chr16:42725701-42875587 | 1248 | 4933427J22Rik | NR_040716.1 | chr4:139926110-139943519 |
| 1154 | 4932413F04Rik | NR_040764.1 | chr9:103557089-103565891 | 1249 | 4933428C19Rik | NR_040644.1 | chr4:40482839-40525548 |
| 1155 | 4932414J04Rik | NR_028259.1 | chr1:21494729-21511180 | 1250 | 4933428G20Rik | NM_001289118.1 | chr1:97496782-97500340 |
| 1156 | 4932414N04Rik | NM_183113.3 | chr2:68657883-68748465 | 1251 | 4933429K18Rik | NR_045307.1 | chr19:45726554-45730558 |
| 1157 | 4932415M13Rik | NR_073205.1 | chr17:53716508-53733843 | 1252 | 4933429O19Rik | NR_033783.1 | chr14:48887872-48887112 |
| 1158 | 4932416H05Rik | NR_029452.1 | chr2:129798368-129801459 | 1253 | 4933430H16Rik | NR_045855.1 | chr7:82937937-82971391 |
| 1159 | 4932416K20Rik | NM_001002775.2 | chr8:104795236-104798792 | 1254 | 4933430I17Rik | NM_177607.3 | chr4:62525368-62547993 |
| 1160 | 4932418E24Rik | NM_177841.3 | chr2:26271646-26294557 | 1255 | 4933430M04Rik | NR_045857.2 | chr11:24481908-24569951 |
| 1161 | 4932429P05Rik | NM_001085511.1 | chrX:89752267-89755491 | 1256 | 4933430N04Rik | NR_045854.1 | chr8:9125411-9132288 |
| 1162 | 4932435O22Rik | NR_027643.2 | chr11:114413404-114448860 | 1257 | 4933431E20Rik | NR_015459.1 | chr3:107888549-107896213 |
| 1163 | 4932438A13Rik | NM_172679.2 | chr3:36863105-37053033 | 1258 | 4933431G14Rik | NR_045163.1 | chr6:72120212-72122940 |
| 1164 | 4932438H23Rik | NM_001163695.1 | chr16:91053934-91069145 | 1259 | 4933432G23Rik | NR_040716.1 | chr9:118429838-118437048 |
| 1165 | 4932441J04Rik | NR_015588.2 | chr5:57570083-57717919 | 1260 | 4933432I03Rik | NR_045657.1 | chr14:102987411-103033803 |
| 1166 | 4932443I19Rik | NM_001101519.1 | chr8:13705888-13743066 | 1261 | 4933432I09Rik | NR_015575.1 | chr16:18209685-18213863 |
| 1167 | 4932702P03Rik | NR_045182.1 | chr13:24905599-24911780 | 1262 | 4933432K03Rik | NR_102286.1 | chr7:121587385-121589836 |
| 1168 | 4933400A11Rik | NR_003635.1 | chrX:169776377-169779635 | 1263 | 4933433C11Rik | NM_028961.1 | chr2:25212558-25214630 |
| 1169 | 4933400B14Rik | NR_045432.1 | chr17:89320226-89327333 | 1264 | 4933433F19Rik | NR_045856.1 | chr8:30568394-30575573 |
| 1170 | 4933400C23Rik | NR_040770.1 | chr9:92718715-92795711 | 1265 | 4933433G08Rik | NR_105026.1 | chr9:61103011-61105386 |
| 1171 | 4933400F21Rik | NR_015540.1 | chr1:89676506-89683892 | 1266 | 4933433G15Rik | NR_040719.1 | chr13:75410183-75415537 |
| 1172 | 4933400L20Rik | NR_045730.1 | chr8:103603798-103680382 | 1267 | 4933433G19Rik | NR_045851.1 | chr13:66996817-67032405 |
| 1173 | 4933401B06Rik | NR_033580.1 | chrX:107542581-107543800 | 1268 | 4933433H22Rik | NR_045458.1 | chr17:84078659-84089875 |
| 1174 | 4933401D09Rik | NR_045431.1 | chr17:15631787-15641102 | 1269 | 4933434E20Rik | NM_001287086.1 | chr3:90052801-90063341 |
| 1175 | 4933401H06Rik | NR_040540.1 | chr3:135833693-135840269 | 1270 | 4933434I20Rik | NM_026233.2 | chr8:83348471-83379402 |
| 1176 | 4933402C06Rik | NR_045504.1 | chr7:40674736-40691260 | 1271 | 4933436E23Rik | NR_040455.1 | chr1:139379451-139402852 |
| 1177 | 4933402D24Rik | NM_001256158.1 | chr1:63754908-63769267 | 1272 | 4933436H12Rik | NR_046208.1 | chr7:68417423-68426133 |
| 1178 | 4933402E13Rik | NM_001199996.1 | chrX:62287141-62292078 | 1273 | 4933436I01Rik | NR_025741.1 | chrX:67919863-67921450 |
| 1179 | 4933402J07Rik | NM_177901.3 | chr8:87563906-87589197 | 1274 | 4933438B17Rik | NR_040685.1 | chr5:127030788-127088529 |
| 1180 | 4933402J10Rik | NR_040682.1 | chr5:59963118-59986002 | 1275 | 4933438K21Rik | NR_045446.1 | chr4:147063365-147068436 |
| 1181 | 4933402J15Rik | NR_046059.1 | chr14:74355526-74369741 | 1276 | 4933439C10Rik | NR_015585.2 | chr11:59505684-59511067 |
| 1182 | 4933402N03Rik | NM_173409.4 | chr7:131138346-131146283 | 1277 | 4933439K11Rik | NR_040558.1 | chr1:172541619-172550806 |
| 1183 | 4933402N22Rik | NM_001177510.1 | chr5:11918042-11922804 | 1278 | 4933440J02Rik | NR_045344.1 | chr10:111586718-111594273 |
| 1184 | 4933402P03Rik | NM_175368.1 | chr1:69816565-69818440 | 1279 | 4933440M06Rik | NR_045803.1 | chr7:125331781-125349786 |
| 1185 | 4933403O08Rik | NM_001177389.1 | chrX:112239048-112243852 | 1280 | 5031410O06Rik | NM_207657.3 | chr5:26098867-26105314 |
| 1186 | 4933404G15Rik | NR_045920.1 | chr16:16707686-16718121 | 1281 | 5031414D18Rik | NM_198642.2 | chr14:75016026-75052532 |
| 1187 | 4933404K08Rik | NR_046038.1 | chr13:23278349-23282267 | 1282 | 5031425E22Rik | NR_040469.1 | chr5:23431807-23434353 |
| 1188 | 4933404O12Rik | NR_015555.1 | chr5:136919145-136937109 | 1283 | 5031425F14Rik | NR_015558.2 | chr2:166447450-166458770 |
| 1189 | 4933405D12Rik | NR_046036.1 | chr3:122882591-122924116 | 1284 | 5031426O15Rik | NR_027894.1 | chr2:6922701-6928722 |
| 1190 | 4933405E24Rik | NR_045506.1 | chr1:54177771-54213288 | 1285 | 5031434C07Rik | NR_045986.1 | chr6:112286793-112290319 |
| 1191 | 4933405L10Rik | NM_027655.1 | chr8:105708302-105710168 | 1286 | 5031434O11Rik | NR_033624.1 | chr3:51559756-51567116 |
| 1192 | 4933405O20Rik | NM_172901.2 | chr7:50599189-50600528 | 1287 | 5031439G07Rik | NM_001033273.2 | chr5:84945719-84987971 |
| 1193 | 4933406C10Rik | NR_044986.1 | chr12:32919383-32953789 | 1288 | 5033403H07Rik | NR_040413.1 | chr5:52973011-52992292 |
| 1194 | 4933406D12Rik | NR_040502.1 | chr2:146542930-146546108 | 1289 | 5033404E19Rik | NR_033600.1 | chr1:185497305-185498014 |
| 1195 | 4933406F09Rik | NR_015568.2 | chr14:7412472-7422685 | 1290 | 5033406O09Rik | NR_029464.1 | chr12:111941990-111944482 |
| 1196 | 4933406G16Rik | NR_046037.1 | chr1:19065274-19075740 | 1291 | 5133400J02Rik | NR_110444.1 | chr11:51189832-51220418 |
| 1197 | 4933406J18Rik | NR_029437.1 | chr7:114315478-114415161 | 1292 | 5330411J11Rik | NR_040510.1 | chr2:59382492-59386682 |
| 1198 | 4933406J08Rik | NM_028914.5 | chr2:122186271-122206393 | 1293 | 5330413P13Rik | NR_029431.1 | chr2:131820005-131847656 |
| 1199 | 4933406J10Rik | NR_046004.1 | chr7:82743345-82755644 | 1294 | 5330417C22Rik | NM_001033304.1 | chr3:108458068-108536522 |
| 1200 | 4933406K04Rik | NR_015612.2 | chr12:106685606-106716324 | 1295 | 5330426P16Rik | NR_028300.1 | chr16:50726750-50732773 |
| 1201 | 4933406M09Rik | NM_173771.4 | chr1:134385993-134390983 | 1296 | 5330434G04Rik | NR_015552.1 | chrX:105372993-105391754 |
| 1202 | 4933407E24Rik | NR_045819.1 | chr4:124569178-124575538 | 1297 | 5330439B14Rik | NR_037679.1 | chr6:142614594-142626462 |
| 1203 | 4933407G14Rik | NR_045841.1 | chr10:75449509-75463104 | 1298 | 5430401F13Rik | NM_001244628.1 | chr6:131543761-131553757 |
| 1204 | 4933407I08Rik | NR_040731.1 | chr9:51914428-51927003 | 1299 | 5430402E10Rik | NM_027768.3 | chrX:77919785-77925062 |
| 1205 | 4933407K13Rik | NR_029443.1 | chrX:75725457-75764699 | 1300 | 5430402O13Rik | NR_015581.1 | chr6:50566642-50594865 |
| 1206 | 4933407L21Rik | NR_037623.1 | chr1:85928482-85931756 | 1301 | 5430401A15Rik | NR_046181.1 | chr3:35864084-35882957 |
| 1207 | 4933408B17Rik | NM_177773.4 | chr18:34579845-34597468 | 1302 | 5430405H02Rik | NR_015591.1 | chr2:156852402-156862945 |
| 1208 | 4933408J17Rik | NR_045810.1 | chr10:93589412-93605245 | 1303 | 5430416N02Rik | NR_034038.1 | chr5:100420841-100429535 |
| 1209 | 4933408N05Rik | NR_045834.2 | chr8:114341160-114351478 | 1304 | 5430416O09Rik | NR_033551.1 | chr4:43730033-43734534 |
| 1210 | 4933409G03Rik | NM_177651.3 | chr2:68582412-68616463 | 1305 | 5430417L22Rik | NM_001301269.1 | chr2:118745758-118748810 |
| 1211 | 4933409K07Rik | NR_033123.1 | chr4:60800-42462993 | 1306 | 5430419D17Rik | NM_175166.3 | chr7:131174401-131250945 |
| 1212 | 4933411E08Rik | NR_045342.1 | chr10:117925458-117948307 | 1307 | 5430421F17Rik | NR_040352.1 | chr8:25302649-25306270 |
| 1213 | 5433411G06Rik | NR_045158.1 | chr10:51756173-51757194 | 1308 | 5430421N21Rik | NM_001201323.1 | chr15:101485129-101491512 |
| 1214 | 4933411G11Rik | NM_177880.4 | chr5:143181016-143205068 | 1309 | 5430425K12Rik | NR_103550.1 | chr13:80940402-80948597 |
| 1215 | 4933411K16Rik | NM_025752.2 | chr19:42052227-42053628 | 1310 | 5430427M07Rik | NR_045858.1 | chr12:91045847-91056635 |
| 1216 | 4933411K20Rik | NR_025747.3 | chr8:46169555-46195590 | 1311 | 5430427O19Rik | NM_001163539.1 | chrX:85870272-85891499 |
| 1217 | 4933412E12Rik | NR_038025.1 | chr10:116950561-116963279 | 1312 | 5430428K19Rik | NR_045426.1 | chrX:6452375-6574663 |
| 1218 | 4933412E24Rik | NM_027568.1 | chr15:60014865-60016618 | 1313 | 5430429G15Rik | NR_040541.1 | chr3:38203150-38208119 |
| 1219 | 4933412G06Rik | NR_045657.1 | chr13:15781663-15802630 | 1314 | 5430435G22Rik | NM_145509.3 | chr1:131688694-131715439 |
| 1220 | 4933413G19Rik | NM_027697.1 | chr6:128375509-128385144 | 1315 | 5430437I10Rik | NR_045274.1 | chr15:5496317-5594983 |
| 1221 | 4933413I09Rik | NR_038005.1 | chr14:26357546-26400456 | 1316 | 5430440P10Rik | NR_045859.1 | chr14:105427558-105437716 |
| 1222 | 4933413L06Rik | NR_045508.1 | chr13:117706763-117720011 | 1317 | 5530400C23Rik | NR_027784.1 | chr6:133292215-133295790 |
| 1223 | 4933415F23Rik | NM_025774.2 | chr1:23100473-23102253 | 1318 | 5530401B14Rik | NR_038010.1 | chr11:81860676-81894582 |
| 1224 | 4933416C03Rik | NM_001161855.1 | chr10:116111663-116113917 | 1319 | 5530601H04Rik | NR_015467.1 | chrX:105040853-105070124 |
| 1225 | 4933416E03Rik | NR_040498.1 | chr2:159947340-159981289 | 1320 | 5730403I07Rik | NR_040378.1 | chr9:77366411-77399416 |
| 1226 | 4933416I08Rik | NR_027700.1 | chrX:53686490-53691332 | 1321 | 5730407K24Rik | NR_038158.1 | chrX:13042014-13045296 |
| 1227 | 4933416M06Rik | NR_045846.2 | chr3:101254318-101293396 | 1322 | 5730408K05Rik | NR_027866.1 | chr19:8888386-8888770 |
| 1228 | 4933416M07Rik | NR_045840.1 | chr8:27142909-27149706 | 1323 | 5730409E04Rik | NM_001013755.3 | chr4:126609853-126614371 |
| 1229 | 4933417A14Rik | NM_025750.3 | chr13:34924408-34953196 | 1324 | 5730412P04Rik | NR_045424.1 | chrX:136104602-136115420 |
| 1230 | 4933417D19Rik | NR_045849.1 | chr8:123235090-123242359 | 1325 | 5730416F02Rik | NR_033596.1 | chr1:109004484-109002296 |
| 1231 | 4933417E11Rik | NR_040454.1 | chr1:71958997-72005195 | 1326 | 5730420D15Rik | NR_045338.1 | chr10:95417374-95428640 |

Fig. 26 - 8

| | | | | | | | |
|---|---|---|---|---|---|---|---|
| 1327 | 5730422E09Rik | NR_015478.2 | chr5:149119564-149182036 | 1422 | 9030617O03Rik | NM_145448.4 | chr12:100779122-100872610 |
| 1328 | 5730435O14Rik | NR_046341.1 | chr10:41568015-41576476 | 1423 | 9030619P08Rik | NR_108041.1 | chr15:75427605-75431829 |
| 1329 | 5730455P16Rik | NM_027472.3 | chr11:80360491-80378015 | 1424 | 9030624G23Rik | NM_001256489.1 | chr12:24043201-24097269 |
| 1330 | 5730457N03Rik | NM_038163.1 | chr6:52308388-52314832 | 1425 | 9030624J02Rik | NM_027815.4 | chr7:118740270-118841491 |
| 1331 | 5730460C07Rik | NR_045801.1 | chr3:153789304-153792087 | 1426 | 9030625G05Rik | NR_110446.1 | chr18:74972763-74981547 |
| 1332 | 5730480H06Rik | NR_045500.1 | chr5:48395572-48414294 | 1427 | 9130008F23Rik | NM_027834.3 | chr17:40875481-40880558 |
| 1333 | 5730488B01Rik | NR_073462.1 | chr4:44702799-44705110 | 1428 | 9130011E15Rik | NM_198296.2 | chr19:45818143-45998488 |
| 1334 | 5730507C01Rik | NM_001033157.4 | chr12:18514509-18535254 | 1429 | 9130015A21Rik | NR_045050.1 | chr2:35672290-35695118 |
| 1335 | 5730508B09Rik | NM_027482.3 | chr3:127869687-127896323 | 1430 | 9130015L21Rik | NM_040499.1 | chr2:160016652-160040620 |
| 1336 | 5730522E02Rik | NR_027973.1 | chr11:25616845-26210576 | 1431 | 9130019O22Rik | NM_030226.3 | chr7:127382259-127387166 |
| 1337 | 5730559C18Rik | NM_028872.3 | chr1:136213521-136234280 | 1432 | 9130019P16Rik | NR_033635.1 | chr6:54269680-54430221 |
| 1338 | 5830403L16Rik | NM_178243.3 | chr1:153849541-153851195 | 1433 | 9130023H24Rik | NM_177001.3 | chr7:128234450-128238031 |
| 1339 | 5830411N06Rik | NM_001128145.1 | chr7:140247380-140299791 | 1434 | 9130024F11Rik | NR_024325.1 | chr1:56971468-56975196 |
| 1340 | 5830415F09Rik | NM_029086.2 | chr4:46376974-46389423 | 1435 | 9130204L05Rik | NM_001101461.2 | chr3:91088136-91090805 |
| 1341 | 5830416J19Rik | NR_045384.1 | chr5:64044972-64050226 | 1436 | 9130209A04Rik | NR_033453.1 | chr18:47452567-47470868 |
| 1342 | 5830416P10Rik | NR_028427.1 | chr19:53441211-53464796 | 1437 | 9130213F21Rik | NR_046180.1 | chr6:72013895-72042528 |
| 1343 | 5830417I10Rik | NR_028359.1 | chr3:88777056-88829371 | 1438 | 9130221H12Rik | NR_046001.1 | chr7:25228722-25230264 |
| 1344 | 5830418K08Rik | NM_176976.4 | chr9:15316913-15357788 | 1439 | 9130227L01Rik | NR_045837.1 | chr1:55931240-55972098 |
| 1345 | 5830418P13Rik | NR_040466.1 | chr9:103423577-103461260 | 1440 | 9130230L23Rik | NR_027961.1 | chr5:65987927-66004285 |
| 1346 | 5830428M24Rik | NR_038060.1 | chr2:69464786-69475550 | 1441 | 9130401M01Rik | NM_029418.4 | chr15:58022270-58034294 |
| 1347 | 5830432E09Rik | NR_015548.1 | chr7:135648456-135652314 | 1442 | 9130409J23Rik | NM_001033819.1 | chr1:181051236-181060667 |
| 1348 | 5830444B04Rik | NR_102283.1 | chr4:155408308-155421704 | 1443 | 9230009I02Rik | NR_045865.1 | chr11:51085086-51091835 |
| 1349 | 5830454E08Rik | NR_073359.1 | chr9:120577330-120578073 | 1444 | 9230102K24Rik | NR_028438.1 | chr10:110600649-110615961 |
| 1350 | 5830473C10Rik | NM_001252661.1 | chr5:90561208-90597906 | 1445 | 9230102O04Rik | NR_040511.1 | chr2:9883040-9889540 |
| 1351 | 5930403L14Rik | NR_045643.1 | chr4:154630690-154636367 | 1446 | 9230104L09Rik | NM_029960.3 | chr2:148846713-148850934 |
| 1352 | 5930412G12Rik | NR_015517.2 | chr5:128579129-128600687 | 1447 | 9230105E05Rik | NR_040626.1 | chr10:120389522-120392793 |
| 1353 | 5930430L01Rik | NR_102383.1 | chr5:148990055-148995214 | 1448 | 9230110C19Rik | NM_199017.2 | chr9:8021671-8042823 |
| 1354 | 5930438M14Rik | NR_046158.1 | chr13:101232126-101247551 | 1449 | 9230110F15Rik | NM_029843.1 | chr9:35838328-35844150 |
| 1355 | 6030407O03Rik | NR_045311.1 | chr1:73618380-73864466 | 1450 | 9230112D13Rik | NM_030062.1 | chr14:34511620-34522801 |
| 1356 | 6030408B16Rik | NR_033803.1 | chr15:101293211-101297426 | 1451 | 9230112J17Rik | NR_040463.1 | chr9:60523966-60545882 |
| 1357 | 6030419C18Rik | NM_176921.3 | chr9:58488460-58499742 | 1452 | 9230114K14Rik | NR_015537.2 | chr5:52190680-52197984 |
| 1358 | 6030440G07Rik | NR_036598.1 | chr12:110994397-111013872 | 1453 | 9230116L04Rik | NR_110486.1 | chr12:79088704-79103939 |
| 1359 | 6030443J06Rik | NR_102315.1 | chr5:22550412-22558171 | 1454 | 9230116N13Rik | NR_024328.1 | chr1:136413915-136415519 |
| 1360 | 6030458C11Rik | NM_001166360.1 | chr15:12819903-12824657 | 1455 | 9330020H09Rik | NR_028442.1 | chr15:98567323-98570864 |
| 1361 | 6030466F02Rik | NR_040702.1 | chr8:123733957-123739941 | 1456 | 9330102E08Rik | NR_077223.1 | chr6:128169699-128183803 |
| 1362 | 6030468B19Rik | NM_029964.3 | chr11:117797659-117807308 | 1457 | 9330111N05Rik | NR_015587.2 | chr13:80964073-81079857 |
| 1363 | 6030469F06Rik | NR_102715.1 | chr12:31168861-31185922 | 1458 | 9330117O12Rik | NR_045400.1 | chr18:54611743-54639870 |
| 1364 | 6030498E09Rik | NM_183126.2 | chrX:38772779-38962688 | 1459 | 9330133G14Rik | NR_045696.1 | chr8:122448655-122446476 |
| 1365 | 6230406O17Rik | NR_029446.1 | chr14:20702011-20703099 | 1460 | 9330151L19Rik | NR_033222.1 | chr12:69197210-69199868 |
| 1366 | 6330403A02Rik | NM_001081227.2 | chr1:180432372-180483504 | 1461 | 9330158H04Rik | NR_015589.1 | chr6:36333137-36388234 |
| 1367 | 6330403K07Rik | NM_134022.2 | chr1:71033940-71033617 | 1462 | 9330159F19Rik | NM_001162537.2 | chr10:29211642-29230779 |
| 1368 | 6330407A03Rik | NR_028126.1 | chr4:3714963-3716806 | 1463 | 9330159M08Rik | NR_037982.1 | chr9:88841797-88858801 |
| 1369 | 6330408A02Rik | NM_177312.4 | chr7:13258966-13278721 | 1464 | 9330160Z12Rik | NR_102323.1 | chr13:24937400-24939049 |
| 1370 | 6330409D20Rik | NM_027529.1 | chr2:32732620-32741016 | 1465 | 9330162B11Rik | NR_038007.1 | chr1:188008575-188008990 |
| 1371 | 6330410L21Rik | NR_040589.1 | chr3:129753757-129763882 | 1466 | 9330175E14Rik | NR_015311.1 | chr8:94433126-94435103 |
| 1372 | 6330415B21Rik | NR_045141.1 | chr6:77380256-77382475 | 1467 | 9330175M20Rik | NR_045151.2 | chr1:51218385-51333779 |
| 1373 | 6330416G13Rik | NM_144905.3 | chr4:63560359-63586353 | 1468 | 9330178D15Rik | NR_040553.1 | chr3:155976353-156008592 |
| 1374 | 6330418K02Rik | NR_045821.1 | chr5:138264044-138266661 | 1469 | 9330179Q01Rik | NR_040273.1 | chr6:127149625-127212419 |
| 1375 | 6330419J24Rik | NR_028086.1 | chrX:56374585-56378470 | 1470 | 9330182L06Rik | NM_172706.3 | chr5:9266192-9480717 |
| 1376 | 6330549D23Rik | NR_003619.2 | chr3:96606661-96629819 | 1471 | 9330182O14Rik | NM_001256056.1 | chr15:40134364-40150010 |
| 1377 | 6430411K18Rik | NR_002848.3 | chr12:109591536-109592851 | 1472 | 9330188P03Rik | NR_102319.1 | chr14:105589548-105593929 |
| 1378 | 6430503K07Rik | NR_108091.1 | chr2:147187423-147188482 | 1473 | 9430007A20Rik | NM_198662.3 | chr4:144519821-144529353 |
| 1379 | 6430531B16Rik | NM_001033465.2 | chr7:139972302-139978755 | 1474 | 9430008C03Rik | NR_015461.1 | chr2:158353699-158361509 |
| 1380 | 6430548M08Rik | NM_001163760.1 | chr8:120144928-120165307 | 1475 | 9430014N10Rik | NR_045737.1 | chr15:93904855-93927111 |
| 1381 | 6430550D23Rik | NM_001145351.1 | chr3:156000442-156004427 | 1476 | 9430015G10Rik | NM_145557.3 | chr4:156109997-156127263 |
| 1382 | 6430562O15Rik | NR_015515.2 | chr3:99410835-99412826 | 1477 | 9430016H08Rik | NM_001081181.2 | chr1:57406547-57415958 |
| 1383 | 6430571L13Rik | NM_175486.3 | chr9:107340639-107349683 | 1478 | 9430018G01Rik | NR_045988.1 | chr6:43442428-43474318 |
| 1384 | 6430573F11Rik | NM_176952.4 | chr8:36489190-36513013 | 1479 | 9430019J16Rik | NR_040635.1 | chr2:75436056-75444179 |
| 1385 | 6430584L05Rik | NR_046179.1 | chr6:55396886-55412285 | 1480 | 9430020K01Rik | NM_001081963.1 | chr18:4634928-4682869 |
| 1386 | 6430706D22Rik | NR_040291.1 | chr1:88263112-88269408 | 1481 | 9430021M05Rik | NR_033569.1 | chr2:162661162-162675204 |
| 1387 | 6430710C18Rik | NR_102348.1 | chr2:72745845-72813717 | 1482 | 9430037G07Rik | NR_040766.1 | chr9:88595324-88599243 |
| 1388 | 6530402F18Rik | NR_029460.1 | chr2:29245115-29252993 | 1483 | 9430038B01Rik | NM_029882.2 | chr7:137375568-137410756 |
| 1389 | 6530411M01Rik | NR_027881.1 | chr17:9147718-9168022 | 1484 | 9430041J12Rik | NR_033568.1 | chr7:4074124-4120728 |
| 1390 | 6720416L17Rik | NR_110445.1 | chr2:74748421-74762896 | 1485 | 9430060J03Rik | NR_015525.1 | chr1:92933542-92950590 |
| 1391 | 6720468P15Rik | NR_040306.1 | chr19:57508563-57512788 | 1486 | 9430069E07Rik | NM_001256161.1 | chr15:34349050-34357872 |
| 1392 | 6720483E21Rik | NR_040492.1 | chr1:20888649-20890473 | 1487 | 9430076C15Rik | NR_015553.2 | chr6:53287294-53397216 |
| 1393 | 6720489N17Rik | NM_173381.1 | chr13:62603014-62624182 | 1488 | 9430083A17Rik | NR_029463.1 | chr13:51097737-51100727 |
| 1394 | 6820408C15Rik | NM_001289738.1 | chr2:152415586-152444330 | 1489 | 9430091E24Rik | NR_040363.1 | chr8:111127443-111145498 |
| 1395 | 6820431F20Rik | NM_030708.1 | chr8:20268285-20297432 | 1490 | 9530002B09Rik | NR_023865.3 | chr4:122689258-122705135 |
| 1396 | 7420426K07Rik | NM_001033983.1 | chr9:98903118-98904622 | 1491 | 9530003J22Rik | NM_029903.3 | chr10:117233752-117238681 |
| 1397 | 7420461P10Rik | NM_001177581.1 | chr1:162647242-162658219 | 1492 | 9530026F06Rik | NR_040483.1 | chr1:61378431-61395904 |
| 1398 | 7420700N18Rik | NR_046272.1 | chr8:31367748-31382438 | 1493 | 9530026P05Rik | NR_015530.2 | chr6:92940581-93111749 |
| 1399 | 7420701O03Rik | NR_045860.1 | chr12:11047812-11078741 | 1494 | 9530027J07Rik | NR_045916.1 | chrX:48276791-48285426 |
| 1400 | 7530416G11Rik | NM_001256072.1 | chr15:85492735-85503227 | 1495 | 9530036O11Rik | NR_015562.1 | chr5:28466983-28719209 |
| 1401 | 7630403G23Rik | NR_040744.1 | chr9:34042370-34059019 | 1496 | 9530051G07Rik | NR_040272.1 | chrX:153037628-153072915 |
| 1402 | 7630411F24Rik | NM_030135.2 | chr2:148782008-148785936 | 1497 | 9530052E02Rik | NR_046017.1 | chr8:11007849-11054541 |
| 1403 | 8030423F21Rik | NR_045738.1 | chr5:52607549-52619011 | 1498 | 9530053A07Rik | NM_001164655.1 | chr7:28129465-28164811 |
| 1404 | 8030423J24Rik | NM_029873.1 | chr13:70882947-70884503 | 1499 | 9530059O14Rik | NR_015610.1 | chr9:122572500-122580647 |
| 1405 | 8030442B05Rik | NR_040615.1 | chr2:11338365-11398500 | 1500 | 9530068E07Rik | NM_153117.2 | chr11:52396427-52408723 |
| 1406 | 8030443G20Rik | NR_040664.1 | chr4:108942842-108972077 | 1501 | 9530077C05Rik | NM_026739.1 | chr9:22413576-22444679 |
| 1407 | 8030462N17Rik | NM_178670.3 | chr18:77633280-77714010 | 1502 | 9530080O11Rik | NR_045776.1 | chr4:95959710-95967655 |
| 1408 | 8430408G22Rik | NM_001166580.1 | chr6:116650683-116652847 | 1503 | 9530082P21Rik | NR_015472.1 | chr17:23749235-23754065 |
| 1409 | 8430419L09Rik | NM_028982.4 | chr1:135197986-135236240 | 1504 | 9530091C08Rik | NR_033299.1 | chr9:68765345-68773322 |
| 1410 | 8430422H06Rik | NR_045373.1 | chr18:14232305-14278542 | 1505 | 9630001P10Rik | NR_102378.1 | chr5:45639274-45645469 |
| 1411 | 8430423G03Rik | NR_040686.1 | chr5:148950249-148951658 | 1506 | 9630013A20Rik | NR_015539.1 | chr14:84458837-84476424 |
| 1412 | 8430426J06Rik | NR_077229.1 | chr15:81242653-81247971 | 1507 | 9630028B13Rik | NR_038006.1 | chr1:185429356-185441819 |
| 1413 | 8430427H17Rik | NM_001001986.2 | chr2:153447460-153444479 | 1508 | 9630028B16Rik | NR_015544.2 | chr15:135583220-135583220 |
| 1414 | 8430429K09Rik | NR_028317.1 | chr11:3452436-3479831 | 1509 | 9630033F20Rik | NM_177003.1 | chr6:127085115-127109552 |
| 1415 | 8430431K14Rik | NR_002849.1 | chr19:31213542-31216396 | 1510 | 9830107B12Rik | NM_001177896.1 | chr17:48125604-48146307 |
| 1416 | 8430436N08Rik | NR_040645.1 | chr4:7560687-7573801 | 1511 | 9830132P13Rik | NR_040552.1 | chr3:127916170-127955220 |
| 1417 | 8430437L04Rik | NR_040503.1 | chr2:72703509-72729468 | 1512 | 9830147E19Rik | NM_001242388.1 | chr7:42609525-42642604 |
| 1418 | 9030025P20Rik | NM_001123370.1 | chr17:14978863-14991577 | 1513 | 9830166K06Rik | NR_045314.1 | chr19:8651795-8663335 |
| 1419 | 9030204H09Rik | NR_040618.1 | chr2:35819189-35823385 | 1514 | 9930012K11Rik | NM_001004155.2 | chr14:70154404-70159502 |
| 1420 | 9030404E10Rik | NR_045878.1 | chr16:30021841-30039479 | 1515 | 9930014A18Rik | NR_030696.1 | chr15:60822964-60831400 |
| 1421 | 9030612E09Rik | NR_102361.1 | chr10:43174698-43176565 | 1516 | 9930021J03Rik | NM_172836.3 | chr19:29714401-29806009 |

Fig. 26 - 9

| | | | | | | | | |
|---|---|---|---|---|---|---|---|---|
| 1517 | 9930104L06Rik | NM_177573.3 | chr4:124937047-124944661 | | 1612 | A730020E08Rik | NR_040287.1 | chr6:61175603-61180810 |
| 1518 | 9930111H07Rik | NR_108086.1 | chr1:85775270-85784694 | | 1613 | A730020M07Rik | NR_036456.1 | chr3:121634935-121643485 |
| 1519 | 9930111J21Rik1 | NM_001114679.1 | chr11:48946149-48979381 | | 1614 | A730036J17Rik | NR_045838.1 | chr2:129218968-129235606 |
| 1520 | 9930111J21Rik2 | NM_173434.1 | chr11:48965816-49051242 | | 1615 | A730043L09Rik | NR_040769.1 | chr9:62242595-62244100 |
| 1521 | a | NM_015770.3 | chr2:155013569-155051012 | | 1616 | A730046L19Rik | NR_040271.1 | chrX:144153694-144166274 |
| 1522 | A130010J15Rik | NM_001160359.1 | chr1:193173576-193177832 | | 1617 | A730056A06Rik | NR_040324.1 | chr7:73313805-73375774 |
| 1523 | A130077B15Rik | NR_040616.1 | chr10:122565022-122569891 | | 1618 | A730082K24Rik | NR_040317.1 | chr7:114948649-114983967 |
| 1524 | A1bg | NM_001081067.1 | chr15:60917588-60921270 | | 1619 | A730085K08Rik | NR_045967.1 | chr9:122382021-122398801 |
| 1525 | A1cf | NM_001081074.1 | chr19:31868760-31949406 | | 1620 | A730090H04Rik | NR_040279.1 | chr11:95145052-95159047 |
| 1526 | A230001M10Rik | NR_040391.1 | chr3:102262404-102288771 | | 1621 | A730090N16Rik | NR_040390.1 | chr3:65324019-65349429 |
| 1527 | A230009B12Rik | NR_077237.1 | chr17:10456215-10493057 | | 1622 | A730098P11Rik | NR_038091.1 | chr16:24529313-24534472 |
| 1528 | A230020J21Rik | NR_027298.1 | chr1:191025350-191029781 | | 1623 | A830009L08Rik | NR_045161.1 | chr13:91368989-91388085 |
| 1529 | A230028O05Rik | NR_040374.1 | chr16:25059638-25069058 | | 1624 | A830010M20Rik | NM_001007574.2 | chr5:107497744-107512556 |
| 1530 | A230046K03Rik | NM_001033375.2 | chr10:83543940-83596473 | | 1625 | A830018L16Rik | NM_001160369.2 | chr1:11414104-11975902 |
| 1531 | A230050P20Rik | NM_175687.2 | chr9:20868641-20874307 | | 1626 | A830019L24Rik | NR_040551.1 | chr3:143243054-143257996 |
| 1532 | A230056I06Rik | NR_045633.1 | chr13:59580175-59585223 | | 1627 | A830052O11Rik | NR_045403.1 | chr18:32359056-32378284 |
| 1533 | A230056P14Rik | NR_015245.2 | chr7:55962530-55980096 | | 1628 | A830080D01Rik | NM_001033472.2 | chrX:159532667-159593081 |
| 1534 | A230057D06Rik | NR_015533.2 | chr7:61705849-61927574 | | 1629 | A830082K12Rik | NR_045195.1 | chr13:78198016-78236564 |
| 1535 | A230065H16Rik | NM_001105103.1 | chr12:111406808-111412077 | | 1630 | A830082N09Rik | NR_015526.2 | chr10:33987215-33995055 |
| 1536 | A230070E04Rik | NR_045897.1 | chr14:68123751-68131371 | | 1631 | A930001A20Rik | NR_040549.1 | chr3:14971200-15002727 |
| 1537 | A230072C01Rik | NR_027445.1 | chrX:20961675-20987349 | | 1632 | A930001C03Rik | NR_045989.1 | chr19:4439558-4448325 |
| 1538 | A230072E10Rik | NR_015600.2 | chrX:151313334-151341879 | | 1633 | A930003A15Rik | NR_015488.1 | chr16:19876567-19884274 |
| 1539 | A230073K19Rik | NR_033229.1 | chr7:59281879-59289166 | | 1634 | A930003O13Rik | NR_027362.1 | chr5:22738910-22746884 |
| 1540 | A230077H06Rik | NR_040329.1 | chr7:40849152-40898324 | | 1635 | A930004D18Rik | NR_028376.1 | chr2:18025188-18037741 |
| 1541 | A230103J11Rik | NR_110581.1 | chr8:85053159-85060460 | | 1636 | A930005H10Rik | NR_015487.1 | chr3:115881578-115888130 |
| 1542 | A230108P19Rik | NR_040333.1 | chr2:6193250-6321611 | | 1637 | A930006I01Rik | NR_040332.1 | chr2:103338600-103372764 |
| 1543 | A2m | NM_175628.3 | chr6:121636172-121679238 | | 1638 | A930006K02Rik | NR_077219.1 | chr16:91465103-91470123 |
| 1544 | A330009N23Rik | NR_045326.1 | chr15:101221190-101224121 | | 1639 | A930007J19Rik | NR_015567.2 | chr19:29503662-29521987 |
| 1545 | A330021E22Rik | NM_172447.2 | chr5:5580981-5664232 | | 1640 | A930009A15Rik | NM_029982.1 | chr10:115569985-115582454 |
| 1546 | A330023F24Rik | NR_015566.2 | chr1:195017398-195037908 | | 1641 | A930011G23Rik | NR_030692.1 | chr5:99297243-99729060 |
| 1547 | A330032B11Rik | NR_045329.1 | chr19:37173842-37196541 | | 1642 | A930011O12Rik | NR_040709.1 | chr14:64588114-64593961 |
| 1548 | A330033J07Rik | NR_102303.1 | chr13:48044230-48262623 | | 1643 | A930012L18Rik | NR_026853.1 | chr18:44661664-44676271 |
| 1549 | A330035P11Rik | NR_015586.2 | chr14:122097938-122106974 | | 1644 | A930013F10Rik | NR_027886.1 | chr8:22634383-22636809 |
| 1550 | A330040F15Rik | NR_015503.1 | chr19:12585867-12596366 | | 1645 | A930015D03Rik | NR_015618.2 | chr17:35994503-36038174 |
| 1551 | A330041J22Rik | NR_045835.1 | chr9:86695441-86701253 | | 1646 | A930016O22Rik | NR_073014.1 | chr7:19417465-19421417 |
| 1552 | A330048O09Rik | NR_045162.1 | chr13:48272417-48273884 | | 1647 | A930017M01Rik | NR_033609.1 | chr15:44881393-44884743 |
| 1553 | A330049N07Rik | NR_040646.1 | chr10:72973302-73086705 | | 1648 | A930018P22Rik | NM_026634.2 | chr2:104122768-104124746 |
| 1554 | A330050F15Rik | NM_001145192.1 | chr17:69439325-69489233 | | 1649 | A930019D19Rik | NR_040619.1 | chr2:146259285-146267160 |
| 1555 | A330069I16Rik | NR_015464.1 | chr2:91237145-91238357 | | 1650 | A930024E05Rik | NR_045820.1 | chr5:122989353-122998341 |
| 1556 | A330070K13Rik | NM_198665.1 | chr5:130378850-130384631 | | 1651 | A930041C12Rik | NR_046195.1 | chr5:107630249-107633850 |
| 1557 | A330074K22Rik | NR_110496.1 | chr8:120204433-120228230 | | 1652 | AA387883 | NR_030678.1 | chr19:52923180-52926931 |
| 1558 | A330076C08Rik | NR_045088.1 | chr13:44193588-44216487 | | 1653 | AA388235 | NR_033305.1 | chr17:33981491-33985358 |
| 1559 | A330076H02Rik | NR_015599.2 | chr7:61943900-61982303 | | 1654 | AA413626 | NR_102683.1 | chr11:4918515-4918918 |
| 1560 | A330093E20Rik | NR_040342.1 | chr18:45683486-46045260 | | 1655 | AA414768 | NM_001272033.1 | chrX:12936872-12938541 |
| 1561 | A330102I10Rik | NR_045073.1 | chr13:29016254-29040336 | | 1656 | AA415398 | NM_001004178.1 | chr4:119530314-119538769 |
| 1562 | A3galt2 | NM_001099819.2 | chr4:128759257-128769298 | | 1657 | AA465934 | NR_028363.1 | chr11:83291698-83294637 |
| 1563 | A430005L14Rik | NM_001163019.1 | chr4:153957236-153961924 | | 1658 | AA467197 | NM_001004174.1 | chr2:122637886-122641076 |
| 1564 | A430033K04Rik | NM_180325.2 | chr5:138622858-138648905 | | 1659 | AA474331 | NR_033628.1 | chr10:39892759-39899238 |
| 1565 | A430035B10Rik | NR_040452.1 | chr6:8507058-8509161 | | 1660 | AA536875 | NR_045143.1 | chr14:123169185-123176176 |
| 1566 | A430078G23Rik | NM_001033378.3 | chr8:3353414-3390299 | | 1661 | AA543186 | NR_027448.1 | chr2:25327449-25332571 |
| 1567 | A430088P11Rik | NR_045309.1 | chr15:80691024-80697610 | | 1662 | AA543401 | NR_102273.1 | chr9:107192806-107194061 |
| 1568 | A430089I19Rik | NM_177913.4 | chr5:5184-94955288 | | 1663 | AA545190 | NR_033776.1 | chr6:10971467-10974378 |
| 1569 | A430093L17Rik | NR_045836.1 | chr13:114124347-114151592 | | 1664 | AA619741 | NR_033627.1 | chr1:346633534-346636210 |
| 1570 | A430093F15Rik | NR_027805.1 | chr19:10740946-10786043 | | 1665 | AA792892 | NM_178894.4 | chr5:94377339-94384334 |
| 1571 | A430105J19Rik | NM_001001982.2 | chr1:118754144-118762661 | | 1666 | AA986860 | NM_176604.3 | chr1:130731975-130744622 |
| 1572 | A430107P09Rik | NM_001105242.1 | chr14:53666005-53666506 | | 1667 | AA987161 | NM_001163246.2 | chr13:67589438-67609707 |
| 1573 | A4galt | NM_001004150.3 | chr15:83226721-83251774 | | 1668 | Aaas | NM_153416.2 | chr15:102338246-102350759 |
| 1574 | A4gnt | NM_001077424.2 | chr9:99612501-99622367 | | 1669 | Aacs | NM_030210.1 | chr5:125475872-125517403 |
| 1575 | A530006G24Rik | NR_046014.1 | chr2:147710692-147717632 | | 1670 | Aadac | NM_023383.1 | chr3:60031787-60040157 |
| 1576 | A530013C23Rik | NR_015500.3 | chr2:167691176-167697413 | | 1671 | Aadacl2 | NM_001128091.1 | chr3:60006742-60025420 |
| 1577 | A530016L24Rik | NM_177039.4 | chr12:112489447-112499927 | | 1672 | Aadacl3 | NM_001085503.2 | chr4:144453770-144463756 |
| 1578 | A530032D15Rik | NR_213615.2 | chr5:85088138-85108853 | | 1673 | Aadat | NM_018834.2 | chr8:60506123-60545677 |
| 1579 | A530046M15Rik | NR_046131.1 | chr13:15807242-15827537 | | 1674 | Aaed1 | NM_025370.2 | chr13:64291835-64312710 |
| 1580 | A530050N04Rik | NR_045419.1 | chr18:61470224-61484607 | | 1675 | Aagab | NM_025857.1 | chr9:63602654-63641889 |
| 1581 | A530053G22Rik | NR_015565.2 | chr6:60279042-60403707 | | 1676 | Aak1 | NM_001040106.2 | chr6:86849516-87003227 |
| 1582 | A530054K11Rik | NM_183146.3 | chr13:67617000-67837753 | | 1677 | Aamdc | NM_001177945.1 | chr7:97550330-97579497 |
| 1583 | A530058N18Rik | NR_028423.1 | chr2:114013564-114032292 | | 1678 | Aamp | NM_001190444.1 | chr1:74279839-74284738 |
| 1584 | A530064D06Rik | NM_001113556.1 | chr7:48151895-48167257 | | 1679 | Aanat | NM_009591.3 | chr11:116593686-116597680 |
| 1585 | A530065N20Rik | NR_046142.1 | chr13:60029710-60116669 | | 1680 | Aar2 | NM_001164818.1 | chr2:156547575-156568972 |
| 1586 | A530072M11Rik | NR_045765.2 | chr4:16164109-16266225 | | 1681 | Aard | NM_175503.3 | chr15:52040106-52045722 |
| 1587 | A530088E08Rik | NR_029458.1 | chr17:32403013-32404808 | | 1682 | Aars | NM_146217.4 | chr8:111033841-111055569 |
| 1588 | A530099J19Rik | NM_175688.4 | chr13:19727416-19732951 | | 1683 | Aars2 | NM_198608.2 | chr17:45506840-45520843 |
| 1589 | A630012I22Rik | NM_177055.3 | chr1:85717082-85736606 | | 1684 | Aarsd1 | NM_144829.1 | chr11:101408839-101417433 |
| 1590 | A630007B06Rik | NM_170757.1 | chr9:56790962-56813683 | | 1685 | Aasdh | NM_173765.3 | chr5:76875934-76905514 |
| 1591 | A630010A05Rik | NR_033556.1 | chr16:14562316-14621284 | | 1686 | Aasdhppt | NM_026276.3 | chr9:4294792-4309494 |
| 1592 | A630012P03Rik | NR_045367.2 | chrX:52575842-52619047 | | 1687 | Aass | NM_013930.4 | chr6:23072272-23132986 |
| 1593 | A630019I02Rik | NR_046182.1 | chr15:93094832-93098968 | | 1688 | Aatf | NM_019816.1 | chr11:84422855-84513501 |
| 1594 | A630020A06 | NR_045740.1 | chr15:3996038-4015858 | | 1689 | Aatk | NM_001198785.1 | chr11:120007315-120047145 |
| 1595 | A630023A22Rik | NM_001215843.1 | chr14:34051129-34102754 | | 1690 | AB041803 | NR_110469.1 | chr6:31165522-31218474 |
| 1596 | A630023P12Rik | NR_102290.1 | chr5:110514922-110525979 | | 1691 | AB124611 | NM_001198794.1 | chr9:21526176-21545331 |
| 1597 | A630033H20Rik | NM_001122595.1 | chrX:107149453-107173661 | | 1692 | Abat | NM_001170978.1 | chr16:8513428-8621567 |
| 1598 | A630066F11Rik | NR_030698.1 | chr10:7663370-7664623 | | 1693 | Abca1 | NM_013454.3 | chr4:53030788-53159895 |
| 1599 | A630072M18Rik | NR_030699.1 | chr5:20950988-20956398 | | 1694 | Abca12 | NM_175210.3 | chr1:71243089-71414910 |
| 1600 | A630073D07Rik | NM_001142969.1 | chr6:132625110-132627511 | | 1695 | Abca13 | NM_178259.3 | chr11:9191941-9684259 |
| 1601 | A630075F10Rik | NR_033632.1 | chr2:170061457-170070778 | | 1696 | Abca14 | NM_026458.4 | chr7:120203963-120325352 |
| 1602 | A630076J17Rik | NM_001256174.1 | chr3:107230613-107234031 | | 1697 | Abca15 | NM_177213.3 | chr7:120328683-120407687 |
| 1603 | A630077J23Rik | NR_015491.1 | chr4:43751858-43759464 | | 1698 | Abca16 | NM_001278943.1 | chr7:120409646-120544813 |
| 1604 | A630089N07Rik | NR_015491.1 | chr16:98062511-98082439 | | 1699 | Abca17 | NM_001031621.2 | chr17:24264278-24347252 |
| 1605 | A630095E13Rik | NM_001033325.2 | chr9:36635753-36638602 | | 1700 | Abca2 | NM_007379.2 | chr2:25428673-25448539 |
| 1606 | A630095N17Rik | NM_001243090.1 | chr17:75220094-75232093 | | 1701 | Abca3 | NM_001039581.2 | chr17:24352022-24410204 |
| 1607 | A730006G06Rik | NR_110485.1 | chr17:48064788-48090378 | | 1702 | Abca4 | NM_007378.1 | chr3:122044459-122180061 |
| 1608 | A730008H23Rik | NM_172505.4 | chr1:88264827-88277557 | | 1703 | Abca5 | NM_147219.2 | chr11:110269368-110337716 |
| 1609 | A730017C20Rik | NM_001167925.2 | chr18:59062380-59076960 | | 1704 | Abca6 | NM_001166556.1 | chr11:110236422-110251776 |
| 1610 | A730017L22Rik | NR_015523.2 | chr2:130872540-130906396 | | 1705 | Abca7 | NM_013850.1 | chr10:79997614-80015572 |
| 1611 | A730018C14Rik | NR_036459.1 | chr12:112411022-112423198 | | 1706 | Abca8a | NM_153145.4 | chr11:110025633-110095937 |

Fig. 26 - 10

| | | | | | | |
|---|---|---|---|---|---|---|
| 1707 | Abca8b | NM_013851.2 | chr11:109933405-109995816 | 1802 | Acbd3 | NM_133225.3 | chr1:180726042-180754204 |
| 1708 | Abca9 | NM_147220.2 | chr11:110100821-110168153 | 1803 | Acbd4 | NM_025988.2 | chr11:103101687-103112199 |
| 1709 | Abcb10 | NM_019552.2 | chr8:123952458-123983122 | 1804 | Acbd5 | NM_001102436.1 | chr2:23068200-23114512 |
| 1710 | Abcb11 | NM_021022.3 | chr2:69238281-69342616 | 1805 | Acbd6 | NM_001145781.1 | chr1:155558119-155587794 |
| 1711 | Abcb1a | NM_011076.2 | chr5:8660091-8748570 | 1806 | Acbd7 | NM_030063.2 | chr2:3336167-3340997 |
| 1712 | Abcb1b | NM_011075.2 | chr5:8798146-8866314 | 1807 | Accs | NM_001290782.1 | chr2:93833466-93849943 |
| 1713 | Abcb4 | NM_008830.2 | chr5:8893720-8959226 | 1808 | Accsl | NM_001033452.4 | chr2:93853359-93869157 |
| 1714 | Abcb5 | NM_029961.2 | chr12:118867823-118966421 | 1809 | Acd | NM_001012638.1 | chr8:105698158-105701095 |
| 1715 | Abcb6 | NM_023732.3 | chr1:75171640-75180392 | 1810 | Ace | NM_001281819.1 | chr11:105967944-105989964 |
| 1716 | Abcb7 | NM_009592.1 | chrX:104280564-104415846 | 1811 | Ace2 | NM_001130513.1 | chrX:164139341-164188418 |
| 1717 | Abcb8 | NM_029020.2 | chr5:24394155-24409947 | 1812 | Ace3 | NM_001101453.2 | chr11:105994674-106005443 |
| 1718 | Abcb9 | NM_019875.2 | chr5:124061856-124095798 | 1813 | Acer1 | NM_175731.4 | chr17:56953489-56982126 |
| 1719 | Abcc1 | NM_008576.3 | chr16:14361557-14474878 | 1814 | Acer2 | NM_001290541.1 | chr4:86874413-86920883 |
| 1720 | Abcc10 | NM_145140.2 | chr17:46303229-46325766 | 1815 | Acer3 | NM_025408.2 | chr7:98213659-98309527 |
| 1721 | Abcc12 | NM_172912.4 | chr8:86504840-86566590 | 1816 | Ache | NM_001290010.1 | chr5:137288253-137294466 |
| 1722 | Abcc2 | NM_013806.2 | chr19:43782307-43838218 | 1817 | Acin1 | NM_001085472.2 | chr14:54642160-54653701 |
| 1723 | Abcc3 | NM_029600.3 | chr11:94343294-94392976 | 1818 | Ackr1 | NM_010045.2 | chr1:173331885-173333503 |
| 1724 | Abcc4 | NM_001033336.3 | chr14:118482691-118706219 | 1819 | Ackr2 | NM_001276719.1 | chr9:121898354-121911071 |
| 1725 | Abcc5 | NM_013790.2 | chr16:20331303-20426394 | 1820 | Ackr3 | NM_001271607.1 | chr1:90203979-90215722 |
| 1726 | Abcc6 | NM_018795.2 | chr7:45976379-46030286 | 1821 | Ackr4 | NM_145700.2 | chr9:104098137-104126643 |
| 1727 | Abcc8 | NM_011510.3 | chr7:46104522-46180033 | 1822 | Acly | NM_001199296.1 | chr11:100476351-100528000 |
| 1728 | Abcc9 | NM_001044720.1 | chr6:142587861-142702274 | 1823 | Acmsd | NM_001033041.2 | chr1:127729412-127767564 |
| 1729 | Abcd1 | NM_007435.1 | chrX:73716596-73738287 | 1824 | Acn9 | NM_001077713.1 | chr6:6956017-7039220 |
| 1730 | Abcd2 | NM_011994.2 | chr15:91145870-91191807 | 1825 | Acnat1 | NM_001164565.1 | chr4:49443531-49451109 |
| 1731 | Abcd3 | NM_008593.2 | chr3:121758909-121815215 | 1826 | Acnat2 | NM_145368.2 | chr4:49379844-49408151 |
| 1732 | Abcd4 | NM_008992.2 | chr12:84602530-84617466 | 1827 | Aco1 | NM_007386.2 | chr4:40143264-40199009 |
| 1733 | Abce1 | NM_015751.2 | chr8:79683441-79711740 | 1828 | Aco2 | NM_080633.2 | chr15:81872462-81915137 |
| 1734 | Abcf1 | NM_013854.1 | chr17:35956818-35969750 | 1829 | Acot1 | NM_012006.2 | chr12:84009501-84017669 |
| 1735 | Abcf2 | NM_001190443.1 | chr5:24565340-24577467 | 1830 | Acot10 | NM_028816.2 | chr15:20665213-20666750 |
| 1736 | Abcf3 | NM_013852.2 | chr16:20548602-20561603 | 1831 | Acot11 | NM_025590.4 | chr4:106744560-106799831 |
| 1737 | Abcg1 | NM_009593.2 | chr17:31057593-31117981 | 1832 | Acot12 | NM_028790.3 | chr13:91741520-91786148 |
| 1738 | Abcg2 | NM_011920.3 | chr6:58596671-58692451 | 1833 | Acot13 | NM_025790.2 | chr13:24817954-24831489 |
| 1739 | Abcg3 | NM_030239.2 | chr5:104935056-104982717 | 1834 | Acot2 | NM_134188.3 | chr12:83987860-83993875 |
| 1740 | Abcg4 | NM_138955.3 | chr9:44273189-44288244 | 1835 | Acot3 | NM_134246.3 | chr12:84052150-84059564 |
| 1741 | Abcg5 | NM_031884.1 | chr17:84658233-84682923 | 1836 | Acot4 | NM_134247.3 | chr12:84038378-84044723 |
| 1742 | Abcg8 | NM_001286005.1 | chr17:84676301-84700333 | 1837 | Acot5 | NM_145444.3 | chr12:84069324-84076019 |
| 1743 | Abhd1 | NM_021304.3 | chr5:30950105-30955091 | 1838 | Acot6 | NM_172580.1 | chr12:84100653-84109783 |
| 1744 | Abhd10 | NM_001272070.1 | chr16:45729724-45742955 | 1839 | Acot7 | NM_001146057.1 | chr4:152186133-152271855 |
| 1745 | Abhd11 | NM_001190437.1 | chr5:135009151-135012195 | 1840 | Acot8 | NM_133240.2 | chr2:164792767-164804881 |
| 1746 | Abhd11os | NR_026688.1 | chr5:135012121-135013157 | 1841 | Acot9 | NM_019736.4 | chrX:155262442-155297654 |
| 1747 | Abhd12 | NM_024465.3 | chr2:150832514-150904731 | 1842 | Acox1 | NM_001271898.1 | chr11:116171882-116199045 |
| 1748 | Abhd12b | NM_001195033.1 | chr12:70154170-70183206 | 1843 | Acox2 | NM_001161667.1 | chr14:8225510-8258839 |
| 1749 | Abhd13 | NM_001081119.1 | chr8:9977716-9992154 | 1844 | Acox3 | NM_030721.2 | chr5:35583059-35613801 |
| 1750 | Abhd14a | NM_001110271.1 | chr9:106440050-106447678 | 1845 | Acoxl | NM_028765.3 | chr2:127854627-128123892 |
| 1751 | Abhd14b | NM_029193.3 | chr9:106446639-106452918 | 1846 | Acp1 | NM_001110239.1 | chr12:30893325-30911612 |
| 1752 | Abhd15 | NM_026185.4 | chr11:77515116-77520628 | 1847 | Acp2 | NM_007387.2 | chr2:91202911-91214098 |
| 1753 | Abhd16a | NM_178592.3 | chr17:35089290-35102987 | 1848 | Acp5 | NM_001102404.1 | chr9:22126726-22131865 |
| 1754 | Abhd16b | NM_183181.2 | chr2:181493205-181494980 | 1849 | Acp6 | NM_019800.4 | chr3:97158776-97176576 |
| 1755 | Abhd17a | NM_145421.2 | chr10:80583648-80590341 | 1850 | Acpp | NM_019807.2 | chr9:104298999-104337722 |
| 1756 | Abhd17b | NM_146096.3 | chr19:21653308-21685637 | 1851 | Acpt | NM_001195034.1 | chr7:44253086-44257204 |
| 1757 | Abhd17c | NM_133722.2 | chr7:84109355-84151893 | 1852 | Acr | NM_001205049.1 | chr15:89568325-89574585 |
| 1758 | Abhd2 | NM_018811.6 | chr7:79273265-79361601 | 1853 | Acrbp | NM_001127340.1 | chr6:125049976-125054193 |
| 1759 | Abhd3 | NM_134130.1 | chr18:10644410-10706696 | 1854 | Acrv1 | NM_007391.2 | chr9:36893219-36898837 |
| 1760 | Abhd4 | NM_001205181.1 | chr14:54254128-54269169 | 1855 | Acsbg1 | NM_053178.2 | chr9:54604996-54661885 |
| 1761 | Abhd5 | NM_026179.2 | chr9:122351615-122381523 | 1856 | Acsbg2 | NM_001039114.1 | chr17:56843103-56874447 |
| 1762 | Abhd6 | NM_025341.3 | chr14:8002901-8056555 | 1857 | Acsf2 | NM_153807.2 | chr11:94557101-94601786 |
| 1763 | Abhd8 | NM_022419.3 | chr8:71456699-71463657 | 1858 | Acsf3 | NM_144932.3 | chr8:122775504-122817881 |
| 1764 | Abi1 | NM_001077190.2 | chr2:22939988-23040241 | 1859 | Acsl1 | NM_007981.4 | chr8:46471036-46536051 |
| 1765 | Abi2 | NM_001198570.1 | chr1:60409618-60481163 | 1860 | Acsl3 | NM_001033606.2 | chr1:78657824-78707743 |
| 1766 | Abi3 | NM_001163464.1 | chr11:95830071-95842476 | 1861 | Acsl4 | NM_001033600.1 | chrX:142317992-142390535 |
| 1767 | Abi3bp | NM_001014399.2 | chr16:56477845-56690135 | 1862 | Acsl5 | NM_027976.2 | chr19:55253368-55296628 |
| 1768 | Abl1 | NM_001112703.2 | chr2:31688536-31804362 | 1863 | Acsl6 | NM_001033597.1 | chr11:54304203-54361539 |
| 1769 | Abl2 | NM_001136104.1 | chr1:156558786-156649619 | 1864 | Acsm1 | NM_054094.5 | chr7:119617827-119662515 |
| 1770 | Ablim1 | NM_001103177.2 | chr19:57033263-57197631 | 1865 | Acsm2 | NM_001177977.1 | chr7:119546339-119600694 |
| 1771 | Ablim2 | NM_001177696.1 | chr5:35757879-35884979 | 1866 | Acsm3 | NM_016870.3 | chr7:119760922-119784896 |
| 1772 | Ablim3 | NM_001164491.1 | chr18:61799392-61911852 | 1867 | Acsm4 | NM_178414.3 | chr7:119690025-119714566 |
| 1773 | Abo | NM_001290444.1 | chr2:26842502-26864995 | 1868 | Acsm5 | NM_178758.3 | chr7:119526264-119543360 |
| 1774 | Abr | NM_001291186.1 | chr11:76416731-76468465 | 1869 | Acss1 | NM_080575.2 | chr2:150618110-150668240 |
| 1775 | Abra | NM_175456.4 | chr15:41865292-41869720 | 1870 | Acss2 | NM_019811.3 | chr2:155518042-155562743 |
| 1776 | Abracl | NM_028440.1 | chr10:18011259-18023252 | 1871 | Acss2os | NR_040613.1 | chr2:155547039-155556930 |
| 1777 | Abt1 | NM_013924.3 | chr13:23418360-23423866 | 1872 | Acss3 | NM_001142804.1 | chr10:106936163-107123664 |
| 1778 | Abtb1 | NM_030251.3 | chr6:88835913-88841935 | 1873 | Acta1 | NM_001272041.1 | chr8:123891757-123894775 |
| 1779 | Abtb2 | NM_178890.3 | chr2:103566309-103718423 | 1874 | Acta2 | NM_007392.3 | chr19:34240335-34255373 |
| 1780 | Acaa1a | NM_130864.3 | chr9:119341293-119350295 | 1875 | Actb | NM_007393.5 | chr5:142903114-142906754 |
| 1781 | Acaa1b | NM_146230.3 | chr9:119148042-119157093 | 1876 | Actbl2 | NM_175497.3 | chr13:111255012-111257749 |
| 1782 | Acaa2 | NM_177470.3 | chr18:74779211-74806207 | 1877 | Actc1 | NM_009608.3 | chr2:114047283-114052875 |
| 1783 | Acaca | NM_133360.2 | chr11:84195437-84401651 | 1878 | Actg1 | NM_009609.3 | chr11:120345686-120348495 |
| 1784 | Acacb | NM_133904.2 | chr5:114165517-114257758 | 1879 | Actg2 | NM_009610.2 | chr6:83512908-83536251 |
| 1785 | Acad10 | NM_028037.4 | chr5:121621028-121660510 | 1880 | Actl10 | NM_001171640.1 | chr2:154551775-154553276 |
| 1786 | Acad11 | NM_175324.3 | chr9:104063702-104127646 | 1881 | Actl11 | NM_026338.3 | chr9:107928468-107932461 |
| 1787 | Acad12 | NM_178799.3 | chr5:121598280-121618938 | 1882 | Actl6a | NM_019673.2 | chr3:32708545-32726971 |
| 1788 | Acad8 | NM_025862.2 | chr9:26974138-26999549 | 1883 | Actl6b | NM_031404.4 | chr5:137553554-137569573 |
| 1789 | Acad9 | NM_172678.3 | chr3:36065999-36092857 | 1884 | Actl7a | NM_009611.3 | chr4:56743421-56744925 |
| 1790 | Acadl | NM_007381.4 | chr1:66830838-66863309 | 1885 | Actl7b | NM_025271.2 | chr4:56740004-56741425 |
| 1791 | Acadm | NM_007382.4 | chr3:153922352-153944643 | 1886 | Actl9 | NM_183282.2 | chr17:33432898-33434262 |
| 1792 | Acads | NM_007383.3 | chr5:115110298-115119346 | 1887 | Actn1 | NM_134156.2 | chr12:80167541-80260371 |
| 1793 | Acadsb | NM_025826.4 | chr7:131410600-131446211 | 1888 | Actn2 | NM_033268.4 | chr13:12269426-12340732 |
| 1794 | Acadvl | NM_017366.3 | chr11:70010182-70015428 | 1889 | Actn3 | NM_013456.2 | chr19:4861215-4877909 |
| 1795 | Acan | NM_007424.2 | chr7:79053482-79115099 | 1890 | Actn4 | NM_021895.2 | chr7:28893253-28962280 |
| 1796 | Acap1 | NM_153788.3 | chr11:69881566-69895539 | 1891 | Actr10 | NM_019785.2 | chr12:70937856-70964717 |
| 1797 | Acap2 | NM_030138.2 | chr16:31092412-31201238 | 1892 | Actr1a | NM_016860.1 | chr19:46376813-46395735 |
| 1798 | Acap3 | NM_207223.1 | chr4:155891874-155907251 | 1893 | Actr1b | NM_146107.2 | chr1:36699201-36709925 |
| 1799 | Acat1 | NM_144784.3 | chr9:53580521-53610350 | 1894 | Actr2 | NM_146243.2 | chr11:20062303-20112951 |
| 1800 | Acat2 | NM_009338.3 | chr17:12943041-12960725 | 1895 | Actr3 | NM_001205385.1 | chr1:125392904-125435727 |
| 1801 | Acat3 | NM_153151.3 | chr17:12923958-12940396 | 1896 | Actr3b | NM_001004365.2 | chr5:25759972-25850691 |

Fig. 26 - 11

| | | | | | | |
|---|---|---|---|---|---|---|
| 1897 | Actr5 | NM_175419.4 | chr2:158624912-158639211 | 1992 | Adcy3 | NM_001159536.1 | chr12:4133396-4213524 |
| 1898 | Actr6 | NM_025914.2 | chr10:89711972-89732295 | 1993 | Adcy4 | NM_080435.1 | chr14:55769091-55784019 |
| 1899 | Actr8 | NM_027493.3 | chr14:29978336-29993221 | 1994 | Adcy5 | NM_001012765.4 | chr16:35155635-35304549 |
| 1900 | Actrt1 | NM_028514.3 | chrX:46329006-46330345 | 1995 | Adcy6 | NM_007405.2 | chr15:98589985-98607633 |
| 1901 | Actrt2 | NM_028513.3 | chr4:154666427-154667867 | 1996 | Adcy7 | NM_001037723.3 | chr8:88289065-88329962 |
| 1902 | Actrt3 | NM_029690.2 | chr3:30597072-30599870 | 1997 | Adcy8 | NM_001291903.1 | chr15:64699034-64922296 |
| 1903 | Acvr1 | NM_001110204.1 | chr2:58446437-58566828 | 1998 | Adcy9 | NM_001291910.1 | chr16:4284885-4420498 |
| 1904 | Acvr1b | NM_007395.3 | chr15:101174124-101212601 | 1999 | Adcyap1 | NM_009625.3 | chr17:93199421-93205489 |
| 1905 | Acvr1c | NM_001033369.3 | chr2:58267452-58324807 | 2000 | Adcyap1r1 | NM_001025372.2 | chr6:55451977-55501455 |
| 1906 | Acvr2a | NM_007396.4 | chr2:48814108-48903264 | 2001 | Add1 | NM_001024458.3 | chr5:34573713-34632305 |
| 1907 | Acvr2b | NM_007397.3 | chr9:119402177-119442148 | 2002 | Add2 | NM_001271857.1 | chr6:86028680-86124409 |
| 1908 | Acvrl1 | NM_001277255.1 | chr15:101128521-101145336 | 2003 | Add3 | NM_001164099.2 | chr19:53140442-53247326 |
| 1909 | Acy1 | NM_001276442.1 | chr9:106432980-106438236 | 2004 | Adgb | NM_001127353.2 | chr10:10335702-10472314 |
| 1910 | Acy3 | NM_001302479.1 | chr19:3986570-3990007 | 2005 | Adh1 | NM_007409.2 | chr3:138277644-138290691 |
| 1911 | Acyp1 | NM_025421.2 | chr12:85272397-85280435 | 2006 | Adh4 | NM_011996.2 | chr3:138415496-138430892 |
| 1912 | Acyp2 | NM_029344.3 | chr11:30505991-30649396 | 2007 | Adh5 | NM_001288578.1 | chr3:138437199-138455499 |
| 1913 | Ada | NM_001272052.1 | chr2:163726570-163750239 | 2008 | Adh6a | NM_028945.1 | chr3:138313285-138331134 |
| 1914 | Adad1 | NM_009350.3 | chr3:37063655-37111512 | 2009 | Adh6-ps1 | NR_033581.1 | chr3:138374120-138388291 |
| 1915 | Adad2 | NM_029428.1 | chr8:119612746-119616926 | 2010 | Adh7 | NM_009626.4 | chr3:138217772-138232042 |
| 1916 | Adal | NM_001290811.1 | chr2:121140427-121156680 | 2011 | Adhfe1 | NM_175236.4 | chr1:9548045-9577968 |
| 1917 | Adam10 | NM_007399.3 | chr9:70679000-70780229 | 2012 | Adi1 | NM_134052.2 | chr12:28675206-28682174 |
| 1918 | Adam11 | NM_001110778.1 | chr11:102761438-102780262 | 2013 | Adig | NM_145635.2 | chr2:158502611-158508198 |
| 1919 | Adam12 | NM_007400.2 | chr7:133883198-134225097 | 2014 | Adipoq | NM_009605.4 | chr16:23146535-23157968 |
| 1920 | Adam15 | NM_001037722.2 | chr3:89339639-89350010 | 2015 | Adipor1 | NM_028320.4 | chr1:134415377-134433350 |
| 1921 | Adam17 | NM_001277269.1 | chr12:21323508-21373632 | 2016 | Adipor2 | NM_197985.3 | chr6:119353149-119417483 |
| 1922 | Adam18 | NM_010084.2 | chr8:24602245-24674755 | 2017 | Adk | NM_001243041.1 | chr14:21076151-21448569 |
| 1923 | Adam19 | NM_001291890.1 | chr11:46054501-46147347 | 2018 | Adm | NM_009627.1 | chr7:110627668-110629819 |
| 1924 | Adam1a | NM_172126.2 | chr5:121518603-121521695 | 2019 | Adm2 | NM_182928.5 | chr15:89322719-89324730 |
| 1925 | Adam1b | NM_172125.2 | chr5:121500096-121502980 | 2020 | Adnp | NM_009628.3 | chr2:168180964-168207112 |
| 1926 | Adam2 | NM_009618.2 | chr14:66027328-66077733 | 2021 | Adnp2 | NM_175028.1 | chr18:80127134-80151482 |
| 1927 | Adam20 | NM_001009548.2 | chr8:40793272-40797303 | 2022 | Ado | NM_001005419.2 | chr10:67544510-67548955 |
| 1928 | Adam21 | NM_020330.4 | chr12:81558583-81568474 | 2023 | Adora1 | NM_001008533.3 | chr1:134199214-134235457 |
| 1929 | Adam22 | NM_001007220.3 | chr5:8092259-8368160 | 2024 | Adora2a | NM_009630.3 | chr10:75316876-75334792 |
| 1930 | Adam23 | NM_001177600.1 | chr1:63445903-63573219 | 2025 | Adora2b | NM_007413.4 | chr11:62248983-62266452 |
| 1931 | Adam24 | NM_010086.4 | chr8:40675093-40682199 | 2026 | Adora3 | NM_001174169.2 | chr3:105870857-105908928 |
| 1932 | Adam25 | NM_011781.2 | chr8:40752207-40756176 | 2027 | Adpgk | NM_028121.2 | chr9:59291571-59316200 |
| 1933 | Adam26a | NM_010085.2 | chr8:43568275-43576707 | 2028 | Adprh | NM_007414.3 | chr16:38445398-38452689 |
| 1934 | Adam26b | NM_001009547.2 | chr8:43519863-43528137 | 2029 | Adprhl1 | NM_172750.3 | chr8:13235661-13254162 |
| 1935 | Adam28 | NM_001040175.2 | chr14:68604997-68655842 | 2030 | Adprhl2 | NM_133883.2 | chr4:126316350-126321703 |
| 1936 | Adam29 | NM_175939.3 | chr8:55870911-55906964 | 2031 | Adprm | NM_025510.3 | chr11:67037879-67052618 |
| 1937 | Adam3 | NM_009619.4 | chr8:24677233-24725825 | 2032 | Adra1a | NM_001271759.1 | chr14:66663250-66733462 |
| 1938 | Adam30 | NM_027665.1 | chr3:98160811-98163173 | 2033 | Adra1b | NM_001284380.1 | chr11:43774604-43901237 |
| 1939 | Adam32 | NM_153397.2 | chr8:24836142-24948804 | 2034 | Adra1d | NM_013460.4 | chr2:131543356-131562285 |
| 1940 | Adam33 | NM_001163529.1 | chr2:131050816-131063814 | 2035 | Adra2a | NM_007417.4 | chr19:54045181-54048982 |
| 1941 | Adam34 | NM_145745.2 | chr8:43650308-43665560 | 2036 | Adra2b | NM_009633.3 | chr2:127363285-127367221 |
| 1942 | Adam39 | NM_001025380.3 | chr8:40823008-40826861 | 2037 | Adra2c | NM_007418.3 | chr5:35278565-35281763 |
| 1943 | Adam4 | NM_009620.1 | chr12:81419548-81421878 | 2038 | Adrb1 | NM_007419.2 | chr19:56722371-56724862 |
| 1944 | Adam5 | NM_001272057.1 | chr8:24732983-24824369 | 2039 | Adrb2 | NM_007420.3 | chr18:62177712-62179981 |
| 1945 | Adam6a | NM_174885.3 | chr12:113543907-113546414 | 2040 | Adrb3 | NM_013462.3 | chr8:27225775-27229588 |
| 1946 | Adam6b | NM_001009545.1 | chr12:113489564-113491835 | 2041 | Adrbk1 | NM_001290818.1 | chr19:4285998-4306222 |
| 1947 | Adam7 | NM_007402.2 | chr14:68497336-68533689 | 2042 | Adrbk2 | NM_001285806.1 | chr5:112910477-113015538 |
| 1948 | Adam8 | NM_001291066.2 | chr7:139978931-139992562 | 2043 | Adrm1 | NM_019822.3 | chr2:180171587-180176283 |
| 1949 | Adam9 | NM_001270996.1 | chr8:24949610-25016922 | 2044 | Adsl | NM_009634.6 | chr15:80948489-80970947 |
| 1950 | Adamdec1 | NM_021475.2 | chr14:68563386-68582072 | 2045 | Adss | NM_007422.3 | chr1:177763177-177796509 |
| 1951 | Adamts1 | NM_009621.5 | chr16:85793827-85803113 | 2046 | Adssl1 | NM_007421.2 | chr12:112620046-112641355 |
| 1952 | Adamts10 | NM_172619.3 | chr17:33524195-33553782 | 2047 | Adtrp | NM_001145875.1 | chr13:41763147-41847616 |
| 1953 | Adamts12 | NM_175501.2 | chr15:11064789-11346867 | 2048 | Aebp1 | NM_001291857.2 | chr11:5861865-5872248 |
| 1954 | Adamts13 | NM_001001322.2 | chr2:26973415-27009625 | 2049 | Aebp2 | NM_001005605.2 | chr6:140623501-140655481 |
| 1955 | Adamts14 | NM_001081127.1 | chr10:61197111-61273438 | 2050 | Aen | NM_001162939.1 | chr7:78895926-78908833 |
| 1956 | Adamts15 | NM_001024139.1 | chr9:30899154-30922452 | 2051 | Aes | NM_001276288.1 | chr10:81559443-81566371 |
| 1957 | Adamts16 | NM_172053.2 | chr13:70727807-70841810 | 2052 | AF067061 | NM_199060.2 | chr13:120263094-120264517 |
| 1958 | Adamts17 | NM_001083877.4 | chr7:66839734-67152625 | 2053 | AF067063 | NM_001001449.2 | chr13:119827960-119830217 |
| 1959 | Adamts18 | NM_172466.2 | chr8:113698136-113848839 | 2054 | AF251705 | NM_134158.1 | chr11:114996768-115001880 |
| 1960 | Adamts19 | NM_175806.3 | chr18:58836763-59095678 | 2055 | AF357355 | NR_028433.2 | chr12:109654626-109654697 |
| 1961 | Adamts2 | NM_175643.3 | chr11:50602085-50807573 | 2056 | AF357359 | NR_028434.1 | chr12:109650708-109650738 |
| 1962 | Adamts20 | NM_001164785.1 | chr15:94320331-94404350 | 2057 | AF357399 | NR_028129.1 | chr7:28351539-28351633 |
| 1963 | Adamts3 | NM_001081401.2 | chr5:89673840-89883334 | 2058 | AF357425 | NR_046302.1 | chr12:109636011-109636080 |
| 1964 | Adamts4 | NM_172845.2 | chr1:171250421-171259922 | 2059 | AF357426 | NR_046303.1 | chr12:109642837-109642904 |
| 1965 | Adamts5 | NM_011782.2 | chr16:85858156-85901125 | 2060 | AF366264 | NM_153093.3 | chr18:13835230-13838089 |
| 1966 | Adamts6 | NM_001051020.1 | chr13:104287872-104494763 | 2061 | AF529169 | NM_153509.2 | chr9:89590304-89622986 |
| 1967 | Adamts7 | NM_001003911.2 | chr9:90162977-90200102 | 2062 | Afap1 | NM_027373.2 | chr5:35893318-36003922 |
| 1968 | Adamts8 | NM_013906.2 | chr9:30942562-30962858 | 2063 | Afap1l1 | NM_178928.4 | chr18:61730261-61786662 |
| 1969 | Adamts9 | NM_175314.3 | chr6:92772698-92901441 | 2064 | Afap1l2 | NM_001177796.1 | chr19:56912353-57008575 |
| 1970 | Adamtsl1 | NM_029967.3 | chr4:86053914-86428382 | 2065 | Aff1 | NM_001080798.2 | chr5:103754572-103855322 |
| 1971 | Adamtsl2 | NM_029981.1 | chr2:27079380-27108613 | 2066 | Aff2 | NM_008032.3 | chrX:69360330-69868037 |
| 1972 | Adamtsl3 | NM_001190374.1 | chr7:82355693-82614448 | 2067 | Aff3 | NM_001290814.1 | chr1:38175990-38627244 |
| 1973 | Adamtsl4 | NM_144899.3 | chr3:95676200-95687917 | 2068 | Aff4 | NM_033565.2 | chr11:53350766-53421830 |
| 1974 | Adamtsl5 | NM_001285435.1 | chr10:80339792-80348448 | 2069 | Afg3l1 | NM_054070.3 | chr8:123477861-123503916 |
| 1975 | Adap1 | NM_172723.4 | chr5:139217875-139325464 | 2070 | Afg3l2 | NM_027130.1 | chr18:67404763-67449136 |
| 1976 | Adap2 | NM_172133.1 | chr11:80154161-80178827 | 2071 | Afm | NM_145146.2 | chr5:90518948-90553544 |
| 1977 | Adar | NM_001038587.4 | chr3:89715021-89753455 | 2072 | Afmid | NM_027827.3 | chr11:117825918-117839908 |
| 1978 | Adarb1 | NM_001024837.2 | chr10:77290726-77418273 | 2073 | Afp | NM_007423.4 | chr5:90490713-90508907 |
| 1979 | Adarb2 | NM_001289530.1 | chr13:8202865-8760442 | 2074 | Aftph | NM_001252503.2 | chr11:20685084-20741556 |
| 1980 | Adat1 | NM_013925.4 | chr8:111966907-111992302 | 2075 | Aga | NM_001005847.2 | chr8:53511701-53523422 |
| 1981 | Adat2 | NM_001135299.1 | chr10:13552996-13563376 | 2076 | Agap1 | NM_001037136.1 | chr1:89454810-89895282 |
| 1982 | Adat3 | NM_001100606.1 | chr10:80602879-80607654 | 2077 | Agap2 | NM_001033263.5 | chr10:127078806-127093170 |
| 1983 | Adc | NM_172675.4 | chr4:128932016-128962455 | 2078 | Agap3 | NM_001256431.1 | chr5:24452176-24483184 |
| 1984 | Adck1 | NM_001277296.1 | chr12:88360513-88461726 | 2079 | Agbl1 | NM_001199224.1 | chr7:76229886-77124698 |
| 1985 | Adck2 | NM_178873.3 | chr6:39573875-39588769 | 2080 | Agbl2 | NM_178755.3 | chr2:90782743-90816231 |
| 1986 | Adck3 | NM_001163290.1 | chr1:180165237-180193485 | 2081 | Agbl3 | NM_001289656.1 | chr6:34780431-34859459 |
| 1987 | Adck4 | NM_133770.2 | chr7:27233012-27257949 | 2082 | Agbl4 | NM_001048189.4 | chr4:110397697-111657519 |
| 1988 | Adck5 | NM_172960.3 | chr15:76576358-76595811 | 2083 | Agbl5 | NM_001048192.2 | chr5:30889005-30906666 |
| 1989 | Adcy1 | NM_009622.1 | chr11:7063488-7178505 | 2084 | Ager | NM_001271422.1 | chr17:34597849-34600937 |
| 1990 | Adcy10 | NM_173029.3 | chr1:165485182-165576773 | 2085 | Agfg1 | NM_010472.3 | chr1:82839459-82901001 |
| 1991 | Adcy2 | NM_153534.2 | chr13:68620042-68999541 | 2086 | Agfg2 | NM_001303266.1 | chr5:137650463-137684806 |

Fig. 26 - 12

| | | | |
|---|---|---|---|
| 2087 | Aggf1 | NM_025630.3 | chr13:95350682-95375357 |
| 2088 | Agk | NM_023538.2 | chr6:40325477-40396762 |
| 2089 | Agl | NM_001081326.1 | chr3:116739998-116808166 |
| 2090 | Agmat | NM_001081408.1 | chr4:141746674-141759263 |
| 2091 | Agmo | NM_178767.5 | chr12:37241638-37581932 |
| 2092 | Ago1 | NM_153403.2 | chr4:126435012-126468421 |
| 2093 | Ago2 | NM_153178.4 | chr15:73101624-73184947 |
| 2094 | Ago3 | NM_153402.2 | chr4:126340677-126429542 |
| 2095 | Ago4 | NM_153177.3 | chr4:126489542-126533458 |
| 2096 | Agpat1 | NM_001163379.1 | chr17:34605860-34611449 |
| 2097 | Agpat2 | NM_026212.2 | chr2:26593056-26604417 |
| 2098 | Agpat3 | NM_053014.3 | chr10:78271562-78351700 |
| 2099 | Agpat4 | NM_026644.2 | chr17:12119283-12219640 |
| 2100 | Agpat5 | NM_026792.3 | chr8:18846278-18884413 |
| 2101 | Agpat6 | NM_018743.4 | chr8:23172945-23208453 |
| 2102 | Agpat9 | NM_172715.3 | chr5:100846228-100899102 |
| 2103 | Agps | NM_172666.3 | chr2:75832176-75931350 |
| 2104 | Agr2 | NM_011783.2 | chr12:35992924-36004081 |
| 2105 | Agr3 | NM_207531.3 | chr12:35925620-35949730 |
| 2106 | Agrn | NM_021604.3 | chr4:156165289-156197488 |
| 2107 | Agrp | NM_001271806.1 | chr8:105566694-105579845 |
| 2108 | Agt | NM_007428.3 | chr8:124556586-124569707 |
| 2109 | Agtpbp1 | NM_001048008.2 | chr13:59493403-59557347 |
| 2110 | Agtr1a | NM_177322.3 | chr13:30336355-30382867 |
| 2111 | Agtr1b | NM_175086.3 | chr3:20314472-20367177 |
| 2112 | Agtr2 | NM_007429.5 | chrX:21484623-21488833 |
| 2113 | Agtrap | NM_009642.4 | chr4:148077060-148088064 |
| 2114 | Agxt | NM_001276710.1 | chr1:93135239-93145421 |
| 2115 | Agxt2 | NM_001031851.1 | chr15:10358578-10409738 |
| 2116 | Ahctf1 | NM_026375.2 | chr1:179744903-179804015 |
| 2117 | Ahcy | NM_016661.3 | chr2:155059311-155074497 |
| 2118 | Ahcyl1 | NM_145542.3 | chr3:107663119-107696548 |
| 2119 | Ahcyl2 | NM_001171000.2 | chr6:29768442-29912310 |
| 2120 | Ahdc1 | NM_146155.3 | chr4:133011505-133078110 |
| 2121 | Ahi1 | NM_001177776.1 | chr10:21040819-21080429 |
| 2122 | Ahnak | NM_001039959.2 | chr19:8989283-9076926 |
| 2123 | Ahr | NM_013464.4 | chr12:35497978-35534989 |
| 2124 | Ahrr | NM_009644.2 | chr13:74211117-74292309 |
| 2125 | Ahsa1 | NM_146036.1 | chr12:87266727-87273952 |
| 2126 | Ahsa2 | NM_001200654.1 | chr11:23487881-23498039 |
| 2127 | Ahsg | NM_001276449.1 | chr16:22892014-22898451 |
| 2128 | AI115009 | NR_040386.1 | chr3:152666912-152681432 |
| 2129 | AI118078 | NM_172923.3 | chr9:55326948-55438344 |
| 2130 | AI182371 | NM_001243102.1 | chr2:35081860-35100685 |
| 2131 | AI197445 | NR_045083.1 | chr13:107469821-107479188 |
| 2132 | AI314180 | NM_172381.2 | chr4:58800030-58912725 |
| 2133 | AI314278 | NR_102276.1 | chr7:89426305-89432077 |
| 2134 | AI317395 | NM_144821.4 | chr10:40001572-40025268 |
| 2135 | AI413582 | NM_001002895.2 | chr17:27563768-27565727 |
| 2136 | AI414108 | NR_027907.1 | chr9:27352684-27357543 |
| 2137 | AI427809 | NR_033139.1 | chr4:53261355-53270232 |
| 2138 | AI429214 | NM_001039220.3 | chr8:36993574-36995533 |
| 2139 | AI450353 | NR_028364.1 | chr11:83293429-83284929 |
| 2140 | AI462493 | NM_001160356.1 | chr19:8880013-8880933 |
| 2141 | AI463170 | NR_046044.1 | chr12:76546971-76547925 |
| 2142 | AI464131 | NM_001086515.2 | chr4:41495600-41503075 |
| 2143 | AI467606 | NM_178901.3 | chr7:127091435-127094049 |
| 2144 | AI504432 | NR_033498.1 | chr3:107039503-107054322 |
| 2145 | AI506816 | NR_035554.2 | chr5:23692260-23712667 |
| 2146 | AI507597 | NR_033566.1 | chr4:141614369-141615604 |
| 2147 | AI593442 | NM_001286641.1 | chr9:52673031-52679780 |
| 2148 | AI597479 | NM_133818.1 | chr1:43098709-43115946 |
| 2149 | AI606473 | NR_040387.1 | chr3:154330820-154334687 |
| 2150 | AI607873 | NM_001204910.1 | chr1:173723427-173741809 |
| 2151 | AI646519 | NM_040330.1 | chr2:147361542-147362793 |
| 2152 | AI661453 | NM_145489.2 | chr17:47436638-47470638 |
| 2153 | AI662270 | NR_015519.1 | chr11:83223575-83226584 |
| 2154 | AI747448 | NM_001033199.3 | chr3:144910920-144932529 |
| 2155 | AI837181 | NM_001256515.1 | chr19:5425143-5427316 |
| 2156 | AI839979 | NR_102275.1 | chr5:31569591-31571397 |
| 2157 | AI846148 | NM_001033139.3 | chr19:7356463-7383026 |
| 2158 | AI847159 | NR_045264.1 | chr2:129178147-129180673 |
| 2159 | AI848285 | NM_001207021.1 | chr15:82206951-82212815 |
| 2160 | AI854517 | NR_040311.1 | chr7:79500025-79534403 |
| 2161 | AI854703 | NR_027236.1 | chr6:48628166-48633688 |
| 2162 | AI987944 | NM_001199330.1 | chr7:41392929-41393379 |
| 2163 | Aicda | NM_009645.2 | chr6:122553808-122564180 |
| 2164 | Aida | NM_181732.4 | chr1:183297059-183324501 |
| 2165 | Aif1 | NM_019467.2 | chr17:35170991-35176001 |
| 2166 | Aif1l | NM_145144.1 | chr2:31950302-31973442 |
| 2167 | Aifm1 | NM_001290364.1 | chrX:48474943-48513563 |
| 2168 | Aifm2 | NM_001081954.1 | chr10:61715262-61738652 |
| 2169 | Aifm3 | NM_001291070.1 | chr16:17491920-17507482 |
| 2170 | Aig1 | NM_025446.3 | chr10:13652708-13868830 |
| 2171 | Aim1 | NM_172393.3 | chr10:43950396-44004846 |
| 2172 | Aim1l | NM_001162970.1 | chr4:134068451-134092504 |
| 2173 | Aim2 | NM_001013779.2 | chr1:173420603-173466036 |
| 2174 | Aimp1 | NM_007926.2 | chr3:132660497-132683879 |
| 2175 | Aimp2 | NM_001172146.1 | chr5:143902703-143909839 |
| 2176 | Aip | NM_001276284.1 | chr19:4113755-4121575 |
| 2177 | Aipl1 | NM_053245.2 | chr11:72028721-72037509 |
| 2178 | Aire | NM_001271549.1 | chr10:78030021-78043610 |
| 2179 | Airn | NR_028532 | chr17:12741310-12815557 |
| 2180 | Ajap1 | NM_001099299.1 | chr4:153373220-153482830 |
| 2181 | Ajuba | NM_010590.5 | chr14:54567468-54577661 |
| 2182 | AK010878 | NM_001142938.1 | chr12:102753274-102757810 |
| 2183 | Ak1 | NM_001198790.1 | chr2:32621757-32635058 |
| 2184 | AK129341 | NM_001045524.1 | chr9:8076632-8134294 |
| 2185 | Ak2 | NM_001033966.4 | chr4:128993223-129008723 |
| 2186 | Ak3 | NM_021299.1 | chr19:29020831-29047902 |
| 2187 | Ak4 | NM_001177602.1 | chr4:101419288-101467771 |
| 2188 | Ak5 | NM_001081277.1 | chr3:152462814-152668140 |
| 2189 | Ak6 | NM_027592.3 | chr13:100651342-100666415 |
| 2190 | Ak7 | NM_030187.1 | chr12:105705981-105782447 |
| 2191 | Ak8 | NM_001033874.2 | chr2:28700160-28813165 |
| 2192 | Akap1 | NM_001042541.1 | chr11:88830791-88864586 |
| 2193 | Akap10 | NM_019921.3 | chr11:61871306-61930257 |
| 2194 | Akap11 | NM_001164503.1 | chr14:78492245-78536860 |
| 2195 | Akap12 | NM_031185.3 | chr10:4268328-4359471 |
| 2196 | Akap13 | NM_029332.1 | chr7:75455533-75754609 |
| 2197 | Akap14 | NM_001033785.2 | chrX:37150697-37168842 |
| 2198 | Akap17b | NM_001081956.1 | chrX:36608182-36645414 |
| 2199 | Akap2 | NM_001035532.2 | chr4:57845247-57896984 |
| 2200 | Akap3 | NM_009650.2 | chr6:126853097-126874308 |
| 2201 | Akap4 | NM_001042542.2 | chrX:7068209-7078606 |
| 2202 | Akap5 | NM_001101471.1 | chr12:76324890-76334151 |
| 2203 | Akap6 | NM_198111.2 | chr12:52699982-53151015 |
| 2204 | Akap7 | NM_018747.4 | chr10:25169089-25299163 |
| 2205 | Akap8 | NM_019774.5 | chr17:32303671-32321238 |
| 2206 | Akap8l | NM_017476.2 | chr17:32321423-32350577 |
| 2207 | Akap9 | NM_194462.2 | chr5:3928185-4080204 |
| 2208 | Akip1 | NM_020616.1 | chr7:109703736-109712181 |
| 2209 | Akirin1 | NM_023423.3 | chr4:123735194-123750299 |
| 2210 | Akirin2 | NM_001007589.3 | chr4:34550614-34566908 |
| 2211 | Akna | NM_001045514.3 | chr4:63367122-63403445 |
| 2212 | Aknad1 | NM_177859.3 | chr3:108799657-108782309 |
| 2213 | Akp3 | NM_007432.2 | chr1:87125007-87127912 |
| 2214 | Akr1a1 | NM_021473.3 | chr4:116636509-116651674 |
| 2215 | Akr1b10 | NM_172398.3 | chr6:34384246-34396949 |
| 2216 | Akr1b3 | NM_009658.3 | chr6:34303929-34317489 |
| 2217 | Akr1b7 | NM_009731.2 | chr6:34412861-34423137 |
| 2218 | Akr1b8 | NM_008012.1 | chr6:34354163-34368454 |
| 2219 | Akr1c12 | NM_013777.2 | chr13:4268171-4279399 |
| 2220 | Akr1c13 | NM_013778.2 | chr13:4191186-4205603 |
| 2221 | Akr1c14 | NM_134072.1 | chr13:4059590-4090422 |
| 2222 | Akr1c18 | NM_134066.2 | chr13:4132626-4150631 |
| 2223 | Akr1c19 | NM_001013785.3 | chr13:4233739-4248359 |
| 2224 | Akr1c20 | NM_054080.1 | chr13:4507158-4523333 |
| 2225 | Akr1c21 | NM_029901.2 | chr13:4574074-4586543 |
| 2226 | Akr1c6 | NM_030611.3 | chr13:4434342-4457530 |
| 2227 | Akr1d1 | NM_027582.4 | chr6:65013077-65032759 |
| 2228 | Akr1d1 | NM_145364.2 | chr6:37530172-37568815 |
| 2229 | Akr1e1 | NM_018859.2 | chr13:4592489-4609164 |
| 2230 | Akr7a5 | NM_025337.3 | chr4:139310743-139318786 |
| 2231 | Akt1 | NM_001165894.1 | chr12:112653820-112674276 |
| 2232 | Akt1s1 | NM_001253920.1 | chr7:44850006-44855421 |
| 2233 | Akt2 | NM_001110208.1 | chr7:27591559-27639453 |
| 2234 | Akt3 | NM_011785.3 | chr1:177022114-177248767 |
| 2235 | Aktip | NM_010241.5 | chr8:91123498-91135494 |
| 2236 | Alad | NM_001276446.1 | chr4:62505983-62519909 |
| 2237 | Alas1 | NM_001291835.1 | chr9:106233454-106247730 |
| 2238 | Alas2 | NM_001102446.1 | chrX:150547416-150570622 |
| 2239 | Alb | NM_009654.4 | chr5:90460888-90476603 |
| 2240 | Alcam | NM_009655.2 | chr16:52248995-52452997 |
| 2241 | Aldh16a1 | NM_145954.1 | chr7:45141839-45154538 |
| 2242 | Aldh18a1 | NM_019698.2 | chr19:40550256-40588463 |
| 2243 | Aldh1a1 | NM_013467.3 | chr19:20601981-20643462 |
| 2244 | Aldh1a2 | NM_009022.4 | chr9:71215788-71296243 |
| 2245 | Aldh1a3 | NM_053080.3 | chr7:66390892-66427477 |
| 2246 | Aldh1a7 | NM_011921.2 | chr19:20692952-20727556 |
| 2247 | Aldh1b1 | NM_028270.4 | chr4:45799021-45804608 |
| 2248 | Aldh1l1 | NM_027406.1 | chr6:90550847-90599171 |
| 2249 | Aldh1l2 | NM_153543.2 | chr10:83487446-83534140 |
| 2250 | Aldh2 | NM_009656.4 | chr5:121566026-121593824 |
| 2251 | Aldh3a1 | NM_001112725.1 | chr11:61208741-61218416 |
| 2252 | Aldh3a2 | NM_007437.5 | chr11:61244751-61267186 |
| 2253 | Aldh3b1 | NM_026316.2 | chr19:3913490-3929716 |
| 2254 | Aldh3b2 | NM_001177438.1 | chr19:3972327-3981665 |
| 2255 | Aldh4a1 | NM_175438.4 | chr4:139622893-139649691 |
| 2256 | Aldh5a1 | NM_172532.3 | chr13:24907578-24937661 |
| 2257 | Aldh6a1 | NM_134042.3 | chr12:84430720-84451024 |
| 2258 | Aldh7a1 | NM_001127338.1 | chr18:56525735-56572939 |
| 2259 | Aldh8a1 | NM_178713.4 | chr10:21377299-21396578 |
| 2260 | Aldh9a1 | NM_019993.3 | chr1:167349990-167368530 |
| 2261 | Aldoa | NM_001177307.1 | chr7:126795233-126799178 |
| 2262 | Aldoart1 | NM_001199270.1 | chr4:72850582-72852634 |
| 2263 | Aldoart2 | NM_001277340.1 | chr12:55565204-55566896 |
| 2264 | Aldob | NM_144903.3 | chr4:49535992-49549546 |
| 2265 | Aldoc | NM_009657.4 | chr11:78324197-78327778 |
| 2266 | Alg1 | NM_145362.2 | chr16:5233620-5244907 |
| 2267 | Alg10b | NM_001033441.3 | chr15:90224310-90230554 |
| 2268 | Alg11 | NM_001243161.1 | chr8:22060720-22071627 |
| 2269 | Alg12 | NM_001142357.1 | chr15:88805242-88819318 |
| 2270 | Alg13 | NM_026247.3 | chrX:144317965-144325197 |
| 2271 | Alg14 | NM_024178.2 | chr3:121291816-121362011 |
| 2272 | Alg2 | NM_019998.3 | chr4:47469832-47474367 |
| 2273 | Alg3 | NM_145939.2 | chr16:20605457-20610749 |
| 2274 | Alg5 | NM_025442.3 | chr3:54735538-54749795 |
| 2275 | Alg6 | NM_001081264.1 | chr4:99715629-99763460 |
| 2276 | Alg8 | NM_199035.2 | chr7:97371616-97392158 |

Fig. 26 - 13

| # | Gene | Accession | Location |
|---|---|---|---|
| 2277 | Alg9 | NM_133981.2 | chr9:50775224-50843639 |
| 2278 | Alk | NM_007439.2 | chr17:71868987-72604307 |
| 2279 | Alkbh1 | NM_001102565.1 | chr12:87428077-87443839 |
| 2280 | Alkbh2 | NM_175016.2 | chr5:114123933-114128176 |
| 2281 | Alkbh3 | NM_026944.1 | chr2:93980633-94010730 |
| 2282 | Alkbh4 | NM_028070.1 | chr5:136138786-136141614 |
| 2283 | Alkbh5 | NM_172943.4 | chr11:60537682-60558512 |
| 2284 | Alkbh6 | NM_198027.2 | chr7:30308752-30314303 |
| 2285 | Alkbh7 | NM_025538.3 | chr17:56997338-56999336 |
| 2286 | Alkbh8 | NM_026303.1 | chr9:3335230-3385846 |
| 2287 | Allc | NM_053156.2 | chr12:28553755-28582483 |
| 2288 | Alms1 | NM_145223.2 | chr6:85587530-85702751 |
| 2289 | Alms1-ps2 | NR_040440.2 | chr6:85792116-85804057 |
| 2290 | Alox12 | NM_007440.4 | chr11:70241454-70255341 |
| 2291 | Alox12b | NM_009659.2 | chr11:69157071-69169791 |
| 2292 | Alox12e | NM_145684.1 | chr11:70315612-70322518 |
| 2293 | Alox15 | NM_009660.3 | chr11:70344146-70352031 |
| 2294 | Alox5 | NM_009662.2 | chr6:116410070-116461178 |
| 2295 | Alox5ap | NM_009663.2 | chr5:149265003-149288153 |
| 2296 | Alox8 | NM_009661.4 | chr11:69183884-69197843 |
| 2297 | Aloxe3 | NM_011786.2 | chr11:69126376-69149115 |
| 2298 | Alpi | NM_001081082.2 | chr1:87098001-87101606 |
| 2299 | Alpk1 | NM_027808.1 | chr3:127670309-127780527 |
| 2300 | Alpk2 | NM_001037294.1 | chr18:65265530-65393888 |
| 2301 | Alpk3 | NM_054085.2 | chr7:81057599-81105612 |
| 2302 | Alpl | NM_001287172.1 | chr4:137741730-137766475 |
| 2303 | Alppl2 | NM_007433.3 | chr1:87086690-87089928 |
| 2304 | Als2 | NM_001159948.2 | chr1:59162755-59237093 |
| 2305 | Als2cl | NM_001146059.1 | chr9:110880173-110909530 |
| 2306 | Als2cr11 | NM_175200.4 | chr1:59050505-59094900 |
| 2307 | Als2cr12 | NM_175370.5 | chr1:58658120-58695989 |
| 2308 | Alx1 | NM_172553.4 | chr10:103007846-103028777 |
| 2309 | Alx3 | NM_007441.3 | chr3:107595030-107605875 |
| 2310 | Alx4 | NM_007442.3 | chr2:93642433-93681339 |
| 2311 | Alyref | NM_011568.1 | chr11:120594515-120598365 |
| 2312 | Alyref2 | NM_019484.4 | chr1:171503477-171504750 |
| 2313 | Amacr | NM_008537.4 | chr15:10981755-10996624 |
| 2314 | Ambn | NM_009664.2 | chr5:88455990-88468529 |
| 2315 | Ambp | NM_007443.4 | chr4:63143278-63154142 |
| 2316 | Ambra1 | NM_001080754.1 | chr2:91730137-91918849 |
| 2317 | Amd1 | NM_009665.5 | chr10:40287457-40302188 |
| 2318 | Amd2 | NM_007464.4 | chr10:40287464-40302186 |
| 2319 | Amdhd1 | NM_027908.1 | chr10:93523337-93540033 |
| 2320 | Amdhd2 | NM_172935.4 | chr17:24155832-24163733 |
| 2321 | Amelx | NM_001081978.2 | chrX:169176113-169187209 |
| 2322 | Amer1 | NM_175179.4 | chrX:95420313-95444840 |
| 2323 | Amer2 | NM_001164705.1 | chr14:60378285-60381003 |
| 2324 | Amer3 | NM_213727.2 | chr1:34579692-34590944 |
| 2325 | Amfr | NM_011787.2 | chr8:93971587-94012640 |
| 2326 | Amh | NM_007445.2 | chr10:80805247-80807648 |
| 2327 | Amhr2 | NM_144547.2 | chr15:102445356-102454639 |
| 2328 | Amica1 | NM_001005421.4 | chr9:45079182-45108531 |
| 2329 | Amigo1 | NM_001042932 | chr3:108186288-108192286 |
| 2330 | Amigo2 | NM_001164563.1 | chr15:97244073-97247287 |
| 2331 | Amigo3 | NM_177275.4 | chr9:108053158-108055701 |
| 2332 | Ammecr1 | NM_019496.3 | chrX:142853473-142966728 |
| 2333 | Ammecr1l | NM_001242430.1 | chr18:31760615-31784083 |
| 2334 | Amn | NM_033603.3 | chr12:111271095-111276426 |
| 2335 | Amn1 | NM_001113424.1 | chr6:149157576-149188712 |
| 2336 | Amot | NM_001290274.1 | chrX:145451867-145487639 |
| 2337 | Amotl1 | NM_001081395.1 | chr9:14541966-14615000 |
| 2338 | Amotl2 | NM_019764.2 | chr12:102717803-102733417 |
| 2339 | Ampd1 | NM_001303303.2 | chr3:103074013-103099720 |
| 2340 | Ampd2 | NM_001289719.1 | chr3:108074061-108086666 |
| 2341 | Ampd3 | NM_001276301.1 | chr7:110768205-110812408 |
| 2342 | Amph | NM_001289546.1 | chr13:18948350-19150919 |
| 2343 | Amt | NM_001013814.1 | chr9:108296921-108301597 |
| 2344 | Amth | NM_883876.107 | chr6:88376107-88385916 |
| 2345 | Amy1 | NM_001110505.1 | chr3:113555951-113577750 |
| 2346 | Amy2a2 | NM_001260152.1 | chr3:113279836-113356658 |
| 2347 | Amy2a5 | NM_001042711.2 | chr3:113249177-113356520 |
| 2348 | Amy2b | NM_001190403.1 | chr3:113147655-113156727 |
| 2349 | Amz1 | NM_173544.2 | chr5:140724126-140753312 |
| 2350 | Amz2 | NM_001252193.1 | chr11:109426219-109438148 |
| 2351 | Anapc1 | NM_008569.2 | chr2:128610082-128687395 |
| 2352 | Anapc10 | NM_026904.2 | chr8:79711819-79777321 |
| 2353 | Anapc11 | NM_001088230.2 | chr11:120598531-120608198 |
| 2354 | Anapc13 | NM_181394.3 | chr9:102626295-102634244 |
| 2355 | Anapc15 | NM_001286062.1 | chr7:101896330-101899545 |
| 2356 | Anapc16 | NM_025514.2 | chr10:59987908-60003112 |
| 2357 | Anapc2 | NM_175300.4 | chr2:25272465-25285916 |
| 2358 | Anapc4 | NM_024213.2 | chr5:52834134-52866734 |
| 2359 | Anapc5 | NM_001042491.2 | chr5:122787460-122821342 |
| 2360 | Anapc7 | NM_019805.4 | chr5:122422443-122444911 |
| 2361 | Ang | NM_001161731.2 | chr14:51091076-51102009 |
| 2362 | Ang2 | NM_007449.2 | chr14:51195485-51195923 |
| 2363 | Ang3 | NM_001123394.2 | chr14:43957068-43963080 |
| 2364 | Ang4 | NM_177544.4 | chr14:51763891-51773590 |
| 2365 | Ang5 | NM_007448.3 | chr14:43957068-43963080 |
| 2366 | Ang6 | NM_001011876.2 | chr14:44001663-44006418 |
| 2367 | Angel1 | NM_144524.2 | chr12:86700501-86726460 |
| 2368 | Angel2 | NM_001199020.1 | chr1:190925107-190946491 |
| 2369 | Angpt1 | NM_001286062.1 | chr15:42424666-42676977 |
| 2370 | Angpt2 | NM_007426.4 | chr8:18690262-18741562 |
| 2371 | Angpt4 | NM_009641.1 | chr2:151911331-151944654 |
| 2372 | Angptl1 | NM_028333.2 | chr1:156839022-156861079 |
| 2373 | Angptl2 | NM_011923.4 | chr2:33215960-33247714 |
| 2374 | Angptl3 | NM_013913.4 | chr4:99030953-99038192 |
| 2375 | Angptl4 | NM_020581.2 | chr17:33774899-33781575 |
| 2376 | Angptl6 | NM_145154.2 | chr9:20873808-20879710 |
| 2377 | Angptl7 | NM_001039554.3 | chr4:148495279-148500462 |
| 2378 | Ank | NM_020332.4 | chr15:27466676-27594907 |
| 2379 | Ank1 | NM_001110783.3 | chr8:22974835-23150497 |
| 2380 | Ank2 | NM_001034168.1 | chr3:126921606-126943386 |
| 2381 | Ank3 | NM_009670.4 | chr10:69925531-70027436 |
| 2382 | Ankar | NM_176980.4 | chr1:72642979-72700564 |
| 2383 | Ankdd1b | NM_001042714.1 | chr13:96416133-96471160 |
| 2384 | Ankef1 | NM_175667.4 | chr2:136532320-136555854 |
| 2385 | Ankfn1 | NM_001080933.1 | chr11:89421085-89538555 |
| 2386 | Ankfy1 | NM_009671.5 | chr11:72690001-72772146 |
| 2387 | Ankhd1 | NM_175375.3 | chr18:36560802-36658908 |
| 2388 | Ankib1 | NM_001003909.4 | chr5:3689998-3803124 |
| 2389 | Ankk1 | NM_172922.3 | chr9:49415221-49427021 |
| 2390 | Ankle1 | NM_172755.4 | chr8:71406011-71410542 |
| 2391 | Ankle2 | NM_001253814.1 | chr5:110231003-110256651 |
| 2392 | Ankmy1 | NM_172850.3 | chr1:92870128-92902906 |
| 2393 | Ankmy2 | NM_146033.3 | chr12:36157123-36197291 |
| 2394 | Ankra2 | NM_001271388.1 | chr13:98263075-98273918 |
| 2395 | Ankrd1 | NM_013468.3 | chr19:36111964-36119844 |
| 2396 | Ankrd10 | NM_001167967.2 | chr8:11613840-11635757 |
| 2397 | Ankrd11 | NM_001081379.2 | chr8:122883821-123042284 |
| 2398 | Ankrd12 | NM_001025572.1 | chr17:65967500-66077046 |
| 2399 | Ankrd13a | NM_026718.2 | chr5:114775139-114805820 |
| 2400 | Ankrd13b | NM_172945.2 | chr11:77470486-77489678 |
| 2401 | Ankrd13c | NM_001013806.1 | chr3:157947465-158006837 |
| 2402 | Ankrd13d | NM_026720.2 | chr9:4270179-4283137 |
| 2403 | Ankrd16 | NM_177268.4 | chr2:11777752-11790323 |
| 2404 | Ankrd17 | NM_030886.2 | chr5:90227165-90366185 |
| 2405 | Ankrd2 | NM_020033.1 | chr19:42036037-42045110 |
| 2406 | Ankrd22 | NM_024204.6 | chr19:34122548-34166041 |
| 2407 | Ankrd23 | NM_153502.4 | chr1:36530192-36535739 |
| 2408 | Ankrd24 | NM_027480.3 | chr10:81628539-81647612 |
| 2409 | Ankrd26 | NM_001081112.1 | chr6:118502563-118562256 |
| 2410 | Ankrd27 | NM_145633.3 | chr7:35586246-35639237 |
| 2411 | Ankrd28 | NM_001024604.2 | chr14:31700014-31830415 |
| 2412 | Ankrd29 | NM_001190371.1 | chr18:12252356-12305720 |
| 2413 | Ankrd32 | NM_134071.3 | chr13:77043087-77135468 |
| 2414 | Ankrd33 | NM_144790.1 | chr15:101115754-101120024 |
| 2415 | Ankrd33b | NM_001164441.1 | chr15:31291478-31367759 |
| 2416 | Ankrd34a | NM_001024851.3 | chr3:96596635-96599778 |
| 2417 | Ankrd34b | NM_175455.4 | chr13:92425968-92441658 |
| 2418 | Ankrd34c | NM_207260.2 | chr9:89728248-89738475 |
| 2419 | Ankrd35 | NM_001081139.1 | chr3:96670130-96691034 |
| 2420 | Ankrd36 | NM_023816.2 | chr11:5569683-5689337 |
| 2421 | Ankrd37 | NM_001039562.1 | chr8:45996907-45999850 |
| 2422 | Ankrd39 | NM_026241.4 | chr1:36538170-36547252 |
| 2423 | Ankrd40 | NM_027799.2 | chr11:94328000-94341847 |
| 2424 | Ankrd42 | NM_028665.4 | chr7:92584182-92637142 |
| 2425 | Ankrd44 | NM_001081433.2 | chr1:54645339-54926387 |
| 2426 | Ankrd45 | NM_028664.1 | chr1:161142711-161170507 |
| 2427 | Ankrd46 | NM_175134.4 | chr15:36477667-36496791 |
| 2428 | Ankrd49 | NM_019683.3 | chr9:14780197-14782964 |
| 2429 | Ankrd50 | NM_001167883.1 | chr3:38449260-38484816 |
| 2430 | Ankrd52 | NM_172790.2 | chr10:128327123-128394006 |
| 2431 | Ankrd53 | NM_029245.3 | chr6:83762645-83768326 |
| 2432 | Ankrd54 | NM_144849.1 | chr15:79053093-79062859 |
| 2433 | Ankrd55 | NM_001168403.1 | chr13:112288450-112384002 |
| 2434 | Ankrd6 | NM_001012450.1 | chr4:32804034-32923505 |
| 2435 | Ankrd60 | NM_001199955.1 | chr2:173572389-173578341 |
| 2436 | Ankrd61 | NM_025732.2 | chr5:143890740-143895067 |
| 2437 | Ankrd63 | NM_001081971.1 | chr2:118699102-118703963 |
| 2438 | Ankrd66 | NM_001254953.1 | chr17:43534173-43543639 |
| 2439 | Ankrd7 | NM_001167757.1 | chr6:18866317-18879584 |
| 2440 | Ankrd9 | NM_175207.1 | chr12:110975352-110979021 |
| 2441 | Anks1 | NM_001286040.1 | chr17:27909305-28062779 |
| 2442 | Anks1b | NM_001128086.2 | chr10:89873508-90972984 |
| 2443 | Anks3 | NM_028301.4 | chr16:4941414-4964237 |
| 2444 | Anks4b | NM_028085.2 | chr7:120173857-120183716 |
| 2445 | Anks6 | NM_001024136.1 | chr4:47015688-47057306 |
| 2446 | Ankub1 | NM_001033349.2 | chr3:57667421-57692537 |
| 2447 | Ankzf1 | NM_001267620.1 | chr1:75192159-75195538 |
| 2448 | Anln | NM_028390.3 | chr9:22331213-22389206 |
| 2449 | Ano1 | NM_001242349.1 | chr7:144588548-144738592 |
| 2450 | Ano10 | NM_001171873.1 | chr9:122175873-122294423 |
| 2451 | Ano2 | NM_153589.2 | chr6:125690418-126040128 |
| 2452 | Ano3 | NM_001128103.2 | chr2:110655200-110950244 |
| 2453 | Ano4 | NM_001277188.1 | chr10:88948993-89257790 |
| 2454 | Ano5 | NM_001271879.1 | chr7:51511028-51598707 |
| 2455 | Ano6 | NM_001253813.1 | chr15:95799842-95975472 |
| 2456 | Ano7 | NM_001271884.1 | chr1:93373895-93404304 |
| 2457 | Ano8 | NM_001164679.1 | chr8:71476018-71486067 |
| 2458 | Ano9 | NM_178381.3 | chr7:141101218-141137806 |
| 2459 | Anp32a | NM_009672.3 | chr9:62341342-62378805 |
| 2460 | Anp32b | NM_130889.2 | chr4:46451116-46472523 |
| 2461 | Anp32e | NM_001253757.1 | chr3:95929256-95947387 |
| 2462 | Anpep | NM_008486.2 | chr7:79821802-79842352 |
| 2463 | Antxr1 | NM_054041.2 | chr6:87133852-87335775 |
| 2464 | Antxr2 | NM_133738.1 | chr5:97884687-98030962 |
| 2465 | Antxrl | NM_172808.2 | chr14:34053469-34075999 |
| 2466 | Anxa1 | NM_010730.2 | chr19:20373433-20390671 |

Fig. 26 - 14

| | | | |
|---|---|---|---|
| 2467 | Anxa10 | NM_001136089.2 | chr8:62057041-62123193 |
| 2468 | Anxa11 | NM_013469.2 | chr14:25842154-25886804 |
| 2469 | Anxa13 | NM_027211.2 | chr15:58341463-58389274 |
| 2470 | Anxa2 | NM_007585.3 | chr9:69453682-69491785 |
| 2471 | Anxa3 | NM_013470.2 | chr5:96793384-96845968 |
| 2472 | Anxa4 | NM_013471.2 | chr6:86736839-86793584 |
| 2473 | Anxa5 | NM_009673.2 | chr3:36448923-36475887 |
| 2474 | Anxa6 | NM_001110211.1 | chr11:54978961-55033471 |
| 2475 | Anxa7 | NM_001110794.1 | chr14:20455260-20480133 |
| 2476 | Anxa8 | NM_001281845.1 | chr14:34085978-34100568 |
| 2477 | Anxa9 | NM_001085383.1 | chr3:95296093-95306804 |
| 2478 | Aoah | NM_001281854.1 | chr13:20794112-20851907 |
| 2479 | Aoc1 | NM_001161621.1 | chr6:48904985-48909187 |
| 2480 | Aoc2 | NM_178932.3 | chr11:101325062-101329694 |
| 2481 | Aoc3 | NM_009675.2 | chr11:101330605-101339430 |
| 2482 | Aox1 | NM_009676.2 | chr1:58029968-58106410 |
| 2483 | Aox2 | NM_001008419.2 | chr1:58278325-58379264 |
| 2484 | Aox3 | NM_023617.2 | chr1:58113135-58200452 |
| 2485 | Aox4 | NM_023631.2 | chr1:58210396-58268696 |
| 2486 | Ap1ar | NM_145964.2 | chr3:127807264-127837492 |
| 2487 | Ap1b1 | NM_001243043.1 | chr11:4947520-5042794 |
| 2488 | Ap1g1 | NM_009677.6 | chr8:109778582-109864209 |
| 2489 | Ap1g2 | NM_007455.5 | chr14:55098834-55106593 |
| 2490 | Ap1m1 | NM_007456.4 | chr8:72240131-72257379 |
| 2491 | Ap1m2 | NM_001130300.1 | chr9:21295456-21312333 |
| 2492 | Ap1s1 | NM_007457.2 | chr5:137034993-137046060 |
| 2493 | Ap1s2 | NM_001290378.1 | chrX:163909016-163933666 |
| 2494 | Ap1s3 | NM_183027.2 | chr1:79606875-79671972 |
| 2495 | Ap2a1 | NM_001077264.1 | chr7:44900372-44929490 |
| 2496 | Ap2a2 | NM_007459.3 | chr7:141562179-141633011 |
| 2497 | Ap2b1 | NM_001035854.2 | chr11:83302696-83405033 |
| 2498 | Ap2m1 | NM_009679.3 | chr16:20535479-20544909 |
| 2499 | Ap2s1 | NM_196613.2 | chr7:16738443-16749290 |
| 2500 | Ap3b1 | NM_009680.3 | chr13:94358959-94566316 |
| 2501 | Ap3b2 | NM_021492.3 | chr7:81460398-81493925 |
| 2502 | Ap3d1 | NM_007645.4 | chr10:80706977-80742211 |
| 2503 | Ap3m1 | NM_018829.4 | chr14:21033741-21052442 |
| 2504 | Ap3m2 | NM_001122820.1 | chr8:22787353-22805654 |
| 2505 | Ap3s1 | NM_009681.5 | chr18:46741875-46790826 |
| 2506 | Ap3s2 | NM_009682.3 | chr7:79875324-79920640 |
| 2507 | Ap4b1 | NM_001163552.1 | chr3:103809516-103822025 |
| 2508 | Ap4e1 | NM_175550.3 | chr2:127008710-127069814 |
| 2509 | Ap4m1 | NM_021392.4 | chr5:138172020-138178685 |
| 2510 | Ap4s1 | NM_021710.3 | chr12:51690965-51738939 |
| 2511 | Ap5m1 | NM_001033448.2 | chr19:5568073-5571261 |
| 2512 | Ap5m1 | NM_144535.4 | chr14:49066494-49087723 |
| 2513 | Ap5s1 | NM_001291031.1 | chr2:131210359-131213514 |
| 2514 | Ap5z1 | NM_172725.2 | chr5:142463930-142478715 |
| 2515 | Apaf1 | NM_001042558.1 | chr10:90989310-91082743 |
| 2516 | Apba1 | NM_177034.3 | chr19:23758875-23949597 |
| 2517 | Apba2 | NM_001291166.1 | chr7:64502137-64753876 |
| 2518 | Apba3 | NM_018758.2 | chr10:81268171-81273247 |
| 2519 | Apbb1 | NM_001033885.1 | chr7:105558464-105581491 |
| 2520 | Apbb1ip | NM_019456.2 | chr2:22774326-22875653 |
| 2521 | Apbb2 | NM_001201413.1 | chr5:66298724-66618817 |
| 2522 | Apbb3 | NM_146085.1 | chr18:36671158-36679366 |
| 2523 | Apc | NM_007462.3 | chr18:34220983-34322190 |
| 2524 | Apc2 | NM_011789.2 | chr10:80301819-80308256 |
| 2525 | Apcdd1 | NM_133237.3 | chr18:62922326-62953195 |
| 2526 | Apcs | NM_011318.2 | chr1:172893960-172895054 |
| 2527 | Apeh | NM_146226.2 | chr9:108085413-108094480 |
| 2528 | Apela | NM_001297554.1 | chr6:65028417-65037336 |
| 2529 | Apex1 | NM_009687.2 | chr14:50924948-50927188 |
| 2530 | Apex2 | NM_029943.2 | chrX:150571506-150588155 |
| 2531 | Aph1a | NM_146104.3 | chr3:95893920-95898592 |
| 2532 | Aph1b | NM_177583.4 | chr9:66775486-66795423 |
| 2533 | Aph1c | NM_026674.3 | chr9:66814993-66834706 |
| 2534 | Api5 | NM_007645.3 | chr2:94411726-94438186 |
| 2535 | Apip | NM_019735.4 | chr2:103073674-103092649 |
| 2536 | Apitd1 | NM_027623.2 | chr4:149128348-149137600 |
| 2537 | Aplf | NM_001170489.1 | chr6:87628428-87672168 |
| 2538 | Apln | NM_013912.3 | chrX:48025145-48034852 |
| 2539 | Aplnr | NM_011784.3 | chr2:85136359-85139923 |
| 2540 | Aplp1 | NM_007467.3 | chr7:30434979-30445582 |
| 2541 | Aplp2 | NM_001102455.1 | chr9:31149556-31211815 |
| 2542 | Apmap | NM_029677.2 | chr2:150583080-150608523 |
| 2543 | Apoa1 | NM_009692.4 | chr9:46228629-46230469 |
| 2544 | Apoa1bp | NM_144897.3 | chr3:88056522-88058495 |
| 2545 | Apoa2 | NM_013474.3 | chr1:171225053-171226379 |
| 2546 | Apoa4 | NM_007468.2 | chr9:46240843-46243458 |
| 2547 | Apoa5 | NM_080434.3 | chr9:46268607-46271919 |
| 2548 | Apob | NM_009693.2 | chr12:7977676-8016839 |
| 2549 | Apobec1 | NM_001134391.1 | chr6:122577791-122602444 |
| 2550 | Apobec2 | NM_009694.4 | chr17:48419236-48432728 |
| 2551 | Apobec3 | NM_030255.3 | chr15:79892407-79908429 |
| 2552 | Apobec4 | NM_001081197.1 | chr1:152750556-152757544 |
| 2553 | Apobr | NM_138310.3 | chr7:126585007-126589092 |
| 2554 | Apoc1 | NM_001110009.1 | chr7:19689479-19692659 |
| 2555 | Apoc2 | NM_001277944.1 | chr7:19671578-19677941 |
| 2556 | Apoc3 | NM_023114.3 | chr9:46233049-46235299 |
| 2557 | Apoc4 | NM_007385.3 | chr7:19678083-19681460 |
| 2558 | Apod | NM_007470.4 | chr16:31296191-31314808 |
| 2559 | Apoe | NM_009696.4 | chr7:19696243-19699188 |
| 2560 | Apof | NM_133997.2 | chr10:128267996-128270151 |
| 2561 | Apoh | NM_013475.4 | chr11:108395296-108414396 |
| 2562 | Apol10a | NM_177744.4 | chr15:77477046-77491069 |
| 2563 | Apol10b | NM_177820.4 | chr15:77584157-77596125 |
| 2564 | Apol11a | NM_001177533.1 | chr15:77508270-77517319 |
| 2565 | Apol11b | NM_001143686.1 | chr15:77633950-77643286 |
| 2566 | Apol6 | NM_001163621.1 | chr15:77045074-77052351 |
| 2567 | Apol7a | NM_001164640.1 | chr15:77388216-77399110 |
| 2568 | Apol7b | NM_001024848.2 | chr15:77422208-77447460 |
| 2569 | Apol7c | NM_175391.4 | chr15:77524866-77533315 |
| 2570 | Apol7d | NR_040308.1 | chr1:71653334-71662843 |
| 2571 | Apol7e | NM_001134802.1 | chr15:77698888-77719288 |
| 2572 | Apol8 | NM_001081970.1 | chr15:77748612-77755229 |
| 2573 | Apol9a | NM_001162883.1 | chr15:77403788-77411080 |
| 2574 | Apol9b | NM_001168660.1 | chr15:77729120-77736382 |
| 2575 | Apold1 | NM_001109914.1 | chr6:134982000-134986836 |
| 2576 | Apom | NM_018816.1 | chr17:35128996-35131752 |
| 2577 | Apon | NM_133996.3 | chr10:128754130-128255901 |
| 2578 | Apoo | NM_001199337.1 | chrX:94367153-94417092 |
| 2579 | Apool | NM_026565.3 | chrX:112311351-112372755 |
| 2580 | Apoo-ps | NR_004438.1 | chrX:94367123-94398202 |
| 2581 | Apopt1 | NM_001163388.1 | chr12:111713268-111755055 |
| 2582 | App | NM_001198823.1 | chr16:84954435-85173707 |
| 2583 | Appbp2 | NM_025825.3 | chr11:85191309-85235120 |
| 2584 | Appl1 | NM_145221.2 | chr14:26918987-26970551 |
| 2585 | Appl2 | NM_145220.2 | chr10:83600033-83648664 |
| 2586 | Aprt | NM_009698.2 | chr8:122574636-122576907 |
| 2587 | Aptx | NM_001025444.3 | chr4:40682077-40703194 |
| 2588 | Aqp1 | NM_007472.2 | chr6:55336298-55348555 |
| 2589 | Aqp11 | NM_175105.3 | chr7:97726378-97738247 |
| 2590 | Aqp12 | NM_001159658.1 | chr1:93006333-93012269 |
| 2591 | Aqp2 | NM_009699.3 | chr15:99579055-99584545 |
| 2592 | Aqp3 | NM_016689.2 | chr4:41092723-41098183 |
| 2593 | Aqp4 | NM_009700.2 | chr18:15389393-15403684 |
| 2594 | Aqp5 | NM_009701.4 | chr15:99591027-99594829 |
| 2595 | Aqp6 | NM_175087.4 | chr15:99601399-99605477 |
| 2596 | Aqp7 | NM_007473.4 | chr4:41033073-41048136 |
| 2597 | Aqp8 | NM_001109045.1 | chr7:123462293-123468003 |
| 2598 | Aqp9 | NM_001271843.1 | chr9:71110658-71162633 |
| 2599 | Agr | NM_001290788.1 | chr2:114105161-114175339 |
| 2600 | Ar | NM_013476.4 | chrX:98148756-98323218 |
| 2601 | Araf | NM_001159645.1 | chrX:20848542-20852905 |
| 2602 | Arap1 | NM_001040111.1 | chr7:101348068-101412586 |
| 2603 | Arap2 | NM_178407.3 | chr5:62602446-62766177 |
| 2604 | Arap3 | NM_001205336.1 | chr18:37972622-37998969 |
| 2605 | Arc | NM_001276684.1 | chr15:74669080-74672570 |
| 2606 | Arcn1 | NM_145985.4 | chr9:44742143-44767808 |
| 2607 | Areg | NM_009704.4 | chr5:91139958-91148432 |
| 2608 | Arel1 | NM_178065.4 | chr12:84918148-84970886 |
| 2609 | Arf1 | NM_001130408.1 | chr11:59211411-59228162 |
| 2610 | Arf2 | NM_007477.5 | chr11:103968870-103985350 |
| 2611 | Arf3 | NM_007478.3 | chr15:98737625-98763118 |
| 2612 | Arf4 | NM_007479.3 | chr14:26638196-26657258 |
| 2613 | Arf5 | NM_007480.1 | chr6:28423639-28426499 |
| 2614 | Arf6 | NM_007481.3 | chr12:69372149-69375980 |
| 2615 | Arfgap1 | NM_001177706.1 | chr2:180967299-180982524 |
| 2616 | Arfgap2 | NM_001166024.1 | chr2:91265114-91277371 |
| 2617 | Arfgap3 | NM_025445.4 | chr15:83299739-83350247 |
| 2618 | Arfgef1 | NM_001102430.1 | chr1:10137506-10232670 |
| 2619 | Arfgef2 | NM_001085495.2 | chr2:166805580-166898051 |
| 2620 | Arfip1 | NM_001081093.2 | chr3:84496092-84582625 |
| 2621 | Arfip2 | NM_029802.4 | chr7:105634200-105640416 |
| 2622 | Arfrp1 | NM_001165991.1 | chr2:181357689-181365404 |
| 2623 | Arg1 | NM_007482.3 | chr10:24915206-24927470 |
| 2624 | Arg2 | NM_009705.3 | chr12:79130787-79156301 |
| 2625 | Arglu1 | NM_176849.3 | chr8:8666575-8690637 |
| 2626 | Arhgap1 | NM_001145902.1 | chr2:91650117-91672320 |
| 2627 | Arhgap10 | NM_030113.2 | chr8:77250365-77517907 |
| 2628 | Arhgap11a | NM_181416.3 | chr2:113831491-113848661 |
| 2629 | Arhgap12 | NM_001036692.1 | chr18:6024449-6136098 |
| 2630 | Arhgap15 | NM_001301831.1 | chr2:43748783-44395953 |
| 2631 | Arhgap15os | NR_040622.1 | chr2:44059237-44065324 |
| 2632 | Arhgap17 | NM_001122640.1 | chr7:123279148-123369915 |
| 2633 | Arhgap18 | NM_176837.2 | chr10:26772511-26918648 |
| 2634 | Arhgap19 | NM_001163495.1 | chr19:41766587-41802084 |
| 2635 | Arhgap20 | NM_175535.3 | chr9:51765351-51853059 |
| 2636 | Arhgap20os | NR_033560.1 | chr9:51839492-51875885 |
| 2637 | Arhgap21 | NM_001081364.3 | chr2:20847918-20967721 |
| 2638 | Arhgap22 | NM_153800.4 | chr14:33216822-33369936 |
| 2639 | Arhgap23 | NM_021493.2 | chr11:97450159-97502400 |
| 2640 | Arhgap24 | NM_001286468.1 | chr5:102768809-102897937 |
| 2641 | Arhgap25 | NM_001037727.2 | chr6:87458544-87533259 |
| 2642 | Arhgap26 | NM_175164.4 | chr18:38993144-39376285 |
| 2643 | Arhgap27 | NM_001205236.1 | chr11:103351483-103363692 |
| 2644 | Arhgap27os3 | NR_045346.1 | chr11:103344752-103350126 |
| 2645 | Arhgap28 | NM_172964.4 | chr17:67842707-68004108 |
| 2646 | Arhgap29 | NM_172525.2 | chr3:121953325-122016153 |
| 2647 | Arhgap30 | NM_001005508.2 | chr1:171388959-171410239 |
| 2648 | Arhgap31 | NM_020260.2 | chr16:38598342-38713035 |
| 2649 | Arhgap32 | NM_001195632.1 | chr9:32116135-32265511 |
| 2650 | Arhgap33 | NM_001289670.1 | chr7:30522225-30535060 |
| 2651 | Arhgap33os | NR_036630.1 | chr7:30515121-30522193 |
| 2652 | Arhgap35 | NM_172739.4 | chr7:16494472-16614993 |
| 2653 | Arhgap36 | NM_001081123.1 | chrX:49470449-49500250 |
| 2654 | Arhgap39 | NM_001168288.1 | chr15:76723984-76818170 |
| 2655 | Arhgap4 | NM_001162423.1 | chrX:73694351-73911298 |
| 2656 | Arhgap40 | NM_001145015.1 | chr2:158512795-158550628 |

Fig. 26 - 15

| | | | |
|---|---|---|---|
| 2657 | Arhgap42 | NM_027823.1 | chr9:8994952-9239013 |
| 2658 | Arhgap44 | NM_001099288.1 | chr11:65002038-65162961 |
| 2659 | Arhgap5 | NM_009706.2 | chr12:52516076-52567851 |
| 2660 | Arhgap6 | NM_001287530.1 | chrX:169112877-169304440 |
| 2661 | Arhgap8 | NM_001164627.1 | chr15:84720051-84772207 |
| 2662 | Arhgap9 | NM_001285785.1 | chr10:127321963-127329943 |
| 2663 | Arhgdia | NM_133796.7 | chr11:120577234-120581620 |
| 2664 | Arhgdib | NM_007486.5 | chr6:136923660-136941756 |
| 2665 | Arhgdig | NM_008113.3 | chr17:26199182-26201350 |
| 2666 | Arhgef1 | NM_001130150.1 | chr7:24902985-24926591 |
| 2667 | Arhgef10 | NM_001037736.2 | chr8:14911662-15001085 |
| 2668 | Arhgef10l | NM_001112722.1 | chr4:140514484-140665905 |
| 2669 | Arhgef11 | NM_001003912.1 | chr3:87618750-87738033 |
| 2670 | Arhgef12 | NM_027144.2 | chr9:42963841-43105718 |
| 2671 | Arhgef15 | NM_177566.3 | chr11:68943153-68956858 |
| 2672 | Arhgef16 | NM_001112744.1 | chr4:154278469-154299895 |
| 2673 | Arhgef17 | NM_001081116.1 | chr7:100869745-100932161 |
| 2674 | Arhgef18 | NM_133962.3 | chr8:3393007-3456600 |
| 2675 | Arhgef19 | NM_172520.2 | chr4:141242883-141257562 |
| 2676 | Arhgef2 | NM_001198911.1 | chr3:88616206-88648052 |
| 2677 | Arhgef25 | NM_001166413.1 | chr10:127182520-127189823 |
| 2678 | Arhgef26 | NM_001081295.1 | chr3:62338776-62462221 |
| 2679 | Arhgef28 | NM_012026.2 | chr13:97898594-98206165 |
| 2680 | Arhgef3 | NM_001289686.1 | chr14:27143992-27403911 |
| 2681 | Arhgef33 | NM_001145424.1 | chr17:80307406-80388689 |
| 2682 | Arhgef37 | NM_177828.4 | chr18:61493793-61536536 |
| 2683 | Arhgef38 | NM_029953.1 | chr3:133159530-133234889 |
| 2684 | Arhgef39 | NM_001013377.2 | chr4:43486143-43499660 |
| 2685 | Arhgef4 | NM_183019.2 | chr1:34801721-34812754 |
| 2686 | Arhgef40 | NM_001145921.1 | chr14:51984832-52006247 |
| 2687 | Arhgef5 | NM_133674.1 | chr6:43265643-43289320 |
| 2688 | Arhgef6 | NM_152801.2 | chrX:57231484-57338729 |
| 2689 | Arhgef7 | NM_001113517.1 | chr8:11728104-11827152 |
| 2690 | Arhgef9 | NM_001013329.3 | chrX:95048934-95166539 |
| 2691 | Arid1a | NM_001080819.1 | chr4:133679007-133753611 |
| 2692 | Arid1b | NM_001085355.1 | chr17:4995073-5347656 |
| 2693 | Arid2 | NM_175251.4 | chr15:96287521-96405463 |
| 2694 | Arid3a | NM_001288625.1 | chr10:79927340-79955018 |
| 2695 | Arid3b | NM_019689.2 | chr9:57790504-57834234 |
| 2696 | Arid3c | NM_001017362.2 | chr4:41723835-41731142 |
| 2697 | Arid4a | NM_001081195.1 | chr12:71015966-71099351 |
| 2698 | Arid4b | NM_194262.2 | chr13:14063783-14199603 |
| 2699 | Arid5a | NM_001172205.1 | chr1:36307732-36324029 |
| 2700 | Arid5b | NM_023598.2 | chr10:68095592-68708726 |
| 2701 | Arih1 | NM_019927.2 | chr9:59388553-59486374 |
| 2702 | Arih2 | NM_011790.4 | chr9:108602942-108649380 |
| 2703 | Arl1 | NM_025859.3 | chr10:88731413-88743202 |
| 2704 | Arl10 | NM_019968.2 | chr13:54575012-54581128 |
| 2705 | Arl11 | NM_177337.3 | chr14:61309752-61311936 |
| 2706 | Arl13a | NM_028947.1 | chrX:134187500-134208030 |
| 2707 | Arl13b | NM_026577.3 | chr16:62793688-62847040 |
| 2708 | Arl14 | NM_027843.1 | chr3:69222418-69223618 |
| 2709 | Arl14ep | NM_025102.1 | chr2:106962528-106974397 |
| 2710 | Arl14epl | NM_001033446.2 | chr18:46921814-46934222 |
| 2711 | Arl15 | NM_172595.4 | chr13:113794507-114157461 |
| 2712 | Arl16 | NM_197995.2 | chr11:120464325-120467600 |
| 2713 | Arl2 | NM_019722.3 | chr19:6134388-6141137 |
| 2714 | Arl2bp | NM_024191.2 | chr8:94666599-94674457 |
| 2715 | Arl3 | NM_019718.2 | chr19:46531108-46573085 |
| 2716 | Arl4a | NM_001039515.1 | chr12:40033290-40037987 |
| 2717 | Arl4c | NM_177305.4 | chr1:88698225-88702191 |
| 2718 | Arl4d | NM_025404.3 | chr11:101665540-101667832 |
| 2719 | Arl5a | NM_182994.2 | chr2:52397950-52424874 |
| 2720 | Arl5b | NM_029466.4 | chr2:15055361-15079191 |
| 2721 | Arl5c | NM_207231.1 | chr11:97989579-97996173 |
| 2722 | Arl6 | NM_019665.3 | chr16:59613320-59639339 |
| 2723 | Arl6ip1 | NM_019419.2 | chr7:118118889-118129625 |
| 2724 | Arl6ip4 | NM_144509.2 | chr5:124116107-124118195 |
| 2725 | Arl6ip5 | NM_022992.2 | chr6:97210791-97233315 |
| 2726 | Arl6ip6 | NM_028999.4 | chr2:53192083-53219221 |
| 2727 | Arl8a | NM_026823.2 | chr1:135146833-135156268 |
| 2728 | Arl8b | NM_026011.3 | chr6:108783058-108823723 |
| 2729 | Arl9 | NM_206935.1 | chr5:77004054-77009478 |
| 2730 | Armc1 | NM_028840.2 | chr3:19132143-19163065 |
| 2731 | Armc10 | NM_026034.4 | chr5:21645983-21662592 |
| 2732 | Armc12 | NM_026290.3 | chr17:28530860-28538975 |
| 2733 | Armc2 | NM_001034858.3 | chr10:41914989-42018382 |
| 2734 | Armc3 | NM_001081083.2 | chr2:19199117-19310243 |
| 2735 | Armc4 | NM_001081393.1 | chr18:7088232-7297901 |
| 2736 | Armc5 | NM_146205.2 | chr7:128237356-128245100 |
| 2737 | Armc6 | NM_139972.2 | chr8:70220192-70234422 |
| 2738 | Armc7 | NM_177778.4 | chr11:115475676-115480466 |
| 2739 | Armc8 | NM_001166138.1 | chr9:99518244-99568899 |
| 2740 | Armc9 | NM_027456.2 | chr1:86154779-86252491 |
| 2741 | Armcx1 | NM_001166377.1 | chrX:134717937-134721912 |
| 2742 | Armcx2 | NM_001166397.1 | chrX:134804141-134809223 |
| 2743 | Armcx3 | NM_027870.3 | chrX:134756567-134761456 |
| 2744 | Armcx4 | NM_001202500.3 | chrX:134686518-134697772 |
| 2745 | Armcx5 | NM_001009575.5 | chrX:135742691-135747326 |
| 2746 | Armcx6 | NM_001007578.2 | chrX:134748454-134751419 |
| 2747 | Arnt | NM_001037737.2 | chr3:95434389-95497239 |
| 2748 | Arnt2 | NM_007488.3 | chr7:84246274-84410038 |
| 2749 | Arntl | NM_001243048.1 | chr7:113207464-113314126 |
| 2750 | Arntl2 | NM_001289679.1 | chr6:146805529-146833529 |
| 2751 | Arpc1a | NM_019767.2 | chr5:145083868-145108756 |

| | | | |
|---|---|---|---|
| 2752 | Arpc1b | NM_023142.2 | chr5:145114255-145128186 |
| 2753 | Arpc2 | NM_029711.1 | chr1:74236549-74268213 |
| 2754 | Arpc3 | NM_019824.3 | chr5:122391927-122406178 |
| 2755 | Arpc4 | NM_001170485.1 | chr6:113378112-113390447 |
| 2756 | Arpc5 | NM_026369.2 | chr1:152786541-152775580 |
| 2757 | Arpc5l | NM_028809.1 | chr2:39008138-39015872 |
| 2758 | Arpp19 | NM_001142655.1 | chr9:75037613-75060313 |
| 2759 | Arpp21 | NM_001177615.1 | chr9:112180031-112187926 |
| 2760 | Arr3 | NM_133205.3 | chrX:106605496-100618493 |
| 2761 | Arrb1 | NM_177231.2 | chr7:99535485-99606771 |
| 2762 | Arrb2 | NM_001271358.1 | chr11:70432579-70440828 |
| 2763 | Arrdc1 | NM_001162485.1 | chr2:24925351-24935281 |
| 2764 | Arrdc2 | NM_027560.1 | chr8:70835137-70839720 |
| 2765 | Arrdc3 | NM_001042591.1 | chr13:80883421-80896043 |
| 2766 | Arrdc4 | NM_001042592.2 | chr7:68736993-68749238 |
| 2767 | Arrdc5 | NM_029799.1 | chr17:56294110-56300286 |
| 2768 | Arsa | NM_009713.4 | chr15:89472475-89477424 |
| 2769 | Arsb | NM_009712.3 | chr13:93771678-93943016 |
| 2770 | Arsg | NM_001166770.1 | chr11:109543710-109573329 |
| 2771 | Arsi | NM_001038499.1 | chr18:60912239-60917768 |
| 2772 | Arsj | NM_173451.3 | chr3:126363851-126440374 |
| 2773 | Arsk | NM_029847.4 | chr13:76060421-76098660 |
| 2774 | Art1 | NM_009710.4 | chr7:102101742-102111148 |
| 2775 | Art2a-ps | NM_007490.1 | chr7:101552775-101555802 |
| 2776 | Art2b | NM_019915.2 | chr7:101578859-101581161 |
| 2777 | Art3 | NM_181728.3 | chr5:92388133-92414627 |
| 2778 | Art4 | NM_026639.2 | chr6:136848450-136857600 |
| 2779 | Art5 | NM_001291354.1 | chr7:102096878-102100229 |
| 2780 | Artn | NM_001284191.1 | chr4:117926159-117929763 |
| 2781 | Arv1 | NM_026855.4 | chr8:124722138-124734123 |
| 2782 | Arvcf | NM_001272028.1 | chr16:18380782-18407074 |
| 2783 | Arx | NM_007492.4 | chrX:93286506-93298355 |
| 2784 | Arxes1 | NM_029541.3 | chrX:136033366-136034946 |
| 2785 | Arxes2 | NM_029823.2 | chrX:135993819-135995359 |
| 2786 | As3mt | NM_020577.2 | chr19:46707442-46741095 |
| 2787 | Asah1 | NM_019734.3 | chr8:41340642-41374697 |
| 2788 | Asah2 | NM_018830.1 | chr19:31984650-32103140 |
| 2789 | Asap1 | NM_001276461.1 | chr15:64086839-64382919 |
| 2790 | Asap2 | NM_001004364.2 | chr12:21113755-21270171 |
| 2791 | Asap3 | NM_001008232.2 | chr4:136206364-136246573 |
| 2792 | Asb1 | NM_001039126.2 | chr1:91540564-91559590 |
| 2793 | Asb10 | NM_080444.5 | chr5:24532696-24540457 |
| 2794 | Asb11 | NM_026853.2 | chrX:164436993-164459170 |
| 2795 | Asb12 | NM_080858.3 | chrX:95470198-95478129 |
| 2796 | Asb13 | NM_001267724.1 | chr13:3634031-3651779 |
| 2797 | Asb14 | NM_001170748.1 | chr14:26894603-26915257 |
| 2798 | Asb15 | NM_080847.3 | chr6:24528143-24573164 |
| 2799 | Asb16 | NM_148953.2 | chr11:102268822-102278061 |
| 2800 | Asb17 | NM_025758.4 | chr3:153844246-153853615 |
| 2801 | Asb17os | NR_040373.1 | chr3:153850373-153852424 |
| 2802 | Asb18 | NM_139152.1 | chr1:89952677-90014577 |
| 2803 | Asb2 | NM_023049.1 | chr12:103321141-103356001 |
| 2804 | Asb3 | NM_023906.3 | chr11:30954397-31102704 |
| 2805 | Asb4 | NM_023048.5 | chr6:5383385-5433021 |
| 2806 | Asb5 | NM_029569.3 | chr8:54550330-54587836 |
| 2807 | Asb6 | NM_133346.2 | chr2:30823097-30828300 |
| 2808 | Asb7 | NM_080443.2 | chr7:66644566-66689561 |
| 2809 | Asb8 | NM_001170710.1 | chr15:98134639-98145702 |
| 2810 | Asb9 | NM_027027.2 | chrX:164497902-164539752 |
| 2811 | Ascc1 | NM_001199187.1 | chr10:60003326-60099990 |
| 2812 | Ascc2 | NM_029291.1 | chr11:4637792-4683386 |
| 2813 | Ascc3 | NM_198007.2 | chr10:50592668-50851202 |
| 2814 | Ascl1 | NM_008553.4 | chr10:87491040-87493660 |
| 2815 | Ascl2 | NM_008554.3 | chr7:142966821-142969264 |
| 2816 | Ascl3 | NM_020051.1 | chr7:109727464-109731732 |
| 2817 | Ascl4 | NM_001163614.1 | chr10:85928480-85929647 |
| 2818 | Ascl5 | NM_001270609.1 | chr1:136056803-136051370 |
| 2819 | Asf1a | NM_025541.3 | chr10:53596960-53609215 |
| 2820 | Asf1b | NM_024184.2 | chr8:83955693-83970195 |
| 2821 | Asgr1 | NM_001291131.1 | chr11:70054123-70057895 |
| 2822 | Asgr2 | NM_007493.3 | chr11:70092643-70106186 |
| 2823 | Ash1l | NM_138679.5 | chr3:88965811-89079375 |
| 2824 | Ash2l | NM_001080793.2 | chr8:25816000-25847694 |
| 2825 | Asic1 | NM_001289791.1 | chr15:99691754-99701130 |
| 2826 | Asic2 | NM_001034013.2 | chr11:80880164-81968396 |
| 2827 | Asic3 | NM_183000.2 | chr5:24413450-24417834 |
| 2828 | Asic4 | NM_183022.3 | chr1:75450509-75474340 |
| 2829 | Asic5 | NM_021370.2 | chr3:81996921-82021233 |
| 2830 | Asl | NM_133768.4 | chr5:130011502-130024331 |
| 2831 | Asmt | NM_001199212.1 | chrX:170672644-170678054 |
| 2832 | Asna1 | NM_019652.1 | chr8:85017930-85025278 |
| 2833 | Asns | NM_012055.3 | chr6:7675170-7693182 |
| 2834 | Asnsd1 | NM_001290984.1 | chr1:53344616-53352752 |
| 2835 | Aspa | NM_023113.5 | chr11:73304987-73326637 |
| 2836 | Aspdh | NM_026690.1 | chr7:44465434-44467751 |
| 2837 | Aspg | NM_001081169.1 | chr12:112106682-112127573 |
| 2838 | Asph | NM_001177849.1 | chr4:9449084-9669162 |
| 2839 | Asphd1 | NM_001039645.1 | chr7:126946007-126949581 |
| 2840 | Asphd2 | NM_028386.1 | chr5:112385444-112394213 |
| 2841 | Aspm | NM_009791.4 | chr1:139454772-139494088 |
| 2842 | Aspn | NM_001172431.1 | chr13:49544442-49567562 |
| 2843 | Asprv1 | NM_026414.2 | chr6:86628173-86629704 |
| 2844 | Aspscr1 | NM_001164224.1 | chr11:120676660-120709446 |
| 2845 | Asrgl1 | NM_025610.3 | chr19:9111718-9135566 |
| 2846 | Ass1 | NM_007494.3 | chr2:31470269-31520670 |

Fig. 26 - 16

| | | | |
|---|---|---|---|
| 2847 | Aste1 | NM_001164828.1 | chr9:105400787-105405756 |
| 2848 | Astl | NM_001291003.1 | chr2:127341635-127357656 |
| 2849 | Astn1 | NM_001205204.1 | chr1:158362303-158691786 |
| 2850 | Astn2 | NM_019514.3 | chr4:65380802-66404483 |
| 2851 | Asun | NM_138757.2 | chr6:146549631-146577835 |
| 2852 | Asxl1 | NM_001039939.1 | chr2:153346138-153404007 |
| 2853 | Asxl2 | NM_001270988.1 | chr12:3426856-3506849 |
| 2854 | Asxl3 | NM_001167777.1 | chr18:22345088-22530227 |
| 2855 | Asz1 | NM_023729.3 | chr6:18050963-18109061 |
| 2856 | Atad1 | NM_026487.3 | chr19:32672562-32712298 |
| 2857 | Atad2 | NM_027435.2 | chr15:58094046-58135082 |
| 2858 | Atad2b | NM_001098628.1 | chr12:4917352-5047410 |
| 2859 | Atad3a | NM_179203.3 | chr4:155740639-155761098 |
| 2860 | Atad3aos | NR_027971.1 | chr4:155761191-155762260 |
| 2861 | Atad5 | NM_001029856.2 | chr11:80089399-80135791 |
| 2862 | Atat1 | NM_001142744.1 | chr17:35897597-35910068 |
| 2863 | Atcay | NM_178662.3 | chr10:81204512-81230779 |
| 2864 | Atcayos | NR_015477.1 | chr10:81194690-81208370 |
| 2865 | Ate1 | NM_001029895.3 | chr7:130391493-130520369 |
| 2866 | Atf1 | NM_007497.3 | chr15:100227858-100261248 |
| 2867 | Atf2 | NM_001025093.2 | chr2:73816508-73892639 |
| 2868 | Atf3 | NM_007498.3 | chr1:191170296-191183333 |
| 2869 | Atf4 | NM_001287180.1 | chr15:80255183-80257545 |
| 2870 | Atf5 | NM_030693.2 | chr7:44812255-44815658 |
| 2871 | Atf6 | NM_001081304.1 | chr1:170704456-170867771 |
| 2872 | Atf6b | NM_017406.4 | chr17:34647145-34655074 |
| 2873 | Atf7 | NM_001310066.1 | chr15:102536643-102625421 |
| 2874 | Atf7ip | NM_019426.2 | chr6:136518850-136607379 |
| 2875 | Atf7ip2 | NM_029253.1 | chr16:10192905-10237287 |
| 2876 | Atg10 | NM_025770.3 | chr13:90935348-91223987 |
| 2877 | Atg101 | NM_026566.2 | chr15:101284300-101290934 |
| 2878 | Atg12 | NM_026217.3 | chr18:46732416-46741579 |
| 2879 | Atg13 | NM_145528.3 | chr2:91674611-91710592 |
| 2880 | Atg14 | NM_172599.4 | chr14:47540892-47568434 |
| 2881 | Atg16l1 | NM_001205391.1 | chr1:87756010-87792428 |
| 2882 | Atg16l2 | NM_001111111.1 | chr7:101289615-101302088 |
| 2883 | Atg2a | NM_194348.3 | chr19:6241667-6262304 |
| 2884 | Atg2b | NM_029654.4 | chr12:105613539-105685241 |
| 2885 | Atg3 | NM_026402.3 | chr16:45158828-45188538 |
| 2886 | Atg4a | NM_174875.3 | chr3:103643952-103646068 |
| 2887 | Atg4b | NM_174874.3 | chr1:93755032-93789529 |
| 2888 | Atg4c | NM_145967.1 | chr4:99194146-99259787 |
| 2889 | Atg4d | NM_153583.10 | chr9:21265284-21274837 |
| 2890 | Atg5 | NM_053069.6 | chr10:44268338-44364299 |
| 2891 | Atg7 | NM_001253717.1 | chr6:114643096-114860614 |
| 2892 | Atg9a | NM_001003917.4 | chr1:75180860-75192010 |
| 2893 | Atg9b | NM_001002897.3 | chr5:24884180-24892143 |
| 2894 | Athl1 | NM_145387.4 | chr7:140941580-140947658 |
| 2895 | Atic | NM_026195.3 | chr1:71557155-71579403 |
| 2896 | Atl1 | NM_178628.5 | chr12:69893104-69964085 |
| 2897 | Atl2 | NM_001286647.1 | chr17:79848389-79896123 |
| 2898 | Atl3 | NM_001163505.1 | chr19:7494039-7538609 |
| 2899 | Atm | NM_007499.2 | chr9:53437121-53536671 |
| 2900 | Atmin | NM_177700.4 | chr8:116943392-116960445 |
| 2901 | Atn1 | NM_007881.4 | chr6:124742543-124756487 |
| 2902 | Atoh1 | NM_007500.4 | chr6:64729145-64731235 |
| 2903 | Atoh7 | NM_016864.1 | chr10:63100155-63100605 |
| 2904 | Atoh8 | NM_153778.3 | chr6:72206176-72235577 |
| 2905 | Atox1 | NM_009720.2 | chr11:55446642-55461138 |
| 2906 | Atp10a | NM_009728.2 | chr7:58658201-58829426 |
| 2907 | Atp10b | NM_176999.3 | chr11:43149876-43262286 |
| 2908 | Atp10d | NM_153389.3 | chr5:72203342-72298758 |
| 2909 | Atp11a | NM_015804.3 | chr8:12757015-12868728 |
| 2910 | Atp11b | NM_029570.3 | chr3:35754137-35856276 |
| 2911 | Atp11c | NM_001001798.2 | chrX:60223289-60403981 |
| 2912 | Atp12a | NM_138652.2 | chr14:56365067-56388551 |
| 2913 | Atp13a1 | NM_133224.2 | chr8:69791162-69807748 |
| 2914 | Atp13a2 | NM_001164366.1 | chr4:140986872-141007701 |
| 2915 | Atp13a3 | NM_001128094.1 | chr16:30312423-30388530 |
| 2916 | Atp13a4 | NM_001164612.1 | chr16:29396037-29541483 |
| 2917 | Atp13a5 | NM_001284375.1 | chr16:29231913-29378732 |
| 2918 | Atp1a1 | NM_144900.2 | chr3:101576218-101604707 |
| 2919 | Atp1a2 | NM_178405.3 | chr1:172271708-172298064 |
| 2920 | Atp1a3 | NM_001290469.1 | chr7:24978168-25005937 |
| 2921 | Atp1a4 | NM_013734.1 | chr1:172223507-172258424 |
| 2922 | Atp1b1 | NM_009721.3 | chr1:164437098-164458355 |
| 2923 | Atp1b2 | NM_013415.5 | chr11:69599749-69605960 |
| 2924 | Atp1b3 | NM_007502.4 | chr9:96332674-96364299 |
| 2925 | Atp1b4 | NM_001163121.1 | chrX:38316121-38336784 |
| 2926 | Atp2a1 | NM_007504.2 | chr7:126445859-126463073 |
| 2927 | Atp2a2 | NM_001110140.3 | chr5:122456323-122502225 |
| 2928 | Atp2a3 | NM_001163336.1 | chr11:72961168-72993043 |
| 2929 | Atp2b1 | NM_026482.2 | chr10:98915151-99026143 |
| 2930 | Atp2b2 | NM_001036684.2 | chr6:113745667-113891376 |
| 2931 | Atp2b3 | NM_177236.4 | chrX:73503085-73573270 |
| 2932 | Atp2b4 | NM_001167949.2 | chr1:133702673-133753747 |
| 2933 | Atp2c1 | NM_001253831.1 | chr9:105411361-105521257 |
| 2934 | Atp2c2 | NM_026922.1 | chr8:119700008-119757718 |
| 2935 | Atp4a | NM_001290627.1 | chr7:30712208-30725534 |
| 2936 | Atp4b | NM_009724.2 | chr8:13386208-13396778 |
| 2937 | Atp5a1 | NM_007505.2 | chr18:77773767-77782868 |
| 2938 | Atp5b | NM_016774.3 | chr10:128083306-128090388 |
| 2939 | Atp5c1 | NM_001112738.1 | chr2:10056030-10080510 |
| 2940 | Atp5d | NM_025313.2 | chr10:80142314-80145818 |
| 2941 | Atp5e | NM_025983.3 | chr2:174461074-174464101 |
| 2942 | Atp5f1 | NM_009725.4 | chr3:105942677-105960248 |
| 2943 | Atp5g1 | NM_001161419.1 | chr11:96072792-96075631 |
| 2944 | Atp5g2 | NM_026468.2 | chr15:102862867-102671047 |
| 2945 | Atp5g3 | NM_175015.3 | chr2:73908446-73911326 |
| 2946 | Atp5h | NM_027862.1 | chr11:115415696-115419919 |
| 2947 | Atp5j | NM_016755.3 | chr16:84827870-84835625 |
| 2948 | Atp5j2 | NM_020582.2 | chr5:145183705-145191592 |
| 2949 | Atp5k | NM_007507.2 | chr5:108433252-108434378 |
| 2950 | Atp5l | NM_013795.5 | chr9:44913247-44920742 |
| 2951 | Atp5o | NM_138597.2 | chr16:91925222-91931630 |
| 2952 | Atp5s | NM_026536.1 | chr12:69724961-69744658 |
| 2953 | Atp5sl | NM_001290487.1 | chr7:25619413-25625550 |
| 2954 | Atp6ap1 | NM_018794.4 | chrX:74297096-74304721 |
| 2955 | Atp6ap1l | NM_001145879.1 | chr13:90883448-90905355 |
| 2956 | Atp6ap2 | NM_027439.4 | chrX:12587758-12617051 |
| 2957 | Atp6v0a1 | NM_001243049.1 | chr11:101009451-101063717 |
| 2958 | Atp6v0a2 | NM_011596.5 | chr5:124629051-124724455 |
| 2959 | Atp6v0a4 | NM_080467.3 | chr6:38048482-38124586 |
| 2960 | Atp6v0b | NM_033617.3 | chr4:117884329-117887329 |
| 2961 | Atp6v0c | NM_009729.3 | chr17:24163865-24169429 |
| 2962 | Atp6v0c-ps2 | NR_037854.1 | chr17:24163864-24169395 |
| 2963 | Atp6v0d1 | NM_013477.3 | chr8:105524469-105566040 |
| 2964 | Atp6v0d2 | NM_175406.3 | chr4:19876837-19922566 |
| 2965 | Atp6v0e | NM_025272.2 | chr17:26676395-26699646 |
| 2966 | Atp6v0e2 | NM_133764.3 | chr6:48537568-48541800 |
| 2967 | Atp6v1a | NM_007508.5 | chr16:44085403-44139019 |
| 2968 | Atp6v1b1 | NM_134157.2 | chr6:83743016-83758810 |
| 2969 | Atp6v1b2 | NM_007509.3 | chr8:69088735-69113717 |
| 2970 | Atp6v1c1 | NM_025494.3 | chr15:38661903-38692444 |
| 2971 | Atp6v1c2 | NM_001159632.1 | chr12:17284720-17324730 |
| 2972 | Atp6v1d | NM_023721.2 | chr12:78842981-78861638 |
| 2973 | Atp6v1e1 | NM_007510.2 | chr6:120795243-120822685 |
| 2974 | Atp6v1e2 | NM_029121.3 | chr17:86944108-86947887 |
| 2975 | Atp6v1f | NM_025381.2 | chr6:29467782-29470509 |
| 2976 | Atp6v1g1 | NM_024173.2 | chr4:63544764-63550701 |
| 2977 | Atp6v1g2 | NM_023179.3 | chr17:35236595-35238768 |
| 2978 | Atp6v1g3 | NM_177397.3 | chr1:138273737-138289462 |
| 2979 | Atp6v1h | NM_133826.5 | chr15:5083085-5162549 |
| 2980 | Atp7a | NM_001109757.2 | chrX:106027223-106128160 |
| 2981 | Atp7b | NM_007511.2 | chr8:21994347-22060074 |
| 2982 | Atp8a1 | NM_001038999.2 | chr5:67618138-67847431 |
| 2983 | Atp8a2 | NM_015803.2 | chr14:59647740-60086834 |
| 2984 | Atp8b1 | NM_001004488.3 | chr18:64528978-64661000 |
| 2985 | Atp8b2 | NM_001081182.2 | chr3:89939480-89963332 |
| 2986 | Atp8b3 | NM_026094.3 | chr10:80519584-80539124 |
| 2987 | Atp8b4 | NM_001080944.3 | chr2:126320972-126491553 |
| 2988 | Atp8b5 | NM_177195.3 | chr4:43267158-43373831 |
| 2989 | Atp9a | NM_001289445.1 | chr2:168634437-168734339 |
| 2990 | Atp9b | NM_001201569.1 | chr18:80734140-80934058 |
| 2991 | Atpaf1 | NM_183040.4 | chr4:115784813-115812314 |
| 2992 | Atpaf2 | NM_145427.2 | chr11:60400623-60417099 |
| 2993 | Atpif1 | NM_007512.4 | chr4:132530554-132535414 |
| 2994 | Atr | NM_019864.1 | chr9:95867596-95951644 |
| 2995 | Atraid | NM_027855.4 | chr5:31048639-31054633 |
| 2996 | Atrip | NM_172774.3 | chr9:109059746-109074124 |
| 2997 | Atrn | NM_009730.2 | chr2:130906495-131030326 |
| 2998 | Atrnl1 | NM_181415.4 | chr19:57611033-58133340 |
| 2999 | Atrx | NM_009530.2 | chrX:105797614-105929372 |
| 3000 | Atxn1 | NM_001199304.1 | chr13:45549755-45964991 |
| 3001 | Atxn10 | NM_016843.3 | chr15:85336380-85463836 |
| 3002 | Atxn1l | NM_001080930.1 | chr8:109726450-109737739 |
| 3003 | Atxn2 | NM_009125.2 | chr5:121711608-121814950 |
| 3004 | Atxn2l | NM_183020.1 | chr7:126491707-126503302 |
| 3005 | Atxn3 | NM_001167914.1 | chr12:101932923-101958243 |
| 3006 | Atxn7 | NM_139227.4 | chr14:14012490-14107301 |
| 3007 | Atxn7l1 | NM_001033436.3 | chr12:33302514-33368277 |
| 3008 | Atxn7l2 | NM_001289545.1 | chr3:108202227-108210527 |
| 3009 | Atxn7l3 | NM_001098836.1 | chr11:102289299-102296629 |
| 3010 | Atxn7l3b | NM_001033474.2 | chr10:112925427-112929026 |
| 3011 | AU015228 | NM_001033197.2 | chr2:130100393-130103375 |
| 3012 | AU015791 | NR_102381.1 | chr12:105513432-105515248 |
| 3013 | AU015836 | NR_028320.1 | chrX:93968655-93975470 |
| 3014 | AU016765 | NR_045899.1 | chr17:64514088-64555590 |
| 3015 | AU018091 | NM_001004153.2 | chr7:3154658-3169203 |
| 3016 | AU018829 | NM_001200055.1 | chr5:82183-95195342 |
| 3017 | AU019823 | NM_001134902.1 | chr9:50605239-50617464 |
| 3018 | AU019990 | NR_033468.1 | chr2:132598195-132653064 |
| 3019 | AU021063 | NR_045996.1 | chr15:101221246-101222155 |
| 3020 | AU022102 | NM_001033220.3 | chr16:5211818-5222299 |
| 3021 | AU022252 | NM_001012400.2 | chr4:119225137-119232724 |
| 3022 | AU022751 | NM_001033211.3 | chrX:6081217-6083420 |
| 3023 | AU022754 | NM_040433.1 | chr15:85581141-85593708 |
| 3024 | AU022793 | NR_045719.1 | chr15:39962648-39967515 |
| 3025 | AU023762 | NR_040760.1 | chr9:113496745-113587152 |
| 3026 | AU040320 | NM_001035525.1 | chr4:126753554-126866694 |
| 3027 | AU040972 | NR_045305.1 | chr11:79481722-79484031 |
| 3028 | AU041133 | NM_001163064.1 | chr10:82128012-82153065 |
| 3029 | Auh | NM_016709.2 | chr13:52835510-52929677 |
| 3030 | Aup1 | NM_007517.4 | chr6:83054520-83057682 |
| 3031 | Aurka | NM_001291185.1 | chr2:172356189-172370570 |
| 3032 | Aurkaip1 | NM_025338.4 | chr4:155831268-155833098 |
| 3033 | Aurkb | NM_011496.2 | chr11:69045642-69051662 |
| 3034 | Aurkc | NM_001080965.1 | chr7:6995384-7003091 |
| 3035 | Auts2 | NM_177047.3 | chr5:131437681-132542343 |
| 3036 | AV039307 | NR_038349.1 | chr2:120850655-120866690 |

Fig. 26 - 17

| | | | |
|---|---|---|---|
| 3037 | AV051173 | NR_040442.1 | chr4:116684964-116686022 |
| 3038 | AV320801 | NM_177918.1 | chrX:135167623-135504594 |
| 3039 | Aven | NM_001165935.1 | chr2:112559681-112631253 |
| 3040 | Avil | NM_009835.3 | chr10:127000708-127020994 |
| 3041 | Avil9 | NM_030235.1 | chr6:56714904-56761911 |
| 3042 | Avp | NM_009732.2 | chr2:130580619-130582588 |
| 3043 | Avpi1 | NM_027106.4 | chr19:42123274-42128993 |
| 3044 | Avpr1a | NM_016847.2 | chr10:122448498-122453453 |
| 3045 | Avpr1b | NM_011924.2 | chr1:131599113-131612000 |
| 3046 | Avpr2 | NM_001276298.1 | chrX:73892101-73894428 |
| 3047 | AW011738 | NR_030671.1 | chr4:156203283-156206028 |
| 3048 | AW046200 | NR_040698.1 | chr8:57651752-57663430 |
| 3049 | AW112010 | NR_102366.1 | chr19:11047611-11090566 |
| 3050 | AW146154 | NM_001033530.3 | chr7:41478873-41499890 |
| 3051 | AW209491 | NM_001104646.1 | chr13:14630244-14638202 |
| 3052 | AW495222 | NR_045086.1 | chr13:93706099-93719175 |
| 3053 | AW549542 | NM_045702.1 | chr5:119570128-119580358 |
| 3054 | AW549877 | NM_145930.2 | chr15:3982034-3995752 |
| 3055 | AW551984 | NM_001159598.1 | chr9:39587395-39603652 |
| 3056 | AW554918 | NM_001033532.3 | chr18:25169019-25467321 |
| 3057 | AW822252 | NR_110489.1 | chrX:53696921-53716578 |
| 3058 | Awat1 | NM_001081136.1 | chrX:100572246-100578206 |
| 3059 | Awat2 | NM_001290395.1 | chrX:100402221-100442717 |
| 3060 | Axin1 | NM_001159598.1 | chr17:26138685-26195811 |
| 3061 | Axin2 | NM_015732.4 | chr11:108920348-108950781 |
| 3062 | Axl | NM_001190974.1 | chr7:25756499-25788733 |
| 3063 | AY074887 | NM_145229.2 | chr9:54950256-54950954 |
| 3064 | AY358078 | NM_194347.1 | chr14:51800045-51826359 |
| 3065 | AY512915 | NR_033559.1 | chr6:95290573-95333993 |
| 3066 | AY512931 | NR_033588.1 | chr8:45060701-45065418 |
| 3067 | AY761184 | NM_001007582.3 | chr8:21702523-21703647 |
| 3068 | AY761185 | NM_001012640.2 | chr8:20943693-20944748 |
| 3069 | Aym1 | NM_001012726.2 | chr5:113357293-113357821 |
| 3070 | Azgp1 | NM_013478.2 | chr5:137981520-137990232 |
| 3071 | Azi2 | NM_001048146.2 | chr9:118040521-118060484 |
| 3072 | Azin1 | NM_001102458.1 | chr15:38487429-38519266 |
| 3073 | B020004C17Rik | NM_001256060.1 | chr14:57015133-57018982 |
| 3074 | B020004J07Rik | NM_001033790.3 | chr4:101834968-101844022 |
| 3075 | B020014A21Rik | NR_045964.1 | chr10:3125090-3133193 |
| 3076 | B020018J22Rik | NR_045950.1 | chr12:112428283-112435338 |
| 3077 | B020031M17Rik | NM_001033769.2 | chr13:119949356-119950806 |
| 3078 | B130006D01Rik | NR_028263.1 | chr1:95723585-95726773 |
| 3079 | B130024G19Rik | NR_045850.1 | chr7:70365382-70411146 |
| 3080 | B130034C11Rik | NR_040375.1 | chr16:87496072-87504038 |
| 3081 | B230112J18Rik | NR_110475.1 | chr5:116312359-116318274 |
| 3082 | B230118H07Rik | NM_026592.3 | chr2:101560780-101628986 |
| 3083 | B230119M05Rik | NR_045454.1 | chrX:134684561-134686462 |
| 3084 | B230206H05Rik | NR_033532.1 | chr7:141359177-141365110 |
| 3085 | B230208H11Rik | NR_038027.1 | chr10:12916645-12923127 |
| 3086 | B230209E15Rik | NR_045727.1 | chr7:61529409-61615327 |
| 3087 | B230214G05Rik | NR_045281.1 | chr15:88314873-88372651 |
| 3088 | B230216G23Rik | NM_001242345.1 | chr6:142413430-142419740 |
| 3089 | B230216N24Rik | NR_037993.1 | chr1:98031122-98047793 |
| 3090 | B230217C12Rik | NM_001080935.1 | chr11:97840779-97843043 |
| 3091 | B230217Q12Rik | NR_040316.1 | chr19:57323196-57360899 |
| 3092 | B230219D22Rik | NM_181278.2 | chr13:55693123-55703500 |
| 3093 | B230312C02Rik | NR_040745.1 | chr2:180370857-180385885 |
| 3094 | B230319C09Rik | NR_028382.1 | chr6:83441754-83448322 |
| 3095 | B230323A14Rik | NR_040765.1 | chr9:69761145-69830199 |
| 3096 | B2m | NM_009735.3 | chr2:122147686-122153082 |
| 3097 | B330016D10Rik | NR_030695.1 | chr4:141546161-141548313 |
| 3098 | B3galnt1 | NM_020026.4 | chr3:69573918-69598960 |
| 3099 | B3galnt2 | NM_178640.2 | chr13:13954673-13999068 |
| 3100 | B3galt1 | NM_020283.4 | chr2:68104671-68122882 |
| 3101 | B3galt2 | NM_020025.4 | chr1:143640696-143649937 |
| 3102 | B3galt4 | NM_019420.2 | chr17:33949911-33951488 |
| 3103 | B3galt5 | NM_001122993.1 | chr16:96235800-96319858 |
| 3104 | B3galt6 | NM_080445.4 | chr4:155989465-155992678 |
| 3105 | B3gat1 | NM_029792.1 | chr9:26751561-26761338 |
| 3106 | B3gat2 | NM_172124.2 | chr1:23761925-23847858 |
| 3107 | B3gat3 | NM_024256.2 | chr19:8920392-8927236 |
| 3108 | B3glct | NM_001081204.1 | chr5:149678256-149762599 |
| 3109 | B3gnt1 | NM_175383.2 | chr19:503882S-5041134 |
| 3110 | B3gnt2 | NM_001169114.1 | chr11:22834738-22860336 |
| 3111 | B3gnt3 | NM_028189.3 | chr8:71691719-71701800 |
| 3112 | B3gnt4 | NM_198611.2 | chr5:123510459-123511882 |
| 3113 | B3gnt5 | NM_001159407.1 | chr16:19760233-19772753 |
| 3114 | B3gnt6 | NM_001081167.1 | chr7:98192414-98199475 |
| 3115 | B3gnt7 | NM_145229.2 | chr1:86303220-86307305 |
| 3116 | B3gnt8 | NM_001036740.2 | chr7:25627623-25629490 |
| 3117 | B3gnt9 | NM_001271915.1 | chr8:105252637-105255153 |
| 3118 | B3gntl1 | NM_178664.5 | chr11:121616207-121673151 |
| 3119 | B430010I23Rik | NR_015457.1 | chr8:41017467-41024216 |
| 3120 | B430212C06Rik | NR_033214.1 | chr18:67321208-67344103 |
| 3121 | B430306N03Rik | NM_177083.4 | chr17:48316161-48326511 |
| 3122 | B430319G15Rik | NR_029474.1 | chr9:92538800-92542869 |
| 3123 | B4galnt1 | NM_001127165.1 | chr10:127165155-127168523 |
| 3124 | B4galnt2 | NM_008081.3 | chr11:95863558-95914871 |
| 3125 | B4galnt3 | NM_198884.1 | chr6:120203809-120294559 |
| 3126 | B4galnt4 | NM_177897.3 | chr7:141061273-141072119 |
| 3127 | B4galt1 | NM_022305.4 | chr4:40804581-40854537 |
| 3128 | B4galt2 | NM_001253381.1 | chr4:117872999-117883476 |
| 3129 | B4galt3 | NM_020579.2 | chr1:171270327-171276895 |
| 3130 | B4galt4 | NM_001285793.1 | chr16:38742258-38769054 |
| 3131 | B4galt5 | NM_019835.2 | chr2:167298444-167349178 |

| | | | |
|---|---|---|---|
| 3132 | B4galt6 | NM_019737.2 | chr18:20684598-20746404 |
| 3133 | B4galt7 | NM_146045.2 | chr13:55599895-55610443 |
| 3134 | B630005N14Rik | NM_175312.4 | chr6:13625674-13677966 |
| 3135 | B630019K06Rik | NR_045448.1 | chrX:8892352-8894964 |
| 3136 | B830017H08Rik | NR_027959.1 | chr16:17833118-17835019 |
| 3137 | B930003M22Rik | NR_037588.1 | chr17:10319918-10321141 |
| 3138 | B930018H19Rik | NR_040706.1 | chr8:34589419-34640316 |
| 3139 | B930022SP03Rik | NR_040705.1 | chr8:10870421-10882454 |
| 3140 | B930041F14Rik | NM_178699.4 | chr4:155694341-155696483 |
| 3141 | B930059L03Rik | NR_033340.1 | chr12:110591373-110592679 |
| 3142 | B930092H01Rik | NR_045334.1 | chr9:61259226-61293809 |
| 3143 | B9d1 | NM_013717.2 | chr11:61505171-61512927 |
| 3144 | B9d2 | NM_172148.1 | chr7:25681157-25686558 |
| 3145 | Baalc | NM_080640.5 | chr15:38933908-38952916 |
| 3146 | Baat | NM_007519.2 | chr4:49489417-49506558 |
| 3147 | Babam1 | NM_026636.2 | chr8:71396854-71404772 |
| 3148 | Bace1 | NM_001145947.1 | chr9:45838528-45862484 |
| 3149 | Bace2 | NM_019517.4 | chr16:97356727-97439012 |
| 3150 | Bach1 | NM_007520.2 | chr16:87698953-87733346 |
| 3151 | Bach2 | NM_001109661.1 | chr4:32417434-32586108 |
| 3152 | Bach2os | NR_026843.1 | chr4:32559679-32571662 |
| 3153 | Bad | NM_001285453.1 | chr19:6942561-6951905 |
| 3154 | Bag1 | NM_001171739.1 | chr4:40936397-40948294 |
| 3155 | Bag2 | NM_145392.2 | chr1:33745483-33757750 |
| 3156 | Bag3 | NM_013863.5 | chr7:128523582-128546979 |
| 3157 | Bag4 | NM_026121.3 | chr8:25764538-25785209 |
| 3158 | Bag5 | NM_027404.2 | chr12:111709489-111713256 |
| 3159 | Bag6 | NM_001252468.1 | chr17:35135177-35147322 |
| 3160 | Bahcc1 | NM_198423.3 | chr11:120232946-120292297 |
| 3161 | Bahd1 | NM_001045523.1 | chr2:118901614-118924524 |
| 3162 | Bai1 | NM_174991.3 | chr15:74516195-74589464 |
| 3163 | Bai2 | NM_001199696.1 | chr4:129985077-130022633 |
| 3164 | Bai3 | NM_175642.4 | chr1:25067475-25829707 |
| 3165 | Baiap2 | NM_001037754.3 | chr11:119943091-120002618 |
| 3166 | Baiap2l1 | NM_025833.3 | chr5:144264524-144358112 |
| 3167 | Baiap2l2 | NM_177580.3 | chr15:79258194-79285509 |
| 3168 | Baiap3 | NM_001163270.1 | chr17:25242658-25256364 |
| 3169 | Bak1 | NM_007523.2 | chr17:27019811-27028626 |
| 3170 | Bambi | NM_026585.2 | chr18:3507956-3516404 |
| 3171 | Bambi-ps1 | NR_027919.1 | chr2:122466582-122467797 |
| 3172 | Banf1 | NM_001032231.2 | chr19:5364632-5366363 |
| 3173 | Banf2 | NM_001044750.1 | chr2:144033101-144073979 |
| 3174 | Bank1 | NM_001033350.3 | chr3:136053363-136326066 |
| 3175 | Banp | NM_001110100.2 | chr8:121950491-122029260 |
| 3176 | Bap1 | NM_027088.2 | chr14:31251488-31259929 |
| 3177 | Bard1 | NM_007525.3 | chr1:71027534-71102972 |
| 3178 | Barhl1 | NM_001164186.1 | chr2:28907679-28916440 |
| 3179 | Barhl2 | NM_001005477.1 | chr5:106452522-106458166 |
| 3180 | Barx1 | NM_007526.4 | chr13:48683035-48666507 |
| 3181 | Barx2 | NM_013800.2 | chr9:31846043-31913285 |
| 3182 | Bosp1 | NM_025729.5 | chr15:25363276-25413764 |
| 3183 | Batf | NM_016767.2 | chr12:85686719-85709087 |
| 3184 | Batf2 | NM_028967.1 | chr19:6164457-6172475 |
| 3185 | Batf3 | NM_030060.2 | chr1:191098413-191108943 |
| 3186 | Bax | NM_007527.3 | chr7:45461694-45466898 |
| 3187 | Baz1a | NM_013815.2 | chr12:54892988-54986336 |
| 3188 | Baz1b | NM_011714.2 | chr5:135187322-135246129 |
| 3189 | Baz2a | NM_054078.2 | chr10:128092782-128129309 |
| 3190 | Baz2b | NM_001001182.3 | chr2:59899362-60125740 |
| 3191 | BB014433 | NR_037972.1 | chr8:15041445-15046078 |
| 3192 | BB019430 | NR_033565.1 | chr16:58696744-58704277 |
| 3193 | BB031773 | NR_028391.1 | chr4:103004105-103011965 |
| 3194 | BB123696 | NR_027893.1 | chr13:52729369-52757205 |
| 3195 | BB283400 | NR_038124.1 | chr6:30178622-30178040 |
| 3196 | BB287469 | NM_001177573.1 | chr12:87618867-87820676 |
| 3197 | BB557941 | NR_040356.1 | chr2:57127476-57181754 |
| 3198 | Bbc3 | NM_133234.2 | chr7:16309582-16318334 |
| 3199 | Bbip1 | NM_001195338.1 | chr19:53919658-53944627 |
| 3200 | Bbox1 | NM_130452.1 | chr2:110265082-110305725 |
| 3201 | Bbs1 | NM_001033128.3 | chr19:4886881-4906627 |
| 3202 | Bbs10 | NM_027914.1 | chr10:111298678-111301736 |
| 3203 | Bbs12 | NM_001008502.2 | chr3:37812553-37821451 |
| 3204 | Bbs2 | NM_026116.2 | chr8:94067953-94098811 |
| 3205 | Bbs4 | NM_175325.3 | chr9:59321965-59353508 |
| 3206 | Bbs5 | NM_028284.2 | chr2:69647254-69667569 |
| 3207 | Bbs7 | NM_027810.3 | chr3:36573142-36613389 |
| 3208 | Bbs9 | NM_178415.1 | chr9:22475714-22888280 |
| 3209 | Bbx | NM_027444.3 | chr16:50191843-50432389 |
| 3210 | BC002163 | NR_002445.2 | chr4:42955579-123718161 |
| 3211 | BC003331 | NM_001077237.1 | chr1:150361310-150393055 |
| 3212 | BC003965 | NM_183150.2 | chr17:25184560-25187662 |
| 3213 | BC004004 | NM_030561.3 | chr7:29268787-29302887 |
| 3214 | BC005537 | NM_024473.3 | chr13:24801656-24812899 |
| 3215 | BC005561 | NM_001166581.1 | chr5:104508351-104522383 |
| 3216 | BC005624 | NM_144885.2 | chr2:30972832-30981941 |
| 3217 | BC005764 | NM_001170935.1 | chr10:79860474-79874634 |
| 3218 | BC006965 | NR_024085.1 | chr11:112663926-112711356 |
| 3219 | BC016579 | NM_145389.2 | chr16:45626847-45654118 |
| 3220 | BC017158 | NM_145590.2 | chr7:128271378-128298131 |
| 3221 | BC017643 | NM_001252548.1 | chr11:121222588-121229309 |
| 3222 | BC018242 | NM_001290299.1 | chr9:21937009-21948907 |
| 3223 | BC018473 | NR_003364.1 | chr11:116752166-116757883 |
| 3224 | BC018507 | NM_144837.3 | chr13:70588688-70637634 |
| 3225 | BC020402 | NR_033219.1 | chr10:7678970-7681158 |
| 3226 | BC021614 | NM_144869.2 | chr19:4057486-4059294 |

Fig. 26 - 18

| | | | |
|---|---|---|---|
| 3227 | BC021767 | NR_033629.1 | chr3:94660588-94667152 |
| 3228 | BC021785 | NM_001001489.3 | chr10:39968152-39986646 |
| 3229 | BC021891 | NM_145608.2 | chr8:125910449-125947439 |
| 3230 | BC022687 | NM_145450.3 | chr12:112808974-112816245 |
| 3231 | BC023829 | NM_001033328.2 | chrX:70460055-70477043 |
| 3232 | BC024139 | NM_001142968.1 | chr15:76119517-76126556 |
| 3233 | BC024386 | NR_015583.1 | chr7:140906063-140907967 |
| 3234 | BC024978 | NM_001243688.1 | chr7:27195780-27204320 |
| 3235 | BC025920 | NR_030677.1 | chr10:81606307-81609836 |
| 3236 | BC026585 | NM_001033284.1 | chr1:157458581-157488733 |
| 3237 | BC027072 | NM_146082.3 | chr7:71743554-71752885 |
| 3238 | BC027231 | NM_145972.4 | chr16:44724300-44737284 |
| 3239 | BC028528 | NM_153513.2 | chr3:95884972-95891930 |
| 3240 | BC029214 | NM_153557.3 | chr2:25459487-25461094 |
| 3241 | BC029722 | NR_015528.1 | chr2:155817731-155819203 |
| 3242 | BC030307 | NM_001003910.2 | chr10:86705810-86776843 |
| 3243 | BC030336 | NM_001164580.1 | chr7:120677619-120734854 |
| 3244 | BC030499 | NM_001287206.1 | chr11:78290840-78296805 |
| 3245 | BC030500 | NM_173411.2 | chr8:58911754-58914298 |
| 3246 | BC030867 | NM_153544.3 | chr11:102248881-102265183 |
| 3247 | BC030870 | NR_033217.1 | chr8:65085614-65129537 |
| 3248 | BC031181 | NM_001001181.3 | chr18:75005899-75009933 |
| 3249 | BC031361 | NR_033221.1 | chr16:38085063-38089260 |
| 3250 | BC033916 | NR_040470.1 | chr17:33905194-33906675 |
| 3251 | BC035044 | NM_001254964.1 | chr6:128848043-128891124 |
| 3252 | BC037032 | NR_028266.1 | chr15:4020110-4027406 |
| 3253 | BC037034 | NM_153161.3 | chr5:138259657-138264052 |
| 3254 | BC037704 | NM_045645.1 | chr19:43675177-43677170 |
| 3255 | BC039771 | NR_033220.1 | chr2:145701194-145753672 |
| 3256 | BC039966 | NR_040670.1 | chr4:153948454-153950476 |
| 3257 | BC048403 | NM_173022.2 | chr10:121739936-121752859 |
| 3258 | BC048502 | NM_177631.3 | chr15:103438959-103448459 |
| 3259 | BC048507 | NM_001001185.3 | chr13:67863325-67863923 |
| 3260 | BC048546 | NM_001001179.3 | chr6:128538921-128581606 |
| 3261 | BC048562 | NM_001004192.1 | chr9:108436481-108446083 |
| 3262 | BC048602 | NR_045280.1 | chr5:35307009-35328535 |
| 3263 | BC048609 | NM_001111317.1 | chr19:6080037-6080785 |
| 3264 | BC048644 | NM_001033485.2 | chr8:121907832-121918428 |
| 3265 | BC048671 | NM_177738.2 | chr6:90301269-90305448 |
| 3266 | BC048679 | NM_001193274.1 | chr7:81494273-81498330 |
| 3267 | BC049352 | NM_001198971.1 | chr9:45195765-45249985 |
| 3268 | BC049635 | NM_177785.4 | chr4:42868002-42874203 |
| 3269 | BC049715 | NM_178776.3 | chr6:136828842-136840557 |
| 3270 | BC049730 | NM_199150.1 | chr7:24709258-24714535 |
| 3271 | BC049762 | NM_177567.3 | chr11:51253650-51262951 |
| 3272 | BC051019 | NM_001040700.2 | chr7:109712180-109723771 |
| 3273 | BC051142 | NM_001001177.2 | chr17:34398819-34460734 |
| 3274 | BC051226 | NR_045146.1 | chr17:33908181-33909178 |
| 3275 | BC051537 | NR_046183.1 | chr17:34083842-34095309 |
| 3276 | BC051628 | NM_199312.3 | chr2:181220015-181222851 |
| 3277 | BC051665 | NM_199148.2 | chr13:60781886-60786864 |
| 3278 | BC052040 | NM_001145898.1 | chr2:155581715-155778768 |
| 3279 | BC052688 | NR_028430.1 | chr13:61771579-61787282 |
| 3280 | BC053393 | NM_001025435.3 | chr11:46571512-46589232 |
| 3281 | BC053749 | NM_183321.1 | chr7:30539133-30552272 |
| 3282 | BC055111 | NM_183182.3 | chr4:106590908-106617238 |
| 3283 | BC055324 | NM_201364.1 | chr1:163954007-163994781 |
| 3284 | BC055402 | NR_037990.1 | chr1:57200644-57214996 |
| 3285 | BC061194 | NM_001001334.2 | chr2:18699021-18749605 |
| 3286 | BC061195 | NR_105038.1 | chrX:93156153-93183944 |
| 3287 | BC061212 | NM_198667.1 | chr5:94066454-94070545 |
| 3288 | BC063237 | NM_198673.2 | chr14:44500121-44506345 |
| 3289 | BC064078 | NR_015455.1 | chr6:128993019-129006649 |
| 3290 | BC065397 | NR_033324.1 | chrX:136742956-136803361 |
| 3291 | BC068157 | NM_207203.2 | chr8:4209542-4217312 |
| 3292 | BC068281 | NM_001170858.1 | chr12:4843302-4856967 |
| 3293 | BC080695 | NM_001007579.3 | chr4:143567466-143573798 |
| 3294 | BC089491 | NM_175033.3 | chr7:28284651-28291134 |
| 3295 | BC089597 | NM_145424.2 | chr10:127866475-127877319 |
| 3296 | BC094916 | NM_001024721.2 | chr1:173521310-173535957 |
| 3297 | Bc1 | NR_038088.1 | chrX:79697304-163352564 |
| 3298 | BC100451 | NM_021840.2 | chr11:118332359-118342534 |
| 3299 | BC100530 | NM_001082546.1 | chr16:36359381-36367570 |
| 3300 | BC107364 | NM_001256180.1 | chr3:96433787-96452306 |
| 3301 | BC117090 | NM_001001332.2 | chr16:36321664-36334332 |
| 3302 | BC147527 | NM_001037925.2 | chr13:120300391-120308841 |
| 3303 | Bcam | NM_020486.2 | chr7:19756137-19770532 |
| 3304 | Bcan | NM_001109758.1 | chr3:87992513-88000356 |
| 3305 | Bcap29 | NM_001164090.1 | chr12:31595353-31634658 |
| 3306 | Bcap31 | NM_012060.5 | chrX:73686177-73716204 |
| 3307 | Bcar1 | NM_001198839.1 | chr8:111710474-111732136 |
| 3308 | Bcar3 | NM_013867.2 | chr3:122419779-122530182 |
| 3309 | Bcas1 | NM_001164369.1 | chr2:170346990-170427845 |
| 3310 | Bcas1os2 | NR_040610.1 | chr2:170356360-170380435 |
| 3311 | Bcas2 | NM_026602.3 | chr3:103171710-103179154 |
| 3312 | Bcas3 | NM_001166642.1 | chr11:85353163-85826058 |
| 3313 | Bcas3os1 | NR_045875.1 | chr11:85702199-85719744 |
| 3314 | Bcas3os2 | NR_046194.1 | chr11:85766838-85775680 |
| 3315 | Bcat1 | NM_001024468.3 | chr6:144993834-145048812 |
| 3316 | Bcat2 | NM_001243052.1 | chr7:45571278-45588710 |
| 3317 | Bccip | NM_025392.2 | chr7:133709332-133721145 |
| 3318 | Bcdin3d | NM_029236.2 | chr15:99470083-99474730 |
| 3319 | Bche | NM_009738.3 | chr3:73635808-73708415 |
| 3320 | Bckdha | NM_007533.5 | chr7:25629851-25658761 |
| 3321 | Bckdhb | NM_199195.1 | chr9:83948780-84124240 |

| | | | |
|---|---|---|---|
| 3322 | Bckdk | NM_009739.3 | chr7:127904072-127909664 |
| 3323 | Bcl10 | NM_009740.2 | chr3:145924261-145934364 |
| 3324 | Bcl11a | NM_001159289.1 | chr11:24078055-24173558 |
| 3325 | Bcl11b | NM_001079883.1 | chr12:107910402-108003414 |
| 3326 | Bcl2 | NM_009741.5 | chr1:106538175-106714290 |
| 3327 | Bcl2a1a | NM_009742.3 | chr9:88956919-88962416 |
| 3328 | Bcl2a1b | NM_007534.3 | chr9:89199272-89207838 |
| 3329 | Bcl2a1c | NM_007535.2 | chr9:114330134-114330578 |
| 3330 | Bcl2a1d | NM_007536.2 | chr9:88723287-88731850 |
| 3331 | Bcl2l1 | NM_001289716.1 | chr2:152780663-152830717 |
| 3332 | Bcl2l10 | NM_013479.2 | chr9:75347757-75351640 |
| 3333 | Bcl2l11 | NM_001284410.2 | chr2:128127574-128131498 |
| 3334 | Bcl2l12 | NM_029410.3 | chr7:44991221-44997579 |
| 3335 | Bcl2l13 | NM_153576.2 | chr6:120836229-120892842 |
| 3336 | Bcl2l14 | NM_025778.3 | chr6:134396328-134438724 |
| 3337 | Bcl2l15 | NM_001142959.1 | chr3:103832695-103838648 |
| 3338 | Bcl2l2 | NM_007537.1 | chr14:54883424-54888234 |
| 3339 | Bcl3 | NM_033601.3 | chr7:19808461-19822755 |
| 3340 | Bcl6 | NM_009744.3 | chr16:23965051-23988612 |
| 3341 | Bcl6b | NM_007528.3 | chr11:70224126-70229798 |
| 3342 | Bcl7a | NM_029850.3 | chr5:123344447-123374083 |
| 3343 | Bcl7b | NM_009745.2 | chr5:135168371-135181852 |
| 3344 | Bcl7c | NM_009746.2 | chr7:127704977-127708766 |
| 3345 | Bcl9 | NM_029933.4 | chr3:97203661-97227364 |
| 3346 | Bcl9l | NM_030256.2 | chr9:44499135-44510412 |
| 3347 | Bclaf1 | NM_001025392.1 | chr10:20312468-20342501 |
| 3348 | Bcmo1 | NM_001163028.1 | chr8:117095864-117133720 |
| 3349 | Bco2 | NM_133217.3 | chr9:50533086-50555138 |
| 3350 | Bcor | NM_001168321.1 | chrX:12036737-12160355 |
| 3351 | Bcorl1 | NM_178782.4 | chrX:48341357-48406728 |
| 3352 | Bcr | NM_001081412.2 | chr10:75060895-75184923 |
| 3353 | Bcs1l | NM_025784.5 | chr1:74588288-74592443 |
| 3354 | Bdh1 | NM_001122683.1 | chr16:31428752-31458901 |
| 3355 | Bdh2 | NM_001172055.1 | chr3:135281220-135304425 |
| 3356 | Bdkrb1 | NM_007539.2 | chr12:105604090-105605428 |
| 3357 | Bdkrb2 | NM_009747.2 | chr12:105563171-105593071 |
| 3358 | Bdnf | NM_001048139.1 | chr2:109675896-109727043 |
| 3359 | Bdp1 | NM_001081061.1 | chr13:100017993-100104070 |
| 3360 | Bean1 | NM_001141922.1 | chr8:104170512-104219097 |
| 3361 | Becn1 | NM_019584.3 | chr11:101288266-101302267 |
| 3362 | Becn2 | NM_001206692.1 | chr1:175920328-175922225 |
| 3363 | Begain | NM_001163175.1 | chr12:109032181-109068217 |
| 3364 | Bend3 | NM_199028.2 | chr10:43479139-43515417 |
| 3365 | Bend4 | NM_001164806.1 | chr5:67392146-67427799 |
| 3366 | Bend5 | NM_026279.3 | chr4:111415005-111460298 |
| 3367 | Bend6 | NM_177235.3 | chr1:33852051-33907621 |
| 3368 | Bend7 | NM_001190400.1 | chr2:4717830-4802146 |
| 3369 | Best1 | NM_011913.2 | chr19:9985171-10001633 |
| 3370 | Best2 | NM_001130194.1 | chr8:85007202-85014408 |
| 3371 | Best3 | NM_001007583.1 | chr10:116986313-117025040 |
| 3372 | Bet1 | NM_009748.2 | chr5:4076903-4086927 |
| 3373 | Bet1l | NM_018742.5 | chr7:140853383-140856383 |
| 3374 | Bex1 | NM_009052.2 | chrX:136213971-136215513 |
| 3375 | Bex2 | NM_009749.2 | chrX:136066564-136068236 |
| 3376 | Bex4 | NM_212457.2 | chrX:136139044-136140437 |
| 3377 | Bex6 | NM_001035539.2 | chr16:32179799-32186944 |
| 3378 | Bfar | NM_001177552.1 | chr16:136671857-13703612 |
| 3379 | Bfsp1 | NM_001291061.1 | chr2:143826527-143863173 |
| 3380 | Bfsp2 | NM_001002896.2 | chr9:103424923-103480328 |
| 3381 | Bglap | NM_001037939.2 | chr3:88383494-88384466 |
| 3382 | Bglap2 | NM_001032298.3 | chr3:88377735-88378701 |
| 3383 | Bglap3 | NM_031368.5 | chr3:88368615-88369831 |
| 3384 | Bgn | NM_007542.5 | chrX:73483834-73495936 |
| 3385 | Bhlha15 | NM_010800.4 | chr5:144190285-144194441 |
| 3386 | Bhlha9 | NM_177182.4 | chr11:76672469-76673676 |
| 3387 | Bhlhb9 | NM_001098222.1 | chrX:135885850-135891081 |
| 3388 | Bhlhe22 | NM_021560.4 | chr3:18054324-18057514 |
| 3389 | Bhlhe23 | NM_080641.5 | chr2:180774380-180776900 |
| 3390 | Bhlhe40 | NM_011498.4 | chr6:108660628-108666925 |
| 3391 | Bhlhe41 | NM_001271768.1 | chr6:145858242-145865420 |
| 3392 | Bhmt | NM_016668.3 | chr13:93916890-93637758 |
| 3393 | Bhmt2 | NM_023884.2 | chr13:93656096-93674302 |
| 3394 | Bicc1 | NM_031397.2 | chr10:70925095-71159634 |
| 3395 | Bicd1 | NM_001112796.2 | chr6:149408983-149566326 |
| 3396 | Bicd2 | NM_001039179.2 | chr13:49341548-49387026 |
| 3397 | Bid | NM_007544.3 | chr6:120893118-120916820 |
| 3398 | Bik | NM_007546.2 | chr15:83526851-83544635 |
| 3399 | Bin1 | NM_001083334.1 | chr18:32377216-32435740 |
| 3400 | Bin2 | NM_001270537.1 | chr15:100641081-100669500 |
| 3401 | Bin3 | NM_021328.3 | chr14:70100144-70138206 |
| 3402 | Birc2 | NM_007465.3 | chr9:7818225-7837057 |
| 3403 | Birc3 | NM_007464.3 | chr9:7848700-7873170 |
| 3404 | Birc5 | NM_001012273.1 | chr11:117849236-117855743 |
| 3405 | Birc6 | NM_007566.3 | chr17:74528294-74703356 |
| 3406 | Birc7 | NM_001163247.1 | chr2:180929022-180934010 |
| 3407 | Bivm | NM_144558.4 | chr1:44119967-44144771 |
| 3408 | Blcap | NM_016916.3 | chr2:157556361-157566361 |
| 3409 | Blk | NM_007549.2 | chr14:63372836-63417187 |
| 3410 | Blm | NM_001042527.2 | chr7:80454992-80535119 |
| 3411 | Blmh | NM_178645.4 | chr11:76945655-76987389 |
| 3412 | Blnk | NM_008528.4 | chr19:40928926-40994535 |
| 3413 | Bloc1s1 | NM_015740.3 | chr10:128919913-128923524 |
| 3414 | Bloc1s2 | NM_028607.1 | chr19:44139246-44146446 |
| 3415 | Bloc1s3 | NM_177692.3 | chr7:19505803-19508331 |
| 3416 | Bloc1s4 | NM_133724.3 | chr5:36747373-36748679 |

Fig. 26 - 19

| | | | |
|---|---|---|---|
| 3417 | Bloc1s5 | NM_139063.1 | chr13:38602705-38635109 |
| 3418 | Bloc1s6 | NM_019788.3 | chr2:122738504-122749487 |
| 3419 | Blvra | NM_026678.4 | chr2:127070656-127097084 |
| 3420 | Blvrb | NM_001290525.1 | chr7:27452417-27465981 |
| 3421 | Blzf1 | NM_001160208.1 | chr1:164289799-164307484 |
| 3422 | Bmf | NM_138313.3 | chr2:118528756-118549678 |
| 3423 | Bmi1 | NM_007552.4 | chr2:18677017-18686629 |
| 3424 | Bmp1 | NM_009755.3 | chr14:70474554-70520260 |
| 3425 | Bmp10 | NM_009756.3 | chr6:87428993-87434512 |
| 3426 | Bmp15 | NM_009757.4 | chrX:6314105-6320723 |
| 3427 | Bmp2 | NM_007553.3 | chr2:133552158-133562896 |
| 3428 | Bmp2k | NM_080708.1 | chr5:96997668-97091048 |
| 3429 | Bmp3 | NM_173404.5 | chr5:98854414-98880960 |
| 3430 | Bmp4 | NM_007554.3 | chr14:46383519-46390599 |
| 3431 | Bmp5 | NM_007555.4 | chr9:75775364-75899017 |
| 3432 | Bmp6 | NM_007556.3 | chr13:38345715-38499728 |
| 3433 | Bmp7 | NM_007557.3 | chr2:172868011-172940321 |
| 3434 | Bmp8a | NM_001256019.1 | chr4:123312649-123343252 |
| 3435 | Bmp8b | NM_007559.4 | chr4:123105164-123126091 |
| 3436 | Bmper | NM_028472.2 | chr9:23223075-23485215 |
| 3437 | Bmpr1a | NM_009758.4 | chr14:34411067-34502546 |
| 3438 | Bmpr1b | NM_001277216.1 | chr3:141837135-142169228 |
| 3439 | Bmpr2 | NM_007561.4 | chr1:59764278-59878081 |
| 3440 | Bms1 | NM_194339.1 | chr6:118883380-118919417 |
| 3441 | Bmx | NM_009759.4 | chrX:164192841-164256193 |
| 3442 | Bmyc | NM_023326.2 | chr2:25706878-25707719 |
| 3443 | Bnc1 | NM_007562.2 | chr7:81966661-81992299 |
| 3444 | Bnc2 | NM_172870.4 | chr4:84272541-84675086 |
| 3445 | Bnip1 | NM_172149.5 | chr17:26781078-26792521 |
| 3446 | Bnip2 | NM_001008238.3 | chr9:69989465-70011659 |
| 3447 | Bnip3 | NM_009760.4 | chr7:138890835-138909506 |
| 3448 | Bnip3l | NM_009761.3 | chr14:66985239-67008877 |
| 3449 | Bnipl | NM_001168356.1 | chr3:95241292-95251193 |
| 3450 | Boc | NM_172506.2 | chr16:44485044-44558870 |
| 3451 | Bod1 | NM_001024919.1 | chr11:31665149-31671862 |
| 3452 | Bod1l | NM_001081422.3 | chr5:41787539-41844315 |
| 3453 | Bok | NM_016778.3 | chr1:93685574-93695770 |
| 3454 | Bola1 | NM_026975.2 | chr3:96196587-96197586 |
| 3455 | Bola2 | NM_175103.3 | chr7:126695999-126696693 |
| 3456 | Bola3 | NM_175277.4 | chr6:83349483-83358392 |
| 3457 | Boll | NM_001113367.1 | chr1:55300068-55362707 |
| 3458 | Bop1 | NM_013481.1 | chr15:76452995-76477269 |
| 3459 | Bora | NM_175265.4 | chr14:99046376-99074107 |
| 3460 | Bpgm | NM_007563.4 | chr6:34476355-34505610 |
| 3461 | Bphl | NM_026512.1 | chr13:34037640-34074074 |
| 3462 | Bpi | NM_177850.3 | chr2:158258240-158284531 |
| 3463 | Bpifa1 | NM_011126.3 | chr2:154142879-154149217 |
| 3464 | Bpifa2 | NM_008953.2 | chr2:154008275-154016073 |
| 3465 | Bpifa3 | NM_001291079.1 | chr2:154130335-154138359 |
| 3466 | Bpifa5 | NM_025990.4 | chr2:154162606-154168446 |
| 3467 | Bpifa6 | NM_001080811.1 | chr2:153974944-154000495 |
| 3468 | Bpifb1 | NM_001012392.1 | chr2:154190817-154220343 |
| 3469 | Bpifb2 | NM_025635.3 | chr2:153875044-153895270 |
| 3470 | Bpifb3 | NM_194357.1 | chr2:153918229-153932996 |
| 3471 | Bpifb4 | NM_001034875.3 | chr2:153940861-153963852 |
| 3472 | Bpifb5 | NM_144890.2 | chr2:154223741-154240902 |
| 3473 | Bpifb6 | NM_199303.2 | chr2:153900387-153912793 |
| 3474 | Bpifb9a | NM_175167.3 | chr2:154257878-154271243 |
| 3475 | Bpifb9b | NM_001025574.1 | chr2:154307243-154320642 |
| 3476 | Bpifc | NM_177772.4 | chr10:85959690-86011860 |
| 3477 | Bpnt1 | NM_011794.3 | chr1:185332158-185357769 |
| 3478 | Bptf | NM_176850.2 | chr11:107033080-107131922 |
| 3479 | Braf | NM_139294.5 | chr6:39603236-39725463 |
| 3480 | Brap | NM_001289543.1 | chr5:121660562-121687249 |
| 3481 | Brat1 | NM_001276287.1 | chr5:140705065-140719378 |
| 3482 | Brca1 | NM_009764.3 | chr11:101488763-101551955 |
| 3483 | Brca2 | NM_001081001.2 | chr5:150522620-150570146 |
| 3484 | Brcc3 | NM_001166457.1 | chrX:75416627-75454001 |
| 3485 | Brd1 | NM_001033274.3 | chr15:88687034-88734219 |
| 3486 | Brd2 | NM_001037293.1 | chr17:34112018-34122607 |
| 3487 | Brd3 | NM_001113573.1 | chr2:27445580-27475673 |
| 3488 | Brd4 | NM_001286630.1 | chr17:32196271-32284133 |
| 3489 | Brd7 | NM_012047.2 | chr8:88332310-88362191 |
| 3490 | Brd8 | NM_001289606.1 | chr18:34598614-34624863 |
| 3491 | Brd9 | NM_001024508.3 | chr13:73937810-73960889 |
| 3492 | Brdt | NM_001079873.1 | chr5:58331193-107350741 |
| 3493 | Bre | NM_144541.1 | chr5:31698049-32084739 |
| 3494 | Brf1 | NM_028193.3 | chr12:112959861-113000621 |
| 3495 | Brf2 | NM_025686.2 | chr8:27123831-27128632 |
| 3496 | Bri3 | NM_001163709.1 | chr5:144244436-144264573 |
| 3497 | Bri3bp | NM_029752.2 | chr5:125441567-125460885 |
| 3498 | Bricd5 | NM_175586.2 | chr17:24473883-24475469 |
| 3499 | Brinp1 | NM_019967.2 | chr4:68761371-68954397 |
| 3500 | Brinp2 | NM_207583.2 | chr1:158245268-158356260 |
| 3501 | Brinp3 | NM_001145807.1 | chr1:146497686-146902472 |
| 3502 | Brip1 | NM_178309.2 | chr11:86058135-86201193 |
| 3503 | Brix1 | NM_026396.3 | chr15:10474778-10485937 |
| 3504 | Brk1 | NM_133937.1 | chr6:113604771-113616951 |
| 3505 | Brms1 | NM_134155.1 | chr19:5041403-5049917 |
| 3506 | Brms1l | NM_001037756.2 | chr12:55836365-55869735 |
| 3507 | Brox | NM_027861.2 | chr1:183276341-183297008 |
| 3508 | Brpf1 | NM_001282126.1 | chr6:113307136-113324862 |
| 3509 | Brpf3 | NM_001037765.1 | chr17:28801125-28838789 |
| 3510 | Brs3 | NM_009766.3 | chrX:57043073-57048758 |
| 3511 | Brsk1 | NM_001003920.3 | chr7:4690927-4715997 |

| | | | |
|---|---|---|---|
| 3512 | Brsk2 | NM_001009929.3 | chr7:141949750-142004243 |
| 3513 | Brwd1 | NM_001103179.1 | chr16:96001547-96082428 |
| 3514 | Brwd3 | NM_001081477.1 | chrX:108742207-108834355 |
| 3515 | Bscl2 | NM_001136064.3 | chr19:8837466-8848683 |
| 3516 | Bsdc1 | NM_133889.2 | chr4:129461678-129488432 |
| 3517 | Bsg | NM_001077184.1 | chr10:79704357-79711979 |
| 3518 | Bsn | NM_007567.2 | chr9:108096021-108190383 |
| 3519 | Bsnd | NM_080458.2 | chr4:106483457-106492243 |
| 3520 | Bsph1 | NM_001033418.4 | chr7:13450840-13473450 |
| 3521 | Bsph2 | NM_001080942.2 | chr7:13554865-13571067 |
| 3522 | Bspry | NM_138653.1 | chr4:62480066-62497298 |
| 3523 | Bst1 | NM_009763.3 | chr5:43818892-43843468 |
| 3524 | Bst2 | NM_198095.2 | chr8:71534261-71537437 |
| 3525 | Bsx | NM_178245.3 | chr9:40874126-40877972 |
| 3526 | Btaf1 | NM_001080706.1 | chr19:36926078-37014057 |
| 3527 | Btbd1 | NM_146193.2 | chr7:81792073-81829431 |
| 3528 | Btbd10 | NM_133700.2 | chr7:113315643-113369339 |
| 3529 | Btbd11 | NM_001017525.1 | chr10:85598410-85660292 |
| 3530 | Btbd16 | NM_001081038.2 | chr7:130774068-130825899 |
| 3531 | Btbd17 | NM_028055.4 | chr11:114790668-114795892 |
| 3532 | Btbd18 | NM_001145100.1 | chr2:84659078-84668781 |
| 3533 | Btbd19 | NR_024078.1 | chr4:117119217-117125725 |
| 3534 | Btbd2 | NM_145361.2 | chr10:80642616-80657071 |
| 3535 | Btbd3 | NM_001025431.1 | chr2:138256583-138287422 |
| 3536 | Btbd6 | NM_001145900.1 | chr12:112976481-112978940 |
| 3537 | Btbd7 | NM_172806.2 | chr12:102784647-102878406 |
| 3538 | Btbd8 | NM_001255991.1 | chr5:107437996-107491596 |
| 3539 | Btbd9 | NM_027060.1 | chr17:30215523-30576287 |
| 3540 | Btc | NM_007568.5 | chr5:91367260-91402994 |
| 3541 | Btd | NM_025295.4 | chr14:31641056-31668197 |
| 3542 | Btf3 | NM_001170540.1 | chr13:98309896-98317006 |
| 3543 | Btf3l4 | NM_027453.2 | chr4:108814294-108833584 |
| 3544 | Btg1 | NM_007569.2 | chr10:96617000-96622811 |
| 3545 | Btg2 | NM_007570.2 | chr1:134074864-134079155 |
| 3546 | Btg3 | NM_009770.3 | chr16:78359859-78376810 |
| 3547 | Btg4 | NM_019493.3 | chr9:51116000-51119700 |
| 3548 | Btk | NM_013482.2 | chrX:134542340-134583140 |
| 3549 | Btla | NM_001037719.2 | chr16:45224336-45252895 |
| 3550 | Btn1a1 | NM_013483.3 | chr13:23456992-23465901 |
| 3551 | Btn2a2 | NM_001289614.1 | chr13:23477062-23488857 |
| 3552 | Btnl1 | NM_001111094.1 | chr17:34377131-34386028 |
| 3553 | Btnl10 | NM_138678.2 | chr11:58918056-58926965 |
| 3554 | Btnl2 | NM_079835.2 | chr17:34354821-34369492 |
| 3555 | Btnl4 | NM_030746.1 | chr17:34469041-34475937 |
| 3556 | Btnl5-ps | NR_004051.1 | chr17:34487405-34497429 |
| 3557 | Btnl6 | NM_030747.1 | chr17:34507934-34517352 |
| 3558 | Btnl9 | NM_172793.2 | chr11:49168324-49187089 |
| 3559 | Btrc | NM_001037758.2 | chr19:45363733-45533343 |
| 3560 | Bub1 | NM_001113179.1 | chr2:127800199-127831859 |
| 3561 | Bub1b | NM_009773.3 | chr2:118598210-118641592 |
| 3562 | Bub3 | NM_009774.3 | chr7:131560390-131571898 |
| 3563 | Bud13 | NM_146000.2 | chr9:46283011-46298783 |
| 3564 | Bud31 | NM_001008705.2 | chr5:145140375-145148078 |
| 3565 | Bves | NM_024285.2 | chr10:45335761-45369708 |
| 3566 | Bysl | NM_016859.3 | chr17:47599530-47611492 |
| 3567 | Bzrap1 | NM_172449.2 | chr11:87760540-87785928 |
| 3568 | Bzw1 | NM_025824.3 | chr1:58393135-58406548 |
| 3569 | Bzw2 | NM_025840.3 | chr12:36091834-36156825 |
| 3570 | C030006K11Rik | NM_145472.2 | chr15:76721464-76723845 |
| 3571 | C030007H22Rik | NR_040482.1 | chr1:89360343-89406133 |
| 3572 | C030013G03Rik | NR_077216.1 | chr17:12466843-12479577 |
| 3573 | C030016D13Rik | NR_027987.1 | chr19:27430036-27432631 |
| 3574 | C030018K13Rik | NR_045411.1 | chr5:64477007-64479746 |
| 3575 | C030023E24Rik | NR_033502.1 | chrX:61191292-61194164 |
| 3576 | C030029H02Rik | NR_102277.1 | chr7:136268323-136318511 |
| 3577 | C030034I22Rik | NR_026848.1 | chr17:69416446-69419192 |
| 3578 | C030034L19Rik | NR_015499.2 | chr3:9409077-9413903 |
| 3579 | C030037D09Rik | NR_038058.1 | chr11:88718642-88728572 |
| 3580 | C030039L03Rik | NM_001112731.1 | chr7:27689339-27706482 |
| 3581 | C030046E11Rik | NM_001081319.1 | chr19:29522281-29605921 |
| 3582 | C130021I20Rik | NR_046275.1 | chr2:33641192-33645663 |
| 3583 | C130026E21Rik | NM_001037909.3 | chr1:85246343-85270566 |
| 3584 | C130026L21Rik | NR_015546.2 | chr5:111581560-111587153 |
| 3585 | C130030K03Rik | NR_046212.1 | chr10:49093680-49095843 |
| 3586 | C130036L24Rik | NR_015507.2 | chr1:86359573-86367964 |
| 3587 | C130046K22Rik | NR_102388.1 | chr11:103697723-103725573 |
| 3588 | C130050O18Rik | NM_177000.3 | chr5:139406386-139416092 |
| 3589 | C130060C02Rik | NR_045355.1 | chr19:15985074-16010912 |
| 3590 | C130060K24Rik | NM_175524.4 | chr8:65381293-65458150 |
| 3591 | C130071C03Rik | NR_015561.2 | chr13:83728105-83735669 |
| 3592 | C130074G19Rik | NM_178692.3 | chr1:184871925-184893036 |
| 3593 | C130079D12Rik | NM_177661.3 | chr5:59915213-59937949 |
| 3594 | C130080G10Rik | NM_028422.2 | chr2:114054395-114061502 |
| 3595 | C130083M11Rik | NR_040717.1 | chr5:52199983-52216433 |
| 3596 | C1d | NM_020558.3 | chr11:17257617-17269176 |
| 3597 | C1galt1 | NM_052993.3 | chr6:7845223-7872042 |
| 3598 | C1galt1c1 | NM_021550.3 | chrX:38630782-38635143 |
| 3599 | C1qa | NM_007572.2 | chr4:136895915-136898844 |
| 3600 | C1qb | NM_009777.2 | chr4:136880524-136886177 |
| 3601 | C1qbp | NM_007573.2 | chr11:70977845-70983026 |
| 3602 | C1qc | NM_007574.2 | chr4:136889801-136892914 |
| 3603 | C1ql1 | NM_011795.2 | chr11:102939263-102946461 |
| 3604 | C1ql2 | NM_207233.1 | chr1:120340581-120343174 |
| 3605 | C1ql3 | NM_153155.2 | chr2:13001886-13010864 |
| 3606 | C1ql4 | NM_001024702.1 | chr15:99084753-99087728 |

Fig. 26 - 20

| | | | |
|---|---|---|---|
| 3607 | C1qtnf1 | NM_001204129.1 | chr11:118428456-118451782 |
| 3608 | C1qtnf2 | NM_026979.5 | chr1:43474305-43491525 |
| 3609 | C1qtnf3 | NM_001204134.1 | chr15:10952356-10980162 |
| 3610 | C1qtnf4 | NM_026161.3 | chr2:90885785-90890526 |
| 3611 | C1qtnf5 | NM_001040631.2 | chr9:44107244-44109187 |
| 3612 | C1qtnf6 | NM_001204152.1 | chr15:78523345-78529651 |
| 3613 | C1qtnf7 | NM_001135172.1 | chr5:43515568-43616586 |
| 3614 | C1qtnf9 | NM_183175.4 | chr14:60768133-60780869 |
| 3615 | C1ra | NM_023143.3 | chr6:124512620-124523440 |
| 3616 | C1rb | NM_001113356.1 | chr6:124570429-124581044 |
| 3617 | C1rl | NM_181344.5 | chr6:124493112-124510643 |
| 3618 | C1s1 | NM_001097617.1 | chr6:124530343-124542359 |
| 3619 | C1s2 | NM_173864.2 | chr6:124624624-124636085 |
| 3620 | C2 | NM_013484.2 | chr17:34862601-34882100 |
| 3621 | C230004F18Rik | NR_030706.1 | chrX:61116377-61119460 |
| 3622 | C230024C17Rik | NR_046171.1 | chr1:153721239-153737829 |
| 3623 | C230029M16 | NR_110482.1 | chr10:118920380-118927143 |
| 3624 | C230035I16Rik | NR_015492.1 | chr13:23427975-23431017 |
| 3625 | C230037L18Rik | NR_077233.1 | chr15:89476251-89484850 |
| 3626 | C230052I12Rik | NM_178643.5 | chr7:35392151-35396767 |
| 3627 | C230079O03Rik | NR_040459.1 | chr7:136332215-136349415 |
| 3628 | C230091D08Rik | NR_015491.1 | chr7:59307923-59324149 |
| 3629 | C2cd2 | NM_174847.2 | chr16:97855208-97922633 |
| 3630 | C2cd2l | NM_027909.2 | chr9:44309236-44320282 |
| 3631 | C2cd3 | NM_001170232.1 | chr7:100372232-100470159 |
| 3632 | C2cd4a | NM_001163143.1 | chr9:67830531-67832330 |
| 3633 | C2cd4b | NM_001081314.2 | chr9:67759436-67760933 |
| 3634 | C2cd4c | NM_001168624.1 | chr10:79606853-79614025 |
| 3635 | C2cd4d | NM_001136117.1 | chr3:94362443-94364567 |
| 3636 | C2cd5 | NM_001109688.2 | chr6:143010919-143100152 |
| 3637 | C3 | NM_009778.3 | chr17:57203966-57228136 |
| 3638 | C330006A16Rik | NM_001256521.1 | chr2:26136807-26140506 |
| 3639 | C330007P06Rik | NM_029951.1 | chrX:36848543-36864246 |
| 3640 | C330011F03Rik | NR_046166.1 | chr17:51425208-51448269 |
| 3641 | C330013E15Rik | NR_045701.1 | chr15:100614139-100615110 |
| 3642 | C330013F16Rik | NR_045455.1 | chrX:139240225-139356770 |
| 3643 | C330018D20Rik | NM_029909.1 | chr18:56955830-56975379 |
| 3644 | C330021F23Rik | NM_001024728.2 | chr8:3567997-3584776 |
| 3645 | C330022C24Rik | NR_045717.1 | chr7:140837220-140845689 |
| 3646 | C330024C12Rik | NR_046016.1 | chr17:87192215-87194942 |
| 3647 | C330024D21Rik | NR_015582.2 | chr5:67463897-67470831 |
| 3648 | C330027C09Rik | NM_172616.2 | chr16:48994187-49019705 |
| 3649 | C330046G13Rik | NR_040858.1 | chr10:84547416-84553338 |
| 3650 | C3ar1 | NM_009779.2 | chr6:122847139-122856157 |
| 3651 | C430002E04Rik | NR_040385.1 | chr3:41487680-41493199 |
| 3652 | C430002N11Rik | NR_102293.1 | chr9:96765561-96774397 |
| 3653 | C430049B03Rik | NR_038184.1 | chrX:53053111-53057190 |
| 3654 | C4a | NM_011413.2 | chr17:34809091-34823454 |
| 3655 | C4b | NM_009780.2 | chr17:34728380-34743897 |
| 3656 | C4bp | NM_007576.3 | chr1:130635920-130661618 |
| 3657 | C4bp-ps1 | NR_028304.1 | chr1:130670201-130681571 |
| 3658 | C530005A16Rik | NR_029450.1 | chr4:116589732-116597630 |
| 3659 | C530008M17Rik | NM_001163793.1 | chr5:76840598-76873554 |
| 3660 | C530044C16Rik | NR_045984.1 | chr6:50776114-50814894 |
| 3661 | C5ar1 | NM_001173550.1 | chr7:16246744-16259338 |
| 3662 | C5ar2 | NM_001146005.1 | chr7:16234584-16242331 |
| 3663 | C6 | NM_016704.2 | chr15:4727209-4804045 |
| 3664 | C630028M04Rik | NR_040668.1 | chr4:51968093-52051110 |
| 3665 | C630031E19Rik | NR_046080.1 | chr12:29675629-29686445 |
| 3666 | C630043F03Rik | NR_027923.1 | chr4:72201243-72203930 |
| 3667 | C7 | NM_001243837.1 | chr15:4988761-5063773 |
| 3668 | C730002L08Rik | NR_045778.1 | chr19:20534526-20552330 |
| 3669 | C730027H18Rik | NR_038040.1 | chr10:71168736-71182040 |
| 3670 | C730036E19Rik | NR_038011.1 | chr1:151138033-151144095 |
| 3671 | C77080 | NM_001033189.3 | chr4:129219577-129248403 |
| 3672 | C77370 | NM_001077354.2 | chrX:104077434-104201117 |
| 3673 | C78339 | NM_001033192.2 | chr13:46669521-46675773 |
| 3674 | C86187 | NR_015609.1 | chr4:46967746-46975911 |
| 3675 | C86695 | NM_001081662.1 | chr8:21958713-21964303 |
| 3676 | C87198 | NR_046002.1 | chr12:56591058-56594554 |
| 3677 | C87414 | NM_001164284.1 | chr5:93635184-93671463 |
| 3678 | C87436 | NM_001243741.1 | chr5:86438645-86470387 |
| 3679 | C87499 | NM_198633.3 | chr4:88627319-88634186 |
| 3680 | C87977 | NM_001177542.1 | chr4:144206761-144213017 |
| 3681 | C8a | NM_001290645.1 | chr4:104815685-104876395 |
| 3682 | C8b | NM_133882.2 | chr4:104766316-104804548 |
| 3683 | C8g | NM_001271777.1 | chr2:25498649-25501719 |
| 3684 | C9 | NM_013485.1 | chr15:6445332-6498476 |
| 3685 | C920006O11Rik | NR_040401.1 | chr9:78175913-78178882 |
| 3686 | C920009B18Rik | NR_015465.2 | chr10:22306719-22312942 |
| 3687 | C920021L13Rik | NR_040446.1 | chr3:95871521-95889093 |
| 3688 | C920025E04Rik | NR_027921005.1 | chr17:36109029-36111676 |
| 3689 | Caap1 | NM_026368.2 | chr4:94500078-94556796 |
| 3690 | Cab39 | NM_133781.4 | chr1:85793446-85851577 |
| 3691 | Cab39l | NM_026063.3 | chr14:59440980-59548903 |
| 3692 | Cabin1 | NM_172549.3 | chr10:75646109-75764357 |
| 3693 | Cables1 | NM_001146287.1 | chr18:11839273-11945627 |
| 3694 | Cables2 | NM_145851.2 | chr2:180258538-180273465 |
| 3695 | Cabp1 | NM_013879.2 | chr5:115168690-115186121 |
| 3696 | Cabp2 | NM_001160252.1 | chr19:4083518-4087339 |
| 3697 | Cabp4 | NM_144532.2 | chr19:4135422-4139609 |
| 3698 | Cabp5 | NM_013877.3 | chr7:13398154-13408878 |
| 3699 | Cabp7 | NM_138948.3 | chr11:4738820-4746778 |
| 3700 | Cabs1 | NM_027631.2 | chr5:87979450-87981541 |
| 3701 | Cabyr | NM_001042418.1 | chr18:12741354-12755142 |

| | | | |
|---|---|---|---|
| 3702 | Cachd1 | NM_001243239.1 | chr2:27009925-27016849 |
| 3703 | Cacfd1 | NM_198037.1 | chr4:100776678-101003748 |
| 3704 | Cacna1a | NM_001252059.1 | chr8:84415363-84640249 |
| 3705 | Cacna1b | NM_001042528.2 | chr2:24603888-24763152 |
| 3706 | Cacna1c | NM_001159533.2 | chr6:118587239-119108495 |
| 3707 | Cacna1d | NM_001083616.2 | chr14:30039940-30353486 |
| 3708 | Cacna1e | NM_009782.3 | chr1:154392518-154725920 |
| 3709 | Cacna1f | NM_019582.2 | chrX:7607102-7635196 |
| 3710 | Cacna1g | NM_001112813.2 | chr11:94408390-94474198 |
| 3711 | Cacna1h | NM_001163691.1 | chr17:25374286-25433783 |
| 3712 | Cacna1i | NM_001044308.2 | chr15:80287237-80398292 |
| 3713 | Cacna1s | NM_001081023.1 | chr1:136052900-136119822 |
| 3714 | Cacna2d1 | NM_001110843.1 | chr5:15934690-16374511 |
| 3715 | Cacna2d2 | NM_001174047.1 | chr9:107399879-107529343 |
| 3716 | Cacna2d3 | NM_009785.1 | chr14:28904942-29721864 |
| 3717 | Cacna2d4 | NM_001033382.2 | chr6:119236525-119352407 |
| 3718 | Cacnb1 | NM_001159319.1 | chr11:98004924-98022627 |
| 3719 | Cacnb2 | NM_001252533.1 | chr2:14824091-14987908 |
| 3720 | Cacnb3 | NM_001044741.3 | chr15:98632327-98644536 |
| 3721 | Cacnb4 | NM_001037099.2 | chr2:52428319-52676609 |
| 3722 | Cacng1 | NM_007582.2 | chr11:107703217-107716476 |
| 3723 | Cacng2 | NM_007583.2 | chr15:77993622-78119280 |
| 3724 | Cacng3 | NM_019430.2 | chr7:122671743-122769394 |
| 3725 | Cacng4 | NM_019431.2 | chr11:107734779-107794464 |
| 3726 | Cacng5 | NM_001199301.1 | chr11:107874604-107915055 |
| 3727 | Cacng6 | NM_133183.1 | chr7:3424661-3434940 |
| 3728 | Cacng7 | NM_133189.3 | chr7:3336584-3366948 |
| 3729 | Cacng8 | NM_133190.1 | chr7:3394116-3415605 |
| 3730 | Cactin | NM_027381.2 | chr10:81321102-81326251 |
| 3731 | Cacul1 | NM_001172096.1 | chr19:60524695-60581023 |
| 3732 | Cacybp | NM_009786.2 | chr1:160202366-160212892 |
| 3733 | Cad | NM_001289522.1 | chr5:31054779-31078479 |
| 3734 | Cadm1 | NM_001025600.1 | chr9:47530351-47853385 |
| 3735 | Cadm2 | NM_001145977.1 | chr16:66655420-67620908 |
| 3736 | Cadm3 | NM_053199.3 | chr1:173334253-173367695 |
| 3737 | Cadm4 | NM_153112.3 | chr7:24482022-24504533 |
| 3738 | Cadps | NM_001042617.1 | chr14:12372562-12823079 |
| 3739 | Cadps2 | NM_001252105.1 | chr6:23262773-23839421 |
| 3740 | Cage1 | NM_027724.2 | chr13:38006051-38036937 |
| 3741 | Calb1 | NM_009788.4 | chr4:15881263-15906709 |
| 3742 | Calb2 | NM_007586.1 | chr8:110142537-110168206 |
| 3743 | Calca | NM_001013954.3 | chr7:114631477-114636357 |
| 3744 | Calcb | NM_054084.2 | chr7:114718642-114723365 |
| 3745 | Calcoco1 | NM_026192.3 | chr15:102706776-102722178 |
| 3746 | Calcoco2 | NM_001271018.1 | chr11:96098915-96111962 |
| 3747 | Calcr | NM_001042725.1 | chr6:3685719-3763623 |
| 3748 | Calcrl | NM_018782.2 | chr2:84330626-84425266 |
| 3749 | Cald1 | NM_145575.3 | chr6:34709443-34775469 |
| 3750 | Calhm1 | NM_001081271.1 | chr19:47141034-47144174 |
| 3751 | Calhm2 | NM_133746.5 | chr19:47132231-47138294 |
| 3752 | Calm1 | NM_009790.5 | chr12:100199434-100209824 |
| 3753 | Calm2 | NM_007589.5 | chr17:87433400-87446935 |
| 3754 | Calm3 | NM_007590.3 | chr7:16915378-16924032 |
| 3755 | Calm4 | NM_020036.4 | chr13:3837756-3838671 |
| 3756 | Calm5 | NM_001008706.2 | chr13:3854172-3854761 |
| 3757 | Calml3 | NM_027416.3 | chr13:3802892-3804318 |
| 3758 | Calml4 | NM_001102468.1 | chr9:62858103-62875917 |
| 3759 | Caln1 | NM_021371.2 | chr5:130448791-130840645 |
| 3760 | Calr | NM_007591.3 | chr8:84842087-84846931 |
| 3761 | Calr3 | NM_028500.3 | chr9:72424182-72443778 |
| 3762 | Calr4 | NM_001033226.4 | chr4:109235631-109254577 |
| 3763 | Calu | NM_001285412.1 | chr6:29348105-29376675 |
| 3764 | Caly | NM_001190385.1 | chr7:140069879-140082548 |
| 3765 | Camk1 | NM_133926.2 | chr6:113334123-113343922 |
| 3766 | Camk1d | NM_001290374.1 | chr2:5293456-5714762 |
| 3767 | Camk1g | NM_144817.2 | chr1:193346345-193370282 |
| 3768 | Camk2a | NM_001286809.1 | chr18:60963553-60988152 |
| 3769 | Camk2b | NM_001174053.1 | chr11:5969665-6065748 |
| 3770 | Camk2d | NM_001025438.2 | chr3:126596950-126846326 |
| 3771 | Camk2g | NM_001039138.2 | chr14:20734872-20794088 |
| 3772 | Camk2n1 | NM_025451.2 | chr4:138455147-138460126 |
| 3773 | Camk2n2 | NM_028420.2 | chr16:20619214-20621278 |
| 3774 | Camk4 | NM_009793.3 | chr18:32939040-33195767 |
| 3775 | Camkk1 | NM_018883.2 | chr11:73019007-73042065 |
| 3776 | Camkk2 | NM_001199676.1 | chr5:122731169-122779410 |
| 3777 | Camkmt | NM_028576.2 | chr17:85090699-85458580 |
| 3778 | Camkv | NM_145621.2 | chr9:107935919-107949691 |
| 3779 | Caml | NM_007596.2 | chr13:55623004-55632416 |
| 3780 | Camp | NM_009921.2 | chr9:109847376-109849456 |
| 3781 | Camsap1 | NM_001276359.1 | chr2:25926837-25983282 |
| 3782 | Camsap2 | NM_001081360.1 | chr1:136268122-136346104 |
| 3783 | Camsap3 | NM_001163749.1 | chr8:3587449-3609075 |
| 3784 | Camta1 | NM_001081557.3 | chr4:151059522-151861768 |
| 3785 | Camta2 | NM_001190376.1 | chr11:70669462-70688105 |
| 3786 | Cand1 | NM_027994.1 | chr10:119198811-119240055 |
| 3787 | Cand2 | NM_025958.2 | chr6:115774556-115805555 |
| 3788 | Cant1 | NM_001025617.2 | chr11:118406288-118419118 |
| 3789 | Canx | NM_001110499.1 | chr11:50293956-50325673 |
| 3790 | Cap1 | NM_007598.4 | chr4:122859047-122886057 |
| 3791 | Cap2 | NM_026056.4 | chr13:46501902-46650281 |
| 3792 | Capg | NM_001042534.3 | chr6:72549272-72562983 |
| 3793 | Capn1 | NM_001110504.1 | chr19:5988544-6015825 |
| 3794 | Capn10 | NM_011796.2 | chr1:92934407-92947948 |
| 3795 | Capn11 | NM_001013767.2 | chr17:45630203-45659309 |
| 3796 | Capn12 | NM_001110807.1 | chr7:28881655-28893585 |

Fig. 26 - 21

| | | | |
|---|---|---|---|
| 3797 | Capn13 | NM_001033444.2 | chr17:73306463-73399296 |
| 3798 | Capn15 | NM_015830.1 | chr3:25959555-25965505 |
| 3799 | Capn2 | NM_009794.3 | chr1:182467258-182517483 |
| 3800 | Capn3 | NM_001109761.2 | chr2:120476908-120504919 |
| 3801 | Capn5 | NM_007602.4 | chr7:98121558-98178274 |
| 3802 | Capn6 | NM_007603.3 | chrX:143802236-143827412 |
| 3803 | Capn7 | NM_009796.2 | chr14:31336723-31371983 |
| 3804 | Capn8 | NM_001145806.1 | chr1:182565006-182606526 |
| 3805 | Capn9 | NM_023709.4 | chr8:124576110-124618731 |
| 3806 | Capns1 | NM_009795.3 | chr7:30186941-30195048 |
| 3807 | Capns2 | NM_027112.1 | chr8:92901394-92902409 |
| 3808 | Caprin1 | NM_001111289.1 | chr2:103762944-103797078 |
| 3809 | Caprin2 | NM_181541.4 | chr6:148842491-148896237 |
| 3810 | Caps2 | NM_178278.4 | chr10:112165675-112216555 |
| 3811 | Capsl | NM_029341.1 | chr15:9436027-9466035 |
| 3812 | Capza1 | NM_009797.2 | chr3:104822784-104864505 |
| 3813 | Capza2 | NM_007604.2 | chr6:17637097-17666536 |
| 3814 | Capza3 | NM_007605.4 | chr6:140041524-140042786 |
| 3815 | Capzb | NM_001037761.2 | chr4:139192898-139291820 |
| 3816 | Car1 | NM_001083957.1 | chr3:14766213-14778460 |
| 3817 | Car10 | NM_028296.3 | chr11:93099289-93601751 |
| 3818 | Car11 | NM_009800.4 | chr7:45699966-45704661 |
| 3819 | Car12 | NM_178396.5 | chr9:66713685-66766845 |
| 3820 | Car13 | NM_024495.5 | chr3:14641726-14663002 |
| 3821 | Car14 | NM_011797.2 | chr3:95897799-95904639 |
| 3822 | Car15 | NM_030558.2 | chr16:17835275-17838186 |
| 3823 | Car2 | NM_009801.4 | chr3:14886425-14900770 |
| 3824 | Car3 | NM_007606.3 | chr3:14863537-14872373 |
| 3825 | Car4 | NM_007607.2 | chr11:84957753-84966054 |
| 3826 | Car5a | NM_007608.2 | chr8:121916137-121944912 |
| 3827 | Car5b | NM_181315.4 | chrX:163976821-164028010 |
| 3828 | Car6 | NM_009802.2 | chr4:150187015-150201135 |
| 3829 | Car7 | NM_053070.3 | chr8:104540806-104550343 |
| 3830 | Car8 | NM_007592.3 | chr4:8141492-8239041 |
| 3831 | Car9 | NM_139305.2 | chr4:43507025-43513725 |
| 3832 | Card10 | NM_130859.2 | chr15:78775135-78803042 |
| 3833 | Card11 | NM_175362.2 | chr5:140872998-141000596 |
| 3834 | Card14 | NM_130886.3 | chr11:119314786-119345375 |
| 3835 | Card6 | NM_001163138.1 | chr15:5097438-5108533 |
| 3836 | Card9 | NM_001037747.1 | chr2:26352311-26359547 |
| 3837 | Carf | NM_001285463.1 | chr1:60098246-60153953 |
| 3838 | Carhsp1 | NM_025821.2 | chr16:8658586-8672153 |
| 3839 | Carkd | NM_001190357.1 | chr8:11497505-11513286 |
| 3840 | Carm1 | NM_021531.6 | chr9:21546893-21589465 |
| 3841 | Carns1 | NM_134148.2 | chr19:4164323-4175479 |
| 3842 | Cars | NM_001252593.1 | chr7:143557229-143600090 |
| 3843 | Cars2 | NM_024248.1 | chr8:11514016-11550771 |
| 3844 | Cartpt | NM_001081493.2 | chr13:99898482-99900683 |
| 3845 | Casc1 | NM_177222.4 | chr6:145174871-145210970 |
| 3846 | Casc3 | NM_138660.2 | chr11:98809807-98833807 |
| 3847 | Casc4 | NM_001205369.1 | chr2:121866969-121936207 |
| 3848 | Casc5 | NM_029617.2 | chr2:119047118-119104121 |
| 3849 | Casd1 | NM_145398.2 | chr6:4601006-4643381 |
| 3850 | Cask | NM_001284503.1 | chrX:13517080-13846556 |
| 3851 | Caskin1 | NM_027937.2 | chr17:24488782-24508907 |
| 3852 | Caskin2 | NM_080643.2 | chr11:115799351-115813592 |
| 3853 | Casp1 | NM_009807.2 | chr9:5298516-5307281 |
| 3854 | Casp12 | NM_009808.4 | chr9:5345475-5373034 |
| 3855 | Casp14 | NM_009809.5 | chr10:78711994-78718293 |
| 3856 | Casp2 | NM_007610.2 | chr6:42264984-42282508 |
| 3857 | Casp3 | NM_001284409.1 | chr8:46617290-46639698 |
| 3858 | Casp4 | NM_007609.3 | chr9:5308848-5336791 |
| 3859 | Casp6 | NM_009811.4 | chr3:129901414-129914112 |
| 3860 | Casp7 | NM_007611.2 | chr19:56397128-56442343 |
| 3861 | Casp8 | NM_001080125.1 | chr1:58802501-58847503 |
| 3862 | Casp8ap2 | NM_001122978.1 | chr4:32615472-32653265 |
| 3863 | Casp9 | NM_001277932.1 | chr4:141793611-141815978 |
| 3864 | Casq1 | NM_009813.2 | chr1:172209893-172219895 |
| 3865 | Casq2 | NM_009814.3 | chr3:102086454-102146512 |
| 3866 | Casr | NM_013803.3 | chr16:36493695-36562134 |
| 3867 | Cass4 | NM_001080820.2 | chr2:172393793-172433757 |
| 3868 | Cast | NM_009817.4 | chr13:74693293-74807960 |
| 3869 | Casz1 | NM_001159344.1 | chr4:148804391-148954892 |
| 3870 | Cat | NM_009804.2 | chr2:103453903-103485153 |
| 3871 | Catip | NM_001033345.2 | chr1:74362107-74369321 |
| 3872 | Catsper1 | NM_139361.2 | chr19:5335740-5344153 |
| 3873 | Catsper2 | NM_153075.3 | chr2:121394354-121413792 |
| 3874 | Catsper3 | NM_001252487.1 | chr13:55784578-55808000 |
| 3875 | Catsper4 | NM_001130030.1 | chr4:134211967-134227383 |
| 3876 | Catsperb | NM_173023.2 | chr12:101404672-101626009 |
| 3877 | Catsperd | NM_175350.3 | chr17:56628142-56664456 |
| 3878 | Catsperg1 | NM_001164665.1 | chr7:29181531-29214033 |
| 3879 | Catsperg2 | NM_029714.3 | chr7:29697218-29727015 |
| 3880 | Cav1 | NM_001243064.1 | chr6:17307639-17341328 |
| 3881 | Cav2 | NM_001277756.1 | chr6:17281184-17282684 |
| 3882 | Cav3 | NM_007617.3 | chr6:112459504-112472872 |
| 3883 | Cbfa2t2 | NM_001246483.1 | chr2:154436483-154539356 |
| 3884 | Cbfa2t3 | NM_001109873.1 | chr8:122625135-122678175 |
| 3885 | Cbfb | NM_001161456.1 | chr8:105170673-105217988 |
| 3886 | Cbl | NM_007619.2 | chr9:44149261-44234046 |
| 3887 | Cblb | NM_001033238.1 | chr16:52031548-52208046 |
| 3888 | Cblc | NM_001161844.1 | chr7:19779717-19796809 |
| 3889 | Cbll1 | NM_001205869.1 | chr12:31484828-31499616 |
| 3890 | Cbln1 | NM_019626.3 | chr8:87468852-87472592 |
| 3891 | Cbln2 | NM_172633.4 | chr18:86712064-86718283 |

| | | | |
|---|---|---|---|
| 3892 | Cbln3 | NM_019820.3 | chr14:55878919-55884256 |
| 3893 | Cbln4 | NM_175631.3 | chr2:172036335-172043466 |
| 3894 | Cbr1 | NM_007620.2 | chr16:93607836-93610349 |
| 3895 | Cbr2 | NM_007621.2 | chr11:120729484-120732021 |
| 3896 | Cbr3 | NM_173047.3 | chr16:93683218-93690991 |
| 3897 | Cbr4 | NM_145595.2 | chr8:61487733-61503500 |
| 3898 | Cbs | NM_001271353.1 | chr17:31612622-31637205 |
| 3899 | Cbwd1 | NM_146097.3 | chr19:24919915-24961616 |
| 3900 | Cbx1 | NM_007622.3 | chr11:96789135-96808640 |
| 3901 | Cbx2 | NM_007623.3 | chr11:119023020-119031275 |
| 3902 | Cbx3 | NM_007624.3 | chr6:51470615-51483704 |
| 3903 | Cbx4 | NM_007625.2 | chr11:119077570-119086237 |
| 3904 | Cbx5 | NM_001076789.1 | chr15:103191545-103239816 |
| 3905 | Cbx6 | NM_028763.3 | chr15:79823897-79834333 |
| 3906 | Cbx7 | NM_144811.3 | chr15:79915806-79932646 |
| 3907 | Cbx8 | NM_013926.1 | chr11:119038435-119040913 |
| 3908 | Cby1 | NM_028634.3 | chr15:79659226-79667660 |
| 3909 | Cc2d1a | NM_145970.1 | chr8:84132827-84147753 |
| 3910 | Cc2d1b | NM_177045.3 | chr4:108619955-108634122 |
| 3911 | Cc2d2a | NM_172274.2 | chr5:43662378-43740970 |
| 3912 | Ccar1 | NM_026201.3 | chr10:62743927-62792368 |
| 3913 | Ccar2 | NM_146055.3 | chr14:70138168-70153791 |
| 3914 | Ccbe1 | NM_178793.4 | chr18:66056855-66291838 |
| 3915 | Ccbl1 | NM_172404.2 | chr2:30185130-30205699 |
| 3916 | Ccbl2 | NM_173763.4 | chr3:142701047-142744911 |
| 3917 | Ccdc101 | NM_029339.3 | chr7:126649308-126672779 |
| 3918 | Ccdc102a | NM_001033533.3 | chr8:94902868-94918098 |
| 3919 | Ccdc103 | NM_028492.2 | chr11:102881243-102885215 |
| 3920 | Ccdc104 | NM_025740.3 | chr11:29221535-29247272 |
| 3921 | Ccdc105 | NM_027630.1 | chr10:78746923-78753067 |
| 3922 | Ccdc106 | NM_001290429.1 | chr7:5056151-5060784 |
| 3923 | Ccdc107 | NM_001037913.2 | chr4:43493364-43495921 |
| 3924 | Ccdc108 | NM_001039495.1 | chr1:74902079-74935599 |
| 3925 | Ccdc109b | NM_025779.3 | chr3:129914959-129970206 |
| 3926 | Ccdc11 | NM_028948.2 | chr18:74283099-74359984 |
| 3927 | Ccdc110 | NM_001033246.2 | chr8:45934648-45944145 |
| 3928 | Ccdc112 | NM_001160399.1 | chr18:46282150-46311928 |
| 3929 | Ccdc113 | NM_172914.2 | chr8:95534099-95558888 |
| 3930 | Ccdc114 | NM_001033243.2 | chr7:45928897-45948956 |
| 3931 | Ccdc115 | NM_027159.2 | chr1:34436669-34439672 |
| 3932 | Ccdc116 | NM_001306169.1 | chr16:1713906-17147146 |
| 3933 | Ccdc117 | NM_134033.2 | chr11:5528887-5542217 |
| 3934 | Ccdc12 | NM_028312.3 | chr9:110656502-110711593 |
| 3935 | Ccdc120 | NM_207202.2 | chrX:7731713-7741324 |
| 3936 | Ccdc121 | NM_207280.3 | chr1:181509632-181511451 |
| 3937 | Ccdc122 | NM_175369.4 | chr14:77036771-77112263 |
| 3938 | Ccdc124 | NM_026964.3 | chr8:70868226-70873490 |
| 3939 | Ccdc125 | NM_001168386.2 | chr13:100669480-100697240 |
| 3940 | Ccdc126 | NM_175098.6 | chr6:49319273-49341586 |
| 3941 | Ccdc127 | NM_001168658.1 | chr13:74350316-74365783 |
| 3942 | Ccdc129 | NM_001081665.1 | chr6:55837017-55978598 |
| 3943 | Ccdc13 | NM_028384.1 | chr9:121797676-121839461 |
| 3944 | Ccdc130 | NM_026350.3 | chr8:84257766-84270402 |
| 3945 | Ccdc132 | NM_001167750.1 | chr6:3498392-3603531 |
| 3946 | Ccdc134 | NM_172428.2 | chr15:82127921-82142202 |
| 3947 | Ccdc135 | NM_001042715.3 | chr8:95055102-95078141 |
| 3948 | Ccdc136 | NM_001201378.1 | chr6:29398925-29426995 |
| 3949 | Ccdc137 | NM_152807.3 | chr11:120458128-120464353 |
| 3950 | Ccdc138 | NM_001162956.1 | chr10:58497936-58576244 |
| 3951 | Ccdc14 | NM_172824.3 | chr16:34696615-34725194 |
| 3952 | Ccdc141 | NM_001025576.3 | chr2:77009905-77170635 |
| 3953 | Ccdc142 | NM_001081266.1 | chr6:83101515-83109121 |
| 3954 | Ccdc144b | NM_178418.4 | chr3:36007246-36053547 |
| 3955 | Ccdc146 | NM_029195.1 | chr5:21292960-21424677 |
| 3956 | Ccdc147 | NM_001163267.1 | chr19:47937711-48035379 |
| 3957 | Ccdc148 | NM_001001178.1 | chr2:58821697-59018606 |
| 3958 | Ccdc149 | NM_001256059.1 | chr5:52374650-52471543 |
| 3959 | Ccdc15 | NM_001081429.1 | chr9:37275834-37348392 |
| 3960 | Ccdc150 | NM_030025.2 | chr1:54250682-54368727 |
| 3961 | Ccdc151 | NM_001163787.1 | chr9:21989870-22002634 |
| 3962 | Ccdc152 | NM_001166063.2 | chr15:3280626-3303526 |
| 3963 | Ccdc153 | NM_001081269.2 | chr9:44240676-44247306 |
| 3964 | Ccdc154 | NM_001079929.2 | chr17:25162460-25171913 |
| 3965 | Ccdc155 | NM_201374.2 | chr7:45183675-45204892 |
| 3966 | Ccdc157 | NM_001164620.1 | chr11:4141123-4160293 |
| 3967 | Ccdc158 | NM_177230.3 | chr5:92608294-92675127 |
| 3968 | Ccdc159 | NM_001164614.1 | chr9:21927470-21935872 |
| 3969 | Ccdc160 | NM_001034059.1 | chrX:52791199-52799468 |
| 3970 | Ccdc162 | NM_001303469.1 | chr10:41536409-41716568 |
| 3971 | Ccdc163 | NM_026714.2 | chr4:116708929-116715104 |
| 3972 | Ccdc166 | NM_001163518.1 | chr15:75979871-75982285 |
| 3973 | Ccdc167 | NM_001163741.2 | chr17:29695976-29717017 |
| 3974 | Ccdc169 | NM_001290138.1 | chr3:55137338-55172936 |
| 3975 | Ccdc17 | NM_001037916.3 | chr4:116596729-116600266 |
| 3976 | Ccdc170 | NM_001195672.1 | chr10:4509871-4561111 |
| 3977 | Ccdc171 | NM_001081012.1 | chr4:83525544-83864670 |
| 3978 | Ccdc172 | NM_029372.2 | chr19:58512001-58553085 |
| 3979 | Ccdc173 | NM_001077684.1 | chr2:69758056-69789486 |
| 3980 | Ccdc174 | NM_172730.2 | chr6:91878052-91899848 |
| 3981 | Ccdc175 | NM_028687.1 | chr12:72101291-72185029 |
| 3982 | Ccdc176 | NM_028377.3 | chr12:84409067-84433780 |
| 3983 | Ccdc177 | NM_001008423.2 | chr12:80755446-80760715 |
| 3984 | Ccdc178 | NM_027616.3 | chr18:21810896-22171396 |
| 3985 | Ccdc18 | NM_028481.1 | chr5:108132913-108232949 |
| 3986 | Ccdc181 | NM_029115.3 | chr1:164275597-164287847 |

Fig. 26 - 22

| | | | | | | | | |
|---|---|---|---|---|---|---|---|---|
| 3987 | Ccdc183 | NM_029859.1 | chr2:25608628-25617678 | | 4082 | Ccl24 | NM_019577.4 | chr5:135569936-135573043 |
| 3988 | Ccdc184 | NM_177716.3 | chr15:98167805-98170134 | | 4083 | Ccl25 | NM_009138.3 | chr8:4349587-4360020 |
| 3989 | Ccdc185 | NM_001033547.2 | chr1:182747125-182749180 | | 4084 | Ccl26 | NM_001013412.2 | chr5:135560447-135563569 |
| 3990 | Ccdc19 | NM_027972.1 | chr1:172521129-172545870 | | 4085 | Ccl27a | NM_001048179.1 | chr4:41769469-41774134 |
| 3991 | Ccdc22 | NM_138603.3 | chrX:7593808-7605420 | | 4086 | Ccl27b | NM_001199959.1 | chr4:3059-42656005 |
| 3992 | Ccdc23 | NM_001038998.2 | chr4:119195524-119201298 | | 4087 | Ccl28 | NM_020279.3 | chr13:119623818-119654358 |
| 3993 | Ccdc24 | NM_001034876.1 | chr4:117869259-117872470 | | 4088 | Ccl3 | NM_011337.2 | chr11:83647842-83649378 |
| 3994 | Ccdc25 | NM_145944.4 | chr14:65837301-65866604 | | 4089 | Ccl4 | NM_013652.2 | chr11:83662583-83664681 |
| 3995 | Ccdc27 | NM_001033455.2 | chr4:154026643-154042677 | | 4090 | Ccl5 | NM_013653.3 | chr11:83525778-83530518 |
| 3996 | Ccdc28a | NM_144820.3 | chr10:18213684-18234981 | | 4091 | Ccl6 | NM_009139.3 | chr11:83587885-83593087 |
| 3997 | Ccdc28b | NM_025455.2 | chr4:129619273-129623908 | | 4092 | Ccl7 | NM_013654.3 | chr11:82045711-82047523 |
| 3998 | Ccdc3 | NM_028804.1 | chr2:5137775-5230866 | | 4093 | Ccl8 | NM_021443.3 | chr11:82115184-82116799 |
| 3999 | Ccdc30 | NM_001270435.1 | chr4:119322892-119415521 | | 4094 | Ccl9 | NM_011338.2 | chr11:83572916-83578636 |
| 4000 | Ccdc32 | NM_199310.2 | chr2:119017778-119029393 | | 4095 | Ccm2 | NM_001190343.1 | chr11:6546886-6596761 |
| 4001 | Ccdc33 | NM_001166282.1 | chr9:58028681-58118823 | | 4096 | Ccm2l | NM_145536.3 | chr2:153065954-153081735 |
| 4002 | Ccdc34 | NM_026613.4 | chr2:110017816-110045325 | | 4097 | Ccna1 | NM_007628.3 | chr3:55045468-55055055 |
| 4003 | Ccdc34os | NR_040508.1 | chr2:110031249-110050479 | | 4098 | Ccna2 | NM_009828.2 | chr3:36564864-36571996 |
| 4004 | Ccdc36 | NM_001135198.1 | chr9:108403632-108428482 | | 4099 | Ccnb1 | NM_172301.3 | chr13:100778738-100786486 |
| 4005 | Ccdc37 | NM_173775.3 | chr6:90403735-90428480 | | 4100 | Ccnb1ip1 | NM_001111119.1 | chr14:50789248-50795728 |
| 4006 | Ccdc38 | NM_175488.6 | chr10:93540631-93584326 | | 4101 | Ccnb2 | NM_007630.2 | chr9:70407688-70421554 |
| 4007 | Ccdc39 | NM_026222.2 | chr3:33812360-33844310 | | 4102 | Ccnb3 | NM_183015.3 | chrX:6979651-7041619 |
| 4008 | Ccdc40 | NM_175430.4 | chr11:119228571-119265212 | | 4103 | Ccnc | NM_001122982.2 | chr4:21727700-21747962 |
| 4009 | Ccdc42 | NM_177779.3 | chr11:68587036-68597951 | | 4104 | Ccnd1 | NM_007631.2 | chr7:144929930-144939925 |
| 4010 | Ccdc42b | NM_001195094.1 | chr5:120628334-120634236 | | 4105 | Ccnd2 | NM_009829.3 | chr6:127125708-127151048 |
| 4011 | Ccdc43 | NM_025918.3 | chr11:106284687-102697725 | | 4106 | Ccnd3 | NM_001081635.1 | chr17:47505050-47599688 |
| 4012 | Ccdc47 | NM_026009.2 | chr11:106199355-106216367 | | 4107 | Ccndbp1 | NM_010761.2 | chr7:121008407-121016912 |
| 4013 | Ccdc50 | NM_001025615.3 | chr16:27388955-27452218 | | 4108 | Ccne1 | NM_007633.2 | chr7:38097983-38107490 |
| 4014 | Ccdc51 | NM_025689.4 | chr9:109082495-109093363 | | 4109 | Ccne2 | NM_001037134.2 | chr4:11191350-11204779 |
| 4015 | Ccdc53 | NM_001122960.1 | chr10:88201096-88246158 | | 4110 | Ccnf | NM_007634.4 | chr17:24223231-24251409 |
| 4016 | Ccdc54 | NM_027046.3 | chr16:50589858-50591154 | | 4111 | Ccng1 | NM_009831.2 | chr11:40748551-40755286 |
| 4017 | Ccdc55 | NM_001012309.2 | chr11:77044291-77078437 | | 4112 | Ccng2 | NM_007635.4 | chr5:93267572-93276231 |
| 4018 | Ccdc57 | NM_027745.1 | chr11:120826541-120932872 | | 4113 | Ccnh | NM_023243.5 | chr13:85189476-85213723 |
| 4019 | Ccdc58 | NM_001159421.1 | chr16:36071659-36092118 | | 4114 | Ccni | NM_017367.3 | chr5:93181932-93206495 |
| 4020 | Ccdc59 | NM_025602.3 | chr10:105841478-105847510 | | 4115 | Ccnj | NM_172839.4 | chr19:40831278-40848570 |
| 4021 | Ccdc6 | NM_001111121.1 | chr10:70097120-70193200 | | 4116 | Ccnjl | NM_001045530.2 | chr11:43528748-43586999 |
| 4022 | Ccdc60 | NM_177759.3 | chr5:116125580-116288985 | | 4117 | Ccnk | NM_009832.2 | chr12:108179737-108203359 |
| 4023 | Ccdc61 | NM_001033314.3 | chr7:18890883-18910404 | | 4118 | Ccnl1 | NM_019937.3 | chr3:65946150-65958225 |
| 4024 | Ccdc62 | NM_001134767.1 | chr5:123930688-123969895 | | 4119 | Ccnl2 | NM_207678.1 | chr4:155812488-155824543 |
| 4025 | Ccdc63 | NM_001289809.1 | chr5:122108051-122134893 | | 4120 | Ccno | NM_001081062.1 | chr13:112987801-112990778 |
| 4026 | Ccdc64 | NM_001080808.1 | chr5:115649285-115731559 | | 4121 | Ccnt1 | NM_009833.1 | chr15:98543210-98567636 |
| 4027 | Ccdc64b | NM_153784.2 | chr17:23660522-23668619 | | 4122 | Ccnt2 | NM_028399.1 | chr1:127774163-127804837 |
| 4028 | Ccdc65 | NM_153518.1 | chr15:98708226-98723333 | | 4123 | Ccny | NM_026484.3 | chr18:9314043-9450150 |
| 4029 | Ccdc66 | NM_177111.3 | chr14:27482404-27508460 | | 4124 | Ccnyl1 | NM_001097644.1 | chr1:64691344-64725642 |
| 4030 | Ccdc67 | NM_181816.2 | chr9:15559863-15627933 | | 4125 | Ccp110 | NM_182995.1 | chr7:118712610-118737018 |
| 4031 | Ccdc68 | NM_201362.2 | chr18:69925558-69969484 | | 4126 | Ccpg1 | NM_001114328.2 | chr9:72985503-73013938 |
| 4032 | Ccdc69 | NM_177471.4 | chr11:55049737-55078131 | | 4127 | Ccpg1os | NM_001198789.1 | chr9:72979724-72985376 |
| 4033 | Ccdc7 | NM_001197041.1 | chr8:129045476-129065492 | | 4128 | Ccr1 | NM_009912.4 | chr9:123962125-123968692 |
| 4034 | Ccdc70 | NM_026459.3 | chr8:21970595-21974041 | | 4129 | Ccr10 | NM_007719.4 | chr11:101172997-101175443 |
| 4035 | Ccdc71 | NM_133744.4 | chr9:108460517-108465945 | | 4130 | Ccrl1 | NM_007718.3 | chr9:123976948-123978408 |
| 4036 | Ccdc71l | NM_001162903.1 | chr12:32378788-32382943 | | 4131 | Ccr2 | NM_009915.2 | chr9:124102182-124109140 |
| 4037 | Ccdc73 | NM_177600.4 | chr2:104886323-104999737 | | 4132 | Ccr3 | NM_009914.4 | chr9:124021970-124031689 |
| 4038 | Ccdc74a | NM_001166164.1 | chr16:17646469-17650738 | | 4133 | Ccr4 | NM_009916.2 | chr9:114490315-114496544 |
| 4039 | Ccdc77 | NM_028028.5 | chr6:120324321-120357469 | | 4134 | Ccr5 | NM_009917.5 | chr9:124121542-124127183 |
| 4040 | Ccdc78 | NM_001165929.1 | chr17:25786579-25790513 | | 4135 | Ccr6 | NM_001190333.1 | chr17:8236042-8257129 |
| 4041 | Ccdc79 | NM_180958.3 | chr8:104446718-104509887 | | 4136 | Ccr7 | NM_007719.2 | chr11:99144198-99155077 |
| 4042 | Ccdc8 | NM_001101535.1 | chr7:16994587-16996645 | | 4137 | Ccr8 | NM_007720.2 | chr9:120092132-120094906 |
| 4043 | Ccdc80 | NM_026439.2 | chr16:45094052-45127924 | | 4138 | Ccr9 | NM_001166625.1 | chr9:123767210-123783457 |
| 4044 | Ccdc81 | NM_001162979.1 | chr7:89866147-89903629 | | 4139 | Ccrl2 | NM_017466.5 | chr9:111054833-111057270 |
| 4045 | Ccdc82 | NM_025534.2 | chr9:13246978-13292353 | | 4140 | Ccrn4l | NM_009834.2 | chr3:51224446-51251654 |
| 4046 | Ccdc83 | NM_029256.3 | chr7:90235760-90265432 | | 4141 | Ccs | NM_016892.3 | chr19:4825365-4839322 |
| 4047 | Ccdc84 | NM_201372.3 | chr9:44410163-44418007 | | 4142 | Ccsap | NM_028536.1 | chr8:123840543-123860209 |
| 4048 | Ccdc85a | NM_001166661.2 | chr11:28385683-28584324 | | 4143 | Ccser1 | NM_001164316.1 | chr6:61180324-62382863 |
| 4049 | Ccdc85b | NM_001243307.1 | chr19:5453162-5457563 | | 4144 | Ccser2 | NM_027045.1 | chr14:36874935-36968764 |
| 4050 | Ccdc85c | NM_001159910.1 | chr12:108206344-108275417 | | 4145 | Cct2 | NM_007636.2 | chr10:117050997-117063814 |
| 4051 | Ccdc86 | NM_023731.3 | chr19:10941480-10949266 | | 4146 | Cct3 | NM_009836.1 | chr3:88297134-88321766 |
| 4052 | Ccdc87 | NM_207268.3 | chr19:4839365-4842528 | | 4147 | Cct4 | NM_009837.1 | chr11:22990592-23003336 |
| 4053 | Ccdc88a | NM_176841.4 | chr11:29374171-29510808 | | 4148 | Cct5 | NM_007637.2 | chr15:31590883-31601804 |
| 4054 | Ccdc88b | NM_001081291.1 | chr19:6844622-6858211 | | 4149 | Cct6a | NM_009838.2 | chr5:129787355-129846443 |
| 4055 | Ccdc88c | NM_026681.4 | chr12:100912699-101028983 | | 4150 | Cct6b | NM_001291242.1 | chr11:82719247-82764321 |
| 4056 | Ccdc89 | NM_027298.1 | chr7:90426311-90428664 | | 4151 | Cct7 | NM_007638.4 | chr6:85451504-85468477 |
| 4057 | Ccdc9 | NM_001136471.1 | chr7:16274041-16286795 | | 4152 | Cct8 | NM_009840.3 | chr16:87483324-87495869 |
| 4058 | Ccdc90b | NM_001162918.1 | chr7:92561348-92582294 | | 4153 | Cct8l1 | NM_198621.2 | chr5:25516066-25518027 |
| 4059 | Ccdc91 | NM_025911.2 | chr6:147475876-147632612 | | 4154 | Ccz1 | NM_177682.3 | chr5:143987908-144014853 |
| 4060 | Ccdc92 | NM_144819.2 | chr5:124834431-124862221 | | 4155 | Cd101 | NM_001167906.1 | chr3:100993529-101029495 |
| 4061 | Ccdc93 | NM_001025156.2 | chr1:121431066-121506460 | | 4156 | Cd109 | NM_153098.3 | chr9:78615545-78716260 |
| 4062 | Ccdc94 | NM_028381.3 | chr17:55959186-55967951 | | 4157 | Cd14 | NM_009841.4 | chr18:36725663-36726815 |
| 4063 | Ccdc96 | NM_025725.2 | chr5:36484587-36488171 | | 4158 | Cd151 | NM_001110491.1 | chr7:141467361-141471481 |
| 4064 | Ccdc97 | NM_028771.2 | chr7:25711116-25719053 | | 4159 | Cd160 | NM_001163496.1 | chr3:96798762-96829351 |
| 4065 | Ccer1 | NM_025724.2 | chr10:97693058-97694926 | | 4160 | Cd163 | NM_001170395.1 | chr6:124304650-124330527 |
| 4066 | Ccher1 | NM_146248.2 | chr17:35517115-35531015 | | 4161 | Cd163l1 | NM_172909.4 | chr7:140218266-140231145 |
| 4067 | Ccin | NM_001002787.2 | chr4:43983503-43985533 | | 4162 | Cd164 | NM_016898.2 | chr10:41519499-41531042 |
| 4068 | Cck | NM_031284508.2 | chr9:121489823-121495694 | | 4163 | Cd164l2 | NM_027152.1 | chr4:133220808-133224554 |
| 4069 | Cckar | NM_009827.3 | chr5:53698484-53707704 | | 4164 | Cd177 | NM_026862.3 | chr7:24743982-24760311 |
| 4070 | Cckbr | NM_007627.5 | chr7:105425730-105436339 | | 4165 | Cd180 | NM_008533.2 | chr13:102693557-102706631 |
| 4071 | Ccl1 | NM_011329.3 | chr11:82176665-82179812 | | 4166 | Cd19 | NM_009844.2 | chr7:126408447-126414870 |
| 4072 | Ccl11 | NM_011330.3 | chr11:82057831-82062955 | | 4167 | Cd1d1 | NM_007639.3 | chr3:86995835-86999340 |
| 4073 | Ccl12 | NM_011331.2 | chr11:82101844-82103399 | | 4168 | Cd1d2 | NM_001289449.1 | chr3:86986585-86989532 |
| 4074 | Ccl17 | NM_011332.3 | chr8:94810452-94812036 | | 4169 | Cd2 | NM_013486.2 | chr3:101275907-101287939 |
| 4075 | Ccl19 | NM_011888.2 | chr4:102333-42756518 | | 4170 | Cd200 | NM_010818.3 | chr16:45382134-45409053 |
| 4076 | Ccl2 | NM_011333.3 | chr11:82035576-82037452 | | 4171 | Cd200r1 | NM_021325.3 | chr16:44765735-44794977 |
| 4077 | Ccl20 | NM_001159738.1 | chr1:83116765-83119167 | | 4172 | Cd200r2 | NM_206535.1 | chr16:44867096-44915840 |
| 4078 | Ccl21a | NM_011124.4 | chr4:120654-42773991 | | 4173 | Cd200r3 | NM_001128132.1 | chr16:44943677-44966290 |
| 4079 | Ccl21b | NM_011335.2 | chr4:0-42613253 | | 4174 | Cd200r4 | NM_027244.2 | chr16:44820727-44839150 |
| 4080 | Ccl21c | NM_023052.2 | chr4:0-42613253 | | 4175 | Cd207 | NM_144943.3 | chr6:83671206-83677857 |
| 4081 | Ccl22 | NM_009137.2 | chr8:94745683-94751388 | | 4176 | Cd209a | NM_133238.5 | chr8:3743394-3748984 |

Fig. 26 - 23

| | | | |
|---|---|---|---|
| 4177 | Cd209b | NM_001037800.3 | chr8:3917654-3926841 |
| 4178 | Cd209c | NM_130903.3 | chr8:3940221-3946863 |
| 4179 | Cd209d | NM_130904.2 | chr8:3871823-3878499 |
| 4180 | Cd209e | NM_130905.2 | chr8:3847972-3854286 |
| 4181 | Cd209f | NM_026956.2 | chr8:4102792-4105764 |
| 4182 | Cd209g | NM_027343.3 | chr8:4134735-4137787 |
| 4183 | Cd22 | NM_001043317.2 | chr7:30865403-30880342 |
| 4184 | Cd226 | NM_001039149.1 | chr18:89197426-89270327 |
| 4185 | Cd244 | NM_018729.2 | chr1:171559192-171585316 |
| 4186 | Cd247 | NM_001113391.2 | chr1:165788686-165862112 |
| 4187 | Cd248 | NM_054042.2 | chr19:5068077-5070639 |
| 4188 | Cd24a | NM_009846.2 | chr10:43579168-43584265 |
| 4189 | Cd27 | NM_001033126.2 | chr6:125232621-125237027 |
| 4190 | Cd274 | NM_021893.3 | chr19:29367437-29388094 |
| 4191 | Cd276 | NM_133983.4 | chr9:58524299-58540940 |
| 4192 | Cd28 | NM_007642.4 | chr1:60746387-60773359 |
| 4193 | Cd2ap | NM_009847.3 | chr17:42792950-42876424 |
| 4194 | Cd2bp2 | NM_001285905.1 | chr7:127191659-127196077 |
| 4195 | Cd300a | NM_170758.3 | chr11:114890040-114904651 |
| 4196 | Cd300c | NM_199225.1 | chr11:114956277-114960417 |
| 4197 | Cd300e | NM_172050.2 | chr11:115051916-115062038 |
| 4198 | Cd300lb | NM_199221.2 | chr11:114922780-114934386 |
| 4199 | Cd300ld | NM_145437.2 | chr11:114982445-114989886 |
| 4200 | Cd300lf | NM_001169153.1 | chr11:115116213-115133992 |
| 4201 | Cd300lg | NM_001160711.1 | chr11:102041510-102055617 |
| 4202 | Cd300lh | NM_199201.1 | chr11:115031485-115048295 |
| 4203 | Cd302 | NM_001290660.1 | chr2:60251992-60284484 |
| 4204 | Cd320 | NM_019421.3 | chr17:33843090-33849774 |
| 4205 | Cd33 | NM_001111058.1 | chr7:43527455-43583171 |
| 4206 | Cd34 | NM_001111059.1 | chr1:194938820-194961292 |
| 4207 | Cd36 | NM_001159555.1 | chr5:17781689-17835896 |
| 4208 | Cd37 | NM_001290802.1 | chr7:45233631-45239115 |
| 4209 | Cd38 | NM_007646.5 | chr5:43868808-43912374 |
| 4210 | Cd3d | NM_013487.3 | chr9:44981785-44987052 |
| 4211 | Cd3e | NM_007648.4 | chr9:44998742-45009590 |
| 4212 | Cd3eap | NM_145822.2 | chr7:19356008-19359483 |
| 4213 | Cd3g | NM_009850.2 | chr9:44969571-44980431 |
| 4214 | Cd4 | NM_013488.2 | chr6:124864692-124888209 |
| 4215 | Cd40 | NM_011611.2 | chr2:165055635-165071654 |
| 4216 | Cd40lg | NM_011616.2 | chrX:57212142-57224042 |
| 4217 | Cd44 | NM_001039150.1 | chr2:102811141-102901665 |
| 4218 | Cd46 | NM_010778.4 | chr1:195041237-195092248 |
| 4219 | Cd47 | NM_010581.3 | chr16:49855653-49911683 |
| 4220 | Cd48 | NM_007649.4 | chr1:171682054-171705257 |
| 4221 | Cd5 | NM_007650.2 | chr19:10718142-10738974 |
| 4222 | Cd52 | NM_013706.2 | chr4:134093537-134095073 |
| 4223 | Cd53 | NM_007651.3 | chr3:106758860-106790149 |
| 4224 | Cd55 | NM_010016.2 | chr1:130439029-130462740 |
| 4225 | Cd59a | NM_001111060.2 | chr2:104095800-104115410 |
| 4226 | Cd59b | NM_181858.1 | chr2:104071009-104084957 |
| 4227 | Cd5l | NM_009690.2 | chr3:87357880-87371074 |
| 4228 | Cd6 | NM_001037801.2 | chr19:10789338-10830058 |
| 4229 | Cd63 | NM_001042580.1 | chr10:128908918-128912818 |
| 4230 | Cd68 | NM_001291058.1 | chr11:69664212-69666170 |
| 4231 | Cd69 | NM_001033122.3 | chr6:129267324-129275369 |
| 4232 | Cd7 | NM_009854.2 | chr11:121036748-121039478 |
| 4233 | Cd70 | NM_011617.2 | chr7:57145996-57149777 |
| 4234 | Cd72 | NM_001110320.1 | chr4:43447723-43454626 |
| 4235 | Cd74 | NM_001042605.1 | chr18:60803848-60812652 |
| 4236 | Cd79a | NM_007655.3 | chr7:24897510-24902197 |
| 4237 | Cd79b | NM_008339.3 | chr11:106311340-106314562 |
| 4238 | Cd80 | NM_009855.2 | chr16:38458932-38486932 |
| 4239 | Cd81 | NM_133655.2 | chr7:143052749-143067930 |
| 4240 | Cd82 | NM_001136055.2 | chr2:93419101-93462950 |
| 4241 | Cd83 | NM_012899.2 | chr13:43785111-43803133 |
| 4242 | Cd84 | NM_001252472.1 | chr1:171839696-171855097 |
| 4243 | Cd86 | NM_019388.3 | chr16:36603868-36666077 |
| 4244 | Cd8a | NM_001081110.2 | chr6:71373426-71379171 |
| 4245 | Cd8b1 | NM_009858.2 | chr6:71322811-71337451 |
| 4246 | Cd9 | NM_007657.3 | chr6:125460265-125494755 |
| 4247 | Cd93 | NM_010740.3 | chr2:148436650-148443535 |
| 4248 | Cd96 | NM_032465.2 | chr16:46035656-46120248 |
| 4249 | Cd97 | NM_011636029.1 | chr8:83723250-83741311 |
| 4250 | Cd99l2 | NM_001199349.1 | chrX:71420059-71492849 |
| 4251 | Cda | NM_028176.1 | chr4:138338527-138367955 |
| 4252 | Cdadc1 | NM_001168535.1 | chr14:59559387-59597959 |
| 4253 | Cdan1 | NM_026891.2 | chr2:120716153-120731517 |
| 4254 | Cdc123 | NM_133837.4 | chr2:5794293-5844960 |
| 4255 | Cdc14a | NM_001080818.2 | chr3:116272552-116424032 |
| 4256 | Cdc14b | NM_001122989.1 | chr13:64192544-64248538 |
| 4257 | Cdc16 | NM_027276.2 | chr8:13757689-13781882 |
| 4258 | Cdc20 | NM_023223.2 | chr4:118432900-118437343 |
| 4259 | Cdc20b | NM_001281487.1 | chr13:113035378-113091135 |
| 4260 | Cdc23 | NM_178347.4 | chr18:34631682-34651736 |
| 4261 | Cdc25a | NM_007658.3 | chr9:109875578-109893890 |
| 4262 | Cdc25b | NM_001111075.4 | chr2:131186947-131198511 |
| 4263 | Cdc25c | NM_009860.3 | chr18:34732994-34751533 |
| 4264 | Cdc26 | NM_139291.3 | chr4:62394588-62408623 |
| 4265 | Cdc27 | NM_001285988.1 | chr11:104502525-104550620 |
| 4266 | Cdc34 | NM_177613.2 | chr10:79682194-79688398 |
| 4267 | Cdc37 | NM_016742.4 | chr9:21138540-21149906 |
| 4268 | Cdc37l1 | NM_025950.3 | chr19:28990351-29020237 |
| 4269 | Cdc40 | NM_027879.2 | chr10:40831621-40883143 |
| 4270 | Cdc42 | NM_001243769.1 | chr4:137321762-137357759 |
| 4271 | Cdc42bpa | NM_001033285.1 | chr1:179961088-180165602 |
| 4272 | Cdc42bpb | NM_183016.2 | chr12:111292971-111377718 |
| 4273 | Cdc42bpg | NM_001033842.1 | chr19:6306456-6325652 |
| 4274 | Cdc42ep1 | NM_027219.3 | chr15:78842646-78850902 |
| 4275 | Cdc42ep2 | NM_026772.2 | chr19:5917555-5924816 |
| 4276 | Cdc42ep3 | NM_026514.2 | chr17:79334024-79355091 |
| 4277 | Cdc42ep4 | NM_001163346.1 | chr11:113726849-113751815 |
| 4278 | Cdc42ep5 | NM_021454.3 | chr7:4151259-4164699 |
| 4279 | Cdc42se1 | NM_001038708.3 | chr3:95228942-95236424 |
| 4280 | Cdc42se2 | NM_178626.3 | chr11:54717414-54787703 |
| 4281 | Cdc45 | NM_001161623.1 | chr16:18780446-18811639 |
| 4282 | Cdc5l | NM_152810.2 | chr17:45391887-45433707 |
| 4283 | Cdc6 | NM_001025779.1 | chr11:98907088-98923942 |
| 4284 | Cdc7 | NM_001271566.1 | chr5:106964560-106984439 |
| 4285 | Cdc73 | NM_145991.2 | chr1:143608275-143702893 |
| 4286 | Cdca2 | NM_001110162.1 | chr14:67676353-67715610 |
| 4287 | Cdca3 | NM_013538.5 | chr6:124830175-124833701 |
| 4288 | Cdca4 | NM_028023.3 | chr12:112820234-112829389 |
| 4289 | Cdca5 | NM_026410.3 | chr19:6085096-6091773 |
| 4290 | Cdca7 | NM_025866.3 | chr2:72476218-72486890 |
| 4291 | Cdca7l | NM_146040.1 | chr12:117843860-117878706 |
| 4292 | Cdca8 | NM_026560.4 | chr4:124918464-124936917 |
| 4293 | Cdcp1 | NM_133974.3 | chr9:123172284-123216038 |
| 4294 | Cdcp2 | NM_172873.3 | chr4:107096890-107107748 |
| 4295 | Cdh1 | NM_009864.2 | chr8:106603367-106670246 |
| 4296 | Cdh10 | NM_009865.2 | chr15:18820328-19014234 |
| 4297 | Cdh11 | NM_009866.5 | chr8:102632094-102785111 |
| 4298 | Cdh12 | NM_001008420.2 | chr15:21111451-21589533 |
| 4299 | Cdh13 | NM_019707.4 | chr8:118283754-119323448 |
| 4300 | Cdh15 | NM_007662.2 | chr8:122848373-122867397 |
| 4301 | Cdh16 | NM_001252627.1 | chr8:104614137-104624396 |
| 4302 | Cdh17 | NM_019753.4 | chr4:11758156-11817905 |
| 4303 | Cdh18 | NM_001081299.1 | chr15:23036462-23474418 |
| 4304 | Cdh19 | NM_001081386.1 | chr1:110889194-110977372 |
| 4305 | Cdh2 | NM_007664.4 | chr18:16588876-16809049 |
| 4306 | Cdh20 | NM_011800.4 | chr1:104768818-104895481 |
| 4307 | Cdh22 | NM_174988.3 | chr2:165111506-165234737 |
| 4308 | Cdh23 | NM_001252635.1 | chr10:60302749-60696490 |
| 4309 | Cdh24 | NM_199470.2 | chr14:54631991-54641364 |
| 4310 | Cdh26 | NM_001291189.1 | chr2:178430514-178487366 |
| 4311 | Cdh3 | NM_001037809.5 | chr8:106510851-106556911 |
| 4312 | Cdh4 | NM_009867.2 | chr2:179442477-179899375 |
| 4313 | Cdh5 | NM_009868.4 | chr8:104101624-104144502 |
| 4314 | Cdh6 | NM_007666.3 | chr15:13034199-13173639 |
| 4315 | Cdh7 | NM_172853.2 | chr1:109983736-110193001 |
| 4316 | Cdh8 | NM_001039154.2 | chr8:99028768-99416471 |
| 4317 | Cdh9 | NM_009869.1 | chr15:16778100-16856777 |
| 4318 | Cdhr1 | NM_130878.2 | chr14:37077848-37098311 |
| 4319 | Cdhr2 | NM_001033364.3 | chr13:54701462-54736662 |
| 4320 | Cdhr3 | NM_001024478.1 | chr12:33033795-33092875 |
| 4321 | Cdhr5 | NM_001114322.1 | chr7:141269084-141276786 |
| 4322 | Cdip1 | NM_025670.4 | chr16:4765460-4789935 |
| 4323 | Cdipt | NM_026638.3 | chr7:126975913-126980501 |
| 4324 | Cdk1 | NM_007659.3 | chr10:69336634-69352912 |
| 4325 | Cdk10 | NM_194444.2 | chr8:123224840-123232256 |
| 4326 | Cdk11b | NM_007661.3 | chr4:155624868-155649932 |
| 4327 | Cdk12 | NM_001109626.1 | chr11:98203304-98253540 |
| 4328 | Cdk13 | NM_001081058.2 | chr13:17715961-17805097 |
| 4329 | Cdk14 | NM_011074.3 | chr5:4803383-5380251 |
| 4330 | Cdk15 | NM_001033373.2 | chr1:59256906-59352369 |
| 4331 | Cdk16 | NM_011049.5 | chrX:20688425-20699879 |
| 4332 | Cdk17 | NM_146239.2 | chr10:93160875-93241342 |
| 4333 | Cdk18 | NM_008795.2 | chr1:132113546-132139685 |
| 4334 | Cdk19 | NM_001168304.1 | chr10:40349307-40483818 |
| 4335 | Cdk2 | NM_016756.4 | chr10:128697938-128705051 |
| 4336 | Cdk20 | NM_053180.1 | chr13:64432552-64439721 |
| 4337 | Cdk2ap1 | NM_013812.2 | chr5:124345438-124354628 |
| 4338 | Cdk2ap2 | NM_026373 | chr19:4097350-4099017 |
| 4339 | Cdk3-ps | NR_004853.1 | chr11:116116001-116220287 |
| 4340 | Cdk4 | NM_009870.3 | chr10:127063602-127067282 |
| 4341 | Cdk5 | NM_007668.3 | chr5:24418241-24423530 |
| 4342 | Cdk5r1 | NM_009871.2 | chr11:80477049-80481179 |
| 4343 | Cdk5r2 | NM_009872.3 | chr1:74855028-74857732 |
| 4344 | Cdk5rap1 | NM_025876.2 | chr2:154335385-154372719 |
| 4345 | Cdk5rap2 | NM_145990.4 | chr4:70216854-70410435 |
| 4346 | Cdk5rap3 | NM_030248.2 | chr11:96907424-96916514 |
| 4347 | Cdk6 | NM_009873.3 | chr5:3343892-3531005 |
| 4348 | Cdk7 | NM_009874.3 | chr13:100697024-100730942 |
| 4349 | Cdk8 | NM_153599.3 | chr5:146231674-146302874 |
| 4350 | Cdk9 | NM_130860.3 | chr2:32705781-32712784 |
| 4351 | Cdkal1 | NM_144536.3 | chr13:29325300-29855673 |
| 4352 | Cdkl1 | NM_183294.2 | chr12:69746847-69790707 |
| 4353 | Cdkl2 | NM_001276315.1 | chr5:92006073-92042696 |
| 4354 | Cdkl3 | NM_001166653.1 | chr11:52004220-52038165 |
| 4355 | Cdkl4 | NM_001033443.4 | chr17:80523549-80563834 |
| 4356 | Cdkl5 | NM_001024624.2 | chrX:160784307-160994681 |
| 4357 | Cdkn1a | NM_001111099.2 | chr17:29090978-29100722 |
| 4358 | Cdkn1b | NM_009875.4 | chr6:134920400-134925525 |
| 4359 | Cdkn1c | NM_001161624.1 | chr7:143458338-143461050 |
| 4360 | Cdkn2a | NM_001040654.1 | chr4:89274472-89282192 |
| 4361 | Cdkn2aip | NM_172407.3 | chr8:47709343-47713931 |
| 4362 | Cdkn2aipnl | NM_029976.3 | chr11:51967630-51977336 |
| 4363 | Cdkn2b | NM_007670.4 | chr4:89306288-89311032 |
| 4364 | Cdkn2c | NM_007671.3 | chr4:109660875-109665372 |
| 4365 | Cdkn2d | NM_009878.3 | chr9:21288463-21291209 |
| 4366 | Cdkn3 | NM_028222.1 | chr14:46760540-46771525 |

Fig. 26 - 24

| | | | |
|---|---|---|---|
| 4367 | Cdnf | NM_177647.4 | chr2:3513064-3526376 |
| 4368 | Cdo1 | NM_033037.3 | chr18:46713204-46728342 |
| 4369 | Cdon | NM_021339.2 | chr9:35452075-35507652 |
| 4370 | Cdpf1 | NM_001164625.1 | chr15:85806971-85811697 |
| 4371 | Cdr1 | NM_001166658.1 | chrX:61183245-61185558 |
| 4372 | Cdr2 | NM_007672.2 | chr7:120957036-120982312 |
| 4373 | Cdr2l | NM_001080929.1 | chr11:115381915-115396132 |
| 4374 | Cdt4 | NM_025496.1 | chr11:62951192-62993095 |
| 4375 | Cds1 | NM_173370.3 | chr5:101765129-101823852 |
| 4376 | Cds2 | NM_001291039.1 | chr2:132285938-132312050 |
| 4377 | Cdsn | NM_001008424.2 | chr17:35552127-35557180 |
| 4378 | Cdt1 | NM_026014.3 | chr8:122568014-122573130 |
| 4379 | Cdv3 | NM_001134426.1 | chr9:103353101-103365780 |
| 4380 | Cdx1 | NM_009880.3 | chr18:61018861-61036199 |
| 4381 | Cdx2 | NM_007673.3 | chr5:147300899-147307249 |
| 4382 | Cdx4 | NM_007674.3 | chrX:103321397-103330224 |
| 4383 | Cdyl | NM_001123386.1 | chr13:35741401-35874064 |
| 4384 | Cdyl2 | NM_029441.3 | chr8:116568723-116732991 |
| 4385 | Ceacam1 | NM_001039185.1 | chr7:25461701-25477625 |
| 4386 | Ceacam10 | NM_007675.4 | chr7:24777203-24784655 |
| 4387 | Ceacam11 | NM_023289.1 | chr7:17972166-17978556 |
| 4388 | Ceacam12 | NM_001162523 | chr7:18065928-18077986 |
| 4389 | Ceacam13 | NM_027210 | chr7:18009888-18019220 |
| 4390 | Ceacam14 | NM_025957 | chr7:17812681-17815627 |
| 4391 | Ceacam15 | NM_175315.1 | chr7:16671330-16675705 |
| 4392 | Ceacam16 | NM_001033419.1 | chr7:19852096-19861299 |
| 4393 | Ceacam18 | NM_028236.1 | chr7:43634738-43649294 |
| 4394 | Ceacam19 | NM_177036.5 | chr7:19875741-19887965 |
| 4395 | Ceacam2 | NM_001113368.1 | chr7:25516041-25540004 |
| 4396 | Ceacam20 | NM_027839.2 | chr7:19965411-19991111 |
| 4397 | Ceacam3 | NM_054059.1 | chr7:17150399-17163231 |
| 4398 | Ceacam5 | NM_028480.2 | chr7:17713251-17761121 |
| 4399 | Ceacam9 | NM_011927.4 | chr7:16721928-16726110 |
| 4400 | Ceacam-ps1 | NR_003247.2 | chr7:16649029-16657478 |
| 4401 | Cebpa | NM_001287514.1 | chr7:35119292-35121928 |
| 4402 | Cebpb | NM_009883.4 | chr2:167668914-167690432 |
| 4403 | Cebpd | NM_007679.4 | chr16:15887285-15889545 |
| 4404 | Cebpe | NM_207131.1 | chr14:54710362-54712174 |
| 4405 | Cebpg | NM_009884.3 | chr7:35046421-35056566 |
| 4406 | Cebpz | NM_001024806.2 | chr17:78919002-78937070 |
| 4407 | Cebpzos | NM_001177402.1 | chr17:78916498-78921048 |
| 4408 | Cecr2 | NM_001128151.1 | chr6:120666420-120771191 |
| 4409 | Cecr5 | NM_144815.2 | chr6:120509493-120531299 |
| 4410 | Cecr6 | NM_033567.1 | chr6:120488938-120493807 |
| 4411 | Cel | NM_009885.2 | chr2:28555819-28563403 |
| 4412 | Cela1 | NM_033612.2 | chr15:100674421-100687920 |
| 4413 | Cela2a | NM_007919.2 | chr4:141814962-141826003 |
| 4414 | Cela3b | NM_026419.2 | chr4:137421007-137430520 |
| 4415 | Celf1 | NM_001244891.1 | chr2:90940396-91019497 |
| 4416 | Celf2 | NM_001110228.1 | chr2:6539698-6884996 |
| 4417 | Celf3 | NM_001143723.1 | chr3:94478548-94492198 |
| 4418 | Celf4 | NM_001146292.1 | chr18:25477619-25753983 |
| 4419 | Celf5 | NM_178954.3 | chr10:81459227-81482709 |
| 4420 | Celf6 | NM_175235.3 | chr9:59578336-59607292 |
| 4421 | Celrr | NR_038008.1 | chr1:121087404-121120975 |
| 4422 | Celsr1 | NM_009886.2 | chr15:85898757-86033777 |
| 4423 | Celsr2 | NM_001004177.2 | chr3:108390847-108415494 |
| 4424 | Celsr3 | NM_080437.2 | chr9:108826319-108852969 |
| 4425 | Cemip | NM_030728.4 | chr7:83932856-84086505 |
| 4426 | Cend1 | NM_021316.4 | chr7:141426450-141429420 |
| 4427 | Cenpa | NM_007681 | chr5:30666885-30674837 |
| 4428 | Cenpb | NM_007682 | chr2:131177288-131180012 |
| 4429 | Cenpc1 | NM_007683.3 | chr5:86012024-86065583 |
| 4430 | Cenpe | NM_173762 | chr3:135212562-135273540 |
| 4431 | Cenpf | NM_001081363.2 | chr1:189640613-189688086 |
| 4432 | Cenph | NM_021886.1 | chr13:100759685-100775899 |
| 4433 | Cenpi | NM_145924.3 | chrX:134308083-134363104 |
| 4434 | Cenpj | NM_001014996 | chr14:56526760-56571846 |
| 4435 | Cenpk | NM_021790.2 | chr13:104229387-104249622 |
| 4436 | Cenpl | NM_001159930.2 | chr1:161070766-161086724 |
| 4437 | Cenpm | NM_001080158.1 | chr15:82233775-82244336 |
| 4438 | Cenpn | NM_028131.3 | chr8:116921739-116941503 |
| 4439 | Cenpo | NM_134046.5 | chr12:4211671-4234294 |
| 4440 | Cenpq | NM_025495.3 | chr13:49464058-49652731 |
| 4441 | Cenpq | NM_031863.3 | chr17:40923054-40934551 |
| 4442 | Cenpt | NM_177150.2 | chr8:105844677-105852008 |
| 4443 | Cenpu | NM_027973.3 | chr8:46552068-46579584 |
| 4444 | Cenpv | NM_028448.1 | chr11:62524943-62539261 |
| 4445 | Cenpw | NM_001109747.1 | chr10:30196008-30200540 |
| 4446 | Cep104 | NM_177673.2 | chr4:153975560-154007225 |
| 4447 | Cep112 | NM_029586.2 | chr11:108682617-108860615 |
| 4448 | Cep120 | NM_178686.3 | chr18:53681722-53744547 |
| 4449 | Cep128 | NM_181815.3 | chr12:90998491-91384409 |
| 4450 | Cep131 | NM_009734.3 | chr11:120064429-120086827 |
| 4451 | Cep135 | NM_199032.2 | chr5:76917713-76646466 |
| 4452 | Cep152 | NM_001081091.1 | chr2:125563087-125625113 |
| 4453 | Cep162 | NM_199316.2 | chr9:87191962-87255532 |
| 4454 | Cep164 | NM_001081373.2 | chr9:45766945-45828638 |
| 4455 | Cep170 | NM_001099637.2 | chr1:176733652-176807124 |
| 4456 | Cep170b | NM_001246602.3 | chr12:112722173-112746591 |
| 4457 | Cep19 | NM_025892.2 | chr16:32099801-32108054 |
| 4458 | Cep192 | NM_027556.1 | chr18:67800106-67885170 |
| 4459 | Cep250 | NM_001129999.1 | chr2:155956557-155998900 |
| 4460 | Cep290 | NM_146009.2 | chr10:100488288-100573655 |
| 4461 | Cep350 | NM_001039184.1 | chr1:155844963-155973255 |
| 4462 | Cep41 | NM_031998.3 | chr6:30653456-30693749 |
| 4463 | Cep44 | NM_001009951.1 | chr8:56531521-56550566 |
| 4464 | Cep55 | NM_001164362.1 | chr19:38055041-38074425 |
| 4465 | Cep57 | NM_026665.4 | chr9:13807787-13827107 |
| 4466 | Cep57l1 | NM_001243074.1 | chr10:41718839-41809868 |
| 4467 | Cep63 | NM_001081122.1 | chr9:102586577-102626124 |
| 4468 | Cep68 | NM_172260.3 | chr11:20227036-20249424 |
| 4469 | Cep70 | NM_023873.3 | chr9:99243467-99300403 |
| 4470 | Cep72 | NM_028959.3 | chr13:74036494-74062285 |
| 4471 | Cep76 | NM_001081073.1 | chr18:67617396-67641336 |
| 4472 | Cep78 | NM_198019.2 | chr19:15955772-15984989 |
| 4473 | Cep83 | NM_029852.2 | chr10:94688789-94790336 |
| 4474 | Cep83os | NR_015524.1 | chr10:94673492-94688613 |
| 4475 | Cep85 | NM_144527.3 | chr4:134129857-134187085 |
| 4476 | Cep85l | NM_001204983.1 | chr10:53278080-53379851 |
| 4477 | Cep89 | NM_028120.2 | chr7:35397092-35438684 |
| 4478 | Cep95 | NM_001166685.1 | chr11:106789251-106818861 |
| 4479 | Cep97 | NM_001159364.1 | chr16:55924360-55934848 |
| 4480 | Cept1 | NM_133869.4 | chr3:106502259-106547802 |
| 4481 | Cer1 | NM_009887.2 | chr4:82881750-82885151 |
| 4482 | Cercam | NM_207298.2 | chr2:29869493-29882840 |
| 4483 | Cerk | NM_145475.4 | chr15:86139100-86186141 |
| 4484 | Cerkl | NM_001048176.1 | chr2:79332490-79428988 |
| 4485 | Cers1 | NM_138647.3 | chr8:70315774-70331588 |
| 4486 | Cers2 | NM_029789.1 | chr3:95315251-95323568 |
| 4487 | Cers3 | NM_001164201.1 | chr7:66743503-66823692 |
| 4488 | Cers4 | NM_026058.4 | chr8:4493404-4526079 |
| 4489 | Cers5 | NM_028015.2 | chr15:99735591-99772515 |
| 4490 | Cers6 | NM_172856.3 | chr2:68861556-69111290 |
| 4491 | Ces1a | NM_001013764.2 | chr8:93020214-93048192 |
| 4492 | Ces1b | NM_001081372.1 | chr8:93056726-93080017 |
| 4493 | Ces1c | NM_007954.4 | chr8:93099015-93131283 |
| 4494 | Ces1d | NM_053200.2 | chr8:93166071-93197804 |
| 4495 | Ces1e | NM_133660.3 | chr8:93201217-93229619 |
| 4496 | Ces1f | NM_144930.2 | chr8:93256235-93279736 |
| 4497 | Ces1g | NM_021456.4 | chr8:93302868-93337209 |
| 4498 | Ces2a | NM_001190330.1 | chr8:104734002-104741634 |
| 4499 | Ces2b | NM_198171.2 | chr8:104831643-104838652 |
| 4500 | Ces2c | NM_145603.2 | chr8:104847067-104854452 |
| 4501 | Ces2d-ps | NR_033726.1 | chr8:104867423-104874082 |
| 4502 | Ces2e | NM_001163756.1 | chr8:104926259-104934672 |
| 4503 | Ces2f | NM_001079865.2 | chr8:104947355-104955962 |
| 4504 | Ces2g | NM_197999.2 | chr8:104961717-104969537 |
| 4505 | Ces2h | NM_001272045.1 | chr8:105000852-105020410 |
| 4506 | Ces3a | NM_001164681.1 | chr8:105048598-105058414 |
| 4507 | Ces3b | NM_001159415.1 | chr8:105083754-105093591 |
| 4508 | Ces4a | NM_146213.2 | chr8:105131799-105150109 |
| 4509 | Ces5a | NM_001003951.2 | chr8:93499212-93535707 |
| 4510 | Cetn1 | NM_007593.5 | chr18:9618418-9619469 |
| 4512 | Cetn2 | NM_019405.6 | chrX:72913564-72918344 |
| 4512 | Cetn3 | NM_007684.3 | chr13:81783291-81797157 |
| 4513 | Cetn4 | NM_145825.2 | chr3:37308626-37312446 |
| 4514 | Cfb | NM_001142706.1 | chr17:34856373-34862514 |
| 4515 | Cfc1 | NM_007685.2 | chr1:34535647-34544311 |
| 4516 | Cfd | NM_001291915.1 | chr10:79890852-79892660 |
| 4517 | Cfdp1 | NM_011801.1 | chr8:111768472-111854310 |
| 4518 | Cfh | NM_009888.3 | chr1:140085854-140183411 |
| 4519 | Cfhr1 | NM_015780.2 | chr1:139547063-139560222 |
| 4520 | Cfhr2 | NM_001025575.2 | chr1:139810291-139858699 |
| 4521 | Cfi | NM_007686.2 | chr3:129836738-129875328 |
| 4522 | Cfl1 | NM_007687.5 | chr19:5490454-5494031 |
| 4523 | Cfl2 | NM_007688 | chr12:54858818-54862877 |
| 4524 | Cflar | NM_001289704 | chr1:58711490-58759209 |
| 4525 | Cfp | NM_008823.4 | chrX:20925453-20931555 |
| 4526 | Cftr | NM_021050.2 | chr6:18170686-18322769 |
| 4527 | Cga | NM_009889.2 | chr4:34893778-34907374 |
| 4528 | Cggbp1 | NM_178647.2 | chr16:64852084-64859491 |
| 4529 | Cgn | NM_001037711.2 | chr3:94760069-94786515 |
| 4530 | Cgnl1 | NM_026599.5 | chr9:71626506-71771602 |
| 4531 | Cgref1 | NM_001160149.1 | chr5:30933142-30945427 |
| 4532 | Cgrrf1 | NM_026832.3 | chr14:46832243-46854190 |
| 4533 | Ch25h | NM_009890.1 | chr19:34473783-34475135 |
| 4534 | Chac1 | NM_026929.4 | chr2:119351241-139354327 |
| 4535 | Chac2 | NM_001290667.1 | chr11:30976706-30986365 |
| 4536 | Chad | NM_007689.4 | chr11:94565073-94569127 |
| 4537 | Chadl | NM_001164320.1 | chr15:81686166-81697287 |
| 4538 | Chaf1a | NM_013733.3 | chr17:56040415-56068026 |
| 4539 | Chaf1b | NM_028083.4 | chr16:93883900-93906106 |
| 4540 | Champ1 | NM_181854.2 | chr8:13869640-13881639 |
| 4541 | Chat | NM_009891.2 | chr14:32408202-32465909 |
| 4542 | Chchd1 | NM_025366.3 | chr14:20703026-20704425 |
| 4543 | Chchd10 | NM_175329.3 | chr10:75935572-75937734 |
| 4544 | Chchd2 | NM_024166.6 | chr5:129881160-129887470 |
| 4545 | Chchd3 | NM_025336.1 | chr6:32792226-33060152 |
| 4546 | Chchd4 | NM_133928.2 | chr6:91464275-91473423 |
| 4547 | Chchd5 | NM_025395.3 | chr2:129129699-129134111 |
| 4548 | Chchd6 | NM_001167736.1 | chr6:89383145-89595652 |
| 4549 | Chchd7 | NM_001190322.2 | chr4:3938887-3943525 |
| 4550 | Chd1 | NM_007690.3 | chr17:15704986-15772612 |
| 4551 | Chd1l | NM_026539.2 | chr3:97560747-97610190 |
| 4552 | Chd2 | NM_001081345.2 | chr7:73426651-73541746 |
| 4553 | Chd3 | NM_146019.4 | chr11:69343272-69369426 |
| 4554 | Chd3os | NR_027827.1 | chr11:69340768-69342647 |
| 4555 | Chd4 | NM_145979.2 | chr6:125096162-125130501 |
| 4556 | Chd5 | NM_001081376.1 | chr4:152338650-152390194 |

Fig. 26 - 25

| | | | | | | | | |
|---|---|---|---|---|---|---|---|---|
| 4557 | Chd6 | NM_173368.1 | chr2:160946977-161109086 | | 4652 | Cib1 | NM_001291275.1 | chr7:80227155-80232805 |
| 4558 | Chd7 | NM_001277149.1 | chr4:8690405-8868449 | | 4653 | Cib2 | NM_019686.5 | chr9:54545351-54560079 |
| 4559 | Chd8 | NM_201637.2 | chr14:52198150-52237572 | | 4654 | Cib3 | NM_001080812.1 | chr8:72204334-72212837 |
| 4560 | Chd9 | NM_177224.2 | chr8:90828834-91054508 | | 4655 | Cib4 | NM_028483.1 | chr5:30485583-30545836 |
| 4561 | Chdh | NM_001336240.1 | chr14:30008999-30040466 | | 4656 | Cic | NM_001302811.1 | chr7:25267657-25294159 |
| 4562 | Chek1 | NM_007691.5 | chr9:36708481-36726658 | | 4657 | Cidea | NM_007702.2 | chr18:67343563-67367794 |
| 4563 | Chek2 | NM_016681.3 | chr5:110840016-110874133 | | 4658 | Cideb | NM_009894.3 | chr14:55754054-55758424 |
| 4564 | Cherp | NM_138585.3 | chr8:72460482-72475233 | | 4659 | Cidec | NM_178373.3 | chr8:113424635-113435755 |
| 4565 | Chfr | NM_001289577.1 | chr5:110135829-110171973 | | 4660 | Ciita | NM_001243760.2 | chr16:10480071-10527640 |
| 4566 | Chga | NM_007693.1 | chr12:102554968-102565027 | | 4661 | Cilp | NM_173385.2 | chr9:65265179-65280605 |
| 4567 | Chgb | NM_007694.4 | chr2:132781277-132795072 | | 4662 | Cilp2 | NM_026818 | chr8:69880365-69887392 |
| 4568 | Chia1 | NM_023186.3 | chr3:106113381-106132116 | | 4663 | Cinp | NM_026048.4 | chr12:110872609-110889145 |
| 4569 | Chic1 | NM_009767.2 | chrX:103356475-103396118 | | 4664 | Cipc | NM_001289429.1 | chr12:86947040-86965366 |
| 4570 | Chic2 | NM_028850.5 | chr5:75005003-75044643 | | 4665 | Cir1 | NM_025854 | chr2:73283871-73312592 |
| 4571 | Chid1 | NM_001142681.1 | chr7:141493135-141539857 | | 4666 | Cirbp | NM_007705.2 | chr10:80167840-80171653 |
| 4572 | Chil1 | NM_007695.3 | chr1:134182403-134190031 | | 4667 | Cirh1a | NM_011574.2 | chr8:106893839-106923094 |
| 4573 | Chil3 | NM_009892.3 | chr3:106147553-106167564 | | 4668 | Cisd1 | NM_134007.4 | chr10:71330493-71344849 |
| 4574 | Chil4 | NM_145126.2 | chr3:106201490-106219479 | | 4669 | Cisd2 | NM_025902.3 | chr3:135406411-135423433 |
| 4575 | Chil6 | NM_178412.2 | chr3:106187383-106406182 | | 4670 | Cisd3 | NM_001085500.2 | chr11:97685951-97688625 |
| 4576 | Chit1 | NM_001284524.1 | chr1:134111241-134151540 | | 4671 | Cish | NM_009895.3 | chr9:107296688-107301961 |
| 4577 | Chka | NM_001271496.1 | chr19:3851772-3894369 | | 4672 | Cistr-act | NR_104334.1 | chr15:102746440-102746909 |
| 4578 | Chkb | NM_007692.6 | chr15:89426348-89429927 | | 4673 | Cit | NM_007708.3 | chr5:115845655-116006341 |
| 4579 | ChkbCpt1b | NR_064843.2 | chr15:89416404-89429927 | | 4674 | Cited1 | NM_001276466.1 | chrX:102247377-102252181 |
| 4580 | Chl1 | NM_007697.2 | chr6:103510875-103733035 | | 4675 | Cited2 | NM_010828.3 | chr10:17723227-17725674 |
| 4581 | Chm | NM_018818.2 | chrX:113040591-113185515 | | 4676 | Cited4 | NM_019563.2 | chr4:120666562-120667820 |
| 4582 | Chml | NM_021350.2 | chr1:175682237-175688353 | | 4677 | Ciz1 | NM_001252534.1 | chr2:32363197-32378313 |
| 4583 | Chmp1a | NM_145606.3 | chr8:123204260-123212788 | | 4678 | CK137956 | NM_001134733.1 | chr4:127927591-127970841 |
| 4584 | Chmp1b | NM_024290.2 | chr18:67205358-67207887 | | 4679 | Ckap2 | NM_001004140.2 | chr22:22168151-22185819 |
| 4585 | Chmp2a | NM_026885.3 | chr7:13032005-13034777 | | 4680 | Ckap2l | NM_181589.3 | chr2:129268209-129297212 |
| 4586 | Chmp2b | NM_026879.2 | chr16:65539132-65562697 | | 4681 | Ckap4 | NM_175451.1 | chr10:84526304-84533888 |
| 4587 | Chmp3 | NM_025783.3 | chr6:71543853-71581574 | | 4682 | Ckap5 | NM_001165989.1 | chr2:91546321-91620665 |
| 4588 | Chmp4b | NM_029362.3 | chr2:154657025-154694783 | | 4683 | Ckb | NM_021273.4 | chr12:111669354-111672338 |
| 4589 | Chmp4c | NM_025519.2 | chr3:10366972-10391005 | | 4684 | Ckf | NM_001037841.3 | chr8:104250860-104264936 |
| 4590 | Chmp5 | NM_029814.1 | chr4:40948552-40965302 | | 4685 | Ckm | NM_007710.2 | chr7:19411093-19421583 |
| 4591 | Chmp6 | NM_001085498.2 | chr11:119913809-119919552 | | 4686 | Cknt1 | NM_099897.2 | chr2:121358640-121363737 |
| 4592 | Chmp7 | NM_134078.4 | chr14:69716978-69732570 | | 4687 | Ckmt2 | NM_198415.2 | chr13:91853386-91876885 |
| 4593 | Chn1 | NM_001113246.2 | chr2:73610659-73775346 | | 4688 | Cks1b | NM_016904.1 | chr3:89415471-89418291 |
| 4594 | Chn1os3 | NR_040623.1 | chr2:73596525-73616012 | | 4689 | Cks1brt | NM_001037922.3 | chr8:85151923-85173622 |
| 4595 | Chn2 | NM_001163640.1 | chr6:54039931-54301812 | | 4690 | Cks2 | NM_025415.3 | chr13:51645231-51650662 |
| 4596 | Chodl | NM_139134.3 | chr16:78930947-78951728 | | 4691 | Clasp1 | NM_001293300.1 | chr1:118389058-118609462 |
| 4597 | Chordc1 | NM_025844.2 | chr9:18292266-18314000 | | 4692 | Clasp2 | NM_001081960.1 | chr9:113812585-113919697 |
| 4598 | Chp1 | NM_019769.3 | chr2:119547706-119587022 | | 4693 | Clasrp | NM_016680.5 | chr7:19581037-19604486 |
| 4599 | Chp2 | NM_027363.1 | chr7:122219495-122222539 | | 4694 | Clca1 | NM_009899.4 | chr3:144729676-144760977 |
| 4600 | Chpf | NM_001001565.2 | chr1:75474568-75479471 | | 4695 | Clca2 | NM_030601.3 | chr3:144796558-144819494 |
| 4601 | Chpf2 | NM_133913.2 | chr5:24586749-24592486 | | 4696 | Clca3 | NM_017474.2 | chr3:145004536-145032776 |
| 4602 | Chpt1 | NM_001146690.1 | chr10:88472812-88503970 | | 4697 | Clca4 | NM_139148.2 | chr3:144822623-144849302 |
| 4603 | Chrac1 | NM_053068.3 | chr15:73090411-73094075 | | 4698 | Clca5 | NM_178697.4 | chr3:145070264-145099041 |
| 4604 | Chrd | NM_001278041.1 | chr16:20733126-20742384 | | 4699 | Clca6 | NM_207208.3 | chr3:144952485-144975045 |
| 4605 | Chrdl1 | NM_001114385.1 | chrX:143285673-143394262 | | 4700 | Clec1 | NM_001177770.1 | chr3:108653989-108678011 |
| 4606 | Chrdl2 | NM_001291320.1 | chr7:100009917-100034726 | | 4701 | Clcf1 | NM_019952.5 | chr19:4214237-4223505 |
| 4607 | Chrm1 | NM_001112697.1 | chr19:8664004-8683602 | | 4702 | Clcn1 | NM_013491.2 | chr6:42286684-42314656 |
| 4608 | Chrm2 | NM_203491.3 | chr6:36388083-36524774 | | 4703 | Clcn2 | NM_009900.2 | chr16:20702965-20716636 |
| 4609 | Chrm3 | NM_033269.4 | chr13:9876612-10360803 | | 4704 | Clcn3 | NM_007711.3 | chr8:60910388-60983311 |
| 4610 | Chrm4 | NM_007699.2 | chr2:91922188-91929829 | | 4705 | Clcn4-2 | NM_011334.4 | chr7:7282308-7299557 |
| 4611 | Chrm5 | NM_205783.2 | chr2:112479071-112480817 | | 4706 | Clcn5 | NM_001243762.1 | chrX:7158411-7319358 |
| 4612 | Chrna1 | NM_007389.5 | chr2:73563280-73580338 | | 4707 | Clcn6 | NM_011929.3 | chr4:148004258-148038813 |
| 4613 | Chrna10 | NM_001081424.1 | chr7:102111265-102116713 | | 4708 | Clcn7 | NM_011930.3 | chr17:25133393-25162099 |
| 4614 | Chrna2 | NM_144803.2 | chr14:66140959-66152948 | | 4709 | Clcnka | NM_001146307.1 | chr4:141384610-141398099 |
| 4615 | Chrna3 | NM_145129.2 | chr9:55011342-55026559 | | 4710 | Clcnkb | NM_019701.2 | chr4:141404356-141415988 |
| 4616 | Chrna4 | NM_015730.5 | chr2:181022310-181039177 | | 4711 | Cldn1 | NM_016674.4 | chr16:26356645-26371839 |
| 4617 | Chrna5 | NM_176844.4 | chr9:54980879-55007779 | | 4712 | Cldn10 | NM_001160096.1 | chr14:118787870-118874525 |
| 4618 | Chrna6 | NM_021369.2 | chr8:27403211-27413944 | | 4713 | Cldn11 | NM_008770.3 | chr3:31149919-31164326 |
| 4619 | Chrna7 | NM_007390.3 | chr7:63098691-63212526 | | 4714 | Cldn12 | NM_001193659.1 | chr5:5505014-5514849 |
| 4620 | Chrna9 | NM_001081104.1 | chr5:65967123-65977486 | | 4715 | Cldn13 | NM_020504.4 | chr5:134914249-134915530 |
| 4621 | Chrnb1 | NM_009601.4 | chr11:69784035-69795937 | | 4716 | Cldn14 | NM_001165925.1 | chr16:93919030-93929567 |
| 4622 | Chrnb2 | NM_009602.4 | chr3:89753447-89784632 | | 4717 | Cldn15 | NM_021719.4 | chr5:136967868-136975845 |
| 4623 | Chrnb3 | NM_027454.4 | chr8:27368710-27399730 | | 4718 | Cldn16 | NM_053241.5 | chr16:26463134-26482764 |
| 4624 | Chrnb4 | NM_148944.4 | chr9:55028155-55048544 | | 4719 | Cldn17 | NM_181490.3 | chr16:88505806-88506978 |
| 4625 | Chrnd | NM_021600.3 | chr1:87190596-87200070 | | 4720 | Cldn18 | NM_001194921.1 | chr9:99690796-99717267 |
| 4626 | Chrne | NM_009603.1 | chr11:70614882-70619194 | | 4721 | Cldn19 | NM_001038590.1 | chr4:119255468-119259855 |
| 4627 | Chrng | NM_009604.3 | chr1:87205810-87211835 | | 4722 | Cldn2 | NM_016675.4 | chrX:139800807-139811388 |
| 4628 | Chst1 | NM_023850.2 | chr2:92599706-92615252 | | 4723 | Cldn20 | NM_001101560.1 | chr17:3532553-3533213 |
| 4629 | Chst10 | NM_145142.2 | chr1:38868872-38898160 | | 4724 | Cldn22 | NM_029383.1 | chr8:47824481-47825475 |
| 4630 | Chst11 | NM_021439.2 | chr10:82985496-83195891 | | 4725 | Cldn23 | NM_027998.4 | chr8:35824708-35826559 |
| 4631 | Chst12 | NM_021528.3 | chr5:140506608-140525238 | | 4726 | Cldn24 | NM_001111318.1 | chr8:47822142-47822805 |
| 4632 | Chst13 | NM_027928.1 | chr6:90308350-90325185 | | 4727 | Cldn25 | NM_001252450.1 | chr16:58727909-58734247 |
| 4633 | Chst14 | NM_028117.3 | chr2:118926496-118928583 | | 4728 | Cldn26 | NM_029070.2 | chr16:8409275-8425136 |
| 4634 | Chst15 | NM_029935.5 | chr7:132236254-132317155 | | 4729 | Cldn3 | NM_009902.4 | chr5:134986213-134987476 |
| 4635 | Chst2 | NM_018763.2 | chr9:95400925-95407270 | | 4730 | Cldn4 | NM_009903.2 | chr5:134945123-134946934 |
| 4636 | Chst3 | NM_016803.3 | chr10:60181527-60219260 | | 4731 | Cldn5 | NM_013805.4 | chr16:18776846-18778262 |
| 4637 | Chst4 | NM_011998.4 | chr8:110029074-110039334 | | 4732 | Cldn6 | NM_018777.4 | chr17:23679364-23682446 |
| 4638 | Chst5 | NM_019950.4 | chr8:111889134-111910199 | | 4733 | Cldn7 | NM_001193619.1 | chr11:69964778-69967886 |
| 4639 | Chst7 | NM_021715.1 | chrX:20059569-20097520 | | 4734 | Cldn8 | NM_018778.3 | chr16:88560825-88563183 |
| 4640 | Chst8 | NM_175140.4 | chr7:34674467-34812711 | | 4735 | Cldn9 | NM_020293.3 | chr17:23682583-23684026 |
| 4641 | Chst9 | NM_199055.2 | chr18:15452174-15718046 | | 4736 | Cldnd2 | NM_028849.1 | chr7:43440815-43443320 |
| 4642 | Chsy1 | NM_001081163.1 | chr7:66109514-66173798 | | 4737 | Clec10a | NM_001204252.1 | chr11:70166622-70170836 |
| 4643 | Chsy3 | NM_001081328.1 | chr18:59175339-59411336 | | 4738 | Clec11a | NM_009131.3 | chr7:44303765-44306959 |
| 4644 | Chtf18 | NM_145409.2 | chr17:25719029-25727415 | | 4739 | Clec12a | NM_177686.4 | chr6:129350243-129365303 |
| 4645 | Chtf8 | NM_145412.3 | chr8:106883862-106893593 | | 4740 | Clec12b | NM_001204223.1 | chr6:129375512-129385874 |
| 4646 | Chtop | NM_023215.6 | chr3:90498538-90509498 | | 4741 | Clec14a | NM_025809.5 | chr12:58264719-58269258 |
| 4647 | Chuk | NM_001162410.1 | chr19:44073333-44107477 | | 4742 | Clec16a | NM_001204229.1 | chr16:10545338-10744878 |
| 4648 | Churc1 | NM_206534.1 | chr12:76765572-76783178 | | 4743 | Clec18a | NM_181549.3 | chr8:111069496-111081708 |
| 4649 | Ciao1 | NM_025296.4 | chr2:127240937-127247816 | | 4744 | Clec1a | NM_175526.3 | chr6:129426683-129452000 |
| 4650 | Ciapin1 | NM_134141.4 | chr8:94819817-94838340 | | 4745 | Clec1b | NM_001204239.1 | chr6:129397296-129405413 |
| 4651 | Ciart | NM_001033302.2 | chr3:95878504-95882228 | | 4746 | Clec2d | NM_053109.3 | chr6:129180614-129186535 |

Fig. 26 - 26

| | | | |
|---|---|---|---|
| 4747 | Clec2e | NM_153506.4 | chr6:129091815-129100903 |
| 4748 | Clec2f | NM_001277202.1 | chr6:129014111-129020527 |
| 4749 | Clec2g | NM_001168223.1 | chr6:128971159-128984707 |
| 4750 | Clec2h | NM_053165.5 | chr6:128662384-128677374 |
| 4751 | Clec2i | NM_001289706.1 | chr6:128887586-128898167 |
| 4752 | Clec2l | NM_001101507.1 | chr6:38663068-38680865 |
| 4753 | Clec3a | NM_001007223.3 | chr8:114418033-114428133 |
| 4754 | Clec3b | NM_011606.2 | chr9:123150945-123157432 |
| 4755 | Clec4a1 | NM_199311.2 | chr6:122921847-122934619 |
| 4756 | Clec4a2 | NM_001170332.1 | chr6:123122689-123143999 |
| 4757 | Clec4a3 | NM_001204241.1 | chr6:122952514-122969878 |
| 4758 | Clec4a4 | NM_001005860.2 | chr6:122990366-123024421 |
| 4759 | Clec4b1 | NM_001190310.1 | chr6:123049961-123071555 |
| 4760 | Clec4b2 | NM_001004159.2 | chr6:123173022-123204671 |
| 4761 | Clec4d | NM_001163161.1 | chr6:123262106-123275268 |
| 4762 | Clec4e | NM_019948.2 | chr6:123281788-123289871 |
| 4763 | Clec4f | NM_016751.3 | chr6:83644541-83656116 |
| 4764 | Clec4g | NM_029465.3 | chr8:3716070-3720651 |
| 4765 | Clec4n | NM_001190320.1 | chr6:123229842-123247024 |
| 4766 | Clec5a | NM_001038604.1 | chr6:40574897-40585805 |
| 4767 | Clec7a | NM_020008.3 | chr6:129461590-129472779 |
| 4768 | Clec9a | NM_001205363.1 | chr6:129408861-129424764 |
| 4769 | Clgn | NM_009904.2 | chr8:83389890-83426829 |
| 4770 | Clhc1 | NM_001081099.1 | chr4:134510998-134523922 |
| 4771 | Clic1 | NM_033444.2 | chr17:35050242-35058719 |
| 4772 | Clic3 | NM_027085.3 | chr2:25456842-25458772 |
| 4773 | Clic4 | NM_013885.2 | chr4:135213969-135272760 |
| 4774 | Clic5 | NM_172621.2 | chr17:44188571-44280168 |
| 4775 | Clic6 | NM_172469.3 | chr16:92498146-92541241 |
| 4776 | Clint1 | NM_001045520.3 | chr11:45851963-45910625 |
| 4777 | Clip1 | NM_001291229.1 | chr5:123577793-123684361 |
| 4778 | Clip2 | NM_001039162.2 | chr5:134489382-134552434 |
| 4779 | Clip3 | NM_001081114.1 | chr7:30291752-30308367 |
| 4780 | Clip4 | NM_001271483.1 | chr17:71781298-71864210 |
| 4781 | Clk1 | NM_001042634.2 | chr1:58411987-58424088 |
| 4782 | Clk2 | NM_001163432.2 | chr3:89164794-89177087 |
| 4783 | Clk3 | NM_007713.4 | chr9:57750710-57765860 |
| 4784 | Clk4 | NM_007714.6 | chr11:51263113-51281770 |
| 4785 | Clmn | NM_001040682.1 | chr12:104763113-104865076 |
| 4786 | Clmp | NM_133733.4 | chr9:40685963-40784046 |
| 4787 | Cln3 | NM_001146311.1 | chr7:126573399-126584280 |
| 4788 | Cln5 | NM_001033242.1 | chr14:103070215-103077630 |
| 4789 | Cln6 | NM_001033175.2 | chr9:62838786-62852002 |
| 4790 | Cln8 | NM_012000.3 | chr8:14888535-14901719 |
| 4791 | Clnk | NM_025469.2 | chr5:38706456-38876693 |
| 4792 | Clns1a | NM_023671.2 | chr7:97696656-97720793 |
| 4793 | Clock | NM_001289826.1 | chr5:76209867-76304792 |
| 4794 | Clp1 | NM_133840.2 | chr2:84723121-84727268 |
| 4795 | Clpb | NM_009191.3 | chr7:101663767-101790168 |
| 4796 | Clpp | NM_017393.2 | chr17:56990263-56996371 |
| 4797 | Clps | NM_025469.2 | chr17:28558213-28560714 |
| 4798 | Clpsl2 | NM_001034871.2 | chr17:28549486-28552618 |
| 4799 | Clptm1 | NM_019649.2 | chr7:19631579-19665030 |
| 4800 | Clptm1l | NM_146047.2 | chr13:73604001-73620639 |
| 4801 | Clpx | NM_001044389.2 | chr9:65294259-65330658 |
| 4802 | Clrn1 | NM_153384.3 | chr3:58844027-58885212 |
| 4803 | Clrn2 | NM_001163317.1 | chr5:45453750-45464149 |
| 4804 | Clrn3 | NM_178869.5 | chr7:135511455-135528654 |
| 4805 | Clspn | NM_175554.4 | chr4:126556979-126593903 |
| 4806 | Clstn1 | NM_001290989.1 | chr4:149586467-149648899 |
| 4807 | Clstn2 | NM_022319.2 | chr9:97444394-98033167 |
| 4808 | Clstn3 | NM_153508.4 | chr6:124464784-124464784 |
| 4809 | Clta | NM_001080384.1 | chr4:44012642-44032846 |
| 4810 | Cltb | NM_028870.3 | chr13:54592938-54611272 |
| 4811 | Cltc | NM_001003908.1 | chr11:86694652-86757492 |
| 4812 | Clu | NM_013492.2 | chr14:65968482-65981545 |
| 4813 | Cluap1 | NM_029738.2 | chr16:3909008-3941147 |
| 4814 | Cluh | NM_001081158.2 | chr11:74649494-74670847 |
| 4815 | Clvs1 | NM_028940.2 | chr4:9269316-9451691 |
| 4816 | Clvs2 | NM_175448.3 | chr10:33512333-33624600 |
| 4817 | Clybl | NM_029556.3 | chr14:122181693-122402234 |
| 4818 | Cma1 | NM_010780.2 | chr14:55941450-55946661 |
| 4819 | Cma2 | NM_001024714.2 | chr14:55951427-55973995 |
| 4820 | Cmah | NM_001111110.2 | chr13:24327403-24477289 |
| 4821 | Cmas | NM_009908.2 | chr6:142756685-142775714 |
| 4822 | Cmbl | NM_181588.3 | chr15:31568911-31590119 |
| 4823 | Cmc1 | NM_026442.3 | chr9:118064526-118150196 |
| 4824 | Cmc2 | NM_026844.3 | chr8:116888684-116921436 |
| 4825 | Cmip | NM_001183262.1 | chr8:117257018-117461505 |
| 4826 | Cmklr1 | NM_008153.3 | chr5:113612354-113650390 |
| 4827 | Cml1 | NM_023160.2 | chr6:85910153-85915677 |
| 4828 | Cml2 | NM_053096.3 | chr6:85865421-85869137 |
| 4829 | Cml3 | NM_001037842.3 | chr6:85760630-85765744 |
| 4830 | Cml5 | NM_023493.2 | chr6:85817217-85820972 |
| 4831 | Cmpk1 | NM_025647.3 | chr4:114960612-114987228 |
| 4832 | Cmpk2 | NM_020557.4 | chr12:26469214-26479837 |
| 4833 | Cmss1 | NM_025599.3 | chr16:57301999-57606867 |
| 4834 | Cmtm1 | NM_181990.4 | chr8:104293541-104310145 |
| 4835 | Cmtm2a | NM_027022.2 | chr8:104281041-104293181 |
| 4836 | Cmtm2b | NM_028524.1 | chr8:104322226-104330764 |
| 4837 | Cmtm3 | NM_024217 | chr8:104340593-104347672 |
| 4838 | Cmtm4 | NM_153582.5 | chr8:104348192-104395807 |
| 4839 | Cmtm5 | NM_026066.2 | chr14:54936469-54939277 |
| 4840 | Cmtm6 | NM_026036.3 | chr9:114731202-114749343 |
| 4841 | Cmtm7 | NM_001252479.1 | chr9:114756835-114781993 |

| | | | |
|---|---|---|---|
| 4842 | Cmtm8 | NM_027294.1 | chr9:114789344-114844152 |
| 4843 | Cmtr1 | NM_028791.6 | chr17:29660594-29705979 |
| 4844 | Cmtr2 | NM_146215.4 | chr8:110217959-110224489 |
| 4845 | Cmya5 | NM_023821.3 | chr13:93040714-93144724 |
| 4846 | Cnbd2 | NM_027585.2 | chr2:156312472-156375638 |
| 4847 | Cnbp | NM_001109745.1 | chr6:87842614-87851106 |
| 4848 | Cndp1 | NM_177450.4 | chr18:84610508-84650095 |
| 4849 | Cndp2 | NM_001289531.1 | chr18:84667464-84682059 |
| 4850 | Cnep1r1 | NM_029074.3 | chr8:88118758-88135197 |
| 4851 | Cnfn | NM_001081375.1 | chr7:25367615-25369724 |
| 4852 | Cnga1 | NM_007723.2 | chr5:72603696-72642752 |
| 4853 | Cnga2 | NM_007724.3 | chrX:71991848-72010218 |
| 4854 | Cnga3 | NM_001282010.1 | chr1:37218277-37263384 |
| 4855 | Cnga4 | NM_001033317.3 | chr7:105404567-105408738 |
| 4856 | Cngb1 | NM_001195413.1 | chr8:95239042-95306585 |
| 4857 | Cngb3 | NM_013927.2 | chr4:19280849-19510623 |
| 4858 | Cnih1 | NM_009919.2 | chr14:46775567-46788357 |
| 4859 | Cnih2 | NM_009920.4 | chr19:5092867-5098521 |
| 4860 | Cnih3 | NM_001160211.1 | chr1:181352627-181460641 |
| 4861 | Cnih4 | NM_030131.3 | chr1:181150930-181168994 |
| 4862 | Cnksr1 | NM_001081047.1 | chr4:134228041-134238399 |
| 4863 | Cnksr2 | NM_177751.3 | chrX:157822572-158043197 |
| 4864 | Cnksr3 | NM_172546.2 | chr10:7119861-7212237 |
| 4865 | Cnn1 | NM_009922.4 | chr9:22099252-22109221 |
| 4866 | Cnn2 | NM_007725.2 | chr10:79988599-79995400 |
| 4867 | Cnn3 | NM_028044.2 | chr3:121426540-121458205 |
| 4868 | Cnnm1 | NM_031396.2 | chr19:43440435-43497213 |
| 4869 | Cnnm2 | NM_001102471.1 | chr19:46761608-46878580 |
| 4870 | Cnnm3 | NM_001039551.3 | chr1:36511875-36528237 |
| 4871 | Cnnm4 | NM_033570.2 | chr1:36471596-36508776 |
| 4872 | Cnot1 | NM_001205226.1 | chr8:95719450-95807462 |
| 4873 | Cnot10 | NM_153585.5 | chr9:114585873-114640200 |
| 4874 | Cnot11 | NM_028043.2 | chr1:39535801-39546877 |
| 4875 | Cnot2 | NM_001037846.3 | chr10:116485160-116581511 |
| 4876 | Cnot3 | NM_146176.3 | chr7:3645268-3661109 |
| 4877 | Cnot4 | NM_001164411.1 | chr6:35042706-35113737 |
| 4878 | Cnot6 | NM_001290741.1 | chr11:49671496-49702654 |
| 4879 | Cnot6l | NM_001285511.1 | chr5:96070332-96161547 |
| 4880 | Cnot7 | NM_001271542.1 | chr8:40492537-40515847 |
| 4881 | Cnot8 | NM_026949.3 | chr11:58104152-58118594 |
| 4882 | Cnp | NM_001146318.1 | chr11:100575890-100581739 |
| 4883 | Cnppd1 | NM_026977.2 | chr1:75135214-75142368 |
| 4884 | Cnpy1 | NM_001310511.1 | chr5:28200826-28237873 |
| 4885 | Cnpy2 | NM_019953.1 | chr10:128322458-128327187 |
| 4886 | Cnpy3 | NM_028065.4 | chr17:46735710-46752214 |
| 4887 | Cnpy4 | NM_178612.4 | chr5:138187534-138193894 |
| 4888 | Cnr1 | NM_007726.3 | chr4:33924631-33948831 |
| 4889 | Cnr2 | NM_009924.4 | chr4:135895188-135920219 |
| 4890 | Cnrip1 | NM_029861.2 | chr11:17051933-17079372 |
| 4891 | Cnst | NM_146105.3 | chr1:179546528-179627473 |
| 4892 | Cntd1 | NM_026562.2 | chr11:101279202-101288701 |
| 4893 | Cntf | NM_170786.2 | chr19:12763527-12765632 |
| 4894 | Cntfr | NM_001136056.2 | chr4:41657497-41695445 |
| 4895 | Cntln | NM_175275.4 | chr4:84884308-85131921 |
| 4896 | Cntn1 | NM_001159647.1 | chr15:92161356-92341967 |
| 4897 | Cntn2 | NM_177129.5 | chr1:132509424-132542940 |
| 4898 | Cntn3 | NM_008779.2 | chr6:102163305-102464667 |
| 4899 | Cntn4 | NM_001109749.1 | chr6:105677744-106699305 |
| 4900 | Cntn5 | NM_001033959.2 | chr9:9660890-10904726 |
| 4901 | Cntn6 | NM_017383.3 | chr6:104493043-104863405 |
| 4902 | Cntnap1 | NM_016782.2 | chr11:101176116-101190720 |
| 4903 | Cntnap2 | NM_001004357.2 | chr6:45060060-47301371 |
| 4904 | Cntnap3 | NM_001081129.1 | chr13:64737590-64903888 |
| 4905 | Cntnap4 | NM_130457.2 | chr8:112570042-112882707 |
| 4906 | Cntnap5a | NM_001077425.1 | chr1:115685136-116580674 |
| 4907 | Cntnap5b | NM_172851.2 | chr1:99772764-100485942 |
| 4908 | Cntnap5c | NM_001081653.1 | chr17:57769569-58410342 |
| 4909 | Cntrl | NM_001290635.1 | chr2:35132233-35147671 |
| 4910 | Cntrob | NM_172560.3 | chr11:69299495-69323873 |
| 4911 | Coa3 | NM_026618.2 | chr11:101277969-101278948 |
| 4912 | Coa4 | NM_183270.2 | chr7:100537099-100539812 |
| 4913 | Coa5 | NM_198006.4 | chr1:37417084-37430103 |
| 4914 | Coa6 | NM_174987.4 | chr2:126422500-126425435 |
| 4915 | Coa7 | NM_027250.4 | chr4:108328151-108340718 |
| 4916 | Coasy | NM_001305982.1 | chr11:101082562-101086619 |
| 4917 | Cobl | NM_001282993.1 | chr11:122236675-122464960 |
| 4918 | Cobll1 | NM_027225.1 | chr2:65088338-65238626 |
| 4919 | Coch | NM_001198835.1 | chr12:51593340-51605773 |
| 4920 | Cog1 | NM_013581.3 | chr11:113649528-113662401 |
| 4921 | Cog2 | NM_029746.3 | chr8:124520766-124552007 |
| 4922 | Cog3 | NM_177381.3 | chr14:75702350-75754493 |
| 4923 | Cog4 | NM_133973.2 | chr8:110847023-110882234 |
| 4924 | Cog5 | NM_001163126.1 | chr12:31654868-31937630 |
| 4925 | Cog6 | NM_026225.3 | chr3:52982122-53017223 |
| 4926 | Cog7 | NM_001033318.3 | chr7:121922838-121981693 |
| 4927 | Cog8 | NM_139229.4 | chr8:107048708-107056737 |
| 4928 | Coil | NM_016706.2 | chr11:88973934-88993613 |
| 4929 | Col10a1 | NM_009925.4 | chr10:34389980-34397085 |
| 4930 | Col11a1 | NM_007729.2 | chr3:114030539-114220326 |
| 4931 | Col11a2 | NM_009926.1 | chr17:34039436-34066242 |
| 4932 | Col12a1 | NM_001290308.1 | chr9:79598986-79718722 |
| 4933 | Col13a1 | NM_007731.3 | chr10:61838233-61979108 |
| 4934 | Col14a1 | NM_181277.3 | chr15:55307749-55520803 |
| 4935 | Col15a1 | NM_009928.3 | chr4:47208011-47313165 |
| 4936 | Col16a1 | NM_028266.5 | chr4:130047839-130099277 |

Fig. 26 - 27

| | | | |
|---|---|---|---|
| 4937 | Col17a1 | NM_001290825.1 | chr19:47646340-47692042 |
| 4938 | Col18a1 | NM_001109991.1 | chr10:77052178-77113705 |
| 4939 | Col19a1 | NM_007733.2 | chr1:24257682-24587437 |
| 4940 | Col1a1 | NM_007742.4 | chr11:94936223-94953042 |
| 4941 | Col1a2 | NM_007743.2 | chr6:4505696-4541543 |
| 4942 | Col20a1 | NM_028518.1 | chr2:180986534-181017540 |
| 4943 | Col22a1 | NM_027174.1 | chr15:71798475-72034227 |
| 4944 | Col23a1 | NM_153393.2 | chr11:51289919-51583925 |
| 4945 | Col24a1 | NM_027770.2 | chr3:145292471-145552005 |
| 4946 | Col25a1 | NM_001244952.1 | chr3:130180844-130599883 |
| 4947 | Col26a1 | NM_024474.2 | chr5:136741763-136883107 |
| 4948 | Col27a1 | NM_025685.3 | chr4:63215411-63334990 |
| 4949 | Col28a1 | NM_001037865.1 | chr6:7997807-8192617 |
| 4950 | Col2a1 | NM_001113515.2 | chr15:97975601-98004724 |
| 4951 | Col3a1 | NM_009930.2 | chr1:45311537-45349706 |
| 4952 | Col4a1 | NM_009931.2 | chr8:11198422-11312826 |
| 4953 | Col4a2 | NM_009932.3 | chr8:11312804-11449287 |
| 4954 | Col4a3 | NM_007734.2 | chr1:82586920-82722059 |
| 4955 | Col4a3bp | NM_001164222.1 | chr13:96542734-96640167 |
| 4956 | Col4a4 | NM_007735.2 | chr1:82450722-82586849 |
| 4957 | Col4a5 | NM_001163155.1 | chrX:141475418-141689235 |
| 4958 | Col4a6 | NM_053185.2 | chrX:141165402-141474076 |
| 4959 | Col5a1 | NM_015734.2 | chr2:27886424-28039510 |
| 4960 | Col5a2 | NM_007737.2 | chr1:45374330-45503282 |
| 4961 | Col5a3 | NM_016919.2 | chr9:20770049-20815034 |
| 4962 | Col6a1 | NM_009933.4 | chr10:76708791-76726044 |
| 4963 | Col6a2 | NM_146007.2 | chr10:76595755-76623404 |
| 4964 | Col6a3 | NM_001243008.1 | chr1:90766859-90843971 |
| 4965 | Col6a4 | NM_026763.2 | chr9:105990317-106096691 |
| 4966 | Col6a5 | NM_001167923.1 | chr9:105856069-105960643 |
| 4967 | Col6a6 | NM_001102607.1 | chr9:105689416-105828085 |
| 4968 | Col7a1 | NM_007738.3 | chr9:108953744-108984875 |
| 4969 | Col8a1 | NM_007739.2 | chr16:57624255-57754737 |
| 4970 | Col8a2 | NM_199473.2 | chr4:126286793-126314330 |
| 4971 | Col9a1 | NM_001290691.1 | chr1:24195202-24252738 |
| 4972 | Col9a2 | NM_007741.2 | chr4:121039565-121055325 |
| 4973 | Col9a3 | NM_009936.2 | chr2:180598221-180622185 |
| 4974 | Colec10 | NM_173422.3 | chr15:54410773-54466358 |
| 4975 | Colec11 | NM_027866.2 | chr12:28594171-28623330 |
| 4976 | Colec12 | NM_130449.2 | chr18:9707647-9877995 |
| 4977 | Colgalt2 | NM_177756.4 | chr1:152399866-152510695 |
| 4978 | Colq | NM_009937.2 | chr14:31523083-31577383 |
| 4979 | Commd1 | NM_144514.2 | chr11:22899727-22982284 |
| 4980 | Commd10 | NM_178377.4 | chr18:46958875-47087994 |
| 4981 | Commd2 | NM_175095.4 | chr3:57644348-57651684 |
| 4982 | Commd3 | NM_147778.3 | chr2:18672461-18676216 |
| 4983 | Commd4 | NM_025417.2 | chr9:57155040-57158299 |
| 4984 | Commd5 | NM_025536.2 | chr15:76899940-76901297 |
| 4985 | Commd6 | NM_001033132.3 | chr14:101633765-101640471 |
| 4986 | Commd7 | NM_001195390.1 | chr2:153616929-153632781 |
| 4987 | Commd8 | NM_178599.4 | chr5:72156999-72168183 |
| 4988 | Commd9 | NM_029635.3 | chr2:101886261-101901639 |
| 4989 | Comp | NM_016685.2 | chr8:70373547-70382066 |
| 4990 | Comt | NM_001111062.1 | chr16:18406881-18426716 |
| 4991 | Comtd1 | NM_026965.2 | chr14:21845860-21848910 |
| 4992 | Copa | NM_009934.4 | chr1:172082528-172122332 |
| 4993 | Copb1 | NM_033370.3 | chr7:114215558-114254680 |
| 4994 | Copb2 | NM_015827.2 | chr9:98563730-98588375 |
| 4995 | Cope | NM_021538.1 | chr8:70302784-70312990 |
| 4996 | Copg1 | NM_017477.2 | chr6:87887939-87913594 |
| 4997 | Copg2 | NM_017478.3 | chr6:30747953-30896794 |
| 4998 | Coprs | NM_025556.3 | chr8:13884787-13890271 |
| 4999 | Cops2 | NM_001285507.1 | chr2:125830301-125859082 |
| 5000 | Cops3 | NM_011991.1 | chr11:59817803-59839767 |
| 5001 | Cops4 | NM_012001.2 | chr5:100518308-100547802 |
| 5002 | Cops5 | NM_001277101.1 | chr1:10024599-10038159 |
| 5003 | Cops6 | NM_012002.3 | chr5:138161101-138163984 |
| 5004 | Cops7a | NM_001164089.1 | chr6:124958410-124965529 |
| 5005 | Cops7b | NM_172974.2 | chr1:86587099-86606500 |
| 5006 | Cops8 | NM_133863.2 | chr1:90603424-90613341 |
| 5007 | Copz1 | NM_019817.1 | chr15:103272917-103299864 |
| 5008 | Copz2 | NM_019877.2 | chr11:96849875-96861202 |
| 5009 | Coq10a | NM_001081040.1 | chr10:128363096-128370037 |
| 5010 | Coq10b | NM_001039710.1 | chr1:55052769-55072702 |
| 5011 | Coq2 | NM_027978.2 | chr5:100654725-100674256 |
| 5012 | Coq3 | NM_172683.1 | chr4:21879674-21912126 |
| 5013 | Coq4 | NM_178693.4 | chr2:29788262-29797743 |
| 5014 | Coq5 | NM_026504.2 | chr5:115279701-115296972 |
| 5015 | Coq6 | NM_172594.1 | chr12:84361967-84373796 |
| 5016 | Coq7 | NM_009940.3 | chr7:118525061-118533356 |
| 5017 | Coq9 | NM_026452.2 | chr8:94838416-94854895 |
| 5018 | Corin | NM_001122756.1 | chr5:72300024-72504640 |
| 5019 | Coro1a | NM_009898.3 | chr7:126699773-126704816 |
| 5020 | Coro1b | NM_011778.1 | chr19:4148662-4154035 |
| 5021 | Coro1c | NM_011779.3 | chr5:113842438-113908706 |
| 5022 | Coro2a | NM_001164804.1 | chr4:46536936-46601929 |
| 5023 | Coro2b | NM_175424.3 | chr9:62419491-62537044 |
| 5024 | Coro6 | NM_139128.1 | chr11:77463912-77469501 |
| 5025 | Coro7 | NM_030205.4 | chr16:4626883-4679720 |
| 5026 | Cort | NM_007745.3 | chr4:149125190-149126741 |
| 5027 | Cotl1 | NM_028071.3 | chr8:119809213-119840579 |
| 5028 | Cox10 | NM_178379.3 | chr11:63962626-64079472 |
| 5029 | Cox11 | NM_199008.2 | chr11:90638183-90645977 |
| 5030 | Cox14 | NM_183256.3 | chr15:99725617-99728136 |
| 5031 | Cox15 | NM_144874.4 | chr19:43733253-43753000 |
| 5032 | Cox16 | NM_025461.6 | chr12:81470602-81485137 |
| 5033 | Cox17 | NM_001017429.2 | chr16:38346998-38352763 |
| 5034 | Cox18 | NM_001033310.3 | chr5:90214724-90223996 |
| 5035 | Cox19 | NM_197980.1 | chr5:139337821-139345166 |
| 5036 | Cox20 | NM_025511.2 | chr1:178319152-178322693 |
| 5037 | Cox4i1 | NM_009941.3 | chr8:120668224-120674209 |
| 5038 | Cox4i2 | NM_053091.2 | chr2:152754172-152765037 |
| 5039 | Cox5a | NM_007747 | chr9:57521231-57532426 |
| 5040 | Cox5b | NM_009942.2 | chr1:36691486-36693388 |
| 5041 | Cox6a1 | NM_007748.3 | chr5:115345653-115348955 |
| 5042 | Cox6a2 | NM_009943.2 | chr7:128205434-128206366 |
| 5043 | Cox6b1 | NM_025628.2 | chr7:30616973-30626151 |
| 5044 | Cox6b2 | NM_001289848.1 | chr7:4751791-4753094 |
| 5045 | Cox6c | NM_053071.2 | chr15:35931975-35938246 |
| 5046 | Cox7a1 | NM_009944.3 | chr7:30184170-30186030 |
| 5047 | Cox7a2 | NM_009945.3 | chr9:79755240-79759853 |
| 5048 | Cox7a2l | NM_001159529.1 | chr17:83501916-83514333 |
| 5049 | Cox7b | NM_025379.2 | chrX:106015699-106022450 |
| 5050 | Cox7b2 | NM_030052.3 | chr5:71442822-71548205 |
| 5051 | Cox7c | NM_007749.3 | chr13:86044797-86046795 |
| 5052 | Cox8a | NM_007750.2 | chr19:7215157-7217616 |
| 5053 | Cox8b | NM_007751.3 | chr7:140888941-140900446 |
| 5054 | Cox8c | NM_001039049.1 | chr12:102899305-102900534 |
| 5055 | Cp | NM_001276248.1 | chr3:19957053-20007609 |
| 5056 | Cpa1 | NM_025350.3 | chr6:30639220-30645361 |
| 5057 | Cpa2 | NM_001024698.2 | chr6:30541641-30564473 |
| 5058 | Cpa3 | NM_007753.2 | chr3:20215615-20242181 |
| 5059 | Cpa4 | NM_027926.2 | chr6:30568375-30591747 |
| 5060 | Cpa5 | NM_145537.3 | chr6:30611009-30631521 |
| 5061 | Cpa6 | NM_001289497.1 | chr1:10324718-10719945 |
| 5062 | Cpb1 | NM_029706.1 | chr3:20249483-20275729 |
| 5063 | Cpb2 | NM_019775.3 | chr14:75242286-75283553 |
| 5064 | Cpd | NM_007754.2 | chr11:76777207-76847008 |
| 5065 | Cpe | NM_013494.3 | chr8:64592550-64693040 |
| 5066 | Cpeb1 | NM_001252525.1 | chr7:81347025-81454758 |
| 5067 | Cpeb2 | NM_001177379.1 | chr5:43233462-43289724 |
| 5068 | Cpeb3 | NM_001290826.1 | chr19:37021290-37176063 |
| 5069 | Cpeb4 | NM_001290676.1 | chr11:31870939-31935635 |
| 5070 | Cped1 | NM_001081351.1 | chr6:21985999-22256606 |
| 5071 | Cphx1 | NM_175342.3 | chr14:25942543-26235735 |
| 5072 | Cphx2 | NM_001270506.1 | chr14:25942539-26235740 |
| 5073 | Cplx1 | NM_007755.3 | chr5:108518553-108550027 |
| 5074 | Cplx2 | NM_009946.3 | chr13:54371348-54383917 |
| 5075 | Cplx3 | NM_146223.3 | chr9:57599991-57606281 |
| 5076 | Cplx4 | NM_145493.1 | chr18:65955721-65970178 |
| 5077 | Cpm | NM_027468.1 | chr10:117629499-117687352 |
| 5078 | Cpn1 | NM_030703.2 | chr19:43956307-43986520 |
| 5079 | Cpn2 | NM_027904.3 | chr16:30256378-30267532 |
| 5080 | Cpne1 | NM_170588.3 | chr2:156071840-156111965 |
| 5081 | Cpne2 | NM_153507.2 | chr8:94533027-94570529 |
| 5082 | Cpne3 | NM_027769.2 | chr4:19519251-19570104 |
| 5083 | Cpne4 | NM_028719.1 | chr9:104569787-105034544 |
| 5084 | Cpne5 | NM_153166.2 | chr17:29156520-29237790 |
| 5085 | Cpne6 | NM_001136057.2 | chr14:55510447-55517431 |
| 5086 | Cpne7 | NM_170684.2 | chr8:123137373-123135185 |
| 5087 | Cpne8 | NM_001033851.1 | chr15:90643322-90679388 |
| 5088 | Cpne9 | NM_170673.3 | chr6:113282306-113305571 |
| 5089 | Cpox | NM_007757.2 | chr16:58670207-58680389 |
| 5090 | Cpped1 | NM_146067.3 | chr16:11803720-11909423 |
| 5091 | Cpq | NM_018755.2 | chr15:33083128-33594552 |
| 5092 | Cps1 | NM_001080809.2 | chr1:67123026-67231267 |
| 5093 | Cpsf1 | NM_001164173.1 | chr15:76595807-76607591 |
| 5094 | Cpsf2 | NM_016856.3 | chr12:101975973-102005993 |
| 5095 | Cpsf3 | NM_018813.3 | chr12:21286296-21315056 |
| 5096 | Cpsf3l | NM_028020.3 | chr4:155869566-155889103 |
| 5097 | Cpsf4 | NM_001291248.1 | chr5:145187212-145182041 |
| 5098 | Cpsf4l | NM_001164592.1 | chr11:113698170-113709526 |
| 5099 | Cpsf6 | NM_001013391.2 | chr10:117344667-117376973 |
| 5100 | Cpsf7 | NM_001164272.1 | chr19:10525243-10547735 |
| 5101 | Cpt1a | NM_013495.2 | chr19:3323300-3385753 |
| 5102 | Cpt1b | NM_009948.2 | chr15:89416404-89425862 |
| 5103 | Cpt1c | NM_001252470.1 | chr7:44959371-44974851 |
| 5104 | Cpt2 | NM_009949.2 | chr4:107903981-107923589 |
| 5105 | Cpvl | NM_001289713.1 | chr6:53873278-53978673 |
| 5106 | Cpxcr1 | NM_001033471.3 | chrX:116448943-116478783 |
| 5107 | Cpxm1 | NM_019696.2 | chr2:130390774-130397629 |
| 5108 | Cpxm2 | NM_018867.5 | chr7:132042809-132154741 |
| 5109 | Cpz | NM_153107.2 | chr5:35502217-35525626 |
| 5110 | Cr1l | NM_013499.2 | chr1:195103787-195131570 |
| 5111 | Cr2 | NM_007758.2 | chr1:195136810-195176715 |
| 5112 | Crabp1 | NM_001284507.1 | chr9:54764747-54773110 |
| 5113 | Crabp2 | NM_007759.2 | chr3:87948692-87953372 |
| 5114 | Cradd | NM_009950.2 | chr10:95174745-95324097 |
| 5115 | Cramp1l | NM_020608.3 | chr17:24961225-25015230 |
| 5116 | Crat | NM_007760.3 | chr2:30400475-30415748 |
| 5117 | Crb1 | NM_133239.2 | chr1:139198253-139377076 |
| 5118 | Crb2 | NM_001163566.1 | chr2:37776248-37799103 |
| 5119 | Crb3 | NM_177638.4 | chr17:57062276-57065914 |
| 5120 | Crbn | NM_021449.3 | chr6:106778244-106800087 |
| 5121 | Crcp | NM_007761.2 | chr5:130029305-130060783 |
| 5122 | Crct1 | NM_028798.3 | chr3:93014204-93015686 |
| 5123 | Creb1 | NM_001037726.1 | chr1:64532803-64604548 |
| 5124 | Creb3 | NM_013497.3 | chr4:43562633-43567060 |
| 5125 | Creb3l1 | NM_011957.2 | chr2:91982327-92024170 |
| 5126 | Creb3l2 | NM_178661.4 | chr6:37331020-37442148 |

Fig. 26 - 28

| | | | |
|---|---|---|---|
| 5127 | Creb3l3 | NM_145365.3 | chr10:81084332-81098872 |
| 5128 | Creb3l4 | NM_030080.3 | chr3:90237497-90243512 |
| 5129 | Creb5 | NM_172728.2 | chr6:53573373-53695832 |
| 5130 | Crebbp | NM_001025432.1 | chr16:4084047-4213404 |
| 5131 | Crebl2 | NM_177687.3 | chr6:134830198-134857883 |
| 5132 | Crebrf | NM_029870.2 | chr17:26715649-26776626 |
| 5133 | Crebzf | NM_145151.3 | chr7:90442780-90448043 |
| 5134 | Creg1 | NM_011804.2 | chr1:165763779-165775304 |
| 5135 | Creg2 | NM_170597.4 | chr1:39618405-39651182 |
| 5136 | Creld1 | NM_133930.1 | chr6:113483568-113493338 |
| 5137 | Creld2 | NM_029720.2 | chr15:88819645-88826681 |
| 5138 | Crem | NM_001110850.2 | chr18:3266353-3327591 |
| 5139 | Crh | NM_205769.3 | chr3:19693400-19695396 |
| 5140 | Crhbp | NM_198408.3 | chr13:95431375-95444831 |
| 5141 | Crhr1 | NM_007762.5 | chr11:104132780-104175523 |
| 5142 | Crhr2 | NM_001288618.1 | chr6:55090048-55133016 |
| 5143 | Crim1 | NM_015800.3 | chr17:78200247-78376592 |
| 5144 | Crip1 | NM_007763.3 | chr12:113152011-113153879 |
| 5145 | Crip2 | NM_024223.2 | chr12:113140236-113145506 |
| 5146 | Crip3 | NM_053250.2 | chr17:46428941-46431771 |
| 5147 | Cript | NM_019936.3 | chr17:87025560-87035808 |
| 5148 | Crisp1 | NM_009638.3 | chr17:40293757-40319207 |
| 5149 | Crisp2 | NM_001204071.1 | chr17:40764733-40794146 |
| 5150 | Crisp3 | NM_009639.2 | chr17:40221776-40242258 |
| 5151 | Crisp4 | NM_030033.1 | chr1:18115190-18137051 |
| 5152 | Crispld1 | NM_031402.2 | chr1:17727416-17766207 |
| 5153 | Crispld2 | NM_030209.4 | chr8:119992437-120052794 |
| 5154 | Crk | NM_001277219.1 | chr11:75679258-75708428 |
| 5155 | Crkl | NM_001277231.1 | chr16:17451984-17487440 |
| 5156 | Crlf1 | NM_018827.2 | chr8:70493155-70504081 |
| 5157 | Crlf2 | NM_001164735.1 | chr5:109554708-109558993 |
| 5158 | Crlf3 | NM_001277106.1 | chr11:80046492-80080991 |
| 5159 | Crls1 | NM_001024385.1 | chr2:132846665-132866768 |
| 5160 | Crmp1 | NM_001136058.2 | chr5:37242057-37292163 |
| 5161 | Crnde | NR_033641.3 | chr8:92326030-92356120 |
| 5162 | Crnkl1 | NM_025820.3 | chr2:145917481-145934700 |
| 5163 | Crnn | NM_001081200.1 | chr3:93144786-93149471 |
| 5164 | Crocc | NM_001145958.1 | chr4:141016636-141060545 |
| 5165 | Crot | NM_023733.3 | chr5:8966047-8997146 |
| 5166 | Crp | NM_007768.4 | chr1:172698055-172699966 |
| 5167 | Crtac1 | NM_145123.4 | chr19:42283036-42431783 |
| 5168 | Crtam | NM_001281954.1 | chr9:40972797-41004628 |
| 5169 | Crtap | NM_019922.2 | chr9:114375130-114390712 |
| 5170 | Crtc1 | NM_001004062.2 | chr8:70382357-70439573 |
| 5171 | Crtc2 | NM_028881.2 | chr3:90254280-90264125 |
| 5172 | Crtc3 | NM_173863.2 | chr7:80586631-80688877 |
| 5173 | Crx | NM_001113330.1 | chr7:15865946-15872385 |
| 5174 | Crxos | NM_001033638.2 | chr7:15896123-15904030 |
| 5175 | Cry1 | NM_007771.3 | chr10:85131699-85185054 |
| 5176 | Cry2 | NM_009963.4 | chr2:92403646-92434069 |
| 5177 | Cryaa | NM_001278569.1 | chr17:31677930-31681730 |
| 5178 | Cryab | NM_001289782.1 | chr9:50751324-50756635 |
| 5179 | Cryba1 | NM_009965.3 | chr11:77718613-77725293 |
| 5180 | Cryba2 | NM_021541.3 | chr1:74889933-74893143 |
| 5181 | Cryba4 | NM_021351.2 | chr5:112246491-112252518 |
| 5182 | Crybb1 | NM_023695.3 | chr5:112255819-112269585 |
| 5183 | Crybb2 | NM_007773.4 | chr5:113058257-113070117 |
| 5184 | Crybb3 | NM_001159650.1 | chr5:113075838-113081584 |
| 5185 | Crybg3 | NM_174848.3 | chr16:59490774-59555752 |
| 5186 | Cryga | NM_007774.3 | chr1:65100388-65103363 |
| 5187 | Crygb | NM_144761.2 | chr1:65080221-65082290 |
| 5188 | Crygc | NM_001082573.2 | chr1:65071524-65073532 |
| 5189 | Crygd | NM_007776.2 | chr1:65061837-65063440 |
| 5190 | Cryge | NM_007777.3 | chr1:65048556-65051163 |
| 5191 | Crygf | NM_027010.2 | chr1:65926521-65928304 |
| 5192 | Crygn | NM_153076.2 | chr5:24751001-24757843 |
| 5193 | Crygs | NM_009967.2 | chr16:22805202-22811410 |
| 5194 | Cryl1 | NM_030043.3 | chr14:57275033-57398483 |
| 5195 | Crym | NM_016669.1 | chr7:120186883-120201988 |
| 5196 | Cryz | NM_009968.3 | chr3:154596710-154623182 |
| 5197 | Cryzl1 | NM_026994.1 | chr16:91689321-91728802 |
| 5198 | Cs | NM_026444.3 | chr10:128337831-128362479 |
| 5199 | Csad | NM_144942.4 | chr15:102176997-102189043 |
| 5200 | Csdc2 | NM_145473.3 | chr15:81936758-81950941 |
| 5201 | Csde1 | NM_001161854.2 | chr3:103020545-103058186 |
| 5202 | Cse1l | NM_023565.3 | chr2:166906095-166946389 |
| 5203 | Csf1 | NM_001113529.1 | chr3:107741047-107760469 |
| 5204 | Csf1r | NM_001037859.2 | chr18:61105571-61131139 |
| 5205 | Csf2 | NM_009969.4 | chr11:54247289-54249899 |
| 5206 | Csf2ra | NM_009970.2 | chr19:61224401-61228418 |
| 5207 | Csf2rb | NM_007780.4 | chr15:78325989-78351001 |
| 5208 | Csf2rb2 | NM_001287389.1 | chr15:78282507-78305721 |
| 5209 | Csf3 | NM_009971.1 | chr11:98701312-98703629 |
| 5210 | Csf3r | NM_001252651.1 | chr4:126024658-126044975 |
| 5211 | Csgalnact1 | NM_001252623.1 | chr8:68356780-68735146 |
| 5212 | Csgalnact2 | NM_030165.3 | chr6:118107451-118139140 |
| 5213 | Csk | NM_007783.3 | chr9:57626645-57645653 |
| 5214 | Csl | NM_027945.3 | chr10:99757704-99759658 |
| 5215 | Csmd1 | NM_053171.2 | chr8:15892544-17535385 |
| 5216 | Csmd2 | NM_001281955.1 | chr4:127988043-128567656 |
| 5217 | Csmd2os | NM_029137.1 | chr4:128133522-128166597 |
| 5218 | Csmd3 | NM_001081391.2 | chr15:47580637-48791989 |
| 5219 | Csn1s1 | NM_001286015.1 | chr5:87666207-87682577 |
| 5220 | Csn1s2a | NM_007785.2 | chr5:87774449-87788798 |
| 5221 | Csn1s2b | NM_009973.3 | chr5:87808120-87844421 |
| 5222 | Csn2 | NM_001286020.1 | chr5:87692618-87699425 |
| 5223 | Csn3 | NM_007786.4 | chr5:87925632-87932264 |
| 5224 | Csnk1a1 | NM_146087.2 | chr18:61555581-61588299 |
| 5225 | Csnk1d | NM_027874.2 | chr11:120961740-120991333 |
| 5226 | Csnk1e | NM_001289898.1 | chr15:79417851-79442057 |
| 5227 | Csnk1g1 | NM_173185.2 | chr9:65909009-66045014 |
| 5228 | Csnk1g2 | NM_001159591.1 | chr10:80629655-80640771 |
| 5229 | Csnk1g3 | NM_152809.2 | chr18:53862112-53955684 |
| 5230 | Csnk2a1 | NM_007788.3 | chr2:152226839-152281851 |
| 5231 | Csnk2a2 | NM_009974.3 | chr8:95446095-95488820 |
| 5232 | Csnk2b | NM_009975.3 | chr17:35116194-35121292 |
| 5233 | Csnka2ip | NM_173861.2 | chr16:64477810-64479134 |
| 5234 | Cspg4 | NM_139001.2 | chr9:56865193-56899870 |
| 5235 | Cspg5 | NM_001166273.1 | chr9:110243782-110262576 |
| 5236 | Cspp1 | NM_026493.3 | chr1:10038217-10136768 |
| 5237 | Csprs | NM_033616.3 | chr1_GL456221_random:111571-163011 |
| 5238 | Csrnp1 | NM_153287.3 | chr9:119971165-119984658 |
| 5239 | Csrnp2 | NM_153407.2 | chr15:100479569-100495239 |
| 5240 | Csrnp3 | NM_001290665.3 | chr2:65931864-66031546 |
| 5241 | Csrp1 | NM_007791.5 | chr1:135729196-135752229 |
| 5242 | Csrp2 | NM_007792.4 | chr10:110920175-110939514 |
| 5243 | Csrp2bp | NM_001166640.1 | chr2:144369031-144407675 |
| 5244 | Csrp3 | NM_001198841.1 | chr7:48830397-48848051 |
| 5245 | Cst10 | NM_021405.2 | chr2:149405248-149410278 |
| 5246 | Cst11 | NM_030059.2 | chr2:148768617-148771497 |
| 5247 | Cst12 | NM_027054.1 | chr2:148789360-148793437 |
| 5248 | Cst13 | NM_027024.3 | chr2:148820098-148830410 |
| 5249 | Cst3 | NM_009976.4 | chr2:148871721-148875512 |
| 5250 | Cst6 | NM_028623.5 | chr19:5344704-5349574 |
| 5251 | Cst7 | NM_009977.3 | chr2:150578414-150578944 |
| 5252 | Cst8 | NM_009978.2 | chr2:148798838-148805584 |
| 5253 | Cst9 | NM_009979.1 | chr2:148835146-148838737 |
| 5254 | Csta1 | NM_001033239.3 | chr16:36119945-36131189 |
| 5255 | Cstad | NM_030137.2 | chr2:30595043-30608945 |
| 5256 | Cstb | NM_007793.3 | chr10:78425669-78427622 |
| 5257 | Cstf1 | NM_024199.2 | chr2:172371002-172381086 |
| 5258 | Cstf2 | NM_001290398.1 | chrX:134059175-134086822 |
| 5259 | Cstf2t | NM_031249.2 | chr19:31082840-31086592 |
| 5260 | Cstf3 | NM_001037326.2 | chr2:104590483-104609429 |
| 5261 | Cstl1 | NM_177655.3 | chr2:148750360-148755378 |
| 5262 | Ctag2 | NM_027302.2 | chrX:65047643-65049017 |
| 5263 | Ctage5 | NM_001165253.1 | chr12:59131452-59190220 |
| 5264 | Ctbp1 | NM_001198859.1 | chr5:33247722-33275004 |
| 5265 | Ctbp2 | NM_001170744.1 | chr7:132987010-133035247 |
| 5266 | Ctbs | NM_028836.4 | chr3:146450466-146465848 |
| 5267 | Ctcl | NM_001013256.2 | chr11:69015910-69036473 |
| 5268 | Ctcf | NM_181322.3 | chr8:105636537-105682922 |
| 5269 | Ctcfl | NM_001081387.2 | chr2:173093608-173119525 |
| 5270 | Ctcflos | NR_040321.1 | chr2:173124748-173133204 |
| 5271 | Ctdnep1 | NM_026017.2 | chr11:69981167-69990600 |
| 5272 | Ctdp1 | NM_026295.2 | chr18:80407958-80469667 |
| 5273 | Ctdsp1 | NM_153088.2 | chr1:74391608-74397285 |
| 5274 | Ctdsp2 | NM_001113470.1 | chr10:126978716-126999975 |
| 5275 | Ctdspl | NM_133710.3 | chr9:118926535-119044119 |
| 5276 | Ctdspl2 | NM_001290991.1 | chr2:121956000-122015326 |
| 5277 | Ctf1 | NM_007795.1 | chr7:127712735-127718185 |
| 5278 | Ctf2 | NM_198858.1 | chr7:127718959-127725616 |
| 5279 | Ctgf | NM_010217.2 | chr10:24595441-24598682 |
| 5280 | Cth | NM_145953.2 | chr3:157894247-157925063 |
| 5281 | Cthrc1 | NM_026778.2 | chr15:39076931-39087119 |
| 5282 | Ctif | NM_201354.2 | chr18:75431220-75697696 |
| 5283 | Ctla2a | NM_001145799.1 | chr13:60934916-60936566 |
| 5284 | Ctla2b | NM_001145801.1 | chr13:60909350-60897447 |
| 5285 | Ctla4 | NM_001281976.1 | chr1:60909024-60915832 |
| 5286 | Ctnna1 | NM_009818.1 | chr18:35118911-35254775 |
| 5287 | Ctnna2 | NM_001109764.1 | chr6:76881636-77979667 |
| 5288 | Ctnna3 | NM_001164376.1 | chr10:63457510-65003667 |
| 5289 | Ctnnal1 | NM_018761.3 | chr4:56810934-56865211 |
| 5290 | Ctnnb1 | NM_001165902.1 | chr9:120933577-120960507 |
| 5291 | Ctnnbip1 | NM_001141930.1 | chr4:149545116-149566437 |
| 5292 | Ctnnbl1 | NM_025680.4 | chr2:157737400-157891903 |
| 5293 | Ctnnd1 | NM_001085448.1 | chr2:84600780-84650740 |
| 5294 | Ctnnd2 | NM_008729.2 | chr15:30172592-31029343 |
| 5295 | Ctns | NM_031251.4 | chr11:73183132-73199019 |
| 5296 | Ctps | NM_016748.2 | chr4:120539867-120570276 |
| 5297 | Ctps2 | NM_001168568.1 | chrX:162901559-163034541 |
| 5298 | Ctr9 | NM_009431.2 | chr7:111028950-111056377 |
| 5299 | Ctrb1 | NM_025583.2 | chr8:111686509-111691010 |
| 5300 | Ctrc | NM_001033875.2 | chr4:141838239-141846859 |
| 5301 | Ctrcos | NR_040641.1 | chr4:141844320-141846990 |
| 5302 | Ctrl | NM_023182.2 | chr8:105983993-105993862 |
| 5303 | Cts3 | NM_026906.3 | chr13:61564629-61570127 |
| 5304 | Cts6 | NM_021445.1 | chr13:61195146-61203392 |
| 5305 | Cts7 | NM_019539.3 | chr13:61352450-61358170 |
| 5306 | Cts8 | NM_019541.3 | chr13:61246746-61255348 |
| 5307 | Cts8-ps | NR_027871.2 | chr13:61281379-61288850 |
| 5308 | Ctsa | NM_001038492.2 | chr2:164832871-164841032 |
| 5309 | Ctsb | NM_007798.3 | chr14:63122461-63149923 |
| 5310 | Ctsc | NM_009982.5 | chr7:88278084-88315861 |
| 5311 | Ctsd | NM_009983.2 | chr7:142375915-142387870 |
| 5312 | Ctse | NM_007799.3 | chr1:131638313-131675507 |
| 5313 | Ctsf | NM_019861.1 | chr19:4855128-4860912 |
| 5314 | Ctsg | NM_007800.2 | chr14:56099884-56102574 |
| 5315 | Ctsh | NM_007801.3 | chr9:90054266-90076095 |

Fig. 26 - 29

| | | | |
|---|---|---|---|
| 5316 | Ctsj | NM_012007.1 | chr13:61000277-61005911 |
| 5317 | Ctsk | NM_007802.4 | chr3:95499209-95509387 |
| 5318 | Ctsl | NM_009984.4 | chr13:64361889-64370520 |
| 5319 | Ctsll3 | NM_027344.3 | chr13:60798249-60802844 |
| 5320 | Ctsm | NM_022326.3 | chr13:61536443-61541839 |
| 5321 | Ctso | NM_177662.2 | chr3:81932615-81956725 |
| 5322 | Ctsq | NM_029636.3 | chr13:61035037-61040597 |
| 5323 | Ctsr | NM_020284.1 | chr13:61159214-61164188 |
| 5324 | Ctss | NM_001267695.2 | chr3:95526785-95556405 |
| 5325 | Ctsw | NM_009985.5 | chr19:5465042-5468507 |
| 5326 | Ctsz | NM_022325.5 | chr2:174427493-174439039 |
| 5327 | Cttn | NM_001252572.1 | chr7:144435723-144470935 |
| 5328 | Cttnbp2 | NM_080285.1 | chr6:18366476-18514825 |
| 5329 | Cttnbp2nl | NM_001163332.1 | chr3:105001914-105052953 |
| 5330 | Ctu1 | NM_145582.1 | chr7:43672030-43678297 |
| 5331 | Ctu2 | NM_153775.2 | chr8:122476142-122483092 |
| 5332 | Ctxn1 | NM_183315.2 | chr8:4257645-4259274 |
| 5333 | Ctxn2 | NM_001162934.1 | chr2:125136691-125147841 |
| 5334 | Ctxn3 | NM_001134697.1 | chr18:57468485-57478134 |
| 5335 | Cubn | NM_001081084.2 | chr2:13276337-13491876 |
| 5336 | Cuedc1 | NM_001172099.1 | chr11:88169564-88194140 |
| 5337 | Cuedc2 | NM_001164290.1 | chr19:46329811-46338660 |
| 5338 | Cul1 | NM_012042.3 | chr6:47454323-47526139 |
| 5339 | Cul2 | NM_029402.3 | chr18:3383224-3436700 |
| 5340 | Cul3 | NM_016716.5 | chr1:80264922-80340690 |
| 5341 | Cul4a | NM_146207.2 | chr8:13105720-13147939 |
| 5342 | Cul4b | NM_001110142.1 | chrX:38531620-38576196 |
| 5343 | Cul5 | NM_001161618.1 | chr9:53614581-53667507 |
| 5344 | Cul7 | NM_025611.5 | chr17:46650337-46664364 |
| 5345 | Cul9 | NM_001081335.2 | chr17:46500608-46546388 |
| 5346 | Cuta | NM_026307.3 | chr17:26937971-26939538 |
| 5347 | Cutal | NM_030021.3 | chr2:34874395-34892133 |
| 5348 | Cutc | NM_001113562.1 | chr19:43753022-43768638 |
| 5349 | Cux1 | NM_001291233.1 | chr5:136266409-136565981 |
| 5350 | Cux2 | NM_007804.2 | chr5:121860215-122047825 |
| 5351 | Cuzd1 | NM_008411.3 | chr7:131308553-131322292 |
| 5352 | Cwc15 | NM_023153.3 | chr9:14500618-14510620 |
| 5353 | Cwc22 | NM_001290740.1 | chr2:77895652-77946356 |
| 5354 | Cwc25 | NM_026186.4 | chr11:97745469-97766613 |
| 5355 | Cwc27 | NM_026072.1 | chr13:104631326-104816953 |
| 5356 | Cwf19l1 | NM_001081077.1 | chr19:44108636-44135876 |
| 5357 | Cwf19l2 | NM_027545.2 | chr9:3404084-3479236 |
| 5358 | Cwh43 | NM_181323.2 | chr5:73406077-73453425 |
| 5359 | Cx3cl1 | NM_009142.3 | chr8:94772179-94782426 |
| 5360 | Cx3cr1 | NM_009987.4 | chr9:120048682-120068296 |
| 5361 | Cxadr | NM_001025192.3 | chr16:78301670-78340759 |
| 5362 | Cxcl1 | NM_008176.3 | chr5:90891244-90893115 |
| 5363 | Cxcl10 | NM_021274.2 | chr5:92346638-92348889 |
| 5364 | Cxcl11 | NM_019494.1 | chr5:92359544-92363277 |
| 5365 | Cxcl12 | NM_001012477.2 | chr6:117168534-117181368 |
| 5366 | Cxcl13 | NM_018866.2 | chr5:95956938-95961068 |
| 5367 | Cxcl14 | NM_019568.2 | chr13:56288642-56296551 |
| 5368 | Cxcl15 | NM_011331.2 | chr5:90794533-90803067 |
| 5369 | Cxcl16 | NM_023158.6 | chr11:70454233-70459984 |
| 5370 | Cxcl17 | NM_153576.2 | chr7:25400052-25412886 |
| 5371 | Cxcl2 | NM_009140.2 | chr5:90903898-90905938 |
| 5372 | Cxcl3 | NM_203320.3 | chr5:90786100-90788093 |
| 5373 | Cxcl5 | NM_009141.3 | chr5:90759297-90761625 |
| 5374 | Cxcl9 | NM_008599.4 | chr5:92321330-92328079 |
| 5375 | Cxcr1 | NM_178241.4 | chr1:74191785-74194631 |
| 5376 | Cxcr2 | NM_009909.3 | chr1:74153993-74161246 |
| 5377 | Cxcr3 | NM_009910.3 | chrX:101731534-101734147 |
| 5378 | Cxcr4 | NM_009911.3 | chr1:128588198-128592299 |
| 5379 | Cxcr5 | NM_007551.2 | chr9:44511786-44526421 |
| 5380 | Cxcr6 | NM_030712.4 | chr9:123806476-123811754 |
| 5381 | Cxx1a | NM_024170.2 | chrX:53642488-53643763 |
| 5382 | Cxx1b | NM_001018063.1 | chrX:53669176-53670408 |
| 5383 | Cxx1c | NM_028375.3 | chrX:53667921-53669134 |
| 5384 | Cxxc1 | NM_028868.3 | chr18:74216211-74221491 |
| 5385 | Cxxc4 | NM_001004367.4 | chr3:134236494-134262089 |
| 5386 | Cxxc5 | NM_133687.2 | chr18:35829817-35861688 |
| 5387 | Cyb5 | NM_025797.3 | chr18:84851413-84879863 |
| 5388 | Cyb561 | NM_007820.4 | chr11:105933703-105944147 |
| 5389 | Cyb561a3 | NM_001282064.1 | chr19:10577156-105590401 |
| 5390 | Cyb561d1 | NM_001081320.2 | chr3:108195770-108200834 |
| 5391 | Cyb561d2 | NM_019720.4 | chr9:10579010-107541865 |
| 5392 | Cyb5b | NM_025558.5 | chr8:107150660-107187470 |
| 5393 | Cyb5d1 | NM_001045525.1 | chr11:69393611-69395346 |
| 5394 | Cyb5d2 | NM_001024926.3 | chr11:72777231-72795839 |
| 5395 | Cyb5r1 | NM_028057.2 | chr1:134405989-134411738 |
| 5396 | Cyb5r2 | NM_001205227.1 | chr7:107748454-107758032 |
| 5397 | Cyb5r3 | NM_029787.2 | chr15:83153500-83172208 |
| 5398 | Cyb5r4 | NM_024195.2 | chr9:87022028-87077774 |
| 5399 | Cyb5rl | NM_175471.2 | chr4:107070167-107084805 |
| 5400 | Cyba | NM_007806.4 | chr8:122424770-122432940 |
| 5401 | Cybb | NM_007807.5 | chrX:9435253-9469324 |
| 5402 | Cybrd1 | NM_028834.3 | chr2:71118053-71142926 |
| 5403 | Cyc1 | NM_025567.2 | chr15:76343522-76345934 |
| 5404 | Cycs | NM_007808.4 | chr6:50562562-50566474 |
| 5405 | Cyct | NM_009989.3 | chr2:76353941-76360463 |
| 5406 | Cyfip1 | NM_001164661.1 | chr7:55842070-55932633 |
| 5407 | Cyfip2 | NM_001252459.1 | chr11:46193848-46312859 |
| 5408 | Cygb | NM_030206.4 | chr11:116645594-116654313 |
| 5409 | Cyhr1 | NM_001276321.1 | chr15:76646926-76656901 |
| 5410 | Cyic1 | NM_026134.2 | chrX:111110417-111123874 |
| 5411 | Cyic2 | NM_001162865.1 | chr4:51216677-51229928 |
| 5412 | Cyld | NM_001128170.2 | chr8:88697027-88751946 |
| 5413 | Cym | NM_001111143.1 | chr3:107211294-107217732 |
| 5414 | Cyp11a1 | NM_019779.3 | chr9:58015016-58027023 |
| 5415 | Cyp11b1 | NM_001033229.3 | chr15:74834891-74841643 |
| 5416 | Cyp11b2 | NM_009991.3 | chr15:74851009-74856318 |
| 5417 | Cyp17a1 | NM_007809.3 | chr19:46667164-46673000 |
| 5418 | Cyp19a1 | NM_007810.3 | chr9:54185936-54193442 |
| 5419 | Cyp1a1 | NM_001136059.2 | chr9:57697612-57703824 |
| 5420 | Cyp1a2 | NM_009993.3 | chr9:57676936-57683655 |
| 5421 | Cyp1b1 | NM_009994.1 | chr17:79796952-79715041 |
| 5422 | Cyp20a1 | NM_030013.3 | chr1:60343299-60388060 |
| 5423 | Cyp21a1 | NM_009995.2 | chr17:34801347-34804426 |
| 5424 | Cyp24a1 | NM_009996.4 | chr2:170482956-170497145 |
| 5425 | Cyp26a1 | NM_007811.2 | chr19:37697807-37701536 |
| 5426 | Cyp26b1 | NM_001177713.1 | chr6:84571413-84593908 |
| 5427 | Cyp26c1 | NM_001105201.1 | chr19:37685679-37693307 |
| 5428 | Cyp27a1 | NM_024264.5 | chr1:74713534-74737897 |
| 5429 | Cyp27b1 | NM_010009.2 | chr10:127048245-127053006 |
| 5430 | Cyp2a12 | NM_133657.1 | chr7:27029089-27036815 |
| 5431 | Cyp2a22 | NM_001101467.1 | chr7:26933630-26939386 |
| 5432 | Cyp2a4 | NM_009997.2 | chr7:26307191-26315088 |
| 5433 | Cyp2a5 | NM_007812.4 | chr7:26835338-26843264 |
| 5434 | Cyp2ab1 | NM_183158.3 | chr16:20308386-20325404 |
| 5435 | Cyp2b10 | NM_009999.4 | chr7:25897657-25926624 |
| 5436 | Cyp2b13 | NM_007813.2 | chr7:26061494-26096196 |
| 5437 | Cyp2b19 | NM_007814.2 | chr7:26757141-26772630 |
| 5438 | Cyp2b23 | NM_001081148.1 | chr7:26665226-26686430 |
| 5439 | Cyp2b9 | NM_010000.2 | chr7:26173408-26210660 |
| 5440 | Cyp2c29 | NM_007815.3 | chr19:39287084-39330713 |
| 5441 | Cyp2c37 | NM_010001.2 | chr19:39992423-40012243 |
| 5442 | Cyp2c38 | NM_010002.3 | chr19:39389555-39463075 |
| 5443 | Cyp2c39 | NM_010003.2 | chr19:39510821-39568529 |
| 5444 | Cyp2c40 | NM_010004.2 | chr19:39767072-39812814 |
| 5445 | Cyp2c44 | NM_001001446.3 | chr19:44005021-44029247 |
| 5446 | Cyp2c50 | NM_001167875.1 | chr19:40089678-40113955 |
| 5447 | Cyp2c53-ps | NR_033614.1 | chr19:39229253-39274737 |
| 5448 | Cyp2c54 | NM_206537.2 | chr19:40037939-40073813 |
| 5449 | Cyp2c55 | NM_028089.3 | chr19:39007018-39042687 |
| 5450 | Cyp2c65 | NM_028191.2 | chr19:39061005-39093948 |
| 5451 | Cyp2c66 | NM_001017107.1 | chr19:39113897-39186756 |
| 5452 | Cyp2c67 | NM_001024719.2 | chr19:39608858-39649042 |
| 5453 | Cyp2c68 | NM_001039555.2 | chr19:39688835-39741101 |
| 5454 | Cyp2c69 | NM_001104525.1 | chr19:39842659-39886769 |
| 5455 | Cyp2c70 | NM_145499.2 | chr19:40153360-40187286 |
| 5456 | Cyp2d10 | NM_010005.3 | chr15:82402845-82407194 |
| 5457 | Cyp2d11 | NM_001104531.1 | chr15:82389159-82394022 |
| 5458 | Cyp2d12 | NM_201360.1 | chr15:82555097-82559413 |
| 5459 | Cyp2d13 | NR_003552.1 | chr15:82636749-82642045 |
| 5460 | Cyp2d22 | NM_001163472.1 | chr15:82370526-82380260 |
| 5461 | Cyp2d26 | NM_029562.2 | chr15:82790106-82794245 |
| 5462 | Cyp2d34 | NM_145474.2 | chr15:82615964-82620907 |
| 5463 | Cyp2d37-ps | NR_033515.1 | chr15:82688749-82690058 |
| 5464 | Cyp2d40 | NM_023623.2 | chr15:82759832-82764122 |
| 5465 | Cyp2d9 | NM_010006.2 | chr15:82452376-82456827 |
| 5466 | Cyp2e1 | NM_021282.2 | chr7:140763831-140774977 |
| 5467 | Cyp2f2 | NM_007817.2 | chr7:27119954-27133660 |
| 5468 | Cyp2g1 | NM_033809.1 | chr7:26808926-26821197 |
| 5469 | Cyp2j11 | NM_001004141.2 | chr4:96294508-96348680 |
| 5470 | Cyp2j12 | NM_001100182.2 | chr4:96099317-96141152 |
| 5471 | Cyp2j13 | NM_145548.4 | chr4:96042659-96077540 |
| 5472 | Cyp2j5 | NM_010007.4 | chr4:96627431-96664119 |
| 5473 | Cyp2j6 | NM_010008.4 | chr4:96516137-96553651 |
| 5474 | Cyp2j8 | NM_001104927.1 | chr4:96444587-96507386 |
| 5475 | Cyp2j9 | NM_028979.2 | chr4:96568428-96591485 |
| 5476 | Cyp2r1 | NM_177382.4 | chr7:114550162-114562972 |
| 5477 | Cyp2s1 | NM_028775.3 | chr7:25802475-25816530 |
| 5478 | Cyp2t4 | NM_001100184.1 | chr7:27153713-27158564 |
| 5479 | Cyp2u1 | NM_027816.3 | chr3:131290430-131303227 |
| 5480 | Cyp2w1 | NM_001160265.1 | chr5:139352616-139357033 |
| 5481 | Cyp39a1 | NM_001285947.1 | chr17:43667371-43751431 |
| 5482 | Cyp3a11 | NM_007818.3 | chr5:145854606-145879854 |
| 5483 | Cyp3a13 | NM_007819.4 | chr5:137892932-137921619 |
| 5484 | Cyp3a16 | NM_007820.2 | chr5:145436308-145469723 |
| 5485 | Cyp3a25 | NM_019792.2 | chr5:145977193-146009617 |
| 5486 | Cyp3a41a | NM_017936.3 | chr5:145694049-145720136 |
| 5487 | Cyp3a41b | NM_001105159.1 | chr5:145558663-145584730 |
| 5488 | Cyp3a44 | NM_177380.3 | chr5:145773982-145805874 |
| 5489 | Cyp3a57 | NM_001100180.1 | chr5:145345269-145390512 |
| 5490 | Cyp3a59 | NM_001105160.1 | chr5:146079257-146113283 |
| 5491 | Cyp46a1 | NM_010010.1 | chr12:108334380-108362234 |
| 5492 | Cyp4a10 | NM_010011.3 | chr4:115518286-115533649 |
| 5493 | Cyp4a12a | NM_177406.3 | chr4:115299045-115332815 |
| 5494 | Cyp4a12b | NM_172306.2 | chr4:115441623-115439034 |
| 5495 | Cyp4a14 | NM_007822.2 | chr4:115486199-115496141 |
| 5496 | Cyp4a29 | NM_001100183.1 | chr4:115422083-115254557 |
| 5497 | Cyp4a30b | NM_001100185.1 | chr4:115452603-115471062 |
| 5498 | Cyp4a31 | NM_001252539.1 | chr4:115563648-115579015 |
| 5499 | Cyp4a32 | NM_001100181.1 | chr4:115600937-115622366 |
| 5500 | Cyp4b1 | NM_007823.2 | chr4:115624727-115647705 |
| 5501 | Cyp4b1-ps2 | NR_033575.1 | chr4:115582037-115583127 |
| 5502 | Cyp4f13 | NM_130882.1 | chr17:32924687-32947361 |
| 5503 | Cyp4f14 | NM_001204333.1 | chr17:32905069-32917329 |
| 5504 | Cyp4f15 | NM_134127.1 | chr17:32685658-32703349 |
| 5505 | Cyp4f16 | NM_024442.1 | chr17:32536628-32551797 |

Fig. 26 - 30

| | | | |
|---|---|---|---|
| 5506 | Cyp4f17 | NM_001101445.1 | chr17:32506461-32528894 |
| 5507 | Cyp4f18 | NM_024444.2 | chr8:71988481-72009626 |
| 5508 | Cyp4f37 | NM_001100187.1 | chr17:32621318-32636184 |
| 5509 | Cyp4f39 | NM_177307.3 | chr17:32452722-32493320 |
| 5510 | Cyp4f40 | NM_001101588.1 | chr17:32659482-32676480 |
| 5511 | Cyp4f41-ps | NR_033585.1 | chr17:32950966-32965716 |
| 5512 | Cyp4v3 | NM_133969.2 | chr8:45305801-45333196 |
| 5513 | Cyp4x1 | NM_001003947.1 | chr4:115108681-115133977 |
| 5514 | Cyp51 | NM_020010.2 | chr5:4080673-4104697 |
| 5515 | Cyp7a1 | NM_007824.2 | chr4:6265611-6275631 |
| 5516 | Cyp7b1 | NM_007825.4 | chr3:18071949-18243338 |
| 5517 | Cyp8b1 | NM_010012.3 | chr9:121914355-121916305 |
| 5518 | Cypt1 | NM_025738.3 | chrX:16522868-16523691 |
| 5519 | Cypt12 | NM_029289.1 | chr17:17948443-17948952 |
| 5520 | Cypt14 | NM_001191032.1 | chrX:39862918-39863604 |
| 5521 | Cypt15 | NM_001177380.1 | chrX:39346265-39346961 |
| 5522 | Cypt2 | NM_173436.2 | chrX:105499771-105500637 |
| 5523 | Cypt3 | NM_173367.3 | chrX:153558592-153559435 |
| 5524 | Cypt4 | NM_173412.2 | chr9:24625184-24625828 |
| 5525 | Cypt7 | NM_001039943.2 | chrX:16522880-16523615 |
| 5526 | Cypt8 | NM_001039941.2 | chrX:16522880-16523615 |
| 5527 | Cypt9 | NM_001039942.2 | chr9:24625203-24625737 |
| 5528 | Cyr61 | NM_010516.2 | chr3:145646970-145649985 |
| 5529 | Cys1 | NM_001004455.2 | chr12:24665837-24681795 |
| 5530 | Cysltr1 | NM_001281859.1 | chrX:106576508-106603679 |
| 5531 | Cysltr2 | NM_001162412.1 | chr14:73029127-73049114 |
| 5532 | Cystm1 | NM_001081365.1 | chr18:36348623-36393370 |
| 5533 | Cyth1 | NM_001112699.1 | chr11:118164165-118248592 |
| 5534 | Cyth2 | NM_001112701.1 | chr7:45806636-45814316 |
| 5535 | Cyth3 | NM_001163548.1 | chr5:143651240-143710248 |
| 5536 | Cyth4 | NM_028195.3 | chr15:78597046-78622019 |
| 5537 | Cytip | NM_139200.4 | chr2:58129138-58160122 |
| 5538 | Cytl1 | NM_001081106.1 | chr5:37735518-37739820 |
| 5539 | Cyyr1 | NM_144853.3 | chr16:85456243-85550373 |
| 5540 | D030018L15Rik | NR_126492.1 | chr15:96051616-96079553 |
| 5541 | D030024E09Rik | NR_040350.1 | chr15:61699283-61774451 |
| 5542 | D030025E07Rik | NR_045704.1 | chr3:128117014-128231605 |
| 5543 | D030025P21Rik | NR_028577.1 | chr12:84875801-84879755 |
| 5544 | D030028L42Rik | NR_026393.1 | chr11:96944145-96965060 |
| 5545 | D030040B21Rik | NR_037998.1 | chr1:16657551-16662278 |
| 5546 | D030045P18Rik | NR_040624.1 | chr10:45807703-45852018 |
| 5547 | D030047H15Rik | NR_033548.1 | chr7:4126339-4136926 |
| 5548 | D030056L22Rik | NM_177640.4 | chr19:18713235-18718428 |
| 5549 | D10Bwg1379e | NM_001033258.4 | chr10:18588010-18743758 |
| 5550 | D10Jhu81e | NM_138601.2 | chr10:78162066-78169768 |
| 5551 | D10Wsu102e | NM_026579.3 | chr10:83360220-83368835 |
| 5552 | D11Wsu47e | NM_177777.5 | chr11:113684411-113694647 |
| 5553 | D130009J18Rik | NR_015593.2 | chr14:104639146-104966783 |
| 5554 | D130017N08Rik | NR_015486.2 | chr5:143758353-143764942 |
| 5555 | D130020L05Rik | NR_038047.1 | chr12:101082450-101088927 |
| 5556 | D130040H23Rik | NM_172419.2 | chr8:69271079-69303375 |
| 5557 | D130043K22Rik | NM_001081051.2 | chr13:24845130-24901439 |
| 5558 | D130058E03 | NR_073373.1 | chr6:127296185-127307967 |
| 5559 | D14Ertd670e | NR_105025.1 | chr14:19838924-19844677 |
| 5560 | D15Ertd621e | NM_145959.3 | chr15:58415467-58457801 |
| 5561 | D16Ertd472e | NM_001252438.1 | chr16:78540335-78576688 |
| 5562 | D16Ertd519e | NR_040474.1 | chr16:70616424-70624822 |
| 5563 | D17Ertd648e | NR_045808.1 | chr17:11863069-11883189 |
| 5564 | D17H6S53E | NM_033477.2 | chr17:35126401-35128855 |
| 5565 | D17Wsu104e | NM_080837.2 | chr17:56176540-56183920 |
| 5566 | D17Wsu92e | NM_001033279.3 | chr17:27751231-27820542 |
| 5567 | D19Bwg1357e | NM_177474.5 | chr19:27388697-27429908 |
| 5568 | D1Ertd622e | NM_133825.3 | chr1:97643901-97662018 |
| 5569 | D1Pas1 | NM_033077.3 | chr1:186967415-186970627 |
| 5570 | D230025D16Rik | NM_145464.2 | chr8:105225187-105253051 |
| 5571 | D230030E09Rik | NR_045947.1 | chr12:118518296-118530193 |
| 5572 | D2hgdh | NM_178882.4 | chr1:93825239-93852361 |
| 5573 | D2Wsu81e | NM_172660.4 | chr2:30173446-30178459 |
| 5574 | D330023K18Rik | NR_040334.1 | chr2:31151048-31152291 |
| 5575 | D330041H03Rik | NR_033554.1 | chr1:7244049480-24414513 |
| 5576 | D330045A20Rik | NM_175326.5 | chrX:139480366-139554580 |
| 5577 | D330050G23Rik | NR_040335.1 | chr2:116900151-116912791 |
| 5578 | D330050H6Rik | NR_033224.1 | chr19:5388335-5390069 |
| 5579 | D3Bwg0562e | NM_177664.5 | chr3:117319145-117360876 |
| 5580 | D3Ertd254e | NM_001101478.1 | chr3:36151079-36170341 |
| 5581 | D3Ertd751e | NM_001109379.1 | chr3:41742617-41758939 |
| 5582 | D430019H16Rik | NM_001252508.1 | chr12:105453855-105493095 |
| 5583 | D430020J02Rik | NR_028421.1 | chr12:116401946-116405161 |
| 5584 | D430036J16Rik | NR_040393.1 | chr9:81631929-81645156 |
| 5585 | D430041D05Rik | NM_001033347.2 | chr2:104143074-104410310 |
| 5586 | D430042O09Rik | NM_001081022.1 | chr7:125707875-125874797 |
| 5587 | D4Ertd617e | NR_029469.1 | chr4:118626403-118631915 |
| 5588 | D530049I02Rik | NR_040605.1 | chr1:73398967-73430779 |
| 5589 | D5Ertd577e | NM_177187.4 | chr5:95456805-95485589 |
| 5590 | D5Ertd579e | NM_001081232.3 | chr5:36686021-36696021 |
| 5591 | D5Ertd605e | NR_033625.1 | chr5:147418819-147423044 |
| 5592 | D630003M21Rik | NR_131021.2 | chr2:158182532-158229249 |
| 5593 | D630010B17Rik | NR_045629.1 | chr15:94247201-94255606 |
| 5594 | D630013N20Rik | NR_045291.1 | chr10:70601048-70651925 |
| 5595 | D630023F18Rik | NR_030081.1 | chr1:65107312-65123214 |
| 5596 | D630024D03Rik | NR_102310.1 | chr1:31817983-31824547 |
| 5597 | D630029K05Rik | NR_027846.1 | chr10:116966273-116969107 |
| 5598 | D630032N06Rik | NR_028329.1 | chr5:85225165-85238304 |
| 5599 | D630033O11Rik | NM_001243261.1 | chr9:43259878-43280075 |
| 5600 | D630039A03Rik | NM_178727.2 | chr4:57908383-57916264 |
| 5601 | D630041G03Rik | NR_028416.1 | chr7:4467244-4470984 |
| 5602 | D630045I12Rik | NM_194061.2 | chr6:38123173-38254009 |
| 5603 | D630045M09Rik | NR_045293.1 | chr13:73344664-73347384 |
| 5604 | D6Ertd474e | NR_027803.1 | chr6:143245887-143297879 |
| 5605 | D6Ertd527e | NM_001167937.1 | chr6:87104745-87113003 |
| 5606 | D6Wsu163e | NM_138594.3 | chr6:126939965-126975704 |
| 5607 | D730001G18Rik | NR_027836.1 | chr15:74770907-74778859 |
| 5608 | D730005E14Rik | NR_030675.1 | chr15:79889531-79893138 |
| 5609 | D730045A05Rik | NR_045390.1 | chr18:74017906-74020088 |
| 5610 | D730048I06Rik | NM_026593.3 | chr9:35788049-35790112 |
| 5611 | D730050B12Rik | NR_046196.1 | chr13:72809600-72816763 |
| 5612 | D7Ertd143e | NR_028425.1 | chr7:3218783-3221015 |
| 5613 | D7Ertd443e | NM_001081331.1 | chr7:134266261-134376828 |
| 5614 | D7Ertd715e | NR_015456.1 | chr7:59969576-59974431 |
| 5615 | D830005E20Rik | NR_040657.1 | chr10:33222344-33256357 |
| 5616 | D830013O20Rik | NR_046013.1 | chr12:73364074-73409963 |
| 5617 | D830015G02Rik | NR_033497.1 | chr14:54968786-54974349 |
| 5618 | D830026H12Rik | NR_102304.1 | chr6:17198106-17205695 |
| 5619 | D830030K20Rik | NM_177135.4 | chr4:3224439-3856080 |
| 5620 | D830031N03Rik | NM_001167918.1 | chr4:123403600-123411911 |
| 5621 | D830032E09Rik | NR_102306.1 | chr1:107917258-107950947 |
| 5622 | D830046C22Rik | NR_033147.1 | chr5:139377696-139380053 |
| 5623 | D8Ertd738e | NM_001007571.2 | chr8:84246234-84249761 |
| 5624 | D8Ertd82e | NM_172911.3 | chr8:36094827-36147787 |
| 5625 | D930007P13Rik | NR_045743.1 | chr15:103123069-103146828 |
| 5626 | D930015E06Rik | NM_172681.4 | chr3:83898286-84040161 |
| 5627 | D930015M05Rik | NR_040621.1 | chr2:92408891-92432308 |
| 5628 | D930016D06Rik | NR_030673.1 | chr5:104525734-104554211 |
| 5629 | D930020B18Rik | NM_177335.4 | chr10:121841700-121693914 |
| 5630 | D930028M14Rik | NR_045847.1 | chr7:25152456-25156630 |
| 5631 | D930032P07Rik | NR_045330.1 | chr19:28676223-28720027 |
| 5632 | D930048N14Rik | NR_027958.1 | chr11:51650953-51657681 |
| 5633 | Daam1 | NM_001286452.1 | chr12:71889542-71992376 |
| 5634 | Daam2 | NM_001008231.2 | chr17:49456021-49564337 |
| 5635 | Dab1 | NM_010014.3 | chr4:104367537-104680389 |
| 5636 | Dab2 | NM_001008702.2 | chr15:6299788-6440709 |
| 5637 | Dab2ip | NM_001001602.2 | chr2:35691993-35730994 |
| 5638 | Dach1 | NM_001038610.2 | chr14:97786845-98169765 |
| 5639 | Dach2 | NM_001284570.1 | chrX:113298255-113835091 |
| 5640 | Dact1 | NM_001190466.1 | chr12:71309883-71320107 |
| 5641 | Dact2 | NM_172826.3 | chr17:14195229-14203831 |
| 5642 | Dact3 | NM_001034651.1 | chr7:16875316-16887301 |
| 5643 | Dad1 | NM_001113358.1 | chr14:54235484-54253929 |
| 5644 | Daf2 | NM_007827.2 | chr1:130388527-130422999 |
| 5645 | Dag1 | NM_001276481.1 | chr9:108204860-108263815 |
| 5646 | Dagla | NM_198114.2 | chr19:10245264-10304877 |
| 5647 | Daglb | NM_144915.3 | chr5:143464492-143504442 |
| 5648 | Dak | NM_145496.1 | chr19:10592196-10604258 |
| 5649 | Daird3 | NM_026378.3 | chr9:108569891-108572771 |
| 5650 | Dancr | NR_015531.1 | chr5:74093082-74094336 |
| 5651 | Dand5 | NM_201227.3 | chr8:84815404-84822823 |
| 5652 | Dao | NM_001286396.1 | chr5:114040807-114025675 |
| 5653 | Dap | NM_146057.3 | chr15:31224384-31274338 |
| 5654 | Dap3 | NM_001164533.1 | chr3:88920802-88950282 |
| 5655 | Dapk1 | NM_001285917.1 | chr13:60601946-60763191 |
| 5656 | Dapk2 | NM_010019.3 | chr9:66158225-66272242 |
| 5657 | Dapk3 | NM_001190473.1 | chr10:81183262-81193197 |
| 5658 | Dapl1 | NM_029723.3 | chr2:59484652-59505020 |
| 5659 | Dapp1 | NM_011932.3 | chr3:137931006-137981549 |
| 5660 | Dars | NM_145507.2 | chr1:128412117-128417416 |
| 5661 | Dars2 | NM_172644.4 | chr1:161040600-161070660 |
| 5662 | Daw1 | NM_027725.3 | chr1:83159761-83210572 |
| 5663 | Daxx | NM_001199733.1 | chr17:33909600-33915590 |
| 5664 | Dazap1 | NM_001122604.1 | chr10:80264990-80288413 |
| 5665 | Dazap2 | NM_011873.2 | chr15:100615661-100620761 |
| 5666 | Dazl | NM_001277863.1 | chr17:50279392-50293620 |
| 5667 | Dbf4 | NM_001190717.1 | chr5:8396968-8422716 |
| 5668 | Dbh | NM_138942.3 | chr2:27165506-27183204 |
| 5669 | Dbhos | NR_040524.1 | chr2:27144897-27162703 |
| 5670 | Dbi | NM_001037999.2 | chr1:120113279-120120919 |
| 5671 | Dbi-rs | NM_021294.2 | chr11:76217612-76218665 |
| 5672 | Dbn1 | NM_001177371.1 | chr13:55473427-55488076 |
| 5673 | Dbndd1 | NM_001160975.2 | chr8:123505686-123515455 |
| 5674 | Dbndd2 | NM_001048227.1 | chr2:164486139-164493323 |
| 5675 | Dbnl | NM_001146308.1 | chr11:5788482-5800980 |
| 5676 | Dbp | NM_016974.3 | chr7:45705246-45710203 |
| 5677 | Dbpht2 | NM_198866.2 | chr12:74297473-74300468 |
| 5678 | Dbr1 | NM_031403.3 | chr9:99575798-99584343 |
| 5679 | Dbt | NM_010023.3 | chr3:116513078-116549981 |
| 5680 | Dbx1 | NM_001005232.1 | chr7:49631498-49636835 |
| 5681 | Dbx2 | NM_207533.2 | chr15:95623562-95654771 |
| 5682 | Dcaf10 | NM_153167.2 | chr4:45342100-45379722 |
| 5683 | Dcaf11 | NM_001199009.1 | chr14:55560922-55570065 |
| 5684 | Dcaf12 | NM_026893.3 | chr4:41291299-41314901 |
| 5685 | Dcaf12l1 | NM_001190718.1 | chrX:44786566-44790161 |
| 5686 | Dcaf12l2 | NM_175539.3 | chrX:44365456-44368337 |
| 5687 | Dcaf13 | NM_198606.2 | chr15:39112873-39146855 |
| 5688 | Dcaf15 | NM_172502.3 | chr8:84097071-84104762 |
| 5689 | Dcaf17 | NM_001165980.1 | chr2:71055743-71095858 |
| 5690 | Dcaf4 | NM_001165256.1 | chr12:83526048-83541992 |
| 5691 | Dcaf5 | NM_001081.3 | chr12:80335846-80436601 |
| 5692 | Dcaf6 | NM_028759.1 | chr1:165329500-165460463 |
| 5693 | Dcaf7 | NM_027946.3 | chr11:106036871-106059323 |
| 5694 | Dcaf8 | NM_153555.2 | chr1:172148014-172196393 |
| 5695 | Dcakd | NM_026551.3 | chr11:102994055-103017147 |

Fig. 26 - 31

| | | | |
|---|---|---|---|
| 5696 | Dcbld1 | NM_025705.3 | chr10:52233618-52321377 |
| 5697 | Dcbld2 | NM_028523.3 | chr16:58408534-58469745 |
| 5698 | Dcc | NM_007831.3 | chr18:71253631-72351069 |
| 5699 | Dcdc2a | NM_001195617.1 | chr13:25056003-25121521 |
| 5700 | Dcdc2b | NM_001195730.1 | chr4:129608330-129614257 |
| 5701 | Dcdc2c | NM_001177964.2 | chr12:28437794-28548337 |
| 5702 | Dchs1 | NM_001162943.1 | chr7:105752988-105787550 |
| 5703 | Dck | NM_007832.4 | chr5:88765012-88783277 |
| 5704 | Dclk1 | NM_001111051.1 | chr3:55461757-55539068 |
| 5705 | Dclk2 | NM_001195496.1 | chr3:86786149-86920884 |
| 5706 | Dclk3 | NM_172928.5 | chr9:111439080-111489611 |
| 5707 | Dcre1a | NM_018831.4 | chr19:56529160-56548222 |
| 5708 | Dcre1b | NM_001025312.1 | chr3:103800604-103809387 |
| 5709 | Dcre1c | NM_001110214.1 | chr2:3424130-3461116 |
| 5710 | Dcn | NM_001190451.2 | chr10:97479499-97518163 |
| 5711 | Dcp1a | NM_133761.3 | chr14:30479564-30527056 |
| 5712 | Dcp1b | NM_001033379.3 | chr6:119175252-119221614 |
| 5713 | Dcp2 | NM_027490.1 | chr18:44380499-44424969 |
| 5714 | Dcpp1 | NM_019910.2 | chr17:23880875-23882853 |
| 5715 | Dcpp2 | NM_001039238.2 | chr17:23898721-23900787 |
| 5716 | Dcpp3 | NM_001077633.1 | chr17:23917457-23919441 |
| 5717 | Dcps | NM_027030.2 | chr9:35124413-35175987 |
| 5718 | Dcst1 | NM_029974.2 | chr3:89350218-89365253 |
| 5719 | Dcstamp | NM_001289506.1 | chr15:39745929-39760938 |
| 5720 | Dct | NM_010024.3 | chr14:118012789-118052246 |
| 5721 | Dctd | NM_001161515.1 | chr8:48110012-48141667 |
| 5722 | Dctn1 | NM_001198866.1 | chr6:83165923-83200117 |
| 5723 | Dctn2 | NM_001190453.1 | chr10:127266261-127281959 |
| 5724 | Dctn3 | NM_001159565.1 | chr4:41714797-41723163 |
| 5725 | Dctn4 | NM_026302.3 | chr18:60526220-60558762 |
| 5726 | Dctn5 | NM_021608.3 | chr7:122133040-122149044 |
| 5727 | Dctn6 | NM_011722.4 | chr8:34090420-34108712 |
| 5728 | Dctpp1 | NM_023203.1 | chr7:127256958-127260667 |
| 5729 | Dcun1d1 | NM_001026361.1 | chr3:35892104-35932966 |
| 5730 | Dcun1d2 | NM_001024504.2 | chr8:13255962-13288126 |
| 5731 | Dcun1d3 | NM_001163703.1 | chr7:119853162-119895745 |
| 5732 | Dcun1d4 | NM_001190733.1 | chr5:73491025-73560794 |
| 5733 | Dcun1d5 | NM_029775.2 | chr9:7184565-7207031 |
| 5734 | Dcx | NM_001110222.1 | chrX:143855841-143933124 |
| 5735 | Dcxr | NM_026428.2 | chr11:120725372-120727281 |
| 5736 | Dda1 | NM_025600.2 | chr8:71469193-71476097 |
| 5737 | Ddah1 | NM_026993.3 | chr3:145758691-145894277 |
| 5738 | Ddah2 | NM_001190449.1 | chr17:35059034-35062099 |
| 5739 | Ddb1 | NM_015735.1 | chr19:10605624-10629821 |
| 5740 | Ddb2 | NM_028119.5 | chr2:91211581-91237066 |
| 5741 | Ddc | NM_001190448.1 | chr11:11814100-11898144 |
| 5742 | Ddhd1 | NM_001039106.3 | chr14:45593170-45658143 |
| 5743 | Ddhd2 | NM_028102.1 | chr8:25725323-25754280 |
| 5744 | Ddi1 | NM_027942.1 | chr9:6265027-6266947 |
| 5745 | Ddi2 | NM_001017966.2 | chr4:141683562-141723419 |
| 5746 | Ddit3 | NM_001290183.1 | chr10:127290792-127296288 |
| 5747 | Ddit4 | NM_029083.2 | chr10:59949674-59951770 |
| 5748 | Ddit4l | NM_030143.4 | chr3:137623671-137628332 |
| 5749 | Ddn | NM_001013741.1 | chr15:98803781-98807925 |
| 5750 | Ddo | NM_027442.5 | chr10:40630010-40649931 |
| 5751 | Ddost | NM_007829.2 | chr4:138304737-138312611 |
| 5752 | Ddr1 | NM_001198831.1 | chr17:35681566-35702044 |
| 5753 | Ddr2 | NM_022563.2 | chr1:169972306-170088944 |
| 5754 | Ddrgk1 | NM_029832.2 | chr2:130654082-130664645 |
| 5755 | Ddt | NM_010027.1 | chr10:75771232-75773374 |
| 5756 | Ddx1 | NM_134040.1 | chr12:13219306-13249174 |
| 5757 | Ddx10 | NM_029936.2 | chr9:53098453-53248112 |
| 5758 | Ddx11 | NM_001003919.1 | chr17:66123519-66152168 |
| 5759 | Ddx17 | NM_001040187.1 | chr15:79527695-79546741 |
| 5760 | Ddx18 | NM_025860.3 | chr1:121553834-121567980 |
| 5761 | Ddx19a | NM_007916.2 | chr8:110974990-110997823 |
| 5762 | Ddx19b | NM_001190786.1 | chr8:111003185-111031751 |
| 5763 | Ddx20 | NM_017397.3 | chr3:105678461-105687571 |
| 5764 | Ddx21 | NM_019553.2 | chr10:62580246-62602298 |
| 5765 | Ddx23 | NM_001080981.1 | chr15:98645506-98662889 |
| 5766 | Ddx24 | NM_001159502.1 | chr12:103407975-103425780 |
| 5767 | Ddx25 | NM_013932.4 | chr9:35541847-35558470 |
| 5768 | Ddx26b | NM_172779.4 | chrX:56454838-56507843 |
| 5769 | Ddx27 | NM_153065.3 | chr2:167015312-167034945 |
| 5770 | Ddx28 | NM_028038.3 | chr8:106009615-106011486 |
| 5771 | Ddx31 | NM_001033294.3 | chr2:28840405-28905575 |
| 5772 | Ddx39 | NM_197982.3 | chr8:83715176-83723351 |
| 5773 | Ddx39b | NM_001252457.1 | chr17:35242816-35253707 |
| 5774 | Ddx3x | NM_010028.3 | chrX:13281021-13293983 |
| 5775 | Ddx3y | NM_012008.2 | chrY:1260714-1286613 |
| 5776 | Ddx4 | NM_001145885.1 | chr13:112598332-112652310 |
| 5777 | Ddx41 | NM_134040.4 | chr13:55530409-55536658 |
| 5778 | Ddx42 | NM_028074.4 | chr11:106216925-106249140 |
| 5779 | Ddx43 | NM_001191044.1 | chr9:78395776-78423589 |
| 5780 | Ddx46 | NM_001282055.1 | chr13:55634908-55681267 |
| 5781 | Ddx47 | NM_026360.3 | chr6:135011611-135023776 |
| 5782 | Ddx49 | NM_001024922.2 | chr8:70292865-70302452 |
| 5783 | Ddx5 | NM_007840.3 | chr11:106780355-106788494 |
| 5784 | Ddx50 | NM_053183.2 | chr10:62616022-62651198 |
| 5785 | Ddx51 | NM_025996.2 | chr5:110653450-110660496 |
| 5786 | Ddx52 | NM_030096.2 | chr11:83942089-83963086 |
| 5787 | Ddx54 | NM_028041.2 | chr5:120613129-120628592 |
| 5788 | Ddx55 | NM_001190795.1 | chr5:124552863-124569660 |
| 5789 | Ddx56 | NM_026538.3 | chr11:6257544-6267729 |
| 5790 | Ddx58 | NM_172689.3 | chr4:40203776-40239825 |
| 5791 | Ddx59 | NM_026500.3 | chr1:136415270-136440220 |
| 5792 | Ddx6 | NM_001110826.1 | chr9:44604891-44640731 |
| 5793 | Ddx60 | NM_001293783.1 | chr8:61928066-62037704 |
| 5794 | Deaf1 | NM_001282072.1 | chr7:141297175-141327725 |
| 5795 | Dear1 | NM_001040461.2 | chr3:84965055-84965580 |
| 5796 | Deb1 | NM_026794.2 | chr9:121710388-121712921 |
| 5797 | Decr1 | NM_026172.3 | chr4:15917239-15945507 |
| 5798 | Decr2 | NM_011933.2 | chr17:26081210-26090164 |
| 5799 | Dedd | NM_001128609.1 | chr1:171329144-171342501 |
| 5800 | Dedd2 | NM_207677.3 | chr7:25202839-25219859 |
| 5801 | Def6 | NM_027185.3 | chr17:28207777-28228608 |
| 5802 | Def8 | NM_001253783.1 | chr8:123442955-123463899 |
| 5803 | Defa17 | NM_001167790.1 | chr8:21655766-21656736 |
| 5804 | Defa2 | NM_001195634.2 | chr8:21378516-21379495 |
| 5805 | Defa20 | NM_183268.4 | chr8:21509257-21510237 |
| 5806 | Defa21 | NM_183253.3 | chr8:21025544-21026517 |
| 5807 | Defa22 | NM_207658.4 | chr8:21162276-21163249 |
| 5808 | Defa23 | NM_001012307.2 | chr8:21055039-21192549 |
| 5809 | Defa24 | NM_001024225.2 | chr8:21734493-21735471 |
| 5810 | Defa25 | NM_007849.1 | chr8:21084441-21085285 |
| 5811 | Defa26 | NM_001079933.2 | chr8:21618167-21618972 |
| 5812 | Defa3 | NM_007850.2 | chr8:21287408-21288377 |
| 5813 | Defa4 | NM_010039.2 | chr8:21065065-21065232 |
| 5814 | Defa5 | NM_007851.2 | chr8:21297393-21298375 |
| 5815 | Defa6 | NM_007852.1 | chr8:21734536-21735377 |
| 5816 | Defa-ps1 | NR_003146.1 | chr8:21695011-21695853 |
| 5817 | Defa-ps12 | NR_002878.2 | chr8:19210461-19212760 |
| 5818 | Defa-ps13 | NR_002881.2 | chr8:19300676-19304794 |
| 5819 | Defa-rs1 | NM_007844.2 | chr8:21325887-21327020 |
| 5820 | Defa-rs7 | NM_007848.2 | chr8:21055039-21192550 |
| 5821 | Defb1 | NM_007843.3 | chr8:21776554-21795185 |
| 5822 | Defb10 | NM_139225.1 | chr8:21858900-21862010 |
| 5823 | Defb11 | NM_139221.2 | chr8:21905373-21906432 |
| 5824 | Defb12 | NM_152802.3 | chr8:19111930-19114833 |
| 5825 | Defb13 | NM_139223.3 | chr8:21946761-21948622 |
| 5826 | Defb14 | NM_183026.2 | chr8:19194327-19195309 |
| 5827 | Defb15 | NM_139222.3 | chr8:21929812-21932710 |
| 5828 | Defb18 | NM_001039123.1 | chr1:18236472-18237443 |
| 5829 | Defb19 | NM_145157.3 | chr2:152576085-152580312 |
| 5830 | Defb2 | NM_010030.1 | chr8:21839925-21843481 |
| 5831 | Defb20 | NM_176950.3 | chr2:152477062-152479934 |
| 5832 | Defb21 | NM_207276.2 | chr2:152572743-152574943 |
| 5833 | Defb22 | NM_001002791.2 | chr2:152485665-152490138 |
| 5834 | Defb23 | NM_001037933.2 | chr2:152459054-152464620 |
| 5835 | Defb25 | NM_001039122.1 | chr2:152622355-152623053 |
| 5836 | Defb26 | NM_001039120.2 | chr2:152507755-152511736 |
| 5837 | Defb28 | NM_001037502.2 | chr2:152518254-152521447 |
| 5838 | Defb29 | NM_001001444.2 | chr2:152538713-152540041 |
| 5839 | Defb3 | NM_013756.2 | chr8:19293360-19295339 |
| 5840 | Defb30 | NM_001039566.2 | chr14:63034086-63037846 |
| 5841 | Defb33 | NM_001039119.2 | chr8:20892666-20897723 |
| 5842 | Defb34 | NM_183035.1 | chr8:19123751-19126540 |
| 5843 | Defb35 | NM_183038.1 | chr8:21938351-21940878 |
| 5844 | Defb36 | NM_001037247.4 | chr2:152604326-152612729 |
| 5845 | Defb37 | NM_181683.2 | chr8:18986232-18991055 |
| 5846 | Defb38 | NM_183036.1 | chr8:19023463-19026529 |
| 5847 | Defb39 | NM_183038.2 | chr8:19052825-19064810 |
| 5848 | Defb4 | NM_019728.4 | chr8:19198703-19201547 |
| 5849 | Defb40 | NM_183039.3 | chr8:18974939-18978116 |
| 5850 | Defb41 | NM_183124.3 | chr8:18250977-18265138 |
| 5851 | Defb42 | NM_001034910.3 | chr14:63046990-63048606 |
| 5852 | Defb43 | NM_001039121.1 | chr14:63011770-63018088 |
| 5853 | Defb44-ps | NR_002879.2 | chr1:18210052-18223564 |
| 5854 | Defb45 | NM_001037752.2 | chr2:152593190-152596485 |
| 5855 | Defb46 | NM_001025351.1 | chr8:19239915-19242143 |
| 5856 | Defb47 | NM_001039125.2 | chr14:62998076-63001160 |
| 5857 | Defb48 | NM_001037751.3 | chr14:62977523-62984510 |
| 5858 | Defb5 | NM_030734.2 | chr8:19247591-19250828 |
| 5859 | Defb50 | NM_199067.1 | chr8:21823538-21831296 |
| 5860 | Defb6 | NM_054074.1 | chr8:19225477-19228209 |
| 5861 | Defb7 | NM_139220.1 | chr8:19495096-19497775 |
| 5862 | Defb8 | NM_153108.4 | chr8:19445769-19447606 |
| 5863 | Defb9 | NM_139219.2 | chr8:21881712-21885434 |
| 5864 | Degs1 | NM_007853.4 | chr1:182275769-182282759 |
| 5865 | Degs2 | NM_001171002.1 | chr12:108686791-108702305 |
| 5866 | Dek | NM_025900.2 | chr13:47084766-47106221 |
| 5867 | Dennd1a | NM_146122.3 | chr2:37798989-38287384 |
| 5868 | Dennd1b | NM_001166501.1 | chr1:138963708-139176042 |
| 5869 | Dennd1c | NM_133551.1 | chr17:57086054-57078510 |
| 5870 | Dennd2a | NM_172477.4 | chr6:39462377-39557834 |
| 5871 | Dennd2c | NM_177857.1 | chr3:103127555-103169733 |
| 5872 | Dennd2d | NM_001093754.2 | chr3:106482430-106503030 |
| 5873 | Dennd3 | NM_001081066.1 | chr15:73512559-73572242 |
| 5874 | Dennd4a | NM_001162917.1 | chr9:64811010-64919667 |
| 5875 | Dennd4b | NM_201407.4 | chr3:90266513-90280665 |
| 5876 | Dennd4c | NM_184088.1 | chr4:86748554-86850602 |
| 5877 | Dennd5a | NM_021494.1 | chr7:109893780-109960422 |
| 5878 | Dennd5b | NM_177192.3 | chr6:148988068-149101680 |
| 5879 | Dennd6a | NM_001134465.2 | chr14:26579549-26634322 |
| 5880 | Dennd6b | NM_027081.3 | chr15:89182212-89196474 |
| 5881 | Denr | NM_026603.4 | chr5:123907274-123928832 |
| 5882 | Depdc1a | NM_001172092.1 | chr3:159495432-159529955 |
| 5883 | Depdc1b | NM_178683.4 | chr13:108316336-108389557 |
| 5884 | Depdc5 | NM_001025426.2 | chr5:32863720-32994233 |
| 5885 | Depdc7 | NM_144804.1 | chr2:104721786-104742801 |

Fig. 26 - 32

| | | | |
|---|---|---|---|
| 5886 | Deptor | NM_001037937.3 | chr15:55133435-55259273 |
| 5887 | Dera | NM_172733.1 | chr6:137754576-137837872 |
| 5888 | Derl1 | NM_024207.4 | chr15:57869501-57892418 |
| 5889 | Derl2 | NM_001291146.1 | chr11:71007439-71019841 |
| 5890 | Derl3 | NM_024440.2 | chr10:75893397-75895941 |
| 5891 | Des | NM_010043.2 | chr1:75360291-75368579 |
| 5892 | Desi1 | NM_134095.2 | chr15:81992522-82016140 |
| 5893 | Desi2 | NM_024282.3 | chr1:178187416-178252597 |
| 5894 | Det1 | NM_029585.3 | chr7:78827473-78847211 |
| 5895 | Dexi | NM_021428.4 | chr16:10530206-10543054 |
| 5896 | Dffa | NM_001025296.2 | chr4:149104141-149120653 |
| 5897 | Dffb | NM_007859.4 | chr4:153964448-153975081 |
| 5898 | Dfna5 | NM_018769.3 | chr6:50207402-50261769 |
| 5899 | Dfnb59 | NM_001080711.2 | chr2:76650272-76658554 |
| 5900 | Dgat1 | NM_010046.2 | chr15:76502014-76511818 |
| 5901 | Dgat2 | NM_026384.3 | chr7:99153662-99182713 |
| 5902 | Dgat2l6 | NM_001114084.1 | chrX:100524837-100546108 |
| 5903 | Dgcr14 | NM_001081633.1 | chr16:17900708-17911348 |
| 5904 | Dgcr2 | NM_001109750.1 | chr16:17840355-17891728 |
| 5905 | Dgcr6 | NM_001289813.1 | chr16:18066402-18071632 |
| 5906 | Dgcr8 | NM_033324.2 | chr16:18253964-18289168 |
| 5907 | Dgka | NM_016811.2 | chr10:128720135-128744056 |
| 5908 | Dgkb | NM_178681.4 | chr12:37880704-38633410 |
| 5909 | Dgkd | NM_177646.3 | chr1:87853286-87944489 |
| 5910 | Dgke | NM_019505.3 | chr1:89037581-89060748 |
| 5911 | Dgkeos | NR_110336.1 | chr1:89060750-89067884 |
| 5912 | Dgkg | NM_138650.2 | chr16:22466568-22657231 |
| 5913 | Dgkh | NM_001081336.1 | chr14:78569608-78725089 |
| 5914 | Dgki | NM_001081206.1 | chr6:36846021-37299976 |
| 5915 | Dgkk | NM_177914.3 | chrX:6873483-6948363 |
| 5916 | Dgkq | NM_199011.1 | chr5:108647043-108660769 |
| 5917 | Dgkz | NM_001166597.1 | chr2:91932826-91950348 |
| 5918 | Dguok | NM_001162521.1 | chr6:83480213-83506969 |
| 5919 | Dhcr24 | NM_053272.2 | chr4:106561037-106589113 |
| 5920 | Dhcr7 | NM_007856.2 | chr7:143823166-143848410 |
| 5921 | Dhdds | NM_026144.4 | chr4:133969056-134000864 |
| 5922 | Dhdh | NM_027903.3 | chr7:45473562-45488796 |
| 5923 | Dhfr | NM_010049.3 | chr13:92354782-92389053 |
| 5924 | Dhh | NM_007874.4 | chr15:98893026-98898540 |
| 5925 | Dhodh | NM_020046.3 | chr8:109593247-109608673 |
| 5926 | Dhps | NM_001039514.1 | chr8:85071756-85075161 |
| 5927 | Dhrs1 | NM_026819.2 | chr14:55739019-55745684 |
| 5928 | Dhrs11 | NM_177564.5 | chr11:84820727-84829003 |
| 5929 | Dhrs13 | NM_183286.2 | chr11:78032312-78037864 |
| 5930 | Dhrs2 | NM_175512.2 | chr14:55222006-55241440 |
| 5931 | Dhrs3 | NM_001172424.1 | chr4:144892826-144927645 |
| 5932 | Dhrs4 | NM_001037938.2 | chr14:55478757-55490340 |
| 5933 | Dhrs7 | NM_025522.5 | chr12:72650352-72664828 |
| 5934 | Dhrs7b | NM_001172112.1 | chr11:60830630-60858423 |
| 5935 | Dhrs7c | NM_001013013.2 | chr11:67798270-67816002 |
| 5936 | Dhrs9 | NM_175512.2 | chr2:69380461-69403086 |
| 5937 | Dhrsx | NM_001033326.2 | chr4_GL456216_random:158 80-36213 |
| 5938 | Dhtkd1 | NM_001081131.2 | chr2:5898059-5942792 |
| 5939 | Dhx15 | NM_001042620.2 | chr5:52153323-52190546 |
| 5940 | Dhx16 | NM_026987.2 | chr17:35879777-35892668 |
| 5941 | Dhx29 | NM_172594.2 | chr13:112927792-112969187 |
| 5942 | Dhx30 | NM_001252682.1 | chr9:110084318-110117616 |
| 5943 | Dhx32 | NM_001286030.1 | chr7:133720934-133760269 |
| 5944 | Dhx33 | NM_178367.4 | chr11:70984090-71004432 |
| 5945 | Dhx34 | NM_001285931.1 | chr7:16197220-16221993 |
| 5946 | Dhx35 | NM_001291144.1 | chr2:158794806-158858220 |
| 5947 | Dhx36 | NM_028136.2 | chr3:62468641-62506988 |
| 5948 | Dhx37 | NM_203319.3 | chr5:125414403-125434048 |
| 5949 | Dhx38 | NM_178360.1 | chr8:109548023-109565601 |
| 5950 | Dhx40 | NM_026191.2 | chr11:86768848-86807660 |
| 5951 | Dhx57 | NM_001163759.1 | chr17:80238303-80290476 |
| 5952 | Dhx58 | NM_030150.2 | chr11:100694883-100704271 |
| 5953 | Dhx8 | NM_144831.2 | chr11:101732955-101767357 |
| 5954 | Dhx9 | NM_007842.2 | chr1:153455757-153487660 |
| 5955 | Diablo | NM_023232.3 | chr5:123511329-123524164 |
| 5956 | Diap1 | NM_007858.3 | chr18:37843600-37935423 |
| 5957 | Diap2 | NM_172493.2 | chrX:129749741-130465833 |
| 5958 | Diap3 | NM_019670.1 | chr14:86656322-87141114 |
| 5959 | Dicer1 | NM_148948.2 | chr12:104687741-104751952 |
| 5960 | Dido1 | NM_001291432.1 | chr2:180680953-180709999 |
| 5961 | Diexf | NM_145415.2 | chr1:193104402-193130251 |
| 5962 | Dimt1 | NM_025447.4 | chr13:106947128-106960224 |
| 5963 | Dio1 | NM_007860.3 | chr4:107291464-107307143 |
| 5964 | Dio2 | NM_010050.2 | chr12:90724551-90738438 |
| 5965 | Dio3 | NM_172119.2 | chr12:110279229-110281097 |
| 5966 | Dio3os | NR_002866.2 | chr12:110275384-110278068 |
| 5967 | Dip2a | NM_001081419.2 | chr10:76263048-76345291 |
| 5968 | Dip2b | NM_001159361.1 | chr15:100038663-100219473 |
| 5969 | Dip2c | NM_001081426.2 | chr13:9276524-9668926 |
| 5970 | Diras1 | NM_145217.2 | chr10:81019589-81025377 |
| 5971 | Diras2 | NM_001024474.2 | chr13:52504374-52530836 |
| 5972 | Dirc2 | NM_153550.3 | chr16:35694902-35769356 |
| 5973 | Dis3 | NM_028315.2 | chr14:99076633-99099770 |
| 5974 | Dis3l | NM_001001295.2 | chr9:64306755-64341257 |
| 5975 | Dis3l2 | NM_001172157.1 | chr1:86703803-87050097 |
| 5976 | Disc1 | NM_174853.2 | chr8:125054194-125261151 |
| 5977 | Disp1 | NM_001278218.1 | chr1:183086263-183221529 |
| 5978 | Disp2 | NM_170593.3 | chr2:118779718-118795175 |
| 5979 | Dixdc1 | NM_178118.2 | chr9:50662752-50727984 |
| 5980 | Dkc1 | NM_001030307.2 | chrX:75095853-75109776 |
| 5981 | Dkk1 | NM_010051.3 | chr19:30545884-30549496 |
| 5982 | Dkk2 | NM_020265.4 | chr3:132085291-132180304 |
| 5983 | Dkk3 | NM_015814.2 | chr7:112116018-112159057 |
| 5984 | Dkk4 | NM_145592.2 | chr8:22624042-22627546 |
| 5985 | Dkkl1 | NM_015789.3 | chr7:45207524-45211883 |
| 5986 | Dlat | NM_145614.4 | chr9:50634632-50659780 |
| 5987 | Dlc1 | NM_001194940.2 | chr8:36567738-36952442 |
| 5988 | Dld | NM_007861.5 | chr12:31331561-31351471 |
| 5989 | Dlec1 | NM_177117.3 | chr9:119102477-119147694 |
| 5990 | Dleu2 | NR_028264.1 | chr14:61602835-61682373 |
| 5991 | Dleu7 | NM_173419.2 | chr14:62276228-62292979 |
| 5992 | Dlg1 | NM_001252433.1 | chr16:31663934-31873356 |
| 5993 | Dlg2 | NM_001243046.1 | chr7:92062393-92449246 |
| 5994 | Dlg3 | NM_001177778.2 | chrX:100767721-100818410 |
| 5995 | Dlg4 | NM_001109752.1 | chr11:70018804-70045531 |
| 5996 | Dlg5 | NM_001163513.1 | chr14:24133952-24245920 |
| 5997 | Dlgap1 | NM_001128180.1 | chr17:70522109-70821413 |
| 5998 | Dlgap2 | NM_001145965.1 | chr8:14095874-14847686 |
| 5999 | Dlgap3 | NM_198618.5 | chr4:127169203-127237022 |
| 6000 | Dlgap4 | NM_001042487.1 | chr2:156721278-156764363 |
| 6001 | Dlgap5 | NM_144553.2 | chr14:47387778-47418407 |
| 6002 | Dlk1 | NM_001190703.1 | chr12:109453454-109463336 |
| 6003 | Dlk2 | NM_001286013.1 | chr17:46297927-46303271 |
| 6004 | Dll1 | NM_007865.3 | chr17:15367353-15375823 |
| 6005 | Dll3 | NM_007866.2 | chr7:28293554-28301785 |
| 6006 | Dll4 | NM_019454.3 | chr2:119325783-119335666 |
| 6007 | Dlst | NM_030225.4 | chr12:85110832-85134091 |
| 6008 | Dlx1 | NM_010053.2 | chr2:71529444-71533981 |
| 6009 | Dlx1as | NR_002854.2 | chr2:71530637-71537891 |
| 6010 | Dlx2 | NM_010054.2 | chr2:71534407-71546754 |
| 6011 | Dlx3 | NM_010055.3 | chr11:95120116-95125291 |
| 6012 | Dlx4 | NM_007867.4 | chr11:95140446-95145801 |
| 6013 | Dlx5 | NM_010056.3 | chr6:6877800-6882068 |
| 6014 | Dlx6 | NM_010057.2 | chr6:6863333-6867970 |
| 6015 | Dlx6as2 | NR_002839.2 | chr6:6863796-6865150 |
| 6016 | Dlx6os1 | NR_015388.1 | chr6:6820545-6869533 |
| 6017 | Dmap1 | NM_023178.2 | chr4:117674685-117682225 |
| 6018 | Dmbt1 | NM_007769.2 | chr7:131032075-131121628 |
| 6019 | Dmbx1 | NM_001025567.1 | chr4:115915118-115939926 |
| 6020 | Dmc1 | NM_001278226.1 | chr15:79561497-79605109 |
| 6021 | Dmd | NM_007868.6 | chrX:82948869-85205050 |
| 6022 | Dmgdh | NM_028772.3 | chr13:93674435-93752823 |
| 6023 | Dmkn | NM_001166173.1 | chr7:30763755-30781066 |
| 6024 | Dmp1 | NM_016779.2 | chr5:104202616-104214102 |
| 6025 | Dmpk | NM_001190490.1 | chr7:19083848-19093820 |
| 6026 | Dmr | NR_102372.1 | chr5:144358524-144361005 |
| 6027 | Dmrt1 | NM_015826.5 | chr19:25505705-25604328 |
| 6028 | Dmrt2 | NM_145831.3 | chr19:25672410-25678991 |
| 6029 | Dmrt3 | NM_177360.3 | chr19:25610536-25623921 |
| 6030 | Dmrta1 | NM_177647.3 | chr4:89688197-89694766 |
| 6031 | Dmrta2 | NM_172296.2 | chr4:109978024-109983684 |
| 6032 | Dmrtb1 | NM_019872.1 | chr4:107676289-107684162 |
| 6033 | Dmrtc1a | NM_001038616.2 | chrX:102903220-102906557 |
| 6034 | Dmrtc1b | NM_001039116.2 | chrX:102707880-102715209 |
| 6035 | Dmrtc1c2 | NM_001142690.2 | chrX:102802962-102854616 |
| 6036 | Dmrtc2 | NM_027732.2 | chr7:24870056-24877651 |
| 6037 | Dmtf1 | NM_001110327.1 | chr5:9118867-9161776 |
| 6038 | Dmtn | NM_001252662.1 | chr14:70602183-70627065 |
| 6039 | Dmwd | NM_010058.2 | chr7:19076199-19082775 |
| 6040 | Dmxl1 | NM_001081371.2 | chr18:49832996-49965473 |
| 6041 | Dmxl2 | NM_172771.2 | chr9:54365157-54501626 |
| 6042 | Dna2 | NM_177372.3 | chr10:62947028-62974188 |
| 6043 | Dnaaf1 | NM_026648.4 | chr8:119575234-119598454 |
| 6044 | Dnaaf2 | NM_027269.4 | chr12:69189086-69198429 |
| 6045 | Dnaaf3 | NM_001033548.2 | chr7:4522956-4532442 |
| 6046 | Dnah1 | NM_001033668.1 | chr14:31260374-31323896 |
| 6047 | Dnah10 | NM_019536.1 | chr5:124725084-124834308 |
| 6048 | Dnah11 | NM_010060.3 | chr12:117877981-118199043 |
| 6049 | Dnah17 | NM_001167746.1 | chr11:118021722-118129219 |
| 6050 | Dnah2 | NM_001081330.1 | chr11:69420808-69549108 |
| 6051 | Dnah5 | NM_133365.3 | chr15:28203765-28472045 |
| 6052 | Dnah6 | NM_001164669.1 | chr6:73017606-73221631 |
| 6053 | Dnah7a | NM_001252070.1 | chr1:53397001-53706784 |
| 6054 | Dnah7b | NM_001160386.1 | chr1:46066737-46373550 |
| 6055 | Dnah8 | NM_013811.3 | chr17:30626935-30875264 |
| 6056 | Dnah9 | NM_001099633.1 | chr11:65831523-66168551 |
| 6057 | Dnaic1 | NM_175138.4 | chr4:41569793-41638158 |
| 6058 | Dnaic2 | NM_001034878.2 | chr11:114727411-114757886 |
| 6059 | Dnaja1 | NM_001164671.2 | chr4:40722921-40734965 |
| 6060 | Dnaja2 | NM_019794.4 | chr8:85537639-85555271 |
| 6061 | Dnaja3 | NM_001135112.1 | chr16:4684069-4707693 |
| 6062 | Dnaja4 | NM_021422.4 | chr9:54699558-54716317 |
| 6063 | Dnajb1 | NM_018808.3 | chr8:83608174-83612653 |
| 6064 | Dnajb11 | NM_001190804.1 | chr16:22857844-22872465 |
| 6065 | Dnajb12 | NM_019965.2 | chr10:59879590-59898016 |
| 6066 | Dnajb13 | NM_153527.2 | chr7:100503019-100514815 |
| 6067 | Dnajb14 | NM_001033155.1 | chr3:137867674-137908931 |
| 6068 | Dnajb2 | NM_001159883.1 | chr1:75236422-75245692 |
| 6069 | Dnajb3 | NM_008299.3 | chr1:88204731-88205748 |
| 6070 | Dnajb4 | NM_025926.4 | chr3:152183870-152193845 |
| 6071 | Dnajb5 | NM_019874.3 | chr4:42953093-42958732 |
| 6072 | Dnajb6 | NM_001037940.4 | chr5:29735897-29786478 |
| 6073 | Dnajb7 | NM_021317.2 | chr15:81407087-81408273 |
| 6074 | Dnajb8 | NM_019964.1 | chr6:88222267-88223256 |

Fig. 26 - 33

| | | | |
|---|---|---|---|
| 6075 | Dnajb9 | NM_013760.4 | chr12:44205896-44210068 |
| 6076 | Dnajc1 | NM_001190817.1 | chr2:18206332-18392630 |
| 6077 | Dnajc10 | NM_024181.2 | chr2:80315465-80354055 |
| 6078 | Dnajc11 | NM_172704.1 | chr4:151933719-151981959 |
| 6079 | Dnajc12 | NM_001253685.1 | chr10:63382442-63408840 |
| 6080 | Dnajc13 | NM_001163026.1 | chr9:104151596-104262930 |
| 6081 | Dnajc14 | NM_028873.4 | chr10:128805675-128819446 |
| 6082 | Dnajc15 | NM_025384.3 | chr14:77826216-77874917 |
| 6083 | Dnajc16 | NM_172338.2 | chr4:141761997-141790644 |
| 6084 | Dnajc17 | NM_139139.2 | chr2:119172499-119208795 |
| 6085 | Dnajc18 | NM_029669.4 | chr18:35671104-35703144 |
| 6086 | Dnajc19 | NM_001026211.2 | chr3:34057279-34081354 |
| 6087 | Dnajc2 | NM_009584.4 | chr5:21757276-21785165 |
| 6088 | Dnajc21 | NM_030046.2 | chr15:10446762-10470516 |
| 6089 | Dnajc22 | NM_176835.2 | chr15:99099483-99104707 |
| 6090 | Dnajc24 | NM_026992.3 | chr2:105966707-108003549 |
| 6091 | Dnajc25 | NM_001033165.3 | chr4:59003192-59023398 |
| 6092 | Dnajc27 | NM_153082.4 | chr12:4082573-4110612 |
| 6093 | Dnajc28 | NM_001099738.1 | chr16:91614256-91618999 |
| 6094 | Dnajc3 | NM_008929.3 | chr14:118937931-118981702 |
| 6095 | Dnajc30 | NM_025362.3 | chr5:135064205-135065365 |
| 6096 | Dnajc4 | NM_020566.1 | chr19:6987910-6992272 |
| 6097 | Dnajc5 | NM_001271584.1 | chr2:181520484-181552880 |
| 6098 | Dnajc5b | NM_001163536.1 | chr3:19508594-19610862 |
| 6099 | Dnajc5g | NM_177677.3 | chr5:31108318-31112524 |
| 6100 | Dnajc6 | NM_001164583.1 | chr4:101550593-101642799 |
| 6101 | Dnajc7 | NM_019795.4 | chr11:100582835-100620168 |
| 6102 | Dnajc8 | NM_172400.3 | chr4:132535558-132553742 |
| 6103 | Dnajc9 | NM_134081.5 | chr14:20384637-20388910 |
| 6104 | Dnal1 | NM_028821.3 | chr12:84114327-84143510 |
| 6105 | Dnal4 | NM_010099738.1 | chr15:79761448-79774467 |
| 6106 | Dnali1 | NM_175223.4 | chr4:125055338-125065657 |
| 6107 | Dnase1 | NM_010061.5 | chr16:4037144-4040024 |
| 6108 | Dnase1l1 | NM_001172154.1 | chrX:74273216-74282333 |
| 6109 | Dnase1l2 | NM_025718.3 | chr17:24440767-24443101 |
| 6110 | Dnase1l3 | NM_007870.3 | chr14:7965189-7994182 |
| 6111 | Dnase2a | NM_010062.3 | chr8:84908623-84911461 |
| 6112 | Dnase2b | NM_019957.4 | chr3:146581372-146615598 |
| 6113 | Dnd1 | NM_173383.1 | chr18:36763670-36766214 |
| 6114 | Dner | NM_152915.1 | chr1:84369838-84696221 |
| 6115 | Dnlz | NM_001139503.1 | chr2:26348117-26352110 |
| 6116 | Dnm1 | NM_010065.3 | chr2:32308470-32353329 |
| 6117 | Dnm1l | NM_001025947.2 | chr16:16312227-16359031 |
| 6118 | Dnm2 | NM_001039520.2 | chr9:21424907-21507146 |
| 6119 | Dnm3 | NM_001038720.1 | chr1:161987301-162478030 |
| 6120 | Dnm3os | NR_002870.2 | chr1:162217622-162225550 |
| 6121 | Dnmbp | NM_028029.4 | chr19:43846814-43940198 |
| 6122 | Dnmt1 | NM_001199431.1 | chr9:20907205-20952979 |
| 6123 | Dnmt3a | NM_001271753.1 | chr12:3807159-3914443 |
| 6124 | Dnmt3aos | NR_045884.1 | chr12:3859292-3862244 |
| 6125 | Dnmt3b | NM_001003960.4 | chr2:153649448-153687730 |
| 6126 | Dnmt3l | NM_001081695.2 | chr10:78042286-78063622 |
| 6127 | Dnpep | NM_001100565.1 | chr1:75308564-75317637 |
| 6128 | Dnph1 | NM_207161.3 | chr17:46496788-46499618 |
| 6129 | Dntt | NM_001043228.1 | chr19:41029274-41059525 |
| 6130 | Dnttip1 | NM_133763.1 | chr2:164746014-164768219 |
| 6131 | Dnttip2 | NM_153806.1 | chr3:122274413-122285271 |
| 6132 | Doc2a | NM_010069.1 | chr7:126847552-126852705 |
| 6133 | Doc2b | NM_007873.3 | chr11:75768270-75796060 |
| 6134 | Doc2g | NM_021791.3 | chr19:4003384-4007005 |
| 6135 | Dock1 | NM_001033420.2 | chr7:134670686-135173647 |
| 6136 | Dock10 | NM_001285927.1 | chr1:80501067-80685352 |
| 6137 | Dock11 | NM_001009947.3 | chrX:35888831-36076562 |
| 6138 | Dock2 | NM_033374.3 | chr11:34226820-34783905 |
| 6139 | Dock3 | NM_153413.2 | chr9:106892824-107231909 |
| 6140 | Dock4 | NM_172803.2 | chr12:40446052-40846488 |
| 6141 | Dock5 | NM_177780.3 | chr14:67751927-67933572 |
| 6142 | Dock6 | NM_177030.3 | chr9:108200179-21852635 |
| 6143 | Dock7 | NM_001290636.1 | chr4:98936658-99120915 |
| 6144 | Dock8 | NM_028755.3 | chr19:24999528-25202432 |
| 6145 | Dock9 | NM_001081039.1 | chr14:121542038-121698417 |
| 6146 | Dohh | NM_133964.2 | chr10:81384427-81388352 |
| 6147 | Dok1 | NM_001291799.1 | chr6:83030935-83033471 |
| 6148 | Dok2 | NM_010071.2 | chr14:70774380-70778494 |
| 6149 | Dok3 | NM_013739.2 | chr13:55523234-55528538 |
| 6150 | Dok4 | NM_053246.3 | chr8:94863827-94876312 |
| 6151 | Dok5 | NM_001163686.1 | chr2:170731806-170879775 |
| 6152 | Dok6 | NM_001039173.1 | chr18:89301134-89769136 |
| 6153 | Dok7 | NM_172708.3 | chr5:35057083-35087831 |
| 6154 | Dolk | NM_177648.3 | chr2:30284228-30286354 |
| 6155 | Dolpp1 | NM_001290508.1 | chr2:30392253-30400529 |
| 6156 | Donson | NM_021720.3 | chr16:91679264-91688728 |
| 6157 | Dopey1 | NM_177208.3 | chr9:86467153-86555806 |
| 6158 | Dopey2 | NM_026700.2 | chr16:93711906-93740278 |
| 6159 | Dos | NM_001195268.1 | chr10:80130433-80137387 |
| 6160 | Dot1l | NM_199322.1 | chr10:80755205-80794347 |
| 6161 | Doxl2 | NM_001099987.1 | chr6:48975142-48978745 |
| 6162 | Dpagt1 | NM_007875.2 | chr9:44326844-44333600 |
| 6163 | Dpcd | NM_172839.2 | chr19:45560614-45578287 |
| 6164 | Dpcr1 | NM_001033366.3 | chr17:35635754-35643695 |
| 6165 | Dpep1 | NM_007876.2 | chr8:123186234-123201813 |
| 6166 | Dpep2 | NM_176913.4 | chr8:105984945-105996423 |
| 6167 | Dpep3 | NM_027960.2 | chr8:105973519-105979419 |
| 6168 | Dpf1 | NM_013874.2 | chr7:29304004-29317586 |
| 6169 | Dpf2 | NM_001291078.1 | chr19:5896515-5912871 |

| | | | |
|---|---|---|---|
| 6170 | Dpf3 | NM_001267625.1 | chr12:83213750-83487736 |
| 6171 | Dph1 | NM_144491.2 | chr11:75177642-75190483 |
| 6172 | Dph2 | NM_026344.3 | chr4:117888642-117892003 |
| 6173 | Dph3 | NM_001047433.2 | chr14:32080516-32085692 |
| 6174 | Dph5 | NM_027193.2 | chr3:115888182-115929323 |
| 6175 | Dph6 | NM_025675.4 | chr2:114516417-114654928 |
| 6176 | Dph7 | NM_026044.3 | chr2:24962421-24973471 |
| 6177 | Dpm1 | NM_010072.4 | chr2:168209047-168230379 |
| 6178 | Dpm2 | NM_010073.2 | chr2:32570857-32573571 |
| 6179 | Dpm3 | NM_026767.4 | chr3:89266460-89267079 |
| 6180 | Dpp10 | NM_199021.3 | chr1:123332137-124045559 |
| 6181 | Dpp3 | NM_133803.2 | chr19:4907228-4928287 |
| 6182 | Dpp4 | NM_001159543.1 | chr2:62333222-62412231 |
| 6183 | Dpp6 | NM_001136060.2 | chr5:27261934-27727500 |
| 6184 | Dpp7 | NM_031843.2 | chr2:25352289-25356332 |
| 6185 | Dpp8 | NM_028906.2 | chr9:65032457-65082651 |
| 6186 | Dpp9 | NM_172624.3 | chr17:56186681-56218889 |
| 6187 | Dppa1 | NM_001163358.1 | chr11:46607009-46629274 |
| 6188 | Dppa2 | NM_028615.1 | chr16:48316273-48319513 |
| 6189 | Dppa3 | NM_139218.1 | chr6:122626423-122630271 |
| 6190 | Dppa4 | NM_001018002.1 | chr16:48283734-48294292 |
| 6191 | Dppa5a | NM_025274.3 | chr9:78367053-78368199 |
| 6192 | Dpt | NM_019759.2 | chr1:164796731-164824266 |
| 6193 | Dpy19l1 | NM_172920.4 | chr9:24411778-24503140 |
| 6194 | Dpy19l2 | NM_001166207.1 | chr9:24557047-24696293 |
| 6195 | Dpy19l3 | NM_178704.3 | chr7:35685499-35754454 |
| 6196 | Dpy19l4 | NM_001081201.1 | chr4:11265078-11322131 |
| 6197 | Dpy30 | NM_001146222.1 | chr17:74299473-74316394 |
| 6198 | Dpyd | NM_170778.2 | chr3:118562177-119432918 |
| 6199 | Dpys | NM_001164466.1 | chr15:39782696-39857470 |
| 6200 | Dpysl2 | NM_009955.3 | chr14:66802863-66868600 |
| 6201 | Dpysl3 | NM_001136086.2 | chr18:43320978-43373272 |
| 6202 | Dpysl4 | NM_011993.4 | chr7:139086000-139101791 |
| 6203 | Dpysl5 | NM_023047.2 | chr5:30711894-30799369 |
| 6204 | DQ267100 | NR_046304.1 | chr12:109649616-109649687 |
| 6205 | DQ267101 | NR_046305.1 | chr12:109651423-109651495 |
| 6206 | DQ267102 | NR_046306.1 | chr12:109656344-109656415 |
| 6207 | Dqx1 | NM_033606.3 | chr6:83057843-83067219 |
| 6208 | Dr1 | NM_026106.4 | chr18:268896-108280521 |
| 6209 | Dram1 | NM_027878.2 | chr10:88322803-88357075 |
| 6210 | Dram2 | NM_001025582.2 | chr3:106547797-106575341 |
| 6211 | Drap1 | NM_001291080.1 | chr19:5422803-5424979 |
| 6212 | Draxin | NM_027426.3 | chr4:148098436-148130698 |
| 6213 | Drc1 | NM_001033460.3 | chr5:30341662-30366708 |
| 6214 | Drd1a | NM_001291801.1 | chr13:54051183-54054780 |
| 6215 | Drd2 | NM_010077.2 | chr9:49340661-49407214 |
| 6216 | Drd3 | NM_007877.1 | chr16:43762241-43822839 |
| 6217 | Drd4 | NM_007878.2 | chr7:141292605-141295001 |
| 6218 | Drd5 | NM_013503.3 | chr5:38319508-38322523 |
| 6219 | Dreh | NR_105051.1 | chr17:64767110-64767931 |
| 6220 | Drg1 | NM_007879.1 | chr11:3249921-3266386 |
| 6221 | Drg2 | NM_021354.1 | chr11:60454616-60468705 |
| 6222 | Drosha | NM_001130149.1 | chr15:12824814-12935291 |
| 6223 | Drp2 | NM_010078.3 | chrX:134404779-134456573 |
| 6224 | Dsc1 | NM_001291804.1 | chr18:20083470-20114773 |
| 6225 | Dsc2 | NM_013505.3 | chr18:20030797-20059505 |
| 6226 | Dsc3 | NM_001291809.1 | chr18:19960929-20002097 |
| 6227 | Dscam | NM_031174.4 | chr16:96592078-97170735 |
| 6228 | Dscaml1 | NM_001081270.1 | chr9:45430292-45753713 |
| 6229 | Dscc1 | NM_183089.2 | chr15:55076100-55090478 |
| 6230 | Dscr3 | NM_007834.3 | chr16:94487723-94526629 |
| 6231 | Dse | NM_172508.2 | chr10:34151392-34207551 |
| 6232 | Dsel | NM_001081316.1 | chr1:111858701-111864918 |
| 6233 | Dsg1a | NM_010079.2 | chr18:20310872-20343353 |
| 6234 | Dsg1b | NM_181682.1 | chr18:20376834-20409741 |
| 6235 | Dsg1c | NM_181680.1 | chr18:20247339-20283923 |
| 6236 | Dsg2 | NM_007883.2 | chr18:20558115-20604526 |
| 6237 | Dsg3 | NM_030596.3 | chr18:20510303-20541310 |
| 6238 | Dsg4 | NM_181564.2 | chr18:20436174-20471821 |
| 6239 | Dsn1 | NM_025853.3 | chr2:156995061-157007075 |
| 6240 | Dsp | NM_023842.2 | chr13:38151293-38198577 |
| 6241 | Dspp | NM_010080.2 | chr5:104170711-104180127 |
| 6242 | Dst | NM_001276764.1 | chr1:33908224-34308662 |
| 6243 | Dstn | NM_019771.2 | chr2:143915330-143943324 |
| 6244 | Dstyk | NM_172516.4 | chr1:132417452-132466959 |
| 6245 | Dtd1 | NM_025314.3 | chr2:144599952-144768747 |
| 6246 | Dtd2 | NM_029545.2 | chr12:51997506-52006501 |
| 6247 | Dthd1 | NM_001170705.1 | chr5:62813822-62888318 |
| 6248 | Dtl | NM_029766.3 | chr1:191537355-191575544 |
| 6249 | Dtna | NM_001285807.1 | chr18:23415408-23659719 |
| 6250 | Dtnb | NM_001162465.1 | chr12:3572390-3781398 |
| 6251 | Dtnbp1 | NM_025772.4 | chr13:44922079-45002096 |
| 6252 | Dtwd1 | NM_026981.2 | chr2:126152140-126165277 |
| 6253 | Dtwd2 | NM_001170960.1 | chr18:49696144-49755601 |
| 6254 | Dtx1 | NM_008052.3 | chr5:120680263-120711669 |
| 6255 | Dtx2 | NM_001256096.1 | chr5:135994799-136032880 |
| 6256 | Dtx3 | NM_030714.2 | chr10:127190377-127195709 |
| 6257 | Dtx3l | NM_001013371.2 | chr16:35926514-35939027 |
| 6258 | Dtx4 | NM_172442.3 | chr19:12466335-12501996 |
| 6259 | Dtymk | NM_001105667.1 | chr1:93792575-93801934 |
| 6260 | Duox1 | NM_001099297.1 | chr2:122315671-122347972 |
| 6261 | Duox2 | NM_177610.2 | chr2:122280436-122298165 |
| 6262 | Duoxa1 | NM_001305262.1 | chr2:122303540-122313744 |
| 6263 | Duoxa2 | NM_025777.2 | chr2:122298899-122302885 |
| 6264 | Dusp1 | NM_001013826.2 | chr14:21676571-21714576 |

Fig. 26 - 34

| | | | |
|---|---|---|---|
| 6265 | Dus1l | NM_026824.4 | chr11:120789261-120796395 |
| 6266 | Dus2 | NM_025518.2 | chr8:106011477-106053840 |
| 6267 | Dus3l | NM_144858.2 | chr17:56764750-56770093 |
| 6268 | Dus4l | NM_028002.2 | chr12:31640054-31654826 |
| 6269 | Dusp1 | NM_013642.3 | chr17:26505590-26508472 |
| 6270 | Dusp10 | NM_022019.5 | chr1:184034460-184075636 |
| 6271 | Dusp11 | NM_028099.4 | chr6:85942268-85961667 |
| 6272 | Dusp12 | NM_023173.2 | chr1:170874187-170885540 |
| 6273 | Dusp13 | NM_001007268.1 | chr14:21733394-21748622 |
| 6274 | Dusp14 | NM_019819.3 | chr11:84048044-84068357 |
| 6275 | Dusp15 | NM_001159376.1 | chr2:152940994-152951582 |
| 6276 | Dusp16 | NM_001048054.2 | chr6:134715467-134792628 |
| 6277 | Dusp18 | NM_173745.5 | chr11:3895239-3901296 |
| 6278 | Dusp19 | NM_024438.4 | chr2:80617213-80631661 |
| 6279 | Dusp2 | NM_010090.2 | chr2:127336158-127338377 |
| 6280 | Dusp21 | NM_028568.1 | chrX:18145869-18146692 |
| 6281 | Dusp22 | NM_001037955.4 | chr13:30660058-30711232 |
| 6282 | Dusp23 | NM_026725.2 | chr1:172630768-172632974 |
| 6283 | Dusp26 | NM_025869.3 | chr8:31089661-31097047 |
| 6284 | Dusp27 | NM_001033344.3 | chr1:166098147-166127898 |
| 6285 | Dusp28 | NM_175118.3 | chr1:92906988-92908620 |
| 6286 | Dusp3 | NM_028207.3 | chr11:101971143-101984791 |
| 6287 | Dusp4 | NM_176933.4 | chr8:34807609-34819894 |
| 6288 | Dusp5 | NM_001085390.1 | chr19:53529317-53541322 |
| 6289 | Dusp6 | NM_026268.3 | chr10:99263230-99267489 |
| 6290 | Dusp7 | NM_153459.4 | chr9:106368631-106375723 |
| 6291 | Dusp8 | NM_008748.3 | chr7:142079486-142095284 |
| 6292 | Dusp9 | NM_029352.3 | chrX:73639440-73643514 |
| 6293 | Dut | NM_001159646.1 | chr2:125247247-125259049 |
| 6294 | Dux | NM_001081954.1 | chr10:58230650-58232675 |
| 6295 | Duxbl1 | NM_183389.1 | chr14:25983004-26269100 |
| 6296 | Duxbl2 | NM_001177538.1 | chr14:25983004-26269434 |
| 6297 | Duxbl3 | NM_001177539.1 | chr14:26258303-26269434 |
| 6298 | Dvl1 | NM_010091.4 | chr4:155847316-155859303 |
| 6299 | Dvl2 | NM_007888.3 | chr11:70000625-70010109 |
| 6300 | Dvl3 | NM_007889.2 | chr16:20517063-20532187 |
| 6301 | DXBay18 | NM_001025384.3 | chrX:73117046-73149450 |
| 6302 | Dxo | NM_001163770.1 | chr17:34837018-34839186 |
| 6303 | Dydc1 | NM_027094.1 | chr14:41072910-41092197 |
| 6304 | Dydc2 | NM_027717.1 | chr14:41049208-41069074 |
| 6305 | Dym | NM_027727.2 | chr18:75018771-75286966 |
| 6306 | Dynap | NM_029346.1 | chr18:70240428-70244584 |
| 6307 | Dync1h1 | NM_030238.2 | chr12:110601394-110666944 |
| 6308 | Dync1i1 | NM_001191023.1 | chr6:5725638-6028036 |
| 6309 | Dync1i2 | NM_001198872.1 | chr2:71211705-71263302 |
| 6310 | Dync1li1 | NM_146229.2 | chr9:114688830-114723777 |
| 6311 | Dync1li2 | NM_001013380.2 | chr8:104417673-104443047 |
| 6312 | Dync2h1 | NM_029851.2 | chr9:6928502-7177046 |
| 6313 | Dync2li1 | NM_172256.1 | chr17:84626498-84655564 |
| 6314 | Dynll1 | NM_019682.4 | chr5:115297109-115300990 |
| 6315 | Dynll2 | NM_001168471.1 | chr11:87979524-87998298 |
| 6316 | Dynlrb1 | NM_001291108.1 | chr2:155236607-155250277 |
| 6317 | Dynlrb2 | NM_029297.1 | chr8:116505014-116515915 |
| 6318 | Dynlt1a | NM_001166629.2 | chr17:6306343-6317474 |
| 6319 | Dynlt1b | NM_009342.2 | chr17:6430111-6436295 |
| 6320 | Dynlt1c | NM_001166630.1 | chr17:6601778-6655831 |
| 6321 | Dynlt1f | NM_001166627.1 | chr17:6601670-6655939 |
| 6322 | Dynlt3 | NM_025975.5 | chrX:9654269-9662983 |
| 6323 | Dyrk1a | NM_001113389.1 | chr16:94570906-94695519 |
| 6324 | Dyrk1b | NM_001037957.3 | chr7:28179482-28187298 |
| 6325 | Dyrk2 | NM_001014390.2 | chr10:118859348-118868903 |
| 6326 | Dyrk3 | NM_145508.2 | chr1:131128440-131138234 |
| 6327 | Dyrk4 | NM_207210.2 | chr6:126876198-126921839 |
| 6328 | Dysf | NM_001077694.2 | chr6:84008597-84211059 |
| 6329 | Dytn | NM_001081685.1 | chr1:63622850-63686927 |
| 6330 | Dyx1c1 | NM_001183725.1 | chr9:72958784-72973067 |
| 6331 | Dzank1 | NM_172859.2 | chr2:144470556-144527398 |
| 6332 | Dzip1 | NM_025943.3 | chr14:118875519-118925470 |
| 6333 | Dzip1l | NM_028258.4 | chr9:99629530-99670075 |
| 6334 | Dzip3 | NM_001110017.1 | chr16:48924227-48994112 |
| 6335 | E030002O03Rik | NM_172905.2 | chr7:104153012-104164816 |
| 6336 | E030003E18Rik | NR_015502.1 | chr15:20492714-20566410 |
| 6337 | E030011O05Rik | NR_015511.2 | chr9:96731574-96752831 |
| 6338 | E030013I19Rik | NR_040353.1 | chr2:12301245-12312315 |
| 6339 | E030018B13Rik | NM_001256311.1 | chr7:63916856-63920539 |
| 6340 | E030019B06Rik | NM_001032546.1 | chr7:139600914-139683815 |
| 6341 | E030019B13Rik | NR_045082.1 | chr12:56490427-56529420 |
| 6342 | E030024N20Rik | NR_033228.1 | chr19:16164097-16170458 |
| 6343 | E030025P04Rik | NR_037978.1 | chr11:109139290-109144369 |
| 6344 | E030030B06Rik | NM_001254744.1 | chr10:22113049-22149270 |
| 6345 | E030044B06Rik | NR_045343.1 | chr19:40868315-40882639 |
| 6346 | E030036D01Rik | NR_045832.1 | chr5:111734283-111761728 |
| 6347 | E030008D07Rik | NR_045153.1 | chr7:43149356-43158291 |
| 6348 | E130012A19Rik | NR_175332.3 | chr11:97627386-97629716 |
| 6349 | E130018N17Rik | NR_040277.1 | chr2:168152602-168154513 |
| 6350 | E130102H24Rik | NR_040708.1 | chr4:101346523-101356248 |
| 6351 | E130112N10Rik | NR_015604.2 | chr6:125231275-125239934 |
| 6352 | E130114P18Rik | NR_015513.2 | chr4:97567874-97584591 |
| 6353 | E130201H02Rik | NR_024324.1 | chr7:120597624-120598475 |
| 6354 | E130215H24Rik | NR_040331.1 | chr2:150667493-150668932 |
| 6355 | E130218I03Rik | NR_040435.1 | chr4:134243762-134245873 |
| 6356 | E130304I02Rik | NR_033567.1 | chr7:35802591-35838074 |
| 6357 | E130307A14Rik | NR_038037.1 | chr16:39621410-39732007 |
| 6358 | E130308A19Rik | NM_001015681.2 | chr4:59626210-59754303 |
| 6359 | E130309D02Rik | NM_172726.4 | chr5:143301071-143315360 |
| 6360 | E130309F12Rik | NM_001013784.1 | chr11:74619604-74641516 |
| 6361 | E130309F12Rik | NM_178756.4 | chr4:49059461-49340261 |
| 6362 | E130310I04Rik | NR_045722.1 | chr16:34952025-34958864 |
| 6363 | E130311K13Rik | NM_177856.4 | chr3:63914695-63929385 |
| 6364 | E130317F20Rik | NR_029447.1 | chr10:79851376-79854971 |
| 6365 | E230008N13Rik | NM_198660.2 | chr4:45890302-45950774 |
| 6366 | E230016K23Rik | NR_036452.1 | chr11:83582060-83623693 |
| 6367 | E230016M11Rik | NR_040278.1 | chr6:67036598-67080652 |
| 6368 | E230019M04Rik | NM_177921.3 | chrX:140062878-140106797 |
| 6369 | E230025N22Rik | NM_172831.2 | chr18:36684922-36695925 |
| 6370 | E230029C05Rik | NR_110364.1 | chr7:90029158-90049071 |
| 6371 | E2f1 | NM_001291105.1 | chr2:154559399-154569426 |
| 6372 | E2f2 | NM_177733.7 | chr4:136172273-136196056 |
| 6373 | E2f3 | NM_001289920.1 | chr13:29906574-29984391 |
| 6374 | E2f4 | NM_148952.1 | chr8:105297662-105305370 |
| 6375 | E2f5 | NM_007892.2 | chr3:14578670-14606309 |
| 6376 | E2f6 | NM_033270.2 | chr12:16810964-16826752 |
| 6377 | E2f7 | NM_178609.4 | chr10:110745464-110787384 |
| 6378 | E2f8 | NM_001013368.5 | chr7:48866428-48881041 |
| 6379 | E330009J07Rik | NM_175528.4 | chr6:40407497-40436133 |
| 6380 | E330011O21Rik | NR_045698.1 | chr18:78250862-78255454 |
| 6381 | E330012B07Rik | NR_033640.1 | chr6:147180240-147208294 |
| 6382 | E330013P04Rik | NM_026942.1 | chr19:60144674-60162591 |
| 6383 | E330014E10Rik | NM_001122668.1 | chr5:82563-95804230 |
| 6384 | E330017A01Rik | NM_175011.2 | chr16:58635261-58638403 |
| 6385 | E330017L17Rik | NR_045190.2 | chr4:129906225-129908996 |
| 6386 | E330020D12Rik | NR_033736.1 | chr1:153404185-153414233 |
| 6387 | E330021D16Rik | NM_001201390.1 | chr6:136400318-136415569 |
| 6388 | E330023G01Rik | NR_045332.1 | chr9:98748598-98820087 |
| 6389 | E330033B04Rik | NR_030690.1 | chr15:96268563-96275275 |
| 6390 | E330034G19Rik | NM_001033214.2 | chr14:24293363-24309959 |
| 6391 | E430016F16Rik | NR_015542.1 | chr7:78581065-78718220 |
| 6392 | E430018J23Rik | NM_198011.2 | chr7:127390835-127393621 |
| 6393 | E430025E21Rik | NM_153548.2 | chr15:59393996-59374352 |
| 6394 | E4f1 | NM_007893.4 | chr17:24443777-24455392 |
| 6395 | E530001K10Rik | NR_002167.2 | chrX:105184377-105165505 |
| 6396 | E530011L22Rik | NR_033503.1 | chr9:121756639-121759943 |
| 6397 | Eaf1 | NM_028932.4 | chr14:31495078-31509858 |
| 6398 | Eaf2 | NM_001113401.1 | chr16:36792883-36828259 |
| 6399 | Eapp | NM_025456.3 | chr12:54673646-54695865 |
| 6400 | Ear1 | NM_007894.2 | chr14:43818764-43819639 |
| 6401 | Ear10 | NM_053112.1 | chr14:43922897-43923368 |
| 6402 | Ear14 | NM_017389.2 | chr14:51203694-51204156 |
| 6403 | Ear2 | NM_007895.2 | chr14:44102653-44103531 |
| 6404 | Ear3 | NM_017388.1 | chr14:44102886-44103357 |
| 6405 | Ear4 | NM_001017422.1 | chr14:51203689-51204156 |
| 6406 | Ear6 | NM_053111.2 | chr14:51853767-51854642 |
| 6407 | Ear7 | NM_017385.1 | chr14:51853997-51854465 |
| 6408 | Ears2 | NM_026140.3 | chr7:122034161-122067086 |
| 6409 | Ebag9 | NM_019480.4 | chr15:44619640-44641026 |
| 6410 | Ebf1 | NM_001290709.1 | chr11:44618099-45008096 |
| 6411 | Ebf2 | NM_001276387.1 | chr14:67233291-67430952 |
| 6412 | Ebf3 | NM_001113414.1 | chr7:137193670-137314445 |
| 6413 | Ebf4 | NM_001110513.1 | chr2:130295938-130370481 |
| 6414 | Ebi3 | NM_015766.2 | chr17:55952622-55957022 |
| 6415 | Ebna1bp2 | NM_026932.4 | chr4:118620798-118627776 |
| 6416 | Ebp | NM_007898.3 | chrX:8185328-8193512 |
| 6417 | Ebpl | NM_026598.3 | chr14:61339762-61360445 |
| 6418 | Ecd | NM_027475.3 | chr14:20319858-20348121 |
| 6419 | Ece1 | NM_199307.2 | chr4:137862236-137965229 |
| 6420 | Ece2 | NM_025462.2 | chr16:20611600-20618869 |
| 6421 | Ecel1 | NM_001277925.1 | chr1:87147654-87156136 |
| 6422 | Ech1 | NM_016772.1 | chr7:28825337-28832239 |
| 6423 | Echdc1 | NM_001110195.1 | chr10:29313165-29346661 |
| 6424 | Echdc2 | NM_001254754.1 | chr4:108165436-108179308 |
| 6425 | Echdc3 | NM_024208.4 | chr2:6188464-6212994 |
| 6426 | Echs1 | NM_053119.2 | chr7:140105722-140116423 |
| 6427 | Eci1 | NM_010023.4 | chr17:24426682-24439316 |
| 6428 | Eci2 | NM_001110331.1 | chr13:34977747-34994144 |
| 6429 | Eci3 | NM_026947.4 | chr13:34946613-34963809 |
| 6430 | Ecm1 | NM_001252653.1 | chr3:95734147-95739569 |
| 6431 | Ecm2 | NM_001012224.2 | chr13:49504809-49532789 |
| 6432 | Ecscr | NM_001033141.1 | chr18:35713088-35721491 |
| 6433 | Ecsit | NM_001253897.1 | chr9:22072245-22085427 |
| 6434 | Ect2 | NM_001177625.1 | chr3:27097221-27153854 |
| 6435 | Ect2l | NM_001195036.1 | chr10:18129621-18210890 |
| 6436 | Eda | NM_001177937.1 | chrX:99975605-100400760 |
| 6437 | Eda2r | NM_001161432.1 | chrX:97333840-97377209 |
| 6438 | Edar | NM_010190.3 | chr10:58600787-58675696 |
| 6439 | Edaradd | NM_133643.4 | chr13:12471208-12520450 |
| 6440 | Edc3 | NM_153799.3 | chr9:57708568-57750162 |
| 6441 | Edc4 | NM_181594.3 | chr8:105880880-105893225 |
| 6442 | Eddm3b | NM_203508.1 | chr14:51116552-51117791 |
| 6443 | Edem1 | NM_138677.2 | chr6:108828640-108859356 |
| 6444 | Edem2 | NM_145537.2 | chr2:155701672-155729475 |
| 6445 | Edem3 | NM_010039644.2 | chr1:151755373-151822328 |
| 6446 | Edf1 | NM_021519.1 | chr2:25557899-25562082 |
| 6447 | Edil3 | NM_001037987.1 | chr13:88821471-89323225 |
| 6448 | Edn1 | NM_010104.3 | chr13:42301289-42307989 |
| 6449 | Edn2 | NM_007902.2 | chr4:120161423-120167360 |
| 6450 | Edn3 | NM_007903.4 | chr2:174760757-174784042 |
| 6451 | Ednra | NM_010332.2 | chr8:77663028-77724452 |
| 6452 | Ednrb | NM_001136061.2 | chr14:103814614-103844476 |
| 6453 | Edrf1 | NM_178115.4 | chr7:133637674-133673017 |
| 6454 | Eea1 | NM_001001932.3 | chr10:95940662-96045518 |

Fig. 26 - 35

| | | | |
|---|---|---|---|
| 6455 | Eed | NM_021876.3 | chr7:89954653-89980976 |
| 6456 | Eef1a1 | NM_010106.2 | chr9:78478453-78481724 |
| 6457 | Eef1a2 | NM_007906.2 | chr2:181147691-181157015 |
| 6458 | Eef1b2 | NM_018796.3 | chr1:63176830-63180486 |
| 6459 | Eef1d | NM_001285429.1 | chr15:75894796-75909556 |
| 6460 | Eef1e1 | NM_025380.2 | chr13:38645690-38659028 |
| 6461 | Eef1g | NM_026007.4 | chr19:8967040-8978180 |
| 6462 | Eef2 | NM_007907.2 | chr10:81176630-81182509 |
| 6463 | Eef2k | NM_001267710.1 | chr7:120843599-120907219 |
| 6464 | Eefsec | NM_023060.3 | chr6:88257333-88446539 |
| 6465 | Eepd1 | NM_026189.3 | chr9:25481596-25604110 |
| 6466 | Efcab1 | NM_025769.3 | chr16:14906646-14924522 |
| 6467 | Efcab10 | NM_029152.1 | chr12:33394853-33401269 |
| 6468 | Efcab11 | NM_030172.2 | chr12:99717536-99883442 |
| 6469 | Efcab12 | NM_001110506.1 | chr6:115810728-115838412 |
| 6470 | Efcab14 | NM_172986.2 | chr4:115738072-115777327 |
| 6471 | Efcab2 | NM_026626.2 | chr1:178405880-178483249 |
| 6472 | Efcab3 | NM_001081046.1 | chr11:105092218-105117537 |
| 6473 | Efcab4a | NM_001025103.2 | chr7:141461093-141466602 |
| 6474 | Efcab4b | NM_001033464.3 | chr6:127577974-127629938 |
| 6475 | Efcab5 | NM_176965.3 | chr11:77089914-77188968 |
| 6476 | Efcab6 | NM_001161628.1 | chr15:83866711-83936095 |
| 6477 | Efcab7 | NM_145549.1 | chr4:99829499-99912783 |
| 6478 | Efcab8 | NR_036629.1 | chr2:153780878-153795182 |
| 6479 | Efcab9 | NM_027031.3 | chr1:32522732-32527574 |
| 6480 | Efcc1 | NM_001159697.1 | chr6:87730868-87755911 |
| 6481 | Efcc1 | NM_146015.2 | chr11:28853204-28926743 |
| 6482 | Efemp1 | NM_001164352.1 | chr19:5474734-5481854 |
| 6483 | Efemp2 | NM_172497.3 | chr17:53398888-53463321 |
| 6484 | Efhb | NM_027974.1 | chr1:20951625-20990841 |
| 6485 | Efhc1 | NM_028916.4 | chrX:17132048-17319368 |
| 6486 | Efhc2 | NM_028889.2 | chr1:87264363-87310791 |
| 6487 | Efhd1 | NM_025994.3 | chr4:141858141-141874920 |
| 6488 | Efhd2 | NM_001162425.1 | chr3:89217729-89280951 |
| 6489 | Efna1 | NM_007909.3 | chr10:80179481-80190010 |
| 6490 | Efna2 | NM_010108.1 | chr3:89314950-89322879 |
| 6491 | Efna3 | NM_007910.2 | chr3:89333392-89338028 |
| 6492 | Efna4 | NM_010109.3 | chr17:62602956-62881317 |
| 6493 | Efna5 | NM_010110.5 | chrX:99136060-99149022 |
| 6494 | Efnb1 | NM_010111.5 | chr8:8617438-8660773 |
| 6495 | Efnb2 | NM_007911.5 | chr11:69554091-69560237 |
| 6496 | Efnb3 | NM_133766.3 | chr15:65787040-65873812 |
| 6497 | Efr3a | NM_001082483.1 | chr12:3962553-4038915 |
| 6498 | Efr3b | NM_010112.4 | chr14:54916542-54926788 |
| 6499 | Efs | NM_001159671.1 | chr7:82648613-82777852 |
| 6500 | Eftud1 | NM_001109995.1 | chr11:102838471-102880975 |
| 6501 | Eftud2 | NM_010113.4 | chr3:129677576-129755322 |
| 6502 | Egf | NM_010115.6 | chr7:44012696-44016968 |
| 6503 | Egfbp2 | NM_001167748.1 | chr3:29082576-29691056 |
| 6504 | Egfem1 | NM_019397.3 | chrX:166523006-166585716 |
| 6505 | Egfl6 | NM_001164564.1 | chr2:26586629-26592682 |
| 6506 | Egfl7 | NM_152922.3 | chr17:34613349-34615971 |
| 6507 | Egfl8 | NM_001289496.1 | chr15:7206119-7398390 |
| 6508 | Egflam | NM_007912.4 | chr11:16752202-16887658 |
| 6509 | Egfr | NM_053207.2 | chr8:124908586-124949254 |
| 6510 | Egln1 | NM_053208.4 | chr7:27158657-27166802 |
| 6511 | Egln2 | NM_028133.2 | chr12:54178980-54203874 |
| 6512 | Egln3 | NM_007913.5 | chr18:34861206-34864956 |
| 6513 | Egr1 | NM_010114.3 | chr10:67537868-67542168 |
| 6514 | Egr2 | NM_001289925.1 | chr14:70077444-70082613 |
| 6515 | Egr3 | NM_020596.2 | chr6:85511121-85513542 |
| 6516 | Egr4 | NM_001252515.1 | chr11:22005825-22286795 |
| 6517 | Ehbp1 | NM_001114595.1 | chr19:5707373-5726317 |
| 6518 | Ehbp1l1 | NM_010119.5 | chr19:6276895-6300096 |
| 6519 | Ehd1 | NM_153068.3 | chr17:15948986-15967535 |
| 6520 | Ehd2 | NM_020578.3 | chr17:73804840-73832093 |
| 6521 | Ehd3 | NM_133838.4 | chr2:120089486-120154575 |
| 6522 | Ehd4 | NM_007914.5 | chr2:103263432-103303196 |
| 6523 | Ehf | NM_023737.3 | chr16:21761284-21787834 |
| 6524 | Ehhadh | NM_001167518.3 | chr2:24790768-24919609 |
| 6525 | Ehmt1 | NM_001286573.1 | chr17:34898973-34914050 |
| 6526 | Ehmt2 | NM_001199494.1 | chr9:36779152-36797393 |
| 6527 | Ei24 | NM_025613.3 | chr7:28253099-125675642 |
| 6528 | Eid1 | NM_198425.2 | chr7:28267880-28269168 |
| 6529 | Eid2 | NM_001177427.1 | chr7:28277705-28280129 |
| 6530 | Eid2b | NM_025499.2 | chr7:10:82866625-82867929 |
| 6531 | Eid3 | NM_011508.1 | chr11:100319995-100322096 |
| 6532 | Eif1 | NM_010120.5 | chr18:46597703-46610225 |
| 6533 | Eif1a | NM_027236.2 | chr19:5368672-5371511 |
| 6534 | Eif1ad | NM_025437.4 | chrX:159372194-159385699 |
| 6535 | Eif1ax | NM_026892.3 | chr9:120492605-120495327 |
| 6536 | Eif1b | NM_001010023.2 | chr3:58525820-58557501 |
| 6537 | Eif2a | NM_013557.2 | chr5:143871861-143902717 |
| 6538 | Eif2ak1 | NM_011163.4 | chr17:78852549-78882572 |
| 6539 | Eif2ak2 | NM_010121.3 | chr17:70844514-70905241 |
| 6540 | Eif2ak3 | NM_001177806.1 | chr2:118389111-118475234 |
| 6541 | Eif2ak4 | NM_145371.4 | chr5:124570213-124579131 |
| 6542 | Eif2b1 | NM_145445.4 | chr12:85219480-85226628 |
| 6543 | Eif2b2 | NM_001111277.1 | chr4:117019407-117086852 |
| 6544 | Eif2b3 | NM_001127355.1 | chr5:31187557-31193139 |
| 6545 | Eif2b4 | NM_172265.2 | chr16:20498816-20509325 |
| 6546 | Eif2b5 | NM_001136070.1 | chr1:131153206-131173471 |
| 6547 | Eif2d | NM_026114.3 | chr12:78862071-78887010 |
| 6548 | Eif2s1 | NM_026030.2 | chr2:154871409-154892906 |
| 6549 | Eif2s2 | NM_012010.3 | chrX:94188708-94212651 |
| 6550 | Eif2s3x | NM_012011.1 | chrY:1010611-1028598 |
| 6551 | Eif2s3y | NM_010123.3 | chr19:60761115-60790693 |
| 6552 | Eif3a | NM_133916.2 | chr5:140419304-140443358 |
| 6553 | Eif3b | NM_146200.1 | chr7:126546910-126566366 |
| 6554 | Eif3c | NM_018749.2 | chr15:77958997-77970824 |
| 6555 | Eif3d | NM_008388.2 | chr15:43250039-43282736 |
| 6556 | Eif3e | NM_025344.2 | chr7:108934414-108941942 |
| 6557 | Eif3f | NM_016876.3 | chr9:20894348-20898590 |
| 6558 | Eif3g | NM_080635.1 | chr15:51786562-51865461 |
| 6559 | Eif3h | NM_018799.2 | chr4:129591973-129600648 |
| 6560 | Eif3i | NM_144545.4 | chr2:122028579-122053632 |
| 6561 | Eif3j2 | NM_001256055.1 | chr2:122028582-122053631 |
| 6562 | Eif3k | NM_001285942.1 | chr7:28971371-28981888 |
| 6563 | Eif3l | NM_145139.2 | chr15:79075222-79094400 |
| 6564 | Eif3m | NM_145380.2 | chr2:104999656-105017027 |
| 6565 | Eif4a1 | NM_001159375.1 | chr11:69666935-69672423 |
| 6566 | Eif4a2 | NM_001123037.2 | chr16:23107467-23114132 |
| 6567 | Eif4a3 | NM_138669.1 | chr11:119288362-119300043 |
| 6568 | Eif4b | NM_145625.3 | chr15:102073772-102097173 |
| 6569 | Eif4e | NM_007917.4 | chr3:138526190-138559696 |
| 6570 | Eif4e1b | NM_001033269.3 | chr13:54783997-54788458 |
| 6571 | Eif4e2 | NM_001039169.1 | chr1:87213938-87228858 |
| 6572 | Eif4e3 | NM_025829.4 | chr6:99625136-99666771 |
| 6573 | Eif4ebp1 | NM_007918.3 | chr8:27260326-27275656 |
| 6574 | Eif4ebp2 | NM_010124.2 | chr10:61432496-61452669 |
| 6575 | Eif4ebp3 | NM_201256.4 | chr18:36664059-36666324 |
| 6576 | Eif4enif1 | NM_001166547.1 | chr11:3202994-3244588 |
| 6577 | Eif4g1 | NM_001304432.1 | chr16:20672720-20692883 |
| 6578 | Eif4g2 | NM_010040131.2 | chr7:111067984-111083030 |
| 6579 | Eif4g3 | NM_001256195.1 | chr4:137993455-138207079 |
| 6580 | Eif4h | NM_033561.2 | chr5:134619871-134639409 |
| 6581 | Eif5 | NM_173363.5 | chr12:111538100-111546753 |
| 6582 | Eif5a | NM_001166589.1 | chr11:69916711-69921386 |
| 6583 | Eif5a2 | NM_177586.5 | chr3:28781310-28798846 |
| 6584 | Eif5b | NM_198303.2 | chr1:37998009-38055579 |
| 6585 | Eif6 | NM_010579.2 | chr2:155819836-155826925 |
| 6586 | Elac1 | NM_053255.3 | chr18:73735037-73754479 |
| 6587 | Elac2 | NM_023479.2 | chr11:64979034-65002076 |
| 6588 | Elane | NM_015779.2 | chr10:79886311-79888216 |
| 6589 | Elavl1 | NM_010485.3 | chr8:4284781-4325100 |
| 6590 | Elavl2 | NM_001177833.1 | chr4:91250766-91376496 |
| 6591 | Elavl3 | NM_010487.2 | chr9:22015004-22052023 |
| 6592 | Elavl4 | NM_001038698.1 | chr4:110203736-110287511 |
| 6593 | Elf1 | NM_001286411.1 | chr14:79515673-79582491 |
| 6594 | Elf2 | NM_001291059.1 | chr3:51252719-51340644 |
| 6595 | Elf3 | NM_001163131.1 | chr1:135253573-135258472 |
| 6596 | Elf4 | NM_019680.2 | chrX:48411048-48463132 |
| 6597 | Elf5 | NM_001145813.1 | chr2:103412097-103450988 |
| 6598 | Elfn1 | NM_175522.3 | chr5:139907942-139974724 |
| 6599 | Elfn2 | NM_183141.2 | chr15:78670006-78718113 |
| 6600 | Elk1 | NM_007922.5 | chrX:20933394-20950608 |
| 6601 | Elk3 | NM_001282967.1 | chr10:93247415-93311159 |
| 6602 | Elk4 | NM_007923.2 | chr1:132007604-132025684 |
| 6603 | Ell | NM_007924.2 | chr8:70539674-70592858 |
| 6604 | Ell2 | NM_138953.2 | chr13:75707483-75772358 |
| 6605 | Ell3 | NM_145973.2 | chr2:121439026-121442691 |
| 6606 | Elmo1 | NM_080288.2 | chr13:20090506-20608353 |
| 6607 | Elmo2 | NM_080287.2 | chr2:165288030-165326479 |
| 6608 | Elmo3 | NM_172760.3 | chr8:105305600-105310623 |
| 6609 | Elmod1 | NM_177769.4 | chr9:53911459-53975301 |
| 6610 | Elmod2 | NM_001170691.1 | chr8:83312631-83332486 |
| 6611 | Elmod3 | NM_001253692.1 | chr6:72565921-72598413 |
| 6612 | Elmsan1 | NM_001163501.1 | chr12:84149173-84218881 |
| 6613 | Eln | NM_007925.4 | chr5:134702594-134747323 |
| 6614 | Elof1 | NM_170777.3 | chr9:22112988-22114169 |
| 6615 | Elovl1 | NM_001039175.2 | chr4:118428092-118432952 |
| 6616 | Elovl2 | NM_019423.2 | chr13:41182381-41220403 |
| 6617 | Elovl3 | NM_007703.2 | chr19:46131898-46135694 |
| 6618 | Elovl4 | NM_148941.2 | chr9:83778691-83806305 |
| 6619 | Elovl5 | NM_134255.3 | chr9:77917364-77984519 |
| 6620 | Elovl6 | NM_130450.2 | chr3:129532385-129638493 |
| 6621 | Elovl7 | NM_029001.5 | chr13:108214403-108287107 |
| 6622 | Elp2 | NM_021448.2 | chr18:24603960-24638830 |
| 6623 | Elp3 | NM_001253812.1 | chr14:65530445-65593112 |
| 6624 | Elp4 | NM_023876.4 | chr2:105697319-105904564 |
| 6625 | Elp5 | NM_001253700.1 | chr11:69968225-69980330 |
| 6626 | Elp6 | NM_001081381.1 | chr9:110305191-110322102 |
| 6627 | Eltd1 | NM_133222.3 | chr3:151437881-151545081 |
| 6628 | Emb | NM_010330.4 | chr13:117220572-117274415 |
| 6629 | Emc1 | NM_001039200.2 | chr4:139352586-139378735 |
| 6630 | Emc10 | NM_197991.2 | chr7:44489937-44496513 |
| 6631 | Emc2 | NM_025736.2 | chr15:43477228-43527777 |
| 6632 | Emc3 | NM_175101.3 | chr6:113514886-113531638 |
| 6633 | Emc4 | NM_026519.3 | chr2:112363018-112368027 |
| 6634 | Emc6 | NM_001168470.1 | chr11:73175502-73177008 |
| 6635 | Emc7 | NM_133749.2 | chr2:112455024-112467436 |
| 6636 | Emc8 | NM_010926.5 | chr8:120653913-120668112 |
| 6637 | Emc9 | NM_033146.1 | chr14:55581523-55585254 |
| 6638 | Emcn | NM_001163522.1 | chr3:137341077-137431069 |
| 6639 | Emd | NM_007927.3 | chrX:74254686-74257893 |
| 6640 | Emel | NM_177752.4 | chr11:94645001-94653754 |
| 6641 | Eme2 | NM_001163102.1 | chr17:24892151-24895087 |
| 6642 | Emg1 | NM_033536.2 | chr6:124704369-124712178 |
| 6643 | Emid1 | NM_080595.2 | chr11:5106265-5152222 |
| 6644 | Emilin1 | NM_133918.2 | chr5:30913785-30921273 |

Fig. 26 - 36

| | | | |
|---|---|---|---|
| 6645 | Emilin2 | NM_145158.3 | chr17:71252175-71310965 |
| 6646 | Emilin3 | NM_001291145.1 | chr2:160906437-160912339 |
| 6647 | Eml1 | NM_001043335.1 | chr12:108422815-108539564 |
| 6648 | Eml2 | NM_001162996.1 | chr7:19181169-19206482 |
| 6649 | Eml3 | NM_144872.1 | chr19:8929693-8941582 |
| 6650 | Eml4 | NM_001114361.1 | chr17:83350930-83480359 |
| 6651 | Eml5 | NM_001081191.1 | chr12:98786603-98901484 |
| 6652 | Eml6 | NM_146016.2 | chr11:29743050-30026033 |
| 6653 | Emp1 | NM_001288627.1 | chr6:135367492-135383173 |
| 6654 | Emp2 | NM_007929.2 | chr16:10281748-10313968 |
| 6655 | Emp3 | NM_001146344.1 | chr7:45918022-45920849 |
| 6656 | Emr1 | NM_010130.4 | chr17:57358685-57483529 |
| 6657 | Emr4 | NM_139138.3 | chr17:55749983-55853662 |
| 6658 | Emx1 | NM_010131.2 | chr6:85187930-85204463 |
| 6659 | Emx2 | NM_010132.2 | chr19:59458689-59465357 |
| 6660 | Emx2os | NR_002883.2 | chr19:59425103-59458655 |
| 6661 | En1 | NM_010133.2 | chr1:120602486-120607991 |
| 6662 | En2 | NM_010134.3 | chr5:28165695-28172166 |
| 6663 | Enah | NM_001083120.2 | chr1:181896385-182019980 |
| 6664 | Enam | NM_017468.3 | chr5:88487974-88506049 |
| 6665 | Enc1 | NM_007930.4 | chr13:97241104-97253040 |
| 6666 | Endod1 | NM_028013.3 | chr9:14353989-14381242 |
| 6667 | Endog | NM_007931.1 | chr2:30171523-30174069 |
| 6668 | Endou | NM_001168693.1 | chr15:97711018-97731405 |
| 6669 | Endov | NM_001164636.1 | chr11:119491346-119511465 |
| 6670 | Eng | NM_001146348.1 | chr2:32646594-32682669 |
| 6671 | Engase | NM_172573.2 | chr11:118476959-118489198 |
| 6672 | Enho | NM_027147.1 | chr4:41638143-41640302 |
| 6673 | Enkd1 | NM_198299.1 | chr8:105703651-105708168 |
| 6674 | Enkur | NM_027728.2 | chr2:21180730-21205365 |
| 6675 | Eno1 | NM_023119.2 | chr4:150237196-150248873 |
| 6676 | Eno1b | NM_001025388.1 | chr4:48045334-150248873 |
| 6677 | Eno2 | NM_013509.3 | chr6:124760052-124769673 |
| 6678 | Eno3 | NM_001136062.2 | chr11:70657175-70662513 |
| 6679 | Eno4 | NM_178689.4 | chr19:58943424-58971421 |
| 6680 | Enoph1 | NM_001163035.1 | chr5:100039993-100068765 |
| 6681 | Enox1 | NM_001253759.1 | chr14:77156762-77721763 |
| 6682 | Enox2 | NM_001271447.1 | chrX:49009706-49288242 |
| 6683 | Enpep | NM_007934.3 | chr3:129269176-129332749 |
| 6684 | Enpp1 | NM_008813.4 | chr10:24637913-24712159 |
| 6685 | Enpp2 | NM_001136077.3 | chr15:54838900-54920146 |
| 6686 | Enpp3 | NM_134005.2 | chr10:24773815-24836195 |
| 6687 | Enpp4 | NM_199016.2 | chr17:44096309-44105808 |
| 6688 | Enpp5 | NM_001168620.1 | chr17:44078847-44086561 |
| 6689 | Enpp6 | NM_177304.3 | chr8:46986924-47094895 |
| 6690 | Enpp7 | NM_001030291.1 | chr11:118968187-118992841 |
| 6691 | Ensa | NM_001026212.1 | chr3:95624979-95630493 |
| 6692 | Enthd1 | NM_001163189.1 | chr15:80452239-80560470 |
| 6693 | Enthd2 | NM_183137.2 | chr11:120090521-120098731 |
| 6694 | Entpd1 | NM_009848.4 | chr19:40659769-40741602 |
| 6695 | Entpd2 | NM_009849.2 | chr2:25395873-25401323 |
| 6696 | Entpd3 | NM_178676.4 | chr9:120539817-120568326 |
| 6697 | Entpd4 | NM_026174.3 | chr14:69337150-69584992 |
| 6698 | Entpd5 | NM_001026214.2 | chr12:84373875-84409029 |
| 6699 | Entpd6 | NM_172117.5 | chr2:150749080-150771674 |
| 6700 | Entpd7 | NM_053103.5 | chr19:43689688-43733853 |
| 6701 | Entpd8 | NM_028093.1 | chr2:25080322-25085719 |
| 6702 | Eny2 | NM_175009.3 | chr15:44428110-44437685 |
| 6703 | Eogt | NM_175313.2 | chr6:97110943-97148883 |
| 6704 | Eomes | NM_001164789.1 | chr9:118478188-118486132 |
| 6705 | Ep300 | NM_177821.6 | chr15:81586213-81652077 |
| 6706 | Ep400 | NM_029337.2 | chr5:110664372-110770717 |
| 6707 | Epas1 | NM_010137.3 | chr17:86753863-86833410 |
| 6708 | Epb4.1 | NM_001128606.1 | chr4:131923428-132049078 |
| 6709 | Epb4.1l1 | NM_001006664.3 | chr2:156420487-156543214 |
| 6710 | Epb4.1l2 | NM_001199265.1 | chr10:25359797-25523518 |
| 6711 | Epb4.1l3 | NM_013813.1 | chr17:69156809-69289987 |
| 6712 | Epb4.1l4a | NM_013512.2 | chr18:33796326-34007206 |
| 6713 | Epb4.1l4b | NM_019427.2 | chr4:57061725-57143156 |
| 6714 | Epb4.1l5 | NM_001143416.1 | chr1:119594823-119649000 |
| 6715 | Epb4.2 | NM_013513.3 | chr2:121017896-121036877 |
| 6716 | Epc1 | NM_001276350.1 | chr18:6488891-6496857 |
| 6717 | Epc2 | NM_172863.4 | chr2:49451485-49551609 |
| 6718 | Epcam | NM_008532.2 | chr17:87635978-87651127 |
| 6719 | Epdr1 | NM_134065.4 | chr13:19591707-19619830 |
| 6720 | Epg5 | NM_001195633.1 | chr18:77936466-78035027 |
| 6721 | Epgn | NM_053087.2 | chr5:91027516-91035212 |
| 6722 | Epha1 | NM_023580.4 | chr6:42358486-42373268 |
| 6723 | Epha10 | NM_177256432.1 | chr4:124881784-124917800 |
| 6724 | Epha2 | NM_010139.3 | chr4:141301220-141329384 |
| 6725 | Epha3 | NM_010140.3 | chr16:63545217-63864157 |
| 6726 | Epha4 | NM_007936.3 | chr1:77367184-77515088 |
| 6727 | Epha5 | NM_007937.3 | chr5:84054764-84417382 |
| 6728 | Epha6 | NM_007938.2 | chr16:59653482-60605531 |
| 6729 | Epha7 | NM_001122889.1 | chr4:28813144-28947453 |
| 6730 | Epha8 | NM_007939.2 | chr4:136929418-136956816 |
| 6731 | Ephb1 | NM_001168296.1 | chr9:101922127-102354693 |
| 6732 | Ephb2 | NM_001290753.2 | chr4:136647540-136836012 |
| 6733 | Ephb3 | NM_010143.1 | chr16:21204794-21223304 |
| 6734 | Ephb4 | NM_001159571.1 | chr5:137350108-137374522 |
| 6735 | Ephb6 | NM_001146351.1 | chr6:41605481-41620507 |
| 6736 | Ephx1 | NM_010145.3 | chr1:180989555-181017569 |
| 6737 | Ephx2 | NM_001271402.1 | chr14:66084371-66124522 |
| 6738 | Ephx3 | NM_001033163.3 | chr17:32183769-32189463 |
| 6739 | Ephx4 | NM_001001804.2 | chr5:107403512-107430031 |

| | | | |
|---|---|---|---|
| 6740 | Epm2a | NM_010146.2 | chr10:11343444-11457477 |
| 6741 | Epm2aip1 | NM_175266.4 | chr9:111271844-111279091 |
| 6742 | Epn1 | NM_001252454.1 | chr7:5080234-5098178 |
| 6743 | Epn2 | NM_001252188.1 | chr11:61517248-61579687 |
| 6744 | Epn3 | NM_027984.3 | chr11:94489598-94499974 |
| 6745 | Epo | NM_007942.2 | chr5:137483019-137485816 |
| 6746 | Epor | NM_010149.3 | chr9:21958898-21963576 |
| 6747 | Eppin | NM_029325.2 | chr2:164588342-164593571 |
| 6748 | Eppk1 | NM_144848.2 | chr15:76101487-76120195 |
| 6749 | Eprs | NM_029735.1 | chr1:185363094-185428355 |
| 6750 | Eps15 | NM_001159964.1 | chr4:109343055-109387816 |
| 6751 | Eps15l1 | NM_001128832.1 | chr8:72377416-72421474 |
| 6752 | Eps8 | NM_001271587.1 | chr6:137477244-137571009 |
| 6753 | Eps8l1 | NM_001290416.1 | chr7:4464848-4480487 |
| 6754 | Eps8l2 | NM_133191.2 | chr7:141339001-141363016 |
| 6755 | Eps8l3 | NM_133867.2 | chr3:107877229-107892900 |
| 6756 | Epsti1 | NM_029495.2 | chr14:77904238-78002656 |
| 6757 | Ept1 | NM_027652.2 | chr5:30232617-30272430 |
| 6758 | Epx | NM_007946.2 | chr11:87863997-87875536 |
| 6759 | Epyc | NM_007884.2 | chr10:97644067-97681900 |
| 6760 | Eqtn | NM_001290623.1 | chr4:94907266-94928843 |
| 6761 | Eral1 | NM_022313.2 | chr11:78073375-78080383 |
| 6762 | Erap1 | NM_030711.4 | chr13:74639871-74691875 |
| 6763 | Eras | NM_181548.2 | chrX:7924275-7928607 |
| 6764 | Erbb2 | NM_001003817.1 | chr11:98412483-98437716 |
| 6765 | Erbb2ip | NM_001005868.2 | chr13:103818785-103920586 |
| 6766 | Erbb3 | NM_010153.1 | chr10:128569367-128589501 |
| 6767 | Erbb4 | NM_010154.2 | chr1:68032186-69108059 |
| 6768 | Erc1 | NM_053204.2 | chr6:119570795-119848150 |
| 6769 | Erc2 | NM_177814.4 | chr14:27622441-28478537 |
| 6770 | Ercc1 | NM_001127924.1 | chr7:19345070-19354830 |
| 6771 | Ercc2 | NM_007949.4 | chr7:19382038-19395692 |
| 6772 | Ercc3 | NM_133658.1 | chr18:32240330-32270147 |
| 6773 | Ercc4 | NM_015769.2 | chr16:13109735-13152009 |
| 6774 | Ercc5 | NM_017729.2 | chr1:44147743-44181260 |
| 6775 | Ercc6 | NM_001081221.1 | chr14:32513520-32580989 |
| 6776 | Ercc6l | NM_146235.3 | chrX:102142819-102157091 |
| 6777 | Ercc6l2 | NM_001013608.2 | chr13:63815319-63900301 |
| 6778 | Ercc8 | NM_028042.3 | chr13:108158737-108194981 |
| 6779 | Erdr1 | NM_133362.2 | chrY:90785441-90816465 |
| 6780 | Ereg | NM_007950.2 | chr5:91074616-91093649 |
| 6781 | Erf | NM_010155.3 | chr7:25242559-25250758 |
| 6782 | Erg | NM_133659.3 | chr16:95359168-95530365 |
| 6783 | Ergic1 | NM_026170.2 | chr17:26561511-26656933 |
| 6784 | Ergic2 | NM_001286560.1 | chr6:148179317-148212374 |
| 6785 | Ergic3 | NM_025516.4 | chr2:156008124-156018279 |
| 6786 | Erh | NM_007951.3 | chr12:80634022-80643861 |
| 6787 | Eri1 | NM_026067.3 | chr8:35465264-35495533 |
| 6788 | Eri2 | NM_027698.5 | chr7:119783825-119794058 |
| 6789 | Eri3 | NM_001285899.1 | chr4:117550364-117674297 |
| 6790 | Erich1 | NM_001034462.2 | chr8:14027564-14090327 |
| 6791 | Erich2 | NM_025744.2 | chr2:70508818-70540884 |
| 6792 | Erich3 | NM_175176.1 | chr3:154711132-154749012 |
| 6793 | Erich4 | NM_001039243 | chr7:25614620-25615892 |
| 6794 | Erich5 | NM_173421 | chr15:34453311-34473892 |
| 6795 | Erich6 | NM_001081262.1 | chr3:58616299-58637207 |
| 6796 | Erlec1 | NM_025745.2 | chr11:30929783-30954131 |
| 6797 | Erlin1 | NM_001164359.1 | chr19:44034942-44069775 |
| 6798 | Erlin2 | NM_153592 | chr8:27023798-27039435 |
| 6799 | Ermap | NM_013848.1 | chr4:119175456-119190011 |
| 6800 | Ermard | NM_001034891.3 | chr17:15053058-15064232 |
| 6801 | Ermn | NM_029972.3 | chr2:58045114-58052752 |
| 6802 | Ermp1 | NM_001081213.1 | chr19:29609882-29648420 |
| 6803 | Ern1 | NM_023913.2 | chr11:106397619-106487796 |
| 6804 | Ern2 | NM_012016.2 | chr7:122169892-122186216 |
| 6805 | Ero1l | NM_015774.3 | chr14:45283086-45318572 |
| 6806 | Ero1lb | NM_026184.2 | chr13:12565882-12609528 |
| 6807 | Erp27 | NM_026983.2 | chr6:136907386-136922180 |
| 6808 | Erp29 | NM_026129.2 | chr5:121444752-121452474 |
| 6809 | Erp44 | NM_029572.2 | chr4:48193330-48279589 |
| 6810 | Errfi1 | NM_133753.1 | chr4:150855090-150868880 |
| 6811 | Erv3 | NM_001166206.1 | chr2:131853677-131859747 |
| 6812 | Esam | NM_027102.3 | chr9:37528088-37538319 |
| 6813 | Esco1 | NM_001081222.1 | chr18:10566511-10610352 |
| 6814 | Esco2 | NM_028039.2 | chr14:65819026-65833969 |
| 6815 | Esd | NM_001285423.1 | chr14:74732296-74750765 |
| 6816 | Esf1 | NM_001081090.1 | chr2:140119880-140170558 |
| 6817 | Esm1 | NM_023612.3 | chr13:113209658-113218104 |
| 6818 | Esp1 | NM_001038500.2 | chr17:40727119-40731782 |
| 6819 | Esp15 | NM_001244651.1 | chr17:39640956-39645667 |
| 6820 | Esp16 | NM_001255977.1 | chr17:39536141-39540847 |
| 6821 | Esp18 | NM_001244763.1 | chr17:39406358-39410992 |
| 6822 | Esp23 | NM_001177582.1 | chr17:39073690-39077037 |
| 6823 | Esp24 | NM_001256050.1 | chr17:39036694-39040227 |
| 6824 | Esp3 | NM_001251916.1 | chr17:40632074-40637060 |
| 6825 | Esp31 | NM_001177586.1 | chr17:38639446-38645653 |
| 6826 | Esp34 | NM_001177585.1 | chr17:38554191-38560621 |
| 6827 | Esp36 | NM_001177587.1 | chr17:38416473-38420185 |
| 6828 | Esp38 | NM_001256051.1 | chr17:39950519-39955287 |
| 6829 | Esp4 | NM_001177583.1 | chr17:40598593-40602617 |
| 6830 | Esp5 | NM_001287194.1 | chr17:40574710-40579549 |
| 6831 | Esp6 | NM_001177529.1 | chr17:40561506-40565624 |
| 6832 | Esp6-esp5 | NM_001287195.1 | chr17:40561506-40579549 |
| 6833 | Esp8 | NM_001177584.1 | chr17:40520021-40530702 |
| 6834 | Espl1 | NM_001014976.2 | chr15:102296292-102324356 |

Fig. 26 - 37

| | | | |
|---|---|---|---|
| 6835 | Espn | NM_019585.3 | chr4:152120875-152128925 |
| 6836 | Espnl | NM_001033292 | chr1:91322074-91348303 |
| 6837 | Esr1 | NM_007956.5 | chr10:4611988-5005633 |
| 6838 | Esr2 | NM_010157.3 | chr12:76120418-76177259 |
| 6839 | Esrp1 | NM_001290383.1 | chr4:11331932-11386783 |
| 6840 | Esrp2 | NM_176838.2 | chr8:106131182-106136974 |
| 6841 | Esrra | NM_007953.2 | chr19:6910976-6921808 |
| 6842 | Esrrb | NM_001159500.1 | chr12:86361116-86521628 |
| 6843 | Esrrg | NM_001243792.1 | chr1:187609005-188214884 |
| 6844 | Esx1 | NM_007957.2 | chrX:137115396-137120326 |
| 6845 | Esyt1 | NM_011843.2 | chr10:128510249-128525859 |
| 6846 | Esyt2 | NM_028731.5 | chr12:116281221-116373098 |
| 6847 | Esyt3 | NM_177775.3 | chr9:99309966-99358530 |
| 6848 | Etaa1 | NM_026576.3 | chr11:17938748-17953875 |
| 6849 | Etd | NR_034074.1 | chrX:53434917-53443576 |
| 6850 | Etf1 | NM_144866.3 | chr18:34902784-34932003 |
| 6851 | Etfa | NM_145615.4 | chr9:55454435-55512243 |
| 6852 | Etfb | NM_026695.3 | chr7:43444071-43457800 |
| 6853 | Etfdh | NM_025794.2 | chr3:79603787-79628767 |
| 6854 | Ethe1 | NM_023154.3 | chr7:24587542-24608926 |
| 6855 | Etl4 | NM_001081006.1 | chr2:20289912-20810535 |
| 6856 | Etnk1 | NM_029250.2 | chr6:143167229-143208547 |
| 6857 | Etnk2 | NM_175443.2 | chr1:133363571-133380319 |
| 6858 | Etnppl | NM_001163587.1 | chr3:130617447-130635750 |
| 6859 | Etohd2 | NR_015349.2 | chr13:59769965-59773680 |
| 6860 | Etohi1 | NM_001177399.1 | chr2:178023283-178035859 |
| 6861 | Ets1 | NM_001038642.1 | chr9:32696041-32757820 |
| 6862 | Ets2 | NM_011809.3 | chr16:95702408-95721049 |
| 6863 | Etv1 | NM_001163154.1 | chr12:38783710-38868215 |
| 6864 | Etv2 | NM_007959.2 | chr7:30633615-30635852 |
| 6865 | Etv3 | NM_001033318.2 | chr3:87525577-87540158 |
| 6866 | Etv4 | NM_008815.3 | chr11:101769741-101785310 |
| 6867 | Etv5 | NM_023794.2 | chr16:22381312-22439570 |
| 6868 | Etv6 | NM_007961.4 | chr6:134035699-134270147 |
| 6869 | EU599041 | NM_001177525.1 | chr7:43214038-43226842 |
| 6870 | Eva1a | NM_145570.2 | chr6:82041627-82093099 |
| 6871 | Eva1b | NM_172145.3 | chr4:126148002-126149874 |
| 6872 | Eva1c | NM_001199210.1 | chr6:90830858-90904885 |
| 6873 | Evc | NM_021292.2 | chr5:37299170-37336881 |
| 6874 | Evc2 | NM_145920.3 | chr5:37338477-37425054 |
| 6875 | Evi2a | NM_001033711.1 | chr11:79526560-79530609 |
| 6876 | Evi2a-evi2b | NM_146023.4 | chr11:79513384-79530609 |
| 6877 | Evi2b | NM_001077496.1 | chr11:79513384-79523762 |
| 6878 | Evi5 | NM_007964.2 | chr5:107744794-107875107 |
| 6879 | Evi5l | NM_001039578.3 | chr8:4166566-4193701 |
| 6880 | Evl | NM_001163394.1 | chr12:108554719-108686515 |
| 6881 | Evpl | NM_025276.3 | chr11:116220558-116238091 |
| 6882 | Evx1 | NM_007966.4 | chr6:52313497-52318378 |
| 6883 | Evx2 | NM_007967.3 | chr2:74652990-74659557 |
| 6884 | Ewsr1 | NM_001283061.1 | chr11:5069686-5099088 |
| 6885 | Exd1 | NM_172874.2 | chr2:119519403-119547627 |
| 6886 | Exd2 | NM_133798.3 | chr12:80463094-80498135 |
| 6887 | Exo1 | NM_012012.4 | chr1:175808777-175911396 |
| 6888 | Exo5 | NM_001160043.1 | chr4:120921201-120925005 |
| 6889 | Exoc1 | NM_001289770.1 | chr5:76529310-76570298 |
| 6890 | Exoc2 | NM_025588.2 | chr13:30813917-30974047 |
| 6891 | Exoc3 | NM_177333.3 | chr13:74169804-74208700 |
| 6892 | Exoc3l | NM_177788.2 | chr8:105289923-105296098 |
| 6893 | Exoc3l4 | NM_001289487.1 | chr12:111417429-111431680 |
| 6894 | Exoc4 | NM_009148 | chr6:33249149-33972930 |
| 6895 | Exoc5 | NM_207214 | chr14:49012143-49066667 |
| 6896 | Exoc6 | NM_175353.2 | chr19:37550417-37683249 |
| 6897 | Exoc6b | NM_177077.2 | chr6:84618485-85069513 |
| 6898 | Exoc7 | NM_001162872.1 | chr11:116287997-116306738 |
| 6899 | Exoc8 | NM_198103.2 | chr8:124890298-124897705 |
| 6900 | Exog | NM_001172136.1 | chr9:119444922-119465518 |
| 6901 | Exosc1 | NM_001164561.1 | chr19:41922979-41933314 |
| 6902 | Exosc10 | NM_016699.2 | chr4:148558426-148582400 |
| 6903 | Exosc2 | NM_144886.2 | chr2:31670736-31681307 |
| 6904 | Exosc3 | NM_025553.3 | chr4:45316629-45320603 |
| 6905 | Exosc4 | NM_175399.4 | chr15:76327396-76330670 |
| 6906 | Exosc5 | NM_138586.3 | chr7:25659152-25668032 |
| 6907 | Exosc6 | NM_026874.3 | chr8:111056338-111057664 |
| 6908 | Exosc7 | NM_001081188.1 | chr9:123113230-123136129 |
| 6909 | Exosc8 | NM_001163570.1 | chr3:54728678-54735364 |
| 6910 | Exosc9 | NM_019933.2 | chr3:36552605-36565727 |
| 6911 | Exph5 | NM_176846.3 | chr9:53301669-53381158 |
| 6912 | Ext1 | NM_010162.2 | chr15:53068260-53346183 |
| 6913 | Ext2 | NM_010333.3 | chr2:93695630-93822568 |
| 6914 | Extl1 | NM_019578.2 | chr4:134356372-134372547 |
| 6915 | Extl2 | NM_001163514.1 | chr3:116008296-116029016 |
| 6916 | Extl3 | NM_018788.3 | chr14:65052058-65098106 |
| 6917 | Eya1 | NM_001252192.1 | chr1:14168957-14310199 |
| 6918 | Eya2 | NM_001271962.1 | chr2:165630344-165771727 |
| 6919 | Eya3 | NM_010665.3 | chr4:132635045-132724765 |
| 6920 | Eya4 | NM_010167.4 | chr10:23104167-23349903 |
| 6921 | Ezh1 | NM_007970.3 | chr11:101191114-101226463 |
| 6922 | Ezh2 | NM_001146689.1 | chr6:47530273-47595030 |
| 6923 | Ezr | NM_009510.2 | chr17:6738130-6782760 |
| 6924 | F10 | NM_001242368.1 | chr8:13037307-13056676 |
| 6925 | F11 | NM_028066.2 | chr8:45241167-45262031 |
| 6926 | F11r | NM_172647.2 | chr1:171437560-171464593 |
| 6927 | F12 | NM_021489.3 | chr13:55417957-55426804 |
| 6928 | F13a1 | NM_001166391.1 | chr3:36867177-37050244 |
| 6929 | F13b | NM_031164.2 | chr1:139501706-139523756 |
| 6930 | F2 | NM_010168.3 | chr2:91625319-91636457 |
| 6931 | F2r | NM_010169.3 | chr13:95601788-95618433 |
| 6932 | F2rl1 | NM_007974.4 | chr13:95511729-95525240 |
| 6933 | F2rl2 | NM_010170.4 | chr13:95696919-95702768 |
| 6934 | F2rl3 | NM_007975.3 | chr8:72761879-72763885 |
| 6935 | F3 | NM_010171.3 | chr3:121723536-121735052 |
| 6936 | F420014N23Rik | NR_045715.1 | chr10:127195248-127202643 |
| 6937 | F5 | NM_007976.3 | chr1:164151834-164220277 |
| 6938 | F630028O10Rik | NR_030718.1 | chrX:96239925-96243642 |
| 6939 | F630042J09Rik | NR_033540.1 | chr13:67278593-67283361 |
| 6940 | F630111L10Rik | NR_045641.1 | chr3:59146295-59153628 |
| 6941 | F630206G17Rik | NR_045876.1 | chr11:45808082-45842878 |
| 6942 | F7 | NM_010172.4 | chr8:13026033-13035805 |
| 6943 | F730035M05Rik | NR_045174.1 | chr12:70227840-70234165 |
| 6944 | F730043M19Rik | NR_015602.2 | chr12:33111710-33147586 |
| 6945 | F8 | NM_001161373.1 | chrX:75172714-75380041 |
| 6946 | F830002L21Rik | NR_033558.1 | chr10:43593426-43630913 |
| 6947 | F830016B08Rik | NM_001101475.2 | chr18:60293379-60303016 |
| 6948 | F830045P16Rik | NM_177653.3 | chr2:129458358-129536602 |
| 6949 | F8a | NM_007978.3 | chrX:73228305-73230795 |
| 6950 | F9 | NM_007979.2 | chrX:59999463-60030760 |
| 6951 | F930015N05Rik | NR_028445.1 | chr11:64433134-64436674 |
| 6952 | Fa2h | NM_178086.3 | chr8:111345137-111393821 |
| 6953 | Faah | NM_010173.4 | chr4:115986655-116017902 |
| 6954 | Fabp1 | NM_017399.4 | chr6:71199887-71205023 |
| 6955 | Fabp12 | NM_029310.1 | chr3:10284208-10301183 |
| 6956 | Fabp2 | NM_007980.3 | chr3:122895071-122899506 |
| 6957 | Fabp3 | NM_010174.1 | chr4:130308777-130315463 |
| 6958 | Fabp4 | NM_024406.2 | chr3:10204342-10208576 |
| 6959 | Fabp5 | NM_001272097.1 | chr3:10012584-10016610 |
| 6960 | Fabp6 | NM_008375.2 | chr11:43596039-43601562 |
| 6961 | Fabp7 | NM_021272.3 | chr10:57784922-57788450 |
| 6962 | Fabp9 | NM_011598.3 | chr3:10193623-10197283 |
| 6963 | Fadd | NM_010175.5 | chr7:144578322-144582436 |
| 6964 | Fads1 | NM_146094.2 | chr19:10182887-10196872 |
| 6965 | Fads2 | NM_019699.1 | chr19:10064163-10101503 |
| 6966 | Fads3 | NM_021890.3 | chr19:10041547-10059671 |
| 6967 | Fads6 | NM_178035.4 | chr11:115283365-115297546 |
| 6968 | Faf1 | NM_007983.2 | chr4:109676626-109963960 |
| 6969 | Faf2 | NM_178397.3 | chr13:54621783-54664063 |
| 6970 | Fah | NM_010176.4 | chr7:84585158-84605942 |
| 6971 | Fahd1 | NM_023480.2 | chr17:24848895-24850302 |
| 6972 | Fahd2a | NM_029629.2 | chr2:127436214-127444565 |
| 6973 | Faim | NM_001122851.1 | chr9:98986372-99002019 |
| 6974 | Faim2 | NM_001038658.2 | chr15:99497004-99528165 |
| 6975 | Faim3 | NM_026976.2 | chr1:130865776-130880790 |
| 6976 | Fam101a | NM_028443.2 | chr5:125003474-125012547 |
| 6977 | Fam101b | NM_029658.1 | chr11:76019194-76027782 |
| 6978 | Fam102a | NM_153560.4 | chr2:32535358-32569750 |
| 6979 | Fam102b | NM_001163567.1 | chr3:108970996-109027607 |
| 6980 | Fam103a1 | NM_025997.2 | chr7:81762952-81769490 |
| 6981 | Fam104a | NM_138598.5 | chr11:113661318-113684151 |
| 6982 | Fam105a | NM_001242423.1 | chr15:27655070-27681542 |
| 6983 | Fam107a | NM_183187.3 | chr14:8296277-8309776 |
| 6984 | Fam107b | NM_025626.4 | chr2:3713457-3782134 |
| 6985 | Fam109a | NM_175474.3 | chr5:121849027-121854599 |
| 6986 | Fam109b | NM_177391.4 | chr15:82341178-82345710 |
| 6987 | Fam110a | NM_001289150.1 | chr2:151969395-151973981 |
| 6988 | Fam110b | NM_173426.2 | chr4:5644178-5799944 |
| 6989 | Fam110c | NM_027828.2 | chr12:31073967-31079940 |
| 6990 | Fam111a | NM_026640.2 | chr19:12573524-12589696 |
| 6991 | Fam114a1 | NM_026667.3 | chr5:64970074-65041901 |
| 6992 | Fam114a2 | NM_001168667.1 | chr11:57482989-57518644 |
| 6993 | Fam115a | NM_029930.2 | chr6:42672546-42693059 |
| 6994 | Fam115c | NM_146174.1 | chr6:42623042-42645041 |
| 6995 | Fam115e | NM_203396.1 | chr6:42587212-42597372 |
| 6996 | Fam117a | NM_172543.4 | chr11:95337017-95381872 |
| 6997 | Fam117b | NM_001037725.3 | chr1:59913005-59985348 |
| 6998 | Fam118a | NM_133750.4 | chr15:85037061-85062830 |
| 6999 | Fam118b | NM_001286604.1 | chr9:35216964-35267805 |
| 7000 | Fam120a | NM_001033268.2 | chr13:48879216-48967828 |
| 7001 | Fam120aos | NR_015601.1 | chr13:48968111-48969605 |
| 7002 | Fam120b | NM_024203.3 | chr17:15396245-15433581 |
| 7003 | Fam120c | NM_198105.2 | chrX:151344222-151474134 |
| 7004 | Fam122a | NM_026520.3 | chr19:24475778-24477474 |
| 7005 | Fam122b | NM_001166365.2 | chrX:53243414-53269805 |
| 7006 | Fam122c | NM_028671.2 | chrX:53273432-53301501 |
| 7007 | Fam124a | NM_001243857.1 | chr14:62555736-62608485 |
| 7008 | Fam124b | NM_173425.3 | chr1:80198698-80213944 |
| 7009 | Fam126a | NM_053090.3 | chr5:23960935-24030690 |
| 7010 | Fam126b | NM_172513.3 | chr1:58522805-58586333 |
| 7011 | Fam129a | NM_022018.3 | chr1:151571372-151719347 |
| 7012 | Fam129b | NM_146119.2 | chr2:32876133-32925253 |
| 7013 | Fam129c | NM_001166213.1 | chr8:71597645-71608149 |
| 7014 | Fam131a | NM_133778.2 | chr16:20695056-20703036 |
| 7015 | Fam131b | NM_001113327.2 | chr6:42315304-42324640 |
| 7016 | Fam131c | NM_001085513.2 | chr4:141368191-141384174 |
| 7017 | Fam132a | NM_026125.3 | chr4:155962311-155966629 |
| 7018 | Fam132b | NM_173395.2 | chr1:91366429-91374217 |
| 7019 | Fam133b | NM_001042501.1 | chr5:3543832-3570546 |
| 7020 | Fam134a | NM_170755.2 | chr5:75142785-75147909 |
| 7021 | Fam134b | NM_001034851.2 | chr15:25843297-25973696 |
| 7022 | Fam134c | NM_026501.2 | chr11:101096515-101119824 |
| 7023 | Fam135b | NM_026604.4 | chr1:24010757-24100341 |
| 7024 | Fam135b | NM_177819.3 | chr15:71445677-71727838 |

Fig. 26 - 38

| | | | | | | | |
|---|---|---|---|---|---|---|---|
| 7025 | Fam136a | NM_025591.2 | chr6:86365682-86370058 | 7120 | Fam213b | NM_025582.3 | chr4:154896429-154899043 |
| 7026 | Fam13a | NM_153574.2 | chr6:58933535-59024502 | 7121 | Fam214a | NM_001113283.1 | chr9:74953052-75032468 |
| 7027 | Fam13b | NM_146084.1 | chr18:34442350-34506823 | 7122 | Fam214b | NM_001253353.1 | chr4:43032413-43040301 |
| 7028 | Fam13c | NM_001143776.1 | chr10:70440909-70558732 | 7123 | Fam216a | NM_026883.3 | chr5:122364583-122371963 |
| 7029 | Fam149a | NM_153535.2 | chr8:45336714-45382291 | 7124 | Fam216b | NM_177629.4 | chr14:78081023-78089007 |
| 7030 | Fam149b | NM_001024512.2 | chr14:20348161-20383491 | 7125 | Fam217a | NM_027967.1 | chr13:34909963-34919992 |
| 7031 | Fam150a | NM_001195732.1 | chr1:6359330-6394731 | 7126 | Fam217b | NM_001081289.1 | chr2:178414533-178422161 |
| 7032 | Fam150b | NM_001159743.1 | chr12:30884323-30893854 | 7127 | Fam219a | NM_001159583.1 | chr4:41518928-41569527 |
| 7033 | Fam151a | NM_146149.1 | chr4:106733914-106748292 | 7128 | Fam219aos | NR_045726.1 | chr4:41517436-41518929 |
| 7034 | Fam151b | NM_001163627.1 | chr13:92449619-92484031 | 7129 | Fam219b | NM_001166364.1 | chr9:57537527-57543187 |
| 7035 | Fam154a | NM_001081096.1 | chr4:86444697-86558303 | 7130 | Fam220a | NM_026050.2 | chr5:143548705-143564525 |
| 7036 | Fam154b | NM_177894.4 | chr7:82632959-82648528 | 7131 | Fam221a | NM_001172216.1 | chr6:49367738-49389904 |
| 7037 | Fam155a | NM_173446.2 | chr8:9206009-9771023 | 7132 | Fam221b | NM_175517.3 | chr4:43659621-43668859 |
| 7038 | Fam159a | NM_001099303.2 | chr4:108367776-108383655 | 7133 | Fam222a | NM_001004180.1 | chr5:114568250-114613218 |
| 7039 | Fam159b | NM_029984.1 | chr13:104845282-104863893 | 7134 | Fam222b | NM_145430.2 | chr11:78094672-78157339 |
| 7040 | Fam160a1 | NM_172682.3 | chr3:85660062-85746209 | 7135 | Fam227a | NM_029407.1 | chr15:79609575-79658956 |
| 7041 | Fam160a2 | NM_001242363.2 | chr7:105371210-105400054 | 7136 | Fam227b | NM_029455.3 | chr2:125983482-126152004 |
| 7042 | Fam160b1 | NM_145505.4 | chr19:57361008-57389594 | 7137 | Fam228a | NM_029107.2 | chr12:4713804-4738383 |
| 7043 | Fam160b2 | NM_194345.1 | chr14:70583294-70599835 | 7138 | Fam228b | NM_175431.4 | chr4:746215-4769267 |
| 7044 | Fam161a | NM_028672.2 | chr11:23013386-23023741 | 7139 | Fam229a | NM_001085491.2 | chr4:129491189-129491956 |
| 7045 | Fam161b | NM_172581.2 | chr12:84345316-84361821 | 7140 | Fam229b | NM_183254.1 | chr10:39118807-39133895 |
| 7046 | Fam162a | NM_026321.4 | chr16:36043843-36071515 | 7141 | Fam24a | NM_183272.2 | chr7:131334621-131336716 |
| 7047 | Fam162b | NM_029894.1 | chr10:51585449-51590460 | 7142 | Fam25c | NM_183278.2 | chr14:34351881-34355393 |
| 7048 | Fam163a | NM_177838.3 | chr1:156075955-156205026 | 7143 | Fam26d | NM_001081165.1 | chr10:34038783-34044313 |
| 7049 | Fam163b | NM_175427.4 | chr2:27110378-27142477 | 7144 | Fam26e | NM_178908.3 | chr10:34091351-34096519 |
| 7050 | Fam166a | NM_026624.3 | chr2:25218744-25222281 | 7145 | Fam26f | NM_175449.4 | chr10:34126066-34127972 |
| 7051 | Fam166b | NM_001162381.1 | chr4:43427019-43429134 | 7146 | Fam32a | NM_026455.4 | chr8:72219729-72223775 |
| 7052 | Fam167a | NM_178762.4 | chr14:63436393-63465502 | 7147 | Fam35a | NM_029389.2 | chr14:34237034-34310503 |
| 7053 | Fam167b | NM_182783.2 | chr4:129576814-129578580 | 7148 | Fam3a | NM_025473.4 | chrX:74384719-74393274 |
| 7054 | Fam168a | NM_178764.3 | chr7:100706701-100841630 | 7149 | Fam3b | NM_020622.2 | chr16:97471085-97504936 |
| 7055 | Fam168b | NM_001160235.1 | chr1:34813217-34843050 | 7150 | Fam3c | NM_138587.4 | chr6:22306521-22356081 |
| 7056 | Fam169a | NM_001100458.1 | chr13:97071642-97129522 | 7151 | Fam43a | NM_177632.3 | chr16:30599722-30602797 |
| 7057 | Fam169b | NM_001013811.2 | chr7:68273838-68363092 | 7152 | Fam43b | NM_001081672.2 | chr4:138394091-138396458 |
| 7058 | Fam170a | NM_001004061.1 | chr18:50278368-50283019 | 7153 | Fam45a | NM_001167829.1 | chr19:60811569-60836229 |
| 7059 | Fam170b | NM_001164485.1 | chr14:32833961-32836788 | 7154 | Fam46a | NM_001160378.1 | chr9:85320438-85327124 |
| 7060 | Fam171a1 | NM_001081161.1 | chr2:3118387-3227809 | 7155 | Fam46b | NM_175307.6 | chr4:133480132-133487940 |
| 7061 | Fam171a2 | NM_199200.2 | chr11:102436980-102447663 | 7156 | Fam46c | NM_001142952.1 | chr3:100471535-100489192 |
| 7062 | Fam171b | NM_175514.2 | chr2:83812727-83881358 | 7157 | Fam46d | NM_001163104.2 | chrX:107816476-107872911 |
| 7063 | Fam172a | NM_001163419.1 | chr13:77708689-78166240 | 7158 | Fam47c | NM_001164739.1 | chrX:78737762-78739410 |
| 7064 | Fam173a | NM_001285982.1 | chr17:25790499-25792387 | 7159 | Fam47e | NM_001033478.2 | chr5:92571536-92591284 |
| 7065 | Fam173b | NM_026546.3 | chr15:31602115-31617535 | 7160 | Fam49a | NM_001146119.1 | chr12:12262138-12376361 |
| 7066 | Fam174a | NM_026321.4 | chr1:95313627-95335284 | 7161 | Fam49b | NM_144846.5 | chr15:63929093-64060448 |
| 7067 | Fam174b | NM_001162532.1 | chr7:73740306-73776919 | 7162 | Fam50a | NM_138607.3 | chrX:74313032-74320149 |
| 7068 | Fam175a | NM_172405.3 | chr5:100804801-100820935 | 7163 | Fam50b | NM_138746.2 | chr13:34739641-34747622 |
| 7069 | Fam175b | NM_198017.3 | chr7:132859224-132885114 | 7164 | Fam53a | NM_138390.3 | chr5:33600352-33629635 |
| 7070 | Fam178a | NM_001081225.1 | chr19:44931118-44983787 | 7165 | Fam53b | NM_175268.4 | chr7:132712083-132786935 |
| 7071 | Fam178b | NM_001126046.1 | chr1:36562695-36683183 | 7166 | Fam53c | NM_175104.4 | chr18:34758905-34773760 |
| 7072 | Fam179a | NM_177087.4 | chr17:71672260-71729669 | 7167 | Fam57a | NM_027773.3 | chr11:76202055-76208257 |
| 7073 | Fam179b | NM_177805.3 | chr12:64965741-65022573 | 7168 | Fam57b | NM_001146347.1 | chr7:126824652-126830219 |
| 7074 | Fam180a | NM_173375.1 | chr6:35312745-35326141 | 7169 | Fam58b | NM_197989.1 | chr11:78750505-78751729 |
| 7075 | Fam181a | NM_001195726.1 | chr12:103314958-103317065 | 7170 | Fam60a | NM_019643.3 | chr6:148921058-148946432 |
| 7076 | Fam181b | NM_021427.2 | chr7:93079878-93081721 | 7171 | Fam63a | NM_133858.4 | chr3:95282934-95296164 |
| 7077 | Fam183b | NM_001162817.1 | chr1:58792801-58801960 | 7172 | Fam63b | NM_172772.2 | chr9:70599013-70657174 |
| 7078 | Fam184a | NM_001081428.1 | chr10:53633144-53750909 | 7173 | Fam64a | NM_144526.3 | chr11:72042501-72047370 |
| 7079 | Fam184b | NM_021416.3 | chr5:45529704-45639501 | 7174 | Fam65a | NM_001081241.2 | chr8:105605228-105622218 |
| 7080 | Fam185a | NM_177869.4 | chr5:21424902-21482124 | 7175 | Fam65b | NM_001080381.1 | chr13:24638647-24706001 |
| 7081 | Fam186b | NM_001081254.1 | chr15:99271017-99287180 | 7176 | Fam65c | NM_001080708.2 | chr2:167980785-168010593 |
| 7082 | Fam187a | NM_025766.2 | chr11:102885168-102886731 | 7177 | Fam69a | NM_026062.4 | chr5:107908041-107987077 |
| 7083 | Fam187b | NM_001242647.1 | chr7:30981920-30989725 | 7178 | Fam69b | NM_019833.3 | chr2:26628456-26636497 |
| 7084 | Fam188a | NM_024185.4 | chr2:12347263-12419460 | 7179 | Fam69c | NM_173770.4 | chr18:84720241-84740436 |
| 7085 | Fam188b | NM_001142781.1 | chr6:55203382-55320222 | 7180 | Fam71a | NM_001109759.1 | chr1:191162583-191164817 |
| 7086 | Fam189a1 | NM_183087.4 | chr7:64756095-65156528 | 7181 | Fam71b | NM_001013783.2 | chr11:46404727-46407985 |
| 7087 | Fam189a2 | NM_001114174.1 | chr19:23972749-24031019 | 7182 | Fam71d | NM_027597.4 | chr12:78691534-78734519 |
| 7088 | Fam189b | NM_001014995.1 | chr3:89183224-89189289 | 7183 | Fam71e1 | NM_028169.1 | chr7:44496587-44501134 |
| 7089 | Fam192a | NM_028221.4 | chr8:94574940-94601726 | 7184 | Fam71e2 | NM_172895.3 | chr4:4753225-4771270 |
| 7090 | Fam193a | NM_001243123.1 | chr5:34369932-34486458 | 7185 | Fam71f1 | NM_001289663.1 | chr6:29319139-29336022 |
| 7091 | Fam193b | NM_145382.4 | chr13:55539915-55571120 | 7186 | Fam71f2 | NM_001101486.1 | chr6:29281140-29290676 |
| 7092 | Fam195a | NM_026633.3 | chr7:125863697-25868738 | 7187 | Fam72a | NM_175382.3 | chr1:131527988-131539872 |
| 7093 | Fam195b | NM_001033231.2 | chr11:120542887-120549727 | 7188 | Fam73a | NM_001162375.1 | chr3:152273459-152340407 |
| 7094 | Fam196a | NM_001143802.1 | chr7:134881907-134938430 | 7189 | Fam73b | NM_001242492.1 | chr2:30364232-30385519 |
| 7095 | Fam196b | NM_001025382.2 | chr11:34314821-34422640 | 7190 | Fam76a | NM_001163792.1 | chr4:132899212-132922551 |
| 7096 | Fam198a | NM_001199927.1 | chr9:121951019-121980208 | 7191 | Fam76b | NM_176836.3 | chr9:13827726-13846522 |
| 7097 | Fam198b | NM_133187.3 | chr3:79885929-79946278 | 7192 | Fam78a | NM_175511.4 | chr2:32066884-32083705 |
| 7098 | Fam199x | NM_146261.2 | chrX:137049593-137082501 | 7193 | Fam78b | NM_001160261.1 | chr1:167001416-167091302 |
| 7099 | Fam19a1 | NM_182808.3 | chr6:96113153-96657198 | 7194 | Fam81a | NM_029784.2 | chr9:70089309-70141557 |
| 7100 | Fam19a2 | NM_001226425.1 | chr10:123164875-123741204 | 7195 | Fam83a | NM_173862.2 | chr15:57985902-58010702 |
| 7101 | Fam19a3 | NM_183224.3 | chr3:104767404-104777547 | 7196 | Fam83b | NM_001045518.1 | chr9:76490704-76545804 |
| 7102 | Fam19a4 | NM_177233.5 | chr6:96831208-97060411 | 7197 | Fam83c | NM_027788.2 | chr2:155829182-155834854 |
| 7103 | Fam19a5 | NM_001252301.1 | chr15:87544298-87759364 | 7198 | Fam83d | NM_027975.2 | chr2:158768098-158786637 |
| 7104 | Fam203a | NM_021555.2 | chr15:76368897-76371411 | 7199 | Fam83e | NM_001033170.4 | chr7:45721219-45729492 |
| 7105 | Fam204a | NM_029648.6 | chr19:60198585-60226697 | 7200 | Fam83f | NM_145986.2 | chr15:80671846-80700425 |
| 7106 | Fam206a | NM_001081420.1 | chr4:56802328-56809605 | 7201 | Fam83g | NM_178618.3 | chr11:61684409-61709950 |
| 7107 | Fam207a | NM_133998.3 | chr10:77486654-77515813 | 7202 | Fam83h | NM_001168253.1 | chr15:76001091-76009498 |
| 7108 | Fam208a | NM_001114879.1 | chr14:27428846-27483554 | 7203 | Fam84a | NM_029007.2 | chr12:14147597-14152038 |
| 7109 | Fam208b | NM_134063.3 | chr13:3566034-3611108 | 7204 | Fam84b | NM_001162926.1 | chr15:60818995-60825080 |
| 7110 | Fam209 | NM_029608.1 | chr2:172472553-172474316 | 7205 | Fam86 | NM_027446.2 | chr16:5244154-5255956 |
| 7111 | Fam20a | NM_153782.1 | chr11:109672925-109722256 | 7206 | Fam89a | NM_001081120.1 | chr8:124740256-124751809 |
| 7112 | Fam20b | NM_145413.4 | chr1:156678570-156718910 | 7207 | Fam89b | NM_023166.2 | chr19:5728086-5729666 |
| 7113 | Fam20c | NM_030565.6 | chr5:138755080-138810063 | 7208 | Fam92a | NM_026558.5 | chr4:12153141-12172015 |
| 7114 | Fam21 | NM_026585.3 | chr6:116208032-116262671 | 7209 | Fam92b | NM_001033980.2 | chr8:120166396-120177469 |
| 7115 | Fam210a | NM_153794.4 | chr18:68260184-68300333 | 7210 | Fam96a | NM_026635.3 | chr9:66126610-66138968 |
| 7116 | Fam210b | NM_025912.4 | chr2:172345576-172355749 | 7211 | Fam96b | NM_026753.2 | chr8:104639838-104641728 |
| 7117 | Fam212a | NM_026597.3 | chr9:107984223-107985916 | 7212 | Fam98a | NM_133747.2 | chr17:75537085-75551946 |
| 7118 | Fam212b | NM_001168356.1 | chr3:105705457-105720842 | 7213 | Fam98b | NM_026620.3 | chr2:117249738-117271540 |
| 7119 | Fam213a | NM_027464.3 | chr14:40993739-41013775 | 7214 | Fam98c | NM_001146023.1 | chr7:29152509-29156210 |

Fig. 26 - 39

| | | | |
|---|---|---|---|
| 7215 | Fan1 | NM_177893.3 | chr7:64346757-64374095 |
| 7216 | Fanca | NM_016925.3 | chr8:123268243-123318576 |
| 7217 | Fancb | NM_001146081.1 | chrX:164980591-164997272 |
| 7218 | Fancc | NM_001042673.2 | chr13:63304708-63431745 |
| 7219 | Fancd2 | NM_001033244.3 | chr6:113531681-113596285 |
| 7220 | Fancd2os | NM_027633.3 | chr6:113596761-113600715 |
| 7221 | Fance | NM_001163819.1 | chr17:28313529-28326574 |
| 7222 | Fancf | NM_001115087.1 | chr7:51860576-51862267 |
| 7223 | Fancg | NM_001163233.1 | chr4:43002336-43010301 |
| 7224 | Fanci | NM_145946.2 | chr7:79392337-79450264 |
| 7225 | Fancl | NM_001277273.1 | chr11:26387083-26471883 |
| 7226 | Fancm | NM_178912.3 | chr12:65075605-65132058 |
| 7227 | Fank1 | NM_025850.2 | chr7:133776890-133881532 |
| 7228 | Fap | NM_007986.3 | chr2:62500935-62574021 |
| 7229 | Far1 | NM_001285831.1 | chr7:113513833-113570888 |
| 7230 | Far2 | NM_178797.3 | chr6:148047415-148182760 |
| 7231 | Farp1 | NM_134082.3 | chr14:121035573-121283726 |
| 7232 | Farp2 | NM_145519.2 | chr1:93512103-93621976 |
| 7233 | Fars2 | NM_001039189.2 | chr13:36117642-36537595 |
| 7234 | Farsa | NM_025648.3 | chr8:84856985-84869257 |
| 7235 | Farsb | NM_001278075.1 | chr1:78417957-78488897 |
| 7236 | Fas | NM_001146708.1 | chr19:34290658-34309350 |
| 7237 | Fasl | NM_001205243.1 | chr1:161780691-161788495 |
| 7238 | Fasn | NM_007988.3 | chr11:120805957-120824547 |
| 7239 | Fastk | NM_023229.2 | chr5:24441039-24445235 |
| 7240 | Fastkd1 | NM_177244.3 | chr2:69686823-69712606 |
| 7241 | Fastkd2 | NM_172422.3 | chr1:63730624-63753385 |
| 7242 | Fastkd3 | NM_027123.4 | chr13:68582247-68592279 |
| 7243 | Fastkd5 | NM_001146084.1 | chr2:130613837-130630027 |
| 7244 | Fat1 | NM_001081286.2 | chr8:44950207-45052257 |
| 7245 | Fat2 | NM_001029882.2 | chr11:55250609-55312257 |
| 7246 | Fat3 | NM_001080814.1 | chr9:15910192-16378231 |
| 7247 | Fat4 | NM_183221.3 | chr3:38886939-39011983 |
| 7248 | Fate1 | NR_003243.2 | chrX:71972985-71989046 |
| 7249 | Fau | NM_001160239.2 | chr19:6057887-6059524 |
| 7250 | Faxc | NM_175234.4 | chr4:21991325-22001461 |
| 7251 | Fbf1 | NM_172571.3 | chr11:116142284-116168178 |
| 7252 | Fbl | NM_077991.3 | chr7:28169747-28179269 |
| 7253 | Fblim1 | NM_001163256.1 | chr4:141576061-141599924 |
| 7254 | Fbln1 | NM_001004147.3 | chr11:35797379-35798884 |
| 7255 | Fbln1 | NM_010180.2 | chr15:85206007-85286294 |
| 7256 | Fbln2 | NM_001001437.1 | chr6:91212763-91272540 |
| 7257 | Fbln5 | NM_011812.4 | chr12:101746564-101819119 |
| 7258 | Fbln7 | NM_024237.4 | chr2:128863931-128897034 |
| 7259 | Fbn1 | NM_007993.2 | chr2:125300593-125506438 |
| 7260 | Fbn2 | NM_010181.2 | chr18:58008622-58209926 |
| 7261 | Fbp1 | NM_019395.3 | chr13:62864752-62888282 |
| 7262 | Fbp2 | NM_007994.3 | chr13:62836884-62858370 |
| 7263 | Fbrs | NM_010183.1 | chr7:127485220-127491513 |
| 7264 | Fbrsl1 | NM_001142642.1 | chr5:110361751-110448503 |
| 7265 | Fbxl12 | NM_001002846.2 | chr9:20637748-20644767 |
| 7266 | Fbxl12os | NR_033729.1 | chr9:20607474-20617271 |
| 7267 | Fbxl13 | NM_001199632.1 | chr5:21483846-21645605 |
| 7268 | Fbxl14 | NM_133940.3 | chr6:119479667-119483886 |
| 7269 | Fbxl15 | NM_133694.2 | chr19:46328183-46330446 |
| 7270 | Fbxl16 | NM_001164225.1 | chr17:25809084-25821265 |
| 7271 | Fbxl17 | NM_015794.1 | chr17:63045951-63500580 |
| 7272 | Fbxl18 | NM_001033312.3 | chr5:142871788-142895238 |
| 7273 | Fbxl19 | NM_172748.2 | chr7:127746774-127768928 |
| 7274 | Fbxl2 | NM_178624.6 | chr9:113976957-114026751 |
| 7275 | Fbxl20 | NM_028149.1 | chr11:98082553-98149616 |
| 7276 | Fbxl21 | NM_178794.3 | chr13:56522507-56537786 |
| 7277 | Fbxl22 | NM_175206.4 | chr9:66508458-66514593 |
| 7278 | Fbxl3 | NM_015822.2 | chr14:103080238-103099509 |
| 7279 | Fbxl4 | NM_172988.4 | chr4:22357542-22434091 |
| 7280 | Fbxl5 | NM_001159963.1 | chr5:43744617-43782149 |
| 7281 | Fbxl6 | NM_013909.2 | chr15:76535727-76538746 |
| 7282 | Fbxl7 | NM_175763.3 | chr15:26540458-26895564 |
| 7283 | Fbxl8 | NM_015821.2 | chr8:105264647-105269326 |
| 7284 | Fbxo10 | NM_001024142.1 | chr4:45034247-45084604 |
| 7285 | Fbxo11 | NM_001081034.1 | chr17:87990858-88065285 |
| 7286 | Fbxo15 | NM_015798.3 | chr18:84935024-84981392 |
| 7287 | Fbxo16 | NM_015798.2 | chr14:65266700-65321502 |
| 7288 | Fbxo17 | NM_015796.2 | chr7:28716789-28738140 |
| 7289 | Fbxo18 | NM_015792.1 | chr2:11742572-11777527 |
| 7290 | Fbxo2 | NM_176848.1 | chr4:148160667-148166417 |
| 7291 | Fbxo21 | NM_145564.3 | chr5:117976769-118010191 |
| 7292 | Fbxo22 | NM_028049.2 | chr9:55208934-55224433 |
| 7293 | Fbxo24 | NM_027229.4 | chr5:137612504-137625078 |
| 7294 | Fbxo25 | NM_025785.2 | chr8:13907805-13940521 |
| 7295 | Fbxo27 | NM_001163702.1 | chr7:28693143-28699337 |
| 7296 | Fbxo28 | NM_175127.2 | chr1:182313101-182341606 |
| 7297 | Fbxo3 | NM_020593.2 | chr2:104027798-104055127 |
| 7298 | Fbxo30 | NM_001168297.1 | chr10:11281586-11297969 |
| 7299 | Fbxo31 | NM_133765.4 | chr8:121549442-121578806 |
| 7300 | Fbxo32 | NM_026346.3 | chr15:58175878-58214892 |
| 7301 | Fbxo33 | NM_001033156.4 | chr12:59200654-59219483 |
| 7302 | Fbxo34 | NM_001146085.1 | chr14:47472566-47531962 |
| 7303 | Fbxo36 | NM_025386.3 | chr1:84839840-84900486 |
| 7304 | Fbxo38 | NM_134136.3 | chr18:62504058-62548743 |
| 7305 | Fbxo39 | NM_001099688.2 | chr17:72314443-72319419 |
| 7306 | Fbxo4 | NM_134099.2 | chr15:3963563-3979573 |
| 7307 | Fbxo40 | NM_001037321.1 | chr16:36966072-36979136 |
| 7308 | Fbxo41 | NM_001001160.3 | chr6:85469575-85502994 |
| 7309 | Fbxo42 | NM_172518.3 | chr4:141147921-141204062 |
| 7310 | Fbxo43 | NM_001081253.1 | chr15:36150059-36164884 |
| 7311 | Fbxo44 | NM_001161851.2 | chr4:148152798-148159589 |
| 7312 | Fbxo45 | NM_173439.2 | chr16:32230111-32247025 |
| 7313 | Fbxo46 | NM_175530.3 | chr7:19119858-19139261 |
| 7314 | Fbxo47 | NM_001081435.1 | chr11:97854306-97884154 |
| 7315 | Fbxo48 | NM_176982.2 | chr11:16951409-16954772 |
| 7316 | Fbxo5 | NM_025995.2 | chr10:5799157-5805465 |
| 7317 | Fbxo6 | NM_001163704.1 | chr4:148145715-148151925 |
| 7318 | Fbxo7 | NM_153195.2 | chr10:86021928-86048328 |
| 7319 | Fbxo8 | NM_015791.3 | chr8:56551133-56593939 |
| 7320 | Fbxo9 | NM_001081490.2 | chr9:78081499-78109065 |
| 7321 | Fbxw10 | NM_001033669.2 | chr11:62847122-62877462 |
| 7322 | Fbxw11 | NM_001271347.1 | chr11:32642554-32746814 |
| 7323 | Fbxw13 | NM_177598.3 | chr9:109179226-109195975 |
| 7324 | Fbxw14 | NM_015793.2 | chr9:109271124-109287676 |
| 7325 | Fbxw15 | NM_199036.2 | chr9:109552801-109568262 |
| 7326 | Fbxw16 | NM_177070.3 | chr9:109432317-109449140 |
| 7327 | Fbxw17 | NM_175401.3 | chr13:50417876-50433769 |
| 7328 | Fbxw18 | NM_001033794.3 | chr9:109676733-109702700 |
| 7329 | Fbxw19 | NM_177703.3 | chr9:109478574-109495854 |
| 7330 | Fbxw2 | NM_001164768.1 | chr2:34804363-34823181 |
| 7331 | Fbxw20 | NM_001008428.3 | chr9:109217431-109234754 |
| 7332 | Fbxw21 | NM_177069.2 | chr9:109139453-109162022 |
| 7333 | Fbxw22 | NM_001014395.2 | chr9:109378408-109404294 |
| 7334 | Fbxw24 | NM_001013776.4 | chr9:109601115-109626059 |
| 7335 | Fbxw26 | NM_198674.2 | chr9:109717565-109746089 |
| 7336 | Fbxw28 | NM_001177419.1 | chr9:109322885-109339659 |
| 7337 | Fbxw4 | NM_013907.2 | chr19:45578256-45660193 |
| 7338 | Fbxw5 | NM_013908.4 | chr2:25500777-25505470 |
| 7339 | Fbxw7 | NM_001177773.1 | chr3:84815576-84979198 |
| 7340 | Fbxw8 | NM_172721.2 | chr5:118064980-118155458 |
| 7341 | Fbxw9 | NM_026791.2 | chr8:85060118-85067120 |
| 7342 | Fcamr | NM_001170632.1 | chr1:130800901-130814740 |
| 7343 | Fcer1a | NM_010184.2 | chr1:173221270-173227229 |
| 7344 | Fcer1g | NM_010185.4 | chr1:171229571-171234349 |
| 7345 | Fcer2a | NM_013517.3 | chr8:3681786-3690861 |
| 7346 | Fcf1 | NM_028632.2 | chr12:84970929-84983303 |
| 7347 | Fcgbp | NM_001126603.1 | chr7:28071235-28120864 |
| 7348 | Fcgr1 | NM_010186.5 | chr3:96282908-96293969 |
| 7349 | Fcgr2b | NM_001077189.1 | chr1:170960558-170976071 |
| 7350 | Fcgr3 | NM_010188.5 | chr1:171051168-171059403 |
| 7351 | Fcgr4 | NM_144559.2 | chr1:171018925-171029761 |
| 7352 | Fcgrt | NM_010189.3 | chr7:45092992-45103822 |
| 7353 | Fcho1 | NM_028715.3 | chr8:71708386-71725681 |
| 7354 | Fcho2 | NM_172591.3 | chr13:98723405-98815449 |
| 7355 | Fchsd1 | NM_175684.4 | chr18:37957433-37969731 |
| 7356 | Fchsd2 | NM_001146010.1 | chr7:101108774-101284405 |
| 7357 | Fcna | NM_007995.3 | chr2:25624666-25627974 |
| 7358 | Fcnb | NM_010190.1 | chr2:28076478-28084878 |
| 7359 | Fcrl1 | NM_001136236.1 | chr3:87376386-87392133 |
| 7360 | Fcrl5 | NM_001113238.1 | chr3:87435781-87500678 |
| 7361 | Fcrl6 | NM_001164725.1 | chr1:172596639-172602551 |
| 7362 | Fcrla | NM_001160215.1 | chr1:170917593-170927583 |
| 7363 | Fcrlb | NM_001029984.2 | chr1:170907272-170912941 |
| 7364 | Fcrls | NM_030707.3 | chr3:87250964-87263524 |
| 7365 | Fdft1 | NM_010191.3 | chr14:63145150-63179578 |
| 7366 | Fdps | NM_001253751.1 | chr3:89093587-89101967 |
| 7367 | Fdx1 | NM_007996.2 | chr9:51943024-51963602 |
| 7368 | Fdx1l | NM_001039824.2 | chr9:21067519-21073514 |
| 7369 | Fdxacb1 | NM_198675.2 | chr9:50768237-50772670 |
| 7370 | Fdxr | NM_007997.1 | chr11:115268024-115276969 |
| 7371 | Fech | NM_007998.6 | chr18:64456549-64489066 |
| 7372 | Fem1a | NM_010192.4 | chr17:56256792-56263608 |
| 7373 | Fem1b | NM_010193.4 | chr9:62791829-62811648 |
| 7374 | Fem1c | NM_173423.4 | chr18:46504605-46525971 |
| 7375 | Fen1 | NM_001271614.1 | chr19:10199131-10203943 |
| 7376 | Fendrr | NR_045471.2 | chr8:121054881-121083110 |
| 7377 | Fer1l4 | NM_001136556.1 | chr2:156019139-156052947 |
| 7378 | Fer1l5 | NM_001277076.1 | chr1:36372290-36422110 |
| 7379 | Ferd3l | NM_033522.2 | chr12:33928424-33929309 |
| 7380 | Fermt1 | NM_198029.2 | chr2:132904178-132946036 |
| 7381 | Fermt2 | NM_146054.2 | chr14:45458791-45530065 |
| 7382 | Fermt3 | NM_153795.2 | chr19:6998957-7019469 |
| 7383 | Fert2 | NM_001037997.3 | chr17:63863980-64139496 |
| 7384 | Fes | NM_010194.2 | chr7:80377757-80387946 |
| 7385 | Fetub | NM_001083904.1 | chr16:22920221-22939768 |
| 7386 | Fev | NM_153111.2 | chr1:74881508-74885408 |
| 7387 | Fez1 | NM_183171.4 | chr9:36843658-36878640 |
| 7388 | Fez2 | NM_001285940.1 | chr17:78377877-78418152 |
| 7389 | Fezf1 | NM_028462.1 | chr6:23245046-23248264 |
| 7390 | Fezf2 | NM_080433.3 | chr14:12341891-12345865 |
| 7391 | Ffar1 | NM_194057.2 | chr7:30860567-30861470 |
| 7392 | Ffar2 | NM_001168509.1 | chr7:30818356-30821648 |
| 7393 | Ffar3 | NM_001033316.2 | chr7:30854329-30856178 |
| 7394 | Ffar4 | NM_181748.2 | chr19:38097078-38114263 |
| 7395 | Fga | NM_001111048.2 | chr3:83026152-83033617 |
| 7396 | Fgb | NM_181849.2 | chr3:83042304-83049790 |
| 7397 | Fgd1 | NM_008001.4 | chrX:151047169-151089686 |
| 7398 | Fgd2 | NM_001159538.1 | chr17:29360913-29379535 |
| 7399 | Fgd3 | NM_175759.2 | chr13:49263109-49309208 |
| 7400 | Fgd4 | NM_139232.3 | chr16:16416914-16560219 |
| 7401 | Fgd5 | NM_172731.2 | chr6:91987109-92076005 |
| 7402 | Fgd6 | NM_053072.3 | chr10:94036000-94145339 |
| 7403 | Fgf1 | NM_010197.3 | chr18:38838672-38918699 |
| 7404 | Fgf10 | NM_008002.4 | chr13:118714698-118792573 |

Fig. 26 - 40

| | | | |
|---|---|---|---|
| 7405 | Fgf11 | NM_001291104.1 | chr11:69796067-69801716 |
| 7406 | Fgf12 | NM_001276419.2 | chr16:28157782-28564951 |
| 7407 | Fgf13 | NM_001290414.1 | chrX:59062145-59585572 |
| 7408 | Fgf14 | NM_010201.4 | chr14:123928290-124192546 |
| 7409 | Fgf15 | NM_008003.2 | chr7:144896531-144900951 |
| 7410 | Fgf16 | NM_030614.2 | chrX:105764476-105776532 |
| 7411 | Fgf17 | NM_008004.4 | chr14:70636204-70642268 |
| 7412 | Fgf18 | NM_008005.2 | chr11:33116977-33147400 |
| 7413 | Fgf2 | NM_008006.2 | chr3:37348652-37404830 |
| 7414 | Fgf20 | NM_030610.2 | chr8:40279165-40286953 |
| 7415 | Fgf21 | NM_020013.4 | chr7:45613889-45615490 |
| 7416 | Fgf22 | NM_023304.3 | chr10:79755118-79756961 |
| 7417 | Fgf23 | NM_022657.4 | chr6:127072901-127082296 |
| 7418 | Fgf3 | NM_008007.2 | chr7:144838611-144843348 |
| 7419 | Fgf4 | NM_010202.5 | chr7:144861385-144865243 |
| 7420 | Fgf5 | NM_001277268.1 | chr5:98254183-98277033 |
| 7421 | Fgf6 | NM_010204.1 | chr6:127015541-127024718 |
| 7422 | Fgf7 | NM_008008.4 | chr2:126034657-126091185 |
| 7423 | Fgf8 | NM_001166361.1 | chr19:45736797-45742884 |
| 7424 | Fgf9 | NM_013518.4 | chr14:58072685-58112720 |
| 7425 | Fgfbp1 | NM_001271616.1 | chr5:43978857-43981799 |
| 7426 | Fgfbp3 | NM_028263.1 | chr19:36917549-36919549 |
| 7427 | Fgfr1 | NM_001079908.2 | chr8:25518758-25575718 |
| 7428 | Fgfr1op | NM_001197046.1 | chr17:8165517-8196470 |
| 7429 | Fgfr1op2 | NM_026123.2 | chr6:146577910-146599198 |
| 7430 | Fgfr2 | NM_010207.2 | chr7:130162450-130266808 |
| 7431 | Fgfr3 | NM_001163215.2 | chr5:33721723-33737068 |
| 7432 | Fgfr4 | NM_008011.2 | chr13:55152817-55168759 |
| 7433 | Fgfrl1 | NM_001164259.1 | chr5:108694228-108706950 |
| 7434 | Fgg | NM_133862.1 | chr3:83007895-83015049 |
| 7435 | Fggy | NM_001113412.1 | chr4:95557506-95926939 |
| 7436 | Fgl1 | NM_145594.2 | chr8:41191433-41215156 |
| 7437 | Fgl2 | NM_008013.4 | chr5:21372672-21378386 |
| 7438 | Fgr | NM_010208.4 | chr4:132974094-133001882 |
| 7439 | Fh1 | NM_010209.2 | chr1:175601377-175625635 |
| 7440 | Fhad1 | NM_177699.4 | chr4:141890622-142011651 |
| 7441 | Fhadlos1 | NR_040672.1 | chr4:141982991-141986797 |
| 7442 | Fhdc1 | NM_001033301.4 | chr3:84442195-84480439 |
| 7443 | Fhit | NM_010213.3 | chr14:9550093-11162035 |
| 7444 | Fhl1 | NM_001077361.1 | chrX:56731956-56793346 |
| 7445 | Fhl2 | NM_001289533.1 | chr1:43123070-43196761 |
| 7446 | Fhl3 | NM_010213.3 | chr4:124700698-124708611 |
| 7447 | Fhl4 | NM_010214.4 | chr10:85097018-85102495 |
| 7448 | Fhl5 | NM_021318.3 | chr4:25199908-25242876 |
| 7449 | Fhod1 | NM_177699.4 | chr8:105329159-105347970 |
| 7450 | Fhod3 | NM_001289654.1 | chr18:24708622-25133507 |
| 7451 | Fibcd1 | NM_178887.4 | chr2:31813289-31846005 |
| 7452 | Fibin | NM_026271.1 | chr2:110360924-110362993 |
| 7453 | Fibp | NM_001253832.1 | chr19:5460606-5465052 |
| 7454 | Ficd | NM_001010825.3 | chr5:113735781-113740607 |
| 7455 | Fig4 | NM_133999.1 | chr10:41188171-41303241 |
| 7456 | Figf | NM_010216.2 | chrX:164373521-164402650 |
| 7457 | Figla | NM_012013.1 | chr6:86017190-86020996 |
| 7458 | Fign | NM_001267846.1 | chr2:63971507-64098038 |
| 7459 | Fignl1 | NM_001163359.1 | chr11:11800287-11808962 |
| 7460 | Fignl2 | NM_001214911.2 | chr15:101050191-101054399 |
| 7461 | Filip1 | NM_001081243.1 | chr9:79815561-79977882 |
| 7462 | Filip1l | NM_001040397.4 | chr16:57353276-57572804 |
| 7463 | Fip1l1 | NM_001159573.1 | chr5:74535481-74597124 |
| 7464 | Firre | NR_015505.2 | chrX:50563119-50635321 |
| 7465 | Fis1 | NM_001163243.1 | chr5:136953274-136966234 |
| 7466 | Fitm1 | NM_028808.1 | chr14:55575673-55576952 |
| 7467 | Fitm2 | NM_173397.4 | chr2:163468702-163472629 |
| 7468 | Fiz1 | NM_001110328.1 | chr7:5007055-5014697 |
| 7469 | Fjx1 | NM_010218.2 | chr2:102449365-102461792 |
| 7470 | Fkbp10 | NM_001163481.1 | chr11:100415893-100424840 |
| 7471 | Fkbp11 | NM_024169.3 | chr15:98724367-98728198 |
| 7472 | Fkbp14 | NM_153775.3 | chr6:54577604-54593128 |
| 7473 | Fkbp15 | NM_001045528.1 | chr4:62300341-62360548 |
| 7474 | Fkbp1a | NM_008019.3 | chr2:151542482-151561691 |
| 7475 | Fkbp1b | NM_016863.3 | chr12:4833173-4841595 |
| 7476 | Fkbp2 | NM_001166368.1 | chr19:6977738-6980461 |
| 7477 | Fkbp3 | NM_013902.4 | chr12:65062431-65073938 |
| 7478 | Fkbp4 | NM_010219.3 | chr6:128430106-128438631 |
| 7479 | Fkbp5 | NM_010220.4 | chr17:28398752-28486149 |
| 7480 | Fkbp6 | NM_001277891.1 | chr5:135373364-135350044 |
| 7481 | Fkbp7 | NM_010222.2 | chr2:76663033-76673098 |
| 7482 | Fkbp8 | NM_001111066.1 | chr8:70527742-70535328 |
| 7483 | Fkbp9 | NM_012056.2 | chr6:56832058-56879360 |
| 7484 | Fkbpl | NM_019873.2 | chr17:34644882-34646327 |
| 7485 | Fkrp | NM_173430.2 | chr7:16809266-16816732 |
| 7486 | Fktn | NM_139309.4 | chr4:53714181-53763271 |
| 7487 | Flad1 | NM_177041.3 | chr3:89402672-89411863 |
| 7488 | Flcn | NM_001271356.1 | chr11:59791407-59810039 |
| 7489 | Flg2 | NM_001138041.1 | chr3:93197272-93221376 |
| 7490 | Fli1 | NM_008026.5 | chr9:32422203-32541452 |
| 7491 | Flii | NM_022009.2 | chr11:60714145-60727263 |
| 7492 | Flna | NM_001290421.1 | chrX:74223460-74246534 |
| 7493 | Flnb | NM_001081427.1 | chr14:7817956-7951587 |
| 7494 | Flnc | NM_001081185.1 | chr6:29433152-29461888 |
| 7495 | Flot1 | NM_008027.2 | chr17:35823356-35832787 |
| 7496 | Flot2 | NM_001040403.1 | chr11:78037940-78060432 |
| 7497 | Flrt1 | NM_201411.2 | chr19:7092010-7105729 |
| 7498 | Flrt2 | NM_201518.4 | chr12:95692225-95785213 |
| 7499 | Flrt3 | NM_001172160.1 | chr2:140658197-140671476 |
| 7500 | Flt1 | NM_010228.3 | chr5:147562195-147725988 |
| 7501 | Flt3 | NM_010229.2 | chr5:147330741-147400489 |
| 7502 | Flt3l | NM_013520.3 | chr7:45131188-45136432 |
| 7503 | Flt4 | NM_008029.3 | chr11:49806678-49862739 |
| 7504 | Flywch1 | NM_153791.2 | chr17:23755422-23771591 |
| 7505 | Flywch2 | NM_029798.3 | chr17:23776917-23786077 |
| 7506 | Fmn1 | NM_001285458.1 | chr2:113327735-113716767 |
| 7507 | Fmn2 | NM_019445.2 | chr1:174501824-174822729 |
| 7508 | Fmnl1 | NM_001077698.1 | chr11:103171137-103198900 |
| 7509 | Fmnl2 | NM_172409.2 | chr2:52857867-53134202 |
| 7510 | Fmnl3 | NM_017117.2 | chr15:99317211-99370482 |
| 7511 | Fmo1 | NM_010231.2 | chr1:162829560-162860648 |
| 7512 | Fmo2 | NM_018881.3 | chr1:162875046-162898712 |
| 7513 | Fmo3 | NM_008030.2 | chr1:162953798-162984528 |
| 7514 | Fmo4 | NM_144878.2 | chr1:162793882-162812549 |
| 7515 | Fmo5 | NM_001161763.1 | chr3:97628803-97655287 |
| 7516 | Fmo6 | NM_001178038.1 | chr1:162916550-162937225 |
| 7517 | Fmo9 | NM_172844.2 | chr1:166662054-166681845 |
| 7518 | Fnod | NM_021355.3 | chr1:134037514-134048277 |
| 7519 | Fmr1 | NM_001290424.1 | chrX:68678540-68717961 |
| 7520 | Fmr1nb | NM_001166619.1 | chrX:68761838-68804560 |
| 7521 | Fn1 | NM_001276408.1 | chr1:71585472-71653234 |
| 7522 | Fn3k | NM_001038699.2 | chr11:121434952-121443505 |
| 7523 | Fn3krp | NM_181420.3 | chr11:121421372-121430768 |
| 7524 | Fnbp1 | NM_001038700.2 | chr2:31026205-31142008 |
| 7525 | Fnbp1l | NM_001114665.2 | chr3:122538718-122619714 |
| 7526 | Fnbp4 | NM_018828.2 | chr2:90745369-90781020 |
| 7527 | Fndc3c2 | NM_001033424.3 | chrX:106235245-106255372 |
| 7528 | Fndc1 | NM_010831416.1 | chr17:7738567-7804974 |
| 7529 | Fndc3a | NM_207636.2 | chr14:72537952-72710003 |
| 7530 | Fndc3b | NM_173182.2 | chr3:27416161-27710439 |
| 7531 | Fndc3c1 | NM_001007580.1 | chrX:106420042-106485229 |
| 7532 | Fndc4 | NM_022424.5 | chr5:31292245-31295877 |
| 7533 | Fndc5 | NM_027402.3 | chr4:129137059-129144593 |
| 7534 | Fndc7 | NM_001165965.1 | chr3:108853677-108890008 |
| 7535 | Fndc8 | NM_030824.1 | chr11:82892144-82900737 |
| 7536 | Fndc9 | NM_177075.4 | chr11:46235556-46239871 |
| 7537 | Fnip1 | NM_173753.4 | chr11:54438178-54518241 |
| 7538 | Fnip2 | NM_001162999.2 | chr3:79455970-79567679 |
| 7539 | Fnta | NM_008033.3 | chr8:25998721-26015601 |
| 7540 | Fntb | NM_145927.2 | chr12:76837446-76921412 |
| 7541 | Focad | NM_001081184.1 | chr4:88094629-88411011 |
| 7542 | Folh1 | NM_001159706.1 | chr7:86718975-86775864 |
| 7543 | Folr1 | NM_001252552.1 | chr7:101858330-101870788 |
| 7544 | Folr2 | NM_008035.2 | chr7:101839987-101845331 |
| 7545 | Folr4 | NM_022888.2 | chr9:14900022-14903951 |
| 7546 | Fopnl | NM_025345.2 | chr16:14299243-14317332 |
| 7547 | Fos | NM_010234.2 | chr12:85473900-85477270 |
| 7548 | Fosb | NM_008036.2 | chr7:19302695-19310045 |
| 7549 | Fosl1 | NM_010235.2 | chr19:5447697-5455938 |
| 7550 | Fosl2 | NM_008037.4 | chr5:32136471-32157839 |
| 7551 | Foxa1 | NM_008259.3 | chr12:57540631-57546121 |
| 7552 | Foxa2 | NM_001291065.1 | chr2:148042876-148045948 |
| 7553 | Foxa3 | NM_008260.2 | chr7:19013282-19023539 |
| 7554 | Foxb1 | NM_023378.3 | chr9:69757709-69760940 |
| 7555 | Foxb2 | NM_008203.1 | chr19:16872315-16873830 |
| 7556 | Foxc1 | NM_008592.2 | chr13:31806645-31810635 |
| 7557 | Foxc2 | NM_013519.2 | chr8:121116170-121118894 |
| 7558 | Foxd1 | NM_008242.2 | chr13:98354244-98356705 |
| 7559 | Foxd2 | NM_008593.3 | chr4:114906279-114908898 |
| 7560 | Foxd2os | NR_030721.1 | chr4:114909288-114921118 |
| 7561 | Foxd3 | NM_010425.3 | chr4:99656298-99658671 |
| 7562 | Foxd4 | NM_008022.2 | chr19:24898964-24901309 |
| 7563 | Foxe1 | NM_183298.1 | chr4:46344193-46345309 |
| 7564 | Foxe3 | NM_015758.2 | chr4:114925146-114926013 |
| 7565 | Foxf1 | NM_010426.2 | chr8:121084385-121088154 |
| 7566 | Foxf2 | NM_010225.2 | chr13:31625815-31631406 |
| 7567 | Foxg1 | NM_001160112.1 | chr12:49382882-49386867 |
| 7568 | Foxh1 | NM_007989.4 | chr15:76668223-76669948 |
| 7569 | Foxi1 | NM_023907.4 | chr11:34204340-34208089 |
| 7570 | Foxi2 | NM_183193.2 | chr7:135410366-135413615 |
| 7571 | Foxi3 | NM_001101464.1 | chr6:70956605-70961066 |
| 7572 | Foxj1 | NM_008240.3 | chr11:116330703-116335354 |
| 7573 | Foxj2 | NM_021899.3 | chr6:122820183-122845366 |
| 7574 | Foxj3 | NM_001290696.1 | chr4:119539660-119629119 |
| 7575 | Foxk1 | NM_199068.2 | chr5:142401496-142462015 |
| 7576 | Foxk2 | NM_001080932.2 | chr11:121259986-121309896 |
| 7577 | Foxl1 | NM_008024.2 | chr8:121127684-121130644 |
| 7578 | Foxl2 | NM_012020.2 | chr9:98955606-98958126 |
| 7579 | Foxl2os | NR_003248.3 | chr9:98949154-98955310 |
| 7580 | Foxm1 | NM_008021.4 | chr6:128362993-128375886 |
| 7581 | Foxn1 | NM_001277290.1 | chr11:78357576-78386608 |
| 7582 | Foxn2 | NM_180974.4 | chr17:88440711-88490533 |
| 7583 | Foxn3 | NM_183186.2 | chr12:99195093-99450074 |
| 7584 | Foxn4 | NM_148935.2 | chr5:114254163-114273761 |
| 7585 | Foxo1 | NM_019739.3 | chr3:52268336-52350109 |
| 7586 | Foxo3 | NM_019740.2 | chr10:42185785-42276742 |
| 7587 | Foxo4 | NM_018789.2 | chrX:101254527-101260873 |
| 7588 | Foxo6 | NM_194060.1 | chr4:120267077-120287261 |
| 7589 | Foxp1 | NM_001197321.1 | chr6:98925341-99266515 |
| 7590 | Foxp2 | NM_001286607.1 | chr6:15185505-15441977 |
| 7591 | Foxp3 | NM_001199347.1 | chrX:7579675-7595243 |
| 7592 | Foxp4 | NM_001110824.1 | chr17:47867132-47924632 |
| 7593 | Foxq1 | NM_008239.4 | chr13:31558169-31560974 |
| 7594 | Foxr1 | NM_001033469.2 | chr9:44434233-44440868 |

Fig. 26 - 41

| | | | |
|---|---|---|---|
| 7595 | Foxr2 | NM_001034894.3 | chrX:153118787-153132861 |
| 7596 | Foxred1 | NM_001291448.1 | chr9:35204220-35211055 |
| 7597 | Foxred2 | NM_001017983.2 | chr15:77940521-77956722 |
| 7598 | Foxs1 | NM_010226.2 | chr2:152931897-152933208 |
| 7599 | Fpgs | NM_010236.2 | chr2:32682608-32694175 |
| 7600 | Fpgt | NM_029330.2 | chr3:155084918-155093378 |
| 7601 | Fpr1 | NM_013521.2 | chr17:17876470-17883939 |
| 7602 | Fpr2 | NM_008039.2 | chr17:17887823-17893952 |
| 7603 | Fpr3 | NM_008042.2 | chr17:17970457-17971677 |
| 7604 | Fpr-rs3 | NM_008040.2 | chr17:20623845-20624877 |
| 7605 | Fpr-rs4 | NM_008041.2 | chr17:18021732-18022704 |
| 7606 | Fpr-rs6 | NM_177316.2 | chr17:20182077-20183097 |
| 7607 | Fra10ac1 | NM_001081075.1 | chr19:38188478-38224132 |
| 7608 | Fras1 | NM_175473.3 | chr5:96373954-96784728 |
| 7609 | Frat1 | NM_008043.3 | chr19:41829969-41832583 |
| 7610 | Frat2 | NM_177603.3 | chr19:41845975-41848132 |
| 7611 | Frem1 | NM_001198811.1 | chr4:82897919-83052167 |
| 7612 | Frem2 | NM_172862.3 | chr3:53513937-53657355 |
| 7613 | Frem3 | NM_001167898.1 | chr8:80611038-80695657 |
| 7614 | Frg1 | NM_013522.3 | chr8:41397453-41417118 |
| 7615 | Frk | NM_001159544.1 | chr10:34483399-34611230 |
| 7616 | Frmd3 | NM_001163732.1 | chr4:74013602-74202214 |
| 7617 | Frmd4a | NM_001177843.1 | chr2:4400975-4614043 |
| 7618 | Frmd4b | NM_145148.2 | chr6:97286866-97617657 |
| 7619 | Frmd5 | NM_172673.3 | chr2:121545528-121807057 |
| 7620 | Frmd6 | NM_028127.3 | chr12:70825513-70902234 |
| 7621 | Frmd7 | NM_001190332.1 | chrX:50892644-50942710 |
| 7622 | Frmd8 | NM_026169.4 | chr19:5850973-5875208 |
| 7623 | Frmpd1 | NM_001081172.2 | chr4:45184905-45285936 |
| 7624 | Frmpd1os | NR_040666.1 | chr4:45234722-45243990 |
| 7625 | Frmpd3 | NM_172794.2 | chrX:140367493-140394520 |
| 7626 | Frmpd4 | NM_001033330.3 | chrX:167471305-168577233 |
| 7627 | Frrs1 | NM_001113478.1 | chr3:116859566-116903750 |
| 7628 | Frrs1l | NM_001142965.1 | chr4:56960135-56990391 |
| 7629 | Frs2 | NM_177798.3 | chr10:117070126-117148474 |
| 7630 | Frs3 | NM_144939.2 | chr17:47695206-47704286 |
| 7631 | Frs3os | NR_045912.1 | chr17:47699968-47701996 |
| 7632 | Fry | NM_172887.2 | chr5:150259929-150497753 |
| 7633 | Fryl | NM_028194.2 | chr5:73020190-73256618 |
| 7634 | Frzb | NM_011356.4 | chr2:80411969-80447396 |
| 7635 | Fsbb | NM_001256142.1 | chr4:11579661-11587802 |
| 7636 | Fscb | NM_001168271.1 | chr12:64471332-64474898 |
| 7637 | Fscn1 | NM_007984.2 | chr5:142960354-142973189 |
| 7638 | Fscn2 | NM_172802.4 | chr11:120361533-120368173 |
| 7639 | Fscn3 | NM_019459.2 | chr6:28427900-28438622 |
| 7640 | Fsd1 | NM_183178.2 | chr17:55988510-55996881 |
| 7641 | Fsd1l | NM_001195284.1 | chr4:53631470-53707009 |
| 7642 | Fsd2 | NM_172904.2 | chr7:81534353-81566981 |
| 7643 | Fshb | NM_008045.3 | chr2:107055985-107059651 |
| 7644 | Fshr | NM_013523.3 | chr17:88984951-89200675 |
| 7645 | Fsip1 | NM_027759.3 | chr2:118204887-118256966 |
| 7646 | Fst | NM_008046.3 | chr13:114452261-114458951 |
| 7647 | Fstl1 | NM_008047.5 | chr16:37777054-37836516 |
| 7648 | Fstl3 | NM_031380.2 | chr10:79777273-79782630 |
| 7649 | Fstl4 | NM_177059.3 | chr11:52764705-53187347 |
| 7650 | Fstl5 | NM_001253719.1 | chr3:76075582-76710005 |
| 7651 | Ftcd | NM_080845.2 | chr10:76575647-76590338 |
| 7652 | Fth1 | NM_010239.2 | chr19:9982645-9985111 |
| 7653 | Fthl17 | NM_031261.2 | chrX:9033485-9034333 |
| 7654 | Ftl1 | NM_010240.2 | chr7:45457943-45459886 |
| 7655 | Ftmt | NM_026286.3 | chr18:52331535-52332996 |
| 7656 | Fto | NM_011936.2 | chr8:91313524-91668433 |
| 7657 | Ftsj1 | NM_001290430.1 | chrX:8238667-8252406 |
| 7658 | Ftsj2 | NM_026810.1 | chr5:140327973-140331898 |
| 7659 | Ftsj3 | NM_025324.2 | chr11:106249143-106255802 |
| 7660 | Ftx | NR_028380.1 | chrX:103569504-103623754 |
| 7661 | Fubp1 | NM_057172.3 | chr3:152210457-152236830 |
| 7662 | Fubp3 | NM_001033389.4 | chr2:31572650-31617526 |
| 7663 | Fuca1 | NM_024243.4 | chr4:135920725-135940300 |
| 7664 | Fuca2 | NM_025799.4 | chr10:13501027-13517275 |
| 7665 | Fuk | NM_172283.3 | chr8:110882455-110902488 |
| 7666 | Fundc1 | NM_026058.4 | chrX:17555599-17572325 |
| 7667 | Fundc2 | NM_026126.4 | chrX:75382398-75397158 |
| 7668 | Fuom | NM_001286217.1 | chr7:140097814-140102441 |
| 7669 | Furin | NM_001081454.2 | chr7:80389193-80405436 |
| 7670 | Fus | NM_139149.2 | chr7:127967478-127982031 |
| 7671 | Fut1 | NM_001271981.1 | chr7:45617605-45621059 |
| 7672 | Fut10 | NM_001012517.5 | chr8:31187330-31261924 |
| 7673 | Fut11 | NM_028428.2 | chr14:20694967-20700197 |
| 7674 | Fut2 | NM_001271993.1 | chr7:45648590-45666394 |
| 7675 | Fut4 | NM_010242.3 | chr9:14748458-14752122 |
| 7676 | Fut4-ps1 | NR_033644.1 | chr17:56734227-56739292 |
| 7677 | Fut7 | NM_001177366.1 | chr2:25423693-25426373 |
| 7678 | Fut8 | NM_001252614.1 | chr12:77238103-77475896 |
| 7679 | Fut9 | NM_010243.3 | chr4:25609332-25800003 |
| 7680 | Fuz | NM_027376.3 | chr7:44896078-44900624 |
| 7681 | Fv1 | NM_010244.3 | chr4:147868978-147870358 |
| 7682 | Fxn | NM_008044.2 | chr19:24261452-24280586 |
| 7683 | Fxr1 | NM_001113188.1 | chr3:34020078-34069344 |
| 7684 | Fxr2 | NM_011814.2 | chr11:69632970-69653297 |
| 7685 | Fxyd1 | NM_019503.4 | chr7:31051677-31055656 |
| 7686 | Fxyd2 | NM_007503.3 | chr9:45406076-45410278 |
| 7687 | Fxyd3 | NM_008557.2 | chr7:31070534-31076697 |
| 7688 | Fxyd4 | NM_001173372.1 | chr6:117935558-117937335 |
| 7689 | Fxyd5 | NM_001111073.2 | chr7:31032722-31041839 |
| 7690 | Fxyd6 | NM_022004.6 | chr9:45370184-45396159 |
| 7691 | Fxyd7 | NM_022007.1 | chr7:31042514-31051454 |
| 7692 | Fyb | NM_001278269.1 | chr15:6579846-6665608 |
| 7693 | Fyco1 | NM_001110253.2 | chr9:123789499-123851899 |
| 7694 | Fyn | NM_001122892.1 | chr10:39369798-39565374 |
| 7695 | Fyttd1 | NM_001159349.1 | chr16:32877783-32908963 |
| 7696 | Fzd1 | NM_021457.3 | chr5:4753838-4758216 |
| 7697 | Fzd10 | NM_175284.3 | chr5:128601105-128604093 |
| 7698 | Fzd2 | NM_020510.2 | chr11:102604430-102608058 |
| 7699 | Fzd3 | NM_021458.2 | chr14:65192440-65262463 |
| 7700 | Fzd4 | NM_008055.4 | chr7:89404365-89410110 |
| 7701 | Fzd5 | NM_001042659.1 | chr1:64730657-64737750 |
| 7702 | Fzd6 | NM_001162494.1 | chr15:39006279-39038190 |
| 7703 | Fzd7 | NM_008057.3 | chr1:59482146-59486955 |
| 7704 | Fzd8 | NM_008058.2 | chr18:9212855-9216201 |
| 7705 | Fzd9 | NM_010246.1 | chr5:135248937-135251047 |
| 7706 | Fzr1 | NM_019757.1 | chr10:81366878-81378370 |
| 7707 | G0s2 | NM_008059.3 | chr1:193272159-193273188 |
| 7708 | G2e3 | NM_001015099.2 | chr12:51348229-51376986 |
| 7709 | G3bp1 | NM_013716.2 | chr11:55469751-55500887 |
| 7710 | G3bp2 | NM_001080794.2 | chr5:92052144-92083598 |
| 7711 | G530011O06Rik | NR_029457.1 | chrX:169975042-169978917 |
| 7712 | G630025P09Rik | NR_027913.1 | chr11:69803668-69806038 |
| 7713 | G630055G22Rik | NR_045404.1 | chr18:47922840-48107980 |
| 7714 | G630071F17Rik | NR_045401.1 | chr18:60663409-60671624 |
| 7715 | G630090E17Rik | NM_001173500.2 | chr10:39946911-39960153 |
| 7716 | G630093K05Rik | NR_045156.1 | chr13:47910434-47934301 |
| 7717 | G6b | NM_001033221.3 | chr17:35062692-35066184 |
| 7718 | G6bos | NR_001462.1 | chr17:35064436-35065596 |
| 7719 | G6pc | NM_008061.4 | chr11:101367715-101377903 |
| 7720 | G6pc2 | NM_021289856.1 | chr2:69211072-69227993 |
| 7721 | G6pc3 | NM_175935.3 | chr11:102189698-102194081 |
| 7722 | G6pd2 | NM_019468.2 | chr5:61808842-61810477 |
| 7723 | G6pdx | NM_008062.2 | chrX:74409485-74429161 |
| 7724 | G730013B05Rik | NR_040379.1 | chr16:50528501-50559459 |
| 7725 | Gaa | NM_001159324.1 | chr11:119267966-119285698 |
| 7726 | Gab1 | NM_021356.2 | chr8:80764433-80880479 |
| 7727 | Gab2 | NM_001162477.1 | chr7:97081750-97308951 |
| 7728 | Gab3 | NM_181584.4 | chrX:74988544-75084905 |
| 7729 | Gabarap | NM_019749.4 | chr11:69991369-69994949 |
| 7730 | Gabarapl1 | NM_020590.4 | chr6:129533191-129542331 |
| 7731 | Gabarapl2 | NM_026693.5 | chr11:77162750-77152915 |
| 7732 | Gabbr1 | NM_019439.3 | chr17:37043665-37074305 |
| 7733 | Gabbr2 | NM_001081141.1 | chr4:46663897-46991714 |
| 7734 | Gabpa | NM_008065.2 | chr16:84835123-84863778 |
| 7735 | Gabpb1 | NM_001271467.1 | chr2:126628906-126675592 |
| 7736 | Gabpb2 | NM_029885.1 | chr3:95181765-95217942 |
| 7737 | Gabra1 | NM_010250.5 | chr11:42130939-42182930 |
| 7738 | Gabra2 | NM_008066.3 | chr5:70961056-71095849 |
| 7739 | Gabra3 | NM_008067.4 | chrX:72432675-72656246 |
| 7740 | Gabra4 | NM_010251.2 | chr7:71569733-71658308 |
| 7741 | Gabra5 | NM_176942.4 | chr7:57407668-57510009 |
| 7742 | Gabra6 | NM_001099641.2 | chr11:42306436-42321072 |
| 7743 | Gabrb1 | NM_008069.4 | chr5:71700015-72137244 |
| 7744 | Gabrb2 | NM_008070.3 | chr11:42419756-42632591 |
| 7745 | Gabrb3 | NM_001038701.2 | chr7:57590517-57828801 |
| 7746 | Gabrd | NM_008072.2 | chr4:155384978-155398069 |
| 7747 | Gabre | NM_017369.2 | chrX:72257431-72274721 |
| 7748 | Gabrg1 | NM_010252.4 | chr5:70751046-70842617 |
| 7749 | Gabrg2 | NM_008073.3 | chr11:41910189-42000714 |
| 7750 | Gabrg3 | NM_008074.2 | chr7:56724241-57386871 |
| 7751 | Gabrp | NM_146017.3 | chr11:33550780-33578957 |
| 7752 | Gabrq | NM_001290435.1 | chrX:72825177-72842602 |
| 7753 | Gabrr1 | NM_008075.2 | chr4:33132555-33163588 |
| 7754 | Gabrr2 | NM_008076.3 | chr4:33063111-33095865 |
| 7755 | Gabrr3 | NM_001081190.1 | chr16:59407381-59461739 |
| 7756 | Gad1 | NM_008077.5 | chr2:70562128-70602014 |
| 7757 | Gad1os | NR_040496.1 | chr2:70489939-70563357 |
| 7758 | Gad2 | NM_008078.2 | chr2:22622326-22693877 |
| 7759 | Gadd45a | NM_007836.1 | chr6:67035095-67037407 |
| 7760 | Gadd45b | NM_008655.1 | chr10:80930090-80932204 |
| 7761 | Gadd45g | NM_011817.2 | chr13:51846674-51848474 |
| 7762 | Gadd45gip1 | NM_183358.4 | chr8:84832281-84835482 |
| 7763 | Gadl1 | NM_028638.1 | chr9:115909454-116076176 |
| 7764 | Gak | NM_001282051.1 | chr5:108569106-108629777 |
| 7765 | Gal | NM_010253.3 | chr19:3409916-3414457 |
| 7766 | Gal3st1 | NM_001177691.1 | chr11:3989932-3999328 |
| 7767 | Gal3st2 | NM_199366.4 | chr1:93861343-93876494 |
| 7768 | Gal3st3 | NM_001024717.2 | chr19:5298330-5308739 |
| 7769 | Gal3st4 | NM_001033416.2 | chr5:138264924-138272754 |
| 7770 | Galc | NM_008079.4 | chr12:98202299-98259459 |
| 7771 | Gale | NM_178389.3 | chr4:135965164-135968178 |
| 7772 | Galk1 | NM_016905.2 | chr11:116008356-116012719 |
| 7773 | Galk2 | NM_001291002.1 | chr2:125866222-125984298 |
| 7774 | Galn | NM_176963.4 | chr17:80127470-80185032 |
| 7775 | Galns | NM_001193645.1 | chr8:122578236-122611487 |
| 7776 | Galnt1 | NM_001160404.1 | chr18:24205993-24286816 |
| 7777 | Galnt10 | NM_134189.2 | chr11:57645441-57787500 |
| 7778 | Galnt11 | NM_144908.3 | chr5:25222892-25265918 |
| 7779 | Galnt12 | NM_172693.3 | chr4:47091952-47123042 |
| 7780 | Galnt13 | NM_173030.2 | chr2:54436386-55117744 |
| 7781 | Galnt14 | NM_027864.2 | chr17:73493750-73710451 |
| 7782 | Galnt15 | NM_030166.3 | chr14:32029102-32058326 |
| 7783 | Galnt16 | NM_001081421.1 | chr12:80518989-80603896 |
| 7784 | Galnt18 | NM_173739.3 | chr7:111471660-111779977 |

Fig. 26 - 42

| | | | | | | | |
|---|---|---|---|---|---|---|---|
| 7785 | Galnt2 | NM_139272.2 | chr8:124231393-124345723 | 7880 | Gcsam | NM_001159297.1 | chr16:45610439-45622867 |
| 7786 | Galnt3 | NM_015736.2 | chr2:66082765-66124793 | 7881 | Gcsh | NM_026572.3 | chr8:116981827-116993449 |
| 7787 | Galnt4 | NM_015737.4 | chr10:99108134-99113247 | 7882 | Gda | NM_010266.2 | chr19:21391306-21472661 |
| 7788 | Galnt5 | NM_172855.3 | chr2:57998154-58039171 | 7883 | Gdap1 | NM_010267.3 | chr1:17145372-17164270 |
| 7789 | Galnt6 | NM_001161767.1 | chr15:100689914-100729376 | 7884 | Gdap10 | NR_045032.1 | chr12:32824115-32826908 |
| 7790 | Galnt7 | NM_001167981.1 | chr8:57523824-57653055 | 7885 | Gdap1l1 | NM_144891.2 | chr2:163438466-163455324 |
| 7791 | Galnt9 | NM_001122639.2 | chr5:110603504-110621383 | 7886 | Gdap2 | NM_010269.3 | chr3:100162462-100206989 |
| 7792 | Galnt15 | NM_026449.3 | chr5:25181479-25220289 | 7887 | Gde1 | NM_019580.4 | chr7:118688557-118705738 |
| 7793 | Galnt16 | NM_175032.3 | chr8:57774051-58911627 | 7888 | Gdf1 | NM_001163282.2 | chr8:70315774-70331592 |
| 7794 | Galp | NM_178028.2 | chr7:6197089-6216137 | 7889 | Gdf10 | NM_145741.2 | chr14:33923586-33935282 |
| 7795 | Galr1 | NM_008082.2 | chr18:82392495-82406777 | 7890 | Gdf11 | NM_010272.1 | chr10:128884545-128891718 |
| 7796 | Galr2 | NM_010254.4 | chr11:116280938-116283938 | 7891 | Gdf15 | NM_011819.2 | chr8:70629393-70631635 |
| 7797 | Galr3 | NM_015738.2 | chr15:79041884-79043558 | 7892 | Gdf2 | NM_019506.4 | chr14:33941038-33947198 |
| 7798 | Galt | NM_016658.3 | chr4:41755227-41759224 | 7893 | Gdf3 | NM_008108.4 | chr6:122605402-122610071 |
| 7799 | Gamt | NM_010255.3 | chr10:80258150-80260968 | 7894 | Gdf5 | NM_008109.2 | chr2:155941024-155945364 |
| 7800 | Gan | NM_001081151.1 | chr8:117158134-117205186 | 7895 | Gdf6 | NM_013526.1 | chr4:9844371-9862345 |
| 7801 | Ganab | NM_008060.2 | chr19:8898056-8916742 | 7896 | Gdf7 | NM_013527.1 | chr12:8297917-8301954 |
| 7802 | Ganc | NM_172672.2 | chr2:120403895-120460852 | 7897 | Gdf9 | NM_008110.2 | chr11:53433285-53437902 |
| 7803 | Gap43 | NM_008083.2 | chr16:42248560-42340651 | 7898 | Gdi1 | NM_010273.4 | chrX:74305011-74311867 |
| 7804 | Gapdh | NM_001289726.1 | chr6:125161851-125166467 | 7899 | Gdi2 | NM_008112.4 | chr13:3538074-3566261 |
| 7805 | Gapdhs | NM_001290631.1 | chr7:30729778-30743681 | 7900 | Gdnf | NM_010275.3 | chr15:7810047-7837580 |
| 7806 | Gapt | NM_177713.3 | chr13:110352614-110357172 | 7901 | Gdpd1 | NM_025638.2 | chr11:87033793-87074137 |
| 7807 | Gapvd1 | NM_025709.2 | chr2:34676982-34755232 | 7902 | Gdpd2 | NM_023608.4 | chrX:100729846-100738901 |
| 7808 | Gar1 | NM_026578.3 | chr3:129824911-129831396 | 7903 | Gdpd3 | NM_024228.2 | chr7:126766413-126775645 |
| 7809 | Garem | NM_001033445.2 | chr18:21127341-21300139 | 7904 | Gdpd4 | NM_177696.3 | chr7:97919957-98049663 |
| 7810 | Gareml | NM_001167879.1 | chr5:30105195-30118380 | 7905 | Gdpd5 | NM_201352.2 | chr7:99381548-99460984 |
| 7811 | Garnl3 | NM_178888.4 | chr2:32986365-33087204 | 7906 | Gdpgp1 | NM_178752.3 | chr7:80232892-80241420 |
| 7812 | Gars | NM_180678.3 | chr6:55038000-55079504 | 7907 | Gem | NM_010276.4 | chr4:11704446-11714993 |
| 7813 | Gart | NM_010256.2 | chr16:91621396-91646972 | 7908 | Gemin2 | NM_025656.5 | chr12:59013390-59028470 |
| 7814 | Gas1 | NM_008086.2 | chr13:60174404-60177535 | 7909 | Gemin4 | NM_177367.3 | chr11:76210570-76217572 |
| 7815 | Gas2 | NM_008087.2 | chr7:51879144-51994458 | 7910 | Gemin5 | NM_001166669.1 | chr11:58120000-58168539 |
| 7816 | Gas2l1 | NM_001190406.1 | chr11:5054130-5065327 | 7911 | Gemin6 | NM_026053.3 | chr17:80224488-80228497 |
| 7817 | Gas2l2 | NM_001013759.2 | chr11:83421634-83429521 | 7912 | Gemin7 | NM_027189.2 | chr7:19564948-19573343 |
| 7818 | Gas2l3 | NM_001033331.2 | chr10:89408822-89443967 | 7913 | Gemin8 | NM_146238.4 | chrX:166170453-166190512 |
| 7819 | Gas5 | NR_002840.2 | chr1:161035165-161038537 | 7914 | Gen1 | NM_177331.4 | chr12:11240925-11265787 |
| 7820 | Gas6 | NM_019521.2 | chr8:13465373-13494535 | 7915 | Get4 | NM_001163316.1 | chr5:139253496-139270050 |
| 7821 | Gas7 | NM_001109657.3 | chr11:67586499-67688992 | 7916 | Gfap | NM_001131020.1 | chr11:102890165-102897200 |
| 7822 | Gas8 | NM_018855.2 | chr8:123518834-123536650 | 7917 | Gfer | NM_023040.3 | chr17:24693190-24696156 |
| 7823 | Gast | NM_010257.1 | chr11:100334411-100336996 | 7918 | Gfi1 | NM_001267621.1 | chr5:107716654-107725805 |
| 7824 | Gata1 | NM_008089.2 | chrX:7959259-7967910 | 7919 | Gfi1b | NM_001160406.1 | chr2:28609449-28621982 |
| 7825 | Gata2 | NM_008090.5 | chr6:88198663-88207032 | 7920 | Gfm1 | NM_138591.2 | chr3:67430114-67475068 |
| 7826 | Gata3 | NM_008091.3 | chr2:9857077-9878600 | 7921 | Gfm2 | NM_001146043.2 | chr13:97137936-97181196 |
| 7827 | Gata4 | NM_008092.4 | chr14:63198913-63245271 | 7922 | Gfod1 | NM_001033399.4 | chr13:43195518-43304172 |
| 7828 | Gata5 | NM_008093.2 | chr2:180325087-180334679 | 7923 | Gfod2 | NM_027469.4 | chr8:105716112-105758607 |
| 7829 | Gata5os | NR_045877.1 | chr2:180332856-180340732 | 7924 | Gfpt1 | NM_013528.3 | chr6:87042845-87092207 |
| 7830 | Gata6 | NM_010258.3 | chr18:11052509-11085635 | 7925 | Gfpt2 | NM_013529.3 | chr11:49794154-49838620 |
| 7831 | Gatad1 | NM_026033.2 | chr5:3639960-3647936 | 7926 | Gfra1 | NM_001285457.1 | chr19:58235604-58454594 |
| 7832 | Gatad2a | NM_001113346.1 | chr8:69907068-69974383 | 7927 | Gfra2 | NM_008115.3 | chr14:70890106-70979840 |
| 7833 | Gatad2b | NM_139304.1 | chr3:90341653-90358120 | 7928 | Gfra3 | NM_010280.4 | chr18:34689897-34720387 |
| 7834 | Gatc | NM_029645.3 | chr5:115333241-115341161 | 7929 | Gfra4 | NM_001136063.2 | chr2:131039631-131043088 |
| 7835 | Gatm | NM_025961.5 | chr2:122594472-122611277 | 7930 | Gfral | NM_205844.3 | chr9:76164101-76213657 |
| 7836 | Gatsl2 | NM_030719.2 | chr5:134099747-134141758 | 7931 | Gfy | NM_001195255.1 | chr7:45176348-45179597 |
| 7837 | Gatsl3 | NM_028022.1 | chr11:4218250-4222409 | 7932 | Gga1 | NM_145929.2 | chr15:78877189-78894585 |
| 7838 | Gba | NM_001077411.2 | chr3:89202924-89208966 | 7933 | Gga2 | NM_028758.2 | chr7:121986721-122021198 |
| 7839 | Gba2 | NM_172692.3 | chr4:43566927-43578864 | 7934 | Gga3 | NM_001252067.1 | chr11:115584254-115603916 |
| 7840 | Gbas | NM_008095.4 | chr5:129725074-129758325 | 7935 | Ggact | NM_145466.2 | chr14:122890859-122913165 |
| 7841 | Gbe1 | NM_028803.4 | chr16:70313948-70569720 | 7936 | Ggct | NM_026637.3 | chr6:54985094-54992867 |
| 7842 | Gbf1 | NM_178930.3 | chr19:46152557-46286510 | 7937 | Ggcx | NM_019802.5 | chr6:72414307-72431106 |
| 7843 | Gbgt1 | NM_139197.2 | chr2:28496890-28505415 | 7938 | Ggh | NM_010281.2 | chr4:20042051-20066111 |
| 7844 | Gbp10 | NM_001039646.2 | chr5:105215698-105239533 | 7939 | Ggn | NM_182694.2 | chr7:29170209-29173933 |
| 7845 | Gbp11 | NM_001039647.3 | chr5:105323025-105346472 | 7940 | Ggnbp1 | NM_001251881.1 | chr17:27018034-27036377 |
| 7846 | Gbp2 | NM_010260.1 | chr3:142620662-142638008 | 7941 | Ggnbp2 | NM_153144.2 | chr11:84832360-84870738 |
| 7847 | Gbp2b | NM_010259.2 | chr3:142594846-142619176 | 7942 | Ggps1 | NM_010282.2 | chr13:14052444-14063401 |
| 7848 | Gbp3 | NM_001289492.1 | chr3:142560051-142573212 | 7943 | Ggt1 | NM_008116.3 | chr10:75573494-75586191 |
| 7849 | Gbp4 | NM_001256005.1 | chr5:105115766-105139586 | 7944 | Ggt5 | NM_011820.4 | chr10:75583380-75616968 |
| 7850 | Gbp5 | NM_153564.2 | chr3:142496933-142522344 | 7945 | Ggt6 | NM_027819.2 | chr11:72435525-72438404 |
| 7851 | Gbp6 | NM_194336.2 | chr5:105270701-105293699 | 7946 | Ggt7 | NM_144786.2 | chr2:155490379-155514846 |
| 7852 | Gbp7 | NM_001083312.2 | chr5:105240335-142550151 | 7947 | Ggta1 | NM_001145421.2 | chr2:35400378-35461449 |
| 7853 | Gbp8 | NM_029509.4 | chr5:105014152-105053561 | 7948 | Gh | NM_008117.3 | chr11:106300260-106301896 |
| 7854 | Gbp9 | NM_172777.3 | chr5:105078393-105110292 | 7949 | Ghdc | NM_031871.1 | chr11:100766331-100770957 |
| 7855 | Gbx1 | NM_015739.2 | chr5:24504425-24526848 | 7950 | Ghitm | NM_001199122.1 | chr14:37120444-37135139 |
| 7856 | Gbx2 | NM_010262.3 | chr1:89927961-89931176 | 7951 | Ghr | NM_001048178.2 | chr15:3327524-3583352 |
| 7857 | Gc | NM_008096.4 | chr5:89417510-89457898 | 7952 | Ghrh | NM_010285.2 | chr2:157329495-157346655 |
| 7858 | Gca | NM_145523.3 | chr2:62664326-62694109 | 7953 | Ghrhr | NM_001003685.3 | chr6:55376294-55388530 |
| 7859 | Gcat | NM_001161712.1 | chr15:79030873-79042531 | 7954 | Ghrl | NM_001286404.1 | chr6:113716118-113719454 |
| 7860 | Gcc1 | NM_028900.4 | chr6:28416602-28421724 | 7955 | Ghsr | NM_177330.4 | chr3:27371350-27378010 |
| 7861 | Gcc2 | NM_027375.2 | chr10:58255525-58305592 | 7956 | Gid4 | NM_025757.4 | chr11:60417144-60445277 |
| 7862 | Gcdh | NM_001044744.1 | chr8:84886386-84893921 | 7957 | Gid8 | NM_001289651.1 | chr2:180710327-180721599 |
| 7863 | Gcfc2 | NM_177884.2 | chr6:81923668-81959098 | 7958 | Gif | NM_008118.3 | chr19:11747558-11763447 |
| 7864 | Gcg | NM_008100.4 | chr2:62474529-62483653 | 7959 | Gigyf1 | NM_031408.2 | chr5:137518879-137527935 |
| 7865 | Gcgr | NM_008101.2 | chr11:120530726-120538984 | 7960 | Gigyf2 | NM_001110212.2 | chr1:87326997-87450810 |
| 7866 | Gch1 | NM_008103.2 | chr14:47153894-47189402 | 7961 | Gimap1 | NM_008376.3 | chr6:48739046-48743795 |
| 7867 | Gchfr | NM_177157.4 | chr2:119167787-119172389 | 7962 | Gimap3 | NM_031247.3 | chr6:48764463-48770851 |
| 7868 | Gck | NM_001287386.1 | chr11:5900820-5915135 | 7963 | Gimap4 | NM_001243199.1 | chr6:48684577-48692062 |
| 7869 | Gckr | NM_144909.1 | chr5:31297589-31327302 | 7964 | Gimap5 | NM_175035.5 | chr6:48746196-48754200 |
| 7870 | Gclc | NM_010295.2 | chr9:77754534-77794489 | 7965 | Gimap6 | NM_153175.3 | chr6:48701582-48708244 |
| 7871 | Gclm | NM_008129.4 | chr3:122245556-122267215 | 7966 | Gimap7 | NM_146167.3 | chr6:48718620-48724636 |
| 7872 | Gcm1 | NM_008103.3 | chr9:78051957-78065624 | 7967 | Gimap8 | NM_001077410.1 | chr6:48647233-48660875 |
| 7873 | Gcm2 | NM_008104.2 | chr13:41101426-41109988 | 7968 | Gimap9 | NM_174960.2 | chr6:48676134-48678704 |
| 7874 | Gcn1l1 | NM_172719.2 | chr5:115565282-115622654 | 7969 | Gin1 | NM_026250.3 | chr1:97770171-97793708 |
| 7875 | Gcnt1 | NM_001136484.3 | chr19:17326140-17339505 | 7970 | Ginm1 | NM_145418.4 | chr10:7767946-7780917 |
| 7876 | Gcnt2 | NM_008105.3 | chr13:40886757-40960892 | 7971 | Gins1 | NM_001163476.1 | chr2:150909593-150926079 |
| 7877 | Gcnt3 | NM_028087.2 | chr9:70031495-70038088 | 7972 | Gins2 | NM_178856.1 | chr8:120581265-120589075 |
| 7878 | Gcnt4 | NM_001166065.1 | chr13:96924688-96950914 | 7973 | Gins3 | NM_030198.3 | chr8:95633558-95645059 |
| 7879 | Gcnt7 | NM_001039560.3 | chr2:172450312-172458596 | 7974 | Gins4 | NM_024240.6 | chr8:23226609-23237668 |

Fig. 26 - 43

| | | | | | | | | |
|---|---|---|---|---|---|---|---|---|
| 7975 | Gip | NM_008119.2 | chr11:96024544-96030828 | | 8070 | Gm10033 | NR_038043.1 | chr8:69371024-69395544 |
| 7976 | Gipc1 | NM_018771.3 | chr8:83652677-83664789 | | 8071 | Gm10046 | NR_033484.1 | chr7:27765672-27770972 |
| 7977 | Gipc2 | NM_016867.1 | chr3:152093840-152165900 | | 8072 | Gm10052 | NR_002885.3 | chr15:103240431-103244584 |
| 7978 | Gipc3 | NM_148951.1 | chr10:81337761-81343266 | | 8073 | Gm10057 | NM_001243016.1 | chrX:154001589-154055041 |
| 7979 | Gipr | NM_001080815.1 | chr7:19157124-19166127 | | 8074 | Gm10058 | NM_001109969.2 | chrX:24948455-35427089 |
| 7980 | Git1 | NM_001004144.1 | chr11:77493411-77507774 | | 8075 | Gm10069 | NR_028592.1 | chr6:128438756-128475845 |
| 7981 | Git2 | NM_001077359.1 | chr5:114727407-114773492 | | 8076 | Gm10081 | NM_001162940.1 | chr7:107105911-107106859 |
| 7982 | Gja1 | NM_010288.3 | chr10:56377299-56390419 | | 8077 | Gm10094 | NM_001142441.1 | chr14:57798217-57802330 |
| 7983 | Gja10 | NM_010289.2 | chr4:32600864-32602382 | | 8078 | Gm10096 | NM_001102678.2 | chrX:24948454-35427090 |
| 7984 | Gja3 | NM_001271623.1 | chr14:57034459-57057723 | | 8079 | Gm101 | NM_001115074.1 | chr1:119923518-119995210 |
| 7985 | Gja4 | NM_008120.3 | chr4:127311419-127314099 | | 8080 | Gm10100 | NM_001205033.1 | chr10:77726485-77726848 |
| 7986 | Gja5 | NM_001271628.1 | chr3:97032401-97053634 | | 8081 | Gm10104 | NM_001177481.1 | chr3:21065037-21066001 |
| 7987 | Gja6 | NM_001001496.2 | chrX:160902115-160907052 | | 8082 | Gm10125 | NR_033552.1 | chr18:5491560-5592437 |
| 7988 | Gja8 | NM_008123.3 | chr3:96913565-96926053 | | 8083 | Gm10142 | NM_001205035.1 | chr10:77715806-77716169 |
| 7989 | Gjb1 | NM_008124.3 | chrX:101377234-101385629 | | 8084 | Gm10147 | NM_001099919.2 | chrX:24948454-35427090 |
| 7990 | Gjb2 | NM_008125.3 | chr14:57098601-57104702 | | 8085 | Gm10190 | NR_028385.1 | chr17:80371856-80373542 |
| 7991 | Gjb3 | NM_001160012.1 | chr4:127325234-127330836 | | 8086 | Gm10220 | NM_001134299.1 | chr5:26114763-26121425 |
| 7992 | Gjb4 | NM_008127.4 | chr4:127351085-127354081 | | 8087 | Gm10228 | NM_001270487.1 | chr16:89040922-89041472 |
| 7993 | Gjb5 | NM_010291.3 | chr4:127354808-127358164 | | 8088 | Gm10229 | NM_001199334.2 | chr16:89015276-89015846 |
| 7994 | Gjb6 | NM_001010937.2 | chr14:57123300-57133611 | | 8089 | Gm10230 | NM_001099347.2 | chrX:24948450-35427093 |
| 7995 | Gjc1 | NM_001159382.1 | chr11:102799477-102819159 | | 8090 | Gm10248 | NR_033550.1 | chr14:23038194-23094571 |
| 7996 | Gjc2 | NM_080454.4 | chr11:59175563-59183213 | | 8091 | Gm10267 | NM_001281470.1 | chr18:44156402-44159885 |
| 7997 | Gjc3 | NM_080450.4 | chr5:137953808-137962959 | | 8092 | Gm10272 | NR_026831.1 | chr10:77706586-77706986 |
| 7998 | Gjd2 | NM_010290.2 | chr2:114009600-114013619 | | 8093 | Gm10280 | NR_033584.1 | chr8:113067261-113093333 |
| 7999 | Gjd3 | NM_178596.3 | chr11:98982179-98983016 | | 8094 | Gm10318 | NM_001162944.1 | chr10:77852858-77853788 |
| 8000 | Gjd4 | NM_153086.5 | chr18:9278606-9282809 | | 8095 | Gm10319 | NR_003624.2 | chr6:122136627-122150958 |
| 8001 | Gje1 | NM_029722.1 | chr10:14715625-14718214 | | 8096 | Gm10324 | NM_001177832.1 | chr13:66113452-66122836 |
| 8002 | Gk2 | NM_024245.4 | chr5:97455160-97457008 | | 8097 | Gm10334 | NM_001103153.1 | chr6:41442213-41446097 |
| 8003 | Gk5 | NM_177352.2 | chr9:96119428-96182953 | | 8098 | Gm10336 | NR_045170.1 | chr13:121182716-121186488 |
| 8004 | Gkap1 | NM_019832.3 | chr13:58233350-58274188 | | 8099 | Gm10354 | NM_001281514.1 | chr5:14974496-14978899 |
| 8005 | Gkn1 | NM_025466.1 | chr6:87345652-87350915 | | 8100 | Gm10364 | NR_073535.1 | chr14:55038461-55042976 |
| 8006 | Gkn2 | NM_025467.1 | chr6:87373364-87379494 | | 8101 | Gm10373 | NR_046064.1 | chr15:43430942-43477036 |
| 8007 | Gkn3 | NM_026860.1 | chr6:87383318-87388935 | | 8102 | Gm10375 | NM_001098269.2 | chr14:43602626-43608013 |
| 8008 | Gla | NM_013463.2 | chrX:134588168-134601005 | | 8103 | Gm10377 | NM_001244671.1 | chr14:41767171-43015576 |
| 8009 | Glb1 | NM_009752.2 | chr9:114401077-114474379 | | 8104 | Gm10389 | NR_033541.1 | chr15:10600292-10611651 |
| 8010 | Glb1l | NM_029030.1 | chr1:75198234-75210778 | | 8105 | Gm10390 | NR_045793.1 | chr5:120121095-120139263 |
| 8011 | Glb1l2 | NM_153803.1 | chr9:26763043-26806417 | | 8106 | Gm10400 | NR_033555.1 | chr6:141340552-141344387 |
| 8012 | Glb1l3 | NM_001113323.1 | chr9:26817952-26860823 | | 8107 | Gm10406 | NM_001164727.1 | chr14:7006114-7027449 |
| 8013 | Glcci1 | NM_001161738.1 | chr6:8520057-8597549 | | 8108 | Gm10408 | NM_001256501.1 | chr14:3449311-3698681 |
| 8014 | Glce | NM_033320.4 | chr9:62057248-62070606 | | 8109 | Gm10409 | NR_033121.1 | chr14:3412613-3673272 |
| 8015 | Gldc | NM_138595.2 | chr19:30098440-30175441 | | 8110 | Gm10413 | NM_029288.3 | chr14:3395092-3642952 |
| 8016 | Gldn | NM_177350.5 | chr9:54286485-54341777 | | 8111 | Gm10415 | NR_045480.1 | chr6:126286648-126328686 |
| 8017 | Gldnos | NR_045805.1 | chr9:54268579-54301570 | | 8112 | Gm10416 | NR_027964.1 | chr5:109833500-109834142 |
| 8018 | Gle1 | NM_028923.3 | chr2:29935408-29959432 | | 8113 | Gm10421 | NR_033538.1 | chr12:117144522-117151269 |
| 8019 | Glg1 | NM_009149.2 | chr8:111157557-111259202 | | 8114 | Gm10432 | NR_045741.1 | chr12:100276608-100300908 |
| 8020 | Gli1 | NM_010296.2 | chr10:127329881-127341579 | | 8115 | Gm10433 | NR_045282.1 | chr12:100187967-100193538 |
| 8021 | Gli2 | NM_001081125.1 | chr1:118834060-119053619 | | 8116 | Gm10436 | NM_001105254.1 | chr12:88175588-88181894 |
| 8022 | Gli3 | NM_008130.2 | chr13:15463722-15730025 | | 8117 | Gm10439 | NM_001037716.2 | chrX:149594600-149636621 |
| 8023 | Glipr1 | NM_028608.3 | chr10:111985447-111997264 | | 8118 | Gm10440 | NR_038045.1 | chr5:54349991-54358542 |
| 8024 | Glipr1l1 | NM_027018.1 | chr10:112060188-112078510 | | 8119 | Gm10445 | NR_046063.1 | chr6:84412941-84423838 |
| 8025 | Glipr1l2 | NM_026623.2 | chr10:112083353-112108098 | | 8120 | Gm10451 | NM_001177577.1 | chr5:91987472-91995317 |
| 8026 | Glipr2 | NM_027450.3 | chr4:43957701-43979118 | | 8121 | Gm10451 | NR_028520.1 | chr12:76444496-76448698 |
| 8027 | Glis1 | NM_147221.2 | chr4:107344718-107635059 | | 8122 | Gm10466 | NR_033491.1 | chr11:24721005-24730722 |
| 8028 | Glis2 | NM_031184.3 | chr16:4594712-4615957 | | 8123 | Gm10471 | NM_001177579.1 | chr5:26082171-26089264 |
| 8029 | Glis3 | NM_175459.6 | chr19:28258850-28680077 | | 8124 | Gm10474 | NR_033481.1 | chrX:68667513-68678399 |
| 8030 | Glmn | NM_001160718.1 | chr5:107548966-107597888 | | 8125 | Gm10486 | NM_001109970.1 | chrX:24948451-35427093 |
| 8031 | Glo1 | NM_001113560.1 | chr17:30591861-30612659 | | 8126 | Gm10487 | NM_001100609.1 | chrX:30820542-30843469 |
| 8032 | Glod4 | NM_026029.3 | chr11:76220394-76243699 | | 8127 | Gm10488 | NM_001099325.2 | chrX:27472052-35427074 |
| 8033 | Glod5 | NM_027227.2 | chrX:8004200-8018492 | | 8128 | Gm10494 | NR_033462.1 | chr17:79506048-79510486 |
| 8034 | Glp1r | NM_021332.2 | chr17:30901866-30936510 | | 8129 | Gm10509 | NR_045766.1 | chr17:21690211-21692213 |
| 8035 | Glp2r | NM_175681.3 | chr11:67706429-67771153 | | 8130 | Gm10510 | NR_033511.1 | chr17:15350812-15354461 |
| 8036 | Glra1 | NM_001290821.1 | chr11:55514238-55608198 | | 8131 | Gm10512 | NR_033458.1 | chr17:13205041-13206211 |
| 8037 | Glra2 | NM_183427.4 | chrX:165129016-165326981 | | 8132 | Gm10516 | NR_033536.1 | chr1:192136897-192151025 |
| 8038 | Glra3 | NM_080438.2 | chr8:55940824-56125352 | | 8133 | Gm10532 | NR_045879.1 | chr18:75514644-75522806 |
| 8039 | Glra4 | NM_010747.2 | chrX:136757673-136779721 | | 8134 | Gm10536 | NR_033455.1 | chr18:56936258-56940518 |
| 8040 | Glrb | NM_001281969.1 | chr3:80843598-80913614 | | 8135 | Gm10538 | NR_045892.1 | chr1:132729352-132732826 |
| 8041 | Glrp1 | NM_008132.2 | chr1:88499870-88510066 | | 8136 | Gm10548 | NR_040534.1 | chr18:34207774-34221772 |
| 8042 | Glrx | NM_053108.4 | chr13:75839885-75850151 | | 8137 | Gm10549 | NR_045415.1 | chr18:33464612-33474710 |
| 8043 | Glrx2 | NM_001038592.1 | chr1:143739567-143749678 | | 8138 | Gm10556 | NR_045881.1 | chr18:4812485-4850959 |
| 8044 | Glrx3 | NM_023410.4 | chr7:137437547-137468594 | | 8139 | Gm10560 | NR_040563.1 | chr4:156021644-156023824 |
| 8045 | Glrx5 | NM_028419.3 | chr12:105032617-105040911 | | 8140 | Gm10578 | NR_045885.1 | chr7:137234682-137242609 |
| 8046 | Gls | NM_001081081.2 | chr1:52163449-52233232 | | 8141 | Gm10584 | NR_028578.1 | chr7:132315663-132318291 |
| 8047 | Gls2 | NM_001033264.3 | chr10:128194634-128210004 | | 8142 | Gm10593 | NM_001193668.1 | chr4:42612123-42613253 |
| 8048 | Glt1d1 | NM_177005.4 | chr5:127632261-127707520 | | 8143 | Gm10619 | NR_077222.1 | chr7:73808221-73816503 |
| 8049 | Glt25d1 | NM_146211.3 | chr8:71611023-71624911 | | 8144 | Gm10635 | NR_045336.1 | chr9:79444036-79519302 |
| 8050 | Glt28d2 | NM_177130.3 | chr3:85869645-85887518 | | 8145 | Gm10636 | NR_033542.1 | chr3:146367152-146378944 |
| 8051 | Glt6d1 | NM_001039095.1 | chr2:25793966-25815836 | | 8146 | Gm10637 | NR_040697.1 | chr8:87169746-87199850 |
| 8052 | Glt8d1 | NM_001165930.1 | chr14:31001392-31012441 | | 8147 | Gm10638 | NR_027829.1 | chr8:86745698-86747060 |
| 8053 | Glt8d2 | NM_029102.3 | chr10:82650432-82690650 | | 8148 | Gm10639 | NM_001122660.1 | chr9:78289927-78305525 |
| 8054 | Gltp | NM_019821.2 | chr5:114669499-114690935 | | 8149 | Gm10640 | NR_046062.1 | chr7:31162357-31170641 |
| 8055 | Gltpd1 | NM_024472.4 | chr4:155864722-155869440 | | 8150 | Gm10649 | NR_028579.1 | chr8:76749086-76900173 |
| 8056 | Gltpd2 | NM_146020.1 | chr11:70519208-70520736 | | 8151 | Gm10653 | NR_003965.2 | chr6:62841476-62862024 |
| 8057 | Gltscr1 | NM_001081418.1 | chr7:15971261-15999495 | | 8152 | Gm10658 | NR_045886.1 | chr9:57056896-57071966 |
| 8058 | Gltscr1l | NM_001100452.1 | chr17:46798115-46831413 | | 8153 | Gm10662 | NM_001201364.1 | chr7:21909433-23144478 |
| 8059 | Gltscr2 | NM_133831.3 | chr7:15937585-15946108 | | 8154 | Gm10665 | NM_001167160.1 | chr7:20473959-22464075 |
| 8060 | Glud1 | NM_008133.4 | chr14:34310726-34345033 | | 8155 | Gm10666 | NM_001167573.1 | chr7:20138122-22134741 |
| 8061 | Glul | NM_008131.4 | chr1:153899928-153909723 | | 8156 | Gm10670 | NM_001167161.1 | chr7:20473960-20474925 |
| 8062 | Glyat | NM_145935.3 | chr19:12633307-12651737 | | 8157 | Gm10677 | NR_046048.1 | chr9:47799159-47818208 |
| 8063 | Glyatl3 | NM_001145060.1 | chr7:40904740-40914350 | | 8158 | Gm10681 | NM_001270429.1 | chr3:98498070-98564009 |
| 8064 | Glycam1 | NM_001289587.1 | chr15:103562759-103565081 | | 8159 | Gm10684 | NR_033547.1 | chr9:45107175-45135606 |
| 8065 | Glyctk | NM_001039586.1 | chr9:106152859-106158138 | | 8160 | Gm10696 | NM_001146107.1 | chr3:94174411-94178193 |
| 8066 | Glyr1 | NM_001079814.1 | chr16:5013901-5049910 | | 8161 | Gm10714 | NR_040530.1 | chr2:174125037-174183918 |
| 8067 | Gm10007 | NR_040449.1 | chr19:58296203-58300348 | | 8162 | Gm10731 | NR_045392.1 | chr3:40853475-40855285 |
| 8068 | Gm10012 | NR_028042.1 | chr7:25901855-25902227 | | 8163 | Gm10745 | NR_040751.1 | chr3:11823228-11844359 |
| 8069 | Gm10024 | NM_001081452.2 | chr10:77711445-77712009 | | 8164 | Gm10754 | NR_033537.1 | chr10:97681413-97967090 |

Fig. 26 - 44

| | | | |
|---|---|---|---|
| 8165 | Gm10767 | NM_001177750.1 | chr13:66905414-66909166 |
| 8166 | Gm10768 | NR_033472.1 | chr19:43838802-43840845 |
| 8167 | Gm10778 | NM_001142963.1 | chr10:81649068-81826490 |
| 8168 | Gm10782 | NR_046061.1 | chr13:56362899-56368857 |
| 8169 | Gm10785 | NR_040389.1 | chr16:91688897-91715755 |
| 8170 | Gm10787 | NR_045882.1 | chr10:77011994-77022214 |
| 8171 | Gm10789 | NR_033476.1 | chr16:90141236-90146827 |
| 8172 | Gm10790 | NR_033545.1 | chr13:41865914-41913092 |
| 8173 | Gm10791 | NR_045889.1 | chr16:84972210-84979451 |
| 8174 | Gm10804 | NR_040532.1 | chr2:93452818-93469874 |
| 8175 | Gm10814 | NR_045783.1 | chr19:6012619-6018459 |
| 8176 | Gm10823 | NR_033475.1 | chr16:27849929-27926128 |
| 8177 | Gm10825 | NR_028580.1 | chr10:22402812-22407470 |
| 8178 | Gm10845 | NR_033535.1 | chr14:79860520-79869176 |
| 8179 | Gm10857 | NR_033470.1 | chr2:6132868-6140570 |
| 8180 | Gm10863 | NR_029470.1 | chr15:79166065-79216401 |
| 8181 | Gm10865 | NR_045746.1 | chr15:78994954-79011041 |
| 8182 | Gm10872 | NR_045747.1 | chr15:76266786-76269839 |
| 8183 | Gm10921 | NM_001085553.1 | chrX:4289285-31383918 |
| 8184 | Gm10922 | NM_001085554.1 | chrX:4370635-4372595 |
| 8185 | Gm10941 | NR_026944.1 | chr10:77257772-77259223 |
| 8186 | Gm1110 | NM_001281475.1 | chr9:26879566-26923081 |
| 8187 | Gm11110 | NR_033508.1 | chr17:57092022-57105942 |
| 8188 | Gm11127 | NM_001199967.1 | chr17:36055815-36058371 |
| 8189 | Gm11128 | NM_001201389.1 | chr6:85808050-85809877 |
| 8190 | Gm11149 | NR_029465.1 | chr9:49518287-49568025 |
| 8191 | Gm11166 | NR_024558.1 | chr17:13096659-13098472 |
| 8192 | Gm11186 | NR_046041.1 | chr11:53111450-53120056 |
| 8193 | Gm11190 | NR_033549.1 | chr11:77912126-77929288 |
| 8194 | Gm11201 | NR_045873.1 | chr11:79023596-79035005 |
| 8195 | Gm11213 | NR_028583.1 | chr4:63596900-63605261 |
| 8196 | Gm1123 | NM_001080776.1 | chr9:99006964-99035690 |
| 8197 | Gm11237 | NM_001256481.2 | chr4:73605543-73672395 |
| 8198 | Gm11240 | NR_046041.1 | chr4:73791243-73798378 |
| 8199 | Gm11346 | NR_024599.1 | chr13:24598124-24604767 |
| 8200 | Gm11351 | NR_045062.1 | chr13:25921034-25966316 |
| 8201 | Gm1340 | NM_001126317.1 | chrX:67682899-67706350 |
| 8202 | Gm1141 | NR_027801.1 | chrX:71932437-71940871 |
| 8203 | Gm11413 | NR_045450.1 | chr4:83378316-83380668 |
| 8204 | Gm11426 | NR_033582.1 | chr1:82633352-82636309 |
| 8205 | Gm11437 | NM_001037932.2 | chr1:84148360-84167476 |
| 8206 | Gm11468 | NR_033467.1 | chr2:166273907-166294831 |
| 8207 | Gm11487 | NM_001013393.1 | chr4:73401031-73405072 |
| 8208 | Gm11517 | NR_033523.1 | chr11:96795331-96798156 |
| 8209 | Gm11529 | NR_033524.1 | chr11:96446898-96464547 |
| 8210 | Gm11538 | NR_108029.1 | chr11:96203453-96205480 |
| 8211 | Gm11541 | NM_001007584.2 | chr11:94694497-94704499 |
| 8212 | Gm11544 | NM_001205073.1 | chr11:94844830-94849593 |
| 8213 | Gm11545 | NM_001105561.1 | chr11:94755135-94761182 |
| 8214 | Gm11548 | NR_040590.1 | chr3:36499803-36506809 |
| 8215 | Gm11549 | NR_040411.1 | chr3:36515056-36521445 |
| 8216 | Gm11554 | NM_001099313.2 | chr11:99798185-99809892 |
| 8217 | Gm11559 | NM_001177484.2 | chr11:99864475-99865571 |
| 8218 | Gm11562 | NM_001177537.2 | chr11:99619597-99620404 |
| 8219 | Gm11563 | NM_001126320.2 | chr11:99657941-99658959 |
| 8220 | Gm11564 | NM_001100614.1 | chr11:99814975-99815666 |
| 8221 | Gm11565 | NM_001126323.1 | chr11:99914750-99915671 |
| 8222 | Gm11567 | NM_001101613.1 | chr11:99879186-99880229 |
| 8223 | Gm11568 | NM_001205030.1 | chr11:99857916-99859060 |
| 8224 | Gm11569 | NM_001099312.1 | chr11:99803547-99804446 |
| 8225 | Gm11570 | NM_001256057.1 | chr11:99984702-99986593 |
| 8226 | Gm11595 | NM_001126322.1 | chr11:99771713-99772913 |
| 8227 | Gm11596 | NM_001099311.2 | chr11:99792674-99793292 |
| 8228 | Gm11627 | NR_040286.1 | chr11:102576398-102579119 |
| 8229 | Gm11651 | NR_040047.1 | chr11:105965606-105985694 |
| 8230 | Gm11696 | NR_038097.1 | chr11:109354777-109363654 |
| 8231 | Gm11710 | NM_001101656.2 | chr11:115020688-115037690 |
| 8232 | Gm11744 | NM_001163318.1 | chr11:116657107-116668389 |
| 8233 | Gm11747 | NR_045902.1 | chr11:118444199-118454995 |
| 8234 | Gm11757 | NM_001085538.2 | chr4:73872219-73905921 |
| 8235 | Gm11758 | NM_001097978.2 | chr4:73872218-73905953 |
| 8236 | Gm11762 | NR_045099.1 | chr11:119548629-119569046 |
| 8237 | Gm11780 | NM_001077919.1 | chr4:4527773-4529458 |
| 8238 | Gm11837 | NM_001243100.1 | chr4:14930640-14953030 |
| 8239 | Gm11937 | NM_001099346.1 | chr11:99609793-99610189 |
| 8240 | Gm11938 | NR_027354.1 | chr11:99602645-99603308 |
| 8241 | Gm11944 | NR_045708.1 | chr1:3308999-3320722 |
| 8242 | Gm11961 | NR_027797.1 | chr11:4625375-4630011 |
| 8243 | Gm11974 | NR_045893.1 | chr11:6525590-6528760 |
| 8244 | Gm11978 | NR_028586.1 | chr11:6650147-6660236 |
| 8245 | Gm11981 | NR_046025.1 | chr11:6716000-6720037 |
| 8246 | Gm11985 | NR_045101.1 | chr11:7183156-7188569 |
| 8247 | Gm11992 | NM_001037928.3 | chr11:9048591-9069354 |
| 8248 | Gm12 | NM_001195544.1 | chr11:98598290-98599586 |
| 8249 | Gm12060 | NR_004857.1 | chr11:23558059-23558842 |
| 8250 | Gm12070 | NR_002890.1 | chr11:26785107-26787859 |
| 8251 | Gm12130 | NR_040295.1 | chr11:38491547-38520045 |
| 8252 | Gm12159 | NR_045100.1 | chr11:45102865-45116928 |
| 8253 | Gm12169 | NM_001163357.1 | chr11:46524250-46538156 |
| 8254 | Gm12171 | NR_046025.1 | chr11:46548412-46556068 |
| 8255 | Gm12185 | NM_001045540.2 | chr11:48904655-48927182 |
| 8256 | Gm12191 | NR_028101.1 | chr15:34440505-34443233 |
| 8257 | Gm12216 | NR_033332.1 | chr15:53785488-53859256 |
| 8258 | Gm12238 | NR_028480.1 | chr11:55482705-55482829 |
| 8259 | Gm12250 | NM_001135115.1 | chr11:58183842-58190198 |
| 8260 | Gm12253 | NM_001045542.1 | chr11:58432558-58441622 |
| 8261 | Gm12295 | NR_040280.1 | chr11:65277653-65287833 |
| 8262 | Gm12298 | NR_033539.1 | chr11:66905631-66947086 |
| 8263 | Gm12338 | NR_110477.1 | chr11:75599645-75600231 |
| 8264 | Gm12359 | NR_033551.1 | chr11:98798308-98810089 |
| 8265 | Gm12409 | NR_046068.1 | chr4:45762376-45764223 |
| 8266 | Gm12429 | NM_001277167.1 | chr4:42848070-42853888 |
| 8267 | Gm12504 | NR_040414.1 | chr4:44121892-44124123 |
| 8268 | Gm12505 | NR_040674.1 | chr4:55410442-55418842 |
| 8269 | Gm12522 | NR_040560.1 | chr3:108379276-108383741 |
| 8270 | Gm12530 | NR_040669.1 | chr4:57172070-57176554 |
| 8271 | Gm12603 | NR_033533.1 | chr4:89050306-89084610 |
| 8272 | Gm12633 | NR_033610.1 | chr4:90359624-90361314 |
| 8273 | Gm12657 | NM_001081019.1 | chr4:94593649-94600319 |
| 8274 | Gm12669 | NR_033611.1 | chr7:137437673-137467980 |
| 8275 | Gm12695 | NM_001081284.1 | chr4:96723886-96785160 |
| 8276 | Gm12709 | NR_040444.1 | chr4:102967265-102989755 |
| 8277 | Gm12718 | NR_040673.1 | chr4:103382499-103492188 |
| 8278 | Gm12789 | NM_001086520.2 | chr4:101986839-101990231 |
| 8279 | Gm12794 | NM_001085516.1 | chr4:101940406-101943183 |
| 8280 | Gm128 | NM_001024841.3 | chr9:95236919-95241109 |
| 8281 | Gm12830 | NR_033617.1 | chr4:114821719-114856166 |
| 8282 | Gm12886 | NM_001144948.1 | chr4:121414734-121423099 |
| 8283 | Gm12887 | NM_001099309.1 | chr4:121614003-121622125 |
| 8284 | Gm12888 | NM_001033791.3 | chr4:121316315-121324917 |
| 8285 | Gm12942 | NM_001099319.2 | chr4:127126042-127129660 |
| 8286 | Gm12992 | NR_102393.1 | chr4:131899477-131920029 |
| 8287 | Gm13003 | NR_040443.1 | chr4:137159081-137165066 |
| 8288 | Gm13011 | NM_001126318.1 | chr4:137401553-137409791 |
| 8289 | Gm13023 | NM_001007077.2 | chr4:143789333-143795585 |
| 8290 | Gm13031 | NR_045911.1 | chr4:140947665-140957902 |
| 8291 | Gm13032 | NR_045944.1 | chr4:140810992-140817511 |
| 8292 | Gm13034 | NR_030771.1 | chr4:146067523-146068718 |
| 8293 | Gm13040 | NM_001113736.1 | chr4:143535954-143542471 |
| 8294 | Gm13043 | NM_001039595.2 | chr4:143511342-143517831 |
| 8295 | Gm13051 | NM_001037926.2 | chr4:146097311-146126623 |
| 8296 | Gm13057 | NM_001113735.1 | chr4:143511311-143558236 |
| 8297 | Gm13078 | NM_001085412.2 | chr4:143719450-143729158 |
| 8298 | Gm13083 | NM_001126324.1 | chr4:143615002-143618595 |
| 8299 | Gm13084 | NM_001005371.3 | chr4:143809990-143816093 |
| 8300 | Gm13088 | NM_001126325.1 | chr4:143653759-143657246 |
| 8301 | Gm13102 | NM_001085419.1 | chr4:144099879-144110101 |
| 8302 | Gm13103 | NM_177571.3 | chr4:143846496-143853637 |
| 8303 | Gm13119 | NM_001034101.2 | chr4:144357963-144364419 |
| 8304 | Gm13124 | NM_001085542.1 | chr4:144554999-144565134 |
| 8305 | Gm13125 | NM_001115077.1 | chr4:144372759-144377933 |
| 8306 | Gm13128 | NM_001085541.1 | chr4:144330248-144333465 |
| 8307 | Gm13139 | NM_001083918.1 | chr4:145781542-146468233 |
| 8308 | Gm13152 | NM_001039209.2 | chr4:147175865-147513420 |
| 8309 | Gm13154 | NM_001014397.4 | chr4:147553276-147585201 |
| 8310 | Gm13157 | NM_001127189.3 | chr4:147753973-147809788 |
| 8311 | Gm13177 | NM_001081248.1 | chr4:144613706-144623398 |
| 8312 | Gm13178 | NM_001085536.1 | chr4:144703190-144721404 |
| 8313 | Gm13212 | NM_001205101.1 | chr4:145617145-145624394 |
| 8314 | Gm1322 | NM_001034477.3 | chr2:67173833-67186212 |
| 8315 | Gm13238 | NR_033612.1 | chr4:145837218-145837992 |
| 8316 | Gm13242 | NM_001103158.2 | chr4:145670696-145704437 |
| 8317 | Gm13247 | NM_001243138.1 | chr4:146501999-146539395 |
| 8318 | Gm13251 | NM_001085522.2 | chr4:146449029-146469440 |
| 8319 | Gm13271 | NM_001085528.1 | chr4:88754867-88755416 |
| 8320 | Gm13272 | NM_001161608.1 | chr4:88779849-88780660 |
| 8321 | Gm13275 | NM_001085533.2 | chr4:88793741-88801130 |
| 8322 | Gm13276 | NM_001085532.3 | chr4:88785053-88786515 |
| 8323 | Gm13277 | NM_001098840.3 | chr4:88787976-88789438 |
| 8324 | Gm13278 | NM_001098841.3 | chr4:88790894-88798203 |
| 8325 | Gm13279 | NM_001243166.1 | chr4:88791389-88798204 |
| 8326 | Gm13283 | NM_001085531.2 | chr4:88760773-88761584 |
| 8327 | Gm13285 | NM_001161609.1 | chr4:87873993-88806734 |
| 8328 | Gm13286 | NM_001243150.1 | chr4:88757843-88758392 |
| 8329 | Gm13288 | NM_001243167.1 | chr4:88805530-88808380 |
| 8330 | Gm13290 | NM_001243155.1 | chr4:88773833-88806993 |
| 8331 | Gm13293 | NR_040369.1 | chr2:11339488-11344106 |
| 8332 | Gm13298 | NM_001085530.1 | chr4:144078-42528237 |
| 8333 | Gm13304 | NM_001193666.1 | chr4:42114787-42115917 |
| 8334 | Gm13305 | NM_001099348.1 | chr4:3809-42665762 |
| 8335 | Gm13306 | NM_001164046.1 | chr4:3059-42656005 |
| 8336 | Gm13308 | NM_001177580.1 | chr4:173251-42440009 |
| 8337 | Gm13315 | NR_028497.1 | chr2:14720641-14722622 |
| 8338 | Gm13363 | NR_002688.1 | chr1:30941591-30949710 |
| 8339 | Gm13375 | NR_033225.1 | chr2:20968873-20970348 |
| 8340 | Gm13446 | NR_045894.1 | chr2:35549533-35558702 |
| 8341 | Gm13483 | NR_040361.1 | chr2:50296809-50365000 |
| 8342 | Gm13490 | NR_040639.1 | chr2:51656965-51732009 |
| 8343 | Gm13497 | NR_040636.1 | chr2:51241830-51295945 |
| 8344 | Gm13498 | NR_033595.1 | chr2:50909683-50911846 |
| 8345 | Gm13539 | NR_045340.1 | chr2:25784616-25787022 |
| 8346 | Gm13544 | NR_040365.1 | chr2:58276778-58286902 |
| 8347 | Gm13546 | NR_045895.1 | chr2:58163973-58177063 |
| 8348 | Gm13547 | NM_001177392.1 | chr2:29761527-29764089 |
| 8349 | Gm13580 | NR_046065.1 | chr2:60411524-60412574 |
| 8350 | Gm13582 | NR_045335.1 | chr2:60964375-60975151 |
| 8351 | Gm136 | NM_001033255.2 | chr4:34743787-34756259 |
| 8352 | Gm13629 | NR_033495.1 | chr2:66440879-66547472 |
| 8353 | Gm13710 | NR_046046.1 | chr2:84500747-84506873 |
| 8354 | Gm13749 | NR_027824.1 | chr1:63964726-63968999 |

Fig. 26 - 45

| | | | |
|---|---|---|---|
| 8355 | Gm13752 | NR_040370.1 | chr2:80391363-80398216 |
| 8356 | Gm13769 | NM_001270423.1 | chr2:90322222-90325126 |
| 8357 | Gm13807 | NR_040529.1 | chr5:93403546-93417830 |
| 8358 | Gm13826 | NM_001271590.1 | chr5:115102921-115110268 |
| 8359 | Gm13871 | NM_001177578.2 | chr4:73872218-73906921 |
| 8360 | Gm13889 | NM_001145034.1 | chr2:93955809-93957100 |
| 8361 | Gm13939 | NR_033473.1 | chr2:109902395-109913319 |
| 8362 | Gm13944 | NR_040368.1 | chr2:77462643-77480938 |
| 8363 | Gm14005 | NR_028589.1 | chr2:128298662-128429351 |
| 8364 | Gm14015 | NR_040637.1 | chr2:106463822-106523103 |
| 8365 | Gm14023 | NR_040371.1 | chr2:129297369-129307826 |
| 8366 | Gm14057 | NR_024097.1 | chr2:130801965-130804101 |
| 8367 | Gm14085 | NM_001085518.1 | chr2:122484940-122528040 |
| 8368 | Gm14092 | NM_001037929.2 | chr2:145549454-145554982 |
| 8369 | Gm14124 | NM_001142410.1 | chr2:150257916-150270300 |
| 8370 | Gm14137 | NM_001039223.3 | chr2:119174508-119177575 |
| 8371 | Gm14139 | NM_001145863.1 | chr2:150181754-150193279 |
| 8372 | Gm14151 | NM_001097977.1 | chr2:151086785-151103809 |
| 8373 | Gm14164 | NR_033505.1 | chr2:152345668-152375322 |
| 8374 | Gm14169 | NR_040372.1 | chr2:156609197-156613422 |
| 8375 | Gm14204 | NR_040358.1 | chr2:158598172-158610723 |
| 8376 | Gm14207 | NR_030683.1 | chr2:119321198-119326197 |
| 8377 | Gm14288 | NM_001033123.3 | chr2:175275123-176432381 |
| 8378 | Gm14295 | NM_001205057.2 | chr2:176798599-176808704 |
| 8379 | Gm14305 | NM_001099327.1 | chr2:176708352-176721813 |
| 8380 | Gm14306 | NM_001242944.1 | chr2:175470024-175480553 |
| 8381 | Gm14308 | NM_001099349.2 | chr2:175321833-175636319 |
| 8382 | Gm14322 | NM_001243903.1 | chr2:177759287-177773275 |
| 8383 | Gm14325 | NM_001024849.2 | chr2:177828990-177840318 |
| 8384 | Gm14326 | NM_001190302.2 | chr2:177944590-177957288 |
| 8385 | Gm14327 | NR_038101.2 | chr2:177897162-177927850 |
| 8386 | Gm14345 | NM_001085545.1 | chrX:3700233-3702192 |
| 8387 | Gm14346 | NM_001085551.1 | chrX:3441731-3443690 |
| 8388 | Gm14347 | NM_001085543.1 | chrX:4196575-4198535 |
| 8389 | Gm14351 | NM_001085552.2 | chrX:3750931-3752885 |
| 8390 | Gm14374 | NM_001085523.1 | chrX:5669066-5671026 |
| 8391 | Gm14378 | NM_001195258.1 | chr8:4248213-4251423 |
| 8392 | Gm14379 | NR_026741.1 | chrX:7375924-7378042 |
| 8393 | Gm14391 | NM_001099308.2 | chr2:175194278-175881883 |
| 8394 | Gm14393 | NM_001085546.2 | chr2:175061548-175067769 |
| 8395 | Gm14403 | NR_036450.1 | chr2:177498225-177512311 |
| 8396 | Gm14405 | NR_040256.1 | chr2:176289942-176864437 |
| 8397 | Gm14420 | NM_001177568.1 | chr2:177464741-177479194 |
| 8398 | Gm14431 | NM_001177404.1 | chr2:176521004-176533821 |
| 8399 | Gm14436 | NM_001242943.1 | chr2:175470059-175483322 |
| 8400 | Gm14440 | NM_001199308.1 | chr2:175275124-175801037 |
| 8401 | Gm14446 | NM_001101605.1 | chr19:34592887-34601968 |
| 8402 | Gm14458 | NM_001099326.2 | chrX:8985939-8986672 |
| 8403 | Gm14459 | NM_001126491.1 | chrX:8514051-8524954 |
| 8404 | Gm14461 | NM_177843.3 | chr2:78237546-78302230 |
| 8405 | Gm14474 | NM_001242947.1 | chrX:11302431-11302921 |
| 8406 | Gm14475 | NM_001242954.1 | chrX:11324659-11324976 |
| 8407 | Gm14476 | NM_001242950.1 | chrX:11299320-11324976 |
| 8408 | Gm14477 | NM_001242949.1 | chrX:11305655-11305972 |
| 8409 | Gm14478 | NM_001242953.1 | chrX:11318285-11321894 |
| 8410 | Gm14479 | NM_001242951.1 | chrX:11315158-11315475 |
| 8411 | Gm14482 | NM_001242952.1 | chrX:11308754-11321931 |
| 8412 | Gm14483 | NM_001111037.1 | chrX:11299256-11309260 |
| 8413 | Gm14484 | NM_001205260.2 | chrX:11311933-11312427 |
| 8414 | Gm14496 | NM_001205282.1 | chr2:181991225-182001087 |
| 8415 | Gm14499 | NM_001277184.1 | chrX:8975717-9004410 |
| 8416 | Gm14501 | NM_001085537.2 | chrX:9350598-9351137 |
| 8417 | Gm14511 | NM_001085525.2 | chrX:8975717-8978559 |
| 8418 | Gm14525 | NM_001162364.2 | chrX:26672779-26702638 |
| 8419 | Gm14548 | NM_001166672.1 | chr7:3884213-3898092 |
| 8420 | Gm14625 | NM_001220498.1 | chr2:55430234-55446892 |
| 8421 | Gm14632 | NM_001100610.2 | chrX:30329715-30352646 |
| 8422 | Gm14634 | NR_045852.1 | chrX:12762277-12821492 |
| 8423 | Gm14635 | NM_045321.1 | chrX:12339778-12354936 |
| 8424 | Gm14685 | NM_001205283.2 | chrX:73123067-73143424 |
| 8425 | Gm14692 | NM_001163195.1 | chrX:67682991-67706258 |
| 8426 | Gm14718 | NR_038463.1 | chrX:57200636-57204376 |
| 8427 | Gm14725 | NM_001081476.1 | chrX:70545557-70546385 |
| 8428 | Gm14743 | NM_001126321.2 | chr8:78240461-78245921 |
| 8429 | Gm14744 | NM_001085544.1 | chrX:77864757-77870033 |
| 8430 | Gm14781 | NM_001205268.1 | chrX:91632193-91636571 |
| 8431 | Gm14812 | NR_033544.2 | chrX:99405330-99443797 |
| 8432 | Gm14819 | NM_001110250.2 | chrX:24948450-35427093 |
| 8433 | Gm14827 | NR_045323.1 | chrX:94442731-94447727 |
| 8434 | Gm14850 | NM_001177522.1 | chr8:21427427-21566350 |
| 8435 | Gm14851 | NM_001177482.1 | chr8:21094970-21096050 |
| 8436 | Gm14858 | NR_040285.1 | chrX:102252650-102257689 |
| 8437 | Gm14920 | NM_001102665.1 | chrX:117014756-117015104 |
| 8438 | Gm15008 | NR_045917.1 | chrX:36910833-36911985 |
| 8439 | Gm15023 | NM_001099321.2 | chrX:135169304-135502913 |
| 8440 | Gm15055 | NR_110440.1 | chr6:52102948-52113684 |
| 8441 | Gm15056 | NM_001177471.1 | chr8:20900605-20901973 |
| 8442 | Gm15091 | NM_001122735.1 | chrX:149941654-149984982 |
| 8443 | Gm15093 | NM_001099920.1 | chrX:148822133-149487784 |
| 8444 | Gm15097 | NM_149798.2 | chrX:149784503-148826694 |
| 8445 | Gm15104 | NM_001101501.1 | chrX:150312950-150313364 |
| 8446 | Gm15107 | NM_001081648.1 | chrX:148180723-148224710 |
| 8447 | Gm15114 | NM_148488948-148521446 | chrX:148488948-148521446 |
| 8448 | Gm15127 | NM_001114400.2 | chrX:148663603-149984982 |
| 8449 | Gm15133 | NR_040749.1 | chr7:104315030-104324838 |
| 8450 | Gm15140 | NM_001243017.1 | chrX:154109633-154120688 |
| 8451 | Gm15179 | NR_037976.1 | chr1:75368209-75375015 |
| 8452 | Gm15217 | NR_037981.1 | chr14:46379523-46383606 |
| 8453 | Gm1527 | NM_001034479.4 | chr3:28892616-28926724 |
| 8454 | Gm15284 | NM_001177485.1 | chr8:21134649-21135598 |
| 8455 | Gm15292 | NM_001177487.1 | chr8:21249761-21250461 |
| 8456 | Gm15293 | NM_001177486.1 | chr8:21201603-21202446 |
| 8457 | Gm15299 | NM_001170955.1 | chr8:21315545-21316387 |
| 8458 | Gm15308 | NM_001177521.1 | chr8:21529029-21530012 |
| 8459 | Gm15315 | NM_001177528.1 | chr8:21665796-21666733 |
| 8460 | Gm15319 | NM_001177408.1 | chr8:20337663-20363202 |
| 8461 | Gm15328 | NR_045399.1 | chr18:16816406-16822783 |
| 8462 | Gm15348 | NR_033546.1 | chr8:12706943-12719127 |
| 8463 | Gm15350 | NR_045775.1 | chr8:12828337-12831919 |
| 8464 | Gm15386 | NM_001040027.2 | chr1:18260523-18265138 |
| 8465 | Gm15401 | NR_040421.1 | chr5:72629830-72637717 |
| 8466 | Gm15408 | NR_040429.1 | chr5:149006961-149012776 |
| 8467 | Gm15412 | NR_046043.1 | chr7:96339482-96341964 |
| 8468 | Gm15413 | NR_045874.1 | chr7:96791432-96801549 |
| 8469 | Gm15417 | NR_040403.1 | chr3:89391863-89398779 |
| 8470 | Gm15423 | NR_004442.1 | chr5:22528220-22529030 |
| 8471 | Gm15441 | NR_040409.1 | chr3:96555767-96566801 |
| 8472 | Gm15446 | NR_040366.1 | chr5:109933562-109941710 |
| 8473 | Gm15455 | NM_001161816.1 | chr1:33835898-33838914 |
| 8474 | Gm15471 | NR_040412.1 | chr10:103808128-103808440 |
| 8475 | Gm1553 | NM_001255990.1 | chr10:82486532-82492618 |
| 8476 | Gm15545 | NR_045266.1 | chr7:44986899-44994601 |
| 8477 | Gm156 | NM_001014997.1 | chr6:129766646-129775849 |
| 8478 | Gm15612 | NR_045880.1 | chr6:88842853-88847274 |
| 8479 | Gm15564 | NM_001127576.2 | chr11:102565584-102682238 |
| 8480 | Gm15645 | NR_033578.1 | chr7:105861780-105863327 |
| 8481 | Gm15663 | NR_038032.1 | chr10:105574550-105583870 |
| 8482 | Gm15679 | NR_110579.1 | chr8:99011886-99032741 |
| 8483 | Gm15698 | NR_003564.1 | chr11:88964665-88966917 |
| 8484 | Gm15706 | NR_045598.1 | chr6:145250551-145251856 |
| 8485 | Gm15708 | NR_040432.1 | chr5:144277060-144280514 |
| 8486 | Gm15713 | NR_046026.1 | chr16:43410517-43420196 |
| 8487 | Gm15760 | NR_036670.1 | chr16:20545111-20548556 |
| 8488 | Gm15772 | NR_003373.1 | chr11:68901588-68904534 |
| 8489 | Gm15787 | NR_040430.1 | chr5:110167507-110176504 |
| 8490 | Gm15800 | NM_181421.4 | chr5:121220218-121368577 |
| 8491 | Gm15816 | NM_001282148.1 | chr8:23138784-23149585 |
| 8492 | Gm15850 | NR_046167.1 | chr1:136127718-136131183 |
| 8493 | Gm1587 | NM_001033440.2 | chr14:77793944-77798968 |
| 8494 | Gm15880 | NR_040343.1 | chr7:80636016-80644384 |
| 8495 | Gm15881 | NM_001177534.2 | chr8:58698848-58700796 |
| 8496 | Gm15910 | NR_038023.1 | chr10:120857628-120863328 |
| 8497 | Gm15915 | NR_038017.1 | chr10:98674217-93683322 |
| 8498 | Gm15941 | NR_045283.1 | chr15:37421132-37432664 |
| 8499 | Gm15987 | NR_045009.2 | chr6:128952352-128975029 |
| 8500 | Gm15997 | NR_045145.1 | chr5:149489055-149538030 |
| 8501 | Gm16023 | NR_040441.1 | chr4:155608296-155624755 |
| 8502 | Gm16039 | NM_001302353.1 | chr6:8259288-8428767 |
| 8503 | Gm16046 | NM_001033442.3 | chr17:7025542-8101228 |
| 8504 | Gm16062 | NR_045686.1 | chr11:59810079-59818362 |
| 8505 | Gm16063 | NR_046171.1 | chr5:119625941-119634462 |
| 8506 | Gm16130 | NM_001243265.1 | chr9:58032273-58048997 |
| 8507 | Gm16157 | NR_040340.1 | chr7:68266338-68276594 |
| 8508 | Gm16287 | NR_033543.1 | chr4:139175406-139180655 |
| 8509 | Gm16293 | NR_045788.1 | chr15:39797044-39812377 |
| 8510 | Gm16294 | NR_046185.1 | chr15:40511321-40527277 |
| 8511 | Gm1631 | NR_037979.1 | chr2:71719416-71730966 |
| 8512 | Gm16325 | NR_045949.1 | chr3:146641931-146651715 |
| 8513 | Gm16336 | NR_046267.1 | chr7:110904984-110905851 |
| 8514 | Gm16367 | NM_001031622.2 | chr5:82194-95194489 |
| 8515 | Gm16381 | NM_001166062.2 | chr12:87644119-87846716 |
| 8516 | Gm16386 | NR_030709.2 | chr17:22776229-22817747 |
| 8517 | Gm16390 | NM_001097980.1 | chrX:154886802-154890267 |
| 8518 | Gm16404 | NM_001220497.1 | chrX:55551595-55568457 |
| 8519 | Gm16405 | NM_001166646.1 | chrX:54531207-54639016 |
| 8520 | Gm16430 | NM_001166601.1 | chrX:54622211-54639016 |
| 8521 | Gm16432 | NM_001034899.3 | chr1:177991434-178048291 |
| 8522 | Gm16445 | NM_001243032.1 | chrX:154152570-154156887 |
| 8523 | Gm16451 | NM_001167149.1 | chr7:20121655-22118245 |
| 8524 | Gm1647 | NR_126533.1 | chr8:69181233-69157177 |
| 8525 | Gm16497 | NR_045603.1 | chr12:14261533-14285684 |
| 8526 | Gm16501 | NM_001113395.1 | chrY:2599098-2720674 |
| 8527 | Gm16515 | NM_025294.5 | chr11:60902245-80913792 |
| 8528 | Gm16523 | NR_033526.1 | chr2:39157485-39162235 |
| 8529 | Gm1653 | NR_040591.1 | chr3:149274736-149279980 |
| 8530 | Gm16532 | NM_001134752.1 | chr7:6415174-6431086 |
| 8531 | Gm16548 | NR_037987.1 | chr1:164148575-164152217 |
| 8532 | Gm16551 | NR_045284.1 | chr9:74848436-74852872 |
| 8533 | Gm16576 | NR_045069.1 | chr15:79742697-79757394 |
| 8534 | Gm16596 | NR_045751.1 | chr12:108536401-108555618 |
| 8535 | Gm166 | NM_001033040.3 | chr7:127582382-127588595 |
| 8536 | Gm1661 | NM_001033774.2 | chr4:117215189-117251917 |
| 8537 | Gm16617 | NR_045728.1 | chr14:51986388-51988829 |
| 8538 | Gm16675 | NR_045750.1 | chr8:46730969-46739515 |
| 8539 | Gm16697 | NR_045091.1 | chr14:69329706-69555381 |
| 8540 | Gm16701 | NR_037988.1 | chr1:166974022-166999730 |
| 8541 | Gm16702 | NR_045795.1 | chr17:8379044-8389468 |
| 8542 | Gm16712 | NR_108021.1 | chr17:55954770-55959401 |
| 8543 | Gm1673 | NM_001033458.4 | chr5:33983432-33985009 |
| 8544 | Gm16740 | NR_108026.1 | chr3:95217456-95226658 |

Fig. 26 - 46

| | | | | | | | | |
|---|---|---|---|---|---|---|---|---|
| 8545 | Gm16793 | NR_040376.1 | chr8:35582502-35589020 | | 8640 | Gm20324 | NR_045068.1 | chr15:82899079-82905816 |
| 8546 | Gm16796 | NR_040367.1 | chr2:170499356-170511927 | | 8641 | Gm20337 | NR_045057.1 | chr12:80942651-80945399 |
| 8547 | Gm16833 | NR_045754.1 | chr9:9236287-9260885 | | 8642 | Gm20356 | NR_040450.1 | chr3:74009218-74017277 |
| 8548 | Gm16845 | NR_040406.1 | chr9:22071001-22086131 | | 8643 | Gm20362 | NR_040301.1 | chr8:79032041-79035869 |
| 8549 | Gm16853 | NR_045742.1 | chr9:21405241-21411720 | | 8644 | Gm2042 | NM_001270792.1 | chr12:87602664-87960682 |
| 8550 | Gm16861 | NR_037666.1 | chr16:4935163-4939585 | | 8645 | Gm20554 | NR_030701.1 | chr13:72623465-72628564 |
| 8551 | Gm16863 | NR_046162.1 | chr16:21247498-21296872 | | 8646 | Gm20556 | NR_040347.1 | chr15:84714628-84720266 |
| 8552 | Gm16880 | NR_037986.1 | chr1:136696210-136725728 | | 8647 | Gm20594 | NM_001190732.1 | chr8:79818030-79818364 |
| 8553 | Gm16894 | NR_037980.1 | chr1:40076211-40085851 | | 8648 | Gm20597 | NR_037973.1 | chr10:53498442-53518989 |
| 8554 | Gm16897 | NR_033564.1 | chr1:194955758-194976959 | | 8649 | Gm20604 | NM_001142939.1 | chr12:102739829-102757810 |
| 8555 | Gm16907 | NR_045794.1 | chr3:63289153-63297147 | | 8650 | Gm20605 | NR_033148.1 | chr5:137629122-137642896 |
| 8556 | Gm16938 | NR_045969.1 | chr7:98177193-98184799 | | 8651 | Gm2061 | NR_040305.1 | chr1:185447115-185455568 |
| 8557 | Gm16973 | NR_046209.1 | chr14:56696274-56701000 | | 8652 | Gm20611 | NR_040638.1 | chr10:61031302-61038080 |
| 8558 | Gm16982 | NR_040357.1 | chr7:141610065-141613747 | | 8653 | Gm20735 | NR_015497.2 | chr8:122445267-122451322 |
| 8559 | Gm16998 | NR_038016.1 | chr10:54075921-54081081 | | 8654 | Gm20736 | NM_001037748.1 | chrY:22835090-82251414 |
| 8560 | Gm17019 | NM_182957.1 | chr5:15028949-15033007 | | 8655 | Gm20738 | NM_207162.2 | chrY:37957819-65207518 |
| 8561 | Gm17066 | NR_040628.1 | chr14:105106727-105114676 | | 8656 | Gm20740 | NR_045279.1 | chr15:63414396-63479608 |
| 8562 | Gm1715 | NR_045333.1 | chr9:52679862-52798772 | | 8657 | Gm20741 | NR_045150.1 | chr16:88811439-88812220 |
| 8563 | Gm1720 | NR_046015.1 | chrX:166662024-166689812 | | 8658 | Gm20743 | NR_040303.1 | chr1:164863120-164871438 |
| 8564 | Gm17252 | NM_001199953.1 | chr9:35685078-35687371 | | 8659 | Gm20744 | NR_045744.1 | chr7:82070386-82081758 |
| 8565 | Gm17296 | NM_001159907.1 | chr8:126426651-126475065 | | 8660 | Gm20745 | NR_045745.1 | chr9:68017963-68025714 |
| 8566 | Gm17359 | NM_001142953.1 | chr3:79345375-79464128 | | 8661 | Gm20747 | NM_001025241.3 | chrY:21164953-81801497 |
| 8567 | Gm17365 | NM_001167592.2 | chr9:35645112-35648202 | | 8662 | Gm20748 | NR_045420.2 | chr18:61639652-61647485 |
| 8568 | Gm17455 | NM_001164374.1 | chr10:60399725-60403558 | | 8663 | Gm20750 | NR_040555.1 | chr3:52906755-52927666 |
| 8569 | Gm17644 | NR_045297.1 | chr1:12667562-12673090 | | 8664 | Gm20751 | NR_046022.1 | chr13:43716790-43719038 |
| 8570 | Gm17660 | NM_001163772.1 | chr5:104070059-104077608 | | 8665 | Gm20752 | NR_040750.1 | chr3:159076363-159308080 |
| 8571 | Gm17677 | NM_001167588.1 | chr9:35741048-35742252 | | 8666 | Gm20753 | NR_040630.1 | chr1:106152624-106171524 |
| 8572 | Gm17689 | NM_001142956.1 | chr9:36581277-36582635 | | 8667 | Gm20754 | NR_040557.1 | chr3:73066350-73594830 |
| 8573 | Gm17727 | NM_001167673.1 | chr9:35776523-35778109 | | 8668 | Gm20755 | NR_040559.1 | chr3:37898812-37992728 |
| 8574 | Gm17745 | NR_038014.1 | chr10:93336231-93348879 | | 8669 | Gm20756 | NR_040771.1 | chr6:25931425-25977227 |
| 8575 | Gm17746 | NR_045844.1 | chr12:25129173-25132274 | | 8670 | Gm20757 | NR_046027.1 | chr10:92171300-92375373 |
| 8576 | Gm17751 | NR_038012.1 | chr1:76489132-76502028 | | 8671 | Gm20758 | NR_046029.1 | chr10:111854520-111874376 |
| 8577 | Gm17757 | NR_040453.1 | chr7:105294343-106190099 | | 8672 | Gm20759 | NR_046030.1 | chr11:86002657-86024350 |
| 8578 | Gm17762 | NR_028378.1 | chr2:18027248-18030577 | | 8673 | Gm20765 | NM_001270644.1 | chr10:104185533-104188000 |
| 8579 | Gm17769 | NR_027377.1 | chr10:77418375-77420939 | | 8674 | Gm20767 | NM_001039648.3 | chr13:120140245-120155335 |
| 8580 | Gm17801 | NR_027452.1 | chr17:25274123-25275528 | | 8675 | Gm20806 | NM_001160135.2 | chrY:67339048-80757210 |
| 8581 | Gm17821 | NR_033146.1 | chr12:67656741-67669271 | | 8676 | Gm20809 | NM_001160137.1 | chrY:23943165-72820507 |
| 8582 | Gm17830 | NR_033486.1 | chr17:49304478-49312960 | | 8677 | Gm20815 | NM_001017394.2 | chrY:8832248-8835169 |
| 8583 | Gm1821 | NR_002875.2 | chr11:46084026-62553206 | | 8678 | Gm20816 | NM_001160144.1 | chrY:64301782-64786299 |
| 8584 | Gm18409 | NR_038018.1 | chr10:99638730-99641920 | | 8679 | Gm20822 | NM_001199331.1 | chrY:11197161-15883245 |
| 8585 | Gm18853 | NR_040456.1 | chr7:105924334-106190099 | | 8680 | Gm20823 | NM_001160143.1 | chrY:37957810-72384781 |
| 8586 | Gm19276 | NR_040357.1 | chr5:10829050-10832713 | | 8681 | Gm20826 | NM_001101623.1 | chrY:7167019-7636973 |
| 8587 | Gm19277 | NR_040360.1 | chr15:85149253-85156132 | | 8682 | Gm2083 | NM_001134644.1 | chr4:60658465-61782223 |
| 8588 | Gm19299 | NR_045748.1 | chr9:67133560-67163788 | | 8683 | Gm20831 | NM_001103152.1 | chrY:13252390-17967598 |
| 8589 | Gm19303 | NR_045092.1 | chr15:51231689-51395610 | | 8684 | Gm20854 | NM_001160131.1 | chrY:83789753-85529519 |
| 8590 | Gm19345 | NM_001270489.1 | chr7:19852002-19858355 | | 8685 | Gm20857 | NR_038297.1 | chrY:24188658-26267093 |
| 8591 | Gm19395 | NR_038015.1 | chr10:53280269-53283687 | | 8686 | Gm20858 | NR_038298.1 | chrY:24188658-26267093 |
| 8592 | Gm19402 | NM_001205032.1 | chr10:77689956-77690757 | | 8687 | Gm20865 | NM_001160141.1 | chrY:21242965-73240030 |
| 8593 | Gm19424 | NR_040320.1 | chr19:41746960-41750097 | | 8688 | Gm20867 | NM_001160142.1 | chrY:64301784-64786299 |
| 8594 | Gm1943 | NR_002928.2 | chr8:109339799-109340908 | | 8689 | Gm2087 | NR_102437.1 | chr9:83431546-83454574 |
| 8595 | Gm19434 | NR_040296.1 | chr6:135188479-135194959 | | 8690 | Gm20871 | NR_038299.1 | chrY:30497728-59632758 |
| 8596 | Gm19461 | NR_037984.1 | chr1:133249851-133269808 | | 8691 | Gm20877 | NM_001199332.1 | chr12:12381988-17095887 |
| 8597 | Gm19466 | NR_040349.1 | chr18:53648150-53705418 | | 8692 | Gm20878 | NM_001270431.1 | chr4:173286-42439974 |
| 8598 | Gm19510 | NR_045076.1 | chr15:59788416-59794959 | | 8693 | Gm20917 | NM_001160136.1 | chrY:23031058-79149787 |
| 8599 | Gm19522 | NR_040402.1 | chr16:42884369-42912070 | | 8694 | Gm20939 | NM_001024731.2 | chr17:94864917-94878321 |
| 8600 | Gm19557 | NR_045322.1 | chr19:47512981-47516578 | | 8695 | Gm21002 | NM_001270555.1 | chr8:213391810-21392792 |
| 8601 | Gm19583 | NR_045792.1 | chr5:75110320-75147107 | | 8696 | Gm21057 | NR_045695.1 | chr7:80062709-80075257 |
| 8602 | Gm19589 | NR_037971.1 | chr1:88551516-88562166 | | 8697 | Gm2109 | NR_046066.1 | chr9:83691474-83693247 |
| 8603 | Gm19619 | NR_040428.1 | chr5:91257570-91283076 | | 8698 | Gm21119 | NM_001270553.1 | chr8:19729575-20640703 |
| 8604 | Gm1965 | NR_121593.1 | chr6:8914099-89147370 | | 8699 | Gm2115 | NR_045098.1 | chr7:84528953-84578339 |
| 8605 | Gm1966 | NM_001277179.1 | chr7:106595548-106644645 | | 8700 | Gm21221 | NR_077242.1 | chr5:149801989-149811751 |
| 8606 | Gm19668 | NM_001205030.1 | chr10:77798386-77799133 | | 8701 | Gm21269 | NR_102375.1 | chr7:73825923-73836549 |
| 8607 | Gm1968 | NR_037689.1 | chr16:29957926-29979124 | | 8702 | Gm21276 | NR_073038.1 | chr7:38762405-38770304 |
| 8608 | Gm19689 | NR_045094.1 | chr17:83033591-83078225 | | 8703 | Gm21283 | NR_105058.1 | chr8:110495365-110502356 |
| 8609 | Gm19705 | NR_045324.1 | chr1:136683395-136690805 | | 8704 | Gm21284 | NR_078345.1 | chr6:83568038-83588126 |
| 8610 | Gm19710 | NR_045749.1 | chr3:89998759-90001325 | | 8705 | Gm21293 | XM_006512979.2 | chr10:104142987-104145427 |
| 8611 | Gm19757 | NR_040297.1 | chr6:105481265-105492668 | | 8706 | Gm21304 | NM_001270901.1 | chr10:104142986-104196493 |
| 8612 | Gm1976 | NR_045963.1 | chr17:94750941-94834799 | | 8707 | Gm21312 | NM_001270642.1 | chr10:104142986-104196522 |
| 8613 | Gm19782 | NR_045071.1 | chr15:69924232-70078204 | | 8708 | Gm21319 | NM_001270722.1 | chr12:87772424-87775755 |
| 8614 | Gm19784 | NR_046041.1 | chr18:66924761-66949961 | | 8709 | Gm21498 | NM_001270613.1 | chr8:214427427-21566344 |
| 8615 | Gm1979 | NM_001281519.1 | chr5:26000171-26004727 | | 8710 | Gm21541 | NM_001270360.1 | chr4:0-42613253 |
| 8616 | Gm1987 | NM_001193667.1 | chr4:120654-42773893 | | 8711 | Gm21586 | NM_001270432.1 | chr4:42438945-42439974 |
| 8617 | Gm19897 | NR_040349.1 | chr7:28774898-28781514 | | 8712 | Gm21637 | NM_001270685.1 | chrX:31960926-31962821 |
| 8618 | Gm1993 | NM_001102677.2 | chrX:25548500-25570449 | | 8713 | Gm21671 | NM_001281516.1 | chr5:25948796-25954344 |
| 8619 | Gm1995 | NR_033562.1 | chr12:87861349-87865690 | | 8714 | Gm21693 | NM_001270514.1 | chrY:3326746-3345434 |
| 8620 | Gm19990 | NR_045048.1 | chr12:56253242-56266381 | | 8715 | Gm21708 | NM_001270519.1 | chrY:2830679-3783271 |
| 8621 | Gm2002 | NM_001100596.1 | chr4:3084-13572 | | 8716 | Gm2176 | NR_028424.1 | chr18:80541891-80544546 |
| 8622 | Gm20063 | NR_045049.1 | chr12:61499659-61521820 | | 8717 | Gm21943 | NM_001017393.3 | chrY:55557520-73537718 |
| 8623 | Gm20098 | NR_045095.1 | chr17:51882726-51965257 | | 8718 | Gm21944 | NR_022880.1 | chr8:20876498-20889113 |
| 8624 | Gm2011 | NR_038067.1 | chr3:40846998-40875609 | | 8719 | Gm21949 | NM_001113419.2 | chr3:67892219-68626482 |
| 8625 | Gm20110 | NR_038019.1 | chr10:99609170-99658134 | | 8720 | Gm21950 | NM_001270667.1 | chrX:3076919-3078823 |
| 8626 | Gm2012 | NM_001104946.2 | chrX:26200882-26231323 | | 8721 | Gm21951 | NM_001270669.1 | chr12:32726136-32728057 |
| 8627 | Gm20125 | NR_038020.1 | chr10:16951093-17095782 | | 8722 | Gm2373 | NR_110430.1 | chr13:97482700-97497664 |
| 8628 | Gm20139 | NR_038021.1 | chr10:19141748-19207947 | | 8723 | Gm2381 | NR_046214.1 | chr7:42816826-42867234 |
| 8629 | Gm2016 | NM_001212662.1 | chr12:87874071-87877859 | | 8724 | Gm2382 | NM_001128601.1 | chr9:88688604-88719798 |
| 8630 | Gm20172 | NM_001204913.1 | chr12:25276403-25277954 | | 8725 | Gm2447 | NR_038079.1 | chr3:52739723-52776654 |
| 8631 | Gm20187 | NR_045067.1 | chr12:27090236-27114995 | | 8726 | Gm2516 | NR_046067.1 | chr8:50368111-50416089 |
| 8632 | Gm20199 | NR_045640.1 | chr9:59477744-59481741 | | 8727 | Gm2518 | NR_015538.1 | chr19:8774484-8776962 |
| 8633 | Gm2022 | NM_001177574.1 | chr12:87892833-87896722 | | 8728 | Gm266 | NM_001033248.3 | chr12:111484608-111485823 |
| 8634 | Gm20257 | NR_045007.1 | chr1:58652640-58655831 | | 8729 | Gm2663 | NM_001102660.1 | chr6:40995821-40999479 |
| 8635 | Gm20268 | NR_037989.1 | chr1:101155767-101175202 | | 8730 | Gm2694 | NR_033430.1 | chr8:87472811-87525554 |
| 8636 | Gm2027 | NR_045113.1 | chr12:44221355-44224380 | | 8731 | Gm2696 | NM_001205009.1 | chr10:77814681-77815404 |
| 8637 | Gm2030 | NM_001100445.2 | chrX:26287198-26310044 | | 8732 | Gm2721 | NR_045085.1 | chr12:105394855-105403760 |
| 8638 | Gm20300 | NR_045008.1 | chr10:30603194-30606634 | | 8733 | Gm2762 | NR_037991.1 | chr13:53393688-53455630 |
| 8639 | Gm20319 | NR_105063.1 | chr16:26714681-26755502 | | 8734 | Gm2799 | NM_001168334.1 | chrX:32278393-32562004 |

Fig. 26 - 47

| # | Gene | Accession | Location |
|---|---|---|---|
| 8735 | Gm2825 | NM_001168337.1 | chrX:32973896-32975846 |
| 8736 | Gm2837 | NR_040388.1 | chrX:33056285-33057063 |
| 8737 | Gm2848 | NR_046069.1 | chr13:52569879-52573225 |
| 8738 | Gm2863 | NM_001099333.3 | chrX:33313337-33315288 |
| 8739 | Gm2897 | NM_001177715.2 | chr14:3049284-3076838 |
| 8740 | Gm2913 | NM_001243015.1 | chrX:3750925-3357346 |
| 8741 | Gm2927 | NM_001282034.1 | chrX:33657139-33659082 |
| 8742 | Gm2933 | NM_001145038.1 | chrX:33575613-33702349 |
| 8743 | Gm2a | NM_010299.3 | chr11:55097984-55113028 |
| 8744 | Gm3002 | NR_033388.1 | chr14:3814912-3830681 |
| 8745 | Gm3020 | NR_033117.1 | chr14:3412613-3669589 |
| 8746 | Gm3086 | NR_036607.1 | chr12:69963408-69969744 |
| 8747 | Gm3139 | NM_001243937.1 | chr5:40898-94538367 |
| 8748 | Gm3143 | NR_038847.1 | chr3:34699639-34716662 |
| 8749 | Gm3219 | NR_027380.1 | chr14:34345054-34345658 |
| 8750 | Gm3230 | NR_033642.1 | chr2:19655805-19657897 |
| 8751 | Gm3238 | NM_001101630.1 | chr10:77770632-77771325 |
| 8752 | Gm3258 | NM_011509.2 | chr10:31413725-31414435 |
| 8753 | Gm3259 | NM_001270456.1 | chr5:95305922-95343675 |
| 8754 | Gm3264 | NM_001242945.1 | chr14:4430991-4875851 |
| 8755 | Gm3279 | NR_046071.1 | chr6:55684570-55694574 |
| 8756 | Gm3285 | NM_001101631.1 | chr10:77861974-77862638 |
| 8757 | Gm3286 | NM_001122678.2 | chr5:82558-95804235 |
| 8758 | Gm3317 | NM_001242941.2 | chr14:5163641-5522929 |
| 8759 | Gm3336 | NM_001195253.1 | chr8:70718542-70722635 |
| 8760 | Gm3383 | NM_001291093.1 | chr14:5763194-5814642 |
| 8761 | Gm3402 | NM_001243111.1 | chr5:146514122-146558915 |
| 8762 | Gm3404 | NM_001243114.1 | chr5:146525800-146528553 |
| 8763 | Gm3409 | NM_001243113.1 | chr5:146537647-146540427 |
| 8764 | Gm3414 | NR_027993.1 | chr5:45719666-45727578 |
| 8765 | Gm3415 | NM_001243114.1 | chr5:146502376-146558915 |
| 8766 | Gm3417 | NM_001123368.1 | chr17:14964188-15041559 |
| 8767 | Gm3428 | NR_030730.1 | chr9:35848544-35849880 |
| 8768 | Gm3434 | NR_030729.1 | chr9:36134286-36135630 |
| 8769 | Gm3435 | NM_001123372.1 | chr17:15009839-15022449 |
| 8770 | Gm3458 | NR_110518.1 | chr9:71211912-71215386 |
| 8771 | Gm3488 | NM_001256885.1 | chr14:5501623-5522929 |
| 8772 | Gm3500 | NM_001256886.1 | chr14:5365791-5741602 |
| 8773 | Gm3558 | NM_001270842.1 | chr4:47545150-7568566 |
| 8774 | Gm3604 | NM_001162910.1 | chr13:62367715-62383174 |
| 8775 | Gm362 | NM_001195271.1 | chrX:43590988-43593530 |
| 8776 | Gm364 | NM_001128625.2 | chrX:57409148-57488771 |
| 8777 | Gm3646 | NM_001177348.1 | chr1:39804140-39805332 |
| 8778 | Gm3696 | NM_001024712.2 | chr14:7083024-7105457 |
| 8779 | Gm3701 | NM_001243015.1 | chrX:3953043-3957002 |
| 8780 | Gm3706 | NM_001243001.1 | chrX:3441735-34161584 |
| 8781 | Gm3716 | NR_045078.1 | chr5:64593862-64610699 |
| 8782 | Gm3750 | NM_001099643.2 | chrX:4800411-4802359 |
| 8783 | Gm3763 | NM_001243024.1 | chrX:4952134-4954077 |
| 8784 | Gm3776 | NM_001243092.1 | chr9:78257128-78269166 |
| 8785 | Gm382 | NM_001033241.3 | chrX:127039971-127063986 |
| 8786 | Gm3893 | NR_033506.1 | chr4:41889794-42233950 |
| 8787 | Gm3985 | NM_001177589.1 | chr8:32888504-32950026 |
| 8788 | Gm4013 | NR_033452.1 | chr18:42274379-42275197 |
| 8789 | Gm4027 | NM_001177564.1 | chr12:87618908-87622143 |
| 8790 | Gm4070 | NM_001037242.1 | chr7:105895118-106215337 |
| 8791 | Gm41 | NR_036689.1 | chrX:86345474-86354994 |
| 8792 | Gm4133 | NM_001167158.1 | chr7:20333141-22329717 |
| 8793 | Gm4175 | NM_001167165.1 | chr7:21760513-21761475 |
| 8794 | Gm4201 | NM_001167162.1 | chr7:20575320-22565343 |
| 8795 | Gm4214 | NM_001167164.1 | chr7:22983729-22984673 |
| 8796 | Gm4216 | NM_001167165.1 | chr7:21795810-23019923 |
| 8797 | Gm4224 | NR_046074.1 | chr7:12221315-12225807 |
| 8798 | Gm4251 | NR_046075.1 | chr14:71251272-71271059 |
| 8799 | Gm4262 | NR_040518.1 | chr16:11008897-11015184 |
| 8800 | Gm4265 | NR_046077.1 | chr7:129962164-129978669 |
| 8801 | Gm4278 | NR_046078.1 | chr14:74975085-74987104 |
| 8802 | Gm428 | NM_001081644.1 | chr4:73653245-73687959 |
| 8803 | Gm4285 | NR_045294.1 | chr14:75842917-75844964 |
| 8804 | Gm4297 | NM_001004462 | chrX:24552249-24573305 |
| 8805 | Gm4301 | NM_001166637.1 | chr10:100335675-100382560 |
| 8806 | Gm4302 | NM_001166634.1 | chr10:100345969-100362247 |
| 8807 | Gm4303 | NM_001166638.1 | chr10:100345972-100346881 |
| 8808 | Gm4307 | NM_001166641.1 | chr10:100340837-100362247 |
| 8809 | Gm4312 | NM_001166636.1 | chr10:100381647-100382560 |
| 8810 | Gm4340 | NM_001177535.1 | chr10:104142986-104188000 |
| 8811 | Gm4349 | NR_033637.1 | chr3:95427348-95431085 |
| 8812 | Gm436 | NM_001085504.1 | chr4:144669936-144686368 |
| 8813 | Gm4371 | NR_028511.1 | chr15:96182799-96203470 |
| 8814 | Gm438 | NM_001126316.1 | chr4:144777203-144786583 |
| 8815 | Gm44 | NM_001101450.1 | chrX:90892141-90893134 |
| 8816 | Gm4432 | NR_102329.1 | chr17:32241919-32242855 |
| 8817 | Gm4461 | NM_001199062.1 | chr7:33215260-33216351 |
| 8818 | Gm4477 | NM_001253910.2 | chr6:85706706-85708561 |
| 8819 | Gm4489 | NR_027637.1 | chr10:122119696-122130558 |
| 8820 | Gm4532 | NR_030674.1 | chr7:127232417-127233130 |
| 8821 | Gm4541 | NR_033693.1 | chr7:20610883-23178761 |
| 8822 | Gm4559 | NM_001199309.1 | chr7:142273763-142274363 |
| 8823 | Gm4566 | NR_028023.1 | chr7:71333200-71341804 |
| 8824 | Gm4567 | NM_001037248.3 | chr7:20724511-22719710 |
| 8825 | Gm4598 | NR_030681.1 | chr7:24661293-24663109 |
| 8826 | Gm4710 | NR_033456.1 | chr17:75861022-75889039 |
| 8827 | Gm4719 | NR_045952.1 | chr17:89379240-89384993 |
| 8828 | Gm4724 | NM_001256480.1 | chr2:175419391-175435777 |
| 8829 | Gm4736 | NM_053251.1 | chr6:132114220-132364135 |
| 8830 | Gm4745 | NM_001038676.1 | chr7:14659707-14665996 |
| 8831 | Gm4759 | NR_003967.2 | chr7:106421549-106441073 |
| 8832 | Gm4763 | NM_177593.1 | chr7:24722493-24724290 |
| 8833 | Gm4776 | NR_037690.1 | chr1:46020414-46030437 |
| 8834 | Gm4787 | NM_001038995.2 | chr12:81376990-81379486 |
| 8835 | Gm4788 | NM_001029977.3 | chr1:139697918-139781239 |
| 8836 | Gm4791 | NM_001243258.1 | chr9:46998740-47003860 |
| 8837 | Gm4792 | NR_033209.1 | chr10:94293662-94298703 |
| 8838 | Gm4794 | NM_001101452.1 | chr10:33766423-33782115 |
| 8839 | Gm4814 | NR_036451.1 | chr13:93073303-93074755 |
| 8840 | Gm4827 | NR_045935.1 | chr16:50019657-50072852 |
| 8841 | Gm4832 | NM_001190356.1 | chr17:88125511-88131116 |
| 8842 | Gm4836 | NM_009529.3 | chrX:27472050-35427076 |
| 8843 | Gm4841 | NM_001034859.3 | chr18:60268300-60273267 |
| 8844 | Gm4846 | NM_001164306.1 | chr1:166483612-166497588 |
| 8845 | Gm4847 | NM_001164312.1 | chr1:166628970-166647693 |
| 8846 | Gm4850 | NR_015347.1 | chr1:31264846-31268061 |
| 8847 | Gm4858 | NM_001034860.2 | chr3:93068822-93075505 |
| 8848 | Gm4861 | NM_177665.3 | chr3:137550044-137552622 |
| 8849 | Gm4871 | NM_001101463.1 | chr5:145029599-145032764 |
| 8850 | Gm4872 | NR_073371.1 | chr6:53221163-53224975 |
| 8851 | Gm4884 | NM_183166.2 | chr7:41032718-41045302 |
| 8852 | Gm4890 | NR_045822.1 | chr8:79295077-79307774 |
| 8853 | Gm4894 | NM_177701.3 | chr9:49250530-49280594 |
| 8854 | Gm4906 | NM_001114529.1 | chrX:11327821-11328151 |
| 8855 | Gm4907 | NM_001034864.3 | chrX:23892762-23907550 |
| 8856 | Gm4922 | NM_177706.4 | chr10:18779726-18786793 |
| 8857 | Gm4925 | NM_001037166.2 | chr10:88729540-88731101 |
| 8858 | Gm4926 | NR_028066.1 | chr11:46636505-46645006 |
| 8859 | Gm4937 | NM_001013760.2 | chrX:76264305-76267673 |
| 8860 | Gm4944 | NM_001205095.1 | chr17:22197264-22225614 |
| 8861 | Gm4951 | NM_001033767.3 | chr18:60212076-60247820 |
| 8862 | Gm4952 | NM_001013762.2 | chr19:12600015-12627616 |
| 8863 | Gm4956 | NR_002858.1 | chr1:21285245-21298312 |
| 8864 | Gm4961 | NR_045694.2 | chr5:30092939-30097686 |
| 8865 | Gm4971 | NR_033604.1 | chr7:73686491-73686563 |
| 8866 | Gm4975 | NM_001195687.1 | chr8:63924693-63952170 |
| 8867 | Gm4980 | NM_001195529.1 | chr7:99624066-99627103 |
| 8868 | Gm4981 | NM_001034869.2 | chr10:58234847-58236660 |
| 8869 | Gm4984 | NM_001101484.1 | chrX:12651882-12652820 |
| 8870 | Gm5 | NR_024513.1 | chr5:150499746-150502219 |
| 8871 | Gm5039 | NR_036647.2 | chr12:88320121-88321762 |
| 8872 | Gm5065 | NR_003622.2 | chr7:5350541-5360682 |
| 8873 | Gm5069 | NR_003623.1 | chr1:180326968-180330549 |
| 8874 | Gm5071 | NM_001256004.1 | chrX:91931945-91932980 |
| 8875 | Gm5072 | NM_001114678.1 | chrX:91392499-91481160 |
| 8876 | Gm5082 | NM_001145878.1 | chr13:41650761-41656777 |
| 8877 | Gm5083 | NR_045285.1 | chr13:44121166-44125179 |
| 8878 | Gm5084 | NR_036449.1 | chr13:60205470-60216018 |
| 8879 | Gm5086 | NR_046157.1 | chr13:97559999-97583994 |
| 8880 | Gm5087 | NR_121588.1 | chr14:13157388-13284638 |
| 8881 | Gm5088 | NR_002862.3 | chr14:89896223-89899447 |
| 8882 | Gm5089 | NR_033325.1 | chr14:122434853-122451115 |
| 8883 | Gm5091 | NR_046164.1 | chr17:15231584-15240783 |
| 8884 | Gm5095 | NR_033454.1 | chr18:47537734-47718636 |
| 8885 | Gm5105 | NR_037975.1 | chr3:138048760-138067388 |
| 8886 | Gm5108 | NM_001256184.1 | chr5:67941668-67977070 |
| 8887 | Gm5111 | NM_183309.3 | chr6:48589444-48590584 |
| 8888 | Gm5113 | NM_001033540.2 | chr7:30169921-30180209 |
| 8889 | Gm5114 | NM_177890.3 | chr7:39407293-39413160 |
| 8890 | Gm5122 | NR_040767.1 | chr9:61017068-61019797 |
| 8891 | Gm5124 | NR_045668.1 | chrX:21360864-21364624 |
| 8892 | Gm5126 | NR_026596.1 | chrX:102932046-102934223 |
| 8893 | Gm5127 | NM_001033541.2 | chrX:106583185-106710557 |
| 8894 | Gm5129 | NR_028426.1 | chr5:29735333-29735936 |
| 8895 | Gm5132 | NM_001085517.2 | chr9:9571959-9572391 |
| 8896 | Gm5134 | NM_198635.3 | chr10:75954513-76009589 |
| 8897 | Gm5136 | NM_203660.2 | chr10:108699043-108700160 |
| 8898 | Gm5141 | NM_001256065.1 | chr13:62772199-62785808 |
| 8899 | Gm5142 | NM_001004158.2 | chr14:59158502-59178749 |
| 8900 | Gm5148 | NM_198657.2 | chr3:37714189-37724360 |
| 8901 | Gm5150 | NM_001081687.1 | chr3:15948069-16006332 |
| 8902 | Gm5166 | NR_027707.1 | chrX:102791195-102798389 |
| 8903 | Gm5168 | NM_001025607.3 | chrX:26028213-26051041 |
| 8904 | Gm5169 | NM_001040669.1 | chrX:25277482-25301455 |
| 8905 | Gm5176 | NR_033603.1 | chr16:111550787-111501345 |
| 8906 | Gm5177 | NR_033630.1 | chr10:10605944-10616313 |
| 8907 | Gm525 | NM_001033266.2 | chr11:89073840-89093064 |
| 8908 | Gm527 | NM_001025605.1 | chr12:64917910-64924591 |
| 8909 | Gm5294 | NM_001195128.1 | chr5:138820079-138821619 |
| 8910 | Gm53 | NR_037977.1 | chr11:96251659-96264484 |
| 8911 | Gm5334 | NR_003648.2 | chr7:68618455-68620009 |
| 8912 | Gm5346 | NM_001025240.1 | chr8:43624974-43627185 |
| 8913 | Gm5347 | NM_001079931.2 | chr8:43673657-43699491 |
| 8914 | Gm5382 | NM_001034100.1 | chrX:14211147-14211657 |
| 8915 | Gm5409 | NM_001003664.2 | chr6:41415306-41419593 |
| 8916 | Gm5414 | NM_001003670.1 | chr15:101624027-101628188 |
| 8917 | Gm5415 | NM_001164286.1 | chr1:32543545-32547293 |
| 8918 | Gm5416 | NM_001082542.1 | chr16:36210402-36217788 |
| 8919 | Gm5420 | NR_045843.1 | chr10:21690844-21693978 |
| 8920 | Gm5424 | NR_002687.1 | chr2:31470307-31520629 |
| 8921 | Gm5431 | NM_001024230.2 | chr11:48887421-48902152 |
| 8922 | Gm5434 | NR_003649.1 | chr12:36090378-36091829 |
| 8923 | Gm5441 | NR_044987.1 | chr12:117234520-117337012 |
| 8924 | Gm5458 | NM_001024706.2 | chr14:19594137-19602587 |

Fig. 26 - 48

| | | | | | | | | |
|---|---|---|---|---|---|---|---|---|
| 8925 | Gm5460 | NM_001034880.2 | chr14:34041077-34046981 | | 9020 | Gm6367 | NR_044992.1 | chr5:587624-95026536 |
| 8926 | Gm5464 | NM_001034881.3 | chr14:66868849-66871005 | | 9021 | Gm6370 | NM_001243110.1 | chr5:146491362-146494132 |
| 8927 | Gm5468 | NR_027376.1 | chr15:25414191-25452418 | | 9022 | Gm6377 | NM_001037917.2 | chrX:109196755-109200445 |
| 8928 | Gm5475 | NR_040351.1 | chr15:100423192-100428150 | | 9023 | Gm6402 | NR_030688.1 | chr17:30394824-30396180 |
| 8929 | Gm5476 | NR_002868.1 | chr15:101587316-101588572 | | 9024 | Gm6406 | NM_001134661.1 | chr9:98856590-98857352 |
| 8930 | Gm5477 | NR_002869.1 | chr15:101608873-101610479 | | 9025 | Gm6408 | NM_001243104.1 | chr5:146481942-146484702 |
| 8931 | Gm5478 | NR_003960.1 | chr15:101643019-101647380 | | 9026 | Gm6416 | NR_046023.1 | chr13:117130024-117135884 |
| 8932 | Gm5483 | NM_001082845.1 | chr16:36184211-36188110 | | 9027 | Gm6432 | NM_001244762.1 | chr9:99229375-99237239 |
| 8933 | Gm5485 | NR_015373.1 | chr16:48399452-48412416 | | 9028 | Gm6455 | NR_003596.2 | chr5:10865028-10870808 |
| 8934 | Gm5512 | NR_002891.1 | chr10:4403170-12906985 | | 9029 | Gm6460 | NM_001037919.3 | chr5:11594955-11599480 |
| 8935 | Gm5523 | NR_004447.1 | chr1:13785684-13786929 | | 9030 | Gm648 | NM_001033372.2 | chrX:56543873-56549606 |
| 8936 | Gm5531 | NM_001008426.3 | chr1:153874344-153876871 | | 9031 | Gm6484 | NM_001080940.1 | chr9:21835509-21837347 |
| 8937 | Gm5535 | NM_001033778.1 | chr2:144173149-144189290 | | 9032 | Gm6498 | NR_003630.2 | chr14:48198715-48228413 |
| 8938 | Gm5538 | NM_001101531.1 | chr3:59729785-59752397 | | 9033 | Gm6524 | NR_028307.1 | chr5:11692981-11694514 |
| 8939 | Gm5544 | NM_001033779.2 | chr3:97930172-97967018 | | 9034 | Gm6525 | NR_036654.1 | chr3:84174637-84175193 |
| 8940 | Gm5547 | NR_045845.1 | chr3:105815566-105817359 | | 9035 | Gm6537 | NM_001195091.1 | chr7:28756173-28758964 |
| 8941 | Gm5549 | NM_001270430.1 | chr3:132630190-132644649 | | 9036 | Gm6548 | NR_003363.1 | chr17:78850504-78852544 |
| 8942 | Gm5577 | NR_026990.1 | chr6:87981682-87984180 | | 9037 | Gm6559 | NR_110455.1 | chr6:51379709-51392791 |
| 8943 | Gm5591 | NM_001013810.2 | chr7:38518138-38528193 | | 9038 | Gm6567 | NR_046024.1 | chr7:73097751-73102068 |
| 8944 | Gm5592 | NM_001033782.3 | chr7:41284326-41290183 | | 9039 | Gm6568 | NR_040420.2 | chrX:157540803-157541750 |
| 8945 | Gm5595 | NM_001008427.1 | chr7:42660107-42692718 | | 9040 | Gm6578 | NR_003631.2 | chr6:12099520-12109580 |
| 8946 | Gm5607 | NR_027975.2 | chr8:12385770-12436732 | | 9041 | Gm6583 | NM_001039228.4 | chr5:112353772-112356033 |
| 8947 | Gm561 | NM_001033297.2 | chr2:144594064-144595365 | | 9042 | Gm6588 | NM_001177504.1 | chr5:112449425-112451738 |
| 8948 | Gm5615 | NM_001033783.2 | chr9:36532402-36541963 | | 9043 | Gm6592 | NM_001081564.1 | chrX:8843993-8849607 |
| 8949 | Gm5617 | NM_001004191.3 | chr9:48495342-48495975 | | 9044 | Gm6602 | NR_045362.1 | chr3:111881902-112082001 |
| 8950 | Gm5622 | NM_001013816.1 | chr14:51552789-51662953 | | 9045 | Gm6607 | NR_033622.2 | chr9:22330138-22330690 |
| 8951 | Gm5627 | NR_033301.1 | chr9:102739647-102756685 | | 9046 | Gm6614 | NM_001081318.1 | chr6:141972195-142008745 |
| 8952 | Gm5634 | NM_001085524.1 | chrX:8962133-8962975 | | 9047 | Gm6623 | NR_033619.1 | chr17:36178776-36181364 |
| 8953 | Gm5635 | NM_001038697.2 | chrX:9063089-9063822 | | 9048 | Gm6634 | NR_040556.1 | chr3:70772378-70807291 |
| 8954 | Gm5640 | NM_001099302.1 | chrX:74639118-74645635 | | 9049 | Gm6639 | NR_040748.1 | chr3:35597151-35666163 |
| 8955 | Gm5643 | NR_002883.1 | chrX:103240453-142299237 | | 9050 | Gm6642 | NR_033643.2 | chr9:30930385-30930962 |
| 8956 | Gm5662 | NM_001013824.3 | chr12:88270634-88274497 | | 9051 | Gm6644 | NR_037965.1 | chr6:34303933-34317443 |
| 8957 | Gm5712 | NR_033594.1 | chr3:129433672-129434712 | | 9052 | Gm6654 | NR_038089.1 | chr6:146647176-146647802 |
| 8958 | Gm572 | NM_001085505.1 | chr4:148643316-148671572 | | 9053 | Gm6682 | NR_033599.1 | chr12:4782170-4783512 |
| 8959 | Gm5725 | NM_001166711.1 | chr7:21843343-23067456 | | 9054 | Gm6696 | NM_001177523.1 | chr8:21583026-21583867 |
| 8960 | Gm5726 | NM_001164834.1 | chr7:20544834-20545757 | | 9055 | Gm6710 | NM_001164689.1 | chr2:175192979-175883182 |
| 8961 | Gm5728 | NM_001166713.1 | chr7:20374492-22371039 | | 9056 | Gm6756 | NR_076393.1 | chr18:36920304-36922207 |
| 8962 | Gm5741 | NM_001195531.1 | chr8:85067567-85067982 | | 9057 | Gm6760 | NM_001177377.1 | chrX:64151404-64152198 |
| 8963 | Gm5766 | NR_003628.1 | chr16:4229228-4231205 | | 9058 | Gm6763 | NM_001270899.1 | chr10:104142986-104196493 |
| 8964 | Gm5771 | NM_001038997.2 | chr6:41392355-41397256 | | 9059 | Gm6787 | NR_003632.2 | chrX:8097086-8106701 |
| 8965 | Gm5779 | NR_033602.1 | chr10:75352054-75352961 | | 9060 | Gm6792 | NM_001177416.1 | chr7:6252709-6281861 |
| 8966 | Gm5795 | NM_001270786.1 | chr14:3188283-3800987 | | 9061 | Gm6793 | NR_033513.1 | chr2:75669289-75665756 |
| 8967 | Gm5796 | NM_001029930.2 | chr14:4023940-4041368 | | 9062 | Gm6812 | NM_001098842.2 | chrX:68892372-68893053 |
| 8968 | Gm5797 | NM_001025085.2 | chr14:7323987-7332395 | | 9063 | Gm6815 | NR_102685.1 | chr16:36194479-36197886 |
| 8969 | Gm5800 | NM_001034102.2 | chr14:51711643-51717132 | | 9064 | Gm684 | NM_001195681.1 | chr9:51270257-51278554 |
| 8970 | Gm5801 | NR_002889.2 | chr4:56010291-155957601 | | 9065 | Gm6878 | NM_001037931.3 | chr14:67304887-67314711 |
| 8971 | Gm5803 | NM_001165971.1 | chr15:22713819-22714984 | | 9066 | Gm6880 | NM_001099305.1 | chrX:74480286-74481399 |
| 8972 | Gm5820 | NM_001033789.2 | chr18:38892455-38971274 | | 9067 | Gm6890 | NM_001099306.1 | chr4:74740926-74742188 |
| 8973 | Gm5833 | NR_040304.1 | chr1:138640094-138682075 | | 9068 | Gm6902 | NM_001270494.1 | chr7:20724511-23275243 |
| 8974 | Gm5860 | NR_040659.1 | chr4:82065379-82102807 | | 9069 | Gm6904 | NM_001164329.1 | chr14:59244440-59260216 |
| 8975 | Gm5862 | NM_001281525.1 | chr5:26018420-26022891 | | 9070 | Gm6927 | NM_001101585.1 | chrX:77674813-77675452 |
| 8976 | Gm5868 | NM_001024147.2 | chr5:72581638-72587550 | | 9071 | Gm6936 | NR_045001.1 | chr16:49980459-49997475 |
| 8977 | Gm5878 | NM_001034023.2 | chr6:85111415-85126094 | | 9072 | Gm6938 | NR_033482.1 | chrX:21312209-21334727 |
| 8978 | Gm5885 | NM_001185040.1 | chr6:133529188-133532762 | | 9073 | Gm694 | NM_001033374.3 | chr4:141432671-141436105 |
| 8979 | Gm5886 | NM_001177652.2 | chr6:133763997-133767408 | | 9074 | Gm6981 | NR_023357.1 | chr9:52002060-52048705 |
| 8980 | Gm5891 | NM_001034904.2 | chr7:21909433-23144480 | | 9075 | Gm6994 | NR_033141.1 | chr14:77479482-77506868 |
| 8981 | Gm5893 | NR_045096.1 | chr7:24818794-24840275 | | 9076 | Gm7008 | NR_045157.1 | chr12:40223363-40229183 |
| 8982 | Gm590 | NM_001195437.1 | chr9:110914738-110916861 | | 9077 | Gm7030 | NM_001177467.1 | chr17:36127608-36129425 |
| 8983 | Gm5901 | NM_001195727.1 | chr7:105375097-105378287 | | 9078 | Gm7056 | NR_037571.1 | chr5:89616435-89622611 |
| 8984 | Gm5916 | NM_001167587.1 | chr9:36119933-36128779 | | 9079 | Gm7073 | NM_001039240.3 | chrX:60436051-60456195 |
| 8985 | Gm5925 | NR_040410.1 | chrX:4515588-4517543 | | 9080 | Gm7102 | NM_001177513.1 | chr19:61174685-61176309 |
| 8986 | Gm5934 | NM_001100444.2 | chrX:24474307-24499163 | | 9081 | Gm7104 | NR_033570.1 | chr12:88282866-88287070 |
| 8987 | Gm5935 | NM_001081657.1 | chrX:24753161-24775164 | | 9082 | Gm711 | NM_198628.2 | chr2:26934068-26953496 |
| 8988 | Gm5936 | NM_001081670.2 | chrX:74837195-74843369 | | 9083 | Gm7120 | NM_001039244.3 | chr13:119488038-119610459 |
| 8989 | Gm5938 | NM_001053466.2 | chr8:78130403 | | 9084 | Gm7134 | NR_033597.1 | chrX:110372752-110375156 |
| 8990 | Gm5941 | NM_001034103.1 | chrX:92489948-92490679 | | 9085 | Gm715 | NM_001271548.1 | chr6:60548007-60549216 |
| 8991 | Gm595 | NM_001085499.1 | chrX:48841465-48877713 | | 9086 | Gm7157 | NM_001199311.1 | chrX:152563333-152563969 |
| 8992 | Gm597 | NM_001013750.1 | chr1:28776121-28780252 | | 9087 | Gm7168 | NM_001122977.1 | chr17:13948372-13950678 |
| 8993 | Gm6026 | NM_001177569.1 | chrY:2599098-2720674 | | 9088 | Gm7173 | NM_001099307.1 | chr5:79482567-79517285 |
| 8994 | Gm6034 | NM_001034909.3 | chr17:36042960-36058645 | | 9089 | Gm7244 | NM_001101597.2 | chr9:31271400-31275385 |
| 8995 | Gm6040 | NM_001025353.2 | chr8:20916489-20922071 | | 9090 | Gm7257 | NM_001167586.1 | chr9:36431883-36434938 |
| 8996 | Gm6042 | NR_002872.1 | chr5:101503815-101506313 | | 9091 | Gm7271 | NR_033501.1 | chr5:76484076-76516628 |
| 8997 | Gm608 | NM_001039289.2 | chr14:44173396-44227466 | | 9092 | Gm732 | NM_001033252.2 | chrX:107945734-107948436 |
| 8998 | Gm6083 | NR_102704.1 | chr5:29537948-29538624 | | 9093 | Gm7325 | NM_001177468.1 | chr17:45600966-45602067 |
| 8999 | Gm6086 | NM_001039219.2 | chr1:93990508-94011539 | | 9094 | Gm7334 | NR_002700.1 | chr16:78359862-78376757 |
| 9000 | Gm609 | NM_001005254.2 | chr16:45416754-45492969 | | 9095 | Gm7337 | NR_003652.2 | chr5:87850358-87853012 |
| 9001 | Gm6116 | NR_045866.1 | chr5:74949193-74966368 | | 9096 | Gm7361 | NM_001281527.1 | chr5:26257761-26262188 |
| 9002 | Gm6121 | NM_001114754.1 | chrX:26912743-26935669 | | 9097 | Gm7367 | NR_003376.2 | chr11:116434212-116439031 |
| 9003 | Gm614 | NM_001033262.2 | chrX:101261376-101263992 | | 9098 | Gm7444 | NR_033529.1 | chr9:56027635-56031573 |
| 9004 | Gm6150 | NR_038036.1 | chr10:9684721-9691909 | | 9099 | Gm7457 | NR_045707.1 | chr8:142814230-142833494 |
| 9005 | Gm6164 | NM_001167153.1 | chr7:20204683-22201264 | | 9100 | Gm7534 | NM_001080712.1 | chr4:134190803-134203004 |
| 9006 | Gm6194 | NR_033512.1 | chr3:84611386-8463098 | | 9101 | Gm7538 | NR_046033.1 | chr5:119194312-119200018 |
| 9007 | Gm6213 | NR_044988.1 | chr8:39297979-39368268 | | 9102 | Gm7550 | NR_033689.1 | chr12:54387732-54391318 |
| 9008 | Gm6225 | NR_033457.1 | chr18:3336415-3366863 | | 9103 | Gm7609 | NM_001081746.1 | chr1:85199610-85213762 |
| 9009 | Gm6249 | NR_046021.1 | chr7:136667954-136710604 | | 9104 | Gm7616 | NM_001101600.1 | chr9:59951293-59959044 |
| 9010 | Gm6251 | NM_001101561.2 | chr10:20208438-20209030 | | 9105 | Gm765 | NM_001128092.3 | chr6:98238013-98342754 |
| 9011 | Gm6260 | NR_040405.1 | chr3:143670891-143712143 | | 9106 | Gm766 | NM_001145390.1 | chr6:142785780-142804466 |
| 9012 | Gm6268 | NR_044989.1 | chrX:36403476-36404654 | | 9107 | Gm7694 | NM_001198955.1 | chr1:170298192-170306332 |
| 9013 | Gm6277 | NR_045421.1 | chr18:11821087-11839377 | | 9108 | Gm7714 | NM_001110779.1 | chr8:88268918-88282835 |
| 9014 | Gm6289 | NR_126537.1 | chr3:144879322-144896011 | | 9109 | Gm773 | NM_001033423.2 | chrX:56189826-56212881 |
| 9015 | Gm6297 | NR_077221.1 | chr4:40720153-40722317 | | 9110 | Gm7788 | NR_110491.1 | chr18:23217595-23217818 |
| 9016 | Gm6300 | NR_033591.2 | chr3:14363116-14374239 | | 9111 | Gm7849 | NM_001177518.1 | chr5:21455426-21594465 |
| 9017 | Gm6307 | NR_045331.1 | chr2:180385603-180401802 | | 9112 | Gm7854 | NR_028417.1 | chr5:43151685-43235354 |
| 9018 | Gm6313 | NR_045867.1 | chr6:148606785-148614309 | | 9113 | Gm7861 | NM_001177526.1 | chr5:21455538-21594465 |
| 9019 | Gm6329 | NR_040690.1 | chr8:45160493-45165145 | | 9114 | Gm7903 | NM_001242937.1 | chrX:135373283-135383393 |

Fig. 26 - 49

| | | | |
|---|---|---|---|
| 9115 | Gm7904 | NR_003372.1 | chr9:21607083-21608329 |
| 9116 | Gm7977 | NR_040408.1 | chr3:48026011-48026759 |
| 9117 | Gm7978 | NM_001270457.1 | chr5:95732092-95736173 |
| 9118 | Gm805 | NR_046081.1 | chr12:86169340-86195102 |
| 9119 | Gm806 | NM_001033400.2 | chr13:50467306-50475355 |
| 9120 | Gm8096 | NR_033590.1 | chr8:28083193-28084853 |
| 9121 | Gm813 | NM_001033404.2 | chr16:58613685-58616978 |
| 9122 | Gm815 | NM_001033407.2 | chr19:26885924-26888647 |
| 9123 | Gm8179 | NR_046039.1 | chr8:32151894-32181847 |
| 9124 | Gm8221 | NR_033577.1 | chr15:77618967-77627398 |
| 9125 | Gm8234 | NR_004433.3 | chr3:58652041-58654041 |
| 9126 | Gm826 | NM_001033411.3 | chr2:160311400-160327494 |
| 9127 | Gm8267 | NM_001162954.1 | chr14:44717166-44724987 |
| 9128 | Gm829 | NM_001033412.2 | chr4:45683588-45723706 |
| 9129 | Gm8298 | NM_001243003.1 | chr3:59861050-59877313 |
| 9130 | Gm8300 | NM_001177565.1 | chr12:87514315-87518265 |
| 9131 | Gm833 | NR_033138.1 | chr4:152697539-152700922 |
| 9132 | Gm8363 | NR_073378.1 | chr17:5480988-5483069 |
| 9133 | Gm8369 | NM_001164200.1 | chr9:11492037-11512577 |
| 9134 | Gm839 | NR_033190.1 | chr6:89212196-89216179 |
| 9135 | Gm8439 | NM_001101603.1 | chr4:120588744-120609672 |
| 9136 | Gm853 | NM_001034872.2 | chr4:130209108-130222295 |
| 9137 | Gm8579 | NR_036696.1 | chr6:3288518-3317019 |
| 9138 | Gm8580 | NR_027478.1 | chr10:93665243-93665854 |
| 9139 | Gm8615 | NR_028061.1 | chr5:149154127-149156192 |
| 9140 | Gm8633 | NR_045179.1 | chr10:98299926-98351867 |
| 9141 | Gm867 | NM_001277132.1 | chr10:75937722-75940672 |
| 9142 | Gm8677 | NM_001167147.1 | chr7:22533964-22534887 |
| 9143 | Gm8693 | NM_001167154.1 | chr7:22691396-22692317 |
| 9144 | Gm8709 | NR_033633.1 | chr10:26673445-26674651 |
| 9145 | Gm8765 | NM_001244649.1 | chr13:50698328-50703409 |
| 9146 | Gm8773 | NR_033499.1 | chr5:5573798-5576203 |
| 9147 | Gm8787 | NM_001099310.1 | chrX:79330512-79358068 |
| 9148 | Gm8801 | NR_028278.1 | chr17:35947153-35953317 |
| 9149 | Gm8817 | NM_001101606.1 | chrX:167063448-167070370 |
| 9150 | Gm884 | NM_001033434.2 | chr11:103534576-103614739 |
| 9151 | Gm8882 | NM_001177588.1 | chr6:132361104-132364134 |
| 9152 | Gm8883 | NR_027658.1 | chr1:71888111-71891204 |
| 9153 | Gm8884 | NR_026561.1 | chr9:48454343-48454727 |
| 9154 | Gm8898 | NM_001177405.1 | chr2:175372461-176533821 |
| 9155 | Gm8909 | NM_001081032.2 | chr17:36164443-36168537 |
| 9156 | Gm8979 | NR_030719.1 | chr7:106075730-106079148 |
| 9157 | Gm8989 | NR_030720.1 | chr7:106075731-106324528 |
| 9158 | Gm8994 | NM_001142734.1 | chr6:136327538-136329983 |
| 9159 | Gm9 | NM_001033234.2 | chrX:37208501-37211041 |
| 9160 | Gm904 | NM_001033770.1 | chr13:50643227-50645838 |
| 9161 | Gm9047 | NM_001145360.1 | chr6:29471436-29473429 |
| 9162 | Gm9054 | NR_045872.1 | chr3:95985509-95986967 |
| 9163 | Gm906 | NM_001033438.2 | chr13:50245180-50250308 |
| 9164 | Gm9079 | NR_004052.1 | chr10:122078111-122079879 |
| 9165 | Gm9112 | NM_001177365.1 | chrX:102706887-102707670 |
| 9166 | Gm9125 | NM_001163730.2 | chr3:93936632-94054885 |
| 9167 | Gm9159 | NR_033393.1 | chrX:103545499-103547699 |
| 9168 | Gm9199 | NR_027860.1 | chr14:73025602-73026890 |
| 9169 | Gm9268 | NM_001105061.1 | chr7:43018797-43048106 |
| 9170 | Gm933 | NM_001256309.1 | chr16:32804887-32810446 |
| 9171 | Gm9376 | NM_001101609.1 | chr14:118267157-118267770 |
| 9172 | Gm94 | NM_001033280.2 | chr18:43777195-43792878 |
| 9173 | Gm9513 | NM_001128510.1 | chr9:36475637-36477180 |
| 9174 | Gm9573 | NM_001244654.1 | chr17:35617922-35626637 |
| 9175 | Gm960 | NM_001033447.3 | chr19:4625840-4698668 |
| 9176 | Gm9696 | NR_037189.1 | chr3:59952308-59973594 |
| 9177 | Gm973 | NM_001013771.2 | chr1:59516263-59634509 |
| 9178 | Gm9731 | NR_003107.1 | chr8:27296044-27297200 |
| 9179 | Gm9733 | NM_001076679.2 | chr3:15296550-15332302 |
| 9180 | Gm9758 | NM_198666.3 | chr5:14910123-14914889 |
| 9181 | Gm9767 | NR_028030.2 | chr10:26078254-26079447 |
| 9182 | Gm9776 | NR_045619.1 | chr13:94356748-94358923 |
| 9183 | Gm9833 | NR_045710.1 | chr3:10088276-10092562 |
| 9184 | Gm9855 | NM_001199956.1 | chr1:32519562-32520999 |
| 9185 | Gm9855 | NR_037190.1 | chr10:82629841-82650277 |
| 9186 | Gm9866 | NR_045868.1 | chr12:27140795-27160516 |
| 9187 | Gm9871 | NR_027989.1 | chr6:101774248-101801982 |
| 9188 | Gm9895 | NR_045687.1 | chr19:29067300-29069503 |
| 9189 | Gm9899 | NR_040427.1 | chr5:30573986-30588619 |
| 9190 | Gm9920 | NR_045063.1 | chr15:55095916-55113582 |
| 9191 | Gm9926 | NR_040528.1 | chr18:66504177-66511737 |
| 9192 | Gm9958 | NR_045618.1 | chr5:90366996-90368488 |
| 9193 | Gm996 | NM_001005424.2 | chr2:25575415-25580099 |
| 9194 | Gm9961 | NR_033509.1 | chr16:11901363-11930594 |
| 9195 | Gm9962 | NR_033504.1 | chr7:57387271-57409941 |
| 9196 | Gm9992 | NM_001142539.1 | chr17:73623711-73685305 |
| 9197 | Gm9994 | NM_001205249.1 | chr1:93918436-93941239 |
| 9198 | Gm9999 | NR_033461.1 | chr7:46976631-46987803 |
| 9199 | Gmcl1 | NM_011818.3 | chr6:86691767-86733378 |
| 9200 | Gmcl1l | NR_027955.3 | chrX:32560054-32562009 |
| 9201 | Gmds | NM_146153.1 | chr13:31819585-32338544 |
| 9202 | Gmeb1 | NM_001122992.1 | chr4:132221024-132261549 |
| 9203 | Gmeb2 | NM_198169.2 | chr2:181251450-181287966 |
| 9204 | Gmfb | NM_022023.2 | chr14:46808148-46822242 |
| 9205 | Gmfg | NM_001039192.1 | chr7:28440936-28446895 |
| 9206 | Gmip | NM_198101.1 | chr8:69808686-69821870 |
| 9207 | Gml | NM_001177524.1 | chr15:74813454-74818815 |
| 9208 | Gmnc | NM_001013761.2 | chr16:26957234-26991652 |
| 9209 | Gmnn | NM_020567.2 | chr13:24751844-24751937 |

| | | | |
|---|---|---|---|
| 9210 | Gmppa | NM_133708.3 | chr1:75435942-75443176 |
| 9211 | Gmppb | NM_177910.3 | chr9:108049289-108051936 |
| 9212 | Gmpr | NM_025508.5 | chr13:45507443-45546386 |
| 9213 | Gmpr2 | NM_177992.2 | chr14:55672234-55678751 |
| 9214 | Gmps | NM_001033300.2 | chr3:63976642-64019078 |
| 9215 | Gna11 | NM_010301.3 | chr10:81528731-81545046 |
| 9216 | Gna12 | NM_010302.2 | chr5:140759943-140830431 |
| 9217 | Gna13 | NM_010303.3 | chr11:109362793-109401369 |
| 9218 | Gna14 | NM_008137.4 | chr19:16435666-16610818 |
| 9219 | Gna15 | NM_010304.3 | chr10:81502313-81524225 |
| 9220 | Gnai1 | NM_010305.1 | chr5:18265134-18360413 |
| 9221 | Gnai2 | NM_008138.4 | chr9:107614137-107635342 |
| 9222 | Gnai3 | NM_010306.3 | chr3:108107274-108146152 |
| 9223 | Gnal | NM_010307.3 | chr18:67133559-67226791 |
| 9224 | Gnao1 | NM_001113384.1 | chr8:93810837-93960694 |
| 9225 | Gnaq | NM_008139.5 | chr19:16132830-16387453 |
| 9226 | Gnas | NM_001077507.2 | chr2:174297858-174346742 |
| 9227 | Gnat1 | NM_008140.2 | chr9:107674473-107679592 |
| 9228 | Gnat2 | NM_008141.3 | chr3:108093065-108101430 |
| 9229 | Gnat3 | NM_001081143.1 | chr5:17962569-18019668 |
| 9230 | Gnaz | NM_010311.3 | chr10:74967230-75015877 |
| 9231 | Gnb1 | NM_001160016.1 | chr4:155491360-155559269 |
| 9232 | Gnb1l | NM_001081682.2 | chr16:18498712-18566680 |
| 9233 | Gnb2 | NM_010312.4 | chr5:137528128-137533229 |
| 9234 | Gnb2l1 | NM_008143.3 | chr11:48800359-48806241 |
| 9235 | Gnb3 | NM_013530.5 | chr6:124834239-124840275 |
| 9236 | Gnb4 | NM_013531.4 | chr3:32583527-32616535 |
| 9237 | Gnb5 | NM_010313.2 | chr9:75306287-75345923 |
| 9238 | Gne | NM_001190414.1 | chr4:44038622-44072673 |
| 9239 | Gng10 | NM_025277.3 | chr4:59035155-59041899 |
| 9240 | Gng11 | NM_025331.2 | chr6:4003986-4008446 |
| 9241 | Gng12 | NM_001177556.1 | chr6:66896396-67021361 |
| 9242 | Gng13 | NM_022422.5 | chr17:25717171-25719102 |
| 9243 | Gng2 | NM_001038637.1 | chr14:19872558-19977249 |
| 9244 | Gng3 | NM_010316.3 | chr19:8836928-8839246 |
| 9245 | Gng4 | NM_010317.3 | chr13:13784306-13827895 |
| 9246 | Gng5 | NM_010318.2 | chr3:146499835-146505543 |
| 9247 | Gng7 | NM_001038655.1 | chr10:80948623-81001365 |
| 9248 | Gng8 | NM_010320.3 | chr7:16891785-16895435 |
| 9249 | Gngt1 | NM_010314.2 | chr6:3994011-3997436 |
| 9250 | Gngt2 | NM_001038664.2 | chr11:95842667-95845731 |
| 9251 | Gni1 | NM_008136.2 | chr17:35979954-35989462 |
| 9252 | Gnl2 | NM_145552.2 | chr4:125030013-125055382 |
| 9253 | Gnl3 | NM_153547.6 | chr14:31012432-31019131 |
| 9254 | Gnl3l | NM_001168600.1 | chrX:150983132-151017293 |
| 9255 | Gnmt | NM_010321.1 | chr17:46725663-46729165 |
| 9256 | Gnpat | NM_010322.3 | chr8:124863032-124890057 |
| 9257 | Gnpda1 | NM_011937.2 | chr18:38327536-38338993 |
| 9258 | Gnpda2 | NM_001038015.1 | chr5:69575001-69592285 |
| 9259 | Gnpnat1 | NM_019425.2 | chr14:45376420-45388796 |
| 9260 | Gnptab | NM_001004164.2 | chr10:88379411-88447329 |
| 9261 | Gnptg | NM_172529.3 | chr17:25234317-25240116 |
| 9262 | Gnrh1 | NM_008145.3 | chr14:67745228-67744936 |
| 9263 | Gnrhr | NM_010323.2 | chr5:86180753-86197901 |
| 9264 | Gns | NM_029364.3 | chr10:121365089-121397245 |
| 9265 | Golga1 | NM_001290649.1 | chr2:39016155-39065541 |
| 9266 | Golga2 | NM_001080968.1 | chr2:32288252-32307921 |
| 9267 | Golga3 | NM_008146.3 | chr5:110176700-110223155 |
| 9268 | Golga4 | NM_018748.3 | chr9:118506317-118582519 |
| 9269 | Golga5 | NM_001199004.1 | chr12:102469133-102497907 |
| 9270 | Golga7 | NM_001042484.1 | chr8:23241325-23257080 |
| 9271 | Golga7b | NM_001141983.1 | chr19:42247577-42270348 |
| 9272 | Golgb1 | NM_030035.1 | chr16:36885010-36933085 |
| 9273 | Golim4 | NM_001291069.1 | chr3:75876182-75956949 |
| 9274 | Golm1 | NM_001035122.2 | chr13:59634995-59675784 |
| 9275 | Golph3 | NM_025673.2 | chr15:12321495-12351267 |
| 9276 | Golph3l | NM_001177669.1 | chr3:95588933-95619247 |
| 9277 | Golt1a | NM_026680.4 | chr1:133309822-133323026 |
| 9278 | Golt1b | NM_025872.4 | chr6:142387242-142403858 |
| 9279 | Gon4l | NM_001242372.1 | chr3:88835230-88910099 |
| 9280 | Gopc | NM_001199272.1 | chr10:52337023-52382124 |
| 9281 | Gorab | NM_178883.6 | chr1:163384902-163403669 |
| 9282 | Gorasp1 | NM_028976.2 | chr9:119925672-119937558 |
| 9283 | Gorasp2 | NM_027352.4 | chr2:70661508-70691725 |
| 9284 | Gosr1 | NM_016810.3 | chr11:76726601-76763555 |
| 9285 | Gosr2 | NM_019650.3 | chr11:103676848-103697710 |
| 9286 | Got1 | NM_010324.3 | chr19:43499752-43524605 |
| 9287 | Got1l1 | NM_029674.1 | chr8:27197458-27202547 |
| 9288 | Got2 | NM_010325.2 | chr8:95864136-95888365 |
| 9289 | Gp1ba | NM_010326.2 | chr11:70639121-70642055 |
| 9290 | Gp1bb | NM_001001999.1 | chr16:18620318-18622403 |
| 9291 | Gp2 | NM_025989.3 | chr7:119442543-119459272 |
| 9292 | Gp49a | NM_001291892.1 | chr10:51480611-51486329 |
| 9293 | Gp5 | NM_008148.4 | chr16:30307684-30310781 |
| 9294 | Gp6 | NM_001163014.1 | chr7:4368712-4397744 |
| 9295 | Gp9 | NM_018762.1 | chr6:87778135-87779762 |
| 9296 | Gpa33 | NM_021610.1 | chr1:166130459-166166510 |
| 9297 | Gpaa1 | NM_010331.2 | chr15:76331293-76334899 |
| 9298 | Gpalpp1 | NM_026177.3 | chr14:76086231-76110815 |
| 9299 | Gpam | NM_008149.3 | chr19:55069733-55099447 |
| 9300 | Gpank1 | NM_001128597.1 | chr17:35121495-35124815 |
| 9301 | Gpat2 | NM_001081089.2 | chr2:127425198-127436092 |
| 9302 | Gpatch1 | NM_026181.1 | chr7:35276543-35318440 |
| 9303 | Gpatch11 | NM_181649.6 | chr17:78835515-78848308 |
| 9304 | Gpatch2 | NM_026367.4 | chr1:187215510-187351429 |

Fig. 26 - 50

| | | | |
|---|---|---|---|
| 9305 | Gpatch2l | NM_027405.2 | chr12:86241877-86291368 |
| 9306 | Gpatch3 | NM_172876.2 | chr4:133574744-133584242 |
| 9307 | Gpatch4 | NM_001110809.2 | chr3:88043105-88055994 |
| 9308 | Gpatch8 | NM_001159492.1 | chr11:102475915-102556158 |
| 9309 | Gpbar1 | NM_174985.1 | chr1:74278599-74279589 |
| 9310 | Gpbp1 | NM_001122963.1 | chr13:111425679-111490041 |
| 9311 | Gpbp1l1 | NM_029868.2 | chr4:116557726-116593882 |
| 9312 | Gpc1 | NM_016696.4 | chr1:92831685-92860196 |
| 9313 | Gpc2 | NM_172412.2 | chr5:138273659-138279937 |
| 9314 | Gpc3 | NM_016697.3 | chrX:52272426-52613974 |
| 9315 | Gpc4 | NM_008150.2 | chrX:52053017-52164923 |
| 9316 | Gpc5 | NM_175500.4 | chr14:115092214-116525192 |
| 9317 | Gpc6 | NM_001079844.2 | chr14:116925296-117979529 |
| 9318 | Gpcpd1 | NM_001042672.1 | chr2:132529082-132578282 |
| 9319 | Gpd1 | NM_010271.2 | chr15:99717592-99725007 |
| 9320 | Gpd1l | NM_175380.5 | chr9:114899338-114933987 |
| 9321 | Gpd2 | NM_001145820.1 | chr2:57237677-57370719 |
| 9322 | Gper1 | NM_029771.3 | chr5:139423178-139427800 |
| 9323 | Gpha2 | NM_130453.3 | chr19:6226400-6227768 |
| 9324 | Gphb5 | NM_175644.3 | chr12:75411719-75416781 |
| 9325 | Gphn | NM_145965.2 | chr12:78226654-78684769 |
| 9326 | Gpi1 | NM_008155.4 | chr7:34201326-34230336 |
| 9327 | Gpihbp1 | NM_026730.1 | chr15:75596657-75598213 |
| 9328 | Gpkow | NM_173747.3 | chrX:7697133-7710259 |
| 9329 | Gpld1 | NM_008156.2 | chr13:24943151-24991936 |
| 9330 | Gpm6a | NM_001253754.1 | chr8:54779433-55060878 |
| 9331 | Gpm6b | NM_001177955.1 | chrX:166344552-166389033 |
| 9332 | Gpn1 | NM_133756.4 | chr5:31494760-31511627 |
| 9333 | Gpn2 | NM_001290742.1 | chr4:133584372-133591735 |
| 9334 | Gpn3 | NM_024216.1 | chr5:122372507-122382769 |
| 9335 | Gpnmb | NM_053110.4 | chr6:49036517-49058182 |
| 9336 | Gpr1 | NM_146250.2 | chr1:63182570-63214281 |
| 9337 | Gpr101 | NM_001033360.3 | chrX:57496667-57503757 |
| 9338 | Gpr107 | NM_178760.4 | chr2:31152315-31216567 |
| 9339 | Gpr108 | NM_030084.4 | chr17:57234914-57247689 |
| 9340 | Gpr110 | NM_133776.2 | chr17:43270346-43324406 |
| 9341 | Gpr111 | NM_001033493.2 | chr17:42708936-42742179 |
| 9342 | Gpr113 | NM_001014394.2 | chr5:30193480-30205722 |
| 9343 | Gpr114 | NM_001033468.3 | chr8:94923693-94943290 |
| 9344 | Gpr115 | NM_001289499.1 | chr17:42656886-42692284 |
| 9345 | Gpr116 | NM_001081178.1 | chr17:43389465-43459557 |
| 9346 | Gpr119 | NM_181751.2 | chrX:48667978-48674478 |
| 9347 | Gpr12 | NM_001010941.2 | chr5:146582149-146585239 |
| 9348 | Gpr123 | NM_177489.3 | chr7:139834173-139878088 |
| 9349 | Gpr124 | NM_054044.2 | chr8:27085840-27123436 |
| 9350 | Gpr125 | NM_139911.1 | chr5:49959950-50058996 |
| 9351 | Gpr126 | NM_001002268.3 | chr10:14402584-14545036 |
| 9352 | Gpr128 | NM_172825.3 | chr16:56724608-56795858 |
| 9353 | Gpr132 | NM_019925.4 | chr12:112850875-112860916 |
| 9354 | Gpr133 | NM_001081342.1 | chr5:129046749-129204599 |
| 9355 | Gpr135 | NM_181752.1 | chr12:72069617-72070991 |
| 9356 | Gpr137 | NM_001177360.1 | chr19:6938069-6941193 |
| 9357 | Gpr137b | NM_139976.2 | chr13:13357619-13393624 |
| 9358 | Gpr137b-ps | NR_003568.1 | chr13:12614064-12650395 |
| 9359 | Gpr137c | NM_027518.2 | chr14:45219716-45280976 |
| 9360 | Gpr139 | NM_001044138.1 | chr7:119144322-119184374 |
| 9361 | Gpr141 | NM_181754.4 | chr13:19749681-19824257 |
| 9362 | Gpr142 | NM_181749.1 | chr11:114798923-114806745 |
| 9363 | Gpr143 | NM_010951.3 | chrX:152781920-152808646 |
| 9364 | Gpr146 | NM_001038703.2 | chr5:139389903-139396414 |
| 9365 | Gpr149 | NM_177346.4 | chr3:62529962-62665140 |
| 9366 | Gpr15 | NM_001162955.1 | chr16:58717434-58718724 |
| 9367 | Gpr150 | NM_175495.2 | chr13:76054850-76056996 |
| 9368 | Gpr151 | NM_181543.1 | chr18:42578019-42579652 |
| 9369 | Gpr152 | NM_206973.2 | chr19:4139798-4145740 |
| 9370 | Gpr153 | NM_178406.2 | chr4:152274361-152285337 |
| 9371 | Gpr155 | NM_001190297.2 | chr2:73341505-73386480 |
| 9372 | Gpr156 | NM_153394.2 | chr16:37916495-38007529 |
| 9373 | Gpr157 | NM_177366.3 | chr4:150087502-150105927 |
| 9374 | Gpr158 | NM_001004761.1 | chr2:21367566-21830542 |
| 9375 | Gpr160 | NM_001134385.2 | chr3:30855949-30897194 |
| 9376 | Gpr161 | NM_001081126.2 | chr1:165295765-165326745 |
| 9377 | Gpr162 | NM_013533.3 | chr6:124858444-124863917 |
| 9378 | Gpr165 | NM_029536.3 | chrX:96713467-96719388 |
| 9379 | Gpr17 | NM_001025381.2 | chr18:31942998-31949636 |
| 9380 | Gpr171 | NM_173398.3 | chr3:59096447-59101821 |
| 9381 | Gpr173 | NM_027543.4 | chrX:152343598-152368704 |
| 9382 | Gpr174 | NM_001033251.4 | chrX:107256027-107296769 |
| 9383 | Gpr176 | NM_201367.3 | chr2:118277097-118373419 |
| 9384 | Gpr179 | NM_001081220.1 | chr11:97332108-97352073 |
| 9385 | Gpr18 | NM_182806.1 | chr14:121911433-121915774 |
| 9386 | Gpr180 | NM_021434.5 | chr14:118137126-118164232 |
| 9387 | Gpr182 | NM_007412.2 | chr10:127749601-127751798 |
| 9388 | Gpr183 | NM_183031.2 | chr14:121952330-121965193 |
| 9389 | Gpr19 | NM_001167694.2 | chr6:134869091-134897925 |
| 9390 | Gpr20 | NM_173365.2 | chr15:73694606-73707505 |
| 9391 | Gpr21 | NM_175175.4 | chr2:37516625-37519281 |
| 9392 | Gpr22 | NM_175191.4 | chr12:31706866-31713926 |
| 9393 | Gpr25 | NM_001101516.1 | chr1:136258913-136260873 |
| 9394 | Gpr26 | NM_173410.3 | chr7:131966459-131985633 |
| 9395 | Gpr27 | NM_008158.1 | chr6:99692678-99693818 |
| 9396 | Gpr3 | NM_008154.3 | chr4:133209339-133212536 |
| 9397 | Gpr31b | NM_001013832.2 | chr17:13051320-13052280 |
| 9398 | Gpr33 | NM_008159.2 | chr12:52023003-52028063 |
| 9399 | Gpr34 | NM_011823.4 | chrX:13632768-13640858 |
| 9400 | Gpr35 | NM_001104529.1 | chr1:92973118-92986391 |
| 9401 | Gpr37 | NM_010338.2 | chr6:25668522-25689980 |
| 9402 | Gpr37l1 | NM_134438.3 | chr1:135160249-135167681 |
| 9403 | Gpr39 | NM_027677.2 | chr1:125676995-125873861 |
| 9404 | Gpr4 | NM_175668.4 | chr7:19212537-19224176 |
| 9405 | Gpr45 | NM_053107.4 | chr1:42952871-43035449 |
| 9406 | Gpr50 | NM_010340.2 | chrX:71663666-71669257 |
| 9407 | Gpr52 | NM_001146330.1 | chr1:160576667-160577753 |
| 9408 | Gpr55 | NM_001033290.2 | chr1:85939536-85961055 |
| 9409 | Gpr56 | NM_001198894.1 | chr8:94977108-95014208 |
| 9410 | Gpr6 | NM_199058.1 | chr10:41070492-41071584 |
| 9411 | Gpr61 | NM_001305461.1 | chr3:108148321-108154986 |
| 9412 | Gpr62 | NM_001159652.1 | chr9:106463959-106465940 |
| 9413 | Gpr63 | NM_030733.3 | chr4:24973418-25009233 |
| 9414 | Gpr64 | NM_001079847.2 | chrX:160390689-160498076 |
| 9415 | Gpr65 | NM_008152 | chr12:98268634-98276722 |
| 9416 | Gpr68 | NM_001177673.1 | chr12:100876681-100908198 |
| 9417 | Gpr75 | NM_175490.4 | chr11:30885357-30893725 |
| 9418 | Gpr82 | NM_175669.3 | chrX:13661362-13667433 |
| 9419 | Gpr83 | NM_010287.3 | chr9:14860209-14870789 |
| 9420 | Gpr84 | NM_030720.1 | chr15:103308234-103310438 |
| 9421 | Gpr85 | NM_145066.4 | chr6:13835073-13839848 |
| 9422 | Gpr87 | XM_006502394.2 | chr3:59178904-59195468 |
| 9423 | Gpr88 | NM_022427.2 | chr3:116249653-116253484 |
| 9424 | Gpr89 | NM_026229.4 | chr3:96871065-96905298 |
| 9425 | Gpr97 | NM_173036.3 | chr8:95017691-95045249 |
| 9426 | Gpr98 | NM_054053.3 | chr13:81095067-81633144 |
| 9427 | Gprasp1 | NM_001004359.2 | chrX:135742691-135803468 |
| 9428 | Gprasp2 | NM_001163015.1 | chrX:135839033-135844730 |
| 9429 | Gprc5a | NM_181444.5 | chr6:135065661-135084708 |
| 9430 | Gprc5b | NM_001195774.1 | chr7:118972039-118995211 |
| 9431 | Gprc5c | NM_001110337.1 | chr11:114851531-114872617 |
| 9432 | Gprc5d | NM_001205396.1 | chr6:135105990-135118283 |
| 9433 | Gprc6a | NM_153071.1 | chr10:51614822-51631458 |
| 9434 | Gprin1 | NM_020014.3 | chr13:54736672-54749669 |
| 9435 | Gprin2 | NM_183209.2 | chr14:34194440-34201633 |
| 9436 | Gprin3 | NM_183183.2 | chr6:59352460-59426290 |
| 9437 | Gps1 | NM_001177874.1 | chr11:120784271-120789102 |
| 9438 | Gps2 | NM_019726.3 | chr11:69914191-69916591 |
| 9439 | Gpsm1 | NM_001199146.1 | chr2:26315532-26348237 |
| 9440 | Gpsm2 | NM_029522.2 | chr3:108678637-108722299 |
| 9441 | Gpsm3 | NM_134116.5 | chr17:34589805-34591754 |
| 9442 | Gpt | NM_182805.2 | chr15:76696763-76699675 |
| 9443 | Gpt2 | NM_173866.3 | chr8:85492616-85527558 |
| 9444 | Gpx1 | NM_008160.1 | chr9:108339079-108340344 |
| 9445 | Gpx2 | NM_030677.2 | chr12:76792334-76795554 |
| 9446 | Gpx2-ps1 | NR_033563.1 | chr7:100264543-100265561 |
| 9447 | Gpx3 | NM_008161.3 | chr11:54902853-54910382 |
| 9448 | Gpx4 | NM_001037741.3 | chr10:80054018-80056439 |
| 9449 | Gpx5 | NM_010343.2 | chr13:21286428-21292686 |
| 9450 | Gpx6 | NM_145451.3 | chr13:21312202-21319624 |
| 9451 | Gpx7 | NM_024198.3 | chr4:108400216-108406713 |
| 9452 | Gpx8 | NM_027127.2 | chr13:113042762-113046388 |
| 9453 | Gramd1a | NM_027898.3 | chr7:31130126-31151050 |
| 9454 | Gramd1b | NM_172768.1 | chr9:40297906-40455764 |
| 9455 | Gramd1c | NM_001172107.1 | chr16:43980349-44027945 |
| 9456 | Gramd2 | NM_001033498.1 | chr9:59707763-59716424 |
| 9457 | Gramd3 | NM_026240.2 | chr18:56432131-56503792 |
| 9458 | Gramd4 | NM_001205353.1 | chr15:86058726-86137636 |
| 9459 | Grap | NM_027817.3 | chr11:61665320-61672777 |
| 9460 | Grap2 | NM_001289442.1 | chr15:80572596-80652854 |
| 9461 | Grasp | NM_199518.3 | chr15:101224206-101232756 |
| 9462 | Grb10 | NM_001177629.1 | chr11:11930498-12027971 |
| 9463 | Grb14 | NM_016719.1 | chr2:64912481-65022766 |
| 9464 | Grb2 | NM_008163.4 | chr11:115644044-115708597 |
| 9465 | Grb7 | NM_010346.2 | chr11:98446833-98455373 |
| 9466 | Grcc10 | NM_013535.1 | chr6:124739183-124741079 |
| 9467 | Greb1 | NM_001252071.1 | chr12:16670614-16757239 |
| 9468 | Greb1l | NM_001083628.1 | chr18:10325178-10562941 |
| 9469 | Grem1 | NM_011824.4 | chr2:113748674-113758648 |
| 9470 | Grem2 | NM_011825.1 | chr1:174833784-174921819 |
| 9471 | Grhl1 | NM_001161406.1 | chr12:24572286-24617391 |
| 9472 | Grhl2 | NM_026496.4 | chr15:37233035-37363968 |
| 9473 | Grhl3 | NM_001013756.1 | chr4:135541887-135573620 |
| 9474 | Grhpr | NM_080289.2 | chr4:44981393-44990734 |
| 9475 | Gria1 | NM_001113325.2 | chr11:57011617-57330244 |
| 9476 | Gria2 | NM_001039195.1 | chr3:80691491-80802791 |
| 9477 | Gria3 | NM_001281929.1 | chrX:41401300-41678601 |
| 9478 | Gria4 | NM_001113180.1 | chr9:4417892-4796234 |
| 9479 | Grid1 | NM_008166.2 | chr14:34820135-35581115 |
| 9480 | Grid2 | NM_008167.2 | chr6:63256856-64666279 |
| 9481 | Grid2ip | NM_001159321.1 | chr5:143357337-143391468 |
| 9482 | Grifin | NM_030022.1 | chr5:140563188-140565067 |
| 9483 | Grik1 | NM_010348.3 | chr16:87895896-88290258 |
| 9484 | Grik2 | NM_001111268.1 | chr10:49099462-49788754 |
| 9485 | Grik3 | NM_001081097.2 | chr4:125499830-125714173 |
| 9486 | Grik4 | NM_175481.5 | chr9:42520411-42944371 |
| 9487 | Grik5 | NM_008168.2 | chr7:25009850-25072369 |
| 9488 | Grin1 | NM_001177656.2 | chr2:25291178-25319187 |
| 9489 | Grin1os | NM_001242940.1 | chr2:25291219-25298928 |
| 9490 | Grin2a | NM_008170.2 | chr16:9577709-9992533 |
| 9491 | Grin2b | NM_008171.3 | chr6:135729804-136173511 |
| 9492 | Grin2c | NM_010350.2 | chr11:115249168-115267243 |
| 9493 | Grin2d | NM_008172.2 | chr7:45832482-45866681 |
| 9494 | Grin3a | NM_001033351.2 | chr4:49661610-49845769 |

Fig. 26 - 51

| | | | |
|---|---|---|---|
| 9495 | Grin3b | NM_130455.2 | chr10:79970723-79977190 |
| 9496 | Grina | NM_023168.3 | chr15:76246806-76249904 |
| 9497 | Grip1 | NM_001277292.1 | chr10:119454033-120077161 |
| 9498 | Grip1os2 | NR_045359.1 | chr10:119746061-119761699 |
| 9499 | Grip2 | NM_001159507.1 | chr6:91761509-91807393 |
| 9500 | Gripap1 | NM_001290455.1 | chrX:7789992-7820567 |
| 9501 | Grk1 | NM_011881 | chr8:13405080-13421949 |
| 9502 | Grk4 | NM_001080743.1 | chr5:34660378-34701088 |
| 9503 | Grk5 | NM_018869.3 | chr19:60889748-61092555 |
| 9504 | Grk6 | NM_001038018.4 | chr13:55445338-55460927 |
| 9505 | Grm1 | NM_001114333.2 | chr10:10686058-11082331 |
| 9506 | Grm2 | NM_001160353.1 | chr9:106644533-106656109 |
| 9507 | Grm3 | NM_181850.2 | chr5:9485235-9725352 |
| 9508 | Grm4 | NM_001013385.2 | chr17:27422387-27503533 |
| 9509 | Grm5 | NM_001081414.2 | chr7:87584167-88135063 |
| 9510 | Grm6 | NM_173372.2 | chr11:50850684-50866208 |
| 9511 | Grm7 | NM_177328.3 | chr6:110645597-111567230 |
| 9512 | Grm8 | NM_008174.2 | chr6:27275120-28134369 |
| 9513 | Grn | NM_008175.4 | chr11:102430321-102436089 |
| 9514 | Grp | NM_175012.4 | chr18:65873485-65886596 |
| 9515 | Grpel1 | NM_024478.2 | chr5:36465184-36474077 |
| 9516 | Grpel2 | NM_021296.2 | chr18:61712423-61726331 |
| 9517 | Grpr | NM_008177.3 | chrX:163513903-163549736 |
| 9518 | Grrp1 | NM_001099296.2 | chr4:134251109-134254106 |
| 9519 | Grsf1 | NM_001098476.2 | chr5:88669232-88675580 |
| 9520 | Grtp1 | NM_025768.2 | chr8:13176868-13200624 |
| 9521 | Grwd1 | NM_153419.2 | chr7:45825222-45830789 |
| 9522 | Grxcr1 | NM_001031834.2 | chr5:68031834-68166398 |
| 9523 | Grxcr2 | NM_001033426.2 | chr18:41986200-41999049 |
| 9524 | Gsap | NM_175437.3 | chr5:21186266-21291701 |
| 9525 | Gsc | NM_010351.1 | chr12:104471208-104473236 |
| 9526 | Gsc2 | NM_029469.1 | chr16:17913553-17915059 |
| 9527 | Gsdma | NM_021347.4 | chr11:98646350-98677708 |
| 9528 | Gsdma2 | NM_029727.2 | chr11:98646758-98657957 |
| 9529 | Gsdma3 | NM_001007461.1 | chr11:98626359-98638089 |
| 9530 | Gsdmc | NM_031378.3 | chr15:63775970-63808739 |
| 9531 | Gsdmc2 | NM_001168274.1 | chr15:63824345-63845176 |
| 9532 | Gsdmc3 | NM_183194.3 | chr15:63857724-63878558 |
| 9533 | Gsdmc4 | NM_028992.1 | chr15:63891264-63912297 |
| 9534 | Gsdmcl1 | NR_108051.1 | chr15:63847308-63850942 |
| 9535 | Gsdmcl2 | NR_108053.1 | chr15:63880706-63889073 |
| 9536 | Gsdmcl-ps | NR_029414.1 | chr15:63914460-63925453 |
| 9537 | Gsdmd | NM_026960.4 | chr15:75862338-75867404 |
| 9538 | Gse1 | NM_001145896.1 | chr8:120537408-120581383 |
| 9539 | Gsg1 | NM_001080552.1 | chr6:135237329-135247884 |
| 9540 | Gsg1l | NM_001101488.1 | chr7:125878418-126082411 |
| 9541 | Gsg2 | NM_010353.2 | chr11:73135483-73138294 |
| 9542 | Gsk3a | NM_001031667.1 | chr7:25228258-25237851 |
| 9543 | Gsk3b | NM_019827.4 | chr16:38089000-38246079 |
| 9544 | Gskip | NM_178613.3 | chr12:105685351-105703057 |
| 9545 | Gsn | NM_001206367.1 | chr2:35256358-35307902 |
| 9546 | Gspt1 | NM_001130008.1 | chr16:11216240-11254325 |
| 9547 | Gspt2 | NM_008179.2 | chrX:94636068-94638561 |
| 9548 | Gsr | NM_010344.4 | chr8:33653237-33698162 |
| 9549 | Gss | NM_001291111.1 | chr2:155563180-155592810 |
| 9550 | Gsta1 | NM_008181.3 | chr9:78230668-78242683 |
| 9551 | Gsta2 | NM_008182.3 | chr9:78331019-78347145 |
| 9552 | Gsta3 | NM_001077353.2 | chr1:21240584-21265575 |
| 9553 | Gsta4 | NM_010357.3 | chr9:78191965-78209349 |
| 9554 | Gstcd | NM_026231.2 | chr3:132982550-133091740 |
| 9555 | Gstk1 | NM_029555.2 | chr6:42245934-42250441 |
| 9556 | Gstm1 | NM_010358.5 | chr3:108012249-108017973 |
| 9557 | Gstm2 | NM_008183.3 | chr3:107981701-107986436 |
| 9558 | Gstm3 | NM_010359.2 | chr3:107963695-107969174 |
| 9559 | Gstm4 | NM_001160411.1 | chr3:108040407-108044859 |
| 9560 | Gstm5 | NM_010360.3 | chr3:107895853-107898685 |
| 9561 | Gstm6 | NM_008184.3 | chr3:107938847-107943749 |
| 9562 | Gstm7 | NM_026672.2 | chr3:107926333-107931745 |
| 9563 | Gsto1 | NM_010362.2 | chr19:47854988-47864788 |
| 9564 | Gsto2 | NM_026619.2 | chr19:47865793-47886305 |
| 9565 | Gstp1 | NM_013541.1 | chr19:4035410-4037912 |
| 9566 | Gstp2 | NM_181796.2 | chr19:4040287-4042221 |
| 9567 | Gstt1 | NM_008185.3 | chr10:75783812-75798584 |
| 9568 | Gstt2 | NM_010361.2 | chr10:75831844-75834881 |
| 9569 | Gstt3 | NM_133994.3 | chr10:75774121-75781414 |
| 9570 | Gstt4 | NM_029472.3 | chr10:75814943-75822543 |
| 9571 | Gstz1 | NM_001252555.1 | chr12:87147164-87164723 |
| 9572 | Gsx1 | NM_008178.2 | chr5:147188695-147190946 |
| 9573 | Gsx2 | NM_133324.2 | chr5:75075600-75077893 |
| 9574 | Gt(ROSA)26Sor | NR_027008.1 | chr6:113070398-113077244 |
| 9575 | Gtdc1 | NM_172662.3 | chr2:44564411-44861622 |
| 9576 | Gtf2a1 | NM_001291075.1 | chr12:91555261-91589649 |
| 9577 | Gtf2a1l | NM_023630.2 | chr17:88668659-88715150 |
| 9578 | Gtf2a2 | NM_001039519.2 | chr9:70012547-70022866 |
| 9579 | Gtf2b | NM_145546.1 | chr3:142765246-142783605 |
| 9580 | Gtf2e1 | NM_028812.3 | chr16:37509795-37539769 |
| 9581 | Gtf2e2 | NM_001167921.1 | chr8:33731913-33777173 |
| 9582 | Gtf2f1 | NM_133801.2 | chr17:57003401-57011288 |
| 9583 | Gtf2f2 | NM_026816.3 | chr14:75896936-76010865 |
| 9584 | Gtf2h1 | NM_001291075.1 | chr7:46796670-46823800 |
| 9585 | Gtf2h2 | NM_022011.4 | chr13:100468576-100492609 |
| 9586 | Gtf2h3 | NM_181410.3 | chr5:124579147-124597680 |
| 9587 | Gtf2h4 | NM_001064727.1 | chr17:35667727-35673743 |
| 9588 | Gtf2h5 | NM_181392.3 | chr17:6079827-6085485 |
| 9589 | Gtf2i | NM_001080746.2 | chr5:134237831-134314760 |
| 9590 | Gtf2ird1 | NM_001081462.2 | chr5:134357660-134456716 |
| 9591 | Gtf2ird2 | NM_053266.1 | chr5:134184037-134218143 |
| 9592 | Gtf3a | NM_025652.3 | chr5:146948656-146955614 |
| 9593 | Gtf3c1 | NM_207239.1 | chr7:125640953-125707688 |
| 9594 | Gtf3c2 | NM_027901.2 | chr5:31156005-31180144 |
| 9595 | Gtf3c3 | NM_001033194.3 | chr1:54395876-54439026 |
| 9596 | Gtf3c4 | NM_001166033.1 | chr2:28822299-28840360 |
| 9597 | Gtf3c5 | NM_001290484.1 | chr2:28566244-28583279 |
| 9598 | Gtf3c6 | NM_026113.4 | chr10:40249202-40257665 |
| 9599 | Gtl3 | NM_008187.2 | chr8:95420249-95434869 |
| 9600 | Gtpbp1 | NM_013818.2 | chr15:79690895-79721479 |
| 9601 | Gtpbp10 | NM_153116.1 | chr5:5537456-5559501 |
| 9602 | Gtpbp2 | NM_001145979.1 | chr17:46161631-46169370 |
| 9603 | Gtpbp3 | NM_032544.3 | chr8:71488102-71493400 |
| 9604 | Gtpbp4 | NM_027000.4 | chr13:8972477-8996012 |
| 9605 | Gtpbp6 | NM_145147.5 | chr5:110103976-110108197 |
| 9606 | Gtpbp8 | NM_001159329.1 | chr16:44738878-44746363 |
| 9607 | Gtse1 | NM_001168672.1 | chr15:85859706-85876573 |
| 9608 | Gtsf1 | NM_028797.1 | chr15:103402458-103430427 |
| 9609 | Gtsf1l | NM_026630.2 | chr2:163087030-163089601 |
| 9610 | Guca1a | NM_008189.2 | chr17:47394557-47400584 |
| 9611 | Guca1b | NM_146079.1 | chr17:47385392-47392967 |
| 9612 | Guca2a | NM_008190.1 | chr4:119637731-119639465 |
| 9613 | Guca2b | NM_008191.2 | chr4:119656602-119658945 |
| 9614 | Gucd1 | NM_175133.1 | chr10:75506813-75517322 |
| 9615 | Gucy1a2 | NM_001033322.2 | chr9:3532348-3905787 |
| 9616 | Gucy1a3 | NM_021896.5 | chr3:82092426-82145877 |
| 9617 | Gucy1b2 | NM_001204340.1 | chr14:62392669-62456289 |
| 9618 | Gucy1b3 | NM_001161796.1 | chr3:82032003-82074711 |
| 9619 | Gucy2c | NM_001127134.1 | chr6:136697283-136781742 |
| 9620 | Gucy2d | NM_001130693.3 | chr7:98440415-98477478 |
| 9621 | Gucy2e | NM_008192.3 | chr11:69218116-69237022 |
| 9622 | Gucy2f | NM_001007576.2 | chrX:142079288-142196936 |
| 9623 | Gucy2g | NM_001081076.2 | chr19:55198097-55241236 |
| 9624 | Guf1 | NM_172711.3 | chr5:69556923-69574652 |
| 9625 | Guk1 | NM_001159410.1 | chr11:59183854-59187741 |
| 9626 | Gulo | NM_178747.3 | chr14:65986786-66009210 |
| 9627 | Gulp1 | NM_028450.3 | chr1:44551670-44796836 |
| 9628 | Gusb | NM_010368.1 | chr5:129989026-130002828 |
| 9629 | Gvin1 | NM_001039160.2 | chr7:105895118-106215340 |
| 9630 | Gxylt1 | NM_001033275.4 | chr15:93239741-93275084 |
| 9631 | Gxylt2 | NM_198612.2 | chr6:100704733-100805081 |
| 9632 | Gyg | NM_013755.3 | chr3:20122083-20155116 |
| 9633 | Gyk | NM_008194.3 | chrX:85701936-85776819 |
| 9634 | Gykl1 | NM_010293.3 | chr18:52693678-52695593 |
| 9635 | Gyltl1b | NM_001166633.2 | chr2:92365045-92371057 |
| 9636 | Gypa | NM_010369.3 | chr8:80494044-80510785 |
| 9637 | Gypc | NM_001048207.1 | chr18:32528319-32560034 |
| 9638 | Gys1 | NM_030678.3 | chr7:45434838-45456617 |
| 9639 | Gys2 | NM_145572.2 | chr6:142422612-142473109 |
| 9640 | Gzf1 | NM_028986.3 | chr2:148681119-148692949 |
| 9641 | Gzma | NM_010370.2 | chr13:113093826-113109981 |
| 9642 | Gzmb | NM_013542.2 | chr14:56258857-56262250 |
| 9643 | Gzmc | NM_010371.3 | chr14:56231400-56234657 |
| 9644 | Gzmd | NM_010372.2 | chr14:56129567-56132593 |
| 9645 | Gzme | NM_010373.3 | chr14:56117618-56120625 |
| 9646 | Gzmf | NM_010374.3 | chr14:56205262-56211407 |
| 9647 | Gzmg | NM_010375.2 | chr14:56156580-56159579 |
| 9648 | Gzmk | NM_008196.1 | chr13:113171873-113180897 |
| 9649 | Gzmm | NM_008504.3 | chr10:79689019-79695261 |
| 9650 | Gzmn | NM_153052.2 | chr14:56165795-56174599 |
| 9651 | H13 | NM_001159551.1 | chr2:152669460-152708668 |
| 9652 | H19 | NR_130973.1 | chr7:142575532-142578146 |
| 9653 | H1f0 | NM_008197.3 | chr15:79028211-79030500 |
| 9654 | H1fnt | NM_027304.2 | chr15:98255981-98257307 |
| 9655 | H1foo | NM_138311.3 | chr6:115944930-115950242 |
| 9656 | H1fx | NM_198622.1 | chr6:87980420-87981482 |
| 9657 | H2-Aa | NM_010378.2 | chr17:34282750-34287771 |
| 9658 | H2-Ab1 | NM_207105.3 | chr17:34263226-34269418 |
| 9659 | H2afb1 | NM_026627.2 | chr2:17996416-17996958 |
| 9660 | H2afb2 | NM_001281530.1 | chrX:116681177-116681525 |
| 9661 | H2afb3 | NM_001281531.1 | chrX:120317747-120318095 |
| 9662 | H2afj | NM_177688.4 | chr6:136808247-136810074 |
| 9663 | H2afv | NM_029938.1 | chr11:6427225-6444443 |
| 9664 | H2afx | NM_010436.2 | chr9:44334714-44336073 |
| 9665 | H2afy | NM_001159513.1 | chr13:56073621-56135550 |
| 9666 | H2afv2 | NM_207000.2 | chr10:61738646-61783864 |
| 9667 | H2afy3 | NR_003523.1 | chr15:62217540-62219451 |
| 9668 | H2afz | NM_016750.3 | chr3:137864486-137866922 |
| 9669 | H2bfm | NM_027067.2 | chr136:927324-136928373 |
| 9670 | H2-Bl | NM_008199.2 | chr17:36080188-36084249 |
| 9671 | H2-D1 | NM_010380.3 | chr17:35263093-35267497 |
| 9672 | H2-DMa | NM_010386.4 | chr17:34122831-34139101 |
| 9673 | H2-DMb1 | NM_010387.3 | chr17:34153190-34160229 |
| 9674 | H2-DMb2 | NM_010388.4 | chr17:34145415-34151095 |
| 9675 | H2-Ea-ps | NM_010381.2 | chr17:34342211-34344645 |
| 9676 | H2-Eb1 | NM_010382.2 | chr17:34305866-34316674 |
| 9677 | H2-Eb2 | NM_001033978.3 | chr17:34325674-34341410 |
| 9678 | H2-K1 | NM_001001892.2 | chr17:33996011-34000333 |
| 9679 | H2-K2 | NR_004446.1 | chr17:33974658-33978791 |
| 9680 | H2-Ke2 | NM_001185182.1 | chr17:33938908-33940330 |
| 9681 | H2-Ke6 | NM_013543.2 | chr17:34026032-34028055 |
| 9682 | H2-L | NM_001267808.1 | chr17:35263122-35266730 |
| 9683 | H2-M1 | NM_177636.3 | chr17:36670007-36672197 |
| 9684 | H2-M10.1 | NM_013544.3 | chr17:36322859-36326150 |

Fig. 26 - 52

| | | | | | | | |
|---|---|---|---|---|---|---|---|
| 9685 | H2-M10.2 | NM_177923.1 | chr17:36284280-36286421 | 9780 | Hcls1 | NM_008225.2 | chr16:36934982-36963214 |
| 9686 | H2-M10.3 | NM_201808.2 | chr17:36365003-36368417 | 9781 | Hcn1 | NM_010408.3 | chr13:117602319-117981028 |
| 9687 | H2-M10.4 | NM_177634.1 | chr17:36460163-36462329 | 9782 | Hcn2 | NM_008226.2 | chr10:79716633-79736108 |
| 9688 | H2-M10.5 | NM_177837.3 | chr17:36772909-36776235 | 9783 | Hcn3 | NM_008227.1 | chr3:89146774-89160157 |
| 9689 | H2-M10.6 | NM_201611.2 | chr17:36812174-36815566 | 9784 | Hcn4 | NM_001081192.1 | chr9:58823511-58860955 |
| 9690 | H2-M11 | NM_177635.1 | chr17:36547074-36549252 | 9785 | Hcrt | NM_010410.2 | chr11:100761692-100762931 |
| 9691 | H2-M2 | NM_008204.2 | chr17:37480850-37483529 | 9786 | Hcrtr1 | NM_001163027.1 | chr4:130130216-130138551 |
| 9692 | H2-M3 | NM_013819.2 | chr17:37270233-37274485 | 9787 | Hcrtr2 | NM_198962.3 | chr9:76225879-76323578 |
| 9693 | H2-M5 | NM_001115075.1 | chr17:36986854-36989504 | 9788 | Hcst | NM_011827.3 | chr7:30417711-30419854 |
| 9694 | H2-M9 | NM_008205.1 | chr17:36640424-36642644 | 9789 | Hdac1 | NM_008228.2 | chr4:129516103-129542646 |
| 9695 | H2-Oa | NM_008206.2 | chr17:34092378-34095234 | 9790 | Hdac10 | NM_199198.2 | chr15:89123302-89128700 |
| 9696 | H2-Ob | NM_010389.3 | chr17:34238904-34245908 | 9791 | Hdac11 | NM_144919.2 | chr6:91156814-91174683 |
| 9697 | H2-Q1 | NM_010390.3 | chr17:35320557-35325099 | 9792 | Hdac2 | NM_008229.2 | chr10:36974543-37001888 |
| 9698 | H2-Q10 | NM_010391.4 | chr17:35470088-35474563 | 9793 | Hdac3 | NM_010411.2 | chr18:37936970-37954988 |
| 9699 | H2-Q2 | NM_010392.2 | chr17:35342332-35345722 | 9794 | Hdac4 | NM_207225.2 | chr1:91928778-92180341 |
| 9700 | H2-Q4 | NM_001143689.1 | chr17:35379615-35384674 | 9795 | Hdac5 | NM_001077696.1 | chr11:102195746-102230172 |
| 9701 | H2-Q5 | NR_051981.1 | chr17:35394098-35395630 | 9796 | Hdac6 | NM_001130416.1 | chrX:7930121-7947989 |
| 9702 | H2-Q6 | NM_207648.1 | chr17:35424876-35428361 | 9797 | Hdac7 | NM_001204275.1 | chr15:97792663-97844502 |
| 9703 | H2-Q7 | NM_001198560.1 | chr17:35439154-35443773 | 9798 | Hdac8 | NM_027382.4 | chrX:102284637-102505158 |
| 9704 | H2-Q8 | NM_023124.5 | chr17:35424846-35428361 | 9799 | Hdac9 | NM_001271386.1 | chr12:34047581-34917095 |
| 9705 | H2-Q9 | NM_001201460.1 | chr17:35439166-35443770 | 9800 | Hdc | NM_008230.6 | chr2:126593659-126618678 |
| 9706 | H2-T10 | NM_010395.7 | chr17:36115875-36121435 | 9801 | Hddc2 | NM_027168.2 | chr10:31313404-31328086 |
| 9707 | H2-T22 | NM_010397.4 | chr17:36038408-36042702 | 9802 | Hddc3 | NM_026812.2 | chr7:80343136-80346097 |
| 9708 | H2-T23 | NM_010398.3 | chr17:36029976-36032701 | 9803 | Hdgf | NM_008231.4 | chr3:87906320-87916132 |
| 9709 | H2-T24 | NM_008207.3 | chr17:36005694-36020560 | 9804 | Hdgfl1 | NM_008232.3 | chr13:26768171-26770165 |
| 9710 | H2-T3 | NM_008208.4 | chr17:36185570-36190151 | 9805 | Hdgfrp2 | NM_008233.3 | chr17:56079630-56100604 |
| 9711 | H2-T9 | NM_010399.2 | chr17:36038408-36042692 | 9806 | Hdgfrp3 | NM_013886.4 | chr7:81881255-81934459 |
| 9712 | H3f3a | NM_008210.4 | chr1:180802567-180813603 | 9807 | Hdhd1a | NM_026108.3 | chr18:50567655-50568699 |
| 9713 | H3f3b | NM_008211.3 | chr11:116021960-116024504 | 9808 | Hdhd2 | NM_001039201.1 | chr18:76944417-76972171 |
| 9714 | H60b | NM_001177775.1 | chr10:22273473-22288848 | 9809 | Hdhd3 | NM_024257.1 | chr4:62499053-62502200 |
| 9715 | H60c | NM_001204916.2 | chr10:3256207-3267771 | 9810 | Hdlbp | NM_133808.5 | chr1:93405939-93478917 |
| 9716 | H6pd | NM_001291004.1 | chr4:149979473-150003236 | 9811 | Hdx | NM_001080549.2 | chrX:111575203-111697079 |
| 9717 | Haao | NM_025325.2 | chr17:83831353-83846790 | 9812 | Heatr1 | NM_144835.4 | chr13:12395374-12438893 |
| 9718 | Habp2 | NM_146101.1 | chr19:56287937-56320089 | 9813 | Heatr2 | NM_001081265.1 | chr5:139150222-139186505 |
| 9719 | Habp4 | NM_019986 | chr13:64161865-64186537 | 9814 | Heatr3 | NM_172757.3 | chr8:88137884-88171943 |
| 9720 | Hace1 | NM_172473.2 | chr10:45577828-45712345 | 9815 | Heatr5a | NM_177171.4 | chr12:51875872-51971321 |
| 9721 | Hacl1 | NM_019975.3 | chr14:31607225-31640965 | 9816 | Heatr5b | NM_001081179.1 | chr17:78752905-78835381 |
| 9722 | Hadh | NM_008212.4 | chr3:131233419-131272101 | 9817 | Heatr6 | NM_145432.3 | chr11:83753636-83783754 |
| 9723 | Hadha | NM_178878.2 | chr5:30118303-30154980 | 9818 | Heatr9 | NM_001045543.2 | chr11:83511678-83522099 |
| 9724 | Hadhb | NM_001289798.1 | chr5:30155252-30184593 | 9819 | Hebp1 | NM_013546.2 | chr6:135137518-135168215 |
| 9725 | Hagh | NM_001159626.1 | chr17:24850666-24864450 | 9820 | Hebp2 | NM_019487.3 | chr10:18540122-18546076 |
| 9726 | Haghl | NM_001271433.1 | chr17:25782786-25785586 | 9821 | Heca | NM_001033432.3 | chr10:17900465-17940067 |
| 9727 | Hal | NM_010401.3 | chr10:93488767-93516743 | 9822 | Hectd1 | NM_144788.2 | chr12:51743721-51829536 |
| 9728 | Hamp | NM_032541.1 | chr7:30942368-30944017 | 9823 | Hectd2 | NM_001163471.1 | chr19:36554638-36621135 |
| 9729 | Hamp2 | NM_183257.3 | chr7:30922371-30924181 | 9824 | Hectd3 | NM_175244.3 | chr4:116995347-117005277 |
| 9730 | Hand1 | NM_008213.2 | chr11:57828712-57832147 | 9825 | Hecw1 | NM_001081348.3 | chr13:14226437-14523226 |
| 9731 | Hand2 | NM_010402.4 | chr8:57320982-57324517 | 9826 | Hecw2 | NM_001001883.3 | chr1:53806873-54195034 |
| 9732 | Hao1 | NM_010403.2 | chr2:134497360-134554352 | 9827 | Heg1 | NM_175256.5 | chr16:33684465-33768195 |
| 9733 | Hao2 | NM_019545.4 | chr3:98874518-98893230 | 9828 | Hells | NM_080446.2 | chr10:120083607-120112965 |
| 9734 | Hap1 | NM_010404.3 | chr11:100347326-100356141 | 9829 | Helq | NM_008234.3 | chr19:38930989-38968277 |
| 9735 | Hapln1 | NM_013500.4 | chr13:89540635-89611832 | 9830 | Helt | NM_001081107.1 | chr5:100762147-100798600 |
| 9736 | Hapln2 | NM_022031.2 | chr3:88021749-88027511 | 9831 | Helz | NM_173789.4 | chr11:107547959-107686943 |
| 9737 | Hapln3 | NM_178255.3 | chr7:79117028-79131018 | 9832 | Helz2 | NM_198298.1 | chr2:181227614-181242027 |
| 9738 | Hapln4 | NM_177900.4 | chr8:70083528-70090862 | 9833 | Hemgn | NM_053149.2 | chr4:46393988-46404183 |
| 9739 | Harbi1 | NM_178724.4 | chr2:91710949-91721566 | 9834 | Hemk1 | NM_133984.2 | chr9:107327081-107338350 |
| 9740 | Hars | NM_008766.2 | chr18:36766527-36783205 | 9835 | Hemt1 | NM_010416.2 | chr15:74819075-74824436 |
| 9741 | Hars2 | NM_080636.2 | chr18:36783208-36792560 | 9836 | Henmt1 | NM_001078646.1 | chr3:108940556-108960776 |
| 9742 | Has1 | NM_008215.2 | chr17:17843325-17855188 | 9837 | Hepacam | NM_175189.4 | chr9:37367605-37386571 |
| 9743 | Has2 | NM_008216.3 | chr15:56665626-56694546 | 9838 | Hepacam2 | NM_178899.5 | chr6:3457088-3494498 |
| 9744 | Has2os | NR_002874.2 | chr15:56689943-56694460 | 9839 | Heph | NM_001159627.1 | chrX:96456345-96574484 |
| 9745 | Has3 | NM_008217.4 | chr8:106870241-106882902 | 9840 | Hephl1 | NM_001164797.1 | chr9:15051840-15112108 |
| 9746 | Hat1 | NM_026115.4 | chr2:71389259-71441622 | 9841 | Herc1 | NM_145617.3 | chr9:66350449-66508775 |
| 9747 | Haus1 | NM_146089.2 | chr18:77757566-77767780 | 9842 | Herc2 | NM_010418.2 | chr7:56050154-56231798 |
| 9748 | Haus2 | NM_001290807.1 | chr2:120609594-120621559 | 9843 | Herc3 | NM_028705.3 | chr6:58833699-58920396 |
| 9749 | Haus3 | NM_146196.1 | chr5:34153896-34169424 | 9844 | Herc4 | NM_026101.4 | chr10:63243796-63317881 |
| 9750 | Haus4 | NM_145462.2 | chr14:54541784-54554361 | 9845 | Herc6 | NM_025992.2 | chr6:57580991-57665136 |
| 9751 | Haus5 | NM_027999.1 | chr7:30653707-30664994 | 9846 | Herpud1 | NM_022331.1 | chr8:94386499-94395358 |
| 9752 | Haus6 | NM_173400.2 | chr4:86581284-86612022 | 9847 | Herpud2 | NM_020586.2 | chr9:25108129-25151781 |
| 9753 | Haus7 | NM_028633.3 | chrX:73437314-73459029 | 9848 | Hes1 | NM_008235.2 | chr16:30065356-30067796 |
| 9754 | Haus8 | NM_001163042.1 | chr8:71251123-71272590 | 9849 | Hes2 | NM_008236.4 | chr4:152158866-152162469 |
| 9755 | Havcr1 | NM_001166631.1 | chr11:46750510-46779578 | 9850 | Hes3 | NM_008237.4 | chr4:152285971-152291662 |
| 9756 | Havcr2 | NM_134250.2 | chr11:46454930-46481254 | 9851 | Hes5 | NM_010419.4 | chr4:154969922-154962371 |
| 9757 | Hax1 | NM_001282031.1 | chr3:89995445-89998716 | 9852 | Hes6 | NM_019479.3 | chr1:91411482-91413222 |
| 9758 | Hba-a1 | NM_008218.2 | chr11:32283671-32297303 | 9853 | Hes7 | NM_033041.4 | chr11:69120452-69123259 |
| 9759 | Hba-a2 | NM_001083955.1 | chr11:32283674-32297310 | 9854 | Hesx1 | NM_010420.2 | chr14:27000361-27002325 |
| 9760 | Hba-x | NM_010405.2 | chr11:32276599-32278115 | 9855 | Hexa | NM_010421.4 | chr9:59539666-59565105 |
| 9761 | Hbb-b1 | NM_001278161.1 | chr7:103826531-103827929 | 9856 | Hexb | NM_010422.2 | chr13:97176330-97198357 |
| 9762 | Hbb-bh1 | NM_008219.3 | chr7:103841637-103843162 | 9857 | Hexdc | NM_001001333.2 | chr11:121204432-121222656 |
| 9763 | Hbb-bh2 | NM_001071686.1 | chr7:103839123-103840521 | 9858 | Hexim1 | NM_138753.2 | chr11:103116324-103119724 |
| 9764 | Hbb-bs | NM_001201391.1 | chr7:103826522-103827928 | 9859 | Hexim2 | NM_001130515.1 | chr11:103133352-103139908 |
| 9765 | Hbb-bt | NM_008220.5 | chr7:103812523-103813923 | 9860 | Hey1 | NM_010423.2 | chr8:8663358-8667038 |
| 9766 | Hbb-y | NM_008221.4 | chr7:103851753-103853207 | 9861 | Hey2 | NM_013904.1 | chr10:30832358-30842783 |
| 9767 | Hbegf | NM_010415.2 | chr18:36504926-36515805 | 9862 | Heyl | NM_013905.3 | chr4:123233555-123249870 |
| 9768 | Hbp1 | NM_153198.2 | chr12:31926454-31950535 | 9863 | Hfe | NM_010424.4 | chr13:23703840-23710811 |
| 9769 | Hbq1a | NM_175000.2 | chr11:32300068-32300873 | 9864 | Hfe2 | NM_027126.4 | chr3:96525184-96529216 |
| 9770 | Hbq1b | NM_001033981 | chr11:32286963-32287912 | 9865 | Hfm1 | NM_001252516.1 | chr5:106901888-106925890 |
| 9771 | Hbs1l | NM_001245978.1 | chr10:21295978-21368889 | 9866 | Hgd | NM_013547.3 | chr16:37580152-37632026 |
| 9772 | Hc | NM_010406.2 | chr2:34983330-35061441 | 9867 | Hgf | NM_001289458.1 | chr5:16553494-16619439 |
| 9773 | Hcar1 | NM_175520.4 | chr5:123876735-123880020 | 9868 | Hgfac | NM_019447.3 | chr5:35041508-35048461 |
| 9774 | Hcar2 | NM_030701.3 | chr5:123863569-123865516 | 9869 | Hgs | NM_001159328.1 | chr11:120467634-120483984 |
| 9775 | Hccs | NM_008222.4 | chrX:169311530-169320343 | 9870 | Hgsnat | NM_029884.1 | chr8:25944458-25976744 |
| 9776 | Hcfc1 | NM_008224.4 | chrX:73942791-73966357 | 9871 | Hhat | NM_144881.4 | chr1:192512827-192771219 |
| 9777 | Hcfc1r1 | NM_181821.1 | chr17:23673607-23675524 | 9872 | Hhatl | NM_029095.2 | chr9:121784015-121792507 |
| 9778 | Hcfc2 | NM_001081218.1 | chr10:82699006-82741392 | 9873 | Hhex | NM_008245.3 | chr19:37434840-37440731 |
| 9779 | Hck | NM_010407.4 | chr2:153108467-153151441 | | | | |

Fig. 26 - 53

| | | | |
|---|---|---|---|
| 9875 | Hhip | NM_020259.4 | chr8:79965850-80058008 |
| 9876 | Hhipl1 | NM_001044380.1 | chr12:108306269-108328300 |
| 9877 | Hhipl2 | NM_030175.5 | chr1:183418469-183437053 |
| 9878 | Hhla1 | NM_001145096.1 | chr15:65922442-65976804 |
| 9879 | Hiat1 | NM_008246.2 | chr3:116631166-116662677 |
| 9880 | Hiatl1 | NM_001083901.1 | chr13:65065029-65112982 |
| 9881 | Hibadh | NM_145567.1 | chr6:52546129-52640300 |
| 9882 | Hibch | NM_146108.2 | chr1:52845037-52920986 |
| 9883 | Hic1 | NM_001098203.1 | chr11:75164564-75168152 |
| 9884 | Hic2 | NM_178922.3 | chr16:17233586-17263430 |
| 9885 | Hid1 | NM_175454.2 | chr11:115347708-115367719 |
| 9886 | Hif1a | NM_010431.2 | chr12:73907866-73947530 |
| 9887 | Hif1an | NM_176958.3 | chr19:44562853-44576274 |
| 9888 | Hif3a | NM_001162950.1 | chr7:17030992-17062427 |
| 9889 | Higd1a | NM_019814.4 | chr9:121848559-121858000 |
| 9890 | Higd1b | NM_080846.1 | chr11:102836295-102838039 |
| 9891 | Higd1c | NM_001002900.1 | chr15:100364584-100383955 |
| 9892 | Higd2a | NM_025933.3 | chr13:54590230-54591147 |
| 9893 | Hilpda | NM_001190461.1 | chr6:29272487-29275449 |
| 9894 | Hils1 | NM_018792.2 | chr11:94967592-94968456 |
| 9895 | Hinfp | NM_172162.3 | chr9:44295672-44305671 |
| 9896 | Hint1 | NM_008248.2 | chr11:54866437-54870496 |
| 9897 | Hint2 | NM_026871.1 | chr4:43654226-43656445 |
| 9898 | Hint3 | NM_025798.3 | chr10:30608206-30618366 |
| 9899 | Hip1 | NM_146001.2 | chr5:135406518-135545122 |
| 9900 | Hip1r | NM_145070.3 | chr5:123973627-124003215 |
| 9901 | Hipk1 | NM_010432.2 | chr3:103739814-103791275 |
| 9902 | Hipk2 | NM_001136065.2 | chr6:38697839-38837311 |
| 9903 | Hipk3 | NM_001145824.1 | chr2:104426481-104494489 |
| 9904 | Hipk4 | NM_001033315.2 | chr7:27523260-27531174 |
| 9905 | Hira | NM_010439.2 | chr16:18876749-18970308 |
| 9906 | Hirip3 | NM_172746.3 | chr7:126861971-126865122 |
| 9907 | Hist1h1a | NM_030609.3 | chr13:23763667-23764412 |
| 9908 | Hist1h1b | NM_020034.2 | chr13:21779831-21780625 |
| 9909 | Hist1h1c | NM_015786.3 | chr13:23738806-23739531 |
| 9910 | Hist1h1d | NM_145713.4 | chr13:23555031-23555807 |
| 9911 | Hist1h1e | NM_015787.4 | chr13:23621776-23622558 |
| 9912 | Hist1h1t | NM_010377.3 | chr13:23695810-23696545 |
| 9913 | Hist1h2aa | NM_175654.2 | chr13:23934461-23934913 |
| 9914 | Hist1h2ab | NM_175660.3 | chr13:23751087-23751592 |
| 9915 | Hist1h2ac | NM_178189.5 | chr13:23683472-23683959 |
| 9916 | Hist1h2ad | NM_178188.4 | chr13:23574380-23574915 |
| 9917 | Hist1h2ae | NM_178187.4 | chr13:23570662-23571220 |
| 9918 | Hist1h2af | NM_175661.2 | chr13:23533910-23534378 |
| 9919 | Hist1h2ag | NM_178186.3 | chr13:22042477-22042949 |
| 9920 | Hist1h2ah | NM_175659.2 | chr13:22035121-22035643 |
| 9921 | Hist1h2ai | NM_178182.2 | chr13:21716411-21716859 |
| 9922 | Hist1h2ak | NM_178183.2 | chr13:21753376-21753912 |
| 9923 | Hist1h2an | NM_178184.2 | chr13:21786771-21787218 |
| 9924 | Hist1h2ao | NM_001177544.2 | chr13:21810366-21810575 |
| 9925 | Hist1h2ap | NM_178185.2 | chr13:21810466-21833475 |
| 9926 | Hist1h2ba | NM_175663.2 | chr13:23933724-23934156 |
| 9927 | Hist1h2bb | NM_175664.3 | chr13:23746733-23747223 |
| 9928 | Hist1h2bc | NM_001290380.1 | chr13:23684198-23684667 |
| 9929 | Hist1h2be | NM_001177653.1 | chr13:23583669-23621094 |
| 9930 | Hist1h2bf | NM_178195.2 | chr13:23573759-23574190 |
| 9931 | Hist1h2bg | NM_178196.4 | chr13:23571399-23571863 |
| 9932 | Hist1h2bh | NM_178197.2 | chr13:23542922-23543444 |
| 9933 | Hist1h2bj | NM_178198.3 | chr13:22043229-22043658 |
| 9934 | Hist1h2bk | NM_175665.2 | chr13:22035820-22036320 |
| 9935 | Hist1h2bl | NM_178199.2 | chr13:21715712-21716143 |
| 9936 | Hist1h2bm | NM_172022.2 | chr13:21722043-21722526 |
| 9937 | Hist1h2bn | NM_178201.2 | chr13:21754122-21754553 |
| 9938 | Hist1h2bp | NM_001290466.1 | chr13:21787487-21787943 |
| 9939 | Hist1h2bq | NM_001009979.2 | chr13:21806411-21837530 |
| 9940 | Hist1h3a | NM_013550.3 | chr13:23761884-23762386 |
| 9941 | Hist1h3b | NM_178203.2 | chr13:23752379-23752840 |
| 9942 | Hist1h3c | NM_175074.2 | chr13:23745041-23745521 |
| 9943 | Hist1h3d | NM_178204.2 | chr13:23575762-23576266 |
| 9944 | Hist1h3e | NM_178205.2 | chr13:23561895-23562365 |
| 9945 | Hist1h3f | NM_013548.4 | chr13:23544051-23544954 |
| 9946 | Hist1h3g | NM_145073.2 | chr13:23535417-23535909 |
| 9947 | Hist1h3h | NM_178206.2 | chr13:21717627-21718115 |
| 9948 | Hist1h3i | NM_178207.2 | chr13:21782914-21783397 |
| 9949 | Hist1h4a | NM_178192.2 | chr13:23760794-23761249 |
| 9950 | Hist1h4b | NM_175214.2 | chr13:23753936-23757386 |
| 9951 | Hist1h4c | NM_178208.2 | chr13:23698083-23698458 |
| 9952 | Hist1h4d | NM_175654.2 | chr13:23581601-23581969 |
| 9953 | Hist1h4f | NM_175215.2 | chr13:23551285-23551643 |
| 9954 | Hist1h4h | NM_153173.4 | chr13:23531043-23531478 |
| 9955 | Hist1h4i | NM_175656.3 | chr13:22040959-22041362 |
| 9956 | Hist1h4j | NM_178210.2 | chr13:21735033-21735456 |
| 9957 | Hist1h4k | NM_178211.2 | chr13:21750144-21750553 |
| 9958 | Hist1h4m | NM_001195421.1 | chr13:21811745-21812150 |
| 9959 | Hist1h4n | NM_175657.2 | chr13:21811783-21832158 |
| 9960 | Hist2h2aa1 | NM_013549.2 | chr3:96239778-96240052 |
| 9961 | Hist2h2aa2 | NM_178213.4 | chr3:96239778-96240052 |
| 9962 | Hist2h2ab | NM_178213.4 | chr3:96219915-96220353 |
| 9963 | Hist2h2ac | NM_175662.2 | chr3:96220412-96220880 |
| 9964 | Hist2h2be | NM_178214.4 | chr3:96269699-96270192 |
| 9965 | Hist2h2bb | NM_178214.4 | chr3:96221071-96223738 |
| 9966 | Hist2h3b | NM_178215.2 | chr3:96268653-96269155 |
| 9967 | Hist2h3c1 | NM_178216.3 | chr3:96238478-96247348 |
| 9968 | Hist2h3c2 | NM_054045.4 | chr3:96238478-96247348 |
| 9969 | Hist2h4 | NM_033596.3 | chr3:96262933-96263317 |
| 9970 | Hist3h2a | NM_178218.4 | chr11:58954684-58955192 |
| 9971 | Hist3h2ba | NM_030082.4 | chr11:58948910-58949372 |
| 9972 | Hist3h2bb-ps | NM_206882.1 | chr11:58954047-58954512 |
| 9973 | Hist4h4 | NM_175652.3 | chr6:136803992-136804431 |
| 9974 | Hivep1 | NM_007772.2 | chr13:42052020-42185026 |
| 9975 | Hivep2 | NM_010437.2 | chr10:13966378-14151378 |
| 9976 | Hivep3 | NM_010657.3 | chr4:119814677-120135411 |
| 9977 | Hjurp | NM_198652.2 | chr1:88258855-88277579 |
| 9978 | Hk1 | NM_001146100.1 | chr10:62268854-62340421 |
| 9979 | Hk1os | NR_038038.1 | chr10:62340606-62349866 |
| 9980 | Hk2 | NM_013820.3 | chr6:82725026-82774454 |
| 9981 | Hk3 | NM_001033245.4 | chr13:55005984-55021385 |
| 9982 | Hkdc1 | NM_145419.1 | chr10:62383136-62422457 |
| 9983 | Hics | NM_139145.4 | chr16:94129305-94287856 |
| 9984 | Hlf | NM_172563.3 | chr11:90336534-90390917 |
| 9985 | Hltf | NM_009210.3 | chr3:20057810-20118491 |
| 9986 | Hlx | NM_008250.2 | chr1:184727144-184732493 |
| 9987 | Hmbox1 | NM_177338.5 | chr14:64822217-64949847 |
| 9988 | Hmbs | NM_001110251.1 | chr9:44336347-44342381 |
| 9989 | Hmces | NM_173737.2 | chr6:87913975-87936613 |
| 9990 | Hmcn1 | NM_001024720.3 | chr1:150562501-150993435 |
| 9991 | Hmg20a | NM_025812.2 | chr9:56418845-56496936 |
| 9992 | Hmg20b | NM_001163165.1 | chr10:81346045-81350426 |
| 9993 | Hmga1 | NM_001025427.3 | chr17:27556573-27563672 |
| 9994 | Hmga1-rs1 | NM_001166476.3 | chr17:27556652-27563671 |
| 9995 | Hmga2 | NM_010441.2 | chr10:120361274-120476935 |
| 9996 | Hmga2-ps1 | NR_037996.1 | chr1:176834623-176836133 |
| 9997 | Hmgb1 | NM_010439.4 | chr5:149046701-149053057 |
| 9998 | Hmgb1-rs17 | NR_033589.1 | chr8:33484310-33485757 |
| 9999 | Hmgb2 | NM_008252.3 | chr8:57511842-57515999 |
| 10000 | Hmgb3 | NM_008253.4 | chrX:71555916-71560673 |
| 10001 | Hmgb4 | NM_027036.3 | chr4:128260211-128260895 |
| 10002 | Hmgcl | NM_008254.2 | chr4:135946452-135962617 |
| 10003 | Hmgcll1 | NM_173731.2 | chr9:76014976-76136350 |
| 10004 | Hmgcr | NM_008255.2 | chr13:96648961-96670936 |
| 10005 | Hmgcs1 | NM_001146439.1 | chr13:119690350-119708260 |
| 10006 | Hmgcs2 | NM_008256.4 | chr3:98280430-98310738 |
| 10007 | Hmgn1 | NM_008251.3 | chr16:96121587-96127725 |
| 10008 | Hmgn2 | NM_016957.3 | chr4:133964738-133967991 |
| 10009 | Hmgn3 | NM_026122.4 | chr9:83109941-83146607 |
| 10010 | Hmgn5 | NM_016710.2 | chrX:109004536-109013380 |
| 10011 | Hmgxb3 | NM_134134.2 | chr18:61131276-61177050 |
| 10012 | Hmgxb4 | NM_178017.1 | chr8:74993702-75031972 |
| 10013 | Hnrnpa1 | NM_001142701.1 | chr10:80016671-80031471 |
| 10014 | Hnmr | NM_013552.2 | chr11:40701387-40733437 |
| 10015 | Hmox1 | NM_010442.2 | chr8:75093617-75100593 |
| 10016 | Hmox2 | NM_001136066.2 | chr16:4726360-4766249 |
| 10017 | Hmx1 | NM_010445.2 | chr5:35389116-35392872 |
| 10018 | Hmx2 | NM_145998.3 | chr7:131554061-131556582 |
| 10019 | Hmx3 | NM_008257.3 | chr7:131542962-131544931 |
| 10020 | Hn1 | NM_008258.1 | chr11:115497352-115514370 |
| 10021 | Hn1l | NM_198937.2 | chr17:24942469-24960623 |
| 10022 | Hnf1a | NM_009327.3 | chr5:114948979-114971062 |
| 10023 | Hnf1b | NM_001291268.1 | chr11:83850868-83905917 |
| 10024 | Hnf4a | NM_008261.3 | chr2:163547154-163572907 |
| 10025 | Hnf4aos | NR_027970.1 | chr2:163493803-163541721 |
| 10026 | Hnf4g | NM_013920.2 | chr3:3508029-3659800 |
| 10027 | Hnrnt | NM_080462.2 | chr2:24002912-24049379 |
| 10028 | Hnrnpa0 | NM_029872.1 | chr13:58125878-58128556 |
| 10029 | Hnrnpa1 | NM_001039129.4 | chr15:103240396-103244962 |
| 10030 | Hnrnpa2b1 | NM_016806.3 | chr6:51460434-51469894 |
| 10031 | Hnrnpa3 | NM_053263.1 | chr2:75659258-75669407 |
| 10032 | Hnrnpab | NM_010048061.1 | chr11:51600099-51606881 |
| 10033 | Hnrnpc | NM_001170981.1 | chr14:52073379-52104028 |
| 10034 | Hnrnpd | NM_001077265.2 | chr5:99955934-99978938 |
| 10035 | Hnrnpdl | NM_016690.4 | chr5:100035578-100039222 |
| 10036 | Hnrnpf | NM_001166427.1 | chr6:117917293-117925622 |
| 10037 | Hnrnph1 | NM_021510.2 | chr11:50377718-50386528 |
| 10038 | Hnrnph2 | NM_019868.4 | chrX:134601178-134607057 |
| 10039 | Hnrnph3 | NM_001079824.1 | chr10:63014663-63023849 |
| 10040 | Hnrnpk | NM_025279.3 | chr13:58391131-58402512 |
| 10041 | Hnrnpl | NM_177301.5 | chr7:28810889-28822266 |
| 10042 | Hnrnpll | NM_144803.4 | chr17:80029486-80062268 |
| 10043 | Hnrnpm | NM_001109913.1 | chr17:33646232-33685458 |
| 10044 | Hnrnpr | NM_001277121.1 | chr4:136310941-136345979 |
| 10045 | Hnrnpu | NM_016805.2 | chr1:178328299-178337784 |
| 10046 | Hnrnpul1 | NM_144922.2 | chr7:25722038-25754720 |
| 10047 | Hnrnpul2 | NM_001081196.1 | chr19:8819400-8834142 |
| 10048 | Hoga1 | NM_026152.1 | chr19:42045850-42070939 |
| 10049 | Homer1 | NM_001284189.1 | chr13:93304494-93405129 |
| 10050 | Homer2 | NM_001164086.1 | chr7:81600480-81706925 |
| 10051 | Homer3 | NM_001146153.1 | chr8:70282998-70294361 |
| 10052 | Homez | NM_001177705.1 | chr14:54852736-54864158 |
| 10053 | Hook1 | NM_030014.2 | chr4:95967378-96024274 |
| 10054 | Hook2 | NM_001167991.1 | chr8:84990594-85003364 |
| 10055 | Hook3 | NM_207659.3 | chr8:26021420-26119224 |
| 10056 | Hopx | NM_001159900.1 | chr5:77086985-77095267 |
| 10057 | Hormad1 | NM_001289532.1 | chr3:95559676-95587860 |
| 10058 | Hormad2 | NM_029458.1 | chr11:4346382-4441082 |
| 10059 | Hotair | NR_047528.1 | chr15:102944061-102947946 |
| 10060 | Hottip | NR_110441.1 | chr6:52262774-52267603 |
| 10061 | Hoxa1 | NM_010449.4 | chr6:52155366-52158317 |
| 10062 | Hoxa10 | NM_001122950.2 | chr6:52231196-52240854 |
| 10063 | Hoxa11 | NM_010450.3 | chr6:52242104-52245810 |
| 10064 | Hoxa11os | NR_015348.1 | chr6:52245242-52249769 |

Fig. 26 - 54

| | | | | | | | |
|---|---|---|---|---|---|---|---|
| 10065 | Hoxa13 | NM_008264.1 | chr6:52258852-52260880 | 10160 | Hsd17b4 | NM_008292.4 | chr18:50128200-50196270 |
| 10066 | Hoxa2 | NM_010451.2 | chr6:52162416-52164631 | 10161 | Hsd17b6 | NM_013786.2 | chr10:127990935-128007508 |
| 10067 | Hoxa3 | NM_010452.3 | chr6:52169061-52213067 | 10162 | Hsd17b7 | NM_010476.3 | chr1:169949536-169969205 |
| 10068 | Hoxa4 | NM_008265.3 | chr6:52189686-52191703 | 10163 | Hsd3b1 | NM_008293.4 | chr3:98852193-98859794 |
| 10069 | Hoxa5 | NM_010453.5 | chr6:52201753-52204587 | 10164 | Hsd3b2 | NM_153193.3 | chr3:98711106-98724543 |
| 10070 | Hoxa6 | NM_010454.1 | chr6:52206364-52208624 | 10165 | Hsd3b3 | NM_001012306.2 | chr3:98741475-98762410 |
| 10071 | Hoxa7 | NM_010455.2 | chr6:52215623-52218573 | 10166 | Hsd3b4 | NM_001111336.1 | chr3:98445683-98563943 |
| 10072 | Hoxa9 | NM_001277228.1 | chr6:52223096-52227370 | 10167 | Hsd3b5 | NM_008295.2 | chr3:98618635-98645534 |
| 10073 | Hoxb1 | NM_008266.5 | chr11:96365757-96368253 | 10168 | Hsd3b6 | NM_013821.3 | chr3:98805503-98814443 |
| 10074 | Hoxb13 | NM_008267.3 | chr11:96194366-96196599 | 10169 | Hsd3b7 | NM_001040684.1 | chr7:127800608-127803802 |
| 10075 | Hoxb2 | NM_134032.2 | chr11:96351631-96354014 | 10170 | Hsd1 | NM_175185.4 | chr8:119563977-119575200 |
| 10076 | Hoxb3 | NM_001079869.1 | chr11:96323125-96347930 | 10171 | Hsdl2 | NM_024255.3 | chr4:59581562-59618694 |
| 10077 | Hoxb4 | NM_010459.7 | chr11:96318266-96321638 | 10172 | Hsf1 | NM_008296.2 | chr15:76477444-76500972 |
| 10078 | Hoxb5 | NM_008268.2 | chr11:96303511-96306121 | 10173 | Hsf2 | NM_008297.3 | chr10:57486384-57513143 |
| 10079 | Hoxb6 | NM_008269.1 | chr11:96299170-96301569 | 10174 | Hsf2bp | NM_028902.1 | chr17:31944768-32034508 |
| 10080 | Hoxb7 | NM_010460.2 | chr11:96286645-96290163 | 10175 | Hsf3 | NM_172931.4 | chrX:96306177-96456294 |
| 10081 | Hoxb8 | NM_010461.2 | chr11:96281904-96285325 | 10176 | Hsf4 | NM_001256042.1 | chr8:105269800-105275845 |
| 10082 | Hoxb9 | NM_008270.2 | chr11:96271329-96276593 | 10177 | Hsf5 | NM_001045527.1 | chr11:87617163-87659542 |
| 10083 | Hoxc10 | NM_010462.5 | chr15:102966795-102971897 | 10178 | Hsfy2 | NM_027661.2 | chr5:66636650-66637451 |
| 10084 | Hoxc11 | NM_001024842.1 | chr15:102954525-102956701 | 10179 | Msh2d | NM_197944.1 | chr8:72189667-72200958 |
| 10085 | Hoxc12 | NM_010463.1 | chr15:102936852-102938517 | 10180 | Hsp90aa1 | NM_010480.5 | chr12:110691035-110696395 |
| 10086 | Hoxc13 | NM_010464.2 | chr15:102921130-102928814 | 10181 | Hsp90ab1 | NM_008302.3 | chr17:45567777-45573261 |
| 10087 | Hoxc4 | NM_013553.2 | chr15:103034394-103036852 | 10182 | Hsp90b1 | NM_011631.1 | chr10:86696840-86705444 |
| 10088 | Hoxc5 | NM_175730.5 | chr15:103014907-103017429 | 10183 | Hspa12a | NM_175199.3 | chr19:58795750-58860984 |
| 10089 | Hoxc6 | NM_010465.2 | chr15:103009561-103011881 | 10184 | Hspa12b | NM_028306.3 | chr2:131127411-131145983 |
| 10090 | Hoxc8 | NM_010466.2 | chr15:102990538-102994254 | 10185 | Hspa13 | NM_030201.3 | chr16:75755190-75766818 |
| 10091 | Hoxc9 | NM_008272.3 | chr15:102977031-102984444 | 10186 | Hspa14 | NM_015765.2 | chr2:3488853-3512814 |
| 10092 | Hoxd1 | NM_010467.2 | chr2:74762979-74765142 | 10187 | Hspa1a | NM_010479.2 | chr17:34969358-34972156 |
| 10093 | Hoxd10 | NM_013554.5 | chr2:74691890-74695106 | 10188 | Hspa1b | NM_010478.2 | chr17:34956428-34959238 |
| 10094 | Hoxd11 | NM_008273.2 | chr2:74682322-74687016 | 10189 | Hspa1l | NM_013558.2 | chr17:34972702-34979228 |
| 10095 | Hoxd12 | NM_008274.3 | chr2:74675012-74677705 | 10190 | Hspa2 | NM_001002012.1 | chr12:76404175-76406936 |
| 10096 | Hoxd13 | NM_008275.3 | chr2:74668309-74671589 | 10191 | Hspa4 | NM_008300.3 | chr11:53259813-53300479 |
| 10097 | Hoxd3 | NM_010468.2 | chr2:74711992-74748271 | 10192 | Hspa4l | NM_011020.3 | chr3:40745612-40790365 |
| 10098 | Hoxd3os1 | NR_027899.1 | chr2:74710043-74716130 | 10193 | Hspa5 | NM_001163434.1 | chr2:34772089-34776529 |
| 10099 | Hoxd4 | NM_010469.2 | chr2:74721977-74729159 | 10194 | Hspa8 | NM_031165.4 | chr9:40801272-40805199 |
| 10100 | Hoxd8 | NM_001199730.1 | chr2:74705488-74707932 | 10195 | Hspa9 | NM_010481.2 | chr18:34937414-34954351 |
| 10101 | Hoxd9 | NM_013555.4 | chr2:74697762-74700208 | 10196 | Hspb1 | NM_013560.2 | chr5:135887918-135889563 |
| 10102 | Hp | NM_017370.2 | chr8:109575127-109579172 | 10197 | Hspb11 | NM_028394.2 | chr4:107253933-107279888 |
| 10103 | Hp1bp3 | NM_001122896.2 | chr4:138216611-138244682 | 10198 | Hspb2 | NM_001164708.1 | chr9:50751071-50752354 |
| 10104 | Hpca | NM_001130419.2 | chr4:129111569-129121747 | 10199 | Hspb3 | NM_019960.2 | chr13:113662895-113663676 |
| 10105 | Hpca1 | NM_016677.4 | chr12:17690813-17791926 | 10200 | Hspb6 | NM_001124012 | chr7:30553301-30555439 |
| 10106 | Hpcal4 | NM_174984.3 | chr4:123183503-123194699 | 10201 | Hspb7 | NM_013868.4 | chr4:141420778-141425310 |
| 10107 | Hpd | NM_008277.2 | chr5:123171806-123182686 | 10202 | Hspb8 | NM_030704.3 | chr5:116408490-116422864 |
| 10108 | Hpdl | NM_146256.3 | chr4:116819906-116821508 | 10203 | Hspb9 | NM_029307.1 | chr11:100713849-100714575 |
| 10109 | Hpgd | NM_008278.2 | chr8:56294551-56321046 | 10204 | Hspbap1 | NM_175111.3 | chr16:35770385-35828462 |
| 10110 | Hpgds | NM_019455.4 | chr6:65117292-65144730 | 10205 | Hspbp1 | NM_024172.3 | chr7:4660520-4684963 |
| 10111 | Hpn | NM_001110252.2 | chr7:31098724-31115326 | 10206 | Hspd1 | NM_010477.4 | chr1:55077833-55087932 |
| 10112 | Hprt | NM_013556.2 | chrX:52988077-53021660 | 10207 | Hspe1 | NM_008303.4 | chr1:55088147-55091317 |
| 10113 | Hps1 | NM_019424.2 | chr19:42755195-42779976 | 10208 | Hspg2 | NM_008305.3 | chr4:137468802-137570630 |
| 10114 | Hps3 | NM_001146323.1 | chr3:19995944-20035310 | 10209 | Hsph1 | NM_013559.2 | chr5:149616844-149636315 |
| 10115 | Hps4 | NM_138646.3 | chr5:112343094-112378424 | 10210 | Htatip2 | NM_001146049.1 | chr7:49759105-49773999 |
| 10116 | Hps5 | NM_001005247.2 | chr7:46760465-46795881 | 10211 | Htatsf1 | NM_028242.2 | chrX:57053569-57067182 |
| 10117 | Hps6 | NM_176785.3 | chr19:46003477-46006173 | 10212 | Htr1b | NM_008308.4 | chr13:105443692-105448133 |
| 10118 | Hpse | NM_152803.4 | chr5:100679485-100719683 | 10213 | Htr1b | NM_010482.1 | chr9:81631391-81632552 |
| 10119 | Hpse2 | NM_001081257.2 | chr19:42788594-43388355 | 10214 | Htr1d | NM_001285482.1 | chr4:136423523-136444401 |
| 10120 | Hpx | NM_017371.2 | chr7:105591610-105600116 | 10215 | Htr1f | NM_008310.3 | chr16:64924728-65105784 |
| 10121 | Hr | NM_021877.3 | chr14:70554055-70573548 | 10216 | Htr2a | NM_172812.2 | chr14:74640839-74706859 |
| 10122 | Hras | NM_001130443.1 | chr7:141189933-141194004 | 10217 | Htr2b | NM_008311.2 | chr1:86099036-86111970 |
| 10123 | Hrasls | NM_013751.5 | chr16:29209694-29230630 | 10218 | Htr2c | NM_008312.4 | chrX:146962512-147197277 |
| 10124 | Hrasls5 | NM_025731.2 | chr19:7612568-7639238 | 10219 | Htr3a | NM_001099644.1 | chr9:48899212-48911099 |
| 10125 | Hrc | NM_010473.2 | chr7:45335268-45338972 | 10220 | Htr3b | NM_020274.4 | chr9:48935007-48964990 |
| 10126 | Hrct1 | NM_027511.1 | chr4:43727197-43728110 | 10221 | Htr4 | NM_008313.4 | chr18:62324203-62467802 |
| 10127 | Hrg | NM_053176.2 | chr16:22951071-22961659 | 10222 | Htr5a | NM_008314.2 | chr5:27841946-27855086 |
| 10128 | Hrh1 | NM_001252642.1 | chr6:114403665-114483296 | 10223 | Htr5b | NM_010483.3 | chr1:121509772-121528465 |
| 10129 | Hrh2 | NM_001010973.2 | chr13:54192128-54222432 | 10224 | Htr6 | NM_021358.2 | chr4:139061408-139074789 |
| 10130 | Hrh3 | NM_133849.3 | chr2:180099464-180104407 | 10225 | Htr7 | NM_008315.2 | chr19:35958728-36057360 |
| 10131 | Hrh4 | NM_153087.2 | chr18:13006989-13022882 | 10226 | Htra1 | NM_019564.3 | chr7:130936202-130985658 |
| 10132 | Hrk | NM_007765.2 | chr5:118169763-118189478 | 10227 | Htra2 | NM_019752.3 | chr6:83051266-83054571 |
| 10133 | Hrnr | NM_133698.2 | chr3:93319748-93333572 | 10228 | Htra3 | NM_001042615.2 | chr5:35661558-35679780 |
| 10134 | Hrsp12 | NM_008287.3 | chr15:34484021-34495246 | 10229 | Htra4 | NM_001081187.3 | chr8:25024927-25038962 |
| 10135 | Hs1bp3 | NM_021429.3 | chr12:8313432-8343824 | 10230 | Htt | NM_010414.3 | chr5:34761739-34912534 |
| 10136 | Hs2st1 | NM_011828.3 | chr3:144431106-144570216 | 10231 | Hunk | NM_015755.2 | chr16:90386396-90499553 |
| 10137 | Hs3st1 | NM_010474.2 | chr5:39613934-39644631 | 10232 | Hus1 | NM_008316.5 | chr11:8993136-9011191 |
| 10138 | Hs3st2 | NM_001081327.1 | chr7:121392295-121501768 | 10233 | Hus1b | NM_153072.2 | chr13:30946575-30947761 |
| 10139 | Hs3st3a1 | NM_178870.5 | chr11:64435331-64522835 | 10234 | Huwe1 | NM_021523.4 | chrX:151803281-151935417 |
| 10140 | Hs3st3b1 | NM_018805.2 | chr11:63884692-63922284 | 10235 | Hvcn1 | NM_001042489.2 | chr5:122209728-122242297 |
| 10141 | Hs3st4 | NM_001252072.1 | chr7:123983180-124398989 | 10236 | Hyal1 | NM_008317.4 | chr9:107576951-107580133 |
| 10142 | Hs3st5 | NM_001081208.2 | chr10:36506806-36834394 | 10237 | Hyal2 | NM_010489.2 | chr9:107569162-107572778 |
| 10143 | Hs3st6 | NM_001012402.1 | chr17:24753002-24758684 | 10238 | Hyal3 | NM_178020.3 | chr9:107581295-107587359 |
| 10144 | Hs6st1 | NM_015818.2 | chr1:36068399-36106446 | 10239 | Hyal4 | NM_029848.1 | chr6:24748366-24766519 |
| 10145 | Hs6st2 | NM_001077202.2 | chrX:51386636-51681602 | 10240 | Hyal5 | NM_028957.2 | chr6:24857996-24891958 |
| 10146 | Hs6st3 | NM_015820.3 | chr14:119138264-119869815 | 10241 | Hyal6 | NM_028920.2 | chr6:24733244-24745452 |
| 10147 | Hsbp1 | NM_024219.1 | chr8:119344537-119348929 | 10242 | Hydin | NM_172916.2 | chr8:110266976-110610253 |
| 10148 | Hsbp1l1 | NM_001136181.1 | chr18:80229755-80247102 | 10243 | Hyi | NM_026601.3 | chr4:118359998-118362744 |
| 10149 | Hscb | NM_153571.2 | chr5:110128069-110839777 | 10244 | Hykk | NM_177351.4 | chr9:54917289-54949924 |
| 10150 | Hsd11b1 | NM_001044751.1 | chr1:193221640-193242360 | 10245 | Hyls1 | NM_029762.1 | chr9:35560820-35570069 |
| 10151 | Hsd11b2 | NM_008289.2 | chr8:105518745-105523988 | 10246 | Hyou1 | NM_021395.4 | chr9:44379489-44392369 |
| 10152 | Hsd17b1 | NM_010475.1 | chr11:101078410-101080505 | 10247 | Hypk | NM_026318.3 | chr2:121457087-121458440 |
| 10153 | Hsd17b10 | NM_016763.2 | chrX:152001895-152004442 | 10248 | 1700028E13Rik | NR_045705.1 | chr9:61138514-61145259 |
| 10154 | Hsd17b11 | NM_053262.3 | chr5:103989764-104021796 | 10249 | 1700030J21Rik | NR_045781.1 | chr15:100730504-100732737 |
| 10155 | Hsd17b12 | NM_019657.4 | chr2:94032696-94157909 | 10250 | 1830012O16Rik | NM_001005858.3 | chr19:34607956-34613401 |
| 10156 | Hsd17b13 | NM_001163486.1 | chr5:103963464-103977388 | 10251 | 1830077J02Rik | NM_001033780.3 | chr3:105925890-105932664 |
| 10157 | Hsd17b14 | NM_025330.3 | chr7:45554927-45567321 | 10252 | iah1 | NM_026347.3 | chr12:21316391-21323607 |
| 10158 | Hsd17b2 | NM_008290.2 | chr8:117701945-117759029 | 10253 | iapp | NM_010491.2 | chr6:142298424-142303819 |
| 10159 | Hsd17b3 | NM_008291.3 | chr13:64058273-64089201 | 10254 | iars | NM_172015.3 | chr13:49682129-49734267 |

Fig. 26 - 55

| | | | | | | | | |
|---|---|---|---|---|---|---|---|---|
| 10255 | Iars2 | NM_198653.2 | chr1:185286661-185329401 | | 10350 | Ift22 | NM_026073.3 | chr5:136908149-136913244 |
| 10256 | Iba57 | NM_001270791.1 | chr15:79161118-59163745 | | 10351 | Ift27 | NM_025931.2 | chr15:78159462-78174108 |
| 10257 | Ibsp | NM_008318.3 | chr5:104299286-104311472 | | 10352 | Ift43 | NM_001199843.1 | chr12:86082560-86162459 |
| 10258 | Ibtk | NM_001081282.2 | chr9:85687359-85749334 | | 10353 | Ift46 | NM_023831.3 | chr9:44773008-44792714 |
| 10259 | Ica1 | NM_001252266.1 | chr6:8630526-8758458 | | 10354 | Ift52 | NM_172150.4 | chr2:163017471-163046135 |
| 10260 | Ica1l | NM_027407.3 | chr1:59989067-60043087 | | 10355 | Ift57 | NM_028680.3 | chr16:49699293-49765126 |
| 10261 | Icam1 | NM_010493.2 | chr9:21015959-21028796 | | 10356 | Ift74 | NM_001290568.1 | chr4:94614490-94664698 |
| 10262 | Icam2 | NM_010494.1 | chr11:106377655-106382641 | | 10357 | Ift80 | NM_026641.2 | chr3:68892498-69004570 |
| 10263 | Icam4 | NM_023892.2 | chr9:21029372-21030531 | | 10358 | Ift81 | NM_009879.3 | chr5:122550203-122614518 |
| 10264 | Icam5 | NM_008319.2 | chr9:21032037-21039036 | | 10359 | Ift88 | NM_009376.2 | chr14:57424070-57517936 |
| 10265 | Ick | NM_001163780.1 | chr9:78109191-78172109 | | 10360 | Igbp1 | NM_008784 | chrX:100494290-100516125 |
| 10266 | Icmt | NM_133788.2 | chr4:152297213-152307126 | | 10361 | Igbp1b | NM_015777.2 | chr6:138657091-138658444 |
| 10267 | Icos | NM_017480.2 | chr1:60977913-61000321 | | 10362 | Igdcc3 | NM_008988.2 | chr9:65141188-65185870 |
| 10268 | Icosl | NM_015790.3 | chr10:78069367-78079525 | | 10363 | Igdcc4 | NM_001290315.1 | chr9:65101485-65137947 |
| 10269 | Ict1 | NM_026729.1 | chr11:115403765-115410913 | | 10364 | Igf1 | NM_001111274.1 | chr10:87861110-87937047 |
| 10270 | Id1 | NM_010495.3 | chr2:152736250-152737410 | | 10365 | Igf1r | NM_010513.2 | chr7:67952256-68233667 |
| 10271 | Id2 | NM_010496.3 | chr12:25093798-25096092 | | 10366 | Igf2 | NM_001122736.2 | chr7:142650767-142661271 |
| 10272 | Id3 | NM_008321.2 | chr4:136143821-136145392 | | 10367 | Igf2bp1 | NM_009951.4 | chr11:95957163-96005944 |
| 10273 | Id4 | NM_031166.2 | chr13:48261426-48264036 | | 10368 | Igf2bp2 | NM_183029.2 | chr16:22059008-22163299 |
| 10274 | Ide | NM_031156.3 | chr19:37268740-37330613 | | 10369 | Igf2bp3 | NM_023670.3 | chr6:49085217-49214954 |
| 10275 | Idh1 | NM_001111320.1 | chr1:65158615-65186479 | | 10370 | Igf2os | NR_002855.2 | chr7:142659692-142670356 |
| 10276 | Idh2 | NM_173011.2 | chr7:80094846-80115350 | | 10371 | Igf2r | NM_010515.2 | chr17:12682405-12769706 |
| 10277 | Idh3a | NM_029573.2 | chr9:54586510-54604662 | | 10372 | Igfals | NM_008340.3 | chr17:24878769-24882008 |
| 10278 | Idh3b | NM_130884.4 | chr2:130279308-130284451 | | 10373 | Igfbp1 | NM_008341.4 | chr11:7197786-7202546 |
| 10279 | Idh3g | NM_008323.1 | chrX:73778962-73786897 | | 10374 | Igfbp2 | NM_008342.3 | chr1:72824479-72852471 |
| 10280 | Idi1 | NM_145360.2 | chr13:8885605-8892396 | | 10375 | Igfbp3 | NM_008343.2 | chr11:7206090-7213923 |
| 10281 | Idi2 | NM_177197.4 | chr13:8952862-8960935 | | 10376 | Igfbp4 | NM_010517.3 | chr11:99041259-99052643 |
| 10282 | Idnk | NM_001048060.2 | chr13:58157648-58164693 | | 10377 | Igfbp5 | NM_010518.2 | chr1:72858064-72874865 |
| 10283 | Ido1 | NM_008324.2 | chr8:24584132-24596952 | | 10378 | Igfbp6 | NM_008344.3 | chr15:102144185-102149512 |
| 10284 | Ido2 | NM_145949.2 | chr8:24531891-24576333 | | 10379 | Igfbp7 | NM_001159518.1 | chr5:77349239-77408045 |
| 10285 | Ids | NM_070343.069-70365085 | | | 10380 | Igfbpl1 | NM_018741.2 | chr4:45809506-45826827 |
| 10286 | Idua | NM_008325.4 | chr5:108660330-108685446 | | 10381 | Igf3 | NM_001003393.1 | chr7:18176493-18181862 |
| 10287 | Ier2 | NM_010499.4 | chr8:84661330-84662852 | | 10382 | Igflr1 | NM_145580.2 | chr7:30565426-30567962 |
| 10288 | Ier3 | NM_133662.2 | chr17:35821712-35822911 | | 10383 | Ighn1 | NM_177642.3 | chr1:135953577-136006342 |
| 10289 | Ier3ip1 | NM_025409.3 | chr18:76930026-76941614 | | 10384 | Ighmbp2 | NM_009212.2 | chr19:3259075-3283030 |
| 10290 | Ier5 | NM_010500.2 | chr1:155096366-155099636 | | 10385 | Igip | NM_001267796.1 | chr18:36300100-36301478 |
| 10291 | Ier5l | NM_030244.3 | chr2:30472640-30474199 | | 10386 | Igj | NM_152839.3 | chr5:88519808-88527897 |
| 10292 | Iffo1 | NM_001039669.3 | chr6:125145223-125161782 | | 10387 | Igll1 | NM_001190325.1 | chr16:16860670-16863985 |
| 10293 | Iffo2 | NM_001076175.1 | chr4:139574719-139620382 | | 10388 | Iglon5 | NM_001164518.1 | chr7:43472906-43490023 |
| 10294 | Ifi202b | NM_008327.2 | chr1:173962568-173982844 | | 10389 | Igsf1 | NM_177591.4 | chrX:49782536-49797745 |
| 10295 | Ifi203 | NM_001302649.1 | chr1:173920400-173942847 | | 10390 | Igsf10 | NM_001162884.1 | chr3:59316734-59344256 |
| 10296 | Ifi204 | NM_008329.2 | chr1:173747293-173766919 | | 10391 | Igsf11 | NM_170599.2 | chr16:38902344-39027157 |
| 10297 | Ifi205 | NM_172648.3 | chr1:174011997-174031755 | | 10392 | Igsf21 | NM_198610.2 | chr4:140026851-140246811 |
| 10298 | Ifi27 | NM_026790.2 | chr12:103434188-103440245 | | 10393 | Igsf23 | NM_027308.2 | chr7:19937304-19950743 |
| 10299 | Ifi27l2a | NM_001281830.1 | chr12:103443872-103443680 | | 10394 | Igsf3 | NM_207205.2 | chr3:101377124-101463060 |
| 10300 | Ifi27l2b | NM_145449.2 | chr12:103450897-103457223 | | 10395 | Igsf5 | NM_001177886.1 | chr16:96361760-96422121 |
| 10301 | Ifi30 | NM_023065.3 | chr8:70762772-70766663 | | 10396 | Igsf6 | NM_030691.1 | chr7:121064066-121074530 |
| 10302 | Ifi35 | NM_027320.4 | chr11:101448411-101458701 | | 10397 | Igsf8 | NM_080419.2 | chr1:172312366-172319843 |
| 10303 | Ifi44 | NM_133871.2 | chr3:151730922-151749959 | | 10398 | Igsf9 | NM_001145800.1 | chr1:172482212-172498877 |
| 10304 | Ifi44l | NM_031367.1 | chr3:151758736-151762891 | | 10399 | Igsf9b | NM_001033323.3 | chr9:27299227-27330135 |
| 10305 | Ifi47 | NM_001271676.1 | chr1:149087016-49096987 | | 10400 | Igtp | NM_018738.4 | chr11:58199555-58207592 |
| 10306 | Ifih1 | NM_001164477.1 | chr2:62595792-62646255 | | 10401 | Ihh | NM_010544.3 | chr1:74945314-74951672 |
| 10307 | Ift1 | NM_008331.1 | chr19:34640888-34650009 | | 10402 | Iigp1 | NM_001146275.1 | chr18:60376028-60392629 |
| 10308 | Ift2 | NM_008332.3 | chr19:34550693-34576534 | | 10403 | Ik | NM_011879.2 | chr18:36744655-36757639 |
| 10309 | Ift3 | NM_010501.2 | chr19:34583528-34588982 | | 10404 | Ikbip | NM_026166.2 | chr10:91083038-91098658 |
| 10310 | Iftm1 | NM_001112715.1 | chr7:140968075-140969827 | | 10405 | Ikbkap | NM_026079.3 | chr4:56749679-56802331 |
| 10311 | Iftm10 | NM_177265.4 | chr7:142326109-142372259 | | 10406 | Ikbkb | NM_001159774.1 | chr8:22659204-22706583 |
| 10312 | Iftm2 | NM_030694.1 | chr7:140954838-140955961 | | 10407 | Ikbke | NM_019777.3 | chr1:131254601-131279563 |
| 10313 | Iftm3 | NM_025378.2 | chr7:141009589-141010744 | | 10408 | Ikbkg | NM_001136067.2 | chrX:74424611-74453778 |
| 10314 | Iftm5 | NM_053088.2 | chr7:140948961-140950239 | | 10409 | Ikzf1 | NM_001025597.2 | chr11:11685924-11772926 |
| 10315 | Iftm6 | NM_001033632.1 | chr7:141015811-141016892 | | 10410 | Ikzf2 | NM_011770.4 | chr1:69531209-69685960 |
| 10316 | Iftm7 | NM_001270718.1 | chr16:13981701-13986867 | | 10411 | Ikzf3 | NM_011771.1 | chr11:98464692-98546031 |
| 10317 | Iftd1 | NM_028742.2 | chr6:145397234-145434925 | | 10412 | Ikzf4 | NM_011772.2 | chr10:128632414-128645993 |
| 10318 | Ifna1 | NM_010502.2 | chr4:88850086-88850656 | | 10413 | Ikzf5 | NM_175115.4 | chr7:131388648-131410478 |
| 10319 | Ifna11 | NM_008333.2 | chr4:88819918-88820565 | | 10414 | Il10 | NM_010548.2 | chr1:131019844-131024970 |
| 10320 | Ifna12 | NM_177361.2 | chr4:88602579-88603376 | | 10415 | Il10ra | NM_008348.2 | chr9:45253838-45269146 |
| 10321 | Ifna13 | NM_177347.2 | chr4:88643640-88644459 | | 10416 | Il10rb | NM_008349.5 | chr16:91406234-91425834 |
| 10322 | Ifna14 | NM_206975.1 | chr4:88571228-88571798 | | 10417 | Il11 | NM_001290423.1 | chr7:4772377-4782857 |
| 10323 | Ifna15 | NM_206870.1 | chr4:88557672-88558245 | | 10418 | Il11ra1 | NM_001163401.1 | chr4:41760442-41769473 |
| 10324 | Ifna16 | NM_206867.1 | chr4:88676286-88676856 | | 10419 | Il11ra2 | NM_010550.3 | chr4:3083-42665763 |
| 10325 | Ifna2 | NM_010503.2 | chr4:88683206-88683779 | | 10420 | Il12a | NM_001159424.2 | chr3:68690643-68698550 |
| 10326 | Ifna4 | NM_010504.2 | chr4:88841815-88842459 | | 10421 | Il12b | NM_001303244.1 | chr11:44400063-44414677 |
| 10327 | Ifna5 | NM_010505.2 | chr4:88835524-88836094 | | 10422 | Il12rb1 | NM_008353.2 | chr8:70808448-70821423 |
| 10328 | Ifna6 | NM_206871.1 | chr4:88827415-88827985 | | 10423 | Il12rb2 | NM_008354.3 | chr6:67292017-67376137 |
| 10329 | Ifna7 | NM_008334.3 | chr4:88816224-88816800 | | 10424 | Il13 | NM_008355.3 | chr11:53631322-53634702 |
| 10330 | Ifna9 | NM_010507.1 | chr4:88591812-88592385 | | 10425 | Il13ra1 | NM_133990.5 | chrX:36112167-36171261 |
| 10331 | Ifnab | NM_008336.2 | chr4:88690598-88691268 | | 10426 | Il13ra2 | NM_008356.4 | chrX:147383477-147429192 |
| 10332 | Ifnar1 | NM_010508.2 | chr16:91485214-91510522 | | 10427 | Il15 | NM_001254747.1 | chr8:82331623-82402586 |
| 10333 | Ifnar2 | NM_001010498.1 | chr16:91373782-91394043 | | 10428 | Il15ra | NM_001271497.1 | chr2:11705292-11733985 |
| 10334 | Ifnb1 | NM_010510.1 | chr4:88520024-88522794 | | 10429 | Il16 | NM_010551.3 | chr7:83643062-83735490 |
| 10335 | Ifne | NM_177348.2 | chr4:88879537-88880201 | | 10430 | Il17a | NM_010552.3 | chr1:20730904-20734496 |
| 10336 | Ifng | NM_008337.4 | chr10:118441045-118445894 | | 10431 | Il17b | NM_019508.1 | chr18:61687934-61692537 |
| 10337 | Ifngr1 | NM_010511.2 | chr10:19591957-19610225 | | 10432 | Il17c | NM_145834.3 | chr8:122422084-122423639 |
| 10338 | Ifngr2 | NM_008338.3 | chr16:91547093-91564007 | | 10433 | Il17d | NM_145837.3 | chr14:57524828-57543166 |
| 10339 | Ifnk | NM_199157.2 | chr12:35152054-35154019 | | 10434 | Il17f | NM_145856.2 | chr1:20777145-20784270 |
| 10340 | Ifnl2 | NM_001024673.2 | chr7:28508860-28510360 | | 10435 | Il17ra | NM_008359.2 | chr6:120463196-120483727 |
| 10341 | Ifnl3 | NM_174851.3 | chr7:28522835-28524322 | | 10436 | Il17rb | NM_019583.3 | chr14:29996167-30008896 |
| 10342 | Ifnlr1 | NM_174851.3 | chr4:135686456-135708180 | | 10437 | Il17rc | NM_134159.4 | chr6:113471454-113483140 |
| 10343 | Ifnz | NM_197889.2 | chr4:88782130-88783592 | | 10438 | Il17rd | NM_134437.3 | chr14:27039000-27107286 |
| 10344 | Ifrd1 | NM_013562.2 | chr12:40203128-40223189 | | 10439 | Il17re | NM_001034029.1 | chr6:113458894-113470143 |
| 10345 | Ifrd2 | NM_025903.2 | chr9:107587717-107593038 | | 10440 | Il18 | NM_008360.1 | chr9:50565367-50581837 |
| 10346 | Ift122 | NM_001167763.1 | chr6:115853527-115926699 | | 10441 | Il18bp | NM_010531.1 | chr7:102015076-102018155 |
| 10347 | Ift140 | NM_134126.3 | chr17:25016085-25099497 | | 10442 | Il18r1 | NM_001161842.1 | chr1:40465551-40491578 |
| 10348 | Ift172 | NM_026298.5 | chr5:31253278-31291114 | | 10443 | Il18rap | NM_010553.4 | chr1:40515361-40551705 |
| 10349 | Ift20 | NM_018854.4 | chr11:78536435-78541473 | | 10444 | Il19 | NM_001009940.1 | chr1:130932655-130939241 |

Fig. 26 - 56

| | | | |
|---|---|---|---|
| 10445 | il1a | NM_010554.4 | chr2:129299609-129309972 |
| 10446 | il1b | NM_008361.4 | chr2:129364577-129371139 |
| 10447 | il1bos | NR_015474.1 | chr2:129369901-129375733 |
| 10448 | il1f10 | NM_153077.2 | chr2:24291195-24293820 |
| 10449 | il1f5 | NM_001146087.1 | chr2:24276953-24282432 |
| 10450 | il1f6 | NM_019450.3 | chr2:24215416-24225701 |
| 10451 | il1f8 | NM_027163.4 | chr2:24153171-24160103 |
| 10452 | il1f9 | NM_153511.3 | chr2:24186475-24193567 |
| 10453 | il1r1 | NM_001123382.1 | chr1:40266585-40316177 |
| 10454 | il1r2 | NM_010555.4 | chr1:40084767-40125226 |
| 10455 | il1rap | NM_001159317.1 | chr16:26581704-26725147 |
| 10456 | il1rapl1 | NM_001160403.1 | chrX:86747241-88115623 |
| 10457 | il1rapl2 | NM_030688.2 | chrX:137570753-138849077 |
| 10458 | il1rl1 | NM_001025602.3 | chr1:40439628-40465414 |
| 10459 | il1rl2 | NM_133193.3 | chr1:40324626-40365471 |
| 10460 | il1rn | NM_001039701.3 | chr2:24345370-24351491 |
| 10461 | il2 | NM_008366.3 | chr3:37120715-37125954 |
| 10462 | il20 | NM_021380.2 | chr1:130906984-130911296 |
| 10463 | il20ra | NM_172786.2 | chr10:19712586-19760053 |
| 10464 | il20rb | NM_001033543.1 | chr9:100457718-100486473 |
| 10465 | il21 | NM_001291041.1 | chr3:37222758-37232636 |
| 10466 | il21r | NM_021887.2 | chr7:125603428-125633570 |
| 10467 | il22 | NM_016971.2 | chr10:118204963-118210046 |
| 10468 | il22ra1 | NM_178257.2 | chr4:135728158-135755383 |
| 10469 | il22ra2 | NM_178258.5 | chr10:19212027-19634681 |
| 10470 | il23a | NM_031252.2 | chr10:128296139-128298084 |
| 10471 | il23r | NM_144548.1 | chr6:67422931-67491855 |
| 10472 | il24 | NM_053095.2 | chr1:130882073-130887411 |
| 10473 | il25 | NM_080729.3 | chr14:54932694-54935836 |
| 10474 | il27 | NM_145636.1 | chr7:126589294-126594910 |
| 10475 | il27ra | NM_016671.3 | chr8:84030285-84042575 |
| 10476 | il2ra | NM_008367.3 | chr2:11642791-11693194 |
| 10477 | il2rb | NM_008368.4 | chr15:78480548-78495606 |
| 10478 | il2rg | NM_013563.4 | chrX:101264384-101268255 |
| 10479 | il3 | NM_010556.4 | chr11:54265084-54267279 |
| 10480 | il31 | NM_029594.3 | chr5:123480152-123482101 |
| 10481 | il31ra | NM_139299.2 | chr13:112522806-112580662 |
| 10482 | il33 | NM_001164724.1 | chr19:29945789-29960715 |
| 10483 | il34 | NM_001135100.2 | chr8:110741828-110805924 |
| 10484 | il3ra | NM_008369.1 | chr14:14346494-14355490 |
| 10485 | il4 | NM_021283.2 | chr11:53612460-53618665 |
| 10486 | il4i1 | NM_010215.3 | chr7:44836287-44840809 |
| 10487 | il4ra | NM_001008700.3 | chr7:125552281-125579474 |
| 10488 | il5 | NM_010558.1 | chr11:53720793-53725103 |
| 10489 | il5ra | NM_008370.2 | chr6:106710378-106749037 |
| 10490 | il6 | NM_031168.2 | chr5:30013113-30019975 |
| 10491 | il6ra | NM_010559.3 | chr3:89869323-89913196 |
| 10492 | il6st | NM_010560.3 | chr13:112464069-112506860 |
| 10493 | il7 | NM_008371.5 | chr3:7572027-7613760 |
| 10494 | il7r | NM_008372.4 | chr15:9506158-9529876 |
| 10495 | il9 | NM_008373.1 | chr13:56479276-56482246 |
| 10496 | il9r | NM_001134458.1 | chr11:32188996-32200279 |
| 10497 | ildr1 | NM_001285788.1 | chr16:36693977-36726804 |
| 10498 | ildr2 | NM_001164528.1 | chr1:166254138-166316832 |
| 10499 | ilf2 | NM_026374.3 | chr3:90476200-90488379 |
| 10500 | ilf3 | NM_001042707.2 | chr9:21367870-21405363 |
| 10501 | ilk | NM_001161724.1 | chr7:105736589-105742925 |
| 10502 | ilkap | NM_023343.2 | chr1:91375830-91398783 |
| 10503 | ilirfb | NM_054079.2 | chr10:118289629-118295038 |
| 10504 | ilvbl | NM_173751.4 | chr10:78574499-78584502 |
| 10505 | immp1l | NM_028260.2 | chr2:105904637-105965558 |
| 10506 | immp2l | NM_053122.4 | chr12:41024089-41955588 |
| 10507 | immt | NM_001253681.1 | chr6:71831319-71875266 |
| 10508 | imp3 | NM_133976.2 | chr9:56937499-56938398 |
| 10509 | imp4 | NM_178601.3 | chr1:34439828-34445747 |
| 10510 | impa1 | NM_018864.6 | chr3:10311955-10331439 |
| 10511 | impa2 | NM_053261.2 | chr18:67289222-67318841 |
| 10512 | impact | NM_008378.2 | chr18:12971251-12992948 |
| 10513 | impad1 | NM_177730.3 | chr4:4764356-4793306 |
| 10514 | impdh1 | NM_011830.3 | chr6:29200436-29212297 |
| 10515 | impdh2 | NM_011830.3 | chr9:108560500-108565566 |
| 10516 | impg1 | NM_022016.3 | chr9:80313829-80465438 |
| 10517 | impg2 | NM_174876.3 | chr16:56204312-56273753 |
| 10518 | ina | NM_146100.4 | chr19:47014697-47024346 |
| 10519 | inadl | NM_001005784.1 | chr4:98395825-98497633 |
| 10520 | inca1 | NM_001252482.1 | chr11:70688360-70700155 |
| 10521 | incenp | NM_016692.3 | chr19:9872296-9899533 |
| 10522 | inf2 | NM_198411.2 | chr12:112588783-112615957 |
| 10523 | ing1 | NM_011919.5 | chr8:11556456-11563251 |
| 10524 | ing2 | NM_023503.3 | chr8:47667177-47675159 |
| 10525 | ing3 | NM_023626.4 | chr6:21949614-21976037 |
| 10526 | ing4 | NM_133345.2 | chr6:125039847-125049264 |
| 10527 | ing5 | NM_025454.2 | chr1:93803964-93822100 |
| 10528 | inha | NM_010564.4 | chr1:75507076-75510354 |
| 10529 | inhba | NM_008380.1 | chr13:16014474-16027211 |
| 10530 | inhbb | NM_008381.3 | chr1:119415464-119422248 |
| 10531 | inhbc | NM_010565.3 | chr10:127356325-127370544 |
| 10532 | inhbe | NM_008382.2 | chr10:127349401-127351772 |
| 10533 | inip | NM_001013577.1 | chr4:59769646-59783855 |
| 10534 | inmt | NM_009349.3 | chr6:55170626-55174990 |
| 10535 | ino80 | NM_026574.3 | chr2:119373041-119477629 |
| 10536 | ino80b | NM_023547.1 | chr6:83121827-83125029 |
| 10537 | ino80c | NM_172625.2 | chr18:24104760-24121819 |
| 10538 | ino80d | NM_001081436.2 | chr1:63047800-63114267 |
| 10539 | ino80dos | NR_045914.1 | chr1:63114739-63158295 |
| 10540 | ino80e | NM_153580.1 | chr7:126852432-126861463 |
| 10541 | inpp1 | NM_008384.2 | chr1:52789419-52817688 |
| 10542 | inpp4a | NM_001290797.1 | chr1:37299837-37410740 |
| 10543 | inpp4b | NM_001024617.3 | chr8:81342561-82122570 |
| 10544 | inpp5a | NM_001127363.1 | chr7:139389108-139579652 |
| 10545 | inpp5b | NM_008385.4 | chr4:124741849-124801511 |
| 10546 | inpp5d | NM_001110192.2 | chr1:87620311-87720510 |
| 10547 | inpp5e | NM_001290437.1 | chr2:26396248-26409127 |
| 10548 | inpp5f | NM_178641.5 | chr7:128611364-128696436 |
| 10549 | inpp5j | NM_172439.3 | chr11:3494271-3504821 |
| 10550 | inpp5k | NM_008916.2 | chr11:75631019-75648865 |
| 10551 | inppl1 | NM_001122739.1 | chr7:101822631-101837824 |
| 10552 | ins1 | NM_008386.4 | chr19:52264296-52265009 |
| 10553 | ins2 | NM_001185083.2 | chr7:142678655-142679726 |
| 10554 | insc | NM_173767.3 | chr7:114745765-114850380 |
| 10555 | insig1 | NM_153526.5 | chr5:28071411-28078662 |
| 10556 | insig2 | NM_001271531.1 | chr1:121304352-121327678 |
| 10557 | insl3 | NM_013564.7 | chr8:71689251-71690577 |
| 10558 | insl5 | NM_001290648.1 | chr4:103017872-103026842 |
| 10559 | insl6 | NM_013754.1 | chr19:29321353-29325318 |
| 10560 | instm1 | NM_016889.3 | chr2:146221996-146225018 |
| 10561 | insm2 | NM_020287.2 | chr12:55598916-55602017 |
| 10562 | insr | NM_010568.2 | chr8:3150921-3279617 |
| 10563 | insrr | NM_013832.2 | chr3:87796950-87816101 |
| 10564 | ints1 | NM_026748.2 | chr5:139751281-139775678 |
| 10565 | ints10 | NM_027590.4 | chr8:68793928-68829410 |
| 10566 | ints12 | NM_027927.3 | chr3:133091952-133110985 |
| 10567 | ints2 | NM_027421.2 | chr11:86210682-86257568 |
| 10568 | ints3 | NM_145540.3 | chr3:90391379-90433636 |
| 10569 | ints4 | NM_027256.2 | chr7:97480955-97541398 |
| 10570 | ints5 | NM_176843.3 | chr19:8892986-8897890 |
| 10571 | ints6 | NM_008715.2 | chr14:62676324-62761112 |
| 10572 | ints7 | NM_178632.6 | chr1:191575635-191623690 |
| 10573 | ints8 | NM_001159595.1 | chr4:11202927-11254259 |
| 10574 | ints9 | NM_001253731.1 | chr14:64950044-65039835 |
| 10575 | intu | NM_175515.5 | chr3:40540766-40704774 |
| 10576 | invs | NM_001281977.1 | chr4:48279759-48431953 |
| 10577 | ip6k1 | NM_013785.2 | chr9:108002647-108048782 |
| 10578 | ip6k2 | NM_029634.2 | chr9:108795993-108806333 |
| 10579 | ip6k3 | NM_173027.2 | chr17:27143970-27167764 |
| 10580 | ipcef1 | NM_001033391.2 | chr10:6913542-7023185 |
| 10581 | ipmk | NM_027184.1 | chr10:71347792-71385885 |
| 10582 | ipo11 | NM_029665.3 | chr13:106794438-106936915 |
| 10583 | ipo13 | NM_146152.3 | chr4:117894492-117914999 |
| 10584 | ipo4 | NM_024267.6 | chr14:55625628-55635678 |
| 10585 | ipo5 | NM_023579.4 | chr14:120911193-120948044 |
| 10586 | ipo7 | NM_181517.3 | chr7:110018424-110055114 |
| 10587 | ipo8 | NM_001081113.1 | chr6:148770683-148831467 |
| 10588 | ipo9 | NM_153774.1 | chr1:135382314-135430491 |
| 10589 | ipp | NM_008389.3 | chr4:116507548-116538235 |
| 10590 | ippk | NM_001276399.1 | chr13:49421613-49463060 |
| 10591 | ipw | NR_015351.1 | chr7:59619157-59678878 |
| 10592 | iqca | NM_029122.2 | chr1:90042131-90153401 |
| 10593 | iqcb1 | NM_177128.4 | chr16:36828399-36872715 |
| 10594 | iqcc | NM_198026.2 | chr4:129615616-129619093 |
| 10595 | iqcd | NM_029408.2 | chr5:120589022-120607113 |
| 10596 | iqce | NM_028833.3 | chr5:140663504-140702378 |
| 10597 | iqcf1 | NM_001146701.1 | chr9:106499966-106502250 |
| 10598 | iqcf3 | NM_026645.3 | chr9:106543388-106561625 |
| 10599 | iqcf4 | NM_026090.2 | chr9:106568318-106570967 |
| 10600 | iqcf5 | NM_029300.1 | chr9:106514572-106516003 |
| 10601 | iqck | NM_001101628.1 | chr9:106626581-106627612 |
| 10602 | iqcg | NM_178378.3 | chr16:33014269-33056186 |
| 10603 | iqch | NM_030068.2 | chr9:63421448-63602493 |
| 10604 | iqci | NM_177585.3 | chr3:67892219-68056593 |
| 10605 | iqck | NM_001081446.1 | chr7:118855774-118972652 |
| 10606 | iqgap1 | NM_016721.2 | chr7:80711582-80803331 |
| 10607 | iqgap2 | NM_027711.1 | chr13:95627176-95891922 |
| 10608 | iqgap3 | NM_001033484.1 | chr3:88082050-88121048 |
| 10609 | iqsec1 | NM_001134383.1 | chr6:90659597-90716529 |
| 10610 | iqsec2 | NM_001005475.2 | chrX:152179008-152225237 |
| 10611 | iqsec3 | NM_001033254.3 | chr12:121372927-121473678 |
| 10612 | iqub | NM_172535.3 | chr6:24444864-24515067 |
| 10613 | irak1 | NM_001177973.1 | chrX:74013913-74023921 |
| 10614 | irak1bp1 | NM_001168240.1 | chr9:82829805-82847688 |
| 10615 | irak2 | NM_001113553.1 | chr6:113638466-113695027 |
| 10616 | irak3 | NM_028679.3 | chr10:120141653-120201537 |
| 10617 | irak4 | NM_029926.5 | chr15:94543659-94568316 |
| 10618 | ireb2 | NM_022655.3 | chr9:54863754-54912534 |
| 10619 | irf1 | NM_001159393.1 | chr11:53770013-53778374 |
| 10620 | irf2 | NM_008391.4 | chr8:46739744-46847458 |
| 10621 | irf2bp1 | NM_178757.3 | chr7:19004064-19006763 |
| 10622 | irf2bp2 | NM_001164598.1 | chr8:126588295-126593436 |
| 10623 | irf2bpl | NM_145836.2 | chr12:86880702-86884814 |
| 10624 | irf3 | NM_016849.4 | chr7:44997647-45002848 |
| 10625 | irf4 | NM_013674.1 | chr13:30749257-30766927 |
| 10626 | irf5 | NM_001252382.1 | chr6:29529281-29537320 |
| 10627 | irf6 | NM_016851.2 | chr1:193153111-193172035 |
| 10628 | irf7 | NM_001252600.1 | chr7:141263182-141266424 |
| 10629 | irf8 | NM_008320.4 | chr8:120736357-120756692 |
| 10630 | irf9 | NM_001159417.1 | chr14:55603984-55610030 |
| 10631 | irg1 | NM_008392.1 | chr14:103047011-103056573 |
| 10632 | irgc | NM_199013.2 | chr7:24431925-24445682 |
| 10633 | irgm1 | NM_008326.1 | chr11:48865248-48871346 |
| 10634 | irgm2 | NM_019440.3 | chr11:58214976-58222783 |

Fig. 26 - 57

| | | | |
|---|---|---|---|
| 10635 | Irgq | NM_153134.3 | chr7:24530647-24538600 |
| 10636 | Irs1 | NM_010570.4 | chr1:82233104-82291439 |
| 10637 | Irs2 | NM_001081212.1 | chr8:10986963-11008430 |
| 10638 | Irs3 | NM_010571.3 | chr5:137643031-137645714 |
| 10639 | Irs4 | NM_010572.2 | chrX:141710997-141725217 |
| 10640 | Irx1 | NM_010573.2 | chr13:71958231-71963723 |
| 10641 | Irx2 | NM_010574.2 | chr13:72628977-72634194 |
| 10642 | Irx3 | NM_001253822.1 | chr8:91798510-91801654 |
| 10643 | Irx4 | NM_018885.2 | chr13:73260496-73269620 |
| 10644 | Irx5 | NM_018826.2 | chr8:92357795-92361456 |
| 10645 | Irx6 | NM_022428.3 | chr8:92674288-92680956 |
| 10646 | Isca1 | NM_026921.4 | chr13:59755414-59769789 |
| 10647 | Isca2 | NM_028863.1 | chr12:84773269-84775089 |
| 10648 | Iscu | NM_025526.4 | chr5:113772811-113778282 |
| 10649 | Isg15 | NM_015783.3 | chr4:156199423-156200818 |
| 10650 | Isg20 | NM_001113527.1 | chr7:78914234-78920396 |
| 10651 | Isg20l2 | NM_177663.4 | chr3:87930313-87940686 |
| 10652 | Isl1 | NM_021459.4 | chr13:116298269-116309688 |
| 10653 | Isl2 | NM_027397.3 | chr9:55541148-55546178 |
| 10654 | Islr | NM_001195431.1 | chr9:58156263-58158554 |
| 10655 | Islr2 | NM_001161535.1 | chr9:58196296-58201715 |
| 10656 | Ism1 | NM_001276489.1 | chr2:139678177-139758581 |
| 10657 | Ism2 | NM_001290302.1 | chr12:87278637-87299705 |
| 10658 | Iso1 | NM_025478.3 | chr18:58659481-58679570 |
| 10659 | Isoc2a | NM_001101598.1 | chr7:4877052-4895716 |
| 10660 | Isoc2b | NM_026158.2 | chr7:4844959-4866179 |
| 10661 | Ispd | NM_001289502.1 | chr12:36381449-36689503 |
| 10662 | Ist1 | NM_028018.2 | chr8:109671320-109693294 |
| 10663 | Isx | NM_027837.3 | chr8:74873173-74893506 |
| 10664 | Isy1 | NM_133934.4 | chr6:87818447-87838759 |
| 10665 | Isyna1 | NM_023627.1 | chr8:70594480-70597290 |
| 10666 | Itch | NM_001243712.1 | chr2:155133480-155226855 |
| 10667 | Itfg1 | NM_028007.3 | chr8:85717556-85840949 |
| 10668 | Itfg2 | NM_133927.3 | chr6:128409443-128424910 |
| 10669 | Itfg3 | NM_001206335.1 | chr17:26212691-26244242 |
| 10670 | Itga1 | NM_001033228.3 | chr13:114958080-115101964 |
| 10671 | Itga10 | NM_001302471.1 | chr3:96645584-96664519 |
| 10672 | Itga11 | NM_176922.5 | chr9:62677854-62783979 |
| 10673 | Itga2 | NM_008396.2 | chr13:114835911-114932041 |
| 10674 | Itga2b | NM_010575.2 | chr11:102453296-102469883 |
| 10675 | Itga3 | NM_013565.3 | chr11:95044474-95076714 |
| 10676 | Itga4 | NM_010576.3 | chr2:79255425-79333114 |
| 10677 | Itga5 | NM_010577.4 | chr15:103344285-103366791 |
| 10678 | Itga6 | NM_001277970.1 | chr2:71786938-71858427 |
| 10679 | Itga7 | NM_008398.2 | chr10:128933812-128958284 |
| 10680 | Itga8 | NM_001001309.2 | chr2:12106659-12301920 |
| 10681 | Itga9 | NM_001113514.1 | chr9:118711691-118901003 |
| 10682 | Itgad | NM_001029872.3 | chr7:128173945-128205503 |
| 10683 | Itgae | NM_008399.2 | chr11:73090594-73147449 |
| 10684 | Itgal | NM_001253872.1 | chr7:127296259-127335137 |
| 10685 | Itgam | NM_001082960.1 | chr7:128062639-128118491 |
| 10686 | Itgav | NM_008402.3 | chr2:83724396-83806917 |
| 10687 | Itgax | NM_021334.2 | chr7:128129667-128150657 |
| 10688 | Itgb1 | NM_010578.2 | chr8:128685653-128733579 |
| 10689 | Itgb1bp1 | NM_008403.4 | chr12:21269805-21286237 |
| 10690 | Itgb1bp2 | NM_013712.2 | chrX:101449108-101453541 |
| 10691 | Itgb2 | NM_008404.4 | chr10:77530347-77565674 |
| 10692 | Itgb2l | NM_008405.3 | chr16:96422297-96443614 |
| 10693 | Itgb3 | NM_016780.2 | chr11:104607999-104670471 |
| 10694 | Itgb3bp | NM_026348.3 | chr4:99765401-99829118 |
| 10695 | Itgb4 | NM_001005608.2 | chr11:115974724-116008411 |
| 10696 | Itgb5 | NM_001145884.1 | chr16:33829664-33949338 |
| 10697 | Itgb6 | NM_001159564.1 | chr2:60598291-60722603 |
| 10698 | Itgb7 | NM_013566.2 | chr15:102215994-102231935 |
| 10699 | Itgb8 | NM_177290.3 | chr12:119162802-119238276 |
| 10700 | Itgbl1 | NM_145467.2 | chr14:123660139-123974079 |
| 10701 | Itih1 | NM_008406.3 | chr14:30929179-30943289 |
| 10702 | Itih2 | NM_010582.3 | chr2:10094590-10330683 |
| 10703 | Itih3 | NM_008407.2 | chr14:30908573-30923587 |
| 10704 | Itih4 | NM_001159299.2 | chr14:30886475-30901986 |
| 10705 | Itih5 | NM_172471.2 | chr2:10153542-10256529 |
| 10706 | Itk | NM_001281965.1 | chr11:46325147-46389515 |
| 10707 | Itln1 | NM_010585.3 | chr1:171518123-171535294 |
| 10708 | Itm2a | NM_008409.2 | chrX:107397194-107403360 |
| 10709 | Itm2b | NM_008410.2 | chr14:73362231-73385271 |
| 10710 | Itm2c | NM_022417.3 | chr1:85894509-85908698 |
| 10711 | Itpa | NM_025922.2 | chr2:130667840-130681614 |
| 10712 | Itpk1 | NM_172584.3 | chr12:102568582-102704869 |
| 10713 | Itpka | NM_146125.2 | chr2:119742336-119751253 |
| 10714 | Itpkb | NM_001081175.1 | chr1:180330475-180423659 |
| 10715 | Itpkc | NM_181593.2 | chr7:27207169-27228597 |
| 10716 | Itpr1 | NM_010585.5 | chr6:108213095-108551116 |
| 10717 | Itpr2 | NM_010586.2 | chr6:146108298-146502223 |
| 10718 | Itpr3 | NM_080553.3 | chr17:27057303-27112223 |
| 10719 | Itprip | NM_001001738.2 | chr19:47894595-47919299 |
| 10720 | Itpripl1 | NM_001163527.1 | chr2:127138768-127143457 |
| 10721 | Itpripl2 | NM_001289450.1 | chr7:118485111-118491975 |
| 10722 | Itsn1 | NM_001110275.1 | chr16:91729370-91871655 |
| 10723 | Itsn2 | NM_001198968.2 | chr12:4593007-4713952 |
| 10724 | Ivd | NM_019826.3 | chr2:118861999-118881357 |
| 10725 | Ivl | NM_008412.3 | chr3:92570899-92573735 |
| 10726 | Ivns1abp | NM_001039511.1 | chr1:151344497-151356798 |
| 10727 | Iws1 | NM_173441.3 | chr18:32067733-32104331 |
| 10728 | Iyd | NM_027391.3 | chr10:3540278-3554877 |
| 10729 | Izumo1 | NM_001018013.1 | chr7:45621810-45627242 |
| 10730 | Izumo2 | NM_029317.1 | chr7:44708742-44719842 |
| 10731 | Izumo3 | NM_027034.1 | chr4:92144317-92147221 |
| 10732 | Izumo4 | NM_027829.3 | chr10:80702692-80705382 |
| 10733 | Jade1 | NM_001130184.1 | chr3:41555733-41616864 |
| 10734 | Jade2 | NM_199299.3 | chr11:51813455-51857481 |
| 10735 | Jade3 | NM_001289684.1 | chrX:20425687-20519939 |
| 10736 | Jag1 | NM_013822.5 | chr2:137081450-137116520 |
| 10737 | Jag2 | NM_010588.2 | chr12:112908589-112929495 |
| 10738 | Jagn1 | NM_001205025.1 | chr6:113442516-113448229 |
| 10739 | Jak1 | NM_146145.2 | chr4:101151973-101265282 |
| 10740 | Jak2 | NM_001048177.2 | chr19:29251802-29313080 |
| 10741 | Jak3 | NM_001190830.1 | chr7:71676382-71688313 |
| 10742 | Jakmip1 | NM_178394.4 | chr5:37050856-37125298 |
| 10743 | Jakmip2 | NM_001163637.1 | chr18:43531407-43687773 |
| 10744 | Jakmip3 | NM_028708.2 | chr7:138940729-139083976 |
| 10745 | Jam2 | NM_023844.5 | chr16:84774122-84826375 |
| 10746 | Jam3 | NM_023277.4 | chr9:27097383-27155421 |
| 10747 | Jarid2 | NM_001205043.1 | chr13:44731270-44921643 |
| 10748 | Jazf1 | NM_001168277.1 | chr6:52768067-52909620 |
| 10749 | Jdp2 | NM_001205052.1 | chr12:85599104-85639878 |
| 10750 | Jkamp | NM_001205067.1 | chr12:72085838-72101527 |
| 10751 | Jmjd1c | NM_001242396.1 | chr10:67185749-67256326 |
| 10752 | Jmjd4 | NM_001205068.1 | chr11:59450044-59458567 |
| 10753 | Jmjd6 | NM_033398.2 | chr11:116837431-116843449 |
| 10754 | Jmjd7 | NM_001114637.1 | chr2:120027482-120032604 |
| 10755 | Jmjd7-pla2g4b | NR_104353.1 | chr2:120027482-120043032 |
| 10756 | Jmjd8 | NM_028101.4 | chr17:25829042-25831843 |
| 10757 | Jmy | NM_021310.3 | chr13:93430096-93499808 |
| 10758 | Josd1 | NM_028792.3 | chr15:79674249-79687872 |
| 10759 | Josd2 | NM_001205070.1 | chr7:44467979-44471658 |
| 10760 | Jph1 | NM_020604.2 | chr1:16994939-17097889 |
| 10761 | Jph2 | NM_001205076.1 | chr2:163336241-163397993 |
| 10762 | Jph3 | NM_020605.3 | chr8:121730558-121791083 |
| 10763 | Jph4 | NM_177049.5 | chr14:55106825-55116935 |
| 10764 | Jpx | NR_015508.3 | chrX:103493557-103506425 |
| 10765 | Jrk | NM_008415.6 | chr15:74702411-74709322 |
| 10766 | Jrkl | NM_001033181.1 | chr9:13242789-13246741 |
| 10767 | Jsrp1 | NM_028001.3 | chr10:80808495-80813498 |
| 10768 | Jtb | NM_206924.2 | chr3:90231596-90235840 |
| 10769 | Jun | NM_010591.2 | chr4:95049035-95052222 |
| 10770 | Junb | NM_008416.3 | chr8:84976908-84978748 |
| 10771 | Jund | NM_001286944.1 | chr8:70697738-70700616 |
| 10772 | Jup | NM_010593.2 | chr11:100368855-100397790 |
| 10773 | Kairn | NM_001164268.1 | chr16:34152024-34514027 |
| 10774 | Kank1 | NM_181404.5 | chr19:25237201-25434496 |
| 10775 | Kank2 | NM_145611.4 | chr9:21766772-21798546 |
| 10776 | Kank3 | NM_030697.2 | chr17:33810522-33822914 |
| 10777 | Kank4 | NM_172872.3 | chr4:98754891-98817537 |
| 10778 | Kank4os | NR_040437.1 | chr4:98793767-98799037 |
| 10779 | Kansl1 | NM_001081045.1 | chr11:104333228-104442291 |
| 10780 | Kansl1l | NM_001122738.1 | chr1:66719242-66817595 |
| 10781 | Kansl2 | NM_001289437.1 | chr15:98517657-98534269 |
| 10782 | Kansl3 | NM_172652.3 | chr1:36335729-36369181 |
| 10783 | Kap | NM_010594.2 | chr6:133849854-133853667 |
| 10784 | Kars | NM_001130868.2 | chr8:111993438-112011354 |
| 10785 | Kat2a | NM_001038010.2 | chr11:100704745-100712467 |
| 10786 | Kat2b | NM_001190846.1 | chr17:53584125-53672721 |
| 10787 | Kat5 | NM_001199247.1 | chr19:5603013-5610094 |
| 10788 | Kat6a | NM_001081149.1 | chr8:22859538-22943262 |
| 10789 | Kat6b | NM_001205241.1 | chr14:21499769-21672478 |
| 10790 | Kat7 | NM_001195003.1 | chr11:95271852-95310246 |
| 10791 | Kat8 | NM_026370.1 | chr7:127912516-127925762 |
| 10792 | Katna1 | NM_011835.2 | chr10:7725999-7763150 |
| 10793 | Katnal1 | NM_153572.2 | chr5:148871583-148928647 |
| 10794 | Katnal2 | NM_027721.2 | chr18:76983199-77047296 |
| 10795 | Katnb1 | NM_028805.2 | chr8:95081200-95099874 |
| 10796 | Katnbl1 | NM_024254.3 | chr2:112379210-112414237 |
| 10797 | Kazald1 | NM_178929.4 | chr19:45076138-45079289 |
| 10798 | Kazn | NM_001109684.1 | chr4:142139239-142210208 |
| 10799 | Kbtbd11 | NM_029116.2 | chr8:15011024-15033332 |
| 10800 | Kbtbd12 | NM_001278671.1 | chr6:88547721-88627448 |
| 10801 | Kbtbd13 | NM_028974.1 | chr9:65388683-65391652 |
| 10802 | Kbtbd2 | NM_145958.2 | chr6:56777524-56797813 |
| 10803 | Kbtbd3 | NM_001164574.1 | chr9:4309742-4331732 |
| 10804 | Kbtbd4 | NM_025991.3 | chr2:90904785-90910560 |
| 10805 | Kbtbd7 | NM_001024135.2 | chr14:79426510-79431038 |
| 10806 | Kbtbd8 | NM_001008785.5 | chr9:95117879-95129793 |
| 10807 | Kcmf1 | NM_019715.2 | chr6:72841113-72899979 |
| 10808 | Kcna1 | NM_010595.3 | chr6:126636462-126645801 |
| 10809 | Kcna10 | NM_001081140.1 | chr3:107183142-107195721 |
| 10810 | Kcna2 | NM_008417.5 | chr3:107101566-107115005 |
| 10811 | Kcna3 | NM_008418.2 | chr3:107036161-107038129 |
| 10812 | Kcna4 | NM_021275.4 | chr2:107290588-107298504 |
| 10813 | Kcna5 | NM_145983.2 | chr6:126632550-126635555 |
| 10814 | Kcna6 | NM_013568.6 | chr6:126708328-126740674 |
| 10815 | Kcna7 | NM_010596.2 | chr7:45405959-45411382 |
| 10816 | Kcnab1 | NM_001289450.1 | chr3:65188102-65378225 |
| 10817 | Kcnab2 | NM_001252654.1 | chr4:152390739-152477549 |
| 10818 | Kcnab3 | NM_010599.4 | chr11:69328257-69333041 |
| 10819 | Kcnb1 | NM_008420.4 | chr2:167095968-167188818 |
| 10820 | Kcnb2 | NM_001098528.2 | chr1:15312451-15714214 |
| 10821 | Kcnc1 | NM_001112739.2 | chr7:46396467-46438704 |
| 10822 | Kcnc2 | NM_001025581.1 | chr10:112271122-112466304 |
| 10823 | Kcnc3 | NM_001290682.1 | chr7:44590885-44604751 |
| 10824 | Kcnc4 | NM_145922.2 | chr3:107438302-107458898 |

Fig. 26 - 58

| | | | |
|---|---|---|---|
| 10825 | Kcnd1 | NM_008423.2 | chrX:7823758-7838278 |
| 10826 | Kcnd2 | NM_019697.3 | chr6:21216108-21729805 |
| 10827 | Kcnd3 | NM_001039347.1 | chr3:105452329-105674002 |
| 10828 | Kcnd3os | NR_040759.1 | chr3:105448189-105452955 |
| 10829 | Kcne1 | NM_008424.3 | chr16:92346000-92359468 |
| 10830 | Kcne1l | NM_021487.1 | chrX:142304752-142306198 |
| 10831 | Kcne2 | NM_134110.3 | chr16:92291388-92298133 |
| 10832 | Kcne3 | NM_001190869.1 | chr7:100176669-100184869 |
| 10833 | Kcne4 | NM_021342.1 | chr1:78816948-78820025 |
| 10834 | Kcnf1 | NM_201531.3 | chr12:17172099-17176888 |
| 10835 | Kcng1 | NM_001081134.1 | chr2:168261697-168269331 |
| 10836 | Kcng2 | NM_001190373.1 | chr18:80294543-80364254 |
| 10837 | Kcng3 | NM_153512.1 | chr17:83585956-83631895 |
| 10838 | Kcng4 | NM_025734.2 | chr8:119623853-119635680 |
| 10839 | Kcnh1 | NM_001038607.2 | chr1:192190776-192510159 |
| 10840 | Kcnh2 | NM_013569.2 | chr5:24319588-24351604 |
| 10841 | Kcnh3 | NM_010601.3 | chr15:99224975-99242817 |
| 10842 | Kcnh4 | NM_001081194.2 | chr11:100740377-100759778 |
| 10843 | Kcnh5 | NM_172805.3 | chr12:74897216-75177332 |
| 10844 | Kcnh6 | NM_001037712.1 | chr11:106008202-106034064 |
| 10845 | Kcnh7 | NM_133207.2 | chr2:62702945-63184287 |
| 10846 | Kcnh8 | NM_001031811.2 | chr17:52602708-52979194 |
| 10847 | Kcnip1 | NM_001190885.1 | chr11:33629340-33843585 |
| 10848 | Kcnip2 | NM_001276358.1 | chr19:45792345-45812291 |
| 10849 | Kcnip3 | NM_001111331.1 | chr2:127456497-127482499 |
| 10850 | Kcnip4 | NM_001199242.1 | chr5:48389502-48569761 |
| 10851 | Kcnj1 | NM_001168354.1 | chr9:32393984-32399194 |
| 10852 | Kcnj10 | NM_001039484.1 | chr1:172341209-172374085 |
| 10853 | Kcnj11 | NM_001204411.1 | chr7:46097122-46100764 |
| 10854 | Kcnj12 | NM_001267593.1 | chr11:61022563-61073267 |
| 10855 | Kcnj13 | NM_001110227.2 | chr1:87384576-87394729 |
| 10856 | Kcnj14 | NM_145963.2 | chr7:45816466-45824747 |
| 10857 | Kcnj15 | NM_001039056.2 | chr16:95257557-95300258 |
| 10858 | Kcnj16 | NM_010604.2 | chr11:110968032-111027967 |
| 10859 | Kcnj2 | NM_008425.4 | chr11:111066163-111076825 |
| 10860 | Kcnj3 | NM_008426.2 | chr2:55435969-55598145 |
| 10861 | Kcnj4 | NM_008427.4 | chr15:79483713-79505241 |
| 10862 | Kcnj5 | NM_010605.4 | chr9:32314782-32344237 |
| 10863 | Kcnj6 | NM_001252658.1 | chr16:94748682-94997696 |
| 10864 | Kcnj8 | NM_008428.4 | chr6:142564938-142571356 |
| 10865 | Kcnj9 | NM_008429.2 | chr1:172321032-172329263 |
| 10866 | Kcnk1 | NM_008430.2 | chr8:125995101-126030688 |
| 10867 | Kcnk10 | NM_029911.5 | chr12:98433993-98577940 |
| 10868 | Kcnk12 | NM_199251.1 | chr17:87745820-87797994 |
| 10869 | Kcnk13 | NM_001144626.1 | chr12:99964498-100062682 |
| 10870 | Kcnk15 | NM_001030292.1 | chr2:163853749-163858874 |
| 10871 | Kcnk16 | NM_029006.1 | chr14:20262755-20269162 |
| 10872 | Kcnk18 | NM_207261.3 | chr19:59219647-59237370 |
| 10873 | Kcnk2 | NM_001159850.1 | chr1:189207929-189343353 |
| 10874 | Kcnk3 | NM_010608.2 | chr5:30588169-30625270 |
| 10875 | Kcnk4 | NM_008431.2 | chr19:6925689-6934515 |
| 10876 | Kcnk5 | NM_021542.4 | chr14:20140057-20181782 |
| 10877 | Kcnk6 | NM_001033525.3 | chr7:29221927-29232522 |
| 10878 | Kcnk7 | NM_010609.2 | chr19:5704475-5707101 |
| 10879 | Kcnk9 | NM_001033876.1 | chr15:72512118-72546279 |
| 10880 | Kcnma1 | NM_001253358.1 | chr14:23298693-24004205 |
| 10881 | Kcnmb1 | NM_031169.4 | chr11:33963012-33973638 |
| 10882 | Kcnmb2 | NM_028231.2 | chr3:31902702-32200180 |
| 10883 | Kcnmb3 | NM_001195074.1 | chr3:32472320-32491969 |
| 10884 | Kcnmb4 | NM_021452.1 | chr10:116417867-116473523 |
| 10885 | Kcnmb4os1 | NR_028107.1 | chr10:116418120-116421235 |
| 10886 | Kcnn1 | NM_032397.2 | chr8:70842048-70857008 |
| 10887 | Kcnn2 | NM_080465.2 | chr18:45560153-45685883 |
| 10888 | Kcnn3 | NM_080466.2 | chr3:89520163-89672494 |
| 10889 | Kcnn4 | NM_001163510.1 | chr7:24370262-24385212 |
| 10890 | Kcnq1 | NM_008434.2 | chr7:143107253-143427042 |
| 10891 | Kcnq1ot1 | NR_001461.5 | chr7:143213110-143296547 |
| 10892 | Kcnq2 | NM_001003824.2 | chr2:181075578-181135289 |
| 10893 | Kcnq3 | NM_152923.2 | chr15:65994914-66286224 |
| 10894 | Kcnq4 | NM_001081142.1 | chr4:120697472-120747176 |
| 10895 | Kcnq5 | NM_001160139.1 | chr1:21398402-21961942 |
| 10896 | Kcnrg | NM_001039105.3 | chr14:61607456-61612833 |
| 10897 | Kcns1 | NM_008435.2 | chr2:164163618-164171113 |
| 10898 | Kcns2 | NM_001271704.1 | chr15:34838048-34843407 |
| 10899 | Kcns3 | NM_001168564.1 | chr12:11090201-11150842 |
| 10900 | Kcnt1 | NM_001145403.2 | chr2:25863794-25918273 |
| 10901 | Kcnt2 | NM_001081027.2 | chr1:140246256-140610261 |
| 10902 | Kcnu1 | NM_008432.3 | chr8:25849622-25937934 |
| 10903 | Kcnv1 | NM_026220.3 | chr15:45106283-45114934 |
| 10904 | Kcnv2 | NM_183179.1 | chr19:27322618-27337179 |
| 10905 | Kcp | NM_001029985.4 | chr6:29482035-29507952 |
| 10906 | Kctd1 | NM_001142751.1 | chr18:14968684-15063582 |
| 10907 | Kctd10 | NM_001159941.1 | chr5:114363571-114380505 |
| 10908 | Kctd11 | NM_153143.4 | chr11:69878263-69880985 |
| 10909 | Kctd12 | NM_177715.4 | chr14:102976580-102982637 |
| 10910 | Kctd12b | NM_175429.3 | chrX:153685153-153696280 |
| 10911 | Kctd13 | NM_172747.2 | chr7:126928878-126945609 |
| 10912 | Kctd14 | NM_001010826.3 | chr7:97453203-97459557 |
| 10913 | Kctd15 | NM_146188.1 | chr7:34639015-34652841 |
| 10914 | Kctd16 | NM_026135.1 | chr18:40258360-40531184 |
| 10915 | Kctd17 | NM_001289671.1 | chr15:78428563-78439303 |
| 10916 | Kctd18 | NM_001159864.1 | chr1:57955100-57970084 |
| 10917 | Kctd19 | NM_177791.3 | chr8:105382806-105413502 |
| 10918 | Kctd2 | NM_183285.3 | chr11:115420125-115431274 |
| 10919 | Kctd20 | NM_025888.5 | chr17:28953215-28967937 |

| | | | |
|---|---|---|---|
| 10920 | Kctd21 | NM_001039039.3 | chr7:97332322-97350216 |
| 10921 | Kctd3 | NM_172650.2 | chr1:188971097-189007840 |
| 10922 | Kctd4 | NM_026214.3 | chr14:75955002-75965217 |
| 10923 | Kctd5 | NM_027008.2 | chr17:24047719-24073485 |
| 10924 | Kctd6 | NM_027782.3 | chr14:8214080-8223569 |
| 10925 | Kctd7 | NM_172509.3 | chr5:130144887-130155808 |
| 10926 | Kctd8 | NM_175519.5 | chr5:69109284-69341709 |
| 10927 | Kctd9 | NM_001111028.1 | chr14:67716097-67742310 |
| 10928 | Kdelc1 | NM_023645.3 | chr1:44106545-44118773 |
| 10929 | Kdelc2 | NM_212445.2 | chr9:53384022-53401867 |
| 10930 | Kdelr1 | NM_133950.2 | chr7:45872839-45883726 |
| 10931 | Kdelr2 | NM_025841.4 | chr5:143403819-143421904 |
| 10932 | Kdelr3 | NM_134090.2 | chr15:79516407-79527739 |
| 10933 | Kdf1 | NM_001083916.1 | chr4:133518962-133530790 |
| 10934 | Kdm1a | NM_133872.2 | chr4:136550532-136602723 |
| 10935 | Kdm1b | NM_172262.3 | chr13:47043498-47085279 |
| 10936 | Kdm2a | NM_001001984.2 | chr19:4316146-4397077 |
| 10937 | Kdm2b | NM_001003953.2 | chr5:122870675-122989099 |
| 10938 | Kdm3a | NM_001038695.3 | chr6:71588969-71632917 |
| 10939 | Kdm3b | NM_001081256.1 | chr18:34777007-34839370 |
| 10940 | Kdm4a | NM_001161823.1 | chr4:118137003-118180043 |
| 10941 | Kdm4b | NM_172132.2 | chr17:56326049-56402873 |
| 10942 | Kdm4c | NM_001172095.1 | chr4:74242496-74405864 |
| 10943 | Kdm4d | NM_173433.2 | chr9:14462580-14500482 |
| 10944 | Kdm5a | NM_145997.2 | chr6:120364098-120444574 |
| 10945 | Kdm5b | NM_152895.2 | chr1:134560177-134632878 |
| 10946 | Kdm5c | NM_013668.4 | chrX:152233226-152279099 |
| 10947 | Kdm6a | NM_011419.3 | chrX:897787-943811 |
| 10948 | Kdm6a | NM_009483.2 | chrX:18162574-18279936 |
| 10949 | Kdm6b | NM_001017426.1 | chr11:69398517-69413675 |
| 10950 | Kdm7a | NM_001034430.4 | chr6:39136619-39206773 |
| 10951 | Kdm8 | NM_029842.5 | chr7:125446619-125462268 |
| 10952 | Kdr | NM_010612.2 | chr5:75933269-75978428 |
| 10953 | Kdsr | NM_027534.2 | chr1:106720409-106759742 |
| 10954 | Keap1 | NM_001110305.1 | chr9:21229729-21239332 |
| 10955 | Keg1 | NM_029550.4 | chr19:12695789-12719896 |
| 10956 | Kel | NM_032540.3 | chr6:41686329-41704325 |
| 10957 | Kera | NM_008438.3 | chr10:97607204-97613688 |
| 10958 | Khdc1a | NM_183322.2 | chr1:21349676-21352199 |
| 10959 | Khdc1b | NM_001113187.1 | chr1:21383555-21386384 |
| 10960 | Khdc1c | NM_001033904.1 | chr1:21368330-21369743 |
| 10961 | Khdc3 | NM_025890.3 | chr9:73102397-73104443 |
| 10962 | Khdrbs1 | NM_011317.4 | chr4:129713814-129742303 |
| 10963 | Khdrbs2 | NM_133235.2 | chr1:32172805-32657738 |
| 10964 | Khdrbs3 | NM_010158.2 | chr15:68928419-69093518 |
| 10965 | Khk | NM_008439.4 | chr5:30921558-30931248 |
| 10966 | Khnyn | NM_027143.2 | chr14:55884968-55896781 |
| 10967 | Khsrp | NM_010613.3 | chr17:57021048-57031507 |
| 10968 | Kidins220 | NM_001081378.1 | chr12:24974931-25059697 |
| 10969 | Kif11 | NM_010615.1 | chr19:37376402-37421859 |
| 10970 | Kif12 | NM_010616.2 | chr4:63165636-63172131 |
| 10971 | Kif13a | NM_010617.2 | chr13:46749087-46929718 |
| 10972 | Kif13b | NM_001081177.1 | chr14:64652530-64806296 |
| 10973 | Kif14 | NM_001287179.2 | chr1:136467847-136530819 |
| 10974 | Kif15 | NM_010620.1 | chr9:122951080-123018733 |
| 10975 | Kif16b | NM_001081133.2 | chr2:142618344-142901464 |
| 10976 | Kif17 | NM_001190978.1 | chr4:138262250-138301973 |
| 10977 | Kif18a | NM_139303.1 | chr2:109280737-109341746 |
| 10978 | Kif18b | NM_197959.2 | chr11:102905518-102925124 |
| 10979 | Kif19a | NM_001102615.1 | chr11:114765388-114790575 |
| 10980 | Kif1a | NM_001110315.2 | chr1:93015454-93101874 |
| 10981 | Kif1b | NM_001290995.1 | chr4:149176318-149307733 |
| 10982 | Kif1c | NM_153103.2 | chr11:70700547-70731970 |
| 10983 | Kif20a | NM_001166406.1 | chr18:34625032-34633277 |
| 10984 | Kif20b | NM_183046.1 | chr19:34922357-34975731 |
| 10985 | Kif21a | NM_001109040.2 | chr15:90933274-91049951 |
| 10986 | Kif21b | NM_001039472.1 | chr1:136131400-136178014 |
| 10987 | Kif22 | NM_145588.1 | chr7:127027730-127042420 |
| 10988 | Kif23 | NM_024245.4 | chr9:61917277-61946799 |
| 10989 | Kif24 | NM_024241.2 | chr4:41390747-41464848 |
| 10990 | Kif26a | NM_001097621.1 | chr12:112146207-112181747 |
| 10991 | Kif26b | NM_001161665.1 | chr1:178529124-178932857 |
| 10992 | Kif27 | NM_175214.3 | chr13:58287515-58354862 |
| 10993 | Kif2a | NM_001145779.1 | chr13:106960584-107022114 |
| 10994 | Kif2b | NM_028547.2 | chr11:91575285-91577555 |
| 10995 | Kif2c | NM_001290662.1 | chr4:117159632-117178772 |
| 10996 | Kif3a | NM_001290805.1 | chr11:53567368-53604246 |
| 10997 | Kif3b | NM_008444.4 | chr2:153291415-153333389 |
| 10998 | Kif3c | NM_008445.2 | chr12:3365131-3406494 |
| 10999 | Kif4 | NM_008446.2 | chrX:100626064-100727271 |
| 11000 | Kif4-ps | NR_033653.1 | chr12:101145608-101149273 |
| 11001 | Kif5a | NM_001039000.4 | chr10:127225694-127263363 |
| 11002 | Kif5b | NM_008448.3 | chr18:6201004-6241524 |
| 11003 | Kif5c | NM_008449.2 | chr2:49619313-49774778 |
| 11004 | Kif6 | NM_177052.3 | chr17:49615171-49909847 |
| 11005 | Kif7 | NM_001291222.1 | chr7:79698097-79714186 |
| 11006 | Kif9 | NM_001163569.1 | chr9:110476993-110524440 |
| 11007 | Kifap3 | NM_010629.3 | chr1:163779582-163917107 |
| 11008 | Kifc1 | NM_001195298.1 | chr17:338755265-33890633 |
| 11009 | Kifc2 | NM_010630.2 | chr15:76660640-76668196 |
| 11010 | Kifc3 | NM_001145831.1 | chr8:95099827-95142540 |
| 11011 | Kifc5b | NM_053173.2 | chr17:26917090-26932579 |
| 11012 | Kin | NM_025280.2 | chr2:10080611-10092701 |
| 11013 | Kir3dl1 | NM_177749.4 | chrX:136517998-136534306 |
| 11014 | Kir3dl2 | NM_177748.2 | chrX:136448106-136469041 |

Fig. 26 - 59

| | | | |
|---|---|---|---|
| 11015 | Kirrel | NM_001170985.1 | chr3:87078591-87174747 |
| 11016 | Kirrel2 | NM_172898.3 | chr7:30447765-30457515 |
| 11017 | Kirrel3 | NM_001190911.1 | chr9:34488730-35036307 |
| 11018 | Kis2 | NR_003188.1 | chrX:52742562-52744593 |
| 11019 | Kiss1 | NM_178260.3 | chr1:133327211-133329722 |
| 11020 | Kiss1r | NM_053244.5 | chr10:79916976-79922272 |
| 11021 | Kit | NM_001122733.1 | chr5:75574986-75656721 |
| 11022 | Kitl | NM_013598.2 | chr10:100015823-100100412 |
| 11023 | Kiz | NM_001033298.3 | chr2:146855888-146970089 |
| 11024 | Kl | NM_013823.2 | chr5:150952606-150993817 |
| 11025 | Klb | NM_031180.2 | chr5:65348410-65384003 |
| 11026 | Klc1 | NM_001025358.2 | chr12:111758867-111794899 |
| 11027 | Klc2 | NM_008451.2 | chr19:5107745-5118408 |
| 11028 | Klc3 | NM_001286038.1 | chr7:19394439-19399921 |
| 11029 | Klc4 | NM_029091.2 | chr17:46630630-46645144 |
| 11030 | Klf1 | NM_010635.2 | chr8:84901927-84905295 |
| 11031 | Klf10 | NM_001289471.1 | chr15:38291463-38306711 |
| 11032 | Klf11 | NM_178357.3 | chr12:24651370-24662782 |
| 11033 | Klf12 | NM_010636.3 | chr14:99870639-100149796 |
| 11034 | Klf13 | NM_021366.3 | chr7:63886350-63938915 |
| 11035 | Klf14 | NM_001135093.1 | chr6:30956020-30958990 |
| 11036 | Klf15 | NM_023184.3 | chr6:90462625-90475209 |
| 11037 | Klf16 | NM_078477.2 | chr10:80567126-80577296 |
| 11038 | Klf17 | NM_029416.2 | chr4:117756658-117765666 |
| 11039 | Klf2 | NM_008452.2 | chr8:72319061-72321654 |
| 11040 | Klf3 | NM_008453.5 | chr5:64803522-64830129 |
| 11041 | Klf4 | NM_010637.3 | chr4:55527136-55532475 |
| 11042 | Klf5 | NM_009769.4 | chr14:99298690-99313409 |
| 11043 | Klf6 | NM_011803.2 | chr13:5861488-5870393 |
| 11044 | Klf7 | NM_033563.2 | chr1:64035670-64121389 |
| 11045 | Klf8 | NM_173780.4 | chrX:153238044-153396134 |
| 11046 | Klf9 | NM_010638.4 | chr19:23141225-23166911 |
| 11047 | Klhdc1 | NM_178253.5 | chr12:69241831-69283961 |
| 11048 | Klhdc10 | NM_029742.3 | chr6:30401854-30455174 |
| 11049 | Klhdc2 | NM_027117.3 | chr12:69296680-69310687 |
| 11050 | Klhdc3 | NM_001163729.2 | chr17:46674550-46680930 |
| 11051 | Klhdc4 | NM_145605.2 | chr8:121796307-121829569 |
| 11052 | Klhdc7a | NM_173427.2 | chr4:139962172-139968026 |
| 11053 | Klhdc7b | NM_001160178.1 | chr15:89386890-89388708 |
| 11054 | Klhdc8a | NM_144810.4 | chr1:132298625-132307357 |
| 11055 | Klhdc8b | NM_030075.2 | chr9:108447638-108461581 |
| 11056 | Klhdc9 | NM_001033039.2 | chr1:171358448-171360798 |
| 11057 | Klhl1 | NM_053105.2 | chr14:96105264-96519034 |
| 11058 | Klhl10 | NM_025727.3 | chr11:100441923-100457024 |
| 11059 | Klhl11 | NM_172565.2 | chr11:100462611-100472782 |
| 11060 | Klhl12 | NM_153128.3 | chr1:134455530-134490873 |
| 11061 | Klhl13 | NM_001290476.2 | chrX:23219270-23285559 |
| 11062 | Klhl14 | NM_001081403.1 | chr18:21550376-21652368 |
| 11063 | Klhl15 | NM_001039059.1 | chrX:94234929-94255968 |
| 11064 | Klhl17 | NM_198305.2 | chr4:156229043-156234857 |
| 11065 | Klhl18 | NM_177771.5 | chr9:110425925-110476694 |
| 11066 | Klhl2 | NM_178633.3 | chr8:64739674-64849924 |
| 11067 | Klhl20 | NM_001039482.1 | chr1:161088377-161131479 |
| 11068 | Klhl21 | NM_001033352.3 | chr4:152008890-152017677 |
| 11069 | Klhl22 | NM_145479.4 | chr16:17759620-17793382 |
| 11070 | Klhl23 | NM_177784.4 | chr2:69822369-69836651 |
| 11071 | Klhl24 | NM_029436.3 | chr16:20097553-20127744 |
| 11072 | Klhl25 | NM_001122780.1 | chr7:75848337-75874130 |
| 11073 | Klhl26 | NM_001122830.1 | chr8:70450227-70476943 |
| 11074 | Klhl28 | NM_025707.3 | chr12:64942439-64965536 |
| 11075 | Klhl29 | NM_001164493.1 | chr12:5077465-5375682 |
| 11076 | Klhl3 | NM_001195075.1 | chr13:58004956-58102428 |
| 11077 | Klhl30 | NM_027551.2 | chr1:91351072-91362404 |
| 11078 | Klhl31 | NM_172925.2 | chr9:77636731-77660122 |
| 11079 | Klhl32 | NM_001033531.3 | chr4:24617272-24851086 |
| 11080 | Klhl33 | NM_001166651.1 | chr14:50891388-50893255 |
| 11081 | Klhl34 | NM_001081667.2 | chrX:157818434-157821060 |
| 11082 | Klhl35 | NM_028145.1 | chr7:99466003-99474020 |
| 11083 | Klhl36 | NM_146219.1 | chr8:119862304-119876989 |
| 11084 | Klhl38 | NM_177755.3 | chr15:58314572-58324169 |
| 11085 | Klhl4 | NM_001290477.1 | chrX:114473332-114561129 |
| 11086 | Klhl40 | NM_028202.3 | chr9:121777606-121783819 |
| 11087 | Klhl41 | NM_001081087.1 | chr2:69670119-69684239 |
| 11088 | Klhl42 | NM_001081237.1 | chr6:147091074-147112778 |
| 11089 | Klhl5 | NM_175174.4 | chr5:65131230-65168142 |
| 11090 | Klhl6 | NM_183839.2 | chr16:19946491-19983049 |
| 11091 | Klhl7 | NM_001161800.1 | chr5:24100589-24161231 |
| 11092 | Klhl8 | NM_178741.3 | chr5:103862049-103911229 |
| 11093 | Klhl9 | NM_172871.2 | chr4:88718291-88722508 |
| 11094 | Klk1 | NM_010639.7 | chr7:44225436-44229617 |
| 11095 | Klk10 | NM_133712.2 | chr7:43781053-43785410 |
| 11096 | Klk11 | NM_001177373.1 | chr7:43774616-43779262 |
| 11097 | Klk12 | NM_027097.1 | chr7:43769099-43773481 |
| 11098 | Klk13 | NM_001039042.2 | chr7:43712566-43726758 |
| 11099 | Klk14 | NM_174866.3 | chr7:43690417-43695536 |
| 11100 | Klk15 | NM_174865.3 | chr7:43933770-43939590 |
| 11101 | Klk1b1 | NM_001043966767-43971315 | chr7:43966767-43971315 |
| 11102 | Klk1b11 | NM_010640.1 | chr7:43995878-43999875 |
| 11103 | Klk1b16 | NM_008454.2 | chr7:44136766-44141604 |
| 11104 | Klk1b21 | NM_010642.2 | chr7:44160291-44166579 |
| 11105 | Klk1b22 | NM_010114.1 | chr7:44112682-44116876 |
| 11106 | Klk1b24 | NM_010643.1 | chr7:44188262-44192451 |
| 11107 | Klk1b26 | NM_010644.3 | chr7:44012677-44016969 |
| 11108 | Klk1b27 | NM_020268.3 | chr7:44052289-44056711 |
| 11109 | Klk1b3 | NM_008693.2 | chr7:44198190-44202351 |

| | | | |
|---|---|---|---|
| 11110 | Klk1b4 | NM_010915.3 | chr7:44207434-44211754 |
| 11111 | Klk1b5 | NM_008456.3 | chr7:44216474-44220703 |
| 11112 | Klk1b7-ps | NR_033120.1 | chr7:43945011-43945927 |
| 11113 | Klk1b8 | NM_008457.2 | chr7:43950671-43954938 |
| 11114 | Klk1b9 | NM_010116.1 | chr7:43976860-43980376 |
| 11115 | Klk4 | NM_019928.2 | chr7:43881171-43885804 |
| 11116 | Klk5 | NM_026806.2 | chr7:43842268-43851181 |
| 11117 | Klk6 | NM_001164696.1 | chr7:43824543-43832027 |
| 11118 | Klk7 | NM_011872.2 | chr7:43811443-43816359 |
| 11119 | Klk8 | NM_008940.2 | chr7:43797576-43803822 |
| 11120 | Klk9 | NM_028660.3 | chr7:43791890-43796756 |
| 11121 | Klkb1 | NM_008455.2 | chr8:45269450-45294835 |
| 11122 | Klra1 | NM_016659.3 | chr6:130363917-130386874 |
| 11123 | Klra10 | NM_008459 | chr6:130269193-130281928 |
| 11124 | Klra12 | NM_010646.1 | chr6:130044023-130306481 |
| 11125 | Klra13-ps | NR_033451.1 | chr6:130291160-130306432 |
| 11126 | Klra14-ps | NR_104105.1 | chr6:130149105-130160748 |
| 11127 | Klra15 | NM_013793.2 | chr6:129972092-130380662 |
| 11128 | Klra17 | NM_133203.5 | chr6:129831153-129876672 |
| 11129 | Klra18 | NM_053153.2 | chr6:130043744-130067258 |
| 11130 | Klra19 | NM_053154.2 | chr6:130013033-130026960 |
| 11131 | Klra2 | NM_001170851.1 | chr6:131219234-131247362 |
| 11132 | Klra21 | NM_053151.1 | chr6:130115218-130129879 |
| 11133 | Klra22 | NM_053152.2 | chr6:129972081-130380808 |
| 11134 | Klra23 | NM_024470.1 | chr6:130291160-130308361 |
| 11135 | Klra3 | NM_001289604.1 | chr6:130323288-130337626 |
| 11136 | Klra33 | NM_001039118.1 | chr6:130009732-130030995 |
| 11137 | Klra4 | NM_001252577.1 | chr6:130044016-130067271 |
| 11138 | Klra5 | NM_008463.2 | chr6:129898991-129913224 |
| 11139 | Klra6 | NM_008464.2 | chr6:130013032-130026954 |
| 11140 | Klra7 | NM_001110323.1 | chr6:130218830-130233322 |
| 11141 | Klra8 | NM_001101620.1 | chr6:130115225-130129898 |
| 11142 | Klra9 | NM_010651.3 | chr6:130178681-130193112 |
| 11143 | Klrb1 | NM_001099918.1 | chr6:128706507-128723046 |
| 11144 | Klrb1a | NM_001159902.1 | chr6:128609226-128622934 |
| 11145 | Klrb1b | NM_030599.4 | chr6:128813705-128826315 |
| 11146 | Klrb1c | NM_001159904.1 | chr6:128778484-128788641 |
| 11147 | Klrb1f | NM_153094.2 | chr6:129045900-129057471 |
| 11148 | Klrb1-ps1 | NR_073569.1 | chr6:129116517-129129446 |
| 11149 | Klrc1 | NM_001136068.2 | chr6:129666015-129678973 |
| 11150 | Klrc2 | NM_001098669.1 | chr6:129656345-129660596 |
| 11151 | Klrc3 | NM_021378.1 | chr6:129639084-129643288 |
| 11152 | Klrd1 | NM_010654.3 | chr6:129591810-129598775 |
| 11153 | Klre1 | NM_153590.3 | chr6:129578285-129585827 |
| 11154 | Klrg1 | NM_016970.1 | chr6:122270596-122282833 |
| 11155 | Klrg2 | NM_001033171.2 | chr6:38626659-38637239 |
| 11156 | Klri1 | NM_001012502.2 | chr6:129697217-129717132 |
| 11157 | Klri2 | NM_177155.4 | chr6:129729040-129740484 |
| 11158 | Klrk1 | NM_001083322.2 | chr6:129610322-129623864 |
| 11159 | Kmo | NM_133809.1 | chr1:175632192-175660853 |
| 11160 | Kmt2a | NM_001081049.1 | chr9:44803354-44881274 |
| 11161 | Kmt2b | NM_001290573.1 | chr7:30568854-30588726 |
| 11162 | Kmt2c | NM_001081383.1 | chr5:25271793-25498783 |
| 11163 | Kmt2d | NM_001033276.3 | chr15:98831668-98871205 |
| 11164 | Kmt2e | NM_026984.1 | chr5:23434428-23504229 |
| 11165 | Kncn | NM_001039124.3 | chr4:115884399-115887964 |
| 11166 | Kndc1 | NM_177261.4 | chr7:139894695-139941540 |
| 11167 | Kng1 | NM_001102411.1 | chr16:23058299-23080006 |
| 11168 | Kng2 | NM_001102409.1 | chr16:22985851-23029101 |
| 11169 | Knop1 | NM_001168218.1 | chr7:118842217-118855998 |
| 11170 | Knstrn | NM_026412.3 | chr2:118814002-118836212 |
| 11171 | Kntc1 | NM_001042421.1 | chr5:123749725-123823593 |
| 11172 | Kpna1 | NM_008465.5 | chr16:35983362-36036162 |
| 11173 | Kpna2 | NM_010655.3 | chr11:106988628-106999525 |
| 11174 | Kpna3 | NM_008466.5 | chr14:61365185-61439947 |
| 11175 | Kpna4 | NM_008467.4 | chr3:69072220-69127092 |
| 11176 | Kpna6 | NM_008468.4 | chr4:129643978-129672767 |
| 11177 | Kpna7 | NM_001013774.2 | chr5:144983743-145009636 |
| 11178 | Kpnb1 | NM_008379.3 | chr11:97159709-97187892 |
| 11179 | Kprp | NM_028629.1 | chr3:92823073-92827247 |
| 11180 | Kptn | NM_133727.2 | chr7:16119875-16127516 |
| 11181 | Kras | NM_021284 | chr6:145216698-145250231 |
| 11182 | Krba1 | NM_133923.3 | chr6:48395585-48419855 |
| 11183 | Krcc1 | NM_145568.3 | chr6:71272018-71285319 |
| 11184 | Kremen1 | NM_032396.3 | chr11:5191552-5261610 |
| 11185 | Kremen2 | NM_028416.1 | chr17:23741198-23745829 |
| 11186 | Kri1 | NM_145416.3 | chr9:21273456-21287969 |
| 11187 | Krit1 | NM_001170552.1 | chr5:3803164-3844515 |
| 11188 | Krr1 | NM_178610.4 | chr10:111972694-111988430 |
| 11189 | Krt1 | NM_008473.2 | chr15:101845425-101850786 |
| 11190 | Krt10 | NM_010660.2 | chr11:99385255-99389364 |
| 11191 | Krt12 | NM_010661.2 | chr11:99415663-99422259 |
| 11192 | Krt13 | NM_010662.2 | chr11:100117327-100121566 |
| 11193 | Krt14 | NM_016958.2 | chr11:100203161-100207510 |
| 11194 | Krt15 | NM_008469.2 | chr11:100131758-100135949 |
| 11195 | Krt16 | NM_008470.1 | chr11:100246090-100248902 |
| 11196 | Krt17 | NM_010663.3 | chr11:100256214-100261029 |
| 11197 | Krt18 | NM_010664.3 | chr15:102028215-102032026 |
| 11198 | Krt19 | NM_008471.3 | chr11:100140810-100145926 |
| 11199 | Krt2 | NM_010668.3 | chr15:101810688-101818169 |
| 11200 | Krt20 | NM_023256.5 | chr11:99428402-99438153 |
| 11201 | Krt222 | NM_172946.2 | chr11:99233097-99244067 |
| 11202 | Krt23 | NM_033373.1 | chr11:99477972-99493110 |
| 11203 | Krt24 | NM_029393.1 | chr11:99280092-99285238 |
| 11204 | Krt25 | NM_133730.1 | chr11:99315843-99332941 |

Fig. 26 - 60

| | | | |
|---|---|---|---|
| 11205 | Krt26 | NM_001033397.5 | chr11:99328483-99337965 |
| 11206 | Krt27 | NM_010666.2 | chr11:99345564-99351118 |
| 11207 | Krt28 | NM_027574.1 | chr11:99365006-99374903 |
| 11208 | Krt31 | NM_010659.2 | chr11:100046646-100050551 |
| 11209 | Krt32 | NM_001159374.2 | chr11:100080847-100088226 |
| 11210 | Krt33a | NM_027983.3 | chr11:100011198-100016212 |
| 11211 | Krt33b | NM_013570.1 | chr11:100023633-100029868 |
| 11212 | Krt34 | NM_027563.4 | chr11:100037347-100041554 |
| 11213 | Krt35 | NM_016880.2 | chr11:100092191-100096224 |
| 11214 | Krt36 | NM_001174099.1 | chr11:100102012-100105626 |
| 11215 | Krt39 | NM_213730.2 | chr11:99514623-99521258 |
| 11216 | Krt4 | NM_008475.2 | chr15:101918534-101924735 |
| 11217 | Krt40 | NM_001039666.1 | chr11:99537484-99543158 |
| 11218 | Krt42 | NM_212483.2 | chr11:100262881-100269871 |
| 11219 | Krt5 | NM_027011.2 | chr15:101707069-101712891 |
| 11220 | Krt6a | NM_008476.3 | chr15:101689927-101694305 |
| 11221 | Krt6b | NM_010669.2 | chr15:101676022-101680289 |
| 11222 | Krt7 | NM_033073.3 | chr15:101412402-101427806 |
| 11223 | Krt71 | NM_019956.1 | chr15:101733948-101743007 |
| 11224 | Krt72 | NM_213728.1 | chr15:101776559-101786458 |
| 11225 | Krt73 | NM_212485.2 | chr15:101793307-101802332 |
| 11226 | Krt74 | NR_033444.1 | chr15:101754258-101763504 |
| 11227 | Krt75 | NM_133357.3 | chr15:101563342-101573904 |
| 11228 | Krt76 | NM_001033177.2 | chr15:101884350-101892920 |
| 11229 | Krt77 | NM_001003667.1 | chr15:101859855-101869618 |
| 11230 | Krt78 | NM_212487.4 | chr15:101946003-101954287 |
| 11231 | Krt79 | NM_146063.1 | chr15:101929331-101940324 |
| 11232 | Krt8 | NM_031170.2 | chr15:101996710-102004342 |
| 11233 | Krt80 | NM_028770.2 | chr15:101349570-101370125 |
| 11234 | Krt81 | NM_001166157.1 | chr15:101459060-101463765 |
| 11235 | Krt82 | NM_053249.3 | chr15:101541220-101550659 |
| 11236 | Krt83 | NM_001003668.2 | chr15:101431489-101438804 |
| 11237 | Krt84 | NM_008474.2 | chr15:101525025-101532820 |
| 11238 | Krt85 | NM_016879.2 | chr15:101431013-101491303 |
| 11239 | Krt86 | NM_010667.2 | chr15:101473477-101479983 |
| 11240 | Krt9 | NM_201255.2 | chr11:100186780-100193246 |
| 11241 | Krtap10-10 | NM_001024709.3 | chr10:77835946-77837251 |
| 11242 | Krtap10-4 | NM_001135991.1 | chr10:77826168-77827070 |
| 11243 | Krtap11-1 | NM_001143406.1 | chr16:89570175-89571183 |
| 11244 | Krtap12-1 | NM_010670.1 | chr10:77720585-77721256 |
| 11245 | Krtap13 | NM_010671.1 | chr16:88750743-88751628 |
| 11246 | Krtap13-1 | NM_001085526.2 | chr11:99590460-99591377 |
| 11247 | Krtap13-1 | NM_183189.1 | chr16:88728861-88729611 |
| 11248 | Krtap14 | NM_013707.2 | chr16:88825290-88826145 |
| 11249 | Krtap1-4 | NM_001039521.2 | chr11:99582548-99583677 |
| 11250 | Krtap15 | NM_013713.1 | chr16:88829008-88829844 |
| 11251 | Krtap1-5 | NM_027157.3 | chr11:99579976-99581016 |
| 11252 | Krtap16-1 | NM_130870.1 | chr16:88873664-88874269 |
| 11253 | Krtap16-3 | NM_183296.1 | chr16:88962303-88962873 |
| 11254 | Krtap17-1 | NM_001099774.2 | chr11:99993231-99993994 |
| 11255 | Krtap19-1 | NM_130876.3 | chr16:88868917-88869410 |
| 11256 | Krtap19-3 | NM_130857.2 | chr16:88877512-88878038 |
| 11257 | Krtap19-4 | NM_130874.1 | chr16:88884785-88885089 |
| 11258 | Krtap19-5 | NM_010676.2 | chr16:88895967-88896449 |
| 11259 | Krtap19-9b | NM_133359.1 | chr16:88931803-88932264 |
| 11260 | Krtap20-2 | NM_001163615.1 | chr16:89205860-89206394 |
| 11261 | Krtap21-1 | NM_028621.3 | chr16:89403026-89403774 |
| 11262 | Krtap22-2 | NM_001191018.1 | chr16:89010379-89010759 |
| 11263 | Krtap2-4 | NM_027800.1 | chr11:99614016-99614846 |
| 11264 | Krtap24-1 | NM_001163141.1 | chr16:88610708-88612279 |
| 11265 | Krtap26-1 | NM_027105.2 | chr16:88646823-88647796 |
| 11266 | Krtap27-1 | NM_001163105.1 | chr16:88671045-88671654 |
| 11267 | Krtap3-1 | NM_023511.1 | chr11:99566026-99566630 |
| 11268 | Krtap31-1 | NM_027568.2 | chr11:99907919-99908890 |
| 11269 | Krtap31-2 | NM_001026424.3 | chr11:99936290-99937225 |
| 11270 | Krtap3-2 | NM_025720.3 | chr11:99555822-99556853 |
| 11271 | Krtap3-3 | NM_025524.2 | chr11:99550131-99550863 |
| 11272 | Krtap4-1 | NM_001048196.1 | chr11:99627228-99628239 |
| 11273 | Krtap4-13 | NM_027087.3 | chr11:99809077-99809896 |
| 11274 | Krtap4-16 | NM_001013823.1 | chr11:99850654-99851605 |
| 11275 | Krtap4-2 | NM_026807.2 | chr11:99634113-99635084 |
| 11276 | Krtap4-6 | NM_026834.2 | chr11:99665042-99665960 |
| 11277 | Krtap4-7 | NM_029613.3 | chr11:99643311-99644089 |
| 11278 | Krtap4-8 | NM_001085547.2 | chr11:99780013-99780643 |
| 11279 | Krtap4-9 | NM_001085548.2 | chr11:99785199-99786257 |
| 11280 | Krtap5-1 | NM_015808.3 | chr7:142296376-142297069 |
| 11281 | Krtap5-2 | NM_027844.4 | chr7:142174531-142176005 |
| 11282 | Krtap5-3 | NM_023860.1 | chr7:142201363-142203015 |
| 11283 | Krtap5-4 | NM_015809.2 | chr7:142303501-142304503 |
| 11284 | Krtap5-5 | NM_001037822.1 | chr7:142228794-142229971 |
| 11285 | Krtap6-1 | NM_010672.3 | chr16:89031698-89032292 |
| 11286 | Krtap6-2 | NM_010673.2 | chr16:89419322-89420111 |
| 11287 | Krtap6-5 | NM_130856.2 | chr16:89047288-89047899 |
| 11288 | Krtap7-1 | NM_027771.1 | chr16:89507702-89508323 |
| 11289 | Krtap8-1 | NM_010675.1 | chr16:89487373-89487952 |
| 11290 | Krtap9-1 | NM_015741.2 | chr16:99873388-99874000 |
| 11291 | Krtap9-3 | NM_029351.2 | chr11:99597347-99598106 |
| 11292 | Krtap9-5 | NM_001085527.1 | chr11:99948474-99949551 |
| 11293 | Krtcap2 | NM_025327.3 | chr3:89246437-89249729 |
| 11294 | Krtcap3 | NM_027221.3 | chr5:31251705-31253197 |
| 11295 | Krtdap | NM_001033131.3 | chr7:30787904-30791083 |
| 11296 | Ksr1 | NM_013571.2 | chr11:79014800-79146354 |
| 11297 | Ksr2 | NM_001312914.1 | chr5:117413770-117775004 |
| 11298 | Kti12 | NM_029571.2 | chr4:108847856-108849412 |
| 11299 | Ktn1 | NM_008477.2 | chr14:47663755-47736564 |
| 11300 | Kxd1 | NM_029366.2 | chr8:70513395-70523180 |
| 11301 | Ky | NM_024291.3 | chr9:102506137-102546239 |
| 11302 | Kynu | NM_001289593.1 | chr2:43555324-43680216 |
| 11303 | L1cam | NM_008478.3 | chrX:73853779-73880834 |
| 11304 | L1td1 | NM_001081202.1 | chr4:98726753-98738486 |
| 11305 | L2hgdh | NM_145443.2 | chr12:69690435-69724874 |
| 11306 | L3hypdh | NM_026038.2 | chr12:72073427-72085313 |
| 11307 | L3mbtl1 | NM_001081338.1 | chr2:162943464-162974522 |
| 11308 | L3mbtl2 | NM_001289711.1 | chr15:81663888-81688315 |
| 11309 | L3mbtl3 | NM_172787.2 | chr10:26275451-26375185 |
| 11310 | L3mbtl4 | NM_177278.5 | chr17:68273796-68780086 |
| 11311 | l7Rn6 | NM_001291286.1 | chr7:89918684-89941204 |
| 11312 | Lacc1 | NM_172488.2 | chr14:77024200-77036617 |
| 11313 | Lace1 | NM_145743.2 | chr10:42312584-42478565 |
| 11314 | Lactb | NM_030717.1 | chr9:66955392-66975484 |
| 11315 | Lactb2 | NM_145381.2 | chr1:13625899-13660509 |
| 11316 | Lactbl1 | NM_001243262.1 | chr4:136622620-136638110 |
| 11317 | Lad1 | NM_133664.3 | chr1:135818597-135833341 |
| 11318 | Lag3 | NM_008479.2 | chr6:124904358-124911705 |
| 11319 | Lage3 | NM_025410.2 | chrX:74352161-74353618 |
| 11320 | Lair1 | NM_001113474.1 | chr7:4007072-4063204 |
| 11321 | Lalba | NM_010679.1 | chr15:98480399-98482683 |
| 11322 | Lama1 | NM_008480.2 | chr17:67697264-67822645 |
| 11323 | Lama2 | NM_008481.2 | chr10:26981284-27616942 |
| 11324 | Lama3 | NM_010680.1 | chr18:12834023-12583012 |
| 11325 | Lama4 | NM_010681.4 | chr10:38965514-39110188 |
| 11326 | Lama5 | NM_001081171.2 | chr2:180176372-180225859 |
| 11327 | Lamb1 | NM_008482.2 | chr12:31265293-31329639 |
| 11328 | Lamb2 | NM_008483.3 | chr9:108479861-108490530 |
| 11329 | Lamb3 | NM_001277928.1 | chr1:193302242-193343878 |
| 11330 | Lamc1 | NM_010683.2 | chr1:153218921-153332786 |
| 11331 | Lamc2 | NM_008485.3 | chr1:153122755-153186447 |
| 11332 | Lamc3 | NM_011836.3 | chr2:31887280-31946535 |
| 11333 | Lamp1 | NM_010684.2 | chr8:13159134-13175338 |
| 11334 | Lamp2 | NM_001017959.2 | chrX:38405048-38456460 |
| 11335 | Lamp3 | NM_177356.3 | chr16:19653380-19706365 |
| 11336 | Lamp5 | NM_029530.2 | chr2:136057926-136069917 |
| 11337 | Lamtor1 | NM_025605.3 | chr7:101905836-101911903 |
| 11338 | Lamtor2 | NM_031248.3 | chr3:88549818-88552927 |
| 11339 | Lamtor3 | NM_019920.2 | chr3:137918554-137928762 |
| 11340 | Lamtor4 | NM_001081108.2 | chr5:138255481-138259395 |
| 11341 | Lamtor5 | NM_026774.2 | chr3:107278857-107284081 |
| 11342 | Lancl1 | NM_001190984.1 | chr1:67000516-67038834 |
| 11343 | Lancl2 | NM_133737.2 | chr6:57702454-57739449 |
| 11344 | Lancl3 | NM_173414.3 | chrX:9199972-9268085 |
| 11345 | Lao1 | NM_133892.4 | chr4:118961966-118968910 |
| 11346 | Lap3 | NM_024434.6 | chr5:45493373-45512691 |
| 11347 | Laptm4a | NM_008640.2 | chr12:8921306-8938741 |
| 11348 | Laptm4b | NM_033521.3 | chr15:34238025-34284295 |
| 11349 | Laptm5 | NM_010686.3 | chr4:130913333-130936148 |
| 11350 | Large | NM_010687.1 | chr8:72814598-73352556 |
| 11351 | Larp1 | NM_028451.1 | chr11:58009063-58062032 |
| 11352 | Larp1b | NM_001040399.1 | chr3:40950630-40977793 |
| 11353 | Larp4 | NM_001024526.2 | chr15:99972779-100016358 |
| 11354 | Larp4b | NM_172585.3 | chr13:9093880-9174451 |
| 11355 | Larp6 | NM_026235.4 | chr9:60713120-60738801 |
| 11356 | Larp7 | NM_138593.2 | chr3:127536713-127553349 |
| 11357 | Lars | NM_134137.2 | chr18:42202348-42262071 |
| 11358 | Lars2 | NM_153168.2 | chr9:123366939-123462664 |
| 11359 | Las1l | NM_152822.3 | chrX:95935312-95956974 |
| 11360 | Lasp1 | NM_010688.4 | chr11:97799671-97838764 |
| 11361 | Lat | NM_010689.2 | chr7:126363827-126369534 |
| 11362 | Lat2 | NM_020044 | chr5:134600102-134615025 |
| 11363 | Lats1 | NM_010690.1 | chr10:7681208-7716461 |
| 11364 | Lats2 | NM_015771.2 | chr14:57689661-57746123 |
| 11365 | Lax1 | NM_001159649.1 | chr1:133679028-133690108 |
| 11366 | Layn | NM_001035534.1 | chr9:51056779-51077094 |
| 11367 | Lbh | NM_029999.4 | chr17:72918304-72941946 |
| 11368 | Lbp | NM_008489.2 | chr2:158306492-158332852 |
| 11369 | Lbr | NM_133815.2 | chr1:181815314-181842401 |
| 11370 | Lbx1 | NM_010691.5 | chr19:45233727-45235236 |
| 11371 | Lbx2 | NM_010692.3 | chr6:83086364-83088241 |
| 11372 | Lca5 | NM_027448.2 | chr9:83393415-83441099 |
| 11373 | Lca5l | NM_001001492.2 | chr16:96158405-96192257 |
| 11374 | Lcat | NM_008490.2 | chr8:105939550-105943402 |
| 11375 | Lce1a1 | NM_025984.2 | chr3:92646531-92648307 |
| 11376 | Lce1a2 | NM_028625.2 | chr3:92668612-92670315 |
| 11377 | Lce1b | NM_028822.1 | chr3:92655649-92656926 |
| 11378 | Lce1c | NM_028622.2 | chr3:92679246-92680918 |
| 11379 | Lce1d | NM_027137.2 | chr3:92685498-92687210 |
| 11380 | Lce1e | NM_026811.2 | chr3:92707399-92709074 |
| 11381 | Lce1f | NM_026394.3 | chr3:92718695-92720350 |
| 11382 | Lce1g | NM_025413.2 | chr3:92750150-92752338 |
| 11383 | Lce1h | NM_026335.2 | chr3:92763214-92765065 |
| 11384 | Lce1i | NM_029667.2 | chr3:92777209-92778899 |
| 11385 | Lce1j | NM_001281499.1 | chr3:92788844-92790514 |
| 11386 | Lce1k | NM_001254760.1 | chr3:92806290-92807891 |
| 11387 | Lce1l | NM_028628.2 | chr3:92849948-92851286 |
| 11388 | Lce1m | NM_025420.2 | chr3:93017806-93019060 |
| 11389 | Lce3a | NM_001039594.1 | chr3:92925286-92926230 |
| 11390 | Lce3b | NM_025501.3 | chr3:92932978-92934096 |
| 11391 | Lce3c | NM_033175.3 | chr3:92944485-92945730 |
| 11392 | Lce3d | NM_001270426.1 | chr3:92957389-92958574 |
| 11393 | Lce3e | NM_001254725.1 | chr3:92967060-92968281 |
| 11394 | Lce3f | NM_001018079.1 | chr3:92992225-92993426 |

Fig. 26 - 61

| | | | |
|---|---|---|---|
| 11395 | Lce6a | NM_001166172.1 | chr3:92620084-92621660 |
| 11396 | Lck | NM_001162432.1 | chr4:129548343-129568372 |
| 11397 | Lclat1 | NM_001081071.2 | chr17:73107984-73243366 |
| 11398 | Lcmt1 | NM_025304.3 | chr7:123377981-123430358 |
| 11399 | Lcmt2 | NM_177846.3 | chr2:121137291-121140698 |
| 11400 | Lcn10 | NM_178036.4 | chr2:25682725-25686080 |
| 11401 | Lcn11 | NM_001100455.2 | chr2:25777016-25780279 |
| 11402 | Lcn12 | NM_029958.1 | chr2:25490844-25493911 |
| 11403 | Lcn2 | NM_008491.1 | chr2:32384636-32387739 |
| 11404 | Lcn3 | NM_010694.1 | chr2:25765568-25768099 |
| 11405 | Lcn4 | NM_010695.1 | chr2:26667673-26671282 |
| 11406 | Lcn5 | NM_001042630.2 | chr2:25657951-25662230 |
| 11407 | Lcn6 | NM_001276448.1 | chr2:25676785-25681607 |
| 11408 | Lcn8 | NM_033145.1 | chr2:25653117-25656216 |
| 11409 | Lcn9 | NM_029959.2 | chr2:25823152-25825537 |
| 11410 | Lcor | NM_172154.4 | chr19:41549638-41559781 |
| 11411 | Lcorl | NM_001163073.1 | chr5:45730331-45857540 |
| 11412 | Lcp1 | NM_001247984.1 | chr14:75131122-75230842 |
| 11413 | Lcp2 | NM_010696.3 | chr11:34047200-34092280 |
| 11414 | Lct | NM_001081078.2 | chr1:128284755-128328318 |
| 11415 | Lctl | NM_145835.2 | chr9:64117146-64138118 |
| 11416 | Ldb1 | NM_001113408.1 | chr19:46032600-46045211 |
| 11417 | Ldb2 | NM_001077398.2 | chr5:44472132-44799746 |
| 11418 | Ldb3 | NM_001039071.2 | chr14:34526698-34588681 |
| 11419 | Ldha | NM_001136069.2 | chr7:46847081-46855627 |
| 11420 | Ldhal6b | NM_175349.2 | chr17:5417322-5418767 |
| 11421 | Ldhb | NM_008492.3 | chr6:142490248-142507957 |
| 11422 | Ldhc | NM_013580.4 | chr7:46861262-46878142 |
| 11423 | Ldhd | NM_025570.3 | chr8:111626270-111630322 |
| 11424 | Ldlr | NM_001252658.1 | chr9:21723575-21749918 |
| 11425 | Ldlrad1 | NM_001081272.1 | chr4:107209179-107217914 |
| 11426 | Ldlrad2 | NM_001033979.1 | chr4:137570875-137575180 |
| 11427 | Ldlrad3 | NM_001290784.1 | chr2:101950200-102186460 |
| 11428 | Ldlrad4 | NM_172631.3 | chr18:67933256-68255549 |
| 11429 | Ldlrap1 | NM_145554.2 | chr4:134745411-134768004 |
| 11430 | Ldoc1 | NM_001018087.1 | chrX:61710615-61710950 |
| 11431 | Ldoc1l | NM_177630.3 | chr15:84553397-84557823 |
| 11432 | Leap2 | NM_153069.3 | chr11:53422180-53423136 |
| 11433 | Lect1 | NM_010701.3 | chr14:79637692-79662183 |
| 11434 | Lect2 | NM_010702.2 | chr13:56542459-56548538 |
| 11435 | Lef1 | NM_001276402.1 | chr3:131110296-131224357 |
| 11436 | Lefty1 | NM_010094.3 | chr1:180935038-180938401 |
| 11437 | Lefty2 | NM_177099.4 | chr1:180893107-180899107 |
| 11438 | Lekr1 | NM_001037923.4 | chr3:65666227-65686181 |
| 11439 | Lelp1 | NM_027042.1 | chr3:92134993-92142754 |
| 11440 | Lemd1 | NM_001033250.4 | chr1:132191435-132257382 |
| 11441 | Lemd2 | NM_146075.2 | chr17:27189599-27204438 |
| 11442 | Lemd3 | NM_001081193.2 | chr10:120923410-120979330 |
| 11443 | Lenep | NM_020517.4 | chr3:89401895-89402650 |
| 11444 | Leng1 | NM_027203.3 | chr7:3660106-3665840 |
| 11445 | Leng8 | NM_172736.3 | chr7:4137055-4148173 |
| 11446 | Leng9 | NM_175529.3 | chr7:4148182-4149872 |
| 11447 | Leo1 | NM_001039522.1 | chr9:75441523-75466432 |
| 11448 | Lep | NM_008493.3 | chr6:29060220-29073876 |
| 11449 | Lepr | NM_001122899.1 | chr4:101717406-101813667 |
| 11450 | Leprel | NM_001042411.1 | chr4:119233828-119248977 |
| 11451 | Leprel1 | NM_173379.2 | chr16:25960322-26105784 |
| 11452 | Leprel2 | NM_013534.4 | chr6:124841094-124857687 |
| 11453 | Leprel4 | NM_176830.2 | chr11:100408749-100414819 |
| 11454 | Leprot | NM_175036.4 | chr4:101647782-101659358 |
| 11455 | Leprotl1 | NM_026609.2 | chr8:34135571-34146739 |
| 11456 | Letm1 | NM_019694.1 | chr5:33741351-33782704 |
| 11457 | Letm2 | NM_173012.3 | chr8:25578489-25597487 |
| 11458 | Letmd1 | NM_134093.2 | chr15:100469033-100479252 |
| 11459 | Lfng | NM_008494.3 | chr5:140607340-140615545 |
| 11460 | Lgals1 | NM_008495.2 | chr15:78926724-78930465 |
| 11461 | Lgals12 | NM_019516.3 | chr19:7596660-7607176 |
| 11462 | Lgals2 | NM_025622.2 | chr15:78850859-78855529 |
| 11463 | Lgals3 | NM_001145953.1 | chr14:47373859-47386167 |
| 11464 | Lgals3bp | NM_011150.2 | chr11:118392751-118401931 |
| 11465 | Lgals4 | NM_010706.2 | chr7:28833793-28841703 |
| 11466 | Lgals6 | NM_010707.2 | chr7:28834181-28841633 |
| 11467 | Lgals7 | NM_008496.4 | chr7:28864385-28866284 |
| 11468 | Lgals8 | NM_001199043.1 | chr13:12439414-12461738 |
| 11469 | Lgals9 | NM_001159301.1 | chr11:78962978-78984924 |
| 11470 | Lgalsl | NM_172589.2 | chr11:20823354-20831108 |
| 11471 | Lgi1 | NM_020278.2 | chr19:38264781-38308939 |
| 11472 | Lgi2 | NM_144945.3 | chr5:52533516-52566306 |
| 11473 | Lgi3 | NM_145219.4 | chr14:70530820-70538324 |
| 11474 | Lgi4 | NM_144556.2 | chr7:31059934-31070935 |
| 11475 | Lgmn | NM_011175.2 | chr12:102394097-102439697 |
| 11476 | Lgr4 | NM_172671.2 | chr2:109917646-110014257 |
| 11477 | Lgr5 | NM_010195.2 | chr10:115450313-115587780 |
| 11478 | Lgr6 | NM_001033409.3 | chr1:134986352-135105276 |
| 11479 | Lgsn | NM_153601.1 | chr13:31176434-31204725 |
| 11480 | Lhb | NM_008497.2 | chr7:45420945-45421854 |
| 11481 | Lhcgr | NM_013582.2 | chr17:88741548-88791976 |
| 11482 | Lhfp | NM_175386.3 | chr3:53041546-53261679 |
| 11483 | Lhfpl1 | NM_178358.3 | chrX:145290358-145348894 |
| 11484 | Lhfpl2 | NM_172589.2 | chr13:94057795-94195409 |
| 11485 | Lhfpl3 | NM_001081231.2 | chr5:22746192-23275597 |
| 11486 | Lhfpl4 | NM_177763.3 | chr6:113168086-113195384 |
| 11487 | Lhfpl5 | NM_026571.2 | chr17:28575718-28583593 |
| 11488 | Lhpp | NM_029609.1 | chr7:132610642-132706419 |
| 11489 | Lhx1 | NM_008498.2 | chr11:84519378-84525534 |
| 11490 | Lhx1os | NR_038057.1 | chr11:84525659-84535831 |
| 11491 | Lhx2 | NM_001290646.1 | chr2:38339280-38369737 |
| 11492 | Lhx3 | NM_001039653.2 | chr2:26200211-26206575 |
| 11493 | Lhx4 | NM_010712.2 | chr1:155701693-155742027 |
| 11494 | Lhx5 | NM_008499.5 | chr5:120431885-120441457 |
| 11495 | Lhx6 | NM_001083125.1 | chr2:36081952-36105408 |
| 11496 | Lhx8 | NM_010713.2 | chr3:154306293-154330560 |
| 11497 | Lhx9 | NM_001025565.2 | chr1:138825185-138842444 |
| 11498 | Lias | NM_024471.5 | chr5:65391496-65410423 |
| 11499 | Lif | NM_001039537.2 | chr11:4266795-4272514 |
| 11500 | Lifr | NM_001113386.1 | chr15:7129571-7185343 |
| 11501 | Lig1 | NM_001083188.1 | chr7:13279264-13311427 |
| 11502 | Lig3 | NM_001291245.1 | chr11:82781108-82804274 |
| 11503 | Lig4 | NM_176953.3 | chr8:9970019-9976323 |
| 11504 | Lifra5 | NM_001081239.2 | chr7:4237753-4243463 |
| 11505 | Lifra6 | NM_011090.2 | chr7:3908279-3915501 |
| 11506 | Lilrb4 | NM_001291894.1 | chr10:51490897-51496611 |
| 11507 | Lim2 | NM_177693.3 | chr7:43430100-43435991 |
| 11508 | Lima1 | NM_001113545.1 | chr15:99778467-99875456 |
| 11509 | Limch1 | NM_001001980.2 | chr5:66745839-67057159 |
| 11510 | Limd1 | NM_013860.2 | chr9:123478700-123521552 |
| 11511 | Limd2 | NM_172397.3 | chr11:106156255-106160142 |
| 11512 | Lime1 | NM_023684.2 | chr2:181381234-181388628 |
| 11513 | Limk1 | NM_010717.3 | chr5:134656038-134688590 |
| 11514 | Limk2 | NM_001034030.2 | chr11:3343296-3356141 |
| 11515 | Lims1 | NM_001193303.1 | chr10:58394372-58424691 |
| 11516 | Lims2 | NM_144862.3 | chr18:31931506-31958619 |
| 11517 | Lin28a | NM_145833.1 | chr4:134003329-134018816 |
| 11518 | Lin28b | NM_001031772.2 | chr10:45376618-45470201 |
| 11519 | Lin37 | NM_001290569.1 | chr7:30555440-30559646 |
| 11520 | Lin52 | NM_173756.4 | chr12:84451507-84531533 |
| 11521 | Lin54 | NM_001115010.1 | chr5:100442034-100498573 |
| 11522 | Lin7a | NM_001033223.2 | chr10:107271830-107425143 |
| 11523 | Lin7b | NM_011698.1 | chr7:45367890-45370564 |
| 11524 | Lin7c | NM_013699.3 | chr2:109890877-109900936 |
| 11525 | Lin9 | NM_001103182.2 | chr1:180641149-180690687 |
| 11526 | Lincrna-cox2 | NR_110420.1 | chr1:150159042-150164948 |
| 11527 | Lingo1 | NM_181074.4 | chr9:56618474-56685253 |
| 11528 | Lingo2 | NM_001165999.1 | chr4:35706647-38951744 |
| 11529 | Lingo3 | NM_001013758.2 | chr10:80832800-80844039 |
| 11530 | Lingo4 | NM_177250.2 | chr3:94389218-94404501 |
| 11531 | Lins | NM_001191001.1 | chr7:66689888-66717256 |
| 11532 | Lipa | NM_001111100.1 | chr19:34492315-34527474 |
| 11533 | Lipc | NM_008280.2 | chr9:70798127-70934808 |
| 11534 | Lipe | NM_001039507.2 | chr7:25379526-25390112 |
| 11535 | Lipf | NM_026334.3 | chr19:33961247-33976813 |
| 11536 | Lipg | NM_010720.3 | chr18:74939321-74961263 |
| 11537 | Liph | NM_001083894.1 | chr16:21953817-21995542 |
| 11538 | Lipi | NM_001252513.1 | chr16:75540513-75586061 |
| 11539 | Lipk | NM_001205349.1 | chr19:34008253-34047903 |
| 11540 | Lipm | NM_023903.1 | chr19:34100942-34122687 |
| 11541 | Lipn | NM_027340.2 | chr19:34067357-34084918 |
| 11542 | Lipo1 | NM_001013770.3 | chr19:33555280-33590311 |
| 11543 | Lipt1 | NM_001037918.3 | chr1:37872205-37876298 |
| 11544 | Lipt2 | NM_026010.2 | chr7:100159276-100160931 |
| 11545 | Litaf | NM_019980.2 | chr16:10959272-10993121 |
| 11546 | Lix1 | NM_025681.2 | chr17:17402685-17459388 |
| 11547 | Lix1l | NM_001163170.1 | chr3:96601132-96625352 |
| 11548 | Lkaaear1 | NM_199023.3 | chr2:181696794-181698442 |
| 11549 | Llgl1 | NM_001159404.1 | chr11:60699689-60714188 |
| 11550 | Llgl2 | NM_001252532.1 | chr11:115824057-115855780 |
| 11551 | Llph | NM_025431.2 | chr10:120227059-120232070 |
| 11552 | Lman1 | NM_001172062.1 | chr18:65983686-66002635 |
| 11553 | Lman1l | NM_199222.3 | chr9:57607032-57620774 |
| 11554 | Lman2 | NM_025828.3 | chr13:55343832-55362783 |
| 11555 | Lman2l | NM_001013374.2 | chr1:36423185-36445271 |
| 11556 | Lmbr1 | NM_020295.3 | chr5:29229801-29378390 |
| 11557 | Lmbr1l | NM_029098.3 | chr15:98903920-98918098 |
| 11558 | Lmbrd1 | NM_026719.2 | chr1:24678543-24766301 |
| 11559 | Lmbrd2 | NM_177178.3 | chr15:9140569-9197450 |
| 11560 | Lmcd1 | NM_144799.2 | chr6:112273757-112330423 |
| 11561 | Lmf1 | NM_029624.4 | chr17:25579173-25662826 |
| 11562 | Lmf2 | NM_178919.4 | chr15:89351003-89355659 |
| 11563 | Lmln | NM_172823.2 | chr16:33062520-33125659 |
| 11564 | Lmna | NM_001002011.3 | chr3:88481147-88503352 |
| 11565 | Lmnb1 | NM_010721.2 | chr18:56707812-56753424 |
| 11566 | Lmnb2 | NM_010722.5 | chr10:80901362-80918245 |
| 11567 | Lmo1 | NM_057173.3 | chr7:109138564-109170519 |
| 11568 | Lmo2 | NM_001142335.1 | chr2:103970286-103981878 |
| 11569 | Lmo3 | NM_207222.2 | chr6:138364480-138581968 |
| 11570 | Lmo4 | NM_001161769.1 | chr3:144188529-144202396 |
| 11571 | Lmo7 | NM_201529.2 | chr14:101729927-101934693 |
| 11572 | Lmod1 | NM_053106.2 | chr1:135324812-135368065 |
| 11573 | Lmod2 | NM_053098.2 | chr6:24597770-24605414 |
| 11574 | Lmod3 | NM_001081157.1 | chr6:97238527-97252780 |
| 11575 | Lmtk2 | NM_001081109.3 | chr5:144100435-144188204 |
| 11576 | Lmtk3 | NM_001005511.3 | chr7:45783946-45804142 |
| 11577 | Lmx1a | NM_033652.5 | chr1:167689557-167848733 |
| 11578 | Lmx1b | NM_010725.2 | chr2:33564535-33640511 |
| 11579 | Lnp | NM_001110209.1 | chr2:74514836-74578948 |
| 11580 | Lnpep | NM_172827.3 | chr17:17527722-17624489 |
| 11581 | Lnx1 | NM_001159577.1 | chr5:74597103-74702903 |
| 11582 | Lnx2 | NM_080795.4 | chr5:147016654-147076572 |
| 11583 | LOC100038947 | NM_001173459.2 | chr3:15795146-15848487 |
| 11584 | LOC100040786 | NM_001160129.1 | chrY:54185856-66742170 |

Fig. 26 - 62

| | | | |
|---|---|---|---|
| 11585 | LOC100043315 | NR_015482.1 | chr15:95097621-95149318 |
| 11586 | LOC100048884 | NM_001199333.1 | chr4:61670177-61674094 |
| 11587 | LOC100502896 | NM_001277512.1 | chr4:73650909-73657292 |
| 11588 | LOC100503280 | NM_001251890.1 | chrX:74966843-74969125 |
| 11589 | LOC100503496 | NR_040680.1 | chr11:109440077-109453359 |
| 11590 | LOC100503676 | NR_103491.1 | chr8:84913334-84922915 |
| 11591 | LOC100504039 | NR_102724.1 | chrX:53686526-53691325 |
| 11592 | LOC100504608 | NM_001205036.1 | chr10:127032904-127041394 |
| 11593 | LOC100504703 | NR_040660.1 | chr10:127070480-127071101 |
| 11594 | LOC100505025 | NR_105062.1 | chr7:73310379-73315193 |
| 11595 | LOC100861615 | NM_001270812.1 | chr14:6259746-6287250 |
| 11596 | LOC100861978 | NM_001267703.1 | chr4:16836-22237 |
| 11597 | LOC100862015 | NM_001277531.1 | chr4:73635785-73642163 |
| 11598 | LOC100862268 | NR_105029.1 | chr3:127161304-127168290 |
| 11599 | LOC101055769 | NR_105031.1 | chr4:59260050-59269144 |
| 11600 | LOC101055863 | NM_001277487.1 | chr4:73605543-73687560 |
| 11601 | LOC101056043 | NR_105032.1 | chr5:110429874-110431955 |
| 11602 | LOC101056136 | NR_105055.1 | chr14:42254658-42260048 |
| 11603 | LOC101056149 | NR_105041.1 | chr13:34652922-34666774 |
| 11604 | LOC101056236 | NR_105054.1 | chr16:92377070-92382683 |
| 11605 | LOC101243624 | NR_102297.1 | chr3:132842201-132878596 |
| 11606 | LOC101669761 | NR_105513.1 | chr16:31986830-31987791 |
| 11607 | LOC102308570 | NM_001286103.1 | chr19:8883877-8890759 |
| 11608 | LOC102631757 | NR_110502.1 | chr17:31152751-31163052 |
| 11609 | LOC102632423 | NR_110507.1 | chr6:118300166-118308719 |
| 11610 | LOC102632430 | NR_110508.1 | chr16:22874982-22894386 |
| 11611 | LOC102633035 | NR_110509.1 | chr9:101342193-101348017 |
| 11612 | LOC102633315 | NR_110510.1 | chr8:25548672-25556083 |
| 11613 | LOC102634101 | NR_110511.1 | chr10:67005074-67041326 |
| 11614 | LOC102634401 | NR_110447.1 | chr2:74752683-74753742 |
| 11615 | LOC102634431 | NR_110513.1 | chr9:8644077-8740988 |
| 11616 | LOC102634753 | NR_110516.1 | chr3:99049821-99053742 |
| 11617 | LOC102635087 | NR_110517.1 | chr9:71168775-71208122 |
| 11618 | LOC102636514 | NR_110474.1 | chr8:57304413-57320859 |
| 11619 | LOC106740 | NR_027905.1 | chr17:14947735-14948823 |
| 11620 | LOC171588 | NR_038065.1 | chr2:144465175-144466732 |
| 11621 | LOC381967 | NR_103487.1 | chr7:99260480-99267218 |
| 11622 | LOC666331 | NM_001256318.1 | chr11:101610699-101615956 |
| 11623 | Loh12cr1 | NM_001170479.1 | chr6:134639511-134711184 |
| 11624 | Lonp1 | NM_028782.2 | chr17:56614297-56626903 |
| 11625 | Lonp2 | NM_001168591.1 | chr8:86651568-86716638 |
| 11626 | Lonrf1 | NM_001161150.1 | chr8:36216063-36249516 |
| 11627 | Lonrf2 | NM_001029878.1 | chr1:38794508-38821215 |
| 11628 | Lonrf3 | NM_028894.1 | chrX:36328408-36366856 |
| 11629 | Lor | NM_008508.2 | chr3:92080270-92083142 |
| 11630 | Lox | NM_001286181.1 | chr18:52516059-52529721 |
| 11631 | Loxhd1 | NM_172834.2 | chr18:77281957-77442257 |
| 11632 | Loxl1 | NM_010729.3 | chr9:58287722-58313212 |
| 11633 | Loxl2 | NM_033325.2 | chr14:69609475-69695834 |
| 11634 | Loxl3 | NM_013586.4 | chr6:83084223-83052564 |
| 11635 | Loxl4 | NM_001164311.1 | chr19:42592278-42612806 |
| 11636 | Lpar1 | NM_001290486.1 | chr4:58435251-58499403 |
| 11637 | Lpar2 | NM_020028.3 | chr8:69822564-69831102 |
| 11638 | Lpar3 | NM_022983.4 | chr3:146220960-146286214 |
| 11639 | Lpar4 | NM_175271.4 | chrX:106920624-106933899 |
| 11640 | Lpar5 | NM_001163268.1 | chr6:125071276-125082472 |
| 11641 | Lpar6 | NM_175116.4 | chr14:73237890-73240358 |
| 11642 | Lpcat1 | NM_145376.5 | chr13:73467382-73514538 |
| 11643 | Lpcat2 | NM_173014.1 | chr8:92855349-92919279 |
| 11644 | Lpcat2b | NM_027599.3 | chr5:107431548-107435039 |
| 11645 | Lpcat3 | NM_145130.2 | chr6:124663103-124704716 |
| 11646 | Lpcat4 | NM_207206.2 | chr2:112239840-112247111 |
| 11647 | Lpgat1 | NM_001134829.1 | chr1:191718394-191784257 |
| 11648 | Lphn1 | NM_181039.2 | chr8:83900097-83941954 |
| 11649 | Lphn2 | NM_001081298.1 | chr3:148815585-148954635 |
| 11650 | Lphn3 | NM_198702.2 | chr5:81021592-81795730 |
| 11651 | Lpin1 | NM_001130412.1 | chr12:16535668-16589770 |
| 11652 | Lpin2 | NM_001164885.1 | chr17:71204653-71249818 |
| 11653 | Lpin3 | NM_001199118.1 | chr2:160888167-160906000 |
| 11654 | Lpl | NM_008509.2 | chr8:68880554-68906932 |
| 11655 | Lpo | NM_080420.2 | chr11:87806427-87826114 |
| 11656 | Lpp | NM_001145952.1 | chr16:24448090-24992578 |
| 11657 | Lpxn | NM_134152.3 | chr19:12798608-12833808 |
| 11658 | Lrat | NM_023624.4 | chr3:82892581-82903974 |
| 11659 | Lrba | NM_001077687.1 | chr3:86224689-86746710 |
| 11660 | Lrch1 | NM_001164574.1 | chr14:74672-74947877 |
| 11661 | Lrch2 | NM_001081173.1 | chrX:147471693-147554081 |
| 11662 | Lrch3 | NM_001081255.1 | chr16:32914099-33016029 |
| 11663 | Lrch4 | NM_001188626.1 | chr5:137629122-137641099 |
| 11664 | Lrcol1 | NM_001310709.1 | chr5:110344507-110356094 |
| 11665 | Lrfn1 | NM_001141921.1 | chr7:28452237-28467548 |
| 11666 | Lrfn2 | NM_027452.3 | chr17:48932581-49097590 |
| 11667 | Lrfn3 | NM_175478.2 | chr7:30355513-30362772 |
| 11668 | Lrfn4 | NM_153888.4 | chr19:4611783-4615667 |
| 11669 | Lrfn5 | NM_178714.5 | chr12:61523166-61845258 |
| 11670 | Lrg1 | NM_029796.2 | chr17:56119677-56121946 |
| 11671 | Lrguk | NM_028886.1 | chr6:34029447-34134034 |
| 11672 | Lrif1 | NM_001039478.1 | chr3:106684986-106736576 |
| 11673 | Lrig1 | NM_008377.2 | chr6:94604528-94700145 |
| 11674 | Lrig2 | NM_001025067.2 | chr3:104453982-104511918 |
| 11675 | Lrig3 | NM_177152.5 | chr10:125966218-126015359 |
| 11676 | Lrit1 | NM_146245.2 | chr14:37054829-37064938 |
| 11677 | Lrit2 | NM_173418.3 | chr17:57068048-37073735 |
| 11678 | Lrit3 | NM_001287224.1 | chr3:129788290-129804030 |
| 11679 | Lrmp | NM_001281980.1 | chr6:145115635-145174928 |

| | | | |
|---|---|---|---|
| 11680 | Lrp1 | NM_008512.2 | chr10:127538157-127621148 |
| 11681 | Lrp10 | NM_022993.3 | chr14:54464146-54470291 |
| 11682 | Lrp11 | NM_172784.3 | chr10:7589799-7625477 |
| 11683 | Lrp12 | NM_172814.3 | chr15:39870602-39943757 |
| 11684 | Lrp1b | NM_053011.2 | chr2:40596772-42653598 |
| 11685 | Lrp2 | NM_001081088.1 | chr2:69424334-69586067 |
| 11686 | Lrp2bp | NM_026278.3 | chr8:46010601-46029476 |
| 11687 | Lrp3 | NM_001024707.2 | chr7:35200877-35215345 |
| 11688 | Lrp4 | NM_001145857.1 | chr2:91457530-91479287 |
| 11689 | Lrp5 | NM_008513.3 | chr19:3584824-3686564 |
| 11690 | Lrp6 | NM_008514.4 | chr6:134446477-134566913 |
| 11691 | Lrp8 | NM_001080926.1 | chr4:107802258-107876840 |
| 11692 | Lrpap1 | NM_013587.2 | chr5:35091565-35105697 |
| 11693 | Lrpprc | NM_028233.2 | chr17:84705246-84790786 |
| 11694 | Lrr1 | NM_001081406.1 | chr12:69168813-69179010 |
| 11695 | Lrrc1 | NM_001146048.1 | chr9:77430822-77544852 |
| 11696 | Lrrc10 | NM_146242.2 | chr10:117045340-117046768 |
| 11697 | Lrrc10b | NM_001111140.2 | chr19:10455370-10457447 |
| 11698 | Lrrc14 | NM_145471.2 | chr15:76716739-76715091 |
| 11699 | Lrrc14b | NM_001033042.3 | chr13:74359581-74364000 |
| 11700 | Lrrc15 | NM_028973.2 | chr16:30269301-30283254 |
| 11701 | Lrrc16a | NM_026825.3 | chr13:24012483-24280790 |
| 11702 | Lrrc16b | NM_001024645.1 | chr14:55491092-55508264 |
| 11703 | Lrrc17 | NM_028977.1 | chr5:21543526-21575902 |
| 11704 | Lrrc18 | NM_001146021.1 | chr14:32991381-33009398 |
| 11705 | Lrrc19 | NM_175305.4 | chr4:94636659-94650144 |
| 11706 | Lrrc2 | NM_028838.2 | chr9:110951544-110984064 |
| 11707 | Lrrc20 | NM_153542.1 | chr10:61475832-61582228 |
| 11708 | Lrrc23 | NM_001302555.1 | chr6:124769869-124780341 |
| 11709 | Lrrc24 | NM_198119.2 | chr15:76715275-76722173 |
| 11710 | Lrrc25 | NM_153074.3 | chr8:70616843-70620850 |
| 11711 | Lrrc26 | NM_146117.2 | chr2:25289910-25291193 |
| 11712 | Lrrc27 | NM_001143755.1 | chr7:139213274-139229012 |
| 11713 | Lrrc28 | NM_027413.1 | chr7:67594398-67645236 |
| 11714 | Lrrc29 | NM_174449.3 | chr8:105312339-105326276 |
| 11715 | Lrrc3 | NM_145152.4 | chr10:77897575-77902536 |
| 11716 | Lrrc30 | NM_001033340.3 | chr17:67630964-67632723 |
| 11717 | Lrrc32 | NM_001113379.1 | chr7:98494221-98501830 |
| 11718 | Lrrc34 | NM_027941.1 | chr3:30624266-30647818 |
| 11719 | Lrrc36 | NM_001033371.3 | chr8:105427639-105464086 |
| 11720 | Lrrc38 | NM_001162983.1 | chr4:143349749-143371028 |
| 11721 | Lrrc39 | NM_027321.3 | chr3:116562972-116573112 |
| 11722 | Lrrc3b | NM_146052.4 | chr14:15357515-15438987 |
| 11723 | Lrrc4 | NM_138682.2 | chr6:28828125-28831747 |
| 11724 | Lrrc40 | NM_001289524.1 | chr3:158036681-158067090 |
| 11725 | Lrrc41 | NM_153521.2 | chr4:116075268-116097109 |
| 11726 | Lrrc42 | NM_029985.2 | chr4:107233513-107253533 |
| 11727 | Lrrc43 | NM_001034461.3 | chr5:123489324-123508205 |
| 11728 | Lrrc45 | NM_153545.2 | chr11:120713952-120721127 |
| 11729 | Lrrc46 | NM_027026.2 | chr11:97034601-97041369 |
| 11730 | Lrrc47 | NM_201226.1 | chr4:154011802-154021512 |
| 11731 | Lrrc48 | NM_029044.2 | chr11:60353379-60394333 |
| 11732 | Lrrc49 | NM_001146046.1 | chr9:60587234-60688134 |
| 11733 | Lrrc4b | NM_198250.1 | chr7:44442486-44463344 |
| 11734 | Lrrc4c | NM_001289742.1 | chr2:96318168-97631664 |
| 11735 | Lrrc51 | NM_001162973.1 | chr7:101912988-101933857 |
| 11736 | Lrrc52 | NM_001013382.2 | chr1:167445674-167466780 |
| 11737 | Lrrc55 | NM_001033346.2 | chr2:85188070-85196699 |
| 11738 | Lrrc56 | NM_001172064.1 | chr7:141194129-141210055 |
| 11739 | Lrrc57 | NM_001159609.1 | chr2:120604237-120609508 |
| 11740 | Lrrc58 | NM_177093.3 | chr16:37868399-37888857 |
| 11741 | Lrrc59 | NM_133807.1 | chr11:94629823-94645216 |
| 11742 | Lrrc6 | NM_019457.2 | chr15:66379857-66500910 |
| 11743 | Lrrc61 | NM_001110160.1 | chr6:48554798-48570722 |
| 11744 | Lrrc63 | NM_027581.1 | chr14:75084302-75130883 |
| 11745 | Lrrc66 | NM_153568.1 | chr5:73608641-73632421 |
| 11746 | Lrrc68 | NM_028499.2 | chr4:14665753-14796052 |
| 11747 | Lrrc7 | NM_001081358.2 | chr3:158082894-158562221 |
| 11748 | Lrrc71 | NM_028971.1 | chr3:87736922-87748623 |
| 11749 | Lrrc72 | NM_001177877.1 | chr12:36209562-36253398 |
| 11750 | Lrrc73 | NM_001111142.1 | chr17:46254164-46257316 |
| 11751 | Lrrc74 | NM_001195767.1 | chr12:86734368-86763795 |
| 11752 | Lrrc75a | NM_198861.1 | chr11:62604883-62648523 |
| 11753 | Lrrc75b | NM_198860.2 | chr10:75550124-75560330 |
| 11754 | Lrrc8a | NM_177725.4 | chr2:30237768-30263790 |
| 11755 | Lrrc8b | NM_001033550.2 | chr5:105415774-105486189 |
| 11756 | Lrrc8c | NM_133897.2 | chr5:105519470-105608954 |
| 11757 | Lrrc8d | NM_001122768.1 | chr5:105699868-105815215 |
| 11758 | Lrrc8e | NM_028175.2 | chr8:4226826-4237470 |
| 11759 | Lrrc9 | NM_001142728.1 | chr12:72441856-72510565 |
| 11760 | Lrrcc1 | NM_001163579.1 | chr3:14533787-14568303 |
| 11761 | Lrrd1 | NM_172879.3 | chr5:3845172-3866596 |
| 11762 | Lrrfip1 | NM_001111311.1 | chr1:91053443-91117322 |
| 11763 | Lrrfip2 | NM_001164838.1 | chr9:111118110-111125668 |
| 11764 | Lrriq1 | NM_001163559.1 | chr10:103063197-103236322 |
| 11765 | Lrriq3 | NM_028938.2 | chr3:155093433-155194278 |
| 11766 | Lrriq4 | NM_001290510.1 | chr3:30647885-30672431 |
| 11767 | Lrrk1 | NM_146191.3 | chr7:66258746-66388341 |
| 11768 | Lrrk2 | NM_025730.3 | chr15:91673223-91816124 |
| 11769 | Lrrn1 | NM_008516.2 | chr6:107529725-107570228 |
| 11770 | Lrrn2 | NM_010732.4 | chr1:132880354-132940005 |
| 11771 | Lrrn3 | NM_001271708.1 | chr12:41451667-41486057 |
| 11772 | Lrrn4 | NM_177303.4 | chr2:132868515-132880862 |
| 11773 | Lrrn4cl | NM_001013019.2 | chr19:8850784-8853909 |
| 11774 | Lrrtm1 | NM_028880.3 | chr6:77242716-77245517 |

Fig. 26 - 63

| | | | |
|---|---|---|---|
| 11775 | Lrrtm2 | NM_178005.4 | chr18:35209005-35215024 |
| 11776 | Lrrtm3 | NM_178678.4 | chr10:63928496-64096255 |
| 11777 | Lrrtm4 | NM_001134743.1 | chr6:80018876-80810143 |
| 11778 | Lrsam1 | NM_199302.2 | chr2:32925214-32961255 |
| 11779 | Lrtm1 | NM_176920.4 | chr14:29018207-29033642 |
| 11780 | Lrtm2 | NM_001172207.1 | chr6:119315132-119329204 |
| 11781 | Lrwd1 | NM_027891.4 | chr5:136123065-136136074 |
| 11782 | Lsamp | NM_175548.3 | chr16:41533341-42146213 |
| 11783 | Lsg1 | NM_178069.5 | chr16:30561368-30587589 |
| 11784 | Lsm1 | NM_026032.1 | chr8:25785590-25803975 |
| 11785 | Lsm10 | NM_001163266.1 | chr4:126096652-126098584 |
| 11786 | Lsm11 | NM_028185.2 | chr11:45928268-45944935 |
| 11787 | Lsm12 | NM_172947.3 | chr11:102163488-102185256 |
| 11788 | Lsm14a | NM_025948.2 | chr7:34344719-34389540 |
| 11789 | Lsm14b | NM_177727.4 | chr2:180024986-180035461 |
| 11790 | Lsm2 | NM_001110101.2 | chr17:34981853-34985893 |
| 11791 | Lsm3 | NM_026309.2 | chr6:91516034-91522620 |
| 11792 | Lsm4 | NM_015816.4 | chr8:70673230-70678752 |
| 11793 | Lsm5 | NM_025520.3 | chr6:56701062-56704699 |
| 11794 | Lsm6 | NM_001191004.1 | chr8:78804867-78821152 |
| 11795 | Lsm7 | NM_025349.2 | chr10:80852824-80855209 |
| 11796 | Lsm8 | NM_139939.1 | chr6:18848634-18854052 |
| 11797 | Lsmem1 | NM_001033437.2 | chr12:40176385-40199315 |
| 11798 | Lsp1 | NM_001136071.2 | chr7:142460811-142494868 |
| 11799 | Lsr | NM_001164184.1 | chr7:30957769-30973469 |
| 11800 | Lss | NM_146006.2 | chr10:76531804-76557139 |
| 11801 | Lst1 | NM_010734.2 | chr17:35185094-35188440 |
| 11802 | Lta | NM_010735.2 | chr17:35203164-35205351 |
| 11803 | Lta4h | NM_008517.2 | chr10:93453395-93484896 |
| 11804 | Ltb | NM_008518.2 | chr17:35194506-35196305 |
| 11805 | Ltb4r1 | NM_008519.3 | chr14:55765961-55768492 |
| 11806 | Ltb4r2 | NM_020490.2 | chr14:55761427-55763229 |
| 11807 | Ltbp1 | NM_019919.3 | chr17:75005528-75392967 |
| 11808 | Ltbp2 | NM_013589.3 | chr12:84783211-84876495 |
| 11809 | Ltbp3 | NM_008520.2 | chr19:5740903-5758532 |
| 11810 | Ltbp4 | NM_001113549.1 | chr7:27305140-27333648 |
| 11811 | Ltbr | NM_010736.3 | chr6:125306570-125313870 |
| 11812 | Ltc4s | NM_008521.2 | chr11:50236460-50238532 |
| 11813 | Ltf | NM_008522.3 | chr9:111019291-111042766 |
| 11814 | Ltk | NM_008523.2 | chr2:119751325-119758525 |
| 11815 | Ltn1 | NM_001081068.1 | chr16:87376650-87432606 |
| 11816 | Ltv1 | NM_181470.4 | chr10:13178637-13193157 |
| 11817 | Luc7l | NM_025881.3 | chr17:26252909-26280730 |
| 11818 | Luc7l2 | NM_001170848.1 | chr6:38551443-38609470 |
| 11819 | Luc7l3 | NM_026313.3 | chr11:94291138-94321911 |
| 11820 | Lum | NM_008524.2 | chr10:97565500-97572703 |
| 11821 | Lurap1 | NM_026547.1 | chr4:116136727-116144616 |
| 11822 | Lurap1l | NM_026821.5 | chr4:80910685-80954301 |
| 11823 | Luzp1 | NM_024452.2 | chr4:136469760-136549318 |
| 11824 | Luzp2 | NM_178705.5 | chr7:54835244-55268888 |
| 11825 | Luzp4 | NM_001114383.1 | chrX:148882575-148924139 |
| 11826 | Lxn | NM_016753.4 | chr3:67457998-67463907 |
| 11827 | Ly6a | NM_001271416.1 | chr15:74994876-74998031 |
| 11828 | Ly6c1 | NM_001252055.1 | chr15:75045014-75048837 |
| 11829 | Ly6c2 | NM_001099217.1 | chr15:75108160-75111949 |
| 11830 | Ly6d | NM_010741.2 | chr15:74762055-74763567 |
| 11831 | Ly6e | NM_001164036.1 | chr15:74955070-74959905 |
| 11832 | Ly6f | NM_008530.2 | chr15:75268420-75272234 |
| 11833 | Ly6g5b | NM_148939.2 | chr17:35113945-35115400 |
| 11834 | Ly6g5c | NM_148947.1 | chr17:35108299-35111953 |
| 11835 | Ly6g6c | NM_023463.3 | chr17:35067324-35070048 |
| 11836 | Ly6g6d | NM_033478.2 | chr17:35071347-35074464 |
| 11837 | Ly6g6e | NM_027366.1 | chr17:35076941-35078804 |
| 11838 | Ly6g6f | NM_001163192.1 | chr17:35080537-35085595 |
| 11839 | Ly6h | NM_001135668.1 | chr15:75564744-75566856 |
| 11840 | Ly6i | NM_020498.2 | chr15:74979811-74983430 |
| 11841 | Ly6k | NM_029627.2 | chr15:74796873-74799968 |
| 11842 | Ly75 | NM_013825.3 | chr2:60293759-60383231 |
| 11843 | Ly86 | NM_010745.2 | chr13:37345344-37419036 |
| 11844 | Ly9 | NM_001177968.1 | chr1:171588612-171607410 |
| 11845 | Ly96 | NM_001159711.1 | chr1:16688455-16709605 |
| 11846 | Lyar | NM_025281.3 | chr5:38220481-38234306 |
| 11847 | Lyg1 | NM_027111.3 | chr1:37946737-37957759 |
| 11848 | Lyg2 | NM_001033427.3 | chr1:37905922-37916493 |
| 11849 | Lyl1 | NM_008535.2 | chr8:84701456-84704716 |
| 11850 | Lyn | NM_001111096.1 | chr4:3678120-3791612 |
| 11851 | Lynx1 | NM_011838.4 | chr15:74747855-74752979 |
| 11852 | Lypd1 | NM_145100.4 | chr1:125867621-125912214 |
| 11853 | Lypd2 | NM_026671.1 | chr15:74732251-74734313 |
| 11854 | Lypd3 | NM_133743.1 | chr7:24636569-24641118 |
| 11855 | Lypd4 | NM_182785.3 | chr7:24864619-24869691 |
| 11856 | Lypd5 | NM_029806.1 | chr7:24349223-24353833 |
| 11857 | Lypd6 | NM_177139.5 | chr2:50066428-50193569 |
| 11858 | Lypd6b | NM_027990.3 | chr2:49787685-49948846 |
| 11859 | Lypd8 | NM_001083884.1 | chr11:58379031-58390541 |
| 11860 | Lypla1 | NM_008866.2 | chr1:4807892-4846735 |
| 11861 | Lypla2 | NM_011942.1 | chr4:135968224-135972594 |
| 11862 | Lyplal1 | NM_146106.2 | chr1:186087731-186117310 |
| 11863 | Lyrm1 | NM_001285959.1 | chr7:119895860-119916756 |
| 11864 | Lyrm2 | NM_175364.4 | chr4:32800258-32802254 |
| 11865 | Lyrm4 | NM_201358.2 | chr13:35978796-36117357 |
| 11866 | Lyrm5 | NM_001163628.1 | chr6:145211133-145216542 |
| 11867 | Lyrm7 | NM_029327.3 | chr11:54839288-54860591 |
| 11868 | Lyrm7os | NR_040284.1 | chr11:54819918-54824967 |
| 11869 | Lyrm9 | NM_001076681.2 | chr11:78826594-78843899 |
| 11870 | Lysmd1 | NM_153121.2 | chr3:95134087-95139525 |
| 11871 | Lysmd2 | NM_027309.2 | chr9:75625731-75637773 |
| 11872 | Lysmd3 | NM_030257.1 | chr13:81657805-81671890 |
| 11873 | Lysmd4 | NM_001191051.1 | chr7:67222615-67228468 |
| 11874 | Lyst | NM_010748.2 | chr13:13590408-13777440 |
| 11875 | Lyve1 | NM_053247.4 | chr7:110850606-110862953 |
| 11876 | Lyz1 | NM_013590.4 | chr10:117287794-117292868 |
| 11877 | Lyz2 | NM_017372.3 | chr10:117277540-117282272 |
| 11878 | Lyzl1 | NM_026092.3 | chr18:4165831-4182236 |
| 11879 | Lyzl4 | NM_026915.2 | chr9:121577842-121641566 |
| 11880 | Lyzl4os | NR_040740.1 | chr9:121587019-121614255 |
| 11881 | Lyzl6 | NM_027083.1 | chr11:103631074-103638874 |
| 11882 | Lzic | NM_026963.5 | chr4:149485332-149496667 |
| 11883 | Lztfl1 | NM_033322.2 | chr9:123697592-123717557 |
| 11884 | Lrrtr1 | NM_025808.3 | chr16:17508970-17526330 |
| 11885 | Lzts1 | NM_199364.2 | chr8:69135502-69140953 |
| 11886 | Lzts2 | NM_001130525.1 | chr19:45015209-45027104 |
| 11887 | Lzts3 | NM_001291027.1 | chr2:130632764-130642844 |
| 11888 | M1ap | NM_033079.2 | chr8:82946921-83030309 |
| 11889 | M6pr | NM_010749.6 | chr6:122309009-122317677 |
| 11890 | Maats1 | NM_001081025.1 | chr18:38297753-38341860 |
| 11891 | Mab21l1 | NM_010750.3 | chr3:55782509-55785287 |
| 11892 | Mab21l2 | NM_011839.3 | chr3:86545580-86548283 |
| 11893 | Mab21l3 | NM_172295.4 | chr3:101813075-101836223 |
| 11894 | Macc1 | NM_001163136.1 | chr12:119443409-119466932 |
| 11895 | Macf1 | NM_001199136.1 | chr4:123349632-123684360 |
| 11896 | Macrod1 | NM_134147.4 | chr19:7056767-7198062 |
| 11897 | Macrod2 | NM_001013802.3 | chr2:140395429-142390050 |
| 11898 | Mad1l1 | NM_010752.3 | chr5:140008688-140321552 |
| 11899 | Mad2l1 | NM_019499.4 | chr6:66535467-66540991 |
| 11900 | Mad2l1bp | NM_025649.3 | chr17:46147384-46153551 |
| 11901 | Mad2l2 | NM_027985.3 | chr4:148140489-148145704 |
| 11902 | Madcam1 | NM_013591.2 | chr10:79664573-79668536 |
| 11903 | Madd | NM_001177719.1 | chr2:91137359-91183047 |
| 11904 | Maea | NM_021500.2 | chr5:33335571-33373294 |
| 11905 | Mael | NM_175296.4 | chr1:166261384-166238744 |
| 11906 | Maf | NM_001025577.2 | chr8:115703252-115706894 |
| 11907 | Maf1 | NM_001164607.1 | chr15:76351293-76354378 |
| 11908 | Mafa | NM_194350.1 | chr15:75746842-75747922 |
| 11909 | Mafb | NM_010658.3 | chr2:160363676-160367065 |
| 11910 | Maff | NM_010755.4 | chr15:79347519-79359076 |
| 11911 | Mafg | NM_010756.3 | chr11:120628350-120633547 |
| 11912 | Mafk | NM_010757.2 | chr5:139791535-139802652 |
| 11913 | Mag | NM_010758.2 | chr7:30899182-30914832 |
| 11914 | Magea1 | NM_020015.2 | chrX:155088518-155089790 |
| 11915 | Magea10 | NM_001085506.1 | chrX:72381869-72386858 |
| 11916 | Magea2 | NM_020016.1 | chrX:155027200-155033292 |
| 11917 | Magea3 | NM_020017.2 | chrX:154948462-154949569 |
| 11918 | Magea4 | NM_020280.2 | chrX:72222016-72222964 |
| 11919 | Magea5 | NM_020018.1 | chrX:155053060-155061553 |
| 11920 | Magea6 | NM_020019.3 | chrX:154924011-154926115 |
| 11921 | Magea8 | NM_020020.4 | chrX:154985774-154995850 |
| 11922 | Mageb1 | NM_010759.1 | chrX:91331754-92016333 |
| 11923 | Mageb16 | NM_001113734.1 | chrX:79623230-79635582 |
| 11924 | Mageb16-ps1 | NR_033647.1 | chrX:144552757-144556239 |
| 11925 | Mageb18 | NM_173783.3 | chrX:92118878-92599572 |
| 11926 | Mageb2 | NM_031171.1 | chrX:91331904-92016183 |
| 11927 | Mageb3 | NM_008545.2 | chr2:121953770-121956092 |
| 11928 | Mageb4 | NM_001033492.2 | chr8:86256255-86256219 |
| 11929 | Mageb5 | NM_028847.1 | chrX:91779607-91782976 |
| 11930 | Maged1 | NM_019791.2 | chrX:94535473-94542074 |
| 11931 | Maged2 | NM_001199246.1 | chrX:150806420-150813703 |
| 11932 | Magee1 | NM_053201.4 | chrX:105120377-105123961 |
| 11933 | Magee2 | NM_053206.2 | chrX:104854951-104857267 |
| 11934 | Mageh1 | NM_023788.3 | chrX:153036165-153037563 |
| 11935 | Magel2 | NM_013779.2 | chr7:62376978-62381640 |
| 11936 | Magi1 | NM_001029850.4 | chr6:93675452-94283917 |
| 11937 | Magi2 | NM_001170745.1 | chr5:19907517-20704792 |
| 11938 | Magi3 | NM_001159354.1 | chr3:104013264-104220406 |
| 11939 | Magix | NM_018832.2 | chrX:7673165-7681089 |
| 11940 | Magoh | NM_001282737.1 | chr4:107879754-107887424 |
| 11941 | Magohb | NM_025564.2 | chr6:131284388-131293244 |
| 11942 | Magt1 | NM_001190409.1 | chrX:105968084-106011899 |
| 11943 | Mak | NM_001145802.1 | chr13:41025119-41079706 |
| 11944 | Mak16 | NM_026453.3 | chr8:31159467-31168724 |
| 11945 | Mal | NM_001171187.1 | chr2:127633225-127656695 |
| 11946 | Mal2 | NM_178920.4 | chr15:54571365-54602846 |
| 11947 | Malat1 | NR_002847.2 | chr19:5795689-5802671 |
| 11948 | Mall | NM_145532.3 | chr2:127704389-127729897 |
| 11949 | Malsu1 | NM_029353.1 | chr6:49073794-49084717 |
| 11950 | Malt1 | NM_172833.2 | chr18:65430996-65478792 |
| 11951 | Mamdc2 | NM_174857.3 | chr19:23302608-23448322 |
| 11952 | Mamdc4 | NM_001081199.1 | chr2:25563114-25571316 |
| 11953 | Maml1 | NM_175334.3 | chr11:50255634-50292336 |
| 11954 | Maml2 | NM_001013813.3 | chr9:13619988-13709533 |
| 11955 | Maml3 | NM_001004176.2 | chr3:51687612-52105006 |
| 11956 | Mamld1 | NM_001081354.2 | chrX:71050255-71154717 |
| 11957 | Mamstr | NM_172418.2 | chr7:45639976-45645768 |
| 11958 | Man1a | NM_008548.4 | chr10:53906032-54075796 |
| 11959 | Man1a2 | NM_010763.2 | chr3:100562204-100685473 |
| 11960 | Man1b1 | NM_001029983.2 | chr2:25332742-25352213 |
| 11961 | Man1c1 | NM_207237.3 | chr4:134561689-134704290 |
| 11962 | Man2a1 | NM_008549.2 | chr17:64601648-64755110 |
| 11963 | Man2a2 | NM_172303.4 | chr7:80349096-80371375 |
| 11964 | Man2b1 | NM_010764.2 | chr8:85083268-85098739 |

Fig. 26 - 64

| | | | |
|---|---|---|---|
| 11965 | Man2b2 | NM_008550.2 | chr5:36806812-36830649 |
| 11966 | Man2c1 | NM_028636.2 | chr9:57180776-57142210 |
| 11967 | Man2c1os | NR_102289.1 | chr9:57129981-57131290 |
| 11968 | Manba | NM_027288.3 | chr3:135485610-135571403 |
| 11969 | Manbal | NM_026968.3 | chr2:157367593-157396763 |
| 11970 | Manea | NM_172865.2 | chr4:26324508-26346652 |
| 11971 | Maneal | NM_001007573.2 | chr4:124855238-124862171 |
| 11972 | Manf | NM_029103.3 | chr9:106887414-106891938 |
| 11973 | Manr | NR_110437.1 | chr3:29891016-29924191 |
| 11974 | Mansc1 | NM_026345.4 | chr6:134609206-134632488 |
| 11975 | Mansc4 | NM_001034903.3 | chr6:147075061-147087032 |
| 11976 | Maoa | NM_173740.3 | chrX:16619697-16687812 |
| 11977 | Maob | NM_172778.2 | chrX:16709280-16817366 |
| 11978 | Map10 | NM_028908.3 | chr8:125669817-125673365 |
| 11979 | Map1a | NM_001173506.1 | chr2:121295453-121310832 |
| 11980 | Map1b | NM_008634.2 | chr13:99421463-99516602 |
| 11981 | Map1lc3a | NM_025735.3 | chr2:155276363-155278073 |
| 11982 | Map1lc3b | NM_026160.4 | chr8:121590467-121598047 |
| 11983 | Map1s | NM_173013.3 | chr8:70905973-70917529 |
| 11984 | Map2 | NM_001039934 | chr1:66175328-66442583 |
| 11985 | Map2k1 | NM_008927 | chr9:64185792-64253605 |
| 11986 | Map2k2 | NM_023138.1 | chr10:81105946-81124697 |
| 11987 | Map2k3 | NM_008928.4 | chr11:60932056-60952803 |
| 11988 | Map2k3os | NR_027800.1 | chr11:60920940-60931867 |
| 11989 | Map2k4 | NM_009157.5 | chr11:65688243-65788297 |
| 11990 | Map2k5 | NM_011840.2 | chr9:63163769-63377852 |
| 11991 | Map2k6 | NM_011943.2 | chr11:110399121-110513637 |
| 11992 | Map2k7 | NM_001042557.2 | chr8:4238739-4247892 |
| 11993 | Map3k1 | NM_011945.2 | chr13:111746434-111808983 |
| 11994 | Map3k10 | NM_001290528.1 | chr7:27656375-27674607 |
| 11995 | Map3k11 | NM_022012.3 | chr19:5689130-5702864 |
| 11996 | Map3k12 | NM_001163643.1 | chr15:102497646-102517004 |
| 11997 | Map3k13 | NM_172821.3 | chr16:21891968-21931877 |
| 11998 | Map3k14 | NM_016896.3 | chr11:103219763-103267401 |
| 11999 | Map3k15 | NM_001163085.2 | chrX:159988432-160123351 |
| 12000 | Map3k19 | NM_011737.3 | chr1:127815270-127840290 |
| 12001 | Map3k2 | NM_011946.3 | chr18:32163088-32236751 |
| 12002 | Map3k3 | NM_011947.3 | chr11:106084901-106155434 |
| 12003 | Map3k4 | NM_011948.4 | chr17:12227620-12318660 |
| 12004 | Map3k5 | NM_008580.4 | chr10:19934525-20142750 |
| 12005 | Map3k6 | NM_016693.5 | chr4:133240817-133252928 |
| 12006 | Map3k7 | NM_009316.1 | chr4:31964106-32023466 |
| 12007 | Map3k7cl | NM_144854.2 | chr16:87553329-87595336 |
| 12008 | Map3k8 | NM_007746.2 | chr18:4331326-4352953 |
| 12009 | Map3k9 | NM_001165567.2 | chr12:81714949-81781170 |
| 12010 | Map4 | NM_001205130.1 | chr9:109931773-110083954 |
| 12011 | Map4k1 | NM_008279.2 | chr7:28982853-29003278 |
| 12012 | Map4k2 | NM_001291787.1 | chr19:6341159-6355619 |
| 12013 | Map4k3 | NM_001290345.1 | chr17:80580612-80728025 |
| 12014 | Map4k4 | NM_001252200.1 | chr1:39990912-40026310 |
| 12015 | Map4k5 | NM_201519.2 | chr12:69803756-69893163 |
| 12016 | Map6 | NM_001043355.2 | chr7:99268345-99337137 |
| 12017 | Map6d1 | NM_198599.2 | chr16:20233308-20241358 |
| 12018 | Map7 | NM_001198635.1 | chr10:20148919-20281590 |
| 12019 | Map7d1 | NM_001145970.1 | chr4:126232167-126256319 |
| 12020 | Map7d2 | NM_001081124.2 | chrX:159414571-159498757 |
| 12021 | Map9 | NM_001081230.1 | chr3:82358071-82395268 |
| 12022 | Mapk1 | NM_011949.3 | chr16:16983381-17039040 |
| 12023 | Mapk10 | NM_001081567.2 | chr5:102908548-103211334 |
| 12024 | Mapk11 | NM_011161.5 | chr15:89142483-89149606 |
| 12025 | Mapk12 | NM_013871.3 | chr15:89130583-89140703 |
| 12026 | Mapk13 | NM_011950.2 | chr17:28769316-28778704 |
| 12027 | Mapk14 | NM_001168508.1 | chr17:28691341-28748405 |
| 12028 | Mapk15 | NM_177922.2 | chr15:75993768-75999153 |
| 12029 | Mapk8ip1 | NM_001045483.1 | chr2:138855817-138846267 |
| 12030 | Mapk8ip1l | NM_178684.5 | chr14:47298313-47323091 |
| 12031 | Mapk3 | NM_011952.2 | chr7:126759625-126765816 |
| 12032 | Mapk4 | NM_172632.2 | chr18:73928485-74064949 |
| 12033 | Mapk6 | NM_015806.5 | chr9:75386781-75410016 |
| 12034 | Mapk7 | NM_001291033.1 | chr11:61488811-61494266 |
| 12035 | Mapk8 | NM_016700.4 | chr14:33377898-33447158 |
| 12036 | Mapk8ip1 | NM_001202445.1 | chr2:92383675-92392683 |
| 12037 | Mapk8ip2 | NM_021921.3 | chr15:89453910-89462447 |
| 12038 | Mapk8ip3 | NM_001163447.1 | chr17:24897505-24936977 |
| 12039 | Mapk9 | NM_001163671.1 | chr11:49846750-49896421 |
| 12040 | Mapkap1 | NM_001290625.1 | chr2:34406770-34624958 |
| 12041 | Mapkapk2 | NM_008551.2 | chr1:131053700-131097843 |
| 12042 | Mapkapk3 | NM_178907.3 | chr9:107254926-107289877 |
| 12043 | Mapkapk5 | NM_010017.5 | chr5:121525050-121545892 |
| 12044 | Mapkbp1 | NM_011941.3 | chr2:119972698-120027403 |
| 12045 | Mapre1 | NM_007896.3 | chr2:153741286-153773314 |
| 12046 | Mapre2 | NM_001162941.1 | chr18:23753724-23893861 |
| 12047 | Mapre3 | NM_133350.2 | chr5:30814640-30866106 |
| 12048 | Mapt | NM_001038609.2 | chr11:104231435-104332089 |
| 12049 | Marc1 | NM_029073.1 | chr1:184786766-184811300 |
| 12050 | Marc2 | NM_133684.3 | chr1:184813067-184845847 |
| 12051 | March1 | NM_001166372.1 | chr8:65618039-66471637 |
| 12052 | March10 | NM_001039242.2 | chr11:105401653-105456735 |
| 12053 | March11 | NM_177597.6 | chr15:26809047-26409575 |
| 12054 | March2 | NM_001252480.1 | chr17:33691504-33718677 |
| 12055 | March3 | NM_177115.2 | chr18:56761715-56925548 |
| 12056 | March4 | NM_001045533.1 | chr1:72427111-72536564 |
| 12057 | March5 | NM_001164336.1 | chr19:37207544-37221076 |
| 12058 | March6 | NM_172606.2 | chr15:31455898-31531037 |
| 12059 | March7 | NM_020575.2 | chr2:60209935-60248385 |

| | | | |
|---|---|---|---|
| 12060 | March8 | NM_027920.5 | chr6:116338021-116409541 |
| 12061 | March9 | NM_001033262.2 | chr10:127056049-127060184 |
| 12062 | Marcks | NM_008538.2 | chr10:37133242-37138926 |
| 12063 | Marcksl1 | NM_010807.4 | chr4:129513580-129515981 |
| 12064 | Marcksl1-ps4 | NR_028405.1 | chr13:4248734-4249777 |
| 12065 | Marco | NM_010766.2 | chr1:120474537-120505084 |
| 12066 | Marf1 | NM_001081154.2 | chr16:14109165-14159274 |
| 12067 | Mark1 | NM_145515.2 | chr1:184896423-184999549 |
| 12068 | Mark2 | NM_001080388.2 | chr19:7275395-7341860 |
| 12069 | Mark3 | NM_021516.4 | chr12:111574509-111656227 |
| 12070 | Mark4 | NM_172279.1 | chr7:19426074-19458494 |
| 12071 | Mars | NM_001003913.2 | chr10:127296220-127311786 |
| 12072 | Mars2 | NM_175439 | chr1:55237176-55240058 |
| 12073 | Marveld1 | NM_183195 | chr19:42147388-42151703 |
| 12074 | Marveld2 | NM_001038602 | chr13:100595956-100616971 |
| 12075 | Marveld3 | NM_028584.3 | chr8:109952908-109962205 |
| 12076 | Mas1 | NM_008552.4 | chr17:12841004-12868143 |
| 12077 | Masp1 | NM_008555.2 | chr16:23451784-23520590 |
| 12078 | Masp2 | NM_001003893.2 | chr4:148602543-148615480 |
| 12079 | Mast1 | NM_019452 | chr8:84911852-84937353 |
| 12080 | Mast2 | NM_001042743.2 | chr4:116306759-116464181 |
| 12081 | Mast3 | NM_199308.2 | chr8:70778116-70792433 |
| 12082 | Mast4 | NM_175171.3 | chr13:102732488-103334492 |
| 12083 | Mastl | NM_025979.4 | chr2:23116543-23156024 |
| 12084 | Mat1a | NM_133653.3 | chr14:41105032-41124428 |
| 12085 | Mat2a | NM_145569.4 | chr6:72432798-72439558 |
| 12086 | Mat2b | NM_001199274.1 | chr11:40679313-40695203 |
| 12087 | Matk | NM_001285853.1 | chr10:81257298-81262981 |
| 12088 | Matn1 | NM_010769.2 | chr4:130944384-130955476 |
| 12089 | Matn2 | NM_016762.2 | chr15:34306680-34436240 |
| 12090 | Matn3 | NM_010770.4 | chr12:8947928-8972028 |
| 12091 | Matn4 | NM_001252563.1 | chr2:164389392-164405160 |
| 12092 | Matr3 | NM_010771.6 | chr18:35562157-35592045 |
| 12093 | Mau2 | NM_001167939.1 | chr8:70016122-70042734 |
| 12094 | Mavs | NM_001206382.1 | chr2:131234062-131248024 |
| 12095 | Max | NM_001146176.1 | chr12:76937268-76962248 |
| 12096 | Maz | NM_010772.3 | chr7:127022136-127026479 |
| 12097 | Mb | NM_001164047.1 | chr15:77015486-77022787 |
| 12098 | Mb21d1 | NM_173888.3 | chr9:78430517-78443237 |
| 12099 | Mb21d2 | NM_177718.3 | chr16:28826175-28929698 |
| 12100 | Mbd1 | NM_013594.2 | chr18:74268287-74282684 |
| 12101 | Mbd2 | NM_010773.2 | chr18:70568291-70626131 |
| 12102 | Mbd3 | NM_013595.3 | chr10:80392538-80399531 |
| 12103 | Mbd3l1 | NM_028557.2 | chr9:18478394-18485292 |
| 12104 | Mbd3l2 | NM_144934.3 | chr9:18430614-18446316 |
| 12105 | Mbd4 | NM_010774.2 | chr6:115840696-115853341 |
| 12106 | Mbd5 | NM_001290656.1 | chr2:49245899-49317069 |
| 12107 | Mbd6 | NM_033072.2 | chr10:127281955-127288771 |
| 12108 | Mbip | NM_145442.2 | chr12:56328306-56345894 |
| 12109 | Mbl1 | NM_010775.2 | chr14:41151455-41158959 |
| 12110 | Mbl2 | NM_010776.2 | chr19:30232956-30239682 |
| 12111 | Mblac1 | NM_177878.3 | chr5:138194313-138195621 |
| 12112 | Mblac2 | NM_028372.1 | chr13:81711416-81753275 |
| 12113 | Mbnl1 | NM_001253708.2 | chr3:60501178-60629750 |
| 12114 | Mbnl2 | NM_175341.4 | chr14:120275668-120431698 |
| 12115 | Mbnl3 | NM_134163.5 | chrX:51113493-51205990 |
| 12116 | Mboat1 | NM_153546.4 | chr13:30136489-30246694 |
| 12117 | Mboat2 | NM_001083341.1 | chr12:24831598-24960299 |
| 12118 | Mboat4 | NM_001126314.2 | chr8:34115029-34125185 |
| 12119 | Mboat7 | NM_029934.3 | chr7:3677788-3693525 |
| 12120 | Mbp | NM_001025245.1 | chr18:82475122-82558703 |
| 12121 | Mbtd1 | NM_134012.3 | chr11:93886218-93946984 |
| 12122 | Mbtps1 | NM_001167910.1 | chr8:119508151-119558761 |
| 12123 | Mbtps2 | NM_172307.3 | chrX:157547821-157598715 |
| 12124 | Mc1r | NM_008559.2 | chr8:123407081-123410744 |
| 12125 | Mc2r | NM_001271716.1 | chr18:68406898-68429320 |
| 12126 | Mc3r | NM_008561.3 | chr2:172248491-172251114 |
| 12127 | Mc4r | NM_016977.4 | chr18:66857704-66860487 |
| 12128 | Mc5r | NM_013596.2 | chr18:68337602-68339711 |
| 12129 | Mcam | NM_023061.2 | chr9:44134657-44142726 |
| 12130 | Mcat | NM_001030014.2 | chr15:83546796-83555711 |
| 12131 | Mcc | NM_001085373.1 | chr18:44425059-44812182 |
| 12132 | Mccc1 | NM_023644.4 | chr3:35959305-36000678 |
| 12133 | Mccclos | NR_029456.1 | chr3:35999912-36008828 |
| 12134 | Mccc2 | NM_030026.2 | chr13:99948531-100015639 |
| 12135 | Mcee | NM_028626.1 | chr7:64392770-64412119 |
| 12136 | Mcemp1 | NM_026985.1 | chr3:3665761-3668905 |
| 12137 | Mcf2 | NM_001289730.1 | chrX:60055955-60147700 |
| 12138 | Mcf2l | NM_001159485.1 | chr8:12949417-13020509 |
| 12139 | Mcfd2 | NM_139295.3 | chr17:87254442-87265947 |
| 12140 | Mchr1 | NM_145132.2 | chr15:81235498-81238964 |
| 12141 | Mcidas | NM_001037914.3 | chr13:112993867-113000394 |
| 12142 | Mcl1 | NM_008562.3 | chr3:95658720-95663178 |
| 12143 | Mcm10 | NM_027290.3 | chr2:4990723-5012791 |
| 12144 | Mcm2 | NM_008564.2 | chr6:88883473-88898780 |
| 12145 | Mcm3 | NM_008563.3 | chr1:20803013-20820213 |
| 12146 | Mcm3ap | NM_019434.2 | chr10:76468970-76515857 |
| 12147 | Mcm4 | NM_008565.3 | chr16:15623896-15637400 |
| 12148 | Mcm5 | NM_008566.3 | chr8:75109508-75128439 |
| 12149 | Mcm6 | NM_008567.3 | chr1:128831574-128859705 |
| 12150 | Mcm7 | NM_008568.2 | chr5:138164588-138171862 |
| 12151 | Mcm8 | NM_001291054.1 | chr2:132816140-132844188 |
| 12152 | Mcm9 | NM_027830.2 | chr10:53537323-53630439 |
| 12153 | Mcmbp | NM_145955.3 | chr7:128696458-128740429 |
| 12154 | Mcmdc2 | NM_177722.3 | chr1:9908637-9940954 |

Fig. 26 - 65

| | | | | | | | |
|---|---|---|---|---|---|---|---|
| 12155 | Mcoln1 | NM_053177.1 | chr8:3500518-3515231 | 12250 | Mep1b | NM_008586.2 | chr18:21072343-21100199 |
| 12156 | Mcoln2 | NM_001005846.2 | chr3:146150173-146195512 | 12251 | Mepce | NM_144913.3 | chr5:137781905-137786701 |
| 12157 | Mcoln3 | NM_134160.1 | chr3:146121790-146140646 | 12252 | Mepe | NM_053172.2 | chr5:104325328-104338611 |
| 12158 | Mcph1 | NM_173189.2 | chr8:18595172-18803188 | 12253 | Mertk | NM_008587.1 | chr2:128698996-128802188 |
| 12159 | Mcpt1 | NM_008570.1 | chr14:56017963-56020391 | 12254 | Mesdc1 | NM_030705.4 | chr7:83880494-83884341 |
| 12160 | Mcpt2 | NM_008571.1 | chr14:56042122-56044634 | 12255 | Mesdc2 | NM_023403.3 | chr7:83891999-83901532 |
| 12161 | Mcpt4 | NM_010779.2 | chr14:56059743-56062310 | 12256 | Mesp1 | NM_008588.2 | chr7:79792240-79793590 |
| 12162 | Mcpt8 | NM_008572.1 | chr14:56082163-56085197 | 12257 | Mesp2 | NM_008589.2 | chr7:79810726-79813431 |
| 12163 | Mcpt9 | NM_010782.3 | chr14:56026863-56030495 | 12258 | Mest | NM_001252292.1 | chr6:30738052-30748466 |
| 12164 | Mcpt-ps1 | NR_028284.1 | chr14:55949808-55952371 | 12259 | Met | NM_008591.2 | chr6:17463956-17573980 |
| 12165 | Mcrs1 | NM_001164156.1 | chr15:99242816-99251961 | 12260 | Metap1 | NM_175224.4 | chr3:138458959-138489382 |
| 12166 | Mctp1 | NM_030174.2 | chr13:76384960-77031810 | 12261 | Metap1d | NM_026533.3 | chr2:71453337-71525191 |
| 12167 | Mctp2 | NM_001024703.1 | chr7:72077829-72306595 | 12262 | Metap2 | NM_019648.3 | chr10:93858489-93891202 |
| 12168 | Mcts1 | NM_026902.3 | chrX:38600657-38613522 | 12263 | Metrn | NM_133719.2 | chr17:25794570-25797045 |
| 12169 | Mcts2 | NM_025543.2 | chr2:152687147-152687942 | 12264 | Metrnl | NM_144797.3 | chr11:121702426-121717389 |
| 12170 | Mcu | NM_001033259.4 | chr10:59446983-59616692 | 12265 | Mettl1 | NM_010792.1 | chr10:127041931-127045461 |
| 12171 | Mcur1 | NM_001081059.3 | chr13:43538405-43560191 | 12266 | Mettl10 | NM_028095.1 | chr7:132827460-132852647 |
| 12172 | Mdc1 | NM_001010833.2 | chr17:35841497-35859670 | 12267 | Mettl11b | NM_001143956.1 | chr1:163702992-163725232 |
| 12173 | Mdfi | NM_001109973.2 | chr17:47815327-47834691 | 12268 | Mettl13 | NM_144877.1 | chr1:162533671-162548345 |
| 12174 | Mdfic | NM_175088.5 | chr6:15720660-15802169 | 12269 | Mettl14 | NM_201638.2 | chr3:123368294-123385990 |
| 12175 | Mdga1 | NM_001081160.1 | chr17:29827957-29887882 | 12270 | Mettl15 | NM_029790.3 | chr2:109092299-109278290 |
| 12176 | Mdga2 | NM_001193266.1 | chr12:66466058-67222549 | 12271 | Mettl16 | NM_026197.3 | chr11:74770862-74818692 |
| 12177 | Mdh1 | NM_008618.3 | chr11:21556691-21571934 | 12272 | Mettl17 | NM_001029990.1 | chr14:51884841-51891868 |
| 12178 | Mdh1b | NM_029696.4 | chr1:63698826-63730318 | 12273 | Mettl18 | NM_027279.2 | chr1:163994944-163997244 |
| 12179 | Mdh2 | NM_008617.2 | chr5:135778648-135790386 | 12274 | Mettl2 | NM_172567.3 | chr11:105126424-105141146 |
| 12180 | Mdk | NM_001012335.2 | chr2:91929804-91931702 | 12275 | Mettl20 | NM_001252094.1 | chr6:149141512-149151170 |
| 12181 | Mdm1 | NM_001162904.1 | chr10:118141786-118168999 | 12276 | Mettl21a | NM_025964.3 | chr1:64606479-64617168 |
| 12182 | Mdm2 | NM_001288586.1 | chr10:117688874-117710758 | 12277 | Mettl21c | NM_001013799.1 | chr1:44009407-44020006 |
| 12183 | Mdm4 | NM_008575.4 | chr1:132986104-133025416 | 12278 | Mettl21e | NM_207281.3 | chr1:44204069-44218931 |
| 12184 | Mdn1 | NM_001081392.1 | chr4:32657118-32775217 | 12279 | Mettl22 | NM_146247.1 | chr16:8470812-8490197 |
| 12185 | Mdp1 | NM_023397.4 | chr14:55657878-55660508 | 12280 | Mettl23 | NM_028865.3 | chr11:116843514-116849740 |
| 12186 | Me1 | NM_001198933.1 | chr9:86581362-86687277 | 12281 | Mettl24 | NM_177793.3 | chr10:40683281-40811083 |
| 12187 | Me2 | NM_145494.2 | chr18:73770039-73815392 | 12282 | Mettl25 | NM_207522.2 | chr10:105763184-105841380 |
| 12188 | Me3 | NM_181407.4 | chr7:89632817-89854359 | 12283 | Mettl3 | NM_019721.2 | chr14:52294841-52305124 |
| 12189 | Mea1 | NM_001277309.1 | chr17:46680985-46683126 | 12284 | Mettl4 | NM_176917.4 | chr17:94727079-94749892 |
| 12190 | Meaf6 | NM_020701.1 | chr4:125085133-125110070 | 12285 | Mettl5 | NM_029280.4 | chr2:69871194-69885615 |
| 12191 | Mecom | NM_007963.2 | chr3:29951295-30013204 | 12286 | Mettl6 | NM_025907.3 | chr14:31478797-31494977 |
| 12192 | Mecp2 | NM_001081979.2 | chrX:74026591-74085690 | 12287 | Mettl7a1 | NM_027334.3 | chr15:100304816-100314348 |
| 12193 | Mecr | NM_025297.2 | chr4:131843470-131867787 | 12288 | Mettl7a2 | NM_199477.2 | chr15:100353199-100361819 |
| 12194 | Med1 | NM_001080118.1 | chr11:98153660-98193293 | 12289 | Mettl7a2Higd1c | NM_001024672.3 | chr15:100353199-100384435 |
| 12195 | Med10 | NM_138596.2 | chr13:69809881-69816094 | 12290 | Mettl7a3 | NM_001081471.1 | chr15:100334928-100340169 |
| 12196 | Med11 | NM_025397.2 | chr11:70451930-70453726 | 12291 | Mettl7b | NM_027853.2 | chr10:128958276-128960988 |
| 12197 | Med12 | NM_021521.2 | chrX:101274090-101298934 | 12292 | Mettl8 | NM_001110512.1 | chr2:70964561-71018374 |
| 12198 | Med12l | NM_177855.3 | chr3:59006977-59318412 | 12293 | Mettl9 | NM_021554.2 | chr7:121034444-121076835 |
| 12199 | Med13 | NM_001080931.1 | chr11:86265714-86357525 | 12294 | Mex3a | NM_001029890.2 | chr3:88532394-88541394 |
| 12200 | Med13l | NM_172424.4 | chr5:118560718-118765437 | 12295 | Mex3b | NM_175366.3 | chr7:82867332-82871576 |
| 12201 | Med14 | NM_001048208.1 | chrX:12675370-12761973 | 12296 | Mex3c | NM_001039214.4 | chr18:73572704-73592578 |
| 12202 | Med15 | NM_001040683.2 | chr16:17651207-17722947 | 12297 | Mex3d | NM_198615.2 | chr10:80380354-80387651 |
| 12203 | Med16 | NM_001163276.1 | chr10:79894706-79908938 | 12298 | Mfap1a | NM_026220.4 | chr2:121492680-121506656 |
| 12204 | Med17 | NM_144933.1 | chr9:15260350-15279867 | 12299 | Mfap1b | NM_001081975.3 | chr2:121461665-121474023 |
| 12205 | Med18 | NM_026039.3 | chr4:132458728-132463921 | 12300 | Mfap2 | NM_001161799.1 | chr4:141010423-141015984 |
| 12206 | Med19 | NM_025885.3 | chr2:84678401-84688215 | 12301 | Mfap3 | NM_145426.2 | chr11:57518664-57533817 |
| 12207 | Med20 | NM_020048.3 | chr17:47611596-47624418 | 12302 | Mfap3l | NM_001177881.1 | chr8:60655103-60676731 |
| 12208 | Med21 | NM_025315.3 | chr6:146642578-146650600 | 12303 | Mfap4 | NM_029568.2 | chr11:61485443-61488704 |
| 12209 | Med22 | NM_001033908.1 | chr2:26905266-26910642 | 12304 | Mfap5 | NM_015776.2 | chr6:122513675-122529287 |
| 12210 | Med23 | NM_001166416.1 | chr10:24869985-24913529 | 12305 | Mff | NM_029409.3 | chr1:82724889-82752389 |
| 12211 | Med24 | NM_011869.2 | chr11:98704590-98729435 | 12306 | Mfge8 | NM_001045489.1 | chr7:79133767-79149060 |
| 12212 | Med25 | NM_029365.2 | chr7:44879385-44892366 | 12307 | Mfhas1 | NM_001081279.1 | chr8:35587797-35679449 |
| 12213 | Med26 | NM_029462.2 | chr8:72494558-72548310 | 12308 | Mfi2 | NM_013900.2 | chr16:31878809-31899019 |
| 12214 | Med27 | NM_001290489.1 | chr2:29378513-29524790 | 12309 | Mfn1 | NM_024200.4 | chr3:32529481-32579225 |
| 12215 | Med28 | NM_025895.4 | chr5:45520228-45529284 | 12310 | Mfn2 | NM_001285920.1 | chr4:147873585-147904909 |
| 12216 | Med29 | NM_026042 | chr7:28385246-28392690 | 12311 | Mfng | NM_008595.2 | chr15:78755882-78773445 |
| 12217 | Med30 | NM_027212.2 | chr15:52712444-52730431 | 12312 | Mfrp | NM_001190314.1 | chr9:44101769-44109187 |
| 12218 | Med31 | NM_026068 | chr11:72211723-72215592 | 12313 | Mfsd1 | NM_025813.3 | chr3:67582767-67604231 |
| 12219 | Med4 | NM_026119 | chr14:73510048-73518545 | 12314 | Mfsd10 | NM_026660.2 | chr5:34633646-34637114 |
| 12220 | Med6 | NM_027213.2 | chr12:81573563-81594958 | 12315 | Mfsd11 | NM_178620.3 | chr11:116854014-116875637 |
| 12221 | Med7 | NM_001104530.1 | chr11:46436946-46442721 | 12316 | Mfsd12 | NM_028657.3 | chr10:81357569-81364035 |
| 12222 | Med8 | NM_001409336-118415824 | chr4:118409336-118415824 | 12317 | Mfsd2a | NM_029662.2 | chr4:122946850-122961188 |
| 12223 | Med9 | NM_138675.3 | chr11:59948213-59963306 | 12318 | Mfsd2b | NM_001033488.2 | chr12:4862437-4874259 |
| 12224 | Med9os | NR_045174.1 | chr11:59946891-59948147 | 12319 | Mfsd3 | NM_027122.3 | chr15:76701541-76704239 |
| 12225 | Medag | NM_027519.3 | chr5:149411805-149431703 | 12320 | Mfsd4 | NM_001114662.1 | chr1:132036782-132068062 |
| 12226 | Mef2a | NM_001033713.2 | chr7:67231162-67372858 | 12321 | Mfsd5 | NM_134100.4 | chr15:102279455-102281744 |
| 12227 | Mef2b | NM_001045284.2 | chr8:70152760-70167488 | 12322 | Mfsd6 | NM_133829.2 | chr1:52656304-52727318 |
| 12228 | Mef2c | NM_001170537.1 | chr13:83504033-83667079 | 12323 | Mfsd6l | NM_146004.1 | chr11:68556185-68558245 |
| 12229 | Mef2d | NM_133665.4 | chr3:88142371-88172091 | 12324 | Mfsd7a | NM_172883.2 | chr5:108441053-108448891 |
| 12230 | Mefv | NM_010791.1 | chr16:3707214-3718124 | 12325 | Mfsd7b | NM_001081259.1 | chr1:191005631-191026190 |
| 12231 | Meg3 | NR_003633.3 | chr12:109545397-109568650 | 12326 | Mfsd7c | NM_145447.2 | chr12:85746538-85813585 |
| 12232 | Megf10 | NM_001001979.2 | chr18:57133089-57297467 | 12327 | Mfsd8 | NM_028140.4 | chr3:40818171-40846854 |
| 12233 | Megf11 | NM_001134369.1 | chr9:64385625-64709205 | 12328 | Mfsd9 | NM_172499.2 | chr1:40772039-40790657 |
| 12234 | Megf6 | NM_001162977.1 | chr4:154170712-154275721 | 12329 | Mga | NM_001164274.1 | chr2:119897227-119969581 |
| 12235 | Megf8 | NM_001160400.1 | chr7:25317163-25365917 | 12330 | Mgam | NM_001171003.1 | chr6:40628830-40769123 |
| 12236 | Megf9 | NM_172694.2 | chr4:70431926-70534928 | 12331 | Mgarp | NM_026358.3 | chr3:51388412-51396547 |
| 12237 | Mei1 | NM_028897.3 | chr15:82070116-82126814 | 12332 | Mgat1 | NM_001110148.1 | chr11:49244190-49263024 |
| 12238 | Mei4 | NM_175213.3 | chr9:81863743-82027491 | 12333 | Mgat2 | NM_146035.2 | chr12:69184157-69186773 |
| 12239 | Meig1 | NM_009042 | chr2:3409042-3422648 | 12334 | Mgat3 | NM_010795.4 | chr15:80173720-80215519 |
| 12240 | Meiob | NM_029197.1 | chr17:24804381-24839787 | 12335 | Mgat4a | NM_001290801.1 | chr1:37439339-37536404 |
| 12241 | Meis1 | NM_001193271.1 | chr11:18880427-19018969 | 12336 | Mgat4b | NM_145926.3 | chr11:50225334-50235105 |
| 12242 | Meis2 | NM_001136072.2 | chr2:115861263-116065058 | 12337 | Mgat4c | NM_001162368.1 | chr10:102158857-102391468 |
| 12243 | Meis3 | NM_001277988.2 | chr7:16175394-16186508 | 12338 | Mgat5 | NM_145128.3 | chr1:127204605-127482972 |
| 12244 | Melk | NM_010790.2 | chr4:44300916-44364675 | 12339 | Mgat5b | NM_172948.3 | chr11:116918862-116986944 |
| 12245 | Memo1 | NM_133771.2 | chr17:74200699-74294863 | 12340 | Mgea5 | NM_023799.3 | chr19:45750258-45783291 |
| 12246 | Men1 | NM_001168488.1 | chr19:6334978-6340894 | 12341 | Mgl2 | NM_145137.2 | chr11:70130356-70137542 |
| 12247 | Meox1 | NM_010791.3 | chr11:101877509-101894354 | 12342 | Mgll | NM_001166249.1 | chr6:88724411-88828360 |
| 12248 | Meox2 | NM_008584.3 | chr3:37108545-37179528 | 12343 | Mgme1 | NM_001289630.1 | chr2:144270903-144281227 |
| 12249 | Mep1a | NM_008585.2 | chr17:43474328-43502773 | 12344 | Mgmt | NM_008598.2 | chr7:136894610-137128188 |

Fig. 26 - 66

| | | | |
|---|---|---|---|
| 12345 | Mgp | NM_008597.3 | chr6:136872434-136875805 |
| 12346 | Mgrn1 | NM_001252437.1 | chr16:4886099-4938296 |
| 12347 | Mgst1 | NM_019946.4 | chr6:138140536-138156752 |
| 12348 | Mgst2 | NM_174995.3 | chr3:51661178-51682674 |
| 12349 | Mgst3 | NM_025569.1 | chr1:167372383-167393797 |
| 12350 | Mia | NM_019394.3 | chr7:27179740-27181149 |
| 12351 | Mia2 | NM_177321.2 | chr12:59095799-59109130 |
| 12352 | Mia3 | NM_177389.3 | chr1:183326235-183369565 |
| 12353 | Miat | NR_003718.2 | chr5:112213227-112228948 |
| 12354 | Mib1 | NM_144860.2 | chr18:10725624-10812217 |
| 12355 | Mib2 | NM_001256107.1 | chr4:155654469-155669254 |
| 12356 | Mical1 | NM_001164433.1 | chr10:41476313-41487030 |
| 12357 | Mical2 | NM_001193305.1 | chr7:112225895-112353975 |
| 12358 | Mical3 | NM_001270475.1 | chr6:120931545-121131022 |
| 12359 | Micalcl | NM_027587.2 | chr7:112368307-112413104 |
| 12360 | Micall1 | NM_177461.1 | chr15:79108982-79136901 |
| 12361 | Micall2 | NM_174850.3 | chr5:139706692-139736333 |
| 12362 | Micu1 | NM_001291442.1 | chr10:59702562-59864134 |
| 12363 | Micu2 | NM_028643.3 | chr14:57916279-57999262 |
| 12364 | Micu3 | NM_030110.1 | chr8:40308050-40386304 |
| 12365 | Mid1 | NM_001290504.1 | chrX:169828158-169990797 |
| 12366 | Mid1ip1 | NM_001166635.1 | chrX:10717364-10719702 |
| 12367 | Mid2 | NM_011845.2 | chrX:140678027-140767715 |
| 12368 | Midn | NM_021565.2 | chr10:80148271-80158368 |
| 12369 | Mief1 | NM_178719.5 | chr15:80234079-80253371 |
| 12370 | Mief2 | NM_001009927.2 | chr11:60728397-60732951 |
| 12371 | Mien1 | NM_025559.2 | chr11:98437707-98438988 |
| 12372 | Mier1 | NM_001039081.2 | chr4:103119389-103165754 |
| 12373 | Mier2 | NM_027422.3 | chr10:79540244-79555091 |
| 12374 | Mier3 | NM_172593.3 | chr13:111686177-111718594 |
| 12375 | Mif | NM_010798.2 | chr10:75859352-75860250 |
| 12376 | Mif4gd | NM_001243584.1 | chr11:115607918-115612969 |
| 12377 | Miip | NM_001025365.2 | chr4:147860777-147868719 |
| 12378 | Mill1 | NM_153749.4 | chr7:18245346-18266092 |
| 12379 | Mill2 | NM_153760.2 | chr7:18839965-18858653 |
| 12380 | Milr1 | NM_001033435.3 | chr11:106751225-106767765 |
| 12381 | Mina | NM_025910.3 | chr16:59471774-59492451 |
| 12382 | Mink1 | NM_001045959.1 | chr11:70562880-70614482 |
| 12383 | Minos1 | NM_001163006.2 | chr4:139101813-139131113 |
| 12384 | Minpp1 | NM_010799.2 | chr19:32485768-32515370 |
| 12385 | Mios | NM_145374.2 | chr6:8209226-8236273 |
| 12386 | Miox | NM_019791.2 | chr15:89334472-89337007 |
| 12387 | Mip | NM_008600.5 | chr10:128225809-128231812 |
| 12388 | Mipep | NM_027436.3 | chr14:60784565-60903613 |
| 12389 | Mipol1 | NM_001164370.1 | chr12:57230424-57457241 |
| 12390 | Mir100 | NR_029790.1 | chr9:41531424-41531504 |
| 12391 | Mir101a | NR_029537.1 | chr4:101346944-101347027 |
| 12392 | Mir101b | NR_029774.1 | chr19:29135278-29135375 |
| 12393 | Mir101c | NR_039546.1 | chr9:3038668-3038743 |
| 12394 | Mir103-1 | NR_029754.1 | chr11:35782395-35782481 |
| 12395 | Mir103-2 | NR_029758.1 | chr2:131288051-131288137 |
| 12396 | Mir105 | NR_030546.1 | chrX:72591499-72591579 |
| 12397 | Mir106a | NR_029657.1 | chrX:52742502-52742567 |
| 12398 | Mir106b | NR_029658.1 | chr5:138165736-138165818 |
| 12399 | Mir107 | NR_029783.1 | chr19:34820686-34820773 |
| 12400 | Mir10a | NR_029784.1 | chr11:96317164-96317274 |
| 12401 | Mir10b | NR_029566.1 | chr2:74726069-74726137 |
| 12402 | Mir1187 | NR_035415.1 | chr5:82798943-82799065 |
| 12403 | Mir1188 | NR_035419.1 | chr12:109611821-109611941 |
| 12404 | Mir1190 | NR_035421 | chr12:101021672-101021768 |
| 12405 | Mir1191 | NR_035422.1 | chr5:76206228-76206319 |
| 12406 | Mir1191b | NR_106101.1 | chr10:81416239-81416297 |
| 12407 | Mir1192 | NR_035423.1 | chr19:23149480-23149551 |
| 12408 | Mir1193 | NR_035424.1 | chr12:109715670-109715791 |
| 12409 | Mir1195 | NR_035427 | chr16:30920553-31275697 |
| 12410 | Mir1197 | NR_035429.1 | chr12:109712316-109712436 |
| 12411 | Mir1198 | NR_035430.1 | chr12:55370694-55491306 |
| 12412 | Mir1199 | NR_035431.1 | chr8:84011514-84011633 |
| 12413 | Mir1224 | NR_035407.1 | chr16:20604451-20604536 |
| 12414 | Mir122a | NR_029600.1 | chr18:65248860-65248926 |
| 12415 | Mir1231 | NR_049188.1 | chr1:135454602-135454683 |
| 12416 | Mir1247 | NR_037204.1 | chr12:110278047-110278129 |
| 12417 | Mir1249 | NR_037206.1 | chr15:84951525-84951623 |
| 12418 | Mir124a-1 | NR_029813.1 | chr14:64590656-64590741 |
| 12419 | Mir124a-2 | NR_029814.1 | chr3:17795661-17795770 |
| 12420 | Mir124a-3 | NR_029538.1 | chr2:180894039-180894107 |
| 12421 | Mir1251 | NR_037219.1 | chr10:92137139-92137223 |
| 12422 | Mir1258 | NR_106160.1 | chr18:56538138-56538198 |
| 12423 | Mir125a | NR_029539.1 | chr17:17830811-17830879 |
| 12424 | Mir125b-1 | NR_029822.1 | chr9:41581925-41582002 |
| 12425 | Mir125b-2 | NR_029540.1 | chr16:77646272-77646343 |
| 12426 | Mir126 | NR_029541.1 | chr2:26591356-26591429 |
| 12427 | Mir1264 | NR_037205.1 | chrX:147010600-147010686 |
| 12428 | Mir126b | NR_106155.1 | chr2:26591362-26591420 |
| 12429 | Mir127 | NR_029752.1 | chr12:109592845-109592915 |
| 12430 | Mir128-1 | NR_029543.1 | chr1:128202366-128202430 |
| 12431 | Mir128-2 | NR_029823.1 | chr9:112118635-112118711 |
| 12432 | Mir1291 | NR_106171.1 | chr15:98519761-98519878 |
| 12433 | Mir129-1 | NR_029567.1 | chr6:29022618-29022691 |
| 12434 | Mir129-2 | NR_029752.1 | chr2:94241363-94241453 |
| 12435 | Mir1298 | NR_037210.1 | chrX:147064904-147065002 |
| 12436 | Mir129b | NR_106139.1 | chr2:94241377-94241442 |
| 12437 | Mir1306 | NR_035467.2 | chr16:18284238-18284317 |
| 12438 | Mir130a | NR_029544.1 | chr2:84741114-84741178 |
| 12439 | Mir130b | NR_029659.1 | chr16:17124060-17124142 |
| 12440 | Mir130c | NR_105807.1 | chr9:53400804-53400886 |
| 12441 | Mir132 | NR_029546.1 | chr11:75173681-75173747 |
| 12442 | Mir133a-1 | NR_029547.1 | chr18:10782908-10782976 |
| 12443 | Mir133a-2 | NR_029901.1 | chr2:180398378-180398482 |
| 12444 | Mir133b | NR_029902.1 | chr1:20682768-20682887 |
| 12445 | Mir133c | NR_105753.1 | chr2:29475214-29475294 |
| 12446 | Mir134 | NR_029548.1 | chr12:109734138-109734209 |
| 12447 | Mir135a-1 | NR_029549.1 | chr9:106154123-106154213 |
| 12448 | Mir135a-2 | NR_029812.1 | chr10:92072085-92072185 |
| 12449 | Mir135b | NR_029777.1 | chr1:132198087-132198184 |
| 12450 | Mir136 | NR_029550.1 | chr12:109595326-109595388 |
| 12451 | Mir137 | NR_029551.1 | chr3:118433856-118433929 |
| 12452 | Mir138-1 | NR_029819.1 | chr9:122682875-122682974 |
| 12453 | Mir138-2 | NR_029552.1 | chr8:94324310-94324381 |
| 12454 | Mir139 | NR_029791.1 | chr7:101475375-101475443 |
| 12455 | Mir140 | NR_029553.1 | chr8:107551243-107551313 |
| 12456 | Mir141 | NR_029554.1 | chr6:124717913-124717985 |
| 12457 | Mir142 | NR_029555.1 | chr11:87756863-87756927 |
| 12458 | Mir142b | NR_106176.1 | chr11:87756840-87756955 |
| 12459 | Mir143 | NR_029601.1 | chr18:61649195-61649258 |
| 12460 | Mir143hg | NR_045402.1 | chr18:61645877-61665538 |
| 12461 | Mir144 | NR_029556.1 | chr11:78073004-78073070 |
| 12462 | Mir145 | NR_029557.1 | chr18:61647824-61647894 |
| 12463 | Mir145b | NR_105780.1 | chr18:69022198-69022273 |
| 12464 | Mir146 | NR_029558.1 | chr11:43374396-43374461 |
| 12465 | Mir146b | NR_030468.1 | chr19:46342761-46342870 |
| 12466 | Mir147 | NR_030547.1 | chr2:122640802-122640881 |
| 12467 | Mir148a | NR_029719.1 | chr6:51269811-51269910 |
| 12468 | Mir148b | NR_029766.1 | chr15:103285124-103285221 |
| 12469 | Mir149 | NR_029559.1 | chr1:92850377-92850443 |
| 12470 | Mir150 | NR_029560.1 | chr7:45121756-45121821 |
| 12471 | Mir152 | NR_029562.1 | chr11:96850392-96850465 |
| 12472 | Mir153 | NR_029563.1 | chr12:117250816-117250885 |
| 12473 | Mir154 | NR_029564.1 | chr12:109738432-109738498 |
| 12474 | Mir155 | NR_029565.1 | chr16:84714139-84714204 |
| 12475 | Mir15a | NR_029733.1 | chr14:61632026-61632110 |
| 12476 | Mir15b | NR_029529.1 | chr3:69009771-69009835 |
| 12477 | Mir16-1 | NR_029734.1 | chr14:61631879-61631972 |
| 12478 | Mir16-2 | NR_029735.1 | chr3:69009901-69009996 |
| 12479 | Mir1668 | NR_106188.1 | chr8:83723877-83723984 |
| 12480 | Mir17 | NR_029785.1 | chr14:115043670-115043754 |
| 12481 | Mir17hg | NR_029382.1 | chr14:115044389-115046728 |
| 12482 | Mir18 | NR_029736.1 | chr14:115043850-115043946 |
| 12483 | Mir181a-1 | NR_029795.1 | chr1:137966454-137966541 |
| 12484 | Mir181a-2 | NR_029568.1 | chr2:38852734-38852810 |
| 12485 | Mir181b-1 | NR_029820.1 | chr1:137966638-137966718 |
| 12486 | Mir181b-2 | NR_029904.1 | chr2:38853829-38853915 |
| 12487 | Mir181c | NR_029821.1 | chr8:84178872-84178961 |
| 12488 | Mir181d | NR_030534.1 | chr8:84178715-84178787 |
| 12489 | Mir182 | NR_029569.1 | chr6:30165917-30165992 |
| 12490 | Mir183 | NR_030713.1 | chr6:30169667-30169737 |
| 12491 | Mir1839 | NR_035501.1 | chr7:81529915-81529988 |
| 12492 | Mir184 | NR_029570.1 | chr9:89802259-89802328 |
| 12493 | Mir1843 | NR_037207.1 | chr12:80391612-80391677 |
| 12494 | Mir1843b | NR_039543.1 | chr1:159340357-159340423 |
| 12495 | Mir185 | NR_029571.1 | chr16:18327400-18327470 |
| 12496 | Mir186 | NR_029572.1 | chr3:157544278-157544349 |
| 12497 | Mir187 | NR_029573.1 | chr18:24429109-24429170 |
| 12498 | Mir188 | NR_029574.1 | chrX:7247988-7248056 |
| 12499 | Mir1892 | NR_035439.1 | chr12:54645932-54646012 |
| 12500 | Mir1893 | NR_035446.1 | chr16:6490563-6490646 |
| 12501 | Mir1894 | NR_035445.1 | chr17:35917888-35917969 |
| 12502 | Mir1895 | NR_035435.1 | chr2:134240504-134240583 |
| 12503 | Mir1896 | NR_035441.1 | chr13:21445159-21445240 |
| 12504 | Mir1897 | NR_035433.1 | chr3:34638463-34638542 |
| 12505 | Mir1898 | NR_035443.1 | chr15:121171491-121171574 |
| 12506 | Mir1899 | NR_035437.1 | chr9:8246785-8246881 |
| 12507 | Mir18b | NR_030548.1 | chrX:52742330-52742413 |
| 12508 | Mir190 | NR_029576.1 | chr9:67236659-67236726 |
| 12509 | Mir1900 | NR_035438.1 | chr9:21032250-21032328 |
| 12510 | Mir1901 | NR_035447.1 | chr18:11840360-11840438 |
| 12511 | Mir1902 | NR_035432.1 | chr2:104428860-104428940 |
| 12512 | Mir1903 | NR_035436.1 | chr8:128359240-128359320 |
| 12513 | Mir1904 | NR_035442.1 | chr13:109903808-109903888 |
| 12514 | Mir1905 | NR_035434.1 | chr3:88536300-88536382 |
| 12515 | Mir1906-1 | NR_035440.1 | chrX:88759473-109544620 |
| 12516 | Mir1907 | NR_035444.1 | chr15:50889024-50889114 |
| 12517 | Mir190b | NR_030543.1 | chr3:90070019-90070099 |
| 12518 | Mir191 | NR_029577.1 | chr9:108568318-108568392 |
| 12519 | Mir1912 | NR_037300.1 | chrX:147009440-147009527 |
| 12520 | Mir192 | NR_029720.1 | chr19:6264843-6264932 |
| 12521 | Mir1928 | NR_035449.1 | chr7:74206553-74206620 |
| 12522 | Mir1929 | NR_035450.1 | chr10:44359675-44359768 |
| 12523 | Mir193 | NR_029579.1 | chr11:79711968-79712034 |
| 12524 | Mir1930 | NR_035451.1 | chr10:77641223-77641307 |
| 12525 | Mir1931 | NR_035452.1 | chr10:93162784-93162903 |
| 12526 | Mir1932 | NR_035453.1 | chr11:119390471-119390561 |
| 12527 | Mir1933 | NR_035454.1 | chr11:21344587-21344675 |
| 12528 | Mir1934 | NR_035455.1 | chr11:69663042-69663125 |
| 12529 | Mir1936 | NR_035457.1 | chr12:102684927-102685020 |
| 12530 | Mir1938 | NR_035459.1 | chr12:40222711-40222811 |
| 12531 | Mir193b | NR_030549.1 | chr16:13449522-13449601 |
| 12532 | Mir1940 | NR_035461.1 | chr13:95330580-95330683 |
| 12533 | Mir1941 | NR_035462.1 | chr15:101369351-101369434 |
| 12534 | Mir194-1 | NR_029580.1 | chr1:185313318-185313385 |

Fig. 26 - 67

| | | | | | | | | |
|---|---|---|---|---|---|---|---|---|
| 12535 | Mir1942 | NR_035463.1 | chr15:76215610-76215673 | | 12630 | Mir27a | NR_029746.1 | chr8:84208671-84208758 |
| 12536 | Mir194-2 | NR_029830.1 | chr19:6264642-6264728 | | 12631 | Mir27b | NR_029531.1 | chr13:63300711-63300784 |
| 12537 | Mir1943 | NR_035464.1 | chr15:79375227-79375300 | | 12632 | Mir28 | NR_029788.1 | chr18:52123524-52123546 |
| 12538 | Mir1945 | NR_035466.1 | chr16:11254367-11254445 | | 12633 | Mir2861 | NR_037217.1 | chr2:32712806-32712888 |
| 12539 | Mir1946a | NR_035468.1 | chr16:32267449-32267583 | | 12634 | Mir2b | NR_039551.1 | chr8:73016511-73016591 |
| 12540 | Mir1946b | NR_035496.1 | chr3:96080595-96148402 | | 12635 | Mir28c | NR_039538.1 | chr8:96545953-96545973 |
| 12541 | Mir1947 | NR_035469.1 | chr16:33105360-33105445 | | 12636 | Mir290 | NR_029640.1 | chr7:3218625-3218708 |
| 12542 | Mir1948 | NR_035471.1 | chr18:12714810-12714895 | | 12637 | Mir290b | NR_106158.1 | chr7:3218637-3218695 |
| 12543 | Mir1949 | NR_035472.1 | chr18:35554566-35564636 | | 12638 | Mir291a | NR_029641.1 | chr7:3218918-3219000 |
| 12544 | Mir195 | NR_029581.1 | chr11:70235041-70235135 | | 12639 | Mir291b | NR_030276.1 | chr7:3219481-3219560 |
| 12545 | Mir1950 | NR_035473.1 | chr6:40529090-40910666 | | 12640 | Mir292 | NR_029642.1 | chr7:3219188-3219270 |
| 12546 | Mir1951 | NR_035476.1 | chr2:115638724-115638813 | | 12641 | Mir292b | NR_106140.1 | chr7:3219197-3219259 |
| 12547 | Mir1952 | NR_035477.1 | chr2:138819928-138820007 | | 12642 | Mir293 | NR_029643.1 | chr7:3220342-3220422 |
| 12548 | Mir1953 | NR_035478.1 | chr2:151967528-151967617 | | 12643 | Mir294 | NR_029644.1 | chr7:3220640-3220724 |
| 12549 | Mir1954 | NR_035479.1 | chr2:113220186-113423560 | | 12644 | Mir295 | NR_029645.1 | chr7:3220772-3220843 |
| 12550 | Mir1955 | NR_035480.1 | chr2:92191976-92192074 | | 12645 | Mir296 | NR_029646.1 | chr2:174267046-174267125 |
| 12551 | Mir1956 | NR_035481.1 | chr3:138526420-138526485 | | 12646 | Mir297-1 | NR_029647.1 | chr14:34645143-34653574 |
| 12552 | Mir1957 | NR_035483.1 | chr6:24484966-94782876 | | 12647 | Mir297-2 | NR_029648.2 | chr2:10472253-10472343 |
| 12553 | Mir1957b | NR_105819.1 | chr8:111450199-111450322 | | 12648 | Mir297a-3 | NR_030551.1 | chr2:10472253-10511772 |
| 12554 | Mir1958 | NR_035484.1 | chr1:63980972-63984483 | | 12649 | Mir297a-4 | NR_030552.1 | chr2:10472253-10472340 |
| 12555 | Mir195b | NR_105751.1 | chr2:56785810-56785907 | | 12650 | Mir297b | NR_030474.1 | chr2:10511666-10511775 |
| 12556 | Mir1960 | NR_035486.1 | chr5:30170738-30170816 | | 12651 | Mir297c | NR_030555.1 | chr1:185537335-185988795 |
| 12557 | Mir1961 | NR_035487.1 | chr5:92788450-92788562 | | 12652 | Mir298 | NR_029649.1 | chr2:174267503-174267585 |
| 12558 | Mir1962 | NR_035488.1 | chr7:135566161-135566282 | | 12653 | Mir299 | NR_029650.1 | chr12:109710637-109710700 |
| 12559 | Mir1963 | NR_035489.1 | chr7:29083635-29083694 | | 12654 | Mir299b | NR_049185.1 | chr12:109710644-109710693 |
| 12560 | Mir1964 | NR_035490.1 | chr7:29773293-29773376 | | 12655 | Mir29a | NR_029744.1 | chr6:31062659-31062747 |
| 12561 | Mir1966 | NR_035492 | chr8:105615465-105615573 | | 12656 | Mir29b-1 | NR_029532.1 | chr6:31063022-31063093 |
| 12562 | Mir1967 | NR_035493.1 | chr8:124022640-124022722 | | 12657 | Mir29b-2 | NR_029809.1 | chr1:195037039-195037120 |
| 12563 | Mir1968 | NR_035494.1 | chr8:13189030-13189098 | | 12658 | Mir29c | NR_029745.1 | chr1:195037546-195037634 |
| 12564 | Mir1969 | NR_035495.1 | chr8:70925524-70925618 | | 12659 | Mir300 | NR_029651.1 | chr12:109724312-109724391 |
| 12565 | Mir196a-1 | NR_029721.1 | chr11:96265163-96265265 | | 12660 | Mir301 | NR_029652.1 | chr11:87113003-87113089 |
| 12566 | Mir196a-2 | NR_029722.1 | chr15:102973349-102973434 | | 12661 | Mir301b | NR_030415.1 | chr16:17124399-17124496 |
| 12567 | Mir196b | NR_029912.1 | chr6:52230080-52230165 | | 12662 | Mir302a | NR_029653.1 | chr3:127545495-127545564 |
| 12568 | Mir1970 | NR_035497.1 | chr7:107284774-107580276 | | 12663 | Mir302b | NR_030403.1 | chr3:127545227-127545301 |
| 12569 | Mir1971 | NR_035499.1 | chr14:78191372-78191478 | | 12664 | Mir302c | NR_030404.1 | chr3:127545362-127545430 |
| 12570 | Mir1981 | NR_035502.1 | chr1:184824206-184822488 | | 12665 | Mir302d | NR_030405.1 | chr3:127545623-127545689 |
| 12571 | Mir1982 | NR_035503.1 | chr10:80828796-80828870 | | 12666 | Mir3057 | NR_037218.1 | chr10:81271596-81271687 |
| 12572 | Mir1983 | NR_035500.1 | chr13:21896917-21897049 | | 12667 | Mir3058 | NR_037212.1 | chr10:95559230-95559321 |
| 12573 | Mir199a-1 | NR_029585.1 | chr9:21496494-21496564 | | 12668 | Mir3059 | NR_037211.1 | chr10:101772691-101772772 |
| 12574 | Mir199a-2 | NR_029810.1 | chr1:162217813-162217923 | | 12669 | Mir3060 | NR_037220.1 | chr11:4139363-4139446 |
| 12575 | Mir199b | NR_029811.1 | chr2:32318459-32318569 | | 12670 | Mir3061 | NR_037221.1 | chr11:52126745-52126836 |
| 12576 | Mir19a | NR_029786.1 | chr14:115043999-115044081 | | 12671 | Mir3062 | NR_037222.1 | chr11:68990573-68990678 |
| 12577 | Mir19b-1 | NR_029815.1 | chr14:115044304-115044391 | | 12672 | Mir3063 | NR_037223.1 | chr11:95963291-95963383 |
| 12578 | Mir19b-2 | NR_029715.1 | chrX:52741982-52742066 | | 12673 | Mir3064 | NR_037224.1 | chr11:106782692-106782759 |
| 12579 | Mir1a-1 | NR_029528.1 | chr2:180389047-180389124 | | 12674 | Mir3065 | NR_037225.1 | chr11:120014766-120014853 |
| 12580 | Mir1a-2 | NR_029781.1 | chr18:10785480-10785552 | | 12675 | Mir3066 | NR_037226.1 | chr12:17355391-17355474 |
| 12581 | Mir1b | NR_035413.1 | chr18:10785445-10785567 | | 12676 | Mir3067 | NR_037227.1 | chr12:81166150-81166234 |
| 12582 | Mir200a | NR_029723.1 | chr4:156054895-156054985 | | 12677 | Mir3068 | NR_037228.1 | chr12:87437679-87437757 |
| 12583 | Mir200b | NR_029587.1 | chr4:156055680-156055750 | | 12678 | Mir3069 | NR_037229.1 | chr12:105031076-105031141 |
| 12584 | Mir200c | NR_029792.1 | chr6:124718321-124718390 | | 12679 | Mir3070a | NR_037230.1 | chr12:109587942-109588031 |
| 12585 | Mir201 | NR_029588.1 | chrX:67988095-67988161 | | 12680 | Mir3070b | NR_037231.1 | chr12:109588591-109588680 |
| 12586 | Mir202 | NR_029589.1 | chr7:139957688-139957760 | | 12681 | Mir3071 | NR_037232.1 | chr12:109595317-109595397 |
| 12587 | Mir203 | NR_029590.1 | chr12:112130879-112130955 | | 12682 | Mir3072 | NR_037233.1 | chr12:109747877-109747960 |
| 12588 | Mir204 | NR_029591.1 | chr19:22750604-22750672 | | 12683 | Mir3073 | NR_037234.1 | chr12:112109237-112109322 |
| 12589 | Mir205 | NR_029592.1 | chr1:193507462-193507530 | | 12684 | Mir3073b | NR_049197.1 | chr12:112109249-112109309 |
| 12590 | Mir206 | NR_029593.1 | chr1:20679009-20679082 | | 12685 | Mir3074-1 | NR_037235.1 | chr13:63301198-63301283 |
| 12591 | Mir207 | NR_029594.1 | chr4:40722916-40722995 | | 12686 | Mir3074-2 | NR_037294.1 | chr8:84208824-84208907 |
| 12592 | Mir208a | NR_029724.1 | chr14:54949059-54949142 | | 12687 | Mir3075 | NR_037236.1 | chr14:25534438-25534523 |
| 12593 | Mir208b | NR_030607.1 | chr14:54975976-54975776 | | 12688 | Mir3076 | NR_037237.1 | chr14:30572148-30572208 |
| 12594 | Mir20a | NR_029737.1 | chr14:115044156-115044263 | | 12689 | Mir3077 | NR_037238.1 | chr14:57798423-57798487 |
| 12595 | Mir20b | NR_030273.1 | chrX:52742112-52742192 | | 12690 | Mir3078 | NR_037239.1 | chr14:64591184-64591271 |
| 12596 | Mir21 | NR_029738.1 | chr11:86584086-86584158 | | 12691 | Mir3079 | NR_037240.1 | chr11:5254597-5254622 |
| 12597 | Mir210 | NR_029793.1 | chr7:141221383-141221493 | | 12692 | Mir3081 | NR_037242.1 | chr16:44558045-44558129 |
| 12598 | Mir211 | NR_029805.1 | chr7:64205805-64205911 | | 12693 | Mir3082 | NR_037243.1 | chr17:25831364-25831428 |
| 12599 | Mir212 | NR_029794.1 | chr11:75173387-75173478 | | 12694 | Mir3083 | NR_037244.1 | chr17:26948055-26948119 |
| 12600 | Mir2136 | NR_035516.1 | chr9:104426112-104426187 | | 12695 | Mir3084 | NR_037245.1 | chr19:24942235-24942303 |
| 12601 | Mir2137 | NR_035517.1 | chrX:72992078-72992144 | | 12696 | Mir3084-2 | NR_105743.1 | chr19:24942235-60774397 |
| 12602 | Mir2139 | NR_035519.1 | chr4:139967525-139967620 | | 12697 | Mir3085 | NR_037246.1 | chr19:42280081-42280170 |
| 12603 | Mir214 | NR_029796.1 | chr1:162223367-162223477 | | 12698 | Mir3086 | NR_037247.1 | chr19:58911672-58911759 |
| 12604 | Mir215 | NR_029908.1 | chr1:185313580-185313691 | | 12699 | Mir3087 | NR_037270.1 | chr2:25442778-25442814 |
| 12605 | Mir216a | NR_029797.1 | chr11:28757011-28757083 | | 12700 | Mir3088 | NR_037271.1 | chr2:28733277-28733351 |
| 12606 | Mir216b | NR_030419.1 | chr11:28746190-28746276 | | 12701 | Mir3089 | NR_037272.1 | chr2:30721209-30721293 |
| 12607 | Mir216c | NR_106162.1 | chr11:28746197-28746266 | | 12702 | Mir3091 | NR_037274.1 | chr2:180257535-180257611 |
| 12608 | Mir217 | NR_029828.1 | chr11:28763727-28763835 | | 12703 | Mir3092 | NR_037275.1 | chr3:27584899-27584995 |
| 12609 | Mir218-1 | NR_029798.1 | chr5:48223941-48224051 | | 12704 | Mir3093 | NR_037276.1 | chr3:88215170-88215257 |
| 12610 | Mir218-2 | NR_029799.1 | chr11:35616815-35616925 | | 12705 | Mir3094 | NR_037277.1 | chr4:40993694-40993758 |
| 12611 | Mir219-1 | NR_029800.1 | chr17:34024982-34025092 | | 12706 | Mir3095 | NR_037278.1 | chr4:58441011-58441098 |
| 12612 | Mir219-2 | NR_029838.1 | chr2:29845630-29845727 | | 12707 | Mir3097 | NR_037280.1 | chr5:35021048-35021115 |
| 12613 | Mir219b | NR_106110.1 | chr2:29845646-29845711 | | 12708 | Mir3098 | NR_037281.1 | chr2:131142468-131604824 |
| 12614 | Mir219c | NR_106154.1 | chr17:34025011-34025071 | | 12709 | Mir3099 | NR_037213.1 | chr7:6803586-6803670 |
| 12615 | Mir21b | NR_105796.1 | chr3:29636743-29636851 | | 12710 | Mir30a | NR_029533.1 | chr1:23272268-23272339 |
| 12616 | Mir21c | NR_105822.1 | chr8:128278147-128278225 | | 12711 | Mir30b | NR_029534.1 | chr15:68337414-68337510 |
| 12617 | Mir22 | NR_029739.1 | chr11:75463715-75463810 | | 12712 | Mir30c-1 | NR_029716.1 | chr4:120769533-120769622 |
| 12618 | Mir221 | NR_029806.1 | chrX:19146293-19146388 | | 12713 | Mir30c-2 | NR_029717.1 | chr1:23291700-23291784 |
| 12619 | Mir222 | NR_029807.1 | chrX:19146892-19146971 | | 12714 | Mir30d | NR_029718.1 | chr15:68341207-68341289 |
| 12620 | Mir223 | NR_029801.1 | chrX:96242816-96242926 | | 12715 | Mir30f | NR_105851.1 | chr4:120772605-120772697 |
| 12621 | Mir22hg | NR_029711.1 | chr11:75461538-75466690 | | 12716 | Mir31 | NR_029747.1 | chr4:88910556-88910662 |
| 12622 | Mir23a | NR_029740.1 | chr8:84208517-84208592 | | 12717 | Mir3100 | NR_037282.1 | chr7:19086827-19086892 |
| 12623 | Mir23b | NR_029530.1 | chr13:63300483-63300557 | | 12718 | Mir3101 | NR_037283.1 | chr7:27176005-27176093 |
| 12624 | Mir24-1 | NR_029575.1 | chr13:63301207-63301275 | | 12719 | Mir3102 | NR_037289.1 | chr7:100882305-100882409 |
| 12625 | Mir24-2 | NR_029741.1 | chr8:84208814-84208921 | | 12720 | Mir3103 | NR_037290.1 | chr7:128288368-128288435 |
| 12626 | Mir25 | NR_029787.1 | chr5:138165320-138165404 | | 12721 | Mir3104 | NR_037291.1 | chr7:141992178-141992241 |
| 12627 | Mir26a-1 | NR_029742.1 | chr9:119031795-119031885 | | 12722 | Mir3106 | NR_037214.1 | chr8:16168756-16168838 |
| 12628 | Mir26a-2 | NR_029803.1 | chr10:126995529-126995613 | | 12723 | Mir3107 | NR_037293.1 | chr8:23142572-23142662 |
| 12629 | Mir26b | NR_029743.1 | chr1:74394309-74394394 | | 12724 | Mir3108 | NR_037295.1 | chr8:108936859-108936938 |

Fig. 26 - 68

| | | | |
|---|---|---|---|
| 12725 | Mir3109 | NR_037296.1 | chr9:69456943-69457031 |
| 12726 | Mir3110 | NR_037297.1 | chrX:38210440-38210520 |
| 12727 | Mir3112 | NR_037299.1 | chrX:134075315-134075397 |
| 12728 | Mir32 | NR_029789.1 | chr4:56895228-56895298 |
| 12729 | Mir320 | NR_029802.1 | chr14:70443509-70443591 |
| 12730 | Mir322 | NR_029756.1 | chrX:53054254-53054349 |
| 12731 | Mir323 | NR_029757.1 | chr12:109712507-109712593 |
| 12732 | Mir324 | NR_029758.1 | chr11:70012042-70012131 |
| 12733 | Mir325 | NR_029759.1 | chr13:107761060-107761087 |
| 12734 | Mir326 | NR_029760.1 | chr7:99552268-99552363 |
| 12735 | Mir328 | NR_029761.1 | chr8:105308363-105308460 |
| 12736 | Mir329 | NR_029762.1 | chr12:109713480-109713577 |
| 12737 | Mir33 | NR_029804.1 | chr15:82198121-82198190 |
| 12738 | Mir330 | NR_029763.1 | chr7:19181464-19181562 |
| 12739 | Mir331 | NR_029764.1 | chr10:93963767-93963863 |
| 12740 | Mir335 | NR_029900.1 | chr6:30741298-30741396 |
| 12741 | Mir337 | NR_029765.1 | chr12:109585788-109585885 |
| 12742 | Mir338 | NR_029767.1 | chr11:120014764-120014862 |
| 12743 | Mir339 | NR_029768.1 | chr5:139369649-139369745 |
| 12744 | Mir340 | NR_029769.1 | chr11:50069701-50069799 |
| 12745 | Mir341 | NR_029770.1 | chr12:109611499-109611595 |
| 12746 | Mir343 | NR_030759.1 | chr7:19386642-19386717 |
| 12747 | Mir344 | NR_029772.1 | chr7:61877769-61877864 |
| 12748 | Mir344-2 | NR_030557.1 | chr7:61940026-61940106 |
| 12749 | Mir344b | NR_037285.1 | chr7:61685271-61685351 |
| 12750 | Mir344c | NR_037286.1 | chr7:61837310-61837402 |
| 12751 | Mir344d-1 | NR_037215.1 | chr7:61683123-61683192 |
| 12752 | Mir344d-2 | NR_037216.1 | chr7:61685271-61685351 |
| 12753 | Mir344d-3 | NR_037209.1 | chr7:61726248-61726328 |
| 12754 | Mir344e | NR_037284.1 | chr7:61735536-61735602 |
| 12755 | Mir344f | NR_037288.1 | chr7:62046180-62046248 |
| 12756 | Mir344g | NR_037287.1 | chr7:61982288-61982359 |
| 12757 | Mir344h-1 | NR_049201.1 | chr7:61739369-61742425 |
| 12758 | Mir344i | NR_049204.1 | chr7:62085222-62085310 |
| 12759 | Mir345 | NR_029773.1 | chr12:108836972-108837068 |
| 12760 | Mir346 | NR_029774.1 | chr14:34894608-34894706 |
| 12761 | Mir3470a | NR_037301.1 | chr11:3239901-3462990 |
| 12762 | Mir3470b | NR_037302.1 | chr7:143948404-144443433 |
| 12763 | Mir3471-1 | NR_037304.1 | chr5:23813937-24129968 |
| 12764 | Mir3473 | NR_037311.1 | chrX:13719852-162874995 |
| 12765 | Mir3473c | NR_039566.1 | chr1:191998553-191998634 |
| 12766 | Mir3473d | NR_039583.1 | chr8:111016449-111016530 |
| 12767 | Mir3473e | NR_105859.1 | chr5:31667230-31667340 |
| 12768 | Mir3473f | NR_106164.1 | chr1:106546495-106546631 |
| 12769 | Mir3473g | NR_106202.1 | chr2:126902249-126902385 |
| 12770 | Mir3474 | NR_037312.1 | chr2:158638582-158638640 |
| 12771 | Mir3475 | NR_037208.1 | chrX:140310947-140311012 |
| 12772 | Mir34a | NR_029655.1 | chr4:150068453-150068555 |
| 12773 | Mir34b | NR_029655.1 | chr9:51103561-51103645 |
| 12774 | Mir34c | NR_029654.1 | chr9:51103033-51103110 |
| 12775 | Mir350 | NR_029775.1 | chr1:176772324-176772423 |
| 12776 | Mir351 | NR_029776.1 | chrX:53053254-53053353 |
| 12777 | Mir3535 | NR_106184.1 | chr1:86351980-86352127 |
| 12778 | Mir3544 | NR_049184.1 | chr12:109585812-109585873 |
| 12779 | Mir3547 | NR_105931.1 | chr17:25245550-25245638 |
| 12780 | Mir3569 | NR_106134.1 | chr7:30589379-30589437 |
| 12781 | Mir3572 | NR_039587.1 | chr3:3655961-3656047 |
| 12782 | Mir362 | NR_029851.1 | chrX:7241982-7242046 |
| 12783 | Mir3620 | NR_106147.1 | chrX:150547384-150547445 |
| 12784 | Mir363 | NR_029853.1 | chrX:52741692-52741767 |
| 12785 | Mir365-1 | NR_029855.1 | chr16:13453839-13453926 |
| 12786 | Mir365-2 | NR_029659.1 | chr11:79726399-79726511 |
| 12787 | Mir367 | NR_030268.1 | chr3:127545732-127545807 |
| 12788 | Mir369 | NR_030272.1 | chr12:109743417-109743496 |
| 12789 | Mir370 | NR_029618.1 | chr12:109618257-109618336 |
| 12790 | Mir374 | NR_030418.1 | chrX:103573059-103573154 |
| 12791 | Mir374c | NR_037298.1 | chrX:103573084-103573133 |
| 12792 | Mir375 | NR_029876.1 | chr1:74900657-74900721 |
| 12793 | Mir376a | NR_029877.1 | chr12:109723780-109723848 |
| 12794 | Mir376b | NR_029878.1 | chr12:109723457-109723539 |
| 12795 | Mir376c | NR_030270.1 | chr12:109722717-109722802 |
| 12796 | Mir377 | NR_029878.1 | chr12:109740509-109740577 |
| 12797 | Mir378 | NR_029879.1 | chr9:71963440-71963460 |
| 12798 | Mir378b | NR_039545.1 | chr11:88352772-88352864 |
| 12799 | Mir378c | NR_105813.1 | chr3:97309255-97411316 |
| 12800 | Mir379 | NR_029880.1 | chr12:109709059-109709125 |
| 12801 | Mir380 | NR_029881.1 | chr12:109711802-109711863 |
| 12802 | Mir381 | NR_029882.1 | chr12:109726821-109726896 |
| 12803 | Mir382 | NR_029883.1 | chr12:109733770-109733846 |
| 12804 | Mir383 | NR_029884.1 | chr8:38252132-38252202 |
| 12805 | Mir384 | NR_029910.1 | chrX:105344281-105344369 |
| 12806 | Mir3960 | NR_039536.1 | chr2:32712899-32712972 |
| 12807 | Mir3962 | NR_039539.1 | chr7:144932115-144932135 |
| 12808 | Mir3963 | NR_039540.1 | chr2:135405829-135405850 |
| 12809 | Mir3964 | NR_039542.1 | chr14:109460229-109490814 |
| 12810 | Mir3965 | NR_039544.1 | chr7:99641529-99641549 |
| 12811 | Mir3966 | NR_039543.1 | chr10:97482477-97423562 |
| 12812 | Mir3967 | NR_039548.1 | chr2:22654282-22654350 |
| 12813 | Mir3968 | NR_039549.1 | chr1:115447980-115448060 |
| 12814 | Mir3969 | NR_039550.1 | chr5:87595901-87595993 |
| 12815 | Mir3970 | NR_039552.1 | chr3:27010322-27010345 |
| 12816 | Mir3971 | NR_039553.1 | chr11:75551428-75551511 |
| 12817 | Mir409 | NR_029743.1 | chr12:109743157-109743236 |
| 12818 | Mir410 | NR_029914.1 | chr12:109743714-109743795 |
| 12819 | Mir411 | NR_029916.1 | chr12:109710374-109710256 |
| 12820 | Mir412 | NR_029917.1 | chr12:109743288-109743368 |
| 12821 | Mir421 | NR_030558.1 | chrX:103572920-103572996 |
| 12822 | Mir423 | NR_030756.1 | chr11:77078063-77078172 |
| 12823 | Mir425 | NR_029947.1 | chr9:108568776-108568861 |
| 12824 | Mir429 | NR_029958.1 | chr4:156053904-156053987 |
| 12825 | Mir431 | NR_029951.1 | chr12:109590446-109590537 |
| 12826 | Mir432 | NR_035526.1 | chr12:109594955-109595030 |
| 12827 | Mir433 | NR_029952.1 | chr12:109591714-109591838 |
| 12828 | Mir434 | NR_029953.1 | chr12:109594505-109594599 |
| 12829 | Mir448 | NR_029956.1 | chrX:147158209-147158321 |
| 12830 | Mir449a | NR_029961.1 | chr13:113037533-113037624 |
| 12831 | Mir449b | NR_030602.1 | chr13:113037418-113037498 |
| 12832 | Mir449c | NR_030452.1 | chr13:113035982-113036091 |
| 12833 | Mir450-1 | NR_029963.1 | chrX:53048153-53048244 |
| 12834 | Mir450-2 | NR_030274.1 | chrX:53048298-53048367 |
| 12835 | Mir450b | NR_030494.1 | chrX:53047996-53048078 |
| 12836 | Mir451 | NR_029971.1 | chr11:78073169-78073241 |
| 12837 | Mir452 | NR_029974.1 | chrX:72262223-72262308 |
| 12838 | Mir453 | NR_030559.1 | chr12:109735618-109735700 |
| 12839 | Mir455 | NR_030477.1 | chr4:63256850-63256932 |
| 12840 | Mir463 | NR_030147.1 | chrX:66799222-66799297 |
| 12841 | Mir464 | NR_030149.1 | chrX:66839051-66839125 |
| 12842 | Mir465b-1 | NR_030560.1 | chrX:66829201-66835842 |
| 12843 | Mir465c-1 | NR_030562.1 | chrX:66825954-66832597 |
| 12844 | Mir465d | NR_106148.1 | chrX:66822655-66822713 |
| 12845 | Mir466 | NR_030150.1 | chr14:112021429-112058438 |
| 12846 | Mir4660 | NR_037248.1 | chr12:70808504-70669399 |
| 12847 | Mir466b-2 | NR_030564.1 | chr2:3523300-3523321 |
| 12848 | Mir466b-3 | NR_030565.1 | chr2:10503564-10503645 |
| 12849 | Mir466d | NR_030601.1 | chr2:5379389-5483389 |
| 12850 | Mir466f-1 | NR_030566.1 | chr19:12071789-12413554 |
| 12851 | Mir466f-2 | NR_030567.1 | chr7:28452226-28482345 |
| 12852 | Mir466f-3 | NR_030568.1 | chr14:75004109-75388146 |
| 12853 | Mir466g | NR_030569.1 | chr2:10514594-10514674 |
| 12854 | Mir466h | NR_030570.1 | chr4:81476308-81487013 |
| 12855 | Mir466i | NR_035412.1 | chr13:17747472-17747593 |
| 12856 | Mir466n | NR_037269.1 | chr11:114344525-114749749 |
| 12857 | Mir466p | NR_105742.1 | chr18:65195452-65619615 |
| 12858 | Mir467a-1 | NR_035406.1 | chr2:10476345-10503350 |
| 12859 | Mir467a-10 | NR_037267.1 | chr2:10503273-10503355 |
| 12860 | Mir467a-2 | NR_037249.1 | chr2:10478798-10478880 |
| 12861 | Mir467a-3 | NR_037252.1 | chr2:10483677-10503355 |
| 12862 | Mir467a-5 | NR_037256.1 | chr2:10476341-10500904 |
| 12863 | Mir467a-7 | NR_037261.1 | chr2:10493510-10493592 |
| 12864 | Mir467a-9 | NR_037265.1 | chr2:10498393-10498475 |
| 12865 | Mir467b | NR_030472.1 | chr2:10481247-10481320 |
| 12866 | Mir467c | NR_030571.1 | chr11:86415843-86520291 |
| 12867 | Mir467d | NR_030572.1 | chr2:10507629-10507714 |
| 12868 | Mir467e | NR_030645.1 | chr1:10708386-10865874 |
| 12869 | Mir467f | NR_035420.1 | chr18:52822107-52902647 |
| 12870 | Mir468 | NR_030151.1 | chr6:81896598-81896676 |
| 12871 | Mir470 | NR_030153.1 | chrX:66813950-66814025 |
| 12872 | Mir471 | NR_030154.1 | chrX:66792594-66792661 |
| 12873 | Mir483 | NR_030251.1 | chr7:142654923-142654996 |
| 12874 | Mir484 | NR_030252.1 | chr16:14159625-14159692 |
| 12875 | Mir485 | NR_030253.1 | chr12:109734901-109734974 |
| 12876 | Mir486 | NR_030254.1 | chr8:23142554-23142682 |
| 12877 | Mir487b | NR_030271.1 | chr12:109727332-109727414 |
| 12878 | Mir488 | NR_030441.1 | chr1:158505624-158505733 |
| 12879 | Mir489 | NR_030250.1 | chr6:3721896-3722003 |
| 12880 | Mir490 | NR_030524.1 | chr6:36421741-36421825 |
| 12881 | Mir491 | NR_030478.1 | chr4:88122039-88122125 |
| 12882 | Mir493 | NR_030573.1 | chr12:109580232-109580315 |
| 12883 | Mir494 | NR_030269.1 | chr12:109715317-109715402 |
| 12884 | Mir495 | NR_030446.1 | chr12:109718753-109718816 |
| 12885 | Mir496 | NR_030437.1 | chr12:109739118-109739197 |
| 12886 | Mir496b | NR_105832.1 | chr19:16314891-16315004 |
| 12887 | Mir497 | NR_030444.1 | chr11:70234716-70234800 |
| 12888 | Mir497b | NR_106178.1 | chr11:70234691-70234816 |
| 12889 | Mir499 | NR_030757.1 | chr2:155622879-155622958 |
| 12890 | Mir500 | NR_030495.1 | chrX:7237682-7237774 |
| 12891 | Mir501 | NR_030496.1 | chrX:7241242-7241351 |
| 12892 | Mir503 | NR_030275.1 | chrX:53053983-53054054 |
| 12893 | Mir504 | NR_030574.1 | chrX:59097657-59097736 |
| 12894 | Mir5046 | NR_039555.1 | chr19:6829885-6829944 |
| 12895 | Mir505 | NR_030499.1 | chrX:60894462-60894492 |
| 12896 | Mir509 | NR_030575.1 | chrX:68010104-68010179 |
| 12897 | Mir5098 | NR_039557.1 | chr2:28127350-119928917 |
| 12898 | Mir5100 | NR_039559.1 | chr11:60728662-60728726 |
| 12899 | Mir5101 | NR_039560.1 | chr12:75909102-75909185 |
| 12900 | Mir5103 | NR_039562.1 | chr1:34433120-34433199 |
| 12901 | Mir5104 | NR_039563.1 | chr10:7836380-7836474 |
| 12902 | Mir5106 | NR_039565.1 | chr4:44221194-44221267 |
| 12903 | Mir5107 | NR_039567.1 | chr18:60812075-60812163 |
| 12904 | Mir5108 | NR_039568.1 | chr10:61774736-61774821 |
| 12905 | Mir511 | NR_030609.1 | chr2:14261002-14261081 |
| 12906 | Mir5112 | NR_039572.1 | chr18:82720280-82720340 |
| 12907 | Mir5113 | NR_039573.1 | chr15:80940038-80940120 |
| 12908 | Mir5114 | NR_039574.1 | chr19:44303170-44303231 |
| 12909 | Mir5116 | NR_039576.1 | chrX:56587851-56587914 |
| 12910 | Mir5119 | NR_039579.1 | chr11:98262605-98262662 |
| 12911 | Mir5120 | NR_039580.1 | chr9:107436735-107436755 |
| 12912 | Mir5121 | NR_039581.1 | chr7:45126917-45126991 |
| 12913 | Mir5122 | NR_039582.1 | chr4:133369775-133369864 |
| 12914 | Mir5123 | NR_039584.1 | chr4:40850055-40850138 |

Fig. 26 - 69

| | | | | | | | | |
|---|---|---|---|---|---|---|---|---|
| 12915 | Mir5124 | NR_039585.1 | chr3:93428490-93428511 | | 13010 | Mir6384 | NR_105805.1 | chrX:52378126-52378181 |
| 12916 | Mir5125 | NR_039587.1 | chr12:48219729-48301462 | | 13011 | Mir6385 | NR_105806.1 | chr9:58221149-58221254 |
| 12917 | Mir5126 | NR_039588.1 | chr1:84695838-84695915 | | 13012 | Mir6386 | NR_105808.1 | chr9:92267257-92267361 |
| 12918 | Mir5127 | NR_039589.1 | chr18:81992009-81992080 | | 13013 | Mir6387 | NR_105809.1 | chr12:15800993-15801101 |
| 12919 | Mir5128 | NR_039590.1 | chr9:113951595-113993800 | | 13014 | Mir6388 | NR_105810.1 | chr12:115695719-115695794 |
| 12920 | Mir5129 | NR_039591.1 | chr2:45023099-45023177 | | 13015 | Mir6389 | NR_105812.1 | chr7:57581060-57581162 |
| 12921 | Mir5130 | NR_039592.1 | chr14:102982548-102982632 | | 13016 | Mir6390 | NR_105814.1 | chr14:105623641-105623770 |
| 12922 | Mir5131 | NR_039593.1 | chr14:45657960-45658053 | | 13017 | Mir6391 | NR_105815.1 | chr14:118592368-118592472 |
| 12923 | Mir5132 | NR_039594.1 | chrX:74023527-74023598 | | 13018 | Mir6392 | NR_105816.1 | chr15:84168269-84168377 |
| 12924 | Mir5133 | NR_039595.1 | chr9:62122517-62122594 | | 13019 | Mir6393 | NR_105817.1 | chr15:87795849-87795943 |
| 12925 | Mir5134 | NR_039596.1 | chr7:24234526-24234604 | | 13020 | Mir6394 | NR_105818.1 | chr7:96305666-96305765 |
| 12926 | Mir5135 | NR_039597.1 | chr12:76533133-76533212 | | 13021 | Mir6395 | NR_105820.1 | chr8:34166621-34166712 |
| 12927 | Mir5136 | NR_039598.1 | chr19:8888698-8888774 | | 13022 | Mir6396 | NR_105821.1 | chr8:122622264-122622375 |
| 12928 | Mir532 | NR_030242.1 | chrX:7248401-7248497 | | 13023 | Mir6397 | NR_105823.1 | chr4:108087356-108087449 |
| 12929 | Mir539 | NR_030262.1 | chr12:109728128-109728202 | | 13024 | Mir6398 | NR_105824.1 | chr4:123616419-123616521 |
| 12930 | Mir540 | NR_030260.1 | chr12:109586079-109586146 | | 13025 | Mir6399 | NR_105825.1 | chr4:138163208-138163292 |
| 12931 | Mir541 | NR_030263.1 | chr12:109742408-109742498 | | 13026 | Mir6400 | NR_105826.1 | chr4:15942899-15942991 |
| 12932 | Mir542 | NR_030264.1 | chrX:53049402-53049487 | | 13027 | Mir6401 | NR_105827.1 | chr7:139779017-139779126 |
| 12933 | Mir543 | NR_030261.1 | chr12:109717257-109717333 | | 13028 | Mir6402 | NR_105828.1 | chr4:91373283-91373363 |
| 12934 | Mir544 | NR_030610.1 | chr12:109729324-109729402 | | 13029 | Mir6403 | NR_105829.1 | chr4:134567722-134567851 |
| 12935 | Mir546 | NR_030259.1 | chr10:126998439-126998560 | | 13030 | Mir6404 | NR_105830.1 | chr7:143933114-143933208 |
| 12936 | Mir547 | NR_030265.1 | chrX:67988373-67988451 | | 13031 | Mir6405 | NR_105831.1 | chr19:44808405-44808529 |
| 12937 | Mir551b | NR_030422.1 | chr3:29416822-29416920 | | 13032 | Mir6406 | NR_105833.1 | chr11:68226891-68221011 |
| 12938 | Mir5615-1 | NR_049186.1 | chr10:81104613-81104673 | | 13033 | Mir6407 | NR_105834.1 | chr19:53010655-53010756 |
| 12939 | Mir5615-2 | NR_049187.1 | chr10:81104615-81104675 | | 13034 | Mir6408 | NR_105835.1 | chr10:60923022-60923113 |
| 12940 | Mir5616 | NR_049189.1 | chr4:149537862-149537922 | | 13035 | Mir6409 | NR_105836.1 | chr10:76008925-76009017 |
| 12941 | Mir5617 | NR_049190.1 | chrX:20863125-20863182 | | 13036 | Mir6410 | NR_105837.1 | chr10:78434798-78434902 |
| 12942 | Mir5618 | NR_049191.1 | chr9:7784389-7784440 | | 13037 | Mir6411 | NR_105838.1 | chr10:104287268-104287376 |
| 12943 | Mir5619 | NR_049192.1 | chr5:104048002-104048063 | | 13038 | Mir6412 | NR_105839.1 | chr17:30256456-30256535 |
| 12944 | Mir5620 | NR_049193.1 | chr7:7298890-7298946 | | 13039 | Mir6413 | NR_105840.1 | chr10:20297580-20297688 |
| 12945 | Mir5621 | NR_049194.1 | chr1:115795823-115795886 | | 13040 | Mir6414 | NR_105842.1 | chr5:41891341-41891423 |
| 12946 | Mir5622 | NR_049195.1 | chr2:152865066-152865126 | | 13041 | Mir6415 | NR_105843.1 | chr5:92458556-92458656 |
| 12947 | Mir5623 | NR_049196.1 | chr19:58051166-58051236 | | 13042 | Mir6416 | NR_105844.1 | chr7:64249982-64250099 |
| 12948 | Mir5624 | NR_049198.1 | chr13:93790776-93790837 | | 13043 | Mir6417 | NR_105845.1 | chr5:52135901-52136017 |
| 12949 | Mir5625 | NR_049199.1 | chr5:30647935-30648015 | | 13044 | Mir6418 | NR_105846.1 | chr5:137529479-137529594 |
| 12950 | Mir5626 | NR_049200.1 | chr9:70405693-70405753 | | 13045 | Mir6419 | NR_105847.1 | chr2:17563513-17563626 |
| 12951 | Mir5627 | NR_049203.1 | chr12:44210312-44210373 | | 13046 | Mir6420 | NR_105848.1 | chr17:64440805-64440907 |
| 12952 | Mir568 | NR_030576.1 | chr16:43640654-43640737 | | 13047 | Mir6481 | NR_105852.1 | chr3:99199344-99199453 |
| 12953 | Mir5709 | NR_049205.1 | chr17:67026146-67026235 | | 13048 | Mir6516 | NR_105853.1 | chr11:117077347-117077457 |
| 12954 | Mir5710 | NR_049206.1 | chr9:54708312-54708381 | | 13049 | Mir653 | NR_030612.1 | chr6:3721300-3721385 |
| 12955 | Mir574 | NR_030577.1 | chr5:64970317-64970395 | | 13050 | Mir6537 | NR_105855.1 | chr7:25097065-25097175 |
| 12956 | Mir582 | NR_030644.1 | chr13:109324743-109324823 | | 13051 | Mir6538 | NR_105856.1 | chr12:26414900-26415010 |
| 12957 | Mir592 | NR_030420.1 | chr6:27936654-27936750 | | 13052 | Mir6539 | NR_105857.1 | chr14:67859635-67859745 |
| 12958 | Mir598 | NR_030611.1 | chr14:63727188-63727267 | | 13053 | Mir654 | NR_030578.1 | chr12:109723217-109723301 |
| 12959 | Mir599 | NR_035527.1 | chr5:35660830-35660918 | | 13054 | Mir6540 | NR_105858.1 | chr16:42303361-42303469 |
| 12960 | Mir615 | NR_030526.1 | chr15:103014909-103015001 | | 13055 | Mir6541 | NR_105860.1 | chr14:62865541-62865651 |
| 12961 | Mir6236 | NR_105744.1 | chr9:110281286-110281409 | | 13056 | Mir6546 | NR_106103.1 | chr1:171064590-171064652 |
| 12962 | Mir6237 | NR_105745.1 | chr9:9894480-9894621 | | 13057 | Mir664 | NR_035529.1 | chr1:185242974-185243043 |
| 12963 | Mir6238 | NR_105746.1 | chr7:53891760-53891889 | | 13058 | Mir665 | NR_030425.1 | chr12:109586313-109586407 |
| 12964 | Mir6239 | NR_105747.1 | chr14:117953742-117953847 | | 13059 | Mir666 | NR_030435.1 | chr12:109717084-109717183 |
| 12965 | Mir6241 | NR_105749.1 | chr14:118258633-118258736 | | 13060 | Mir667 | NR_030426.1 | chr12:109720005-109720097 |
| 12966 | Mir6244 | NR_105750.1 | chr9:52115622-52115739 | | 13061 | Mir668 | NR_030424.1 | chr12:109734731-109734797 |
| 12967 | Mir6335 | NR_105752.1 | chr2:67781042-67781140 | | 13062 | Mir669a-1 | NR_035408.1 | chr2:10476852-10503883 |
| 12968 | Mir6336 | NR_105754.1 | chr2:42447438-42447568 | | 13063 | Mir669a-2 | NR_030470.1 | chr2:10476850-10510260 |
| 12969 | Mir6337 | NR_105755.1 | chr2:65364295-65364400 | | 13064 | Mir669a-3 | NR_030471.1 | chr2:10474432-10474541 |
| 12970 | Mir6338 | NR_105756.1 | chr11:72388755-72388864 | | 13065 | Mir669a-4 | NR_037250.1 | chr17:51277987-51613053 |
| 12971 | Mir6339 | NR_105757.1 | chr2:130016291-130016408 | | 13066 | Mir669b | NR_030469.1 | chr3:114863252-115027151 |
| 12972 | Mir6340 | NR_105758.1 | chr2:173701029-173701148 | | 13067 | Mir669c | NR_030473.1 | chr12:91110228-91123337 |
| 12973 | Mir6341 | NR_105759.1 | chr1:12425985-12426106 | | 13068 | Mir669e | NR_035426.1 | chr8:39467447-40227787 |
| 12974 | Mir6342 | NR_105760.1 | chr1:29421487-29421612 | | 13069 | Mir669g | NR_035411.1 | chr2:10477149-10477272 |
| 12975 | Mir6343 | NR_105761.1 | chr1:76509559-76509643 | | 13070 | Mir669h | NR_035418.1 | chr10:113586577-113614774 |
| 12976 | Mir6344 | NR_105762.1 | chr1:82131915-82132019 | | 13071 | Mir669i | NR_035417.1 | chr2:10517603-10517730 |
| 12977 | Mir6345 | NR_105763.1 | chr1:93352157-93352285 | | 13072 | Mir669j | NR_035416.1 | chr2:10477909-10478030 |
| 12978 | Mir6348 | NR_105766.1 | chr1:168490642-168490762 | | 13073 | Mir669k | NR_035410.1 | chr2:10475299-10475426 |
| 12979 | Mir6349 | NR_105767.1 | chr1:39186895-39186992 | | 13074 | Mir669m-1 | NR_035474.1 | chr5:78929669-79515904 |
| 12980 | Mir6350 | NR_105768.1 | chr1:47467020-47467125 | | 13075 | Mir669m-2 | NR_035475.1 | chrX:77164402-77475936 |
| 12981 | Mir6352 | NR_105770.1 | chr1:77496652-77496768 | | 13076 | Mir669p-1 | NR_037257.1 | chr17:51277987-51613053 |
| 12982 | Mir6353 | NR_105771.1 | chr1:84218848-84218961 | | 13077 | Mir670 | NR_030431.1 | chr2:94261299-94261399 |
| 12983 | Mir6354 | NR_105772.1 | chr1:62960060-63386069 | | 13078 | Mir671 | NR_030423.1 | chr5:24592113-24592211 |
| 12984 | Mir6355 | NR_105773.1 | chr18:59579629-59579735 | | 13079 | Mir671s | NR_106146.1 | chr19:55192677-55192734 |
| 12985 | Mir6356 | NR_105774.1 | chr18:68739399-68739501 | | 13080 | Mir672 | NR_030430.1 | chrX:104116174-104116274 |
| 12986 | Mir6357 | NR_105775.1 | chr18:70516785-70516889 | | 13081 | Mir673 | NR_030438.1 | chr12:109571989-109572080 |
| 12987 | Mir6358 | NR_105776.1 | chr18:76170551-76170652 | | 13082 | Mir674 | NR_030440.1 | chr2:117185126-117185226 |
| 12988 | Mir6359 | NR_105777.1 | chr18:88972029-88972110 | | 13083 | Mir675 | NR_030416.1 | chr7:142577063-142577147 |
| 12989 | Mir6360 | NR_105778.1 | chr18:23774863-23774989 | | 13084 | Mir676 | NR_030525.1 | chrX:100381096-100381185 |
| 12990 | Mir6361 | NR_105779.1 | chr18:32880572-32880673 | | 13085 | Mir6769b | NR_106035.1 | chr8:71631046-71631106 |
| 12991 | Mir6362 | NR_105781.1 | chr5:29789010-29970488 | | 13086 | Mir677 | NR_030442.1 | chr10:128085285-128085363 |
| 12992 | Mir6363 | NR_105782.1 | chr16:50727131-50727245 | | 13087 | Mir678 | NR_030443.1 | chr10:76207325-76207409 |
| 12993 | Mir6364 | NR_105783.1 | chr2:166672717-166722152 | | 13088 | Mir679 | NR_030445.1 | chr12:109715576-109715650 |
| 12994 | Mir6365 | NR_105784.1 | chr16:13471079-13471180 | | 13089 | Mir680-2 | NR_030448.1 | chr2:220577712-22379223 |
| 12995 | Mir6366 | NR_105785.1 | chr16:18165088-18165170 | | 13090 | Mir680-3 | NR_030449.1 | chr10:25867369-25894505 |
| 12996 | Mir6367 | NR_105786.1 | chr19:9017903-9017931 | | 13091 | Mir681 | NR_030450.1 | chr12:69763834-69763944 |
| 12997 | Mir6368 | NR_105787.1 | chr13:28710780-28710873 | | 13092 | Mir682 | NR_030451.1 | chr13:75645045-75645141 |
| 12998 | Mir6369 | NR_105788.1 | chr13:58313043-58313149 | | 13093 | Mir683-1 | NR_030453.1 | chr13:50544626-50544734 |
| 12999 | Mir6370 | NR_105789.1 | chr19:19555341-19555461 | | 13094 | Mir683-2 | NR_030647.1 | chr13:50600972-50601080 |
| 13000 | Mir6372 | NR_105791.1 | chr1:26202239-26202348 | | 13095 | Mir684-1 | NR_030454.1 | chr2:7753088-129665839 |
| 13001 | Mir6373 | NR_105792.1 | chr6:102794383-102794485 | | 13096 | Mir684-2 | NR_030455.1 | chr4:11134056-11134182 |
| 13002 | Mir6374 | NR_105793.1 | chr6:83400995-83401102 | | 13097 | Mir686 | NR_030457.1 | chr14:54616676-54616785 |
| 13003 | Mir6375 | NR_105794.1 | chr6:85790139-85790234 | | 13098 | Mir687 | NR_030459.1 | chr14:73206782-73206851 |
| 13004 | Mir6376 | NR_105795.1 | chr6:88104127-88104258 | | 13099 | Mir688 | NR_030460.1 | chr15:102671791-102671866 |
| 13005 | Mir6378 | NR_105802.1 | chr3:34922544-34922651 | | 13100 | Mir6896 | NR_105861.1 | chr1:34117358-34117431 |
| 13006 | Mir6380 | NR_105801.1 | chr11:47739591-48074583 | | 13101 | Mir6897 | NR_105862.1 | chr1:36144251-36144313 |
| 13007 | Mir6381 | NR_105803.1 | chr3:142623859-142623946 | | 13102 | Mir6898 | NR_105863.1 | chr1:36348681-36348758 |
| 13008 | Mir6382 | NR_105803.1 | chrX:106309825-106309935 | | 13103 | Mir6899 | NR_105864.1 | chr1:64042437-64042501 |
| 13009 | Mir6383 | NR_105804.1 | chrX:136183244-136183360 | | 13104 | Mir690 | NR_030463.1 | chr16:28599934-28600043 |

Fig. 26 - 70

| | | | | | | | | |
|---|---|---|---|---|---|---|---|---|
| 13105 | Mir6900 | NR_105865.1 | chr1:92464482-92464542 | | 13200 | Mir6987 | NR_105953.1 | chr19:5679003-5679076 |
| 13106 | Mir6901 | NR_105866.1 | chr1:93274548-93274610 | | 13201 | Mir6988 | NR_105954.1 | chr19:6051333-6051392 |
| 13107 | Mir6902 | NR_105867.1 | chr1:93346091-93346155 | | 13202 | Mir6989 | NR_105955.1 | chr11:46232134-46581905 |
| 13108 | Mir6903 | NR_105868.1 | chr1:133726557-133726645 | | 13203 | Mir6990 | NR_105956.1 | chr19:6914195-6914286 |
| 13109 | Mir6904 | NR_105869.1 | chr1:180587200-180587267 | | 13204 | Mir6991 | NR_105957.1 | chr19:7422572-7422642 |
| 13110 | Mir6905 | NR_105870.1 | chr10:24910663-24910733 | | 13205 | Mir6992 | NR_105958.1 | chr19:8742970-8743079 |
| 13111 | Mir6906 | NR_105871.1 | chr10:60126775-60126833 | | 13206 | Mir6993 | NR_105959.1 | chr19:10191374-10191439 |
| 13112 | Mir6907 | NR_105872.1 | chr10:78408474-78408545 | | 13207 | Mir6994 | NR_105960.1 | chr19:11923727-11923800 |
| 13113 | Mir6908 | NR_105873.1 | chr10:78445094-78445157 | | 13208 | Mir6995 | NR_105961.1 | chr19:47273518-47273589 |
| 13114 | Mir6909 | NR_105874.1 | chr10:79531028-79531090 | | 13209 | Mir6996 | NR_105962.1 | chr2:26470058-26470119 |
| 13115 | Mir691 | NR_030464.1 | chr16:74341989-74342067 | | 13210 | Mir6997 | NR_105963.1 | chr2:29995949-29996020 |
| 13116 | Mir6910 | NR_105875.1 | chr10:79862586-79862652 | | 13211 | Mir6998 | NR_105964.1 | chr2:31612420-31612484 |
| 13117 | Mir6911 | NR_105876.1 | chr10:80278163-80278232 | | 13212 | Mir6999 | NR_105965.1 | chr2:91944869-91944930 |
| 13118 | Mir6912 | NR_105877.1 | chr10:80609259-80609329 | | 13213 | Mir700 | NR_030481.1 | chr4:135416554-135416633 |
| 13119 | Mir6913 | NR_105878.1 | chr10:81386346-81386412 | | 13214 | Mir7000 | NR_105966.1 | chr2:92387383-92387446 |
| 13120 | Mir6914 | NR_105879.1 | chr10:128382837-128382906 | | 13215 | Mir7001 | NR_105967.1 | chr2:93421928-93422007 |
| 13121 | Mir6915 | NR_105880.1 | chr10:128388831-128388900 | | 13216 | Mir7002 | NR_105968.1 | chr2:114150515-114150570 |
| 13122 | Mir6916 | NR_105881.1 | chr10:128511967-128512030 | | 13217 | Mir7003 | NR_105970.1 | chr2:163068089-163068155 |
| 13123 | Mir6917 | NR_105882.1 | chr10:128584436-128584497 | | 13218 | Mir7004 | NR_105971.1 | chr2:168640695-168640759 |
| 13124 | Mir6918 | NR_105883.1 | chr11:4891344-4891402 | | 13219 | Mir7005 | NR_105972.1 | chr2:180179754-180179823 |
| 13125 | Mir6919 | NR_105884.1 | chr11:50232244-50232306 | | 13220 | Mir7006 | NR_105973.1 | chr2:181587899-181587968 |
| 13126 | Mir6920 | NR_105885.1 | chr11:53409196-53409267 | | 13221 | Mir7007 | NR_105974.1 | chr3:20222289-20222359 |
| 13127 | Mir6921 | NR_105886.1 | chr11:60200537-60200617 | | 13222 | Mir7008 | NR_105975.1 | chr3:31038965-31039028 |
| 13128 | Mir692-1 | NR_030465.1 | chr17:6895228-6895337 | | 13223 | Mir7009 | NR_105976.1 | chr3:36475460-36475524 |
| 13129 | Mir6922 | NR_105887.1 | chr11:60202261-60202327 | | 13224 | Mir701 | NR_030482.1 | chr5:111004143-111004252 |
| 13130 | Mir692-2b | NR_035409.1 | chr4:74407064-125504857 | | 13225 | Mir7010 | NR_105977.1 | chr3:82106246-82106309 |
| 13131 | Mir6923 | NR_105888.1 | chr11:67099803-67099875 | | 13226 | Mir7011 | NR_105978.1 | chr3:88440878-88440951 |
| 13132 | Mir6924 | NR_105889.1 | chr11:69882031-69882094 | | 13227 | Mir7012 | NR_105979.1 | chr3:90270148-90270212 |
| 13133 | Mir6925 | NR_105890.1 | chr11:70705989-70706059 | | 13228 | Mir7013 | NR_105980.1 | chr3:95004167-95004239 |
| 13134 | Mir6926 | NR_105891.1 | chr11:74868126-74868194 | | 13229 | Mir7014 | NR_105981.1 | chr3:95734910-95734973 |
| 13135 | Mir6927 | NR_105892.1 | chr11:97677059-97677130 | | 13230 | Mir7015 | NR_105982.1 | chr4:120973258-120973322 |
| 13136 | Mir6928 | NR_105893.1 | chr11:101030339-101030409 | | 13231 | Mir7016 | NR_105983.1 | chr4:129684499-129684571 |
| 13137 | Mir6929 | NR_105894.1 | chr11:101419186-101419253 | | 13232 | Mir7017 | NR_105984.1 | chr4:133195654-133195716 |
| 13138 | Mir693 | NR_030475.1 | chr17:46231530-46231619 | | 13233 | Mir7018 | NR_105985.1 | chr4:137538285-137538370 |
| 13139 | Mir6930 | NR_105895.1 | chr11:102404919-102404987 | | 13234 | Mir7019 | NR_105986.1 | chr4:138316131-138316200 |
| 13140 | Mir6931 | NR_105896.1 | chr11:102999847-102999921 | | 13235 | Mir702 | NR_030483.1 | chr4:136991432-136991541 |
| 13141 | Mir6932 | NR_105897.1 | chr11:107637721-107637779 | | 13236 | Mir7020 | NR_105987.1 | chr4:139644041-139644111 |
| 13142 | Mir6933 | NR_105898.1 | chr11:118002269-118002350 | | 13237 | Mir7021 | NR_105988.1 | chr4:143136099-143136162 |
| 13143 | Mir6934 | NR_105899.1 | chr11:119154075-119154137 | | 13238 | Mir7022 | NR_105989.1 | chr4:148146935-148146996 |
| 13144 | Mir6935 | NR_105900.1 | chr11:120347349-120347413 | | 13239 | Mir7023 | NR_105990.1 | chr4:149655503-149655567 |
| 13145 | Mir6936 | NR_105901.1 | chr11:120624822-120624876 | | 13240 | Mir7024 | NR_105991.1 | chr5:33898909-33898971 |
| 13146 | Mir6937 | NR_105902.1 | chr12:28679324-28679389 | | 13241 | Mir7025 | NR_105992.1 | chr5:75176830-75176904 |
| 13147 | Mir6938 | NR_105903.1 | chr12:85245922-85245985 | | 13242 | Mir7026 | NR_105993.1 | chr5:110666074-110666141 |
| 13148 | Mir6939 | NR_105904.1 | chr12:112659276-112659351 | | 13243 | Mir7027 | NR_105994.1 | chr5:114404467-114404539 |
| 13149 | Mir694 | NR_030474.1 | chr18:66219263-66219333 | | 13244 | Mir7028 | NR_105995.1 | chr5:114719514-114719578 |
| 13150 | Mir6940 | NR_105905.1 | chr12:112733321-112733391 | | 13245 | Mir7029 | NR_105996.1 | chr5:115580948-115581009 |
| 13151 | Mir6941 | NR_105906.1 | chr12:112920482-112920541 | | 13246 | Mir703 | NR_030484.1 | chr5:98475555-98475664 |
| 13152 | Mir6942 | NR_105907.1 | chr13:21396577-21396638 | | 13247 | Mir7030 | NR_105997.1 | chr5:115645572-115645632 |
| 13153 | Mir6943 | NR_105908.1 | chr13:55453105-55453171 | | 13248 | Mir7031 | NR_105998.1 | chr5:121819208-121819273 |
| 13154 | Mir6944 | NR_105909.1 | chr13:55477680-55477776 | | 13249 | Mir7032 | NR_105999.1 | chr5:123996851-123996930 |
| 13155 | Mir6945 | NR_105910.1 | chr13:55507624-55507692 | | 13250 | Mir7033 | NR_106000.1 | chr5:135383729-135383810 |
| 13156 | Mir6946 | NR_105911.1 | chr14:20690634-20690703 | | 13251 | Mir7034 | NR_106001.1 | chr5:135735805-135735889 |
| 13157 | Mir6947 | NR_105912.1 | chr14:29988887-29988952 | | 13252 | Mir7035 | NR_106002.1 | chr5:136105521-136105603 |
| 13158 | Mir6948 | NR_105913.1 | chr14:54643048-54643110 | | 13253 | Mir7036 | NR_106003.1 | chr5:137296623-137296688 |
| 13159 | Mir6949 | NR_105914.1 | chr14:56082400-56082468 | | 13254 | Mir7036b | NR_106111.1 | chr5:34574150-34574213 |
| 13160 | Mir695 | NR_030475.1 | chr2:155356816-155356925 | | 13255 | Mir7037 | NR_106004.1 | chr5:139767878-139767943 |
| 13161 | Mir6950 | NR_105915.1 | chr14:69692247-69692320 | | 13256 | Mir7038 | NR_106005.1 | chr5:140427338-140427409 |
| 13162 | Mir6951 | NR_105916.1 | chr15:38490472-38490547 | | 13257 | Mir7039 | NR_106006.1 | chr5:144896731-144896816 |
| 13163 | Mir6952 | NR_105917.1 | chr15:76064827-76064888 | | 13258 | Mir704 | NR_030485.1 | chr6:47803575-47803652 |
| 13164 | Mir6953 | NR_105918.1 | chr15:76248190-76248258 | | 13259 | Mir7040 | NR_106007.1 | chr6:83049710-83049773 |
| 13165 | Mir6954 | NR_105919.1 | chr15:76433213-76433273 | | 13260 | Mir7041 | NR_106008.1 | chr6:94606363-94606415 |
| 13166 | Mir6955 | NR_105920.1 | chr15:78891839-78891913 | | 13261 | Mir7042 | NR_106009.1 | chr6:113707207-113707265 |
| 13167 | Mir6956 | NR_105921.1 | chr15:79002222-79002284 | | 13262 | Mir7043 | NR_106010.1 | chr6:116645977-116646047 |
| 13168 | Mir6957 | NR_105922.1 | chr15:80646072-80646136 | | 13263 | Mir7044 | NR_106011.1 | chr6:118085191-118085263 |
| 13169 | Mir6958 | NR_105923.1 | chr15:89185464-89185537 | | 13264 | Mir7045 | NR_106012.1 | chr6:125097023-125097086 |
| 13170 | Mir6959 | NR_105924.1 | chr15:89305657-89305732 | | 13265 | Mir7046 | NR_106013.1 | chr7:24970009-24970075 |
| 13171 | Mir6960 | NR_105925.1 | chr15:99080804-99080865 | | 13266 | Mir7047 | NR_106014.1 | chr7:24987603-24987667 |
| 13172 | Mir6961 | NR_105926.1 | chr15:100649162-100649229 | | 13267 | Mir7048 | NR_106015.1 | chr7:25217667-25217725 |
| 13173 | Mir6962 | NR_105927.1 | chr15:101193868-101193931 | | 13268 | Mir7049 | NR_106016.1 | chr7:28560924-28560984 |
| 13174 | Mir6963 | NR_105928.1 | chr15:103350454-103350525 | | 13269 | Mir705 | NR_030486.1 | chr6:85336291-85336373 |
| 13175 | Mir6964 | NR_105929.1 | chr16:97877232-97877291 | | 13270 | Mir7050 | NR_106017.1 | chr7:31040257-31040317 |
| 13176 | Mir6965 | NR_105930.1 | chr17:24240883-24240947 | | 13271 | Mir7051 | NR_106018.1 | chr7:43457496-43457569 |
| 13177 | Mir6966 | NR_105932.1 | chr17:25780807-25780879 | | 13272 | Mir7052 | NR_106019.1 | chr7:44470346-44470411 |
| 13178 | Mir6968 | NR_105934.1 | chr17:26935471-26935539 | | 13273 | Mir7053 | NR_106020.1 | chr7:44538105-44538178 |
| 13179 | Mir6969 | NR_105935.1 | chr17:28558440-28558501 | | 13274 | Mir7054 | NR_106021.1 | chr7:45012425-45012487 |
| 13180 | Mir697 | NR_030476.1 | chr4:124731693-124731802 | | 13275 | Mir7055 | NR_106022.1 | chr7:45173302-45173361 |
| 13181 | Mir6970 | NR_105936.1 | chr17:34845100-34845167 | | 13276 | Mir7056 | NR_106023.1 | chr7:47083165-47083224 |
| 13182 | Mir6971 | NR_105937.1 | chr17:34841808-34841871 | | 13277 | Mir7057 | NR_106024.1 | chr7:66381666-66381724 |
| 13183 | Mir6972 | NR_105938.1 | chr17:34857568-34857632 | | 13278 | Mir7058 | NR_106025.1 | chr7:126367970-126368045 |
| 13184 | Mir6973a | NR_105939.1 | chr17:35194971-35195049 | | 13279 | Mir7059 | NR_106026.1 | chr7:126579473-126579532 |
| 13185 | Mir6973b | NR_105969.1 | chr2:131040318-131040398 | | 13280 | Mir706 | NR_030487.1 | chr6:120034227-120034311 |
| 13186 | Mir6974 | NR_105940.1 | chr17:35204474-35204557 | | 13281 | Mir7060 | NR_106027.1 | chr7:127489250-127489387 |
| 13187 | Mir6975 | NR_105941.1 | chr17:35244074-35244135 | | 13282 | Mir7061 | NR_106028.1 | chr7:130908267-130908335 |
| 13188 | Mir6976 | NR_105942.1 | chr17:46553826-46553889 | | 13283 | Mir7062 | NR_106029.1 | chr7:139986808-139986874 |
| 13189 | Mir6977 | NR_105943.1 | chr17:56418845-56418909 | | 13284 | Mir7063 | NR_106030.1 | chr7:141620700-141620791 |
| 13190 | Mir6978 | NR_105944.1 | chr17:57217171-57217228 | | 13285 | Mir7064 | NR_106031.1 | chr7:143570670-143570759 |
| 13191 | Mir6979 | NR_105945.1 | chr18:37854604-37854660 | | 13286 | Mir7065 | NR_106032.1 | chr8:13136071-13136132 |
| 13192 | Mir698 | NR_030480.1 | chr4:124743780-124743889 | | 13287 | Mir7066 | NR_106033.1 | chr8:70102523-70102586 |
| 13193 | Mir6980 | NR_105946.1 | chr18:37990886-37990945 | | 13288 | Mir7067 | NR_106034.1 | chr8:70895507-70895570 |
| 13194 | Mir6981 | NR_105947.1 | chr18:37974502-37974617 | | 13289 | Mir7068 | NR_106036.1 | chr8:72470015-72470089 |
| 13195 | Mir6982 | NR_105948.1 | chr18:60958072-60958140 | | 13290 | Mir7069 | NR_106037.1 | chr8:84867946-84868008 |
| 13196 | Mir6983 | NR_105949.1 | chr18:61117467-61117531 | | 13291 | Mir707 | NR_030488.1 | chr7:44849698-44849771 |
| 13197 | Mir6984 | NR_105950.1 | chr19:3288919-3288983 | | 13292 | Mir7070 | NR_106038.1 | chr8:85062085-85062171 |
| 13198 | Mir6985 | NR_105951.1 | chr19:4263817-4263878 | | 13293 | Mir7071 | NR_106039.1 | chr8:88138205-88138274 |
| 13199 | Mir6986 | NR_105952.1 | chr19:4623897-4623955 | | 13294 | Mir7072 | NR_106040.1 | chr8:94505045-94505105 |

Fig. 26 - 71

| | | | | | | | | |
|---|---|---|---|---|---|---|---|---|
| 13295 | Mir7073 | NR_106041.1 | chr8:95753150-95753214 | | 13390 | Mir7658 | NR_106118.1 | chr4:156230058-156230115 |
| 13296 | Mir7074 | NR_106042.1 | chr8:105951636-105951699 | | 13391 | Mir7661 | NR_106121.1 | chr6:108489742-108489803 |
| 13297 | Mir7075 | NR_106043.1 | chr8:107096024-107096106 | | 13392 | Mir7662 | NR_106122.1 | chr10:62194166-62194227 |
| 13298 | Mir7076 | NR_106044.1 | chr8:111689600-111689674 | | 13393 | Mir7663 | NR_106123.1 | chr10:22729371-22729432 |
| 13299 | Mir7077 | NR_106045.1 | chr8:117453022-117453079 | | 13394 | Mir7665 | NR_106125.1 | chr2:120017516-120017579 |
| 13300 | Mir7078 | NR_106046.1 | chr8:117459264-117459328 | | 13395 | Mir7666 | NR_106126.1 | chr8:40307874-40307929 |
| 13301 | Mir7079 | NR_106047.1 | chr8:123104974-123105043 | | 13396 | Mir7667 | NR_106127.1 | chr9:21168377-21226281 |
| 13302 | Mir708 | NR_030489.1 | chr7:96249423-96249532 | | 13397 | Mir7668 | NR_106128.1 | chr7:29906508-29906567 |
| 13303 | Mir7080 | NR_106048.1 | chr8:123130105-123130172 | | 13398 | Mir7669 | NR_106129.1 | chr3:90011152-90011210 |
| 13304 | Mir7081 | NR_106049.1 | chr9:20914089-20914164 | | 13399 | Mir767 | NR_035528.1 | chrX:72589987-72590094 |
| 13305 | Mir7082 | NR_106050.1 | chr9:21075496-21075588 | | 13400 | Mir7670 | NR_106130.1 | chr6:38507324-38507393 |
| 13306 | Mir7083 | NR_106051.1 | chr9:21809940-21810000 | | 13401 | Mir7671 | NR_106131.1 | chr11:53763596-53763654 |
| 13307 | Mir7084 | NR_106052.1 | chr9:22113949-22114013 | | 13402 | Mir7672 | NR_106132.1 | chr14:26669546-26669608 |
| 13308 | Mir7085 | NR_106053.1 | chr9:44400422-44400488 | | 13403 | Mir7673 | NR_106133.1 | chrX:94274573-94274637 |
| 13309 | Mir7086 | NR_106054.1 | chr9:45266642-45266707 | | 13404 | Mir7674 | NR_106135.1 | chr2:32050945-32051008 |
| 13310 | Mir7087 | NR_106055.1 | chr9:45939520-45939590 | | 13405 | Mir7675 | NR_106136.1 | chr12:11299886-11299944 |
| 13311 | Mir7088 | NR_106056.1 | chr9:108081497-108081583 | | 13406 | Mir7676-2 | NR_106138.1 | chr15:78284787-78348660 |
| 13312 | Mir7089 | NR_106057.1 | chr9:109889642-109889710 | | 13407 | Mir7677 | NR_106142.1 | chr17:27091244-27091311 |
| 13313 | Mir709 | NR_030490.1 | chr8:84086098-84086186 | | 13408 | Mir7678 | NR_106143.1 | chr2:164354312-164354383 |
| 13314 | Mir7090 | NR_106058.1 | chr9:120955085-120955147 | | 13409 | Mir7679 | NR_106144.1 | chr11:82985002-82985065 |
| 13315 | Mir7091 | NR_106059.1 | chrX:74274026-74274105 | | 13410 | Mir7680 | NR_106145.1 | chr18:21256012-21256066 |
| 13316 | Mir7092 | NR_106060.1 | chrX:74317361-74317429 | | 13411 | Mir7681 | NR_106149.1 | chr1:53849423-53849495 |
| 13317 | Mir7093 | NR_106061.1 | chrX:134757630-134757731 | | 13412 | Mir7682 | NR_106150.1 | chr1:151442392-151442450 |
| 13318 | Mir7094-1 | NR_106062.1 | chr12:114469406-114469466 | | 13413 | Mir7684 | NR_106153.1 | chr15:82393918-82393978 |
| 13319 | Mir7094-2 | NR_106063.1 | chr12:114513634-114513694 | | 13414 | Mir7685 | NR_106156.1 | chr2:158243503-158243565 |
| 13320 | Mir7-1 | NR_029825.1 | chr13:58392778-58392886 | | 13415 | Mir7686 | NR_106157.1 | chr7:139957565-139957622 |
| 13321 | Mir710 | NR_030491.1 | chr8:64514331-64514441 | | 13416 | Mir7687 | NR_106159.1 | chr8:120538695-120538754 |
| 13322 | Mir711 | NR_030492.1 | chr9:108969921-108970003 | | 13417 | Mir770 | NR_030427.1 | chr12:109563691-109563785 |
| 13323 | Mir7115 | NR_106064.1 | chr11:70438254-70438318 | | 13418 | Mir7b | NR_029827.1 | chr17:56242987-56243098 |
| 13324 | Mir7117 | NR_106065.1 | chr15:27571493-27571558 | | 13419 | Mir802 | NR_030429.1 | chr16:93369719-93369816 |
| 13325 | Mir7118 | NR_106066.1 | chr5:89162847-89162908 | | 13420 | Mir804 | NR_030529.1 | chr11:50357784-50357879 |
| 13326 | Mir7119 | NR_106067.1 | chr4:126559859-126559918 | | 13421 | Mir8091 | NR_106166.1 | chr19:41588650-41588789 |
| 13327 | Mir713 | NR_030493.1 | chr13:62760738-62760846 | | 13422 | Mir8092 | NR_106167.1 | chr19:40894702-40894789 |
| 13328 | Mir717 | NR_030497.1 | chrX:52422406-52422515 | | 13423 | Mir8093 | NR_106168.1 | chr2:32687629-32687766 |
| 13329 | Mir718 | NR_030758.1 | chrX:74023848-74023936 | | 13424 | Mir8094 | NR_106169.1 | chr17:35251288-35251405 |
| 13330 | Mir719 | NR_030458.1 | chr14:60228805-60228915 | | 13425 | Mir8095 | NR_106170.1 | chr16:22532055-22532184 |
| 13331 | Mir7-2 | NR_029826.1 | chr7:78888276-78888373 | | 13426 | Mir8096 | NR_106172.1 | chr1:85751947-85752074 |
| 13332 | Mir721 | NR_030500.1 | chr5:136375715-136375803 | | 13427 | Mir8097 | NR_106173.1 | chr15:36240045-36240164 |
| 13333 | Mir7210 | NR_106069.1 | chr14:24088876-24088930 | | 13428 | Mir8098 | NR_106174.1 | chr14:62837726-62837857 |
| 13334 | Mir7211 | NR_106070.1 | chr10:94586136-94586199 | | 13429 | Mir8099-1 | NR_106175.1 | chr3:93927337-95139186 |
| 13335 | Mir7212 | NR_106071.1 | chr15:25948226-25948287 | | 13430 | Mir8100 | NR_106177.1 | chr11:46102268-46102390 |
| 13336 | Mir7213 | NR_106072.1 | chr15:79998969-79999026 | | 13431 | Mir8101 | NR_106179.1 | chr11:102230039-102230150 |
| 13337 | Mir7214 | NR_106073.1 | chr17:27317034-27317095 | | 13432 | Mir8102 | NR_106180.1 | chr11:97744896-97745035 |
| 13338 | Mir7215 | NR_106074.1 | chr10:62682507-62682558 | | 13433 | Mir8103 | NR_106181.1 | chr11:97063767-97063874 |
| 13339 | Mir7216 | NR_106075.1 | chr17:27328384-27328460 | | 13434 | Mir8104 | NR_106182.1 | chr10:122679314-122679415 |
| 13340 | Mir7217 | NR_106076.1 | chr17:27355737-27355799 | | 13435 | Mir8105 | NR_106183.1 | chr10:128458679-128458768 |
| 13341 | Mir7218 | NR_106077.1 | chr17:27358096-27358155 | | 13436 | Mir8106 | NR_106185.1 | chr9:122273889-122274028 |
| 13342 | Mir7219 | NR_106078.1 | chr18:68260919-68260973 | | 13437 | Mir8107 | NR_106186.1 | chr9:110635998-110636115 |
| 13343 | Mir7220 | NR_106079.1 | chr18:60953872-60953932 | | 13438 | Mir8108 | NR_106187.1 | chr8:25159124-25159233 |
| 13344 | Mir7221 | NR_106080.1 | chr2:92592205-92592277 | | 13439 | Mir8109 | NR_106189.1 | chr8:85700904-85701023 |
| 13345 | Mir7222 | NR_106081.1 | chr2:92594601-92594676 | | 13440 | Mir8110 | NR_106190.1 | chr8:89024734-89024831 |
| 13346 | Mir7223 | NR_106082.1 | chr11:107996847-107996916 | | 13441 | Mir8111 | NR_106191.1 | chr8:84005627-84005764 |
| 13347 | Mir7224 | NR_106083.1 | chr2:67675456-67675516 | | 13442 | Mir8112 | NR_106192.1 | chr6:71271670-71271801 |
| 13348 | Mir7225 | NR_106084.1 | chr3:97690508-97690562 | | 13443 | Mir8113 | NR_106193.1 | chr6:125234683-125234812 |
| 13349 | Mir7226 | NR_106085.1 | chr4:118210504-118210564 | | 13444 | Mir8114 | NR_106194.1 | chr1:153899925-153900036 |
| 13350 | Mir7227 | NR_106086.1 | chr4:133717049-133717108 | | 13445 | Mir8115 | NR_106195.1 | chr11:86656070-87483748 |
| 13351 | Mir7228 | NR_106087.1 | chr5:134572075-134572114 | | 13446 | Mir8116 | NR_106196.1 | chr5:137293779-137293876 |
| 13352 | Mir7229 | NR_106088.1 | chr5:113324492-113324545 | | 13447 | Mir8118 | NR_106198.1 | chr4:33438080-33438209 |
| 13353 | Mir7230 | NR_106089.1 | chr5:113337589-113337645 | | 13448 | Mir8119 | NR_106199.1 | chr4:129557682-129557811 |
| 13354 | Mir7231 | NR_106090.1 | chr6:122831376-122831437 | | 13449 | Mir8120 | NR_106200.1 | chr3:65659287-65659426 |
| 13355 | Mir7232 | NR_106091.1 | chr6:81895589-81895663 | | 13450 | Mir871 | NR_030536.1 | chrX:66810427-66810504 |
| 13356 | Mir7233 | NR_106092.1 | chr6:127788083-127788143 | | 13451 | Mir872 | NR_030604.1 | chr4:94665156-94665237 |
| 13357 | Mir7234 | NR_106093.1 | chr7:73819589-73819641 | | 13452 | Mir873b | NR_105849.1 | chr4:36668509-36668586 |
| 13358 | Mir7235 | NR_106094.1 | chr11:97146363-97146419 | | 13453 | Mir874 | NR_030544.1 | chr13:58023124-58023200 |
| 13359 | Mir7236 | NR_106095.1 | chr11:121387144-121387204 | | 13454 | Mir875 | NR_030606.1 | chr15:35660969-35661047 |
| 13360 | Mir7237 | NR_106096.1 | chr8:121978023-121978086 | | 13455 | Mir876 | NR_030545.1 | chr4:36645372-36645453 |
| 13361 | Mir7238 | NR_106097.1 | chr8:11635693-11635736 | | 13456 | Mir877 | NR_030608.1 | chr17:35960729-35960814 |
| 13362 | Mir7239 | NR_106098.1 | chr11:46170086-46170143 | | 13457 | Mir878 | NR_030603.1 | chrX:66801507-66801585 |
| 13363 | Mir7240 | NR_106099.1 | chr8:70798134-70798192 | | 13458 | Mir879 | NR_030537.1 | chr5:9375703-9375779 |
| 13364 | Mir7241 | NR_106100.1 | chr9:67727716-67727780 | | 13459 | Mir880 | NR_030538.1 | chrX:66800529-66800607 |
| 13365 | Mir7242 | NR_106101.1 | chr9:67729498-67729577 | | 13460 | Mir881 | NR_030539.1 | chrX:66801943-66802021 |
| 13366 | Mir7243 | NR_106163.1 | chr9:102304923-102304975 | | 13461 | Mir882 | NR_030540.1 | chr12:109682196-109682273 |
| 13367 | Mir741 | NR_030530.1 | chrX:66796804-66796875 | | 13462 | Mir883a | NR_030541.1 | chrX:66780757-66780833 |
| 13368 | Mir742 | NR_030531.1 | chrX:66780372-66780437 | | 13463 | Mir883b | NR_030542.1 | chrX:66789889-66789967 |
| 13369 | Mir743 | NR_030532.1 | chrX:66776756-66776818 | | 13464 | Mir9-1 | NR_029817.1 | chr3:88215597-88215686 |
| 13370 | Mir743b | NR_030535.1 | chrX:66777255-66777332 | | 13465 | Mir9-2 | NR_029545.1 | chr13:83738813-83738885 |
| 13371 | Mir744 | NR_030417.1 | chr11:65734732-65734832 | | 13466 | Mir92-1 | NR_029816.1 | chr14:115044426-115044506 |
| 13372 | Mir7578 | NR_106102.1 | chr2:27450548-27450630 | | 13467 | Mir92-2 | NR_029748.1 | chrX:52741837-52741928 |
| 13373 | Mir758 | NR_030421.1 | chr12:109712809-109712890 | | 13468 | Mir92b | NR_030579.1 | chr3:89227115-89227198 |
| 13374 | Mir759 | NR_030436.1 | chr14:79738430-79738528 | | 13469 | Mir93 | NR_029749.1 | chr5:138165522-138165610 |
| 13375 | Mir760 | NR_030439.1 | chr3:122293584-122293703 | | 13470 | Mir9-3 | NR_029818.1 | chr7:79505263-79505353 |
| 13376 | Mir761 | NR_030432.1 | chr4:109017654-109017730 | | 13471 | Mir96 | NR_029750.1 | chr6:30169445-30169551 |
| 13377 | Mir762 | NR_030428.1 | chr7:127708486-127708562 | | 13472 | Mir98 | NR_029753.1 | chrX:151913213-151913321 |
| 13378 | Mir764 | NR_030433.1 | chrX:147002258-147002366 | | 13473 | Mir99a | NR_029535.1 | chr16:77598935-77599000 |
| 13379 | Mir7646 | NR_106104.1 | chrX:135746715-135746769 | | 13474 | Mir99b | NR_029536.1 | chr17:17830187-17830257 |
| 13380 | Mir7647 | NR_106105.1 | chr5:123522636-123522695 | | 13475 | Mira | NR_045199.1 | chr6:52214491-52215288 |
| 13381 | Mir7648 | NR_106106.1 | chr15:90224359-90224412 | | 13476 | Mrg | NR_028265.1 | chr12:109734980-109749457 |
| 13382 | Mir7649 | NR_106107.1 | chr6:128931792-128974895 | | 13477 | Mirlet7a-1 | NR_029725.1 | chr13:48538178-48538272 |
| 13383 | Mir7650 | NR_106108.1 | chr6:15312610-15312669 | | 13478 | Mirlet7a-2 | NR_029726.1 | chr9:41536715-41536811 |
| 13384 | Mir7652 | NR_106112.1 | chr1:150024280-150052202 | | 13479 | Mirlet7b | NR_029727.1 | chr15:85707318-85707403 |
| 13385 | Mir7653 | NR_106113.1 | chr1:78178826-78178887 | | 13480 | Mirlet7bhg | NR_110483.1 | chr15:85703772-85707524 |
| 13386 | Mir7654 | NR_106114.1 | chr8:8690092-8690162 | | 13481 | Mirlet7c-1 | NR_029728.1 | chr16:77599656-77599750 |
| 13387 | Mir7655 | NR_106115.1 | chr2:18057845-18057903 | | 13482 | Mirlet7c-2 | NR_029729.1 | chr15:85706602-85706697 |
| 13388 | Mir7656 | NR_106116.1 | chr9:94751828-94751890 | | 13483 | Mirlet7d | NR_029656.1 | chr13:48536011-48536114 |
| 13389 | Mir7657 | NR_106117.1 | chr3:122541624-122541681 | | 13484 | Mirlet7e | NR_029730.1 | chr17:17830351-17830444 |

Fig. 26 - 72

| | | | | | | | |
|---|---|---|---|---|---|---|---|
| 13485 | Mirlet7f-1 | NR_029731.1 | chr13:48537828-48537917 | 13580 | Mob1b | NM_026735.2 | chr5:88720870-88758455 |
| 13486 | Mirlet7f-2 | NR_029732.1 | chrX:151912345-151912428 | 13581 | Mob2 | NM_028308.2 | chr7:142008552-142061034 |
| 13487 | Mirlet7g | NR_029526.1 | chr9:106178839-106178927 | 13582 | Mob3a | NM_172457.2 | chr10:80685252-80701820 |
| 13488 | Mirlet7i | NR_029527.1 | chr10:122985639-122985724 | 13583 | Mob3b | NM_178061.5 | chr4:34949073-35157484 |
| 13489 | Mirlet7j | NR_105798.1 | chr3:140028248-140028370 | 13584 | Mob3c | NM_175308.4 | chr4:115828091-115836183 |
| 13490 | Mirlet7k | NR_105854.1 | chr5:147283188-147283298 | 13585 | Mob4 | NM_025283.3 | chr1:55131244-55154899 |
| 13491 | Mis12 | NM_025993.2 | chr1:71019610-71027134 | 13586 | Mobp | NM_001039864.2 | chr9:120149741-120176091 |
| 13492 | Mis18a | NM_025642.1 | chr16:90719311-90727371 | 13587 | Mocos | NM_026779.1 | chr18:24653690-24701556 |
| 13493 | Mis18bp1 | NM_172578.2 | chr12:65132734-65172580 | 13588 | Mocs1 | NM_020042.2 | chr17:49428363-49455430 |
| 13494 | Misp | NM_030218.2 | chr10:79821020-79830452 | 13589 | Mocs2 | NM_001113374.1 | chr13:114818236-114829420 |
| 13495 | Mitd1 | NM_026913.2 | chr1:37878889-37890411 | 13590 | Mocs3 | NM_001160330.1 | chr2:168230621-168232303 |
| 13496 | Mitf | NM_001113198.1 | chr6:97807057-98021358 | 13591 | Mog | NM_010814.2 | chr17:37010739-37023398 |
| 13497 | Mixl1 | NM_013729.3 | chr1:180693047-180697034 | 13592 | Mogat1 | NM_026713.3 | chr1:78511059-78538173 |
| 13498 | Mki67 | NM_001081117.2 | chr7:135689787-135716379 | 13593 | Mogat2 | NM_177448.4 | chr7:99219083-99238611 |
| 13499 | Mkks | NM_001141946.1 | chr2:136873780-136891406 | 13594 | Mogs | NM_020619.2 | chr6:83115505-83118898 |
| 13500 | Mkl1 | NM_001082536.1 | chr15:81012280-81190757 | 13595 | Mok | NM_011973.2 | chr12:110807797-110840939 |
| 13501 | Mkl2 | NM_001122667.2 | chr16:13256480-13417529 | 13596 | Mon1a | NM_028369.3 | chr9:107888128-107903139 |
| 13502 | Mkln1 | NM_013791.2 | chr6:31398827-31509477 | 13597 | Mon1b | NM_001048143.2 | chr8:113635585-113645192 |
| 13503 | Mkln1os | NR_040300.1 | chr6:31366884-31398773 | 13598 | Mon2 | NM_001163024.1 | chr10:122992060-123076505 |
| 13504 | Mknk1 | NM_001285487.1 | chr4:115839197-115879256 | 13599 | Morc1 | NM_010816.1 | chr16:48431236-48630905 |
| 13505 | Mknk2 | NM_021462.4 | chr10:80665317-80676293 | 13600 | Morc2a | NM_001159288.1 | chr11:3649493-3690370 |
| 13506 | Mkrn1 | NM_018810.2 | chr6:39397820-39420369 | 13601 | Morc2b | NM_177719.4 | chr17:33135589-33139683 |
| 13507 | Mkrn2 | NM_023290.2 | chr6:115601937-115618670 | 13602 | Morc3 | NM_001045529.3 | chr16:93832120-93876073 |
| 13508 | Mkrn3 | NM_011746.2 | chr7:62417592-62420139 | 13603 | Morc4 | NM_001193309.1 | chrX:139821634-139871654 |
| 13509 | Mks1 | NM_001039684.2 | chr11:87853224-87863679 | 13604 | Morf4l1 | NM_001039147.2 | chr9:90091668-90114820 |
| 13510 | Mkx | NM_177595.4 | chr18:6934985-7004779 | 13605 | Morf4l2 | NM_001168225.1 | chr7:136732947-136741155 |
| 13511 | Mlana | NM_029993.1 | chr19:29697940-29708306 | 13606 | Morn1 | NM_001081100.1 | chr4:155086576-155145507 |
| 13512 | Mlc1 | NM_133241.2 | chr15:88955883-88978553 | 13607 | Morn2 | NM_194269.2 | chr17:80290211-80297476 |
| 13513 | Mlec | NM_175403.3 | chr5:115142980-115158176 | 13608 | Morn3 | NM_029112.1 | chr5:123037126-123046820 |
| 13514 | Mlf1 | NM_001039543.2 | chr3:67374096-67400000 | 13609 | Morn4 | NM_198108.2 | chr19:42074938-42086370 |
| 13515 | Mlf2 | NM_001170341.1 | chr6:124931387-124936149 | 13610 | Morn5 | NM_029309.2 | chr2:36049472-36079709 |
| 13516 | Mlh1 | NM_026810.2 | chr9:111228227-111271608 | 13611 | Mos | NM_020021.2 | chr4:3870657-3872105 |
| 13517 | Mlh3 | NM_175337.2 | chr12:85234465-85270599 | 13612 | Mospd1 | NM_001290514.1 | chrX:53344593-53370559 |
| 13518 | Mlip | NM_027710.2 | chr9:77102083-77347870 | 13613 | Mospd2 | NM_001290523.1 | chrX:164936170-164980375 |
| 13519 | Mlkl | NM_029005.3 | chr8:111311797-111338205 | 13614 | Mospd3 | NM_001254762.1 | chr5:137596646-137600708 |
| 13520 | Mllt1 | NM_022328.2 | chr17:56892610-56935388 | 13615 | Mospd4 | NR_045438.1 | chr18:46464933-46465816 |
| 13521 | Mllt10 | NM_001252560.1 | chr2:18064584-18212390 | 13616 | Mov10 | NM_001163440.1 | chr3:104794833-104818563 |
| 13522 | Mllt11 | NM_019914.4 | chr3:95218543-95228677 | 13617 | Mov10l1 | NM_031260.2 | chr15:88982993-89055152 |
| 13523 | Mllt3 | NM_001286158.1 | chr4:87769924-87806323 | 13618 | Moxd1 | NM_021509.5 | chr10:24223516-24302783 |
| 13524 | Mllt4 | NM_010806.1 | chr17:13760540-13905794 | 13619 | Moxd2 | NM_139296.2 | chr6:40878793-40887494 |
| 13525 | Mllt6 | NM_139311.2 | chr11:97663411-97685458 | 13620 | Mpc1 | NM_018819.4 | chr17:8283812-8297661 |
| 13526 | Mlph | NM_053015.3 | chr1:90915099-90951142 | 13621 | Mpc2 | NM_027430.2 | chr1:165461207-165481214 |
| 13527 | Mlst8 | NM_001252463.1 | chr17:24473549-24479078 | 13622 | Mpdu1 | NM_011900.4 | chr11:69656698-69662649 |
| 13528 | Mlx | NM_001159384.1 | chr11:101087289-101092207 | 13623 | Mpdz | NM_010820.3 | chr4:81278498-81442815 |
| 13529 | Mlxip | NM_133917.3 | chr5:123394797-123457931 | 13624 | Mpeg1 | NM_010821.1 | chr19:12460778-12465285 |
| 13530 | Mlxipl | NM_021455.4 | chr5:135106890-135138382 | 13625 | Mpg | NM_010822.3 | chr11:32226504-32232702 |
| 13531 | Mlycd | NM_019966.2 | chr8:119394891-119411088 | 13626 | Mphosph10 | NM_026483.2 | chr7:64376540-64392236 |
| 13532 | Mmaa | NM_133823.4 | chr8:79266423-79294956 | 13627 | Mphosph6 | NM_026758.3 | chr8:117791644-117801929 |
| 13533 | Mmab | NM_029956.3 | chr5:114431033-114444027 | 13628 | Mphosph8 | NM_023773.2 | chr14:56668247-56697429 |
| 13534 | Mmachc | NM_025962.3 | chr4:116702433-116708385 | 13629 | Mphosph9 | NM_001081323.2 | chr5:124250958-124327972 |
| 13535 | Mmadhc | NM_133839.2 | chr2:50279880-50296677 | 13630 | Mpi | NM_025837.2 | chr9:57544267-57552752 |
| 13536 | Mmd | NM_026178.2 | chr11:90249475-90278573 | 13631 | Mpl | NM_001122949.2 | chr4:118442414-118457513 |
| 13537 | Mmd2 | NM_175217.6 | chr5:142563480-142608752 | 13632 | Mplkip | NM_025479.5 | chr13:17695412-17699105 |
| 13538 | Mme | NM_001289462.1 | chr3:63295434-63383713 | 13633 | Mpnd | NM_028530.5 | chr17:56009200-56016783 |
| 13539 | Mmel1 | NM_013783.2 | chr4:154869584-154895530 | 13634 | Mpo | NM_010824.2 | chr11:87793783-87804412 |
| 13540 | Mmgt1 | NM_146234.3 | chrX:56585511-56597919 | 13635 | Mpp1 | NM_008621.3 | chrX:75109732-75131016 |
| 13541 | Mmgt2 | NM_175002.1 | chr11:62648663-62666359 | 13636 | Mpp2 | NM_016695.3 | chr11:102057016-102088515 |
| 13542 | Mmp10 | NM_019471.3 | chr9:7502341-7510242 | 13637 | Mpp3 | NM_007863.2 | chr11:101999652-102026955 |
| 13543 | Mmp11 | NM_008606.3 | chr10:75923221-75932502 | 13638 | Mpp4 | NM_001164682.1 | chr1:59120934-59163389 |
| 13544 | Mmp12 | NM_008605.3 | chr9:7347373-7360461 | 13639 | Mpp5 | NM_019579.3 | chr12:78748946-78840713 |
| 13545 | Mmp13 | NM_008607.2 | chr9:7272513-7283333 | 13640 | Mpp6 | NM_001164733.1 | chr6:50110240-50198598 |
| 13546 | Mmp14 | NM_008608.3 | chr14:54431603-54441258 | 13641 | Mpp7 | NM_001081287.2 | chr18:7347961-7626863 |
| 13547 | Mmp15 | NM_008609.3 | chr8:95352336-95374293 | 13642 | Mppe1 | NM_172630.2 | chr18:67225529-67245830 |
| 13548 | Mmp16 | NM_019724.3 | chr4:17853481-18118734 | 13643 | Mpped1 | NM_172610.3 | chr15:83780022-83858474 |
| 13549 | Mmp17 | NM_011846.4 | chr5:129584213-129608211 | 13644 | Mpped2 | NM_001143683.1 | chr2:106693458-106868360 |
| 13550 | Mmp19 | NM_001164197.1 | chr10:128790909-128800824 | 13645 | Mprip | NM_012027.2 | chr11:59662494-59780860 |
| 13551 | Mmp1a | NM_032006.3 | chr9:7464140-7476869 | 13646 | Mpst | NM_001162492.1 | chr15:78406800-78414015 |
| 13552 | Mmp1b | NM_032007.3 | chr9:7367669-7388026 | 13647 | Mptx1 | NM_025470.3 | chr1:174330517-174332877 |
| 13553 | Mmp2 | NM_008610.2 | chr8:92827327-92853420 | 13648 | Mptx2 | NM_001205011.2 | chr1:173274460-173277756 |
| 13554 | Mmp20 | NM_013903.2 | chr9:7628230-7674968 | 13649 | Mpv17 | NM_008622.6 | chr5:31140662-31154251 |
| 13555 | Mmp21 | NM_152944.1 | chr7:133674269-133680061 | 13650 | Mpv17l | NM_001289561.1 | chr16:13940664-13949619 |
| 13556 | Mmp23 | NM_011985.2 | chr4:155650654-155653384 | 13651 | Mpv17l2 | NM_183170.2 | chr8:70758648-70760921 |
| 13557 | Mmp24 | NM_010808.3 | chr2:155775343-155818366 | 13652 | Mpz | NM_008623.5 | chr1:171150712-171161123 |
| 13558 | Mmp25 | NM_001033339.3 | chr17:23629457-23645269 | 13653 | Mpzl1 | NM_001001880.2 | chr1:165592180-165634541 |
| 13559 | Mmp27 | NM_001030289.1 | chr9:7571457-7581393 | 13654 | Mpzl2 | NM_007962.4 | chr9:45042343-45054043 |
| 13560 | Mmp28 | NM_080455.2 | chr11:83441875-83462961 | 13655 | Mpzl3 | NM_001093749.2 | chr9:45055150-45075042 |
| 13561 | Mmp3 | NM_010809.2 | chr9:7445821-7455974 | 13656 | Mr1 | NM_008209.4 | chr1:155127877-155146780 |
| 13562 | Mmp7 | NM_010810.4 | chr9:7692110-7699416 | 13657 | Mrap | NM_029844.3 | chr16:90738323-90749776 |
| 13563 | Mmp8 | NM_008611.4 | chr9:7558428-7568486 | 13658 | Mrap2 | NM_001101482.2 | chr9:87144305-87184045 |
| 13564 | Mmp9 | NM_013599.3 | chr2:164948218-164955849 | 13659 | Mras | NM_008624.3 | chr9:99385419-99436712 |
| 13565 | Mmrn1 | NM_001163507.1 | chr6:60944316-60989378 | 13660 | Mrc1 | NM_008625.2 | chr2:14229413-14332023 |
| 13566 | Mmrn2 | NM_153127.3 | chr14:34375503-34404286 | 13661 | Mrc2 | NM_008626.3 | chr11:105292645-105351145 |
| 13567 | Mms19 | NM_028152.3 | chr19:41943706-41981136 | 13662 | Mre11a | NM_018736.3 | chr9:14784653-14837126 |
| 13568 | Mms22l | NM_199467.2 | chr4:24496461-24602948 | 13663 | Mreg | NM_001005423.2 | chr1:72159232-72212307 |
| 13569 | Mn1 | NM_001081235.1 | chr5:111418165-111457025 | 13664 | Mrfap1 | NM_026242.3 | chr5:36794866-36796754 |
| 13570 | Mnat1 | NM_008612.2 | chr12:73123716-73273988 | 13665 | Mrgbp | NM_028479.1 | chr2:180581303-180585634 |
| 13571 | Mnd1 | NM_029797.3 | chr3:84087933-84155786 | 13666 | Mrgpra1 | NM_153095.2 | chr7:47334874-47354240 |
| 13572 | Mnd1-ps | NR_030680.1 | chr14:9884094-9886868 | 13667 | Mrgpra2a | NM_001172588.1 | chr7:47426328-47452139 |
| 13573 | Mnda | NM_001033450.4 | chr1:173896340-173913046 | 13668 | Mrgpra2b | NM_153101.3 | chr7:47463806-47489582 |
| 13574 | Mndal | NM_001170853.1 | chr1:173857219-173880187 | 13669 | Mrgpra3 | NM_153067.2 | chr7:47588949-47601572 |
| 13575 | Mns1 | NM_008613.3 | chr9:72438528-72458576 | 13670 | Mrgpra4 | NM_153524.2 | chr7:47980793-47982296 |
| 13576 | Mnt | NM_010813.3 | chr11:74830923-74845725 | 13671 | Mrgpra6 | NM_001308537.1 | chr7:47185766-47189355 |
| 13577 | Mnx1 | NM_019944.2 | chr5:29473822-29478470 | 13672 | Mrgpra9 | NM_001288801.1 | chr7:47234918-47252848 |
| 13578 | Moap1 | NM_001142937.2 | chr12:102739829-102743661 | 13673 | Mrgprb1 | NM_205810.4 | chr7:48444112-48456342 |
| 13579 | Mob1a | NM_145571.2 | chr6:83326038-83340949 | 13674 | Mrgprb2 | NM_175531.4 | chr7:48550965-48558086 |

Fig. 26 - 73

| | | | |
|---|---|---|---|
| 13675 | Mrgprb3 | NM_207537.1 | chr7:48642862-48643801 |
| 13676 | Mrgprb4 | NM_205795.1 | chr7:48198212-48199178 |
| 13677 | Mrgprb5 | NM_207538.1 | chr7:48168016-48168985 |
| 13678 | Mrgprb8 | NM_207539.2 | chr7:48388525-48389648 |
| 13679 | Mrgprd | NM_203490.3 | chr7:145314834-145324059 |
| 13680 | Mrgpre | NM_175534.3 | chr7:143778362-143784500 |
| 13681 | Mrgprf | NM_145379.2 | chr7:145300908-145309557 |
| 13682 | Mrgprg | NM_203492.2 | chr7:143763709-143766993 |
| 13683 | Mrgprh | NM_030726.1 | chr17:12876033-12877842 |
| 13684 | Mrgprx1 | NM_207540.2 | chr7:48020970-48027597 |
| 13685 | Mrgprx2 | NM_001034868.3 | chr7:48478618-48499270 |
| 13686 | Mri1 | NM_026423.4 | chr8:84250575-84257324 |
| 13687 | Mrm1 | NM_145433.1 | chr11:84813060-84819515 |
| 13688 | Mro | NM_027741.3 | chr18:73859384-73879134 |
| 13689 | Mroh1 | NM_001162489.1 | chr15:76390030-76439744 |
| 13690 | Mroh2a | NM_001281466.1 | chr1:88227019-88262289 |
| 13691 | Mroh2b | NM_001166066.1 | chr15:4898736-4962201 |
| 13692 | Mroh4 | NM_001177437.1 | chr15:74606027-74636318 |
| 13693 | Mroh5 | NM_001033365.2 | chr15:73786935-73839671 |
| 13694 | Mroh6 | NM_001282443.1 | chr15:75882933-75888723 |
| 13695 | Mroh7 | NM_001126487.1 | chr4:106680416-106727930 |
| 13696 | Mroh8 | NM_001039557.4 | chr2:157208547-157279549 |
| 13697 | Mroh9 | NM_030071.1 | chr1:163024301-163085670 |
| 13698 | Mrpl1 | NM_001039084.1 | chr5:96210114-96239684 |
| 13699 | Mrpl10 | NM_026154.1 | chr11:97041585-97049213 |
| 13700 | Mrpl11 | NM_025553.4 | chr19:4962305-4966995 |
| 13701 | Mrpl12 | NM_027204.2 | chr11:120484668-120488754 |
| 13702 | Mrpl13 | NM_026759.3 | chr15:55534094-55557312 |
| 13703 | Mrpl14 | NM_026732.2 | chr17:45686371-45698495 |
| 13704 | Mrpl15 | NM_001177658.1 | chr1:4773199-4785726 |
| 13705 | Mrpl16 | NM_025606.3 | chr19:11770414-11774946 |
| 13706 | Mrpl17 | NM_025301.2 | chr7:105803781-105811087 |
| 13707 | Mrpl18 | NM_026310.3 | chr17:12911354-12916091 |
| 13708 | Mrpl19 | NM_026490.2 | chr6:81957841-81965949 |
| 13709 | Mrpl2 | NM_025302.4 | chr17:46646247-46650132 |
| 13710 | Mrpl20 | NM_025570.2 | chr4:155803617-155808829 |
| 13711 | Mrpl21 | NM_172252.3 | chr19:3283046-3292837 |
| 13712 | Mrpl22 | NM_175001.3 | chr11:58171653-58179581 |
| 13713 | Mrpl23 | NM_011288.1 | chr7:142533116-142540742 |
| 13714 | Mrpl24 | NM_026591.3 | chr3:87919543-87923433 |
| 13715 | Mrpl27 | NM_053161.2 | chr11:94653790-94660087 |
| 13716 | Mrpl28 | NM_024227.3 | chr17:26123502-26126613 |
| 13717 | Mrpl3 | NM_053159.3 | chr9:105053267-105077476 |
| 13718 | Mrpl30 | NM_027098.2 | chr1:37890552-37898333 |
| 13719 | Mrpl32 | NM_024177.3 | chr13:14610300-14613037 |
| 13720 | Mrpl33 | NM_025796.3 | chr5:31613950-31622644 |
| 13721 | Mrpl34 | NM_053162.2 | chr8:71464925-71465753 |
| 13722 | Mrpl35 | NM_025430.3 | chr6:71812996-71823784 |
| 13723 | Mrpl36 | NM_053163.1 | chr13:73331008-73332178 |
| 13724 | Mrpl37 | NM_025500.2 | chr4:107055873-107066866 |
| 13725 | Mrpl38 | NM_023167.2 | chr11:116131816-116138868 |
| 13726 | Mrpl39 | NM_017404.4 | chr16:84717579-84735302 |
| 13727 | Mrpl4 | NM_023167.2 | chr9:21002736-21008837 |
| 13728 | Mrpl40 | NM_010922.2 | chr16:18872017-18876637 |
| 13729 | Mrpl41 | NM_001031808.2 | chr2:24972469-24975098 |
| 13730 | Mrpl42 | NM_026065.3 | chr10:95480805-95501927 |
| 13731 | Mrpl43 | NM_053164.3 | chr19:45005013-45006442 |
| 13732 | Mrpl44 | NM_001081210.1 | chr1:79776017-79781445 |
| 13733 | Mrpl45 | NM_025927.4 | chr11:97315715-97329920 |
| 13734 | Mrpl46 | NM_023331.2 | chr7:78775340-78783089 |
| 13735 | Mrpl47 | NM_029017.2 | chr3:32727496-32736755 |
| 13736 | Mrpl48 | NM_198233.1 | chr7:100549116-100583130 |
| 13737 | Mrpl49 | NM_026246.3 | chr19:6053629-6057751 |
| 13738 | Mrpl50 | NM_178603.4 | chr4:49512596-49521083 |
| 13739 | Mrpl51 | NM_025595.5 | chr6:125192199-125194392 |
| 13740 | Mrpl52 | NM_026851.2 | chr14:54426908-54429750 |
| 13741 | Mrpl53 | NM_026744.3 | chr6:83109107-83109932 |
| 13742 | Mrpl54 | NM_025317.2 | chr10:81264721-81266926 |
| 13743 | Mrpl55 | NM_026035.3 | chr11:59202485-59206135 |
| 13744 | Mrpl57 | NM_026401.2 | chr14:57826238-57828745 |
| 13745 | Mrpl9 | NM_030116.2 | chr3:94443335-94448708 |
| 13746 | Mrps10 | NM_001146211.1 | chr7:47368886-47378679 |
| 13747 | Mrps11 | NM_026498.2 | chr7:78783130-78792988 |
| 13748 | Mrps12 | NM_011885.4 | chr7:28739640-28741781 |
| 13749 | Mrps14 | NM_025474.3 | chr1:160195259-160201186 |
| 13750 | Mrps15 | NM_001166031.2 | chr4:126046927-126055536 |
| 13751 | Mrps16 | NM_025440.2 | chr14:20391230-20393555 |
| 13752 | Mrps17 | NM_025450.4 | chr5:129715527-129718691 |
| 13753 | Mrps18a | NM_026768.3 | chr17:46111003-46128908 |
| 13754 | Mrps18b | NM_025878.1 | chr17:35910384-35916369 |
| 13755 | Mrps18c | NM_026826.1 | chr5:100798758-100804467 |
| 13756 | Mrps2 | NM_001166031.2 | chr2:28468065-28471177 |
| 13757 | Mrps21 | NM_078479.3 | chr3:95862651-95870619 |
| 13758 | Mrps22 | NM_025485.3 | chr9:98588729-98601679 |
| 13759 | Mrps23 | NM_001091270.1 | chr8:88194105-88211507 |
| 13760 | Mrps24 | NM_026080.2 | chr11:5703982-5707699 |
| 13761 | Mrps25 | NM_025578.4 | chr6:92169522-92184023 |
| 13762 | Mrps26 | NM_207207.1 | chr2:130563756-130565394 |
| 13763 | Mrps27 | NM_173757.3 | chr13:99344785-99415561 |
| 13764 | Mrps28 | NM_025434.3 | chr3:8802145-8923857 |
| 13765 | Mrps30 | NM_021556.3 | chr13:118380109-118387252 |
| 13766 | Mrps31 | NM_020560.2 | chr8:22411339-22429665 |
| 13767 | Mrps33 | NM_001010930.1 | chr6:39801806-39810936 |
| 13768 | Mrps34 | NM_023260.1 | chr7:24895119-24896273 |
| 13769 | Mrps35 | NM_145573.2 | chr6:147042769-147070902 |
| 13770 | Mrps36 | NM_001190264.1 | chr13:100735939-100744659 |
| 13771 | Mrps5 | NM_029963.2 | chr2:127587425-127603986 |
| 13772 | Mrps6 | NM_080456.1 | chr16:92058335-92112227 |
| 13773 | Mrps7 | NM_025305.2 | chr11:115604150-115607624 |
| 13774 | Mrps9 | NM_023514.4 | chr1:42851232-42905683 |
| 13775 | Mrrf | NM_026422.2 | chr2:36136397-36190283 |
| 13776 | Mrs2 | NM_001013889.2 | chr13:24992294-25020317 |
| 13777 | Mrto4 | NM_001290810.1 | chr4:139347439-139352576 |
| 13778 | Mrvi1 | NM_010826.5 | chr7:110868257-110946187 |
| 13779 | Ms4a1 | NM_007641.5 | chr19:11250602-11266151 |
| 13780 | Ms4a10 | NM_023529.2 | chr19:10962294-10974670 |
| 13781 | Ms4a13 | NM_198224.3 | chr19:11169417-11196723 |
| 13782 | Ms4a15 | NM_001034898.2 | chr19:10978306-10993250 |
| 13783 | Ms4a18 | NM_001251849.1 | chr19:10997024-11017963 |
| 13784 | Ms4a2 | NM_001276328.1 | chr19:11615520-11623719 |
| 13785 | Ms4a3 | NM_133246.5 | chr19:11629498-11640851 |
| 13786 | Ms4a4b | NM_021718.2 | chr19:11443557-11463548 |
| 13787 | Ms4a4c | NM_029499.3 | chr19:11407660-11427246 |
| 13788 | Ms4a4d | NM_025658.4 | chr19:11536848-11558466 |
| 13789 | Ms4a5 | NM_183190.2 | chr19:11273865-11283813 |
| 13790 | Ms4a6b | NM_027209.3 | chr19:11518558-11530403 |
| 13791 | Ms4a6c | NM_001166376.1 | chr19:11469367-11472736 |
| 13792 | Ms4a6d | NM_026835.2 | chr19:11586605-11604804 |
| 13793 | Ms4a7 | NM_001025610.4 | chr19:11321038-11336146 |
| 13794 | Ms4a8a | NM_022430.2 | chr19:11067470-11081103 |
| 13795 | Msantd1 | NM_207277.1 | chr5:34915914-34923839 |
| 13796 | Msantd2 | NM_146222.2 | chr9:37489320-37524150 |
| 13797 | Msantd3 | NM_001145924.1 | chr4:48540080-48561920 |
| 13798 | Msantd4 | NM_145609.1 | chr9:4383536-4386869 |
| 13799 | Msc | NM_010827.2 | chr1:14753345-14755966 |
| 13800 | Msgn1 | NM_019544.1 | chr12:11208381-11208948 |
| 13801 | Msh2 | NM_008628.2 | chr17:87672556-87723713 |
| 13802 | Msh3 | NM_010829.2 | chr13:92211880-92355003 |
| 13803 | Msh4 | NM_001282054.1 | chr3:153857140-153904891 |
| 13804 | Msh5 | NM_001146215.2 | chr17:35028604-35046745 |
| 13805 | Msh6 | NM_010830.2 | chr17:87975049-87990892 |
| 13806 | Msi1 | NM_008629.1 | chr5:115429684-115454202 |
| 13807 | Msi2 | NM_001201341.1 | chr11:88685953-88718267 |
| 13808 | Msl1 | NM_028722.2 | chr11:98795768-98807859 |
| 13809 | Msl2 | NM_001100451.2 | chr9:101074761-101104799 |
| 13810 | Msl3 | NM_010832.5 | chrX:168653098-168673902 |
| 13811 | Msl3l2 | NM_001163833.1 | chr10:56106916-56116880 |
| 13812 | Msln | NM_018857.1 | chr17:25748612-25754327 |
| 13813 | Mslnl | NM_177822.3 | chr17:25736039-25748330 |
| 13814 | Msmb | NM_020597.3 | chr14:32142022-32158326 |
| 13815 | Msmo1 | NM_025436.2 | chr8:64718144-64733978 |
| 13816 | Msmp | NM_001099314.1 | chr4:43583215-43584494 |
| 13817 | Msn | NM_010833.2 | chrX:96096044-96168553 |
| 13818 | Msr1 | NM_001113326.1 | chr8:39581699-39642678 |
| 13819 | Msra | NM_001253712.1 | chr14:64122620-64441040 |
| 13820 | Msrb1 | NM_013759.2 | chr17:24736641-24742778 |
| 13821 | Msrb2 | NM_029619.2 | chr2:19371635-19394971 |
| 13822 | Msrb3 | NM_177092.4 | chr10:120781100-120898971 |
| 13823 | Mss51 | NM_029104.3 | chr14:20482863-20496901 |
| 13824 | Mst1 | NM_008243.3 | chr9:108080435-108085027 |
| 13825 | Mst1r | NM_001287261.1 | chr9:107915002-107920383 |
| 13826 | Mstn | NM_010834.3 | chr1:53061639-53068079 |
| 13827 | Msto1 | NM_144898.2 | chr3:88909615-88913950 |
| 13828 | Msx1 | NM_010835.2 | chr5:37820490-37824585 |
| 13829 | Msx1os | NR_027920.1 | chr5:37820563-37822751 |
| 13830 | Msx2 | NM_013601.2 | chr13:53466880-53472780 |
| 13831 | Msx3 | NM_010836.3 | chr7:140046156-140049088 |
| 13832 | Mt1 | NM_013602.3 | chr8:94179088-94180327 |
| 13833 | Mt2 | NM_008630.2 | chr8:94172617-94173567 |
| 13834 | Mt3 | NM_013603.2 | chr8:94152606-94154148 |
| 13835 | Mt4 | NM_008631.3 | chr8:94137203-94139031 |
| 13836 | Mta1 | NM_054081.2 | chr12:113098277-113137206 |
| 13837 | Mta2 | NM_011842.3 | chr19:8941919-8952300 |
| 13838 | Mta3 | NM_001171052.1 | chr17:83706162-83805422 |
| 13839 | Mtag2 | NR_015480.1 | chr7:45366162-45367948 |
| 13840 | Mtap | NM_024433.2 | chr4:89137369-89181090 |
| 13841 | Mtap7d3 | NM_177293.3 | chrX:56797952-56822325 |
| 13842 | Mtbp | NM_001168250.1 | chr15:55557407-55610813 |
| 13843 | Mtch1 | NM_019880.3 | chr17:29332075-29347904 |
| 13844 | Mtch2 | NM_019758.2 | chr2:90847154-90866634 |
| 13845 | Mtcl1 | NM_001114098.1 | chr17:66336981-66449750 |
| 13846 | Mtcp1 | NM_001039373.5 | chrX:75410441-75416584 |
| 13847 | Mtdh | NM_026002.4 | chr15:34082718-34142385 |
| 13848 | Mterf1a | NM_001013023.2 | chr5:3890580-3893933 |
| 13849 | Mterf1b | NM_001042670.1 | chr5:4192366-4197651 |
| 13850 | Mterfd1 | NM_025547.3 | chr13:66912097-66933072 |
| 13851 | Mterfd2 | NM_178051.4 | chr1:93301204-93305879 |
| 13852 | Mterfd3 | NM_028832.3 | chr10:85119432-85128027 |
| 13853 | Mtf1 | NM_008636.4 | chr4:124802548-124849800 |
| 13854 | Mtf2 | NM_001253877.1 | chr5:108065673-108109219 |
| 13855 | Mtfmt | NM_027134.3 | chr9:65435781-65453054 |
| 13856 | Mtfp1 | NM_026443.4 | chr11:4091480-4095431 |
| 13857 | Mtfr1 | NM_001253390.1 | chr3:19187328-19220817 |
| 13858 | Mtfr1l | NM_001256112.1 | chr4:134525554-134535268 |
| 13859 | Mtfr2 | NM_027930.3 | chr10:20347818-20361669 |
| 13860 | Mtg1 | NM_199301.2 | chr7:140137563-140150786 |
| 13861 | Mtg2 | NM_001083328.1 | chr2:180070592-180085902 |
| 13862 | Mthfd1 | NM_138745.2 | chr12:76255231-76319820 |
| 13863 | Mthfd1l | NM_001170785.1 | chr10:3973074-4167081 |
| 13864 | Mthfd2 | NM_008638.2 | chr6:83305703-83317604 |

Fig. 26 - 74

| | | | | | | | | |
|---|---|---|---|---|---|---|---|---|
| 13865 | Mthfd2l | NM_026788.1 | chr5:90931195-91021370 | | 13960 | Myadml2 | NM_001204820.1 | chr11:120646030-120648337 |
| 13866 | Mthfr | NM_001161798.1 | chr4:148041188-148059562 | | 13961 | Myb | NM_001198914.1 | chr10:21124929-21160984 |
| 13867 | Mthfs | NM_026829.2 | chr9:89211189-89240225 | | 13962 | Mybbp1a | NM_016776.2 | chr11:72441377-72451550 |
| 13868 | Mthfsd | NM_001166482.1 | chr8:121097556-121108379 | | 13963 | Mybl1 | NM_001290397.1 | chr1:9667410-9700209 |
| 13869 | Mtif2 | NM_001282118.1 | chr11:29526396-29545447 | | 13964 | Mybl2 | NM_008652.2 | chr2:163054634-163084687 |
| 13870 | Mtif3 | NM_001256100.1 | chr5:146951577-146963797 | | 13965 | Mybpc1 | NM_001252372.1 | chr10:88518278-88605152 |
| 13871 | Mtl5 | NM_001039657.2 | chr3:3388856-3407823 | | 13966 | Mybpc2 | NM_146189.3 | chr7:44501698-44524669 |
| 13872 | Mtm1 | NM_001164190.1 | chrX:71210766-71315295 | | 13967 | Mybpc3 | NM_008653.2 | chr2:91118143-91136516 |
| 13873 | Mtmr1 | NM_016985.2 | chrX:71364759-71419196 | | 13968 | Mybph | NM_016749.2 | chr1:134193447-134201232 |
| 13874 | Mtmr10 | NM_172742.2 | chr7:64287669-64340806 | | 13969 | Mybphl | NM_026831.1 | chr3:108364910-108380057 |
| 13875 | Mtmr11 | NM_181409.3 | chr3:96161969-96171718 | | 13970 | Myc | NM_001177354.1 | chr15:61985340-61990361 |
| 13876 | Mtmr12 | NM_172958.3 | chr15:12205093-12272240 | | 13971 | Mycbp | NM_019660.3 | chr4:123905012-123912250 |
| 13877 | Mtmr14 | NM_026849.2 | chr6:113237842-113281392 | | 13972 | Mycbp2 | NM_207215.2 | chr14:103113410-103346800 |
| 13878 | Mtmr2 | NM_023858.3 | chr9:13749180-13806481 | | 13973 | Mycbpap | NM_170671.2 | chr11:94501346-94521502 |
| 13879 | Mtmr3 | NM_028860.2 | chr11:4480867-4594815 | | 13974 | Mycl | NM_008506.3 | chr4:122995930-123002480 |
| 13880 | Mtmr4 | NM_133215.1 | chr11:87592215-87616296 | | 13975 | Mycn | NM_008709.3 | chr12:12936092-12941836 |
| 13881 | Mtmr6 | NM_144843.4 | chr14:60265204-60302371 | | 13976 | Mycs | NM_010850.2 | chrX:5466903-5469265 |
| 13882 | Mtmr7 | NM_001040699.1 | chr8:40550158-40634792 | | 13977 | Myct1 | NM_026793.2 | chr10:5593727-5606791 |
| 13883 | Mtmr9 | NM_175594.1 | chr14:63523609-63543953 | | 13978 | Myd88 | NM_010851.2 | chr9:119335987-119340040 |
| 13884 | Mtnr1a | NM_008639.2 | chr8:45069209-45088506 | | 13979 | Myef2 | NM_001162417.1 | chr2:125086270-125123660 |
| 13885 | Mtnr1b | NM_145712.2 | chr9:15862613-15874556 | | 13980 | Myeov2 | NM_001163425.1 | chr1:92637144-92641985 |
| 13886 | Mto1 | NM_026658.2 | chr9:78448209-78474152 | | 13981 | Myf5 | NM_008656.5 | chr10:107482907-107486134 |
| 13887 | Mtor | NM_020009.2 | chr4:148448581-148557685 | | 13982 | Myf6 | NM_008657.2 | chr10:107492859-107494729 |
| 13888 | Mtpap | NM_026157.2 | chr18:4375591-4397330 | | 13983 | Myg1 | NM_021713.2 | chr15:102331708-102338138 |
| 13889 | Mtpn | NM_008098.4 | chr6:35508823-35539888 | | 13984 | Myh1 | NM_030679.1 | chr11:67200113-67224575 |
| 13890 | Mtr | NM_001081128.3 | chr13:12186539-12258113 | | 13985 | Myh10 | NM_175260.2 | chr11:68691914-68816624 |
| 13891 | Mtrf1 | NM_145960.4 | chr14:79397771-79423650 | | 13986 | Myh11 | NM_001161775.1 | chr16:14194526-14291408 |
| 13892 | Mtrf1l | NM_175374.3 | chr10:5811886-5823943 | | 13987 | Myh13 | NM_001081250.1 | chr11:67327102-67371502 |
| 13893 | Mtrr | NM_172483.3 | chr13:68560779-68582169 | | 13988 | Myh14 | NM_001271538.1 | chr7:44605802-44665503 |
| 13894 | Mtss1 | NM_001146180.1 | chr15:58941233-59082026 | | 13989 | Myh15 | NM_001166210.1 | chr16:49057485-49199104 |
| 13895 | Mtss1l | NM_198625.2 | chr8:110721475-110741401 | | 13990 | Myh2 | NM_001039545.2 | chr11:67171026-67197517 |
| 13896 | Mttp | NM_001163457.1 | chr3:138089854-138143388 | | 13991 | Myh3 | NM_001099635.1 | chr11:67078299-67102291 |
| 13897 | Mturn | NM_001289740.1 | chr6:54681623-54703855 | | 13992 | Myh4 | NM_010855.3 | chr11:67237811-67260447 |
| 13898 | Mtus1 | NM_001005863.2 | chr8:40990911-41133726 | | 13993 | Myh6 | NM_001164171.1 | chr14:54941920-54966607 |
| 13899 | Mtus2 | NM_029920.7 | chr5:147957319-148316065 | | 13994 | Myh7 | NM_080728.2 | chr14:54970687-54994549 |
| 13900 | Mtx1 | NM_001161824.1 | chr3:89209080-89214335 | | 13995 | Myh7b | NM_001085378.2 | chr2:155611242-155634307 |
| 13901 | Mtx2 | NM_016804.4 | chr2:74825811-74876748 | | 13996 | Myh8 | NM_177369.3 | chr11:67277123-67308633 |
| 13902 | Mtx3 | NM_001162945.1 | chr13:92844786-92858230 | | 13997 | Myh9 | NM_022410.3 | chr15:77760584-77842175 |
| 13903 | Muc1 | NM_013605.2 | chr3:89229055-89233381 | | 13998 | Myl1 | NM_001133387.1 | chr1:66924295-66935366 |
| 13904 | Muc13 | NM_010739.2 | chr16:33794036-33819927 | | 13999 | Myl10 | NM_001085387.2 | chr5:136694176-136701094 |
| 13905 | Muc15 | NM_001290786.1 | chr2:110721493-110739537 | | 14000 | Myl12a | NM_026064.2 | chr17:70993792-71002533 |
| 13906 | Muc19 | NM_207245.2 | chr15:91838325-91934555 | | 14001 | Myl12b | NM_023402.2 | chr17:70973962-70990516 |
| 13907 | Muc2 | NM_023566.3 | chr7:141690339-141754694 | | 14002 | Myl2 | NM_010861.3 | chr5:122100979-122106854 |
| 13908 | Muc20 | NM_001145874.1 | chr16:32777418-32797435 | | 14003 | Myl3 | NM_010859.2 | chr9:110763680-110769794 |
| 13909 | Muc4 | NM_080457.3 | chr16:32735885-32782390 | | 14004 | Myl4 | NM_010858.4 | chr11:104550662-104587219 |
| 13910 | Muc5ac | NM_010844.1 | chr7:141789010-141819135 | | 14005 | Myl6 | NM_010860.3 | chr10:128490860-128493825 |
| 13911 | Muc5b | NM_028801.2 | chr7:141839071-141873085 | | 14006 | Myl6b | NM_172259.1 | chr10:128494156-128498685 |
| 13912 | Muc6 | NM_181729.2 | chr7:141634048-141655308 | | 14007 | Myl7 | NM_022879.2 | chr11:5896636-5898782 |
| 13913 | Mucl1 | NM_009268.1 | chr15:103751922-103899300 | | 14008 | Myl9 | NM_172118.1 | chr2:156775463-156781657 |
| 13914 | Mug1 | NM_008645.3 | chr6:121838540-121889057 | | 14009 | Mylip | NM_153789.3 | chr13:45389741-45411940 |
| 13915 | Mug2 | NM_008646.3 | chr6:122006797-122085967 | | 14010 | Mylk | NM_139300.3 | chr16:34784949-35002434 |
| 13916 | Mug-ps1 | NR_027619.1 | chr6:122176052-122248566 | | 14011 | Mylk2 | NM_001081044.2 | chr2:152911351-152923065 |
| 13917 | Mul1 | NM_026689.3 | chr4:138434671-138442265 | | 14012 | Mylk3 | NM_175441.5 | chr8:85324928-85365324 |
| 13918 | Mum1 | NM_023431.5 | chr10:80226597-80245144 | | 14013 | Mylk4 | NM_001166030.1 | chr13:32700826-32781779 |
| 13919 | Mum1l1 | NM_001164630.1 | chrX:139210043-139238335 | | 14014 | Mylpf | NM_016754.5 | chr7:127216607-127214287 |
| 13920 | Mup1 | NM_001163010.1 | chr4:60498933-60501960 | | 14015 | Mynn | NM_001289621.1 | chr3:30602086-30619873 |
| 13921 | Mup10 | NM_001122647.1 | chr4:60578260-60582155 | | 14016 | Myo10 | NM_019472.2 | chr15:25622549-25813671 |
| 13922 | Mup11 | NM_001164526.1 | chr4:60658465-60662395 | | 14017 | Myo15 | NM_001103171.1 | chr11:60469338-60528368 |
| 13923 | Mup12 | NM_001199995.1 | chr4:60737380-60741281 | | 14018 | Myo16 | NM_001081397.1 | chr8:10153922-10633950 |
| 13924 | Mup13 | NM_001134674.1 | chr4:61224306-61228286 | | 14019 | Myo18a | NM_001291212.1 | chr11:77777234-77865988 |
| 13925 | Mup14 | NM_001199999.1 | chr4:61300036-61303998 | | 14020 | Myo18b | NM_028901.2 | chr5:112688575-112896362 |
| 13926 | Mup15 | NM_001200001.1 | chr4:60606468-61439704 | | 14021 | Myo19 | NM_025414.3 | chr11:84880219-84911131 |
| 13927 | Mup16 | NM_001199936.1 | chr4:61515592-61519486 | | 14022 | Myo1a | NM_001081219.2 | chr10:127705255-127720940 |
| 13928 | Mup17 | NM_001200006.1 | chr4:61591930-61595832 | | 14023 | Myo1b | NM_001161817.2 | chr1:51749757-51915978 |
| 13929 | Mup19 | NM_001135127.1 | chr4:61778327-61782224 | | 14024 | Myo1c | NM_001080774.1 | chr11:75652149-75674634 |
| 13930 | Mup2 | NM_001045550.2 | chr4:60136846-61439702 | | 14025 | Myo1d | NM_177390.3 | chr11:80482126-80780025 |
| 13931 | Mup20 | NM_001012323.1 | chr4:62050234-62054117 | | 14026 | Myo1e | NM_181072.3 | chr9:70207349-70400067 |
| 13932 | Mup21 | NM_001009550.2 | chr4:62147831-62150841 | | 14027 | Myo1f | NM_053214.2 | chr17:33555706-33607764 |
| 13933 | Mup3 | NM_001039544.1 | chr4:62083475-62087312 | | 14028 | Myo1g | NM_178440.4 | chr11:6506547-6520958 |
| 13934 | Mup4 | NM_008648.1 | chr4:59956805-59960665 | | 14029 | Myo1h | NM_001164573.1 | chr5:114314940-114364576 |
| 13935 | Mup5 | NM_008649.2 | chr4:61831318-61835180 | | 14030 | Myo3a | NM_148413.3 | chr2:22227502-22423370 |
| 13936 | Mup6 | NM_001081285.1 | chr4:60003548-60006214 | | 14031 | Myo3b | NM_177376.4 | chr2:70039125-70429395 |
| 13937 | Mup7 | NM_001134675.1 | chr4:60066468-60070475 | | 14032 | Myo5a | NM_010864.2 | chr9:75071205-75223687 |
| 13938 | Mup8 | NM_001134676.1 | chr4:60218620-60222599 | | 14033 | Myo5b | NM_201600.2 | chr18:74442618-74771477 |
| 13939 | Mup9 | NM_001281979.1 | chr4:60418045-60421952 | | 14034 | Myo5c | NM_001081322.1 | chr9:75232013-75305450 |
| 13940 | Murc | NM_026280.3 | chr4:48665513-48673492 | | 14035 | Myo6 | NM_001039546.2 | chr9:80165033-80311729 |
| 13941 | Mus81 | NM_027877.3 | chr19:5482839-5488336 | | 14036 | Myo7a | NM_001256081.1 | chr7:98051053-98119493 |
| 13942 | Musk | NM_001037127.2 | chr4:58285961-58374303 | | 14037 | Myo7b | NM_032394.3 | chr18:31959233-32036931 |
| 13943 | Mustn1 | NM_181390.3 | chr14:30879256-30881610 | | 14038 | Myo9a | NM_173018.2 | chr9:59751173-59928866 |
| 13944 | Mut | NM_008650.3 | chr17:40934684-40961989 | | 14039 | Myo9b | NM_001142322.1 | chr8:71272713-71360712 |
| 13945 | Mutyh | NM_001159581.1 | chr4:116807733-116819431 | | 14040 | Myoc | NM_010865.3 | chr1:162639149-162649694 |
| 13946 | Mvb12a | NM_028617.2 | chr8:71542929-71548026 | | 14041 | Myocd | NM_145136.4 | chr11:65176570-65269989 |
| 13947 | Mvb12b | NM_175184.4 | chr2:33729955-33887946 | | 14042 | Myod1 | NM_010866.2 | chr7:46376473-46379092 |
| 13948 | Mvd | NM_138656.2 | chr8:122433595-122443422 | | 14043 | Myof | NM_001099634.1 | chr19:37899035-38043577 |
| 13949 | Mvk | NM_023556.4 | chr5:114444268-114460590 | | 14044 | Myog | NM_031189.2 | chr1:134290003-134292548 |
| 13950 | Mvp | NM_080638.3 | chr7:126986859-127014594 | | 14045 | Myom1 | NM_001083934.1 | chr17:71019556-71126856 |
| 13951 | Mx1 | NM_010846.1 | chr16:97447036-97462905 | | 14046 | Myom2 | NM_008664.2 | chr8:15057652-15133419 |
| 13952 | Mx2 | NM_013606.1 | chr16:97536082-97560899 | | 14047 | Myom3 | NM_001085509.2 | chr4:135759714-135815567 |
| 13953 | Mxd1 | NM_010751.3 | chr6:86647044-86669159 | | 14048 | Myot | NM_001033621.3 | chr18:44334073-44355722 |
| 13954 | Mxd3 | NM_016662.4 | chr13:55325167-55329730 | | 14049 | Myoz1 | NM_021508.3 | chr14:20649101-20656540 |
| 13955 | Mxd4 | NM_010753.2 | chr5:34176579-34187710 | | 14050 | Myoz2 | NM_021503.2 | chr3:123006205-123034987 |
| 13956 | Mxi1 | NM_001008542.2 | chr19:53310505-53375810 | | 14051 | Myoz3 | NM_133363.3 | chr18:60573716-60591716 |
| 13957 | Mxra7 | NM_026280.3 | chr11:116803399-116828046 | | 14052 | Mypn | NM_182992.2 | chr10:63115794-63203952 |
| 13958 | Mxra8 | NM_024263.4 | chr4:155839679-155844102 | | 14053 | Mypop | NM_145579.3 | chr7:18991244-19001766 |
| 13959 | Myadm | NM_001093764.1 | chr7:3289037-3299349 | | 14054 | Myrf | NM_001033481.1 | chr19:10208270-10240748 |

Fig. 26 - 75

| | | | |
|---|---|---|---|
| 14055 | Myrf1 | NM_001033333.3 | chr10:116776544-116896879 |
| 14056 | Myrip | NM_144557.5 | chr9:120304072-120474834 |
| 14057 | Mysm1 | NM_177239.2 | chr4:94942040-94979100 |
| 14058 | Myt1 | NM_001171615.1 | chr2:181763331-181827775 |
| 14059 | Myt1l | NM_001093775.1 | chr12:29528383-29923209 |
| 14060 | Myzap | NM_001033208.4 | chr9:71504346-71592360 |
| 14061 | Mzb1 | NM_027222.3 | chr18:35647264-35649367 |
| 14062 | Mzf1 | NM_001290452.1 | chr7:13042302-13054764 |
| 14063 | Mzt1 | NM_175245.4 | chr14:99034543-99046136 |
| 14064 | Mzt2 | NM_029354.2 | chr16:15848440-15863322 |
| 14065 | N28178 | NM_172690.2 | chr4:42917250-42941607 |
| 14066 | N4bp1 | NM_030563.2 | chr8:86841138-86885258 |
| 14067 | N4bp2 | NM_001024917.1 | chr5:65763520-65826784 |
| 14068 | N4bp2l1 | NM_133898.4 | chr5:150571642-150594525 |
| 14069 | N4bp2l2 | NM_201369.3 | chr5:150635972-150665612 |
| 14070 | N4bp3 | NM_145974.3 | chr11:51643088-51651073 |
| 14071 | N6amt1 | NM_001159331.1 | chr16:87354184-87368649 |
| 14072 | N6amt2 | NM_026526.2 | chr14:57549597-57571569 |
| 14073 | Naa10 | NM_001177965.1 | chrX:73916869-73921944 |
| 14074 | Naa11 | NM_001033191.2 | chr5:97382208-97392330 |
| 14075 | Naa15 | NM_053089.3 | chr3:51416015-51475985 |
| 14076 | Naa16 | NM_025832.2 | chr14:79334506-79390668 |
| 14077 | Naa20 | NM_001141965.1 | chr2:145903240-145916425 |
| 14078 | Naa25 | NM_172722.3 | chr5:121397981-121440133 |
| 14079 | Naa30 | NM_001081430.1 | chr14:49172226-49191031 |
| 14080 | Naa35 | NM_030153.2 | chr13:59585332-59634781 |
| 14081 | Naa38 | NM_030083.2 | chr11:69395790-69396671 |
| 14082 | Naa40 | NM_027643.1 | chr9:7225667-7241222 |
| 14083 | Naa50 | NM_028108.3 | chr16:44139808-44163364 |
| 14084 | Naa60 | NM_001290689.1 | chr16:3884618-3904781 |
| 14085 | Naaa | NM_001163687.1 | chr5:92257659-92278181 |
| 14086 | Naalad2 | NM_028279.3 | chr9:18823020-18385928 |
| 14087 | Naaladl1 | NM_001009546.1 | chr19:6105797-6135555 |
| 14088 | Nab1 | NM_008667.3 | chr1:52455848-52500448 |
| 14089 | Nab2 | NM_001222895.1 | chr10:127660917-127666703 |
| 14090 | Nabp1 | NM_028696.3 | chr1:51469487-51478399 |
| 14091 | Nabp2 | NM_027257.1 | chr10:128401394-128409796 |
| 14092 | Naca | NM_001113199.1 | chr10:128035345-128048637 |
| 14093 | Nacad | NM_001081652.1 | chr11:6597822-6606054 |
| 14094 | Nacc1 | NM_025788.3 | chr8:84670478-84687862 |
| 14095 | Nacc2 | NM_001037098.1 | chr2:26055535-26092396 |
| 14096 | Nadk | NM_001159637.1 | chr4:155563814-155591001 |
| 14097 | Nadk2 | NM_001040395.4 | chr15:9071259-9110496 |
| 14098 | Nadsyn1 | NM_030221.2 | chr7:143795590-143822852 |
| 14099 | Nae1 | NM_144931.3 | chr8:104511027-104534637 |
| 14100 | Naf1 | NM_001163564.1 | chr8:66860216-66890564 |
| 14101 | Naga | NM_008669.4 | chr15:82329531-82338826 |
| 14102 | Nagk | NM_001164187.1 | chr6:83795157-83802556 |
| 14103 | Naglu | NM_013792.2 | chr11:101070093-101077671 |
| 14104 | Nagpa | NM_013796.3 | chr16:5195279-5204012 |
| 14105 | Nags | NM_145829.2 | chr11:102145512-102149528 |
| 14106 | Naif1 | NM_194335.2 | chr2:32450456-32455476 |
| 14107 | Naip1 | NM_008670.2 | chr13:100407769-100452864 |
| 14108 | Naip2 | NM_001126182.2 | chr13:100144062-100202122 |
| 14109 | Naip5 | NM_010870.3 | chr13:100211739-100247336 |
| 14110 | Naip6 | NM_010871.2 | chr13:100281120-100316616 |
| 14111 | Naip7 | NM_021545.1 | chr13:100283114-100317688 |
| 14112 | Nalcn | NM_177393.4 | chr14:123276640-123627144 |
| 14113 | Nampt | NM_021524.2 | chr12:32820334-32853369 |
| 14114 | Nanog | NM_001289828.1 | chr6:122707564-122714633 |
| 14115 | Nanos1 | NM_178421.3 | chr19:60755986-60759914 |
| 14116 | Nanos2 | NM_194064.2 | chr7:18987523-18988962 |
| 14117 | Nanos3 | NM_194059.2 | chr8:84173732-84176552 |
| 14118 | Nanp | NM_026086.2 | chr2:151029684-151039379 |
| 14119 | Nans | NM_053179.3 | chr4:46489328-46503438 |
| 14120 | Nap1l1 | NM_001146707.1 | chr10:111480616-111498150 |
| 14121 | Nap1l2 | NM_008671.2 | chrX:103184058-103186664 |
| 14122 | Nap1l3 | NM_138742.1 | chrX:122394560-122397385 |
| 14123 | Nap1l4 | NM_001285489.1 | chr7:143513578-143549120 |
| 14124 | Nap1l5 | NM_021432.2 | chr6:58905232-58907126 |
| 14125 | Napa | NM_025898.3 | chr7:16098642-16117975 |
| 14126 | Napb | NM_019632.3 | chr2:148694656-148732420 |
| 14127 | Napepld | NM_178728.3 | chr5:21662902-21701345 |
| 14128 | Napg | NM_028017.1 | chr18:62977915-62999451 |
| 14129 | Naprt1 | NM_172607.3 | chr15:75890963-75894481 |
| 14130 | Napsa | NM_001001985.3 | chr7:44572444-44586846 |
| 14131 | Narf | NM_026272.3 | chr11:121237235-121255856 |
| 14132 | Narfl | NM_026238.4 | chr17:25773775-25783332 |
| 14133 | Narg2 | NM_145618.3 | chr9:69397997-69433074 |
| 14134 | Nars | NM_001142950.1 | chr18:64499646-64516557 |
| 14135 | Nars2 | NM_153591.4 | chr7:96951526-97064757 |
| 14136 | Nasp | NM_001081051.1 | chr4:116601051-116627497 |
| 14137 | Nat1 | NM_008673.1 | chr8:67490757-67492103 |
| 14138 | Nat10 | NM_153126.2 | chr2:103721258-103761250 |
| 14139 | Nat14 | NM_201355.3 | chr7:4922250-4925006 |
| 14140 | Nat2 | NM_001168577.1 | chr8:67494874-67502578 |
| 14141 | Nat3 | NM_008674.2 | chr8:67523853-67548627 |
| 14142 | Nat6 | NM_019703.3 | chr9:107580169-107584048 |
| 14143 | Nat8 | NM_023455.3 | chr6:85830386-85831890 |
| 14144 | Nat8l | NM_001001985.3 | chr5:33995983-34005916 |
| 14145 | Nat9 | NM_025400.3 | chr11:115182831-115187316 |
| 14146 | Nav1 | NM_173437.2 | chr1:135434579-135585355 |
| 14147 | Nav2 | NM_001111016.1 | chr7:48959072-49610088 |
| 14148 | Nav3 | NM_001081035.1 | chr10:109683438-110000219 |
| 14149 | Nbas | NM_027706.1 | chr12:13269126-13583811 |

| | | | |
|---|---|---|---|
| 14150 | Nbea | NM_030595.1 | chr3:55625197-56183701 |
| 14151 | Nbeal1 | NM_173444.2 | chr1:60180598-60334705 |
| 14152 | Nbeal2 | NM_183276.2 | chr9:110624788-110654161 |
| 14153 | Nbl1 | NM_008675.2 | chr4:139082291-139092970 |
| 14154 | Nbn | NM_013752.3 | chr4:15957966-15992589 |
| 14155 | Nbr1 | NM_001252220.1 | chr11:101552106-101581951 |
| 14156 | Ncald | NM_001170866.1 | chr15:37366174-37792000 |
| 14157 | Ncam1 | NM_001081445.1 | chr9:49502145-49799069 |
| 14158 | Ncam2 | NM_001113208.1 | chr16:81200696-81624287 |
| 14159 | Ncan | NM_007789.3 | chr8:70093084-70120844 |
| 14160 | Ncapd2 | NM_146171.1 | chr6:125168006-125191586 |
| 14161 | Ncapd3 | NM_178113.3 | chr9:27030174-27095315 |
| 14162 | Ncapg | NM_019438.1 | chr5:45669924-45700547 |
| 14163 | Ncapg2 | NM_133762.3 | chr12:116405401-116463531 |
| 14164 | Ncaph | NM_144818.3 | chr2:127103809-127133954 |
| 14165 | Ncaph2 | NM_001115132.2 | chr15:89355718-89372850 |
| 14166 | Ncbp1 | NM_001033201.3 | chr4:46138510-46172402 |
| 14167 | Ncbp2 | NM_026554.4 | chr16:31948545-31958472 |
| 14168 | Nccrp1 | NM_001081115.1 | chr7:28543595-28547254 |
| 14169 | Ncdn | NM_011986.4 | chr4:126743749-126753429 |
| 14170 | Nceh1 | NM_178772.3 | chr3:27183003-27244911 |
| 14171 | Ncf1 | NM_001286037.1 | chr5:134220258-134229625 |
| 14172 | Ncf2 | NM_010877.5 | chr1:152800152-152836990 |
| 14173 | Ncf4 | NM_008677.2 | chr15:78244810-78262580 |
| 14174 | Nck1 | NM_010878.2 | chr9:100495002-100546053 |
| 14175 | Nck2 | NM_010879.3 | chr1:43345750-43570518 |
| 14176 | Nckap1 | NM_001290745.1 | chr2:80500511-80581182 |
| 14177 | Nckap1l | NM_153505.4 | chr15:103453824-103498800 |
| 14178 | Nckap5 | NM_001081756.1 | chr1:125913635-126830632 |
| 14179 | Nckap5l | NM_001001884.1 | chr15:99422033-99457748 |
| 14180 | Nckipsd | NM_030729.4 | chr9:108808379-108818366 |
| 14181 | Ncl | NM_010880.3 | chr1:86344718-86359455 |
| 14182 | Ncln | NM_134009.3 | chr10:81486458-81496363 |
| 14183 | Ncmap | NM_001168498.1 | chr4:135369576-135385672 |
| 14184 | Ncoa1 | NM_010881.2 | chr12:4247361-4477182 |
| 14185 | Ncoa2 | NM_001302702.1 | chr1:13139105-13374691 |
| 14186 | Ncoa3 | NM_008679.3 | chr2:165992636-166073242 |
| 14187 | Ncoa4 | NM_001033988.2 | chr14:32159886-32179855 |
| 14188 | Ncoa5 | NM_144892.1 | chr2:165000356-165034779 |
| 14189 | Ncoa6 | NM_001242558.1 | chr2:155390655-155440783 |
| 14190 | Ncoa7 | NM_001111267.2 | chr10:30645581-30655867 |
| 14191 | Ncor1 | NM_001252313.1 | chr11:62316425-62438515 |
| 14192 | Ncor2 | NM_001253904.1 | chr5:125017152-125179214 |
| 14193 | Ncr1 | NM_010746.3 | chr7:4337723-4345164 |
| 14194 | Ncs1 | NM_019681.3 | chr2:31245922-31295471 |
| 14195 | Ncstn | NM_021607.3 | chr1:172066012-172082749 |
| 14196 | Nctc1 | NR_002452.2 | chr7:142544608-142558598 |
| 14197 | Ndc1 | NM_028355.3 | chr4:107367783-107414338 |
| 14198 | Ndc80 | NM_023294.2 | chr17:71496099-71526857 |
| 14199 | Nde1 | NM_001114085.1 | chr16:14163274-14192923 |
| 14200 | Ndel1 | NM_023668.2 | chr11:68821445-68853131 |
| 14201 | Ndfip1 | NM_022996.1 | chr18:38418974-38464406 |
| 14202 | Ndfip2 | NM_001190989.1 | chr14:105258672-105309298 |
| 14203 | Ndn | NM_010882.3 | chr7:62348276-62349927 |
| 14204 | Ndnf | NM_172399.3 | chr6:65671610-65706930 |
| 14205 | Ndnl2 | NM_023239.4 | chr7:64871649-64872040 |
| 14206 | Ndor1 | NM_001082476.2 | chr2:25244812-25255414 |
| 14207 | Ndp | NM_010883.3 | chrX:16885520-16911774 |
| 14208 | Ndrg1 | NM_008681.2 | chr15:66929317-66969641 |
| 14209 | Ndrg2 | NM_001145959.1 | chr14:51905270-51913488 |
| 14210 | Ndrg3 | NM_013865.2 | chr2:156927341-156992111 |
| 14211 | Ndrg4 | NM_001195006.1 | chr8:95703036-95715139 |
| 14212 | Ndst1 | NM_008306.4 | chr18:60685975-60713389 |
| 14213 | Ndst2 | NM_010811.2 | chr14:20723729-20734562 |
| 14214 | Ndst3 | NM_031186.3 | chr3:123526165-123672477 |
| 14215 | Ndst4 | NM_022565.2 | chr3:125404090-125724986 |
| 14216 | Ndufa1 | NM_019443.2 | chrX:37187588-37191238 |
| 14217 | Ndufa10 | NM_024197.1 | chr1:92439718-92473758 |
| 14218 | Ndufa11 | NM_027244.1 | chr17:56717761-56724248 |
| 14219 | Ndufa12 | NM_025551.3 | chr10:94199008-94220948 |
| 14220 | Ndufa13 | NM_023312.2 | chr8:69894181-69902558 |
| 14221 | Ndufa2 | NM_010885.5 | chr18:36742331-36744587 |
| 14222 | Ndufa3 | NM_025348.2 | chr7:3617372-3620161 |
| 14223 | Ndufa4 | NM_010886.2 | chr6:11900372-11907446 |
| 14224 | Ndufa4l2 | NM_001098789.1 | chr10:127514938-127517156 |
| 14225 | Ndufa5 | NM_026614.2 | chr6:24518665-24527687 |
| 14226 | Ndufa6 | NM_025987.3 | chr15:82350138-82354291 |
| 14227 | Ndufa7 | NM_023202.4 | chr17:33824571-33838316 |
| 14228 | Ndufa8 | NM_026703.2 | chr2:36036333-36049292 |
| 14229 | Ndufa9 | NM_025358.3 | chr6:126821862-126849144 |
| 14230 | Ndufab1 | NM_028177.3 | chr7:122088043-122101848 |
| 14231 | Ndufaf1 | NM_027175.3 | chr2:119655450-119662798 |
| 14232 | Ndufaf2 | NM_001127346.1 | chr13:108052588-108158625 |
| 14233 | Ndufaf3 | NM_023247.1 | chr9:108565864-108567342 |
| 14234 | Ndufaf4 | NM_026742.4 | chr4:24898082-24905001 |
| 14235 | Ndufaf5 | NM_027093.4 | chr2:140170645-140205252 |
| 14236 | Ndufaf6 | NM_001085493.2 | chr11:051045-11076205 |
| 14237 | Ndufaf7 | NM_028611.3 | chr17:78937134-78948052 |
| 14238 | Ndufb10 | NM_026684.2 | chr17:24722686-24724388 |
| 14239 | Ndufb11 | NM_019435.4 | chrX:20615325-20617564 |
| 14240 | Ndufb2 | NM_026612.3 | chr6:39592582-39599471 |
| 14241 | Ndufb3 | NM_025597.3 | chr1:58586396-58595964 |
| 14242 | Ndufb4 | NM_026610.1 | chr16:37647601-37654368 |
| 14243 | Ndufb5 | NM_025316.2 | chr3:32737062-32751559 |
| 14244 | Ndufb6 | NM_001033305.3 | chr4:40270590-40279421 |

Fig. 26 - 76

| | | | | | | | |
|---|---|---|---|---|---|---|---|
| 14245 | Ndufb7 | NM_025843.3 | chr8:83566757-83571623 | 14340 | Nfib | NM_001113209.2 | chr4:82290172-82505779 |
| 14246 | Ndufb8 | NM_026061.2 | chr19:44550253-44555415 | 14341 | Nfic | NM_008688.3 | chr10:81396190-81427173 |
| 14247 | Ndufb9 | NM_023172.3 | chr15:58933809-58939489 | 14342 | Nfil3 | NM_017373.3 | chr13:52967208-52981039 |
| 14248 | Ndufc1 | NM_025523.1 | chr3:51405478-51408955 | 14343 | Nfix | NM_001081981.2 | chr8:84704711-84774369 |
| 14249 | Ndufc2 | NM_024220.2 | chr7:97400002-97407800 | 14344 | Nfkb1 | NM_008689.2 | chr3:135584654-135691547 |
| 14250 | Ndufs1 | NM_001160038.1 | chr1:63143591-63176822 | 14345 | Nfkb2 | NM_001177369.1 | chr19:46304736-46312090 |
| 14251 | Ndufs2 | NM_153064.5 | chr1:171234852-171247122 | 14346 | Nfkbia | NM_010907.2 | chr12:55489408-55492647 |
| 14252 | Ndufs3 | NM_026688.2 | chr2:90894635-90904721 | 14347 | Nfkbib | NM_010908.5 | chr7:28758250-28766644 |
| 14253 | Ndufs4 | NM_010887.2 | chr13:114287794-114388094 | 14348 | Nfkbid | NM_172142.3 | chr7:30423303-30428746 |
| 14254 | Ndufs5 | NM_001030274.1 | chr4:123712709-123718186 | 14349 | Nfkbie | NM_008690.4 | chr17:45555699-45563168 |
| 14255 | Ndufs6 | NM_010888.2 | chr13:73319875-73328482 | 14350 | Nfkbil1 | NM_010909.4 | chr17:35220174-35235815 |
| 14256 | Ndufs7 | NM_029272.3 | chr10:80249451-80256792 | 14351 | Nfkbiz | NM_001159394.1 | chr16:55811376-55822138 |
| 14257 | Ndufs8 | NM_001271443.1 | chr19:3908862-3912774 | 14352 | Nfrkb | NM_172766.3 | chr9:31386191-31421334 |
| 14258 | Ndufv1 | NM_133666.3 | chr19:4007498-4012755 | 14353 | Nfs1 | NM_010911.2 | chr2:156123636-156144186 |
| 14259 | Ndufv2 | NM_001278415.1 | chr17:66078794-66101559 | 14354 | Nfu1 | NM_001170591.1 | chr6:87009835-87028461 |
| 14260 | Ndufv3 | NM_001083891.1 | chr17:31520114-31531325 | 14355 | Nfx1 | NM_001290448.1 | chr4:40970905-41013873 |
| 14261 | Neat1 | NR_003513.3 | chr19:5842295-5845480 | 14356 | Nfxl1 | NM_133921.2 | chr5:72513303-72559645 |
| 14262 | Neb | NM_010889.1 | chr2:52136646-52338798 | 14357 | Nfya | NM_001110832.1 | chr17:48386884-48409820 |
| 14263 | Nebl | NM_028757.2 | chr2:17346733-17731068 | 14358 | Nfyb | NM_010914.2 | chr10:82748699-82764141 |
| 14264 | Necab1 | NM_178617.4 | chr4:14952244-15149131 | 14359 | Nfyc | NM_001048168.2 | chr4:120757434-120831579 |
| 14265 | Necab2 | NM_054095.2 | chr8:119446718-119472635 | 14360 | Ngb | NM_022414.2 | chr12:87097530-87102539 |
| 14266 | Necab3 | NM_021546.3 | chr2:154544404-154558853 | 14361 | Ngdn | NM_026890.2 | chr14:55015453-55024137 |
| 14267 | Necap1 | NM_026267.2 | chr6:122874556-122888941 | 14362 | Ngef | NM_001111314.1 | chr1:87476828-87573870 |
| 14268 | Necap2 | NM_025383.3 | chr4:141066511-141078345 | 14363 | Ngf | NM_001112698.2 | chr3:102469918-102521013 |
| 14269 | Nedd1 | NM_008682.2 | chr10:92684744-92722418 | 14364 | Ngfr | NM_033217.3 | chr11:95568820-95587698 |
| 14270 | Nedd4 | NM_010890.3 | chr9:72662346-72749848 | 14365 | Ngfrap1 | NM_001110233.1 | chrX:136270252-136271978 |
| 14271 | Nedd4l | NM_001114386.1 | chr18:64887755-65217826 | 14366 | Ngly1 | NM_021504.3 | chr14:16249313-16311926 |
| 14272 | Nedd8 | NM_008683.3 | chr14:55662266-55671906 | 14367 | Ngp | NM_008694.2 | chr9:110419807-110423012 |
| 14273 | Nedd9 | NM_001111324.2 | chr13:41309915-41487360 | 14368 | Ngrn | NM_031375.4 | chr7:80261214-80265378 |
| 14274 | Nefh | NM_010904.3 | chr11:4938755-4948064 | 14369 | Nhej1 | NM_029342.4 | chr1:74967345-75046639 |
| 14275 | Nefl | NM_010910.1 | chr14:68083883-68087737 | 14370 | Nhlh1 | NM_010916.2 | chr1:172052291-172057596 |
| 14276 | Nefm | NM_008691.2 | chr14:68119544-68125004 | 14371 | Nhlh2 | NM_178777.3 | chr3:102010144-102015492 |
| 14277 | Negr1 | NM_001039094.3 | chr3:156561793-157316464 | 14372 | Nhlrc1 | NM_175340.4 | chr13:47012556-47014850 |
| 14278 | Neil1 | NM_028347.2 | chr9:57143255-57147034 | 14373 | Nhlrc2 | NM_025811.3 | chr19:56548260-56598846 |
| 14279 | Neil2 | NM_201610.2 | chr14:63182444-63193525 | 14374 | Nhlrc3 | NM_172501.2 | chr3:53451995-53463258 |
| 14280 | Neil3 | NM_146208.2 | chr8:53536866-53639065 | 14375 | Nhlrc4 | NM_001039038.2 | chr17:25942232-25944931 |
| 14281 | Nek1 | NM_175089.4 | chr8:60993192-61131346 | 14376 | Nhp2 | NM_026631.3 | chr11:51619772-51623714 |
| 14282 | Nek10 | NM_001195229.1 | chr14:14820814-15006693 | 14377 | Nhp2l1 | NM_011482.4 | chr15:82041344-82047598 |
| 14283 | Nek11 | NM_172461.3 | chr9:105162466-105395287 | 14378 | Nhs | NM_001081052.2 | chrX:161836429-162159441 |
| 14284 | Nek2 | NM_010892.3 | chr1:191821472-191833049 | 14379 | Nhsl1 | NM_001163592.1 | chr10:18469980-18533891 |
| 14285 | Nek3 | NM_001162947.1 | chr8:22128285-22162494 | 14380 | Nhsl2 | NM_001163610.1 | chrX:101849384-102092055 |
| 14286 | Nek4 | NM_011849.3 | chr14:30951376-30988821 | 14381 | Nicn1 | NM_025449.3 | chr9:108290456-108296496 |
| 14287 | Nek5 | NM_177898.4 | chr8:22073615-22125053 | 14382 | Nid1 | NM_010917.2 | chr13:13437601-13512275 |
| 14288 | Nek6 | NM_001159631.1 | chr2:38511875-38587490 | 14383 | Nid2 | NM_008695.2 | chr14:19751256-19811787 |
| 14289 | Nek7 | NM_021605.4 | chr1:138483836-138619757 | 14384 | Nif3l1 | NM_022988.2 | chr1:58447632-58462276 |
| 14290 | Nek8 | NM_080849.3 | chr11:78166105-78176666 | 14385 | Nifk | NM_026472.4 | chr1:118321842-118333831 |
| 14291 | Nek9 | NM_145138.2 | chr12:85299513-85339362 | 14386 | Nim1k | NM_175538.3 | chr13:119710093-119755882 |
| 14292 | Nelfa | NM_011914.2 | chr5:33898179-33936258 | 14387 | Nin | NM_001081453.1 | chr12:70011434-70102854 |
| 14293 | Nelfb | NM_021393.3 | chr2:25199711-25211489 | 14388 | Ninj1 | NM_013610.2 | chr13:49187546-49196251 |
| 14294 | Nelfcd | NM_020580.3 | chr2:174415803-174427502 | 14389 | Ninj2 | NM_016718.2 | chr6:120093379-120200338 |
| 14295 | Nelfe | NM_001045863.1 | chr17:34850390-34856372 | 14390 | Ninl | NM_207204.2 | chr2:150934518-151009398 |
| 14296 | Nell1 | NM_001037906.2 | chr7:49975349-50863289 | 14391 | Nip7 | NM_001164472.1 | chr8:107056876-107060928 |
| 14297 | Nell1os | NR_045928.1 | chr7:50517308-50575884 | 14392 | Nipa1 | NM_153578.2 | chr7:55978483-56019573 |
| 14298 | Nell2 | NM_001289653.1 | chr15:95219439-95528252 | 14393 | Nipa2 | NM_001256130.1 | chr7:55931265-55962493 |
| 14299 | Nemf | NM_025441.3 | chr12:69311542-69357176 | 14394 | Nipal1 | NM_001081205.1 | chr5:72647795-72671078 |
| 14300 | Nenf | NM_025424.2 | chr1:191306796-191318118 | 14395 | Nipal2 | NM_145469.5 | chr15:34572798-34678706 |
| 14301 | Neo1 | NM_001042752.1 | chr9:58874679-59036441 | 14396 | Nipal3 | NM_028995.3 | chr4:135448800-135494504 |
| 14302 | Nepn | NM_025684.2 | chr10:52391607-52404604 | 14397 | Nipal4 | NM_172524.3 | chr11:46148154-46166359 |
| 14303 | Nes | NM_016701.3 | chr3:87971092-87980451 | 14398 | Nipbl | NM_027707.3 | chr15:8289823-8444463 |
| 14304 | Nespas | NR_002846.2 | chr2:174281236-174295436 | 14399 | Nipsnap1 | NM_008698.2 | chr11:4874002-4894200 |
| 14305 | Net1 | NM_001047159.2 | chr13:3882017-3893581 | 14400 | Nipsnap3a | NM_028529.1 | chr4:52989283-53000854 |
| 14306 | Neto1 | NM_144946.4 | chr18:86394951-86501897 | 14401 | Nipsnap3b | NM_025623.2 | chr4:53011923-53022059 |
| 14307 | Neto2 | NM_001081324.1 | chr8:85636587-85691009 | 14402 | Nisch | NM_022656.2 | chr14:31170927-31206826 |
| 14308 | Neu1 | NM_010893.3 | chr17:34931252-34937297 | 14403 | Nit1 | NM_001242580.1 | chr1:171342236-171345645 |
| 14309 | Neu2 | NM_001160163.1 | chr1:86394026-87587840 | 14404 | Nit2 | NM_023175.1 | chr16:57156664-57167332 |
| 14310 | Neu3 | NM_016720.2 | chr7:99814438-99828417 | 14405 | Nkain1 | NM_025998.3 | chr4:130530130-130574036 |
| 14311 | Neu4 | NM_173772.3 | chr1:94020492-94028330 | 14406 | Nkain2 | NM_001013411.2 | chr10:31689318-32889915 |
| 14312 | Neurl1a | NM_001163480.1 | chr19:47228842-47259441 | 14407 | Nkain3 | NM_001290410.1 | chr4:20118873-20778668 |
| 14313 | Neurl1b | NM_001081656.2 | chr17:26414964-26446342 | 14408 | Nkain4 | NM_001141933.1 | chr2:180934771-180954699 |
| 14314 | Neurl2 | NM_001072974.2 | chr2:164830729-164833596 | 14409 | Nkap | NM_025937.4 | chrX:37126762-37150746 |
| 14315 | Neurl3 | NM_153408.2 | chr1:36264601-36273425 | 14410 | Nkapl | NM_025719.3 | chr13:21467046-21468501 |
| 14316 | Neurl4 | NM_001013414.3 | chr11:69901815-69913824 | 14411 | Nkd1 | NM_001163660.1 | chr8:88527632-88594887 |
| 14317 | Neurod1 | NM_010894.2 | chr2:79452640-79456636 | 14412 | Nkd2 | NM_028186.4 | chr13:73819327-73847631 |
| 14318 | Neurod2 | NM_010895.3 | chr11:98325416-98329645 | 14413 | Nkg7 | NM_024253.4 | chr7:43437137-43438246 |
| 14319 | Neurod4 | NM_007501.4 | chr10:130268151-130280240 | 14414 | Nkiras1 | NM_023526.4 | chr14:18271141-18284000 |
| 14320 | Neurod6 | NM_009717.2 | chr6:55677818-55681263 | 14415 | Nkiras2 | NM_028024.2 | chr11:100622954-100627602 |
| 14321 | Neurog1 | NM_010896.2 | chr13:56250497-56252163 | 14416 | Nkpd1 | NM_027116.1 | chr7:19518730-19525050 |
| 14322 | Neurog2 | NM_009718.2 | chr3:127633144-127635631 | 14417 | Nkrf | NM_029891.2 | chrX:36887541-36902899 |
| 14323 | Neurog3 | NM_009719.6 | chr10:62133089-62134763 | 14418 | Nktr | NM_010918.2 | chr9:121719180-121756841 |
| 14324 | Nexn | NM_199465.2 | chr3:152236983-152266320 | 14419 | Nkx1-1 | NM_011320.1 | chr5:33430733-33434090 |
| 14325 | Nf1 | NM_010897.2 | chr11:79339891-79581609 | 14420 | Nkx1-2 | NM_009123.2 | chr7:132596238-132599637 |
| 14326 | Nf2 | NM_001252250.1 | chr11:4765844-4849544 | 14421 | Nkx2-1 | NM_001146198.1 | chr12:56531934-56535106 |
| 14327 | Nfam1 | NM_001271411.1 | chr15:82996735-83033397 | 14422 | Nkx2-2 | NM_001077632.1 | chr2:147177545-147186402 |
| 14328 | Nfasc | NM_001160316.1 | chr1:132564689-132642858 | 14423 | Nkx2-2os | NR_030769.2 | chr2:147184082-147331681 |
| 14329 | Nfat5 | NM_001081324.1 | chr8:107293469-107379517 | 14424 | Nkx2-3 | NM_008699.2 | chr19:43612324-43615892 |
| 14330 | Nfatc1 | NM_001164109.1 | chr18:80647434-80713071 | 14425 | Nkx2-4 | NM_023504.1 | chr2:147088875-147085345 |
| 14331 | Nfatc2 | NM_001037177.2 | chr2:168518198-168590365 | 14426 | Nkx2-5 | NM_008700.1 | chr17:26838664-26843565 |
| 14332 | Nfatc2ip | NM_010900.2 | chr7:126382853-126396737 | 14427 | Nkx2-6 | NM_010920.2 | chr14:69171801-69175540 |
| 14333 | Nfatc3 | NM_010901.2 | chr8:106059602-106130537 | 14428 | Nkx2-9 | NM_008701.2 | chr12:56611396-56613284 |
| 14334 | Nfatc4 | NM_001168346.1 | chr14:55824794-55833943 | 14429 | Nkx3-1 | NM_010921.3 | chr14:69190691-69194658 |
| 14335 | Nfe2 | NM_008685.3 | chr15:103248211-103255439 | 14430 | Nkx3-2 | NM_007524.3 | chr5:41761482-41764220 |
| 14336 | Nfe2l1 | NM_001130450.1 | chr11:96817413-96829502 | 14431 | Nkx6-1 | NM_144955.2 | chr5:101659196-101664711 |
| 14337 | Nfe2l2 | NM_010902.3 | chr2:75675512-75704663 | 14432 | Nkx6-2 | NM_183248.3 | chr7:139581219-139582797 |
| 14338 | Nfe2l3 | NM_010903.1 | chr6:51432669-51458768 | 14433 | Nkx6-3 | NM_029002.2 | chr8:23153270-23158948 |
| 14339 | Nfia | NM_001122952.1 | chr4:97581942-98118876 | 14434 | Nle1 | NM_145431.2 | chr11:82900767-82908395 |

Fig. 26 - 77

| | | | |
|---|---|---|---|
| 14435 | Nlgn1 | NM_001163387.1 | chr3:25431840-26153307 |
| 14436 | Nlgn2 | NM_198862.2 | chr11:69823122-69834849 |
| 14437 | Nlgn3 | NM_172932.4 | chrX:101299178-101321350 |
| 14438 | Nlk | NM_008702.3 | chr11:78567167-78697425 |
| 14439 | Nlrh | NM_029447.2 | chr13:104023438-104109614 |
| 14440 | Nlrc3 | NM_001081280.1 | chr16:3946932-3976632 |
| 14441 | Nlrc4 | NM_001033367.3 | chr17:74426294-74459108 |
| 14442 | Nlrc5 | NM_001033207.3 | chr8:94472762-94527272 |
| 14443 | Nlrp10 | NM_175532.3 | chr7:108921852-108930158 |
| 14444 | Nlrp12 | NM_001033431.1 | chr7:3221509-3249740 |
| 14445 | Nlrp14 | NM_001002894.2 | chr7:107166989-107198103 |
| 14446 | Nlrp1a | NM_001004142.2 | chr11:71091196-71144704 |
| 14447 | Nlrp1b | NM_001040696.1 | chr11:71153101-71230733 |
| 14448 | Nlrp1c-ps | NR_027858.1 | chr11:71242429-71285232 |
| 14449 | Nlrp2 | NM_177690.3 | chr7:5298546-5351035 |
| 14450 | Nlrp3 | NM_145827.3 | chr11:59542685-59566956 |
| 14451 | Nlrp4a | NM_172896.2 | chr7:26435112-26475458 |
| 14452 | Nlrp4b | NM_172481.2 | chr7:10687792-10730158 |
| 14453 | Nlrp4c | NM_031389.2 | chr7:6045160-6105149 |
| 14454 | Nlrp4e | NM_001004194.2 | chr7:23301191-23362277 |
| 14455 | Nlrp4f | NM_175290.4 | chr13:65177110-65205716 |
| 14456 | Nlrp4g | NM_001004145.2 | chr9:124348830-124354483 |
| 14457 | Nlrp5 | NM_001039143.2 | chr7:23385888-23441923 |
| 14458 | Nlrp5-ps | NR_045119.1 | chr7:14561170-14623066 |
| 14459 | Nlrp6 | NM_133946.2 | chr7:140920901-140929192 |
| 14460 | Nlrp9a | NM_001048219.2 | chr7:26535022-26574146 |
| 14461 | Nlrp9b | NM_194058.2 | chr7:20008022-20062938 |
| 14462 | Nlrp9c | NM_001042612.1 | chr7:26364886-26394243 |
| 14463 | Nlrx1 | NM_001163742.1 | chr9:44252712-44268599 |
| 14464 | Nmb | NM_001291280.1 | chr7:80902226-80905062 |
| 14465 | Nmbr | NM_008703.2 | chr10:14760288-14770556 |
| 14466 | Nmd3 | NM_133787.2 | chr3:69722054-69749046 |
| 14467 | Nme1 | NM_008704.2 | chr11:93958924-93968521 |
| 14468 | Nme2 | NM_001077529.2 | chr11:93949813-93955783 |
| 14469 | Nme3 | NM_019730.2 | chr17:24896499-24897529 |
| 14470 | Nme4 | NM_019731.1 | chr17:26091744-26095470 |
| 14471 | Nme5 | NM_080637.3 | chr18:34562640-34579106 |
| 14472 | Nme6 | NM_018757.1 | chr9:109832793-109842961 |
| 14473 | Nme7 | NM_138314.4 | chr1:164307671-164437300 |
| 14474 | Nme8 | NM_001167909.1 | chr13:19645078-19697760 |
| 14475 | Nme9 | NM_001165957.1 | chr9:99456242-99479899 |
| 14476 | Nni | NM_001141948.1 | chr2:51948498-51973208 |
| 14477 | Nmnat1 | NM_133435.1 | chr4:149468786-149485142 |
| 14478 | Nmnat2 | NM_175460.3 | chr1:152955100-153119261 |
| 14479 | Nmnat3 | NM_144533.2 | chr9:98296582-98411428 |
| 14480 | Nmral1 | NM_001290761.1 | chr16:4711317-4719356 |
| 14481 | Nmrk1 | NM_145497.2 | chr19:18632015-18652184 |
| 14482 | Nmrk2 | NM_027120.2 | chr10:81198169-81202037 |
| 14483 | Nms | NM_001016684.2 | chr1:38939148-38950276 |
| 14484 | Nmt1 | NM_008707.3 | chr11:103028561-103066105 |
| 14485 | Nmt2 | NM_001290368.1 | chr2:3284211-3328877 |
| 14486 | Nmu | NM_019515.1 | chr5:76333494-76363777 |
| 14487 | Nmur1 | NM_010341.1 | chr1:86386324-86388141 |
| 14488 | Nmur2 | NM_153079.4 | chr11:56024989-56040987 |
| 14489 | Nnat | NM_001291128.1 | chr2:157560077-157562525 |
| 14490 | Nnmt | NM_010914.3 | chr9:48591876-48605173 |
| 14491 | Nnt | NM_008710.3 | chr13:119334316-119409011 |
| 14492 | Noa1 | NM_019836.3 | chr5:77294168-77310086 |
| 14493 | Nob1 | NM_026277.3 | chr8:107421488-107425038 |
| 14494 | Nobox | NM_130869.3 | chr6:43303673-43309554 |
| 14495 | Noc2l | NM_021303.2 | chr4:156236009-156247616 |
| 14496 | Noc3l | NM_021315.2 | chr19:38788127-38819237 |
| 14497 | Noc4l | NM_153570.2 | chr5:110648418-110653382 |
| 14498 | Nod1 | NM_001171007.1 | chr6:54923941-54971661 |
| 14499 | Nod2 | NM_145857.2 | chr8:88647346-88688474 |
| 14500 | Nodal | NM_013611.4 | chr10:61417971-61425337 |
| 14501 | Nog | NM_008711.2 | chr11:89300637-89302559 |
| 14502 | Nol10 | NM_001008421.1 | chr12:17348492-17430095 |
| 14503 | Nol11 | NM_001161329.1 | chr11:107166660-107189381 |
| 14504 | Nol12 | NM_133800.3 | chr15:78934932-78941910 |
| 14505 | Nol3 | NM_030152.4 | chr8:105276446-105281939 |
| 14506 | Nol4 | NM_001161483.1 | chr18:22693154-23038663 |
| 14507 | Nol6 | NM_139236.3 | chr4:41114426-41124339 |
| 14508 | Nol7 | NM_023554.2 | chr13:43398375-43402858 |
| 14509 | Nol8 | NM_001271397.1 | chr13:49653077-49679016 |
| 14510 | Nol9 | NM_001159569.2 | chr4:152039320-152060038 |
| 14511 | Nolc1 | NM_001039351.2 | chr19:46075846-46085543 |
| 14512 | Nom1 | NM_001033457.2 | chr5:29434666-29452169 |
| 14513 | Nomo1 | NM_153057.4 | chr7:46033695-46084212 |
| 14514 | None | NM_001252518.1 | chrX:101479650-101448593 |
| 14515 | Nop10 | NM_025403.4 | chr2:112261925-112262898 |
| 14516 | Nop14 | NM_029278.2 | chr5:34638535-34660148 |
| 14517 | Nop16 | NM_178605.4 | chr13:54584190-54590074 |
| 14518 | Nop2 | NM_138747.2 | chr6:125131882-125144753 |
| 14519 | Nop56 | NM_024193.4 | chr2:130274411-130279313 |
| 14520 | Nop58 | NM_018868.2 | chr1:59685005-59711510 |
| 14521 | Nop9 | NM_026403.3 | chr14:54545692-55755634 |
| 14522 | Nos1 | NM_008712.3 | chr5:117866838-117958840 |
| 14523 | Nos1ap | NM_001109985.1 | chr1:170317495-170589849 |
| 14524 | Nos2 | NM_010927.4 | chr11:78920786-78960226 |
| 14525 | Nos3 | NM_008713.4 | chr5:24364818-24384474 |
| 14526 | Nosip | NM_001163684.1 | chr7:45062428-45078503 |
| 14527 | Nostrin | NM_181547.3 | chr2:69135799-69189329 |
| 14528 | Notch1 | NM_008714.3 | chr2:26457901-26503822 |
| 14529 | Notch2 | NM_010928.2 | chr3:98013537-98150367 |

| | | | |
|---|---|---|---|
| 14530 | Notch3 | NM_008716.2 | chr17:32120892-32166852 |
| 14531 | Notch4 | NM_010929.2 | chr17:34564294-34588543 |
| 14532 | Noto | NM_001007472.2 | chr6:85423885-85428877 |
| 14533 | Notum | NM_175263.4 | chr11:120653788-120660837 |
| 14534 | Nov | NM_010930.4 | chr15:54745927-54753761 |
| 14535 | Nova1 | NM_021361.1 | chr12:46694516-46818775 |
| 14536 | Nova2 | NM_001029877.3 | chr7:18925887-18965319 |
| 14537 | Nox1 | NM_172203.2 | chrX:134086420-134111854 |
| 14538 | Nox3 | NM_198058.2 | chr17:3635239-3696261 |
| 14539 | Nox4 | NM_001285833.1 | chr7:87246648-87398708 |
| 14540 | Noxa1 | NM_001163626.1 | chr2:25085669-25095205 |
| 14541 | Noxo1 | NM_027988.4 | chr17:24696233-24700529 |
| 14542 | Noxred1 | NM_027744.1 | chr12:87221122-87238601 |
| 14543 | Npas1 | NM_008718.2 | chr7:16455720-16476780 |
| 14544 | Npas2 | NM_008719.2 | chr1:39194271-39363240 |
| 14545 | Npas3 | NM_013780.2 | chr12:53248876-54072175 |
| 14546 | Npas4 | NM_153553.4 | chr19:4984354-4989971 |
| 14547 | Npat | NM_001081152.1 | chr9:53537046-53575627 |
| 14548 | Npb | NM_153288.3 | chr11:120608476-120609100 |
| 14549 | Npbwr1 | NM_010342.1 | chr1:5913706-5917398 |
| 14550 | Npc1 | NM_008720.2 | chr18:12189693-12236386 |
| 14551 | Npc1l1 | NM_207242.2 | chr11:6211010-6230245 |
| 14552 | Npc2 | NM_023409.4 | chr12:84754558-84773112 |
| 14553 | Npcd | NM_001033360.2 | chr15:79786350-79834333 |
| 14554 | Npdc1 | NM_008721.4 | chr2:25403049-25409494 |
| 14555 | Npepl1 | NM_213733.2 | chr2:174110350-174122702 |
| 14556 | Npepps | NM_008942.2 | chr11:97205805-97280576 |
| 14557 | Npff | NM_018787.1 | chr15:102523838-102524621 |
| 14558 | Npffr1 | NM_001177511.1 | chr10:61595483-61626385 |
| 14559 | Npffr2 | NM_133192.3 | chr5:89527428-89583740 |
| 14560 | Nphp1 | NM_001291012.1 | chr2:127740731-127788891 |
| 14561 | Nphp3 | NM_028721.3 | chr9:104002543-104043811 |
| 14562 | Nphp4 | NM_153424.2 | chr4:152478141-152563184 |
| 14563 | Nphs1 | NM_019459.2 | chr7:30460057-30488609 |
| 14564 | Nphs1os | NR_004443.1 | chr7:30462163-30465591 |
| 14565 | Nphs2 | NM_130456.4 | chr1:156310718-156328035 |
| 14566 | Npl | NM_028749.1 | chr1:153503015-153549714 |
| 14567 | Nploc4 | NM_001195023.1 | chr11:120379797-120437700 |
| 14568 | Npm1 | NM_001252260.1 | chr11:33152497-33163206 |
| 14569 | Npm2 | NM_181345.3 | chr14:70647301-70653084 |
| 14570 | Npm3 | NM_008723.1 | chr19:45747733-45749563 |
| 14571 | Npm3-ps1 | NR_002702.1 | chr6:85076140-85077126 |
| 14572 | Npnt | NM_001029836.2 | chr3:132881744-132950291 |
| 14573 | Nppa | NM_008725.3 | chr4:148000745-148002067 |
| 14574 | Nppb | NM_001287348.1 | chr4:147985787-147987205 |
| 14575 | Nppc | NM_010933.5 | chr1:86666292-86670973 |
| 14576 | Npr1 | NM_008727.5 | chr3:90450591-90465866 |
| 14577 | Npr2 | NM_173788.3 | chr4:43631934-43651240 |
| 14578 | Npr3 | NM_001039181.3 | chr15:11839886-11905674 |
| 14579 | Nprl2 | NM_018879.2 | chr9:107542208-107545706 |
| 14580 | Nprl3 | NM_001284359.1 | chr11:32231962-32267707 |
| 14581 | Nps | NM_001163611.1 | chr7:135268618-135272942 |
| 14582 | Npsr1 | NM_175678.3 | chr9:24098017-24316398 |
| 14583 | Nptn | NM_009145.2 | chr9:58582239-58652879 |
| 14584 | Nptx1 | NM_008730.2 | chr11:119538718-119547820 |
| 14585 | Nptx2 | NM_016789.3 | chr5:144545886-144557478 |
| 14586 | Nptxr | NM_030689.4 | chr15:79786350-79804709 |
| 14587 | Npvf | NM_021892.1 | chr6:50650870-50654393 |
| 14588 | Npw | NM_001099664.1 | chr17:24657329-24658425 |
| 14589 | Npy | NM_023456.3 | chr6:49822728-49829505 |
| 14590 | Npy1r | NM_010934.4 | chr8:66697421-66706798 |
| 14591 | Npy2r | NM_001205099.1 | chr3:82538382-82548085 |
| 14592 | Npy4r | NM_008919.4 | chr14:34145645-34152419 |
| 14593 | Npy5r | NM_016708.3 | chr8:66679964-66688094 |
| 14594 | Npy6r | NM_010935.3 | chr18:44270126-44277700 |
| 14595 | Nqo1 | NM_008706.5 | chr8:107388224-107403205 |
| 14596 | Nqo2 | NM_001163239.1 | chr13:33964658-33988465 |
| 14597 | Nr0b1 | NM_007430.5 | chrX:86191774-86195946 |
| 14598 | Nr0b2 | NM_011850.3 | chr4:133553375-133556686 |
| 14599 | Nr1d1 | NM_145434.4 | chr11:98767931-98775377 |
| 14600 | Nr1d2 | NM_011584.4 | chr14:18204055-18239106 |
| 14601 | Nr1h2 | NM_001285517.1 | chr7:44549615-44553965 |
| 14602 | Nr1h3 | NM_001177730.1 | chr2:91184060-91195116 |
| 14603 | Nr1h4 | NM_001163504.1 | chr10:89454233-89533622 |
| 14604 | Nr1h5 | NM_198658.2 | chr3:102939657-102964133 |
| 14605 | Nr1i2 | NM_001098404.1 | chr16:38248348-38294824 |
| 14606 | Nr1i3 | NM_001243062.1 | chr1:171213969-171218845 |
| 14607 | Nr2c1 | NM_011629.3 | chr10:94147930-94197214 |
| 14608 | Nr2c2 | NM_011630.3 | chr6:92091417-92173058 |
| 14609 | Nr2c2ap | NM_001025586.2 | chr8:70131326-70133751 |
| 14610 | Nr2e1 | NM_152229.2 | chr10:42561970-42583588 |
| 14611 | Nr2e3 | NM_013708.1 | chr9:59942770-59950079 |
| 14612 | Nr2f1 | NM_010151.2 | chr13:78188972-78198982 |
| 14613 | Nr2f2 | NM_009697.3 | chr7:70351949-70360593 |
| 14614 | Nr2f6 | NM_010150.2 | chr8:71374118-71381952 |
| 14615 | Nr3c1 | NM_008173.3 | chr18:39410544-39487245 |
| 14616 | Nr3c2 | NM_001083906.1 | chr8:76902507-77243639 |
| 14617 | Nr4a1 | NM_010444.2 | chr15:101266845-101274794 |
| 14618 | Nr4a2 | NM_001139509.1 | chr2:57107225-57124003 |
| 14619 | Nr4a3 | NM_015743.3 | chr4:48045304-48086446 |
| 14620 | Nr5a1 | NM_139051.3 | chr2:38692659-38714542 |
| 14621 | Nr5a2 | NM_001159769.2 | chr1:136843583-136953630 |
| 14622 | Nr6a1 | NM_001159548.1 | chr2:38723373-38784515 |
| 14623 | Nradd | NM_026012.2 | chr9:110621134-110624393 |
| 14624 | Nrap | NM_001286552.1 | chr19:56320040-56390038 |

Fig. 26 - 78

| | | | | | | | |
|---|---|---|---|---|---|---|---|
| 14625 | Nrarp | NM_025980.2 | chr2:25180757-25183332 | 14720 | Nudcd2 | NM_001290697.1 | chr11:40733660-40740046 |
| 14626 | Nras | NM_010937.2 | chr3:103058284-103067914 | 14721 | Nudcd3 | NM_173748.4 | chr11:6105691-6200451 |
| 14627 | Nrbf2 | NM_001036293.2 | chr10:67266688-67285281 | 14722 | Nudt1 | NM_008637.1 | chr5:140331921-140338135 |
| 14628 | Nrbp1 | NM_147201.2 | chr5:31240917-31251562 | 14723 | Nudt10 | NM_001031664.1 | chrX:6168696-6172991 |
| 14629 | Nrbp2 | NM_144847.1 | chr15:76085593-76090013 | 14724 | Nudt11 | NM_021431.2 | chrX:6047506-6054751 |
| 14630 | Nrcam | NM_001146031.1 | chr12:44328884-44601846 | 14725 | Nudt12 | NM_026497.2 | chr17:59001400-59013322 |
| 14631 | Nrd1 | NM_146150.2 | chr4:109000804-109061771 | 14726 | Nudt13 | NM_026341.2 | chr14:20294689-20317575 |
| 14632 | Nrde2 | NM_001290303.1 | chr12:100125449-100159653 | 14727 | Nudt14 | NM_025399.4 | chr12:112934732-112942118 |
| 14633 | Nrep | NM_001109988.1 | chr18:33437018-33464029 | 14728 | Nudt15 | NM_172527.2 | chr14:73519863-73548242 |
| 14634 | Nrf1 | NM_001164226.1 | chr6:30047987-30153458 | 14729 | Nudt16 | NM_029385.2 | chr9:105129337-105131805 |
| 14635 | Nrg1 | NM_178591.2 | chr8:31818027-31918203 | 14730 | Nudt16l1 | NM_025839.4 | chr16:4939110-4941020 |
| 14636 | Nrg2 | NM_001167891.1 | chr18:36017657-36197160 | 14731 | Nudt17 | NM_001162925.1 | chr3:96705891-96708560 |
| 14637 | Nrg3 | NM_001190187.1 | chr14:38368950-39473088 | 14732 | Nudt18 | NM_153136.4 | chr14:70577846-70582571 |
| 14638 | Nrg3os | NR_045713.1 | chr14:38898301-38958794 | 14733 | Nudt19 | NM_033080.2 | chr7:35547184-35555928 |
| 14639 | Nrg4 | NM_032002.2 | chr9:55220221-55283625 | 14734 | Nudt2 | NM_025539.2 | chr4:41465147-41480926 |
| 14640 | Nrgn | NM_022029.2 | chr9:37544492-37552745 | 14735 | Nudt21 | NM_026623.3 | chr8:94019402-94037039 |
| 14641 | Nrip1 | NM_173440.2 | chr16:76290861-76373049 | 14736 | Nudt22 | NM_026675.2 | chr19:6993018-6996037 |
| 14642 | Nrip2 | NM_001162858.1 | chr6:128399765-128408935 | 14737 | Nudt3 | NM_001291046.1 | chr17:27579381-27622964 |
| 14643 | Nrip3 | NM_020610.1 | chr7:109758055-109781545 | 14738 | Nudt4 | NM_027722.4 | chr10:95547006-95564167 |
| 14644 | Nrk | NM_013724.2 | chrX:138914429-139009090 | 14739 | Nudt5 | NM_016918.3 | chr2:5845033-5868736 |
| 14645 | Nrl | NM_001136074.2 | chr14:55518977-55524981 | 14740 | Nudt6 | NM_001291044.1 | chr3:37404981-37419596 |
| 14646 | Nrm | NM_134122.2 | chr17:35861317-35865400 | 14741 | Nudt7 | NM_001290180.1 | chr8:114133573-114152312 |
| 14647 | Nrn1 | NM_153529.2 | chr13:36725621-36734477 | 14742 | Nudt8 | NM_025529.3 | chr19:4000579-4002102 |
| 14648 | Nrn1l | NM_175024.4 | chr8:105893566-105895023 | 14743 | Nudt9 | NM_028794.4 | chr5:104046863-104065378 |
| 14649 | Nron | NR_045729.1 | chr2:33805815-33813593 | 14744 | Nuf2 | NM_023284.3 | chr1:169497933-169531464 |
| 14650 | Nrp | NM_001013372.2 | chr12:87442847-87444017 | 14745 | Nufip1 | NM_013745.5 | chr14:76110690-76137379 |
| 14651 | Nrp1 | NM_008737.2 | chr8:128359072-128505475 | 14746 | Nufip2 | NM_001024205.2 | chr11:77686138-77717966 |
| 14652 | Nrp2 | NM_001077403.1 | chr1:62703316-62818692 | 14747 | Nuggc | NM_001195674.2 | chr14:65605266-65648443 |
| 14653 | Nrros | NM_146069.4 | chr16:32142824-32165476 | 14748 | Numa1 | NM_1339473 | chr7:101969842-102014959 |
| 14654 | Nrsn1 | NM_009513.2 | chr13:25252038-25269996 | 14749 | Numb | NM_001136075.2 | chr12:83794033-83842358 |
| 14655 | Nrsn2 | NM_001009948.1 | chr2:152368757-152376566 | 14750 | Numbl | NM_010950.2 | chr7:27258760-27282150 |
| 14656 | Nrtn | NM_008738.2 | chr17:56751324-56757530 | 14751 | Nup107 | NM_134010.2 | chr10:117750642-117792705 |
| 14657 | Nrxn1 | NM_020252.3 | chr17:90033643-91092802 | 14752 | Nup133 | NM_172288.2 | chr8:123897122-123949265 |
| 14658 | Nrxn2 | NM_001205234.1 | chr19:6418737-6533217 | 14753 | Nup153 | NM_175749.2 | chr13:46679901-46727849 |
| 14659 | Nrxn3 | NM_001198587.3 | chr12:88794503-90334933 | 14754 | Nup155 | NM_133227.3 | chr15:8109312-8159859 |
| 14660 | Nsa2 | NM_021552.5 | chr13:97129426-97137926 | 14755 | Nup160 | NM_021512.4 | chr2:90677214-90736328 |
| 14661 | Nsd1 | NM_008739.3 | chr13:55209781-55318325 | 14756 | Nup188 | NM_198304.2 | chr2:30286432-30344262 |
| 14662 | Nsdhl | NM_010941.3 | chrX:72918520-72958528 | 14757 | Nup205 | NM_027513.1 | chr6:35177615-35247598 |
| 14663 | Nsf | NM_008740.4 | chr11:103821782-103954056 | 14758 | Nup210 | NM_018815.2 | chr6:91013066-91116826 |
| 14664 | Nsfl1c | NM_001091074.1 | chr2:151494181-151511310 | 14759 | Nup210l | NM_029937.1 | chr3:90104131-90212017 |
| 14665 | Nsg1 | NM_010942.3 | chr5:38137192-38159467 | 14760 | Nup214 | NM_172268.2 | chr2:31974449-32053975 |
| 14666 | Nsg2 | NM_001290650.1 | chr11:32000699-32059211 | 14761 | Nup35 | NM_001190179.1 | chr2:80639263-80660071 |
| 14667 | Nsl1 | NM_198654.3 | chr1:191063020-191084558 | 14762 | Nup37 | NM_027191.2 | chr10:88146991-88178395 |
| 14668 | Nsmaf | NM_010945.2 | chr4:6396207-6454271 | 14763 | Nup43 | NM_145706.2 | chr10:7667503-7678886 |
| 14669 | Nsmce1 | NM_026330.3 | chr7:125467639-125491542 | 14764 | Nup50 | NM_016714.2 | chr15:84923427-84942963 |
| 14670 | Nsmce2 | NM_001164604.1 | chr15:59374197-59539666 | 14765 | Nup54 | NM_183392.2 | chr5:92415539-92435199 |
| 14671 | Nsmce4a | NM_001162855.1 | chr7:130532525-130547381 | 14766 | Nup62 | NM_053074.2 | chr7:44816087-44831836 |
| 14672 | Nsmf | NM_001039386.1 | chr2:25054378-25062881 | 14767 | Nup62cl | NM_001081668.1 | chrX:140007672-140062568 |
| 14673 | Nsun2 | NM_145354.5 | chr13:69612015-69635779 | 14768 | Nup62-il41 | NM_001171024.1 | chr7:44816369-44840803 |
| 14674 | Nsun3 | NM_178925.3 | chr16:62734851-62786716 | 14769 | Nup85 | NM_001002929.4 | chr11:115564443-115583924 |
| 14675 | Nsun4 | NM_028142.4 | chr4:116031769-116053876 | 14770 | Nup88 | NM_001083331.2 | chr11:70943057-70969973 |
| 14676 | Nsun5 | NM_145414.2 | chr5:135369952-135376797 | 14771 | Nup93 | NM_172410.2 | chr8:94214600-94315066 |
| 14677 | Nsun6 | NM_001165941.1 | chr2:14995130-15054872 | 14772 | Nup98 | NM_001287164.1 | chr7:102119399-102210166 |
| 14678 | Nsun7 | NM_027602.2 | chr5:66260840-66298028 | 14773 | Nupl1 | NM_170591.1 | chr14:60219467-60251378 |
| 14679 | Nt5c | NM_015807.1 | chr11:115490425-115491814 | 14774 | Nupl2 | NM_153092.4 | chr5:24164962-24184008 |
| 14680 | Nt5c1a | NM_001085502.1 | chr4:123201552-123216207 | 14775 | Nupr1 | NM_019738.1 | chr7:126623245-126625470 |
| 14681 | Nt5c1b | NM_027588.3 | chr12:10369970-10390174 | 14776 | Nupr1l | NM_026916.3 | chr5:129908539-129911281 |
| 14682 | Nt5c2 | NM_001164363.1 | chr19:46886836-47015189 | 14777 | Nus1 | NM_030250.2 | chr10:52417546-52440192 |
| 14683 | Nt5c3 | NM_001252374.1 | chr6:56882401-56901886 | 14778 | Nusap1 | NM_001042652.1 | chr2:119618297-119650160 |
| 14684 | Nt5c3b | NM_001102650.1 | chr11:100429351-100441089 | 14779 | Nutf2 | NM_026532.3 | chr8:105866633-105880401 |
| 14685 | Nt5dc1 | NM_176968.4 | chr10:34303611-34418528 | 14780 | Nutf2-ps1 | NR_033574.1 | chr8:105866659-105879337 |
| 14686 | Nt5dc2 | NM_027289.1 | chr14:31134852-31139124 | 14781 | Nutm1 | NM_172521.1 | chr2:112247947-112259291 |
| 14687 | Nt5dc3 | NM_175331.3 | chr10:86779004-86838389 | 14782 | Nvl | NM_026171.2 | chr1:181087137-181144204 |
| 14688 | Nt5e | NM_011851.4 | chr9:88327608-88372089 | 14783 | Nwd1 | NM_176940.5 | chr8:72646710-72714748 |
| 14689 | Nt5m | NM_134029.2 | chr11:59848072-59876533 | 14784 | Nwd2 | NM_177006.3 | chr5:63649102-63810543 |
| 14690 | Ntan1 | NM_010946.3 | chr16:13819276-13835451 | 14785 | Nxf1 | NM_001276704.1 | chr19:8757116-8770910 |
| 14691 | Ntf3 | NM_001164034.1 | chr6:126101411-126166744 | 14786 | Nxf2 | NM_001289735.1 | chrX:134944525-134964754 |
| 14692 | Ntf5 | NM_198190.1 | chr7:45413694-45417179 | 14787 | Nxf3 | NM_001024141.4 | chrX:136072098-136085255 |
| 14693 | Nthl1 | NM_008743.2 | chr17:24632681-24638838 | 14788 | Nxf7 | NM_130838.1 | chrX:135579786-135593855 |
| 14694 | Ntm | NM_172290.3 | chr9:28995963-29963129 | 14789 | Nxn | NM_008750.5 | chr11:76257225-76399141 |
| 14695 | Ntmt1 | NM_170592.2 | chr2:30807976-30823014 | 14790 | Nxnl1 | NM_145598.2 | chr8:71560554-71566649 |
| 14696 | Ntn1 | NM_008744.2 | chr11:68209363-68386826 | 14791 | Nxnl2 | NM_029173.4 | chr13:51171024-51175187 |
| 14697 | Ntn3 | NM_010947.3 | chr17:24203842-24209387 | 14792 | Nxpe2 | NM_030069.3 | chr9:48318603-48340898 |
| 14698 | Ntn4 | NM_021320.3 | chr10:93641048-93745972 | 14793 | Nxpe3 | NM_001134457.1 | chr16:55839952-55895279 |
| 14699 | Ntn5 | NM_001033856.3 | chr7:45684021-45694556 | 14794 | Nxpe4 | NM_172921.3 | chr9:48362040-48400025 |
| 14700 | Ntng1 | NM_001145804.1 | chr3:109780049-110143472 | 14795 | Nxpe5 | NM_001013773.3 | chr5:138225903-138251875 |
| 14701 | Ntng2 | NM_133500.2 | chr2:29194725-29248099 | 14796 | Nxph1 | NM_008751.3 | chr6:8950018-9248578 |
| 14702 | Ntpcr | NM_025636.5 | chr8:125734202-125748235 | 14797 | Nxph2 | NM_008752 | chr2:23321245-23401973 |
| 14703 | Ntrk1 | NM_001012331.1 | chr3:87778243-87795162 | 14798 | Nxph3 | NM_130858 | chr11:95509845-95514565 |
| 14704 | Ntrk2 | NM_001025074.2 | chr13:58807696-59113970 | 14799 | Nxph4 | NM_183297 | chr10:127525472-127534559 |
| 14705 | Ntrk3 | NM_008746.5 | chr7:78192113-78577838 | 14800 | Nxt1 | NM_001110159.1 | chr2:148672640-148676026 |
| 14706 | Nts | NM_024435.2 | chr10:102481755-102480418 | 14801 | Nxt2 | NM_001161430.2 | chrX:142227936-142239700 |
| 14707 | Ntsr1 | NM_018766.2 | chr2:180499975-180544979 | 14802 | Nyap1 | NM_175521.3 | chr5:137730962-137739998 |
| 14708 | Ntsr2 | NM_008747.2 | chr12:16653469-16660236 | 14803 | Nyap2 | NM_172849.3 | chr1:81077316-81271651 |
| 14709 | Nuak1 | NM_001004363.1 | chr10:84371318-84440471 | 14804 | Nynrin | NM_001040072.1 | chr14:55854114-55874736 |
| 14710 | Nuak2 | NM_001195025.1 | chr1:132316124-132333488 | 14805 | Nyx | NM_173415.4 | chrX:13467671-13489313 |
| 14711 | Nubl | NM_025814.2 | chr5:24685814-24710378 | 14806 | Oacyl | NM_177028.3 | chr18:65698267-65751537 |
| 14712 | Nubp1 | NM_011955.1 | chr16:10411937-10424425 | 14807 | Oaf | NM_178644.3 | chr9:43221277-43239816 |
| 14713 | Nubp2 | NM_011956.3 | chr17:24882610-24886350 | 14808 | Oard1 | NM_001289490.1 | chr17:48409999-48417270 |
| 14714 | Nubpl | NM_029760.2 | chr12:52097745-52310959 | 14809 | Oas1a | NM_145211.2 | chr5:120896256-120907525 |
| 14715 | Nucb1 | NM_001163662.1 | chr7:45492673-45510408 | 14810 | Oas1b | NM_001083925.1 | chr5:120812637-120824160 |
| 14716 | Nucb2 | NM_001130479.2 | chr7:116504368-116540588 | 14811 | Oas1c | NM_033541.4 | chr5:120800198-120812514 |
| 14717 | Nucks1 | NM_001145804.1 | chr1:131910457-131936321 | 14812 | Oas1d | NM_133893.3 | chr5:120914817-120921647 |
| 14718 | Nudc | NM_010948.3 | chr4:133532541-133546027 | 14813 | Oas1e | NM_145210.2 | chr5:120786311-120795530 |
| 14719 | Nudcd1 | NM_001113554.1 | chr15:44375226-44428307 | 14814 | Oas1f | NM_145153.3 | chr5:120847366-120857986 |

Fig. 26 - 79

| | | | | | | | | |
|---|---|---|---|---|---|---|---|---|
| 14815 | Oas1g | NM_011852.3 | chr5:120876141-120887613 | | 14910 | Olfr1033 | NM_146578.2 | chr2:86020639-86044808 |
| 14816 | Oas1h | NM_001159934.1 | chr5:120861421-120873505 | | 14911 | Olfr1034 | NM_001011872.2 | chr2:86046443-86047466 |
| 14817 | Oas2 | NM_145227.3 | chr5:120730332-120749848 | | 14912 | Olfr1036 | NM_207142.2 | chr2:86074703-86075718 |
| 14818 | Oas3 | NM_145226.2 | chr5:120753097-120777659 | | 14913 | Olfr1037 | NM_001011532.2 | chr2:86084729-86085854 |
| 14819 | Oasl1 | NM_145209.3 | chr5:114923239-114937911 | | 14914 | Olfr1038-ps | NM_147013.2 | chr2:86120223-86123037 |
| 14820 | Oasl2 | NM_011854.2 | chr5:114896933-114912245 | | 14915 | Olfr1039 | NM_001011784.2 | chr2:86130701-86131661 |
| 14821 | Oat | NM_016978.2 | chr7:132557474-132576398 | | 14916 | Olfr1040 | NM_207561.2 | chr2:86145790-86146732 |
| 14822 | Oaz1 | NM_008753.4 | chr10:80826655-80829290 | | 14917 | Olfr1042 | NM_001011777.2 | chr2:86159344-86160441 |
| 14823 | Oaz1-ps | NR_027656.1 | chr10:80826695-80829217 | | 14918 | Olfr1043 | NM_146577.2 | chr2:86162002-86162947 |
| 14824 | Oaz2 | NM_010952.3 | chr9:65676547-65690300 | | 14919 | Olfr1044 | NM_147011.1 | chr2:86170870-86171815 |
| 14825 | Oaz3 | NM_016901.3 | chr3:94433387-94436651 | | 14920 | Olfr1045 | NM_147017.2 | chr2:86197802-86198750 |
| 14826 | Obfc1 | NM_175360.2 | chr19:47501047-47537020 | | 14921 | Olfr1046 | NM_146582.2 | chr2:86216757-86217708 |
| 14827 | Obox1 | NM_027802.2 | chr7:15547256-15556846 | | 14922 | Olfr1047 | NM_147012.1 | chr2:86228009-86228969 |
| 14828 | Obox2 | NM_145708.2 | chr7:15388850-15398543 | | 14923 | Olfr1048 | NM_147014.1 | chr2:86235870-86236833 |
| 14829 | Obox3 | NM_145707.3 | chr7:15625305-15639777 | | 14924 | Olfr1049 | NM_147016.2 | chr2:86254764-86255691 |
| 14830 | Obox5 | NM_145709.2 | chr7:15750369-15759274 | | 14925 | Olfr1051 | NM_207562.2 | chr2:86275558-86276485 |
| 14831 | Obox6 | NM_145710.2 | chr7:15833249-15839679 | | 14926 | Olfr1052 | NM_147010.2 | chr2:86297817-86298756 |
| 14832 | Obp1a | NM_008754.2 | chrX:78085504-78091374 | | 14927 | Olfr1053 | NM_001177857.1 | chr2:86314342-86315285 |
| 14833 | Obp2a | NM_153558.1 | chr2:25700073-25703326 | | 14928 | Olfr1054 | NM_147019.1 | chr2:86332415-86333354 |
| 14834 | Obp2b | NM_001099301.1 | chr2:25737008-25740097 | | 14929 | Olfr1055 | NM_147021.1 | chr2:86346825-86347764 |
| 14835 | Obscn | NM_001171512.2 | chr11:58994255-59136375 | | 14930 | Olfr1056 | NM_147018.2 | chr2:86355358-86356437 |
| 14836 | Obsl1 | NM_178884.5 | chr1:75485824-75506652 | | 14931 | Olfr1057 | NM_207563.2 | chr2:86374462-86375410 |
| 14837 | Oc90 | NM_010953.2 | chr15:65876052-65912287 | | 14932 | Olfr1058 | NM_146391.2 | chr2:86385465-86386416 |
| 14838 | Oca2 | NM_021879.2 | chr7:56239770-56536517 | | 14933 | Olfr1061 | NM_207134.1 | chr2:86413198-86414050 |
| 14839 | Ocel1 | NM_029021.5 | chr8:71371297-71373689 | | 14934 | Olfr1062 | NM_147078.2 | chr2:86422718-86423674 |
| 14840 | Ociad1 | NM_001159887.1 | chr5:73292793-73314077 | | 14935 | Olfr1065 | NM_146408.2 | chr2:86445012-86446004 |
| 14841 | Ociad2 | NM_026950.4 | chr5:73322197-73338947 | | 14936 | Olfr1066 | NM_001011735.2 | chr2:86455327-86456269 |
| 14842 | Ocln | NM_008756.2 | chr13:100497366-100552498 | | 14937 | Olfr107 | NM_146511.2 | chr17:37405476-37406509 |
| 14843 | Ocm | NM_033039.3 | chr5:144019806-144050609 | | 14938 | Olfr1076 | NM_146406.2 | chr2:86508460-86509402 |
| 14844 | Ocrl | NM_177215.3 | chrX:47912455-47965866 | | 14939 | Olfr1077-ps1 | NR_033507.1 | chr2:86525661-86528427 |
| 14845 | Ocstamp | NM_029021.1 | chr2:165395449-165400394 | | 14940 | Olfr1079 | NM_146407.3 | chr2:86537965-86538913 |
| 14846 | Odam | NM_027128.2 | chr5:87885694-87892742 | | 14941 | Olfr108 | NM_146465.1 | chr17:37445479-37446517 |
| 14847 | Odc1 | NM_013614.2 | chr12:17544872-17551502 | | 14942 | Olfr1080 | NM_146409.2 | chr2:86553180-86558138 |
| 14848 | Odf1 | NM_008757.3 | chr15:38219202-38226735 | | 14943 | Olfr1082 | NM_207674.2 | chr2:86593884-86598809 |
| 14849 | Odf2 | NM_001113213.1 | chr2:29889719-29931746 | | 14944 | Olfr1084 | NM_207135.2 | chr2:86638764-86639718 |
| 14850 | Odf2l | NM_001162538.1 | chr3:145118588-145153915 | | 14945 | Olfr1085 | NM_146590.2 | chr2:86657514-86658456 |
| 14851 | Odf3 | NM_027019.3 | chr7:140847915-140850925 | | 14946 | Olfr1086 | NM_146592.1 | chr2:86676398-86677331 |
| 14852 | Odf3b | NM_001013022.1 | chr15:89377448-89379254 | | 14947 | Olfr1087 | NM_146846.2 | chr2:86690031-86690973 |
| 14853 | Odf3l1 | NM_198673.2 | chr9:56848658-56851963 | | 14948 | Olfr1089 | NM_001011771.2 | chr2:86732874-86733610 |
| 14854 | Odf3l2 | NM_001033473.2 | chr10:79639525-79645738 | | 14949 | Olfr109 | NM_146835.1 | chr17:37466207-37467152 |
| 14855 | Odf4 | NM_145746.2 | chr11:68921834-68927081 | | 14950 | Olfr1090 | NM_146847.1 | chr2:86753794-86754736 |
| 14856 | Ofcc1 | NM_172143.2 | chr13:40001881-40288011 | | 14951 | Olfr1093 | NM_146366.1 | chr2:86785731-86786700 |
| 14857 | Ofd1 | NM_177429.3 | chrX:166390032-166440704 | | 14952 | Olfr1094 | NM_146365.2 | chr2:86828675-86829822 |
| 14858 | Ogdh | NM_001252282.1 | chr11:6291596-6359094 | | 14953 | Olfr1095 | NM_146730.2 | chr2:86850769-86851696 |
| 14859 | Ogdhl | NM_001081130.1 | chr14:32322018-32347820 | | 14954 | Olfr1097 | NM_146843.2 | chr2:86890225-86892163 |
| 14860 | Ogfod1 | NM_001093757.1 | chr8:94037197-94067922 | | 14955 | Olfr1098 | NM_146845.2 | chr2:86922582-86923530 |
| 14861 | Ogfod2 | NM_025671.2 | chr5:124112337-124115476 | | 14956 | Olfr1099 | NM_146768.1 | chr2:86958517-86959456 |
| 14862 | Ogfod3 | NM_025402.2 | chr11:121177592-121204648 | | 14957 | Olfr11 | NM_146542.2 | chr13:21638579-21639521 |
| 14863 | Ogfr | NM_031373.3 | chr2:180589406-180595837 | | 14958 | Olfr110 | NM_146328.2 | chr17:37492467-37499674 |
| 14864 | Ogfrl1 | NM_001081079.1 | chr1:23366423-23383175 | | 14959 | Olfr1100 | NM_146594.1 | chr2:86977828-86978794 |
| 14865 | Ogg1 | NM_010957.4 | chr6:113326975-113334186 | | 14960 | Olfr1101 | NM_146591.2 | chr2:86988241-86989174 |
| 14866 | Ogn | NM_008760.4 | chr13:49608070-49624500 | | 14961 | Olfr1102 | NM_207154.2 | chr2:87001931-87002994 |
| 14867 | Ogt | NM_001290535.1 | chrX:101640217-101684351 | | 14962 | Olfr1104 | NM_146767.2 | chr2:87021609-87022542 |
| 14868 | Olp5 | NM_001042653.1 | chr2:119609531-119618505 | | 14963 | Olfr1105 | NM_001011825.1 | chr2:87033280-87034219 |
| 14869 | Oit1 | NM_146050.2 | chr14:8348947-8378763 | | 14964 | Olfr1106 | NM_146752.2 | chr2:87048295-87049234 |
| 14870 | Oit3 | NM_010959.2 | chr10:59422959-59441779 | | 14965 | Olfr1107 | NM_146844.2 | chr2:87071115-87072223 |
| 14871 | Ola1 | NM_025942.2 | chr2:73092800-73214447 | | 14966 | Olfr1109 | NM_146766.2 | chr2:87092456-87093395 |
| 14872 | Olah | NM_145921.1 | chr2:3341987-3366569 | | 14967 | Olfr111 | NM_001005485.2 | chr17:37529956-37530997 |
| 14873 | Olfm1 | NM_001038612.1 | chr2:28205688-28214431 | | 14968 | Olfr1110 | NM_146769.1 | chr2:87135308-87136319 |
| 14874 | Olfm2 | NM_173777.3 | chr9:20667985-20728214 | | 14969 | Olfr1111 | NM_146593.1 | chr2:87149719-87150659 |
| 14875 | Olfm3 | NM_001286750.1 | chr3:114904634-115125764 | | 14970 | Olfr1112 | NM_146661.2 | chr2:87191888-87192645 |
| 14876 | Olfm4 | NM_001030294.1 | chr14:80000301-80021930 | | 14971 | Olfr1113 | NM_207565.1 | chr2:87212893-87213874 |
| 14877 | Olfml1 | NM_172907.3 | chr7:107567432-107591365 | | 14972 | Olfr1115 | NM_146297.2 | chr2:87251839-87252941 |
| 14878 | Olfml2a | NM_172854.2 | chr2:38931979-38960585 | | 14973 | Olfr1116-ps | NM_001011734.1 | chr2:87268845-87269769 |
| 14879 | Olfml2b | NM_177068.4 | chr1:170644531-170682789 | | 14974 | Olfr1118 | NM_207632.2 | chr2:87308763-87309759 |
| 14880 | Olfml3 | NM_133859.2 | chr3:103735393-103738001 | | 14975 | Olfr112 | NM_001013575.4 | chr17:37563238-37569451 |
| 14881 | Olfr1 | NM_146921.2 | chr11:73395075-73399495 | | 14976 | Olfr1120 | NM_147029.1 | chr2:87357445-87358390 |
| 14882 | Olfr10 | NM_206822.1 | chr11:49317547-49318483 | | 14977 | Olfr1121 | NM_146348.2 | chr2:87371533-87372478 |
| 14883 | Olfr100 | NM_207673.1 | chr17:37313455-37314382 | | 14978 | Olfr1122 | NM_147031.1 | chr2:87387706-87388687 |
| 14884 | Olfr1000 | NM_001011695.1 | chr2:85607963-85608908 | | 14979 | Olfr1123 | NM_146350.2 | chr2:87416049-87419021 |
| 14885 | Olfr1002 | NM_146573.2 | chr2:85647362-85648319 | | 14980 | Olfr1124 | NM_147028.2 | chr2:87434488-87435445 |
| 14886 | Olfr1006 | NM_146570.2 | chr2:85674210-85678741 | | 14981 | Olfr1126 | NM_146837.2 | chr2:87457166-87458111 |
| 14887 | Olfr1008 | NM_146866.1 | chr2:85689430-85690372 | | 14982 | Olfr1128 | NM_146349.2 | chr2:87544606-87545542 |
| 14888 | Olfr1009 | NM_146572.2 | chr2:85721406-85722351 | | 14983 | Olfr1129 | NM_001011836.2 | chr2:87575085-87576030 |
| 14889 | Olfr101 | NM_146834.1 | chr17:37299493-37300420 | | 14984 | Olfr113 | NM_146289.1 | chr17:37574482-37575421 |
| 14890 | Olfr1010 | NM_207149.2 | chr2:85753362-85754306 | | 14985 | Olfr1130 | NM_146838.2 | chr2:87606211-87608334 |
| 14891 | Olfr1012 | NM_146568.2 | chr2:85759438-85760374 | | 14986 | Olfr1131 | NM_146658.2 | chr2:87628464-87629394 |
| 14892 | Olfr1013 | NM_146762.2 | chr2:85769802-85770720 | | 14987 | Olfr1132 | NM_146836.1 | chr2:87634818-87635745 |
| 14893 | Olfr1014 | NM_146569.2 | chr2:85776585-85777503 | | 14988 | Olfr1133 | NM_146351.2 | chr2:87645179-87646121 |
| 14894 | Olfr1015 | NM_146571.2 | chr2:85785473-85786489 | | 14989 | Olfr1134 | NM_147030.2 | chr2:87655924-87658457 |
| 14895 | Olfr1016 | NM_001011758.2 | chr2:85799338-85800268 | | 14990 | Olfr1135 | NM_146660.2 | chr2:87671432-87672365 |
| 14896 | Olfr1018 | NM_146586.2 | chr2:85822972-85823908 | | 14991 | Olfr1136 | NM_146659.3 | chr2:87692880-87693947 |
| 14897 | Olfr1019 | NM_147015.1 | chr2:85840856-85841789 | | 14992 | Olfr1137 | NM_001011833.1 | chr2:87710971-87711904 |
| 14898 | Olfr102 | NM_001011721.2 | chr17:37313410-37314437 | | 14993 | Olfr1138 | NM_146639.1 | chr2:87737386-87738322 |
| 14899 | Olfr1020 | NM_146580.2 | chr2:85849419-85850498 | | 14994 | Olfr114 | NM_146287.1 | chr17:37589412-37590351 |
| 14900 | Olfr1022 | NM_146589.2 | chr2:85868593-85869541 | | 14995 | Olfr1140 | NM_146642.2 | chr2:87746160-87747180 |
| 14901 | Olfr1023 | NM_146586801-85887737 | NM_146586801-85887737 | | 14996 | Olfr1141 | NM_146637.1 | chr2:87753055-87753991 |
| 14902 | Olfr1024 | NM_001005230.2 | chr2:85904068-85905052 | | 14997 | Olfr1143 | NM_146293.2 | chr2:87802390-87803335 |
| 14903 | Olfr1026 | NM_146584.2 | chr2:85923269-85924193 | | 14998 | Olfr1145 | NM_146320.2 | chr2:87809821-87810799 |
| 14904 | Olfr1028 | NM_146587.2 | chr2:85951064-85952039 | | 14999 | Olfr1148 | NM_001011519.1 | chr2:87833040-87833985 |
| 14905 | Olfr1029 | NM_001011852.2 | chr2:85975212-85976273 | | 15000 | Olfr115 | NM_001011753.2 | chr17:37609784-37610779 |
| 14906 | Olfr103 | NM_146833.1 | chr17:37336288-37337230 | | 15001 | Olfr1151 | NM_146638.1 | chr2:87857176-87858103 |
| 14907 | Olfr1030 | NM_146588.2 | chr2:85959311-85984798 | | 15002 | Olfr1152 | NM_001011834.1 | chr2:87867992-87868925 |
| 14908 | Olfr1031 | NM_001011759.2 | chr2:85991818-85992829 | | 15003 | Olfr1153 | NM_146640.2 | chr2:87896176-87897133 |
| 14909 | Olfr1032 | NM_146579.2 | chr2:86007777-86008710 | | 15004 | Olfr1154 | NM_146647.2 | chr2:87902741-87903674 |

Fig. 26 - 80

| | | | | | | | | |
|---|---|---|---|---|---|---|---|---|
| 15005 | Olfr1155 | NM_146643.2 | chr2:87942681-87943626 | | 15100 | Olfr1261 | NM_146474.1 | chr2:89993394-89994315 |
| 15006 | Olfr1156 | NM_146817.2 | chr2:87949189-87950265 | | 15101 | Olfr1262 | NM_146974.1 | chr2:90002407-90003322 |
| 15007 | Olfr1157 | NM_146849.2 | chr2:87961951-87968257 | | 15102 | Olfr1263 | NM_146794.1 | chr2:90014931-90015852 |
| 15008 | Olfr1158 | NM_146645.2 | chr2:87990112-87991054 | | 15103 | Olfr1264 | NM_021368.1 | chr2:90021137-90022064 |
| 15009 | Olfr116 | NM_146632.1 | chr17:37623667-37624633 | | 15104 | Olfr1265 | NM_146343.1 | chr2:90036920-90037850 |
| 15010 | Olfr1160 | NM_146649.2 | chr2:88005816-88006776 | | 15105 | Olfr1269 | NM_146342.1 | chr2:90118666-90119596 |
| 15011 | Olfr1161 | NM_146848.2 | chr2:88024701-88025713 | | 15106 | Olfr127 | NM_146377.1 | chr17:37903547-37904519 |
| 15012 | Olfr1162 | NM_001011835.1 | chr2:88049677-88050622 | | 15107 | Olfr1270 | NM_146985.2 | chr2:90149018-90150036 |
| 15013 | Olfr1163 | NM_146644.2 | chr2:88070364-88071407 | | 15108 | Olfr1271 | NM_146793.1 | chr2:90265510-90266428 |
| 15014 | Olfr1164 | NM_146641.2 | chr2:88092854-88093966 | | 15109 | Olfr1272 | NM_146980.1 | chr2:90281646-90282573 |
| 15015 | Olfr1166 | NM_146650.2 | chr2:88123361-88124993 | | 15110 | Olfr1273-ps | NM_146975.1 | chr2:90295935-90296859 |
| 15016 | Olfr1167 | NM_146294.2 | chr2:88148983-88150083 | | 15111 | Olfr1274-ps | NM_146263.2 | chr2:90400639-90401674 |
| 15017 | Olfr1168 | NM_146531.2 | chr2:88184878-88185817 | | 15112 | Olfr1275 | NM_001011795.1 | chr2:111230852-111231791 |
| 15018 | Olfr117 | NM_207155.2 | chr17:37659377-37660331 | | 15113 | Olfr1276 | NM_146395.1 | chr2:111257116-111258055 |
| 15019 | Olfr1170 | NM_146532.1 | chr2:88224079-88225030 | | 15114 | Olfr1277 | NM_146396.1 | chr2:111269453-111270365 |
| 15020 | Olfr1173 | NM_207566.1 | chr2:88274108-88275047 | | 15115 | Olfr1278 | NM_146394.1 | chr2:111292269-111293211 |
| 15021 | Olfr1176 | NM_146771.1 | chr2:88339566-88340514 | | 15116 | Olfr1279 | NM_146393.1 | chr2:111306200-111307142 |
| 15022 | Olfr1178 | NM_001011868.1 | chr2:88391248-88392220 | | 15117 | Olfr128 | NM_206816.1 | chr17:37923567-37924494 |
| 15023 | Olfr1179 | NM_146917.2 | chr2:88402008-88402932 | | 15118 | Olfr1280 | NM_146908.1 | chr2:111315480-111316398 |
| 15024 | Olfr118 | NM_213721.2 | chr17:37672024-37672990 | | 15119 | Olfr1281 | NM_001005568.1 | chr2:111328420-111329338 |
| 15025 | Olfr1180 | NM_146918.2 | chr2:88411626-88412689 | | 15120 | Olfr1282 | NM_146907.2 | chr2:111335158-111336076 |
| 15026 | Olfr1181 | NM_001011816.1 | chr2:88423087-88424023 | | 15121 | Olfr1283 | NM_207236.1 | chr2:111368633-111369551 |
| 15027 | Olfr1182 | NM_001011535.2 | chr2:88446018-88449121 | | 15122 | Olfr1284 | NM_146381.1 | chr2:111379001-111379937 |
| 15028 | Olfr1183 | NM_146529.2 | chr2:88461341-88462253 | | 15123 | Olfr1286 | NM_207254.1 | chr2:111420031-111420949 |
| 15029 | Olfr1184 | NM_148486.3 | chr2:88486733-88487669 | | 15124 | Olfr1287 | NM_001011773.1 | chr2:111449141-111450059 |
| 15030 | Olfr1186 | NM_146530.2 | chr2:88525500-88526590 | | 15125 | Olfr1288 | NM_146400.2 | chr2:111478785-111479724 |
| 15031 | Olfr1188 | NM_146919.2 | chr2:88559450-88560418 | | 15126 | Olfr1289 | NM_146404.1 | chr2:111483431-111484328 |
| 15032 | Olfr1189 | NM_146772.2 | chr2:88591805-88592726 | | 15127 | Olfr129 | NM_146327.2 | chr17:38054598-38059784 |
| 15033 | Olfr119 | NM_001011830.2 | chr17:37696684-37701637 | | 15128 | Olfr1290 | NM_001278787.1 | chr2:111489217-111493815 |
| 15034 | Olfr1193 | NM_001011517.2 | chr2:88677856-88678813 | | 15129 | Olfr1294 | NM_146885.1 | chr2:111537348-111538287 |
| 15035 | Olfr1195 | NM_146753.2 | chr2:88682803-88683730 | | 15130 | Olfr1295 | NM_146403.1 | chr2:111564503-111565442 |
| 15036 | Olfr1196 | NM_146464.2 | chr2:88700382-88701327 | | 15131 | Olfr1297 | NM_146888.1 | chr2:111621133-111622072 |
| 15037 | Olfr1197 | NM_001005225.1 | chr2:88728652-88729597 | | 15132 | Olfr1298 | NM_146886.1 | chr2:111645056-111645995 |
| 15038 | Olfr1198 | NM_207567.1 | chr2:88745959-88746886 | | 15133 | Olfr1299 | NM_146884.2 | chr2:111661452-111665166 |
| 15039 | Olfr1199 | NM_146458.1 | chr2:88755740-88756673 | | 15134 | Olfr13 | NM_146652.1 | chr6:43173987-43174920 |
| 15040 | Olfr12 | NM_208896.2 | chr1:92619880-92621001 | | 15135 | Olfr130 | NM_146487.1 | chr17:38067172-38068126 |
| 15041 | Olfr120 | NM_146631.1 | chr17:37725998-37726991 | | 15136 | Olfr1300-ps1 | NR_033534.1 | chr2:111667436-111693319 |
| 15042 | Olfr1200 | NM_001005227.2 | chr2:88767302-88768313 | | 15137 | Olfr1301 | NM_146887.1 | chr2:111754250-111755189 |
| 15043 | Olfr1201 | NM_146893.1 | chr2:88794383-88795307 | | 15138 | Olfr1302 | NM_146889.2 | chr2:111780312-111781260 |
| 15044 | Olfr1202 | NM_146462.1 | chr2:88817172-88818102 | | 15139 | Olfr1303 | NM_146402.2 | chr2:111813785-111814724 |
| 15045 | Olfr1204 | NM_146463.2 | chr2:88851951-88852881 | | 15140 | Olfr1305 | NM_146401.2 | chr2:111872914-111873853 |
| 15046 | Olfr1205 | NM_146896.3 | chr2:88829756-88832042 | | 15141 | Olfr1306 | NM_001011803.2 | chr2:111911989-111912928 |
| 15047 | Olfr1206 | NM_001011810.2 | chr2:88864606-88865530 | | 15142 | Olfr1307 | NM_001011787.1 | chr2:111944515-111945454 |
| 15048 | Olfr1208 | NM_146778.1 | chr2:88896668-88897595 | | 15143 | Olfr1308 | NM_207151.1 | chr2:111960108-111961071 |
| 15049 | Olfr1209 | NM_146461.2 | chr2:88909458-88910391 | | 15144 | Olfr1309 | NM_146447.1 | chr2:111983133-111984096 |
| 15050 | Olfr121 | NM_146629.2 | chr17:37748865-37753004 | | 15145 | Olfr131 | NM_146867.1 | chr17:38082031-38082976 |
| 15051 | Olfr1211 | NM_001011804.1 | chr2:88929377-88930313 | | 15146 | Olfr1310 | NM_146449.1 | chr2:112008245-112009184 |
| 15052 | Olfr1212 | NM_207140.1 | chr2:88958467-88959403 | | 15147 | Olfr1311 | NM_146274.1 | chr2:112020913-112021852 |
| 15053 | Olfr1213 | NM_146898.2 | chr2:88972953-88980267 | | 15148 | Olfr1312 | NM_146362.1 | chr2:112042076-112043030 |
| 15054 | Olfr1214 | NM_146897.2 | chr2:88987264-88988200 | | 15149 | Olfr1313 | NM_207150.1 | chr2:112071645-112072581 |
| 15055 | Olfr1215 | NM_146459.2 | chr2:89001347-89002290 | | 15150 | Olfr1314 | NM_146450.2 | chr2:112091760-112092699 |
| 15056 | Olfr1216 | NM_146893.2 | chr2:89013126-89014062 | | 15151 | Olfr1316 | NM_146742.1 | chr2:112129870-112130815 |
| 15057 | Olfr1217 | NM_146917.2 | chr2:89022994-89024099 | | 15152 | Olfr1317 | NM_146448.1 | chr2:112141946-112142897 |
| 15058 | Olfr1218 | NM_146818.2 | chr2:89054488-89055424 | | 15153 | Olfr1318 | NM_001011802.2 | chr2:112155897-112157007 |
| 15059 | Olfr1219 | NM_146899.1 | chr2:89074153-89075089 | | 15154 | Olfr132 | NM_001005481.1 | chr17:38130248-38131190 |
| 15060 | Olfr122 | NM_146288.3 | chr17:37768641-37772620 | | 15155 | Olfr1320 | NM_207240.2 | chrX:49683503-49684463 |
| 15061 | Olfr1220 | NM_146900.2 | chr2:89096937-89097963 | | 15156 | Olfr1321 | NM_207631.1 | chrX:49726972-49727932 |
| 15062 | Olfr1221 | NM_146902.2 | chr2:89111574-89112510 | | 15157 | Olfr1322 | NM_001011794.1 | chrX:49885468-49886401 |
| 15063 | Olfr1222 | NM_001011860.1 | chr2:89124793-89125729 | | 15158 | Olfr1323 | NM_146390.1 | chrX:50009305-50010235 |
| 15064 | Olfr1223 | NM_146892.2 | chr2:89144085-89151336 | | 15159 | Olfr1324 | NM_146292.1 | chrX:50425495-50426494 |
| 15065 | Olfr1225 | NM_146891.2 | chr2:89170218-89171245 | | 15160 | Olfr1325 | NM_146398.1 | chrX:74594327-74595275 |
| 15066 | Olfr1226 | NM_146967.1 | chr2:89193099-89194032 | | 15161 | Olfr1328 | NM_146399.2 | chr4:118933898-118934840 |
| 15067 | Olfr1228 | NM_146971.1 | chr2:89248720-89249692 | | 15162 | Olfr1329 | NM_001011870.2 | chr4:118916523-118917465 |
| 15068 | Olfr1229 | NM_001011761.1 | chr2:89282195-89283131 | | 15163 | Olfr133 | NM_146831.1 | chr17:38148589-38149528 |
| 15069 | Olfr123 | NM_146630.1 | chr17:37795445-37796375 | | 15164 | Olfr1330 | NM_146334.2 | chr4:118893084-118894032 |
| 15070 | Olfr1230 | NM_146789.1 | chr2:89296350-89297268 | | 15165 | Olfr1331 | NM_001011856.2 | chr4:118868782-118869736 |
| 15071 | Olfr1231 | NM_146454.2 | chr2:89302648-89303590 | | 15166 | Olfr1333 | NM_207157.2 | chr4:118829484-118830438 |
| 15072 | Olfr1232 | NM_146323.1 | chr2:89325242-89326178 | | 15167 | Olfr1335 | NM_207703.1 | chr4:118808854-118809862 |
| 15073 | Olfr1233 | NM_146972.1 | chr2:89339382-89340300 | | 15168 | Olfr1336 | NM_146915.1 | chr7:6460510-6461455 |
| 15074 | Olfr1234 | NM_146973.2 | chr2:89362482-89363427 | | 15169 | Olfr1337 | NM_146309.3 | chr4:118781635-118782586 |
| 15075 | Olfr1238 | NM_146790.1 | chr2:89406129-89407077 | | 15170 | Olfr1338 | NM_207152.2 | chr4:118753594-118754536 |
| 15076 | Olfr1239 | NM_146970.1 | chr2:89417493-89418411 | | 15171 | Olfr1339 | NM_146852.2 | chr4:118734530-118735478 |
| 15077 | Olfr124 | NM_146796.1 | chr17:37805068-37806190 | | 15172 | Olfr134 | NM_146832.1 | chr17:38175085-38176024 |
| 15078 | Olfr1240 | NM_146808.2 | chr2:89439269-89440343 | | 15173 | Olfr1340 | NM_146304.2 | chr4:118726248-118727196 |
| 15079 | Olfr1241 | NM_146455.1 | chr2:89482188-89483133 | | 15174 | Olfr1341 | NM_146853.2 | chr4:118709408-118710347 |
| 15080 | Olfr1242 | NM_146983.2 | chr2:89493293-89494346 | | 15175 | Olfr1342 | NM_146713.1 | chr4:118689502-118690450 |
| 15081 | Olfr1243 | NM_146969.1 | chr2:89527490-89528408 | | 15176 | Olfr1344 | NM_177061.3 | chr7:6439901-6440867 |
| 15082 | Olfr1245 | NM_146788.2 | chr2:89574711-89575773 | | 15177 | Olfr1346 | NM_146916.1 | chr7:6474111-6475053 |
| 15083 | Olfr1246 | NM_146711.2 | chr2:89590068-89591146 | | 15178 | Olfr1347 | NM_146385.1 | chr7:6487912-6488872 |
| 15084 | Olfr1247 | NM_146566.2 | chr2:89609088-89610153 | | 15179 | Olfr1348 | NM_146913.1 | chr7:6501285-6502224 |
| 15085 | Olfr1248 | NM_146791.1 | chr2:89617167-89618245 | | 15180 | Olfr1349 | NM_207136.1 | chr7:6514473-6515427 |
| 15086 | Olfr1249 | NM_001011796.2 | chr2:89629939-89630896 | | 15181 | Olfr135 | NM_146332.1 | chr17:38208246-38209185 |
| 15087 | Olfr125 | NM_146290.2 | chr17:37834910-37836028 | | 15182 | Olfr1350 | NM_146389.1 | chr7:6569992-6570919 |
| 15088 | Olfr1250 | NM_146965.1 | chr2:89656494-89657439 | | 15183 | Olfr1351 | NM_147040.1 | chr10:79017323-79018283 |
| 15089 | Olfr1251 | NM_001011529.1 | chr2:89666927-89667884 | | 15184 | Olfr1352 | NM_147071.1 | chr10:78983049-78984721 |
| 15090 | Olfr1252 | NM_207568.1 | chr2:89721164-89722109 | | 15185 | Olfr1353 | NM_147042.2 | chr10:78963508-78970612 |
| 15091 | Olfr1253 | NM_146476.1 | chr2:89751869-89752826 | | 15186 | Olfr1354 | NM_001199840.1 | chr10:78916841-78917936 |
| 15092 | Olfr1254 | NM_146476.1 | chr2:89788405-89789350 | | 15187 | Olfr1355 | NM_207571.2 | chr10:78875548-78880106 |
| 15093 | Olfr1255 | NM_146977.2 | chr2:89816327-89817260 | | 15188 | Olfr1356 | NM_146308.2 | chr10:78846950-78847913 |
| 15094 | Olfr1256 | NM_146835022-89835943 | | | 15189 | Olfr1357 | NM_001011737.2 | chr10:78611668-78618074 |
| 15095 | Olfr1257 | NM_146982.1 | chr2:89880827-89881757 | | 15190 | Olfr1359 | NM_001011820.1 | chr13:21674000-21703944 |
| 15096 | Olfr1258 | NM_146978.1 | chr2:89929810-89930746 | | 15191 | Olfr136 | NM_146807.1 | chr17:38335158-38336097 |
| 15097 | Olfr1259 | NM_146341.1 | chr2:89943183-89944113 | | 15192 | Olfr1360 | NM_146543.2 | chr13:21674000-21674980 |
| 15098 | Olfr126 | NM_146890.2 | chr17:37850593-37851553 | | 15193 | Olfr1361 | NM_146541.2 | chr13:21658367-21659321 |
| 15099 | Olfr1260 | NM_146981.1 | chr2:89977779-89978712 | | 15194 | Olfr1362 | NM_146744.2 | chr13:21611019-21612004 |

Fig. 26 - 81

| | | | | | | | | |
|---|---|---|---|---|---|---|---|---|
| 15195 | Olfr1364 | NM_146540.2 | chr13:21573509-21574454 | | 15290 | Olfr1489 | NM_146635.1 | chr19:13633112-13634054 |
| 15196 | Olfr1366 | NM_146283.2 | chr13:21536973-21538027 | | 15291 | Olfr149 | NM_207138.1 | chr9:39701831-39702767 |
| 15197 | Olfr1367 | NM_146533.1 | chr13:21346929-21347880 | | 15292 | Olfr1490 | NM_001011832.1 | chr19:13654445-13655396 |
| 15198 | Olfr1368 | NM_146534.1 | chr13:21142110-21143055 | | 15293 | Olfr1491 | NM_146345.1 | chr19:13704828-13705788 |
| 15199 | Olfr137 | NM_146488.1 | chr17:38304520-38305459 | | 15294 | Olfr1494 | NM_146990.1 | chr19:13749107-13750055 |
| 15200 | Olfr1370 | NM_146535.1 | chr13:21072348-21073299 | | 15295 | Olfr1495 | NM_146344.1 | chr19:13768343-13769303 |
| 15201 | Olfr1371 | NM_207253.1 | chr11:52213051-52213987 | | 15296 | Olfr1496 | NM_146989.2 | chr19:13780547-13781614 |
| 15202 | Olfr1372-ps1 | NR_034155.1 | chr11:52154875-52157907 | | 15297 | Olfr1497 | NM_146741.1 | chr19:13794664-13795609 |
| 15203 | Olfr1373 | NM_207227.1 | chr11:52144592-52145528 | | 15298 | Olfr1499 | NM_146796.1 | chr19:13814643-13815588 |
| 15204 | Olfr1377 | NM_146911.1 | chr11:50984702-50985626 | | 15299 | Olfr15 | NM_008762.2 | chr16:3838974-3839913 |
| 15205 | Olfr1378 | NM_146910.1 | chr11:50969019-50969967 | | 15300 | Olfr150 | NM_146609.2 | chr9:39736816-39737755 |
| 15206 | Olfr138 | NM_130868.1 | chr17:38274772-38275711 | | 15301 | Olfr1500 | NM_001011831.1 | chr19:13827458-13828394 |
| 15207 | Olfr1380 | NM_207573.1 | chr11:49563922-49564858 | | 15302 | Olfr1501 | NM_146633.1 | chr19:13838223-13839171 |
| 15208 | Olfr1381 | NM_146469.2 | chr11:49551748-49552684 | | 15303 | Olfr1502 | NM_146797.1 | chr19:13861794-13862745 |
| 15209 | Olfr1382 | NM_001011790.1 | chr11:49535186-49536122 | | 15304 | Olfr1504 | NM_146634.1 | chr19:13887260-13888208 |
| 15210 | Olfr1383 | NM_207574.1 | chr11:49523724-49524660 | | 15305 | Olfr1505 | NM_001011850.1 | chr19:13919021-13919972 |
| 15211 | Olfr1384 | NM_146472.2 | chr11:49513617-49514651 | | 15306 | Olfr1506 | NM_146265.2 | chr2:90221566-90325126 |
| 15212 | Olfr1385 | NM_001011805.1 | chr11:49494534-49495464 | | 15307 | Olfr1507 | NM_001170918.1 | chr14:52489934-52495695 |
| 15213 | Olfr1386 | NM_001011741.2 | chr11:49470053-49471181 | | 15308 | Olfr1508 | NM_020513.2 | chr14:52462720-52467461 |
| 15214 | Olfr1387 | NM_146473.1 | chr11:49459680-49460616 | | 15309 | Olfr1509 | NM_020514.2 | chr14:52450392-52451402 |
| 15215 | Olfr1388 | NM_146467.1 | chr11:49443852-49444788 | | 15310 | Olfr151 | NM_207664.2 | chr9:37729976-37731061 |
| 15216 | Olfr1389 | NM_147066.2 | chr11:49430426-49431499 | | 15311 | Olfr1510 | NM_146431.2 | chr14:52409888-52410927 |
| 15217 | Olfr139 | NM_147003.1 | chr11:74044324-74045272 | | 15312 | Olfr1511 | NM_146271.2 | chr14:52389814-52390771 |
| 15218 | Olfr1390 | NM_147065.1 | chr11:49340533-49341469 | | 15313 | Olfr1512 | NM_146432.2 | chr14:52372109-52373051 |
| 15219 | Olfr1391 | NM_146468.1 | chr11:49327412-49328348 | | 15314 | Olfr1513 | NM_001012269.2 | chr14:52349102-52350044 |
| 15220 | Olfr1392 | NM_146470.2 | chr11:49293396-49294322 | | 15315 | Olfr152 | NM_146646.2 | chr2:87782535-87783486 |
| 15221 | Olfr1393 | NM_146471.1 | chr11:49280149-49281085 | | 15316 | Olfr153 | NM_206823.1 | chr2:87532034-87532958 |
| 15222 | Olfr1394 | NM_146276.1 | chr11:49160015-49160954 | | 15317 | Olfr1532-ps1 | NM_001011542.1 | chr7:106914199-106915123 |
| 15223 | Olfr1395 | NM_146877.1 | chr11:49148258-49149212 | | 15318 | Olfr1535 | NM_207572.1 | chr13:21555039-21556020 |
| 15224 | Olfr1396 | NM_146337.1 | chr11:49112776-49113757 | | 15319 | Olfr1537 | NM_207665.1 | chr9:39237486-39238431 |
| 15225 | Olfr140 | NM_020515.1 | chr2:90051413-90052322 | | 15320 | Olfr154 | NM_013728.2 | chr2:85663376-85664455 |
| 15226 | Olfr1402 | NM_146275.1 | chr3:97410216-97411179 | | 15321 | Olfr155 | NM_019473.1 | chr4:43854291-43855463 |
| 15227 | Olfr1404 | NM_146881.2 | chr1:173215606-173216640 | | 15322 | Olfr156 | NM_019474.2 | chr4:43820334-43821433 |
| 15228 | Olfr1406 | NM_146763.2 | chr1:173183441-173184504 | | 15323 | Olfr157 | NM_019475.3 | chr4:43834751-43836517 |
| 15229 | Olfr1408 | NM_146764.1 | chr1:173130282-173131215 | | 15324 | Olfr159 | NM_019476.3 | chr4:43770049-43771009 |
| 15230 | Olfr141 | NM_181818.2 | chr2:86806020-86806997 | | 15325 | Olfr16 | NM_008763.2 | chr1:172956767-172957817 |
| 15231 | Olfr1410 | NM_146493.1 | chr1:92607838-92608807 | | 15326 | Olfr160 | NM_030553.2 | chr9:37711347-37712280 |
| 15232 | Olfr1411 | NM_146490.1 | chr1:92596520-92597492 | | 15327 | Olfr161 | NM_146860.1 | chr16:3592397-3593339 |
| 15233 | Olfr1412 | NM_146277.1 | chr1:92588831-92589297 | | 15328 | Olfr164 | NM_146451.1 | chr16:19285793-19286741 |
| 15234 | Olfr1413 | NM_147037.2 | chr1:92573124-92574206 | | 15329 | Olfr165 | NM_146466.1 | chr16:19407075-19408017 |
| 15235 | Olfr1414 | NM_147039.2 | chr1:92511047-92518515 | | 15330 | Olfr166 | NM_147068.1 | chr16:19486838-19487778 |
| 15236 | Olfr1415 | NM_001011525.1 | chr1:92490817-92491753 | | 15331 | Olfr167 | NM_146935.1 | chr16:19514695-19515634 |
| 15237 | Olfr1416 | NM_147038.1 | chr1:92479680-92480619 | | 15332 | Olfr168 | NM_146357.1 | chr16:19529979-19530918 |
| 15238 | Olfr1417 | NM_146936.1 | chr19:11828076-11829024 | | 15333 | Olfr169 | NM_001011855.1 | chr16:19565939-19566881 |
| 15239 | Olfr1418 | NM_001011524.1 | chr19:11854994-11855951 | | 15334 | Olfr17 | NM_020598.2 | chr7:107097466-107098414 |
| 15240 | Olfr1419 | NM_001011775.1 | chr19:11870182-11871214 | | 15335 | Olfr170 | NM_146957.1 | chr16:19605724-19606666 |
| 15241 | Olfr142 | NM_146984.1 | chr2:90252068-90252986 | | 15336 | Olfr171 | NM_146958.2 | chr16:19624156-19625101 |
| 15242 | Olfr1420 | NM_146410.1 | chr19:11896022-11896952 | | 15337 | Olfr172 | NM_147001.2 | chr16:58760152-58761240 |
| 15243 | Olfr1423 | NM_146680.1 | chr19:12035807-12036740 | | 15338 | Olfr173 | NM_147000.1 | chr16:58796778-58797942 |
| 15244 | Olfr1424 | NM_146681.1 | chr19:12058808-12059750 | | 15339 | Olfr175-ps1 | NM_147002.2 | chr16:58823780-58826761 |
| 15245 | Olfr1425 | NM_001011853.1 | chr19:12073694-12074630 | | 15340 | Olfr176 | NM_146993.1 | chr16:58872214-58873148 |
| 15246 | Olfr1426 | NM_146809.2 | chr19:12087609-12091847 | | 15341 | Olfr177 | NM_146996.2 | chr16:58872218-58873148 |
| 15247 | Olfr1427 | NM_146679.1 | chr19:12098701-12099637 | | 15342 | Olfr179 | NM_146997.2 | chr16:58889258-58890218 |
| 15248 | Olfr1428 | NM_146678.2 | chr19:12108599-12109544 | | 15343 | Olfr18 | NM_146563.1 | chr9:20313891-20336094 |
| 15249 | Olfr143 | NM_146806.2 | chr9:38253418-38254360 | | 15344 | Olfr180 | NM_001011662.2 | chr16:58915685-58918486 |
| 15250 | Olfr1431 | NM_146744.1 | chr19:12209567-12210506 | | 15345 | Olfr181 | NM_146999.2 | chr16:58925556-58928644 |
| 15251 | Olfr1433 | NM_146685.3 | chr19:12279853-12283988 | | 15346 | Olfr183 | NM_146485.2 | chr16:58995403-59000616 |
| 15252 | Olfr1434 | NM_146685.3 | chr19:12957098-12958036 | | 15347 | Olfr186 | NM_146321.1 | chr16:59026975-59027905 |
| 15253 | Olfr1436 | NM_146687.2 | chr19:12298182-12299130 | | 15348 | Olfr187 | NM_146322.2 | chr16:59035779-59039749 |
| 15254 | Olfr1437 | NM_001011839.1 | chr19:12321886-12322825 | | 15349 | Olfr19 | NM_146335.1 | chr16:16673049-16673979 |
| 15255 | Olfr1440 | NM_146684.1 | chr19:12394264-12395212 | | 15350 | Olfr190 | NM_146397.2 | chr16:59074154-59075078 |
| 15256 | Olfr1441 | NM_146683.1 | chr19:12422310-12423267 | | 15351 | Olfr191 | NM_001011807.2 | chr16:59085551-59086481 |
| 15257 | Olfr1442 | NM_146697.2 | chr19:12674178-12675243 | | 15352 | Olfr192 | NM_207549.1 | chr16:59098065-59098990 |
| 15258 | Olfr1443 | NM_146698.2 | chr19:12678166-12683846 | | 15353 | Olfr193 | NM_001011791.1 | chr16:59109678-59110608 |
| 15259 | Olfr1444 | NM_146702.1 | chr19:12861776-12862736 | | 15354 | Olfr194 | NM_001005524.2 | chr16:59119147-59120068 |
| 15260 | Olfr1445 | NM_146699.1 | chr19:12883882-12884827 | | 15355 | Olfr195 | NM_146998.1 | chr16:59148851-59149778 |
| 15261 | Olfr1446 | NM_146704.1 | chr19:12889648-12890575 | | 15356 | Olfr196 | NM_146779.2 | chr16:59167211-59168141 |
| 15262 | Olfr1447 | NM_200848.1 | chr19:12900848-12901778 | | 15357 | Olfr197 | NM_146484.1 | chr16:59185555-59186481 |
| 15263 | Olfr1448 | NM_146701.1 | chr19:12919362-12920307 | | 15358 | Olfr198 | NM_001011808.1 | chr16:59201503-59202424 |
| 15264 | Olfr1449 | NM_146683.1 | chr19:12934739-12935684 | | 15359 | Olfr199 | NM_207550.2 | chr16:59215684-59216611 |
| 15265 | Olfr145 | NM_146313.1 | chr9:37897405-37898338 | | 15360 | Olfr2 | NM_010983.2 | chr7:107000874-107002605 |
| 15266 | Olfr1450 | NM_146371.1 | chr19:12953590-12954568 | | 15361 | Olfr20 | NM_146923.2 | chr11:73350858-73354699 |
| 15267 | Olfr1451 | NM_146765.1 | chr19:12999987-12999920 | | 15362 | Olfr201 | NM_146994.2 | chr16:59268738-59269665 |
| 15268 | Olfr1453 | NM_146700.1 | chr19:13027403-13028327 | | 15363 | Olfr202 | NM_146995.1 | chr16:59283571-59284495 |
| 15269 | Olfr1454 | NM_146692.1 | chr19:13063412-13064336 | | 15364 | Olfr203 | NM_146486.2 | chr16:59303154-59304075 |
| 15270 | Olfr1457 | NM_146535.1 | chr19:13094692-13095646 | | 15365 | Olfr204 | NM_146992.2 | chr16:59314487-59315405 |
| 15271 | Olfr1459 | NM_146689.1 | chr19:13145733-13146657 | | 15366 | Olfr205 | NM_001011736.1 | chr16:59328589-59329507 |
| 15272 | Olfr146 | NM_146747.1 | chr9:39018618-39019539 | | 15367 | Olfr206 | NM_146991.1 | chr16:59344778-59345699 |
| 15273 | Olfr1461 | NM_146302.1 | chr19:13165015-13165954 | | 15368 | Olfr209 | NM_207551.2 | chr16:59361298-59362216 |
| 15274 | Olfr1462 | NM_146693.1 | chr19:13190668-13191592 | | 15369 | Olfr211 | NM_148912.1 | chr6:116493610-116494540 |
| 15275 | Olfr1463 | NM_001011840.1 | chr19:13234251-13235184 | | 15370 | Olfr212 | NM_001011800.2 | chr6:116506515-116517965 |
| 15276 | Olfr1465 | NM_001011841.1 | chr19:13313359-13314283 | | 15371 | Olfr213 | NM_001011801.1 | chr6:116540454-116541438 |
| 15277 | Olfr1466 | NM_146694.1 | chr19:13341759-13342692 | | 15372 | Olfr214 | NM_146759.1 | chr6:116556426-116557389 |
| 15278 | Olfr1467 | NM_146691.1 | chr19:13364629-13365556 | | 15373 | Olfr215 | NM_146446.1 | chr6:116582011-116582944 |
| 15279 | Olfr1469 | NM_146695.1 | chr19:13410570-13411500 | | 15374 | Olfr218 | NM_001001809.2 | chr1:173203357-173204290 |
| 15280 | Olfr147 | NM_146869.2 | chr9:38401710-38403829 | | 15375 | Olfr220 | NM_207694.1 | chr1:174448624-174449602 |
| 15281 | Olfr1471 | NM_146945013 | chr19:13445013-13445958 | | 15376 | Olfr221 | NM_001001808.2 | chr14:52035173-52036109 |
| 15282 | Olfr1472 | NM_146690.2 | chr19:13453570-13454515 | | 15377 | Olfr222 | NM_001011789.1 | chr11:59570781-59571738 |
| 15283 | Olfr1474 | NM_001011842.1 | chr19:13470971-13471916 | | 15378 | Olfr223 | NM_146429.1 | chr11:59589127-59590087 |
| 15284 | Olfr1475 | NM_146301.1 | chr19:13479251-13480196 | | 15379 | Olfr224 | NM_207695.1 | chr11:58586398-58567343 |
| 15285 | Olfr1477 | NM_146896.2 | chr19:13500545-13503292 | | 15380 | Olfr225 | NM_001011740.2 | chr11:59612965-59614225 |
| 15286 | Olfr148 | NM_146505.1 | chr9:39613568-39614501 | | 15381 | Olfr228 | NM_146405.2 | chr2:86482798-86483740 |
| 15287 | Olfr1480 | NM_207575.1 | chr19:13529674-13530622 | | 15382 | Olfr229 | NM_146613.1 | chr9:39909804-39910728 |
| 15288 | Olfr1484 | NM_146291.1 | chr19:13585305-13586253 | | 15383 | Olfr23 | NM_010970.1 | chr11:73940247-73941225 |
| 15289 | Olfr1487 | NM_146636.1 | chr19:13619163-13620111 | | 15384 | Olfr231 | NM_001005520.2 | chr1:174117090-174118014 |

Fig. 26 - 82

| | | | | | | | | |
|---|---|---|---|---|---|---|---|---|
| 15385 | Olfr235 | NM_146686.2 | chr19:12268231-12269170 | | 15480 | Olfr367-ps | NM_001081010.2 | chr2:37266950-37271387 |
| 15386 | Olfr237-ps1 | NM_146854.1 | chr6:43153306-43154239 | | 15481 | Olfr368 | NM_146374.1 | chr2:37331748-37332732 |
| 15387 | Olfr239 | NM_207175.2 | chr17:33199061-33200009 | | 15482 | Olfr370 | NM_146270.2 | chr8:83541092-83542188 |
| 15388 | Olfr24 | NM_146806.1 | chr9:18754691-18755633 | | 15483 | Olfr371 | NM_146859.2 | chr8:85230496-85231435 |
| 15389 | Olfr242 | NM_010974.1 | chr9:39144101-39145018 | | 15484 | Olfr372 | NM_207555.2 | chr8:72067659-72068675 |
| 15390 | Olfr243 | NM_001025386.1 | chr7:103716595-103717546 | | 15485 | Olfr373 | NM_146539.2 | chr8:72099761-72100706 |
| 15391 | Olfr247 | NM_146269.2 | chr10:129974604-129984424 | | 15486 | Olfr374 | NM_146338.2 | chr8:72107039-72110509 |
| 15392 | Olfr248 | NM_146714.2 | chr1:174391045-174392055 | | 15487 | Olfr376 | NM_001172686.1 | chr11:73371245-73375704 |
| 15393 | Olfr25 | NM_146870.2 | chr9:38329491-38330559 | | 15488 | Olfr378 | NM_147024.2 | chr11:73425036-73428477 |
| 15394 | Olfr259 | NM_146770.2 | chr2:87107446-87108385 | | 15489 | Olfr38 | NM_146986.1 | chr6:42762053-42763007 |
| 15395 | Olfr26 | NM_146783.2 | chr9:38855059-38855990 | | 15490 | Olfr380 | NM_147025.1 | chr11:73453274-73454210 |
| 15396 | Olfr262 | NM_146688.1 | chr19:12240720-12241659 | | 15491 | Olfr381 | NM_147022.2 | chr11:73485886-73486822 |
| 15397 | Olfr263 | NM_010984.1 | chr13:21132776-21133730 | | 15492 | Olfr382 | NM_146443.1 | chr11:73516258-73517197 |
| 15398 | Olfr266 | NM_146489.1 | chr3:106821606-106822557 | | 15493 | Olfr384 | NM_207224.1 | chr11:73602581-73603520 |
| 15399 | Olfr267 | NM_146920.2 | chr4:58784778-58785720 | | 15494 | Olfr385 | NM_147023.1 | chr11:73588797-73589736 |
| 15400 | Olfr27 | NM_148829.2 | chr9:39138166-39145070 | | 15495 | Olfr389 | NM_147009.3 | chr11:73776386-73780589 |
| 15401 | Olfr270 | NM_146607.1 | chr4:52970628-52971567 | | 15496 | Olfr39 | NM_148825.2 | chr9:20282350-20286648 |
| 15402 | Olfr272 | NM_146839.1 | chr4:52910832-52911792 | | 15497 | Olfr390 | NM_146347.1 | chr11:73786939-73787875 |
| 15403 | Olfr273 | NM_146824.1 | chr4:52855557-52856511 | | 15498 | Olfr391-ps | NM_001159975.1 | chr11:73798752-73802984 |
| 15404 | Olfr275 | NM_146858.2 | chr4:52825398-52826358 | | 15499 | Olfr392 | NM_147006.2 | chr11:73814141-73816877 |
| 15405 | Olfr279 | NM_001001807.1 | chr15:98497473-98498406 | | 15500 | Olfr393 | NM_147008.2 | chr11:73847184-73848123 |
| 15406 | Olfr281 | NM_146280.1 | chr15:98456311-98457247 | | 15501 | Olfr394 | NM_147007.1 | chr11:73887437-73888370 |
| 15407 | Olfr282 | NM_146457.2 | chr15:98437469-98438397 | | 15502 | Olfr395 | NM_147005.1 | chr11:73906551-73907490 |
| 15408 | Olfr283 | NM_147036.1 | chr15:98378178-98379108 | | 15503 | Olfr397 | NM_146346.1 | chr11:73964609-73965557 |
| 15409 | Olfr284 | NM_146315.1 | chr15:98340021-98340939 | | 15504 | Olfr398 | NM_146710.1 | chr11:73983661-73984606 |
| 15410 | Olfr285 | NM_001011778.1 | chr15:98312588-98313548 | | 15505 | Olfr399 | NM_147004.2 | chr11:74053775-74054778 |
| 15411 | Olfr286 | NM_001011779.1 | chr15:98226674-98228450 | | 15506 | Olfr401 | NM_146706.1 | chr11:74121290-74122238 |
| 15412 | Olfr287 | NM_001011780.1 | chr15:98206970-98221056 | | 15507 | Olfr402 | NM_146708.1 | chr11:74155155-74156103 |
| 15413 | Olfr288 | NM_001011733.2 | chr15:98186012-98195542 | | 15508 | Olfr403 | NM_207622.1 | chr11:74195504-74196446 |
| 15414 | Olfr290 | NM_146416.2 | chr7:84915780-84916728 | | 15509 | Olfr406 | NM_001011863.1 | chr11:74269390-74270362 |
| 15415 | Olfr291 | NM_146415.2 | chr7:84853570-84857318 | | 15510 | Olfr410 | NM_146707.1 | chr11:74334281-74335229 |
| 15416 | Olfr292 | NM_146620.2 | chr7:86688340-86695384 | | 15511 | Olfr411 | NM_146709.2 | chr11:74346623-74347672 |
| 15417 | Olfr293 | NM_001011752.1 | chr7:86663663-86664674 | | 15512 | Olfr412 | NM_001011851.1 | chr11:74364670-74365609 |
| 15418 | Olfr294 | NM_001011750.2 | chr7:86615635-86616643 | | 15513 | Olfr414 | NM_146761.2 | chr1:174430429-174431384 |
| 15419 | Olfr295 | NM_146851.2 | chr7:86585276-86586206 | | 15514 | Olfr417 | NM_207137.3 | chr1:174368918-174369848 |
| 15420 | Olfr297 | NM_146618.2 | chr7:86526758-86527691 | | 15515 | Olfr418-ps1 | NM_146651.2 | chr1:173270146-173271137 |
| 15421 | Olfr298 | NM_001011751.1 | chr7:86488550-86489549 | | 15516 | Olfr419 | NM_146715.2 | chr1:174249888-174250976 |
| 15422 | Olfr299 | NM_001011767.1 | chr7:86465412-86466405 | | 15517 | Olfr420 | NM_146305.2 | chr1:174158721-174159767 |
| 15423 | Olfr29-ps1 | NR_033638.1 | chr4:43781364-43782327 | | 15518 | Olfr421-ps1 | NR_047667.1 | chr1:174151480-174152530 |
| 15424 | Olfr3 | NM_208903.1 | chr2:36812148-36813090 | | 15519 | Olfr424 | NM_146721.2 | chr1:174136745-174137693 |
| 15425 | Olfr30 | NM_146878.2 | chr11:58454914-58455980 | | 15520 | Olfr426 | NM_001206926.1 | chr1:174099459-174100410 |
| 15426 | Olfr301 | NM_212436.2 | chr7:86403848-86413299 | | 15521 | Olfr427 | NM_207158.1 | chr1:174099469-174100407 |
| 15427 | Olfr303 | NM_146619.1 | chr7:86394536-86395496 | | 15522 | Olfr429 | NM_146722.2 | chr1:174089037-174089980 |
| 15428 | Olfr304 | NM_001011828.1 | chr7:86385656-86386658 | | 15523 | Olfr43 | NM_146711.2 | chr11:74206197-74207289 |
| 15429 | Olfr305 | NM_146616.2 | chr7:86363675-86364335 | | 15524 | Olfr430 | NM_146718.2 | chr1:174069299-174070253 |
| 15430 | Olfr307 | NM_146617.1 | chr7:86335452-86336394 | | 15525 | Olfr432 | NM_146716.2 | chr1:174050374-174051313 |
| 15431 | Olfr308 | NM_146621.1 | chr7:86321023-86321950 | | 15526 | Olfr433 | NM_146717.2 | chr1:174041932-174042936 |
| 15432 | Olfr309 | NM_001011866.1 | chr7:86306184-86307111 | | 15527 | Olfr434 | NM_146369.1 | chr6:43216914-43217880 |
| 15433 | Olfr31 | NM_147027.2 | chr14:14328112-14329066 | | 15528 | Olfr435 | NM_146653.1 | chr6:43201645-43202587 |
| 15434 | Olfr310 | NM_001011520.2 | chr7:86268729-86269811 | | 15529 | Olfr437 | NM_146296.1 | chr6:43167059-43167992 |
| 15435 | Olfr311 | NM_146537.2 | chr11:58841115-58842042 | | 15530 | Olfr44 | NM_146830.2 | chr9:39484203-39493988 |
| 15436 | Olfr312 | NM_001011819.2 | chr11:58831155-58832082 | | 15531 | Olfr441 | NM_146655.1 | chr6:43115743-43116676 |
| 15437 | Olfr313 | NM_146836.2 | chr11:58816927-58818001 | | 15532 | Olfr444 | NM_146656.1 | chr6:42955439-42956432 |
| 15438 | Olfr314 | NM_001011760.2 | chr11:58786138-58787269 | | 15533 | Olfr446 | NM_148295.1 | chr6:42927232-42928159 |
| 15439 | Olfr315 | NM_146538.2 | chr11:58778088-58779086 | | 15534 | Olfr447 | NM_146988.1 | chr6:42911524-42912457 |
| 15440 | Olfr316 | NM_001011818.2 | chr11:58757666-58758587 | | 15535 | Olfr448 | NM_146273.1 | chr6:42896652-42897385 |
| 15441 | Olfr317 | NM_001011769.2 | chr11:58731095-58733223 | | 15536 | Olfr449 | NM_147064.1 | chr6:42837882-42838818 |
| 15442 | Olfr318 | NM_146501.2 | chr11:58720068-58721094 | | 15537 | Olfr45 | NM_146963.1 | chr7:140690906-140691842 |
| 15443 | Olfr319 | NM_146500.2 | chr11:58701702-58702623 | | 15538 | Olfr450 | NM_146445.1 | chr6:42817472-42818405 |
| 15444 | Olfr32 | NM_010980.2 | chr2:90138179-90142293 | | 15539 | Olfr452 | NM_001011869.1 | chr6:42790040-42790994 |
| 15445 | Olfr320 | NM_207230.1 | chr11:58683874-58684795 | | 15540 | Olfr453 | NM_001011799.1 | chr6:42744038-42744992 |
| 15446 | Olfr322 | NM_207693.1 | chr11:58665560-58666544 | | 15541 | Olfr455 | NM_001081301.2 | chr6:42538066-42539020 |
| 15447 | Olfr323 | NM_146376.2 | chr11:58625072-58626044 | | 15542 | Olfr456 | NM_001015528.2 | chr6:42486162-42487214 |
| 15448 | Olfr324 | NM_001011743.2 | chr11:58597344-58598466 | | 15543 | Olfr457 | NM_146987.1 | chr6:42471234-42472176 |
| 15449 | Olfr325 | NM_207153.2 | chr11:58580836-58581877 | | 15544 | Olfr458 | NM_146444.1 | chr6:42460075-42461017 |
| 15450 | Olfr328 | NM_148502.2 | chr11:58551304-58552237 | | 15545 | Olfr459 | NM_146576.1 | chr6:41771352-41772297 |
| 15451 | Olfr329-ps | NM_001011531.3 | chr11:58542446-58543483 | | 15546 | Olfr46 | NM_146934.2 | chr7:140601339-140611124 |
| 15452 | Olfr33 | NM_147073.1 | chr7:102713454-102714411 | | 15547 | Olfr460 | NM_146383.1 | chr6:40571387-40572332 |
| 15453 | Olfr330 | NM_146879.2 | chr11:58528928-58534825 | | 15548 | Olfr461 | NM_146382.1 | chr6:40544035-40544977 |
| 15454 | Olfr331 | NM_001011861.3 | chr11:58501597-58502572 | | 15549 | Olfr462 | NM_146411.2 | chr11:87888958-87889894 |
| 15455 | Olfr332 | NM_001011770.2 | chr11:58489718-58492499 | | 15550 | Olfr463 | NM_146413.2 | chr11:87892986-87893922 |
| 15456 | Olfr338 | NM_146947.1 | chr2:36376777-36377698 | | 15551 | Olfr464 | NM_146412.2 | chr11:87913919-87915003 |
| 15457 | Olfr339 | NM_146693.1 | chr2:36421399-36422329 | | 15552 | Olfr466 | NM_146819.2 | chr13:65152225-65153152 |
| 15458 | Olfr340 | NM_146951.1 | chr2:36452586-36453525 | | 15553 | Olfr467 | NM_001005488.1 | chr7:107814585-107815506 |
| 15459 | Olfr341 | NM_146950.1 | chr2:36479186-36480128 | | 15554 | Olfr469 | NM_146426.1 | chr7:107822522-107823467 |
| 15460 | Olfr342 | NM_146948.1 | chr2:36527413-36528352 | | 15555 | Olfr47 | NM_146370.1 | chr6:43235609-43236575 |
| 15461 | Olfr344 | NM_146628.1 | chr2:36568599-36569529 | | 15556 | Olfr470 | NM_146425.1 | chr7:107844786-107845731 |
| 15462 | Olfr345 | NM_146945.1 | chr2:36640040-36640876 | | 15557 | Olfr472 | NM_146774.1 | chr7:107902718-107903651 |
| 15463 | Olfr346 | NM_148003.1 | chr2:36688003-36688933 | | 15558 | Olfr473 | NM_146775.1 | chr7:107933521-107934454 |
| 15464 | Olfr347 | NM_146943.1 | chr2:36734322-36735261 | | 15559 | Olfr474 | NM_146495.1 | chr7:107954642-107955575 |
| 15465 | Olfr348 | NM_146944.1 | chr2:36786526-36787468 | | 15560 | Olfr476 | NM_146924.1 | chr7:107967398-107968331 |
| 15466 | Olfr350 | NM_146627.1 | chr2:36850047-36850986 | | 15561 | Olfr478 | NM_146926.1 | chr7:107990366-107991299 |
| 15467 | Olfr351 | NM_146942.1 | chr2:36859413-36860346 | | 15562 | Olfr478 | NM_146734.1 | chr7:108031396-108032341 |
| 15468 | Olfr352 | NM_146940.1 | chr2:36869567-36870515 | | 15563 | Olfr479 | NM_001011742.1 | chr7:108054983-108055967 |
| 15469 | Olfr353 | NM_146941.1 | chr2:36889910-36890846 | | 15564 | Olfr48 | NM_010990.1 | chr2:89844065-89844971 |
| 15470 | Olfr354 | NM_146939.1 | chr2:36906947-36907901 | | 15565 | Olfr480 | NM_020291.1 | chr7:108065767-108066796 |
| 15471 | Olfr355 | NM_146925.1 | chr2:36927179-36928112 | | 15566 | Olfr481 | NM_146925.1 | chr7:108080795-108081734 |
| 15472 | Olfr356 | NM_146624.1 | chr2:36937120-36938068 | | 15567 | Olfr482 | NM_146733.1 | chr7:108094596-108095568 |
| 15473 | Olfr357 | NM_146623.1 | chr2:36996811-36997738 | | 15568 | Olfr483 | NM_146735.1 | chr7:108103310-108104258 |
| 15474 | Olfr358 | NM_207235.1 | chr2:37004619-37005612 | | 15569 | Olfr484 | NM_146499.1 | chr7:108124295-108125261 |
| 15475 | Olfr360 | NM_146822.1 | chr2:37068306-37069260 | | 15570 | Olfr485 | NM_001011810.1 | chr7:108158917-108159871 |
| 15476 | Olfr361 | NM_146368.1 | chr2:37084777-37085746 | | 15571 | Olfr486 | NM_146496.1 | chr7:108171797-108172742 |
| 15477 | Olfr362 | NM_147051.1 | chr2:37104694-37105648 | | 15572 | Olfr487 | NM_001011811.1 | chr7:108211582-108212527 |
| 15478 | Olfr365 | NM_146662.1 | chr2:37201242-37202181 | | 15573 | Olfr488 | NM_146732.1 | chr7:108255191-108256136 |
| 15479 | Olfr366 | NM_001005569.1 | chr2:37219490-37220420 | | 15574 | Olfr49 | NM_010991.2 | chr14:54281895-54282925 |

Fig. 26 - 83

| | | | | | | | | |
|---|---|---|---|---|---|---|---|---|
| 15575 | Olfr490 | NM_146498.1 | chr7:108286179-108287124 | | 15670 | Olfr600 | NM_147046.2 | chr7:103345981-103346926 |
| 15576 | Olfr491 | NM_146736.1 | chr7:108316895-108317828 | | 15671 | Olfr601 | NM_146314.2 | chr7:103358223-103359213 |
| 15577 | Olfr492 | NM_146497.1 | chr7:108322729-108323674 | | 15672 | Olfr603 | NM_147070.2 | chr7:103383061-103384000 |
| 15578 | Olfr493 | NM_146310.1 | chr7:108346034-108346979 | | 15673 | Olfr605 | NM_001011854.2 | chr7:103442139-103443150 |
| 15579 | Olfr494 | NM_146737.1 | chr7:108367491-108368436 | | 15674 | Olfr606 | NM_147094.1 | chr7:103451338-103452298 |
| 15580 | Olfr495 | NM_146364.1 | chr7:108395121-108396114 | | 15675 | Olfr608 | NM_146756.2 | chr7:103470040-103470991 |
| 15581 | Olfr497 | NM_146738.1 | chr7:108422572-108423517 | | 15676 | Olfr609 | NM_147082.2 | chr7:103491916-103492876 |
| 15582 | Olfr498 | NM_146307.2 | chr7:108465325-108466318 | | 15677 | Olfr61 | NM_146964.1 | chr7:140637702-140638638 |
| 15583 | Olfr5 | NM_146914.2 | chr7:6480215-6486813 | | 15678 | Olfr610 | NM_147081.2 | chr7:103505996-103506944 |
| 15584 | Olfr50 | NM_146946.1 | chr2:36793237-36794176 | | 15679 | Olfr611 | NM_146727.2 | chr7:103517410-103518382 |
| 15585 | Olfr502 | NM_146739.1 | chr7:108523003-108523948 | | 15680 | Olfr612 | NM_001200027.1 | chr7:103538260-103539232 |
| 15586 | Olfr503 | NM_001011527.1 | chr7:108544526-108545498 | | 15681 | Olfr613 | NM_147100.3 | chr7:103550367-103555504 |
| 15587 | Olfr504 | NM_001011858.1 | chr7:108564836-108565793 | | 15682 | Olfr615 | NM_147080.2 | chr7:103560478-103561420 |
| 15588 | Olfr506 | NM_001011871.1 | chr7:108612308-108613253 | | 15683 | Olfr616 | NM_147099.2 | chr7:103564323-103565277 |
| 15589 | Olfr507 | NM_146743.1 | chr7:108621813-108622764 | | 15684 | Olfr617 | NM_146841.1 | chr7:103584023-103584980 |
| 15590 | Olfr508 | NM_146773.1 | chr7:108629993-108630926 | | 15685 | Olfr618 | NM_147047.2 | chr7:103597317-103598274 |
| 15591 | Olfr509 | NM_146372.1 | chr7:108645608-108646574 | | 15686 | Olfr619 | NM_147076.2 | chr7:103603588-103604711 |
| 15592 | Olfr51 | NM_146909.1 | chr11:51006973-51007897 | | 15687 | Olfr62 | NM_146315.2 | chr4:118665518-118666466 |
| 15593 | Olfr510 | NM_146311.1 | chr7:108667417-108668362 | | 15688 | Olfr620 | NM_146812.2 | chr7:103611409-103612351 |
| 15594 | Olfr512 | NM_146724.1 | chr7:108713354-108714335 | | 15689 | Olfr622 | NM_147083.1 | chr7:103639184-103640138 |
| 15595 | Olfr513 | NM_146723.1 | chr7:108754857-108755787 | | 15690 | Olfr623 | NM_147122.2 | chr7:103660243-103661318 |
| 15596 | Olfr514 | NM_146726.1 | chr7:108825064-108825997 | | 15691 | Olfr624 | NM_001011865.2 | chr7:103670102-103671029 |
| 15597 | Olfr516 | NM_146725.1 | chr7:108845063-108846008 | | 15692 | Olfr628 | NM_147097.2 | chr7:103731927-103732878 |
| 15598 | Olfr517 | NM_001011846.1 | chr7:108868207-108869152 | | 15693 | Olfr629 | NM_146821.2 | chr7:103740200-103741322 |
| 15599 | Olfr518 | NM_146306.1 | chr7:108880602-108881604 | | 15694 | Olfr63 | NM_146937.1 | chr17:33268725-33269676 |
| 15600 | Olfr519 | NM_207160.1 | chr7:108893460-108894405 | | 15695 | Olfr630 | NM_147098.2 | chr7:103754149-103757350 |
| 15601 | Olfr52 | NM_146583.1 | chr2:86181149-86182109 | | 15696 | Olfr631 | NM_001271020.1 | chr7:103915061-103929911 |
| 15602 | Olfr520 | NM_147063.2 | chr7:99735144-99736095 | | 15697 | Olfr632 | NM_147119.1 | chr7:103937381-103938335 |
| 15603 | Olfr521 | NM_146356.2 | chr7:99767163-99768129 | | 15698 | Olfr633 | NM_146354.1 | chr7:103946567-103947506 |
| 15604 | Olfr522 | NM_146952.1 | chr7:140162009-140162948 | | 15699 | Olfr635 | NM_147118.2 | chr7:103979175-103980141 |
| 15605 | Olfr523 | NM_146518.1 | chr7:140176103-140177057 | | 15700 | Olfr638 | NM_147120.1 | chr7:104003258-104004224 |
| 15606 | Olfr524 | NM_001011814.1 | chr7:140201811-140202768 | | 15701 | Olfr639 | NM_147084.1 | chr7:104011749-104012700 |
| 15607 | Olfr525 | NM_146956.1 | chr7:140322700-140323630 | | 15702 | Olfr64 | NM_013617.3 | chr7:103892809-103894471 |
| 15608 | Olfr527 | NM_001011776.1 | chr7:140335863-140336781 | | 15703 | Olfr640 | NM_146822.2 | chr7:104021371-104022316 |
| 15609 | Olfr53 | NM_146960.2 | chr7:140646451-140652919 | | 15704 | Olfr641 | NM_147072.1 | chr7:104039797-104040736 |
| 15610 | Olfr530 | NM_146519.1 | chr7:140372684-140373608 | | 15705 | Olfr642 | NM_146329.1 | chr7:104049407-104050352 |
| 15611 | Olfr531 | NM_146953.1 | chr7:140400129-140401044 | | 15706 | Olfr643 | NM_147077.1 | chr7:104058655-104059600 |
| 15612 | Olfr532 | NM_147026.1 | chr7:140418841-140419771 | | 15707 | Olfr644 | NM_147121.1 | chr7:104068084-104069029 |
| 15613 | Olfr533 | NM_001011583.1 | chr7:140466202-140467165 | | 15708 | Olfr645 | NM_207144.1 | chr7:104084130-104085078 |
| 15614 | Olfr535 | NM_146954.1 | chr7:140492639-140493578 | | 15709 | Olfr646 | NM_147056.1 | chr7:104106280-104107219 |
| 15615 | Olfr536 | NM_146520.2 | chr7:140500852-140507318 | | 15710 | Olfr648 | NM_146751.1 | chr7:104179455-104180406 |
| 15616 | Olfr538 | NM_001011867.1 | chr7:140574154-140575087 | | 15711 | Olfr649 | NM_147055.1 | chr7:104189266-104190205 |
| 15617 | Olfr539 | NM_146961.1 | chr7:140667288-140668248 | | 15712 | Olfr65 | NM_013616.4 | chr7:103906341-103907447 |
| 15618 | Olfr54 | NM_010997.1 | chr11:51027003-51027945 | | 15713 | Olfr651 | NM_146813.2 | chr7:104552883-104553952 |
| 15619 | Olfr541 | NM_146962.1 | chr7:140704252-140705191 | | 15714 | Olfr652 | NM_147048.2 | chr7:104564151-104565212 |
| 15620 | Olfr543 | NM_001011782.2 | chr7:102476772-102477902 | | 15715 | Olfr653 | NM_147074.2 | chr7:104579623-104580669 |
| 15621 | Olfr544 | NM_020289.2 | chr7:102484113-102488307 | | 15716 | Olfr654 | NM_146379.1 | chr7:104587754-104588780 |
| 15622 | Olfr545 | NM_146840.1 | chr7:102493822-102494773 | | 15717 | Olfr655 | NM_146820.2 | chr7:104596252-104597179 |
| 15623 | Olfr547 | NM_147079.2 | chr7:102534748-102535688 | | 15718 | Olfr656 | NM_147075.1 | chr7:104617656-104618646 |
| 15624 | Olfr549 | NM_147101.2 | chr7:102554285-102555236 | | 15719 | Olfr657 | NM_146312.2 | chr7:104635675-104636635 |
| 15625 | Olfr55 | NM_010998.2 | chr17:33176415-33177363 | | 15720 | Olfr658 | NM_147049.4 | chr7:104642879-104647305 |
| 15626 | Olfr550 | NM_147104.2 | chr7:102578468-102579506 | | 15721 | Olfr659 | NM_147050.1 | chr7:104670703-104671672 |
| 15627 | Olfr551 | NM_146755.2 | chr7:102587740-102588819 | | 15722 | Olfr66 | NM_013618.3 | chr7:103881305-103882241 |
| 15628 | Olfr552 | NM_147102.2 | chr7:102604355-102605309 | | 15723 | Olfr661 | NM_146748.1 | chr7:104688016-104688976 |
| 15629 | Olfr553 | NM_207621.1 | chr7:102614006-102614987 | | 15724 | Olfr663 | NM_001011757.1 | chr7:104703568-104704603 |
| 15630 | Olfr554 | NM_146325.2 | chr7:102640247-102641201 | | 15725 | Olfr665 | NM_146814.1 | chr7:104880708-104881659 |
| 15631 | Olfr555 | NM_147103.2 | chr7:102658822-102659770 | | 15726 | Olfr666 | NM_147096.1 | chr7:104892669-104893626 |
| 15632 | Olfr556 | NM_146754.2 | chr7:102669900-102670923 | | 15727 | Olfr667 | NM_147060.2 | chr7:104916313-104917294 |
| 15633 | Olfr557 | NM_146361.2 | chr7:102698215-102699272 | | 15728 | Olfr668 | NM_147059.1 | chr7:104914805-104925762 |
| 15634 | Olfr558 | NM_147093.3 | chr7:102702322-102712054 | | 15729 | Olfr669 | NM_147043.1 | chr7:104938527-104939481 |
| 15635 | Olfr59 | NM_147112.1 | chr7:102723531-102724488 | | 15730 | Olfr67 | NM_013619.3 | chr7:103787211-103791830 |
| 15636 | Olfr56 | NM_010999.2 | chr11:49050732-49135387 | | 15731 | Olfr670 | NM_207146.1 | chr7:104959791-104960730 |
| 15637 | Olfr560 | NM_147113.2 | chr7:102752982-102753927 | | 15732 | Olfr671 | NM_001011755.1 | chr7:104975041-104975983 |
| 15638 | Olfr561 | NM_147092.1 | chr7:102774525-102775470 | | 15733 | Olfr672 | NM_146760.1 | chr7:104995963-104996902 |
| 15639 | Olfr564 | NM_146359.2 | chr7:102803479-102804430 | | 15734 | Olfr675 | NM_001011848.1 | chr7:105024024-105024966 |
| 15640 | Olfr566 | NM_001011536.1 | chr7:102856320-102857271 | | 15735 | Olfr676 | NM_147095.1 | chr7:105035199-105036153 |
| 15641 | Olfr568 | NM_147091.2 | chr7:102877121-102878063 | | 15736 | Olfr677 | NM_146358.1 | chr7:105056247-105057186 |
| 15642 | Olfr569 | NM_147088.2 | chr7:102887206-102888151 | | 15737 | Olfr678 | NM_146758.1 | chr7:105069468-105070410 |
| 15643 | Olfr57 | NM_147041.2 | chr10:79034722-79035802 | | 15738 | Olfr679 | NM_147044.1 | chr7:105085717-105086665 |
| 15644 | Olfr570 | NM_147110.1 | chr7:102900368-102901307 | | 15739 | Olfr68 | NM_013620.2 | chr7:103777395-103778343 |
| 15645 | Olfr571 | NM_147085.2 | chr7:102908868-102909837 | | 15740 | Olfr681 | NM_207557.2 | chr7:105121458-105122406 |
| 15646 | Olfr572 | NM_147089.2 | chr7:102927529-102928586 | | 15741 | Olfr683 | NM_147045.1 | chr7:105143349-105144309 |
| 15647 | Olfr574 | NM_146360.2 | chr7:102948466-102949507 | | 15742 | Olfr684 | NM_207249.1 | chr7:105156741-105157680 |
| 15648 | Olfr575 | NM_147114.2 | chr7:102954663-102955620 | | 15743 | Olfr685 | NM_001011857.1 | chr7:105180360-105181311 |
| 15649 | Olfr576 | NM_001011805.2 | chr7:102965101-102966040 | | 15744 | Olfr686 | NM_147069.1 | chr7:105203387-105204341 |
| 15650 | Olfr577 | NM_147109.1 | chr7:102973051-102973990 | | 15745 | Olfr688 | NM_001011533.2 | chr7:105288094-105289060 |
| 15651 | Olfr578 | NM_147115.1 | chr7:102984220-102985162 | | 15746 | Olfr689 | NM_146750.1 | chr7:105314005-105314968 |
| 15652 | Olfr58 | NM_011001.2 | chr9:19780282-19784064 | | 15747 | Olfr69 | NM_013621.3 | chr7:103767276-103771594 |
| 15653 | Olfr582 | NM_147053.2 | chr7:103041480-103042440 | | 15748 | Olfr690 | NM_020290.2 | chr7:105329216-105330278 |
| 15654 | Olfr583 | NM_146757.1 | chr7:103051299-103052259 | | 15749 | Olfr691 | NM_147061.2 | chr7:105336745-105337714 |
| 15655 | Olfr584 | NM_147054.1 | chr7:103085519-103086479 | | 15750 | Olfr692 | NM_146355.1 | chr7:105368327-105369317 |
| 15656 | Olfr585 | NM_147087.2 | chr7:103097742-103098699 | | 15751 | Olfr693 | NM_146453.2 | chr7:106687533-106678485 |
| 15657 | Olfr586 | NM_147111.1 | chr7:103121828-103122782 | | 15752 | Olfr694 | NM_146452.2 | chr7:106688781-106689729 |
| 15658 | Olfr589 | NM_147052.1 | chr7:103154791-103155745 | | 15753 | Olfr695 | NM_146598.2 | chr7:106713731-106716345 |
| 15659 | Olfr59 | NM_011002.2 | chr11:74283808-74289646 | | 15754 | Olfr697 | NM_146599.2 | chr7:106740907-106741956 |
| 15660 | Olfr591 | NM_001011847.1 | chr7:103172690-103173635 | | 15755 | Olfr698 | NM_146602.2 | chr7:106752450-106753386 |
| 15661 | Olfr592 | NM_207556.2 | chr7:103186602-103187541 | | 15756 | Olfr699 | NM_001011862.1 | chr7:106790048-106790999 |
| 15662 | Olfr593 | NM_146380.1 | chr7:103211861-103212845 | | 15757 | Olfr70 | NM_019485.1 | chr4:43694999-43700807 |
| 15663 | Olfr594 | NM_207143.1 | chr7:103219719-103220655 | | 15758 | Olfr700 | NM_146600.1 | chr7:106805509-106806460 |
| 15664 | Olfr596 | NM_001190381.1 | chr7:103309722-103310661 | | 15759 | Olfr701 | NM_028910.3 | chr7:106814143-106820709 |
| 15665 | Olfr597 | NM_001011845.2 | chr7:103320412-103321360 | | 15760 | Olfr702 | NM_146597.2 | chr7:106823488-106826743 |
| 15666 | Olfr598 | NM_001011793.1 | chr7:103328487-103329447 | | 15761 | Olfr703 | NM_146596.1 | chr7:106844612-106845572 |
| 15667 | Olfr599 | NM_146731.1 | chr7:103338055-103339003 | | 15762 | Olfr704 | NM_001011749.1 | chr7:106864981-106865929 |
| 15668 | Olfr6 | NM_206897.2 | chr7:106955983-106956934 | | 15763 | Olfr705 | NM_147032.2 | chr7:106873292-106874243 |
| 15669 | Olfr60 | NM_146955.1 | chr7:140345051-140345987 | | 15764 | Olfr706 | NM_146353.2 | chr7:106885864-106886815 |

Fig. 26 - 84

| | | | | | | | | |
|---|---|---|---|---|---|---|---|---|
| 15765 | Olfr707 | NM_001005570.2 | chr7:106891183-106892107 | | 15860 | Olfr824 | NM_146674.1 | chr10:130126107-130127055 |
| 15766 | Olfr71 | NM_019486.1 | chr4:43705627-43706566 | | 15861 | Olfr825 | NM_146677.1 | chr10:130162361-130163324 |
| 15767 | Olfr710 | NM_146601.1 | chr7:106944066-106948312 | | 15862 | Olfr826 | NM_146676.1 | chr10:130179936-130180878 |
| 15768 | Olfr711 | NM_147035.2 | chr7:106971367-106975451 | | 15863 | Olfr827 | NM_146300.1 | chr10:130210159-130211128 |
| 15769 | Olfr713 | NM_147034.1 | chr7:107036135-107037110 | | 15864 | Olfr828 | NM_146605.1 | chr9:18815353-18816292 |
| 15770 | Olfr714 | NM_147033.2 | chr7:107073829-107074783 | | 15865 | Olfr829 | NM_147067.1 | chr9:18856626-18857592 |
| 15771 | Olfr715 | NM_146780.2 | chr7:107128351-107129482 | | 15866 | Olfr830 | NM_146566.1 | chr9:18875328-18876276 |
| 15772 | Olfr716 | NM_146604.1 | chr7:107147317-107148262 | | 15867 | Olfr832 | NM_001011824.1 | chr9:18944649-18945588 |
| 15773 | Olfr720 | NM_146392.1 | chr14:14175129-14176080 | | 15868 | Olfr834 | NM_001011823.1 | chr9:18987989-18988928 |
| 15774 | Olfr722 | NM_146494.2 | chr14:49894257-49901941 | | 15869 | Olfr835 | NM_001012266.1 | chr9:19035124-19036060 |
| 15775 | Olfr723 | NM_001011530.2 | chr14:49928562-49929568 | | 15870 | Olfr836 | NM_146564.2 | chr9:19120956-19121911 |
| 15776 | Olfr724 | NM_146492.2 | chr14:49960090-49961096 | | 15871 | Olfr837 | NM_146565.2 | chr9:19136927-19137967 |
| 15777 | Olfr725 | NM_146317.2 | chr14:50034390-50035500 | | 15872 | Olfr843 | NM_146567.2 | chr9:19248356-19249463 |
| 15778 | Olfr726 | NM_146316.2 | chr14:50083713-50084679 | | 15873 | Olfr845 | NM_207145.2 | chr9:19338458-19339400 |
| 15779 | Olfr727 | NM_146319.2 | chr14:50126552-50127587 | | 15874 | Olfr846 | NM_146282.2 | chr9:19360414-19361356 |
| 15780 | Olfr728 | NM_001011809.1 | chr14:50139701-50140637 | | 15875 | Olfr847 | NM_146585.1 | chr9:19374940-19375879 |
| 15781 | Olfr729 | NM_146278.1 | chr14:50147900-50148872 | | 15876 | Olfr849 | NM_146527.1 | chr9:19440914-19441853 |
| 15782 | Olfr73 | NM_054090.1 | chr2:88034195-88035137 | | 15877 | Olfr850 | NM_146523.1 | chr9:19477300-19478248 |
| 15783 | Olfr730 | NM_146493.2 | chr14:50186261-50187218 | | 15878 | Olfr851 | NM_146905.2 | chr9:19496749-19497688 |
| 15784 | Olfr731 | NM_146363.2 | chr14:50237902-50238883 | | 15879 | Olfr853 | NM_146906.1 | chr9:19537010-19537928 |
| 15785 | Olfr732 | NM_146665.2 | chr14:50281227-50282271 | | 15880 | Olfr854 | NM_146522.1 | chr9:19566434-19567382 |
| 15786 | Olfr733 | NM_146663.2 | chr14:50292836-50293930 | | 15881 | Olfr855 | NM_146524.2 | chr9:19584510-19585502 |
| 15787 | Olfr734 | NM_146864.1 | chr14:50319891-50320833 | | 15882 | Olfr856-ps1 | NR_033621.1 | chr9:19657638-19658680 |
| 15788 | Olfr735 | NM_001011754.2 | chr14:50345375-50346440 | | 15883 | Olfr857 | NM_001012265.1 | chr9:19712828-19713758 |
| 15789 | Olfr736 | NM_146666.1 | chr14:50392757-50393696 | | 15884 | Olfr859 | NM_146526.2 | chr9:19808319-19809249 |
| 15790 | Olfr738 | NM_146420.2 | chr14:50413545-50414481 | | 15885 | Olfr860 | NM_146528.2 | chr9:19845622-19849747 |
| 15791 | Olfr739 | NM_146668.2 | chr14:50424520-50425450 | | 15886 | Olfr862 | NM_146562.1 | chr9:19883382-19884303 |
| 15792 | Olfr74 | NM_054091.2 | chr2:87973706-87974663 | | 15887 | Olfr866 | NM_146558.2 | chr9:20026958-20028035 |
| 15793 | Olfr740 | NM_146667.2 | chr14:50453053-50453989 | | 15888 | Olfr867 | NM_001011748.1 | chr9:20054465-20055461 |
| 15794 | Olfr741 | NM_207133.2 | chr14:50473056-50486395 | | 15889 | Olfr868 | NM_146559.2 | chr9:20098625-20101690 |
| 15795 | Olfr742 | NM_146430.2 | chr14:50515120-50516240 | | 15890 | Olfr869 | NM_146557.2 | chr9:20129119-20138089 |
| 15796 | Olfr743 | NM_001177508.1 | chr14:50533413-50534349 | | 15891 | Olfr870 | NM_146904.1 | chr9:20170633-20171569 |
| 15797 | Olfr744 | NM_001011738.1 | chr14:50618223-50619195 | | 15892 | Olfr871 | NM_146903.2 | chr9:20212206-20213353 |
| 15798 | Olfr745 | NM_146266.2 | chr14:50642194-50643369 | | 15893 | Olfr872 | NM_146560.2 | chr9:20237161-20260913 |
| 15799 | Olfr746 | NM_146298.2 | chr14:50653238-50654183 | | 15894 | Olfr873 | NM_146561.1 | chr9:20300210-20301170 |
| 15800 | Olfr747 | NM_207156.2 | chr14:50680690-50681645 | | 15895 | Olfr874 | NM_146882.2 | chr9:37746135-37747068 |
| 15801 | Olfr748 | NM_001011837.2 | chr14:50710331-50711255 | | 15896 | Olfr875 | NM_146749.2 | chr9:37772636-37773640 |
| 15802 | Olfr749 | NM_020288.2 | chr14:50736218-50744324 | | 15897 | Olfr876 | NM_146883.2 | chr9:37803888-37804936 |
| 15803 | Olfr750 | NM_207558.2 | chr14:51070310-51071442 | | 15898 | Olfr877 | NM_146417.1 | chr9:37854819-37855755 |
| 15804 | Olfr75-ps1 | NR_002859.2 | chr11:73405449-73409823 | | 15899 | Olfr878 | NM_146798.2 | chr9:37918547-37919612 |
| 15805 | Olfr76 | NM_146682.1 | chr9:12119720-12120674 | | 15900 | Olfr881 | NM_146418.2 | chr9:37992491-37993439 |
| 15806 | Olfr761 | NM_001011829.1 | chr7:37952050-37953022 | | 15901 | Olfr883 | NM_146419.2 | chr9:38025870-38026737 |
| 15807 | Olfr763 | NM_146862.1 | chr10:129011286-129012216 | | 15902 | Olfr884 | NM_001011798.1 | chr9:38047223-38048153 |
| 15808 | Olfr765 | NM_001085477.1 | chr10:129046131-129047061 | | 15903 | Olfr885 | NM_001011739.1 | chr9:38061321-38062251 |
| 15809 | Olfr767 | NM_146318.2 | chr10:129079031-129079961 | | 15904 | Olfr887 | NM_146423.1 | chr9:38084837-38085767 |
| 15810 | Olfr768 | NM_146864.1 | chr10:129093033-129093972 | | 15905 | Olfr888 | NM_146424.1 | chr9:38108687-38109632 |
| 15811 | Olfr769 | NM_146267.1 | chr10:129111484-129112423 | | 15906 | Olfr889 | NM_146482.1 | chr9:38115797-38116727 |
| 15812 | Olfr77 | NM_146339.3 | chr9:19917228-19922510 | | 15907 | Olfr890 | NM_146481.2 | chr9:38143136-38144081 |
| 15813 | Olfr770 | NM_146863.1 | chr10:129132830-129133766 | | 15908 | Olfr891 | NM_146478.2 | chr9:38179870-38180821 |
| 15814 | Olfr771 | NM_146547.1 | chr10:129160028-129160982 | | 15909 | Olfr893 | NM_146336.2 | chr9:38209051-38209993 |
| 15815 | Olfr772 | NM_146266.2 | chr10:129174050-129175054 | | 15910 | Olfr894 | NM_146868.2 | chr9:38218817-38219766 |
| 15816 | Olfr773 | NM_207008.2 | chr10:129186483-129187419 | | 15911 | Olfr895 | NM_146875.2 | chr9:38268514-38269465 |
| 15817 | Olfr774 | NM_207620.1 | chr10:129238150-129239089 | | 15912 | Olfr897 | NM_146871.2 | chr9:38349084-38350035 |
| 15818 | Olfr775 | NM_146545.2 | chr10:129250535-129251474 | | 15913 | Olfr899 | NM_146479.1 | chr9:38367547-38368543 |
| 15819 | Olfr776 | NM_207559.1 | chr10:129260962-129261901 | | 15914 | Olfr9 | NM_146861.1 | chr10:128989913-128990852 |
| 15820 | Olfr777 | NM_146386.5 | chr10:129268385-129269321 | | 15915 | Olfr90 | NM_146477.2 | chr17:37085190-37086236 |
| 15821 | Olfr78 | NM_001168503.1 | chr7:102740720-102759471 | | 15916 | Olfr900 | NM_146874.1 | chr9:38377882-38378833 |
| 15822 | Olfr780 | NM_146284.1 | chr10:129321624-129322563 | | 15917 | Olfr901 | NM_001011806.1 | chr9:38430283-38431219 |
| 15823 | Olfr781 | NM_146728.1 | chr10:129332882-129333818 | | 15918 | Olfr902 | NM_146802.2 | chr9:38448791-38449847 |
| 15824 | Olfr782 | NM_001011797.1 | chr10:129350564-129351509 | | 15919 | Olfr904 | NM_146801.2 | chr9:38464042-38464975 |
| 15825 | Olfr784 | NM_146729.1 | chr10:129387634-129388594 | | 15920 | Olfr905 | NM_146804.2 | chr9:38472748-38473681 |
| 15826 | Olfr786 | NM_146549.1 | chr10:129436813-129437752 | | 15921 | Olfr906 | NM_146803.2 | chr9:38488030-38488966 |
| 15827 | Olfr787 | NM_001011822.1 | chr10:129462677-129463616 | | 15922 | Olfr907 | NM_146805.2 | chr9:38498670-38499603 |
| 15828 | Olfr788 | NM_146851.1 | chr10:129472693-129473629 | | 15923 | Olfr908 | NM_146872.1 | chr9:38516033-38516965 |
| 15829 | Olfr790 | NM_146930.1 | chr10:129500885-129501854 | | 15924 | Olfr91 | NM_182714.2 | chr17:37092933-37093872 |
| 15830 | Olfr791 | NM_146930.1 | chr10:129526228-129527167 | | 15925 | Olfr910 | NM_146811.2 | chr9:38537881-38539829 |
| 15831 | Olfr792 | NM_001011849.1 | chr10:129540538-129541474 | | 15926 | Olfr911-ps1 | NM_146873.2 | chr9:38523729-38524669 |
| 15832 | Olfr794 | NM_146378.1 | chr10:129570656-129571619 | | 15927 | Olfr912 | NM_146810.2 | chr9:38580243-38582211 |
| 15833 | Olfr796 | NM_146931.1 | chr10:129607546-129608479 | | 15928 | Olfr913 | NM_001011523.2 | chr9:38592802-38595161 |
| 15834 | Olfr798 | NM_146606.2 | chr10:129625123-129626055 | | 15929 | Olfr914 | NM_146786.2 | chr9:38606466-38607417 |
| 15835 | Olfr799 | NM_146927.1 | chr10:129647129-129648065 | | 15930 | Olfr915 | NM_146785.2 | chr9:38646589-38647522 |
| 15836 | Olfr8 | NM_207201.1 | chr10:78955206-78956139 | | 15931 | Olfr916 | NM_146784.1 | chr9:38657457-38658390 |
| 15837 | Olfr800 | NM_146548.1 | chr10:129659807-129660743 | | 15932 | Olfr917 | NM_001011864.1 | chr9:38664912-38665842 |
| 15838 | Olfr801 | NM_146285.1 | chr10:129669560-129670517 | | 15933 | Olfr918 | NM_146375.2 | chr9:38672503-38673481 |
| 15839 | Olfr802 | NM_146932.1 | chr10:129681798-129682737 | | 15934 | Olfr919 | NM_146440.1 | chr9:38697428-38698376 |
| 15840 | Olfr803 | NM_146554.1 | chr10:129691112-129692039 | | 15935 | Olfr92 | NM_146456.2 | chr17:37111041-37111980 |
| 15841 | Olfr804 | NM_001011821.1 | chr10:129704879-129705824 | | 15936 | Olfr920 | NM_146787.2 | chr9:38752795-38756863 |
| 15842 | Olfr805 | NM_146555.1 | chr10:129722582-129723542 | | 15937 | Olfr921 | NM_146782.2 | chr9:38773087-38776354 |
| 15843 | Olfr806 | NM_146553.1 | chr10:129737973-129738915 | | 15938 | Olfr922 | NM_146781.2 | chr9:38815407-38816539 |
| 15844 | Olfr807 | NM_146929.1 | chr10:129754512-129755448 | | 15939 | Olfr923 | NM_146816.2 | chr9:38827614-38828682 |
| 15845 | Olfr808 | NM_146928.1 | chr10:129767497-129768436 | | 15940 | Olfr924 | NM_207560.1 | chr9:38848115-38849042 |
| 15846 | Olfr809 | NM_146324.1 | chr10:129775870-129776857 | | 15941 | Olfr926 | NM_146815.1 | chr9:38877177-38878104 |
| 15847 | Olfr810 | NM_146550.1 | chr10:129790648-129791587 | | 15942 | Olfr93 | NM_001011813.1 | chr17:37151031-37151970 |
| 15848 | Olfr811 | NM_146552.1 | chr10:129801563-129802523 | | 15943 | Olfr930 | NM_146272.1 | chr9:38930172-38931099 |
| 15849 | Olfr812 | NM_146795.1 | chr10:129842107-129843040 | | 15944 | Olfr933 | NM_146441.1 | chr9:38975677-38976604 |
| 15850 | Olfr813 | NM_207147.1 | chr10:129856519-129857452 | | 15945 | Olfr934 | NM_146442.1 | chr9:38982109-38983042 |
| 15851 | Olfr814 | NM_207159.1 | chr10:129873822-129874755 | | 15946 | Olfr935 | NM_146746.1 | chr9:38994506-38995433 |
| 15852 | Olfr815 | NM_146670.1 | chr10:129901775-129902726 | | 15947 | Olfr936 | NM_207139.1 | chr9:39046613-39047549 |
| 15853 | Olfr816 | NM_146672.1 | chr10:129911337-129912276 | | 15948 | Olfr937 | NM_146439.1 | chr9:39059728-39060664 |
| 15854 | Olfr818 | NM_146777.1 | chr10:129945103-129946060 | | 15949 | Olfr938 | NM_146438.1 | chr9:39077795-39078743 |
| 15855 | Olfr819 | NM_001165944.1 | chr10:129965735-129966698 | | 15950 | Olfr94 | NM_001011518.1 | chr17:37196805-37197966 |
| 15856 | Olfr820 | NM_146675.1 | chr10:130017352-130018301 | | 15951 | Olfr943 | NM_146326.3 | chr9:39166309-39185124 |
| 15857 | Olfr821 | NM_130033627-130034560 | chr10:130033627-130034560 | | 15952 | Olfr944 | NM_146507.1 | chr9:39217358-39218294 |
| 15858 | Olfr822 | NM_146671.1 | chr10:130074411-130075350 | | 15953 | Olfr945 | NM_146506.1 | chr9:39257719-39258679 |
| 15859 | Olfr823 | NM_146673.2 | chr10:130111840-130112788 | | 15954 | Olfr947-ps1 | NR_033620.1 | chr9:39287923-39299481 |

Fig. 26 - 85

| | | | |
|---|---|---|---|
| 15955 | Olfr948 | NM_001011756.1 | chr9:39318646-39319612 |
| 15956 | Olfr95 | NM_146513.1 | chr17:37210912-37211851 |
| 15957 | Olfr951 | NM_001011812.1 | chr9:39393792-39394737 |
| 15958 | Olfr952 | NM_146503.1 | chr9:39426124-39427069 |
| 15959 | Olfr954 | NM_146331.1 | chr9:39461432-39462377 |
| 15960 | Olfr955 | NM_207141.1 | chr9:39469779-39470724 |
| 15961 | Olfr957 | NM_146745.2 | chr9:39510782-39511718 |
| 15962 | Olfr958 | NM_146330.1 | chr9:39549930-39550869 |
| 15963 | Olfr959 | NM_146508.1 | chr9:39572321-39573257 |
| 15964 | Olfr96 | NM_146514.1 | chr17:37225126-37226068 |
| 15965 | Olfr960 | NM_146279.1 | chr9:39623124-39624075 |
| 15966 | Olfr961 | NM_146504.1 | chr9:39646727-39647672 |
| 15967 | Olfr963 | NM_001011827.1 | chr9:39669058-39669994 |
| 15968 | Olfr965 | NM_001011859.1 | chr9:39719228-39720167 |
| 15969 | Olfr967 | NM_001011826.1 | chr9:39750387-39751320 |
| 15970 | Olfr968 | NM_146312.2 | chr9:39771771-39772798 |
| 15971 | Olfr969 | NM_146826.1 | chr9:39795376-39796312 |
| 15972 | Olfr97 | NM_146512.1 | chr17:37231435-37232368 |
| 15973 | Olfr970 | NM_146611.1 | chr9:39819640-39820576 |
| 15974 | Olfr971 | NM_146614.1 | chr9:39839435-39840359 |
| 15975 | Olfr972 | NM_146610.1 | chr9:39873276-39874221 |
| 15976 | Olfr974 | NM_147107.1 | chr9:39942261-39943194 |
| 15977 | Olfr975 | NM_146828.1 | chr9:39949836-39950769 |
| 15978 | Olfr976 | NM_146367.2 | chr9:39954256-39957069 |
| 15979 | Olfr978 | NM_147105.2 | chr9:39993811-39994747 |
| 15980 | Olfr979 | NM_147108.2 | chr9:40000205-40001250 |
| 15981 | Olfr98 | NM_146510.1 | chr17:37262732-37263662 |
| 15982 | Olfr980 | NM_147106.2 | chr9:40005993-40007029 |
| 15983 | Olfr981 | NM_146286.1 | chr9:40022394-40023327 |
| 15984 | Olfr982 | NM_146854.1 | chr9:40074296-40075262 |
| 15985 | Olfr983 | NM_146827.2 | chr9:40092016-40093558 |
| 15986 | Olfr984 | NM_146608.1 | chr9:40100543-40101488 |
| 15987 | Olfr985 | NM_146855.2 | chr9:40126923-40128039 |
| 15988 | Olfr986 | NM_146615.2 | chr9:40187078-40188094 |
| 15989 | Olfr987 | NM_001011785.1 | chr2:85330966-85331896 |
| 15990 | Olfr988 | NM_001011534.1 | chr2:85352994-85353924 |
| 15991 | Olfr99 | NM_146515.2 | chr17:37279500-37280418 |
| 15992 | Olfr992 | NM_146865.1 | chr2:85399601-85400531 |
| 15993 | Olfr993 | NM_146435.1 | chr2:85413932-85414877 |
| 15994 | Olfr994 | NM_146433.1 | chr2:85429882-85430827 |
| 15995 | Olfr995 | NM_146434.1 | chr2:85438208-85439156 |
| 15996 | Olfr996 | NM_146437.2 | chr2:85579214-85580282 |
| 15997 | Olfr998 | NM_146436.2 | chr2:85590509-85591521 |
| 15998 | Olig1 | NM_016968.4 | chr16:91269768-91271939 |
| 15999 | Olig2 | NM_016967.2 | chr16:91225549-91228677 |
| 16000 | Olig3 | NM_053008.2 | chr10:19356558-19358604 |
| 16001 | Olr1 | NM_138648.2 | chr6:129485246-129507165 |
| 16002 | Oma1 | NM_025909.3 | chr4:103313845-103366428 |
| 16003 | Omd | NM_012050.2 | chr13:49582746-49592609 |
| 16004 | Omg | NM_019409.2 | chr11:79500981-79504082 |
| 16005 | Omp | NM_011010.2 | chr7:98143358-98145447 |
| 16006 | Omt2a | NM_001111286.1 | chr9:78311971-78314048 |
| 16007 | Omt2b | NM_205822.2 | chr9:78328020-78328620 |
| 16008 | Onecut1 | NM_008262.3 | chr9:74861920-74889647 |
| 16009 | Onecut2 | NM_194268.2 | chr18:64340363-64398488 |
| 16010 | Onecut3 | NM_139226.3 | chr10:80494905-80517260 |
| 16011 | Ooep | NM_026480.3 | chr9:78376902-78378588 |
| 16012 | Oog1 | NM_178657.5 | chr12:87602664-87608845 |
| 16013 | Oog2 | NM_198661.3 | chr4:144190716-144196934 |
| 16014 | Oog3 | NM_201258.2 | chr4:144157555-144162651 |
| 16015 | Oog4 | NM_173773.1 | chr4:143437163-143450302 |
| 16016 | Oosp1 | NM_133353.3 | chr19:11667459-11691051 |
| 16017 | Oosp2 | NM_001037634.3 | chr19:11647283-11660559 |
| 16018 | Oosp3 | NM_001033283.2 | chr19:11697054-11711858 |
| 16019 | Opa1 | NM_001199177.1 | chr16:29579333-29654602 |
| 16020 | Opa3 | NM_207525.3 | chr7:19228388-19246817 |
| 16021 | Opalin | NM_153520.1 | chr19:41063419-41077113 |
| 16022 | Opcml | NM_177906.4 | chr9:27791268-28925048 |
| 16023 | Ophn1 | NM_052976.4 | chrX:98554279-98891025 |
| 16024 | Oplah | NM_153122.2 | chr15:76296602-76307245 |
| 16025 | Opn1mw | NM_008106.2 | chrX:74127465-74150755 |
| 16026 | Opn1sw | NM_007538.3 | chr6:29376670-29380513 |
| 16027 | Opn3 | NM_010098.3 | chr1:175662426-175692632 |
| 16028 | Opn4 | NM_001128599.1 | chr14:34590617-34600142 |
| 16029 | Opn5 | NM_181753.4 | chr17:42556782-42611313 |
| 16030 | Oprd1 | NM_013622.3 | chr4:132110725-132144486 |
| 16031 | Oprk1 | NM_001204371.1 | chr1:5588492-5606133 |
| 16032 | Oprl1 | NM_001252565.1 | chr2:181715347-181720985 |
| 16033 | Oprm1 | NM_001039652.2 | chr10:6788575-7038209 |
| 16034 | Optc | NM_001160420.2 | chr1:133897193-133907999 |
| 16035 | Optn | NM_181848.4 | chr2:5020641-5063938 |
| 16036 | Orai1 | NM_175423.3 | chr5:123015073-123030452 |
| 16037 | Orai2 | NM_178751.3 | chr5:136147460-136170656 |
| 16038 | Orai3 | NM_198424.3 | chr7:127769814-127775150 |
| 16039 | Oraov1 | NM_028184.3 | chr7:144915193-144921137 |
| 16040 | Orc1 | NM_011015.2 | chr4:108579453-108614831 |
| 16041 | Orc2 | NM_001025378.2 | chr1:58462770-58501426 |
| 16042 | Orc3 | NM_001159563.1 | chr4:34566780-34614942 |
| 16043 | Orc4 | NM_001177313.1 | chr2:48931746-48949267 |
| 16044 | Orc5 | NM_011959.2 | chr5:22486488-22550331 |
| 16045 | Orc6 | NM_001163791.1 | chr8:85299631-85308279 |
| 16046 | Orm1 | NM_008768.2 | chr4:63344555-63348163 |
| 16047 | Orm2 | NM_011016.2 | chr4:63362448-63365877 |
| 16048 | Orm3 | NM_013623.2 | chr4:63356161-63359511 |
| 16049 | Ormdl1 | NM_145517.4 | chr1:53297094-53310245 |

| | | | |
|---|---|---|---|
| 16050 | Ormdl2 | NM_024180.5 | chr10:128817456-128821631 |
| 16051 | Ormdl3 | NM_025661.4 | chr11:98581293-98587245 |
| 16052 | Os9 | NM_001171026.1 | chr10:127094258-127121160 |
| 16053 | Osbp | NM_001033174.1 | chr19:11965843-11994114 |
| 16054 | Osbp2 | NM_152818.2 | chr11:3703730-3863903 |
| 16055 | Osbpl10 | NM_148958.2 | chr9:115067278-115232223 |
| 16056 | Osbpl11 | NM_176840.3 | chr16:33185070-33243312 |
| 16057 | Osbpl1a | NM_001252489.1 | chr18:12755311-12879979 |
| 16058 | Osbpl2 | NM_144500.3 | chr2:180119365-180162680 |
| 16059 | Osbpl3 | NM_001163645.1 | chr6:50293326-50456170 |
| 16060 | Osbpl5 | NM_001199227.1 | chr7:143688761-143740360 |
| 16061 | Osbpl6 | NM_001290733.1 | chr2:76406507-76600647 |
| 16062 | Osbpl7 | NM_001081434.1 | chr11:97050819-97068904 |
| 16063 | Osbpl8 | NM_001003717.1 | chr10:111164801-111297247 |
| 16064 | Osbpl9 | NM_001134791.2 | chr4:109061144-109118036 |
| 16065 | Oscar | NM_001290377.1 | chr7:3609814-3616157 |
| 16066 | Oscp1 | NM_172701.2 | chr4:126058564-126089334 |
| 16067 | Oser1 | NM_025699.2 | chr2:163405821-163419470 |
| 16068 | Osgep | NM_133676.2 | chr14:50915373-50924893 |
| 16069 | Osgepl1 | NM_001285839.1 | chr1:53313623-53326342 |
| 16070 | Osgin1 | NM_027950.1 | chr8:119437161-119446256 |
| 16071 | Osgin2 | NM_145950.4 | chr4:15997120-16013877 |
| 16072 | Osm | NM_001013365.2 | chr11:4236784-4241026 |
| 16073 | Osmr | NM_011019.3 | chr15:6813576-6874313 |
| 16074 | Osr1 | NM_011859.3 | chr12:9574441-9581500 |
| 16075 | Osr2 | NM_054049.2 | chr15:35296111-35303305 |
| 16076 | Ost4 | NM_001134692.2 | chr5:30906515-30907788 |
| 16077 | Ostc | NM_025509.3 | chr3:130695916-130709444 |
| 16078 | Ostf1 | NM_017375.3 | chr19:18580363-18631814 |
| 16079 | Ostm1 | NM_172416.3 | chr10:42678915-42702462 |
| 16080 | Ostn | NM_198112.2 | chr16:27307640-27351209 |
| 16081 | Otc | NM_008769.4 | chrX:10252304-10321024 |
| 16082 | Otoa | NM_139310.1 | chr7:121083437-121163089 |
| 16083 | Otof | NM_001100395.1 | chr5:30367065-30461932 |
| 16084 | Otog | NM_013624.2 | chr7:46240986-46311434 |
| 16085 | Otogl | NM_001177567.1 | chr10:107762309-107912134 |
| 16086 | Otol1 | NM_001018031.2 | chr3:70007612-70028708 |
| 16087 | Otop1 | NM_172709.3 | chr5:38277403-38304217 |
| 16088 | Otop2 | NM_172801.2 | chr11:115307162-115332303 |
| 16089 | Otop3 | NM_027132.2 | chr11:115334733-115346926 |
| 16090 | Otor | NM_020595.2 | chr2:143078491-143081699 |
| 16091 | Otos | NM_153114.2 | chr1:92644217-92648841 |
| 16092 | Otp | NM_011021.3 | chr13:94875626-94883681 |
| 16093 | Ott | NM_011022.1 | chrX:147992992-149487784 |
| 16094 | OTTMUSG00000 016609 | NM_001100416.2 | chr2:175323786-176636311 |
| 16095 | Otub1 | NM_134150.2 | chr19:7198205-7206284 |
| 16096 | Otub2 | NM_001177841.1 | chr12:103388681-103406350 |
| 16097 | Otud1 | NM_027715.1 | chr2:19658061-19660590 |
| 16098 | Otud3 | NM_028453.1 | chr4:138895378-138913947 |
| 16099 | Otud4 | NM_001081164.1 | chr8:79639675-79677755 |
| 16100 | Otud5 | NM_001290536.1 | chrX:7841830-7876626 |
| 16101 | Otud6a | NM_001163191.1 | chrX:100429012-100429885 |
| 16102 | Otud6b | NM_152812.3 | chr4:14809504-14826587 |
| 16103 | Otud7a | NM_130880.1 | chr7:63444771-63759027 |
| 16104 | Otud7b | NM_001056613.1 | chr3:96146526-96161129 |
| 16105 | Otulin | NM_001013792.2 | chr15:27605920-27630693 |
| 16106 | Otx1 | NM_011023.3 | chr11:21994763-22003651 |
| 16107 | Otx2 | NM_001286481.1 | chr14:48657676-48667644 |
| 16108 | Otx2os1 | NR_029384.1 | chr14:48669287-48793348 |
| 16109 | Ovca2 | NM_027136.3 | chr11:75175942-75178808 |
| 16110 | Ovch2 | NM_172908.3 | chr7:107781543-107801179 |
| 16111 | Ovgp1 | NM_007696.2 | chr3:105973801-105987423 |
| 16112 | Ovol1 | NM_019935.3 | chr19:5549136-5560575 |
| 16113 | Ovol2 | NM_026924.3 | chr2:144305175-144332080 |
| 16114 | Ovol3 | NM_001289817.1 | chr7:30233296-30236765 |
| 16115 | Oxa1l | NM_026936.3 | chr14:54360840-54369669 |
| 16116 | Oxct1 | NM_024188.6 | chr15:4026427-4155344 |
| 16117 | Oxct2a | NM_022033.4 | chr4:123321874-123323679 |
| 16118 | Oxct2b | NM_181859.3 | chr4:123116247-123118000 |
| 16119 | Oxgr1 | NM_001001490.3 | chr14:120019584-120042435 |
| 16120 | Oxld1 | NM_025560.2 | chr11:120458603-120458063 |
| 16121 | Oxnad1 | NM_145460.2 | chr14:32085727-32103203 |
| 16122 | Oxr1 | NM_001130163.1 | chr15:41789514-41861047 |
| 16123 | Oxsm | NM_027695.3 | chr14:16238658-16249808 |
| 16124 | Oxsr1 | NM_133985.2 | chr9:119238432-119322427 |
| 16125 | Oxt | NM_011025.4 | chr2:130576168-130577053 |
| 16126 | Oxtr | NM_001081147.1 | chr6:112473683-112489808 |
| 16127 | P2rx1 | NM_008771.3 | chr11:72999144-73015197 |
| 16128 | P2rx2 | NM_001164833.1 | chr5:110339811-110343035 |
| 16129 | P2rx3 | NM_145526.2 | chr2:84996551-85035834 |
| 16130 | P2rx4 | NM_011026.3 | chr5:122707543-122729738 |
| 16131 | P2rx5 | NM_033321.3 | chr11:73180529-73172687 |
| 16132 | P2rx6 | NM_001159561.1 | chr16:17561884-17572012 |
| 16133 | P2rx7 | NM_001038839.2 | chr5:122643910-122684289 |
| 16134 | P2ry1 | NM_001282016.1 | chr3:61002784-61008982 |
| 16135 | P2ry10 | NM_172435.3 | chrX:107089334-107104970 |
| 16136 | P2ry12 | NM_027571.3 | chr3:59216270-59262831 |
| 16137 | P2ry13 | NM_028808.3 | chr3:59307893-59210882 |
| 16138 | P2ry14 | NM_001008497.2 | chr3:59114622-59130762 |
| 16139 | P2ry2 | NM_008773.4 | chr7:100996567-101001998 |
| 16140 | P2ry4 | NM_020621.4 | chrX:100590153-100594869 |
| 16141 | P2ry6 | NM_183168.2 | chr7:100937633-100964366 |
| 16142 | P4ha1 | NM_011030.2 | chr10:59323295-59373304 |
| 16143 | P4ha2 | NM_001136076.2 | chr11:54100923-54131667 |

Fig. 26 - 86

| | | | | | | | |
|---|---|---|---|---|---|---|---|
| 16144 | P4ha3 | NM_177161.4 | chr7:100285519-100319699 | 16239 | Parp10 | NM_001163575.1 | chr15:76232994-76243440 |
| 16145 | P4hb | NM_011032.2 | chr11:120560303-120572936 | 16240 | Parp11 | NM_181402.3 | chr6:127453722-127494239 |
| 16146 | P4htm | NM_028944.3 | chr9:108578825-108597600 | 16241 | Parp12 | NM_172893.3 | chr6:39086411-39118349 |
| 16147 | Pa2g4 | NM_011119.3 | chr10:128557785-128565934 | 16242 | Parp14 | NM_001039530.3 | chr16:35832877-35871382 |
| 16148 | Pabpc1 | NM_008774.3 | chr15:36595657-36608973 | 16243 | Parp16 | NM_177460.4 | chr9:65214689-65239219 |
| 16149 | Pabpc1l | NM_001114079.2 | chr2:164025223-164050538 | 16244 | Parp2 | NM_009632.2 | chr14:50807945-50821300 |
| 16150 | Pabpc2 | NM_011033.2 | chr18:39773496-39776082 | 16245 | Parp3 | NM_145619.3 | chr9:106470321-106476949 |
| 16151 | Pabpc4 | NM_130881.2 | chr4:123282910-123298835 | 16246 | Parp4 | NM_001145978.2 | chr14:56575618-56659798 |
| 16152 | Pabpc4l | NM_001101479.1 | chr3:46442196-46447941 | 16247 | Parp6 | NM_001205239.1 | chr9:59617283-59650290 |
| 16153 | Pabpc5 | NM_053114.2 | chrX:119927195-119930165 | 16248 | Parp8 | NM_001081009.1 | chr13:116854823-117025516 |
| 16154 | Pabpc6 | NM_001163836.1 | chr17:9666496-9669704 | 16249 | Parp9 | NM_030253.3 | chr16:35938469-35972621 |
| 16155 | Pabpn1 | NM_019402.2 | chr14:54894142-54898927 | 16250 | Parpbp | NM_029249.2 | chr10:88091397-88146941 |
| 16156 | Pabpn1l | NM_001007462.1 | chr8:122619470-122622735 | 16251 | Pars2 | NM_001083887.2 | chr4:106651068-106665282 |
| 16157 | Pacrg | NM_027032.2 | chr17:10403011-10840191 | 16252 | Parva | NM_020606.5 | chr7:112427705-112591688 |
| 16158 | Pacrgl | NM_025755.3 | chr5:48372391-48388756 | 16253 | Parvb | NM_133167.3 | chr15:84232042-84315609 |
| 16159 | Pacs1 | NM_153129.2 | chr19:5133684-5273119 | 16254 | Parvg | NM_001162500.1 | chr15:84326118-84342978 |
| 16160 | Pacs2 | NM_001081170.1 | chr12:113014507-113074401 | 16255 | Pask | NM_080850.2 | chr1:93309436-93342788 |
| 16161 | Pacsin1 | NM_001286743.1 | chr17:27655590-27711117 | 16256 | Pate2 | NM_001034421.3 | chr9:35669638-35672889 |
| 16162 | Pacsin2 | NM_001159509.1 | chr15:83375606-83464606 | 16257 | Pate4 | NM_020264.4 | chr9:35607092-35611885 |
| 16163 | Pacsin3 | NM_001289677.1 | chr2:91256164-91264680 | 16258 | Pat1 | NM_172635.3 | chr19:11912398-11945096 |
| 16164 | Padi1 | NM_011059.2 | chr4:140812980-140845778 | 16259 | Patl2 | NM_026251.2 | chr2:122120107-122186189 |
| 16165 | Padi2 | NM_008812.2 | chr4:140906359-140952586 | 16260 | Patz1 | NM_001253690.1 | chr11:3290456-3309083 |
| 16166 | Padi3 | NM_011060.4 | chr4:140785368-140810648 | 16261 | Paupar | NR_117095.1 | chr2:105657861-105661343 |
| 16167 | Padi4 | NM_011061.2 | chr4:140745507-140774203 | 16262 | Pawr | NM_054056.2 | chr10:108332188-108414391 |
| 16168 | Padi6 | NM_153106.2 | chr4:140727354-140742648 | 16263 | Pax1 | NM_008780.2 | chr2:147364993-147375048 |
| 16169 | Paf1 | NM_019458.3 | chr7:28392995-28399383 | 16264 | Pax2 | NM_011037.4 | chr19:44757393-44837869 |
| 16170 | Pafah1b1 | NM_013625.4 | chr11:74673948-74724384 | 16265 | Pax3 | NM_001159520.1 | chr1:78101266-78197136 |
| 16171 | Pafah1b2 | NM_008775.3 | chr9:45965310-45984871 | 16266 | Pax4 | NM_011095925.1 | chr6:28442333-28449340 |
| 16172 | Pafah1b3 | NM_008776.2 | chr7:25295048-25297955 | 16267 | Pax5 | NM_008782.2 | chr4:44531505-44710440 |
| 16173 | Pafah2 | NM_001285872.1 | chr4:134347470-134427412 | 16268 | Pax6 | NM_001244198.2 | chr2:105668895-105698410 |
| 16174 | Pag1 | NM_001195031.1 | chr3:9687481-9833679 | 16269 | Pax6os1 | NR_002867.2 | chr2:105536079-105670330 |
| 16175 | Pagr1a | NM_030240.1 | chr7:127015050-127017352 | 16270 | Pax7 | NM_011039.2 | chr4:139738080-139832968 |
| 16176 | Pah | NM_008777.3 | chr10:87521794-87584137 | 16271 | Pax8 | NM_011040.4 | chr2:24420550-24475599 |
| 16177 | Paics | NM_025939.2 | chr5:76951410-76967565 | 16272 | Pax9 | NM_011041.3 | chr12:56695470-56712822 |
| 16178 | Paip1 | NM_001079849.2 | chr13:119428599-119460323 | 16273 | Paxbp1 | NM_026110.2 | chr16:91014036-91044379 |
| 16179 | Paip2 | NM_026420.2 | chr18:35598666-35617185 | 16274 | Paxip1 | NM_018878.3 | chr5:27740080-27791550 |
| 16180 | Paip2b | NM_146169.2 | chr6:83806058-83831741 | 16275 | Pbdc1 | NM_001281871.1 | chrX:105079755-105117090 |
| 16181 | Pak1 | NM_011035.2 | chr7:97842938-97912381 | 16276 | Pbk | NM_023209.2 | chr14:65805910-65817822 |
| 16182 | Pak1ip1 | NM_026550.3 | chr13:41001009-41013033 | 16277 | Pbld1 | NM_026701.2 | chr10:63061616-63077536 |
| 16183 | Pak2 | NM_177326.3 | chr16:32016289-32079342 | 16278 | Pbld2 | NM_026085.2 | chr10:63024511-63058812 |
| 16184 | Pak3 | NM_001195046.1 | chrX:143693286-143797796 | 16279 | Pbp2 | NM_029595.3 | chr6:135309128-135310384 |
| 16185 | Pak4 | NM_027470.2 | chr7:28558818-28598184 | 16280 | Pbrm1 | NM_001081251.1 | chr14:31019137-31121592 |
| 16186 | Pak6 | NM_001033254.3 | chr2:118663576-118698020 | 16281 | Pbsn | NM_017471.2 | chrX:77837897-77853500 |
| 16187 | Pak7 | NM_172858.2 | chr2:136081087-136387967 | 16282 | Pbx1 | NM_001291508.1 | chr1:168153526-168432169 |
| 16188 | Palb2 | NM_001081238.2 | chr7:122107261-122132946 | 16283 | Pbx2 | NM_017463.2 | chr17:34592470-34597341 |
| 16189 | Pald1 | NM_013753.2 | chr10:61319656-61383523 | 16284 | Pbx3 | NM_001290576.1 | chr2:34171456-34372045 |
| 16190 | Pald | NM_001081390.1 | chr8:61515020-61902690 | 16285 | Pbxip1 | NM_001024954.1 | chr3:69832703-69872292 |
| 16191 | Palm | NM_001161747.1 | chr10:79793571-79820896 | 16286 | Pbxip1 | NM_146131.2 | chr3:89436703-89450952 |
| 16192 | Palm2 | NM_172868.3 | chr4:57568247-57717128 | 16287 | Pcbd1 | NM_025273.4 | chr10:61089330-61094329 |
| 16193 | Palm3 | NM_028877.1 | chr8:84021473-84030295 | 16288 | Pcbd2 | NM_028281.1 | chr13:55727367-55776830 |
| 16194 | Palmd | NM_023245.3 | chr3:116918261-116968952 | 16289 | Pcbp1 | NM_011865.3 | chr6:86524496-86526165 |
| 16195 | Pam | NM_013626.3 | chr1:97821093-98095632 | 16290 | Pcbp2 | NM_001103165.1 | chr15:102470631-102500059 |
| 16196 | Pam16 | NM_025571.1 | chr16:4616465-4624946 | 16291 | Pcbp3 | NM_021568.2 | chr10:76761853-76961947 |
| 16197 | Pamr1 | NM_173749.4 | chr2:102550020-102643040 | 16292 | Pcbp4 | NM_021567.5 | chr9:106453837-106464011 |
| 16198 | Pan2 | NM_001252326.1 | chr10:128303334-128321358 | 16293 | Pcca | NM_144844.2 | chr14:122534327-122889944 |
| 16199 | Pan3 | NM_028291.4 | chr5:147030579-147548501 | 16294 | Pccb | NM_025835.3 | chr9:100982031-101034884 |
| 16200 | Pank1 | NM_001114339.2 | chr19:34806935-34879455 | 16295 | Pcdh1 | NM_029357.3 | chr18:38196693-38209762 |
| 16201 | Pank2 | NM_153501.2 | chr2:131262499-131299188 | 16296 | Pcdh10 | NM_001098170.1 | chr3:45378397-45434579 |
| 16202 | Pank3 | NM_145962.2 | chr11:35769494-35791285 | 16297 | Pcdh11x | NM_001271809.1 | chrX:120290326-120910618 |
| 16203 | Pank4 | NM_172990.5 | chr4:154964122-154980938 | 16298 | Pcdh12 | NM_017378.2 | chr18:38267091-38284401 |
| 16204 | Panx1 | NM_019482.2 | chr9:15005784-15045478 | 16299 | Pcdh15 | NM_001142735.1 | chr10:73821866-74634765 |
| 16205 | Panx2 | NM_001002005.2 | chr15:89059725-89070907 | 16300 | Pcdh17 | NM_001013753.2 | chr14:84443562-84537060 |
| 16206 | Panx3 | NM_172454.2 | chr9:37659901-37669222 | 16301 | Pcdh18 | NM_130448.3 | chr3:49743295-49757316 |
| 16207 | Paox | NM_153783.4 | chr7:140125684-140134334 | 16302 | Pcdh19 | NM_001105245.1 | chrX:133582860-133688993 |
| 16208 | Papd4 | NM_133905.3 | chr13:93147399-93192283 | 16303 | Pcdh20 | NM_178685.5 | chr14:88464746-88471396 |
| 16209 | Papd5 | NM_001164497.1 | chr8:88199212-88259722 | 16304 | Pcdh7 | NM_001122758.2 | chr5:57718080-58133235 |
| 16210 | Papd7 | NM_001169131.1 | chr13:69497958-69533864 | 16305 | Pcdh8 | NM_001042726.3 | chr14:79766771-79771312 |
| 16211 | Papl | NM_175319.4 | chr7:26607636-28631015 | 16306 | Pcdh9 | NM_001081377.2 | chr14:93013699-93888888 |
| 16212 | Paplh | NM_001205343.1 | chr12:83763633-83792384 | 16307 | Pcdha1 | NM_054072.1 | chr18:36930284-37187657 |
| 16213 | Papola | NM_011032.8 | chr12:105784701-105838943 | 16308 | Pcdha10 | NM_009961.1 | chr18:37005319-37187657 |
| 16214 | Papolb | NM_019943.2 | chr5:142527739-142530076 | 16309 | Pcdha11 | NM_009960.1 | chr18:37010857-37187657 |
| 16215 | Papolg | NM_172555.2 | chr11:23862645-23895270 | 16310 | Pcdha12 | NM_138663.2 | chr18:37020229-37187657 |
| 16216 | Pappa | NM_021362.1 | chr4:65124173-65357509 | 16311 | Pcdha2 | NM_198117.2 | chr18:36939204-37187660 |
| 16217 | Pappa2 | NM_001085376.2 | chr1:158711730-158957438 | 16312 | Pcdha3 | NM_138662.1 | chr18:36946206-37187657 |
| 16218 | Papss1 | NM_001289477.1 | chr3:131566031-131643671 | 16313 | Pcdha4 | NM_007766.2 | chr18:36952688-37187657 |
| 16219 | Papss2 | NM_011868.1 | chr19:32595714-32667187 | 16314 | Pcdha-g | NM_001174154.2 | chr18:36952647-37841872 |
| 16220 | Paqr3 | NM_198422.2 | chr5:97082328-97111596 | 16315 | Pcdha5 | NM_009959.1 | chr18:36960439-37187657 |
| 16221 | Paqr4 | NM_023824.3 | chr17:23736185-23740330 | 16316 | Pcdha6 | NM_007767.3 | chr18:36967755-37187657 |
| 16222 | Paqr5 | NM_028748.2 | chr9:61953737-62026790 | 16317 | Pcdha7 | NM_009957.1 | chr18:36973923-37187657 |
| 16223 | Paqr6 | NM_198410.3 | chr3:88364588-88368541 | 16318 | Pcdha8 | NM_201243.1 | chr18:36992466-37187657 |
| 16224 | Paqr7 | NM_001285845.1 | chr4:134496760-134510237 | 16319 | Pcdha9 | NM_138661.1 | chr18:36997879-37187657 |
| 16225 | Paqr8 | NM_028829.3 | chr1:120890621-20938756 | 16320 | Pcdhac1 | NM_001003671.1 | chr18:37090135-37187657 |
| 16226 | Paqr9 | NM_198414.2 | chr9:95559816-95562121 | 16321 | Pcdhac2 | NM_001003672.1 | chr18:37143968-37187657 |
| 16227 | Pard3 | NM_001013580.3 | chr8:127299651-127402059 | 16322 | Pcdhb1 | NM_053126.1 | chr18:37264997-37267454 |
| 16228 | Pard3b | NM_001081050.2 | chr1:61638823-62642284 | 16323 | Pcdhb10 | NM_053135.2 | chr18:37411679-37414514 |
| 16229 | Pard6a | NM_001047435.2 | chr8:105701646-105703494 | 16324 | Pcdhb11 | NM_053136.3 | chr18:37421417-37425032 |
| 16230 | Pard6b | NM_021409.2 | chr2:168081003-168101203 | 16325 | Pcdhb12 | NM_053137.2 | chr18:37435620-37438654 |
| 16231 | Pard6g | NM_053117.3 | chr18:80046894-80119640 | 16326 | Pcdhb13 | NM_053138.2 | chr18:37442516-37446209 |
| 16232 | Parg | NM_011960.2 | chr14:32201970-32297549 | 16327 | Pcdhb14 | NM_053139.3 | chr18:37447656-37451094 |
| 16233 | Park2 | NM_016694.3 | chr17:10840383-12063360 | 16328 | Pcdhb15 | NM_053140.3 | chr18:37473545-37476340 |
| 16234 | Park7 | NM_020569.3 | chr4:150897132-150909921 | 16329 | Pcdhb16 | NM_053141.3 | chr18:37477767-37483037 |
| 16235 | Parl | NM_001005767.4 | chr16:20279820-20302362 | 16330 | Pcdhb17 | NM_053142.3 | chr18:37485020-37488290 |
| 16236 | Parn1 | NM_145562.2 | chr5:91517699-91623996 | 16331 | Pcdhb18 | NM_053143.2 | chr18:37489464-37494503 |
| 16237 | Parn | NM_028761.3 | chr16:13537963-13668170 | 16332 | Pcdhb19 | NM_053144.2 | chr18:37496997-37501711 |
| 16238 | Parp1 | NM_007415.2 | chr1:180568974-180601254 | 16333 | Pcdhb2 | NM_053127.2 | chr18:37294839-37297614 |

Fig. 26 - 87

| | | | |
|---|---|---|---|
| 16334 | Pcdhb20 | NM_053145.2 | chr18:37504263-37507661 |
| 16335 | Pcdhb21 | NM_053146.2 | chr18:37513651-37516363 |
| 16336 | Pcdhb22 | NM_053147.3 | chr18:37518352-37521419 |
| 16337 | Pcdhb3 | NM_053128.2 | chr18:37300798-37304585 |
| 16338 | Pcdhb4 | NM_053129.3 | chr18:37307454-37311173 |
| 16339 | Pcdhb5 | NM_053130.3 | chr18:37320386-37323913 |
| 16340 | Pcdhb6 | NM_053131.1 | chr18:37334027-37336346 |
| 16341 | Pcdhb7 | NM_053132.3 | chr18:37341701-37345207 |
| 16342 | Pcdhb8 | NM_053133.1 | chr18:37355270-37357610 |
| 16343 | Pcdhb9 | NM_053134.3 | chr18:37400854-37403909 |
| 16344 | Pcdhga1 | NM_033584.1 | chr18:37661944-37841870 |
| 16345 | Pcdhga10 | NM_033593.3 | chr18:37747187-37841870 |
| 16346 | Pcdhga11 | NM_033594.2 | chr18:37755772-37841872 |
| 16347 | Pcdhga12 | NM_033595.4 | chr18:37765579-37841872 |
| 16348 | Pcdhga2 | NM_033585.1 | chr18:37669104-37841870 |
| 16349 | Pcdhga3 | NM_033586.2 | chr18:37674334-37841872 |
| 16350 | Pcdhga4 | NM_033587.3 | chr18:37685399-37841870 |
| 16351 | Pcdhga5 | NM_033588.4 | chr18:37694500-37841870 |
| 16352 | Pcdhga6 | NM_033589.1 | chr18:37707228-37841870 |
| 16353 | Pcdhga7 | NM_033590.3 | chr18:37714833-37841872 |
| 16354 | Pcdhga8 | NM_033591.3 | chr18:37725705-37841872 |
| 16355 | Pcdhga9 | NM_033592.3 | chr18:37736935-37841863 |
| 16356 | Pcdhgb1 | NM_033574.3 | chr18:37680457-37841870 |
| 16357 | Pcdhgb2 | NM_033575.3 | chr18:37689858-37841872 |
| 16358 | Pcdhgb4 | NM_033576.1 | chr18:37720553-37841870 |
| 16359 | Pcdhgb5 | NM_033577.1 | chr18:37731153-37841870 |
| 16360 | Pcdhgb6 | NM_033578.3 | chr18:37742093-37841872 |
| 16361 | Pcdhgb7 | NM_033579.1 | chr18:37751778-37841870 |
| 16362 | Pcdhgb8 | NM_033580.2 | chr18:37761800-37841870 |
| 16363 | Pcdhgc3 | NM_033581.3 | chr18:37806409-37841870 |
| 16364 | Pcdhgc4 | NM_033582.2 | chr18:37815078-37841872 |
| 16365 | Pcdhgc5 | NM_033583.3 | chr18:37819545-37841872 |
| 16366 | Pced1a | NM_001114541.1 | chr2:130417683-130424641 |
| 16367 | Pced1b | NM_172293.4 | chr15:97247106-97385691 |
| 16368 | Pcf11 | NM_029078.3 | chr7:92643711-92669912 |
| 16369 | Pcgf1 | NM_197992.1 | chr6:83078389-83080855 |
| 16370 | Pcgf2 | NM_001163307.1 | chr11:97688822-97699384 |
| 16371 | Pcgf3 | NM_172716.4 | chr5:108461331-108503099 |
| 16372 | Pcgf5 | NM_020569.3 | chr19:36379066-36456204 |
| 16373 | Pcgf6 | NM_027654.3 | chr19:47033618-47050845 |
| 16374 | Pcid2 | NM_178708.3 | chr8:13077524-13105343 |
| 16375 | Pcif1 | NM_146129.3 | chr2:164879367-164891437 |
| 16376 | Pck1 | NM_011044.2 | chr2:173153072-173159253 |
| 16377 | Pck2 | NM_028994.2 | chr14:55540265-55550017 |
| 16378 | Pclo | NM_011076.2 | chr5:14514917-14796042 |
| 16379 | Pcm1 | NM_023662.3 | chr8:41239758-41334087 |
| 16380 | Pcmt1 | NM_008786.2 | chr10:7630235-7663584 |
| 16381 | Pcmtd1 | NM_183028.3 | chr1:7088919-7173628 |
| 16382 | Pcmtd2 | NM_001291211.1 | chr2:181837853-181857460 |
| 16383 | Pcna | NM_011045.2 | chr2:132249285-132253180 |
| 16384 | Pcnp | NM_001024622.2 | chr16:56015507-56029717 |
| 16385 | Pcnt | NM_001282992.1 | chr10:76351253-76442912 |
| 16386 | Pcnx | NM_018814.3 | chr12:81860029-82000924 |
| 16387 | Pcnxl2 | NM_175561.4 | chr8:125751507-125898317 |
| 16388 | Pcnxl3 | NM_144868.3 | chr19:5664634-5688908 |
| 16389 | Pcnxl4 | NM_026327.3 | chr12:72536356-72580213 |
| 16390 | Pcolce | NM_008788.2 | chr5:137605106-137611404 |
| 16391 | Pcolce2 | NM_029620.2 | chr9:95637627-95695551 |
| 16392 | Pcp2 | NM_001129803.1 | chr8:3623373-3625545 |
| 16393 | Pcp4 | NM_008791.2 | chr16:96467605-96525793 |
| 16394 | Pcp4l1 | NM_025557.1 | chr1:171173263-171196268 |
| 16395 | Pcsk3 | NM_013628.2 | chr13:75089986-75132498 |
| 16396 | Pcsk1n | NM_013892.3 | chrX:7919821-7924410 |
| 16397 | Pcsk2 | NM_008792.4 | chr2:143546132-143816282 |
| 16398 | Pcsk2os1 | NR_040354.1 | chr2:143535475-143547827 |
| 16399 | Pcsk2os2 | NR_040625.1 | chr2:143747582-143789186 |
| 16400 | Pcsk4 | NM_008793.2 | chr10:80321282-80329473 |
| 16401 | Pcsk5 | NM_013163144.1 | chr19:17558158-17837632 |
| 16402 | Pcsk6 | NM_001291184.1 | chr7:65862135-66050386 |
| 16403 | Pcsk7 | NM_001291934.1 | chr9:45906568-45929722 |
| 16404 | Pcsk9 | NM_153565.2 | chr4:106442333-106464325 |
| 16405 | Pctp | NM_008796.3 | chr11:89983416-90002894 |
| 16406 | Pcx | NM_001162946.1 | chr19:4510471-4621752 |
| 16407 | Pcyox1 | NM_025823.4 | chr6:86386005-86397150 |
| 16408 | Pcyox1l | NM_172832.4 | chr18:61696836-61707635 |
| 16409 | Pcyt1a | NM_001163159.1 | chr16:32431019-32475065 |
| 16410 | Pcyt1b | NM_177546.2 | chrX:93654862-93749948 |
| 16411 | Pcyt2 | NM_024229.2 | chr11:120610086-120617890 |
| 16412 | Pdap1 | NM_001033313.3 | chr5:145128769-145140089 |
| 16413 | Pdc | NM_001159730.1 | chr1:150319416-150333906 |
| 16414 | Pdcd1 | NM_008798.2 | chr1:94038304-94052553 |
| 16415 | Pdcd10 | NM_019745.4 | chr3:75516489-75556852 |
| 16416 | Pdcd11 | NM_011053.2 | chr19:47090765-47131145 |
| 16417 | Pdcd1lg2 | NM_021396.2 | chr19:29410918-29472927 |
| 16418 | Pdcd2 | NM_008799.2 | chr17:15521574-15527301 |
| 16419 | Pdcd2l | NM_026549.3 | chr7:34184496-34196647 |
| 16420 | Pdcd4 | NM_001168491.1 | chr19:53903350-53929861 |
| 16421 | Pdcd5 | NM_019746.4 | chr7:35641984-35647482 |
| 16422 | Pdcd6 | NM_011051.3 | chr13:74803120-74813726 |
| 16423 | Pdcd6ip | NM_001164677.1 | chr9:113651743-113708259 |
| 16424 | Pdcd7 | NM_016688.2 | chr9:65346067-65359643 |
| 16425 | Pdcl | NM_026176.3 | chr2:37350073-37359332 |
| 16426 | Pdcl2 | NM_023508.2 | chr5:76312115-76331156 |
| 16427 | Pdcl3 | NM_026850.4 | chr1:38987813-38997236 |
| 16428 | Pddc1 | NM_172116.4 | chr7:141408183-141414125 |
| 16429 | Pde10a | NM_001290707.1 | chr17:8526800-8986648 |
| 16430 | Pde11a | NM_001081033.1 | chr2:75991131-76338653 |
| 16431 | Pde12 | NM_178668.3 | chr14:26664116-26669846 |
| 16432 | Pde1a | NM_001009978.1 | chr2:79859024-79908399 |
| 16433 | Pde1b | NM_001285890.1 | chr15:103514976-103530056 |
| 16434 | Pde1c | NM_001025568.2 | chr6:56100439-56362392 |
| 16435 | Pde2a | NM_001008548.4 | chr7:101421690-101512829 |
| 16436 | Pde3a | NM_018779.1 | chr6:141249268-141499351 |
| 16437 | Pde3b | NM_011055.2 | chr7:114415253-114537937 |
| 16438 | Pde4a | NM_019798.5 | chr9:21196704-21213248 |
| 16439 | Pde4b | NM_001177980.1 | chr4:102570059-102607262 |
| 16440 | Pde4c | NM_201607.2 | chr8:70724063-70751176 |
| 16441 | Pde4d | NM_011056.3 | chr13:108654176-109955969 |
| 16442 | Pde4dip | NM_001039376.2 | chr3:97689828-97888707 |
| 16443 | Pde5a | NM_153422.2 | chr3:122729157-122859374 |
| 16444 | Pde6a | NM_146086.2 | chr18:61220498-61289718 |
| 16445 | Pde6b | NM_008806.2 | chr5:108388372-108431742 |
| 16446 | Pde6c | NM_001170959.1 | chr19:38132780-38183951 |
| 16447 | Pde6d | NM_008801.2 | chr1:86543014-86582501 |
| 16448 | Pde6g | NM_012065.3 | chr11:120447606-120453500 |
| 16449 | Pde6h | NM_023898.4 | chr6:136954522-136963483 |
| 16450 | Pde7a | NM_001122759.2 | chr3:19223108-19311322 |
| 16451 | Pde7b | NM_013875.5 | chr10:20398003-20725068 |
| 16452 | Pde8a | NM_008803.2 | chr7:81213803-81333622 |
| 16453 | Pde8b | NM_001170669.1 | chr13:95024104-95223050 |
| 16454 | Pde9a | NM_001163748.1 | chr17:31386233-31476309 |
| 16455 | Pdf | NM_026513.2 | chr8:107046289-107048614 |
| 16456 | Pdgfa | NM_008808.3 | chr5:138976971-138994953 |
| 16457 | Pdgfb | NM_011057.3 | chr15:79995875-80014808 |
| 16458 | Pdgfc | NM_019971.2 | chr3:81036415-81214031 |
| 16459 | Pdgfd | NM_027924.2 | chr9:6168611-6377519 |
| 16460 | Pdgfra | NM_001083316.1 | chr5:75156165-75198204 |
| 16461 | Pdgfrb | NM_001146268.1 | chr18:61045149-61085067 |
| 16462 | Pdgfrl | NM_026840.3 | chr8:40926232-40960770 |
| 16463 | Pdha1 | NM_008810.3 | chrX:160122218-160138430 |
| 16464 | Pdha2 | NM_008811.2 | chr3:141210003-141212355 |
| 16465 | Pdhb | NM_024221.3 | chr14:8165990-8172992 |
| 16466 | Pdhx | NM_175094.5 | chr2:103021056-103073513 |
| 16467 | Pdia2 | NM_001081070.1 | chr17:26195998-26199007 |
| 16468 | Pdia3 | NM_007952.2 | chr2:121413901-121438686 |
| 16469 | Pdia4 | NM_009787.2 | chr6:47796140-47813512 |
| 16470 | Pdia5 | NM_028295.1 | chr16:35397311-35490873 |
| 16471 | Pdia6 | NM_027959.3 | chr12:17266594-17284770 |
| 16472 | Pdik1l | NM_001163794.1 | chr4:134275004-134287253 |
| 16473 | Pdilt | NM_027943.1 | chr7:119486586-119523482 |
| 16474 | Pdk1 | NM_172665.5 | chr2:71873223-71903858 |
| 16475 | Pdk2 | NM_133667.2 | chr11:95026257-95041371 |
| 16476 | Pdk3 | NM_145630.2 | chrX:93764615-93832095 |
| 16477 | Pdk4 | NM_013743.2 | chr6:5483350-5496278 |
| 16478 | Pdlim1 | NM_016861.4 | chr19:40222238-40271616 |
| 16479 | Pdlim2 | NM_001253736.1 | chr14:70164217-70176815 |
| 16480 | Pdlim3 | NM_016798.3 | chr8:45885484-45919546 |
| 16481 | Pdlim4 | NM_019417.3 | chr11:54054927-54069017 |
| 16482 | Pdlim5 | NM_001190852.1 | chr3:142239584-142395696 |
| 16483 | Pdlim7 | NM_001114087.2 | chr13:55506772-55513446 |
| 16484 | Pdp1 | NM_001033453.3 | chr4:11958184-11966450 |
| 16485 | Pdp2 | NM_001024606.1 | chr8:104591467-104596849 |
| 16486 | Pdpk1 | NM_001080773.2 | chr17:24073679-24141594 |
| 16487 | Pdpn | NM_001290822.1 | chr4:143267408-143299564 |
| 16488 | Pdpr | NM_198308.1 | chr8:111094744-111135144 |
| 16489 | Pdrg1 | NM_178939.2 | chr2:153008889-153015383 |
| 16490 | Pds5a | NM_001081321.1 | chr5:65615259-65697856 |
| 16491 | Pds5b | NM_175310.6 | chr5:150673826-150810669 |
| 16492 | Pdss1 | NM_019501.3 | chr2:22895521-22940259 |
| 16493 | Pdss2 | NM_001168289.1 | chr10:43221485-43464882 |
| 16494 | Pdx1 | NM_008814.3 | chr5:147270130-147275149 |
| 16495 | Pdxdc1 | NM_001039533.2 | chr16:13833572-13903145 |
| 16496 | Pdxk | NM_172134.2 | chr10:78436746-78464948 |
| 16497 | Pdxk-ps | NR_027316.1 | chr17:32076082-32091423 |
| 16498 | Pdxp | NM_020271.3 | chr15:78913918-78919517 |
| 16499 | Pdyn | NM_001286502.1 | chr2:129686548-129698658 |
| 16500 | Pdzd11 | NM_028303.3 | chrX:100622905-100625907 |
| 16501 | Pdzd2 | NM_001081064.1 | chr15:12357053-12592556 |
| 16502 | Pdzd3 | NM_133226.2 | chr9:44247311-44251464 |
| 16503 | Pdzd4 | NM_001029868.2 | chrX:73793356-73824969 |
| 16504 | Pdzd7 | NM_001195265.1 | chr19:45026906-45045772 |
| 16505 | Pdzd8 | NM_001033222.1 | chr19:59296083-59345780 |
| 16506 | Pdzd9 | NM_001040136.2 | chr7:120659295-120670343 |
| 16507 | Pdzk1 | NM_001146001.1 | chr3:96832673-96870926 |
| 16508 | Pdzk1ip1 | NM_001164557.1 | chr4:115088707-115093894 |
| 16509 | Pdzrn3 | NM_018884.2 | chr6:101149606-101377897 |
| 16510 | Pdzrn4 | NM_001164593.1 | chr15:92396809-92771819 |
| 16511 | Pea15a | NM_011063.2 | chr1:172196728-172206781 |
| 16512 | Pea15b | NR_027806.1 | chr5:77510039-77513003 |
| 16513 | Peak1 | NM_172924.3 | chr9:56201128-56418050 |
| 16514 | Pear1 | NM_001032413.3 | chr3:87749096-87768953 |
| 16515 | Pebp1 | NM_018858.2 | chr5:117282650-117287564 |
| 16516 | Pebp4 | NM_028526.4 | chr14:69840406-69851960 |
| 16517 | Pecam1 | NM_001032378.2 | chr11:106654212-106715281 |
| 16518 | Pecr | NM_023523.5 | chr1:72259172-72284314 |
| 16519 | Pef1 | NM_026441.4 | chr4:130107555-130128134 |
| 16520 | Peg10 | NM_130877.2 | chr6:4747305-4760516 |
| 16521 | Peg12 | NM_013788.2 | chr7:62461870-62464510 |
| 16522 | Peg13 | NR_002864.1 | chr15:72805599-72810324 |
| 16523 | Peg3 | NM_008817.2 | chr7:6705959-6730419 |

Fig. 26 - 88

| | | | | | | | | |
|---|---|---|---|---|---|---|---|---|
| 16524 | Peg3os | NR_023846.1 | chr7:6706759-6707624 | | 16619 | Phb2 | NM_007531.2 | chr6:124712288-124716945 |
| 16525 | Peli1 | NM_023324.2 | chr1:21091323-21150327 | | 16620 | Phc1 | NM_001042623.2 | chr6:122317730-122339657 |
| 16526 | Peli2 | NM_033602.2 | chr14:48120868-48260883 | | 16621 | Phc2 | NM_001195083.1 | chr4:128727570-128752881 |
| 16527 | Peli3 | NM_172835.3 | chr19:4931854-4943092 | | 16622 | Phc3 | NM_001165954.1 | chr3:30899294-30969415 |
| 16528 | Pelo | NM_134058.3 | chr13:115088354-115090158 | | 16623 | Phex | NM_011077.2 | chrX:157162074-157415286 |
| 16529 | Pelp1 | NM_029231.4 | chr11:70392886-70410031 | | 16624 | Phf1 | NM_009343.3 | chr17:26933126-26937908 |
| 16530 | Pemt | NM_001290011.1 | chr11:59970613-60046489 | | 16625 | Phf10 | NM_024250.4 | chr17:14944994-14961260 |
| 16531 | Penk | NM_001002927.2 | chr4:4133535-4138445 | | 16626 | Phf11a | NM_172603.3 | chr14:59276912-59297522 |
| 16532 | Peo1 | NM_153796.3 | chr19:45006557-45012762 | | 16627 | Phf11b | NM_001164327.1 | chr14:59320983-59341330 |
| 16533 | Pepd | NM_008820.2 | chr7:34912406-35044708 | | 16628 | Phf11c | NM_001164289.1 | chr14:59380832-59393512 |
| 16534 | Per1 | NM_001159367.1 | chr11:69100157-69109957 | | 16629 | Phf11d | NM_199015.4 | chr14:59347406-59365490 |
| 16535 | Per2 | NM_011066.3 | chr1:91415981-91459328 | | 16630 | Phf12 | NM_174852.3 | chr11:77982815-78030535 |
| 16536 | Per3 | NM_001289877.1 | chr4:151003654-151044665 | | 16631 | Phf13 | NM_172705.2 | chr4:151989630-151996179 |
| 16537 | Peril | NR_110488.1 | chr3:34772074-34782346 | | 16632 | Phf14 | NM_001168382.1 | chr6:11925880-12081198 |
| 16538 | Perm1 | NM_172417.3 | chr4:156215926-156221307 | | 16633 | Phf19 | NM_028716.4 | chr2:34893754-34913976 |
| 16539 | Perp | NM_022032.4 | chr10:18845070-18857072 | | 16634 | Phf2 | NM_011078.3 | chr13:48801749-48870885 |
| 16540 | Pes1 | NM_022889.3 | chr11:3963974-3980004 | | 16635 | Phf20 | NM_172674.2 | chr2:156196646-156309953 |
| 16541 | Pet100 | NM_001195244.1 | chr8:3621550-3624235 | | 16636 | Phf20l1 | NM_001081409.1 | chr15:66977571-66645255 |
| 16542 | Pet112 | NM_144896.4 | chr3:85574128-85654470 | | 16637 | Phf21a | NM_001109690.1 | chr2:92221561-92364666 |
| 16543 | Pet117 | NM_001164813.1 | chr2:144368982-144373337 | | 16638 | Phf21b | NM_001081166.2 | chr15:84785375-84856129 |
| 16544 | Pet2 | NM_008821.2 | chrX:89403847-89409689 | | 16639 | Phf23 | NM_001291125.1 | chr11:69995765-70000011 |
| 16545 | Pex1 | NM_027777.2 | chr5:3596065-3637230 | | 16640 | Phf3 | NM_001081080.1 | chr1:30802341-30863256 |
| 16546 | Pex10 | NM_001042407.1 | chr4:155067029-155072406 | | 16641 | Phf5a | NM_026737.3 | chr15:81864515-81871892 |
| 16547 | Pex11a | NM_011068.1 | chr7:79737263-79743025 | | 16642 | Phf6 | NM_001290546.1 | chrX:52912213-52956961 |
| 16548 | Pex11b | NM_001162387.1 | chr3:96635429-96645381 | | 16643 | Phf7 | NM_027949.1 | chr14:31237695-31251218 |
| 16549 | Pex11g | NM_026951.2 | chr8:3458816-3467648 | | 16644 | Phf8 | NM_001133354.1 | chrX:151520671-151633857 |
| 16550 | Pex12 | NM_134025.3 | chr11:83294644-83298977 | | 16645 | Phgdh | NM_016966.3 | chr3:98313170-98339969 |
| 16551 | Pex13 | NM_023651.4 | chr11:23646478-23665935 | | 16646 | Phgr1 | NM_001146644.1 | chr2:118772768-118778164 |
| 16552 | Pex14 | NM_019781.2 | chr4:148960534-149099812 | | 16647 | Phip | NM_001081216.1 | chr9:82866158-82975489 |
| 16553 | Pex16 | NM_145122.2 | chr2:92375238-92381220 | | 16648 | Phka1 | NM_008832.2 | chrX:102513974-102644246 |
| 16554 | Pex19 | NM_001159525.1 | chr1:172126754-172136497 | | 16649 | Phka2 | NM_001177826.1 | chrX:160502433-160598878 |
| 16555 | Pex2 | NM_001163301.2 | chr3:5560187-5576248 | | 16650 | Phkb | NM_199446.1 | chr8:85841001-86060642 |
| 16556 | Pex26 | NM_028730.6 | chr6:121183666-121196192 | | 16651 | Phkg1 | NM_011079.2 | chr5:129863434-129879083 |
| 16557 | Pex3 | NM_001164195.1 | chr10:13523841-13553142 | | 16652 | Phkg2 | NM_026888.3 | chr7:127573347-127583307 |
| 16558 | Pex5 | NM_001277330.1 | chr6:124396815-124414863 | | 16653 | Phlda1 | NM_009344.3 | chr10:111506285-111508649 |
| 16559 | Pex5l | NM_001163516.3 | chr3:32947925-33143191 | | 16654 | Phlda2 | NM_009434.2 | chr7:143501547-143502524 |
| 16560 | Pex6 | NM_145488.1 | chr17:46711462-46725541 | | 16655 | Phlda3 | NM_013750.2 | chr1:135766084-135769134 |
| 16561 | Pex7 | NM_001161825.1 | chr10:19860089-19907674 | | 16656 | Phldb1 | NM_153537.4 | chr9:44686307-44735198 |
| 16562 | Pf4 | NM_019410.3 | chr5:90772434-90773383 | | 16657 | Phldb2 | NM_001252442.1 | chr16:45746230-45844378 |
| 16563 | Pfas | NM_001159519.1 | chr11:68985700-69098460 | | 16658 | Phldb3 | NM_001102613.1 | chr7:24611327-24629297 |
| 16564 | Pfdn1 | NM_026027.3 | chr18:36403678-36434495 | | 16659 | Phlpp1 | NM_133821.3 | chr1:106171868-106394245 |
| 16565 | Pfdn2 | NM_011070.3 | chr1:171345598-171358170 | | 16660 | Phlpp2 | NM_001122594.2 | chr8:109868602-109944671 |
| 16566 | Pfdn4 | NM_001013369.2 | chr2:170496427-170519070 | | 16661 | Phospho1 | NM_153104.3 | chr11:95824499-95832140 |
| 16567 | Pfdn5 | NM_027044.3 | chr15:102326115-102331489 | | 16662 | Phospho2 | NM_028521.2 | chr2:69789736-69797168 |
| 16568 | Pfkfb1 | NM_008824.3 | chrX:150589920-150643878 | | 16663 | Phox2a | NM_008887.2 | chr7:101818312-101822726 |
| 16569 | Pfkfb2 | NM_001262415.1 | chr1:130889042-130929253 | | 16664 | Phox2b | NM_008888.3 | chr5:67094396-67099126 |
| 16570 | Pfkfb3 | NM_001177752.1 | chr2:11471430-11502090 | | 16665 | Phpt1 | NM_029293.2 | chr2:25573430-25574871 |
| 16571 | Pfkfb4 | NM_173019.5 | chr9:108991901-109032225 | | 16666 | Phrf1 | NM_001081118.1 | chr7:141228787-141262751 |
| 16572 | Pfkl | NM_008826.4 | chr10:77986948-78009796 | | 16667 | Phtf1 | NM_001163467.3 | chr3:103968109-104007491 |
| 16573 | Pfkm | NM_001163487.1 | chr15:98108470-98132447 | | 16668 | Phtf1os | NR_030676.1 | chr3:103964535-103968316 |
| 16574 | Pfkp | NM_001291071.1 | chr13:6579873-6648771 | | 16669 | Phtf2 | NM_172992.3 | chr5:20758663-20882124 |
| 16575 | Pfn1 | NM_011072.4 | chr11:70651846-70654650 | | 16670 | Phxr4 | NR_028271.1 | chr9:13431360-13432740 |
| 16576 | Pfn2 | NM_019410.3 | chr3:57841894-57847757 | | 16671 | Phyh | NM_010726.2 | chr2:4918995-4938743 |
| 16577 | Pfn3 | NM_029303.2 | chr13:55414687-55415232 | | 16672 | Phyhd1 | NM_001252568.2 | chr2:30266202-30282149 |
| 16578 | Pfn4 | NM_028376.3 | chr12:4769294-4778266 | | 16673 | Phyhip | NM_145981.3 | chr14:70457516-70468824 |
| 16579 | Pfpl | NM_029410.2 | chr19:12427904-12432110 | | 16674 | Phyhipl | NM_001162846.1 | chr10:70557685-70592812 |
| 16580 | Pga5 | NM_021453.4 | chr19:10668956-10678071 | | 16675 | Phykpl | NM_028398.2 | chr11:51584756-51603269 |
| 16581 | Pgam1 | NM_023418.2 | chr19:41911870-41918665 | | 16676 | Pi15 | NM_053191.2 | chr1:17601900-17630939 |
| 16582 | Pgam2 | NM_018870.3 | chr11:5801636-5803796 | | 16677 | Pi16 | NM_023734.3 | chr17:29318881-29328902 |
| 16583 | Pgam5 | NM_001163538.1 | chr5:110259134-110269899 | | 16678 | Pi4k2a | NM_145501.2 | chr19:42090434-42122218 |
| 16584 | Pgap1 | NM_001163314.2 | chr1:54472999-54557684 | | 16679 | Pi4k2b | NM_025951.3 | chr5:52741573-52769344 |
| 16585 | Pgap2 | NM_001291358.1 | chr7:102110334-102238564 | | 16680 | Pi4ka | NM_001001983.2 | chr16:17280350-17406314 |
| 16586 | Pgap3 | NM_001035537.2 | chr11:98388671-98400490 | | 16681 | Pi4kb | NM_175356.3 | chr3:94974730-95006937 |
| 16587 | Pgbd1 | NM_001012311.2 | chr13:21421274-21441053 | | 16682 | Pianp | NM_001145926.1 | chr6:124998699-125003097 |
| 16588 | Pgbd5 | NM_171824.2 | chr8:124389048-124433936 | | 16683 | Pias1 | NM_019663.3 | chr9:62880076-62980879 |
| 16589 | Pgc | NM_025973.3 | chr17:47726841-47734478 | | 16684 | Pias2 | NM_001164167.1 | chr18:77085207-77155708 |
| 16590 | Pgd | NM_001081274.1 | chr4:149149984-149166707 | | 16685 | Pias3 | NM_001165949.1 | chr3:96697075-96706070 |
| 16591 | Pgf | NM_001271705.1 | chr12:85166638-85175982 | | 16686 | Pias4 | NM_021501.4 | chr10:81153965-81167720 |
| 16592 | Pggt1b | NM_172627.3 | chr18:46299948-46280850 | | 16687 | Pibf1 | NM_029320.3 | chr14:99099423-99254494 |
| 16593 | Pgk1 | NM_008828.3 | chrX:106187099-106203699 | | 16688 | Picalm | NM_001252520.1 | chr7:90130231-90209447 |
| 16594 | Pgk2 | NM_031190.2 | chr17:40207017-40208609 | | 16689 | Pick1 | NM_001045558.1 | chr15:79229381-79249466 |
| 16595 | Pgis | NM_025396.3 | chr8:71592183-71596267 | | 16690 | Pid1 | NM_001003948.2 | chr1:84036292-84284645 |
| 16596 | Pglyrp1 | NM_009402.2 | chr7:18884689-18890438 | | 16691 | Pidd1 | NM_022654.1 | chr7:141438514-141443355 |
| 16597 | Pglyrp2 | NM_001271476.1 | chr17:32412460-32424167 | | 16692 | Piezo1 | NM_001037298.1 | chr8:122481697-122551329 |
| 16598 | Pglyrp3 | NM_207247.4 | chr3:92014582-92031984 | | 16693 | Piezo2 | NM_001039485.4 | chr18:63010212-63387183 |
| 16599 | Pglyrp4 | NM_001165968.1 | chr3:90726905-90741517 | | 16694 | Pif1 | NM_172453.3 | chr9:65587204-65595962 |
| 16600 | Pgm1 | NM_025700.2 | chr5:64092949-64128158 | | 16695 | Pifo | NM_001200028.1 | chr3:105996956-106014646 |
| 16601 | Pgm2 | NM_028132.3 | chr4:99929450-99987294 | | 16696 | Piga | NM_011081.2 | chrX:164419786-164433915 |
| 16602 | Pgm2l1 | NM_027629.3 | chr7:100227606-100278872 | | 16697 | Pigb | NM_018889.3 | chr9:73015695-73039699 |
| 16603 | Pgm3 | NM_001163746.1 | chr9:86552475-86571842 | | 16698 | Pigc | NM_001039045.1 | chr1:161969187-161973435 |
| 16604 | Pgm5 | NM_175013.2 | chr19:24678260-24861842 | | 16699 | Pigf | NM_008838.1 | chr17:86997258-87025401 |
| 16605 | Pgp | NM_025954.3 | chr17:24470472-24471596 | | 16700 | Pigg | NM_001081234.2 | chr5:108312924-108349355 |
| 16606 | Pgpep1 | NM_023217.4 | chr8:70646435-70659738 | | 16701 | Pigh | NM_029988.2 | chr12:79080669-79089670 |
| 16607 | Pgpep1l | NM_030101.1 | chr7:68236607-68264233 | | 16702 | Pigk | NM_025662.5 | chr3:152714099-152789013 |
| 16608 | Pgr | NM_008829.2 | chr9:8899832-8968611 | | 16703 | Pigl | NM_001039536.2 | chr11:62458459-62513900 |
| 16609 | Pgr15l | NM_001033361.3 | chrX:97072595-97082104 | | 16704 | Pigm | NM_026234.4 | chr1:172376530-172384099 |
| 16610 | Pgrmc1 | NM_016783.4 | chrX:36598192-36606079 | | 16705 | Pign | NM_013784.3 | chr1:105518421-105663676 |
| 16611 | Pgrmc2 | NM_027558.1 | chr3:41066325-41083046 | | 16706 | Pigo | NM_020035.3 | chr4:43017625-43025774 |
| 16612 | Pgs1 | NM_133757.2 | chr11:117986856-118024011 | | 16707 | Pigp | NM_001159616.1 | chr16:94364451-94370710 |
| 16613 | Phactr1 | NM_001057740.1 | chr13:42709580-43138512 | | 16708 | Pigq | NM_001291025.1 | chr17:25926419-25941989 |
| 16614 | Phactr2 | NM_001033257.4 | chr10:13207718-13324160 | | 16709 | Pigr | NM_011082.3 | chr1:130826683-130852249 |
| 16615 | Phactr3 | NM_001007154.3 | chr2:178193083-178338492 | | 16710 | Pigs | NM_201406.1 | chr11:78328421-78342776 |
| 16616 | Phactr4 | NM_001161797.1 | chr4:132355924-132422446 | | 16711 | Pigt | NM_133779.2 | chr2:164497524-164508301 |
| 16617 | Phax | NM_001162989.1 | chr18:56562568-56587712 | | 16712 | Pigu | NM_001004721.1 | chr2:155278251-155357424 |
| 16618 | Phb | NM_008831.4 | chr11:95666956-95680773 | | 16713 | Pigv | NM_001145955.1 | chr4:133661424-133672647 |

Fig. 26 - 89

| | | | |
|---|---|---|---|
| 16714 | Pigw | NM_001077636.1 | chr11:84876312-84880285 |
| 16715 | Pigx | NM_001111025.1 | chr16:32084415-32099727 |
| 16716 | Pigyl | NM_001082532.1 | chr9:22156845-22158354 |
| 16717 | Pigz | NM_172822.3 | chr16:31933850-31946046 |
| 16718 | Pih1d1 | NM_001278207.1 | chr7:45154302-45160064 |
| 16719 | Pih1d2 | NM_028300.2 | chr9:50617320-50625000 |
| 16720 | Pih1d3 | NM_029062.2 | chr1:31222838-31224287 |
| 16721 | Pik3ap1 | NM_031376.3 | chr19:41274217-41385070 |
| 16722 | Pik3c2a | NM_011083.2 | chr7:116337275-116443458 |
| 16723 | Pik3c2b | NM_001099276.2 | chr1:133046011-133108688 |
| 16724 | Pik3c2g | NM_011084.2 | chr6:139841444-139969283 |
| 16725 | Pik3c3 | NM_181414.5 | chr18:30272895-30348120 |
| 16726 | Pik3ca | NM_008839.2 | chr3:32436150-32468486 |
| 16727 | Pik3cb | NM_029094.3 | chr9:99038401-99140211 |
| 16728 | Pik3cd | NM_001029837.2 | chr4:149649167-149701629 |
| 16729 | Pik3cg | NM_001146200.1 | chr12:32173396-32208649 |
| 16730 | Pik3ip1 | NM_178149.4 | chr11:3330730-3342971 |
| 16731 | Pik3r1 | NM_001024955.2 | chr13:101680760-101692630 |
| 16732 | Pik3r2 | NM_008841.2 | chr8:70768180-70776712 |
| 16733 | Pik3r3 | NM_181585.5 | chr4:116221913-116303056 |
| 16734 | Pik3r4 | NM_001081309.1 | chr9:105642994-105687655 |
| 16735 | Pik3r5 | NM_177320.2 | chr11:68432124-68497846 |
| 16736 | Pik3r6 | NM_001004435.3 | chr11:68503018-68552695 |
| 16737 | Pikfyve | NM_011086.2 | chr1:65186684-65278696 |
| 16738 | Pilra | NM_153510.3 | chr5:137821951-137836278 |
| 16739 | Pilrb1 | NM_133209.2 | chr5:137852146-137858049 |
| 16740 | Pilrb2 | NM_001024932.2 | chr5:137865828-137871758 |
| 16741 | Pim1 | NM_008842.3 | chr17:29491044-29495459 |
| 16742 | Pim2 | NM_138606.2 | chrX:7878305-7883432 |
| 16743 | Pim3 | NM_145478.2 | chr15:88862193-88866726 |
| 16744 | Pin1 | NM_023371.3 | chr9:20652129-20666584 |
| 16745 | Pin1rt1 | NM_001033768.2 | chr2:104713925-104716290 |
| 16746 | Pin4 | NM_027181.1 | chrX:102119464-102127673 |
| 16747 | Pinc | NR_003202.1 | chr1:73391384-73407569 |
| 16748 | Pink1 | NM_026880.2 | chr4:138313409-138326296 |
| 16749 | Pinlyp | NM_001037143.2 | chr7:24541657-24546005 |
| 16750 | Pinx1 | NM_028228.3 | chr14:63860311-63919859 |
| 16751 | Pip | NM_008843.3 | chr6:41847548-41852062 |
| 16752 | Pip4k2a | NM_008845.4 | chr2:18842255-18998121 |
| 16753 | Pip4k2b | NM_054051.1 | chr11:97715156-97744704 |
| 16754 | Pip4k2c | NM_054097.3 | chr10:127197086-127211622 |
| 16755 | Pip5k1a | NM_008847.3 | chr3:95058529-95106930 |
| 16756 | Pip5k1b | NM_008846.2 | chr19:24294795-24555827 |
| 16757 | Pip5k1c | NM_001146687.2 | chr10:81292962-81319974 |
| 16758 | Pip5kl1 | NM_198191.2 | chr2:32575818-32583779 |
| 16759 | Pipox | NM_008952.2 | chr11:77880614-77893872 |
| 16760 | Pir | NM_027153.3 | chrX:164269430-164373013 |
| 16761 | Pira1 | NM_011087.1 | chr7:3836814-3915484 |
| 16762 | Pira11 | NM_011088.1 | chr7:3838153-3898093 |
| 16763 | Pira2 | NM_011089.2 | chr7:3836809-3845051 |
| 16764 | Pira4 | NM_011091.1 | chr7:3838125-3898092 |
| 16765 | Pira6 | NM_001289428.1 | chr7:3731632-3898150 |
| 16766 | Pira7 | NM_011094.1 | chr7:3838120-3898120 |
| 16767 | Pirb | NM_011095.2 | chr7:3712504-3720382 |
| 16768 | Pirt | NM_178656.3 | chr11:66911990-66970700 |
| 16769 | Pisd | NM_177298.3 | chr5:32736813-32785626 |
| 16770 | Pisd-ps1 | NR_003517.1 | chr1:3124020-3131944 |
| 16771 | Pisd-ps2 | NR_003519.3 | chr17:3064317-3084183 |
| 16772 | Pisd-ps3 | NR_003518.2 | chrUn_JH584304:52673-59689 |
| 16773 | Pithd1 | NM_025411.4 | chr4:135975601-135987244 |
| 16774 | Pitpna | NM_008850.2 | chr11:75588078-75628804 |
| 16775 | Pitpnb | NM_019640.5 | chr5:111330696-111388359 |
| 16776 | Pitpnc1 | NM_145823.2 | chr11:107207891-107470720 |
| 16777 | Pitpnm1 | NM_008851.4 | chr19:4100621-4113965 |
| 16778 | Pitpnm2 | NM_001289472.1 | chr5:124118688-124187182 |
| 16779 | Pitpnm2os1 | NR_045369.1 | chr5:124229724-124237137 |
| 16780 | Pitpnm3 | NM_001024927.2 | chr11:72047527-72135889 |
| 16781 | Pitrm1 | NM_145131.1 | chr13:6548156-6580149 |
| 16782 | Pitx1 | NM_011097.2 | chr13:55825053-55831425 |
| 16783 | Pitx2 | NM_001042502.2 | chr3:129213931-129219594 |
| 16784 | Pitx3 | NM_008852.4 | chr19:46135685-46148325 |
| 16785 | Piwil1 | NM_021311.3 | chr5:128736245-128755474 |
| 16786 | Piwil2 | NM_021308.1 | chr14:70372479-70429094 |
| 16787 | Piwil4 | NM_177905.3 | chr9:14702357-14740733 |
| 16788 | Pja1 | NM_001083110.2 | chrX:99465733-99470735 |
| 16789 | Pja2 | NM_001025309.1 | chr17:64281005-64331883 |
| 16790 | Pkd1 | NM_013630.2 | chr17:24549949-24596514 |
| 16791 | Pkd1l2 | NM_029686.4 | chr8:116995678-117082449 |
| 16792 | Pkd1l3 | NM_001039700.2 | chr8:109614516-109672592 |
| 16793 | Pkd2 | NM_008861.3 | chr5:104459456-104505819 |
| 16794 | Pkd2l1 | NM_181422.3 | chr19:44147836-44192442 |
| 16795 | Pkd2l2 | NM_001163004.1 | chr18:34409422-34441794 |
| 16796 | Pkdcc | NM_134117.2 | chr17:83215282-83225069 |
| 16797 | Pkdrej | NM_011105.2 | chr15:85814675-85821733 |
| 16798 | Pkhd1 | NM_153179.3 | chr1:20057778-20618057 |
| 16799 | Pkhd1l1 | NM_138674.2 | chr15:44475552-44597135 |
| 16800 | Pkia | NM_008862.3 | chr3:7366603-7445365 |
| 16801 | Pkib | NM_001039050.1 | chr10:57650980-57741112 |
| 16802 | Pkig | NM_001039390.2 | chr2:163658385-163726158 |
| 16803 | Pklr | NM_001099779.1 | chr3:89136622-89146594 |
| 16804 | Pkm | NM_001253883.1 | chr9:59656367-59679375 |
| 16805 | Pkmyt1 | NM_023058.3 | chr17:23726335-23736729 |
| 16806 | Pkn1 | NM_001199593.1 | chr8:83669761-83694061 |
| 16807 | Pkn2 | NM_178654.4 | chr3:142790901-142882004 |
| 16808 | Pkn3 | NM_153805.1 | chr2:30078765-30091019 |
| 16809 | Pknox1 | NM_016670.3 | chr17:31564772-31607693 |
| 16810 | Pknox2 | NM_001029838.2 | chr9:36890978-37147322 |
| 16811 | Pkp1 | NM_019645.3 | chr1:135871393-135919207 |
| 16812 | Pkp2 | NM_026163.2 | chr16:16213344-16272712 |
| 16813 | Pkp3 | NM_001162924.1 | chr7:141078228-141090510 |
| 16814 | Pkp4 | NM_026361.2 | chr2:59160849-59355205 |
| 16815 | Pla1a | NM_134102.4 | chr16:38396116-38433145 |
| 16816 | Pla2g10 | NM_001291009.2 | chr16:13715056-13730484 |
| 16817 | Pla2g10os | NR_040574.1 | chr16:13729835-13739471 |
| 16818 | Pla2g12a | NM_001286948.1 | chr3:129878605-129895825 |
| 16819 | Pla2g12b | NM_023530.2 | chr10:59403684-59421976 |
| 16820 | Pla2g15 | NM_133792.2 | chr8:106150398-106164715 |
| 16821 | Pla2g16 | NM_139269.2 | chr19:7557458-7588545 |
| 16822 | Pla2g1b | NM_011107.1 | chr5:115466265-115474717 |
| 16823 | Pla2g2a | NM_001082531.1 | chr4:138831875-138835189 |
| 16824 | Pla2g2c | NM_008868.3 | chr4:138725324-138744575 |
| 16825 | Pla2g2d | NM_011109.2 | chr4:138775734-138782143 |
| 16826 | Pla2g2e | NM_012044.2 | chr4:138877941-138882814 |
| 16827 | Pla2g2f | NM_012045.4 | chr4:138750532-138757598 |
| 16828 | Pla2g3 | NM_172791.2 | chr11:3488226-3494166 |
| 16829 | Pla2g4a | NM_008869.4 | chr1:149829618-149961290 |
| 16830 | Pla2g4b | NM_145378.4 | chr2:120033432-120043032 |
| 16831 | Pla2g4c | NM_001004762.3 | chr7:13329321-13360668 |
| 16832 | Pla2g4d | NM_001024137.1 | chr2:120265868-120289069 |
| 16833 | Pla2g4e | NM_177845.4 | chr2:120166411-120245335 |
| 16834 | Pla2g4f | NM_001024145.2 | chr2:120299956-120314165 |
| 16835 | Pla2g5 | NM_001122954.1 | chr4:138799246-138863469 |
| 16836 | Pla2g6 | NM_001199023.1 | chr15:79286227-79328371 |
| 16837 | Pla2g7 | NM_013737.5 | chr17:43568450-43612201 |
| 16838 | Pla2r1 | NM_008867.2 | chr2:60417542-60553308 |
| 16839 | Plaa | NM_172695.2 | chr4:94565138-94603247 |
| 16840 | Plac1 | NM_019538.4 | chrX:53070001-53114405 |
| 16841 | Plac8 | NM_139198.2 | chr5:100553732-100572205 |
| 16842 | Plac8l1 | NM_027072.1 | chr18:42178674-42196709 |
| 16843 | Plac9a | NM_207229.1 | chr14:25888402-26182273 |
| 16844 | Plac9b | NM_001270503.1 | chr14:25887933-26182351 |
| 16845 | Plag1 | NM_019969.3 | chr4:3901157-3938405 |
| 16846 | Plagl1 | NM_009538.2 | chr10:13090787-13131695 |
| 16847 | Plagl2 | NM_018807.5 | chr2:153227768-153241358 |
| 16848 | Plat | NM_008872.3 | chr8:22757721-22782848 |
| 16849 | Plau | NM_008873.3 | chr14:20836661-20843388 |
| 16850 | Plaur | NM_011113.3 | chr7:24462499-24475873 |
| 16851 | Plb1 | NM_001081407.1 | chr5:32239083-32364356 |
| 16852 | Plbd1 | NM_025806.2 | chr6:136612070-136661893 |
| 16853 | Plbd2 | NM_023625.4 | chr5:120483892-120503623 |
| 16854 | Plcb1 | NM_001145830.1 | chr2:134786163-135475258 |
| 16855 | Plcb2 | NM_001290790.1 | chr2:118707516-118728438 |
| 16856 | Plcb3 | NM_001290349.1 | chr19:6953712-6969814 |
| 16857 | Plcb4 | NM_013829.2 | chr2:135741829-136013068 |
| 16858 | Plcd1 | NM_019676.3 | chr9:119071527-119093502 |
| 16859 | Plcd3 | NM_152813.3 | chr11:103070295-103101658 |
| 16860 | Plcd4 | NM_001081456.1 | chr1:74542888-74565977 |
| 16861 | Plce1 | NM_019588.2 | chr19:38524196-38785100 |
| 16862 | Plcg1 | NM_021280.3 | chr2:160731309-160775760 |
| 16863 | Plcg2 | NM_172285.1 | chr8:117498290-117635142 |
| 16864 | Plch1 | NM_001177732.1 | chr3:63696233-63850991 |
| 16865 | Plch2 | NM_001113360.2 | chr4:154983114-155010984 |
| 16866 | Plcl1 | NM_001114663.1 | chr1:55405945-55754285 |
| 16867 | Plcl2 | NM_013880.4 | chr17:50509546-50688494 |
| 16868 | Plcxd1 | NM_001281812.1 | chr5:110100558-110105952 |
| 16869 | Plcxd2 | NM_001134480.1 | chr16:45959260-46010413 |
| 16870 | Plcxd3 | NM_177355.3 | chr15:4375490-4575579 |
| 16871 | Plcz1 | NM_054066.4 | chr6:139989721-140041417 |
| 16872 | Pld1 | NM_001164056.1 | chr3:27938679-28133362 |
| 16873 | Pld2 | NM_008876.3 | chr11:70540271-70558110 |
| 16874 | Pld3 | NM_011116.1 | chr7:27532017-27553112 |
| 16875 | Pld4 | NM_178911.4 | chr12:112760654-112768986 |
| 16876 | Pld5 | NM_001195816.1 | chr1:175962305-176213942 |
| 16877 | Pld6 | NM_001290283.1 | chr11:59783892-59787657 |
| 16878 | Pldi | NR_033616.1 | chr10:60928225-60938132 |
| 16879 | Plec | NM_001163540.1 | chr15:76170973-76206321 |
| 16880 | Plek | NM_019549.2 | chr11:16971205-17008718 |
| 16881 | Plek2 | NM_013738.3 | chr12:78888696-78906938 |
| 16882 | Plekha1 | NM_133942.2 | chr7:130865909-130913302 |
| 16883 | Plekha2 | NM_031257.3 | chr8:25039143-25101811 |
| 16884 | Plekha3 | NM_031256.3 | chr2:76675314-76697335 |
| 16885 | Plekha4 | NM_148927.2 | chr7:45526329-45554229 |
| 16886 | Plekha5 | NM_144920.3 | chr6:140424098-140594906 |
| 16887 | Plekha6 | NM_001160268.1 | chr1:133246096-133303435 |
| 16888 | Plekha7 | NM_172743.3 | chr7:116123484-116189841 |
| 16889 | Plekha8 | NM_001001335.2 | chr6:54603146-54645822 |
| 16890 | Plekhb1 | NM_001163182.1 | chr7:100643895-100662394 |
| 16891 | Plekhb2 | NM_145516.2 | chr1:34849958-34879585 |
| 16892 | Plekhd1 | NM_001177503.1 | chr12:80692600-80724216 |
| 16893 | Plekhd1os | NR_037995.1 | chr12:80686374-80692466 |
| 16894 | Plekhf1 | NM_024413.2 | chr7:38220653-38227994 |
| 16895 | Plekhf2 | NM_175175.4 | chr4:10988661-11007619 |
| 16896 | Plekhg1 | NM_001033253.3 | chr10:3872866-3967302 |
| 16897 | Plekhg2 | NM_001083912.1 | chr7:28359603-28372662 |
| 16898 | Plekhg3 | NM_153804.4 | chr12:76533559-76579039 |
| 16899 | Plekhg4 | NM_001081333.1 | chr8:105375380-105382862 |
| 16900 | Plekhg5 | NM_001285999.1 | chr4:152096718-152115404 |
| 16901 | Plekhg6 | NM_198604.2 | chr6:125362650-125380504 |
| 16902 | Plekhh1 | NM_181073.3 | chr12:79029162-79081655 |

Fig. 26 - 90

| | | | | | | | |
|---|---|---|---|---|---|---|---|
| 16903 | Plekhh2 | NM_177606.4 | chr17:84511894-84622142 | 16998 | Pnpla5 | NM_029427.1 | chr15:84112620-84123175 |
| 16904 | Plekhh3 | NM_146030.2 | chr11:101162679-101171302 | 16999 | Pnpla6 | NM_001122818.2 | chr8:3515383-3544267 |
| 16905 | Plekhj1 | NM_023900.2 | chr10:80796098-80798626 | 17000 | Pnpla7 | NM_146251.4 | chr2:24976032-25054072 |
| 16906 | Plekhm1 | NM_183034.1 | chr11:103365091-103412664 | 17001 | Pnpla8 | NM_026164.2 | chr12:44269153-44313435 |
| 16907 | Plekhm2 | NM_001033150.1 | chr4:141625733-141664115 | 17002 | Pnpo | NM_134021.2 | chr11:96937815-96944019 |
| 16908 | Plekhm3 | NM_001039493.1 | chr1:64789120-64956824 | 17003 | Pnpt1 | NM_027869.1 | chr11:29130750-29161828 |
| 16909 | Plekhn1 | NM_001008233.3 | chr4:156221455-156228542 | 17004 | Pnrc1 | NM_001033225.2 | chr4:33245422-33248787 |
| 16910 | Plekho1 | NM_023320.2 | chr3:95988835-95995839 | 17005 | Pnrc2 | NM_026383.3 | chr4:135870925-135873846 |
| 16911 | Plekho2 | NM_153119.3 | chr9:65552576-65580087 | 17006 | Poc1a | NM_027354.2 | chr9:106281060-106349891 |
| 16912 | Plekhs1 | NM_001164263.1 | chr19:56461636-56486729 | 17007 | Poc1b | NM_027740.6 | chr10:99107170-99197988 |
| 16913 | Plet1 | NM_029639.2 | chr9:50494524-50505639 | 17008 | Poc5 | NM_026173.3 | chr13:96388293-96415587 |
| 16914 | Plet1os | NR_040714.1 | chr9:50488798-50504805 | 17009 | Podn | NM_001285956.1 | chr4:108014792-108030986 |
| 16915 | Plg | NM_008877.3 | chr17:12378608-12419384 | 17010 | Podnl1 | NM_001013384.2 | chr8:84125988-84132517 |
| 16916 | Pigrkt | NM_026362.2 | chr19:29348676-29361871 | 17011 | Podxl | NM_013723.3 | chr6:31519492-31563937 |
| 16917 | Plin1 | NM_001113471.1 | chr7:79721163-79732776 | 17012 | Podxl2 | NM_176973.4 | chr6:88842557-88874044 |
| 16918 | Plin2 | NM_007408.3 | chr4:86656564-86670059 | 17013 | Pof1b | NM_181579.1 | chrX:112638426-112698651 |
| 16919 | Plin3 | NM_025836.3 | chr17:56278961-56290511 | 17014 | Pofut1 | NM_080463.3 | chr2:153241531-153270249 |
| 16920 | Plin4 | NM_020568.3 | chr17:56100590-56109802 | 17015 | Pofut2 | NM_030262.3 | chr10:77259299-77269586 |
| 16921 | Plin5 | NM_001077348.1 | chr17:56111600-56117298 | 17016 | Pogk | NM_001142948.1 | chr1:166393611-166409828 |
| 16922 | Plk1 | NM_011121.4 | chr7:122159434-122169884 | 17017 | Pogiut1 | NM_172380.4 | chr16:38525057-38550256 |
| 16923 | Plk2 | NM_152804.2 | chr13:110395043-110400843 | 17018 | Pogz | NM_001165948.1 | chr3:94837566-94883567 |
| 16924 | Plk3 | NM_013807.3 | chr4:117128654-117133963 | 17019 | Pola1 | NM_008892.2 | chrX:93304765-93632155 |
| 16925 | Plk4 | NM_011495.2 | chr3:40799950-40816883 | 17020 | Pola2 | NM_001164057.1 | chr19:5941104-5964206 |
| 16926 | Plk5 | NM_183152.3 | chr10:80356458-80365489 | 17021 | Polb | NM_011130.2 | chr8:22628118-22653437 |
| 16927 | Plp | NM_026385.4 | chr8:94674894-94696242 | 17022 | Pold1 | NM_011131.3 | chr7:44532743-44548815 |
| 16928 | Pln | NM_001141927.1 | chr10:53337685-53345999 | 17023 | Pold2 | NM_008894.2 | chr11:5872179-5878256 |
| 16929 | Plod3 | NM_011122.3 | chr4:147909752-147936776 | 17024 | Pold3 | NM_133692.2 | chr7:100082112-100121500 |
| 16930 | Plod2 | NM_001143016.1 | chr9:92542222-92608427 | 17025 | Pold4 | NM_027196.4 | chr9:4231892-4233634 |
| 16931 | Plod3 | NM_011962.3 | chr5:136987018-136996646 | 17026 | Poldip2 | NM_026389.3 | chr11:78512295-78522736 |
| 16932 | Plp1 | NM_001290561.1 | chrX:136822745-136838582 | 17027 | Poldip3 | NM_178627.3 | chr15:83125977-83149336 |
| 16933 | Plp2 | NM_019755.5 | chrX:7667940-7671390 | 17028 | Pole | NM_011132.2 | chr5:110286318-110337453 |
| 16934 | Plrg1 | NM_016784.3 | chr3:83055537-83072291 | 17029 | Pole2 | NM_011133.2 | chr12:69201778-69228190 |
| 16935 | Pls1 | NM_001033210.3 | chr9:95752641-95845279 | 17030 | Pole3 | NM_021498.2 | chr4:62523800-62525014 |
| 16936 | Pls3 | NM_001164453.1 | chrX:75785653-75875170 | 17031 | Pole4 | NM_025882.3 | chr6:82646711-82652865 |
| 16937 | Plscr1 | NM_011636.2 | chr9:92250193-92272561 | 17032 | Polg | NM_017462.2 | chr7:79449382-79466273 |
| 16938 | Plscr2 | NM_001195084.1 | chr9:92275601-92297752 | 17033 | Polg2 | NM_015810.2 | chr11:106768203-106779537 |
| 16939 | Plscr3 | NM_001168497.1 | chr11:69846371-69852058 | 17034 | Polh | NM_030715.3 | chr17:46171992-46202625 |
| 16940 | Plscr4 | NM_178711.3 | chr9:92457377-92492516 | 17035 | Poli | NM_001136090.2 | chr18:70508679-70530321 |
| 16941 | Plscr5 | NM_001195693.1 | chr9:92192935-92209698 | 17036 | Polk | NM_012048.2 | chr13:96480688-96542485 |
| 16942 | Pltp | NM_011125.2 | chr2:164839517-164857708 | 17037 | Poll | NM_020032.2 | chr19:45552275-45560543 |
| 16943 | Plvap | NM_032398.2 | chr8:71497752-71511769 | 17038 | Polm | NM_017401.2 | chr11:5827859-5838016 |
| 16944 | Plxdc1 | NM_001163608.1 | chr11:97923236-97986446 | 17039 | Poln | NM_001289803.1 | chr5:34007178-34169526 |
| 16945 | Plxdc2 | NM_026162.6 | chr2:16356303-16755839 | 17040 | Polq | NM_001159369.1 | chr16:37011785-37095417 |
| 16946 | Plxna1 | NM_008881.2 | chr6:89316313-89362613 | 17041 | Polr1a | NM_009088.3 | chr6:71909052-71979360 |
| 16947 | Plxna2 | NM_008882.2 | chr1:194619828-194816868 | 17042 | Polr1b | NM_009086.2 | chr2:129100995-129126595 |
| 16948 | Plxna3 | NM_008853.2 | chrX:74329065-74344689 | 17043 | Polr1c | NM_009085.2 | chr17:46243919-46248045 |
| 16949 | Plxna4 | NM_175750.3 | chr6:32144556-32588192 | 17044 | Polr1d | NM_009087.2 | chr5:147077345-147079086 |
| 16950 | Plxna4os1 | NR_040277.1 | chr6:32511140-32515576 | 17045 | Polr1e | NM_001285800.1 | chr4:45018608-45034279 |
| 16951 | Plxnb1 | NM_172775.2 | chr9:109095435-109119915 | 17046 | Polr2a | NM_001291068.3 | chr11:69733998-69758633 |
| 16952 | Plxnb2 | NM_001159521.2 | chr15:89155545-89173951 | 17047 | Polr2b | NM_153798.2 | chr5:77310463-77349328 |
| 16953 | Plxnb3 | NM_019587.2 | chrX:73757102-73772510 | 17048 | Polr2c | NM_009090.5 | chr8:94857449-94864240 |
| 16954 | Plxnc1 | NM_018797.2 | chr10:94790865-94944578 | 17049 | Polr2d | NM_027002.2 | chr18:31789158-31796642 |
| 16955 | Plxnd1 | NM_026376.3 | chr6:115954810-115995005 | 17050 | Polr2e | NM_025554.2 | chr10:80035952-80039659 |
| 16956 | Pm20d1 | NM_178079.3 | chr1:131797394-131818115 | 17051 | Polr2f | NM_027231.2 | chr15:79141366-79151767 |
| 16957 | Pm20d2 | NM_001034867.2 | chr4:33170405-33189737 | 17052 | Polr2g | NM_026329.2 | chr19:8793128-8798557 |
| 16958 | Pmaip1 | NM_021451.2 | chr18:66458603-66465558 | 17053 | Polr2h | NM_145632.2 | chr16:20717825-20722265 |
| 16959 | Pmch | NM_029971.2 | chr10:88091071-88092374 | 17054 | Polr2i | NM_027259.1 | chr7:30232073-30233387 |
| 16960 | Pmel | NM_021882.4 | chr10:128760257-128720238 | 17055 | Polr2j | NM_011293.2 | chr5:136116690-136122947 |
| 16961 | Pmepa1 | NM_022995.3 | chr2:173224464-173276533 | 17056 | Polr2k | NM_001039368.2 | chr15:36174009-36177012 |
| 16962 | Pmf1 | NM_025928.4 | chr3:88394137-88410397 | 17057 | Polr2l | NM_025593.1 | chr7:141471859-141475153 |
| 16963 | Pmfbp1 | NM_019938.3 | chr8:109494026-109542642 | 17058 | Polr2m | NM_001164793.1 | chr9:71478436-71484958 |
| 16964 | Pmis2 | NR_027848.1 | chr7:30670721-30671605 | 17059 | Polr3a | NM_001081247.1 | chr14:24448693-24487046 |
| 16965 | Pml | NM_008884.5 | chr9:58217179-58249786 | 17060 | Polr3b | NM_027423.1 | chr10:84622436-84727178 |
| 16966 | Pmm1 | NM_001282040.1 | chr15:81951105-81960930 | 17061 | Polr3c | NM_028925.1 | chr3:96711894-96727439 |
| 16967 | Pmm2 | NM_016881.2 | chr16:8637706-8657524 | 17062 | Polr3d | NM_001164082.1 | chr14:70438747-70443227 |
| 16968 | Pmp2 | NM_001030305.2 | chr3:10179850-10183885 | 17063 | Polr3e | NM_001164096.1 | chr7:120917743-120947432 |
| 16969 | Pmp22 | NM_008885.3 | chr11:63131456-63159547 | 17064 | Polr3f | NM_029763.3 | chr2:144527744-144541779 |
| 16970 | Pmpca | NM_173180.3 | chr2:26389347-26397121 | 17065 | Polr3g | NM_001081176.1 | chr13:81673836-81711013 |
| 16971 | Pmpcb | NM_028431.2 | chr5:21737159-21757152 | 17066 | Polr3gl | NM_027241.4 | chr3:96577871-96594181 |
| 16972 | Pms1 | NM_153155.3 | chr1:53189188-53297028 | 17067 | Polr3h | NM_030229.4 | chr15:81915029-81926213 |
| 16973 | Pms2 | NM_008886.2 | chr5:143910000-143931756 | 17068 | Polr3k | NM_025901.3 | chr2:181864359-181870826 |
| 16974 | Pmvk | NM_026784.3 | chr3:89459117-89469009 | 17069 | Polrmt | NM_172551.3 | chr10:79736124-79746581 |
| 16975 | Pnck | NM_001199251.1 | chrX:73655991-73695854 | 17070 | Pom121 | NM_148932.2 | chr5:135376139-135394546 |
| 16976 | Pnisr | NM_025669.1 | chr4:21847582-21876475 | 17071 | Pom121l12 | NM_001164166.1 | chr11:14509239-14600316 |
| 16977 | Pnkd | NM_001039509.1 | chr1:74285033-74353692 | 17072 | Pom121l2 | NM_001162928.1 | chr13:21981180-21985903 |
| 16978 | Pnkp | NM_029764.1 | chr7:44857145-44862929 | 17073 | Pomc | NM_001278581.1 | chr12:3954944-3960643 |
| 16979 | Pnldc1 | NM_001034866.1 | chr17:12888901-12910000 | 17074 | Pomgnt1 | NM_001290658.1 | chr4:116151430-116159844 |
| 16980 | Pnlip | NM_026925.3 | chr19:58670364-58681788 | 17075 | Pomgnt2 | NM_001289558.1 | chr9:121981605-121996026 |
| 16981 | Pnliprp1 | NM_018874.2 | chr19:58722886-58744169 | 17076 | Pomk | NM_029037.4 | chr8:25980603-25994121 |
| 16982 | Pnliprp2 | NM_011128.2 | chr19:58759722-58777534 | 17077 | Pomp | NM_025624.2 | chr5:147860627-147875778 |
| 16983 | Pnma1 | NM_027438.3 | chr12:84146130-84148489 | 17078 | Pomt1 | NM_145145.1 | chr2:32236682-32255005 |
| 16984 | Pnma2 | NM_175498.4 | chr14:66911207-66920061 | 17079 | Pomt2 | NM_153415.4 | chr12:87106860-87147902 |
| 16985 | Pnma3 | NM_153169.2 | chrX:73064786-73068191 | 17080 | Pon1 | NM_011134.3 | chr6:5168689-5193946 |
| 16986 | Pnma5 | NM_001100461.3 | chrX:73033980-73037103 | 17081 | Pon2 | NM_183308.2 | chr6:5264623-5298373 |
| 16987 | Pnmal1 | NM_001007569.1 | chr7:16959794-16962320 | 17082 | Pon3 | NM_173006.1 | chr6:5220851-5256233 |
| 16988 | Pnmal2 | NM_001096636.2 | chr7:16944681-16948828 | 17083 | Pop1 | NM_026340.3 | chr15:34495310-34530653 |
| 16989 | Pnmt | NM_008890.1 | chr11:98386631-98388097 | 17084 | Pop4 | NM_025390.4 | chr7:38262819-38271348 |
| 16990 | Pnn | NM_008891.2 | chr12:59066918-59074017 | 17085 | Pop5 | NM_026398.4 | chr5:115235850-115240970 |
| 16991 | Pno1 | NM_025443.2 | chr1:17203199-17211589 | 17086 | Pop7 | NM_028753.2 | chr5:137501438-137502429 |
| 16992 | Pnoc | NM_001205075.1 | chr14:65400672-65425472 | 17087 | Popdc2 | NM_001081984.2 | chr16:38362189-38378216 |
| 16993 | Pnp | NM_013632.4 | chr14:50944302-50953412 | 17088 | Popdc3 | NM_024286.1 | chr10:45289304-45318450 |
| 16994 | Pnp2 | NM_001123371.2 | chr14:50956140-50964749 | 17089 | Por | NM_008898.2 | chr5:135689144-135735326 |
| 16995 | Pnpla1 | NM_001034885.3 | chr17:28858410-28890308 | 17090 | Porcn | NM_016913.4 | chrX:8193845-8206525 |
| 16996 | Pnpla2 | NM_001163689.1 | chr7:141455187-141460743 | 17091 | Postn | NM_001198765.1 | chr3:54361106-54391041 |
| 16997 | Pnpla3 | NM_054088.3 | chr15:84167815-84189521 | 17092 | Pot1a | NM_133931.4 | chr6:25743734-25809226 |

Fig. 26 - 91

| | | | | | | | |
|---|---|---|---|---|---|---|---|
| 17093 | Pot1b | NM_028370.1 | chr17:55652024-55712628 | 17188 | Ppp1r15b | NM_133819.3 | chr1:133131165-133139800 |
| 17094 | Poreg | NM_026256.2 | chr8:27447669-27464112 | 17189 | Ppp1r16a | NM_033371.2 | chr15:76671679-76694915 |
| 17095 | Pou1f1 | NM_008849.4 | chr16:65520628-65533981 | 17190 | Ppp1r16b | NM_001159662.1 | chr2:158667134-158766334 |
| 17096 | Pou2af1 | NM_011136.2 | chr9:51213689-51240079 | 17191 | Ppp1r17 | NM_011153.3 | chr8:56017514-56032688 |
| 17097 | Pou2f1 | NM_011137.3 | chr1:165865153-166002634 | 17192 | Ppp1r18 | NM_001146710.1 | chr17:35866127-35875596 |
| 17098 | Pou2f2 | NM_001163554.1 | chr7:25091114-25132460 | 17193 | Ppp1r1a | NM_021391.3 | chr15:103530278-103537992 |
| 17099 | Pou2f3 | NM_011139.2 | chr9:43123938-43205755 | 17194 | Ppp1r1b | NM_144828.2 | chr11:98348405-98357796 |
| 17100 | Pou3f1 | NM_011141.2 | chr4:124657645-124660655 | 17195 | Ppp1r1c | NM_001290743.1 | chr2:79707779-79818546 |
| 17101 | Pou3f2 | NM_008899.2 | chr4:22482094-22488366 | 17196 | Ppp1r2 | NM_025800.3 | chr16:31275540-31275277 |
| 17102 | Pou3f3 | NM_008900.2 | chr1:42697145-42700209 | 17197 | Ppp1r21 | NM_028658.4 | chr17:88530123-88588367 |
| 17103 | Pou3f3os | NR_027826.1 | chr1:42648199-42694825 | 17198 | Ppp1r26 | NM_001005420.1 | chr2:28447940-28455508 |
| 17104 | Pou3f4 | NM_008901.2 | chrX:110814378-110819108 | 17199 | Ppp1r27 | NM_026814.3 | chr11:120549974-120551132 |
| 17105 | Pou4f1 | NM_011143.4 | chr14:104462324-104467999 | 17200 | Ppp1r2-ps3 | NR_003650.1 | chr19:30538875-30539679 |
| 17106 | Pou4f2 | NM_138944.2 | chr8:78433008-78436652 | 17201 | Ppp1r2-ps7 | NR_033731.1 | chrX:22461595-22463543 |
| 17107 | Pou4f3 | NM_138945.2 | chr18:42394596-42396093 | 17202 | Ppp1r2-ps9 | NR_033171.1 | chrX:15110585-15111489 |
| 17108 | Pou5f1 | NM_001252452.1 | chr17:35508806-35510777 | 17203 | Ppp1r32 | NM_133689.1 | chr19:10474256-10482897 |
| 17109 | Pou5f2 | NM_029315.1 | chr13:78024901-78026296 | 17204 | Ppp1r35 | NM_027242.4 | chr5:137778917-137780107 |
| 17110 | Pou6f1 | NM_010127.3 | chr15:100575317-100586365 | 17205 | Ppp1r36 | NM_001163103.1 | chr12:76417598-76439491 |
| 17111 | Pou6f2 | NM_175006.2 | chr13:18124959-18382039 | 17206 | Ppp1r37 | NM_199149.3 | chr7:19530966-19562398 |
| 17112 | Pp2d1 | NM_173449.3 | chr17:53507459-53539451 | 17207 | Ppp1r3a | NM_080464.2 | chr6:14713821-14755274 |
| 17113 | Ppa1 | NM_026438.4 | chr10:61648620-61674165 | 17208 | Ppp1r3b | NM_177741.3 | chr8:35375740-35388137 |
| 17114 | Ppa2 | NM_146141.2 | chr3:133310109-133378235 | 17209 | Ppp1r3c | NM_016854.2 | chr19:36731730-36736604 |
| 17115 | Ppan | NM_145610.2 | chr9:20888174-20892179 | 17210 | Ppp1r3d | NM_001085501.2 | chr2:178411205-178414463 |
| 17116 | Ppap2a | NM_008247.3 | chr13:112800776-112867894 | 17211 | Ppp1r3e | NM_001167908.1 | chr14:54875596-54877538 |
| 17117 | Ppap2b | NM_080555.3 | chr4:105157346-105232767 | 17212 | Ppp1r3f | NM_001290574.1 | chrX:7558561-7574281 |
| 17118 | Ppap2c | NM_015817.3 | chr10:79526423-79533787 | 17213 | Ppp1r3fos | NR_029473.1 | chrX:7573599-7581016 |
| 17119 | Ppapdc1a | NM_001080963.1 | chr7:129257093-129391307 | 17214 | Ppp1r3g | NM_029628.1 | chr13:35967905-35970388 |
| 17120 | Ppapdc1b | NM_028000.1 | chr8:25720047-25724887 | 17215 | Ppp1r42 | NM_145692.2 | chr1:9968622-10013541 |
| 17121 | Ppapdc2 | NM_028922.3 | chr19:28963919-28966801 | 17216 | Ppp1r7 | NM_023200.2 | chr1:93343644-93367618 |
| 17122 | Ppapdc3 | NM_145521.3 | chr2:32095650-32110820 | 17217 | Ppp1r8 | NM_001290725.1 | chr4:132826923-132843169 |
| 17123 | Ppara | NM_011144.6 | chr15:85735563-85806851 | 17218 | Ppp1r9a | NM_181595.3 | chr6:4903319-5165661 |
| 17124 | Ppard | NM_011145.3 | chr17:28232753-28301469 | 17219 | Ppp1r9b | NM_172261.3 | chr11:94991211-95006898 |
| 17125 | Pparg | NM_001127330.2 | chr6:115360950-115490401 | 17220 | Ppp2ca | NM_019411.4 | chr11:52098823-52122749 |
| 17126 | Ppargc1a | NM_008904.2 | chr5:51454248-51553921 | 17221 | Ppp2cb | NM_017374.3 | chr8:33599620-33619804 |
| 17127 | Ppargc1b | NM_133249.2 | chr18:61298135-61400431 | 17222 | Ppp2r1a | NM_016891.3 | chr17:20945453-20965905 |
| 17128 | Ppar | NM_172146.2 | chr5:76913248-76951578 | 17223 | Ppp2r1b | NM_001034085.2 | chr9:50856923-50894229 |
| 17129 | Ppbp | NM_023785.2 | chr5:90768517-90770060 | 17224 | Ppp2r2a | NM_001205188.1 | chr14:67014655-67072471 |
| 17130 | Ppcdc | NM_176831.4 | chr9:57412659-57440114 | 17225 | Ppp2r2b | NM_028392.3 | chr18:42645220-43059471 |
| 17131 | Ppcs | NM_026494.3 | chr4:119418532-119422420 | 17226 | Ppp2r2c | NM_172994.2 | chr5:36868569-36955078 |
| 17132 | Pndpf | NM_025598.2 | chr2:181187342-181188504 | 17227 | Ppp2r2cos | NR_045505.1 | chr5:36873594-36876879 |
| 17133 | Ppef1 | NM_011147.1 | chrX:160623093-160719972 | 17228 | Ppp2r2d | NM_026391.2 | chr7:138846385-138883056 |
| 17134 | Ppef2 | NM_011148.3 | chr5:92226973-92253195 | 17229 | Ppp2r3a | NM_001161362.3 | chr9:101104988-101251832 |
| 17135 | Ppfia1 | NM_001033319.2 | chr7:144476754-144553729 | 17230 | Ppp2r3c | NM_021529.3 | chr12:55280813-55303000 |
| 17136 | Ppfia2 | NM_001205341.1 | chr10:106470309-106933468 | 17231 | Ppp2r3d | NM_001163415.1 | chr9:124474345-124476862 |
| 17137 | Ppfia3 | NM_029741.2 | chr7:45339125-45367019 | 17232 | Ppp2r4 | NM_138748.5 | chr2:30416049-30447807 |
| 17138 | Ppfia4 | NM_001144855.1 | chr1:134296782-134332928 | 17233 | Ppp2r5a | NM_144880.4 | chr1:191351980-191397041 |
| 17139 | Ppfibp1 | NM_001170433.1 | chr6:146888493-147032023 | 17234 | Ppp2r5b | NM_198168.3 | chr19:6227766-6235840 |
| 17140 | Ppfibp2 | NM_001061515.1 | chr7:107606843-107748583 | 17235 | Ppp2r5c | NM_001081457.2 | chr12:110485738-110583074 |
| 17141 | Pphln1 | NM_001083114.1 | chr15:93398349-93491912 | 17236 | Ppp2r5d | NM_009358.3 | chr17:46682990-46705002 |
| 17142 | Ppia | NM_008907.1 | chr11:6415869-6419810 | 17237 | Ppp2r5e | NM_012024.2 | chr12:75450880-75596200 |
| 17143 | Ppib | NM_011149.2 | chr9:66060168-66086629 | 17238 | Ppp3ca | NM_008913.5 | chr3:136670065-136937727 |
| 17144 | Ppic | NM_008908.4 | chr18:53406340-53418007 | 17239 | Ppp3cb | NM_008914.3 | chr14:20499363-20546573 |
| 17145 | Ppid | NM_026352.3 | chr3:79591388-79603650 | 17240 | Ppp3cc | NM_008915.3 | chr14:70217864-70289497 |
| 17146 | Ppie | NM_019489.5 | chr4:123127124-123139941 | 17241 | Ppp3r1 | NM_024459.2 | chr11:17159297-17200380 |
| 17147 | Ppif | NM_134084.1 | chr14:25694169-25700466 | 17242 | Ppp3r2 | NM_001004025.4 | chr4:49678746-49681983 |
| 17148 | Ppifos | NR_028021.1 | chr14:25696355-25701282 | 17243 | Ppp4c | NM_019674.3 | chr7:126785867-126792471 |
| 17149 | Ppig | NM_001081086.1 | chr2:69723087-69754059 | 17244 | Ppp4r1 | NM_001114131.1 | chr17:65783354-65841926 |
| 17150 | Ppih | NM_001110129.1 | chr4:119306289-119320523 | 17245 | Ppp4r1l-ps | NR_027957.1 | chr2:173579319-173659539 |
| 17151 | Ppil1 | NM_026845.4 | chr17:29250834-29263971 | 17246 | Ppp4r2 | NM_182939.4 | chr6:100833637-100863717 |
| 17152 | Ppil2 | NM_001252444.1 | chr16:17086655-17111252 | 17247 | Ppp4r4 | NM_028980.2 | chr12:103532564-103613832 |
| 17153 | Ppil3 | NM_001285826.1 | chr1:58430992-58445486 | 17248 | Ppp5c | NM_011155.2 | chr7:17004640-17027914 |
| 17154 | Ppil4 | NM_026141.3 | chr10:7792893-7822563 | 17249 | Ppp6c | NM_024209.2 | chr2:39196797-39226338 |
| 17155 | Ppil6 | NM_028430.1 | chr10:41490438-41514288 | 17250 | Ppp6r1 | NM_172894.2 | chr7:4631494-4658950 |
| 17156 | PpipSk1 | NM_178795.4 | chr2:121310560-121351013 | 17251 | Ppp6r2 | NM_026813.1 | chr15:89211568-89286261 |
| 17157 | PpipSk2 | NM_172760.5 | chr1:97706042-97770092 | 17252 | Ppp6r3 | NM_001164159.1 | chr19:3454928-3575749 |
| 17158 | Ppl | NM_008909.2 | chr16:5086290-5132481 | 17253 | Pprc1 | NM_001081214.1 | chr19:46056538-46072909 |
| 17159 | Ppm1a | NM_008910.3 | chr12:72761210-72794940 | 17254 | Ppt1 | NM_008917.3 | chr4:122836226-122859175 |
| 17160 | Ppm1b | NM_011159496.1 | chr7:84958000-85014776 | 17255 | Ppt2 | NM_019441.5 | chr17:34616661-34627148 |
| 17161 | Ppm1d | NM_016910.3 | chr11:85311253-85347071 | 17256 | Pptc7 | NM_177242.4 | chr5:122884397-122924281 |
| 17162 | Ppm1e | NM_177167.4 | chr11:87226905-87358994 | 17257 | Ppwd1 | NM_172807.4 | chr13:104205121-104228844 |
| 17163 | Ppm1f | NM_176833.4 | chr16:16896468-16927375 | 17258 | Ppy | NM_008918.1 | chr11:102099930-102101300 |
| 17164 | Ppm1g | NM_008014.3 | chr5:31202667-31220545 | 17259 | Pqbp1 | NM_001252528.1 | chrX:7894518-7899000 |
| 17165 | Ppm1h | NM_001010218.1 | chr10:122678761-122945793 | 17260 | Pqlc1 | NM_001164420.1 | chr18:80255244-80292724 |
| 17166 | Ppm1j | NM_027982.2 | chr3:104781055-104786037 | 17261 | Pqlc2 | NM_145384.2 | chr4:139298004-139330700 |
| 17167 | Ppm1k | NM_175523.4 | chr6:57506501-57535426 | 17262 | Pqlc3 | NM_001161111.3 | chr12:16992960-17000118 |
| 17168 | Ppm1l | NM_178726.3 | chr3:69316917-69555396 | 17263 | Pradc1 | NM_001163427.1 | chr6:85446754-85451302 |
| 17169 | Ppm1m | NM_026447.4 | chr9:106194952-106199233 | 17264 | Praf2 | NM_138602.4 | chrX:7728570-7731063 |
| 17170 | Ppm1n | NM_177691.3 | chr7:19276806-19280049 | 17265 | Pram1 | NM_001002842.2 | chr17:33638055-33645706 |
| 17171 | Ppme1 | NM_028292.2 | chr7:106308736-100371896 | 17266 | Prame | NM_029459.2 | chrX:135613001-135627705 |
| 17172 | Ppox | NM_008911.2 | chr1:171276991-171281186 | 17267 | Pramef12 | NM_029948.2 | chr4:143391673-144408464 |
| 17173 | Ppp1ca | NM_031868.2 | chr19:4192173-4195419 | 17268 | Pramef17 | NM_001085540.2 | chr4:143991126-143994369 |
| 17174 | Ppp1cb | NM_172797.3 | chr5:32458969-32493712 | 17269 | Pramef25 | NM_001126315.2 | chr4:143948182-143951016 |
| 17175 | Ppp1cc | NM_013636.3 | chr5:122158278-122175269 | 17270 | Pramef6 | NM_001085414.2 | chr4:143894236-143900380 |
| 17176 | Ppp1r10 | NM_001163818.1 | chr17:35917195-35932283 | 17271 | Pramef8 | NM_172877.2 | chr4:143412425-143421087 |
| 17177 | Ppp1r11 | NM_029632.3 | chr17:36948354-36951792 | 17272 | Pramel1 | NM_031377.2 | chr4:143394440-143399819 |
| 17178 | Ppp1r12a | NM_027892.2 | chr10:108162399-108277575 | 17273 | Pramel3 | NM_031390.2 | chr4:135302315-135312636 |
| 17179 | Ppp1r12b | NM_001081307.1 | chr1:134765942-134955940 | 17274 | Pramel4 | NM_001001319.3 | chr4:144059125-144069318 |
| 17180 | Ppp1r12c | NM_029834.3 | chr7:4481520-4501680 | 17275 | Pramel5 | NM_001085418.2 | chr4:144270632-144280466 |
| 17181 | Ppp1r13b | NM_011625.1 | chr12:111828457-111908055 | 17276 | Pramel6 | NM_178249.2 | chr2:87508457-87510865 |
| 17182 | Ppp1r13l | NM_001010836.3 | chr7:19361215-19378533 | 17277 | Pramel7 | NM_178250.2 | chr2:87489087-87492418 |
| 17183 | Ppp1r14a | NM_026731.3 | chr7:29289319-29293390 | 17278 | Prap1 | NM_009475.2 | chr7:140093395-140097203 |
| 17184 | Ppp1r14b | NM_008889.2 | chr19:6975047-6977324 | 17279 | Prb1 | NM_198669.1 | chr6:132206794-132210521 |
| 17185 | Ppp1r14c | NM_133485.4 | chr10:3366149-3464975 | 17280 | Prc1 | NM_001285997.1 | chr7:80294450-80316259 |
| 17186 | Ppp1r14d | NM_001290796.1 | chr2:119218118-119229865 | 17281 | Prcc | NM_033573.2 | chr3:87858902-87885562 |
| 17187 | Ppp1r15a | NM_008654.2 | chr7:45522916-45526268 | 17282 | Prcp | NM_028243.3 | chr7:92875252-92934581 |

Fig. 26 - 92

| | | | |
|---|---|---|---|
| 17283 | Prdm1 | NM_007548.4 | chr10:44437173-44458748 |
| 17284 | Prdm10 | NM_001080817.1 | chr9:31315106-31378543 |
| 17285 | Prdm11 | NM_001177536.1 | chr2:92974905-93046144 |
| 17286 | Prdm12 | NM_001123362.1 | chr2:31640036-31655795 |
| 17287 | Prdm13 | NM_001080771.1 | chr4:21677479-21685963 |
| 17288 | Prdm14 | NM_001081209.2 | chr1:13113427-13127163 |
| 17289 | Prdm15 | NM_144789.2 | chr16:97791466-97851227 |
| 17290 | Prdm16 | NM_001177995.1 | chr4:154316124-154636873 |
| 17291 | Prdm2 | NM_001081355.3 | chr4:143107390-143212709 |
| 17292 | Prdm4 | NM_181650.3 | chr10:85891967-85916729 |
| 17293 | Prdm5 | NM_027547.2 | chr6:65778961-65936377 |
| 17294 | Prdm6 | NM_001033281.3 | chr18:53464545-53575857 |
| 17295 | Prdm8 | NM_029947.2 | chr5:98180868-98187448 |
| 17296 | Prdm9 | NM_144809.2 | chr17:15543078-15563323 |
| 17297 | Prdx1 | NM_011034.4 | chr4:116685598-116700000 |
| 17298 | Prdx2 | NM_011563.5 | chr8:84969647-84974313 |
| 17299 | Prdx3 | NM_007452.2 | chr19:60864065-60874538 |
| 17300 | Prdx4 | NM_016764.5 | chrX:155323917-155338460 |
| 17301 | Prdx5 | NM_012021.2 | chr19:6906818-6909645 |
| 17302 | Prdx6 | NM_007453.4 | chr1:161240111-161251210 |
| 17303 | Prdx6b | NM_177256.5 | chr2:80292469-80295358 |
| 17304 | Preb | NM_016703.3 | chr5:30951666-30960327 |
| 17305 | Prelid1 | NM_025596.5 | chr13:55322054-55325272 |
| 17306 | Prelid2 | NM_029942.1 | chr18:41875695-41951194 |
| 17307 | Prelp | NM_054077.4 | chr1:133910303-133921401 |
| 17308 | Prep | NM_011156.2 | chr10:45067213-45158995 |
| 17309 | Prepl | NM_001163622.1 | chr17:85063476-85090267 |
| 17310 | Prex1 | NM_177782.3 | chr2:166566344-166713832 |
| 17311 | Prex2 | NM_001033636.4 | chr1:11263962-11303682 |
| 17312 | Prf1 | NM_011073.3 | chr10:61297835-61304263 |
| 17313 | Prg2 | NM_008920.4 | chr2:84980460-84983632 |
| 17314 | Prg3 | NM_016914.2 | chr2:84988214-84993886 |
| 17315 | Prg4 | NM_001110146.1 | chr1:150449411-150466165 |
| 17316 | Prh1 | NM_011174.2 | chr6:132569841-132572401 |
| 17317 | Prickle1 | NM_001033217.4 | chr15:93499113-93595891 |
| 17318 | Prickle2 | NM_001081146.2 | chr6:92370891-92706184 |
| 17319 | Prickle3 | NM_001290624.1 | chrX:7657378-7668186 |
| 17320 | Prickle4 | NM_001290337.1 | chr17:47688473-47694736 |
| 17321 | Prim1 | NM_008921.2 | chr10:128105214-128030030 |
| 17322 | Prim2 | NM_008922.2 | chr1:33453807-33669794 |
| 17323 | Prima1 | NM_133364.2 | chr12:103196907-103242146 |
| 17324 | Primpol | NM_001001184.1 | chr8:46575593-46617200 |
| 17325 | Prkaa1 | NM_001013367.3 | chr15:5143860-5181899 |
| 17326 | Prkaa2 | NM_178143.2 | chr4:105029649-105109898 |
| 17327 | Prkab1 | NM_031869.2 | chr5:116013589-116024428 |
| 17328 | Prkab2 | NM_182997.2 | chr3:97658211-97673067 |
| 17329 | Prkaca | NM_001277898.1 | chr8:83976882-83996442 |
| 17330 | Prkacb | NM_001164198.1 | chr3:146729578-146770238 |
| 17331 | Prkag1 | NM_016781.2 | chr15:98812796-98831508 |
| 17332 | Prkag2 | NM_001170555.1 | chr5:24862734-24908509 |
| 17333 | Prkag2os1 | NR_040684.1 | chr5:24902568-24906849 |
| 17334 | Prkag3 | NM_153744.3 | chr1:74738921-74748955 |
| 17335 | Prkar1a | NM_021880.3 | chr11:109650920-109669663 |
| 17336 | Prkar1b | NM_001253890.1 | chr5:139017303-139130386 |
| 17337 | Prkar2a | NM_008924.2 | chr9:108692142-108749511 |
| 17338 | Prkar2b | NM_011160.3 | chr12:31958478-32061279 |
| 17339 | Prkca | NM_011101.3 | chr11:107933386-108343888 |
| 17340 | Prkcb | NM_008855.2 | chr7:122289124-122634401 |
| 17341 | Prkcd | NM_011103.3 | chr14:30595353-30626208 |
| 17342 | Prkcdbp | NM_028444.1 | chr7:105480615-105482197 |
| 17343 | Prkce | NM_011104.3 | chr17:86167784-86657919 |
| 17344 | Prkcg | NM_001291434.1 | chr7:3303531-3331097 |
| 17345 | Prkch | NM_008856.4 | chr12:73584795-73778184 |
| 17346 | Prkci | NM_008857.3 | chr3:30995770-31052740 |
| 17347 | Prkcq | NM_008438.2 | chr2:11172381-11301226 |
| 17348 | Prkcsh | NM_008925.2 | chr9:22002987-22014245 |
| 17349 | Prkcz | NM_001039079.2 | chr4:155260117-155345789 |
| 17350 | Prkd1 | NM_008423.1 | chr12:50341231-50649223 |
| 17351 | Prkd2 | NM_001252458.1 | chr7:16842901-16870461 |
| 17352 | Prkd3 | NM_001171004.1 | chr17:78949404-79020816 |
| 17353 | Prkdc | NM_011159.2 | chr16:15637865-15842239 |
| 17354 | Prkg1 | NM_001013833.3 | chr19:30564486-31765033 |
| 17355 | Prkg2 | NM_008410.1 | chr5:98929772-99037079 |
| 17356 | Prkra | NM_011871.2 | chr2:76629936-76647994 |
| 17357 | Prkrip1 | NM_025774.3 | chr5:136180856-136198954 |
| 17358 | Prkrir | NM_028410.1 | chr7:98703362-98718061 |
| 17359 | Prkx | NM_016979.1 | chrX:77762029-77795960 |
| 17360 | Prl | NM_001163530.1 | chr13:27057569-27065203 |
| 17361 | Prl2a1 | NM_019191.3 | chr13:27801654-27808716 |
| 17362 | Prl2b1 | NM_025532.3 | chr13:27383344-27390846 |
| 17363 | Prl2c1 | NM_001045532.2 | chr13:27849341-27857708 |
| 17364 | Prl2c2 | NM_031191.1 | chr13:12996123-13005330 |
| 17365 | Prl2c3 | NM_011118.2 | chr13:12790820-12800079 |
| 17366 | Prl2c4 | NM_011954.2 | chr13:12790817-12800058 |
| 17367 | Prl2c5 | NM_181852.2 | chr13:13182715-13191925 |
| 17368 | Prl3a1 | NM_025896.2 | chr13:27259488-27276660 |
| 17369 | Prl3b1 | NM_008865.3 | chr13:27242429-27249740 |
| 17370 | Prl3c1 | NM_001163218.1 | chr13:27198902-27203750 |
| 17371 | Prl3d1 | NM_001205322.1 | chr13:27094188-27100260 |
| 17372 | Prl3d2 | NM_172155.1 | chr13:27121703-27127482 |
| 17373 | Prl3d3 | NM_172156.2 | chr13:27156798-27162520 |
| 17374 | Prl4a1 | NM_011165.3 | chr13:28016222-28023546 |
| 17375 | Prl5a1 | NM_023746.4 | chr13:28142483-28151595 |
| 17376 | Prl6a1 | NM_011166.2 | chr13:27312626-27319252 |
| 17377 | Prl7a1 | NM_001164058.1 | chr13:27633363-27642493 |
| 17378 | Prl7a2 | NM_011168.4 | chr13:27658583-27668036 |
| 17379 | Prl7b1 | NM_029355.2 | chr13:27601818-27610582 |
| 17380 | Prl7c1 | NM_026206.2 | chr13:27773494-27780804 |
| 17381 | Prl7d1 | NM_011120.2 | chr13:27708997-27716737 |
| 17382 | Prl8a1 | NM_028477.2 | chr13:27573921-27582171 |
| 17383 | Prl8a2 | NM_001289919.1 | chr13:27345672-27354215 |
| 17384 | Prl8a6 | NM_001271378.1 | chr13:27432680-27438688 |
| 17385 | Prl8a8 | NM_023741.2 | chr13:27507071-27513213 |
| 17386 | Prl8a9 | NM_023332.4 | chr13:27558000-27564604 |
| 17387 | Prlh | NM_001101647.1 | chr1:90953107-90954012 |
| 17388 | Prlhr | NM_201615.2 | chr19:60466732-60468304 |
| 17389 | Prlr | NM_001253781.1 | chr15:10223905-10349180 |
| 17390 | Prm1 | NM_013637.4 | chr16:10796331-10796823 |
| 17391 | Prm2 | NM_008933.2 | chr16:10791376-10792105 |
| 17392 | Prm3 | NM_013638.2 | chr16:10790507-10790914 |
| 17393 | Prmt1 | NM_001252476.1 | chr7:44976754-44986420 |
| 17394 | Prmt10 | NM_001081240.3 | chr8:77549396-77581338 |
| 17395 | Prmt2 | NM_001077638.2 | chr10:76207225-76237865 |
| 17396 | Prmt3 | NM_133740.2 | chr7:49778357-49858265 |
| 17397 | Prmt5 | NM_013768.3 | chr14:54507181-54517470 |
| 17398 | Prmt6 | NM_178891.5 | chr3:110248524-110250999 |
| 17399 | Prmt7 | NM_145404.1 | chr8:106211053-106251694 |
| 17400 | Prmt8 | NM_201371.2 | chr6:127689008-127769159 |
| 17401 | Prn | NM_001278258.1 | chr2:131909927-131956131 |
| 17402 | Prnd | NM_001126338.2 | chr2:131950860-131956131 |
| 17403 | Prnp | NM_001278256.1 | chr2:131909927-131938436 |
| 17404 | Prob1 | NM_001270646.1 | chr18:35650350-35655199 |
| 17405 | Proc | NM_001042767.3 | chr18:32123125-32139570 |
| 17406 | Procal | NM_001045516.2 | chr11:78193391-78205763 |
| 17407 | Procr | NM_011171.2 | chr2:155751216-155755478 |
| 17408 | Prodh | NM_011172.2 | chr16:18071725-18089190 |
| 17409 | Prodh2 | NM_019546.5 | chr7:30493657-30513402 |
| 17410 | Prok1 | NM_001044382.1 | chr3:107235530-107239707 |
| 17411 | Prok2 | NM_001037539.2 | chr6:99711298-99726392 |
| 17412 | Prokr1 | NM_021381.3 | chr6:87578591-87590701 |
| 17413 | Prokr2 | NM_144944.3 | chr2:132370328-132385447 |
| 17414 | Prol1 | NM_008644.2 | chr5:88317311-88328817 |
| 17415 | Prom1 | NM_001163577.1 | chr5:43993621-44101736 |
| 17416 | Prom2 | NM_138750.2 | chr2:127528952-127541417 |
| 17417 | Prop1 | NM_008936.1 | chr11:50950805-50953632 |
| 17418 | Prorsd1 | NM_001163454.2 | chr11:29511756-29515033 |
| 17419 | Pros1 | NM_011173.3 | chr16:62854306-62929342 |
| 17420 | Prosc | NM_001039077.2 | chr8:27042554-27050241 |
| 17421 | Proser1 | NM_173382.1 | chr3:53463816-53481755 |
| 17422 | Proser2 | NM_001159657.1 | chr2:6098499-6130185 |
| 17423 | Prox1 | NM_008937.2 | chr1:190121776-190170680 |
| 17424 | Prox2 | NM_175198.4 | chr12:85086813-85106431 |
| 17425 | Proz | NM_025834.3 | chr8:13060907-13075006 |
| 17426 | Prp2 | NM_031499.2 | chr6:132595945-132600702 |
| 17427 | Prpf18 | NM_026045.3 | chr2:4622166-4652086 |
| 17428 | Prpf19 | NM_001253843.1 | chr19:10895230-10909559 |
| 17429 | Prpf3 | NM_027541.4 | chr3:95830621-95855753 |
| 17430 | Prpf31 | NM_001159714.1 | chr7:3629984-3642484 |
| 17431 | Prpf38a | NM_172697.3 | chr4:108564866-108579336 |
| 17432 | Prpf38b | NM_025845.2 | chr3:108902806-108911704 |
| 17433 | Prpf39 | NM_177806.3 | chr12:65036333-65063386 |
| 17434 | Prpf4 | NM_027297.3 | chr4:62408782-62426990 |
| 17435 | Prpf40a | NM_018785.2 | chr2:53138475-53191187 |
| 17436 | Prpf40b | NM_018786.2 | chr15:99295408-99317007 |
| 17437 | Prpf4b | NM_013830.2 | chr13:34875493-34902878 |
| 17438 | Prpf6 | NM_133701.2 | chr2:181601318-181655661 |
| 17439 | Prpf8 | NM_138659.2 | chr11:75486776-75509447 |
| 17440 | Prph | NM_001163588.1 | chr15:99055173-99058978 |
| 17441 | Prph2 | NM_008938.1 | chr17:46910484-46924926 |
| 17442 | Prpmp5 | NM_001024705.2 | chr6:132311589-132314743 |
| 17443 | Prps1 | NM_021463.4 | chrX:140456602-140476140 |
| 17444 | Prps1l1 | NM_029294.2 | chr12:34984760-34986436 |
| 17445 | Prps1l3 | NM_001037746.3 | chr12:57230411-57242168 |
| 17446 | Prps2 | NM_026662.5 | chrX:167346319-167382749 |
| 17447 | Prpsap1 | NM_026364.1 | chr11:116470815-116490346 |
| 17448 | Prpsap2 | NM_001164242.1 | chr11:61729649-61762088 |
| 17449 | Prr11 | NM_175563.5 | chr11:87089155-87108714 |
| 17450 | Prr12 | NM_175022.2 | chr7:45027706-45052881 |
| 17451 | Prr13 | NM_001170911.1 | chr15:102459169-102462806 |
| 17452 | Prr14 | NM_145589.2 | chr7:127471613-127474758 |
| 17453 | Prr14l | NM_194340.2 | chr5:32789266-32854230 |
| 17454 | Prr15 | NM_030024.2 | chr6:54327011-54330200 |
| 17455 | Prr15l | NM_146026.1 | chr11:96929323-96935647 |
| 17456 | Prr16 | NM_001081224.2 | chr18:51117897-51304641 |
| 17457 | Prr18 | NM_178774.4 | chr17:8340738-8344113 |
| 17458 | Prr19 | NM_001081294.1 | chr7:25301358-25304133 |
| 17459 | Prr22 | NM_001195673.1 | chr17:56770275-56772134 |
| 17460 | Prr23a | NM_001134660.1 | chr9:98842586-98843645 |
| 17461 | Prr24 | NM_001136270.1 | chr7:16272012-16273692 |
| 17462 | Prr27 | NM_001163551.1 | chr5:87825696-87846386 |
| 17463 | Prr3 | NM_001165892.3 | chr17:35977755-35979467 |
| 17464 | Prr30 | NM_029680.1 | chr14:101197689-101200069 |
| 17465 | Prr32 | NM_026841.1 | chrX:45090903-45092790 |
| 17466 | Prr33 | NR_033261.1 | chr7:142491079-142506771 |
| 17467 | Prr5 | NM_146061.4 | chr15:84680997-84703673 |
| 17468 | Prr5l | NM_001083810.2 | chr2:101714284-101797707 |
| 17469 | Prr7 | NM_001030296.4 | chr13:55464266-55473155 |
| 17470 | Prr9 | NM_175424.3 | chr3:92122203-92123947 |
| 17471 | Prrc1 | NM_028447.3 | chr18:57354732-57392719 |
| 17472 | Prrc2a | NM_001199044.1 | chr17:35149085-35164877 |

Fig. 26 - 93

| | | | |
|---|---|---|---|
| 17473 | Prrc2b | NM_001159634.1 | chr2:32151147-32234537 |
| 17474 | Prrc2c | NM_001081290.1 | chr1:162671784-162740556 |
| 17475 | Prrg1 | NM_001164275.2 | chrX:78449609-78583805 |
| 17476 | Prrg2 | NM_022999.1 | chr7:45053606-45061652 |
| 17477 | Prrg3 | NM_001081135.2 | chrX:71962981-71972722 |
| 17478 | Prrg4 | NM_178695.5 | chr2:104830740-104849850 |
| 17479 | Prrt1 | NM_030890.1 | chr17:34629685-34632260 |
| 17480 | Prrt2 | NM_001102563.1 | chr7:127017541-127021211 |
| 17481 | Prrt3 | NM_001289699.1 | chr6:113493638-113501931 |
| 17482 | Prrt4 | NM_001101443.1 | chr6:29169229-29179584 |
| 17483 | Prrx1 | NM_001025570.1 | chr1:163255276-163313650 |
| 17484 | Prrx2 | NM_009116.2 | chr2:30845366-30881247 |
| 17485 | Prrxl1 | NM_001001796.4 | chr14:32599926-32649246 |
| 17486 | Prss1 | NM_053243.2 | chr6:41458929-41463786 |
| 17487 | Prss12 | NM_008939.2 | chr3:123446912-123506602 |
| 17488 | Prss16 | NM_019429.2 | chr13:22002175-22009741 |
| 17489 | Prss2 | NM_009430.2 | chr6:41521775-41525079 |
| 17490 | Prss21 | NM_020487.4 | chr17:23868071-23873113 |
| 17491 | Prss22 | NM_133731.2 | chr17:23993533-23998100 |
| 17492 | Prss23 | NM_029614.3 | chr7:89507784-89517586 |
| 17493 | Prss27 | NM_175440.4 | chr17:24038242-24045949 |
| 17494 | Prss28 | NM_053259.2 | chr17:25308645-25311876 |
| 17495 | Prss29 | NM_053260.3 | chr17:25318653-25322684 |
| 17496 | Prss3 | NM_011645.2 | chr6:41373758-41377613 |
| 17497 | Prss30 | NM_013921.3 | chr17:23972126-23975230 |
| 17498 | Prss32 | NM_027220.2 | chr17:23853771-23859776 |
| 17499 | Prss33 | NM_001081399.2 | chr17:23833360-23835767 |
| 17500 | Prss34 | NM_178372.2 | chr17:25298393-25300161 |
| 17501 | Prss35 | NM_178738.3 | chr9:86743632-86757506 |
| 17502 | Prss36 | NM_001081374.1 | chr7:127932637-127946725 |
| 17503 | Prss37 | NM_026317.2 | chr6:40514823-40519508 |
| 17504 | Prss38 | NM_001045521.1 | chr11:59372668-59375653 |
| 17505 | Prss39 | NM_009355.2 | chr1:34498429-34503062 |
| 17506 | Prss40 | NM_009356.2 | chr1:34552330-34560943 |
| 17507 | Prss41 | NM_027644.1 | chr17:23836784-23844156 |
| 17508 | Prss42 | NM_153099.3 | chr9:110798184-110803744 |
| 17509 | Prss43 | NM_199471.1 | chr9:110826689-110831504 |
| 17510 | Prss44 | NM_148940.3 | chr9:110813993-110817999 |
| 17511 | Prss45 | NM_153172.1 | chr9:110834587-110841310 |
| 17512 | Prss46 | NM_183103.2 | chr9:110844505-110856522 |
| 17513 | Prss48 | NM_001016150.1 | chr3:85993809-86002491 |
| 17514 | Prss50 | NM_146227.4 | chr9:110857966-110864628 |
| 17515 | Prss51 | NM_001193631.1 | chr14:64093695-64097672 |
| 17516 | Prss52 | NM_028525.2 | chr14:64104322-64113751 |
| 17517 | Prss53 | NM_001081268.1 | chr7:127885443-127890970 |
| 17518 | Prss54 | NM_027640.1 | chr8:95559291-95575197 |
| 17519 | Prss55 | NM_001081063.1 | chr14:64075442-64085389 |
| 17520 | Prss56 | NM_027084.2 | chr1:87183313-87188405 |
| 17521 | Prss57 | NM_001042710.1 | chr10:79781473-79788985 |
| 17522 | Prss58 | NM_175020.3 | chr6:40895261-40900387 |
| 17523 | Prss8 | NM_133351.3 | chr7:127925716-127930113 |
| 17524 | Prtg | NM_175485.4 | chr9:72807273-72917307 |
| 17525 | Prtn3 | NM_011178.2 | chr10:79879666-79883172 |
| 17526 | Prune | NM_173347.2 | chr3:95253673-95282076 |
| 17527 | Prune2 | NM_181348.4 | chr9:16956117-17223932 |
| 17528 | Prx | NM_019412.2 | chr7:27499323-27520041 |
| 17529 | Psap | NM_001146120.1 | chr10:60277627-60302600 |
| 17530 | Psapl1 | NM_175249.3 | chr5:36204020-36206567 |
| 17531 | Psat1 | NM_001205339.1 | chr10:39505122-39524622 |
| 17532 | Psca | NM_028216.2 | chr15:74714838-74717065 |
| 17533 | Psd | NM_028627.2 | chr19:46312086-46327156 |
| 17534 | Psd2 | NM_001289600.1 | chr18:35964829-36014716 |
| 17535 | Psd3 | NM_027626.1 | chr8:67689081-67818295 |
| 17536 | Psd4 | NM_177611.3 | chr2:24385396-24408729 |
| 17537 | Psen1 | NM_008943.2 | chr12:83688562-83735199 |
| 17538 | Psen2 | NM_001128605.1 | chr1:180227003-180256300 |
| 17539 | Psenen | NM_025498.2 | chr7:30561865-30563184 |
| 17540 | Psg16 | NM_007676.4 | chr7:17074039-17098971 |
| 17541 | Psg17 | NM_007677.2 | chr7:18813936-18821591 |
| 17542 | Psg18 | NM_001163685.1 | chr7:18348201-18354993 |
| 17543 | Psg19 | NM_011964.2 | chr7:18789124-18798510 |
| 17544 | Psg20 | NM_054058.1 | chr7:18674365-18685992 |
| 17545 | Psg21 | NM_027403.4 | chr7:18646653-18656725 |
| 17546 | Psg22 | NM_001004152.2 | chr7:18718089-18727248 |
| 17547 | Psg23 | NM_020261.4 | chr7:18606342-18616501 |
| 17548 | Psg25 | NM_054060.1 | chr7:18519701-18532227 |
| 17549 | Psg26 | NM_001029893.1 | chr7:18474581-18484149 |
| 17550 | Psg27 | NM_001037168.1 | chr7:18556513-18567305 |
| 17551 | Psg28 | NM_054063.4 | chr7:18422535-18432055 |
| 17552 | Psg29 | NM_054064.3 | chr7:17203476-17215756 |
| 17553 | Psg-ps1 | NR_002857.1 | chr7:17672312-17682060 |
| 17554 | Psip1 | NM_001290527.1 | chr4:83461878-83486448 |
| 17555 | Pskh1 | NM_173432.2 | chr8:105900473-105931802 |
| 17556 | Psma1 | NM_011965.2 | chr7:114264549-114276116 |
| 17557 | Psma2 | NM_008944.2 | chr13:14613241-14625673 |
| 17558 | Psma3 | NM_011184.5 | chr12:70974622-70995877 |
| 17559 | Psma4 | NM_011966.3 | chr9:54950858-54958030 |
| 17560 | Psma5 | NM_011967.3 | chr3:108256925-108279952 |
| 17561 | Psma6 | NM_011968.3 | chr12:55398824-55418459 |
| 17562 | Psma7 | NM_001289476.1 | chr2:180036386-180042464 |
| 17563 | Psma8 | NM_001163609.1 | chr18:14706150-14762299 |
| 17564 | Psmb1 | NM_011185.3 | chr17:15475720-15498276 |
| 17565 | Psmb10 | NM_013640.3 | chr8:105935727-105938392 |
| 17566 | Psmb11 | NM_175204.4 | chr14:54625309-54629556 |
| 17567 | Psmb2 | NM_011970.4 | chr4:126677642-126709715 |
| 17568 | Psmb3 | NM_011971.4 | chr11:97703433-97713500 |
| 17569 | Psmb4 | NM_008945.3 | chr3:94884323-94886958 |
| 17570 | Psmb5 | NM_011186.1 | chr14:54614119-54617995 |
| 17571 | Psmb6 | NM_008946.4 | chr11:70525356-70527858 |
| 17572 | Psmb7 | NM_011187.1 | chr2:38588045-38643906 |
| 17573 | Psmb8 | NM_010724.2 | chr17:34198194-34201454 |
| 17574 | Psmb9 | NM_013585.2 | chr17:34182098-34187330 |
| 17575 | Psmc1 | NM_008947.3 | chr12:100112330-100123364 |
| 17576 | Psmc2 | NM_011188.3 | chr5:21785282-21803784 |
| 17577 | Psmc3 | NM_008948.2 | chr2:91054015-91059438 |
| 17578 | Psmc3ip | NM_008949.3 | chr11:101092140-101095435 |
| 17579 | Psmc4 | NM_011874.2 | chr7:28041701-28050092 |
| 17580 | Psmc5 | NM_008950.1 | chr11:106256184-106263112 |
| 17581 | Psmc6 | NM_025959.3 | chr14:45329823-45349071 |
| 17582 | Psmd1 | NM_027357.2 | chr1:86064618-86139295 |
| 17583 | Psmd10 | NM_001164177.1 | chrX:140948424-140956711 |
| 17584 | Psmd11 | NM_178616.3 | chr11:80428614-80472133 |
| 17585 | Psmd12 | NM_025894.2 | chr11:107479527-107498036 |
| 17586 | Psmd13 | NM_011875.4 | chr7:140882393-140898642 |
| 17587 | Psmd14 | NM_021526.2 | chr2:61711693-61800376 |
| 17588 | Psmd2 | NM_134101.2 | chr16:20651651-20663414 |
| 17589 | Psmd3 | NM_009439.1 | chr11:98682553-98695978 |
| 17590 | Psmd4 | NM_001282017.1 | chr3:95032690-95042614 |
| 17591 | Psmd5 | NM_080554.2 | chr2:34852088-34870962 |
| 17592 | Psmd6 | NM_025550.2 | chr14:14112184-14120904 |
| 17593 | Psmd7 | NM_010817.2 | chr8:107580379-107588482 |
| 17594 | Psmd8 | NM_026545.3 | chr7:29174186-29180673 |
| 17595 | Psmd9 | NM_026000.2 | chr5:123228189-123250125 |
| 17596 | Psme1 | NM_011189.1 | chr14:55578493-55581527 |
| 17597 | Psme2 | NM_001029855.1 | chr14:55587439-55591101 |
| 17598 | Psme2b | NM_001281472.1 | chr11:48945351-48946410 |
| 17599 | Psme3 | NM_011192.3 | chr11:101316250-101323530 |
| 17600 | Psme4 | NM_134013.3 | chr11:30771774-30880361 |
| 17601 | Psmf1 | NM_212446.2 | chr2:151716061-151741310 |
| 17602 | Psmg1 | NM_019537.2 | chr16:95979934-95990903 |
| 17603 | Psmg2 | NM_134138.1 | chr18:67641598-67654162 |
| 17604 | Psmg3 | NM_025604.3 | chr5:139823593-139826843 |
| 17605 | Psmg4 | NM_001101430.2 | chr13:34162963-34178172 |
| 17606 | Psorsic2 | NM_020576.2 | chr17:35533200-35534648 |
| 17607 | Pspc1 | NM_025682.3 | chr14:56722448-56778316 |
| 17608 | Psph | NM_133900.4 | chr5:129765557-129787253 |
| 17609 | Pspn | NM_008954.2 | chr17:56999456-57000018 |
| 17610 | Psrc1 | NM_001190161.1 | chr3:108383803-108388231 |
| 17611 | Pstk | NM_001039534.1 | chr7:131371145-131387838 |
| 17612 | Pstpip1 | NM_011193.2 | chr9:56089975-56128890 |
| 17613 | Pstpip2 | NM_013831.4 | chr18:77794549-77882879 |
| 17614 | Ptafr | NM_001081211.2 | chr4:132564066-132582686 |
| 17615 | Ptar1 | NM_028208.1 | chr19:23687399-23721129 |
| 17616 | Ptbp1 | NM_001077363.2 | chr10:79854431-79864435 |
| 17617 | Ptbp2 | NM_019550.2 | chr3:119718741-119783388 |
| 17618 | Ptbp3 | NM_144904.2 | chr4:59471867-59549364 |
| 17619 | Ptcd1 | NM_133735.2 | chr5:145147377-145167104 |
| 17620 | Ptcd2 | NM_026873.2 | chr13:99319648-99344678 |
| 17621 | Ptcd3 | NM_027275.3 | chr6:71880637-71908762 |
| 17622 | Ptch1 | NM_008957.2 | chr13:63511532-63565520 |
| 17623 | Ptch2 | NM_008958.3 | chr4:117096055-117116101 |
| 17624 | Ptchd1 | NM_001093750.1 | chrX:155569735-155623327 |
| 17625 | Ptchd2 | NM_001083342.1 | chr4:148236856-148287965 |
| 17626 | Ptchd3 | NM_029049.1 | chr11:121830217-121843436 |
| 17627 | Ptchd4 | NM_028474.1 | chr17:42315946-42507741 |
| 17628 | Ptcra | NM_011195.2 | chr17:46755662-46763712 |
| 17629 | Ptdss1 | NM_008959.3 | chr13:66932829-66998401 |
| 17630 | Ptdss2 | NM_013782.4 | chr7:141131285-141156154 |
| 17631 | Pten | NM_008960.2 | chr19:32757576-32826160 |
| 17632 | Pter | NM_008961.3 | chr2:12924040-13003454 |
| 17633 | Ptf1a | NM_018809.2 | chr2:19445662-19477501 |
| 17634 | Ptgdr | NM_008962.4 | chr14:44851234-44859375 |
| 17635 | Ptgdr2 | NM_009962.3 | chr19:10937159-10942511 |
| 17636 | Ptgds | NM_008963.2 | chr2:25486711-25469749 |
| 17637 | Ptger1 | NM_013641.2 | chr8:83666639-83670103 |
| 17638 | Ptger2 | NM_008964.4 | chr14:44988110-45003820 |
| 17639 | Ptger3 | NM_011196.2 | chr3:157566891-157644758 |
| 17640 | Ptger4 | NM_001136079.2 | chr15:5233398-5244187 |
| 17641 | Ptges | NM_022415.3 | chr2:30888470-30903297 |
| 17642 | Ptges2 | NM_133783.2 | chr2:32395889-32402740 |
| 17643 | Ptges3 | NM_019766.4 | chr10:128058981-128077254 |
| 17644 | Ptges3l | NM_026865.2 | chr11:101418813-101425333 |
| 17645 | Ptgfr | NM_008966.3 | chr3:151798609-151837528 |
| 17646 | Ptgfrn | NM_011197.3 | chr3:101040235-101110166 |
| 17647 | Ptgir | NM_008967.3 | chr7:16906489-16910905 |
| 17648 | Ptgis | NM_008968.3 | chr2:167203195-167240537 |
| 17649 | Ptgr1 | NM_025968.3 | chr4:58965589-58987078 |
| 17650 | Ptgr2 | NM_001252625.1 | chr12:84285295-84315832 |
| 17651 | Ptgs1 | NM_008969.4 | chr2:36230425-36252271 |
| 17652 | Ptgs2 | NM_011198.4 | chr1:150100030-150108234 |
| 17653 | Ptgs2os | NR_015466.3 | chr1:150074872-150099874 |
| 17654 | Pth | NM_020623.2 | chr7:113385575-113388573 |
| 17655 | Pth1r | NM_001083935.1 | chr9:110722084-110743686 |
| 17656 | Pth2 | NM_053256.2 | chr7:45180994-45181838 |
| 17657 | Pth2r | NM_139270.2 | chr1:65311256-65389244 |
| 17658 | Pthlh | NM_008970.4 | chr6:147252108-147264013 |
| 17659 | Ptk2 | NM_001130409.1 | chr15:73215556-73423191 |
| 17660 | Ptk2b | NM_001162365.1 | chr14:66153256-66281052 |
| 17661 | Ptk6 | NM_009184.5 | chr2:181195123-181202789 |
| 17662 | Ptk7 | NM_175168.4 | chr17:46564450-46629504 |

Fig. 26 - 94

| | | | |
|---|---|---|---|
| 17663 | Ptma | NM_008972.2 | chr1:86526735-86530698 |
| 17664 | Ptms | NM_026988.2 | chr6:124913674-124917946 |
| 17665 | Ptn | NM_008973.2 | chr6:36715662-36811361 |
| 17666 | Ptov1 | NM_133949.1 | chr7:44863067-44869788 |
| 17667 | Ptp4a1 | NM_011200.2 | chr1:30940302-30949755 |
| 17668 | Ptp4a2 | NM_001164745.1 | chr4:129820707-129850003 |
| 17669 | Ptp4a3 | NM_001166388.1 | chr15:73724929-73758766 |
| 17670 | Ptpdc1 | NM_207232.2 | chr13:48577868-48625672 |
| 17671 | Ptpla | NM_001012396.2 | chr2:14026830-14056035 |
| 17672 | Ptplad1 | NM_023345.2 | chr9:64986982-65021717 |
| 17673 | Ptplad2 | NM_025760.4 | chr4:88412929-88438926 |
| 17674 | Ptplb | NM_023587.2 | chr6:35022420-35109175 |
| 17675 | Ptpmt1 | NM_025576.2 | chr2:90910712-90918050 |
| 17676 | Ptpn1 | NM_011201.3 | chr2:167932326-167979385 |
| 17677 | Ptpn11 | NM_001109992.1 | chr5:121130532-121191397 |
| 17678 | Ptpn12 | NM_011203.2 | chr5:20986644-21055797 |
| 17679 | Ptpn13 | NM_011204.2 | chr5:103425191-103598361 |
| 17680 | Ptpn14 | NM_008976.2 | chr1:189728267-189876693 |
| 17681 | Ptpn18 | NM_011206.2 | chr1:34459745-34473779 |
| 17682 | Ptpn2 | NM_001127177.1 | chr18:67665500-67724621 |
| 17683 | Ptpn20 | NM_008978.2 | chr14:33589269-33640754 |
| 17684 | Ptpn21 | NM_001146199.1 | chr12:98676740-98737405 |
| 17685 | Ptpn22 | NM_008979.2 | chr3:103860276-103912252 |
| 17686 | Ptpn23 | NM_001081043.1 | chr9:110385088-110408210 |
| 17687 | Ptpn3 | NM_011207.2 | chr4:57190840-57301837 |
| 17688 | Ptpn4 | NM_019933.2 | chr1:119658092-119837071 |
| 17689 | Ptpn5 | NM_001163565.1 | chr7:47077799-47132598 |
| 17690 | Ptpn6 | NM_001077705.2 | chr6:124720706-124738709 |
| 17691 | Ptpn7 | NM_177081.3 | chr1:135132724-135145320 |
| 17692 | Ptpn9 | NM_019651.2 | chr9:56994967-57062807 |
| 17693 | Ptpra | NM_001163668.1 | chr2:130450277-130554300 |
| 17694 | Ptprb | NM_029928.2 | chr10:116301373-116389538 |
| 17695 | Ptprc | NM_001111316.2 | chr1:138062858-138175126 |
| 17696 | Ptprcap | NM_016933.3 | chr19:4154645-4156710 |
| 17697 | Ptprd | NM_011211.3 | chr4:75941236-78211895 |
| 17698 | Ptpre | NM_011212.3 | chr7:135537823-135686294 |
| 17699 | Ptprf | NM_011213.2 | chr4:118208212-118291397 |
| 17700 | Ptprg | NM_008981.3 | chr14:11553552-12242039 |
| 17701 | Ptprh | NM_207270.2 | chr7:4548613-4604041 |
| 17702 | Ptprj | NM_001135657.1 | chr2:90429755-90479174 |
| 17703 | Ptprk | NM_008983.2 | chr10:28074819-28597397 |
| 17704 | Ptprm | NM_008984.2 | chr17:66666847-67354459 |
| 17705 | Ptprn | NM_008985.2 | chr1:75247040-75264208 |
| 17706 | Ptprn2 | NM_011215.2 | chr12:116485719-117278167 |
| 17707 | Ptpro | NM_001164401.1 | chr6:137252298-137464633 |
| 17708 | Ptprq | NM_001081432.1 | chr10:107517359-107720027 |
| 17709 | Ptprr | NM_001161837.1 | chr10:116143897-116274929 |
| 17710 | Ptprs | NM_001252453.1 | chr17:56412425-56476480 |
| 17711 | Ptprt | NM_001291149.1 | chr2:161521987-162661147 |
| 17712 | Ptprtos | NR_040617.1 | chr2:162390812-162393946 |
| 17713 | Ptpru | NM_001083119.2 | chr4:131768456-131838278 |
| 17714 | Ptprv | NM_007955.3 | chr1:135108497-135132575 |
| 17715 | Ptprz1 | NM_001081306.1 | chr6:22875501-23052916 |
| 17716 | Ptrf | NM_008986.2 | chr11:100956735-100970617 |
| 17717 | Ptrh1 | NM_178595.3 | chr2:32775820-32777593 |
| 17718 | Ptrh2 | NM_001098810.2 | chr11:86684080-86692457 |
| 17719 | Ptrhd1 | NM_001204912.1 | chr12:4234026-4240123 |
| 17720 | Pts | NM_011220.2 | chr9:50521616-50528641 |
| 17721 | Pttg1 | NM_001131054.1 | chr11:43420247-43426648 |
| 17722 | Pttg1ip | NM_145925.2 | chr10:77581766-77598732 |
| 17723 | Ptx3 | NM_008987.3 | chr3:66219886-66225806 |
| 17724 | Ptx4 | NM_001163416.1 | chr17:25120759-25125268 |
| 17725 | Puf60 | NM_001164600.1 | chr15:76070181-76080870 |
| 17726 | Pum1 | NM_001159603.1 | chr4:130663358-130781565 |
| 17727 | Pum2 | NM_001160219.1 | chr12:8674258-8752583 |
| 17728 | Pura | NM_008989.3 | chr18:36281161-36288244 |
| 17729 | Purb | NM_011221.3 | chr11:6467598-6476076 |
| 17730 | Purg | NM_001098233.1 | chr8:33386324-33417469 |
| 17731 | Pus1 | NM_001025561.3 | chr5:110773666-110780596 |
| 17732 | Pus10 | NM_001033654.2 | chr11:23665673-23732876 |
| 17733 | Pus3 | NM_023292.4 | chr9:35559465-35567400 |
| 17734 | Pus7 | NM_001289780.1 | chr5:23740164-23783711 |
| 17735 | Pus7l | NM_172437.3 | chr15:94522639-94543507 |
| 17736 | Pusl1 | NM_001033490.1 | chr4:155888859-155891762 |
| 17737 | Pvalb | NM_013645.3 | chr15:78191117-78206351 |
| 17738 | Pvr | NM_027514.2 | chr7:19903577-19921143 |
| 17739 | Pvrl1 | NM_021424.2 | chr9:43744575-43807461 |
| 17740 | Pvrl2 | NM_001159724.1 | chr7:19724160-19749573 |
| 17741 | Pvrl3 | NM_021495.4 | chr16:46447160-46496967 |
| 17742 | Pvrl4 | NM_001122680.1 | chr1:171370172-171388287 |
| 17743 | Pvt1 | NR_003368.2 | chr15:62037985-62250976 |
| 17744 | Pwp1 | NM_133969.3 | chr10:85871830-85889103 |
| 17745 | Pwp2 | NM_029546.2 | chr10:78170909-78185149 |
| 17746 | Pwwp2a | NM_001164231.1 | chr11:43681997-43722633 |
| 17747 | Pwwp2b | NM_001033206.2 | chr7:139248481-139267253 |
| 17748 | Pxdc1 | NM_025831.3 | chr13:34627840-34652681 |
| 17749 | Pxdn | NM_181395.2 | chr12:29938035-30017658 |
| 17750 | Pxk | NM_145458.3 | chr14:8098212-8165111 |
| 17751 | Pxmp2 | NM_008993.2 | chr5:110274285-110286168 |
| 17752 | Pxmp4 | NM_021534.3 | chr2:154587043-154603673 |
| 17753 | Pxn | NM_011223.3 | chr5:115506675-115555987 |
| 17754 | Pxt1 | NM_153390.1 | chr17:28933985-28934262 |
| 17755 | Pxylp1 | NM_001289645.1 | chr9:96823342-96889474 |
| 17756 | Pycard | NM_023258.4 | chr7:127991372-127993867 |
| 17757 | Pycr1 | NM_144795.3 | chr11:120635711-120643670 |
| 17758 | Pycr2 | NM_133705.2 | chr1:180904273-180908088 |
| 17759 | Pycrl | NM_025412.2 | chr15:75916462-75923560 |
| 17760 | Pydc3 | NM_001162938.1 | chr1:173673679-173698392 |
| 17761 | Pydc4 | NM_001177349.1 | chr1:173591956-173599274 |
| 17762 | Pygb | NM_153781.1 | chr2:150786795-150831748 |
| 17763 | Pygl | NM_133198.2 | chr12:70190814-70227683 |
| 17764 | Pygm | NM_011224.1 | chr19:6384428-6398459 |
| 17765 | Pygo1 | NM_028116.2 | chr9:72925649-72946015 |
| 17766 | Pygo2 | NM_026869.3 | chr3:89430836-89435130 |
| 17767 | Pyhin1 | NM_175026.3 | chr1:173630858-173647928 |
| 17768 | Pyroxd1 | NM_183165.3 | chr6:142345696-142362624 |
| 17769 | Pyroxd2 | NM_029011.2 | chr19:42725857-42752775 |
| 17770 | Pyurf | NM_025574.3 | chr6:57684738-57692078 |
| 17771 | Pyy | NM_145435.1 | chr11:102106675-102107776 |
| 17772 | Pzp | NM_007376.4 | chr6:128483566-128526720 |
| 17773 | Qars | NM_001168270.1 | chr9:108509478-108515941 |
| 17774 | Qdpr | NM_024236.2 | chr5:45434031-45450229 |
| 17775 | Qk | NM_001159516.1 | chr17:10210179-10319361 |
| 17776 | Qpct | NM_027455.3 | chr17:79051985-79090243 |
| 17777 | Qpctl | NM_026111.3 | chr7:19140216-19149196 |
| 17778 | Qprt | NM_133686.1 | chr7:127107769-127122029 |
| 17779 | Qrfp | NM_183424.4 | chr2:31806167-31810580 |
| 17780 | Qrfpr | NM_198192.2 | chr3:36179425-36222275 |
| 17781 | Qrich1 | NM_001114119.1 | chr9:108517086-108560167 |
| 17782 | Qrich2 | NM_001033267.2 | chr11:116441324-116454347 |
| 17783 | Qrsl1 | NM_001081054.2 | chr10:43874189-43901736 |
| 17784 | Qser1 | NM_001123327.2 | chr2:104754792-104816696 |
| 17785 | Qsox1 | NM_001024945.1 | chr1:155778154-155812899 |
| 17786 | Qsox2 | NM_153559.3 | chr2:26209123-26237399 |
| 17787 | Qtrt1 | NM_023888.2 | chr9:21411836-21420279 |
| 17788 | Qtrtd1 | NM_029128.2 | chr16:43864412-43889676 |
| 17789 | R3hcc1 | NM_001146012.2 | chr14:69697303-69707584 |
| 17790 | R3hcc1l | NM_177464.4 | chr19:42518804-42592256 |
| 17791 | R3hdm1 | NM_181750.2 | chr1:128103305-128237735 |
| 17792 | R3hdm2 | NM_001168292.1 | chr10:127390310-127499384 |
| 17793 | R3hdm4 | NM_177994.4 | chr10:79910052-79916930 |
| 17794 | R3hdml | NM_001099331.2 | chr2:163492317-163502612 |
| 17795 | R74862 | NR_015529.2 | chr7:143032620-143053686 |
| 17796 | Rab1 | NM_008996.3 | chr11:20201601-20226856 |
| 17797 | Rab10 | NM_016676.5 | chr12:3247427-3309969 |
| 17798 | Rab10os | NR_015551.1 | chr12:3235790-3250374 |
| 17799 | Rab11a | NM_017382.5 | chr9:64715299-64737756 |
| 17800 | Rab11b | NM_008997.3 | chr17:33742483-33760486 |
| 17801 | Rab11fip1 | NM_001080813.2 | chr8:27138772-27174646 |
| 17802 | Rab11fip2 | NM_001033172.3 | chr19:59902883-59943364 |
| 17803 | Rab11fip3 | NM_001162868.1 | chr17:25989035-26069177 |
| 17804 | Rab11fip4 | NM_175543.3 | chr11:79591211-79694012 |
| 17805 | Rab11fip4os1 | NR_003283.1 | chr11:79607078-79623163 |
| 17806 | Rab11fip4os2 | NR_045898.2 | chr11:79670372-79675086 |
| 17807 | Rab11fip5 | NM_001003955.2 | chr6:85334961-85374634 |
| 17808 | Rab12 | NM_024448.2 | chr17:66494511-66519670 |
| 17809 | Rab13 | NM_026677.4 | chr3:90220783-90226387 |
| 17810 | Rab14 | NM_026697.3 | chr2:35180204-35201120 |
| 17811 | Rab15 | NM_134050.4 | chr12:76797962-76822524 |
| 17812 | Rab17 | NM_001159725.2 | chr1:90958132-90967667 |
| 17813 | Rab18 | NM_001278447.1 | chr18:6765166-6791606 |
| 17814 | Rab19 | NM_011226.1 | chr6:39381427-39390379 |
| 17815 | Rab1b | NM_029576.3 | chr19:5099206-5106996 |
| 17816 | Rab20 | NM_011227.1 | chr8:11453976-11478499 |
| 17817 | Rab21 | NM_024454.1 | chr10:115289861-115315591 |
| 17818 | Rab22a | NM_024436.3 | chr2:173659644-173702182 |
| 17819 | Rab23 | NM_001159729.1 | chr1:33720418-33742564 |
| 17820 | Rab24 | NM_009000.3 | chr13:55319222-55321980 |
| 17821 | Rab25 | NM_016899.4 | chr3:88542028-88548279 |
| 17822 | Rab26 | NM_177375.1 | chr17:24529053-24533747 |
| 17823 | Rab26os | NR_045289.1 | chr17:24528250-24528744 |
| 17824 | Rab27a | NM_023635.6 | chr9:73044809-73097614 |
| 17825 | Rab27b | NM_001082553.2 | chr18:69979130-70141605 |
| 17826 | Rab28 | NM_027295.3 | chr5:41624972-41708179 |
| 17827 | Rab2a | NM_021518.3 | chr4:8535643-8607702 |
| 17828 | Rab2b | NM_172601.3 | chr14:52261758-52279395 |
| 17829 | Rab30 | NM_029494.2 | chr7:92741713-92837117 |
| 17830 | Rab31 | NM_133685.2 | chr17:65651725-65772752 |
| 17831 | Rab32 | NM_026405.3 | chr10:10545038-10558207 |
| 17832 | Rab33a | NM_011228.2 | chrX:48519284-48530240 |
| 17833 | Rab33b | NM_016858.2 | chr3:51483965-51496212 |
| 17834 | Rab34 | NM_001159482.1 | chr11:78188426-78192193 |
| 17835 | Rab35 | NM_198163.1 | chr5:115631986-115647158 |
| 17836 | Rab36 | NM_029781.3 | chr10:75037088-75054100 |
| 17837 | Rab37 | NM_001163753.1 | chr11:115091430-115162240 |
| 17838 | Rab38 | NM_028238.7 | chr7:88430272-88491572 |
| 17839 | Rab39 | NM_175562.3 | chr9:53684109-53706232 |
| 17840 | Rab39b | NM_175122.6 | chrX:75572044-75578231 |
| 17841 | Rab3a | NM_001166399.2 | chr8:70754678-70758686 |
| 17842 | Rab3b | NM_023537.5 | chr4:108879069-108943324 |
| 17843 | Rab3c | NM_023852.5 | chr13:110054186-110280206 |
| 17844 | Rab3d | NM_031874.4 | chr9:21907510-21918131 |
| 17845 | Rab3gap1 | NM_178690.4 | chr1:127868772-127943876 |
| 17846 | Rab3gap2 | NM_001163754.1 | chr1:185204187-185286746 |
| 17847 | Rab3il1 | NM_144538.2 | chr19:10018227-10035586 |
| 17848 | Rab3ip | NM_001003950.2 | chr10:116905783-116950380 |
| 17849 | Rab40b | NM_139147.3 | chr11:121356120-121388251 |
| 17850 | Rab40c | NM_139154.2 | chr17:25882113-25919714 |
| 17851 | Rab42 | NM_001081651.1 | chr4:132302193-132303356 |
| 17852 | Rab43 | NM_001039394.1 | chr6:87788852-87811779 |

Fig. 26 - 95

| | | | |
|---|---|---|---|
| 17853 | Rab44 | NM_001002786.2 | chr17:29135055-29148976 |
| 17854 | Rab4a | NM_009003.3 | chr8:123805995-123835291 |
| 17855 | Rab4b | NM_029391.2 | chr7:27168432-27178883 |
| 17856 | Rab5a | NM_025887.4 | chr17:53479233-53507678 |
| 17857 | Rab5b | NM_177411.4 | chr10:128677182-128696268 |
| 17858 | Rab5c | NM_024456.5 | chr11:100715002-100738215 |
| 17859 | Rab6a | NM_001163663.1 | chr7:100607585-100641268 |
| 17860 | Rab6b | NM_173781.4 | chr9:103112073-103185270 |
| 17861 | Rab7 | NM_009005.3 | chr6:87999105-88045270 |
| 17862 | Rab7l1 | NM_144875.2 | chr1:131867276-131872889 |
| 17863 | Rab8a | NM_023126.2 | chr8:72161199-72181366 |
| 17864 | Rab8b | NM_173413.3 | chr9:66843663-66919705 |
| 17865 | Rab9 | NM_019773.2 | chrX:166457251-166479867 |
| 17866 | Rab9b | NM_176971.2 | chrX:136858150-136868540 |
| 17867 | Rabac1 | NM_010261.2 | chr7:24969749-24972728 |
| 17868 | Rabep1 | NM_001291141.1 | chr11:70844760-70943105 |
| 17869 | Rabep2 | NM_030566.2 | chr7:126428766-126445907 |
| 17870 | Rabepk | NM_145522.4 | chr2:34778665-34799912 |
| 17871 | Rabgap1 | NM_001033960.1 | chr2:37452253-37544962 |
| 17872 | Rabgap1l | NM_001038621.2 | chr1:160219173-160351571 |
| 17873 | Rabgef1 | NM_001199059.1 | chr5:130171818-130214337 |
| 17874 | Rabggta | NM_019519.2 | chr14:55715876-55722176 |
| 17875 | Rabggtb | NM_001163478.1 | chr3:153907288-153912966 |
| 17876 | Rabif | NM_145510.1 | chr1:134494659-134507884 |
| 17877 | Rabl2 | NM_026817.3 | chr15:89582526-89591923 |
| 17878 | Rabl3 | NM_001042499.1 | chr16:37539893-37572385 |
| 17879 | Rabl6 | NM_001024616.1 | chr2:25583017-25608446 |
| 17880 | Rac1 | NM_009007.2 | chr5:143605480-143527993 |
| 17881 | Rac2 | NM_009008.3 | chr15:78559168-78572783 |
| 17882 | Rac3 | NM_133223.4 | chr11:120721467-120723969 |
| 17883 | Racgap1 | NM_001253808.1 | chr15:99620495-99651656 |
| 17884 | Rad1 | NM_001289447.1 | chr15:10486037-10493695 |
| 17885 | Rad17 | NM_001044371.2 | chr13:100617163-100651061 |
| 17886 | Rad18 | NM_001167730.1 | chr6:112619850-112696670 |
| 17887 | Rad21 | NM_009009.4 | chr15:51962603-51991760 |
| 17888 | Rad23l | NM_001276400.1 | chr2:151645403-151668533 |
| 17889 | Rad23a | NM_009010.5 | chr8:84834651-84840665 |
| 17890 | Rad23b | NM_009011.4 | chr4:55350041-55392237 |
| 17891 | Rad50 | NM_009013.2 | chr11:53649518-53707319 |
| 17892 | Rad51 | NM_011234.4 | chr2:119112816-119136070 |
| 17893 | Rad51ap1 | NM_009013.3 | chr6:126923418-126939555 |
| 17894 | Rad51ap2 | NM_001111118.1 | chr12:11456078-11462928 |
| 17895 | Rad51b | NM_001252562.1 | chr12:79297350-79508654 |
| 17896 | Rad51c | NM_001291440.1 | chr11:87377606-87404954 |
| 17897 | Rad51d | NM_001173062.1 | chr11:82873062-82890624 |
| 17898 | Rad52 | NM_001166381.1 | chr6:119902697-119922823 |
| 17899 | Rad54b | NM_001039556.3 | chr4:11558919-11615808 |
| 17900 | Rad54l | NM_001122958.1 | chr4:116096954-116123689 |
| 17901 | Rad54l2 | NM_030730.2 | chr9:106688079-106789213 |
| 17902 | Rad9a | NM_011237.2 | chr19:4195197-4201603 |
| 17903 | Rad9b | NM_144912.3 | chr5:122325507-122354195 |
| 17904 | Radil | NM_001289588.1 | chr5:142484838-142551098 |
| 17905 | Rael | NM_175152.5 | chr2:173000116-173015739 |
| 17906 | Raet1a | NM_009016.1 | chr10:22158608-22374139 |
| 17907 | Raet1b | NM_009017.1 | chr10:22173874-22374113 |
| 17908 | Raet1c | NM_009018.1 | chr10:22173901-22374139 |
| 17909 | Raet1d | NM_020030.2 | chr10:22361893-22374139 |
| 17910 | Raet1e | NM_198193.2 | chr10:22173520-22183914 |
| 17911 | Raf1 | NM_029870.3 | chr6:115618572-115676635 |
| 17912 | Rag1 | NM_009019.2 | chr2:101638251-101649532 |
| 17913 | Rag2 | NM_009020.3 | chr2:101624747-101632528 |
| 17914 | Rai1 | NM_001037764.1 | chr11:60140081-60199195 |
| 17915 | Rai14 | NM_001166408.1 | chr15:10568977-10714631 |
| 17916 | Rai2 | NM_001103367.1 | chrX:161717035-161779494 |
| 17917 | Rala | NM_019491.5 | chr13:17880574-17944217 |
| 17918 | Ralb | NM_022327.5 | chr1:119470304-119504782 |
| 17919 | Ralbp1 | NM_001198949.1 | chr17:65848427-65884923 |
| 17920 | Ralgapa1 | NM_001039179.2 | chr12:55602889-55821516 |
| 17921 | Ralgapa2 | NM_001033348.3 | chr2:146241298-146512004 |
| 17922 | Ralgapb | NM_001291137.1 | chr2:158409852-158499253 |
| 17923 | Ralgds | NM_001145834.1 | chr2:28513166-28553082 |
| 17924 | Ralgps1 | NM_001290570.1 | chr2:33133418-33371494 |
| 17925 | Ralgps2 | NM_001159965.1 | chr1:156804165-156939626 |
| 17926 | Raly | NM_001139511.1 | chr2:154791109-154867261 |
| 17927 | Ralyl | NM_001163328.1 | chr3:13471654-14182287 |
| 17928 | Ramp1 | NM_016894.1 | chr1:91179821-91206790 |
| 17929 | Ramp2 | NM_019444.2 | chr11:101246333-101248250 |
| 17930 | Ramp3 | NM_019511.3 | chr11:6658532-6677475 |
| 17931 | Ran | NM_009391.3 | chr5:129020155-129024321 |
| 17932 | Ranbp1 | NM_011239.2 | chr16:18239978-18248694 |
| 17933 | Ranbp10 | NM_145824.4 | chr8:105768307-105827350 |
| 17934 | Ranbp17 | NM_023146.2 | chr11:33211793-33513746 |
| 17935 | Ranbp2 | NM_011240.3 | chr10:58446851-58494154 |
| 17936 | Ranbp3 | NM_022466.1 | chr17:56673224-56711769 |
| 17937 | Ranbp3l | NM_198024.2 | chr15:8967948-9067333 |
| 17938 | Ranbp6 | NM_177721.4 | chr19:29808107-29812974 |
| 17939 | Ranbp9 | NM_019923.2 | chr13:43402672-43480973 |
| 17940 | Rangap1 | NM_001146174.1 | chr15:81704247-81729919 |
| 17941 | Rangrf | NM_001285441.1 | chr11:68972483-68975185 |
| 17942 | Rap1a | NM_145541.5 | chr3:105727259-105801381 |
| 17943 | Rap1b | NM_024457.2 | chr10:117814596-117845974 |
| 17944 | Rap1gap | NM_001081155.2 | chr4:137681666-137729861 |
| 17945 | Rap1gap2 | NM_001035046.2 | chr11:74383482-74590158 |
| 17946 | Rap1gds1 | NM_001040690.2 | chr3:138925896-139075201 |
| 17947 | Rap2a | NM_029519.3 | chr14:120478460-120507192 |
| 17948 | Rap2b | NM_028712.4 | chr3:61364506-61368703 |
| 17949 | Rap2c | NM_172413.2 | chrX:51003913-51018018 |
| 17950 | Rapgef1 | NM_001039086.1 | chr2:29619719-29740363 |
| 17951 | Rapgef2 | NM_001099624.3 | chr3:79062510-79145875 |
| 17952 | Rapgef3 | NM_001177810.1 | chr15:97744769-97767666 |
| 17953 | Rapgef4 | NM_001204165.1 | chr2:71981214-72257474 |
| 17954 | Rapgef5 | NM_175930.5 | chr12:117516478-117756978 |
| 17955 | Rapgef6 | NM_001252494.1 | chr11:54522844-54699286 |
| 17956 | Rapgefl1 | NM_001080925.1 | chr11:98836784-98853005 |
| 17957 | Raph1 | NM_001045513.3 | chr1:60483184-60566765 |
| 17958 | Rapsn | NM_009023.3 | chr2:91035626-91045729 |
| 17959 | Rara | NM_001176528.1 | chr11:98960470-98974942 |
| 17960 | Rarb | NM_001289760.1 | chr14:16430839-17082331 |
| 17961 | Rarg | NM_001042727.2 | chr15:102234937-102246500 |
| 17962 | Rarres1 | NM_001164763.1 | chr3:67478885-67515523 |
| 17963 | Rarres2 | NM_027852.2 | chr6:48569697-48572670 |
| 17964 | Rars | NM_025936.3 | chr11:35808380-35834528 |
| 17965 | Rars2 | NM_181406.3 | chr4:34614957-34660167 |
| 17966 | Rasa1 | NM_145452.3 | chr13:85214698-85289486 |
| 17967 | Rasa2 | NM_053268.2 | chr9:96539299-96631503 |
| 17968 | Rasa3 | NM_009025.2 | chr8:13567217-13677587 |
| 17969 | Rasa4 | NM_001039103.3 | chr5:136083915-136111861 |
| 17970 | Rasal1 | NM_001281999.1 | chr5:120649187-120679610 |
| 17971 | Rasal2 | NM_177644.5 | chr1:157135182-157412595 |
| 17972 | Rasal3 | NM_178785.3 | chr17:32390660-32403581 |
| 17973 | Rasd1 | NM_009026.5 | chr11:59963180-59964944 |
| 17974 | Rasd2 | NM_029182.1 | chr8:75213943-75224113 |
| 17975 | Rasef | NM_001017427.1 | chr4:73714578-73790602 |
| 17976 | Rasgef1a | NM_027526.1 | chr6:118066384-118091546 |
| 17977 | Rasgef1b | NM_145839.2 | chr5:99217419-99252927 |
| 17978 | Rasgef1c | NM_029004.1 | chr11:49901834-49980223 |
| 17979 | Rasgrf1 | NM_001039655.1 | chr9:89909774-89915847 |
| 17980 | Rasgrf2 | NM_009027.3 | chr13:91880406-91988042 |
| 17981 | Rasgrp1 | NM_011246.2 | chr2:117279992-117342877 |
| 17982 | Rasgrp2 | NM_011242.2 | chr19:6400582-6415216 |
| 17983 | Rasgrp3 | NM_001166493.1 | chr17:75435904-75529053 |
| 17984 | Rasgrp4 | NM_001174155.1 | chr7:29134932-29153955 |
| 17985 | Rasip1 | NM_028544.1 | chr7:45627536-45639092 |
| 17986 | Rasl10a | NM_145216.3 | chr11:5058127-5060383 |
| 17987 | Rasl10b | NM_001013386.2 | chr11:83410071-83421038 |
| 17988 | Rasl11a | NM_026864.1 | chr5:146845070-146847726 |
| 17989 | Rasl11b | NM_026878.1 | chr5:74195325-74199477 |
| 17990 | Rasl12 | NM_001033158.2 | chr9:65398487-65412707 |
| 17991 | Rasl2-9 | NM_009028.2 | chr7:5124941-5125950 |
| 17992 | Rassf1 | NM_001243748.1 | chr9:107551554-107562267 |
| 17993 | Rassf10 | NM_175279.3 | chr7:112953961-112957458 |
| 17994 | Rassf2 | NM_175445.4 | chr2:131992849-132029988 |
| 17995 | Rassf3 | NM_138956.5 | chr10:121410350-121476250 |
| 17996 | Rassf4 | NM_178045.4 | chr6:116633007-116673836 |
| 17997 | Rassf5 | NM_018750.4 | chr1:131176409-131245178 |
| 17998 | Rassf6 | NM_028478.3 | chr5:90603075-90640527 |
| 17999 | Rassf7 | NM_025886.3 | chr7:141215859-141218658 |
| 18000 | Rassf8 | NM_027760.2 | chr6:145808382-145817584 |
| 18001 | Rassf9 | NM_146240.4 | chr10:102512221-102546560 |
| 18002 | Raver1 | NM_079911.3 | chr9:21074163-21091988 |
| 18003 | Raver1-fdx1l | NR_038081.2 | chr9:21067513-21092008 |
| 18004 | Raver2 | NM_183024.1 | chr4:101069037-101152370 |
| 18005 | Rax | NM_013833.2 | chr18:65934638-65939089 |
| 18006 | Rb1 | NM_009029.2 | chr14:73195501-73325791 |
| 18007 | Rb1cc1 | NM_009826.4 | chr1:6214661-6276104 |
| 18008 | Rbak | NM_001045482.2 | chr5:143172185-143180775 |
| 18009 | Rbakdn | NR_040424.1 | chr5:143164778-143165751 |
| 18010 | Rbbp4 | NM_009030.3 | chr4:129307099-129335370 |
| 18011 | Rbbp5 | NM_172517.2 | chr1:132477366-132505665 |
| 18012 | Rbbp6 | NM_011247.2 | chr7:122970563-123002572 |
| 18013 | Rbbp7 | NM_009031.3 | chrX:162780371-162779090 |
| 18014 | Rbbp8 | NM_001081223.2 | chr18:11657348-11743207 |
| 18015 | Rbbp8nl | NM_173031.3 | chr2:180277645-180289879 |
| 18016 | Rbbp9 | NM_015754.2 | chr2:144542264-144550859 |
| 18017 | Rbck1 | NM_001083921.1 | chr2:152316333-152332425 |
| 18018 | Rbfa | NM_199197.1 | chr18:80192263-80200619 |
| 18019 | Rbfox1 | NM_021477.5 | chr16:5884792-7412480 |
| 18020 | Rbfox2 | NM_001110827.2 | chr15:77078989-77307053 |
| 18021 | Rbfox3 | NM_001024931.2 | chr11:118489759-118909572 |
| 18022 | Rbks | NM_153196.1 | chr5:31624438-31697610 |
| 18023 | Rbl1 | NM_001139516.1 | chr2:157174995-157204534 |
| 18024 | Rbl2 | NM_001282000.1 | chr8:91070056-91123844 |
| 18025 | Rbm10 | NM_001167775.1 | chrX:20617502-20650905 |
| 18026 | Rbm11 | NM_198302.2 | chr16:75592890-75602825 |
| 18027 | Rbm12 | NM_029397.3 | chr2:156094881-156111965 |
| 18028 | Rbm12b1 | NM_028226.2 | chr4:12146116-12146746 |
| 18029 | Rbm12b2 | NM_198957.2 | chr4:12089369-12096271 |
| 18030 | Rbm14 | NM_019869.3 | chr19:4800565-4811634 |
| 18031 | Rbm14-rbm4 | NM_001290127.1 | chr19:4784292-4811634 |
| 18032 | Rbm15 | NM_001045807.1 | chr9:107326109-107333289 |
| 18033 | Rbm15b | NM_175402.4 | chr9:106883984-106887000 |
| 18034 | Rbm17 | NM_152824.1 | chr2:11585438-11603199 |
| 18035 | Rbm18 | NM_001159635.1 | chr2:36116078-36136704 |
| 18036 | Rbm19 | NM_028762.1 | chr5:120118512-120198971 |
| 18037 | Rbm20 | NM_001170847.1 | chr19:53677305-53867080 |
| 18038 | Rbm22 | NM_025776.2 | chr18:60560785-60572729 |
| 18039 | Rbm24 | NM_001081425.1 | chr13:46418299-46431099 |
| 18040 | Rbm25 | NM_027349.3 | chr12:83632233-83683123 |
| 18041 | Rbm26 | NM_134077.4 | chr14:105114518-105177327 |
| 18042 | Rbm27 | NM_172626.2 | chr18:42275352-42341540 |

Fig. 26 - 96

| | | | |
|---|---|---|---|
| 18043 | Rbm28 | NM_133925.1 | chr6:29123572-29164724 |
| 18044 | Rbm3 | NM_001166409.2 | chrX:8142355-8145880 |
| 18045 | Rbm31y | NM_028970.1 | chrY:12688109-17402718 |
| 18046 | Rbm33 | NM_028234.1 | chr5:28317188-28419242 |
| 18047 | Rbm34 | NM_172762.2 | chr8:126947172-126971079 |
| 18048 | Rbm38 | NM_019547.2 | chr2:173021901-173034731 |
| 18049 | Rbm39 | NM_001291114.1 | chr2:156147240-156180238 |
| 18050 | Rbm3os | NR_033561.1 | chrX:8145426-8147963 |
| 18051 | Rbm4 | NM_001290122.1 | chr19:4784292-4794009 |
| 18052 | Rbm41 | NM_001172147.1 | chrX:139941527-139998595 |
| 18053 | Rbm42 | NM_133693.2 | chr7:30640994-30650228 |
| 18054 | Rbm43 | NM_001141981.1 | chr2:51924448-51935009 |
| 18055 | Rbm44 | NM_001033408.4 | chr1:91145102-91170795 |
| 18056 | Rbm45 | NM_144948.5 | chr9:48488696-48495330 |
| 18057 | Rbm46 | NM_001277170.1 | chr3:82836522-82876483 |
| 18058 | Rbm46os | NR_040381.1 | chr3:82904476-82943638 |
| 18059 | Rbm47 | NM_001127382.2 | chr5:66016548-66151954 |
| 18060 | Rbm48 | NM_172991.4 | chr5:3583977-3596547 |
| 18061 | Rbm4b | NM_025717.3 | chr19:4756524-4765941 |
| 18062 | Rbm5 | NM_148930.3 | chr9:107740494-107771002 |
| 18063 | Rbm6 | NM_011251.3 | chr9:107773558-107872819 |
| 18064 | Rbm7 | NM_144445.4 | chr9:48488696-48495330 |
| 18065 | Rbm8a | NM_001102407.1 | chr3:96629927-96633791 |
| 18066 | Rbms1 | NM_001141931.1 | chr2:60751952-60881438 |
| 18067 | Rbms2 | NM_001039080.1 | chr10:128129469-128180297 |
| 18068 | Rbms3 | NM_001172121.1 | chr9:116572746-117629913 |
| 18069 | Rbmx | NM_001166623.1 | chrX:57386029-57393036 |
| 18070 | Rbmx2 | NM_173776.3 | chrX:48695003-48710719 |
| 18071 | Rbmxl1 | NM_001252089.1 | chr8:78505268-78508928 |
| 18072 | Rbmxl2 | NM_029660.2 | chr7:107209444-107210916 |
| 18073 | Rbmy | NM_011253.2 | chrY:2830679-3783271 |
| 18074 | Rbp1 | NM_011254.5 | chr9:98422960-98446550 |
| 18075 | Rbp2 | NM_009034.4 | chr9:98490536-98509771 |
| 18076 | Rbp3 | NM_015745.2 | chr14:33954021-33964216 |
| 18077 | Rbp4 | NM_001159487.1 | chr19:38116619-38125321 |
| 18078 | Rbp7 | NM_022020.2 | chr4:149449701-149454968 |
| 18079 | Rbpj | NM_001080927.2 | chr5:53590485-53657445 |
| 18080 | Rbpjl | NM_009036.1 | chr2:164403193-164415448 |
| 18081 | Rbpms | NM_001042674.2 | chr8:33782643-33929863 |
| 18082 | Rbpms2 | NM_028030.3 | chr9:65630581-65660518 |
| 18083 | Rbx1 | NM_019712.3 | chr15:81466315-81476369 |
| 18084 | Rc3h1 | NM_001024952.2 | chr1:160906410-160974976 |
| 18085 | Rc3h2 | NM_001100591.1 | chr2:37370070-37422903 |
| 18086 | Rcan1 | NM_001081549.2 | chr16:92391950-92466169 |
| 18087 | Rcan2 | NM_001266653.1 | chr17:43804002-44039516 |
| 18088 | Rcan3 | NM_022980.4 | chr4:135412308-135433805 |
| 18089 | Rcbtb1 | NM_027764.2 | chr14:59201227-59237265 |
| 18090 | Rcbtb2 | NM_001170694.1 | chr14:73142509-73184054 |
| 18091 | Rcc1 | NM_001197082.1 | chr4:132331918-132345750 |
| 18092 | Rcc2 | NM_173867.5 | chr4:140701472-140723220 |
| 18093 | Rccd1 | NM_173444.4 | chr7:80316615-80324454 |
| 18094 | Rce1 | NM_023131.1 | chr19:4622550-4625617 |
| 18095 | Rchy1 | NM_001271797.1 | chr5:91948841-91963068 |
| 18096 | Rcl1 | NM_021525.2 | chr19:29101374-29143843 |
| 18097 | Rcn1 | NM_009037.2 | chr2:105385947-105399319 |
| 18098 | Rcn2 | NM_001278274.1 | chr9:56041844-56043245 |
| 18099 | Rcn3 | NM_026555.2 | chr7:45082913-45092213 |
| 18100 | Rcor1 | NM_198023.2 | chr12:111039797-111113386 |
| 18101 | Rcor2 | NM_054048.3 | chr19:7269763-7275225 |
| 18102 | Rcor3 | NM_001290278.1 | chr1:192098545-192138040 |
| 18103 | Rcsd1 | NM_001038846.1 | chr1:165648944-165708094 |
| 18104 | Rcvrn | NM_009038.2 | chr11:67695325-67703355 |
| 18105 | Rd3 | NM_001177900.2 | chr1:191977369-191988282 |
| 18106 | Rd3l | NM_001127685.1 | chr12:111979322-111980751 |
| 18107 | Rdh1 | NM_080436.3 | chr10:127759762-127768299 |
| 18108 | Rdh10 | NM_133832.3 | chr1:16105881-16132550 |
| 18109 | Rdh11 | NM_021557.5 | chr12:79175550-79191819 |
| 18110 | Rdh12 | NM_030017.4 | chr12:79208912-79222664 |
| 18111 | Rdh13 | NM_001290409.1 | chr7:4425664-4445657 |
| 18112 | Rdh14 | NM_023697.2 | chr12:10390779-10395562 |
| 18113 | Rdh16 | NM_009040.3 | chr10:127801152-127815839 |
| 18114 | Rdh16-ps | NR_037604.1 | chr10:127824215-127846565 |
| 18115 | Rdh19 | NM_147222.2 | chr10:127849927-127861176 |
| 18116 | Rdh5 | NM_134006.4 | chr10:128913590-128919297 |
| 18117 | Rdh7 | NM_001150749.1 | chr10:127884026-127888733 |
| 18118 | Rdh8 | NM_001030290.1 | chr9:20818503-20826163 |
| 18119 | Rdh9 | NM_153133.2 | chr10:127776404-127792697 |
| 18120 | Rdm1 | NM_025654.2 | chr11:101627948-101636081 |
| 18121 | Rdx | NM_001104616.1 | chr9:52047149-52088738 |
| 18122 | Rec8 | NM_020002.3 | chr14:55618165-55625395 |
| 18123 | Reck | NM_016678.2 | chr4:43875529-43944806 |
| 18124 | Recql | NM_001204906.1 | chr6:142356946-142387087 |
| 18125 | Recql4 | NM_058214.3 | chr15:76703552-76710559 |
| 18126 | Recql5 | NM_130454.2 | chr11:115892594-115933492 |
| 18127 | Redrum | NR_040348.1 | chr8:54422294-54453294 |
| 18128 | Reep1 | NM_178608.4 | chr6:71707680-71810705 |
| 18129 | Reep2 | NM_001204914.1 | chr18:34840588-34847463 |
| 18130 | Reep3 | NM_001204915.1 | chr10:67009188-67096988 |
| 18131 | Reep4 | NM_180588.2 | chr14:70545250-70568935 |
| 18132 | Reep5 | NM_007874.3 | chr18:34344885-34373415 |
| 18133 | Reep6 | NM_001204931.1 | chr10:80330144-80336441 |
| 18134 | Reg1 | NM_009042.1 | chr6:78425982-78428666 |
| 18135 | Reg2 | NM_009043.1 | chr6:78405154-78408097 |
| 18136 | Reg3a | NM_011259.1 | chr6:78380708-78383839 |
| 18137 | Reg3b | NM_011036.1 | chr6:78370884-78373466 |
| 18138 | Reg3d | NM_001161741.1 | chr6:78375873-78378865 |
| 18139 | Reg3g | NM_011260.1 | chr6:78466267-78468874 |
| 18140 | Reg4 | NM_026328.2 | chr3:98222155-98236748 |
| 18141 | Rel | NM_009044.2 | chr11:23741728-23770970 |
| 18142 | Rela | NM_009045.4 | chr19:5637489-5648130 |
| 18143 | Relb | NM_001290457.1 | chr7:19606222-19629438 |
| 18144 | Rell1 | NM_145923.4 | chr5:63968897-63968897 |
| 18145 | Rell2 | NM_153793.2 | chr18:37955558-37959179 |
| 18146 | Reln | NM_011261.2 | chr5:21884453-22344705 |
| 18147 | Relt | NM_177073.6 | chr7:100845847-100863413 |
| 18148 | Rem1 | NM_009047.5 | chr2:152627007-152635191 |
| 18149 | Rem2 | NM_080726.3 | chr14:54476099-54480434 |
| 18150 | Ren1 | NM_031192.3 | chr1:133350673-133360319 |
| 18151 | Ren2 | NM_031193.2 | chr1:133350565-133360323 |
| 18152 | Renbp | NM_001164704.1 | chrX:73922120-73930850 |
| 18153 | Rep15 | NM_025620.2 | chr6:147032536-147033518 |
| 18154 | Repin1 | NM_001079901.1 | chr6:48593882-48599082 |
| 18155 | Reps1 | NM_001111065.1 | chr10:18055939-18125155 |
| 18156 | Reps2 | NM_001290633.1 | chrX:162411951-162643658 |
| 18157 | Rer1 | NM_026395.1 | chr4:155074111-155086297 |
| 18158 | Rere | NM_001085492.1 | chr4:150281915-150621966 |
| 18159 | Rerg | NM_001164212.1 | chr6:137054824-137169718 |
| 18160 | Rergl | NM_001128090.1 | chr6:139493181-139501909 |
| 18161 | Resp18 | NM_009049.1 | chr1:75272201-75278380 |
| 18162 | Rest | NM_011263.2 | chr5:77265493-77283697 |
| 18163 | Ret | NM_001080780.1 | chr6:118151747-118197744 |
| 18164 | Retn | NM_001204959.1 | chr8:3655769-3659818 |
| 18165 | Retnla | NM_020509.3 | chr16:48842551-48844461 |
| 18166 | Retnlb | NM_023881.4 | chr16:48816855-48818892 |
| 18167 | Retnlg | NM_181596.4 | chr16:48872607-48874498 |
| 18168 | Retsat | NM_026159.4 | chr6:72598627-72607488 |
| 18169 | Rev1 | NM_019570.3 | chr1:38052785-38129662 |
| 18170 | Rev3l | NM_011264.3 | chr10:39732159-39875205 |
| 18171 | Rex2 | NM_001177767.1 | chr4:147021849-147060799 |
| 18172 | Rexo1 | NM_025852.3 | chr10:80540925-80561560 |
| 18173 | Rexo2 | NM_024233.3 | chr9:48468513-48480611 |
| 18174 | Rexo4 | NM_207234.2 | chr2:26953562-26964386 |
| 18175 | Rfc1 | NM_011258.2 | chr5:65261851-65335639 |
| 18176 | Rfc2 | NM_020022.2 | chr5:134582689-134598828 |
| 18177 | Rfc3 | NM_027009.2 | chr5:151642823-151651208 |
| 18178 | Rfc4 | NM_145480.1 | chr16:23113947-23127730 |
| 18179 | Rfc5 | NM_028128.1 | chr5:117379144-117389023 |
| 18180 | Rfesd | NM_001131068.1 | chr13:76001534-76018606 |
| 18181 | Rffl | NM_001007465.3 | chr11:82803818-82871210 |
| 18182 | Rfx | NM_019437.3 | chr19:17394042-17401349 |
| 18183 | Rfng | NM_009053.2 | chr11:120780744-120784204 |
| 18184 | Rfpl3s | NM_183111.2 | chr9:55962588-55980932 |
| 18185 | Rfpl4 | NM_001145013.1 | chr7:5109786-5116911 |
| 18186 | Rfpl4b | NM_001177783.3 | chr10:38820540-38821779 |
| 18187 | Rft1 | NM_177815.3 | chr14:30654374-30691313 |
| 18188 | Rftn1 | NM_181397.2 | chr17:49993306-50190497 |
| 18189 | Rftn2 | NM_028713.1 | chr1:55170159-55226782 |
| 18190 | Rfwd2 | NM_011931.3 | chr1:159232325-159347580 |
| 18191 | Rfwd3 | NM_146218.4 | chr8:111270943-111300222 |
| 18192 | Rfx1 | NM_009055.4 | chr8:84066835-84096992 |
| 18193 | Rfx2 | NM_009056.2 | chr17:56775896-56831008 |
| 18194 | Rfx3 | NM_001166414.1 | chr19:27761720-27982948 |
| 18195 | Rfx4 | NM_001024918.1 | chr10:84756047-84906536 |
| 18196 | Rfx5 | NM_017395.2 | chr3:94955014-94961561 |
| 18197 | Rfx6 | NM_001159389.1 | chr10:51677759-51730429 |
| 18198 | Rfx7 | NM_001033536.1 | chr9:72532239-72622949 |
| 18199 | Rfx8 | NM_001145660.1 | chr1:39665300-39720989 |
| 18200 | Rfxank | NM_001025589.1 | chr8:70130805-70139197 |
| 18201 | Rfxap | NM_132231.2 | chr3:54803114-54807791 |
| 18202 | Rgag1 | NM_001404434.2 | chrX:143099593-143104335 |
| 18203 | Rgag4 | NM_001278534.1 | chrX:102086541-102071307 |
| 18204 | Rgcc | NM_025427.2 | chr14:79288749-79301635 |
| 18205 | Rgl1 | NM_016846.3 | chr1:152517529-152625111 |
| 18206 | Rgl2 | NM_009059.2 | chr17:33929893-33937687 |
| 18207 | Rgl3 | NM_023622.4 | chr9:21971526-21989453 |
| 18208 | Rgma | NM_177740.5 | chr7:73375519-73419899 |
| 18209 | Rgmb | NM_178615.3 | chr17:15806252-15826586 |
| 18210 | Rgn | NM_009060.2 | chrX:20549817-20562087 |
| 18211 | Rgp1 | NM_172866.3 | chr4:43578734-43587487 |
| 18212 | Rgr | NM_021340.4 | chr14:37034908-37049014 |
| 18213 | Rgs1 | NM_015811.2 | chr1:144244668-144249104 |
| 18214 | Rgs10 | NM_026418.2 | chr7:128373624-128418172 |
| 18215 | Rgs11 | NM_001081069.1 | chr17:26202961-26211324 |
| 18216 | Rgs12 | NM_001163512.1 | chr5:34990077-35033593 |
| 18217 | Rgs13 | NM_153171.4 | chr1:144138666-144177372 |
| 18218 | Rgs14 | NM_016758.3 | chr13:55369731-55384687 |
| 18219 | Rgs16 | NM_011267.3 | chr1:153740352-153745468 |
| 18220 | Rgs17 | NM_001161822.1 | chr10:5825663-5922400 |
| 18221 | Rgs18 | NM_022881.4 | chr1:144752840-144775421 |
| 18222 | Rgs19 | NM_001291205.1 | chr2:181688418-181691817 |
| 18223 | Rgs2 | NM_009061.4 | chr1:143999337-144004149 |
| 18224 | Rgs20 | NM_001177795.1 | chr4:4909575-5070285 |
| 18225 | Rgs21 | NM_001290269.1 | chr1:144519689-144567667 |
| 18226 | Rgs22 | NM_001195748.1 | chr15:36009476-36140400 |
| 18227 | Rgs3 | NM_001081650.2 | chr4:62619671-62659847 |
| 18228 | Rgs4 | NM_009062.3 | chr1:169747476-169747642 |
| 18229 | Rgs5 | NM_009063.5 | chr1:169655500-169695813 |
| 18230 | Rgs6 | NM_001282061.2 | chr12:82617488-83162056 |
| 18231 | Rgs7 | NM_001199003.1 | chr1:175059075-175492545 |
| 18232 | Rgs7bp | NM_029879.2 | chr13:104947152-105054930 |

Fig. 26 - 97

| | | | | | | | |
|---|---|---|---|---|---|---|---|
| 18233 | Rgs8 | NM_026380.3 | chr1:153653036-153697665 | 18328 | Riok1 | NM_024242.3 | chr13:38036988-38061433 |
| 18234 | Rgs9 | NM_001165934.1 | chr11:109229855-109298181 | 18329 | Riok2 | NM_025934.2 | chr17:17374331-17394899 |
| 18235 | Rgs9bp | NM_145840.3 | chr7:35578995-35585582 | 18330 | Riok3 | NM_024182.4 | chr18:12128849-12157367 |
| 18236 | Rgsl1 | NM_001243223.1 | chr1:153779386-153844141 | 18331 | Ripk1 | NM_009068.3 | chr13:34002873-34035170 |
| 18237 | Rhag | NM_011269.2 | chr17:40811148-40840754 | 18332 | Ripk2 | NM_138952.3 | chr4:16123374-16163498 |
| 18238 | Rhbdd1 | NM_001122685.1 | chr1:82339048-82445367 | 18333 | Ripk3 | NM_001164107.1 | chr14:55784994-55788857 |
| 18239 | Rhbdd2 | NM_146002.2 | chr5:135632653-135646376 | 18334 | Ripk4 | NM_023663.6 | chr16:97741941-97763755 |
| 18240 | Rhbdd3 | NM_001290491.1 | chr11:5099272-5108100 | 18335 | Ripply1 | NM_001037915.2 | chrX:139779680-139782353 |
| 18241 | Rhbdf1 | NM_001291818.1 | chr11:32209584-32222293 | 18336 | Ripply2 | NM_001037907.1 | chr9:87015536-87019916 |
| 18242 | Rhbdf2 | NM_001167680.1 | chr11:116598165-116624252 | 18337 | Ripply3 | NM_133229.2 | chr16:94328421-94336935 |
| 18243 | Rhbdl1 | NM_144816.1 | chr7:25834464-25837127 | 18338 | Rit1 | NM_001163310.1 | chr3:88716853-88731048 |
| 18244 | Rhbdl2 | NM_183163.2 | chr4:123787874-123829904 | 18339 | Rit2 | NM_009065.2 | chr18:30974313-31317128 |
| 18245 | Rhbdl3 | NM_139228.3 | chr11:80300911-80355986 | 18340 | Rita1 | NM_029096.3 | chr5:120609059-120612589 |
| 18246 | Rhbg | NM_021375.3 | chr3:88242873-88254684 | 18341 | Rlbp1 | NM_001173483.1 | chr7:79374869-79387027 |
| 18247 | Rhcg | NM_019799.3 | chr7:79593362-79617657 | 18342 | Rlf | NM_001081013.1 | chr4:121145372-121188534 |
| 18248 | Rhd | NM_011270.3 | chr4:134864535-134896172 | 18343 | Rlim | NM_011256.3 | chrX:103957166-103981284 |
| 18249 | Rheb | NM_053075.3 | chr5:24802822-24842361 | 18344 | Rln1 | NM_011272.2 | chr19:29331754-29334670 |
| 18250 | Rhebl1 | NM_026967.4 | chr15:98877759-98881414 | 18345 | Rln3 | NM_173184.1 | chr8:84043066-84044979 |
| 18251 | Rhno1 | NR_027359.1 | chr6:128356999-128362897 | 18346 | Rltpr | NM_001033320.2 | chr8:105690905-105698165 |
| 18252 | Rho | NM_145383.1 | chr6:115931926-115938830 | 18347 | Rmdn1 | NM_025476.6 | chr4:19575065-19606932 |
| 18253 | Rhoa | NM_016802.5 | chr9:108306159-108337943 | 18348 | Rmdn2 | NM_201361.2 | chr17:79614899-79682152 |
| 18254 | Rhob | NM_007483.2 | chr12:8497758-8499985 | 18349 | Rmdn3 | NM_001033136.3 | chr2:119136997-119157034 |
| 18255 | Rhobtb1 | NM_001081347.1 | chr10:69212656-69291784 | 18350 | Rmi1 | NM_001168248.1 | chr13:58402596-58411149 |
| 18256 | Rhobtb2 | NM_153514.5 | chr14:69784989-69805545 | 18351 | Rmi2 | NM_001162932.1 | chr16:10835058-10843235 |
| 18257 | Rhobtb3 | NM_028493.2 | chr13:75869536-75943824 | 18352 | Rmnd1 | NM_025343.5 | chr10:4403168-4432252 |
| 18258 | Rhoc | NM_001291859.1 | chr3:104789033-104794459 | 18353 | Rmnd5a | NM_024288.2 | chr6:71388633-71406637 |
| 18259 | Rhod | NM_007485.4 | chr19:4425456-4439424 | 18354 | Rmnd5b | NM_025346.1 | chr11:51623672-51635896 |
| 18260 | Rhof | NM_175092.3 | chr5:123118179-123132629 | 18355 | Rmrp | NR_001460.1 | chr4:43492784-43493059 |
| 18261 | Rhog | NM_019566.3 | chr7:102239122-102250118 | 18356 | Rmst | NR_028262.1 | chr10:92081745-92165178 |
| 18262 | Rhoh | NM_001081105.1 | chr5:65863568-65896700 | 18357 | Rn4.5s | NR_002841.1 | chr6:47654920-47752925 |
| 18263 | Rhoj | NM_023275.2 | chr12:75308312-75401455 | 18358 | Rn45s | NR_046233.2 | chr17:39842996-39848829 |
| 18264 | Rhoq | NM_145491.2 | chr17:86963110-87000069 | 18359 | Rnase1 | NM_011271.2 | chr14:51145001-51146767 |
| 18265 | Rhot1 | NM_001163354.1 | chr11:80209054-80267907 | 18360 | Rnase10 | NM_001162863.1 | chr14:51007750-51010758 |
| 18266 | Rhot2 | NM_145949.2 | chr17:25838837-25844851 | 18361 | Rnase11 | NM_001011877.2 | chr14:51049450-51050163 |
| 18267 | Rhou | NM_133955.4 | chr8:123653928-123663880 | 18362 | Rnase12 | NM_001011875.2 | chr14:51056697-51057242 |
| 18268 | Rhov | NM_145530.2 | chr2:119269200-119271226 | 18363 | Rnase13 | NM_001011687.2 | chr14:51922159-51922773 |
| 18269 | Rhox1 | NM_001025084.2 | chrX:37213804-37222258 | 18364 | Rnase2a | NM_053113.2 | chr14:51255261-51256112 |
| 18270 | Rhox10 | NM_001024850.2 | chrX:38066474-38071688 | 18365 | Rnase2b | NM_019398.2 | chr14:51162259-51163018 |
| 18271 | Rhox11 | NM_198598.2 | chrX:38076597-38085139 | 18366 | Rnase4 | NM_021472.4 | chr14:51091076-51106151 |
| 18272 | Rhox12 | NM_001025083.2 | chrX:38104061-38110907 | 18367 | Rnase6 | NM_030098.2 | chr14:51129067-51131121 |
| 18273 | Rhox13 | NM_001185002.1 | chrX:38120839-38129966 | 18368 | Rnase9 | NM_183032.2 | chr14:51038458-51041867 |
| 18274 | Rhox2a | NM_029203.2 | chrX:37244991-37249690 | 18369 | Rnaseh1 | NM_001286865.1 | chr12:28649601-28659591 |
| 18275 | Rhox2b | NM_001099316.1 | chrX:37412104-37416806 | 18370 | Rnaseh2a | NM_027187.3 | chr8:84956609-84966011 |
| 18276 | Rhox2c | NM_001099318.1 | chrX:37453658-37458375 | 18371 | Rnaseh2b | NM_026001.2 | chr14:62332104-62372992 |
| 18277 | Rhox2d | NM_001081669.2 | chrX:37493409-37497715 | 18372 | Rnaseh2c | NM_026616.2 | chr19:5601872-5602959 |
| 18278 | Rhox2e | NM_001085348.1 | chrX:37530467-37541809 | 18373 | Rnasek | NM_173742.3 | chr11:70238122-70239852 |
| 18279 | Rhox2f | NM_001085356.1 | chrX:37571420-37576159 | 18374 | Rnasel | NM_011882.2 | chr1:153749425-153764221 |
| 18280 | Rhox2g | NM_001114153.1 | chrX:37639111-37643470 | 18375 | Rnaset2a | NM_001083938.2 | chr17:8128597-8147788 |
| 18281 | Rhox2h | NM_001100465.1 | chrX:37668996-37673277 | 18376 | Rnaset2b | NM_026611.2 | chr17:6978859-8147832 |
| 18282 | Rhox3a | NM_194063.3 | chrX:37249918-37258978 | 18377 | Rnd1 | NM_172612.3 | chr15:98669204-98677461 |
| 18283 | Rhox3c | NM_001012457.4 | chrX:37469867-37473961 | 18378 | Rnd2 | NM_009708.1 | chr11:101468337-101471306 |
| 18284 | Rhox3e | NM_001184969.1 | chrX:37254877-37550897 | 18379 | Rnd3 | NM_028810.2 | chr2:51130438-51149111 |
| 18285 | Rhox3f | NM_001040089.3 | chrX:37581351-37585496 | 18380 | Rnf10 | NM_016698.2 | chr5:115241769-115272895 |
| 18286 | Rhox3g | NM_001145406.3 | chrX:37623430-37628139 | 18381 | Rnf103 | NM_009543.3 | chr6:71493876-71510880 |
| 18287 | Rhox3h | NM_001114157.1 | chrX:37657687-37668764 | 18382 | Rnf11 | NM_013876.3 | chr4:109452856-109476505 |
| 18288 | Rhox4a | NM_001039693.3 | chrX:37265374-37395620 | 18383 | Rnf111 | NM_033604.2 | chr9:70425428-70503725 |
| 18289 | Rhox4b | NM_021300.2 | chrX:37432493-37437278 | 18384 | Rnf112 | NM_001291024.1 | chr11:61448416-61453992 |
| 18290 | Rhox4c | NM_001039689.1 | chrX:37480336-37485124 | 18385 | Rnf113a1 | NM_153503.2 | chrX:37191221-37192465 |
| 18291 | Rhox4d | NM_001039695.1 | chrX:37514534-37519175 | 18386 | Rnf113a2 | NM_025525.2 | chr12:84417199-84418578 |
| 18292 | Rhox4e | NM_201236.3 | chrX:37557411-37562282 | 18387 | Rnf114 | NM_030743.5 | chr2:167492644-167516166 |
| 18293 | Rhox4f | NM_001039696.1 | chrX:37602894-37607686 | 18388 | Rnf115 | NM_026406.3 | chr3:96727610-96791355 |
| 18294 | Rhox4g | NM_001039698.1 | chrX:37646500-37651327 | 18389 | Rnf121 | NM_029211.2 | chr7:102019871-102065132 |
| 18295 | Rhox5 | NM_008818.2 | chrX:37754607-37808878 | 18390 | Rnf122 | NM_175136.2 | chr8:31111845-31131473 |
| 18296 | Rhox6 | NM_008955.1 | chrX:37827054-37829857 | 18391 | Rnf123 | NM_032543.2 | chr9:108051671-108079375 |
| 18297 | Rhox7 | NM_001039586.2 | chrX:37831685-37841171 | 18392 | Rnf125 | NM_026301.2 | chr18:20944624-20983848 |
| 18298 | Rhox8 | NM_001004193.2 | chrX:37874775-37878944 | 18393 | Rnf126 | NM_144528.3 | chr10:79758514-79766952 |
| 18299 | Rhox9 | NM_023894.1 | chrX:37899096-37901770 | 18394 | Rnf128 | NM_001254761.1 | chrX:139563339-139673145 |
| 18300 | Rhpn1 | NM_001163465.1 | chr15:75704287-75714419 | 18395 | Rnf13 | NM_001113413.2 | chr3:57736061-57835425 |
| 18301 | Rhpn2 | NM_027897.4 | chr7:35334236-35392287 | 18396 | Rnf130 | NM_001290749.1 | chr11:50025330-50104759 |
| 18302 | Rian | NR_028261.1 | chr12:109603944-109661711 | 18397 | Rnf133 | NM_198251.2 | chr6:23648868-23650305 |
| 18303 | Ribc1 | NM_025660.2 | chrX:152004583-152016295 | 18398 | Rnf135 | NM_028019.3 | chr11:80183871-80199753 |
| 18304 | Ribc2 | NM_026357.2 | chr15:85132098-85144569 | 18399 | Rnf138 | NM_019706.3 | chr18:21001299-21028224 |
| 18305 | Ric3 | NM_001033418.1 | chr7:109034318-109083324 | 18400 | Rnf138rt1 | NM_028842.3 | chrX:163766138-163761332 |
| 18306 | Ric8 | NM_053194.4 | chr7:140857396-140863731 | 18401 | Rnf139 | NM_175226.4 | chr15:58889228-58902390 |
| 18307 | Ric8b | NM_001013441.2 | chr10:84917612-85018337 | 18402 | Rnf14 | NM_001164621.1 | chr18:38296804-38317849 |
| 18308 | Rictor | NM_030163.1 | chr15:6708380-6800400 | 18403 | Rnf141 | NM_025999.3 | chr7:110816534-110844381 |
| 18309 | Rif1 | NM_175238.5 | chr2:52072836-52122381 | 18404 | Rnf144a | NM_001081977.2 | chr12:26306793-26415262 |
| 18310 | Riiad1 | NM_025506.2 | chr3:94464984-94473591 | 18405 | Rnf144b | NM_001170643.1 | chr13:47194002-47247991 |
| 18311 | Rilp | NM_001029938.2 | chr11:75510093-75513166 | 18406 | Rnf145 | NM_001166553.1 | chr11:44519376-44554977 |
| 18312 | Rilpl1 | NM_021430.2 | chr5:124493079-124531391 | 18407 | Rnf146 | NM_001110196.1 | chr10:29344175-29362442 |
| 18313 | Rilpl2 | NM_030259.1 | chr5:124463264-124478235 | 18408 | Rnf148 | NM_027754.1 | chr6:23653894-23655136 |
| 18314 | Rimbp2 | NM_001081388.2 | chr5:128757787-128953486 | 18409 | Rnf149 | NM_001033135.3 | chr1:39551295-39577347 |
| 18315 | Rimbp3 | NM_001033338.3 | chr16:17208134-17213982 | 18410 | Rnf150 | NM_177378.4 | chr8:82863355-83091271 |
| 18316 | Rimkla | NM_177572.4 | chr4:119465284-119492598 | 18411 | Rnf151 | NM_026205.3 | chr17:24715839-24718057 |
| 18317 | Rimklb | NM_027664.1 | chr6:122453608-122486305 | 18412 | Rnf152 | NM_001160368.1 | chr1:105276916-105356710 |
| 18318 | Rims1 | NM_001162623.1 | chr1:22288421-22805724 | 18413 | Rnf157 | NM_027258.1 | chr11:116336344-116413032 |
| 18319 | Rims2 | NM_001256382.1 | chr15:39198285-39684372 | 18414 | Rnf165 | NM_001164504.1 | chr18:77456109-77565136 |
| 18320 | Rims3 | NM_182929.2 | chr4:120877868-120891560 | 18415 | Rnf166 | NM_001033142.2 | chr8:122466146-122476064 |
| 18321 | Rims4 | NM_183023.1 | chr2:163863880-163918683 | 18416 | Rnf167 | NM_027445.2 | chr11:70647588-70651414 |
| 18322 | Rin1 | NM_145495.2 | chr19:5050807-5057071 | 18417 | Rnf168 | NM_027355.2 | chr16:32277460-32301439 |
| 18323 | Rin2 | NM_028724.4 | chr2:145786115-145887616 | 18418 | Rnf169 | NM_175388.3 | chr7:99920253-99980458 |
| 18324 | Rin3 | NM_001161365.1 | chr12:102283640-102390854 | 18419 | Rnf17 | NM_001033043.1 | chr14:56402696-56525031 |
| 18325 | Ring1 | NM_009066.3 | chr17:34020791-34024680 | 18420 | Rnf170 | NM_029965.2 | chr8:26119379-26143869 |
| 18326 | Rinl | NM_177158.5 | chr7:28788968-28798966 | 18421 | Rnf180 | NM_027934.2 | chr13:105147493-105293014 |
| 18327 | Rint1 | NM_177323.4 | chr5:23787870-23820369 | 18422 | Rnf181 | NM_025607.3 | chr6:72359713-72362381 |

Fig. 26 - 98

| | | | | | | | | |
|---|---|---|---|---|---|---|---|---|
| 18423 | Rnf182 | NM_183204.4 | chr13:43615796-43670944 | | 18518 | Rpl12 | NM_009076.3 | chr2:32961711-32964045 |
| 18424 | Rnf183 | NM_153504.3 | chr4:62427541-62434726 | | 18519 | Rpl13 | NM_016738.5 | chr8:123102349-123105242 |
| 18425 | Rnf185 | NM_001290472.1 | chr11:3415972-3452956 | | 18520 | Rpl13a | NM_009438.5 | chr7:45125562-45128745 |
| 18426 | Rnf186 | NM_025786.3 | chr4:138967111-138968366 | | 18521 | Rpl14 | NM_025974.2 | chr9:120571516-120574653 |
| 18427 | Rnf187 | NM_022423.2 | chr11:58932287-58938906 | | 18522 | Rpl14-ps1 | NR_110499.1 | chr7:45324957-45325651 |
| 18428 | Rnf19a | NM_013923.2 | chr15:36239933-36283147 | | 18523 | Rpl15 | NM_025586.3 | chr14:18267822-18270986 |
| 18429 | Rnf19b | NM_029219.1 | chr4:129058270-129084526 | | 18524 | Rpl17 | NM_001002239.3 | chr18:75000476-75003381 |
| 18430 | Rnf2 | NM_011277.2 | chr1:151469405-151500823 | | 18525 | Rpl18 | NM_009077.2 | chr7:45718070-45720835 |
| 18431 | Rnf20 | NM_001163263.1 | chr4:49632059-49656886 | | 18526 | Rpl18a | NM_029751.4 | chr8:70894721-70897443 |
| 18432 | Rnf207 | NM_001033489.2 | chr4:152307022-152318625 | | 18527 | Rpl19 | NM_001159483.1 | chr11:98026709-98030493 |
| 18433 | Rnf208 | NM_176834.2 | chr2:25242928-25244261 | | 18528 | Rpl21 | NM_019647.6 | chr5:146832889-146837032 |
| 18434 | Rnf214 | NM_178709.4 | chr9:45863690-45906877 | | 18529 | Rpl22 | NM_001277113.1 | chr4:152324435-152334082 |
| 18435 | Rnf215 | NM_027859.2 | chr11:4135159-4141192 | | 18530 | Rpl22l1 | NM_026517.2 | chr3:28805510-28807415 |
| 18436 | Rnf216 | NM_080561.4 | chr5:142990892-143113020 | | 18531 | Rpl23 | NM_022891.3 | chr11:97777525-97782439 |
| 18437 | Rnf217 | NM_001146349.1 | chr10:31501886-31509725 | | 18532 | Rpl23a | NM_207523.2 | chr11:78180935-78183584 |
| 18438 | Rnf219 | NM_026047.4 | chr14:104477533-104522666 | | 18533 | Rpl24 | NM_024218.4 | chr16:55966274-55971437 |
| 18439 | Rnf220 | NM_025739.3 | chr4:117271462-117497052 | | 18534 | Rpl26 | NM_009080.2 | chr11:68901565-68904534 |
| 18440 | Rnf222 | NM_177080.3 | chr11:68888552-68895015 | | 18535 | Rpl27 | NM_011289.3 | chr11:101442244-101445596 |
| 18441 | Rnf223 | NM_001220499.1 | chr4:156132169-156133419 | | 18536 | Rpl27a | NM_011975.3 | chr7:109519194-109522369 |
| 18442 | Rnf224 | NM_001033410.2 | chr2:25234475-25236787 | | 18537 | Rpl28 | NM_009081.2 | chr7:4792964-4794547 |
| 18443 | Rnf24 | NM_178607.4 | chr2:131298487-131352892 | | 18538 | Rpl29 | NM_009082.2 | chr9:106429538-106431567 |
| 18444 | Rnf25 | NM_021313.1 | chr1:74593747-74601397 | | 18539 | Rpl3 | NM_013762.2 | chr15:80077780-80083406 |
| 18445 | Rnf26 | NM_153762.3 | chr9:44110780-44113051 | | 18540 | Rpl30 | NM_001163485.1 | chr15:34446507-34443276 |
| 18446 | Rnf31 | NM_194346.2 | chr14:55591789-55606671 | | 18541 | Rpl31 | NM_001252218.1 | chr1:39367850-39371910 |
| 18447 | Rnf32 | NM_001289751.1 | chr5:29195992-29225524 | | 18542 | Rpl31-ps12 | NM_001258458.3 | chr16:16819712-16820196 |
| 18448 | Rnf34 | NM_030564.1 | chr5:122850187-122868945 | | 18543 | Rpl32 | NM_172086.2 | chr6:115805513-115808743 |
| 18449 | Rnf38 | NM_001038993.3 | chr4:44126211-44168283 | | 18544 | Rpl34 | NM_001005859.3 | chr3:130726826-130730398 |
| 18450 | Rnf39 | NM_001099632.1 | chr17:36940350-36947986 | | 18545 | Rpl34-ps1 | NM_001199350.1 | chr3:130726836-130730329 |
| 18451 | Rnf4 | NM_011278.5 | chr5:34336249-34353445 | | 18546 | Rpl35 | NM_025592.3 | chr2:39001580-39005131 |
| 18452 | Rnf40 | NM_172281.2 | chr7:127588697-127603605 | | 18547 | Rpl35a | NM_001130484.1 | chr16:33056481-33060188 |
| 18453 | Rnf41 | NM_001164237.1 | chr10:128411615-128441441 | | 18548 | Rpl36 | NM_018730.3 | chr17:56613394-56614246 |
| 18454 | Rnf43 | NM_172448.3 | chr11:87663086-87735539 | | 18549 | Rpl36a | NM_019865.5 | chrX:134585653-134588062 |
| 18455 | Rnf44 | NM_001146025.1 | chr13:54679398-54687808 | | 18550 | Rpl36al | NM_025589.4 | chr12:69182733-69184067 |
| 18456 | Rnf5 | NM_019403.3 | chr17:34601098-34603561 | | 18551 | Rpl37 | NM_026069.3 | chr15:5116612-5119140 |
| 18457 | Rnf6 | NM_001256085.1 | chr5:146209193-146220971 | | 18552 | Rpl37a | NM_009084.4 | chr1:72711259-72713813 |
| 18458 | Rnf7 | NM_011279.3 | chr9:96470936-96478675 | | 18553 | Rpl38 | NM_001048057.1 | chr11:114668542-114673331 |
| 18459 | Rnf8 | NM_021419.2 | chr17:29614788-29641664 | | 18554 | Rpl39 | NM_026055.2 | chrX:37082517-37085222 |
| 18460 | Rnft1 | NM_029788.5 | chr1:86484656-86499007 | | 18555 | Rpl39l | NM_026594.2 | chr16:10170227-10174911 |
| 18461 | Rnft2 | NM_001099902.1 | chr5:118190735-118245025 | | 18556 | Rpl3l | NM_001163945.1 | chr17:24727828-24736149 |
| 18462 | Rngtt | NM_011884.3 | chr4:33310310-33502614 | | 18557 | Rpl4 | NM_024212.4 | chr9:64173386-64178562 |
| 18463 | Rnh1 | NM_001172100.1 | chr7:141160325-141172851 | | 18558 | Rpl41 | NM_018860.4 | chr10:128548109-128549168 |
| 18464 | Rnls | NM_001146242.2 | chr19:33137744-33392295 | | 18559 | Rpl5 | NM_016980.2 | chr5:107900527-107909005 |
| 18465 | Rnmt | NM_001170953.1 | chr18:68300354-68324852 | | 18560 | Rpl6 | NM_011290.5 | chr5:121204500-121209241 |
| 18466 | Rnmtl1 | NM_183283.5 | chr11:76243735-76250622 | | 18561 | Rpl7 | NM_011291.5 | chr1:16101295-16104433 |
| 18467 | Rnpc3 | NM_001038696.1 | chr3:113605066-113630149 | | 18562 | Rpl7a | NM_013721.3 | chr2:26910806-26913311 |
| 18468 | Rnpep | NM_001159624.1 | chr1:135262698-135284084 | | 18563 | Rpl7l1 | NM_025433.3 | chr17:46773906-46782656 |
| 18469 | Rnpepl1 | NM_181405.4 | chr1:92910824-92920585 | | 18564 | Rpl8 | NM_012053.2 | chr15:76904070-76906318 |
| 18470 | Rnps1 | NM_001080127.1 | chr17:24414674-24425897 | | 18565 | Rpl9 | NM_011292.2 | chr5:65388363-65391431 |
| 18471 | Rnu11 | NR_002865.2 | chr4:132270078-132270186 | | 18566 | Rplp0 | NM_007475.5 | chr5:115559466-115563729 |
| 18472 | Rnu12 | NR_004432.2 | chr15:83149644-83149794 | | 18567 | Rplp1 | NM_018853.3 | chr9:61913282-61914510 |
| 18473 | Rnu6 | NR_003027.2 | chr19:14438479-14438506 | | 18568 | Rplp2 | NM_026020.6 | chr7:141447649-141451342 |
| 18474 | Rnu7 | NR_024201.3 | chr5:53698563-53698588 | | 18569 | Rplp2-ps1 | NR_038063.1 | chr12:75630924-75631749 |
| 18475 | Rnu73b | NR_004418.1 | chr3:86140616-86140687 | | 18570 | Rpn1 | NM_133933.4 | chr6:88084472-88105304 |
| 18476 | Robo1 | NM_019413.2 | chr16:72663148-73046100 | | 18571 | Rpn2 | NM_019642.4 | chr2:157279097-157326318 |
| 18477 | Robo2 | NM_175549.4 | chr16:73892305-74410912 | | 18572 | Rpp14 | NM_025938.4 | chr14:8080312-8091846 |
| 18478 | Robo3 | NM_001164767.1 | chr9:37416044-37433175 | | 18573 | Rpp21 | NM_026308.2 | chr17:36255672-36257846 |
| 18479 | Robo4 | NM_028783.3 | chr9:37401896-37414023 | | 18574 | Rpp25 | NM_133982.1 | chr9:57504101-57505447 |
| 18480 | Rock1 | NM_009071.2 | chr18:10064400-10181792 | | 18575 | Rpp25l | NM_027278.3 | chr4:41712032-41713517 |
| 18481 | Rock2 | NM_009072.2 | chr12:16894977-16988274 | | 18576 | Rpp30 | NM_019428.3 | chr19:36083715-36104773 |
| 18482 | Rogdi | NM_133185.2 | chr16:5008728-5013553 | | 18577 | Rpp38 | NM_001013076.2 | chr2:3328948-3332628 |
| 18483 | Rom1 | NM_009073.4 | chr19:8927381-8929356 | | 18578 | Rpp40 | NM_145938.4 | chr13:35895103-35906347 |
| 18484 | Romo1 | NM_001164216.1 | chr2:156144152-156145794 | | 18579 | Rpph1 | NR_002142.2 | chr14:50807446-50807771 |
| 18485 | Ropn1 | NM_030744.2 | chr16:34651210-34678610 | | 18580 | Rprd1a | NM_144861.2 | chr18:24484961-24530204 |
| 18486 | Ropn1l | NM_145852.2 | chr15:31441209-31493689 | | 18581 | Rprd1b | NM_001291134.1 | chr2:158028496-158078207 |
| 18487 | Ror1 | NM_013845.5 | chr4:100495790-100444806 | | 18582 | Rprd2 | NM_001081293.1 | chr3:95758872-95818953 |
| 18488 | Ror2 | NM_013846.3 | chr13:53109316-53286109 | | 18583 | Rpril | NR_044434.3 | chr6:69326936-69327174 |
| 18489 | Rora | NM_001289916.1 | chr9:69289840-69388246 | | 18584 | Rpril2 | NR_004439.2 | chr3:22251369-22251607 |
| 18490 | Rorb | NM_001043554.2 | chr19:18930608-19111196 | | 18585 | Rpril3 | NR_024198.2 | chr8:3803124-3803361 |
| 18491 | Rorc | NM_011281.3 | chr3:94372793-94398274 | | 18586 | Rprm | NM_023396.4 | chr2:54084092-54085552 |
| 18492 | Ros1 | NM_011274.2 | chr10:52045925-52195244 | | 18587 | Rprml | NM_001033212.2 | chr11:103649508-103650580 |
| 18493 | Rp1 | NM_001195663.1 | chr1:4290845-4409241 | | 18588 | Rps10 | NM_025963.3 | chr17:27630428-27635242 |
| 18494 | Rp1l1 | NM_146246.3 | chr14:63992430-64033506 | | 18589 | Rps11 | NM_013725.4 | chr7:45122387-45124389 |
| 18495 | Rp2h | NM_001290643.1 | chrX:20364480-20400858 | | 18590 | Rps12 | NM_011295.6 | chr10:23785182-23787209 |
| 18496 | Rp9 | NM_018739.2 | chr9:22448311-22468356 | | 18591 | Rps13 | NM_026533.3 | chr7:116331506-116334190 |
| 18497 | Rpa1 | NM_001164223.1 | chr11:75300258-75348383 | | 18592 | Rps14 | NM_020600.4 | chr18:60774595-60778546 |
| 18498 | Rpa2 | NM_011284.3 | chr4:132768359-132778746 | | 18593 | Rps15 | NM_009091.2 | chr10:80292430-80294114 |
| 18499 | Rpa3 | NM_026632.4 | chr6:8255935-8259141 | | 18594 | Rps15a | NM_170669.2 | chr7:118104375-118116147 |
| 18500 | Rpain | NM_001252413.1 | chr11:70970199-70977933 | | 18595 | Rps15a-ps4 | NR_036572.1 | chr4:132219892-132220589 |
| 18501 | Rpap1 | NM_001164061.1 | chr2:119763958-119787537 | | 18596 | Rps15a-ps6 | NR_029471.2 | chr11:6172507-6173331 |
| 18502 | Rpap2 | NM_001163461.2 | chr5:107597695-107642918 | | 18597 | Rps16 | NM_013647.2 | chr7:28350688-28352698 |
| 18503 | Rpap3 | NM_028003.2 | chr15:97675104-97705822 | | 18598 | Rps17 | NM_009092.3 | chr7:81342732-81345234 |
| 18504 | Rpe | NM_025683.3 | chr1:66700830-66719805 | | 18599 | Rps18 | NM_011296.2 | chr17:33951998-33955641 |
| 18505 | Rpe65 | NM_029987.2 | chr3:159599180-159625307 | | 18600 | Rps19 | NM_023133.2 | chr7:24884713-24889802 |
| 18506 | Rpf1 | NM_027332.3 | chr3:146510794-146521423 | | 18601 | Rps19bp1 | NM_175109.3 | chr15:80266613-80284306 |
| 18507 | Rpf2 | NM_001042556.1 | chr10:40223245-40246979 | | 18602 | Rps19-ps3 | NR_033639.1 | chr4:147821776-147822202 |
| 18508 | Rpgr | NM_001177950.1 | chrX:10158215-10216795 | | 18603 | Rps2 | NM_008503.5 | chr17:24720062-24721927 |
| 18509 | Rpgrip1 | NM_146168515.1 | chr14:52110902-52161339 | | 18604 | Rps20 | NM_026147.5 | chr4:3834472-3835600 |
| 18510 | Rpgrip1l | NM_173431.2 | chr8:91217029-91313222 | | 18605 | Rps21 | NM_025587.2 | chr2:180257378-180258444 |
| 18511 | Rph3a | NM_011286.3 | chr5:120940499-121009588 | | 18606 | Rps23 | NM_024175.3 | chr13:90923216-90924732 |
| 18512 | Rph3al | NM_001242159.1 | chr11:75899724-75925891 | | 18607 | Rps24 | NM_011297.2 | chr14:24490680-24496146 |
| 18513 | Rpia | NM_009075.3 | chr6:70765719-70792175 | | 18608 | Rps25 | NM_024266.3 | chr9:44407713-44410406 |
| 18514 | Rpl10 | NM_052835.3 | chrX:74270815-74273135 | | 18609 | Rps26 | NM_013765.2 | chr10:128624528-128626506 |
| 18515 | Rpl10a | NM_011287.2 | chr17:28328470-28331033 | | 18610 | Rps27 | NM_027015.4 | chr3:90212666-90213648 |
| 18516 | Rpl10l | NM_001162933.1 | chr12:66283378-66284401 | | 18611 | Rps27a | NM_001033865.1 | chr11:29545841-29548040 |
| 18517 | Rpl11 | NM_025919.2 | chr4:136049947-136053371 | | 18612 | Rps27l | NM_026467.4 | chr9:66946075-66949522 |

Fig. 26 - 99

| | | | | | | | |
|---|---|---|---|---|---|---|---|
| 18613 | Rps27rt | NM_001190258.1 | chr3:90212666-90213647 | 18708 | Rtn4 | NM_024226.4 | chr11:29718562-29744414 |
| 18614 | Rps28 | NM_016844.2 | chr17:33823036-33824498 | 18709 | Rtn4ip1 | NM_130892.4 | chr10:43901806-43947862 |
| 18615 | Rps29 | NM_009093.2 | chr12:69157721-69159186 | 18710 | Rtn4r | NM_022982.2 | chr16:18127705-18152408 |
| 18616 | Rps3 | NM_012052.2 | chr7:99477896-99483709 | 18711 | Rtn4rl1 | NM_177708.5 | chr11:75193992-75267762 |
| 18617 | Rps3a1 | NM_016959.4 | chr3:86137939-86142668 | 18712 | Rtn4rl2 | NM_199223.1 | chr2:84871946-84886692 |
| 18618 | Rps4l | NR_003634.2 | chr6:148354655-148355596 | 18713 | Rtp1 | NM_001004151.2 | chr16:23429132-23433960 |
| 18619 | Rps4x | NM_009094.2 | chrX:102184940-102189391 | 18714 | Rtp2 | NM_001008230.3 | chr16:23925547-23930794 |
| 18620 | Rps5 | NM_009095.2 | chr7:12922310-12926686 | 18715 | Rtp3 | NM_153100.2 | chr9:110984942-110989713 |
| 18621 | Rps6 | NM_009096.3 | chr4:86854098-86857367 | 18716 | Rtp4 | NM_023386.5 | chr16:23609918-23614222 |
| 18622 | Rps6ka1 | NM_001285505.1 | chr4:133847296-133887797 | 18717 | Rttn | NM_175542.3 | chr18:88971789-89131014 |
| 18623 | Rps6ka2 | NM_011299.4 | chr17:7170114-7303316 | 18718 | Rubie | NR_046459.1 | chr14:46568330-46575851 |
| 18624 | Rps6ka3 | NM_148945.2 | chrX:159255781-159368244 | 18719 | Rufy1 | NM_172557.2 | chr11:50389302-50431111 |
| 18625 | Rps6ka4 | NM_019924.2 | chr19:6829083-6840627 | 18720 | Rufy2 | NM_027425.3 | chr10:62980222-63016742 |
| 18626 | Rps6ka5 | NM_153587.2 | chr12:100549777-100725028 | 18721 | Rufy3 | NM_001289774.1 | chr5:88565039-88651417 |
| 18627 | Rps6ka6 | NM_025949.3 | chrX:111387836-111537959 | 18722 | Rufy4 | NM_001034060.3 | chr1:74125540-74148223 |
| 18628 | Rps6kb1 | NM_001114334.1 | chr11:86499010-86544807 | 18723 | Rundc1 | NM_172566.4 | chr11:101425084-101435665 |
| 18629 | Rps6kb2 | NM_021485.2 | chr19:4156976-4163245 | 18724 | Rundc3a | NM_001252347.1 | chr11:102393402-102402939 |
| 18630 | Rps6kc1 | NM_178775.4 | chr1:190772878-190911770 | 18725 | Rundc3b | NM_198620.1 | chr5:8490335-8622952 |
| 18631 | Rps6kl1 | NM_146244.4 | chr12:85135595-85151264 | 18726 | Runx1 | NM_001111021.2 | chr16:92601465-92826074 |
| 18632 | Rps7 | NM_011300.3 | chr12:28630846-28635953 | 18727 | Runx1t1 | NM_001111026.2 | chr4:13743301-13895055 |
| 18633 | Rps8 | NM_009098.2 | chr4:117153835-117156132 | 18728 | Runx2 | NM_001145920.2 | chr17:44603988-44736648 |
| 18634 | Rps9 | NM_029767.2 | chr7:3704040-3706897 | 18729 | Runx3 | NM_019732.2 | chr4:135120644-135177990 |
| 18635 | Rpsa | NM_011029.4 | chr9:120127765-120132369 | 18730 | Rusc1 | NM_001083807.1 | chr3:89083978-89093363 |
| 18636 | Rptn | NM_009100.2 | chr3:93393698-93399442 | 18731 | Rusc2 | NM_001037709.2 | chr4:43381981-43427092 |
| 18637 | Rptor | NM_028898.3 | chr11:119602904-119899591 | 18732 | Ruvbl1 | NM_019685.2 | chr6:88465422-88497566 |
| 18638 | Rptoros | NR_045312.1 | chr11:119820810-119834365 | 18733 | Ruvbl2 | NM_011304.3 | chr7:45421897-45434464 |
| 18639 | Rpusd1 | NM_028009.3 | chr17:25727750-25731456 | 18734 | Rwdd1 | NM_025614.3 | chr10:33996554-34019616 |
| 18640 | Rpusd2 | NM_173450.3 | chr2:119034789-119042197 | 18735 | Rwdd2a | NM_001145968.1 | chr9:86572052-86574899 |
| 18641 | Rpusd3 | NM_001033204.1 | chr6:113415218-113419340 | 18736 | Rwdd2b | NM_016924.2 | chr16:87433330-87440592 |
| 18642 | Rpusd4 | NM_028040.2 | chr9:35267880-35275957 | 18737 | Rwdd3 | NM_025637.3 | chr3:121155401-121171695 |
| 18643 | Rqcd1 | NM_021383.5 | chr1:74506059-74530842 | 18738 | Rwdd4a | NM_203507.3 | chr8:47533644-47552837 |
| 18644 | Rrad | NM_019662.2 | chr8:104628065-104631321 | 18739 | Rxfp1 | NM_212452.1 | chr5:79644715-79737794 |
| 18645 | Rraga | NM_178376.3 | chr4:86575672-86577283 | 18740 | Rxfp2 | NM_001289564.1 | chr5:150018674-150082186 |
| 18646 | Rragb | NM_001004154.2 | chrX:153139957-153171943 | 18741 | Rxfp3 | NM_178717.3 | chr15:11033716-11037968 |
| 18647 | Rragc | NM_017475.2 | chr4:123917432-123936997 | 18742 | Rxfp4 | NM_181817.3 | chr3:88651897-88653142 |
| 18648 | Rragd | NM_027491.2 | chr4:32982997-33022180 | 18743 | Rxra | NM_001290481.1 | chr2:27709291-27763319 |
| 18649 | Rras | NM_009101.2 | chr7:45018006-45021644 | 18744 | Rxrb | NM_001205214.1 | chr17:34031811-34038403 |
| 18650 | Rras2 | NM_025846.2 | chr7:114046781-114117781 | 18745 | Rxrg | NM_001159731.1 | chr1:167618264-167639623 |
| 18651 | Rrbp1 | NM_024281.2 | chr2:143947394-144011263 | 18746 | Rybp | NM_019743.3 | chr6:100228564-100287358 |
| 18652 | Rreb1 | NM_001039188.1 | chr13:37827392-37935534 | 18747 | Ryk | NM_001042607.1 | chr9:102834919-102908307 |
| 18653 | Rrh | NM_009102.3 | chr3:129808574-129822505 | 18748 | Ryr1 | NM_009109.2 | chr7:29003339-29125151 |
| 18654 | Rrm1 | NM_009103.3 | chr7:102441694-102469771 | 18749 | Ryr2 | NM_023868.2 | chr13:11553102-12106945 |
| 18655 | Rrm2 | NM_009104.2 | chr12:24708253-24714146 | 18750 | Ryr3 | NM_177652.2 | chr2:112631381-113030331 |
| 18656 | Rrm2b | NM_199476.1 | chr15:37923952-37961055 | 18751 | S100a1 | NM_011309.3 | chr3:90511033-90514330 |
| 18657 | Rrn3 | NM_001039521.1 | chr16:13780698-13814841 | 18752 | S100a10 | NM_009112.2 | chr3:93555116-93564645 |
| 18658 | Rrnad1 | NM_153562.4 | chr3:87922600-87930195 | 18753 | S100a11 | NM_016740.3 | chr3:93520495-93526288 |
| 18659 | Rrp1 | NM_010925.2 | chr10:78400361-78413043 | 18754 | S100a13 | NM_009113.4 | chr3:90514434-90524581 |
| 18660 | Rrp12 | NM_199447.2 | chr19:41862850-41896153 | 18755 | S100a14 | NM_001163525.2 | chr3:90526848-90528835 |
| 18661 | Rrp15 | NM_026041.2 | chr1:186721086-186749358 | 18756 | S100a16 | NM_026416.2 | chr3:90541222-90543151 |
| 18662 | Rrp1b | NM_001163734.1 | chr17:32048284-32062862 | 18757 | S100a2 | NM_001195760.1 | chr3:90590246-90591508 |
| 18663 | Rrp36 | NM_144857.1 | chr7:46667452-46674255 | 18758 | S100a3 | NM_011310.2 | chr3:90600214-90602702 |
| 18664 | Rrp7a | NM_029101.4 | chr15:83115845-83112801 | 18759 | S100a4 | NM_011311.2 | chr3:90603769-90606045 |
| 18665 | Rrp8 | NM_025987.2 | chr7:105731729-105736584 | 18760 | S100a5 | NM_011312.2 | chr3:90608521-90611780 |
| 18666 | Rrp9 | NM_145620.4 | chr9:106477308-106485415 | 18761 | S100a6 | NM_011313.2 | chr3:90612893-90614414 |
| 18667 | Rrs1 | NM_021511.2 | chr9:9545407-9547455 | 18762 | S100a7a | NM_199422.1 | chr3:90654301-90658130 |
| 18668 | Rs1 | NM_011302.3 | chrX:160768012-160799663 | 18763 | S100a8 | NM_013650.2 | chr3:90669070-90670034 |
| 18669 | Rsad1 | NM_001013381.2 | chr11:94539797-94549207 | 18764 | S100a9 | NM_001281852.1 | chr3:90692629-90695721 |
| 18670 | Rsad2 | NM_021384.4 | chr12:26442742-26456452 | 18765 | S100b | NM_009115.3 | chr10:76253835-76261319 |
| 18671 | Rsbn1 | NM_172684.2 | chr3:103914219-103966620 | 18766 | S100g | NM_009789.1 | chrX:162961991-162964599 |
| 18672 | Rsbn1l | NM_001080977.1 | chr5:20893023-20951822 | 18767 | S100pbp | NM_029036.2 | chr4:129156824-129189482 |
| 18673 | Rsc1a1 | NM_023544.5 | chr4:141683562-141685716 | 18768 | S100z | NM_001081159.1 | chr13:95477300-95478655 |
| 18674 | Rsf1 | NM_001081267.2 | chr7:97579895-97692782 | 18769 | S1pr1 | NM_007901.5 | chr3:115710432-115715055 |
| 18675 | Rsg1 | NM_001081174.2 | chr4:141213955-141220114 | 18770 | S1pr2 | NM_010333.4 | chr9:20965951-20976793 |
| 18676 | Rsl1 | NM_001013769.1 | chr13:67173181-67183498 | 18771 | S1pr3 | NM_010101.4 | chr13:51408617-51422797 |
| 18677 | Rsl1d1 | NM_025546.2 | chr16:11193036-11203292 | 18772 | S1pr4 | NM_010102.2 | chr10:81487744-81500137 |
| 18678 | Rsl24d1 | NM_198609.2 | chr9:73113468-73123333 | 18773 | S1pr5 | NM_053190.2 | chr9:21242916-21248443 |
| 18679 | Rslcan18 | NM_001256052.1 | chr13:67096612-67114028 | 18774 | Saa1 | NM_009117.3 | chr7:46740498-46742980 |
| 18680 | Rsph1 | NM_025290.3 | chr17:31255019-31277356 | 18775 | Saa2 | NM_011314.2 | chr7:46751832-46754314 |
| 18681 | Rsph3a | NM_025789.5 | chr17:7945613-7979556 | 18776 | Saa3 | NM_011315.3 | chr7:46711997-46715676 |
| 18682 | Rsph3b | NM_001083945.1 | chr7:6904715-6948356 | 18777 | Saa4 | NM_011316.3 | chr7:46727998-46732543 |
| 18683 | Rsph4a | NM_001162957.1 | chr10:33905110-33916021 | 18778 | Saal1 | NM_030233.1 | chr7:46686107-46710651 |
| 18684 | Rsph6a | NM_001159671.1 | chr7:19054686-19074447 | 18779 | Sac3d1 | NM_136678.3 | chr19:6116003-6118586 |
| 18685 | Rsph9 | NM_029338.3 | chr17:46129276-46144198 | 18780 | Sacm1l | NM_030692.4 | chr9:123529881-123592598 |
| 18686 | Rspo1 | NM_138683.2 | chr4:124986429-125009099 | 18781 | Sacs | NM_172809.3 | chr14:61138456-61240693 |
| 18687 | Rspo2 | NM_172815.3 | chr15:43020794-43170818 | 18782 | Sae1 | NM_001285891.1 | chr7:16320235-16387896 |
| 18688 | Rspo3 | NM_028351.3 | chr10:29453106-29535867 | 18783 | Safb | NM_001163300.1 | chr17:56584981-56606294 |
| 18689 | Rspo4 | NM_001040689.1 | chr2:151842926-151874668 | 18784 | Safb2 | NM_001029979.2 | chr17:56562941-56584583 |
| 18690 | Rspry1 | NM_026274.4 | chr8:94601940-94660276 | 18785 | Sag | NM_009118.2 | chr1:87803679-87845157 |
| 18691 | Rsrc1 | NM_025822.3 | chr3:66985671-67358403 | 18786 | Sall1 | NM_021390.3 | chr8:89027242-89044162 |
| 18692 | Rsrc2 | NM_001005525.2 | chr5:123728425-123749414 | 18787 | Sall2 | NM_001244916.1 | chr14:52311176-52316323 |
| 18693 | Rsrp1 | NM_029665.3 | chr4:134923624-134927370 | 18788 | Sall3 | NM_178280.3 | chr18:80966373-80986578 |
| 18694 | Rsu1 | NM_009105.4 | chr2:13076966-13271415 | 18789 | Sall4 | NM_175303.4 | chr2:168748331-168767201 |
| 18695 | Rtbdn | NM_144929.2 | chr8:84946990-84956603 | 18790 | Samd1 | NM_001081415.1 | chr8:83997671-84000386 |
| 18696 | Rtca | NM_025517.3 | chr3:116488963-116508175 | 18791 | Samd10 | NM_172676.2 | chr2:181595217-181599147 |
| 18697 | Rtcb | NM_145422.4 | chr10:85938636-85957793 | 18792 | Samd11 | NM_001110516.1 | chr4:156246965-156255338 |
| 18698 | Rtdr1 | NM_001165533.1 | chr10:74957476-75032586 | 18793 | Samd12 | NM_177225.4 | chr15:53461800-53902436 |
| 18699 | Rtel1 | NM_001081882.3 | chr2:181319723-181356616 | 18794 | Samd14 | NM_146025.2 | chr11:95009878-95026087 |
| 18700 | Rffl | NM_030112.2 | chr2:119675067-119735407 | 18795 | Samd15 | NM_001290288.1 | chr12:87200542-87213538 |
| 18701 | Rtfdc1 | NM_025542.2 | chr2:172440577-172469899 | 18796 | Samd3 | NM_001013766.2 | chr10:26229706-26260804 |
| 18702 | Rtkn | NM_001136227.1 | chr6:83135807-83152579 | 18797 | Samd4 | NM_001037221.2 | chr14:46882964-47105817 |
| 18703 | Rtkn2 | NM_001081346.1 | chr10:67979597-68043864 | 18798 | Samd4b | NM_175021.3 | chr7:28399521-28436191 |
| 18704 | Rtl1 | NM_184109.1 | chr12:109590168-109595403 | 18799 | Samd5 | NM_177271.3 | chr10:9627258-9675208 |
| 18705 | Rtn1 | NM_001007596.2 | chr12:72211748-72236727 | 18800 | Samd7 | NM_029489.3 | chr3:30746292-30767174 |
| 18706 | Rtn2 | NM_001025364.3 | chr7:19291068-19296164 | 18801 | Samd8 | NM_026283.2 | chr14:21750530-21798725 |
| 18707 | Rtn3 | NM_001003933.2 | chr19:7425894-7483291 | 18802 | Samd9l | NM_010156.3 | chr6:3372257-3399571 |

Fig. 26 - 100

| | | | |
|---|---|---|---|
| 18803 | Samhd1 | NM_001139520.1 | chr2:157097528-157135222 |
| 18804 | Samm50 | NM_178614.4 | chr15:84192232-84214303 |
| 18805 | Samsn1 | NM_023380.2 | chr16:75858793-75909266 |
| 18806 | Samt2 | NM_001037167.1 | chrX:154575227-154579330 |
| 18807 | Samt3 | NM_028554.3 | chrX:86044198-86047313 |
| 18808 | Samt4 | NM_029199.2 | chrX:154482001-154484682 |
| 18809 | Sap130 | NM_172965.2 | chr18:31634382-31723061 |
| 18810 | Sap18 | NM_009119.3 | chr14:57798188-57804980 |
| 18811 | Sap25 | NM_001081962.2 | chr5:137641472-137642902 |
| 18812 | Sap30 | NM_021788.2 | chr8:57482701-57487860 |
| 18813 | Sap30bp | NM_020483 | chr11:115933658-115965534 |
| 18814 | Sap30l | NM_001081168 | chr11:57801636-57810615 |
| 18815 | Sapcd1 | NM_023893.4 | chr17:35025972-35028016 |
| 18816 | Sapcd2 | NM_001081085.2 | chr2:25372034-25378213 |
| 18817 | Sar1a | NM_009120.2 | chr10:61680320-61693297 |
| 18818 | Sar1b | NM_025535.2 | chr11:51763662-51791953 |
| 18819 | Sardh | NM_138665.2 | chr2:27188392-27247303 |
| 18820 | Sarm1 | NM_001168521.1 | chr11:78473329-78497754 |
| 18821 | Sarnp | NM_025364.2 | chr10:128821770-128877638 |
| 18822 | Sars | NM_001204979.1 | chr3:108424863-108445259 |
| 18823 | Sars2 | NM_023637.3 | chr7:28741967-28753879 |
| 18824 | Sart1 | NM_016852.3 | chr19:53775522-53788703 |
| 18825 | Sart3 | NM_016926.1 | chr5:113742445-113771649 |
| 18826 | Sash1 | NM_175155.4 | chr10:8722218-8886070 |
| 18827 | Sash3 | NM_028773.4 | chrX:48146435-48161566 |
| 18828 | Sass6 | NM_001289568.1 | chr3:116594957-116630986 |
| 18829 | Sat1 | NM_001291865.1 | chrX:155213125-155216449 |
| 18830 | Sat2 | NM_026991.2 | chr11:69622108-69623869 |
| 18831 | Satb1 | NM_001163630.1 | chr17:51736186-51812054 |
| 18832 | Satb2 | NM_139146.2 | chr1:56793980-56971334 |
| 18833 | Satl1 | NM_028655.1 | chrX:112384304-112406779 |
| 18834 | Sav1 | NM_022028.2 | chr12:69965012-69987002 |
| 18835 | Saysd1 | NM_026209.1 | chr14:20075635-20083172 |
| 18836 | Sbds | NM_023248.1 | chr5:130245731-130255462 |
| 18837 | Sbf1 | NM_001081030.2 | chr15:89288235-89315311 |
| 18838 | Sbf2 | NM_177324.2 | chr7:110308012-110614920 |
| 18839 | Sbk1 | NM_145587.2 | chr7:126272618-126294999 |
| 18840 | Sbk2 | NM_001146329.1 | chr7:4957080-4964348 |
| 18841 | Sbk3 | NM_001200041.1 | chr7:4965259-4970961 |
| 18842 | Sbno1 | NM_001081203.1 | chr5:124368701-124425914 |
| 18843 | Sbno2 | NM_183426.1 | chr10:80057013-80102702 |
| 18844 | Sbp | NM_011313.3 | chr17:23941995-23945607 |
| 18845 | Sbpl | NM_001077421.1 | chr17:23953084-23955273 |
| 18846 | Sbsn | NM_001083903.1 | chr7:30751470-30756134 |
| 18847 | Sbspon | NM_001033328.3 | chr1:15853861-15892722 |
| 18848 | Sc5d | NM_172769.2 | chr9:42254176-42264300 |
| 18849 | Scaf1 | NM_001008422.1 | chr7:45002949-45016249 |
| 18850 | Scaf11 | NM_028148.2 | chr15:96411697-96460843 |
| 18851 | Scaf4 | NM_178923.3 | chr16:90229143-90284425 |
| 18852 | Scaf8 | NM_134123.3 | chr17:3114971-3198859 |
| 18853 | Scai | NM_178778.3 | chr2:39066214-39190730 |
| 18854 | Scamp1 | NM_029153.1 | chr13:94201432-94285281 |
| 18855 | Scamp2 | NM_022813.3 | chr7:57560943-57588798 |
| 18856 | Scamp3 | NM_011886.3 | chr3:89177390-89182770 |
| 18857 | Scamp4 | NM_019575.4 | chr10:80602881-80615783 |
| 18858 | Scamp5 | NM_020270.3 | chr9:57441326-57468060 |
| 18859 | Scand1 | NM_020255.3 | chr2:156311845-156312704 |
| 18860 | Scap | NM_001001144.3 | chr9:110333355-110384949 |
| 18861 | Scaper | NM_001081341.1 | chr9:55549882-55938115 |
| 18862 | Scara3 | NM_172604.3 | chr14:65919394-65953744 |
| 18863 | Scara5 | NM_001168318.1 | chr14:65666402-65744943 |
| 18864 | Scarb1 | NM_001205082.1 | chr5:125277086-125341094 |
| 18865 | Scarb2 | NM_007644.4 | chr5:92441310-92505657 |
| 18866 | Scarf1 | NM_001004157.2 | chr11:75513540-75526680 |
| 18867 | Scarf2 | NM_153790.2 | chr16:17797281-17808287 |
| 18868 | Scarlettltr | NR_040743.1 | chr9:64080760-64088045 |
| 18869 | Scarna10 | NR_028517.2 | chr6:125186360-125186431 |
| 18870 | Scarna13 | NR_028576.1 | chr12:105031074-105031349 |
| 18871 | Scarna17 | NR_028560.1 | chr18:74778393-74778455 |
| 18872 | Scarna2 | NR_028538.1 | chr3:108554341-108554402 |
| 18873 | Scarna3a | NR_028518.1 | chr1:159340306-159340424 |
| 18874 | Scarna3b | NR_028544.1 | chr1:80391613-80391737 |
| 18875 | Scarna6 | NR_028519.1 | chr1:87784570-87784818 |
| 18876 | Scarna8 | NR_028545.1 | chr4:86586452-86586570 |
| 18877 | Scarna9 | NR_028568.2 | chr9:15326288-15326330 |
| 18878 | Sccpdh | NM_178653.3 | chr1:179668230-179687184 |
| 18879 | Scd1 | NM_009127.4 | chr19:44394449-44407709 |
| 18880 | Scd2 | NM_009128.2 | chr19:44293675-44306862 |
| 18881 | Scd3 | NM_024450.2 | chr19:44203287-44244016 |
| 18882 | Scd4 | NM_183216.3 | chr19:44433325-44446743 |
| 18883 | Scei | NM_022886.2 | chr14:103513340-103613346 |
| 18884 | Scfd1 | NM_029825.3 | chr12:51377512-51450102 |
| 18885 | Scfd2 | NM_001114660.2 | chr5:74204815-74531742 |
| 18886 | Scg2 | NM_009129.2 | chr1:79434668-79440090 |
| 18887 | Scg3 | NM_145784790.1 | chr9:75643365-75684056 |
| 18888 | Scg5 | NM_009162.3 | chr2:113776312-113829091 |
| 18889 | Scgb1a1 | NM_011681.2 | chr19:9083641-9087956 |
| 18890 | Scgb1b19 | NM_001281526.1 | chr7:33287306-33288491 |
| 18891 | Scgb1b2 | NM_020563.3 | chr7:31290518-31291816 |
| 18892 | Scgb1b20 | NM_001270543.1 | chr7:33373233-33374558 |
| 18893 | Scgb1b24 | NM_001099329.2 | chr7:33743798-33745103 |
| 18894 | Scgb1b27 | NM_009596.1 | chr7:34021566-34022881 |
| 18895 | Scgb1b29 | NM_001256066.1 | chr7:32441540-32442844 |
| 18896 | Scgb1b3 | NM_001256073.1 | chr7:31375591-31376916 |
| 18897 | Scgb1b30 | NM_001099330.2 | chr7:34095430-34100837 |
| 18898 | Scgb1b7 | NM_001270542.1 | chr7:31712664-31713980 |
| 18899 | Scgb1c1 | NM_001099742.1 | chr7:140845564-140846769 |
| 18900 | Scgb2b12 | NM_001281508.1 | chr7:32325285-32327245 |
| 18901 | Scgb2b15 | NM_001281523.1 | chr7:32827682-33056552 |
| 18902 | Scgb2b17 | NM_001281524.1 | chr7:33054582-33056552 |
| 18903 | Scgb2b19 | NM_001199336.1 | chr7:33278365-33280341 |
| 18904 | Scgb2b2 | NM_207262.2 | chr7:31302768-31304977 |
| 18905 | Scgb2b20 | NM_001009952.2 | chr7:33364342-33366319 |
| 18906 | Scgb2b23-ps | NR_045685.1 | chr7:33625144-33653281 |
| 18907 | Scgb2b24 | NM_177446.2 | chr7:33737192-33739295 |
| 18908 | Scgb2b26 | NM_178308.2 | chr7:33942996-33944985 |
| 18909 | Scgb2b27 | NM_001100464.1 | chr7:34011918-34013942 |
| 18910 | Scgb2b3 | NM_001270541 | chr7:31359037-31362072 |
| 18911 | Scgb2b7 | NM_001198871.1 | chr7:31703778-31705754 |
| 18912 | Scgb3a1 | NM_054037.2 | chr11:49635594-49665118 |
| 18913 | Scgb3a2 | NM_001289643.1 | chr18:43764300-43767399 |
| 18914 | Scgn | NM_145399.1 | chr13:23953456-23991214 |
| 18915 | Schip1 | NM_001113420.1 | chr3:68064801-68626482 |
| 18916 | Scimp | NM_001045526.2 | chr11:70790931-70812561 |
| 18917 | Scin | NM_001146196.1 | chr12:40059770-40134228 |
| 18918 | Sclt1 | NM_001081411.1 | chr3:41626704-41742514 |
| 18919 | Scly | NM_016717.3 | chr1:91298337-91321080 |
| 18920 | Scmh1 | NM_001159630.1 | chr4:120405280-120530199 |
| 18921 | Scml2 | NM_001290651.1 | chrX:161162749-161258213 |
| 18922 | Scml4 | NM_172938.3 | chr10:42860511-42960782 |
| 18923 | Scn10a | NM_001205321.1 | chr9:119608455-119719032 |
| 18924 | Scn11a | NM_011887.3 | chr9:119753764-119825456 |
| 18925 | Scn1a | NM_018733.2 | chr2:66270781-66440837 |
| 18926 | Scn1b | NM_011322.2 | chr7:31116523-31126945 |
| 18927 | Scn2a1 | NM_001099298.2 | chr2:65670444-65767447 |
| 18928 | Scn2b | NM_001014761.2 | chr9:45117875-45130070 |
| 18929 | Scn3a | NM_018732.3 | chr2:65457117-65567492 |
| 18930 | Scn3b | NM_001083917.1 | chr9:40269215-40291618 |
| 18931 | Scn4a | NM_133199.2 | chr11:106318592-106349390 |
| 18932 | Scn4b | NM_001013390.2 | chr9:45139041-45154061 |
| 18933 | Scn5a | NM_001253860.1 | chr9:119483407-119562678 |
| 18934 | Scn7a | NM_009135.2 | chr2:66673425-66784910 |
| 18935 | Scn8a | NM_001077499.2 | chr15:100870644-101045938 |
| 18936 | Scn9a | NM_001290674.1 | chr2:66480080-66634962 |
| 18937 | Scnm1 | NM_001163573.1 | chr3:95129718-95134012 |
| 18938 | Scnn1a | NM_011324.2 | chr6:125321339-125344942 |
| 18939 | Scnn1b | NM_001272023.1 | chr7:121865037-121918728 |
| 18940 | Scnn1g | NM_011326.3 | chr7:121734506-121768477 |
| 18941 | Sco1 | NM_001040026.1 | chr11:67052669-67067440 |
| 18942 | Sco2 | NM_001111288.1 | chr15:89371636-89373818 |
| 18943 | Scoc | NM_001039137.3 | chr8:83434491-83458396 |
| 18944 | Scp2 | NM_011327.4 | chr4:108043829-108118547 |
| 18945 | Scp2d1 | NM_025490.2 | chr2:144823665-144824415 |
| 18946 | Scpep1 | NM_029023.3 | chr11:88924019-88955442 |
| 18947 | Scpeplos | NR_045955.1 | chr11:88905927-88936061 |
| 18948 | Scrg1 | NM_009136.3 | chr8:57455922-57477585 |
| 18949 | Scrib | NM_134089.2 | chr15:76047162-76069784 |
| 18950 | Scrn1 | NM_027268.2 | chr6:54508815-54566382 |
| 18951 | Scrn2 | NM_146027.2 | chr11:97029951-97033960 |
| 18952 | Scrn3 | NM_029022 | chr2:73312651-73337807 |
| 18953 | Scrt1 | NM_130893 | chr15:76516202-76522129 |
| 18954 | Scrt2 | NM_001160410.1 | chr2:152081528-152095802 |
| 18955 | Sct | NM_001287171.1 | chr7:141278328-141279133 |
| 18956 | Sctr | NM_001012922.2 | chr1:120006979-120063532 |
| 18957 | Scube1 | NM_001271472.1 | chr15:83602582-83725039 |
| 18958 | Scube2 | NM_020052.2 | chr7:109798690-109865679 |
| 18959 | Scube3 | NM_001004366.1 | chr17:28142525-28171345 |
| 18960 | Scx | NM_198885.3 | chr15:76457437-76459468 |
| 18961 | Scyl1 | NM_023912.2 | chr19:5758426-5771401 |
| 18962 | Scyl2 | NM_198021.2 | chr10:89640106-89686285 |
| 18963 | Scyl3 | NM_001286002.1 | chr1:163929099-163955126 |
| 18964 | Sdad1 | NM_172713.2 | chr5:92284009-92310024 |
| 18965 | Sdc1 | NM_011519.2 | chr12:8771395-8793687 |
| 18966 | Sdc2 | NM_008304.2 | chr15:32920722-33034721 |
| 18967 | Sdc3 | NM_011520.3 | chr4:130792536-130826318 |
| 18968 | Sdc4 | NM_011521.2 | chr2:164424246-164443188 |
| 18969 | Sdcbp | NM_001098227.1 | chr4:6365679-6396122 |
| 18970 | Sdcbp2 | NM_145535.2 | chr2:151572822-151590005 |
| 18971 | Sdccag3 | NM_001085407.1 | chr2:26382799-26389316 |
| 18972 | Sdccag8 | NM_029756.3 | chr1:176814659-177020432 |
| 18973 | Sde2 | NM_145943.1 | chr1:180851150-180868114 |
| 18974 | Sdf2 | NM_009143.3 | chr11:78245745-78255496 |
| 18975 | Sdf2l1 | NM_022324.3 | chr16:17130137-17132383 |
| 18976 | Sdf4 | NM_011341.5 | chr4:155992842-156013610 |
| 18977 | Sdha | NM_023281.1 | chr13:74322254-74350240 |
| 18978 | Sdhaf1 | NM_001033140.3 | chr7:30321408-30322375 |
| 18979 | Sdhaf2 | NM_025333.4 | chr19:10500511-10525209 |
| 18980 | Sdhb | NM_023374.3 | chr4:140961270-140979192 |
| 18981 | Sdhc | NM_025321.3 | chr1:171129156-171150603 |
| 18982 | Sdhd | NM_025848.3 | chr9:50596339-50603849 |
| 18983 | Sdk1 | NM_177879.5 | chr5:141241553-142213791 |
| 18984 | Sdk2 | NM_172800.2 | chr11:113780789-114065951 |
| 18985 | Sdpr | NM_138741.1 | chr1:51289125-51302960 |
| 18986 | Sdr16c5 | NM_181989.1 | chr4:3995941-4019663 |
| 18987 | Sdr16c6 | NM_001080710.2 | chr4:4056665-4077514 |
| 18988 | Sdr39u1 | NM_001082975.1 | chr14:55897284-55900232 |
| 18989 | Sdr42e1 | NM_028725.3 | chr8:117661398-117671515 |
| 18990 | Sdr9c7 | NM_027301.3 | chr10:127898534-127911759 |
| 18991 | Sds | NM_145565.1 | chr5:120476546-120483905 |
| 18992 | Sdsl | NM_133902.2 | chr5:120458201-120472763 |

Fig. 26 - 101

| | | | | | | | | |
|---|---|---|---|---|---|---|---|---|
| 18993 | Sebox | NM_008759.2 | chr11:78503512-78505081 | | 19088 | Serac1 | NM_001111017.1 | chr17:6040570-6079739 |
| 18994 | Sec1 | NM_175677685-45694402 | chr7:45677685-45694402 | | 19089 | Serbp1 | NM_001113564.1 | chr6:67266978-67289302 |
| 18995 | Sec11a | NM_019951.1 | chr7:80915378-80947550 | | 19090 | Serf1 | NM_011353.2 | chr13:100108018-100114233 |
| 18996 | Sec11c | NM_025468.2 | chr18:65800577-65817657 | | 19091 | Serf2 | NM_001290837.1 | chr2:121449197-121453420 |
| 18997 | Sec13 | NM_024206.4 | chr6:113728051-113740681 | | 19092 | Sergef | NM_013789.2 | chr7:46443158-46639807 |
| 18998 | Sec14l1 | NM_001166506.1 | chr11:117115171-117159268 | | 19093 | Serhl | NM_023475.3 | chr15:83100204-83116671 |
| 18999 | Sec14l2 | NM_144520.2 | chr11:4097039-4118729 | | 19094 | Serinc1 | NM_019760.3 | chr10:57515774-57532529 |
| 19000 | Sec14l3 | NM_001029937.2 | chr11:4064852-4078990 | | 19095 | Serinc2 | NM_001253386.1 | chr4:130253496-130275220 |
| 19001 | Sec14l4 | NM_146013.1 | chr11:4031781-4048009 | | 19096 | Serinc3 | NM_012032.4 | chr2:163623272-163645143 |
| 19002 | Sec14l5 | NM_001127725.1 | chr16:5147108-5183934 | | 19097 | Serinc4 | NM_001025371.2 | chr2:121451176-121456764 |
| 19003 | Sec16a | NM_153125.2 | chr2:26409430-26445216 | | 19098 | Serinc5 | NM_172588.2 | chr13:92611137-92711946 |
| 19004 | Sec16b | NM_001159986.1 | chr1:157526169-157568424 | | 19099 | Serp1 | NM_030685.3 | chr3:58521970-58525884 |
| 19005 | Sec22a | NM_133704.4 | chr16:35311130-35363918 | | 19100 | Serp2 | NM_001160326.1 | chr14:76532811-76556687 |
| 19006 | Sec22b | NM_011342.4 | chr3:97901226-97922318 | | 19101 | Serpina10 | NM_144834.4 | chr12:103616674-103631444 |
| 19007 | Sec22c | NM_001164562.1 | chr9:121680044-121705029 | | 19102 | Serpina11 | NM_001166350.1 | chr12:103980242-103989957 |
| 19008 | Sec23a | NM_009147.2 | chr12:58958383-59012017 | | 19103 | Serpina12 | NM_026535.2 | chr12:104028768-104044443 |
| 19009 | Sec23b | NM_001252543.1 | chr2:144556228-144580753 | | 19104 | Serpina1a | NM_001252569.1 | chr12:103853294-103863619 |
| 19010 | Sec23ip | NM_001029982.2 | chr7:128744869-128784835 | | 19105 | Serpina1b | NM_009244.4 | chr12:103728155-103738189 |
| 19011 | Sec24a | NM_001290763.1 | chr11:51692262-51756834 | | 19106 | Serpina1c | NM_009245.2 | chr12:103894925-103904950 |
| 19012 | Sec24b | NM_207209.2 | chr3:129983184-130060907 | | 19107 | Serpina1d | NM_009246.3 | chr12:103763586-103773633 |
| 19013 | Sec24c | NM_001168273.1 | chr14:20674320-20694850 | | 19108 | Serpina1e | NM_009247.2 | chr12:103946931-103956897 |
| 19014 | Sec24d | NM_027135.2 | chr3:123267495-123365636 | | 19109 | Serpina1f | NM_001164742.1 | chr12:103688043-103694689 |
| 19015 | Sec31a | NM_026969.1 | chr5:100361648-100416234 | | 19110 | Serpina3a | NM_001167705.1 | chr12:104112723-104121896 |
| 19016 | Sec31b | NM_001033343.1 | chr19:44516956-44545848 | | 19111 | Serpina3b | NM_173024.3 | chr12:104127995-104139545 |
| 19017 | Sec61a1 | NM_016906.4 | chr6:88503606-88518800 | | 19112 | Serpina3c | NM_008458.2 | chr12:104146806-104153872 |
| 19018 | Sec61a2 | NM_021305.3 | chr2:5870986-5895353 | | 19113 | Serpina3f | NM_001033335.3 | chr12:104214632-104221129 |
| 19019 | Sec61b | NM_024171.2 | chr4:47474660-47483233 | | 19114 | Serpina3g | NM_009251.1 | chr12:104214543-104241934 |
| 19020 | Sec61g | NM_001109971.1 | chr11:16501637-16508484 | | 19115 | Serpina3h | NR_033450.1 | chr12:104247895-104254405 |
| 19021 | Sec62 | NM_027016.2 | chr3:30792875-30821263 | | 19116 | Serpina3i | NM_001199940.1 | chr12:104263121-104269365 |
| 19022 | Sec63 | NM_153055.3 | chr10:42761495-42832514 | | 19117 | Serpina3j | NM_001101472.2 | chr12:104314569-104320586 |
| 19023 | Secisbp2 | NM_029279.2 | chr13:51651707-51684044 | | 19118 | Serpina3k | NM_011458.2 | chr12:104338485-104345739 |
| 19024 | Secisbp2l | NM_177608.3 | chr2:125736985-125782870 | | 19119 | Serpina3m | NM_009253.2 | chr12:104387163-104394257 |
| 19025 | Sectm1a | NM_145373.2 | chr11:121067402-121081139 | | 19120 | Serpina3n | NM_009252.2 | chr12:104406707-104414329 |
| 19026 | Sectm1b | NM_026907.3 | chr11:121053422-121063569 | | 19121 | Serpina4-ps1 | NR_002861.2 | chr12:104077958-104086920 |
| 19027 | Sehl1 | NM_001039088.1 | chr18:67774875-67795487 | | 19122 | Serpina5 | NM_172953.3 | chr12:104101112-104106137 |
| 19028 | Sel1l | NM_001039089.1 | chr12:91806042-91849157 | | 19123 | Serpina6 | NM_007618.3 | chr12:103846630-103657218 |
| 19029 | Sel1l2 | NM_001033296.2 | chr2:140229857-140389710 | | 19124 | Serpina7 | NM_177920.5 | chrX:139079249-139085236 |
| 19030 | Sel1l3 | NM_172710.3 | chr5:53107082-53213452 | | 19125 | Serpina9 | NM_027997.2 | chr12:103996619-104013652 |
| 19031 | Sele | NM_011345.2 | chr1:164048233-164057677 | | 19126 | Serpinb10 | NM_001160307.1 | chr1:107529002-107549271 |
| 19032 | Selenbp1 | NM_009150.3 | chr3:94933082-94944758 | | 19127 | Serpinb11 | NM_025867.2 | chr1:107362313-107380475 |
| 19033 | Selenbp2 | NM_019414.2 | chr3:94693572-94704406 | | 19128 | Serpinb12 | NM_001199213.1 | chr1:106938956-106957080 |
| 19034 | Selk | NM_019979.2 | chr14:29968379-29975074 | | 19129 | Serpinb13 | NM_172852.3 | chr1:106980983-107001195 |
| 19035 | Sell | NM_001164059.1 | chr1:164062075-164080785 | | 19130 | Serpinb1a | NM_025429.2 | chr13:32842091-32851185 |
| 19036 | Selm | NM_053267.2 | chr11:3514701-3517351 | | 19131 | Serpinb1b | NM_173052.2 | chr13:33084102-33094380 |
| 19037 | Selo | NM_027905.2 | chr15:89089106-89100340 | | 19132 | Serpinb1c | NM_173051.2 | chr13:32881396-32898140 |
| 19038 | Selp | NM_011347.2 | chr1:164115263-164150026 | | 19133 | Serpinb2 | NM_001174170.1 | chr1:107511422-107525600 |
| 19039 | Selplg | NM_009151.3 | chr5:113817797-113830501 | | 19134 | Serpinb3a | NM_009126.3 | chr1:107045586-107052303 |
| 19040 | Selt | NM_001040396.2 | chr3:58576657-58593546 | | 19135 | Serpinb3b | NM_198680.2 | chr1:107153960-107161114 |
| 19041 | Sema3a | NM_001243072.1 | chr5:13396783-13603485 | | 19136 | Serpinb3c | NM_201363.2 | chr1:107271200-107278371 |
| 19042 | Sema3b | NM_001042779.2 | chr9:107597673-107609241 | | 19137 | Serpinb3d | NM_201376.1 | chr1:107078192-107083480 |
| 19043 | Sema3c | NM_013661.5 | chr5:17574815-17730267 | | 19138 | Serpinb5 | NM_009257.3 | chr1:106861179-106883348 |
| 19044 | Sema3d | NM_028882.4 | chr5:12383165-12588943 | | 19139 | Serpinb6a | NM_001164117.1 | chr13:33917917-33936083 |
| 19045 | Sema3e | NM_011348.2 | chr5:14025275-14256689 | | 19140 | Serpinb6b | NM_011454.1 | chr13:32965512-32979037 |
| 19046 | Sema3f | NM_011349.3 | chr9:107681501-107710475 | | 19141 | Serpinb6c | NM_148942.2 | chr13:33879815-33905708 |
| 19047 | Sema3g | NM_001025379.1 | chr14:31217872-31229511 | | 19142 | Serpinb6d | NM_001076790.2 | chr13:33661404-33671585 |
| 19048 | Sema4a | NM_001163489.1 | chr3:88435961-88461182 | | 19143 | Serpinb6e | NM_001045535.2 | chr13:33832344-33843408 |
| 19049 | Sema4b | NM_013659.4 | chr7:80186840-80226524 | | 19144 | Serpinb7 | NM_027548.3 | chr1:107422688-107452689 |
| 19050 | Sema4c | NM_001126047.3 | chr1:36548638-36558381 | | 19145 | Serpinb8 | NM_001159748.1 | chr1:107590005-107606150 |
| 19051 | Sema4d | NM_001281880.1 | chr13:51701247-51793747 | | 19146 | Serpinb9 | NM_009256.3 | chr13:33004540-33017955 |
| 19052 | Sema4f | NM_001308374.1 | chr6:82911884-829397 | | 19147 | Serpinb9b | NM_011452.2 | chr13:33027413-33040558 |
| 19053 | Sema4g | NM_011976.1 | chr19:44989343-45003395 | | 19148 | Serpinb9c | NM_001164524.1 | chr13:33149274-33159754 |
| 19054 | Sema5a | NM_009154.2 | chr15:32244812-32696341 | | 19149 | Serpinb9d | NM_011460.2 | chr13:33192958-33203980 |
| 19055 | Sema5b | NM_013661.2 | chr16:35541361-35664258 | | 19150 | Serpinb9e | NM_011456.2 | chr13:33249609-33260846 |
| 19056 | Sema6a | NM_018744.2 | chr18:47245253-47368868 | | 19151 | Serpinb9f | NM_183197.1 | chr13:33324076-33335366 |
| 19057 | Sema6b | NM_001304456.1 | chr17:56123084-56140343 | | 19152 | Serpinb9g | NM_011455.3 | chr13:33484789-33496000 |
| 19058 | Sema6c | NM_001272024.1 | chr3:95160419-95174050 | | 19153 | Serpinc1 | NM_080844.4 | chr1:160978605-161003014 |
| 19059 | Sema6d | NM_001290997.1 | chr2:124089968-124667789 | | 19154 | Serpind1 | NM_008223.3 | chr16:17331370-17343572 |
| 19060 | Sema7a | NM_011352.2 | chr9:57940134-57962865 | | 19155 | Serpine1 | NM_008871.2 | chr5:137061505-137072272 |
| 19061 | Senp1 | NM_144851.5 | chr15:98038743-98093569 | | 19156 | Serpine2 | NM_009255.4 | chr1:79794320-79858665 |
| 19062 | Senp2 | NM_029457.3 | chr16:22009483-22049269 | | 19157 | Serpine3 | NM_001199945.1 | chr14:62663666-62692243 |
| 19063 | Senp3 | NM_001163571.1 | chr11:69673109-69682084 | | 19158 | Serpinf1 | NM_011340.3 | chr11:75410028-75422623 |
| 19064 | Senp5 | NM_177103.4 | chr16:31959669-32003287 | | 19159 | Serpinf2 | NM_008878.2 | chr11:75431735-75439501 |
| 19065 | Senp6 | NM_146623.2 | chr9:80066902-80144780 | | 19160 | Serping1 | NM_009776.3 | chr2:84765359-84775429 |
| 19066 | Senp7 | NM_001003972.2 | chr16:56072059-56190011 | | 19161 | Serpinh1 | NM_001111043.1 | chr7:99345374-99353239 |
| 19067 | Senp8 | NM_001172068.1 | chr9:59734258-59750649 | | 19162 | Serpini1 | NM_009250.2 | chr3:75557532-75642523 |
| 19068 | Sephs1 | NM_175400.6 | chr2:4881563-4910556 | | 19163 | Serpini2 | NM_026460.3 | chr15:75242356-75270078 |
| 19069 | Sephs2 | NM_009266.3 | chr7:127271878-127274059 | | 19164 | Sertad1 | NM_018820.4 | chr7:27486952-27490314 |
| 19070 | Sepn1 | NM_029100.2 | chr4:134537891-134552166 | | 19165 | Sertad2 | NM_001038625.1 | chr11:20631976-20653023 |
| 19071 | Sepp1 | NM_001042613.1 | chr15:3270766-3280508 | | 19166 | Sertad3 | NM_133210.2 | chr7:27473839-27477364 |
| 19072 | Sepsecs | NM_172490.3 | chr5:52643406-52669701 | | 19167 | Sertad4 | NM_001177794.1 | chr1:192844487-192851747 |
| 19073 | Sept1 | NM_017461.2 | chr7:127214441-127218445 | | 19168 | Sertm1 | NM_177854.4 | chr9:54897068-54915887 |
| 19074 | Sept10 | NM_001024910.3 | chr10:59141626-59221847 | | 19169 | Sesn1 | NM_001013370.2 | chr10:41887438-41908436 |
| 19075 | Sept11 | NM_001009818.2 | chr5:93093415-93175075 | | 19170 | Sesn2 | NM_144907.1 | chr4:132492806-132510456 |
| 19076 | Sept12 | NM_027669.3 | chr16:4986857-4997852 | | 19171 | Sesn3 | NM_030261.4 | chr9:14276300-14326134 |
| 19077 | Sept14 | NM_028828.1 | chr5:129683390-129708511 | | 19172 | Sestd1 | NM_175465.6 | chr2:77180339-77280592 |
| 19078 | Sept15 | NM_053102.2 | chr3:144570426-144597676 | | 19173 | Set | NM_001204875.1 | chr2:30066473-30072577 |
| 19079 | Sept2 | NM_001159717.1 | chr1:93478992-93509732 | | 19174 | Setbp1 | NM_053099.2 | chr18:78750377-79109391 |
| 19080 | Sept3 | NM_011889.2 | chr15:82274934-82294442 | | 19175 | Setd1a | NM_178029.3 | chr7:127777388-127800119 |
| 19081 | Sept4 | NM_001284392.1 | chr11:87581060-87590539 | | 19176 | Setd1b | NM_001040398.2 | chr5:123142192-123168630 |
| 19082 | Sept5 | NM_213614.2 | chr16:18621810-18629938 | | 19177 | Setd2 | NM_001081340.2 | chr9:110532596-110618633 |
| 19083 | Sept6 | NM_001177323.2 | chrX:36911271-36989695 | | 19178 | Setd3 | NM_028262.3 | chr12:108106430-108179284 |
| 19084 | Sept7 | NM_001205367.1 | chr9:25252438-25308571 | | 19179 | Setd4 | NM_145482.3 | chr16:93583460-93603815 |
| 19085 | Sept8 | NM_001252332.1 | chr11:53519735-53544096 | | 19180 | Setd5 | NM_028385.1 | chr6:113077638-113153424 |
| 19086 | Sept9 | NM_001113486.1 | chr11:117199660-117362325 | | 19181 | Setd6 | NM_001035123.3 | chr8:95715912-95719004 |
| 19087 | Sepw1 | NM_009156.2 | chr7:15917207-15922371 | | 19182 | Setd7 | NM_080793.5 | chr3:51515317-51560823 |

Fig. 26 - 102

| | | | |
|---|---|---|---|
| 19183 | Setd8 | NM_030241.3 | chr5:124439929-124462311 |
| 19184 | Setdb1 | NM_001163641.1 | chr3:95323524-95357202 |
| 19185 | Setdb2 | NM_001081024.1 | chr14:59402010-59440877 |
| 19186 | Setmar | NM_001276356.1 | chr6:108065044-108077127 |
| 19187 | Setx | NM_198033.2 | chr2:29124991-29182471 |
| 19188 | Sez6 | NM_001291225.1 | chr11:77930838-77979052 |
| 19189 | Sez6l | NM_001253916.1 | chr5:112419150-112577198 |
| 19190 | Sez6l2 | NM_001252566.1 | chr7:126950534-126970606 |
| 19191 | Sf1 | NM_001110791.1 | chr19:6363689-6378038 |
| 19192 | Sf3a1 | NM_026175.5 | chr11:4160353-4182541 |
| 19193 | Sf3a2 | NM_013651.4 | chr10:80798734-80804922 |
| 19194 | Sf3a3 | NM_029157.3 | chr4:124714860-124732422 |
| 19195 | Sf3b1 | NM_031179.2 | chr1:54985169-55027478 |
| 19196 | Sf3b2 | NM_030109.2 | chr19:5273920-5295455 |
| 19197 | Sf3b3 | NM_133953.2 | chr8:110810491-110846803 |
| 19198 | Sf3b4 | NM_153053.4 | chr3:96172505-96177564 |
| 19199 | Sf3b5 | NM_175102.4 | chr10:13008449-13009183 |
| 19200 | Sf3b6 | NM_025323.2 | chr12:4817607-4827659 |
| 19201 | Sfi1 | NM_030027.2 | chr11:3131849-3193463 |
| 19202 | Sfmbt1 | NM_001166531.1 | chr14:30715166-30822721 |
| 19203 | Sfmbt2 | NM_001198808.1 | chr2:10370450-10595253 |
| 19204 | Sfn | NM_018754.2 | chr4:133600555-133602168 |
| 19205 | Sfpq | NM_023603.3 | chr4:127021300-127031236 |
| 19206 | Sfr1 | NM_026377.2 | chr19:47731755-47735588 |
| 19207 | Sfrp1 | NM_013834.3 | chr8:23411501-23449632 |
| 19208 | Sfrp2 | NM_009144.2 | chr3:83766320-83774314 |
| 19209 | Sfrp4 | NM_016687.3 | chr13:19623174-19632823 |
| 19210 | Sfrp5 | NM_018759.3 | chr19:42197970-42202252 |
| 19211 | Sfswap | NM_172276.3 | chr5:129501230-129571384 |
| 19212 | Sft2d1 | NM_134114.2 | chr17:8311102-8327442 |
| 19213 | Sft2d2 | NM_145512.4 | chr1:165174340-165194433 |
| 19214 | Sft2d3 | NM_026006.1 | chr18:31909093-31911903 |
| 19215 | Sfta2 | NM_001163194.1 | chr17:35649707-35650569 |
| 19216 | Sftpa1 | NM_023134.4 | chr14:41131787-41136373 |
| 19217 | Sftpb | NM_001282071.1 | chr6:72304609-72314373 |
| 19218 | Sftpc | NM_011359.2 | chr14:70520941-70524081 |
| 19219 | Sftpd | NM_009160.2 | chr14:41172211-41185198 |
| 19220 | Sfxn2 | NM_027324.5 | chr13:54071844-54108345 |
| 19221 | Sfxn2 | NM_053196.3 | chr19:46573364-46596900 |
| 19222 | Sfxn3 | NM_001178012.1 | chr19:45047575-45056383 |
| 19223 | Sfxn4 | NM_053198.3 | chr19:60837276-60861430 |
| 19224 | Sfxn5 | NM_178639.4 | chr6:85213050-85333422 |
| 19225 | Sgca | NM_009161.4 | chr11:94962776-94976327 |
| 19226 | Sgcb | NM_011890.4 | chr5:73632748-73647731 |
| 19227 | Sgcd | NM_011891.4 | chr11:46978782-47379302 |
| 19228 | Sgce | NM_001130188.1 | chr6:4674349-4747204 |
| 19229 | Sgcg | NM_011892.3 | chr14:61219114-61258490 |
| 19230 | Sgcz | NM_145841.2 | chr8:37522553-38661508 |
| 19231 | Sgip1 | NM_001285852.1 | chr4:102760134-102972682 |
| 19232 | Sgk1 | NM_001161845.2 | chr10:21882183-21999902 |
| 19233 | Sgk2 | NM_001291152.1 | chr2:162991414-163014139 |
| 19234 | Sgk3 | NM_001037759.1 | chr1:9848280-9902568 |
| 19235 | Sgms1 | NM_001168525.1 | chr19:32122726-32349316 |
| 19236 | Sgms2 | NM_028943.5 | chr3:131318985-131344923 |
| 19237 | Sgol1 | NM_028232.2 | chr17:53674786-53689315 |
| 19238 | Sgol2 | NM_001177867.1 | chr1:57985339-58025897 |
| 19239 | Sgpl1 | NM_009163.4 | chr10:61098641-61147665 |
| 19240 | Sgpp1 | NM_030750.3 | chr12:75714247-75755729 |
| 19241 | Sgpp2 | NM_001004173.4 | chr1:78310345-78420286 |
| 19242 | Sgsh | NM_018822.3 | chr11:119343488-119355510 |
| 19243 | Sgsm1 | NM_001162965.1 | chr5:113257473-113310786 |
| 19244 | Sgsm2 | NM_197943.2 | chr11:74849263-74897080 |
| 19245 | Sgsm3 | NM_134091.2 | chr15:80977764-81012290 |
| 19246 | Sgta | NM_024499.1 | chr10:81044072-81060154 |
| 19247 | Sgtb | NM_144838.1 | chr13:104109789-104141441 |
| 19248 | Sh2b1 | NM_001081459.2 | chr7:126466992-126475130 |
| 19249 | Sh2b2 | NM_018825.4 | chr5:136218148-136244940 |
| 19250 | Sh2b3 | NM_008507.4 | chr5:121815480-121836859 |
| 19251 | Sh2d1a | NM_011364.4 | chrX:42502564-42522095 |
| 19252 | Sh2d1b1 | NM_001004120.4 | chr1:170277323-170285662 |
| 19253 | Sh2d1b2 | NM_001033499.1 | chr1:170232870-170251587 |
| 19254 | Sh2d2a | NM_001025571.2 | chr3:87846754-87855722 |
| 19255 | Sh2d3c | NM_001252487.1 | chr2:32727688-32755007 |
| 19256 | Sh2d4a | NM_028182.1 | chr8:68276527-68347704 |
| 19257 | Sh2d4b | NM_177816.3 | chr14:40815867-40892965 |
| 19258 | Sh2d5 | NM_001099631.1 | chr4:138250410-138260968 |
| 19259 | Sh2d7 | NM_173778.3 | chr9:54538983-54545020 |
| 19260 | Sh3bgr | NM_015825.2 | chr16:96200469-96226933 |
| 19261 | Sh3bgrl | NM_019989.2 | chrX:109095406-109162467 |
| 19262 | Sh3bgrl2 | NM_172507.5 | chr9:83548337-83600291 |
| 19263 | Sh3bgrl3 | NM_080559.1 | chr4:134127405-134128753 |
| 19264 | Sh3bp1 | NM_009164.3 | chr15:78899785-78912052 |
| 19265 | Sh3bp2 | NM_001145858.1 | chr5:34543364-34563639 |
| 19266 | Sh3bp4 | NM_133816.2 | chr1:89070461-89153793 |
| 19267 | Sh3bp5 | NM_011894.2 | chr14:31317963-31436033 |
| 19268 | Sh3bp5l | NM_001161338.2 | chr11:58330706-58347728 |
| 19269 | Sh3d19 | NM_001082414.2 | chr3:86084433-86130521 |
| 19270 | Sh3d21 | NM_001162533.1 | chr4:126150601-126163341 |
| 19271 | Sh3gl1 | NM_001252471.1 | chr17:56016749-56036637 |
| 19272 | Sh3gl2 | NM_019535.2 | chr4:85205455-85389379 |
| 19273 | Sh3gl3 | NM_001277954.1 | chr7:82259907-82307420 |
| 19274 | Sh3glb1 | NM_001282037.1 | chr3:144686901-144720335 |
| 19275 | Sh3glb2 | NM_001289709.1 | chr2:30344776-30359316 |
| 19276 | Sh3kbp1 | NM_001135727.2 | chrX:159627271-159975920 |
| 19277 | Sh3pxd2a | NM_001164717.1 | chr19:47260173-47464411 |

| | | | |
|---|---|---|---|
| 19278 | Sh3pxd2b | NM_177364.3 | chr11:32347810-32428183 |
| 19279 | Sh3rf1 | NM_021506.2 | chr8:61224170-61396072 |
| 19280 | Sh3rf2 | NM_001146299.1 | chr18:42053709-42158695 |
| 19281 | Sh3rf3 | NM_172788.3 | chr10:58813358-59138916 |
| 19282 | Sh3tc1 | NM_194344.2 | chr5:35697179-35729276 |
| 19283 | Sh3tc2 | NM_172628.2 | chr18:61953074-62015719 |
| 19284 | Sh3yl1 | NM_001289480.1 | chr12:30911668-30960160 |
| 19285 | Shank1 | NM_001034115.1 | chr7:44310263-44358353 |
| 19286 | Shank2 | NM_001081370.2 | chr7:144284384-144422675 |
| 19287 | Shank3 | NM_021423.3 | chr15:89499856-89560260 |
| 19288 | Sharpin | NM_025340.2 | chr15:76347039-76351110 |
| 19289 | Shb | NM_001033306.1 | chr4:45423275-45530828 |
| 19290 | Shbg | NM_011367.2 | chr11:69614815-69617905 |
| 19291 | Shc1 | NM_001113331.2 | chr3:89421620-89430029 |
| 19292 | Shc2 | NM_001024539.1 | chr10:79617937-79637918 |
| 19293 | Shc3 | NM_009167.3 | chr13:51431041-51567084 |
| 19294 | Shc4 | NM_199022.2 | chr2:125627446-125724148 |
| 19295 | Shcbp1 | NM_011369.2 | chr8:4735979-4779534 |
| 19296 | Shcbp1l | NM_001033162.2 | chr1:153425208-153452574 |
| 19297 | Shd | NM_001159523.1 | chr17:55970481-55976619 |
| 19298 | She | NM_172530.3 | chr3:89831369-89858846 |
| 19299 | Shf | NM_001013829.2 | chr2:122348891-122368918 |
| 19300 | Shfm1 | NM_009169.2 | chr6:6558274-6578658 |
| 19301 | Shh | NM_009170.3 | chr5:28456839-28467101 |
| 19302 | Shisa2 | NM_145463.5 | chr14:59625280-59631660 |
| 19303 | Shisa3 | NM_001033415.3 | chr5:67607882-67613987 |
| 19304 | Shisa4 | NM_175259.4 | chr1:135371455-135375063 |
| 19305 | Shisa5 | NM_001284332.1 | chr9:109038566-109057792 |
| 19306 | Shisa6 | NM_001034874.3 | chr11:66211724-66526126 |
| 19307 | Shisa7 | NM_001290291.1 | chr7:4825551-4844696 |
| 19308 | Shisa9 | NM_001174086.1 | chr16:11984112-12270904 |
| 19309 | Shkbp1 | NM_138676.2 | chr7:27342132-27356008 |
| 19310 | Shmt1 | NM_009171.2 | chr11:60788896-60811265 |
| 19311 | Shmt2 | NM_001252316.1 | chr10:127517122-127522444 |
| 19312 | Shoc2 | NM_001168505.1 | chr19:53944305-54033278 |
| 19313 | Shox2 | NM_013665.1 | chr3:66973265-66981771 |
| 19314 | Shpk | NM_029031.3 | chr11:73199481-73224506 |
| 19315 | Shprh | NM_001077707.1 | chr10:11149429-11215273 |
| 19316 | Shq1 | NM_181590.5 | chr6:100571810-100671157 |
| 19317 | Shroom1 | NM_001290789.1 | chr11:53457204-53467766 |
| 19318 | Shroom2 | NM_001290684.1 | chrX:152609608-152769486 |
| 19319 | Shroom3 | NM_001077595.2 | chr5:92809381-92965759 |
| 19320 | Shroom4 | NM_001040459.2 | chrX:6400031-6637454 |
| 19321 | Siae | NM_011734.3 | chr9:37613846-37648318 |
| 19322 | Siah1a | NM_009172.2 | chr8:86723937-86746006 |
| 19323 | Siah1b | NM_009173.2 | chrX:164070702-164076135 |
| 19324 | Siah2 | NM_009174.3 | chr3:58674948-58692388 |
| 19325 | Siah3 | NM_001128093.1 | chr14:75455981-75526141 |
| 19326 | Sidt1 | NM_001159419.1 | chr16:44240179-44332838 |
| 19327 | Sidt2 | NM_001289668.1 | chr9:45937856-45955249 |
| 19328 | Sigirr | NM_023059.3 | chr7:141091174-141100546 |
| 19329 | Siglec1 | NM_011426.3 | chr2:131069219-131086765 |
| 19330 | Siglec15 | NM_001101038.1 | chr18:78043613-78057268 |
| 19331 | Siglec5 | NM_001271019.1 | chr7:43351340-43359470 |
| 19332 | Siglece | NM_031181.2 | chr7:43651069-43660161 |
| 19333 | Siglecg | NM_172900.3 | chr7:43408279-43418349 |
| 19334 | Siglech | NM_178706.5 | chr7:55768183-55778925 |
| 19335 | Sigmar1 | NM_001286528.1 | chr4:41738492-41741359 |
| 19336 | Sik1 | NM_010831.2 | chr17:31844249-31855792 |
| 19337 | Sik2 | NM_178710.3 | chr9:50892800-51009073 |
| 19338 | Sik3 | NM_027498.3 | chr9:46012819-46224194 |
| 19339 | Sike1 | NM_025679.3 | chr3:102995739-103009914 |
| 19340 | Sil1 | NM_030749.2 | chr18:35266395-35498925 |
| 19341 | Sim1 | NM_011376.3 | chr10:50895650-50989152 |
| 19342 | Sim2 | NM_011377.2 | chr16:94085259-94127032 |
| 19343 | Simc1 | NM_176987.4 | chr13:54503804-54551290 |
| 19344 | Sin3a | NM_001110350.1 | chr9:57076375-57128368 |
| 19345 | Sin3b | NM_001113248.2 | chr8:72723269-72739914 |
| 19346 | Sipa1 | NM_001164480.1 | chr19:5651184-5663707 |
| 19347 | Sipa1l1 | NM_001167983.1 | chr12:82170015-82451784 |
| 19348 | Sipa1l2 | NM_001081337.1 | chr8:125418062-125492710 |
| 19349 | Sipa1l3 | NM_001081028.1 | chr7:29320377-29505460 |
| 19350 | Sirpa | NM_001177647.2 | chr2:129592606-129632228 |
| 19351 | Sirpb1a | NM_001002898.1 | chr3:15371826-15426427 |
| 19352 | Sirpb1b | NM_001173460.1 | chr3:15495753-15575065 |
| 19353 | Sirt1 | NM_001159589.2 | chr10:63319004-63339035 |
| 19354 | Sirt2 | NM_001122765.1 | chr7:28766751-28788665 |
| 19355 | Sirt3 | NM_001127351.1 | chr7:140863642-140881869 |
| 19356 | Sirt4 | NM_001167691.1 | chr5:115478009-115484297 |
| 19357 | Sirt5 | NM_178848.3 | chr13:43359715-43395203 |
| 19358 | Sirt6 | NM_001163430.1 | chr10:81623785-81627322 |
| 19359 | Sirt7 | NM_153056.2 | chr11:120618371-120625002 |
| 19360 | Sis | NM_001081137.1 | chr3:72888559-72966866 |
| 19361 | Sit1 | NM_019436.3 | chr4:43482082-43483709 |
| 19362 | Siva1 | NM_001161737.1 | chr12:112644827-112649152 |
| 19363 | Six1 | NM_009189.3 | chr12:73041826-73046712 |
| 19364 | Six2 | NM_011380.2 | chr17:85684267-85688254 |
| 19365 | Six3 | NM_011381.4 | chr17:85620833-85626191 |
| 19366 | Six3os1 | NR_015385.2 | chr17:85609089-85618396 |
| 19367 | Six4 | NM_011382.2 | chr12:73100258-73113245 |
| 19368 | Six5 | NM_011383.1 | chr7:19094543-19098345 |
| 19369 | Six6 | NM_011384.5 | chr12:72939881-72944899 |
| 19370 | Ska1 | NM_001164355.1 | chr18:74195298-74207818 |
| 19371 | Ska2 | NM_025377.3 | chr11:87109260-87122974 |
| 19372 | Ska3 | NM_198605.3 | chr14:57806560-57826163 |

Fig. 26 - 103

| | | | | | | | | |
|---|---|---|---|---|---|---|---|---|
| 19373 | Skap1 | NM_001033186.3 | chr11:96464590-96759622 | | 19468 | Slc1a1 | NM_009199.2 | chr19:28835165-28913960 |
| 19374 | Skap2 | NM_018773.2 | chr6:51859164-52012549 | | 19469 | Slc1a2 | NM_001077514.3 | chr2:102658682-102790784 |
| 19375 | Ski | NM_011385.2 | chr4:155154074-155222535 | | 19470 | Slc1a3 | NM_148938.3 | chr15:8634123-8710807 |
| 19376 | Skida1 | NM_028317.2 | chr2:18044086-18048449 | | 19471 | Slc1a4 | NM_018861.3 | chr11:20302179-20332713 |
| 19377 | Skil | NM_001039090.2 | chr3:31095057-31122923 | | 19472 | Slc1a5 | NM_009201.2 | chr7:16781345-16798274 |
| 19378 | Skint1 | NM_001102662.1 | chr4:112006268-112029538 | | 19473 | Slc1a6 | NM_009200.3 | chr10:78780495-78814825 |
| 19379 | Skint10 | NM_177668.2 | chr4:112710829-112774861 | | 19474 | Slc1a7 | NM_146255.2 | chr4:107968333-108015532 |
| 19380 | Skint11 | NM_001166027.1 | chr4:114163383-114245028 | | 19475 | Slc20a1 | NM_001159593.1 | chr2:129198772-129205104 |
| 19381 | Skint2 | NM_001285963.1 | chr4:112613739-112652248 | | 19476 | Slc20a2 | NM_011394.3 | chr8:22476699-22569616 |
| 19382 | Skint3 | NM_001102474.1 | chr4:112232420-112298245 | | 19477 | Slc22a1 | NM_009202.5 | chr17:12648874-12675838 |
| 19383 | Skint4 | NM_178786.4 | chr4:112081469-112168076 | | 19478 | Slc22a12 | NM_009203.3 | chr19:6535855-6543070 |
| 19384 | Skint5 | NM_001167876.1 | chr4:113477890-113989503 | | 19479 | Slc22a13 | NM_133980.3 | chr9:119192977-119209105 |
| 19385 | Skint6 | NM_001103199.1 | chr4:112804615-113286973 | | 19480 | Slc22a13b-ps | NR_033303.1 | chr9:119220490-119231692 |
| 19386 | Skint7 | NM_001142775.1 | chr4:111972926-111986221 | | 19481 | Slc22a14 | NM_001037749.2 | chr9:119169455-119190393 |
| 19387 | Skint8 | NM_001100466.1 | chr4:111919554-111950356 | | 19482 | Slc22a15 | NM_001039371.2 | chr3:101855770-101924453 |
| 19388 | Skint9 | NM_177864.2 | chr4:112385968-112433985 | | 19483 | Slc22a16 | NM_027572.1 | chr10:40570361-40604132 |
| 19389 | Skiv2l | NM_021337.2 | chr17:34839225-34850204 | | 19484 | Slc22a17 | NM_021551.4 | chr14:54906726-54913132 |
| 19390 | Skiv2l2 | NM_028151.2 | chr13:112867779-112927380 | | 19485 | Slc22a18 | NM_010042760.1 | chr7:143475115-143499332 |
| 19391 | Skor1 | NM_001163755.1 | chr9:63138163-63147011 | | 19486 | Slc22a19 | NM_144785.2 | chr19:7673675-7711310 |
| 19392 | Skor2 | NM_001109743.1 | chr18:76856404-76900342 | | 19487 | Slc22a2 | NM_013667.2 | chr17:12584188-12628488 |
| 19393 | Skp1a | NM_011543.4 | chr11:52231994-52246858 | | 19488 | Slc22a20 | NM_198650.2 | chr19:5970233-5986143 |
| 19394 | Skp2 | NM_001285980.1 | chr15:9111981-9155425 | | 19489 | Slc22a21 | NM_019723.2 | chr11:53950823-53980027 |
| 19395 | Sla | NM_001029841.4 | chr15:66780818-66831829 | | 19490 | Slc22a22 | NM_172378.2 | chr15:57243770-57477625 |
| 19396 | Sla2 | NM_029983.5 | chr2:156872921-156887078 | | 19491 | Slc22a23 | NM_001033167.3 | chr13:34179157-34345182 |
| 19397 | Slain1 | NM_198014.2 | chr14:103650242-103704799 | | 19492 | Slc22a26 | NM_146232.1 | chr19:7781980-7802667 |
| 19398 | Slain1os | NR_045148.1 | chr14:103692982-103699432 | | 19493 | Slc22a27 | NM_134256.1 | chr19:7864368-7966027 |
| 19399 | Slain2 | NM_001113423.2 | chr5:72914361-72978841 | | 19494 | Slc22a28 | NM_001013820.3 | chr19:8062208-8131982 |
| 19400 | Slamf1 | NM_013730.4 | chr1:171767131-171801184 | | 19495 | Slc22a29 | NM_172776.2 | chr19:8160167-8218839 |
| 19401 | Slamf6 | NM_030710.2 | chr1:171917536-171943868 | | 19496 | Slc22a3 | NM_011395.2 | chr17:12419973-12507704 |
| 19402 | Slamf7 | NM_144539.5 | chr1:171632402-171653037 | | 19497 | Slc22a30 | NM_177002.3 | chr19:8335622-8405105 |
| 19403 | Slamf8 | NM_029084.3 | chr1:172581376-172590568 | | 19498 | Slc22a4 | NM_019687.3 | chr11:53983125-54028090 |
| 19404 | Slamf9 | NM_029612.4 | chr1:172475359-172478409 | | 19499 | Slc22a5 | NM_011396.2 | chr11:53864541-53891703 |
| 19405 | Slbp | NM_001289724.1 | chr5:33640054-33652574 | | 19500 | Slc22a6 | NM_008766.3 | chr19:8617995-8628299 |
| 19406 | Slc10a1 | NM_001177561.1 | chr12:80953184-80968079 | | 19501 | Slc22a7 | NM_144856.2 | chr17:46432184-46438477 |
| 19407 | Slc10a2 | NM_011388.2 | chr8:5085622-5105232 | | 19502 | Slc22a8 | NM_001164634.1 | chr19:8591253-8611835 |
| 19408 | Slc10a3 | NM_001256104.1 | chrX:74369218-74373349 | | 19503 | Slc23a1 | NM_011397.4 | chr18:35614603-35627227 |
| 19409 | Slc10a3-ubl4 | NM_001278271.1 | chrX:74367446-74373349 | | 19504 | Slc23a2 | NM_018824.2 | chr2:132052495-132145108 |
| 19410 | Slc10a4 | NM_173403.2 | chr5:73006903-73012955 | | 19505 | Slc23a3 | NM_194333.3 | chr1:75125541-75133890 |
| 19411 | Slc10a5 | NM_001010524.2 | chr3:10331733-10335656 | | 19506 | Slc24a1 | NM_144813.1 | chr9:64922860-64951607 |
| 19412 | Slc10a6 | NM_029415.2 | chr5:103605710-103629403 | | 19507 | Slc24a2 | NM_001110240.1 | chr4:86983125-87227963 |
| 19413 | Slc10a7 | NM_001099981.2 | chr8:78509327-78734012 | | 19508 | Slc24a3 | NM_053195.2 | chr2:145242610-145641939 |
| 19414 | Slc11a1 | NM_013612.2 | chr1:74375202-74386051 | | 19509 | Slc24a4 | NM_172152.2 | chr12:102129418-102266749 |
| 19415 | Slc11a2 | NM_001146161.1 | chr15:100392657-100423055 | | 19510 | Slc24a5 | NM_175034.3 | chr2:125068126-125088677 |
| 19416 | Slc12a1 | NM_001079690.1 | chr2:125152599-125230001 | | 19511 | Slc25a1 | NM_153150.2 | chr16:17925210-17928219 |
| 19417 | Slc12a2 | NM_009194.3 | chr18:57878677-57946821 | | 19512 | Slc25a10 | NM_013770.2 | chr11:120491836-120501161 |
| 19418 | Slc12a3 | NM_001205311.1 | chr8:94329207-94366221 | | 19513 | Slc25a11 | NM_024211.3 | chr11:70644026-70647039 |
| 19419 | Slc12a4 | NM_001253804.1 | chr8:105943589-105966115 | | 19514 | Slc25a12 | NM_172436.3 | chr2:71274294-71367554 |
| 19420 | Slc12a5 | NM_020333.2 | chr2:164967987-164999731 | | 19515 | Slc25a13 | NM_001175572.1 | chr6:6041217-6217173 |
| 19421 | Slc12a6 | NM_133648.2 | chr2:112284687-112363163 | | 19516 | Slc25a14 | NM_001166450.2 | chrX:48623673-48662298 |
| 19422 | Slc12a7 | NM_011390.2 | chr13:73763696-73816742 | | 19517 | Slc25a15 | NM_183325.4 | chr8:22375549-22398621 |
| 19423 | Slc12a8 | NM_001083902.1 | chr16:33518594-33664135 | | 19518 | Slc25a16 | NM_175194.2 | chr10:62920632-62946494 |
| 19424 | Slc12a9 | NM_031406.3 | chr5:137314557-137333582 | | 19519 | Slc25a17 | NM_011399.3 | chr15:81318920-81360765 |
| 19425 | Slc13a1 | NM_019412.2 | chr6:24088282-24168092 | | 19520 | Slc25a18 | NM_001081048.2 | chr6:120773767-120793982 |
| 19426 | Slc13a2 | NM_022411.3 | chr11:78397275-78422185 | | 19521 | Slc25a19 | NM_001252384.1 | chr11:115614180-115628295 |
| 19427 | Slc13a2os | NR_003282.2 | chr1:78394484-78405657 | | 19522 | Slc25a2 | NM_001159275.1 | chr18:37637377-37638723 |
| 19428 | Slc13a3 | NM_054055.2 | chr2:165405294-165473197 | | 19523 | Slc25a20 | NM_020520.4 | chr9:108662097-108684641 |
| 19429 | Slc13a4 | NM_172892.3 | chr6:35267952-35308126 | | 19524 | Slc25a21 | NM_001167976.1 | chr12:56712633-57160643 |
| 19430 | Slc13a5 | NM_001004148.4 | chr11:72241993-72266604 | | 19525 | Slc25a22 | NM_001177576.1 | chr7:141429748-141434594 |
| 19431 | Slc14a1 | NM_001171010.1 | chr18:78100090-78123426 | | 19526 | Slc25a23 | NM_025877.4 | chr17:57043710-57059863 |
| 19432 | Slc14a2 | NM_001110273.1 | chr18:78146143-78179172 | | 19527 | Slc25a24 | NM_172685.3 | chr3:109123148-109168409 |
| 19433 | Slc15a1 | NM_053079.2 | chr14:121459620-121505254 | | 19528 | Slc25a25 | NM_001164357.1 | chr2:32414486-32451470 |
| 19434 | Slc15a2 | NM_001145899.1 | chr16:36771876-36784962 | | 19529 | Slc25a26 | NM_026255.5 | chr6:94500313-94604652 |
| 19435 | Slc15a3 | NM_023044.2 | chr19:10842543-10857915 | | 19530 | Slc25a27 | NM_028711.3 | chr17:43641899-43667015 |
| 19436 | Slc15a4 | NM_133895.1 | chr5:127595665-127617392 | | 19531 | Slc25a28 | NM_145156.1 | chr19:43663800-43674881 |
| 19437 | Slc15a5 | NM_137983589-138079916 | chr6:137983589-138079916 | | 19532 | Slc25a29 | NM_181328.3 | chr12:108825877-108835876 |
| 19438 | Slc16a1 | NM_009196.4 | chr3:104638663-104658462 | | 19533 | Slc25a3 | NM_133668.3 | chr10:91116577-91123963 |
| 19439 | Slc16a10 | NM_001114332.1 | chr10:40033534-40142254 | | 19534 | Slc25a30 | NM_026232.3 | chr14:75761998-75787037 |
| 19440 | Slc16a11 | NM_153081.3 | chr11:70213909-70216414 | | 19535 | Slc25a31 | NM_178386.3 | chr3:40708870-40726094 |
| 19441 | Slc16a12 | NM_172838.3 | chr19:34668405-34747111 | | 19536 | Slc25a32 | NM_172402.2 | chr15:39094190-39112716 |
| 19442 | Slc16a13 | NM_172523.3 | chr11:70216791-70220994 | | 19537 | Slc25a33 | NM_027460.2 | chr4:149744035-149774267 |
| 19443 | Slc16a14 | NM_027921.1 | chr3:84906704-84935083 | | 19538 | Slc25a34 | NM_001013780.1 | chr4:141618824-141623834 |
| 19444 | Slc16a2 | NM_009197.2 | chrX:103697413-103821988 | | 19539 | Slc25a35 | NM_028048.2 | chr11:68968130-68972515 |
| 19445 | Slc16a3 | NM_001038653.1 | chr11:120949066-120959000 | | 19540 | Slc25a36 | NM_138756.4 | chr9:97076010-97111041 |
| 19446 | Slc16a4 | NM_146136.1 | chr3:107291291-107312116 | | 19541 | Slc25a37 | NM_026331.3 | chr14:69241850-69285103 |
| 19447 | Slc16a5 | NM_001080934.1 | chr11:115462472-115474398 | | 19542 | Slc25a38 | NM_144793.1 | chr9:120110398-120124319 |
| 19448 | Slc16a6 | NM_001160855.1 | chr11:109450855-109473596 | | 19543 | Slc25a39 | NM_026542.3 | chr11:102402975-102407517 |
| 19449 | Slc16a7 | NM_011391.1 | chr10:125227484-125328535 | | 19544 | Slc25a4 | NM_007450.4 | chr8:46207340-46211009 |
| 19450 | Slc16a8 | NM_020516.2 | chr15:79251015-79254748 | | 19545 | Slc25a40 | NM_001289595.1 | chr5:8422837-8454839 |
| 19451 | Slc16a9 | NM_025807.3 | chr10:70245275-70285951 | | 19546 | Slc25a41 | NM_175333.3 | chr17:57032771-57041654 |
| 19452 | Slc17a1 | NM_001170638.1 | chr13:23870272-23895730 | | 19547 | Slc25a42 | NM_001007570.2 | chr8:70184339-70212281 |
| 19453 | Slc17a2 | NM_144856.2 | chr13:23807026-23823525 | | 19548 | Slc25a43 | NM_001085497.2 | chrX:36743631-36777307 |
| 19454 | Slc17a3 | NM_001164743.1 | chr13:23839433-23860714 | | 19549 | Slc25a44 | NM_001145876.2 | chr3:88410493-88425141 |
| 19455 | Slc17a4 | NM_177016.3 | chr13:23897888-23915007 | | 19550 | Slc25a45 | NM_134154.3 | chr19:5878465-5885768 |
| 19456 | Slc17a5 | NM_176452.4 | chr9:78536486-78586045 | | 19551 | Slc25a46 | NM_026165.3 | chr18:31580167-31609902 |
| 19457 | Slc17a6 | NM_080853.3 | chr7:51621829-51671126 | | 19552 | Slc25a47 | NM_001012310.2 | chr12:108851128-108866815 |
| 19458 | Slc17a7 | NM_182993.2 | chr7:45163920-45176139 | | 19553 | Slc25a48 | NM_177809.4 | chr13:56438354-56472363 |
| 19459 | Slc17a8 | NM_182959.6 | chr10:89574019-89621049 | | 19554 | Slc25a5 | NM_007451.4 | chr6:36795996-36798808 |
| 19460 | Slc17a9 | NM_183161.3 | chr2:180725338-180742278 | | 19555 | Slc25a51 | NM_001009949.3 | chr4:45395923-45408766 |
| 19461 | Slc18a1 | NM_153054.2 | chr8:69087707-69089222 | | 19556 | Slc25a53 | NM_001082412.2 | chrX:136981115-137068302 |
| 19462 | Slc18a2 | NM_172523.3 | chr19:59260877-59296012 | | 19557 | Slc25a54 | NM_029054.1 | chr3:109080498-109116582 |
| 19463 | Slc18a3 | NM_021712.2 | chr14:32462436-32464850 | | 19558 | Slc26a1 | NM_174870.4 | chr5:108669880-108675365 |
| 19464 | Slc18b1 | NM_183116.2 | chr10:23796985-23837968 | | 19559 | Slc26a10 | NM_176615.3 | chr10:127172425-127180645 |
| 19465 | Slc19a1 | NM_001199271.1 | chr10:77032738-77050432 | | 19560 | Slc26a11 | NM_178743.3 | chr11:119355556-119381076 |
| 19466 | Slc19a2 | NM_026455.1 | chr1:164249045-164265385 | | 19561 | Slc26a2 | NM_007885.2 | chr18:61196853-61211596 |
| 19467 | Slc19a3 | NM_030556.2 | chr1:83012522-83038448 | | 19562 | Slc26a3 | NM_021353.3 | chr12:31438218-31473919 |

Fig. 26 - 104

| | | | | | | | | |
|---|---|---|---|---|---|---|---|---|
| 19563 | Slc26a4 | NM_011867.3 | chr12:31519818-31559969 | | 19658 | Slc38a9 | NM_178746.4 | chr13:112660765-112738752 |
| 19564 | Slc26a5 | NM_001289787.1 | chr5:21809000-21862006 | | 19659 | Slc39a1 | NM_013901.2 | chr3:90248191-90253612 |
| 19565 | Slc26a6 | NM_134420.4 | chr9:108854042-108862143 | | 19660 | Slc39a10 | NM_172653.2 | chr1:46807543-46853509 |
| 19566 | Slc26a7 | NM_145947.2 | chr4:14505196-14621778 | | 19661 | Slc39a11 | NM_001166503.1 | chr11:113244854-113565815 |
| 19567 | Slc26a8 | NM_001290320.1 | chr17:28637778-28689987 | | 19662 | Slc39a12 | NM_001012305.2 | chr2:14388397-14494977 |
| 19568 | Slc26a9 | NM_177243.4 | chr1:131744021-131770405 | | 19663 | Slc39a13 | NM_001290765.1 | chr2:91061780-91070315 |
| 19569 | Slc27a1 | NM_011977.3 | chr8:71568926-71586708 | | 19664 | Slc39a14 | NM_001135151.1 | chr14:70303466-70351424 |
| 19570 | Slc27a2 | NM_011978.2 | chr2:126553023-126588243 | | 19665 | Slc39a2 | NM_001039676.2 | chr14:51893609-51896745 |
| 19571 | Slc27a3 | NM_011988.3 | chr3:90385232-90389927 | | 19666 | Slc39a3 | NM_134135.1 | chr10:81028539-81033912 |
| 19572 | Slc27a4 | NM_011989.4 | chr2:29802679-29817522 | | 19667 | Slc39a4 | NM_028064.2 | chr15:76612382-76616852 |
| 19573 | Slc27a5 | NM_009512.2 | chr7:12988345-12998192 | | 19668 | Slc39a5 | NM_001136237.1 | chr10:128395930-128401224 |
| 19574 | Slc27a6 | NM_001081072.1 | chr18:58556239-58612869 | | 19669 | Slc39a6 | NM_139143.3 | chr18:24579880-24603817 |
| 19575 | Slc28a1 | NM_001004184.3 | chr7:81114798-81170416 | | 19670 | Slc39a7 | NM_001077709.1 | chr17:34028265-34031690 |
| 19576 | Slc28a2 | NM_172980.2 | chr2:122426476-122461130 | | 19671 | Slc39a8 | NM_001135149.1 | chr3:135825656-135888572 |
| 19577 | Slc28a3 | NM_022317.3 | chr13:58553307-58610877 | | 19672 | Slc39a9 | NM_026244.2 | chr12:80644214-80683342 |
| 19578 | Slc29a1 | NM_001199113.1 | chr17:45585199-45593640 | | 19673 | Slc3a1 | NM_009205.2 | chr17:85028346-85064241 |
| 19579 | Slc29a2 | NM_007854.3 | chr19:5024005-5031972 | | 19674 | Slc3a2 | NM_001161413.1 | chr19:8706881-8723369 |
| 19580 | Slc29a3 | NM_023596.3 | chr10:60712071-60752782 | | 19675 | Slc40a1 | NM_016917.2 | chr1:45908069-45925594 |
| 19581 | Slc29a4 | NM_146257.2 | chr5:142702100-142722490 | | 19676 | Slc41a1 | NM_173865.3 | chr1:131828011-131848864 |
| 19582 | Slc2a1 | NM_011400.3 | chr4:119108744-119137329 | | 19677 | Slc41a2 | NM_177388.3 | chr10:83231138-83337817 |
| 19583 | Slc2a10 | NM_130451.3 | chr2:165503896-165519917 | | 19678 | Slc41a3 | NM_001037493.2 | chr6:90619245-90646412 |
| 19584 | Slc2a12 | NM_178934.4 | chr10:22645010-22703880 | | 19679 | Slc43a1 | NM_001081349.2 | chr2:84839407-84863586 |
| 19585 | Slc2a13 | NM_001033633.3 | chr15:91267690-91573261 | | 19680 | Slc43a2 | NM_001199283.1 | chr11:75532111-75577572 |
| 19586 | Slc2a2 | NM_031197.2 | chr3:28697902-28728360 | | 19681 | Slc43a3 | NM_023398.3 | chr2:84936645-84958509 |
| 19587 | Slc2a3 | NM_011401.4 | chr6:122727808-122742745 | | 19682 | Slc44a1 | NM_001159633.3 | chr4:53440412-53550164 |
| 19588 | Slc2a4 | NM_009204.2 | chr11:69942285-69948190 | | 19683 | Slc44a2 | NM_001199186.1 | chr9:21320718-21355028 |
| 19589 | Slc2a4rg-ps | NR_045164.1 | chr2:181384249-181387596 | | 19684 | Slc44a3 | NM_145394.3 | chr3:121459527-121532344 |
| 19590 | Slc2a5 | NM_019741.3 | chr4:150119343-150144168 | | 19685 | Slc44a4 | NM_023557.3 | chr17:34914465-34930436 |
| 19591 | Slc2a6 | NM_001177627.1 | chr2:27021366-27027998 | | 19686 | Slc44a5 | NM_001081263.1 | chr3:153973435-154271720 |
| 19592 | Slc2a7 | NM_001085529.1 | chr4:150148971-150168482 | | 19687 | Slc45a1 | NM_173774.3 | chr4:150629395-150652174 |
| 19593 | Slc2a8 | NM_019488.4 | chr2:32972988-32982056 | | 19688 | Slc45a2 | NM_053077.3 | chr15:11000720-11029233 |
| 19594 | Slc2a9 | NM_001012363.2 | chr5:38849272-38483385 | | 19689 | Slc45a3 | NM_001177628.2 | chr1:131962914-131982972 |
| 19595 | Slc30a1 | NM_009579.3 | chr1:191906780-191913247 | | 19690 | Slc45a4 | NM_001033219.3 | chr15:73580290-73624744 |
| 19596 | Slc30a10 | NM_001033286.2 | chr1:185454847-185468761 | | 19691 | Slc46a1 | NM_026740.2 | chr11:78465700-78471945 |
| 19597 | Slc30a2 | NM_001039677.2 | chr4:134343045-134354484 | | 19692 | Slc46a2 | NM_021053.4 | chr4:59905898-59915056 |
| 19598 | Slc30a3 | NM_011773.3 | chr5:31086105-31093527 | | 19693 | Slc46a3 | NM_027872.3 | chr5:147878440-147894802 |
| 19599 | Slc30a4 | NM_001290993.1 | chr2:122681232-122702663 | | 19694 | Slc47a1 | NM_026183.5 | chr11:61343399-61378075 |
| 19600 | Slc30a5 | NM_022885.2 | chr13:100802647-100833427 | | 19695 | Slc47a2 | NM_001035542.2 | chr11:61301630-61342860 |
| 19601 | Slc30a6 | NM_001252478.1 | chr17:74395607-74424229 | | 19696 | Slc48a1 | NM_026353.4 | chr15:97784364-97792692 |
| 19602 | Slc30a7 | NM_023214.7 | chr3:115938972-116007406 | | 19697 | Slc4a1 | NM_011403.2 | chr11:102348819-102365281 |
| 19603 | Slc30a8 | NM_172816.3 | chr15:52295552-52335733 | | 19698 | Slc4a10 | NM_001242378.1 | chr2:62046514-62326743 |
| 19604 | Slc30a9 | NM_178651.4 | chr5:67306954-67356142 | | 19699 | Slc4a11 | NM_001081162.1 | chr2:130684107-130697519 |
| 19605 | Slc31a1 | NM_175090.4 | chr4:62360700-62391769 | | 19700 | Slc4a1ap | NM_009206.2 | chr5:31526994-31554038 |
| 19606 | Slc31a2 | NM_001290518.1 | chr4:62291546-62298412 | | 19701 | Slc4a2 | NM_001253892.1 | chr5:24427520-24440947 |
| 19607 | Slc32a1 | NM_009508.2 | chr2:158610757-158615747 | | 19702 | Slc4a3 | NM_009208.3 | chr1:75546265-75559431 |
| 19608 | Slc33a1 | NM_001272035.1 | chr3:63942323-63964733 | | 19703 | Slc4a4 | NM_001136260.1 | chr5:88887259-89239656 |
| 19609 | Slc34a1 | NM_011392.2 | chr13:55399647-55414695 | | 19704 | Slc4a5 | NM_001166067.1 | chr6:83237374-83304945 |
| 19610 | Slc34a2 | NM_011402.3 | chr5:53049352-53071663 | | 19705 | Slc4a7 | NM_001033270.2 | chr14:14703024-14799943 |
| 19611 | Slc34a3 | NM_080854.3 | chr2:25228896-25234234 | | 19706 | Slc4a8 | NM_021530.2 | chr15:100761746-100823971 |
| 19612 | Slc35a1 | NM_011895.3 | chr4:34663256-34687438 | | 19707 | Slc4a9 | NM_001271544.1 | chr18:36528151-36544608 |
| 19613 | Slc35a2 | NM_001083317.1 | chrX:7884243-7894027 | | 19708 | Slc50a1 | NM_009057.3 | chr3:89268245-89270570 |
| 19614 | Slc35a3 | NM_144902.3 | chr3:116670797-116712280 | | 19709 | Slc51a | NM_145932.3 | chr16:32475577-32487879 |
| 19615 | Slc35a4 | NM_001083317.1 | chr18:36679214-36683862 | | 19710 | Slc51b | NM_178933.2 | chr9:65412752-65422773 |
| 19616 | Slc35a5 | NM_028756.4 | chr16:45139572-45158673 | | 19711 | Slc52a2 | NM_029643.3 | chr15:76538942-76542130 |
| 19617 | Slc35b1 | NM_016752.1 | chr11:95384921-95391652 | | 19712 | Slc52a3 | NM_001164819.1 | chr2:151999865-152009258 |
| 19618 | Slc35b2 | NM_028662.2 | chr17:45564151-45567669 | | 19713 | Slc5a1 | NM_019810.4 | chr5:33104218-33162699 |
| 19619 | Slc35b3 | NM_001170430.1 | chr13:38932139-38960537 | | 19714 | Slc5a10 | NM_001033227.2 | chr11:61672781-61720799 |
| 19620 | Slc35b4 | NM_021435.3 | chr6:34155878-34177054 | | 19715 | Slc5a11 | NM_146198.2 | chr7:123214865-123273251 |
| 19621 | Slc35c1 | NM_145832.3 | chr2:92452764-92460518 | | 19716 | Slc5a12 | NM_001003915.2 | chr2:110597298-110649345 |
| 19622 | Slc35c2 | NM_001252573.1 | chr2:165276521-165287787 | | 19717 | Slc5a2 | NM_133254.3 | chr7:128265696-128272433 |
| 19623 | Slc35d1 | NM_177732.4 | chr4:103171717-103214884 | | 19718 | Slc5a3 | NM_017391.3 | chr16:92058321-92087473 |
| 19624 | Slc35d2 | NM_001001321.3 | chr13:64096309-64129330 | | 19719 | Slc5a4a | NM_133184.2 | chr10:76147450-76189265 |
| 19625 | Slc35d3 | NM_029529.3 | chr10:19847916-19851459 | | 19720 | Slc5a4b | NM_023219.2 | chr10:76058620-76111018 |
| 19626 | Slc35e1 | NM_177766.3 | chr8:72477994-72492614 | | 19721 | Slc5a5 | NM_053248.2 | chr8:70882888-70892757 |
| 19627 | Slc35e2 | NM_177675.4 | chr4:155601415-155623340 | | 19722 | Slc5a6 | NM_001177621.1 | chr5:31036035-31048562 |
| 19628 | Slc35e3 | NM_029875.2 | chr10:117733677-117746358 | | 19723 | Slc5a7 | NM_022025.4 | chr17:54273589-54299034 |
| 19629 | Slc35e4 | NM_153142.3 | chr11:3907021-3914664 | | 19724 | Slc5a8 | NM_145423.2 | chr10:88885991-88929515 |
| 19630 | Slc35f1 | NM_178675.4 | chr10:52690500-53111622 | | 19725 | Slc5a9 | NM_145551.4 | chr4:111875376-111902796 |
| 19631 | Slc35f2 | NM_028060.3 | chr9:53771534-53818161 | | 19726 | Slc6a1 | NM_178703.4 | chr6:114282634-114317525 |
| 19632 | Slc35f3 | NM_175434.3 | chr8:126298578-126395977 | | 19727 | Slc6a11 | NM_172890.3 | chr6:114131240-114249886 |
| 19633 | Slc35f4 | NM_029238.2 | chr14:49298519-49525837 | | 19728 | Slc6a12 | NM_133661.3 | chr6:121346696-121365773 |
| 19634 | Slc35f5 | NM_028787.4 | chr1:125561015-125595684 | | 19729 | Slc6a13 | NM_144512.2 | chr6:121300295-121337718 |
| 19635 | Slc35f6 | NM_175763.3 | chr5:30647938-30659729 | | 19730 | Slc6a14 | NM_020049.4 | chrX:21714899-21742357 |
| 19636 | Slc35g1 | NM_175507.3 | chr19:38395979-38405607 | | 19731 | Slc6a15 | NM_001252330.1 | chr10:103367807-103419379 |
| 19637 | Slc35g2 | NM_001101483.1 | chr9:100552187-100571085 | | 19732 | Slc6a17 | NM_172271.2 | chr3:107467547-107518018 |
| 19638 | Slc35g3 | NM_167598.5 | chr11:69759885-69761844 | | 19733 | Slc6a18 | NM_001040692.3 | chr13:73661749-73678023 |
| 19639 | Slc36a1 | NM_153139.4 | chr11:55204339-55236330 | | 19734 | Slc6a19 | NM_028878.3 | chr13:73681156-73700695 |
| 19640 | Slc36a1os | NR_046034.1 | chr11:55191718-55197682 | | 19735 | Slc6a19os | NM_027780.1 | chr13:73698925-73709856 |
| 19641 | Slc36a2 | NM_153170.3 | chr11:55158467-55185077 | | 19736 | Slc6a2 | NM_009209.3 | chr8:92961046-93001667 |
| 19642 | Slc36a3 | NM_172258.3 | chr11:55124822-55151706 | | 19737 | Slc6a20a | NM_139142.3 | chr9:123636906-123678832 |
| 19643 | Slc36a4 | NM_172289.4 | chr9:15709768-15738789 | | 19738 | Slc6a20b | NM_011731.3 | chr9:123593819-123632565 |
| 19644 | Slc37a1 | NM_001242467.1 | chr17:31296223-31350698 | | 19739 | Slc6a3 | NM_010020.3 | chr13:73536746-73578672 |
| 19645 | Slc37a2 | NM_001145960.1 | chr9:37229148-37255738 | | 19740 | Slc6a4 | NM_010484.2 | chr11:76998596-77032343 |
| 19646 | Slc37a3 | NM_028123.3 | chr6:39334770-39377707 | | 19741 | Slc6a5 | NM_001146013.1 | chr7:49910298-49959493 |
| 19647 | Slc37a4 | NM_008063.2 | chr9:44398175-44402965 | | 19742 | Slc6a6 | NM_009320.4 | chr6:91684066-91759063 |
| 19648 | Slc38a1 | NM_001166456.1 | chr15:96571417-96642343 | | 19743 | Slc6a7 | NM_201353.1 | chr18:60995379-61014199 |
| 19649 | Slc38a10 | NM_146174798.1 | chr11:120103950-120151351 | | 19744 | Slc6a8 | NM_001142809.1 | chrX:73673132-73682500 |
| 19650 | Slc38a11 | NM_177074.2 | chr2:65316632-65364026 | | 19745 | Slc6a9 | NM_008135.4 | chr4:117835257-117869305 |
| 19651 | Slc38a2 | NM_175121.3 | chr15:96687391-96699698 | | 19746 | Slc7a1 | NM_007513.4 | chr5:148327409-148399904 |
| 19652 | Slc38a3 | NM_001199217.1 | chr9:107651154-107667399 | | 19747 | Slc7a10 | NM_017394.4 | chr7:35186384-35201111 |
| 19653 | Slc38a4 | NM_027052.3 | chr15:96994822-97055956 | | 19748 | Slc7a11 | NM_011990.2 | chr3:50364935-50443613 |
| 19654 | Slc38a5 | NM_172479.3 | chrX:8271380-8280176 | | 19749 | Slc7a12 | NM_080852.2 | chr3:14480698-14505818 |
| 19655 | Slc38a6 | NM_001037717.3 | chr12:73286847-73354045 | | 19750 | Slc7a13 | NM_028746.3 | chr4:19818726-19842213 |
| 19656 | Slc38a7 | NM_172758.4 | chr8:95835922-95853491 | | 19751 | Slc7a14 | NM_172861.3 | chr3:31202855-31310319 |
| 19657 | Slc38a8 | NM_001009950.1 | chr8:119479602-119501698 | | 19752 | Slc7a15 | NM_001038660.2 | chr12:8528482-8539566 |

Fig. 26 - 105

| | | | | | | | | |
|---|---|---|---|---|---|---|---|---|
| 19753 | Slc7a2 | NM_001044740.2 | chr8:40862366-40922070 | | 19848 | Smarcal1 | NM_018817.2 | chr1:72583250-72636790 |
| 19754 | Slc7a3 | NM_007515.3 | chrX:101079209-101085405 | | 19849 | Smarch1 | NM_001161853.1 | chr10:75896768-75923614 |
| 19755 | Slc7a4 | NM_144852.3 | chr16:17572017-17576671 | | 19850 | Smarcc1 | NM_009211.2 | chr9:110132023-110240178 |
| 19756 | Slc7a5 | NM_011404.3 | chr8:121881145-121907686 | | 19851 | Smarcc2 | NM_001114096.1 | chr10:128459235-128490174 |
| 19757 | Slc7a6 | NM_178798.3 | chr8:106168874-106198704 | | 19852 | Smarcd1 | NM_031842.2 | chr15:99702286-99713995 |
| 19758 | Slc7a6os | NM_001007567.2 | chr8:106200437-106210933 | | 19853 | Smarcd2 | NM_001130187.1 | chr11:106263170-106272972 |
| 19759 | Slc7a7 | NM_001253679.1 | chr14:54369441-54417679 | | 19854 | Smarcd3 | NM_025891.3 | chr5:24592621-24602002 |
| 19760 | Slc7a8 | NM_016972.2 | chr14:54722214-54781886 | | 19855 | Smarce1 | NM_020618.4 | chr11:99209047-99231017 |
| 19761 | Slc7a9 | NM_001199015.1 | chr7:35449091-35466034 | | 19856 | Smc1a | NM_019710.2 | chrX:152016427-152061973 |
| 19762 | Slc8a1 | NM_001112798.2 | chr17:81373104-81738387 | | 19857 | Smc1b | NM_080470.1 | chr15:85064688-85131957 |
| 19763 | Slc8a2 | NM_148946.2 | chr7:16130299-16160511 | | 19858 | Smc2 | NM_008017.4 | chr4:52439220-52488365 |
| 19764 | Slc8a3 | NM_001167920.1 | chr12:81197914-81333180 | | 19859 | Smc2os | NR_045175.1 | chr4:52430283-52438964 |
| 19765 | Slc8b1 | NM_001177594.1 | chr5:120511191-120534024 | | 19860 | Smc3 | NM_007790.3 | chr19:53600395-53645831 |
| 19766 | Slc9a1 | NM_016981.2 | chr4:133369771-133423698 | | 19861 | Smc4 | NM_133786.3 | chr3:69004971-69034623 |
| 19767 | Slc9a2 | NM_001033289.2 | chr1:40681711-40768885 | | 19862 | Smc5 | NM_001252684.1 | chr19:23206440-23273897 |
| 19768 | Slc9a3 | NM_001081060.1 | chr13:74121514-74166064 | | 19863 | Smc6 | NM_025695.4 | chr12:11265885-11319785 |
| 19769 | Slc9a3r1 | NM_012030.2 | chr11:115163340-115181178 | | 19864 | Smchd1 | NM_028887.3 | chr17:71344492-71475343 |
| 19770 | Slc9a3r2 | NM_023055.2 | chr17:24639281-24650305 | | 19865 | Smco1 | NM_183283.2 | chr16:32271608-32274779 |
| 19771 | Slc9a4 | NM_177084.3 | chr1:40580226-40630731 | | 19866 | Smco2 | NM_027059.1 | chr6:146850109-146871404 |
| 19772 | Slc9a5 | NM_001081332.1 | chr8:105348257-105369881 | | 19867 | Smco3 | NM_001039588.2 | chr6:136829930-136835450 |
| 19773 | Slc9a6 | NM_172780.3 | chrX:56609834-56664230 | | 19868 | Smco4 | NM_133214.2 | chr9:15505494-15545259 |
| 19774 | Slc9a7 | NM_177353.3 | chrX:20105754-20291764 | | 19869 | Smcp | NM_008574.3 | chr3:92583865-92589024 |
| 19775 | Slc9a8 | NM_148929.3 | chr2:167421709-167477000 | | 19870 | Smcr8 | NM_001085440.1 | chr11:60777524-60788287 |
| 19776 | Slc9a9 | NM_177909.5 | chr9:94669891-95230452 | | 19871 | Smdt1 | NM_026914.1 | chr15:82346045-82349062 |
| 19777 | Slc9b1 | NM_028946.3 | chr3:135348036-135397827 | | 19872 | Smek1 | NM_001160214.1 | chr12:101039408-101083702 |
| 19778 | Slc9b2 | NM_178877.6 | chr3:135307699-135342767 | | 19873 | Smek2 | NM_134034.2 | chr11:29172906-29220797 |
| 19779 | Slc9c1 | NM_198106.4 | chr16:45535265-45607001 | | 19874 | Smg1 | NM_001031814.1 | chr7:118131311-118243637 |
| 19780 | Slco1a1 | NM_013797.5 | chr6:141907280-141946962 | | 19875 | Smg5 | NM_178246.3 | chr3:88336259-88362337 |
| 19781 | Slco1a4 | NM_030687.1 | chr6:141805439-141856171 | | 19876 | Smg6 | NM_001002764.1 | chr11:74925871-75164448 |
| 19782 | Slco1a5 | NM_001267707.1 | chr6:142234226-142278874 | | 19877 | Smg7 | NM_001005507.2 | chr1:152836994-152902646 |
| 19783 | Slco1a6 | NM_023718.3 | chr6:142085767-142186149 | | 19878 | Smg8 | NM_024262.1 | chr11:87077731-87086771 |
| 19784 | Slco1b2 | NM_020495.1 | chr6:141629517-141686635 | | 19879 | Smg9 | NM_028047.2 | chr7:24399627-24422777 |
| 19785 | Slco1c1 | NM_001177772.1 | chr6:141524385-141570177 | | 19880 | Smgc | NM_198927.3 | chr15:91838327-91861435 |
| 19786 | Slco2a1 | NM_033314.3 | chr9:103008488-103087849 | | 19881 | Smim1 | NM_001163721.1 | chr4:154020469-154026044 |
| 19787 | Slco2b1 | NM_001252530.1 | chr7:99657803-99706842 | | 19882 | Smim11 | NM_138743.2 | chr16:92301302-92313041 |
| 19788 | Slco3a1 | NM_001038643.1 | chr7:74275417-74554780 | | 19883 | Smim12 | NM_030252.2 | chr4:127243783-127247809 |
| 19789 | Slco4a1 | NM_148933.1 | chr2:180460977-180474853 | | 19884 | Smim13 | NM_001135577.2 | chr13:41249843-41276577 |
| 19790 | Slco4c1 | NM_172658.3 | chr1:96818783-96872171 | | 19885 | Smim14 | NM_133697.3 | chr5:65448754-65492835 |
| 19791 | Slco5a1 | NM_172841.2 | chr1:12866549-12991135 | | 19886 | Smim15 | NM_001048250.2 | chr13:108044473-108049146 |
| 19792 | Slco6b1 | NR_120500.1 | chr1:96906176-96997560 | | 19887 | Smim18 | NM_001206849.1 | chr8:33742111-33747770 |
| 19793 | Slco6c1 | NM_028942.4 | chr1:97059448-97128303 | | 19888 | Smim19 | NM_001012667.2 | chr2:22462613-22476879 |
| 19794 | Slco6d1 | NM_001145433.1 | chr1:98421123-98509380 | | 19889 | Smim20 | NM_001145433.1 | chr5:53267105-53278540 |
| 19795 | Slfn1 | NM_011407.1 | chr11:83116844-83122659 | | 19890 | Smim22 | NM_001253796.1 | chr16:5007315-5008308 |
| 19796 | Slfn10-ps | NR_073523.1 | chr11:83028125-83040042 | | 19891 | Smim23 | NM_027050.1 | chr11:32820375-32824594 |
| 19797 | Slfn14 | NM_001166028.1 | chr11:83275111-83286726 | | 19892 | Smim24 | NM_001099917.1 | chr10:81393063-81395079 |
| 19798 | Slfn2 | NM_011408.1 | chr11:83065111-83070678 | | 19893 | Smim3 | NM_134133.2 | chr18:60474190-60501983 |
| 19799 | Slfn3 | NM_011409.1 | chr11:83191329-83215154 | | 19894 | Smim4 | NM_001308091.1 | chr14:31124505-31128930 |
| 19800 | Slfn4 | NM_011410.3 | chr11:83175185-83190216 | | 19895 | Smim5 | NM_183259.3 | chr11:115906138-115906269 |
| 19801 | Slfn5 | NM_183201.4 | chr11:82952101-82964850 | | 19896 | Smim6 | NM_001162998.1 | chr11:115912016-115913917 |
| 19802 | Slfn5os | NR_045932.1 | chr11:82942340-82960681 | | 19897 | Smim7 | NM_172396.3 | chr8:72565197-72571048 |
| 19803 | Slfn8 | NM_001167743.1 | chr11:83002157-83020722 | | 19898 | Smim8 | NM_025471.2 | chr4:34768671-34778337 |
| 19804 | Slfn9 | NM_172796.2 | chr11:82980302-82991830 | | 19899 | Smim9 | NM_001033786.2 | chrX:75146056-75163751 |
| 19805 | Slfnl1 | NM_175570.3 | chr4:120532230-120536661 | | 19900 | Smlr1 | NM_001195596.1 | chr10:25527942-25536272 |
| 19806 | Slirp | NM_026958.3 | chr12:87443895-87449924 | | 19901 | Smn1 | NM_001252629.1 | chr13:100123204-100137698 |
| 19807 | Slit1 | NM_015748.3 | chr19:41600256-41743856 | | 19902 | Smndc1 | NM_172429.2 | chr19:53379213-53390573 |
| 19808 | Slit2 | NM_001291227.2 | chr5:47983154-48307736 | | 19903 | Smo | NM_176996.4 | chr6:29735496-29761366 |
| 19809 | Slit3 | NM_011412.3 | chr11:35121455-35708507 | | 19904 | Smoc1 | NM_001146217.1 | chr12:81026807-81186414 |
| 19810 | Slitrk1 | NM_199065.2 | chr14:108909988-108914239 | | 19905 | Smoc2 | NM_022315.2 | chr17:14279505-14404790 |
| 19811 | Slitrk2 | NM_001161431.1 | chrX:66649317-66661402 | | 19906 | Smok2a | NM_013741.1 | chr17:13221187-13227658 |
| 19812 | Slitrk3 | NM_198864.2 | chr3:73048124-73056943 | | 19907 | Smok2b | NM_001167913.2 | chr17:13230262-13237189 |
| 19813 | Slitrk4 | NM_178740.4 | chrX:64269443-64276996 | | 19908 | Smok3a | NM_001126045.1 | chr5:138021428-138034665 |
| 19814 | Slitrk5 | NM_198865.1 | chr14:111675114-111683135 | | 19909 | Smok3b | NM_001039889.3 | chr5:138037223-138050633 |
| 19815 | Slitrk6 | NM_175499.4 | chr14:110748577-110755149 | | 19910 | Smok4a | NR_030763.1 | chr17:13521455-13528434 |
| 19816 | Slk | NM_001164639.1 | chr19:47580018-47645246 | | 19911 | Smox | NM_001177833.1 | chr2:131491861-131525183 |
| 19817 | Slmap | NM_032008.4 | chr14:26413167-26534624 | | 19912 | Smpd1 | NM_011421.2 | chr7:105554359-105558389 |
| 19818 | Slmo1 | NM_144867.2 | chr18:67464848-67480581 | | 19913 | Smpd2 | NM_009213.2 | chr10:41487171-41490340 |
| 19819 | Slmo2 | NM_025531.2 | chr2:174465090-174472941 | | 19914 | Smpd3 | NM_021491.3 | chr8:106252547-106337988 |
| 19820 | Sln | NM_025540.2 | chr9:53580250-53853849 | | 19915 | Smpd4 | NM_001164609.1 | chr16:17619353-17644830 |
| 19821 | Slpi | NM_011414.3 | chr2:164354069-164356507 | | 19916 | Smpd5 | NM_001195537.1 | chr15:76294433-76296896 |
| 19822 | Sltm | NM_026590.3 | chr9:70542869-70592232 | | 19917 | Smpdl3a | NM_020561.2 | chr10:57794543-57811830 |
| 19823 | Slu7 | NM_148673.3 | chr11:43433730-43447981 | | 19918 | Smpdl3b | NM_133888.2 | chr4:132732965-132757171 |
| 19824 | Slurp1 | NM_020519.1 | chr15:74726643-74728026 | | 19919 | Smpx | NM_001252591.2 | chrX:157698972-157752591 |
| 19825 | Six | NM_001136476.1 | chrX:26522656-26545565 | | 19920 | Smr2 | NM_001252679.1 | chr5:88086555-88109053 |
| 19826 | Slx1b | NM_029420.2 | chr7:126688926-126695783 | | 19921 | Smr3a | NM_011422.3 | chr5:88002524-88008534 |
| 19827 | Slx4 | NM_177472.5 | chr16:3979105-4001678 | | 19922 | Sms | NM_009214.3 | chrX:157443953-157492046 |
| 19828 | Slx4ip | NM_001038641.1 | chr2:136899350-137069778 | | 19923 | Smtn | NM_001169284.1 | chr11:3517521-3539292 |
| 19829 | Slxl1 | NM_029181.1 | chrX:55226875-55243736 | | 19924 | Smtnl1 | NM_024230.2 | chr2:84811175-84822652 |
| 19830 | Sly | NM_201530.2 | chrY:55213719-75222053 | | 19925 | Smtnl2 | NM_177776.3 | chr11:72390113-72411713 |
| 19831 | Smad1 | NM_008539.3 | chr8:79383397-79399468 | | 19926 | Smu1 | NM_021535.4 | chr4:40735648-40757885 |
| 19832 | Smad2 | NM_001252481.1 | chr18:76261120-76311747 | | 19927 | Smug1 | NM_027885.3 | chr15:103153289-103163284 |
| 19833 | Smad3 | NM_016769.4 | chr9:63646766-63757994 | | 19928 | Smurf1 | NM_001038627.1 | chr5:144876494-144965830 |
| 19834 | Smad4 | NM_008540.2 | chr18:73639012-73703741 | | 19929 | Smurf2 | NM_025481.2 | chr11:106820063-106920715 |
| 19835 | Smad5 | NM_001164041.1 | chr13:56703051-56742378 | | 19930 | Smyd1 | NM_001160127.1 | chr6:71213939-71262281 |
| 19836 | Smad6 | NM_008542.3 | chr9:63953075-64022059 | | 19931 | Smyd2 | NM_026796.1 | chr1:189880491-189922288 |
| 19837 | Smad7 | NM_001042660.1 | chr18:75367364-75395934 | | 19932 | Smyd3 | NM_027188.3 | chr1:178965038-179518003 |
| 19838 | Smad9 | NM_019483.5 | chr3:54755581-54801269 | | 19933 | Smyd4 | NM_001102611.1 | chr11:75348432-75405705 |
| 19839 | Smagp | NM_001033872.2 | chr15:100621339-100636940 | | 19934 | Smyd5 | NM_144918.2 | chr6:85413975-85446429 |
| 19840 | Smap1 | NM_001290683.1 | chr1:23845624-23909736 | | 19935 | Snai1 | NM_011427.2 | chr2:167538226-167542811 |
| 19841 | Smap2 | NM_133716.3 | chr4:120968316-121017247 | | 19936 | Snai2 | NM_011415.2 | chr16:14705858-14709382 |
| 19842 | Smarca1 | NM_001290708.1 | chrX:47809369-47892552 | | 19937 | Snai3 | NM_013914.2 | chr8:122454205-122460692 |
| 19843 | Smarca2 | NM_011416.2 | chr19:26605159-26778321 | | 19938 | Snap23 | NM_001177792.1 | chr2:120567670-120600722 |
| 19844 | Smarca4 | NM_001174078.1 | chr9:21616168-21704230 | | 19939 | Snap25 | NM_001291056.1 | chr2:136713449-136782428 |
| 19845 | Smarca5 | NM_053124.2 | chr8:80699942-80739459 | | 19940 | Snap29 | NM_023348.4 | chr16:17405999-17430826 |
| 19846 | Smarca5-ps | NR_002888.2 | chr4:145464209-145467961 | | 19941 | Snap47 | NM_144521.2 | chr11:59407149-59449956 |
| 19847 | Smarcad1 | NM_001253392.1 | chr6:65043205-65116049 | | 19942 | Snap91 | NM_001277982.1 | chr9:86765926-86880397 |

Fig. 26 - 106

| | | | | | | | | |
|---|---|---|---|---|---|---|---|---|
| 19943 | Snapc1 | NM_178392.4 | chr12:73964529-73984820 | | 20038 | Snord42a | NR_037682.1 | chr11:78181301-78181346 |
| 19944 | Snapc2 | NM_133968.1 | chr4:4253101-4256220 | | 20039 | Snord42b | NR_037683.1 | chr11:78183058-78183113 |
| 19945 | Snapc3 | NM_029949.3 | chr4:83417743-83453340 | | 20040 | Snord43 | NR_028281.1 | chr15:80082858-80082906 |
| 19946 | Snapc4 | NM_172339.4 | chr2:26362764-26380653 | | 20041 | Snord45b | NR_028561.1 | chr3:153910586-153910611 |
| 19947 | Snapc5 | NM_183316.2 | chr9:64179296-64182688 | | 20042 | Snord45c | NR_028525.1 | chr3:153912128-153912189 |
| 19948 | Snapin | NM_133854.3 | chr3:90488025-90491013 | | 20043 | Snord47 | NR_028543.1 | chr1:161038091-161038156 |
| 19949 | Snca | NM_001042451.2 | chr6:60731572-60829004 | | 20044 | Snord49a | NR_028550.1 | chr11:62603459-62603521 |
| 19950 | Sncaip | NM_001199151.1 | chr18:52767810-52915931 | | 20045 | Snord49b | NR_028526.1 | chr11:62603085-62603148 |
| 19951 | Sncb | NM_033610.2 | chr13:54758859-54766440 | | 20046 | Snord4a | NR_030702.1 | chr11:78181686-78181756 |
| 19952 | Sncg | NM_011430.3 | chr14:34370273-34374669 | | 20047 | Snord52 | NR_028527.1 | chr17:34950949-34951008 |
| 19953 | Snd1 | NM_019776.2 | chr6:28480347-28888832 | | 20048 | Snord53 | NR_028551.1 | chr7:71640888-110848315 |
| 19954 | Sned1 | NM_172463.4 | chr1:93235896-93296448 | | 20049 | Snord55 | NR_030704.1 | chr4:117155770-117155848 |
| 19955 | Snf8 | NM_033568.2 | chr11:96034916-96047405 | | 20050 | Snord57 | NR_028528.1 | chr2:130278025-130278088 |
| 19956 | Snhg1 | NR_002896.3 | chr19:8723486-8726326 | | 20051 | Snord58b | NR_028552.1 | chr14:52069314-75001122 |
| 19957 | Snhg10 | NR_003145.3 | chr12:105030616-105032279 | | 20052 | Snord61 | NR_002903.1 | chrX:57391447-57391509 |
| 19958 | Snhg11 | NM_175692.3 | chr2:158375637-158386145 | | 20053 | Snord64 | NR_028529.1 | chr7:59678810-59978856 |
| 19959 | Snhg12 | NR_029468.1 | chr4:132308677-132311024 | | 20054 | Snord65 | NR_028541.1 | chr11:62604529-62604586 |
| 19960 | Snhg18 | NR_038186.1 | chr15:32240567-32244662 | | 20055 | Snord66 | NR_028530.1 | chr16:20684255-20684313 |
| 19961 | Snhg3 | NR_003270.2 | chr4:132351932-132353686 | | 20056 | Snord67 | NR_028531.1 | chr2:91596080-91596178 |
| 19962 | Snhg4 | NR_038073.1 | chr18:35553409-35558316 | | 20057 | Snord7 | NR_028128.1 | chr8:123103057-123103105 |
| 19963 | Snhg5 | NR_040721.1 | chr9:88521052-88522897 | | 20058 | Snord69 | NR_028531.1 | chr14:31014292-31014351 |
| 19964 | Snhg6 | NR_024067.2 | chr1:9942024-9944118 | | 20059 | Snord7 | NR_028362.1 | chr11:83294303-83294399 |
| 19965 | Snhg7 | NR_024068.2 | chr2:26637175-26640244 | | 20060 | Snord70 | NR_028554.1 | chr1:59691957-59692010 |
| 19966 | Snhg8 | NR_028574.1 | chr3:123507551-123508336 | | 20061 | Snord71 | NR_028532.1 | chr8:109839311-109839375 |
| 19967 | Snhg9 | NR_027900.2 | chr7:24719530-24719965 | | 20062 | Snord72 | NR_028091.1 | chr15:5118420-5118480 |
| 19968 | Snip1 | NM_175246.4 | chr4:125066692-125074043 | | 20063 | Snord73a | NR_004417.1 | chr3:86138790-86138858 |
| 19969 | Snn | NM_009223.3 | chr16:11066297-11074986 | | 20064 | Snord8 | NR_028542.1 | chr14:52209785-52209884 |
| 19970 | Snora15 | NR_003681.1 | chr5:129794560-129794676 | | 20065 | Snord82 | NR_002851.1 | chr1:86356259-86356327 |
| 19971 | Snora16a | NR_029412.1 | chr4:132309464-132309600 | | 20066 | Snord83b | NR_028282.1 | chr15:80078502-80078579 |
| 19972 | Snora17 | NR_028571.1 | chr2:26639189-26639321 | | 20067 | Snord85 | NR_028565.1 | chr4:130749637-130749702 |
| 19973 | Snora19 | NR_034047.1 | chr19:24942235-60774385 | | 20068 | Snord87 | NR_004410.1 | chr1:9942469-9942543 |
| 19974 | Snora20 | NR_028479.1 | chr17:12922856-12922917 | | 20069 | Snord88a | NR_028533.1 | chr7:44250149-44250221 |
| 19975 | Snora21 | NR_028078.1 | chr11:97781638-97781766 | | 20070 | Snord88c | NR_028534.1 | chr7:44249854-44249938 |
| 19976 | Snora23 | NR_033336.1 | chr7:110046363-110046547 | | 20071 | Snord89 | NR_028555.2 | chr1:39548746-39548840 |
| 19977 | Snora24 | NR_028573.1 | chr3:123507936-123508066 | | 20072 | Snord90 | NR_028535.1 | chr2:37400060-37400128 |
| 19978 | Snora26 | NR_037758.1 | chr5:74093529-74093650 | | 20073 | Snord91a | NR_028562.1 | chr11:74905445-74905505 |
| 19979 | Snora28 | NR_033168.1 | chr12:111540945-111541066 | | 20074 | Snord92 | NR_028556.2 | chr17:71631278-71631361 |
| 19980 | Snora2b | NR_034052.1 | chr15:98526347-98526459 | | 20075 | Snord93 | NR_028536.1 | chr5:23852232-23852277 |
| 19981 | Snora3 | NR_028079.1 | chr7:109520131-109520251 | | 20076 | Snord96 | NR_028564.1 | chr11:48803138-48803206 |
| 19982 | Snora30 | NR_034045.1 | chr7:127527896-127528003 | | 20077 | Snord96a | NR_028563.1 | chr11:48802032-48802109 |
| 19983 | Snora31 | NR_028481.1 | chr14:75847922-75848034 | | 20078 | Snord98 | NR_028557.1 | chr10:62765578-62765606 |
| 19984 | Snora33 | NR_037680.1 | chr10:23785346-23785451 | | 20079 | Snord99 | NR_028537.1 | chr4:132310702-132310758 |
| 19985 | Snora34 | NR_034051.1 | chr15:98519716-98519834 | | 20080 | Snph | NM_001291076.1 | chr2:151590548-151632593 |
| 19986 | Snora35 | NR_028446.1 | chrX:146994389-146994508 | | 20081 | Snrk | NM_001164572.1 | chr9:122117265-122169702 |
| 19987 | Snora36b | NR_034044.1 | chr1:185242925-185243038 | | 20082 | Snrnp200 | NM_177214.4 | chr2:127208403-127240451 |
| 19988 | Snora41 | NR_028558.1 | chr1:63179022-63179135 | | 20083 | Snrnp25 | NM_030093.3 | chr11:32205414-32208995 |
| 19989 | Snora43 | NR_028572.1 | chr2:26637846-26637985 | | 20084 | Snrnp27 | NM_025665.2 | chr6:86675168-86684491 |
| 19990 | Snora44 | NR_034050.1 | chr4:132309952-132310069 | | 20085 | Snrnp35 | NM_029532.2 | chr5:124483154-124491122 |
| 19991 | Snora47 | NR_034043.1 | chr13:95330610-95330736 | | 20086 | Snrnp40 | NM_025645.2 | chr4:130360131-130390030 |
| 19992 | Snora52 | NR_034049.2 | chr7:141448802-141448936 | | 20087 | Snrnp48 | NM_026382.2 | chr13:38204938-38227663 |
| 19993 | Snora5c | NR_034042.1 | chr11:6620318-6620419 | | 20088 | Snrnp70 | NM_009224.3 | chr7:45376453-45395742 |
| 19994 | Snora61 | NR_034046.1 | chr4:132310306-132310368 | | 20089 | Snrpa | NM_001046637.1 | chr7:27187005-27195760 |
| 19995 | Snora62 | NR_002902.2 | chr9:120130433-120130561 | | 20090 | Snrpa1 | NM_021336.4 | chr7:66060335-66074587 |
| 19996 | Snora64 | NR_002897.1 | chr17:24720788-24720905 | | 20091 | Snrpb | NM_009225.2 | chr2:130171635-130179364 |
| 19997 | Snora65 | NR_002898.2 | chr1:32963300-32963418 | | 20092 | Snrpb2 | NM_021335.3 | chr2:143063068-143072052 |
| 19998 | Snora68 | NR_002900.1 | chr8:70895758-70895856 | | 20093 | Snrpc | NM_011432.2 | chr17:27840086-27851967 |
| 19999 | Snora69 | NR_002900.1 | chr5:37082911-37083033 | | 20094 | Snrpd1 | NM_009226.4 | chr18:10617795-10628230 |
| 20000 | Snora70 | NR_002899.1 | chrX:74272491-74272620 | | 20095 | Snrpd2 | NM_026943.1 | chr7:19149837-19152726 |
| 20001 | Snora74a | NR_029053.3 | chr18:35557029-35557227 | | 20096 | Snrpd3 | NM_026095.4 | chr10:75518041-75535440 |
| 20002 | Snora75 | NR_028478.1 | chr1:86351169-86351285 | | 20097 | Snrpe | NM_009227.3 | chr1:133603870-133610280 |
| 20003 | Snora78 | NR_028515.1 | chr17:24719675-24719832 | | 20098 | Snrpf | NM_027246.1 | chr10:93583028-93589658 |
| 20004 | Snora7a | NR_028546.1 | chr6:115807974-115808103 | | 20099 | Snrpg | NM_026506.2 | chr6:86371539-86378902 |
| 20005 | Snora81 | NR_034048.1 | chr16:23110769-23110933 | | 20100 | Snrpn | NM_001082961.1 | chr7:59982501-60097608 |
| 20006 | Snord100 | NR_037681.1 | chr10:23785753-23785821 | | 20101 | Snta1 | NM_009228.2 | chr2:154376313-154408084 |
| 20007 | Snord104 | NR_030703.1 | chr11:106500990-106501063 | | 20102 | Sntb1 | NM_016667.3 | chr15:55639153-55906949 |
| 20008 | Snord11 | NR_028521.1 | chr1:59704807-59704870 | | 20103 | Sntb2 | NM_009229.4 | chr8:106935749-107014192 |
| 20009 | Snord110 | NR_028547.1 | chr2:130275514-130275573 | | 20104 | Sntg1 | NM_001290390.1 | chr1:8359738-9299877 |
| 20010 | Snord111 | NR_028559.1 | chr8:110838534-110838598 | | 20105 | Sntg2 | NM_172951.3 | chr2:30174556-30373375 |
| 20011 | Snord116 | NR_002895.2 | chr7:59675990-59676079 | | 20106 | Sntn | NM_177624.3 | chr14:13670875-13683148 |
| 20012 | Snord116l1 | NR_028778.1 | chr7:59894622-59894711 | | 20107 | Snupn | NM_178374.3 | chr9:56950923-56983199 |
| 20013 | Snord116l2 | NR_033779.1 | chr7:59675989-59751580 | | 20108 | Snurf | NM_033174.3 | chr7:59982500-60005156 |
| 20014 | Snord118 | NR_028566.1 | chr19:7478517-7478561 | | 20109 | Snw1 | NM_025507.2 | chr12:87449809-87472299 |
| 20015 | Snord12 | NR_028540.1 | chr2:167065292-167065358 | | 20110 | Snx1 | NM_019727.2 | chr9:66088126-66124486 |
| 20016 | Snord123 | NR_028575.2 | chr15:32241844-32241932 | | 20111 | Snx10 | NM_001127348.1 | chr6:51544522-51590670 |
| 20017 | Snord14a | NR_028273.1 | chr2:32777987-32778009 | | 20112 | Snx11 | NM_001163389.1 | chr11:96767548-96777555 |
| 20018 | Snord14c | NR_028276.1 | chr10:46244748-46244770 | | 20113 | Snx12 | NM_001010310.1 | chrX:101211960-101222563 |
| 20019 | Snord14d | NR_028274.1 | chr10:46244747-46244770 | | 20114 | Snx13 | NM_001014973.2 | chr12:35047188-35147477 |
| 20020 | Snord15a | NR_002172.1 | chr7:99482784-99482932 | | 20115 | Snx14 | NM_172926.3 | chr9:88376746-88438951 |
| 20021 | Snord15b | NR_002173.1 | chr7:99479766-99479707 | | 20116 | Snx15 | NM_026912.1 | chr19:6119403-6128215 |
| 20022 | Snord16a | NR_028548.1 | chr9:64175431-64175522 | | 20117 | Snx16 | NM_001127191.2 | chr3:10417816-10440130 |
| 20023 | Snord17 | NR_030762.1 | chr2:144265981-144266202 | | 20118 | Snx17 | NM_153680.2 | chr5:31193303-31198900 |
| 20024 | Snord19 | NR_028523.1 | chr4:131016218-31016272 | | 20119 | Snx18 | NM_130796.4 | chr13:113592178-113618564 |
| 20025 | Snord1a | NR_028570.1 | chr11:116674596-116674672 | | 20120 | Snx19 | NM_028874.2 | chr9:30427328-30466726 |
| 20026 | Snord1b | NR_028567.1 | chr11:116674146-116674223 | | 20121 | Snx2 | NM_026386.1 | chr18:53176364-53220860 |
| 20027 | Snord1c | NR_028569.1 | chr11:116672504-116672582 | | 20122 | Snx20 | NM_027840.3 | chr8:88626827-88636128 |
| 20028 | Snord2 | NR_030705.1 | chr16:23108952-23109020 | | 20123 | Snx21 | NM_133924.3 | chr2:164786020-164792770 |
| 20029 | Snord22 | NR_004465.1 | chr19:8725865-8725991 | | 20124 | Snx22 | NM_001025612.2 | chr9:66065175-66069731 |
| 20030 | Snord23 | NR_028539.1 | chr7:15938761-15938860 | | 20125 | Snx24 | NM_029394.3 | chr18:53245661-53390825 |
| 20031 | Snord32a | NR_000002.8 | chr7:45127382-45127463 | | 20126 | Snx25 | NM_207213.2 | chr8:46033260-46124146 |
| 20032 | Snord33 | NR_001277.2 | chr7:45126863-45126945 | | 20127 | Snx27 | NM_001082484.2 | chr3:94497541-94582716 |
| 20033 | Snord34 | NR_002455.1 | chr7:45126602-45126668 | | 20128 | Snx29 | NM_001290148.1 | chr16:11405647-11755473 |
| 20034 | Snord35a | NR_000003.8 | chr7:45126346-45126435 | | 20129 | Snx3 | NM_017472.4 | chr10:42502053-42535369 |
| 20035 | Snord35b | NR_000004.8 | chr4:45123025-45123111 | | 20130 | Snx30 | NM_172468.2 | chr4:59805649-59904740 |
| 20036 | Snord37 | NR_028549.1 | chr10:81178960-81179013 | | 20131 | Snx31 | NM_025712.4 | chr15:36504061-36555572 |
| 20037 | Snord38a | NR_028524.1 | chr4:117154515-117154574 | | 20132 | Snx32 | NM_001024560.2 | chr19:5495277-5510489 |

Fig. 26 - 107

| | | | |
|---|---|---|---|
| 20133 | Snx33 | NM_175483.5 | chr9:56917199-56928371 |
| 20134 | Snx4 | NM_080557.2 | chr16:33251455-33299562 |
| 20135 | Snx5 | NM_001199188.1 | chr2:144250123-144270902 |
| 20136 | Snx6 | NM_026998.3 | chr12:54746356-54795662 |
| 20137 | Snx7 | NM_001190156.1 | chr3:117781496-117868936 |
| 20138 | Snx8 | NM_172777.2 | chr5:140340307-140389247 |
| 20139 | Snx9 | NM_025664.5 | chr17:5841379-5930711 |
| 20140 | Soat1 | NM_009230.3 | chr1:156426107-156474328 |
| 20141 | Soat2 | NM_146064.1 | chr15:102150574-102163436 |
| 20142 | Sobp | NM_175407.3 | chr10:43002499-43174530 |
| 20143 | Socs1 | NM_001271603.1 | chr16:10783808-10785536 |
| 20144 | Socs2 | NM_001168655.1 | chr10:95411489-95416212 |
| 20145 | Socs3 | NM_007707.3 | chr11:117966086-117969366 |
| 20146 | Socs4 | NM_080843.2 | chr14:47277142-47291591 |
| 20147 | Socs5 | NM_019654.2 | chr17:87107678-87137588 |
| 20148 | Socs6 | NM_018821.4 | chr18:88867879-88894207 |
| 20149 | Socs7 | NM_138657.3 | chr11:97362550-97398542 |
| 20150 | Sod1 | NM_011434.1 | chr16:90220741-90226324 |
| 20151 | Sod2 | NM_013671.3 | chr17:13007838-13018119 |
| 20152 | Sod3 | NM_011435.3 | chr5:52363803-52369738 |
| 20153 | Soga1 | NM_001164663.1 | chr2:157010441-157079265 |
| 20154 | Soga3 | NM_026138.2 | chr10:29143995-29199628 |
| 20155 | Sohlh1 | NM_001001714.1 | chr2:25842996-25847248 |
| 20156 | Sohlh2 | NM_028937.3 | chr3:55182043-55209957 |
| 20157 | Son | NM_019973.2 | chr16:91647823-91663318 |
| 20158 | Sorbs1 | NM_001034962.1 | chr19:40292039-40451398 |
| 20159 | Sorbs2 | NM_001205219.1 | chr8:45507787-45827906 |
| 20160 | Sorbs2os | NR_045739.1 | chr8:45723324-45819297 |
| 20161 | Sorbs3 | NM_001271407.1 | chr14:70180467-70206022 |
| 20162 | Sorcs1 | NM_001252501.1 | chr19:50143300-50678646 |
| 20163 | Sorcs2 | NM_030889.2 | chr5:36017180-36398139 |
| 20164 | Sorcs3 | NM_025696.3 | chr19:48206024-48805505 |
| 20165 | Sord | NM_146126.4 | chr2:122234838-122265337 |
| 20166 | Sort1 | NM_011436.3 | chr9:41968488-42124289 |
| 20167 | Sortl | NM_001271599.1 | chr3:108284063-108361519 |
| 20168 | Sos1 | NM_009231.2 | chr17:80393751-80480453 |
| 20169 | Sos2 | NM_001135559.1 | chr12:69583760-69681852 |
| 20170 | Sost | NM_024449.6 | chr11:101962457-101967015 |
| 20171 | Sostdc1 | NM_025312.3 | chr12:36314168-36318452 |
| 20172 | Sowaha | NM_183173.2 | chr11:53476577-53480195 |
| 20173 | Sowahb | NM_175270.4 | chr5:93041122-93045022 |
| 20174 | Sowahc | NM_172939.3 | chr10:59221921-59226433 |
| 20175 | Sowahd | NM_173779.3 | chrX:37048844-37050418 |
| 20176 | Sox1 | NM_009233.3 | chr8:12395518-12399555 |
| 20177 | Sox10 | NM_011437.1 | chr15:79154912-79164490 |
| 20178 | Sox11 | NM_009234.6 | chr12:27334267-27342718 |
| 20179 | Sox12 | NM_011438.2 | chr2:152393611-152398046 |
| 20180 | Sox13 | NM_011439.2 | chr1:133382299-133424212 |
| 20181 | Sox14 | NM_011440.1 | chr9:99874105-99876170 |
| 20182 | Sox15 | NM_009235.2 | chr11:69655036-69656727 |
| 20183 | Sox17 | NM_001289464.1 | chr1:4490927-4497354 |
| 20184 | Sox18 | NM_009236.2 | chr2:181669836-181671640 |
| 20185 | Sox2 | NM_011443.4 | chr3:34649994-34652460 |
| 20186 | Sox21 | NM_177753.3 | chr14:118233233-118237030 |
| 20187 | Sox2ot | NR_015580.2 | chr3:34560380-34677993 |
| 20188 | Sox3 | NM_009237.2 | chrX:60891365-60893430 |
| 20189 | Sox30 | NM_173384.2 | chr11:45980309-46017992 |
| 20190 | Sox4 | NM_009238.2 | chr13:28950729-28953682 |
| 20191 | Sox5 | NM_001164669.2 | chr6:143828424-144209568 |
| 20192 | Sox5os3 | NR_040519.1 | chr6:144672867-144693832 |
| 20193 | Sox6 | NM_001025559.3 | chr7:115470871-116038744 |
| 20194 | Sox7 | NM_011414.1 | chr14:63943705-63950732 |
| 20195 | Sox8 | NM_011447.3 | chr17:25565892-25570686 |
| 20196 | Sox9 | NM_011448.4 | chr11:112782209-112787757 |
| 20197 | Sp1 | NM_013672.2 | chr15:102406315-102436404 |
| 20198 | Sp100 | NM_013673.4 | chr1:85649987-85709997 |
| 20199 | Sp110 | NM_030194.1 | chr1:85576898-85598810 |
| 20200 | Sp140 | NM_001013817.2 | chr1:85600702-85645036 |
| 20201 | Sp2 | NM_001080964.1 | chr11:96953337-96977688 |
| 20202 | Sp3 | NM_001018042.3 | chr2:72936431-72980446 |
| 20203 | Sp3os | NR_045269.2 | chr2:72979431-72989249 |
| 20204 | Sp4 | NM_001166385.2 | chr12:118231685-118301440 |
| 20205 | Sp5 | NM_022435.2 | chr2:70474922-70477726 |
| 20206 | Sp6 | NM_031183.2 | chr11:97013568-97024738 |
| 20207 | Sp7 | NM_130458.3 | chr15:102357176-102366271 |
| 20208 | Sp8 | NM_177082.4 | chr12:118846326-118852578 |
| 20209 | Sp9 | NM_001005343.2 | chr2:73271925-73275771 |
| 20210 | Spa17 | NM_011449.2 | chr9:37603293-37613720 |
| 20211 | Spaca1 | NM_001290443.1 | chr4:34024871-34050065 |
| 20212 | Spaca3 | NM_029367.1 | chr11:80858388-80867814 |
| 20213 | Spaca4 | NM_027055.3 | chr7:45725106-45725816 |
| 20214 | Spaca5 | NM_001085393.2 | chrX:21062487-21077959 |
| 20215 | Spaca6 | NM_001162909.1 | chr17:17830974-17839071 |
| 20216 | Spaca7 | NM_024279.2 | chr8:12573048-12600738 |
| 20217 | Spag1 | NM_012093.1 | chr15:36179529-36235177 |
| 20218 | Spag11a | NM_153115.1 | chr8:19157886-19159578 |
| 20219 | Spag11b | NM_001034905.2 | chr8:19140759-19143010 |
| 20220 | Spag16 | NM_001271533.1 | chr1:69826969-69926250 |
| 20221 | Spag17 | NM_028892.4 | chr3:99885416-100143322 |
| 20222 | Spag4 | NM_139142.3 | chr2:156065212-156069499 |
| 20223 | Spag5 | NM_017407.2 | chr11:78301590-78322454 |
| 20224 | Spag6 | NM_015773.2 | chr16:16753015-16829363 |
| 20225 | Spag7 | NM_016763.2 | chr7:70669416-70669416 |
| 20226 | Spag8 | NM_001007463.1 | chr4:43651728-43653552 |
| 20227 | Spag9 | NM_001025428.1 | chr11:94044204-94146082 |

| | | | |
|---|---|---|---|
| 20228 | Spam1 | NM_001079875.2 | chr6:24791187-24801048 |
| 20229 | Sparc | NM_001290817.1 | chr11:55394158-55420080 |
| 20230 | Sparcl1 | NM_010097.4 | chr5:104079108-104114088 |
| 20231 | Spast | NM_001162870.1 | chr17:74338986-74391113 |
| 20232 | Spata1 | NM_027617.3 | chr3:146457202-146499753 |
| 20233 | Spata13 | NM_001033272.2 | chr14:60634704-60764556 |
| 20234 | Spata16 | NM_027583.3 | chr3:26637630-26927481 |
| 20235 | Spata17 | NM_028848.3 | chr1:187048406-187215446 |
| 20236 | Spata18 | NM_178387.3 | chr5:73651379-73679484 |
| 20237 | Spata19 | NM_029299.3 | chr9:27396806-27401711 |
| 20238 | Spata2 | NM_170756.2 | chr2:167481135-167492874 |
| 20239 | Spata20 | NM_144827.4 | chr11:94478903-94485310 |
| 20240 | Spata21 | NM_177867.3 | chr4:141088344-141112759 |
| 20241 | Spata22 | NM_001045531.1 | chr11:73329740-73346044 |
| 20242 | Spata24 | NM_027733.5 | chr18:35660015-35662186 |
| 20243 | Spata25 | NM_029337.3 | chr2:164827381-164828534 |
| 20244 | Spata2l | NM_030176.2 | chr8:123232257-123236209 |
| 20245 | Spata3 | NM_001122732.1 | chr1:86021941-86029958 |
| 20246 | Spata31 | NM_030047.2 | chr13:64917405-64923195 |
| 20247 | Spata31d1a | NM_028157.2 | chr13:59700082-59706197 |
| 20248 | Spata31d1b | NM_001167593.1 | chr13:59712283-59719289 |
| 20249 | Spata31d1c | NM_001083890.2 | chr13:65033057-65038004 |
| 20250 | Spata31d1d | NM_177711.3 | chr13:59725924-59731752 |
| 20251 | Spata32 | NM_177801.3 | chr11:103208126-103218432 |
| 20252 | Spata33 | NM_177279.4 | chr8:123212857-123222045 |
| 20253 | Spata4 | NM_133711.3 | chr8:54660780-54610098 |
| 20254 | Spata45 | NM_029336.1 | chr1:191036821-191042941 |
| 20255 | Spata5 | NM_001163511.2 | chr3:37419949-37579096 |
| 20256 | Spata5l1 | NM_001033256.3 | chr2:122630624-122632704 |
| 20257 | Spata6 | NM_026470.3 | chr4:111720009-111829140 |
| 20258 | Spata7 | NM_001289572.1 | chr12:98628141-98669819 |
| 20259 | Spata9 | NM_029343.3 | chr13:75967738-75998968 |
| 20260 | Spatc1 | NM_028852.1 | chr15:76268088-76292572 |
| 20261 | Spatc1l | NM_029661.1 | chr10:76562271-76570200 |
| 20262 | Spats1 | NM_027649.3 | chr17:45448936-45474938 |
| 20263 | Spats2 | NM_139140.1 | chr15:99126844-99212466 |
| 20264 | Spats2l | NM_001164566.1 | chr1:57845570-57948397 |
| 20265 | Spc24 | NM_026282.5 | chr9:21755441-21760286 |
| 20266 | Spc25 | NM_001199123.2 | chr2:69193894-69206213 |
| 20267 | Spcs1 | NM_026911.3 | chr14:30999825-31001666 |
| 20268 | Spcs2 | NM_025668.3 | chr7:99837568-99858883 |
| 20269 | Spcs3 | NM_029701.1 | chr8:54520432-54529998 |
| 20270 | Spdef | NM_013891.4 | chr17:27714446-27728951 |
| 20271 | Spdl1 | NM_027411.2 | chr11:34809184-34833641 |
| 20272 | Spdya | NM_001142631.1 | chr17:71552060-71578700 |
| 20273 | Spdyb | NM_029048.3 | chr5:143216315-143225882 |
| 20274 | Speccl | NM_001029936.3 | chr11:62077023-62223013 |
| 20275 | Speccl1 | NM_001145826.1 | chr10:75212389-75312400 |
| 20276 | Speer1-ps1 | NR_001586.3 | chr5:11340407-11346273 |
| 20277 | Speer2 | NM_173069.3 | chr16:69856873-69863744 |
| 20278 | Speer3 | NM_027650.3 | chr5:13791618-13796819 |
| 20279 | Speer4a | NM_029376.2 | chr5:26034269-26039505 |
| 20280 | Speer4b | NM_028561.2 | chr5:27495808-27501392 |
| 20281 | Speer4c | NM_001281511.1 | chr5:15709504-15714271 |
| 20282 | Speer4d | NM_025759.3 | chr5:15619098-15623864 |
| 20283 | Speer4e | NM_001122661.1 | chr5:14933630-14938475 |
| 20284 | Speer4f | NM_027609.2 | chr5:17476121-17480936 |
| 20285 | Speer5-ps1 | NR_001582.2 | chr10:44170446-44219585 |
| 20286 | Speer6-ps1 | NR_001581.2 | chr13:3149474-3189678 |
| 20287 | Speer7-ps1 | NR_001585.3 | chr5:15680709-15714596 |
| 20288 | Speer8-ps1 | NR_001584.3 | chr5:14945293-14978541 |
| 20289 | Speer9-ps1 | NR_001583.3 | chr7:3128145-3144992 |
| 20290 | Spef1 | NM_027641.2 | chr2:131170260-131174810 |
| 20291 | Spef2 | NM_177123.4 | chr15:9661545-9748868 |
| 20292 | Speg | NM_001085370.1 | chr1:75385609-75432304 |
| 20293 | Spem1 | NM_028855.1 | chr11:69820870-69822165 |
| 20294 | Spen | NM_019763.2 | chr4:141467889-141538597 |
| 20295 | Spert | NM_001164139.1 | chr14:75582833-75593116 |
| 20296 | Spesp1 | NM_025721.2 | chr9:62270728-62282179 |
| 20297 | Spg11 | NM_145531.2 | chr2:122053525-122118386 |
| 20298 | Spg20 | NM_001144987.1 | chr3:55112165-55137332 |
| 20299 | Spg21 | NM_138584.2 | chr9:65460936-65484470 |
| 20300 | Spg7 | NM_153176.4 | chr8:123065507-123097751 |
| 20301 | Sphk1 | NM_001172472.1 | chr11:116532443-116536675 |
| 20302 | Sphk2 | NM_001172561.1 | chr7:45709462-45718002 |
| 20303 | Sphkap | NM_172430.3 | chr1:83255750-83408200 |
| 20304 | Spi1 | NM_011355.1 | chr2:91096796-91115756 |
| 20305 | Spib | NM_019866.1 | chr7:44525984-44532071 |
| 20306 | Spic | NM_011461.3 | chr10:88675269-88683023 |
| 20307 | Spice1 | NM_144550.4 | chr16:44347400-44388492 |
| 20308 | Spidr | NM_146068.4 | chr16:15889224-16146851 |
| 20309 | Spin1 | NM_001283028.1 | chr13:51100879-51152562 |
| 20310 | Spin2c | NM_001005370.1 | chrX:153832292-153834240 |
| 20311 | Spin2d | NM_001243002.1 | chrX:73175301-73176989 |
| 20312 | Spin2-ps1 | NM_029106.2 | chrX:3835879-3836656 |
| 20313 | Spin4 | NM_178753.4 | chrX:95022506-95026682 |
| 20314 | Spink10 | NM_177829.3 | chr18:62548910-62661388 |
| 20315 | Spink11 | NM_001048217.3 | chr18:44190044-44196177 |
| 20316 | Spink12 | NM_030061.3 | chr18:44104522-44108543 |
| 20317 | Spink13 | NM_001168423.2 | chr18:62607539-62741387 |
| 20318 | Spink14 | NM_001039218.2 | chr18:44027988-44032208 |
| 20319 | Spink2 | NM_001289764.1 | chr5:77205106-77211259 |
| 20320 | Spink3 | NM_009258.5 | chr18:43728068-43737237 |
| 20321 | Spink4 | NM_011463.2 | chr4:40920055-40931395 |
| 20322 | Spink5 | NM_001081180.1 | chr18:43963240-44022487 |

Fig. 26 - 108

| | | | |
|---|---|---|---|
| 20323 | Spink6 | NM_001013797.1 | chr18:44071392-44083610 |
| 20324 | Spink7 | NM_001001803.2 | chr18:62592412-62596264 |
| 20325 | Spink8 | NM_183136.2 | chr9:109816626-109826627 |
| 20326 | Spinkl | NM_183123.2 | chr18:44166357-44175073 |
| 20327 | Spint1 | NM_016907.3 | chr2:119237359-119249513 |
| 20328 | Spint2 | NM_001082548.1 | chr7:29256329-29281977 |
| 20329 | Spint3 | NM_001774401.1 | chr2:164569694-164573456 |
| 20330 | Spint4 | NM_030058.2 | chr2:164698500-164702448 |
| 20331 | Spint5 | NM_001040055.1 | chr2:164715304-164718068 |
| 20332 | Spire1 | NM_176832.2 | chr18:67488208-67589173 |
| 20333 | Spire2 | NM_172287.2 | chr8:123332712-123369518 |
| 20334 | Spn | NM_001037810.2 | chr7:127133463-127137823 |
| 20335 | Spn-ps | NR_033583.1 | chr15:90891395-90898476 |
| 20336 | Spns1 | NM_023712.3 | chr7:126370059-126377934 |
| 20337 | Spns2 | NM_001276383.1 | chr11:72451637-72475027 |
| 20338 | Spns3 | NM_029932.3 | chr11:72498155-72550246 |
| 20339 | Spo11 | NM_001083959.1 | chr2:172979841-172993576 |
| 20340 | Spock1 | NM_001166463.1 | chr13:57426090-57908332 |
| 20341 | Spock2 | NM_052994.2 | chr10:60106256-60133913 |
| 20342 | Spock3 | NM_001252620.1 | chr8:62951231-63357096 |
| 20343 | Spon1 | NM_145584.2 | chr7:113765997-114043375 |
| 20344 | Spon2 | NM_133903.3 | chr5:33213517-33218238 |
| 20345 | Spop | NM_025287.2 | chr11:95414082-95493410 |
| 20346 | Spopl | NM_001165997.1 | chr2:23510053-23572104 |
| 20347 | Spp1 | NM_001204201.1 | chr5:104435110-104441053 |
| 20348 | Spp2 | NM_029269.3 | chr1:88407009-88426438 |
| 20349 | Sppl2a | NM_023220.2 | chr2:126890394-126933235 |
| 20350 | Sppl2b | NM_175915.3 | chr10:80855274-80868708 |
| 20351 | Sppl2c | NM_001082535.1 | chr11:104186326-104191166 |
| 20352 | Sppl3 | NM_029012.2 | chr5:115011523-115098790 |
| 20353 | Spr | NM_011467.2 | chr6:85133679-85137764 |
| 20354 | Spred1 | NM_001277256.1 | chr2:117121070-117172853 |
| 20355 | Spred2 | NM_033523.4 | chr11:19924441-20022597 |
| 20356 | Spred3 | NM_182927.3 | chr7:29158828-29168647 |
| 20357 | Sprn | NM_183147.2 | chr7:140150627-140154659 |
| 20358 | Sprr1a | NM_009264.2 | chr3:92483953-92485881 |
| 20359 | Sprr1b | NM_009265.3 | chr3:92486808-92488779 |
| 20360 | Sprr2a1 | NM_011468.4 | chr3:92215835-92222491 |
| 20361 | Sprr2a2 | NM_001164787.1 | chr3:92215834-92257304 |
| 20362 | Sprr2b | NM_011469.3 | chr3:92316704-92318085 |
| 20363 | Sprr2d | NM_011470.2 | chr3:92339139-92340873 |
| 20364 | Sprr2e | NM_011471.2 | chr3:92352142-92353449 |
| 20365 | Sprr2f | NM_011472.2 | chr3:92365186-92366442 |
| 20366 | Sprr2g | NR_003548.1 | chr3:92373914-92375229 |
| 20367 | Sprr2h | NM_011474.3 | chr3:92385684-92387319 |
| 20368 | Sprr2i | NM_011475.3 | chr3:92407990-92409271 |
| 20369 | Sprr2j-ps | NR_003185.1 | chr3:92418086-92419396 |
| 20370 | Sprr2k | NM_011477.3 | chr3:92432581-92433927 |
| 20371 | Sprr3 | NM_001204427.1 | chr3:92456501-92458720 |
| 20372 | Sprr4 | NM_173070.1 | chr3:92500262-92500493 |
| 20373 | Sprtn | NM_001111141.1 | chr8:124897885-124903813 |
| 20374 | Spry1 | NM_011896.3 | chr3:37639946-37644599 |
| 20375 | Spry2 | NM_011897.3 | chr14:105891946-105896839 |
| 20376 | Spry3 | NM_001030293.2 | chrX_GL456233_random:101351-106392 |
| 20377 | Spry4 | NM_011898.2 | chr18:38586264-38601268 |
| 20378 | Spryd3 | NM_001033277.3 | chr15:102116527-102136215 |
| 20379 | Spryd4 | NM_025716.2 | chr10:128209909-128211794 |
| 20380 | Spryd7 | NM_025697.4 | chr14:61531850-61556886 |
| 20381 | Spsb1 | NM_029035.2 | chr4:149896283-149955006 |
| 20382 | Spsb2 | NM_013539.2 | chr6:124808917-124810616 |
| 20383 | Spsb3 | NM_001163750.1 | chr17:24886673-24892147 |
| 20384 | Spsb4 | NM_145134.3 | chr9:96943481-97018355 |
| 20385 | Spt1 | NM_009267.2 | chr15:103895855-103899312 |
| 20386 | Spta1 | NM_011465.4 | chr1:174172775-174248449 |
| 20387 | Sptan1 | NM_001177667.1 | chr2:29965553-30031451 |
| 20388 | Sptb | NM_013675.3 | chr12:76580487-76710547 |
| 20389 | Sptbn1 | NM_009260.2 | chr11:30106842-30198257 |
| 20390 | Sptbn2 | NM_021287.1 | chr19:4711222-4752352 |
| 20391 | Sptbn4 | NM_001199234.1 | chr7:27305382-27396198 |
| 20392 | Sptlc1 | NM_009269.2 | chr13:53332747-53377361 |
| 20393 | Sptlc2 | NM_011479.4 | chr12:87305057-87388355 |
| 20394 | Sptlc3 | NM_175467.3 | chr2:139493919-139637674 |
| 20395 | Sptssa | NM_134054.2 | chr12:54645373-54656572 |
| 20396 | Sptssb | NM_001164210.2 | chr3:69819538-69859894 |
| 20397 | Spty2d1 | NM_175318.4 | chr7:46990395-47008414 |
| 20398 | Spz1 | NM_030237.3 | chr13:92574631-92576232 |
| 20399 | Sqle | NM_009270.3 | chr15:59315091-59331193 |
| 20400 | Sqrdl | NM_001162503.1 | chr2:122765358-122809551 |
| 20401 | Sqstm1 | NM_001290769.1 | chr11:50200151-50210820 |
| 20402 | Sra1 | NM_001164406.1 | chr18:36667186-36670311 |
| 20403 | Srbd1 | NM_030133.3 | chr17:85984664-86145175 |
| 20404 | Src | NM_001025395.2 | chr2:157424292-157471838 |
| 20405 | Srcin1 | NM_018873.2 | chr11:97509339-97575126 |
| 20406 | Srcrb4d | NM_001160366.1 | chr5:135960222-135974476 |
| 20407 | Srd5a1 | NM_175283.3 | chr13:69573448-69611463 |
| 20408 | Srd5a2 | NM_053188.2 | chr17:74017705-74047916 |
| 20409 | Srd5a3 | NM_020611.4 | chr5:76140272-76155503 |
| 20410 | Srebf1 | NM_011480.4 | chr11:60199083-60220627 |
| 20411 | Srebf2 | NM_033218.1 | chr15:82147268-82204960 |
| 20412 | Srek1 | NM_172592.2 | chr13:103741614-103764582 |
| 20413 | Srek1ip1 | NM_001017238.1 | chr13:104817218-104838659 |
| 20414 | Srf | NM_020493.2 | chr17:46546838-46556162 |
| 20415 | Srfbp1 | NM_026040.3 | chr18:52465692-52490738 |
| 20416 | Srgap1 | NM_001081037.2 | chr10:121780990-122047315 |
| 20417 | Srgap2 | NM_001081011.2 | chr1:131285250-131527361 |
| 20418 | Srgap3 | NM_080448.4 | chr6:112717971-112947266 |
| 20419 | Srgn | NM_011157.2 | chr10:62494427-62507755 |
| 20420 | Sri | NM_001080974.2 | chr5:8056541-8089314 |
| 20421 | Srl | NM_175347.4 | chr16:4480227-4523053 |
| 20422 | Srm | NM_009272.4 | chr4:148591512-148594619 |
| 20423 | Srms | NM_011481.3 | chr2:181205562-181213171 |
| 20424 | Srp14 | NM_009273.4 | chr2:118475842-118479696 |
| 20425 | Srp19 | NM_025527.3 | chr18:34331144-34336599 |
| 20426 | Srp54a | NM_011899.4 | chr12:55080495-55115367 |
| 20427 | Srp54b | NM_001100109.1 | chr12:55155103-55263480 |
| 20428 | Srp54c | NM_001100110.1 | chr12:55230477-55263020 |
| 20429 | Srp68 | NM_146032.3 | chr11:116245165-116274217 |
| 20430 | Srp72 | NM_025691.1 | chr5:76974700-76999935 |
| 20431 | Srp9 | NM_012058.3 | chr1:182124736-182132415 |
| 20432 | Srpk1 | NM_016795.3 | chr17:28589591-28622454 |
| 20433 | Srpk2 | NM_009274.2 | chr5:23503355-23616571 |
| 20434 | Srpk3 | NM_019684.2 | chrX:73774404-73778924 |
| 20435 | Srpr | NM_026130.1 | chr9:35211202-35217003 |
| 20436 | Srprb | NM_009275.4 | chr9:103188032-103202065 |
| 20437 | Srpx | NM_016911.4 | chrX:10037976-10117661 |
| 20438 | Srpx2 | NM_001083895.3 | chrX:139908424-133932446 |
| 20439 | Srr | NM_011163311.1 | chr11:74906358-74925798 |
| 20440 | Srrd | NM_027323.2 | chr5:112337390-112343040 |
| 20441 | Srrm1 | NM_001130477.1 | chr4:135320483-135353214 |
| 20442 | Srrm2 | NM_175229.3 | chr17:23803186-23824743 |
| 20443 | Srrm3 | NM_021403.3 | chr5:135818105-135874772 |
| 20444 | Srrm4 | NM_026886.3 | chr5:116439272-116591817 |
| 20445 | Srrm4os | NR_015595.2 | chr5:116438721-116465487 |
| 20446 | Srrt | NM_001109909.1 | chr5:137295703-137307674 |
| 20447 | Srsf1 | NM_001078167.2 | chr11:88047372-88053757 |
| 20448 | Srsf10 | NM_001080387.2 | chr4:135856070-135865818 |
| 20449 | Srsf11 | NM_001093752.1 | chr3:158010492-158036639 |
| 20450 | Srsf12 | NM_177774.4 | chr4:33208990-33233340 |
| 20451 | Srsf2 | NM_013358.2 | chr11:116849896-116853094 |
| 20452 | Srsf3 | NM_013663.5 | chr17:29032659-29043372 |
| 20453 | Srsf4 | NM_020587.2 | chr4:131873638-131901725 |
| 20454 | Srsf5 | NM_001079694.1 | chr12:80945503-80950507 |
| 20455 | Srsf6 | NM_026499.4 | chr2:162931507-162937120 |
| 20456 | Srsf7 | NM_001195485.1 | chr17:80200079-80207305 |
| 20457 | Srsf9 | NM_025573.3 | chr5:115327176-115333080 |
| 20458 | Srxn1 | NM_029688.5 | chr2:152105523-152111376 |
| 20459 | Sry | NM_011564.1 | chrY:2662470-2663658 |
| 20460 | Ss18 | NM_001161369.1 | chr18:14625628-14682914 |
| 20461 | Ss18l1 | NM_178750.5 | chr2:180042482-180070201 |
| 20462 | Ssb | NM_001110145.1 | chr2:69861561-69871846 |
| 20463 | Ssbp1 | NM_001286663.1 | chr6:40471467-40481823 |
| 20464 | Ssbp2 | NM_024186.4 | chr13:91461096-91706175 |
| 20465 | Ssbp3 | NM_023672.2 | chr4:106911469-107049694 |
| 20466 | Ssbp4 | NM_133772.2 | chr8:70597489-70608314 |
| 20467 | Ssc5d | NM_173008.2 | chr7:4925843-4944797 |
| 20468 | Ssfa2 | NM_080558.4 | chr2:79635424-79672964 |
| 20469 | Ssh1 | NM_198109.4 | chr5:113942218-113993757 |
| 20470 | Ssh2 | NM_001291190.1 | chr11:77348279-77460219 |
| 20471 | Ssh3 | NM_198113.2 | chr19:4261668-4269172 |
| 20472 | Ssmem1 | NM_027073.1 | chr6:30509848-30520253 |
| 20473 | Ssna1 | NM_023464.2 | chr2:25271038-25272418 |
| 20474 | Sspn | NM_010656.2 | chr6:145934146-145965225 |
| 20475 | Sspo | NM_173428.3 | chr6:48448228-48501250 |
| 20476 | Ssr1 | NM_025965.3 | chr13:37971400-37994190 |
| 20477 | Ssr2 | NM_025448.3 | chr3:88579670-88588413 |
| 20478 | Ssr3 | NM_026155.3 | chr3:65379656-65392553 |
| 20479 | Ssr4 | NM_001166480.1 | chrX:73787027-73790828 |
| 20480 | Ssrp1 | NM_001136081.2 | chr2:85037450-85047114 |
| 20481 | Sssca1 | NM_020491.5 | chr19:5730305-5731732 |
| 20482 | Sst | NM_009215.1 | chr16:23889580-23890844 |
| 20483 | Sstr1 | NM_009216.3 | chr12:58211803-58216036 |
| 20484 | Sstr2 | NM_001042606.2 | chr11:113619480-113625366 |
| 20485 | Sstr3 | NM_009218.3 | chr15:78537014-78544345 |
| 20486 | Sstr4 | NM_009219.3 | chr2:148395376-148396764 |
| 20487 | Sstr5 | NM_001191008.1 | chr17:25489874-25497288 |
| 20488 | Ssty1 | NM_009220.2 | chrY:13376412-21097715 |
| 20489 | Ssty2 | NM_023546.3 | chrY:22512350-80465434 |
| 20490 | Ssu2 | NM_175525.3 | chr6:112359323-112388023 |
| 20491 | Ssu72 | NM_026899.3 | chr4:155704814-155733873 |
| 20492 | Ssx2ip | NM_001253768.1 | chr3:146404641-146440137 |
| 20493 | Ssx9 | NM_199063.2 | chrX:8748429-8754587 |
| 20494 | Ssxb1 | NM_026492.3 | chrX:8413304-8422157 |
| 20495 | Ssxb10 | NM_199064.1 | chrX:8327423-8336235 |
| 20496 | Ssxb2 | NM_001001450.4 | chrX:8454342-8461726 |
| 20497 | Ssxb3 | NM_198898.2 | chrX:8583543-8589246 |
| 20498 | Ssxb5 | NM_199319.3 | chrX:8803690-8809386 |
| 20499 | Ssxb6 | NM_001205108.1 | chrX:8542603-8548255 |
| 20500 | Ssxb8 | NM_001081565.3 | chrX:8685330-8690844 |
| 20501 | Ssxb9 | NM_199066.2 | chrX:8366977-8375388 |
| 20502 | St13 | NM_133726.2 | chr15:81365043-81399694 |
| 20503 | St14 | NM_011176.4 | chr9:31088589-31131799 |
| 20504 | St18 | NM_001244692.1 | chr1:6487230-6860940 |
| 20505 | St3gal1 | NM_009177.4 | chr15:67102874-67176882 |
| 20506 | St3gal2 | NM_009179.3 | chr8:110919864-110972497 |
| 20507 | St3gal3 | NM_001161774.2 | chr4:117932152-118134946 |
| 20508 | St3gal4 | NM_009178.3 | chr9:35046578-35116810 |
| 20509 | St3gal5 | NM_001035228.2 | chr6:72097607-72154570 |
| 20510 | St3gal6 | NM_018784.2 | chr16:58470540-58523312 |
| 20511 | St5 | NM_001001326.1 | chr7:109523910-109617147 |

Fig. 26 - 109

| | | | | | | | |
|---|---|---|---|---|---|---|---|
| 20512 | St6gal1 | NM_001252505.1 | chr16:23226020-23360350 | 20607 | Stoml2 | NM_023231.2 | chr4:43027689-43031384 |
| 20513 | St6gal2 | NM_172829.2 | chr17:55445716-55499226 | 20608 | Stoml3 | NM_153156.1 | chr3:53488792-53507652 |
| 20514 | St6galnac1 | NM_011371.2 | chr11:116765024-116775507 | 20609 | Ston1 | NM_029858.2 | chr17:88626554-88645724 |
| 20515 | St6galnac2 | NM_009180.3 | chr11:116676704-116694660 | 20610 | Ston2 | NM_175367.6 | chr12:91833008-91786436 |
| 20516 | St6galnac3 | NM_011372.2 | chr3:153202508-153725133 | 20611 | Stox1 | NM_001033260.1 | chr10:62659421-62726099 |
| 20517 | St6galnac4 | NM_001276425.1 | chr2:32587077-32599696 | 20612 | Stox2 | NM_001114311.1 | chr8:47180047-47289402 |
| 20518 | St6galnac5 | NM_012028.4 | chr3:152820709-152982207 | 20613 | Stpg1 | NM_030189.3 | chr4:135495986-135537803 |
| 20519 | St6galnac6 | NM_001025310.2 | chr2:32606984-32620809 | 20614 | Stpg2 | NM_198659.2 | chr3:139205892-139710299 |
| 20520 | St7 | NM_001083315.2 | chr6:17749169-17943023 | 20615 | Stra13 | NM_016665.2 | chr11:120710940-120713767 |
| 20521 | St7l | NM_001253702.1 | chr3:104864505-104930063 | 20616 | Stra6 | NM_001162475.1 | chr9:58129087-58153997 |
| 20522 | St8sia1 | NM_011374.2 | chr6:142821540-142964452 | 20617 | Stra8 | NM_009292.1 | chr6:34920959-34939342 |
| 20523 | St8sia2 | NM_009181.2 | chr7:73939119-74013682 | 20618 | Strada | NM_001252448.1 | chr11:106162973-106193603 |
| 20524 | St8sia3 | NM_009182.3 | chr18:64254358-64276144 | 20619 | Stradb | NM_172656.5 | chr1:58973570-58995121 |
| 20525 | St8sia3os | NR_045366.1 | chr18:64157723-64277180 | 20620 | Strap | NM_011499.3 | chr6:137735081-137751930 |
| 20526 | St8sia4 | NM_001159745.1 | chr1:95627242-95667594 | 20621 | Strbp | NM_009261.3 | chr2:37569867-37647285 |
| 20527 | St8sia5 | NM_013666.2 | chr18:77185846-77255450 | 20622 | Strc | NM_080459.2 | chr2:121363726-121380940 |
| 20528 | St8sia6 | NM_145838.1 | chr2:13654935-13793520 | 20623 | Strip1 | NM_153563.2 | chr3:107612531-107631710 |
| 20529 | Stab1 | NM_138672.2 | chr14:31139016-31168641 | 20624 | Strip2 | NM_001037740.1 | chr6:29917012-29959680 |
| 20530 | Stab2 | NM_138673.2 | chr10:86841209-87007942 | 20625 | Strn | NM_011500.2 | chr17:78653963-78736560 |
| 20531 | Stac | NM_016853.2 | chr9:111561433-111690216 | 20626 | Strn3 | NM_001172098.1 | chr12:51608540-51691914 |
| 20532 | Stac2 | NM_146028.4 | chr11:98036623-98053462 | 20627 | Strn4 | NM_001039878.2 | chr7:16815888-16840931 |
| 20533 | Stac3 | NM_177707.3 | chr10:127501716-127508815 | 20628 | Stt3a | NM_008408.4 | chr9:36732412-36767578 |
| 20534 | Stag1 | NM_009282.3 | chr9:100643622-100958544 | 20629 | Stt3b | NM_024222.2 | chr9:115242581-115310421 |
| 20535 | Stag2 | NM_001077712.2 | chrX:42149411-42277186 | 20630 | Stub1 | NM_019719.3 | chr17:25830635-25833361 |
| 20536 | Stag3 | NM_016964.2 | chr5:138208508-138312393 | 20631 | Stx11 | NM_001163590.1 | chr10:12939982-12964259 |
| 20537 | Stam | NM_011484.2 | chr2:14074111-14148330 | 20632 | Stx12 | NM_133887.4 | chr4:132854063-132884458 |
| 20538 | Stam2 | NM_019667.2 | chr2:52692205-52742149 | 20633 | Stx16 | NM_001102423.1 | chr2:174077050-174099771 |
| 20539 | Stambp | NM_024239.2 | chr6:83543205-83572504 | 20634 | Stx17 | NM_026343.2 | chr4:48124918-48186506 |
| 20540 | Stambpl1 | NM_029682.4 | chr19:34192289-34240328 | 20635 | Stx18 | NM_001289535.1 | chr5:38039229-38137769 |
| 20541 | Stamcs | NR_038162.1 | chr2:14070332-14073934 | 20636 | Stx19 | NM_026588.1 | chr16:62814675-62822722 |
| 20542 | Stap1 | NM_019992.4 | chr5:86071745-86104000 | 20637 | Stx1a | NM_016801.3 | chr5:135023571-135051099 |
| 20543 | Stap2 | NM_145934.2 | chr17:55997075-56005606 | 20638 | Stx1b | NM_024414.2 | chr7:127806843-127824531 |
| 20544 | Star | NM_011485.4 | chr8:25808512-25815982 | 20639 | Stx2 | NM_001286033.1 | chr5:128984557-129008572 |
| 20545 | Stard10 | NM_019990.4 | chr7:101321318-101346312 | 20640 | Stx3 | NM_001025307.1 | chr19:11775117-11819403 |
| 20546 | Stard13 | NM_001163493.1 | chr5:151037514-151190193 | 20641 | Stx4a | NM_009294.3 | chr7:127841807-127848965 |
| 20547 | Stard3 | NM_021547.3 | chr11:98358367-98381112 | 20642 | Stx5a | NM_001167799.1 | chr19:8741423-8755642 |
| 20548 | Stard3nl | NM_024270.3 | chr13:19357675-19395813 | 20643 | Stx6 | NM_021433.3 | chr1:155158702-155203517 |
| 20549 | Stard4 | NM_133774.4 | chr18:33201420-33233816 | 20644 | Stx7 | NM_016797.4 | chr10:24149316-24188959 |
| 20550 | Stard5 | NM_023377.4 | chr7:83632016-83642328 | 20645 | Stx8 | NM_018768.2 | chr11:67966482-68207148 |
| 20551 | Stard6 | NM_001289648.1 | chr18:70472571-70501065 | 20646 | Stxbp1 | NM_001113569.1 | chr2:32787606-32847237 |
| 20552 | Stard7 | NM_139308.2 | chr2:127270228-127298934 | 20647 | Stxbp2 | NM_011503.4 | chr8:3631159-3643644 |
| 20553 | Stard8 | NM_199018.2 | chrX:99042580-99074728 | 20648 | Stxbp3a | NM_011504.1 | chr3:108793179-108840502 |
| 20554 | Stat1 | NM_001205313.1 | chr1:52119621-52161865 | 20649 | Stxbp3b | NR_073559.1 | chr19:9557805-9559248 |
| 20555 | Stat2 | NM_019963.1 | chr10:128270575-128292849 | 20650 | Stxbp4 | NM_011505.2 | chr11:90476492-90638108 |
| 20556 | Stat3 | NM_011486.5 | chr11:100886805-100939540 | 20651 | Stxbp5 | NM_001081344.2 | chr10:9755546-9901040 |
| 20557 | Stat4 | NM_011487.5 | chr1:52008239-52107189 | 20652 | Stxbp5l | NM_001114611.1 | chr16:37107309-37384958 |
| 20558 | Stat5a | NM_001164062.1 | chr11:100860483-100885169 | 20653 | Stxbp6 | NM_144552.3 | chr12:44852485-45074483 |
| 20559 | Stat5b | NM_001113563.1 | chr11:100780730-100850585 | 20654 | Styk1 | NM_172891.2 | chr6:131299143-131313827 |
| 20560 | Stat6 | NM_009284.2 | chr10:127642985-127660987 | 20655 | Styx | NM_019637.3 | chr14:45351185-45376884 |
| 20561 | Stau1 | NM_001109905.2 | chr2:166947548-166996299 | 20656 | Styxl1 | NM_001289554.1 | chr5:135747219-135778301 |
| 20562 | Stau2 | NM_001111272.1 | chr1:16228809-16519302 | 20657 | Sub1 | NM_011294.3 | chr15:11981338-11996007 |
| 20563 | Stbd1 | NM_175096.3 | chr5:92603050-92606579 | 20658 | Sucla2 | NM_011506.3 | chr14:73552785-73596142 |
| 20564 | Stc1 | NM_009285.3 | chr14:69029288-69041401 | 20659 | Suclg1 | NM_019879.3 | chr6:73248504-73276907 |
| 20565 | Stc2 | NM_011491.3 | chr11:31359440-31370061 | 20660 | Suclg2 | NM_011507.3 | chr6:95473008-95718846 |
| 20566 | Steap1 | NM_027399.3 | chr5:5736321-5749317 | 20661 | Sucnr1 | NM_032400.2 | chr3:60081868-60087566 |
| 20567 | Steap2 | NM_001103156.1 | chr5:5664828-5694089 | 20662 | Suco | NM_172645.2 | chr1:161816111-161876661 |
| 20568 | Steap3 | NM_001085409.1 | chr1:120226415-120271082 | 20663 | Suds3 | NM_001122666.2 | chr5:117091677-117115993 |
| 20569 | Steap4 | NM_054098.3 | chr5:7960471-7982213 | 20664 | Sufu | NM_001025391.2 | chr19:46396895-46488804 |
| 20570 | Stfa1 | NM_001082543.1 | chr16:36277147-36285371 | 20665 | Sugct | NM_138654.3 | chr13:16857474-17694765 |
| 20571 | Stfa2 | NM_001082545.1 | chr16:36403945-36408363 | 20666 | Sugp1 | NM_027481.2 | chr8:70042812-70071953 |
| 20572 | Stfa2l1 | NM_173869.3 | chr16:36156810-36161948 | 20667 | Sugp2 | NM_001168290.1 | chr8:70234225-70261044 |
| 20573 | Stfa3 | NM_025288.2 | chr16:36450536-36455392 | 20668 | Sugt1 | NM_026474.5 | chr14:79587680-79629755 |
| 20574 | Stil | NM_009185.3 | chr4:115000117-115043198 | 20669 | Sulf1 | NM_001198565.1 | chr1:12692429-12860372 |
| 20575 | Stim1 | NM_009287.4 | chr7:102267823-102436855 | 20670 | Sulf2 | NM_001252578.1 | chr2:166073898-166155285 |
| 20576 | Stim2 | NM_001081103.2 | chr5:53998522-54121057 | 20671 | Sult1a1 | NM_133670.1 | chr7:126672869-126676357 |
| 20577 | Stip1 | NM_016737.2 | chr19:7020695-7040026 | 20672 | Sult1b1 | NM_019878.4 | chr5:87513338-87538195 |
| 20578 | Stk10 | NM_009288.2 | chr11:32533265-32624595 | 20673 | Sult1c1 | NM_018751.2 | chr17:53961614-53990631 |
| 20579 | Stk11 | NM_011492.4 | chr10:80115802-80130685 | 20674 | Sult1c2 | NM_026935.4 | chr17:53819636-53845958 |
| 20580 | Stk11ip | NM_027886.3 | chr1:75521528-75537335 | 20675 | Sult1d1 | NM_016771.3 | chr5:87554649-87569006 |
| 20581 | Stk16 | NM_001145827.1 | chr1:75210828-75215606 | 20676 | Sult1e1 | NM_023135.2 | chr5:87575967-87591611 |
| 20582 | Stk17b | NM_133810.3 | chr1:53755511-53785215 | 20677 | Sult2a1 | NM_001111296.2 | chr7:13796245-13837410 |
| 20583 | Stk19 | NM_019442.3 | chr17:34823992-34836903 | 20678 | Sult2a2 | NM_009286.2 | chr7:13733505-13779637 |
| 20584 | Stk24 | NM_145485.2 | chr14:121286340-121379230 | 20679 | Sult2a3 | NM_001101586.2 | chr7:14067554-14122993 |
| 20585 | Stk25 | NM_021537.3 | chr1:93620750-93635727 | 20680 | Sult2a4 | NM_001101534.1 | chr7:13909676-13989588 |
| 20586 | Stk3 | NM_019635.2 | chr15:34875498-35155806 | 20681 | Sult2a5 | NM_001184980.1 | chr7:13623966-13670807 |
| 20587 | Stk31 | NM_029916.2 | chr6:49395603-49469502 | 20682 | Sult2a6 | NM_001081325.2 | chr7:14222462-14254870 |
| 20588 | Stk32a | NM_178749.3 | chr18:43207696-43317481 | 20683 | Sult2a7 | NM_001184981.1 | chr7:14465158-14492926 |
| 20589 | Stk32b | NM_022416.2 | chr5:37446824-37717153 | 20684 | Sult2b1 | NM_017465.2 | chr7:45729982-45759555 |
| 20590 | Stk32c | NM_001162540.1 | chr7:139103637-139213307 | 20685 | Sult3a1 | NM_020565.2 | chr10:33857721-33879475 |
| 20591 | Stk33 | NM_054103.1 | chr7:109279215-109439053 | 20686 | Sult4a1 | NM_013873.3 | chr15:84076096-84105754 |
| 20592 | Stk35 | NM_001038635.2 | chr2:129800516-129832285 | 20687 | Sult5a1 | NM_020564.3 | chr8:123142846-123158280 |
| 20593 | Stk36 | NM_175031.3 | chr1:74601454-74636893 | 20688 | Sult6b1 | NM_001163625.1 | chr17:78883937-78906992 |
| 20594 | Stk38 | NM_134115.2 | chr17:28970884-29079937 | 20689 | Sumf1 | NM_145937.3 | chr6:108107020-108185583 |
| 20595 | Stk38l | NM_172734.3 | chr6:146724929-146778814 | 20690 | Sumf2 | NM_026445.2 | chr5:129846989-129863951 |
| 20596 | Stk39 | NM_016854.6.2 | chr2:68210446-68471981 | 20691 | Sumo1 | NM_009460.2 | chr1:59639433-59670834 |
| 20597 | Stk4 | NM_021420.3 | chr2:164074177-164155521 | 20692 | Sumo2 | NM_133354.2 | chr11:115523108-115536230 |
| 20598 | Stk40 | NM_001145827.1 | chr4:126103956-126141029 | 20693 | Sumo3 | NM_019929.4 | chr10:77606096-77618331 |
| 20599 | Stmn1 | NM_019641.4 | chr4:134468319-134473843 | 20694 | Sun1 | NM_001256115.1 | chr5:139200636-139249839 |
| 20600 | Stmn1-rs1 | NR_029430.1 | chr5:115281091-115282070 | 20695 | Sun2 | NM_001205345.1 | chr15:79724067-79742536 |
| 20601 | Stmn2 | NM_025285.2 | chr3:8509626-8561604 | 20696 | Sun3 | NM_001290519.1 | chr11:9018053-9039591 |
| 20602 | Stmn3 | NM_009133.3 | chr2:181306458-181314500 | 20697 | Sun5 | NM_029599.2 | chr2:153856187-153871084 |
| 20603 | Stmn4 | NM_019675.3 | chr14:66344295-66361680 | 20698 | Suox | NM_173733.3 | chr10:128669886-128673918 |
| 20604 | Stmnd1 | NM_001005422.1 | chr13:46273720-46300115 | 20699 | Supt16 | NM_033618.3 | chr14:52160418-52197239 |
| 20605 | Stom | NM_013515.2 | chr2:35313989-35337009 | 20700 | Supt20 | NM_019995.3 | chr3:54693104-54716837 |
| 20606 | Stoml1 | NM_026942.3 | chr9:58253163-58262524 | 20701 | Supt3 | NM_178652.2 | chr17:44777170-45119284 |

Fig. 26 - 110

| | | | | | | |
|---|---|---|---|---|---|---|
| 20702 | Supt4a | NM_009296.1 | chr11:87737564-87743617 | 20797 | Syt15 | NM_176931.2 | chr14:34220045-34227740 |
| 20703 | Supt5 | NM_013676.1 | chr7:28314895-28338719 | 20798 | Syt16 | NM_172804.2 | chr12:73997786-74267916 |
| 20704 | Supt6 | NM_009297.2 | chr11:78206748-78245703 | 20799 | Syt17 | NM_138649.1 | chr7:118381855-118443552 |
| 20705 | Supt7l | NM_028150.2 | chr5:31514568-31526762 | 20800 | Syt2 | NM_009307.3 | chr1:134646680-134749417 |
| 20706 | Supv3l1 | NM_181423.2 | chr10:62429377-62449693 | 20801 | Syt3 | NM_001114116.1 | chr7:44384125-44400030 |
| 20707 | Surf1 | NM_001271724.1 | chr2:26913377-26916530 | 20802 | Syt4 | NM_009308.3 | chr18:31437807-31447415 |
| 20708 | Surf2 | NM_013678.2 | chr2:26916420-26920170 | 20803 | Syt5 | NM_016908.2 | chr7:4539764-4546567 |
| 20709 | Surf4 | NM_011512.3 | chr2:26920040-26933511 | 20804 | Syt6 | NM_001276676.1 | chr3:103575281-103635179 |
| 20710 | Surf6 | NM_009298.3 | chr2:26890771-26902813 | 20805 | Syt7 | NM_018801.3 | chr19:10389089-10453181 |
| 20711 | Susd1 | NM_001163288.2 | chr4:59314682-59438633 | 20806 | Syt8 | NM_001285857.1 | chr7:142434976-142440396 |
| 20712 | Susd2 | NM_001162913.1 | chr10:75636618-75644008 | 20807 | Syt9 | NM_021889.4 | chr7:107370789-107548655 |
| 20713 | Susd3 | NM_025491.3 | chr13:49230832-49248163 | 20808 | Sytl1 | NM_031393.2 | chr4:133253089-133263087 |
| 20714 | Susd4 | NM_144796.4 | chr1:182764905-182895654 | 20809 | Sytl2 | NM_001040085.2 | chr7:90302354-90410719 |
| 20715 | Susd5 | NM_001101510.1 | chr9:114057353-114098733 | 20810 | Sytl3 | NM_031395.2 | chr17:6673609-6738044 |
| 20716 | Suv39h1 | NM_001290716.1 | chrX:8061170-8074313 | 20811 | Sytl4 | NM_001290717.1 | chrX:133936384-133981812 |
| 20717 | Suv39h2 | NM_022724.4 | chr2:3455814-3474986 | 20812 | Sytl5 | NM_001290728.1 | chrX:9885620-9998864 |
| 20718 | Suv420h1 | NM_001167884.1 | chr19:3767420-3806324 | 20813 | Syvn1 | NM_001164709.1 | chr19:6047144-6053718 |
| 20719 | Suv420h2 | NM_001115018.1 | chr7:4740126-4747514 | 20814 | Szrd1 | NM_001025608.2 | chr4:141112977-141139796 |
| 20720 | Suz12 | NM_001163018.1 | chr11:79993105-80034123 | 20815 | Szt2 | NM_198170.4 | chr4:118362739-118409263 |
| 20721 | Sv2a | NM_022030.3 | chr3:96181226-96195180 | 20816 | T | NM_009309.2 | chr17:8434422-8442496 |
| 20722 | Sv2b | NM_001109753.1 | chr7:75114894-75308386 | 20817 | T2 | NM_001161832.1 | chr17:8372395-8422726 |
| 20723 | Sv2c | NM_029210.1 | chr13:95959442-96132557 | 20818 | Taar1 | NM_053205.1 | chr10:23920405-23921404 |
| 20724 | Sva | NM_009299.2 | chr6:42038393-42042851 | 20819 | Taar2 | NM_001007266.1 | chr10:23938571-23941583 |
| 20725 | Svai1 | NM_027832.3 | chr6:41951627-41956098 | 20820 | Taar3 | NM_001008429.1 | chr10:23949557-23950589 |
| 20726 | Svai2 | NM_032542.1 | chr6:41860338-41864322 | 20821 | Taar4 | NM_001008499.1 | chr10:23960493-23961537 |
| 20727 | Svai3 | NM_001003952.1 | chr6:41968139-41973090 | 20822 | Taar5 | NM_001009574.1 | chr10:23970705-23971719 |
| 20728 | Svep1 | NM_022814.2 | chr4:58042795-58206596 | 20823 | Taar6 | NM_001010823.1 | chr10:23984608-23985646 |
| 20729 | Svil | NM_153153.3 | chr18:5046588-5119293 | 20824 | Taar7a | NM_001010829.1 | chr10:23992404-23993481 |
| 20730 | Svip | NM_001180345.1 | chr7:51997160-52006018 | 20825 | Taar7b | NM_001010827.1 | chr10:23999938-24001015 |
| 20731 | Svop | NM_026805.1 | chr5:114026912-114091380 | 20826 | Taar7d | NM_001010838.1 | chr10:24027221-24028298 |
| 20732 | Svopl | NM_177200.4 | chr6:37983738-38046996 | 20827 | Taar7e | NM_001010835.1 | chr10:24028613-24036690 |
| 20733 | Svs1 | NM_172888.3 | chr6:48986860-48991724 | 20828 | Taar7f | NM_001010839.1 | chr10:24049509-24050586 |
| 20734 | Svs2 | NM_017390.4 | chr2:164235928-164238341 | 20829 | Taar8a | NM_001010830.1 | chr10:24076499-24077534 |
| 20735 | Svs3a | NM_021363.2 | chr2:164291500-164291500 | 20830 | Taar8b | NM_001010837.1 | chr10:24091259-24092294 |
| 20736 | Svs3b | NM_173377.2 | chr2:164254362-164256643 | 20831 | Taar8c | NM_001010840.2 | chr10:24100842-24101951 |
| 20737 | Svs4 | NM_009300.3 | chr2:164275955-164278307 | 20832 | Taar9 | NM_001010831.1 | chr10:24108487-24109534 |
| 20738 | Svs5 | NM_009301.2 | chr2:164332764-164334394 | 20833 | Tab1 | NM_025609.2 | chr15:80133153-80161702 |
| 20739 | Svs6 | NM_013679.2 | chr2:164316750-164318450 | 20834 | Tab2 | NM_138667.3 | chr10:7905647-7956123 |
| 20740 | Swap70 | NM_009302.3 | chr7:110221702-110283506 | 20835 | Tab3 | NM_025729.4 | chrX:85574021-85634469 |
| 20741 | Swi5 | NM_001290552.1 | chr2:32278804-32288069 | 20836 | Tac1 | NM_009311.2 | chr6:7555070-7562973 |
| 20742 | Swsap1 | NM_025870.1 | chr9:21955752-21958270 | 20837 | Tac2 | NM_009311.2 | chr10:127724477-127731768 |
| 20743 | Swt1 | NM_025819.4 | chr1:151367698-151428435 | 20838 | Tac4 | NM_053093.1 | chr11:95261528-95269261 |
| 20744 | Syap1 | NM_025932.2 | chrX:162856842-162888462 | 20839 | Tacc1 | NM_177089.5 | chr8:25154551-25201542 |
| 20745 | Sybu | NM_001032727.1 | chr15:44671855-44748063 | 20840 | Tacc2 | NM_001004468.2 | chr7:130577483-130764782 |
| 20746 | Syce1 | NM_001143765.1 | chr7:140777228-140787854 | 20841 | Tacc3 | NM_001040435.3 | chr5:33658127-33672202 |
| 20747 | Syce1l | NM_001048145.1 | chr8:113643212-113655533 | 20842 | Taco1 | NM_027346.1 | chr11:106066106-106073612 |
| 20748 | Syce2 | NM_001168244.1 | chr8:84872257-84887446 | 20843 | Tacr1 | NM_009313.5 | chr6:82402474-82560104 |
| 20749 | Syce3 | NM_001162880.1 | chr15:89390173-89410503 | 20844 | Tacr2 | NM_009314.4 | chr10:62252437-62265990 |
| 20750 | Sycn | NM_026716.3 | chr7:28540884-28542210 | 20845 | Tacr3 | NM_021382.6 | chr3:134829006-134934581 |
| 20751 | Sycp1 | NM_011516.2 | chr3:102818498-102936100 | 20846 | Tacstd2 | NM_020047.3 | chr6:67534058-67535822 |
| 20752 | Sycp1-ps1 | NR_024208.1 | chr7:18786301-18789414 | 20847 | Tada1 | NM_030245.3 | chr1:166379166-166393620 |
| 20753 | Sycp2 | NM_177191.3 | chr2:178345295-178407658 | 20848 | Tada2a | NM_172562.3 | chr11:84078919-84129568 |
| 20754 | Sycp3 | NM_011420.1 | chr10:88459586-88473236 | 20849 | Tada2b | NM_001170454.1 | chr5:36473669-36484285 |
| 20755 | Syde1 | NM_027875.1 | chr10:78584502-78591964 | 20850 | Tada3 | NM_133932.2 | chr6:113366656-113377520 |
| 20756 | Syde2 | NM_001166064.1 | chr3:145987869-146021720 | 20851 | Taf1 | NM_001290729.1 | chrX:101527574-101601789 |
| 20757 | Syf2 | NM_026780.3 | chr4:134930979-134937537 | 20852 | Taf10 | NM_020024.3 | chr7:105742893-105744338 |
| 20758 | Syk | NM_001198977.1 | chr13:52583436-52648792 | 20853 | Taf11 | NM_026836.2 | chr17:27901127-27907724 |
| 20759 | Sympk | NM_026805.2 | chr7:19024376-19054622 | 20854 | Taf12 | NM_025579.3 | chr4:132274374-132293330 |
| 20760 | Syn1 | NM_001110780.1 | chrX:20860510-20920918 | 20855 | Taf13 | NM_025444.2 | chr3:108571698-108582068 |
| 20761 | Syn2 | NM_001111015.1 | chr6:115134901-115282626 | 20856 | Taf15 | NM_027427.2 | chr11:83473107-83506740 |
| 20762 | Syn3 | NM_001164495.1 | chr10:86291592-86498896 | 20857 | Taf1a | NM_001277957.1 | chr1:183388884-183410206 |
| 20763 | Syna | NM_001013751.2 | chr5:134557253-134560171 | 20858 | Taf1b | NM_029614.2 | chr12:24498580-24558571 |
| 20764 | Synb | NM_173420.3 | chr14:69290397-69512549 | 20859 | Taf1c | NM_021441.2 | chr8:119597973-119605240 |
| 20765 | Sync | NM_023485.3 | chr4:129287520-129308559 | 20860 | Taf1d | NM_027261.3 | chr9:15306213-15312105 |
| 20766 | Syncrip | NM_001284328.1 | chr9:88449363-88482397 | 20861 | Taf2 | NM_001081288.1 | chr15:55015128-55072152 |
| 20767 | Syndig1 | NM_001085521.2 | chr2:149830782-150004392 | 20862 | Taf3 | NM_027748.3 | chr2:9914551-10048609 |
| 20768 | Syndig1l | NM_001033334.2 | chr12:84677277-84698807 | 20863 | Taf4a | NM_001081092.1 | chr2:179912145-179976646 |
| 20769 | Syne1 | NM_001079686.1 | chr10:5020195-5194707 | 20864 | Taf4b | NM_001100449.1 | chr18:14783244-14900359 |
| 20770 | Syne2 | NM_001005510.2 | chr12:75818317-76110928 | 20865 | Taf5 | NM_177342.3 | chr19:47067747-47083479 |
| 20771 | Syne3 | NM_001042699.2 | chr12:104929932-104998677 | 20866 | Taf5l | NM_133966.2 | chr8:123996312-124021309 |
| 20772 | Syne4 | NM_001290565.1 | chr7:30314815-30319046 | 20867 | Taf6 | NM_009315.3 | chr5:138178616-138187186 |
| 20773 | Syngap1 | NM_001281491.1 | chr17:26941451-26970645 | 20868 | Taf6l | NM_001177798.1 | chr19:8774853-8786417 |
| 20774 | Syngr1 | NM_009303.2 | chr15:80091333-80113440 | 20869 | Taf7 | NM_175770.4 | chr18:37640490-37644204 |
| 20775 | Syngr2 | NM_009304.2 | chr11:117809666-117814286 | 20870 | Taf7l | NM_028958.4 | chrX:134460115-134476490 |
| 20776 | Syngr3 | NM_011522.3 | chr17:24685091-24689949 | 20871 | Taf8 | NM_022015.3 | chr17:47488049-47502287 |
| 20777 | Syngr4 | NM_029191064.1 | chr7:45886844-45896711 | 20872 | Taf9 | NM_001015889.2 | chr13:100651606-100656060 |
| 20778 | Synj1 | NM_001045515.1 | chr16:90936100-91011095 | 20873 | Taf9b | NM_001001176.2 | chrX:106206873-106219842 |
| 20779 | Synj2 | NM_001113351.1 | chr17:5975585-6044280 | 20874 | Tagap | NM_145968.2 | chr17:7925999-7934897 |
| 20780 | Synj2bp | NM_025292.7 | chr12:81492193-81532911 | 20875 | Tagap1 | NM_147155.2 | chr17:6954964-6961156 |
| 20781 | Synm | NM_183312.3 | chr7:67730160-67759742 | 20876 | Tagln | NM_011526.5 | chr9:45929627-45936058 |
| 20782 | Synpo | NM_001109975.1 | chr18:60600205-60610104 | 20877 | Tagln2 | NM_178598.2 | chr1:172500245-172507375 |
| 20783 | Synpo2 | NM_080451.3 | chr3:123076518-123236149 | 20878 | Tagln3 | NM_019754.3 | chr16:45711229-45724531 |
| 20784 | Synpo2l | NM_175132.4 | chr14:20658947-20668354 | 20879 | Tal1 | NM_001287388.1 | chr4:115057710-115071755 |
| 20785 | Synpr | NM_001163032.1 | chr14:13453957-13615469 | 20880 | Tal2 | NM_009317.3 | chr4:53779704-53786885 |
| 20786 | Synrg | NM_194341.2 | chr11:83964430-84044576 | 20881 | Taldo1 | NM_011528.4 | chr7:141392159-141402976 |
| 20787 | Syp | NM_009305.2 | chrX:7638579-7653256 | 20882 | Tamm41 | NM_026894.1 | chr6:115040380-115037874 |
| 20788 | Sypl | NM_013635.3 | chr12:32953944-32979500 | 20883 | Tanc1 | NM_001290659.1 | chr2:59646768-59846213 |
| 20789 | Sypl2 | NM_008596.1 | chr3:108212265-108226599 | 20884 | Tanc2 | NM_181071.3 | chr11:105589985-105929303 |
| 20790 | Sys1 | NM_025575.3 | chr2:164460970-164465510 | 20885 | Tango2 | NM_138583.2 | chr16:18300824-18343932 |
| 20791 | Syt1 | NM_001252341.1 | chr10:108497649-109010975 | 20886 | Tango6 | NM_173037.1 | chr8:106683067-106851439 |
| 20792 | Syt10 | NM_018803.2 | chr15:89782392-89841860 | 20887 | Tank | NM_001164071.1 | chr2:61593096-61654169 |
| 20793 | Syt11 | NM_018804.3 | chr3:88744700-88772599 | 20888 | Taok1 | NM_144825.2 | chr11:77529161-77607815 |
| 20794 | Syt12 | NM_134164.5 | chr19:4445907-4477143 | 20889 | Taok2 | NM_001163774.1 | chr7:126865676-126884967 |
| 20795 | Syt13 | NM_030725.4 | chr2:92915100-92956051 | 20890 | Taok3 | NM_001081308.2 | chr5:117133587-117279098 |
| 20796 | Syt14 | NM_181546.3 | chr1:192891233-193035775 | 20891 | Tap1 | NM_001161730.1 | chr17:34187555-34197225 |

Fig. 26 - 111

| | | | | | | | | |
|---|---|---|---|---|---|---|---|---|
| 20892 | Tap2 | NM_011530.3 | chr17:34204478-34216321 | | 20987 | Tbck | NM_001163455.2 | chr3:132684143-132841688 |
| 20893 | Tapbp | NM_001025313.1 | chr17:33919477-33929290 | | 20988 | Tbk1 | NM_019786.4 | chr10:121546455-121586794 |
| 20894 | Tapbpl | NM_145391.2 | chr6:125224211-125231860 | | 20989 | Tbkbp1 | NM_198100.2 | chr11:97136170-97149712 |
| 20895 | Tapt1 | NM_173764.3 | chr5:44175161-44226606 | | 20990 | Tbl1x | NM_020601.2 | chrX:77511226-77660265 |
| 20896 | Tarbp2 | NM_001253795.1 | chr15:102518191-102523676 | | 20991 | Tbl1xr1 | NM_030732.3 | chr3:22076651-22216594 |
| 20897 | Tardbp | NM_001003898.3 | chr4:148612381-148626996 | | 20992 | Tbl2 | NM_013763.2 | chr5:135149710-135162662 |
| 20898 | Tarm1 | NM_177363.3 | chr7:3489075-3502552 | | 20993 | Tbl3 | NM_145396.4 | chr17:24700662-24707653 |
| 20899 | Tars | NM_033074.3 | chr15:11383662-11399658 | | 20994 | Tbp | NM_013684.3 | chr17:15498887-15517427 |
| 20900 | Tars2 | NM_001163617.1 | chr3:95739973-95754977 | | 20995 | Tbpl1 | NM_011603.5 | chr10:22703876-22731447 |
| 20901 | Tarsl2 | NM_172310.2 | chr7:65644897-65692093 | | 20996 | Tbpl2 | NM_001289689.1 | chr2:24071365-24096595 |
| 20902 | Tas1r1 | NM_031867.2 | chr4:152027913-152038490 | | 20997 | Tbr1 | NM_009322.3 | chr2:61804452-61814113 |
| 20903 | Tas1r2 | NM_031873.1 | chr4:139653537-139670279 | | 20998 | Tbrg1 | NM_025289.3 | chr9:37649181-37657312 |
| 20904 | Tas1r3 | NM_031872.2 | chr4:155859269-155863353 | | 20999 | Tbrg3 | NR_027799.1 | chr15:82890482-82898461 |
| 20905 | Tas2r102 | NM_199153.2 | chr6:132762136-132763174 | | 21000 | Tbrg4 | NM_001130457.1 | chr11:6615597-6626067 |
| 20906 | Tas2r103 | NM_053211.1 | chr6:133036162-133037101 | | 21001 | Tbx1 | NM_001285472.1 | chr16:18587703-18590671 |
| 20907 | Tas2r104 | NM_207011.1 | chr6:131684835-131685744 | | 21002 | Tbx10 | NM_001001320.1 | chr19:3992751-3999512 |
| 20908 | Tas2r105 | NM_020501.1 | chr6:131686560-131687463 | | 21003 | Tbx15 | NM_009323.2 | chr3:99253759-99354260 |
| 20909 | Tas2r106 | NM_207016.1 | chr6:131677959-131678886 | | 21004 | Tbx18 | NM_023814.4 | chr9:87702799-87731260 |
| 20910 | Tas2r107 | NM_199154.1 | chr6:131659157-131660084 | | 21005 | Tbx19 | NM_032005.4 | chr1:165137852-165160773 |
| 20911 | Tas2r108 | NM_020502.1 | chr6:40493591-40494485 | | 21006 | Tbx2 | NM_009324.2 | chr11:85832614-85841948 |
| 20912 | Tas2r109 | NM_207017.1 | chr6:132980014-132980965 | | 21007 | Tbx20 | NM_001205085.1 | chr9:24740247-24774303 |
| 20913 | Tas2r110 | NM_199155.2 | chr6:132868007-132869009 | | 21008 | Tbx21 | NM_019507.2 | chr11:97098006-97115331 |
| 20914 | Tas2r113 | NM_207018.1 | chr6:132893010-132893940 | | 21009 | Tbx22 | NM_001290747.1 | chrX:107679014-107688980 |
| 20915 | Tas2r114 | NM_207019.1 | chr6:131689133-131690063 | | 21010 | Tbx3 | NM_011535.3 | chr5:119671232-119684724 |
| 20916 | Tas2r115 | NM_207020.1 | chr6:132737053-132737986 | | 21011 | Tbx3os2 | NR_040416.1 | chr5:119685087-119691218 |
| 20917 | Tas2r116 | NM_053212.1 | chr6:132855437-132856355 | | 21012 | Tbx4 | NM_011536.2 | chr11:85890062-85916097 |
| 20918 | Tas2r117 | NM_207021.1 | chr6:132802900-132803893 | | 21013 | Tbx5 | NM_011537.3 | chr5:119834662-119885218 |
| 20919 | Tas2r118 | NM_207022.1 | chr6:23969160-23970060 | | 21014 | Tbx6 | NM_011538.2 | chr7:126781482-126785548 |
| 20920 | Tas2r119 | NM_020503.2 | chr15:32177288-32178294 | | 21015 | Tbxa2r | NM_001277265.1 | chr10:81328702-81335174 |
| 20921 | Tas2r120 | NM_207023.1 | chr6:132656956-132657844 | | 21016 | Tbxas1 | NM_011539.3 | chr6:38918985-39084579 |
| 20922 | Tas2r121 | NM_207024.1 | chr6:132700089-132701007 | | 21017 | Tc2n | NM_001082976.2 | chr12:101645445-101718523 |
| 20923 | Tas2r122 | NM_001039128.1 | chr6:132710998-132711928 | | 21018 | Tcaim | NM_001013405.2 | chr9:122805546-122836332 |
| 20924 | Tas2r123 | NM_207025.1 | chr6:132847141-132848143 | | 21019 | Tcam1 | NM_029467.3 | chr11:106276671-106288143 |
| 20925 | Tas2r124 | NM_207026.1 | chr6:132754729-132755659 | | 21020 | Tcap | NM_011540.2 | chr11:98383810-98384953 |
| 20926 | Tas2r125 | NM_207027.1 | chr6:132909650-132910586 | | 21021 | Tcea1 | NM_011591.50.1 | chr1:4857693-4897909 |
| 20927 | Tas2r126 | NM_207028.3 | chr6:42434534-42435461 | | 21022 | Tcea2 | NM_009326.2 | chr2:181680309-181688051 |
| 20928 | Tas2r129 | NM_207029.1 | chr6:132951101-132952064 | | 21023 | Tcea3 | NM_011542.2 | chr4:136247956-136274899 |
| 20929 | Tas2r130 | NM_199156.1 | chr6:131629891-131630830 | | 21024 | Tceal1 | NM_146236.1 | chrX:136708064-136709866 |
| 20930 | Tas2r131 | NM_207030.1 | chr6:132956911-132957844 | | 21025 | Tceal3 | NM_001029978.2 | chrX:136666374-136668377 |
| 20931 | Tas2r134 | NM_199158.1 | chr2:51627510-51628407 | | 21026 | Tceal5 | NM_177919.2 | chrX:136200950-136203851 |
| 20932 | Tas2r135 | NM_199159.1 | chr6:42405528-42406494 | | 21027 | Tceal6 | NM_025355.4 | chrX:135208585-135210687 |
| 20933 | Tas2r136 | NM_181276.1 | chr6:132777178-132778162 | | 21028 | Tceal7 | NM_001127169.1 | chrX:136224040-136226100 |
| 20934 | Tas2r137 | NM_001025385.1 | chr6:40491237-40492239 | | 21029 | Tceal8 | NM_001168578.1 | chrX:136168983-136172251 |
| 20935 | Tas2r138 | NM_001001451.1 | chr6:40612314-40613310 | | 21030 | Tceanc | NM_001007577.2 | chrX:166499814-166510478 |
| 20936 | Tas2r139 | NM_181275.1 | chr6:42140935-42141895 | | 21031 | Tceanc2 | NM_025617.2 | chr4:107134161-107178366 |
| 20937 | Tas2r140 | NM_021562.1 | chr6:133054854-133055793 | | 21032 | Tceb1 | NM_026456.3 | chr1:16642764-16656865 |
| 20938 | Tas2r143 | NM_001001452.1 | chr6:42400237-42401119 | | 21033 | Tceb2 | NM_026305.2 | chr17:23824739-23829109 |
| 20939 | Tas2r144 | NM_001001453.1 | chr6:42215327-42216287 | | 21034 | Tceb3 | NM_013736.4 | chr4:136003369-136021649 |
| 20940 | Taspl | NM_001159640.2 | chr2:139833478-140066805 | | 21035 | Tcerg1 | NM_001039474.1 | chr18:42511486-42575785 |
| 20941 | Tat | NM_146214.3 | chr8:109990435-109999804 | | 21036 | Tcerg1l | NM_183289.3 | chr7:138208971-138397730 |
| 20942 | Tatdn1 | NM_175151.4 | chr15:58890152-58933730 | | 21037 | Tcf12 | NM_001253862.1 | chr9:71844251-72111201 |
| 20943 | Tatdn2 | NM_001033463.3 | chr6:113697498-113711068 | | 21038 | Tcf15 | NM_009328.2 | chr2:152143608-152149096 |
| 20944 | Tatdn3 | NM_001163421.1 | chr1:191045829-191062932 | | 21039 | Tcf19 | NM_001163763.1 | chr17:35512734-35516824 |
| 20945 | Tax1bp1 | NM_025816.3 | chr6:52713728-52766779 | | 21040 | Tcf20 | NM_001114140.1 | chr15:82808625-82912134 |
| 20946 | Tax1bp3 | NM_029564.2 | chr1:73177082-73182046 | | 21041 | Tcf21 | NM_011545.1 | chr10:22817274-22820128 |
| 20947 | Taz | NM_001173547.2 | chrX:74282717-74290151 | | 21042 | Tcf23 | NM_053085.2 | chr5:30968676-30977018 |
| 20948 | Tbata | NM_001017407.1 | chr10:61175261-61180680 | | 21043 | Tcf24 | NM_001285425.1 | chr1:9960162-9967485 |
| 20949 | Tbc1d1 | NM_001289514.1 | chr5:64230356-64351486 | | 21044 | Tcf25 | NM_001037877.3 | chr8:123373710-123404174 |
| 20950 | Tbc1d10a | NM_134023.1 | chr11:4186832-4215505 | | 21045 | Tcf3 | NM_001164147.1 | chr10:80409164-80433653 |
| 20951 | Tbc1d10b | NM_144522.5 | chr7:127197458-127208468 | | 21046 | Tcf4 | NM_001083967.1 | chr18:69345720-69687967 |
| 20952 | Tbc1d10c | NM_178650.3 | chr19:4184356-4191047 | | 21047 | Tcf7 | NM_009331.4 | chr11:52252282-52282595 |
| 20953 | Tbc1d12 | NM_145952.3 | chr19:38836578-38919923 | | 21048 | Tcf7l1 | NM_001079822.2 | chr6:72626370-72789045 |
| 20954 | Tbc1d13 | NM_146252.2 | chr2:30133870-30152013 | | 21049 | Tcf7l2 | NM_001142918.1 | chr19:55741809-55933655 |
| 20955 | Tbc1d14 | NM_001113362.1 | chr5:36490603-36586226 | | 21050 | Tcfl5 | NM_178254.3 | chr2:180621956-180642691 |
| 20956 | Tbc1d15 | NM_025706.3 | chr10:115197870-115251493 | | 21051 | Tchh | NM_001163098.1 | chr3:93442329-93449077 |
| 20957 | Tbc1d16 | NM_172443.3 | chr11:119143042-119228499 | | 21052 | Tchhl1 | NM_027762.3 | chr3:93468753-93471980 |
| 20958 | Tbc1d17 | NM_001042655.1 | chr7:44840775-44849079 | | 21053 | Tchp | NM_029992.2 | chr5:114707778-114722327 |
| 20959 | Tbc1d19 | NM_144517.4 | chr5:53809626-53904380 | | 21054 | Tcirg1 | NM_001136091.2 | chr19:3896049-3907133 |
| 20960 | Tbc1d2 | NM_198864.3 | chr4:46604389-46650139 | | 21055 | Tcl1 | NM_001289468.1 | chr12:105216754-105222737 |
| 20961 | Tbc1d20 | NM_024329.2 | chr2:152293871-152312590 | | 21056 | Tcl1b1 | NM_013773.2 | chr12:105159703-105166625 |
| 20962 | Tbc1d21 | NM_028854.3 | chr9:58359803-58370369 | | 21057 | Tcl1b2 | NM_013775.1 | chr12:105147032-105155225 |
| 20963 | Tbc1d22a | NM_145476.2 | chr15:86214458-86498503 | | 21058 | Tcl1b3 | NM_013772.2 | chr12:105191044-105195399 |
| 20964 | Tbc1d22b | NM_198647.3 | chr17:29549801-29606808 | | 21059 | Tcl1b4 | NM_013774.2 | chr12:105202421-105206993 |
| 20965 | Tbc1d22bos | NR_045447.1 | chr17:29578815-29596305 | | 21060 | Tcl1b5 | NM_013776.1 | chr12:105176357-105181145 |
| 20966 | Tbc1d23 | NM_026254.2 | chr16:57168863-57231466 | | 21061 | Tcn2 | NM_001130458.1 | chr11:3917079-3932078 |
| 20967 | Tbc1d24 | NM_001163647.1 | chr17:24175430-24205562 | | 21062 | Tcof1 | NM_001189984.1 | chr18:60813755-60848964 |
| 20968 | Tbc1d25 | NM_001166437.1 | chrX:8154471-8176181 | | 21063 | Tcp1 | NM_001290712.1 | chr17:12916328-12925067 |
| 20969 | Tbc1d2b | NM_194334.2 | chr9:90202048-90270769 | | 21064 | Tcp10a | NM_011553.4 | chr17:7324659-7345860 |
| 20970 | Tbc1d30 | NM_029057.1 | chr10:121263819-121311189 | | 21065 | Tcp10b | NM_009341.2 | chr17:13061110-13082226 |
| 20971 | Tbc1d31 | NM_001081396.2 | chr15:57912198-57970068 | | 21066 | Tcp10c | NM_001167578.1 | chr17:13354571-13377223 |
| 20972 | Tbc1d32 | NM_001033385.3 | chr10:56014293-56228689 | | 21067 | Tcp11 | NM_001085555.1 | chr17:28066746-28080639 |
| 20973 | Tbc1d4 | NM_001081278.2 | chr14:101442359-101609191 | | 21068 | Tcp11l1 | NM_177190.5 | chr2:104679979-104712162 |
| 20974 | Tbc1d5 | NM_001285991.1 | chr17:50733126-51179352 | | 21069 | Tcp11l2 | NM_146008.2 | chr10:84576946-84614355 |
| 20975 | Tbc1d7 | NM_001252639.1 | chr13:43151741-43171501 | | 21070 | Tcstv1 | NM_018756.3 | chr13:119893386-119894785 |
| 20976 | Tbc1d8 | NM_018775.4 | chr1:39371495-39478747 | | 21071 | Tcstv3 | NM_153523.3 | chr13:120316861-120318261 |
| 20977 | Tbc1d8b | NM_001081499.2 | chrX:139684995-139754218 | | 21072 | Tcta | NM_133986.2 | chr9:108302954-108306159 |
| 20978 | Tbc1d9 | NM_001113304.1 | chr8:83165351-83272940 | | 21073 | Tcte1 | NM_013688.2 | chr17:45523433-45542677 |
| 20979 | Tbc1d9b | NM_001290759.1 | chr11:50131359-50172785 | | 21074 | Tcte2 | NM_022311.2 | chr17:13716435-13761394 |
| 20980 | Tbca | NM_009321.2 | chr13:94788942-94842899 | | 21075 | Tcte3 | NM_011560.3 | chr17:15027153-15041559 |
| 20981 | Tbcb | NM_025548.3 | chr7:30224130-30232029 | | 21076 | Tctex1d1 | NM_001163767.1 | chr4:102986378-103005594 |
| 20982 | Tbcc | NM_178385.3 | chr17:46890620-46892463 | | 21077 | Tctex1d2 | NM_025329.3 | chr16:32419701-32428892 |
| 20983 | Tbccd1 | NM_001081368.2 | chr16:22813214-22857569 | | 21078 | Tctex1d4 | NM_175030.2 | chr4:117126812-117128730 |
| 20984 | Tbcd | NM_029878.1 | chr11:121451948-121617170 | | 21079 | Tctn1 | NM_001039153.3 | chr5:122239494-122264460 |
| 20985 | Tbce | NM_178337.3 | chr13:13997950-14039638 | | 21080 | Tctn2 | NM_026486.3 | chr5:124598748-124627738 |
| 20986 | Tbcel | NM_173038.3 | chr9:42412316-42472226 | | 21081 | Tctn3 | NM_026260.2 | chr19:40596445-40612215 |

Fig. 26 - 112

| | | | |
|---|---|---|---|
| 21082 | Tdg | NM_011561.2 | chr10:82629837-82650494 |
| 21083 | Tdgf1 | NM_011562.2 | chr9:110939607-110946158 |
| 21084 | Tdh | NM_021480.5 | chr14:63492346-63509092 |
| 21085 | Tdo2 | NM_019911.2 | chr3:81958413-81975728 |
| 21086 | Tdp1 | NM_028354.4 | chr12:99884514-99955216 |
| 21087 | Tdp2 | NM_019551.2 | chr13:24831658-24842153 |
| 21088 | Tdpoz1 | NM_148949.2 | chr3:93669332-93676283 |
| 21089 | Tdpoz2 | NM_001007222.3 | chr3:93651541-93652686 |
| 21090 | Tdpoz3 | NM_207271.2 | chr3:93826019-93827117 |
| 21091 | Tdpoz4 | NM_207272.2 | chr3:93796397-93797510 |
| 21092 | Tdpoz5 | NM_207273.2 | chr3:93960291-94072644 |
| 21093 | Tdrd1 | NM_001002238.2 | chr19:56826208-56870012 |
| 21094 | Tdrd12 | NM_028034.2 | chr7:35493609-35537744 |
| 21095 | Tdrd3 | NM_001253755.1 | chr14:87416582-87515192 |
| 21096 | Tdrd5 | NM_001134741.1 | chr1:156255295-156303348 |
| 21097 | Tdrd6 | NM_001161366.1 | chr17:43615334-43630299 |
| 21098 | Tdrd7 | NM_001290475.1 | chr4:45965334-46034765 |
| 21099 | Tdrd9 | NM_029056.1 | chr12:111971558-112068854 |
| 21100 | Tdrkh | NM_028307.1 | chr3:94413317-94431499 |
| 21101 | Tdrp | NM_173744.4 | chr8:13952007-13974777 |
| 21102 | Tead1 | NM_009166584.1 | chr7:112679319-112906805 |
| 21103 | Tead2 | NM_001285498.1 | chr7:45215752-45233619 |
| 21104 | Tead3 | NM_001098226.3 | chr17:28331672-28350600 |
| 21105 | Tead4 | NM_001080979.1 | chr6:128227142-128300813 |
| 21106 | Tec | NM_001113460.2 | chr5:72755717-72868448 |
| 21107 | Tecpr1 | NM_027410.1 | chr5:144195346-144223578 |
| 21108 | Tecpr2 | NM_001081057.2 | chr12:110889263-110972394 |
| 21109 | Tecr | NM_027179.1 | chr8:83571697-83594491 |
| 21110 | Tecrl | NM_153801.3 | chr5:83278121-83355195 |
| 21111 | Tecta | NM_009347.2 | chr9:42329621-42399929 |
| 21112 | Tectb | NM_009348.3 | chr19:55180884-55196313 |
| 21113 | Teddm1 | NM_178244.3 | chr1:153891645-153893060 |
| 21114 | Tef | NM_017376.3 | chr15:81811413-81826863 |
| 21115 | Tefm | NM_183275.2 | chr7:80136677-80142153 |
| 21116 | Tek | NM_001290549.1 | chr4:94739288-94874976 |
| 21117 | Tekt1 | NM_001282006.1 | chr11:72344716-72362442 |
| 21118 | Tekt2 | NM_011902.2 | chr4:126322120-126325199 |
| 21119 | Tekt3 | NM_027660.1 | chr11:63061658-63094960 |
| 21120 | Tekt4 | NM_020548.2 | chr17:25471589-25476594 |
| 21121 | Tekt5 | NM_001099275.1 | chr16:10361253-10395448 |
| 21122 | Telo2 | NM_001163661.1 | chr17:25099568-25115967 |
| 21123 | Ten1 | NM_027107.1 | chr11:116198854-116215318 |
| 21124 | Tenc1 | NM_153533.2 | chr15:102102987-102116401 |
| 21125 | Tenm1 | NM_011855.4 | chrX:42532392-43274784 |
| 21126 | Tenm2 | NM_001290702.1 | chr11:36006655-36944241 |
| 21127 | Tenm3 | NM_001145937.1 | chr8:48225664-48674690 |
| 21128 | Tenm4 | NM_011858.4 | chr7:96210636-96911092 |
| 21129 | Tep1 | NM_009351.2 | chr14:50824060-50870554 |
| 21130 | Tepp | NM_028532.3 | chr8:95311597-95321329 |
| 21131 | Terc | NR_001579.1 | chr3:96414436-96414833 |
| 21132 | Terf1 | NM_001286628.1 | chr1:15805645-15844052 |
| 21133 | Terf2 | NM_001083118.2 | chr8:107075516-107096545 |
| 21134 | Terf2ip | NM_026084.2 | chr8:112011358-112020528 |
| 21135 | Tert | NM_009354.1 | chr13:73627000-73649041 |
| 21136 | Tes | NM_207176.3 | chr6:17065148-17105825 |
| 21137 | Tesc | NM_021344.3 | chr5:118027823-118061870 |
| 21138 | Tescl | NM_001163810.1 | chr7:24333079-24333965 |
| 21139 | Tesk1 | NM_011571.3 | chr4:43442276-43448075 |
| 21140 | Tesk2 | NM_146151.4 | chr4:116720954-116804248 |
| 21141 | Tespa1 | NM_183264.4 | chr10:130322851-130362642 |
| 21142 | Tet1 | NM_001253857.1 | chr10:62804569-62880014 |
| 21143 | Tet2 | NM_001040400.2 | chr3:133463676-133544390 |
| 21144 | Tet3 | NM_183138.2 | chr6:83362373-83441678 |
| 21145 | Tex10 | NM_172304.3 | chr4:48430955-48473422 |
| 21146 | Tex101 | NM_019189.2 | chr7:24668011-24672050 |
| 21147 | Tex11 | NM_001167997.1 | chrX:100877881-101059639 |
| 21148 | Tex12 | NM_025687.3 | chr9:50557147-50561268 |
| 21149 | Tex13 | NM_031381.2 | chrX:140808306-140813433 |
| 21150 | Tex13a | NM_026469.2 | chrX:138208164-138209580 |
| 21151 | Tex14 | NM_001199293.1 | chr11:87427590-87555823 |
| 21152 | Tex15 | NM_031374.2 | chr8:33570543-33585585 |
| 21153 | Tex16 | NM_031382.2 | chrX:112093519-112127326 |
| 21154 | Tex19.1 | NM_028602.2 | chr11:121146142-121148313 |
| 21155 | Tex19.2 | NM_027622.3 | chr11:121116214-121118677 |
| 21156 | Tex2 | NM_198292.3 | chr11:106502138-106612930 |
| 21157 | Tex21 | NM_001159715.1 | chr12:76203984-76246746 |
| 21158 | Tex22 | NM_029381.1 | chr12:113074501-113088914 |
| 21159 | Tex24 | NM_001013609.2 | chr8:27344393-27349188 |
| 21160 | Tex26 | NM_029426.4 | chr5:149439659-149470979 |
| 21161 | Tex261 | NM_009357.2 | chr6:83770413-83775812 |
| 21162 | Tex264 | NM_001081654.2 | chr9:106658745-106685952 |
| 21163 | Tex28 | NM_001126488.2 | chrX:74150943-74167838 |
| 21164 | Tex29 | NM_029326.2 | chr8:11840520-11855761 |
| 21165 | Tex30 | NM_029368.3 | chr1:44086616-44102388 |
| 21166 | Tex33 | NM_001163612.2 | chr15:78378399-78395912 |
| 21167 | Tex35 | NM_028540.3 | chr1:157099146-157108650 |
| 21168 | Tex36 | NM_029494.2 | chr7:133587023-133602115 |
| 21169 | Tex37 | NM_028825.3 | chr6:70913088-70918922 |
| 21170 | Tex38 | NM_029196.1 | chr4:115779833-115781084 |
| 21171 | Tex40 | NM_001039494.2 | chr19:6922425-6925380 |
| 21172 | Tex43 | NM_026099.3 | chr18:56588347-56594779 |
| 21173 | Tex9 | NM_009359.4 | chr9:72458054-72491959 |
| 21174 | Tfam | NM_009360.4 | chr10:71225476-71238044 |
| 21175 | Tfap2a | NM_001122948.2 | chr13:40715302-40730457 |
| 21176 | Tfap2b | NM_001025305.2 | chr1:19212053-19238845 |
| 21177 | Tfap2c | NM_001159696.1 | chr2:172550990-172558621 |
| 21178 | Tfap2d | NM_153154.2 | chr1:19103021-19166332 |
| 21179 | Tfap2e | NM_198960.2 | chr4:126716002-126736269 |
| 21180 | Tfap4 | NM_031182.2 | chr16:4544660-4559720 |
| 21181 | Tfb1m | NM_146074.1 | chr17:3519255-3557713 |
| 21182 | Tfb2m | NM_008249.4 | chr1:179528055-179546267 |
| 21183 | Tfcp2 | NM_001289603.1 | chr15:100502747-100552008 |
| 21184 | Tfcp2l1 | NM_023755.2 | chr1:118627944-118685168 |
| 21185 | Tfdp1 | NM_001291765.1 | chr8:13338750-13378448 |
| 21186 | Tfdp2 | NM_001184706.1 | chr9:96196274-96323646 |
| 21187 | Tfe3 | NM_001105196.1 | chrX:7762660-7775202 |
| 21188 | Tfeb | NM_001161722.1 | chr17:47737036-47792416 |
| 21189 | Tfec | NM_031198.3 | chr6:16833380-16898441 |
| 21190 | Tff1 | NM_009362.2 | chr17:31161395-31165053 |
| 21191 | Tff2 | NM_009363.3 | chr17:31141061-31144282 |
| 21192 | Tff3 | NM_011575.2 | chr17:31125305-31129611 |
| 21193 | Tfg | NM_001252443.1 | chr16:56690328-56717450 |
| 21194 | Tfip11 | NM_018783.4 | chr5:112326368-112338073 |
| 21195 | Tfpi | NM_001177319.1 | chr2:84440722-84476759 |
| 21196 | Tfpi2 | NM_009364.3 | chr6:3962594-3968354 |
| 21197 | Tfpt | NM_001290381.1 | chr7:3620323-3629929 |
| 21198 | Tfr2 | NM_001289507.1 | chr5:137570804-137588081 |
| 21199 | Tfrc | NM_011638.4 | chr16:32608895-32632794 |
| 21200 | Tg | NM_009375.2 | chr15:66670769-66850720 |
| 21201 | Tgds | NM_029578.3 | chr14:118111910-118132765 |
| 21202 | Tgfa | NM_031199.4 | chr6:86195226-86275743 |
| 21203 | Tgfb1 | NM_011577.2 | chr7:25687001-25795077 |
| 21204 | Tgfb1i1 | NM_001289550.1 | chr7:128246811-128255699 |
| 21205 | Tgfb2 | NM_009367.3 | chr1:186623185-186705992 |
| 21206 | Tgfb3 | NM_009368.3 | chr12:86056742-86079041 |
| 21207 | Tgfbi | NM_009369.4 | chr13:56609602-56639339 |
| 21208 | Tgfbr1 | NM_009370.3 | chr4:47353221-47414924 |
| 21209 | Tgfbr2 | NM_009371.3 | chr9:116087694-116175363 |
| 21210 | Tgfbr3 | NM_011578.3 | chr5:107106569-107289595 |
| 21211 | Tgfbrap1 | NM_001013025.2 | chr1:43047268-43098622 |
| 21212 | Tgif1 | NM_001164074.1 | chr17:70844204-70853532 |
| 21213 | Tgif2 | NM_001291124.1 | chr2:156840606-156855569 |
| 21214 | Tgif2lx1 | NM_153109.1 | chrX:118427234-118480729 |
| 21215 | Tgif2lx2 | NM_001142750.1 | chrX:118427226-118480737 |
| 21216 | Tgm1 | NM_001161714.1 | chr14:55700008-55713492 |
| 21217 | Tgm2 | NM_009373.3 | chr2:158116404-158146392 |
| 21218 | Tgm3 | NM_009374.3 | chr2:130012339-130050399 |
| 21219 | Tgm4 | NM_177911.4 | chr9:123034740-123067558 |
| 21220 | Tgm5 | NM_028799.2 | chr2:121046110-121085759 |
| 21221 | Tgm6 | NM_001289747.1 | chr2:130123274-130154232 |
| 21222 | Tgm7 | NM_001160424.1 | chr2:121093588-121109791 |
| 21223 | Tgoln1 | NM_009443.3 | chr6:72608420-72617000 |
| 21224 | Tgoln2 | NM_009444.1 | chr6:72610956-72616748 |
| 21225 | Tgs1 | NM_054089.4 | chr4:3574878-3616623 |
| 21226 | Tgtp1 | NM_011579.3 | chr11:48985328-48992246 |
| 21227 | Tgtp2 | NM_001145164.1 | chr11:49057195-49064212 |
| 21228 | Th | NM_009377.1 | chr7:142892775-142899966 |
| 21229 | Tha1 | NM_027919.4 | chr11:117867948-117873526 |
| 21230 | Thada | NM_183021.3 | chr17:84190055-84466208 |
| 21231 | Thap1 | NM_199042.2 | chr8:26158168-26164151 |
| 21232 | Thap11 | NM_021513.2 | chr8:105855102-105856950 |
| 21233 | Thap2 | NM_025780.3 | chr10:115369965-115384435 |
| 21234 | Thap3 | NM_001145929.1 | chr4:151982637-151988986 |
| 21235 | Thap4 | NM_025920.3 | chr1:93705390-93754838 |
| 21236 | Thap6 | NR_028429.1 | chr5:91962881-91972137 |
| 21237 | Thap7 | NM_026909.2 | chr16:17527981-17531052 |
| 21238 | Thbd | NM_009378.3 | chr2:148404470-148408188 |
| 21239 | Thbs1 | NM_011580.4 | chr2:118111875-118127133 |
| 21240 | Thbs2 | NM_011581.3 | chr17:14665499-14694262 |
| 21241 | Thbs3 | NM_013691.2 | chr3:89215186-89226837 |
| 21242 | Thbs4 | NM_011582.3 | chr13:92751585-92794818 |
| 21243 | Theg | NM_011583.3 | chr10:79576476-79587136 |
| 21244 | Them4 | NM_029431.1 | chr3:94310131-94332532 |
| 21245 | Them5 | NM_025416.3 | chr3:94342098-94347352 |
| 21246 | Them6 | NM_198607.1 | chr15:74721233-74724373 |
| 21247 | Them7 | NM_001159638.1 | chr2:105224341-105379860 |
| 21248 | Themis | NM_178666.6 | chr10:28668359-28833818 |
| 21249 | Themis2 | NM_001033308.2 | chr4:132782356-132796364 |
| 21250 | Themis3 | NM_028998.1 | chr17:66555251-66594622 |
| 21251 | Thg1l | NM_001080969.3 | chr11:45945305-45955503 |
| 21252 | Thnsl1 | NM_001001297.2 | chr2:21205723-21215009 |
| 21253 | Thnsl2 | NM_001033929.2 | chr6:71128165-71144380 |
| 21254 | Thoc1 | NM_153552.3 | chr18:9958179-9995484 |
| 21255 | Thoc2 | NM_001033422.1 | chrX:41794993-41911901 |
| 21256 | Thoc3 | NM_028597.3 | chr13:54458836-54468840 |
| 21257 | Thoc5 | NM_172438.3 | chr11:4895342-4928865 |
| 21258 | Thoc6 | NM_001084251.1 | chr17:23668618-23673770 |
| 21259 | Thoc7 | NM_001285780.1 | chr14:13994001-13961313 |
| 21260 | Thop1 | NM_022653.4 | chr10:81070082-81082360 |
| 21261 | Thpo | NM_001173505.1 | chr16:20724453-20730598 |
| 21262 | Thra | NM_178060.4 | chr11:98741784-98765113 |
| 21263 | Thrap3 | NM_146153.3 | chr4:126164082-126220710 |
| 21264 | Thrb | NM_001113417.1 | chr14:17660959-18038088 |
| 21265 | Thrsp | NM_009381.2 | chr7:97412956-97417510 |
| 21266 | Thsd1 | NM_001205253.1 | chr8:22227302-22261332 |
| 21267 | Thsd4 | NM_001040426.2 | chr9:59966930-60511035 |
| 21268 | Thsd7a | NM_001164805.1 | chr6:12311607-12749253 |
| 21269 | Thsd7b | NM_172485.3 | chr1:129273303-130219278 |
| 21270 | Thtpa | NM_153083.5 | chr14:55094783-55098995 |
| 21271 | Thumpd1 | NM_145585.2 | chr7:119715093-119720798 |

Fig. 26 - 113

| | | | | | | | |
|---|---|---|---|---|---|---|---|
| 21272 | Thumpd2 | NM_028138.1 | chr17:81026326-81065085 | 21367 | Tm6sf1 | NM_001291282.1 | chr7:81862686-81884079 |
| 21273 | Thumpd3 | NM_008188.2 | chr6:113046326-113068273 | 21368 | Tm6sf2 | NM_183540.4 | chr8:70072923-70080066 |
| 21274 | Thy1 | NM_009382.3 | chr9:44043383-44048579 | 21369 | Tm7sf2 | NM_028454.2 | chr19:6062820-6067850 |
| 21275 | Thyn1 | NM_144543.2 | chr9:26999676-27007334 | 21370 | Tm7sf3 | NM_026281.2 | chr6:146602275-146634592 |
| 21276 | Tia1 | NM_001164078.1 | chr6:86404218-86433405 | 21371 | Tm9sf1 | NM_028780.3 | chr14:55635965-55643806 |
| 21277 | Tial1 | NM_009383.2 | chr7:128439776-128461513 | 21372 | Tm9sf2 | NM_080556.3 | chr14:122107081-122159603 |
| 21278 | Tiam1 | NM_001145886.1 | chr16:89787110-89974699 | 21373 | Tm9sf3 | NM_133352.2 | chr19:41210841-41264004 |
| 21279 | Tiam2 | NM_001122998.1 | chr17:3326572-3519397 | 21374 | Tm9sf4 | NM_133847.3 | chr2:153161300-153210463 |
| 21280 | Ticam1 | NM_174989.4 | chr17:56269461-56276767 | 21375 | Tma16 | NM_025465.2 | chr8:66476345-66486507 |
| 21281 | Ticam2 | NM_173394.3 | chr18:46558236-46574533 | 21376 | Tma7 | NM_183250.2 | chr9:109077987-109082381 |
| 21282 | Ticrr | NM_029835.1 | chr7:79660195-79698145 | 21377 | Tmbim1 | NM_027154.5 | chr1:74288246-74304336 |
| 21283 | Tie1 | NM_011587.2 | chr4:118471190-118489849 | 21378 | Tmbim4 | NM_026617.3 | chr10:120208825-120224897 |
| 21284 | Tifa | NM_145133.3 | chr3:127789912-127798389 | 21379 | Tmbim6 | NM_001171034.1 | chr15:99392946-99410049 |
| 21285 | Tifab | NM_001168615.1 | chr3:56173702-56178885 | 21380 | Tmbim7 | NM_029141.4 | chr5:3657003-3679544 |
| 21286 | Tigd2 | NM_001081145.1 | chr6:59208869-59212033 | 21381 | Tmc1 | NM_028953.2 | chr19:20783457-20954202 |
| 21287 | Tigd3 | NM_198634.1 | chr19:5891137-5894107 | 21382 | Tmc2 | NM_138655.1 | chr2:130195193-130264445 |
| 21288 | Tigd4 | NM_207278.2 | chr3:84593573-84597032 | 21383 | Tmc3 | NM_177695.4 | chr7:83584930-83623709 |
| 21289 | Tigd5 | NM_178646.4 | chr15:75909734-75914535 | 21384 | Tmc4 | NM_181820.2 | chr7:3665753-3677553 |
| 21290 | Tigit | NM_001146325.1 | chr16:43648860-43664184 | 21385 | Tmc5 | NM_001105252.1 | chr7:118597296-118675085 |
| 21291 | Timd2 | NM_001161355.1 | chr11:46668959-46698830 | 21386 | Tmc6 | NM_145439.2 | chr11:117765984-117780683 |
| 21292 | Timd4 | NM_178759.4 | chr11:46810798-46844333 | 21387 | Tmc7 | NM_172476.4 | chr7:118535843-118584686 |
| 21293 | Timeless | NM_001136082.2 | chr10:128232062-128252941 | 21388 | Tmc8 | NM_001195088.1 | chr11:117782657-117793137 |
| 21294 | Timm10 | NM_013899.2 | chr2:84827020-84830213 | 21389 | Tmcc1 | NM_177412.1 | chr6:116018617-116193374 |
| 21295 | Timm10b | NM_019502.2 | chr7:105640539-105641845 | 21390 | Tmcc2 | NM_178874.3 | chr1:132356314-132391386 |
| 21296 | Timm13 | NM_013895.4 | chr10:80990449-80990969 | 21391 | Tmcc3 | NM_001168684.1 | chr10:94575256-94590954 |
| 21297 | Timm17a | NM_011590.2 | chr1:135301534-135313737 | 21392 | Tmco1 | NM_001039483.1 | chr1:167308669-167333978 |
| 21298 | Timm17b | NM_011591.5 | chrX:7899335-7907652 | 21393 | Tmco2 | NM_001081312.1 | chr4:121105650-121109226 |
| 21299 | Timm21 | NM_025969.4 | chr18:84947293-84951524 | 21394 | Tmco3 | NM_172282.2 | chr8:13288012-13322924 |
| 21300 | Timm22 | NM_001291161.1 | chr11:76406924-76416313 | 21395 | Tmco4 | NM_029857.3 | chr4:138972904-139059171 |
| 21301 | Timm23 | NM_016897.3 | chr14:32180165-32201891 | 21396 | Tmco5 | NM_026104.4 | chr2:116878690-116892500 |
| 21302 | Timm44 | NM_011652.2 | chr8:4259730-4275905 | 21397 | Tmco5b | NM_029232.2 | chr2:113285731-113297190 |
| 21303 | Timm50 | NM_025616.3 | chr7:28305825-28312046 | 21398 | Tmco6 | NM_028036.3 | chr18:36735069-36742391 |
| 21304 | Timm8a1 | NM_013898.3 | chrX:11609223-134541670 | 21399 | Tmed1 | NM_010744.3 | chr9:21507379-21510186 |
| 21305 | Timm8a2 | NM_001077744.1 | chr14:122034673-122038422 | 21400 | Tmed10 | NM_026775.4 | chr12:85340613-85374717 |
| 21306 | Timm8b | NM_013897.2 | chr9:50603900-50605320 | 21401 | Tmed11 | NM_026109.2 | chr5:108777234-108795363 |
| 21307 | Timm9 | NM_001024853.1 | chr12:71123171-71136675 | 21402 | Tmed2 | NM_019770.2 | chr5:124540790-124550603 |
| 21308 | Timmdc1 | NM_024273.2 | chr16:38497842-38522663 | 21403 | Tmed3 | NM_025360.2 | chr9:89699292-89705043 |
| 21309 | Timp1 | NM_001044384.1 | chrX:20870165-20874737 | 21404 | Tmed4 | NM_134020.1 | chr11:6270713-6274837 |
| 21310 | Timp2 | NM_011594.3 | chr11:118301060-118355411 | 21405 | Tmed5 | NM_028876.2 | chr5:108121646-108132591 |
| 21311 | Timp3 | NM_011595.2 | chr10:86300411-86349505 | 21406 | Tmed6 | NM_025458.2 | chr8:107061483-107065644 |
| 21312 | Timp4 | NM_080639.3 | chr6:115245615-115251849 | 21407 | Tmed7 | NM_025698.1 | chr18:46585927-46597535 |
| 21313 | Tinag | NM_021324.3 | chr9:76951697-77045781 | 21408 | Tmed8 | NM_001033475.3 | chr12:87166241-87200229 |
| 21314 | Tinagl1 | NM_001168333.1 | chr4:130165599-130174802 | 21409 | Tmed9 | NM_026211.3 | chr13:55593134-55597694 |
| 21315 | Tinf2 | NM_145705.3 | chr14:55679079-55681817 | 21410 | Tmeff1 | NM_021436.2 | chr4:48585192-48663131 |
| 21316 | Tiparp | NM_178892.5 | chr3:65528446-65555518 | 21411 | Tmeff2 | NM_019790.4 | chr5:S0927522-51187270 |
| 21317 | Tipin | NM_025372.3 | chr9:64281606-64304792 | 21412 | Tmem100 | NM_026433.2 | chr11:90030347-90036505 |
| 21318 | Tipr1 | NM_145513.4 | chr1:165212285-165236958 | 21413 | Tmem101 | NM_029649.2 | chr11:102152546-102156407 |
| 21319 | Tirap | NM_001177845.1 | chr9:35184390-35200291 | 21414 | Tmem102 | NM_001034433.4 | chr11:69803594-69805624 |
| 21320 | Tjap1 | NM_001252473.1 | chr17:46257850-46283026 | 21415 | Tmem104 | NM_001033393.2 | chr11:115187486-115247025 |
| 21321 | Tjp1 | NM_001163574.1 | chr7:65296164-65371244 | 21416 | Tmem106a | NM_144830.3 | chr11:101582241-101591785 |
| 21322 | Tjp2 | NM_001198985.1 | chr19:24094501-24174140 | 21417 | Tmem106b | NM_027992.3 | chr13:1306975B-13089269 |
| 21323 | Tjp3 | NM_001282095.1 | chr10:81273187-81291581 | 21418 | Tmem106c | NM_001252153.1 | chr15:97964228-97970286 |
| 21324 | Tk1 | NM_001171729.1 | chr11:117815518-117826014 | 21419 | Tmem107 | NM_025838.2 | chr11:69070808-69073293 |
| 21325 | Tk2 | NM_021028.3 | chr8:104226690-104248558 | 21420 | Tmem108 | NM_178638.4 | chr9:103482935-103761837 |
| 21326 | Tkt | NM_009388.6 | chr14:30549130-30574726 | 21421 | Tmem109 | NM_134142.1 | chr19:10870660-10881743 |
| 21327 | Tktl1 | NM_031379.2 | chrX:74177258-74208498 | 21422 | Tmem11 | NM_001168507.1 | chr11:60864451-80879038 |
| 21328 | Tktl2 | NM_001271574.1 | chr8:66511739-66519199 | 21423 | Tmem110 | NM_028839.4 | chr14:30825593-30877210 |
| 21329 | Tlcd1 | NM_001291235.1 | chr11:78178148-78180819 | 21424 | Tmem115 | NM_019704.2 | chr9:107533944-107538656 |
| 21330 | Tlcd2 | NM_001291156.1 | chr11:75468049-75470899 | 21425 | Tmem116 | NM_001161626.1 | chr5:121463180-121495421 |
| 21331 | Tldc1 | NM_028883.2 | chr8:119760586-119778416 | 21426 | Tmem117 | NM_178789.4 | chr15:94629184-95096097 |
| 21332 | Tldc2 | NM_001177439.1 | chr2:157087054-157096481 | 21427 | Tmem119 | NM_146162.2 | chr5:113793728-113800352 |
| 21333 | Tle1 | NM_001285529.1 | chr4:72109944-72200893 | 21428 | Tmem120a | NM_172541.2 | chr5:135735489-135744172 |
| 21334 | Tle2 | NM_001252401.1 | chr10:81575286-81590473 | 21429 | Tmem120b | NM_001039723.2 | chr5:123076274-123117445 |
| 21335 | Tle3 | NM_001083927.1 | chr9:61372365-61418497 | 21430 | Tmem121 | NM_153776.2 | chr12:113185902-113189522 |
| 21336 | Tle4 | NM_011600.3 | chr19:14448071-14598183 | 21431 | Tmem123 | NM_133739.2 | chr9:7764076-7794332 |
| 21337 | Tle6 | NM_053254.2 | chr10:81590904-81600900 | 21432 | Tmem125 | NM_172383.3 | chr4:118540940-118543726 |
| 21338 | Tlk1 | NM_172664.3 | chr2:70712407-70825480 | 21433 | Tmem126a | NM_025460.2 | chr7:90450711-90457208 |
| 21339 | Tlk2 | NM_001112705.2 | chr11:105181526-105283959 | 21434 | Tmem126b | NM_026734.1 | chr7:90468828-90475995 |
| 21340 | Tll1 | NM_009390.2 | chr8:64014769-64205993 | 21435 | Tmem127 | NM_175145.3 | chr2:127147974-127260764 |
| 21341 | Tll2 | NM_011083980.1 | chr19:41083980-41206774 | 21436 | Tmem128 | NM_025480.3 | chr5:38260374-38269618 |
| 21342 | Tln1 | NM_011602.5 | chr4:43531512-43562583 | 21437 | Tmem129 | NM_026698.2 | chr5:33653215-33657832 |
| 21343 | Tln2 | NM_001081242.2 | chr9:67217084-67559703 | 21438 | Tmem130 | NM_177735.4 | chr5:144735914-144761578 |
| 21344 | Tlr1 | NM_030682.1 | chr5:64924679-64933658 | 21439 | Tmem131 | NM_018872.2 | chr1:36792188-36939527 |
| 21345 | Tlr11 | NM_205819.3 | chr14:50357913-50363663 | 21440 | Tmem132a | NM_133804.2 | chr19:10857628-10869779 |
| 21346 | Tlr12 | NM_205823.2 | chr4:128615446-128618619 | 21441 | Tmem132b | NM_001190352.1 | chr5:125532417-125792583 |
| 21347 | Tlr13 | NM_205820.1 | chrX:106143274-106160493 | 21442 | Tmem132c | NM_175432.3 | chr5:127241525-127565790 |
| 21348 | Tlr2 | NM_011905.3 | chr3:83836271-83841608 | 21443 | Tmem132cos | NR_038127.1 | chr5:127256859-127281623 |
| 21349 | Tlr3 | NM_126166.4 | chr8:45395664-45410539 | 21444 | Tmem132d | NM_172885.2 | chr5:127783490-128433077 |
| 21350 | Tlr4 | NM_021297.3 | chr4:66827550-66846581 | 21445 | Tmem132e | NM_001304439.1 | chr11:82387446-82447618 |
| 21351 | Tlr5 | NM_016928.3 | chr1:182954787-182976044 | 21446 | Tmem134 | NM_001078649.1 | chr19:41255959-4132307 |
| 21352 | Tlr6 | NM_011604.3 | chr5:64953094-64960034 | 21447 | Tmem135 | NM_028343.4 | chr7:89134720-89338787 |
| 21353 | Tlr7 | NM_001290755.1 | chrX:167304925-167330571 | 21448 | Tmem136 | NM_001034863.3 | chr9:43108652-43116570 |
| 21354 | Tlr8 | NM_133212.3 | chrX:167241122-167264329 | 21449 | Tmem138 | NM_028411.4 | chr19:10570477-10577386 |
| 21355 | Tlr9 | NM_031178.2 | chr9:106222597-106226876 | 21450 | Tmem139 | NM_175408.4 | chr6:42261969-42264555 |
| 21356 | Tlx1 | NM_021300.3 | chr19:45150714-45156943 | 21451 | Tmem140 | NM_197986.2 | chr6:34863145-34874946 |
| 21357 | Tlx2 | NM_009392.2 | chr6:83068324-83070225 | 21452 | Tmem141 | NM_001040130.3 | chr2:25620065-25622002 |
| 21358 | Tlx3 | NM_019916.2 | chr11:33200751-33203588 | 21453 | Tmem143 | NM_144801.2 | chr7:45897068-45917413 |
| 21359 | Tm2d1 | NM_053157.2 | chr4:98355369-98383265 | 21454 | Tmem144 | NM_027495.4 | chr3:79813152-79842662 |
| 21360 | Tm2d2 | NM_027194.3 | chr8:25017310-25023260 | 21455 | Tmem145 | NM_183311.2 | chr7:25306107-25316195 |
| 21361 | Tm2d3 | NM_026795.3 | chr7:65693416-65701913 | 21456 | Tmem147 | NM_027215.2 | chr7:30727700-30729534 |
| 21362 | Tm4sf1 | NM_008536.3 | chr3:57287063-57301919 | 21457 | Tmem147a | NM_001290679.1 | chr1:21218574-21230167 |
| 21363 | Tm4sf19 | NM_001160402.1 | chr16:32400505-32408227 | 21458 | Tmem14c | NM_025387.3 | chr13:41016249-41022582 |
| 21364 | Tm4sf20 | NM_025453.3 | chr1:82756648-82768456 | 21459 | Tmem150a | NM_144916.3 | chr6:72355482-72359762 |
| 21365 | Tm4sf4 | NM_145539.2 | chr3:57425409-57441675 | 21460 | Tmem150b | NM_001142792.1 | chr7:4716001-4725082 |
| 21366 | Tm4sf5 | NM_029360.3 | chr11:70505273-70511183 | 21461 | Tmem150c | NM_182841.1 | chr5:100077872-100159808 |

Fig. 26 - 114

| | | | | | | | | |
|---|---|---|---|---|---|---|---|---|
| 21462 | Tmem156os | NR_045993.1 | chr5:100077961-100095273 | | 21557 | Tmem242 | NM_027457.4 | chr17:5410863-5440260 |
| 21463 | Tmem151a | NM_001001885.1 | chr19:5079336-5085477 | | 21558 | Tmem243 | NM_001081029.1 | chr5:9100736-9118983 |
| 21464 | Tmem151b | NM_001013749.2 | chr17:45541939-45549677 | | 21559 | Tmem245 | NM_175518.5 | chr4:56876012-56947429 |
| 21465 | Tmem154 | NM_177260.2 | chr3:84666191-84704575 | | 21560 | Tmem246 | NM_025944.3 | chr4:49584505-49597870 |
| 21466 | Tmem158 | NM_001002267.2 | chr9:123259056-123260789 | | 21561 | Tmem247 | NM_001277980.1 | chr17:86917347-86922367 |
| 21467 | Tmem159 | NM_145586.1 | chr7:120102425-120120986 | | 21562 | Tmem248 | NM_001081394.1 | chr5:130219743-130243765 |
| 21468 | Tmem160 | NM_026938.1 | chr7:16452778-16455490 | | 21563 | Tmem25 | NM_027865.2 | chr9:44793778-44799216 |
| 21469 | Tmem161a | NM_145597.4 | chr8:70172407-70183681 | | 21564 | Tmem251 | NM_177140.3 | chr12:102743759-102745397 |
| 21470 | Tmem161b | NM_175187.5 | chr13:84222295-84295966 | | 21565 | Tmem252 | NM_183160.3 | chr19:24674007-24679661 |
| 21471 | Tmem163 | NM_028135.2 | chr1:127490341-127678021 | | 21566 | Tmem253 | NM_001033805.3 | chr14:52016864-52019787 |
| 21472 | Tmem164 | NM_001199357.1 | chrX:142681399-142843494 | | 21567 | Tmem254a | NM_025311.3 | chr14:25923297-26206619 |
| 21473 | Tmem165 | NM_011626.2 | chr5:76183879-76209244 | | 21568 | Tmem254b | NM_001270495.1 | chr14:25923996-26207025 |
| 21474 | Tmem167 | NM_025335.3 | chr13:90089666-90114921 | | 21569 | Tmem254c | NM_001270498.1 | chr14:25923997-26207041 |
| 21475 | Tmem167b | NM_026369.2 | chr3:108556424-108562466 | | 21570 | Tmem255a | NM_001289727.1 | chrX:38196572-38252481 |
| 21476 | Tmem168 | NM_028990.4 | chr6:13580688-13608063 | | 21571 | Tmem255b | NM_001143671.1 | chr8:13435458-13461451 |
| 21477 | Tmem169 | NM_175564.4 | chr1:72284372-72302995 | | 21572 | Tmem256 | NM_026982.1 | chr11:69838524-69839558 |
| 21478 | Tmem17 | NM_153596.3 | chr11:22512282-22519231 | | 21573 | Tmem258 | NM_001163431.1 | chr19:10206032-10207824 |
| 21479 | Tmem170 | NM_025781.2 | chr8:111864897-111876675 | | 21574 | Tmem259 | NM_001003949.3 | chr10:79977119-79984330 |
| 21480 | Tmem170b | NM_001163572.1 | chr13:41606215-41641357 | | 21575 | Tmem26 | NM_177794.3 | chr10:68723745-68782654 |
| 21481 | Tmem171 | NM_001025606.1 | chr13:98686237-98694831 | | 21576 | Tmem260 | NM_172600.4 | chr14:48446351-48515130 |
| 21482 | Tmem173 | NM_001289591.1 | chr18:35733677-35740554 | | 21577 | Tmem261 | NM_025849.3 | chr4:75277353-75278286 |
| 21483 | Tmem174 | NM_026065.2 | chr13:98634977-98637410 | | 21578 | Tmem263 | NM_001013028.2 | chr10:85102626-85117747 |
| 21484 | Tmem175 | NM_001163531.1 | chr5:108629809-108647770 | | 21579 | Tmem27 | NM_020626.2 | chrX:164096186-164118859 |
| 21485 | Tmem176a | NM_001098271.1 | chr6:48841655-48845364 | | 21580 | Tmem28 | NM_001081283.1 | chrX:99821058-99846345 |
| 21486 | Tmem176b | NM_001164207.1 | chr6:48833811-48841374 | | 21581 | Tmem29 | NM_001164683.1 | chrX:150397772-150459150 |
| 21487 | Tmem177 | NM_175106.3 | chr1:119907898-119913168 | | 21582 | Tmem30a | NM_133718.4 | chr9:79768940-79793430 |
| 21488 | Tmem178 | NM_026516.2 | chr17:80944631-81001816 | | 21583 | Tmem30b | NM_178715.3 | chr12:73543113-73546395 |
| 21489 | Tmem178b | NM_001004182.3 | chr6:40110252-40248353 | | 21584 | Tmem30c | NM_027651.1 | chr16:57266138-57292851 |
| 21490 | Tmem179 | NM_178915.3 | chr12:112500183-112511160 | | 21585 | Tmem33 | NM_001285452.1 | chr5:67260564-67291461 |
| 21491 | Tmem179b | NM_026325.3 | chr19:8772521-8774467 | | 21586 | Tmem35 | NM_026239.2 | chrX:134295224-134305969 |
| 21492 | Tmem18 | NM_172049.2 | chr12:30584442-30591219 | | 21587 | Tmem37 | NM_019432.2 | chr1:120067376-120073780 |
| 21493 | Tmem180 | NM_029186.2 | chr19:46356879-46375254 | | 21588 | Tmem38a | NM_144534.1 | chr8:72572102-72587284 |
| 21494 | Tmem181a | NM_001033178.3 | chr17:6270469-6308314 | | 21589 | Tmem38b | NM_028053.2 | chr4:53826044-53862018 |
| 21495 | Tmem181b-ps | NR_033520.1 | chr17:6439001-6450994 | | 21590 | Tmem39a | NM_001205286.1 | chr16:38558697-38592162 |
| 21496 | Tmem181c-ps | NR_028305.2 | chr17:6610102-6620925 | | 21591 | Tmem39b | NM_199305.3 | chr4:129676354-129696838 |
| 21497 | Tmem182 | NM_001081198.1 | chr6:115729136-115762466 | | 21592 | Tmem40 | NM_001168256.1 | chr6:115729136-115762466 |
| 21498 | Tmem183a | NM_001042485.1 | chr1:134846096-134861999 | | 21593 | Tmem41a | NM_025693.4 | chr16:21934326-21947552 |
| 21499 | Tmem184a | NM_001161548.1 | chr5:139804951-139814283 | | 21594 | Tmem41b | NM_153525.5 | chr7:109972186-109986230 |
| 21500 | Tmem184b | NM_001213317.1 | chr15:79360683-79402919 | | 21595 | Tmem42 | NM_001164823.1 | chr9:123021325-123023491 |
| 21501 | Tmem184c | NM_145599.4 | chr8:77595977-77610653 | | 21596 | Tmem43 | NM_028766.2 | chr6:91473750-91488458 |
| 21502 | Tmem185b | NM_146103.2 | chr1:119526153-119528983 | | 21597 | Tmem44 | NM_172614.3 | chr16:30511854-30550578 |
| 21503 | Tmem186 | NM_025704.4 | chr16:8633730-8637701 | | 21598 | Tmem45a | NM_019631.3 | chr16:56805160-56886163 |
| 21504 | Tmem189 | NM_145538.2 | chr2:167643224-167661544 | | 21599 | Tmem45b | NM_144936.1 | chr9:31426195-31464238 |
| 21505 | Tmem19 | NM_133683.3 | chr10:115340739-115362262 | | 21600 | Tmem47 | NM_138751.2 | chrX:81070643-81097875 |
| 21506 | Tmem190 | NM_030028.1 | chr7:4782939-4784340 | | 21601 | Tmem5 | NM_153059.1 | chr10:122081259-122097102 |
| 21507 | Tmem191c | NM_177473.3 | chr16:17276299-17278661 | | 21602 | Tmem50a | NM_029335.2 | chr4:134897848-134914916 |
| 21508 | Tmem192 | NM_001163747.1 | chr8:64947184-64969037 | | 21603 | Tmem50b | NM_030018.3 | chr16:91574507-91597680 |
| 21509 | Tmem194 | NM_001113211.1 | chr10:127677064-127701047 | | 21604 | Tmem51 | NM_145402.3 | chr4:142030992-142084304 |
| 21510 | Tmem194b | NM_001142647.1 | chr11:52630704-52651919 | | 21605 | Tmem51os1 | NR_027137.1 | chr4:142084297-142088101 |
| 21511 | Tmem196 | NM_001160385.2 | chr12:119945961-120021245 | | 21606 | Tmem52 | NM_001253856.1 | chr4:155469113-155470858 |
| 21512 | Tmem198 | NM_177955.4 | chr1:75479531-75485693 | | 21607 | Tmem52b | NM_001081186.1 | chr5:129512556-129519227 |
| 21513 | Tmem198b | NM_178066.2 | chr10:128800035-128804370 | | 21608 | Tmem53 | NM_001285812.1 | chr4:117251950-117268588 |
| 21514 | Tmem199 | NM_199199.3 | chr11:78507054-78512168 | | 21609 | Tmem54 | NM_001290706.1 | chr4:129105547-129111624 |
| 21515 | Tmem2 | NM_001033759.2 | chr19:21778339-21858360 | | 21610 | Tmem55a | NM_028264.4 | chr4:14864218-14915260 |
| 21516 | Tmem200a | NM_029881.3 | chr10:25991185-26079052 | | 21611 | Tmem55b | NM_001033271.5 | chr14:50927214-50930849 |
| 21517 | Tmem200b | NM_001201367.1 | chr4:131921770-131923140 | | 21612 | Tmem56 | NM_178936.3 | chr3:121202009-121263316 |
| 21518 | Tmem200c | NM_001206661.1 | chr17:68837135-68843138 | | 21613 | Tmem57 | NM_025382.6 | chr4:134802759-134853345 |
| 21519 | Tmem201 | NM_001284270.1 | chr4:149715374-149738068 | | 21614 | Tmem59 | NM_029565.3 | chr4:107178629-107200996 |
| 21520 | Tmem202 | NM_178388.2 | chr9:59518684-59525501 | | 21615 | Tmem59l | NM_182991.2 | chr8:70483866-70487358 |
| 21521 | Tmem203 | NM_177344.3 | chr2:25255438-25256352 | | 21616 | Tmem60 | NM_177601.3 | chr5:20882452-20886870 |
| 21522 | Tmem204 | NM_001001183.1 | chr17:25057701-25081114 | | 21617 | Tmem62 | NM_175285.3 | chr2:120977961-121007842 |
| 21523 | Tmem205 | NM_001201253.1 | chr9:21921008-21927535 | | 21618 | Tmem63a | NM_144794.2 | chr1:180942517-180975104 |
| 21524 | Tmem206 | NM_025864.3 | chr1:191325964-191352925 | | 21619 | Tmem63b | NM_198167.3 | chr17:45660176-45686218 |
| 21525 | Tmem207 | NM_001101640.1 | chr16:26503792-26526771 | | 21620 | Tmem63c | NM_172583.2 | chr12:87026563-87090039 |
| 21526 | Tmem208 | NM_025486.2 | chr8:105326363-105329057 | | 21621 | Tmem64 | NM_181401.3 | chr4:15265819-15286753 |
| 21527 | Tmem209 | NM_178625.4 | chr6:30481232-30509783 | | 21622 | Tmem65 | NM_175212.4 | chr15:58782268-58823427 |
| 21528 | Tmem210 | NM_030055.1 | chr2:25288144-25289187 | | 21623 | Tmem66 | NM_026432.3 | chr8:34154562-34170847 |
| 21529 | Tmem211 | NM_001033428.2 | chr5:113226908-113239263 | | 21624 | Tmem67 | NM_177861.4 | chr4:12039355-12087957 |
| 21530 | Tmem212 | NM_001164437.1 | chr3:278866064-27896368 | | 21625 | Tmem68 | NM_028097.3 | chr4:3549040-3574768 |
| 21531 | Tmem213 | NM_029921.1 | chr6:38109352-38115806 | | 21626 | Tmem69 | NM_177670.4 | chr4:116551527-116555943 |
| 21532 | Tmem214 | NM_144525.3 | chr5:30869646-30877467 | | 21627 | Tmem70 | NM_026392.1 | chr1:16665190-16678275 |
| 21533 | Tmem215 | NM_001166009.1 | chr4:40473129-40475653 | | 21628 | Tmem71 | NM_172514.3 | chr15:66526211-66561046 |
| 21534 | Tmem216 | NM_001201367.1 | chr19:10550460-10555763 | | 21629 | Tmem72 | NM_178768.4 | chr6:116692724-116716758 |
| 21535 | Tmem217 | NM_001162901.1 | chr17:29526017-29549593 | | 21630 | Tmem74 | NM_175502.3 | chr15:43886694-43870029 |
| 21536 | Tmem218 | NM_025464.3 | chr9:37208222-37223228 | | 21631 | Tmem74b | NM_001160363.1 | chr2:151702007-151707310 |
| 21537 | Tmem219 | NM_026821.1 | chr7:126886218-126896278 | | 21632 | Tmem79 | NM_024246.5 | chr3:88328652-88334433 |
| 21538 | Tmem220 | NM_001021042.1 | chr11:67025153-67040312 | | 21633 | Tmem8 | NM_021793.2 | chr17:26113315-26123253 |
| 21539 | Tmem221 | NM_001100462.1 | chr8:71554302-71558871 | | 21634 | Tmem80 | NM_001141950.1 | chr7:141328129-141337155 |
| 21540 | Tmem222 | NM_025867.3 | chr4:133266044-133277790 | | 21635 | Tmem81 | NM_029025.3 | chr1:132506229-132508639 |
| 21541 | Tmem223 | NM_025791.1 | chr19:8770995-8772475 | | 21636 | Tmem82 | NM_145987.2 | chr4:141614232-141618633 |
| 21542 | Tmem225 | NM_029379.1 | chr9:40148121-40150878 | | 21637 | Tmem86a | NM_026436.3 | chr7:47050639-47054776 |
| 21543 | Tmem229a | NM_177013.3 | chr6:24951140-24956125 | | 21638 | Tmem86b | NM_023440.2 | chr7:4628039-4630482 |
| 21544 | Tmem229b | NM_001170401.1 | chr12:78961794-78983478 | | 21639 | Tmem87a | NM_001110496.1 | chr2:120355308-120404116 |
| 21545 | Tmem230 | NM_001141971.1 | chr2:132239491-132247788 | | 21640 | Tmem87b | NM_028248.2 | chr2:128818302-128854261 |
| 21546 | Tmem231 | NM_001133321.1 | chr8:111912017-111933791 | | 21641 | Tmem88 | NM_029915.4 | chr11:69396515-69398234 |
| 21547 | Tmem232 | NM_001608973.2 | chr17:65256004-65540782 | | 21642 | Tmem88b | NM_001033394.3 | chr4:155781550-155785874 |
| 21548 | Tmem233 | NM_001001546.1 | chr5:116040533-116083246 | | 21643 | Tmem89 | NM_027066.1 | chr9:108914618-108915563 |
| 21549 | Tmem234 | NM_029748.2 | chr4:129600706-129607879 | | 21644 | Tmem8b | NM_001085508.2 | chr4:43668970-43692667 |
| 21550 | Tmem235 | NM_001085535.1 | chr1:117860751-117865548 | | 21645 | Tmem8c | NM_001159602.1 | chr2:27061635-27067868 |
| 21551 | Tmem236 | NM_001081310.2 | chr2:14174523-14221893 | | 21646 | Tmem9 | NM_001160145.1 | chr1:136008218-136035030 |
| 21552 | Tmem237 | NM_001033449.1 | chr1:59100592-59120096 | | 21647 | Tmem91 | NM_001290497.1 | chr7:25669139-25675166 |
| 21553 | Tmem238 | NM_029384.1 | chr7:4784784-4789560 | | 21648 | Tmem92 | NM_001034896.2 | chr11:94777216-94782703 |
| 21554 | Tmem239 | NM_025753.3 | chr2:130406521-130407794 | | 21649 | Tmem95 | NM_001195710.1 | chr11:69876683-69878018 |
| 21555 | Tmem240 | NM_001101506.1 | chr4:155734803-155740564 | | 21650 | Tmem97 | NM_133706.2 | chr11:78541816-78550735 |
| 21556 | Tmem241 | NM_001289666.1 | chr18:11981302-12121537 | | 21651 | Tmem98 | NM_029537.1 | chr11:80810414-80822033 |

Fig. 26 - 115

| | | | |
|---|---|---|---|
| 21652 | Tmem9b | NM_020050.1 | chr7:109735835-109752263 |
| 21653 | Tmevpg1 | NR_104123.1 | chr10:118502034-118556525 |
| 21654 | Tmf1 | NM_001081111.2 | chr6:97151949-97179124 |
| 21655 | Tmie | NM_146260.2 | chr9:110866045-110880083 |
| 21656 | Tmigd1 | NM_025655.2 | chr11:76904544-76916586 |
| 21657 | Tmlhe | NM_138758.1 | chrX_GL456233_random:159646-334187 |
| 21658 | Tmod1 | NM_021883.2 | chr4:46089221-46116032 |
| 21659 | Tmod2 | NM_001038710.1 | chr9:75565621-75599133 |
| 21660 | Tmod3 | NM_016963.2 | chr9:75497783-75559657 |
| 21661 | Tmod4 | NM_016712.3 | chr3:95124513-95129208 |
| 21662 | Tmpo | NM_001080129.2 | chr10:91147570-91171619 |
| 21663 | Tmppe | NM_001200002.1 | chr9:114401094-114411201 |
| 21664 | Tmprss11a | NM_001033233.2 | chr5:86410409-86468990 |
| 21665 | Tmprss11bnl | NM_177024.4 | chr5:86659521-86676298 |
| 21666 | Tmprss11c | NM_001030297.2 | chr5:86231480-86289308 |
| 21667 | Tmprss11d | NM_145561.2 | chr5:86302853-86373387 |
| 21668 | Tmprss11e | NM_172880.2 | chr5:86705185-86745807 |
| 21669 | Tmprss11f | NM_178730.3 | chr5:86521225-86632424 |
| 21670 | Tmprss11g | NM_177182.4 | chr5:86485876-86518600 |
| 21671 | Tmprss12 | NM_183109.3 | chr15:100280836-100293053 |
| 21672 | Tmprss13 | NM_001013373.2 | chr9:45319099-45347580 |
| 21673 | Tmprss15 | NM_008941.3 | chr16:78953007-79091097 |
| 21674 | Tmprss2 | NM_015775.2 | chr16:97564681-97611195 |
| 21675 | Tmprss3 | NM_001163776.1 | chr17:31179267-31198974 |
| 21676 | Tmprss4 | NM_145403.2 | chr9:45172725-45204075 |
| 21677 | Tmprss5 | NM_030709.2 | chr9:49102778-49117587 |
| 21678 | Tmprss6 | NM_027902.2 | chr15:78439666-78468634 |
| 21679 | Tmprss7 | NM_172455.3 | chr16:45656316-45693658 |
| 21680 | Tmprss9 | NM_001081688.2 | chr10:80879815-80899494 |
| 21681 | Tmsb10 | NM_001039392.2 | chr6:72957346-72958232 |
| 21682 | Tmsb15a | NM_030106.2 | chrX:135718666-135720673 |
| 21683 | Tmsb15b1 | NM_001081983.1 | chrX:136974021-136976874 |
| 21684 | Tmsb15b2 | NM_001080967.4 | chrX:136954987-136957979 |
| 21685 | Tmsb15l | NM_207267.4 | chrX:136954987-136976874 |
| 21686 | Tmsb4x | NM_021278.2 | chrX:167207093-167209218 |
| 21687 | Tmtc1 | NM_198967.5 | chr6:148232429-148444352 |
| 21688 | Tmtc2 | NM_177368.4 | chr10:105187663-105574479 |
| 21689 | Tmtc3 | NM_001033332.2 | chr10:100448183-100487347 |
| 21690 | Tmtc4 | NM_028651.2 | chr14:122918974-122983261 |
| 21691 | Tmub1 | NM_022418.3 | chr5:24445462-24447846 |
| 21692 | Tmub2 | NM_028076.3 | chr11:102284938-102289427 |
| 21693 | Tmx1 | NM_028339.1 | chr12:70453153-70467624 |
| 21694 | Tmx2 | NM_001290751.1 | chr2:84671310-84678174 |
| 21695 | Tmx3 | NM_198295.2 | chr18:90510153-90543267 |
| 21696 | Tmx4 | NM_029148.1 | chr2:134594501-134644121 |
| 21697 | Tnc | NM_011607.3 | chr4:63959784-64047015 |
| 21698 | Tnf | NM_001278601.1 | chr17:35199366-35202007 |
| 21699 | Tnfaip1 | NM_001159392.1 | chr11:78522849-78536260 |
| 21700 | Tnfaip2 | NM_009396.2 | chr12:111442660-111455018 |
| 21701 | Tnfaip3 | NM_001166402.1 | chr10:19000909-19011963 |
| 21702 | Tnfaip6 | NM_009398.2 | chr2:52038112-52056681 |
| 21703 | Tnfaip8 | NM_001177759.1 | chr18:49979426-50093229 |
| 21704 | Tnfaip8l1 | NM_025566.3 | chr17:56162490-56173955 |
| 21705 | Tnfaip8l2 | NM_027206.2 | chr3:95139520-95142360 |
| 21706 | Tnfaip8l3 | NM_001033535.3 | chr9:54025605-54068411 |
| 21707 | Tnfrsf10b | NM_020275.4 | chr14:69767471-69784411 |
| 21708 | Tnfrsf11a | NM_009399.3 | chr1:105780722-105847981 |
| 21709 | Tnfrsf11b | NM_008764.3 | chr15:54250618-54278484 |
| 21710 | Tnfrsf12a | NM_001161746.1 | chr17:23675444-23677449 |
| 21711 | Tnfrsf13b | NM_021349.1 | chr11:61140834-61147642 |
| 21712 | Tnfrsf13c | NM_028075.2 | chr15:82221743-82224336 |
| 21713 | Tnfrsf14 | NM_178931.2 | chr4:154922209-154928077 |
| 21714 | Tnfrsf17 | NM_011608.1 | chr16:11313808-11320068 |
| 21715 | Tnfrsf18 | NM_009400.2 | chr4:156026341-156028891 |
| 21716 | Tnfrsf19 | NM_001164155.1 | chr14:60963833-61037987 |
| 21717 | Tnfrsf1a | NM_011609.4 | chr6:125349722-125362483 |
| 21718 | Tnfrsf1b | NM_011610.3 | chr4:145212367-145246870 |
| 21719 | Tnfrsf21 | NM_178589.3 | chr17:43016554-43089188 |
| 21720 | Tnfrsf22 | NM_023680.4 | chr7:143644807-143649664 |
| 21721 | Tnfrsf23 | NM_024290.4 | chr7:143665808-143685875 |
| 21722 | Tnfrsf25 | NM_001291010.1 | chr4:152115933-152120119 |
| 21723 | Tnfrsf26 | NM_175649.5 | chr7:143607684-143627845 |
| 21724 | Tnfrsf4 | NM_011659.2 | chr4:156013694-156016589 |
| 21725 | Tnfrsf8 | NM_009401.2 | chr4:145268975-145315147 |
| 21726 | Tnfrsf9 | NM_001077508.1 | chr4:150920154-150946102 |
| 21727 | Tnfsf10 | NM_009425.2 | chr3:27317076-27339665 |
| 21728 | Tnfsf11 | NM_011613.3 | chr14:78277445-78308043 |
| 21729 | Tnfsf12 | NM_011614.3 | chr11:69686239-69696098 |
| 21730 | Tnfsf12Tnfsf13 | NM_001034097.2 | chr11:69682576-69696098 |
| 21731 | Tnfsf13 | NM_001159505.1 | chr11:69682576-69685554 |
| 21732 | Tnfsf13b | NM_033622.1 | chr8:10006632-10035999 |
| 21733 | Tnfsf14 | NM_019418.3 | chr17:57189473-57194181 |
| 21734 | Tnfsf15 | NM_177371.3 | chr4:63724602-63745113 |
| 21735 | Tnfsf18 | NM_183391.3 | chr1:161494656-161505290 |
| 21736 | Tnfsf4 | NM_009452.2 | chr1:161395437-161418206 |
| 21737 | Tnfsf8 | NM_009403.3 | chr4:63832823-63861284 |
| 21738 | Tnfsf9 | NM_009404.3 | chr17:57105384-57107757 |
| 21739 | Tnik | NM_001163007.1 | chr3:28263213-28670585 |
| 21740 | Tnip1 | NM_001199275.2 | chr11:54910786-54962940 |
| 21741 | Tnip2 | NM_139064.2 | chr5:34496095-34513979 |
| 21742 | Tnip3 | NM_001001495.2 | chr6:65590397-65634608 |
| 21743 | Tnk1 | NM_031880.3 | chr11:69850562-69858730 |
| 21744 | Tnk2 | NM_001110147.1 | chr16:32644642-32683493 |
| 21745 | Tnk2os | NR_033493.1 | chr16:32665222-32668197 |
| 21746 | Tnks | NM_175091.3 | chr8:34829178-34965690 |
| 21747 | Tnks1bp1 | NM_001081260.2 | chr2:85050459-85073048 |
| 21748 | Tnks2 | NM_001163635.1 | chr19:36834231-36893477 |
| 21749 | Tnmd | NM_022322.2 | chrX:133851007-133865578 |
| 21750 | Tnn | NM_177839.3 | chr1:160085031-160153575 |
| 21751 | Tnnc1 | NM_009393.2 | chr14:31208311-31211711 |
| 21752 | Tnnc2 | NM_009394.2 | chr2:164777161-164779734 |
| 21753 | Tnni1 | NM_001112702.1 | chr1:135799510-135810989 |
| 21754 | Tnni2 | NM_009405.2 | chr7:142442467-142444405 |
| 21755 | Tnni3 | NM_009406.3 | chr7:4518307-4522443 |
| 21756 | Tnni3k | NM_177066.5 | chr3:154786290-155055407 |
| 21757 | Tnnt1 | NM_001277903.1 | chr7:4504069-4515975 |
| 21758 | Tnnt2 | NM_001130174.2 | chr1:135836333-135852268 |
| 21759 | Tnnt3 | NM_001163664.1 | chr7:142498835-142516009 |
| 21760 | Tnp1 | NM_009407.2 | chr1:73015074-73015899 |
| 21761 | Tnp2 | NM_013694.4 | chr16:10787934-10788655 |
| 21762 | Tnpo1 | NM_001048267.1 | chr13:98842080-98891042 |
| 21763 | Tnpo2 | NM_001122843.1 | chr8:85037167-85057582 |
| 21764 | Tnpo3 | NM_177226.4 | chr6:29540826-29609607 |
| 21765 | Tnr | NM_022312.3 | chr1:159523768-159924922 |
| 21766 | Tnrc18 | NM_001122730.2 | chr5:142724604-142817387 |
| 21767 | Tnrc6a | NM_144925.3 | chr7:123123884-123195296 |
| 21768 | Tnrc6b | NM_144812.2 | chr15:80711312-80941086 |
| 21769 | Tnrc6c | NM_198022.2 | chr11:117654288-117763441 |
| 21770 | Tns1 | NM_001289895.1 | chr1:73910230-74124449 |
| 21771 | Tns3 | NM_001083587.1 | chr11:8431651-8664535 |
| 21772 | Tns4 | NM_172564.3 | chr11:99065677-99089306 |
| 21773 | Tnxb | NM_031176.2 | chr17:34670534-34719815 |
| 21774 | Tob1 | NM_009427.2 | chr11:94211453-94215492 |
| 21775 | Tob2 | NM_020507.3 | chr15:81848269-81858326 |
| 21776 | Toe1 | NM_026654.2 | chr4:116804002-116807559 |
| 21777 | Tollip | NM_023764.3 | chr7:141881584-141902406 |
| 21778 | Tom1 | NM_001136259.1 | chr8:75033685-75070121 |
| 21779 | Tom1l1 | NM_028011.2 | chr11:90645690-90687601 |
| 21780 | Tom1l2 | NM_001039092.3 | chr11:60226713-60352905 |
| 21781 | Tomm20 | NM_024214.2 | chr8:126930663-126945921 |
| 21782 | Tomm20l | NM_029227.1 | chr12:71111427-71123222 |
| 21783 | Tomm22 | NM_172609.3 | chr15:79670867-79672862 |
| 21784 | Tomm34 | NM_001291155.1 | chr2:164053539-164071169 |
| 21785 | Tomm40 | NM_001109748.1 | chr7:19701312-19715429 |
| 21786 | Tomm40l | NM_001037170.2 | chr1:171217802-171222514 |
| 21787 | Tomm5 | NM_001099675.1 | chr4:45105209-45108113 |
| 21788 | Tomm6 | NM_001164729.1 | chr17:47686644-47688386 |
| 21789 | Tomm6os | NR_045945.1 | chr17:47687609-47691092 |
| 21790 | Tomm7 | NM_025394.3 | chr5:23838943-23844145 |
| 21791 | Tomm70a | NM_138599.5 | chr16:57121713-57154530 |
| 21792 | Tomt | NM_001081679.1 | chr7:101899807-101906359 |
| 21793 | Tonsl | NM_183091.3 | chr15:76626236-76639929 |
| 21794 | Top1 | NM_009408.2 | chr2:160645896-160722763 |
| 21795 | Top1mt | NM_028404.2 | chr15:75657032-75678790 |
| 21796 | Top2a | NM_011623.2 | chr11:98992946-99024189 |
| 21797 | Top2b | NM_009409.2 | chr14:16365205-16430787 |
| 21798 | Top3a | NM_009410.2 | chr11:60740058-60777365 |
| 21799 | Top3b | NM_011624.2 | chr16:16870890-16892986 |
| 21800 | Topaz1 | NM_001199736.1 | chr9:122747345-122802074 |
| 21801 | Topbp1 | NM_176979.5 | chr9:103305326-103350427 |
| 21802 | Topors | NM_134097.3 | chr4:40259605-40269841 |
| 21803 | Toporsl | NM_026652.2 | chr4:52596273-52612163 |
| 21804 | Toporsos | NR_045265.1 | chr4:40269578-40270221 |
| 21805 | Tor1a | NM_144884.2 | chr2:30960560-30967918 |
| 21806 | Tor1aip1 | NM_001160018.1 | chr1:156004598-156036480 |
| 21807 | Tor1aip2 | NM_001160180.1 | chr1:156035726-156053736 |
| 21808 | Tor1b | NM_133673.3 | chr2:30953000-30959015 |
| 21809 | Tor2a | NM_152800.3 | chr2:32757233-32762244 |
| 21810 | Tor3a | NM_023141.2 | chr1:156653616-156674339 |
| 21811 | Tor4a | NM_146115.4 | chr2:25192719-25196813 |
| 21812 | Tox | NM_145711.4 | chr4:6687385-6990723 |
| 21813 | Tox2 | NM_001098799.1 | chr2:163225453-163323102 |
| 21814 | Tox3 | NM_172913.3 | chr8:90247111-90348252 |
| 21815 | Tox4 | NM_023434.3 | chr14:52279145-52295509 |
| 21816 | Tpbg | NM_001164792.1 | chr9:85842851-85847055 |
| 21817 | Tpbpa | NM_009411.3 | chr13:60938691-60943935 |
| 21818 | Tpbpb | NM_026429.4 | chr13:60901294-60904847 |
| 21819 | Tpcn1 | NM_145853.2 | chr5:120534156-120588613 |
| 21820 | Tpcn2 | NM_146206.5 | chr7:145253922-145284011 |
| 21821 | Tpd52 | NM_001025261.1 | chr3:8929435-8964054 |
| 21822 | Tpd52l1 | NM_009413.1 | chr10:31332379-31445921 |
| 21823 | Tpd52l2 | NM_001291197.1 | chr2:181497141-181517962 |
| 21824 | Tpgs1 | NM_148934.2 | chr10:79689409-79676126 |
| 21825 | Tpgs2 | NM_001004361.2 | chr18:25136038-25168877 |
| 21826 | Tph1 | NM_001136084.2 | chr7:46644640-46667377 |
| 21827 | Tph2 | NM_173391.3 | chr10:115078640-115185022 |
| 21828 | Tpi1 | NM_009415.2 | chr6:124810591-124814296 |
| 21829 | Tpk1 | NM_013861.4 | chr6:43345000-43666278 |
| 21830 | Tpm1 | NM_001164248.1 | chr9:67027889-67049213 |
| 21831 | Tpm2 | NM_001277875.1 | chr4:43513725-43523554 |
| 21832 | Tpm3 | NM_001253738.1 | chr3:90079520-90100902 |
| 21833 | Tpm4 | NM_001001491.1 | chr8:72135291-72153129 |
| 21834 | Tpmt | NM_016785.2 | chr13:47023542-47043217 |
| 21835 | Tpo | NM_009417.3 | chr12:30054660-30132624 |
| 21836 | Tpp1 | NM_009906.5 | chr7:105744846-105752207 |
| 21837 | Tpp2 | NM_009418.3 | chr1:43933993-44003000 |
| 21838 | Tppp | NM_182839.2 | chr13:74009418-74035753 |
| 21839 | Tppp2 | NM_001128634.1 | chr14:51918760-51920700 |
| 21840 | Tppp3 | NM_026481.3 | chr8:105467491-105471422 |

Fig. 26 - 116

| | | | | | | | | |
|---|---|---|---|---|---|---|---|---|
| 21841 | Tpr | NM_133780.3 | chr1:150392837-150449935 | | 21936 | Trim29 | NM_023655.2 | chr9:43310762-43336125 |
| 21842 | Tpra1 | NM_011906.2 | chr6:88902250-88912240 | | 21937 | Trim3 | NM_001285870.1 | chr7:105610647-105633571 |
| 21843 | Tprg | NM_175165.3 | chr16:25286816-25422344 | | 21938 | Trim30a | NM_009099.2 | chr7:104409025-104465193 |
| 21844 | Tprgl | NM_026388.2 | chr4:154157484-154160684 | | 21939 | Trim30b | NM_175648.2 | chr7:104355397-104358646 |
| 21845 | Tprkb | NM_001170488.1 | chr6:85915718-85930284 | | 21940 | Trim30d | NM_001167828.1 | chr7:104470013-104507849 |
| 21846 | Tprn | NM_175286.4 | chr2:25262597-25269886 | | 21941 | Trim30e-ps1 | NR_033673.1 | chr7:104532958-104535361 |
| 21847 | Tpsab1 | NM_031187.4 | chr17:25343244-25345562 | | 21942 | Trim31 | NM_146077.2 | chr17:36898129-36910217 |
| 21848 | Tpsb2 | NM_010781.3 | chr17:25366332-25368092 | | 21943 | Trim32 | NM_001161782.1 | chr4:65604985-65616240 |
| 21849 | Tpsg1 | NM_012034.3 | chr17:25370552-25374442 | | 21944 | Trim33 | NM_001079830.2 | chr3:103279292-103358770 |
| 21850 | Tpst1 | NM_001130476.2 | chr5:130079369-130135733 | | 21945 | Trim34a | NM_030684.3 | chr7:104244456-104262236 |
| 21851 | Tpst2 | NM_009419.3 | chr5:112276706-112315356 | | 21946 | Trim34b | NM_001243916.1 | chr7:104329470-104336617 |
| 21852 | Tpt1 | NM_009429.3 | chr14:75845255-75848303 | | 21947 | Trim35 | NM_029979.3 | chr14:66297024-66311424 |
| 21853 | Tpre | NM_199257.2 | chr8:22283440-22371418 | | 21948 | Trim36 | NM_001170855.1 | chr18:46165299-46198818 |
| 21854 | Tpx2 | NM_001141975.1 | chr2:152847963-152895321 | | 21949 | Trim37 | NM_197987.2 | chr11:87177074-87220686 |
| 21855 | Tra2a | NM_198102.2 | chr6:49243920-49264052 | | 21950 | Trim38 | NM_001029935.2 | chr13:23782540-23791528 |
| 21856 | Tra2b | NM_009186.4 | chr16:22245740-22265929 | | 21951 | Trim39 | NM_024468.2 | chr17:36258872-36272004 |
| 21857 | Trabd | NM_026485.2 | chr15:89076063-89087075 | | 21952 | Trim40 | NM_001033235.3 | chr17:36881597-36890125 |
| 21858 | Trabd2b | NM_001085549.1 | chr4:114406723-114615098 | | 21953 | Trim41 | NM_145377.2 | chr11:48806403-48817391 |
| 21859 | Tradd | NM_001033161.2 | chr8:105258574-105264594 | | 21954 | Trim42 | NM_030219.2 | chr9:97349561-97369958 |
| 21860 | Traf1 | NM_009421.3 | chr2:34943257-34961772 | | 21955 | Trim43a | NM_001034906.2 | chr9:88581035-88588819 |
| 21861 | Traf2 | NM_001290413.1 | chr2:25517981-25546940 | | 21956 | Trim43b | NM_001170884.1 | chr9:89084623-89092835 |
| 21862 | Traf3 | NM_001286122.1 | chr12:111166369-111267155 | | 21957 | Trim43c | NM_001178858.1 | chr9:88839163-88848190 |
| 21863 | Traf3ip1 | NM_028718.2 | chr1:91494667-91529307 | | 21958 | Trim44 | NM_020267.2 | chr2:102303118-102400900 |
| 21864 | Traf3ip2 | NM_134000.3 | chr10:39612933-39655307 | | 21959 | Trim45 | NM_001165952.1 | chr3:100922492-100936925 |
| 21865 | Traf3ip3 | NM_153137.4 | chr1:193175503-193201546 | | 21960 | Trim46 | NM_001039466.1 | chr3:89234176-89245199 |
| 21866 | Traf4 | NM_009423.4 | chr11:78158422-78165550 | | 21961 | Trim47 | NM_001205081.1 | chr11:116105749-116110235 |
| 21867 | Traf5 | NM_011633.2 | chr1:191997202-192092599 | | 21962 | Trim50 | NM_178240.2 | chr5:135353295-135367654 |
| 21868 | Traf6 | NM_009424.3 | chr2:101678419-101701668 | | 21963 | Trim52 | NM_198601.3 | chr14:106106197-106109280 |
| 21869 | Traf7 | NM_001172113.1 | chr17:24508849-24527938 | | 21964 | Trim54 | NM_021447.2 | chr5:31118611-31137626 |
| 21870 | Trafd1 | NM_001163470.1 | chr5:121371724-121385615 | | 21965 | Trim55 | NM_001081281.1 | chr3:19644459-19691599 |
| 21871 | Traip | NM_011634.3 | chr9:107950962-107972268 | | 21966 | Trim56 | NM_201373.4 | chr5:137111285-137116207 |
| 21872 | Trak1 | NM_175114.3 | chr9:121366957-121474918 | | 21967 | Trim58 | NM_001039047.1 | chr11:58640464-58652404 |
| 21873 | Trak2 | NM_172406.3 | chr1:58900449-58973482 | | 21968 | Trim59 | NM_025863.3 | chr3:69035293-69044742 |
| 21874 | Tram1 | NM_028173.5 | chr1:13564692-13589910 | | 21969 | Trim6 | NM_001013616.2 | chr7:104218794-104235152 |
| 21875 | Tram1l1 | NM_146140.3 | chr3:124321036-124323260 | | 21970 | Trim60 | NM_153097.2 | chr8:64998447-65018688 |
| 21876 | Tram2 | NM_177409.3 | chr1:21001396-21079225 | | 21971 | Trim61 | NM_001177551.1 | chr8:65012975-65018688 |
| 21877 | Trank1 | NM_001164659.1 | chr9:111311738-111395775 | | 21972 | Trim62 | NM_178130.2 | chr4:128884139-128911326 |
| 21878 | Trap1 | NM_026508.2 | chr16:4039976-4077810 | | 21973 | Trim63 | NM_001039048.2 | chr4:134315119-134329629 |
| 21879 | Trap1a | NM_011635.1 | chrX:139333682-139338165 | | 21974 | Trim65 | NM_001016124707-116131128 | chr11:116124707-116131128 |
| 21880 | Trappc1 | NM_001024206.2 | chr11:69323985-69325793 | | 21975 | Trim66 | NM_001170912.1 | chr7:109449000-109508134 |
| 21881 | Trappc10 | NM_001081055.1 | chr10:78186725-78244642 | | 21976 | Trim67 | NM_198632.2 | chr8:124793618-124834704 |
| 21882 | Trappc11 | NM_177012.1 | chr8:47490127-47533470 | | 21977 | Trim68 | NM_198012.3 | chr7:102677584-102687327 |
| 21883 | Trappc12 | NM_001161410.1 | chr12:28690627-28750394 | | 21978 | Trim69 | NM_080510.2 | chr2:122160699-122179027 |
| 21884 | Trappc13 | NM_001093759.1 | chr13:104142152-104178466 | | 21979 | Trim7 | NM_053166.2 | chr11:48826137-48850195 |
| 21885 | Trappc2 | NM_025432.4 | chrX:166440754-166453140 | | 21980 | Trim71 | NM_001042503.2 | chr9:114511272-114564369 |
| 21886 | Trappc2l | NM_021502.2 | chr8:122611625-122615591 | | 21981 | Trim72 | NM_001079932.3 | chr7:128804377-128811393 |
| 21887 | Trappc3 | NM_013718.2 | chr4:126262404-126275883 | | 21982 | Trim75 | NM_001033429.2 | chr8:64981650-64987644 |
| 21888 | Trappc3l | NM_001162934.1 | chr10:34037596-34109815 | | 21983 | Trim8 | NM_053100.2 | chr19:46501647-46516455 |
| 21889 | Trappc4 | NM_021789.2 | chr9:44403758-44407548 | | 21984 | Trim9 | NM_001110202.1 | chr12:70244534-70347614 |
| 21890 | Trappc5 | NM_025701.4 | chr8:3676476-3680921 | | 21985 | Triml1 | NM_177742.4 | chr8:43129806-43141486 |
| 21891 | Trappc6a | NM_025960.3 | chr7:19508728-19516145 | | 21986 | Triml2 | NM_001160412.1 | chr8:43183121-43193884 |
| 21892 | Trappc6b | NM_030057.3 | chr12:59043091-59061472 | | 21987 | Trio | NM_001081302.1 | chr15:27730648-28025848 |
| 21893 | Trappc8 | NM_029491.2 | chr18:20846144-20896078 | | 21988 | Triobp | NM_001024716.1 | chr15:78983055-79005864 |
| 21894 | Trappc9 | NM_001164641.1 | chr15:72799523-73061204 | | 21989 | Trip10 | NM_001242389.1 | chr17:57249450-57263697 |
| 21895 | Trat1 | NM_198297.3 | chr16:48734689-48771956 | | 21990 | Trip11 | NM_028446.1 | chr12:101837371-101913171 |
| 21896 | Trcg1 | NM_001014398.2 | chr9:57236555-57249864 | | 21991 | Trip12 | NM_133975.4 | chr1:84721188-84839304 |
| 21897 | Trdmt1 | NM_010067.4 | chr2:13510160-13534664 | | 21992 | Trip13 | NM_027182.2 | chr13:73912461-73937767 |
| 21898 | Trdn | NM_029726.2 | chr10:33083482-33476709 | | 21993 | Trip4 | NM_001170907.1 | chr9:65828925-65885173 |
| 21899 | Treh | NM_001277847.1 | chr9:44673232-44686305 | | 21994 | Trip6 | NM_011639.3 | chr5:137309898-137314241 |
| 21900 | Trem1 | NM_021406.5 | chr17:48232738-48246924 | | 21995 | Triqk | NM_001171801.1 | chr4:12906836-12981485 |
| 21901 | Trem2 | NM_001272078.1 | chr17:48346460-48352276 | | 21996 | Trit1 | NM_025873.2 | chr4:123016596-123054934 |
| 21902 | Trem3 | NM_021407.3 | chr17:48247728-48258647 | | 21997 | Trmt1 | NM_001164559.1 | chr8:84689246-84699808 |
| 21903 | Treml1 | NM_001289451.1 | chr17:48359915-48367176 | | 21998 | Trmt10a | NM_175389.4 | chr3:138143537-138159820 |
| 21904 | Treml2 | NM_001033405.2 | chr17:48300037-48312534 | | 21999 | Trmt10b | NM_027266.4 | chr4:45297167-45316131 |
| 21905 | Treml4 | NM_001033922.2 | chr17:48264294-48275358 | | 22000 | Trmt10c | NM_029092.3 | chr16:56033719-56037774 |
| 21906 | Trerf1 | NM_001097623.1 | chr17:47140941-47359458 | | 22001 | Trmt11 | NM_028604.2 | chr10:30534224-30600749 |
| 21907 | Trex1 | NM_001012236.1 | chr9:109057931-109059251 | | 22002 | Trmt112 | NM_001166370.1 | chr19:6909697-6911026 |
| 21908 | Trex2 | NM_011907.4 | chrX:73433704-73435343 | | 22003 | Trmt12 | NM_026642.2 | chr15:58872648-58876781 |
| 21909 | Trf | NM_133977.2 | chr9:103208875-103230286 | | 22004 | Trmt13 | NM_030016.2 | chr3:116581335-116614587 |
| 21910 | Trh | NM_009426.3 | chr6:92242060-92244650 | | 22005 | Trmt1l | NM_026876.3 | chr1:151428647-151458183 |
| 21911 | Trhde | NM_146241.2 | chr10:114398820-114801370 | | 22006 | Trmt2a | NM_001080999.2 | chr16:18248882-18254772 |
| 21912 | Trhr | NM_013696.2 | chr15:44196134-44235912 | | 22007 | Trmt2b | NM_001167994.1 | chrX:134223954-134276984 |
| 21913 | Trhr2 | NM_133202.2 | chr8:122356966-122360746 | | 22008 | Trmt44 | NM_030208.3 | chr5:35556208-35575070 |
| 21914 | Triap1 | NM_026933.2 | chr5:115341246-115343552 | | 22009 | Trmt5 | NM_029580.3 | chr12:73280409-73286711 |
| 21915 | Trib1 | NM_144549.4 | chr15:59648653-59657099 | | 22010 | Trmt6 | NM_175113.3 | chr2:132804214-132816054 |
| 21916 | Trib2 | NM_144551.5 | chr12:15791726-15816785 | | 22011 | Trmt61a | NM_001099792.1 | chr12:111675104-111683902 |
| 21917 | Trib3 | NM_175093.2 | chr2:152337424-152344060 | | 22012 | Trmt61b | NR_015549.1 | chr17:71557076-71598761 |
| 21918 | Tril | NM_025817.4 | chr6:53815467-53820825 | | 22013 | Trmu | NM_028063.2 | chr15:85897393-85897393 |
| 21919 | Trim10 | NM_011280.2 | chr17:36869553-36877833 | | 22014 | Trnau1ap | NM_027925.3 | chr4:132311762-132329538 |
| 21920 | Trim11 | NM_001090988.1 | chr11:58978092-58991462 | | 22015 | Trnp1 | NM_001081156.2 | chr4:133491099-133498550 |
| 21921 | Trim12a | NM_023835.2 | chr7:104299896-104315495 | | 22016 | Trnt1 | NM_001242358.1 | chr6:106769137-106782474 |
| 21922 | Trim12c | NM_001146007.1 | chr7:104338753-104353358 | | 22017 | Tro | NM_001002272.3 | chrX:150644709-150657436 |
| 21923 | Trim13 | NM_001164220.1 | chr14:61598225-61605945 | | 22018 | Troap | NM_001162506.1 | chr15:99074972-99083409 |
| 21924 | Trim14 | NM_029077.4 | chr4:46505071-46536141 | | 22019 | Trove2 | NM_013835.2 | chr1:143756790-143777051 |
| 21925 | Trim15 | NM_001024134.2 | chr17:36860690-36867187 | | 22020 | Trp53 | NM_001127233.1 | chr11:69580358-69591873 |
| 21926 | Trim16 | NM_053169.2 | chr11:62820252-62842948 | | 22021 | Trp53bp1 | NM_001290830.1 | chr2:121194834-121271407 |
| 21927 | Trim17 | NM_031172.4 | chr11:58963780-58971729 | | 22022 | Trp53bp2 | NM_173378.2 | chr1:182409166-182462436 |
| 21928 | Trim2 | NM_001271725.1 | chr3:84160438-84270783 | | 22023 | Trp53cor1 | NR_036469.2 | chr17:29057473-29079126 |
| 21929 | Trim21 | NM_001082552.2 | chr7:102557919-102565482 | | 22024 | Trp53i11 | NM_001025246.1 | chr2:93187583-93201757 |
| 21930 | Trim23 | NM_030731.3 | chr13:104179097-104202048 | | 22025 | Trp53i13 | NM_001024920.1 | chr11:77508098-77513273 |
| 21931 | Trim24 | NM_001272064.1 | chr6:37870810-37968445 | | 22026 | Trp53inp1 | NM_001199105.1 | chr4:11156440-11174377 |
| 21932 | Trim25 | NM_009546.2 | chr11:88999402-89004293 | | 22027 | Trp53inp2 | NM_178111.3 | chr2:155381855-155389847 |
| 21933 | Trim26 | NM_001025999.3 | chr17:36837145-36859398 | | 22028 | Trp53rk | NM_023815.4 | chr2:166793766-166799492 |
| 21934 | Trim27 | NM_009054.3 | chr13:21179930-21194723 | | 22029 | Trp53tg5 | NM_001271575.1 | chr2:164470303-164473724 |
| 21935 | Trim28 | NM_011588.3 | chr7:13024151-13031032 | | 22030 | Trp63 | NM_001127259.1 | chr16:25683764-25892088 |

Fig. 26 - 117

| | | | |
|---|---|---|---|
| 22031 | Trp73 | NM_001126330.1 | chr4:154056248-154097173 |
| 22032 | Trpa1 | NM_177781.4 | chr1:14872647-14918862 |
| 22033 | Trpc1 | NM_011643.3 | chr9:95705066-95790358 |
| 22034 | Trpc2 | NM_001109897.2 | chr7:102083115-102096864 |
| 22035 | Trpc3 | NM_019510.2 | chr3:36620481-36690167 |
| 22036 | Trpc4 | NM_001253682.1 | chr3:54156056-54318471 |
| 22037 | Trpc4ap | NM_001163452.1 | chr2:155634276-155692384 |
| 22038 | Trpc5 | NM_009428.3 | chrX:144377326-144688180 |
| 22039 | Trpc5os | NM_001195579.1 | chrX:144456581-144477063 |
| 22040 | Trpc6 | NM_001282086.1 | chr9:8544141-8680741 |
| 22041 | Trpc7 | NM_012035.3 | chr13:56773097-56895789 |
| 22042 | Trpd52l3 | NM_025741.2 | chr19:30003789-30006020 |
| 22043 | Trpm1 | NM_001039104.2 | chr7:64153834-64269759 |
| 22044 | Trpm2 | NM_138301.2 | chr10:77907721-77969872 |
| 22045 | Trpm3 | NM_001035239.2 | chr19:22139116-22989882 |
| 22046 | Trpm4 | NM_175130.4 | chr7:45303154-45333780 |
| 22047 | Trpm5 | NM_020277.2 | chr7:143071528-143084642 |
| 22048 | Trpm6 | NM_153417.1 | chr19:18749982-18892511 |
| 22049 | Trpm7 | NM_001164325.1 | chr2:126791557-126876261 |
| 22050 | Trpm8 | NM_134252.3 | chr1:88306711-88388851 |
| 22051 | Trps1 | NM_032000.2 | chr15:50654758-50890041 |
| 22052 | Trpt1 | NM_153597.2 | chr19:6996130-6999046 |
| 22053 | Trpv1 | NM_001001445.2 | chr11:73234148-73261322 |
| 22054 | Trpv2 | NM_011706.2 | chr11:62574485-62600305 |
| 22055 | Trpv3 | NM_145099.2 | chr11:73627619-73297200 |
| 22056 | Trpv4 | NM_022017.3 | chr5:114622153-114658421 |
| 22057 | Trpv5 | NM_001007572.2 | chr6:41652769-41680723 |
| 22058 | Trpv6 | NM_022413.4 | chr6:41620618-41636405 |
| 22059 | Trrap | NM_001081362.1 | chr5:144768791-144859773 |
| 22060 | Trub1 | NM_028115.3 | chr19:57452905-57491005 |
| 22061 | Trub2 | NM_001290495.1 | chr2:29774683-29787671 |
| 22062 | Try10 | NM_001038996.2 | chr6:41354104-41357944 |
| 22063 | Try4 | NM_011646.5 | chr6:41302271-41305533 |
| 22064 | Try5 | NM_001003405.4 | chr6:41311231-41314710 |
| 22065 | Tsacc | NM_029801.2 | chr3:88282759-88296838 |
| 22066 | Tsc1 | NM_001289575.1 | chr2:28641232-28691172 |
| 22067 | Tsc2 | NM_001039363.2 | chr17:24595815-24632627 |
| 22068 | Tsc22d1 | NM_001177751.2 | chr14:76488435-76507765 |
| 22069 | Tsc22d2 | NM_001081229.1 | chr3:58415688-58466787 |
| 22070 | Tsc22d3 | NM_001077364.1 | chrX:140539528-140600522 |
| 22071 | Tsc22d4 | NM_023910.6 | chr15:137745968-137759747 |
| 22072 | Tsen15 | NM_025677.3 | chr1:152370735-152386682 |
| 22073 | Tsen2 | NM_199033.1 | chr6:115544703-115578336 |
| 22074 | Tsen34 | NM_001164204.1 | chr7:3693609-3701035 |
| 22075 | Tsen54 | NM_029557.1 | chr11:115814738-115823102 |
| 22076 | Tsfm | NM_025537.3 | chr10:127022331-127030814 |
| 22077 | Tsg101 | NM_021884.3 | chr7:46889026-46919930 |
| 22078 | Tsga10 | NM_001290720.1 | chr1:37760823-37865298 |
| 22079 | Tsga13 | NM_054073.2 | chr6:30896980-30915573 |
| 22080 | Tsga8 | NM_021898.2 | chrX:83486675-83487924 |
| 22081 | Tshb | NM_001165939.1 | chr3:102777397-102782714 |
| 22082 | Tshr | NM_001113404.1 | chr12:91400992-91522541 |
| 22083 | Tshz1 | NM_001081300.1 | chr18:84011626-84086562 |
| 22084 | Tshz2 | NM_080455.2 | chr2:169633645-169888504 |
| 22085 | Tshz3 | NM_172298.2 | chr7:36698117-36773457 |
| 22086 | Tsix | NR_002844.2 | chrX:103431516-103484957 |
| 22087 | Tsks | NM_001077591.1 | chr7:44943239-44958037 |
| 22088 | Tsku | NM_001024619.3 | chr7:98350667-98361288 |
| 22089 | Tslp | NM_021367.2 | chr18:32815382-32819799 |
| 22090 | Tsn | NM_011650.3 | chr1:118298517-118311132 |
| 22091 | Tsnax | NM_016909.2 | chr8:125012996-125034192 |
| 22092 | Tsnaxip1 | NM_024445.4 | chr8:105827743-105844676 |
| 22093 | Tspan1 | NM_133681.4 | chr4:116161880-116167598 |
| 22094 | Tspan10 | NM_145363.2 | chr11:120442630-120447321 |
| 22095 | Tspan11 | NM_026743.3 | chr6:127887621-127953031 |
| 22096 | Tspan12 | NM_173007.3 | chr6:21771394-21852515 |
| 22097 | Tspan13 | NM_025359.3 | chr12:36014554-36042478 |
| 22098 | Tspan14 | NM_145928.2 | chr14:40906443-40966807 |
| 22099 | Tspan15 | NM_197996.2 | chr10:62185395-62231218 |
| 22100 | Tspan17 | NM_028841.3 | chr13:54789404-54796775 |
| 22101 | Tspan18 | NM_183180.2 | chr2:93201759-93334487 |
| 22102 | Tspan2 | NM_001243132.1 | chr3:102735214-102772310 |
| 22103 | Tspan2os | NR_040588.1 | chr3:102720230-102735417 |
| 22104 | Tspan3 | NM_019793.3 | chr9:56135888-56161070 |
| 22105 | Tspan31 | NM_025982.4 | chr10:127067289-127070261 |
| 22106 | Tspan32 | NM_001128080.2 | chr7:143005045-143019485 |
| 22107 | Tspan33 | NM_146173.3 | chr6:29694213-29718558 |
| 22108 | Tspan4 | NM_001252588.1 | chr7:141476379-141493427 |
| 22109 | Tspan6 | NM_019571.5 | chr3:138742207-138904433 |
| 22110 | Tspan6 | NM_019656.3 | chrX:133891069-133898429 |
| 22111 | Tspan7 | NM_019634.2 | chrX:10485115-10596604 |
| 22112 | Tspan8 | NM_001168679.1 | chr10:115817283-115849893 |
| 22113 | Tspan9 | NM_175414.4 | chr6:127961399-128143578 |
| 22114 | Tspear | NM_028707074.1 | chr10:77686568-77886769 |
| 22115 | Tspo | NM_009775.4 | chr15:83563572-83574203 |
| 22116 | Tspo2 | NM_027292.2 | chr17:48448434-48451501 |
| 22117 | Tspyl1 | NM_009433.3 | chr10:34282189-34284885 |
| 22118 | Tspyl2 | NM_029836.3 | chrX:152336851-152342484 |
| 22119 | Tspyl3 | NM_198617.2 | chr2:153222369-153225441 |
| 22120 | Tspyl4 | NM_030203.2 | chr10:34297420-34301320 |
| 22121 | Tspyl5 | NM_001085421.1 | chr15:33683874-33687883 |
| 22122 | Tspy-ps | NR_027507.1 | chrY:1055763-1058868 |
| 22123 | Tsr1 | NM_177325.3 | chr11:74898079-74909340 |
| 22124 | Tsr2 | NM_001164578.1 | chrX:151087093-151096543 |
| 22125 | Tsr3 | NM_001163718.1 | chr17:25240169-25242799 |

| | | | |
|---|---|---|---|
| 22126 | Tssc1 | NM_201357.2 | chr12:28751827-28867491 |
| 22127 | Tssc4 | NM_001115085.1 | chr7:143069367-143071087 |
| 22128 | Tssk1 | NM_009435.2 | chr16:17894202-17895653 |
| 22129 | Tssk2 | NM_009436.2 | chr16:17898636-17900024 |
| 22130 | Tssk3 | NM_080442.2 | chr4:129489007-129490770 |
| 22131 | Tssk4 | NM_001253888.1 | chr14:55650183-55652539 |
| 22132 | Tssk5 | NM_183099.2 | chr15:76371957-76374938 |
| 22133 | Tssk6 | NM_032004.1 | chr8:69902214-69903518 |
| 22134 | Tst | NM_009437.4 | chr15:78399555-78405859 |
| 22135 | Tsta3 | NM_031201.1 | chr15:75924682-75929730 |
| 22136 | Tstd1 | NM_001164525.1 | chr1:171419032-171420352 |
| 22137 | Tstd2 | NM_173033.3 | chr4:46114745-46138475 |
| 22138 | Tstd3 | NM_029840.1 | chr4:21757381-21767211 |
| 22139 | Tsx | NM_009440.2 | chrX:103414466-103424583 |
| 22140 | Ttbk1 | NM_001162864.1 | chr17:46442447-46487675 |
| 22141 | Ttbk2 | NM_001024856.2 | chr2:120732816-120850418 |
| 22142 | Ttc1 | NM_133795.1 | chr11:43730805-43747973 |
| 22143 | Ttc12 | NM_172770.3 | chr9:49436960-49486225 |
| 22144 | Ttc13 | NM_145607.3 | chr8:124671326-124721975 |
| 22145 | Ttc14 | NM_001290500.1 | chr3:33800182-33814860 |
| 22146 | Ttc16 | NM_001290563.1 | chr2:32757025-32775633 |
| 22147 | Ttc17 | NM_183106.2 | chr2:94300765-94406689 |
| 22148 | Ttc18 | NM_001163638.1 | chr14:20394189-20452225 |
| 22149 | Ttc19 | NM_028360.2 | chr11:62281472-62316424 |
| 22150 | Ttc21a | NM_028735.3 | chr9:119937605-119967793 |
| 22151 | Ttc21b | NM_001047604.2 | chr2:66184326-66256617 |
| 22152 | Ttc22 | NM_177667.4 | chr4:106622448-106640187 |
| 22153 | Ttc23 | NM_001168475.1 | chr7:67647409-67726576 |
| 22154 | Ttc23l | NM_029430.1 | chr15:10503946-10558668 |
| 22155 | Ttc24 | NM_172526.3 | chr3:88069409-88078304 |
| 22156 | Ttc25 | NM_028918.2 | chr11:100545631-100572566 |
| 22157 | Ttc26 | NM_153600.2 | chr6:38381523-38427647 |
| 22158 | Ttc27 | NM_152817.3 | chr17:74717749-74863570 |
| 22159 | Ttc28 | NM_001267622.1 | chr5:110879802-111289779 |
| 22160 | Ttc29 | NM_183096.3 | chr8:78213341-78394326 |
| 22161 | Ttc3 | NM_009441.2 | chr16:94370738-94469221 |
| 22162 | Ttc30a1 | NM_030188.3 | chr2:75979105-75981967 |
| 22163 | Ttc30a2 | NM_001081228.1 | chr2:75976171-75978179 |
| 22164 | Ttc30b | NM_028235.1 | chr2:75935848-75938462 |
| 22165 | Ttc32 | NM_029321.2 | chr12:9029996-9036394 |
| 22166 | Ttc33 | NM_026213.3 | chr15:5185559-5218332 |
| 22167 | Ttc34 | NM_172878.3 | chr4:154856199-154867127 |
| 22168 | Ttc36 | NM_138951.1 | chr9:44799399-44802951 |
| 22169 | Ttc37 | NM_001081352.1 | chr13:76098733-76187983 |
| 22170 | Ttc38 | NM_001033337.4 | chr15:85832303-85858822 |
| 22171 | Ttc39a | NM_001145948.1 | chr4:109415646-109444745 |
| 22172 | Ttc39b | NM_027238.2 | chr4:83220300-83324189 |
| 22173 | Ttc39c | NM_028341.4 | chr18:12643532-12737052 |
| 22174 | Ttc39d | NM_026351.2 | chr17:80215913-80217936 |
| 22175 | Ttc4 | NM_001172073.1 | chr4:106661807-106678686 |
| 22176 | Ttc5 | NM_001080949.2 | chr14:50765408-50785520 |
| 22177 | Ttc7 | NM_028639.3 | chr17:87282885-87381770 |
| 22178 | Ttc7b | NM_001033213.1 | chr12:100300769-100520822 |
| 22179 | Ttc8 | NM_029553.3 | chr12:98920573-98983238 |
| 22180 | Ttc9 | NM_001033149.3 | chr12:81631248-81667557 |
| 22181 | Ttc9b | NM_028417.1 | chr7:27653923-27656207 |
| 22182 | Ttc9c | NM_027412.3 | chr19:8809074-8819294 |
| 22183 | Ttf1 | NM_009442.3 | chr2:29060262-29087650 |
| 22184 | Ttf2 | NM_001013026.2 | chr3:100938859-100969663 |
| 22185 | Tti1 | NM_029282.1 | chr2:157981802-158009360 |
| 22186 | Tti2 | NM_001199988.1 | chr8:31150315-31164703 |
| 22187 | Ttk | NM_001110265.1 | chr9:83834688-83869493 |
| 22188 | Ttl | NM_027192.2 | chr2:129065946-129096283 |
| 22189 | Ttll1 | NM_178869.4 | chr15:83483768-83510907 |
| 22190 | Ttll10 | NM_029264.2 | chr4:156034836-156050817 |
| 22191 | Ttll11 | NM_029774.2 | chr2:35751225-35979624 |
| 22192 | Ttll12 | NM_183017.2 | chr15:83575093-83595157 |
| 22193 | Ttll13 | NM_177765.3 | chr7:80246375-80260821 |
| 22194 | Ttll2 | NM_001098267.1 | chr17:7350903-7352696 |
| 22195 | Ttll3 | NM_001142732.1 | chr6:113389259-113399448 |
| 22196 | Ttll4 | NM_001014974.1 | chr1:74661753-74697973 |
| 22197 | Ttll5 | NM_001081423.2 | chr12:85824949-86053760 |
| 22198 | Ttll6 | NM_172799.4 | chr11:96133785-96165452 |
| 22199 | Ttll7 | NM_001302957.1 | chr3:146852136-146984009 |
| 22200 | Ttll8 | NM_172818.3 | chr15:88913897-88954418 |
| 22201 | Ttll9 | NM_001083618.1 | chr2:152962484-153008482 |
| 22202 | Ttn | NM_011652.3 | chr2:76703983-76982547 |
| 22203 | Ttpa | NM_015767.3 | chr4:20008427-20030785 |
| 22204 | Ttpal | NM_163602313-163619013 | chr2:163602313-163619013 |
| 22205 | Ttr | NM_013697.5 | chr18:20665249-20674326 |
| 22206 | Ttyh1 | NM_001001454.4 | chr7:4119529-4135407 |
| 22207 | Ttyh2 | NM_053273.2 | chr11:114675467-114720984 |
| 22208 | Ttyh3 | NM_175274.5 | chr5:140620576-140649031 |
| 22209 | Tub | NM_021885.4 | chr7:109010879-109034459 |
| 22210 | Tuba1a | NM_011653.2 | chr15:98949846-98953501 |
| 22211 | Tuba1b | NM_011654.2 | chr15:98931430-98934390 |
| 22212 | Tuba1c | NM_009448.4 | chr15:99029890-99038105 |
| 22213 | Tuba3a | NM_009446.2 | chr6:125278273-125286042 |
| 22214 | Tuba3b | NM_009449.3 | chr6:145615962-145621477 |
| 22215 | Tuba4a | NM_009447.4 | chr1:75214971-75219294 |
| 22216 | Tuba8 | NM_017379.2 | chr6:121210733-121226098 |
| 22217 | Tubal3 | NM_001033879.3 | chr13:3924694-3935277 |
| 22218 | Tubb1 | NM_001080971.2 | chr2:174450594-174458380 |
| 22219 | Tubb2a | NM_009450.2 | chr13:34074279-34078008 |
| 22220 | Tubb2a-ps2 | NR_003964.2 | chr12:11882195-11882899 |

Fig. 26 - 118

| | | | | | | | |
|---|---|---|---|---|---|---|---|
| 22221 | Tubb2b | NM_023716.2 | chr13:34127007-34130354 | 22316 | Ubash3b | NM_176860.5 | chr9:41013640-41157494 |
| 22222 | Tubb3 | NM_023279.2 | chr8:123411563-123422010 | 22317 | Ubb | NM_011664.4 | chr11:62551170-62553213 |
| 22223 | Tubb4a | NM_009451.3 | chr17:57080066-57087782 | 22318 | Ubc | NM_019639.4 | chr5:125385964-125390017 |
| 22224 | Tubb4b | NM_146116.2 | chr2:25222157-25224702 | 22319 | Ubd | NM_023137.3 | chr17:37193891-37196101 |
| 22225 | Tubb5 | NM_011655.5 | chr17:35833919-35838301 | 22320 | Ube2a | NM_019668.4 | chrX:36874294-36884220 |
| 22226 | Tubb6 | NM_026473.2 | chr18:67390730-67402749 | 22321 | Ube2b | NM_009458.4 | chr11:51985145-52000466 |
| 22227 | Tubd1 | NM_001199045.1 | chr11:86544990-86567360 | 22322 | Ube2c | NM_026785.2 | chr2:164769928-164772902 |
| 22228 | Tube1 | NM_028006.2 | chr10:39134022-39151058 | 22323 | Ube2cbp | NM_027394.2 | chr9:86307233-86464916 |
| 22229 | Tubg1 | NM_134024.2 | chr11:101120130-101126419 | 22324 | Ube2d1 | NM_145420.2 | chr10:71254979-71285262 |
| 22230 | Tubg2 | NM_134028.2 | chr11:101155883-101161787 | 22325 | Ube2d2a | NM_019912.2 | chr18:35771558-35807172 |
| 22231 | Tubgcp2 | NM_001286007.1 | chr7:139995954-140036674 | 22326 | Ube2d2b | NM_001276397.1 | chr5:107830161-107831777 |
| 22232 | Tubgcp3 | NM_198031.1 | chr8:12614276-12672100 | 22327 | Ube2d3 | NM_025356.4 | chr3:135438758-135467178 |
| 22233 | Tubgcp4 | NM_001290824.1 | chr2:121171167-121198770 | 22328 | Ube2dnl1 | NM_001276396.1 | chrX:114905611-114905941 |
| 22234 | Tubgcp5 | NM_146190.2 | chr7:55794147-55831447 | 22329 | Ube2dnl2 | NM_001081661.1 | chrX:114907581-114908510 |
| 22235 | Tubgcp6 | NM_001163319.1 | chr15:89099097-89123150 | 22330 | Ube2e1 | NM_009455.3 | chr14:18282728-18331844 |
| 22236 | Tufm | NM_001163713.1 | chr7:126487354-126490731 | 22331 | Ube2e2 | NM_144839.1 | chr14:18573576-18893627 |
| 22237 | Tuft1 | NM_011656.3 | chr3:94612752-94658872 | 22332 | Ube2e3 | NM_009454.2 | chr2:78869046-78920583 |
| 22238 | Tug1 | NR_002321.2 | chr11:3639784-3648814 | 22333 | Ube2f | NM_026454.3 | chr1:91250318-91286025 |
| 22239 | Tulp1 | NM_021478.1 | chr17:28351518-28365143 | 22334 | Ube2g1 | NM_025985.4 | chr11:72607260-72686481 |
| 22240 | Tulp2 | NM_001045555.2 | chr7:45513705-45522927 | 22335 | Ube2g2 | NM_019803.3 | chr10:77622320-77645990 |
| 22241 | Tulp3 | NM_011657.2 | chr6:128321160-128355851 | 22336 | Ube2h | NM_001169576.1 | chr6:30211289-30304539 |
| 22242 | Tulp4 | NM_001103181.1 | chr17:6106829-6240637 | 22337 | Ube2i | NM_001177609.1 | chr17:25260510-25273914 |
| 22243 | Tunar | NR_045047.1 | chr12:105336593-105383932 | 22338 | Ube2j1 | NM_019586.3 | chr4:33031424-33052364 |
| 22244 | Tusc1 | NM_026954.1 | chr4:93334147-93335611 | 22339 | Ube2j2 | NM_001039157.2 | chr4:155943812-155959604 |
| 22245 | Tusc2 | NM_001285673.1 | chr9:107563254-107566108 | 22340 | Ube2k | NM_016786.4 | chr5:65537244-65598989 |
| 22246 | Tusc3 | NM_030254.3 | chr8:39005866-39130817 | 22341 | Ube2l3 | NM_009456.2 | chr16:17152014-17201492 |
| 22247 | Tusc5 | NM_177709.3 | chr11:76679872-76698664 | 22342 | Ube2l6 | NM_019949.2 | chr2:84798827-84810003 |
| 22248 | Tut1 | NM_197993.2 | chr19:8953849-8966210 | 22343 | Ube2m | NM_001168469.2 | chr7:13035119-13038275 |
| 22249 | Tvp23a | NM_001013778.1 | chr16:10420558-10447350 | 22344 | Ube2n | NM_080560.3 | chr10:95515161-95545658 |
| 22250 | Tvp23b | NM_026210.4 | chr11:62879489-62895184 | 22345 | Ube2o | NM_173755.3 | chr11:116537752-116581447 |
| 22251 | Twf1 | NM_008971.4 | chr15:94577947-94589824 | 22346 | Ube2q1 | NM_027315.4 | chr3:89773608-89783997 |
| 22252 | Twf2 | NM_011876.3 | chr9:106203107-106215387 | 22347 | Ube2q2 | NM_180600.3 | chr9:55149368-55207529 |
| 22253 | Twist1 | NM_011658.2 | chr12:33957670-33959831 | 22348 | Ube2ql1 | NM_001145162.1 | chr13:69702831-69739897 |
| 22254 | Twist2 | NM_007855.3 | chr1:91801460-91848034 | 22349 | Ube2r2 | NM_026275.4 | chr4:41136020-41193370 |
| 22255 | Twistnb | NM_172253.2 | chr12:33429623-33439380 | 22350 | Ube2s | NM_133777.2 | chr7:4808033-4812340 |
| 22256 | Twsg1 | NM_023053.3 | chr17:65923064-65951187 | 22351 | Ube2t | NM_001278115.1 | chr1:134962564-134974179 |
| 22257 | Txk | NM_001122754.2 | chr5:72695977-72752777 | 22352 | Ube2u | NM_001033773.4 | chr4:100478866-100550145 |
| 22258 | Txlna | NM_001005506.3 | chr4:129626076-129640805 | 22353 | Ube2v1 | NM_023230.2 | chr2:167607638-167632005 |
| 22259 | Txlnb | NM_138628.3 | chr10:17796218-17845663 | 22354 | Ube2v2 | NM_001159351.1 | chr16:15550985-15594518 |
| 22260 | Txlng | NM_001290776.1 | chrX:162778916-162829454 | 22355 | Ube2w | NM_001271016.1 | chr1:16540787-16619338 |
| 22261 | Txn1 | NM_011660.3 | chr4:57943372-57956411 | 22356 | Ube2z | NM_172300.3 | chr11:96047430-96065364 |
| 22262 | Txn2 | NM_019772.5 | chr15:77915050-77928994 | 22357 | Ube3a | NM_001033962.1 | chr7:59228751-59306727 |
| 22263 | Txndc11 | NM_029582.2 | chr16:11074910-11134532 | 22358 | Ube3b | NM_054093.2 | chr5:114380606-114421166 |
| 22264 | Txndc12 | NM_025334.3 | chr4:108834677-108862119 | 22359 | Ube3c | NM_133907.3 | chr5:29569241-29676077 |
| 22265 | Txndc15 | NM_145400.3 | chr13:55714649-55726228 | 22360 | Ube4a | NM_145400.3 | chr9:44923126-44965600 |
| 22266 | Txndc16 | NM_172597.3 | chr14:45134447-45219425 | 22361 | Ube4b | NM_020022.3 | chr4:149328415-149426631 |
| 22267 | Txndc17 | NM_026559.2 | chr11:72207553-72210487 | 22362 | Ubfd1 | NM_138589.2 | chr7:122067197-122082199 |
| 22268 | Txndc2 | NM_001146002.1 | chr17:65637504-65642204 | 22363 | Ubiad1 | NM_027873.2 | chr4:148484496-148484751 |
| 22269 | Txndc5 | NM_001289598.1 | chr13:38500270-38528824 | 22364 | Ubl3 | NM_011908.2 | chr5:148604630-148552788 |
| 22270 | Txndc8 | NM_026132.2 | chr4:57984028-58009124 | 22365 | Ubl4 | NM_145405.2 | chrX:74365717-74368548 |
| 22271 | Txndc9 | NM_172054.4 | chr1:37983866-37997208 | 22366 | Ubl4b | NM_026261.2 | chr3:107553697-107555073 |
| 22272 | Txnip | NM_001009935.2 | chr3:96557956-96561857 | 22367 | Ubl5 | NM_025401.3 | chr9:20643317-20646789 |
| 22273 | Txnl1 | NM_016792.4 | chr18:63662800-63692359 | 22368 | Ubl7 | NM_001122873.1 | chr9:57910985-57929968 |
| 22274 | Txnl4a | NM_001038608.2 | chr18:80206797-80212732 | 22369 | Ubtcp1 | NM_024475.5 | chr11:44454570-44470548 |
| 22275 | Txnl4b | NM_175646.3 | chr8:109565985-109574051 | 22370 | Ubn1 | NM_026666.3 | chr16:5050067-5086285 |
| 22276 | Txnrd1 | NM_001042513.1 | chr10:82859205-82897724 | 22371 | Ubn2 | NM_177185.4 | chr6:38433924-38512763 |
| 22277 | Txnrd2 | NM_013711.3 | chr16:18426416-18479073 | 22372 | Ubox5 | NM_001255993.1 | chr2:130589995-130630038 |
| 22278 | Txnrd3 | NM_001178058.1 | chr6:89643987-89675529 | 22373 | Ubp1 | NM_001083319.1 | chr9:113930933-113977201 |
| 22279 | Tyk2 | NM_001205312.1 | chr9:21104067-21131275 | 22374 | Ubqln1 | NM_026842.4 | chr13:58176155-58215653 |
| 22280 | Tymp | NM_138302.1 | chr15:89371930-89377037 | 22375 | Ubqln2 | NM_018798.2 | chrX:153498231-153501558 |
| 22281 | Tyms | NM_021288.4 | chr5:30058199-30073625 | 22376 | Ubqln3 | NM_198623.2 | chr7:104140622-104143272 |
| 22282 | Tyms-ps | NR_000040.2 | chr10:87966670-87968017 | 22377 | Ubqln4 | NM_033526.2 | chr3:88553715-88569725 |
| 22283 | Tyr | NM_011661.4 | chr7:87427404-87493411 | 22378 | Ubqlnl | NM_198624.3 | chr7:104148258-104150556 |
| 22284 | Tyro3 | NM_001290800.1 | chr2:119797739-119818103 | 22379 | Ubr1 | NM_009461.2 | chr2:120860275-120970715 |
| 22285 | Tyrobp | NM_011662.2 | chr7:30413787-30417579 | 22380 | Ubr2 | NM_001177374.1 | chr17:46928290-47010532 |
| 22286 | Tyrp1 | NM_001282014.1 | chr4:80834212-80851736 | 22381 | Ubr3 | NM_001303033.1 | chr2:69886989-70024010 |
| 22287 | Tysnd1 | NM_001272090.1 | chr10:61695513-61702773 | 22382 | Ubr4 | NM_001160319.1 | chr4:139380658-139489532 |
| 22288 | Tyw1 | NM_001015876.2 | chr5:130257036-130341567 | 22383 | Ubr5 | NM_001081359.3 | chr15:37967327-38078854 |
| 22289 | Tyw3 | NM_001168358.1 | chr3:154576519-154597098 | 22384 | Ubr7 | NM_025666.2 | chr12:102757974-102777701 |
| 22290 | Tyw5 | NM_001173592.1 | chr1:57388243-57406674 | 22385 | Ubtd1 | NM_145500.3 | chr19:41981762-42034641 |
| 22291 | U2af1 | NM_001163769.1 | chr17:31647081-31658754 | 22386 | Ubtd2 | NM_173784.3 | chr11:32455371-32518709 |
| 22292 | U2af1l4 | NM_170760.3 | chr7:30563339-30565364 | 22387 | Ubtf | NM_001044283.2 | chr11:102304562-102317287 |
| 22293 | U2af2 | NM_001205231.1 | chr7:5062142-5079945 | 22388 | Ubtfl1 | NM_001033793.3 | chr9:18404417-18411502 |
| 22294 | U2surp | NM_001114977.1 | chr9:95456893-95511996 | 22389 | Ubxn1 | NM_146093.1 | chr19:8871558-8875656 |
| 22295 | U90926 | NR_033483.1 | chr5:92209894-92215408 | 22390 | Ubxn10 | NM_001285928.1 | chr4:138718525-138737167 |
| 22296 | Uaca | NM_028283.2 | chr9:60794547-60880370 | 22391 | Ubxn11 | NM_026257.3 | chr4:134102582-134126780 |
| 22297 | Uap1 | NM_133806.5 | chr1:170141222-170174964 | 22392 | Ubxn2a | NM_145441.3 | chr12:4879031-4907520 |
| 22298 | Uap1l1 | NM_001033293.2 | chr2:25361491-25365626 | 22393 | Ubxn2b | NM_026534.2 | chr4:6191104-6219788 |
| 22299 | Uba1 | NM_001146295.2 | chrX:20662895-20683179 | 22394 | Ubxn4 | NM_026390.2 | chr1:128244180-128279377 |
| 22300 | Uba1y | NM_011667.2 | chrY:818712-844224 | 22395 | Ubxn6 | NM_024432.2 | chr17:56068252-56074989 |
| 22301 | Uba2 | NM_016682.2 | chr7:34140696-34168529 | 22396 | Ubxn7 | NM_177633.4 | chr16:32332251-32393747 |
| 22302 | Uba3 | NM_011111106.2 | chr6:97183631-97205647 | 22397 | Ubxn8 | NM_178648.2 | chr8:33619585-33641976 |
| 22303 | Uba5 | NM_025692.3 | chr9:104046587-104063121 | 22398 | Uchl1 | NM_011670.4 | chr5:66676120-66687234 |
| 22304 | Uba52 | NM_019883.3 | chr8:70508265-70510367 | 22399 | Uchl1os | NR_102714.1 | chr5:66626494-66676497 |
| 22305 | Uba6 | NM_172712.2 | chr5:86110729-86172743 | 22400 | Uchl3 | NM_016723.2 | chr14:101663966-101696125 |
| 22306 | Uba7 | NM_023738.4 | chr9:107975566-107984056 | 22401 | Uchl4 | NM_033607.1 | chr9:64235200-64236362 |
| 22307 | Ubac1 | NM_133853.3 | chr2:25996957-26021760 | 22402 | Uchl5 | NM_001159866.1 | chr1:143777277-143807466 |
| 22308 | Ubac2 | NM_026861.2 | chr14:121878665-122021035 | 22403 | Uck1 | NM_011675.2 | chr2:32255001-32260105 |
| 22309 | Ubald1 | NM_145359.2 | chr16:48747778-4879851 | 22404 | Uck2 | NM_030724.3 | chr1:167226083-167285127 |
| 22310 | Ubald2 | NM_178902.3 | chr11:116434093-116439077 | 22405 | Uckl1 | NM_026765.3 | chr2:181569152-181581973 |
| 22311 | Ubap1 | NM_001290454.1 | chr4:41348895-41389766 | 22406 | Uckl1os | NR_027289.1 | chr2:181578479-181585115 |
| 22312 | Ubap1l | NM_001111145.1 | chr9:65361059-65380377 | 22407 | Ucma | NM_001113558.2 | chr2:4976121-4985748 |
| 22313 | Ubap2 | NM_026872.1 | chr4:41194314-41275135 | 22408 | Ucn | NM_021290.2 | chr5:31337988-31338895 |
| 22314 | Ubap2l | NM_001165983.1 | chr3:90000287-90052475 | 22409 | Ucn2 | NM_145077.1 | chr9:108986162-108987164 |
| 22315 | Ubash3a | NM_177823.4 | chr17:31208065-31242403 | 22410 | Ucn3 | NM_031250.5 | chr13:3940687-3945349 |

Fig. 26 - 119

| | | | |
|---|---|---|---|
| 22411 | Ucp1 | NM_009463.3 | chr8:83290347-83298456 |
| 22412 | Ucp2 | NM_011671.5 | chr7:100493357-100499629 |
| 22413 | Ucp3 | NM_009464.3 | chr7:100472990-100486432 |
| 22414 | Uevld | NM_001040695.1 | chr7:46923215-46958518 |
| 22415 | Ufc1 | NM_025388.2 | chr1:171288563-171294982 |
| 22416 | Ufd1l | NM_011672.4 | chr16:18812293-18835261 |
| 22417 | Uffl | NM_026194.4 | chr4:25248585-25281821 |
| 22418 | Ufm1 | NM_026435.5 | chr3:53853375-53863807 |
| 22419 | Ufsp1 | NM_027356.2 | chr5:137294668-137295664 |
| 22420 | Ufsp2 | NM_138668.2 | chr8:45975527-45996956 |
| 22421 | Ugcg | NM_011673.3 | chr4:59189549-59222833 |
| 22422 | Ugdh | NM_009466.2 | chr5:65413221-65435842 |
| 22423 | Uggt1 | NM_198899.2 | chr1:36140027-36244302 |
| 22424 | Uggt2 | NM_001081252.2 | chr14:118984984-119099434 |
| 22425 | Ugp2 | NM_001290634.1 | chr11:21321125-21371267 |
| 22426 | Ugt1a1 | NM_201645.2 | chr1:88211958-88220002 |
| 22427 | Ugt1a10 | NM_201614.2 | chr1:88055410-88220002 |
| 22428 | Ugt1a2 | NM_013701.3 | chr1:88200610-88220002 |
| 22429 | Ugt1a5 | NM_201643.2 | chr1:88166011-88220002 |
| 22430 | Ugt1a6a | NM_145079.3 | chr1:88134808-88220002 |
| 22431 | Ugt1a6b | NM_201410.3 | chr1:88103256-88218998 |
| 22432 | Ugt1a7c | NM_201642.4 | chr1:88095000-88220002 |
| 22433 | Ugt1a9 | NM_201644.2 | chr1:88070778-88220002 |
| 22434 | Ugt2a1 | NM_053184.2 | chr5:87459489-87490871 |
| 22435 | Ugt2a2 | NM_001024148.1 | chr5:87459492-87482258 |
| 22436 | Ugt2a3 | NM_028094.3 | chr5:87324971-87337195 |
| 22437 | Ugt2b1 | NM_152811.1 | chr5:86916638-86926503 |
| 22438 | Ugt2b34 | NM_153598.2 | chr5:86889769-86906937 |
| 22439 | Ugt2b35 | NM_172881.3 | chr5:87000859-87013274 |
| 22440 | Ugt2b36 | NM_001029867.1 | chr5:87065926-87092555 |
| 22441 | Ugt2b37 | NM_053215.3 | chr5:87240491-87254788 |
| 22442 | Ugt2b38 | NM_133894.2 | chr5:87409939-87424203 |
| 22443 | Ugt2b5 | NM_009467.3 | chr5:87124946-87140340 |
| 22444 | Ugt3a1 | NM_207216.2 | chr5:9279828-9315036 |
| 22445 | Ugt3a2 | NM_144845.3 | chr15:9335597-9370870 |
| 22446 | Ugt8a | NM_011674.4 | chr3:125846342-125938550 |
| 22447 | Uhmk1 | NM_010633.3 | chr1:170199255-170215393 |
| 22448 | Uhrf1 | NM_001111078.1 | chr17:56304812-56332486 |
| 22449 | Uhrf1bp1 | NM_001080769.1 | chr17:27856506-27900040 |
| 22450 | Uhrf1bp1l | NM_029166.2 | chr10:89744990-89819869 |
| 22451 | Uhrf2 | NM_144873.2 | chr19:30030512-30093724 |
| 22452 | Uimc1 | NM_011307.2 | chr13:55027879-55100295 |
| 22453 | Ulbp1 | NM_029975.2 | chr10:7444872-7473477 |
| 22454 | Ulk1 | NM_009469.3 | chr5:110784488-110810081 |
| 22455 | Ulk2 | NM_013814.1 | chr11:61775597-61855092 |
| 22456 | Ulk3 | NM_027895.1 | chr9:57589451-57596233 |
| 22457 | Ulk4 | NM_177589.3 | chr9:120964453-121277172 |
| 22458 | Umod | NM_001278605.1 | chr7:119462707-119479262 |
| 22459 | Umodl1 | NM_177485.4 | chr17:30954682-31010710 |
| 22460 | Umps | NM_009471.2 | chr16:33955011-33967003 |
| 22461 | Unc119 | NM_011676.3 | chr11:78343494-78349164 |
| 22462 | Unc119b | NM_175352.4 | chr5:115122565-115134975 |
| 22463 | Unc13a | NM_001029871.2 | chr8:71626711-71671757 |
| 22464 | Unc13b | NM_001081413.2 | chr4:43058952-43264873 |
| 22465 | Unc13c | NM_001081153.1 | chr9:73479423-73933567 |
| 22466 | Unc13d | NM_001009573.2 | chr11:116062095-116077961 |
| 22467 | Unc45a | NM_133952.2 | chr7:80325291-80340219 |
| 22468 | Unc45b | NM_178680.4 | chr11:82911252-82943406 |
| 22469 | Unc50 | NM_026123.3 | chr1:37430171-37439124 |
| 22470 | Unc5a | NM_153131.3 | chr13:54949431-55006018 |
| 22471 | Unc5b | NM_029770.2 | chr10:60762594-60831581 |
| 22472 | Unc5c | NM_009472.2 | chr3:141465563-141834924 |
| 22473 | Unc5cl | NM_152823.4 | chr17:48454900-48468684 |
| 22474 | Unc5d | NM_153135.3 | chr8:28646716-29219636 |
| 22475 | Unc79 | NM_001081017.2 | chr12:102948858-103183997 |
| 22476 | Unc80 | NM_175510.3 | chr1:66468446-66699148 |
| 22477 | Unc93a | NM_199252.2 | chr17:13108616-13131791 |
| 22478 | Unc93b1 | NM_001161428.1 | chr19:3935185-3949340 |
| 22479 | Uncx | NM_013702.3 | chr5:139543897-139548178 |
| 22480 | Ung | NM_001040691.1 | chr5:114130434-114139321 |
| 22481 | Unk | NM_001286006.1 | chr11:116030315-116061214 |
| 22482 | Unkl | NM_001197024.1 | chr17:25188399-25234442 |
| 22483 | Uox | NM_009474.5 | chr3:146597148-146631483 |
| 22484 | Upb1 | NM_133995.4 | chr10:75406910-75441679 |
| 22485 | Upf1 | NM_001122829.1 | chr8:70831521-70853273 |
| 22486 | Upf2 | NM_001081132.1 | chr2:5951468-6056703 |
| 22487 | Upf3a | NM_025924.2 | chr8:13785614-13798537 |
| 22488 | Upf3b | NM_026573.3 | chrX:37091677-37110322 |
| 22489 | Upk1a | NM_026815.3 | chr7:30603091-30612734 |
| 22490 | Upk1b | NM_178924.4 | chr16:38773183-38800203 |
| 22491 | Upk2 | NM_009476.2 | chr9:44452714-44454767 |
| 22492 | Upk3a | NM_023478.2 | chr15:85017140-85022560 |
| 22493 | Upk3b | NM_175309.4 | chr5:136038495-136044993 |
| 22494 | Upk3bl | NM_027158.3 | chr5:136057266-136064324 |
| 22495 | Upp1 | NM_009491.1 | chr11:9187007-9136170 |
| 22496 | Upp2 | NM_001289659.1 | chr2:58755183-58791242 |
| 22497 | Uprt | NM_001081189.1 | chrX:104482781-104506262 |
| 22498 | Uqcc1 | NM_018888.4 | chr2:155846885-155930310 |
| 22499 | Uqcc2 | NM_026063.2 | chr17:27122664-27133891 |
| 22500 | Uqcr10 | NM_197979.2 | chr11:4701967-4704344 |
| 22501 | Uqcr11 | NM_025650.2 | chr10:80402996-80406821 |
| 22502 | Uqcrb | NM_026219.1 | chr13:66900620-66905350 |
| 22503 | Uqcrc1 | NM_025407.2 | chr9:108936647-108949641 |
| 22504 | Uqcrc2 | NM_025899.2 | chr7:120635188-120659523 |
| 22505 | Uqcrfs1 | NM_025710.2 | chr13:30540311-30545316 |
| 22506 | Uqcrh | NM_025641.3 | chr4:116066964-116075070 |
| 22507 | Uqcrq | NM_025352.2 | chr11:53428947-53430831 |
| 22508 | Urad | NM_001039678.2 | chr5:147314983-147322440 |
| 22509 | Urah | NM_029821.2 | chr7:140835495-140837968 |
| 22510 | Urb1 | NM_029497.1 | chr16:90751526-90810413 |
| 22511 | Urb2 | NM_001029876.1 | chr8:124023472-124048504 |
| 22512 | Urgcp | NM_001077661.1 | chr11:5713416-5762376 |
| 22513 | Uri1 | NM_011274.5 | chr7:37959991-38019552 |
| 22514 | Urm1 | NM_026615.4 | chr2:29827388-29844996 |
| 22515 | Uroc1 | NM_144940.2 | chr6:90333288-90364548 |
| 22516 | Urod | NM_009478.4 | chr4:116989964-116994413 |
| 22517 | Uros | NM_009479.3 | chr7:133686354-133709295 |
| 22518 | Usb1 | NM_133954.2 | chr8:95332283-95347513 |
| 22519 | Use1 | NM_001145780.1 | chr8:71366847-71369732 |
| 22520 | Usf1 | NM_009480.3 | chr1:171411680-171418759 |
| 22521 | Usf2 | NM_011680.2 | chr7:30945247-30956803 |
| 22522 | Ush1c | NM_001163733.1 | chr7:46195350-46238490 |
| 22523 | Ush1g | NM_176847.3 | chr11:115315191-115321918 |
| 22524 | Ush2a | NM_021408.3 | chr1:188262837-188965039 |
| 22525 | Ushbp1 | NM_181418.3 | chr8:71384273-71395801 |
| 22526 | Usmg5 | NM_023211.4 | chr19:47083470-47090625 |
| 22527 | Uso1 | NM_019490.1 | chr5:92137937-92202795 |
| 22528 | Usp1 | NM_146144.4 | chr4:98923809-98935542 |
| 22529 | Usp10 | NM_009462.2 | chr8:119910359-119957559 |
| 22530 | Usp11 | NM_145628.4 | chrX:20703908-20720539 |
| 22531 | Usp12 | NM_011669.3 | chr5:146734811-146794956 |
| 22532 | Usp13 | NM_001013024.2 | chr3:32817625-32935257 |
| 22533 | Usp14 | NM_001038589.2 | chr18:9993614-10030149 |
| 22534 | Usp15 | NM_027604.4 | chr10:123105005-123197019 |
| 22535 | Usp16 | NM_024258.2 | chr16:87454984-87483513 |
| 22536 | Usp17la | NM_007887.2 | chr7:104857015-104862667 |
| 22537 | Usp17lb | NM_201409.2 | chr7:104840311-104842504 |
| 22538 | Usp17lc | NM_010089.3 | chr7:103416695-103419174 |
| 22539 | Usp17ld | NM_001001559.2 | chr7:103250085-103252505 |
| 22540 | Usp17le | NM_001256973.1 | chr7:104768048-104777470 |
| 22541 | Usp18 | NM_011909.2 | chr6:121245905-121270917 |
| 22542 | Usp19 | NM_001168371.2 | chr9:108490675-108502337 |
| 22543 | Usp2 | NM_016808.2 | chr9:44069428-44095627 |
| 22544 | Usp20 | NM_028846.5 | chr2:30982278-31022655 |
| 22545 | Usp21 | NM_013919.4 | chr1:171281952-171287961 |
| 22546 | Usp22 | NM_001004143.4 | chr11:61151780-61175059 |
| 22547 | Usp24 | NM_183225.2 | chr4:106316212-106441327 |
| 22548 | Usp25 | NM_013918.2 | chr16:77014068-77116780 |
| 22549 | Usp26 | NM_031388.2 | chrX:51753958-51801233 |
| 22550 | Usp27x | NM_019461.4 | chrX:7372590-7375830 |
| 22551 | Usp28 | NM_175482.3 | chr9:48985384-49042517 |
| 22552 | Usp29 | NM_001290994.1 | chr7:6730582-6967219 |
| 22553 | Usp3 | NM_144937.4 | chr9:66514638-66593115 |
| 22554 | Usp30 | NM_001033202.3 | chr5:114100332-114122924 |
| 22555 | Usp31 | NM_001033173.1 | chr7:121642020-121707253 |
| 22556 | Usp32 | NM_001029934.1 | chr11:84984487-85139955 |
| 22557 | Usp33 | NM_001076676.2 | chr3:152346477-152393614 |
| 22558 | Usp34 | NM_001190401.2 | chr11:23306884-23490560 |
| 22559 | Usp35 | NM_001177412.1 | chr7:97309379-97325964 |
| 22560 | Usp36 | NM_001035528.1 | chr11:118259652-118290244 |
| 22561 | Usp37 | NM_178972.4 | chr1:74435509-74544286 |
| 22562 | Usp38 | NM_027554.2 | chr8:80980732-81014906 |
| 22563 | Usp39 | NM_138592.4 | chr6:72318675-72345175 |
| 22564 | Usp4 | NM_011678.2 | chr9:108347830-108392529 |
| 22565 | Usp40 | NM_001033291.2 | chr1:87945120-88008551 |
| 22566 | Usp42 | NM_029749.2 | chr5:143710325-143732280 |
| 22567 | Usp43 | NM_001291049.1 | chr11:67854522-67922153 |
| 22568 | Usp44 | NM_001206851.1 | chr10:93831554-93858087 |
| 22569 | Usp45 | NM_001290425.1 | chr4:21776269-21837872 |
| 22570 | Usp46 | NM_177561.5 | chr5:74000037-74068411 |
| 22571 | Usp47 | NM_133758.3 | chr7:112023505-112111386 |
| 22572 | Usp48 | NM_130879.2 | chr4:137594188-137658537 |
| 22573 | Usp49 | NM_198421.1 | chr17:47630689-47684067 |
| 22574 | Usp5 | NM_013700.1 | chr6:124815018-124829447 |
| 22575 | Usp50 | NM_029163.3 | chr2:126761049-126783460 |
| 22576 | Usp51 | NM_001137547.1 | chrX:153006468-153009459 |
| 22577 | Usp53 | NM_133857.3 | chr3:122933600-122984447 |
| 22578 | Usp54 | NM_030180.2 | chr14:20548911-20618354 |
| 22579 | Usp6nl | NM_001080548.1 | chr2:6322756-6443820 |
| 22580 | Usp7 | NM_001003918.2 | chr16:8688721-8738342 |
| 22581 | Usp8 | NM_001252580.1 | chr2:126707327-126759314 |
| 22582 | Usp9x | NM_009481.2 | chrX:13071497-13173327 |
| 22583 | Usp9y | NM_148943.2 | chrY:1298960-1459782 |
| 22584 | Usp1 | NM_001013378.2 | chr5:149184559-149215434 |
| 22585 | Ust | NM_177387.3 | chr10:8204752-8518825 |
| 22586 | Utf1 | NM_009482.2 | chr7:139943855-139945112 |
| 22587 | Utp11l | NM_026031.3 | chr4:124678763-124693554 |
| 22588 | Utp14a | NM_028276.2 | chrX:48256933-48282449 |
| 22589 | Utp14b | NM_001001981.3 | chr1:78657824-78667601 |
| 22590 | Utp15 | NM_178918.3 | chr13:98246844-98262992 |
| 22591 | Utp18 | NM_001013375.3 | chr11:93859242-93885766 |
| 22592 | Utp20 | NM_175158.3 | chr10:88746606-88826814 |
| 22593 | Utp23 | NM_030132.5 | chr15:51877440-51884622 |
| 22594 | Utp3 | NM_023054.1 | chr5:88554482-88556083 |
| 22595 | Utp6 | NM_144826.3 | chr11:79933955-79962387 |
| 22596 | Utrn | NM_011682.4 | chr10:12382187-12861735 |
| 22597 | Uts2 | NM_011910.2 | chr4:150997091-151001810 |
| 22598 | Uts2b | NM_198166.3 | chr16:27353321-27370239 |
| 22599 | Uts2r | NM_145440.1 | chr11:121160270-121161973 |
| 22600 | Uty | NM_009484.2 | chrY:1097143-1245738 |

Fig. 26 - 120

| | | | |
|---|---|---|---|
| 22601 | Uvrag | NM_178635.3 | chr7:98886742-99141144 |
| 22602 | Uvssa | NM_001081101.2 | chr5:33378695-33419754 |
| 22603 | Uxs1 | NM_026430.3 | chr1:43750230-43827708 |
| 22604 | Uxt | NM_013840.3 | chrX:20951664-20961978 |
| 22605 | V1ra8 | NM_053223.1 | chr6:90202816-90203656 |
| 22606 | V1rd18 | NM_207618.2 | chr7:24003090-24004247 |
| 22607 | V1rd19 | NM_207619.2 | chr7:24003110-24004028 |
| 22608 | Vac14 | NM_146216.2 | chr8:110618637-110720398 |
| 22609 | Vamp1 | NM_001080557.1 | chr6:125215580-125222306 |
| 22610 | Vamp2 | NM_009497.3 | chr11:69088527-69092381 |
| 22611 | Vamp3 | NM_009498.4 | chr4:151047304-151057953 |
| 22612 | Vamp4 | NM_016796.3 | chr1:162570827-162599078 |
| 22613 | Vamp5 | NM_001080742.2 | chr6:72368048-72380468 |
| 22614 | Vamp7 | NM_011515.5 | chrX_GL456233_random:107 36-35191 |
| 22615 | Vamp8 | NM_016794.3 | chr6:72385220-72390667 |
| 22616 | Vangl1 | NM_177545.5 | chr3:102155899-102205011 |
| 22617 | Vangl2 | NM_033509.4 | chr1:172000959-172027295 |
| 22618 | Vapa | NM_013933.3 | chr17:65580052-65613555 |
| 22619 | Vapb | NM_019806.5 | chr2:173737570-173784336 |
| 22620 | Vars | NM_011690.3 | chr17:35000906-35016329 |
| 22621 | Vars2 | NM_175137.4 | chr17:35655634-35667592 |
| 22622 | Vash1 | NM_177354.4 | chr12:86678899-86695681 |
| 22623 | Vash2 | NM_144879.2 | chr1:190947645-190978998 |
| 22624 | Vasn | NM_139307.3 | chr16:4639944-4651166 |
| 22625 | Vasp | NM_001282021.1 | chr7:19256929-19271854 |
| 22626 | Vat1 | NM_012403.2 | chr11:101458747-101466199 |
| 22627 | Vat1l | NM_173016.3 | chr8:114205639-114374070 |
| 22628 | Vault rc5 | NR_027885.1 | chr18:36801762-36802107 |
| 22629 | Vav1 | NM_001163815.1 | chr17:57279099-57329236 |
| 22630 | Vav2 | NM_009500.3 | chr2:27263634-27426825 |
| 22631 | Vav3 | NM_020505.2 | chr3:109340682-109685694 |
| 22632 | Vax1 | NM_009501.1 | chr19:59166186-59170029 |
| 22633 | Vax2 | NM_011912.3 | chr6:83711263-83738304 |
| 22634 | Vax2os | NR_002871.1 | chr6:83692805-83712201 |
| 22635 | Vbp1 | NM_011692.2 | chrX:75514296-75534946 |
| 22636 | Vcam1 | NM_011693.3 | chr3:116110019-116129688 |
| 22637 | Vcan | NM_001081249.1 | chr13:89655309-89742512 |
| 22638 | Vcl | NM_009502.4 | chr14:20929432-21033673 |
| 22639 | Vcp | NM_009503.4 | chr4:42979963-43000507 |
| 22640 | Vcpip1 | NM_173443.2 | chr1:9718621-9748382 |
| 22641 | Vcpkmt | NM_001033236.2 | chr12:69577627-69583028 |
| 22642 | Vdac1 | NM_011694.5 | chr11:52360861-52389397 |
| 22643 | Vdac2 | NM_011695.2 | chr14:21831566-21845879 |
| 22644 | Vdac3 | NM_001198998.1 | chr8:22577074-22593813 |
| 22645 | Vdr | NM_009504.4 | chr15:97854426-97908296 |
| 22646 | Vegfa | NM_001025250.3 | chr17:46016992-46032377 |
| 22647 | Vegfb | NM_001185164.1 | chr19:6982471-6987651 |
| 22648 | Vegfc | NM_009506.2 | chr8:54077531-54186454 |
| 22649 | Veph1 | NM_145820.3 | chr3:66053557-66296837 |
| 22650 | Vezf1 | NM_016686.4 | chr11:88068278-88084729 |
| 22651 | Vezt | NM_172538.5 | chr10:93961521-94035799 |
| 22652 | Vgf | NM_001039385.1 | chr5:137030294-137033351 |
| 22653 | Vgll1 | NM_133251.2 | chrX:57088105-57106540 |
| 22654 | Vgll2 | NM_153786.2 | chr10:52022501-52028471 |
| 22655 | Vgll3 | NM_028572.1 | chr16:65815632-65863066 |
| 22656 | Vgll4 | NM_177683.2 | chr6:114862091-114921752 |
| 22657 | Vhl | NM_009507.3 | chr6:113624020-113641633 |
| 22658 | Vil1 | NM_009509.2 | chr1:74409383-74435560 |
| 22659 | Vill | NM_001164567.1 | chr9:119052777-119071525 |
| 22660 | Vim | NM_011701.4 | chr2:13574310-13592826 |
| 22661 | Vimp | NM_024439.3 | chr7:66079648-66089405 |
| 22662 | Vip | NM_011702.3 | chr10:5639217-5647616 |
| 22663 | Vipas39 | NM_001142580.1 | chr12:87238874-87266286 |
| 22664 | Vipr1 | NM_011703.4 | chr9:121642715-121672954 |
| 22665 | Vipr2 | NM_009511.2 | chr12:116077725-116146261 |
| 22666 | Vit | NM_001197028.1 | chr17:78508062-78627409 |
| 22667 | Vkorc1 | NM_178600.2 | chr7:127893062-127895617 |
| 22668 | Vkorc1l1 | NM_001001327.2 | chr5:129942108-129986692 |
| 22669 | Vldlr | NM_001161420.1 | chr19:27217019-27254231 |
| 22670 | Vma21 | NM_001081356.3 | chrX:71816757-71824706 |
| 22671 | Vmac | NM_001166474.1 | chr17:56713931-56717699 |
| 22672 | Vmn1r1 | NM_001166726.1 | chr1:182157177-182158098 |
| 22673 | Vmn1r10 | NM_053231.2 | chr6:57113424-57114360 |
| 22674 | Vmn1r100 | NM_001166644.1 | chr7:20417941-22414506 |
| 22675 | Vmn1r101 | NM_001166836.1 | chr7:20441669-22438229 |
| 22676 | Vmn1r103 | NM_001166737.1 | chr7:20509616-20510534 |
| 22677 | Vmn1r104 | NM_001166738.1 | chr7:20533836-22523890 |
| 22678 | Vmn1r107 | NM_001166759.1 | chr7:20668917-23218255 |
| 22679 | Vmn1r11 | NM_053233.2 | chr6:57137352-57138252 |
| 22680 | Vmn1r112 | NM_001166847.1 | chr7:20771184-20772078 |
| 22681 | Vmn1r113 | NM_001166716.1 | chr7:20787284-20788208 |
| 22682 | Vmn1r114 | NM_001166837.1 | chr7:20811220-20812186 |
| 22683 | Vmn1r115 | NM_001166745.1 | chr7:20844097-20844985 |
| 22684 | Vmn1r116 | NM_001166744.1 | chr7:20872255-20873179 |
| 22685 | Vmn1r117 | NM_001166743.1 | chr7:20883197-20884121 |
| 22686 | Vmn1r118 | NM_001166724.1 | chr7:20232907-22229484 |
| 22687 | Vmn1r119 | NM_001166708.1 | chr7:21011531-21012455 |
| 22688 | Vmn1r12 | NM_001101579.1 | chr6:57158919-57159843 |
| 22689 | Vmn1r120 | NM_001166715.1 | chr7:21052866-21053784 |
| 22690 | Vmn1r121 | NM_001166741.1 | chr7:21097568-21098513 |
| 22691 | Vmn1r122 | NM_001166714.1 | chr7:21133210-21134128 |
| 22692 | Vmn1r123 | NM_001166707.1 | chr7:21162184-21163108 |
| 22693 | Vmn1r124 | NM_001166757.1 | chr7:21259693-21260617 |
| 22694 | Vmn1r125 | NM_001166740.1 | chr7:21272178-21273102 |
| 22695 | Vmn1r126 | NM_001166838.1 | chr7:21300501-21301467 |
| 22696 | Vmn1r127 | NM_001166726.1 | chr7:21318943-21319861 |
| 22697 | Vmn1r128 | NM_001166739.1 | chr7:21349372-21350296 |
| 22698 | Vmn1r129 | NM_001166725.1 | chr7:21360367-21361291 |
| 22699 | Vmn1r13 | NM_053235.2 | chr6:57209857-57210760 |
| 22700 | Vmn1r130 | NM_001166848.1 | chr7:21511780-21512703 |
| 22701 | Vmn1r132 | NM_001122682.1 | chr7:21612744-22097921 |
| 22702 | Vmn1r135 | NM_001166747.1 | chr7:21832350-23056463 |
| 22703 | Vmn1r137 | NM_001166849.1 | chr7:21994587-21995510 |
| 22704 | Vmn1r138 | NM_001167169.1 | chr7:22027977-22028897 |
| 22705 | Vmn1r139 | NM_001166748.1 | chr7:21614091-22097760 |
| 22706 | Vmn1r14 | NM_053237.2 | chr6:57233438-57234350 |
| 22707 | Vmn1r142 | NM_001166749.1 | chr7:20167459-22164035 |
| 22708 | Vmn1r148 | NM_030736.2 | chr7:22412230-22414668 |
| 22709 | Vmn1r15 | NM_053236.2 | chr6:57258148-57259048 |
| 22710 | Vmn1r151 | NM_001166712.1 | chr7:22498780-22499678 |
| 22711 | Vmn1r152 | NM_001166752.1 | chr7:20533836-22523890 |
| 22712 | Vmn1r157 | NM_001166754.1 | chr7:22761696-22762590 |
| 22713 | Vmn1r158 | NM_001166841.1 | chr7:22789858-22790782 |
| 22714 | Vmn1r159 | NM_001167581.1 | chr7:22842687-22843605 |
| 22715 | Vmn1r16 | NM_134184.2 | chr6:57322723-57323635 |
| 22716 | Vmn1r160 | NM_001166724.1 | chr7:22871223-22872147 |
| 22717 | Vmn1r163 | NM_001166755.1 | chr7:23055540-23056463 |
| 22718 | Vmn1r165 | NM_001166850.1 | chr7:23217332-23218255 |
| 22719 | Vmn1r166 | NM_001167168.1 | chr7:23250762-23251682 |
| 22720 | Vmn1r167 | NM_001101562.1 | chr7:23504641-23505589 |
| 22721 | Vmn1r168 | NM_001166842.1 | chr7:23540719-23541649 |
| 22722 | Vmn1r169 | NM_001166843.1 | chr7:23577184-23578099 |
| 22723 | Vmn1r17 | NM_134171.1 | chr6:57360466-57361378 |
| 22724 | Vmn1r170 | NM_001166722.1 | chr7:23606174-23607089 |
| 22725 | Vmn1r171 | NM_030737.2 | chr7:23631987-23633568 |
| 22726 | Vmn1r172 | NM_030735.1 | chr7:23658315-23660663 |
| 22727 | Vmn1r173 | NM_001166718.1 | chr7:23702341-23703283 |
| 22728 | Vmn1r174 | NM_207548.2 | chr7:23753910-23754852 |
| 22729 | Vmn1r175 | NM_001166727.1 | chr7:23808285-23809200 |
| 22730 | Vmn1r176 | NM_001166721.1 | chr7:23834811-23835726 |
| 22731 | Vmn1r177 | NM_206872.2 | chr7:23865519-23866449 |
| 22732 | Vmn1r178 | NM_206868.1 | chr7:23893528-23894443 |
| 22733 | Vmn1r179 | NM_207545.1 | chr7:23928385-23929357 |
| 22734 | Vmn1r18 | NM_134181.1 | chr6:57389667-57390567 |
| 22735 | Vmn1r180 | NM_206869.2 | chr7:23952386-23953356 |
| 22736 | Vmn1r181 | NM_207546.2 | chr7:23983960-23985048 |
| 22737 | Vmn1r183 | NM_203489.1 | chr7:24054773-24055691 |
| 22738 | Vmn1r184 | NM_001167540.1 | chr7:26266830-26267775 |
| 22739 | Vmn1r185 | NM_134231.1 | chr7:26611118-26612078 |
| 22740 | Vmn1r186 | NM_001167567.1 | chr7:94185-5676224 |
| 22741 | Vmn1r187 | NM_001167568.1 | chr7:149260-5803631 |
| 22742 | Vmn1r188 | NM_145850.1 | chr13:22087877-22088804 |
| 22743 | Vmn1r189 | NM_145844.1 | chr13:22101726-22102665 |
| 22744 | Vmn1r19 | NM_134182.1 | chr6:57404463-57405390 |
| 22745 | Vmn1r191 | NM_145849.1 | chr13:22178685-22179582 |
| 22746 | Vmn1r192 | NM_145845.1 | chr13:22187145-22188048 |
| 22747 | Vmn1r193 | NM_134225.1 | chr13:22218860-22219820 |
| 22748 | Vmn1r194 | NM_001080972.1 | chr13:22244214-22245105 |
| 22749 | Vmn1r195 | NM_134223.2 | chr13:22278316-22279404 |
| 22750 | Vmn1r196 | NM_001167541.1 | chr13:22293192-22294098 |
| 22751 | Vmn1r197 | NM_134244.1 | chr13:22327910-22328807 |
| 22752 | Vmn1r198 | NM_134220.1 | chr13:22354345-22355248 |
| 22753 | Vmn1r199 | NM_134213.1 | chr13:22382537-22383641 |
| 22754 | Vmn1r2 | NM_001167534.1 | chr4:3172082-3173003 |
| 22755 | Vmn1r20 | NM_001101533.1 | chr6:57431690-57432602 |
| 22756 | Vmn1r200 | NM_134212.1 | chr13:22395028-22395967 |
| 22757 | Vmn1r201 | NM_134221.1 | chr13:22474617-22475520 |
| 22758 | Vmn1r202 | NM_134224.1 | chr13:22501336-22502245 |
| 22759 | Vmn1r203 | NM_134236.1 | chr13:22524050-22524986 |
| 22760 | Vmn1r204 | NM_001045544.1 | chr13:22556200-22557109 |
| 22761 | Vmn1r205 | NM_134217.1 | chr13:22591979-22592930 |
| 22762 | Vmn1r206 | NM_134216.1 | chr13:22620096-22621035 |
| 22763 | Vmn1r207-ps | NM_001166709.1 | chr13:22725683-22726622 |
| 22764 | Vmn1r208 | NM_134218.1 | chr13:22772398-22773325 |
| 22765 | Vmn1r209 | NM_001013787.1 | chr13:22805579-22806518 |
| 22766 | Vmn1r21 | NM_134183.1 | chr6:57843563-57844457 |
| 22767 | Vmn1r210 | NM_134235.1 | chr13:22827193-22828114 |
| 22768 | Vmn1r211 | NM_134243.1 | chr13:22851598-22852495 |
| 22769 | Vmn1r212 | NM_134241.1 | chr13:22883087-22884161 |
| 22770 | Vmn1r213 | NM_134215.1 | chr13:23011248-23012403 |
| 22771 | Vmn1r214 | NM_134214.1 | chr13:23034337-23035441 |
| 22772 | Vmn1r215 | NM_134219.1 | chr13:23075791-23076694 |
| 22773 | Vmn1r216 | NM_134245.1 | chr13:23099148-23100045 |
| 22774 | Vmn1r217 | NM_134239.1 | chr13:23113833-23114730 |
| 22775 | Vmn1r218 | NM_134222.1 | chr13:23136484-23137381 |
| 22776 | Vmn1r219 | NM_134238.1 | chr13:23162642-23163581 |
| 22777 | Vmn1r22 | NM_134178.1 | chr6:57900081-57900990 |
| 22778 | Vmn1r220 | NM_134237.1 | chr13:23183627-23184524 |
| 22779 | Vmn1r221 | NM_001167542.1 | chr13:23217372-23218311 |
| 22780 | Vmn1r222 | NM_134240.1 | chr13:23232114-23233041 |
| 22781 | Vmn1r223 | NM_001083311.1 | chr13:23249237-23250323 |
| 22782 | Vmn1r224 | NM_001166735.1 | chr17:20419162-20420059 |
| 22783 | Vmn1r225 | NM_134194.1 | chr17:20502298-20503195 |
| 22784 | Vmn1r226 | NM_134191.1 | chr17:20687507-20688404 |
| 22785 | Vmn1r227 | NM_134195.1 | chr17:20735099-20736126 |
| 22786 | Vmn1r228 | NM_134192.3 | chr17:20776058-20777501 |
| 22787 | Vmn1r229 | NM_134190.1 | chr17:20814494-20815415 |
| 22788 | Vmn1r23 | NM_134179.1 | chr6:57925882-57926791 |
| 22789 | Vmn1r230 | NM_134197.1 | chr17:20846550-20847501 |

Fig. 26 - 121

| | | | |
|---|---|---|---|
| 22790 | Vmn1r231 | NM_134196.1 | chr17:20889715-20890651 |
| 22791 | Vmn1r232 | NM_134193.2 | chr17:20913204-20914363 |
| 22792 | Vmn1r233 | NM_134202.1 | chr17:20993726-20994686 |
| 22793 | Vmn1r234 | NM_134198.1 | chr17:21228825-21229815 |
| 22794 | Vmn1r235 | NM_134199.3 | chr17:21260426-21262863 |
| 22795 | Vmn1r236 | NM_134201.2 | chr17:21286532-21287653 |
| 22796 | Vmn1r237 | NM_134200.1 | chr17:21314016-21314886 |
| 22797 | Vmn1r238 | NM_001167539.1 | chr18:3122491-3123412 |
| 22798 | Vmn1r24 | NM_134173.2 | chr6:57955640-57956531 |
| 22799 | Vmn1r25 | NM_053238.2 | chr6:57978393-57979302 |
| 22800 | Vmn1r26 | NM_134172.1 | chr6:58008182-58009202 |
| 22801 | Vmn1r27 | NM_134436.2 | chr6:58215105-58216017 |
| 22802 | Vmn1r28 | NM_134180.1 | chr6:58265173-58266082 |
| 22803 | Vmn1r29 | NM_053232.3 | chr6:58307296-58308208 |
| 22804 | Vmn1r3 | NM_001167535.1 | chr4:3184384-3185305 |
| 22805 | Vmn1r30 | NM_134177.1 | chr6:58434936-58435845 |
| 22806 | Vmn1r31 | NM_001166729.1 | chr6:58471966-58472878 |
| 22807 | Vmn1r32 | NM_134170.3 | chr6:66552182-66559708 |
| 22808 | Vmn1r33 | NM_134169.1 | chr6:66611650-66612568 |
| 22809 | Vmn1r34 | NM_001166719.1 | chr6:66636822-66637752 |
| 22810 | Vmn1r35 | NM_134167.1 | chr6:66678793-66679684 |
| 22811 | Vmn1r36 | NM_134166.1 | chr6:66715971-66716889 |
| 22812 | Vmn1r37 | NM_134165.1 | chr6:66731391-66732300 |
| 22813 | Vmn1r38 | NM_134168.1 | chr6:66776221-66777130 |
| 22814 | Vmn1r39 | NM_001166720.1 | chr6:66804414-66805332 |
| 22815 | Vmn1r4 | NM_134176.1 | chr6:56956512-56957406 |
| 22816 | Vmn1r40 | NM_053228.1 | chr6:89714202-89715135 |
| 22817 | Vmn1r41 | NM_053230.2 | chr6:89740887-89747414 |
| 22818 | Vmn1r42 | NM_053221.2 | chr6:89844517-89845615 |
| 22819 | Vmn1r43 | NM_053220.2 | chr6:89869480-89870529 |
| 22820 | Vmn1r44 | NM_053227.2 | chr6:89893273-89894206 |
| 22821 | Vmn1r45 | NM_011684.2 | chr6:89931649-89940507 |
| 22822 | Vmn1r46 | NM_053229.1 | chr6:89976170-89977100 |
| 22823 | Vmn1r47 | NM_053219.2 | chr6:90021887-90022820 |
| 22824 | Vmn1r48 | NM_053218.1 | chr6:90035932-90036841 |
| 22825 | Vmn1r49 | NM_011911.1 | chr6:90072085-90073018 |
| 22826 | Vmn1r5 | NM_134174.2 | chr6:56985341-56986289 |
| 22827 | Vmn1r50 | NM_053225.1 | chr6:90107274-90108207 |
| 22828 | Vmn1r51 | NM_011683.2 | chr6:90122642-90130645 |
| 22829 | Vmn1r52 | NM_053222.1 | chr6:90178715-90179645 |
| 22830 | Vmn1r53 | NM_053226.2 | chr6:90223316-90224438 |
| 22831 | Vmn1r54 | NM_053224.1 | chr6:90269105-90270053 |
| 22832 | Vmn1r55 | NM_001166706.1 | chr7:5146489-5147422 |
| 22833 | Vmn1r56 | NM_030740.1 | chr7:5194915-5196747 |
| 22834 | Vmn1r57 | NM_001166734.1 | chr7:5220477-5221410 |
| 22835 | Vmn1r58 | NM_030739.2 | chr7:5408889-5413145 |
| 22836 | Vmn1r59 | NM_207543.1 | chr7:5453826-5454759 |
| 22837 | Vmn1r6 | NM_134175.1 | chr6:57002354-57003266 |
| 22838 | Vmn1r60 | NM_001166732.1 | chr7:5544196-5545099 |
| 22839 | Vmn1r61 | NM_001166733.1 | chr7:5610410-5611313 |
| 22840 | Vmn1r62 | NM_030741.2 | chr7:93810-5676597 |
| 22841 | Vmn1r63 | NM_030742.1 | chr7:148880-5805445 |
| 22842 | Vmn1r64 | NM_207544.1 | chr7:5883579-5884542 |
| 22843 | Vmn1r65 | NM_030738.2 | chr7:6007749-6011010 |
| 22844 | Vmn1r66 | NM_134230.3 | chr7:10273827-10275351 |
| 22845 | Vmn1r67 | NM_134229.2 | chr7:10446788-10447787 |
| 22846 | Vmn1r68 | NM_001172072.1 | chr7:10527209-10528169 |
| 22847 | Vmn1r69 | NM_145842.3 | chr7:10579755-10581487 |
| 22848 | Vmn1r7 | NM_001166710.1 | chr6:57024337-57025273 |
| 22849 | Vmn1r70 | NM_134228.1 | chr7:10633586-10634483 |
| 22850 | Vmn1r71 | NM_145848.3 | chr7:10747501-10749538 |
| 22851 | Vmn1r72 | NM_145843.1 | chr7:11669598-11670519 |
| 22852 | Vmn1r73 | NM_134203.1 | chr7:11756256-11757168 |
| 22853 | Vmn1r74 | NM_134206.1 | chr7:11846774-11847689 |
| 22854 | Vmn1r75 | NM_134207.1 | chr7:11880342-11881260 |
| 22855 | Vmn1r76 | NM_134205.2 | chr7:11930310-11931285 |
| 22856 | Vmn1r77 | NM_001166731.1 | chr7:12041298-12042219 |
| 22857 | Vmn1r78 | NM_134208.2 | chr7:12152463-12153405 |
| 22858 | Vmn1r79 | NM_001166835.1 | chr7:12176192-12177113 |
| 22859 | Vmn1r8 | NM_134173.3 | chr6:57035912-57037125 |
| 22860 | Vmn1r80 | NM_134204.2 | chr7:12192964-12193891 |
| 22861 | Vmn1r81 | NM_134210.1 | chr7:12259758-12260679 |
| 22862 | Vmn1r82 | NM_134234.1 | chr7:12304804-12305719 |
| 22863 | Vmn1r83 | NM_134209.1 | chr7:12321207-12322128 |
| 22864 | Vmn1r84 | NM_134233.1 | chr7:12361807-12362764 |
| 22865 | Vmn1r85 | NM_145847.1 | chr7:13084288-13085215 |
| 22866 | Vmn1r86 | NM_001167536.1 | chr7:13101996-13102947 |
| 22867 | Vmn1r87 | NM_134227.1 | chr7:13131470-13132358 |
| 22868 | Vmn1r88 | NM_001167537.1 | chr7:13177718-13178669 |
| 22869 | Vmn1r89 | NM_134226.1 | chr7:13219338-13220289 |
| 22870 | Vmn1r9 | NM_134185.2 | chr6:57070894-57071945 |
| 22871 | Vmn1r90 | NM_001244031.1 | chr7:14561241-14562171 |
| 22872 | Vmn1r91 | NM_001166736.1 | chr7:20101157-20102081 |
| 22873 | Vmn1r94 | NM_001167723.1 | chr7:20167459-20164035 |
| 22874 | Vmn1r95 | NM_001167538.1 | chr7:20193709-22190300 |
| 22875 | Vmn1r-ps103 | NM_134211.2 | chr13:22441271-22442243 |
| 22876 | Vmn1r-ps79 | NR_030707.1 | chr7:20356625-22354555 |
| 22877 | Vmn2r1 | NM_019918.2 | chr3:64081641-64105458 |
| 22878 | Vmn2r10 | NM_009491.3 | chr5:108995538-109006436 |
| 22879 | Vmn2r100 | NM_001104562.1 | chr17:19504810-19532060 |
| 22880 | Vmn2r101 | NM_001104563.1 | chr17:19577230-19612317 |
| 22881 | Vmn2r102 | NM_001104564.1 | chr17:19660398-19694748 |
| 22882 | Vmn2r103 | NM_001104565.1 | chr17:19773362-19812536 |
| 22883 | Vmn2r104 | NM_001104566.1 | chr17:20029424-20048205 |
| 22884 | Vmn2r105 | NM_001104567.1 | chr17:20208229-20234872 |
| 22885 | Vmn2r106 | NM_001104568.1 | chr17:20267546-20285430 |
| 22886 | Vmn2r107 | NM_001104569.1 | chr17:20345424-20375772 |
| 22887 | Vmn2r108 | NM_001104570.1 | chr17:20462372-20481236 |
| 22888 | Vmn2r109 | NM_001104571.1 | chr17:20540516-20564756 |
| 22889 | Vmn2r11 | NM_001104622.1 | chr5:109046872-109059452 |
| 22890 | Vmn2r110 | NM_001104572.1 | chr17:20573828-20596259 |
| 22891 | Vmn2r111 | NM_001104573.1 | chr17:22547940-22573273 |
| 22892 | Vmn2r112 | NM_001104575.1 | chr17:22601147-22619133 |
| 22893 | Vmn2r113 | NM_001104578.1 | chr17:22943183-22958814 |
| 22894 | Vmn2r114 | NM_001102584.1 | chr17:23290933-23312313 |
| 22895 | Vmn2r115 | NM_001104579.1 | chr17:23343976-23360128 |
| 22896 | Vmn2r116 | NM_001104580.1 | chr17:23384802-23401864 |
| 22897 | Vmn2r117 | NM_001104581.1 | chr17:23459674-23479597 |
| 22898 | Vmn2r118 | NM_001104582.1 | chr17:55592340-55624672 |
| 22899 | Vmn2r12 | NM_001104623.1 | chr5:109085848-109097864 |
| 22900 | Vmn2r120 | NM_001104591.1 | chr17:57508782-57545314 |
| 22901 | Vmn2r121 | NM_001100616.1 | chrX:124127338-124135910 |
| 22902 | Vmn2r122 | NM_009488.2 | chr4_JH584292_random:3535-11935 |
| 22903 | Vmn2r123 | NM_009485.1 | chr4:156331125-156339496 |
| 22904 | Vmn2r124 | NM_001271883.1 | chr17:18049483-18074220 |
| 22905 | Vmn2r13 | NM_001104624.1 | chr5:109156067-109192107 |
| 22906 | Vmn2r14 | NM_001104625.1 | chr5:109215501-109224622 |
| 22907 | Vmn2r15 | NM_001104626.1 | chr5:109286268-109297556 |
| 22908 | Vmn2r16 | NM_001104627.1 | chr5:109330380-109364481 |
| 22909 | Vmn2r17 | NM_001104628.1 | chr5:109420012-109453387 |
| 22910 | Vmn2r18 | NM_001102582.1 | chr5:151561660-151586924 |
| 22911 | Vmn2r19 | NM_001104632.1 | chr6:123308332-123336537 |
| 22912 | Vmn2r2 | NM_001104592.1 | chr3:64116431-64137480 |
| 22913 | Vmn2r20 | NM_001104634.1 | chr6:123385261-123418061 |
| 22914 | Vmn2r21 | NM_001104635.1 | chr6:123492507-123533406 |
| 22915 | Vmn2r22 | NM_001104637.1 | chr6:123609757-123650635 |
| 22916 | Vmn2r23 | NM_001104638.1 | chr6:123702820-123742239 |
| 22917 | Vmn2r24 | NM_001104639.1 | chr6:123778970-123816280 |
| 22918 | Vmn2r25 | NM_001104641.1 | chr6:123822813-123853190 |
| 22919 | Vmn2r26 | NM_019917.2 | chr6:124024757-124062035 |
| 22920 | Vmn2r27 | NM_001104642.1 | chr6:124191595-124231784 |
| 22921 | Vmn2r28 | NM_001081405.1 | chr7:5480455-5493851 |
| 22922 | Vmn2r29 | NM_001113468.1 | chr7:7231326-7247328 |
| 22923 | Vmn2r3 | NM_001104614.1 | chr3:64258960-64287417 |
| 22924 | Vmn2r30 | NM_009490.3 | chr7:7312273-7337493 |
| 22925 | Vmn2r31 | NM_001105062.1 | chr7:7383984-7399627 |
| 22926 | Vmn2r32 | NM_001105063.1 | chr7:7463968-7479973 |
| 22927 | Vmn2r33 | NM_001105065.2 | chr7:7550966-7566786 |
| 22928 | Vmn2r34 | NM_001105066.1 | chr7:7671828-7689398 |
| 22929 | Vmn2r35 | NM_001105067.1 | chr7:7786150-7819867 |
| 22930 | Vmn2r36 | NM_001105068.1 | chr7:7876652-7902462 |
| 22931 | Vmn2r37 | NM_009489.2 | chr7:9205548-9223653 |
| 22932 | Vmn2r38 | NM_001105070.1 | chr7:9074795-9097765 |
| 22933 | Vmn2r39 | NM_001105071.1 | chr7:9014749-9030682 |
| 22934 | Vmn2r4 | NM_001104615.1 | chr3:64388620-64410057 |
| 22935 | Vmn2r40 | NM_001105072.1 | chr7:8907733-8931402 |
| 22936 | Vmn2r41 | NM_001105073.1 | chr7:8137904-8161551 |
| 22937 | Vmn2r42 | NM_009493.2 | chr7:8183268-8200320 |
| 22938 | Vmn2r43 | NM_198961.2 | chr7:8244350-8260599 |
| 22939 | Vmn2r44 | NM_001105074.1 | chr7:8367459-8383238 |
| 22940 | Vmn2r45 | NM_001105075.1 | chr7:8471468-8488959 |
| 22941 | Vmn2r46 | NM_001105076.1 | chr7:9485564-9770573 |
| 22942 | Vmn2r47 | NM_001105151.1 | chr7:8010338-9841325 |
| 22943 | Vmn2r48 | NM_001105152.1 | chr7:9927623-9953585 |
| 22944 | Vmn2r49 | NM_001105156.1 | chr7:9976244-9992139 |
| 22945 | Vmn2r5 | NM_001104618.1 | chr3:64490820-64507685 |
| 22946 | Vmn2r50 | NM_001105178.1 | chr7:10037234-10053178 |
| 22947 | Vmn2r51 | NM_001105179.1 | chr7:10087197-10105659 |
| 22948 | Vmn2r52 | NM_001105191.1 | chr7:10158651-10176286 |
| 22949 | Vmn2r53 | NM_001104644.1 | chr7:12581469-12606544 |
| 22950 | Vmn2r54 | NM_001081449.2 | chr7:12615232-12636134 |
| 22951 | Vmn2r55 | NM_001104645.1 | chr7:12651705-12684991 |
| 22952 | Vmn2r56 | NM_001104648.1 | chr7:12693997-12733105 |
| 22953 | Vmn2r57 | NM_177764.4 | chr7:41399731-41448641 |
| 22954 | Vmn2r58 | NM_001105055.1 | chr7:41836880-41872670 |
| 22955 | Vmn2r59 | NM_001105056.1 | chr7:42011791-42058981 |
| 22956 | Vmn2r6 | NM_001104619.1 | chr3:64537560-64559818 |
| 22957 | Vmn2r60 | NM_001105057.1 | chr7:42116470-42195776 |
| 22958 | Vmn2r61 | NM_001105058.1 | chr7:42260052-42300755 |
| 22959 | Vmn2r62 | NM_001105059.1 | chr7:42764437-42793496 |
| 22960 | Vmn2r63 | NM_001105060.1 | chr7:42903250-42933789 |
| 22961 | Vmn2r65 | NM_001105180.1 | chr7:84940168-84964009 |
| 22962 | Vmn2r66 | NM_001033878.3 | chr7:84994644-85012020 |
| 22963 | Vmn2r67 | NM_001102579.1 | chr7:85136339-85155902 |
| 22964 | Vmn2r68 | NM_001105181.1 | chr7:85221517-85237704 |
| 22965 | Vmn2r69 | NM_001105182.1 | chr7:85406375-85415676 |
| 22966 | Vmn2r7 | NM_175674.3 | chr3:64690659-64719602 |
| 22967 | Vmn2r70 | NM_001105183.1 | chr7:85558762-85569088 |
| 22968 | Vmn2r71 | NM_001105184.1 | chr7:85615461-85624547 |
| 22969 | Vmn2r72 | NM_001105185.1 | chr7:85737783-85754981 |
| 22970 | Vmn2r73 | NM_001105186.1 | chr7:85857546-85875938 |
| 22971 | Vmn2r74 | NM_001105187.1 | chr7:85951866-85961482 |
| 22972 | Vmn2r75 | NM_001102578.1 | chr7:86148041-86171724 |
| 22973 | Vmn2r76 | NM_001102580.1 | chr7:86205205-86246201 |
| 22974 | Vmn2r77 | NM_001105188.1 | chr7:86795140-86812032 |
| 22975 | Vmn2r78 | NM_001105189.1 | chr7:86915348-86955177 |
| 22976 | Vmn2r79 | NM_001105190.1 | chr7:86996464-87037968 |
| 22977 | Vmn2r8 | NM_001104620.1 | chr5:108797192-108808754 |
| 22978 | Vmn2r80 | NM_001103368.1 | chr10:79148815-79194933 |

Fig. 26 - 122

| | | | |
|---|---|---|---|
| 22979 | Vmn2r81 | NM_175936.1 | chr10:79247776-79294535 |
| 22980 | Vmn2r82 | NM_001101572.1 | chr10:79356590-79396766 |
| 22981 | Vmn2r83 | NM_001104537.1 | chr10:79468957-79492154 |
| 22982 | Vmn2r84 | NM_001081448.1 | chr10:130385799-130394241 |
| 22983 | Vmn2r85 | NM_001102602.1 | chr10:130418260-130429612 |
| 22984 | Vmn2r86 | NM_001103365.1 | chr10:130446198-130455894 |
| 22985 | Vmn2r87 | NM_001103366.1 | chr10:130471820-130497379 |
| 22986 | Vmn2r88 | NM_011686.1 | chr14:51411000-51418882 |
| 22987 | Vmn2r89 | NM_009486.3 | chr14:51451961-51461293 |
| 22988 | Vmn2r9 | NM_001104621.1 | chr5:108842946-108852510 |
| 22989 | Vmn2r90 | NM_001104539.1 | chr17:17703940-17734167 |
| 22990 | Vmn2r91 | NM_001104540.1 | chr17:18085056-18136643 |
| 22991 | Vmn2r92 | NM_001104541.1 | chr17:18151929-18185178 |
| 22992 | Vmn2r93 | NM_001104541.1 | chr17:18229828-18326441 |
| 22993 | Vmn2r94 | NM_001104543.1 | chr17:18243569-18277566 |
| 22994 | Vmn2r95 | NM_001102581.1 | chr17:18424103-18452324 |
| 22995 | Vmn2r96 | NM_001104547.1 | chr17:18581726-18598157 |
| 22996 | Vmn2r97 | NM_001104549.1 | chr17:18914321-18948071 |
| 22997 | Vmn2r98 | NM_001104550.1 | chr17:19053492-19081311 |
| 22998 | Vmn2r99 | NM_001104551.2 | chr17:19362134-19394590 |
| 22999 | Vmn2r-ps11 | NR_003962.1 | chr3:64632862-64844743 |
| 23000 | Vmn2r-ps129 | NR_033648.1 | chr7:23004970-23006659 |
| 23001 | Vmn2r-ps159 | NR_028141.1 | chr4:156331102-156339499 |
| 23002 | Vmn2r-ps54 | NR_004441.1 | chr7:41648013-41727193 |
| 23003 | Vmn2r-ps60 | NR_028441.1 | chr7:42430104-42430369 |
| 23004 | Vmo1 | NM_001013607.1 | chr11:70513515-70514616 |
| 23005 | Vmp1 | NM_029478.3 | chr11:86583864-86683822 |
| 23006 | Vnn1 | NM_011704.3 | chr10:23894687-23905343 |
| 23007 | Vnn3 | NM_011979.2 | chr10:23851461-23869843 |
| 23008 | Vopp1 | NM_146168.1 | chr6:57752263-57825125 |
| 23009 | Vprbp | NM_001015592.2 | chr9:106821975-106880992 |
| 23010 | Vpreb1 | NM_016982.2 | chr16:16868400-16869255 |
| 23011 | Vpreb2 | NM_016983.1 | chr16:17980564-17981080 |
| 23012 | Vpreb3 | NM_009514.4 | chr10:75948311-75949646 |
| 23013 | Vps11 | NM_027889.1 | chr9:44348104-44361670 |
| 23014 | Vps13a | NM_173628.4 | chr19:16615365-16780933 |
| 23015 | Vps13b | NM_177151.3 | chr15:35371545-35931229 |
| 23016 | Vps13c | NM_177184.3 | chr9:67840395-67995634 |
| 23017 | Vps13d | NM_001276465.1 | chr4:144972621-145195005 |
| 23018 | Vps16 | NM_030559.3 | chr2:130424319-130444269 |
| 23019 | Vps18 | NM_172269.3 | chr2:119288741-119298453 |
| 23020 | Vps25 | NM_001284411.1 | chr11:101253706-101259547 |
| 23021 | Vps26a | NM_001113355.1 | chr10:62454842-62486598 |
| 23022 | Vps26b | NM_178027.4 | chr9:27004501-27030094 |
| 23023 | Vps28 | NM_025842.4 | chr15:76622085-76626084 |
| 23024 | Vps29 | NM_019780.1 | chr5:122354412-122363287 |
| 23025 | Vps33a | NM_029929.3 | chr5:123528759-123573015 |
| 23026 | Vps33b | NM_178070.4 | chr7:80269654-80291579 |
| 23027 | Vps35 | NM_022997.4 | chr8:85260391-85299497 |
| 23028 | Vps36 | NM_027338.1 | chr8:22192859-22218697 |
| 23029 | Vps37a | NM_033560.3 | chr8:40511782-40551134 |
| 23030 | Vps37b | NM_177876.4 | chr5:124004640-124032260 |
| 23031 | Vps37c | NM_181403.2 | chr19:10688814-10714419 |
| 23032 | Vps37d | NM_001199677.1 | chr5:135072899-135078266 |
| 23033 | Vps39 | NM_147153.3 | chr2:120316460-120353133 |
| 23034 | Vps41 | NM_172120.4 | chr13:18717291-18866811 |
| 23035 | Vps45 | NM_013841.3 | chr3:95999831-96058455 |
| 23036 | Vps4a | NM_126165.1 | chr8:107031325-107045756 |
| 23037 | Vps4b | NM_009190.4 | chr1:106770787-106796725 |
| 23038 | Vps51 | NM_001081041.1 | chr19:6067841-6077187 |
| 23039 | Vps52 | NM_172620.3 | chr17:33955881-33966488 |
| 23040 | Vps53 | NM_028664.3 | chr11:76046225-76179630 |
| 23041 | Vps54 | NM_001200628.1 | chr11:21239031-21321133 |
| 23042 | Vps72 | NM_009336.2 | chr3:95111041-95123051 |
| 23043 | Vps8 | NM_001285893.1 | chr16:21423117-21644681 |
| 23044 | Vps9d1 | NM_028200.2 | chr8:123242355-123254222 |
| 23045 | Vrk1 | NM_001029843.1 | chr12:106010262-106077410 |
| 23046 | Vrk2 | NM_001252447.1 | chr11:26471401-26593920 |
| 23047 | Vrk3 | NM_133945.1 | chr7:44748628-44777514 |
| 23048 | Vtn | NM_001037776.2 | chr11:78642895-84651455 |
| 23049 | Vsig1 | NM_026103.1 | chrX:140923188-140939472 |
| 23050 | Vsig10 | NM_001033311.3 | chr5:117319265-117355006 |
| 23051 | Vsig10l | NM_001290316.1 | chr7:43463232-43472014 |
| 23052 | Vsig2 | NM_020518.2 | chr9:37539254-37544205 |
| 23053 | Vsig4 | NM_177789.4 | chrX:96247202-96293438 |
| 23054 | Vsig8 | NM_177723.4 | chr1:172559937-172563717 |
| 23055 | Vsnl1 | NM_012038.4 | chr12:11325244-11436649 |
| 23056 | Vstm2a | NM_001290539.1 | chr11:16257723-16284551 |
| 23057 | Vstm2b | NM_021387.3 | chr7:40899277-40929968 |
| 23058 | Vstm2l | NM_198627.2 | chr2:157914652-157944719 |
| 23059 | Vstm4 | NM_178791.4 | chr14:32856755-32939489 |
| 23060 | Vstm5 | NM_026955.2 | chr9:15239044-15259413 |
| 23061 | Vsx1 | NM_054068.2 | chr2:150680701-150689137 |
| 23062 | Vsx2 | NM_007701.3 | chr12:84569827-84595457 |
| 23063 | Vta1 | NM_025418.3 | chr10:14655332-14705489 |
| 23064 | Vtcn1 | NM_178594.3 | chr3:100825458-100896922 |
| 23065 | Vt1a | NM_016862.4 | chr19:55316056-55627461 |
| 23066 | Vt1b | NM_016800.3 | chr12:79156016-79172458 |
| 23067 | Vtn | NM_011707.2 | chr11:78499119-78502325 |
| 23068 | Vwa1 | NM_147776.4 | chr4:155768494-155774561 |
| 23069 | Vwa2 | NM_172840.2 | chr19:56874415-56912078 |
| 23070 | Vwa3a | NM_177697.3 | chr7:120739556-120805540 |
| 23071 | Vwa5a | NM_001145957.1 | chr9:38718267-38743337 |
| 23072 | Vwa5b1 | NM_029401.2 | chr4:138568968-138623992 |
| 23073 | Vwa5b2 | NM_001144953.1 | chr16:20589581-20605377 |

| | | | |
|---|---|---|---|
| 23074 | Vwa7 | NM_138582.1 | chr17:35016578-35026741 |
| 23075 | Vwa8 | NM_027906.1 | chr14:78849177-79202310 |
| 23076 | Vwa9 | NM_001077631.2 | chr9:64960831-64986981 |
| 23077 | Vwc2 | NM_177033.3 | chr11:11114015-11263526 |
| 23078 | Vwc2l | NM_177164.3 | chr1:70725714-70885397 |
| 23079 | Vwce | NM_027913.1 | chr19:10634232-10665210 |
| 23080 | Vwde | NM_001137757.2 | chr6:13185610-13224965 |
| 23081 | Vwf | NM_011708.4 | chr6:125552947-125686679 |
| 23082 | Wac | NM_001146298.2 | chr18:7869196-7929028 |
| 23083 | Wap | NM_011709.5 | chr11:6635482-6638649 |
| 23084 | Wapal | NM_001004436.4 | chr14:34673927-34747983 |
| 23085 | Wars | NM_001164314.1 | chr12:108860029-108894174 |
| 23086 | Wars2 | NM_027462.4 | chr3:99141089-99220203 |
| 23087 | Was | NM_009515.2 | chrX:8081465-8090491 |
| 23088 | Wasf1 | NM_031877.3 | chr10:40885533-40938569 |
| 23089 | Wasf2 | NM_153423.6 | chr4:133130832-133198330 |
| 23090 | Wasf3 | NM_145155.3 | chr5:146385005-146471125 |
| 23091 | Wash | NM_001037757.1 | chr17:66111644-66120503 |
| 23092 | Wasl | NM_001167745.1 | chr6:24632685-24664995 |
| 23093 | Wbp1 | NM_001083922.1 | chr6:83119043-83121461 |
| 23094 | Wbp11 | NM_021714.4 | chr6:136813653-136828216 |
| 23095 | Wbp1l | NM_001177812.1 | chr19:46599105-46657389 |
| 23096 | Wbp2 | NM_016852.2 | chr11:116078572-116086964 |
| 23097 | Wbp2nl | NM_029066.1 | chr15:82298983-82314558 |
| 23098 | Wbp4 | NM_018765.3 | chr14:79459936-79481268 |
| 23099 | Wbp5 | NM_017712.2 | chrX:136245079-136247139 |
| 23100 | Wbscr16 | NM_033572.2 | chr5:134148057-134176767 |
| 23101 | Wbscr17 | NM_145218.3 | chr5:130874950-131307522 |
| 23102 | Wbscr22 | NM_025375.3 | chr5:135052956-135064666 |
| 23103 | Wbscr26 | NR_026907.1 | chr5:134987432-135001350 |
| 23104 | Wbscr27 | NM_024479.2 | chr5:134932372-134942637 |
| 23105 | Wbscr28 | NM_029681.3 | chr5:134901592-134906733 |
| 23106 | Wdfy1 | NM_001111279.1 | chr1:79702261-79761769 |
| 23107 | Wdfy2 | NM_175546.4 | chr14:62837689-62956886 |
| 23108 | Wdfy3 | NM_172882.3 | chr5:101832952-102069921 |
| 23109 | Wdfy4 | NM_001146022.2 | chr14:32959546-33185066 |
| 23110 | Wdhd1 | NM_172598.3 | chr14:47240943-47276857 |
| 23111 | Wdpcp | NM_145425.3 | chr11:21572280-21898686 |
| 23112 | Wdr1 | NM_011715.2 | chr5:38526812-38561595 |
| 23113 | Wdr11 | NM_172255.3 | chr7:129591862-129635738 |
| 23114 | Wdr12 | NM_011199060.1 | chr1:60076867-60098500 |
| 23115 | Wdr13 | NM_001290783.1 | chrX:8123300-8132858 |
| 23116 | Wdr16 | NM_027963.2 | chr11:67924805-67965642 |
| 23117 | Wdr17 | NM_001172152.1 | chr8:54629615-54724368 |
| 23118 | Wdr18 | NM_175450.4 | chr10:79960151-79969246 |
| 23119 | Wdr19 | NM_153391.2 | chr5:65199695-65260415 |
| 23120 | Wdr20 | NM_027149.2 | chr12:110737948-110795028 |
| 23121 | Wdr20rt | NM_027614.1 | chr12:65225516-65228454 |
| 23122 | Wdr24 | NM_173741.3 | chr17:25823626-25828730 |
| 23123 | Wdr25 | NM_177602.3 | chr12:108894271-109028452 |
| 23124 | Wdr26 | NM_145514.5 | chr1:181173225-181211978 |
| 23125 | Wdr27 | NM_175173.3 | chr17:14818671-14943124 |
| 23126 | Wdr3 | NM_175552.4 | chr3:100138179-100162403 |
| 23127 | Wdr31 | NM_001290521.1 | chr4:62452631-62470895 |
| 23128 | Wdr33 | NM_001170966.1 | chr18:31804056-31835435 |
| 23129 | Wdr34 | NM_001008498.2 | chr2:30031557-30048879 |
| 23130 | Wdr35 | NM_001159527.1 | chr12:8974000-9028847 |
| 23131 | Wdr36 | NM_001110015.1 | chr18:32837224-32866420 |
| 23132 | Wdr37 | NM_001039988.2 | chr13:8802965-8871736 |
| 23133 | Wdr38 | NM_029687.3 | chr2:38998308-39001584 |
| 23134 | Wdr4 | NM_021322.2 | chr17:31494321-31512487 |
| 23135 | Wdr41 | NM_172590.3 | chr13:94976343-95023316 |
| 23136 | Wdr43 | NM_175639.1 | chr17:71616214-71659031 |
| 23137 | Wdr44 | NM_175180.3 | chrX:23693050-23806001 |
| 23138 | Wdr45 | NM_001290792.1 | chrX:7722219-7728201 |
| 23139 | Wdr45b | NM_025793.3 | chr11:121327202-121354447 |
| 23140 | Wdr46 | NM_020603.2 | chr17:33940722-33949695 |
| 23141 | Wdr47 | NM_181400.3 | chr3:108591277-108645719 |
| 23142 | Wdr48 | NM_026236.3 | chr9:119894834-119926579 |
| 23143 | Wdr5 | NM_080848.2 | chr2:27515146-27536538 |
| 23144 | Wdr52 | NM_001033247.1 | chr16:44394798-44482428 |
| 23145 | Wdr53 | NM_001185162.1 | chr16:32247226-32257083 |
| 23146 | Wdr54 | NM_023790.2 | chr6:83152709-83156379 |
| 23147 | Wdr55 | NM_026464.2 | chr18:36760238-36763708 |
| 23148 | Wdr59 | NM_001170742.1 | chr8:111448783-111522107 |
| 23149 | Wdr5b | NM_027113.2 | chr16:36041189-36042974 |
| 23150 | Wdr6 | NM_031392.5 | chr9:108572312-108578670 |
| 23151 | Wdr60 | NM_146039.3 | chr12:116207049-116263025 |
| 23152 | Wdr61 | NM_001025375.2 | chr9:54717152-54734549 |
| 23153 | Wdr62 | NM_146186.3 | chr7:30240137-30280421 |
| 23154 | Wdr63 | NM_172864.3 | chr3:146040525-146108036 |
| 23155 | Wdr64 | NM_029453.2 | chr1:175698592-175815733 |
| 23156 | Wdr65 | NM_026789.4 | chr4:118554550-118620405 |
| 23157 | Wdr7 | NM_001014981.1 | chr18:63708694-63889759 |
| 23158 | Wdr70 | NM_001081402.1 | chr15:7873054-8099209 |
| 23159 | Wdr72 | NM_001033500.3 | chr9:74110833-74283203 |
| 23160 | Wdr73 | NM_028026.2 | chr7:80890722-80901269 |
| 23161 | Wdr74 | NM_134139.1 | chr19:8735838-8740624 |
| 23162 | Wdr75 | NM_028599.2 | chr1:45795500-45823613 |
| 23163 | Wdr76 | NM_001290986.1 | chr2:121506722-121544859 |
| 23164 | Wdr77 | NM_027432.3 | chr3:105959497-105969760 |
| 23165 | Wdr78 | NM_146254.4 | chr4:103038064-103104299 |
| 23166 | Wdr8 | NM_021499.2 | chr4:154142371-154156818 |
| 23167 | Wdr81 | NM_138950.2 | chr11:75440942-75454717 |
| 23168 | Wdr82 | NM_029896.1 | chr9:106170928-106191706 |

Fig. 26 - 123

| | | | |
|---|---|---|---|
| 23169 | Wdr83 | NM_028399.2 | chr8:85075034-85080746 |
| 23170 | Wdr83os | NM_001091493.2 | chr8:85080962-85082339 |
| 23171 | Wdr86 | NM_001081441.1 | chr5:24712268-24730680 |
| 23172 | Wdr89 | NM_028203.1 | chr12:75630593-75669537 |
| 23173 | Wdr90 | NM_001163766.1 | chr17:25844733-25861515 |
| 23174 | Wdr91 | NM_001013366.1 | chr6:34880425-34910831 |
| 23175 | Wdr92 | NM_178909.4 | chr11:17211892-17235200 |
| 23176 | Wdr93 | NM_001037927.1 | chr7:79743162-79785950 |
| 23177 | Wdr95 | NM_029440.3 | chr5:149528678-149611894 |
| 23178 | Wdr96 | NM_027559.2 | chr19:47736856-47837361 |
| 23179 | Wdsub1 | NM_001159636.1 | chr2:59855193-59882606 |
| 23180 | Wdtc1 | NM_199306.4 | chr4:133292465-133339315 |
| 23181 | Wdyhv1 | NM_029734.1 | chr15:58141495-58158654 |
| 23182 | Wee1 | NM_009516.3 | chr7:110122058-110143299 |
| 23183 | Wee2 | NM_201370.2 | chr6:40442862-40466815 |
| 23184 | Wfdc1 | NM_023395.2 | chr8:119666364-119688020 |
| 23185 | Wfdc10 | NM_001039501.2 | chr2:164656045-164657368 |
| 23186 | Wfdc11 | NM_001161806.1 | chr2:164662893-164674087 |
| 23187 | Wfdc12 | NM_138684.2 | chr2:164689230-164690558 |
| 23188 | Wfdc13 | NM_001012704.1 | chr2:164685106-164687706 |
| 23189 | Wfdc15a | NM_183271.2 | chr2:164198871-164200117 |
| 23190 | Wfdc15b | NM_001045554.1 | chr2:164214453-164221663 |
| 23191 | Wfdc16 | NM_001012723.2 | chr2:164634707-164638802 |
| 23192 | Wfdc17 | NM_001081957.1 | chr11:83704055-83706269 |
| 23193 | Wfdc18 | NM_007969.4 | chr11:83709003-83711360 |
| 23194 | Wfdc2 | NM_026323.2 | chr2:164562715-164568506 |
| 23195 | Wfdc3 | NM_027961.1 | chr2:164731225-164743267 |
| 23196 | Wfdc5 | NM_145369.3 | chr2:164176324-164182742 |
| 23197 | Wfdc6a | NM_001033240.4 | chr2:164579518-164585447 |
| 23198 | Wfdc6b | NM_001012725.2 | chr2:164613699-164618213 |
| 23199 | Wfdc8 | NM_001080550.2 | chr2:164596457-164613656 |
| 23200 | Wfdc9 | NM_001160414.1 | chr2:164649624-164654966 |
| 23201 | Wfikkn1 | NM_001100454.1 | chr17:25877627-25880858 |
| 23202 | Wfikkn2 | NM_181819.2 | chr11:94235951-94242579 |
| 23203 | Wfs1 | NM_011716.2 | chr5:36966103-36988982 |
| 23204 | Whamm | NM_001004185.3 | chr7:81571291-81596836 |
| 23205 | Whrn | NM_001008791.2 | chr4:63414909-63495991 |
| 23206 | Whsc1 | NM_001081102.2 | chr5:33843111-33897966 |
| 23207 | Whsc1l1 | NM_001001735.2 | chr8:25602283-25677972 |
| 23208 | Wibg | NM_001170869.2 | chr10:128748454-128766568 |
| 23209 | Wif1 | NM_011915.2 | chr10:121034003-121100642 |
| 23210 | Wipf1 | NM_001289722.1 | chr2:73429609-73453889 |
| 23211 | Wipf2 | NM_197940.2 | chr11:98863597-98905578 |
| 23212 | Wipf3 | NM_001167860.1 | chr6:54452882-54503768 |
| 23213 | Wipi1 | NM_145940.2 | chr11:109573520-109611389 |
| 23214 | Wipi2 | NM_178398.4 | chr5:142629583-142669370 |
| 23215 | Wisp1 | NM_018865.2 | chr15:66891392-66923199 |
| 23216 | Wisp2 | NM_016873.2 | chr2:163820833-163833147 |
| 23217 | Wisp3 | NM_001127376.1 | chr10:39150970-39163794 |
| 23218 | Wiz | NM_011717.4 | chr17:32354049-32388950 |
| 23219 | Wls | NM_026582.4 | chr3:159839694-159935175 |
| 23220 | Wnk1 | NM_001185020.1 | chr6:119923968-120038655 |
| 23221 | Wnk2 | NM_001290311.1 | chr13:49037600-49148328 |
| 23222 | Wnk3 | NM_001271678.1 | chrX:151198077-151320192 |
| 23223 | Wnk4 | NM_175638.3 | chr11:101260566-101277409 |
| 23224 | Wnt1 | NM_021279.4 | chr15:98789856-98793830 |
| 23225 | Wnt10a | NM_009518.2 | chr1:74792018-74804175 |
| 23226 | Wnt10b | NM_011718.2 | chr15:98771751-98778150 |
| 23227 | Wnt11 | NM_001285792.1 | chr7:98835111-98854747 |
| 23228 | Wnt16 | NM_053116.4 | chr6:22288226-22298522 |
| 23229 | Wnt2 | NM_023653.5 | chr6:17988939-18030445 |
| 23230 | Wnt2b | NM_009520.3 | chr3:104944804-104961709 |
| 23231 | Wnt3 | NM_009521.2 | chr11:103774174-103818021 |
| 23232 | Wnt3a | NM_009522.2 | chr11:59248041-59290751 |
| 23233 | Wnt4 | NM_009523.2 | chr4:137277634-137299501 |
| 23234 | Wnt5a | NM_001256224.1 | chr14:28511404-28525515 |
| 23235 | Wnt5b | NM_001271757.1 | chr6:119432530-119449386 |
| 23236 | Wnt6 | NM_009526.3 | chr1:74771891-74785319 |
| 23237 | Wnt7a | NM_009527.3 | chr6:91363982-91411369 |
| 23238 | Wnt7b | NM_001163633.1 | chr15:85535436-85580729 |
| 23239 | Wnt8a | NM_009290.2 | chr18:34542327-34548061 |
| 23240 | Wnt8b | NM_011720.3 | chr19:44493471-44514273 |
| 23241 | Wnt9a | NM_139298.2 | chr11:59306929-59333552 |
| 23242 | Wnt9b | NM_011719.4 | chr11:103727362-103749821 |
| 23243 | Wrap53 | NM_144824.2 | chr11:69561753-69579324 |
| 23244 | Wrb | NM_027301.2 | chr16:96145418-96157852 |
| 23245 | Wrn | NM_001122822.1 | chr8:33234372-33385527 |
| 23246 | Wrnip1 | NM_030215.3 | chr13:32802029-32822610 |
| 23247 | Wsb1 | NM_001042565.3 | chr11:79239382-79243024 |
| 23248 | Wsb2 | NM_021539.4 | chr5:117357304-117378589 |
| 23249 | Wscd1 | NM_177618.4 | chr11:71750702-71789646 |
| 23250 | Wscd2 | NM_177292.3 | chr5:113550419-113589725 |
| 23251 | Wt1 | NM_144783.2 | chr2:105126528-105173614 |
| 23252 | Wt1os | NR_015462.1 | chr2:105076537-105126510 |
| 23253 | Wtap | NM_001113532.1 | chr17:12971019-12992259 |
| 23254 | Wtip | NM_207212.2 | chr7:34109549-34133268 |
| 23255 | Wwc1 | NM_170779.1 | chr11:35839177-35980089 |
| 23256 | Wwc2 | NM_133791.4 | chr8:47827605-47990551 |
| 23257 | Wwox | NM_019573.3 | chr8:114439651-115352712 |
| 23258 | Wwp1 | NM_001276292.1 | chr4:19608299-19709004 |
| 23259 | Wwp2 | NM_025830.3 | chr8:107436397-107558595 |
| 23260 | Wwtr1 | NM_001168281.1 | chr3:57455643-57575910 |
| 23261 | Xab2 | NM_026156.2 | chr8:3610089-3621296 |
| 23262 | Xaf1 | NM_001037713.4 | chr17:72301628-72313733 |
| 23263 | Xbp1 | NM_001271730.1 | chr11:5520640-5525993 |
| 23264 | Xcl1 | NM_008510.1 | chr1:164931647-164935510 |
| 23265 | Xcr1 | NM_011798.4 | chr9:123852314-123862029 |
| 23266 | Xdh | NM_011723.3 | chr17:73883894-73950196 |
| 23267 | Xiap | NM_009688.3 | chrX:42067835-42109664 |
| 23268 | Xirp1 | NM_011724.3 | chr9:120013754-120023598 |
| 23269 | Xirp2 | NM_001024618.2 | chr2:67446001-67526606 |
| 23270 | Xist | NR_001463.3 | chrX:103460372-103483233 |
| 23271 | Xk | NM_023500.2 | chrX:9272783-9313245 |
| 23272 | Xkr4 | NM_001011874.1 | chr1:3214481-3671498 |
| 23273 | Xkr5 | NM_001113350.2 | chr8:18932728-18950975 |
| 23274 | Xkr6 | NM_173393.2 | chr14:63606529-63820410 |
| 23275 | Xkr7 | NM_001011732.1 | chr2:153031851-153055775 |
| 23276 | Xkr8 | NM_201368.1 | chr4:132724903-132732546 |
| 23277 | Xkr9 | NM_001011873.2 | chr1:13668770-13701723 |
| 23278 | Xkrx | NM_183319.2 | chrX:134149044-134161928 |
| 23279 | Xlr | NM_001291747.1 | chrX:53783734-53797706 |
| 23280 | Xlr3a | NM_001110784.1 | chrX:73086292-73097095 |
| 23281 | Xlr3b | NM_001081643.1 | chrX:73192178-73202930 |
| 23282 | Xlr3c | NM_011727.2 | chrX:73254539-73265390 |
| 23283 | Xlr4a | NM_001081642.1 | chrX:73074344-73082507 |
| 23284 | Xlr4b | NM_021365.3 | chrX:73214332-73222453 |
| 23285 | Xlr4c | NM_183094.3 | chrX:73234075-73243130 |
| 23286 | Xlr5a | NM_001045539.2 | chrX:73107634-73117702 |
| 23287 | Xlr5b | NM_001111293.1 | chrX:73148840-73158399 |
| 23288 | Xlr5c | NM_031493.1 | chrX:73285196-73290515 |
| 23289 | Xndc1 | NM_001286689.1 | chr7:102065490-102083762 |
| 23290 | Xntrpc | NM_011644.3 | chr7:102071218-102096864 |
| 23291 | Xpa | NM_011728.2 | chr4:46175221-46196311 |
| 23292 | Xpc | NM_009531.2 | chr6:91489306-91515888 |
| 23293 | Xpnpep1 | NM_133216.3 | chr19:52991179-53038654 |
| 23294 | Xpnpep2 | NM_001289729.1 | chrX:48108724-48136981 |
| 23295 | Xpnpep3 | NM_177310.2 | chr15:81400187-81454888 |
| 23296 | Xpo4 | NM_001035226.1 | chr14:57582270-57664956 |
| 23297 | Xpo4 | NM_020506.1 | chr14:57582270-57664956 |
| 23298 | Xpo5 | NM_028198.2 | chr17:46202854-46242299 |
| 23299 | Xpo6 | NM_028816.2 | chr7:126101718-126200408 |
| 23300 | Xpo7 | NM_023045.2 | chr14:70654245-70766628 |
| 23301 | Xpot | NM_001081056.1 | chr10:121587379-121626316 |
| 23302 | Xpr1 | NM_011273.2 | chr1:155275656-155417444 |
| 23303 | Xrcc1 | NM_009532.4 | chr7:24547149-24573438 |
| 23304 | Xrcc2 | NM_020570.2 | chr5:25689815-25705797 |
| 23305 | Xrcc3 | NM_028875.3 | chr12:111803191-111813879 |
| 23306 | Xrcc4 | NM_028012.4 | chr13:89848913-90089608 |
| 23307 | Xrcc5 | NM_009533.2 | chr1:72307420-72394953 |
| 23308 | Xrcc6 | NM_010247.2 | chr15:82016368-82040084 |
| 23309 | Xrcc6bp1 | NM_001159559.1 | chr10:126887247-126901371 |
| 23310 | Xrn1 | NM_011916.3 | chr9:95954759-96057806 |
| 23311 | Xrn2 | NM_011917.2 | chr2:147013059-147077997 |
| 23312 | Xrra1 | NM_001164258.1 | chr7:99859217-99917824 |
| 23313 | Xxylt1 | NM_198626.2 | chr16:30955502-31081432 |
| 23314 | Xylb | NM_001033209.3 | chr9:119357380-119393797 |
| 23315 | Xylt1 | NM_175645.3 | chr7:117380978-117667630 |
| 23316 | Xylt2 | NM_145828.3 | chr11:94663846-94677493 |
| 23317 | Yaeld1 | NM_025904.3 | chr13:17986639-17993351 |
| 23318 | Yaf2 | NM_024189.6 | chr15:93283832-93336935 |
| 23319 | Yap1 | NM_001171147.1 | chr9:7932000-8004596 |
| 23320 | Yars | NM_134151.4 | chr4:129189794-129219607 |
| 23321 | Yars2 | NM_198246.2 | chr16:16302964-16309640 |
| 23322 | Ybey | NM_172550.4 | chr10:76459566-76469114 |
| 23323 | Ybx1 | NM_011732.2 | chr4:119277326-119294513 |
| 23324 | Ybx2 | NM_016875.2 | chr11:69935898-69941599 |
| 23325 | Ybx3 | NM_011733.2 | chr6:131364857-131388450 |
| 23326 | Ydjc | NM_026940.4 | chr16:17148966-17148857 |
| 23327 | Yeats2 | NM_001033237.2 | chr16:20141062-20232573 |
| 23328 | Yeats4 | NM_026570.4 | chr10:117215140-117224507 |
| 23329 | Yes1 | NM_001205132.1 | chr5:32611170-32687066 |
| 23330 | Yif1a | NM_026553.4 | chr19:5088537-5092879 |
| 23331 | Yif1b | NM_001110201.1 | chr7:29238322-29247532 |
| 23332 | Yipf1 | NM_001205156.1 | chr4:107314362-107359823 |
| 23333 | Yipf2 | NM_001205157.1 | chr9:21588681-21592831 |
| 23334 | Yipf3 | NM_145353.2 | chr17:46248079-46252537 |
| 23335 | Yipf4 | NM_026417.4 | chr17:74489492-74500277 |
| 23336 | Yipf5 | NM_023311.3 | chr18:40204864-40219399 |
| 23337 | Yipf6 | NM_207633.2 | chrX:98937780-98949020 |
| 23338 | Yipf7 | NM_023784.5 | chr5:69516669-69542647 |
| 23339 | Ykt6 | NM_019661.4 | chr11:5955757-5967781 |
| 23340 | Ylpm1 | NM_178363.3 | chr12:84996320-85070515 |
| 23341 | Ymeil1 | NM_013771.5 | chr2:23156504-23199260 |
| 23342 | Yod1 | NM_178691.4 | chr1:130717326-130722057 |
| 23343 | Ypel1 | NM_001291047.1 | chr16:17070138-17086736 |
| 23344 | Ypel2 | NM_001005341.3 | chr11:86936424-86993762 |
| 23345 | Ypel3 | NM_025347.2 | chr7:126776974-126780514 |
| 23346 | Ypel4 | NM_001005342.2 | chr2:84734203-84737877 |
| 23347 | Ypel5 | NM_027166.5 | chr17:72836703-72851195 |
| 23348 | Yrdc | NM_153566.2 | chr4:124850758-124855242 |
| 23349 | Ythdc1 | NM_177680.3 | chr5:86804489-86836657 |
| 23350 | Ythdc2 | NM_001163013.1 | chr18:44828664-44889720 |
| 23351 | Ythdf1 | NM_173761.3 | chr2:180904376-180920936 |
| 23352 | Ythdf2 | NM_145393.4 | chr4:132184915-132212256 |
| 23353 | Ythdf3 | NM_001145919.1 | chr3:16183182-16217037 |
| 23354 | Ywhab | NM_018753.6 | chr2:163995196-164018587 |
| 23355 | Ywhae | NM_009536.4 | chr11:75732886-75765841 |
| 23356 | Ywhag | NM_018871.3 | chr5:135908378-135934641 |
| 23357 | Ywhah | NM_011738.2 | chr5:33018815-33027966 |
| 23358 | Ywhaq | NM_011739.3 | chr12:21390328-21417436 |

Fig. 26 - 124

| | | | |
|---|---|---|---|
| 23359 | Ywhaz | NM_001253805.1 | chr15:36770261-36794538 |
| 23360 | Yy1 | NM_009537.3 | chr12:108793310-108816632 |
| 23361 | Yy2 | NM_001098723.1 | chrX:157566118-157568985 |
| 23362 | Zadh2 | NM_146090.5 | chr18:84088157-84097514 |
| 23363 | Zak | NM_001164791.1 | chr2:72285700-72407501 |
| 23364 | Zan | NM_011741.2 | chr5:137378636-137477064 |
| 23365 | Zap70 | NM_001289612.1 | chr1:36778983-36782820 |
| 23366 | Zar1 | NM_174877.3 | chr5:72577113-72581084 |
| 23367 | Zar1l | NM_001159693.1 | chr5:150507068-150518159 |
| 23368 | Zbbx | NM_172515.3 | chr3:75037894-75143772 |
| 23369 | Zbed3 | NM_028106.3 | chr3:95324824-95337842 |
| 23370 | Zbed4 | NM_181412.3 | chr15:88751710-88784516 |
| 23371 | Zbed5 | NM_183088.2 | chr5:129895722-129903622 |
| 23372 | Zbed6 | NM_001166552.1 | chr1:133655878-133660885 |
| 23373 | Zbp1 | NM_001139519.1 | chr2:173213735-173218922 |
| 23374 | Zbtb1 | NM_178744.2 | chr12:76370265-76388747 |
| 23375 | Zbtb10 | NM_177660.3 | chr3:9250566-9285332 |
| 23376 | Zbtb11 | NM_173026.2 | chr16:55973803-56008912 |
| 23377 | Zbtb12 | NM_198886.3 | chr17:34894558-34896844 |
| 23378 | Zbtb14 | NM_009547.2 | chr17:69383977-69390544 |
| 23379 | Zbtb16 | NM_001033324.2 | chr9:48654296-48835945 |
| 23380 | Zbtb17 | NM_009541.2 | chr4:141444672-141467937 |
| 23381 | Zbtb18 | NM_001012330.1 | chr1:177444660-177450764 |
| 23382 | Zbtb2 | NM_001033466.3 | chr10:4367073-4388108 |
| 23383 | Zbtb20 | NM_001258805.1 | chr16:42907644-43619123 |
| 23384 | Zbtb21 | NM_001081684.1 | chr16:97947434-97962621 |
| 23385 | Zbtb22 | NM_020625.1 | chr17:33916175-33919325 |
| 23386 | Zbtb24 | NM_001177229.1 | chr10:41450357-41465582 |
| 23387 | Zbtb25 | NM_001172104.1 | chr12:76348899-76369464 |
| 23388 | Zbtb26 | NM_199025.2 | chr2:37432167-37443121 |
| 23389 | Zbtb3 | NM_001008237.1 | chr19:8802529-8804854 |
| 23390 | Zbtb32 | NM_021397.2 | chr7:30589680-30592942 |
| 23391 | Zbtb33 | NM_001079513.1 | chrX:38189792-38197046 |
| 23392 | Zbtb34 | NM_001085507.1 | chr2:33406107-33431324 |
| 23393 | Zbtb37 | NM_173424.3 | chr1:161017755-161034259 |
| 23394 | Zbtb38 | NM_175537.3 | chr9:96685422-96731675 |
| 23395 | Zbtb39 | NM_198035.1 | chr10:127739537-127747339 |
| 23396 | Zbtb4 | NM_029348.2 | chr11:69765911-69784026 |
| 23397 | Zbtb40 | NM_198248.1 | chr4:136979731-137048695 |
| 23398 | Zbtb41 | NM_172643.5 | chr1:139422382-139453007 |
| 23399 | Zbtb42 | NM_001100460.1 | chr12:112678839-112682747 |
| 23400 | Zbtb43 | NM_001025594.1 | chr2:33450287-33468532 |
| 23401 | Zbtb44 | NM_001115130.1 | chr9:31030643-31075885 |
| 23402 | Zbtb45 | NM_001024699.1 | chr7:13005665-13009800 |
| 23403 | Zbtb46 | NM_027656.2 | chr2:181390885-181420438 |
| 23404 | Zbtb48 | NM_133879.2 | chr4:152019775-152027671 |
| 23405 | Zbtb49 | NM_029162.2 | chr5:38200043-38220428 |
| 23406 | Zbtb5 | NM_001163863.1 | chr4:44991242-45012412 |
| 23407 | Zbtb6 | NM_146253.5 | chr2:37425499-37430919 |
| 23408 | Zbtb7a | NM_010731.3 | chr10:81136270-81151657 |
| 23409 | Zbtb7b | NM_009565.4 | chr3:89377645-89393203 |
| 23410 | Zbtb7c | NM_145356.3 | chr18:75820177-76148564 |
| 23411 | Zbtb8a | NM_028603.4 | chr4:129353631-129378028 |
| 23412 | Zbtb8b | NM_153541.3 | chr4:129425764-129440818 |
| 23413 | Zbtb8os | NM_025970.3 | chr4:129336025-129347029 |
| 23414 | Zbtb9 | NM_001005916.2 | chr17:26973178-26976203 |
| 23415 | Zbtbd6 | NM_001034882.3 | chr14:79451834-79454816 |
| 23416 | Zc2hc1a | NM_173181.3 | chr3:7503425-7553848 |
| 23417 | Zc2hc1b | NM_029172.1 | chr10:13149643-13178023 |
| 23418 | Zc2hc1c | NM_172414.4 | chr12:85288590-85299358 |
| 23419 | Zc3h10 | NM_134003.1 | chr10:128543564-128547744 |
| 23420 | Zc3h11a | NM_001276767.1 | chr1:133619870-133661399 |
| 23421 | Zc3h12a | NM_153159.2 | chr4:125118413-125127881 |
| 23422 | Zc3h12b | NM_001034907.2 | chrX:95711677-95927970 |
| 23423 | Zc3h12c | NM_001162921.1 | chr9:52111984-52168111 |
| 23424 | Zc3h12d | NM_172785.3 | chr10:7832460-7870397 |
| 23425 | Zc3h13 | NM_026083.2 | chr14:75284372-75344426 |
| 23426 | Zc3h14 | NM_001008506.2 | chr12:98746967-98787774 |
| 23427 | Zc3h15 | NM_026934.3 | chr2:83644577-83664616 |
| 23428 | Zc3h18 | NM_001029993.1 | chr8:122376615-122417360 |
| 23429 | Zc3h3 | NM_172121.1 | chr15:75754446-75841908 |
| 23430 | Zc3h4 | NM_198631.2 | chr7:16401195-16437696 |
| 23431 | Zc3h6 | NM_178464.3 | chr2:128967401-129018563 |
| 23432 | Zc3h7a | NM_145931.2 | chr16:11136593-11176393 |
| 23433 | Zc3h7b | NM_001081016.1 | chr15:81744847-81796269 |
| 23434 | Zc3h8 | NM_020594.2 | chr2:128925267-128944020 |
| 23435 | Zc3hav1 | NM_028421.1 | chr6:38310496-38354603 |
| 23436 | Zc3hav1l | NM_172467.3 | chr6:38287393-38299259 |
| 23437 | Zc3hc1 | NM_172735.2 | chr6:30366387-30391010 |
| 23438 | Zc4h2 | NM_001003916.2 | chrX:95639193-95658509 |
| 23439 | Zcchc10 | NM_026479.4 | chr11:53324688-53333301 |
| 23440 | Zcchc11 | NM_175472.3 | chr4:108459425-108559415 |
| 23441 | Zcchc12 | NM_028325.3 | chrX:36195903-36199158 |
| 23442 | Zcchc13 | NM_029158.2 | chrX:103630585-103631664 |
| 23443 | Zcchc14 | NM_080855.2 | chr8:121598760-121651933 |
| 23444 | Zcchc16 | NM_001033795.4 | chrX:144688906-145122410 |
| 23445 | Zcchc17 | NM_153160.4 | chr4:130316084-130359943 |
| 23446 | Zcchc18 | NM_001035509.1 | chrX:136993154-136996923 |
| 23447 | Zcchc2 | NM_001122675.1 | chr1:105990405-106034079 |
| 23448 | Zcchc24 | NM_001101433.1 | chr14:25711639-25768856 |
| 23449 | Zcchc3 | NM_175126.4 | chr2:152411955-152415044 |
| 23450 | Zcchc4 | NM_030185.3 | chr5:52783054-52823571 |
| 23451 | Zcchc5 | NM_199468.1 | chrX:106837081-106840643 |
| 23452 | Zcchc6 | NM_153538.3 | chr13:59771878-59823147 |
| 23453 | Zcchc7 | NM_138590.4 | chr4:44756558-44932214 |
| 23454 | Zcchc8 | NM_027494.3 | chr5:123698301-123721044 |
| 23455 | Zcchc9 | NM_145453.2 | chr13:91796532-91807696 |
| 23456 | Zcrb1 | NM_026025.2 | chr15:93386112-93398290 |
| 23457 | Zcwpw1 | NM_001005426.2 | chr5:137787801-137822621 |
| 23458 | Zdbf2 | NM_001267872.1 | chr1:63273268-63314575 |
| 23459 | Zdhhc1 | NM_175160.3 | chr8:105472424-105496870 |
| 23460 | Zdhhc11 | NM_027704.2 | chr13:73963861-73992840 |
| 23461 | Zdhhc12 | NM_001037762.1 | chr2:30090943-30093635 |
| 23462 | Zdhhc13 | NM_028031.3 | chr7:48785002-48827437 |
| 23463 | Zdhhc14 | NM_146073.3 | chr17:5492599-5753891 |
| 23464 | Zdhhc15 | NM_175358.4 | chrX:104536969-104671064 |
| 23465 | Zdhhc16 | NM_023740.2 | chr19:41933471-41944103 |
| 23466 | Zdhhc17 | NM_172554.2 | chr10:110941779-111010066 |
| 23467 | Zdhhc18 | NM_001017968.2 | chr4:133660991-133633429 |
| 23468 | Zdhhc19 | NM_199309.2 | chr16:32496280-32507214 |
| 23469 | Zdhhc2 | NM_178395.3 | chr8:40423814-40484842 |
| 23470 | Zdhhc20 | NM_029492.4 | chr14:57832701-57890262 |
| 23471 | Zdhhc21 | NM_026647.3 | chr4:82798737-82859661 |
| 23472 | Zdhhc22 | NM_001080943.2 | chr12:86983380-86988676 |
| 23473 | Zdhhc23 | NM_001007460.1 | chr16:43969145-43979050 |
| 23474 | Zdhhc24 | NM_001168516.1 | chr19:4878667-4885397 |
| 23475 | Zdhhc25 | NM_027306.3 | chr15:88600301-88601669 |
| 23476 | Zdhhc3 | NM_026917.5 | chr9:123072309-123113205 |
| 23477 | Zdhhc4 | NM_028379.5 | chr5:143316488-143329238 |
| 23478 | Zdhhc5 | NM_144887.4 | chr2:84687919-84715164 |
| 23479 | Zdhhc6 | NM_001035573.1 | chr19:55298295-55316032 |
| 23480 | Zdhhc7 | NM_133967.3 | chr8:120081094-120101472 |
| 23481 | Zdhhc8 | NM_172151.4 | chr16:18220752-18235136 |
| 23482 | Zdhhc9 | NM_172465.4 | chrX:48171970-48208702 |
| 23483 | Zeb1 | NM_011546.3 | chr18:5591859-5775468 |
| 23484 | Zeb2 | NM_001289521.1 | chr2:44983511-45110277 |
| 23485 | Zeb2os | NR_110571.1 | chr2:45112259-45114084 |
| 23486 | Zer1 | NM_001290503.1 | chr2:30097282-30124611 |
| 23487 | Zf12 | NR_003547.2 | chrX_GL456233_random:268798-270075 |
| 23488 | Zfand1 | NM_025512.2 | chr3:10339955-10351301 |
| 23489 | Zfand2a | NM_001159908.1 | chr5:139471215-139484491 |
| 23490 | Zfand2b | NM_001159905.1 | chr1:75168645-75171626 |
| 23491 | Zfand3 | NM_148926.2 | chr17:30090086-30210020 |
| 23492 | Zfand4 | NM_001290338.1 | chr6:116264218-116330304 |
| 23493 | Zfand5 | NM_009551.5 | chr19:21272277-21286840 |
| 23494 | Zfand6 | NM_022985.6 | chr7:84615053-84679351 |
| 23495 | Zfa-ps | NR_037920.1 | chr10:52542319-52545739 |
| 23496 | Zfat | NM_001145888.1 | chr15:68083737-68258856 |
| 23497 | Zfc3h1 | NM_001033261.2 | chr10:115384958-115432771 |
| 23498 | Zfhx2 | NM_001039198.1 | chr14:55061658-55092048 |
| 23499 | Zfhx2os | NR_004444.2 | chr14:55073090-55075874 |
| 23500 | Zfhx3 | NM_007496.2 | chr8:108714643-108961636 |
| 23501 | Zfhx4 | NM_030708.2 | chr3:5218553-5415855 |
| 23502 | Zfml | NM_001166371.1 | chr6:83914352-83986871 |
| 23503 | Zfp1 | NM_001037665.2 | chr8:111643442-111671008 |
| 23504 | Zfp101 | NM_009542.2 | chr17:33380178-33394637 |
| 23505 | Zfp105 | NM_009544.2 | chr9:122923077-122931028 |
| 23506 | Zfp106 | NM_011743.2 | chr2:120506829-120563831 |
| 23507 | Zfp108 | NM_018791.2 | chr7:24254793-24262444 |
| 23508 | Zfp109 | NM_020262.3 | chr7:24227794-24237598 |
| 23509 | Zfp11 | NM_172462.4 | chr5:129654564-129670088 |
| 23510 | Zfp110 | NM_022981.4 | chr7:12834809-12850584 |
| 23511 | Zfp111 | NM_019940.2 | chr7:24193214-24208149 |
| 23512 | Zfp112 | NM_021307.2 | chr7:24112319-24127952 |
| 23513 | Zfp113 | NM_019747.4 | chr5:138139701-138155744 |
| 23514 | Zfp114 | NM_001029933.2 | chr7:24175044-24182318 |
| 23515 | Zfp119a | NM_145546.6 | chr17:55864891-55878953 |
| 23516 | Zfp119b | NM_146249.4 | chr17:55938372-55945259 |
| 23517 | Zfp12 | NM_001289589.1 | chr5:143235162-143248834 |
| 23518 | Zfp120 | NM_023266.4 | chr2:150114406-150136678 |
| 23519 | Zfp128 | NM_153802.4 | chr7:12881177-12893422 |
| 23520 | Zfp13 | NM_011747.2 | chr17:23575851-23599487 |
| 23521 | Zfp131 | NM_028245.4 | chr13:119785185-119790806 |
| 23522 | Zfp133-ps | NR_033459.1 | chr2:144459279-144467794 |
| 23523 | Zfp14 | NM_011748.2 | chr7:30036358-30051396 |
| 23524 | Zfp142 | NM_029888.3 | chr1:74566425-74588028 |
| 23525 | Zfp143 | NM_009281.3 | chr7:110061701-110095392 |
| 23526 | Zfp146 | NM_011980.3 | chr7:30161267-30169727 |
| 23527 | Zfp148 | NM_011749.4 | chr16:33380774-33503903 |
| 23528 | Zfp157 | NM_028130.3 | chr5:138441475-138460694 |
| 23529 | Zfp160 | NM_145483.2 | chr17:21008940-21028856 |
| 23530 | Zfp169 | NM_001164575.1 | chr13:48487659-48513410 |
| 23531 | Zfp174 | NM_001081217.1 | chr16:3847222-3858880 |
| 23532 | Zfp180 | NM_001045486.2 | chr7:24081896-24107708 |
| 23533 | Zfp182 | NM_001013387.2 | chrX:21026183-21062038 |
| 23534 | Zfp184 | NM_183014.1 | chr13:21945093-21960485 |
| 23535 | Zfp185 | NM_001109043.1 | chrX:72987338-73031543 |
| 23536 | Zfp189 | NM_001289901.1 | chr4:49521175-49531558 |
| 23537 | Zfp191 | NM_021559.2 | chr18:24012266-24020771 |
| 23538 | Zfp2 | NM_001044697.2 | chr11:50898711-50916176 |
| 23539 | Zfp202 | NM_030713.2 | chr9:40192315-40213604 |
| 23540 | Zfp207 | NM_001130169.1 | chr11:80383278-80396248 |
| 23541 | Zfp212 | NM_001145881.1 | chr6:47920567-47932637 |
| 23542 | Zfp213 | NM_001033496.3 | chr17:23556766-23564226 |
| 23543 | Zfp217 | NM_001033299.3 | chr2:170108642-170131220 |
| 23544 | Zfp219 | NM_001253694.1 | chr14:52006085-52019713 |
| 23545 | Zfp229 | NM_001164676.1 | chr17:21733793-21748969 |
| 23546 | Zfp235 | NM_019941.2 | chr7:24134162-24143241 |
| 23547 | Zfp236 | NM_177832.3 | chr18:82593596-82692734 |

Fig. 26 - 125

| | | | | | | | | |
|---|---|---|---|---|---|---|---|---|
| 23548 | Zfp239 | NM_001001792.1 | chr6:117863076-117872766 | | 23643 | Zfp46 | NM_009557.3 | chr4:136286068-136293942 |
| 23549 | Zfp248 | NM_028335.2 | chr6:118427318-118455506 | | 23644 | Zfp462 | NM_172867.3 | chr4:54947944-55083563 |
| 23550 | Zfp251 | NM_001007568.2 | chr15:76852140-76871435 | | 23645 | Zfp467 | NM_001085415.1 | chr6:48436612-48445090 |
| 23551 | Zfp26 | NM_011753.3 | chr9:20428317-20460160 | | 23646 | Zfp472 | NM_153063.3 | chr17:32965830-32979211 |
| 23552 | Zfp260 | NM_011981.4 | chr7:30095075-30107614 | | 23647 | Zfp473 | NM_001289836.1 | chr7:44731481-44748349 |
| 23553 | Zfp263 | NM_148924.3 | chr16:3744098-3750788 | | 23648 | Zfp474 | NM_025749.3 | chr18:52615914-52639830 |
| 23554 | Zfp266 | NM_001082485.1 | chr9:20495068-20521419 | | 23649 | Zfp488 | NM_001013777.2 | chr14:33967069-33978764 |
| 23555 | Zfp27 | NM_001037707.1 | chr7:29893336-29906104 | | 23650 | Zfp493 | NM_028402.2 | chr13:67779692-67789080 |
| 23556 | Zfp273 | NM_198322.3 | chr13:67813815-67827000 | | 23651 | Zfp503 | NM_145459.3 | chr14:21983961-21989601 |
| 23557 | Zfp275 | NM_001160229.1 | chrX:73342620-73359079 | | 23652 | Zfp507 | NM_177739.3 | chr7:35772345-35802989 |
| 23558 | Zfp276 | NM_020497.2 | chr8:123254194-123270551 | | 23653 | Zfp51 | NM_009558.4 | chr17:21450373-21465589 |
| 23559 | Zfp277 | NM_172575.3 | chr12:40315045-40445790 | | 23654 | Zfp511 | NM_027201.1 | chr7:140036390-140040605 |
| 23560 | Zfp28 | NM_175247.3 | chr7:6383317-6396637 | | 23655 | Zfp512 | NM_172993.3 | chr5:31452435-31481753 |
| 23561 | Zfp280b | NM_177475.3 | chr10:76032611-76042969 | | 23656 | Zfp513 | NM_001177901.1 | chr5:31198980-31202042 |
| 23562 | Zfp280c | NM_001166648.1 | chrX:48541625-48594373 | | 23657 | Zfp516 | NM_001177464.1 | chr18:82914631-83005314 |
| 23563 | Zfp280d | NM_146224.5 | chr9:72274887-72363771 | | 23658 | Zfp518a | NM_028319.1 | chr19:40894704-40917947 |
| 23564 | Zfp281 | NM_001160251.1 | chr1:136624900-136630391 | | 23659 | Zfp518b | NM_001081144.2 | chr5:38668483-38684826 |
| 23565 | Zfp282 | NM_146175.3 | chr6:47877554-47908484 | | 23660 | Zfp52 | NM_144515.2 | chr17:21535538-21562601 |
| 23566 | Zfp286 | NM_138949.3 | chr11:62778386-62789417 | | 23661 | Zfp521 | NM_145492.4 | chr18:13687013-13972733 |
| 23567 | Zfp287 | NM_133208.2 | chr11:62711485-62729093 | | 23662 | Zfp523 | NM_172617.3 | chr17:28177417-28205886 |
| 23568 | Zfp292 | NM_013889.2 | chr4:34803109-34882948 | | 23663 | Zfp524 | NM_025324.2 | chr7:5015507-5018488 |
| 23569 | Zfp296 | NM_022409.2 | chr7:19577286-19580656 | | 23664 | Zfp526 | NM_175436.5 | chr7:25221424-25227495 |
| 23570 | Zfp3 | NM_177565.3 | chr11:70764446-70772928 | | 23665 | Zfp53 | NM_013843.3 | chr17:21488987-21510477 |
| 23571 | Zfp30 | NM_013705.1 | chr7:29784789-29794540 | | 23666 | Zfp532 | NM_207255.2 | chr18:65580229-65689436 |
| 23572 | Zfp300 | NM_183185.3 | chrX:21079149-21089229 | | 23667 | Zfp534 | NM_001127188.2 | chr4:147674224-147702631 |
| 23573 | Zfp316 | NM_017467.3 | chr5:143249694-143270022 | | 23668 | Zfp536 | NM_172385.2 | chr7:37479108-37769752 |
| 23574 | Zfp317 | NM_172918.4 | chr9:19622090-19649731 | | 23669 | Zfp54 | NM_011760.2 | chr17:21423226-21435384 |
| 23575 | Zfp318 | NM_021346.2 | chr17:46383765-46420918 | | 23670 | Zfp541 | NM_001099277.1 | chr7:16071941-16096328 |
| 23576 | Zfp319 | NM_024487.3 | chr8:95326135-95331950 | | 23671 | Zfp551 | NM_001033820.3 | chr7:12415148-12422491 |
| 23577 | Zfp322a | NM_001111107.2 | chr13:23353102-23369208 | | 23672 | Zfp553 | NM_146201.1 | chr7:127233442-127237860 |
| 23578 | Zfp324 | NM_178732.3 | chr7:12965863-12973822 | | 23673 | Zfp558 | NM_028935.1 | chr9:18454053-18473559 |
| 23579 | Zfp326 | NM_018759.2 | chr5:105876567-105915820 | | 23674 | Zfp560 | NM_001004190.3 | chr9:20345135-20385158 |
| 23580 | Zfp329 | NM_026046.3 | chr7:12803779-12818860 | | 23675 | Zfp563 | NM_001024950.2 | chr17:33089366-33110704 |
| 23581 | Zfp330 | NM_145600.1 | chr8:82768619-82774126 | | 23676 | Zfp566 | NM_152814.2 | chr7:30077336-30090510 |
| 23582 | Zfp334 | NM_178411.3 | chr2:165377435-165388259 | | 23677 | Zfp568 | NM_001033355.3 | chr7:29983954-30028282 |
| 23583 | Zfp335 | NM_199027.2 | chr2:164891891-164911750 | | 23678 | Zfp57 | NM_001013745.2 | chr17:37002524-37010729 |
| 23584 | Zfp341 | NM_199304.1 | chr2:154613367-154646817 | | 23679 | Zfp572 | NR_045613.1 | chr15:59306947-59312013 |
| 23585 | Zfp345 | NM_001034900.3 | chr2:150470990-150485063 | | 23680 | Zfp574 | NM_001168506.1 | chr7:25077204-25083492 |
| 23586 | Zfp346 | NM_012017.2 | chr13:55105308-55135071 | | 23681 | Zfp575 | NM_001033205.3 | chr7:24583837-24587641 |
| 23587 | Zfp35 | NM_011755.2 | chr18:23989633-24005371 | | 23682 | Zfp579 | NM_026741.2 | chr7:4992851-4996101 |
| 23588 | Zfp352 | NM_153102.3 | chr4:90218819-90225687 | | 23683 | Zfp58 | NM_001007575.2 | chr13:67490166-67500522 |
| 23589 | Zfp354a | NM_009329.3 | chr11:51059256-51072799 | | 23684 | Zfp580 | NM_026900.1 | chr7:5051531-5053723 |
| 23590 | Zfp354b | NM_013744.3 | chr11:50921785-50931635 | | 23685 | Zfp583 | NM_001033249.3 | chr7:6315664-6330434 |
| 23591 | Zfp354c | NM_013922.4 | chr11:50811084-50827731 | | 23686 | Zfp59 | NM_011762.3 | chr7:27388583-27856774 |
| 23592 | Zfp358 | NM_080461.2 | chr8:3493137-3497208 | | 23687 | Zfp592 | NM_178707.4 | chr7:80993683-81045162 |
| 23593 | Zfp36 | NM_011756.4 | chr7:28376783-28379228 | | 23688 | Zfp593 | NM_024215.2 | chr4:134243305-134245591 |
| 23594 | Zfp362 | NM_001081098.1 | chr4:128773084-128806112 | | 23689 | Zfp595 | NM_176622.3 | chr13:67312997-67332560 |
| 23595 | Zfp365 | NM_178679.2 | chr10:67886104-67912662 | | 23690 | Zfp597 | NM_001033159.2 | chr16:3861543-3872374 |
| 23596 | Zfp366 | NM_001004149.1 | chr13:99184822-99247032 | | 23691 | Zfp598 | NM_183149.1 | chr17:24669751-24682016 |
| 23597 | Zfp367 | NM_175494.4 | chr13:64133056-64153199 | | 23692 | Zfp599 | NM_183149.3 | chr9:22247429-22259895 |
| 23598 | Zfp369 | NM_165278853.5 | chr13:65278853-65297795 | | 23693 | Zfp6 | NM_009560.2 | chr7:27731408-27751689 |
| 23599 | Zfp36l1 | NM_007564.5 | chr12:80107759-80113013 | | 23694 | Zfp600 | NM_001177545.2 | chr4:146157689-146198756 |
| 23600 | Zfp36l2 | NM_001001806.2 | chr17:84183927-84187947 | | 23695 | Zfp605 | NM_001163996.1 | chr5:110110091-110129794 |
| 23601 | Zfp36l3 | NM_001009549.2 | chrX:53772685-53776394 | | 23696 | Zfp606 | NM_001039951.2 | chr7:12478304-12482714 |
| 23602 | Zfp37 | NM_001290350.1 | chr4:62189536-62208546 | | 23697 | Zfp607 | NM_001024726.2 | chr7:27860584-27880825 |
| 23603 | Zfp382 | NM_001081007.1 | chr7:30121947-30135032 | | 23698 | Zfp608 | NM_175751.4 | chr18:54888044-54990180 |
| 23604 | Zfp383 | NM_001243908.1 | chr7:29908516-29916813 | | 23699 | Zfp609 | NM_172536.3 | chr9:65691582-65827564 |
| 23605 | Zfp384 | NM_001252083.1 | chr6:125009237-125037870 | | 23700 | Zfp61 | NM_009561.2 | chr7:24291045-24299549 |
| 23606 | Zfp385a | NM_013866.2 | chr15:103313894-103340086 | | 23701 | Zfp612 | NM_175480.4 | chr8:110079733-110092752 |
| 23607 | Zfp385b | NM_001113399.1 | chr2:77410626-77703272 | | 23702 | Zfp616 | NM_001177570.1 | chr11:74079169-74087301 |
| 23608 | Zfp385c | NM_177790.4 | chr11:100628215-100650693 | | 23703 | Zfp617 | NM_133358.3 | chr8:71922824-71934630 |
| 23609 | Zfp386 | NM_001040066.3 | chr12:116047723-116063207 | | 23704 | Zfp618 | NM_028326.1 | chr4:62965573-63134030 |
| 23610 | Zfp389 | NR_026798.1 | chr13:21504315-21506524 | | 23705 | Zfp619 | NM_001004139.2 | chr7:39517765-39540415 |
| 23611 | Zfp39 | NM_011758.2 | chr11:58888152-58904226 | | 23706 | Zfp62 | NM_001024846.1 | chr11:49203499-49218816 |
| 23612 | Zfp395 | NM_199029.2 | chr14:65358675-65398930 | | 23707 | Zfp622 | NM_144523.2 | chr15:25984365-25998482 |
| 23613 | Zfp397 | NM_027007.2 | chr18:23954687-23964670 | | 23708 | Zfp623 | NM_030199.3 | chr15:75940951-75949400 |
| 23614 | Zfp398 | NM_027477.3 | chr6:47835660-47868257 | | 23709 | Zfp628 | NM_170759.2 | chr7:4915216-4922003 |
| 23615 | Zfp40 | NM_009555.2 | chr17:23173868-23193228 | | 23710 | Zfp629 | NM_177226.5 | chr7:127607034-127614433 |
| 23616 | Zfp407 | NM_001033341.2 | chr18:84207701-84589504 | | 23711 | Zfp637 | NM_177684.2 | chr6:117841241-117845956 |
| 23617 | Zfp408 | NM_001034517.2 | chr2:91643687-91649791 | | 23712 | Zfp639 | NM_001161818.1 | chr3:32510549-32520833 |
| 23618 | Zfp41 | NM_001044718.2 | chr15:75616683-75625900 | | 23713 | Zfp64 | NM_009564.3 | chr2:168925360-168955587 |
| 23619 | Zfp410 | NM_001252582.1 | chr12:84316858-84334119 | | 23714 | Zfp641 | NM_173769.3 | chr15:98286121-98296083 |
| 23620 | Zfp414 | NM_026712.3 | chr17:33629091-33631714 | | 23715 | Zfp644 | NM_026856.2 | chr5:106616740-106696830 |
| 23621 | Zfp418 | NM_146179.2 | chr7:7171352-7183560 | | 23716 | Zfp646 | NM_172749.4 | chr7:127877700-127885996 |
| 23622 | Zfp42 | NM_009556.3 | chr8:43295066-43307009 | | 23717 | Zfp647 | NM_001168276.1 | chr15:76910369-76925448 |
| 23623 | Zfp420 | NM_172740.2 | chr7:29859978-29877302 | | 23718 | Zfp648 | NM_001204908.1 | chr1:154201186-154205674 |
| 23624 | Zfp422 | NM_026057.3 | chr6:116624015-116628999 | | 23719 | Zfp65 | NM_145622.2 | chr13:67705305-67729173 |
| 23625 | Zfp423 | NM_033327.2 | chr8:87661809-87959595 | | 23720 | Zfp651 | NM_001166644.1 | chr9:121760032-121771742 |
| 23626 | Zfp426 | NM_001110309.1 | chr9:20468548-20492746 | | 23721 | Zfp652 | NM_201609.2 | chr11:95749066-95764713 |
| 23627 | Zfp428 | NM_001290461.1 | chr7:24507086-24515682 | | 23722 | Zfp652os | NR_045780.1 | chr11:95700105-95712754 |
| 23628 | Zfp429 | NM_001080941.1 | chr13:67389327-67399767 | | 23723 | Zfp653 | NM_177318.3 | chr9:22055410-22071376 |
| 23629 | Zfp433 | NM_001243067.1 | chr10:81704824-81881086 | | 23724 | Zfp654 | NM_028059.2 | chr16:64780346-64786321 |
| 23630 | Zfp438 | NM_178722.5 | chr18:5210030-5334439 | | 23725 | Zfp655 | NM_001083958.1 | chr5:145237714-145238322 |
| 23631 | Zfp442 | XM_006500041.2 | chr2:150406372-150451530 | | 23726 | Zfp658 | NM_001008549.2 | chr7:43562369-43575461 |
| 23632 | Zfp444 | NM_001146024.1 | chr7:6172512-6193104 | | 23727 | Zfp661 | NM_001111029.1 | chr2:127575534-127584677 |
| 23633 | Zfp445 | NM_173364.5 | chr9:122848909-122866006 | | 23728 | Zfp663 | NM_001005425.1 | chr2:165351296-165362119 |
| 23634 | Zfp446 | NM_001168561.1 | chr7:12977847-12985716 | | 23729 | Zfp667 | NM_001081750.1 | chr5:124862704-124888630 |
| 23635 | Zfp449 | NM_030139.4 | chrX:56346399-56365674 | | 23730 | Zfp668 | NM_001024928.2 | chr7:6286579-6307883 |
| 23636 | Zfp451 | NM_001290699.1 | chr1:33761540-33814595 | | 23731 | Zfp669 | NM_146259.3 | chr7:127865358-127876823 |
| 23637 | Zfp454 | NM_172794.2 | chr11:50872722-50887443 | | 23732 | Zfp672 | NM_001256516.1 | chr11:58315113-58323365 |
| 23638 | Zfp455 | NM_001048204.1 | chr13:67194505-67209298 | | 23733 | Zfp677 | NM_172486.2 | chr17:21383747-21399265 |
| 23639 | Zfp456 | NM_001001186.3 | chr13:67363583-67375763 | | 23734 | Zfp68 | NM_001044747.2 | chr5:138603651-138619743 |
| 23640 | Zfp457 | NM_001003666.2 | chr13:67292450-67306412 | | 23735 | Zfp687 | NM_030074.2 | chr3:95006701-95015238 |
| 23641 | Zfp458 | NM_001001152.2 | chr13:67254917-67269068 | | 23736 | Zfp688 | NM_026999.4 | chr7:127418965-127422034 |
| 23642 | Zfp459 | NM_177811.4 | chr13:67405712-67421418 | | 23737 | Zfp689 | NM_175163.3 | chr7:127442135-127449158 |

Fig. 26 - 126

| | | | |
|---|---|---|---|
| 23738 | Zfp69 | NM_001005788.3 | chr4:120930136-120951701 |
| 23739 | Zfp691 | NM_001145935.1 | chr4:119169517-119173856 |
| 23740 | Zfp692 | NM_001040686.1 | chr11:58307068-58314613 |
| 23741 | Zfp697 | NM_172863.4 | chr3:98382480-98431949 |
| 23742 | Zfp7 | NM_145916.2 | chr15:76879275-76892394 |
| 23743 | Zfp703 | NM_001101502.1 | chr8:26977335-26981462 |
| 23744 | Zfp704 | NM_133218.2 | chr3:9427009-9610085 |
| 23745 | Zfp706 | NM_026521.4 | chr15:36997026-37007402 |
| 23746 | Zfp707 | NM_001081065.1 | chr15:75969184-75975865 |
| 23747 | Zfp708 | NM_001012325.2 | chr13:67069397-67097976 |
| 23748 | Zfp709 | NM_145624.4 | chr8:71882067-71892565 |
| 23749 | Zfp710 | NM_001145999.1 | chr7:80024813-80092751 |
| 23750 | Zfp711 | NM_177747.3 | chrX:112600525-112635062 |
| 23751 | Zfp712 | NM_001166218.1 | chr13:67038593-67061170 |
| 23752 | Zfp715 | NM_027264.3 | chr7:43296522-43313261 |
| 23753 | Zfp719 | NM_172482.1 | chr7:43579585-43593710 |
| 23754 | Zfp72 | NM_001081680.1 | chr13:74371425-74376566 |
| 23755 | Zfp735 | NM_001126489.2 | chr11:73688777-73713808 |
| 23756 | Zfp738 | NM_001001187.3 | chr13:67667440-67683512 |
| 23757 | Zfp74 | NM_178384.3 | chr7:29932790-29951893 |
| 23758 | Zfp740 | NM_001289690.1 | chr15:102204570-102215610 |
| 23759 | Zfp746 | NM_001163475.1 | chr6:48062894-48086593 |
| 23760 | Zfp747 | NM_175560.3 | chr7:127372536-127376050 |
| 23761 | Zfp748 | NM_001035231.3 | chr13:67538640-67553152 |
| 23762 | Zfp750 | NM_178763.4 | chr11:121510975-121519342 |
| 23763 | Zfp758 | NM_145484.2 | chr17:22361452-22377281 |
| 23764 | Zfp759 | NM_172392.3 | chr13:67128227-67141787 |
| 23765 | Zfp760 | NM_001008501.2 | chr17:21707740-21725636 |
| 23766 | Zfp763 | NM_028543.3 | chr17:33016863-33033381 |
| 23767 | Zfp764 | NM_001167832.1 | chr7:127403667-127406822 |
| 23768 | Zfp768 | NM_146202.1 | chr7:127342794-127345314 |
| 23769 | Zfp770 | NM_175466.4 | chr2:114193460-114201432 |
| 23770 | Zfp771 | NM_177362.3 | chr7:127244525-127254801 |
| 23771 | Zfp772 | NM_145577.2 | chr7:7202121-7209998 |
| 23772 | Zfp773 | NM_029584.1 | chr7:7130677-7136755 |
| 23773 | Zfp775 | NM_173429.2 | chr6:48613179-48623227 |
| 23774 | Zfp777 | NM_001081382.1 | chr6:48024187-48048114 |
| 23775 | Zfp78 | NM_001025163.1 | chr7:6363307-6382605 |
| 23776 | Zfp780b | NM_001081021.1 | chr7:27959799-27979157 |
| 23777 | Zfp781 | NM_199062.1 | chr10:81742820-81930480 |
| 23778 | Zfp783 | NR_027963.1 | chr6:47943174-47954549 |
| 23779 | Zfp784 | NM_001039532.2 | chr7:5034445-5038446 |
| 23780 | Zfp786 | NM_177882.4 | chr6:47819265-47830505 |
| 23781 | Zfp787 | NM_001013012.1 | chr7:6131488-6155971 |
| 23782 | Zfp788 | NM_183453.0-41651532 | chr7:41635450-41651532 |
| 23783 | Zfp790 | NM_001145880.1 | chr7:29816071-29832042 |
| 23784 | Zfp791 | NM_001037745.1 | chr8:85109166-85123095 |
| 23785 | Zfp799 | NM_177359.5 | chr17:32815452-32830261 |
| 23786 | Zfp800 | NM_001081678.1 | chr6:28239930-28261601 |
| 23787 | Zfp804a | NM_175513.3 | chr2:82053657-82259878 |
| 23788 | Zfp804b | NM_001163223.1 | chr5:6769029-7344378 |
| 23789 | Zfp808 | NM_001039239.2 | chr13:62129889-62173936 |
| 23790 | Zfp809 | NM_001164624.1 | chr9:22225711-22239693 |
| 23791 | Zfp81 | NM_207541.1 | chr17:33333727-33358878 |
| 23792 | Zfp810 | NM_145612.2 | chr9:22276747-22307638 |
| 23793 | Zfp811 | NM_001267583.1 | chr17:32795675-32809931 |
| 23794 | Zfp819 | NM_028913.3 | chr7:43607168-43618279 |
| 23795 | Zfp82 | NM_001252519.1 | chr7:30056033-30072823 |
| 23796 | Zfp820 | NM_029281.2 | chr17:21816875-21845759 |
| 23797 | Zfp821 | NM_001167946.2 | chr8:109705545-109724932 |
| 23798 | Zfp825 | NM_146231.1 | chr13:74480056-74493950 |
| 23799 | Zfp827 | NM_178267.3 | chr8:79028436-79193766 |
| 23800 | Zfp830 | NM_025884.4 | chr11:82764344-82767622 |
| 23801 | Zfp831 | NM_001099328.1 | chr2:174643533-174710830 |
| 23802 | Zfp839 | NM_001199785.1 | chr12:110850278-110869998 |
| 23803 | Zfp84 | NM_023750.2 | chr7:29768551-29781419 |
| 23804 | Zfp846 | NM_172919.1 | chr9:20581327-20595193 |
| 23805 | Zfp85 | NM_001001130.2 | chr13:67747799-67755134 |
| 23806 | Zfp850 | NM_001254951.1 | chr7:27984470-28014115 |
| 23807 | Zfp859 | NR_027969.1 | chr13:67729261-67756838 |
| 23808 | Zfp862-ps | NR_015597.1 | chr6:48504338-48534831 |
| 23809 | Zfp865 | NM_001033383.2 | chr7:5020375-5033223 |
| 23810 | Zfp866 | NM_177899.3 | chr8:69761323-69774911 |
| 23811 | Zfp867 | NM_178417.3 | chr11:59461196-59472474 |
| 23812 | Zfp868 | NM_001045553.1 | chr8:69610653-69625175 |
| 23813 | Zfp869 | NM_001039965.1 | chr8:69705136-69716502 |
| 23814 | Zfp87 | NM_133228.3 | chr13:67515781-67526231 |
| 23815 | Zfp870 | NM_207245.2 | chr17:32879220-32891603 |
| 23816 | Zfp871 | NM_172458.3 | chr17:32765496-32788287 |
| 23817 | Zfp872 | NM_001033813.4 | chr9:22188165-22202123 |
| 23818 | Zfp873 | NM_001024626.2 | chr10:82048126-82061586 |
| 23819 | Zfp874a | NM_177712.4 | chr13:67440430-67451624 |
| 23820 | Zfp874b | NM_001076791.2 | chr13:67471512-67484253 |
| 23821 | Zfp879 | NM_001290779.1 | chr11:50832030-50841552 |
| 23822 | Zfp882 | NM_001166645.1 | chr8:71908605-71918851 |
| 23823 | Zfp9 | NM_011763.2 | chr6:118461949-118479273 |
| 23824 | Zfp90 | NM_011764.8 | chr8:106415338-106425089 |
| 23825 | Zfp91 | NM_053009.3 | chr19:12766938-12796123 |
| 23826 | Zfp91cntf | NR_024093.1 | chr19:12763527-12796123 |
| 23827 | Zfp92 | NM_009566.5 | chrX:73411095-73426998 |
| 23828 | Zfp93 | NM_009567.4 | chr7:24270417-24277794 |
| 23829 | Zfp930 | NM_001013379.2 | chr8:69209045-69230539 |
| 23830 | Zfp931 | NM_001162922.1 | chr2:178066877-178078425 |
| 23831 | Zfp932 | NM_145563.2 | chr5:109998526-110010411 |
| 23832 | Zfp933 | NM_198619.2 | chr4:147822985-147848375 |

| | | | |
|---|---|---|---|
| 23833 | Zfp934 | NM_001162911.1 | chr13:62516796-62558599 |
| 23834 | Zfp935 | NM_001136496.1 | chr13:62453015-62466812 |
| 23835 | Zfp936 | NM_001034893.1 | chr7:43177587-43192109 |
| 23836 | Zfp937 | NM_001142411.2 | chr2:150218098-150244874 |
| 23837 | Zfp938 | NM_001105557.2 | chr10:82224855-82241275 |
| 23838 | Zfp939 | NM_001243021.1 | chr7:39449517-39477416 |
| 23839 | Zfp94 | NM_001199321.1 | chr7:24301703-24316666 |
| 23840 | Zfp940 | NM_173738.2 | chr7:29843935-29853648 |
| 23841 | Zfp941 | NM_001001180.2 | chr7:140809676-140822178 |
| 23842 | Zfp942 | NM_001199048.1 | chr17:21926962-21962464 |
| 23843 | Zfp943 | NM_001025373.2 | chr17:21962558-21994366 |
| 23844 | Zfp944 | NM_176962.4 | chr17:22337988-22361400 |
| 23845 | Zfp945 | NM_001110254.1 | chr17:22846696-22867134 |
| 23846 | Zfp946 | NM_198003.2 | chr17:22424267-22456689 |
| 23847 | Zfp947 | NM_177596.3 | chr17:22144358-22165977 |
| 23848 | Zfp948 | NM_001002008.1 | chr17:21567045-21588682 |
| 23849 | Zfp949 | NM_001142943.1 | chr9:88548019-88571086 |
| 23850 | Zfp951 | NM_001039231.3 | chr5:104813167-104860068 |
| 23851 | Zfp952 | NM_001045559.1 | chr17:32993138-33005457 |
| 23852 | Zfp953 | NM_001038651.3 | chr13:67339308-67360572 |
| 23853 | Zfp954 | NM_172738.3 | chr7:7114682-7121476 |
| 23854 | Zfp955a | NM_029952.3 | chr17:33239506-33255145 |
| 23855 | Zfp955b | NM_001142957.1 | chr17:33289543-33304689 |
| 23856 | Zfp956 | NM_178898.4 | chr6:47953389-47965299 |
| 23857 | Zfp957 | NM_001033215.3 | chr14:79212354-79247367 |
| 23858 | Zfp958 | NM_145591.4 | chr8:4613169-4630231 |
| 23859 | Zfp959 | NM_145490.4 | chr17:55892092-55898930 |
| 23860 | Zfp960 | NM_001005358.2 | chr17:17064102-17089631 |
| 23861 | Zfp961 | NM_001164581.1 | chr8:71951065-71970333 |
| 23862 | Zfp963 | NM_001200023.1 | chr8:69741638-69749962 |
| 23863 | Zfp964 | NM_001177527.1 | chr8:69654555-69664453 |
| 23864 | Zfp97 | NM_011765.5 | chr17:17121382-17146878 |
| 23865 | Zfpl1 | NM_024231.2 | chr19:6080762-6084891 |
| 23866 | Zfpm1 | NM_009569.3 | chr8:122282140-122337247 |
| 23867 | Zfpm2 | NM_011766.5 | chr15:40655041-41104592 |
| 23868 | Zfr | NM_011767.2 | chr15:12117850-12185449 |
| 23869 | Zfr2 | NM_001034895.3 | chr10:81233162-81252123 |
| 23870 | Zfx | NM_001044386.1 | chrX:94074630-94123407 |
| 23871 | Zfy1 | NM_009570.4 | chrY:725206-797409 |
| 23872 | Zfy2 | NM_009571.2 | chrY:2106174-2170409 |
| 23873 | Zfyve1 | NM_183154.3 | chr12:83546940-83597147 |
| 23874 | Zfyve16 | NM_173392.4 | chr13:92487748-92530810 |
| 23875 | Zfyve19 | NM_001164827.1 | chr2:119208719-119217050 |
| 23876 | Zfyve20 | NM_030081.2 | chr6:92186711-92214811 |
| 23877 | Zfyve21 | NM_026752.4 | chr12:111814169-111828388 |
| 23878 | Zfyve26 | NM_001008550.1 | chr12:79232346-79296282 |
| 23879 | Zfyve27 | NM_001164531.1 | chr19:42170566-42194592 |
| 23880 | Zfyve28 | NM_001015039.1 | chr5:34194893-34288324 |
| 23881 | Zfyve9 | NM_183300.2 | chr4:108639258-108723876 |
| 23882 | Zg16 | NM_026918.2 | chr7:127050155-127051977 |
| 23883 | Zglp1 | NM_001103168.1 | chr9:21062392-21067093 |
| 23884 | Zgpat | NM_001048148.1 | chr2:181365422-181380793 |
| 23885 | Zgrf1 | NM_197997.2 | chr3:127553488-127618023 |
| 23886 | Zhx1 | NM_001042438.2 | chr15:58047002-58076508 |
| 23887 | Zhx2 | NM_199449.2 | chr15:57694696-57839832 |
| 23888 | Zhx3 | NM_177263.4 | chr2:160770446-160872990 |
| 23889 | Zic1 | NM_009573.3 | chr9:91360344-91365799 |
| 23890 | Zic2 | NM_009574.3 | chr14:122475383-122480328 |
| 23891 | Zic3 | NM_009575.2 | chrX:58030627-58036630 |
| 23892 | Zic4 | NM_009576.2 | chr9:91368971-91389348 |
| 23893 | Zic5 | NM_022987.3 | chr14:122459159-122465658 |
| 23894 | Zik1 | NM_009577.3 | chr7:10487223-10495381 |
| 23895 | Zim1 | NM_011769.4 | chr7:6675442-6696432 |
| 23896 | Zim3 | NR_036631.2 | chr7:6955685-6976662 |
| 23897 | Zkscan1 | NM_029869.1 | chr5:138085083-138107822 |
| 23898 | Zkscan14 | NM_023322.2 | chr5:145194945-145201882 |
| 23899 | Zkscan16 | NM_001099323.2 | chr4:58943627-58958355 |
| 23900 | Zkscan17 | NM_001130529.2 | chr11:59485520-59506640 |
| 23901 | Zkscan2 | NM_001081329.1 | chr7:123478638-123500449 |
| 23902 | Zkscan3 | NM_001145778.1 | chr13:21387003-21402755 |
| 23903 | Zkscan4 | NM_001039115.2 | chr13:21478848-21485505 |
| 23904 | Zkscan5 | NM_001167944.1 | chr5:145204558-145221750 |
| 23905 | Zkscan6 | NM_026107.3 | chr11:65807174-65829239 |
| 23906 | Zkscan7 | NM_001177505.1 | chr9:122898470-122896124 |
| 23907 | Zkscan8 | NM_001251833.1 | chr13:21513220-21531114 |
| 23908 | Zmat1 | NM_175446.3 | chrX:134971372-135009209 |
| 23909 | Zmat2 | NM_025594.3 | chr18:36793922-36799660 |
| 23910 | Zmat3 | NM_009517.2 | chr3:32334793-32365665 |
| 23911 | Zmat4 | NM_001277239.1 | chr8:23669660-24063116 |
| 23912 | Zmat5 | NM_028015.2 | chr11:4704677-4737666 |
| 23913 | Zmiz1 | NM_183208.4 | chr14:25459184-25666743 |
| 23914 | Zmiz2 | NM_001005867.1 | chr11:6395124-6406162 |
| 23915 | Zmpste24 | NM_172700.2 | chr4:121059237-121098243 |
| 23916 | Zmym1 | NM_026670.4 | chr4:127047093-127061132 |
| 23917 | Zmym2 | NM_029498.3 | chr14:56887794-56962579 |
| 23918 | Zmym3 | NM_001177985.1 | chrX:101404393-101419914 |
| 23919 | Zmym4 | NM_001114399.1 | chr4:126861819-126967923 |
| 23920 | Zmym5 | NM_001253752.1 | chr14:56790584-56811716 |
| 23921 | Zmym6 | NM_001285885.1 | chr4:127077382-127124374 |
| 23922 | Zmynd10 | NM_053253.3 | chr9:107547309-107551319 |
| 23923 | Zmynd11 | NM_001199141.1 | chr13:9684835-9765314 |
| 23924 | Zmynd12 | NM_001014900.2 | chr4:119422683-119453899 |
| 23925 | Zmynd15 | NM_001029929.2 | chr11:70459621-70466199 |
| 23926 | Zmynd19 | NM_026021.4 | chr2:24949776-24960870 |
| 23927 | Zmynd8 | NM_001252584.2 | chr2:165784151-165884838 |

Fig. 26 - 127

| | | | |
|---|---|---|---|
| 23928 | Znf41-ps | NR_040355.1 | chr4:145789514-145831978 |
| 23929 | Znf512b | NM_001164597.1 | chr2:181582102-181592461 |
| 23930 | Znfx1 | NM_001033196.2 | chr2:167035796-167063015 |
| 23931 | Znhit1 | NM_027318.4 | chr5:136982193-136987959 |
| 23932 | Znhit2 | NM_013859.2 | chr19:6061206-6062468 |
| 23933 | Znhit3 | NM_001005223.2 | chr11:84910954-84916356 |
| 23934 | Znhit6 | NM_001081094.1 | chr3:145576207-145605245 |
| 23935 | Znrd1 | NM_023162.4 | chr17:36954357-36958428 |
| 23936 | Znrd1as | NM_029602.1 | chr17:36958591-36965623 |
| 23937 | Znrf1 | NM_001168621.1 | chr8:111536639-111626030 |
| 23938 | Znrf2 | NM_199143.2 | chr6:54816915-54890224 |
| 23939 | Znrf3 | NM_001080924.2 | chr11:5276328-5444847 |
| 23940 | Znrf4 | NM_011483.2 | chr17:56511247-56512483 |
| 23941 | Zp1 | NM_009580.2 | chr19:10914295-10920601 |
| 23942 | Zp2 | NM_011775.6 | chr7:120132360-120145290 |
| 23943 | Zp3 | NM_011776.1 | chr5:135980104-135988624 |
| 23944 | Zp3r | NM_009581.2 | chr1:130576705-130629606 |
| 23945 | Zp4-ps | NR_027813.1 | chr13:11522051-11525682 |
| 23946 | Zpbp | NM_001185153.1 | chr11:11280039-11462419 |
| 23947 | Zpbp2 | NM_001166494.1 | chr11:98551096-98558665 |
| 23948 | Zpld1 | NM_178720.4 | chr16:55225174-55283237 |
| 23949 | Zpr1 | NM_011752.2 | chr9:46273063-46282642 |
| 23950 | Zranb1 | NM_207302.1 | chr7:132949621-132983951 |
| 23951 | Zranb2 | NM_017381.2 | chr3:157534396-157548339 |
| 23952 | Zranb3 | NM_001285945.1 | chr1:127954178-128103047 |
| 23953 | Zrsr1 | NM_011663.3 | chr11:22972004-22976496 |
| 23954 | Zrsr2 | NM_009453.3 | chrX:163935442-163958666 |
| 23955 | Zscan10 | NM_001033425.4 | chr17:23600825-23611019 |
| 23956 | Zscan12 | NM_016684.2 | chr13:21362819-21372302 |
| 23957 | Zscan18 | NM_001017955.2 | chr7:12768091-12775658 |
| 23958 | Zscan2 | NM_009553.2 | chr7:80862107-80876513 |
| 23959 | Zscan20 | NM_177758.4 | chr4:128583538-128610098 |
| 23960 | Zscan21 | NM_001044703.2 | chr5:138116904-138134265 |
| 23961 | Zscan22 | NM_001001447.3 | chr7:12897808-12909083 |
| 23962 | Zscan25 | NM_001081431.1 | chr5:145283342-145291469 |
| 23963 | Zscan26 | NM_001013786.2 | chr13:21442174-21453727 |
| 23964 | Zscan29 | NM_001290819.1 | chr2:121158272-121171125 |
| 23965 | Zscan4a | NR_033707.1 | chr7:10794240-10799065 |
| 23966 | Zscan4b | NM_001185173.1 | chr7:10900739-10905050 |
| 23967 | Zscan4c | NM_001013765.2 | chr7:11005744-11010547 |
| 23968 | Zscan4d | NM_001100186.1 | chr7:11161642-11166148 |
| 23969 | Zscan4e | NM_001161802.1 | chr7:11306369-11310682 |
| 23970 | Zscan4f | NM_001110316.2 | chr7:11397914-11402318 |
| 23971 | Zscan5b | NM_133204.2 | chr7:6222277-6239412 |
| 23972 | Zswim1 | NM_028028.2 | chr2:164822685-164826867 |
| 23973 | Zswim2 | NM_027964.2 | chr2:83915078-83941226 |
| 23974 | Zswim3 | NM_178375.2 | chr2:164805113-164822127 |
| 23975 | Zswim4 | NM_172503.3 | chr8:84210941-84237042 |
| 23976 | Zswim5 | NM_001029912.2 | chr4:116877401-116989105 |
| 23977 | Zswim6 | NM_145456.2 | chr13:107724616-107890064 |
| 23978 | Zswim7 | NM_027198.1 | chr11:62267223-62281395 |
| 23979 | Zswim8 | NM_001252081.1 | chr14:20707551-20723619 |
| 23980 | Zufsp | NM_028287.2 | chr10:33926935-33951212 |
| 23981 | Zw10 | NM_012039.2 | chr9:49055580-49078773 |
| 23982 | Zwilch | NM_026507.4 | chr9:64137143-64172931 |
| 23983 | Zwint | NM_025635.4 | chr10:72654845-72669792 |
| 23984 | Zxda | NR_003292.1 | chrX:94791284-94798289 |
| 23985 | Zxdb | NM_001081473.1 | chrX:94724568-94730191 |
| 23986 | Zxdc | NM_030260.3 | chr6:90369493-90385394 |
| 23987 | Zyg11a | NM_001167936.1 | chr4:108181933-108217922 |
| 23988 | Zyg11b | NM_001033634.3 | chr4:108227754-108301090 |
| 23989 | Zyx | NM_001289617.1 | chr6:42349827-42360213 |
| 23990 | Zzef1 | NM_001045536.2 | chr11:72796225-72927120 |
| 23991 | Zzz3 | NM_001080755.2 | chr3:152396002-152462826 |

Fig. 27 - 1

| A |
|---|
| 4-Acetamidobutanoic acid |
| Acetoacetamide |
| Acetoacetic acid |
| Acetohydrazide |
| N-Acetyl-β-alanine |
| Acetyl CoA |
| 3-Acetylacrylic acid |
| N-Acetylalanine |
| 4-(β-Acetylaminoethyl)imidazole |
| N-Acetylasparagine |
| N-Acetylaspartic acid |
| O-Acetylcarnitine |
| Acetylcholine |
| N-Acetylcysteine |
| N-Acetylgalactosamine |
| N-Acetylglucosamine |
| N-Acetylglucosamine 1-phosphate |
| N-Acetylglucosamine 6-phosphate |
| N-Acetylglucosylamine |
| N-Acetylglutamic acid |
| N-Acetylglycine |
| N-Acetylhistidine |
| O-Acetylhomoserine |
| N-Acetylleucine |
| $N^6$-Acetyllysine |
| N-Acetyllysine |
| N-Acetylmannosamine |
| N-Acetylmethionine |
| N-Acetylmuramic acid |
| N-Acetylneuraminic acid |
| N-Acetylornithine |
| N-Acetylphenylalanine |
| N-Acetylputrescine |
| O-Acetylserine |
| N-Acetylserine |
| $N^8$-Acetylspermidine |
| $N^1$-Acetylspermine |
| N-Acetyltryptophan |
| cis-Aconitic acid |
| trans-Aconitic acid |
| Adenine |
| Adenosine |
| Adenosine 5'-[γ-thio]triphosphate |
| Adenosine 5'-phosphosulfate |
| S-Adenosylhomocysteine |
| S-Adenosylmethionine |
| Adenylosuccinic acid |
| Adipic acid |
| ADMA |
| ADP-glucose |
| ADP-ribose |
| ADP |
| 3',5'-ADP |
| Adrenaline |
| Agmatine |
| Ala-Ala |
| β-Ala-Lys |
| Ala |
| β-Ala |
| Albendazole |
| Allantoic acid |
| Allantoin |
| Alliin |
| Allocryptopine |
| Amiloride |
| 2-Amino-2-(hydroxymethyl)-1,3-propanediol |
| 2-Amino-2-methyl-1,3-propanediol |
| 2-Amino-2-methylbutyric acid |
| 4-Amino-3-hydroxybutyric acid |
| 2-Amino-3-phosphonopropionic acid |
| 5-Amino-4-oxovaleric acid |
| 3-Amino-5-hydroxypyrazole |
| 2-Aminoadipic acid |
| 2-Aminobenzenesulfonic acid |
| p-Aminobenzoic acid |
| 2-Aminobutyric acid |
| 3-Aminobutyric acid |
| 1-Aminocyclopentanecarboxylic acid |

| |
|---|
| 1-Aminocyclopropane-1-carboxylic acid |
| 2-Aminoethylphosphonic acid |
| 1-Aminoethylphosphonic acid |
| 6-Aminohexanoic acid |
| 4-Aminohippuric acid |
| 5-Aminoimidazole-4-carboxamide ribotide |
| 3-Aminoisobutyric acid |
| 2-Aminoisobutyric acid |
| 6-Aminopenicillanic acid |
| o-Aminophenol |
| p-Aminophenol |
| m-Aminophenol |
| 4-Aminophenylsulfone |
| Aminophylline |
| 3-Aminopropane-1,2-diol |
| 3-Aminopropionitrile |
| Aminopyrine |
| 4-Aminosalicylic acid |
| 5-Aminovaleric acid |
| AMP |
| 3'-AMP |
| Anabasine |
| Aniline |
| p-Anisic acid |
| Anserine |
| Anthranilic acid |
| Arg-Glu |
| Arg |
| Argininosuccinic acid |
| Ascorbic acid |
| Asn |
| Asp |
| ATP |
| Atrolactic acid |
| Azelaic acid |
| Azetidine 2-carboxylic acid |
| B |
| Barbituric acid |
| Bentazone |
| Benzamide |
| Benzocaine |
| Benzoic acid |
| Benzoylformic acid |
| $N^6$-Benzyladenine |
| Benzylsuccinic acid |
| Betaine |
| Betaine aldehyde |
| Biopterin |
| Biotin |
| Bis(p-nitrophenyl)phosphate |
| 4-Bromophenylalanine |
| Buformin |
| Butyric acid |
| γ-Butyrobetaine |
| Butyrylcarnitine |
| C |
| Cadaverine |
| Caffeine |
| cAMP |
| Canavanine |
| N-Carbamoylaspartic acid |
| Carbamoylphosphate |
| N-Carbamylglutamic acid |
| β-Carboline |
| 2-Carboxybenzaldehyde |
| S-Carboxymethylcysteine |
| Carboxymethyllysine |
| Carnitine |
| Carnosine |
| cCMP |
| 2',3'-cCMP |
| CDP-choline |
| CDP |
| cGMP |
| p-Chlorophenylacetic acid |
| Cholic acid |
| Choline |
| Cimetidine |

Fig. 27 - 2

| |
|---|
| cIMP |
| trans-Cinnamic acid |
| Citraconic acid |
| Citramalic acid |
| Citric acid |
| Citrulline |
| CMP-N-acetylneuraminate |
| CMP |
| 3'-CMP |
| 2'-CMP |
| CoA |
| p-Coumaric acid |
| o-Coumaric acid |
| Creatine |
| 2-(Creatinine-3-yl)propionic acid |
| Creatinine |
| Crotonic acid |
| cTMP |
| CTP |
| Cumic acid |
| β-Cyanoalanine |
| 3',5'-Cyclic dAMP |
| Cyclohexanecarboxylic acid |
| Cyclohexylamine |
| Cys-Gly |
| Cys |
| Cystathionine |
| Cysteamine |
| Cysteic acid |
| Cysteine glutathione disulfide |
| Cysteinesulfinic acid |
| Cystine |
| Cytidine |
| Cytosine |
| D |
| dADP |
| DAMGO |
| Daminozide |
| dAMP |
| dATP |
| dCDP |
| dCMP |
| dCTP |
| Deamido-NAD+ |
| Decanoic acid |
| 3-Dehydroshikimic acid |
| 5'-Deoxy-5'-methylthioadenosine |
| 2'-Deoxyadenosine |
| 5'-Deoxyadenosine |
| 2'-Deoxycytidine |
| 2-Deoxyglucose 6-phosphate |
| 2'-Deoxyguanosine |
| 2-Deoxyribose 1-phosphate |
| 2'-Deoxyuridine |
| 3'-Dephospho CoA |
| Desthiobiotin |
| dGDP |
| dGMP |
| dGTP |
| P1, P4-Di(adenosine-5') tetraphosphate |
| 2,4-Diaminobutyric acid |
| 2,6-Diaminopimelic acid |
| 1,3-Diaminopropane |
| 2,3-Diaminopropionic acid |
| Diazoxide |
| Diethanolamine |
| Diethylaminomalonic acid |
| 2,6-Diethylaniline |
| Digalacturonic acid |
| 7,8-Dihydrobiopterin |
| 7,8-Dihydrofolic acid |
| 7,8-Dihydroneopterin |
| Dihydroorotic acid |
| Dihydrouracil |
| Dihydroxyacetone phosphate |
| 2,5-Dihydroxybenzoic acid |
| 2,4-Dihydroxybenzoic acid |
| 5,6-Dihydroxyindole |
| 3,4-Dihydroxyphenylglycol |

| |
|---|
| 2,4-Dihydroxypyrimidine-5-carboxylic acid |
| N,N-Dimethylaniline |
| 5,6-Dimethylbenzimidazole |
| N,N-Dimethylglycine |
| N,N-Dimethylhistidine |
| 2,5-Dimethylpyrazine |
| dIMP |
| Diphenylamine |
| 2,3-Diphosphoglyceric acid |
| dITP |
| Dodecanedioic acid |
| DOPA |
| Dopamine |
| dTDP-glucose |
| dTDP |
| dTMP |
| dTTP |
| dUDP |
| dUMP |
| dUTP |
| E |
| Ectoine |
| EDTA |
| Ergothioneine |
| Erythrose 4-phosphate |
| Ethanolamine |
| Ethanolamine phosphate |
| Ethionine |
| m-Ethoxybenzoic acid |
| Ethyl glucuronide |
| Ethylacetimidate |
| $N^2$-Ethylglutamine |
| N-Ethylglycine |
| N-Ethylmaleimide |
| Etidronic acid |
| F |
| FAD |
| Ferulic acid |
| Folic acid |
| Formylanthranilic acid |
| N-Formylaspartic acid |
| N-Formylglycine |
| N-Formylmethionine |
| Fructose 1,6-diphosphate |
| Fructose 6-phosphate |
| Fumaric acid |
| Fumaric acid monomethyl ester |
| 2-Furoic acid |
| G |
| GABA |
| Galactosamine |
| Galacturonate 1-phosphate |
| Galacturonic acid |
| GDP-fucose |
| GDP-galactose |
| GDP-glucose |
| GDP-mannose |
| GDP |
| 3',5'-GDP |
| Gibberellic acid |
| Gln |
| γ-Glu-2-aminobutyric acid |
| γ-Glu-Cys |
| Glu-Glu |
| γ-Glu-Val-Gly |
| Glu |
| Glucaric acid |
| Gluconic acid |
| Gluconolactone |
| Glucosamine |
| Glucosamine 6-phosphate |
| Glucosamine 6-sulfuric acid |
| Glucosaminic acid |
| Glucose 1-phosphate |
| Glucose 6-phosphate |
| Glucurone |
| Glucuronic acid |
| trans-Glutaconic acid |
| Glutaric acid |

Fig. 27 - 3

| |
|---|
| Glutaryl CoA |
| Glutathione (GSH) |
| Glutathione (GSSG) |
| Gly-Asp |
| Gly-Gly |
| Gly-Leu |
| Gly |
| Glyceraldehyde 3-phosphate |
| Glyceric acid |
| Glycerol |
| Glycerol 2-phosphate |
| Glycerol 3-phosphate |
| Glycerophosphocholine |
| Glycine anhydride |
| Glycocholic acid |
| Glycolic acid |
| Glycyrrhetinic acid |
| Glyoxylic acid |
| GMP |
| GTP |
| 2-Guanidinobenzimidazole |
| 4-Guanidinobutyric acid |
| 3-Guanidinopropionic acid |
| Guanidinosuccinic acid |
| Guanidoacetic acid |
| Guanine |
| Guanosine |
| Guanosine 5'-[γ-thio]triphosphate |
| Gulonic acid |
| Gulonolactone |
| H |
| Harmaline |
| Heptanoic acid |
| Hercynine |
| Hexamine |
| Hexanoic acid |
| Hexylamine |
| S-Hexylglutathione |
| Hippuric acid |
| His-Glu |
| His |
| Histamine |
| Histidinol |
| Homoarginine |
| Homocarnosine |
| Homocitrulline |
| Homocysteic acid |
| Homocysteine |
| Homocysteinesulfinic acid |
| Homocysteinethiolactone |
| Homocystine |
| Homoserine |
| Homoserinelactone |
| Homovanillic acid |
| Hordenine |
| 3-Hydroxy-3-methylglutaric acid |
| 2-Hydroxy-4-methylvaleric acid |
| 8-Hydroxy-2'-deoxyguanosine |
| 3-Hydroxyanthranilic acid |
| threo-3-Hydroxyaspartic acid |
| p-Hydroxybenzoic acid |
| m-Hydroxybenzoic acid |
| o-Hydroxybenzoic acid |
| 3-Hydroxybutyric acid |
| 2-Hydroxybutyric acid |
| 10-Hydroxydecanoic acid |
| 6-Hydroxydopamine |
| 2-Hydroxyglutaric acid |
| 6-Hydroxyhexanoic acid |
| o-Hydroxyhippuric acid |
| Hydroxyindole |
| 5-Hydroxyindoleacetic acid |
| 2-Hydroxyisobutyric acid |
| 3-Hydroxykynurenine |
| 5-Hydroxylysine |
| p-Hydroxymandelic acid |
| 5-Hydroxymethyluracil |
| 6-Hydroxynicotinic acid |
| 2-Hydroxyoctanoic acid |

| |
|---|
| 3-Hydroxyoctanoic acid |
| 3-(4-Hydroxyphenyl)propionic acid |
| 3-(2-Hydroxyphenyl)propionic acid |
| 4-Hydroxyphenylacetaldehyde |
| p-Hydroxyphenylacetic acid |
| o-Hydroxyphenylacetic acid |
| 4-Hydroxyphenylglycine |
| 4-Hydroxyphenylglyoxylic acid |
| p-Hydroxyphenylpyruvic acid |
| Hydroxyproline |
| cis-4-Hydroxyproline |
| 3-Hydroxypropionic acid |
| 4-Hydroxyquinoline |
| 5-Hydroxytryptophan |
| Hydroxyurea |
| 2-Hydroxyvaleric acid |
| Hypotaurine |
| Hypoxanthine |
| I |
| IDP |
| Ile |
| Imidazole-4-acetic acid |
| Imidazole-4-methanol |
| 1H-imidazole-4-propionic acid |
| Imidazolelactic acid |
| IMP |
| Indole-3-acetaldehyde |
| Indole-3-acetaldoxime |
| Indole-3-acetamide |
| Indole-3-acetic acid |
| Indole-3-ethanol |
| 3-Indolebutyric acid |
| 3-Indoxylsulfuric acid |
| Inosine |
| Isatin |
| Isethionic acid |
| Isoamylamine |
| Isobutylamine |
| Isobutyric acid |
| Isobutyryl CoA |
| Isobutyrylcarnitine |
| Isocitric acid |
| Isoferulic acid |
| Isonicotinamide |
| Isonicotinic acid |
| Isopropanolamine |
| 2-Isopropylmalic acid |
| Isovaleric acid |
| Isovalerylcarnitine |
| Itaconic acid |
| ITP |
| K |
| Kinetin |
| Kojic acid |
| Kynurenic acid |
| Kynurenine |
| L |
| Lactic acid |
| S-Lactoylglutathione |
| Lauric acid |
| Lauroyl CoA |
| Lauroylcarnitine |
| Leu-Leu-Tyr |
| Leu |
| β-Leucine |
| Lipoamide |
| Lumazine |
| Lys |
| Lysinamide |
| M |
| Maleamic acid |
| Maleic acid |
| Malic acid |
| Malonic acid |
| Malonyl CoA |
| Mandelic acid |
| Mannosamine |
| Melatonin |
| 6-Mercaptopurine |

Fig. 27 - 4

| |
|---|
| MES |
| Mesaconic acid |
| Met |
| Metanilic acid |
| Methanesulfonic acid |
| Methionine sulfoxide |
| Methionine sulfoximine |
| 3-Methoxy-4-hydroxyphenylethyleneglycol |
| 5-Methoxy-N,N-dimethyltryptamine |
| 3-Methoxyanthranilic acid |
| 5-Methoxyindoleacetic acid |
| p-Methoxyphenylacetic acid |
| 5-Methoxytryptamine |
| 3-Methoxytyramine |
| 3-Methoxytyrosine |
| 4-Methyl-2-oxovaleric acid |
| 3-Methyl-2-oxovaleric acid |
| 1-Methyl-4-imidazoleacetic acid |
| $N^1$-Methyl-4-pyridone-5-carboxamide |
| 4-Methyl-5-thiazoleethanol |
| 4-Methyl-1,2,5-oxadiazol-3-amine |
| $N^6$-Methyl-2'-deoxyadenosine |
| 5-Methyl-2'-deoxycytidine |
| 15-Methyl prostaglandin F2α |
| Methyl sulfate |
| 3-Methyladenine |
| $N^6$-Methyladenine |
| 1-Methyladenosine |
| N-Methylalanine |
| N-Methylaniline |
| N-Methylanthranilic acid |
| $N_\omega$-Methylarginine |
| N-Methylaspartic acid |
| threo-β-Methylaspartic acid |
| 2-Methylcholine |
| 3-Methylcrotonyl CoA |
| S-Methylcysteine |
| 5-Methylcytosine |
| N-Methylglutamic acid |
| Methylguanidine |
| 3-Methylguanine |
| 7-Methylguanine |
| 1-Methylhistamine |
| 3-Methylhistamine |
| 3-Methylhistidine |
| 1-Methylhistidine |
| 1-Methylhydantoin |
| $N^6$-Methyllysine |
| Methylmalonic acid |
| Methylmalonyl CoA |
| S-Methylmethionine |
| 1-Methylnicotinamide |
| N-Methylnicotinamide |
| N-Methylnorsalsolinol |
| N-Methylproline |
| N-Methylputrescine |
| 4-Methylpyrazole |
| 2-Methylserine |
| N-Methylserotonin |
| 5-Methyltetrahydrofolic acid |
| 4-Methylthio-2-oxobutyric acid |
| (Methylthio)acetic acid |
| N-Methyltryptamine |
| N-Methyltryptophan |
| N-Methyltyramine |
| Mevalolactone |
| Mevalonic acid |
| Mimosine |
| Minocycline |
| Mucic acid |
| cis,cis-Muconic acid |
| Muramic acid |
| myo-Inositol 1-phosphate |
| myo-Inositol 2-phosphate |
| myo-Inositol 3-phosphate |
| Myosmine |
| Myristoleic acid |
| N |
| NAADP |

| |
|---|
| $NAD^+$ |
| NADH |
| $NADP^+$ |
| NADPH |
| Neamine |
| Nicotinamide |
| Nicotinamide hypoxanthine dinucleotide |
| Nicotine |
| Nicotinic acid |
| p-Nitrophenyl phosphate |
| N-Nitrosodiethanolamine |
| S-Nitrosoglutathione |
| 3-Nitrotyrosine |
| NMN |
| Noradrenaline |
| Normetanephrine |
| Nornicotine |
| Norspermidine |
| Norvaline |
| O |
| Octanoic acid |
| Octanoyl CoA |
| Octanoylcarnitine |
| Octopamine |
| Octopine |
| Octylamine |
| Ophthalmic acid |
| Ornithine |
| Orotic acid |
| Orotidine 5'-monophosphate |
| Oxamic acid |
| 5-Oxo-2-tetrahydrofurancarboxylic acid |
| 2-Oxoadipic acid |
| 2-Oxobutyric acid |
| 2-Oxoglutaric acid |
| 5-Oxohexanoic acid |
| 4-Oxohexanoic acid |
| 2-Oxoisovaleric acid |
| 2-Oxooctanoic acid |
| 5-Oxoproline |
| 4-Oxovaleric acid |
| 2-Oxovaleric acid |
| P |
| Palmatine |
| Palmitoylcarnitine |
| Pantothenic acid |
| Paraxanthine |
| Pelargonic acid |
| Penicillamine |
| Pentamidine |
| Perillic acid |
| Phe |
| Phenaceturic acid |
| o-Phenanthroline |
| Phenoxyacetic acid |
| Phenoxybenzamine |
| Phenyl phosphate |
| $N^2$-Phenylacetylglutamine |
| 1,3-Phenylenediamine |
| Phenylethanolamine |
| 1-Phenylethylamine |
| 2-Phenylethylamine |
| Phenylhydrazine |
| 3-Phenyllactic acid |
| 3-Phenylpropionic acid |
| Phenylpyruvic acid |
| Phosphocreatine |
| Phosphoenolpyruvic acid |
| 6-Phosphogluconic acid |
| 3-Phosphoglyceric acid |
| 2-Phosphoglyceric acid |
| Phosphoglycolic acid |
| Phosphonoacetic acid |
| Phosphorylcholine |
| O-Phosphoserine |
| Phytic acid |
| Picolinamide |
| Picolinic acid |
| Pimelic acid |

Fig. 27 - 5

| | |
|---|---|
| Pipecolic acid | Taurocyamine |
| Piperidine | 5,6,7,8-Tetrahydrobiopterin |
| Porphobilinogen | Tetrahydropalmatine |
| ppGpp | Theobromine |
| Pristanic acid | Theophylline |
| Pro | Thiabendazole |
| Procaine | Thiamine |
| Propionic acid | Thiamine diphosphate |
| Propionyl CoA | Thiamine phosphate |
| Propylthiouracil | Thiaproline |
| Prostaglandin $E_2$ | 6,8-Thioctic acid |
| Prostaglandin $F_{2\alpha}$ | 2-Thiopheneacetic acid |
| PRPP | Thiourea |
| Psychosine | Thr-Asp |
| Pterin | Thr |
| Purine | Threonic acid |
| Purine riboside | allo-Threonine |
| Putrescine | Thymidine |
| Pyrazinamide | Thymine |
| Pyrazole | Tiglic acid |
| Pyridine-2-carboxylic acid butyl ester | Tioconazole |
| Pyridine | o-Toluic acid |
| Pyridoxal | p-Toluic acid |
| Pyridoxal 5-phosphate | m-Toluic acid |
| Pyridoxamine | Topiramic acid |
| Pyridoxamine 5'-phosphate | Trehalose 6-phosphate |
| 4-Pyridoxic acid | TRH |
| Pyridoxine | Trigonelline |
| Pyrimidine | Trimethylamine |
| Pyrophosphate | Trimethylamine N-oxide |
| Pyrrole-2-carboxylic acid | $N^\alpha,N^\alpha,N^\alpha$-Trimethyllysine |
| 2,5-Pyrroledione | Trimethylsulfonium |
| 1-Pyrroline 5-carboxylic acid | Tropic acid |
| Pyruvic acid | Tropine |
| Q | Tropinone |
| Quinic acid | Trp |
| Quinoline | Tryptamine |
| 2-Quinolinecarboxylic acid | Tryptophanamide |
| Quinolinic acid | Tyr-Arg |
| R | Tyr-Glu |
| Riboflavin | Tyr |
| Ribose 1-phosphate | β-Tyr |
| Ribose 5-phosphate | Tyramine |
| Ribulose 1,5-diphosphate | U |
| Ribulose 5-phosphate | UDP-galactose |
| S | UDP-glucose |
| Saccharopine | UDP-glucuronic acid |
| Sarcosine | UDP-N-acetylgalactosamine |
| SDMA | UDP-N-acetylglucosamine |
| Sedoheptulose 7-phosphate | UDP |
| Semicarbazide | UMP |
| Sepiapterin | Undecanoic acid |
| Ser-Glu | Uracil |
| Ser | Urea |
| Serotonin | 3-Ureidopropionic acid |
| Shikimate 3-phosphate | Uric acid |
| Shikimic acid | Uridine |
| Sinapic acid | Urocanic acid |
| Sorbitol 6-phosphate | UTP |
| Spermidine | V |
| Spermine | Val |
| Streptomycin sulfate | Valeric acid |
| Suberic acid | Vanillic acid |
| Succinic acid | Vanillylmandelic acid |
| Succinic semialdehyde | X |
| Succinyl CoA | Xanthine |
| Succinylcholine | Xanthosine |
| O-Succinylhomoserine | Xanthurenic acid |
| Sucrose 6'-phosphate | XMP |
| Sulfanilic acid | XTP |
| S-Sulfocysteine | Xylulose 5-phosphate |
| O-Sulfoserine | Z |
| Sulfotyrosine | trans-Zeatin |
| Syringic acid | Steroid derivative |
| T | 11β-Hydroxyandrost-4-ene-3,17-dione |
| Tartaric acid | 16-Epiestriol |
| meso-Tartaric acid | 16α-Hydroxyestrone |
| Taurine | 17α-Estradiol |
| Taurocholic acid | 17α-Hydroxypregnenolone |

Fig. 27 - 6

| |
|---|
| 17α-Hydroxyprogesterone |
| 18-Hydroxycorticosterone |
| 19-Hydroxyandrostenedione |
| 19-Hydroxytestosterone |
| 20α-Hydroxycholesterol |
| 20α-Hydroxyprogesterone |
| 21-Deoxycortisol |
| 21-Hydroxypregnenolone |
| 22-Hydroxycholesterol |
| 2-Hydroxyestradiol |
| 2-Hydroxyestrone |
| 3α,21-Dihydroxy-5α-pregnan-20-one |
| 4-Androsten-3,17-dione |
| 5α-Cholestan-3-one |
| 5α-Pregnan-20α-ol-3-one |
| 5α-Pregnan-3α-ol-20-one |
| 5α-Pregnane-3,20-dione |
| 5β-pregnane-3α,21-diol-11,20-dione |
| 7-Dehydrocholesterol |
| Adrenosterone |
| Aldosterone |
| Androstanediol |
| Androstanolone |
| Androsterone |
| Asiatic acid |
| Betulinic acid |
| Brassinolide |
| Campesterol |
| Cepharanthine |
| Chlorotrianisene |
| Cholesterol |
| Cholesterol sulfate |
| Cholesteryl palmitate |
| Cortexolone |
| Corticosterone |
| Cortisol |
| Cortisone |
| Cycloartenol |
| Dehydroisoandrosterone |
| Dehydroisoandrosterone 3-sulfate |
| Deoxycorticosterone |
| Desmosterol |
| Diosgenin |
| Ergocalciferol |
| Ergosterol |
| Estriol |
| Estriol 16α-glucuronide |
| Estriol 3-glucuronide |
| Estrone |
| Estrone 3-glucuronide |
| Estrone 3-sulfate |
| Ethynyl estradiol |
| Etiocholan-3α-ol-17-one |
| Etiocholan-3α-ol-17-one glucuronide |
| Etiocholan-3α-ol-17-one sulfate |
| Hecogenin |
| Hydroxyprogesterone caproate |
| Lanosterol |
| Lathosterol |
| Medroxyprogesterone |
| Methoxyestradiol |
| Ouabain |
| Pregnenolone |
| Pregnenolone sulfate |
| Progesterone |
| Sitosterol |
| Solanidine |
| Stigmasterol |
| Testosterone |
| Testosterone acetate |
| Testosterone glucuronide |
| β-Estradiol |
| β-Estradiol 17-glucuronide |
| Bile acid |
| Chenodeoxycholic acid |
| Deoxycholic acid |
| Glycochenodeoxycholic acid |
| Glycodeoxycholic acid |
| Glycolithocholic acid |

| |
|---|
| Glycoursodeoxycholic acid |
| Lithocholic acid |
| Taurochenodeoxycholic acid |
| Taurodeoxycholic acid |
| Taurolithocholic acid |
| Taurolithocholic acid 3-sulfate |
| Tauroursodeoxycholic acid |
| Ursodeoxycholic acid |
| Simple/complex lipid |
| N-Acetylsphingosine |
| 1,2-Dipalmitoyl-glycero-3-phosphoethanolamine |
| 1,2-Dipalmitoyl-glycero-3-phosphoglycerol |
| 1,2-Distearoyl-glycero-3-phosphocholine |
| 1-Hexadecyl-2-acetyl-glycero-3-phosphocholine |
| 1-Myristoyl-glycero-3-phosphocholine |
| 1-Myristoyl-glycero-3-phosphoethanolamine |
| 1-Oleoyl-glycero-3-phosphocholine |
| 1-Palmitoyl-glycero-3-phosphocholine |
| 1-Palmitoyl-glycero-3-phosphoethanolamine |
| 1-Stearoyl-glycero-3-phosphocholine |
| Anandamide |
| Ethyl arachidonate |
| Linoleyl ethanolamide |
| N-Hexanoylsphingosine |
| Oleoyl ethanolamine |
| Palmitoylethanolamide |
| Phytosphingosine |
| Sphinganine |
| Sphinganine 1-phosphate |
| Sphingomyelin(d18:1/16:0) |
| Sphingomyelin(d18:1/18:0) |
| Sphingosine |
| Sphingosine 1-phosphate |
| Stearoyl ethanolamide |
| TG(16:0/16:0/16:0) |
| Trilaurin |
| Polyphenol |
| 7,8-Dihydroxycoumarin |
| 7-Hydroxycoumarin |
| Apigenin 7-glucoside |
| Apigenin 8-glucoside |
| Arctigenin |
| Baicalein |
| Baicalin |
| Capillarisin |
| Catechin |
| Chlorogenic acid |
| Chrysin |
| Chrysoeriol |
| Curcumin |
| Daidzein |
| Datiscetin |
| Delphinidin |
| Eleutheroside B |
| Eleutheroside B1 |
| Eleutheroside E |
| Epicatechin |
| Epicatechin gallate |
| Epigallocatechin gallate |
| Eriocitrin |
| Eriodictyol |
| Eriodictyol 7-neohesperidoside |
| Flavanone |
| Formononetin |
| Formononetin 7-glucoside |
| Galangin |
| Gallocatechin |
| Genistein |
| Glycitein |
| Hesperidin |
| Isofraxidin |
| Isoliquiritigenin |
| Isoorientin |
| Kaempferol |
| Liquiritigenin |
| Luteolin |
| Luteolin 7-glucoside |
| Malvidin |
| Myricetin 3-rhamnoside |

Fig. 27 - 7

| |
|---|
| Naringenin |
| Naringenin 7-neohesperidoside |
| Peonidin 3-glucoside |
| Phyllodulcin |
| Poncirin |
| Quercetin |
| Quercetin 3-rutinoside |
| Resveratrol |
| Saponarin |
| Scytalone |
| Taxifolin |
| Theaflavin |
| Theaflavin-3-gallate |
| Fatty acid/acylcarnitine |
| Arachidic acid |
| Arachidonic acid |
| cis-5,8,11,14,17-Eicosapentaenoic acid |
| Erucic acid |
| Heneicosanoic acid |
| Heptadecanoic acid |
| Linoleic acid |
| Linolenic acid |
| Myristic acid |
| Nervonic acid |
| Oleic acid |
| Palmitic acid |
| Palmitoleic acid |
| Pentadecanoic acid |
| Ricinoleic acid |
| Stearic acid |
| Stearidonic acid |
| Tricosanoic acid |
| 15(S)-HETE |
| cis-11,14-Eicosadienoic acid |
| cis-11-Eicosenoic acid |
| cis-13-Eicosenoic acid |
| cis-4,7,10,13,16,19-Docosahexaenoic acid |
| cis-8,11,14-Eicosatrienoic acid |
| Leukotriene B4 |
| 19-Methylarachidic acid |
| 2-Hydroxytetradecanoic acid |
| 3-Hydroxytetradecanoic acid |
| FA(12:0) |
| FA(12:1) |
| FA(13:0) |
| FA(14:0) |
| FA(14:1)-1 |
| FA(14:1)-2 |
| FA(14:2) |
| FA(14:3) |
| FA(15:0)-1 |
| FA(15:0)-2 |
| FA(15:1)-1 |
| FA(15:1)-2 |
| FA(16:2) |
| FA(16:3) |
| FA(17:0) |
| FA(17:1) |
| FA(17:2) |
| FA(17:3) |
| FA(18:3) |
| FA(19:0) |
| FA(19:1) |
| FA(19:2) |
| FA(20:3) |
| FA(20:5) |
| FA(22:0) |
| FA(22:1) |
| FA(22:2) |
| FA(22:3) |
| FA(22:4) |
| FA(22:5) |
| FA(24:0) |
| FA(24:2) |
| FA(24:4) |
| FA(24:5) |
| FA(25:0) |
| FA(25:3) |
| FA(26:0) |

| |
|---|
| FA(26:2) |
| AC(12:0) |
| AC(12:1) |
| AC(13:1) |
| AC(14:0) |
| AC(14:1) |
| AC(14:2) |
| AC(14:3) |
| AC(15:0) |
| AC(16:1) |
| AC(16:2) |
| AC(17:0) |
| AC(17:1) |
| AC(18:0) |
| AC(18:1) |
| AC(18:2) |
| AC(20:0) |
| AC(20:1) |
| AC(21:0) |
| AC(22:0) |
| AC(23:0) |
| Others |
| 6-Hydroxymelatonin |
| 6-Ketoprostaglandin E1 |
| Abietic acid |
| Astaxanthin |
| Carvone |
| Indole-3-carboxaldehyde |
| N-Acetylserotonin |
| N-Acetyltyrosine ethyl ester |
| N-Formylanthranilic acid |
| N-Methylphenylethanolamine |
| Prostaglandin B2 |
| Prostaglandin D1 |
| Prostaglandin D2 |
| Prostaglandin E1 |
| Retinol |
| Thyroxine |
| Triptolide |
| α-Tocopherol |
| α-Tocopherol acetate |
| γ-Tocopherol |

Fig. 28 - 1

| line No. | Compound name |
|---|---|
| 1 | 1,5-Anhydro-glucitol |
| 2 | 1,6-Anhydroglucose |
| 3 | 1-Hexadecanol |
| 4 | 2,3-Bisphosphoglyceric acid |
| 5 | 2-Aminoadipic acid |
| 6 | 2-Aminobutyric acid |
| 7 | 2-Aminoethanol |
| 8 | 2-Aminoisobutyric acid |
| 9 | 2-Aminopimelic acid |
| 10 | 2-Deoxy-glucose |
| 11 | 2-Deoxytetronic acid |
| 12 | 2'-Deoxyuridine |
| 13 | 2-Furoic acid |
| 14 | 2-Hexenedioic acid |
| 15 | 2-Hydroxy-3-methylvaleric acid |
| 16 | 2-Hydroxyadipic acid |
| 17 | 2-Hydroxybutyric acid |
| 18 | 2-Hydroxyglutaric acid |
| 19 | 2-Hydroxyhippuric acid |
| 20 | 2-Hydroxyisobutyric acid |
| 21 | 2-Hydroxyisocaproic acid |
| 22 | 2-Hydroxyisovaleric acid |
| 23 | 2-Hydroxyphenylacetic acid |
| 24 | 2-Hydroxysebacic acid |
| 25 | 2-Isopropylmalic acid |
| 26 | 2-Ketoadipic acid |
| 27 | 2-Ketoglutaric acid |
| 28 | 2-Ketoisocaproic acid |
| 29 | 2-Keto-isovaleric acid |
| 30 | 2-Methyl-3-hydroxybutyric acid |
| 31 | 2-Methyl-3-hydroxyvaleric acid |
| 32 | 2-Octenoic acid |
| 33 | 2-Phosphoglyceric acid |
| 34 | 2-Propyl-3-hydroxy-pentanoic acid |
| 35 | 2-Propyl-5-hydroxy-pentanoic acid |
| 36 | 2-Propyl-glutaric acid |
| 37 | 2-Propylhydroxyglutaric acid-oxime |
| 38 | 3-(3-Hydroxyphenyl)-3-hydroxypropionic acid |
| 39 | 3,4-Dihydroxymandelic acid |
| 40 | 3,6-Epoxydodecanedioic acid |
| 41 | 3-Aminoglutaric acid |
| 42 | 3-Aminoisobutyric acid |
| 43 | 3-Aminopropanoic acid |
| 44 | 3-Hydroxy-3-methylglutaric acid |
| 45 | 3-Hydroxyadipic acid |
| 46 | 3-Hydroxybenzoic acid |
| 47 | 3-Hydroxybutyric acid |
| 48 | 3-Hydroxydodecanedioic acid |
| 49 | 3-Hydroxyisobutyric acid |
| 50 | 3-Hydroxyisovaleric acid |
| 51 | 3-Hydroxy-kynurenine |
| 52 | 3-Hydroxyphenylacetic acid |
| 53 | 3-Hydroxypropionic acid |
| 54 | 3-Hydroxysebacic acid |
| 55 | 3-Hydroxyvaleric acid |
| 56 | 3-Methoxy-4-hydroxybenzoic acid |
| 57 | 3-Methyl-2-oxovaleric acid |
| 58 | 3-Methyladipic acid |
| 59 | 3-Methylcrotonoylglycine |
| 60 | 3-Methylglutaconic acid(E) |
| 61 | 3-Methylglutaconic acid(Z) |
| 62 | 3-Methylglutaconic acid |
| 63 | 3-Methylglutaric acid |
| 64 | 3-Phosphoglyceric acid |
| 65 | 3-Sulfinoalanine |
| 66 | 4-Aminobutyric acid |
| 67 | 4-Cresol |
| 68 | 4-Hydroxybenzoic acid |
| 69 | 4-Hydroxybutyric acid |
| 70 | 4-Hydroxyphenylacetic acid |
| 71 | 4-Hydroxyphenyllactic acid |
| 72 | 4-Hydroxyproline |
| 73 | 5-Aminovaleric acid |
| 74 | 5-Dehydroquinic acid |
| 75 | 5-Hydroxy-2-furoic acid |
| 76 | 5-Hydroxy-tryptophan |
| 77 | 5-Methoxytryptamine |
| 78 | 5'-Methylthioadenosine |
| 79 | 5-Oxoproline |
| 80 | 7-Hydroxoctanoic acid |
| 81 | 7-Methylguanine |
| 82 | Acetoacetic acid |
| 83 | Acetoacetic acid-oxime |
| 84 | Acetylglycine |
| 85 | Acetylsalicylic acid |
| 86 | Aconitic acid |
| 87 | Adenine |
| 88 | Adenosine monophosphate |
| 89 | Adenosine |
| 90 | Adipic acid |
| 91 | Alanine |
| 92 | allo-Isoleucine |
| 93 | Allose |
| 94 | Anthranilic acid |
| 95 | Arabinose |
| 96 | Arabitol |
| 97 | Arachidonic acid |
| 98 | Arginine |
| 99 | Ascorbic acid |
| 100 | Asparagine |
| 101 | Aspartic acid |
| 102 | Azelaic acid |
| 103 | Benzoic acid |
| 104 | Boric acid |
| 105 | Cadaverine |
| 106 | Caffeine |
| 107 | Caproic acid |
| 108 | Catechol |
| 109 | Chloramphenicol |
| 110 | Cholecalciferol |
| 111 | Cholesterol |
| 112 | Cinnamic acid |
| 113 | Citraconic acid |
| 114 | Citramalic acid |
| 115 | Citric acid |
| 116 | Citrulline |
| 117 | Coniferyl alcohol |
| 118 | Coniferyl aldehyde |
| 119 | Creatinine |
| 120 | Cyclohexanediol |

Fig. 28 - 2

| | | | | |
|---|---|---|---|---|
| 121 | Cystamine | | 182 | Homovanillic acid |
| 122 | Cystathionine | | 183 | Hydroxylysine (2 isomers) |
| 123 | Cysteic acid | | 184 | Hypotaurine |
| 124 | Cysteine | | 185 | Hypoxanthine |
| 125 | Cystine | | 186 | Indol-3-acetic acid |
| 126 | Cytidine | | 187 | Indolelactic acid |
| 127 | Cytosine | | 188 | Inosine monophosphate |
| 128 | Decadienedioic acid | | 189 | Inosine |
| 129 | Decanoic acid | | 190 | Inositol |
| 130 | Dihydroxyacetone phosphate | | 191 | Isobutyrylglycine |
| 131 | Dihydroxyacetone | | 192 | Isocitric acid |
| 132 | Dodecanedioic acid | | 193 | Isoleucine |
| 133 | Dopa | | 194 | Isomaltose |
| 134 | Dopamine | | 195 | Isovalerylglycine |
| 135 | Eicosapentaenoic acid | | 196 | Kynurenic acid |
| 136 | Elaidic acid | | 197 | Kynurenine |
| 137 | Erythrose 4-phosphate | | 198 | Lactic acid |
| 138 | Erythrulose | | 199 | Lactitol |
| 139 | Ethylhydracrylic acid | | 200 | Lactose |
| 140 | Ethylmalonic acid | | 201 | Lauric acid |
| 141 | Fructose 1-phosphate | | 202 | Leucine |
| 142 | Fructose 6-phosphate | | 203 | Linoleic acid |
| 143 | Fructose | | 204 | Lysine |
| 144 | Fucose | | 205 | Lyxose |
| 145 | Fumaric acid | | 206 | Maleic acid |
| 146 | Galactitol | | 207 | Malic acid |
| 147 | Galactosamine | | 208 | Malonic acid |
| 148 | Galactose | | 209 | Maltitol |
| 149 | Galacturonic acid | | 210 | Maltose |
| 150 | Glucaric acid | | 211 | Mandelic acid |
| 151 | Gluconic acid | | 212 | Mannitol |
| 152 | Glucono-1,4-lactone | | 213 | Mannose |
| 153 | Glucosamine | | 214 | Margaric acid |
| 154 | Glucose 6-phosphate | | 215 | Mesaconic acid |
| 155 | Glucose | | 216 | meso-Erythritol |
| 156 | Glucuronic acid lactone | | 217 | Methionine |
| 157 | Glucuronic acid | | 218 | Methylcitric acid |
| 158 | Glutaconic acid | | 219 | Methylmalonic acid |
| 159 | Glutamic acid | | 220 | Methylsuccinic acid |
| 160 | Glutamine | | 221 | Mevalonic lactone |
| 161 | Glutaric acid | | 222 | Monostearin |
| 162 | Glyceraldehyde 3-phosphate | | 223 | Myristic acid |
| 163 | Glyceraldehyde | | 224 | N-Acetylaspartic acid |
| 164 | Glyceric acid | | 225 | N-Acetyl-Lysine |
| 165 | Glycerol 2-phosphate | | 226 | N-Acetylmannosamine |
| 166 | Glycerol 3-phosphate | | 227 | N-Acetyl-Ornithine |
| 167 | Glycerol | | 228 | N-Acetylserine |
| 168 | Glycine | | 229 | N-Acetyltyrosine |
| 169 | Glycolic acid | | 230 | Naproxen |
| 170 | Glycyl-Glycine | | 231 | Niacinamide |
| 171 | Glyoxylic acid-oxime | | 232 | Nonanoic acid |
| 172 | Guanine | | 233 | Norvaline |
| 173 | Guanosine | | 234 | Octadecanol |
| 174 | Hexanoylglycine | | 235 | Octanoic acid |
| 175 | Hippuric acid | | 236 | Octenedioic acid |
| 176 | Histamine | | 237 | Oleic acid |
| 177 | Histidine | | 238 | O-Phosphoethanolamine |
| 178 | Homocysteine | | 239 | O-Phospho-Serine |
| 179 | Homocystine | | 240 | Ornithine |
| 180 | Homogentisic acid | | 241 | Orotic acid |
| 181 | Homoserine | | 242 | Oxalacetic acid |

Fig. 28 - 3

| | |
|---|---|
| 243 | Oxalic acid |
| 244 | Palmitic acid |
| 245 | Palmitoleic acid |
| 246 | p-Aminohippuric acid |
| 247 | Pantothenic acid |
| 248 | ParaXanthine |
| 249 | Phenol |
| 250 | Phenylacetic acid |
| 251 | Phenylalanine |
| 252 | Phenyllactic acid |
| 253 | Phosphoenolpyruvic acid |
| 254 | Phosphoric acid |
| 255 | Pimelic acid |
| 256 | p-Nitrophenol |
| 257 | Proline |
| 258 | Propionylglycine |
| 259 | Psicose |
| 260 | Putrescine |
| 261 | Pyrogallol |
| 262 | Pyruvic acid |
| 263 | Pyruvic acid-oxime |
| 264 | Rhamnose |
| 265 | Ribitol |
| 266 | Ribonolactone |
| 267 | Ribose 5-phosphate |
| 268 | Ribose |
| 269 | Ribulose 5-phosphate |
| 270 | Ribulose |
| 271 | Sarcosine |
| 272 | S-Benzyl-Cysteine |
| 273 | Sebacic acid |
| 274 | Sedoheptulose 7-phosphate |
| 275 | Serine |
| 276 | Shikimic acid |
| 277 | Sorbitol |
| 278 | Sorbose |
| 279 | Spermidine |
| 280 | Stearic acid |
| 281 | Suberic acid |
| 282 | Succinic acid |
| 283 | Succinylacetone-ox-origin fragment |
| 284 | Sucrose |
| 285 | Tagatose |
| 286 | Tartaric acid |
| 287 | Taurine |
| 288 | Theophylline |
| 289 | Thiodiglycolic acid |
| 290 | Threitol |
| 291 | Threo-b-hydroxyaspartic acid |
| 292 | Threonic acid |
| 293 | Threonine |
| 294 | Thymidine |
| 295 | Thymine |
| 296 | Tiglylglycine |
| 297 | Trehalose |
| 298 | Tricarballylic acid |
| 299 | Trichloroacetic acid |
| 300 | Tropic acid |
| 301 | Tryptamine |
| 302 | Tryptophan |
| 303 | Tyrosine |

| | |
|---|---|
| 304 | Uracil |
| 305 | Urea |
| 306 | Uric acid |
| 307 | Uridine monophosphate |
| 308 | Uridine |
| 309 | Valine |
| 310 | Valproic acid |
| 311 | Vanilmandelic acid |
| 312 | Xanthine |
| 313 | Xanthosine |
| 314 | Xylitol |
| 315 | Xylose |
| 316 | Xylulose |

Fig. 29 - 1

|  | Heart | | | Brain | | | Kidney | | |
| --- | --- | --- | --- | --- | --- | --- | --- | --- | --- |
| Name of Compounds | 1 d | 1 w | 8 w | 1 d | 1 w | 8 w | 1 d | 1 w | 8 w |
| 2-Aminoethanol | 1.17 | 1.35 | 0.73 | 1.03 | 1.02 | 0.95 | 1.09 | 1.21 | 0.89 |
| 2-Octenoic acid | 0.98 | 0.94 | 0.92 | 0.93 | 0.99 | 1.04 | 0.92 | 1.01 | 0.91 |
| 3-Aminopropanoic acid | 1.64 | 2.05 | 1.48 | 0.98 | 1.16 | 1.03 | 1.61 | 1.36 | 0.96 |
| 3-Hydroxybutyric acid | 1.21 | 1.12 | 1.07 | 1.17 | 1.00 | 1.23 | 1.25 | 1.08 | 1.34 |
| 5-Oxoproline | 0.79 | 0.70 | 0.66 | 1.02 | 1.08 | 1.01 | 1.15 | 0.91 | 1.00 |
| Alanine | 1.12 | 0.87 | 0.79 | 0.98 | 1.02 | 0.99 | 1.02 | 1.12 | 0.87 |
| allo-Isoleucine | 1.54 | 1.36 | 1.39 | 1.04 | 0.93 | 0.94 | 1.26 | 1.01 | 1.00 |
| Allose | 2.16 | 2.03 | 2.85 | 0.97 | 1.13 | 1.35 | 1.09 | 1.05 | 1.04 |
| Aspartic acid | 1.48 | 2.45 | 2.50 | 0.90 | 1.08 | 1.16 | 1.16 | 1.14 | 0.77 |
| Benzoic acid | 0.94 | 0.96 | 1.10 | 0.95 | 1.04 | 1.03 | 0.90 | 1.11 | 0.86 |
| Boric acid | 0.80 | 0.87 | 0.91 | 0.42 | 1.13 | 0.62 | 0.83 | 1.38 | 0.94 |
| Citric acid | 1.32 | 1.56 | 1.73 | 1.07 | 0.98 | 0.99 | 1.23 | 1.48 | 6.85 |
| Creatinine | 0.59 | 0.53 | 0.58 | 0.87 | 0.90 | 1.13 | 1.18 | 0.98 | 1.75 |
| Cysteine | 1.41 | 1.10 | 1.88 | 1.02 | 1.03 | 1.04 | 1.43 | 1.05 | 2.62 |
| Fumaric acid | 1.17 | 2.24 | 1.55 | 0.97 | 1.06 | 0.96 | 1.63 | 0.94 | 1.03 |
| Galactose | 2.47 | 2.02 | 3.42 | 0.97 | 1.13 | 1.35 | 1.20 | 1.05 | 1.03 |
| Glucose | 2.47 | 2.02 | 3.42 | 0.97 | 1.13 | 1.35 | 1.20 | 1.05 | 1.03 |
| Glutamic acid | 1.01 | 1.29 | 0.92 | 0.97 | 1.04 | 0.97 | 1.24 | 1.01 | 0.90 |
| Glutamine | 0.66 | 0.65 | 0.61 | 0.94 | 0.94 | 1.17 | 0.82 | 1.13 | 0.89 |
| Glycerol 3-phosphate | 0.52 | 0.69 | 0.91 | 0.94 | 1.03 | 0.91 | 1.10 | 1.04 | 0.58 |
| Glycine | 1.15 | 1.28 | 0.89 | 1.02 | 1.04 | 0.88 | 1.11 | 0.87 | 0.80 |
| Hypotaurine | 0.64 | 1.15 | 0.73 | 1.32 | 1.14 | 0.98 | 1.34 | 1.55 | 0.95 |
| Hypoxanthine | 0.90 | 0.94 | 0.67 | 1.23 | 0.97 | 0.94 | 0.74 | 0.75 | 0.55 |
| Inositol | 0.61 | 1.66 | 1.95 | 0.96 | 1.12 | 0.92 | 0.89 | 1.44 | 0.85 |
| Isoleucine | 1.54 | 1.36 | 1.39 | 1.04 | 0.93 | 0.94 | 1.26 | 1.01 | 1.00 |
| Lactic acid | 0.87 | 0.85 | 1.24 | 0.92 | 1.03 | 1.08 | 1.03 | 0.93 | 0.86 |
| Leucine | 1.51 | 1.45 | 1.42 | 1.03 | 1.04 | 1.15 | 0.98 | 1.02 | 0.88 |
| Lysine | 0.83 | 0.97 | 0.88 | 0.90 | 1.05 | 0.96 | 0.89 | 1.14 | 0.96 |
| Malic acid | 0.88 | 0.92 | 1.03 | 1.10 | 0.94 | 1.14 | 1.70 | 7.06 | 2.01 |
| Mannose | 2.14 | 2.03 | 2.82 | 0.97 | 1.13 | 1.35 | 1.08 | 1.05 | 1.04 |
| Niacinamide | 0.68 | 0.88 | 0.86 | 0.97 | 1.18 | 0.94 | 1.01 | 1.07 | 0.86 |
| O-Phosphoethanolamine | 0.94 | 2.40 | 1.20 | 0.95 | 1.08 | 1.00 | 1.00 | 1.14 | 0.65 |
| Ornithine | 1.55 | 1.56 | 1.56 | 1.00 | 1.00 | 1.00 | 0.98 | 1.10 | 0.89 |
| Palmitic acid | 0.81 | 0.88 | 0.91 | 1.18 | 1.16 | 1.07 | 1.08 | 1.04 | 0.90 |
| Pantothenic acid | 0.87 | 0.62 | 0.94 | 1.00 | 1.00 | 1.00 | 1.00 | 1.00 | 1.00 |
| Phenylalanine | 1.19 | 1.23 | 1.08 | 1.06 | 0.96 | 1.06 | 1.14 | 1.06 | 0.86 |
| Phosphoric acid | 0.90 | 0.87 | 0.73 | 0.98 | 1.05 | 0.98 | 0.99 | 0.96 | 0.87 |
| Proline | 1.94 | 1.69 | 1.50 | 1.08 | 0.91 | 0.97 | 0.83 | 0.95 | 0.89 |
| Pyruvic acid | 0.91 | 1.42 | 1.70 | 0.91 | 0.97 | 1.09 | 1.13 | 0.83 | 1.58 |
| Serine | 2.42 | 1.40 | 0.88 | 0.94 | 1.05 | 1.04 | 0.93 | 1.08 | 0.80 |
| Stearic acid | 0.80 | 0.89 | 0.92 | 1.24 | 1.18 | 1.03 | 1.09 | 1.11 | 0.89 |
| Succinic acid | 0.80 | 0.61 | 0.59 | 1.06 | 1.05 | 0.95 | 1.11 | 0.97 | 1.13 |
| Taurine | 1.00 | 1.00 | 1.00 | 0.96 | 1.05 | 1.00 | 1.02 | 1.29 | 0.87 |
| Threonic acid | 1.10 | 1.51 | 1.23 | 0.79 | 1.19 | 1.20 | 1.06 | 1.74 | 0.98 |
| Threonine | 1.36 | 1.47 | 1.24 | 0.93 | 1.18 | 1.13 | 0.90 | 0.96 | 0.96 |
| Urea | 1.65 | 1.86 | 1.37 | 1.05 | 1.51 | 1.04 | 1.00 | 1.00 | 1.00 |
| Valine | 1.67 | 1.61 | 1.52 | 1.07 | 1.04 | 1.30 | 1.25 | 1.10 | 0.98 |

Fig. 29 - 2

|  | Liver | | | Pancreas | | | Muscle | | |
|---|---|---|---|---|---|---|---|---|---|
| Name of Compounds | 1 d | 1 w | 8 w | 1 d | 1 w | 8 w | 1 d | 1 w | 8 w |
| 2-Aminoethanol | 1.49 | 1.24 | 0.99 | 1.35 | 0.83 | 0.91 | 1.59 | 1.04 | 0.92 |
| 2-Octenoic acid | 1.09 | 1.20 | 0.81 | 1.04 | 0.99 | 0.99 | 1.16 | 1.18 | 0.91 |
| 3-Aminopropanoic acid | 1.15 | 0.89 | 1.45 | 1.01 | 1.39 | 0.99 | 1.48 | 1.63 | 0.90 |
| 3-Hydroxybutyric acid | 1.17 | 1.37 | 0.97 | 0.79 | 0.89 | 0.91 | 1.47 | 1.43 | 1.43 |
| 5-Oxoproline | 0.87 | 1.01 | 1.19 | 1.18 | 1.26 | 1.17 | 0.95 | 1.05 | 1.35 |
| Alanine | 1.28 | 0.91 | 1.19 | 0.90 | 1.07 | 1.49 | 1.21 | 1.05 | 1.08 |
| allo-Isoleucine | 1.32 | 0.88 | 1.05 | 0.66 | 1.30 | 0.91 | 0.87 | 1.05 | 1.24 |
| Allose | 1.03 | 0.95 | 1.11 | 1.01 | 1.02 | 0.88 | 1.36 | 1.59 | 1.76 |
| Aspartic acid | 1.16 | 1.21 | 0.73 | 1.10 | 0.94 | 0.84 | 1.00 | 1.00 | 1.00 |
| Benzoic acid | 1.08 | 1.18 | 0.81 | 1.15 | 0.96 | 1.09 | 1.12 | 1.25 | 0.96 |
| Boric acid | 1.38 | 1.36 | 0.67 | 0.79 | 1.22 | 1.11 | 1.30 | 1.05 | 0.74 |
| Citric acid | 1.04 | 2.13 | 0.85 | 0.71 | 1.17 | 1.23 | 1.32 | 1.32 | 0.41 |
| Creatinine | 1.00 | 1.00 | 1.00 | 0.88 | 1.70 | 0.79 | 1.18 | 1.01 | 1.00 |
| Cysteine | 1.50 | 1.04 | 1.94 | 1.26 | 1.27 | 1.03 | 1.20 | 1.24 | 1.33 |
| Fumaric acid | 1.45 | 1.28 | 0.98 | 0.97 | 1.00 | 1.03 | 0.84 | 0.99 | 1.25 |
| Galactose | 1.08 | 0.97 | 0.87 | 1.13 | 0.92 | 1.00 | 1.26 | 1.67 | 2.04 |
| Glucose | 1.08 | 0.97 | 0.87 | 1.13 | 0.92 | 1.00 | 1.26 | 1.67 | 2.04 |
| Glutamic acid | 1.33 | 0.94 | 1.96 | 1.03 | 0.93 | 0.78 | 0.74 | 1.16 | 1.24 |
| Glutamine | 0.69 | 0.85 | 0.84 | 1.04 | 1.30 | 1.07 | 0.98 | 0.96 | 1.40 |
| Glycerol 3-phosphate | 1.05 | 0.98 | 0.91 | 1.04 | 0.85 | 0.65 | 1.19 | 1.07 | 1.01 |
| Glycine | 1.00 | 0.96 | 1.00 | 1.06 | 1.22 | 1.08 | 0.91 | 0.90 | 1.48 |
| Hypotaurine | 1.74 | 1.66 | 3.35 | 1.51 | 1.55 | 0.89 | 1.28 | 1.12 | 0.83 |
| Hypoxanthine | 0.78 | 0.80 | 0.30 | 0.87 | 0.90 | 0.83 | 0.76 | 1.28 | 0.68 |
| Inositol | 1.05 | 1.13 | 0.99 | 1.32 | 1.07 | 1.06 | 0.85 | 0.92 | 1.01 |
| Isoleucine | 1.32 | 0.88 | 1.05 | 0.66 | 1.30 | 0.91 | 0.87 | 1.05 | 1.24 |
| Lactic acid | 1.24 | 0.95 | 0.90 | 0.89 | 1.03 | 1.56 | 1.26 | 1.07 | 1.09 |
| Leucine | 1.35 | 0.89 | 1.09 | 1.00 | 1.21 | 0.96 | 0.98 | 1.09 | 1.38 |
| Lysine | 0.97 | 0.71 | 1.15 | 1.01 | 1.04 | 1.12 | 1.60 | 0.98 | 2.09 |
| Malic acid | 1.53 | 2.03 | 0.76 | 0.71 | 0.96 | 1.19 | 0.94 | 1.16 | 1.37 |
| Mannose | 1.03 | 0.94 | 1.11 | 1.00 | 1.04 | 0.89 | 1.38 | 1.62 | 1.73 |
| Niacinamide | 1.12 | 0.96 | 0.94 | 1.26 | 1.01 | 1.05 | 1.16 | 1.27 | 1.01 |
| O-Phosphoethanolamine | 1.27 | 0.95 | 1.17 | 1.46 | 0.99 | 0.84 | 1.00 | 1.00 | 1.00 |
| Ornithine | 1.32 | 0.88 | 1.70 | 1.08 | 1.11 | 0.98 | 1.10 | 1.22 | 1.81 |
| Palmitic acid | 1.07 | 1.04 | 0.86 | 0.87 | 1.01 | 0.95 | 1.14 | 1.12 | 0.90 |
| Pantothenic acid | 1.00 | 1.00 | 1.00 | 1.00 | 1.00 | 1.00 | 1.00 | 1.00 | 1.00 |
| Phenylalanine | 1.25 | 0.86 | 1.06 | 0.96 | 1.53 | 1.64 | 1.18 | 0.98 | 1.19 |
| Phosphoric acid | 1.29 | 1.03 | 0.93 | 1.01 | 1.10 | 0.84 | 1.09 | 1.03 | 1.07 |
| Proline | 1.45 | 0.83 | 1.14 | 0.92 | 1.30 | 0.94 | 1.24 | 1.10 | 1.58 |
| Pyruvic acid | 6.35 | 0.34 | 7.04 | 1.69 | 1.71 | 1.34 | 0.98 | 1.71 | 1.62 |
| Serine | 0.91 | 1.06 | 0.97 | 1.07 | 1.21 | 0.92 | 1.01 | 0.95 | 1.36 |
| Stearic acid | 1.03 | 1.07 | 0.87 | 0.82 | 1.05 | 0.96 | 1.12 | 1.15 | 0.91 |
| Succinic acid | 1.39 | 0.94 | 1.04 | 0.89 | 0.93 | 0.99 | 1.05 | 1.00 | 1.02 |
| Taurine | 1.13 | 0.95 | 1.49 | 1.52 | 1.02 | 0.60 | 1.00 | 1.00 | 1.00 |
| Threonic acid | 1.24 | 1.02 | 0.71 | 1.40 | 1.10 | 1.12 | 0.86 | 1.10 | 0.89 |
| Threonine | 1.24 | 0.91 | 1.16 | 1.24 | 1.35 | 0.97 | 1.01 | 0.99 | 1.44 |
| Urea | 1.34 | 1.32 | 1.24 | 0.65 | 0.95 | 1.50 | 1.36 | 1.46 | 1.27 |
| Valine | 1.37 | 0.90 | 1.18 | 1.01 | 1.30 | 0.95 | 1.07 | 1.09 | 1.40 |

Fig. 29 - 3

| Name of Compounds | Fat | | | Plasma | | | Spleen | | |
|---|---|---|---|---|---|---|---|---|---|
| | 1 d | 1 w | 8 w | 1 d | 1 w | 8 w | 1 d | 1 w | 8 w |
| 2-Aminoethanol | 1.26 | 1.21 | 1.31 | 0.85 | 1.19 | 1.00 | 1.25 | 0.92 | 1.12 |
| 2-Octenoic acid | 1.02 | 1.00 | 1.06 | 0.98 | 1.02 | 1.06 | 1.20 | 1.10 | 0.83 |
| 3-Aminopropanoic acid | 1.08 | 1.51 | 1.28 | 1.00 | 1.00 | 1.00 | 1.16 | 1.28 | 0.92 |
| 3-Hydroxybutyric acid | 1.96 | 1.72 | 2.09 | 1.34 | 1.25 | 0.29 | 1.65 | 1.44 | 2.15 |
| 5-Oxoproline | 1.24 | 1.41 | 1.74 | 0.83 | 1.28 | 1.31 | 0.94 | 0.92 | 0.99 |
| Alanine | 1.71 | 1.38 | 2.04 | 0.80 | 1.08 | 1.30 | 1.07 | 1.13 | 1.09 |
| allo-Isoleucine | 1.33 | 1.38 | 2.12 | 0.85 | 1.24 | 1.31 | 1.11 | 0.81 | 1.06 |
| Allose | 1.25 | 1.53 | 1.56 | 1.21 | 0.89 | 1.15 | 1.03 | 1.24 | 1.68 |
| Aspartic acid | 1.35 | 1.54 | 1.65 | 1.00 | 1.00 | 1.00 | 1.13 | 0.82 | 1.05 |
| Benzoic acid | 1.00 | 0.86 | 1.01 | 1.03 | 1.02 | 1.06 | 1.30 | 1.15 | 0.74 |
| Boric acid | 1.02 | 1.00 | 1.00 | 0.90 | 0.94 | 0.79 | 1.25 | 1.11 | 0.77 |
| Citric acid | 0.72 | 1.50 | 4.03 | 1.17 | 1.25 | 0.89 | 0.99 | 1.21 | 1.07 |
| Creatinine | 1.00 | 1.00 | 1.00 | 0.96 | 1.73 | 1.06 | 0.68 | 1.30 | 1.09 |
| Cysteine | 1.14 | 1.26 | 2.03 | 0.72 | 0.99 | 1.38 | 1.13 | 1.09 | 1.09 |
| Fumaric acid | 1.29 | 1.35 | 1.80 | 1.19 | 1.45 | 1.26 | 1.43 | 1.07 | 1.19 |
| Galactose | 1.40 | 1.46 | 1.70 | 1.23 | 0.91 | 1.58 | 1.07 | 1.24 | 1.84 |
| Glucose | 1.40 | 1.46 | 1.70 | 1.23 | 0.91 | 1.58 | 1.07 | 1.24 | 1.84 |
| Glutamic acid | 1.44 | 1.27 | 1.79 | 1.00 | 1.00 | 1.00 | 1.02 | 0.94 | 1.10 |
| Glutamine | 1.27 | 1.51 | 2.50 | 0.83 | 1.12 | 1.06 | 0.85 | 0.92 | 0.96 |
| Glycerol 3-phosphate | 0.90 | 2.05 | 8.88 | 1.00 | 1.00 | 1.00 | 1.07 | 0.89 | 0.96 |
| Glycine | 1.45 | 1.46 | 2.36 | 0.77 | 1.22 | 1.14 | 0.99 | 0.89 | 0.98 |
| Hypotaurine | 0.76 | 1.50 | 10.95 | 0.76 | 1.65 | 2.10 | 1.45 | 1.41 | 0.91 |
| Hypoxanthine | 0.84 | 0.98 | 1.22 | 1.00 | 1.00 | 1.00 | 1.15 | 0.65 | 0.85 |
| Inositol | 1.21 | 0.84 | 2.47 | 0.98 | 1.11 | 1.25 | 0.82 | 0.99 | 1.04 |
| Isoleucine | 1.33 | 1.38 | 2.12 | 0.85 | 1.24 | 1.31 | 1.11 | 0.81 | 1.06 |
| Lactic acid | 1.43 | 1.25 | 1.24 | 0.90 | 0.95 | 1.34 | 1.16 | 0.86 | 0.96 |
| Leucine | 1.41 | 1.37 | 2.13 | 0.89 | 1.15 | 1.22 | 1.03 | 0.74 | 1.06 |
| Lysine | 1.02 | 1.74 | 2.13 | 0.87 | 1.17 | 1.87 | 0.92 | 0.84 | 1.14 |
| Malic acid | 1.27 | 1.20 | 1.86 | 1.23 | 1.46 | 1.64 | 1.35 | 1.12 | 1.49 |
| Mannose | 1.25 | 1.54 | 1.57 | 1.21 | 0.90 | 1.15 | 0.98 | 1.23 | 1.67 |
| Niacinamide | 1.10 | 1.31 | 1.15 | 1.00 | 1.00 | 1.00 | 0.96 | 0.93 | 0.99 |
| O-Phosphoethanolamine | 1.17 | 1.64 | 2.61 | 1.00 | 1.00 | 1.00 | 1.10 | 0.91 | 1.13 |
| Ornithine | 1.11 | 1.48 | 2.02 | 0.80 | 1.27 | 1.89 | 1.15 | 0.87 | 1.30 |
| Palmitic acid | 0.78 | 0.99 | 0.84 | 1.03 | 1.01 | 1.07 | 1.10 | 1.10 | 0.84 |
| Pantothenic acid | 1.32 | 1.63 | 2.00 | 1.00 | 1.00 | 1.00 | 1.00 | 1.00 | 1.00 |
| Phenylalanine | 1.37 | 1.37 | 2.15 | 0.85 | 1.24 | 1.32 | 1.11 | 0.86 | 1.00 |
| Phosphoric acid | 1.10 | 1.23 | 1.34 | 0.95 | 1.05 | 0.96 | 1.10 | 0.93 | 1.13 |
| Proline | 1.31 | 1.59 | 1.64 | 0.77 | 1.18 | 1.34 | 1.02 | 0.90 | 1.09 |
| Pyruvic acid | 1.77 | 1.40 | 2.85 | 1.13 | 0.76 | 0.84 | 1.13 | 1.33 | 0.93 |
| Serine | 1.16 | 1.36 | 1.66 | 0.68 | 1.35 | 1.51 | 0.98 | 0.83 | 1.02 |
| Stearic acid | 0.79 | 0.98 | 0.85 | 1.01 | 1.01 | 1.06 | 1.04 | 1.14 | 0.82 |
| Succinic acid | 0.97 | 0.99 | 2.23 | 0.99 | 1.15 | 1.15 | 1.29 | 0.95 | 1.18 |
| Taurine | 1.90 | 4.30 | 1.87 | 1.00 | 1.00 | 1.00 | 1.04 | 1.03 | 0.96 |
| Threonic acid | 1.84 | 1.53 | 1.31 | 0.94 | 1.23 | 1.27 | 0.78 | 1.22 | 0.82 |
| Threonine | 1.35 | 1.48 | 2.46 | 0.82 | 1.23 | 1.52 | 0.95 | 0.91 | 1.29 |
| Urea | 1.28 | 1.63 | 1.83 | 1.05 | 1.11 | 0.65 | 1.19 | 1.44 | 1.36 |
| Valine | 1.53 | 1.55 | 2.52 | 0.92 | 1.18 | 1.65 | 1.17 | 0.94 | 1.24 |

Fig. 29 - 4

| Name of Compounds | Lung | | | Testis | | | Thymus | | |
|---|---|---|---|---|---|---|---|---|---|
| | 1 d | 1 w | 8 w | 1 d | 1 w | 8 w | 1 d | 1 w | 8 w |
| 2-Aminoethanol | 1.02 | 1.08 | 0.88 | 1.36 | 1.06 | 0.70 | 0.91 | 0.70 | 1.02 |
| 2-Octenoic acid | 0.90 | 0.88 | 0.89 | 0.97 | 1.04 | 1.01 | 0.81 | 0.79 | 0.78 |
| 3-Aminopropanoic acid | 1.07 | 0.90 | 1.08 | 0.81 | 0.97 | 1.05 | 1.00 | 1.00 | 1.00 |
| 3-Hydroxybutyric acid | 1.76 | 1.59 | 1.64 | 1.27 | 1.18 | 1.11 | 0.81 | 0.90 | 1.22 |
| 5-Oxoproline | 0.85 | 1.03 | 0.96 | 1.03 | 1.01 | 0.89 | 1.01 | 0.90 | 1.31 |
| Alanine | 0.99 | 1.30 | 1.07 | 0.94 | 1.02 | 1.07 | 1.01 | 0.99 | 1.12 |
| allo-Isoleucine | 0.87 | 0.89 | 1.16 | 1.05 | 1.15 | 1.12 | 1.07 | 0.95 | 1.03 |
| Allose | 1.07 | 1.00 | 1.32 | 0.95 | 1.07 | 1.18 | 1.11 | 1.33 | 0.93 |
| Aspartic acid | 0.99 | 1.39 | 1.24 | 0.98 | 1.14 | 0.97 | 1.07 | 1.04 | 1.11 |
| Benzoic acid | 0.82 | 0.87 | 1.01 | 0.92 | 1.10 | 0.99 | 0.83 | 0.76 | 0.70 |
| Boric acid | 0.52 | 1.09 | 0.91 | 1.08 | 0.91 | 1.06 | 0.76 | 0.73 | 0.66 |
| Citric acid | 0.88 | 1.23 | 1.45 | 1.42 | 0.69 | 2.14 | 1.06 | 0.84 | 1.26 |
| Creatinine | 0.78 | 1.08 | 0.86 | 1.02 | 0.94 | 1.13 | 0.99 | 0.95 | 1.13 |
| Cysteine | 0.85 | 1.68 | 1.29 | 0.99 | 1.13 | 0.89 | 1.14 | 0.85 | 1.27 |
| Fumaric acid | 1.31 | 1.24 | 1.01 | 1.03 | 1.12 | 0.95 | 0.85 | 0.87 | 1.26 |
| Galactose | 1.24 | 0.90 | 1.52 | 0.89 | 1.16 | 1.31 | 1.34 | 1.57 | 0.87 |
| Glucose | 1.24 | 0.90 | 1.52 | 0.89 | 1.16 | 1.31 | 1.34 | 1.57 | 0.87 |
| Glutamic acid | 0.81 | 1.37 | 1.13 | 1.00 | 1.01 | 1.00 | 1.18 | 0.98 | 1.13 |
| Glutamine | 0.74 | 0.93 | 1.08 | 1.13 | 0.91 | 0.93 | 0.92 | 0.99 | 1.08 |
| Glycerol 3-phosphate | 0.78 | 1.27 | 0.76 | 1.03 | 0.99 | 1.01 | 1.18 | 0.80 | 1.24 |
| Glycine | 0.88 | 0.89 | 0.89 | 1.00 | 0.99 | 0.94 | 1.00 | 0.88 | 1.21 |
| Hypotaurine | 0.80 | 1.09 | 0.91 | 1.06 | 0.90 | 1.10 | 0.85 | 1.09 | 1.33 |
| Hypoxanthine | 1.00 | 1.00 | 1.00 | 1.24 | 0.94 | 0.81 | 1.00 | 1.00 | 1.00 |
| Inositol | 0.81 | 1.07 | 1.11 | 0.98 | 0.97 | 0.97 | 1.05 | 1.16 | 1.10 |
| Isoleucine | 0.87 | 0.89 | 1.16 | 1.05 | 1.15 | 1.12 | 1.07 | 0.95 | 1.03 |
| Lactic acid | 1.27 | 1.25 | 1.00 | 1.02 | 0.97 | 0.90 | 0.61 | 0.72 | 1.26 |
| Leucine | 1.11 | 1.04 | 1.32 | 1.02 | 1.04 | 0.98 | 0.99 | 0.87 | 1.24 |
| Lysine | 1.10 | 1.22 | 1.46 | 0.95 | 1.08 | 0.93 | 1.22 | 0.97 | 1.30 |
| Malic acid | 1.10 | 1.30 | 1.11 | 1.19 | 1.22 | 1.09 | 0.88 | 0.82 | 1.21 |
| Mannose | 1.07 | 1.01 | 1.30 | 0.93 | 1.08 | 1.26 | 1.18 | 1.31 | 0.94 |
| Niacinamide | 0.86 | 0.92 | 0.93 | 0.99 | 1.08 | 0.85 | 0.98 | 0.92 | 1.35 |
| O-Phosphoethanolamine | 0.83 | 1.13 | 1.07 | 1.09 | 1.02 | 1.04 | 1.13 | 0.84 | 1.46 |
| Ornithine | 1.11 | 1.22 | 1.39 | 1.30 | 1.05 | 0.75 | 1.31 | 1.19 | 0.94 |
| Palmitic acid | 0.86 | 1.06 | 0.87 | 0.97 | 0.98 | 0.87 | 0.79 | 0.74 | 0.77 |
| Pantothenic acid | 1.00 | 1.00 | 1.00 | 1.16 | 1.18 | 1.38 | 1.00 | 1.00 | 1.00 |
| Phenylalanine | 1.12 | 1.07 | 1.15 | 1.08 | 1.09 | 0.81 | 1.04 | 0.89 | 1.45 |
| Phosphoric acid | 0.89 | 1.06 | 0.98 | 1.01 | 1.00 | 0.96 | 1.09 | 0.89 | 1.26 |
| Proline | 1.00 | 1.32 | 1.15 | 1.00 | 1.09 | 1.03 | 0.98 | 0.92 | 0.94 |
| Pyruvic acid | 1.23 | 1.29 | 1.45 | 1.07 | 0.89 | 0.78 | 0.75 | 0.90 | 0.99 |
| Serine | 0.97 | 1.25 | 0.87 | 1.00 | 1.11 | 0.81 | 1.15 | 0.85 | 1.09 |
| Stearic acid | 0.91 | 1.06 | 0.81 | 0.95 | 1.00 | 0.87 | 0.81 | 0.75 | 0.77 |
| Succinic acid | 1.00 | 1.00 | 1.00 | 1.17 | 1.08 | 0.96 | 0.81 | 0.84 | 1.33 |
| Taurine | 0.79 | 0.84 | 0.92 | 1.03 | 1.15 | 1.30 | 1.00 | 1.00 | 1.00 |
| Threonic acid | 1.43 | 0.77 | 0.83 | 0.71 | 0.94 | 1.49 | 0.84 | 0.92 | 0.64 |
| Threonine | 0.83 | 1.29 | 1.28 | 0.98 | 1.06 | 1.09 | 1.14 | 1.12 | 1.10 |
| Urea | 1.01 | 1.39 | 1.22 | 1.09 | 1.37 | 1.24 | 1.25 | 1.11 | 1.40 |
| Valine | 1.14 | 1.08 | 1.41 | 1.14 | 1.19 | 1.06 | 1.08 | 0.95 | 1.01 |

Fig. 30 - 1

| Line No. | Groups | | | | | | Sub-Groups | Gene Name | Human Gene ID | Updated |
|---|---|---|---|---|---|---|---|---|---|---|
| 1 | 3 | 4 | 5 | 6 | 7 | 8 | VIII | Adrb3 | 155 | 4-May-15 |
| 2 | 3 | 4 | 5 | 6 | 7 | 8 | VIII | Ager | 177 | 17-May-15 |
| 3 | 3 | 4 | 5 | 6 | 7 | 8 | VIII | Alas2 | 212 | 4-May-15 |
| 4 | 3 | 4 | 5 | 6 | 7 | 8 | VIII | Alb | 213 | 7-Jun-15 |
| 5 | 3 | 4 | 5 | 6 | 7 | 8 | VIII | Aldob | 229 | 12-May-15 |
| 6 | 3 | 4 | 5 | 6 | 7 | 8 | VIII | Angptl4 | 51129 | 4-May-15 |
| 7 | 3 | 4 | 5 | 6 | 7 | 8 | VIII | Ano3 | 63982 | 21-May-15 |
| 8 | 3 | 4 | 5 | 6 | 7 | 8 | VIII | Aqp5 | 362 | 4-May-15 |
| 9 | 3 | 4 | 5 | 6 | 7 | 8 | VIII | Arg1 | 383 | 7-Jun-15 |
| 10 | 3 | 4 | 5 | 6 | 7 | 8 | VIII | Arntl | 406 | 12-May-15 |
| 11 | 3 | 4 | 5 | 6 | 7 | 8 | VIII | Arrdc2 | 27106 | 4-May-15 |
| 12 | 3 | 4 | 5 | 6 | 7 | 8 | VIII | Arrdc3 | 57561 | 4-May-15 |
| 13 | 3 | 4 | 5 | 6 | 7 | 8 | VIII | Atp6v0d2 | 245972 | 4-May-15 |
| 14 | 3 | 4 | 5 | 6 | 7 | 8 | VIII | Cebpd | 1052 | 4-May-15 |
| 15 | 3 | 4 | 5 | 6 | 7 | 8 | VIII | Ciart | 148523 | 12-May-15 |
| 16 | 3 | 4 | 5 | 6 | 7 | 8 | VIII | Cidea | 1149 | 4-May-15 |
| 17 | 3 | 4 | 5 | 6 | 7 | 8 | VIII | Cwc22 | 57703 | 4-May-15 |
| 18 | 3 | 4 | 5 | 6 | 7 | 8 | VIII | Dbp | 1628 | 7-Jun-15 |
| 19 | 3 | 4 | 5 | 6 | 7 | 8 | VIII | Ddit4 | 54541 | 4-May-15 |
| 20 | 3 | 4 | 5 | 6 | 7 | 8 | VIII | Elovl3 | 83401 | 4-May-15 |
| 21 | 3 | 4 | 5 | 6 | 7 | 8 | VIII | Fabp4 | 2167 | 24-May-15 |
| 22 | 3 | 4 | 5 | 6 | 7 | 8 | VIII | Fabp5 | 2171 | 7-Jun-15 |
| 23 | 3 | 4 | 5 | 6 | 7 | 8 | VIII | Foxo1 | 2308 | 17-May-15 |
| 24 | 3 | 4 | 5 | 6 | 7 | 8 | VIII | Fst | 10468 | 12-May-15 |
| 25 | 3 | 4 | 5 | 6 | 7 | 8 | VIII | Ftcd | 10841 | 4-May-15 |
| 26 | 3 | 4 | 5 | 6 | 7 | 8 | VIII | Gdpd3 | 79153 | 21-May-15 |
| 27 | 3 | 4 | 5 | 6 | 7 | 8 | VIII | Gnmt | 27232 | 12-May-15 |
| 28 | 3 | 4 | 5 | 6 | 7 | 8 | VIII | Gpnmb | 10457 | 12-May-15 |
| 29 | 3 | 4 | 5 | 6 | 7 | 8 | VIII | Hba-a2 | 3039 | 7-Jun-15 |
| 30 | 3 | 4 | 5 | 6 | 7 | 8 | VIII | Hbb-b1 | 3043 | 9-Jun-15 |
| 31 | 3 | 4 | 5 | 6 | 7 | 8 | VIII | Hbb-bs | 3044 | 9-Jun-15 |
| 32 | 3 | 4 | 5 | 6 | 7 | 8 | VIII | Hbb-bt | 3045 | 9-Jun-17 |
| 33 | 3 | 4 | 5 | 6 | 7 | 8 | VIII | Hif3a | 64344 | 4-May-15 |
| 34 | 3 | 4 | 5 | 6 | 7 | 8 | VIII | Hlf | 3131 | 7-Jun-15 |
| 35 | 3 | 4 | 5 | 6 | 7 | 8 | VIII | Hmgcs2 | 3158 | 12-May-15 |
| 36 | 3 | 4 | 5 | 6 | 7 | 8 | VIII | Hpcal4 | 51440 | 4-May-15 |
| 37 | 3 | 4 | 5 | 6 | 7 | 8 | VIII | Hpd | 3242 | 4-May-15 |
| 38 | 3 | 4 | 5 | 6 | 7 | 8 | VIII | Ky | 339855 | 4-May-15 |
| 39 | 3 | 4 | 5 | 6 | 7 | 8 | VIII | Mmp12 | 4321 | 4-May-15 |
| 40 | 3 | 4 | 5 | 6 | 7 | 8 | VIII | Nmrk2 | 27231 | 4-May-15 |
| 41 | 3 | 4 | 5 | 6 | 7 | 8 | VIII | Nppa | 4878 | 12-May-15 |
| 42 | 3 | 4 | 5 | 6 | 7 | 8 | VIII | Nppb | 4879 | 17-May-15 |
| 43 | 3 | 4 | 5 | 6 | 7 | 8 | VIII | Pah | 5053 | 23-May-15 |
| 44 | 3 | 4 | 5 | 6 | 7 | 8 | VIII | Pdk4 | 5166 | 4-May-15 |
| 45 | 3 | 4 | 5 | 6 | 7 | 8 | VIII | Plin4 | 729359 | 4-May-15 |
| 46 | 3 | 4 | 5 | 6 | 7 | 8 | VIII | Prm1 | 5619 | 7-Jun-15 |
| 47 | 3 | 4 | 5 | 6 | 7 | 8 | VIII | Saa1 | 6288 | 17-May-15 |
| 48 | 3 | 4 | 5 | 6 | 7 | 8 | VIII | Saa2 | 6289 | 7-Jun-15 |
| 49 | 3 | 4 | 5 | 6 | 7 | 8 | VIII | Scgb1a1 | 7356 | 4-May-15 |
| 50 | 3 | 4 | 5 | 6 | 7 | 8 | VIII | Sftpc | 6440 | 23-May-15 |
| 51 | 3 | 4 | 5 | 6 | 7 | 8 | VIII | Snap25 | 6616 | 7-Jun-15 |
| 52 | 3 | 4 | 5 | 6 | 7 | 8 | VIII | Snph | 9751 | 4-May-15 |
| 53 | 3 | 4 | 5 | 6 | 7 | 8 | VIII | Spp1 | 6696 | 7-Jun-15 |
| 54 | 3 | 4 | 5 | 6 | 7 | 8 | VIII | Sult5a1 | | |
| 55 | 3 | 4 | 5 | 6 | 7 | 8 | VIII | Thrsp | 7069 | 4-May-15 |
| 56 | 3 | 4 | 5 | 6 | 7 | 8 | VIII | Tnnc2 | 7125 | 12-May-15 |
| 57 | 3 | 4 | 5 | 6 | 7 | 8 | VIII | Umod | 7369 | 23-May-15 |
| 58 | 3 | 4 | 5 | 6 | 7 | 8 | VIII | Vgll2 | 245806 | 4-May-15 |
| 59 | 3 | 4 | 5 | 6 | 7 | | VII-2 | 1110017D15Rik | | |
| 60 | 3 | 4 | 5 | 6 | 7 | | VII-2 | 1700001C02Rik | | |
| 61 | 3 | 4 | 5 | 6 | 7 | | VII-2 | 1700007K13Rik | | |
| 62 | 3 | 4 | 5 | 6 | 7 | | VII-2 | 1700009P17Rik | | |
| 63 | 3 | 4 | 5 | 6 | 7 | | VII-2 | 1700024G13Rik | | |
| 64 | 3 | 4 | 5 | 6 | 7 | | VII-2 | 1810007D17Rik | | |
| 65 | 3 | 4 | 5 | 6 | 7 | | VII-2 | 1810065E05Rik | | |
| 66 | 3 | 4 | 5 | 6 | 7 | | VII-2 | 2210010C04Rik | | |
| 67 | 3 | 4 | 5 | 6 | 7 | | VII-2 | 2310007L24Rik | | |
| 68 | 3 | 4 | 5 | 6 | 7 | | VII-2 | 2410004P03Rik | | |
| 69 | 3 | 4 | 5 | 6 | 7 | | VII-2 | 2610305D13Rik | | |
| 70 | 3 | 4 | 5 | 6 | 7 | | VII-2 | 2610507I01Rik | | |
| 71 | 3 | 4 | 5 | 6 | 7 | | VII-2 | 4930401O12Rik | | |
| 72 | 3 | 4 | 5 | 6 | 7 | | VII-2 | AF357426 | | |
| 73 | 3 | 4 | 5 | 6 | 7 | | VII-2 | Alox15 | 246 | 4-May-15 |
| 74 | 3 | 4 | 5 | 6 | 7 | | VII-2 | Amy1 | 276, 277, 278 | 7-Jun-15 |
| 75 | 3 | 4 | 5 | 6 | 7 | | VII-2 | Amy2a2 | 279 | 7-Jun-15 |
| 76 | 3 | 4 | 5 | 6 | 7 | | VII-2 | Amy2a4 | 279 | 7-Jun-15 |
| 77 | 3 | 4 | 5 | 6 | 7 | | VII-2 | Amy2b | 280 | 4-May-15 |
| 78 | 3 | 4 | 5 | 6 | 7 | | VII-2 | Anapc11 | 51529 | 2-Jun-15 |
| 79 | 3 | 4 | 5 | 6 | 7 | | VII-2 | Apol7b | | |
| 80 | 3 | 4 | 5 | 6 | 7 | | VII-2 | Aqp12 | 375318 | 4-May-15 |
| 81 | 3 | 4 | 5 | 6 | 7 | | VII-2 | Arhgdig | 398 | 4-May-15 |
| 82 | 3 | 4 | 5 | 6 | 7 | | VII-2 | Atp6v0c-ps2 | | |
| 83 | 3 | 4 | 5 | 6 | 7 | | VII-2 | Bdh2 | 56898 | 4-May-15 |
| 84 | 3 | 4 | 5 | 6 | 7 | | VII-2 | Bglap | 632 | 17-May-15 |
| 85 | 3 | 4 | 5 | 6 | 7 | | VII-2 | Bglap2 | | |
| 86 | 3 | 4 | 5 | 6 | 7 | | VII-2 | Bmp10 | 27302 | 4-May-15 |
| 87 | 3 | 4 | 5 | 6 | 7 | | VII-2 | Camk2b | 816 | 4-May-15 |
| 88 | 3 | 4 | 5 | 6 | 7 | | VII-2 | Carns1 | 57571 | 4-May-15 |
| 89 | 3 | 4 | 5 | 6 | 7 | | VII-2 | Ccdc108 | 255101 | 4-May-15 |
| 90 | 3 | 4 | 5 | 6 | 7 | | VII-2 | Ccdc153 | 283152 | 4-May-15 |
| 91 | 3 | 4 | 5 | 6 | 7 | | VII-2 | Cckar | 886 | 12-May-15 |
| 92 | 3 | 4 | 5 | 6 | 7 | | VII-2 | Ccl28 | 56477 | 7-Jun-15 |
| 93 | 3 | 4 | 5 | 6 | 7 | | VII-2 | Cd5l | 922 | 4-May-15 |
| 94 | 3 | 4 | 5 | 6 | 7 | | VII-2 | Cda | 978 | 4-May-15 |
| 95 | 3 | 4 | 5 | 6 | 7 | | VII-2 | Cdhr5 | 53841 | 4-May-15 |
| 96 | 3 | 4 | 5 | 6 | 7 | | VII-2 | Cel | 1056 | 12-May-15 |
| 97 | 3 | 4 | 5 | 6 | 7 | | VII-2 | Cela1 | 1990 | 4-May-15 |
| 98 | 3 | 4 | 5 | 6 | 7 | | VII-2 | Cela3b | 23436 | 4-May-15 |
| 99 | 3 | 4 | 5 | 6 | 7 | | VII-2 | Celsr1 | 9620 | 12-May-15 |
| 100 | 3 | 4 | 5 | 6 | 7 | | VII-2 | Chac1 | 79094 | 23-May-15 |
| 101 | 3 | 4 | 5 | 6 | 7 | | VII-2 | Cideb | 27141 | 12-May-15 |
| 102 | 3 | 4 | 5 | 6 | 7 | | VII-2 | Cish | 1154 | 4-May-15 |
| 103 | 3 | 4 | 5 | 6 | 7 | | VII-2 | Cldn10 | 9071 | 4-May-15 |
| 104 | 3 | 4 | 5 | 6 | 7 | | VII-2 | Clec3a | 10143 | 14-May-15 |
| 105 | 3 | 4 | 5 | 6 | 7 | | VII-2 | Clps | 1208 | 4-May-15 |
| 106 | 3 | 4 | 5 | 6 | 7 | | VII-2 | Cpa1 | 1357 | 4-May-15 |
| 107 | 3 | 4 | 5 | 6 | 7 | | VII-2 | Cpa2 | 1358 | 4-May-15 |
| 108 | 3 | 4 | 5 | 6 | 7 | | VII-2 | Cpb1 | 1360 | 4-May-15 |
| 109 | 3 | 4 | 5 | 6 | 7 | | VII-2 | Crabp1 | 1381 | 4-May-15 |
| 110 | 3 | 4 | 5 | 6 | 7 | | VII-2 | Crtac1 | 55118 | 4-May-15 |
| 111 | 3 | 4 | 5 | 6 | 7 | | VII-2 | Cryab | 1410 | 23-May-15 |
| 112 | 3 | 4 | 5 | 6 | 7 | | VII-2 | Ctrc | 11330 | 23-May-15 |
| 113 | 3 | 4 | 5 | 6 | 7 | | VII-2 | Ctrros | | |
| 114 | 3 | 4 | 5 | 6 | 7 | | VII-2 | Ctrl | 1506 | 4-May-15 |
| 115 | 3 | 4 | 5 | 6 | 7 | | VII-2 | Ctsg | 1511 | 12-May-15 |
| 116 | 3 | 4 | 5 | 6 | 7 | | VII-2 | Cxcl11 | 6373 | 3-May-15 |
| 117 | 3 | 4 | 5 | 6 | 7 | | VII-2 | Cyp2b9 | 1555, 1556 | 7-Jun-15 |
| 118 | 3 | 4 | 5 | 6 | 7 | | VII-2 | Cyp2d12 | | |
| 119 | 3 | 4 | 5 | 6 | 7 | | VII-2 | Cyp2d9 | | |
| 120 | 3 | 4 | 5 | 6 | 7 | | VII-2 | Cypt8 | | |
| 121 | 3 | 4 | 5 | 6 | 7 | | VII-2 | Dao | 1610 | 7-Jun-15 |
| 122 | 3 | 4 | 5 | 6 | 7 | | VII-2 | Dcdc2a | 51473 | 24-May-15 |
| 123 | 3 | 4 | 5 | 6 | 7 | | VII-2 | Dmbt1 | 1755 | 12-May-15 |
| 124 | 3 | 4 | 5 | 6 | 7 | | VII-2 | Dnajc22 | 79962 | 12-May-15 |
| 125 | 3 | 4 | 5 | 6 | 7 | | VII-2 | Dnali1 | 7802 | 4-May-15 |
| 126 | 3 | 4 | 5 | 6 | 7 | | VII-2 | Dydc2 | 84332 | 4-May-15 |
| 127 | 3 | 4 | 5 | 6 | 7 | | VII-2 | Dynlrb2 | 83657 | 12-May-15 |
| 128 | 3 | 4 | 5 | 6 | 7 | | VII-2 | Ear3 | 7025 | 4-May-15 |
| 129 | 3 | 4 | 5 | 6 | 7 | | VII-2 | Eif3j2 | | |
| 130 | 3 | 4 | 5 | 6 | 7 | | VII-2 | Elane | 1991 | 23-May-15 |
| 131 | 3 | 4 | 5 | 6 | 7 | | VII-2 | Erp27 | 121506 | 4-May-15 |
| 132 | 3 | 4 | 5 | 6 | 7 | | VII-2 | F5 | 2153 | 23-May-15 |
| 133 | 3 | 4 | 5 | 6 | 7 | | VII-2 | Fam166b | 730112 | 4-May-15 |
| 134 | 3 | 4 | 5 | 6 | 7 | | VII-2 | Fam167a | 83648 | 4-May-15 |
| 135 | 3 | 4 | 5 | 6 | 7 | | VII-2 | Fam183b | 340286 | 21-May-15 |
| 136 | 3 | 4 | 5 | 6 | 7 | | VII-2 | Fam213b | 127281 | 4-May-15 |
| 137 | 3 | 4 | 5 | 6 | 7 | | VII-2 | Fbp1 | 2203 | 12-May-15 |
| 138 | 3 | 4 | 5 | 6 | 7 | | VII-2 | Fbp2 | 8789 | 7-Jun-15 |
| 139 | 3 | 4 | 5 | 6 | 7 | | VII-2 | Fcer2a | | |
| 140 | 3 | 4 | 5 | 6 | 7 | | VII-2 | Fermt1 | 55612 | 12-May-15 |
| 141 | 3 | 4 | 5 | 6 | 7 | | VII-2 | Fgfr4 | 2264 | 18-May-15 |
| 142 | 3 | 4 | 5 | 6 | 7 | | VII-2 | Fndc7 | 163479 | 4-May-15 |
| 143 | 3 | 4 | 5 | 6 | 7 | | VII-2 | Foxj1 | 2302 | 12-May-15 |
| 144 | 3 | 4 | 5 | 6 | 7 | | VII-2 | Ggta1 | 2681 | 4-May-15 |
| 145 | 3 | 4 | 5 | 6 | 7 | | VII-2 | Gipc2 | 54810 | 4-May-15 |
| 146 | 3 | 4 | 5 | 6 | 7 | | VII-2 | Gm10334 | | |
| 147 | 3 | 4 | 5 | 6 | 7 | | VII-2 | Gm11549 | | |
| 148 | 3 | 4 | 5 | 6 | 7 | | VII-2 | Gm12185 | | |
| 149 | 3 | 4 | 5 | 6 | 7 | | VII-2 | Gm13011 | | |
| 150 | 3 | 4 | 5 | 6 | 7 | | VII-2 | Gm21637 | | |
| 151 | 3 | 4 | 5 | 6 | 7 | | VII-2 | Gm5409 | | |
| 152 | 3 | 4 | 5 | 6 | 7 | | VII-2 | Gm5771 | | |
| 153 | 3 | 4 | 5 | 6 | 7 | | VII-2 | Gp2 | 2813 | 4-May-15 |
| 154 | 3 | 4 | 5 | 6 | 7 | | VII-2 | Guca2a | 2980 | 4-May-15 |
| 155 | 3 | 4 | 5 | 6 | 7 | | VII-2 | Haao | 23498 | 4-May-15 |
| 156 | 3 | 4 | 5 | 6 | 7 | | VII-2 | Hal | 3034 | 12-May-15 |
| 157 | 3 | 4 | 5 | 6 | 7 | | VII-2 | Hamp2 | | |
| 158 | 3 | 4 | 5 | 6 | 7 | | VII-2 | Hdc | 3067 | 7-Jun-15 |
| 159 | 3 | 4 | 5 | 6 | 7 | | VII-2 | Hmgcr | 3156 | 4-May-15 |
| 160 | 3 | 4 | 5 | 6 | 7 | | VII-2 | Hnf4a | 3172 | 23-May-15 |
| 161 | 3 | 4 | 5 | 6 | 7 | | VII-2 | Igfals | 3483 | 12-May-15 |
| 162 | 3 | 4 | 5 | 6 | 7 | | VII-2 | Igsf11 | 152404 | 4-May-15 |
| 163 | 3 | 4 | 5 | 6 | 7 | | VII-2 | Ihh | 3549 | 12-May-15 |
| 164 | 3 | 4 | 5 | 6 | 7 | | VII-2 | Iqcg | 84223 | 4-May-15 |
| 165 | 3 | 4 | 5 | 6 | 7 | | VII-2 | Iyd | 389434 | 4-May-15 |
| 166 | 3 | 4 | 5 | 6 | 7 | | VII-2 | Klk1 | 3816 | 12-May-15 |
| 167 | 3 | 4 | 5 | 6 | 7 | | VII-2 | Klk1b11 | | |
| 168 | 3 | 4 | 5 | 6 | 7 | | VII-2 | Klk1b21 | | |
| 169 | 3 | 4 | 5 | 6 | 7 | | VII-2 | Klk1b3 | | |
| 170 | 3 | 4 | 5 | 6 | 7 | | VII-2 | Klk1b4 | | |
| 171 | 3 | 4 | 5 | 6 | 7 | | VII-2 | Klk1b5 | | |
| 172 | 3 | 4 | 5 | 6 | 7 | | VII-2 | Krt12 | 3859 | 4-May-15 |
| 173 | 3 | 4 | 5 | 6 | 7 | | VII-2 | LOC100048884 | | |
| 174 | 3 | 4 | 5 | 6 | 7 | | VII-2 | Lrrc23 | 10233 | 4-May-15 |
| 175 | 3 | 4 | 5 | 6 | 7 | | VII-2 | Ltf | 4057 | 23-May-15 |
| 176 | 3 | 4 | 5 | 6 | 7 | | VII-2 | Ly6d | 8581 | 7-Jun-15 |
| 177 | 3 | 4 | 5 | 6 | 7 | | VII-2 | Lyve1 | 10894 | 4-May-15 |
| 178 | 3 | 4 | 5 | 6 | 7 | | VII-2 | Mapk15 | 225689 | 3-May-15 |
| 179 | 3 | 4 | 5 | 6 | 7 | | VII-2 | Mcpt8 | | |
| 180 | 3 | 4 | 5 | 6 | 7 | | VII-2 | Mettl7b | 196410 | 4-May-15 |
| 181 | 3 | 4 | 5 | 6 | 7 | | VII-2 | Mid1 | 4281 | 7-Jun-15 |
| 182 | 3 | 4 | 5 | 6 | 7 | | VII-2 | Mir101c | | |
| 183 | 3 | 4 | 5 | 6 | 7 | | VII-2 | Mir128-2 | 406916 | 21-May-15 |
| 184 | 3 | 4 | 5 | 6 | 7 | | VII-2 | Mir1291 | 100302221 | 21-May-15 |
| 185 | 3 | 4 | 5 | 6 | 7 | | VII-2 | Mir129-1 | 406917 | 21-May-15 |
| 186 | 3 | 4 | 5 | 6 | 7 | | VII-2 | Mir130b | 406920 | 21-May-15 |

Fig. 30 - 2

| # | | | | | | | Name | ID | Date |
|---|---|---|---|---|---|---|---|---|---|
| 187 | 3 | 4 | 5 | 6 | 7 | VII-2 | Mir135b | 442891 | 21-May-15 |
| 188 | 3 | 4 | 5 | 6 | 7 | VII-2 | Mir137 | 406928 | 21-May-15 |
| 189 | 3 | 4 | 5 | 6 | 7 | VII-2 | Mir145b | | |
| 190 | 3 | 4 | 5 | 6 | 7 | VII-2 | Mir152 | 406943 | 21-May-15 |
| 191 | 3 | 4 | 5 | 6 | 7 | VII-2 | Mir16-2 | 406951 | 21-May-15 |
| 192 | 3 | 4 | 5 | 6 | 7 | VII-2 | Mir1896 | | |
| 193 | 3 | 4 | 5 | 6 | 7 | VII-2 | Mir18b | 574033 | 21-May-15 |
| 194 | 3 | 4 | 5 | 6 | 7 | VII-2 | Mir1903 | | |
| 195 | 3 | 4 | 5 | 6 | 7 | VII-2 | Mir1947 | | |
| 196 | 3 | 4 | 5 | 6 | 7 | VII-2 | Mir195b | | |
| 197 | 3 | 4 | 5 | 6 | 7 | VII-2 | Mir196a-1 | | |
| 198 | 3 | 4 | 5 | 6 | 7 | VII-2 | Mir1a-1 | | |
| 199 | 3 | 4 | 5 | 6 | 7 | VII-2 | Mir1b | | |
| 200 | 3 | 4 | 5 | 6 | 7 | VII-2 | Mir208a | 406990 | 4-May-15 |
| 201 | 3 | 4 | 5 | 6 | 7 | VII-2 | Mir2137 | | |
| 202 | 3 | 4 | 5 | 6 | 7 | VII-2 | Mir218-1 | 407000 | 21-May-15 |
| 203 | 3 | 4 | 5 | 6 | 7 | VII-2 | Mir219b | 100616335 | 21-May-15 |
| 204 | 3 | 4 | 5 | 6 | 7 | VII-2 | Mir223 | 407008 | 21-May-15 |
| 205 | 3 | 4 | 5 | 6 | 7 | VII-2 | Mir296 | 407022 | 21-May-15 |
| 206 | 3 | 4 | 5 | 6 | 7 | VII-2 | Mir298 | 100126296 | 4-May-15 |
| 207 | 3 | 4 | 5 | 6 | 7 | VII-2 | Mir29b-1 | | |
| 208 | 3 | 4 | 5 | 6 | 7 | VII-2 | Mir3070b | | |
| 209 | 3 | 4 | 5 | 6 | 7 | VII-2 | Mir3073b | | |
| 210 | 3 | 4 | 5 | 6 | 7 | VII-2 | Mir3099 | | |
| 211 | 3 | 4 | 5 | 6 | 7 | VII-2 | Mir30c-1 | | |
| 212 | 3 | 4 | 5 | 6 | 7 | VII-2 | Mir31 | 407035 | 21-May-15 |
| 213 | 3 | 4 | 5 | 6 | 7 | VII-2 | Mir3101 | | |
| 214 | 3 | 4 | 5 | 6 | 7 | VII-2 | Mir3108 | | |
| 215 | 3 | 4 | 5 | 6 | 7 | VII-2 | Mir3110 | | |
| 216 | 3 | 4 | 5 | 6 | 7 | VII-2 | Mir341 | | |
| 217 | 3 | 4 | 5 | 6 | 7 | VII-2 | Mir344 | | |
| 218 | 3 | 4 | 5 | 6 | 7 | VII-2 | Mir344-2 | | |
| 219 | 3 | 4 | 5 | 6 | 7 | VII-2 | Mir344b | | |
| 220 | 3 | 4 | 5 | 6 | 7 | VII-2 | Mir344d-2 | | |
| 221 | 3 | 4 | 5 | 6 | 7 | VII-2 | Mir344e | | |
| 222 | 3 | 4 | 5 | 6 | 7 | VII-2 | Mir344f | | |
| 223 | 3 | 4 | 5 | 6 | 7 | VII-2 | Mir370 | 442915 | 21-May-15 |
| 224 | 3 | 4 | 5 | 6 | 7 | VII-2 | Mir384 | 494333 | 4-May-15 |
| 225 | 3 | 4 | 5 | 6 | 7 | VII-2 | Mir449a | 554213 | 21-May-15 |
| 226 | 3 | 4 | 5 | 6 | 7 | VII-2 | Mir450-1 | | |
| 227 | 3 | 4 | 5 | 6 | 7 | VII-2 | Mir452 | 574412 | 21-May-15 |
| 228 | 3 | 4 | 5 | 6 | 7 | VII-2 | Mir468 | | |
| 229 | 3 | 4 | 5 | 6 | 7 | VII-2 | Mir500 | 574502 | 21-May-15 |
| 230 | 3 | 4 | 5 | 6 | 7 | VII-2 | Mir504 | 574507 | 21-May-15 |
| 231 | 3 | 4 | 5 | 6 | 7 | VII-2 | Mir509 | | |
| 232 | 3 | 4 | 5 | 6 | 7 | VII-2 | Mir5122 | 574459 | 21-May-15 |
| 233 | 3 | 4 | 5 | 6 | 7 | VII-2 | Mir539 | 664612 | 21-May-15 |
| 234 | 3 | 4 | 5 | 6 | 7 | VII-2 | Mir542 | 664617 | 21-May-15 |
| 235 | 3 | 4 | 5 | 6 | 7 | VII-2 | Mir543 | 100126335 | 21-May-15 |
| 236 | 3 | 4 | 5 | 6 | 7 | VII-2 | Mir615 | 693200 | 21-May-15 |
| 237 | 3 | 4 | 5 | 6 | 7 | VII-2 | Mir6345 | | |
| 238 | 3 | 4 | 5 | 6 | 7 | VII-2 | Mir6351 | | |
| 239 | 3 | 4 | 5 | 6 | 7 | VII-2 | Mir6353 | | |
| 240 | 3 | 4 | 5 | 6 | 7 | VII-2 | Mir6361 | | |
| 241 | 3 | 4 | 5 | 6 | 7 | VII-2 | Mir6374 | | |
| 242 | 3 | 4 | 5 | 6 | 7 | VII-2 | Mir6375 | | |
| 243 | 3 | 4 | 5 | 6 | 7 | VII-2 | Mir6381 | | |
| 244 | 3 | 4 | 5 | 6 | 7 | VII-2 | Mir6385 | | |
| 245 | 3 | 4 | 5 | 6 | 7 | VII-2 | Mir6393 | | |
| 246 | 3 | 4 | 5 | 6 | 7 | VII-2 | Mir6394 | | |
| 247 | 3 | 4 | 5 | 6 | 7 | VII-2 | Mir6409 | | |
| 248 | 3 | 4 | 5 | 6 | 7 | VII-2 | Mir6410 | | |
| 249 | 3 | 4 | 5 | 6 | 7 | VII-2 | Mir6516 | 102466864 | 4-May-15 |
| 250 | 3 | 4 | 5 | 6 | 7 | VII-2 | Mir668 | 768214 | 4-May-15 |
| 251 | 3 | 4 | 5 | 6 | 7 | VII-2 | Mir669a-2 | | |
| 252 | 3 | 4 | 5 | 6 | 7 | VII-2 | Mir670 | 100313777 | 4-May-15 |
| 253 | 3 | 4 | 5 | 6 | 7 | VII-2 | Mir677 | | |
| 254 | 3 | 4 | 5 | 6 | 7 | VII-2 | Mir680-3 | | |
| 255 | 3 | 4 | 5 | 6 | 7 | VII-2 | Mir683-1 | | |
| 256 | 3 | 4 | 5 | 6 | 7 | VII-2 | Mir6899 | | |
| 257 | 3 | 4 | 5 | 6 | 7 | VII-2 | Mir6901 | | |
| 258 | 3 | 4 | 5 | 6 | 7 | VII-2 | Mir6906 | | |
| 259 | 3 | 4 | 5 | 6 | 7 | VII-2 | Mir693 | | |
| 260 | 3 | 4 | 5 | 6 | 7 | VII-2 | Mir6949 | | |
| 261 | 3 | 4 | 5 | 6 | 7 | VII-2 | Mir695 | | |
| 262 | 3 | 4 | 5 | 6 | 7 | VII-2 | Mir6952 | | |
| 263 | 3 | 4 | 5 | 6 | 7 | VII-2 | Mir6955 | | |
| 264 | 3 | 4 | 5 | 6 | 7 | VII-2 | Mir6956 | | |
| 265 | 3 | 4 | 5 | 6 | 7 | VII-2 | Mir6965 | | |
| 266 | 3 | 4 | 5 | 6 | 7 | VII-2 | Mir6971 | | |
| 267 | 3 | 4 | 5 | 6 | 7 | VII-2 | Mir698 | | |
| 268 | 3 | 4 | 5 | 6 | 7 | VII-2 | Mir6983 | | |
| 269 | 3 | 4 | 5 | 6 | 7 | VII-2 | Mir6987 | | |
| 270 | 3 | 4 | 5 | 6 | 7 | VII-2 | Mir7038 | | |
| 271 | 3 | 4 | 5 | 6 | 7 | VII-2 | Mir705 | | |
| 272 | 3 | 4 | 5 | 6 | 7 | VII-2 | Mir7055 | | |
| 273 | 3 | 4 | 5 | 6 | 7 | VII-2 | Mir7056 | | |
| 274 | 3 | 4 | 5 | 6 | 7 | VII-2 | Mir7060 | | |
| 275 | 3 | 4 | 5 | 6 | 7 | VII-2 | Mir7065 | | |
| 276 | 3 | 4 | 5 | 6 | 7 | VII-2 | Mir7076 | | |
| 277 | 3 | 4 | 5 | 6 | 7 | VII-2 | Mir7094-1 | | |
| 278 | 3 | 4 | 5 | 6 | 7 | VII-2 | Mir7094-2 | | |
| 279 | 3 | 4 | 5 | 6 | 7 | VII-2 | Mir7-2 | 407044 | 21-May-15 |
| 280 | 3 | 4 | 5 | 6 | 7 | VII-2 | Mir721 | | |
| 281 | 3 | 4 | 5 | 6 | 7 | VII-2 | Mir7235 | | |
| 282 | 3 | 4 | 5 | 6 | 7 | VII-2 | Mir743 | | |
| 283 | 3 | 4 | 5 | 6 | 7 | VII-2 | Mir7667 | | |
| 284 | 3 | 4 | 5 | 6 | 7 | VII-2 | Mir770 | 768222 | 4-May-15 |
| 285 | 3 | 4 | 5 | 6 | 7 | VII-2 | Mir8091 | | |
| 286 | 3 | 4 | 5 | 6 | 7 | VII-2 | Mir8101 | | |
| 287 | 3 | 4 | 5 | 6 | 7 | VII-2 | Mir8109 | | |
| 288 | 3 | 4 | 5 | 6 | 7 | VII-2 | Mir8110 | | |
| 289 | 3 | 4 | 5 | 6 | 7 | VII-2 | Mir9-3 | 407051 | 21-May-15 |
| 290 | 3 | 4 | 5 | 6 | 7 | VII-2 | Mirlet7a-2 | | |
| 291 | 3 | 4 | 5 | 6 | 7 | VII-2 | Mmd2 | 221938 | 4-May-15 |
| 292 | 3 | 4 | 5 | 6 | 7 | VII-2 | Mmp7 | 4316 | 17-May-15 |
| 293 | 3 | 4 | 5 | 6 | 7 | VII-2 | Mpo | 4353 | 23-May-15 |
| 294 | 3 | 4 | 5 | 6 | 7 | VII-2 | Mrs2 | 57380 | 4-May-15 |
| 295 | 3 | 4 | 5 | 6 | 7 | VII-2 | Ms4a1 | 931 | 7-Jun-15 |
| 296 | 3 | 4 | 5 | 6 | 7 | VII-2 | Mt3 | 4504 | 24-May-15 |
| 297 | 3 | 4 | 5 | 6 | 7 | VII-2 | Mup1 | 60386 | 23-May-15 |
| 298 | 3 | 4 | 5 | 6 | 7 | VII-2 | Mup10 | | |
| 299 | 3 | 4 | 5 | 6 | 7 | VII-2 | Mup11 | | |
| 300 | 3 | 4 | 5 | 6 | 7 | VII-2 | Mup12 | | |
| 301 | 3 | 4 | 5 | 6 | 7 | VII-2 | Mup13 | | |
| 302 | 3 | 4 | 5 | 6 | 7 | VII-2 | Mup14 | | |
| 303 | 3 | 4 | 5 | 6 | 7 | VII-2 | Mup15 | | |
| 304 | 3 | 4 | 5 | 6 | 7 | VII-2 | Mup16 | | |
| 305 | 3 | 4 | 5 | 6 | 7 | VII-2 | Mup17 | | |
| 306 | 3 | 4 | 5 | 6 | 7 | VII-2 | Mup19 | | |
| 307 | 3 | 4 | 5 | 6 | 7 | VII-2 | Mup2 | | |
| 308 | 3 | 4 | 5 | 6 | 7 | VII-2 | Mup7 | | |
| 309 | 3 | 4 | 5 | 6 | 7 | VII-2 | Mup8 | | |
| 310 | 3 | 4 | 5 | 6 | 7 | VII-2 | Mup9 | | |
| 311 | 3 | 4 | 5 | 6 | 7 | VII-2 | Nlrp6 | 171389 | 4-May-15 |
| 312 | 3 | 4 | 5 | 6 | 7 | VII-2 | Nme5 | 8382 | 4-May-15 |
| 313 | 3 | 4 | 5 | 6 | 7 | VII-2 | Noturn | 147111 | 9-May-15 |
| 314 | 3 | 4 | 5 | 6 | 7 | VII-2 | Nrep | 9315 | 12-May-15 |
| 315 | 3 | 4 | 5 | 6 | 7 | VII-2 | Oaz1 | 4946 | 12-May-15 |
| 316 | 3 | 4 | 5 | 6 | 7 | VII-2 | Odf3b | 440836 | 4-May-15 |
| 317 | 3 | 4 | 5 | 6 | 7 | VII-2 | Padi4 | 23569 | 21-May-15 |
| 318 | 3 | 4 | 5 | 6 | 7 | VII-2 | Pate4 | 399968 | 12-May-15 |
| 319 | 3 | 4 | 5 | 6 | 7 | VII-2 | Pdia2 | 64714 | 12-May-15 |
| 320 | 3 | 4 | 5 | 6 | 7 | VII-2 | Pet117 | 100303755 | 4-May-15 |
| 321 | 3 | 4 | 5 | 6 | 7 | VII-2 | Pglyrp1 | 8993 | 4-May-15 |
| 322 | 3 | 4 | 5 | 6 | 7 | VII-2 | Pipox | 51268 | 4-May-15 |
| 323 | 3 | 4 | 5 | 6 | 7 | VII-2 | Pklr | 5313 | 17-May-15 |
| 324 | 3 | 4 | 5 | 6 | 7 | VII-2 | Pla2g1b | 5319 | 12-May-15 |
| 325 | 3 | 4 | 5 | 6 | 7 | VII-2 | Plet1 | 349633 | 4-May-15 |
| 326 | 3 | 4 | 5 | 6 | 7 | VII-2 | Pnlip | 5406 | 12-May-15 |
| 327 | 3 | 4 | 5 | 6 | 7 | VII-2 | Pnliprp1 | 5407 | 12-May-15 |
| 328 | 3 | 4 | 5 | 6 | 7 | VII-2 | Pnliprp2 | 5408 | 4-May-15 |
| 329 | 3 | 4 | 5 | 6 | 7 | VII-2 | Ppil6 | 285755 | 4-May-15 |
| 330 | 3 | 4 | 5 | 6 | 7 | VII-2 | Ppp1r1b | 84152 | 4-May-15 |
| 331 | 3 | 4 | 5 | 6 | 7 | VII-2 | Prg4 | 10216 | 7-Jun-15 |
| 332 | 3 | 4 | 5 | 6 | 7 | VII-2 | Prm2 | 5620 | 12-May-15 |
| 333 | 3 | 4 | 5 | 6 | 7 | VII-2 | Prss1 | 5644 | 7-Jun-15 |
| 334 | 3 | 4 | 5 | 6 | 7 | VII-2 | Prss2 | 5645 | 23-May-15 |
| 335 | 3 | 4 | 5 | 6 | 7 | VII-2 | Prss3 | 5646 | 4-May-15 |
| 336 | 3 | 4 | 5 | 6 | 7 | VII-2 | Prss34 | | |
| 337 | 3 | 4 | 5 | 6 | 7 | VII-2 | Ptprr | 5801 | 17-May-15 |
| 338 | 3 | 4 | 5 | 6 | 7 | VII-2 | Rap1gap | 5909 | 4-May-15 |
| 339 | 3 | 4 | 5 | 6 | 7 | VII-2 | Rdh16 | 8608 | 12-May-15 |
| 340 | 3 | 4 | 5 | 6 | 7 | VII-2 | Reg1 | | |
| 341 | 3 | 4 | 5 | 6 | 7 | VII-2 | Reg3a | 5068 | 12-May-15 |
| 342 | 3 | 4 | 5 | 6 | 7 | VII-2 | Reg3b | | |
| 343 | 3 | 4 | 5 | 6 | 7 | VII-2 | Reg3d | | |
| 344 | 3 | 4 | 5 | 6 | 7 | VII-2 | Retnlb | 84666 | 4-May-15 |
| 345 | 3 | 4 | 5 | 6 | 7 | VII-2 | Rnase1 | 6035 | 4-May-15 |
| 346 | 3 | 4 | 5 | 6 | 7 | VII-2 | Rnase2a | | |
| 347 | 3 | 4 | 5 | 6 | 7 | VII-2 | Rnase2b | | |
| 348 | 3 | 4 | 5 | 6 | 7 | VII-2 | Rsph4a | 345895 | 23-May-15 |
| 349 | 3 | 4 | 5 | 6 | 7 | VII-2 | Sap25 | 100316904 | 4-May-15 |
| 350 | 3 | 4 | 5 | 6 | 7 | VII-2 | Scarna2 | 677766 | 12-May-15 |
| 351 | 3 | 4 | 5 | 6 | 7 | VII-2 | Scarna3a | | |
| 352 | 3 | 4 | 5 | 6 | 7 | VII-2 | Serpina9 | 327657 | 4-May-15 |
| 353 | 3 | 4 | 5 | 6 | 7 | VII-2 | Serpini2 | 5276 | 4-May-15 |
| 354 | 3 | 4 | 5 | 6 | 7 | VII-2 | Siglece | | |
| 355 | 3 | 4 | 5 | 6 | 7 | VII-2 | Slc30a3 | 7781 | 4-May-15 |
| 356 | 3 | 4 | 5 | 6 | 7 | VII-2 | Slc39a5 | 283375 | 4-May-15 |
| 357 | 3 | 4 | 5 | 6 | 7 | VII-2 | Slc7a9 | 11136 | 12-May-15 |
| 358 | 3 | 4 | 5 | 6 | 7 | VII-2 | Slc9a3 | 6550 | 17-May-15 |
| 359 | 3 | 4 | 5 | 6 | 7 | VII-2 | Slc9a3r2 | 9351 | 4-May-15 |
| 360 | 3 | 4 | 5 | 6 | 7 | VII-2 | Slfn5os | | |
| 361 | 3 | 4 | 5 | 6 | 7 | VII-2 | Slurp1 | 57152 | 4-May-15 |
| 362 | 3 | 4 | 5 | 6 | 7 | VII-2 | Snai3 | 333929 | 4-May-15 |
| 363 | 3 | 4 | 5 | 6 | 7 | VII-2 | Snora3 | 619562 | 4-May-15 |
| 364 | 3 | 4 | 5 | 6 | 7 | VII-2 | Snora30 | 677813 | 4-May-15 |
| 365 | 3 | 4 | 5 | 6 | 7 | VII-2 | Snora31 | 677814 | 4-May-15 |
| 366 | 3 | 4 | 5 | 6 | 7 | VII-2 | Snora65 | 26783 | 4-May-15 |
| 367 | 3 | 4 | 5 | 6 | 7 | VII-2 | Snora70 | 26778 | 4-May-15 |
| 368 | 3 | 4 | 5 | 6 | 7 | VII-2 | Snord116 | | |
| 369 | 3 | 4 | 5 | 6 | 7 | VII-2 | Snord15b | 114599 | 4-May-15 |
| 370 | 3 | 4 | 5 | 6 | 7 | VII-2 | Snord33 | 26818 | 4-May-15 |
| 371 | 3 | 4 | 5 | 6 | 7 | VII-2 | Snord35a | 26816 | 4-May-15 |
| 372 | 3 | 4 | 5 | 6 | 7 | VII-2 | Snord43 | 26807 | 4-May-15 |

Fig. 30 - 3

| | | | | | | | | | | | | | | | | | | |
|---|---|---|---|---|---|---|---|---|---|---|---|---|---|---|---|---|---|---|
| 373 | 3 | 4 | 5 | 6 | 7 | VII-2 | Sntn | 132203 | 4-May-15 | 469 | 3 | 4 | 5 | 6 | 7 | VII-1 | AY761185 | | |
| 374 | 3 | 4 | 5 | 6 | 7 | VII-2 | Sorcs2 | 57537 | 4-May-15 | 470 | 3 | 4 | 5 | 6 | 7 | VII-1 | Azgp1 | 563 | 24-May-15 |
| 375 | 3 | 4 | 5 | 6 | 7 | VII-2 | Spink3 | 6690 | 23-May-15 | 471 | 3 | 4 | 5 | 6 | 7 | VII-1 | Basp1 | 10409 | 4-May-15 |
| 376 | 3 | 4 | 5 | 6 | 7 | VII-2 | Stbd1 | 8987 | 4-May-15 | 472 | 3 | 4 | 5 | 6 | 7 | VII-1 | BC018473 | | |
| 377 | 3 | 4 | 5 | 6 | 7 | VII-2 | Svs2 | | | 473 | 3 | 4 | 5 | 6 | 7 | VII-1 | BC035044 | | |
| 378 | 3 | 4 | 5 | 6 | 7 | VII-2 | Svs4 | | | 474 | 3 | 4 | 5 | 6 | 7 | VII-1 | BC048679 | | |
| 379 | 3 | 4 | 5 | 6 | 7 | VII-2 | Svs6 | | | 475 | 3 | 4 | 5 | 6 | 7 | VII-1 | BC094916 | | |
| 380 | 3 | 4 | 5 | 6 | 7 | VII-2 | Sycn | 342898 | 4-May-15 | 476 | 3 | 4 | 5 | 6 | 7 | VII-1 | Bcl11a | 53335 | 4-May-15 |
| 381 | 3 | 4 | 5 | 6 | 7 | VII-2 | Tcerg1l | 256536 | 4-May-15 | 477 | 3 | 4 | 5 | 6 | 7 | VII-1 | Bcl2l15 | 440603 | 4-May-15 |
| 382 | 3 | 4 | 5 | 6 | 7 | VII-2 | Tctex1d4 | 343521 | 4-May-15 | 478 | 3 | 4 | 5 | 6 | 7 | VII-1 | Bglap3 | | |
| 383 | 3 | 4 | 5 | 6 | 7 | VII-2 | Tekt1 | 83659 | 21-May-15 | 479 | 3 | 4 | 5 | 6 | 7 | VII-1 | Birc5 | 332 | 24-May-15 |
| 384 | 3 | 4 | 5 | 6 | 7 | VII-2 | Tesc | 54997 | 17-May-15 | 480 | 3 | 4 | 5 | 6 | 7 | VII-1 | Blnk | 29760 | 17-May-15 |
| 385 | 3 | 4 | 5 | 6 | 7 | VII-2 | Tff3 | 7033 | 24-May-15 | 481 | 3 | 4 | 5 | 6 | 7 | VII-1 | Bpifa1 | 51297 | 10-May-15 |
| 386 | 3 | 4 | 5 | 6 | 7 | VII-2 | Tmed6 | 146456 | 4-May-15 | 482 | 3 | 4 | 5 | 6 | 7 | VII-1 | Bpifb1 | 92747 | 4-May-15 |
| 387 | 3 | 4 | 5 | 6 | 7 | VII-2 | Tmem212 | 389177 | 4-May-15 | 483 | 3 | 4 | 5 | 6 | 7 | VII-1 | Bsph1 | 100131, 137 | 4-May-15 |
| 388 | 3 | 4 | 5 | 6 | 7 | VII-2 | Tnp1 | 7141 | 12-May-15 | 484 | 3 | 4 | 5 | 6 | 7 | VII-1 | Bub1b | 701 | 24-May-15 |
| 389 | 3 | 4 | 5 | 6 | 7 | VII-2 | Tnp2 | 7142 | 4-May-15 | 485 | 3 | 4 | 5 | 6 | 7 | VII-1 | C1qa | 712 | 17-May-15 |
| 390 | 3 | 4 | 5 | 6 | 7 | VII-2 | Try10 | | | 486 | 3 | 4 | 5 | 6 | 7 | VII-1 | C1qtnf3 | 114899 | 4-May-15 |
| 391 | 3 | 4 | 5 | 6 | 7 | VII-2 | Try4 | 5647 | | 487 | 3 | 4 | 5 | 6 | 7 | VII-1 | C330027C09Rik | | |
| 392 | 3 | 4 | 5 | 6 | 7 | VII-2 | Try5 | 168330 | 4-May-15 | 488 | 3 | 4 | 5 | 6 | 7 | VII-1 | C4bp | 722, 725 | 7-Jun-15 |
| 393 | 3 | 4 | 5 | 6 | 7 | VII-2 | Ubash3a | 53347 | 24-May-15 | 489 | 3 | 4 | 5 | 6 | 7 | VII-1 | C730036E19Rik | | |
| 394 | 3 | 4 | 5 | 6 | 7 | VII-2 | Vil1 | 7429 | 12-May-15 | 490 | 3 | 4 | 5 | 6 | 7 | VII-1 | Cacna1e | 777 | 12-May-15 |
| 395 | 3 | 4 | 5 | 6 | 7 | VII-2 | Vmn2r29 | | | 491 | 3 | 4 | 5 | 6 | 7 | VII-1 | Cadm1 | 23705 | 12-May-15 |
| 396 | 3 | 4 | 5 | 6 | 7 | VII-2 | Wdr52 | 55779 | 4-May-15 | 492 | 3 | 4 | 5 | 6 | 7 | VII-1 | Camp | 820 | 7-Jun-15 |
| 397 | 3 | 4 | 5 | 6 | 7 | VII-2 | Zg16 | 653808 | 4-May-15 | 493 | 3 | 4 | 5 | 6 | 7 | VII-1 | Capn3 | 825 | 23-May-15 |
| 398 | 3 | 4 | 5 | 6 | 7 | VII-1 | 1190002F15Rik | | | 494 | 3 | 4 | 5 | 6 | 7 | VII-1 | Car12 | | |
| 399 | 3 | 4 | 5 | 6 | 7 | VII-1 | 1500011B03Rik | | | 495 | 3 | 4 | 5 | 6 | 7 | VII-1 | Car3 | 761 | 17-May-15 |
| 400 | 3 | 4 | 5 | 6 | 7 | VII-1 | 1500015O10Rik | | | 496 | 3 | 4 | 5 | 6 | 7 | VII-1 | Cd4 | 6351 | 3-May-15 |
| 401 | 3 | 4 | 5 | 6 | 7 | VII-1 | 1700018G05Rik | | | 497 | 3 | 4 | 5 | 6 | 7 | VII-1 | Cd5 | 6352 | 17-May-15 |
| 402 | 3 | 4 | 5 | 6 | 7 | VII-1 | 1700027J07Rik | | | 498 | 3 | 4 | 5 | 6 | 7 | VII-1 | Cd8 | 6355 | 4-May-15 |
| 403 | 3 | 4 | 5 | 6 | 7 | VII-1 | 1700049E15Rik | | | 499 | 3 | 4 | 5 | 6 | 7 | VII-1 | Ccna2 | 890 | 24-May-15 |
| 404 | 3 | 4 | 5 | 6 | 7 | VII-1 | 1700095A21Rik | | | 500 | 3 | 4 | 5 | 6 | 7 | VII-1 | Ccnb1 | 891 | 24-May-15 |
| 405 | 3 | 4 | 5 | 6 | 7 | VII-1 | 1700097N02Rik | | | 501 | 3 | 4 | 5 | 6 | 7 | VII-1 | Ccnb2 | 9133 | 12-May-15 |
| 406 | 3 | 4 | 5 | 6 | 7 | VII-1 | 1700120C14Rik | | | 502 | 3 | 4 | 5 | 6 | 7 | VII-1 | Ccnf | 899 | 4-May-15 |
| 407 | 3 | 4 | 5 | 6 | 7 | VII-1 | 1810009J06Rik | | | 503 | 3 | 4 | 5 | 6 | 7 | VII-1 | Ccno | 10309 | 4-May-15 |
| 408 | 3 | 4 | 5 | 6 | 7 | VII-1 | 1810019D21Rik | | | 504 | 3 | 4 | 5 | 6 | 7 | VII-1 | Cd177 | 57126 | 4-May-15 |
| 409 | 3 | 4 | 5 | 6 | 7 | VII-1 | 2010109A12Rik | | | 505 | 3 | 4 | 5 | 6 | 7 | VII-1 | Cd180 | 4064 | 17-May-15 |
| 410 | 3 | 4 | 5 | 6 | 7 | VII-1 | 2310002J15Rik | | | 506 | 3 | 4 | 5 | 6 | 7 | VII-1 | Cd19 | 930 | 12-May-15 |
| 411 | 3 | 4 | 5 | 6 | 7 | VII-1 | 2700099C18Rik | | | 507 | 3 | 4 | 5 | 6 | 7 | VII-1 | Cd24a | 100133941 | 21-May-15 |
| 412 | 3 | 4 | 5 | 6 | 7 | VII-1 | 2810417H13Rik | | | 508 | 3 | 4 | 5 | 6 | 7 | VII-1 | Cd300lf | 146722 | 4-May-15 |
| 413 | 3 | 4 | 5 | 6 | 7 | VII-1 | 4931429I13Rik | | | 509 | 3 | 4 | 5 | 6 | 7 | VII-1 | Cd37 | 951 | 4-May-15 |
| 414 | 3 | 4 | 5 | 6 | 7 | VII-1 | 5033403H07Rik | | | 510 | 3 | 4 | 5 | 6 | 7 | VII-1 | Cd52 | 1043 | 12-May-15 |
| 415 | 3 | 4 | 5 | 6 | 7 | VII-1 | 8430408G22Rik | | | 511 | 3 | 4 | 5 | 6 | 7 | VII-1 | Cd69 | 969 | 4-May-15 |
| 416 | 3 | 4 | 5 | 6 | 7 | VII-1 | 9130230L23Rik | | | 512 | 3 | 4 | 5 | 6 | 7 | VII-1 | Cd72 | 971 | 4-May-15 |
| 417 | 3 | 4 | 5 | 6 | 7 | VII-1 | 9230104L09Rik | | | 513 | 3 | 4 | 5 | 6 | 7 | VII-1 | Cd79a | 973 | 12-May-15 |
| 418 | 3 | 4 | 5 | 6 | 7 | VII-1 | AA467197 | | | 514 | 3 | 4 | 5 | 6 | 7 | VII-1 | Cd79b | 974 | 4-May-15 |
| 419 | 3 | 4 | 5 | 6 | 7 | VII-1 | Aass | 10157 | 4-May-15 | 515 | 3 | 4 | 5 | 6 | 7 | VII-1 | Cdc45 | 8318 | 4-May-15 |
| 420 | 3 | 4 | 5 | 6 | 7 | VII-1 | Acmsd | | | 516 | 3 | 4 | 5 | 6 | 7 | VII-1 | Cdca3 | 83461 | 12-May-15 |
| 421 | 3 | 4 | 5 | 6 | 7 | VII-1 | Acta1 | 58 | 23-May-15 | 517 | 3 | 4 | 5 | 6 | 7 | VII-1 | Cdca5 | 113130 | 17-May-15 |
| 422 | 3 | 4 | 5 | 6 | 7 | VII-1 | Actc1 | 70 | 23-May-15 | 518 | 3 | 4 | 5 | 6 | 7 | VII-1 | Cdca8 | 55143 | 4-May-15 |
| 423 | 3 | 4 | 5 | 6 | 7 | VII-1 | Actn2 | 88 | 23-May-15 | 519 | 3 | 4 | 5 | 6 | 7 | VII-1 | Cdk1 | 983 | 24-May-15 |
| 424 | 3 | 4 | 5 | 6 | 7 | VII-1 | Adam7 | 8756 | 4-May-15 | 520 | 3 | 4 | 5 | 6 | 7 | VII-1 | Cdkn1a | 1026 | 24-May-15 |
| 425 | 3 | 4 | 5 | 6 | 7 | VII-1 | Adam8 | 101 | 4-May-15 | 521 | 3 | 4 | 5 | 6 | 7 | VII-1 | Cdkn2a | 1029 | 24-May-15 |
| 426 | 3 | 4 | 5 | 6 | 7 | VII-1 | Adamts4 | 9507 | 7-Jun-15 | 522 | 3 | 4 | 5 | 6 | 7 | VII-1 | Cela2a | 63036 | 4-May-15 |
| 427 | 3 | 4 | 5 | 6 | 7 | VII-1 | Adamts8 | 11095 | 4-May-15 | 523 | 3 | 4 | 5 | 6 | 7 | VII-1 | Cemip | 57214 | 12-May-15 |
| 428 | 3 | 4 | 5 | 6 | 7 | VII-1 | Adamtsl2 | 9719 | 23-May-15 | 524 | 3 | 4 | 5 | 6 | 7 | VII-1 | Cenpa | 1058 | 17-May-15 |
| 429 | 3 | 4 | 5 | 6 | 7 | VII-1 | Adh7 | 131 | 12-May-15 | 525 | 3 | 4 | 5 | 6 | 7 | VII-1 | Cenpe | 1062 | 17-May-15 |
| 430 | 3 | 4 | 5 | 6 | 7 | VII-1 | Adipoq | 9370 | 24-May-15 | 526 | 3 | 4 | 5 | 6 | 7 | VII-1 | Cenpf | 1063 | 21-May-15 |
| 431 | 3 | 4 | 5 | 6 | 7 | VII-1 | AF251705 | | | 527 | 3 | 4 | 5 | 6 | 7 | VII-1 | Cenph | 64946 | 4-May-15 |
| 432 | 3 | 4 | 5 | 6 | 7 | VII-1 | AF357355 | | | 528 | 3 | 4 | 5 | 6 | 7 | VII-1 | Cenpn | 55839 | 4-May-15 |
| 433 | 3 | 4 | 5 | 6 | 7 | VII-1 | AF357399 | | | 529 | 3 | 4 | 5 | 6 | 7 | VII-1 | Cep55 | 55165 | 4-May-15 |
| 434 | 3 | 4 | 5 | 6 | 7 | VII-1 | AF357425 | | | 530 | 3 | 4 | 5 | 6 | 7 | VII-1 | Ces5a | 221223 | 4-May-15 |
| 435 | 3 | 4 | 5 | 6 | 7 | VII-1 | Agr2 | 10551 | 17-May-15 | 531 | 3 | 4 | 5 | 6 | 7 | VII-1 | Cfd | 3675 | 7-Jun-15 |
| 436 | 3 | 4 | 5 | 6 | 7 | VII-1 | Aldh3a1 | 218 | 23-May-15 | 532 | 3 | 4 | 5 | 6 | 7 | VII-1 | Ch25h | 9023 | 4-May-15 |
| 437 | 3 | 4 | 5 | 6 | 7 | VII-1 | Alpl | 249 | 23-May-15 | 533 | 3 | 4 | 5 | 6 | 7 | VII-1 | Chad | 1101 | 4-May-15 |
| 438 | 3 | 4 | 5 | 6 | 7 | VII-1 | Alppl2 | 251 | 4-May-15 | 534 | 3 | 4 | 5 | 6 | 7 | VII-1 | Chi1 | | |
| 439 | 3 | 4 | 5 | 6 | 7 | VII-1 | Amd1 | 262 | 4-May-15 | 535 | 3 | 4 | 5 | 6 | 7 | VII-1 | Chi3 | | |
| 440 | 3 | 4 | 5 | 6 | 7 | VII-1 | Amy2a5 | | | 536 | 3 | 4 | 5 | 6 | 7 | VII-1 | Chi4 | | |
| 441 | 3 | 4 | 5 | 6 | 7 | VII-1 | Angptl7 | 10218 | 12-May-15 | 537 | 3 | 4 | 5 | 6 | 7 | VII-1 | Cidec | 63924 | 4-May-15 |
| 442 | 3 | 4 | 5 | 6 | 7 | VII-1 | Ankef1 | 63926 | 4-May-15 | 538 | 3 | 4 | 5 | 6 | 7 | VII-1 | Cilp | 8483 | 12-May-15 |
| 443 | 3 | 4 | 5 | 6 | 7 | VII-1 | Ankrd1 | 27063 | 23-May-15 | 539 | 3 | 4 | 5 | 6 | 7 | VII-1 | Cited1 | 4435 | 4-May-15 |
| 444 | 3 | 4 | 5 | 6 | 7 | VII-1 | Ankrd2 | 26287 | 4-May-15 | 540 | 3 | 4 | 5 | 6 | 7 | VII-1 | Ckap2 | 26586 | 4-May-15 |
| 445 | 3 | 4 | 5 | 6 | 7 | VII-1 | Ap1s2 | 8905 | 21-May-15 | 541 | 3 | 4 | 5 | 6 | 7 | VII-1 | Ckap2l | 150468 | 12-May-15 |
| 446 | 3 | 4 | 5 | 6 | 7 | VII-1 | Ap3b2 | 8120 | 4-May-15 | 542 | 3 | 4 | 5 | 6 | 7 | VII-1 | Ckm | 1158 | 24-May-15 |
| 447 | 3 | 4 | 5 | 6 | 7 | VII-1 | Apitd1 | 378708 | 4-May-15 | 543 | 3 | 4 | 5 | 6 | 7 | VII-1 | Cks2 | 1164 | 4-May-15 |
| 448 | 3 | 4 | 5 | 6 | 7 | VII-1 | Apln | 8862 | 17-May-15 | 544 | 3 | 4 | 5 | 6 | 7 | VII-1 | Clca3 | 9629 | 4-May-15 |
| 449 | 3 | 4 | 5 | 6 | 7 | VII-1 | Apobec1 | 339 | 23-May-15 | 545 | 3 | 4 | 5 | 6 | 7 | VII-1 | Cldn18 | 51208 | 12-May-15 |
| 450 | 3 | 4 | 5 | 6 | 7 | VII-1 | Apobec2 | 10930 | 4-May-15 | 546 | 3 | 4 | 5 | 6 | 7 | VII-1 | Cldn3 | 1365 | 4-May-15 |
| 451 | 3 | 4 | 5 | 6 | 7 | VII-1 | Apol11a | | | 547 | 3 | 4 | 5 | 6 | 7 | VII-1 | Cldn4 | 1364 | 3-May-15 |
| 452 | 3 | 4 | 5 | 6 | 7 | VII-1 | Apol11b | | | 548 | 3 | 4 | 5 | 6 | 7 | VII-1 | Cldn8 | 9073 | 4-May-15 |
| 453 | 3 | 4 | 5 | 6 | 7 | VII-1 | Apol7c | | | 549 | 3 | 4 | 5 | 6 | 7 | VII-1 | Clec4e | 26253 | 4-May-15 |
| 454 | 3 | 4 | 5 | 6 | 7 | VII-1 | Apol8 | | | 550 | 3 | 4 | 5 | 6 | 7 | VII-1 | Clpsl2 | 389383 | 4-May-15 |
| 455 | 3 | 4 | 5 | 6 | 7 | VII-1 | Aqp1d1 | 81575 | 4-May-15 | 551 | 3 | 4 | 5 | 6 | 7 | VII-1 | Clu | 1191 | 12-May-15 |
| 456 | 3 | 4 | 5 | 6 | 7 | VII-1 | Aqp6 | 363 | 4-May-15 | 552 | 3 | 4 | 5 | 6 | 7 | VII-1 | Cmtm7 | 112616 | 4-May-15 |
| 457 | 3 | 4 | 5 | 6 | 7 | VII-1 | Arhgdib | 397 | 17-May-15 | 553 | 3 | 4 | 5 | 6 | 7 | VII-1 | Cnfn | 84518 | 4-May-15 |
| 458 | 3 | 4 | 5 | 6 | 7 | VII-1 | Asb11 | 140456 | 4-May-15 | 554 | 3 | 4 | 5 | 6 | 7 | VII-1 | Cnksr2 | 22866 | 13-May-15 |
| 459 | 3 | 4 | 5 | 6 | 7 | VII-1 | Asf1b | 55723 | 4-May-15 | 555 | 3 | 4 | 5 | 6 | 7 | VII-1 | Col11a1 | 1301 | 23-May-15 |
| 460 | 3 | 4 | 5 | 6 | 7 | VII-1 | Aspm | 259266 | 23-May-15 | 556 | 3 | 4 | 5 | 6 | 7 | VII-1 | Col12a1 | 1303 | 12-May-15 |
| 461 | 3 | 4 | 5 | 6 | 7 | VII-1 | Atf3 | 467 | 12-May-15 | 557 | 3 | 4 | 5 | 6 | 7 | VII-1 | Col6a5 | 256076 | 4-May-15 |
| 462 | 3 | 4 | 5 | 6 | 7 | VII-1 | Atp2a1 | 487 | 12-May-15 | 558 | 3 | 4 | 5 | 6 | 7 | VII-1 | Col8a1 | 1295 | 4-May-15 |
| 463 | 3 | 4 | 5 | 6 | 7 | VII-1 | Atp2b3 | 492 | 4-May-15 | 559 | 3 | 4 | 5 | 6 | 7 | VII-1 | Col8a2 | 1296 | 23-May-15 |
| 464 | 3 | 4 | 5 | 6 | 7 | VII-1 | Atp6v1g3 | 127124 | 4-May-15 | 560 | 3 | 4 | 5 | 6 | 7 | VII-1 | Comp | 1311 | 23-May-15 |
| 465 | 3 | 4 | 5 | 6 | 7 | VII-1 | AU015791 | | | 561 | 3 | 4 | 5 | 6 | 7 | VII-1 | Coro1a | 11151 | 4-May-15 |
| 466 | 3 | 4 | 5 | 6 | 7 | VII-1 | AU040972 | | | 562 | 3 | 4 | 5 | 6 | 7 | VII-1 | Cpb2 | 1361 | 4-May-15 |
| 467 | 3 | 4 | 5 | 6 | 7 | VII-1 | Aurkb | 9212 | 17-May-15 | | | | | | | | | | |
| 468 | 3 | 4 | 5 | 6 | 7 | VII-1 | AW549542 | | | | | | | | | | | | |

Fig. 30 - 4

| | | | | | | | | | | | | | | | | | |
|---|---|---|---|---|---|---|---|---|---|---|---|---|---|---|---|---|---|
| 563 | 3 | 4 | 5 | 6 | 7 | VII-1 | Cplx2 | 10814 | 12-May-15 | 659 | 3 | 4 | 5 | 6 | 7 | VII-1 | Fggy | 55277 | 4-May-15 |
| 564 | 3 | 4 | 5 | 6 | 7 | VII-1 | Cpn1 | 1369 | 7-Jun-15 | 660 | 3 | 4 | 5 | 6 | 7 | VII-1 | Fignl1 | 63979 | 4-May-15 |
| 565 | 3 | 4 | 5 | 6 | 7 | VII-1 | Cpne5 | 57699 | 4-May-15 | 661 | 3 | 4 | 5 | 6 | 7 | VII-1 | Fmod | 2331 | 12-May-15 |
| 566 | 3 | 4 | 5 | 6 | 7 | VII-1 | Cr2 | 1380 | 7-Jun-15 | 662 | 3 | 4 | 5 | 6 | 7 | VII-1 | Fos | 2353 | 4-May-15 |
| 567 | 3 | 4 | 5 | 6 | 7 | VII-1 | Crct1 | 54544 | 4-May-15 | 663 | 3 | 4 | 5 | 6 | 7 | VII-1 | Foxi3 | 2299 | 23-May-15 |
| 568 | 3 | 4 | 5 | 6 | 7 | VII-1 | Crhbp | 1393 | 4-May-15 | 664 | 3 | 4 | 5 | 6 | 7 | VII-1 | Foxm1 | 2305 | 17-May-15 |
| 569 | 3 | 4 | 5 | 6 | 7 | VII-1 | Crisp4 | | | 665 | 3 | 4 | 5 | 6 | 7 | VII-1 | Fut1 | 2523 | 12-May-15 |
| 570 | 3 | 4 | 5 | 6 | 7 | VII-1 | Crlf1 | 9244 | 23-May-15 | 666 | 3 | 4 | 5 | 6 | 7 | VII-1 | Gal3st4 | 79690 | 4-May-15 |
| 571 | 3 | 4 | 5 | 6 | 7 | VII-1 | Crtam | 56253 | 12-May-15 | 667 | 3 | 4 | 5 | 6 | 7 | VII-1 | Galnt12 | 79695 | 4-May-15 |
| 572 | 3 | 4 | 5 | 6 | 7 | VII-1 | Cryba4 | 1413 | 4-May-15 | 668 | 3 | 4 | 5 | 6 | 7 | VII-1 | Gbp2b | | |
| 573 | 3 | 4 | 5 | 6 | 7 | VII-1 | Csrp3 | 8048 | 23-May-15 | 669 | 3 | 4 | 5 | 6 | 7 | VII-1 | Gc | 2638 | 17-May-15 |
| 574 | 3 | 4 | 5 | 6 | 7 | VII-1 | Cst11 | 140880 | 4-May-15 | 670 | 3 | 4 | 5 | 6 | 7 | VII-1 | Gdf15 | 9518 | 4-May-15 |
| 575 | 3 | 4 | 5 | 6 | 7 | VII-1 | Ctgf | 1490 | 12-May-15 | 671 | 3 | 4 | 5 | 6 | 7 | VII-1 | Gdf6 | 392255 | 12-May-15 |
| 576 | 3 | 4 | 5 | 6 | 7 | VII-1 | Ctrb1 | 1504 | 4-May-15 | 672 | 3 | 4 | 5 | 6 | 7 | VII-1 | Gfra1 | 2674 | 12-May-15 |
| 577 | 3 | 4 | 5 | 6 | 7 | VII-1 | Ctse | 1510 | 12-May-15 | 673 | 3 | 4 | 5 | 6 | 7 | VII-1 | Gh | 2688 | 7-Jun-15 |
| 578 | 3 | 4 | 5 | 6 | 7 | VII-1 | Ctss | 1920 | 24-May-15 | 674 | 3 | 4 | 5 | 6 | 7 | VII-1 | Gldc | 2731 | 23-May-15 |
| 579 | 3 | 4 | 5 | 6 | 7 | VII-1 | Cuzd1 | 50624 | 4-May-15 | 675 | 3 | 4 | 5 | 6 | 7 | VII-1 | Glycam1 | 644076 | 4-May-15 |
| 580 | 3 | 4 | 5 | 6 | 7 | VII-1 | Cxcl13 | 10563 | 3-May-15 | 676 | 3 | 4 | 5 | 6 | 7 | VII-1 | Gm1110 | | |
| 581 | 3 | 4 | 5 | 6 | 7 | VII-1 | Cxcl15 | | | 677 | 3 | 4 | 5 | 6 | 7 | VII-1 | Gm11346 | | |
| 582 | 3 | 4 | 5 | 6 | 7 | VII-1 | Cxcl17 | 284340 | 4-May-15 | 678 | 3 | 4 | 5 | 6 | 7 | VII-1 | Gm12191 | | |
| 583 | 3 | 4 | 5 | 6 | 7 | VII-1 | Cxcl2 | 2920 | 12-May-15 | 679 | 3 | 4 | 5 | 6 | 7 | VII-1 | Gm12238 | | |
| 584 | 3 | 4 | 5 | 6 | 7 | VII-1 | Cxcl3 | 2921 | 12-May-15 | 680 | 3 | 4 | 5 | 6 | 7 | VII-1 | Gm15056 | | |
| 585 | 3 | 4 | 5 | 6 | 7 | VII-1 | Cxcr2 | 3579 | 17-May-15 | 681 | 3 | 4 | 5 | 6 | 7 | VII-1 | Gm15386 | | |
| 586 | 3 | 4 | 5 | 6 | 7 | VII-1 | Cxcr4 | 7852 | 21-May-15 | 682 | 3 | 4 | 5 | 6 | 7 | VII-1 | Gm17727 | | |
| 587 | 3 | 4 | 5 | 6 | 7 | VII-1 | Cxcr5 | 643 | 17-May-15 | 683 | 3 | 4 | 5 | 6 | 7 | VII-1 | Gm1987 | | |
| 588 | 3 | 4 | 5 | 6 | 7 | VII-1 | Cxcr6 | 10663 | 14-May-15 | 684 | 3 | 4 | 5 | 6 | 7 | VII-1 | Gm2083 | | |
| 589 | 3 | 4 | 5 | 6 | 7 | VII-1 | Cyb561 | 1534 | 12-May-15 | 685 | 3 | 4 | 5 | 6 | 7 | VII-1 | Gm266 | | |
| 590 | 3 | 4 | 5 | 6 | 7 | VII-1 | Cyp2a5 | | | 686 | 3 | 4 | 5 | 6 | 7 | VII-1 | Gm2663 | | |
| 591 | 3 | 4 | 5 | 6 | 7 | VII-1 | Cyp2e1 | 1571 | 24-May-15 | 687 | 3 | 4 | 5 | 6 | 7 | VII-1 | Gm4759 | | |
| 592 | 3 | 4 | 5 | 6 | 7 | VII-1 | Cyp2f2 | | | 688 | 3 | 4 | 5 | 6 | 7 | VII-1 | Gm4846 | | |
| 593 | 3 | 4 | 5 | 6 | 7 | VII-1 | Cyp46a1 | 10858 | 4-May-15 | 689 | 3 | 4 | 5 | 6 | 7 | VII-1 | Gm4952 | | |
| 594 | 3 | 4 | 5 | 6 | 7 | VII-1 | Cyp4a10 | | | 690 | 3 | 4 | 5 | 6 | 7 | VII-1 | Gm5483 | | |
| 595 | 3 | 4 | 5 | 6 | 7 | VII-1 | Cyp4a14 | | | 691 | 3 | 4 | 5 | 6 | 7 | VII-1 | Gm5531 | | |
| 596 | 3 | 4 | 5 | 6 | 7 | VII-1 | D730048I06Rik | | | 692 | 3 | 4 | 5 | 6 | 7 | VII-1 | Gm6040 | | |
| 597 | 3 | 4 | 5 | 6 | 7 | VII-1 | Dck | 1633 | 12-May-15 | 693 | 3 | 4 | 5 | 6 | 7 | VII-1 | Gm6642 | | |
| 598 | 3 | 4 | 5 | 6 | 7 | VII-1 | Defb1 | 1672 | 10-May-15 | 694 | 3 | 4 | 5 | 6 | 7 | VII-1 | Gm6792 | | |
| 599 | 3 | 4 | 5 | 6 | 7 | VII-1 | Defb10 | 245913 | 4-May-15 | 695 | 3 | 4 | 5 | 6 | 7 | VII-1 | Gm7325 | | |
| 600 | 3 | 4 | 5 | 6 | 7 | VII-1 | Defb12 | 245915 | 4-May-15 | 696 | 3 | 4 | 5 | 6 | 7 | VII-1 | Gm7334 | | |
| 601 | 3 | 4 | 5 | 6 | 7 | VII-1 | Defb13 | 245927 | 4-May-15 | 697 | 3 | 4 | 5 | 6 | 7 | VII-1 | Gm933 | | |
| 602 | 3 | 4 | 5 | 6 | 7 | VII-1 | Defb15 | 245929 | 4-May-15 | 698 | 3 | 4 | 5 | 6 | 7 | VII-1 | Gpc2 | 221914 | 4-May-15 |
| 603 | 3 | 4 | 5 | 6 | 7 | VII-1 | Defb18 | 117285 | 4-May-15 | 699 | 3 | 4 | 5 | 6 | 7 | VII-1 | Gpr35 | 2859 | 4-May-15 |
| 604 | 3 | 4 | 5 | 6 | 7 | VII-1 | Defb19 | 245932 | 4-May-15 | 700 | 3 | 4 | 5 | 6 | 7 | VII-1 | Gpr82 | 27197 | 12-May-15 |
| 605 | 3 | 4 | 5 | 6 | 7 | VII-1 | Defb2 | 1673 | 10-May-15 | 701 | 3 | 4 | 5 | 6 | 7 | VII-1 | Gprc5a | 9052 | 4-May-15 |
| 606 | 3 | 4 | 5 | 6 | 7 | VII-1 | Defb20 | 245932 | 4-May-15 | 702 | 3 | 4 | 5 | 6 | 7 | VII-1 | Gpx5 | 2880 | 4-May-15 |
| 607 | 3 | 4 | 5 | 6 | 7 | VII-1 | Defb21 | 245934 | 4-May-15 | 703 | 3 | 4 | 5 | 6 | 7 | VII-1 | Grhl2 | 79977 | 24-May-15 |
| 608 | 3 | 4 | 5 | 6 | 7 | VII-1 | Defb23 | 245936 | 4-May-15 | 704 | 3 | 4 | 5 | 6 | 7 | VII-1 | Gtse1 | 51512 | 12-May-15 |
| 609 | 3 | 4 | 5 | 6 | 7 | VII-1 | Defb25 | 245938 | 4-May-15 | 705 | 3 | 4 | 5 | 6 | 7 | VII-1 | Gvin1 | 387751 | 4-May-15 |
| 610 | 3 | 4 | 5 | 6 | 7 | VII-1 | Defb26 | 81623 | 4-May-15 | 706 | 3 | 4 | 5 | 6 | 7 | VII-1 | H2-Ea-ps | | |
| 611 | 3 | 4 | 5 | 6 | 7 | VII-1 | Defb28 | 245939 | 4-May-15 | 707 | 3 | 4 | 5 | 6 | 7 | VII-1 | H2-Eb1 | | |
| 612 | 3 | 4 | 5 | 6 | 7 | VII-1 | Defb29 | 140881 | 4-May-15 | 708 | 3 | 4 | 5 | 6 | 7 | VII-1 | H2-M2 | | |
| 613 | 3 | 4 | 5 | 6 | 7 | VII-1 | Defb30 | 245940 | 4-May-15 | 709 | 3 | 4 | 5 | 6 | 7 | VII-1 | Havcr1 | 26762 | 13-May-15 |
| 614 | 3 | 4 | 5 | 6 | 7 | VII-1 | Defb35 | | | 710 | 3 | 4 | 5 | 6 | 7 | VII-1 | Hba-a1 | | |
| 615 | 3 | 4 | 5 | 6 | 7 | VII-1 | Defb39 | | | 711 | 3 | 4 | 5 | 6 | 7 | VII-1 | Hbb-bh2 | | |
| 616 | 3 | 4 | 5 | 6 | 7 | VII-1 | Defb4 | 1673 | 7-Jun-15 | 712 | 3 | 4 | 5 | 6 | 7 | VII-1 | Hmgb2 | 3148 | 4-May-15 |
| 617 | 3 | 4 | 5 | 6 | 7 | VII-1 | Defb41 | | | 713 | 3 | 4 | 5 | 6 | 7 | VII-1 | Hmmr | 3161 | 23-May-15 |
| 618 | 3 | 4 | 5 | 6 | 7 | VII-1 | Defb42 | | | 714 | 3 | 4 | 5 | 6 | 7 | VII-1 | Hp | 3240 | 7-Jun-15 |
| 619 | 3 | 4 | 5 | 6 | 7 | VII-1 | Defb45 | | | 715 | 3 | 4 | 5 | 6 | 7 | VII-1 | Hspa1a | 3303 | 20-May-15 |
| 620 | 3 | 4 | 5 | 6 | 7 | VII-1 | Defb47 | | | 716 | 3 | 4 | 5 | 6 | 7 | VII-1 | Hspa1b | 3304 | 20-May-15 |
| 621 | 3 | 4 | 5 | 6 | 7 | VII-1 | Defb48 | | | 717 | 3 | 4 | 5 | 6 | 7 | VII-1 | Ido1 | 3620 | 24-May-15 |
| 622 | 3 | 4 | 5 | 6 | 7 | VII-1 | Depdc7 | 91614 | 4-May-15 | 718 | 3 | 4 | 5 | 6 | 7 | VII-1 | Ifi27l2a | | |
| 623 | 3 | 4 | 5 | 6 | 7 | VII-1 | Derl3 | 91319 | 3-May-15 | 719 | 3 | 4 | 5 | 6 | 7 | VII-1 | Igfbp1 | 3484 | 17-May-15 |
| 624 | 3 | 4 | 5 | 6 | 7 | VII-1 | Dio1 | 1733 | 10-Jun-15 | 720 | 3 | 4 | 5 | 6 | 7 | VII-1 | Igj | 3512 | 12-May-15 |
| 625 | 3 | 4 | 5 | 6 | 7 | VII-1 | Dio2 | 1734 | 17-May-15 | 721 | 3 | 4 | 5 | 6 | 7 | VII-1 | Igll1 | 3543 | 12-May-15 |
| 626 | 3 | 4 | 5 | 6 | 7 | VII-1 | Dlgap5 | 9787 | 4-May-15 | 722 | 3 | 4 | 5 | 6 | 7 | VII-1 | Ikzf3 | 22806 | 4-May-15 |
| 627 | 3 | 4 | 5 | 6 | 7 | VII-1 | Dmrtc1a | | | 723 | 3 | 4 | 5 | 6 | 7 | VII-1 | Il12a | 3592 | 17-May-15 |
| 628 | 3 | 4 | 5 | 6 | 7 | VII-1 | Dnase1l2 | 1775 | 12-May-15 | 724 | 3 | 4 | 5 | 6 | 7 | VII-1 | Il1b | 3553 | 24-May-15 |
| 629 | 3 | 4 | 5 | 6 | 7 | VII-1 | DQ267100 | | | 725 | 3 | 4 | 5 | 6 | 7 | VII-1 | Il1r2 | 7850 | 23-May-15 |
| 630 | 3 | 4 | 5 | 6 | 7 | VII-1 | DQ267101 | | | 726 | 3 | 4 | 5 | 6 | 7 | VII-1 | Il1rn | 3557 | 23-May-15 |
| 631 | 3 | 4 | 5 | 6 | 7 | VII-1 | DQ267102 | | | 727 | 3 | 4 | 5 | 6 | 7 | VII-1 | Il22ra2 | 116379 | 4-May-15 |
| 632 | 3 | 4 | 5 | 6 | 7 | VII-1 | Dtl | 51514 | 7-Jun-15 | 728 | 3 | 4 | 5 | 6 | 7 | VII-1 | Il2ra | 3559 | 17-May-15 |
| 633 | 3 | 4 | 5 | 6 | 7 | VII-1 | Dusp2 | 1844 | 4-May-15 | 729 | 3 | 4 | 5 | 6 | 7 | VII-1 | Il6 | 3569 | 24-May-15 |
| 634 | 3 | 4 | 5 | 6 | 7 | VII-1 | E2f8 | 79733 | 12-May-15 | 730 | 3 | 4 | 5 | 6 | 7 | VII-1 | Il7r | 3575 | 4-May-15 |
| 635 | 3 | 4 | 5 | 6 | 7 | VII-1 | E330020D12Rik | | | 731 | 3 | 4 | 5 | 6 | 7 | VII-1 | Inha | 3623 | 12-May-15 |
| 636 | 3 | 4 | 5 | 6 | 7 | VII-1 | Ear7 | 7067 | 12-May-15 | 732 | 3 | 4 | 5 | 6 | 7 | VII-1 | Inhbb | 3625 | 4-May-15 |
| 637 | 3 | 4 | 5 | 6 | 7 | VII-1 | Ebf1 | 1879 | 12-May-15 | 733 | 3 | 4 | 5 | 6 | 7 | VII-1 | Inpp5d | 3635 | 12-May-15 |
| 638 | 3 | 4 | 5 | 6 | 7 | VII-1 | Eddm3b | 64184 | 4-May-15 | 734 | 3 | 4 | 5 | 6 | 7 | VII-1 | Irf4 | 3662 | 24-May-15 |
| 639 | 3 | 4 | 5 | 6 | 7 | VII-1 | Eef1a2 | 1917 | 4-May-15 | 735 | 3 | 4 | 5 | 6 | 7 | VII-1 | Irg1 | 730249 | 4-May-15 |
| 640 | 3 | 4 | 5 | 6 | 7 | VII-1 | Egr2 | 1959 | 23-May-15 | 736 | 3 | 4 | 5 | 6 | 7 | VII-1 | Isg20 | 3669 | 12-May-15 |
| 641 | 3 | 4 | 5 | 6 | 7 | VII-1 | Eif3j1 | | | 737 | 3 | 4 | 5 | 6 | 7 | VII-1 | Ism1 | 140862 | 4-May-15 |
| 642 | 3 | 4 | 5 | 6 | 7 | VII-1 | Eln | 2006 | 23-May-15 | 738 | 3 | 4 | 5 | 6 | 7 | VII-1 | Itih4 | 3700 | 17-May-15 |
| 643 | 3 | 4 | 5 | 6 | 7 | VII-1 | Elovl2 | 54898 | 4-May-15 | 739 | 3 | 4 | 5 | 6 | 7 | VII-1 | Itln1 | 55600 | 17-May-15 |
| 644 | 3 | 4 | 5 | 6 | 7 | VII-1 | Enpp1 | 5167 | 23-May-15 | 740 | 3 | 4 | 5 | 6 | 7 | VII-1 | Jakmip1 | 152789 | 12-May-15 |
| 645 | 3 | 4 | 5 | 6 | 7 | VII-1 | Esco2 | 157570 | 23-May-15 | 741 | 3 | 4 | 5 | 6 | 7 | VII-1 | Kap | | |
| 646 | 3 | 4 | 5 | 6 | 7 | VII-1 | Esrp2 | 80004 | 4-May-15 | 742 | 3 | 4 | 5 | 6 | 7 | VII-1 | Kcnc4 | 3749 | 4-May-15 |
| 647 | 3 | 4 | 5 | 6 | 7 | VII-1 | Ezh2 | 2146 | 23-May-15 | 743 | 3 | 4 | 5 | 6 | 7 | VII-1 | Kcnh3 | 23416 | 4-May-15 |
| 648 | 3 | 4 | 5 | 6 | 7 | VII-1 | F10 | 2159 | 7-Jun-15 | 744 | 3 | 4 | 5 | 6 | 7 | VII-1 | Kcnmb4 | 27345 | 4-May-15 |
| 649 | 3 | 4 | 5 | 6 | 7 | VII-1 | Faim2 | 23017 | 4-May-15 | 745 | 3 | 4 | 5 | 6 | 7 | VII-1 | Kif11 | 3832 | 4-May-15 |
| 650 | 3 | 4 | 5 | 6 | 7 | VII-1 | Fam101a | 144347 | 4-May-15 | 746 | 3 | 4 | 5 | 6 | 7 | VII-1 | Kif15 | 56992 | 17-May-15 |
| 651 | 3 | 4 | 5 | 6 | 7 | VII-1 | Fam129c | 199786 | 4-May-15 | 747 | 3 | 4 | 5 | 6 | 7 | VII-1 | Kif18b | 146909 | 4-May-15 |
| 652 | 3 | 4 | 5 | 6 | 7 | VII-1 | Fam64a | 54478 | 4-May-15 | 748 | 3 | 4 | 5 | 6 | 7 | VII-1 | Kif22 | 3835 | 4-May-15 |
| 653 | 3 | 4 | 5 | 6 | 7 | VII-1 | Fam84a | 151354 | 12-May-15 | 749 | 3 | 4 | 5 | 6 | 7 | VII-1 | Kif2c | 11004 | 4-May-15 |
| 654 | 3 | 4 | 5 | 6 | 7 | VII-1 | Fcgr4 | | | 750 | 3 | 4 | 5 | 6 | 7 | VII-1 | Kifc1 | 3833 | 4-May-15 |
| 655 | 3 | 4 | 5 | 6 | 7 | VII-1 | Fcho1 | 23149 | 4-May-15 | 751 | 3 | 4 | 5 | 6 | 7 | VII-1 | Kifc5b | | |
| 656 | 3 | 4 | 5 | 6 | 7 | VII-1 | Fcna | 84824 | 4-May-15 | 752 | 3 | 4 | 5 | 6 | 7 | VII-1 | Klhl23 | 151230 | 4-May-15 |
| 657 | 3 | 4 | 5 | 6 | 7 | VII-1 | Fetub | 26998 | 12-May-15 | 753 | 3 | 4 | 5 | 6 | 7 | VII-1 | Klhl34 | 257240 | 4-May-15 |
| 658 | 3 | 4 | 5 | 6 | 7 | VII-1 | Ffar1 | 2864 | 17-May-15 | 754 | 3 | 4 | 5 | 6 | 7 | VII-1 | Klhl6 | 89857 | 7-Jun-15 |

Fig. 30 - 5

| # | | | | | | | Gene | ID | Date | # | | | | | | | Gene | ID | Date |
|---|---|---|---|---|---|---|---|---|---|---|---|---|---|---|---|---|---|---|---|
| 755 | 3 | 4 | 5 | 6 | 7 | VII-1 | Knstrn | 90417 | 4-May-15 | 845 | 3 | 4 | 5 | 6 | 7 | VII-1 | Mir140 | 406932 | 21-May-15 |
| 756 | 3 | 4 | 5 | 6 | 7 | VII-1 | Krt33 | 3860 | 7-Jun-15 | 846 | 3 | 4 | 5 | 6 | 7 | VII-1 | Mir141 | 406933 | 21-May-15 |
| 757 | 3 | 4 | 5 | 6 | 7 | VII-1 | Krt14 | 3861 | 23-May-15 | 847 | 3 | 4 | 5 | 6 | 7 | VII-1 | Mir142 | 406934 | 21-May-15 |
| 758 | 3 | 4 | 5 | 6 | 7 | VII-1 | Krt35 | 3866 | 4-May-15 | 848 | 3 | 4 | 5 | 6 | 7 | VII-1 | Mir142b | | |
| 759 | 3 | 4 | 5 | 6 | 7 | VII-1 | Krt18 | 3875 | 24-May-15 | 849 | 3 | 4 | 5 | 6 | 7 | VII-1 | Mir143 | 406935 | 21-May-15 |
| 760 | 3 | 4 | 5 | 6 | 7 | VII-1 | Krt4 | 3851 | 4-May-15 | 850 | 3 | 4 | 5 | 6 | 7 | VII-1 | Mir144 | 406936 | 21-May-15 |
| 761 | 3 | 4 | 5 | 6 | 7 | VII-1 | Krt5 | 3852 | 23-May-15 | 851 | 3 | 4 | 5 | 6 | 7 | VII-1 | Mir145 | 406937 | 24-May-15 |
| 762 | 3 | 4 | 5 | 6 | 7 | VII-1 | krt78 | 196374 | 4-May-15 | 852 | 3 | 4 | 5 | 6 | 7 | VII-1 | Mir146 | | |
| 763 | 3 | 4 | 5 | 6 | 7 | VII-1 | Laptm5 | 7805 | 4-May-15 | 853 | 3 | 4 | 5 | 6 | 7 | VII-1 | Mir147 | 406939 | 4-May-15 |
| 764 | 3 | 4 | 5 | 6 | 7 | VII-1 | Lars2 | 23395 | 4-May-15 | 854 | 3 | 4 | 5 | 6 | 7 | VII-1 | Mir149 | 406941 | 21-May-15 |
| 765 | 3 | 4 | 5 | 6 | 7 | VII-1 | Lce1a1 | | | 855 | 3 | 4 | 5 | 6 | 7 | VII-1 | Mir150 | 406942 | 21-May-15 |
| 766 | 3 | 4 | 5 | 6 | 7 | VII-1 | Lce1a2 | | | 856 | 3 | 4 | 5 | 6 | 7 | VII-1 | Mir154 | 406946 | 21-May-15 |
| 767 | 3 | 4 | 5 | 6 | 7 | VII-1 | Lce1b | 353132 | 4-May-15 | 857 | 3 | 4 | 5 | 6 | 7 | VII-1 | Mir155 | 406947 | 21-May-15 |
| 768 | 3 | 4 | 5 | 6 | 7 | VII-1 | Lce1d | 353134 | 4-May-15 | 858 | 3 | 4 | 5 | 6 | 7 | VII-1 | Mir15a | 406948 | 21-May-15 |
| 769 | 3 | 4 | 5 | 6 | 7 | VII-1 | Lce3a | 353142 | 4-May-15 | 859 | 3 | 4 | 5 | 6 | 7 | VII-1 | Mir16-1 | 406950 | 21-May-15 |
| 770 | 3 | 4 | 5 | 6 | 7 | VII-1 | Lce3b | 353143 | 4-May-15 | 860 | 3 | 4 | 5 | 6 | 7 | VII-1 | Mir1668 | | |
| 771 | 3 | 4 | 5 | 6 | 7 | VII-1 | Lce3c | 353144 | 4-May-15 | 861 | 3 | 4 | 5 | 6 | 7 | VII-1 | Mir17 | 406952 | 24-May-15 |
| 772 | 3 | 4 | 5 | 6 | 7 | VII-1 | Lce3d | 84648 | 4-May-15 | 862 | 3 | 4 | 5 | 6 | 7 | VII-1 | Mir18 | 406953 | 21-May-15 |
| 773 | 3 | 4 | 5 | 6 | 7 | VII-1 | Lce3e | 353145 | 4-May-15 | 863 | 3 | 4 | 5 | 6 | 7 | VII-1 | Mir181a-1 | | |
| 774 | 3 | 4 | 5 | 6 | 7 | VII-1 | Lce3f | | | 864 | 3 | 4 | 5 | 6 | 7 | VII-1 | Mir181a-2 | | |
| 775 | 3 | 4 | 5 | 6 | 7 | VII-1 | Lcn12 | 286256 | 4-May-15 | 865 | 3 | 4 | 5 | 6 | 7 | VII-1 | Mir181b-1 | | |
| 776 | 3 | 4 | 5 | 6 | 7 | VII-1 | Lcn2 | 3934 | 17-May-15 | 866 | 3 | 4 | 5 | 6 | 7 | VII-1 | Mir181b-2 | | |
| 777 | 3 | 4 | 5 | 6 | 7 | VII-1 | Lcn5 | 353176 | | 867 | 3 | 4 | 5 | 6 | 7 | VII-1 | Mir181c | 406957 | 21-May-15 |
| 778 | 3 | 4 | 5 | 6 | 7 | VII-1 | Lcn6 | 158062 | 4-May-15 | 868 | 3 | 4 | 5 | 6 | 7 | VII-1 | Mir181d | 574457 | 21-May-15 |
| 779 | 3 | 4 | 5 | 6 | 7 | VII-1 | Lcn8 | 138307 | 12-May-15 | 869 | 3 | 4 | 5 | 6 | 7 | VII-1 | Mir1839 | | |
| 780 | 3 | 4 | 5 | 6 | 7 | VII-1 | Lcn9 | 392399 | 4-May-15 | 870 | 3 | 4 | 5 | 6 | 7 | VII-1 | Mir1843 | | |
| 781 | 3 | 4 | 5 | 6 | 7 | VII-1 | Ldb3 | 11155 | 23-May-15 | 871 | 3 | 4 | 5 | 6 | 7 | VII-1 | Mir1843b | | |
| 782 | 3 | 4 | 5 | 6 | 7 | VII-1 | Lef1 | 51176 | 12-May-15 | 872 | 3 | 4 | 5 | 6 | 7 | VII-1 | Mir185 | 406961 | 24-May-15 |
| 783 | 3 | 4 | 5 | 6 | 7 | VII-1 | Lgals3 | 3958 | 24-May-15 | 873 | 3 | 4 | 5 | 6 | 7 | VII-1 | Mir186 | 406962 | 21-May-15 |
| 784 | 3 | 4 | 5 | 6 | 7 | VII-1 | Lgr5 | 8549 | 17-May-15 | 874 | 3 | 4 | 5 | 6 | 7 | VII-1 | Mir187 | 406963 | 21-May-15 |
| 785 | 3 | 4 | 5 | 6 | 7 | VII-1 | Lingo1 | 84894 | 12-May-15 | 875 | 3 | 4 | 5 | 6 | 7 | VII-1 | Mir1892 | | |
| 786 | 3 | 4 | 5 | 6 | 7 | VII-1 | Llpg | 9388 | 12-May-15 | 876 | 3 | 4 | 5 | 6 | 7 | VII-1 | Mir1893 | | |
| 787 | 3 | 4 | 5 | 6 | 7 | VII-1 | Lmnb1 | 4001 | 4-May-15 | 877 | 3 | 4 | 5 | 6 | 7 | VII-1 | Mir1894 | | |
| 788 | 3 | 4 | 5 | 6 | 7 | VII-1 | LOC547349 | | | 878 | 3 | 4 | 5 | 6 | 7 | VII-1 | Mir1895 | | |
| 789 | 3 | 4 | 5 | 6 | 7 | VII-1 | Lor | 4014 | 4-May-15 | 879 | 3 | 4 | 5 | 6 | 7 | VII-1 | Mir1897 | | |
| 790 | 3 | 4 | 5 | 6 | 7 | VII-1 | Lox | 4015 | 12-May-15 | 880 | 3 | 4 | 5 | 6 | 7 | VII-1 | Mir1898 | | |
| 791 | 3 | 4 | 5 | 6 | 7 | VII-1 | Loxl3 | 84695 | 23-May-15 | 881 | 3 | 4 | 5 | 6 | 7 | VII-1 | Mir1899 | | |
| 792 | 3 | 4 | 5 | 6 | 7 | VII-1 | Lpin1 | 23175 | 4-May-15 | 882 | 3 | 4 | 5 | 6 | 7 | VII-1 | Mir1900 | | |
| 793 | 3 | 4 | 5 | 6 | 7 | VII-1 | Lrcol1 | 100507055 | 4-May-15 | 883 | 3 | 4 | 5 | 6 | 7 | VII-1 | Mir1901 | | |
| 794 | 3 | 4 | 5 | 6 | 7 | VII-1 | Lrmp | 4033 | 4-May-15 | 884 | 3 | 4 | 5 | 6 | 7 | VII-1 | Mir1902 | | |
| 795 | 3 | 4 | 5 | 6 | 7 | VII-1 | Ltbp2 | 4053 | 7-Jun-15 | 885 | 3 | 4 | 5 | 6 | 7 | VII-1 | Mir1904 | | |
| 796 | 3 | 4 | 5 | 6 | 7 | VII-1 | Ly6g5b | 58496 | 21-May-15 | 886 | 3 | 4 | 5 | 6 | 7 | VII-1 | Mir1905 | | |
| 797 | 3 | 4 | 5 | 6 | 7 | VII-1 | Ly6g5c | 80741 | 4-May-15 | 887 | 3 | 4 | 5 | 6 | 7 | VII-1 | Mir1906-1 | | |
| 798 | 3 | 4 | 5 | 6 | 7 | VII-1 | Ly9 | 4063 | 4-May-15 | 888 | 3 | 4 | 5 | 6 | 7 | VII-1 | Mir1906-2 | | |
| 799 | 3 | 4 | 5 | 6 | 7 | VII-1 | Mal | 4118 | 7-Jun-15 | 889 | 3 | 4 | 5 | 6 | 7 | VII-1 | Mir1907 | | |
| 800 | 3 | 4 | 5 | 6 | 7 | VII-1 | Man1a | | | 890 | 3 | 4 | 5 | 6 | 7 | VII-1 | Mir191 | 406966 | 21-May-15 |
| 801 | 3 | 4 | 5 | 6 | 7 | VII-1 | Marco | 8685 | 17-May-15 | 891 | 3 | 4 | 5 | 6 | 7 | VII-1 | Mir192 | 406967 | 21-May-15 |
| 802 | 3 | 4 | 5 | 6 | 7 | VII-1 | Matn4 | 8785 | 4-May-15 | 892 | 3 | 4 | 5 | 6 | 7 | VII-1 | Mir1929 | | |
| 803 | 3 | 4 | 5 | 6 | 7 | VII-1 | Mb | 4151 | 12-May-15 | 893 | 3 | 4 | 5 | 6 | 7 | VII-1 | Mir193 | | |
| 804 | 3 | 4 | 5 | 6 | 7 | VII-1 | Mbnl3 | 55796 | 4-May-15 | 894 | 3 | 4 | 5 | 6 | 7 | VII-1 | Mir1930 | | |
| 805 | 3 | 4 | 5 | 6 | 7 | VII-1 | Mboat2 | 129642 | 4-May-15 | 895 | 3 | 4 | 5 | 6 | 7 | VII-1 | Mir1932 | | |
| 806 | 3 | 4 | 5 | 6 | 7 | VII-1 | Mfap4 | 4239 | 4-May-15 | 896 | 3 | 4 | 5 | 6 | 7 | VII-1 | Mir1933 | | |
| 807 | 3 | 4 | 5 | 6 | 7 | VII-1 | Mfrp | 83552 | 4-May-15 | 897 | 3 | 4 | 5 | 6 | 7 | VII-1 | Mir1934 | | |
| 808 | 3 | 4 | 5 | 6 | 7 | VII-1 | Mfsd2a | 84879 | 4-May-15 | 898 | 3 | 4 | 5 | 6 | 7 | VII-1 | Mir1936 | | |
| 809 | 3 | 4 | 5 | 6 | 7 | VII-1 | Mir100 | 406892 | 21-May-15 | 899 | 3 | 4 | 5 | 6 | 7 | VII-1 | Mir1938 | | |
| 810 | 3 | 4 | 5 | 6 | 7 | VII-1 | Mir101b | | | 900 | 3 | 4 | 5 | 6 | 7 | VII-1 | Mir193b | 574455 | 21-May-15 |
| 811 | 3 | 4 | 5 | 6 | 7 | VII-1 | Mir103-2 | 406896 | 21-May-15 | 901 | 3 | 4 | 5 | 6 | 7 | VII-1 | Mir1940 | | |
| 812 | 3 | 4 | 5 | 6 | 7 | VII-1 | Mir106b | 406900 | 21-May-15 | 902 | 3 | 4 | 5 | 6 | 7 | VII-1 | Mir1941 | 406969 | 21-May-15 |
| 813 | 3 | 4 | 5 | 6 | 7 | VII-1 | Mir107 | 406901 | 21-May-15 | 903 | 3 | 4 | 5 | 6 | 7 | VII-1 | Mir194-1 | 406969 | 21-May-15 |
| 814 | 3 | 4 | 5 | 6 | 7 | VII-1 | Mir10a | 406902 | 21-May-15 | 904 | 3 | 4 | 5 | 6 | 7 | VII-1 | Mir1942 | 406970 | 21-May-15 |
| 815 | 3 | 4 | 5 | 6 | 7 | VII-1 | Mir10b | 406903 | 21-May-15 | 905 | 3 | 4 | 5 | 6 | 7 | VII-1 | Mir194-2 | 406970 | 21-May-15 |
| 816 | 3 | 4 | 5 | 6 | 7 | VII-1 | Mir1190 | | | 906 | 3 | 4 | 5 | 6 | 7 | VII-1 | Mir1943 | | |
| 817 | 3 | 4 | 5 | 6 | 7 | VII-1 | Mir1191b | | | 907 | 3 | 4 | 5 | 6 | 7 | VII-1 | Mir1945 | | |
| 818 | 3 | 4 | 5 | 6 | 7 | VII-1 | Mir1192 | | | 908 | 3 | 4 | 5 | 6 | 7 | VII-1 | Mir1948 | | |
| 819 | 3 | 4 | 5 | 6 | 7 | VII-1 | Mir1199 | 102466515 | 4-May-15 | 909 | 3 | 4 | 5 | 6 | 7 | VII-1 | Mir1949 | | |
| 820 | 3 | 4 | 5 | 6 | 7 | VII-1 | Mir1224 | 100187716 | 21-May-15 | 910 | 3 | 4 | 5 | 6 | 7 | VII-1 | Mir195 | 406971 | 21-May-15 |
| 821 | 3 | 4 | 5 | 6 | 7 | VII-1 | Mir1231 | 100302158 | 4-May-15 | 911 | 3 | 4 | 5 | 6 | 7 | VII-1 | Mir1953 | | |
| | | | | | | | | | | 912 | 3 | 4 | 5 | 6 | 7 | VII-1 | Mir1955 | | |
| 822 | 3 | 4 | 5 | 6 | 7 | VII-1 | Mir1247 | 100302145 | 21-May-15 | 913 | 3 | 4 | 5 | 6 | 7 | VII-1 | Mir1956 | | |
| 823 | 3 | 4 | 5 | 6 | 7 | VII-1 | Mir1249 | 100302149 | 4-May-15 | 914 | 3 | 4 | 5 | 6 | 7 | VII-1 | Mir1957b | | |
| 824 | 3 | 4 | 5 | 6 | 7 | VII-1 | Mir124a-3 | | | 915 | 3 | 4 | 5 | 6 | 7 | VII-1 | Mir1960 | | |
| 825 | 3 | 4 | 5 | 6 | 7 | VII-1 | Mir1251 | 100302289 | 4-May-15 | 916 | 3 | 4 | 5 | 6 | 7 | VII-1 | Mir1964 | | |
| | | | | | | | | | | 917 | 3 | 4 | 5 | 6 | 7 | VII-1 | Mir1966 | | |
| 826 | 3 | 4 | 5 | 6 | 7 | VII-1 | Mir1258 | 100302172 | 21-May-15 | 918 | 3 | 4 | 5 | 6 | 7 | VII-1 | Mir1967 | | |
| | | | | | | | | | | 919 | 3 | 4 | 5 | 6 | 7 | VII-1 | Mir1968 | | |
| 827 | 3 | 4 | 5 | 6 | 7 | VII-1 | Mir125a | 406910 | 24-May-15 | 920 | 3 | 4 | 5 | 6 | 7 | VII-1 | Mir1969 | | |
| 828 | 3 | 4 | 5 | 6 | 7 | VII-1 | Mir125b-1 | | | 921 | 3 | 4 | 5 | 6 | 7 | VII-1 | Mir196b | 442920 | 21-May-15 |
| 829 | 3 | 4 | 5 | 6 | 7 | VII-1 | Mir125b-2 | | | 922 | 3 | 4 | 5 | 6 | 7 | VII-1 | Mir1981 | | |
| 830 | 3 | 4 | 5 | 6 | 7 | VII-1 | Mir126 | 406913 | 21-May-15 | 923 | 3 | 4 | 5 | 6 | 7 | VII-1 | Mir199a-1 | | |
| 831 | 3 | 4 | 5 | 6 | 7 | VII-1 | Mir126b | | | 924 | 3 | 4 | 5 | 6 | 7 | VII-1 | Mir199b | 406978 | 21-May-15 |
| 832 | 3 | 4 | 5 | 6 | 7 | VII-1 | Mir127 | 406914 | 21-May-15 | 925 | 3 | 4 | 5 | 6 | 7 | VII-1 | Mir19a | 406979 | 24-May-15 |
| 833 | 3 | 4 | 5 | 6 | 7 | VII-1 | Mir129-2 | 406918 | 21-May-15 | 926 | 3 | 4 | 5 | 6 | 7 | VII-1 | Mir19b-1 | | |
| 834 | 3 | 4 | 5 | 6 | 7 | VII-1 | Mir130b | 100302197 | 21-May-15 | 927 | 3 | 4 | 5 | 6 | 7 | VII-1 | Mir200a | 406983 | 21-May-15 |
| | | | | | | | | | | 928 | 3 | 4 | 5 | 6 | 7 | VII-1 | Mir200b | 406984 | 21-May-15 |
| 835 | 3 | 4 | 5 | 6 | 7 | VII-1 | Mir130a | 406919 | 24-May-15 | 929 | 3 | 4 | 5 | 6 | 7 | VII-1 | Mir200c | 406985 | 21-May-15 |
| 836 | 3 | 4 | 5 | 6 | 7 | VII-1 | Mir130c | | | 930 | 3 | 4 | 5 | 6 | 7 | VII-1 | Mir202 | 574448 | 21-May-15 |
| 837 | 3 | 4 | 5 | 6 | 7 | VII-1 | Mir132 | 406921 | 21-May-15 | 931 | 3 | 4 | 5 | 6 | 7 | VII-1 | Mir203 | 406986 | 21-May-15 |
| 838 | 3 | 4 | 5 | 6 | 7 | VII-1 | Mir133a-1 | | | 932 | 3 | 4 | 5 | 6 | 7 | VII-1 | Mir205 | 406988 | 21-May-15 |
| 839 | 3 | 4 | 5 | 6 | 7 | VII-1 | Mir133a-2 | | | 933 | 3 | 4 | 5 | 6 | 7 | VII-1 | Mir206 | 406989 | 21-May-15 |
| 840 | 3 | 4 | 5 | 6 | 7 | VII-1 | Mir133c | | | 934 | 3 | 4 | 5 | 6 | 7 | VII-1 | Mir207 | | |
| 841 | 3 | 4 | 5 | 6 | 7 | VII-1 | Mir134 | 406924 | 21-May-15 | 935 | 3 | 4 | 5 | 6 | 7 | VII-1 | Mir208b | 100126336 | 21-May-15 |
| 842 | 3 | 4 | 5 | 6 | 7 | VII-1 | Mir135a-1 | | | 936 | 3 | 4 | 5 | 6 | 7 | VII-1 | Mir20a | 406982 | 21-May-15 |
| 843 | 3 | 4 | 5 | 6 | 7 | VII-1 | Mir135a-2 | | | 937 | 3 | 4 | 5 | 6 | 7 | VII-1 | Mir210 | 406992 | 24-May-15 |
| 844 | 3 | 4 | 5 | 6 | 7 | VII-1 | Mir138-1 | 406929 | 21-May-15 | 938 | 3 | 4 | 5 | 6 | 7 | VII-1 | Mir211 | 406993 | 21-May-15 |
| | | | | | | | | | | 939 | 3 | 4 | 5 | 6 | 7 | VII-1 | Mir212 | 406994 | 21-May-15 |

Fig. 30 - 6

| | | | | | | | | | | | | | | | | | | | |
|---|---|---|---|---|---|---|---|---|---|---|---|---|---|---|---|---|---|---|---|
| 940 | 3 | 4 | 5 | 6 | 7 | VII-1 | Mir2139 | | | 1034 | 3 | 4 | 5 | 6 | 7 | VII-1 | Mir344c | | |
| 941 | 3 | 4 | 5 | 6 | 7 | VII-1 | Mir214 | 406996 | 21-May-15 | 1035 | 3 | 4 | 5 | 6 | 7 | VII-1 | Mir344d-1 | | |
| 942 | 3 | 4 | 5 | 6 | 7 | VII-1 | Mir215 | 406997 | 21-May-15 | 1036 | 3 | 4 | 5 | 6 | 7 | VII-1 | Mir344d-3 | | |
| 943 | 3 | 4 | 5 | 6 | 7 | VII-1 | Mir217 | 406999 | 21-May-15 | 1037 | 3 | 4 | 5 | 6 | 7 | VII-1 | Mir344g | | |
| 944 | 3 | 4 | 5 | 6 | 7 | VII-1 | Mir218-2 | 407001 | 21-May-15 | 1038 | 3 | 4 | 5 | 6 | 7 | VII-1 | Mir344i | | |
| 945 | 3 | 4 | 5 | 6 | 7 | VII-1 | Mir219-1 | 407002 | 21-May-15 | 1039 | 3 | 4 | 5 | 6 | 7 | VII-1 | Mir345 | 442910 | 21-May-15 |
| 946 | 3 | 4 | 5 | 6 | 7 | VII-1 | Mir219-2 | 407003 | 21-May-15 | 1040 | 3 | 4 | 5 | 6 | 7 | VII-1 | Mir3471-1 | | |
| 947 | 3 | 4 | 5 | 6 | 7 | VII-1 | Mir219c | | | 1041 | 3 | 4 | 5 | 6 | 7 | VII-1 | Mir3473 | | |
| 948 | 3 | 4 | 5 | 6 | 7 | VII-1 | Mir22 | 407004 | 24-May-15 | 1042 | 3 | 4 | 5 | 6 | 7 | VII-1 | Mir3473c | | |
| 949 | 3 | 4 | 5 | 6 | 7 | VII-1 | Mir221 | 407006 | 21-May-15 | 1043 | 3 | 4 | 5 | 6 | 7 | VII-1 | Mir3473d | | |
| 950 | 3 | 4 | 5 | 6 | 7 | VII-1 | Mir222 | 407007 | 21-May-15 | 1044 | 3 | 4 | 5 | 6 | 7 | VII-1 | Mir3473e | | |
| 951 | 3 | 4 | 5 | 6 | 7 | VII-1 | Mir224 | 407009 | 4-May-15 | 1045 | 3 | 4 | 5 | 6 | 7 | VII-1 | Mir3473g | | |
| 952 | 3 | 4 | 5 | 6 | 7 | VII-1 | Mir23a | 407010 | 24-May-15 | 1046 | 3 | 4 | 5 | 6 | 7 | VII-1 | Mir3474 | | |
| 953 | 3 | 4 | 5 | 6 | 7 | VII-1 | Mir23b | 407011 | 21-May-15 | 1047 | 3 | 4 | 5 | 6 | 7 | VII-1 | Mir34a | 407040 | 21-May-15 |
| 954 | 3 | 4 | 5 | 6 | 7 | VII-1 | Mir24-1 | 407012 | 21-May-15 | 1048 | 3 | 4 | 5 | 6 | 7 | VII-1 | Mir34c | 407042 | 21-May-15 |
| 955 | 3 | 4 | 5 | 6 | 7 | VII-1 | Mir24-2 | 407013 | 21-May-15 | 1049 | 3 | 4 | 5 | 6 | 7 | VII-1 | Mir350 | | |
| 956 | 3 | 4 | 5 | 6 | 7 | VII-1 | Mir25 | 407014 | 21-May-15 | 1050 | 3 | 4 | 5 | 6 | 7 | VII-1 | Mir351 | | |
| 957 | 3 | 4 | 5 | 6 | 7 | VII-1 | Mir26a-1 | | | 1051 | 3 | 4 | 5 | 6 | 7 | VII-1 | Mir3547 | | |
| 958 | 3 | 4 | 5 | 6 | 7 | VII-1 | Mir26a-2 | | | 1052 | 3 | 4 | 5 | 6 | 7 | VII-1 | Mir3569 | | |
| 959 | 3 | 4 | 5 | 6 | 7 | VII-1 | Mir26b | 407017 | 21-May-15 | 1053 | 3 | 4 | 5 | 6 | 7 | VII-1 | Mir3572 | | |
| 960 | 3 | 4 | 5 | 6 | 7 | VII-1 | Mir27a | 407018 | 21-May-15 | 1054 | 3 | 4 | 5 | 6 | 7 | VII-1 | Mir3620 | 100500 810 | 21-May-15 |
| 961 | 3 | 4 | 5 | 6 | 7 | VII-1 | Mir27b | 407019 | 21-May-15 | 1055 | 3 | 4 | 5 | 6 | 7 | VII-1 | Mir363 | 574031 | 21-May-15 |
| 962 | 3 | 4 | 5 | 6 | 7 | VII-1 | Mir290 | | | 1056 | 3 | 4 | 5 | 6 | 7 | VII-1 | Mir365-1 | 100126 355 | 21-May-15 |
| 963 | 3 | 4 | 5 | 6 | 7 | VII-1 | Mir290b | | | 1057 | 3 | 4 | 5 | 6 | 7 | VII-1 | Mir365-2 | 100126 356 | 21-May-15 |
| 964 | 3 | 4 | 5 | 6 | 7 | VII-1 | Mir291a | | | 1058 | 3 | 4 | 5 | 6 | 7 | VII-1 | Mir367 | 442912 | 17-May-15 |
| 965 | 3 | 4 | 5 | 6 | 7 | VII-1 | Mir291b | | | 1059 | 3 | 4 | 5 | 6 | 7 | VII-1 | Mir369 | 442914 | 21-May-15 |
| 966 | 3 | 4 | 5 | 6 | 7 | VII-1 | Mir292 | | | 1060 | 3 | 4 | 5 | 6 | 7 | VII-1 | Mir374 | | |
| 967 | 3 | 4 | 5 | 6 | 7 | VII-1 | Mir292b | | | 1061 | 3 | 4 | 5 | 6 | 7 | VII-1 | Mir374c | 100500 807 | 21-May-15 |
| 968 | 3 | 4 | 5 | 6 | 7 | VII-1 | Mir293 | | | 1062 | 3 | 4 | 5 | 6 | 7 | VII-1 | Mir376a | | |
| 969 | 3 | 4 | 5 | 6 | 7 | VII-1 | Mir294 | | | 1063 | 3 | 4 | 5 | 6 | 7 | VII-1 | Mir377 | 494326 | 21-May-15 |
| 970 | 3 | 4 | 5 | 6 | 7 | VII-1 | Mir295 | | | 1064 | 3 | 4 | 5 | 6 | 7 | VII-1 | Mir378b | 100422 933 | 4-May-15 |
| 971 | 3 | 4 | 5 | 6 | 7 | VII-1 | Mir29a | 407021 | 21-May-15 | 1065 | 3 | 4 | 5 | 6 | 7 | VII-1 | Mir381 | 494330 | 21-May-15 |
| 972 | 3 | 4 | 5 | 6 | 7 | VII-1 | Mir29b-2 | | | 1066 | 3 | 4 | 5 | 6 | 7 | VII-1 | Mir382 | 494331 | 21-May-15 |
| 973 | 3 | 4 | 5 | 6 | 7 | VII-1 | Mir29c | 407026 | 21-May-15 | 1067 | 3 | 4 | 5 | 6 | 7 | VII-1 | Mir3960 | 100616 250 | 5-May-15 |
| 974 | 3 | 4 | 5 | 6 | 7 | VII-1 | Mir301 | 407027 | 21-May-15 | 1068 | 3 | 4 | 5 | 6 | 7 | VII-1 | Mir3966 | | |
| 975 | 3 | 4 | 5 | 6 | 7 | VII-1 | Mir301b | 100126 318 | 21-May-15 | 1069 | 3 | 4 | 5 | 6 | 7 | VII-1 | Mir3968 | | |
| 976 | 3 | 4 | 5 | 6 | 7 | VII-1 | Mir302a | 407028 | 21-May-15 | 1070 | 3 | 4 | 5 | 6 | 7 | VII-1 | Mir3971 | | |
| 977 | 3 | 4 | 5 | 6 | 7 | VII-1 | Mir302b | 442894 | 21-May-15 | 1071 | 3 | 4 | 5 | 6 | 7 | VII-1 | Mir409 | 574413 | 21-May-15 |
| 978 | 3 | 4 | 5 | 6 | 7 | VII-1 | Mir302c | 442895 | 21-May-15 | 1072 | 3 | 4 | 5 | 6 | 7 | VII-1 | Mir410 | 574434 | 21-May-15 |
| 979 | 3 | 4 | 5 | 6 | 7 | VII-1 | Mir302d | 442896 | 21-May-15 | 1073 | 3 | 4 | 5 | 6 | 7 | VII-1 | Mir412 | 574433 | 21-May-15 |
| 980 | 3 | 4 | 5 | 6 | 7 | VII-1 | Mir3057 | | | 1074 | 3 | 4 | 5 | 6 | 7 | VII-1 | Mir421 | 693122 | 4-May-15 |
| 981 | 3 | 4 | 5 | 6 | 7 | VII-1 | Mir3058 | | | 1075 | 3 | 4 | 5 | 6 | 7 | VII-1 | Mir423 | 494335 | 21-May-15 |
| 982 | 3 | 4 | 5 | 6 | 7 | VII-1 | Mir3060 | | | 1076 | 3 | 4 | 5 | 6 | 7 | VII-1 | Mir425 | 494337 | 21-May-15 |
| 983 | 3 | 4 | 5 | 6 | 7 | VII-1 | Mir3061 | | | 1077 | 3 | 4 | 5 | 6 | 7 | VII-1 | Mir429 | 554210 | 21-May-15 |
| 984 | 3 | 4 | 5 | 6 | 7 | VII-1 | Mir3062 | | | 1078 | 3 | 4 | 5 | 6 | 7 | VII-1 | Mir431 | 574038 | 21-May-15 |
| 985 | 3 | 4 | 5 | 6 | 7 | VII-1 | Mir3063 | | | 1079 | 3 | 4 | 5 | 6 | 7 | VII-1 | Mir432 | 574451 | 21-May-15 |
| 986 | 3 | 4 | 5 | 6 | 7 | VII-1 | Mir3065 | 100422 915 | 21-May-15 | 1080 | 3 | 4 | 5 | 6 | 7 | VII-1 | Mir433 | 574034 | 21-May-15 |
| 987 | 3 | 4 | 5 | 6 | 7 | VII-1 | Mir3066 | | | 1081 | 3 | 4 | 5 | 6 | 7 | VII-1 | Mir434 | | |
| 988 | 3 | 4 | 5 | 6 | 7 | VII-1 | Mir3067 | | | 1082 | 3 | 4 | 5 | 6 | 7 | VII-1 | Mir450b | 100126 302 | 21-May-15 |
| 989 | 3 | 4 | 5 | 6 | 7 | VII-1 | Mir3068 | | | 1083 | 3 | 4 | 5 | 6 | 7 | VII-1 | Mir451 | 574411 | 21-May-15 |
| 990 | 3 | 4 | 5 | 6 | 7 | VII-1 | Mir3069 | | | 1084 | 3 | 4 | 5 | 6 | 7 | VII-1 | Mir453 | 574410 | 21-May-15 |
| 991 | 3 | 4 | 5 | 6 | 7 | VII-1 | Mir3070a | | | 1085 | 3 | 4 | 5 | 6 | 7 | VII-1 | Mir4660 | 100616 350 | 4-May-15 |
| 992 | 3 | 4 | 5 | 6 | 7 | VII-1 | Mir3071 | | | 1086 | 3 | 4 | 5 | 6 | 7 | VII-1 | Mir466i | | |
| 993 | 3 | 4 | 5 | 6 | 7 | VII-1 | Mir3072 | | | 1087 | 3 | 4 | 5 | 6 | 7 | VII-1 | Mir467a-10 | | |
| 994 | 3 | 4 | 5 | 6 | 7 | VII-1 | Mir3073 | | | 1088 | 3 | 4 | 5 | 6 | 7 | VII-1 | Mir467f | | |
| 995 | 3 | 4 | 5 | 6 | 7 | VII-1 | Mir3074-1 | | | 1089 | 3 | 4 | 5 | 6 | 7 | VII-1 | Mir484 | 619553 | 21-May-15 |
| 996 | 3 | 4 | 5 | 6 | 7 | VII-1 | Mir3074-2 | | | 1090 | 3 | 4 | 5 | 6 | 7 | VII-1 | Mir485 | 574436 | 21-May-15 |
| 997 | 3 | 4 | 5 | 6 | 7 | VII-1 | Mir3075 | | | 1091 | 3 | 4 | 5 | 6 | 7 | VII-1 | Mir486 | 619554 | 21-May-15 |
| 998 | 3 | 4 | 5 | 6 | 7 | VII-1 | Mir3076 | | | 1092 | 3 | 4 | 5 | 6 | 7 | VII-1 | Mir487b | 664616 | 21-May-15 |
| 999 | 3 | 4 | 5 | 6 | 7 | VII-1 | Mir3077 | | | 1093 | 3 | 4 | 5 | 6 | 7 | VII-1 | Mir490 | 574443 | 24-May-15 |
| 1000 | 3 | 4 | 5 | 6 | 7 | VII-1 | Mir3081 | | | 1094 | 3 | 4 | 5 | 6 | 7 | VII-1 | Mir491 | 574444 | 24-May-15 |
| 1001 | 3 | 4 | 5 | 6 | 7 | VII-1 | Mir3082 | | | 1095 | 3 | 4 | 5 | 6 | 7 | VII-1 | Mir493 | 574450 | 21-May-15 |
| 1002 | 3 | 4 | 5 | 6 | 7 | VII-1 | Mir3084 | | | 1096 | 3 | 4 | 5 | 6 | 7 | VII-1 | Mir496 | 574454 | 21-May-15 |
| 1003 | 3 | 4 | 5 | 6 | 7 | VII-1 | Mir3086 | | | 1097 | 3 | 4 | 5 | 6 | 7 | VII-1 | Mir499 | 574501 | 21-May-15 |
| 1004 | 3 | 4 | 5 | 6 | 7 | VII-1 | Mir3087 | | | 1098 | 3 | 4 | 5 | 6 | 7 | VII-1 | Mir5046 | | |
| 1005 | 3 | 4 | 5 | 6 | 7 | VII-1 | Mir3089 | | | 1099 | 3 | 4 | 5 | 6 | 7 | VII-1 | Mir505 | 574508 | 21-May-15 |
| 1006 | 3 | 4 | 5 | 6 | 7 | VII-1 | Mir3091 | | | 1100 | 3 | 4 | 5 | 6 | 7 | VII-1 | Mir5098 | | |
| 1007 | 3 | 4 | 5 | 6 | 7 | VII-1 | Mir3092 | | | 1101 | 3 | 4 | 5 | 6 | 7 | VII-1 | Mir5100 | 100847 014 | 4-May-15 |
| 1008 | 3 | 4 | 5 | 6 | 7 | VII-1 | Mir3094 | | | 1102 | 3 | 4 | 5 | 6 | 7 | VII-1 | Mir5103 | | |
| 1009 | 3 | 4 | 5 | 6 | 7 | VII-1 | Mir3095 | | | 1103 | 3 | 4 | 5 | 6 | 7 | VII-1 | Mir5104 | | |
| 1010 | 3 | 4 | 5 | 6 | 7 | VII-1 | Mir3097 | | | 1104 | 3 | 4 | 5 | 6 | 7 | VII-1 | Mir5106 | | |
| 1011 | 3 | 4 | 5 | 6 | 7 | VII-1 | Mir30b | 407030 | 21-May-15 | 1105 | 3 | 4 | 5 | 6 | 7 | VII-1 | Mir5107 | | |
| 1012 | 3 | 4 | 5 | 6 | 7 | VII-1 | Mir30c-2 | | | 1106 | 3 | 4 | 5 | 6 | 7 | VII-1 | Mir5112 | 574445 | 21-May-15 |
| 1013 | 3 | 4 | 5 | 6 | 7 | VII-1 | Mir30d | 407033 | 21-May-15 | 1107 | 3 | 4 | 5 | 6 | 7 | VII-1 | Mir5113 | | |
| 1014 | 3 | 4 | 5 | 6 | 7 | VII-1 | Mir30f | | | 1108 | 3 | 4 | 5 | 6 | 7 | VII-1 | Mir5114 | | |
| 1015 | 3 | 4 | 5 | 6 | 7 | VII-1 | Mir3100 | | | 1109 | 3 | 4 | 5 | 6 | 7 | VII-1 | Mir5116 | | |
| 1016 | 3 | 4 | 5 | 6 | 7 | VII-1 | Mir3102 | | | 1110 | 3 | 4 | 5 | 6 | 7 | VII-1 | Mir5119 | | |
| 1017 | 3 | 4 | 5 | 6 | 7 | VII-1 | Mir3103 | | | 1111 | 3 | 4 | 5 | 6 | 7 | VII-1 | Mir5121 | 574458 | 21-May-15 |
| 1018 | 3 | 4 | 5 | 6 | 7 | VII-1 | Mir3104 | | | 1112 | 3 | 4 | 5 | 6 | 7 | VII-1 | Mir5123 | | |
| 1019 | 3 | 4 | 5 | 6 | 7 | VII-1 | Mir3107 | | | 1113 | 3 | 4 | 5 | 6 | 7 | VII-1 | Mir5126 | | |
| 1020 | 3 | 4 | 5 | 6 | 7 | VII-1 | Mir3109 | | | 1114 | 3 | 4 | 5 | 6 | 7 | VII-1 | Mir5127 | | |
| 1021 | 3 | 4 | 5 | 6 | 7 | VII-1 | Mir3112 | | | 1115 | 3 | 4 | 5 | 6 | 7 | VII-1 | Mir5128 | | |
| 1022 | 3 | 4 | 5 | 6 | 7 | VII-1 | Mir32 | 407036 | 21-May-15 | 1116 | 3 | 4 | 5 | 6 | 7 | VII-1 | Mir5129 | | |
| 1023 | 3 | 4 | 5 | 6 | 7 | VII-1 | Mir320 | | | 1117 | 3 | 4 | 5 | 6 | 7 | VII-1 | Mir5132 | | |
| 1024 | 3 | 4 | 5 | 6 | 7 | VII-1 | Mir324 | 442898 | 21-May-15 | 1118 | 3 | 4 | 5 | 6 | 7 | VII-1 | Mir5133 | | |
| 1025 | 3 | 4 | 5 | 6 | 7 | VII-1 | Mir328 | 442901 | 21-May-15 | 1119 | 3 | 4 | 5 | 6 | 7 | VII-1 | Mir5134 | | |
| 1026 | 3 | 4 | 5 | 6 | 7 | VII-1 | Mir329 | | | 1120 | 3 | 4 | 5 | 6 | 7 | VII-1 | Mir5135 | | |
| 1027 | 3 | 4 | 5 | 6 | 7 | VII-1 | Mir330 | 442903 | 21-May-15 | 1121 | 3 | 4 | 5 | 6 | 7 | VII-1 | Mir5136 | | |
| 1028 | 3 | 4 | 5 | 6 | 7 | VII-1 | Mir331 | 442903 | 21-May-15 | 1122 | 3 | 4 | 5 | 6 | 7 | VII-1 | Mir540 | | |
| 1029 | 3 | 4 | 5 | 6 | 7 | VII-1 | Mir335 | 442904 | 21-May-15 | 1123 | 3 | 4 | 5 | 6 | 7 | VII-1 | Mir541 | 100126 | 21-May-15 |
| 1030 | 3 | 4 | 5 | 6 | 7 | VII-1 | Mir337 | 442905 | 21-May-15 | | | | | | | | | | |
| 1031 | 3 | 4 | 5 | 6 | 7 | VII-1 | Mir338 | 442906 | 21-May-15 | | | | | | | | | | |
| 1032 | 3 | 4 | 5 | 6 | 7 | VII-1 | Mir339 | 442907 | 21-May-15 | | | | | | | | | | |
| 1033 | 3 | 4 | 5 | 6 | 7 | VII-1 | Mir343 | | | | | | | | | | | | |

Fig. 30 - 7

| | | | | | | | | 308 | |
|---|---|---|---|---|---|---|---|---|---|
| 1124 | 3 | 4 | 5 | 6 | 7 | VII-1 | Mir547 | | |
| 1125 | 3 | 4 | 5 | 6 | 7 | VII-1 | Mir5615-2 | | |
| 1126 | 3 | 4 | 5 | 6 | 7 | VII-1 | Mir5617 | | |
| 1127 | 3 | 4 | 5 | 6 | 7 | VII-1 | Mir5618 | | |
| 1128 | 3 | 4 | 5 | 6 | 7 | VII-1 | Mir5619 | | |
| 1129 | 3 | 4 | 5 | 6 | 7 | VII-1 | Mir5620 | | |
| 1130 | 3 | 4 | 5 | 6 | 7 | VII-1 | Mir5621 | | |
| 1131 | 3 | 4 | 5 | 6 | 7 | VII-1 | Mir5622 | | |
| 1132 | 3 | 4 | 5 | 6 | 7 | VII-1 | Mir5623 | | |
| 1133 | 3 | 4 | 5 | 6 | 7 | VII-1 | Mir5625 | | |
| 1134 | 3 | 4 | 5 | 6 | 7 | VII-1 | Mir568 | 693153 | 4-May-15 |
| 1135 | 3 | 4 | 5 | 6 | 7 | VII-1 | Mir5709 | | |
| 1136 | 3 | 4 | 5 | 6 | 7 | VII-1 | Mir5710 | | |
| 1137 | 3 | 4 | 5 | 6 | 7 | VII-1 | Mir599 | 693184 | 4-May-15 |
| 1138 | 3 | 4 | 5 | 6 | 7 | VII-1 | Mir6236 | | |
| 1139 | 3 | 4 | 5 | 6 | 7 | VII-1 | Mir6244 | | |
| 1140 | 3 | 4 | 5 | 6 | 7 | VII-1 | Mir6337 | | |
| 1141 | 3 | 4 | 5 | 6 | 7 | VII-1 | Mir6338 | | |
| 1142 | 3 | 4 | 5 | 6 | 7 | VII-1 | Mir6340 | | |
| 1143 | 3 | 4 | 5 | 6 | 7 | VII-1 | Mir6356 | | |
| 1144 | 3 | 4 | 5 | 6 | 7 | VII-1 | Mir6357 | | |
| 1145 | 3 | 4 | 5 | 6 | 7 | VII-1 | Mir6358 | | |
| 1146 | 3 | 4 | 5 | 6 | 7 | VII-1 | Mir6359 | | |
| 1147 | 3 | 4 | 5 | 6 | 7 | VII-1 | Mir6363 | | |
| 1148 | 3 | 4 | 5 | 6 | 7 | VII-1 | Mir6365 | | |
| 1149 | 3 | 4 | 5 | 6 | 7 | VII-1 | Mir6366 | | |
| 1150 | 3 | 4 | 5 | 6 | 7 | VII-1 | Mir6368 | | |
| 1151 | 3 | 4 | 5 | 6 | 7 | VII-1 | Mir6386 | | |
| 1152 | 3 | 4 | 5 | 6 | 7 | VII-1 | Mir6387 | | |
| 1153 | 3 | 4 | 5 | 6 | 7 | VII-1 | Mir6389 | | |
| 1154 | 3 | 4 | 5 | 6 | 7 | VII-1 | Mir6391 | | |
| 1155 | 3 | 4 | 5 | 6 | 7 | VII-1 | Mir6392 | | |
| 1156 | 3 | 4 | 5 | 6 | 7 | VII-1 | Mir6395 | | |
| 1157 | 3 | 4 | 5 | 6 | 7 | VII-1 | Mir6396 | | |
| 1158 | 3 | 4 | 5 | 6 | 7 | VII-1 | Mir6397 | | |
| 1159 | 3 | 4 | 5 | 6 | 7 | VII-1 | Mir6399 | | |
| 1160 | 3 | 4 | 5 | 6 | 7 | VII-1 | Mir6400 | | |
| 1161 | 3 | 4 | 5 | 6 | 7 | VII-1 | Mir6403 | | |
| 1162 | 3 | 4 | 5 | 6 | 7 | VII-1 | Mir6404 | | |
| 1163 | 3 | 4 | 5 | 6 | 7 | VII-1 | Mir6405 | | |
| 1164 | 3 | 4 | 5 | 6 | 7 | VII-1 | Mir6406 | | |
| 1165 | 3 | 4 | 5 | 6 | 7 | VII-1 | Mir6407 | | |
| 1166 | 3 | 4 | 5 | 6 | 7 | VII-1 | Mir6415 | | |
| 1167 | 3 | 4 | 5 | 6 | 7 | VII-1 | Mir6417 | | |
| 1168 | 3 | 4 | 5 | 6 | 7 | VII-1 | Mir6418 | | |
| 1169 | 3 | 4 | 5 | 6 | 7 | VII-1 | Mir6481 | | |
| 1170 | 3 | 4 | 5 | 6 | 7 | VII-1 | Mir6537 | | |
| 1171 | 3 | 4 | 5 | 6 | 7 | VII-1 | Mir6538 | | |
| 1172 | 3 | 4 | 5 | 6 | 7 | VII-1 | Mir6546 | | |
| 1173 | 3 | 4 | 5 | 6 | 7 | VII-1 | Mir664 | 100302234 | 21-May-15 |
| 1174 | 3 | 4 | 5 | 6 | 7 | VII-1 | Mir665 | 100126315 | 21-May-15 |
| 1175 | 3 | 4 | 5 | 6 | 7 | VII-1 | Mir667 | | |
| 1176 | 3 | 4 | 5 | 6 | 7 | VII-1 | Mir671 | 768213 | 21-May-15 |
| 1177 | 3 | 4 | 5 | 6 | 7 | VII-1 | Mir672 | | |
| 1178 | 3 | 4 | 5 | 6 | 7 | VII-1 | Mir674 | | |
| 1179 | 3 | 4 | 5 | 6 | 7 | VII-1 | Mir675 | 100033819 | 4-May-15 |
| 1180 | 3 | 4 | 5 | 6 | 7 | VII-1 | Mir676 | 100500887 | 21-May-15 |
| 1181 | 3 | 4 | 5 | 6 | 7 | VII-1 | Mir6769b | 102466202 | 4-May-15 |
| 1182 | 3 | 4 | 5 | 6 | 7 | VII-1 | Mir678 | | |
| 1183 | 3 | 4 | 5 | 6 | 7 | VII-1 | Mir679 | | |
| 1184 | 3 | 4 | 5 | 6 | 7 | VII-1 | Mir680-1 | | |
| 1185 | 3 | 4 | 5 | 6 | 7 | VII-1 | Mir680-2 | | |
| 1186 | 3 | 4 | 5 | 6 | 7 | VII-1 | Mir681 | | |
| 1187 | 3 | 4 | 5 | 6 | 7 | VII-1 | Mir682 | | |
| 1188 | 3 | 4 | 5 | 6 | 7 | VII-1 | Mir686 | | |
| 1189 | 3 | 4 | 5 | 6 | 7 | VII-1 | Mir687 | | |
| 1190 | 3 | 4 | 5 | 6 | 7 | VII-1 | Mir688 | | |
| 1191 | 3 | 4 | 5 | 6 | 7 | VII-1 | Mir6897 | | |
| 1192 | 3 | 4 | 5 | 6 | 7 | VII-1 | Mir6898 | | |
| 1193 | 3 | 4 | 5 | 6 | 7 | VII-1 | Mir6900 | | |
| 1194 | 3 | 4 | 5 | 6 | 7 | VII-1 | Mir6902 | | |
| 1195 | 3 | 4 | 5 | 6 | 7 | VII-1 | Mir6904 | | |
| 1196 | 3 | 4 | 5 | 6 | 7 | VII-1 | Mir6905 | | |
| 1197 | 3 | 4 | 5 | 6 | 7 | VII-1 | Mir6907 | | |
| 1198 | 3 | 4 | 5 | 6 | 7 | VII-1 | Mir6908 | | |
| 1199 | 3 | 4 | 5 | 6 | 7 | VII-1 | Mir6909 | | |
| 1200 | 3 | 4 | 5 | 6 | 7 | VII-1 | Mir6910 | | |
| 1201 | 3 | 4 | 5 | 6 | 7 | VII-1 | Mir6911 | | |
| 1202 | 3 | 4 | 5 | 6 | 7 | VII-1 | Mir6912 | | |
| 1203 | 3 | 4 | 5 | 6 | 7 | VII-1 | Mir6913 | | |
| 1204 | 3 | 4 | 5 | 6 | 7 | VII-1 | Mir6914 | | |
| 1205 | 3 | 4 | 5 | 6 | 7 | VII-1 | Mir6915 | | |
| 1206 | 3 | 4 | 5 | 6 | 7 | VII-1 | Mir6916 | | |
| 1207 | 3 | 4 | 5 | 6 | 7 | VII-1 | Mir6917 | | |
| 1208 | 3 | 4 | 5 | 6 | 7 | VII-1 | Mir6918 | | |
| 1209 | 3 | 4 | 5 | 6 | 7 | VII-1 | Mir6919 | | |
| 1210 | 3 | 4 | 5 | 6 | 7 | VII-1 | Mir6920 | | |
| 1211 | 3 | 4 | 5 | 6 | 7 | VII-1 | Mir6921 | | |
| 1212 | 3 | 4 | 5 | 6 | 7 | VII-1 | Mir692-1 | | |
| 1213 | 3 | 4 | 5 | 6 | 7 | VII-1 | Mir6922 | | |
| 1214 | 3 | 4 | 5 | 6 | 7 | VII-1 | Mir6924 | | |

| 1215 | 3 | 4 | 5 | 6 | 7 | VII-1 | Mir6925 | | |
|---|---|---|---|---|---|---|---|---|---|
| 1216 | 3 | 4 | 5 | 6 | 7 | VII-1 | Mir6926 | | |
| 1217 | 3 | 4 | 5 | 6 | 7 | VII-1 | Mir6927 | | |
| 1218 | 3 | 4 | 5 | 6 | 7 | VII-1 | Mir6928 | | |
| 1219 | 3 | 4 | 5 | 6 | 7 | VII-1 | Mir6929 | | |
| 1220 | 3 | 4 | 5 | 6 | 7 | VII-1 | Mir6930 | | |
| 1221 | 3 | 4 | 5 | 6 | 7 | VII-1 | Mir6931 | | |
| 1222 | 3 | 4 | 5 | 6 | 7 | VII-1 | Mir6933 | | |
| 1223 | 3 | 4 | 5 | 6 | 7 | VII-1 | Mir6934 | | |
| 1224 | 3 | 4 | 5 | 6 | 7 | VII-1 | Mir6935 | | |
| 1225 | 3 | 4 | 5 | 6 | 7 | VII-1 | Mir6936 | | |
| 1226 | 3 | 4 | 5 | 6 | 7 | VII-1 | Mir6937 | | |
| 1227 | 3 | 4 | 5 | 6 | 7 | VII-1 | Mir6938 | | |
| 1228 | 3 | 4 | 5 | 6 | 7 | VII-1 | Mir6939 | | |
| 1229 | 3 | 4 | 5 | 6 | 7 | VII-1 | Mir6940 | | |
| 1230 | 3 | 4 | 5 | 6 | 7 | VII-1 | Mir6941 | | |
| 1231 | 3 | 4 | 5 | 6 | 7 | VII-1 | Mir6942 | | |
| 1232 | 3 | 4 | 5 | 6 | 7 | VII-1 | Mir6943 | | |
| 1233 | 3 | 4 | 5 | 6 | 7 | VII-1 | Mir6944 | | |
| 1234 | 3 | 4 | 5 | 6 | 7 | VII-1 | Mir6945 | | |
| 1235 | 3 | 4 | 5 | 6 | 7 | VII-1 | Mir6946 | | |
| 1236 | 3 | 4 | 5 | 6 | 7 | VII-1 | Mir6947 | | |
| 1237 | 3 | 4 | 5 | 6 | 7 | VII-1 | Mir6948 | | |
| 1238 | 3 | 4 | 5 | 6 | 7 | VII-1 | Mir6950 | | |
| 1239 | 3 | 4 | 5 | 6 | 7 | VII-1 | Mir6951 | | |
| 1240 | 3 | 4 | 5 | 6 | 7 | VII-1 | Mir6953 | | |
| 1241 | 3 | 4 | 5 | 6 | 7 | VII-1 | Mir6954 | | |
| 1242 | 3 | 4 | 5 | 6 | 7 | VII-1 | Mir6958 | | |
| 1243 | 3 | 4 | 5 | 6 | 7 | VII-1 | Mir6959 | | |
| 1244 | 3 | 4 | 5 | 6 | 7 | VII-1 | Mir6960 | | |
| 1245 | 3 | 4 | 5 | 6 | 7 | VII-1 | Mir6961 | | |
| 1246 | 3 | 4 | 5 | 6 | 7 | VII-1 | Mir6962 | | |
| 1247 | 3 | 4 | 5 | 6 | 7 | VII-1 | Mir6963 | | |
| 1248 | 3 | 4 | 5 | 6 | 7 | VII-1 | Mir6964 | | |
| 1249 | 3 | 4 | 5 | 6 | 7 | VII-1 | Mir6966 | | |
| 1250 | 3 | 4 | 5 | 6 | 7 | VII-1 | Mir6968 | | |
| 1251 | 3 | 4 | 5 | 6 | 7 | VII-1 | Mir6969 | | |
| 1252 | 3 | 4 | 5 | 6 | 7 | VII-1 | Mir697 | | |
| 1253 | 3 | 4 | 5 | 6 | 7 | VII-1 | Mir6970 | | |
| 1254 | 3 | 4 | 5 | 6 | 7 | VII-1 | Mir6972 | | |
| 1255 | 3 | 4 | 5 | 6 | 7 | VII-1 | Mir6973a | | |
| 1256 | 3 | 4 | 5 | 6 | 7 | VII-1 | Mir6973b | | |
| 1257 | 3 | 4 | 5 | 6 | 7 | VII-1 | Mir6974 | | |
| 1258 | 3 | 4 | 5 | 6 | 7 | VII-1 | Mir6975 | | |
| 1259 | 3 | 4 | 5 | 6 | 7 | VII-1 | Mir6976 | | |
| 1260 | 3 | 4 | 5 | 6 | 7 | VII-1 | Mir6977 | | |
| 1261 | 3 | 4 | 5 | 6 | 7 | VII-1 | Mir6979 | | |
| 1262 | 3 | 4 | 5 | 6 | 7 | VII-1 | Mir6980 | | |
| 1263 | 3 | 4 | 5 | 6 | 7 | VII-1 | Mir6981 | | |
| 1264 | 3 | 4 | 5 | 6 | 7 | VII-1 | Mir6984 | | |
| 1265 | 3 | 4 | 5 | 6 | 7 | VII-1 | Mir6985 | | |
| 1266 | 3 | 4 | 5 | 6 | 7 | VII-1 | Mir6986 | | |
| 1267 | 3 | 4 | 5 | 6 | 7 | VII-1 | Mir6988 | | |
| 1268 | 3 | 4 | 5 | 6 | 7 | VII-1 | Mir6989 | | |
| 1269 | 3 | 4 | 5 | 6 | 7 | VII-1 | Mir6991 | | |
| 1270 | 3 | 4 | 5 | 6 | 7 | VII-1 | Mir6993 | | |
| 1271 | 3 | 4 | 5 | 6 | 7 | VII-1 | Mir6994 | | |
| 1272 | 3 | 4 | 5 | 6 | 7 | VII-1 | Mir6995 | | |
| 1273 | 3 | 4 | 5 | 6 | 7 | VII-1 | Mir6996 | | |
| 1274 | 3 | 4 | 5 | 6 | 7 | VII-1 | Mir6997 | | |
| 1275 | 3 | 4 | 5 | 6 | 7 | VII-1 | Mir6998 | | |
| 1276 | 3 | 4 | 5 | 6 | 7 | VII-1 | Mir6999 | | |
| 1277 | 3 | 4 | 5 | 6 | 7 | VII-1 | Mir700 | | |
| 1278 | 3 | 4 | 5 | 6 | 7 | VII-1 | Mir7000 | | |
| 1279 | 3 | 4 | 5 | 6 | 7 | VII-1 | Mir7001 | | |
| 1280 | 3 | 4 | 5 | 6 | 7 | VII-1 | Mir7003 | | |
| 1281 | 3 | 4 | 5 | 6 | 7 | VII-1 | Mir7004 | | |
| 1282 | 3 | 4 | 5 | 6 | 7 | VII-1 | Mir7005 | | |
| 1283 | 3 | 4 | 5 | 6 | 7 | VII-1 | Mir7006 | | |
| 1284 | 3 | 4 | 5 | 6 | 7 | VII-1 | Mir7007 | | |
| 1285 | 3 | 4 | 5 | 6 | 7 | VII-1 | Mir7009 | | |
| 1286 | 3 | 4 | 5 | 6 | 7 | VII-1 | Mir7010 | | |
| 1287 | 3 | 4 | 5 | 6 | 7 | VII-1 | Mir7011 | | |
| 1288 | 3 | 4 | 5 | 6 | 7 | VII-1 | Mir7012 | | |
| 1289 | 3 | 4 | 5 | 6 | 7 | VII-1 | Mir7013 | | |
| 1290 | 3 | 4 | 5 | 6 | 7 | VII-1 | Mir7014 | | |
| 1291 | 3 | 4 | 5 | 6 | 7 | VII-1 | Mir7015 | | |
| 1292 | 3 | 4 | 5 | 6 | 7 | VII-1 | Mir7016 | | |
| 1293 | 3 | 4 | 5 | 6 | 7 | VII-1 | Mir7017 | | |
| 1294 | 3 | 4 | 5 | 6 | 7 | VII-1 | Mir7018 | | |
| 1295 | 3 | 4 | 5 | 6 | 7 | VII-1 | Mir7019 | | |
| 1296 | 3 | 4 | 5 | 6 | 7 | VII-1 | Mir702 | | |
| 1297 | 3 | 4 | 5 | 6 | 7 | VII-1 | Mir7020 | | |
| 1298 | 3 | 4 | 5 | 6 | 7 | VII-1 | Mir7021 | | |
| 1299 | 3 | 4 | 5 | 6 | 7 | VII-1 | Mir7022 | | |
| 1300 | 3 | 4 | 5 | 6 | 7 | VII-1 | Mir7023 | | |
| 1301 | 3 | 4 | 5 | 6 | 7 | VII-1 | Mir7024 | | |
| 1302 | 3 | 4 | 5 | 6 | 7 | VII-1 | Mir7025 | | |
| 1303 | 3 | 4 | 5 | 6 | 7 | VII-1 | Mir7026 | | |
| 1304 | 3 | 4 | 5 | 6 | 7 | VII-1 | Mir7027 | | |
| 1305 | 3 | 4 | 5 | 6 | 7 | VII-1 | Mir7028 | | |
| 1306 | 3 | 4 | 5 | 6 | 7 | VII-1 | Mir7030 | | |
| 1307 | 3 | 4 | 5 | 6 | 7 | VII-1 | Mir7031 | | |
| 1308 | 3 | 4 | 5 | 6 | 7 | VII-1 | Mir7032 | | |
| 1309 | 3 | 4 | 5 | 6 | 7 | VII-1 | Mir7033 | | |
| 1310 | 3 | 4 | 5 | 6 | 7 | VII-1 | Mir7034 | | |

Fig. 30 - 8

| | | | | | | | | | | | | | | | | | | |
|---|---|---|---|---|---|---|---|---|---|---|---|---|---|---|---|---|---|---|
| 1311 | 3 | 4 | 5 | 6 | 7 | VII-1 | Mir7035 | | | 1402 | 3 | 4 | 5 | 6 | 7 | VII-1 | Mir7656 | | |
| 1312 | 3 | 4 | 5 | 6 | 7 | VII-1 | Mir7036 | | | 1403 | 3 | 4 | 5 | 6 | 7 | VII-1 | Mir7658 | | |
| 1313 | 3 | 4 | 5 | 6 | 7 | VII-1 | Mir7036b | | | 1404 | 3 | 4 | 5 | 6 | 7 | VII-1 | Mir7661 | | |
| 1314 | 3 | 4 | 5 | 6 | 7 | VII-1 | Mir7037 | | | 1405 | 3 | 4 | 5 | 6 | 7 | VII-1 | Mir7662 | | |
| 1315 | 3 | 4 | 5 | 6 | 7 | VII-1 | Mir7039 | | | 1406 | 3 | 4 | 5 | 6 | 7 | VII-1 | Mir7663 | | |
| 1316 | 3 | 4 | 5 | 6 | 7 | VII-1 | Mir704 | | | 1407 | 3 | 4 | 5 | 6 | 7 | VII-1 | Mir7665 | | |
| 1317 | 3 | 4 | 5 | 6 | 7 | VII-1 | Mir7041 | | | 1408 | 3 | 4 | 5 | 6 | 7 | VII-1 | Mir7666 | | |
| 1318 | 3 | 4 | 5 | 6 | 7 | VII-1 | Mir7042 | | | 1409 | 3 | 4 | 5 | 6 | 7 | VII-1 | Mir7670 | | |
| 1319 | 3 | 4 | 5 | 6 | 7 | VII-1 | Mir7043 | | | 1410 | 3 | 4 | 5 | 6 | 7 | VII-1 | Mir7673 | | |
| 1320 | 3 | 4 | 5 | 6 | 7 | VII-1 | Mir7044 | | | 1411 | 3 | 4 | 5 | 6 | 7 | VII-1 | Mir7674 | | |
| 1321 | 3 | 4 | 5 | 6 | 7 | VII-1 | Mir7045 | | | 1412 | 3 | 4 | 5 | 6 | 7 | VII-1 | Mir7675 | | |
| 1322 | 3 | 4 | 5 | 6 | 7 | VII-1 | Mir7046 | | | 1413 | 3 | 4 | 5 | 6 | 7 | VII-1 | Mir7676-1 | | |
| 1323 | 3 | 4 | 5 | 6 | 7 | VII-1 | Mir7048 | | | 1414 | 3 | 4 | 5 | 6 | 7 | VII-1 | Mir7676-2 | | |
| 1324 | 3 | 4 | 5 | 6 | 7 | VII-1 | Mir7049 | | | 1415 | 3 | 4 | 5 | 6 | 7 | VII-1 | Mir7677 | | |
| 1325 | 3 | 4 | 5 | 6 | 7 | VII-1 | Mir7050 | | | 1416 | 3 | 4 | 5 | 6 | 7 | VII-1 | Mir7678 | | |
| 1326 | 3 | 4 | 5 | 6 | 7 | VII-1 | Mir7051 | | | 1417 | 3 | 4 | 5 | 6 | 7 | VII-1 | Mir7679 | | |
| 1327 | 3 | 4 | 5 | 6 | 7 | VII-1 | Mir7052 | | | 1418 | 3 | 4 | 5 | 6 | 7 | VII-1 | Mir7681 | | |
| 1328 | 3 | 4 | 5 | 6 | 7 | VII-1 | Mir7053 | | | 1419 | 3 | 4 | 5 | 6 | 7 | VII-1 | Mir7682 | | |
| 1329 | 3 | 4 | 5 | 6 | 7 | VII-1 | Mir7054 | | | 1420 | 3 | 4 | 5 | 6 | 7 | VII-1 | Mir7683 | | |
| 1330 | 3 | 4 | 5 | 6 | 7 | VII-1 | Mir7058 | | | 1421 | 3 | 4 | 5 | 6 | 7 | VII-1 | Mir7686 | | |
| 1331 | 3 | 4 | 5 | 6 | 7 | VII-1 | Mir7059 | | | 1422 | 3 | 4 | 5 | 6 | 7 | VII-1 | Mir7687 | | |
| 1332 | 3 | 4 | 5 | 6 | 7 | VII-1 | Mir7061 | | | 1423 | 3 | 4 | 5 | 6 | 7 | VII-1 | Mir802 | 768219 | 17-May-15 |
| 1333 | 3 | 4 | 5 | 6 | 7 | VII-1 | Mir7062 | | | 1424 | 3 | 4 | 5 | 6 | 7 | VII-1 | Mir804 | | |
| 1334 | 3 | 4 | 5 | 6 | 7 | VII-1 | Mir7063 | | | 1425 | 3 | 4 | 5 | 6 | 7 | VII-1 | Mir8092 | | |
| 1335 | 3 | 4 | 5 | 6 | 7 | VII-1 | Mir7064 | | | 1426 | 3 | 4 | 5 | 6 | 7 | VII-1 | Mir8093 | | |
| 1336 | 3 | 4 | 5 | 6 | 7 | VII-1 | Mir7066 | | | 1427 | 3 | 4 | 5 | 6 | 7 | VII-1 | Mir8096 | | |
| 1337 | 3 | 4 | 5 | 6 | 7 | VII-1 | Mir7067 | | | 1428 | 3 | 4 | 5 | 6 | 7 | VII-1 | Mir8097 | | |
| 1338 | 3 | 4 | 5 | 6 | 7 | VII-1 | Mir7068 | | | 1429 | 3 | 4 | 5 | 6 | 7 | VII-1 | Mir8098 | | |
| 1339 | 3 | 4 | 5 | 6 | 7 | VII-1 | Mir7069 | | | 1430 | 3 | 4 | 5 | 6 | 7 | VII-1 | Mir8099-2 | | |
| 1340 | 3 | 4 | 5 | 6 | 7 | VII-1 | Mir707 | | | 1431 | 3 | 4 | 5 | 6 | 7 | VII-1 | Mir8102 | | |
| 1341 | 3 | 4 | 5 | 6 | 7 | VII-1 | Mir7070 | | | 1432 | 3 | 4 | 5 | 6 | 7 | VII-1 | Mir8103 | | |
| 1342 | 3 | 4 | 5 | 6 | 7 | VII-1 | Mir7071 | | | 1433 | 3 | 4 | 5 | 6 | 7 | VII-1 | Mir8104 | | |
| 1343 | 3 | 4 | 5 | 6 | 7 | VII-1 | Mir7072 | | | 1434 | 3 | 4 | 5 | 6 | 7 | VII-1 | Mir8105 | | |
| 1344 | 3 | 4 | 5 | 6 | 7 | VII-1 | Mir7073 | | | 1435 | 3 | 4 | 5 | 6 | 7 | VII-1 | Mir8107 | | |
| 1345 | 3 | 4 | 5 | 6 | 7 | VII-1 | Mir7074 | | | 1436 | 3 | 4 | 5 | 6 | 7 | VII-1 | Mir8108 | | |
| 1346 | 3 | 4 | 5 | 6 | 7 | VII-1 | Mir7075 | | | 1437 | 3 | 4 | 5 | 6 | 7 | VII-1 | Mir8113 | | |
| 1347 | 3 | 4 | 5 | 6 | 7 | VII-1 | Mir7077 | | | 1438 | 3 | 4 | 5 | 6 | 7 | VII-1 | Mir8114 | | |
| 1348 | 3 | 4 | 5 | 6 | 7 | VII-1 | Mir7078 | | | 1439 | 3 | 4 | 5 | 6 | 7 | VII-1 | Mir8116 | | |
| 1349 | 3 | 4 | 5 | 6 | 7 | VII-1 | Mir7079 | | | 1440 | 3 | 4 | 5 | 6 | 7 | VII-1 | Mir8118 | | |
| 1350 | 3 | 4 | 5 | 6 | 7 | VII-1 | Mir708 | 100126333 | 4-May-15 | 1441 | 3 | 4 | 5 | 6 | 7 | VII-1 | Mir8120 | | |
| 1351 | 3 | 4 | 5 | 6 | 7 | VII-1 | Mir7080 | | | 1442 | 3 | 4 | 5 | 6 | 7 | VII-1 | Mir872 | | |
| 1352 | 3 | 4 | 5 | 6 | 7 | VII-1 | Mir7081 | | | 1443 | 3 | 4 | 5 | 6 | 7 | VII-1 | Mir873 | 100126316 | 21-May-15 |
| 1353 | 3 | 4 | 5 | 6 | 7 | VII-1 | Mir7082 | | | 1444 | 3 | 4 | 5 | 6 | 7 | VII-1 | Mir874 | 100126343 | 21-May-15 |
| 1354 | 3 | 4 | 5 | 6 | 7 | VII-1 | Mir7083 | | | 1445 | 3 | 4 | 5 | 6 | 7 | VII-1 | Mir875 | 100126309 | 4-May-15 |
| 1355 | 3 | 4 | 5 | 6 | 7 | VII-1 | Mir7085 | | | 1446 | 3 | 4 | 5 | 6 | 7 | VII-1 | Mir877 | 100126314 | 21-May-15 |
| 1356 | 3 | 4 | 5 | 6 | 7 | VII-1 | Mir7086 | | | 1447 | 3 | 4 | 5 | 6 | 7 | VII-1 | Mir883a | | |
| 1357 | 3 | 4 | 5 | 6 | 7 | VII-1 | Mir7087 | | | 1448 | 3 | 4 | 5 | 6 | 7 | VII-1 | Mir9-1 | 407046 | 21-May-15 |
| 1358 | 3 | 4 | 5 | 6 | 7 | VII-1 | Mir7088 | | | 1449 | 3 | 4 | 5 | 6 | 7 | VII-1 | Mir92-1 | 407048 | 21-May-15 |
| 1359 | 3 | 4 | 5 | 6 | 7 | VII-1 | Mir7089 | | | 1450 | 3 | 4 | 5 | 6 | 7 | VII-1 | Mir92-2 | | |
| 1360 | 3 | 4 | 5 | 6 | 7 | VII-1 | Mir709 | | | 1451 | 3 | 4 | 5 | 6 | 7 | VII-1 | Mir92b | 693235 | 21-May-15 |
| 1361 | 3 | 4 | 5 | 6 | 7 | VII-1 | Mir7090 | | | 1452 | 3 | 4 | 5 | 6 | 7 | VII-1 | Mir93 | 407050 | 21-May-15 |
| 1362 | 3 | 4 | 5 | 6 | 7 | VII-1 | Mir7091 | | | 1453 | 3 | 4 | 5 | 6 | 7 | VII-1 | Mir99a | 407055 | 21-May-15 |
| 1363 | 3 | 4 | 5 | 6 | 7 | VII-1 | Mir7092 | | | 1454 | 3 | 4 | 5 | 6 | 7 | VII-1 | Mir99b | 407056 | 21-May-15 |
| 1364 | 3 | 4 | 5 | 6 | 7 | VII-1 | Mir7093 | | | 1455 | 3 | 4 | 5 | 6 | 7 | VII-1 | Mirlet7a-1 | | |
| 1365 | 3 | 4 | 5 | 6 | 7 | VII-1 | Mir711 | 100313843 | 4-May-15 | 1456 | 3 | 4 | 5 | 6 | 7 | VII-1 | Mirlet7b | 406884 | 21-May-15 |
| 1366 | 3 | 4 | 5 | 6 | 7 | VII-1 | Mir7115 | | | 1457 | 3 | 4 | 5 | 6 | 7 | VII-1 | Mirlet7c-1 | | |
| 1367 | 3 | 4 | 5 | 6 | 7 | VII-1 | Mir7117 | | | 1458 | 3 | 4 | 5 | 6 | 7 | VII-1 | Mirlet7c-2 | | |
| 1368 | 3 | 4 | 5 | 6 | 7 | VII-1 | Mir7118 | | | 1459 | 3 | 4 | 5 | 6 | 7 | VII-1 | Mirlet7d | 406886 | 21-May-15 |
| 1369 | 3 | 4 | 5 | 6 | 7 | VII-1 | Mir713 | | | 1460 | 3 | 4 | 5 | 6 | 7 | VII-1 | Mirlet7e | 406887 | 21-May-15 |
| 1370 | 3 | 4 | 5 | 6 | 7 | VII-1 | Mir719 | | | 1461 | 3 | 4 | 5 | 6 | 7 | VII-1 | Mirlet7f-1 | | |
| 1371 | 3 | 4 | 5 | 6 | 7 | VII-1 | Mir7210 | | | 1462 | 3 | 4 | 5 | 6 | 7 | VII-1 | Mirlet7g | 406890 | 21-May-15 |
| 1372 | 3 | 4 | 5 | 6 | 7 | VII-1 | Mir7211 | | | 1463 | 3 | 4 | 5 | 6 | 7 | VII-1 | Mirlet7i | 406891 | 21-May-15 |
| 1373 | 3 | 4 | 5 | 6 | 7 | VII-1 | Mir7214 | | | 1464 | 3 | 4 | 5 | 6 | 7 | VII-1 | Mki67 | 4288 | 24-May-15 |
| 1374 | 3 | 4 | 5 | 6 | 7 | VII-1 | Mir7215 | | | 1465 | 3 | 4 | 5 | 6 | 7 | VII-1 | Mpeg1 | 219972 | 12-May-15 |
| 1375 | 3 | 4 | 5 | 6 | 7 | VII-1 | Mir7216 | | | 1466 | 3 | 4 | 5 | 6 | 7 | VII-1 | Ms4a7 | 58475 | 7-Jun-15 |
| 1376 | 3 | 4 | 5 | 6 | 7 | VII-1 | Mir7220 | | | 1467 | 3 | 4 | 5 | 6 | 7 | VII-1 | Mt4 | 84560 | 4-May-15 |
| 1377 | 3 | 4 | 5 | 6 | 7 | VII-1 | Mir7221 | | | 1468 | 3 | 4 | 5 | 6 | 7 | VII-1 | Muc15 | 143662 | 4-May-15 |
| 1378 | 3 | 4 | 5 | 6 | 7 | VII-1 | Mir7223 | | | 1469 | 3 | 4 | 5 | 6 | 7 | VII-1 | Muc5b | 727897 | 23-May-15 |
| 1379 | 3 | 4 | 5 | 6 | 7 | VII-1 | Mir7225 | | | 1470 | 3 | 4 | 5 | 6 | 7 | VII-1 | Mxd3 | 83463 | 4-May-15 |
| 1380 | 3 | 4 | 5 | 6 | 7 | VII-1 | Mir7226 | | | 1471 | 3 | 4 | 5 | 6 | 7 | VII-1 | Myb | 4602 | 24-May-15 |
| 1381 | 3 | 4 | 5 | 6 | 7 | VII-1 | Mir7227 | | | 1472 | 3 | 4 | 5 | 6 | 7 | VII-1 | Myh1 | 4619 | 4-May-15 |
| 1382 | 3 | 4 | 5 | 6 | 7 | VII-1 | Mir7231 | | | 1473 | 3 | 4 | 5 | 6 | 7 | VII-1 | Myh6 | 4624 | 23-May-15 |
| 1383 | 3 | 4 | 5 | 6 | 7 | VII-1 | Mir7232 | | | 1474 | 3 | 4 | 5 | 6 | 7 | VII-1 | Myh8 | 4626 | 12-May-15 |
| 1384 | 3 | 4 | 5 | 6 | 7 | VII-1 | Mir7236 | | | 1475 | 3 | 4 | 5 | 6 | 7 | VII-1 | Myl1 | 4632 | 4-May-15 |
| 1385 | 3 | 4 | 5 | 6 | 7 | VII-1 | Mir7237 | | | 1476 | 3 | 4 | 5 | 6 | 7 | VII-1 | Myl10 | 93408 | 4-May-15 |
| 1386 | 3 | 4 | 5 | 6 | 7 | VII-1 | Mir7240 | | | 1477 | 3 | 4 | 5 | 6 | 7 | VII-1 | Myl3 | 4634 | 23-May-15 |
| 1387 | 3 | 4 | 5 | 6 | 7 | VII-1 | Mir7241 | | | 1478 | 3 | 4 | 5 | 6 | 7 | VII-1 | Myl4 | 4635 | 4-May-15 |
| 1388 | 3 | 4 | 5 | 6 | 7 | VII-1 | Mir7242 | | | 1479 | 3 | 4 | 5 | 6 | 7 | VII-1 | Myl7 | 58498 | 4-May-15 |
| 1389 | 3 | 4 | 5 | 6 | 7 | VII-1 | Mir744 | 100126313 | 21-May-15 | 1480 | 3 | 4 | 5 | 6 | 7 | VII-1 | Myo3b | 140469 | 4-May-15 |
| 1390 | 3 | 4 | 5 | 6 | 7 | VII-1 | Mir7578 | | | 1481 | 3 | 4 | 5 | 6 | 7 | VII-1 | Mzb1 | 51237 | 4-May-15 |
| 1391 | 3 | 4 | 5 | 6 | 7 | VII-1 | Mir758 | 768212 | 21-May-15 | 1482 | 3 | 4 | 5 | 6 | 7 | VII-1 | Napsa | 9476 | 4-May-15 |
| 1392 | 3 | 4 | 5 | 6 | 7 | VII-1 | Mir759 | 100313778 | 4-May-15 | 1483 | 3 | 4 | 5 | 6 | 7 | VII-1 | Ncapg | 64151 | 4-May-15 |
| 1393 | 3 | 4 | 5 | 6 | 7 | VII-1 | Mir760 | 100126348 | 21-May-15 | 1484 | 3 | 4 | 5 | 6 | 7 | VII-1 | Ndc80 | 10403 | 4-May-15 |
| 1394 | 3 | 4 | 5 | 6 | 7 | VII-1 | Mir761 | 100313892 | 5-May-15 | 1485 | 3 | 4 | 5 | 6 | 7 | VII-1 | Neil3 | 55247 | 4-May-15 |
| 1395 | 3 | 4 | 5 | 6 | 7 | VII-1 | Mir762 | 100313837 | 4-May-15 | 1486 | 3 | 4 | 5 | 6 | 7 | VII-1 | Nfe2l3 | 9603 | 4-May-15 |
| 1396 | 3 | 4 | 5 | 6 | 7 | VII-1 | Mir7646 | | | 1487 | 3 | 4 | 5 | 6 | 7 | VII-1 | Ngp | | |
| 1397 | 3 | 4 | 5 | 6 | 7 | VII-1 | Mir7647 | | | 1488 | 3 | 4 | 5 | 6 | 7 | VII-1 | Nipal2 | 79815 | 4-May-15 |
| 1398 | 3 | 4 | 5 | 6 | 7 | VII-1 | Mir7649 | | | 1489 | 3 | 4 | 5 | 6 | 7 | VII-1 | Nov | 4856 | 7-Jun-15 |
| 1399 | 3 | 4 | 5 | 6 | 7 | VII-1 | Mir7650 | | | 1490 | 3 | 4 | 5 | 6 | 7 | VII-1 | Nox4 | 50507 | 10-May-15 |
| 1400 | 3 | 4 | 5 | 6 | 7 | VII-1 | Mir7653 | | | 1491 | 3 | 4 | 5 | 6 | 7 | VII-1 | Nptx1 | 4884 | 3-May-15 |
| 1401 | 3 | 4 | 5 | 6 | 7 | VII-1 | Mir7655 | | | 1492 | 3 | 4 | 5 | 6 | 7 | VII-1 | Npy | 4852 | 17-May-15 |
| | | | | | | | | | | 1493 | 3 | 4 | 5 | 6 | 7 | VII-1 | Nr4a1 | 3164 | 3-May-15 |
| | | | | | | | | | | 1494 | 3 | 4 | 5 | 6 | 7 | VII-1 | Nr4a3 | 8013 | 4-May-15 |

Fig. 30 - 9

| | | | | | | | | | | | | | | | | | | |
|---|---|---|---|---|---|---|---|---|---|---|---|---|---|---|---|---|---|---|
| 1495 | 3 | 4 | 5 | 6 | 7 | VII-1 | Nuf2 | 83540 | 4-May-15 | 1590 | 3 | 4 | 5 | 6 | 7 | VII-1 | Scx | 642658 | 4-May-15 |
| 1496 | 3 | 4 | 5 | 6 | 7 | VII-1 | Nupr1 | 26471 | 4-May-15 | 1591 | 3 | 4 | 5 | 6 | 7 | VII-1 | Sec14l3 | 266629 | 4-May-15 |
| 1497 | 3 | 4 | 5 | 6 | 7 | VII-1 | Nusap1 | 51203 | 4-May-15 | 1592 | 3 | 4 | 5 | 6 | 7 | VII-1 | Serpina1f | | |
| 1498 | 3 | 4 | 5 | 6 | 7 | VII-1 | Nxf3 | 56000 | 12-May-15 | 1593 | 3 | 4 | 5 | 6 | 7 | VII-1 | Serpinb12 | 89777 | 20-May-15 |
| 1499 | 3 | 4 | 5 | 6 | 7 | VII-1 | Nxpe2 | 120406 | 4-May-15 | 1594 | 3 | 4 | 5 | 6 | 7 | VII-1 | Serpinb1c | | |
| 1500 | 3 | 4 | 5 | 6 | 7 | VII-1 | Nxpe5 | | | 1595 | 3 | 4 | 5 | 6 | 7 | VII-1 | Serpinb2 | 5055 | 17-May-15 |
| 1501 | 3 | 4 | 5 | 6 | 7 | VII-1 | Oas2 | 4939 | 4-May-15 | 1596 | 3 | 4 | 5 | 6 | 7 | VII-1 | Serpine1 | 5054 | 24-May-15 |
| 1502 | 3 | 4 | 5 | 6 | 7 | VII-1 | Odf1 | 4956 | 4-May-15 | 1597 | 3 | 4 | 5 | 6 | 7 | VII-1 | Serpinf2 | 5345 | 20-May-15 |
| 1503 | 3 | 4 | 5 | 6 | 7 | VII-1 | Otof | 9381 | 23-May-15 | 1598 | 3 | 4 | 5 | 6 | 7 | VII-1 | Sfrp2 | 6423 | 4-May-15 |
| 1504 | 3 | 4 | 5 | 6 | 7 | VII-1 | Otud1 | 220213 | 4-May-15 | 1599 | 3 | 4 | 5 | 6 | 7 | VII-1 | Sftpa1 | 653509 | 23-May-15 |
| 1505 | 3 | 4 | 5 | 6 | 7 | VII-1 | Ovch2 | 341277 | 4-May-15 | 1600 | 3 | 4 | 5 | 6 | 7 | VII-1 | Sftpb | 6439 | 12-May-15 |
| 1506 | 3 | 4 | 5 | 6 | 7 | VII-1 | P2rx2 | 22953 | 21-May-15 | 1601 | 3 | 4 | 5 | 6 | 7 | VII-1 | Sftpd | 6441 | 12-May-15 |
| 1507 | 3 | 4 | 5 | 6 | 7 | VII-1 | Pate2 | 399967 | 4-May-15 | 1602 | 3 | 4 | 5 | 6 | 7 | VII-1 | Sh2d5 | 400745 | 4-May-15 |
| 1508 | 3 | 4 | 5 | 6 | 7 | VII-1 | Pax2 | 5076 | 23-May-15 | 1603 | 3 | 4 | 5 | 6 | 7 | VII-1 | Sh3gl3 | 6457 | 4-May-15 |
| 1509 | 3 | 4 | 5 | 6 | 7 | VII-1 | Pax5 | 5079 | 17-May-15 | 1604 | 3 | 4 | 5 | 6 | 7 | VII-1 | Siglecg | | |
| 1510 | 3 | 4 | 5 | 6 | 7 | VII-1 | Pbk | 55872 | 24-May-15 | 1605 | 3 | 4 | 5 | 6 | 7 | VII-1 | Slamf6 | 114836 | 4-May-15 |
| 1511 | 3 | 4 | 5 | 6 | 7 | VII-1 | Pck1 | 5105 | 4-May-15 | 1606 | 3 | 4 | 5 | 6 | 7 | VII-1 | Slamf7 | 57823 | 4-May-15 |
| 1512 | 3 | 4 | 5 | 6 | 7 | VII-1 | Pctp | 58488 | 4-May-15 | 1607 | 3 | 4 | 5 | 6 | 7 | VII-1 | Slc15a2 | 6565 | 4-May-15 |
| 1513 | 3 | 4 | 5 | 6 | 7 | VII-1 | Pde2a | 5138 | 21-May-15 | 1608 | 3 | 4 | 5 | 6 | 7 | VII-1 | Slc16a3 | 9123 | 4-May-15 |
| 1514 | 3 | 4 | 5 | 6 | 7 | VII-1 | Pemt | 10400 | 7-Jun-15 | 1609 | 3 | 4 | 5 | 6 | 7 | VII-1 | Slc17a9 | 63910 | 23-May-15 |
| 1515 | 3 | 4 | 5 | 6 | 7 | VII-1 | Pga5 | 5222 | 4-May-15 | 1610 | 3 | 4 | 5 | 6 | 7 | VII-1 | Slc1a5 | 6510 | 4-May-15 |
| 1516 | 3 | 4 | 5 | 6 | 7 | VII-1 | Pgf | 5228 | 21-May-15 | 1611 | 3 | 4 | 5 | 6 | 7 | VII-1 | Slc34a2 | 10568 | 17-May-15 |
| 1517 | 3 | 4 | 5 | 6 | 7 | VII-1 | Phgdh | 26227 | 13-May-15 | 1612 | 3 | 4 | 5 | 6 | 7 | VII-1 | Slc38a5 | 92745 | 4-May-15 |
| 1518 | 3 | 4 | 5 | 6 | 7 | VII-1 | Pip5k1b | 8395 | 12-May-15 | 1613 | 3 | 4 | 5 | 6 | 7 | VII-1 | Slc41a2 | 84102 | 4-May-15 |
| 1519 | 3 | 4 | 5 | 6 | 7 | VII-1 | Pisd-ps1 | | | 1614 | 3 | 4 | 5 | 6 | 7 | VII-1 | Slc46a2 | 57864 | 4-May-15 |
| 1520 | 3 | 4 | 5 | 6 | 7 | VII-1 | Plac8 | 51316 | 7-Jun-15 | 1615 | 3 | 4 | 5 | 6 | 7 | VII-1 | Slc9a2 | 6549 | 12-May-15 |
| 1521 | 3 | 4 | 5 | 6 | 7 | VII-1 | Plaur | 5329 | 17-May-15 | 1616 | 3 | 4 | 5 | 6 | 7 | VII-1 | Slco4a1 | 28231 | 4-May-15 |
| 1522 | 3 | 4 | 5 | 6 | 7 | VII-1 | Plin1 | 5346 | 12-May-15 | 1617 | 3 | 4 | 5 | 6 | 7 | VII-1 | Slfn1 | | |
| 1523 | 3 | 4 | 5 | 6 | 7 | VII-1 | Pln | 5350 | 23-May-15 | 1618 | 3 | 4 | 5 | 6 | 7 | VII-1 | Slfn2 | | |
| 1524 | 3 | 4 | 5 | 6 | 7 | VII-1 | Pomc | 5443 | 23-May-15 | 1619 | 3 | 4 | 5 | 6 | 7 | VII-1 | Slfn4 | | |
| 1525 | 3 | 4 | 5 | 6 | 7 | VII-1 | Pou2af1 | 5450 | 4-May-15 | 1620 | 3 | 4 | 5 | 6 | 7 | VII-1 | Slit1 | 6585 | 7-Jun-15 |
| 1526 | 3 | 4 | 5 | 6 | 7 | VII-1 | Pou3f3os | | | 1621 | 3 | 4 | 5 | 6 | 7 | VII-1 | Smo1 | 10650 | 12-May-15 |
| 1527 | 3 | 4 | 5 | 6 | 7 | VII-1 | Ppbp | 5473 | 12-May-15 | 1622 | 3 | 4 | 5 | 6 | 7 | VII-1 | Sln | 6588 | 12-May-15 |
| 1528 | 3 | 4 | 5 | 6 | 7 | VII-1 | Ppm1e | 22843 | 4-May-15 | 1623 | 3 | 4 | 5 | 6 | 7 | VII-1 | Slpi | 6590 | 4-May-15 |
| 1529 | 3 | 4 | 5 | 6 | 7 | VII-1 | Prelid2 | 153768 | 4-May-15 | 1624 | 3 | 4 | 5 | 6 | 7 | VII-1 | Smcp | 4184 | 4-May-15 |
| 1530 | 3 | 4 | 5 | 6 | 7 | VII-1 | Prg2 | 5553 | 7-Jun-15 | 1625 | 3 | 4 | 5 | 6 | 7 | VII-1 | Smpx | 23676 | 23-May-15 |
| 1531 | 3 | 4 | 5 | 6 | 7 | VII-1 | Prkcb | 5579 | 24-May-15 | 1626 | 3 | 4 | 5 | 6 | 7 | VII-1 | Snn | 8303 | 4-May-15 |
| 1532 | 3 | 4 | 5 | 6 | 7 | VII-1 | Prl | 5617 | 17-May-15 | 1627 | 3 | 4 | 5 | 6 | 7 | VII-1 | Snora15 | 677803 | 4-May-15 |
| 1533 | 3 | 4 | 5 | 6 | 7 | VII-1 | Prokr1 | 10887 | 4-May-15 | 1628 | 3 | 4 | 5 | 6 | 7 | VII-1 | Snora16a | 692073 | 4-May-15 |
| 1534 | 3 | 4 | 5 | 6 | 7 | VII-1 | Prom2 | 150696 | 4-May-15 | 1629 | 3 | 4 | 5 | 6 | 7 | VII-1 | Snora19 | 641451 | 4-May-15 |
| 1535 | 3 | 4 | 5 | 6 | 7 | VII-1 | Prr11 | 55771 | 17-May-15 | 1630 | 3 | 4 | 5 | 6 | 7 | VII-1 | Snora20 | 677806 | 4-May-15 |
| 1536 | 3 | 4 | 5 | 6 | 7 | VII-1 | Prss22 | 64063 | 12-May-15 | 1631 | 3 | 4 | 5 | 6 | 7 | VII-1 | Snora21 | 619505 | 4-May-15 |
| 1537 | 3 | 4 | 5 | 6 | 7 | VII-1 | Prtn3 | 5657 | 17-May-15 | 1632 | 3 | 4 | 5 | 6 | 7 | VII-1 | Snora24 | 677809 | 21-May-15 |
| 1538 | 3 | 4 | 5 | 6 | 7 | VII-1 | Psrc1 | 84722 | 4-May-15 | 1633 | 3 | 4 | 5 | 6 | 7 | VII-1 | Snora26 | 677810 | 4-May-15 |
| 1539 | 3 | 4 | 5 | 6 | 7 | VII-1 | Pstpip1 | 9051 | 12-May-15 | 1634 | 3 | 4 | 5 | 6 | 7 | VII-1 | Snora2b | 677794 | 4-May-15 |
| 1540 | 3 | 4 | 5 | 6 | 7 | VII-1 | Ptgr1 | 22949 | 4-May-15 | 1635 | 3 | 4 | 5 | 6 | 7 | VII-1 | Snora33 | 594839 | 4-May-15 |
| 1541 | 3 | 4 | 5 | 6 | 7 | VII-1 | Ptgs2 | 5743 | 24-May-15 | 1636 | 3 | 4 | 5 | 6 | 7 | VII-1 | Snora35 | 677816 | 4-May-15 |
| 1542 | 3 | 4 | 5 | 6 | 7 | VII-1 | Ptn | 5764 | 17-May-15 | 1637 | 3 | 4 | 5 | 6 | 7 | VII-1 | Snora36b | 677818 | 4-May-15 |
| 1543 | 3 | 4 | 5 | 6 | 7 | VII-1 | Ptpn5 | 84867 | 12-May-15 | 1638 | 3 | 4 | 5 | 6 | 7 | VII-1 | Snora43 | 619569 | 4-May-15 |
| 1544 | 3 | 4 | 5 | 6 | 7 | VII-1 | Ptprcap | 5790 | 4-May-15 | 1639 | 3 | 4 | 5 | 6 | 7 | VII-1 | Snora44 | 677825 | 4-May-15 |
| 1545 | 3 | 4 | 5 | 6 | 7 | VII-1 | Ptx3 | 5806 | 24-May-15 | 1640 | 3 | 4 | 5 | 6 | 7 | VII-1 | Snora47 | 677828 | 4-May-15 |
| 1546 | 3 | 4 | 5 | 6 | 7 | VII-1 | Pygm | 5837 | 23-May-15 | 1641 | 3 | 4 | 5 | 6 | 7 | VII-1 | Snora52 | 619565 | 4-May-15 |
| 1547 | 3 | 4 | 5 | 6 | 7 | VII-1 | Pyhin1 | 149628 | 4-May-15 | 1642 | 3 | 4 | 5 | 6 | 7 | VII-1 | Snora5c | 677796 | 4-May-15 |
| 1548 | 3 | 4 | 5 | 6 | 7 | VII-1 | Rac2 | 5880 | 4-May-15 | 1643 | 3 | 4 | 5 | 6 | 7 | VII-1 | Snora61 | 677838 | 4-May-15 |
| 1549 | 3 | 4 | 5 | 6 | 7 | VII-1 | Rad51 | 5888 | 24-May-15 | 1644 | 3 | 4 | 5 | 6 | 7 | VII-1 | Snora62 | 6044 | 4-May-15 |
| 1550 | 3 | 4 | 5 | 6 | 7 | VII-1 | Rag1 | 5896 | 23-May-15 | 1645 | 3 | 4 | 5 | 6 | 7 | VII-1 | Snora64 | 26784 | 4-May-15 |
| 1551 | 3 | 4 | 5 | 6 | 7 | VII-1 | Ramp3 | 10268 | 12-May-15 | 1646 | 3 | 4 | 5 | 6 | 7 | VII-1 | Snora68 | 26780 | 4-May-15 |
| 1552 | 3 | 4 | 5 | 6 | 7 | VII-1 | Rasgrf1 | 5923 | 4-May-15 | 1647 | 3 | 4 | 5 | 6 | 7 | VII-1 | Snora69 | 26779 | 4-May-15 |
| 1553 | 3 | 4 | 5 | 6 | 7 | VII-1 | Rasl10a | 10633 | 4-May-15 | 1648 | 3 | 4 | 5 | 6 | 7 | VII-1 | Snora75 | 654321 | 4-May-15 |
| 1554 | 3 | 4 | 5 | 6 | 7 | VII-1 | Rbm11 | 54033 | 4-May-15 | 1649 | 3 | 4 | 5 | 6 | 7 | VII-1 | Snord100 | 594838 | 4-May-15 |
| 1555 | 3 | 4 | 5 | 6 | 7 | VII-1 | Reg2 | | | 1650 | 3 | 4 | 5 | 6 | 7 | VII-1 | Snord11 | 692058 | 4-May-15 |
| 1556 | 3 | 4 | 5 | 6 | 7 | VII-1 | Reg3g | 130120 | 4-May-15 | 1651 | 3 | 4 | 5 | 6 | 7 | VII-1 | Snord110 | 692233 | 4-May-15 |
| 1557 | 3 | 4 | 5 | 6 | 7 | VII-1 | Retn | 56729 | 17-May-15 | 1652 | 3 | 4 | 5 | 6 | 7 | VII-1 | Snord111 | 692214 | 4-May-15 |
| 1558 | 3 | 4 | 5 | 6 | 7 | VII-1 | Retnla | | | 1653 | 3 | 4 | 5 | 6 | 7 | VII-1 | Snord116 | | |
| 1559 | 3 | 4 | 5 | 6 | 7 | VII-1 | Retnlg | | | 1654 | 3 | 4 | 5 | 6 | 7 | VII-1 | Snord116l1 | | |
| 1560 | 3 | 4 | 5 | 6 | 7 | VII-1 | Rgs16 | 6004 | 4-May-15 | 1655 | 3 | 4 | 5 | 6 | 7 | VII-1 | Snord12 | 692057 | 4-May-15 |
| 1561 | 3 | 4 | 5 | 6 | 7 | VII-1 | Rhbg | 57127 | 12-May-15 | 1656 | 3 | 4 | 5 | 6 | 7 | VII-1 | Snord123 | 100113384 | 4-May-15 |
| 1562 | 3 | 4 | 5 | 6 | 7 | VII-1 | Rhcg | 51458 | 12-May-15 | 1657 | 3 | 4 | 5 | 6 | 7 | VII-1 | Snord16a | | |
| 1563 | 3 | 4 | 5 | 6 | 7 | VII-1 | Rhoh | 399 | 12-May-15 | 1658 | 3 | 4 | 5 | 6 | 7 | VII-1 | Snord19 | 692089 | 4-May-15 |
| 1564 | 3 | 4 | 5 | 6 | 7 | VII-1 | Rhpn1 | 114822 | 4-May-15 | 1659 | 3 | 4 | 5 | 6 | 7 | VII-1 | Snord1a | 677848 | 4-May-15 |
| 1565 | 3 | 4 | 5 | 6 | 7 | VII-1 | Rn45s | 100861532 | 4-May-15 | 1660 | 3 | 4 | 5 | 6 | 7 | VII-1 | Snord1b | 677849 | 4-May-15 |
| 1566 | 3 | 4 | 5 | 6 | 7 | VII-1 | Rnase11 | 122651 | 4-May-15 | 1661 | 3 | 4 | 5 | 6 | 7 | VII-1 | Snord1c | 677850 | 4-May-15 |
| 1567 | 3 | 4 | 5 | 6 | 7 | VII-1 | Rnase12 | 493901 | 4-May-15 | 1662 | 3 | 4 | 5 | 6 | 7 | VII-1 | Snord23 | 692091 | 4-May-15 |
| 1568 | 3 | 4 | 5 | 6 | 7 | VII-1 | Rnase13 | 440163 | 4-May-15 | 1663 | 3 | 4 | 5 | 6 | 7 | VII-1 | Snord34 | 26817 | 4-May-15 |
| 1569 | 3 | 4 | 5 | 6 | 7 | VII-1 | Rnase9 | 390443 | 4-May-15 | 1664 | 3 | 4 | 5 | 6 | 7 | VII-1 | Snord35b | 84546 | 4-May-15 |
| 1570 | 3 | 4 | 5 | 6 | 7 | VII-1 | Rnf149 | 284996 | 4-May-15 | 1665 | 3 | 4 | 5 | 6 | 7 | VII-1 | Snord37 | 26812 | 4-May-15 |
| 1571 | 3 | 4 | 5 | 6 | 7 | VII-1 | Rnu11 | 26824 | 7-Jun-15 | 1666 | 3 | 4 | 5 | 6 | 7 | VII-1 | Snord38a | 94162 | 12-May-15 |
| 1572 | 3 | 4 | 5 | 6 | 7 | VII-1 | Rnu73b | 114655 | 4-May-15 | 1667 | 3 | 4 | 5 | 6 | 7 | VII-1 | Snord42a | 26809 | 4-May-15 |
| 1573 | 3 | 4 | 5 | 6 | 7 | VII-1 | Ros1 | 6098 | 12-May-15 | 1668 | 3 | 4 | 5 | 6 | 7 | VII-1 | Snord42b | 26808 | 4-May-15 |
| 1574 | 3 | 4 | 5 | 6 | 7 | VII-1 | Rps27 | 6232 | 17-May-15 | 1669 | 3 | 4 | 5 | 6 | 7 | VII-1 | Snord45b | 26804 | 4-May-15 |
| 1575 | 3 | 4 | 5 | 6 | 7 | VII-1 | Rptn | 126638 | 4-May-15 | 1670 | 3 | 4 | 5 | 6 | 7 | VII-1 | Snord45c | 692085 | 4-May-15 |
| 1576 | 3 | 4 | 5 | 6 | 7 | VII-1 | Rrm2 | 6241 | 4-May-15 | 1671 | 3 | 4 | 5 | 6 | 7 | VII-1 | Snord49a | 26800 | 4-May-15 |
| 1577 | 3 | 4 | 5 | 6 | 7 | VII-1 | Rsph1 | 89765 | 4-May-15 | 1672 | 3 | 4 | 5 | 6 | 7 | VII-1 | Snord49b | 692087 | 4-May-15 |
| 1578 | 3 | 4 | 5 | 6 | 7 | VII-1 | S100a8 | 6279 | 3-May-15 | 1673 | 3 | 4 | 5 | 6 | 7 | VII-1 | Snord4a | 26773 | 4-May-15 |
| 1579 | 3 | 4 | 5 | 6 | 7 | VII-1 | S100a9 | 6280 | 24-May-15 | 1674 | 3 | 4 | 5 | 6 | 7 | VII-1 | Snord52 | 26797 | 4-May-15 |
| 1580 | 3 | 4 | 5 | 6 | 7 | VII-1 | S100b | 6285 | 4-May-15 | 1675 | 3 | 4 | 5 | 6 | 7 | VII-1 | Snord53 | 26796 | 4-May-15 |
| 1581 | 3 | 4 | 5 | 6 | 7 | VII-1 | Saa3 | 6290 | 4-May-15 | 1676 | 3 | 4 | 5 | 6 | 7 | VII-1 | Snord55 | 26811 | 4-May-15 |
| 1582 | 3 | 4 | 5 | 6 | 7 | VII-1 | Scarna10 | 692148 | 4-May-15 | 1677 | 3 | 4 | 5 | 6 | 7 | VII-1 | Snord57 | 26792 | 4-May-15 |
| 1583 | 3 | 4 | 5 | 6 | 7 | VII-1 | Scarna17 | 677769 | 12-May-15 | 1678 | 3 | 4 | 5 | 6 | 7 | VII-1 | Snord58b | 26790 | 4-May-15 |
| 1584 | 3 | 4 | 5 | 6 | 7 | VII-1 | Scarna3b | | | 1679 | 3 | 4 | 5 | 6 | 7 | VII-1 | Snord61 | 26787 | 4-May-15 |
| 1585 | 3 | 4 | 5 | 6 | 7 | VII-1 | Scarna8 | 677776 | 4-May-15 | 1680 | 3 | 4 | 5 | 6 | 7 | VII-1 | Snord64 | 347686 | 4-May-15 |
| 1586 | 3 | 4 | 5 | 6 | 7 | VII-1 | Scarna9 | 619383 | 12-May-15 | 1681 | 3 | 4 | 5 | 6 | 7 | VII-1 | Snord65 | 692106 | 4-May-15 |
| 1587 | 3 | 4 | 5 | 6 | 7 | VII-1 | Scgb3a1 | 92304 | 4-May-15 | 1682 | 3 | 4 | 5 | 6 | 7 | VII-1 | Snord66 | 692107 | 4-May-15 |
| 1588 | 3 | 4 | 5 | 6 | 7 | VII-1 | Scgb3a2 | 117156 | 12-May-15 | 1683 | 3 | 4 | 5 | 6 | 7 | VII-1 | Snord67 | 692108 | 4-May-15 |
| 1589 | 3 | 4 | 5 | 6 | 7 | VII-1 | Scn4b | 6330 | 23-May-15 | 1684 | 3 | 4 | 5 | 6 | 7 | VII-1 | Snord68 | 606500 | 4-May-15 |

Fig. 30 - 10

| # | | | | | | Grp | Gene | ID | Date |
|---|---|---|---|---|---|---|---|---|---|
| 1685 | 3 | 4 | 5 | 6 | 7 | VII-1 | Snord69 | 692109 | 4-May-15 |
| 1686 | 3 | 4 | 5 | 6 | 7 | VII-1 | Snord7 | 692076 | 4-May-15 |
| 1687 | 3 | 4 | 5 | 6 | 7 | VII-1 | Snord70 | 692110 | 4-May-15 |
| 1688 | 3 | 4 | 5 | 6 | 7 | VII-1 | Snord71 | 692111 | 4-May-15 |
| 1689 | 3 | 4 | 5 | 6 | 7 | VII-1 | Snord72 | 619564 | 4-May-15 |
| 1690 | 3 | 4 | 5 | 6 | 7 | VII-1 | Snord73a | 8844 | 4-May-15 |
| 1691 | 3 | 4 | 5 | 6 | 7 | VII-1 | Snord8 | 319103 | 4-May-15 |
| 1692 | 3 | 4 | 5 | 6 | 7 | VII-1 | Snord82 | 25826 | 12-May-15 |
| 1693 | 3 | 4 | 5 | 6 | 7 | VII-1 | Snord83b | 116938 | 4-May-15 |
| 1694 | 3 | 4 | 5 | 6 | 7 | VII-1 | Snord85 | 692200 | 4-May-15 |
| 1695 | 3 | 4 | 5 | 6 | 7 | VII-1 | Snord87 | 641648 | 4-May-15 |
| 1696 | 3 | 4 | 5 | 6 | 7 | VII-1 | Snord88a | 692202 | 4-May-15 |
| 1697 | 3 | 4 | 5 | 6 | 7 | VII-1 | Snord88c | 692204 | 4-May-15 |
| 1698 | 3 | 4 | 5 | 6 | 7 | VII-1 | Snord89 | 692205 | 4-May-15 |
| 1699 | 3 | 4 | 5 | 6 | 7 | VII-1 | Snord90 | 692206 | 4-May-15 |
| 1700 | 3 | 4 | 5 | 6 | 7 | VII-1 | Snord92 | 692209 | 4-May-15 |
| 1701 | 3 | 4 | 5 | 6 | 7 | VII-1 | Snord93 | 692210 | 4-May-15 |
| 1702 | 3 | 4 | 5 | 6 | 7 | VII-1 | Snord95 | 619570 | 4-May-15 |
| 1703 | 3 | 4 | 5 | 6 | 7 | VII-1 | Snord99 | 692212 | 4-May-15 |
| 1704 | 3 | 4 | 5 | 6 | 7 | VII-1 | Spag11a | 653423 | 4-May-15 |
| 1705 | 3 | 4 | 5 | 6 | 7 | VII-1 | Spag11b | 10407 | 14-May-15 |
| 1706 | 3 | 4 | 5 | 6 | 7 | VII-1 | Spag5 | 10615 | 4-May-15 |
| 1707 | 3 | 4 | 5 | 6 | 7 | VII-1 | Spata3 | 130560 | 4-May-15 |
| 1708 | 3 | 4 | 5 | 6 | 7 | VII-1 | Spdef | 25803 | 20-May-15 |
| 1709 | 3 | 4 | 5 | 6 | 7 | VII-1 | Sphk1 | 8877 | 12-May-15 |
| 1710 | 3 | 4 | 5 | 6 | 7 | VII-1 | Spib | 6689 | 12-May-15 |
| 1711 | 3 | 4 | 5 | 6 | 7 | VII-1 | Spin2c | | |
| 1712 | 3 | 4 | 5 | 6 | 7 | VII-1 | Spink10 | | |
| 1713 | 3 | 4 | 5 | 6 | 7 | VII-1 | Spink11 | | |
| 1714 | 3 | 4 | 5 | 6 | 7 | VII-1 | Spink12 | | |
| 1715 | 3 | 4 | 5 | 6 | 7 | VII-1 | Spink2 | 6691 | 4-May-15 |
| 1716 | 3 | 4 | 5 | 6 | 7 | VII-1 | Spink5 | 11005 | 12-May-15 |
| 1717 | 3 | 4 | 5 | 6 | 7 | VII-1 | Spink8 | 646424 | 4-May-15 |
| 1718 | 3 | 4 | 5 | 6 | 7 | VII-1 | Spinkl | | |
| 1719 | 3 | 4 | 5 | 6 | 7 | VII-1 | Spint4 | 391253 | 4-May-15 |
| 1720 | 3 | 4 | 5 | 6 | 7 | VII-1 | Spint5 | | |
| 1721 | 3 | 4 | 5 | 6 | 7 | VII-1 | Sprr1a | 6698 | 12-May-15 |
| 1722 | 3 | 4 | 5 | 6 | 7 | VII-1 | Sprr2f | 6705 | 4-May-15 |
| 1723 | 3 | 4 | 5 | 6 | 7 | VII-1 | Sprr3 | 6707 | 12-May-15 |
| 1724 | 3 | 4 | 5 | 6 | 7 | VII-1 | Ss18l1 | 26039 | 4-May-15 |
| 1725 | 3 | 4 | 5 | 6 | 7 | VII-1 | St6gal1 | 6480 | 12-May-15 |
| 1726 | 3 | 4 | 5 | 6 | 7 | VII-1 | St8sia5 | 29906 | 12-May-15 |
| 1727 | 3 | 4 | 5 | 6 | 7 | VII-1 | Stambpl1 | 57559 | 4-May-15 |
| 1728 | 3 | 4 | 5 | 6 | 7 | VII-1 | Stap1 | 26228 | 7-Jun-15 |
| 1729 | 3 | 4 | 5 | 6 | 7 | VII-1 | Stc1 | 6781 | 12-May-15 |
| 1730 | 3 | 4 | 5 | 6 | 7 | VII-1 | Steap4 | 79689 | 4-May-15 |
| 1731 | 3 | 4 | 5 | 6 | 7 | VII-1 | Stfa2l1 | | |
| 1732 | 3 | 4 | 5 | 6 | 7 | VII-1 | Stmn1 | 3925 | 24-May-15 |
| 1733 | 3 | 4 | 5 | 6 | 7 | VII-1 | Sult2b1 | 6820 | 4-May-15 |
| 1734 | 3 | 4 | 5 | 6 | 7 | VII-1 | Susd3 | 64420 | 4-May-15 |
| 1735 | 3 | 4 | 5 | 6 | 7 | VII-1 | Svs5 | | |
| 1736 | 3 | 4 | 5 | 6 | 7 | VII-1 | Syk | 6850 | 10-May-15 |
| 1737 | 3 | 4 | 5 | 6 | 7 | VII-1 | Syndig1l | 646658 | 4-May-15 |
| 1738 | 3 | 4 | 5 | 6 | 7 | VII-1 | Synpr | 132204 | 4-May-15 |
| 1739 | 3 | 4 | 5 | 6 | 7 | VII-1 | Sytl4 | 94121 | 4-May-15 |
| 1740 | 3 | 4 | 5 | 6 | 7 | VII-1 | Tacstd2 | 4070 | 12-May-15 |
| 1741 | 3 | 4 | 5 | 6 | 7 | VII-1 | Tcf7 | 6932 | 12-May-15 |
| 1742 | 3 | 4 | 5 | 6 | 7 | VII-1 | Tchh | 7062 | 12-May-15 |
| 1743 | 3 | 4 | 5 | 6 | 7 | VII-1 | Tdrd5 | 163589 | 4-May-15 |
| 1744 | 3 | 4 | 5 | 6 | 7 | VII-1 | Teddm1 | 127670 | 4-May-15 |
| 1745 | 3 | 4 | 5 | 6 | 7 | VII-1 | Tfap2a | 7020 | 23-May-15 |
| 1746 | 3 | 4 | 5 | 6 | 7 | VII-1 | Tfap2b | 7021 | 23-May-15 |
| 1747 | 3 | 4 | 5 | 6 | 7 | VII-1 | Tff2 | 7032 | 12-May-15 |
| 1748 | 3 | 4 | 5 | 6 | 7 | VII-1 | Tgm3 | 7053 | 12-May-15 |
| 1749 | 3 | 4 | 5 | 6 | 7 | VII-1 | Thbs1 | 7057 | 12-May-15 |
| 1750 | 3 | 4 | 5 | 6 | 7 | VII-1 | Them5 | 284486 | 4-May-15 |
| 1751 | 3 | 4 | 5 | 6 | 7 | VII-1 | Tifa | 92610 | 7-Jun-15 |
| 1752 | 3 | 4 | 5 | 6 | 7 | VII-1 | Timp1 | 7076 | 12-May-15 |
| 1753 | 3 | 4 | 5 | 6 | 7 | VII-1 | Tmem132e | 124842 | 4-May-15 |
| 1754 | 3 | 4 | 5 | 6 | 7 | VII-1 | Tmem150c | 441027 | 4-May-15 |
| 1755 | 3 | 4 | 5 | 6 | 7 | VII-1 | Tmem30b | 161291 | 4-May-15 |
| 1756 | 3 | 4 | 5 | 6 | 7 | VII-1 | Tmem51 | 55092 | 4-May-15 |
| 1757 | 3 | 4 | 5 | 6 | 7 | VII-1 | Tnc | 3371 | 7-Jun-15 |
| 1758 | 3 | 4 | 5 | 6 | 7 | VII-1 | Tnnc1 | 7134 | 7-Jun-15 |
| 1759 | 3 | 4 | 5 | 6 | 7 | VII-1 | Tnni2 | 7136 | 4-May-15 |
| 1760 | 3 | 4 | 5 | 6 | 7 | VII-1 | Tnni3 | 7137 | 23-May-15 |
| 1761 | 3 | 4 | 5 | 6 | 7 | VII-1 | Tnnt2 | 7139 | 23-May-15 |
| 1762 | 3 | 4 | 5 | 6 | 7 | VII-1 | Tnnt3 | 7140 | 12-May-15 |
| 1763 | 3 | 4 | 5 | 6 | 7 | VII-1 | Top2a | 7153 | 12-May-15 |
| 1764 | 3 | 4 | 5 | 6 | 7 | VII-1 | Tox3 | 27324 | 4-May-15 |
| 1765 | 3 | 4 | 5 | 6 | 7 | VII-1 | Tpsab1 | 7177 | 12-May-15 |
| 1766 | 3 | 4 | 5 | 6 | 7 | VII-1 | Tpx2 | 22974 | 4-May-15 |
| 1767 | 3 | 4 | 5 | 6 | 7 | VII-1 | Trank1 | 9881 | 12-May-15 |
| 1768 | 3 | 4 | 5 | 6 | 7 | VII-1 | Trem2 | 54209 | 23-May-15 |
| 1769 | 3 | 4 | 5 | 6 | 7 | VII-1 | Trpc5os | 100329135 | 4-May-15 |
| 1770 | 3 | 4 | 5 | 6 | 7 | VII-1 | Trpm3 | 80036 | 4-May-15 |
| 1771 | 3 | 4 | 5 | 6 | 7 | VII-1 | Trpv6 | 55503 | 20-May-15 |
| 1772 | 3 | 4 | 5 | 6 | 7 | VII-1 | Tspan13 | 27075 | 12-May-15 |
| 1773 | 3 | 4 | 5 | 6 | 7 | VII-1 | Ube2c | 11065 | 4-May-15 |
| 1774 | 3 | 4 | 5 | 6 | 7 | VII-1 | Ubxn10 | 127733 | 4-May-15 |
| 1775 | 3 | 4 | 5 | 6 | 7 | VII-1 | Uchl1 | 7345 | 23-May-15 |
| 1776 | 3 | 4 | 5 | 6 | 7 | VII-1 | Ucp2 | 7351 | 12-May-15 |
| 1777 | 3 | 4 | 5 | 6 | 7 | VII-1 | Uhrf1 | 29128 | 12-May-15 |
| 1778 | 3 | 4 | 5 | 6 | 7 | VII-1 | Unc5cl | 222643 | 4-May-15 |
| 1779 | 3 | 4 | 5 | 6 | 7 | VII-1 | Upk1a | 11045 | 4-May-15 |
| 1780 | 3 | 4 | 5 | 6 | 7 | VII-1 | Vash2 | 79805 | 4-May-15 |
| 1781 | 3 | 4 | 5 | 6 | 7 | VII-1 | Vcan | 1462 | 23-May-15 |
| 1782 | 3 | 4 | 5 | 6 | 7 | VII-1 | Vpreb1 | 7441 | 21-May-15 |
| 1783 | 3 | 4 | 5 | 6 | 7 | VII-1 | Vpreb2 | 3543 | 12-May-15 |
| 1784 | 3 | 4 | 5 | 6 | 7 | VII-1 | Vpreb3 | 29802 | 13-May-15 |
| 1785 | 3 | 4 | 5 | 6 | 7 | VII-1 | Wars | 7453 | 12-May-15 |
| 1786 | 3 | 4 | 5 | 6 | 7 | VII-1 | Wdfy4 | 57705 | 4-May-15 |
| 1787 | 3 | 4 | 5 | 6 | 7 | VII-1 | Wfdc10 | | |
| 1788 | 3 | 4 | 5 | 6 | 7 | VII-1 | Wfdc11 | 259239 | 4-May-15 |
| 1789 | 3 | 4 | 5 | 6 | 7 | VII-1 | Wfdc13 | 164237 | 4-May-15 |
| 1790 | 3 | 4 | 5 | 6 | 7 | VII-1 | Wfdc2 | 10406 | 4-May-15 |
| 1791 | 3 | 4 | 5 | 6 | 7 | VII-1 | Wfdc6a | | |
| 1792 | 3 | 4 | 5 | 6 | 7 | VII-1 | Wfdc6b | | |
| 1793 | 3 | 4 | 5 | 6 | 7 | VII-1 | Wfdc8 | 90199 | 4-May-15 |
| 1794 | 3 | 4 | 5 | 6 | 7 | VII-1 | Wfdc9 | 259240 | 4-May-15 |
| 1795 | 3 | 4 | 5 | 6 | 7 | VII-1 | Wisp2 | 8839 | 4-May-15 |
| 1796 | 3 | 4 | 5 | 6 | 7 | VII-1 | Xkrx | 402415 | 4-May-15 |
| 1797 | 3 | 4 | 5 | 6 | 7 | VII-1 | Zbtb16 | 7704 | 4-May-15 |
| 1798 | 3 | 4 | 5 | 6 | 7 | VII-1 | Zfp648 | | |
| 1799 | 3 | 4 | 5 | 6 | 7 | VII-1 | Zfp697 | | |
| 1800 | 3 | 4 | 5 | 6 | 7 | VII-1 | Zim1 | | |
| 1801 | 3 | 4 | 5 | 6 | 7 | VI-2 | 0610005C13Rik | | |
| 1802 | 3 | 4 | 5 | 6 | | VI-2 | 1110019D14Rik | | |
| 1803 | 3 | 4 | 5 | 6 | | VI-2 | 1110025L11Rik | | |
| 1804 | 3 | 4 | 5 | 6 | | VI-2 | 1110034G24Rik | | |
| 1805 | 3 | 4 | 5 | 6 | | VI-2 | 1110046J04Rik | | |
| 1806 | 3 | 4 | 5 | 6 | | VI-2 | 1600014C23Rik | | |
| 1807 | 3 | 4 | 5 | 6 | | VI-2 | 1600029I14Rik | | |
| 1808 | 3 | 4 | 5 | 6 | | VI-2 | 1700001C19Rik | | |
| 1809 | 3 | 4 | 5 | 6 | | VI-2 | 1700003M02Rik | | |
| 1810 | 3 | 4 | 5 | 6 | | VI-2 | 1700007L15Rik | | |
| 1811 | 3 | 4 | 5 | 6 | | VI-2 | 1700011H14Rik | | |
| 1812 | 3 | 4 | 5 | 6 | | VI-2 | 1700012B09Rik | | |
| 1813 | 3 | 4 | 5 | 6 | | VI-2 | 1700013F07Rik | | |
| 1814 | 3 | 4 | 5 | 6 | | VI-2 | 1700016K19Rik | | |
| 1815 | 3 | 4 | 5 | 6 | | VI-2 | 1700020L24Rik | | |
| 1816 | 3 | 4 | 5 | 6 | | VI-2 | 1700027A15Rik | | |
| 1817 | 3 | 4 | 5 | 6 | | VI-2 | 1700029I15Rik | | |
| 1818 | 3 | 4 | 5 | 6 | | VI-2 | 1700040L02Rik | | |
| 1819 | 3 | 4 | 5 | 6 | | VI-2 | 1700047G03Rik | | |
| 1820 | 3 | 4 | 5 | 6 | | VI-2 | 1700073M16Rik | | |
| 1821 | 3 | 4 | 5 | 6 | | VI-2 | 1700088E04Rik | | |
| 1822 | 3 | 4 | 5 | 6 | | VI-2 | 1700092M07Rik | | |
| 1823 | 3 | 4 | 5 | 6 | | VI-2 | 1700094D03Rik | | |
| 1824 | 3 | 4 | 5 | 6 | | VI-2 | 1700101E01Rik | | |
| 1825 | 3 | 4 | 5 | 6 | | VI-2 | 1810014B01Rik | | |
| 1826 | 3 | 4 | 5 | 6 | | VI-2 | 2010015L04Rik | | |
| 1827 | 3 | 4 | 5 | 6 | | VI-2 | 2010204K13Rik | | |
| 1828 | 3 | 4 | 5 | 6 | | VI-2 | 2210407C18Rik | | |
| 1829 | 3 | 4 | 5 | 6 | | VI-2 | 2210409E12Rik | | |
| 1830 | 3 | 4 | 5 | 6 | | VI-2 | 2310001H17Rik | | |
| 1831 | 3 | 4 | 5 | 6 | | VI-2 | 2310003K24Rik | | |
| 1832 | 3 | 4 | 5 | 6 | | VI-2 | 2310020H05Rik | | |
| 1833 | 3 | 4 | 5 | 6 | | VI-2 | 2310039L15Rik | | |
| 1834 | 3 | 4 | 5 | 6 | | VI-2 | 2310040G24Rik | | |
| 1835 | 3 | 4 | 5 | 6 | | VI-2 | 2310061N02Rik | | |
| 1836 | 3 | 4 | 5 | 6 | | VI-2 | 2310069G16Rik | | |
| 1837 | 3 | 4 | 5 | 6 | | VI-2 | 2610028H24Rik | | |
| 1838 | 3 | 4 | 5 | 6 | | VI-2 | 2610203C22Rik | | |
| 1839 | 3 | 4 | 5 | 6 | | VI-2 | 2810410J24Rik | | |
| 1840 | 3 | 4 | 5 | 6 | | VI-2 | 2810433D01Rik | | |
| 1841 | 3 | 4 | 5 | 6 | | VI-2 | 2900008C10Rik | | |
| 1842 | 3 | 4 | 5 | 6 | | VI-2 | 2900009J06Rik | | |
| 1843 | 3 | 4 | 5 | 6 | | VI-2 | 3110009E18Rik | | |
| 1844 | 3 | 4 | 5 | 6 | | VI-2 | 3110057O12Rik | | |
| 1845 | 3 | 4 | 5 | 6 | | VI-2 | 3110082I17Rik | | |
| 1846 | 3 | 4 | 5 | 6 | | VI-2 | 4430402I18Rik | | |
| 1847 | 3 | 4 | 5 | 6 | | VI-2 | 4632428C04Rik | | |
| 1848 | 3 | 4 | 5 | 6 | | VI-2 | 4833427G06Rik | | |
| 1849 | 3 | 4 | 5 | 6 | | VI-2 | 4930405D11Rik | | |
| 1850 | 3 | 4 | 5 | 6 | | VI-2 | 4930451C15Rik | | |
| 1851 | 3 | 4 | 5 | 6 | | VI-2 | 4930461G14Rik | | |
| 1852 | 3 | 4 | 5 | 6 | | VI-2 | 4930465M20Rik | | |
| 1853 | 3 | 4 | 5 | 6 | | VI-2 | 4930506C21Rik | | |
| 1854 | 3 | 4 | 5 | 6 | | VI-2 | 4930524O05Rik | | |
| 1855 | 3 | 4 | 5 | 6 | | VI-2 | 4930539J05Rik | | |
| 1856 | 3 | 4 | 5 | 6 | | VI-2 | 4930540M03Rik | | |
| 1857 | 3 | 4 | 5 | 6 | | VI-2 | 4930542C21Rik | | |
| 1858 | 3 | 4 | 5 | 6 | | VI-2 | 4930544D05Rik | | |
| 1859 | 3 | 4 | 5 | 6 | | VI-2 | 4930556M19Rik | | |
| 1860 | 3 | 4 | 5 | 6 | | VI-2 | 4930578M01Rik | | |
| 1861 | 3 | 4 | 5 | 6 | | VI-2 | 4932418E24Rik | | |
| 1862 | 3 | 4 | 5 | 6 | | VI-2 | 4932702P03Rik | | |
| 1863 | 3 | 4 | 5 | 6 | | VI-2 | 4933404K08Rik | | |
| 1864 | 3 | 4 | 5 | 6 | | VI-2 | 5031434O11Rik | | |
| 1865 | 3 | 4 | 5 | 6 | | VI-2 | 5330417C22Rik | | |
| 1866 | 3 | 4 | 5 | 6 | | VI-2 | 5430421N21Rik | | |
| 1867 | 3 | 4 | 5 | 6 | | VI-2 | 5730422E09Rik | | |
| 1868 | 3 | 4 | 5 | 6 | | VI-2 | 5830416P10Rik | | |
| 1869 | 3 | 4 | 5 | 6 | | VI-2 | 5930430L01Rik | | |
| 1870 | 3 | 4 | 5 | 6 | | VI-2 | 6330403K07Rik | | |

Fig. 30 - 11

| | | | | | | | | |
|---|---|---|---|---|---|---|---|---|
| 1871 | 3 | 4 | 5 | 6 | VI-2 | 6430571L13Rik | | |
| 1872 | 3 | 4 | 5 | 6 | VI-2 | 6430573F11Rik | | |
| 1873 | 3 | 4 | 5 | 6 | VI-2 | 6720489N17Rik | | |
| 1874 | 3 | 4 | 5 | 6 | VI-2 | 6820408C15Rik | | |
| 1875 | 3 | 4 | 5 | 6 | VI-2 | 9030617O03Rik | | |
| 1876 | 3 | 4 | 5 | 6 | VI-2 | 9030619P08Rik | | |
| 1877 | 3 | 4 | 5 | 6 | VI-2 | 9330102E08Rik | | |
| 1878 | 3 | 4 | 5 | 6 | VI-2 | 9330133O14Rik | | |
| 1879 | 3 | 4 | 5 | 6 | VI-2 | A2m | 2 | 23-May-15 |
| 1880 | 3 | 4 | 5 | 6 | VI-2 | A330035P11Rik | | |
| 1881 | 3 | 4 | 5 | 6 | VI-2 | A330069E16Rik | | |
| 1882 | 3 | 4 | 5 | 6 | VI-2 | A430107P09Rik | | |
| 1883 | 3 | 4 | 5 | 6 | VI-2 | A530064D06Rik | | |
| 1884 | 3 | 4 | 5 | 6 | VI-2 | A630019I02Rik | | |
| 1885 | 3 | 4 | 5 | 6 | VI-2 | A630076J17Rik | | |
| 1886 | 3 | 4 | 5 | 6 | VI-2 | A630095E13Rik | | |
| 1887 | 3 | 4 | 5 | 6 | VI-2 | A730020M07Rik | | |
| 1888 | 3 | 4 | 5 | 6 | VI-2 | A930001C03Rik | | |
| 1889 | 3 | 4 | 5 | 6 | VI-2 | A930016O22Rik | | |
| 1890 | 3 | 4 | 5 | 6 | VI-2 | AA388235 | | |
| 1891 | 3 | 4 | 5 | 6 | VI-2 | AA465934 | | |
| 1892 | 3 | 4 | 5 | 6 | VI-2 | Aadac | 13 | 4-May-15 |
| 1893 | 3 | 4 | 5 | 6 | VI-2 | Abca6 | 23460 | 12-May-15 |
| 1894 | 3 | 4 | 5 | 6 | VI-2 | Abhd3 | 171586 | 21-May-15 |
| 1895 | 3 | 4 | 5 | 6 | VI-2 | Acaa2 | 10449 | 4-May-15 |
| 1896 | 3 | 4 | 5 | 6 | VI-2 | Acad12 | | |
| 1897 | 3 | 4 | 5 | 6 | VI-2 | Acot11 | 26027 | 4-May-15 |
| 1898 | 3 | 4 | 5 | 6 | VI-2 | Acot3 | | |
| 1899 | 3 | 4 | 5 | 6 | VI-2 | Acot4 | 122970 | 4-May-15 |
| 1900 | 3 | 4 | 5 | 6 | VI-2 | Acsbg1 | 23205 | 4-May-15 |
| 1901 | 3 | 4 | 5 | 6 | VI-2 | Acsm5 | 54988 | 4-May-15 |
| 1902 | 3 | 4 | 5 | 6 | VI-2 | Acss1 | 84532 | 4-May-15 |
| 1903 | 3 | 4 | 5 | 6 | VI-2 | Actr3b | 57180 | 4-May-15 |
| 1904 | 3 | 4 | 5 | 6 | VI-2 | Adamts7 | 11173 | 4-May-15 |
| 1905 | 3 | 4 | 5 | 6 | VI-2 | Adamts4 | 54507 | 23-May-15 |
| 1906 | 3 | 4 | 5 | 6 | VI-2 | Adcy8 | 114 | 12-May-15 |
| 1907 | 3 | 4 | 5 | 6 | VI-2 | Adm2 | 79924 | 17-May-15 |
| 1908 | 3 | 4 | 5 | 6 | VI-2 | Adra1a | 148 | 7-Jun-15 |
| 1909 | 3 | 4 | 5 | 6 | VI-2 | Adrb1 | 153 | 24-May-15 |
| 1910 | 3 | 4 | 5 | 6 | VI-2 | Adrbk2 | 157 | 14-May-15 |
| 1911 | 3 | 4 | 5 | 6 | VI-2 | Agmo | 392636 | 4-May-15 |
| 1912 | 3 | 4 | 5 | 6 | VI-2 | AI118078 | | |
| 1913 | 3 | 4 | 5 | 6 | VI-2 | AI197445 | | |
| 1914 | 3 | 4 | 5 | 6 | VI-2 | AI314278 | | |
| 1915 | 3 | 4 | 5 | 6 | VI-2 | AI507597 | | |
| 1916 | 3 | 4 | 5 | 6 | VI-2 | AI839979 | | |
| 1917 | 3 | 4 | 5 | 6 | VI-2 | Aire | 100271873 | 12-May-15 |
| 1918 | 3 | 4 | 5 | 6 | VI-2 | AK129341 | | |
| 1919 | 3 | 4 | 5 | 6 | VI-2 | Ak7 | 122481 | 4-May-15 |
| 1920 | 3 | 4 | 5 | 6 | VI-2 | Akap4 | 8852 | 4-May-15 |
| 1921 | 3 | 4 | 5 | 6 | VI-2 | Akr1c19 | | |
| 1922 | 3 | 4 | 5 | 6 | VI-2 | Akr1e1 | | |
| 1923 | 3 | 4 | 5 | 6 | VI-2 | Aldh1b1 | 219 | 23-May-15 |
| 1924 | 3 | 4 | 5 | 6 | VI-2 | Aldh4a1 | 8659 | 23-May-15 |
| 1925 | 3 | 4 | 5 | 6 | VI-2 | Alg8 | 79053 | 23-May-15 |
| 1926 | 3 | 4 | 5 | 6 | VI-2 | Alox12 | 239 | 17-May-15 |
| 1927 | 3 | 4 | 5 | 6 | VI-2 | Alox12e | 245 | 4-May-15 |
| 1928 | 3 | 4 | 5 | 6 | VI-2 | Alox5 | 240 | 10-May-15 |
| 1929 | 3 | 4 | 5 | 6 | VI-2 | Alpk3 | 57538 | 4-May-15 |
| 1930 | 3 | 4 | 5 | 6 | VI-2 | Amhr2 | 269 | 12-May-15 |
| 1931 | 3 | 4 | 5 | 6 | VI-2 | Amn | 81693 | 7-Jun-15 |
| 1932 | 3 | 4 | 5 | 6 | VI-2 | Ang3 | | |
| 1933 | 3 | 4 | 5 | 6 | VI-2 | Ang4 | 51378 | 4-May-15 |
| 1934 | 3 | 4 | 5 | 6 | VI-2 | Angptl1 | 9068 | 4-May-15 |
| 1935 | 3 | 4 | 5 | 6 | VI-2 | Ank3 | 288 | 17-May-15 |
| 1936 | 3 | 4 | 5 | 6 | VI-2 | Ankrd33b | 651746 | 4-May-15 |
| 1937 | 3 | 4 | 5 | 6 | VI-2 | Ankrd55 | 79722 | 4-May-15 |
| 1938 | 3 | 4 | 5 | 6 | VI-2 | Ankrd66 | 100287718 | 21-May-15 |
| 1939 | 3 | 4 | 5 | 6 | VI-2 | Anks4b | 257629 | 4-May-15 |
| 1940 | 3 | 4 | 5 | 6 | VI-2 | Ano9 | 338440 | 4-May-15 |
| 1941 | 3 | 4 | 5 | 6 | VI-2 | Apbb1 | 322 | 12-May-15 |
| 1942 | 3 | 4 | 5 | 6 | VI-2 | Aplnr | 187 | 3-May-15 |
| 1943 | 3 | 4 | 5 | 6 | VI-2 | Apoa1 | 335 | 31-May-15 |
| 1944 | 3 | 4 | 5 | 6 | VI-2 | Apoa2 | 336 | 7-Jun-15 |
| 1945 | 3 | 4 | 5 | 6 | VI-2 | Apob | 338 | 17-May-15 |
| 1946 | 3 | 4 | 5 | 6 | VI-2 | Apoc3 | 345 | 12-May-15 |
| 1947 | 3 | 4 | 5 | 6 | VI-2 | Apol9b | | |
| 1948 | 3 | 4 | 5 | 6 | VI-2 | Apopt1 | 84334 | 4-May-15 |
| 1949 | 3 | 4 | 5 | 6 | VI-2 | Appbp2 | 10513 | 4-May-15 |
| 1950 | 3 | 4 | 5 | 6 | VI-2 | Aqp4 | 361 | 24-May-15 |
| 1951 | 3 | 4 | 5 | 6 | VI-2 | Arhgap20 | 57569 | 4-May-15 |
| 1952 | 3 | 4 | 5 | 6 | VI-2 | Arhgap9 | 64333 | 4-May-15 |
| 1953 | 3 | 4 | 5 | 6 | VI-2 | Armc2 | 84071 | 4-May-15 |
| 1954 | 3 | 4 | 5 | 6 | VI-2 | Asap3 | 55616 | 4-May-15 |
| 1955 | 3 | 4 | 5 | 6 | VI-2 | Asb10 | 136371 | 4-May-15 |
| 1956 | 3 | 4 | 5 | 6 | VI-2 | Asb14 | 142686 | 4-May-15 |
| 1957 | 3 | 4 | 5 | 6 | VI-2 | Asb15 | 142685 | 4-May-15 |
| 1958 | 3 | 4 | 5 | 6 | VI-2 | Asb2 | 51676 | 4-May-15 |
| 1959 | 3 | 4 | 5 | 6 | VI-2 | Aspdh | 554235 | 4-May-15 |
| 1960 | 3 | 4 | 5 | 6 | VI-2 | Atp1a4 | 480 | 4-May-15 |
| 1961 | 3 | 4 | 5 | 6 | VI-2 | Atp1b1 | 481 | 12-May-15 |
| 1962 | 3 | 4 | 5 | 6 | VI-2 | Atp2a2 | 488 | 24-May-15 |
| 1963 | 3 | 4 | 5 | 6 | VI-2 | Atp6v0a4 | 50617 | 24-May-15 |
| 1964 | 3 | 4 | 5 | 6 | VI-2 | Axl | 10677 | 4-May-15 |
| 1965 | 3 | 4 | 5 | 6 | VI-2 | Aym1 | | |
| 1966 | 3 | 4 | 5 | 6 | VI-2 | B230217O12Rik | | |
| 1967 | 3 | 4 | 5 | 6 | VI-2 | B230313C02Rik | | |
| 1968 | 3 | 4 | 5 | 6 | VI-2 | B4galnt2 | 124872 | 4-May-15 |
| 1969 | 3 | 4 | 5 | 6 | VI-2 | B4galnt3 | 283358 | 4-May-15 |
| 1970 | 3 | 4 | 5 | 6 | VI-2 | Babcc1 | 57597 | 4-May-15 |
| 1971 | 3 | 4 | 5 | 6 | VI-2 | Baiap2l1 | 55971 | 4-May-15 |
| 1972 | 3 | 4 | 5 | 6 | VI-2 | Baiap2l2 | 80115 | 4-May-15 |
| 1973 | 3 | 4 | 5 | 6 | VI-2 | BB019430 | | |
| 1974 | 3 | 4 | 5 | 6 | VI-2 | Bbox1 | 8424 | 12-May-15 |
| 1975 | 3 | 4 | 5 | 6 | VI-2 | BC029722 | | |
| 1976 | 3 | 4 | 5 | 6 | VI-2 | BC048644 | | |
| 1977 | 3 | 4 | 5 | 6 | VI-2 | BC051226 | | |
| 1978 | 3 | 4 | 5 | 6 | VI-2 | Bcar1 | 9564 | 17-May-15 |
| 1979 | 3 | 4 | 5 | 6 | VI-2 | Bche | 590 | 17-May-15 |
| 1980 | 3 | 4 | 5 | 6 | VI-2 | Bcmo1 | 53630 | 4-May-15 |
| 1981 | 3 | 4 | 5 | 6 | VI-2 | Bcorl1 | 63035 | 21-May-15 |
| 1982 | 3 | 4 | 5 | 6 | VI-2 | Bex1 | 55859 | 7-Jun-15 |
| 1983 | 3 | 4 | 5 | 6 | VI-2 | Bhlha15 | 168620 | 14-May-15 |
| 1984 | 3 | 4 | 5 | 6 | VI-2 | Bhlhe40 | 8553 | 4-May-15 |
| 1985 | 3 | 4 | 5 | 6 | VI-2 | Bhlhe41 | 79365 | 4-May-15 |
| 1986 | 3 | 4 | 5 | 6 | VI-2 | Bik | 640 | 17-May-15 |
| 1987 | 3 | 4 | 5 | 6 | VI-2 | Bmp7 | 655 | 17-May-15 |
| 1988 | 3 | 4 | 5 | 6 | VI-2 | Bnc1 | 646 | 7-Jun-15 |
| 1989 | 3 | 4 | 5 | 6 | VI-2 | Bpifb5 | | |
| 1990 | 3 | 4 | 5 | 6 | VI-2 | Btbd6 | 90135 | 4-May-15 |
| 1991 | 3 | 4 | 5 | 6 | VI-2 | C230035J16Rik | | |
| 1992 | 3 | 4 | 5 | 6 | VI-2 | C330011F03Rik | | |
| 1993 | 3 | 4 | 5 | 6 | VI-2 | C330013F16Rik | | |
| 1994 | 3 | 4 | 5 | 6 | VI-2 | C8b | 732 | 4-May-15 |
| 1995 | 3 | 4 | 5 | 6 | VI-2 | Cabp2 | 51475 | 4-May-15 |
| 1996 | 3 | 4 | 5 | 6 | VI-2 | Cacna1h | 8912 | 4-May-15 |
| 1997 | 3 | 4 | 5 | 6 | VI-2 | Camk2a | 815 | 12-May-15 |
| 1998 | 3 | 4 | 5 | 6 | VI-2 | Caps1 | 133690 | 4-May-15 |
| 1999 | 3 | 4 | 5 | 6 | VI-2 | Car14 | | |
| 2000 | 3 | 4 | 5 | 6 | VI-2 | Casc4 | 113201 | 4-May-15 |
| 2001 | 3 | 4 | 5 | 6 | VI-2 | Casr | 846 | 24-May-15 |
| 2002 | 3 | 4 | 5 | 6 | VI-2 | Catip | 375307 | 21-May-15 |
| 2003 | 3 | 4 | 5 | 6 | VI-2 | Cbs | 875 | 23-May-15 |
| 2004 | 3 | 4 | 5 | 6 | VI-2 | Ccdc113 | 29070 | 12-May-15 |
| 2005 | 3 | 4 | 5 | 6 | VI-2 | Ccdc114 | 93233 | 4-May-15 |
| 2006 | 3 | 4 | 5 | 6 | VI-2 | Ccdc122 | 160857 | 4-May-15 |
| 2007 | 3 | 4 | 5 | 6 | VI-2 | Ccdc135 | 84229 | 4-May-15 |
| 2008 | 3 | 4 | 5 | 6 | VI-2 | Ccdc141 | 285025 | 4-May-15 |
| 2009 | 3 | 4 | 5 | 6 | VI-2 | Ccdc148 | 130940 | 12-May-15 |
| 2010 | 3 | 4 | 5 | 6 | VI-2 | Ccdc159 | 126075 | 4-May-15 |
| 2011 | 3 | 4 | 5 | 6 | VI-2 | Ccdc162 | 221262 | 4-May-15 |
| 2012 | 3 | 4 | 5 | 6 | VI-2 | Ccdc170 | 80129 | 4-May-15 |
| 2013 | 3 | 4 | 5 | 6 | VI-2 | Ccdc19 | 25790 | 4-May-15 |
| 2014 | 3 | 4 | 5 | 6 | VI-2 | Ccdc30 | 728621 | 4-May-15 |
| 2015 | 3 | 4 | 5 | 6 | VI-2 | Ccdc39 | 339829 | 23-May-15 |
| 2016 | 3 | 4 | 5 | 6 | VI-2 | Ccdc40 | 55036 | 23-May-15 |
| 2017 | 3 | 4 | 5 | 6 | VI-2 | Ccdc65 | 85478 | 4-May-15 |
| 2018 | 3 | 4 | 5 | 6 | VI-2 | Ccl11 | 6356 | 10-May-15 |
| 2019 | 3 | 4 | 5 | 6 | VI-2 | Ccl27a | | |
| 2020 | 3 | 4 | 5 | 6 | VI-2 | Ccl27b | | |
| 2021 | 3 | 4 | 5 | 6 | VI-2 | Ccnd1 | 595 | 24-May-15 |
| 2022 | 3 | 4 | 5 | 6 | VI-2 | Ccr3 | 1232 | 12-May-15 |
| 2023 | 3 | 4 | 5 | 6 | VI-2 | Ccrl2 | 9034 | 4-May-15 |
| 2024 | 3 | 4 | 5 | 6 | VI-2 | Cd2 | 914 | 12-May-15 |
| 2025 | 3 | 4 | 5 | 6 | VI-2 | Cd209d | | |
| 2026 | 3 | 4 | 5 | 6 | VI-2 | Cd247 | 919 | 21-May-15 |
| 2027 | 3 | 4 | 5 | 6 | VI-2 | Cd28 | 940 | 12-May-15 |
| 2028 | 3 | 4 | 5 | 6 | VI-2 | Cd300e | 342510 | 4-May-15 |
| 2029 | 3 | 4 | 5 | 6 | VI-2 | Cd7 | 924 | 4-May-15 |
| 2030 | 3 | 4 | 5 | 6 | VI-2 | Cdc42ep1 | 11135 | 4-May-15 |
| 2031 | 3 | 4 | 5 | 6 | VI-2 | Cdh16 | 1014 | 7-Jun-15 |
| 2032 | 3 | 4 | 5 | 6 | VI-2 | Cdh18 | 1016 | 12-May-15 |
| 2033 | 3 | 4 | 5 | 6 | VI-2 | Cdhr2 | 54825 | 4-May-15 |
| 2034 | 3 | 4 | 5 | 6 | VI-2 | Cdhr | 441549 | 4-May-15 |
| 2035 | 3 | 4 | 5 | 6 | VI-2 | Ceacam1 | 634 | 12-May-15 |
| 2036 | 3 | 4 | 5 | 6 | VI-2 | Cebpe | 1053 | 4-May-15 |
| 2037 | 3 | 4 | 5 | 6 | VI-2 | Cep128 | 145508 | 12-May-15 |
| 2038 | 3 | 4 | 5 | 6 | VI-2 | Cers1 | 10715 | 21-May-15 |
| 2039 | 3 | 4 | 5 | 6 | VI-2 | Ces1e | | |
| 2040 | 3 | 4 | 5 | 6 | VI-2 | Ces1g | | |
| 2041 | 3 | 4 | 5 | 6 | VI-2 | Ces2c | | |
| 2042 | 3 | 4 | 5 | 6 | VI-2 | Ces2d-ps | | |
| 2043 | 3 | 4 | 5 | 6 | VI-2 | Cftr | 1080 | 24-May-15 |
| 2044 | 3 | 4 | 5 | 6 | VI-2 | Chit1 | 1118 | 4-May-15 |
| 2045 | 3 | 4 | 5 | 6 | VI-2 | Chp2 | 63928 | 4-May-15 |
| 2046 | 3 | 4 | 5 | 6 | VI-2 | Chrd | 8646 | 12-May-15 |
| 2047 | 3 | 4 | 5 | 6 | VI-2 | Chst8 | 64377 | 4-May-15 |
| 2048 | 3 | 4 | 5 | 6 | VI-2 | Ckb | 1152 | 7-Jun-15 |
| 2049 | 3 | 4 | 5 | 6 | VI-2 | Cldn2 | 9075 | 24-May-15 |
| 2050 | 3 | 4 | 5 | 6 | VI-2 | Cldn22 | 53842 | 4-May-15 |
| 2051 | 3 | 4 | 5 | 6 | VI-2 | Cldn24 | 100132463 | 4-May-15 |
| 2052 | 3 | 4 | 5 | 6 | VI-2 | Cldn6 | 9074 | 4-May-15 |
| 2053 | 3 | 4 | 5 | 6 | VI-2 | Clec2h | | |
| 2054 | 3 | 4 | 5 | 6 | VI-2 | Clec4a3 | | |
| 2055 | 3 | 4 | 5 | 6 | VI-2 | Clmn | 79789 | 4-May-15 |
| 2056 | 3 | 4 | 5 | 6 | VI-2 | Clmn3 | 119467 | 4-May-15 |
| 2057 | 3 | 4 | 5 | 6 | VI-2 | Clstn2 | 64084 | 24-May-15 |
| 2058 | 3 | 4 | 5 | 6 | VI-2 | Cmah | 8418 | 3-May-15 |
| 2059 | 3 | 4 | 5 | 6 | VI-2 | Cml3 | 339983 | 4-May-15 |

Fig. 30 - 12

| | | | | | | | | | | | | | | | | | |
|---|---|---|---|---|---|---|---|---|---|---|---|---|---|---|---|---|---|
| 2060 | 3 | 4 | 5 | 6 | | VI-2 | Cmss1 | 84319 | 4-May-15 | 2154 | 3 | 4 | 5 | 6 | | VI-2 | Efhc1 | 114327 | 10-May-15 |
| 2061 | 3 | 4 | 5 | 6 | | VI-2 | Cnga1 | 1259 | 23-May-15 | 2155 | 3 | 4 | 5 | 6 | | VI-2 | Efnb3 | 1949 | 4-May-15 |
| 2062 | 3 | 4 | 5 | 6 | | VI-2 | Cnr1 | 1268 | 7-Jun-15 | 2156 | 3 | 4 | 5 | 6 | | VI-2 | Ehhadh | 1962 | 12-May-15 |
| 2063 | 3 | 4 | 5 | 6 | | VI-2 | Cntn1 | 1272 | 4-May-15 | 2157 | 3 | 4 | 5 | 6 | | VI-2 | Eif3 | 1999 | 12-May-15 |
| 2064 | 3 | 4 | 5 | 6 | | VI-2 | Cntnap2 | 26047 | 12-May-15 | 2158 | 3 | 4 | 5 | 6 | | VI-2 | Eif4n2 | 114794 | 4-May-15 |
| 2065 | 3 | 4 | 5 | 6 | | VI-2 | Cobl | 23242 | 4-May-15 | 2159 | 3 | 4 | 5 | 6 | | VI-2 | Elmod1 | 55531 | 12-May-15 |
| 2066 | 3 | 4 | 5 | 6 | | VI-2 | Col6a6 | 131873 | 4-May-15 | 2160 | 3 | 4 | 5 | 6 | | VI-2 | Enkur | 219670 | 4-May-15 |
| 2067 | 3 | 4 | 5 | 6 | | VI-2 | Colec11 | 78989 | 17-May-15 | 2161 | 3 | 4 | 5 | 6 | | VI-2 | Eno3 | 2027 | 12-May-15 |
| 2068 | 3 | 4 | 5 | 6 | | VI-2 | Coq10b | 80219 | 4-May-15 | 2162 | 3 | 4 | 5 | 6 | | VI-2 | Eno4 | 387712 | 4-May-15 |
| 2069 | 3 | 4 | 5 | 6 | | VI-2 | Corin | 10699 | 10-May-15 | 2163 | 3 | 4 | 5 | 6 | | VI-2 | Enpp2 | 5168 | 12-May-15 |
| 2070 | 3 | 4 | 5 | 6 | | VI-2 | Cox6b2 | 125965 | 4-May-15 | 2164 | 3 | 4 | 5 | 6 | | VI-2 | Entpd8 | 377841 | 4-May-15 |
| 2071 | 3 | 4 | 5 | 6 | | VI-2 | Cpeb1 | 64506 | 4-May-15 | 2165 | 3 | 4 | 5 | 6 | | VI-2 | Ephb1 | 2047 | 17-May-15 |
| 2072 | 3 | 4 | 5 | 6 | | VI-2 | Cpm | 1368 | 12-May-15 | 2166 | 3 | 4 | 5 | 6 | | VI-2 | Ephx1 | 2052 | 17-May-15 |
| 2073 | 3 | 4 | 5 | 6 | | VI-2 | Cpne7 | 27132 | 12-May-15 | 2167 | 3 | 4 | 5 | 6 | | VI-2 | Eps8l2 | 64787 | 4-May-15 |
| 2074 | 3 | 4 | 5 | 6 | | VI-2 | Cpt2 | 1376 | 23-May-15 | 2168 | 3 | 4 | 5 | 6 | | VI-2 | Erich4 | 100170765 | 4-May-15 |
| 2075 | 3 | 4 | 5 | 6 | | VI-2 | Crhr2 | 1395 | 4-May-15 | 2169 | 3 | 4 | 5 | 6 | | VI-2 | Espn | 83715 | 23-May-15 |
| 2076 | 3 | 4 | 5 | 6 | | VI-2 | Crip3 | 403262 | 4-May-15 | 2170 | 3 | 4 | 5 | 6 | | VI-2 | Etv1 | 2115 | 24-May-15 |
| 2077 | 3 | 4 | 5 | 6 | | VI-2 | Crisp2 | 7180 | 21-May-15 | 2171 | 3 | 4 | 5 | 6 | | VI-2 | Eva1a | 84141 | 4-May-15 |
| 2078 | 3 | 4 | 5 | 6 | | VI-2 | Crmp1 | 1400 | 4-May-15 | 2172 | 3 | 4 | 5 | 6 | | VI-2 | Evpl | 2125 | 12-May-15 |
| 2079 | 3 | 4 | 5 | 6 | | VI-2 | Crnn | 49860 | 4-May-15 | 2173 | 3 | 4 | 5 | 6 | | VI-2 | F3 | 2152 | 7-Jun-15 |
| 2080 | 3 | 4 | 5 | 6 | | VI-2 | Crocc | 9696 | 4-May-15 | 2174 | 3 | 4 | 5 | 6 | | VI-2 | F830016B08Rik | | |
| 2081 | 3 | 4 | 5 | 6 | | VI-2 | Cry1 | 1407 | 4-May-15 | 2175 | 3 | 4 | 5 | 6 | | VI-2 | Faah | 2166 | 7-Jun-15 |
| 2082 | 3 | 4 | 5 | 6 | | VI-2 | Cry2 | 1408 | 20-May-15 | 2176 | 3 | 4 | 5 | 6 | | VI-2 | Fabp9 | 646480 | 4-May-15 |
| 2083 | 3 | 4 | 5 | 6 | | VI-2 | Crybb3 | 1417 | 4-May-15 | 2177 | 3 | 4 | 5 | 6 | | VI-2 | Fam163a | 148753 | 14-May-15 |
| 2084 | 3 | 4 | 5 | 6 | | VI-2 | Crym | 1428 | 23-May-15 | 2178 | 3 | 4 | 5 | 6 | | VI-2 | Fam171b | 165215 | 4-May-15 |
| 2085 | 3 | 4 | 5 | 6 | | VI-2 | Cspg4 | 1464 | 4-May-15 | 2179 | 3 | 4 | 5 | 6 | | VI-2 | Fam179a | 165186 | 4-May-15 |
| 2086 | 3 | 4 | 5 | 6 | | VI-2 | Cspg5 | 10675 | 21-May-15 | 2180 | 3 | 4 | 5 | 6 | | VI-2 | Fam216b | 144809 | 4-May-15 |
| 2087 | 3 | 4 | 5 | 6 | | VI-2 | Ctcfl | 140690 | 4-May-15 | 2181 | 3 | 4 | 5 | 6 | | VI-2 | Fam47e | 100129583 | 4-May-15 |
| 2088 | 3 | 4 | 5 | 6 | | VI-2 | Ctla4 | 1493 | 17-May-15 | 2182 | 3 | 4 | 5 | 6 | | VI-2 | Fam69b | 138311 | 4-May-15 |
| 2089 | 3 | 4 | 5 | 6 | | VI-2 | Ctnna2 | 1496 | 12-May-15 | 2183 | 3 | 4 | 5 | 6 | | VI-2 | Fam71b | 153745 | 4-May-15 |
| 2090 | 3 | 4 | 5 | 6 | | VI-2 | Cux2 | 23316 | 4-May-15 | 2184 | 3 | 4 | 5 | 6 | | VI-2 | Fam81a | 145773 | 4-May-15 |
| 2091 | 3 | 4 | 5 | 6 | | VI-2 | Cxadr | 3525 | 17-May-15 | 2185 | 3 | 4 | 5 | 6 | | VI-2 | Fam83a | 84985 | 4-May-15 |
| 2092 | 3 | 4 | 5 | 6 | | VI-2 | Cxcl12 | 6387 | 17-May-15 | 2186 | 3 | 4 | 5 | 6 | | VI-2 | Fbxo44 | 93611 | 12-May-15 |
| 2093 | 3 | 4 | 5 | 6 | | VI-2 | Cyb5r2 | 51700 | 12-May-15 | 2187 | 3 | 4 | 5 | 6 | | VI-2 | Fbxw10 | 10517 | 4-May-15 |
| 2094 | 3 | 4 | 5 | 6 | | VI-2 | Cyp1a1 | 1543 | 12-May-15 | 2188 | 3 | 4 | 5 | 6 | | VI-2 | Ffar4 | 338557 | 24-May-15 |
| 2095 | 3 | 4 | 5 | 6 | | VI-2 | Cyp26a1 | 1592 | 17-May-15 | 2189 | 3 | 4 | 5 | 6 | | VI-2 | Fga | 2243 | 29-May-15 |
| 2096 | 3 | 4 | 5 | 6 | | VI-2 | Cyp2ab1 | | | 2190 | 3 | 4 | 5 | 6 | | VI-2 | Fgf18 | 8817 | 4-May-15 |
| 2097 | 3 | 4 | 5 | 6 | | VI-2 | Cyp2c39 | | | 2191 | 3 | 4 | 5 | 6 | | VI-2 | Fgf21 | 26291 | 17-May-15 |
| 2098 | 3 | 4 | 5 | 6 | | VI-2 | Cyp2c54 | | | 2192 | 3 | 4 | 5 | 6 | | VI-2 | Fgf7 | 2252 | 12-May-15 |
| 2099 | 3 | 4 | 5 | 6 | | VI-2 | Cyp2c55 | | | 2193 | 3 | 4 | 5 | 6 | | VI-2 | Fgfbp1 | 9982 | 4-May-15 |
| 2100 | 3 | 4 | 5 | 6 | | VI-2 | Cyp2g1 | 22952 | 12-May-15 | 2194 | 3 | 4 | 5 | 6 | | VI-2 | Fgfr1l | 53834 | 4-May-15 |
| 2101 | 3 | 4 | 5 | 6 | | VI-2 | Cyp4a12b | | | 2195 | 3 | 4 | 5 | 6 | | VI-2 | Fign | 55137 | 4-May-15 |
| 2102 | 3 | 4 | 5 | 6 | | VI-2 | Cyp7a1 | 1581 | 12-May-15 | 2196 | 3 | 4 | 5 | 6 | | VI-2 | Fkbp4 | 2288 | 7-Jun-15 |
| 2103 | 3 | 4 | 5 | 6 | | VI-2 | Cyp7b1 | 9420 | 17-May-15 | 2197 | 3 | 4 | 5 | 6 | | VI-2 | Fmo1 | 2326 | 12-May-15 |
| 2104 | 3 | 4 | 5 | 6 | | VI-2 | Cys1 | 192668 | 4-May-15 | 2198 | 3 | 4 | 5 | 6 | | VI-2 | Fmo4 | 2329 | 4-May-15 |
| 2105 | 3 | 4 | 5 | 6 | | VI-2 | D430019H16Rik | | | 2199 | 3 | 4 | 5 | 6 | | VI-2 | Fnip1 | 96459 | 4-May-15 |
| 2106 | 3 | 4 | 5 | 6 | | VI-2 | D630003M21Rik | | | 2200 | 3 | 4 | 5 | 6 | | VI-2 | Folr1 | 2348 | 24-May-15 |
| 2107 | 3 | 4 | 5 | 6 | | VI-2 | D630013N20Rik | | | 2201 | 3 | 4 | 5 | 6 | | VI-2 | Fopnl | 123811 | 12-May-15 |
| 2108 | 3 | 4 | 5 | 6 | | VI-2 | D630024D03Rik | | | 2202 | 3 | 4 | 5 | 6 | | VI-2 | Foxf2 | 2295 | 4-May-15 |
| 2109 | 3 | 4 | 5 | 6 | | VI-2 | D630039A03Rik | | | 2203 | 3 | 4 | 5 | 6 | | VI-2 | Frem2 | 341640 | 4-May-15 |
| 2110 | 3 | 4 | 5 | 6 | | VI-2 | D930015M05Rik | | | 2204 | 3 | 4 | 5 | 6 | | VI-2 | Fxyd2 | 486 | 4-May-15 |
| 2111 | 3 | 4 | 5 | 6 | | VI-2 | D930048N14Rik | | | 2205 | 3 | 4 | 5 | 6 | | VI-2 | Fycol | 79443 | 21-May-15 |
| 2112 | 3 | 4 | 5 | 6 | | VI-2 | Dach1 | 1602 | 23-May-15 | 2206 | 3 | 4 | 5 | 6 | | VI-2 | G0s2 | 50486 | 4-May-15 |
| 2113 | 3 | 4 | 5 | 6 | | VI-2 | Dact2 | 168002 | 17-May-15 | 2207 | 3 | 4 | 5 | 6 | | VI-2 | Gabrr2 | 2570 | 4-May-15 |
| 2114 | 3 | 4 | 5 | 6 | | VI-2 | Dapl1 | 92196 | 12-May-15 | 2208 | 3 | 4 | 5 | 6 | | VI-2 | Gal3st1 | 9514 | 4-May-15 |
| 2115 | 3 | 4 | 5 | 6 | | VI-2 | Dbt | 3629 | 23-May-15 | 2209 | 3 | 4 | 5 | 6 | | VI-2 | Gal3st3 | 89792 | 4-May-15 |
| 2116 | 3 | 4 | 5 | 6 | | VI-2 | Dcaf12l1 | 139170 | 30-Apr-15 | 2210 | 3 | 4 | 5 | 6 | | VI-2 | Gas1 | 2619 | 4-May-15 |
| 2117 | 3 | 4 | 5 | 6 | | VI-2 | Dcdc2b | 149069 | 4-May-15 | 2211 | 3 | 4 | 5 | 6 | | VI-2 | Gas6 | 2621 | 18-May-15 |
| 2118 | 3 | 4 | 5 | 6 | | VI-2 | Dclk3 | 85443 | 4-May-15 | 2212 | 3 | 4 | 5 | 6 | | VI-2 | Gata5 | 140628 | 4-May-15 |
| 2119 | 3 | 4 | 5 | 6 | | VI-2 | Dct | 1638 | 21-May-15 | 2213 | 3 | 4 | 5 | 6 | | VI-2 | Gatsl3 | 652968 | 4-May-15 |
| 2120 | 3 | 4 | 5 | 6 | | VI-2 | Ddx60 | 55601 | 4-May-15 | 2214 | 3 | 4 | 5 | 6 | | VI-2 | Gbp10 | | |
| 2121 | 3 | 4 | 5 | 6 | | VI-2 | Decr1 | 1666 | 12-May-15 | 2215 | 3 | 4 | 5 | 6 | | VI-2 | Gbp11 | | |
| 2122 | 3 | 4 | 5 | 6 | | VI-2 | Defa2 | 1667 | 12-May-15 | 2216 | 3 | 4 | 5 | 6 | | VI-2 | Gbp6 | 163351 | 4-May-15 |
| 2123 | 3 | 4 | 5 | 6 | | VI-2 | Degs2 | 123099 | 4-May-15 | 2217 | 3 | 4 | 5 | 6 | | VI-2 | Gbx2 | 2637 | 12-May-15 |
| 2124 | 3 | 4 | 5 | 6 | | VI-2 | Dgat2 | 84649 | 12-May-15 | 2218 | 3 | 4 | 5 | 6 | | VI-2 | Gcat | 23464 | 4-May-15 |
| 2125 | 3 | 4 | 5 | 6 | | VI-2 | Dhrs7c | 201140 | 4-May-15 | 2219 | 3 | 4 | 5 | 6 | | VI-2 | Gdap10 | | |
| 2126 | 3 | 4 | 5 | 6 | | VI-2 | Dio3os | 64150 | 12-May-15 | 2220 | 3 | 4 | 5 | 6 | | VI-2 | Gdf9 | 2661 | 4-May-15 |
| 2127 | 3 | 4 | 5 | 6 | | VI-2 | Dnaaf3 | 352909 | 23-May-15 | 2221 | 3 | 4 | 5 | 6 | | VI-2 | Gfra4 | 64096 | 4-May-15 |
| 2128 | 3 | 4 | 5 | 6 | | VI-2 | Dnah11 | 8701 | 23-May-15 | 2222 | 3 | 4 | 5 | 6 | | VI-2 | Ghrhr | 2692 | 12-May-15 |
| 2129 | 3 | 4 | 5 | 6 | | VI-2 | Dnah5 | 1767 | 23-May-15 | 2223 | 3 | 4 | 5 | 6 | | VI-2 | Gja1 | 2697 | 24-May-15 |
| 2130 | 3 | 4 | 5 | 6 | | VI-2 | Dnajc28 | 54943 | 4-May-15 | 2224 | 3 | 4 | 5 | 6 | | VI-2 | Gjb5 | 2709 | 4-May-15 |
| 2131 | 3 | 4 | 5 | 6 | | VI-2 | Dnase1 | 1773 | 12-May-15 | 2225 | 3 | 4 | 5 | 6 | | VI-2 | Gli2 | 2736 | 23-May-15 |
| 2132 | 3 | 4 | 5 | 6 | | VI-2 | Dnd1 | 373863 | 4-May-15 | 2226 | 3 | 4 | 5 | 6 | | VI-2 | Glis3 | 169792 | 14-May-15 |
| 2133 | 3 | 4 | 5 | 6 | | VI-2 | Dph5 | 51611 | 4-May-15 | 2227 | 3 | 4 | 5 | 6 | | VI-2 | Glp1r | 2740 | 17-May-15 |
| 2134 | 3 | 4 | 5 | 6 | | VI-2 | Dpy19l3 | 147991 | 4-May-15 | 2228 | 3 | 4 | 5 | 6 | | VI-2 | Glt1d1 | 144423 | 4-May-15 |
| 2135 | 3 | 4 | 5 | 6 | | VI-2 | Drc1 | 92749 | 7-Jun-15 | 2229 | 3 | 4 | 5 | 6 | | VI-2 | Glyctk | 132158 | 4-May-15 |
| 2136 | 3 | 4 | 5 | 6 | | VI-2 | Dsg1c | | | 2230 | 3 | 4 | 5 | 6 | | VI-2 | Gm10024 | | |
| 2137 | 3 | 4 | 5 | 6 | | VI-2 | Dsg2 | 1829 | 23-May-15 | 2231 | 3 | 4 | 5 | 6 | | VI-2 | Gm10057 | | |
| 2138 | 3 | 4 | 5 | 6 | | VI-2 | Dtx1 | 1840 | 4-May-15 | 2232 | 3 | 4 | 5 | 6 | | VI-2 | Gm101 | | |
| 2139 | 3 | 4 | 5 | 6 | | VI-2 | Dusp10 | 11221 | 4-May-15 | 2233 | 3 | 4 | 5 | 6 | | VI-2 | Gm10100 | | |
| 2140 | 3 | 4 | 5 | 6 | | VI-2 | Dusp18 | 150290 | 12-May-15 | 2234 | 3 | 4 | 5 | 6 | | VI-2 | Gm10147 | | |
| 2141 | 3 | 4 | 5 | 6 | | VI-2 | Dusp7 | 1849 | 4-May-15 | 2235 | 3 | 4 | 5 | 6 | | VI-2 | Gm10228 | | |
| 2142 | 3 | 4 | 5 | 6 | | VI-2 | Dynlt1b | | | 2236 | 3 | 4 | 5 | 6 | | VI-2 | Gm10229 | | |
| 2143 | 3 | 4 | 5 | 6 | | VI-2 | Dynlt1f | | | 2237 | 3 | 4 | 5 | 6 | | VI-2 | Gm10272 | | |
| 2144 | 3 | 4 | 5 | 6 | | VI-2 | Dzip1l | 199221 | 4-May-15 | 2238 | 3 | 4 | 5 | 6 | | VI-2 | Gm10639 | | |
| 2145 | 3 | 4 | 5 | 6 | | VI-2 | E030019B06Rik | | | 2239 | 3 | 4 | 5 | 6 | | VI-2 | Gm10681 | | |
| 2146 | 3 | 4 | 5 | 6 | | VI-2 | E030030I06Rik | | | 2240 | 3 | 4 | 5 | 6 | | VI-2 | Gm11128 | | |
| 2147 | 3 | 4 | 5 | 6 | | VI-2 | E430016F16Rik | | | 2241 | 3 | 4 | 5 | 6 | | VI-2 | Gm11554 | | |
| 2148 | 3 | 4 | 5 | 6 | | VI-2 | Ear14 | | | 2242 | 3 | 4 | 5 | 6 | | VI-2 | Gm11559 | | |
| 2149 | 3 | 4 | 5 | 6 | | VI-2 | Ech1 | 1891 | 23-May-15 | 2243 | 3 | 4 | 5 | 6 | | VI-2 | Gm11562 | | |
| 2150 | 3 | 4 | 5 | 6 | | VI-2 | Ecl1 | 1632 | 4-May-15 | 2244 | 3 | 4 | 5 | 6 | | VI-2 | Gm11563 | | |
| 2151 | 3 | 4 | 5 | 6 | | VI-2 | Efcab1 | 79645 | 4-May-15 | 2245 | 3 | 4 | 5 | 6 | | VI-2 | Gm11565 | | |
| 2152 | 3 | 4 | 5 | 6 | | VI-2 | Efcab10 | 100130771 | 12-May-15 | 2246 | 3 | 4 | 5 | 6 | | VI-2 | Gm11567 | | |
| 2153 | 3 | 4 | 5 | 6 | | VI-2 | Efcab9 | 285588 | 4-May-15 | 2247 | 3 | 4 | 5 | 6 | | VI-2 | Gm11568 | | |

Fig. 30 - 13

| | | | | | | | | | | | | | | | | | | | |
|---|---|---|---|---|---|---|---|---|---|---|---|---|---|---|---|---|---|---|---|
| 2248 | 3 | 4 | 5 | 6 | | VI-2 | Gm11595 | | | 2344 | 3 | 4 | 5 | 6 | | VI-2 | Hgfac | 3083 | 4-May-15 |
| 2249 | 3 | 4 | 5 | 6 | | VI-2 | Gm11596 | | | 2345 | 3 | 4 | 5 | 6 | | VI-2 | Hhatl | 57467 | 4-May-15 |
| 2250 | 3 | 4 | 5 | 6 | | VI-2 | Gm11937 | | | 2346 | 3 | 4 | 5 | 6 | | VI-2 | Hils1 | 373861 | 12-May-15 |
| 2251 | 3 | 4 | 5 | 6 | | VI-2 | Gm11938 | | | 2347 | 3 | 4 | 5 | 6 | | VI-2 | Hist1h2bf | 8343 | 4-May-15 |
| 2252 | 3 | 4 | 5 | 6 | | VI-2 | Gm12216 | | | 2348 | 3 | 4 | 5 | 6 | | VI-2 | Hist1h3b | 8358 | 4-May-15 |
| 2253 | 3 | 4 | 5 | 6 | | VI-2 | Gm12409 | | | 2349 | 3 | 4 | 5 | 6 | | VI-2 | Hist1h3e | 8353 | 4-May-15 |
| 2254 | 3 | 4 | 5 | 6 | | VI-2 | Gm12429 | | | 2350 | 3 | 4 | 5 | 6 | | VI-2 | Hist1h4b | 8366 | 4-May-15 |
| 2255 | 3 | 4 | 5 | 6 | | VI-2 | Gm12718 | | | 2351 | 3 | 4 | 5 | 6 | | VI-2 | Hist1h4h | 8365 | 12-May-15 |
| 2256 | 3 | 4 | 5 | 6 | | VI-2 | Gm128 | | | 2352 | 3 | 4 | 5 | 6 | | VI-2 | Hist2h2ac | 8338 | 4-May-15 |
| 2257 | 3 | 4 | 5 | 6 | | VI-2 | Gm13298 | | | 2353 | 3 | 4 | 5 | 6 | | VI-2 | Hist2h3c2 | | |
| 2258 | 3 | 4 | 5 | 6 | | VI-2 | Gm13308 | | | 2354 | 3 | 4 | 5 | 6 | | VI-2 | Hk2 | 3099 | 7-Jun-15 |
| 2259 | 3 | 4 | 5 | 6 | | VI-2 | Gm14151 | | | 2355 | 3 | 4 | 5 | 6 | | VI-2 | Hmcn1 | 83872 | 4-May-15 |
| 2260 | 3 | 4 | 5 | 6 | | VI-2 | Gm14295 | | | 2356 | 3 | 4 | 5 | 6 | | VI-2 | Hnf1a | 6927 | 21-May-15 |
| 2261 | 3 | 4 | 5 | 6 | | VI-2 | Gm14308 | | | 2357 | 3 | 4 | 5 | 6 | | VI-2 | Hopx | 84525 | 4-May-15 |
| 2262 | 3 | 4 | 5 | 6 | | VI-2 | Gm14405 | | | 2358 | 3 | 4 | 5 | 6 | | VI-2 | Hoxb9 | 3219 | 24-May-15 |
| 2263 | 3 | 4 | 5 | 6 | | VI-2 | Gm14430 | | | 2359 | 3 | 4 | 5 | 6 | | VI-2 | Hpca | 3208 | 7-Jun-15 |
| 2264 | 3 | 4 | 5 | 6 | | VI-2 | Gm14431 | | | 2360 | 3 | 4 | 5 | 6 | | VI-2 | Hpse2 | 60495 | 12-May-15 |
| 2265 | 3 | 4 | 5 | 6 | | VI-2 | Gm14440 | | | 2361 | 3 | 4 | 5 | 6 | | VI-2 | Hrasls | 57110 | 4-May-15 |
| 2266 | 3 | 4 | 5 | 6 | | VI-2 | Gm14632 | | | 2362 | 3 | 4 | 5 | 6 | | VI-2 | Hrh3 | 11255 | 4-May-15 |
| 2267 | 3 | 4 | 5 | 6 | | VI-2 | Gm15179 | | | 2363 | 3 | 4 | 5 | 6 | | VI-2 | Hs3st5 | 222537 | 7-Jun-15 |
| 2268 | 3 | 4 | 5 | 6 | | VI-2 | Gm15408 | | | 2364 | 3 | 4 | 5 | 6 | | VI-2 | Hsd17b11 | 51170 | 4-May-15 |
| 2269 | 3 | 4 | 5 | 6 | | VI-2 | Gm15663 | | | 2365 | 3 | 4 | 5 | 6 | | VI-2 | Hsd17b2 | 3294 | 12-May-15 |
| 2270 | 3 | 4 | 5 | 6 | | VI-2 | Gm16062 | | | 2366 | 3 | 4 | 5 | 6 | | VI-2 | Hsd3b1 | 3283 | 12-May-15 |
| 2271 | 3 | 4 | 5 | 6 | | VI-2 | Gm16551 | | | 2367 | 3 | 4 | 5 | 6 | | VI-2 | Hsd3b2 | 3284 | 12-May-15 |
| 2272 | 3 | 4 | 5 | 6 | | VI-2 | Gm166 | | | 2368 | 3 | 4 | 5 | 6 | | VI-2 | Hsd3b5 | | |
| 2273 | 3 | 4 | 5 | 6 | | VI-2 | Gm16880 | | | 2369 | 3 | 4 | 5 | 6 | | VI-2 | Hsd3b6 | | |
| 2274 | 3 | 4 | 5 | 6 | | VI-2 | Gm16907 | | | 2370 | 3 | 4 | 5 | 6 | | VI-2 | Hspa12a | 259217 | 12-May-15 |
| 2275 | 3 | 4 | 5 | 6 | | VI-2 | Gm19277 | | | 2371 | 3 | 4 | 5 | 6 | | VI-2 | Hspb6 | 126393 | 12-May-15 |
| 2276 | 3 | 4 | 5 | 6 | | VI-2 | Gm19402 | | | 2372 | 3 | 4 | 5 | 6 | | VI-2 | Htra4 | 203100 | 4-May-15 |
| 2277 | 3 | 4 | 5 | 6 | | VI-2 | Gm19461 | | | 2373 | 3 | 4 | 5 | 6 | | VI-2 | Hvall | 3373 | 7-Jun-15 |
| 2278 | 3 | 4 | 5 | 6 | | VI-2 | Gm19522 | | | 2374 | 3 | 4 | 5 | 6 | | VI-2 | Idh2 | 3418 | 21-May-15 |
| 2279 | 3 | 4 | 5 | 6 | | VI-2 | Gm19668 | | | 2375 | 3 | 4 | 5 | 6 | | VI-2 | Iffo2 | 126917 | 4-May-15 |
| 2280 | 3 | 4 | 5 | 6 | | VI-2 | Gm20878 | | | 2376 | 3 | 4 | 5 | 6 | | VI-2 | Ift81 | 28981 | 4-May-15 |
| 2281 | 3 | 4 | 5 | 6 | | VI-2 | Gm21951 | | | 2377 | 3 | 4 | 5 | 6 | | VI-2 | Igf2 | 3481 | 24-May-15 |
| 2282 | 3 | 4 | 5 | 6 | | VI-2 | Gm2694 | | | 2378 | 3 | 4 | 5 | 6 | | VI-2 | Igfbp2 | 3485 | 12-May-15 |
| 2283 | 3 | 4 | 5 | 6 | | VI-2 | Gm2696 | | | 2379 | 3 | 4 | 5 | 6 | | VI-2 | Igfbp5 | 3488 | 12-May-15 |
| 2284 | 3 | 4 | 5 | 6 | | VI-2 | Gm2837 | | | 2380 | 3 | 4 | 5 | 6 | | VI-2 | Igsf23 | 147710 | 4-May-15 |
| 2285 | 3 | 4 | 5 | 6 | | VI-2 | Gm3238 | | | 2381 | 3 | 4 | 5 | 6 | | VI-2 | Il34 | 146433 | 4-May-15 |
| 2286 | 3 | 4 | 5 | 6 | | VI-2 | Gm3285 | | | 2382 | 3 | 4 | 5 | 6 | | VI-2 | Impa2 | 3613 | 12-May-15 |
| 2287 | 3 | 4 | 5 | 6 | | VI-2 | Gm3317 | | | 2383 | 3 | 4 | 5 | 6 | | VI-2 | Inhbe | 83729 | 12-May-15 |
| 2288 | 3 | 4 | 5 | 6 | | VI-2 | Gm3336 | | | 2384 | 3 | 4 | 5 | 6 | | VI-2 | Inpp5j | 27124 | 4-May-15 |
| 2289 | 3 | 4 | 5 | 6 | | VI-2 | Gm3646 | | | 2385 | 3 | 4 | 5 | 6 | | VI-2 | Ins2 | | |
| 2290 | 3 | 4 | 5 | 6 | | VI-2 | Gm3716 | | | 2386 | 3 | 4 | 5 | 6 | | VI-2 | Insig1 | 3638 | 4-May-15 |
| 2291 | 3 | 4 | 5 | 6 | | VI-2 | Gm3776 | | | 2387 | 3 | 4 | 5 | 6 | | VI-2 | Iqgap2 | 10788 | 17-May-15 |
| 2292 | 3 | 4 | 5 | 6 | | VI-2 | Gm4312 | | | 2388 | 3 | 4 | 5 | 6 | | VI-2 | Irgm2 | | |
| 2293 | 3 | 4 | 5 | 6 | | VI-2 | Gm4477 | | | 2389 | 3 | 4 | 5 | 6 | | VI-2 | Islr2 | 57611 | 4-May-15 |
| 2294 | 3 | 4 | 5 | 6 | | VI-2 | Gm4559 | | | 2390 | 3 | 4 | 5 | 6 | | VI-2 | Isoc2b | | |
| 2295 | 3 | 4 | 5 | 6 | | VI-2 | Gm4841 | | | 2391 | 3 | 4 | 5 | 6 | | VI-2 | Itgb3bp | 23421 | 4-May-15 |
| 2296 | 3 | 4 | 5 | 6 | | VI-2 | Gm4980 | | | 2392 | 3 | 4 | 5 | 6 | | VI-2 | Itgb6 | 3694 | 4-May-15 |
| 2297 | 3 | 4 | 5 | 6 | | VI-2 | Gm53 | | | 2393 | 3 | 4 | 5 | 6 | | VI-2 | Itk | 3702 | 24-May-15 |
| 2298 | 3 | 4 | 5 | 6 | | VI-2 | Gm5547 | | | 2394 | 3 | 4 | 5 | 6 | | VI-2 | Izumo4 | 113177 | 4-May-15 |
| 2299 | 3 | 4 | 5 | 6 | | VI-2 | Gm6416 | | | 2395 | 3 | 4 | 5 | 6 | | VI-2 | Kbtbd13 | 390594 | 23-May-15 |
| 2300 | 3 | 4 | 5 | 6 | | VI-2 | Gm7120 | | | 2396 | 3 | 4 | 5 | 6 | | VI-2 | Kcnd2 | 3751 | 12-May-15 |
| 2301 | 3 | 4 | 5 | 6 | | VI-2 | Gm7337 | | | 2397 | 3 | 4 | 5 | 6 | | VI-2 | Kcng4 | 93107 | 4-May-15 |
| 2302 | 3 | 4 | 5 | 6 | | VI-2 | Gm826 | | | 2398 | 3 | 4 | 5 | 6 | | VI-2 | Kcnh2 | 3757 | 4-May-15 |
| 2303 | 3 | 4 | 5 | 6 | | VI-2 | Gmpr | 2766 | 12-May-15 | 2399 | 3 | 4 | 5 | 6 | | VI-2 | Kcnip2 | 30819 | 12-May-15 |
| 2304 | 3 | 4 | 5 | 6 | | VI-2 | Gnb3 | 2784 | 12-May-15 | 2400 | 3 | 4 | 5 | 6 | | VI-2 | Kcnj16 | 3773 | 4-May-15 |
| 2305 | 3 | 4 | 5 | 6 | | VI-2 | Gnptg | 84572 | 23-May-15 | 2401 | 3 | 4 | 5 | 6 | | VI-2 | Kcnj2 | 3759 | 23-May-15 |
| 2306 | 3 | 4 | 5 | 6 | | VI-2 | Gp5 | 2814 | 4-May-15 | 2402 | 3 | 4 | 5 | 6 | | VI-2 | Kcnj3 | 3760 | 4-May-15 |
| 2307 | 3 | 4 | 5 | 6 | | VI-2 | Gpcpd1 | 56261 | 4-May-15 | 2403 | 3 | 4 | 5 | 6 | | VI-2 | Kcnj5 | 3762 | 23-May-15 |
| 2308 | 3 | 4 | 5 | 6 | | VI-2 | Gpr1 | 2825 | 4-May-15 | 2404 | 3 | 4 | 5 | 6 | | VI-2 | Kcnk5 | 8645 | 4-May-15 |
| 2309 | 3 | 4 | 5 | 6 | | VI-2 | Gpr135 | 64582 | 21-May-15 | 2405 | 3 | 4 | 5 | 6 | | VI-2 | Kcnn1 | 3780 | 12-May-15 |
| 2310 | 3 | 4 | 5 | 6 | | VI-2 | Gpr22 | 2845 | 4-May-15 | 2406 | 3 | 4 | 5 | 6 | | VI-2 | Kcnn2 | 3781 | 4-May-15 |
| 2311 | 3 | 4 | 5 | 6 | | VI-2 | Gpr34 | 2857 | 4-May-15 | 2407 | 3 | 4 | 5 | 6 | | VI-2 | Kcnq4 | 9132 | 23-May-15 |
| 2312 | 3 | 4 | 5 | 6 | | VI-2 | Gpr75 | 10936 | 4-May-15 | 2408 | 3 | 4 | 5 | 6 | | VI-2 | Kcnv2 | 169522 | 4-May-15 |
| 2313 | 3 | 4 | 5 | 6 | | VI-2 | Gpr83 | 10888 | 12-May-15 | 2409 | 3 | 4 | 5 | 6 | | VI-2 | Keg1 | | |
| 2314 | 3 | 4 | 5 | 6 | | VI-2 | Gprc5d | 55507 | 4-May-15 | 2410 | 3 | 4 | 5 | 6 | | VI-2 | Kif9 | 64147 | 4-May-15 |
| 2315 | 3 | 4 | 5 | 6 | | VI-2 | Gprc6a | 222545 | 4-May-15 | 2411 | 3 | 4 | 5 | 6 | | VI-2 | Kl | 9365 | 24-May-15 |
| 2316 | 3 | 4 | 5 | 6 | | VI-2 | Gpt2 | 84706 | 4-May-15 | 2412 | 3 | 4 | 5 | 6 | | VI-2 | Klhdc1 | 122773 | 4-May-15 |
| 2317 | 3 | 4 | 5 | 6 | | VI-2 | Grasp | 160622 | 4-May-15 | 2413 | 3 | 4 | 5 | 6 | | VI-2 | Klhdc4 | 54758 | 4-May-15 |
| 2318 | 3 | 4 | 5 | 6 | | VI-2 | Grb10 | 2887 | 4-May-15 | 2414 | 3 | 4 | 5 | 6 | | VI-2 | Klhdc7a | 127707 | 12-May-15 |
| 2319 | 3 | 4 | 5 | 6 | | VI-2 | Grb7 | 2886 | 12-May-15 | 2415 | 3 | 4 | 5 | 6 | | VI-2 | Klhl29 | 114818 | 4-May-15 |
| 2320 | 3 | 4 | 5 | 6 | | VI-2 | Gria1 | 2890 | 3-May-15 | 2416 | 3 | 4 | 5 | 6 | | VI-2 | Klhl33 | 123103 | 4-May-15 |
| 2321 | 3 | 4 | 5 | 6 | | VI-2 | Grm1 | 2911 | 4-May-15 | 2417 | 3 | 4 | 5 | 6 | | VI-2 | Klk1b27 | | |
| 2322 | 3 | 4 | 5 | 6 | | VI-2 | Grm8 | 2918 | 12-May-15 | 2418 | 3 | 4 | 5 | 6 | | VI-2 | Klra2 | | |
| 2323 | 3 | 4 | 5 | 6 | | VI-2 | Grtp1 | 79774 | 4-May-15 | 2419 | 3 | 4 | 5 | 6 | | VI-2 | Klra21 | | |
| 2324 | 3 | 4 | 5 | 6 | | VI-2 | Gsg1l | 146395 | 4-May-15 | 2420 | 3 | 4 | 5 | 6 | | VI-2 | Kmo | 8564 | 4-May-15 |
| 2325 | 3 | 4 | 5 | 6 | | VI-2 | Gsn | 2934 | 12-May-15 | 2421 | 3 | 4 | 5 | 6 | | VI-2 | Kndc1 | 85442 | 4-May-15 |
| 2326 | 3 | 4 | 5 | 6 | | VI-2 | Gsr | 2936 | 4-May-15 | 2422 | 3 | 4 | 5 | 6 | | VI-2 | Krt25 | 147183 | 4-May-15 |
| 2327 | 3 | 4 | 5 | 6 | | VI-2 | Gsta1 | 2938 | 12-May-15 | 2423 | 3 | 4 | 5 | 6 | | VI-2 | Krt26 | 353288 | 4-May-15 |
| 2328 | 3 | 4 | 5 | 6 | | VI-2 | Gsta2 | 2939 | 12-May-15 | 2424 | 3 | 4 | 5 | 6 | | VI-2 | Krt27 | 342574 | 4-May-15 |
| 2329 | 3 | 4 | 5 | 6 | | VI-2 | Gstp1 | 2950 | 23-May-15 | 2425 | 3 | 4 | 5 | 6 | | VI-2 | Krt28 | 162605 | 4-May-15 |
| 2330 | 3 | 4 | 5 | 6 | | VI-2 | Gstp2 | | | 2426 | 3 | 4 | 5 | 6 | | VI-2 | Krt31 | 3881 | 4-May-15 |
| 2331 | 3 | 4 | 5 | 6 | | VI-2 | Gstt1 | 2952 | 24-May-15 | 2427 | 3 | 4 | 5 | 6 | | VI-2 | Krt33a | 3883 | 4-May-15 |
| 2332 | 3 | 4 | 5 | 6 | | VI-2 | Gstt2 | 2953 | 12-May-15 | 2428 | 3 | 4 | 5 | 6 | | VI-2 | Krt33b | 3884 | 12-May-15 |
| 2333 | 3 | 4 | 5 | 6 | | VI-2 | Gzma | 3001 | 21-May-15 | 2429 | 3 | 4 | 5 | 6 | | VI-2 | Krt34 | 3885 | 12-May-15 |
| 2334 | 3 | 4 | 5 | 6 | | VI-2 | Gzmm | 3004 | 4-May-15 | 2430 | 3 | 4 | 5 | 6 | | VI-2 | Krt35 | 3886 | 4-May-15 |
| 2335 | 3 | 4 | 5 | 6 | | VI-2 | H2afv | 94239 | 2-Jun-15 | 2431 | 3 | 4 | 5 | 6 | | VI-2 | Krt36 | 8689 | 4-May-15 |
| 2336 | 3 | 4 | 5 | 6 | | VI-2 | H2-M10.3 | | | 2432 | 3 | 4 | 5 | 6 | | VI-2 | Krt40 | 125115 | 4-May-15 |
| 2337 | 3 | 4 | 5 | 6 | | VI-2 | H2-Oa | | | 2433 | 3 | 4 | 5 | 6 | | VI-2 | Krt71 | 112802 | 4-May-15 |
| 2338 | 3 | 4 | 5 | 6 | | VI-2 | Habp2 | 3026 | 23-May-15 | 2434 | 3 | 4 | 5 | 6 | | VI-2 | Krt72 | 140807 | 4-May-15 |
| 2339 | 3 | 4 | 5 | 6 | | VI-2 | Hand2 | 9464 | 4-May-15 | 2435 | 3 | 4 | 5 | 6 | | VI-2 | Krt73 | 319101 | 28-May-15 |
| 2340 | 3 | 4 | 5 | 6 | | VI-2 | Hcn3 | 57657 | 4-May-15 | 2436 | 3 | 4 | 5 | 6 | | VI-2 | Krt79 | 338785 | 4-May-15 |
| 2341 | 3 | 4 | 5 | 6 | | VI-2 | Hcn4 | 10021 | 4-May-15 | 2437 | 3 | 4 | 5 | 6 | | VI-2 | Krt80 | 144590 | 4-May-15 |
| 2342 | 3 | 4 | 5 | 6 | | VI-2 | Hdhd3 | 81932 | 12-May-15 | 2438 | 3 | 4 | 5 | 6 | | VI-2 | Krt81 | 3887 | 12-May-15 |
| 2343 | 3 | 4 | 5 | 6 | | VI-2 | Hes2 | 54626 | 4-May-15 | 2439 | 3 | 4 | 5 | 6 | | VI-2 | Krt83 | 3889 | 4-May-15 |

Fig. 30 - 14

| | | | | | | | | | | | | | | | | | | |
|---|---|---|---|---|---|---|---|---|---|---|---|---|---|---|---|---|---|---|
| 2440 | 3 | 4 | 5 | 6 | | VI-2 | Krt85 | 3891 | 4-May-15 | 2533 | 3 | 4 | 5 | 6 | | VI-2 | Marc1 | 64757 | 12-May-15 |
| 2441 | 3 | 4 | 5 | 6 | | VI-2 | Krt86 | 3892 | 12-May-15 | 2534 | 3 | 4 | 5 | 6 | | VI-2 | Marcksl1-ps4 | | |
| 2442 | 3 | 4 | 5 | 6 | | VI-2 | Krtap10-10 | 353333 | 4-May-15 | 2535 | 3 | 4 | 5 | 6 | | VI-2 | Mblac2 | 153364 | 4-May-15 |
| 2443 | 3 | 4 | 5 | 6 | | VI-2 | Krtap11-1 | 337880 | 4-May-15 | 2536 | 3 | 4 | 5 | 6 | | VI-2 | Mcc2 | 64087 | 23-May-15 |
| 2444 | 3 | 4 | 5 | 6 | | VI-2 | Krtap12-1 | 353332 | 4-May-15 | 2537 | 3 | 4 | 5 | 6 | | VI-2 | Mcoln2 | 255231 | 12-May-15 |
| 2445 | 3 | 4 | 5 | 6 | | VI-2 | Krtap1-3 | 81850 | 4-May-15 | 2538 | 3 | 4 | 5 | 6 | | VI-2 | Mcoln3 | 55283 | 12-May-15 |
| 2446 | 3 | 4 | 5 | 6 | | VI-2 | Krtap13-1 | 140258 | 4-May-15 | 2539 | 3 | 4 | 5 | 6 | | VI-2 | Meg3 | 55384 | 7-Jun-15 |
| 2447 | 3 | 4 | 5 | 6 | | VI-2 | Krtap14 | 728255 | 4-May-15 | 2540 | 3 | 4 | 5 | 6 | | VI-2 | Meig1 | 644890 | 4-May-15 |
| 2448 | 3 | 4 | 5 | 6 | | VI-2 | Krtap1-4 | 728255 | 4-May-15 | 2541 | 3 | 4 | 5 | 6 | | VI-2 | Met | 4233 | 7-Jun-15 |
| 2449 | 3 | 4 | 5 | 6 | | VI-2 | Krtap15 | 83895 | 4-May-15 | 2542 | 3 | 4 | 5 | 6 | | VI-2 | Mettl20 | 254013 | 23-May-15 |
| 2450 | 3 | 4 | 5 | 6 | | VI-2 | Krtap1-5 | 83895 | 4-May-15 | 2543 | 3 | 4 | 5 | 6 | | VI-2 | Mettl21e | | |
| 2451 | 3 | 4 | 5 | 6 | | VI-2 | Krtap16-1 | 100505 753 | 4-May-15 | 2544 | 3 | 4 | 5 | 6 | | VI-2 | Mettl7a1 | | |
| 2452 | 3 | 4 | 5 | 6 | | VI-2 | Krtap16-3 | | | 2545 | 3 | 4 | 5 | 6 | | VI-2 | Mettl7a3 | | |
| 2453 | 3 | 4 | 5 | 6 | | VI-2 | Krtap19-1 | 337882 | 4-May-15 | 2546 | 3 | 4 | 5 | 6 | | VI-2 | Mgll | 11343 | 17-May-15 |
| 2454 | 3 | 4 | 5 | 6 | | VI-2 | Krtap19-3 | 337970 | 4-May-15 | 2547 | 3 | 4 | 5 | 6 | | VI-2 | Mia | 8190 | 4-May-15 |
| 2455 | 3 | 4 | 5 | 6 | | VI-2 | Krtap19-4 | 337971 | 4-May-15 | 2548 | 3 | 4 | 5 | 6 | | VI-2 | Mill2 | | |
| 2456 | 3 | 4 | 5 | 6 | | VI-2 | Krtap19-5 | 337972 | 12-May-15 | 2549 | 3 | 4 | 5 | 6 | | VI-2 | Mir1197 | 100302 250 | 21-May-15 |
| 2457 | 3 | 4 | 5 | 6 | | VI-2 | Krtap19-9b | | | 2550 | 3 | 4 | 5 | 6 | | VI-2 | Mir128-1 | 406915 | 21-May-15 |
| 2458 | 3 | 4 | 5 | 6 | | VI-2 | Krtap21-1 | 337977 | 4-May-15 | 2551 | 3 | 4 | 5 | 6 | | VI-2 | Mir138-2 | 406930 | 21-May-15 |
| 2459 | 3 | 4 | 5 | 6 | | VI-2 | Krtap22-2 | 100288 287 | 4-May-15 | 2552 | 3 | 4 | 5 | 6 | | VI-2 | Mir3093 | | |
| | | | | | | | | | | 2553 | 3 | 4 | 5 | 6 | | VI-2 | Mir322 | 494336 | 21-May-15 |
| 2460 | 3 | 4 | 5 | 6 | | VI-2 | Krtap2-4 | 85294 | 4-May-15 | 2554 | 3 | 4 | 5 | 6 | | VI-2 | Mir34b | 407041 | 21-May-15 |
| 2461 | 3 | 4 | 5 | 6 | | VI-2 | Krtap26-1 | 388818 | 4-May-15 | 2555 | 3 | 4 | 5 | 6 | | VI-2 | Mir489 | 574442 | 21-May-15 |
| 2462 | 3 | 4 | 5 | 6 | | VI-2 | Krtap3-1 | 83896 | 4-May-15 | 2556 | 3 | 4 | 5 | 6 | | VI-2 | Mir496b | | |
| 2463 | 3 | 4 | 5 | 6 | | VI-2 | Krtap31-1 | | | 2557 | 3 | 4 | 5 | 6 | | VI-2 | Mir503 | 574506 | 21-May-15 |
| 2464 | 3 | 4 | 5 | 6 | | VI-2 | Krtap31-2 | | | 2558 | 3 | 4 | 5 | 6 | | VI-2 | Mir6238 | | |
| 2465 | 3 | 4 | 5 | 6 | | VI-2 | Krtap3-2 | 83897 | 4-May-15 | 2559 | 3 | 4 | 5 | 6 | | VI-2 | Mir6336 | | |
| 2466 | 3 | 4 | 5 | 6 | | VI-2 | Krtap4-1 | 85285 | 4-May-15 | 2560 | 3 | 4 | 5 | 6 | | VI-2 | Mir6390 | | |
| 2467 | 3 | 4 | 5 | 6 | | VI-2 | Krtap4-13 | 84616 | 4-May-15 | 2561 | 3 | 4 | 5 | 6 | | VI-2 | Mir669c | | |
| 2468 | 3 | 4 | 5 | 6 | | VI-2 | Krtap4-16 | | | 2562 | 3 | 4 | 5 | 6 | | VI-2 | Mir669h | | |
| 2469 | 3 | 4 | 5 | 6 | | VI-2 | Krtap4-2 | 85291 | 4-May-15 | 2563 | 3 | 4 | 5 | 6 | | VI-2 | Mir669k | | |
| 2470 | 3 | 4 | 5 | 6 | | VI-2 | Krtap4-6 | 81871 | 4-May-15 | 2564 | 3 | 4 | 5 | 6 | | VI-2 | Mir701 | | |
| 2471 | 3 | 4 | 5 | 6 | | VI-2 | Krtap4-7 | 100132 476 | 4-May-15 | 2565 | 3 | 4 | 5 | 6 | | VI-2 | Mir703 | | |
| 2472 | 3 | 4 | 5 | 6 | | VI-2 | Krtap4-8 | 728224 | 4-May-15 | 2566 | 3 | 4 | 5 | 6 | | VI-2 | Mir7219 | | |
| 2473 | 3 | 4 | 5 | 6 | | VI-2 | Krtap4-9 | 100132 386 | 4-May-15 | 2567 | 3 | 4 | 5 | 6 | | VI-2 | Mir7229 | | |
| | | | | | | | | | | 2568 | 3 | 4 | 5 | 6 | | VI-2 | Mir7230 | | |
| 2474 | 3 | 4 | 5 | 6 | | VI-2 | Krtap5-1 | 387264 | 4-May-15 | 2569 | 3 | 4 | 5 | 6 | | VI-2 | Mir763 | | |
| 2475 | 3 | 4 | 5 | 6 | | VI-2 | Krtap5-2 | 440021 | 4-May-15 | 2570 | 3 | 4 | 5 | 6 | | VI-2 | Mir8094 | | |
| 2476 | 3 | 4 | 5 | 6 | | VI-2 | Krtap5-3 | 387266 | 4-May-15 | 2571 | 3 | 4 | 5 | 6 | | VI-2 | Mir8106 | | |
| 2477 | 3 | 4 | 5 | 6 | | VI-2 | Krtap5-4 | 387267 | 4-Apr-15 | 2572 | 3 | 4 | 5 | 6 | | VI-2 | Misp | 126353 | 4-May-15 |
| 2478 | 3 | 4 | 5 | 6 | | VI-2 | Krtap5-5 | 439935 | 4-May-15 | 2573 | 3 | 4 | 5 | 6 | | VI-2 | Mlph | 79083 | 7-Jun-15 |
| 2479 | 3 | 4 | 5 | 6 | | VI-2 | Krtap6-1 | 337966 | 4-May-15 | 2574 | 3 | 4 | 5 | 6 | | VI-2 | Mlxipl | 51085 | 23-May-15 |
| 2480 | 3 | 4 | 5 | 6 | | VI-2 | Krtap6-2 | 337967 | 12-May-15 | 2575 | 3 | 4 | 5 | 6 | | VI-2 | Mmab | 326625 | 23-May-15 |
| 2481 | 3 | 4 | 5 | 6 | | VI-2 | Krtap6-5 | | | 2576 | 3 | 4 | 5 | 6 | | VI-2 | Mmp11 | 4320 | 4-May-15 |
| 2482 | 3 | 4 | 5 | 6 | | VI-2 | Krtap7-1 | 337878 | 4-May-15 | 2577 | 3 | 4 | 5 | 6 | | VI-2 | Mmp24 | 10893 | 4-May-15 |
| 2483 | 3 | 4 | 5 | 6 | | VI-2 | Krtap8-1 | 337879 | 4-May-15 | 2578 | 3 | 4 | 5 | 6 | | VI-2 | Mmp25 | 64386 | 7-Jun-15 |
| 2484 | 3 | 4 | 5 | 6 | | VI-2 | Krtap9-1 | 728318 | 4-May-15 | 2579 | 3 | 4 | 5 | 6 | | VI-2 | Morc1 | 27136 | 4-May-15 |
| 2485 | 3 | 4 | 5 | 6 | | VI-2 | Krtap9-3 | 83900 | 12-May-15 | 2580 | 3 | 4 | 5 | 6 | | VI-2 | Morn2 | 729967 | 4-May-15 |
| 2486 | 3 | 4 | 5 | 6 | | VI-2 | Kynu | 8942 | 4-May-15 | 2581 | 3 | 4 | 5 | 6 | | VI-2 | Morn3 | 283385 | 4-May-15 |
| 2487 | 3 | 4 | 5 | 6 | | VI-2 | Lace1 | 246269 | 4-May-15 | 2582 | 3 | 4 | 5 | 6 | | VI-2 | Morn5 | 254956 | 4-May-15 |
| 2488 | 3 | 4 | 5 | 6 | | VI-2 | Lamb3 | 3914 | 23-May-15 | 2583 | 3 | 4 | 5 | 6 | | VI-2 | Mov10l1 | 54456 | 4-May-15 |
| 2489 | 3 | 4 | 5 | 6 | | VI-2 | Lbx2 | 85474 | 12-May-15 | 2584 | 3 | 4 | 5 | 6 | | VI-2 | Mreg | 55686 | 4-May-15 |
| 2490 | 3 | 4 | 5 | 6 | | VI-2 | Lcat | 3931 | 4-May-15 | 2585 | 3 | 4 | 5 | 6 | | VI-2 | Mrgprg | 386746 | 4-May-15 |
| 2491 | 3 | 4 | 5 | 6 | | VI-2 | Ldh2 | 9079 | 12-May-15 | 2586 | 3 | 4 | 5 | 6 | | VI-2 | Mrgprh | | |
| 2492 | 3 | 4 | 5 | 6 | | VI-2 | Ldhb | 3945 | 12-May-15 | 2587 | 3 | 4 | 5 | 6 | | VI-2 | Ms4a3 | 932 | 4-May-15 |
| 2493 | 3 | 4 | 5 | 6 | | VI-2 | Ldlr | 3949 | 17-May-15 | 2588 | 3 | 4 | 5 | 6 | | VI-2 | Ms4a4d | | |
| 2494 | 3 | 4 | 5 | 6 | | VI-2 | Ldlrad3 | 143458 | 12-May-15 | 2589 | 3 | 4 | 5 | 6 | | VI-2 | Msrb3 | 253827 | 4-May-15 |
| 2495 | 3 | 4 | 5 | 6 | | VI-2 | Lifr | 3977 | 12-May-15 | 2590 | 3 | 4 | 5 | 6 | | VI-2 | Mta2 | 9219 | 4-May-15 |
| 2496 | 3 | 4 | 5 | 6 | | VI-2 | Lin7b | 64130 | 12-May-15 | 2591 | 3 | 4 | 5 | 6 | | VI-2 | Mterfd3 | 80298 | 4-May-15 |
| 2497 | 3 | 4 | 5 | 6 | | VI-2 | Lingo3 | 645191 | 4-May-15 | 2592 | 3 | 4 | 5 | 6 | | VI-2 | Mtfp1 | 51537 | 12-May-15 |
| 2498 | 3 | 4 | 5 | 6 | | VI-2 | Lipn | 643418 | 4-May-15 | 2593 | 3 | 4 | 5 | 6 | | VI-2 | Muc13 | 56667 | 4-May-15 |
| 2499 | 3 | 4 | 5 | 6 | | VI-2 | Lmod1 | 25802 | 12-May-15 | 2594 | 3 | 4 | 5 | 6 | | VI-2 | Muc2 | 4583 | 4-May-15 |
| 2500 | 3 | 4 | 5 | 6 | | VI-2 | Lmod3 | 56203 | 12-May-15 | 2595 | 3 | 4 | 5 | 6 | | VI-2 | Mum1 | 84939 | 7-Jun-15 |
| 2501 | 3 | 4 | 5 | 6 | | VI-2 | Lonrf1 | 91694 | 4-May-15 | 2596 | 3 | 4 | 5 | 6 | | VI-2 | Mup20 | | |
| 2502 | 3 | 4 | 5 | 6 | | VI-2 | Lrat | 9227 | 4-May-15 | 2597 | 3 | 4 | 5 | 6 | | VI-2 | Mup5 | | |
| 2503 | 3 | 4 | 5 | 6 | | VI-2 | Lrp2 | 4036 | 23-May-15 | 2598 | 3 | 4 | 5 | 6 | | VI-2 | Mup6 | | |
| 2504 | 3 | 4 | 5 | 6 | | VI-2 | Lrrc10b | 390205 | 4-May-15 | 2599 | 3 | 4 | 5 | 6 | | VI-2 | Mybph | 4608 | 4-May-15 |
| 2505 | 3 | 4 | 5 | 6 | | VI-2 | Lrrc14b | 389257 | 4-May-15 | 2600 | 3 | 4 | 5 | 6 | | VI-2 | Myh7b | 57644 | 4-May-15 |
| 2506 | 3 | 4 | 5 | 6 | | VI-2 | Lrrc15 | 131578 | 4-May-15 | 2601 | 3 | 4 | 5 | 6 | | VI-2 | Naip5 | | |
| 2507 | 3 | 4 | 5 | 6 | | VI-2 | Lrrc16a | 55604 | 17-May-15 | 2602 | 3 | 4 | 5 | 6 | | VI-2 | Nampt | 10135 | 17-May-15 |
| 2508 | 3 | 4 | 5 | 6 | | VI-2 | Lrrc17 | 10234 | 4-May-15 | 2603 | 3 | 4 | 5 | 6 | | VI-2 | Nav2 | 89797 | 4-May-15 |
| 2509 | 3 | 4 | 5 | 6 | | VI-2 | Lrrc18 | 474354 | 12-May-15 | 2604 | 3 | 4 | 5 | 6 | | VI-2 | Nckap5 | 344148 | 4-May-15 |
| 2510 | 3 | 4 | 5 | 6 | | VI-2 | Lrrc36 | 55282 | 4-May-15 | 2605 | 3 | 4 | 5 | 6 | | VI-2 | Ncmap | 400746 | 4-May-15 |
| 2511 | 3 | 4 | 5 | 6 | | VI-2 | Lrrc38 | 126755 | 4-May-15 | 2606 | 3 | 4 | 5 | 6 | | VI-2 | Nepn | 442253 | 4-May-15 |
| 2512 | 3 | 4 | 5 | 6 | | VI-2 | Lrrc39 | 127495 | 4-May-15 | 2607 | 3 | 4 | 5 | 6 | | VI-2 | Ngef | 25791 | 4-May-15 |
| 2513 | 3 | 4 | 5 | 6 | | VI-2 | Lrrc3b | 116135 | 14-May-15 | 2608 | 3 | 4 | 5 | 6 | | VI-2 | Nhej1 | 79840 | 4-May-15 |
| 2514 | 3 | 4 | 5 | 6 | | VI-2 | Lrrc48 | 83450 | 4-May-15 | 2609 | 3 | 4 | 5 | 6 | | VI-2 | Nim1k | 167359 | 4-May-15 |
| 2515 | 3 | 4 | 5 | 6 | | VI-2 | Lrrc4b | 94030 | 4-May-15 | 2610 | 3 | 4 | 5 | 6 | | VI-2 | Nkain1 | 79570 | 4-May-15 |
| 2516 | 3 | 4 | 5 | 6 | | VI-2 | Lrrc52 | 440699 | 4-May-15 | 2611 | 3 | 4 | 5 | 6 | | VI-2 | Nkx6-2 | 84504 | 4-May-15 |
| 2517 | 3 | 4 | 5 | 6 | | VI-2 | Lrrc71 | 149499 | 4-May-15 | 2612 | 3 | 4 | 5 | 6 | | VI-2 | Nmb | 4828 | 7-Jun-15 |
| 2518 | 3 | 4 | 5 | 6 | | VI-2 | Lrtm1 | 57408 | 12-May-15 | 2613 | 3 | 4 | 5 | 6 | | VI-2 | Nme4 | 4833 | 4-May-15 |
| 2519 | 3 | 4 | 5 | 6 | | VI-2 | Lrtm2 | 654429 | 4-May-15 | 2614 | 3 | 4 | 5 | 6 | | VI-2 | Nnt | 23500 | 13-May-15 |
| 2520 | 3 | 4 | 5 | 6 | | VI-2 | Lsmem1 | 286006 | 4-May-15 | 2615 | 3 | 4 | 5 | 6 | | VI-2 | Npff | 8620 | 4-May-15 |
| 2521 | 3 | 4 | 5 | 6 | | VI-2 | Luc7l3 | 51747 | 4-May-15 | 2616 | 3 | 4 | 5 | 6 | | VI-2 | Nphs2 | 7827 | 12-May-15 |
| 2522 | 3 | 4 | 5 | 6 | | VI-2 | Lurap1l | 286343 | 4-May-15 | 2617 | 3 | 4 | 5 | 6 | | VI-2 | Nr1d2 | 9975 | 4-May-15 |
| 2523 | 3 | 4 | 5 | 6 | | VI-2 | Ly6g6d | 58530 | 4-May-15 | 2618 | 3 | 4 | 5 | 6 | | VI-2 | Nr1i3 | 9970 | 4-May-15 |
| 2524 | 3 | 4 | 5 | 6 | | VI-2 | Ly6h | 4062 | 4-May-15 | 2619 | 3 | 4 | 5 | 6 | | VI-2 | Nr3c2 | 4306 | 24-May-15 |
| 2525 | 3 | 4 | 5 | 6 | | VI-2 | Lypd8 | 646627 | 4-May-15 | 2620 | 3 | 4 | 5 | 6 | | VI-2 | Nt5dc3 | 51559 | 23-May-15 |
| 2526 | 3 | 4 | 5 | 6 | | VI-2 | Maats1 | 89876 | 4-May-15 | 2621 | 3 | 4 | 5 | 6 | | VI-2 | Ntf5 | 4909 | 4-May-15 |
| 2527 | 3 | 4 | 5 | 6 | | VI-2 | Maged2 | 10916 | 4-May-15 | 2622 | 3 | 4 | 5 | 6 | | VI-2 | Ntn1 | 9423 | 17-May-15 |
| 2528 | 3 | 4 | 5 | 6 | | VI-2 | Magix | 79917 | 4-May-15 | 2623 | 3 | 4 | 5 | 6 | | VI-2 | Ntsr2 | 23620 | 4-May-15 |
| 2529 | 3 | 4 | 5 | 6 | | VI-2 | Map2k6 | 5608 | 4-May-15 | 2624 | 3 | 4 | 5 | 6 | | VI-2 | Nuak1 | 9891 | 4-May-15 |
| 2530 | 3 | 4 | 5 | 6 | | VI-2 | Mapk10 | 5602 | 3-May-15 | 2625 | 3 | 4 | 5 | 6 | | VI-2 | Nudt12 | 83594 | 4-May-15 |
| 2531 | 3 | 4 | 5 | 6 | | VI-2 | Mapk4 | 5596 | 4-May-15 | 2626 | 3 | 4 | 5 | 6 | | VI-2 | Nudt15 | 55270 | 4-May-15 |
| 2532 | 3 | 4 | 5 | 6 | | VI-2 | Mapt | 4137 | 23-May-15 | 2627 | 3 | 4 | 5 | 6 | | VI-2 | Nudt17 | 200035 | 23-May-15 |

Fig. 30 - 15

| | | | | | | | | | | | | | | | | | | |
|---|---|---|---|---|---|---|---|---|---|---|---|---|---|---|---|---|---|---|
| 2628 | 3 | 4 | 5 | 6 | | VI-2 | Nudt19 | 390916 | 21-May-15 | 2723 | 3 | 4 | 5 | 6 | | VI-2 | Rab36 | 9609 | 23-May-15 |
| 2629 | 3 | 4 | 5 | 6 | | VI-2 | Nudt7 | 283927 | 4-May-15 | 2724 | 3 | 4 | 5 | 6 | | VI-2 | Raet1b | | |
| 2630 | 3 | 4 | 5 | 6 | | VI-2 | Odf3l1 | 161753 | 4-May-15 | 2725 | 3 | 4 | 5 | 6 | | VI-2 | Raet1d | | |
| 2631 | 3 | 4 | 5 | 6 | | VI-2 | Ogdhl | 55753 | 4-May-15 | 2726 | 3 | 4 | 5 | 6 | | VI-2 | Rasd2 | 23551 | 4-May-15 |
| 2632 | 3 | 4 | 5 | 6 | | VI-2 | Olfr1396 | | | 2727 | 3 | 4 | 5 | 6 | | VI-2 | Rasgrp1 | 10125 | 12-May-15 |
| 2633 | 3 | 4 | 5 | 6 | | VI-2 | Olig3 | 167826 | 4-May-15 | 2728 | 3 | 4 | 5 | 6 | | VI-2 | Rasl12 | 51285 | 12-May-15 |
| 2634 | 3 | 4 | 5 | 6 | | VI-2 | Onecut1 | 3175 | 12-May-15 | 2729 | 3 | 4 | 5 | 6 | | VI-2 | Rassf8 | 11228 | 4-May-15 |
| 2635 | 3 | 4 | 5 | 6 | | VI-2 | Orm2 | 5005 | 3-May-15 | 2730 | 3 | 4 | 5 | 6 | | VI-2 | Rassf9 | 9182 | 4-May-15 |
| 2636 | 3 | 4 | 5 | 6 | | VI-2 | Osbpl3 | 26031 | 4-May-15 | 2731 | 3 | 4 | 5 | 6 | | VI-2 | Rbck1 | 10616 | 23-May-15 |
| 2637 | 3 | 4 | 5 | 6 | | VI-2 | Osbpl6 | 114880 | 12-May-15 | 2732 | 3 | 4 | 5 | 6 | | VI-2 | Rbfox1 | 54715 | 12-May-15 |
| 2638 | 3 | 4 | 5 | 6 | | VI-2 | Osgin1 | 29948 | 4-May-15 | 2733 | 3 | 4 | 5 | 6 | | VI-2 | Rbm12b2 | | |
| 2639 | 3 | 4 | 5 | 6 | | VI-2 | Ostn | 344901 | 4-May-15 | 2734 | 3 | 4 | 5 | 6 | | VI-2 | Rbpjl | 11317 | 4-May-15 |
| 2640 | 3 | 4 | 5 | 6 | | VI-2 | Oxld1 | 339229 | 12-May-15 | 2735 | 3 | 4 | 5 | 6 | | VI-2 | Rcor2 | 283248 | 4-May-15 |
| 2641 | 3 | 4 | 5 | 6 | | VI-2 | P2rx1 | 5023 | 17-May-15 | 2736 | 3 | 4 | 5 | 6 | | VI-2 | Rdh11 | 51109 | 4-May-15 |
| 2642 | 3 | 4 | 5 | 6 | | VI-2 | P2rx6 | 9127 | 4-May-15 | 2737 | 3 | 4 | 5 | 6 | | VI-2 | Rdh18-ps | | |
| 2643 | 3 | 4 | 5 | 6 | | VI-2 | P2ry1 | 5028 | 12-May-15 | 2738 | 3 | 4 | 5 | 6 | | VI-2 | Ret | 5979 | 22-May-15 |
| 2644 | 3 | 4 | 5 | 6 | | VI-2 | Pacrg | 135138 | 14-May-15 | 2739 | 3 | 4 | 5 | 6 | | VI-2 | Rex2 | 25996 | 4-May-15 |
| 2645 | 3 | 4 | 5 | 6 | | VI-2 | Padi3 | 51702 | 4-May-15 | 2740 | 3 | 4 | 5 | 6 | | VI-2 | Rgs22 | 26166 | 4-May-15 |
| 2646 | 3 | 4 | 5 | 6 | | VI-2 | Papss2 | 9060 | 4-May-15 | 2741 | 3 | 4 | 5 | 6 | | VI-2 | Rgs5 | 8490 | 12-May-15 |
| 2647 | 3 | 4 | 5 | 6 | | VI-2 | Paqr5 | 54852 | 4-May-15 | 2742 | 3 | 4 | 5 | 6 | | VI-2 | Rgs6 | 9628 | 17-May-15 |
| 2648 | 3 | 4 | 5 | 6 | | VI-2 | Pbx4 | 80714 | 4-May-15 | 2743 | 3 | 4 | 5 | 6 | | VI-2 | Rhbdf1 | 64285 | 4-May-15 |
| 2649 | 3 | 4 | 5 | 6 | | VI-2 | Pcbd1 | 5092 | 4-May-15 | 2744 | 3 | 4 | 5 | 6 | | VI-2 | Rhbdl3 | 162494 | 4-May-15 |
| 2650 | 3 | 4 | 5 | 6 | | VI-2 | Pcbd2 | 84105 | 4-May-15 | 2745 | 3 | 4 | 5 | 6 | | VI-2 | Rnf128 | 79589 | 4-May-15 |
| 2651 | 3 | 4 | 5 | 6 | | VI-2 | Pcdh18 | 54510 | 12-May-15 | 2746 | 3 | 4 | 5 | 6 | | VI-2 | Rnf144a | 9781 | 18-May-15 |
| 2652 | 3 | 4 | 5 | 6 | | VI-2 | Pcdhac2 | 56134 | 4-May-15 | 2747 | 3 | 4 | 5 | 6 | | VI-2 | Rnf186 | 54546 | 4-May-15 |
| 2653 | 3 | 4 | 5 | 6 | | VI-2 | Pcsk4 | 54760 | 4-May-15 | 2748 | 3 | 4 | 5 | 6 | | VI-2 | Rnf207 | 388591 | 4-May-15 |
| 2654 | 3 | 4 | 5 | 6 | | VI-2 | Pde4a | 5141 | 12-May-15 | 2749 | 3 | 4 | 5 | 6 | | VI-2 | Rnf43 | 54894 | 4-May-15 |
| 2655 | 3 | 4 | 5 | 6 | | VI-2 | Pde4c | 5143 | 12-May-15 | 2750 | 3 | 4 | 5 | 6 | | VI-2 | Rnu12 | 267010 | 4-May-15 |
| 2656 | 3 | 4 | 5 | 6 | | VI-2 | Pdilt | 204474 | 4-May-15 | 2751 | 3 | 4 | 5 | 6 | | VI-2 | Rorc | 6097 | 4-May-15 |
| 2657 | 3 | 4 | 5 | 6 | | VI-2 | Pdk1 | 5163 | 7-Jun-15 | 2752 | 3 | 4 | 5 | 6 | | VI-2 | Rpp25 | 54913 | 4-May-15 |
| 2658 | 3 | 4 | 5 | 6 | | VI-2 | Pdp2 | 57546 | 4-May-15 | 2753 | 3 | 4 | 5 | 6 | | VI-2 | Rprml | 388394 | 4-May-15 |
| 2659 | 3 | 4 | 5 | 6 | | VI-2 | Pdzd3 | 79849 | 4-May-15 | 2754 | 3 | 4 | 5 | 6 | | VI-2 | Rps16 | 6217 | 4-May-15 |
| 2660 | 3 | 4 | 5 | 6 | | VI-2 | Pdzd7 | 79955 | 23-May-15 | 2755 | 3 | 4 | 5 | 6 | | VI-2 | Rps2 | 6187 | 4-May-15 |
| 2661 | 3 | 4 | 5 | 6 | | VI-2 | Penk | 5179 | 12-May-15 | 2756 | 3 | 4 | 5 | 6 | | VI-2 | Rsph9 | 221421 | 23-May-15 |
| 2662 | 3 | 4 | 5 | 6 | | VI-2 | Per2 | 8564 | 17-May-15 | 2757 | 3 | 4 | 5 | 6 | | VI-2 | Rtkn2 | 219790 | 4-May-15 |
| 2663 | 3 | 4 | 5 | 6 | | VI-2 | Per3 | 8863 | 17-May-15 | 2758 | 3 | 4 | 5 | 6 | | VI-2 | Rtn1 | 6252 | 12-May-15 |
| 2664 | 3 | 4 | 5 | 6 | | VI-2 | Perm1 | 84808 | 12-May-15 | 2759 | 3 | 4 | 5 | 6 | | VI-2 | Rtn4ip1 | 84816 | 4-May-15 |
| 2665 | 3 | 4 | 5 | 6 | | VI-2 | Perp | 64065 | 4-May-15 | 2760 | 3 | 4 | 5 | 6 | | VI-2 | Rtn4r | 65078 | 4-May-15 |
| 2666 | 3 | 4 | 5 | 6 | | VI-2 | Pex26 | 55670 | 4-May-15 | 2761 | 3 | 4 | 5 | 6 | | VI-2 | Rvr3 | 6263 | 12-May-15 |
| 2667 | 3 | 4 | 5 | 6 | | VI-2 | Pfkfb1 | 5207 | 4-May-15 | 2762 | 3 | 4 | 5 | 6 | | VI-2 | S100a5 | 6276 | 4-May-15 |
| 2668 | 3 | 4 | 5 | 6 | | VI-2 | Pfkfb2 | 5208 | 4-May-15 | 2763 | 3 | 4 | 5 | 6 | | VI-2 | S1pr5 | 53637 | 4-May-15 |
| 2669 | 3 | 4 | 5 | 6 | | VI-2 | Phgr1 | 644844 | 4-May-15 | 2764 | 3 | 4 | 5 | 6 | | VI-2 | Salt1 | 6299 | 23-May-15 |
| 2670 | 3 | 4 | 5 | 6 | | VI-2 | Pifo | 128344 | 4-May-15 | 2765 | 3 | 4 | 5 | 6 | | VI-2 | Sbk3 | 100130 827 | 4-May-15 |
| 2671 | 3 | 4 | 5 | 6 | | VI-2 | Pih1d2 | 120379 | 4-May-15 | 2766 | 3 | 4 | 5 | 6 | | VI-2 | Sbsn | 374897 | 4-May-15 |
| 2672 | 3 | 4 | 5 | 6 | | VI-2 | Pik3c2b | 5287 | 4-May-15 | 2767 | 3 | 4 | 5 | 6 | | VI-2 | Scarletltr | | |
| 2673 | 3 | 4 | 5 | 6 | | VI-2 | Pik3c2g | 5288 | 3-May-15 | 2768 | 3 | 4 | 5 | 6 | | VI-2 | Scgb1c1 | 147199 | 4-May-15 |
| 2674 | 3 | 4 | 5 | 6 | | VI-2 | Pilrb2 | | | 2769 | 3 | 4 | 5 | 6 | | VI-2 | Scgb2b23-ps | | |
| 2675 | 3 | 4 | 5 | 6 | | VI-2 | Pin4 | 5303 | 12-May-15 | 2770 | 3 | 4 | 5 | 6 | | VI-2 | Scgn | 10590 | 4-May-15 |
| 2676 | 3 | 4 | 5 | 6 | | VI-2 | Pirt | 644139 | 12-May-15 | 2771 | 3 | 4 | 5 | 6 | | VI-2 | Scrn1 | 9805 | 4-May-15 |
| 2677 | 3 | 4 | 5 | 6 | | VI-2 | Pitx2 | 5308 | 23-May-15 | 2772 | 3 | 4 | 5 | 6 | | VI-2 | Scube2 | 57758 | 4-May-15 |
| 2678 | 3 | 4 | 5 | 6 | | VI-2 | Pla2g2e | 30814 | 4-May-15 | 2773 | 3 | 4 | 5 | 6 | | VI-2 | Sdr9c7 | 121214 | 4-May-15 |
| 2679 | 3 | 4 | 5 | 6 | | VI-2 | Pla2g4e | 123745 | 4-May-15 | 2774 | 3 | 4 | 5 | 6 | | VI-2 | Sds | 10993 | 21-May-15 |
| 2680 | 3 | 4 | 5 | 6 | | VI-2 | Plch1 | 23236 | 4-May-15 | 2775 | 3 | 4 | 5 | 6 | | VI-2 | Sec14l4 | 284904 | 4-May-15 |
| 2681 | 3 | 4 | 5 | 6 | | VI-2 | Plcd4 | 84812 | 4-May-15 | 2776 | 3 | 4 | 5 | 6 | | VI-2 | Sec14l5 | 9717 | 4-May-15 |
| 2682 | 3 | 4 | 5 | 6 | | VI-2 | Plekha6 | 22874 | 4-May-15 | 2777 | 3 | 4 | 5 | 6 | | VI-2 | Sectm1a | | |
| 2683 | 3 | 4 | 5 | 6 | | VI-2 | Plekhg6 | 55200 | 4-May-15 | 2778 | 3 | 4 | 5 | 6 | | VI-2 | Sectm1b | | |
| 2684 | 3 | 4 | 5 | 6 | | VI-2 | Plekhh1 | 57475 | 12-May-15 | 2779 | 3 | 4 | 5 | 6 | | VI-2 | Sema6c | 10500 | 4-May-15 |
| 2685 | 3 | 4 | 5 | 6 | | VI-2 | Pletios | | | 2780 | 3 | 4 | 5 | 6 | | VI-2 | Sept3 | 55964 | 4-May-15 |
| 2686 | 3 | 4 | 5 | 6 | | VI-2 | Plk2 | 10769 | 17-May-15 | 2781 | 3 | 4 | 5 | 6 | | VI-2 | Serpina11 | 256394 | 4-May-15 |
| 2687 | 3 | 4 | 5 | 6 | | VI-2 | Pllp | 51090 | 4-May-15 | 2782 | 3 | 4 | 5 | 6 | | VI-2 | Serpina12 | 145264 | 12-May-15 |
| 2688 | 3 | 4 | 5 | 6 | | VI-2 | Plp1 | 5354 | 23-May-15 | 2783 | 3 | 4 | 5 | 6 | | VI-2 | Serpina4-ps1 | | |
| 2689 | 3 | 4 | 5 | 6 | | VI-2 | Pls1 | 5357 | 4-May-15 | 2784 | 3 | 4 | 5 | 6 | | VI-2 | Serpinc1 | 462 | 17-May-15 |
| 2690 | 3 | 4 | 5 | 6 | | VI-2 | Plscr2 | 57047 | 4-May-15 | 2785 | 3 | 4 | 5 | 6 | | VI-2 | Serpini1 | 5274 | 12-May-15 |
| 2691 | 3 | 4 | 5 | 6 | | VI-2 | Plxnb1 | 5364 | 4-May-15 | 2786 | 3 | 4 | 5 | 6 | | VI-2 | Sfi1 | 9814 | 4-May-15 |
| 2692 | 3 | 4 | 5 | 6 | | VI-2 | Pm20d1 | 148811 | 4-May-15 | 2787 | 3 | 4 | 5 | 6 | | VI-2 | Sfrp4 | 6424 | 17-May-15 |
| 2693 | 3 | 4 | 5 | 6 | | VI-2 | Pnmt | 5409 | 7-Jun-15 | 2788 | 3 | 4 | 5 | 6 | | VI-2 | Sh3bgrl2 | 83699 | 4-May-15 |
| 2694 | 3 | 4 | 5 | 6 | | VI-2 | Pparg | 5468 | 17-May-15 | 2789 | 3 | 4 | 5 | 6 | | VI-2 | Shank2 | 22941 | 23-May-15 |
| 2695 | 3 | 4 | 5 | 6 | | VI-2 | Ppargc1b | 133522 | 4-May-15 | 2790 | 3 | 4 | 5 | 6 | | VI-2 | Shroom3 | 57619 | 21-May-15 |
| 2696 | 3 | 4 | 5 | 6 | | VI-2 | Ppfibp2 | 8495 | 4-May-15 | 2791 | 3 | 4 | 5 | 6 | | VI-2 | Skint1 | 391037 | 4-May-15 |
| 2697 | 3 | 4 | 5 | 6 | | VI-2 | Ppip5k2 | 23262 | 4-May-15 | 2792 | 3 | 4 | 5 | 6 | | VI-2 | Slc12a2 | 6558 | 4-May-15 |
| 2698 | 3 | 4 | 5 | 6 | | VI-2 | Ppp1r32 | 220004 | 4-May-15 | 2793 | 3 | 4 | 5 | 6 | | VI-2 | Slc13a2 | 9058 | 4-May-15 |
| 2699 | 3 | 4 | 5 | 6 | | VI-2 | Ppp1r36 | 145376 | 4-May-15 | 2794 | 3 | 4 | 5 | 6 | | VI-2 | Slc13a2os | | |
| 2700 | 3 | 4 | 5 | 6 | | VI-2 | Ppp1r3a | 5506 | 12-May-15 | 2795 | 3 | 4 | 5 | 6 | | VI-2 | Slc13a4 | 26266 | 4-May-15 |
| 2701 | 3 | 4 | 5 | 6 | | VI-2 | Ppp2r2b | 5521 | 23-May-15 | 2796 | 3 | 4 | 5 | 6 | | VI-2 | Slc15a5 | 729025 | 4-May-15 |
| 2702 | 3 | 4 | 5 | 6 | | VI-2 | Prdm8 | 56978 | 4-May-15 | 2797 | 3 | 4 | 5 | 6 | | VI-2 | Slc16a5 | 9121 | 4-May-15 |
| 2703 | 3 | 4 | 5 | 6 | | VI-2 | Prickle1 | 144165 | 23-May-15 | 2798 | 3 | 4 | 5 | 6 | | VI-2 | Slc17a2 | 10246 | 4-May-15 |
| 2704 | 3 | 4 | 5 | 6 | | VI-2 | Prodh | 5625 | 4-May-15 | 2799 | 3 | 4 | 5 | 6 | | VI-2 | Slc1a1 | 6505 | 12-May-15 |
| 2705 | 3 | 4 | 5 | 6 | | VI-2 | Prok1 | 84432 | 4-May-15 | 2800 | 3 | 4 | 5 | 6 | | VI-2 | Slc22a14 | 6580 | 17-May-15 |
| 2706 | 3 | 4 | 5 | 6 | | VI-2 | Proz | 8858 | 4-May-15 | 2801 | 3 | 4 | 5 | 6 | | VI-2 | Slc22a14 | 9389 | 4-May-15 |
| 2707 | 3 | 4 | 5 | 6 | | VI-2 | Prps2 | 5634 | 4-May-15 | 2802 | 3 | 4 | 5 | 6 | | VI-2 | Slc22a3 | 6581 | 17-May-15 |
| 2708 | 3 | 4 | 5 | 6 | | VI-2 | Prr32 | 100130 613 | 4-May-15 | 2803 | 3 | 4 | 5 | 6 | | VI-2 | Slc22a7 | 10864 | 17-May-15 |
| 2709 | 3 | 4 | 5 | 6 | | VI-2 | Prrt4 | 401399 | 4-May-15 | 2804 | 3 | 4 | 5 | 6 | | VI-2 | Slc25a15 | 10166 | 23-May-15 |
| 2710 | 3 | 4 | 5 | 6 | | VI-2 | Prss29 | | | 2805 | 3 | 4 | 5 | 6 | | VI-2 | Slc25a29 | 123096 | 4-May-15 |
| 2711 | 3 | 4 | 5 | 6 | | VI-2 | Prss56 | 646960 | 4-May-15 | 2806 | 3 | 4 | 5 | 6 | | VI-2 | Slc25a33 | 84275 | 4-May-15 |
| 2712 | 3 | 4 | 5 | 6 | | VI-2 | Prss57 | 400668 | 23-May-15 | 2807 | 3 | 4 | 5 | 6 | | VI-2 | Slc25a45 | 283130 | 12-May-15 |
| 2713 | 3 | 4 | 5 | 6 | | VI-2 | Psma8 | 143471 | 12-May-15 | 2808 | 3 | 4 | 5 | 6 | | VI-2 | Slc26a3 | 1811 | 4-May-15 |
| 2714 | 3 | 4 | 5 | 6 | | VI-2 | Ptar1 | 375743 | 4-May-15 | 2809 | 3 | 4 | 5 | 6 | | VI-2 | Slc27a6 | 28965 | 4-May-15 |
| 2715 | 3 | 4 | 5 | 6 | | VI-2 | Ptch2 | 8643 | 23-May-15 | 2810 | 3 | 4 | 5 | 6 | | VI-2 | Slc2a12 | 154091 | 17-May-15 |
| 2716 | 3 | 4 | 5 | 6 | | VI-2 | Ptger3 | 5733 | 12-May-15 | 2811 | 3 | 4 | 5 | 6 | | VI-2 | Slc2a13 | 114134 | 4-May-15 |
| 2717 | 3 | 4 | 5 | 6 | | VI-2 | Ptgfr | 5737 | 4-May-15 | 2812 | 3 | 4 | 5 | 6 | | VI-2 | Slc2a5 | 6518 | 12-May-15 |
| 2718 | 3 | 4 | 5 | 6 | | VI-2 | Ptpn4 | 5775 | 4-May-15 | 2813 | 3 | 4 | 5 | 6 | | VI-2 | Slc31a2 | 1318 | 4-May-15 |
| 2719 | 3 | 4 | 5 | 6 | | VI-2 | Pycard | 29108 | 4-May-15 | 2814 | 3 | 4 | 5 | 6 | | VI-2 | Slc35f3 | 148641 | 4-May-15 |
| 2720 | 3 | 4 | 5 | 6 | | VI-2 | Pygb | 5834 | 4-May-15 | 2815 | 3 | 4 | 5 | 6 | | VI-2 | Slc37a1 | 54020 | 4-May-15 |
| 2721 | 3 | 4 | 5 | 6 | | VI-2 | Rab17 | 64284 | 4-May-15 | 2816 | 3 | 4 | 5 | 6 | | VI-2 | Slc38a3 | 10993 | 4-May-15 |
| 2722 | 3 | 4 | 5 | 6 | | VI-2 | Rab27a | 5873 | 14-May-15 | 2817 | 3 | 4 | 5 | 6 | | VI-2 | Slc4a4 | 8671 | 17-May-15 |

Fig. 30 - 16

| | | | | | | | | | | | | | | | | | |
|---|---|---|---|---|---|---|---|---|---|---|---|---|---|---|---|---|---|
| 2818 | 3 | 4 | 5 | 6 | | VI-2 | Slc4a8 | 9498 | 4-May-15 | 2914 | 3 | 4 | 5 | 6 | | VI-2 | Trim38 | 10475 | 12-May-15 |
| 2819 | 3 | 4 | 5 | 6 | | VI-2 | Slc51a | 200931 | 4-May-15 | 2915 | 3 | 4 | 5 | 6 | | VI-2 | Trim6 | 117854 | 4-May-15 |
| 2820 | 3 | 4 | 5 | 6 | | VI-2 | Slc52a3 | 113278 | 4-May-15 | 2916 | 3 | 4 | 5 | 6 | | VI-2 | Trim68 | 55128 | 4-May-15 |
| 2821 | 3 | 4 | 5 | 6 | | VI-2 | Slc5a6 | 8884 | 12-May-15 | 2917 | 3 | 4 | 5 | 6 | | VI-2 | Trp53inp2 | | |
| 2822 | 3 | 4 | 5 | 6 | | VI-2 | Slc6a13 | 6540 | 4-May-15 | 2918 | 3 | 4 | 5 | 6 | | VI-2 | Trpm5 | 29850 | 4-May-15 |
| 2823 | 3 | 4 | 5 | 6 | | VI-2 | Slc6a8 | 6535 | 23-May-15 | 2919 | 3 | 4 | 5 | 6 | | VI-2 | Tsjp | 85480 | 24-May-15 |
| 2824 | 3 | 4 | 5 | 6 | | VI-2 | Slc7a15 | | | 2920 | 3 | 4 | 5 | 6 | | VI-2 | Tspan10 | 83882 | 14-May-15 |
| 2825 | 3 | 4 | 5 | 6 | | VI-2 | Slco5a1 | 81796 | 4-May-15 | 2921 | 3 | 4 | 5 | 6 | | VI-2 | Tspan18 | 90139 | 4-May-15 |
| 2826 | 3 | 4 | 5 | 6 | | VI-2 | Slitrk6 | 84189 | 23-May-15 | 2922 | 3 | 4 | 5 | 6 | | VI-2 | Tspan4 | 7106 | 4-May-15 |
| 2827 | 3 | 4 | 5 | 6 | | VI-2 | Smad6 | 4091 | 12-May-15 | 2923 | 3 | 4 | 5 | 6 | | VI-2 | Tstd1 | 100131187 | 4-May-15 |
| 2828 | 3 | 4 | 5 | 6 | | VI-2 | Smad9 | 4093 | 4-May-15 | 2924 | 3 | 4 | 5 | 6 | | VI-2 | Ttc21a | 199223 | 4-May-15 |
| 2829 | 3 | 4 | 5 | 6 | | VI-2 | Smco1 | 255798 | 4-May-15 | 2925 | 3 | 4 | 5 | 6 | | VI-2 | Ttc22 | 55001 | 4-May-15 |
| 2830 | 3 | 4 | 5 | 6 | | VI-2 | Smim24 | 284422 | 4-May-15 | 2926 | 3 | 4 | 5 | 6 | | VI-2 | Ttc33 | 23548 | 4-May-15 |
| 2831 | 3 | 4 | 5 | 6 | | VI-2 | Smyd2 | 56950 | 21-May-15 | 2927 | 3 | 4 | 5 | 6 | | VI-2 | Ttll1 | 25809 | 4-May-15 |
| 2832 | 3 | 4 | 5 | 6 | | VI-2 | Snap23 | 8773 | 4-May-15 | 2928 | 3 | 4 | 5 | 6 | | VI-2 | Ttll3 | 26140 | 23-May-15 |
| 2833 | 3 | 4 | 5 | 6 | | VI-2 | Sned1 | 25992 | 12-May-15 | 2929 | 3 | 4 | 5 | 6 | | VI-2 | Tuba4a | 7277 | 4-May-15 |
| 2834 | 3 | 4 | 5 | 6 | | VI-2 | Snhg11 | 128439 | 4-May-15 | 2930 | 3 | 4 | 5 | 6 | | VI-2 | Tuba8 | 51807 | 4-May-15 |
| 2835 | 3 | 4 | 5 | 6 | | VI-2 | Snhg6 | 641638 | 12-May-15 | 2931 | 3 | 4 | 5 | 6 | | VI-2 | Tubb4a | 10382 | 12-May-15 |
| 2836 | 3 | 4 | 5 | 6 | | VI-2 | Snrnp25 | 79622 | 4-May-15 | 2932 | 3 | 4 | 5 | 6 | | VI-2 | Tusc5 | 286753 | 4-May-15 |
| 2837 | 3 | 4 | 5 | 6 | | VI-2 | Sod2 | 6648 | 17-May-15 | 2933 | 3 | 4 | 5 | 6 | | VI-2 | Tymp | 1890 | 23-May-15 |
| 2838 | 3 | 4 | 5 | 6 | | VI-2 | Spa17 | 53340 | 4-May-15 | 2934 | 3 | 4 | 5 | 6 | | VI-2 | Ubd | 10537 | 3-May-15 |
| 2839 | 3 | 4 | 5 | 6 | | VI-2 | Spag16 | 79582 | 12-May-15 | 2935 | 3 | 4 | 5 | 6 | | VI-2 | Ubxn11 | 91544 | 4-May-15 |
| 2840 | 3 | 4 | 5 | 6 | | VI-2 | Spag6 | 9576 | 12-May-15 | 2936 | 3 | 4 | 5 | 6 | | VI-2 | Uck1los | 100133386 | 4-May-15 |
| 2841 | 3 | 4 | 5 | 6 | | VI-2 | Spag8 | 26206 | 4-May-15 | 2937 | 3 | 4 | 5 | 6 | | VI-2 | Ugt1a5 | 54579 | 12-May-15 |
| 2842 | 3 | 4 | 5 | 6 | | VI-2 | Spata33 | 124045 | 4-May-15 | 2938 | 3 | 4 | 5 | 6 | | VI-2 | Unc45b | 146862 | 12-May-15 |
| 2843 | 3 | 4 | 5 | 6 | | VI-2 | Spata4 | 132851 | 4-May-15 | 2939 | 3 | 4 | 5 | 6 | | VI-2 | Uox | 391051 | 12-May-15 |
| 2844 | 3 | 4 | 5 | 6 | | VI-2 | Speg | 10290 | 12-May-15 | 2940 | 3 | 4 | 5 | 6 | | VI-2 | Upk3bl | 100134938 | 4-May-15 |
| 2845 | 3 | 4 | 5 | 6 | | VI-2 | Spin2d | | | 2941 | 3 | 4 | 5 | 6 | | VI-2 | Ush1c | 10083 | 23-May-15 |
| 2846 | 3 | 4 | 5 | 6 | | VI-2 | Spns2 | 124976 | 4-May-15 | 2942 | 3 | 4 | 5 | 6 | | VI-2 | Vars2 | 57176 | 7-Jun-15 |
| 2847 | 3 | 4 | 5 | 6 | | VI-2 | Sprr4 | 163778 | 16-May-15 | 2943 | 3 | 4 | 5 | 6 | | VI-2 | Vldlr | 7436 | 23-May-15 |
| 2848 | 3 | 4 | 5 | 6 | | VI-2 | Srd5a1 | 6715 | 12-May-15 | 2944 | 3 | 4 | 5 | 6 | | VI-2 | Vsig8 | 391123 | 4-May-15 |
| 2849 | 3 | 4 | 5 | 6 | | VI-2 | Srfbp1 | 153443 | 4-May-15 | 2945 | 3 | 4 | 5 | 6 | | VI-2 | Vsnl1 | 7447 | 4-May-15 |
| 2850 | 3 | 4 | 5 | 6 | | VI-2 | St8sia1 | 6489 | 4-May-15 | 2946 | 3 | 4 | 5 | 6 | | VI-2 | Vstm2b | 342865 | 4-May-15 |
| 2851 | 3 | 4 | 5 | 6 | | VI-2 | Stk36 | 27148 | 4-May-15 | 2947 | 3 | 4 | 5 | 6 | | VI-2 | Wasf1 | 8936 | 4-May-15 |
| 2852 | 3 | 4 | 5 | 6 | | VI-2 | Stmn2 | 11075 | 4-May-15 | 2948 | 3 | 4 | 5 | 6 | | VI-2 | Wdr16 | 146845 | 4-May-15 |
| 2853 | 3 | 4 | 5 | 6 | | VI-2 | Sult1c2 | 6819 | 7-Jun-15 | 2949 | 3 | 4 | 5 | 6 | | VI-2 | Wdr63 | 126820 | 12-May-15 |
| 2854 | 3 | 4 | 5 | 6 | | VI-2 | Susd2 | 56241 | 4-May-15 | 2950 | 3 | 4 | 5 | 6 | | VI-2 | Wdr78 | 79819 | 4-May-15 |
| 2855 | 3 | 4 | 5 | 6 | | VI-2 | Sva | | | 2951 | 3 | 4 | 5 | 6 | | VI-2 | Wdr95 | | |
| 2856 | 3 | 4 | 5 | 6 | | VI-2 | Svs1 | | | 2952 | 3 | 4 | 5 | 6 | | VI-2 | Wdr96 | 80217 | 4-May-15 |
| 2857 | 3 | 4 | 5 | 6 | | VI-2 | Svs3a | | | 2953 | 3 | 4 | 5 | 6 | | VI-2 | Wee1 | 7465 | 4-May-15 |
| 2858 | 3 | 4 | 5 | 6 | | VI-2 | Svs3b | | | 2954 | 3 | 4 | 5 | 6 | | VI-2 | Whrn | 25861 | 23-May-15 |
| 2859 | 3 | 4 | 5 | 6 | | VI-2 | Sybu | 55638 | 4-May-15 | 2955 | 3 | 4 | 5 | 6 | | VI-2 | Wif1 | 11197 | 4-May-15 |
| 2860 | 3 | 4 | 5 | 6 | | VI-2 | Syde2 | 84144 | 4-May-15 | 2956 | 3 | 4 | 5 | 6 | | VI-2 | Wipf3 | 644150 | 4-May-15 |
| 2861 | 3 | 4 | 5 | 6 | | VI-2 | Syne4 | 163183 | 12-May-15 | 2957 | 3 | 4 | 5 | 6 | | VI-2 | Wnk2 | 65268 | 12-May-15 |
| 2862 | 3 | 4 | 5 | 6 | | VI-2 | Syt12 | 91683 | 7-Jun-15 | 2958 | 3 | 4 | 5 | 6 | | VI-2 | Wnt2 | 7472 | 12-May-15 |
| 2863 | 3 | 4 | 5 | 6 | | VI-2 | Syt15 | 83849 | 4-May-15 | 2959 | 3 | 4 | 5 | 6 | | VI-2 | Wnt2b | 7482 | 17-May-15 |
| 2864 | 3 | 4 | 5 | 6 | | VI-2 | Sytl1 | 84958 | 12-May-15 | 2960 | 3 | 4 | 5 | 6 | | VI-2 | Wnt3a | 89780 | 17-May-15 |
| 2865 | 3 | 4 | 5 | 6 | | VI-2 | Tagap1 | 117289 | 4-May-15 | 2961 | 3 | 4 | 5 | 6 | | VI-2 | Wnt5b | 83029 | 12-May-15 |
| 2866 | 3 | 4 | 5 | 6 | | VI-2 | Tap2 | 6891 | 7-Jun-15 | 2962 | 3 | 4 | 5 | 6 | | VI-2 | Wnt8b | 7479 | 4-May-15 |
| 2867 | 3 | 4 | 5 | 6 | | VI-2 | Tbx10 | 347853 | 4-May-15 | 2963 | 3 | 4 | 5 | 6 | | VI-2 | Wscd2 | 9671 | 4-May-15 |
| 2868 | 3 | 4 | 5 | 6 | | VI-2 | Tcaim | 285343 | 4-May-15 | 2964 | 3 | 4 | 5 | 6 | | VI-2 | Wt1 | 7490 | 24-May-15 |
| 2869 | 3 | 4 | 5 | 6 | | VI-2 | Tchhl1 | 126617 | 12-May-15 | 2965 | 3 | 4 | 5 | 6 | | VI-2 | Xlr3c | | |
| 2870 | 3 | 4 | 5 | 6 | | VI-2 | Tdo2 | 6999 | 4-May-15 | 2966 | 3 | 4 | 5 | 6 | | VI-2 | Xrra1 | 143570 | 4-May-15 |
| 2871 | 3 | 4 | 5 | 6 | | VI-2 | Tecrl | 253017 | 4-May-15 | 2967 | 3 | 4 | 5 | 6 | | VI-2 | Xylb | 9942 | 4-May-15 |
| 2872 | 3 | 4 | 5 | 6 | | VI-2 | Tef | 7008 | 4-May-15 | 2968 | 3 | 4 | 5 | 6 | | VI-2 | Ybx2 | 51087 | 4-May-15 |
| 2873 | 3 | 4 | 5 | 6 | | VI-2 | Tex40 | 25858 | 4-May-15 | 2969 | 3 | 4 | 5 | 6 | | VI-2 | Yipf7 | 285525 | 4-May-15 |
| 2874 | 3 | 4 | 5 | 6 | | VI-2 | Them6 | 51337 | 4-May-15 | 2970 | 3 | 4 | 5 | 6 | | VI-2 | Zbtb32 | 27033 | 4-May-15 |
| 2875 | 3 | 4 | 5 | 6 | | VI-2 | Them7 | | | 2971 | 3 | 4 | 5 | 6 | | VI-2 | Zbtb7c | 201501 | 12-May-15 |
| 2876 | 3 | 4 | 5 | 6 | | VI-2 | Tinag | 27283 | 4-May-15 | 2972 | 3 | 4 | 5 | 6 | | VI-2 | Zc3h6 | 376940 | 4-May-15 |
| 2877 | 3 | 4 | 5 | 6 | | VI-2 | Tlcd2 | 727910 | 4-May-15 | 2973 | 3 | 4 | 5 | 6 | | VI-2 | Zcchc5 | 203430 | 4-May-15 |
| 2878 | 3 | 4 | 5 | 6 | | VI-2 | Tlel | 79816 | 4-May-15 | 2974 | 3 | 4 | 5 | 6 | | VI-2 | Zfand4 | 93550 | 4-May-15 |
| 2879 | 3 | 4 | 5 | 6 | | VI-2 | Tlr12 | | | 2975 | 3 | 4 | 5 | 6 | | VI-2 | Zfp133-ps | | |
| 2880 | 3 | 4 | 5 | 6 | | VI-2 | Tmed11 | | | 2976 | 3 | 4 | 5 | 6 | | VI-2 | Zfp157 | | |
| 2881 | 3 | 4 | 5 | 6 | | VI-2 | Tmem106a | 113277 | 12-May-15 | 2977 | 3 | 4 | 5 | 6 | | VI-2 | Zfp30 | 22835 | |
| 2882 | 3 | 4 | 5 | 6 | | VI-2 | Tmem132b | 114795 | 4-May-15 | 2978 | 3 | 4 | 5 | 6 | | VI-2 | Zfp474 | | |
| 2883 | 3 | 4 | 5 | 6 | | VI-2 | Tmem136 | 219902 | 4-May-15 | 2979 | 3 | 4 | 5 | 6 | | VI-2 | Zfp503 | | |
| 2884 | 3 | 4 | 5 | 6 | | VI-2 | Tmem151b | 441151 | 4-May-15 | 2980 | 3 | 4 | 5 | 6 | | VI-2 | Zfp612 | 7571 | 12-May-15 |
| 2885 | 3 | 4 | 5 | 6 | | VI-2 | Tmem179 | 388021 | 4-May-15 | 2981 | 3 | 4 | 5 | 6 | | VI-2 | Zfp791 | | |
| 2886 | 3 | 4 | 5 | 6 | | VI-2 | Tmem181b-ps | | | 2982 | 3 | 4 | 5 | 6 | | VI-2 | Zmynd10 | 51364 | 21-May-15 |
| 2887 | 3 | 4 | 5 | 6 | | VI-2 | Tmem181c-ps | | | 2983 | 3 | 4 | 5 | 6 | | VI-1 | 0610009L18Rik | | |
| 2888 | 3 | 4 | 5 | 6 | | VI-2 | Tmem200b | 399474 | 4-May-15 | 2984 | 3 | 4 | 5 | 6 | | VI-1 | 0610010B08Rik | | |
| 2889 | 3 | 4 | 5 | 6 | | VI-2 | Tmem213 | 155006 | 4-May-15 | 2985 | 3 | 4 | 5 | 6 | | VI-1 | 0610039K10Rik | | |
| 2890 | 3 | 4 | 5 | 6 | | VI-2 | Tmem232 | 642987 | 4-May-15 | 2986 | 3 | 4 | 5 | 6 | | VI-1 | 0610040J01Rik | | |
| 2891 | 3 | 4 | 5 | 6 | | VI-2 | Tmem233 | 387890 | 4-May-15 | 2987 | 3 | 4 | 5 | 6 | | VI-1 | 1100001G20Rik | | |
| 2892 | 3 | 4 | 5 | 6 | | VI-2 | Tmem25 | 84866 | 4-May-15 | 2988 | 3 | 4 | 5 | 6 | | VI-1 | 1110020A21Rik | | |
| 2893 | 3 | 4 | 5 | 6 | | VI-2 | Tmem254c | | | 2989 | 3 | 4 | 5 | 6 | | VI-1 | 1110038B12Rik | | |
| 2894 | 3 | 4 | 5 | 6 | | VI-2 | Tmem27 | 57393 | 17-May-15 | 2990 | 3 | 4 | 5 | 6 | | VI-1 | 1190007I07Rik | | |
| 2895 | 3 | 4 | 5 | 6 | | VI-2 | Tmem35 | 59353 | 4-May-15 | 2991 | 3 | 4 | 5 | 6 | | VI-1 | 1300002K09Rik | | |
| 2896 | 3 | 4 | 5 | 6 | | VI-2 | Tmem37 | 140738 | 12-May-15 | 2992 | 3 | 4 | 5 | 6 | | VI-1 | 1300017J02Rik | | |
| 2897 | 3 | 4 | 5 | 6 | | VI-2 | Tmem47 | 83604 | 4-May-15 | 2993 | 3 | 4 | 5 | 6 | | VI-1 | 1500009L16Rik | | |
| 2898 | 3 | 4 | 5 | 6 | | VI-2 | Tmem52 | 339456 | 4-May-15 | 2994 | 3 | 4 | 5 | 6 | | VI-1 | 1500012F01Rik | | |
| 2899 | 3 | 4 | 5 | 6 | | VI-2 | Tmem71 | 137835 | 4-May-15 | 2995 | 3 | 4 | 5 | 6 | | VI-1 | 1600002H07Rik | | |
| 2900 | 3 | 4 | 5 | 6 | | VI-2 | Tmem86a | 144110 | 4-May-15 | 2996 | 3 | 4 | 5 | 6 | | VI-1 | 1600014C10Rik | | |
| 2901 | 3 | 4 | 5 | 6 | | VI-2 | Tmem8c | 389827 | 4-May-15 | 2997 | 3 | 4 | 5 | 6 | | VI-1 | 1600016N20Rik | | |
| 2902 | 3 | 4 | 5 | 6 | | VI-2 | Tmigd1 | 388364 | 4-May-15 | 2998 | 3 | 4 | 5 | 6 | | VI-1 | 1700001L05Rik | | |
| 2903 | 3 | 4 | 5 | 6 | | VI-2 | Tmod4 | 29765 | 4-May-15 | 2999 | 3 | 4 | 5 | 6 | | VI-1 | 1700012D14Rik | | |
| 2904 | 3 | 4 | 5 | 6 | | VI-2 | Tmprss11a | 339967 | 12-May-15 | 3000 | 3 | 4 | 5 | 6 | | VI-1 | 1700019D03Rik | | |
| 2905 | 3 | 4 | 5 | 6 | | VI-2 | Tmprss13 | 84000 | 4-May-15 | 3001 | 3 | 4 | 5 | 6 | | VI-1 | 1700019G17Rik | | |
| 2906 | 3 | 4 | 5 | 6 | | VI-2 | Tmprss2 | 7113 | 21-May-15 | 3002 | 3 | 4 | 5 | 6 | | VI-1 | 1700019N19Rik | | |
| 2907 | 3 | 4 | 5 | 6 | | VI-2 | Tnfaip3 | 7128 | 12-May-15 | 3003 | 3 | 4 | 5 | 6 | | VI-1 | 1700028L06Rik | | |
| 2908 | 3 | 4 | 5 | 6 | | VI-2 | Tnfrsf11b | 4982 | 7-Jun-15 | 3004 | 3 | 4 | 5 | 6 | | VI-1 | 1700029F12Rik | | |
| 2909 | 3 | 4 | 5 | 6 | | VI-2 | Tnfsf10 | 8743 | 24-May-15 | 3005 | 3 | 4 | 5 | 6 | | VI-1 | 1700037H04Rik | | |
| 2910 | 3 | 4 | 5 | 6 | | VI-2 | Tnni3k | 51086 | 4-May-15 | 3006 | 3 | 4 | 5 | 6 | | VI-1 | 1700039E22Rik | | |
| 2911 | 3 | 4 | 5 | 6 | | VI-2 | Tnnt1 | 7138 | 23-May-15 | 3007 | 3 | 4 | 5 | 6 | | VI-1 | 1700045H11Rik | | |
| 2912 | 3 | 4 | 5 | 6 | | VI-2 | Tomm40l | 84134 | 4-May-15 | | | | | | | | | | |
| 2913 | 3 | 4 | 5 | 6 | | VI-2 | Trim17 | 51127 | 4-May-15 | | | | | | | | | | |

Fig. 30 - 17

| | | | | | | | | | | | | | | | | |
|---|---|---|---|---|---|---|---|---|---|---|---|---|---|---|---|---|
| 3008 | 3 | 4 | 5 | 6 | | VI-1 | 1700061J17Rik | | | 3101 | 3 | 4 | 5 | 6 | | VI-1 | 9330175E14Rik | | |
| 3009 | 3 | 4 | 5 | 6 | | VI-1 | 1700066O22Rik | | | 3102 | 3 | 4 | 5 | 6 | | VI-1 | 9430083A17Rik | | |
| 3010 | 3 | 4 | 5 | 6 | | VI-1 | 1700086O06Rik | | | 3103 | 3 | 4 | 5 | 6 | | VI-1 | 9530002B09Rik | | |
| 3011 | 3 | 4 | 5 | 6 | | VI-1 | 1700120G07Rik | | | 3104 | 3 | 4 | 5 | 6 | | VI-1 | 9530077C05Rik | | |
| 3012 | 3 | 4 | 5 | 6 | | VI-1 | 1810010O01Rik | | | 3105 | 3 | 4 | 5 | 6 | | VI-1 | A230056P14Rik | | |
| 3013 | 3 | 4 | 5 | 6 | | VI-1 | 1810011H11Rik | | | 3106 | 3 | 4 | 5 | 6 | | VI-1 | A330040F15Rik | | |
| 3014 | 3 | 4 | 5 | 6 | | VI-1 | 1810011O10Rik | | | 3107 | 3 | 4 | 5 | 6 | | VI-1 | A330049N07Rik | | |
| 3015 | 3 | 4 | 5 | 6 | | VI-1 | 1810018F18Rik | | | 3108 | 3 | 4 | 5 | 6 | | VI-1 | A430078G23Rik | | |
| 3016 | 3 | 4 | 5 | 6 | | VI-1 | 1810020O05Rik | | | 3109 | 3 | 4 | 5 | 6 | | VI-1 | A4galt | 53947 | 12-May-15 |
| 3017 | 3 | 4 | 5 | 6 | | VI-1 | 1810044O09Rik | | | 3110 | 3 | 4 | 5 | 6 | | VI-1 | A530016L24Rik | | |
| 3018 | 3 | 4 | 5 | 6 | | VI-1 | 1810046K07Rik | | | 3111 | 3 | 4 | 5 | 6 | | VI-1 | A630001G21Rik | | |
| 3019 | 3 | 4 | 5 | 6 | | VI-1 | 1810055G02Rik | | | 3112 | 3 | 4 | 5 | 6 | | VI-1 | A630023P12Rik | | |
| 3020 | 3 | 4 | 5 | 6 | | VI-1 | 1810064F22Rik | | | 3113 | 3 | 4 | 5 | 6 | | VI-1 | A630033H20Rik | | |
| 3021 | 3 | 4 | 5 | 6 | | VI-1 | 2010005H15Rik | | | 3114 | 3 | 4 | 5 | 6 | | VI-1 | A730017C20Rik | | |
| 3022 | 3 | 4 | 5 | 6 | | VI-1 | 2010016I18Rik | | | 3115 | 3 | 4 | 5 | 6 | | VI-1 | A730036I17Rik | | |
| 3023 | 3 | 4 | 5 | 6 | | VI-1 | 2010106E10Rik | | | 3116 | 3 | 4 | 5 | 6 | | VI-1 | A930006K02Rik | | |
| 3024 | 3 | 4 | 5 | 6 | | VI-1 | 2010300C02Rik | | | 3117 | 3 | 4 | 5 | 6 | | VI-1 | AA414768 | | |
| 3025 | 3 | 4 | 5 | 6 | | VI-1 | 2200002D01Rik | | | 3118 | 3 | 4 | 5 | 6 | | VI-1 | AA986860 | | |
| 3026 | 3 | 4 | 5 | 6 | | VI-1 | 2310014L17Rik | | | 3119 | 3 | 4 | 5 | 6 | | VI-1 | Aacs | 65985 | 12-May-15 |
| 3027 | 3 | 4 | 5 | 6 | | VI-1 | 2310015B20Rik | | | 3120 | 3 | 4 | 5 | 6 | | VI-1 | AB124611 | | |
| 3028 | 3 | 4 | 5 | 6 | | VI-1 | 2310034O05Rik | | | 3121 | 3 | 4 | 5 | 6 | | VI-1 | Abca1 | 19 | 24-May-15 |
| 3029 | 3 | 4 | 5 | 6 | | VI-1 | 2310042E22Rik | | | 3122 | 3 | 4 | 5 | 6 | | VI-1 | Abca2 | 20 | 12-May-15 |
| 3030 | 3 | 4 | 5 | 6 | | VI-1 | 2310057M21Rik | | | 3123 | 3 | 4 | 5 | 6 | | VI-1 | Abca4 | 24 | 23-May-15 |
| | | | | | | | | | | 3124 | 3 | 4 | 5 | 6 | | VI-1 | Abca8a | | |
| 3031 | 3 | 4 | 5 | 6 | | VI-1 | 2410006H16Rik | | | 3125 | 3 | 4 | 5 | 6 | | VI-1 | Abch10 | 23456 | 12-May-15 |
| 3032 | 3 | 4 | 5 | 6 | | VI-1 | 2410017I17Rik | | | 3126 | 3 | 4 | 5 | 6 | | VI-1 | Abcb1b | | |
| 3033 | 3 | 4 | 5 | 6 | | VI-1 | 2410076I21Rik | | | 3127 | 3 | 4 | 5 | 6 | | VI-1 | Abcb4 | 5244 | 12-May-15 |
| 3034 | 3 | 4 | 5 | 6 | | VI-1 | 2610207I16Rik | | | 3128 | 3 | 4 | 5 | 6 | | VI-1 | Abcb5 | 340273 | 4-May-15 |
| 3035 | 3 | 4 | 5 | 6 | | VI-1 | 2610307P16Rik | | | 3129 | 3 | 4 | 5 | 6 | | VI-1 | Abcb6 | 10058 | 12-May-15 |
| 3036 | 3 | 4 | 5 | 6 | | VI-1 | 2610318N02Rik | | | 3130 | 3 | 4 | 5 | 6 | | VI-1 | Abcc3 | 8714 | 17-May-15 |
| 3037 | 3 | 4 | 5 | 6 | | VI-1 | 2610524H06Rik | | | 3131 | 3 | 4 | 5 | 6 | | VI-1 | Abcc9 | 10060 | 23-May-15 |
| 3038 | 3 | 4 | 5 | 6 | | VI-1 | 2610528A11Rik | | | 3132 | 3 | 4 | 5 | 6 | | VI-1 | Abcd2 | 225 | 7-Jun-15 |
| 3039 | 3 | 4 | 5 | 6 | | VI-1 | 2700094K13Rik | | | 3133 | 3 | 4 | 5 | 6 | | VI-1 | Abcg1 | 9619 | 24-May-15 |
| 3040 | 3 | 4 | 5 | 6 | | VI-1 | 2810408A11Rik | | | 3134 | 3 | 4 | 5 | 6 | | VI-1 | Abcg2 | 9429 | 24-May-15 |
| 3041 | 3 | 4 | 5 | 6 | | VI-1 | 2810408J11Rik | | | 3135 | 3 | 4 | 5 | 6 | | VI-1 | Abcg4 | 64137 | 12-May-15 |
| 3042 | 3 | 4 | 5 | 6 | | VI-1 | 2810459M11Rik | | | 3136 | 3 | 4 | 5 | 6 | | VI-1 | Abhd1 | 84696 | 4-May-15 |
| 3043 | 3 | 4 | 5 | 6 | | VI-1 | 2810474O19Rik | | | 3137 | 3 | 4 | 5 | 6 | | VI-1 | Abhd11os | | |
| 3044 | 3 | 4 | 5 | 6 | | VI-1 | 2900005J15Rik | | | 3138 | 3 | 4 | 5 | 6 | | VI-1 | Abhd2 | 11057 | 23-May-15 |
| 3045 | 3 | 4 | 5 | 6 | | VI-1 | 2900079G21Rik | | | 3139 | 3 | 4 | 5 | 6 | | VI-1 | Abi3bp | 25890 | 4-May-15 |
| 3046 | 3 | 4 | 5 | 6 | | VI-1 | 2900092D14Rik | | | 3140 | 3 | 4 | 5 | 6 | | VI-1 | Abo | 28 | 12-May-15 |
| 3047 | 3 | 4 | 5 | 6 | | VI-1 | 3010033K07Rik | | | 3141 | 3 | 4 | 5 | 6 | | VI-1 | Abracl | 58527 | 12-May-15 |
| 3048 | 3 | 4 | 5 | 6 | | VI-1 | 3300005D01Rik | | | 3142 | 3 | 4 | 5 | 6 | | VI-1 | Abtb2 | 25841 | 4-May-15 |
| 3049 | 3 | 4 | 5 | 6 | | VI-1 | 4632434I11Rik | | | 3143 | 3 | 4 | 5 | 6 | | VI-1 | Acaca | 31 | 4-May-15 |
| 3050 | 3 | 4 | 5 | 6 | | VI-1 | 4833403I15Rik | | | 3144 | 3 | 4 | 5 | 6 | | VI-1 | Acap1 | 9744 | 4-May-15 |
| 3051 | 3 | 4 | 5 | 6 | | VI-1 | 4833412C05Rik | | | 3145 | 3 | 4 | 5 | 6 | | VI-1 | Acbd7 | 414149 | 4-May-15 |
| 3052 | 3 | 4 | 5 | 6 | | VI-1 | 4930404A05Rik | | | 3146 | 3 | 4 | 5 | 6 | | VI-1 | Ace | 1636 | 24-May-15 |
| 3053 | 3 | 4 | 5 | 6 | | VI-1 | 4930404N11Rik | | | 3147 | 3 | 4 | 5 | 6 | | VI-1 | Acer2 | 340485 | 4-May-15 |
| 3054 | 3 | 4 | 5 | 6 | | VI-1 | 4930405J17Rik | | | 3148 | 3 | 4 | 5 | 6 | | VI-1 | Ackr1 | 2532 | 21-May-15 |
| 3055 | 3 | 4 | 5 | 6 | | VI-1 | 4930412O13Rik | | | 3149 | 3 | 4 | 5 | 6 | | VI-1 | Ackr2 | 1238 | 4-May-15 |
| 3056 | 3 | 4 | 5 | 6 | | VI-1 | 4930413F20Rik | | | 3150 | 3 | 4 | 5 | 6 | | VI-1 | Ackr4 | 51554 | 4-May-15 |
| 3057 | 3 | 4 | 5 | 6 | | VI-1 | 4930426D05Rik | | | 3151 | 3 | 4 | 5 | 6 | | VI-1 | Acly | 47 | 4-May-15 |
| 3058 | 3 | 4 | 5 | 6 | | VI-1 | 4930427A07Rik | | | 3152 | 3 | 4 | 5 | 6 | | VI-1 | Acmsd | 130013 | 12-May-15 |
| 3059 | 3 | 4 | 5 | 6 | | VI-1 | 4930440I19Rik | | | 3153 | 3 | 4 | 5 | 6 | | VI-1 | Acot1 | 641371 | 4-May-15 |
| 3060 | 3 | 4 | 5 | 6 | | VI-1 | 4930447C04Rik | | | 3154 | 3 | 4 | 5 | 6 | | VI-1 | Acot2 | 10965 | 4-May-15 |
| 3061 | 3 | 4 | 5 | 6 | | VI-1 | 4930449E18Rik | | | 3155 | 3 | 4 | 5 | 6 | | VI-1 | Acot5 | | |
| 3062 | 3 | 4 | 5 | 6 | | VI-1 | 4930451G09Rik | | | 3156 | 3 | 4 | 5 | 6 | | VI-1 | Acp1 | 52 | 12-May-15 |
| 3063 | 3 | 4 | 5 | 6 | | VI-1 | 4930481A15Rik | | | 3157 | 3 | 4 | 5 | 6 | | VI-1 | Acp5 | 54 | 3-May-15 |
| 3064 | 3 | 4 | 5 | 6 | | VI-1 | 4930483K19Rik | | | 3158 | 3 | 4 | 5 | 6 | | VI-1 | Acpp | 55 | 4-May-15 |
| 3065 | 3 | 4 | 5 | 6 | | VI-1 | 4930486L24Rik | | | 3159 | 3 | 4 | 5 | 6 | | VI-1 | Acsl1 | 2180 | 4-May-15 |
| 3066 | 3 | 4 | 5 | 6 | | VI-1 | 4930506M07Rik | | | 3160 | 3 | 4 | 5 | 6 | | VI-1 | Acsl4 | 2182 | 4-May-15 |
| 3067 | 3 | 4 | 5 | 6 | | VI-1 | 4930532M18Rik | | | 3161 | 3 | 4 | 5 | 6 | | VI-1 | Acsl6 | 23305 | 4-May-15 |
| 3068 | 3 | 4 | 5 | 6 | | VI-1 | 4930572O13Rik | | | 3162 | 3 | 4 | 5 | 6 | | VI-1 | Acsm3 | 6296 | 12-May-15 |
| 3069 | 3 | 4 | 5 | 6 | | VI-1 | 4930579G24Rik | | | 3163 | 3 | 4 | 5 | 6 | | VI-1 | Acss2 | 55902 | 4-May-15 |
| 3070 | 3 | 4 | 5 | 6 | | VI-1 | 4930579K19Rik | | | 3164 | 3 | 4 | 5 | 6 | | VI-1 | Acss3 | 79611 | 4-May-15 |
| 3071 | 3 | 4 | 5 | 6 | | VI-1 | 4931406P16Rik | | | 3165 | 3 | 4 | 5 | 6 | | VI-1 | Actb | 60 | 7-Jun-15 |
| 3072 | 3 | 4 | 5 | 6 | | VI-1 | 4931408C20Rik | | | 3166 | 3 | 4 | 5 | 6 | | VI-1 | Actg1 | 71 | 23-May-15 |
| 3073 | 3 | 4 | 5 | 6 | | VI-1 | 4931431C16Rik | | | 3167 | 3 | 4 | 5 | 6 | | VI-1 | Actg2 | 72 | 12-May-15 |
| 3074 | 3 | 4 | 5 | 6 | | VI-1 | 4932438H23Rik | | | 3168 | 3 | 4 | 5 | 6 | | VI-1 | Actn1 | 87 | 14-May-15 |
| 3075 | 3 | 4 | 5 | 6 | | VI-1 | 4933404O12Rik | | | 3169 | 3 | 4 | 5 | 6 | | VI-1 | Actn3 | 89 | 29-May-15 |
| 3076 | 3 | 4 | 5 | 6 | | VI-1 | 4933409K07Rik | | | 3170 | 3 | 4 | 5 | 6 | | VI-1 | Acvr1c | 130399 | 4-May-15 |
| 3077 | 3 | 4 | 5 | 6 | | VI-1 | 4933412E12Rik | | | 3171 | 3 | 4 | 5 | 6 | | VI-1 | Acvrl1 | 94 | 23-May-15 |
| 3078 | 3 | 4 | 5 | 6 | | VI-1 | 4933427J22Rik | | | 3172 | 3 | 4 | 5 | 6 | | VI-1 | Acyp2 | 98 | 5-May-15 |
| 3079 | 3 | 4 | 5 | 6 | | VI-1 | 4933433H22Rik | | | 3173 | 3 | 4 | 5 | 6 | | VI-1 | Ada | 100 | 22-May-15 |
| 3080 | 3 | 4 | 5 | 6 | | VI-1 | 4933439C10Rik | | | 3174 | 3 | 4 | 5 | 6 | | VI-1 | Adam11 | 4185 | 4-May-15 |
| 3081 | 3 | 4 | 5 | 6 | | VI-1 | 5031414D18Rik | | | 3175 | 3 | 4 | 5 | 6 | | VI-1 | Adam12 | 8038 | 4-May-15 |
| 3082 | 3 | 4 | 5 | 6 | | VI-1 | 5033406O09Rik | | | 3176 | 3 | 4 | 5 | 6 | | VI-1 | Adam19 | 8728 | 4-May-15 |
| 3083 | 3 | 4 | 5 | 6 | | VI-1 | 5430416N02Rik | | | 3177 | 3 | 4 | 5 | 6 | | VI-1 | Adam28 | 10863 | 4-May-15 |
| 3084 | 3 | 4 | 5 | 6 | | VI-1 | 5430427O19Rik | | | 3178 | 3 | 4 | 5 | 6 | | VI-1 | Adam33 | 80332 | 4-May-15 |
| 3085 | 3 | 4 | 5 | 6 | | VI-1 | 5430435G22Rik | | | 3179 | 3 | 4 | 5 | 6 | | VI-1 | Adam6b | | |
| 3086 | 3 | 4 | 5 | 6 | | VI-1 | 5730408K05Rik | | | 3180 | 3 | 4 | 5 | 6 | | VI-1 | Adamdec1 | 27299 | 24-May-15 |
| 3087 | 3 | 4 | 5 | 6 | | VI-1 | 5730416F02Rik | | | 3181 | 3 | 4 | 5 | 6 | | VI-1 | Adamts1 | 9510 | 4-May-15 |
| 3088 | 3 | 4 | 5 | 6 | | VI-1 | 5730508B09Rik | | | 3182 | 3 | 4 | 5 | 6 | | VI-1 | Adamts12 | 81792 | 4-May-15 |
| 3089 | 3 | 4 | 5 | 6 | | VI-1 | 5730559C18Rik | | | 3183 | 3 | 4 | 5 | 6 | | VI-1 | Adamts15 | 170689 | 17-May-15 |
| 3090 | 3 | 4 | 5 | 6 | | VI-1 | 5830403L16Rik | | | 3184 | 3 | 4 | 5 | 6 | | VI-1 | Adamts2 | 9509 | 7-Jun-15 |
| 3091 | 3 | 4 | 5 | 6 | | VI-1 | 5830415F09Rik | | | 3185 | 3 | 4 | 5 | 6 | | VI-1 | Adamts5 | 11096 | 4-May-15 |
| 3092 | 3 | 4 | 5 | 6 | | VI-1 | 5830444B04Rik | | | 3186 | 3 | 4 | 5 | 6 | | VI-1 | Adamts6 | 13174 | 4-May-15 |
| 3093 | 3 | 4 | 5 | 6 | | VI-1 | 6030468B19Rik | | | 3187 | 3 | 4 | 5 | 6 | | VI-1 | Adamts9 | 56999 | 4-May-15 |
| 3094 | 3 | 4 | 5 | 6 | | VI-1 | 6330418K02Rik | | | 3188 | 3 | 4 | 5 | 6 | | VI-1 | Adamtsl3 | 57188 | 4-May-15 |
| 3095 | 3 | 4 | 5 | 6 | | VI-1 | 6430706O22Rik | | | 3189 | 3 | 4 | 5 | 6 | | VI-1 | Adap1 | 11033 | 4-May-15 |
| 3096 | 3 | 4 | 5 | 6 | | VI-1 | 6720416L17Rik | | | 3190 | 3 | 4 | 5 | 6 | | VI-1 | Adap2 | 55803 | 4-May-15 |
| 3097 | 3 | 4 | 5 | 6 | | VI-1 | 6720468P15Rik | | | 3191 | 3 | 4 | 5 | 6 | | VI-1 | Adc | | |
| 3098 | 3 | 4 | 5 | 6 | | VI-1 | 9230110F15Rik | | | 3192 | 3 | 4 | 5 | 6 | | VI-1 | Adck3 | 56997 | 4-May-15 |
| 3099 | 3 | 4 | 5 | 6 | | VI-1 | 9230114K14Rik | | | 3193 | 3 | 4 | 5 | 6 | | VI-1 | Adcy3 | 109 | 7-Jun-15 |
| 3100 | 3 | 4 | 5 | 6 | | VI-1 | 9330162O12Rik | | | 3194 | 3 | 4 | 5 | 6 | | VI-1 | Adcy5 | 111 | 23-May-15 |
| | | | | | | | | | | 3195 | 3 | 4 | 5 | 6 | | VI-1 | Adcy7 | 113 | 4-May-15 |
| | | | | | | | | | | 3196 | 3 | 4 | 5 | 6 | | VI-1 | Adcyap1r1 | 117 | 17-May-15 |

Fig. 30 - 18

| # | | | | | | | Name | ID | Date | # | | | | | | | Name | ID | Date |
|---|---|---|---|---|---|---|---|---|---|---|---|---|---|---|---|---|---|---|---|
| 3197 | 3 | 4 | 5 | 6 | | VI-1 | Add2 | 119 | 12-May-15 | 3293 | 3 | 4 | 5 | 6 | | VI-1 | Arhgap19 | 84986 | 4-May-15 |
| 3198 | 3 | 4 | 5 | 6 | | VI-1 | Adh1 | 124 | 4-May-15 | 3294 | 3 | 4 | 5 | 6 | | VI-1 | Arhgap22 | 58504 | 14-May-15 |
| 3199 | 3 | 4 | 5 | 6 | | VI-1 | Adh6-ps1 | | | 3295 | 3 | 4 | 5 | 6 | | VI-1 | Arhgap25 | 9938 | 4-May-15 |
| 3200 | 3 | 4 | 5 | 6 | | VI-1 | Adhfe1 | 137872 | 4-May-15 | 3296 | 3 | 4 | 5 | 6 | | VI-1 | Arhgap27os3 | | |
| 3201 | 3 | 4 | 5 | 6 | | VI-1 | Adig | 149685 | 4-May-15 | 3297 | 3 | 4 | 5 | 6 | | VI-1 | Arhgap30 | 257106 | 12-May-15 |
| 3202 | 3 | 4 | 5 | 6 | | VI-1 | Adm | 133 | 17-May-15 | 3298 | 3 | 4 | 5 | 6 | | VI-1 | Arhgap4 | 393 | 4-May-15 |
| 3203 | 3 | 4 | 5 | 6 | | VI-1 | Adora1 | 134 | 21-May-15 | 3299 | 3 | 4 | 5 | 6 | | VI-1 | Arhgap8 | 23779 | 4-May-15 |
| 3204 | 3 | 4 | 5 | 6 | | VI-1 | Adora2b | 136 | 24-May-15 | 3300 | 3 | 4 | 5 | 6 | | VI-1 | Arhgef19 | 128272 | 4-May-15 |
| 3205 | 3 | 4 | 5 | 6 | | VI-1 | Adprhl1 | 113622 | 4-May-15 | 3301 | 3 | 4 | 5 | 6 | | VI-1 | Arhgef2 | 9181 | 4-May-15 |
| 3206 | 3 | 4 | 5 | 6 | | VI-1 | Aebp1 | 165 | 4-May-15 | 3302 | 3 | 4 | 5 | 6 | | VI-1 | Arhgef26 | 26084 | 4-May-15 |
| 3207 | 3 | 4 | 5 | 6 | | VI-1 | Afap1l2 | 84632 | 4-May-15 | 3303 | 3 | 4 | 5 | 6 | | VI-1 | Arhgef37 | 389337 | 4-May-15 |
| 3208 | 3 | 4 | 5 | 6 | | VI-1 | Aff3 | 3899 | 4-May-15 | 3304 | 3 | 4 | 5 | 6 | | VI-1 | Arhgef39 | 84904 | 4-May-15 |
| 3209 | 3 | 4 | 5 | 6 | | VI-1 | Agap2 | 116986 | 4-May-15 | 3305 | 3 | 4 | 5 | 6 | | VI-1 | Arid5a | 10865 | 4-May-15 |
| 3210 | 3 | 4 | 5 | 6 | | VI-1 | Agmat | 79814 | 4-May-15 | 3306 | 3 | 4 | 5 | 6 | | VI-1 | Arl11 | 115761 | 4-May-15 |
| 3211 | 3 | 4 | 5 | 6 | | VI-1 | Agpat9 | 84803 | 4-May-15 | 3307 | 3 | 4 | 5 | 6 | | VI-1 | Arl2bp | 23568 | 4-May-15 |
| 3212 | 3 | 4 | 5 | 6 | | VI-1 | Agrn | 375790 | 12-May-15 | 3308 | 3 | 4 | 5 | 6 | | VI-1 | Arl4c | 10123 | 4-May-15 |
| 3213 | 3 | 4 | 5 | 6 | | VI-1 | Agt | 183 | 7-Jun-15 | 3309 | 3 | 4 | 5 | 6 | | VI-1 | Arl4d | 379 | 4-May-15 |
| 3214 | 3 | 4 | 5 | 6 | | VI-1 | AI427809 | | | 3310 | 3 | 4 | 5 | 6 | | VI-1 | Arl5b | 221079 | 4-May-15 |
| 3215 | 3 | 4 | 5 | 6 | | VI-1 | AI467606 | | | 3311 | 3 | 4 | 5 | 6 | | VI-1 | Arl5c | 390790 | 4-May-15 |
| 3216 | 3 | 4 | 5 | 6 | | VI-1 | AI504432 | | | 3312 | 3 | 4 | 5 | 6 | | VI-1 | Armcx4 | 100131755 | 12-May-15 |
| 3217 | 3 | 4 | 5 | 6 | | VI-1 | AI506816 | | | 3313 | 3 | 4 | 5 | 6 | | VI-1 | Armcx6 | 54470 | 4-May-15 |
| 3218 | 3 | 4 | 5 | 6 | | VI-1 | AI607873 | | | 3314 | 3 | 4 | 5 | 6 | | VI-1 | Arnt2 | 9915 | 12-May-15 |
| 3219 | 3 | 4 | 5 | 6 | | VI-1 | AI662270 | | | 3315 | 3 | 4 | 5 | 6 | | VI-1 | Arntl2 | 56938 | 4-May-15 |
| 3220 | 3 | 4 | 5 | 6 | | VI-1 | Aicda | 57379 | 4-May-15 | 3316 | 3 | 4 | 5 | 6 | | VI-1 | Arpc5l | 81873 | 12-May-15 |
| 3221 | 3 | 4 | 5 | 6 | | VI-1 | Aif1 | 199 | 4-May-15 | 3317 | 3 | 4 | 5 | 6 | | VI-1 | Arrb2 | 409 | 17-May-15 |
| 3222 | 3 | 4 | 5 | 6 | | VI-1 | Aifm2 | 84883 | 4-May-15 | 3318 | 3 | 4 | 5 | 6 | | VI-1 | Arrdc1 | 92714 | 4-May-15 |
| 3223 | 3 | 4 | 5 | 6 | | VI-1 | Ak1 | 203 | 12-May-15 | 3319 | 3 | 4 | 5 | 6 | | VI-1 | Arsi | 340075 | 23-May-15 |
| 3224 | 3 | 4 | 5 | 6 | | VI-1 | Ak4 | 205 | 12-May-15 | 3320 | 3 | 4 | 5 | 6 | | VI-1 | Arsj | 79642 | 4-May-15 |
| 3225 | 3 | 4 | 5 | 6 | | VI-1 | Akap12 | 9590 | 4-May-15 | 3321 | 3 | 4 | 5 | 6 | | VI-1 | Art1 | 417 | 7-Jun-15 |
| 3226 | 3 | 4 | 5 | 6 | | VI-1 | Akap2 | 11217 | 7-Jun-15 | 3322 | 3 | 4 | 5 | 6 | | VI-1 | Art2b | | |
| 3227 | 3 | 4 | 5 | 6 | | VI-1 | Akap7 | 9465 | 4-May-15 | 3323 | 3 | 4 | 5 | 6 | | VI-1 | Art4 | 420 | 7-Jun-15 |
| 3228 | 3 | 4 | 5 | 6 | | VI-1 | Akna | 80709 | 4-May-15 | 3324 | 3 | 4 | 5 | 6 | | VI-1 | Arvcf | 421 | 12-May-15 |
| 3229 | 3 | 4 | 5 | 6 | | VI-1 | Akr1b3 | | | 3325 | 3 | 4 | 5 | 6 | | VI-1 | Arxes1 | | |
| 3230 | 3 | 4 | 5 | 6 | | VI-1 | Akr1c14 | | | 3326 | 3 | 4 | 5 | 6 | | VI-1 | Arxes2 | | |
| 3231 | 3 | 4 | 5 | 6 | | VI-1 | Akr7a5 | | | 3327 | 3 | 4 | 5 | 6 | | VI-1 | As3mt | 57412 | 4-May-15 |
| 3232 | 3 | 4 | 5 | 6 | | VI-1 | Alad | 210 | 4-May-15 | 3328 | 3 | 4 | 5 | 6 | | VI-1 | Asap2 | 8853 | 12-May-15 |
| 3233 | 3 | 4 | 5 | 6 | | VI-1 | Alas1 | 211 | 12-May-15 | 3329 | 3 | 4 | 5 | 6 | | VI-1 | Asb1 | 51665 | 4-May-15 |
| 3234 | 3 | 4 | 5 | 6 | | VI-1 | Alcam | 214 | 4-May-15 | 3330 | 3 | 4 | 5 | 6 | | VI-1 | Asb17os | | |
| 3235 | 3 | 4 | 5 | 6 | | VI-1 | Aldh1a1 | 216 | 23-May-15 | 3331 | 3 | 4 | 5 | 6 | | VI-1 | Ascl2 | 430 | 4-May-15 |
| 3236 | 3 | 4 | 5 | 6 | | VI-1 | Aldh1a2 | 8854 | 23-May-15 | 3332 | 3 | 4 | 5 | 6 | | VI-1 | Asns | 440 | 12-May-15 |
| 3237 | 3 | 4 | 5 | 6 | | VI-1 | Aldh1a7 | | | 3333 | 3 | 4 | 5 | 6 | | VI-1 | Aspa | 443 | 23-May-15 |
| 3238 | 3 | 4 | 5 | 6 | | VI-1 | Aldh3b1 | 221 | 23-May-15 | 3334 | 3 | 4 | 5 | 6 | | VI-1 | Aspg | 374569 | 4-May-15 |
| 3239 | 3 | 4 | 5 | 6 | | VI-1 | Alms1 | 7840 | 22-May-15 | 3335 | 3 | 4 | 5 | 6 | | VI-1 | Aspn | 54829 | 12-May-15 |
| 3240 | 3 | 4 | 5 | 6 | | VI-1 | Alox12b | 242 | 23-May-15 | 3336 | 3 | 4 | 5 | 6 | | VI-1 | Asprv1 | 151516 | 4-May-15 |
| 3241 | 3 | 4 | 5 | 6 | | VI-1 | Alox5ap | 241 | 4-May-15 | 3337 | 3 | 4 | 5 | 6 | | VI-1 | Ass1 | 445 | 23-May-15 |
| 3242 | 3 | 4 | 5 | 6 | | VI-1 | Als2cr12 | 130540 | 12-May-15 | 3338 | 3 | 4 | 5 | 6 | | VI-1 | Atad2 | 29028 | 4-May-15 |
| 3243 | 3 | 4 | 5 | 6 | | VI-1 | Amd2 | 263 | 4-May-15 | 3339 | 3 | 4 | 5 | 6 | | VI-1 | Atad5 | 79915 | 4-May-15 |
| 3244 | 3 | 4 | 5 | 6 | | VI-1 | Amdhd1 | 144193 | 4-May-15 | 3340 | 3 | 4 | 5 | 6 | | VI-1 | Atcay | 85300 | 4-May-15 |
| 3245 | 3 | 4 | 5 | 6 | | VI-1 | Amica1 | 120425 | 4-May-15 | 3341 | 3 | 4 | 5 | 6 | | VI-1 | Atcayos | | |
| 3246 | 3 | 4 | 5 | 6 | | VI-1 | Ammecr1 | 9949 | 12-May-15 | 3342 | 3 | 4 | 5 | 6 | | VI-1 | Atf4 | 468 | 4-May-15 |
| 3247 | 3 | 4 | 5 | 6 | | VI-1 | Amt | 275 | 23-May-15 | 3343 | 3 | 4 | 5 | 6 | | VI-1 | Atf5 | 22809 | 21-May-15 |
| 3248 | 3 | 4 | 5 | 6 | | VI-1 | Ang | 283 | 4-May-15 | 3344 | 3 | 4 | 5 | 6 | | VI-1 | Atf7 | 11016 | 4-May-15 |
| 3249 | 3 | 4 | 5 | 6 | | VI-1 | Angpt2 | 285 | 24-May-15 | 3345 | 3 | 4 | 5 | 6 | | VI-1 | Atg4a | 115201 | 24-May-15 |
| 3250 | 3 | 4 | 5 | 6 | | VI-1 | Angpt4 | 51378 | 4-May-15 | 3346 | 3 | 4 | 5 | 6 | | VI-1 | Atp10a | 57194 | 21-May-15 |
| 3251 | 3 | 4 | 5 | 6 | | VI-1 | Ank1 | 286 | 12-May-15 | 3347 | 3 | 4 | 5 | 6 | | VI-1 | Atp10b | 23120 | 4-May-15 |
| 3252 | 3 | 4 | 5 | 6 | | VI-1 | Ankib1 | 54467 | 4-May-15 | 3348 | 3 | 4 | 5 | 6 | | VI-1 | Atp1a2 | 477 | 23-May-15 |
| 3253 | 3 | 4 | 5 | 6 | | VI-1 | Ankle1 | 126549 | 4-May-15 | 3349 | 3 | 4 | 5 | 6 | | VI-1 | Atp1a3 | 478 | 23-May-15 |
| 3254 | 3 | 4 | 5 | 6 | | VI-1 | Ankrd28 | 23243 | 4-May-15 | 3350 | 3 | 4 | 5 | 6 | | VI-1 | Atp1b2 | 482 | 4-May-15 |
| 3255 | 3 | 4 | 5 | 6 | | VI-1 | Ankrd37 | 353322 | 21-May-15 | 3351 | 3 | 4 | 5 | 6 | | VI-1 | Atp1b3 | 483 | 4-May-15 |
| 3256 | 3 | 4 | 5 | 6 | | VI-1 | Ankrd6 | 22881 | 4-May-15 | 3352 | 3 | 4 | 5 | 6 | | VI-1 | Atp2a3 | 489 | 12-May-15 |
| 3257 | 3 | 4 | 5 | 6 | | VI-1 | Ankrd9 | 122416 | 4-May-15 | 3353 | 3 | 4 | 5 | 6 | | VI-1 | Atp2b4 | 493 | 17-May-15 |
| 3258 | 3 | 4 | 5 | 6 | | VI-1 | Anln | 54443 | 4-May-15 | 3354 | 3 | 4 | 5 | 6 | | VI-1 | Atp4a | 495 | 4-May-15 |
| 3259 | 3 | 4 | 5 | 6 | | VI-1 | Anpep | 290 | 12-May-15 | 3355 | 3 | 4 | 5 | 6 | | VI-1 | Atp5g1 | 516 | 4-May-15 |
| 3260 | 3 | 4 | 5 | 6 | | VI-1 | Antxr1 | 84168 | 4-May-15 | 3356 | 3 | 4 | 5 | 6 | | VI-1 | Atp5k | 521 | 4-May-15 |
| 3261 | 3 | 4 | 5 | 6 | | VI-1 | Anxa1 | 301 | 24-May-15 | 3357 | 3 | 4 | 5 | 6 | | VI-1 | Atp6v1c2 | 245973 | 4-May-15 |
| 3262 | 3 | 4 | 5 | 6 | | VI-1 | Anxa2 | 302 | 17-May-15 | 3358 | 3 | 4 | 5 | 6 | | VI-1 | Atp6v1h | 51606 | 4-May-15 |
| 3263 | 3 | 4 | 5 | 6 | | VI-1 | Anxa3 | 306 | 12-May-15 | 3359 | 3 | 4 | 5 | 6 | | VI-1 | Atp7b | 540 | 4-May-15 |
| 3264 | 3 | 4 | 5 | 6 | | VI-1 | Anxa8 | 653145 | 7-Jun-15 | 3360 | 3 | 4 | 5 | 6 | | VI-1 | Atp8b4 | 79895 | 4-May-15 |
| 3265 | 3 | 4 | 5 | 6 | | VI-1 | Aoah | 313 | 12-May-15 | 3361 | 3 | 4 | 5 | 6 | | VI-1 | Atpif1 | 93974 | 24-May-15 |
| 3266 | 3 | 4 | 5 | 6 | | VI-1 | Aoc3 | 8639 | 4-May-15 | 3362 | 3 | 4 | 5 | 6 | | VI-1 | Atxn1 | 6310 | 23-May-15 |
| 3267 | 3 | 4 | 5 | 6 | | VI-1 | Aox1 | 316 | 12-May-15 | 3363 | 3 | 4 | 5 | 6 | | VI-1 | AU021092 | | |
| 3268 | 3 | 4 | 5 | 6 | | VI-1 | Ap1m2 | 10053 | 12-May-15 | 3364 | 3 | 4 | 5 | 6 | | VI-1 | Aurka | 6790 | 24-May-15 |
| 3269 | 3 | 4 | 5 | 6 | | VI-1 | Ap1s3 | 130340 | 4-May-15 | 3365 | 3 | 4 | 5 | 6 | | VI-1 | Avpr1a | 552 | 17-May-15 |
| 3270 | 3 | 4 | 5 | 6 | | VI-1 | Apbb1ip | 54518 | 12-May-15 | 3366 | 3 | 4 | 5 | 6 | | VI-1 | AW112010 | | |
| 3271 | 3 | 4 | 5 | 6 | | VI-1 | Apcdd1 | 147495 | 4-May-15 | 3367 | 3 | 4 | 5 | 6 | | VI-1 | B230208H11Rik | | |
| 3272 | 3 | 4 | 5 | 6 | | VI-1 | Apcs | 325 | 4-May-15 | 3368 | 3 | 4 | 5 | 6 | | VI-1 | B2m | 567 | 17-May-15 |
| 3273 | 3 | 4 | 5 | 6 | | VI-1 | Apex1 | 328 | 12-May-15 | 3369 | 3 | 4 | 5 | 6 | | VI-1 | B3galnt1 | 8706 | 14-May-15 |
| 3274 | 3 | 4 | 5 | 6 | | VI-1 | Apobr | 55911 | 4-May-15 | 3370 | 3 | 4 | 5 | 6 | | VI-1 | B3galt2 | 8707 | 23-May-15 |
| 3275 | 3 | 4 | 5 | 6 | | VI-1 | Apoc1 | 341 | 21-May-15 | 3371 | 3 | 4 | 5 | 6 | | VI-1 | B3gnt1 | 10678 | 4-May-15 |
| 3276 | 3 | 4 | 5 | 6 | | VI-1 | Apoc2 | 344 | 4-May-15 | 3372 | 3 | 4 | 5 | 6 | | VI-1 | B3gnt3 | 10331 | 4-May-15 |
| 3277 | 3 | 4 | 5 | 6 | | VI-1 | Apoc4 | 346 | 12-May-15 | 3373 | 3 | 4 | 5 | 6 | | VI-1 | B3gnt5 | 84002 | 4-May-15 |
| 3278 | 3 | 4 | 5 | 6 | | VI-1 | Apoe | 348 | 24-May-15 | 3374 | 3 | 4 | 5 | 6 | | VI-1 | B3gnt8 | 374907 | 4-May-15 |
| 3279 | 3 | 4 | 5 | 6 | | VI-1 | Apol10a | | | 3375 | 3 | 4 | 5 | 6 | | VI-1 | B430010I23Rik | | |
| 3280 | 3 | 4 | 5 | 6 | | VI-1 | Apol6 | 80830 | | 3376 | 3 | 4 | 5 | 6 | | VI-1 | B430306N03Rik | | |
| 3281 | 3 | 4 | 5 | 6 | | VI-1 | Apol9a | | | 3377 | 3 | 4 | 5 | 6 | | VI-1 | B4galnt1 | 2583 | 4-May-15 |
| 3282 | 3 | 4 | 5 | 6 | | VI-1 | Apoo-ps | | | 3378 | 3 | 4 | 5 | 6 | | VI-1 | B4galt4 | 8702 | 4-May-15 |
| 3283 | 3 | 4 | 5 | 6 | | VI-1 | Aqp1 | 358 | 17-May-15 | 3379 | 3 | 4 | 5 | 6 | | VI-1 | B4galt5 | 9334 | 4-May-15 |
| 3284 | 3 | 4 | 5 | 6 | | VI-1 | Aqp2 | 359 | 23-May-15 | 3380 | 3 | 4 | 5 | 6 | | VI-1 | B9d2 | 80776 | 4-May-15 |
| 3285 | 3 | 4 | 5 | 6 | | VI-1 | Aqp7 | 364 | 4-May-15 | 3381 | 3 | 4 | 5 | 6 | | VI-1 | Bach2 | 60468 | 12-May-15 |
| 3286 | 3 | 4 | 5 | 6 | | VI-1 | Aqp8 | 343 | 17-May-15 | 3382 | 3 | 4 | 5 | 6 | | VI-1 | Bag2 | 9532 | 4-May-15 |
| 3287 | 3 | 4 | 5 | 6 | | VI-1 | Aqp9 | 366 | 7-Jun-15 | 3383 | 3 | 4 | 5 | 6 | | VI-1 | Baiap3 | 8938 | 4-May-15 |
| 3288 | 3 | 4 | 5 | 6 | | VI-1 | Arc | 23237 | 7-Jun-15 | 3384 | 3 | 4 | 5 | 6 | | VI-1 | Bank1 | 55024 | 4-May-15 |
| 3289 | 3 | 4 | 5 | 6 | | VI-1 | Areg | 374 | 4-May-15 | 3385 | 3 | 4 | 5 | 6 | | VI-1 | Banp | 54971 | 12-May-15 |
| 3290 | 3 | 4 | 5 | 6 | | VI-1 | Arg2 | 384 | 4-May-15 | 3386 | 3 | 4 | 5 | 6 | | VI-1 | Bard1 | 580 | 24-May-15 |
| 3291 | 3 | 4 | 5 | 6 | | VI-1 | Arhgap11a | 9824 | 4-May-15 | 3387 | 3 | 4 | 5 | 6 | | VI-1 | Batf2 | 116071 | 12-May-15 |
| 3292 | 3 | 4 | 5 | 6 | | VI-1 | Arhgap15 | 55843 | 4-May-15 | | | | | | | | | | |

Fig. 30 - 19

| # | | | | | | | Gene | ID | Date |
|---|---|---|---|---|---|---|---|---|---|
| 3388 | 3 | 4 | 5 | 6 | | VI-1 | Bbc3 | 27113 | 24-May-15 |
| 3389 | 3 | 4 | 5 | 6 | | VI-1 | Bhx | 56987 | 4-May-15 |
| 3390 | 3 | 4 | 5 | 6 | | VI-1 | BC021614 | | |
| 3391 | 3 | 4 | 5 | 6 | | VI-1 | BC021767 | | |
| 3392 | 3 | 4 | 5 | 6 | | VI-1 | BC024139 | | |
| 3393 | 3 | 4 | 5 | 6 | | VI-1 | BC028528 | | |
| 3394 | 3 | 4 | 5 | 6 | | VI-1 | BC030867 | | |
| 3395 | 3 | 4 | 5 | 6 | | VI-1 | BC033916 | | |
| 3396 | 3 | 4 | 5 | 6 | | VI-1 | BC037034 | | |
| 3397 | 3 | 4 | 5 | 6 | | VI-1 | BC048546 | | |
| 3398 | 3 | 4 | 5 | 6 | | VI-1 | BC051537 | | |
| 3399 | 3 | 4 | 5 | 6 | | VI-1 | BC055324 | | |
| 3400 | 3 | 4 | 5 | 6 | | VI-1 | BC061237 | | |
| 3401 | 3 | 4 | 5 | 6 | | VI-1 | BC064078 | | |
| 3402 | 3 | 4 | 5 | 6 | | VI-1 | BC100530 | | |
| 3403 | 3 | 4 | 5 | 6 | | VI-1 | Bcar3 | 8412 | 12-May-15 |
| 3404 | 3 | 4 | 5 | 6 | | VI-1 | Bcat1 | 586 | 4-May-15 |
| 3405 | 3 | 4 | 5 | 6 | | VI-1 | Bcl2a1a | | |
| 3406 | 3 | 4 | 5 | 6 | | VI-1 | Bcl2a1b | | |
| 3407 | 3 | 4 | 5 | 6 | | VI-1 | Bcl2a1d | | |
| 3408 | 3 | 4 | 5 | 6 | | VI-1 | Bcl2l1 | 598 | 24-May-15 |
| 3409 | 3 | 4 | 5 | 6 | | VI-1 | Bcl2l10 | 10017 | 12-May-15 |
| 3410 | 3 | 4 | 5 | 6 | | VI-1 | Bcl3 | 602 | 4-May-15 |
| 3411 | 3 | 4 | 5 | 6 | | VI-1 | Bcl6 | 604 | 17-May-15 |
| 3412 | 3 | 4 | 5 | 6 | | VI-1 | Bcl7a | 605 | 4-May-15 |
| 3413 | 3 | 4 | 5 | 6 | | VI-1 | Bcr | 613 | 24-May-15 |
| 3414 | 3 | 4 | 5 | 6 | | VI-1 | Bdh1 | 622 | 4-May-15 |
| 3415 | 3 | 4 | 5 | 6 | | VI-1 | Bend4 | 389206 | 4-May-15 |
| 3416 | 3 | 4 | 5 | 6 | | VI-1 | Bex2 | 84707 | 7-Jun-15 |
| 3417 | 3 | 4 | 5 | 6 | | VI-1 | Bex4 | 56271 | 4-May-15 |
| 3418 | 3 | 4 | 5 | 6 | | VI-1 | Bfsp1 | 631 | 4-May-15 |
| 3419 | 3 | 4 | 5 | 6 | | VI-1 | Bgn | 633 | 17-May-15 |
| 3420 | 3 | 4 | 5 | 6 | | VI-1 | Bid | 637 | 17-May-15 |
| 3421 | 3 | 4 | 5 | 6 | | VI-1 | Bin2 | 51411 | 12-May-15 |
| 3422 | 3 | 4 | 5 | 6 | | VI-1 | Blm | 641 | 23-May-15 |
| 3423 | 3 | 4 | 5 | 6 | | VI-1 | Blvrb | 645 | 4-May-15 |
| 3424 | 3 | 4 | 5 | 6 | | VI-1 | Bmf | 90427 | 4-May-15 |
| 3425 | 3 | 4 | 5 | 6 | | VI-1 | Bmp2 | 650 | 24-May-15 |
| 3426 | 3 | 4 | 5 | 6 | | VI-1 | Bmp3 | 651 | 12-May-15 |
| 3427 | 3 | 4 | 5 | 6 | | VI-1 | Bmyc | | |
| 3428 | 3 | 4 | 5 | 6 | | VI-1 | Boc | 91653 | 12-May-15 |
| 3429 | 3 | 4 | 5 | 6 | | VI-1 | Bora | 79866 | 4-May-15 |
| 3430 | 3 | 4 | 5 | 6 | | VI-1 | Bpgm | 669 | 12-May-15 |
| 3431 | 3 | 4 | 5 | 6 | | VI-1 | Brca1 | 672 | 25-May-15 |
| 3432 | 3 | 4 | 5 | 6 | | VI-1 | Bri3bp | 140707 | 4-May-15 |
| 3433 | 3 | 4 | 5 | 6 | | VI-1 | Brpf3 | 27154 | 4-May-15 |
| 3434 | 3 | 4 | 5 | 6 | | VI-1 | Bsg | 682 | 17-May-15 |
| 3435 | 3 | 4 | 5 | 6 | | VI-1 | Bsn | 8927 | 4-May-15 |
| 3436 | 3 | 4 | 5 | 6 | | VI-1 | Bspry | 54836 | 4-May-15 |
| 3437 | 3 | 4 | 5 | 6 | | VI-1 | Bst1 | 683 | 7-Jun-15 |
| 3438 | 3 | 4 | 5 | 6 | | VI-1 | Btc | 685 | 4-May-15 |
| 3439 | 3 | 4 | 5 | 6 | | VI-1 | Btg1 | 694 | 7-Jun-15 |
| 3440 | 3 | 4 | 5 | 6 | | VI-1 | Btg2 | 7832 | 26-May-15 |
| 3441 | 3 | 4 | 5 | 6 | | VI-1 | Btg3 | 10950 | 12-May-15 |
| 3442 | 3 | 4 | 5 | 6 | | VI-1 | Btk | 695 | 22-May-15 |
| 3443 | 3 | 4 | 5 | 6 | | VI-1 | Btla | 151888 | 4-May-15 |
| 3444 | 3 | 4 | 5 | 6 | | VI-1 | Btn1a1 | 696 | 20-May-15 |
| 3445 | 3 | 4 | 5 | 6 | | VI-1 | Btnl10 | 100129094 | 4-May-15 |
| 3446 | 3 | 4 | 5 | 6 | | VI-1 | Btnl2 | 56244 | 12-May-15 |
| 3447 | 3 | 4 | 5 | 6 | | VI-1 | Btnl9 | 153579 | 12-May-15 |
| 3448 | 3 | 4 | 5 | 6 | | VI-1 | Bub1 | 699 | 12-May-15 |
| 3449 | 3 | 4 | 5 | 6 | | VI-1 | C130083M11Rik | | |
| 3450 | 3 | 4 | 5 | 6 | | VI-1 | C1galt1 | 56913 | 14-May-15 |
| 3451 | 3 | 4 | 5 | 6 | | VI-1 | C1qb | 713 | 4-May-15 |
| 3452 | 3 | 4 | 5 | 6 | | VI-1 | C1qtnf2 | 114898 | 12-May-15 |
| 3453 | 3 | 4 | 5 | 6 | | VI-1 | C1qtnf4 | 114900 | 4-May-15 |
| 3454 | 3 | 4 | 5 | 6 | | VI-1 | C1qtnf5 | 114902 | 4-May-15 |
| 3455 | 3 | 4 | 5 | 6 | | VI-1 | C1qtnf6 | 114904 | 4-May-15 |
| 3456 | 3 | 4 | 5 | 6 | | VI-1 | C1ra | | |
| 3457 | 3 | 4 | 5 | 6 | | VI-1 | C1rb | | |
| 3458 | 3 | 4 | 5 | 6 | | VI-1 | C1s1 | | |
| 3459 | 3 | 4 | 5 | 6 | | VI-1 | C1s2 | | |
| 3460 | 3 | 4 | 5 | 6 | | VI-1 | C2 | 717 | 7-Jun-15 |
| 3461 | 3 | 4 | 5 | 6 | | VI-1 | C3 | 718 | 23-May-15 |
| 3462 | 3 | 4 | 5 | 6 | | VI-1 | C330013E15Rik | | |
| 3463 | 3 | 4 | 5 | 6 | | VI-1 | C3ar1 | 719 | 4-May-15 |
| 3464 | 3 | 4 | 5 | 6 | | VI-1 | C4a | 720 | 4-May-15 |
| 3465 | 3 | 4 | 5 | 6 | | VI-1 | C4b | 721 | 17-May-15 |
| 3466 | 3 | 4 | 5 | 6 | | VI-1 | C5ar1 | 728 | 12-May-15 |
| 3467 | 3 | 4 | 5 | 6 | | VI-1 | C6 | 729 | 7-Jun-15 |
| 3468 | 3 | 4 | 5 | 6 | | VI-1 | C7 | 730 | 7-Jun-15 |
| 3469 | 3 | 4 | 5 | 6 | | VI-1 | C77370 | | |
| 3470 | 3 | 4 | 5 | 6 | | VI-1 | C920009B18Rik | | |
| 3471 | 3 | 4 | 5 | 6 | | VI-1 | C920025E04Rik | | |
| 3472 | 3 | 4 | 5 | 6 | | VI-1 | Cacna1d | 776 | 10-May-15 |
| 3473 | 3 | 4 | 5 | 6 | | VI-1 | Cacna1g | 8913 | 4-May-15 |
| 3474 | 3 | 4 | 5 | 6 | | VI-1 | Cacna1i | 8911 | 7-Jun-15 |
| 3475 | 3 | 4 | 5 | 6 | | VI-1 | Cacna2d1 | 781 | 12-May-15 |
| 3476 | 3 | 4 | 5 | 6 | | VI-1 | Cacna2d2 | 9254 | 12-May-15 |
| 3477 | 3 | 4 | 5 | 6 | | VI-1 | Cacng1 | 786 | 4-May-15 |
| 3478 | 3 | 4 | 5 | 6 | | VI-1 | Cacng7 | 59284 | 4-May-15 |
| 3479 | 3 | 4 | 5 | 6 | | VI-1 | Cad | 790 | 7-Jun-15 |
| 3480 | 3 | 4 | 5 | 6 | | VI-1 | Cadm3 | 57863 | 4-May-15 |
| 3481 | 3 | 4 | 5 | 6 | | VI-1 | Calm4 | | |
| 3482 | 3 | 4 | 5 | 6 | | VI-1 | Calm5 | | |
| 3483 | 3 | 4 | 5 | 6 | | VI-1 | Calml3 | 810 | 4-May-15 |
| 3484 | 3 | 4 | 5 | 6 | | VI-1 | Calml4 | 91860 | 4-May-15 |
| 3485 | 3 | 4 | 5 | 6 | | VI-1 | Caln1 | 83698 | 4-May-15 |
| 3486 | 3 | 4 | 5 | 6 | | VI-1 | Camk1d | 57118 | 4-May-15 |
| 3487 | 3 | 4 | 5 | 6 | | VI-1 | Camk2d | 817 | 4-May-15 |
| 3488 | 3 | 4 | 5 | 6 | | VI-1 | Camk2n1 | 55450 | 4-May-15 |
| 3489 | 3 | 4 | 5 | 6 | | VI-1 | Camkk1 | 84254 | 4-May-15 |
| 3490 | 3 | 4 | 5 | 6 | | VI-1 | Capg | 822 | 2015/6/7 |
| 3491 | 3 | 4 | 5 | 6 | | VI-1 | Capn5 | 726 | |
| 3492 | 3 | 4 | 5 | 6 | | VI-1 | Capn6 | 827 | |
| 3493 | 3 | 4 | 5 | 6 | | VI-1 | Car1 | 759 | 2015/6/7 |
| 3494 | 3 | 4 | 5 | 6 | | VI-1 | Car13 | | |
| 3495 | 3 | 4 | 5 | 6 | | VI-1 | Car2 | 760 | 2015/6/7 |
| 3496 | 3 | 4 | 5 | 6 | | VI-1 | Car5a | | |
| 3497 | 3 | 4 | 5 | 6 | | VI-1 | Car5b | | |
| 3498 | 3 | 4 | 5 | 6 | | VI-1 | Car7 | | |
| 3499 | 3 | 4 | 5 | 6 | | VI-1 | Car9 | | |
| 3500 | 3 | 4 | 5 | 6 | | VI-1 | Carhsp1 | 23589 | |
| 3501 | 3 | 4 | 5 | 6 | | VI-1 | Cartpt | 9607 | |
| 3502 | 3 | 4 | 5 | 6 | | VI-1 | Casc5 | 57082 | |
| 3503 | 3 | 4 | 5 | 6 | | VI-1 | Casp1 | 834 | |
| 3504 | 3 | 4 | 5 | 6 | | VI-1 | Casp2 | 835 | |
| 3505 | 3 | 4 | 5 | 6 | | VI-1 | Casp3 | 836 | |
| 3506 | 3 | 4 | 5 | 6 | | VI-1 | Casp4 | 837 | |
| 3507 | 3 | 4 | 5 | 6 | | VI-1 | Casq1 | 844 | |
| 3508 | 3 | 4 | 5 | 6 | | VI-1 | Casq2 | 845 | |
| 3509 | 3 | 4 | 5 | 6 | | VI-1 | Cass4 | 57091 | |
| 3510 | 3 | 4 | 5 | 6 | | VI-1 | Cbr2 | | |
| 3511 | 3 | 4 | 5 | 6 | | VI-1 | Ccbe1 | 147372 | |
| 3512 | 3 | 4 | 5 | 6 | | VI-1 | Ccdc136 | 64753 | |
| 3513 | 3 | 4 | 5 | 6 | | VI-1 | Ccdc17 | 149483 | |
| 3514 | 3 | 4 | 5 | 6 | | VI-1 | Ccdc18 | 343099 | |
| 3515 | 3 | 4 | 5 | 6 | | VI-1 | Ccdc183 | 84960 | |
| 3516 | 3 | 4 | 5 | 6 | | VI-1 | Ccdc34 | 91057 | |
| 3517 | 3 | 4 | 5 | 6 | | VI-1 | Ccdc57 | 284001 | |
| 3518 | 3 | 4 | 5 | 6 | | VI-1 | Ccdc6 | 8030 | |
| 3519 | 3 | 4 | 5 | 6 | | VI-1 | Ccdc64 | 92558 | |
| 3520 | 3 | 4 | 5 | 6 | | VI-1 | Ccdc66 | 285331 | |
| 3521 | 3 | 4 | 5 | 6 | | VI-1 | Ccdc68 | 80323 | |
| 3522 | 3 | 4 | 5 | 6 | | VI-1 | Ccdc69 | 26112 | |
| 3523 | 3 | 4 | 5 | 6 | | VI-1 | Ccdc74a | 90557 | |
| 3524 | 3 | 4 | 5 | 6 | | VI-1 | Ccdc77 | 84318 | |
| 3525 | 3 | 4 | 5 | 6 | | VI-1 | Ccdc80 | 151887 | |
| 3526 | 3 | 4 | 5 | 6 | | VI-1 | Ccdc88b | 283234 | |
| 3527 | 3 | 4 | 5 | 6 | | VI-1 | Cck | 885 | 2015/6/7 |
| 3528 | 3 | 4 | 5 | 6 | | VI-1 | Ccl12 | | |
| 3529 | 3 | 4 | 5 | 6 | | VI-1 | Ccl17 | 6361 | |
| 3530 | 3 | 4 | 5 | 6 | | VI-1 | Ccl19 | 6363 | |
| 3531 | 3 | 4 | 5 | 6 | | VI-1 | Ccl2 | 6347 | |
| 3532 | 3 | 4 | 5 | 6 | | VI-1 | Ccl20 | 6364 | 31-May-15 |
| 3533 | 3 | 4 | 5 | 6 | | VI-1 | Ccl21a | | |
| 3534 | 3 | 4 | 5 | 6 | | VI-1 | Ccl21b | | |
| 3535 | 3 | 4 | 5 | 6 | | VI-1 | Ccl21c | | |
| 3536 | 3 | 4 | 5 | 6 | | VI-1 | Ccl24 | 6369 | |
| 3537 | 3 | 4 | 5 | 6 | | VI-1 | Ccl3 | 6348 | |
| 3538 | 3 | 4 | 5 | 6 | | VI-1 | Ccl6 | | |
| 3539 | 3 | 4 | 5 | 6 | | VI-1 | Ccl7 | 6354 | |
| 3540 | 3 | 4 | 5 | 6 | | VI-1 | Ccl9 | | |
| 3541 | 3 | 4 | 5 | 6 | | VI-1 | Ccnb1ip1 | 57820 | |
| 3542 | 3 | 4 | 5 | 6 | | VI-1 | Ccne1 | 898 | |
| 3543 | 3 | 4 | 5 | 6 | | VI-1 | Ccne2 | 9134 | |
| 3544 | 3 | 4 | 5 | 6 | | VI-1 | Ccng2 | 901 | |
| 3545 | 3 | 4 | 5 | 6 | | VI-1 | Ccnj | 79616 | |
| 3546 | 3 | 4 | 5 | 6 | | VI-1 | Ccr1 | 1230 | |
| 3547 | 3 | 4 | 5 | 6 | | VI-1 | Ccr2 | 729230 | |
| 3548 | 3 | 4 | 5 | 6 | | VI-1 | Ccr5 | 1234 | |
| 3549 | 3 | 4 | 5 | 6 | | VI-1 | Ccr6 | 1235 | |
| 3550 | 3 | 4 | 5 | 6 | | VI-1 | Ccm4l | 25819 | |
| 3551 | 3 | 4 | 5 | 6 | | VI-1 | Ccsap | 126731 | |
| 3552 | 3 | 4 | 5 | 6 | | VI-1 | Cd101 | 9398 | |
| 3553 | 3 | 4 | 5 | 6 | | VI-1 | Cd109 | 135228 | |
| 3554 | 3 | 4 | 5 | 6 | | VI-1 | Cd14 | 929 | 2015/6/7 |
| 3555 | 3 | 4 | 5 | 6 | | VI-1 | Cd163 | 9332 | |
| 3556 | 3 | 4 | 5 | 6 | | VI-1 | Cd1d1 | | |
| 3557 | 3 | 4 | 5 | 6 | | VI-1 | Cd1d2 | | |
| 3558 | 3 | 4 | 5 | 6 | | VI-1 | Cd200 | 4345 | |
| 3559 | 3 | 4 | 5 | 6 | | VI-1 | Cd200r1 | 131450 | |
| 3560 | 3 | 4 | 5 | 6 | | VI-1 | Cd200r4 | | |
| 3561 | 3 | 4 | 5 | 6 | | VI-1 | Cd207 | 50489 | |
| 3562 | 3 | 4 | 5 | 6 | | VI-1 | Cd209b | | |
| 3563 | 3 | 4 | 5 | 6 | | VI-1 | Cd209f | | |
| 3564 | 3 | 4 | 5 | 6 | | VI-1 | Cd209g | | |
| 3565 | 3 | 4 | 5 | 6 | | VI-1 | Cd22 | 933 | |
| 3566 | 3 | 4 | 5 | 6 | | VI-1 | Cd244 | 51744 | |
| 3567 | 3 | 4 | 5 | 6 | | VI-1 | Cd248 | 57124 | |
| 3568 | 3 | 4 | 5 | 6 | | VI-1 | Cd276 | 80381 | |
| 3569 | 3 | 4 | 5 | 6 | | VI-1 | Cd300a | 11314 | |
| 3570 | 3 | 4 | 5 | 6 | | VI-1 | Cd300c | 10871 | |
| 3571 | 3 | 4 | 5 | 6 | | VI-1 | Cd300lb | 124599 | |
| 3572 | 3 | 4 | 5 | 6 | | VI-1 | Cd300lg | 146894 | |
| 3573 | 3 | 4 | 5 | 6 | | VI-1 | Cd300lh | | |
| 3574 | 3 | 4 | 5 | 6 | | VI-1 | Cd33 | 945 | |
| 3575 | 3 | 4 | 5 | 6 | | VI-1 | Cd36 | 948 | |
| 3576 | 3 | 4 | 5 | 6 | | VI-1 | Cd38 | 952 | |
| 3577 | 3 | 4 | 5 | 6 | | VI-1 | Cd3e | 916 | |

Fig. 30 - 20

| | | | | | | | | | |
|---|---|---|---|---|---|---|---|---|---|
| 3578 | 3 | 4 | 5 | 6 | | Vi-1 | Cd3g | 917 | 2015/6/7 |
| 3579 | 3 | 4 | 5 | 6 | | Vi-1 | Cd44 | 960 | |
| 3580 | 3 | 4 | 5 | 6 | | Vi-1 | Cd48 | 962 | |
| 3581 | 3 | 4 | 5 | 6 | | Vi-1 | Cd53 | 963 | |
| 3582 | 3 | 4 | 5 | 6 | | Vi-1 | Cd55 | 1604 | |
| 3583 | 3 | 4 | 5 | 6 | | Vi-1 | Cd68 | 968 | |
| 3584 | 3 | 4 | 5 | 6 | | Vi-1 | Cd74 | 972 | |
| 3585 | 3 | 4 | 5 | 6 | | Vi-1 | Cd80 | 941 | |
| 3586 | 3 | 4 | 5 | 6 | | Vi-1 | Cd82 | 3732 | |
| 3587 | 3 | 4 | 5 | 6 | | Vi-1 | Cd83 | 9308 | |
| 3588 | 3 | 4 | 5 | 6 | | Vi-1 | Cd84 | 8832 | |
| 3589 | 3 | 4 | 5 | 6 | | Vi-1 | Cd9 | 928 | |
| 3590 | 3 | 4 | 5 | 6 | | Vi-1 | Cd93 | 22918 | |
| 3591 | 3 | 4 | 5 | 6 | | Vi-1 | Cd97 | 976 | |
| 3592 | 3 | 4 | 5 | 6 | | Vi-1 | Cdc20 | 991 | |
| 3593 | 3 | 4 | 5 | 6 | | Vi-1 | Cdc25b | 994 | |
| 3594 | 3 | 4 | 5 | 6 | | Vi-1 | Cdc25c | 995 | |
| 3595 | 3 | 4 | 5 | 6 | | Vi-1 | Cdc6 | 990 | |
| 3596 | 3 | 4 | 5 | 6 | | Vi-1 | Cdc7 | 8317 | |
| 3597 | 3 | 4 | 5 | 6 | | Vi-1 | Cdca2 | 157313 | |
| 3598 | 3 | 4 | 5 | 6 | | Vi-1 | Cdca4 | 55038 | |
| 3599 | 3 | 4 | 5 | 6 | | Vi-1 | Cdca7 | 83879 | |
| 3600 | 3 | 4 | 5 | 6 | | Vi-1 | Cdca7l | 55536 | |
| 3601 | 3 | 4 | 5 | 6 | | Vi-1 | Cdcp1 | 64866 | |
| 3602 | 3 | 4 | 5 | 6 | | Vi-1 | Cdh1 | 999 | 2015/6/7 |
| 3603 | 3 | 4 | 5 | 6 | | Vi-1 | Cdh11 | 1009 | |
| 3604 | 3 | 4 | 5 | 6 | | Vi-1 | Cdh3 | 1001 | 2015/6/7 |
| 3605 | 3 | 4 | 5 | 6 | | Vi-1 | Cdhr3 | 222256 | |
| 3606 | 3 | 4 | 5 | 6 | | Vi-1 | Cdk14 | 5218 | |
| 3607 | 3 | 4 | 5 | 6 | | Vi-1 | Cdkl4 | 344387 | |
| 3608 | 3 | 4 | 5 | 6 | | Vi-1 | Cdkn1c | 1028 | |
| 3609 | 3 | 4 | 5 | 6 | | Vi-1 | Cdkn2b | 1030 | |
| 3610 | 3 | 4 | 5 | 6 | | Vi-1 | Cdkn2c | 1031 | |
| 3611 | 3 | 4 | 5 | 6 | | Vi-1 | Cdkn2d | 1032 | |
| 3612 | 3 | 4 | 5 | 6 | | Vi-1 | Cdkn3 | 1033 | |
| 3613 | 3 | 4 | 5 | 6 | | Vi-1 | Cdo1 | 1036 | |
| 3614 | 3 | 4 | 5 | 6 | | Vi-1 | Cdon | 50937 | |
| 3615 | 3 | 4 | 5 | 6 | | Vi-1 | Cdr2 | 1039 | |
| 3616 | 3 | 4 | 5 | 6 | | Vi-1 | Cds1 | 1040 | /6/7 |
| 3617 | 3 | 4 | 5 | 6 | | Vi-1 | Cdt1 | 81620 | |
| 3618 | 3 | 4 | 5 | 6 | | Vi-1 | Ceacam10 | | |
| 3619 | 3 | 4 | 5 | 6 | | Vi-1 | Ceacam16 | 388551 | |
| 3620 | 3 | 4 | 5 | 6 | | Vi-1 | Ceacam2 | | |
| 3621 | 3 | 4 | 5 | 6 | | Vi-1 | Cebpa | 1050 | |
| 3622 | 3 | 4 | 5 | 6 | | Vi-1 | Cebpb | 1051 | |
| 3623 | 3 | 4 | 5 | 6 | | Vi-1 | Cecr2 | 27443 | |
| 3624 | 3 | 4 | 5 | 6 | | Vi-1 | Celf2 | 10659 | |
| 3625 | 3 | 4 | 5 | 6 | | Vi-1 | Celf4 | 56853 | |
| 3626 | 3 | 4 | 5 | 6 | | Vi-1 | Cenpi | 2491 | |
| 3627 | 3 | 4 | 5 | 6 | | Vi-1 | Cenpk | 64105 | |
| 3628 | 3 | 4 | 5 | 6 | | Vi-1 | Cenpl | 91687 | |
| 3629 | 3 | 4 | 5 | 6 | | Vi-1 | Cenpm | 79019 | |
| 3630 | 3 | 4 | 5 | 6 | | Vi-1 | Cenpp | 401541 | |
| 3631 | 3 | 4 | 5 | 6 | | Vi-1 | Cenpq | 55166 | |
| 3632 | 3 | 4 | 5 | 6 | | Vi-1 | Cenpt | 80152 | |
| 3633 | 3 | 4 | 5 | 6 | | Vi-1 | Cenpu | 79682 | |
| 3634 | 3 | 4 | 5 | 6 | | Vi-1 | Cenpw | 387103 | |
| 3635 | 3 | 4 | 5 | 6 | | Vi-1 | Cep152 | 22995 | |
| 3636 | 3 | 4 | 5 | 6 | | Vi-1 | Cep72 | 55722 | |
| 3637 | 3 | 4 | 5 | 6 | | Vi-1 | Cep76 | 79959 | |
| 3638 | 3 | 4 | 5 | 6 | | Vi-1 | Cep85l | 387119 | |
| 3639 | 3 | 4 | 5 | 6 | | Vi-1 | Cercam | 51148 | |
| 3640 | 3 | 4 | 5 | 6 | | Vi-1 | Cerk | 64781 | |
| 3641 | 3 | 4 | 5 | 6 | | Vi-1 | Cers5 | 91012 | /5/21 |
| 3642 | 3 | 4 | 5 | 6 | | Vi-1 | Cers6 | 253782 | |
| 3643 | 3 | 4 | 5 | 6 | | Vi-1 | Ces1d | | |
| 3644 | 3 | 4 | 5 | 6 | | Vi-1 | Ces1f | | |
| 3645 | 3 | 4 | 5 | 6 | | Vi-1 | Ces2a | | |
| 3646 | 3 | 4 | 5 | 6 | | Vi-1 | Ces2g | | |
| 3647 | 3 | 4 | 5 | 6 | | Vi-1 | Ces4a | 283848 | |
| 3648 | 3 | 4 | 5 | 6 | | Vi-1 | Cfb | 629 | |
| 3649 | 3 | 4 | 5 | 6 | | Vi-1 | Cfh | 3075 | |
| 3650 | 3 | 4 | 5 | 6 | | Vi-1 | Cfi | 3426 | |
| 3651 | 3 | 4 | 5 | 6 | | Vi-1 | Cga | 1081 | /6/7 |
| 3652 | 3 | 4 | 5 | 6 | | Vi-1 | Cgn | 57530 | |
| 3653 | 3 | 4 | 5 | 6 | | Vi-1 | Cgref1 | 10669 | |
| 3654 | 3 | 4 | 5 | 6 | | Vi-1 | Chac2 | 494143 | |
| 3655 | 3 | 4 | 5 | 6 | | Vi-1 | Chaf1a | 10036 | |
| 3656 | 3 | 4 | 5 | 6 | | Vi-1 | Chaf1b | 8208 | |
| 3657 | 3 | 4 | 5 | 6 | | Vi-1 | Chchd10 | 400916 | |
| 3658 | 3 | 4 | 5 | 6 | | Vi-1 | Chek1 | 1111 | |
| 3659 | 3 | 4 | 5 | 6 | | Vi-1 | Chek2 | 11200 | |
| 3660 | 3 | 4 | 5 | 6 | | Vi-1 | Chga | 1113 | |
| 3661 | 3 | 4 | 5 | 6 | | Vi-1 | Chia1 | | |
| 3662 | 3 | 4 | 5 | 6 | | Vi-1 | Chka | 1119 | |
| 3663 | 3 | 4 | 5 | 6 | | Vi-1 | Chi1 | 10752 | /6/7 |
| 3664 | 3 | 4 | 5 | 6 | | Vi-1 | Chpf | 79586 | |
| 3665 | 3 | 4 | 5 | 6 | | Vi-1 | Chrdl1 | 91851 | |
| 3666 | 3 | 4 | 5 | 6 | | Vi-1 | Chrna4 | 1137 | |
| 3667 | 3 | 4 | 5 | 6 | | Vi-1 | Chst1 | 8534 | |
| 3668 | 3 | 4 | 5 | 6 | | Vi-1 | Chst10 | 9486 | |
| 3669 | 3 | 4 | 5 | 6 | | Vi-1 | Chst12 | 55501 | |
| 3670 | 3 | 4 | 5 | 6 | | Vi-1 | Chst2 | 9435 | |
| 3671 | 3 | 4 | 5 | 6 | | Vi-1 | Chst3 | 9469 | |
| 3672 | 3 | 4 | 5 | 6 | | Vi-1 | Chst4 | 10164 | |
| 3673 | 3 | 4 | 5 | 6 | | Vi-1 | Chtf18 | 63922 | |
| 3674 | 3 | 4 | 5 | 6 | | Vi-1 | Cib3 | 117286 | |
| 3675 | 3 | 4 | 5 | 6 | | Vi-1 | Cit | 11113 | /6/7 |
| 3676 | 3 | 4 | 5 | 6 | | Vi-1 | Cited4 | 163732 | |
| 3677 | 3 | 4 | 5 | 6 | | Vi-1 | Cklf | 51192 | /5/4 |
| 3678 | 3 | 4 | 5 | 6 | | Vi-1 | Ckmt1 | 548596 1159 | /6/7 |
| 3679 | 3 | 4 | 5 | 6 | | Vi-1 | Ckmt2 | 1160 | |
| 3680 | 3 | 4 | 5 | 6 | | Vi-1 | Cks1b | 1163 | |
| 3681 | 3 | 4 | 5 | 6 | | Vi-1 | Clca1 | 1179 | |
| 3682 | 3 | 4 | 5 | 6 | | Vi-1 | Clca2 | 9635 | |
| 3683 | 3 | 4 | 5 | 6 | | Vi-1 | Clcf1 | 23529 | |
| 3684 | 3 | 4 | 5 | 6 | | Vi-1 | Clcn2 | 1181 | |
| 3685 | 3 | 4 | 5 | 6 | | Vi-1 | Clcn5 | 1184 | |
| 3686 | 3 | 4 | 5 | 6 | | Vi-1 | Clcn6 | 1185 | |
| 3687 | 3 | 4 | 5 | 6 | | Vi-1 | Clcnkb | 1188 | |
| 3688 | 3 | 4 | 5 | 6 | | Vi-1 | Cldn1 | 9076 | |
| 3689 | 3 | 4 | 5 | 6 | | Vi-1 | Cldn13 | | |
| 3690 | 3 | 4 | 5 | 6 | | Vi-1 | Cldn15 | 24146 | |
| 3691 | 3 | 4 | 5 | 6 | | Vi-1 | Cldn20 | 49861 | |
| 3692 | 3 | 4 | 5 | 6 | | Vi-1 | Cldn23 | 137075 | |
| 3693 | 3 | 4 | 5 | 6 | | Vi-1 | Cldn5 | 7122 | |
| 3694 | 3 | 4 | 5 | 6 | | Vi-1 | Cldn7 | 1366 | |
| 3695 | 3 | 4 | 5 | 6 | | Vi-1 | Clec11a | 6320 | |
| 3696 | 3 | 4 | 5 | 6 | | Vi-1 | Clec12a | 160364 | |
| 3697 | 3 | 4 | 5 | 6 | | Vi-1 | Clec1a | 51267 | |
| 3698 | 3 | 4 | 5 | 6 | | Vi-1 | Clec2f | | |
| 3699 | 3 | 4 | 5 | 6 | | Vi-1 | Clec2i | | |
| 3700 | 3 | 4 | 5 | 6 | | Vi-1 | Clec3b | 7123 | |
| 3701 | 3 | 4 | 5 | 6 | | Vi-1 | Clec4a1 | | |
| 3702 | 3 | 4 | 5 | 6 | | Vi-1 | Clec4a2 | | |
| 3703 | 3 | 4 | 5 | 6 | | Vi-1 | Clec4a3 | | |
| 3704 | 3 | 4 | 5 | 6 | | Vi-1 | Clec4d | 338339 | |
| 3705 | 3 | 4 | 5 | 6 | | Vi-1 | Clec4g | 339390 | |
| 3706 | 3 | 4 | 5 | 6 | | Vi-1 | Clec4n | 93978 | |
| 3707 | 3 | 4 | 5 | 6 | | Vi-1 | Clec5a | 23601 | |
| 3708 | 3 | 4 | 5 | 6 | | Vi-1 | Clec7a | 64581 | |
| 3709 | 3 | 4 | 5 | 6 | | Vi-1 | Clhc1 | 130162 | |
| 3710 | 3 | 4 | 5 | 6 | | Vi-1 | Clic1 | 1192 | |
| 3711 | 3 | 4 | 5 | 6 | | Vi-1 | Clic3 | 9022 | |
| 3712 | 3 | 4 | 5 | 6 | | Vi-1 | Clic6 | 54102 | |
| 3713 | 3 | 4 | 5 | 6 | | Vi-1 | Clip3 | 25999 | |
| 3714 | 3 | 4 | 5 | 6 | | Vi-1 | Clip4 | 79745 | /6/7 |
| 3715 | 3 | 4 | 5 | 6 | | Vi-1 | Clmp | 79827 | |
| 3716 | 3 | 4 | 5 | 6 | | Vi-1 | Cln8 | 2055 | |
| 3717 | 3 | 4 | 5 | 6 | | Vi-1 | Clpx | 10845 | |
| 3718 | 3 | 4 | 5 | 6 | | Vi-1 | Cispn | 63967 | |
| 3719 | 3 | 4 | 5 | 6 | | Vi-1 | Clybl | 171425 | |
| 3720 | 3 | 4 | 5 | 6 | | Vi-1 | Cma1 | 1215 | |
| 3721 | 3 | 4 | 5 | 6 | | Vi-1 | Cmbl | 134147 | 4-May-15 |
| 3722 | 3 | 4 | 5 | 6 | | Vi-1 | Cmc2 | 56942 | |
| 3723 | 3 | 4 | 5 | 6 | | Vi-1 | Cmklr1 | 1240 | |
| 3724 | 3 | 4 | 5 | 6 | | Vi-1 | Cml5 | | |
| 3725 | 3 | 4 | 5 | 6 | | Vi-1 | Cmpk2 | 129607 | |
| 3726 | 3 | 4 | 5 | 6 | | Vi-1 | Cmya5 | 202333 | |
| 3727 | 3 | 4 | 5 | 6 | | Vi-1 | Cnksr1 | 10256 | |
| 3728 | 3 | 4 | 5 | 6 | | Vi-1 | Cnn1 | 1264 | |
| 3729 | 3 | 4 | 5 | 6 | | Vi-1 | Cnn2 | 1265 | |
| 3730 | 3 | 4 | 5 | 6 | | Vi-1 | Cnnm2 | 54805 | |
| 3731 | 3 | 4 | 5 | 6 | | Vi-1 | Cntfr | 1271 | |
| 3732 | 3 | 4 | 5 | 6 | | Vi-1 | Cntn5 | 53942 | |
| 3733 | 3 | 4 | 5 | 6 | | Vi-1 | Cntrob | 116840 | |
| 3734 | 3 | 4 | 5 | 6 | | Vi-1 | Coch | 1690 | |
| 3735 | 3 | 4 | 5 | 6 | | Vi-1 | Col10a1 | 1300 | |
| 3736 | 3 | 4 | 5 | 6 | | Vi-1 | Col14a1 | 7373 | |
| 3737 | 3 | 4 | 5 | 6 | | Vi-1 | Col15a1 | 1306 | |
| 3738 | 3 | 4 | 5 | 6 | | Vi-1 | Col16a1 | 1307 | |
| 3739 | 3 | 4 | 5 | 6 | | Vi-1 | Col18a1 | 80781 | |
| 3740 | 3 | 4 | 5 | 6 | | Vi-1 | Col1a1 | 1277 | |
| 3741 | 3 | 4 | 5 | 6 | | Vi-1 | Col1a2 | 1278 | |
| 3742 | 3 | 4 | 5 | 6 | | Vi-1 | Col27a1 | 85301 | |
| 3743 | 3 | 4 | 5 | 6 | | Vi-1 | Col2a1 | 1280 | |
| 3744 | 3 | 4 | 5 | 6 | | Vi-1 | Col3a1 | 1281 | |
| 3745 | 3 | 4 | 5 | 6 | | Vi-1 | Col4a1 | 1282 | |
| 3746 | 3 | 4 | 5 | 6 | | Vi-1 | Col4a2 | 1284 | |
| 3747 | 3 | 4 | 5 | 6 | | Vi-1 | Col4a3 | 1285 | |
| 3748 | 3 | 4 | 5 | 6 | | Vi-1 | Col5a1 | 1289 | |
| 3749 | 3 | 4 | 5 | 6 | | Vi-1 | Col5a2 | 1290 | |
| 3750 | 3 | 4 | 5 | 6 | | Vi-1 | Col5a3 | 50509 | |
| 3751 | 3 | 4 | 5 | 6 | | Vi-1 | Col6a1 | 1291 | |
| 3752 | 3 | 4 | 5 | 6 | | Vi-1 | Col6a2 | 1292 | |
| 3753 | 3 | 4 | 5 | 6 | | Vi-1 | Col6a3 | 1293 | |
| 3754 | 3 | 4 | 5 | 6 | | Vi-1 | Col6a4 | 344875 646300 | /5/4 |
| 3755 | 3 | 4 | 5 | 6 | | Vi-1 | Colgalt2 | 23127 | |
| 3756 | 3 | 4 | 5 | 6 | | Vi-1 | Colq | 8292 | |
| 3757 | 3 | 4 | 5 | 6 | | Vi-1 | Coro2a | 7464 | |
| 3758 | 3 | 4 | 5 | 6 | | Vi-1 | Coro6 | 84940 | |
| 3759 | 3 | 4 | 5 | 6 | | Vi-1 | Coro7 | 79585 | |
| 3760 | 3 | 4 | 5 | 6 | | Vi-1 | Cort | 1325 | |
| 3761 | 3 | 4 | 5 | 6 | | Vi-1 | Cotl1 | 23406 | |
| 3762 | 3 | 4 | 5 | 6 | | Vi-1 | Cox6a2 | 1339 | |
| 3763 | 3 | 4 | 5 | 6 | | Vi-1 | Cox6c | 1345 | 4-May-15 |
| 3764 | 3 | 4 | 5 | 6 | | Vi-1 | Cox7a1 | 1346 | |
| 3765 | 3 | 4 | 5 | 6 | | Vi-1 | Cox8b | 404544 | |
| 3766 | 3 | 4 | 5 | 6 | | Vi-1 | Cp | 1356 | |
| 3767 | 3 | 4 | 5 | 6 | | Vi-1 | Cpa3 | 1359 | /5/12 |

Fig. 30 - 21

| | | | | | | | | | |
|---|---|---|---|---|---|---|---|---|---|
| 3768 | 3 | 4 | 5 | 6 | | VI-1 | Cpeb3 | 22849 | |
| 3769 | 3 | 4 | 5 | 6 | | VI-1 | Cpeb4 | 80315 | |
| 3770 | 3 | 4 | 5 | 6 | | VI-1 | Cped1 | 79974 | |
| 3771 | 3 | 4 | 5 | 6 | | VI-1 | Cpne2 | 221184 | |
| 3772 | 3 | 4 | 5 | 6 | | VI-1 | Cpox | 1371 | |
| 3773 | 3 | 4 | 5 | 6 | | VI-1 | Cpt1b | 1375 | /6/7 |
| 3774 | 3 | 4 | 5 | 6 | | VI-1 | Cpxm1 | 56265 | |
| 3775 | 3 | 4 | 5 | 6 | | VI-1 | Crabp2 | 1382 | |
| 3776 | 3 | 4 | 5 | 6 | | VI-1 | Creb3l1 | 90993 | |
| 3777 | 3 | 4 | 5 | 6 | | VI-1 | Creb3l2 | 64764 | |
| 3778 | 3 | 4 | 5 | 6 | | VI-1 | Creld2 | 79174 | |
| 3779 | 3 | 4 | 5 | 6 | | VI-1 | Crip1 | 1396 | /6/7 |
| 3780 | 3 | 4 | 5 | 6 | | VI-1 | Crisp1 | 167 | |
| 3781 | 3 | 4 | 5 | 6 | | VI-1 | Crisp3 | 10321 | |
| 3782 | 3 | 4 | 5 | 6 | | VI-1 | Crispld2 | 83716 | |
| 3783 | 3 | 4 | 5 | 6 | | VI-1 | Crot | 54677 | |
| 3784 | 3 | 4 | 5 | 6 | | VI-1 | Cryaa | 1409 | |
| 3785 | 3 | 4 | 5 | 6 | | VI-1 | Crybb1 | 1414 | |
| 3786 | 3 | 4 | 5 | 6 | | VI-1 | Csf2rb | 1439 | |
| 3787 | 3 | 4 | 5 | 6 | | VI-1 | Csf2rb2 | 23772 | |
| 3788 | 3 | 4 | 5 | 6 | | VI-1 | Csf3r | 1441 | |
| 3789 | 3 | 4 | 5 | 6 | | VI-1 | Csgalnact1 | 55790 | |
| 3790 | 3 | 4 | 5 | 6 | | VI-1 | Csprs | | |
| 3791 | 3 | 4 | 5 | 6 | | VI-1 | Csrp1 | 64651 | |
| 3792 | 3 | 4 | 5 | 6 | | VI-1 | Csrp2 | 1466 | |
| 3793 | 3 | 4 | 5 | 6 | | VI-1 | Cst12 | | |
| 3794 | 3 | 4 | 5 | 6 | | VI-1 | Ctcflos | | |
| 3795 | 3 | 4 | 5 | 6 | | VI-1 | Cthrc1 | 115908 | |
| 3796 | 3 | 4 | 5 | 6 | | VI-1 | Ctla2a | | |
| 3797 | 3 | 4 | 5 | 6 | | VI-1 | Ctps | 1503 | |
| 3798 | 3 | 4 | 5 | 6 | | VI-1 | Ctr9 | 9646 | 12-May-15 |
| 3799 | 3 | 4 | 5 | 6 | | VI-1 | Ctsc | 1075 | |
| 3800 | 3 | 4 | 5 | 6 | | VI-1 | Ctsk | 1513 | |
| 3801 | 3 | 4 | 5 | 6 | | VI-1 | Ctsl | 1514 | |
| 3802 | 3 | 4 | 5 | 6 | | VI-1 | Ctsz | 1522 | |
| 3803 | 3 | 4 | 5 | 6 | | VI-1 | Ctxn3 | 613212 | |
| 3804 | 3 | 4 | 5 | 6 | | VI-1 | Cx3cl1 | 6376 | |
| 3805 | 3 | 4 | 5 | 6 | | VI-1 | Cx3cr1 | 1524 | |
| 3806 | 3 | 4 | 5 | 6 | | VI-1 | Cxcl1 | 2919 | |
| 3807 | 3 | 4 | 5 | 6 | | VI-1 | Cxcl10 | 3627 | |
| 3808 | 3 | 4 | 5 | 6 | | VI-1 | Cxcl14 | 9547 | |
| 3809 | 3 | 4 | 5 | 6 | | VI-1 | Cxcl16 | 58191 | |
| 3810 | 3 | 4 | 5 | 6 | | VI-1 | Cxcl5 | 6374 | |
| 3811 | 3 | 4 | 5 | 6 | | VI-1 | Cxcl9 | 4283 | |
| 3812 | 3 | 4 | 5 | 6 | | VI-1 | Cxcr1 | 3577 | |
| 3813 | 3 | 4 | 5 | 6 | | VI-1 | Cxxc5 | 51523 | |
| 3814 | 3 | 4 | 5 | 6 | | VI-1 | Cyba | 1535 | |
| 3815 | 3 | 4 | 5 | 6 | | VI-1 | Cybb | 1536 | |
| 3816 | 3 | 4 | 5 | 6 | | VI-1 | Cyfip2 | 26999 | |
| 3817 | 3 | 4 | 5 | 6 | | VI-1 | Cyp1b1 | 1545 | |
| 3818 | 3 | 4 | 5 | 6 | | VI-1 | Cyp26b1 | 56603 | |
| 3819 | 3 | 4 | 5 | 6 | | VI-1 | Cyp2a12 | | |
| 3820 | 3 | 4 | 5 | 6 | | VI-1 | Cyp2a22 | | |
| 3821 | 3 | 4 | 5 | 6 | | VI-1 | Cyp2a4 | | |
| 3822 | 3 | 4 | 5 | 6 | | VI-1 | Cyp2b10 | | |
| 3823 | 3 | 4 | 5 | 6 | | VI-1 | Cyp2c38 | | |
| 3824 | 3 | 4 | 5 | 6 | | VI-1 | Cyp2c44 | | |
| 3825 | 3 | 4 | 5 | 6 | | VI-1 | Cyp2d10 | | |
| 3826 | 3 | 4 | 5 | 6 | | VI-1 | Cyp2d11 | | |
| 3827 | 3 | 4 | 5 | 6 | | VI-1 | Cyp2d37-ps | | |
| 3828 | 3 | 4 | 5 | 6 | | VI-1 | Cyp2d40 | | |
| 3829 | 3 | 4 | 5 | 6 | | VI-1 | Cyp2s1 | 29785 | |
| 3830 | 3 | 4 | 5 | 6 | | VI-1 | Cyp2u1 | 113612 | |
| 3831 | 3 | 4 | 5 | 6 | | VI-1 | Cyp39a1 | 51302 | |
| 3832 | 3 | 4 | 5 | 6 | | VI-1 | Cyp3a13 | | |
| 3833 | 3 | 4 | 5 | 6 | | VI-1 | Cyp4a12a | | |
| 3834 | 3 | 4 | 5 | 6 | | VI-1 | Cyp4a31 | | |
| 3835 | 3 | 4 | 5 | 6 | | VI-1 | Cyp4a32 | | |
| 3836 | 3 | 4 | 5 | 6 | | VI-1 | Cyp4b1 | 1580 | |
| 3837 | 3 | 4 | 5 | 6 | | VI-1 | Cyp4b1-ps2 | | |
| 3838 | 3 | 4 | 5 | 6 | | VI-1 | Cyp4f17 | | |
| 3839 | 3 | 4 | 5 | 6 | | VI-1 | Cyp4f18 | | |
| 3840 | 3 | 4 | 5 | 6 | | VI-1 | Cyp51 | 1595 | |
| 3841 | 3 | 4 | 5 | 6 | | VI-1 | Cyr61 | 3491 | |
| 3842 | 3 | 4 | 5 | 6 | | VI-1 | Cyth4 | 27128 | |
| 3843 | 3 | 4 | 5 | 6 | | VI-1 | Cytip | 9595 | |
| 3844 | 3 | 4 | 5 | 6 | | VI-1 | Cytl1 | 54360 | |
| 3845 | 3 | 4 | 5 | 6 | | VI-1 | Cyyr1 | 116159 | |
| 3846 | 3 | 4 | 5 | 6 | | VI-1 | D14Ertd670e | | |
| 3847 | 3 | 4 | 5 | 6 | | VI-1 | D330023K18Rik | | |
| 3848 | 3 | 4 | 5 | 6 | | VI-1 | D430020J02Rik | | |
| 3849 | 3 | 4 | 5 | 6 | | VI-1 | D630015G02Rik | | |
| 3850 | 3 | 4 | 5 | 6 | | VI-1 | D930015E06Rik | | |
| 3851 | 3 | 4 | 5 | 6 | | VI-1 | Dab2 | 1601 | |
| 3852 | 3 | 4 | 5 | 6 | | VI-1 | Daf2 | | |
| 3853 | 3 | 4 | 5 | 6 | | VI-1 | Dancr | 57291 | |
| 3854 | 3 | 4 | 5 | 6 | | VI-1 | Dap | 1611 | /6/7 |
| 3855 | 3 | 4 | 5 | 6 | | VI-1 | Dapk2 | 23604 | 21-May-15 |
| 3856 | 3 | 4 | 5 | 6 | | VI-1 | Dapp1 | 27071 | 12-May-15 |
| 3857 | 3 | 4 | 5 | 6 | | VI-1 | Dbf4 | 10926 | 4-May-15 |
| 3858 | 3 | 4 | 5 | 6 | | VI-1 | Dbi5 | | |
| 3859 | 3 | 4 | 5 | 6 | | VI-1 | Dbn1 | 1627 | 3-May-15 |
| 3860 | 3 | 4 | 5 | 6 | | VI-1 | Dck1 | 9201 | 21-May-15 |
| 3861 | 3 | 4 | 5 | 6 | | VI-1 | Dck2 | 166614 | 4-May-15 |
| 3862 | 3 | 4 | 5 | 6 | | VI-1 | Dctpp1 | 79077 | 4-May-15 |
| 3863 | 3 | 4 | 5 | 6 | | VI-1 | Ddah1 | 23576 | 4-May-15 |

| | | | | | | | | | |
|---|---|---|---|---|---|---|---|---|---|
| 3864 | 3 | 4 | 5 | 6 | | VI-1 | Ddc | 1644 | 12-May-15 |
| 3865 | 3 | 4 | 5 | 6 | | VI-1 | Ddit4l | 115265 | 4-May-15 |
| 3866 | 3 | 4 | 5 | 6 | | VI-1 | Ddr2 | 4921 | 17-May-15 |
| 3867 | 3 | 4 | 5 | 6 | | VI-1 | Def6 | 50619 | /6/7 |
| 3868 | 3 | 4 | 5 | 6 | | VI-1 | Defa-ps12 | | |
| 3869 | 3 | 4 | 5 | 6 | | VI-1 | Defb11 | 245913 | 4-May-15 |
| 3870 | 3 | 4 | 5 | 6 | | VI-1 | Defb14 | 245928 | 4-May-15 |
| 3871 | 3 | 4 | 5 | 6 | | VI-1 | Defb22 | 245935 | 12-May-15 |
| 3872 | 3 | 4 | 5 | 6 | | VI-1 | Defb3 | | |
| 3873 | 3 | 4 | 5 | 6 | | VI-1 | Defb34 | | |
| 3874 | 3 | 4 | 5 | 6 | | VI-1 | Defb37 | | |
| 3875 | 3 | 4 | 5 | 6 | | VI-1 | Defb38 | | |
| 3876 | 3 | 4 | 5 | 6 | | VI-1 | Defb5 | | |
| 3877 | 3 | 4 | 5 | 6 | | VI-1 | Defb8 | | |
| 3878 | 3 | 4 | 5 | 6 | | VI-1 | Dek | 7913 | 4-May-15 |
| 3879 | 3 | 4 | 5 | 6 | | VI-1 | Dennd1c | 79958 | 12-May-15 |
| 3880 | 3 | 4 | 5 | 6 | | VI-1 | Dennd2c | 163259 | 4-May-15 |
| 3881 | 3 | 4 | 5 | 6 | | VI-1 | Dennd4a | 10260 | 4-May-15 |
| 3882 | 3 | 4 | 5 | 6 | | VI-1 | Dennd5b | 160518 | 12-May-15 |
| 3883 | 3 | 4 | 5 | 6 | | VI-1 | Depdc1a | 55635 | 4-May-15 |
| 3884 | 3 | 4 | 5 | 6 | | VI-1 | Depdc1b | 55789 | 4-May-15 |
| 3885 | 3 | 4 | 5 | 6 | | VI-1 | Des | 1674 | 23-May-15 |
| 3886 | 3 | 4 | 5 | 6 | | VI-1 | Dgke | 8526 | 24-May-15 |
| 3887 | 3 | 4 | 5 | 6 | | VI-1 | Dgkeos | | |
| 3888 | 3 | 4 | 5 | 6 | | VI-1 | Dhcr7 | 1717 | 23-May-15 |
| 3889 | 3 | 4 | 5 | 6 | | VI-1 | Dhfr | 1719 | 12-May-15 |
| 3890 | 3 | 4 | 5 | 6 | | VI-1 | Dhh | 50846 | 23-May-15 |
| 3891 | 3 | 4 | 5 | 6 | | VI-1 | Dhrs11 | 79154 | 4-May-15 |
| 3892 | 3 | 4 | 5 | 6 | | VI-1 | Dhx58 | 79132 | 4-May-15 |
| 3893 | 3 | 4 | 5 | 6 | | VI-1 | Diap3 | 81624 | 12-May-15 |
| 3894 | 3 | 4 | 5 | 6 | | VI-1 | Diras2 | 54769 | 4-May-15 |
| 3895 | 3 | 4 | 5 | 6 | | VI-1 | Disp2 | 85455 | 4-May-15 |
| 3896 | 3 | 4 | 5 | 6 | | VI-1 | Dkk3 | 27122 | 4-May-15 |
| 3897 | 3 | 4 | 5 | 6 | | VI-1 | Dkkl1 | 27120 | 4-May-15 |
| 3898 | 3 | 4 | 5 | 6 | | VI-1 | Dlc1 | 10395 | 7-Jun-15 |
| 3899 | 3 | 4 | 5 | 6 | | VI-1 | Dll1 | 28514 | 12-May-15 |
| 3900 | 3 | 4 | 5 | 6 | | VI-1 | Dmkn | 93099 | 21-May-15 |
| 3901 | 3 | 4 | 5 | 6 | | VI-1 | Dmrtb1 | 63948 | 4-May-15 |
| 3902 | 3 | 4 | 5 | 6 | | VI-1 | Dmtn | 2039 | 7-Jun-15 |
| 3903 | 3 | 4 | 5 | 6 | | VI-1 | Dna2 | 1763 | 3-May-15 |
| 3904 | 3 | 4 | 5 | 6 | | VI-1 | Dnah8 | 1769 | 4-May-15 |
| 3905 | 3 | 4 | 5 | 6 | | VI-1 | Dnaja4 | 55466 | 4-May-15 |
| 3906 | 3 | 4 | 5 | 6 | | VI-1 | Dnajb1 | 3337 | 12-May-15 |
| 3907 | 3 | 4 | 5 | 6 | | VI-1 | Dnajb13 | 374407 | 12-May-15 |
| 3908 | 3 | 4 | 5 | 6 | | VI-1 | Dnajb2 | 3300 | 23-May-15 |
| 3909 | 3 | 4 | 5 | 6 | | VI-1 | Dnajb3 | 414061 | 12-May-15 |
| 3910 | 3 | 4 | 5 | 6 | | VI-1 | Dnajc10 | 54431 | 4-May-15 |
| 3911 | 3 | 4 | 5 | 6 | | VI-1 | Dnajc21 | 134218 | 4-May-15 |
| 3912 | 3 | 4 | 5 | 6 | | VI-1 | Dnajc9 | 23234 | 4-May-15 |
| 3913 | 3 | 4 | 5 | 6 | | VI-1 | Dnm3os | 100628315 | 4-May-15 |
| 3914 | 3 | 4 | 5 | 6 | | VI-1 | Dnmt1 | 1786 | 22-May-15 |
| 3915 | 3 | 4 | 5 | 6 | | VI-1 | Dnph1 | 10591 | 23-May-15 |
| 3916 | 3 | 4 | 5 | 6 | | VI-1 | Doc2b | 8447 | 4-May-15 |
| 3917 | 3 | 4 | 5 | 6 | | VI-1 | Dock10 | 55619 | 4-May-15 |
| 3918 | 3 | 4 | 5 | 6 | | VI-1 | Dock11 | 139818 | 12-May-15 |
| 3919 | 3 | 4 | 5 | 6 | | VI-1 | Dock2 | 1794 | 4-May-15 |
| 3920 | 3 | 4 | 5 | 6 | | VI-1 | Dok1 | 1796 | 7-Jun-15 |
| 3921 | 3 | 4 | 5 | 6 | | VI-1 | Dok2 | 9046 | 4-May-15 |
| 3922 | 3 | 4 | 5 | 6 | | VI-1 | Dok3 | 79930 | 21-May-15 |
| 3923 | 3 | 4 | 5 | 6 | | VI-1 | Dok7 | 285489 | 23-May-15 |
| 3924 | 3 | 4 | 5 | 6 | | VI-1 | Dpep1 | 1800 | 12-May-15 |
| 3925 | 3 | 4 | 5 | 6 | | VI-1 | Dpep2 | 64174 | 4-May-15 |
| 3926 | 3 | 4 | 5 | 6 | | VI-1 | Dpf3 | 8110 | 17-May-15 |
| 3927 | 3 | 4 | 5 | 6 | | VI-1 | Dpysl3 | 1809 | 4-May-15 |
| 3928 | 3 | 4 | 5 | 6 | | VI-1 | Dram1 | 55332 | 4-May-15 |
| 3929 | 3 | 4 | 5 | 6 | | VI-1 | Dsc2 | 1824 | 7-Jun-15 |
| 3930 | 3 | 4 | 5 | 6 | | VI-1 | Dscc1 | 79075 | 4-May-15 |
| 3931 | 3 | 4 | 5 | 6 | | VI-1 | Dse | 29940 | 12-May-15 |
| 3932 | 3 | 4 | 5 | 6 | | VI-1 | Dsn1 | 79980 | 4-May-15 |
| 3933 | 3 | 4 | 5 | 6 | | VI-1 | Dtx4 | 23220 | 12-May-15 |
| 3934 | 3 | 4 | 5 | 6 | | VI-1 | Dusp1 | 1843 | 7-Jun-15 |
| 3935 | 3 | 4 | 5 | 6 | | VI-1 | Dusp26 | 78986 | 7-Jun-15 |
| 3936 | 3 | 4 | 5 | 6 | | VI-1 | Dusp3 | 1845 | 4-May-15 |
| 3937 | 3 | 4 | 5 | 6 | | VI-1 | Dusp4 | 1846 | 4-May-15 |
| 3938 | 3 | 4 | 5 | 6 | | VI-1 | Dusp5 | 1847 | 4-May-15 |
| 3939 | 3 | 4 | 5 | 6 | | VI-1 | Dusp8 | 1850 | 4-May-15 |
| 3940 | 3 | 4 | 5 | 6 | | VI-1 | Dusp9 | 1852 | 4-May-15 |
| 3941 | 3 | 4 | 5 | 6 | | VI-1 | Dut | 1854 | 12-May-15 |
| 3942 | 3 | 4 | 5 | 6 | | VI-1 | Dyrk3 | 8444 | 4-May-15 |
| 3943 | 3 | 4 | 5 | 6 | | VI-1 | E030003E18Rik | | |
| 3944 | 3 | 4 | 5 | 6 | | VI-1 | E030011O05Rik | | |
| 3945 | 3 | 4 | 5 | 6 | | VI-1 | E030018B13Rik | | |
| 3946 | 3 | 4 | 5 | 6 | | VI-1 | E130215H24Rik | | |
| 3947 | 3 | 4 | 5 | 6 | | VI-1 | E130309D14Rik | | |
| 3948 | 3 | 4 | 5 | 6 | | VI-1 | E2f1 | 1869 | 7-Jun-15 |
| 3949 | 3 | 4 | 5 | 6 | | VI-1 | E2f2 | 1870 | 4-May-15 |
| 3950 | 3 | 4 | 5 | 6 | | VI-1 | E2f7 | 144455 | 4-May-15 |
| 3951 | 3 | 4 | 5 | 6 | | VI-1 | E330013P04Rik | | |
| 3952 | 3 | 4 | 5 | 6 | | VI-1 | Eaf2 | 55840 | 7-Jun-15 |
| 3953 | 3 | 4 | 5 | 6 | | VI-1 | Ear1 | 9572 | 12-May-15 |
| 3954 | 3 | 4 | 5 | 6 | | VI-1 | Ear10 | | |
| 3955 | 3 | 4 | 5 | 6 | | VI-1 | Ear2 | 2063 | 4-May-15 |
| 3956 | 3 | 4 | 5 | 6 | | VI-1 | Ear6 | | |
| 3957 | 3 | 4 | 5 | 6 | | VI-1 | Ebi3 | 10148 | 12-May-15 |
| 3958 | 3 | 4 | 5 | 6 | | VI-1 | Echdc2 | 55268 | 4-May-15 |

Fig. 30 - 22

| | | | | | | | | | | | | | | | | |
|---|---|---|---|---|---|---|---|---|---|---|---|---|---|---|---|---|
| 3959 | 3 | 4 | 5 | 6 | | VI-1 | Ect2 | 1894 | 4-May-15 | 4054 | 3 | 4 | 5 | 6 | | VI-1 | Fam105a | 54491 | 4-May-15 |
| 3960 | 3 | 4 | 5 | 6 | | VI-1 | Eda2r | 60401 | 4-May-15 | 4055 | 3 | 4 | 5 | 6 | | VI-1 | Fam107a | 11170 | 12-May-15 |
| 3961 | 3 | 4 | 5 | 6 | | VI-1 | Edar | 10913 | 23-May-15 | 4056 | 3 | 4 | 5 | 6 | | VI-1 | Fam107b | 83641 | 4-May-15 |
| 3962 | 3 | 4 | 5 | 6 | | VI-1 | Edaradd | 128178 | 23-May-15 | 4057 | 3 | 4 | 5 | 6 | | VI-1 | Fam109b | 150368 | 4-May-15 |
| 3963 | 3 | 4 | 5 | 6 | | VI-1 | Edn3 | 1908 | 23-May-15 | 4058 | 3 | 4 | 5 | 6 | | VI-1 | Fam110b | 90362 | 4-May-15 |
| 3964 | 3 | 4 | 5 | 6 | | VI-1 | Ednrb | 1910 | 24-May-15 | 4059 | 3 | 4 | 5 | 6 | | VI-1 | Fam111a | 63901 | 4-May-15 |
| 3965 | 3 | 4 | 5 | 6 | | VI-1 | Efcc1 | 79825 | 4-May-15 | 4060 | 3 | 4 | 5 | 6 | | VI-1 | Fam117a | 81558 | 4-May-15 |
| 3966 | 3 | 4 | 5 | 6 | | VI-1 | Efemp2 | 30008 | 23-May-15 | 4061 | 3 | 4 | 5 | 6 | | VI-1 | Fam117b | 150864 | 4-May-15 |
| 3967 | 3 | 4 | 5 | 6 | | VI-1 | Efhd1 | 80303 | 7-May-15 | 4062 | 3 | 4 | 5 | 6 | | VI-1 | Fam126b | 285172 | 4-May-15 |
| 3968 | 3 | 4 | 5 | 6 | | VI-1 | Efhd2 | 79180 | 4-May-15 | 4063 | 3 | 4 | 5 | 6 | | VI-1 | Fam129b | 64855 | 4-May-15 |
| 3969 | 3 | 4 | 5 | 6 | | VI-1 | Efna3 | 1944 | 4-May-15 | 4064 | 3 | 4 | 5 | 6 | | VI-1 | Fam132a | 385581 | 4-May-15 |
| 3970 | 3 | 4 | 5 | 6 | | VI-1 | Efr3b | 22979 | 4-May-15 | 4065 | 3 | 4 | 5 | 6 | | VI-1 | Fam132b | 151176 | 12-May-15 |
| 3971 | 3 | 4 | 5 | 6 | | VI-1 | Efs | 10278 | 4-May-15 | 4066 | 3 | 4 | 5 | 6 | | VI-1 | Fam134b | 54463 | 23-May-15 |
| 3972 | 3 | 4 | 5 | 6 | | VI-1 | Egf | 1950 | 24-May-15 | 4067 | 3 | 4 | 5 | 6 | | VI-1 | Fam13a | 10144 | 24-May-15 |
| 3973 | 3 | 4 | 5 | 6 | | VI-1 | Egfbp2 | | | 4068 | 3 | 4 | 5 | 6 | | VI-1 | Fam13c | 220965 | 4-May-15 |
| 3974 | 3 | 4 | 5 | 6 | | VI-1 | Egfr | 1956 | 24-May-15 | 4069 | 3 | 4 | 5 | 6 | | VI-1 | Fam167b | 84734 | 4-May-15 |
| 3975 | 3 | 4 | 5 | 6 | | VI-1 | Egr1 | 1958 | 24-May-15 | 4070 | 3 | 4 | 5 | 6 | | VI-1 | Fam169a | 26049 | 12-May-15 |
| 3976 | 3 | 4 | 5 | 6 | | VI-1 | Egr3 | 1960 | 12-May-15 | 4071 | 3 | 4 | 5 | 6 | | VI-1 | Fam174b | 400451 | 4-May-15 |
| 3977 | 3 | 4 | 5 | 6 | | VI-1 | Ehd3 | 30845 | 4-May-15 | 4072 | 3 | 4 | 5 | 6 | | VI-1 | Fam178b | 51252 | 4-May-15 |
| 3978 | 3 | 4 | 5 | 6 | | VI-1 | Ehf | 26298 | 4-May-15 | 4073 | 3 | 4 | 5 | 6 | | VI-1 | Fam180a | 389558 | 4-May-15 |
| 3979 | 3 | 4 | 5 | 6 | | VI-1 | Eid3 | 493861 | 7-Jun-15 | 4074 | 3 | 4 | 5 | 6 | | VI-1 | Fam184b | 27146 | 4-May-15 |
| 3980 | 3 | 4 | 5 | 6 | | VI-1 | Eif1a | 1964 | 7-Jun-15 | 4075 | 3 | 4 | 5 | 6 | | VI-1 | Fam187b | 148109 | 4-May-15 |
| 3981 | 3 | 4 | 5 | 6 | | VI-1 | Eif2ak1 | 27102 | 7-Jun-15 | 4076 | 3 | 4 | 5 | 6 | | VI-1 | Fam198a | 729085 | 4-May-15 |
| 3982 | 3 | 4 | 5 | 6 | | VI-1 | Elavl4 | 1996 | 12-May-15 | 4077 | 3 | 4 | 5 | 6 | | VI-1 | Fam198b | 51313 | 4-May-15 |
| 3983 | 3 | 4 | 5 | 6 | | VI-1 | Elf2 | 22936 | 4-May-15 | 4078 | 3 | 4 | 5 | 6 | | VI-1 | Fam20c | 56975 | 17-May-15 |
| 3984 | 3 | 4 | 5 | 6 | | VI-1 | Elf3 | 80237 | 4-May-15 | 4079 | 3 | 4 | 5 | 6 | | VI-1 | Fam210b | 116151 | 4-May-15 |
| 3985 | 3 | 4 | 5 | 6 | | VI-1 | Elovl6 | 79071 | 4-May-15 | 4080 | 3 | 4 | 5 | 6 | | VI-1 | Fam213a | 84293 | 4-May-15 |
| 3986 | 3 | 4 | 5 | 6 | | VI-1 | Emb | 5463 | 4-May-15 | 4081 | 3 | 4 | 5 | 6 | | VI-1 | Fam214a | 56204 | 4-May-15 |
| 3987 | 3 | 4 | 5 | 6 | | VI-1 | Eme1 | 146956 | 4-May-15 | 4082 | 3 | 4 | 5 | 6 | | VI-1 | Fam228b | 375190 | 12-May-15 |
| 3988 | 3 | 4 | 5 | 6 | | VI-1 | Eme2 | 197342 | 4-May-15 | 4083 | 3 | 4 | 5 | 6 | | VI-1 | Fam25c | 644054 | 12-May-15 |
| 3989 | 3 | 4 | 5 | 6 | | VI-1 | Emilin1 | 11117 | 4-May-15 | 4084 | 3 | 4 | 5 | 6 | | VI-1 | Fam26e | 254228 | 4-May-15 |
| 3990 | 3 | 4 | 5 | 6 | | VI-1 | Emilin2 | 84034 | 4-May-15 | 4085 | 3 | 4 | 5 | 6 | | VI-1 | Fam26f | 441168 | 4-May-15 |
| 3991 | 3 | 4 | 5 | 6 | | VI-1 | Emp1 | 2012 | 4-May-15 | 4086 | 3 | 4 | 5 | 6 | | VI-1 | Fam35a | 54537 | 4-May-15 |
| 3992 | 3 | 4 | 5 | 6 | | VI-1 | Emp3 | 2014 | 4-May-15 | 4087 | 3 | 4 | 5 | 6 | | VI-1 | Fam3c | 10447 | 4-May-15 |
| 3993 | 3 | 4 | 5 | 6 | | VI-1 | Emr1 | 2015 | 4-May-15 | 4088 | 3 | 4 | 5 | 6 | | VI-1 | Fam46a | 55603 | 12-May-15 |
| 3994 | 3 | 4 | 5 | 6 | | VI-1 | Emr4 | 326342 | 4-May-15 | 4089 | 3 | 4 | 5 | 6 | | VI-1 | Fam46b | 115572 | 4-May-15 |
| 3995 | 3 | 4 | 5 | 6 | | VI-1 | Emx2 | 2018 | 17-May-15 | 4090 | 3 | 4 | 5 | 6 | | VI-1 | Fam46c | 54855 | 4-May-15 |
| 3996 | 3 | 4 | 5 | 6 | | VI-1 | Endod1 | 23052 | 4-May-15 | 4091 | 3 | 4 | 5 | 6 | | VI-1 | Fam46d | 169966 | 4-May-15 |
| 3997 | 3 | 4 | 5 | 6 | | VI-1 | Endou | 8909 | 23-May-15 | 4092 | 3 | 4 | 5 | 6 | | VI-1 | Fam65b | 9750 | 4-May-15 |
| 3998 | 3 | 4 | 5 | 6 | | VI-1 | Eno1b | | | 4093 | 3 | 4 | 5 | 6 | | VI-1 | Fam71e1 | 112703 | 12-May-15 |
| 3999 | 3 | 4 | 5 | 6 | | VI-1 | Eno2 | 2026 | 4-May-15 | 4094 | 3 | 4 | 5 | 6 | | VI-1 | Fam71f2 | 346653 | 4-May-15 |
| 4000 | 3 | 4 | 5 | 6 | | VI-1 | Enpep | 2028 | 12-May-15 | 4095 | 3 | 4 | 5 | 6 | | VI-1 | Fam72a | 729533 | 4-May-15 |
| 4001 | 3 | 4 | 5 | 6 | | VI-1 | Enpp5 | 59084 | 4-May-15 | 4096 | 3 | 4 | 5 | 6 | | VI-1 | Fam78a | 286336 | 4-May-15 |
| 4002 | 3 | 4 | 5 | 6 | | VI-1 | Entpd2 | 954 | 4-May-15 | 4097 | 3 | 4 | 5 | 6 | | VI-1 | Fam83d | 81610 | 12-May-15 |
| 4003 | 3 | 4 | 5 | 6 | | VI-1 | Entpd7 | 57089 | 4-May-15 | 4098 | 3 | 4 | 5 | 6 | | VI-1 | Fam83h | 286077 | 21-May-15 |
| 4004 | 3 | 4 | 5 | 6 | | VI-1 | Eomes | 8320 | 12-May-15 | 4099 | 3 | 4 | 5 | 6 | | VI-1 | Fam84b | 157638 | 4-May-15 |
| 4005 | 3 | 4 | 5 | 6 | | VI-1 | Epb4.1 | | | 4100 | 3 | 4 | 5 | 6 | | VI-1 | Fam89a | 375061 | 4-May-15 |
| 4006 | 3 | 4 | 5 | 6 | | VI-1 | Epb4.2 | | | 4101 | 3 | 4 | 5 | 6 | | VI-1 | Fanca | 2175 | 23-May-15 |
| 4007 | 3 | 4 | 5 | 6 | | VI-1 | Epcam | 4072 | 24-May-15 | 4102 | 3 | 4 | 5 | 6 | | VI-1 | Fancd2 | 2177 | 23-May-15 |
| 4008 | 3 | 4 | 5 | 6 | | VI-1 | Epdr1 | 54749 | 4-May-15 | 4103 | 3 | 4 | 5 | 6 | | VI-1 | Fanci | 55215 | 23-May-15 |
| 4009 | 3 | 4 | 5 | 6 | | VI-1 | Epha2 | 1969 | 4-May-15 | 4104 | 3 | 4 | 5 | 6 | | VI-1 | Fap | 2191 | 7-Jun-15 |
| 4010 | 3 | 4 | 5 | 6 | | VI-1 | Epha7 | 2045 | 17-May-15 | 4105 | 3 | 4 | 5 | 6 | | VI-1 | Far1 | 84188 | 4-May-15 |
| 4011 | 3 | 4 | 5 | 6 | | VI-1 | Epha8 | 2046 | 3-May-15 | 4106 | 3 | 4 | 5 | 6 | | VI-1 | Fas | 355 | 13-Jun-15 |
| 4012 | 3 | 4 | 5 | 6 | | VI-1 | Ephx2 | 2053 | 12-May-15 | 4107 | 3 | 4 | 5 | 6 | | VI-1 | Fasn | 2194 | 4-May-15 |
| 4013 | 3 | 4 | 5 | 6 | | VI-1 | Epn3 | 55040 | 4-May-15 | 4108 | 3 | 4 | 5 | 6 | | VI-1 | Fat1 | 2195 | 12-May-15 |
| 4014 | 3 | 4 | 5 | 6 | | VI-1 | Epor | 2057 | 12-May-15 | 4109 | 3 | 4 | 5 | 6 | | VI-1 | Fbf1 | 85302 | 4-May-15 |
| 4015 | 3 | 4 | 5 | 6 | | VI-1 | Eppin | 57119 | 4-May-15 | 4110 | 3 | 4 | 5 | 6 | | VI-1 | Fbln1 | 2192 | 12-May-15 |
| 4016 | 3 | 4 | 5 | 6 | | VI-1 | Eppk1 | 83481 | 4-May-15 | 4111 | 3 | 4 | 5 | 6 | | VI-1 | Fbln2 | 2199 | 12-May-15 |
| 4017 | 3 | 4 | 5 | 6 | | VI-1 | Eps8l1 | 54869 | 4-May-15 | 4112 | 3 | 4 | 5 | 6 | | VI-1 | Fbln5 | 10516 | 23-May-15 |
| 4018 | 3 | 4 | 5 | 6 | | VI-1 | Epsti1 | 94240 | 4-May-15 | 4113 | 3 | 4 | 5 | 6 | | VI-1 | Fbln7 | 129804 | 4-May-15 |
| 4019 | 3 | 4 | 5 | 6 | | VI-1 | Epx | 8288 | 12-May-15 | 4114 | 3 | 4 | 5 | 6 | | VI-1 | Fbn1 | 2200 | 23-May-15 |
| 4020 | 3 | 4 | 5 | 6 | | VI-1 | Erbb3 | 2065 | 17-May-15 | 4115 | 3 | 4 | 5 | 6 | | VI-1 | Fbn2 | 2201 | 23-May-15 |
| 4021 | 3 | 4 | 5 | 6 | | VI-1 | Ercc1 | 2067 | 23-May-15 | 4116 | 3 | 4 | 5 | 6 | | VI-1 | Fbxl7 | 23194 | 4-May-15 |
| 4022 | 3 | 4 | 5 | 6 | | VI-1 | Ercc6l | 54821 | 10-May-15 | 4117 | 3 | 4 | 5 | 6 | | VI-1 | Fbxo21 | 23014 | 4-May-15 |
| 4023 | 3 | 4 | 5 | 6 | | VI-1 | Ereg | 2069 | 4-May-15 | 4118 | 3 | 4 | 5 | 6 | | VI-1 | Fbxo30 | 84085 | 7-Jun-15 |
| 4024 | 3 | 4 | 5 | 6 | | VI-1 | Erlec1 | 27248 | 3-May-15 | 4119 | 3 | 4 | 5 | 6 | | VI-1 | Fbxo32 | 114907 | 12-May-15 |
| 4025 | 3 | 4 | 5 | 6 | | VI-1 | Ermap | 114625 | 12-May-15 | 4120 | 3 | 4 | 5 | 6 | | VI-1 | Fbxo34 | 55030 | 4-May-15 |
| 4026 | 3 | 4 | 5 | 6 | | VI-1 | Ermap | | | 4121 | 3 | 4 | 5 | 6 | | VI-1 | Fbxo5 | 26271 | 23-May-15 |
| 4027 | 3 | 4 | 5 | 6 | | VI-1 | Ern1 | 2081 | 24-May-15 | 4122 | 3 | 4 | 5 | 6 | | VI-1 | Fcamr | 83953 | 4-May-15 |
| 4028 | 3 | 4 | 5 | 6 | | VI-1 | Ero1l | 30001 | 23-May-15 | 4123 | 3 | 4 | 5 | 6 | | VI-1 | Fcer1g | 2207 | 12-May-15 |
| 4029 | 3 | 4 | 5 | 6 | | VI-1 | Errfi1 | 54206 | 4-May-15 | 4124 | 3 | 4 | 5 | 6 | | VI-1 | Fcgr1 | | |
| 4030 | 3 | 4 | 5 | 6 | | VI-1 | Esm1 | 11082 | 12-May-15 | 4125 | 3 | 4 | 5 | 6 | | VI-1 | Fcgr2b | 2213 | 17-May-15 |
| 4031 | 3 | 4 | 5 | 6 | | VI-1 | Espl1 | 9700 | 4-May-15 | 4126 | 3 | 4 | 5 | 6 | | VI-1 | Fcgr3 | 2214, 2215 | 7-Jun-15 |
| 4032 | 3 | 4 | 5 | 6 | | VI-1 | Esrp1 | 54845 | 4-May-15 | 4127 | 3 | 4 | 5 | 6 | | VI-1 | Fcna | | |
| 4032 | 3 | 4 | 5 | 6 | | VI-1 | Etl4 | 100144, 434 | 7-Dec-14 | 4128 | 3 | 4 | 5 | 6 | | VI-1 | Fcnb | | |
| 4033 | 3 | 4 | 5 | 6 | | VI-1 | Ets1 | 2113 | 21-May-15 | 4129 | 3 | 4 | 5 | 6 | | VI-1 | Fcrl1 | 115350 | 4-May-15 |
| 4034 | 3 | 4 | 5 | 6 | | VI-1 | Etv5 | 2119 | 24-May-15 | 4130 | 3 | 4 | 5 | 6 | | VI-1 | Fcrl6 | 343413 | 4-May-15 |
| 4035 | 3 | 4 | 5 | 6 | | VI-1 | Evc | 2121 | 12-May-15 | 4131 | 3 | 4 | 5 | 6 | | VI-1 | Fcrlb | 127943 | 4-May-15 |
| 4036 | 3 | 4 | 5 | 6 | | VI-1 | Evi2a | 2123 | 12-May-15 | 4132 | 3 | 4 | 5 | 6 | | VI-1 | Fcrls | | |
| 4037 | 3 | 4 | 5 | 6 | | VI-1 | Evi2b | 2124 | 12-May-15 | 4133 | 3 | 4 | 5 | 6 | | VI-1 | Fdft1 | 2222 | 12-May-15 |
| 4038 | 3 | 4 | 5 | 6 | | VI-1 | Evl | 51466 | 12-May-15 | 4134 | 3 | 4 | 5 | 6 | | VI-1 | Fdps | 2224 | 12-May-15 |
| 4039 | 3 | 4 | 5 | 6 | | VI-1 | Exo1 | 9156 | 12-May-15 | 4135 | 3 | 4 | 5 | 6 | | VI-1 | Fech | 2235 | 23-May-15 |
| 4040 | 3 | 4 | 5 | 6 | | VI-1 | Exoc3l4 | 91828 | 4-May-15 | 4136 | 3 | 4 | 5 | 6 | | VI-1 | Fen1 | 2237 | 3-May-15 |
| 4041 | 3 | 4 | 5 | 6 | | VI-1 | Eya2 | 2139 | 4-May-15 | 4137 | 3 | 4 | 5 | 6 | | VI-1 | Fermt3 | 83706 | 24-May-15 |
| 4042 | 3 | 4 | 5 | 6 | | VI-1 | Ezr | 7430 | 24-May-15 | 4138 | 3 | 4 | 5 | 6 | | VI-1 | Ffar2 | 2867 | 7-Jun-15 |
| 4043 | 3 | 4 | 5 | 6 | | VI-1 | F2r | 2149 | 17-May-15 | 4139 | 3 | 4 | 5 | 6 | | VI-1 | Fgd2 | 221472 | 7-Jun-15 |
| 4044 | 3 | 4 | 5 | 6 | | VI-1 | F630028O10Rik | | | 4140 | 3 | 4 | 5 | 6 | | VI-1 | Fgd3 | 89846 | 7-Jun-15 |
| 4045 | 3 | 4 | 5 | 6 | | VI-1 | F7 | 2155 | 12-May-15 | 4141 | 3 | 4 | 5 | 6 | | VI-1 | Fgf12 | 2257 | 7-Jun-15 |
| 4046 | 3 | 4 | 5 | 6 | | VI-1 | F830002L21Rik | | | 4142 | 3 | 4 | 5 | 6 | | VI-1 | Fgf13 | 2258 | 7-Jun-15 |
| 4047 | 3 | 4 | 5 | 6 | | VI-1 | Fabp1 | 2168 | 12-May-15 | 4143 | 3 | 4 | 5 | 6 | | VI-1 | Fgf14 | 2259 | 23-May-15 |
| 4048 | 3 | 4 | 5 | 6 | | VI-1 | Fabp3 | 2170 | 24-May-15 | 4144 | 3 | 4 | 5 | 6 | | VI-1 | Fgf23 | 8074 | 17-May-15 |
| 4049 | 3 | 4 | 5 | 6 | | VI-1 | Fabp7 | 2173 | 12-May-15 | 4145 | 3 | 4 | 5 | 6 | | VI-1 | Fgf6 | 2251 | 4-May-15 |
| 4050 | 3 | 4 | 5 | 6 | | VI-1 | Fads3 | 3995 | 4-May-15 | 4146 | 3 | 4 | 5 | 6 | | VI-1 | Fgfr1 | 2260 | 4-May-15 |
| 4051 | 3 | 4 | 5 | 6 | | VI-1 | Fahd1 | 81889 | 10-May-15 | 4147 | 3 | 4 | 5 | 6 | | VI-1 | Fgfr2 | 2263 | 24-May-15 |
| 4052 | 3 | 4 | 5 | 6 | | VI-1 | Faim3 | 9214 | 12-May-15 | 4148 | 3 | 4 | 5 | 6 | | VI-1 | Fgfr3 | 2261 | 23-May-15 |
| 4053 | 3 | 4 | 5 | 6 | | VI-1 | Fam101b | 359845 | 4-May-15 | | | | | | | | | | |

Fig. 30 - 23

| | | | | | | | | | | | | | | | |
|---|---|---|---|---|---|---|---|---|---|---|---|---|---|---|---|
| 4149 | 3 | 4 | 5 | 6 | | VI-1 | Fgl2 | 10875 | 12-May-15 | 4245 | 3 | 4 | 5 | 6 | | VI-1 | Gdf1 | 2657 | 4-May-15 |
| 4150 | 3 | 4 | 5 | 6 | | VI-1 | Fgr | 2268 | 12-May-15 | 4246 | 3 | 4 | 5 | 6 | | VI-1 | Gdf10 | 2662 | 4-May-15 |
| 4151 | 3 | 4 | 5 | 6 | | VI-1 | Fhdc1 | 85462 | 21-May-15 | 4247 | 3 | 4 | 5 | 6 | | VI-1 | Gdf13 | 10220 | 21-May-15 |
| 4152 | 3 | 4 | 5 | 6 | | VI-1 | Fhl1 | 2273 | 7-Jun-15 | 4248 | 3 | 4 | 5 | 6 | | VI-1 | Gdpd2 | 54857 | 4-May-15 |
| 4153 | 3 | 4 | 5 | 6 | | VI-1 | Fhl3 | 2275 | 7-Jun-15 | 4249 | 3 | 4 | 5 | 6 | | VI-1 | Gem | 2669 | 7-Jun-15 |
| 4154 | 3 | 4 | 5 | 6 | | VI-1 | Fhl4 | 8676 | 23-May-15 | 4250 | 3 | 4 | 5 | 6 | | VI-1 | Gen1 | 348654 | 4-May-15 |
| 4155 | 3 | 4 | 5 | 6 | | VI-1 | Fibcd1 | 84929 | 4-May-15 | 4251 | 3 | 4 | 5 | 6 | | VI-1 | Gfap | 2670 | 23-May-15 |
| 4156 | 3 | 4 | 5 | 6 | | VI-1 | Fibin | 387758 | 4-May-15 | 4252 | 3 | 4 | 5 | 6 | | VI-1 | Gfi1 | 2672 | 4-May-15 |
| 4157 | 3 | 4 | 5 | 6 | | VI-1 | Figf | 2277 | 17-May-15 | 4253 | 3 | 4 | 5 | 6 | | VI-1 | Gfi1b | 8328 | 23-May-15 |
| 4158 | 3 | 4 | 5 | 6 | | VI-1 | Fitm1 | 161247 | 4-May-15 | 4254 | 3 | 4 | 5 | 6 | | VI-1 | Gfpt2 | 9945 | 4-May-15 |
| 4159 | 3 | 4 | 5 | 6 | | VI-1 | Fjx1 | 24147 | 4-May-15 | 4255 | 3 | 4 | 5 | 6 | | VI-1 | Gfra2 | 2675 | 12-May-15 |
| 4160 | 3 | 4 | 5 | 6 | | VI-1 | Fkbp10 | 60681 | 4-May-15 | 4256 | 3 | 4 | 5 | 6 | | VI-1 | Ggh | 8836 | 12-May-15 |
| 4161 | 3 | 4 | 5 | 6 | | VI-1 | Fkbp11 | 51303 | 21-May-15 | 4257 | 3 | 4 | 5 | 6 | | VI-1 | Ggt1 | 2678 | 17-May-15 |
| 4162 | 3 | 4 | 5 | 6 | | VI-1 | Fkbp1b | 2281 | 4-May-15 | 4258 | 3 | 4 | 5 | 6 | | VI-1 | Ghrl | 51738 | 21-May-15 |
| 4163 | 3 | 4 | 5 | 6 | | VI-1 | Fkbp5 | 2289 | 17-May-15 | 4259 | 3 | 4 | 5 | 6 | | VI-1 | Gimap1 | 170575 | 4-May-15 |
| 4164 | 3 | 4 | 5 | 6 | | VI-1 | Flt1 | 2313 | 7-Jun-15 | 4260 | 3 | 4 | 5 | 6 | | VI-1 | Gimap3 | 474345 | 4-May-15 |
| 4165 | 3 | 4 | 5 | 6 | | VI-1 | Flnc | 2318 | 23-May-15 | 4261 | 3 | 4 | 5 | 6 | | VI-1 | Gimap4 | 55303 | 4-May-15 |
| 4166 | 3 | 4 | 5 | 6 | | VI-1 | Flt4 | 2324 | 23-May-15 | 4262 | 3 | 4 | 5 | 6 | | VI-1 | Gimap6 | 474344 | 4-May-15 |
| 4167 | 3 | 4 | 5 | 6 | | VI-1 | Fmnl1 | 752 | 14-May-15 | 4263 | 3 | 4 | 5 | 6 | | VI-1 | Gimap7 | 168537 | 4-May-15 |
| 4168 | 3 | 4 | 5 | 6 | | VI-1 | Fmo2 | 2327 | 12-May-15 | 4264 | 3 | 4 | 5 | 6 | | VI-1 | Gins1 | 9837 | 12-May-15 |
| 4169 | 3 | 4 | 5 | 6 | | VI-1 | Fmo3 | 2328 | 24-May-15 | 4265 | 3 | 4 | 5 | 6 | | VI-1 | Gins2 | 51659 | 4-May-15 |
| 4170 | 3 | 4 | 5 | 6 | | VI-1 | Fmo5 | 2330 | 4-May-15 | 4266 | 3 | 4 | 5 | 6 | | VI-1 | Gins3 | 64785 | 4-May-15 |
| 4171 | 3 | 4 | 5 | 6 | | VI-1 | Fn1 | 2335 | 24-May-15 | 4267 | 3 | 4 | 5 | 6 | | VI-1 | Gjb1 | 2705 | 23-May-15 |
| 4172 | 3 | 4 | 5 | 6 | | VI-1 | Fn3k | 64122 | 4-May-15 | 4268 | 3 | 4 | 5 | 6 | | VI-1 | Gjb3 | 2707 | 23-May-15 |
| 4173 | 3 | 4 | 5 | 6 | | VI-1 | Fn3krp | 79672 | 4-May-15 | 4269 | 3 | 4 | 5 | 6 | | VI-1 | Gjb4 | 127534 | 4-May-15 |
| 4174 | 3 | 4 | 5 | 6 | | VI-1 | Fndc1 | 84624 | 4-May-15 | 4270 | 3 | 4 | 5 | 6 | | VI-1 | Gla | 2717 | 7-Jun-15 |
| 4175 | 3 | 4 | 5 | 6 | | VI-1 | Fndc5 | 252995 | 17-May-15 | 4271 | 3 | 4 | 5 | 6 | | VI-1 | Glb1l2 | 89944 | 4-May-15 |
| 4176 | 3 | 4 | 5 | 6 | | VI-1 | Fndc9 | 408263 | 4-May-15 | 4272 | 3 | 4 | 5 | 6 | | VI-1 | Glb1l3 | 112937 | 4-May-15 |
| 4177 | 3 | 4 | 5 | 6 | | VI-1 | Fnip2 | 57600 | 4-May-15 | 4273 | 3 | 4 | 5 | 6 | | VI-1 | Gli1 | 2735 | 17-May-15 |
| 4178 | 3 | 4 | 5 | 6 | | VI-1 | Fntb | 2342 | 4-May-15 | 4274 | 3 | 4 | 5 | 6 | | VI-1 | Glipr1 | 11010 | 4-May-15 |
| 4179 | 3 | 4 | 5 | 6 | | VI-1 | Folr2 | 2350 | 12-May-15 | 4275 | 3 | 4 | 5 | 6 | | VI-1 | Glipr2 | 152007 | 4-May-15 |
| 4180 | 3 | 4 | 5 | 6 | | VI-1 | Fosb | 2354 | 12-May-15 | 4276 | 3 | 4 | 5 | 6 | | VI-1 | Glrb | 2743 | 4-May-15 |
| 4181 | 3 | 4 | 5 | 6 | | VI-1 | Fosl1 | 8061 | 17-May-15 | 4277 | 3 | 4 | 5 | 6 | | VI-1 | Glrp1 | | |
| 4182 | 3 | 4 | 5 | 6 | | VI-1 | Fosl2 | 2355 | 12-May-15 | 4278 | 3 | 4 | 5 | 6 | | VI-1 | Glrx5 | 51218 | 4-May-15 |
| 4183 | 3 | 4 | 5 | 6 | | VI-1 | Foxa1 | 3169 | 17-May-15 | 4279 | 3 | 4 | 5 | 6 | | VI-1 | Glul | 2752 | 4-May-15 |
| 4184 | 3 | 4 | 5 | 6 | | VI-1 | Foxc1 | 2296 | 4-May-15 | 4280 | 3 | 4 | 5 | 6 | | VI-1 | Gm10190 | | |
| 4185 | 3 | 4 | 5 | 6 | | VI-1 | Foxc2 | 2303 | 23-May-15 | 4281 | 3 | 4 | 5 | 6 | | VI-1 | Gm10267 | | |
| 4186 | 3 | 4 | 5 | 6 | | VI-1 | Foxd2os | | | 4282 | 3 | 4 | 5 | 6 | | VI-1 | Gm10453 | | |
| 4187 | 3 | 4 | 5 | 6 | | VI-1 | Foxs1 | 2307 | 4-May-15 | 4283 | 3 | 4 | 5 | 6 | | VI-1 | Gm10591 | | |
| 4188 | 3 | 4 | 5 | 6 | | VI-1 | Fpgs | 2356 | 12-May-15 | 4284 | 3 | 4 | 5 | 6 | | VI-1 | Gm10638 | | |
| 4189 | 3 | 4 | 5 | 6 | | VI-1 | Fpr1 | 2357 | 12-May-15 | 4285 | 3 | 4 | 5 | 6 | | VI-1 | Gm10872 | | |
| 4190 | 3 | 4 | 5 | 6 | | VI-1 | Fpr2 | 2358 | 4-May-15 | 4286 | 3 | 4 | 5 | 6 | | VI-1 | Gm11127 | | |
| 4191 | 3 | 4 | 5 | 6 | | VI-1 | Frmpd4 | 9758 | 4-May-15 | 4287 | 3 | 4 | 5 | 6 | | VI-1 | Gm11437 | | |
| 4192 | 3 | 4 | 5 | 6 | | VI-1 | Frzb | 2487 | 4-May-15 | 4288 | 3 | 4 | 5 | 6 | | VI-1 | Gm11627 | | |
| 4193 | 3 | 4 | 5 | 6 | | VI-1 | Fscn1 | 6624 | 24-May-15 | 4289 | 3 | 4 | 5 | 6 | | VI-1 | Gm11651 | | |
| 4194 | 3 | 4 | 5 | 6 | | VI-1 | Fstl1 | 11167 | 4-May-15 | 4290 | 3 | 4 | 5 | 6 | | VI-1 | Gm11837 | | |
| 4195 | 3 | 4 | 5 | 6 | | VI-1 | Fstl3 | 10272 | 4-May-15 | 4291 | 3 | 4 | 5 | 6 | | VI-1 | Gm11974 | | |
| 4196 | 3 | 4 | 5 | 6 | | VI-1 | Ftl1 | | | 4292 | 3 | 4 | 5 | 6 | | VI-1 | Gm12250 | | |
| 4197 | 3 | 4 | 5 | 6 | | VI-1 | Fut4 | 2526 | 12-May-15 | 4293 | 3 | 4 | 5 | 6 | | VI-1 | Gm13003 | | |
| 4198 | 3 | 4 | 5 | 6 | | VI-1 | Fut8 | 2530 | 17-May-15 | 4294 | 3 | 4 | 5 | 6 | | VI-1 | Gm13139 | | |
| 4199 | 3 | 4 | 5 | 6 | | VI-1 | Fv1 | | | 4295 | 3 | 4 | 5 | 6 | | VI-1 | Gm13152 | | |
| 4200 | 3 | 4 | 5 | 6 | | VI-1 | Fxyd1 | 5348 | 12-May-15 | 4296 | 3 | 4 | 5 | 6 | | VI-1 | Gm13154 | | |
| 4201 | 3 | 4 | 5 | 6 | | VI-1 | Fxyd3 | 5349 | 4-May-15 | 4297 | 3 | 4 | 5 | 6 | | VI-1 | Gm13212 | | |
| 4202 | 3 | 4 | 5 | 6 | | VI-1 | Fxyd5 | 53827 | 4-May-15 | 4298 | 3 | 4 | 5 | 6 | | VI-1 | Gm13247 | | |
| 4203 | 3 | 4 | 5 | 6 | | VI-1 | Fxyd6 | 53826 | 4-May-15 | 4299 | 3 | 4 | 5 | 6 | | VI-1 | Gm13251 | | |
| 4204 | 3 | 4 | 5 | 6 | | VI-1 | Fyb | 2533 | 12-May-15 | 4300 | 3 | 4 | 5 | 6 | | VI-1 | Gm13304 | | |
| 4205 | 3 | 4 | 5 | 6 | | VI-1 | Fzd1 | 8321 | 4-May-15 | 4301 | 3 | 4 | 5 | 6 | | VI-1 | Gm13363 | | |
| 4206 | 3 | 4 | 5 | 6 | | VI-1 | Fzd10 | 11211 | 4-May-15 | 4302 | 3 | 4 | 5 | 6 | | VI-1 | Gm13710 | | |
| 4207 | 3 | 4 | 5 | 6 | | VI-1 | Fzd2 | 2535 | 4-May-15 | 4303 | 3 | 4 | 5 | 6 | | VI-1 | Gm13889 | | |
| 4208 | 3 | 4 | 5 | 6 | | VI-1 | Fzd4 | 8322 | 23-May-15 | 4304 | 3 | 4 | 5 | 6 | | VI-1 | Gm14288 | | |
| 4209 | 3 | 4 | 5 | 6 | | VI-1 | Fzr1 | 51343 | 4-May-15 | 4305 | 3 | 4 | 5 | 6 | | VI-1 | Gm14403 | | |
| 4210 | 3 | 4 | 5 | 6 | | VI-1 | G530011O06Rik | | | 4306 | 3 | 4 | 5 | 6 | | VI-1 | Gm14434 | | |
| 4211 | 3 | 4 | 5 | 6 | | VI-1 | Gabra4 | 2557 | 4-May-15 | 4307 | 3 | 4 | 5 | 6 | | VI-1 | Gm14436 | | |
| 4212 | 3 | 4 | 5 | 6 | | VI-1 | Gabrb1 | 2560 | 12-May-15 | 4308 | 3 | 4 | 5 | 6 | | VI-1 | Gm14446 | | |
| 4213 | 3 | 4 | 5 | 6 | | VI-1 | Gabrp | 2568 | 4-May-15 | 4309 | 3 | 4 | 5 | 6 | | VI-1 | Gm14548 | | |
| 4214 | 3 | 4 | 5 | 6 | | VI-1 | Gadd45a | 1647 | 24-May-15 | 4310 | 3 | 4 | 5 | 6 | | VI-1 | Gm15441 | | |
| 4215 | 3 | 4 | 5 | 6 | | VI-1 | Gadd45b | 4616 | 4-May-15 | 4311 | 3 | 4 | 5 | 6 | | VI-1 | Gm15612 | | |
| 4216 | 3 | 4 | 5 | 6 | | VI-1 | Gadd45g | 10912 | 4-May-15 | 4312 | 3 | 4 | 5 | 6 | | VI-1 | Gm15698 | | |
| 4217 | 3 | 4 | 5 | 6 | | VI-1 | Gal | 51083 | 17-May-15 | 4313 | 3 | 4 | 5 | 6 | | VI-1 | Gm15706 | | |
| 4218 | 3 | 4 | 5 | 6 | | VI-1 | Gale | 2582 | 23-May-15 | 4314 | 3 | 4 | 5 | 6 | | VI-1 | Gm15708 | | |
| 4219 | 3 | 4 | 5 | 6 | | VI-1 | Galns | 2588 | 23-May-15 | 4315 | 3 | 4 | 5 | 6 | | VI-1 | Gm15800 | | |
| 4220 | 3 | 4 | 5 | 6 | | VI-1 | Galnt15 | 117248 | 7-Jun-15 | 4316 | 3 | 4 | 5 | 6 | | VI-1 | Gm15816 | | |
| 4221 | 3 | 4 | 5 | 6 | | VI-1 | Galnt16 | 57452 | 4-May-15 | 4317 | 3 | 4 | 5 | 6 | | VI-1 | Gm15915 | | |
| 4222 | 3 | 4 | 5 | 6 | | VI-1 | Galnt7 | 51809 | 7-Jun-15 | 4318 | 3 | 4 | 5 | 6 | | VI-1 | Gm15987 | | |
| 4223 | 3 | 4 | 5 | 6 | | VI-1 | Gamt | 2593 | 23-May-15 | 4319 | 3 | 4 | 5 | 6 | | VI-1 | Gm16617 | | |
| 4224 | 3 | 4 | 5 | 6 | | VI-1 | Gapt | 202309 | 12-May-15 | 4320 | 3 | 4 | 5 | 6 | | VI-1 | Gm1673 | | |
| 4225 | 3 | 4 | 5 | 6 | | VI-1 | Garem | 64762 | 4-May-15 | 4321 | 3 | 4 | 5 | 6 | | VI-1 | Gm16793 | | |
| 4226 | 3 | 4 | 5 | 6 | | VI-1 | Gas2l1 | 10634 | 4-May-15 | 4322 | 3 | 4 | 5 | 6 | | VI-1 | Gm16998 | | |
| 4227 | 3 | 4 | 5 | 6 | | VI-1 | Gas2l3 | 283431 | 12-May-15 | 4323 | 3 | 4 | 5 | 6 | | VI-1 | Gm17252 | | |
| 4228 | 3 | 4 | 5 | 6 | | VI-1 | Gas5 | 60674 | 17-May-15 | 4324 | 3 | 4 | 5 | 6 | | VI-1 | Gm17296 | | |
| 4229 | 3 | 4 | 5 | 6 | | VI-1 | Gas7 | 8522 | 4-May-15 | 4325 | 3 | 4 | 5 | 6 | | VI-1 | Gm17365 | | |
| 4230 | 3 | 4 | 5 | 6 | | VI-1 | Gata1 | 2623 | 23-May-15 | 4326 | 3 | 4 | 5 | 6 | | VI-1 | Gm17757 | | |
| 4231 | 3 | 4 | 5 | 6 | | VI-1 | Gata3 | 2625 | 17-May-15 | 4327 | 3 | 4 | 5 | 6 | | VI-1 | Gm1966 | | |
| 4232 | 3 | 4 | 5 | 6 | | VI-1 | Gatm | 2628 | 23-May-15 | 4328 | 3 | 4 | 5 | 6 | | VI-1 | Gm1976 | | |
| 4233 | 3 | 4 | 5 | 6 | | VI-1 | Gbp2 | 2634 | 4-May-15 | 4329 | 3 | 4 | 5 | 6 | | VI-1 | Gm20257 | | |
| 4234 | 3 | 4 | 5 | 6 | | VI-1 | Gbp3 | 2635 | 4-May-15 | 4330 | 3 | 4 | 5 | 6 | | VI-1 | Gm20319 | | |
| 4235 | 3 | 4 | 5 | 6 | | VI-1 | Gbp5 | 115362 | 4-May-15 | 4331 | 3 | 4 | 5 | 6 | | VI-1 | Gm20554 | | |
| 4236 | 3 | 4 | 5 | 6 | | VI-1 | Gbp7 | 388646 | 4-May-15 | 4332 | 3 | 4 | 5 | 6 | | VI-1 | Gm20604 | | |
| 4237 | 3 | 4 | 5 | 6 | | VI-1 | Gch1 | 2643 | 23-May-15 | 4333 | 3 | 4 | 5 | 6 | | VI-1 | Gm20743 | | |
| 4238 | 3 | 4 | 5 | 6 | | VI-1 | Gck | 2645 | 7-Jun-15 | 4334 | 3 | 4 | 5 | 6 | | VI-1 | Gm2848 | | |
| 4239 | 3 | 4 | 5 | 6 | | VI-1 | Gclc | 2729 | 12-May-15 | 4335 | 3 | 4 | 5 | 6 | | VI-1 | Gm2a | 2760 | 21-May-15 |
| 4240 | 3 | 4 | 5 | 6 | | VI-1 | Gclm | 2730 | 21-May-15 | 4336 | 3 | 4 | 5 | 6 | | VI-1 | Gm3893 | | |
| 4241 | 3 | 4 | 5 | 6 | | VI-1 | Gcnt1 | 2650 | 4-May-15 | 4337 | 3 | 4 | 5 | 6 | | VI-1 | Gm4070 | | |
| 4242 | 3 | 4 | 5 | 6 | | VI-1 | Gcnt2 | 2651 | 23-May-15 | 4338 | 3 | 4 | 5 | 6 | | VI-1 | Gm4788 | | |
| 4243 | 3 | 4 | 5 | 6 | | VI-1 | Gcsam | 257144 | 4-May-15 | 4339 | 3 | 4 | 5 | 6 | | VI-1 | Gm4956 | | |
| 4244 | 3 | 4 | 5 | 6 | | VI-1 | Gda | 9615 | 7-Jun-15 | 4340 | 3 | 4 | 5 | 6 | | VI-1 | Gm5088 | | |

Fig. 30 - 24

| | | | | | | | | | | | | | | | | | | |
|---|---|---|---|---|---|---|---|---|---|---|---|---|---|---|---|---|---|---|
| 4341 | 3 | 4 | 5 | 6 | | VI-1 | Gm5105 | | | 4437 | 3 | 4 | 5 | 6 | | VI-1 | Gstm7 | | |
| 4342 | 3 | 4 | 5 | 6 | | VI-1 | Gm5126 | | | 4438 | 3 | 4 | 5 | 6 | | VI-1 | Gsto1 | 9446 | 4-May-15 |
| 4343 | 3 | 4 | 5 | 6 | | VI-1 | Gm5150 | | | 4439 | 3 | 4 | 5 | 6 | | VI-1 | Gstt3 | | |
| 4344 | 3 | 4 | 5 | 6 | | VI-1 | Gm525 | | | 4440 | 3 | 4 | 5 | 6 | | VI-1 | Gusb | 2990 | 4-May-15 |
| 4345 | 3 | 4 | 5 | 6 | | VI-1 | Gm5416 | | | 4441 | 3 | 4 | 5 | 6 | | VI-1 | Gxylt2 | 727936 | 4-May-15 |
| 4346 | 3 | 4 | 5 | 6 | | VI-1 | Gm5424 | | | 4442 | 3 | 4 | 5 | 6 | | VI-1 | Gyltl1b | 120071 | 23-May-15 |
| 4347 | 3 | 4 | 5 | 6 | | VI-1 | Gm5512 | | | 4443 | 3 | 4 | 5 | 6 | | VI-1 | Gypa | 2993 | 21-May-15 |
| 4348 | 3 | 4 | 5 | 6 | | VI-1 | Gm5544 | | | 4444 | 3 | 4 | 5 | 6 | | VI-1 | Gypc | 2995 | 12-May-15 |
| 4349 | 3 | 4 | 5 | 6 | | VI-1 | Gm5627 | | | 4445 | 3 | 4 | 5 | 6 | | VI-1 | Gys2 | 2998 | 4-May-15 |
| 4350 | 3 | 4 | 5 | 6 | | VI-1 | Gm5741 | | | 4446 | 3 | 4 | 5 | 6 | | VI-1 | Gzmc | | |
| 4351 | 3 | 4 | 5 | 6 | | VI-1 | Gm5820 | | | 4447 | 3 | 4 | 5 | 6 | | VI-1 | H19 | 283120 | 23-May-15 |
| 4352 | 3 | 4 | 5 | 6 | | VI-1 | Gm6307 | | | 4448 | 3 | 4 | 5 | 6 | | VI-1 | H1fx | 8971 | 4-May-15 |
| 4353 | 3 | 4 | 5 | 6 | | VI-1 | Gm6644 | | | 4449 | 3 | 4 | 5 | 6 | | VI-1 | H2-Aa | | |
| 4354 | 3 | 4 | 5 | 6 | | VI-1 | Gm6654 | | | 4450 | 3 | 4 | 5 | 6 | | VI-1 | H2-Ab1 | | |
| 4355 | 3 | 4 | 5 | 6 | | VI-1 | Gm6682 | | | 4451 | 3 | 4 | 5 | 6 | | VI-1 | H2afx | 3014 | 4-May-15 |
| 4356 | 3 | 4 | 5 | 6 | | VI-1 | Gm6904 | | | 4452 | 3 | 4 | 5 | 6 | | VI-1 | H2afz | 3015 | 12-May-15 |
| 4357 | 3 | 4 | 5 | 6 | | VI-1 | Gm7030 | | | 4453 | 3 | 4 | 5 | 6 | | VI-1 | H2-Bl | | |
| 4358 | 3 | 4 | 5 | 6 | | VI-1 | Gm7609 | | | 4454 | 3 | 4 | 5 | 6 | | VI-1 | H2-D1 | | |
| 4359 | 3 | 4 | 5 | 6 | | VI-1 | Gm7694 | | | 4455 | 3 | 4 | 5 | 6 | | VI-1 | H2-DMa | | |
| 4360 | 3 | 4 | 5 | 6 | | VI-1 | Gm773 | | | 4456 | 3 | 4 | 5 | 6 | | VI-1 | H2-DMb1 | | |
| 4361 | 3 | 4 | 5 | 6 | | VI-1 | Gm8221 | | | 4457 | 3 | 4 | 5 | 6 | | VI-1 | H2-DMb2 | | |
| 4362 | 3 | 4 | 5 | 6 | | VI-1 | Gm8369 | | | 4458 | 3 | 4 | 5 | 6 | | VI-1 | H2-K1 | | |
| 4363 | 3 | 4 | 5 | 6 | | VI-1 | Gm8439 | | | 4459 | 3 | 4 | 5 | 6 | | VI-1 | H2-K2 | | |
| 4364 | 3 | 4 | 5 | 6 | | VI-1 | Gm867 | | | 4460 | 3 | 4 | 5 | 6 | | VI-1 | H2-M3 | | |
| 4365 | 3 | 4 | 5 | 6 | | VI-1 | Gm8801 | | | 4461 | 3 | 4 | 5 | 6 | | VI-1 | H2-Ob | | |
| 4366 | 3 | 4 | 5 | 6 | | VI-1 | Gm8898 | | | 4462 | 3 | 4 | 5 | 6 | | VI-1 | H2-Q1 | | |
| 4367 | 3 | 4 | 5 | 6 | | VI-1 | Gm8909 | | | 4463 | 3 | 4 | 5 | 6 | | VI-1 | H2-Q10 | | |
| 4368 | 3 | 4 | 5 | 6 | | VI-1 | Gm8979 | | | 4464 | 3 | 4 | 5 | 6 | | VI-1 | H2-Q2 | | |
| 4369 | 3 | 4 | 5 | 6 | | VI-1 | Gm8989 | | | 4465 | 3 | 4 | 5 | 6 | | VI-1 | H2-Q4 | | |
| 4370 | 3 | 4 | 5 | 6 | | VI-1 | Gm9733 | | | 4466 | 3 | 4 | 5 | 6 | | VI-1 | H2-Q5 | | |
| 4371 | 3 | 4 | 5 | 6 | | VI-1 | Gm9855 | | | 4467 | 3 | 4 | 5 | 6 | | VI-1 | H2-Q6 | | |
| 4372 | 3 | 4 | 5 | 6 | | VI-1 | Gm9895 | | | 4468 | 3 | 4 | 5 | 6 | | VI-1 | H2-Q7 | | |
| 4373 | 3 | 4 | 5 | 6 | | VI-1 | Gmds | 2762 | 4-May-15 | 4469 | 3 | 4 | 5 | 6 | | VI-1 | H2-Q8 | | |
| 4374 | 3 | 4 | 5 | 6 | | VI-1 | Gmfg | 9535 | 12-May-15 | 4470 | 3 | 4 | 5 | 6 | | VI-1 | H2-Q9 | | |
| 4375 | 3 | 4 | 5 | 6 | | VI-1 | Gmnn | 51053 | 24-May-15 | 4471 | 3 | 4 | 5 | 6 | | VI-1 | H2-T22 | | |
| 4376 | 3 | 4 | 5 | 6 | | VI-1 | Gna14 | 9630 | 4-May-15 | 4472 | 3 | 4 | 5 | 6 | | VI-1 | H2-T9 | | |
| 4377 | 3 | 4 | 5 | 6 | | VI-1 | Gng8 | 94235 | #NAME? | 4473 | 3 | 4 | 5 | 6 | | VI-1 | H60b | | |
| 4378 | 3 | 4 | 5 | 6 | | VI-1 | Gngt2 | 2793 | 4-May-15 | 4474 | 3 | 4 | 5 | 6 | | VI-1 | Hagh | 3029 | 12-May-15 |
| 4379 | 3 | 4 | 5 | 6 | | VI-1 | Gnl3 | 26354 | 4-May-15 | 4475 | 3 | 4 | 5 | 6 | | VI-1 | Hamp | 57817 | 24-May-15 |
| 4380 | 3 | 4 | 5 | 6 | | VI-1 | Gnrh1 | 2796 | 31-May-15 | 4476 | 3 | 4 | 5 | 6 | | VI-1 | Hap1 | 9001 | 7-Jun-15 |
| 4381 | 3 | 4 | 5 | 6 | | VI-1 | Golr1a | 127845 | 4-May-15 | 4477 | 3 | 4 | 5 | 6 | | VI-1 | Has1 | 3036 | 4-May-15 |
| 4382 | 3 | 4 | 5 | 6 | | VI-1 | Got1 | 2805 | 7-Jun-15 | 4478 | 3 | 4 | 5 | 6 | | VI-1 | Haus3 | 79441 | 12-May-15 |
| 4383 | 3 | 4 | 5 | 6 | | VI-1 | Got2 | 2806 | 4-May-15 | 4479 | 3 | 4 | 5 | 6 | | VI-1 | Havcr2 | 84868 | 24-May-15 |
| 4384 | 3 | 4 | 5 | 6 | | VI-1 | Gp1bb | 2812 | 12-May-15 | 4480 | 3 | 4 | 5 | 6 | | VI-1 | Hax1 | 10456 | 4-May-15 |
| 4385 | 3 | 4 | 5 | 6 | | VI-1 | Gp49a | | | 4481 | 3 | 4 | 5 | 6 | | VI-1 | Hbegf | 1839 | 12-May-15 |
| 4386 | 3 | 4 | 5 | 6 | | VI-1 | Gp9 | 2815 | 12-May-15 | 4482 | 3 | 4 | 5 | 6 | | VI-1 | Hbq1a | | |
| 4387 | 3 | 4 | 5 | 6 | | VI-1 | Gpam | 57678 | 12-May-15 | 4483 | 3 | 4 | 5 | 6 | | VI-1 | Hbq1b | | |
| 4388 | 3 | 4 | 5 | 6 | | VI-1 | Gpc3 | 2719 | 23-May-15 | 4484 | 3 | 4 | 5 | 6 | | VI-1 | Hc | 727 | 7-Jun-15 |
| 4389 | 3 | 4 | 5 | 6 | | VI-1 | Gpc4 | 2239 | 23-May-15 | 4485 | 3 | 4 | 5 | 6 | | VI-1 | Hcar1 | 27198 | 21-May-15 |
| 4390 | 3 | 4 | 5 | 6 | | VI-1 | Gpc6 | 10082 | 4-May-15 | 4486 | 3 | 4 | 5 | 6 | | VI-1 | Hcar2 | 338442 | 4-May-15 |
| 4391 | 3 | 4 | 5 | 6 | | VI-1 | Gpd1 | 2819 | 4-May-15 | 4487 | 3 | 4 | 5 | 6 | | VI-1 | Hck | 3055 | 12-May-15 |
| 4392 | 3 | 4 | 5 | 6 | | VI-1 | Gpihbp1 | 338328 | 4-May-15 | 4488 | 3 | 4 | 5 | 6 | | VI-1 | Hcls1 | 3059 | 12-May-15 |
| 4393 | 3 | 4 | 5 | 6 | | VI-1 | Gpld1 | 2822 | 4-May-15 | 4489 | 3 | 4 | 5 | 6 | | VI-1 | Hcst | 10870 | 7-Jun-15 |
| 4394 | 3 | 4 | 5 | 6 | | VI-1 | Gpm6b | 2824 | 12-May-15 | 4490 | 3 | 4 | 5 | 6 | | VI-1 | Hdac11 | 79885 | 4-May-15 |
| 4395 | 3 | 4 | 5 | 6 | | VI-1 | Gpr110 | 266977 | 4-May-15 | 4491 | 3 | 4 | 5 | 6 | | VI-1 | Hdac6 | 10013 | 10-May-15 |
| 4396 | 3 | 4 | 5 | 6 | | VI-1 | Gpr132 | 29933 | 4-May-15 | 4492 | 3 | 4 | 5 | 6 | | VI-1 | Hdac7 | 51564 | 7-Jun-15 |
| 4397 | 3 | 4 | 5 | 6 | | VI-1 | Gpr133 | 283383 | 4-May-15 | 4493 | 3 | 4 | 5 | 6 | | VI-1 | Hdac9 | 9734 | 4-May-15 |
| 4398 | 3 | 4 | 5 | 6 | | VI-1 | Gpr137b | 7107 | 4-May-15 | 4494 | 3 | 4 | 5 | 6 | | VI-1 | Hebp2 | 23593 | 4-May-15 |
| 4399 | 3 | 4 | 5 | 6 | | VI-1 | Gpr137b-ps | | | 4495 | 3 | 4 | 5 | 6 | | VI-1 | Hells | 3070 | 4-May-15 |
| 4400 | 3 | 4 | 5 | 6 | | VI-1 | Gpr15 | 2838 | 4-May-15 | 4496 | 3 | 4 | 5 | 6 | | VI-1 | Hemgn | 55363 | 4-May-15 |
| 4401 | 3 | 4 | 5 | 6 | | VI-1 | Gpr171 | 29909 | 4-May-15 | 4497 | 3 | 4 | 5 | 6 | | VI-1 | Hepacam | 220296 | 23-May-15 |
| 4402 | 3 | 4 | 5 | 6 | | VI-1 | Gpr176 | 11245 | 4-May-15 | 4498 | 3 | 4 | 5 | 6 | | VI-1 | Herpud1 | 9709 | 12-May-15 |
| 4403 | 3 | 4 | 5 | 6 | | VI-1 | Gpr18 | 2841 | 4-May-15 | 4499 | 3 | 4 | 5 | 6 | | VI-1 | Hexb | 3074 | 12-May-15 |
| 4404 | 3 | 4 | 5 | 6 | | VI-1 | Gpr182 | 11318 | 4-May-15 | 4500 | 3 | 4 | 5 | 6 | | VI-1 | Hfe2 | 148738 | 23-May-15 |
| 4405 | 3 | 4 | 5 | 6 | | VI-1 | Gpr55 | 9290 | 4-May-15 | 4501 | 3 | 4 | 5 | 6 | | VI-1 | Hgf | 3082 | 7-Jun-15 |
| 4406 | 3 | 4 | 5 | 6 | | VI-1 | Gpr56 | 9289 | 23-May-15 | 4502 | 3 | 4 | 5 | 6 | | VI-1 | Hgs | 9146 | 12-May-15 |
| 4407 | 3 | 4 | 5 | 6 | | VI-1 | Gpr64 | 10149 | 4-May-15 | 4503 | 3 | 4 | 5 | 6 | | VI-1 | Hhex | 3087 | 12-May-15 |
| 4408 | 3 | 4 | 5 | 6 | | VI-1 | Gpr65 | 8477 | 4-May-15 | 4504 | 3 | 4 | 5 | 6 | | VI-1 | Hhip | 64399 | 12-May-15 |
| 4409 | 3 | 4 | 5 | 6 | | VI-1 | Gpr97 | 222487 | 4-May-15 | 4505 | 3 | 4 | 5 | 6 | | VI-1 | Hhipl1 | 84439 | 14-May-15 |
| 4410 | 3 | 4 | 5 | 6 | | VI-1 | Gprc5c | 55890 | 12-May-15 | 4506 | 3 | 4 | 5 | 6 | | VI-1 | Hilpda | 29923 | 12-May-15 |
| 4411 | 3 | 4 | 5 | 6 | | VI-1 | Gprin3 | 285513 | 14-May-15 | 4507 | 3 | 4 | 5 | 6 | | VI-1 | Hist1h1c | 3006 | 12-May-15 |
| 4412 | 3 | 4 | 5 | 6 | | VI-1 | Gpsm2 | 29899 | 4-May-15 | 4508 | 3 | 4 | 5 | 6 | | VI-1 | Hist1h1d | 3007 | 4-May-15 |
| 4413 | 3 | 4 | 5 | 6 | | VI-1 | Gpsm3 | 63940 | 4-May-15 | 4509 | 3 | 4 | 5 | 6 | | VI-1 | Hist1h1e | 3008 | 12-May-15 |
| 4414 | 3 | 4 | 5 | 6 | | VI-1 | Gpt | 2875 | 7-Jun-15 | 4510 | 3 | 4 | 5 | 6 | | VI-1 | Hist1h2ac | 8334 | 4-May-15 |
| 4415 | 3 | 4 | 5 | 6 | | VI-1 | Gpx1 | 2876 | 12-May-15 | 4511 | 3 | 4 | 5 | 6 | | VI-1 | Hist1h2ag | 8969 | 4-May-15 |
| 4416 | 3 | 4 | 5 | 6 | | VI-1 | Gpx2 | 2877 | 4-May-15 | 4512 | 3 | 4 | 5 | 6 | | VI-1 | Hist1h2ao | | |
| 4417 | 3 | 4 | 5 | 6 | | VI-1 | Gpx2-ps1 | | | 4513 | 3 | 4 | 5 | 6 | | VI-1 | Hist1h2ba | 255626 | 4-May-15 |
| 4418 | 3 | 4 | 5 | 6 | | VI-1 | Gpx3 | 2878 | 12-May-15 | 4514 | 3 | 4 | 5 | 6 | | VI-1 | Hist1h2bg | 8339 | 4-May-15 |
| 4419 | 3 | 4 | 5 | 6 | | VI-1 | Gpx6 | 257202 | 12-May-15 | 4515 | 3 | 4 | 5 | 6 | | VI-1 | Hist1h2bl | 8340 | 4-May-15 |
| 4420 | 3 | 4 | 5 | 6 | | VI-1 | Gramd1b | 57476 | 21-May-15 | 4516 | 3 | 4 | 5 | 6 | | VI-1 | Hist1h3g | 8355 | 4-May-15 |
| 4421 | 3 | 4 | 5 | 6 | | VI-1 | Gramd4 | 23151 | 14-May-15 | 4517 | 3 | 4 | 5 | 6 | | VI-1 | Hist1h4c | 8364 | 4-May-15 |
| 4422 | 3 | 4 | 5 | 6 | | VI-1 | Grb14 | 2888 | 17-May-15 | 4518 | 3 | 4 | 5 | 6 | | VI-1 | Hist1h4f | 8361 | 4-May-15 |
| 4423 | 3 | 4 | 5 | 6 | | VI-1 | Greb1 | 9687 | 18-May-15 | 4519 | 3 | 4 | 5 | 6 | | VI-1 | Hist1h4j | 8363 | 4-May-15 |
| 4424 | 3 | 4 | 5 | 6 | | VI-1 | Grem1 | 26585 | 12-May-15 | 4520 | 3 | 4 | 5 | 6 | | VI-1 | Hist1h4k | 8362 | 4-May-15 |
| 4425 | 3 | 4 | 5 | 6 | | VI-1 | Grem2 | 64388 | 4-May-15 | 4521 | 3 | 4 | 5 | 6 | | VI-1 | Hist1h4m | | |
| 4426 | 3 | 4 | 5 | 6 | | VI-1 | Gria3 | 2892 | 12-May-15 | 4522 | 3 | 4 | 5 | 6 | | VI-1 | Hist2h2aa2 | | |
| 4427 | 3 | 4 | 5 | 6 | | VI-1 | Grin2c | 2905 | 4-May-15 | 4523 | 3 | 4 | 5 | 6 | | VI-1 | Hist2h2ab | 317772 | 4-May-15 |
| 4428 | 3 | 4 | 5 | 6 | | VI-1 | Grn | 2896 | 23-May-15 | 4524 | 3 | 4 | 5 | 6 | | VI-1 | Hist2h2bb | 338391 | 4-May-15 |
| 4429 | 3 | 4 | 5 | 6 | | VI-1 | Grp | 2922 | 17-May-15 | 4525 | 3 | 4 | 5 | 6 | | VI-1 | Hist2h3b | | |
| 4430 | 3 | 4 | 5 | 6 | | VI-1 | Gsap | 54103 | 4-May-15 | 4526 | 3 | 4 | 5 | 6 | | VI-1 | Hist2h3c1 | | |
| 4431 | 3 | 4 | 5 | 6 | | VI-1 | Gsdmc3 | | | 4527 | 3 | 4 | 5 | 6 | | VI-1 | Hist2h4 | 8370 | 4-May-15 |
| 4432 | 3 | 4 | 5 | 6 | | VI-1 | Gsg2 | 83903 | 12-May-15 | 4528 | 3 | 4 | 5 | 6 | | VI-1 | Hist3h2ba | 337872 | 4-May-15 |
| 4433 | 3 | 4 | 5 | 6 | | VI-1 | Gspt2 | 23708 | 21-May-15 | 4529 | 3 | 4 | 5 | 6 | | VI-1 | Hist3h2bb-ps | | |
| 4434 | 3 | 4 | 5 | 6 | | VI-1 | Gsta3 | 2940 | 12-May-15 | 4530 | 3 | 4 | 5 | 6 | | VI-1 | Hist1h4 | 121504 | 12-May-15 |
| 4435 | 3 | 4 | 5 | 6 | | VI-1 | Gstm5 | 2949 | 4-May-15 | 4531 | 3 | 4 | 5 | 6 | | VI-1 | Hk3 | 3101 | 7-Jun-15 |
| 4436 | 3 | 4 | 5 | 6 | | VI-1 | Gstm6 | | | 4532 | 3 | 4 | 5 | 6 | | VI-1 | Hmbs | 3145 | 23-May-15 |

Fig. 30 - 25

| | | | | | | | | | |
|---|---|---|---|---|---|---|---|---|---|
| 4533 | 3 | 4 | 5 | 6 | | VI-1 | Hmga1-rs1 | | |
| 4534 | 3 | 4 | 5 | 6 | | VI-1 | Hmga2-ps1 | | |
| 4535 | 3 | 4 | 5 | 6 | | VI-1 | Hmgb1-rs17 | | |
| 4536 | 3 | 4 | 5 | 6 | | VI-1 | Hmgb3 | 3149 | 12-May-15 |
| 4537 | 3 | 4 | 5 | 6 | | VI-1 | Hmgcs1 | 3157 | 4-May-15 |
| 4538 | 3 | 4 | 5 | 6 | | VI-1 | Hmgn2 | 3151 | 4-May-15 |
| 4539 | 3 | 4 | 5 | 6 | | VI-1 | Hmgn3 | 9324 | 4-May-15 |
| 4540 | 3 | 4 | 5 | 6 | | VI-1 | Hmha1 | 23526 | 4-May-15 |
| 4541 | 3 | 4 | 5 | 6 | | VI-1 | Hmox1 | 3162 | 17-May-15 |
| 4542 | 3 | 4 | 5 | 6 | | VI-1 | Hook1 | 51361 | 4-May-15 |
| 4543 | 3 | 4 | 5 | 6 | | VI-1 | Hoxb6 | 3216 | 4-May-15 |
| 4544 | 3 | 4 | 5 | 6 | | VI-1 | Hoxb7 | 3217 | 4-May-15 |
| 4545 | 3 | 4 | 5 | 6 | | VI-1 | Hoxb8 | 3218 | 4-May-15 |
| 4546 | 3 | 4 | 5 | 6 | | VI-1 | Hoxd3 | 3232 | 12-May-15 |
| 4547 | 3 | 4 | 5 | 6 | | VI-1 | Hoxd4 | 3233 | 12-May-15 |
| 4548 | 3 | 4 | 5 | 6 | | VI-1 | Hoxd8 | 3234 | 12-May-15 |
| 4549 | 3 | 4 | 5 | 6 | | VI-1 | Hoxd9 | 3235 | 4-May-15 |
| 4550 | 3 | 4 | 5 | 6 | | VI-1 | Hpdl | 84842 | 7-Jun-15 |
| 4551 | 3 | 4 | 5 | 6 | | VI-1 | Hpgd | 3248 | 17-May-15 |
| 4552 | 3 | 4 | 5 | 6 | | VI-1 | Hpgds | 27306 | 4-May-15 |
| 4553 | 3 | 4 | 5 | 6 | | VI-1 | Hps1 | 3257 | 23-May-15 |
| 4554 | 3 | 4 | 5 | 6 | | VI-1 | Hpse | 10855 | 24-May-15 |
| 4555 | 3 | 4 | 5 | 6 | | VI-1 | Hr | 55806 | 12-May-15 |
| 4556 | 3 | 4 | 5 | 6 | | VI-1 | Hrc | 3270 | 12-May-15 |
| 4557 | 3 | 4 | 5 | 6 | | VI-1 | Hs3st1 | 9957 | 4-May-15 |
| 4558 | 3 | 4 | 5 | 6 | | VI-1 | Hs3st3b1 | 9953 | 4-May-15 |
| 4559 | 3 | 4 | 5 | 6 | | VI-1 | Hs3st6 | 64711 | 4-May-15 |
| 4560 | 3 | 4 | 5 | 6 | | VI-1 | Hsd17b13 | 345275 | 4-May-15 |
| 4561 | 3 | 4 | 5 | 6 | | VI-1 | Hsh2d | 84941 | 4-May-15 |
| 4562 | 3 | 4 | 5 | 6 | | VI-1 | Hsp90aa1 | 3320 | 17-May-15 |
| 4563 | 3 | 4 | 5 | 6 | | VI-1 | Hspa1l | 3305 | 12-May-15 |
| 4564 | 3 | 4 | 5 | 6 | | VI-1 | Hspb1 | 3315 | 23-May-15 |
| 4565 | 3 | 4 | 5 | 6 | | VI-1 | Hspb7 | 27129 | 4-May-15 |
| 4566 | 3 | 4 | 5 | 6 | | VI-1 | Htr2b | 3357 | 12-May-15 |
| 4567 | 3 | 4 | 5 | 6 | | VI-1 | Htra3 | 94031 | 4-May-15 |
| 4568 | 3 | 4 | 5 | 6 | | VI-1 | Hunk | 30811 | 4-May-15 |
| 4569 | 3 | 4 | 5 | 6 | | VI-1 | Hvcn1 | 84329 | 3-May-15 |
| 4570 | 3 | 4 | 5 | 6 | | VI-1 | Hvsl2 | 219844 | 4-May-15 |
| 4571 | 3 | 4 | 5 | 6 | | VI-1 | I830012O16Rik | | |
| 4572 | 3 | 4 | 5 | 6 | | VI-1 | Iapp | 3375 | 17-May-15 |
| 4573 | 3 | 4 | 5 | 6 | | VI-1 | Ibsp7 | 200205 | 4-May-15 |
| 4574 | 3 | 4 | 5 | 6 | | VI-1 | Ibsp | 3381 | 12-May-15 |
| 4575 | 3 | 4 | 5 | 6 | | VI-1 | Icam1 | 3383 | 17-May-15 |
| 4576 | 3 | 4 | 5 | 6 | | VI-1 | Icam4 | 3386 | 12-May-15 |
| 4577 | 3 | 4 | 5 | 6 | | VI-1 | Icos1 | 23308 | 17-May-15 |
| 4578 | 3 | 4 | 5 | 6 | | VI-1 | Idi1 | 3422 | 21-May-15 |
| 4579 | 3 | 4 | 5 | 6 | | VI-1 | Ido2 | 169355 | 4-May-15 |
| 4580 | 3 | 4 | 5 | 6 | | VI-1 | Ier2 | 9592 | 21-May-15 |
| 4581 | 3 | 4 | 5 | 6 | | VI-1 | Ier3 | 8870 | 21-May-15 |
| 4582 | 3 | 4 | 5 | 6 | | VI-1 | Ier5 | 51278 | 12-May-15 |
| 4583 | 3 | 4 | 5 | 6 | | VI-1 | Ifi202b | | |
| 4584 | 3 | 4 | 5 | 6 | | VI-1 | Ifi203 | | |
| 4585 | 3 | 4 | 5 | 6 | | VI-1 | Ifi204 | | |
| 4586 | 3 | 4 | 5 | 6 | | VI-1 | Ifi27 | 3429 | 17-May-15 |
| 4587 | 3 | 4 | 5 | 6 | | VI-1 | Ifi27l2b | | |
| 4588 | 3 | 4 | 5 | 6 | | VI-1 | Ifi30 | 10437 | 4-May-15 |
| 4589 | 3 | 4 | 5 | 6 | | VI-1 | Ifi44 | 10561 | 4-May-15 |
| 4590 | 3 | 4 | 5 | 6 | | VI-1 | Ifi44l | 10964 | 4-May-15 |
| 4591 | 3 | 4 | 5 | 6 | | VI-1 | Ifi47 | | |
| 4592 | 3 | 4 | 5 | 6 | | VI-1 | Ifit1 | 3434 | 4-May-15 |
| 4593 | 3 | 4 | 5 | 6 | | VI-1 | Ifit3 | 3437 | 21-May-15 |
| 4594 | 3 | 4 | 5 | 6 | | VI-1 | Ifitm1 | 8519 | 4-May-15 |
| 4595 | 3 | 4 | 5 | 6 | | VI-1 | Ifitm2 | 10581 | 4-May-15 |
| 4596 | 3 | 4 | 5 | 6 | | VI-1 | Ifitm6 | | |
| 4597 | 3 | 4 | 5 | 6 | | VI-1 | Ifrd1 | 3475 | 26-May-15 |
| 4598 | 3 | 4 | 5 | 6 | | VI-1 | Ifrd2 | 7866 | 12-May-15 |
| 4599 | 3 | 4 | 5 | 6 | | VI-1 | Igf1 | 3479 | 24-May-15 |
| 4600 | 3 | 4 | 5 | 6 | | VI-1 | Igf2bp2 | 10644 | 17-May-15 |
| 4601 | 3 | 4 | 5 | 6 | | VI-1 | Igfbp3 | 3486 | 17-May-15 |
| 4602 | 3 | 4 | 5 | 6 | | VI-1 | Igfbp6 | 3489 | 4-May-15 |
| 4603 | 3 | 4 | 5 | 6 | | VI-1 | Igfbp7 | 3490 | 12-May-15 |
| 4604 | 3 | 4 | 5 | 6 | | VI-1 | Igsf10 | 285313 | 4-May-15 |
| 4605 | 3 | 4 | 5 | 6 | | VI-1 | Igsf5 | 150084 | 21-May-15 |
| 4606 | 3 | 4 | 5 | 6 | | VI-1 | Igsf6 | 10261 | 4-May-15 |
| 4607 | 3 | 4 | 5 | 6 | | VI-1 | Igsf9 | 57549 | 4-May-15 |
| 4608 | 3 | 4 | 5 | 6 | | VI-1 | Igtp | | |
| 4609 | 3 | 4 | 5 | 6 | | VI-1 | Iigp1 | | |
| 4610 | 3 | 4 | 5 | 6 | | VI-1 | Ikzf1 | 10320 | 12-May-15 |
| 4611 | 3 | 4 | 5 | 6 | | VI-1 | Il10ra | 3587 | 4-May-15 |
| 4612 | 3 | 4 | 5 | 6 | | VI-1 | Il11 | 3589 | 4-May-15 |
| 4613 | 3 | 4 | 5 | 6 | | VI-1 | Il13ra1 | 3597 | 8-May-15 |
| 4614 | 3 | 4 | 5 | 6 | | VI-1 | Il16 | 3603 | 4-May-15 |
| 4615 | 3 | 4 | 5 | 6 | | VI-1 | Il17ra | 23765 | 24-May-15 |
| 4616 | 3 | 4 | 5 | 6 | | VI-1 | Il18 | 3606 | 17-May-15 |
| 4617 | 3 | 4 | 5 | 6 | | VI-1 | Il18r1 | 8809 | 24-May-15 |
| 4618 | 3 | 4 | 5 | 6 | | VI-1 | Il18rap | 8807 | 4-May-15 |
| 4619 | 3 | 4 | 5 | 6 | | VI-1 | Il19 | 56300 | 4-May-15 |
| 4620 | 3 | 4 | 5 | 6 | | VI-1 | Il1r1 | 3554 | 12-May-15 |
| 4621 | 3 | 4 | 5 | 6 | | VI-1 | Il1rl1 | 9173 | 12-May-15 |
| 4622 | 3 | 4 | 5 | 6 | | VI-1 | Il22ra1 | 58985 | 4-May-15 |
| 4623 | 3 | 4 | 5 | 6 | | VI-1 | Il2rg | 3561 | 23-May-15 |
| 4624 | 3 | 4 | 5 | 6 | | VI-1 | Il33 | 90865 | 17-May-15 |
| 4625 | 3 | 4 | 5 | 6 | | VI-1 | Il4ra | 3566 | 17-May-15 |
| 4626 | 3 | 4 | 5 | 6 | | VI-1 | Il5ra | 3568 | 12-May-15 |
| 4627 | 3 | 4 | 5 | 6 | | VI-1 | Il6ra | 3570 | 17-May-15 |
| 4628 | 3 | 4 | 5 | 6 | | VI-1 | Il9r | 3581 | 10-May-15 |
| 4629 | 3 | 4 | 5 | 6 | | VI-1 | Ildr1 | 286676 | 4-May-15 |
| 4630 | 3 | 4 | 5 | 6 | | VI-1 | Impact | 55364 | 12-May-15 |
| 4631 | 3 | 4 | 5 | 6 | | VI-1 | Impdh1 | 3614 | 7-Jun-15 |
| 4632 | 3 | 4 | 5 | 6 | | VI-1 | Incenp | 3619 | 4-May-15 |
| 4633 | 3 | 4 | 5 | 6 | | VI-1 | Inhba | 3624 | 4-May-15 |
| 4634 | 3 | 4 | 5 | 6 | | VI-1 | Inmr | 11185 | 4-May-15 |
| 4635 | 3 | 4 | 5 | 6 | | VI-1 | Insig2 | 51141 | 4-May-15 |
| 4636 | 3 | 4 | 5 | 6 | | VI-1 | Insl6 | 11172 | 4-May-15 |
| 4637 | 3 | 4 | 5 | 6 | | VI-1 | Ip6k2 | 51447 | 4-May-15 |
| 4638 | 3 | 4 | 5 | 6 | | VI-1 | Ip6k3 | 117283 | 4-May-15 |
| 4639 | 3 | 4 | 5 | 6 | | VI-1 | Ipcef1 | 26034 | 4-May-15 |
| 4640 | 3 | 4 | 5 | 6 | | VI-1 | Iqcd | 115811 | 4-May-15 |
| 4641 | 3 | 4 | 5 | 6 | | VI-1 | Iqgap1 | 8826 | 17-May-15 |
| 4642 | 3 | 4 | 5 | 6 | | VI-1 | Iqgap3 | 128239 | 17-May-15 |
| 4643 | 3 | 4 | 5 | 6 | | VI-1 | Irak1bp1 | 134724 | 4-May-15 |
| 4644 | 3 | 4 | 5 | 6 | | VI-1 | Irak3 | 11213 | 17-May-15 |
| 4645 | 3 | 4 | 5 | 6 | | VI-1 | Irf2bp2 | 359948 | 12-May-15 |
| 4646 | 3 | 4 | 5 | 6 | | VI-1 | Irf5 | 3663 | 24-May-15 |
| 4647 | 3 | 4 | 5 | 6 | | VI-1 | Irf6 | 3664 | 23-May-15 |
| 4648 | 3 | 4 | 5 | 6 | | VI-1 | Irf7 | 3665 | 21-May-15 |
| 4649 | 3 | 4 | 5 | 6 | | VI-1 | Irf8 | 3394 | 24-May-15 |
| 4650 | 3 | 4 | 5 | 6 | | VI-1 | Irs2 | 8660 | 12-May-15 |
| 4651 | 3 | 4 | 5 | 6 | | VI-1 | Irx1 | 79192 | 7-Jun-15 |
| 4652 | 3 | 4 | 5 | 6 | | VI-1 | Irx3 | 79191 | 24-May-15 |
| 4653 | 3 | 4 | 5 | 6 | | VI-1 | Isca1 | 81689 | 4-May-15 |
| 4654 | 3 | 4 | 5 | 6 | | VI-1 | Isg15 | 9636 | 12-May-15 |
| 4655 | 3 | 4 | 5 | 6 | | VI-1 | Islr | 3671 | 12-May-15 |
| 4656 | 3 | 4 | 5 | 6 | | VI-1 | Isyna1 | 51477 | 12-May-15 |
| 4657 | 3 | 4 | 5 | 6 | | VI-1 | Itga1 | 3672 | 12-May-15 |
| 4658 | 3 | 4 | 5 | 6 | | VI-1 | Itga11 | 22801 | 21-May-15 |
| 4659 | 3 | 4 | 5 | 6 | | VI-1 | Itga2b | 3674 | 12-May-15 |
| 4660 | 3 | 4 | 5 | 6 | | VI-1 | Itga4 | 3676 | 24-May-15 |
| 4661 | 3 | 4 | 5 | 6 | | VI-1 | Itga5 | 3678 | 4-May-15 |
| 4662 | 3 | 4 | 5 | 6 | | VI-1 | Itga6 | 3655 | 23-May-15 |
| 4663 | 3 | 4 | 5 | 6 | | VI-1 | Itga9 | 3680 | 4-May-15 |
| 4664 | 3 | 4 | 5 | 6 | | VI-1 | Itgam | 3684 | 12-May-15 |
| 4665 | 3 | 4 | 5 | 6 | | VI-1 | Itgax | 3687 | 12-May-15 |
| 4666 | 3 | 4 | 5 | 6 | | VI-1 | Itgb1bp2 | 26548 | 4-May-15 |
| 4667 | 3 | 4 | 5 | 6 | | VI-1 | Itgb2 | 3689 | 12-May-15 |
| 4668 | 3 | 4 | 5 | 6 | | VI-1 | Itgb3 | 3690 | 24-May-15 |
| 4669 | 3 | 4 | 5 | 6 | | VI-1 | Itgb5 | 3693 | 17-May-15 |
| 4670 | 3 | 4 | 5 | 6 | | VI-1 | Itgb7 | 3695 | 4-May-15 |
| 4671 | 3 | 4 | 5 | 6 | | VI-1 | Itgh1 | 9358 | 4-May-15 |
| 4672 | 3 | 4 | 5 | 6 | | VI-1 | Itm2a | 9452 | 4-May-15 |
| 4673 | 3 | 4 | 5 | 6 | | VI-1 | Itm2b | 9445 | 3-May-15 |
| 4674 | 3 | 4 | 5 | 6 | | VI-1 | Jade2 | 23338 | 12-May-15 |
| 4675 | 3 | 4 | 5 | 6 | | VI-1 | Jade3 | 9767 | 4-May-15 |
| 4676 | 3 | 4 | 5 | 6 | | VI-1 | Jak3 | 3718 | 10-May-15 |
| 4677 | 3 | 4 | 5 | 6 | | VI-1 | Jdp2 | 122953 | 4-May-15 |
| 4678 | 3 | 4 | 5 | 6 | | VI-1 | Jmjd7 | 100137047 | 4-May-15 |
| 4679 | 3 | 4 | 5 | 6 | | VI-1 | Josd2 | 126119 | 4-May-15 |
| 4680 | 3 | 4 | 5 | 6 | | VI-1 | Jph2 | 57158 | 4-May-15 |
| 4681 | 3 | 4 | 5 | 6 | | VI-1 | Junb | 3726 | 7-Jun-15 |
| 4682 | 3 | 4 | 5 | 6 | | VI-1 | Kansl1l | 151050 | 12-May-15 |
| 4683 | 3 | 4 | 5 | 6 | | VI-1 | Kat8 | 84148 | 4-May-15 |
| 4684 | 3 | 4 | 5 | 6 | | VI-1 | Kcna1 | 3736 | 23-May-15 |
| 4685 | 3 | 4 | 5 | 6 | | VI-1 | Kcna3 | 3738 | 4-May-15 |
| 4686 | 3 | 4 | 5 | 6 | | VI-1 | Kcna5 | 3741 | 17-May-15 |
| 4687 | 3 | 4 | 5 | 6 | | VI-1 | Kcnab2 | 8514 | 4-May-15 |
| 4688 | 3 | 4 | 5 | 6 | | VI-1 | Kcnd1 | 3750 | 12-May-15 |
| 4689 | 3 | 4 | 5 | 6 | | VI-1 | Kcne3 | 10008 | 23-May-15 |
| 4690 | 3 | 4 | 5 | 6 | | VI-1 | Kcne4 | 23704 | 4-May-15 |
| 4691 | 3 | 4 | 5 | 6 | | VI-1 | Kcnf1 | 3754 | 4-May-15 |
| 4692 | 3 | 4 | 5 | 6 | | VI-1 | Kcnh8 | 131096 | 4-May-15 |
| 4693 | 3 | 4 | 5 | 6 | | VI-1 | Kcnip3 | 30818 | 12-May-15 |
| 4694 | 3 | 4 | 5 | 6 | | VI-1 | Kcnj12 | 3768 | 4-May-15 |
| 4695 | 3 | 4 | 5 | 6 | | VI-1 | Kcnj15 | 3772 | 21-May-15 |
| 4696 | 3 | 4 | 5 | 6 | | VI-1 | Kcnk1 | 3775 | 4-May-15 |
| 4697 | 3 | 4 | 5 | 6 | | VI-1 | Kcnk13 | 56659 | 4-May-15 |
| 4698 | 3 | 4 | 5 | 6 | | VI-1 | Kcnk3 | 3777 | 4-May-15 |
| 4699 | 3 | 4 | 5 | 6 | | VI-1 | Kcnk6 | 9424 | 4-May-15 |
| 4700 | 3 | 4 | 5 | 6 | | VI-1 | Kcnn4 | 3783 | 12-May-15 |
| 4701 | 3 | 4 | 5 | 6 | | VI-1 | Kcnq1 | 3784 | 22-May-15 |
| 4702 | 3 | 4 | 5 | 6 | | VI-1 | Kctd11 | 147040 | 4-May-15 |
| 4703 | 3 | 4 | 5 | 6 | | VI-1 | Kctd12 | 115207 | 4-May-15 |
| 4704 | 3 | 4 | 5 | 6 | | VI-1 | Kctd15 | 79047 | 4-May-15 |
| 4705 | 3 | 4 | 5 | 6 | | VI-1 | Kdf1 | 126695 | 4-May-15 |
| 4706 | 3 | 4 | 5 | 6 | | VI-1 | Kdr | 3791 | 17-May-15 |
| 4707 | 3 | 4 | 5 | 6 | | VI-1 | Kel | 3792 | 12-May-15 |
| 4708 | 3 | 4 | 5 | 6 | | VI-1 | Kif14 | 9928 | 17-May-15 |
| 4709 | 3 | 4 | 5 | 6 | | VI-1 | Kif18a | 81930 | 4-May-15 |
| 4710 | 3 | 4 | 5 | 6 | | VI-1 | Kif20a | 10112 | 4-May-15 |
| 4711 | 3 | 4 | 5 | 6 | | VI-1 | Kif20b | 9585 | 21-May-15 |
| 4712 | 3 | 4 | 5 | 6 | | VI-1 | Kif21b | 23046 | 4-May-15 |
| 4713 | 3 | 4 | 5 | 6 | | VI-1 | Kif23 | 9493 | 4-May-15 |
| 4714 | 3 | 4 | 5 | 6 | | VI-1 | Kif24 | 347240 | 4-May-15 |
| 4715 | 3 | 4 | 5 | 6 | | VI-1 | Kif26b | 55083 | 4-May-15 |
| 4716 | 3 | 4 | 5 | 6 | | VI-1 | Kif4 | 24137 | 4-May-15 |
| 4717 | 3 | 4 | 5 | 6 | | VI-1 | Kit | 3815 | 24-May-15 |
| 4718 | 3 | 4 | 5 | 6 | | VI-1 | Kitl | 152831 | 4-May-15 |
| 4719 | 3 | 4 | 5 | 6 | | VI-1 | Klc3 | 147700 | 4-May-15 |
| 4720 | 3 | 4 | 5 | 6 | | VI-1 | Klf1 | 10661 | 4-May-15 |
| 4721 | 3 | 4 | 5 | 6 | | VI-1 | Klf10 | 7071 | 3-May-15 |
| 4722 | 3 | 4 | 5 | 6 | | VI-1 | Klf15 | 28999 | 4-May-15 |
| 4723 | 3 | 4 | 5 | 6 | | VI-1 | Klf2 | 10365 | 12-May-15 |

Fig. 30 - 26

| | | | | | | | | | | | | | | | | | |
|---|---|---|---|---|---|---|---|---|---|---|---|---|---|---|---|---|---|
| 4724 | 3 | 4 | 5 | 6 | | VI-1 | Klf5 | 688 | 17-May-15 | 4819 | 3 | 4 | 5 | 6 | | VI-1 | Lman1l | 79748 | 4-May-15 |
| 4725 | 3 | 4 | 5 | 6 | | VI-1 | Klf6 | 1316 | 4-May-15 | 4820 | 3 | 4 | 5 | 6 | | VI-1 | Lmod1 | 29995 | 4-May-15 |
| 4726 | 3 | 4 | 5 | 6 | | VI-1 | Klhdc8a | 55220 | 4-May-15 | 4821 | 3 | 4 | 5 | 6 | | VI-1 | Lmna | 4000 | 24-May-15 |
| 4727 | 3 | 4 | 5 | 6 | | VI-1 | Klhl12 | 59349 | 4-May-15 | 4822 | 3 | 4 | 5 | 6 | | VI-1 | Lmo2 | 4005 | 21-May-15 |
| 4728 | 3 | 4 | 5 | 6 | | VI-1 | Klhl14 | 57565 | 4-May-15 | 4823 | 3 | 4 | 5 | 6 | | VI-1 | Lmod2 | 442721 | 12-May-15 |
| 4729 | 3 | 4 | 5 | 6 | | VI-1 | Klhl2 | 11275 | 4-May-15 | 4824 | 3 | 4 | 5 | 6 | | VI-1 | Lnx1 | 84708 | 26-May-15 |
| 4730 | 3 | 4 | 5 | 6 | | VI-1 | Klhl32 | 114792 | 4-May-15 | 4825 | 3 | 4 | 5 | 6 | | VI-1 | LOC100038947 | | |
| 4731 | 3 | 4 | 5 | 6 | | VI-1 | Klhl38 | 340359 | 4-May-15 | 4826 | 3 | 4 | 5 | 6 | | VI-1 | LOC100503496 | | |
| 4732 | 3 | 4 | 5 | 6 | | VI-1 | Klhl40 | 131377 | 4-May-15 | 4827 | 3 | 4 | 5 | 6 | | VI-1 | LOC100503676 | | |
| 4733 | 3 | 4 | 5 | 6 | | VI-1 | Klhl41 | 10324 | 4-May-15 | 4828 | 3 | 4 | 5 | 6 | | VI-1 | Lonrf2 | 164832 | 12-May-15 |
| 4734 | 3 | 4 | 5 | 6 | | VI-1 | Klhl7 | 55975 | 23-May-15 | 4829 | 3 | 4 | 5 | 6 | | VI-1 | Lonrf3 | 79836 | 4-May-15 |
| 4735 | 3 | 4 | 5 | 6 | | VI-1 | Klk10 | 5655 | 21-May-15 | 4830 | 3 | 4 | 5 | 6 | | VI-1 | Loxl1 | 4016 | 12-May-15 |
| 4736 | 3 | 4 | 5 | 6 | | VI-1 | Klk11 | 11012 | 4-May-15 | 4831 | 3 | 4 | 5 | 6 | | VI-1 | Loxl2 | 4017 | 12-May-15 |
| 4737 | 3 | 4 | 5 | 6 | | VI-1 | Klk14 | 43847 | 4-May-15 | 4832 | 3 | 4 | 5 | 6 | | VI-1 | Loxl4 | 84171 | 4-May-15 |
| 4738 | 3 | 4 | 5 | 6 | | VI-1 | Klk1b24 | | | 4833 | 3 | 4 | 5 | 6 | | VI-1 | Lpcat2 | 54947 | 12-May-15 |
| 4739 | 3 | 4 | 5 | 6 | | VI-1 | Klk1b26 | | | 4834 | 3 | 4 | 5 | 6 | | VI-1 | Lpin2 | 9663 | 23-May-15 |
| 4740 | 3 | 4 | 5 | 6 | | VI-1 | Klk1b7-ps | | | 4835 | 3 | 4 | 5 | 6 | | VI-1 | Lpin3 | 64900 | 4-May-15 |
| 4741 | 3 | 4 | 5 | 6 | | VI-1 | Klk1b8 | | | 4836 | 3 | 4 | 5 | 6 | | VI-1 | Lpl | 4023 | 7-Jun-15 |
| 4742 | 3 | 4 | 5 | 6 | | VI-1 | Klk1b9 | | | 4837 | 3 | 4 | 5 | 6 | | VI-1 | Lpo | 4025 | 4-May-15 |
| 4743 | 3 | 4 | 5 | 6 | | VI-1 | Klra1 | 10748 | 12-May-15 | 4838 | 3 | 4 | 5 | 6 | | VI-1 | Lpxn | 9404 | 12-May-15 |
| 4744 | 3 | 4 | 5 | 6 | | VI-1 | Klra10 | | | 4839 | 3 | 4 | 5 | 6 | | VI-1 | Lrfn3 | 79414 | 4-May-15 |
| 4745 | 3 | 4 | 5 | 6 | | VI-1 | Klra12 | | | 4840 | 3 | 4 | 5 | 6 | | VI-1 | Lrg1 | 116844 | 4-May-15 |
| 4746 | 3 | 4 | 5 | 6 | | VI-1 | Klra14-ps | | | 4841 | 3 | 4 | 5 | 6 | | VI-1 | Lrig3 | 121227 | 4-May-15 |
| 4747 | 3 | 4 | 5 | 6 | | VI-1 | Klra17 | | | 4842 | 3 | 4 | 5 | 6 | | VI-1 | Lrp1 | 4035 | 7-Jun-15 |
| 4748 | 3 | 4 | 5 | 6 | | VI-1 | Klra23 | | | 4843 | 3 | 4 | 5 | 6 | | VI-1 | Lrp12 | 29967 | 12-May-15 |
| 4749 | 3 | 4 | 5 | 6 | | VI-1 | Klra5 | | | 4844 | 3 | 4 | 5 | 6 | | VI-1 | Lrp8 | 7804 | 12-May-15 |
| 4750 | 3 | 4 | 5 | 6 | | VI-1 | Klra7 | | | 4845 | 3 | 4 | 5 | 6 | | VI-1 | Lrr1 | 122769 | 4-May-15 |
| 4751 | 3 | 4 | 5 | 6 | | VI-1 | Klra8 | | | 4846 | 3 | 4 | 5 | 6 | | VI-1 | Lrrc24 | 441381 | 4-May-15 |
| 4752 | 3 | 4 | 5 | 6 | | VI-1 | Klra9 | | | 4847 | 3 | 4 | 5 | 6 | | VI-1 | Lrrc25 | 126364 | 4-May-15 |
| 4753 | 3 | 4 | 5 | 6 | | VI-1 | Klrb1a | | | 4848 | 3 | 4 | 5 | 6 | | VI-1 | Lrrc26 | 389816 | 12-May-15 |
| 4754 | 3 | 4 | 5 | 6 | | VI-1 | Klre1 | | | 4849 | 3 | 4 | 5 | 6 | | VI-1 | Lrrc30 | 339291 | 4-May-15 |
| 4755 | 3 | 4 | 5 | 6 | | VI-1 | Klrk1 | 22914 | 24-May-15 | 4850 | 3 | 4 | 5 | 6 | | VI-1 | Lrrc46 | 90506 | 4-May-15 |
| 4756 | 3 | 4 | 5 | 6 | | VI-1 | Kntc1 | 9735 | 14-May-15 | 4851 | 3 | 4 | 5 | 6 | | VI-1 | Lrrc58 | 116064 | 4-May-15 |
| 4757 | 3 | 4 | 5 | 6 | | VI-1 | Kpna2 | 3838 | 17-May-15 | 4852 | 3 | 4 | 5 | 6 | | VI-1 | Lrrc8c | 84230 | 12-May-15 |
| 4758 | 3 | 4 | 5 | 6 | | VI-1 | Kprp | 448834 | 4-May-15 | 4853 | 3 | 4 | 5 | 6 | | VI-1 | Lrrc9 | 341883 | 4-May-15 |
| 4759 | 3 | 4 | 5 | 6 | | VI-1 | Krt17 | 3872 | 22-May-15 | 4854 | 3 | 4 | 5 | 6 | | VI-1 | Lrrk2 | 120892 | 23-May-15 |
| 4760 | 3 | 4 | 5 | 6 | | VI-1 | Krt19 | 3880 | 12-May-15 | 4855 | 3 | 4 | 5 | 6 | | VI-1 | Lrrn1 | 57633 | 4-May-15 |
| 4761 | 3 | 4 | 5 | 6 | | VI-1 | Krt6b | 3854 | 4-May-15 | 4856 | 3 | 4 | 5 | 6 | | VI-1 | Lrrn4 | 164312 | 13-Jun-15 |
| 4762 | 3 | 4 | 5 | 6 | | VI-1 | Krt7 | 3855 | 12-May-15 | 4857 | 3 | 4 | 5 | 6 | | VI-1 | Lrrn4cl | 221091 | 4-May-15 |
| 4763 | 3 | 4 | 5 | 6 | | VI-1 | Krt8 | 3856 | 4-May-15 | 4858 | 3 | 4 | 5 | 6 | | VI-1 | Lsm5 | 23658 | 4-May-15 |
| 4764 | 3 | 4 | 5 | 6 | | VI-1 | Krtap17-1 | 83902 | 4-May-15 | 4859 | 3 | 4 | 5 | 6 | | VI-1 | Lsp1 | 4046 | 4-May-15 |
| 4765 | 3 | 4 | 5 | 6 | | VI-1 | Krtdap | 388533 | 4-May-15 | 4860 | 3 | 4 | 5 | 6 | | VI-1 | Lsr | 51599 | 4-May-15 |
| 4766 | 3 | 4 | 5 | 6 | | VI-1 | L3hypdh | 112849 | 12-May-15 | 4861 | 3 | 4 | 5 | 6 | | VI-1 | Lss | 4047 | 7-Jun-15 |
| 4767 | 3 | 4 | 5 | 6 | | VI-1 | Lactbl1 | 646262 | 4-May-15 | 4862 | 3 | 4 | 5 | 6 | | VI-1 | Lst1 | | |
| 4768 | 3 | 4 | 5 | 6 | | VI-1 | Lad1 | 3898 | 7-Jun-15 | 4863 | 3 | 4 | 5 | 6 | | VI-1 | Ltb | 4050 | 12-May-15 |
| 4769 | 3 | 4 | 5 | 6 | | VI-1 | Lag3 | 3902 | 4-May-15 | 4864 | 3 | 4 | 5 | 6 | | VI-1 | Ltb4r1 | 1241 | 17-May-15 |
| 4770 | 3 | 4 | 5 | 6 | | VI-1 | Lair1 | 3903 | 3-May-15 | 4865 | 3 | 4 | 5 | 6 | | VI-1 | Ltbp3 | 4054 | 7-Jun-15 |
| 4771 | 3 | 4 | 5 | 6 | | VI-1 | Lama1 | 284217 | 17-May-15 | 4866 | 3 | 4 | 5 | 6 | | VI-1 | Lum | 4060 | 12-May-15 |
| 4772 | 3 | 4 | 5 | 6 | | VI-1 | Lama4 | 3910 | 4-May-15 | 4867 | 3 | 4 | 5 | 6 | | VI-1 | Lxn | 56925 | 4-May-15 |
| 4773 | 3 | 4 | 5 | 6 | | VI-1 | Lamc2 | 3918 | 23-May-15 | 4868 | 3 | 4 | 5 | 6 | | VI-1 | Ly6a | | |
| 4774 | 3 | 4 | 5 | 6 | | VI-1 | Lamp3 | 27074 | 7-Jun-15 | 4869 | 3 | 4 | 5 | 6 | | VI-1 | Ly6c2 | | |
| 4775 | 3 | 4 | 5 | 6 | | VI-1 | Laptm4b | 55353 | 17-May-15 | 4870 | 3 | 4 | 5 | 6 | | VI-1 | Ly6i | | |
| 4776 | 3 | 4 | 5 | 6 | | VI-1 | Lat2 | 7462 | 7-Jun-15 | 4871 | 3 | 4 | 5 | 6 | | VI-1 | Ly86 | 9450 | 4-May-15 |
| 4777 | 3 | 4 | 5 | 6 | | VI-1 | Lbp | 3929 | 7-Jun-15 | 4872 | 3 | 4 | 5 | 6 | | VI-1 | Lyl1 | 4066 | 12-May-15 |
| 4778 | 3 | 4 | 5 | 6 | | VI-1 | Lbr | 3930 | 12-May-15 | 4873 | 3 | 4 | 5 | 6 | | VI-1 | Lyn | 4067 | 12-May-15 |
| 4779 | 3 | 4 | 5 | 6 | | VI-1 | Lce1c | 353133 | 4-May-15 | 4874 | 3 | 4 | 5 | 6 | | VI-1 | Lypd2 | 137797 | 4-May-15 |
| 4780 | 3 | 4 | 5 | 6 | | VI-1 | Lce1e | 353135 | 4-May-15 | 4875 | 3 | 4 | 5 | 6 | | VI-1 | Lypd3 | 27076 | 4-May-15 |
| 4781 | 3 | 4 | 5 | 6 | | VI-1 | Lce1f | 353137 | 4-May-15 | 4876 | 3 | 4 | 5 | 6 | | VI-1 | Lypd5 | 284348 | 14-May-15 |
| 4782 | 3 | 4 | 5 | 6 | | VI-1 | Lce1g | | | 4877 | 3 | 4 | 5 | 6 | | VI-1 | Lyrm7 | 90624 | 12-May-15 |
| 4783 | 3 | 4 | 5 | 6 | | VI-1 | Lce1h | | | 4878 | 3 | 4 | 5 | 6 | | VI-1 | Lyz1 | | |
| 4784 | 3 | 4 | 5 | 6 | | VI-1 | Lce1i | | | 4879 | 3 | 4 | 5 | 6 | | VI-1 | Lyz2 | | |
| 4785 | 3 | 4 | 5 | 6 | | VI-1 | Lce1j | | | 4880 | 3 | 4 | 5 | 6 | | VI-1 | Mad2l1 | 4085 | 12-May-15 |
| 4786 | 3 | 4 | 5 | 6 | | VI-1 | Lce1k | | | 4881 | 3 | 4 | 5 | 6 | | VI-1 | Madcam1 | 8174 | 4-May-15 |
| 4787 | 3 | 4 | 5 | 6 | | VI-1 | Lce1l | | | 4882 | 3 | 4 | 5 | 6 | | VI-1 | Maff | 23764 | 4-May-15 |
| 4788 | 3 | 4 | 5 | 6 | | VI-1 | Lcn10 | 414332 | 4-May-15 | 4883 | 3 | 4 | 5 | 6 | | VI-1 | Mafk | 7975 | 4-May-15 |
| 4789 | 3 | 4 | 5 | 6 | | VI-1 | Lcp1 | 3936 | 7-Jun-15 | 4884 | 3 | 4 | 5 | 6 | | VI-1 | Magi1 | 9223 | 7-Jun-15 |
| 4790 | 3 | 4 | 5 | 6 | | VI-1 | Lct | 197021 | 4-May-15 | 4885 | 3 | 4 | 5 | 6 | | VI-1 | Magohb | 55110 | 12-May-15 |
| 4791 | 3 | 4 | 5 | 6 | | VI-1 | Ldhc | 3948 | 21-May-15 | 4886 | 3 | 4 | 5 | 6 | | VI-1 | Mal2 | 114569 | 4-May-15 |
| 4792 | 3 | 4 | 5 | 6 | | VI-1 | Ldhd | 197257 | 4-May-15 | 4887 | 3 | 4 | 5 | 6 | | VI-1 | Malat1 | 378938 | 21-May-15 |
| 4793 | 3 | 4 | 5 | 6 | | VI-1 | Lefty1 | 10637 | 4-May-15 | 4888 | 3 | 4 | 5 | 6 | | VI-1 | Malt1 | 10892 | 4-May-15 |
| 4794 | 3 | 4 | 5 | 6 | | VI-1 | Lep | 3952 | 24-May-15 | 4889 | 3 | 4 | 5 | 6 | | VI-1 | Manf | 7873 | 21-May-15 |
| 4795 | 3 | 4 | 5 | 6 | | VI-1 | Lepr | 3953 | 7-Jun-15 | 4890 | 3 | 4 | 5 | 6 | | VI-1 | Maob | 4129 | 17-May-15 |
| 4796 | 3 | 4 | 5 | 6 | | VI-1 | Leprel2 | 10536 | 4-May-15 | 4891 | 3 | 4 | 5 | 6 | | VI-1 | Map1a | 4130 | 7-Jun-15 |
| 4797 | 3 | 4 | 5 | 6 | | VI-1 | Leprel4 | 10609 | 12-May-15 | 4892 | 3 | 4 | 5 | 6 | | VI-1 | Map1b | 4131 | 4-May-15 |
| 4798 | 3 | 4 | 5 | 6 | | VI-1 | Lfng | 3955 | 23-May-15 | 4893 | 3 | 4 | 5 | 6 | | VI-1 | Map3k14 | 9020 | 14-May-15 |
| 4799 | 3 | 4 | 5 | 6 | | VI-1 | Lgals1 | 3956 | 24-May-15 | 4894 | 3 | 4 | 5 | 6 | | VI-1 | Map3k19 | 80122 | 21-May-15 |
| 4800 | 3 | 4 | 5 | 6 | | VI-1 | Lgals3bp | 3959 | 12-May-15 | 4895 | 3 | 4 | 5 | 6 | | VI-1 | Map3k6 | 9064 | 4-May-15 |
| 4801 | 3 | 4 | 5 | 6 | | VI-1 | Lgals4 | 3960 | 4-May-15 | 4896 | 3 | 4 | 5 | 6 | | VI-1 | Map3k7cl | 56911 | 4-May-15 |
| 4802 | 3 | 4 | 5 | 6 | | VI-1 | Lgals6 | | | 4897 | 3 | 4 | 5 | 6 | | VI-1 | Map3k8 | 1326 | 4-May-15 |
| 4803 | 3 | 4 | 5 | 6 | | VI-1 | Lgals7 | 3963, 653499 | 7-Jun-15 | 4898 | 3 | 4 | 5 | 6 | | VI-1 | Map4k3 | 13184 | 4-May-15 |
| | | | | | | | | | | 4899 | 3 | 4 | 5 | 6 | | VI-1 | Map4k4 | 9448 | 4-May-15 |
| 4804 | 3 | 4 | 5 | 6 | | VI-1 | Lgals9 | 3965 | 17-May-15 | 4900 | 3 | 4 | 5 | 6 | | VI-1 | Mapt | 4135 | 4-May-15 |
| 4805 | 3 | 4 | 5 | 6 | | VI-1 | Lgalsl | 29094 | 12-May-15 | 4901 | 3 | 4 | 5 | 6 | | VI-1 | Map7d2 | 256714 | 4-May-15 |
| 4806 | 3 | 4 | 5 | 6 | | VI-1 | Lgi3 | 203190 | 4-May-15 | 4902 | 3 | 4 | 5 | 6 | | VI-1 | Mapk12 | 5600 | 4-May-15 |
| 4807 | 3 | 4 | 5 | 6 | | VI-1 | Lgmn | 5641 | 4-May-15 | 4903 | 3 | 4 | 5 | 6 | | VI-1 | Mapk13 | 5603 | 4-May-15 |
| 4808 | 3 | 4 | 5 | 6 | | VI-1 | Lhb | 3972 | 12-May-15 | 4904 | 3 | 4 | 5 | 6 | | VI-1 | March1 | 55016 | 12-May-15 |
| 4809 | 3 | 4 | 5 | 6 | | VI-1 | Lhfpl2 | 10184 | 4-May-15 | 4905 | 3 | 4 | 5 | 6 | | VI-1 | March2 | 51257 | 4-May-15 |
| 4810 | 3 | 4 | 5 | 6 | | VI-1 | Lhx2 | 9355 | 4-May-15 | 4906 | 3 | 4 | 5 | 6 | | VI-1 | March3 | 115123 | 4-May-15 |
| 4811 | 3 | 4 | 5 | 6 | | VI-1 | Lig1 | 3978 | 7-Jun-15 | 4907 | 3 | 4 | 5 | 6 | | VI-1 | March8 | 220972 | 4-May-15 |
| 4812 | 3 | 4 | 5 | 6 | | VI-1 | Lilra6 | 79168 | 20-May-15 | 4908 | 3 | 4 | 5 | 6 | | VI-1 | Marcks | 4082 | 10-May-15 |
| 4813 | 3 | 4 | 5 | 6 | | VI-1 | Lilrb4 | 11006 | 12-May-15 | 4909 | 3 | 4 | 5 | 6 | | VI-1 | Marcksl1 | 65108 | 4-May-15 |
| 4814 | 3 | 4 | 5 | 6 | | VI-1 | Lims2 | 55679 | 17-May-15 | 4910 | 3 | 4 | 5 | 6 | | VI-1 | Marveld2 | 153562 | 23-May-15 |
| 4815 | 3 | 4 | 5 | 6 | | VI-1 | Lipa | 3988 | 7-Jun-15 | 4911 | 3 | 4 | 5 | 6 | | VI-1 | Marveld3 | 91862 | 4-May-15 |
| 4816 | 3 | 4 | 5 | 6 | | VI-1 | Lipe | 3991 | 12-May-15 | 4912 | 3 | 4 | 5 | 6 | | VI-1 | Masp1 | 5648 | 17-May-15 |
| 4817 | 3 | 4 | 5 | 6 | | VI-1 | Lipi | 149998 | 4-May-15 | 4913 | 3 | 4 | 5 | 6 | | VI-1 | Masp2 | 10747 | 12-May-15 |
| 4818 | 3 | 4 | 5 | 6 | | VI-1 | Litaf | 9516 | 23-May-15 | 4914 | 3 | 4 | 5 | 6 | | VI-1 | Mast1 | 84930 | 4-May-15 |

Fig. 30 - 27

| | | | | | | | | | | | | | | | | | |
|---|---|---|---|---|---|---|---|---|---|---|---|---|---|---|---|---|---|
| 4915 | 3 | 4 | 5 | 6 | | VI-1 | Mbd1 | 4152 | 7-Jun-15 | 5009 | 3 | 4 | 5 | 6 | | VI-1 | Mis18bp1 | 55320 | 4-May-15 |
| 4916 | 3 | 4 | 5 | 6 | | VI-1 | Mbd4 | 8930 | 12-May-15 | 5010 | 3 | 4 | 5 | 6 | | VI-1 | Mkrn1 | 23608 | 12-May-15 |
| 4917 | 3 | 4 | 5 | 6 | | VI-1 | Mboat1 | 154141 | 4-May-15 | 5011 | 3 | 4 | 5 | 6 | | VI-1 | Mlana | 2315 | 4-May-15 |
| 4918 | 3 | 4 | 5 | 6 | | VI-1 | Mc5r | 4161 | 4-May-15 | 5012 | 3 | 4 | 5 | 6 | | VI-1 | Mlf1 | 4291 | 12-May-15 |
| 4919 | 3 | 4 | 5 | 6 | | VI-1 | Mcam | 4162 | 4-May-15 | 5013 | 3 | 4 | 5 | 6 | | VI-1 | Mlxip | 22877 | 4-May-15 |
| 4920 | 3 | 4 | 5 | 6 | | VI-1 | Mcemp1 | 199675 | 4-May-15 | 5014 | 3 | 4 | 5 | 6 | | VI-1 | Mme | 4311 | 7-Jun-15 |
| 4921 | 3 | 4 | 5 | 6 | | VI-1 | Mcf2l | 23263 | 4-May-15 | 5015 | 3 | 4 | 5 | 6 | | VI-1 | Mmp14 | 4323 | 10-May-15 |
| 4922 | 3 | 4 | 5 | 6 | | VI-1 | Mcm10 | 55388 | 4-May-15 | 5016 | 3 | 4 | 5 | 6 | | VI-1 | Mmp19 | 4327 | 12-May-15 |
| 4923 | 3 | 4 | 5 | 6 | | VI-1 | Mcm2 | 4171 | 7-Jun-15 | 5017 | 3 | 4 | 5 | 6 | | VI-1 | Mmp2 | 4313 | 24-May-15 |
| 4924 | 3 | 4 | 5 | 6 | | VI-1 | Mcm3 | 4172 | 4-May-15 | 5018 | 3 | 4 | 5 | 6 | | VI-1 | Mmp23 | | |
| 4925 | 3 | 4 | 5 | 6 | | VI-1 | Mcm4 | 4173 | 4-May-15 | 5019 | 3 | 4 | 5 | 6 | | VI-1 | Mmp3 | 4314 | 17-May-15 |
| 4926 | 3 | 4 | 5 | 6 | | VI-1 | Mcm5 | 4174 | 4-May-15 | 5020 | 3 | 4 | 5 | 6 | | VI-1 | Mmp8 | 4317 | 24-May-15 |
| 4927 | 3 | 4 | 5 | 6 | | VI-1 | Mcm6 | 4175 | 4-May-15 | 5021 | 3 | 4 | 5 | 6 | | VI-1 | Mmp9 | 4318 | 24-May-15 |
| 4928 | 3 | 4 | 5 | 6 | | VI-1 | Mcm7 | 4176 | 10-May-15 | 5022 | 3 | 4 | 5 | 6 | | VI-1 | Mns22l | 253714 | 4-May-15 |
| 4929 | 3 | 4 | 5 | 6 | | VI-1 | Mcph1 | 79648 | 23-May-15 | 5023 | 3 | 4 | 5 | 6 | | VI-1 | Mnd1 | 84057 | 4-May-15 |
| 4930 | 3 | 4 | 5 | 6 | | VI-1 | Mcpt4 | | | 5024 | 3 | 4 | 5 | 6 | | VI-1 | Mnda | 4332 | 4-May-15 |
| 4931 | 3 | 4 | 5 | 6 | | VI-1 | Mctp1 | 79772 | 12-May-15 | 5025 | 3 | 4 | 5 | 6 | | VI-1 | Mndal | | |
| 4932 | 3 | 4 | 5 | 6 | | VI-1 | Mdfi | 4188 | 12-May-15 | 5026 | 3 | 4 | 5 | 6 | | VI-1 | Mns1 | 55329 | 4-May-15 |
| 4933 | 3 | 4 | 5 | 6 | | VI-1 | Mdk | 4192 | 7-Jun-15 | 5027 | 3 | 4 | 5 | 6 | | VI-1 | Mob3a | 126308 | 4-May-15 |
| 4934 | 3 | 4 | 5 | 6 | | VI-1 | Me2 | 4200 | 7-Jun-15 | 5028 | 3 | 4 | 5 | 6 | | VI-1 | Mog | 4340 | 21-May-15 |
| 4935 | 3 | 4 | 5 | 6 | | VI-1 | Med26 | 9441 | 4-May-15 | 5029 | 3 | 4 | 5 | 6 | | VI-1 | Morf4l2 | 9643 | 4-May-15 |
| 4936 | 3 | 4 | 5 | 6 | | VI-1 | Mef2b | 4207 | 7-Jun-15 | 5030 | 3 | 4 | 5 | 6 | | VI-1 | Moxd1 | 26002 | 4-May-15 |
| 4937 | 3 | 4 | 5 | 6 | | VI-1 | Mef2c | 4208 | 12-May-15 | 5031 | 3 | 4 | 5 | 6 | | VI-1 | Mpp2 | 4355 | 7-Jun-15 |
| 4938 | 3 | 4 | 5 | 6 | | VI-1 | Mefv | 4210 | 23-May-15 | 5032 | 3 | 4 | 5 | 6 | | VI-1 | Mpp3 | 4356 | 4-May-15 |
| 4939 | 3 | 4 | 5 | 6 | | VI-1 | Megf6 | 1953 | 12-May-15 | 5033 | 3 | 4 | 5 | 6 | | VI-1 | Mpz | 4359 | 23-May-15 |
| 4940 | 3 | 4 | 5 | 6 | | VI-1 | Melk | 9833 | 4-May-15 | 5034 | 3 | 4 | 5 | 6 | | VI-1 | Mpzl1 | 9019 | 4-May-15 |
| 4941 | 3 | 4 | 5 | 6 | | VI-1 | Memo1 | 51072 | 7-Jun-15 | 5035 | 3 | 4 | 5 | 6 | | VI-1 | Mpzl2 | 10205 | 4-May-15 |
| 4942 | 3 | 4 | 5 | 6 | | VI-1 | Meox1 | 4222 | 12-May-15 | 5036 | 3 | 4 | 5 | 6 | | VI-1 | Mrap | 56246 | 7-Jun-15 |
| 4943 | 3 | 4 | 5 | 6 | | VI-1 | Meox2 | 4223 | 10-May-15 | 5037 | 3 | 4 | 5 | 6 | | VI-1 | Mrap2 | 112609 | 24-May-15 |
| 4944 | 3 | 4 | 5 | 6 | | VI-1 | Mertk | 10461 | 23-May-15 | 5038 | 3 | 4 | 5 | 6 | | VI-1 | Mrc2 | 9902 | 4-May-15 |
| 4945 | 3 | 4 | 5 | 6 | | VI-1 | Mest | 4232 | 12-May-15 | 5039 | 3 | 4 | 5 | 6 | | VI-1 | Mrgpra2a | | |
| 4946 | 3 | 4 | 5 | 6 | | VI-1 | Metap1d | 254042 | 4-May-15 | 5040 | 3 | 4 | 5 | 6 | | VI-1 | Ms4a4b | | |
| 4947 | 3 | 4 | 5 | 6 | | VI-1 | Metap2 | 10988 | 12-May-15 | 5041 | 3 | 4 | 5 | 6 | | VI-1 | Ms4a4c | | |
| 4948 | 3 | 4 | 5 | 6 | | VI-1 | Mettl7a2 | | | 5042 | 3 | 4 | 5 | 6 | | VI-1 | Ms4a6b | | |
| 4949 | 3 | 4 | 5 | 6 | | VI-1 | Mex3a | 92312 | 4-May-15 | 5043 | 3 | 4 | 5 | 6 | | VI-1 | Ms4a6c | | |
| 4950 | 3 | 4 | 5 | 6 | | VI-1 | Mex3b | 84206 | 4-May-15 | 5044 | 3 | 4 | 5 | 6 | | VI-1 | Ms4a6d | | |
| 4951 | 3 | 4 | 5 | 6 | | VI-1 | Mfap2 | 4237 | 4-May-15 | 5045 | 3 | 4 | 5 | 6 | | VI-1 | Ms4a8a | | |
| 4952 | 3 | 4 | 5 | 6 | | VI-1 | Mfap5 | 8076 | 21-May-15 | 5046 | 3 | 4 | 5 | 6 | | VI-1 | Msh5 | 4439 | 12-May-15 |
| 4953 | 3 | 4 | 5 | 6 | | VI-1 | Mfge8 | 4240 | 4-May-15 | 5047 | 3 | 4 | 5 | 6 | | VI-1 | Msln | 10232 | 4-May-15 |
| 4954 | 3 | 4 | 5 | 6 | | VI-1 | Mfsd12 | 126321 | 12-May-15 | 5048 | 3 | 4 | 5 | 6 | | VI-1 | Msmo1 | 6307 | 4-May-15 |
| 4955 | 3 | 4 | 5 | 6 | | VI-1 | Mgp | 4256 | 12-May-15 | 5049 | 3 | 4 | 5 | 6 | | VI-1 | Msn | 4478 | 17-May-15 |
| 4956 | 3 | 4 | 5 | 6 | | VI-1 | Mgst1 | 4257 | 21-May-15 | 5050 | 3 | 4 | 5 | 6 | | VI-1 | Msr1 | 4481 | 17-May-15 |
| 4957 | 3 | 4 | 5 | 6 | | VI-1 | Mgst2 | 4258 | 4-May-15 | 5051 | 3 | 4 | 5 | 6 | | VI-1 | Mss51 | 118490 | 4-May-15 |
| 4958 | 3 | 4 | 5 | 6 | | VI-1 | Mgst3 | 4259 | 4-May-15 | 5052 | 3 | 4 | 5 | 6 | | VI-1 | Mst1r | 4486 | 12-May-15 |
| 4959 | 3 | 4 | 5 | 6 | | VI-1 | Micall2 | 79778 | 4-May-15 | 5053 | 3 | 4 | 5 | 6 | | VI-1 | Mstn | 2660 | 23-May-15 |
| 4960 | 3 | 4 | 5 | 6 | | VI-1 | Mid1ip1 | 58526 | 4-May-15 | 5054 | 3 | 4 | 5 | 6 | | VI-1 | Mt1 | 4489, 4494, 4495 | 7-Jun-15 |
| 4961 | 3 | 4 | 5 | 6 | | VI-1 | Mir1 | 284021 | 12-May-15 | 5055 | 3 | 4 | 5 | 6 | | VI-1 | Mt2 | 4502 | 7-Jun-15 |
| 4962 | 3 | 4 | 5 | 6 | | VI-1 | Minpp1 | 9562 | 4-May-15 | 5056 | 3 | 4 | 5 | 6 | | VI-1 | Mtfr1 | 9650 | 20-May-15 |
| 4963 | 3 | 4 | 5 | 6 | | VI-1 | Mir1188 | | | 5057 | 3 | 4 | 5 | 6 | | VI-1 | Mtfr2 | 113115 | 4-May-15 |
| 4964 | 3 | 4 | 5 | 6 | | VI-1 | Mir1193 | 100422837 | 4-May-15 | 5058 | 3 | 4 | 5 | 6 | | VI-1 | Mthfd1l | 25902 | 4-May-15 |
| 4965 | 3 | 4 | 5 | 6 | | VI-1 | Mir124a-2 | | | 5059 | 3 | 4 | 5 | 6 | | VI-1 | Mthfd2 | 10797 | 4-May-15 |
| 4966 | 3 | 4 | 5 | 6 | | VI-1 | Mir133b | 442890 | 21-May-15 | 5060 | 3 | 4 | 5 | 6 | | VI-1 | Mthfr | 4524 | 4-May-15 |
| 4967 | 3 | 4 | 5 | 6 | | VI-1 | Mir146b | 574447 | 4-May-15 | 5061 | 3 | 4 | 5 | 6 | | VI-1 | Mtus2 | 23281 | 4-May-15 |
| 4968 | 3 | 4 | 5 | 6 | | VI-1 | Mir148a | 406940 | 21-May-15 | 5062 | 3 | 4 | 5 | 6 | | VI-1 | Muc1 | 4582 | 22-May-15 |
| 4969 | 3 | 4 | 5 | 6 | | VI-1 | Mir17hg | 407975 | 17-May-15 | 5063 | 3 | 4 | 5 | 6 | | VI-1 | Muc20 | 200958 | 4-May-15 |
| 4970 | 3 | 4 | 5 | 6 | | VI-1 | Mir1931 | | | 5064 | 3 | 4 | 5 | 6 | | VI-1 | Mum1l1 | 139221 | 4-May-15 |
| 4971 | 3 | 4 | 5 | 6 | | VI-1 | Mir1946a | | | 5065 | 3 | 4 | 5 | 6 | | VI-1 | Mustn1 | 389125 | 12-May-15 |
| 4972 | 3 | 4 | 5 | 6 | | VI-1 | Mir1961 | | | 5066 | 3 | 4 | 5 | 6 | | VI-1 | Mvd | 4597 | 4-May-15 |
| 4973 | 3 | 4 | 5 | 6 | | VI-1 | Mir1983 | | | 5067 | 3 | 4 | 5 | 6 | | VI-1 | Mvk | 4598 | 17-May-15 |
| 4974 | 3 | 4 | 5 | 6 | | VI-1 | Mir199a-2 | | | 5068 | 3 | 4 | 5 | 6 | | VI-1 | Mx1 | 4599 | 12-May-15 |
| 4975 | 3 | 4 | 5 | 6 | | VI-1 | Mir2861 | 100422910 | 9-May-15 | 5069 | 3 | 4 | 5 | 6 | | VI-1 | Mx2 | 4600 | 12-May-15 |
| 4976 | 3 | 4 | 5 | 6 | | VI-1 | Mir3473f | | | 5070 | 3 | 4 | 5 | 6 | | VI-1 | Mxd1 | 4084 | 24-May-15 |
| 4977 | 3 | 4 | 5 | 6 | | VI-1 | Mir3535 | | | 5071 | 3 | 4 | 5 | 6 | | VI-1 | Mxra7 | 439921 | 12-May-15 |
| 4978 | 3 | 4 | 5 | 6 | | VI-1 | Mir449c | 100313923 | 21-May-15 | 5072 | 3 | 4 | 5 | 6 | | VI-1 | Mxra8 | 54587 | 4-May-15 |
| 4979 | 3 | 4 | 5 | 6 | | VI-1 | Mir546 | | | 5073 | 3 | 4 | 5 | 6 | | VI-1 | Mybl1 | 4603 | 12-May-15 |
| 4980 | 3 | 4 | 5 | 6 | | VI-1 | Mir6339 | | | 5074 | 3 | 4 | 5 | 6 | | VI-1 | Mybl2 | 4605 | 4-May-15 |
| 4981 | 3 | 4 | 5 | 6 | | VI-1 | Mir6341 | | | 5075 | 3 | 4 | 5 | 6 | | VI-1 | Mybpc1 | 4604 | 4-May-15 |
| 4982 | 3 | 4 | 5 | 6 | | VI-1 | Mir6342 | | | 5076 | 3 | 4 | 5 | 6 | | VI-1 | Mybpc2 | 4606 | 4-May-15 |
| 4983 | 3 | 4 | 5 | 6 | | VI-1 | Mir6360 | | | 5077 | 3 | 4 | 5 | 6 | | VI-1 | Mybpc3 | 4607 | 23-May-15 |
| 4984 | 3 | 4 | 5 | 6 | | VI-1 | Mir6369 | | | 5078 | 3 | 4 | 5 | 6 | | VI-1 | Mybphl | 343263 | 4-May-15 |
| 4985 | 3 | 4 | 5 | 6 | | VI-1 | Mir6372 | | | 5079 | 3 | 4 | 5 | 6 | | VI-1 | Myc | 4609 | 24-May-15 |
| 4986 | 3 | 4 | 5 | 6 | | VI-1 | Mir6382 | | | 5080 | 3 | 4 | 5 | 6 | | VI-1 | Mycn | 4613 | 23-May-15 |
| 4987 | 3 | 4 | 5 | 6 | | VI-1 | Mir6383 | | | 5081 | 3 | 4 | 5 | 6 | | VI-1 | Myh10 | 4628 | 21-May-15 |
| 4988 | 3 | 4 | 5 | 6 | | VI-1 | Mir6413 | | | 5082 | 3 | 4 | 5 | 6 | | VI-1 | Myh14 | 79784 | 7-Jun-15 |
| 4989 | 3 | 4 | 5 | 6 | | VI-1 | Mir6539 | | | 5083 | 3 | 4 | 5 | 6 | | VI-1 | Myh2 | 4620 | 4-May-15 |
| 4990 | 3 | 4 | 5 | 6 | | VI-1 | Mir6541 | | | 5084 | 3 | 4 | 5 | 6 | | VI-1 | Myh4 | 4622 | 4-May-15 |
| 4991 | 3 | 4 | 5 | 6 | | VI-1 | Mir669e | | | 5085 | 3 | 4 | 5 | 6 | | VI-1 | Myh7 | 4625 | 23-May-15 |
| 4992 | 3 | 4 | 5 | 6 | | VI-1 | Mir669i | | | 5086 | 3 | 4 | 5 | 6 | | VI-1 | Myh9 | 4627 | 23-May-15 |
| 4993 | 3 | 4 | 5 | 6 | | VI-1 | Mir684-2 | | | 5087 | 3 | 4 | 5 | 6 | | VI-1 | Myl2 | 4633 | 23-May-15 |
| 4994 | 3 | 4 | 5 | 6 | | VI-1 | Mir690 | | | 5088 | 3 | 4 | 5 | 6 | | VI-1 | Mylk3 | 91807 | 12-May-15 |
| 4995 | 3 | 4 | 5 | 6 | | VI-1 | Mir692-2a | | | 5089 | 3 | 4 | 5 | 6 | | VI-1 | Mylk4 | 340156 | 4-May-15 |
| 4996 | 3 | 4 | 5 | 6 | | VI-1 | Mir692-2b | | | 5090 | 3 | 4 | 5 | 6 | | VI-1 | Mylpf | 29895 | 4-May-15 |
| 4997 | 3 | 4 | 5 | 6 | | VI-1 | Mir6957 | | | 5091 | 3 | 4 | 5 | 6 | | VI-1 | Myo1f | 4542 | 4-May-15 |
| 4998 | 3 | 4 | 5 | 6 | | VI-1 | Mir6982 | | | 5092 | 3 | 4 | 5 | 6 | | VI-1 | Myo1g | 64005 | 12-May-15 |
| 4999 | 3 | 4 | 5 | 6 | | VI-1 | Mir6990 | | | 5093 | 3 | 4 | 5 | 6 | | VI-1 | Myo5a | 4644 | 4-May-15 |
| 5000 | 3 | 4 | 5 | 6 | | VI-1 | Mir6992 | | | 5094 | 3 | 4 | 5 | 6 | | VI-1 | Myo7a | 4647 | 23-May-15 |
| 5001 | 3 | 4 | 5 | 6 | | VI-1 | Mir7-1 | 407043 | 24-May-15 | 5095 | 3 | 4 | 5 | 6 | | VI-1 | Myoc | 4653 | 16-May-15 |
| 5002 | 3 | 4 | 5 | 6 | | VI-1 | Mir717 | | | 5096 | 3 | 4 | 5 | 6 | | VI-1 | Myof | 26509 | 4-May-15 |
| 5003 | 3 | 4 | 5 | 6 | | VI-1 | Mir7233 | | | 5097 | 3 | 4 | 5 | 6 | | VI-1 | Myog | 4656 | 4-May-15 |
| 5004 | 3 | 4 | 5 | 6 | | VI-1 | Mir8095 | | | 5098 | 3 | 4 | 5 | 6 | | VI-1 | Myom1 | 8736 | 12-May-15 |
| 5005 | 3 | 4 | 5 | 6 | | VI-1 | Mir8100 | | | 5099 | 3 | 4 | 5 | 6 | | VI-1 | Myom2 | 9172 | 24-May-15 |
| 5006 | 3 | 4 | 5 | 6 | | VI-1 | Mir8111 | | | 5100 | 3 | 4 | 5 | 6 | | VI-1 | Myot | 9499 | 23-May-15 |
| 5007 | 3 | 4 | 5 | 6 | | VI-1 | Mir8119 | | | 5101 | 3 | 4 | 5 | 6 | | VI-1 | Myoz1 | 58529 | 12-May-15 |
| 5008 | 3 | 4 | 5 | 6 | | VI-1 | Mir9-2 | 407047 | 21-May-15 | 5102 | 3 | 4 | 5 | 6 | | VI-1 | Myoz2 | 51778 | 12-May-15 |

Fig. 30 - 28

| | | | | | | | | | | | | | | | | | |
|---|---|---|---|---|---|---|---|---|---|---|---|---|---|---|---|---|---|
| 5103 | 3 | 4 | 5 | 6 | | VI-1 | Myrip | 25924 | 4-May-15 | 5198 | 3 | 4 | 5 | 6 | | VI-1 | Nudt10 | 170685 | 7-Jun-15 |
| 5104 | 3 | 4 | 5 | 6 | | VI-1 | Myzap | 100820829 | 4-May-15 | 5199 | 3 | 4 | 5 | 6 | | VI-1 | Nudt4 | 11163 | 12-May-15 |
| 5105 | 3 | 4 | 5 | 6 | | VI-1 | N4bp2 | 55728 | 12-May-15 | 5200 | 3 | 4 | 5 | 6 | | VI-1 | Nup210 | 23225 | 4-May-15 |
| 5106 | 3 | 4 | 5 | 6 | | VI-1 | Naaa | 27163 | 4-May-15 | 5201 | 3 | 4 | 5 | 6 | | VI-1 | Nupr1l | 389493 | 4-May-15 |
| 5107 | 3 | 4 | 5 | 6 | | VI-1 | Naalad2 | 10003 | 4-May-15 | 5202 | 3 | 4 | 5 | 6 | | VI-1 | Nwd1 | 284434 | 9-May-15 |
| 5108 | 3 | 4 | 5 | 6 | | VI-1 | Nabp1 | 64859 | 4-May-15 | 5203 | 3 | 4 | 5 | 6 | | VI-1 | Nxnl1 | 115861 | 4-May-15 |
| 5109 | 3 | 4 | 5 | 6 | | VI-1 | Nadk2 | 133686 | 4-May-15 | 5204 | 3 | 4 | 5 | 6 | | VI-1 | Nxpe3 | 91775 | 4-May-15 |
| 5110 | 3 | 4 | 5 | 6 | | VI-1 | Nags | 162417 | 3-May-15 | 5205 | 3 | 4 | 5 | 6 | | VI-1 | Nxpe4 | 54827 | 4-May-15 |
| 5111 | 3 | 4 | 5 | 6 | | VI-1 | Nanos3 | 342977 | 4-May-15 | 5206 | 3 | 4 | 5 | 6 | | VI-1 | Nxph4 | 11247 | 4-May-15 |
| 5112 | 3 | 4 | 5 | 6 | | VI-1 | Nans | 54187 | 4-May-15 | 5207 | 3 | 4 | 5 | 6 | | VI-1 | Oaf | 220323 | 4-May-15 |
| 5113 | 3 | 4 | 5 | 6 | | VI-1 | Nasp | 4678 | 21-May-15 | 5208 | 3 | 4 | 5 | 6 | | VI-1 | Oas1a | | |
| 5114 | 3 | 4 | 5 | 6 | | VI-1 | Nbl1 | 4681 | 10-May-15 | 5209 | 3 | 4 | 5 | 6 | | VI-1 | Oas1b | | |
| 5115 | 3 | 4 | 5 | 6 | | VI-1 | Ncam1 | 4684 | 12-May-15 | 5210 | 3 | 4 | 5 | 6 | | VI-1 | Oas1g | | |
| 5116 | 3 | 4 | 5 | 6 | | VI-1 | Ncapd2 | 9918 | 21-May-15 | 5211 | 3 | 4 | 5 | 6 | | VI-1 | Oas3 | 4940 | 10-May-15 |
| 5117 | 3 | 4 | 5 | 6 | | VI-1 | Ncapg2 | 54892 | 4-May-15 | 5212 | 3 | 4 | 5 | 6 | | VI-1 | Oasl1 | | |
| 5118 | 3 | 4 | 5 | 6 | | VI-1 | Ncaph | 13397 | 12-May-15 | 5213 | 3 | 4 | 5 | 6 | | VI-1 | Oasl2 | | |
| 5119 | 3 | 4 | 5 | 6 | | VI-1 | Nccrp1 | 342897 | 4-May-15 | 5214 | 3 | 4 | 5 | 6 | | VI-1 | Oaz3 | 51686 | 12-May-15 |
| 5120 | 3 | 4 | 5 | 6 | | VI-1 | Ncf1 | 653361 | 12-May-15 | 5215 | 3 | 4 | 5 | 6 | | VI-1 | Ociad2 | 132299 | 4-May-15 |
| 5121 | 3 | 4 | 5 | 6 | | VI-1 | Ncf2 | 4688 | 12-May-15 | 5216 | 3 | 4 | 5 | 6 | | VI-1 | Ocln | 100506658 | 12-May-15 |
| 5122 | 3 | 4 | 5 | 6 | | VI-1 | Ncf4 | 4689 | 4-May-15 | 5217 | 3 | 4 | 5 | 6 | | VI-1 | Ocstamp | 128506 | 4-May-15 |
| 5123 | 3 | 4 | 5 | 6 | | VI-1 | Nckap1l | 3071 | 4-May-15 | 5218 | 3 | 4 | 5 | 6 | | VI-1 | Odc1 | 4953 | 7-Jun-15 |
| 5124 | 3 | 4 | 5 | 6 | | VI-1 | Ncr1 | 9437 | 4-May-15 | 5219 | 3 | 4 | 5 | 6 | | VI-1 | Ogn | 4969 | 12-May-15 |
| 5125 | 3 | 4 | 5 | 6 | | VI-1 | Ndn | 4692 | 23-May-15 | 5220 | 3 | 4 | 5 | 6 | | VI-1 | Oip5 | 11339 | 4-May-15 |
| 5126 | 3 | 4 | 5 | 6 | | VI-1 | Ndrg1 | 10397 | 23-May-15 | 5221 | 3 | 4 | 5 | 6 | | VI-1 | Olfm4 | 10562 | 4-May-15 |
| 5127 | 3 | 4 | 5 | 6 | | VI-1 | Ndrg4 | 65009 | 4-May-15 | 5222 | 3 | 4 | 5 | 6 | | VI-1 | Olfml3 | 56944 | 4-May-15 |
| 5128 | 3 | 4 | 5 | 6 | | VI-1 | Ndufa4l2 | 56901 | 4-May-15 | 5223 | 3 | 4 | 5 | 6 | | VI-1 | Olfr1338 | | |
| 5129 | 3 | 4 | 5 | 6 | | VI-1 | Neat1 | 283131 | 12-May-15 | 5224 | 3 | 4 | 5 | 6 | | VI-1 | Olfr1342 | | |
| 5130 | 3 | 4 | 5 | 6 | | VI-1 | Nebl | 10529 | 4-May-15 | 5225 | 3 | 4 | 5 | 6 | | VI-1 | Omd | 4958 | 4-May-15 |
| 5131 | 3 | 4 | 5 | 6 | | VI-1 | Nedd9 | 4739 | 4-May-15 | 5226 | 3 | 4 | 5 | 6 | | VI-1 | Optc | 26254 | 4-May-15 |
| 5132 | 3 | 4 | 5 | 6 | | VI-1 | Neil1 | 79661 | 4-May-15 | 5227 | 3 | 4 | 5 | 6 | | VI-1 | Orai2 | 80228 | 4-May-15 |
| 5133 | 3 | 4 | 5 | 6 | | VI-1 | Nek2 | 4751 | 4-May-15 | 5228 | 3 | 4 | 5 | 6 | | VI-1 | Orc1 | 4998 | 7-Jun-15 |
| 5134 | 3 | 4 | 5 | 6 | | VI-1 | Nek6 | 10783 | 4-May-15 | 5229 | 3 | 4 | 5 | 6 | | VI-1 | Orm1 | 5004 | 12-May-15 |
| 5135 | 3 | 4 | 5 | 6 | | VI-1 | Nes | 10763 | 17-May-15 | 5230 | 3 | 4 | 5 | 6 | | VI-1 | Osbpl7 | 114883 | 21-May-15 |
| 5136 | 3 | 4 | 5 | 6 | | VI-1 | Neu3 | 10825 | 3-May-15 | 5231 | 3 | 4 | 5 | 6 | | VI-1 | Osm | 5008 | 7-Jun-15 |
| 5137 | 3 | 4 | 5 | 6 | | VI-1 | Neurl3 | 93082 | 7-Jun-15 | 5232 | 3 | 4 | 5 | 6 | | VI-1 | OTTMUSG00000016609 | | |
| 5138 | 3 | 4 | 5 | 6 | | VI-1 | Nexn | 91624 | 23-May-15 | 5233 | 3 | 4 | 5 | 6 | | VI-1 | Otub2 | 78990 | 4-May-15 |
| 5139 | 3 | 4 | 5 | 6 | | VI-1 | Nfe2 | 4778 | 12-May-15 | 5234 | 3 | 4 | 5 | 6 | | VI-1 | Ovgp1 | 5016 | 12-May-15 |
| 5140 | 3 | 4 | 5 | 6 | | VI-1 | Nfil3 | 4783 | 4-May-15 | 5235 | 3 | 4 | 5 | 6 | | VI-1 | Oxct1 | 5019 | 4-May-15 |
| 5141 | 3 | 4 | 5 | 6 | | VI-1 | Nfkbid | 84807 | 4-May-15 | 5236 | 3 | 4 | 5 | 6 | | VI-1 | P2rx3 | 5024 | 4-May-15 |
| 5142 | 3 | 4 | 5 | 6 | | VI-1 | Nfkbie | 4794 | 12-May-15 | 5237 | 3 | 4 | 5 | 6 | | VI-1 | P2rx5 | 5026 | 24-May-15 |
| 5143 | 3 | 4 | 5 | 6 | | VI-1 | Nfkbiz | 64332 | 4-May-15 | 5238 | 3 | 4 | 5 | 6 | | VI-1 | P2rx7 | 5027 | 17-May-15 |
| 5144 | 3 | 4 | 5 | 6 | | VI-1 | Ngf | 4803 | 24-May-15 | 5239 | 3 | 4 | 5 | 6 | | VI-1 | P2ry10 | 27334 | 4-May-15 |
| 5145 | 3 | 4 | 5 | 6 | | VI-1 | Ngfr | 4804 | 17-May-15 | 5240 | 3 | 4 | 5 | 6 | | VI-1 | P2ry6 | 5031 | 4-May-15 |
| 5146 | 3 | 4 | 5 | 6 | | VI-1 | Ngfrap1 | 27018 | 12-May-15 | 5241 | 3 | 4 | 5 | 6 | | VI-1 | P4ha3 | 283208 | 4-May-15 |
| 5147 | 3 | 4 | 5 | 6 | | VI-1 | Nhlrc3 | 387921 | 4-May-15 | 5242 | 3 | 4 | 5 | 6 | | VI-1 | Pabpc4 | 8761 | 4-May-15 |
| 5148 | 3 | 4 | 5 | 6 | | VI-1 | Nhlrc4 | 283948 | 21-May-15 | 5243 | 3 | 4 | 5 | 6 | | VI-1 | Padi2 | 11240 | 4-May-15 |
| 5149 | 3 | 4 | 5 | 6 | | VI-1 | Nhsl1 | 57224 | 4-May-15 | 5244 | 3 | 4 | 5 | 6 | | VI-1 | Pafah1b3 | 5050 | 4-May-15 |
| 5150 | 3 | 4 | 5 | 6 | | VI-1 | Nid1 | 4811 | 12-May-15 | 5245 | 3 | 4 | 5 | 6 | | VI-1 | Pak1 | 5058 | 7-Jun-15 |
| 5151 | 3 | 4 | 5 | 6 | | VI-1 | Ninl | 22981 | 4-May-15 | 5246 | 3 | 4 | 5 | 6 | | VI-1 | Palm | 5064 | 12-May-15 |
| 5152 | 3 | 4 | 5 | 6 | | VI-1 | Nipa1 | 123606 | 12-May-15 | 5247 | 3 | 4 | 5 | 6 | | VI-1 | Pam | 5066 | 13-Jun-15 |
| 5153 | 3 | 4 | 5 | 6 | | VI-1 | Nipal1 | 152519 | 4-May-15 | 5248 | 3 | 4 | 5 | 6 | | VI-1 | Pamr1 | 25891 | 4-May-15 |
| 5154 | 3 | 4 | 5 | 6 | | VI-1 | Nkain4 | 128414 | 4-May-15 | 5249 | 3 | 4 | 5 | 6 | | VI-1 | Panx1 | 24145 | 4-May-15 |
| 5155 | 3 | 4 | 5 | 6 | | VI-1 | Nkd1 | 85407 | 12-May-15 | 5250 | 3 | 4 | 5 | 6 | | VI-1 | Paqr9 | 344838 | 4-May-15 |
| 5156 | 3 | 4 | 5 | 6 | | VI-1 | Nkd2 | 85409 | 4-May-15 | 5251 | 3 | 4 | 5 | 6 | | VI-1 | Pard6b | 84612 | 4-May-15 |
| 5157 | 3 | 4 | 5 | 6 | | VI-1 | Nkx2-1 | 7080 | 23-May-15 | 5252 | 3 | 4 | 5 | 6 | | VI-1 | Parp12 | 64761 | 4-May-15 |
| 5158 | 3 | 4 | 5 | 6 | | VI-1 | Nlrc3 | 197336 | 4-May-15 | 5253 | 3 | 4 | 5 | 6 | | VI-1 | Parp16 | 54956 | 4-May-15 |
| 5159 | 3 | 4 | 5 | 6 | | VI-1 | Nlrc4 | 58484 | 12-May-15 | 5254 | 3 | 4 | 5 | 6 | | VI-1 | Parpbp | 55010 | 4-May-15 |
| 5160 | 3 | 4 | 5 | 6 | | VI-1 | Nlrc5 | 84166 | 10-May-15 | 5255 | 3 | 4 | 5 | 6 | | VI-1 | Parvg | 64098 | 12-May-15 |
| 5161 | 3 | 4 | 5 | 6 | | VI-1 | Nlrp3 | 114548 | 24-May-15 | 5256 | 3 | 4 | 5 | 6 | | VI-1 | Pask | 23178 | 7-Jun-15 |
| 5162 | 3 | 4 | 5 | 6 | | VI-1 | Nme1 | 4830 | 7-Jun-15 | 5257 | 3 | 4 | 5 | 6 | | VI-1 | Pax8 | 7849 | 24-May-15 |
| 5163 | 3 | 4 | 5 | 6 | | VI-1 | Nme9 | 347736 | 4-May-15 | 5258 | 3 | 4 | 5 | 6 | | VI-1 | Pced1b | 91523 | 4-May-15 |
| 5164 | 3 | 4 | 5 | 6 | | VI-1 | Nmnat3 | 349565 | 4-May-15 | 5259 | 3 | 4 | 5 | 6 | | VI-1 | Pcna | 5111 | 17-May-15 |
| 5165 | 3 | 4 | 5 | 6 | | VI-1 | Nmrall | 57407 | 20-May-15 | 5260 | 3 | 4 | 5 | 6 | | VI-1 | Pcolce | 5118 | 4-May-15 |
| 5166 | 3 | 4 | 5 | 6 | | VI-1 | Nnat | 4826 | 4-May-15 | 5261 | 3 | 4 | 5 | 6 | | VI-1 | Pcolce2 | 26577 | 12-May-15 |
| 5167 | 3 | 4 | 5 | 6 | | VI-1 | Nnmt | 4837 | 17-May-15 | 5262 | 3 | 4 | 5 | 6 | | VI-1 | Pcp4 | 5121 | 4-May-15 |
| 5168 | 3 | 4 | 5 | 6 | | VI-1 | Nop58 | 51602 | 21-May-15 | 5263 | 3 | 4 | 5 | 6 | | VI-1 | Pcp4l1 | 654790 | 4-May-15 |
| 5169 | 3 | 4 | 5 | 6 | | VI-1 | Notch3 | 4854 | 23-May-15 | 5264 | 3 | 4 | 5 | 6 | | VI-1 | Pcsk5 | 5125 | 12-May-15 |
| 5170 | 3 | 4 | 5 | 6 | | VI-1 | Notch4 | 4855 | 4-May-15 | 5265 | 3 | 4 | 5 | 6 | | VI-1 | Pcsk9 | 255738 | 23-May-15 |
| 5171 | 3 | 4 | 5 | 6 | | VI-1 | Npas2 | 4862 | 4-May-15 | 5266 | 3 | 4 | 5 | 6 | | VI-1 | Pcyt1b | 9468 | 4-May-15 |
| 5172 | 3 | 4 | 5 | 6 | | VI-1 | Npc2 | 10577 | 23-May-15 | 5267 | 3 | 4 | 5 | 6 | | VI-1 | Pdcd1 | 5133 | 24-May-15 |
| 5173 | 3 | 4 | 5 | 6 | | VI-1 | Npl | 80896 | 4-May-15 | 5268 | 3 | 4 | 5 | 6 | | VI-1 | Pde11a | 50940 | 12-May-15 |
| 5174 | 3 | 4 | 5 | 6 | | VI-1 | Npnt | 255743 | 4-May-15 | 5269 | 3 | 4 | 5 | 6 | | VI-1 | Pde1b | 5153 | 21-May-15 |
| 5175 | 3 | 4 | 5 | 6 | | VI-1 | Npr3 | 4883 | un-2015 | 5270 | 3 | 4 | 5 | 6 | | VI-1 | Pde3b | 5140 | 4-May-15 |
| 5176 | 3 | 4 | 5 | 6 | | VI-1 | Npy1r | 4886 | 4-May-15 | 5271 | 3 | 4 | 5 | 6 | | VI-1 | Pde4b | 5142 | 4-May-15 |
| 5177 | 3 | 4 | 5 | 6 | | VI-1 | Nqo1 | 1728 | 17-May-15 | 5272 | 3 | 4 | 5 | 6 | | VI-1 | Pde8b | 8622 | 4-May-15 |
| 5178 | 3 | 4 | 5 | 6 | | VI-1 | Nr1d1 | 9572 | 12-May-15 | 5273 | 3 | 4 | 5 | 6 | | VI-1 | Pde9a | 5152 | 4-May-15 |
| 5179 | 3 | 4 | 5 | 6 | | VI-1 | Nrap | 4892 | 7-Jun-15 | 5274 | 3 | 4 | 5 | 6 | | VI-1 | Pdgfc | 56034 | 17-May-15 |
| 5180 | 3 | 4 | 5 | 6 | | VI-1 | Nrg1 | 3084 | 12-May-15 | 5275 | 3 | 4 | 5 | 6 | | VI-1 | Pdgfra | 5156 | 4-May-15 |
| 5181 | 3 | 4 | 5 | 6 | | VI-1 | Nrg4 | 145957 | 4-May-15 | 5276 | 3 | 4 | 5 | 6 | | VI-1 | Pdgfrl | 5157 | 4-May-15 |
| 5182 | 3 | 4 | 5 | 6 | | VI-1 | Nrgn | 4900 | 4-May-15 | 5277 | 3 | 4 | 5 | 6 | | VI-1 | Pdia4 | 9601 | 4-May-15 |
| 5183 | 3 | 4 | 5 | 6 | | VI-1 | Nrip3 | 56675 | 4-May-15 | 5278 | 3 | 4 | 5 | 6 | | VI-1 | Pdia5 | 10954 | 4-May-15 |
| 5184 | 3 | 4 | 5 | 6 | | VI-1 | Nrm | 11270 | 4-May-15 | 5279 | 3 | 4 | 5 | 6 | | VI-1 | Pdlim2 | 64236 | 4-May-15 |
| 5185 | 3 | 4 | 5 | 6 | | VI-1 | Nrros | 375387 | 4-May-15 | 5280 | 3 | 4 | 5 | 6 | | VI-1 | Pdpn | 10630 | 17-May-15 |
| 5186 | 3 | 4 | 5 | 6 | | VI-1 | Nsdhl | 50814 | 23-May-15 | 5281 | 3 | 4 | 5 | 6 | | VI-1 | Pdzk1 | 5174 | 17-May-15 |
| 5187 | 3 | 4 | 5 | 6 | | VI-1 | Nsf1c | 55968 | 21-May-15 | 5282 | 3 | 4 | 5 | 6 | | VI-1 | Pdzk1ip1 | 10158 | 4-May-15 |
| 5188 | 3 | 4 | 5 | 6 | | VI-1 | Nsl1 | 25936 | 7-Jun-15 | 5283 | 3 | 4 | 5 | 6 | | VI-1 | Pebp1 | 5037 | 4-May-15 |
| 5189 | 3 | 4 | 5 | 6 | | VI-1 | Nsmf | 26012 | 4-May-15 | 5284 | 3 | 4 | 5 | 6 | | VI-1 | Peg3 | 5178 | 12-May-15 |
| 5190 | 3 | 4 | 5 | 6 | | VI-1 | Nt5c3 | 51251 | 4-May-15 | 5285 | 3 | 4 | 5 | 6 | | VI-1 | Peg3os | | |
| 5191 | 3 | 4 | 5 | 6 | | VI-1 | Nt5e | 4907 | 4-May-15 | 5286 | 3 | 4 | 5 | 6 | | VI-1 | Per1 | 5187 | 12-May-15 |
| 5192 | 3 | 4 | 5 | 6 | | VI-1 | Ntf3 | 4908 | 3-May-15 | 5287 | 3 | 4 | 5 | 6 | | VI-1 | Pf4 | 5196 | 24-May-15 |
| 5193 | 3 | 4 | 5 | 6 | | VI-1 | Ntrk1 | 4914 | 23-May-15 | 5288 | 3 | 4 | 5 | 6 | | VI-1 | Pfkfb3 | 5209 | 12-May-15 |
| 5194 | 3 | 4 | 5 | 6 | | VI-1 | Ntrk2 | 4915 | 4-May-15 | 5289 | 3 | 4 | 5 | 6 | | VI-1 | Pfkl | 5213 | 12-May-15 |
| 5195 | 3 | 4 | 5 | 6 | | VI-1 | Nts | 4922 | 4-May-15 | 5290 | 3 | 4 | 5 | 6 | | VI-1 | Pfkp | 5214 | 4-May-15 |
| 5196 | 3 | 4 | 5 | 6 | | VI-1 | Nuak2 | 81788 | 4-May-15 | 5291 | 3 | 4 | 5 | 6 | | VI-1 | Pgam2 | 5224 | 4-May-15 |
| 5197 | 3 | 4 | 5 | 6 | | VI-1 | Nucb2 | 4925 | 4-May-15 | | | | | | | | | | |

Fig. 30 - 29

| | | | | | | | | | | | | | | | | |
|---|---|---|---|---|---|---|---|---|---|---|---|---|---|---|---|---|
| 5292 | 3 | 4 | 5 | 6 | | VI-1 | Pgap3 | 80055 | 4-May-15 | 5388 | 3 | 4 | 5 | 6 | | VI-1 | Popdc2 | 64091 | 12-May-15 |
| 5293 | 3 | 4 | 5 | 6 | | VI-1 | Pgap2 | 27315 | 12-May-15 | 5389 | 3 | 4 | 5 | 6 | | VI-1 | Por | 5447 | 7-Jun-15 |
| 5294 | 3 | 4 | 5 | 6 | | VI-1 | Pgls | 25796 | 4-May-15 | 5390 | 3 | 4 | 5 | 6 | | VI-1 | Postn | 10631 | 17-May-15 |
| 5295 | 3 | 4 | 5 | 6 | | VI-1 | Pgm1 | 5236 | 23-May-15 | 5391 | 3 | 4 | 5 | 6 | | VI-1 | Pou2f2 | 5452 | 4-May-15 |
| 5296 | 3 | 4 | 5 | 6 | | VI-1 | Pgrmc1 | 10857 | 3-May-15 | 5392 | 3 | 4 | 5 | 6 | | VI-1 | Pou3f3 | 5455 | 4-May-15 |
| 5297 | 3 | 4 | 5 | 6 | | VI-1 | Phf11a | | | 5393 | 3 | 4 | 5 | 6 | | VI-1 | Ppan | 56342 | 4-May-15 |
| 5298 | 3 | 4 | 5 | 6 | | VI-1 | Phf11b | | | 5394 | 3 | 4 | 5 | 6 | | VI-1 | Ppara | 5465 | 17-May-15 |
| 5299 | 3 | 4 | 5 | 6 | | VI-1 | Phf11c | | | 5395 | 3 | 4 | 5 | 6 | | VI-1 | Ppard | 5467 | 17-May-15 |
| 5300 | 3 | 4 | 5 | 6 | | VI-1 | Phf19 | 26147 | 4-May-15 | 5396 | 3 | 4 | 5 | 6 | | VI-1 | Ppargc1a | 10891 | 24-May-15 |
| 5301 | 3 | 4 | 5 | 6 | | VI-1 | Phf6 | 84295 | 24-May-15 | 5397 | 3 | 4 | 5 | 6 | | VI-1 | Ppfia4 | 8497 | 4-May-15 |
| 5302 | 3 | 4 | 5 | 6 | | VI-1 | Phkg1 | 5260 | 12-May-15 | 5398 | 3 | 4 | 5 | 6 | | VI-1 | Ppic | 5480 | 4-May-15 |
| 5303 | 3 | 4 | 5 | 6 | | VI-1 | Phlda1 | 22822 | 4-May-15 | 5399 | 3 | 4 | 5 | 6 | | VI-1 | Ppil1 | 51645 | 12-May-15 |
| 5304 | 3 | 4 | 5 | 6 | | VI-1 | Phlda3 | 23612 | 14-May-15 | 5400 | 3 | 4 | 5 | 6 | | VI-1 | Ppl | 5493 | 4-May-15 |
| 5305 | 3 | 4 | 5 | 6 | | VI-1 | Phldb2 | 90102 | 4-May-15 | 5401 | 3 | 4 | 5 | 6 | | VI-1 | Ppox | 5498 | 13-Jun-15 |
| 5306 | 3 | 4 | 5 | 6 | | VI-1 | Phospho1 | 162466 | 4-May-15 | 5402 | 3 | 4 | 5 | 6 | | VI-1 | Ppp1r10 | 5514 | 4-May-15 |
| 5307 | 3 | 4 | 5 | 6 | | VI-1 | Phyhip | 9796 | 4-May-15 | 5403 | 3 | 4 | 5 | 6 | | VI-1 | Ppp1r13l | 10848 | 10-May-15 |
| 5308 | 3 | 4 | 5 | 6 | | VI-1 | Pi15 | 51050 | 4-May-15 | 5404 | 3 | 4 | 5 | 6 | | VI-1 | Ppp1r14a | 94274 | 4-May-15 |
| 5309 | 3 | 4 | 5 | 6 | | VI-1 | Pi16 | 221476 | 1-May-15 | 5405 | 3 | 4 | 5 | 6 | | VI-1 | Ppp1r15a | 23645 | 12-May-15 |
| 5310 | 3 | 4 | 5 | 6 | | VI-1 | Pi4k2b | 55300 | 4-May-15 | 5406 | 3 | 4 | 5 | 6 | | VI-1 | Ppp1r18 | 170954 | 4-May-15 |
| 5311 | 3 | 4 | 5 | 6 | | VI-1 | Pianp | 196500 | 4-May-15 | 5407 | 3 | 4 | 5 | 6 | | VI-1 | Ppp1r3b | 79660 | 4-May-15 |
| 5312 | 3 | 4 | 5 | 6 | | VI-1 | Picalm | 8301 | 4-May-15 | 5408 | 3 | 4 | 5 | 6 | | VI-1 | Ppp1r3c | 5507 | 4-May-15 |
| 5313 | 3 | 4 | 5 | 6 | | VI-1 | Pidd1 | 55367 | 12-May-15 | 5409 | 3 | 4 | 5 | 6 | | VI-1 | Ppp2r5b | 5526 | 4-May-15 |
| 5314 | 3 | 4 | 5 | 6 | | VI-1 | Piezo2 | 63895 | 21-May-15 | 5410 | 3 | 4 | 5 | 6 | | VI-1 | Ppp3cc | 5533 | 12-May-15 |
| 5315 | 3 | 4 | 5 | 6 | | VI-1 | Pif1 | 80119 | 24-May-15 | 5411 | 3 | 4 | 5 | 6 | | VI-1 | Pprc1 | 23082 | 4-May-15 |
| 5316 | 3 | 4 | 5 | 6 | | VI-1 | Pign | 9091 | 4-May-15 | 5412 | 3 | 4 | 5 | 6 | | VI-1 | Ppy | 5539 | 4-May-15 |
| 5317 | 3 | 4 | 5 | 6 | | VI-1 | Pigr | 5284 | 12-May-15 | 5413 | 3 | 4 | 5 | 6 | | VI-1 | Pqlc2 | 54896 | 4-May-15 |
| 5318 | 3 | 4 | 5 | 6 | | VI-1 | Pik3ap1 | 118788 | 4-May-15 | 5414 | 3 | 4 | 5 | 6 | | VI-1 | Pram1 | 84106 | 24-May-15 |
| 5319 | 3 | 4 | 5 | 6 | | VI-1 | Pik3cd | 5293 | 7-Jun-15 | 5415 | 3 | 4 | 5 | 6 | | VI-1 | Prc1 | 9055 | 4-May-15 |
| 5320 | 3 | 4 | 5 | 6 | | VI-1 | Pik3cg | 5294 | 12-May-15 | 5416 | 3 | 4 | 5 | 6 | | VI-1 | Prdm5 | 11107 | 12-May-15 |
| 5321 | 3 | 4 | 5 | 6 | | VI-1 | Pik3ip1 | 113791 | 4-May-15 | 5417 | 3 | 4 | 5 | 6 | | VI-1 | Prdx2 | 7001 | 4-May-15 |
| 5322 | 3 | 4 | 5 | 6 | | VI-1 | Pik3r5 | 23533 | 4-May-15 | 5418 | 3 | 4 | 5 | 6 | | VI-1 | Prelp | 5549 | 12-May-15 |
| 5323 | 3 | 4 | 5 | 6 | | VI-1 | Pilra | 29992 | 4-May-15 | 5419 | 3 | 4 | 5 | 6 | | VI-1 | Prex1 | 57580 | 4-May-15 |
| 5324 | 3 | 4 | 5 | 6 | | VI-1 | Pim1 | 5292 | 7-Jun-15 | 5420 | 3 | 4 | 5 | 6 | | VI-1 | Prg3 | 10394 | 4-May-15 |
| 5325 | 3 | 4 | 5 | 6 | | VI-1 | Pir | 8544 | 3-May-15 | 5421 | 3 | 4 | 5 | 6 | | VI-1 | Prim1 | 5557 | 17-May-15 |
| 5326 | 3 | 4 | 5 | 6 | | VI-1 | Pira1 | | | 5422 | 3 | 4 | 5 | 6 | | VI-1 | Prim2 | 5558 | 17-May-15 |
| 5327 | 3 | 4 | 5 | 6 | | VI-1 | Pira11 | | | 5423 | 3 | 4 | 5 | 6 | | VI-1 | Prkar2b | 5577 | 12-May-15 |
| 5328 | 3 | 4 | 5 | 6 | | VI-1 | Pira2 | | | 5424 | 3 | 4 | 5 | 6 | | VI-1 | Prkcd | 5580 | 17-May-15 |
| 5329 | 3 | 4 | 5 | 6 | | VI-1 | Pira4 | | | 5425 | 3 | 4 | 5 | 6 | | VI-1 | Prkd2 | 25865 | 4-May-15 |
| 5330 | 3 | 4 | 5 | 6 | | VI-1 | Pira6 | | | 5426 | 3 | 4 | 5 | 6 | | VI-1 | Procr | 10544 | 4-May-15 |
| 5331 | 3 | 4 | 5 | 6 | | VI-1 | Pira7 | | | 5427 | 3 | 4 | 5 | 6 | | VI-1 | Prok2 | 60675 | 23-May-15 |
| 5332 | 3 | 4 | 5 | 6 | | VI-1 | Pirb | 11025 | 4-May-15 | 5428 | 3 | 4 | 5 | 6 | | VI-1 | Prom1 | 8842 | 23-May-15 |
| 5333 | 3 | 4 | 5 | 6 | | VI-1 | Pisd-ps3 | | | 5429 | 3 | 4 | 5 | 6 | | VI-1 | Prr15 | 222171 | 4-May-15 |
| 5334 | 3 | 4 | 5 | 6 | | VI-1 | Pitx3 | 5309 | 23-May-15 | 5430 | 3 | 4 | 5 | 6 | | VI-1 | Prr15l | 79170 | 4-May-15 |
| 5335 | 3 | 4 | 5 | 6 | | VI-1 | Piwil4 | 143689 | 4-May-15 | 5431 | 3 | 4 | 5 | 6 | | VI-1 | Prr27 | 401137 | 4-May-15 |
| 5336 | 3 | 4 | 5 | 6 | | VI-1 | Pja1 | 64219 | 4-May-15 | 5432 | 3 | 4 | 5 | 6 | | VI-1 | Prr5 | 55615 | 4-May-15 |
| 5337 | 3 | 4 | 5 | 6 | | VI-1 | Pkhd1l1 | 93035 | 12-May-15 | 5433 | 3 | 4 | 5 | 6 | | VI-1 | Prrg1 | 5638 | 4-May-15 |
| 5338 | 3 | 4 | 5 | 6 | | VI-1 | Pkm | 5315 | 17-May-15 | 5434 | 3 | 4 | 5 | 6 | | VI-1 | Prrg3 | 79057 | 14-May-15 |
| 5339 | 3 | 4 | 5 | 6 | | VI-1 | Pkmyt1 | 9088 | 4-May-15 | 5435 | 3 | 4 | 5 | 6 | | VI-1 | Prrt1 | 80863 | 4-May-15 |
| 5340 | 3 | 4 | 5 | 6 | | VI-1 | Pla2g2c | 391013 | 4-May-15 | 5436 | 3 | 4 | 5 | 6 | | VI-1 | Prrx2 | 51450 | 4-May-15 |
| 5341 | 3 | 4 | 5 | 6 | | VI-1 | Pla2g4c | 8605 | 4-May-15 | 5437 | 3 | 4 | 5 | 6 | | VI-1 | Prss12 | 8492 | 4-May-15 |
| 5342 | 3 | 4 | 5 | 6 | | VI-1 | Pla2g5 | 5322 | 4-May-15 | 5438 | 3 | 4 | 5 | 6 | | VI-1 | Prss23 | 11098 | 12-May-15 |
| 5343 | 3 | 4 | 5 | 6 | | VI-1 | Pla2g7 | 7941 | 12-May-15 | 5439 | 3 | 4 | 5 | 6 | | VI-1 | Prss8 | 5652 | 12-May-15 |
| 5344 | 3 | 4 | 5 | 6 | | VI-1 | Plac9a | | | 5440 | 3 | 4 | 5 | 6 | | VI-1 | Psat1 | 29968 | 12-May-15 |
| 5345 | 3 | 4 | 5 | 6 | | VI-1 | Plac9b | | | 5441 | 3 | 4 | 5 | 6 | | VI-1 | Psd4 | 23550 | 4-May-15 |
| 5346 | 3 | 4 | 5 | 6 | | VI-1 | Plcg2 | 5336 | 12-May-15 | 5442 | 3 | 4 | 5 | 6 | | VI-1 | Psmb8 | 5696 | 4-May-15 |
| 5347 | 3 | 4 | 5 | 6 | | VI-1 | Plcl2 | 23228 | 14-May-15 | 5443 | 3 | 4 | 5 | 6 | | VI-1 | Psmb9 | 5698 | 12-May-15 |
| 5348 | 3 | 4 | 5 | 6 | | VI-1 | Pld3 | 23646 | 12-May-15 | 5444 | 3 | 4 | 5 | 6 | | VI-1 | Psmc3ip | 29893 | 4-May-15 |
| 5349 | 3 | 4 | 5 | 6 | | VI-1 | Pld4 | 122618 | 12-May-15 | 5445 | 3 | 4 | 5 | 6 | | VI-1 | Pstpip2 | 9050 | 4-May-15 |
| 5350 | 3 | 4 | 5 | 6 | | VI-1 | Plek | 5341 | 4-May-15 | 5446 | 3 | 4 | 5 | 6 | | VI-1 | Ptafr | 5724 | 4-May-15 |
| 5351 | 3 | 4 | 5 | 6 | | VI-1 | Plek2 | 26499 | 4-May-15 | 5447 | 3 | 4 | 5 | 6 | | VI-1 | Ptdss2 | 81490 | 12-May-15 |
| 5352 | 3 | 4 | 5 | 6 | | VI-1 | Plekha2 | 59339 | 12-May-15 | 5448 | 3 | 4 | 5 | 6 | | VI-1 | Ptgds | 5730 | 12-May-15 |
| 5353 | 3 | 4 | 5 | 6 | | VI-1 | Plekha3 | 65977 | 12-May-15 | 5449 | 3 | 4 | 5 | 6 | | VI-1 | Ptger2 | 5732 | 4-May-15 |
| 5354 | 3 | 4 | 5 | 6 | | VI-1 | Plekha4 | 57664 | 4-May-15 | 5450 | 3 | 4 | 5 | 6 | | VI-1 | Ptger4 | 5734 | 4-May-15 |
| 5355 | 3 | 4 | 5 | 6 | | VI-1 | Plekhb1 | 58473 | 4-May-15 | 5451 | 3 | 4 | 5 | 6 | | VI-1 | Ptgis | 5740 | 12-May-15 |
| 5356 | 3 | 4 | 5 | 6 | | VI-1 | Plekhd1 | 400224 | 4-May-15 | 5452 | 3 | 4 | 5 | 6 | | VI-1 | Pth | 5741 | 7-Jun-15 |
| 5357 | 3 | 4 | 5 | 6 | | VI-1 | Plekhf1 | 79156 | 21-May-15 | 5453 | 3 | 4 | 5 | 6 | | VI-1 | Pth1r | 5745 | 12-May-15 |
| 5358 | 3 | 4 | 5 | 6 | | VI-1 | Plekhn1 | 84069 | 4-May-15 | 5454 | 3 | 4 | 5 | 6 | | VI-1 | Ptk2b | 2185 | 4-May-15 |
| 5359 | 3 | 4 | 5 | 6 | | VI-1 | Plgrkt | 55848 | 4-May-15 | 5455 | 3 | 4 | 5 | 6 | | VI-1 | Ptk7 | 5754 | 4-May-15 |
| 5360 | 3 | 4 | 5 | 6 | | VI-1 | Plin5 | 440503 | 4-May-15 | 5456 | 3 | 4 | 5 | 6 | | VI-1 | Ptp4a1 | 7803 | 17-May-15 |
| 5361 | 3 | 4 | 5 | 6 | | VI-1 | Plk1 | 5347 | 24-May-15 | 5457 | 3 | 4 | 5 | 6 | | VI-1 | Ptp4a3 | 11156 | 24-May-15 |
| 5362 | 3 | 4 | 5 | 6 | | VI-1 | Plk3 | 1263 | 4-May-15 | 5458 | 3 | 4 | 5 | 6 | | VI-1 | Ptpn18 | 26469 | 4-May-15 |
| 5363 | 3 | 4 | 5 | 6 | | VI-1 | Plk4 | 10733 | 24-May-15 | 5459 | 3 | 4 | 5 | 6 | | VI-1 | Ptpn22 | 26191 | 17-May-15 |
| 5364 | 3 | 4 | 5 | 6 | | VI-1 | Plp2 | 5355 | 4-May-15 | 5460 | 3 | 4 | 5 | 6 | | VI-1 | Ptpn3 | 5774 | 4-May-15 |
| 5365 | 3 | 4 | 5 | 6 | | VI-1 | Pls3 | 5358 | 12-May-15 | 5461 | 3 | 4 | 5 | 6 | | VI-1 | Ptpn6 | 5777 | 24-May-15 |
| 5366 | 3 | 4 | 5 | 6 | | VI-1 | Pltp | 5360 | 4-May-15 | 5462 | 3 | 4 | 5 | 6 | | VI-1 | Ptpn7 | 5778 | 4-May-15 |
| 5367 | 3 | 4 | 5 | 6 | | VI-1 | Plvap | 83483 | 4-May-15 | 5463 | 3 | 4 | 5 | 6 | | VI-1 | Ptprc | 5788 | 12-May-15 |
| 5368 | 3 | 4 | 5 | 6 | | VI-1 | Plxdc2 | 84898 | 4-May-15 | 5464 | 3 | 4 | 5 | 6 | | VI-1 | Ptprf | 5792 | 4-May-15 |
| 5369 | 3 | 4 | 5 | 6 | | VI-1 | Plxna2 | 5362 | 4-May-15 | 5465 | 3 | 4 | 5 | 6 | | VI-1 | Ptprn2 | 5799 | 12-May-15 |
| 5370 | 3 | 4 | 5 | 6 | | VI-1 | Plxnc1 | 10154 | 4-May-15 | 5466 | 3 | 4 | 5 | 6 | | VI-1 | Ptpro | 5800 | 7-Jun-15 |
| 5371 | 3 | 4 | 5 | 6 | | VI-1 | Pmaip1 | 5366 | 4-May-15 | 5467 | 3 | 4 | 5 | 6 | | VI-1 | Ptprv | 148713 | 4-May-15 |
| 5372 | 3 | 4 | 5 | 6 | | VI-1 | Pmch | 5367 | 4-May-15 | 5468 | 3 | 4 | 5 | 6 | | VI-1 | Ptrh1 | 138428 | 4-May-15 |
| 5373 | 3 | 4 | 5 | 6 | | VI-1 | Pmepa1 | 56937 | 4-May-15 | 5469 | 3 | 4 | 5 | 6 | | VI-1 | Pttg1 | 9232 | 17-May-15 |
| 5374 | 3 | 4 | 5 | 6 | | VI-1 | Pmf1 | 11243 | 7-Jun-15 | 5470 | 3 | 4 | 5 | 6 | | VI-1 | Pvalb | 5816 | 4-May-15 |
| 5375 | 3 | 4 | 5 | 6 | | VI-1 | Pml | 5371 | 21-May-15 | 5471 | 3 | 4 | 5 | 6 | | VI-1 | Pvr | 5817 | 17-May-15 |
| 5376 | 3 | 4 | 5 | 6 | | VI-1 | Pmp22 | 5376 | 7-Jun-15 | 5472 | 3 | 4 | 5 | 6 | | VI-1 | Pvrl1 | 5818 | 12-May-15 |
| 5377 | 3 | 4 | 5 | 6 | | VI-1 | Pmvk | 10654 | 4-May-15 | 5473 | 3 | 4 | 5 | 6 | | VI-1 | Pvrl4 | 81607 | 4-May-15 |
| 5378 | 3 | 4 | 5 | 6 | | VI-1 | Pnp2 | | | 5474 | 3 | 4 | 5 | 6 | | VI-1 | Pxdc1 | 221749 | 4-May-15 |
| 5379 | 3 | 4 | 5 | 6 | | VI-1 | Pnpla2 | 57104 | 4-May-15 | 5475 | 3 | 4 | 5 | 6 | | VI-1 | Pxmp2 | 5827 | 12-May-15 |
| 5380 | 3 | 4 | 5 | 6 | | VI-1 | Pnpla3 | 80339 | 24-May-15 | 5476 | 3 | 4 | 5 | 6 | | VI-1 | Pxylp1 | 92370 | 4-May-15 |
| 5381 | 3 | 4 | 5 | 6 | | VI-1 | Pnrc1 | 10957 | 12-May-15 | 5477 | 3 | 4 | 5 | 6 | | VI-1 | Pygl | 5836 | 23-May-15 |
| 5382 | 3 | 4 | 5 | 6 | | VI-1 | Podxl2 | 50512 | 4-May-15 | 5478 | 3 | 4 | 5 | 6 | | VI-1 | Pyy | 5697 | 23-May-15 |
| 5383 | 3 | 4 | 5 | 6 | | VI-1 | Pola1 | 5422 | 12-May-15 | 5479 | 3 | 4 | 5 | 6 | | VI-1 | Qsox2 | 169714 | 4-May-15 |
| 5384 | 3 | 4 | 5 | 6 | | VI-1 | Pold1 | 5424 | 21-May-15 | 5480 | 3 | 4 | 5 | 6 | | VI-1 | Rab11fip1 | 80223 | 4-May-15 |
| 5385 | 3 | 4 | 5 | 6 | | VI-1 | Pole | 5426 | 17-May-15 | 5481 | 3 | 4 | 5 | 6 | | VI-1 | Rab11fip4 | 84440 | 12-May-15 |
| 5386 | 3 | 4 | 5 | 6 | | VI-1 | Polq | 10721 | 7-Jun-15 | 5482 | 3 | 4 | 5 | 6 | | VI-1 | Rab15 | 376267 | 12-May-15 |
| 5387 | 3 | 4 | 5 | 6 | | VI-1 | Pon1 | 5444 | 17-May-15 | 5483 | 3 | 4 | 5 | 6 | | VI-1 | Rab19 | 401409 | 4-May-15 |

Fig. 30 - 30

| | | | | | | | | | | | | | | | | | | | |
|---|---|---|---|---|---|---|---|---|---|---|---|---|---|---|---|---|---|---|---|
| 5484 | 3 | 4 | 5 | 6 | | VI-1 | Rab25 | 57111 | 4-May-15 | 5580 | 3 | 4 | 5 | 6 | | VI-1 | Rmrp | 6023 | 23-May-15 |
| 5485 | 3 | 4 | 5 | 6 | | VI-1 | Rab26os | | | 5581 | 3 | 4 | 5 | 6 | | VI-1 | Rn4.5s | | |
| 5486 | 3 | 4 | 5 | 6 | | VI-1 | Rab31 | 11031 | 4-May-15 | 5582 | 3 | 4 | 5 | 6 | | VI-1 | Rnase10 | 338879 | 4-May-15 |
| 5487 | 3 | 4 | 5 | 6 | | VI-1 | Rab32 | 10981 | 4-May-15 | 5583 | 3 | 4 | 5 | 6 | | VI-1 | Rnase4 | 6038 | 7-Jun-15 |
| 5488 | 3 | 4 | 5 | 6 | | VI-1 | Rab3il1 | 5866 | 4-May-15 | 5584 | 3 | 4 | 5 | 6 | | VI-1 | Rnd1 | 27289 | 4-May-15 |
| 5489 | 3 | 4 | 5 | 6 | | VI-1 | Rab44 | 401258 | 4-May-15 | 5585 | 3 | 4 | 5 | 6 | | VI-1 | Rnf115 | 27246 | 4-May-15 |
| 5490 | 3 | 4 | 5 | 6 | | VI-1 | Rab6b | 51560 | 23-May-15 | 5586 | 3 | 4 | 5 | 6 | | VI-1 | Rnf157 | 114804 | 4-May-15 |
| 5491 | 3 | 4 | 5 | 6 | | VI-1 | Rab8b | 51762 | 4-May-15 | 5587 | 3 | 4 | 5 | 6 | | VI-1 | Rnf180 | 285671 | 4-May-15 |
| 5492 | 3 | 4 | 5 | 6 | | VI-1 | Racgap1 | 29127 | 3-May-15 | 5588 | 3 | 4 | 5 | 6 | | VI-1 | Ror2 | 4920 | 7-Jun-15 |
| 5493 | 3 | 4 | 5 | 6 | | VI-1 | Rad18 | 56852 | 12-May-15 | 5589 | 3 | 4 | 5 | 6 | | VI-1 | Rpa2 | 6118 | 7-Jun-15 |
| 5494 | 3 | 4 | 5 | 6 | | VI-1 | Rad23a | 5886 | 4-May-15 | 5590 | 3 | 4 | 5 | 6 | | VI-1 | Rpa3 | 6119 | 4-May-15 |
| 5495 | 3 | 4 | 5 | 6 | | VI-1 | Rad51ap1 | 10635 | 4-May-15 | 5591 | 3 | 4 | 5 | 6 | | VI-1 | Rpl26 | 6154 | 4-May-15 |
| 5496 | 3 | 4 | 5 | 6 | | VI-1 | Rad51b | 5890 | 4-May-15 | 5592 | 3 | 4 | 5 | 6 | | VI-1 | Rpl3l | 6123 | 4-May-15 |
| 5497 | 3 | 4 | 5 | 6 | | VI-1 | Rad54b | 25788 | 4-May-15 | 5593 | 3 | 4 | 5 | 6 | | VI-1 | Rpph1 | 85495 | 4-May-15 |
| 5498 | 3 | 4 | 5 | 6 | | VI-1 | Rad54l | 8438 | 7-Jun-15 | 5594 | 3 | 4 | 5 | 6 | | VI-1 | Rprd1a | 55197 | 12-May-15 |
| 5499 | 3 | 4 | 5 | 6 | | VI-1 | Rad54l2 | 23132 | 4-May-15 | 5595 | 3 | 4 | 5 | 6 | | VI-1 | Rprl3 | | |
| 5500 | 3 | 4 | 5 | 6 | | VI-1 | Rag2 | 5897 | 12-May-15 | 5596 | 3 | 4 | 5 | 6 | | VI-1 | Rprm | 56475 | 4-May-15 |
| 5501 | 3 | 4 | 5 | 6 | | VI-1 | Rai14 | 26064 | 4-May-15 | 5597 | 3 | 4 | 5 | 6 | | VI-1 | Rps26 | 6231 | 7-Jun-15 |
| 5502 | 3 | 4 | 5 | 6 | | VI-1 | Rai2 | 10742 | 4-May-15 | 5598 | 3 | 4 | 5 | 6 | | VI-1 | Rrad | 6236 | 4-May-15 |
| 5503 | 3 | 4 | 5 | 6 | | VI-1 | Ranbp10 | 57610 | 4-May-15 | 5599 | 3 | 4 | 5 | 6 | | VI-1 | Rragb | 10325 | 4-May-15 |
| 5504 | 3 | 4 | 5 | 6 | | VI-1 | Rap2b | 5912 | 4-May-15 | 5600 | 3 | 4 | 5 | 6 | | VI-1 | Rragd | 58528 | 4-May-15 |
| 5505 | 3 | 4 | 5 | 6 | | VI-1 | Rapgef4 | 11069 | 4-May-15 | 5601 | 3 | 4 | 5 | 6 | | VI-1 | Rras2 | 22800 | 4-May-15 |
| 5506 | 3 | 4 | 5 | 6 | | VI-1 | Rapgef5 | 9771 | 4-May-15 | 5602 | 3 | 4 | 5 | 6 | | VI-1 | Rrm1 | 6240 | 4-May-15 |
| 5507 | 3 | 4 | 5 | 6 | | VI-1 | Rapgefl1 | 51195 | 12-May-15 | 5603 | 3 | 4 | 5 | 6 | | VI-1 | Rrp12 | 23223 | 4-May-15 |
| 5508 | 3 | 4 | 5 | 6 | | VI-1 | Rarres1 | 5918 | 4-May-15 | 5604 | 3 | 4 | 5 | 6 | | VI-1 | Rsad2 | 91543 | 4-May-15 |
| 5509 | 3 | 4 | 5 | 6 | | VI-1 | Rarres2 | 5919 | 4-May-15 | 5605 | 3 | 4 | 5 | 6 | | VI-1 | Rspo1 | 284654 | 4-May-15 |
| 5510 | 3 | 4 | 5 | 6 | | VI-1 | Rasa4 | 10156 | 17-May-15 | 5606 | 3 | 4 | 5 | 6 | | VI-1 | Rtn2 | 6253 | 4-May-15 |
| 5511 | 3 | 4 | 5 | 6 | | VI-1 | Rasal3 | 64926 | 4-May-15 | 5607 | 3 | 4 | 5 | 6 | | VI-1 | Rtn4 | 57142 | 10-May-15 |
| 5512 | 3 | 4 | 5 | 6 | | VI-1 | Rasd1 | 51655 | 4-May-15 | 5608 | 3 | 4 | 5 | 6 | | VI-1 | Rtn4rl2 | 349667 | 4-May-15 |
| 5513 | 3 | 4 | 5 | 6 | | VI-1 | Rasef | 158158 | 14-May-15 | 5609 | 3 | 4 | 5 | 6 | | VI-1 | Rtp3 | 83597 | 9-May-15 |
| 5514 | 3 | 4 | 5 | 6 | | VI-1 | Rasgef1b | 153020 | 4-May-15 | 5610 | 3 | 4 | 5 | 6 | | VI-1 | Rtp4 | 64108 | 9-May-15 |
| 5515 | 3 | 4 | 5 | 6 | | VI-1 | Rasgrp2 | 10235 | 4-May-15 | 5611 | 3 | 4 | 5 | 6 | | VI-1 | Rubie | | |
| 5516 | 3 | 4 | 5 | 6 | | VI-1 | Rasgrp3 | 25780 | 12-May-15 | 5612 | 3 | 4 | 5 | 6 | | VI-1 | Rufy4 | 285180 | 4-May-15 |
| 5517 | 3 | 4 | 5 | 6 | | VI-1 | Ras11b | 65997 | 4-May-15 | 5613 | 3 | 4 | 5 | 6 | | VI-1 | Rundc3a | 10900 | 6-May-15 |
| 5518 | 3 | 4 | 5 | 6 | | VI-1 | Rassf1 | 11186 | 17-May-15 | 5614 | 3 | 4 | 5 | 6 | | VI-1 | Rundc3b | 154661 | 4-May-15 |
| 5519 | 3 | 4 | 5 | 6 | | VI-1 | Rassf4 | 83937 | 13-Jun-15 | 5615 | 3 | 4 | 5 | 6 | | VI-1 | Runx1 | 861 | 21-May-15 |
| 5520 | 3 | 4 | 5 | 6 | | VI-1 | Rassf5 | 83593 | 13-Jun-15 | 5616 | 3 | 4 | 5 | 6 | | VI-1 | Runx3 | 864 | 21-May-15 |
| 5521 | 3 | 4 | 5 | 6 | | VI-1 | Rassf6 | 166824 | 4-May-15 | 5617 | 3 | 4 | 5 | 6 | | VI-1 | Rxrg | 6258 | 4-May-15 |
| 5522 | 3 | 4 | 5 | 6 | | VI-1 | Rbm3 | 5935 | 4-May-15 | 5618 | 3 | 4 | 5 | 6 | | VI-1 | S100a10 | 6281 | 12-May-15 |
| 5523 | 3 | 4 | 5 | 6 | | VI-1 | Rbm38 | 55544 | 4-May-15 | 5619 | 3 | 4 | 5 | 6 | | VI-1 | S100a11 | 6282 | 4-May-15 |
| 5524 | 3 | 4 | 5 | 6 | | VI-1 | Rbm43 | 375287 | 4-May-15 | 5620 | 3 | 4 | 5 | 6 | | VI-1 | S100a14 | 57402 | 7-Jun-15 |
| 5525 | 3 | 4 | 5 | 6 | | VI-1 | Rbms3 | 27303 | 4-May-15 | 5621 | 3 | 4 | 5 | 6 | | VI-1 | S100a2 | 6273 | 12-May-15 |
| 5526 | 3 | 4 | 5 | 6 | | VI-1 | Rbp1 | 5947 | 7-Jun-15 | 5622 | 3 | 4 | 5 | 6 | | VI-1 | S100a4 | 6275 | 17-May-15 |
| 5527 | 3 | 4 | 5 | 6 | | VI-1 | Rbp2 | 5948 | 7-Jun-15 | 5623 | 3 | 4 | 5 | 6 | | VI-1 | S100a6 | 6277 | 4-May-15 |
| 5528 | 3 | 4 | 5 | 6 | | VI-1 | Rbp4 | 5950 | 7-Jun-15 | 5624 | 3 | 4 | 5 | 6 | | VI-1 | S100a7a | 338324 | 4-May-15 |
| 5529 | 3 | 4 | 5 | 6 | | VI-1 | Rbp7 | 116362 | 30-Apr-15 | 5625 | 3 | 4 | 5 | 6 | | VI-1 | S1pr1 | 1901 | 12-May-15 |
| 5530 | 3 | 4 | 5 | 6 | | VI-1 | Rcan1 | 1827 | 17-May-15 | 5626 | 3 | 4 | 5 | 6 | | VI-1 | S1pr2 | 9294 | 21-May-15 |
| 5531 | 3 | 4 | 5 | 6 | | VI-1 | Rcan2 | 10231 | 4-May-15 | 5627 | 3 | 4 | 5 | 6 | | VI-1 | S1pr4 | 8698 | 4-May-15 |
| 5532 | 3 | 4 | 5 | 6 | | VI-1 | Rcc1 | 1104 | 4-May-15 | 5628 | 3 | 4 | 5 | 6 | | VI-1 | Sacs | 26278 | 23-May-15 |
| 5533 | 3 | 4 | 5 | 6 | | VI-1 | Rcsd1 | 92241 | 23-May-15 | 5629 | 3 | 4 | 5 | 6 | | VI-1 | Sae1 | 10055 | 4-May-15 |
| 5534 | 3 | 4 | 5 | 6 | | VI-1 | Rd3 | 647286 | 4-May-15 | 5630 | 3 | 4 | 5 | 6 | | VI-1 | Samd10 | 140700 | 4-May-15 |
| 5535 | 3 | 4 | 5 | 6 | | VI-1 | Rdh12 | 145226 | 23-May-15 | 5631 | 3 | 4 | 5 | 6 | | VI-1 | Samd14 | 201191 | 4-May-15 |
| 5536 | 3 | 4 | 5 | 6 | | VI-1 | Recql4 | 9401 | 23-May-15 | 5632 | 3 | 4 | 5 | 6 | | VI-1 | Samd5 | 389432 | 12-May-15 |
| 5537 | 3 | 4 | 5 | 6 | | VI-1 | Redrum | | | 5633 | 3 | 4 | 5 | 6 | | VI-1 | Samd9l | 219285 | 12-May-15 |
| 5538 | 3 | 4 | 5 | 6 | | VI-1 | Reep2 | 51308 | 4-May-15 | 5634 | 3 | 4 | 5 | 6 | | VI-1 | Samsn1 | 64092 | 4-May-15 |
| 5539 | 3 | 4 | 5 | 6 | | VI-1 | Reep6 | 92840 | 4-May-15 | 5635 | 3 | 4 | 5 | 6 | | VI-1 | Sap30 | 8819 | 4-May-15 |
| 5540 | 3 | 4 | 5 | 6 | | VI-1 | Rel | 768211 | 4-May-15 | 5636 | 3 | 4 | 5 | 6 | | VI-1 | Sapcd1 | 401251 | 4-May-15 |
| 5541 | 3 | 4 | 5 | 6 | | VI-1 | Relt | 84957 | 4-May-15 | 5637 | 3 | 4 | 5 | 6 | | VI-1 | Sapcd2 | 89958 | 4-May-15 |
| 5542 | 3 | 4 | 5 | 6 | | VI-1 | Rem1 | 28954 | 4-May-15 | 5638 | 3 | 4 | 5 | 6 | | VI-1 | Sash3 | 54440 | 4-May-15 |
| 5543 | 3 | 4 | 5 | 6 | | VI-1 | Ren1 | | | 5639 | 3 | 4 | 5 | 6 | | VI-1 | Sass6 | 163786 | 4-May-15 |
| 5544 | 3 | 4 | 5 | 6 | | VI-1 | Renbp | 5973 | 4-May-15 | 5640 | 3 | 4 | 5 | 6 | | VI-1 | Sat1 | 6303 | 13-Jun-15 |
| 5545 | 3 | 4 | 5 | 6 | | VI-1 | Rerg | 85004 | 4-May-15 | 5641 | 3 | 4 | 5 | 6 | | VI-1 | Sbk1 | 388228 | 4-May-15 |
| 5546 | 3 | 4 | 5 | 6 | | VI-1 | Retsat | 54884 | 12-May-15 | 5642 | 3 | 4 | 5 | 6 | | VI-1 | Sbk2 | 646643 | 4-May-15 |
| 5547 | 3 | 4 | 5 | 6 | | VI-1 | Rfc2 | 5982 | 4-May-15 | 5643 | 3 | 4 | 5 | 6 | | VI-1 | Sbno2 | 22904 | 4-May-15 |
| 5548 | 3 | 4 | 5 | 6 | | VI-1 | Rfc3 | 5983 | 4-May-15 | 5644 | 3 | 4 | 5 | 6 | | VI-1 | Sc5d | 6309 | 12-May-15 |
| 5549 | 3 | 4 | 5 | 6 | | VI-1 | Rfc4 | 5984 | 4-May-15 | 5645 | 3 | 4 | 5 | 6 | | VI-1 | Scamp5 | 192683 | 4-May-15 |
| 5550 | 3 | 4 | 5 | 6 | | VI-1 | Rfc5 | 5985 | 4-May-15 | 5646 | 3 | 4 | 5 | 6 | | VI-1 | Scara3 | 51435 | 3-May-15 |
| 5551 | 3 | 4 | 5 | 6 | | VI-1 | Rftn1 | 23180 | 4-May-15 | 5647 | 3 | 4 | 5 | 6 | | VI-1 | Scara5 | 286133 | 4-May-15 |
| 5552 | 3 | 4 | 5 | 6 | | VI-1 | Rfx2 | 5990 | 4-May-15 | 5648 | 3 | 4 | 5 | 6 | | VI-1 | Scarf2 | 91179 | 21-May-15 |
| 5553 | 3 | 4 | 5 | 6 | | VI-1 | Rgcc | 28984 | 4-May-15 | 5649 | 3 | 4 | 5 | 6 | | VI-1 | Scarna13 | 677768 | 4-May-15 |
| 5554 | 3 | 4 | 5 | 6 | | VI-1 | Rgn | 9104 | 4-May-15 | 5650 | 3 | 4 | 5 | 6 | | VI-1 | Scarna6 | 677772 | 4-May-15 |
| 5555 | 3 | 4 | 5 | 6 | | VI-1 | Rgs1 | 5996 | 4-May-15 | 5651 | 3 | 4 | 5 | 6 | | VI-1 | Scd1 | 6319 | 4-May-15 |
| 5556 | 3 | 4 | 5 | 6 | | VI-1 | Rgs10 | 6001 | 4-May-15 | 5652 | 3 | 4 | 5 | 6 | | VI-1 | Scgb1b2 | | |
| 5557 | 3 | 4 | 5 | 6 | | VI-1 | Rgs11 | 8786 | 21-May-15 | 5653 | 3 | 4 | 5 | 6 | | VI-1 | Scml4 | 256380 | 12-May-15 |
| 5558 | 3 | 4 | 5 | 6 | | VI-1 | Rgs13 | 6003 | 7-Jun-15 | 5654 | 3 | 4 | 5 | 6 | | VI-1 | Scn10a | 6336 | 4-May-15 |
| 5559 | 3 | 4 | 5 | 6 | | VI-1 | Rgs14 | 10636 | 4-May-15 | 5655 | 3 | 4 | 5 | 6 | | VI-1 | Scn4a | 6329 | 22-May-15 |
| 5560 | 3 | 4 | 5 | 6 | | VI-1 | Rgs18 | 64407 | 4-May-15 | 5656 | 3 | 4 | 5 | 6 | | VI-1 | Scn1a | 6337 | 12-May-15 |
| 5561 | 3 | 4 | 5 | 6 | | VI-1 | Rgs19 | 10287 | 4-May-15 | 5657 | 3 | 4 | 5 | 6 | | VI-1 | Scn2 | 9997 | 4-May-15 |
| 5562 | 3 | 4 | 5 | 6 | | VI-1 | Rgs2 | 5997 | 7-Jun-15 | 5658 | 3 | 4 | 5 | 6 | | VI-1 | Scrn2 | 90507 | 4-May-15 |
| 5563 | 3 | 4 | 5 | 6 | | VI-1 | Rgs4 | 5999 | 4-May-15 | 5659 | 3 | 4 | 5 | 6 | | VI-1 | Scrn3 | 79634 | 12-May-15 |
| 5564 | 3 | 4 | 5 | 6 | | VI-1 | Rgs9 | 8787 | 7-Jun-15 | 5660 | 3 | 4 | 5 | 6 | | VI-1 | Sct | 6343 | 7-Jun-15 |
| 5565 | 3 | 4 | 5 | 6 | | VI-1 | Rhag | 6005 | 12-May-15 | 5661 | 3 | 4 | 5 | 6 | | VI-1 | Sdc1 | 6382 | 17-May-15 |
| 5566 | 3 | 4 | 5 | 6 | | VI-1 | Rhbdd3 | 25807 | 4-May-15 | 5662 | 3 | 4 | 5 | 6 | | VI-1 | Sdc4 | 6385 | 3-May-15 |
| 5567 | 3 | 4 | 5 | 6 | | VI-1 | Rhbdl2 | 54933 | 4-May-15 | 5663 | 3 | 4 | 5 | 6 | | VI-1 | Sdcbp2 | 27111 | 4-May-15 |
| 5568 | 3 | 4 | 5 | 6 | | VI-1 | Rhd | 6007 | 21-May-15 | 5664 | 3 | 4 | 5 | 6 | | VI-1 | Sdf2l1 | 23753 | 4-May-15 |
| 5569 | 3 | 4 | 5 | 6 | | VI-1 | Rhno1 | 83695 | 4-May-15 | 5665 | 3 | 4 | 5 | 6 | | VI-1 | Sdpr | 8436 | 12-May-15 |
| 5570 | 3 | 4 | 5 | 6 | | VI-1 | Rhobtb1 | 9886 | 12-May-15 | 5666 | 3 | 4 | 5 | 6 | | VI-1 | Sdsl | 113675 | 12-May-15 |
| 5571 | 3 | 4 | 5 | 6 | | VI-1 | Rhoj | 57381 | 4-May-15 | 5667 | 3 | 4 | 5 | 6 | | VI-1 | Sec11c | 90701 | 14-May-15 |
| 5572 | 3 | 4 | 5 | 6 | | VI-1 | Rims4 | 140730 | 4-May-15 | 5668 | 3 | 4 | 5 | 6 | | VI-1 | Sec14l2 | 23541 | 4-May-15 |
| 5573 | 3 | 4 | 5 | 6 | | VI-1 | Rin1 | 9610 | 4-May-15 | 5669 | 3 | 4 | 5 | 6 | | VI-1 | Sec31b | 25956 | 4-May-15 |
| 5574 | 3 | 4 | 5 | 6 | | VI-1 | Rin3 | 79890 | 4-May-15 | 5670 | 3 | 4 | 5 | 6 | | VI-1 | Sec61b | 10952 | 4-May-15 |
| 5575 | 3 | 4 | 5 | 6 | | VI-1 | Ripk3 | 11035 | 17-May-15 | 5671 | 3 | 4 | 5 | 6 | | VI-1 | Sel113 | 23231 | 12-May-15 |
| 5576 | 3 | 4 | 5 | 6 | | VI-1 | Ripk4 | 54101 | 10-May-15 | 5672 | 3 | 4 | 5 | 6 | | VI-1 | Sele | 6401 | 17-May-15 |
| 5577 | 3 | 4 | 5 | 6 | | VI-1 | Rlf | 6018 | 7-Jun-15 | 5673 | 3 | 4 | 5 | 6 | | VI-1 | Selenbp1 | 8991 | 4-May-15 |
| 5578 | 3 | 4 | 5 | 6 | | VI-1 | Rltpr | 146206 | 4-May-15 | 5674 | 3 | 4 | 5 | 6 | | VI-1 | Selenbp2 | | |
| 5579 | 3 | 4 | 5 | 6 | | VI-1 | Rmi2 | 116028 | 4-May-15 | 5675 | 3 | 4 | 5 | 6 | | VI-1 | Sell | 6402 | 17-May-15 |

Fig. 30 - 31

| # | | | | | | ID | Gene | Num | Date | # | | | | | | ID | Gene | Num | Date |
|---|---|---|---|---|---|---|---|---|---|---|---|---|---|---|---|---|---|---|---|
| 5676 | 3 | 4 | 5 | 6 | | VI-1 | Selp | 6403 | 7-Jun-15 | 5772 | 3 | 4 | 5 | 6 | | VI-1 | Slc16a11 | 162515 | 4-May-15 |
| 5677 | 3 | 4 | 5 | 6 | | VI-1 | Selplg | 6404 | 12-May-15 | 5773 | 3 | 4 | 5 | 6 | | VI-1 | Slc16a14 | 151473 | 4-May-15 |
| 5678 | 3 | 4 | 5 | 6 | | VI-1 | Sema3d | 223117 | 21-May-15 | 5774 | 3 | 4 | 5 | 6 | | VI-1 | Slc16a2 | 6567 | 23-May-15 |
| 5679 | 3 | 4 | 5 | 6 | | VI-1 | Sema3f | 6405 | 4-May-15 | 5775 | 3 | 4 | 5 | 6 | | VI-1 | Slc16a6 | 9120 | 20-May-15 |
| 5680 | 3 | 4 | 5 | 6 | | VI-1 | Sema4b | 10509 | 4-May-15 | 5776 | 3 | 4 | 5 | 6 | | VI-1 | Slc16a7 | 9194 | 4-May-15 |
| 5681 | 3 | 4 | 5 | 6 | | VI-1 | Sema6b | 10501 | 4-May-15 | 5777 | 3 | 4 | 5 | 6 | | VI-1 | Slc17a8 | 246213 | 23-May-15 |
| 5682 | 3 | 4 | 5 | 6 | | VI-1 | Sema7a | 8482 | 4-May-15 | 5778 | 3 | 4 | 5 | 6 | | VI-1 | Slc19a2 | 10560 | 23-May-15 |
| 5683 | 3 | 4 | 5 | 6 | | VI-1 | Sept1 | 1731 | 4-May-15 | 5779 | 3 | 4 | 5 | 6 | | VI-1 | Slc1a3 | 6507 | 23-May-15 |
| 5684 | 3 | 4 | 5 | 6 | | VI-1 | Sept5 | 5413 | 4-May-15 | 5780 | 3 | 4 | 5 | 6 | | VI-1 | Slc22a23 | 63027 | 10-May-15 |
| 5685 | 3 | 4 | 5 | 6 | | VI-1 | Sept6 | 23157 | 4-May-15 | 5781 | 3 | 4 | 5 | 6 | | VI-1 | Slc22a4 | 6583 | 12-May-15 |
| 5686 | 3 | 4 | 5 | 6 | | VI-1 | Sept8 | 23176 | 4-May-15 | 5782 | 3 | 4 | 5 | 6 | | VI-1 | Slc24a5 | 283652 | 12-May-15 |
| 5687 | 3 | 4 | 5 | 6 | | VI-1 | Serpina10 | 51156 | 12-May-15 | 5783 | 3 | 4 | 5 | 6 | | VI-1 | Slc25a21 | 89874 | 4-May-15 |
| 5688 | 3 | 4 | 5 | 6 | | VI-1 | Serpina1a | | | 5784 | 3 | 4 | 5 | 6 | | VI-1 | Slc25a25 | 114789 | 4-May-15 |
| 5689 | 3 | 4 | 5 | 6 | | VI-1 | Serpina1b | | | 5785 | 3 | 4 | 5 | 6 | | VI-1 | Slc25a30 | 253512 | 4-May-15 |
| 5690 | 3 | 4 | 5 | 6 | | VI-1 | Serpina1c | | | 5786 | 3 | 4 | 5 | 6 | | VI-1 | Slc25a37 | 51312 | 4-May-15 |
| 5691 | 3 | 4 | 5 | 6 | | VI-1 | Serpina1d | | | 5787 | 3 | 4 | 5 | 6 | | VI-1 | Slc25a38 | 54977 | 24-May-15 |
| 5692 | 3 | 4 | 5 | 6 | | VI-1 | Serpina1e | | | 5788 | 3 | 4 | 5 | 6 | | VI-1 | Slc25a39 | 51629 | 4-May-15 |
| 5693 | 3 | 4 | 5 | 6 | | VI-1 | Serpina3a | | | 5789 | 3 | 4 | 5 | 6 | | VI-1 | Slc25a4 | 291 | 4-May-15 |
| 5694 | 3 | 4 | 5 | 6 | | VI-1 | Serpina3c | | | 5790 | 3 | 4 | 5 | 6 | | VI-1 | Slc25a47 | 283600 | 4-May-15 |
| 5695 | 3 | 4 | 5 | 6 | | VI-1 | Serpina3f | | | 5791 | 3 | 4 | 5 | 6 | | VI-1 | Slc25a51 | 92014 | 4-May-15 |
| 5696 | 3 | 4 | 5 | 6 | | VI-1 | Serpina3g | | | 5792 | 3 | 4 | 5 | 6 | | VI-1 | Slc26a1 | 10861 | 4-May-15 |
| 5697 | 3 | 4 | 5 | 6 | | VI-1 | Serpina3h | | | 5793 | 3 | 4 | 5 | 6 | | VI-1 | Slc26a10 | 65012 | 4-May-15 |
| 5698 | 3 | 4 | 5 | 6 | | VI-1 | Serpina3i | | | 5794 | 3 | 4 | 5 | 6 | | VI-1 | Slc26a4 | 5172 | 22-May-15 |
| 5699 | 3 | 4 | 5 | 6 | | VI-1 | Serpina3j | | | 5795 | 3 | 4 | 5 | 6 | | VI-1 | Slc27a2 | 11001 | 4-May-15 |
| 5700 | 3 | 4 | 5 | 6 | | VI-1 | Serpina3k | | | 5796 | 3 | 4 | 5 | 6 | | VI-1 | Slc29a3 | 55315 | 4-May-15 |
| 5701 | 3 | 4 | 5 | 6 | | VI-1 | Serpina3m | | | 5797 | 3 | 4 | 5 | 6 | | VI-1 | Slc2a1 | 6513 | 24-May-15 |
| 5702 | 3 | 4 | 5 | 6 | | VI-1 | Serpina3n | | | 5798 | 3 | 4 | 5 | 6 | | VI-1 | Slc2a10 | 81031 | 23-May-15 |
| 5703 | 3 | 4 | 5 | 6 | | VI-1 | Serpinb11 | 89778 | 12-May-15 | 5799 | 3 | 4 | 5 | 6 | | VI-1 | Slc2a3 | 6515 | 12-May-15 |
| 5704 | 3 | 4 | 5 | 6 | | VI-1 | Serpinb1a | | | 5800 | 3 | 4 | 5 | 6 | | VI-1 | Slc2a4 | 6517 | 17-May-15 |
| 5705 | 3 | 4 | 5 | 6 | | VI-1 | Serpinb3a | | | 5801 | 3 | 4 | 5 | 6 | | VI-1 | Slc30a10 | 55532 | 23-May-15 |
| 5706 | 3 | 4 | 5 | 6 | | VI-1 | Serpinb3c | | | 5802 | 3 | 4 | 5 | 6 | | VI-1 | Slc30a2 | 7780 | 4-May-15 |
| 5707 | 3 | 4 | 5 | 6 | | VI-1 | Serpinb6b | | | 5803 | 3 | 4 | 5 | 6 | | VI-1 | Slc35f2 | 54733 | 4-May-15 |
| 5708 | 3 | 4 | 5 | 6 | | VI-1 | Serpinb9b | | | 5804 | 3 | 4 | 5 | 6 | | VI-1 | Slc35g1 | 159371 | 4-May-15 |
| 5709 | 3 | 4 | 5 | 6 | | VI-1 | Serpine2 | 5270 | 12-May-15 | 5805 | 3 | 4 | 5 | 6 | | VI-1 | Slc36a2 | 153201 | 4-May-15 |
| 5710 | 3 | 4 | 5 | 6 | | VI-1 | Serpinf1 | 5176 | 24-May-15 | 5806 | 3 | 4 | 5 | 6 | | VI-1 | Slc37a2 | 219855 | 4-May-15 |
| 5711 | 3 | 4 | 5 | 6 | | VI-1 | Serping1 | 710 | 12-May-15 | 5807 | 3 | 4 | 5 | 6 | | VI-1 | Slc38a1 | 81539 | 4-May-15 |
| 5712 | 3 | 4 | 5 | 6 | | VI-1 | Sertad1 | 29950 | 4-May-15 | 5808 | 3 | 4 | 5 | 6 | | VI-1 | Slc38a2 | 54407 | 12-May-15 |
| 5713 | 3 | 4 | 5 | 6 | | VI-1 | Sertad2 | 9792 | 21-May-15 | 5809 | 3 | 4 | 5 | 6 | | VI-1 | Slc38a4 | 55089 | 4-May-15 |
| 5714 | 3 | 4 | 5 | 6 | | VI-1 | Sertad4 | 56256 | 4-May-15 | 5810 | 3 | 4 | 5 | 6 | | VI-1 | Slc39a14 | 23516 | 4-May-15 |
| 5715 | 3 | 4 | 5 | 6 | | VI-1 | Sesn1 | 27244 | 4-May-15 | 5811 | 3 | 4 | 5 | 6 | | VI-1 | Slc39a6 | 25800 | 12-May-15 |
| 5716 | 3 | 4 | 5 | 6 | | VI-1 | Setbp1 | 26040 | 17-May-15 | 5812 | 3 | 4 | 5 | 6 | | VI-1 | Slc39a8 | 64116 | 4-May-15 |
| 5717 | 3 | 4 | 5 | 6 | | VI-1 | Setdb1 | 9869 | 4-May-15 | 5813 | 3 | 4 | 5 | 6 | | VI-1 | Slc41a3 | 54946 | 4-May-15 |
| 5718 | 3 | 4 | 5 | 6 | | VI-1 | Setdb2 | 83852 | 4-May-15 | 5814 | 3 | 4 | 5 | 6 | | VI-1 | Slc43a1 | 8501 | 4-May-15 |
| 5719 | 3 | 4 | 5 | 6 | | VI-1 | Sfn | 2810 | 7-Jun-15 | 5815 | 3 | 4 | 5 | 6 | | VI-1 | Slc43a3 | 29015 | 4-May-15 |
| 5720 | 3 | 4 | 5 | 6 | | VI-1 | Sfrp1 | 6422 | 12-May-15 | 5816 | 3 | 4 | 5 | 6 | | VI-1 | Slc44a2 | 57153 | 12-May-15 |
| 5721 | 3 | 4 | 5 | 6 | | VI-1 | Sfrp5 | 6425 | 10-May-15 | 5817 | 3 | 4 | 5 | 6 | | VI-1 | Slc45a3 | 85414 | 4-May-15 |
| 5722 | 3 | 4 | 5 | 6 | | VI-1 | Sfta2 | 389376 | 4-May-15 | 5818 | 3 | 4 | 5 | 6 | | VI-1 | Slc4a1 | 6521 | 14-May-15 |
| 5723 | 3 | 4 | 5 | 6 | | VI-1 | Sgk1 | 6446 | 21-May-15 | 5819 | 3 | 4 | 5 | 6 | | VI-1 | Slc4a11 | 83959 | 23-May-15 |
| 5724 | 3 | 4 | 5 | 6 | | VI-1 | Sgol1 | 151648 | 4-May-15 | 5820 | 3 | 4 | 5 | 6 | | VI-1 | Slc51b | 123264 | 4-May-15 |
| 5725 | 3 | 4 | 5 | 6 | | VI-1 | Sgol2 | 151246 | 4-May-15 | 5821 | 3 | 4 | 5 | 6 | | VI-1 | Slc5a3 | 6526 | 12-May-15 |
| 5726 | 3 | 4 | 5 | 6 | | VI-1 | Sgpp1 | 81537 | 4-May-15 | 5822 | 3 | 4 | 5 | 6 | | VI-1 | Slc5a9 | 200010 | 4-May-15 |
| 5727 | 3 | 4 | 5 | 6 | | VI-1 | Sh2b2 | 10603 | 21-May-15 | 5823 | 3 | 4 | 5 | 6 | | VI-1 | Slc6a12 | 6539 | 4-May-15 |
| 5728 | 3 | 4 | 5 | 6 | | VI-1 | Sh2d4a | 63898 | 4-May-15 | 5824 | 3 | 4 | 5 | 6 | | VI-1 | Slc6a17 | 388662 | 17-May-15 |
| 5729 | 3 | 4 | 5 | 6 | | VI-1 | Sh3bgr | 6450 | 7-Jun-15 | 5825 | 3 | 4 | 5 | 6 | | VI-1 | Slc6a20a | | |
| 5730 | 3 | 4 | 5 | 6 | | VI-1 | Sh3bgrl3 | 83442 | 4-May-15 | 5826 | 3 | 4 | 5 | 6 | | VI-1 | Slc6a4 | 6532 | 17-May-15 |
| 5731 | 3 | 4 | 5 | 6 | | VI-1 | Sh3bp2 | 6452 | 23-May-15 | 5827 | 3 | 4 | 5 | 6 | | VI-1 | Slc6a9 | 6536 | 4-May-15 |
| 5732 | 3 | 4 | 5 | 6 | | VI-1 | Sh3gl2 | 6456 | 12-May-15 | 5828 | 3 | 4 | 5 | 6 | | VI-1 | Slc7a1 | 6541 | 4-May-15 |
| 5733 | 3 | 4 | 5 | 6 | | VI-1 | Sh3pxd2a | 9644 | 4-May-15 | 5829 | 3 | 4 | 5 | 6 | | VI-1 | Slc7a10 | 56301 | 12-May-15 |
| 5734 | 3 | 4 | 5 | 6 | | VI-1 | Sh3pxd2b | 285590 | 12-May-15 | 5830 | 3 | 4 | 5 | 6 | | VI-1 | Slc7a11 | 23657 | 12-May-15 |
| 5735 | 3 | 4 | 5 | 6 | | VI-1 | Sh3rf2 | 153769 | 21-May-15 | 5831 | 3 | 4 | 5 | 6 | | VI-1 | Slc7a2 | 6542 | 4-May-15 |
| 5736 | 3 | 4 | 5 | 6 | | VI-1 | Sh3tc2 | 79628 | 23-May-15 | 5832 | 3 | 4 | 5 | 6 | | VI-1 | Slc7a4 | 6545 | 4-May-15 |
| 5737 | 3 | 4 | 5 | 6 | | VI-1 | Sh3yl1 | 26751 | 12-May-15 | 5833 | 3 | 4 | 5 | 6 | | VI-1 | Slc7a5 | 8140 | 4-May-15 |
| 5738 | 3 | 4 | 5 | 6 | | VI-1 | Shank1 | 50944 | 21-May-15 | 5834 | 3 | 4 | 5 | 6 | | VI-1 | Slc7a8 | 23428 | 4-May-15 |
| 5739 | 3 | 4 | 5 | 6 | | VI-1 | Shb | 6461 | 4-May-15 | 5835 | 3 | 4 | 5 | 6 | | VI-1 | Slc9a6 | 10479 | 7-Jun-15 |
| 5740 | 3 | 4 | 5 | 6 | | VI-1 | Shcbp1 | 79801 | 4-May-15 | 5836 | 3 | 4 | 5 | 6 | | VI-1 | Slc9a7 | 84679 | 4-May-15 |
| 5741 | 3 | 4 | 5 | 6 | | VI-1 | Shh | 6469 | 24-May-15 | 5837 | 3 | 4 | 5 | 6 | | VI-1 | Slco1a5 | | |
| 5742 | 3 | 4 | 5 | 6 | | VI-1 | Shisa2 | 387914 | 4-May-15 | 5838 | 3 | 4 | 5 | 6 | | VI-1 | Slco2a1 | 6578 | 17-May-15 |
| 5743 | 3 | 4 | 5 | 6 | | VI-1 | Shisa3 | 152573 | 4-May-15 | 5839 | 3 | 4 | 5 | 6 | | VI-1 | Slco4c1 | 353189 | 4-May-15 |
| 5744 | 3 | 4 | 5 | 6 | | VI-1 | Shisa4 | 149345 | 4-May-15 | 5840 | 3 | 4 | 5 | 6 | | VI-1 | Slfn14 | 342618 | 4-May-15 |
| 5745 | 3 | 4 | 5 | 6 | | VI-1 | Shmt2 | 6472 | 4-May-15 | 5841 | 3 | 4 | 5 | 6 | | VI-1 | Slfn5 | 162394 | 4-May-15 |
| 5746 | 3 | 4 | 5 | 6 | | VI-1 | Shroom2 | 357 | 4-May-15 | 5842 | 3 | 4 | 5 | 6 | | VI-1 | Slfn8 | | |
| 5747 | 3 | 4 | 5 | 6 | | VI-1 | Siglec1 | 6614 | 4-May-15 | 5843 | 3 | 4 | 5 | 6 | | VI-1 | Slfn9 | | |
| 5748 | 3 | 4 | 5 | 6 | | VI-1 | Sik1 | 150094 | 23-May-15 | 5844 | 3 | 4 | 5 | 6 | | VI-1 | Slit2 | 9353 | 7-Jun-15 |
| 5749 | 3 | 4 | 5 | 6 | | VI-1 | Sin3b | 23309 | 12-May-15 | 5845 | 3 | 4 | 5 | 6 | | VI-1 | Slit3 | 6586 | 7-Jun-15 |
| 5750 | 3 | 4 | 5 | 6 | | VI-1 | Sirpa | 140885 | 17-May-15 | 5846 | 3 | 4 | 5 | 6 | | VI-1 | Smap2 | 64744 | 7-Jun-15 |
| 5751 | 3 | 4 | 5 | 6 | | VI-1 | Sirpb1a | | | 5847 | 3 | 4 | 5 | 6 | | VI-1 | Smarca4 | 6597 | 4-May-15 |
| 5752 | 3 | 4 | 5 | 6 | | VI-1 | Sirpb1b | | | 5848 | 3 | 4 | 5 | 6 | | VI-1 | Smarcd3 | 6604 | 4-May-15 |
| 5753 | 3 | 4 | 5 | 6 | | VI-1 | Sit1 | 27240 | 7-Jun-15 | 5849 | 3 | 4 | 5 | 6 | | VI-1 | Smc2 | 10592 | 7-Jun-15 |
| 5754 | 3 | 4 | 5 | 6 | | VI-1 | Ska1 | 220134 | 4-May-15 | 5850 | 3 | 4 | 5 | 6 | | VI-1 | Smc4 | 10051 | 4-May-15 |
| 5755 | 3 | 4 | 5 | 6 | | VI-1 | Ska2 | 348235 | 24-May-15 | 5851 | 3 | 4 | 5 | 6 | | VI-1 | Smim22 | 440335 | 12-May-15 |
| 5756 | 3 | 4 | 5 | 6 | | VI-1 | Ska3 | 221150 | 4-May-15 | 5852 | 3 | 4 | 5 | 6 | | VI-1 | Smim3 | 85027 | 4-May-15 |
| 5757 | 3 | 4 | 5 | 6 | | VI-1 | Skap1 | 8631 | 4-May-15 | 5853 | 3 | 4 | 5 | 6 | | VI-1 | Smoc1 | 64093 | 4-May-15 |
| 5758 | 3 | 4 | 5 | 6 | | VI-1 | Skil | 6498 | 12-May-15 | 5854 | 3 | 4 | 5 | 6 | | VI-1 | Smox | 54498 | 4-May-15 |
| 5759 | 3 | 4 | 5 | 6 | | VI-1 | Skp2 | 6502 | 17-May-15 | 5855 | 3 | 4 | 5 | 6 | | VI-1 | Smpd3 | 55512 | 12-May-15 |
| 5760 | 3 | 4 | 5 | 6 | | VI-1 | Sla | 6503 | 7-Jun-15 | 5856 | 3 | 4 | 5 | 6 | | VI-1 | Smpdl3b | 27293 | 4-May-15 |
| 5761 | 3 | 4 | 5 | 6 | | VI-1 | Slamf8 | 56833 | 4-May-15 | 5857 | 3 | 4 | 5 | 6 | | VI-1 | Smtnl2 | 342527 | 4-May-15 |
| 5762 | 3 | 4 | 5 | 6 | | VI-1 | Slamf9 | 89886 | 12-May-15 | 5858 | 3 | 4 | 5 | 6 | | VI-1 | Snai1 | 6615 | 17-May-15 |
| 5763 | 3 | 4 | 5 | 6 | | VI-1 | Slbp | 7884 | 12-May-15 | 5859 | 3 | 4 | 5 | 6 | | VI-1 | Snap91 | 9892 | 4-May-15 |
| 5764 | 3 | 4 | 5 | 6 | | VI-1 | Slc10a3-ubl4 | | | 5860 | 3 | 4 | 5 | 6 | | VI-1 | Snca | 6622 | 24-May-15 |
| 5765 | 3 | 4 | 5 | 6 | | VI-1 | Slc10a6 | 345274 | 4-May-15 | 5861 | 3 | 4 | 5 | 6 | | VI-1 | Sncg | 6623 | 4-May-15 |
| 5766 | 3 | 4 | 5 | 6 | | VI-1 | Slc11a1 | 6556 | 12-May-15 | 5862 | 3 | 4 | 5 | 6 | | VI-1 | Snhg1 | 23642 | 4-May-15 |
| 5767 | 3 | 4 | 5 | 6 | | VI-1 | Slc12a3 | 6559 | 12-May-15 | 5863 | 3 | 4 | 5 | 6 | | VI-1 | Snhg12 | 85028 | 12-May-15 |
| 5768 | 3 | 4 | 5 | 6 | | VI-1 | Slc14a2 | 8170 | 3-May-15 | 5864 | 3 | 4 | 5 | 6 | | VI-1 | Snhg3 | 8420 | 4-May-15 |
| 5769 | 3 | 4 | 5 | 6 | | VI-1 | Slc15a3 | 51296 | 4-May-15 | 5865 | 3 | 4 | 5 | 6 | | VI-1 | Snhg4 | 724102 | 4-May-15 |
| 5770 | 3 | 4 | 5 | 6 | | VI-1 | Slc16a1 | 6566 | 21-May-15 | 5866 | 3 | 4 | 5 | 6 | | VI-1 | Snhg5 | 387066 | 12-May-15 |
| 5771 | 3 | 4 | 5 | 6 | | VI-1 | Slc16a10 | 117247 | 4-May-15 | 5867 | 3 | 4 | 5 | 6 | | VI-1 | Snhg6 | | |

Fig. 30 - 32

| | | | | | | | | | | | | | | | | | | |
|---|---|---|---|---|---|---|---|---|---|---|---|---|---|---|---|---|---|---|
| 5868 | 3 | 4 | 5 | 6 | | VI-1 | Snhg9 | 735301 | 12-May-15 | 5964 | 3 | 4 | 5 | 6 | | VI-1 | Suox | 6821 | 12-May-15 |
| 5869 | 3 | 4 | 5 | 6 | | VI-1 | Snora17 | 677804 | 4-May-15 | 5965 | 3 | 4 | 5 | 6 | | VI-1 | Susd3 | 203328 | 12-May-15 |
| 5870 | 3 | 4 | 5 | 6 | | VI-1 | Snora23 | 677808 | 4-May-15 | 5966 | 3 | 4 | 5 | 6 | | VI-1 | Susd4 | 55061 | 4-May-15 |
| 5871 | 3 | 4 | 5 | 6 | | VI-1 | Snora28 | 677811 | 4-May-15 | 5967 | 3 | 4 | 5 | 6 | | VI-1 | Suv39h2 | 79723 | 3-May-15 |
| 5872 | 3 | 4 | 5 | 6 | | VI-1 | Snora34 | 677815 | 4-May-15 | 5968 | 3 | 4 | 5 | 6 | | VI-1 | Svep1 | 79987 | 12-May-15 |
| 5873 | 3 | 4 | 5 | 6 | | VI-1 | Snora43 | 677824 | 4-May-15 | 5969 | 3 | 4 | 5 | 6 | | VI-1 | Svip | 258010 | 3-May-15 |
| 5874 | 3 | 4 | 5 | 6 | | VI-1 | Snora74a | 26821 | 4-May-15 | 5970 | 3 | 4 | 5 | 6 | | VI-1 | Syce2 | 256126 | 4-May-15 |
| 5875 | 3 | 4 | 5 | 6 | | VI-1 | Snora78 | 677844 | 4-May-15 | 5971 | 3 | 4 | 5 | 6 | | VI-1 | Syne1 | 23345 | 23-May-15 |
| 5876 | 3 | 4 | 5 | 6 | | VI-1 | Snora7a | 619563 | 4-May-15 | 5972 | 3 | 4 | 5 | 6 | | VI-1 | Syne3 | 161176 | 4-May-15 |
| 5877 | 3 | 4 | 5 | 6 | | VI-1 | Snord104 | 692227 | 12-May-15 | 5973 | 3 | 4 | 5 | 6 | | VI-1 | Syngr1 | 9145 | 4-May-15 |
| 5878 | 3 | 4 | 5 | 6 | | VI-1 | Snord15a | 6079 | 4-May-15 | 5974 | 3 | 4 | 5 | 6 | | VI-1 | Synpo | 11346 | 4-May-15 |
| 5879 | 3 | 4 | 5 | 6 | | VI-1 | Snord17 | 692086 | 4-May-15 | 5975 | 3 | 4 | 5 | 6 | | VI-1 | Synpo2l | 79933 | 4-May-15 |
| 5880 | 3 | 4 | 5 | 6 | | VI-1 | Snord2 | 619567 | 4-May-15 | 5976 | 3 | 4 | 5 | 6 | | VI-1 | Syt6 | 148281 | 4-May-15 |
| 5881 | 3 | 4 | 5 | 6 | | VI-1 | Snord22 | 9304 | 4-May-15 | 5977 | 3 | 4 | 5 | 6 | | VI-1 | Tac2 | 6863 | 4-May-15 |
| 5882 | 3 | 4 | 5 | 6 | | VI-1 | Snord32a | 26819 | 4-May-15 | 5978 | 3 | 4 | 5 | 6 | | VI-1 | Tacc3 | 10460 | 23-May-15 |
| 5883 | 3 | 4 | 5 | 6 | | VI-1 | Snord47 | 26802 | 4-May-15 | 5979 | 3 | 4 | 5 | 6 | | VI-1 | Taf7 | 6879 | 4-May-15 |
| 5884 | 3 | 4 | 5 | 6 | | VI-1 | Snord91a | 692207 | 12-May-15 | 5980 | 3 | 4 | 5 | 6 | | VI-1 | Tagln | 6876 | 12-May-15 |
| 5885 | 3 | 4 | 5 | 6 | | VI-1 | Snord96a | 619571 | 4-May-15 | 5981 | 3 | 4 | 5 | 6 | | VI-1 | Tagln2 | 8407 | 4-May-15 |
| 5886 | 3 | 4 | 5 | 6 | | VI-1 | Snrpe | 6635 | 12-May-15 | 5982 | 3 | 4 | 5 | 6 | | VI-1 | Tal1 | 6886 | 17-May-15 |
| 5887 | 3 | 4 | 5 | 6 | | VI-1 | Snx20 | 124460 | 4-May-15 | 5983 | 3 | 4 | 5 | 6 | | VI-1 | Tap1 | 6890 | 13-Jun-15 |
| 5888 | 3 | 4 | 5 | 6 | | VI-1 | Snx22 | 79856 | 4-May-15 | 5984 | 3 | 4 | 5 | 6 | | VI-1 | Tapt1 | 202018 | 4-May-15 |
| 5889 | 3 | 4 | 5 | 6 | | VI-1 | Snx5 | 27131 | 12-May-15 | 5985 | 3 | 4 | 5 | 6 | | VI-1 | Tarm1 | 441864 | 4-May-15 |
| 5890 | 3 | 4 | 5 | 6 | | VI-1 | Soat1 | 6646 | 4-May-15 | 5986 | 3 | 4 | 5 | 6 | | VI-1 | Tarsl2 | 123283 | 4-May-15 |
| 5891 | 3 | 4 | 5 | 6 | | VI-1 | Soat2 | 8435 | 12-May-15 | 5987 | 3 | 4 | 5 | 6 | | VI-1 | Tat | 6898 | 7-Jun-15 |
| 5892 | 3 | 4 | 5 | 6 | | VI-1 | Socs1 | 8651 | 4-May-15 | 5988 | 3 | 4 | 5 | 6 | | VI-1 | Tbc1d10c | 374403 | 12-May-15 |
| 5893 | 3 | 4 | 5 | 6 | | VI-1 | Socs2 | 8835 | 14-May-15 | 5989 | 3 | 4 | 5 | 6 | | VI-1 | Tbc1d16 | 125058 | 4-May-15 |
| 5894 | 3 | 4 | 5 | 6 | | VI-1 | Socs3 | 9021 | 23-May-15 | 5990 | 3 | 4 | 5 | 6 | | VI-1 | Tbc1d22bos | | |
| 5895 | 3 | 4 | 5 | 6 | | VI-1 | Sod3 | 6649 | 4-May-15 | 5991 | 3 | 4 | 5 | 6 | | VI-1 | Tbc1d8 | 11138 | 4-May-15 |
| 5896 | 3 | 4 | 5 | 6 | | VI-1 | Sost | 50964 | 24-May-15 | 5992 | 3 | 4 | 5 | 6 | | VI-1 | Tbc1d9 | 23158 | 4-May-15 |
| 5897 | 3 | 4 | 5 | 6 | | VI-1 | Sowaha | 134548 | 4-May-15 | 5993 | 3 | 4 | 5 | 6 | | VI-1 | Tbx1 | 6899 | 23-May-15 |
| 5898 | 3 | 4 | 5 | 6 | | VI-1 | Sox12 | 6666 | 4-May-15 | 5994 | 3 | 4 | 5 | 6 | | VI-1 | Tbx22 | 50945 | 17-May-15 |
| 5899 | 3 | 4 | 5 | 6 | | VI-1 | Sox13 | 9580 | 4-May-15 | 5995 | 3 | 4 | 5 | 6 | | VI-1 | Tbx3 | 6926 | 4-May-15 |
| 5900 | 3 | 4 | 5 | 6 | | VI-1 | Sox2 | 6657 | 24-May-15 | 5996 | 3 | 4 | 5 | 6 | | VI-1 | Tbx3os2 | | |
| 5901 | 3 | 4 | 5 | 6 | | VI-1 | Sox4 | 6659 | 4-May-15 | 5997 | 3 | 4 | 5 | 6 | | VI-1 | Tcap | 8557 | 23-May-15 |
| 5902 | 3 | 4 | 5 | 6 | | VI-1 | Sox5os3 | | | 5998 | 3 | 4 | 5 | 6 | | VI-1 | Tcf15 | 6939 | 10-May-15 |
| 5903 | 3 | 4 | 5 | 6 | | VI-1 | Sox6 | 55553 | 12-May-15 | 5999 | 3 | 4 | 5 | 6 | | VI-1 | Tcf19 | 6941 | 21-May-15 |
| 5904 | 3 | 4 | 5 | 6 | | VI-1 | Sox9 | 6662 | 23-May-15 | 6000 | 3 | 4 | 5 | 6 | | VI-1 | Tcf3 | 6929 | 7-Jun-15 |
| 5905 | 3 | 4 | 5 | 6 | | VI-1 | Sp100 | 6672 | 4-May-15 | 6001 | 3 | 4 | 5 | 6 | | VI-1 | Tcirg1 | 10312 | 12-May-15 |
| 5906 | 3 | 4 | 5 | 6 | | VI-1 | Sp6 | 80320 | 4-May-15 | 6002 | 3 | 4 | 5 | 6 | | VI-1 | Tead2 | 8463 | 4-May-15 |
| 5907 | 3 | 4 | 5 | 6 | | VI-1 | Sparc | 6678 | 17-May-15 | 6003 | 3 | 4 | 5 | 6 | | VI-1 | Tead4 | 7004 | 4-May-15 |
| 5908 | 3 | 4 | 5 | 6 | | VI-1 | Spata18 | 132671 | 4-May-15 | 6004 | 3 | 4 | 5 | 6 | | VI-1 | Tec | 7006 | 7-Jun-15 |
| 5909 | 3 | 4 | 5 | 6 | | VI-1 | Spc24 | 147841 | 4-May-15 | 6005 | 3 | 4 | 5 | 6 | | VI-1 | Tekt4 | 150483 | 4-May-15 |
| 5910 | 3 | 4 | 5 | 6 | | VI-1 | Spc25 | 57405 | 4-May-15 | 6006 | 3 | 4 | 5 | 6 | | VI-1 | Ten1 | 100134934 | 4-May-15 |
| 5911 | 3 | 4 | 5 | 6 | | VI-1 | Spcs2 | 9789 | 4-May-15 | 6007 | 3 | 4 | 5 | 6 | | VI-1 | Tenm3 | 55714 | 4-May-15 |
| 5912 | 3 | 4 | 5 | 6 | | VI-1 | Spdl1 | 54908 | 4-May-15 | 6008 | 3 | 4 | 5 | 6 | | VI-1 | Tes | 26136 | 4-May-15 |
| 5913 | 3 | 4 | 5 | 6 | | VI-1 | Specc1 | 92521 | 4-May-15 | 6009 | 3 | 4 | 5 | 6 | | VI-1 | Tespa1 | 9840 | 4-May-15 |
| 5914 | 3 | 4 | 5 | 6 | | VI-1 | Spi1 | 6688 | 12-May-15 | 6010 | 3 | 4 | 5 | 6 | | VI-1 | Tex15 | 56154 | 4-May-15 |
| 5915 | 3 | 4 | 5 | 6 | | VI-1 | Spint1 | 6692 | 4-May-15 | 6011 | 3 | 4 | 5 | 6 | | VI-1 | Tex30 | 93081 | 4-May-15 |
| 5916 | 3 | 4 | 5 | 6 | | VI-1 | Spint2 | 10653 | 21-May-15 | 6012 | 3 | 4 | 5 | 6 | | VI-1 | Tfcp2l1 | 29842 | 4-May-15 |
| 5917 | 3 | 4 | 5 | 6 | | VI-1 | Spire1 | 56907 | 4-May-15 | 6013 | 3 | 4 | 5 | 6 | | VI-1 | Tfdp2 | 7029 | 5-May-15 |
| 5918 | 3 | 4 | 5 | 6 | | VI-1 | Spn | 6693 | 7-Jun-15 | 6014 | 3 | 4 | 5 | 6 | | VI-1 | Tfec | 22797 | 4-May-15 |
| 5919 | 3 | 4 | 5 | 6 | | VI-1 | Spock1 | 6695 | 4-May-15 | 6015 | 3 | 4 | 5 | 6 | | VI-1 | Tfpi | 7035 | 12-May-15 |
| 5920 | 3 | 4 | 5 | 6 | | VI-1 | Spon2 | 10417 | 4-May-15 | 6016 | 3 | 4 | 5 | 6 | | VI-1 | Tfpi2 | 7980 | 12-May-15 |
| 5921 | 3 | 4 | 5 | 6 | | VI-1 | Sppl2b | 56928 | 4-May-15 | 6017 | 3 | 4 | 5 | 6 | | VI-1 | Tfr2 | 7036 | 23-May-15 |
| 5922 | 3 | 4 | 5 | 6 | | VI-1 | Spred3 | 399473 | 4-May-15 | 6018 | 3 | 4 | 5 | 6 | | VI-1 | Tfrc | 7037 | 24-May-15 |
| 5923 | 3 | 4 | 5 | 6 | | VI-1 | Sprr1b | 6699 | 12-May-15 | 6019 | 3 | 4 | 5 | 6 | | VI-1 | Tgfb1 | 7040 | 4-May-15 |
| 5924 | 3 | 4 | 5 | 6 | | VI-1 | Sprr2a2 | | | 6020 | 3 | 4 | 5 | 6 | | VI-1 | Tgfb2 | 7042 | 23-May-15 |
| 5925 | 3 | 4 | 5 | 6 | | VI-1 | Sprr2b | 6701 | 4-May-15 | 6021 | 3 | 4 | 5 | 6 | | VI-1 | Tgfb3 | 7043 | 23-May-15 |
| 5926 | 3 | 4 | 5 | 6 | | VI-1 | Spry4 | 81848 | 4-May-15 | 6022 | 3 | 4 | 5 | 6 | | VI-1 | Tgfbi | 7045 | 4-May-15 |
| 5927 | 3 | 4 | 5 | 6 | | VI-1 | Spryd3 | 84926 | 12-May-15 | 6023 | 3 | 4 | 5 | 6 | | VI-1 | Tgif1 | 7050 | 23-May-15 |
| 5928 | 3 | 4 | 5 | 6 | | VI-1 | Spsb1 | 80176 | 4-May-15 | 6024 | 3 | 4 | 5 | 6 | | VI-1 | Tgif2lx2 | | |
| 5929 | 3 | 4 | 5 | 6 | | VI-1 | Spsb4 | 92369 | 4-May-15 | 6025 | 3 | 4 | 5 | 6 | | VI-1 | Tgm1 | 7051 | 23-May-15 |
| 5930 | 3 | 4 | 5 | 6 | | VI-1 | Spta1 | 6708 | 12-May-15 | 6026 | 3 | 4 | 5 | 6 | | VI-1 | Tgoln2 | 10618 | 12-May-15 |
| 5931 | 3 | 4 | 5 | 6 | | VI-1 | Sptb | 6710 | 21-May-15 | 6027 | 3 | 4 | 5 | 6 | | VI-1 | Tgtp1 | | |
| 5932 | 3 | 4 | 5 | 6 | | VI-1 | Sqle | 6713 | 4-May-15 | 6028 | 3 | 4 | 5 | 6 | | VI-1 | Tgtp2 | | |
| 5933 | 3 | 4 | 5 | 6 | | VI-1 | Src | 6714 | 17-May-15 | 6029 | 3 | 4 | 5 | 6 | | VI-1 | Thbd | 7056 | 23-May-15 |
| 5934 | 3 | 4 | 5 | 6 | | VI-1 | Srd5a2 | 6716 | 4-May-15 | 6030 | 3 | 4 | 5 | 6 | | VI-1 | Thbs2 | 7058 | 17-May-15 |
| 5935 | 3 | 4 | 5 | 6 | | VI-1 | Srgn | 5552 | 12-May-15 | 6031 | 3 | 4 | 5 | 6 | | VI-1 | Thbs3 | 7059 | 12-May-15 |
| 5936 | 3 | 4 | 5 | 6 | | VI-1 | Srm | 6723 | 7-Jun-15 | 6032 | 3 | 4 | 5 | 6 | | VI-1 | Thbs4 | 7060 | 12-May-15 |
| 5937 | 3 | 4 | 5 | 6 | | VI-1 | Srpk3 | 26576 | 4-May-15 | 6033 | 3 | 4 | 5 | 6 | | VI-1 | Themis2 | 9473 | 4-May-15 |
| 5938 | 3 | 4 | 5 | 6 | | VI-1 | Srpx | 8406 | 21-May-15 | 6034 | 3 | 4 | 5 | 6 | | VI-1 | Thoc6 | 79228 | 4-May-15 |
| 5939 | 3 | 4 | 5 | 6 | | VI-1 | Srpx2 | 27286 | 23-May-15 | 6035 | 3 | 4 | 5 | 6 | | VI-1 | Thy1 | 7070 | 3-May-15 |
| 5940 | 3 | 4 | 5 | 6 | | VI-1 | Srrm4 | 84530 | 4-May-15 | 6036 | 3 | 4 | 5 | 6 | | VI-1 | Tiam1 | 7074 | 17-May-15 |
| 5941 | 3 | 4 | 5 | 6 | | VI-1 | Ssc5d | 284297 | 4-May-15 | 6037 | 3 | 4 | 5 | 6 | | VI-1 | Ticrr | 90381 | 12-May-15 |
| 5942 | 3 | 4 | 5 | 6 | | VI-1 | Sstr4 | 6754 | 12-May-15 | 6038 | 3 | 4 | 5 | 6 | | VI-1 | Tifab | 497189 | 4-May-15 |
| 5943 | 3 | 4 | 5 | 6 | | VI-1 | St14 | 6768 | 23-May-15 | 6039 | 3 | 4 | 5 | 6 | | VI-1 | Tigd3 | 220359 | 21-May-15 |
| 5944 | 3 | 4 | 5 | 6 | | VI-1 | St3gal5 | 8869 | 12-May-15 | 6040 | 3 | 4 | 5 | 6 | | VI-1 | Tigit | 201633 | 3-May-15 |
| 5945 | 3 | 4 | 5 | 6 | | VI-1 | St5 | 6764 | 12-May-15 | 6041 | 3 | 4 | 5 | 6 | | VI-1 | Timd4 | 91937 | 4-May-15 |
| 5946 | 3 | 4 | 5 | 6 | | VI-1 | St6galnac1 | 55808 | 4-May-15 | 6042 | 3 | 4 | 5 | 6 | | VI-1 | Timp2 | 7077 | 24-May-15 |
| 5947 | 3 | 4 | 5 | 6 | | VI-1 | St6galnac2 | 10610 | 4-May-15 | 6043 | 3 | 4 | 5 | 6 | | VI-1 | Timp4 | 7079 | 12-May-15 |
| 5948 | 3 | 4 | 5 | 6 | | VI-1 | St8sia6 | 338596 | 4-May-15 | 6044 | 3 | 4 | 5 | 6 | | VI-1 | Tinagl1 | 64129 | 12-May-15 |
| 5949 | 3 | 4 | 5 | 6 | | VI-1 | Stab1 | 23166 | 12-May-15 | 6045 | 3 | 4 | 5 | 6 | | VI-1 | Tiparp | 25976 | 4-May-15 |
| 5950 | 3 | 4 | 5 | 6 | | VI-1 | Stac2 | 342667 | 12-May-15 | 6046 | 3 | 4 | 5 | 6 | | VI-1 | Tipin | 54962 | 4-May-15 |
| 5951 | 3 | 4 | 5 | 6 | | VI-1 | Stard3nl | 83930 | 12-May-15 | 6047 | 3 | 4 | 5 | 6 | | VI-1 | Tjp3 | 27134 | 4-May-15 |
| 5952 | 3 | 4 | 5 | 6 | | VI-1 | Stat4 | 6775 | 12-May-15 | 6048 | 3 | 4 | 5 | 6 | | VI-1 | Tk1 | 7083 | 4-May-15 |
| 5953 | 3 | 4 | 5 | 6 | | VI-1 | Steap1 | 26872 | 4-May-15 | 6049 | 3 | 4 | 5 | 6 | | VI-1 | Tkd1 | 116238 | 4-May-15 |
| 5954 | 3 | 4 | 5 | 6 | | VI-1 | Steap3 | 55240 | 4-May-15 | 6050 | 3 | 4 | 5 | 6 | | VI-1 | Tle2 | 7089 | 4-May-15 |
| 5955 | 3 | 4 | 5 | 6 | | VI-1 | Stfa1 | | | 6051 | 3 | 4 | 5 | 6 | | VI-1 | Tlr1 | 7096 | 17-May-15 |
| 5956 | 3 | 4 | 5 | 6 | | VI-1 | Stfa2 | | | 6052 | 3 | 4 | 5 | 6 | | VI-1 | Tlr13 | | |
| 5957 | 3 | 4 | 5 | 6 | | VI-1 | Stil | 6491 | 23-May-15 | 6053 | 3 | 4 | 5 | 6 | | VI-1 | Tlr2 | 7097 | 24-May-15 |
| 5958 | 3 | 4 | 5 | 6 | | VI-1 | Stom | 2040 | 12-May-15 | 6054 | 3 | 4 | 5 | 6 | | VI-1 | Tlr7 | 51284 | 17-May-15 |
| 5959 | 3 | 4 | 5 | 6 | | VI-1 | Stx11 | 8676 | 23-May-15 | 6055 | 3 | 4 | 5 | 6 | | VI-1 | Tlr8 | 51311 | 17-May-15 |
| 5960 | 3 | 4 | 5 | 6 | | VI-1 | Stx2 | 2054 | 4-May-15 | 6056 | 3 | 4 | 5 | 6 | | VI-1 | Tlr9 | 54106 | 17-May-15 |
| 5961 | 3 | 4 | 5 | 6 | | VI-1 | Sulf1 | 23213 | 17-May-15 | 6057 | 3 | 4 | 5 | 6 | | VI-1 | Tm4sf19 | 116211 | 4-May-15 |
| 5962 | 3 | 4 | 5 | 6 | | VI-1 | Sult1d1 | 133150 | 4-May-15 | 6058 | 3 | 4 | 5 | 6 | | VI-1 | Tm6sf1 | 53346 | 17-May-15 |
| 5963 | 3 | 4 | 5 | 6 | | VI-1 | Sult1e1 | 6783 | 12-May-15 | | | | | | | | | | |

Fig. 30 - 33

| | | | | | | | | | | | | | | | | | |
|---|---|---|---|---|---|---|---|---|---|---|---|---|---|---|---|---|---|
| 6059 | 3 | 4 | 5 | 6 | | | VI-1 | Tm6sf2 | 53345 | 4-May-15 | 6154 | 3 | 4 | 5 | 6 | | | VI-1 | Trim63 | 84676 | 4-May-15 |
| 6060 | 3 | 4 | 5 | 6 | | | VI-1 | Tm7sf2 | 7108 | 4-May-15 | 6155 | 3 | 4 | 5 | 6 | | | VI-1 | Trim72 | 493829 | 4-May-15 |
| 6061 | 3 | 4 | 5 | 6 | | | VI-1 | Tmc5 | 79838 | 12-May-15 | 6156 | 3 | 4 | 5 | 6 | | | VI-1 | Trip13 | 9319 | 4-May-15 |
| 6062 | 3 | 4 | 5 | 6 | | | VI-1 | Tmc7 | 79905 | 4-May-15 | 6157 | 3 | 4 | 5 | 6 | | | VI-1 | Troap | 10024 | 4-May-15 |
| 6063 | 3 | 4 | 5 | 6 | | | VI-1 | Tmc8 | 147138 | 4-May-15 | 6158 | 3 | 4 | 5 | 6 | | | VI-1 | Trp53i11 | | |
| 6064 | 3 | 4 | 5 | 6 | | | VI-1 | Tmcc2 | 9911 | 12-May-15 | 6159 | 3 | 4 | 5 | 6 | | | VI-1 | Trp53inp1 | | |
| 6065 | 3 | 4 | 5 | 6 | | | VI-1 | Tmem100 | 55273 | 3-May-15 | 6160 | 3 | 4 | 5 | 6 | | | VI-1 | Trp63 | | |
| 6066 | 3 | 4 | 5 | 6 | | | VI-1 | Tmem102 | 284114 | 14-May-15 | 6161 | 3 | 4 | 5 | 6 | | | VI-1 | Trpv2 | 51393 | 4-May-15 |
| 6067 | 3 | 4 | 5 | 6 | | | VI-1 | Tmem119 | 338773 | 4-May-15 | 6162 | 3 | 4 | 5 | 6 | | | VI-1 | Tsc22d1 | 8848 | 12-May-15 |
| 6068 | 3 | 4 | 5 | 6 | | | VI-1 | Tmem120b | 144404 | 4-May-15 | 6163 | 3 | 4 | 5 | 6 | | | VI-1 | Tsc22d3 | 1831 | 4-May-15 |
| 6069 | 3 | 4 | 5 | 6 | | | VI-1 | Tmem125 | 128218 | 4-May-15 | 6164 | 3 | 4 | 5 | 6 | | | VI-1 | Tsga13 | 114960 | 12-May-15 |
| 6070 | 3 | 4 | 5 | 6 | | | VI-1 | Tmem139 | 135932 | 12-May-15 | 6165 | 3 | 4 | 5 | 6 | | | VI-1 | Tshr | 7253 | 12-May-15 |
| 6071 | 3 | 4 | 5 | 6 | | | VI-1 | Tmem158 | 25907 | 4-May-15 | 6166 | 3 | 4 | 5 | 6 | | | VI-1 | Tshz2 | 128553 | 4-May-15 |
| 6072 | 3 | 4 | 5 | 6 | | | VI-1 | Tmem173 | 340061 | 4-May-15 | 6167 | 3 | 4 | 5 | 6 | | | VI-1 | Tsku | 25987 | 4-May-15 |
| 6073 | 3 | 4 | 5 | 6 | | | VI-1 | Tmem176a | 55365 | 4-May-15 | 6168 | 3 | 4 | 5 | 6 | | | VI-1 | Tspan1 | 10103 | 4-May-15 |
| 6074 | 3 | 4 | 5 | 6 | | | VI-1 | Tmem182 | 130827 | 4-May-15 | 6169 | 3 | 4 | 5 | 6 | | | VI-1 | Tspan12 | 23554 | 23-May-15 |
| 6075 | 3 | 4 | 5 | 6 | | | VI-1 | Tmem221 | 100130519 | 4-May-15 | 6170 | 3 | 4 | 5 | 6 | | | VI-1 | Tspan15 | 23555 | 4-May-15 |
| 6076 | 3 | 4 | 5 | 6 | | | VI-1 | Tmem243 | 79161 | 4-May-15 | 6171 | 3 | 4 | 5 | 6 | | | VI-1 | Tspan32 | 10077 | 4-May-15 |
| 6077 | 3 | 4 | 5 | 6 | | | VI-1 | Tmem252 | 169693 | 4-May-15 | 6172 | 3 | 4 | 5 | 6 | | | VI-1 | Tspan33 | 340348 | 4-May-15 |
| 6078 | 3 | 4 | 5 | 6 | | | VI-1 | Tmem255a | 55026 | 4-May-15 | 6173 | 3 | 4 | 5 | 6 | | | VI-1 | Tspan6 | 7105 | 4-May-15 |
| 6079 | 3 | 4 | 5 | 6 | | | VI-1 | Tmem26 | 219623 | 4-May-15 | 6174 | 3 | 4 | 5 | 6 | | | VI-1 | Tspan8 | 7103 | 17-May-15 |
| 6080 | 3 | 4 | 5 | 6 | | | VI-1 | Tmem38a | 79041 | 4-May-15 | 6175 | 3 | 4 | 5 | 6 | | | VI-1 | Tspan9 | 10867 | 4-May-15 |
| 6081 | 3 | 4 | 5 | 6 | | | VI-1 | Tmem40 | 55287 | 4-May-15 | 6176 | 3 | 4 | 5 | 6 | | | VI-1 | Tspo2 | 222642 | 4-May-15 |
| 6082 | 3 | 4 | 5 | 6 | | | VI-1 | Tmem45a | 55076 | 12-May-15 | 6177 | 3 | 4 | 5 | 6 | | | VI-1 | Tssk6 | 83983 | 4-May-15 |
| 6083 | 3 | 4 | 5 | 6 | | | VI-1 | Tmem45b | 120224 | 4-May-15 | 6178 | 3 | 4 | 5 | 6 | | | VI-1 | Tst | 7263 | 4-May-15 |
| 6084 | 3 | 4 | 5 | 6 | | | VI-1 | Tmem51os1 | | | 6179 | 3 | 4 | 5 | 6 | | | VI-1 | Ttc39a | 22996 | 12-May-15 |
| 6085 | 3 | 4 | 5 | 6 | | | VI-1 | Tmem56 | 148534 | 4-May-15 | 6180 | 3 | 4 | 5 | 6 | | | VI-1 | Ttc9 | 23508 | 4-May-15 |
| 6086 | 3 | 4 | 5 | 6 | | | VI-1 | Tmem64 | 169200 | 4-May-15 | 6181 | 3 | 4 | 5 | 6 | | | VI-1 | Ttk | 7272 | 4-May-15 |
| 6087 | 3 | 4 | 5 | 6 | | | VI-1 | Tmem86b | 255043 | 4-May-15 | 6182 | 3 | 4 | 5 | 6 | | | VI-1 | Ttll11 | 158135 | 4-May-15 |
| 6088 | 3 | 4 | 5 | 6 | | | VI-1 | Tmem88b | 643965 | 4-May-15 | 6183 | 3 | 4 | 5 | 6 | | | VI-1 | Ttpa | 7274 | 23-May-15 |
| 6089 | 3 | 4 | 5 | 6 | | | VI-1 | Tmem91 | 641649 | 4-May-15 | 6184 | 3 | 4 | 5 | 6 | | | VI-1 | Ttyh1 | 57348 | 4-May-15 |
| 6090 | 3 | 4 | 5 | 6 | | | VI-1 | Tmod1 | 7111 | 12-May-15 | 6185 | 3 | 4 | 5 | 6 | | | VI-1 | Ttyh3 | 80727 | 4-May-15 |
| 6091 | 3 | 4 | 5 | 6 | | | VI-1 | Tmprss3 | 64699 | 7-Jun-15 | 6186 | 3 | 4 | 5 | 6 | | | VI-1 | Tuba1a | 7846 | 4-May-15 |
| 6092 | 3 | 4 | 5 | 6 | | | VI-1 | Tmsb10 | 9168 | 21-May-15 | 6187 | 3 | 4 | 5 | 6 | | | VI-1 | Tuba1b | 10376 | 4-May-15 |
| 6093 | 3 | 4 | 5 | 6 | | | VI-1 | Tmsb15a | 11013 | 4-May-15 | 6188 | 3 | 4 | 5 | 6 | | | VI-1 | Tuba1c | 84790 | 12-May-15 |
| 6094 | 3 | 4 | 5 | 6 | | | VI-1 | Tmsb15b1 | | | 6189 | 3 | 4 | 5 | 6 | | | VI-1 | Tubb1 | 81027 | 7-Jun-15 |
| 6095 | 3 | 4 | 5 | 6 | | | VI-1 | Tmsb15l | | | 6190 | 3 | 4 | 5 | 6 | | | VI-1 | Tubb2a | 7280 | 12-May-15 |
| 6096 | 3 | 4 | 5 | 6 | | | VI-1 | Tmsb4x | 7114 | 4-May-15 | 6191 | 3 | 4 | 5 | 6 | | | VI-1 | Tubb2a-ps2 | | |
| 6097 | 3 | 4 | 5 | 6 | | | VI-1 | Tnfaip2 | 7127 | 4-May-15 | 6192 | 3 | 4 | 5 | 6 | | | VI-1 | Tubb2b | 347733 | 4-May-15 |
| 6098 | 3 | 4 | 5 | 6 | | | VI-1 | Tnfaip6 | 7130 | 23-May-15 | 6193 | 3 | 4 | 5 | 6 | | | VI-1 | Tubb3 | 10381 | 23-May-15 |
| 6099 | 3 | 4 | 5 | 6 | | | VI-1 | Tnfaip8 | 25816 | 4-May-15 | 6194 | 3 | 4 | 5 | 6 | | | VI-1 | Tubb4b | 10383 | 21-May-15 |
| 6100 | 3 | 4 | 5 | 6 | | | VI-1 | Tnfaip8l2 | 79626 | 4-May-15 | 6195 | 3 | 4 | 5 | 6 | | | VI-1 | Tubb5 | 203068 | 7-Jun-15 |
| 6101 | 3 | 4 | 5 | 6 | | | VI-1 | Tnfrsf12a | 51330 | 4-May-15 | 6196 | 3 | 4 | 5 | 6 | | | VI-1 | Tubb6 | 84617 | 4-May-15 |
| 6102 | 3 | 4 | 5 | 6 | | | VI-1 | Tnfrsf13b | 23495 | 4-May-15 | 6197 | 3 | 4 | 5 | 6 | | | VI-1 | Tuft1 | 7286 | 12-May-15 |
| 6103 | 3 | 4 | 5 | 6 | | | VI-1 | Tnfrsf13c | 115650 | 12-May-15 | 6198 | 3 | 4 | 5 | 6 | | | VI-1 | Twist1 | 7291 | 28-May-15 |
| 6104 | 3 | 4 | 5 | 6 | | | VI-1 | Tnfrsf19 | 55504 | 4-May-15 | 6199 | 3 | 4 | 5 | 6 | | | VI-1 | Txnip | 10628 | 12-May-15 |
| 6105 | 3 | 4 | 5 | 6 | | | VI-1 | Tnfrsf1b | 7133 | 12-May-15 | 6200 | 3 | 4 | 5 | 6 | | | VI-1 | Txnrd2 | 10587 | 4-May-15 |
| 6106 | 3 | 4 | 5 | 6 | | | VI-1 | Tnfrsf22 | | | 6201 | 3 | 4 | 5 | 6 | | | VI-1 | Tyms | 7298 | 17-May-15 |
| 6107 | 3 | 4 | 5 | 6 | | | VI-1 | Tnfrsf23 | | | 6202 | 3 | 4 | 5 | 6 | | | VI-1 | Tyms-ps | | |
| 6108 | 3 | 4 | 5 | 6 | | | VI-1 | Tnfrsf25 | 8718 | 24-May-15 | 6203 | 3 | 4 | 5 | 6 | | | VI-1 | Tyrobp | 7305 | 23-May-15 |
| 6109 | 3 | 4 | 5 | 6 | | | VI-1 | Tnfrsf26 | | | 6204 | 3 | 4 | 5 | 6 | | | VI-1 | Uap1l1 | 91373 | 23-May-15 |
| 6110 | 3 | 4 | 5 | 6 | | | VI-1 | Tnfsf11 | 8600 | 17-May-15 | 6205 | 3 | 4 | 5 | 6 | | | VI-1 | Ubac1 | 10422 | 4-May-15 |
| 6111 | 3 | 4 | 5 | 6 | | | VI-1 | Tnfsf13b | 10673 | 17-May-15 | 6206 | 3 | 4 | 5 | 6 | | | VI-1 | Ubald2 | 283991 | 4-May-15 |
| 6112 | 3 | 4 | 5 | 6 | | | VI-1 | Tnfsf14 | 8740 | 24-May-15 | 6207 | 3 | 4 | 5 | 6 | | | VI-1 | Ubash3b | 84959 | 4-May-15 |
| 6113 | 3 | 4 | 5 | 6 | | | VI-1 | Tnfsf8 | 944 | 17-May-15 | 6208 | 3 | 4 | 5 | 6 | | | VI-1 | Ube2l6 | 9246 | 12-May-15 |
| 6114 | 3 | 4 | 5 | 6 | | | VI-1 | Tnfsf9 | 8744 | 4-May-15 | 6209 | 3 | 4 | 5 | 6 | | | VI-1 | Ube2s | 27338 | 4-May-15 |
| 6115 | 3 | 4 | 5 | 6 | | | VI-1 | Tnik | 23043 | 4-May-15 | 6210 | 3 | 4 | 5 | 6 | | | VI-1 | Ube2t | 29089 | 4-May-15 |
| 6116 | 3 | 4 | 5 | 6 | | | VI-1 | Tnk1 | 8711 | 12-May-15 | 6211 | 3 | 4 | 5 | 6 | | | VI-1 | Ube4a | 9354 | 12-May-15 |
| 6117 | 3 | 4 | 5 | 6 | | | VI-1 | Tnn | 63923 | 4-May-15 | 6212 | 3 | 4 | 5 | 6 | | | VI-1 | Uchl4 | | |
| 6118 | 3 | 4 | 5 | 6 | | | VI-1 | Tns3 | 64759 | 12-May-15 | 6213 | 3 | 4 | 5 | 6 | | | VI-1 | Uck2 | 7371 | 4-May-15 |
| 6119 | 3 | 4 | 5 | 6 | | | VI-1 | Tnxb | 7148 | 8-May-15 | 6214 | 3 | 4 | 5 | 6 | | | VI-1 | Ucp1 | 7350 | 12-May-15 |
| 6120 | 3 | 4 | 5 | 6 | | | VI-1 | Tob2 | 10766 | 12-May-15 | 6215 | 3 | 4 | 5 | 6 | | | VI-1 | Ucp3 | 7352 | 17-May-15 |
| 6121 | 3 | 4 | 5 | 6 | | | VI-1 | Tor3a | 64222 | 12-May-15 | 6216 | 3 | 4 | 5 | 6 | | | VI-1 | Ugt1a6a | | |
| 6122 | 3 | 4 | 5 | 6 | | | VI-1 | Tpbg | 7162 | 4-May-15 | 6217 | 3 | 4 | 5 | 6 | | | VI-1 | Ugt1a6b | | |
| 6123 | 3 | 4 | 5 | 6 | | | VI-1 | Tpd52 | 7163 | 4-May-15 | 6218 | 3 | 4 | 5 | 6 | | | VI-1 | Ugt1a7c | | |
| 6124 | 3 | 4 | 5 | 6 | | | VI-1 | Tpd52l1 | 7164 | 4-May-15 | 6219 | 3 | 4 | 5 | 6 | | | VI-1 | Ugt2b34 | | |
| 6125 | 3 | 4 | 5 | 6 | | | VI-1 | Tpm3 | 7170 | 23-May-15 | 6220 | 3 | 4 | 5 | 6 | | | VI-1 | Ulbp1 | 80329 | 4-May-15 |
| 6126 | 3 | 4 | 5 | 6 | | | VI-1 | Tpm4 | 7171 | 14-May-15 | 6221 | 3 | 4 | 5 | 6 | | | VI-1 | Unc5b | 219699 | 4-May-15 |
| 6127 | 3 | 4 | 5 | 6 | | | VI-1 | Tppp2 | 122664 | 21-May-15 | 6222 | 3 | 4 | 5 | 6 | | | VI-1 | Unc93a | 54346 | 4-May-15 |
| 6128 | 3 | 4 | 5 | 6 | | | VI-1 | Tppp3 | 51673 | 4-May-15 | 6223 | 3 | 4 | 5 | 6 | | | VI-1 | Unc93b1 | 81622 | 4-May-15 |
| 6129 | 3 | 4 | 5 | 6 | | | VI-1 | Tpsb2 | 64499 | 4-May-15 | 6224 | 3 | 4 | 5 | 6 | | | VI-1 | Ung | 7374 | 4-May-15 |
| 6130 | 3 | 4 | 5 | 6 | | | VI-1 | Trafl | 7185 | 4-May-15 | 6225 | 3 | 4 | 5 | 6 | | | VI-1 | Upk1b | 7348 | 4-May-15 |
| 6131 | 3 | 4 | 5 | 6 | | | VI-1 | Traf3ip3 | 80342 | 4-May-15 | 6226 | 3 | 4 | 5 | 6 | | | VI-1 | Upk3b | 80761 | 19-Mar-15 |
| 6132 | 3 | 4 | 5 | 6 | | | VI-1 | Traip | 10293 | 4-May-15 | 6227 | 3 | 4 | 5 | 6 | | | VI-1 | Upp1 | 7378 | 4-May-15 |
| 6133 | 3 | 4 | 5 | 6 | | | VI-1 | Trak2 | 66008 | 4-May-15 | 6228 | 3 | 4 | 5 | 6 | | | VI-1 | Upp2 | 151531 | 21-May-15 |
| 6134 | 3 | 4 | 5 | 6 | | | VI-1 | Trem1 | 54210 | 28-May-15 | 6229 | 3 | 4 | 5 | 6 | | | VI-1 | Uroc1 | 131669 | 14-May-15 |
| 6135 | 3 | 4 | 5 | 6 | | | VI-1 | Treml1 | 340205 | 4-May-15 | 6230 | 3 | 4 | 5 | 6 | | | VI-1 | Urod | 7389 | 23-May-15 |
| 6136 | 3 | 4 | 5 | 6 | | | VI-1 | Treml2 | 79865 | 4-May-15 | 6231 | 3 | 4 | 5 | 6 | | | VI-1 | Uros | 7390 | 4-May-15 |
| 6137 | 3 | 4 | 5 | 6 | | | VI-1 | Treml4 | 285852 | 4-May-15 | 6232 | 3 | 4 | 5 | 6 | | | VI-1 | Usp18 | 11274 | 23-May-15 |
| 6138 | 3 | 4 | 5 | 6 | | | VI-1 | Trex2 | 11219 | 4-May-15 | 6233 | 3 | 4 | 5 | 6 | | | VI-1 | Usp2 | 9099 | 12-May-15 |
| 6139 | 3 | 4 | 5 | 6 | | | VI-1 | Trf | 7018 | 7-Jun-15 | 6234 | 3 | 4 | 5 | 6 | | | VI-1 | Usp20 | 10868 | 4-May-15 |
| 6140 | 3 | 4 | 5 | 6 | | | VI-1 | Trib2 | 28951 | 4-May-15 | 6235 | 3 | 4 | 5 | 6 | | | VI-1 | Usp32 | 84669 | 4-May-15 |
| 6141 | 3 | 4 | 5 | 6 | | | VI-1 | Trib3 | 57761 | 12-May-15 | 6236 | 3 | 4 | 5 | 6 | | | VI-1 | Usp49 | 25862 | 4-May-15 |
| 6142 | 3 | 4 | 5 | 6 | | | VI-1 | Tril | 9865 | 12-May-15 | 6237 | 3 | 4 | 5 | 6 | | | VI-1 | Usp53 | 54532 | 12-May-15 |
| 6143 | 3 | 4 | 5 | 6 | | | VI-1 | Trim10 | 10107 | 4-May-15 | 6238 | 3 | 4 | 5 | 6 | | | VI-1 | Usp54 | 159195 | 4-May-15 |
| 6144 | 3 | 4 | 5 | 6 | | | VI-1 | Trim14 | 9830 | 12-May-15 | 6239 | 3 | 4 | 5 | 6 | | | VI-1 | Utp14a | 10813 | 4-May-15 |
| 6145 | 3 | 4 | 5 | 6 | | | VI-1 | Trim16 | 10626 | 4-May-15 | 6240 | 3 | 4 | 5 | 6 | | | VI-1 | Utp14b | 9724 | 4-May-15 |
| 6146 | 3 | 4 | 5 | 6 | | | VI-1 | Trim30a | | | 6241 | 3 | 4 | 5 | 6 | | | VI-1 | Ufs2b | 257313 | 4-May-15 |
| 6147 | 3 | 4 | 5 | 6 | | | VI-1 | Trim30b | | | 6242 | 3 | 4 | 5 | 6 | | | VI-1 | Vangl1 | 81839 | 4-May-15 |
| 6148 | 3 | 4 | 5 | 6 | | | VI-1 | Trim30d | | | 6243 | 3 | 4 | 5 | 6 | | | VI-1 | Vash1 | 22846 | 21-May-15 |
| 6149 | 3 | 4 | 5 | 6 | | | VI-1 | Trim36 | 55521 | 12-May-15 | 6244 | 3 | 4 | 5 | 6 | | | VI-1 | Vat1l | 57687 | 4-May-15 |
| 6150 | 3 | 4 | 5 | 6 | | | VI-1 | Trim47 | 91107 | 4-May-15 | 6245 | 3 | 4 | 5 | 6 | | | VI-1 | Vav1 | 7409 | 12-May-15 |
| 6151 | 3 | 4 | 5 | 6 | | | VI-1 | Trim54 | 57159 | 4-May-15 | 6246 | 3 | 4 | 5 | 6 | | | VI-1 | Vdr | 7421 | 7-Jun-15 |
| 6152 | 3 | 4 | 5 | 6 | | | VI-1 | Trim58 | 25893 | 4-May-15 | 6247 | 3 | 4 | 5 | 6 | | | VI-1 | Vegfc | 7424 | 4-May-15 |
| 6153 | 3 | 4 | 5 | 6 | | | VI-1 | Trim59 | 286827 | 4-May-15 | 6248 | 3 | 4 | 5 | 6 | | | VI-1 | Vgll3 | 389136 | 4-May-15 |
| | | | | | | | | | | | 6249 | 3 | 4 | 5 | 6 | | | VI-1 | Vim | 7431 | 17-May-15 |

Fig. 30 - 34

| | | | | | | | | | | | | | | | | | |
|---|---|---|---|---|---|---|---|---|---|---|---|---|---|---|---|---|---|
| 6250 | 3 | 4 | 5 | 6 | | VI-1 | Vipr1 | 7433 | 12-May-15 | 6344 | 3 | 4 | 5 | | | V-2 | 1700018B08Rik | |
| 6251 | 3 | 4 | 5 | 6 | | VI-1 | Vmn2r96 | | | 6345 | 3 | 4 | 5 | | | V-2 | 1700019M22Rik | |
| 6252 | 3 | 4 | 5 | 6 | | VI-1 | Vnn1 | 8876 | 4-May-15 | 6346 | 3 | 4 | 5 | | | V-2 | 1700021F07Rik | |
| 6253 | 3 | 4 | 5 | 6 | | VI-1 | Vnn3 | 55350 | 23-May-15 | 6347 | 3 | 4 | 5 | | | V-2 | 1700021N21Rik | |
| 6254 | 3 | 4 | 5 | 6 | | VI-1 | Vopp1 | 81552 | 12-May-15 | 6348 | 3 | 4 | 5 | | | V-2 | 1700023F06Rik | |
| 6255 | 3 | 4 | 5 | 6 | | VI-1 | Vsig2 | 23584 | 4-May-15 | 6349 | 3 | 4 | 5 | | | V-2 | 1700025N23Rik | |
| 6256 | 3 | 4 | 5 | 6 | | VI-1 | Vsig4 | 11326 | 4-May-15 | 6350 | 3 | 4 | 5 | | | V-2 | 1700026O13Rik | |
| 6257 | 3 | 4 | 5 | 6 | | VI-1 | Vstrn5 | 387804 | 4-May-15 | 6351 | 3 | 4 | 5 | | | V-2 | 1700027F09Rik | |
| 6258 | 3 | 4 | 5 | 6 | | VI-1 | Vtn | 7448 | 24-May-15 | 6352 | 3 | 4 | 5 | | | V-2 | 1700028I16Rik | |
| 6259 | 3 | 4 | 5 | 6 | | VI-1 | Vwa2 | 340706 | 4-May-15 | 6353 | 3 | 4 | 5 | | | V-2 | 1700028J19Rik | |
| 6260 | 3 | 4 | 5 | 6 | | VI-1 | Vwa3a | 146177 | 4-May-15 | 6354 | 3 | 4 | 5 | | | V-2 | 1700028K03Rik | |
| 6261 | 3 | 4 | 5 | 6 | | VI-1 | Was | 7454 | 23-May-15 | 6355 | 3 | 4 | 5 | | | V-2 | 1700028P14Rik | |
| 6262 | 3 | 4 | 5 | 6 | | VI-1 | Wbscr25 | | | 6356 | 3 | 4 | 5 | | | V-2 | 1700028P15Rik | |
| 6263 | 3 | 4 | 5 | 6 | | VI-1 | Wdhd1 | 11169 | 4-May-15 | 6357 | 3 | 4 | 5 | | | V-2 | 1700030O20Rik | |
| 6264 | 3 | 4 | 5 | 6 | | VI-1 | Wdr25 | 79446 | 4-May-15 | 6358 | 3 | 4 | 5 | | | V-2 | 1700041C23Rik | |
| 6265 | 3 | 4 | 5 | 6 | | VI-1 | Wfdc12 | 128488 | 4-May-15 | 6359 | 3 | 4 | 5 | | | V-2 | 1700048O20Rik | |
| 6266 | 3 | 4 | 5 | 6 | | VI-1 | Wfdc15b | | | 6360 | 3 | 4 | 5 | | | V-2 | 1700052N19Rik | |
| 6267 | 3 | 4 | 5 | 6 | | VI-1 | Wfdc16 | | | 6361 | 3 | 4 | 5 | | | V-2 | 1700054A03Rik | |
| 6268 | 3 | 4 | 5 | 6 | | VI-1 | Wfdc17 | | | 6362 | 3 | 4 | 5 | | | V-2 | 1700054O13Rik | |
| 6269 | 3 | 4 | 5 | 6 | | VI-1 | Wfikkn2 | 124857 | 12-May-15 | 6363 | 3 | 4 | 5 | | | V-2 | 1700092C10Rik | |
| 6270 | 3 | 4 | 5 | 6 | | VI-1 | Wipf1 | 7456 | 4-May-15 | 6364 | 3 | 4 | 5 | | | V-2 | 1700109H08Rik | |
| 6271 | 3 | 4 | 5 | 6 | | VI-1 | Wipi1 | 55062 | 21-May-15 | 6365 | 3 | 4 | 5 | | | V-2 | 1700121L16Rik | |
| 6272 | 3 | 4 | 5 | 6 | | VI-1 | Wisp1 | 8840 | 17-May-15 | 6366 | 3 | 4 | 5 | | | V-2 | 1700123O12Rik | |
| 6273 | 3 | 4 | 5 | 6 | | VI-1 | Wnt4 | 54361 | 4-May-15 | 6367 | 3 | 4 | 5 | | | V-2 | 1700125G02Rik | |
| 6274 | 3 | 4 | 5 | 6 | | VI-1 | Wwc1 | 23286 | 24-May-15 | 6368 | 3 | 4 | 5 | | | V-2 | 1700125G22Rik | |
| 6275 | 3 | 4 | 5 | 6 | | VI-1 | Xaf1 | 54739 | 4-May-15 | 6369 | 3 | 4 | 5 | | | V-2 | 1700128A07Rik | |
| 6276 | 3 | 4 | 5 | 6 | | VI-1 | Xdh | 7498 | 24-May-15 | 6370 | 3 | 4 | 5 | | | V-2 | 1810008I18Rik | |
| 6277 | 3 | 4 | 5 | 6 | | VI-1 | Xirp1 | 165904 | 17-May-15 | 6371 | 3 | 4 | 5 | | | V-2 | 1810043G02Rik | |
| 6278 | 3 | 4 | 5 | 6 | | VI-1 | Xirp2 | 129446 | 3-May-15 | 6372 | 3 | 4 | 5 | | | V-2 | 2010001E11Rik | |
| 6279 | 3 | 4 | 5 | 6 | | VI-1 | Xk | 7504 | 26-May-15 | 6373 | 3 | 4 | 5 | | | V-2 | 2010003K11Rik | |
| 6280 | 3 | 4 | 5 | 6 | | VI-1 | Xlr | | | 6374 | 3 | 4 | 5 | | | V-2 | 2010012O05Rik | |
| 6281 | 3 | 4 | 5 | 6 | | VI-1 | Xlr3a | | | 6375 | 3 | 4 | 5 | | | V-2 | 2010107G23Rik | |
| 6282 | 3 | 4 | 5 | 6 | | VI-1 | Xlr3b | | | 6376 | 3 | 4 | 5 | | | V-2 | 2010320M18Rik | |
| 6283 | 3 | 4 | 5 | 6 | | VI-1 | Xlr4b | | | 6377 | 3 | 4 | 5 | | | V-2 | 2210414B05Rik | |
| 6284 | 3 | 4 | 5 | 6 | | VI-1 | Xlr4c | | | 6378 | 3 | 4 | 5 | | | V-2 | 2310002F09Rik | |
| 6285 | 3 | 4 | 5 | 6 | | VI-1 | Xpc7 | 23039 | 4-May-15 | 6379 | 3 | 4 | 5 | | | V-2 | 2310008N11Rik | |
| 6286 | 3 | 4 | 5 | 6 | | VI-1 | Xrcc2 | 7516 | 17-May-15 | 6380 | 3 | 4 | 5 | | | V-2 | 2310009B15Rik | |
| 6287 | 3 | 4 | 5 | 6 | | VI-1 | Xrcc6 | 2547 | 24-May-15 | 6381 | 3 | 4 | 5 | | | V-2 | 2310016D03Rik | |
| 6288 | 3 | 4 | 5 | 6 | | VI-1 | Xylt1 | 64131 | 23-May-15 | 6382 | 3 | 4 | 5 | | | V-2 | 2310022A10Rik | |
| 6289 | 3 | 4 | 5 | 6 | | VI-1 | Ypel2 | 388403 | 4-May-15 | 6383 | 3 | 4 | 5 | | | V-2 | 2310061J03Rik | |
| 6290 | 3 | 4 | 5 | 6 | | VI-1 | Ypel4 | 219539 | 4-May-15 | 6384 | 3 | 4 | 5 | | | V-2 | 2310065F04Rik | |
| 6291 | 3 | 4 | 5 | 6 | | VI-1 | Zbed4 | 9889 | 4-May-15 | 6385 | 3 | 4 | 5 | | | V-2 | 2310068I16Rik | |
| 6292 | 3 | 4 | 5 | 6 | | VI-1 | Zbp1 | 81030 | 7-Jun-15 | 6386 | 3 | 4 | 5 | | | V-2 | 2310079G19Rik | |
| 6293 | 3 | 4 | 5 | 6 | | VI-1 | Zc2hc1c | 79696 | 4-May-15 | 6387 | 3 | 4 | 5 | | | V-2 | 2510002D24Rik | |
| 6294 | 3 | 4 | 5 | 6 | | VI-1 | Zc3h12d | 340152 | 4-May-15 | 6388 | 3 | 4 | 5 | | | V-2 | 2610016A17Rik | |
| 6295 | 3 | 4 | 5 | 6 | | VI-1 | Zcchc18 | 644353 | 4-May-15 | 6389 | 3 | 4 | 5 | | | V-2 | 2610206C17Rik | |
| 6296 | 3 | 4 | 5 | 6 | | VI-1 | Zeb2os | | | 6390 | 3 | 4 | 5 | | | V-2 | 2700060E02Rik | |
| 6297 | 3 | 4 | 5 | 6 | | VI-1 | Zfp13 | 7755 | 4-May-15 | 6391 | 3 | 4 | 5 | | | V-2 | 2700086A05Rik | |
| 6298 | 3 | 4 | 5 | 6 | | VI-1 | Zfp185 | | | 6392 | 3 | 4 | 5 | | | V-2 | 2810008D09Rik | |
| 6299 | 3 | 4 | 5 | 6 | | VI-1 | Zfp189 | | | 6393 | 3 | 4 | 5 | | | V-2 | 2810025M15Rik | |
| 6300 | 3 | 4 | 5 | 6 | | VI-1 | Zfp36 | 7538 | 21-May-15 | 6394 | 3 | 4 | 5 | | | V-2 | 2810049E08Rik | |
| 6301 | 3 | 4 | 5 | 6 | | VI-1 | Zfp366 | | | 6395 | 3 | 4 | 5 | | | V-2 | 2810404M03Rik | |
| 6302 | 3 | 4 | 5 | 6 | | VI-1 | Zfp367 | | | 6396 | 3 | 4 | 5 | | | V-2 | 2810429I04Rik | |
| 6303 | 3 | 4 | 5 | 6 | | VI-1 | Zfp568 | | | 6397 | 3 | 4 | 5 | | | V-2 | 2810442I21Rik | |
| 6304 | 3 | 4 | 5 | 6 | | VI-1 | Zfp69 | 339559 | 4-May-15 | 6398 | 3 | 4 | 5 | | | V-2 | 2810442N19Rik | |
| 6305 | 3 | 4 | 5 | 6 | | VI-1 | Zfp692 | 55657 | 4-May-15 | 6399 | 3 | 4 | 5 | | | V-2 | 2900041M22Rik | |
| 6306 | 3 | 4 | 5 | 6 | | VI-1 | Zfp750 | 79755 | 28-May-15 | 6400 | 3 | 4 | 5 | | | V-2 | 3110007F17Rik | |
| 6307 | 3 | 4 | 5 | 6 | | VI-1 | Zfp830 | | | 6401 | 3 | 4 | 5 | | | V-2 | 3110035E14Rik | |
| 6308 | 3 | 4 | 5 | 6 | | VI-1 | Zfp870 | | | 6402 | 3 | 4 | 5 | | | V-2 | 3110062M04Rik | |
| 6309 | 3 | 4 | 5 | 6 | | VI-1 | Zfp948 | | | 6403 | 3 | 4 | 5 | | | V-2 | 3632451O06Rik | |
| 6310 | 3 | 4 | 5 | 6 | | VI-1 | Zfp949 | | | 6404 | 3 | 4 | 5 | | | V-2 | 3830417H13Rik | |
| 6311 | 3 | 4 | 5 | 6 | | VI-1 | Zfpm1 | 161882 | 17-May-15 | 6405 | 3 | 4 | 5 | | | V-2 | 4631405J19Rik | |
| 6312 | 3 | 4 | 5 | 6 | | VI-1 | Zfyve21 | 79038 | 21-May-15 | 6406 | 3 | 4 | 5 | | | V-2 | 4833418N02Rik | |
| 6313 | 3 | 4 | 5 | 6 | | VI-1 | Zfyve28 | 57732 | 4-May-15 | 6407 | 3 | 4 | 5 | | | V-2 | 4833423E24Rik | |
| 6314 | 3 | 4 | 5 | 6 | | VI-1 | Zgrf1 | 55345 | 4-May-15 | 6408 | 3 | 4 | 5 | | | V-2 | 4833428L15Rik | |
| 6315 | 3 | 4 | 5 | 6 | | VI-1 | Zmynd15 | 84225 | 4-May-15 | 6409 | 3 | 4 | 5 | | | V-2 | 4921504E06Rik | |
| 6316 | 3 | 4 | 5 | 6 | | VI-1 | Znf41-ps | | | 6410 | 3 | 4 | 5 | | | V-2 | 4921507P07Rik | |
| 6317 | 3 | 4 | 5 | 6 | | VI-1 | Zranb3 | 84083 | 4-May-15 | 6411 | 3 | 4 | 5 | | | V-2 | 4921509O07Rik | |
| 6318 | 3 | 4 | 5 | 6 | | VI-1 | Zscan18 | 65982 | 28-May-15 | 6412 | 3 | 4 | 5 | | | V-2 | 4921529L05Rik | |
| 6319 | 3 | 4 | 5 | 6 | | VI-1 | Zwilch | 55055 | 29-May-15 | 6413 | 3 | 4 | 5 | | | V-2 | 4921539E11Rik | |
| 6320 | 3 | 4 | 5 | 6 | | VI-1 | Zwint | 11130 | 4-May-15 | 6414 | 3 | 4 | 5 | | | V-2 | 4930402F06Rik | |
| 6321 | 3 | 4 | 5 | 6 | | VI-1 | Zyg11a | 440590 | 12-May-15 | 6415 | 3 | 4 | 5 | | | V-2 | 4930402H24Rik | |
| 6322 | 3 | 4 | 5 | | | V-2 | 0610007P14Rik | | | 6416 | 3 | 4 | 5 | | | V-2 | 4930417O13Rik | |
| 6323 | 3 | 4 | 5 | | | V-2 | 0610009B22Rik | | | 6417 | 3 | 4 | 5 | | | V-2 | 4930417N08Rik | |
| 6324 | 3 | 4 | 5 | | | V-2 | 1110002L01Rik | | | 6418 | 3 | 4 | 5 | | | V-2 | 4930463O16Rik | |
| 6325 | 3 | 4 | 5 | | | V-2 | 1110004E09Rik | | | 6419 | 3 | 4 | 5 | | | V-2 | 4930467D21Rik | |
| 6326 | 3 | 4 | 5 | | | V-2 | 1110007C09Rik | | | 6420 | 3 | 4 | 5 | | | V-2 | 4930473O22Rik | |
| 6327 | 3 | 4 | 5 | | | V-2 | 1110028F11Rik | | | 6421 | 3 | 4 | 5 | | | V-2 | 4930480E11Rik | |
| 6328 | 3 | 4 | 5 | | | V-2 | 1110032F04Rik | | | 6422 | 3 | 4 | 5 | | | V-2 | 4930503L19Rik | |
| 6329 | 3 | 4 | 5 | | | V-2 | 1110036E04Rik | | | 6423 | 3 | 4 | 5 | | | V-2 | 4930511E03Rik | |
| 6330 | 3 | 4 | 5 | | | V-2 | 1110054M08Rik | | | 6424 | 3 | 4 | 5 | | | V-2 | 4930519F16Rik | |
| 6331 | 3 | 4 | 5 | | | V-2 | 1110059E24Rik | | | 6425 | 3 | 4 | 5 | | | V-2 | 4930521E06Rik | |
| 6332 | 3 | 4 | 5 | | | V-2 | 1190003K10Rik | | | 6426 | 3 | 4 | 5 | | | V-2 | 4930524O08Rik | |
| 6333 | 3 | 4 | 5 | | | V-2 | 1600002D24Rik | | | 6427 | 3 | 4 | 5 | | | V-2 | 4930529L06Rik | |
| 6334 | 3 | 4 | 5 | | | V-2 | 1700003E24Rik | | | 6428 | 3 | 4 | 5 | | | V-2 | 4930529M08Rik | |
| 6335 | 3 | 4 | 5 | | | V-2 | 1700003F12Rik | | | 6429 | 3 | 4 | 5 | | | V-2 | 4930542D17Rik | |
| 6336 | 3 | 4 | 5 | | | V-2 | 1700003H04Rik | | | 6430 | 3 | 4 | 5 | | | V-2 | 4930544G11Rik | |
| 6337 | 3 | 4 | 5 | | | V-2 | 1700003M07Rik | | | 6431 | 3 | 4 | 5 | | | V-2 | 4930548K13Rik | |
| 6338 | 3 | 4 | 5 | | | V-2 | 1700007B14Rik | | | 6432 | 3 | 4 | 5 | | | V-2 | 4930550C14Rik | |
| 6339 | 3 | 4 | 5 | | | V-2 | 1700013A15Rik | | | 6433 | 3 | 4 | 5 | | | V-2 | 4930556N09Rik | |
| 6340 | 3 | 4 | 5 | | | V-2 | 1700011I03Rik | | | 6434 | 3 | 4 | 5 | | | V-2 | 4930558K02Rik | |
| 6341 | 3 | 4 | 5 | | | V-2 | 1700012D01Rik | | | | | | | | | | | |
| 6342 | 3 | 4 | 5 | | | V-2 | 1700013D24Rik | | | | | | | | | | | |
| 6343 | 3 | 4 | 5 | | | V-2 | 1700013G24Rik | | | | | | | | | | | |

Fig. 30 - 35

| | | | | | | | | |
|---|---|---|---|---|---|---|---|---|
| 6435 | 3 | 4 | 5 | V-2 | 4930564818Rik | | | |
| 6436 | 3 | 4 | 5 | V-2 | 4930564C03Rik | | | |
| 6437 | 3 | 4 | 5 | V-2 | 4930568G15Rik | | | |
| 6438 | 3 | 4 | 5 | V-2 | 4930578E11Rik | | | |
| 6439 | 3 | 4 | 5 | V-2 | 4930578N18Rik | | | |
| 6440 | 3 | 4 | 5 | V-2 | 4931403G20Rik | | | |
| 6441 | 3 | 4 | 5 | V-2 | 4931440J10Rik | | | |
| 6442 | 3 | 4 | 5 | V-2 | 4932411E22Rik | | | |
| 6443 | 3 | 4 | 5 | V-2 | 4932411N23Rik | | | |
| 6444 | 3 | 4 | 5 | V-2 | 4932429P05Rik | | | |
| 6445 | 3 | 4 | 5 | V-2 | 4933400A11Rik | | | |
| 6446 | 3 | 4 | 5 | V-2 | 4933408J17Rik | | | |
| 6447 | 3 | 4 | 5 | V-2 | 4933411K20Rik | | | |
| 6448 | 3 | 4 | 5 | V-2 | 4933413G19Rik | | | |
| 6449 | 3 | 4 | 5 | V-2 | 4933416M06Rik | | | |
| 6450 | 3 | 4 | 5 | V-2 | 4933417O13Rik | | | |
| 6451 | 3 | 4 | 5 | V-2 | 4933422H20Rik | | | |
| 6452 | 3 | 4 | 5 | V-2 | 4933424G05Rik | | | |
| 6453 | 3 | 4 | 5 | V-2 | 4933436E23Rik | | | |
| 6454 | 3 | 4 | 5 | V-2 | 4933436I01Rik | | | |
| 6455 | 3 | 4 | 5 | V-2 | 5430425X12Rik | | | |
| 6456 | 3 | 4 | 5 | V-2 | 5430427M07Rik | | | |
| 6457 | 3 | 4 | 5 | V-2 | 5730435O14Rik | | | |
| 6458 | 3 | 4 | 5 | V-2 | 5730507C01Rik | | | |
| 6459 | 3 | 4 | 5 | V-2 | 5830428M24Rik | | | |
| 6460 | 3 | 4 | 5 | V-2 | 6030440G07Rik | | | |
| 6461 | 3 | 4 | 5 | V-2 | 6330409D20Rik | | | |
| 6462 | 3 | 4 | 5 | V-2 | 6430548M08Rik | | | |
| 6463 | 3 | 4 | 5 | V-2 | 7420700N18Rik | | | |
| 6464 | 3 | 4 | 5 | V-2 | 9130008F23Rik | | | |
| 6465 | 3 | 4 | 5 | V-2 | 9130018I15Rik | | | |
| 6466 | 3 | 4 | 5 | V-2 | 9130209A04Rik | | | |
| 6467 | 3 | 4 | 5 | V-2 | 9230009I02Rik | | | |
| 6468 | 3 | 4 | 5 | V-2 | 9330111N05Rik | | | |
| 6469 | 3 | 4 | 5 | V-2 | 9530027J09Rik | | | |
| 6470 | 3 | 4 | 5 | V-2 | 9530091C08Rik | | | |
| 6471 | 3 | 4 | 5 | V-2 | 9830107B12Rik | | | |
| 6472 | 3 | 4 | 5 | V-2 | 9930014A18Rik | | | |
| 6473 | 3 | 4 | 5 | V-2 | A130010J15Rik | | | |
| 6474 | 3 | 4 | 5 | V-2 | A130077B15Rik | | | |
| 6475 | 3 | 4 | 5 | V-2 | A230001M10Rik | | | |
| 6476 | 3 | 4 | 5 | V-2 | A230070E04Rik | | | |
| 6477 | 3 | 4 | 5 | V-2 | A330021E22Rik | | | |
| 6478 | 3 | 4 | 5 | V-2 | A330023F24Rik | | | |
| 6479 | 3 | 4 | 5 | V-2 | A330032B11Rik | | | |
| 6480 | 3 | 4 | 5 | V-2 | A330070K13Rik | | | |
| 6481 | 3 | 4 | 5 | V-2 | A330074K22Rik | | | |
| 6482 | 3 | 4 | 5 | V-2 | A430089I19Rik | | | |
| 6483 | 3 | 4 | 5 | V-2 | A530058N18Rik | | | |
| 6484 | 3 | 4 | 5 | V-2 | A630020A06 | | | |
| 6485 | 3 | 4 | 5 | V-2 | A630072M18Rik | | | |
| 6486 | 3 | 4 | 5 | V-2 | A630077J23Rik | | | |
| 6487 | 3 | 4 | 5 | V-2 | A730018C14Rik | | | |
| 6488 | 3 | 4 | 5 | V-2 | A830018L16Rik | | | |
| 6489 | 3 | 4 | 5 | V-2 | A830080D01Rik | | | |
| 6490 | 3 | 4 | 5 | V-2 | A930003A15Rik | | | |
| 6491 | 3 | 4 | 5 | V-2 | A930005H10Rik | | | |
| 6492 | 3 | 4 | 5 | V-2 | A930006I01Rik | | | |
| 6493 | 3 | 4 | 5 | V-2 | A930017M01Rik | | | |
| 6494 | 3 | 4 | 5 | V-2 | AA387883 | | | |
| 6495 | 3 | 4 | 5 | V-2 | Aadacl2 | 344752 | 4-May-15 |
| 6496 | 3 | 4 | 5 | V-2 | Aaed1 | 195827 | 4-May-15 |
| 6497 | 3 | 4 | 5 | V-2 | Aamp | 14 | 12-May-15 |
| 6498 | 3 | 4 | 5 | V-2 | Aasdh | 132949 | 4-May-15 |
| 6499 | 3 | 4 | 5 | V-2 | AB041803 | | |
| 6500 | 3 | 4 | 5 | V-2 | Abca9 | 10350 | 12-May-15 |
| 6501 | 3 | 4 | 5 | V-2 | Abcc5 | 10057 | 21-May-15 |
| 6502 | 3 | 4 | 5 | V-2 | Abcd4 | 5826 | 23-May-15 |
| 6503 | 3 | 4 | 5 | V-2 | Abhd17c | 58489 | 4-May-15 |
| 6504 | 3 | 4 | 5 | V-2 | Abhd4 | 63874 | 4-May-15 |
| 6505 | 3 | 4 | 5 | V-2 | Abhd8 | 79575 | 4-May-15 |
| 6506 | 3 | 4 | 5 | V-2 | Ablim2 | 84448 | 12-May-15 |
| 6507 | 3 | 4 | 5 | V-2 | Ablim3 | 22885 | 12-May-15 |
| 6508 | 3 | 4 | 5 | V-2 | Acad11 | 84129 | 4-May-15 |
| 6509 | 3 | 4 | 5 | V-2 | Acads | 35 | 23-May-15 |
| 6510 | 3 | 4 | 5 | V-2 | Acadsb | 36 | 12-May-15 |
| 6511 | 3 | 4 | 5 | V-2 | Acan | 176 | 4-May-15 |
| 6512 | 3 | 4 | 5 | V-2 | Acat2 | 39 | 7-Jun-15 |
| 6513 | 3 | 4 | 5 | V-2 | Accsl | 390110 | 12-May-15 |
| 6514 | 3 | 4 | 5 | V-2 | Ace3 | 100129123 | 12-May-15 |
| 6515 | 3 | 4 | 5 | V-2 | Acer1 | 125981 | 21-May-15 |
| 6516 | 3 | 4 | 5 | V-2 | Acnat1 | | |
| 6517 | 3 | 4 | 5 | V-2 | Acot7 | 11332 | 4-May-15 |
| 6518 | 3 | 4 | 5 | V-2 | Acot8 | 10005 | 12-May-15 |
| 6519 | 3 | 4 | 5 | V-2 | Acy3 | 91703 | 12-May-15 |
| 6520 | 3 | 4 | 5 | V-2 | Adam23 | 8745 | 4-May-15 |
| 6521 | 3 | 4 | 5 | V-2 | Adcyap1 | 116 | 17-May-15 |
| 6522 | 3 | 4 | 5 | V-2 | Adh5 | 128 | 7-Jun-15 |
| 6523 | 3 | 4 | 5 | V-2 | Adra1d | 146 | 4-May-15 |
| 6524 | 3 | 4 | 5 | V-2 | Adra2a | 150 | 4-May-15 |
| 6525 | 3 | 4 | 5 | V-2 | Adrb2 | 154 | 28-May-15 |
| 6526 | 3 | 4 | 5 | V-2 | Adss | 159 | 4-May-15 |
| 6527 | 3 | 4 | 5 | V-2 | AF067063 | | |
| 6528 | 3 | 4 | 5 | V-2 | AF529169 | | |
| 6529 | 3 | 4 | 5 | V-2 | Agap1 | 116987 | 12-May-15 |
| 6530 | 3 | 4 | 5 | V-2 | Agbl2 | 79841 | 23-May-15 |
| 6531 | 3 | 4 | 5 | V-2 | Agtr1a | | |
| 6532 | 3 | 4 | 5 | V-2 | Agtr2 | 186 | 4-May-15 |
| 6533 | 3 | 4 | 5 | V-2 | Agxt | 189 | 23-May-15 |
| 6534 | 3 | 4 | 5 | V-2 | Ahctf1 | 25909 | 4-May-15 |
| 6535 | 3 | 4 | 5 | V-2 | Ahrr | 57491 | 10-Jun-15 |
| 6536 | 3 | 4 | 5 | V-2 | AI182371 | | |
| 6537 | 3 | 4 | 5 | V-2 | AI314180 | | |
| 6538 | 3 | 4 | 5 | V-2 | AI317395 | | |
| 6539 | 3 | 4 | 5 | V-2 | AI413582 | | |
| 6540 | 3 | 4 | 5 | V-2 | AI593442 | | |
| 6541 | 3 | 4 | 5 | V-2 | AI661453 | | |
| 6542 | 3 | 4 | 5 | V-2 | AI848285 | | |
| 6543 | 3 | 4 | 5 | V-2 | AI854517 | | |
| 6544 | 3 | 4 | 5 | V-2 | Aifm1 | 9131 | 19-May-15 |
| 6545 | 3 | 4 | 5 | V-2 | Aip | 9049 | 7-Jun-15 |
| 6546 | 3 | 4 | 5 | V-2 | Ajap1 | 55966 | 4-May-15 |
| 6547 | 3 | 4 | 5 | V-2 | Ak2 | 204 | 4-May-15 |
| 6548 | 3 | 4 | 5 | V-2 | Akap1 | 8165 | 4-May-15 |
| 6549 | 3 | 4 | 5 | V-2 | Akap10 | 11216 | 12-May-15 |
| 6550 | 3 | 4 | 5 | V-2 | Akap5 | 9495 | 21-May-15 |
| 6551 | 3 | 4 | 5 | V-2 | Akr1c20 | | |
| 6552 | 3 | 4 | 5 | V-2 | Aldh1l2 | 160428 | 23-May-15 |
| 6553 | 3 | 4 | 5 | V-2 | Aldh2 | 217 | 24-May-15 |
| 6554 | 3 | 4 | 5 | V-2 | Aldh5a1 | 7915 | 23-May-15 |
| 6555 | 3 | 4 | 5 | V-2 | Aldh6a1 | 4329 | 23-May-15 |
| 6556 | 3 | 4 | 5 | V-2 | Alg10b | 144245 | 12-May-15 |
| 6557 | 3 | 4 | 5 | V-2 | Alg3 | 10195 | 22-May-15 |
| 6558 | 3 | 4 | 5 | V-2 | Alg9 | 79796 | 23-May-15 |
| 6559 | 3 | 4 | 5 | V-2 | Alkbh3 | 221120 | 4-May-15 |
| 6560 | 3 | 4 | 5 | V-2 | Alkbh5 | 54890 | 4-May-15 |
| 6561 | 3 | 4 | 5 | V-2 | Alkbh6 | 84964 | 4-May-15 |
| 6562 | 3 | 4 | 5 | V-2 | Alkbh8 | 91801 | 4-May-15 |
| 6563 | 3 | 4 | 5 | V-2 | Alyref | 10189 | 4-May-15 |
| 6564 | 3 | 4 | 5 | V-2 | Ambn | 258 | 4-May-15 |
| 6565 | 3 | 4 | 5 | V-2 | Amn1 | 196394 | 4-May-15 |
| 6566 | 3 | 4 | 5 | V-2 | Anapc10 | 10393 | 4-May-15 |
| 6567 | 3 | 4 | 5 | V-2 | Anapc13 | 25847 | 4-May-15 |
| 6568 | 3 | 4 | 5 | V-2 | Anapc15 | 25906 | 4-May-15 |
| 6569 | 3 | 4 | 5 | V-2 | Angptl3 | 27329 | 4-May-15 |
| 6570 | 3 | 4 | 5 | V-2 | Ankra2 | 57763 | 4-May-15 |
| 6571 | 3 | 4 | 5 | V-2 | Ankrd26 | 22852 | 4-May-15 |
| 6572 | 3 | 4 | 5 | V-2 | Ankrd32 | 84250 | 4-May-15 |
| 6573 | 3 | 4 | 5 | V-2 | Ankrd33 | 341405 | 4-May-15 |
| 6574 | 3 | 4 | 5 | V-2 | Ankrd34b | 340120 | 4-May-15 |
| 6575 | 3 | 4 | 5 | V-2 | Ankrd36 | 375248 | 16-May-15 |
| 6576 | 3 | 4 | 5 | V-2 | Ankrd46 | 157567 | 4-May-15 |
| 6577 | 3 | 4 | 5 | V-2 | Ankrd7 | 56311 | 4-May-15 |
| 6578 | 3 | 4 | 5 | V-2 | Anks1b | 56899 | 4-May-15 |
| 6579 | 3 | 4 | 5 | V-2 | Ano2 | 57101 | 4-May-15 |
| 6580 | 3 | 4 | 5 | V-2 | Ano5 | 203859 | 23-May-15 |
| 6581 | 3 | 4 | 5 | V-2 | Ano6 | 196527 | 23-May-15 |
| 6582 | 3 | 4 | 5 | V-2 | Anp32a | 8125 | 2-Jun-15 |
| 6583 | 3 | 4 | 5 | V-2 | Ap1ar | 55435 | 4-May-15 |
| 6584 | 3 | 4 | 5 | V-2 | Ap3m2 | 10947 | 4-May-15 |
| 6585 | 3 | 4 | 5 | V-2 | Ap5b1 | 91056 | 4-May-15 |
| 6586 | 3 | 4 | 5 | V-2 | Apbb3 | 10307 | 4-May-15 |
| 6587 | 3 | 4 | 5 | V-2 | Aplp1 | 333 | 4-May-15 |
| 6588 | 3 | 4 | 5 | V-2 | Apoa1bp | 128240 | 12-May-15 |
| 6589 | 3 | 4 | 5 | V-2 | Apoa4 | 337 | 4-May-15 |
| 6590 | 3 | 4 | 5 | V-2 | Apool | 139322 | 4-May-15 |
| 6591 | 3 | 4 | 5 | V-2 | App | 351 | 31-May-15 |
| 6592 | 3 | 4 | 5 | V-2 | Appl1 | 26060 | 24-May-15 |
| 6593 | 3 | 4 | 5 | V-2 | Arhgap32 | 9743 | 4-May-15 |
| 6594 | 3 | 4 | 5 | V-2 | Arhgap33 | 115703 | 4-May-15 |
| 6595 | 3 | 4 | 5 | V-2 | Arhgap44 | 9912 | 4-May-15 |
| 6596 | 3 | 4 | 5 | V-2 | Arid1a | 8289 | 24-May-15 |
| 6597 | 3 | 4 | 5 | V-2 | Armc3 | 219681 | 4-May-15 |
| 6598 | 3 | 4 | 5 | V-2 | Armcx1 | 51309 | 12-May-15 |
| 6599 | 3 | 4 | 5 | V-2 | Artn | 9048 | 4-May-15 |
| 6600 | 3 | 4 | 5 | V-2 | Asb13 | 79754 | 4-May-15 |
| 6601 | 3 | 4 | 5 | V-2 | Asb16 | 92591 | 4-May-15 |
| 6602 | 3 | 4 | 5 | V-2 | Asb6 | 140459 | 4-May-15 |
| 6603 | 3 | 4 | 5 | V-2 | Ash2l | 9070 | 4-May-15 |
| 6604 | 3 | 4 | 5 | V-2 | Atg101 | 60673 | 21-May-15 |
| 6605 | 3 | 4 | 5 | V-2 | Atp13a5 | 344905 | 4-May-15 |
| 6606 | 3 | 4 | 5 | V-2 | Atp5b | 506 | 12-May-15 |
| 6607 | 3 | 4 | 5 | V-2 | Atp5c1 | 509 | 4-May-15 |
| 6608 | 3 | 4 | 5 | V-2 | Atp5d | 513 | 4-May-15 |
| 6609 | 3 | 4 | 5 | V-2 | Atp5f1 | 515 | 12-May-15 |
| 6610 | 3 | 4 | 5 | V-2 | Atp5h | 10476 | 4-May-15 |
| 6611 | 3 | 4 | 5 | V-2 | Atp5j | 522 | 12-May-15 |
| 6612 | 3 | 4 | 5 | V-2 | Atp5j2 | 9551 | 4-May-15 |
| 6613 | 3 | 4 | 5 | V-2 | Atp5s | 27109 | 4-May-15 |
| 6614 | 3 | 4 | 5 | V-2 | Atp5sl | 55101 | 4-May-15 |
| 6615 | 3 | 4 | 5 | V-2 | Atp6ap1 | 537 | 4-May-15 |
| 6616 | 3 | 4 | 5 | V-2 | Atp6ap2 | 10159 | 3-May-15 |
| 6617 | 3 | 4 | 5 | V-2 | Atp6v1a | 523 | 12-May-15 |
| 6618 | 3 | 4 | 5 | V-2 | Atpaf2 | 91647 | 4-May-15 |
| 6619 | 3 | 4 | 5 | V-2 | Atxn2l | 11273 | 21-May-15 |
| 6620 | 3 | 4 | 5 | V-2 | Auh | 549 | 21-May-15 |

Fig. 30 - 36

| | | | | | | | | | | | | | | | | | |
|---|---|---|---|---|---|---|---|---|---|---|---|---|---|---|---|---|---|
| 6621 | 3 | 4 | 5 | | | V-2 | Aup1 | 550 | 3-May-15 | 6714 | 3 | 4 | 5 | | | V-2 | Ccdc32 | 90416 | 4-May-15 |
| 6622 | 3 | 4 | 5 | | | V-2 | Awat1 | 158833 | 4-May-15 | 6715 | 3 | 4 | 5 | | | V-2 | Ccdc38 | 120935 | 28-May-15 |
| 6623 | 3 | 4 | 5 | | | V-2 | AY512915 | | | 6716 | 3 | 4 | 5 | | | V-2 | Ccdc42 | 146849 | 4-May-15 |
| 6624 | 3 | 4 | 5 | | | V-2 | B130034C11Rik | | | 6717 | 3 | 4 | 5 | | | V-2 | Ccdc42b | 387885 | 4-May-15 |
| 6625 | 3 | 4 | 5 | | | V-2 | B230112J18Rik | | | 6718 | 3 | 4 | 5 | | | V-2 | Ccdc43 | 124808 | 4-May-15 |
| 6626 | 3 | 4 | 5 | | | V-2 | B230119M05Rik | | | 6719 | 3 | 4 | 5 | | | V-2 | Ccdc53 | 51019 | 4-May-15 |
| 6627 | 3 | 4 | 5 | | | V-2 | B230219D22Rik | | | 6720 | 3 | 4 | 5 | | | V-2 | Ccdc82 | 79780 | 4-May-15 |
| 6628 | 3 | 4 | 5 | | | V-2 | B230319C09Rik | | | 6721 | 3 | 4 | 5 | | | V-2 | Ccdc85a | 114800 | 4-May-15 |
| 6629 | 3 | 4 | 5 | | | V-2 | B4galnt4 | 338707 | 4-May-15 | 6722 | 3 | 4 | 5 | | | V-2 | Ccdc85b | 11007 | 4-May-15 |
| 6630 | 3 | 4 | 5 | | | V-2 | Bag4 | 9530 | 3-May-15 | 6723 | 3 | 4 | 5 | | | V-2 | Ccdc86 | 79080 | 4-May-15 |
| 6631 | 3 | 4 | 5 | | | V-2 | Bahd1 | 22893 | 4-May-15 | 6724 | 3 | 4 | 5 | | | V-2 | Ccdc89 | 220388 | 4-May-15 |
| 6632 | 3 | 4 | 5 | | | V-2 | Bai3 | 577 | 4-May-15 | 6725 | 3 | 4 | 5 | | | V-2 | Ccdc97 | 90324 | 4-May-15 |
| 6633 | 3 | 4 | 5 | | | V-2 | Bambi-ps1 | | | 6726 | 3 | 4 | 5 | | | V-2 | Ccl26 | 10344 | 17-May-15 |
| 6634 | 3 | 4 | 5 | | | V-2 | Banf1 | 8815 | 4-May-15 | 6727 | 3 | 4 | 5 | | | V-2 | Ccni | 10983 | 4-May-15 |
| 6635 | 3 | 4 | 5 | | | V-2 | BB031773 | | | 6728 | 3 | 4 | 5 | | | V-2 | Ccrl1 | | |
| 6636 | 3 | 4 | 5 | | | V-2 | BB123696 | | | 6729 | 3 | 4 | 5 | | | V-2 | Ccr4 | 1233 | 7-Jun-15 |
| 6637 | 3 | 4 | 5 | | | V-2 | Bbs1 | 582 | 29-May-15 | 6730 | 3 | 4 | 5 | | | V-2 | Ccr9 | 10803 | 4-May-15 |
| 6638 | 3 | 4 | 5 | | | V-2 | Bbs7 | 55212 | 23-May-15 | 6731 | 3 | 4 | 5 | | | V-2 | Cd209e | | |
| 6639 | 3 | 4 | 5 | | | V-2 | Bbs9 | 27241 | 31-May-15 | 6732 | 3 | 4 | 5 | | | V-2 | Cd274 | 29126 | 24-May-15 |
| 6640 | 3 | 4 | 5 | | | V-2 | BC003331 | | | 6733 | 3 | 4 | 5 | | | V-2 | Cd2ap | 23607 | 4-May-15 |
| 6641 | 3 | 4 | 5 | | | V-2 | BC005537 | | | 6734 | 3 | 4 | 5 | | | V-2 | Cd2bp2 | 10421 | 4-May-15 |
| 6642 | 3 | 4 | 5 | | | V-2 | BC005624 | | | 6735 | 3 | 4 | 5 | | | V-2 | Cd40 | 958 | 12-May-15 |
| 6643 | 3 | 4 | 5 | | | V-2 | BC030307 | | | 6736 | 3 | 4 | 5 | | | V-2 | Cd79 | 970 | 4-May-15 |
| 6644 | 3 | 4 | 5 | | | V-2 | BC031181 | | | 6737 | 3 | 4 | 5 | | | V-2 | Cd8b1 | 926 | 12-May-15 |
| 6645 | 3 | 4 | 5 | | | V-2 | BC048671 | | | 6738 | 3 | 4 | 5 | | | V-2 | Cdc16 | 8881 | 12-May-15 |
| 6646 | 3 | 4 | 5 | | | V-2 | Bcan | 63827 | 12-May-15 | 6739 | 3 | 4 | 5 | | | V-2 | Cdc40 | 51362 | 4-May-15 |
| 6647 | 3 | 4 | 5 | | | V-2 | Bcap31 | 10134 | 24-May-15 | 6740 | 3 | 4 | 5 | | | V-2 | Cdh19 | 28513 | y-2015 |
| 6648 | 3 | 4 | 5 | | | V-2 | Bcas1os2 | | | 6741 | 3 | 4 | 5 | | | V-2 | Cdh2 | 1000 | 24-May-15 |
| 6649 | 3 | 4 | 5 | | | V-2 | Bccip | 56647 | 4-May-15 | 6742 | 3 | 4 | 5 | | | V-2 | Cdh20 | 28316 | 12-May-15 |
| 6650 | 3 | 4 | 5 | | | V-2 | Bckdhb | 594 | 23-May-15 | 6743 | 3 | 4 | 5 | | | V-2 | Cdh5 | 1003 | 31-May-15 |
| 6651 | 3 | 4 | 5 | | | V-2 | Bckdk | 10295 | 4-May-15 | 6744 | 3 | 4 | 5 | | | V-2 | Cdip1 | 29965 | 4-May-15 |
| 6652 | 3 | 4 | 5 | | | V-2 | Bcl2l13 | 23786 | 4-May-15 | 6745 | 3 | 4 | 5 | | | V-2 | Cdk4 | 1019 | 31-May-15 |
| 6653 | 3 | 4 | 5 | | | V-2 | Bcl9l | 283149 | 4-May-15 | 6746 | 3 | 4 | 5 | | | V-2 | Cdk5rap2 | 55755 | 23-May-15 |
| 6654 | 3 | 4 | 5 | | | V-2 | Bco2 | 83875 | 4-May-15 | 6747 | 3 | 4 | 5 | | | V-2 | Cdkl3 | 51265 | 4-May-15 |
| 6655 | 3 | 4 | 5 | | | V-2 | Bdp1 | 55814 | 7-Jun-15 | 6748 | 3 | 4 | 5 | | | V-2 | Cecr6 | 27439 | 4-May-15 |
| 6656 | 3 | 4 | 5 | | | V-2 | Bend3 | 57673 | 20-May-15 | 6749 | 3 | 4 | 5 | | | V-2 | Cep120 | 153241 | 4-May-15 |
| 6657 | 3 | 4 | 5 | | | V-2 | Best1 | 7439 | 23-May-15 | 6750 | 3 | 4 | 5 | | | V-2 | Cep135 | 9662 | 23-May-15 |
| 6658 | 3 | 4 | 5 | | | V-2 | Bet1 | 10282 | 4-May-15 | 6751 | 3 | 4 | 5 | | | V-2 | Cep290 | 80184 | 29-May-15 |
| 6659 | 3 | 4 | 5 | | | V-2 | Bhlhb9 | 80823 | 4-May-15 | 6752 | 3 | 4 | 5 | | | V-2 | Cep350 | 9857 | 12-May-15 |
| 6660 | 3 | 4 | 5 | | | V-2 | Bhmt | 635 | 4-May-15 | 6753 | 3 | 4 | 5 | | | V-2 | Cep85 | 64793 | 4-May-15 |
| 6661 | 3 | 4 | 5 | | | V-2 | Bhmt2 | 23743 | 4-May-15 | 6754 | 3 | 4 | 5 | | | V-2 | Cers2 | 29956 | 4-May-15 |
| 6662 | 3 | 4 | 5 | | | V-2 | Bmp8a | 353500 | 4-May-15 | 6755 | 3 | 4 | 5 | | | V-2 | Ces1c | | |
| 6663 | 3 | 4 | 5 | | | V-2 | Bnc2 | 54796 | 4-May-15 | 6756 | 3 | 4 | 5 | | | V-2 | Ces2f | | |
| 6664 | 3 | 4 | 5 | | | V-2 | Bnip1 | 662 | 4-May-15 | 6757 | 3 | 4 | 5 | | | V-2 | Ces3a | | |
| 6665 | 3 | 4 | 5 | | | V-2 | Brat1 | 221927 | 31-May-15 | 6758 | 3 | 4 | 5 | | | V-2 | Ces3b | | |
| 6666 | 3 | 4 | 5 | | | V-2 | Brdt | 676 | 4-May-15 | 6759 | 3 | 4 | 5 | | | V-2 | Cetn2 | 1069 | 31-May-15 |
| 6667 | 3 | 4 | 5 | | | V-2 | Bscl2 | 26580 | 23-May-15 | 6760 | 3 | 4 | 5 | | | V-2 | Chchd3 | 54927 | 4-May-15 |
| 6668 | 3 | 4 | 5 | | | V-2 | Btbd9 | 114781 | 4-May-15 | 6761 | 3 | 4 | 5 | | | V-2 | Chchd4 | 131474 | 4-May-15 |
| 6669 | 3 | 4 | 5 | | | V-2 | C030007H22Rik | | | 6762 | 3 | 4 | 5 | | | V-2 | Chrm3 | 1131 | 4-May-15 |
| 6670 | 3 | 4 | 5 | | | V-2 | C030034L19Rik | | | 6763 | 3 | 4 | 5 | | | V-2 | Chrm5 | 1133 | 4-May-15 |
| 6671 | 3 | 4 | 5 | | | V-2 | C130036L24Rik | | | 6764 | 3 | 4 | 5 | | | V-2 | Chrna2 | 1135 | 23-May-15 |
| 6672 | 3 | 4 | 5 | | | V-2 | C130050O18Rik | | | 6765 | 3 | 4 | 5 | | | V-2 | Chrnb1 | 1140 | 4-May-15 |
| 6673 | 3 | 4 | 5 | | | V-2 | C1qc | 714 | 4-May-15 | 6766 | 3 | 4 | 5 | | | V-2 | Chrnd | 1144 | 7-May-15 |
| 6674 | 3 | 4 | 5 | | | V-2 | C230037L18Rik | | | 6767 | 3 | 4 | 5 | | | V-2 | Chst9 | 83539 | 4-May-15 |
| 6675 | 3 | 4 | 5 | | | V-2 | C230052I12Rik | | | 6768 | 3 | 4 | 5 | | | V-2 | Ciapin1 | 57019 | 12-May-15 |
| 6676 | 3 | 4 | 5 | | | V-2 | C2cd4d | 100191040 | 4-May-15 | 6769 | 3 | 4 | 5 | | | V-2 | Cisd2 | 493856 | 2-Jun-15 |
| 6677 | 3 | 4 | 5 | | | V-2 | C2cd5 | 9847 | 4-May-15 | 6770 | 3 | 4 | 5 | | | V-2 | Cldnd2 | 125875 | 4-May-15 |
| 6678 | 3 | 4 | 5 | | | V-2 | C330018D20Rik | | | 6771 | 3 | 4 | 5 | | | V-2 | Clec4b1 | | |
| 6679 | 3 | 4 | 5 | | | V-2 | C330021F23Rik | | | 6772 | 3 | 4 | 5 | | | V-2 | Clvs1 | 157807 | 28-May-15 |
| 6680 | 3 | 4 | 5 | | | V-2 | C530005A16Rik | | | 6773 | 3 | 4 | 5 | | | V-2 | Cmas | 55907 | 12-May-15 |
| 6681 | 3 | 4 | 5 | | | V-2 | C530008M17Rik | | | 6774 | 3 | 4 | 5 | | | V-2 | Cmtm1 | 113540 | 4-May-15 |
| 6682 | 3 | 4 | 5 | | | V-2 | C87414 | | | 6775 | 3 | 4 | 5 | | | V-2 | Cnga2 | 1260 | 6-May-15 |
| 6683 | 3 | 4 | 5 | | | V-2 | C8g | 733 | 4-May-15 | 6776 | 3 | 4 | 5 | | | V-2 | Cntf | 1270 | 4-May-15 |
| 6684 | 3 | 4 | 5 | | | V-2 | C920006O11Rik | | | 6777 | 3 | 4 | 5 | | | V-2 | Cntn2 | 6900 | 4-May-15 |
| 6685 | 3 | 4 | 5 | | | V-2 | Cacnb1 | 782 | 12-May-15 | 6778 | 3 | 4 | 5 | | | V-2 | Cntnap3 | 79937 | 4-May-15 |
| 6686 | 3 | 4 | 5 | | | V-2 | Cacnb3 | 784 | 4-May-15 | 6779 | 3 | 4 | 5 | | | V-2 | Coasy | 80347 | 4-May-15 |
| 6687 | 3 | 4 | 5 | | | V-2 | Calm3 | 808 | 12-May-15 | 6780 | 3 | 4 | 5 | | | V-2 | Cobll1 | 22837 | 4-May-15 |
| 6688 | 3 | 4 | 5 | | | V-2 | Camkv | 79012 | 4-May-15 | 6781 | 3 | 4 | 5 | | | V-2 | Col25a1 | 84570 | 4-May-15 |
| 6689 | 3 | 4 | 5 | | | V-2 | Caps2 | 84698 | 4-May-15 | 6782 | 3 | 4 | 5 | | | V-2 | Col7a1 | 1294 | 31-May-15 |
| 6690 | 3 | 4 | 5 | | | V-2 | Card14 | 79092 | 4-May-15 | 6783 | 3 | 4 | 5 | | | V-2 | Commd6 | 170622 | 4-May-15 |
| 6691 | 3 | 4 | 5 | | | V-2 | Casp14 | 23581 | 4-May-15 | 6784 | 3 | 4 | 5 | | | V-2 | Coq10a | 93058 | 4-May-15 |
| 6692 | 3 | 4 | 5 | | | V-2 | Casp8 | 841 | 23-May-15 | 6785 | 3 | 4 | 5 | | | V-2 | Coq3 | 51805 | 9-May-15 |
| 6693 | 3 | 4 | 5 | | | V-2 | Catsper1 | 117144 | 23-May-15 | 6786 | 3 | 4 | 5 | | | V-2 | Coq7 | 10229 | 28-May-15 |
| 6694 | 3 | 4 | 5 | | | V-2 | Cbwd1 | 55871 | 4-May-15 | 6787 | 3 | 4 | 5 | | | V-2 | Coq9 | 57017 | 3-May-15 |
| 6695 | 3 | 4 | 5 | | | V-2 | Cbx8 | 57332 | 4-May-15 | 6788 | 3 | 4 | 5 | | | V-2 | Cox11 | 1353 | 7-Jun-15 |
| 6696 | 3 | 4 | 5 | | | V-2 | Ccar1 | 55749 | 29-May-15 | 6789 | 3 | 4 | 5 | | | V-2 | Cox15 | 1355 | 23-May-15 |
| 6697 | 3 | 4 | 5 | | | V-2 | Ccdc101 | 112869 | 4-May-15 | 6790 | 3 | 4 | 5 | | | V-2 | Cox16 | 51241 | 4-May-15 |
| 6698 | 3 | 4 | 5 | | | V-2 | Ccdc115 | 84317 | 4-May-15 | 6791 | 3 | 4 | 5 | | | V-2 | Cox4i2 | 84701 | 4-May-15 |
| 6699 | 3 | 4 | 5 | | | V-2 | Ccdc126 | 90693 | 4-May-15 | 6792 | 3 | 4 | 5 | | | V-2 | Cox5b | 1329 | 21-May-15 |
| 6700 | 3 | 4 | 5 | | | V-2 | Ccdc13 | 152206 | 29-May-15 | 6793 | 3 | 4 | 5 | | | V-2 | Cox6a1 | 1337 | 12-May-15 |
| 6701 | 3 | 4 | 5 | | | V-2 | Ccdc142 | 84865 | 4-May-15 | 6794 | 3 | 4 | 5 | | | V-2 | Cox7a2l | 9167 | 4-May-15 |
| 6702 | 3 | 4 | 5 | | | V-2 | Ccdc147 | 159686 | 4-May-15 | 6795 | 3 | 4 | 5 | | | V-2 | Cox7b2 | 170712 | 4-May-15 |
| 6703 | 3 | 4 | 5 | | | V-2 | Ccdc150 | 284992 | 4-May-15 | 6796 | 3 | 4 | 5 | | | V-2 | Cox8a | 1351 | 28-May-15 |
| 6704 | 3 | 4 | 5 | | | V-2 | Ccdc152 | 100129792 | 4-May-15 | 6797 | 3 | 4 | 5 | | | V-2 | Cpeb2 | 132864 | 4-May-15 |
| 6705 | 3 | 4 | 5 | | | V-2 | Ccdc154 | 645811 | 4-May-15 | 6798 | 3 | 4 | 5 | | | V-2 | Cphx2 | | |
| 6706 | 3 | 4 | 5 | | | V-2 | Ccdc160 | 347475 | 12-May-15 | 6799 | 3 | 4 | 5 | | | V-2 | Cpsf1 | 29894 | 4-May-15 |
| 6707 | 3 | 4 | 5 | | | V-2 | Ccdc163 | | | 6800 | 3 | 4 | 5 | | | V-2 | Cpvl | 54504 | 23-May-15 |
| 6708 | 3 | 4 | 5 | | | V-2 | Ccdc171 | 203238 | 4-May-15 | 6801 | 3 | 4 | 5 | | | V-2 | Cpz | 8532 | 4-May-15 |
| 6709 | 3 | 4 | 5 | | | V-2 | Ccdc172 | 374355 | 4-May-15 | 6802 | 3 | 4 | 5 | | | V-2 | Cramp1l | 57585 | 4-May-15 |
| 6710 | 3 | 4 | 5 | | | V-2 | Ccdc174 | 51244 | 4-May-15 | 6803 | 3 | 4 | 5 | | | V-2 | Creb3l4 | 148327 | 28-May-15 |
| 6711 | 3 | 4 | 5 | | | V-2 | Ccdc22 | 28952 | 4-May-15 | 6804 | 3 | 4 | 5 | | | V-2 | Cript | 9419 | 4-May-15 |
| 6712 | 3 | 4 | 5 | | | V-2 | Ccdc25 | 55246 | 12-May-15 | 6805 | 3 | 4 | 5 | | | V-2 | Crnde | 643911 | 20-May-15 |
| 6713 | 3 | 4 | 5 | | | V-2 | Ccdc28b | 79140 | 23-May-15 | 6806 | 3 | 4 | 5 | | | V-2 | Crnkl1 | 51340 | 28-May-15 |
| | | | | | | | | | | 6807 | 3 | 4 | 5 | | | V-2 | Crygb | 1419 | 4-May-15 |
| | | | | | | | | | | 6808 | 3 | 4 | 5 | | | V-2 | Crygs | 1427 | 4-May-15 |
| | | | | | | | | | | 6809 | 3 | 4 | 5 | | | V-2 | Cryzl1 | 9946 | 4-May-15 |

Fig. 30 - 37

| | | | | | | | | | | | | | | | | |
|---|---|---|---|---|---|---|---|---|---|---|---|---|---|---|---|---|
| 6810 | 3 | 4 | 5 | | | V-2 | Csad | 51380 | 4-May-15 | 6905 | 3 | 4 | 5 | | | V-2 | Dnajc2 | 27000 | 4-May-15 |
| 6811 | 3 | 4 | 5 | | | V-2 | Csde1 | 7812 | 1-Jun-15 | 6906 | 3 | 4 | 5 | | | V-2 | Dnajc24 | 120526 | 4-May-15 |
| 6812 | 3 | 4 | 5 | | | V-2 | Csmd1 | 64478 | 12-May-15 | 6907 | 3 | 4 | 5 | | | V-2 | Dnajc3 | 5611 | 4-May-15 |
| 6813 | 3 | 4 | 5 | | | V-2 | Csrp | 8530 | 12-May-15 | 6908 | 3 | 4 | 5 | | | V-2 | Dnlz | 728489 | 4-May-15 |
| 6814 | 3 | 4 | 5 | | | V-2 | Cst9 | 128822 | 4-May-15 | 6909 | 3 | 4 | 5 | | | V-2 | Dnmt3l | 29947 | 17-May-15 |
| 6815 | 3 | 4 | 5 | | | V-2 | Ctf2 | | | 6910 | 3 | 4 | 5 | | | V-2 | Dnttip1 | 116092 | 4-May-15 |
| 6816 | 3 | 4 | 5 | | | V-2 | Ctnna3 | 29119 | 12-May-15 | 6911 | 3 | 4 | 5 | | | V-2 | Dock6 | 57572 | 21-May-15 |
| 6817 | 3 | 4 | 5 | | | V-2 | Ctnnal1 | 8727 | 12-May-15 | 6912 | 3 | 4 | 5 | | | V-2 | Dohh | 83475 | 4-May-15 |
| 6818 | 3 | 4 | 5 | | | V-2 | Ctnnb1 | 1499 | 31-May-15 | 6913 | 3 | 4 | 5 | | | V-2 | Dpysl5 | 56896 | 4-May-15 |
| 6819 | 3 | 4 | 5 | | | V-2 | Cux1 | 1523 | 28-May-15 | 6914 | 3 | 4 | 5 | | | V-2 | Drd5 | 1816 | 28-May-15 |
| 6820 | 3 | 4 | 5 | | | V-2 | Cwf19l2 | 143884 | 4-May-15 | 6915 | 3 | 4 | 5 | | | V-2 | Dscam | 1826 | 4-May-15 |
| 6821 | 3 | 4 | 5 | | | V-2 | Cyb5r1 | 51706 | 4-May-15 | 6916 | 3 | 4 | 5 | | | V-2 | Dsg3 | 1830 | 12-May-15 |
| 6822 | 3 | 4 | 5 | | | V-2 | Cyb5r3 | 1727 | 21-May-15 | 6917 | 3 | 4 | 5 | | | V-2 | Dspp | 1834 | 4-May-15 |
| 6823 | 3 | 4 | 5 | | | V-2 | Cyc1 | 1537 | 7-Jun-15 | 6918 | 3 | 4 | 5 | | | V-2 | Dstn | 11034 | 4-May-15 |
| 6824 | 3 | 4 | 5 | | | V-2 | Cycs | 54205 | 12-May-15 | 6919 | 3 | 4 | 5 | | | V-2 | Dtnb | 1838 | 4-May-15 |
| 6825 | 3 | 4 | 5 | | | V-2 | Cyct | | | 6920 | 3 | 4 | 5 | | | V-2 | Dtx3 | 196403 | 2-Jun-15 |
| 6826 | 3 | 4 | 5 | | | V-2 | Cyp1a2 | 1544 | 24-May-15 | 6921 | 3 | 4 | 5 | | | V-2 | Duox2 | 50506 | 24-May-15 |
| 6827 | 3 | 4 | 5 | | | V-2 | Cyp2b19 | | | 6922 | 3 | 4 | 5 | | | V-2 | Dusp19 | 142679 | 4-May-15 |
| 6828 | 3 | 4 | 5 | | | V-2 | Cyp2b23 | | | 6923 | 3 | 4 | 5 | | | V-2 | Dvl3 | 1857 | 12-May-15 |
| 6829 | 3 | 4 | 5 | | | V-2 | Cyp2c53-ps | | | 6924 | 3 | 4 | 5 | | | V-2 | Dym | 54808 | 4-May-15 |
| 6830 | 3 | 4 | 5 | | | V-2 | Cyp2c65 | | | 6925 | 3 | 4 | 5 | | | V-2 | Dynll1 | 8655 | 24-May-15 |
| 6831 | 3 | 4 | 5 | | | V-2 | Cyp2c68 | | | 6926 | 3 | 4 | 5 | | | V-2 | Dynlrb1 | 83658 | 4-May-15 |
| 6832 | 3 | 4 | 5 | | | V-2 | Cyp2c70 | | | 6927 | 3 | 4 | 5 | | | V-2 | Dynlt1c | | |
| 6833 | 3 | 4 | 5 | | | V-2 | Cyp2d22 | | | 6928 | 3 | 4 | 5 | | | V-2 | Dzip1 | 22873 | 4-May-15 |
| 6834 | 3 | 4 | 5 | | | V-2 | Cyp2d34 | | | 6929 | 3 | 4 | 5 | | | V-2 | E030019B13Rik | | |
| 6835 | 3 | 4 | 5 | | | V-2 | Cypt14 | | | 6930 | 3 | 4 | 5 | | | V-2 | E130006D01Rik | | |
| 6836 | 3 | 4 | 5 | | | V-2 | Cysltr1 | 10800 | 4-May-15 | 6931 | 3 | 4 | 5 | | | V-2 | E130018N17Rik | | |
| 6837 | 3 | 4 | 5 | | | V-2 | Cystm1 | 84418 | 12-May-15 | 6932 | 3 | 4 | 5 | | | V-2 | E130112N10Rik | | |
| 6838 | 3 | 4 | 5 | | | V-2 | D10Wsu102e | | | 6933 | 3 | 4 | 5 | | | V-2 | E130114P18Rik | | |
| 6839 | 3 | 4 | 5 | | | V-2 | D130040H23Rik | | | 6934 | 3 | 4 | 5 | | | V-2 | E130201H02Rik | | |
| 6840 | 3 | 4 | 5 | | | V-2 | D130058E03 | | | 6935 | 3 | 4 | 5 | | | V-2 | E230018K23Rik | | |
| 6841 | 3 | 4 | 5 | | | V-2 | D19Bwg1357e | | | 6936 | 3 | 4 | 5 | | | V-2 | E330012B07Rik | | |
| 6842 | 3 | 4 | 5 | | | V-2 | D2Wsu81e | | | 6937 | 3 | 4 | 5 | | | V-2 | E430018J23Rik | | |
| 6843 | 3 | 4 | 5 | | | V-2 | D330050I16Rik | | | 6938 | 3 | 4 | 5 | | | V-2 | Efcab11 | 90141 | 4-May-15 |
| 6844 | 3 | 4 | 5 | | | V-2 | D5Ertd605e | | | 6939 | 3 | 4 | 5 | | | V-2 | Efcab12 | 90288 | 4-May-15 |
| 6845 | 3 | 4 | 5 | | | V-2 | D630010B17Rik | | | 6940 | 3 | 4 | 5 | | | V-2 | Efcab3 | 146779 | 4-May-15 |
| 6846 | 3 | 4 | 5 | | | V-2 | D630023F18Rik | | | 6941 | 3 | 4 | 5 | | | V-2 | Efcab5 | 374786 | 4-May-15 |
| 6847 | 3 | 4 | 5 | | | V-2 | D630045M09Rik | | | 6942 | 3 | 4 | 5 | | | V-2 | Efcab7 | 84455 | 4-May-15 |
| 6848 | 3 | 4 | 5 | | | V-2 | D730005E14Rik | | | 6943 | 3 | 4 | 5 | | | V-2 | Efna5 | 1946 | 24-May-15 |
| 6849 | 3 | 4 | 5 | | | V-2 | D7Ertd715e | | | 6944 | 3 | 4 | 5 | | | V-2 | Efr3a | 23167 | 4-May-15 |
| 6850 | 3 | 4 | 5 | | | V-2 | D830013O20Rik | | | 6945 | 3 | 4 | 5 | | | V-2 | Egln2 | 112398 | 4-May-15 |
| 6851 | 3 | 4 | 5 | | | V-2 | D830030K20Rik | | | 6946 | 3 | 4 | 5 | | | V-2 | Eif4e1b | 253314 | 4-May-15 |
| 6852 | 3 | 4 | 5 | | | V-2 | D830046C22Rik | | | 6947 | 3 | 4 | 5 | | | V-2 | Elk1 | 2002 | 7-Jun-15 |
| 6853 | 3 | 4 | 5 | | | V-2 | D8Ertd738e | | | 6948 | 3 | 4 | 5 | | | V-2 | Elmod2 | 255520 | 4-May-15 |
| 6854 | 3 | 4 | 5 | | | V-2 | Daam1 | 23002 | 14-May-15 | 6949 | 3 | 4 | 5 | | | V-2 | Elp2 | 55250 | 4-May-15 |
| 6855 | 3 | 4 | 5 | | | V-2 | Dab1 | 1600 | 7-Jun-15 | 6950 | 3 | 4 | 5 | | | V-2 | Emcn | 51705 | 4-May-15 |
| 6856 | 3 | 4 | 5 | | | V-2 | Dact3 | 147906 | 4-May-15 | 6951 | 3 | 4 | 5 | | | V-2 | Enpp3 | 5169 | 4-May-15 |
| 6857 | 3 | 4 | 5 | | | V-2 | Daird3 | 55152 | 4-May-15 | 6952 | 3 | 4 | 5 | | | V-2 | Entpd6 | 955 | 4-May-15 |
| 6858 | 3 | 4 | 5 | | | V-2 | Dapk1 | 1612 | 4-May-15 | 6953 | 3 | 4 | 5 | | | V-2 | Eny2 | 56943 | 12-May-15 |
| 6859 | 3 | 4 | 5 | | | V-2 | Daw1 | 164781 | 4-May-15 | 6954 | 3 | 4 | 5 | | | V-2 | Epb4.1l4b | | |
| 6860 | 3 | 4 | 5 | | | V-2 | Dbpht2 | | | 6955 | 3 | 4 | 5 | | | V-2 | Epha10 | 284656 | 4-May-15 |
| 6861 | 3 | 4 | 5 | | | V-2 | Dbx1 | 120237 | 4-May-15 | 6956 | 3 | 4 | 5 | | | V-2 | Epha5 | 2044 | 29-May-15 |
| 6862 | 3 | 4 | 5 | | | V-2 | Dcaf12l2 | 340578 | 4-May-15 | 6957 | 3 | 4 | 5 | | | V-2 | Ephb2 | 2048 | 23-May-15 |
| 6863 | 3 | 4 | 5 | | | V-2 | Dcbld1 | 285761 | 4-May-15 | 6958 | 3 | 4 | 5 | | | V-2 | Epm2aip1 | 9852 | 4-May-15 |
| 6864 | 3 | 4 | 5 | | | V-2 | Dcdc2c | 728597 | 21-May-15 | 6959 | 3 | 4 | 5 | | | V-2 | Eqtn | 54586 | 4-May-15 |
| 6865 | 3 | 4 | 5 | | | V-2 | Dcire1a | 9937 | 12-May-15 | 6960 | 3 | 4 | 5 | | | V-2 | Erich3 | 127254 | 12-May-15 |
| 6866 | 3 | 4 | 5 | | | V-2 | Dcpp2 | | | 6961 | 3 | 4 | 5 | | | V-2 | Erich5 | 203111 | 4-May-15 |
| 6867 | 3 | 4 | 5 | | | V-2 | Dcstamp | 81501 | 12-May-15 | 6962 | 3 | 4 | 5 | | | V-2 | Erp29 | 10961 | 17-May-15 |
| 6868 | 3 | 4 | 5 | | | V-2 | Dctd | 1635 | 4-May-15 | 6963 | 3 | 4 | 5 | | | V-2 | Esrrb | 2103 | 23-May-15 |
| 6869 | 3 | 4 | 5 | | | V-2 | Dcun1d3 | 123879 | 3-May-15 | 6964 | 3 | 4 | 5 | | | V-2 | Esx1 | 80712 | 12-May-15 |
| 6870 | 3 | 4 | 5 | | | V-2 | Dcun1d5 | 84259 | 4-May-15 | 6965 | 3 | 4 | 5 | | | V-2 | Etaa1 | 54465 | 4-May-15 |
| 6871 | 3 | 4 | 5 | | | V-2 | Ddx1 | 1653 | 4-May-15 | 6966 | 3 | 4 | 5 | | | V-2 | Etfb | 2109 | 12-May-15 |
| 6872 | 3 | 4 | 5 | | | V-2 | Deb1 | | | 6967 | 3 | 4 | 5 | | | V-2 | Ethe1 | 23474 | 4-May-15 |
| 6873 | 3 | 4 | 5 | | | V-2 | Defa20 | | | 6968 | 3 | 4 | 5 | | | V-2 | Etv2 | 2116 | 28-May-15 |
| 6874 | 3 | 4 | 5 | | | V-2 | Defa22 | | | 6969 | 3 | 4 | 5 | | | V-2 | Etv3 | 2117 | 28-May-15 |
| 6875 | 3 | 4 | 5 | | | V-2 | Defa24 | | | 6970 | 3 | 4 | 5 | | | V-2 | Eva1b | 55194 | 4-May-15 |
| 6876 | 3 | 4 | 5 | | | V-2 | Defb7 | 245910 | 4-May-15 | 6971 | 3 | 4 | 5 | | | V-2 | Evx1 | 2128 | 4-May-15 |
| 6877 | 3 | 4 | 5 | | | V-2 | Dennd4c | 55667 | 4-May-15 | 6972 | 3 | 4 | 5 | | | V-2 | Ext1 | 2131 | 23-May-15 |
| 6878 | 3 | 4 | 5 | | | V-2 | Dfna5 | 1687 | 23-May-15 | 6973 | 3 | 4 | 5 | | | V-2 | Extl2 | 2135 | 4-May-15 |
| 6879 | 3 | 4 | 5 | | | V-2 | Dfnb59 | 494513 | 23-May-15 | 6974 | 3 | 4 | 5 | | | V-2 | F830045P16Rik | | |
| 6880 | 3 | 4 | 5 | | | V-2 | Dgkh | 160851 | 12-May-15 | 6975 | 3 | 4 | 5 | | | V-2 | Fads1 | 3992 | 12-May-15 |
| 6881 | 3 | 4 | 5 | | | V-2 | Dhdh | 27294 | 4-May-15 | 6976 | 3 | 4 | 5 | | | V-2 | Faf1 | 11124 | 4-May-15 |
| 6882 | 3 | 4 | 5 | | | V-2 | Dhps | 1725 | 12-May-15 | 6977 | 3 | 4 | 5 | | | V-2 | Faim | 55179 | 4-May-15 |
| 6883 | 3 | 4 | 5 | | | V-2 | Dhrs4 | 10901 | 12-May-15 | 6978 | 3 | 4 | 5 | | | V-2 | Fam102b | 284611 | 4-May-15 |
| 6884 | 3 | 4 | 5 | | | V-2 | Dhrs7b | 25979 | 4-May-15 | 6979 | 3 | 4 | 5 | | | V-2 | Fam131b | 9715 | 28-May-15 |
| 6885 | 3 | 4 | 5 | | | V-2 | Dhx15 | 1665 | 3-May-15 | 6980 | 3 | 4 | 5 | | | V-2 | Fam155a | 728215 | 4-May-15 |
| 6886 | 3 | 4 | 5 | | | V-2 | Dip2c | 22982 | 4-May-15 | 6981 | 3 | 4 | 5 | | | V-2 | Fam162a | 26355 | 4-May-15 |
| 6887 | 3 | 4 | 5 | | | V-2 | Dis3l2 | 129563 | 4-May-15 | 6982 | 3 | 4 | 5 | | | V-2 | Fam163b | 642968 | 4-May-15 |
| 6888 | 3 | 4 | 5 | | | V-2 | Dkc1 | 1736 | 31-May-15 | 6983 | 3 | 4 | 5 | | | V-2 | Fam170a | 340069 | 4-May-15 |
| 6889 | 3 | 4 | 5 | | | V-2 | Dlec1 | 9940 | 4-May-15 | 6984 | 3 | 4 | 5 | | | V-2 | Fam171a2 | 284069 | 12-May-15 |
| 6890 | 3 | 4 | 5 | | | V-2 | Dleu2 | 8847 | 12-May-15 | 6985 | 3 | 4 | 5 | | | V-2 | Fam179b | 23116 | 12-May-15 |
| 6891 | 3 | 4 | 5 | | | V-2 | Dlg1 | 1739 | 12-May-15 | 6986 | 3 | 4 | 5 | | | V-2 | Fam181b | 220382 | 4-May-15 |
| 6892 | 3 | 4 | 5 | | | V-2 | Dlg4 | 1742 | 7-Jun-15 | 6987 | 3 | 4 | 5 | | | V-2 | Fam186b | 84070 | 4-May-15 |
| 6893 | 3 | 4 | 5 | | | V-2 | Dlx1 | 1745 | 4-May-15 | 6988 | 3 | 4 | 5 | | | V-2 | Fam20a | 54757 | 30-Apr-15 |
| 6894 | 3 | 4 | 5 | | | V-2 | Dmgdh | 29958 | 4-May-15 | 6989 | 3 | 4 | 5 | | | V-2 | Fam217a | 222826 | 4-May-15 |
| 6895 | 3 | 4 | 5 | | | V-2 | Dmpk | 1760 | 31-May-15 | 6990 | 3 | 4 | 5 | | | V-2 | Fam219a | 203259 | 4-May-15 |
| 6896 | 3 | 4 | 5 | | | V-2 | Dmrt3 | 58524 | 4-May-15 | 6991 | 3 | 4 | 5 | | | V-2 | Fam221b | 392307 | 4-May-15 |
| 6897 | 3 | 4 | 5 | | | V-2 | Dnah1 | 25981 | 28-May-15 | 6992 | 3 | 4 | 5 | | | V-2 | Fam228b | 55731 | 4-May-15 |
| 6898 | 3 | 4 | 5 | | | V-2 | Dnah17 | 8632 | 4-May-15 | 6993 | 3 | 4 | 5 | | | V-2 | Fam228a | 653140 | 4-May-15 |
| 6899 | 3 | 4 | 5 | | | V-2 | Dnah6 | 1768 | 4-May-15 | 6994 | 3 | 4 | 5 | | | V-2 | Fam24a | 118670 | 4-May-15 |
| 6900 | 3 | 4 | 5 | | | V-2 | Dnah7a | | | 6995 | 3 | 4 | 5 | | | V-2 | Fam49a | 81553 | 4-May-15 |
| 6901 | 3 | 4 | 5 | | | V-2 | Dnaic1 | | | 6996 | 3 | 4 | 5 | | | V-2 | Fam83b | 222584 | 4-May-15 |
| 6902 | 3 | 4 | 5 | | | V-2 | Dnaja1 | 3301 | 4-May-15 | 6997 | 3 | 4 | 5 | | | V-2 | Fam83f | 113828 | 12-May-15 |
| 6903 | 3 | 4 | 5 | | | V-2 | Dnaja3 | 9093 | 4-May-15 | 6998 | 3 | 4 | 5 | | | V-2 | Fam96a | 84191 | 4-May-15 |
| 6904 | 3 | 4 | 5 | | | V-2 | Dnajc12 | 56521 | 4-May-15 | 6999 | 3 | 4 | 5 | | | V-2 | Farsa | 2193 | 4-May-15 |
| | | | | | | | | | | 7000 | 3 | 4 | 5 | | | V-2 | Fastkd1 | 79675 | 4-May-15 |

Fig. 30 - 38

| | | | | | | | | | | | | | | | |
|---|---|---|---|---|---|---|---|---|---|---|---|---|---|---|---|
| 7001 | 3 | 4 | 5 | | | V-2 | Fastkd2 | 22868 | 4-May-15 | 7097 | 3 | 4 | 5 | | | V-2 | Gm14164 | | |
| 7002 | 3 | 4 | 5 | | | V-2 | Fastkd3 | 79072 | 4-May-15 | 7098 | 3 | 4 | 5 | | | V-2 | Gm14374 | | |
| 7003 | 3 | 4 | 5 | | | V-2 | Fate1 | 89885 | 4-May-15 | 7099 | 3 | 4 | 5 | | | V-2 | Gm14378 | | |
| 7004 | 3 | 4 | 5 | | | V-2 | Fbxl17 | 64839 | 4-May-15 | 7100 | 3 | 4 | 5 | | | V-2 | Gm15217 | | |
| 7005 | 3 | 4 | 5 | | | V-2 | Fbxl20 | 84961 | 1-Jun-15 | 7101 | 3 | 4 | 5 | | | V-2 | Gm15679 | | |
| 7006 | 3 | 4 | 5 | | | V-2 | Fbxl22 | 283807 | 4-May-15 | 7102 | 3 | 4 | 5 | | | V-2 | Gm16497 | | |
| 7007 | 3 | 4 | 5 | | | V-2 | Fbxo2 | 26232 | 12-May-15 | 7103 | 3 | 4 | 5 | | | V-2 | Gm16596 | | |
| 7008 | 3 | 4 | 5 | | | V-2 | Fbxo45 | 200933 | 4-May-15 | 7104 | 3 | 4 | 5 | | | V-2 | Gm1661 | | |
| 7009 | 3 | 4 | 5 | | | V-2 | Fbxw11 | 23291 | 4-May-15 | 7105 | 3 | 4 | 5 | | | V-2 | Gm16894 | | |
| 7010 | 3 | 4 | 5 | | | V-2 | Fdx1l | 112812 | 4-May-15 | 7106 | 3 | 4 | 5 | | | V-2 | Gm19299 | | |
| 7011 | 3 | 4 | 5 | | | V-2 | Fem1b | 10116 | 4-May-15 | 7107 | 3 | 4 | 5 | | | V-2 | Gm19424 | | |
| 7012 | 3 | 4 | 5 | | | V-2 | Fermt2 | 10979 | 4-May-15 | 7108 | 3 | 4 | 5 | | | V-2 | Gm19466 | | |
| 7013 | 3 | 4 | 5 | | | V-2 | Fgd1 | 2245 | 31-May-15 | 7109 | 3 | 4 | 5 | | | V-2 | Gm19557 | | |
| 7014 | 3 | 4 | 5 | | | V-2 | Fgd5 | 152273 | 12-May-15 | 7110 | 3 | 4 | 5 | | | V-2 | Gm19583 | | |
| 7015 | 3 | 4 | 5 | | | V-2 | Fgf17 | 8822 | 12-May-15 | 7111 | 3 | 4 | 5 | | | V-2 | Gm1968 | | |
| 7016 | 3 | 4 | 5 | | | V-2 | Fhad1 | 114827 | 4-May-15 | 7112 | 3 | 4 | 5 | | | V-2 | Gm19757 | | |
| 7017 | 3 | 4 | 5 | | | V-2 | Flcn | 203163 | 24-May-15 | 7113 | 3 | 4 | 5 | | | V-2 | Gm20748 | | |
| 7018 | 3 | 4 | 5 | | | V-2 | Flt3l | 2323 | 12-May-15 | 7114 | 3 | 4 | 5 | | | V-2 | Gm20750 | | |
| 7019 | 3 | 4 | 5 | | | V-2 | Fmn1 | 342184 | 12-May-15 | 7115 | 3 | 4 | 5 | | | V-2 | Gm21671 | | |
| 7020 | 3 | 4 | 5 | | | V-2 | Fndc8 | 54752 | 4-May-15 | 7116 | 3 | 4 | 5 | | | V-2 | Gm21950 | | |
| 7021 | 3 | 4 | 5 | | | V-2 | Foxb1 | 27023 | 28-May-15 | 7117 | 3 | 4 | 5 | | | V-2 | Gm2373 | | |
| 7022 | 3 | 4 | 5 | | | V-2 | Foxb2 | 442425 | 28-May-15 | 7118 | 3 | 4 | 5 | | | V-2 | Gm2721 | | |
| 7023 | 3 | 4 | 5 | | | V-2 | Foxd4 | 2298 | 28-May-15 | 7119 | 3 | 4 | 5 | | | V-2 | Gm2825 | | |
| 7024 | 3 | 4 | 5 | | | V-2 | Foxg1 | 2290 | 27-May-15 | 7120 | 3 | 4 | 5 | | | V-2 | Gm2897 | | |
| 7025 | 3 | 4 | 5 | | | V-2 | Foxp1 | 27086 | 2-Jun-15 | 7121 | 3 | 4 | 5 | | | V-2 | Gm2913 | | |
| 7026 | 3 | 4 | 5 | | | V-2 | Foxred2 | 80020 | 4-May-15 | 7122 | 3 | 4 | 5 | | | V-2 | Gm2933 | | |
| 7027 | 3 | 4 | 5 | | | V-2 | Frmd6 | 122786 | 4-May-15 | 7123 | 3 | 4 | 5 | | | V-2 | Gm3258 | | |
| 7028 | 3 | 4 | 5 | | | V-2 | Frmpd1 | 22844 | 4-May-15 | 7124 | 3 | 4 | 5 | | | V-2 | Gm3286 | | |
| 7029 | 3 | 4 | 5 | | | V-2 | Frmpd1os | | | 7125 | 3 | 4 | 5 | | | V-2 | Gm3376 | | |
| 7030 | 3 | 4 | 5 | | | V-2 | Frrs1l | 23732 | 4-May-15 | 7126 | 3 | 4 | 5 | | | V-2 | Gm3402 | | |
| 7031 | 3 | 4 | 5 | | | V-2 | Frs3os | | | 7127 | 3 | 4 | 5 | | | V-2 | Gm3428 | | |
| 7032 | 3 | 4 | 5 | | | V-2 | Fry | 10129 | 12-May-15 | 7128 | 3 | 4 | 5 | | | V-2 | Gm3458 | | |
| 7033 | 3 | 4 | 5 | | | V-2 | Fsd2 | 123722 | 4-May-15 | 7129 | 3 | 4 | 5 | | | V-2 | Gm3558 | | |
| 7034 | 3 | 4 | 5 | | | V-2 | Fundc1 | 139341 | 24-May-15 | 7130 | 3 | 4 | 5 | | | V-2 | Gm3696 | | |
| 7035 | 3 | 4 | 5 | | | V-2 | Furin | 5045 | 31-May-15 | 7131 | 3 | 4 | 5 | | | V-2 | Gm3763 | | |
| 7036 | 3 | 4 | 5 | | | V-2 | Fyn | 2534 | 12-May-15 | 7132 | 3 | 4 | 5 | | | V-2 | Gm382 | | |
| 7037 | 3 | 4 | 5 | | | V-2 | Fzd7 | 8324 | 4-May-15 | 7133 | 3 | 4 | 5 | | | V-2 | Gm4265 | | |
| 7038 | 3 | 4 | 5 | | | V-2 | G630093K05Rik | | | 7134 | 3 | 4 | 5 | | | V-2 | Gm4340 | | |
| 7039 | 3 | 4 | 5 | | | V-2 | Gal3st2 | 64090 | 7-Jun-15 | 7135 | 3 | 4 | 5 | | | V-2 | Gm4566 | | |
| 7040 | 3 | 4 | 5 | | | V-2 | Galk2 | 2585 | 4-May-15 | 7136 | 3 | 4 | 5 | | | V-2 | Gm5087 | | |
| 7041 | 3 | 4 | 5 | | | V-2 | Galnt14 | 79623 | 14-May-15 | 7137 | 3 | 4 | 5 | | | V-2 | Gm5113 | | |
| 7042 | 3 | 4 | 5 | | | V-2 | Galp | 85569 | 4-May-15 | 7138 | 3 | 4 | 5 | | | V-2 | Gm5114 | | |
| 7043 | 3 | 4 | 5 | | | V-2 | Gata5os | | | 7139 | 3 | 4 | 5 | | | V-2 | Gm5136 | | |
| 7044 | 3 | 4 | 5 | | | V-2 | Gbe1 | 2632 | 23-May-15 | 7140 | 3 | 4 | 5 | | | V-2 | Gm5334 | | |
| 7045 | 3 | 4 | 5 | | | V-2 | Gbf1 | 8729 | 16-Jun-15 | 7141 | 3 | 4 | 5 | | | V-2 | Gm5549 | | |
| 7046 | 3 | 4 | 5 | | | V-2 | Gbp9 | | | 7142 | 3 | 4 | 5 | | | V-2 | Gm5591 | | |
| 7047 | 3 | 4 | 5 | | | V-2 | Gcc1 | 79571 | 4-May-15 | 7143 | 3 | 4 | 5 | | | V-2 | Gm5615 | | |
| 7048 | 3 | 4 | 5 | | | V-2 | Gcfc2 | 6936 | 4-May-15 | 7144 | 3 | 4 | 5 | | | V-2 | Gm5622 | | |
| 7049 | 3 | 4 | 5 | | | V-2 | Gcgr | 2642 | 4-May-15 | 7145 | 3 | 4 | 5 | | | V-2 | Gm5725 | | |
| 7050 | 3 | 4 | 5 | | | V-2 | Gdf5 | 8200 | 28-May-15 | 7146 | 3 | 4 | 5 | | | V-2 | Gm5797 | | |
| 7051 | 3 | 4 | 5 | | | V-2 | Gdi1 | 2664 | 12-May-15 | 7147 | 3 | 4 | 5 | | | V-2 | Gm5862 | | |
| 7052 | 3 | 4 | 5 | | | V-2 | Gfm2 | 84340 | 4-May-15 | 7148 | 3 | 4 | 5 | | | V-2 | Gm6432 | | |
| 7053 | 3 | 4 | 5 | | | V-2 | Gfod1 | 54438 | 14-May-15 | 7149 | 3 | 4 | 5 | | | V-2 | Gm6524 | | |
| 7054 | 3 | 4 | 5 | | | V-2 | Gid8 | 54994 | 4-May-15 | 7150 | 3 | 4 | 5 | | | V-2 | Gm6614 | | |
| 7055 | 3 | 4 | 5 | | | V-2 | Gipc3 | 126326 | 4-May-15 | 7151 | 3 | 4 | 5 | | | V-2 | Gm6756 | | |
| 7056 | 3 | 4 | 5 | | | V-2 | Gipr | 2696 | 9-May-15 | 7152 | 3 | 4 | 5 | | | V-2 | Gm6760 | | |
| 7057 | 3 | 4 | 5 | | | V-2 | Gjb6 | 10804 | 23-May-15 | 7153 | 3 | 4 | 5 | | | V-2 | Gm6878 | | |
| 7058 | 3 | 4 | 5 | | | V-2 | Gjd3 | 125111 | 4-May-15 | 7154 | 3 | 4 | 5 | | | V-2 | Gm7134 | | |
| 7059 | 3 | 4 | 5 | | | V-2 | Gkn3 | | | 7155 | 3 | 4 | 5 | | | V-2 | Gm7361 | | |
| 7060 | 3 | 4 | 5 | | | V-2 | Glp2r | 9340 | 4-May-15 | 7156 | 3 | 4 | 5 | | | V-2 | Gm766 | | |
| 7061 | 3 | 4 | 5 | | | V-2 | Gltp | 51228 | 12-May-15 | 7157 | 3 | 4 | 5 | | | V-2 | Gm813 | | |
| 7062 | 3 | 4 | 5 | | | V-2 | Glyatl3 | 389396 | 4-May-15 | 7158 | 3 | 4 | 5 | | | V-2 | Gm8579 | | |
| 7063 | 3 | 4 | 5 | | | V-2 | Glyr1 | 84656 | 20-May-15 | 7159 | 3 | 4 | 5 | | | V-2 | Gm8633 | | |
| 7064 | 3 | 4 | 5 | | | V-2 | Gm10033 | | | 7160 | 3 | 4 | 5 | | | V-2 | Gm9731 | | |
| 7065 | 3 | 4 | 5 | | | V-2 | Gm10058 | | | 7161 | 3 | 4 | 5 | | | V-2 | Gm9833 | | |
| 7066 | 3 | 4 | 5 | | | V-2 | Gm10104 | | | 7162 | 3 | 4 | 5 | | | V-2 | Gm9920 | | |
| 7067 | 3 | 4 | 5 | | | V-2 | Gm10142 | | | 7163 | 3 | 4 | 5 | | | V-2 | Gmpr2 | 51292 | 4-May-15 |
| 7068 | 3 | 4 | 5 | | | V-2 | Gm10230 | | | 7164 | 3 | 4 | 5 | | | V-2 | Gnao1 | 2775 | 12-May-15 |
| 7069 | 3 | 4 | 5 | | | V-2 | Gm10280 | | | 7165 | 3 | 4 | 5 | | | V-2 | Gnat2 | 2780 | 23-May-15 |
| 7070 | 3 | 4 | 5 | | | V-2 | Gm10318 | | | 7166 | 3 | 4 | 5 | | | V-2 | Gnb1 | 2782 | 3-May-15 |
| 7071 | 3 | 4 | 5 | | | V-2 | Gm10319 | | | 7167 | 3 | 4 | 5 | | | V-2 | Gng4 | 2786 | 4-May-15 |
| 7072 | 3 | 4 | 5 | | | V-2 | Gm10354 | | | 7168 | 3 | 4 | 5 | | | V-2 | Gnpda2 | 132789 | 12-May-15 |
| 7073 | 3 | 4 | 5 | | | V-2 | Gm10413 | | | 7169 | 3 | 4 | 5 | | | V-2 | Gorasp2 | 26003 | 4-May-15 |
| 7074 | 3 | 4 | 5 | | | V-2 | Gm10532 | | | 7170 | 3 | 4 | 5 | | | V-2 | Gpr101 | 83550 | 4-May-15 |
| 7075 | 3 | 4 | 5 | | | V-2 | Gm10814 | | | 7171 | 3 | 4 | 5 | | | V-2 | Gpr149 | 344758 | 4-May-15 |
| 7076 | 3 | 4 | 5 | | | V-2 | Gm10865 | | | 7172 | 3 | 4 | 5 | | | V-2 | Gpr156 | 165829 | 12-May-15 |
| 7077 | 3 | 4 | 5 | | | V-2 | Gm10922 | | | 7173 | 3 | 4 | 5 | | | V-2 | Gpr158 | 57512 | 31-May-15 |
| 7078 | 3 | 4 | 5 | | | V-2 | Gm10941 | | | 7174 | 3 | 4 | 5 | | | V-2 | Gpr25 | 2848 | 4-May-15 |
| 7079 | 3 | 4 | 5 | | | V-2 | Gm11149 | | | 7175 | 3 | 4 | 5 | | | V-2 | Gpr371 | 9283 | 4-May-15 |
| 7080 | 3 | 4 | 5 | | | V-2 | Gm11186 | | | 7176 | 3 | 4 | 5 | | | V-2 | Gpr39 | 2863 | 12-May-15 |
| 7081 | 3 | 4 | 5 | | | V-2 | Gm1140 | | | 7177 | 3 | 4 | 5 | | | V-2 | Gpr85 | 54329 | 4-May-15 |
| 7082 | 3 | 4 | 5 | | | V-2 | Gm11529 | | | 7178 | 3 | 4 | 5 | | | V-2 | Gpr89 | 653519 | 4-May-15 |
| 7083 | 3 | 4 | 5 | | | V-2 | Gm11564 | | | | | | | | | | | 51463 | 14-May-15 |
| 7084 | 3 | 4 | 5 | | | V-2 | Gm11569 | | | 7179 | 3 | 4 | 5 | | | V-2 | Gprin1 | 114787 | 4-May-15 |
| 7085 | 3 | 4 | 5 | | | V-2 | Gm11570 | | | 7180 | 3 | 4 | 5 | | | V-2 | Gramd2 | 196996 | 4-May-15 |
| 7086 | 3 | 4 | 5 | | | V-2 | Gm11758 | | | 7181 | 3 | 4 | 5 | | | V-2 | Gramd3 | 65983 | 12-May-15 |
| 7087 | 3 | 4 | 5 | | | V-2 | Gm11944 | | | 7182 | 3 | 4 | 5 | | | V-2 | Grap2 | 9402 | 12-May-15 |
| 7088 | 3 | 4 | 5 | | | V-2 | Gm12 | | | 7183 | 3 | 4 | 5 | | | V-2 | Gria2 | 2891 | 4-May-15 |
| 7089 | 3 | 4 | 5 | | | V-2 | Gm12359 | | | 7184 | 3 | 4 | 5 | | | V-2 | Grik5 | 2901 | 12-May-15 |
| 7090 | 3 | 4 | 5 | | | V-2 | Gm12789 | | | 7185 | 3 | 4 | 5 | | | V-2 | Gripap1 | 56850 | 4-May-15 |
| 7091 | 3 | 4 | 5 | | | V-2 | Gm12830 | | | 7186 | 3 | 4 | 5 | | | V-2 | Grk5 | 2869 | 4-May-15 |
| 7092 | 3 | 4 | 5 | | | V-2 | Gm13023 | | | 7187 | 3 | 4 | 5 | | | V-2 | Grm2 | 2912 | 12-May-15 |
| 7093 | 3 | 4 | 5 | | | V-2 | Gm13057 | | | 7188 | 3 | 4 | 5 | | | V-2 | Grpel2 | 134266 | 4-May-15 |
| 7094 | 3 | 4 | 5 | | | V-2 | Gm13315 | | | 7189 | 3 | 4 | 5 | | | V-2 | Grwd1 | 83743 | 12-May-15 |
| 7095 | 3 | 4 | 5 | | | V-2 | Gm13446 | | | 7190 | 3 | 4 | 5 | | | V-2 | Gsdmc2 | | |
| 7096 | 3 | 4 | 5 | | | V-2 | Gm13547 | | | 7191 | 3 | 4 | 5 | | | V-2 | Gsg1 | 83445 | 7-Jun-15 |

Fig. 30 - 39

| | | | | | | | | | | | | | | | |
|---|---|---|---|---|---|---|---|---|---|---|---|---|---|---|---|
| 7192 | 3 | 4 | 5 | | | V-2 | Gstcd | 79807 | 4-May-15 | 7288 | 3 | 4 | 5 | | | V-2 | Jph4 | 84502 | 4-May-15 |
| 7193 | 3 | 4 | 5 | | | V-2 | Gstm1 | 2944 | 24-May-15 | 7289 | 3 | 4 | 5 | | | V-2 | Kalrn | 8997 | 4-May-15 |
| 7194 | 3 | 4 | 5 | | | V-2 | Gtf2h5 | 404672 | 4-Jun-15 | 7290 | 3 | 4 | 5 | | | V-2 | Kank4os | | |
| 7195 | 3 | 4 | 5 | | | V-2 | Gtf3a | 2971 | 4-May-15 | 7291 | 3 | 4 | 5 | | | V-2 | Kbtbd2 | 25948 | 4-May-15 |
| 7196 | 3 | 4 | 5 | | | V-2 | Gtpbp6 | 8225 | 21-May-15 | 7292 | 3 | 4 | 5 | | | V-2 | Kbtbd4 | 55709 | 4-May-15 |
| 7197 | 3 | 4 | 5 | | | V-2 | Guca1b | 2979 | 31-May-15 | 7293 | 3 | 4 | 5 | | | V-2 | Kcnab1 | 7881 | 12-May-15 |
| 7198 | 3 | 4 | 5 | | | V-2 | Gzmn | | | 7294 | 3 | 4 | 5 | | | V-2 | Kcnb1 | 3745 | 4-May-15 |
| 7199 | 3 | 4 | 5 | | | V-2 | H1fnt | 341567 | 4-May-15 | 7295 | 3 | 4 | 5 | | | V-2 | Kcnb2 | 9312 | 12-May-15 |
| 7200 | 3 | 4 | 5 | | | V-2 | H2-L | | | 7296 | 3 | 4 | 5 | | | V-2 | Kcnc2 | 3747 | 31-May-15 |
| 7201 | 3 | 4 | 5 | | | V-2 | H2-M10.4 | | | 7297 | 3 | 4 | 5 | | | V-2 | Kcnd3 | 3752 | 22-May-15 |
| 7202 | 3 | 4 | 5 | | | V-2 | Hadha | 3030 | 31-May-15 | 7298 | 3 | 4 | 5 | | | V-2 | Kcnd3os | | |
| 7203 | 3 | 4 | 5 | | | V-2 | Hand1 | 9421 | 17-May-15 | 7299 | 3 | 4 | 5 | | | V-2 | Kcne2 | 9992 | 23-May-15 |
| 7204 | 3 | 4 | 5 | | | V-2 | Hapln2 | 60484 | 4-May-15 | 7300 | 3 | 4 | 5 | | | V-2 | Kcnj4 | 3761 | 4-May-15 |
| 7205 | 3 | 4 | 5 | | | V-2 | Hcfc1 | 3054 | 23-May-15 | 7301 | 3 | 4 | 5 | | | V-2 | Kcnmb2 | 10242 | 7-Jun-15 |
| 7206 | 3 | 4 | 5 | | | V-2 | Hcrt | 3060 | 17-May-15 | 7302 | 3 | 4 | 5 | | | V-2 | Kcnq5 | 56479 | 12-May-15 |
| 7207 | 3 | 4 | 5 | | | V-2 | Hcrtr1 | 3061 | 17-May-15 | 7303 | 3 | 4 | 5 | | | V-2 | Kcns1 | 3787 | 4-May-15 |
| 7208 | 3 | 4 | 5 | | | V-2 | Hdac5 | 10014 | 31-May-15 | 7304 | 3 | 4 | 5 | | | V-2 | Kcnt1 | 57582 | 7-Jun-15 |
| 7209 | 3 | 4 | 5 | | | V-2 | Hemt1 | | | 7305 | 3 | 4 | 5 | | | V-2 | Kcp | 375616 | 4-May-15 |
| 7210 | 3 | 4 | 5 | | | V-2 | Herc4 | 26091 | 4-May-15 | 7306 | 3 | 4 | 5 | | | V-2 | Kctd13 | 253980 | 4-May-15 |
| 7211 | 3 | 4 | 5 | | | V-2 | Hes3 | 390992 | 4-May-15 | 7307 | 3 | 4 | 5 | | | V-2 | Kctd20 | 222658 | 4-May-15 |
| 7212 | 3 | 4 | 5 | | | V-2 | Hes7 | 84667 | 4-May-15 | 7308 | 3 | 4 | 5 | | | V-2 | Kdm2a | 22992 | 17-May-15 |
| 7213 | 3 | 4 | 5 | | | V-2 | Hey2 | 23493 | 4-May-15 | 7309 | 3 | 4 | 5 | | | V-2 | Kdm8 | 79831 | 4-May-15 |
| 7214 | 3 | 4 | 5 | | | V-2 | Hibch | 26275 | 12-May-15 | 7310 | 3 | 4 | 5 | | | V-2 | Khnyn | 23351 | 12-May-15 |
| 7215 | 3 | 4 | 5 | | | V-2 | Hic1 | 3090 | 4-May-15 | 7311 | 3 | 4 | 5 | | | V-2 | Kif13a | 63971 | 4-May-15 |
| 7216 | 3 | 4 | 5 | | | V-2 | Hic2 | 23119 | 4-May-15 | 7312 | 3 | 4 | 5 | | | V-2 | Kif1c | 10749 | 12-May-15 |
| 7217 | 3 | 4 | 5 | | | V-2 | Higd1b | 51751 | 4-May-15 | 7313 | 3 | 4 | 5 | | | V-2 | Kif2a | 3796 | 3-May-15 |
| 7218 | 3 | 4 | 5 | | | V-2 | Hinfp | 25988 | 4-May-15 | 7314 | 3 | 4 | 5 | | | V-2 | Kifap3 | 22920 | 4-May-15 |
| 7219 | 3 | 4 | 5 | | | V-2 | Hint3 | 135114 | 4-May-15 | 7315 | 3 | 4 | 5 | | | V-2 | Kifc3 | 3801 | 4-May-15 |
| 7220 | 3 | 4 | 5 | | | V-2 | Hip1 | 3092 | 7-Jun-15 | 7316 | 3 | 4 | 5 | | | V-2 | Kif8 | 11279 | 4-May-15 |
| 7221 | 3 | 4 | 5 | | | V-2 | Hist1h2af | | | 7317 | 3 | 4 | 5 | | | V-2 | Klhdc10 | 23008 | 12-May-15 |
| 7222 | 3 | 4 | 5 | | | V-2 | Hist1h3c | 8352 | 4-May-15 | 7318 | 3 | 4 | 5 | | | V-2 | Klhl22 | 84861 | 4-May-15 |
| 7223 | 3 | 4 | 5 | | | V-2 | Hivep3 | 59269 | 4-May-15 | 7319 | 3 | 4 | 5 | | | V-2 | Klhl25 | 64410 | 4-May-15 |
| 7224 | 3 | 4 | 5 | | | V-2 | Hnf1b | 6928 | 31-May-15 | 7320 | 3 | 4 | 5 | | | V-2 | Klhl3 | 26249 | 4-May-15 |
| 7225 | 3 | 4 | 5 | | | V-2 | Hnf4aos | | | 7321 | 3 | 4 | 5 | | | V-2 | Klk7 | 5650 | 7-Jun-15 |
| 7226 | 3 | 4 | 5 | | | V-2 | Hnrnpk | 3190 | 28-May-15 | 7322 | 3 | 4 | 5 | | | V-2 | Klk9 | 284366 | 4-May-15 |
| 7227 | 3 | 4 | 5 | | | V-2 | Homer1 | 9456 | 4-May-15 | 7323 | 3 | 4 | 5 | | | V-2 | Kng1 | 3827 | 4-May-15 |
| 7228 | 3 | 4 | 5 | | | V-2 | Homer3 | 9454 | 4-May-15 | 7324 | 3 | 4 | 5 | | | V-2 | Krt23 | 25984 | 4-May-15 |
| 7229 | 3 | 4 | 5 | | | V-2 | Hook3 | 84376 | 4-May-15 | 7325 | 3 | 4 | 5 | | | V-2 | Krt32 | 3882 | 4-May-15 |
| 7230 | 3 | 4 | 5 | | | V-2 | Hoxc10 | 3226 | 4-May-15 | 7326 | 3 | 4 | 5 | | | V-2 | Krt39 | 390792 | 4-May-15 |
| 7231 | 3 | 4 | 5 | | | V-2 | Hoxc6 | 3223 | 4-May-15 | 7327 | 3 | 4 | 5 | | | V-2 | Krt42 | | |
| 7232 | 3 | 4 | 5 | | | V-2 | Hoxc8 | 3224 | 4-May-15 | 7328 | 3 | 4 | 5 | | | V-2 | Krt74 | 121391 | 7-Jun-15 |
| 7233 | 3 | 4 | 5 | | | V-2 | Hpcal1 | 3241 | 21-May-15 | 7329 | 3 | 4 | 5 | | | V-2 | Krt76 | 51350 | 4-May-15 |
| 7234 | 3 | 4 | 5 | | | V-2 | Hps5 | 11234 | 23-May-15 | 7330 | 3 | 4 | 5 | | | V-2 | Krt82 | 3888 | 4-May-15 |
| 7235 | 3 | 4 | 5 | | | V-2 | Hpx | 3263 | 4-May-15 | 7331 | 3 | 4 | 5 | | | V-2 | Krt84 | 3890 | 4-May-15 |
| 7236 | 3 | 4 | 5 | | | V-2 | Hrasls5 | 117245 | 4-May-15 | 7332 | 3 | 4 | 5 | | | V-2 | Krtap10-4 | 386672 | 4-May-15 |
| 7237 | 3 | 4 | 5 | | | V-2 | Hs1bp3 | 64342 | 4-May-15 | 7333 | 3 | 4 | 5 | | | V-2 | Krtap13 | 81850 | 4-May-15 |
| 7238 | 3 | 4 | 5 | | | V-2 | Hs3st3a1 | 9955 | 4-May-15 | 7334 | 3 | 4 | 5 | | | V-2 | Krtap20-2 | 337976 | 4-May-15 |
| 7239 | 3 | 4 | 5 | | | V-2 | Hsbp1 | 3281 | 17-May-15 | 7335 | 3 | 4 | 5 | | | V-2 | Krtap24-1 | 643803 | 4-May-15 |
| 7240 | 3 | 4 | 5 | | | V-2 | Hsd11b1 | 3290 | 12-May-15 | 7336 | 3 | 4 | 5 | | | V-2 | Krtap27-1 | 643812 | 4-May-15 |
| 7241 | 3 | 4 | 5 | | | V-2 | Hsd17b12 | 51144 | 4-May-15 | 7337 | 3 | 4 | 5 | | | V-2 | Krtap9-5 | 81870 | 4-May-15 |
| 7242 | 3 | 4 | 5 | | | V-2 | Hsd17b4 | 3295 | 12-May-15 | 7338 | 3 | 4 | 5 | | | V-2 | Ksr2 | 283455 | 7-Jun-15 |
| 7243 | 3 | 4 | 5 | | | V-2 | Hsd17b6 | 8630 | 4-May-15 | 7339 | 3 | 4 | 5 | | | V-2 | L1td1 | 54596 | 4-May-15 |
| 7244 | 3 | 4 | 5 | | | V-2 | Hsd3b3 | | | 7340 | 3 | 4 | 5 | | | V-2 | Lactb | 114294 | 4-May-15 |
| 7245 | 3 | 4 | 5 | | | V-2 | Hsf1 | 3297 | 24-May-15 | 7341 | 3 | 4 | 5 | | | V-2 | Lamp1 | 3916 | 29-May-15 |
| 7246 | 3 | 4 | 5 | | | V-2 | Hsf4 | 3299 | 17-May-15 | 7342 | 3 | 4 | 5 | | | V-2 | Layn | 143903 | 4-May-15 |
| 7247 | 3 | 4 | 5 | | | V-2 | Hsf5 | 124535 | 4-May-15 | 7343 | 3 | 4 | 5 | | | V-2 | Lca5 | 167691 | 23-May-15 |
| 7248 | 3 | 4 | 5 | | | V-2 | Hspa12b | 116585 | 4-May-15 | 7344 | 3 | 4 | 5 | | | V-2 | Lcа5l | 150082 | 12-May-15 |
| 7249 | 3 | 4 | 5 | | | V-2 | Hspe1 | 3336 | 4-May-15 | 7345 | 3 | 4 | 5 | | | V-2 | Lclat1 | 253558 | 4-May-15 |
| 7250 | 3 | 4 | 5 | | | V-2 | Hspg2 | 3339 | 12-May-15 | 7346 | 3 | 4 | 5 | | | V-2 | Lcmt1 | 51451 | 4-May-15 |
| 7251 | 3 | 4 | 5 | | | V-2 | Htatsf1 | 27336 | 4-May-15 | 7347 | 3 | 4 | 5 | | | V-2 | Ldlrad4 | 753 | 4-May-15 |
| 7252 | 3 | 4 | 5 | | | V-2 | Htra2 | 27429 | 23-May-15 | 7348 | 3 | 4 | 5 | | | V-2 | Lemd2 | 221496 | 29-May-15 |
| 7253 | 3 | 4 | 5 | | | V-2 | Hyal2 | 8692 | 31-May-15 | 7349 | 3 | 4 | 5 | | | V-2 | Lenep | 55891 | 4-May-15 |
| 7254 | 3 | 4 | 5 | | | V-2 | Idh3a | 3439 | 12-May-15 | 7350 | 3 | 4 | 5 | | | V-2 | Leng1 | 79165 | 4-May-15 |
| 7255 | 3 | 4 | 5 | | | V-2 | Idh3b | 3420 | 23-May-15 | 7351 | 3 | 4 | 5 | | | V-2 | Letm2 | 137994 | 4-May-15 |
| 7256 | 3 | 4 | 5 | | | V-2 | Idh3g | 3421 | 4-May-15 | 7352 | 3 | 4 | 5 | | | V-2 | Letmd1 | 25875 | 12-May-15 |
| 7257 | 3 | 4 | 5 | | | V-2 | Ifna1 | 3439 | 31-May-15 | 7353 | 3 | 4 | 5 | | | V-2 | Lgsn | 51557 | 4-May-15 |
| 7258 | 3 | 4 | 5 | | | V-2 | Ift172 | 26160 | 4-Jun-15 | 7354 | 3 | 4 | 5 | | | V-2 | Lhfp | 10186 | 12-May-15 |
| 7259 | 3 | 4 | 5 | | | V-2 | Ift43 | 112752 | 4-May-15 | 7355 | 3 | 4 | 5 | | | V-2 | Lhpp | 64077 | 4-May-15 |
| 7260 | 3 | 4 | 5 | | | V-2 | Ift80 | 57560 | 4-May-15 | 7356 | 3 | 4 | 5 | | | V-2 | Lhx1 | 3975 | 4-May-15 |
| 7261 | 3 | 4 | 5 | | | V-2 | Ift88 | 8100 | 21-May-15 | 7357 | 3 | 4 | 5 | | | V-2 | Lif | 3976 | 28-May-15 |
| 7262 | 3 | 4 | 5 | | | V-2 | Igf2os | | | 7358 | 3 | 4 | 5 | | | V-2 | Linch1 | 22998 | 12-May-15 |
| 7263 | 3 | 4 | 5 | | | V-2 | Igsf21 | 84966 | 4-May-15 | 7359 | 3 | 4 | 5 | | | V-2 | Limd1 | 8994 | 24-May-15 |
| 7264 | 3 | 4 | 5 | | | V-2 | Il17b | 27190 | 4-May-15 | 7360 | 3 | 4 | 5 | | | V-2 | Lin7c | 55327 | 4-May-15 |
| 7265 | 3 | 4 | 5 | | | V-2 | Il17rc | 84818 | 4-May-15 | 7361 | 3 | 4 | 5 | | | V-2 | Lins | 55180 | 4-May-15 |
| 7266 | 3 | 4 | 5 | | | V-2 | Il17re | 132014 | 12-May-15 | 7362 | 3 | 4 | 5 | | | V-2 | Lipt1 | 51601 | 13-May-15 |
| 7267 | 3 | 4 | 5 | | | V-2 | Il23r | 149233 | 31-May-15 | 7363 | 3 | 4 | 5 | | | V-2 | Lipt2 | 387787 | 4-May-15 |
| 7268 | 3 | 4 | 5 | | | V-2 | Il24 | 11009 | 4-May-15 | 7364 | 3 | 4 | 5 | | | V-2 | Lmbr1 | 64327 | 12-May-15 |
| 7269 | 3 | 4 | 5 | | | V-2 | Il3ra | 3563 | 4-May-15 | 7365 | 3 | 4 | 5 | | | V-2 | Lmo7 | 4008 | 12-May-15 |
| 7270 | 3 | 4 | 5 | | | V-2 | Imp3 | 55272 | 7-Jun-15 | 7366 | 3 | 4 | 5 | | | V-2 | Lmtk2 | 22853 | 12-May-15 |
| 7271 | 3 | 4 | 5 | | | V-2 | Inca1 | 388324 | 4-May-15 | 7367 | 3 | 4 | 5 | | | V-2 | LOC101056149 | | |
| 7272 | 3 | 4 | 5 | | | V-2 | Inip | 58493 | 4-May-15 | 7368 | 3 | 4 | 5 | | | V-2 | LOC101056236 | | |
| 7273 | 3 | 4 | 5 | | | V-2 | Insc | 387755 | 4-May-15 | 7369 | 3 | 4 | 5 | | | V-2 | LOC102308570 | | |
| 7274 | 3 | 4 | 5 | | | V-2 | Invs | 27130 | 14-May-15 | 7370 | 3 | 4 | 5 | | | V-2 | LOC102632430 | | |
| 7275 | 3 | 4 | 5 | | | V-2 | Iqca | 79781 | 4-May-15 | 7371 | 3 | 4 | 5 | | | V-2 | LOC102633315 | | |
| 7276 | 3 | 4 | 5 | | | V-2 | Iqsec2 | 23096 | 2-Jun-15 | 7372 | 3 | 4 | 5 | | | V-2 | LOC106740 | | |
| 7277 | 3 | 4 | 5 | | | V-2 | Irx5 | 10265 | 4-May-15 | 7373 | 3 | 4 | 5 | | | V-2 | Lpar4 | 2846 | 4-May-15 |
| 7278 | 3 | 4 | 5 | | | V-2 | Irx6 | 79190 | 4-May-15 | 7374 | 3 | 4 | 5 | | | V-2 | Lpar6 | 10161 | 17-May-15 |
| 7279 | 3 | 4 | 5 | | | V-2 | Ispd | 729920 | 7-Jun-15 | 7375 | 3 | 4 | 5 | | | V-2 | Lphn2 | 23266 | 12-May-15 |
| 7280 | 3 | 4 | 5 | | | V-2 | Itfg3 | 83986 | 4-May-15 | 7376 | 3 | 4 | 5 | | | V-2 | Lrp3 | 4037 | 4-May-15 |
| 7281 | 3 | 4 | 5 | | | V-2 | Itgae | 3682 | 24-May-15 | 7377 | 3 | 4 | 5 | | | V-2 | Lrrc14 | 9684 | 4-May-15 |
| 7282 | 3 | 4 | 5 | | | V-2 | Itgb4 | 3691 | 23-May-15 | 7378 | 3 | 4 | 5 | | | V-2 | Lrrc19 | 64922 | 4-May-15 |
| 7283 | 3 | 4 | 5 | | | V-2 | Itprip | 85450 | 12-May-15 | 7379 | 3 | 4 | 5 | | | V-2 | Lrrc20 | 55222 | 4-May-15 |
| 7284 | 3 | 4 | 5 | | | V-2 | Ivl | 3713 | 12-May-15 | 7380 | 3 | 4 | 5 | | | V-2 | Lrrc4 | 64101 | 12-May-15 |
| 7285 | 3 | 4 | 5 | | | V-2 | Iws1 | 55677 | 14-May-15 | 7381 | 3 | 4 | 5 | | | V-2 | Lrrc49 | 54839 | 4-May-15 |
| 7286 | 3 | 4 | 5 | | | V-2 | Izumo1 | 284359 | 4-May-15 | 7382 | 3 | 4 | 5 | | | V-2 | Lrrc4c | 57689 | 2-Jun-15 |
| 7287 | 3 | 4 | 5 | | | V-2 | Jag2 | 3714 | 4-May-15 | 7383 | 3 | 4 | 5 | | | V-2 | Lrrc55 | 219527 | 4-May-15 |

Fig. 30 - 40

| | | | | | | | | | | | | | |
|---|---|---|---|---|---|---|---|---|---|---|---|---|---|
| 7384 | 3 | 4 | 5 | | | V-2 | Lrrc56 | 115399 | 4-May-15 | 7478 | 3 | 4 | 5 | | | V-2 | Mirg | | |
| 7385 | 3 | 4 | 5 | | | V-2 | Lrrc63 | 220416 | 4-May-15 | 7479 | 3 | 4 | 5 | | | V-2 | Mixl1 | 83881 | 28-May-15 |
| 7386 | 3 | 4 | 5 | | | V-2 | Lrrc8e | 80131 | 4-May-15 | 7480 | 3 | 4 | 5 | | | V-2 | Mkl1 | 57591 | 17-May-15 |
| 7387 | 3 | 4 | 5 | | | V-2 | Lrwd1 | 222229 | 4-May-15 | 7481 | 3 | 4 | 5 | | | V-2 | Mkl | 197259 | 4-May-15 |
| 7388 | 3 | 4 | 5 | | | V-2 | Ly75 | 4065 | 31-May-15 | 7482 | 3 | 4 | 5 | | | V-2 | Mmachc | 25974 | 23-May-15 |
| 7389 | 3 | 4 | 5 | | | V-2 | Lypd1 | 116372 | 4-May-15 | 7483 | 3 | 4 | 5 | | | V-2 | Mmadhc | 27249 | 23-May-15 |
| 7390 | 3 | 4 | 5 | | | V-2 | Lyrm5 | 144363 | 4-May-15 | 7484 | 3 | 4 | 5 | | | V-2 | Mms19 | 64210 | 4-May-15 |
| 7391 | 3 | 4 | 5 | | | V-2 | Lysmd1 | 388695 | 4-May-15 | 7485 | 3 | 4 | 5 | | | V-2 | Mob3c | 148932 | 4-May-15 |
| 7392 | 3 | 4 | 5 | | | V-2 | Lyst | 1130 | 23-May-15 | 7486 | 3 | 4 | 5 | | | V-2 | Mogs | 7841 | 23-May-15 |
| 7393 | 3 | 4 | 5 | | | V-2 | M1ap | 130951 | 4-May-15 | 7487 | 3 | 4 | 5 | | | V-2 | Mon1a | 84315 | 4-May-15 |
| 7394 | 3 | 4 | 5 | | | V-2 | Mab21l1 | 4081 | 4-May-15 | 7488 | 3 | 4 | 5 | | | V-2 | Morc2a | | |
| 7395 | 3 | 4 | 5 | | | V-2 | Mad1l1 | 8379 | 24-May-15 | 7489 | 3 | 4 | 5 | | | V-2 | Morc4 | 79710 | 12-May-15 |
| 7396 | 3 | 4 | 5 | | | V-2 | Mad2l2 | 10459 | 4-May-15 | 7490 | 3 | 4 | 5 | | | V-2 | Morn4 | 118812 | 4-May-15 |
| 7397 | 3 | 4 | 5 | | | V-2 | Mafb | 9935 | 7-Jun-15 | 7491 | 3 | 4 | 5 | | | V-2 | Mos | 4342 | 7-Jun-15 |
| 7398 | 3 | 4 | 5 | | | V-2 | Mageb3 | 4114 | 4-May-15 | 7492 | 3 | 4 | 5 | | | V-2 | Mospd4 | | |
| 7399 | 3 | 4 | 5 | | | V-2 | Magee1 | 57692 | 7-Jun-15 | 7493 | 3 | 4 | 5 | | | V-2 | Mpdu1 | 9526 | 4-May-15 |
| 7400 | 3 | 4 | 5 | | | V-2 | Magi3 | 260425 | 4-May-15 | 7494 | 3 | 4 | 5 | | | V-2 | Mpkip | 136647 | 7-Jun-15 |
| 7401 | 3 | 4 | 5 | | | V-2 | Magoh | 4116 | 7-Jun-15 | 7495 | 3 | 4 | 5 | | | V-2 | Mpp5 | 64398 | 12-May-15 |
| 7402 | 3 | 4 | 5 | | | V-2 | Man2b1 | 4125 | 23-May-15 | 7496 | 3 | 4 | 5 | | | V-2 | Mpv17l | 255027 | 4-May-15 |
| 7403 | 3 | 4 | 5 | | | V-2 | Man2c1 | 4123 | 4-May-15 | 7497 | 3 | 4 | 5 | | | V-2 | Mpv17l2 | 84769 | 4-May-15 |
| 7404 | 3 | 4 | 5 | | | V-2 | Mansc4 | 100287284 | 4-May-15 | 7498 | 3 | 4 | 5 | | | V-2 | Mrpl10 | 124995 | 4-May-15 |
| 7405 | 3 | 4 | 5 | | | V-2 | Map1lc3b | 81631 | 1-Jun-15 | 7499 | 3 | 4 | 5 | | | V-2 | Mrpl13 | 28998 | 21-May-15 |
| 7406 | 3 | 4 | 5 | | | V-2 | Map2k7 | 5609 | 7-Jun-15 | 7500 | 3 | 4 | 5 | | | V-2 | Mrpl15 | 29088 | 7-Jun-15 |
| 7407 | 3 | 4 | 5 | | | V-2 | Mapk6 | 5597 | 4-May-15 | 7501 | 3 | 4 | 5 | | | V-2 | Mrpl16 | 54948 | 4-May-15 |
| 7408 | 3 | 4 | 5 | | | V-2 | Mapk8ip2 | 23542 | 4-May-15 | 7502 | 3 | 4 | 5 | | | V-2 | Mrpl17 | 63875 | 4-May-15 |
| 7409 | 3 | 4 | 5 | | | V-2 | Mapkap1 | 79109 | 2-Jun-15 | 7503 | 3 | 4 | 5 | | | V-2 | Mrpl19 | 9801 | 4-May-15 |
| 7410 | 3 | 4 | 5 | | | V-2 | Mapkapk5 | 8550 | 4-May-15 | 7504 | 3 | 4 | 5 | | | V-2 | Mrpl2 | 51069 | 13-Jun-15 |
| 7411 | 3 | 4 | 5 | | | V-2 | Mapre3 | 22924 | 12-May-15 | 7505 | 3 | 4 | 5 | | | V-2 | Mrpl20 | 55052 | 4-May-15 |
| 7412 | 3 | 4 | 5 | | | V-2 | Marc2 | 54996 | 4-May-15 | 7506 | 3 | 4 | 5 | | | V-2 | Mrpl23 | 6150 | 4-May-15 |
| 7413 | 3 | 4 | 5 | | | V-2 | Mat2b | 27430 | 12-May-15 | 7507 | 3 | 4 | 5 | | | V-2 | Mrpl3 | 11222 | 7-Jun-15 |
| 7414 | 3 | 4 | 5 | | | V-2 | Matn1 | 4146 | 12-May-15 | 7508 | 3 | 4 | 5 | | | V-2 | Mrpl30 | 51263 | 4-May-15 |
| 7415 | 3 | 4 | 5 | | | V-2 | Max | 4149 | 22-May-15 | 7509 | 3 | 4 | 5 | | | V-2 | Mrpl32 | 64983 | 7-Jun-15 |
| 7416 | 3 | 4 | 5 | | | V-2 | Mbi2 | 4153 | 7-Jun-15 | 7510 | 3 | 4 | 5 | | | V-2 | Mrpl35 | 51318 | 4-May-15 |
| 7417 | 3 | 4 | 5 | | | V-2 | Mbnl1 | 4154 | 4-May-15 | 7511 | 3 | 4 | 5 | | | V-2 | Mrpl36 | 64979 | 4-May-15 |
| 7418 | 3 | 4 | 5 | | | V-2 | Mbtd1 | 54799 | 12-May-15 | 7512 | 3 | 4 | 5 | | | V-2 | Mrpl38 | 64978 | 4-May-15 |
| 7419 | 3 | 4 | 5 | | | V-2 | Mcc | 4163 | 28-May-15 | 7513 | 3 | 4 | 5 | | | V-2 | Mrpl4 | 51073 | 4-May-15 |
| 7420 | 3 | 4 | 5 | | | V-2 | Mccc1os | | | 7514 | 3 | 4 | 5 | | | V-2 | Mrpl40 | 64976 | 4-May-15 |
| 7421 | 3 | 4 | 5 | | | V-2 | Mcee | 84693 | 23-May-15 | 7515 | 3 | 4 | 5 | | | V-2 | Mrpl42 | 28977 | 4-May-15 |
| 7422 | 3 | 4 | 5 | | | V-2 | Mcidas | 345643 | 4-May-15 | 7516 | 3 | 4 | 5 | | | V-2 | Mrpl43 | 84545 | 12-May-15 |
| 7423 | 3 | 4 | 5 | | | V-2 | Mcu | 90550 | 10-May-15 | 7517 | 3 | 4 | 5 | | | V-2 | Mrpl45 | 84311 | 4-May-15 |
| 7424 | 3 | 4 | 5 | | | V-2 | Mdga2 | 161357 | 4-May-15 | 7518 | 3 | 4 | 5 | | | V-2 | Mrpl46 | 26589 | 4-May-15 |
| 7425 | 3 | 4 | 5 | | | V-2 | Mdh1b | 130752 | 4-May-15 | 7519 | 3 | 4 | 5 | | | V-2 | Mrpl47 | 57129 | 4-May-15 |
| 7426 | 3 | 4 | 5 | | | V-2 | Mdm2 | 4193 | 31-May-15 | 7520 | 3 | 4 | 5 | | | V-2 | Mrpl51 | 51258 | 28-May-15 |
| 7427 | 3 | 4 | 5 | | | V-2 | Mdm4 | 4194 | 4-May-15 | 7521 | 3 | 4 | 5 | | | V-2 | Mrpl52 | 122704 | 4-May-15 |
| 7428 | 3 | 4 | 5 | | | V-2 | Mea1 | 4201 | 4-May-15 | 7522 | 3 | 4 | 5 | | | V-2 | Mrps10 | 55173 | 28-May-15 |
| 7429 | 3 | 4 | 5 | | | V-2 | Med1 | 5469 | 7-Jun-15 | 7523 | 3 | 4 | 5 | | | V-2 | Mrps15 | 64960 | 28-May-15 |
| 7430 | 3 | 4 | 5 | | | V-2 | Med13 | 9969 | 4-May-15 | 7524 | 3 | 4 | 5 | | | V-2 | Mrps18b | 28973 | 28-May-15 |
| 7431 | 3 | 4 | 5 | | | V-2 | Medag | 84935 | 4-May-15 | 7525 | 3 | 4 | 5 | | | V-2 | Mrps18c | 51023 | 12-May-15 |
| 7432 | 3 | 4 | 5 | | | V-2 | Meiob | 254528 | 4-May-15 | 7526 | 3 | 4 | 5 | | | V-2 | Mrps23 | 51649 | 4-May-15 |
| 7433 | 3 | 4 | 5 | | | V-2 | Meis2 | 4212 | 4-May-15 | 7527 | 3 | 4 | 5 | | | V-2 | Mrps25 | 64432 | 4-May-15 |
| 7434 | 3 | 4 | 5 | | | V-2 | Mep1b | 4225 | 12-May-15 | 7528 | 3 | 4 | 5 | | | V-2 | Mrps28 | 28957 | 7-Jun-15 |
| 7435 | 3 | 4 | 5 | | | V-2 | Metrnl | 284207 | 4-May-15 | 7529 | 3 | 4 | 5 | | | V-2 | Mrps30 | 10884 | 4-May-15 |
| 7436 | 3 | 4 | 5 | | | V-2 | Mettl13 | 51603 | 23-May-15 | 7530 | 3 | 4 | 5 | | | V-2 | Mrps31 | 10240 | 4-May-15 |
| 7437 | 3 | 4 | 5 | | | V-2 | Mettl16 | 79066 | 12-May-15 | 7531 | 3 | 4 | 5 | | | V-2 | Mrps33 | 51650 | 4-May-15 |
| 7438 | 3 | 4 | 5 | | | V-2 | Mettl22 | 79091 | 4-May-15 | 7532 | 3 | 4 | 5 | | | V-2 | Mrps36 | 92259 | 4-May-15 |
| 7439 | 3 | 4 | 5 | | | V-2 | Mettl24 | 728464 | 4-May-15 | 7533 | 3 | 4 | 5 | | | V-2 | Mrps5 | 64969 | 12-May-15 |
| 7440 | 3 | 4 | 5 | | | V-2 | Mettl8 | 79828 | 4-May-15 | 7534 | 3 | 4 | 5 | | | V-2 | Mrrf | 92399 | 4-May-15 |
| 7441 | 3 | 4 | 5 | | | V-2 | Mfn2 | 9927 | 31-May-15 | 7535 | 3 | 4 | 5 | | | V-2 | Mrvi1 | 10335 | 12-May-15 |
| 7442 | 3 | 4 | 5 | | | V-2 | Mfng | 4242 | 4-May-15 | 7536 | 3 | 4 | 5 | | | V-2 | Msantd4 | 84437 | 4-May-15 |
| 7443 | 3 | 4 | 5 | | | V-2 | Mfsd4 | 148808 | 4-May-15 | 7537 | 3 | 4 | 5 | | | V-2 | Msrb2 | 22921 | 23-May-15 |
| 7444 | 3 | 4 | 5 | | | V-2 | Mfsd8 | 256471 | 23-May-15 | 7538 | 3 | 4 | 5 | | | V-2 | Msx3 | | |
| 7445 | 3 | 4 | 5 | | | V-2 | Mfsd9 | 84804 | 4-May-15 | 7539 | 3 | 4 | 5 | | | V-2 | Mtcp1 | 4515 | 7-Jun-15 |
| 7446 | 3 | 4 | 5 | | | V-2 | Mgarp | 84709 | 4-May-15 | 7540 | 3 | 4 | 5 | | | V-2 | Mterfd1 | 51001 | 4-May-15 |
| 7447 | 3 | 4 | 5 | | | V-2 | Mgat4a | 11320 | 4-May-15 | 7541 | 3 | 4 | 5 | | | V-2 | Mtg2 | 26164 | 4-May-15 |
| 7448 | 3 | 4 | 5 | | | V-2 | Mien1 | 84299 | 4-May-15 | 7542 | 3 | 4 | 5 | | | V-2 | Mthfd1 | 4522 | 21-May-15 |
| 7449 | 3 | 4 | 5 | | | V-2 | Mip | 4284 | 7-Jun-15 | 7543 | 3 | 4 | 5 | | | V-2 | Mtif5 | 9633 | 4-May-15 |
| 7450 | 3 | 4 | 5 | | | V-2 | Mipol1 | 145282 | 12-May-15 | 7544 | 3 | 4 | 5 | | | V-2 | Mtm1 | 4534 | 23-May-15 |
| 7451 | 3 | 4 | 5 | | | V-2 | Mir103-1 | 406895 | 21-May-15 | 7545 | 3 | 4 | 5 | | | V-2 | Mtmr9 | 66036 | 4-May-15 |
| 7452 | 3 | 4 | 5 | | | V-2 | Mir139 | 406931 | 21-May-15 | 7546 | 3 | 4 | 5 | | | V-2 | Mtrf1 | 9617 | 4-May-15 |
| 7453 | 3 | 4 | 5 | | | V-2 | Mir153 | | | 7547 | 3 | 4 | 5 | | | V-2 | Mtss1l | 92154 | 4-May-15 |
| 7454 | 3 | 4 | 5 | | | V-2 | Mir190 | 406965 | 21-May-15 | 7548 | 3 | 4 | 5 | | | V-2 | Mtus1 | 57509 | 12-May-15 |
| 7455 | 3 | 4 | 5 | | | V-2 | Mir1a-2 | | | 7549 | 3 | 4 | 5 | | | V-2 | Mtx3 | 345778 | 4-May-15 |
| 7456 | 3 | 4 | 5 | | | V-2 | Mir297-1 | | | 7550 | 3 | 4 | 5 | | | V-2 | Mup3 | | |
| 7457 | 3 | 4 | 5 | | | V-2 | Mir299 | 407023 | 21-May-15 | 7551 | 3 | 4 | 5 | | | V-2 | Murc | 347273 | 4-May-15 |
| 7458 | 3 | 4 | 5 | | | V-2 | Mir30a | 407029 | 7-Jun-15 | 7552 | 3 | 4 | 5 | | | V-2 | Mus81 | 80198 | 17-May-15 |
| 7459 | 3 | 4 | 5 | | | V-2 | Mir323 | 442897 | 21-May-15 | 7553 | 3 | 4 | 5 | | | V-2 | Mutyh | 4595 | 23-May-15 |
| 7460 | 3 | 4 | 5 | | | V-2 | Mir449b | 693123 | 21-May-15 | 7554 | 3 | 4 | 5 | | | V-2 | Myl12b | 103910 | 4-May-15 |
| 7461 | 3 | 4 | 5 | | | V-2 | Mir450-2 | | | 7555 | 3 | 4 | 5 | | | V-2 | Myo1d | 4642 | 12-May-15 |
| 7462 | 3 | 4 | 5 | | | V-2 | Mir470 | | | 7556 | 3 | 4 | 5 | | | V-2 | Myo9a | 4649 | 4-May-15 |
| 7463 | 3 | 4 | 5 | | | V-2 | Mir497 | 574456 | 7-Jun-15 | 7557 | 3 | 4 | 5 | | | V-2 | Myod1 | 4654 | 28-May-15 |
| 7464 | 3 | 4 | 5 | | | V-2 | Mir501 | 574503 | 21-May-15 | 7558 | 3 | 4 | 5 | | | V-2 | Naip2 | | |
| 7465 | 3 | 4 | 5 | | | V-2 | Mir6239 | | | 7559 | 3 | 4 | 5 | | | V-2 | Nanog | 79923 | 7-Jun-15 |
| 7466 | 3 | 4 | 5 | | | V-2 | Mir6352 | | | 7560 | 3 | 4 | 5 | | | V-2 | Nat8 | 9027 | 4-May-15 |
| 7467 | 3 | 4 | 5 | | | V-2 | Mir6355 | | | 7561 | 3 | 4 | 5 | | | V-2 | Nbeal2 | 23218 | 4-May-15 |
| 7468 | 3 | 4 | 5 | | | V-2 | Mir6362 | | | 7562 | 3 | 4 | 5 | | | V-2 | Nckap5l | 57701 | 4-May-15 |
| 7469 | 3 | 4 | 5 | | | V-2 | Mir6376 | | | 7563 | 3 | 4 | 5 | | | V-2 | Ncoa1 | 8648 | 3-May-15 |
| 7470 | 3 | 4 | 5 | | | V-2 | Mir6411 | | | 7564 | 3 | 4 | 5 | | | V-2 | Ndor1 | 27158 | 4-May-15 |
| 7471 | 3 | 4 | 5 | | | V-2 | Mir669a-1 | | | 7565 | 3 | 4 | 5 | | | V-2 | Ndufa11 | 126328 | 4-May-15 |
| 7472 | 3 | 4 | 5 | | | V-2 | Mir669a-3 | | | 7566 | 3 | 4 | 5 | | | V-2 | Ndufa13 | 51079 | 4-May-15 |
| 7473 | 3 | 4 | 5 | | | V-2 | Mir669m-1 | | | 7567 | 3 | 4 | 5 | | | V-2 | Ndufa2 | 4695 | 23-May-15 |
| 7474 | 3 | 4 | 5 | | | V-2 | Mir7057 | | | 7568 | 3 | 4 | 5 | | | V-2 | Ndufa4 | 4697 | 7-Jun-15 |
| 7475 | 3 | 4 | 5 | | | V-2 | Mir743b | | | 7569 | 3 | 4 | 5 | | | V-2 | Ndufa6 | 4700 | 4-May-15 |
| 7476 | 3 | 4 | 5 | | | V-2 | Mir764 | 100313838 | 4-May-15 | 7570 | 3 | 4 | 5 | | | V-2 | Ndufa7 | 4701 | 29-May-15 |
| 7477 | 3 | 4 | 5 | | | V-2 | Mir96 | 407053 | 7-Jun-15 | 7571 | 3 | 4 | 5 | | | V-2 | Ndufa8 | 4702 | 4-May-15 |
| | | | | | | | | | | 7572 | 3 | 4 | 5 | | | V-2 | Ndufa9 | 4704 | 23-May-15 |
| | | | | | | | | | | 7573 | 3 | 4 | 5 | | | V-2 | Ndufab1 | 4706 | 4-May-15 |

Fig. 30 - 41

| | | | | | | | | | | | | | | | | |
|---|---|---|---|---|---|---|---|---|---|---|---|---|---|---|---|---|
| 7574 | 3 | 4 | 5 | | | V-2 | Ndufaf1 | 51103 | 4-May-15 | 7670 | 3 | 4 | 5 | | | V-2 | Pap1 | 390928 | 4-May-15 |
| 7575 | 3 | 4 | 5 | | | V-2 | Ndufaf2 | 91942 | 23-May-15 | 7671 | 3 | 4 | 5 | | | V-2 | Papola | 10914 | 3-Jun-15 |
| 7576 | 3 | 4 | 5 | | | V-2 | Ndufaf3 | 25915 | 4-May-15 | 7672 | 3 | 4 | 5 | | | V-2 | Pappa2 | 60676 | 17-May-15 |
| 7577 | 3 | 4 | 5 | | | V-2 | Ndufaf5 | 79133 | 23-May-15 | 7673 | 3 | 4 | 5 | | | V-2 | Papss1 | 9061 | 4-May-15 |
| 7578 | 3 | 4 | 5 | | | V-2 | Ndufaf7 | 55471 | 31-May-15 | 7674 | 3 | 4 | 5 | | | V-2 | Paqr6 | 79957 | 4-May-15 |
| 7579 | 3 | 4 | 5 | | | V-2 | Ndufb11 | 54539 | 31-May-15 | 7675 | 3 | 4 | 5 | | | V-2 | Paqr8 | 85315 | 4-May-15 |
| 7580 | 3 | 4 | 5 | | | V-2 | Ndufb3 | 4709 | 23-May-15 | 7676 | 3 | 4 | 5 | | | V-2 | Pard3b | 117583 | 12-May-15 |
| 7581 | 3 | 4 | 5 | | | V-2 | Ndufb4 | 4710 | 4-May-15 | 7677 | 3 | 4 | 5 | | | V-2 | Parg | 8505 | 17-May-15 |
| 7582 | 3 | 4 | 5 | | | V-2 | Ndufb5 | 4711 | 4-May-15 | 7678 | 3 | 4 | 5 | | | V-2 | Parn | 5073 | 4-Jun-15 |
| 7583 | 3 | 4 | 5 | | | V-2 | Ndufb8 | 4714 | 4-May-15 | 7679 | 3 | 4 | 5 | | | V-2 | Parva | 55742 | 4-May-15 |
| 7584 | 3 | 4 | 5 | | | V-2 | Ndufb9 | 4715 | 28-May-15 | 7680 | 3 | 4 | 5 | | | V-2 | Patl1 | 219988 | 4-May-15 |
| 7585 | 3 | 4 | 5 | | | V-2 | Ndufc1 | 4717 | 4-May-15 | 7681 | 3 | 4 | 5 | | | V-2 | Pbld2 | | |
| 7586 | 3 | 4 | 5 | | | V-2 | Ndufc2 | 4718 | 4-May-15 | 7682 | 3 | 4 | 5 | | | V-2 | Pcbp1 | 5093 | 4-May-15 |
| 7587 | 3 | 4 | 5 | | | V-2 | Ndufs2 | 4720 | 21-May-15 | 7683 | 3 | 4 | 5 | | | V-2 | Pccb | 5096 | 23-May-15 |
| 7588 | 3 | 4 | 5 | | | V-2 | Ndufs3 | 4722 | 23-May-15 | 7684 | 3 | 4 | 5 | | | V-2 | Pcdh1 | 5097 | 4-May-15 |
| 7589 | 3 | 4 | 5 | | | V-2 | Ndufs4 | 4724 | 23-May-15 | 7685 | 3 | 4 | 5 | | | V-2 | Pcdh10 | 57575 | 4-May-15 |
| 7590 | 3 | 4 | 5 | | | V-2 | Ndufs5 | 4725 | 4-May-15 | 7686 | 3 | 4 | 5 | | | V-2 | Pcdhb1 | 29930 | 4-May-15 |
| 7591 | 3 | 4 | 5 | | | V-2 | Ndufs7 | 374291 | 23-May-15 | 7687 | 3 | 4 | 5 | | | V-2 | Pcdhga12 | 26025 | 4-May-15 |
| 7592 | 3 | 4 | 5 | | | V-2 | Ndufs8 | 4728 | 23-May-15 | 7688 | 3 | 4 | 5 | | | V-2 | Pcdhga3 | 56112 | 12-May-15 |
| 7593 | 3 | 4 | 5 | | | V-2 | Ndufv1 | 4723 | 12-May-15 | 7689 | 3 | 4 | 5 | | | V-2 | Pcdhga5 | 56110 | 4-May-15 |
| 7594 | 3 | 4 | 5 | | | V-2 | Ndufv2 | 4729 | 4-May-15 | 7690 | 3 | 4 | 5 | | | V-2 | Pcnx | 22990 | 21-May-15 |
| 7595 | 3 | 4 | 5 | | | V-2 | Ndufv3 | 4731 | 4-May-15 | 7691 | 3 | 4 | 5 | | | V-2 | Pdap1 | 11333 | 4-May-15 |
| 7596 | 3 | 4 | 5 | | | V-2 | Net1 | 10276 | n-2015 | 7692 | 3 | 4 | 5 | | | V-2 | Pdcd4 | 27250 | 31-May-15 |
| 7597 | 3 | 4 | 5 | | | V-2 | Neurl2 | 140825 | 4-May-15 | 7693 | 3 | 4 | 5 | | | V-2 | Pde5a | 8654 | 4-May-15 |
| 7598 | 3 | 4 | 5 | | | V-2 | Nfu1 | 27247 | 2-Jun-15 | 7694 | 3 | 4 | 5 | | | V-2 | Pde6b | 5158 | 23-May-15 |
| 7599 | 3 | 4 | 5 | | | V-2 | Ngdn | 25983 | 4-May-15 | 7695 | 3 | 4 | 5 | | | V-2 | Pde6g | 5148 | 23-May-15 |
| 7600 | 3 | 4 | 5 | | | V-2 | Nhlh1 | 4807 | 28-May-15 | 7696 | 3 | 4 | 5 | | | V-2 | Pde7a | 5150 | 4-May-15 |
| 7601 | 3 | 4 | 5 | | | V-2 | Nhlrc2 | 374354 | 4-May-15 | 7697 | 3 | 4 | 5 | | | V-2 | Pde7b | 27115 | 4-May-15 |
| 7602 | 3 | 4 | 5 | | | V-2 | Nin | 51199 | 12-May-15 | 7698 | 3 | 4 | 5 | | | V-2 | Pdha2 | 5161 | 4-May-15 |
| 7603 | 3 | 4 | 5 | | | V-2 | Nipal4 | 348938 | 23-May-15 | 7699 | 3 | 4 | 5 | | | V-2 | Pdhx | 8050 | 29-May-15 |
| 7604 | 3 | 4 | 5 | | | V-2 | Nipbl | 25836 | 23-May-15 | 7700 | 3 | 4 | 5 | | | V-2 | Pdia3 | 2923 | 4-May-15 |
| 7605 | 3 | 4 | 5 | | | V-2 | Nipsnap3a | 25934 | 4-May-15 | 7701 | 3 | 4 | 5 | | | V-2 | Pdk3 | 5165 | 4-May-15 |
| 7606 | 3 | 4 | 5 | | | V-2 | Nkap | 222698 | 4-May-15 | 7702 | 3 | 4 | 5 | | | V-2 | Pdpk1 | 5170 | 4-May-15 |
| 7607 | 3 | 4 | 5 | | | V-2 | Nkiras2 | 28511 | 4-May-15 | 7703 | 3 | 4 | 5 | | | V-2 | Pds5a | 23244 | 4-May-15 |
| 7608 | 3 | 4 | 5 | | | V-2 | Nkx2-6 | 137814 | 4-May-15 | 7704 | 3 | 4 | 5 | | | V-2 | Pdx1 | 3651 | 7-Jun-15 |
| 7609 | 3 | 4 | 5 | | | V-2 | Nkx6-1 | 4825 | 4-May-15 | 7705 | 3 | 4 | 5 | | | V-2 | Pdxk-ps | | |
| 7610 | 3 | 4 | 5 | | | V-2 | Nkx6-3 | 157848 | 4-May-15 | 7706 | 3 | 4 | 5 | | | V-2 | Pdzd4 | 57595 | 12-May-15 |
| 7611 | 3 | 4 | 5 | | | V-2 | Nlrp9a | | | 7707 | 3 | 4 | 5 | | | V-2 | Pdzd8 | 118987 | 4-May-15 |
| 7612 | 3 | 4 | 5 | | | V-2 | Nmnat2 | 23057 | 4-May-15 | 7708 | 3 | 4 | 5 | | | V-2 | Pea15a | | |
| 7613 | 3 | 4 | 5 | | | V-2 | Noa1 | 84273 | 4-May-15 | 7709 | 3 | 4 | 5 | | | V-2 | Pef1 | 553115 | 4-May-15 |
| 7614 | 3 | 4 | 5 | | | V-2 | Nol4 | 8715 | 4-May-15 | 7710 | 3 | 4 | 5 | | | V-2 | Pepd | 5184 | 31-May-15 |
| 7615 | 3 | 4 | 5 | | | V-2 | Noxo1 | 124056 | 4-May-15 | 7711 | 3 | 4 | 5 | | | V-2 | Peril | | |
| 7616 | 3 | 4 | 5 | | | V-2 | Npr3 | 8131 | 29-May-15 | 7712 | 3 | 4 | 5 | | | V-2 | Pex11a | 8800 | 4-May-15 |
| 7617 | 3 | 4 | 5 | | | V-2 | Nr0b1 | 190 | 23-May-15 | 7713 | 3 | 4 | 5 | | | V-2 | Pex3 | 8504 | 28-May-15 |
| 7618 | 3 | 4 | 5 | | | V-2 | Nr1h2 | 7376 | 29-May-15 | 7714 | 3 | 4 | 5 | | | V-2 | Pfn4 | 375189 | 4-May-15 |
| 7619 | 3 | 4 | 5 | | | V-2 | Nr1h5 | 643609 | 4-May-15 | 7715 | 3 | 4 | 5 | | | V-2 | Pglyrp3 | 114771 | 4-May-15 |
| 7620 | 3 | 4 | 5 | | | V-2 | Nrg3 | 10718 | 4-May-15 | 7716 | 3 | 4 | 5 | | | V-2 | Pgm2l1 | 283209 | 4-May-15 |
| 7621 | 3 | 4 | 5 | | | V-2 | Nmi | 123904 | 4-May-15 | 7717 | 3 | 4 | 5 | | | V-2 | Pgpep1l | 145814 | 4-May-15 |
| 7622 | 3 | 4 | 5 | | | V-2 | Nrp | | | 7718 | 3 | 4 | 5 | | | V-2 | Pgr15l | | |
| 7623 | 3 | 4 | 5 | | | V-2 | Nrxn3 | 9369 | 4-May-15 | 7719 | 3 | 4 | 5 | | | V-2 | Phb2 | 11331 | 1-Jun-15 |
| 7624 | 3 | 4 | 5 | | | V-2 | Nsun5 | 55695 | 4-May-15 | 7720 | 3 | 4 | 5 | | | V-2 | Phip | 55023 | 4-May-15 |
| 7625 | 3 | 4 | 5 | | | V-2 | Nt5c3b | 93034 | 4-May-15 | 7721 | 3 | 4 | 5 | | | V-2 | Phrf1 | 57661 | 4-May-15 |
| 7626 | 3 | 4 | 5 | | | V-2 | Nt5dc1 | 221294 | 4-May-15 | 7722 | 3 | 4 | 5 | | | V-2 | Pid1 | 55022 | 3-May-15 |
| 7627 | 3 | 4 | 5 | | | V-2 | Nthl1 | 4913 | 28-May-15 | 7723 | 3 | 4 | 5 | | | V-2 | Pigk | 10026 | 4-May-15 |
| 7628 | 3 | 4 | 5 | | | V-2 | Ntpcr | 84284 | 12-May-15 | 7724 | 3 | 4 | 5 | | | V-2 | Pigp | 51227 | 4-May-15 |
| 7629 | 3 | 4 | 5 | | | V-2 | Nucb1 | 4924 | 4-May-15 | 7725 | 3 | 4 | 5 | | | V-2 | Pigt | 51604 | 12-May-15 |
| 7630 | 3 | 4 | 5 | | | V-2 | Nudt13 | 25961 | 4-May-15 | 7726 | 3 | 4 | 5 | | | V-2 | Pigv | 55650 | 12-May-15 |
| 7631 | 3 | 4 | 5 | | | V-2 | Nudt16 | 131870 | 4-May-15 | 7727 | 3 | 4 | 5 | | | V-2 | Pigz | 80235 | 4-May-15 |
| 7632 | 3 | 4 | 5 | | | V-2 | Nudt18 | 79873 | 4-May-15 | 7728 | 3 | 4 | 5 | | | V-2 | Pih1d3 | 139212 | 4-May-15 |
| 7633 | 3 | 4 | 5 | | | V-2 | Nyap2 | 57624 | 4-May-15 | 7729 | 3 | 4 | 5 | | | V-2 | Pik3c3 | 5289 | 21-May-15 |
| 7634 | 3 | 4 | 5 | | | V-2 | Obp2b | 29989 | 4-May-15 | 7730 | 3 | 4 | 5 | | | V-2 | Pik3ca | 5290 | 31-May-15 |
| 7635 | 3 | 4 | 5 | | | V-2 | Odf2l | 57489 | 4-May-15 | 7731 | 3 | 4 | 5 | | | V-2 | Pinc | | |
| 7636 | 3 | 4 | 5 | | | V-2 | Odf3l2 | 284651 | 4-May-15 | 7732 | 3 | 4 | 5 | | | V-2 | Pink1 | 65018 | 31-May-15 |
| 7637 | 3 | 4 | 5 | | | V-2 | Ogfod1 | 55239 | 12-May-15 | 7733 | 3 | 4 | 5 | | | V-2 | Pinlyp | 390940 | 4-May-15 |
| 7638 | 3 | 4 | 5 | | | V-2 | Oit3 | 170392 | 4-May-15 | 7734 | 3 | 4 | 5 | | | V-2 | Pitrm1 | 10531 | 23-May-15 |
| 7639 | 3 | 4 | 5 | | | V-2 | Ola1 | 29789 | 23-May-15 | 7735 | 3 | 4 | 5 | | | V-2 | Pkdcc | 91461 | 4-May-15 |
| 7640 | 3 | 4 | 5 | | | V-2 | Olfm3 | 118427 | 4-May-15 | 7736 | 3 | 4 | 5 | | | V-2 | Pkdrej | 10343 | 4-May-15 |
| 7641 | 3 | 4 | 5 | | | V-2 | Olfml2a | 169611 | 4-May-15 | 7737 | 3 | 4 | 5 | | | V-2 | Pkhd1 | 5314 | 23-May-15 |
| 7642 | 3 | 4 | 5 | | | V-2 | Olfr140 | | | 7738 | 3 | 4 | 5 | | | V-2 | Pla2g15 | 23659 | 4-May-15 |
| 7643 | 3 | 4 | 5 | | | V-2 | Olfr190 | | | 7739 | 3 | 4 | 5 | | | V-2 | Pla2g2a | 5320 | 4-May-15 |
| 7644 | 3 | 4 | 5 | | | V-2 | Olfr310 | | | 7740 | 3 | 4 | 5 | | | V-2 | Pla2g2f | 64600 | 4-May-15 |
| 7645 | 3 | 4 | 5 | | | V-2 | Olfr524 | | | 7741 | 3 | 4 | 5 | | | V-2 | Pla2g3 | 50487 | 4-May-15 |
| 7646 | 3 | 4 | 5 | | | V-2 | Olfr75-ps1 | | | 7742 | 3 | 4 | 5 | | | V-2 | Pla2g4f | 255189 | 4-May-15 |
| 7647 | 3 | 4 | 5 | | | V-2 | Olig2 | 10215 | 17-May-15 | 7743 | 3 | 4 | 5 | | | V-2 | Plac1 | 10761 | 24-May-15 |
| 7648 | 3 | 4 | 5 | | | V-2 | Olr1 | 4973 | 12-May-15 | 7744 | 3 | 4 | 5 | | | V-2 | Plcd1 | 5333 | 17-May-15 |
| 7649 | 3 | 4 | 5 | | | V-2 | Onecut2 | 9480 | 28-May-15 | 7745 | 3 | 4 | 5 | | | V-2 | Plcd3 | 113026 | 4-May-15 |
| 7650 | 3 | 4 | 5 | | | V-2 | Onecut3 | 390874 | 28-May-15 | 7746 | 3 | 4 | 5 | | | V-2 | Plce1 | 51196 | 31-May-15 |
| 7651 | 3 | 4 | 5 | | | V-2 | Opa3 | 80207 | 23-May-15 | 7747 | 3 | 4 | 5 | | | V-2 | Plcg1 | 5335 | 31-May-15 |
| 7652 | 3 | 4 | 5 | | | V-2 | Opalin | 93377 | 4-May-15 | 7748 | 3 | 4 | 5 | | | V-2 | Plcl1 | 5334 | 4-May-15 |
| 7653 | 3 | 4 | 5 | | | V-2 | Opn1mw | 2652 | 4-May-15 | 7749 | 3 | 4 | 5 | | | V-2 | Pldi | | |
| 7654 | 3 | 4 | 5 | | | V-2 | Opn4 | 94233 | 21-May-15 | 7750 | 3 | 4 | 5 | | | V-2 | Plekha7 | 144100 | 4-May-15 |
| 7655 | 3 | 4 | 5 | | | V-2 | Opn5 | 221391 | 4-May-15 | 7751 | 3 | 4 | 5 | | | V-2 | Plekha8 | 84725 | 4-May-15 |
| 7656 | 3 | 4 | 5 | | | V-2 | Ormdl2 | 29095 | 4-May-15 | 7752 | 3 | 4 | 5 | | | V-2 | Plekhh2 | 130271 | 4-May-15 |
| 7657 | 3 | 4 | 5 | | | V-2 | Osbpl10 | 114884 | 4-May-15 | 7753 | 3 | 4 | 5 | | | V-2 | Plekhj1 | 55111 | 4-May-15 |
| 7658 | 3 | 4 | 5 | | | V-2 | Osbpl5 | 114879 | 4-May-15 | 7754 | 3 | 4 | 5 | | | V-2 | Plg | 5340 | 12-May-15 |
| 7659 | 3 | 4 | 5 | | | V-2 | Otc | 5009 | 23-May-15 | 7755 | 3 | 4 | 5 | | | V-2 | Plod2 | 5352 | 28-May-15 |
| 7660 | 3 | 4 | 5 | | | V-2 | Otud4 | 54726 | 4-May-15 | 7756 | 3 | 4 | 5 | | | V-2 | Plscr3 | 57048 | 4-May-15 |
| 7661 | 3 | 4 | 5 | | | V-2 | Ovol3 | 728044 | 28-May-15 | 7757 | 3 | 4 | 5 | | | V-2 | Plxnb2 | 23654 | 4-May-15 |
| 7662 | 3 | 4 | 5 | | | V-2 | Oxnad1 | 92106 | 4-May-15 | 7758 | 3 | 4 | 5 | | | V-2 | Pms1 | 5378 | 23-May-15 |
| 7663 | 3 | 4 | 5 | | | V-2 | Oxr1 | 55074 | 12-May-15 | 7759 | 3 | 4 | 5 | | | V-2 | Pms2 | 5395 | 22-May-15 |
| 7664 | 3 | 4 | 5 | | | V-2 | Oxsr1 | 9943 | 12-May-15 | 7760 | 3 | 4 | 5 | | | V-2 | Pnisr | 25957 | 12-May-15 |
| 7665 | 3 | 4 | 5 | | | V-2 | Pa2g4 | 5036 | 12-May-15 | 7761 | 3 | 4 | 5 | | | V-2 | Pold3 | 10714 | 4-May-15 |
| 7666 | 3 | 4 | 5 | | | V-2 | Pacrg | 133015 | 4-May-15 | 7762 | 3 | 4 | 5 | | | V-2 | Poli | 27343 | 21-May-15 |
| 7667 | 3 | 4 | 5 | | | V-2 | Pag1 | 55824 | 4-May-15 | 7763 | 3 | 4 | 5 | | | V-2 | Polr2g | 5436 | 4-May-15 |
| 7668 | 3 | 4 | 5 | | | V-2 | Paics | 10606 | 4-May-15 | 7764 | 3 | 4 | 5 | | | V-2 | Polr2h | 5437 | 2-Jun-15 |
| 7669 | 3 | 4 | 5 | | | V-2 | Pank4 | 55229 | 4-May-15 | 7765 | 3 | 4 | 5 | | | V-2 | Polr2l | 5441 | 12-May-15 |

Fig. 30 - 42

| | | | | | | | | | | | | | | | | |
|---|---|---|---|---|---|---|---|---|---|---|---|---|---|---|---|---|
| 7766 | 3 | 4 | 5 | | | V-2 | Pom121 | 9883 | 7-Jun-15 | 7860 | 3 | 4 | 5 | | | V-2 | Rdh5 | 5959 | 4-May-15 |
| 7767 | 3 | 4 | 5 | | | V-2 | Pomk | 84197 | 4-May-15 | 7861 | 3 | 4 | 5 | | | V-2 | Rdh7 | | |
| 7768 | 3 | 4 | 5 | | | V-2 | Pomp | 51371 | 7-Jun-15 | 7862 | 3 | 4 | 5 | | | V-2 | Reln | 5649 | 17-May-15 |
| 7769 | 3 | 4 | 5 | | | V-2 | Pou3f1 | 5453 | 4-May-15 | 7863 | 3 | 4 | 5 | | | V-2 | Resp18 | 389075 | 4-May-15 |
| 7770 | 3 | 4 | 5 | | | V-2 | Ppap2c | 8612 | 4-May-15 | 7864 | 3 | 4 | 5 | | | V-2 | Rev3l | 5980 | 12-May-15 |
| 7771 | 3 | 4 | 5 | | | V-2 | Ppat | 5471 | 7-Jun-15 | 7865 | 3 | 4 | 5 | | | V-2 | Rexo1 | 57455 | 4-May-15 |
| 7772 | 3 | 4 | 5 | | | V-2 | Pphln1 | 51535 | 4-May-15 | 7866 | 3 | 4 | 5 | | | V-2 | Rfl | 117584 | 4-May-15 |
| 7773 | 3 | 4 | 5 | | | V-2 | Ppig | 9360 | 4-May-15 | 7867 | 3 | 4 | 5 | | | V-2 | Rfwd2 | 64326 | 4-May-15 |
| 7774 | 3 | 4 | 5 | | | V-2 | Ppm1l | 151742 | 4-May-15 | 7868 | 3 | 4 | 5 | | | V-2 | Rfx4 | 5992 | 28-May-15 |
| 7775 | 3 | 4 | 5 | | | V-2 | Ppm1m | 132160 | 4-May-15 | 7869 | 3 | 4 | 5 | | | V-2 | Rgmb | 285704 | 4-May-15 |
| 7776 | 3 | 4 | 5 | | | V-2 | Ppme1 | 51400 | 4-May-15 | 7870 | 3 | 4 | 5 | | | V-2 | Rgs3 | 5998 | 12-May-15 |
| 7777 | 3 | 4 | 5 | | | V-2 | Ppp1r2-ps7 | | | 7871 | 3 | 4 | 5 | | | V-2 | Rgs7 | 6000 | 4-May-15 |
| 7778 | 3 | 4 | 5 | | | V-2 | Ppp1r35 | 221908 | 4-May-15 | 7872 | 3 | 4 | 5 | | | V-2 | Rgs7bp | 401190 | 4-May-15 |
| 7779 | 3 | 4 | 5 | | | V-2 | Ppp1r37 | 284352 | 4-May-15 | 7873 | 3 | 4 | 5 | | | V-2 | Rgs8 | 85397 | 4-May-15 |
| 7780 | 3 | 4 | 5 | | | V-2 | Ppp1r3e | 90673 | 4-May-15 | 7874 | 3 | 4 | 5 | | | V-2 | Rhbdf2 | 79651 | 4-May-15 |
| 7781 | 3 | 4 | 5 | | | V-2 | Ppp1r3fos | | | 7875 | 3 | 4 | 5 | | | V-2 | Rhou | 58480 | 4-May-15 |
| 7782 | 3 | 4 | 5 | | | V-2 | Ppp1r9b | 84687 | 4-May-15 | 7876 | 3 | 4 | 5 | | | V-2 | Rhox3f | | |
| 7783 | 3 | 4 | 5 | | | V-2 | Ppp2r2c | 5522 | 12-May-15 | 7877 | 3 | 4 | 5 | | | V-2 | Rictor | 253260 | 4-May-15 |
| 7784 | 3 | 4 | 5 | | | V-2 | Ppp2r2cos | | | 7878 | 3 | 4 | 5 | | | V-2 | Rilpl2 | 196383 | 4-May-15 |
| 7785 | 3 | 4 | 5 | | | V-2 | Ppp2r3c | 55012 | 20-May-15 | 7879 | 3 | 4 | 5 | | | V-2 | Rimbp3 | 85376 | 4-May-15 |
| 7786 | 3 | 4 | 5 | | | V-2 | Ppwd1 | 23398 | 4-May-15 | 7880 | 3 | 4 | 5 | | | V-2 | Rit1 | 6016 | 7-Jun-15 |
| 7787 | 3 | 4 | 5 | | | V-2 | Prdm2 | 7799 | 4-May-15 | 7881 | 3 | 4 | 5 | | | V-2 | Rlbp1 | 6017 | 4-May-15 |
| 7788 | 3 | 4 | 5 | | | V-2 | Prdm9 | 56979 | 12-May-15 | 7882 | 3 | 4 | 5 | | | V-2 | Rmdn3 | 55177 | 12-May-15 |
| 7789 | 3 | 4 | 5 | | | V-2 | Prdx6b | | | 7883 | 3 | 4 | 5 | | | V-2 | Rnase1 | 6041 | 4-May-15 |
| 7790 | 3 | 4 | 5 | | | V-2 | Preb | 10113 | 4-May-15 | 7884 | 3 | 4 | 5 | | | V-2 | Rnaset2b | | |
| 7791 | 3 | 4 | 5 | | | V-2 | Prepl | 9581 | 4-May-15 | 7885 | 3 | 4 | 5 | | | V-2 | Rnf145 | 153830 | 4-May-15 |
| 7792 | 3 | 4 | 5 | | | V-2 | Prf1 | 5551 | 7-Jun-15 | 7886 | 3 | 4 | 5 | | | V-2 | Rnf167 | 26001 | 4-May-15 |
| 7793 | 3 | 4 | 5 | | | V-2 | Prickle2 | 166336 | 4-May-15 | 7887 | 3 | 4 | 5 | | | V-2 | Rnf17 | 56163 | 14-May-15 |
| 7794 | 3 | 4 | 5 | | | V-2 | Primpol | 201973 | 23-May-15 | 7888 | 3 | 4 | 5 | | | V-2 | Rnf208 | 727800 | 4-May-15 |
| 7795 | 3 | 4 | 5 | | | V-2 | Prkab1 | 5564 | 2-Jun-15 | 7889 | 3 | 4 | 5 | | | V-2 | Rnf224 | 643596 | 4-May-15 |
| 7796 | 3 | 4 | 5 | | | V-2 | Prkar1a | 5573 | 23-May-15 | 7890 | 3 | 4 | 5 | | | V-2 | Rnf4 | 6047 | 4-May-15 |
| 7797 | 3 | 4 | 5 | | | V-2 | Prkar2a | 5576 | 4-May-15 | 7891 | 3 | 4 | 5 | | | V-2 | Rnf44 | 22838 | 4-May-15 |
| 7798 | 3 | 4 | 5 | | | V-2 | Prkch | 5583 | 4-May-15 | 7892 | 3 | 4 | 5 | | | V-2 | Rnmt | 8731 | 21-May-15 |
| 7799 | 3 | 4 | 5 | | | V-2 | Prkg2 | 5593 | 17-May-15 | 7893 | 3 | 4 | 5 | | | V-2 | Rnpc3 | 55599 | 4-May-15 |
| 7800 | 3 | 4 | 5 | | | V-2 | Prkra | 8575 | 12-May-15 | 7894 | 3 | 4 | 5 | | | V-2 | Robo4 | 54538 | 4-May-15 |
| 7801 | 3 | 4 | 5 | | | V-2 | Prox2 | 283571 | 4-May-15 | 7895 | 3 | 4 | 5 | | | V-2 | Romo1 | 140823 | 24-May-15 |
| 7802 | 3 | 4 | 5 | | | V-2 | Prpsap1 | 5635 | 21-May-15 | 7896 | 3 | 4 | 5 | | | V-2 | Ror1 | 4919 | 7-Jun-15 |
| 7803 | 3 | 4 | 5 | | | V-2 | Prr18 | 285800 | 4-May-15 | 7897 | 3 | 4 | 5 | | | V-2 | Rorb | 6096 | 4-May-15 |
| 7804 | 3 | 4 | 5 | | | V-2 | Prr19 | 284338 | 20-May-15 | 7898 | 3 | 4 | 5 | | | V-2 | Rpap3 | 79657 | 4-May-15 |
| 7805 | 3 | 4 | 5 | | | V-2 | Prr30 | 339779 | 4-May-15 | 7899 | 3 | 4 | 5 | | | V-2 | Rpl11 | 6135 | 23-May-15 |
| 7806 | 3 | 4 | 5 | | | V-2 | Prr33 | 102724536 | 17-Mar-15 | 7900 | 3 | 4 | 5 | | | V-2 | Rpl27a | 6157 | 4-May-15 |
| 7807 | 3 | 4 | 5 | | | V-2 | Prrc1 | 133619 | 4-May-15 | 7901 | 3 | 4 | 5 | | | V-2 | Rpp25l | 138716 | 4-May-15 |
| 7808 | 3 | 4 | 5 | | | V-2 | Prrt3 | 285368 | 12-May-15 | 7902 | 3 | 4 | 5 | | | V-2 | Rps10 | 6204 | 22-May-15 |
| 7809 | 3 | 4 | 5 | | | V-2 | Prss32 | | | 7903 | 3 | 4 | 5 | | | V-2 | Rps11 | 6205 | 4-May-15 |
| 7810 | 3 | 4 | 5 | | | V-2 | Prss33 | 260429 | 4-May-15 | 7904 | 3 | 4 | 5 | | | V-2 | Rps17 | 6218 | 23-May-15 |
| 7811 | 3 | 4 | 5 | | | V-2 | Prss37 | 136242 | 4-May-15 | 7905 | 3 | 4 | 5 | | | V-2 | Rps19 | 6223 | 21-May-15 |
| 7812 | 3 | 4 | 5 | | | V-2 | Prss46 | 100287362 | 4-May-15 | 7906 | 3 | 4 | 5 | | | V-2 | Rps20 | 6224 | 4-May-15 |
| 7813 | 3 | 4 | 5 | | | V-2 | Prss54 | 221191 | 20-May-15 | 7907 | 3 | 4 | 5 | | | V-2 | Rps28 | 6234 | 28-May-15 |
| 7814 | 3 | 4 | 5 | | | V-2 | Prss58 | 136541 | 4-May-15 | 7908 | 3 | 4 | 5 | | | V-2 | Rps7 | 6201 | 7-Jun-15 |
| 7815 | 3 | 4 | 5 | | | V-2 | Psap | 5660 | 7-Jun-15 | 7909 | 3 | 4 | 5 | | | V-2 | Rpusd1 | 113000 | 4-May-15 |
| 7816 | 3 | 4 | 5 | | | V-2 | Psmb1 | 5689 | 4-May-15 | 7910 | 3 | 4 | 5 | | | V-2 | Rpusd4 | 84881 | 4-May-15 |
| 7817 | 3 | 4 | 5 | | | V-2 | Psmb2 | 5690 | 12-May-15 | 7911 | 3 | 4 | 5 | | | V-2 | Rqcd1 | 9125 | 12-May-15 |
| 7818 | 3 | 4 | 5 | | | V-2 | Psme2 | 5721 | 4-May-15 | 7912 | 3 | 4 | 5 | | | V-2 | Rrs1 | 23212 | 4-May-15 |
| 7819 | 3 | 4 | 5 | | | V-2 | Ptbp1 | 5725 | 4-May-15 | 7913 | 3 | 4 | 5 | | | V-2 | Rsph6a | 81492 | 4-May-15 |
| 7820 | 3 | 4 | 5 | | | V-2 | Ptch1 | 5727 | 23-May-15 | 7914 | 3 | 4 | 5 | | | V-2 | Rspo4 | 343637 | 4-May-15 |
| 7821 | 3 | 4 | 5 | | | V-2 | Ptchd1 | 139411 | 23-May-15 | 7915 | 3 | 4 | 5 | | | V-2 | Rtel1 | 51750 | 4-Jun-15 |
| 7822 | 3 | 4 | 5 | | | V-2 | Ptcra | 171558 | 12-May-15 | 7916 | 3 | 4 | 5 | | | V-2 | Rtl1 | 388015 | 4-May-15 |
| 7823 | 3 | 4 | 5 | | | V-2 | Ptgdr | 5729 | 3-Dec-15 | 7917 | 3 | 4 | 5 | | | V-2 | Runx2 | 860 | 31-May-15 |
| 7824 | 3 | 4 | 5 | | | V-2 | Ptges3 | 10728 | 4-May-15 | 7918 | 3 | 4 | 5 | | | V-2 | Rxfp1 | 59350 | 4-May-15 |
| 7825 | 3 | 4 | 5 | | | V-2 | Ptgfrn | 5738 | 4-May-15 | 7919 | 3 | 4 | 5 | | | V-2 | Saal1 | 113174 | 4-May-15 |
| 7826 | 3 | 4 | 5 | | | V-2 | Ptgs1 | 5742 | 12-May-15 | 7920 | 3 | 4 | 5 | | | V-2 | Satb2 | 23314 | 4-May-15 |
| 7827 | 3 | 4 | 5 | | | V-2 | Ptpladl | 51495 | 4-May-15 | 7921 | 3 | 4 | 5 | | | V-2 | Sbno1 | 55206 | 4-May-15 |
| 7828 | 3 | 4 | 5 | | | V-2 | Ptprt | 11122 | 4-May-15 | 7922 | 3 | 4 | 5 | | | V-2 | Scd4 | 79966 | 4-May-15 |
| 7829 | 3 | 4 | 5 | | | V-2 | Pxn | 5829 | 7-Jun-15 | 7923 | 3 | 4 | 5 | | | V-2 | Scg5 | 6447 | 12-May-15 |
| 7830 | 3 | 4 | 5 | | | V-2 | Pydc3 | | | 7924 | 3 | 4 | 5 | | | V-2 | Scgb2b3 | | |
| 7831 | 3 | 4 | 5 | | | V-2 | R74862 | | | 7925 | 3 | 4 | 5 | | | V-2 | Schip1 | 29970 | 4-May-15 |
| 7832 | 3 | 4 | 5 | | | V-2 | Rab18 | 22931 | 24-May-15 | 7926 | 3 | 4 | 5 | | | V-2 | Scn3a | 6328 | 12-May-15 |
| 7833 | 3 | 4 | 5 | | | V-2 | Rab28 | 9364 | 23-May-15 | 7927 | 3 | 4 | 5 | | | V-2 | Scp2d1 | 140856 | 4-May-15 |
| 7834 | 3 | 4 | 5 | | | V-2 | Rab37 | 326624 | 12-May-15 | 7928 | 3 | 4 | 5 | | | V-2 | Scube3 | 222663 | 4-May-15 |
| 7835 | 3 | 4 | 5 | | | V-2 | Rab39 | 54734 | 7-Jun-15 | 7929 | 3 | 4 | 5 | | | V-2 | Sdhaf1 | 644096 | 4-May-15 |
| 7836 | 3 | 4 | 5 | | | V-2 | Rab3b | 5865 | 21-May-15 | 7930 | 3 | 4 | 5 | | | V-2 | Sdhc | 6391 | 23-May-15 |
| 7837 | 3 | 4 | 5 | | | V-2 | Rab3gap1 | 22930 | 4-May-15 | 7931 | 3 | 4 | 5 | | | V-2 | Sdhd | 6392 | 23-May-15 |
| 7838 | 3 | 4 | 5 | | | V-2 | Rabac1 | 10567 | 4-May-15 | 7932 | 3 | 4 | 5 | | | V-2 | Sdk1 | 221935 | 4-May-15 |
| 7839 | 3 | 4 | 5 | | | V-2 | Raet1c | | | 7933 | 3 | 4 | 5 | | | V-2 | Sdr42e1 | 93517 | 4-May-15 |
| 7840 | 3 | 4 | 5 | | | V-2 | Raet1e | 135250 | 12-May-15 | 7934 | 3 | 4 | 5 | | | V-2 | Sec11a | 23478 | 4-May-15 |
| 7841 | 3 | 4 | 5 | | | V-2 | Ralgps1 | 9649 | 4-May-15 | 7935 | 3 | 4 | 5 | | | V-2 | Sec16a | 9919 | 12-May-15 |
| 7842 | 3 | 4 | 5 | | | V-2 | Raplgds1 | 5910 | 4-May-15 | 7936 | 3 | 4 | 5 | | | V-2 | Sec23a | 10484 | 12-May-15 |
| 7843 | 3 | 4 | 5 | | | V-2 | Rara | 5914 | 17-May-15 | 7937 | 3 | 4 | 5 | | | V-2 | Sec23ip | 11196 | 4-May-15 |
| 7844 | 3 | 4 | 5 | | | V-2 | Rarg | 5916 | 4-May-15 | 7938 | 3 | 4 | 5 | | | V-2 | Sema5a | 9037 | 4-May-15 |
| 7845 | 3 | 4 | 5 | | | V-2 | Rasl11a | 387496 | 4-May-15 | 7939 | 3 | 4 | 5 | | | V-2 | Sema6d | 80031 | 4-May-15 |
| 7846 | 3 | 4 | 5 | | | V-2 | Rax | 30062 | 7-Jun-15 | 7940 | 3 | 4 | 5 | | | V-2 | Sept4 | 5414 | 12-May-15 |
| 7847 | 3 | 4 | 5 | | | V-2 | Rbbp4 | 5928 | 24-May-15 | 7941 | 3 | 4 | 5 | | | V-2 | Serinc1 | 57515 | 28-May-15 |
| 7848 | 3 | 4 | 5 | | | V-2 | Rbfox2 | 23543 | 2-Jun-15 | 7942 | 3 | 4 | 5 | | | V-2 | Serp1 | 27230 | 14-May-15 |
| 7849 | 3 | 4 | 5 | | | V-2 | Rbks | 64080 | 4-May-15 | 7943 | 3 | 4 | 5 | | | V-2 | Serpina5 | 5104 | 12-May-15 |
| 7850 | 3 | 4 | 5 | | | V-2 | Rbm10 | 8241 | 12-May-15 | 7944 | 3 | 4 | 5 | | | V-2 | Serpina6 | 866 | 31-May-15 |
| 7851 | 3 | 4 | 5 | | | V-2 | Rbm14 | 10432 | 1-Jun-15 | 7945 | 3 | 4 | 5 | | | V-2 | Serpina7 | 6906 | 4-May-15 |
| 7852 | 3 | 4 | 5 | | | V-2 | Rbm22 | 55696 | 2-Jun-15 | 7946 | 3 | 4 | 5 | | | V-2 | Serpinb5 | 5268 | 4-May-15 |
| 7853 | 3 | 4 | 5 | | | V-2 | Rbm34 | 23029 | 4-May-15 | 7947 | 3 | 4 | 5 | | | V-2 | Serpinb9g | | |
| 7854 | 3 | 4 | 5 | | | V-2 | Rbm46os | | | 7948 | 3 | 4 | 5 | | | V-2 | Serpind1 | 3053 | 4-May-15 |
| 7855 | 3 | 4 | 5 | | | V-2 | Rbpms | 11030 | 4-May-15 | 7949 | 3 | 4 | 5 | | | V-2 | Sfi1 | 7536 | 7-Jun-15 |
| 7856 | 3 | 4 | 5 | | | V-2 | Rbpms2 | 348093 | 4-May-15 | 7950 | 3 | 4 | 5 | | | V-2 | Sfmbt1 | 51460 | 4-May-15 |
| 7857 | 3 | 4 | 5 | | | V-2 | Rchy1 | 25898 | 2-Jun-15 | 7951 | 3 | 4 | 5 | | | V-2 | Sfxn3 | 81855 | 4-May-15 |
| 7858 | 3 | 4 | 5 | | | V-2 | Rcn2 | 5955 | 7-Jun-15 | 7952 | 3 | 4 | 5 | | | V-2 | Sfxn5 | 94097 | 4-May-15 |
| 7859 | 3 | 4 | 5 | | | V-2 | Rdh19 | | | 7953 | 3 | 4 | 5 | | | V-2 | Sgcd | 6444 | 23-May-15 |
| | | | | | | | | | | 7954 | 3 | 4 | 5 | | | V-2 | Sgcz | 137868 | 17-May-15 |
| | | | | | | | | | | 7955 | 3 | 4 | 5 | | | V-2 | Sh3bp5 | 9467 | 4-May-15 |

Fig. 30 - 43

| | | | | | | | | | | | | | | | | |
|---|---|---|---|---|---|---|---|---|---|---|---|---|---|---|---|---|
| 7956 | 3 | 4 | 5 | | | V-2 | She | 126669 | 4-May-15 | 8051 | 3 | 4 | 5 | | | V-2 | Ssbp3 | 23648 | 12-May-15 |
| 7957 | 3 | 4 | 5 | | | V-2 | Shisa7 | 729956 | 4-May-15 | 8052 | 3 | 4 | 5 | | | V-2 | Ssr2 | 6746 | 4-May-15 |
| 7958 | 3 | 4 | 5 | | | V-2 | Shprh | 257218 | 4-May-15 | 8053 | 3 | 4 | 5 | | | V-2 | St3gal4 | 6484 | 21-May-15 |
| 7959 | 3 | 4 | 5 | | | V-2 | Siah1a | 6477 | 24-May-15 | 8054 | 3 | 4 | 5 | | | V-2 | St8sia2 | 8128 | 4-May-15 |
| 7960 | 3 | 4 | 5 | | | V-2 | Siglec5 | 8778 | 4-May-15 | 8055 | 3 | 4 | 5 | | | V-2 | St8sia3 | 51046 | 23-May-15 |
| 7961 | 3 | 4 | 5 | | | V-2 | Sirt5 | 23408 | 31-May-15 | 8056 | 3 | 4 | 5 | | | V-2 | Stam | 8027 | 4-May-15 |
| 7962 | 3 | 4 | 5 | | | V-2 | Sirt6 | 51548 | 31-May-15 | 8057 | 3 | 4 | 5 | | | V-2 | Stard5 | 80765 | 4-May-15 |
| 7963 | 3 | 4 | 5 | | | V-2 | Six5 | 147912 | 23-May-15 | 8058 | 3 | 4 | 5 | | | V-2 | Stard8 | 9754 | 4-May-15 |
| 7964 | 3 | 4 | 5 | | | V-2 | Skint10 | | | 8059 | 3 | 4 | 5 | | | V-2 | Stk35 | 140901 | 4-May-15 |
| 7965 | 3 | 4 | 5 | | | V-2 | Skint3 | | | 8060 | 3 | 4 | 5 | | | V-2 | Stk38 | 11329 | 20-May-15 |
| 7966 | 3 | 4 | 5 | | | V-2 | Skint4 | | | 8061 | 3 | 4 | 5 | | | V-2 | Stk4 | 6789 | 4-May-15 |
| 7967 | 3 | 4 | 5 | | | V-2 | Slc12a5 | 57468 | 12-May-15 | 8062 | 3 | 4 | 5 | | | V-2 | Stmnd1 | 401346 | 4-May-15 |
| 7968 | 3 | 4 | 5 | | | V-2 | Slc13a3 | 64849 | 4-May-15 | 8063 | 3 | 4 | 5 | | | V-2 | Ston1 | 11037 | 4-May-15 |
| 7969 | 3 | 4 | 5 | | | V-2 | Slc13a5 | 284111 | 31-May-15 | 8064 | 3 | 4 | 5 | | | V-2 | Stox1 | 219736 | 3-May-15 |
| 7970 | 3 | 4 | 5 | | | V-2 | Slc16a13 | 201232 | 4-May-15 | 8065 | 3 | 4 | 5 | | | V-2 | Stra8 | 346673 | 4-May-15 |
| 7971 | 3 | 4 | 5 | | | V-2 | Slc17a3 | 10786 | 4-May-15 | 8066 | 3 | 4 | 5 | | | V-2 | Styk1 | 55359 | 31-May-15 |
| 7972 | 3 | 4 | 5 | | | V-2 | Slc17a4 | 10050 | 4-May-15 | 8067 | 3 | 4 | 5 | | | V-2 | Suclg1 | 8802 | 4-May-15 |
| 7973 | 3 | 4 | 5 | | | V-2 | Slc22a12 | 116085 | 12-May-15 | 8068 | 3 | 4 | 5 | | | V-2 | Suclg2 | 8801 | 4-May-15 |
| 7974 | 3 | 4 | 5 | | | V-2 | Slc22a15 | 55356 | 4-May-15 | 8069 | 3 | 4 | 5 | | | V-2 | Sucnr1 | 56670 | 4-May-15 |
| 7975 | 3 | 4 | 5 | | | V-2 | Slc22a19 | | | 8070 | 3 | 4 | 5 | | | V-2 | Sugct | 79783 | 12-May-15 |
| 7976 | 3 | 4 | 5 | | | V-2 | Slc22a20 | 440044 | 4-May-15 | 8071 | 3 | 4 | 5 | | | V-2 | Sugp1 | 57794 | 4-May-15 |
| 7977 | 3 | 4 | 5 | | | V-2 | Slc22a28 | | | 8072 | 3 | 4 | 5 | | | V-2 | Surf1 | 6834 | 23-May-15 |
| 7978 | 3 | 4 | 5 | | | V-2 | Slc22a29 | | | 8073 | 3 | 4 | 5 | | | V-2 | Suv39h1 | 6839 | 12-May-15 |
| 7979 | 3 | 4 | 5 | | | V-2 | Slc22a8 | 9376 | 12-May-15 | 8074 | 3 | 4 | 5 | | | V-2 | Sv2b | 9899 | 4-May-15 |
| 7980 | 3 | 4 | 5 | | | V-2 | Slc23a2 | 9962 | 7-Jun-15 | 8075 | 3 | 4 | 5 | | | V-2 | Svs1 | | |
| 7981 | 3 | 4 | 5 | | | V-2 | Slc25a12 | 8604 | 4-May-15 | 8076 | 3 | 4 | 5 | | | V-2 | Syce1 | 93426 | 4-May-15 |
| 7982 | 3 | 4 | 5 | | | V-2 | Slc25a13 | 10165 | 23-May-15 | 8077 | 3 | 4 | 5 | | | V-2 | Syde1 | 85360 | 4-May-15 |
| 7983 | 3 | 4 | 5 | | | V-2 | Slc25a14 | 9016 | 4-May-15 | 8078 | 3 | 4 | 5 | | | V-2 | Syf2 | 25949 | 17-May-15 |
| 7984 | 3 | 4 | 5 | | | V-2 | Slc25a2 | 83884 | 4-May-15 | 8079 | 3 | 4 | 5 | | | V-2 | Sypl | 6856 | 4-May-15 |
| 7985 | 3 | 4 | 5 | | | V-2 | Slc25a27 | 9481 | 4-May-15 | 8080 | 3 | 4 | 5 | | | V-2 | Sys1 | 90196 | 4-May-15 |
| 7986 | 3 | 4 | 5 | | | V-2 | Slc25a3 | 5250 | 21-May-15 | 8081 | 3 | 4 | 5 | | | V-2 | Syt11 | 23208 | 16-Jun-15 |
| 7987 | 3 | 4 | 5 | | | V-2 | Slc25a34 | 284723 | 4-May-15 | 8082 | 3 | 4 | 5 | | | V-2 | Syt2 | 127833 | 5-May-15 |
| 7988 | 3 | 4 | 5 | | | V-2 | Slc25a44 | 9673 | 14-May-15 | 8083 | 3 | 4 | 5 | | | V-2 | Syt4 | 6860 | 12-May-15 |
| 7989 | 3 | 4 | 5 | | | V-2 | Slc26a7 | 115111 | 4-May-15 | 8084 | 3 | 4 | 5 | | | V-2 | Syt8 | 90019 | 4-May-15 |
| 7990 | 3 | 4 | 5 | | | V-2 | Slc26a8 | 116369 | 4-May-15 | 8085 | 3 | 4 | 5 | | | V-2 | Taar1 | 134864 | 7-Jun-15 |
| 7991 | 3 | 4 | 5 | | | V-2 | Slc28a1 | 9154 | 12-May-15 | 8086 | 3 | 4 | 5 | | | V-2 | Tacr1 | 6869 | 17-May-15 |
| 7992 | 3 | 4 | 5 | | | V-2 | Slc2a2 | 6514 | 12-May-15 | 8087 | 3 | 4 | 5 | | | V-2 | Tank | 10010 | 4-May-15 |
| 7993 | 3 | 4 | 5 | | | V-2 | Slc2a9 | 56606 | 31-May-15 | 8088 | 3 | 4 | 5 | | | V-2 | Tapbp | 6892 | 17-May-15 |
| 7994 | 3 | 4 | 5 | | | V-2 | Slc30a1 | 7779 | 17-May-15 | 8089 | 3 | 4 | 5 | | | V-2 | Tax1bp1 | 8887 | 12-May-15 |
| 7995 | 3 | 4 | 5 | | | V-2 | Slc30a4 | 7782 | 4-May-15 | 8090 | 3 | 4 | 5 | | | V-2 | Tbc1d1 | 23216 | 4-May-15 |
| 7996 | 3 | 4 | 5 | | | V-2 | Slc30a5 | 64924 | 4-May-15 | 8091 | 3 | 4 | 5 | | | V-2 | Tbc1d10b | 26000 | 4-May-15 |
| 7997 | 3 | 4 | 5 | | | V-2 | Slc35f4 | 341880 | 12-May-15 | 8092 | 3 | 4 | 5 | | | V-2 | Tbc1d31 | 93594 | 4-May-15 |
| 7998 | 3 | 4 | 5 | | | V-2 | Slc36a1os | | | 8093 | 3 | 4 | 5 | | | V-2 | Tbc1d4 | 9882 | 4-May-15 |
| 7999 | 3 | 4 | 5 | | | V-2 | Slc41a1 | 254428 | 4-May-15 | 8094 | 3 | 4 | 5 | | | V-2 | Tbc1d5 | 9779 | 28-May-15 |
| 8000 | 3 | 4 | 5 | | | V-2 | Slc44a5 | 204962 | 14-May-15 | 8095 | 3 | 4 | 5 | | | V-2 | Tbx15 | 6913 | 4-May-15 |
| 8001 | 3 | 4 | 5 | | | V-2 | Slc47a1 | 55244 | 24-May-15 | 8096 | 3 | 4 | 5 | | | V-2 | Tbx5 | 6910 | 31-May-15 |
| 8002 | 3 | 4 | 5 | | | V-2 | Slc4a7 | 9497 | 4-May-15 | 8097 | 3 | 4 | 5 | | | V-2 | Tbx6 | 6911 | 12-May-15 |
| 8003 | 3 | 4 | 5 | | | V-2 | Slc4a9 | 83697 | 4-May-15 | 8098 | 3 | 4 | 5 | | | V-2 | Tcam1 | 146771 | 4-May-15 |
| 8004 | 3 | 4 | 5 | | | V-2 | Slc5a10 | 125206 | 4-May-15 | 8099 | 3 | 4 | 5 | | | V-2 | Tceal5 | 340543 | 4-May-15 |
| 8005 | 3 | 4 | 5 | | | V-2 | Slc6a15 | 55117 | 14-May-15 | 8100 | 3 | 4 | 5 | | | V-2 | Tceal6 | 158931 | 4-May-15 |
| 8006 | 3 | 4 | 5 | | | V-2 | Slc6a19os | | | 8101 | 3 | 4 | 5 | | | V-2 | Tcf12 | 6938 | 28-May-15 |
| 8007 | 3 | 4 | 5 | | | V-2 | Slc8a1 | 6546 | 23-May-15 | 8102 | 3 | 4 | 5 | | | V-2 | Tcf7l2 | 6934 | 31-May-15 |
| 8008 | 3 | 4 | 5 | | | V-2 | Slc8b1 | 80024 | 4-May-15 | 8103 | 3 | 4 | 5 | | | V-2 | Tcof1 | 6949 | 24-May-15 |
| 8009 | 3 | 4 | 5 | | | V-2 | Slc9a3r1 | 9368 | 31-May-15 | 8104 | 3 | 4 | 5 | | | V-2 | Tcp11l2 | 255394 | 12-May-15 |
| 8010 | 3 | 4 | 5 | | | V-2 | Slc9a9 | 285195 | 4-May-15 | 8105 | 3 | 4 | 5 | | | V-2 | Tcstv3 | | |
| 8011 | 3 | 4 | 5 | | | V-2 | Slco1b2 | | | 8106 | 3 | 4 | 5 | | | V-2 | Tcta | 6988 | 4-May-15 |
| 8012 | 3 | 4 | 5 | | | V-2 | Slco3a1 | 28232 | 12-May-15 | 8107 | 3 | 4 | 5 | | | V-2 | Tcte2 | | |
| 8013 | 3 | 4 | 5 | | | V-2 | Slco6b1 | | | 8108 | 3 | 4 | 5 | | | V-2 | Tctex1d2 | 255758 | 4-May-15 |
| 8014 | 3 | 4 | 5 | | | V-2 | Slk | 9748 | 7-Jun-15 | 8109 | 3 | 4 | 5 | | | V-2 | Tdp1 | 55775 | 24-May-15 |
| 8015 | 3 | 4 | 5 | | | V-2 | Slx | | | 8110 | 3 | 4 | 5 | | | V-2 | Tdpoz1 | | |
| 8016 | 3 | 4 | 5 | | | V-2 | Smad4 | 4089 | 23-May-15 | 8111 | 3 | 4 | 5 | | | V-2 | Tdrp | 157695 | 4-May-15 |
| 8017 | 3 | 4 | 5 | | | V-2 | Smad7 | 4092 | 12-May-15 | 8112 | 3 | 4 | 5 | | | V-2 | Tecr | 9524 | 4-May-15 |
| 8018 | 3 | 4 | 5 | | | V-2 | Smagp | 57228 | 4-May-15 | 8113 | 3 | 4 | 5 | | | V-2 | Tecta | 7007 | 4-May-15 |
| 8019 | 3 | 4 | 5 | | | V-2 | Smco2 | 341346 | 4-May-15 | 8114 | 3 | 4 | 5 | | | V-2 | Tefm | 79736 | 4-May-15 |
| 8020 | 3 | 4 | 5 | | | V-2 | Smim5 | 643008 | 4-May-15 | 8115 | 3 | 4 | 5 | | | V-2 | Tek | 7010 | 23-May-15 |
| 8021 | 3 | 4 | 5 | | | V-2 | Smim9 | 100132963 | 4-May-15 | 8116 | 3 | 4 | 5 | | | V-2 | Tekt3 | 64518 | 4-May-15 |
| 8022 | 3 | 4 | 5 | | | V-2 | Smpdl3a | 10924 | 23-May-15 | 8117 | 3 | 4 | 5 | | | V-2 | Tert | 7015 | 4-Jun-15 |
| 8023 | 3 | 4 | 5 | | | V-2 | Smyd3 | 64754 | 21-May-15 | 8118 | 3 | 4 | 5 | | | V-2 | Tet2 | 54790 | 17-May-15 |
| 8024 | 3 | 4 | 5 | | | V-2 | Smyd5 | 10322 | 4-May-15 | 8119 | 3 | 4 | 5 | | | V-2 | Tex12 | 56158 | 4-May-15 |
| 8025 | 3 | 4 | 5 | | | V-2 | Snrpc | 6631 | 7-Jun-15 | 8120 | 3 | 4 | 5 | | | V-2 | Tex43 | 389320 | 4-May-15 |
| 8026 | 3 | 4 | 5 | | | V-2 | Snta1 | 6640 | 23-May-15 | 8121 | 3 | 4 | 5 | | | V-2 | Tfam | 7019 | 31-May-15 |
| 8027 | 3 | 4 | 5 | | | V-2 | Sntb2 | 6645 | 4-May-15 | 8122 | 3 | 4 | 5 | | | V-2 | Tfb1m | 51106 | 4-May-15 |
| 8028 | 3 | 4 | 5 | | | V-2 | Snx32 | 254122 | 12-May-15 | 8123 | 3 | 4 | 5 | | | V-2 | Tfb2m | 64216 | 4-May-15 |
| 8029 | 3 | 4 | 5 | | | V-2 | Sorl1 | 6653 | 23-May-15 | 8124 | 3 | 4 | 5 | | | V-2 | Tfcp2 | 7024 | 4-May-15 |
| 8030 | 3 | 4 | 5 | | | V-2 | Sos1 | 6654 | 23-May-15 | 8125 | 3 | 4 | 5 | | | V-2 | Tgfbrap1 | 9392 | 4-May-15 |
| 8031 | 3 | 4 | 5 | | | V-2 | Sowahc | 65124 | 4-May-15 | 8126 | 3 | 4 | 5 | | | V-2 | Thada | 63892 | 4-May-15 |
| 8032 | 3 | 4 | 5 | | | V-2 | Sox18 | 54345 | 12-May-15 | 8127 | 3 | 4 | 5 | | | V-2 | Themis | 387357 | 12-May-15 |
| 8033 | 3 | 4 | 5 | | | V-2 | Sox3 | 6658 | 23-May-15 | 8128 | 3 | 4 | 5 | | | V-2 | Timm22 | 29928 | 4-May-15 |
| 8034 | 3 | 4 | 5 | | | V-2 | Spaca1 | 81833 | 4-May-15 | 8129 | 3 | 4 | 5 | | | V-2 | Timm44 | 10469 | 21-May-15 |
| 8035 | 3 | 4 | 5 | | | V-2 | Spaca3 | 124912 | 4-May-15 | 8130 | 3 | 4 | 5 | | | V-2 | Timm50 | 92609 | 4-May-15 |
| 8036 | 3 | 4 | 5 | | | V-2 | Spag17 | 200162 | 12-May-15 | 8131 | 3 | 4 | 5 | | | V-2 | Tldc1 | 57707 | 4-May-15 |
| 8037 | 3 | 4 | 5 | | | V-2 | Spag7 | 9552 | 4-May-15 | 8132 | 3 | 4 | 5 | | | V-2 | Tldc2 | 140711 | 4-May-15 |
| 8038 | 3 | 4 | 5 | | | V-2 | Spag9 | 9043 | 4-May-15 | 8133 | 3 | 4 | 5 | | | V-2 | Tlx2 | 7093 | 4-May-15 |
| 8039 | 3 | 4 | 5 | | | V-2 | Spata16 | 83893 | 12-May-15 | 8134 | 3 | 4 | 5 | | | V-2 | Tlx2 | 3196 | 7-Jun-15 |
| 8040 | 3 | 4 | 5 | | | V-2 | Spata2 | 9825 | 12-May-15 | 8135 | 3 | 4 | 5 | | | V-2 | Tlx3 | 30012 | 12-May-15 |
| 8041 | 3 | 4 | 5 | | | V-2 | Spata45 | 149643 | 4-May-15 | 8136 | 3 | 4 | 5 | | | V-2 | Tm4sf5 | 9032 | 4-May-15 |
| 8042 | 3 | 4 | 5 | | | V-2 | Spata9 | 83880 | 4-May-15 | 8137 | 3 | 4 | 5 | | | V-2 | Tmco3 | 55002 | 12-May-15 |
| 8043 | 3 | 4 | 5 | | | V-2 | Spats2 | 65244 | 12-May-15 | 8138 | 3 | 4 | 5 | | | V-2 | Tmem144 | 55314 | 4-May-15 |
| 8044 | 3 | 4 | 5 | | | V-2 | Spem1 | 374768 | 4-May-15 | 8139 | 3 | 4 | 5 | | | V-2 | Tmem14a | 28978 | 4-May-15 |
| 8045 | 3 | 4 | 5 | | | V-2 | Spice1 | 152185 | 4-May-15 | 8140 | 3 | 4 | 5 | | | V-2 | Tmem14c | 51522 | 4-May-15 |
| 8046 | 3 | 4 | 5 | | | V-2 | Spin4 | 139886 | 4-May-15 | 8141 | 3 | 4 | 5 | | | V-2 | Tmem154 | 201799 | 4-May-15 |
| 8047 | 3 | 4 | 5 | | | V-2 | Sppl2a | 84888 | 29-May-15 | 8142 | 3 | 4 | 5 | | | V-2 | Tmem178 | 130733 | 2-Jun-15 |
| 8048 | 3 | 4 | 5 | | | V-2 | Spryd7 | 57233 | 4-May-15 | 8143 | 3 | 4 | 5 | | | V-2 | Tmem181a | | |
| 8049 | 3 | 4 | 5 | | | V-2 | Srgap1 | 57522 | 4-May-15 | 8144 | 3 | 4 | 5 | | | V-2 | Tmem184c | 55751 | 4-May-15 |
| 8050 | 3 | 4 | 5 | | | V-2 | Srp14 | 6727 | 3-Jun-15 | 8145 | 3 | 4 | 5 | | | V-2 | Tmem189 | 387521 | 4-May-15 |
| | | | | | | | | | | 8146 | 3 | 4 | 5 | | | V-2 | Tmem190 | 147744 | 4-May-15 |

Fig. 30 - 44

| # | | | | | | | Name | ID | Date | # | | | | | | | Name | ID | Date |
|---|---|---|---|---|---|---|---|---|---|---|---|---|---|---|---|---|---|---|---|
| 8147 | 3 | 4 | 5 | | | V-2 | Tmem196 | 256130 | 4-May-15 | 8241 | 3 | 4 | 5 | | | V-2 | Ugt2b5 | | |
| 8148 | 3 | 4 | 5 | | | V-2 | Tmem198b | 440104 | 4-May-15 | 8242 | 3 | 4 | 5 | | | V-2 | Ugt3a1 | 133688 | 28-May-15 |
| 8149 | 3 | 4 | 5 | | | V-2 | Tmem202 | 338949 | 4-May-15 | 8243 | 3 | 4 | 5 | | | V-2 | Ugt3a2 | 167127 | 28-May-15 |
| 8150 | 3 | 4 | 5 | | | V-2 | Tmem204 | 79652 | 4-May-15 | 8244 | 3 | 4 | 5 | | | V-2 | Upb1 | 51733 | 17-May-15 |
| 8151 | 3 | 4 | 5 | | | V-2 | Tmem206 | 55248 | 4-May-15 | 8245 | 3 | 4 | 5 | | | V-2 | Uqcc1 | 55245 | 4-May-15 |
| 8152 | 3 | 4 | 5 | | | V-2 | Tmem218 | 219854 | 4-May-15 | 8246 | 3 | 4 | 5 | | | V-2 | Uqcc2 | 84300 | 14-May-15 |
| 8153 | 3 | 4 | 5 | | | V-2 | Tmem219 | 124446 | 4-May-15 | 8247 | 3 | 4 | 5 | | | V-2 | Uqcr11 | 10975 | 4-May-15 |
| 8154 | 3 | 4 | 5 | | | V-2 | Tmem234 | 56063 | 12-May-15 | 8248 | 3 | 4 | 5 | | | V-2 | Uqcrb | 7381 | 12-May-15 |
| 8155 | 3 | 4 | 5 | | | V-2 | Tmem247 | 388946 | 4-May-15 | 8249 | 3 | 4 | 5 | | | V-2 | Uqcrc1 | 7384 | 4-May-15 |
| 8156 | 3 | 4 | 5 | | | V-2 | Tmem251 | 26175 | | 8250 | 3 | 4 | 5 | | | V-2 | Uqcrc2 | 7385 | 4-May-15 |
| 8157 | 3 | 4 | 5 | | | V-2 | Tmem254b | | | 8251 | 3 | 4 | 5 | | | V-2 | Uqcrfs1 | 7386 | 4-May-15 |
| 8158 | 3 | 4 | 5 | | | V-2 | Tmem256 | 254863 | 4-May-15 | 8252 | 3 | 4 | 5 | | | V-2 | Uqcrh | 7388 | 4-May-15 |
| 8159 | 3 | 4 | 5 | | | V-2 | Tmem261 | 90871 | 21-May-15 | 8253 | 3 | 4 | 5 | | | V-2 | Urad | 646625 | 4-May-15 |
| 8160 | 3 | 4 | 5 | | | V-2 | Tmem28 | 27112 | 4-May-15 | 8254 | 3 | 4 | 5 | | | V-2 | Ush1g | 124590 | 23-May-15 |
| 8161 | 3 | 4 | 5 | | | V-2 | Tmem29 | 29057 | 4-May-15 | 8255 | 3 | 4 | 5 | | | V-2 | Ushbp1 | 83878 | 12-May-15 |
| 8162 | 3 | 4 | 5 | | | V-2 | Tmem41b | 440026 | 4-May-15 | 8256 | 3 | 4 | 5 | | | V-2 | Uso1 | 8615 | 12-May-15 |
| 8163 | 3 | 4 | 5 | | | V-2 | Tmem5 | 10329 | 21-May-15 | 8257 | 3 | 4 | 5 | | | V-2 | Usp29 | 57663 | 3-May-15 |
| 8164 | 3 | 4 | 5 | | | V-2 | Tmem54 | 113452 | 4-May-15 | 8258 | 3 | 4 | 5 | | | V-2 | Usp45 | 85015 | 4-May-15 |
| 8165 | 3 | 4 | 5 | | | V-2 | Tmem66 | 53669 | 12-May-15 | 8259 | 3 | 4 | 5 | | | V-2 | Uty | 7404 | 12-May-15 |
| 8166 | 3 | 4 | 5 | | | V-2 | Tmem70 | 54968 | 12-May-15 | 8260 | 3 | 4 | 5 | | | V-2 | Uvssa | 57654 | 21-May-15 |
| 8167 | 3 | 4 | 5 | | | V-2 | Tmem72 | 643236 | 4-May-15 | 8261 | 3 | 4 | 5 | | | V-2 | Vamp1 | 6843 | 23-May-15 |
| 8168 | 3 | 4 | 5 | | | V-2 | Tmem79 | 84283 | 4-May-15 | 8262 | 3 | 4 | 5 | | | V-2 | Vamp2 | 6844 | 4-May-15 |
| 8169 | 3 | 4 | 5 | | | V-2 | Tmem87b | 84910 | 4-May-15 | 8263 | 3 | 4 | 5 | | | V-2 | Vdac2 | 7417 | 12-May-15 |
| 8170 | 3 | 4 | 5 | | | V-2 | Tmem9 | 252839 | 4-May-15 | 8264 | 3 | 4 | 5 | | | V-2 | Vill | 50853 | 12-May-15 |
| 8171 | 3 | 4 | 5 | | | V-2 | Tmem98 | 26022 | 12-May-15 | 8265 | 3 | 4 | 5 | | | V-2 | Vmn1r1 | | |
| 8172 | 3 | 4 | 5 | | | V-2 | Tmpo | 7112 | 23-May-15 | 8266 | 3 | 4 | 5 | | | V-2 | Vmn2r27 | | |
| 8173 | 3 | 4 | 5 | | | V-2 | Tmprss11bnl | 403136 | 4-May-15 | 8267 | 3 | 4 | 5 | | | V-2 | Vmn2r3 | | |
| 8174 | 3 | 4 | 5 | | | V-2 | Tmprss15 | 5651 | 7-Jun-15 | 8268 | 3 | 4 | 5 | | | V-2 | Vmn2r85 | | |
| 8175 | 3 | 4 | 5 | | | V-2 | Tmprss5 | 80975 | 12-May-15 | 8269 | 3 | 4 | 5 | | | V-2 | Vps13b | 157680 | 23-May-15 |
| 8176 | 3 | 4 | 5 | | | V-2 | Tmub1 | 83590 | 29-May-15 | 8270 | 3 | 4 | 5 | | | V-2 | Vps35 | 55737 | 23-May-15 |
| 8177 | 3 | 4 | 5 | | | V-2 | Tmx3 | 54495 | 4-May-15 | 8271 | 3 | 4 | 5 | | | V-2 | Vstm2a | 222008 | 4-May-15 |
| 8178 | 3 | 4 | 5 | | | V-2 | Tnfrsf18 | 8784 | 3-May-15 | 8272 | 3 | 4 | 5 | | | V-2 | Vstm2l | 128434 | 4-May-15 |
| 8179 | 3 | 4 | 5 | | | V-2 | Tnfrsf9 | 3604 | 24-May-15 | 8273 | 3 | 4 | 5 | | | V-2 | Vti1a | 143187 | 21-May-15 |
| 8180 | 3 | 4 | 5 | | | V-2 | Tnfsf18 | 8995 | 30-Apr-15 | 8274 | 3 | 4 | 5 | | | V-2 | Vti1b | 10490 | 21-May-15 |
| 8181 | 3 | 4 | 5 | | | V-2 | Tnk2os | | | 8275 | 3 | 4 | 5 | | | V-2 | Vwa9 | 81556 | 4-May-15 |
| 8182 | 3 | 4 | 5 | | | V-2 | Tomm22 | 56993 | 4-May-15 | 8276 | 3 | 4 | 5 | | | V-2 | Vwde | 221806 | 7-Jun-15 |
| 8183 | 3 | 4 | 5 | | | V-2 | Tomm5 | 401505 | 12-May-15 | 8277 | 3 | 4 | 5 | | | V-2 | Wasf2 | 10163 | 4-May-15 |
| 8184 | 3 | 4 | 5 | | | V-2 | Tomm6 | 100188893 | 4-May-15 | 8278 | 3 | 4 | 5 | | | V-2 | Wash | 100287171 | 7-Jun-15 |
| 8185 | 3 | 4 | 5 | | | V-2 | Tpgs2 | 25941 | 4-May-15 | 8279 | 3 | 4 | 5 | | | V-2 | Wdfy1 | 57590 | 4-May-15 |
| 8186 | 3 | 4 | 5 | | | V-2 | Tpo | 7173 | 12-May-15 | 8280 | 3 | 4 | 5 | | | V-2 | Wdr1 | 9948 | 14-May-15 |
| 8187 | 3 | 4 | 5 | | | V-2 | Tprn | 286262 | 4-May-15 | 8281 | 3 | 4 | 5 | | | V-2 | Wdr17 | 116966 | 4-May-15 |
| 8188 | 3 | 4 | 5 | | | V-2 | Tradd | 8717 | 4-May-15 | 8282 | 3 | 4 | 5 | | | V-2 | Wdr20 | 91833 | 3-May-15 |
| 8189 | 3 | 4 | 5 | | | V-2 | Tram1l1 | 133022 | 4-May-15 | 8283 | 3 | 4 | 5 | | | V-2 | Wdr33 | 55339 | 4-May-15 |
| 8190 | 3 | 4 | 5 | | | V-2 | Trappc3 | 27095 | 2-Jun-15 | 8284 | 3 | 4 | 5 | | | V-2 | Wdr38 | 401551 | 4-May-15 |
| 8191 | 3 | 4 | 5 | | | V-2 | Treh | 11181 | 12-May-15 | 8285 | 3 | 4 | 5 | | | V-2 | Wdr47 | 22911 | 4-May-15 |
| 8192 | 3 | 4 | 5 | | | V-2 | Trim2 | 23321 | 4-May-15 | 8286 | 3 | 4 | 5 | | | V-2 | Wdr53 | 348793 | 4-May-15 |
| 8193 | 3 | 4 | 5 | | | V-2 | Trim33 | 51592 | 23-May-15 | 8287 | 3 | 4 | 5 | | | V-2 | Wdr55 | 54853 | 4-May-15 |
| 8194 | 3 | 4 | 5 | | | V-2 | Trim39 | 56658 | 2-Jun-15 | 8288 | 3 | 4 | 5 | | | V-2 | Wdr64 | 128025 | 4-May-15 |
| 8195 | 3 | 4 | 5 | | | V-2 | Trim56 | 83844 | 4-May-15 | 8289 | 3 | 4 | 5 | | | V-2 | Wdr8 | 49856 | 12-May-15 |
| 8196 | 3 | 4 | 5 | | | V-2 | Trim71 | 131405 | 7-Jun-15 | 8290 | 3 | 4 | 5 | | | V-2 | Wdr89 | 112840 | 4-May-15 |
| 8197 | 3 | 4 | 5 | | | V-2 | Trip11 | 9321 | 6-May-15 | 8291 | 3 | 4 | 5 | | | V-2 | Wdtc1 | 23038 | 21-May-15 |
| 8198 | 3 | 4 | 5 | | | V-2 | Trit1 | 54802 | 4-May-15 | 8292 | 3 | 4 | 5 | | | V-2 | Wiz | 58525 | 4-May-15 |
| 8199 | 3 | 4 | 5 | | | V-2 | Trmt6 | 51605 | 4-May-15 | 8293 | 3 | 4 | 5 | | | V-2 | Wnk3 | 65267 | 4-May-15 |
| 8200 | 3 | 4 | 5 | | | V-2 | Trp53cor1 | 102800311 | 23-May-15 | 8294 | 3 | 4 | 5 | | | V-2 | Wnt11 | 7481 | 12-May-15 |
| 8201 | 3 | 4 | 5 | | | V-2 | Trpa1 | 8989 | 7-Jun-15 | 8295 | 3 | 4 | 5 | | | V-2 | Wnt8a | 7478 | 7-Jun-15 |
| 8202 | 3 | 4 | 5 | | | V-2 | Trpc2 | 7221 | 12-May-15 | 8296 | 3 | 4 | 5 | | | V-2 | Wnt9b | 7484 | 4-May-15 |
| 8203 | 3 | 4 | 5 | | | V-2 | Trpm6 | 140803 | 4-May-15 | 8297 | 3 | 4 | 5 | | | V-2 | Xcr1 | 2829 | 4-May-15 |
| 8204 | 3 | 4 | 5 | | | V-2 | Trpm7 | 54822 | 4-May-15 | 8298 | 3 | 4 | 5 | | | V-2 | Xpo1 | 7514 | 24-May-15 |
| 8205 | 3 | 4 | 5 | | | V-2 | Trpv5 | 56302 | 12-May-15 | 8299 | 3 | 4 | 5 | | | V-2 | Yap1 | 10413 | 31-May-15 |
| 8206 | 3 | 4 | 5 | | | V-2 | Trub2 | 26995 | 12-May-15 | 8300 | 3 | 4 | 5 | | | V-2 | Ybey | 54059 | 4-May-15 |
| 8207 | 3 | 4 | 5 | | | V-2 | Tsc1 | 7248 | 13-Jun-15 | 8301 | 3 | 4 | 5 | | | V-2 | Ybx1 | 4904 | 2-Jun-15 |
| 8208 | 3 | 4 | 5 | | | V-2 | Tsg101 | 7251 | 1-Jun-15 | 8302 | 3 | 4 | 5 | | | V-2 | Ybx3 | 8531 | 12-May-15 |
| 8209 | 3 | 4 | 5 | | | V-2 | Tsn | 7247 | 3-May-15 | 8303 | 3 | 4 | 5 | | | V-2 | Yipf5 | 81555 | 4-May-15 |
| 8210 | 3 | 4 | 5 | | | V-2 | Tspan11 | 441631 | 12-May-15 | 8304 | 3 | 4 | 5 | | | V-2 | Ywhae | 7531 | 4-May-15 |
| 8211 | 3 | 4 | 5 | | | V-2 | Tspan5 | 10098 | 4-May-15 | 8305 | 3 | 4 | 5 | | | V-2 | Zc3h7a | 29066 | 4-May-15 |
| 8212 | 3 | 4 | 5 | | | V-2 | Tspyl5 | 85453 | 4-May-15 | 8306 | 3 | 4 | 5 | | | V-2 | Zc3hav1 | 56829 | 4-May-15 |
| 8213 | 3 | 4 | 5 | | | V-2 | Tsx | | | 8307 | 3 | 4 | 5 | | | V-2 | Zcchc6 | 79670 | 12-May-15 |
| 8214 | 3 | 4 | 5 | | | V-2 | Ttc13 | 79953 | 4-May-15 | 8308 | 3 | 4 | 5 | | | V-2 | Zfand2a | 90637 | 4-May-15 |
| 8215 | 3 | 4 | 5 | | | V-2 | Ttc19 | 54902 | 4-May-15 | 8309 | 3 | 4 | 5 | | | V-2 | Zfhx2os | | |
| 8216 | 3 | 4 | 5 | | | V-2 | Ttc21b | 79809 | 22-May-15 | 8310 | 3 | 4 | 5 | | | V-2 | Zfp101 | | |
| 8217 | 3 | 4 | 5 | | | V-2 | Ttc23 | 64927 | 4-May-15 | 8311 | 3 | 4 | 5 | | | V-2 | Zfp109 | | |
| 8218 | 3 | 4 | 5 | | | V-2 | Ttc23l | 153657 | 22-May-15 | 8312 | 3 | 4 | 5 | | | V-2 | Zfp113 | 7551 | 12-May-15 |
| 8219 | 3 | 4 | 5 | | | V-2 | Ttc27 | 55622 | 12-May-15 | 8313 | 3 | 4 | 5 | | | V-2 | Zfp14 | 57677 | 4-May-15 |
| 8220 | 3 | 4 | 5 | | | V-2 | Ttc30a2 | | | 8314 | 3 | 4 | 5 | | | V-2 | Zfp142 | | |
| 8221 | 3 | 4 | 5 | | | V-2 | Ttc30b | 150737 | 4-May-15 | 8315 | 3 | 4 | 5 | | | V-2 | Zfp160 | | |
| 8222 | 3 | 4 | 5 | | | V-2 | Ttc32 | 130502 | 12-May-15 | 8316 | 3 | 4 | 5 | | | V-2 | Zfp202 | | |
| 8223 | 3 | 4 | 5 | | | V-2 | Ttc34 | 100287898 | 4-May-15 | 8317 | 3 | 4 | 5 | | | V-2 | Zfp326 | 284695 | 4-May-15 |
| 8224 | 3 | 4 | 5 | | | V-2 | Ttc36 | 143941 | 4-May-15 | 8318 | 3 | 4 | 5 | | | V-2 | Zfp385c | | |
| 8225 | 3 | 4 | 5 | | | V-2 | Ttc37 | 9652 | 4-May-15 | 8319 | 3 | 4 | 5 | | | V-2 | Zfp395 | | |
| 8226 | 3 | 4 | 5 | | | V-2 | Ttc39c | 125488 | 12-May-15 | 8320 | 3 | 4 | 5 | | | V-2 | Zfp451 | | |
| 8227 | 3 | 4 | 5 | | | V-2 | Ttc39d | | | 8321 | 3 | 4 | 5 | | | V-2 | Zfp472 | | |
| 8228 | 3 | 4 | 5 | | | V-2 | Ttll10 | 254173 | 12-May-15 | 8322 | 3 | 4 | 5 | | | V-2 | Zfp488 | | |
| 8229 | 3 | 4 | 5 | | | V-2 | Ttll6 | 284076 | 12-May-15 | 8323 | 3 | 4 | 5 | | | V-2 | Zfp534 | | |
| 8230 | 3 | 4 | 5 | | | V-2 | Ttr | 7273 | 23-May-15 | 8324 | 3 | 4 | 5 | | | V-2 | Zfp536 | | |
| 8231 | 3 | 4 | 5 | | | V-2 | Txndc11 | 51061 | 12-May-15 | 8325 | 3 | 4 | 5 | | | V-2 | Zfp605 | | |
| 8232 | 3 | 4 | 5 | | | V-2 | Txnrd1 | 7296 | 14-May-15 | 8326 | 3 | 4 | 5 | | | V-2 | Zfp606 | | |
| 8233 | 3 | 4 | 5 | | | V-2 | Tyw5 | 129450 | 4-May-15 | 8327 | 3 | 4 | 5 | | | V-2 | Zfp646 | | |
| 8234 | 3 | 4 | 5 | | | V-2 | Uap1 | 6675 | 4-May-15 | 8328 | 3 | 4 | 5 | | | V-2 | Zfp647 | 58500 | 4-May-15 |
| 8235 | 3 | 4 | 5 | | | V-2 | Ube2e3 | 10477 | 4-May-15 | 8329 | 3 | 4 | 5 | | | V-2 | Zfp652 | | |
| 8236 | 3 | 4 | 5 | | | V-2 | Ubr3 | 130507 | 4-May-15 | 8330 | 3 | 4 | 5 | | | V-2 | Zfp868 | | |
| 8237 | 3 | 4 | 5 | | | V-2 | Ubxn2a | 165324 | 21-May-15 | 8331 | 3 | 4 | 5 | | | V-2 | Zfp711 | 7552 | 4-May-15 |
| 8238 | 3 | 4 | 5 | | | V-2 | Ugt2b1 | | | 8332 | 3 | 4 | 5 | | | V-2 | Zfp760 | | |
| 8239 | 3 | 4 | 5 | | | V-2 | Ugt2b36 | | | 8333 | 3 | 4 | 5 | | | V-2 | Zfp764 | | |
| 8240 | 3 | 4 | 5 | | | V-2 | Ugt2b38 | | | 8334 | 3 | 4 | 5 | | | V-2 | Zfp771 | | |
| | | | | | | | | | | 8335 | 3 | 4 | 5 | | | V-2 | Zfp784 | | |

Fig. 30 - 45

| | | | | | | | | | | | | | | | | |
|---|---|---|---|---|---|---|---|---|---|---|---|---|---|---|---|---|
| 8336 | 3 | 4 | 5 | | | V-2 | Zfp800 | | | 8429 | 3 | 4 | 5 | | | V-1 | 1700111N16Rik | |
| 8337 | 3 | 4 | 5 | | | V-2 | Zfp821 | | | 8430 | 3 | 4 | 5 | | | V-1 | 1700112H15Rik | |
| 8338 | 3 | 4 | 5 | | | V-2 | Zfp94 | | | 8431 | 3 | 4 | 5 | | | V-1 | 1700120E14Rik | |
| 8339 | 3 | 4 | 5 | | | V-2 | Zfp957 | | | 8432 | 3 | 4 | 5 | | | V-1 | 1700120K04Rik | |
| 8340 | 3 | 4 | 5 | | | V-2 | Zfp961 | | | 8433 | 3 | 4 | 5 | | | V-1 | 1700128F08Rik | |
| 8341 | 3 | 4 | 5 | | | V-2 | Zfpl1 | 7542 | 4-May-15 | 8434 | 3 | 4 | 5 | | | V-1 | 1810009A15Rik | |
| 8342 | 3 | 4 | 5 | | | V-2 | Zfr | 51663 | 12-May-15 | 8435 | 3 | 4 | 5 | | | V-1 | 1810010H24Rik | |
| 8343 | 3 | 4 | 5 | | | V-2 | Zgpat | 84619 | 12-May-15 | 8436 | 3 | 4 | 5 | | | V-1 | 1810012K16Rik | |
| 8344 | 3 | 4 | 5 | | | V-2 | Zkscan8 | 7745 | 14-May-15 | 8437 | 3 | 4 | 5 | | | V-1 | 1810013A23Rik | |
| 8345 | 3 | 4 | 5 | | | V-2 | Zmat2 | 153527 | 4-May-15 | 8438 | 3 | 4 | 5 | | | V-1 | 1810013L24Rik | |
| 8346 | 3 | 4 | 5 | | | V-2 | Znhit2 | 741 | 4-May-15 | 8439 | 3 | 4 | 5 | | | V-1 | 1810021B22Rik | |
| 8347 | 3 | 4 | 5 | | | V-2 | Znrf4 | 148066 | 4-May-15 | 8440 | 3 | 4 | 5 | | | V-1 | 1810022K09Rik | |
| 8348 | 3 | 4 | 5 | | | V-2 | Zscan20 | 7579 | 4-May-15 | 8441 | 3 | 4 | 5 | | | V-1 | 1810024B03Rik | |
| 8349 | 3 | 4 | 5 | | | V-2 | Zscan21 | 7589 | 28-May-15 | 8442 | 3 | 4 | 5 | | | V-1 | 1810034E14Rik | |
| 8350 | 3 | 4 | 5 | | | V-2 | Zswim8 | 23053 | 12-May-15 | 8443 | 3 | 4 | 5 | | | V-1 | 1810037I17Rik | |
| 8351 | 3 | 4 | 5 | | | V-1 | 0610009O20Rik | | | 8444 | 3 | 4 | 5 | | | V-1 | 1810053B23Rik | |
| 8352 | 3 | 4 | 5 | | | V-1 | 0610010F05Rik | | | 8445 | 3 | 4 | 5 | | | V-1 | 1810058I24Rik | |
| 8353 | 3 | 4 | 5 | | | V-1 | 0610037L13Rik | | | 8446 | 3 | 4 | 5 | | | V-1 | 1810062O18Rik | |
| 8354 | 3 | 4 | 5 | | | V-1 | 0610040B10Rik | | | 8447 | 3 | 4 | 5 | | | V-1 | 2010009K17Rik | |
| 8355 | 3 | 4 | 5 | | | V-1 | 0610040F04Rik | | | 8448 | 3 | 4 | 5 | | | V-1 | 2010106C02Rik | |
| 8356 | 3 | 4 | 5 | | | V-1 | 0610043K17Rik | | | 8449 | 3 | 4 | 5 | | | V-1 | 2010107E04Rik | |
| 8357 | 3 | 4 | 5 | | | V-1 | 1110001J03Rik | | | 8450 | 3 | 4 | 5 | | | V-1 | 2010107G12Rik | |
| 8358 | 3 | 4 | 5 | | | V-1 | 1110038F14Rik | | | 8451 | 3 | 4 | 5 | | | V-1 | 2010109I03Rik | |
| 8359 | 3 | 4 | 5 | | | V-1 | 1110051M20Rik | | | 8452 | 3 | 4 | 5 | | | V-1 | 2010308F09Rik | |
| 8360 | 3 | 4 | 5 | | | V-1 | 1190002N15Rik | | | 8453 | 3 | 4 | 5 | | | V-1 | 2200002J24Rik | |
| 8361 | 3 | 4 | 5 | | | V-1 | 1200014J11Rik | | | 8454 | 3 | 4 | 5 | | | V-1 | 2210011C24Rik | |
| 8362 | 3 | 4 | 5 | | | V-1 | 1500004A13Rik | | | 8455 | 3 | 4 | 5 | | | V-1 | 2210013O21Rik | |
| 8363 | 3 | 4 | 5 | | | V-1 | 1500009C09Rik | | | 8456 | 3 | 4 | 5 | | | V-1 | 2230404O09Rik | |
| 8364 | 3 | 4 | 5 | | | V-1 | 1500011K16Rik | | | 8457 | 3 | 4 | 5 | | | V-1 | 2210408F21Rik | |
| 8365 | 3 | 4 | 5 | | | V-1 | 1500012K07Rik | | | 8458 | 3 | 4 | 5 | | | V-1 | 2300003K06Rik | |
| 8366 | 3 | 4 | 5 | | | V-1 | 1500015L24Rik | | | 8459 | 3 | 4 | 5 | | | V-1 | 2300009A05Rik | |
| 8367 | 3 | 4 | 5 | | | V-1 | 1500017E21Rik | | | 8460 | 3 | 4 | 5 | | | V-1 | 2310002D06Rik | |
| 8368 | 3 | 4 | 5 | | | V-1 | 1600002K03Rik | | | 8461 | 3 | 4 | 5 | | | V-1 | 2310002L09Rik | |
| 8369 | 3 | 4 | 5 | | | V-1 | 1600012H06Rik | | | 8462 | 3 | 4 | 5 | | | V-1 | 2310003H01Rik | |
| 8370 | 3 | 4 | 5 | | | V-1 | 1600014K23Rik | | | 8463 | 3 | 4 | 5 | | | V-1 | 2310010J17Rik | |
| 8371 | 3 | 4 | 5 | | | V-1 | 1600019K03Rik | | | 8464 | 3 | 4 | 5 | | | V-1 | 2310011J03Rik | |
| 8372 | 3 | 4 | 5 | | | V-1 | 1600023N17Rik | | | 8465 | 3 | 4 | 5 | | | V-1 | 2310015A10Rik | |
| 8373 | 3 | 4 | 5 | | | V-1 | 1600029O15Rik | | | 8466 | 3 | 4 | 5 | | | V-1 | 2310015D24Rik | |
| 8374 | 3 | 4 | 5 | | | V-1 | 1700001D01Rik | | | 8467 | 3 | 4 | 5 | | | V-1 | 2310030A07Rik | |
| 8375 | 3 | 4 | 5 | | | V-1 | 1700001G11Rik | | | 8468 | 3 | 4 | 5 | | | V-1 | 2310033P09Rik | |
| 8376 | 3 | 4 | 5 | | | V-1 | 1700001L19Rik | | | 8469 | 3 | 4 | 5 | | | V-1 | 2310035C23Rik | |
| 8377 | 3 | 4 | 5 | | | V-1 | 1700001P01Rik | | | 8470 | 3 | 4 | 5 | | | V-1 | 2310043L19Rik | |
| 8378 | 3 | 4 | 5 | | | V-1 | 1700006A11Rik | | | 8471 | 3 | 4 | 5 | | | V-1 | 2310057N15Rik | |
| 8379 | 3 | 4 | 5 | | | V-1 | 1700007P06Rik | | | 8472 | 3 | 4 | 5 | | | V-1 | 2310069B03Rik | |
| 8380 | 3 | 4 | 5 | | | V-1 | 1700010B08Rik | | | 8473 | 3 | 4 | 5 | | | V-1 | 2410003L11Rik | |
| 8381 | 3 | 4 | 5 | | | V-1 | 1700010I14Rik | | | 8474 | 3 | 4 | 5 | | | V-1 | 2410004B18Rik | |
| 8382 | 3 | 4 | 5 | | | V-1 | 1700010J16Rik | | | 8475 | 3 | 4 | 5 | | | V-1 | 2410007B07Rik | |
| 8383 | 3 | 4 | 5 | | | V-1 | 1700012B07Rik | | | 8476 | 3 | 4 | 5 | | | V-1 | 2410018L13Rik | |
| 8384 | 3 | 4 | 5 | | | V-1 | 1700012I11Rik | | | 8477 | 3 | 4 | 5 | | | V-1 | 2410088I16Rik | |
| 8385 | 3 | 4 | 5 | | | V-1 | 1700016D06Rik | | | 8478 | 3 | 4 | 5 | | | V-1 | 2610002M06Rik | |
| 8386 | 3 | 4 | 5 | | | V-1 | 1700016L04Rik | | | 8479 | 3 | 4 | 5 | | | V-1 | 2610005L07Rik | |
| 8387 | 3 | 4 | 5 | | | V-1 | 1700017D01Rik | | | 8480 | 3 | 4 | 5 | | | V-1 | 2610018G03Rik | |
| 8388 | 3 | 4 | 5 | | | V-1 | 1700018L02Rik | | | 8481 | 3 | 4 | 5 | | | V-1 | 2610020C07Rik | |
| 8389 | 3 | 4 | 5 | | | V-1 | 1700019A02Rik | | | 8482 | 3 | 4 | 5 | | | V-1 | 2610027K06Rik | |
| 8390 | 3 | 4 | 5 | | | V-1 | 1700019E08Rik | | | 8483 | 3 | 4 | 5 | | | V-1 | 2610028E06Rik | |
| 8391 | 3 | 4 | 5 | | | V-1 | 1700019G24Rik | | | 8484 | 3 | 4 | 5 | | | V-1 | 2610034B18Rik | |
| 8392 | 3 | 4 | 5 | | | V-1 | 1700019L03Rik | | | 8485 | 3 | 4 | 5 | | | V-1 | 2610100L16Rik | |
| 8393 | 3 | 4 | 5 | | | V-1 | 1700019O17Rik | | | 8486 | 3 | 4 | 5 | | | V-1 | 2610301B20Rik | |
| 8394 | 3 | 4 | 5 | | | V-1 | 1700020M21Rik | | | 8487 | 3 | 4 | 5 | | | V-1 | 2610306M01Rik | |
| 8395 | 3 | 4 | 5 | | | V-1 | 1700021F05Rik | | | 8488 | 3 | 4 | 5 | | | V-1 | 2610316D01Rik | |
| 8396 | 3 | 4 | 5 | | | V-1 | 1700024B18Rik | | | 8489 | 3 | 4 | 5 | | | V-1 | 2610507B11Rik | |
| 8397 | 3 | 4 | 5 | | | V-1 | 1700024F13Rik | | | 8490 | 3 | 4 | 5 | | | V-1 | 2610528J11Rik | |
| 8398 | 3 | 4 | 5 | | | V-1 | 1700024P04Rik | | | 8491 | 3 | 4 | 5 | | | V-1 | 2700029M09Rik | |
| 8399 | 3 | 4 | 5 | | | V-1 | 1700025B11Rik | | | 8492 | 3 | 4 | 5 | | | V-1 | 2700038G22Rik | |
| 8400 | 3 | 4 | 5 | | | V-1 | 1700025K24Rik | | | 8493 | 3 | 4 | 5 | | | V-1 | 2700046A07Rik | |
| 8401 | 3 | 4 | 5 | | | V-1 | 1700028B04Rik | | | 8494 | 3 | 4 | 5 | | | V-1 | 2700049A03Rik | |
| 8402 | 3 | 4 | 5 | | | V-1 | 1700028D13Rik | | | 8495 | 3 | 4 | 5 | | | V-1 | 2700069I18Rik | |
| 8403 | 3 | 4 | 5 | | | V-1 | 1700029H14Rik | | | 8496 | 3 | 4 | 5 | | | V-1 | 2700089E24Rik | |
| 8404 | 3 | 4 | 5 | | | V-1 | 1700029J03Rik | | | 8497 | 3 | 4 | 5 | | | V-1 | 2700097O09Rik | |
| 8405 | 3 | 4 | 5 | | | V-1 | 1700029M20Rik | | | 8498 | 3 | 4 | 5 | | | V-1 | 2810001G20Rik | |
| 8406 | 3 | 4 | 5 | | | V-1 | 1700039E15Rik | | | 8499 | 3 | 4 | 5 | | | V-1 | 2810006K23Rik | |
| 8407 | 3 | 4 | 5 | | | V-1 | 1700046C09Rik | | | 8500 | 3 | 4 | 5 | | | V-1 | 2810007J24Rik | |
| 8408 | 3 | 4 | 5 | | | V-1 | 1700047I17Rik2 | | | 8501 | 3 | 4 | 5 | | | V-1 | 2810013P06Rik | |
| 8409 | 3 | 4 | 5 | | | V-1 | 1700048M11Rik | | | 8502 | 3 | 4 | 5 | | | V-1 | 2810032G03Rik | |
| 8410 | 3 | 4 | 5 | | | V-1 | 1700049E22Rik | | | 8503 | 3 | 4 | 5 | | | V-1 | 2810408M09Rik | |
| 8411 | 3 | 4 | 5 | | | V-1 | 1700063A18Rik | | | 8504 | 3 | 4 | 5 | | | V-1 | 2810428I15Rik | |
| 8412 | 3 | 4 | 5 | | | V-1 | 1700067G17Rik | | | 8505 | 3 | 4 | 5 | | | V-1 | 2810468N07Rik | |
| 8413 | 3 | 4 | 5 | | | V-1 | 1700067P10Rik | | | 8506 | 3 | 4 | 5 | | | V-1 | 2900011O08Rik | |
| 8414 | 3 | 4 | 5 | | | V-1 | 1700072B07Rik | | | 8507 | 3 | 4 | 5 | | | V-1 | 2900055J20Rik | |
| 8415 | 3 | 4 | 5 | | | V-1 | 1700074P13Rik | | | 8508 | 3 | 4 | 5 | | | V-1 | 2900092C05Rik | |
| 8416 | 3 | 4 | 5 | | | V-1 | 1700084F23Rik | | | 8509 | 3 | 4 | 5 | | | V-1 | 2900097C17Rik | |
| 8417 | 3 | 4 | 5 | | | V-1 | 1700085C21Rik | | | 8510 | 3 | 4 | 5 | | | V-1 | 3010001F23Rik | |
| 8418 | 3 | 4 | 5 | | | V-1 | 1700091H14Rik | | | 8511 | 3 | 4 | 5 | | | V-1 | 3100003L05Rik | |
| 8419 | 3 | 4 | 5 | | | V-1 | 1700092E19Rik | | | 8512 | 3 | 4 | 5 | | | V-1 | 3110002H16Rik | |
| 8420 | 3 | 4 | 5 | | | V-1 | 1700093K21Rik | | | 8513 | 3 | 4 | 5 | | | V-1 | 3110009F21Rik | |
| 8421 | 3 | 4 | 5 | | | V-1 | 1700094J05Rik | | | 8514 | 3 | 4 | 5 | | | V-1 | 3110045C21Rik | |
| 8422 | 3 | 4 | 5 | | | V-1 | 1700095B10Rik | | | 8515 | 3 | 4 | 5 | | | V-1 | 3110070M22Rik | |
| 8423 | 3 | 4 | 5 | | | V-1 | 1700100L14Rik | | | 8516 | 3 | 4 | 5 | | | V-1 | 3110079O15Rik | |
| 8424 | 3 | 4 | 5 | | | V-1 | 1700101I11Rik | | | 8517 | 3 | 4 | 5 | | | V-1 | 3110082J24Rik | |
| 8425 | 3 | 4 | 5 | | | V-1 | 1700101O22Rik | | | 8518 | 3 | 4 | 5 | | | V-1 | 3425401B19Rik | |
| 8426 | 3 | 4 | 5 | | | V-1 | 1700102P08Rik | | | 8519 | 3 | 4 | 5 | | | V-1 | 3632454L22Rik | |
| 8427 | 3 | 4 | 5 | | | V-1 | 1700104L18Rik | | | 8520 | 3 | 4 | 5 | | | V-1 | 3830406C13Rik | |
| 8428 | 3 | 4 | 5 | | | V-1 | 1700109I08Rik | | | | | | | | | | | |

Fig. 30 - 46

| | | | | | | | | |
|---|---|---|---|---|---|---|---|---|
| 8521 | 3 | 4 | 5 | | | V-1 | 4632427E13Rik | |
| 8522 | 3 | 4 | 5 | | | V-1 | 4632428N05Rik | |
| 8523 | 3 | 4 | 5 | | | V-1 | 4732416N19Rik | |
| 8524 | 3 | 4 | 5 | | | V-1 | 4732456N10Rik | |
| 8525 | 3 | 4 | 5 | | | V-1 | 4732490B19Rik | |
| 8526 | 3 | 4 | 5 | | | V-1 | 4833411C07Rik | |
| 8527 | 3 | 4 | 5 | | | V-1 | 4833417C18Rik | |
| 8528 | 3 | 4 | 5 | | | V-1 | 4833419F23Rik | |
| 8529 | 3 | 4 | 5 | | | V-1 | 4921508D12Rik | |
| 8530 | 3 | 4 | 5 | | | V-1 | 4921531P14Rik | |
| 8531 | 3 | 4 | 5 | | | V-1 | 4921534H16Rik | |
| 8532 | 3 | 4 | 5 | | | V-1 | 4930404A10Rik | |
| 8533 | 3 | 4 | 5 | | | V-1 | 4930405A10Rik | |
| 8534 | 3 | 4 | 5 | | | V-1 | 4930405L22Rik | |
| 8535 | 3 | 4 | 5 | | | V-1 | 4930413E15Rik | |
| 8536 | 3 | 4 | 5 | | | V-1 | 4930413G21Rik | |
| 8537 | 3 | 4 | 5 | | | V-1 | 4930426L09Rik | |
| 8538 | 3 | 4 | 5 | | | V-1 | 4930428D18Rik | |
| 8539 | 3 | 4 | 5 | | | V-1 | 4930430A15Rik | |
| 8540 | 3 | 4 | 5 | | | V-1 | 4930430F21Rik | |
| 8541 | 3 | 4 | 5 | | | V-1 | 4930432J09Rik | |
| 8542 | 3 | 4 | 5 | | | V-1 | 4930441J16Rik | |
| 8543 | 3 | 4 | 5 | | | V-1 | 4930443O20Rik | |
| 8544 | 3 | 4 | 5 | | | V-1 | 4930447J18Rik | |
| 8545 | 3 | 4 | 5 | | | V-1 | 4930449I24Rik | |
| 8546 | 3 | 4 | 5 | | | V-1 | 4930451I11Rik | |
| 8547 | 3 | 4 | 5 | | | V-1 | 4930455D15Rik | |
| 8548 | 3 | 4 | 5 | | | V-1 | 4930469G21Rik | |
| 8549 | 3 | 4 | 5 | | | V-1 | 4930473A02Rik | |
| 8550 | 3 | 4 | 5 | | | V-1 | 4930480K15Rik | |
| 8551 | 3 | 4 | 5 | | | V-1 | 4930482G09Rik | |
| 8552 | 3 | 4 | 5 | | | V-1 | 4930483O08Rik | |
| 8553 | 3 | 4 | 5 | | | V-1 | 4930487D11Rik | |
| 8554 | 3 | 4 | 5 | | | V-1 | 4930503B20Rik | |
| 8555 | 3 | 4 | 5 | | | V-1 | 4930503E14Rik | |
| 8556 | 3 | 4 | 5 | | | V-1 | 4930503O07Rik | |
| 8557 | 3 | 4 | 5 | | | V-1 | 4930504O13Rik | |
| 8558 | 3 | 4 | 5 | | | V-1 | 4930507D05Rik | |
| 8559 | 3 | 4 | 5 | | | V-1 | 4930513O06Rik | |
| 8560 | 3 | 4 | 5 | | | V-1 | 4930517E11Rik | |
| 8561 | 3 | 4 | 5 | | | V-1 | 4930523O13Rik | |
| 8562 | 3 | 4 | 5 | | | V-1 | 4930525D18Rik | |
| 8563 | 3 | 4 | 5 | | | V-1 | 4930526I15Rik | |
| 8564 | 3 | 4 | 5 | | | V-1 | 4930529C04Rik | |
| 8565 | 3 | 4 | 5 | | | V-1 | 4930533B01Rik | |
| 8566 | 3 | 4 | 5 | | | V-1 | 4930539M17Rik | |
| 8567 | 3 | 4 | 5 | | | V-1 | 4930562C15Rik | |
| 8568 | 3 | 4 | 5 | | | V-1 | 4930563D23Rik | |
| 8569 | 3 | 4 | 5 | | | V-1 | 4930573O16Rik | |
| 8570 | 3 | 4 | 5 | | | V-1 | 4930577N17Rik | |
| 8571 | 3 | 4 | 5 | | | V-1 | 4930581F22Rik | |
| 8572 | 3 | 4 | 5 | | | V-1 | 4931408D14Rik | |
| 8573 | 3 | 4 | 5 | | | V-1 | 4931409K22Rik | |
| 8574 | 3 | 4 | 5 | | | V-1 | 4931428L18Rik | |
| 8575 | 3 | 4 | 5 | | | V-1 | 4931429L15Rik | |
| 8576 | 3 | 4 | 5 | | | V-1 | 4931431F19Rik | |
| 8577 | 3 | 4 | 5 | | | V-1 | 4932441J04Rik | |
| 8578 | 3 | 4 | 5 | | | V-1 | 4933405D12Rik | |
| 8579 | 3 | 4 | 5 | | | V-1 | 4933406D12Rik | |
| 8580 | 3 | 4 | 5 | | | V-1 | 4933406J08Rik | |
| 8581 | 3 | 4 | 5 | | | V-1 | 4933407L21Rik | |
| 8582 | 3 | 4 | 5 | | | V-1 | 4933411E08Rik | |
| 8583 | 3 | 4 | 5 | | | V-1 | 4933412E24Rik | |
| 8584 | 3 | 4 | 5 | | | V-1 | 4933422A05Rik | |
| 8585 | 3 | 4 | 5 | | | V-1 | 4933427D06Rik | |
| 8586 | 3 | 4 | 5 | | | V-1 | 4933428C19Rik | |
| 8587 | 3 | 4 | 5 | | | V-1 | 4933431G14Rik | |
| 8588 | 3 | 4 | 5 | | | V-1 | 4933434E20Rik | |
| 8589 | 3 | 4 | 5 | | | V-1 | 4933438K21Rik | |
| 8590 | 3 | 4 | 5 | | | V-1 | 4933439K11Rik | |
| 8591 | 3 | 4 | 5 | | | V-1 | 5031425E22Rik | |
| 8592 | 3 | 4 | 5 | | | V-1 | 5031439G07Rik | |
| 8593 | 3 | 4 | 5 | | | V-1 | 5033404E19Rik | |
| 8594 | 3 | 4 | 5 | | | V-1 | 5133400J02Rik | |
| 8595 | 3 | 4 | 5 | | | V-1 | 5330426P16Rik | |
| 8596 | 3 | 4 | 5 | | | V-1 | 5330434G04Rik | |
| 8597 | 3 | 4 | 5 | | | V-1 | 5430416O09Rik | |
| 8598 | 3 | 4 | 5 | | | V-1 | 5430417L22Rik | |
| 8599 | 3 | 4 | 5 | | | V-1 | 5430428K19Rik | |
| 8600 | 3 | 4 | 5 | | | V-1 | 5430437J10Rik | |
| 8601 | 3 | 4 | 5 | | | V-1 | 5730409E04Rik | |
| 8602 | 3 | 4 | 5 | | | V-1 | 5730420D15Rik | |
| 8603 | 3 | 4 | 5 | | | V-1 | 5730522E02Rik | |
| 8604 | 3 | 4 | 5 | | | V-1 | 5830411N06Rik | |
| 8605 | 3 | 4 | 5 | | | V-1 | 5830416I19Rik | |
| 8606 | 3 | 4 | 5 | | | V-1 | 5830417I10Rik | |
| 8607 | 3 | 4 | 5 | | | V-1 | 5830418K08Rik | |
| 8608 | 3 | 4 | 5 | | | V-1 | 5830454E08Rik | |
| 8609 | 3 | 4 | 5 | | | V-1 | 5830473C10Rik | |
| 8610 | 3 | 4 | 5 | | | V-1 | 5930412G12Rik | |
| 8611 | 3 | 4 | 5 | | | V-1 | 5930438M14Rik | |
| 8612 | 3 | 4 | 5 | | | V-1 | 6030419C18Rik | |
| 8613 | 3 | 4 | 5 | | | V-1 | 6030469F06Rik | |
| 8614 | 3 | 4 | 5 | | | V-1 | 6330407A03Rik | |
| 8615 | 3 | 4 | 5 | | | V-1 | 6330410L21Rik | |
| 8616 | 3 | 4 | 5 | | | V-1 | 6330419J24Rik | |
| 8617 | 3 | 4 | 5 | | | V-1 | 6330549D23Rik | |
| 8618 | 3 | 4 | 5 | | | V-1 | 6430550D23Rik | |
| 8619 | 3 | 4 | 5 | | | V-1 | 6430584L05Rik | |
| 8620 | 3 | 4 | 5 | | | V-1 | 6430710C18Rik | |
| 8621 | 3 | 4 | 5 | | | V-1 | 6720483E21Rik | |
| 8622 | 3 | 4 | 5 | | | V-1 | 6820431F20Rik | |
| 8623 | 3 | 4 | 5 | | | V-1 | 8430419L09Rik | |
| 8624 | 3 | 4 | 5 | | | V-1 | 8430427H17Rik | |
| 8625 | 3 | 4 | 5 | | | V-1 | 8430429K09Rik | |
| 8626 | 3 | 4 | 5 | | | V-1 | 9030612E09Rik | |
| 8627 | 3 | 4 | 5 | | | V-1 | 9030624G23Rik | |
| 8628 | 3 | 4 | 5 | | | V-1 | 9130024F11Rik | |
| 8629 | 3 | 4 | 5 | | | V-1 | 9130401M01Rik | |
| 8630 | 3 | 4 | 5 | | | V-1 | 9230105E05Rik | |
| 8631 | 3 | 4 | 5 | | | V-1 | 9230112D13Rik | |
| 8632 | 3 | 4 | 5 | | | V-1 | 9230116L04Rik | |
| 8633 | 3 | 4 | 5 | | | V-1 | 9330151L19Rik | |
| 8634 | 3 | 4 | 5 | | | V-1 | 9330158H04Rik | |
| 8635 | 3 | 4 | 5 | | | V-1 | 9330159M07Rik | |
| 8636 | 3 | 4 | 5 | | | V-1 | 9330162B11Rik | |
| 8637 | 3 | 4 | 5 | | | V-1 | 9330175M20Rik | |
| 8638 | 3 | 4 | 5 | | | V-1 | 9430014N10Rik | |
| 8639 | 3 | 4 | 5 | | | V-1 | 9430021M05Rik | |
| 8640 | 3 | 4 | 5 | | | V-1 | 9430041J12Rik | |
| 8641 | 3 | 4 | 5 | | | V-1 | 9430091I24Rik | |
| 8642 | 3 | 4 | 5 | | | V-1 | 9530003J23Rik | |
| 8643 | 3 | 4 | 5 | | | V-1 | 9530080O11Rik | |
| 8644 | 3 | 4 | 5 | | | V-1 | 9630001P10Rik | |
| 8645 | 3 | 4 | 5 | | | V-1 | 9830132P13Rik | |
| 8646 | 3 | 4 | 5 | | | V-1 | 9830147E19Rik | |
| 8647 | 3 | 4 | 5 | | | V-1 | 9930012K11Rik | |
| 8648 | 3 | 4 | 5 | | | V-1 | 9930111J21Rik2 | |
| 8649 | 3 | 4 | 5 | | | V-1 | a | |
| 8650 | 3 | 4 | 5 | | | V-1 | A230056J06Rik | |
| 8651 | 3 | 4 | 5 | | | V-1 | A230057D06Rik | |
| 8652 | 3 | 4 | 5 | | | V-1 | A330009N23Rik | |
| 8653 | 3 | 4 | 5 | | | V-1 | A330041J22Rik | |
| 8654 | 3 | 4 | 5 | | | V-1 | A330050F15Rik | |
| 8655 | 3 | 4 | 5 | | | V-1 | A330076C08Rik | |
| 8656 | 3 | 4 | 5 | | | V-1 | A430033K04Rik | |
| 8657 | 3 | 4 | 5 | | | V-1 | A430035B10Rik | |
| 8658 | 3 | 4 | 5 | | | V-1 | A430088P11Rik | |
| 8659 | 3 | 4 | 5 | | | V-1 | A4gnt | 51146 | 4-May-15 |
| 8660 | 3 | 4 | 5 | | | V-1 | A530032D15Rik | |
| 8661 | 3 | 4 | 5 | | | V-1 | A530046M15Rik | |
| 8662 | 3 | 4 | 5 | | | V-1 | A530054K11Rik | |
| 8663 | 3 | 4 | 5 | | | V-1 | A530065N20Rik | |
| 8664 | 3 | 4 | 5 | | | V-1 | A530099I19Rik | |
| 8665 | 3 | 4 | 5 | | | V-1 | A630007B06Rik | |
| 8666 | 3 | 4 | 5 | | | V-1 | A630066F11Rik | |
| 8667 | 3 | 4 | 5 | | | V-1 | A630089N07Rik | |
| 8668 | 3 | 4 | 5 | | | V-1 | A630095N17Rik | |
| 8669 | 3 | 4 | 5 | | | V-1 | A730017L22Rik | |
| 8670 | 3 | 4 | 5 | | | V-1 | A730043L09Rik | |
| 8671 | 3 | 4 | 5 | | | V-1 | A730090H04Rik | |
| 8672 | 3 | 4 | 5 | | | V-1 | A930003O13Rik | |
| 8673 | 3 | 4 | 5 | | | V-1 | A930007I19Rik | |
| 8674 | 3 | 4 | 5 | | | V-1 | A930015D03Rik | |
| 8675 | 3 | 4 | 5 | | | V-1 | A930041C12Rik | |
| 8676 | 3 | 4 | 5 | | | V-1 | AA413626 | |
| 8677 | 3 | 4 | 5 | | | V-1 | AA415398 | |
| 8678 | 3 | 4 | 5 | | | V-1 | AA474331 | |
| 8679 | 3 | 4 | 5 | | | V-1 | AA987161 | |
| 8680 | 3 | 4 | 5 | | | V-1 | Aarsd1 | 80755 | 4-May-15 |
| 8681 | 3 | 4 | 5 | | | V-1 | Aatf | 26574 | 12-May-15 |
| 8682 | 3 | 4 | 5 | | | V-1 | Aatk | 9625 | 4-May-15 |
| 8683 | 3 | 4 | 5 | | | V-1 | Abat | 18 | 4-May-15 |
| 8684 | 3 | 4 | 5 | | | V-1 | Abca12 | 26154 | 23-May-15 |
| 8685 | 3 | 4 | 5 | | | V-1 | Abca14 | | |
| 8686 | 3 | 4 | 5 | | | V-1 | Abca3 | 21 | 12-May-15 |
| 8687 | 3 | 4 | 5 | | | V-1 | Abca5 | 23461 | 4-May-15 |
| 8688 | 3 | 4 | 5 | | | V-1 | Abca7 | 10347 | 12-May-15 |
| 8689 | 3 | 4 | 5 | | | V-1 | Abca8b | | |
| 8690 | 3 | 4 | 5 | | | V-1 | Abcb11 | 8647 | 23-May-15 |
| 8691 | 3 | 4 | 5 | | | V-1 | Abcb1a | | |
| 8692 | 3 | 4 | 5 | | | V-1 | Abcb7 | 22 | 23-May-15 |
| 8693 | 3 | 4 | 5 | | | V-1 | Abcb8 | 11194 | 12-May-15 |
| 8694 | 3 | 4 | 5 | | | V-1 | Abcb9 | 23457 | 4-May-15 |
| 8695 | 3 | 4 | 5 | | | V-1 | Abcc1 | 4363 | 12-May-15 |
| 8696 | 3 | 4 | 5 | | | V-1 | Abcc12 | 94160 | 4-May-15 |
| 8697 | 3 | 4 | 5 | | | V-1 | Abcc4 | 10257 | 12-May-15 |
| 8698 | 3 | 4 | 5 | | | V-1 | Abcd1 | 215 | 7-Jun-15 |
| 8699 | 3 | 4 | 5 | | | V-1 | Abcd3 | 5825 | 7-Jun-15 |
| 8700 | 3 | 4 | 5 | | | V-1 | Abcg3 | | |
| 8701 | 3 | 4 | 5 | | | V-1 | Abcg5 | 64240 | 23-May-15 |
| 8702 | 3 | 4 | 5 | | | V-1 | Abhd10 | 55347 | 4-May-15 |
| 8703 | 3 | 4 | 5 | | | V-1 | Abhd12 | 26090 | 4-May-15 |
| 8704 | 3 | 4 | 5 | | | V-1 | Abhd16a | 7920 | 4-May-15 |
| 8705 | 3 | 4 | 5 | | | V-1 | Abhd6 | 57406 | 17-May-15 |
| 8706 | 3 | 4 | 5 | | | V-1 | Abl1 | 25 | 24-May-15 |

Fig. 30 - 47

| | | | | | | | | | | | | | | | | |
|---|---|---|---|---|---|---|---|---|---|---|---|---|---|---|---|---|
| 8707 | 3 | 4 | 5 | | | V-1 | Abr | 29 | 4-May-15 | 8803 | 3 | 4 | 5 | | | V-1 | AF357359 | | |
| 8708 | 3 | 4 | 5 | | | V-1 | Abra | 137735 | 12-May-15 | 8804 | 3 | 4 | 5 | | | V-1 | AF366264 | | |
| 8709 | 3 | 4 | 5 | | | V-1 | Abt1 | 29777 | 4-May-15 | 8805 | 3 | 4 | 5 | | | V-1 | Aff1 | 4299 | 12-May-15 |
| 8710 | 3 | 4 | 5 | | | V-1 | Acaa1a | | | 8806 | 3 | 4 | 5 | | | V-1 | Aff2 | 2334 | 12-May-15 |
| 8711 | 3 | 4 | 5 | | | V-1 | Acaa1b | | | 8807 | 3 | 4 | 5 | | | V-1 | Aff4 | 27125 | 22-May-15 |
| 8712 | 3 | 4 | 5 | | | V-1 | Acacb | 32 | 12-May-15 | 8808 | 3 | 4 | 5 | | | V-1 | Afmid | 125061 | 4-May-15 |
| 8713 | 3 | 4 | 5 | | | V-1 | Acad10 | 80724 | 4-May-15 | 8809 | 3 | 4 | 5 | | | V-1 | Afp | 174 | 7-Jun-15 |
| 8714 | 3 | 4 | 5 | | | V-1 | Acad8 | 27034 | 12-May-15 | 8810 | 3 | 4 | 5 | | | V-1 | Agap3 | 116988 | 12-May-15 |
| 8715 | 3 | 4 | 5 | | | V-1 | Acadm | 34 | 23-May-15 | 8811 | 3 | 4 | 5 | | | V-1 | Agfg1 | 3267 | 4-May-15 |
| 8716 | 3 | 4 | 5 | | | V-1 | Acap2 | 23527 | 4-May-15 | 8812 | 3 | 4 | 5 | | | V-1 | Aggf1 | 55109 | 4-May-15 |
| 8717 | 3 | 4 | 5 | | | V-1 | Acat3 | | | 8813 | 3 | 4 | 5 | | | V-1 | Ago1 | 26523 | 4-May-15 |
| 8718 | 3 | 4 | 5 | | | V-1 | Acbd3 | 64746 | 4-May-15 | 8814 | 3 | 4 | 5 | | | V-1 | Agpat3 | 56894 | 4-May-15 |
| 8719 | 3 | 4 | 5 | | | V-1 | Acbd5 | 91452 | 12-May-15 | 8815 | 3 | 4 | 5 | | | V-1 | Agpat5 | 55326 | 4-May-15 |
| 8720 | 3 | 4 | 5 | | | V-1 | Accs | 84680 | 20-May-15 | 8816 | 3 | 4 | 5 | | | V-1 | Agps | 8540 | 4-May-15 |
| 8721 | 3 | 4 | 5 | | | V-1 | Ace2 | 59272 | 17-May-15 | 8817 | 3 | 4 | 5 | | | V-1 | Agr3 | 155465 | 4-May-15 |
| 8722 | 3 | 4 | 5 | | | V-1 | Acer3 | 55331 | 12-May-15 | 8818 | 3 | 4 | 5 | | | V-1 | Agrp | 181 | 4-May-15 |
| 8723 | 3 | 4 | 5 | | | V-1 | Ache | 43 | 28-May-15 | 8819 | 3 | 4 | 5 | | | V-1 | Agtpbp1 | 23287 | 23-May-15 |
| 8724 | 3 | 4 | 5 | | | V-1 | Acin1 | 22985 | 2-Jun-15 | 8820 | 3 | 4 | 5 | | | V-1 | Agtr1b | 185 | 24-May-15 |
| 8725 | 3 | 4 | 5 | | | V-1 | Ackr3 | 57007 | 31-May-15 | 8821 | 3 | 4 | 5 | | | V-1 | Ahcyl1 | 10768 | 3-May-15 |
| 8726 | 3 | 4 | 5 | | | V-1 | Acn9 | 57001 | 4-May-15 | 8822 | 3 | 4 | 5 | | | V-1 | Ahdc1 | 27245 | 4-May-15 |
| 8727 | 3 | 4 | 5 | | | V-1 | Aco1 | 48 | 31-May-15 | 8823 | 3 | 4 | 5 | | | V-1 | Ahr | 196 | 17-May-15 |
| 8728 | 3 | 4 | 5 | | | V-1 | Acot10 | | | 8824 | 3 | 4 | 5 | | | V-1 | AI414108 | | |
| 8729 | 3 | 4 | 5 | | | V-1 | Acot12 | 134526 | 4-May-15 | 8825 | 3 | 4 | 5 | | | V-1 | AI429214 | | |
| 8730 | 3 | 4 | 5 | | | V-1 | Acot6 | 641372 | 4-May-15 | 8826 | 3 | 4 | 5 | | | V-1 | AI462493 | | |
| 8731 | 3 | 4 | 5 | | | V-1 | Acox1 | 51 | 12-May-15 | 8827 | 3 | 4 | 5 | | | V-1 | AI464131 | | |
| 8732 | 3 | 4 | 5 | | | V-1 | Acoxl | 55289 | 4-May-15 | 8828 | 3 | 4 | 5 | | | V-1 | AI646519 | | |
| 8733 | 3 | 4 | 5 | | | V-1 | Acp2 | 53 | 12-May-15 | 8829 | 3 | 4 | 5 | | | V-1 | AI747448 | | |
| 8734 | 3 | 4 | 5 | | | V-1 | Acp6 | 51205 | 4-May-15 | 8830 | 3 | 4 | 5 | | | V-1 | AI846148 | | |
| 8735 | 3 | 4 | 5 | | | V-1 | Acpt | 93650 | 4-May-15 | 8831 | 3 | 4 | 5 | | | V-1 | Aida | 64853 | 7-Jun-15 |
| 8736 | 3 | 4 | 5 | | | V-1 | Acrv1 | 56 | 4-May-15 | 8832 | 3 | 4 | 5 | | | V-1 | Aif1l | 83543 | 4-May-15 |
| 8737 | 3 | 4 | 5 | | | V-1 | Acsbg2 | 81616 | 4-May-15 | 8833 | 3 | 4 | 5 | | | V-1 | Aifm3 | 150209 | 4-May-15 |
| 8738 | 3 | 4 | 5 | | | V-1 | Acsf3 | 197322 | 4-May-15 | 8834 | 3 | 4 | 5 | | | V-1 | Aim1 | 202 | 7-Jun-15 |
| 8739 | 3 | 4 | 5 | | | V-1 | Acsl3 | 2181 | 4-May-15 | 8835 | 3 | 4 | 5 | | | V-1 | Aim1l | 55057 | 4-May-15 |
| 8740 | 3 | 4 | 5 | | | V-1 | Acsl5 | 51703 | 4-May-15 | 8836 | 3 | 4 | 5 | | | V-1 | Aimp1 | 9255 | 17-May-15 |
| 8741 | 3 | 4 | 5 | | | V-1 | Acsm1 | 116285 | 4-May-15 | 8837 | 3 | 4 | 5 | | | V-1 | AK010878 | | |
| 8742 | 3 | 4 | 5 | | | V-1 | Acsm2 | 123876 | 19-May-15 | 8838 | 3 | 4 | 5 | | | V-1 | Ak3 | 50808 | 7-Jun-15 |
| 8743 | 3 | 4 | 5 | | | V-1 | Acsm4 | 341392 | 4-May-15 | 8839 | 3 | 4 | 5 | | | V-1 | Ak5 | 26289 | 4-May-15 |
| 8744 | 3 | 4 | 5 | | | V-1 | Acss2os | | | 8840 | 3 | 4 | 5 | | | V-1 | Ak8 | 158067 | 4-May-15 |
| 8745 | 3 | 4 | 5 | | | V-1 | Acta2 | 59 | 23-May-15 | 8841 | 3 | 4 | 5 | | | V-1 | Akap13 | 11214 | 26-May-15 |
| 8746 | 3 | 4 | 5 | | | V-1 | Actbl2 | 345651 | 4-May-15 | 8842 | 3 | 4 | 5 | | | V-1 | Akap14 | 158798 | 4-May-15 |
| 8747 | 3 | 4 | 5 | | | V-1 | Actl10 | 170487 | 4-May-15 | 8843 | 3 | 4 | 5 | | | V-1 | Akap3 | 10566 | 4-May-15 |
| 8748 | 3 | 4 | 5 | | | V-1 | Actn4 | 81 | 29-May-15 | 8844 | 3 | 4 | 5 | | | V-1 | Akap6 | 9472 | 4-May-15 |
| 8749 | 3 | 4 | 5 | | | V-1 | Actr10 | 55860 | 4-May-15 | 8845 | 3 | 4 | 5 | | | V-1 | Akap8 | 10270 | 4-May-15 |
| 8750 | 3 | 4 | 5 | | | V-1 | Actr5 | 79933 | 4-May-15 | 8846 | 3 | 4 | 5 | | | V-1 | Aknad1 | 254268 | 4-May-15 |
| 8751 | 3 | 4 | 5 | | | V-1 | Acvr1b | 91 | 4-May-15 | 8847 | 3 | 4 | 5 | | | V-1 | Akr1b7 | | |
| 8752 | 3 | 4 | 5 | | | V-1 | Acvr2a | 92 | 4-May-15 | 8848 | 3 | 4 | 5 | | | V-1 | Akr1b8 | | |
| 8753 | 3 | 4 | 5 | | | V-1 | Acvr2b | 93 | 12-May-15 | 8849 | 3 | 4 | 5 | | | V-1 | Akr1c12 | | |
| 8754 | 3 | 4 | 5 | | | V-1 | Acy1 | 95 | 4-May-15 | 8850 | 3 | 4 | 5 | | | V-1 | Akr1c18 | | |
| 8755 | 3 | 4 | 5 | | | V-1 | Acyp1 | 97 | 12-May-15 | 8851 | 3 | 4 | 5 | | | V-1 | Akr1c6 | | |
| 8756 | 3 | 4 | 5 | | | V-1 | Adad1 | 132612 | 4-May-15 | 8852 | 3 | 4 | 5 | | | V-1 | Akt1 | 207 | 31-May-15 |
| 8757 | 3 | 4 | 5 | | | V-1 | Adam15 | 8751 | 4-May-15 | 8853 | 3 | 4 | 5 | | | V-1 | Aktip | 64400 | 12-May-15 |
| 8758 | 3 | 4 | 5 | | | V-1 | Adam17 | 6868 | 24-May-15 | 8854 | 3 | 4 | 5 | | | V-1 | Aldh16a1 | 126133 | 23-May-15 |
| 8759 | 3 | 4 | 5 | | | V-1 | Adam1a | 8759 | 4-May-15 | 8855 | 3 | 4 | 5 | | | V-1 | Aldh1a3 | 220 | 23-May-15 |
| 8760 | 3 | 4 | 5 | | | V-1 | Adam24 | 646479 | 12-May-15 | 8856 | 3 | 4 | 5 | | | V-1 | Aldh1l1 | 10840 | 23-May-15 |
| 8761 | 3 | 4 | 5 | | | V-1 | Adam29 | 11086 | 4-May-15 | 8857 | 3 | 4 | 5 | | | V-1 | Aldh3a2 | 224 | 23-May-15 |
| 8762 | 3 | 4 | 5 | | | V-1 | Adam34 | | | 8858 | 3 | 4 | 5 | | | V-1 | Aldh3b2 | 222 | 23-May-15 |
| 8763 | 3 | 4 | 5 | | | V-1 | Adam9 | 8754 | 17-May-15 | 8859 | 3 | 4 | 5 | | | V-1 | Aldh7a1 | 501 | 23-May-15 |
| 8764 | 3 | 4 | 5 | | | V-1 | Adamts10 | 81794 | 23-May-15 | 8860 | 3 | 4 | 5 | | | V-1 | Aldoart1 | | |
| 8765 | 3 | 4 | 5 | | | V-1 | Adamts13 | 11093 | 31-May-15 | 8861 | 3 | 4 | 5 | | | V-1 | Aldoart2 | | |
| 8766 | 3 | 4 | 5 | | | V-1 | Adamts16 | 170690 | 12-May-15 | 8862 | 3 | 4 | 5 | | | V-1 | Aldoc | 230 | 17-May-15 |
| 8767 | 3 | 4 | 5 | | | V-1 | Adamts18 | 170692 | 12-May-15 | 8863 | 3 | 4 | 5 | | | V-1 | Alg1 | 56052 | 23-May-15 |
| 8768 | 3 | 4 | 5 | | | V-1 | Adamts20 | 80070 | 12-May-15 | 8864 | 3 | 4 | 5 | | | V-1 | Alg13 | 79868 | 23-May-15 |
| 8769 | 3 | 4 | 5 | | | V-1 | Adamts3 | 9508 | May-15 | 8865 | 3 | 4 | 5 | | | V-1 | Alms1-ps2 | | |
| 8770 | 3 | 4 | 5 | | | V-1 | Adamtsl1 | 92949 | 4-May-15 | 8866 | 3 | 4 | 5 | | | V-1 | Alox8 | | |
| 8771 | 3 | 4 | 5 | | | V-1 | Adamtsl5 | 339366 | 4-May-15 | 8867 | 3 | 4 | 5 | | | V-1 | Alpi | 248 | 4-May-15 |
| 8772 | 3 | 4 | 5 | | | V-1 | Adar | 103 | 12-May-15 | 8868 | 3 | 4 | 5 | | | V-1 | Alpk2 | 115701 | 4-May-15 |
| 8773 | 3 | 4 | 5 | | | V-1 | Adarb1 | 104 | 4-May-15 | 8869 | 3 | 4 | 5 | | | V-1 | Als2 | 57679 | 23-May-15 |
| 8774 | 3 | 4 | 5 | | | V-1 | Adarb2 | 105 | 4-May-15 | 8870 | 3 | 4 | 5 | | | V-1 | Als2cl | 259173 | 4-May-15 |
| 8775 | 3 | 4 | 5 | | | V-1 | Adat3 | 113179 | 4-May-15 | 8871 | 3 | 4 | 5 | | | V-1 | Alx1 | 8092 | 12-May-15 |
| 8776 | 3 | 4 | 5 | | | V-1 | Adck1 | 57143 | 4-May-15 | 8872 | 3 | 4 | 5 | | | V-1 | Alyref2 | | |
| 8777 | 3 | 4 | 5 | | | V-1 | Adck4 | 79934 | 23-May-15 | 8873 | 3 | 4 | 5 | | | V-1 | Amdhd2 | 51005 | 4-May-15 |
| 8778 | 3 | 4 | 5 | | | V-1 | Adcy1 | 107 | 4-May-15 | 8874 | 3 | 4 | 5 | | | V-1 | Amelx | 265 | 12-May-15 |
| 8779 | 3 | 4 | 5 | | | V-1 | Adcy10 | 55811 | 4-May-15 | 8875 | 3 | 4 | 5 | | | V-1 | Amer2 | 219287 | 4-May-15 |
| 8780 | 3 | 4 | 5 | | | V-1 | Adcy4 | 196883 | 4-May-15 | 8876 | 3 | 4 | 5 | | | V-1 | Amigo1 | 57463 | 2-Jun-15 |
| 8781 | 3 | 4 | 5 | | | V-1 | Adcy6 | 112 | 23-May-15 | 8877 | 3 | 4 | 5 | | | V-1 | Amigo3 | 386724 | 4-May-15 |
| 8782 | 3 | 4 | 5 | | | V-1 | Adcy9 | 115 | 24-May-15 | 8878 | 3 | 4 | 5 | | | V-1 | Ammecr1l | 83607 | 4-May-15 |
| 8783 | 3 | 4 | 5 | | | V-1 | Add1 | 118 | 17-May-15 | 8879 | 3 | 4 | 5 | | | V-1 | Amot | 154796 | 4-May-15 |
| 8784 | 3 | 4 | 5 | | | V-1 | Add3 | 120 | 12-May-15 | 8880 | 3 | 4 | 5 | | | V-1 | Amotl1 | 154810 | 4-May-15 |
| 8785 | 3 | 4 | 5 | | | V-1 | Adh4 | 127 | 7-Jun-15 | 8881 | 3 | 4 | 5 | | | V-1 | Ampd1 | 270 | 12-May-15 |
| 8786 | 3 | 4 | 5 | | | V-1 | Adi1 | 55256 | 12-May-15 | 8882 | 3 | 4 | 5 | | | V-1 | Ampd3 | 272 | 12-May-15 |
| 8787 | 3 | 4 | 5 | | | V-1 | Adipor1 | 51094 | 31-May-15 | 8883 | 3 | 4 | 5 | | | V-1 | Amph | 273 | 12-May-15 |
| 8788 | 3 | 4 | 5 | | | V-1 | Adk | 132 | 4-May-15 | 8884 | 3 | 4 | 5 | | | V-1 | Amtn | 401138 | 4-May-15 |
| 8789 | 3 | 4 | 5 | | | V-1 | Adnp | 23394 | 4-May-15 | 8885 | 3 | 4 | 5 | | | V-1 | Amz1 | 155185 | 4-May-15 |
| 8790 | 3 | 4 | 5 | | | V-1 | Adora2a | 135 | 12-May-15 | 8886 | 3 | 4 | 5 | | | V-1 | Amz2 | 51321 | 23-May-15 |
| 8791 | 3 | 4 | 5 | | | V-1 | Adora3 | 140 | 12-May-15 | 8887 | 3 | 4 | 5 | | | V-1 | Anapc16 | 119504 | 31-May-15 |
| 8792 | 3 | 4 | 5 | | | V-1 | Adprh | 141 | 12-May-15 | 8888 | 3 | 4 | 5 | | | V-1 | Anapc2 | 29882 | 4-May-15 |
| 8793 | 3 | 4 | 5 | | | V-1 | Adprhl2 | 54936 | 4-May-15 | 8889 | 3 | 4 | 5 | | | V-1 | Ang2 | | |
| 8794 | 3 | 4 | 5 | | | V-1 | Adra1b | 147 | 14-May-15 | 8890 | 3 | 4 | 5 | | | V-1 | Ang5 | 27329 | 4-May-15 |
| 8795 | 3 | 4 | 5 | | | V-1 | Adra2b | 151 | 4-May-15 | 8891 | 3 | 4 | 5 | | | V-1 | Angptl2 | 23452 | 12-May-15 |
| 8796 | 3 | 4 | 5 | | | V-1 | Adrbk1 | 156 | 12-May-15 | 8892 | 3 | 4 | 5 | | | V-1 | Angptl6 | 83854 | 4-May-15 |
| 8797 | 3 | 4 | 5 | | | V-1 | Adrm1 | 11047 | 4-May-15 | 8893 | 3 | 4 | 5 | | | V-1 | Ank | 56172 | 7-Jun-15 |
| 8798 | 3 | 4 | 5 | | | V-1 | Adssl1 | 122622 | 12-May-15 | 8894 | 3 | 4 | 5 | | | V-1 | Ank2 | 287 | 12-May-15 |
| 8799 | 3 | 4 | 5 | | | V-1 | Adtrp | 84830 | 4-May-15 | 8895 | 3 | 4 | 5 | | | V-1 | Ankar | 150709 | 4-May-15 |
| 8800 | 3 | 4 | 5 | | | V-1 | Aebp2 | 121536 | 17-May-15 | 8896 | 3 | 4 | 5 | | | V-1 | Ankfn1 | 162282 | 4-May-15 |
| 8801 | 3 | 4 | 5 | | | V-1 | Aen | 64782 | 23-May-15 | 8897 | 3 | 4 | 5 | | | V-1 | Ankk1 | 255239 | 24-May-15 |
| 8802 | 3 | 4 | 5 | | | V-1 | Aes | 166 | 12-May-15 | 8898 | 3 | 4 | 5 | | | V-1 | Ankle2 | 23141 | 4-May-15 |

Fig. 30 - 48

| | | | | | | | | | | | | | | | | | | | |
|---|---|---|---|---|---|---|---|---|---|---|---|---|---|---|---|---|---|---|---|
| 8899 | 3 | 4 | 5 | | | V-1 | Ankrd10 | 55608 | 12-May-15 | 8993 | 3 | 4 | 5 | | | V-1 | Arhgef38 | 54848 | 4-May-15 |
| 8900 | 3 | 4 | 5 | | | V-1 | Ankrd16 | 54522 | 4-May-15 | 8994 | 3 | 4 | 5 | | | V-1 | Arhgef4 | 50649 | 17-May-15 |
| 8901 | 3 | 4 | 5 | | | V-1 | Ankrd22 | 118932 | 4-May-15 | 8995 | 3 | 4 | 5 | | | V-1 | Arhgef40 | 55701 | 4-May-15 |
| 8902 | 3 | 4 | 5 | | | V-1 | Ankrd23 | 200539 | 4-May-15 | 8996 | 3 | 4 | 5 | | | V-1 | Arhgef5 | 7984 | 4-May-15 |
| 8903 | 3 | 4 | 5 | | | V-1 | Ankrd24 | 170961 | 4-May-15 | 8997 | 3 | 4 | 5 | | | V-1 | Arhgef7 | 8874 | 4-May-15 |
| 8904 | 3 | 4 | 5 | | | V-1 | Ankrd29 | 147463 | 12-May-15 | 8998 | 3 | 4 | 5 | | | V-1 | Arid3b | 10620 | 28-May-15 |
| 8905 | 3 | 4 | 5 | | | V-1 | Ankrd34a | 284615 | 4-May-15 | 8999 | 3 | 4 | 5 | | | V-1 | Arid5b | 84159 | 4-May-15 |
| 8906 | 3 | 4 | 5 | | | V-1 | Ankrd39 | 51239 | 4-May-15 | 9000 | 3 | 4 | 5 | | | V-1 | Arih1 | 25820 | 31-May-15 |
| 8907 | 3 | 4 | 5 | | | V-1 | Ankrd45 | 339416 | 12-May-15 | 9001 | 3 | 4 | 5 | | | V-1 | Arl13a | 392509 | 4-May-15 |
| 8908 | 3 | 4 | 5 | | | V-1 | Ankrd50 | 57182 | 4-May-15 | 9002 | 3 | 4 | 5 | | | V-1 | Arl3 | 403 | 4-May-15 |
| 8909 | 3 | 4 | 5 | | | V-1 | Ankrd60 | 140731 | 12-May-15 | 9003 | 3 | 4 | 5 | | | V-1 | Arl5a | 26225 | 4-May-15 |
| 8910 | 3 | 4 | 5 | | | V-1 | Anks1 | 23294 | 21-May-15 | 9004 | 3 | 4 | 5 | | | V-1 | Arl6 | 84100 | 7-Jun-15 |
| 8911 | 3 | 4 | 5 | | | V-1 | Anks3 | 124401 | 12-May-15 | 9005 | 3 | 4 | 5 | | | V-1 | Arl6ip4 | 51329 | 12-May-15 |
| 8912 | 3 | 4 | 5 | | | V-1 | Anks6 | 203286 | 4-May-15 | 9006 | 3 | 4 | 5 | | | V-1 | Arl8a | 127829 | 4-May-15 |
| 8913 | 3 | 4 | 5 | | | V-1 | Ano1 | 55107 | 29-May-15 | 9007 | 3 | 4 | 5 | | | V-1 | Arl8b | 55207 | 4-May-15 |
| 8914 | 3 | 4 | 5 | | | V-1 | Ano10 | 55129 | 4-May-15 | 9008 | 3 | 4 | 5 | | | V-1 | Armc12 | 221481 | 4-May-15 |
| 8915 | 3 | 4 | 5 | | | V-1 | Ano4 | 123601 | 4-May-15 | 9009 | 3 | 4 | 5 | | | V-1 | Armc7 | 79637 | 12-May-15 |
| 8916 | 3 | 4 | 5 | | | V-1 | Ano7 | 50636 | 4-May-15 | 9010 | 3 | 4 | 5 | | | V-1 | Armc8 | 25852 | 4-May-15 |
| 8917 | 3 | 4 | 5 | | | V-1 | Anp32e | 81611 | 31-May-15 | 9011 | 3 | 4 | 5 | | | V-1 | Armcx2 | 9823 | 4-May-15 |
| 8918 | 3 | 4 | 5 | | | V-1 | Antxr2 | 118429 | 23-May-15 | 9012 | 3 | 4 | 5 | | | V-1 | Armcx3 | 51566 | 4-May-15 |
| 8919 | 3 | 4 | 5 | | | V-1 | Anxa10 | 11199 | 4-May-15 | 9013 | 3 | 4 | 5 | | | V-1 | Armcx5 | 64860 | 4-May-15 |
| 8920 | 3 | 4 | 5 | | | V-1 | Anxa4 | 307 | 4-May-15 | 9014 | 3 | 4 | 5 | | | V-1 | Arpc1a | 10552 | 4-May-15 |
| 8921 | 3 | 4 | 5 | | | V-1 | Anxa5 | 308 | 28-May-15 | 9015 | 3 | 4 | 5 | | | V-1 | Arpc2 | 10109 | 31-May-15 |
| 8922 | 3 | 4 | 5 | | | V-1 | Anxa6 | 309 | 4-May-15 | 9016 | 3 | 4 | 5 | | | V-1 | Arpp19 | 10776 | 12-May-15 |
| 8923 | 3 | 4 | 5 | | | V-1 | Anxa9 | 8416 | 4-May-15 | 9017 | 3 | 4 | 5 | | | V-1 | Arr3 | 407 | 12-May-15 |
| 8924 | 3 | 4 | 5 | | | V-1 | Aoc1 | 26 | 4-May-15 | 9018 | 3 | 4 | 5 | | | V-1 | Arrdc4 | 91947 | 4-May-15 |
| 8925 | 3 | 4 | 5 | | | V-1 | Aoc2 | 314 | 21-May-15 | 9019 | 3 | 4 | 5 | | | V-1 | Arrdc5 | 645432 | 21-May-15 |
| 8926 | 3 | 4 | 5 | | | V-1 | Aox2 | 344454 | 12-May-15 | 9020 | 3 | 4 | 5 | | | V-1 | Arsb | 411 | 13-Jun-15 |
| 8927 | 3 | 4 | 5 | | | V-1 | Aox3 | | | 9021 | 3 | 4 | 5 | | | V-1 | Arsg | 22901 | 20-May-15 |
| 8928 | 3 | 4 | 5 | | | V-1 | Aox4 | | | 9022 | 3 | 4 | 5 | | | V-1 | Arsk | 153642 | 23-May-15 |
| 8929 | 3 | 4 | 5 | | | V-1 | Ap1b1 | 162 | 12-May-15 | 9023 | 3 | 4 | 5 | | | V-1 | Art2a-ps | | |
| 8930 | 3 | 4 | 5 | | | V-1 | Ap1s1 | 1174 | 4-May-15 | 9024 | 3 | 4 | 5 | | | V-1 | Art3 | 419 | 4-May-15 |
| 8931 | 3 | 4 | 5 | | | V-1 | Ap2a1 | 160 | 12-May-15 | 9025 | 3 | 4 | 5 | | | V-1 | Art5 | 116969 | 4-May-15 |
| 8932 | 3 | 4 | 5 | | | V-1 | Ap3d1 | 8943 | 4-May-15 | 9026 | 3 | 4 | 5 | | | V-1 | Arv1 | 64801 | 4-May-15 |
| 8933 | 3 | 4 | 5 | | | V-1 | Ap3s2 | 10239 | 4-May-15 | 9027 | 3 | 4 | 5 | | | V-1 | Arx | 170302 | 23-May-15 |
| 8934 | 3 | 4 | 5 | | | V-1 | Apba1 | 320 | 4-May-15 | 9028 | 3 | 4 | 5 | | | V-1 | Asah1 | 427 | 12-May-15 |
| 8935 | 3 | 4 | 5 | | | V-1 | Apbb2 | 323 | 23-May-15 | 9029 | 3 | 4 | 5 | | | V-1 | Asb12 | 142689 | 4-May-15 |
| 8936 | 3 | 4 | 5 | | | V-1 | Apeh | 327 | 21-May-15 | 9030 | 3 | 4 | 5 | | | V-1 | Asb18 | 401036 | 4-May-15 |
| 8937 | 3 | 4 | 5 | | | V-1 | Apela | 100506013 | 12-May-15 | 9031 | 3 | 4 | 5 | | | V-1 | Asb3 | 51130 | 10-May-15 |
| 8938 | 3 | 4 | 5 | | | V-1 | Apex2 | 27301 | 12-May-15 | 9032 | 3 | 4 | 5 | | | V-1 | Asb5 | 140458 | 4-May-15 |
| 8939 | 3 | 4 | 5 | | | V-1 | Aph1a | 51107 | 4-May-15 | 9033 | 3 | 4 | 5 | | | V-1 | Ascl3 | 56676 | 4-May-15 |
| 8940 | 3 | 4 | 5 | | | V-1 | Api5 | 8539 | 4-May-15 | 9034 | 3 | 4 | 5 | | | V-1 | Asgr1 | 432 | 4-May-15 |
| 8941 | 3 | 4 | 5 | | | V-1 | Apif | 200558 | 4-May-15 | 9035 | 3 | 4 | 5 | | | V-1 | Asl | 435 | 7-Jun-15 |
| 8942 | 3 | 4 | 5 | | | V-1 | Aplp2 | 334 | 12-May-15 | 9036 | 3 | 4 | 5 | | | V-1 | Asna1 | 439 | 4-May-15 |
| 8943 | 3 | 4 | 5 | | | V-1 | Apoa5 | 116519 | 12-May-15 | 9037 | 3 | 4 | 5 | | | V-1 | Asnsd1 | 54529 | 4-May-15 |
| 8944 | 3 | 4 | 5 | | | V-1 | Apobec3 | | | 9038 | 3 | 4 | 5 | | | V-1 | Asph | 444 | 12-May-15 |
| 8945 | 3 | 4 | 5 | | | V-1 | Apobec4 | 403314 | 4-May-15 | 9039 | 3 | 4 | 5 | | | V-1 | Asphd1 | 253982 | 4-May-15 |
| 8946 | 3 | 4 | 5 | | | V-1 | Apod | 347 | 12-May-15 | 9040 | 3 | 4 | 5 | | | V-1 | Asphd2 | 57168 | 23-May-15 |
| 8947 | 3 | 4 | 5 | | | V-1 | Apof | 319 | 4-May-15 | 9041 | 3 | 4 | 5 | | | V-1 | Aspscr1 | 79058 | 4-May-15 |
| 8948 | 3 | 4 | 5 | | | V-1 | Apoh | 350 | 31-May-15 | 9042 | 3 | 4 | 5 | | | V-1 | Aste1 | 28990 | 12-May-15 |
| 8949 | 3 | 4 | 5 | | | V-1 | Apol10b | | | 9043 | 3 | 4 | 5 | | | V-1 | Asxl1 | 171023 | 21-May-15 |
| 8950 | 3 | 4 | 5 | | | V-1 | Apol7a | | | 9044 | 3 | 4 | 5 | | | V-1 | Atad2b | 54454 | 12-May-15 |
| 8951 | 3 | 4 | 5 | | | V-1 | Apol7d | | | 9045 | 3 | 4 | 5 | | | V-1 | Atat1 | 79969 | 4-May-15 |
| 8952 | 3 | 4 | 5 | | | V-1 | Apom | 55937 | 17-May-15 | 9046 | 3 | 4 | 5 | | | V-1 | Ate1 | 11101 | 4-May-15 |
| 8953 | 3 | 4 | 5 | | | V-1 | Apon | | | 9047 | 3 | 4 | 5 | | | V-1 | Atf6 | 22926 | 17-May-15 |
| 8954 | 3 | 4 | 5 | | | V-1 | Aptx | 54840 | 23-May-15 | 9048 | 3 | 4 | 5 | | | V-1 | Atf7ip | 55729 | 12-May-15 |
| 8955 | 3 | 4 | 5 | | | V-1 | Aqp11 | 282679 | 4-May-15 | 9049 | 3 | 4 | 5 | | | V-1 | Atg12 | 9140 | 21-May-15 |
| 8956 | 3 | 4 | 5 | | | V-1 | Aqp3 | 360 | 12-May-15 | 9050 | 3 | 4 | 5 | | | V-1 | Atg2a | 23130 | 21-May-15 |
| 8957 | 3 | 4 | 5 | | | V-1 | Aqr | 9716 | 4-May-15 | 9051 | 3 | 4 | 5 | | | V-1 | Atg4b | 23192 | 23-May-15 |
| 8958 | 3 | 4 | 5 | | | V-1 | Araf | 369 | 4-May-15 | 9052 | 3 | 4 | 5 | | | V-1 | Atg4c | 84938 | 21-May-15 |
| 8959 | 3 | 4 | 5 | | | V-1 | Arap2 | 116984 | 4-May-15 | 9053 | 3 | 4 | 5 | | | V-1 | Atg4d | 84971 | 21-May-15 |
| 8960 | 3 | 4 | 5 | | | V-1 | Arap3 | 64411 | 4-May-15 | 9054 | 3 | 4 | 5 | | | V-1 | Atg5 | 9474 | 21-May-15 |
| 8961 | 3 | 4 | 5 | | | V-1 | Arcn1 | 372 | 4-May-15 | 9055 | 3 | 4 | 5 | | | V-1 | Atg9b | 285973 | 21-May-15 |
| 8962 | 3 | 4 | 5 | | | V-1 | Aretl | 9870 | 4-May-15 | 9056 | 3 | 4 | 5 | | | V-1 | Atic | 471 | 4-May-15 |
| 8963 | 3 | 4 | 5 | | | V-1 | Arf1 | 375 | 7-Jun-15 | 9057 | 3 | 4 | 5 | | | V-1 | Atl2 | 64225 | 23-May-15 |
| 8964 | 3 | 4 | 5 | | | V-1 | Arf2 | 378 | 31-May-15 | 9058 | 3 | 4 | 5 | | | V-1 | Atoh1 | 474 | 4-May-15 |
| 8965 | 3 | 4 | 5 | | | V-1 | Arf6 | 382 | 23-May-15 | 9059 | 3 | 4 | 5 | | | V-1 | Atox1 | 475 | 17-May-15 |
| 8966 | 3 | 4 | 5 | | | V-1 | Arfgap1 | 55738 | 7-Jun-15 | 9060 | 3 | 4 | 5 | | | V-1 | Atp10d | 57205 | 4-May-15 |
| 8967 | 3 | 4 | 5 | | | V-1 | Arfgap2 | 84364 | 4-May-15 | 9061 | 3 | 4 | 5 | | | V-1 | Atp11a | 23250 | 4-May-15 |
| 8968 | 3 | 4 | 5 | | | V-1 | Arfgef1 | 10565 | 4-May-15 | 9062 | 3 | 4 | 5 | | | V-1 | Atp11b | 23200 | 4-May-15 |
| 8969 | 3 | 4 | 5 | | | V-1 | Arglu1 | 55082 | 12-May-15 | 9063 | 3 | 4 | 5 | | | V-1 | Atp13a3 | 79572 | 4-May-15 |
| 8970 | 3 | 4 | 5 | | | V-1 | Arhgap12 | 94134 | 4-May-15 | 9064 | 3 | 4 | 5 | | | V-1 | Atp13a4 | 84239 | 4-May-15 |
| 8971 | 3 | 4 | 5 | | | V-1 | Arhgap15os | | | 9065 | 3 | 4 | 5 | | | V-1 | Atp1b4 | 23439 | 4-May-15 |
| 8972 | 3 | 4 | 5 | | | V-1 | Arhgap20os | | | 9066 | 3 | 4 | 5 | | | V-1 | Atp2b1 | 490 | 24-May-15 |
| 8973 | 3 | 4 | 5 | | | V-1 | Arhgap21 | 57584 | 4-May-15 | 9067 | 3 | 4 | 5 | | | V-1 | Atp2c1 | 27032 | 4-May-15 |
| 8974 | 3 | 4 | 5 | | | V-1 | Arhgap23 | 57636 | 4-May-15 | 9068 | 3 | 4 | 5 | | | V-1 | Atp4b | 496 | 4-May-15 |
| 8975 | 3 | 4 | 5 | | | V-1 | Arhgap24 | 83478 | 4-May-15 | 9069 | 3 | 4 | 5 | | | V-1 | Atp5g2 | 517 | 4-May-15 |
| 8976 | 3 | 4 | 5 | | | V-1 | Arhgap26 | 23092 | 12-May-15 | 9070 | 3 | 4 | 5 | | | V-1 | Atp5l | 10632 | 4-May-15 |
| 8977 | 3 | 4 | 5 | | | V-1 | Arhgap27 | 201176 | 4-May-15 | 9071 | 3 | 4 | 5 | | | V-1 | Atp6v0a1 | 535 | 21-May-15 |
| 8978 | 3 | 4 | 5 | | | V-1 | Arhgap28 | 79822 | 31-May-15 | 9072 | 3 | 4 | 5 | | | V-1 | Atp6v0b | 533 | 3-Jun-15 |
| 8979 | 3 | 4 | 5 | | | V-1 | Arhgap31 | 57514 | 4-May-15 | 9073 | 3 | 4 | 5 | | | V-1 | Atp6v0d1 | 9114 | 4-May-15 |
| 8980 | 3 | 4 | 5 | | | V-1 | Arhgap33os | | | 9074 | 3 | 4 | 5 | | | V-1 | Atp6v0e | 8992 | 4-May-15 |
| 8981 | 3 | 4 | 5 | | | V-1 | Arhgap40 | 343578 | 4-May-15 | 9075 | 3 | 4 | 5 | | | V-1 | Atp6v1b1 | 525 | 24-May-15 |
| 8982 | 3 | 4 | 5 | | | V-1 | Arhgap5 | 394 | 12-May-15 | 9076 | 3 | 4 | 5 | | | V-1 | Atp6v1b2 | 526 | 4-May-15 |
| 8983 | 3 | 4 | 5 | | | V-1 | Arhgdia | 396 | 12-May-15 | 9077 | 3 | 4 | 5 | | | V-1 | Atp6v1d | 51382 | 4-May-15 |
| 8984 | 3 | 4 | 5 | | | V-1 | Arhgef1 | 9138 | 31-May-15 | 9078 | 3 | 4 | 5 | | | V-1 | Atp6v1g2 | 534 | 4-May-15 |
| 8985 | 3 | 4 | 5 | | | V-1 | Arhgef11 | 9826 | 4-May-15 | 9079 | 3 | 4 | 5 | | | V-1 | Atp7a | 538 | 23-May-15 |
| 8986 | 3 | 4 | 5 | | | V-1 | Arhgef15 | 22899 | 4-May-15 | 9080 | 3 | 4 | 5 | | | V-1 | Atp8a1 | 10396 | 12-May-15 |
| 8987 | 3 | 4 | 5 | | | V-1 | Arhgef16 | 27237 | 12-May-15 | 9081 | 3 | 4 | 5 | | | V-1 | Atp8a2 | 51761 | 4-May-15 |
| 8988 | 3 | 4 | 5 | | | V-1 | Arhgef17 | 9828 | 4-May-15 | 9082 | 3 | 4 | 5 | | | V-1 | Atp8b2 | 57198 | 21-May-15 |
| 8989 | 3 | 4 | 5 | | | V-1 | Arhgef18 | 23370 | 4-May-15 | 9083 | 3 | 4 | 5 | | | V-1 | Atp8b3 | 148229 | 4-May-15 |
| 8990 | 3 | 4 | 5 | | | V-1 | Arhgef25 | 115557 | 4-May-15 | 9084 | 3 | 4 | 5 | | | V-1 | Atp8b5 | | |
| 8991 | 3 | 4 | 5 | | | V-1 | Arhgef28 | 64283 | 4-May-15 | 9085 | 3 | 4 | 5 | | | V-1 | Atr | 545 | 13-Jun-15 |
| 8992 | 3 | 4 | 5 | | | V-1 | Arhgef33 | 100271715 | 12-May-15 | 9086 | 3 | 4 | 5 | | | V-1 | Atxn10 | 25814 | 23-May-15 |
| | | | | | | | | | | 9087 | 3 | 4 | 5 | | | V-1 | Atxn1l | 342371 | 4-May-15 |
| | | | | | | | | | | 9088 | 3 | 4 | 5 | | | V-1 | Atxn7l3 | 56970 | 12-May-15 |

Fig. 30 - 49

| | | | | | | | | | | | | | | | | | | | |
|---|---|---|---|---|---|---|---|---|---|---|---|---|---|---|---|---|---|---|---|
| 9089 | 3 | 4 | 5 | | | V-1 | AU015836 | | | 9185 | 3 | 4 | 5 | | | V-1 | Bend6 | 221336 | 4-May-15 |
| 9090 | 3 | 4 | 5 | | | V-1 | AU022252 | | | 9186 | 3 | 4 | 5 | | | V-1 | Bend7 | 222389 | 4-May-15 |
| 9091 | 3 | 4 | 5 | | | V-1 | AU023762 | | | 9187 | 3 | 4 | 5 | | | V-1 | Bex6 | | |
| 9092 | 3 | 4 | 5 | | | V-1 | AU041133 | | | 9188 | 3 | 4 | 5 | | | V-1 | Bfsp2 | 8419 | 17-May-15 |
| 9093 | 3 | 4 | 5 | | | V-1 | Aurkaip1 | 54998 | 4-May-15 | 9189 | 3 | 4 | 5 | | | V-1 | Bhlha9 | 727857 | 4-May-15 |
| 9094 | 3 | 4 | 5 | | | V-1 | Aurkc | 6795 | 21-May-15 | 9190 | 3 | 4 | 5 | | | V-1 | Bicd1 | 636 | 3-May-15 |
| 9095 | 3 | 4 | 5 | | | V-1 | AV039307 | | | 9191 | 3 | 4 | 5 | | | V-1 | Bicd2 | 23299 | 4-May-15 |
| 9096 | 3 | 4 | 5 | | | V-1 | AV051173 | | | 9192 | 3 | 4 | 5 | | | V-1 | Bik | 638 | 12-May-15 |
| 9097 | 3 | 4 | 5 | | | V-1 | AV320801 | | | 9193 | 3 | 4 | 5 | | | V-1 | Bin1 | 274 | 12-May-15 |
| 9098 | 3 | 4 | 5 | | | V-1 | Avil9 | 23080 | 12-May-15 | 9194 | 3 | 4 | 5 | | | V-1 | Bin3 | 55909 | 4-May-15 |
| 9099 | 3 | 4 | 5 | | | V-1 | Avpi1 | 60370 | 21-May-15 | 9195 | 3 | 4 | 5 | | | V-1 | Birc6 | 57448 | 21-May-15 |
| 9100 | 3 | 4 | 5 | | | V-1 | Avpr1b | 553 | 17-May-15 | 9196 | 3 | 4 | 5 | | | V-1 | Birnh | 642 | 23-May-15 |
| 9101 | 3 | 4 | 5 | | | V-1 | AW046200 | | | 9197 | 3 | 4 | 5 | | | V-1 | Bloc1s1 | 2647 | 28-May-15 |
| 9102 | 3 | 4 | 5 | | | V-1 | AW146154 | | | 9198 | 3 | 4 | 5 | | | V-1 | Bizf1 | 8548 | 4-May-15 |
| 9103 | 3 | 4 | 5 | | | V-1 | AW209491 | | | 9199 | 3 | 4 | 5 | | | V-1 | Bmi1 | 648 | 2-Jun-15 |
| 9104 | 3 | 4 | 5 | | | V-1 | AW549877 | | | 9200 | 3 | 4 | 5 | | | V-1 | Bmp15 | 9210 | 3-May-15 |
| 9105 | 3 | 4 | 5 | | | V-1 | Axl | 558 | 17-May-15 | 9201 | 3 | 4 | 5 | | | V-1 | Bmp2k | 55589 | 12-May-15 |
| 9106 | 3 | 4 | 5 | | | V-1 | AY074887 | | | 9202 | 3 | 4 | 5 | | | V-1 | Bmp4 | 652 | 31-May-15 |
| 9107 | 3 | 4 | 5 | | | V-1 | Azi2 | 64343 | 7-Jun-15 | 9203 | 3 | 4 | 5 | | | V-1 | Bmp5 | 653 | 17-May-15 |
| 9108 | 3 | 4 | 5 | | | V-1 | B020004C17Rik | | | 9204 | 3 | 4 | 5 | | | V-1 | Bmpr1a | 657 | 23-May-15 |
| 9109 | 3 | 4 | 5 | | | V-1 | B230209E15Rik | | | 9205 | 3 | 4 | 5 | | | V-1 | Bmpr1b | 658 | 3-May-15 |
| 9110 | 3 | 4 | 5 | | | V-1 | B330016D10Rik | | | 9206 | 3 | 4 | 5 | | | V-1 | Bmpr2 | 659 | 31-May-15 |
| 9111 | 3 | 4 | 5 | | | V-1 | B3galnt2 | 148789 | 4-May-15 | 9207 | 3 | 4 | 5 | | | V-1 | Bnip3l | 665 | 4-May-15 |
| 9112 | 3 | 4 | 5 | | | V-1 | B3galt4 | 8705 | 4-May-15 | 9208 | 3 | 4 | 5 | | | V-1 | Bnipl | 149428 | 4-May-15 |
| 9113 | 3 | 4 | 5 | | | V-1 | B3gnt1 | 10678 | 7-Jun-15 | 9209 | 3 | 4 | 5 | | | V-1 | Bod1 | 91272 | 4-May-15 |
| 9114 | 3 | 4 | 5 | | | V-1 | B3gnt4 | 79369 | 4-May-15 | 9210 | 3 | 4 | 5 | | | V-1 | Bola1 | 51027 | 4-May-15 |
| 9115 | 3 | 4 | 5 | | | V-1 | B3gnt6 | 192134 | 4-May-15 | 9211 | 3 | 4 | 5 | | | V-1 | Bola3 | 388962 | 4-May-15 |
| 9116 | 3 | 4 | 5 | | | V-1 | B3gnt9 | 84752 | 4-May-15 | 9212 | 3 | 4 | 5 | | | V-1 | Boll | 66037 | 4-May-15 |
| 9117 | 3 | 4 | 5 | | | V-1 | B3gntl1 | 146712 | 4-May-15 | 9213 | 3 | 4 | 5 | | | V-1 | Bphl | 670 | 12-May-15 |
| 9118 | 3 | 4 | 5 | | | V-1 | B430212C06Rik | | | 9214 | 3 | 4 | 5 | | | V-1 | Bpifa2 | 140683 | 4-May-15 |
| 9119 | 3 | 4 | 5 | | | V-1 | B430319G15Rik | | | 9215 | 3 | 4 | 5 | | | V-1 | Bpifb2 | 80341 | 4-May-15 |
| 9120 | 3 | 4 | 5 | | | V-1 | B4galt3 | 8703 | 7-Jun-15 | 9216 | 3 | 4 | 5 | | | V-1 | Bpifb6 | 128859 | 4-May-15 |
| 9121 | 3 | 4 | 5 | | | V-1 | B4galt6 | 9331 | 4-May-15 | 9217 | 3 | 4 | 5 | | | V-1 | Brca2 | 675 | 25-May-15 |
| 9122 | 3 | 4 | 5 | | | V-1 | B4galt7 | 11285 | 4-May-15 | 9218 | 3 | 4 | 5 | | | V-1 | Brcc3 | 79184 | 7-Jun-15 |
| 9123 | 3 | 4 | 5 | | | V-1 | B930059L03Rik | | | 9219 | 3 | 4 | 5 | | | V-1 | Bricd5 | 283870 | 4-May-15 |
| 9124 | 3 | 4 | 5 | | | V-1 | Baalc | 79870 | 12-May-15 | 9220 | 3 | 4 | 5 | | | V-1 | Brinp2 | 57795 | 4-May-15 |
| 9125 | 3 | 4 | 5 | | | V-1 | Bach1 | 571 | 13-Jun-15 | 9221 | 3 | 4 | 5 | | | V-1 | Brix1 | 55299 | 4-May-15 |
| 9126 | 3 | 4 | 5 | | | V-1 | Bach2os | | | 9222 | 3 | 4 | 5 | | | V-1 | Brs3 | 680 | 4-May-15 |
| 9127 | 3 | 4 | 5 | | | V-1 | Bag3 | 9531 | 24-May-15 | 9223 | 3 | 4 | 5 | | | V-1 | Brsk2 | 9024 | 28-May-15 |
| 9128 | 3 | 4 | 5 | | | V-1 | Bag5 | 9529 | 28-May-15 | 9224 | 3 | 4 | 5 | | | V-1 | Bsnd | 7809 | 12-May-15 |
| 9129 | 3 | 4 | 5 | | | V-1 | Bak1 | 578 | 17-May-15 | 9225 | 3 | 4 | 5 | | | V-1 | Bsph2 | | |
| 9130 | 3 | 4 | 5 | | | V-1 | Bap1 | 8314 | 7-Jun-15 | 9226 | 3 | 4 | 5 | | | V-1 | Bst2 | 684 | 31-May-15 |
| 9131 | 3 | 4 | 5 | | | V-1 | Barhl1 | 56751 | 28-May-15 | 9227 | 3 | 4 | 5 | | | V-1 | Bsx | 390259 | 4-May-15 |
| 9132 | 3 | 4 | 5 | | | V-1 | Batf | 10538 | 7-Jun-15 | 9228 | 3 | 4 | 5 | | | V-1 | Btbd11 | 121551 | 4-May-15 |
| 9133 | 3 | 4 | 5 | | | V-1 | Batf3 | 55509 | 4-May-15 | 9229 | 3 | 4 | 5 | | | V-1 | Btbd2 | 55643 | 4-May-15 |
| 9134 | 3 | 4 | 5 | | | V-1 | Bax | 581 | 24-May-15 | 9230 | 3 | 4 | 5 | | | V-1 | Btbd7 | 55727 | 4-May-15 |
| 9135 | 3 | 4 | 5 | | | V-1 | Bazib | 9031 | 4-May-15 | 9231 | 3 | 4 | 5 | | | V-1 | Btd | 686 | 7-Jun-15 |
| 9136 | 3 | 4 | 5 | | | V-1 | Bbip1 | 92482 | 4-May-15 | 9232 | 3 | 4 | 5 | | | V-1 | Btg4 | 54766 | 14-May-15 |
| 9137 | 3 | 4 | 5 | | | V-1 | Bbs4 | 585 | 23-May-15 | 9233 | 3 | 4 | 5 | | | V-1 | Btn2a2 | 10385 | 4-May-15 |
| 9138 | 3 | 4 | 5 | | | V-1 | BC002163 | | | 9234 | 3 | 4 | 5 | | | V-1 | Btnl4 | | |
| 9139 | 3 | 4 | 5 | | | V-1 | BC005561 | | | 9235 | 3 | 4 | 5 | | | V-1 | Btrc | 8945 | 4-May-15 |
| 9140 | 3 | 4 | 5 | | | V-1 | BC006965 | | | 9236 | 3 | 4 | 5 | | | V-1 | Bub3 | 9184 | 12-May-15 |
| 9141 | 3 | 4 | 5 | | | V-1 | BC018242 | | | 9237 | 3 | 4 | 5 | | | V-1 | Bzrap1 | 9256 | 4-May-15 |
| 9142 | 3 | 4 | 5 | | | V-1 | BC018507 | | | 9238 | 3 | 4 | 5 | | | V-1 | Bzw1 | 9689 | 4-May-15 |
| 9143 | 3 | 4 | 5 | | | V-1 | BC021785 | | | 9239 | 3 | 4 | 5 | | | V-1 | C030006K11Rik | | |
| 9144 | 3 | 4 | 5 | | | V-1 | BC021891 | | | 9240 | 3 | 4 | 5 | | | V-1 | C030039L03Rik | | |
| 9145 | 3 | 4 | 5 | | | V-1 | BC022687 | | | 9241 | 3 | 4 | 5 | | | V-1 | C130026L21Rik | | |
| 9146 | 3 | 4 | 5 | | | V-1 | BC023829 | | | 9242 | 3 | 4 | 5 | | | V-1 | C130060C02Rik | | |
| 9147 | 3 | 4 | 5 | | | V-1 | BC024386 | | | 9243 | 3 | 4 | 5 | | | V-1 | C130079G13Rik | | |
| 9148 | 3 | 4 | 5 | | | V-1 | BC026585 | | | 9244 | 3 | 4 | 5 | | | V-1 | C1d | 10438 | 4-May-15 |
| 9149 | 3 | 4 | 5 | | | V-1 | BC029214 | | | 9245 | 3 | 4 | 5 | | | V-1 | C1galt1c1 | 29071 | 4-May-15 |
| 9150 | 3 | 4 | 5 | | | V-1 | BC030870 | | | 9246 | 3 | 4 | 5 | | | V-1 | C1qbp | 708 | 4-May-15 |
| 9151 | 3 | 4 | 5 | | | V-1 | BC037032 | | | 9247 | 3 | 4 | 5 | | | V-1 | C1ql3 | 10882 | 4-May-15 |
| 9152 | 3 | 4 | 5 | | | V-1 | BC037704 | | | 9248 | 3 | 4 | 5 | | | V-1 | C1qtnf7 | 114905 | 4-May-15 |
| 9153 | 3 | 4 | 5 | | | V-1 | BC039771 | | | 9249 | 3 | 4 | 5 | | | V-1 | C1qtnf9 | 338872 | 12-May-15 |
| 9154 | 3 | 4 | 5 | | | V-1 | BC048562 | | | 9250 | 3 | 4 | 5 | | | V-1 | C1rl | 51279 | 12-May-15 |
| 9155 | 3 | 4 | 5 | | | V-1 | BC049352 | | | 9251 | 3 | 4 | 5 | | | V-1 | C230004F18Rik | | |
| 9156 | 3 | 4 | 5 | | | V-1 | BC049762 | | | 9252 | 3 | 4 | 5 | | | V-1 | C230079O03Rik | | |
| 9157 | 3 | 4 | 5 | | | V-1 | BC051142 | | | 9253 | 3 | 4 | 5 | | | V-1 | C2cd3 | 26005 | 12-May-15 |
| 9158 | 3 | 4 | 5 | | | V-1 | BC051628 | | | 9254 | 3 | 4 | 5 | | | V-1 | C330006A16Rik | | |
| 9159 | 3 | 4 | 5 | | | V-1 | BC052688 | | | 9255 | 3 | 4 | 5 | | | V-1 | C330046G13Rik | | |
| 9160 | 3 | 4 | 5 | | | V-1 | BC055111 | | | 9256 | 3 | 4 | 5 | | | V-1 | C430002E04Rik | | |
| 9161 | 3 | 4 | 5 | | | V-1 | BC055402 | | | 9257 | 3 | 4 | 5 | | | V-1 | C4bp-ps1 | | |
| 9162 | 3 | 4 | 5 | | | V-1 | BC061212 | | | 9258 | 3 | 4 | 5 | | | V-1 | C530044C16Rik | | |
| 9163 | 3 | 4 | 5 | | | V-1 | BC065397 | | | 9259 | 3 | 4 | 5 | | | V-1 | C5ar2 | 27202 | 4-May-15 |
| 9164 | 3 | 4 | 5 | | | V-1 | Bc1 | | | 9260 | 3 | 4 | 5 | | | V-1 | C630028M04Rik | | |
| 9165 | 3 | 4 | 5 | | | V-1 | BC100451 | | | | | | | | | | | | |
| 9166 | 3 | 4 | 5 | | | V-1 | BC107364 | | | 9261 | 3 | 4 | 5 | | | V-1 | C730002L08Rik | | |
| 9167 | 3 | 4 | 5 | | | V-1 | BC147527 | | | 9262 | 3 | 4 | 5 | | | V-1 | C77080 | | |
| 9168 | 3 | 4 | 5 | | | V-1 | Bcam | 4059 | 7-Jun-15 | 9263 | 3 | 4 | 5 | | | V-1 | C78339 | | |
| 9169 | 3 | 4 | 5 | | | V-1 | Bcas1 | 8537 | 4-May-15 | 9264 | 3 | 4 | 5 | | | V-1 | C9 | 735 | 7-Jun-15 |
| 9170 | 3 | 4 | 5 | | | V-1 | Bcat2 | 587 | 4-May-15 | 9265 | 3 | 4 | 5 | | | V-1 | C920021L13Rik | | |
| 9171 | 3 | 4 | 5 | | | V-1 | Bckdha | 593 | 23-May-15 | 9266 | 3 | 4 | 5 | | | V-1 | Caap1 | 79886 | 12-May-15 |
| 9172 | 3 | 4 | 5 | | | V-1 | Bcl11b | 64919 | 28-May-15 | 9267 | 3 | 4 | 5 | | | V-1 | Cables2 | 81928 | 4-May-15 |
| 9173 | 3 | 4 | 5 | | | V-1 | Bcl2a1c | | | 9268 | 3 | 4 | 5 | | | V-1 | Cabp1 | 9478 | 7-Jun-15 |
| 9174 | 3 | 4 | 5 | | | V-1 | Bcl2l11 | 10018 | 17-May-15 | 9269 | 3 | 4 | 5 | | | V-1 | Cabp4 | 57010 | 14-May-15 |
| 9175 | 3 | 4 | 5 | | | V-1 | Bcl2l12 | 83596 | 4-May-15 | 9270 | 3 | 4 | 5 | | | V-1 | Cabp5 | 56344 | 12-May-15 |
| 9176 | 3 | 4 | 5 | | | V-1 | Bcl2l14 | 79370 | 4-May-15 | 9271 | 3 | 4 | 5 | | | V-1 | Cacfd1 | 11094 | 4-May-15 |
| 9177 | 3 | 4 | 5 | | | V-1 | Bcl2l2 | 599 | 4-May-15 | 9272 | 3 | 4 | 5 | | | V-1 | Cachd1 | 57685 | 12-May-15 |
| 9178 | 3 | 4 | 5 | | | V-1 | Bcl6b | 255877 | 4-May-15 | 9273 | 3 | 4 | 5 | | | V-1 | Cacna1a | 773 | 22-May-15 |
| 9179 | 3 | 4 | 5 | | | V-1 | Bcl7b | 9275 | 4-May-15 | 9274 | 3 | 4 | 5 | | | V-1 | Cacna1b | 774 | 12-May-15 |
| 9180 | 3 | 4 | 5 | | | V-1 | Bcs1l | 617 | 23-May-15 | 9275 | 3 | 4 | 5 | | | V-1 | Cacna1f | 778 | 23-May-15 |
| 9181 | 3 | 4 | 5 | | | V-1 | Bdkrb1 | 623 | 12-May-15 | 9276 | 3 | 4 | 5 | | | V-1 | Cacna1s | 779 | 23-May-15 |
| 9182 | 3 | 4 | 5 | | | V-1 | Bdkrb2 | 624 | 7-Jun-15 | 9277 | 3 | 4 | 5 | | | V-1 | Cacna2d3 | 55799 | 4-May-15 |
| 9183 | 3 | 4 | 5 | | | V-1 | Becn1 | 8678 | 31-May-15 | 9278 | 3 | 4 | 5 | | | V-1 | Cacna2d4 | 93589 | 4-May-15 |
| 9184 | 3 | 4 | 5 | | | V-1 | Bend5 | 79656 | 4-May-15 | 9279 | 3 | 4 | 5 | | | V-1 | Cacnb2 | 783 | 23-May-15 |

Fig. 30 - 50

| | | | | | | | | | | | | | | | | |
|---|---|---|---|---|---|---|---|---|---|---|---|---|---|---|---|---|
| 9280 | 3 | 4 | 5 | | | V-1 | Cacnb4 | 785 | 23-May-15 | 9375 | 3 | 4 | 5 | | V-1 | Ccl25 | 6370 | 4-May-15 |
| 9281 | 3 | 4 | 5 | | | V-1 | Cacng2 | 10369 | 4-May-15 | 9376 | 3 | 4 | 5 | | V-1 | Ccm2 | 83605 | 23-May-15 |
| 9282 | 3 | 4 | 5 | | | V-1 | Cacng8 | 59283 | 4-May-15 | 9377 | 3 | 4 | 5 | | V-1 | Ccm2l | 140706 | 4-May-15 |
| 9283 | 3 | 4 | 5 | | | V-1 | Cadm2 | 253559 | 2-Jun-15 | 9378 | 3 | 4 | 5 | | V-1 | Ccna1 | 8900 | 4-May-15 |
| 9284 | 3 | 4 | 5 | | | V-1 | Cadm4 | 199731 | 1-Jun-15 | 9379 | 3 | 4 | 5 | | V-1 | Ccnb3 | 85417 | 4-May-15 |
| 9285 | 3 | 4 | 5 | | | V-1 | Cadps | 8618 | 4-May-15 | 9380 | 3 | 4 | 5 | | V-1 | Ccnd2 | 894 | 4-May-15 |
| 9286 | 3 | 4 | 5 | | | V-1 | Calcb | 797 | 28-May-15 | 9381 | 3 | 4 | 5 | | V-1 | Ccndbp1 | 23582 | 17-May-15 |
| 9287 | 3 | 4 | 5 | | | V-1 | Cald1 | 800 | 4-May-15 | 9382 | 3 | 4 | 5 | | V-1 | Ccng1 | 900 | 4-May-15 |
| 9288 | 3 | 4 | 5 | | | V-1 | Calhm1 | 255022 | 4-May-15 | 9383 | 3 | 4 | 5 | | V-1 | Ccnh | 902 | 4-May-15 |
| 9289 | 3 | 4 | 5 | | | V-1 | Calm1 | 801 | 17-May-15 | 9384 | 3 | 4 | 5 | | V-1 | Ccnk | 8812 | 4-May-15 |
| 9290 | 3 | 4 | 5 | | | V-1 | Calr | 811 | 17-May-15 | 9385 | 3 | 4 | 5 | | V-1 | Ccnl2 | 81669 | 4-May-15 |
| 9291 | 3 | 4 | 5 | | | V-1 | Camk1g | 57172 | 4-May-15 | 9386 | 3 | 4 | 5 | | V-1 | Ccnt1 | 904 | 4-May-15 |
| 9292 | 3 | 4 | 5 | | | V-1 | Camk2g | 818 | 4-May-15 | 9387 | 3 | 4 | 5 | | V-1 | Ccnt2 | 905 | 4-May-15 |
| 9293 | 3 | 4 | 5 | | | V-1 | Camk2n2 | 94032 | 4-May-15 | 9388 | 3 | 4 | 5 | | V-1 | Ccpg1 | 9236 | 4-May-15 |
| 9294 | 3 | 4 | 5 | | | V-1 | Camk4 | 814 | 4-May-15 | 9389 | 3 | 4 | 5 | | V-1 | Ccr10 | 2826 | 7-Jun-15 |
| 9295 | 3 | 4 | 5 | | | V-1 | Camkk2 | 10645 | 12-May-15 | 9390 | 3 | 4 | 5 | | V-1 | Ccr7 | 1236 | 17-May-15 |
| 9296 | 3 | 4 | 5 | | | V-1 | Camkmt | 79823 | 12-May-15 | 9391 | 3 | 4 | 5 | | V-1 | Ccr8 | 1237 | 4-May-15 |
| 9297 | 3 | 4 | 5 | | | V-1 | Camsap1 | 157922 | 4-May-15 | 9392 | 3 | 4 | 5 | | V-1 | Ccs | 9973 | 12-May-15 |
| 9298 | 3 | 4 | 5 | | | V-1 | Camsap2 | 23271 | 4-May-15 | 9393 | 3 | 4 | 5 | | V-1 | Ccser1 | 401145 | 4-May-15 |
| 9299 | 3 | 4 | 5 | | | V-1 | Camsap3 | 57662 | 4-May-15 | 9394 | 3 | 4 | 5 | | V-1 | Cd151 | 977 | 4-May-15 |
| 9300 | 3 | 4 | 5 | | | V-1 | Camta1 | 23261 | 4-May-15 | 9395 | 3 | 4 | 5 | | V-1 | Cd163l1 | 283316 | 28-May-15 |
| 9301 | 3 | 4 | 5 | | | V-1 | Cant1 | 124583 | 4-May-15 | 9396 | 3 | 4 | 5 | | V-1 | Cd200r2 | 344807 | 4-May-15 |
| 9302 | 3 | 4 | 5 | | | V-1 | Cap2 | 10486 | 7-Jun-15 | 9397 | 3 | 4 | 5 | | V-1 | Cd209a | | |
| 9303 | 3 | 4 | 5 | | | V-1 | Capn1 | 823 | 17-May-15 | 9398 | 3 | 4 | 5 | | V-1 | Cd209c | | |
| 9304 | 3 | 4 | 5 | | | V-1 | Capn11 | 11131 | 4-May-15 | 9399 | 3 | 4 | 5 | | V-1 | Cd226 | 10666 | 12-May-15 |
| 9305 | 3 | 4 | 5 | | | V-1 | Capn13 | 92291 | 4-May-15 | 9400 | 3 | 4 | 5 | | V-1 | Cd27 | 939 | 4-May-15 |
| 9306 | 3 | 4 | 5 | | | V-1 | Capn7 | 23473 | 4-May-15 | 9401 | 3 | 4 | 5 | | V-1 | Cd300ld | 100131 439 | 4-May-15 |
| 9307 | 3 | 4 | 5 | | | V-1 | Capn9 | 10753 | 4-May-15 | 9402 | 3 | 4 | 5 | | V-1 | Cd302 | 9936 | 4-May-15 |
| 9308 | 3 | 4 | 5 | | | V-1 | Caprin1 | 4076 | 4-May-15 | 9403 | 3 | 4 | 5 | | V-1 | Cd320 | 51293 | 4-May-15 |
| 9309 | 3 | 4 | 5 | | | V-1 | Capza1 | 829 | 4-May-15 | 9404 | 3 | 4 | 5 | | V-1 | Cd34 | 947 | 17-May-15 |
| 9310 | 3 | 4 | 5 | | | V-1 | Capza2 | 830 | 4-May-15 | 9405 | 3 | 4 | 5 | | V-1 | Cd3d | 915 | 12-May-15 |
| 9311 | 3 | 4 | 5 | | | V-1 | Car10 | 8038 | 4-May-15 | 9406 | 3 | 4 | 5 | | V-1 | Cd3eap | 10849 | 4-May-15 |
| 9312 | 3 | 4 | 5 | | | V-1 | Car15 | | | 9407 | 3 | 4 | 5 | | V-1 | Cd4 | 920 | 17-May-15 |
| 9313 | 3 | 4 | 5 | | | V-1 | Car4 | 762 | 23-May-15 | 9408 | 3 | 4 | 5 | | V-1 | Cd40lg | 959 | 31-May-15 |
| 9314 | 3 | 4 | 5 | | | V-1 | Car6 | | | 9409 | 3 | 4 | 5 | | V-1 | Cd46 | 4179 | 23-May-15 |
| 9315 | 3 | 4 | 5 | | | V-1 | Car8 | | | 9410 | 3 | 4 | 5 | | V-1 | Cd5 | 921 | 12-May-15 |
| 9316 | 3 | 4 | 5 | | | V-1 | Card10 | 29775 | 4-May-15 | 9411 | 3 | 4 | 5 | | V-1 | Cd59a | | |
| 9317 | 3 | 4 | 5 | | | V-1 | Card11 | 84433 | 4-May-15 | 9412 | 3 | 4 | 5 | | V-1 | Cd59b | | |
| 9318 | 3 | 4 | 5 | | | V-1 | Card9 | 64170 | 24-May-15 | 9413 | 3 | 4 | 5 | | V-1 | Cd6 | 923 | 12-May-15 |
| 9319 | 3 | 4 | 5 | | | V-1 | Carf | 79800 | 7-Jun-15 | 9414 | 3 | 4 | 5 | | V-1 | Cd63 | 967 | 17-May-15 |
| 9320 | 3 | 4 | 5 | | | V-1 | Carkd | 55739 | 4-May-15 | 9415 | 3 | 4 | 5 | | V-1 | Cd81 | 975 | 31-May-15 |
| 9321 | 3 | 4 | 5 | | | V-1 | Cars | 833 | 4-May-15 | 9416 | 3 | 4 | 5 | | V-1 | Cd86 | 942 | 4-May-15 |
| 9322 | 3 | 4 | 5 | | | V-1 | Casc1 | 55259 | 4-May-15 | 9417 | 3 | 4 | 5 | | V-1 | Cd8a | 925 | 4-May-15 |
| 9323 | 3 | 4 | 5 | | | V-1 | Casd1 | 64921 | 4-May-15 | 9418 | 3 | 4 | 5 | | V-1 | Cd96 | 10225 | 12-May-15 |
| 9324 | 3 | 4 | 5 | | | V-1 | Casp12 | 100506 742 | 4-May-15 | 9419 | 3 | 4 | 5 | | V-1 | Cd99l2 | 83692 | 4-May-15 |
| 9325 | 3 | 4 | 5 | | | V-1 | Casp6 | 839 | 4-May-15 | 9420 | 3 | 4 | 5 | | V-1 | Cdaric1 | 81602 | 4-May-15 |
| 9326 | 3 | 4 | 5 | | | V-1 | Casp8ap2 | 9994 | 12-May-15 | 9421 | 3 | 4 | 5 | | V-1 | Cdc14b | 8555 | 13-Jun-15 |
| 9327 | 3 | 4 | 5 | | | V-1 | Cast | 831 | 7-Jun-15 | 9422 | 3 | 4 | 5 | | V-1 | Cdc20b | 166979 | 4-May-15 |
| 9328 | 3 | 4 | 5 | | | V-1 | Catsperb | 79820 | 4-May-15 | 9423 | 3 | 4 | 5 | | V-1 | Cdc26 | 246184 | 4-May-15 |
| 9329 | 3 | 4 | 5 | | | V-1 | Cav2 | 858 | 4-May-15 | 9424 | 3 | 4 | 5 | | V-1 | Cdc42ep2 | 10435 | 4-May-15 |
| 9330 | 3 | 4 | 5 | | | V-1 | Cav3 | 859 | 23-May-15 | 9425 | 3 | 4 | 5 | | V-1 | Cdc42ep3 | 10602 | 4-May-15 |
| 9331 | 3 | 4 | 5 | | | V-1 | Cbfa2t2 | 9139 | 12-May-15 | 9426 | 3 | 4 | 5 | | V-1 | Cdc42ep4 | 23580 | 4-May-15 |
| 9332 | 3 | 4 | 5 | | | V-1 | Cbl | 867 | 12-May-15 | 9427 | 3 | 4 | 5 | | V-1 | Cdc42ep5 | 148170 | 4-May-15 |
| 9333 | 3 | 4 | 5 | | | V-1 | Cblb | 868 | 7-Jun-15 | 9428 | 3 | 4 | 5 | | V-1 | Cdc42se1 | 56882 | 21-May-15 |
| 9334 | 3 | 4 | 5 | | | V-1 | Cblc | 23624 | 7-Jun-15 | 9429 | 3 | 4 | 5 | | V-1 | Cdc42se2 | 56990 | 4-May-15 |
| 9335 | 3 | 4 | 5 | | | V-1 | Cbr3 | 874 | 4-May-15 | 9430 | 3 | 4 | 5 | | V-1 | Cdc6l | 988 | 24-May-15 |
| 9336 | 3 | 4 | 5 | | | V-1 | Cbr4 | 84869 | 4-May-15 | 9431 | 3 | 4 | 5 | | V-1 | Cdc73 | 79577 | 23-May-15 |
| 9337 | 3 | 4 | 5 | | | V-1 | Cbx3 | 11335 | 12-May-15 | 9432 | 3 | 4 | 5 | | V-1 | Cdcp2 | 200008 | 4-May-15 |
| 9338 | 3 | 4 | 5 | | | V-1 | Cbx4 | 8535 | 17-May-15 | 9433 | 3 | 4 | 5 | | V-1 | Cdh10 | 1008 | 4-May-15 |
| 9339 | 3 | 4 | 5 | | | V-1 | Cbx5 | 23468 | 4-May-15 | 9434 | 3 | 4 | 5 | | V-1 | Cdh12 | 1010 | 4-May-15 |
| 9340 | 3 | 4 | 5 | | | V-1 | Cbx6 | 23466 | 12-May-15 | 9435 | 3 | 4 | 5 | | V-1 | Cdh15 | 1013 | 12-May-15 |
| 9341 | 3 | 4 | 5 | | | V-1 | Ccbl1 | 883 | 4-May-15 | 9436 | 3 | 4 | 5 | | V-1 | Cdh17 | 1015 | 17-May-15 |
| 9342 | 3 | 4 | 5 | | | V-1 | Ccbl2 | 56267 | 4-May-15 | 9437 | 3 | 4 | 5 | | V-1 | Cdh26 | 60437 | 4-May-15 |
| 9343 | 3 | 4 | 5 | | | V-1 | Ccdc103 | 388389 | 23-May-15 | 9438 | 3 | 4 | 5 | | V-1 | Cdh4 | 1002 | 4-May-15 |
| 9344 | 3 | 4 | 5 | | | V-1 | Ccdc109b | 55013 | 4-May-15 | 9439 | 3 | 4 | 5 | | V-1 | Cdh6 | 1004 | 12-May-15 |
| 9345 | 3 | 4 | 5 | | | V-1 | Ccdc11 | 220136 | 4-May-15 | 9440 | 3 | 4 | 5 | | V-1 | Cdk10 | 8558 | 12-May-15 |
| 9346 | 3 | 4 | 5 | | | V-1 | Ccdc116 | 164592 | 28-May-15 | 9441 | 3 | 4 | 5 | | V-1 | Cdk15 | 65061 | 4-May-15 |
| 9347 | 3 | 4 | 5 | | | V-1 | Ccdc120 | 90060 | 28-May-15 | 9442 | 3 | 4 | 5 | | V-1 | Cdk19 | 23097 | 12-May-15 |
| 9348 | 3 | 4 | 5 | | | V-1 | Ccdc124 | 115098 | 4-May-15 | 9443 | 3 | 4 | 5 | | V-1 | Cdk20 | 23552 | 4-May-15 |
| 9349 | 3 | 4 | 5 | | | V-1 | Ccdc137 | 339230 | 4-May-15 | 9444 | 3 | 4 | 5 | | V-1 | Cdk2ap1 | 8099 | 4-May-15 |
| 9350 | 3 | 4 | 5 | | | V-1 | Ccdc149 | 91050 | 4-May-15 | 9445 | 3 | 4 | 5 | | V-1 | Cdk5r2 | 8941 | 4-May-15 |
| 9351 | 3 | 4 | 5 | | | V-1 | Ccdc15 | 80071 | 4-May-15 | 9446 | 3 | 4 | 5 | | V-1 | Cdk7 | 1022 | 4-May-15 |
| 9352 | 3 | 4 | 5 | | | V-1 | Ccdc158 | 339965 | 4-May-15 | 9447 | 3 | 4 | 5 | | V-1 | Cdkl2 | 8999 | 4-May-15 |
| 9353 | 3 | 4 | 5 | | | V-1 | Ccdc177 | 56936 | 4-May-15 | 9448 | 3 | 4 | 5 | | V-1 | Cdkl5 | 6792 | 23-May-15 |
| 9354 | 3 | 4 | 5 | | | V-1 | Ccdc181 | 57823 | 4-May-15 | 9449 | 3 | 4 | 5 | | V-1 | Cdkn1b | 1027 | 31-May-15 |
| 9355 | 3 | 4 | 5 | | | V-1 | Ccdc184 | 387856 | 4-May-15 | 9450 | 3 | 4 | 5 | | V-1 | Cdkn2aip | 55602 | 4-May-15 |
| 9356 | 3 | 4 | 5 | | | V-1 | Ccdc185 | 164127 | 4-May-15 | 9451 | 3 | 4 | 5 | | V-1 | Cdpf1 | 150383 | 4-May-15 |
| 9357 | 3 | 4 | 5 | | | V-1 | Ccdc24 | 149473 | 12-May-15 | 9452 | 3 | 4 | 5 | | V-1 | Cdr2l | 30850 | 12-May-15 |
| 9358 | 3 | 4 | 5 | | | V-1 | Ccdc34os | | | 9453 | 3 | 4 | 5 | | V-1 | Cdrt4 | 284040 | 4-May-15 |
| 9359 | 3 | 4 | 5 | | | V-1 | Ccdc58 | 131076 | 21-May-15 | 9454 | 3 | 4 | 5 | | V-1 | Cds2 | 8760 | 4-May-15 |
| 9360 | 3 | 4 | 5 | | | V-1 | Ccdc60 | 160777 | 4-May-15 | 9455 | 3 | 4 | 5 | | V-1 | Cdv3 | 55573 | 4-May-15 |
| 9361 | 3 | 4 | 5 | | | V-1 | Ccdc64b | 146439 | 4-May-15 | 9456 | 3 | 4 | 5 | | V-1 | Ceacam11 | | |
| 9362 | 3 | 4 | 5 | | | V-1 | Ccdc67 | 159989 | 4-May-15 | 9457 | 3 | 4 | 5 | | V-1 | Ceacam18 | 729767 | 4-May-15 |
| 9363 | 3 | 4 | 5 | | | V-1 | Ccdc7 | 79741 | 4-May-15 | 9458 | 3 | 4 | 5 | | V-1 | Ceacam20 | 125931 | 4-May-15 |
| 9364 | 3 | 4 | 5 | | | V-1 | Ccdc73 | 493860 | 4-May-15 | 9459 | 3 | 4 | 5 | | V-1 | Cebpg | 1054 | 28-May-15 |
| 9365 | 3 | 4 | 5 | | | V-1 | Ccdc78 | 124093 | 4-May-15 | 9460 | 3 | 4 | 5 | | V-1 | Cecr5 | 27440 | 4-May-15 |
| 9366 | 3 | 4 | 5 | | | V-1 | Ccdc79 | 283847 | 4-May-15 | 9461 | 3 | 4 | 5 | | V-1 | Celf1 | 10658 | 2-Jun-15 |
| 9367 | 3 | 4 | 5 | | | V-1 | Ccdc81 | 60494 | 28-May-15 | 9462 | 3 | 4 | 5 | | V-1 | Celf3 | 11189 | 4-May-15 |
| 9368 | 3 | 4 | 5 | | | V-1 | Ccdc83 | 220047 | 4-May-15 | 9463 | 3 | 4 | 5 | | V-1 | Celf5 | 60680 | 3-Jun-15 |
| 9369 | 3 | 4 | 5 | | | V-1 | Ccdc87 | 55231 | 4-May-15 | 9464 | 3 | 4 | 5 | | V-1 | Celsr2 | 1952 | 31-May-15 |
| 9370 | 3 | 4 | 5 | | | V-1 | Ccdc88c | 440193 | 12-May-15 | 9465 | 3 | 4 | 5 | | V-1 | Cend1 | 51286 | 4-May-15 |
| 9371 | 3 | 4 | 5 | | | V-1 | Ccdc93 | 54520 | 4-May-15 | 9466 | 3 | 4 | 5 | | V-1 | Cenpb | 1059 | 4-May-15 |
| 9372 | 3 | 4 | 5 | | | V-1 | Ccin | 881 | 4-May-15 | 9467 | 3 | 4 | 5 | | V-1 | Cenpj | 55835 | 31-May-15 |
| 9373 | 3 | 4 | 5 | | | V-1 | Cckbr | 887 | 12-May-15 | 9468 | 3 | 4 | 5 | | V-1 | Cenpo | 79172 | 4-May-15 |
| 9374 | 3 | 4 | 5 | | | V-1 | Ccl22 | 6367 | 4-May-15 | 9469 | 3 | 4 | 5 | | V-1 | Cenpv | 201161 | 4-May-15 |

Fig. 30 - 51

| | | | | | | | | | | | | | | | | |
|---|---|---|---|---|---|---|---|---|---|---|---|---|---|---|---|---|
| 9470 | 3 | 4 | 5 | | | V-1 | Cep104 | 9731 | 4-May-15 | 9565 | 3 | 4 | 5 | | | V-1 | Clip1 | 6249 | 4-May-15 |
| 9471 | 3 | 4 | 5 | | | V-1 | Cep131 | 22994 | 4-May-15 | 9566 | 3 | 4 | 5 | | | V-1 | Clip2 | 7461 | 7-Jun-15 |
| 9472 | 3 | 4 | 5 | | | V-1 | Cep162 | 22832 | 4-May-15 | 9567 | 3 | 4 | 5 | | | V-1 | Clk1 | 1195 | 7-Jun-15 |
| 9473 | 3 | 4 | 5 | | | V-1 | Cep170b | 283638 | 4-May-15 | 9568 | 3 | 4 | 5 | | | V-1 | Cln3 | 1201 | 23-May-15 |
| 9474 | 3 | 4 | 5 | | | V-1 | Cep19 | 84984 | 4-May-15 | 9569 | 3 | 4 | 5 | | | V-1 | Clnk | 116449 | 4-May-15 |
| 9475 | 3 | 4 | 5 | | | V-1 | Cep250 | 11190 | 17-May-15 | 9570 | 3 | 4 | 5 | | | V-1 | Clp1 | 10978 | 16-Jun-15 |
| 9476 | 3 | 4 | 5 | | | V-1 | Cep44 | 80817 | 4-May-15 | 9571 | 3 | 4 | 5 | | | V-1 | Clptm1 | 1209 | 4-May-15 |
| 9477 | 3 | 4 | 5 | | | V-1 | Cep57 | 9702 | 4-May-15 | 9572 | 3 | 4 | 5 | | | V-1 | Clrn1 | 7401 | 23-May-15 |
| 9478 | 3 | 4 | 5 | | | V-1 | Cep63 | 80254 | 4-May-15 | 9573 | 3 | 4 | 5 | | | V-1 | Clstn1 | 22883 | 4-May-15 |
| 9479 | 3 | 4 | 5 | | | V-1 | Cep78 | 84131 | 4-May-15 | 9574 | 3 | 4 | 5 | | | V-1 | Clstn3 | 9746 | 4-May-15 |
| 9480 | 3 | 4 | 5 | | | V-1 | Cep89 | 84902 | 12-May-15 | 9575 | 3 | 4 | 5 | | | V-1 | Clta | 1211 | 4-May-15 |
| 9481 | 3 | 4 | 5 | | | V-1 | Cep95 | 90799 | 12-May-15 | 9576 | 3 | 4 | 5 | | | V-1 | Cluap1 | 23059 | 4-May-15 |
| 9482 | 3 | 4 | 5 | | | V-1 | Cept1 | 10390 | 12-May-15 | 9577 | 3 | 4 | 5 | | | V-1 | Cma2 | | |
| 9483 | 3 | 4 | 5 | | | V-1 | Cerkl | 375298 | 23-May-15 | 9578 | 3 | 4 | 5 | | | V-1 | Cmc1 | 152100 | 4-May-15 |
| 9484 | 3 | 4 | 5 | | | V-1 | Ces1a | | | 9579 | 3 | 4 | 5 | | | V-1 | Cmip | 80799 | 12-May-15 |
| 9485 | 3 | 4 | 5 | | | V-1 | Ces2b | | | 9580 | 3 | 4 | 5 | | | V-1 | Cml1 | 9027 | |
| 9486 | 3 | 4 | 5 | | | V-1 | Ces2e | | | 9581 | 3 | 4 | 5 | | | V-1 | Cml2 | 51471 | 4-May-15 |
| 9487 | 3 | 4 | 5 | | | V-1 | Ces2h | | | 9582 | 3 | 4 | 5 | | | V-1 | Cmpk1 | 51727 | 14-May-15 |
| 9488 | 3 | 4 | 5 | | | V-1 | Cetn1 | 1068 | 4-May-15 | 9583 | 3 | 4 | 5 | | | V-1 | Cmtm4 | 146223 | 4-May-15 |
| 9489 | 3 | 4 | 5 | | | V-1 | Cfc1 | 55997 | 4-May-15 | 9584 | 3 | 4 | 5 | | | V-1 | Cmtm5 | 116173 | 4-May-15 |
| 9490 | 3 | 4 | 5 | | | V-1 | Cfdp1 | 10428 | 4-May-15 | 9585 | 3 | 4 | 5 | | | V-1 | Cmtm8 | 152189 | 4-May-15 |
| 9491 | 3 | 4 | 5 | | | V-1 | Cfhr1 | 3078 | 23-May-15 | 9586 | 3 | 4 | 5 | | | V-1 | Cmtr1 | 23070 | 12-May-15 |
| 9492 | 3 | 4 | 5 | | | V-1 | Cfl1 | 1072 | 7-Jun-15 | 9587 | 3 | 4 | 5 | | | V-1 | Cnbd2 | 140894 | 12-May-15 |
| 9493 | 3 | 4 | 5 | | | V-1 | Cfl2 | 1073 | 23-May-15 | 9588 | 3 | 4 | 5 | | | V-1 | Cndp2 | 55748 | 12-May-15 |
| 9494 | 3 | 4 | 5 | | | V-1 | Cggbp1 | 8545 | 4-May-15 | 9589 | 3 | 4 | 5 | | | V-1 | Cnepir1 | 255919 | 4-May-15 |
| 9495 | 3 | 4 | 5 | | | V-1 | Cgnl1 | 84952 | 12-May-15 | 9590 | 3 | 4 | 5 | | | V-1 | Cnksr3 | 154043 | 4-May-15 |
| 9496 | 3 | 4 | 5 | | | V-1 | Cgrrf1 | 10668 | 21-May-15 | 9591 | 3 | 4 | 5 | | | V-1 | Cnn3 | 1266 | 4-May-15 |
| 9497 | 3 | 4 | 5 | | | V-1 | Chad | 150356 | 12-May-15 | 9592 | 3 | 4 | 5 | | | V-1 | Cnnm1 | 26507 | 4-May-15 |
| 9498 | 3 | 4 | 5 | | | V-1 | Champ1 | 283489 | 4-May-15 | 9593 | 3 | 4 | 5 | | | V-1 | Cnnm3 | 26505 | 4-May-15 |
| 9499 | 3 | 4 | 5 | | | V-1 | Chchd2 | 51142 | 21-May-15 | 9594 | 3 | 4 | 5 | | | V-1 | Cnppd1 | 27013 | 12-May-15 |
| 9500 | 3 | 4 | 5 | | | V-1 | Chchd5 | 84269 | 4-May-15 | 9595 | 3 | 4 | 5 | | | V-1 | Cnr2 | 1269 | 17-May-15 |
| 9501 | 3 | 4 | 5 | | | V-1 | Chd1 | 1105 | 12-May-15 | 9596 | 3 | 4 | 5 | | | V-1 | Cnrip1 | 25927 | 21-May-15 |
| 9502 | 3 | 4 | 5 | | | V-1 | Chd8 | 57680 | 12-May-15 | 9597 | 3 | 4 | 5 | | | V-1 | Cnst | 163882 | 4-May-15 |
| 9503 | 3 | 4 | 5 | | | V-1 | Cherp | 10523 | 4-May-15 | 9598 | 3 | 4 | 5 | | | V-1 | Cntd1 | 124817 | 4-May-15 |
| 9504 | 3 | 4 | 5 | | | V-1 | Chgb | 1114 | 21-May-15 | 9599 | 3 | 4 | 5 | | | V-1 | Cntln | 54875 | 1-Jun-15 |
| 9505 | 3 | 4 | 5 | | | V-1 | Chic1 | 53344 | 4-May-15 | 9600 | 3 | 4 | 5 | | | V-1 | Cntn6 | 27255 | 21-May-15 |
| 9506 | 3 | 4 | 5 | | | V-1 | Chic2 | 26511 | 4-May-15 | 9601 | 3 | 4 | 5 | | | V-1 | Cntrl | 11064 | 4-May-15 |
| 9507 | 3 | 4 | 5 | | | V-1 | Chi6 | | | 9602 | 3 | 4 | 5 | | | V-1 | Coa3 | 28958 | 4-May-15 |
| 9508 | 3 | 4 | 5 | | | V-1 | Chkb | 1120 | 22-May-15 | 9603 | 3 | 4 | 5 | | | V-1 | Cog1 | 9382 | 23-May-15 |
| 9509 | 3 | 4 | 5 | | | V-1 | Chm | 1121 | 7-Jun-15 | 9604 | 3 | 4 | 5 | | | V-1 | Col11a2 | 1302 | 23-May-15 |
| 9510 | 3 | 4 | 5 | | | V-1 | Chodl | 140578 | 12-May-15 | 9605 | 3 | 4 | 5 | | | V-1 | Col13a1 | 1305 | 12-May-15 |
| 9511 | 3 | 4 | 5 | | | V-1 | Chpf2 | 54480 | 4-May-15 | 9606 | 3 | 4 | 5 | | | V-1 | Col17a1 | 1308 | 24-May-15 |
| 9512 | 3 | 4 | 5 | | | V-1 | Chpt1 | 56994 | 4-May-15 | 9607 | 3 | 4 | 5 | | | V-1 | Col19a1 | 1310 | 12-May-15 |
| 9513 | 3 | 4 | 5 | | | V-1 | Chrac1 | 54108 | 12-May-15 | 9608 | 3 | 4 | 5 | | | V-1 | Col20a1 | 57642 | 4-May-15 |
| 9514 | 3 | 4 | 5 | | | V-1 | Chrdl2 | 25884 | 4-May-15 | 9609 | 3 | 4 | 5 | | | V-1 | Col22a1 | 169044 | 12-May-15 |
| 9515 | 3 | 4 | 5 | | | V-1 | Chrm1 | 1128 | 4-May-15 | 9610 | 3 | 4 | 5 | | | V-1 | Col23a1 | 91522 | 12-May-15 |
| 9516 | 3 | 4 | 5 | | | V-1 | Chrm4 | 1132 | 12-May-15 | 9611 | 3 | 4 | 5 | | | V-1 | Col24a1 | 255631 | 21-May-15 |
| 9517 | 3 | 4 | 5 | | | V-1 | Chrna5 | 1138 | 24-May-15 | 9612 | 3 | 4 | 5 | | | V-1 | Col28a1 | 340267 | 4-May-15 |
| 9518 | 3 | 4 | 5 | | | V-1 | Chrna7 | 1139 | 7-Jun-15 | 9613 | 3 | 4 | 5 | | | V-1 | Col4a3bp | 10087 | 21-May-15 |
| 9519 | 3 | 4 | 5 | | | V-1 | Chrnb2 | 1141 | 23-May-15 | 9614 | 3 | 4 | 5 | | | V-1 | Col4a5 | 1287 | 23-May-15 |
| 9520 | 3 | 4 | 5 | | | V-1 | Chrng | 1146 | 4-May-15 | 9615 | 3 | 4 | 5 | | | V-1 | Col4a6 | 1288 | 12-May-15 |
| 9521 | 3 | 4 | 5 | | | V-1 | Chst11 | 50515 | 4-May-15 | 9616 | 3 | 4 | 5 | | | V-1 | Col9a1 | 1297 | 23-May-15 |
| 9522 | 3 | 4 | 5 | | | V-1 | Chst13 | 166012 | 4-May-15 | 9617 | 3 | 4 | 5 | | | V-1 | Colec12 | 81035 | 3-May-15 |
| 9523 | 3 | 4 | 5 | | | V-1 | Chst5 | 23563 | 4-May-15 | 9618 | 3 | 4 | 5 | | | V-1 | Commd1 | 150684 | 4-May-15 |
| 9524 | 3 | 4 | 5 | | | V-1 | Chsy3 | 337876 | #NAME? | 9619 | 3 | 4 | 5 | | | V-1 | Commd2 | 51122 | 4-May-15 |
| 9525 | 3 | 4 | 5 | | | V-1 | Cht8 | 54921 | 12-May-15 | 9620 | 3 | 4 | 5 | | | V-1 | Comt | 1312 | 31-May-15 |
| 9526 | 3 | 4 | 5 | | | V-1 | Cib1 | 10519 | 4-May-15 | 9621 | 3 | 4 | 5 | | | V-1 | Comtd1 | 118881 | 4-May-15 |
| 9527 | 3 | 4 | 5 | | | V-1 | Cib4 | 130106 | 4-May-15 | 9622 | 3 | 4 | 5 | | | V-1 | Copa | 1314 | 4-May-15 |
| 9528 | 3 | 4 | 5 | | | V-1 | Ciita | 4261 | 12-May-15 | 9623 | 3 | 4 | 5 | | | V-1 | Cops2 | 9318 | 4-May-15 |
| 9529 | 3 | 4 | 5 | | | V-1 | Cilp2 | 148113 | 4-May-15 | 9624 | 3 | 4 | 5 | | | V-1 | Coq2 | 27235 | 12-May-15 |
| 9530 | 3 | 4 | 5 | | | V-1 | Cinp | 51550 | 4-May-15 | 9625 | 3 | 4 | 5 | | | V-1 | Coq4 | 51117 | 3-Jun-15 |
| 9531 | 3 | 4 | 5 | | | V-1 | Cirh1a | 84916 | 12-May-15 | 9626 | 3 | 4 | 5 | | | V-1 | Coq6 | 51004 | 23-May-15 |
| 9532 | 3 | 4 | 5 | | | V-1 | Cistr-act | 102216 268 | 12-May-15 | 9627 | 3 | 4 | 5 | | | V-1 | Coro1b | 57175 | 4-May-15 |
| | | | | | | | | | | 9628 | 3 | 4 | 5 | | | V-1 | Coro2b | 10391 | 4-May-15 |
| 9533 | 3 | 4 | 5 | | | V-1 | Cited2 | 10370 | 10-May-15 | 9629 | 3 | 4 | 5 | | | V-1 | Cox10 | 1352 | 22-May-15 |
| 9534 | 3 | 4 | 5 | | | V-1 | Ciz1 | 25792 | 12-May-15 | 9630 | 3 | 4 | 5 | | | V-1 | Cox14 | 84987 | 12-May-15 |
| 9535 | 3 | 4 | 5 | | | V-1 | Ckap4 | 10970 | 4-May-15 | 9631 | 3 | 4 | 5 | | | V-1 | Cox20 | 116228 | 4-May-15 |
| 9536 | 3 | 4 | 5 | | | V-1 | Ckap5 | 9793 | 4-May-15 | 9632 | 3 | 4 | 5 | | | V-1 | Cox5a | 9377 | 4-May-15 |
| 9537 | 3 | 4 | 5 | | | V-1 | Cks1brt | | | 9633 | 3 | 4 | 5 | | | V-1 | Cox6b1 | 1340 | 4-May-15 |
| 9538 | 3 | 4 | 5 | | | V-1 | Clasp1 | 23332 | 28-May-15 | 9634 | 3 | 4 | 5 | | | V-1 | Cox7a2 | 1347 | 4-May-15 |
| 9539 | 3 | 4 | 5 | | | V-1 | Clca4 | 22802 | 12-May-15 | 9635 | 3 | 4 | 5 | | | V-1 | Cox8c | 341947 | 4-May-15 |
| 9540 | 3 | 4 | 5 | | | V-1 | Clca6 | | | 9636 | 3 | 4 | 5 | | | V-1 | Cpa4 | 51200 | 4-May-15 |
| 9541 | 3 | 4 | 5 | | | V-1 | Clcn1 | 1180 | 23-May-15 | 9637 | 3 | 4 | 5 | | | V-1 | Cpd | 1362 | 7-Jun-15 |
| 9542 | 3 | 4 | 5 | | | V-1 | Clcn3 | 1182 | 4-May-15 | 9638 | 3 | 4 | 5 | | | V-1 | Cphx1 | | |
| 9543 | 3 | 4 | 5 | | | V-1 | Clcn4-2 | | | 9639 | 3 | 4 | 5 | | | V-1 | Cplx3 | 594855 | 4-May-15 |
| 9544 | 3 | 4 | 5 | | | V-1 | Clcn7 | 1186 | 23-May-15 | 9640 | 3 | 4 | 5 | | | V-1 | Cpn2 | 1370 | 7-Jun-15 |
| 9545 | 3 | 4 | 5 | | | V-1 | Cldn11 | 5010 | 12-May-15 | 9641 | 3 | 4 | 5 | | | V-1 | Cpne3 | 8895 | 3-May-15 |
| 9546 | 3 | 4 | 5 | | | V-1 | Cldn12 | 9069 | 4-May-15 | 9642 | 3 | 4 | 5 | | | V-1 | Cpne6 | 9362 | 4-May-15 |
| 9547 | 3 | 4 | 5 | | | V-1 | Cldn14 | 23562 | 4-May-15 | 9643 | 3 | 4 | 5 | | | V-1 | Cpne8 | 144402 | 4-May-15 |
| 9548 | 3 | 4 | 5 | | | V-1 | Cldn16 | 10686 | 4-May-15 | 9644 | 3 | 4 | 5 | | | V-1 | Cpne9 | 151835 | 4-May-15 |
| 9549 | 3 | 4 | 5 | | | V-1 | Cldn19 | 149461 | 1-Jun-15 | 9645 | 3 | 4 | 5 | | | V-1 | Cpped1 | 55313 | 4-May-15 |
| 9550 | 3 | 4 | 5 | | | V-1 | Cldn25 | 644672 | 4-May-15 | 9646 | 3 | 4 | 5 | | | V-1 | Cps1 | 1373 | 7-Jun-15 |
| 9551 | 3 | 4 | 5 | | | V-1 | Cldn9 | 9080 | 4-May-15 | 9647 | 3 | 4 | 5 | | | V-1 | Cpsf3 | 51692 | 4-May-15 |
| 9552 | 3 | 4 | 5 | | | V-1 | Clec12b | 387837 | 4-May-15 | 9648 | 3 | 4 | 5 | | | V-1 | Cpsf6 | 13052 | 1-Jun-15 |
| 9553 | 3 | 4 | 5 | | | V-1 | Clec16a | 23274 | 10-May-15 | 9649 | 3 | 4 | 5 | | | V-1 | Cpt1c | 126129 | 28-May-15 |
| 9554 | 3 | 4 | 5 | | | V-1 | Clec1b | 51266 | 4-May-15 | 9650 | 3 | 4 | 5 | | | V-1 | Cpxm2 | 119587 | 4-May-15 |
| 9555 | 3 | 4 | 5 | | | V-1 | Clec2d | 29121 | 4-May-15 | 9651 | 3 | 4 | 5 | | | V-1 | Cradd | 8738 | 4-May-15 |
| 9556 | 3 | 4 | 5 | | | V-1 | Clec2g | | | 9652 | 3 | 4 | 5 | | | V-1 | Crb1 | 23418 | 23-May-15 |
| 9557 | 3 | 4 | 5 | | | V-1 | Clec2i | 154790 | 4-May-15 | 9653 | 3 | 4 | 5 | | | V-1 | Crbn | 51185 | 4-May-15 |
| 9558 | 3 | 4 | 5 | | | V-1 | Clec4b2 | | | 9654 | 3 | 4 | 5 | | | V-1 | Creb1 | 1385 | 2-Jun-15 |
| 9559 | 3 | 4 | 5 | | | V-1 | Clec4f | 165530 | 4-May-15 | 9655 | 3 | 4 | 5 | | | V-1 | Creb3l3 | 84699 | 28-May-15 |
| 9560 | 3 | 4 | 5 | | | V-1 | Clec9a | 283420 | 1-Jun-15 | 9656 | 3 | 4 | 5 | | | V-1 | Crebbp | 1387 | 23-May-15 |
| 9561 | 3 | 4 | 5 | | | V-1 | Clgn | 1047 | 13-Jun-15 | 9657 | 3 | 4 | 5 | | | V-1 | Creg2 | 200407 | 4-May-15 |
| 9562 | 3 | 4 | 5 | | | V-1 | Clic4 | 25932 | 4-May-15 | 9658 | 3 | 4 | 5 | | | V-1 | Creld1 | 78987 | 4-May-15 |
| 9563 | 3 | 4 | 5 | | | V-1 | Clic5 | 53405 | 4-May-15 | 9659 | 3 | 4 | 5 | | | V-1 | Crem | 1390 | 12-May-15 |
| 9564 | 3 | 4 | 5 | | | V-1 | Clint1 | 9685 | 12-May-15 | 9660 | 3 | 4 | 5 | | | V-1 | Crh | 1392 | 4-May-15 |

Fig. 30 - 52

| | | | | | | | | | | | | | | | |
|---|---|---|---|---|---|---|---|---|---|---|---|---|---|---|---|
| 9661 | 3 | 4 | 5 | | | V-1 | Crhr1 | 1394 | 12-May-15 | 9757 | 3 | 4 | 5 | | | V-1 | Cyp4f40 | | |
| 9662 | 3 | 4 | 5 | | | V-1 | Crim1 | 51232 | 12-May-15 | 9758 | 3 | 4 | 5 | | | V-1 | Cyp4x1 | 260293 | 4-May-15 |
| 9663 | 3 | 4 | 5 | | | V-1 | Crip2 | 1397 | 4-May-15 | 9759 | 3 | 4 | 5 | | | V-1 | Cyp8b1 | 1582 | 12-May-15 |
| 9664 | 3 | 4 | 5 | | | V-1 | Crispld1 | 83690 | 4-May-15 | 9760 | 3 | 4 | 5 | | | V-1 | Cyp1 | | |
| 9665 | 3 | 4 | 5 | | | V-1 | Crk | 1398 | 17-May-15 | 9761 | 3 | 4 | 5 | | | V-1 | Cysltr2 | 57105 | 9-May-15 |
| 9666 | 3 | 4 | 5 | | | V-1 | Crlf2 | 64109 | 12-May-15 | 9762 | 3 | 4 | 5 | | | V-1 | Cyth1 | 9267 | 12-May-15 |
| 9667 | 3 | 4 | 5 | | | V-1 | Crlf3 | 51379 | 12-May-15 | 9763 | 3 | 4 | 5 | | | V-1 | Cyth2 | 9266 | 31-May-15 |
| 9668 | 3 | 4 | 5 | | | V-1 | Crls1 | 54675 | 4-May-15 | 9764 | 3 | 4 | 5 | | | V-1 | D030018L15Rik | | |
| 9669 | 3 | 4 | 5 | | | V-1 | Crp | 1401 | #NAME? | 9765 | 3 | 4 | 5 | | | V-1 | D030040B21Rik | | |
| 9670 | 3 | 4 | 5 | | | V-1 | Crtap | 10491 | 4-May-15 | 9766 | 3 | 4 | 5 | | | V-1 | D10Bwg1379e | | |
| 9671 | 3 | 4 | 5 | | | V-1 | Crtc1 | 23373 | 4-May-15 | 9767 | 3 | 4 | 5 | | | V-1 | D10Jhu81e | | |
| 9672 | 3 | 4 | 5 | | | V-1 | Cryba1 | 1411 | 17-May-15 | 9768 | 3 | 4 | 5 | | | V-1 | D1SErtd621e | | |
| 9673 | 3 | 4 | 5 | | | V-1 | Crybb2 | 1415 | 21-May-15 | 9769 | 3 | 4 | 5 | | | V-1 | D1Pas1 | | |
| 9674 | 3 | 4 | 5 | | | V-1 | Crybg3 | 131544 | 4-May-15 | 9770 | 3 | 4 | 5 | | | V-1 | D230030E09Rik | | |
| 9675 | 3 | 4 | 5 | | | V-1 | Cryga | 1418 | 4-May-15 | 9771 | 3 | 4 | 5 | | | V-1 | D330041H03Rik | | |
| 9676 | 3 | 4 | 5 | | | V-1 | Cryz | 1429 | 12-May-15 | 9772 | 3 | 4 | 5 | | | V-1 | D330045A20Rik | | |
| 9677 | 3 | 4 | 5 | | | V-1 | Csdc2 | 27254 | 4-May-15 | 9773 | 3 | 4 | 5 | | | V-1 | D430036J16Rik | | |
| 9678 | 3 | 4 | 5 | | | V-1 | Csf1r | 1436 | 24-May-15 | 9774 | 3 | 4 | 5 | | | V-1 | D430041D05Rik | | |
| 9679 | 3 | 4 | 5 | | | V-1 | Csf2 | 1437 | 4-May-15 | 9775 | 3 | 4 | 5 | | | V-1 | D430042O09Rik | | |
| 9680 | 3 | 4 | 5 | | | V-1 | Csf3 | 1440 | 12-May-15 | 9776 | 3 | 4 | 5 | | | V-1 | D630029K05Rik | | |
| 9681 | 3 | 4 | 5 | | | V-1 | Csgalnact2 | 55454 | 12-May-15 | 9777 | 3 | 4 | 5 | | | V-1 | D630033O11Rik | | |
| 9682 | 3 | 4 | 5 | | | V-1 | Csl | | | 9778 | 3 | 4 | 5 | | | V-1 | D630041G03Rik | | |
| 9683 | 3 | 4 | 5 | | | V-1 | Cspp1 | 79848 | 12-May-15 | 9779 | 3 | 4 | 5 | | | V-1 | D730050B12Rik | | |
| 9684 | 3 | 4 | 5 | | | V-1 | Csrnp2 | 81566 | 28-May-15 | 9780 | 3 | 4 | 5 | | | V-1 | D830026I12Rik | | |
| 9685 | 3 | 4 | 5 | | | V-1 | Csrp2bp | 57325 | 7-Jun-15 | 9781 | 3 | 4 | 5 | | | V-1 | D930016D06Rik | | |
| 9686 | 3 | 4 | 5 | | | V-1 | Cst10 | | | 9782 | 3 | 4 | 5 | | | V-1 | D930020B18Rik | | |
| 9687 | 3 | 4 | 5 | | | V-1 | Cst13 | | | 9783 | 3 | 4 | 5 | | | V-1 | Dab2ip | 153090 | 4-May-15 |
| 9688 | 3 | 4 | 5 | | | V-1 | Cst6 | 1474 | 7-Jun-15 | 9784 | 3 | 4 | 5 | | | V-1 | Dach2 | 117154 | 4-May-15 |
| 9689 | 3 | 4 | 5 | | | V-1 | Cst8 | 10047 | 4-May-15 | 9785 | 3 | 4 | 5 | | | V-1 | Dad1 | 1603 | 12-May-15 |
| 9690 | 3 | 4 | 5 | | | V-1 | Csta1 | | | 9786 | 3 | 4 | 5 | | | V-1 | Dag1 | 1605 | 28-May-15 |
| 9691 | 3 | 4 | 5 | | | V-1 | Cstb | 1476 | 23-May-15 | 9787 | 3 | 4 | 5 | | | V-1 | Dagib | 221955 | 21-May-15 |
| 9692 | 3 | 4 | 5 | | | V-1 | Cstf1 | 1477 | 12-May-15 | 9788 | 3 | 4 | 5 | | | V-1 | Dak | 26007 | 4-May-15 |
| 9693 | 3 | 4 | 5 | | | V-1 | Cstl1 | 128817 | 12-May-15 | 9789 | 3 | 4 | 5 | | | V-1 | Dand5 | 199699 | 4-May-15 |
| 9694 | 3 | 4 | 5 | | | V-1 | Ctdnep1 | 23399 | 4-May-15 | 9790 | 3 | 4 | 5 | | | V-1 | Dap3 | 7818 | 7-Jun-15 |
| 9695 | 3 | 4 | 5 | | | V-1 | Ctdsp1 | 58190 | 4-May-15 | 9791 | 3 | 4 | 5 | | | V-1 | Dapk3 | 1613 | 4-May-15 |
| 9696 | 3 | 4 | 5 | | | V-1 | Ctdspl2 | 51496 | 12-May-15 | 9792 | 3 | 4 | 5 | | | V-1 | Dars | 1615 | 4-May-15 |
| 9697 | 3 | 4 | 5 | | | V-1 | Cth | 1491 | 7-Jun-15 | 9793 | 3 | 4 | 5 | | | V-1 | Dbh | 1621 | 23-May-15 |
| 9698 | 3 | 4 | 5 | | | V-1 | Ctif | 9811 | 12-May-15 | 9794 | 3 | 4 | 5 | | | V-1 | Dbndd1 | 79007 | 4-May-15 |
| 9699 | 3 | 4 | 5 | | | V-1 | Ctla2b | | | 9795 | 3 | 4 | 5 | | | V-1 | Dbndd2 | 55861 | 4-May-15 |
| 9700 | 3 | 4 | 5 | | | V-1 | Ctnna1 | 1495 | 12-May-15 | 9796 | 3 | 4 | 5 | | | V-1 | Dcaf12 | 25853 | 4-May-15 |
| 9701 | 3 | 4 | 5 | | | V-1 | Ctnnbl1 | 56259 | 12-May-15 | 9797 | 3 | 4 | 5 | | | V-1 | Dcaf5 | 8816 | 4-May-15 |
| 9702 | 3 | 4 | 5 | | | V-1 | Ctns | 1497 | 23-May-15 | 9798 | 3 | 4 | 5 | | | V-1 | Dcaf7 | 10238 | 4-May-15 |
| 9703 | 3 | 4 | 5 | | | V-1 | Ctps2 | 56474 | 4-May-15 | 9799 | 3 | 4 | 5 | | | V-1 | Dclre1b | 64858 | 4-May-15 |
| 9704 | 3 | 4 | 5 | | | V-1 | Ctsa | | | 9800 | 3 | 4 | 5 | | | V-1 | Dclre1c | 64421 | 23-May-15 |
| 9705 | 3 | 4 | 5 | | | V-1 | Ctsb | 1508 | 31-May-15 | 9801 | 3 | 4 | 5 | | | V-1 | Dcn | 1634 | 23-May-15 |
| 9706 | 3 | 4 | 5 | | | V-1 | Ctsd | 1509 | 23-May-15 | 9802 | 3 | 4 | 5 | | | V-1 | Dcp1a | 55802 | 4-May-15 |
| 9707 | 3 | 4 | 5 | | | V-1 | Ctsf | 8722 | 4-May-15 | 9803 | 3 | 4 | 5 | | | V-1 | Dctn1 | 1639 | 23-May-15 |
| 9708 | 3 | 4 | 5 | | | V-1 | Ctsh | 1512 | 12-May-15 | 9804 | 3 | 4 | 5 | | | V-1 | Dcun1d1 | 54165 | 2-Jun-15 |
| 9709 | 3 | 4 | 5 | | | V-1 | Ctsj | | | 9805 | 3 | 4 | 5 | | | V-1 | Dcun1d4 | 23142 | 4-May-15 |
| 9710 | 3 | 4 | 5 | | | V-1 | Ctsll3 | 644021 | 4-May-15 | 9806 | 3 | 4 | 5 | | | V-1 | Dcx | 1641 | 31-May-15 |
| 9711 | 3 | 4 | 5 | | | V-1 | Ctsw | 1521 | 4-May-15 | 9807 | 3 | 4 | 5 | | | V-1 | Dda1 | 79016 | 4-May-15 |
| 9712 | 3 | 4 | 5 | | | V-1 | Cttn | 2017 | 17-May-15 | 9808 | 3 | 4 | 5 | | | V-1 | Ddah2 | 23564 | 31-May-15 |
| 9713 | 3 | 4 | 5 | | | V-1 | Cttnbp2 | 83992 | 17-May-15 | 9809 | 3 | 4 | 5 | | | V-1 | Ddb1 | 1642 | 4-May-15 |
| 9714 | 3 | 4 | 5 | | | V-1 | Ctu1 | 90353 | 23-May-15 | 9810 | 3 | 4 | 5 | | | V-1 | Ddhd1 | 80821 | 28-May-15 |
| 9715 | 3 | 4 | 5 | | | V-1 | Ctu2 | 348180 | 4-May-15 | 9811 | 3 | 4 | 5 | | | V-1 | Ddit3 | 1649 | 17-May-15 |
| 9716 | 3 | 4 | 5 | | | V-1 | Ctxn2 | 399697 | 4-May-15 | 9812 | 3 | 4 | 5 | | | V-1 | Ddn | 23109 | 4-May-15 |
| 9717 | 3 | 4 | 5 | | | V-1 | Cubn | 8029 | 12-May-15 | 9813 | 3 | 4 | 5 | | | V-1 | Ddost | 1650 | 23-May-15 |
| 9718 | 3 | 4 | 5 | | | V-1 | Cul4b | 8450 | 23-May-15 | 9814 | 3 | 4 | 5 | | | V-1 | Ddrgk1 | 65992 | 4-May-15 |
| 9719 | 3 | 4 | 5 | | | V-1 | Cul9 | 23113 | 21-May-15 | 9815 | 3 | 4 | 5 | | | V-1 | Ddx17 | 10521 | 4-May-15 |
| 9720 | 3 | 4 | 5 | | | V-1 | Cutc | 51076 | 4-May-15 | 9816 | 3 | 4 | 5 | | | V-1 | Ddx23 | 9416 | 4-May-15 |
| 9721 | 3 | 4 | 5 | | | V-1 | Cwc15 | 51503 | 4-May-15 | 9817 | 3 | 4 | 5 | | | V-1 | Ddx27 | 55661 | 4-May-15 |
| 9722 | 3 | 4 | 5 | | | V-1 | Cwc25 | 54883 | 4-May-15 | 9818 | 3 | 4 | 5 | | | V-1 | Ddx39b | 7919 | 4-May-15 |
| 9723 | 3 | 4 | 5 | | | V-1 | Cxcr3 | 2833 | 12-May-15 | 9819 | 3 | 4 | 5 | | | V-1 | Ddx59 | 83479 | 4-May-15 |
| 9724 | 3 | 4 | 5 | | | V-1 | Cxxc1a | | | 9820 | 3 | 4 | 5 | | | V-1 | Deaf1 | 10522 | 4-May-15 |
| 9725 | 3 | 4 | 5 | | | V-1 | Cyb5 | 1528 | 12-May-15 | 9821 | 3 | 4 | 5 | | | V-1 | Decr2 | 26063 | 4-May-15 |
| 9726 | 3 | 4 | 5 | | | V-1 | Cyb561a3 | 220002 | 4-May-15 | 9822 | 3 | 4 | 5 | | | V-1 | Def8 | 54849 | 4-May-15 |
| 9727 | 3 | 4 | 5 | | | V-1 | Cyb5r4 | 51167 | 4-May-15 | 9823 | 3 | 4 | 5 | | | V-1 | Defa4 | 1669 | 4-May-15 |
| 9728 | 3 | 4 | 5 | | | V-1 | Cyb5rl | 606495 | 4-May-15 | 9824 | 3 | 4 | 5 | | | V-1 | Defa5 | 1670 | 24-May-15 |
| 9729 | 3 | 4 | 5 | | | V-1 | Cybrd1 | 79901 | 4-May-15 | 9825 | 3 | 4 | 5 | | | V-1 | Defa-ps13 | | |
| 9730 | 3 | 4 | 5 | | | V-1 | Cygb | 114757 | 12-May-15 | 9826 | 3 | 4 | 5 | | | V-1 | Defa-rs7 | | |
| 9731 | 3 | 4 | 5 | | | V-1 | Cyhr1 | 50626 | 4-May-15 | 9827 | 3 | 4 | 5 | | | V-1 | Defb33 | | |
| 9732 | 3 | 4 | 5 | | | V-1 | Cyp11b1 | 1584 | 4-May-15 | 9828 | 3 | 4 | 5 | | | V-1 | Defb36 | | |
| 9733 | 3 | 4 | 5 | | | V-1 | Cyp19a1 | 1588 | 21-May-15 | 9829 | 3 | 4 | 5 | | | V-1 | Defb40 | | |
| 9734 | 3 | 4 | 5 | | | V-1 | Cyp20a1 | 57404 | 4-May-15 | 9830 | 3 | 4 | 5 | | | V-1 | Defb43 | | |
| 9735 | 3 | 4 | 5 | | | V-1 | Cyp24a1 | 1591 | 4-May-15 | 9831 | 3 | 4 | 5 | | | V-1 | Defb44-ps | | |
| 9736 | 3 | 4 | 5 | | | V-1 | Cyp26c1 | 340665 | 4-May-15 | 9832 | 3 | 4 | 5 | | | V-1 | Defb46 | | |
| 9737 | 3 | 4 | 5 | | | V-1 | Cyp27b1 | 1594 | 12-May-15 | 9833 | 3 | 4 | 5 | | | V-1 | Defb50 | | |
| 9738 | 3 | 4 | 5 | | | V-1 | Cyp2b13 | | | 9834 | 3 | 4 | 5 | | | V-1 | Defb9 | 245912 | 4-May-15 |
| 9739 | 3 | 4 | 5 | | | V-1 | Cyp2c29 | | | 9835 | 3 | 4 | 5 | | | V-1 | Dennd1a | 57706 | 4-May-15 |
| 9740 | 3 | 4 | 5 | | | V-1 | Cyp2c40 | | | 9836 | 3 | 4 | 5 | | | V-1 | Dennd2a | 27142 | 4-May-15 |
| 9741 | 3 | 4 | 5 | | | V-1 | Cyp2c50 | | | 9837 | 3 | 4 | 5 | | | V-1 | Dennd2d | 79961 | 4-May-15 |
| 9742 | 3 | 4 | 5 | | | V-1 | Cyp2d13 | | | 9838 | 3 | 4 | 5 | | | V-1 | Dennd3 | 22898 | 12-May-15 |
| 9743 | 3 | 4 | 5 | | | V-1 | Cyp2d26 | | | 9839 | 3 | 4 | 5 | | | V-1 | Dennd4b | 9909 | 4-May-15 |
| 9744 | 3 | 4 | 5 | | | V-1 | Cyp2j11 | | | 9840 | 3 | 4 | 5 | | | V-1 | Dennd6a | 201627 | 4-May-15 |
| 9745 | 3 | 4 | 5 | | | V-1 | Cyp2j8 | | | 9841 | 3 | 4 | 5 | | | V-1 | Depdc5 | 9681 | 28-May-15 |
| 9746 | 3 | 4 | 5 | | | V-1 | Cyp2r1 | 120227 | 31-May-15 | 9842 | 3 | 4 | 5 | | | V-1 | Deptor | 64798 | 31-May-15 |
| 9747 | 3 | 4 | 5 | | | V-1 | Cyp2t4 | | | 9843 | 3 | 4 | 5 | | | V-1 | Dera | 51071 | 4-May-15 |
| 9748 | 3 | 4 | 5 | | | V-1 | Cyp2w1 | 54905 | 4-May-15 | 9844 | 3 | 4 | 5 | | | V-1 | Derl1 | 79139 | 29-May-15 |
| 9749 | 3 | 4 | 5 | | | V-1 | Cyp3a11 | | | 9845 | 3 | 4 | 5 | | | V-1 | Desi1 | 27351 | 7-Jun-15 |
| 9750 | 3 | 4 | 5 | | | V-1 | Cyp3a16 | | | 9846 | 3 | 4 | 5 | | | V-1 | Desi2 | 51029 | 7-Jun-15 |
| 9751 | 3 | 4 | 5 | | | V-1 | Cyp3a25 | | | 9847 | 3 | 4 | 5 | | | V-1 | Def1 | 55070 | 4-May-15 |
| 9752 | 3 | 4 | 5 | | | V-1 | Cyp4a29 | | | 9848 | 3 | 4 | 5 | | | V-1 | Dgat2l6 | 347516 | 4-May-15 |
| 9753 | 3 | 4 | 5 | | | V-1 | Cyp4f13 | | | 9849 | 3 | 4 | 5 | | | V-1 | Dgkb | 1607 | 4-May-15 |
| 9754 | 3 | 4 | 5 | | | V-1 | Cyp4f16 | | | 9850 | 3 | 4 | 5 | | | V-1 | Dgkg | 1608 | 12-May-15 |
| 9755 | 3 | 4 | 5 | | | V-1 | Cyp4f37 | | | 9851 | 3 | 4 | 5 | | | V-1 | Dgki | 9162 | 4-May-15 |
| 9756 | 3 | 4 | 5 | | | V-1 | Cyp4f39 | | | 9852 | 3 | 4 | 5 | | | V-1 | Dhdds | 79947 | 29-May-15 |

Fig. 30 - 53

| | | | | | | | | | | | | | | | | | |
|---|---|---|---|---|---|---|---|---|---|---|---|---|---|---|---|---|---|
| 9853 | 3 | 4 | 5 | | | V-1 | Dhodh | 1723 | 4-May-15 | 9949 | 3 | 4 | 5 | | | V-1 | Dusp6 | 1848 | 4-May-15 |
| 9854 | 3 | 4 | 5 | | | V-1 | Dhrs13 | 147015 | 4-May-15 | 9950 | 3 | 4 | 5 | | | V-1 | Dux | | |
| 9855 | 3 | 4 | 5 | | | V-1 | Dhrs2 | 10202 | 4-May-15 | 9951 | 3 | 4 | 5 | | | V-1 | Dync1i1 | 1780 | 12-May-15 |
| 9856 | 3 | 4 | 5 | | | V-1 | Dhrs7 | 51635 | 4-May-15 | 9952 | 3 | 4 | 5 | | | V-1 | Dynll2 | 140735 | 4-May-15 |
| 9857 | 3 | 4 | 5 | | | V-1 | Dhrs9 | 10170 | 4-May-15 | 9953 | 3 | 4 | 5 | | | V-1 | Dynlt1a | | |
| 9858 | 3 | 4 | 5 | | | V-1 | Dhrsx | 207063 | 4-May-15 | 9954 | 3 | 4 | 5 | | | V-1 | Dynlt3 | 6990 | 4-May-15 |
| 9859 | 3 | 4 | 5 | | | V-1 | Dhx8 | 1659 | 12-May-15 | 9955 | 3 | 4 | 5 | | | V-1 | Dyrk4 | 8798 | 4-May-15 |
| 9860 | 3 | 4 | 5 | | | V-1 | Dicer1 | 23405 | 24-May-15 | 9956 | 3 | 4 | 5 | | | V-1 | Dytn | 391475 | 4-May-15 |
| 9861 | 3 | 4 | 5 | | | V-1 | Diexf | 27042 | 4-May-15 | 9957 | 3 | 4 | 5 | | | V-1 | Dzip3 | 9666 | 21-May-15 |
| 9862 | 3 | 4 | 5 | | | V-1 | Dio3 | 1735 | 12-May-15 | 9958 | 3 | 4 | 5 | | | V-1 | E030013J19Rik | | |
| 9863 | 3 | 4 | 5 | | | V-1 | Dip2a | 23181 | 4-May-15 | 9959 | 3 | 4 | 5 | | | V-1 | E030048B06Rik | | |
| 9864 | 3 | 4 | 5 | | | V-1 | Dirc2 | 84925 | 4-May-15 | 9960 | 3 | 4 | 5 | | | V-1 | E130218I03Rik | | |
| 9865 | 3 | 4 | 5 | | | V-1 | Dis3l | 115752 | 12-May-15 | 9961 | 3 | 4 | 5 | | | V-1 | E130308A19Rik | | |
| 9866 | 3 | 4 | 5 | | | V-1 | Dixdc1 | 85458 | 12-May-15 | 9962 | 3 | 4 | 5 | | | V-1 | E130309F12Rik | | |
| 9867 | 3 | 4 | 5 | | | V-1 | Dkk1 | 22943 | 31-May-15 | 9963 | 3 | 4 | 5 | | | V-1 | E130311K13Rik | | |
| 9868 | 3 | 4 | 5 | | | V-1 | Dkk4 | 27121 | 4-May-15 | 9964 | 3 | 4 | 5 | | | V-1 | E130317F20Rik | | |
| 9869 | 3 | 4 | 5 | | | V-1 | Dlat | 1737 | 29-May-15 | 9965 | 3 | 4 | 5 | | | V-1 | E230008N13Rik | | |
| 9870 | 3 | 4 | 5 | | | V-1 | Dld | 1738 | 7-Jun-15 | 9966 | 3 | 4 | 5 | | | V-1 | E2f3 | 1871 | 17-May-15 |
| 9871 | 3 | 4 | 5 | | | V-1 | Dleu7 | 220107 | 12-May-15 | 9967 | 3 | 4 | 5 | | | V-1 | E2f4 | 1874 | 4-May-15 |
| 9872 | 3 | 4 | 5 | | | V-1 | Dlg3 | 1741 | 7-Jun-15 | 9968 | 3 | 4 | 5 | | | V-1 | E2f5 | 1875 | 4-May-15 |
| 9873 | 3 | 4 | 5 | | | V-1 | Dlg5 | 9231 | 12-May-15 | 9969 | 3 | 4 | 5 | | | V-1 | E330009J07Rik | | |
| 9874 | 3 | 4 | 5 | | | V-1 | Dlgap2 | 9228 | 4-May-15 | 9970 | 3 | 4 | 5 | | | V-1 | E330011O21Rik | | |
| 9875 | 3 | 4 | 5 | | | V-1 | Dlk1 | 8788 | 31-May-15 | 9971 | 3 | 4 | 5 | | | V-1 | E330014E10Rik | | |
| 9876 | 3 | 4 | 5 | | | V-1 | Dll3 | 10683 | 23-May-15 | 9972 | 3 | 4 | 5 | | | V-1 | E330021D16Rik | | |
| 9877 | 3 | 4 | 5 | | | V-1 | Dlsr | 1743 | 4-May-15 | 9973 | 3 | 4 | 5 | | | V-1 | E430025E21Rik | | |
| 9878 | 3 | 4 | 5 | | | V-1 | Dlx5 | 1749 | 28-May-15 | 9974 | 3 | 4 | 5 | | | V-1 | Eapp | 55837 | 12-May-15 |
| 9879 | 3 | 4 | 5 | | | V-1 | Dmbx1 | 127343 | 4-May-15 | 9975 | 3 | 4 | 5 | | | V-1 | Ear4 | | |
| 9880 | 3 | 4 | 5 | | | V-1 | Dmp1 | 1758 | 17-May-15 | 9976 | 3 | 4 | 5 | | | V-1 | Ears2 | 124454 | 12-May-15 |
| 9881 | 3 | 4 | 5 | | | V-1 | Dmr | 91833 | 3-May-15 | 9977 | 3 | 4 | 5 | | | V-1 | Ebag9 | 9166 | 17-May-15 |
| 9882 | 3 | 4 | 5 | | | V-1 | Dmrtc1b | 728656 | 4-May-15 | 9978 | 3 | 4 | 5 | | | V-1 | Ebf2 | 64641 | 4-May-15 |
| 9883 | 3 | 4 | 5 | | | V-1 | Dmwd | 1762 | 4-May-15 | 9979 | 3 | 4 | 5 | | | V-1 | Ebf3 | 253738 | 7-Jun-15 |
| 9884 | 3 | 4 | 5 | | | V-1 | Dnaaf1 | 123872 | 23-May-15 | 9980 | 3 | 4 | 5 | | | V-1 | Ebf4 | 57593 | 4-May-15 |
| 9885 | 3 | 4 | 5 | | | V-1 | Dnah9 | 1770 | 12-May-15 | 9981 | 3 | 4 | 5 | | | V-1 | Ebna1bp2 | 10969 | 4-May-15 |
| 9886 | 3 | 4 | 5 | | | V-1 | Dnajb11 | 51726 | 4-May-15 | 9982 | 3 | 4 | 5 | | | V-1 | Ecel1 | 9427 | 12-May-15 |
| 9887 | 3 | 4 | 5 | | | V-1 | Dnajb14 | 79982 | 4-May-15 | 9983 | 3 | 4 | 5 | | | V-1 | Echdc1 | 55862 | 4-May-15 |
| 9888 | 3 | 4 | 5 | | | V-1 | Dnajb4 | 11080 | 4-May-15 | 9984 | 3 | 4 | 5 | | | V-1 | Echdc3 | 79746 | 4-May-15 |
| 9889 | 3 | 4 | 5 | | | V-1 | Dnajb5 | 25822 | 4-May-15 | 9985 | 3 | 4 | 5 | | | V-1 | Echs1 | 1892 | 31-May-15 |
| 9890 | 3 | 4 | 5 | | | V-1 | Dnajc1 | 64215 | 4-May-15 | 9986 | 3 | 4 | 5 | | | V-1 | Eci2 | 10455 | 4-May-15 |
| 9891 | 3 | 4 | 5 | | | V-1 | Dnajc11 | 55735 | 4-May-15 | 9987 | 3 | 4 | 5 | | | V-1 | Eci3 | | |
| 9892 | 3 | 4 | 5 | | | V-1 | Dnajc16 | 23341 | 4-May-15 | 9988 | 3 | 4 | 5 | | | V-1 | Ecm1 | 1893 | 12-May-15 |
| 9893 | 3 | 4 | 5 | | | V-1 | Dnajc18 | 202052 | 4-May-15 | 9989 | 3 | 4 | 5 | | | V-1 | Ecm2 | 1842 | 4-May-15 |
| 9894 | 3 | 4 | 5 | | | V-1 | Dnajc7 | 7266 | 4-May-15 | 9990 | 3 | 4 | 5 | | | V-1 | Ecscr | 641700 | 4-May-15 |
| 9895 | 3 | 4 | 5 | | | V-1 | Dnal1 | 83544 | 23-May-15 | 9991 | 3 | 4 | 5 | | | V-1 | Ecsit | 51295 | 4-May-15 |
| 9896 | 3 | 4 | 5 | | | V-1 | Dnase1l1 | 1774 | 12-May-15 | 9992 | 3 | 4 | 5 | | | V-1 | Ect2l | 345930 | 4-May-15 |
| 9897 | 3 | 4 | 5 | | | V-1 | Dnase1l3 | 1776 | 4-May-15 | 9993 | 3 | 4 | 5 | | | V-1 | Edc3 | 80153 | 4-May-15 |
| 9898 | 3 | 4 | 5 | | | V-1 | Dnase2a | 1777 | 12-May-15 | 9994 | 3 | 4 | 5 | | | V-1 | Edem1 | 9695 | 23-May-15 |
| 9899 | 3 | 4 | 5 | | | V-1 | Dner | 92737 | 4-May-15 | 9995 | 3 | 4 | 5 | | | V-1 | Edem2 | 55741 | 4-May-15 |
| 9900 | 3 | 4 | 5 | | | V-1 | Dnmil | 10059 | 31-May-15 | 9996 | 3 | 4 | 5 | | | V-1 | Edem3 | 80267 | 4-May-15 |
| 9901 | 3 | 4 | 5 | | | V-1 | Dnmbp | 23268 | 4-May-15 | 9997 | 3 | 4 | 5 | | | V-1 | Edn2 | 1907 | 4-May-15 |
| 9902 | 3 | 4 | 5 | | | V-1 | Dnmt3a | 1788 | 21-May-15 | 9998 | 3 | 4 | 5 | | | V-1 | Ednra | 1909 | 31-May-15 |
| 9903 | 3 | 4 | 5 | | | V-1 | Dnt1 | 1791 | 12-May-15 | 9999 | 3 | 4 | 5 | | | V-1 | Edrf1 | 26098 | 4-May-15 |
| 9904 | 3 | 4 | 5 | | | V-1 | Doc2a | 8448 | 4-May-15 | 10000 | 3 | 4 | 5 | | | V-1 | Eef1b2 | 1933 | 4-May-15 |
| 9905 | 3 | 4 | 5 | | | V-1 | Doc2g | | | 10001 | 3 | 4 | 5 | | | V-1 | Eef1g | 1937 | 4-May-15 |
| 9906 | 3 | 4 | 5 | | | V-1 | Dock1 | 1793 | 24-May-15 | 10002 | 3 | 4 | 5 | | | V-1 | Eefsec | 60678 | 4-May-15 |
| 9907 | 3 | 4 | 5 | | | V-1 | Dock3 | 1795 | 12-May-15 | 10003 | 3 | 4 | 5 | | | V-1 | Efemp1 | 2202 | 29-May-15 |
| 9908 | 3 | 4 | 5 | | | V-1 | Dock5 | 80005 | 12-May-15 | 10004 | 3 | 4 | 5 | | | V-1 | Efhb | 151651 | 4-May-15 |
| 9909 | 3 | 4 | 5 | | | V-1 | Dock9 | 23348 | 12-May-15 | 10005 | 3 | 4 | 5 | | | V-1 | Efhc2 | 80258 | 4-May-15 |
| 9910 | 3 | 4 | 5 | | | V-1 | Dok4 | 55715 | 3-May-15 | 10006 | 3 | 4 | 5 | | | V-1 | Efna1 | 1942 | 14-May-15 |
| 9911 | 3 | 4 | 5 | | | V-1 | Dok6 | 220164 | 2-Jun-15 | 10007 | 3 | 4 | 5 | | | V-1 | Efna2 | 1943 | 12-May-15 |
| 9912 | 3 | 4 | 5 | | | V-1 | Dolk | 22845 | 23-May-15 | 10008 | 3 | 4 | 5 | | | V-1 | Efna4 | 1945 | 31-May-15 |
| 9913 | 3 | 4 | 5 | | | V-1 | Dolpp1 | 57171 | 21-May-15 | 10009 | 3 | 4 | 5 | | | V-1 | Efnb2 | 1948 | 4-May-15 |
| 9914 | 3 | 4 | 5 | | | V-1 | Dopey1 | 23033 | 4-May-15 | 10010 | 3 | 4 | 5 | | | V-1 | Eftud1 | 79631 | 4-May-15 |
| 9915 | 3 | 4 | 5 | | | V-1 | Dpep3 | 64180 | 4-May-15 | 10011 | 3 | 4 | 5 | | | V-1 | Egfem1 | | |
| 9916 | 3 | 4 | 5 | | | V-1 | Dph1 | 1801 | 4-May-15 | 10012 | 3 | 4 | 5 | | | V-1 | Egfl7 | 51162 | 4-May-15 |
| 9917 | 3 | 4 | 5 | | | V-1 | Dph6 | 89978 | 4-May-15 | 10013 | 3 | 4 | 5 | | | V-1 | Egfl8 | 80864 | 12-May-15 |
| 9918 | 3 | 4 | 5 | | | V-1 | Dph7 | 92715 | 12-May-15 | 10014 | 3 | 4 | 5 | | | V-1 | Egln1 | 54583 | 12-May-15 |
| 9919 | 3 | 4 | 5 | | | V-1 | Dpp6 | 1804 | 12-May-15 | 10015 | 3 | 4 | 5 | | | V-1 | Egr4 | 1961 | 4-May-15 |
| 9920 | 3 | 4 | 5 | | | V-1 | Dpp8 | 54878 | 21-May-15 | 10016 | 3 | 4 | 5 | | | V-1 | Ehbp1 | 23301 | 4-May-15 |
| 9921 | 3 | 4 | 5 | | | V-1 | Dpy19l1 | 23333 | 4-May-15 | 10017 | 3 | 4 | 5 | | | V-1 | Ehd1 | 10938 | 10-May-15 |
| 9922 | 3 | 4 | 5 | | | V-1 | Dpy19l2 | 283417 | 4-May-15 | 10018 | 3 | 4 | 5 | | | V-1 | Ehd2 | 30846 | 12-May-15 |
| 9923 | 3 | 4 | 5 | | | V-1 | Dpy19l4 | 286148 | 4-May-15 | 10019 | 3 | 4 | 5 | | | V-1 | Ehd4 | 30844 | 4-May-15 |
| 9924 | 3 | 4 | 5 | | | V-1 | Dpy30 | 84661 | 24-May-15 | 10020 | 3 | 4 | 5 | | | V-1 | Ehmt1 | 79813 | 23-May-15 |
| 9925 | 3 | 4 | 5 | | | V-1 | Dpys | 1807 | 4-May-15 | 10021 | 3 | 4 | 5 | | | V-1 | Eid2b | 126272 | 4-May-15 |
| 9926 | 3 | 4 | 5 | | | V-1 | Dpysl4 | 10570 | 4-May-15 | 10022 | 3 | 4 | 5 | | | V-1 | Eif1 | 10209 | 4-May-15 |
| 9927 | 3 | 4 | 5 | | | V-1 | Dqx1 | 165545 | 4-May-15 | 10023 | 3 | 4 | 5 | | | V-1 | Eif1ad | 84285 | 4-May-15 |
| 9928 | 3 | 4 | 5 | | | V-1 | Dr1 | 1810 | 24-May-15 | 10024 | 3 | 4 | 5 | | | V-1 | Eif1b | 10289 | 4-May-15 |
| 9929 | 3 | 4 | 5 | | | V-1 | Dram2 | 128338 | 4-May-15 | 10025 | 3 | 4 | 5 | | | V-1 | Eif2ak2 | 5610 | 31-May-15 |
| 9930 | 3 | 4 | 5 | | | V-1 | Drd1a | 1812 | 28-May-15 | 10026 | 3 | 4 | 5 | | | V-1 | Eif2ak3 | 9451 | 31-May-15 |
| 9931 | 3 | 4 | 5 | | | V-1 | Drd2 | 1813 | 31-May-15 | 10027 | 3 | 4 | 5 | | | V-1 | Eif2ak4 | 440275 | 4-May-15 |
| 9932 | 3 | 4 | 5 | | | V-1 | Dsc3 | 1825 | 13-Jun-15 | 10028 | 3 | 4 | 5 | | | V-1 | Eif3k | 27335 | 12-May-15 |
| 9933 | 3 | 4 | 5 | | | V-1 | Dscr3 | 10311 | 12-May-15 | 10029 | 3 | 4 | 5 | | | V-1 | Eif4a2 | 1974 | 4-May-15 |
| 9934 | 3 | 4 | 5 | | | V-1 | Dsel | 92126 | 4-May-15 | 10030 | 3 | 4 | 5 | | | V-1 | Eif4ebp1 | 1978 | 29-May-15 |
| 9935 | 3 | 4 | 5 | | | V-1 | Dsg1a | | | 10031 | 3 | 4 | 5 | | | V-1 | Eif4ebp2 | 1979 | 4-May-15 |
| 9936 | 3 | 4 | 5 | | | V-1 | Dsp | 1832 | 7-Jun-15 | 10032 | 3 | 4 | 5 | | | V-1 | Eif4enif1 | 56478 | 4-May-15 |
| 9937 | 3 | 4 | 5 | | | V-1 | Dtna | 1837 | 12-May-15 | 10033 | 3 | 4 | 5 | | | V-1 | Eif5a | 1984 | 7-Jun-15 |
| 9938 | 3 | 4 | 5 | | | V-1 | Dtnbp1 | 84062 | 31-May-15 | 10034 | 3 | 4 | 5 | | | V-1 | Elac1 | 55520 | 4-May-15 |
| 9939 | 3 | 4 | 5 | | | V-1 | Dtwd2 | 285605 | 12-May-15 | 10035 | 3 | 4 | 5 | | | V-1 | Elavl1 | 1994 | 2-Jun-15 |
| 9940 | 3 | 4 | 5 | | | V-1 | Dtx2 | 113878 | 4-May-15 | 10036 | 3 | 4 | 5 | | | V-1 | Eif1 | 1997 | 7-Jun-15 |
| 9941 | 3 | 4 | 5 | | | V-1 | Dtymk | 1841 | 4-May-15 | 10037 | 3 | 4 | 5 | | | V-1 | Eif2 | 1998 | 28-May-15 |
| 9942 | 3 | 4 | 5 | | | V-1 | Duox1 | 53905 | 24-May-15 | 10038 | 3 | 4 | 5 | | | V-1 | Eif4 | 2000 | 28-May-15 |
| 9943 | 3 | 4 | 5 | | | V-1 | Duoxa2 | 405753 | 4-May-15 | 10039 | 3 | 4 | 5 | | | V-1 | Elf5 | 2001 | 4-May-15 |
| 9944 | 3 | 4 | 5 | | | V-1 | Dusp11 | 8446 | 4-May-15 | 10040 | 3 | 4 | 5 | | | V-1 | Elfn1 | 392617 | 4-May-15 |
| 9945 | 3 | 4 | 5 | | | V-1 | Dusp15 | 128853 | 4-May-15 | 10041 | 3 | 4 | 5 | | | V-1 | Eli | 8178 | 4-May-15 |
| 9946 | 3 | 4 | 5 | | | V-1 | Dusp21 | 63904 | 4-May-15 | 10042 | 3 | 4 | 5 | | | V-1 | Elmo1 | 9844 | 24-May-15 |
| 9947 | 3 | 4 | 5 | | | V-1 | Dusp27 | 92235 | 4-May-15 | 10043 | 3 | 4 | 5 | | | V-1 | Elmo3 | 79767 | 4-May-15 |
| 9948 | 3 | 4 | 5 | | | V-1 | Dusp28 | 285193 | 4-May-15 | 10044 | 3 | 4 | 5 | | | V-1 | Elof1 | 84337 | 4-May-15 |

Fig. 30 - 54

| | | | | | | | | | | | | | | | | | |
|---|---|---|---|---|---|---|---|---|---|---|---|---|---|---|---|---|---|
| 10045 | 3 | 4 | 5 | | | V-1 | Elovl4 | 6785 | 12-May-15 | 10140 | 3 | 4 | 5 | | | V-1 | Fads6 | 283985 | 7-Jun-15 |
| 10046 | 3 | 4 | 5 | | | V-1 | Elovl7 | 79993 | 12-May-15 | 10141 | 3 | 4 | 5 | | | V-1 | Fahd2a | 51013 | 4-May-15 |
| 10047 | 3 | 4 | 5 | | | V-1 | Eltd1 | 64123 | 12-May-15 | 10142 | 3 | 4 | 5 | | | V-1 | Fam102a | 399665 | 4-May-15 |
| 10048 | 3 | 4 | 5 | | | V-1 | Emx1 | 23065 | 4-May-15 | 10143 | 3 | 4 | 5 | | | V-1 | Fam103a1 | 83640 | 4-May-15 |
| 10049 | 3 | 4 | 5 | | | V-1 | Emd | 2010 | 23-May-15 | 10144 | 3 | 4 | 5 | | | V-1 | Fam109a | 144717 | 4-May-15 |
| 10050 | 3 | 4 | 5 | | | V-1 | Emg1 | 10436 | 14-May-15 | 10145 | 3 | 4 | 5 | | | V-1 | Fam110a | 83541 | 4-May-15 |
| 10051 | 3 | 4 | 5 | | | V-1 | Emid1 | 129080 | 4-May-15 | 10146 | 3 | 4 | 5 | | | V-1 | Fam110c | 642273 | 4-May-15 |
| 10052 | 3 | 4 | 5 | | | V-1 | Emilin3 | 90187 | 7-Jun-15 | 10147 | 3 | 4 | 5 | | | V-1 | Fam114a1 | 92689 | 4-May-15 |
| 10053 | 3 | 4 | 5 | | | V-1 | Eml2 | 24139 | 12-May-15 | 10148 | 3 | 4 | 5 | | | V-1 | Fam114a2 | 10827 | 4-May-15 |
| 10054 | 3 | 4 | 5 | | | V-1 | Eml5 | 161436 | 12-May-15 | 10149 | 3 | 4 | 5 | | | V-1 | Fam115c | 285966 | 4-May-15 |
| 10055 | 3 | 4 | 5 | | | V-1 | Emp2 | 2013 | 12-May-15 | 10150 | 3 | 4 | 5 | | | V-1 | Fam115e | | |
| 10056 | 3 | 4 | 5 | | | V-1 | Emx1 | 2016 | 4-May-15 | 10151 | 3 | 4 | 5 | | | V-1 | Fam118a | 55007 | 4-May-15 |
| 10057 | 3 | 4 | 5 | | | V-1 | Emx2os | 196047 | 12-May-15 | 10152 | 3 | 4 | 5 | | | V-1 | Fam124b | 79843 | 4-May-15 |
| 10058 | 3 | 4 | 5 | | | V-1 | En1 | 2019 | 4-May-15 | 10153 | 3 | 4 | 5 | | | V-1 | Fam126a | 84668 | 23-May-15 |
| 10059 | 3 | 4 | 5 | | | V-1 | Enam | 10117 | 12-May-15 | 10154 | 3 | 4 | 5 | | | V-1 | Fam129a | 116496 | 12-May-15 |
| 10060 | 3 | 4 | 5 | | | V-1 | Endog | 2021 | 4-May-15 | 10155 | 3 | 4 | 5 | | | V-1 | Fam131a | 131408 | 12-May-15 |
| 10061 | 3 | 4 | 5 | | | V-1 | Endov | 284131 | 14-May-15 | 10156 | 3 | 4 | 5 | | | V-1 | Fam133b | 257415 | 4-May-15 |
| 10062 | 3 | 4 | 5 | | | V-1 | Enkd1 | 84080 | 4-May-15 | 10157 | 3 | 4 | 5 | | | V-1 | Fam134c | 162427 | 12-May-15 |
| 10063 | 3 | 4 | 5 | | | V-1 | Eno1 | 2023 | 24-May-15 | 10158 | 3 | 4 | 5 | | | V-1 | Fam13b | 51306 | 28-May-15 |
| 10064 | 3 | 4 | 5 | | | V-1 | Enoph1 | 58478 | 4-May-15 | 10159 | 3 | 4 | 5 | | | V-1 | Fam149a | 25854 | 4-May-15 |
| 10065 | 3 | 4 | 5 | | | V-1 | Enpp6 | 133121 | 12-May-15 | 10160 | 3 | 4 | 5 | | | V-1 | Fam149b | | |
| 10066 | 3 | 4 | 5 | | | V-1 | Enpp7 | 339221 | 4-May-15 | 10161 | 3 | 4 | 5 | | | V-1 | Fam150b | 285016 | 4-May-15 |
| 10067 | 3 | 4 | 5 | | | V-1 | Entpd3 | 956 | 4-May-15 | 10162 | 3 | 4 | 5 | | | V-1 | Fam151a | 338094 | 4-May-15 |
| 10068 | 3 | 4 | 5 | | | V-1 | Ep300 | 2033 | 29-May-15 | 10163 | 3 | 4 | 5 | | | V-1 | Fam160a2 | 84067 | 4-May-15 |
| 10069 | 3 | 4 | 5 | | | V-1 | Epb4.1l1 | | | 10164 | 3 | 4 | 5 | | | V-1 | Fam161b | 145483 | 12-May-15 |
| 10070 | 3 | 4 | 5 | | | V-1 | Epb4.1l2 | | | 10165 | 3 | 4 | 5 | | | V-1 | Fam168a | 23203 | 1-Jun-15 |
| 10071 | 3 | 4 | 5 | | | V-1 | Epb4.1l3 | | | 10166 | 3 | 4 | 5 | | | V-1 | Fam169b | 283777 | 4-May-15 |
| 10072 | 3 | 4 | 5 | | | V-1 | Epb4.1l4a | | | 10167 | 3 | 4 | 5 | | | V-1 | Fam172a | 83989 | 12-May-15 |
| 10073 | 3 | 4 | 5 | | | V-1 | Epb4.1l5 | | | 10168 | 3 | 4 | 5 | | | V-1 | Fam175a | 84142 | 4-May-15 |
| 10074 | 3 | 4 | 5 | | | V-1 | Epc1 | 80314 | 7-Jun-15 | 10169 | 3 | 4 | 5 | | | V-1 | Fam181a | 90050 | 4-May-15 |
| 10075 | 3 | 4 | 5 | | | V-1 | Epg5 | 57724 | 21-May-15 | 10170 | 3 | 4 | 5 | | | V-1 | Fam184a | 79632 | 4-May-15 |
| 10076 | 3 | 4 | 5 | | | V-1 | Epha3 | 2042 | 4-May-15 | 10171 | 3 | 4 | 5 | | | V-1 | Fam185a | 222234 | 4-May-15 |
| 10077 | 3 | 4 | 5 | | | V-1 | Ephb3 | 2049 | 4-May-15 | 10172 | 3 | 4 | 5 | | | V-1 | Fam188a | 80013 | 4-May-15 |
| 10078 | 3 | 4 | 5 | | | V-1 | Ephb4 | 2050 | 31-May-15 | 10173 | 3 | 4 | 5 | | | V-1 | Fam189a1 | 23359 | 4-May-15 |
| 10079 | 3 | 4 | 5 | | | V-1 | Ephb6 | 2051 | 17-May-15 | 10174 | 3 | 4 | 5 | | | V-1 | Fam189b | 10712 | 4-May-15 |
| 10080 | 3 | 4 | 5 | | | V-1 | Ephx3 | 79852 | 4-May-15 | 10175 | 3 | 4 | 5 | | | V-1 | Fam192a | 80011 | 4-May-15 |
| 10081 | 3 | 4 | 5 | | | V-1 | Ephx4 | 253152 | 4-May-15 | 10176 | 3 | 4 | 5 | | | V-1 | Fam195b | 348262 | 4-May-15 |
| 10082 | 3 | 4 | 5 | | | V-1 | Epo | 2056 | 7-Jun-15 | 10177 | 3 | 4 | 5 | | | V-1 | Fam199x | 139231 | 12-May-15 |
| 10083 | 3 | 4 | 5 | | | V-1 | Eprs | 2058 | 4-May-15 | 10178 | 3 | 4 | 5 | | | V-1 | Fam19a5 | 25817 | 4-May-15 |
| 10084 | 3 | 4 | 5 | | | V-1 | Eps8l3 | 79574 | 12-May-15 | 10179 | 3 | 4 | 5 | | | V-1 | Fam204a | 63877 | 4-May-15 |
| 10085 | 3 | 4 | 5 | | | V-1 | Ept1 | 85465 | 28-May-15 | 10180 | 3 | 4 | 5 | | | V-1 | Fam206a | 54942 | 4-May-15 |
| 10086 | 3 | 4 | 5 | | | V-1 | Epyc | 1833 | 4-May-15 | 10181 | 3 | 4 | 5 | | | V-1 | Fam207a | 85395 | 4-May-15 |
| 10087 | 3 | 4 | 5 | | | V-1 | Erbb2ip | 55914 | 28-May-15 | 10182 | 3 | 4 | 5 | | | V-1 | Fam20b | 9917 | 23-May-15 |
| 10088 | 3 | 4 | 5 | | | V-1 | Erbb4 | 2066 | 23-May-15 | 10183 | 3 | 4 | 5 | | | V-1 | Fam21 | | |
| 10089 | 3 | 4 | 5 | | | V-1 | Ercc2 | 2068 | 4-Jun-15 | 10184 | 3 | 4 | 5 | | | V-1 | Fam212a | 389119 | 4-May-15 |
| 10090 | 3 | 4 | 5 | | | V-1 | Ercc6l2 | 375748 | 4-May-15 | 10185 | 3 | 4 | 5 | | | V-1 | Fam214b | 80256 | 4-May-15 |
| 10091 | 3 | 4 | 5 | | | V-1 | Erf | 2077 | 7-Jun-15 | 10186 | 3 | 4 | 5 | | | V-1 | Fam216a | 29902 | 4-May-15 |
| 10092 | 3 | 4 | 5 | | | V-1 | Ergic1 | 57222 | 28-May-15 | 10187 | 3 | 4 | 5 | | | V-1 | Fam219aos | | |
| 10093 | 3 | 4 | 5 | | | V-1 | Eri1 | 90459 | 4-May-15 | 10188 | 3 | 4 | 5 | | | V-1 | Fam219b | 57184 | 4-May-15 |
| 10094 | 3 | 4 | 5 | | | V-1 | Eri2 | 112479 | 4-May-15 | 10189 | 3 | 4 | 5 | | | V-1 | Fam221a | 340277 | 4-May-15 |
| 10095 | 3 | 4 | 5 | | | V-1 | Eri3 | 79033 | 2-Jun-15 | 10190 | 3 | 4 | 5 | | | V-1 | Fam229a | 100128073 | 21-May-15 |
| 10096 | 3 | 4 | 5 | | | V-1 | Erlin1 | 10613 | 28-May-15 | 10191 | 3 | 4 | 5 | | | V-1 | Fam26d | 221301 | 12-May-15 |
| 10097 | 3 | 4 | 5 | | | V-1 | Erlin2 | 11160 | 29-May-15 | 10192 | 3 | 4 | 5 | | | V-1 | Fam32a | 26017 | 4-May-15 |
| 10098 | 3 | 4 | 5 | | | V-1 | Ermard | 55780 | 12-May-15 | 10193 | 3 | 4 | 5 | | | V-1 | Fam3a | 60343 | 4-May-15 |
| 10099 | 3 | 4 | 5 | | | V-1 | Ern2 | 16595 | 12-May-15 | 10194 | 3 | 4 | 5 | | | V-1 | Fam43a | 131583 | 4-May-15 |
| 10100 | 3 | 4 | 5 | | | V-1 | Ero1lb | 56605 | 4-May-15 | 10195 | 3 | 4 | 5 | | | V-1 | Fam43b | 163933 | 4-May-15 |
| 10101 | 3 | 4 | 5 | | | V-1 | Erv3 | 2086 | 21-May-15 | 10196 | 3 | 4 | 5 | | | V-1 | Fam47c | 442444 | 4-May-15 |
| 10102 | 3 | 4 | 5 | | | V-1 | Esco1 | 114799 | 4-May-15 | 10197 | 3 | 4 | 5 | | | V-1 | Fam49b | 51571 | 4-May-15 |
| 10103 | 3 | 4 | 5 | | | V-1 | Esd | 2098 | 4-May-15 | 10198 | 3 | 4 | 5 | | | V-1 | Fam50a | 9130 | 21-May-15 |
| 10104 | 3 | 4 | 5 | | | V-1 | Esp1 | | | 10199 | 3 | 4 | 5 | | | V-1 | Fam53c | 51307 | 12-May-15 |
| 10105 | 3 | 4 | 5 | | | V-1 | Espnl | 339768 | 12-May-15 | 10200 | 3 | 4 | 5 | | | V-1 | Fam57b | 83723 | 4-May-15 |
| 10106 | 3 | 4 | 5 | | | V-1 | Esr2 | 2100 | 31-May-15 | 10201 | 3 | 4 | 5 | | | V-1 | Fam58b | 339521 | 4-May-15 |
| 10107 | 3 | 4 | 5 | | | V-1 | Esrra | 2101 | 10-May-15 | 10202 | 3 | 4 | 5 | | | V-1 | Fam63a | 55793 | 4-May-15 |
| 10108 | 3 | 4 | 5 | | | V-1 | Esrrg | 2104 | 4-May-15 | 10203 | 3 | 4 | 5 | | | V-1 | Fam65a | 79567 | 4-May-15 |
| 10109 | 3 | 4 | 5 | | | V-1 | Esyt2 | 57488 | 4-May-15 | 10204 | 3 | 4 | 5 | | | V-1 | Fam65c | 140876 | 12-May-15 |
| 10110 | 3 | 4 | 5 | | | V-1 | Etfdh | 2110 | 12-May-15 | 10205 | 3 | 4 | 5 | | | V-1 | Fam69a | 388650 | 4-May-15 |
| 10111 | 3 | 4 | 5 | | | V-1 | Etnk1 | 55500 | 4-May-15 | 10206 | 3 | 4 | 5 | | | V-1 | Fam69c | 125704 | 4-May-15 |
| 10112 | 3 | 4 | 5 | | | V-1 | Etnppl | 64850 | 3-May-15 | 10207 | 3 | 4 | 5 | | | V-1 | Fam71d | 161142 | 4-May-15 |
| 10113 | 3 | 4 | 5 | | | V-1 | Etohd2 | | | 10208 | 3 | 4 | 5 | | | V-1 | Fam71e2 | 284418 | 4-May-15 |
| 10114 | 3 | 4 | 5 | | | V-1 | Ets2 | 2114 | 12-May-15 | 10209 | 3 | 4 | 5 | | | V-1 | Fam73a | 374986 | 4-May-15 |
| 10115 | 3 | 4 | 5 | | | V-1 | Etv4 | 2118 | 28-May-15 | 10210 | 3 | 4 | 5 | | | V-1 | Fam78b | 149297 | 4-May-15 |
| 10116 | 3 | 4 | 5 | | | V-1 | Etv6 | 2120 | 31-May-15 | 10211 | 3 | 4 | 5 | | | V-1 | Fam83c | 128876 | 4-May-15 |
| 10117 | 3 | 4 | 5 | | | V-1 | EU599041 | | | 10212 | 3 | 4 | 5 | | | V-1 | Fam83e | 54854 | 4-May-15 |
| 10118 | 3 | 4 | 5 | | | V-1 | Eva1c | 59271 | 4-May-15 | 10213 | 3 | 4 | 5 | | | V-1 | Fam86 | | |
| 10119 | 3 | 4 | 5 | | | V-1 | Evc2 | 132884 | 21-May-15 | 10214 | 3 | 4 | 5 | | | V-1 | Fam89b | 23625 | 4-May-15 |
| 10120 | 3 | 4 | 5 | | | V-1 | Evi2a-evi2b | | | 10215 | 3 | 4 | 5 | | | V-1 | Fam92b | 339145 | 4-May-15 |
| 10121 | 3 | 4 | 5 | | | V-1 | Evi5 | 7813 | 21-May-15 | 10216 | 3 | 4 | 5 | | | V-1 | Fam96b | 51647 | 4-May-15 |
| 10122 | 3 | 4 | 5 | | | V-1 | Evi5l | 115704 | 12-May-15 | 10217 | 3 | 4 | 5 | | | V-1 | Fancb | 2187 | 23-May-15 |
| 10123 | 3 | 4 | 5 | | | V-1 | Exo5 | 64789 | 4-May-15 | 10218 | 3 | 4 | 5 | | | V-1 | Fancc | 2176 | 28-May-15 |
| 10124 | 3 | 4 | 5 | | | V-1 | Exoc1 | 55763 | 7-Jun-15 | 10219 | 3 | 4 | 5 | | | V-1 | Fancd2os | 115795 | 4-May-15 |
| 10125 | 3 | 4 | 5 | | | V-1 | Exoc4 | 60412 | 4-May-15 | 10220 | 3 | 4 | 5 | | | V-1 | Fancl | 55120 | 23-May-15 |
| 10126 | 3 | 4 | 5 | | | V-1 | Exosc3 | 51010 | 23-May-15 | 10221 | 3 | 4 | 5 | | | V-1 | Fank1 | 92565 | 12-May-15 |
| 10127 | 3 | 4 | 5 | | | V-1 | Exosc7 | 23016 | 4-May-15 | 10222 | 3 | 4 | 5 | | | V-1 | Far2 | 55711 | 14-May-15 |
| 10128 | 3 | 4 | 5 | | | V-1 | Eya3 | 2140 | 4-May-15 | 10223 | 3 | 4 | 5 | | | V-1 | Farp1 | 10160 | 4-May-15 |
| 10129 | 3 | 4 | 5 | | | V-1 | F11 | 2160 | 7-Jun-15 | 10224 | 3 | 4 | 5 | | | V-1 | Farp2 | 9855 | 4-May-15 |
| 10130 | 3 | 4 | 5 | | | V-1 | F13b | 2165 | 12-May-15 | 10225 | 3 | 4 | 5 | | | V-1 | Fasl | 356 | 24-May-15 |
| 10131 | 3 | 4 | 5 | | | V-1 | F2rl1 | 2150 | 4-May-15 | 10226 | 3 | 4 | 5 | | | V-1 | Fastk | 10922 | 4-May-15 |
| 10132 | 3 | 4 | 5 | | | V-1 | F2rl2 | 2151 | 4-May-15 | 10227 | 3 | 4 | 5 | | | V-1 | Fat2 | 2196 | 12-May-15 |
| 10133 | 3 | 4 | 5 | | | V-1 | F420014N23Rik | | | 10228 | 3 | 4 | 5 | | | V-1 | Faxc | 84553 | 4-May-15 |
| 10134 | 3 | 4 | 5 | | | V-1 | F630042J09Rik | | | 10229 | 3 | 4 | 5 | | | V-1 | Fbi | 2091 | 4-May-15 |
| 10135 | 3 | 4 | 5 | | | V-1 | F730035M05Rik | | | 10230 | 3 | 4 | 5 | | | V-1 | Fblim1 | 54751 | 4-May-15 |
| 10136 | 3 | 4 | 5 | | | V-1 | F8 | 2157 | 23-May-15 | 10231 | 3 | 4 | 5 | | | V-1 | Fbll1 | 345630 | 3-May-15 |
| 10137 | 3 | 4 | 5 | | | V-1 | Fabp12 | 646486 | 4-May-15 | 10232 | 3 | 4 | 5 | | | V-1 | Fbrs | 64319 | 12-May-15 |
| 10138 | 3 | 4 | 5 | | | V-1 | Fabp6 | 2172 | 4-May-15 | 10233 | 3 | 4 | 5 | | | V-1 | Fbxl2os | | |
| 10139 | 3 | 4 | 5 | | | V-1 | Fadd | 8772 | 31-May-15 | 10234 | 3 | 4 | 5 | | | V-1 | Fbxl2 | 25827 | 4-May-15 |

Fig. 30 - 55

| | | | | | | | | | | | | | | | | |
|---|---|---|---|---|---|---|---|---|---|---|---|---|---|---|---|---|
| 10235 | 3 | 4 | 5 | | | V-1 | Fbxl3 | 26224 | 4-May-15 | 10331 | 3 | 4 | 5 | | | V-1 | Frem3 | 166752 | 12-May-15 |
| 10236 | 3 | 4 | 5 | | | V-1 | Fbxl8 | 55336 | 4-May-15 | 10332 | 3 | 4 | 5 | | | V-1 | Frk | 2444 | 4-May-15 |
| 10237 | 3 | 4 | 5 | | | V-1 | Fbxo11 | 80204 | 2-Jun-15 | 10333 | 3 | 4 | 5 | | | V-1 | Frmd4b | 23150 | 12-May-15 |
| 10238 | 3 | 4 | 5 | | | V-1 | Fbxo18 | 84893 | 4-May-15 | 10334 | 3 | 4 | 5 | | | V-1 | Frmd5 | 84978 | 4-May-15 |
| 10239 | 3 | 4 | 5 | | | V-1 | Fbxo22 | 26263 | 4-May-15 | 10335 | 3 | 4 | 5 | | | V-1 | Frrs1 | 391059 | 4-May-15 |
| 10240 | 3 | 4 | 5 | | | V-1 | Fbxo31 | 79791 | 7-Jun-15 | 10336 | 3 | 4 | 5 | | | V-1 | Fryl | 285527 | 4-May-15 |
| 10241 | 3 | 4 | 5 | | | V-1 | Fbxo33 | 254370 | 4-May-15 | 10337 | 3 | 4 | 5 | | | V-1 | Fsbp | 100861412 | 4-May-15 |
| 10242 | 3 | 4 | 5 | | | V-1 | Fbxo36 | 130888 | 4-May-15 | 10338 | 3 | 4 | 5 | | | V-1 | Fscn2 | 25794 | 23-May-15 |
| 10243 | 3 | 4 | 5 | | | V-1 | Fbxo38 | 81545 | 4-May-15 | 10339 | 3 | 4 | 5 | | | V-1 | Fscn3 | 29999 | 12-May-15 |
| 10244 | 3 | 4 | 5 | | | V-1 | Fbxo40 | 51725 | 4-May-15 | 10340 | 3 | 4 | 5 | | | V-1 | Fshb | 2488 | 12-May-15 |
| 10245 | 3 | 4 | 5 | | | V-1 | Fbxo41 | 150726 | 4-May-15 | 10341 | 3 | 4 | 5 | | | V-1 | Fstl4 | 23105 | 4-May-15 |
| 10246 | 3 | 4 | 5 | | | V-1 | Fbxo43 | 286151 | 4-May-15 | 10342 | 3 | 4 | 5 | | | V-1 | Fth1 | 2495 | 24-May-15 |
| 10247 | 3 | 4 | 5 | | | V-1 | Fbxo6 | 26270 | 4-May-15 | 10343 | 3 | 4 | 5 | | | V-1 | Ftmt | 94033 | 28-May-15 |
| 10248 | 3 | 4 | 5 | | | V-1 | Fbxo8 | 26269 | 4-May-15 | 10344 | 3 | 4 | 5 | | | V-1 | Ftsj2 | 29960 | 30-May-15 |
| 10249 | 3 | 4 | 5 | | | V-1 | Fbxw18 | | | 10345 | 3 | 4 | 5 | | | V-1 | Fubp1 | 8880 | 12-May-15 |
| 10250 | 3 | 4 | 5 | | | V-1 | Fcer1a | 2205 | 12-May-15 | 10346 | 3 | 4 | 5 | | | V-1 | Fuca2 | 2519 | 4-May-15 |
| 10251 | 3 | 4 | 5 | | | V-1 | Fcf1 | 51077 | 12-May-15 | 10347 | 3 | 4 | 5 | | | V-1 | Fuk | 197258 | 4-May-15 |
| 10252 | 3 | 4 | 5 | | | V-1 | Fcgrt | 2217 | 12-May-15 | 10348 | 3 | 4 | 5 | | | V-1 | Fundc2 | 65991 | 12-May-15 |
| 10253 | 3 | 4 | 5 | | | V-1 | Fcho2 | 115548 | 4-May-15 | 10349 | 3 | 4 | 5 | | | V-1 | Fut10 | 84750 | 4-May-15 |
| 10254 | 3 | 4 | 5 | | | V-1 | Fchsd2 | 9873 | 4-May-15 | 10350 | 3 | 4 | 5 | | | V-1 | Fut2 | 2524 | 31-May-15 |
| 10255 | 3 | 4 | 5 | | | V-1 | Fcrl5 | 83416 | 4-May-15 | 10351 | 3 | 4 | 5 | | | V-1 | Fut4-ps1 | | |
| 10256 | 3 | 4 | 5 | | | V-1 | Fdx1 | 2230 | 12-May-15 | 10352 | 3 | 4 | 5 | | | V-1 | Fut9 | 10690 | 12-May-15 |
| 10257 | 3 | 4 | 5 | | | V-1 | Fem1a | 55527 | 7-Jun-15 | 10353 | 3 | 4 | 5 | | | V-1 | Fxn | 2395 | 28-May-15 |
| 10258 | 3 | 4 | 5 | | | V-1 | Fem1c | 56929 | 4-May-15 | 10354 | 3 | 4 | 5 | | | V-1 | Fxr1 | 8087 | 1-Jun-15 |
| 10259 | 3 | 4 | 5 | | | V-1 | Fendrr | 400550 | 16-May-15 | 10355 | 3 | 4 | 5 | | | V-1 | Fxyd4 | 53828 | 4-May-15 |
| 10260 | 3 | 4 | 5 | | | V-1 | Fert2 | | | 10356 | 3 | 4 | 5 | | | V-1 | Fxyd7 | 53822 | 12-May-15 |
| 10261 | 3 | 4 | 5 | | | V-1 | Fev | 54738 | 12-May-15 | 10357 | 3 | 4 | 5 | | | V-1 | Fyttd1 | 84248 | 4-May-15 |
| 10262 | 3 | 4 | 5 | | | V-1 | Ffar3 | 2865 | 4-May-15 | 10358 | 3 | 4 | 5 | | | V-1 | Fzd3 | 7976 | 7-Jun-15 |
| 10263 | 3 | 4 | 5 | | | V-1 | Fgb | 2244 | 29-May-15 | 10359 | 3 | 4 | 5 | | | V-1 | Fzd5 | 7855 | 12-May-15 |
| 10264 | 3 | 4 | 5 | | | V-1 | Fgd4 | 121512 | 23-May-15 | 10360 | 3 | 4 | 5 | | | V-1 | Fzd6 | 8323 | 12-May-15 |
| 10265 | 3 | 4 | 5 | | | V-1 | Fgf1 | 2246 | 12-May-15 | 10361 | 3 | 4 | 5 | | | V-1 | Fzd8 | 8325 | 4-May-15 |
| 10266 | 3 | 4 | 5 | | | V-1 | Fgf10 | 2255 | 12-May-15 | 10362 | 3 | 4 | 5 | | | V-1 | Fzd9 | 8326 | 4-May-15 |
| 10267 | 3 | 4 | 5 | | | V-1 | Fgf11 | 2256 | 4-May-15 | 10363 | 3 | 4 | 5 | | | V-1 | G2e3 | 55632 | 23-May-15 |
| 10268 | 3 | 4 | 5 | | | V-1 | Fgf15 | | | 10364 | 3 | 4 | 5 | | | V-1 | G3bp1 | 10146 | 31-May-15 |
| 10269 | 3 | 4 | 5 | | | V-1 | Fgf2 | 2247 | 7-Jun-15 | 10365 | 3 | 4 | 5 | | | V-1 | G630025P09Rik | | |
| 10270 | 3 | 4 | 5 | | | V-1 | Fgf20 | 26281 | 4-May-15 | 10366 | 3 | 4 | 5 | | | V-1 | G6bos | | |
| 10271 | 3 | 4 | 5 | | | V-1 | Fgf22 | 27006 | 4-May-15 | 10367 | 3 | 4 | 5 | | | V-1 | G6pc2 | 57818 | 4-May-15 |
| 10272 | 3 | 4 | 5 | | | V-1 | Fgf3 | 2248 | 23-May-15 | 10368 | 3 | 4 | 5 | | | V-1 | G6pdx | | |
| 10273 | 3 | 4 | 5 | | | V-1 | Fgf8 | 2253 | 23-May-15 | 10369 | 3 | 4 | 5 | | | V-1 | G730013B05Rik | | |
| 10274 | 3 | 4 | 5 | | | V-1 | Fgfbp3 | 143282 | 4-May-15 | 10370 | 3 | 4 | 5 | | | V-1 | Gab2 | 9846 | 17-May-15 |
| 10275 | 3 | 4 | 5 | | | V-1 | Fgfr1op | 11116 | 4-May-15 | 10371 | 3 | 4 | 5 | | | V-1 | Gab3 | 139716 | 12-May-15 |
| 10276 | 3 | 4 | 5 | | | V-1 | Fgg | 2266 | 31-May-15 | 10372 | 3 | 4 | 5 | | | V-1 | Gabarapl2 | 11345 | 21-May-15 |
| 10277 | 3 | 4 | 5 | | | V-1 | Fgl1 | 2267 | 4-May-15 | 10373 | 3 | 4 | 5 | | | V-1 | Gabpb2 | 126626 | 7-Jun-15 |
| 10278 | 3 | 4 | 5 | | | V-1 | Fh1 | 2317 | 23-May-15 | 10374 | 3 | 4 | 5 | | | V-1 | Gabra5 | 2558 | 28-May-15 |
| 10279 | 3 | 4 | 5 | | | V-1 | Fhit | 2272 | 31-May-15 | 10375 | 3 | 4 | 5 | | | V-1 | Gabrb2 | 2561 | 12-May-15 |
| 10280 | 3 | 4 | 5 | | | V-1 | Fhl2 | 2274 | 31-May-15 | 10376 | 3 | 4 | 5 | | | V-1 | Gabrq | 55879 | 4-May-15 |
| 10281 | 3 | 4 | 5 | | | V-1 | Fhl5 | 9457 | 7-Jun-15 | 10377 | 3 | 4 | 5 | | | V-1 | Gabrr3 | 200959 | 13-May-15 |
| 10282 | 3 | 4 | 5 | | | V-1 | Fibp | 9158 | 2-Jun-15 | 10378 | 3 | 4 | 5 | | | V-1 | Gad1os | | |
| 10283 | 3 | 4 | 5 | | | V-1 | Figla | 344018 | 4-May-15 | 10379 | 3 | 4 | 5 | | | V-1 | Gadd45gip1 | 90480 | 4-May-15 |
| 10284 | 3 | 4 | 5 | | | V-1 | Fignl2 | 401720 | 4-May-15 | 10380 | 3 | 4 | 5 | | | V-1 | Galc | 2581 | 23-May-15 |
| 10285 | 3 | 4 | 5 | | | V-1 | Fikbp1 | 11259 | 4-May-15 | 10381 | 3 | 4 | 5 | | | V-1 | Galk1 | 2584 | 12-May-15 |
| 10286 | 3 | 4 | 5 | | | V-1 | Fip1l1 | 81608 | 3-May-15 | 10382 | 3 | 4 | 5 | | | V-1 | Galnt1 | 2589 | 4-May-15 |
| 10287 | 3 | 4 | 5 | | | V-1 | Fis1 | 51024 | 4-May-15 | 10383 | 3 | 4 | 5 | | | V-1 | Galnt11 | 63917 | 4-May-15 |
| 10288 | 3 | 4 | 5 | | | V-1 | Fitm2 | 128486 | 4-May-15 | 10384 | 3 | 4 | 5 | | | V-1 | Galnt13 | 114805 | 7-Jun-15 |
| 10289 | 3 | 4 | 5 | | | V-1 | Fiz1 | 84922 | 4-May-15 | 10385 | 3 | 4 | 5 | | | V-1 | Galnt18 | 374378 | 14-May-15 |
| 10290 | 3 | 4 | 5 | | | V-1 | Fkbp14 | 55033 | 4-May-15 | 10386 | 3 | 4 | 5 | | | V-1 | Galnt2 | 2590 | 4-May-15 |
| 10291 | 3 | 4 | 5 | | | V-1 | Fkbp15 | 23307 | 4-May-15 | 10387 | 3 | 4 | 5 | | | V-1 | Galnt4 | 8693 | 4-May-15 |
| 10292 | 3 | 4 | 5 | | | V-1 | Fkbp2 | 2286 | 4-May-15 | 10388 | 3 | 4 | 5 | | | V-1 | Galnt9 | 50614 | 4-May-15 |
| 10293 | 3 | 4 | 5 | | | V-1 | Fkbp6 | 8468 | 4-May-15 | 10389 | 3 | 4 | 5 | | | V-1 | Galntl5 | 168391 | 4-May-15 |
| 10294 | 3 | 4 | 5 | | | V-1 | Flg2 | 388698 | 12-May-15 | 10390 | 3 | 4 | 5 | | | V-1 | Gan | 8139 | 23-May-15 |
| 10295 | 3 | 4 | 5 | | | V-1 | Fli | 2314 | 3-Jun-15 | 10391 | 3 | 4 | 5 | | | V-1 | Ganab | 23193 | 4-May-15 |
| 10296 | 3 | 4 | 5 | | | V-1 | Flnb | 2317 | 23-May-15 | 10392 | 3 | 4 | 5 | | | V-1 | Gap43 | 2596 | 12-May-15 |
| 10297 | 3 | 4 | 5 | | | V-1 | Flot1 | 10231 | 31-May-15 | 10393 | 3 | 4 | 5 | | | V-1 | Gapvd1 | 26130 | 12-May-15 |
| 10298 | 3 | 4 | 5 | | | V-1 | Flrt3 | 23767 | 4-May-15 | 10394 | 3 | 4 | 5 | | | V-1 | Garem1 | 150946 | 4-May-15 |
| 10299 | 3 | 4 | 5 | | | V-1 | Flt1 | 2321 | 17-May-15 | 10395 | 3 | 4 | 5 | | | V-1 | Gas2 | 2620 | 4-May-15 |
| 10300 | 3 | 4 | 5 | | | V-1 | Flt3 | 2322 | 31-May-15 | 10396 | 3 | 4 | 5 | | | V-1 | Gas2l2 | 246176 | 4-May-15 |
| 10301 | 3 | 4 | 5 | | | V-1 | Flywch1 | 84256 | 12-May-15 | 10397 | 3 | 4 | 5 | | | V-1 | Gas8 | 2622 | 4-May-15 |
| 10302 | 3 | 4 | 5 | | | V-1 | Flywch2 | 114984 | 4-May-15 | 10398 | 3 | 4 | 5 | | | V-1 | Gata2 | 2624 | 28-May-15 |
| 10303 | 3 | 4 | 5 | | | V-1 | Fmnl2 | 114793 | 4-May-15 | 10399 | 3 | 4 | 5 | | | V-1 | Gata4 | 2626 | 31-May-15 |
| 10304 | 3 | 4 | 5 | | | V-1 | Fmnl3 | 91010 | 4-May-15 | 10400 | 3 | 4 | 5 | | | V-1 | Gatad1 | 57798 | 12-May-15 |
| 10305 | 3 | 4 | 5 | | | V-1 | Fmo6 | 388714 | 4-May-15 | 10401 | 3 | 4 | 5 | | | V-1 | Gatad2b | 57459 | 4-May-15 |
| 10306 | 3 | 4 | 5 | | | V-1 | Fmr1 | 2332 | 7-Jun-15 | 10402 | 3 | 4 | 5 | | | V-1 | Gatsl2 | 729438 | 14-May-15 |
| 10307 | 3 | 4 | 5 | | | V-1 | Fmr1nb | 158521 | 4-May-15 | 10403 | 3 | 4 | 5 | | | V-1 | Gba | 2629 | 31-May-15 |
| 10308 | 3 | 4 | 5 | | | V-1 | Fnbp1 | 23048 | 4-May-15 | 10404 | 3 | 4 | 5 | | | V-1 | Gba2 | 57704 | 4-May-15 |
| 10309 | 3 | 4 | 5 | | | V-1 | Fnd3c2 | | | 10405 | 3 | 4 | 5 | | | V-1 | Gbp4 | 115361 | 4-May-15 |
| 10310 | 3 | 4 | 5 | | | V-1 | Fndc3a | 22862 | 4-May-15 | 10406 | 3 | 4 | 5 | | | V-1 | Gbp8 | | |
| 10311 | 3 | 4 | 5 | | | V-1 | Fndc3c1 | | | 10407 | 3 | 4 | 5 | | | V-1 | Gbx1 | 2636 | 4-May-15 |
| 10312 | 3 | 4 | 5 | | | V-1 | Fnta | 2339 | 4-May-15 | 10408 | 3 | 4 | 5 | | | V-1 | Gca | 25801 | 4-May-15 |
| 10313 | 3 | 4 | 5 | | | V-1 | Focad | 54914 | 4-May-15 | 10409 | 3 | 4 | 5 | | | V-1 | Gchfr | 2644 | 4-May-15 |
| 10314 | 3 | 4 | 5 | | | V-1 | Folr4 | 390243 | 4-May-15 | 10410 | 3 | 4 | 5 | | | V-1 | Gckr | 2646 | 7-Jun-15 |
| 10315 | 3 | 4 | 5 | | | V-1 | Foxa2 | 3170 | 31-May-15 | 10411 | 3 | 4 | 5 | | | V-1 | Gcm1 | 8521 | 4-May-15 |
| 10316 | 3 | 4 | 5 | | | V-1 | Foxd1 | 2297 | 28-May-15 | 10412 | 3 | 4 | 5 | | | V-1 | Gcnt3 | 9245 | 24-May-15 |
| 10317 | 3 | 4 | 5 | | | V-1 | Foxd3 | 27022 | 17-May-15 | 10413 | 3 | 4 | 5 | | | V-1 | Gcsh | 2653 | 23-May-15 |
| 10318 | 3 | 4 | 5 | | | V-1 | Foxe1 | 2304 | 28-May-15 | 10414 | 3 | 4 | 5 | | | V-1 | Gdap1 | 54332 | 23-May-15 |
| 10319 | 3 | 4 | 5 | | | V-1 | Foxi2 | 399823 | 28-May-15 | 10415 | 3 | 4 | 5 | | | V-1 | Gdap1l1 | 78997 | 4-May-15 |
| 10320 | 3 | 4 | 5 | | | V-1 | Foxj2 | 55810 | 28-May-15 | 10416 | 3 | 4 | 5 | | | V-1 | Gdf2 | 2658 | 4-May-15 |
| 10321 | 3 | 4 | 5 | | | V-1 | Foxn1 | 8456 | 4-May-15 | 10417 | 3 | 4 | 5 | | | V-1 | Gdf7 | 151449 | 25-May-15 |
| 10322 | 3 | 4 | 5 | | | V-1 | Foxn3 | 1112 | 4-May-15 | 10418 | 3 | 4 | 5 | | | V-1 | Gdpd4 | 220032 | 4-May-15 |
| 10323 | 3 | 4 | 5 | | | V-1 | Foxo3 | 2309 | 31-May-15 | 10419 | 3 | 4 | 5 | | | V-1 | Gdpgp1 | 390637 | 12-May-15 |
| 10324 | 3 | 4 | 5 | | | V-1 | Foxo4 | 4303 | 12-May-15 | 10420 | 3 | 4 | 5 | | | V-1 | Gemin2 | 8487 | 4-May-15 |
| 10325 | 3 | 4 | 5 | | | V-1 | Foxp3 | 50943 | 31-May-15 | 10421 | 3 | 4 | 5 | | | V-1 | Gemin7 | 79760 | 4-May-15 |
| 10326 | 3 | 4 | 5 | | | V-1 | Foxq1 | 94234 | 28-May-15 | 10422 | 3 | 4 | 5 | | | V-1 | Get4 | 51608 | 29-May-15 |
| 10327 | 3 | 4 | 5 | | | V-1 | Foxr1 | 283150 | 28-May-15 | 10423 | 3 | 4 | 5 | | | V-1 | Gfer | 2671 | 12-May-15 |
| 10328 | 3 | 4 | 5 | | | V-1 | Fpgt | 8790 | 4-May-15 | 10424 | 3 | 4 | 5 | | | V-1 | Gfm1 | 85476 | 12-May-15 |
| 10329 | 3 | 4 | 5 | | | V-1 | Fpr3 | 2359 | 4-May-15 | 10425 | 3 | 4 | 5 | | | V-1 | Gfod2 | 81577 | 4-May-15 |
| 10330 | 3 | 4 | 5 | | | V-1 | Frem1 | 158326 | 23-May-15 | | | | | | | | | | |

Fig. 30 - 56

| | | | | | | | | | | | | | | | |
|---|---|---|---|---|---|---|---|---|---|---|---|---|---|---|---|
| 10426 | 3 | 4 | 5 | | | V-1 | Gfpt1 | 2673 | 23-May-15 | 10522 | 3 | 4 | 5 | | V-1 | Gm14085 |
| 10427 | 3 | 4 | 5 | | | V-1 | Gfra3 | 2676 | 4-May-15 | 10523 | 3 | 4 | 5 | | V-1 | Gm14092 |
| 10428 | 3 | 4 | 5 | | | V-1 | Gfral | 389400 | 4-May-15 | 10524 | 3 | 4 | 5 | | V-1 | Gm14305 |
| 10429 | 3 | 4 | 5 | | | V-1 | Ggcx | 2677 | 31-May-15 | 10525 | 3 | 4 | 5 | | V-1 | Gm14306 |
| 10430 | 3 | 4 | 5 | | | V-1 | Ggn | 199720 | 4-May-15 | 10526 | 3 | 4 | 5 | | V-1 | Gm14322 |
| 10431 | 3 | 4 | 5 | | | V-1 | Ggnbp2 | 79893 | 4-May-15 | 10527 | 3 | 4 | 5 | | V-1 | Gm14379 |
| 10432 | 3 | 4 | 5 | | | V-1 | Ggt5 | 2687 | 4-May-15 | 10528 | 3 | 4 | 5 | | V-1 | Gm14393 |
| 10433 | 3 | 4 | 5 | | | V-1 | Ggt6 | 124975 | 4-May-15 | 10529 | 3 | 4 | 5 | | V-1 | Gm14420 |
| 10434 | 3 | 4 | 5 | | | V-1 | Ghdc | 84514 | 4-May-15 | 10530 | 3 | 4 | 5 | | V-1 | Gm14458 |
| 10435 | 3 | 4 | 5 | | | V-1 | Ghrh | 2691 | 12-May-15 | 10531 | 3 | 4 | 5 | | V-1 | Gm14461 |
| 10436 | 3 | 4 | 5 | | | V-1 | Ghsr | 2693 | 12-May-15 | 10532 | 3 | 4 | 5 | | V-1 | Gm14625 |
| 10437 | 3 | 4 | 5 | | | V-1 | Gif | 2694 | 7-Jun-15 | 10533 | 3 | 4 | 5 | | V-1 | Gm14634 |
| 10438 | 3 | 4 | 5 | | | V-1 | Gimap5 | 55340 | 4-May-15 | 10534 | 3 | 4 | 5 | | V-1 | Gm14827 |
| 10439 | 3 | 4 | 5 | | | V-1 | Gimap8 | 155038 | 4-May-15 | 10535 | 3 | 4 | 5 | | V-1 | Gm15085 |
| 10440 | 3 | 4 | 5 | | | V-1 | Gimap9 | | | 10536 | 3 | 4 | 5 | | V-1 | Gm15091 |
| 10441 | 3 | 4 | 5 | | | V-1 | Gin1 | 54826 | 4-May-15 | 10537 | 3 | 4 | 5 | | V-1 | Gm15292 |
| 10442 | 3 | 4 | 5 | | | V-1 | Ginm1 | 116254 | 4-May-15 | 10538 | 3 | 4 | 5 | | V-1 | Gm15350 |
| 10443 | 3 | 4 | 5 | | | V-1 | Gins4 | 84296 | 4-May-15 | 10539 | 3 | 4 | 5 | | V-1 | Gm15401 |
| 10444 | 3 | 4 | 5 | | | V-1 | Gip | 2695 | 7-Jun-15 | 10540 | 3 | 4 | 5 | | V-1 | Gm15412 |
| 10445 | 3 | 4 | 5 | | | V-1 | Gipc1 | 10755 | 4-May-15 | 10541 | 3 | 4 | 5 | | V-1 | Gm15421 |
| 10446 | 3 | 4 | 5 | | | V-1 | Gja10 | 84694 | 4-May-15 | 10542 | 3 | 4 | 5 | | V-1 | Gm15446 |
| 10447 | 3 | 4 | 5 | | | V-1 | Gja5 | 2702 | 31-May-15 | 10543 | 3 | 4 | 5 | | V-1 | Gm156 |
| 10448 | 3 | 4 | 5 | | | V-1 | Gja6 | | | 10544 | 3 | 4 | 5 | | V-1 | Gm1564 |
| 10449 | 3 | 4 | 5 | | | V-1 | Gjb2 | 2706 | 31-May-15 | 10545 | 3 | 4 | 5 | | V-1 | Gm15713 |
| 10450 | 3 | 4 | 5 | | | V-1 | Gjc1 | 10052 | 7-Jun-15 | 10546 | 3 | 4 | 5 | | V-1 | Gm15787 |
| 10451 | 3 | 4 | 5 | | | V-1 | Gjc2 | 57165 | 12-May-15 | 10547 | 3 | 4 | 5 | | V-1 | Gm15850 |
| 10452 | 3 | 4 | 5 | | | V-1 | Gk5 | 256356 | 4-May-15 | 10548 | 3 | 4 | 5 | | V-1 | Gm1587 |
| 10453 | 3 | 4 | 5 | | | V-1 | Gkn2 | 200504 | 4-May-15 | 10549 | 3 | 4 | 5 | | V-1 | Gm15941 |
| 10454 | 3 | 4 | 5 | | | V-1 | Glb1 | 2720 | 12-May-15 | 10550 | 3 | 4 | 5 | | V-1 | Gm15997 |
| 10455 | 3 | 4 | 5 | | | V-1 | Glb1l | 79411 | 23-May-15 | 10551 | 3 | 4 | 5 | | V-1 | Gm16063 |
| 10456 | 3 | 4 | 5 | | | V-1 | Glcci1 | 113263 | 12-May-15 | 10552 | 3 | 4 | 5 | | V-1 | Gm16287 |
| 10457 | 3 | 4 | 5 | | | V-1 | Glce | 26035 | 4-May-15 | 10553 | 3 | 4 | 5 | | V-1 | Gm16523 |
| 10458 | 3 | 4 | 5 | | | V-1 | Gldn | 342035 | 4-May-15 | 10554 | 3 | 4 | 5 | | V-1 | Gm16576 |
| 10459 | 3 | 4 | 5 | | | V-1 | Gli3 | 2737 | 31-May-15 | 10555 | 3 | 4 | 5 | | V-1 | Gm16675 |
| 10460 | 3 | 4 | 5 | | | V-1 | Glipr1l1 | 256710 | 12-May-15 | 10556 | 3 | 4 | 5 | | V-1 | Gm16677 |
| 10461 | 3 | 4 | 5 | | | V-1 | Glis1 | 148979 | 4-May-15 | 10557 | 3 | 4 | 5 | | V-1 | Gm16740 |
| 10462 | 3 | 4 | 5 | | | V-1 | Glmn | 11146 | 12-May-15 | 10558 | 3 | 4 | 5 | | V-1 | Gm16796 |
| 10463 | 3 | 4 | 5 | | | V-1 | Glod4 | 51031 | 4-May-15 | 10559 | 3 | 4 | 5 | | V-1 | Gm16853 |
| 10464 | 3 | 4 | 5 | | | V-1 | Glrx | 2745 | 12-May-15 | 10560 | 3 | 4 | 5 | | V-1 | Gm16938 |
| 10465 | 3 | 4 | 5 | | | V-1 | Glrx2 | 51022 | 4-May-15 | 10561 | 3 | 4 | 5 | | V-1 | Gm16973 |
| 10466 | 3 | 4 | 5 | | | V-1 | Gls | 2744 | 13-Jun-15 | 10562 | 3 | 4 | 5 | | V-1 | Gm17019 |
| 10467 | 3 | 4 | 5 | | | V-1 | Gls2 | 27165 | 24-May-15 | 10563 | 3 | 4 | 5 | | V-1 | Gm1715 |
| 10468 | 3 | 4 | 5 | | | V-1 | Glt25d1 | 79709 | 4-May-15 | 10564 | 3 | 4 | 5 | | V-1 | Gm17359 |
| 10469 | 3 | 4 | 5 | | | V-1 | Glt28d2 | | | 10565 | 3 | 4 | 5 | | V-1 | Gm17455 |
| 10470 | 3 | 4 | 5 | | | V-1 | Glt6d1 | 360203 | 4-May-15 | 10566 | 3 | 4 | 5 | | V-1 | Gm17745 |
| 10471 | 3 | 4 | 5 | | | V-1 | Gltpd1 | 80772 | 4-May-15 | 10567 | 3 | 4 | 5 | | V-1 | Gm17746 |
| 10472 | 3 | 4 | 5 | | | V-1 | Gltpd2 | 388323 | 4-May-15 | 10568 | 3 | 4 | 5 | | V-1 | Gm17762 |
| 10473 | 3 | 4 | 5 | | | V-1 | Gltscr1l | 23506 | 12-May-15 | 10569 | 3 | 4 | 5 | | V-1 | Gm19276 |
| 10474 | 3 | 4 | 5 | | | V-1 | Glyat | 10249 | 4-May-15 | 10570 | 3 | 4 | 5 | | V-1 | Gm19395 |
| 10475 | 3 | 4 | 5 | | | V-1 | Gm10012 | | | 10571 | 3 | 4 | 5 | | V-1 | Gm19434 |
| 10476 | 3 | 4 | 5 | | | V-1 | Gm10081 | | | 10572 | 3 | 4 | 5 | | V-1 | Gm19710 |
| 10477 | 3 | 4 | 5 | | | V-1 | Gm10220 | | | 10573 | 3 | 4 | 5 | | V-1 | Gm19782 |
| 10478 | 3 | 4 | 5 | | | V-1 | Gm10248 | | | 10574 | 3 | 4 | 5 | | V-1 | Gm19897 |
| 10479 | 3 | 4 | 5 | | | V-1 | Gm10336 | | | 10575 | 3 | 4 | 5 | | V-1 | Gm2002 |
| 10480 | 3 | 4 | 5 | | | V-1 | Gm10377 | | | 10576 | 3 | 4 | 5 | | V-1 | Gm20110 |
| 10481 | 3 | 4 | 5 | | | V-1 | Gm10389 | | | 10577 | 3 | 4 | 5 | | V-1 | Gm20268 |
| 10482 | 3 | 4 | 5 | | | V-1 | Gm10421 | | | 10578 | 3 | 4 | 5 | | V-1 | Gm20324 |
| 10483 | 3 | 4 | 5 | | | V-1 | Gm10466 | | | 10579 | 3 | 4 | 5 | | V-1 | Gm20337 |
| 10484 | 3 | 4 | 5 | | | V-1 | Gm10578 | | | 10580 | 3 | 4 | 5 | | V-1 | Gm20556 |
| 10485 | 3 | 4 | 5 | | | V-1 | Gm10619 | | | 10581 | 3 | 4 | 5 | | V-1 | Gm20597 |
| 10486 | 3 | 4 | 5 | | | V-1 | Gm10640 | | | 10582 | 3 | 4 | 5 | | V-1 | Gm20605 |
| 10487 | 3 | 4 | 5 | | | V-1 | Gm10649 | | | 10583 | 3 | 4 | 5 | | V-1 | Gm2061 |
| 10488 | 3 | 4 | 5 | | | V-1 | Gm10662 | | | 10584 | 3 | 4 | 5 | | V-1 | Gm20740 |
| 10489 | 3 | 4 | 5 | | | V-1 | Gm10684 | | | 10585 | 3 | 4 | 5 | | V-1 | Gm20744 |
| 10490 | 3 | 4 | 5 | | | V-1 | Gm10778 | | | 10586 | 3 | 4 | 5 | | V-1 | Gm20831 |
| 10491 | 3 | 4 | 5 | | | V-1 | Gm10789 | | | 10587 | 3 | 4 | 5 | | V-1 | Gm20871 |
| 10492 | 3 | 4 | 5 | | | V-1 | Gm10857 | | | 10588 | 3 | 4 | 5 | | V-1 | Gm20917 |
| 10493 | 3 | 4 | 5 | | | V-1 | Gm10921 | | | 10589 | 3 | 4 | 5 | | V-1 | Gm2109 |
| 10494 | 3 | 4 | 5 | | | V-1 | Gm11110 | | | 10590 | 3 | 4 | 5 | | V-1 | Gm21221 |
| 10495 | 3 | 4 | 5 | | | V-1 | Gm11351 | | | 10591 | 3 | 4 | 5 | | V-1 | Gm2863 |
| 10496 | 3 | 4 | 5 | | | V-1 | Gm11468 | | | 10592 | 3 | 4 | 5 | | V-1 | Gm3002 |
| 10497 | 3 | 4 | 5 | | | V-1 | Gm11696 | | | 10593 | 3 | 4 | 5 | | V-1 | Gm3139 |
| 10498 | 3 | 4 | 5 | | | V-1 | Gm11710 | | | 10594 | 3 | 4 | 5 | | V-1 | Gm3230 |
| 10499 | 3 | 4 | 5 | | | V-1 | Gm11711 | | | 10595 | 3 | 4 | 5 | | V-1 | Gm3985 |
| 10500 | 3 | 4 | 5 | | | V-1 | Gm11744 | | | 10596 | 3 | 4 | 5 | | V-1 | Gm41 |
| 10501 | 3 | 4 | 5 | | | V-1 | Gm11747 | | | 10597 | 3 | 4 | 5 | | V-1 | Gm4297 |
| 10502 | 3 | 4 | 5 | | | V-1 | Gm11961 | | | 10598 | 3 | 4 | 5 | | V-1 | Gm436 |
| 10503 | 3 | 4 | 5 | | | V-1 | Gm11978 | | | 10599 | 3 | 4 | 5 | | V-1 | Gm4489 |
| 10504 | 3 | 4 | 5 | | | V-1 | Gm12253 | | | 10600 | 3 | 4 | 5 | | V-1 | Gm4541 |
| 10505 | 3 | 4 | 5 | | | V-1 | Gm12298 | | | 10601 | 3 | 4 | 5 | | V-1 | Gm4763 |
| 10506 | 3 | 4 | 5 | | | V-1 | Gm12504 | | | 10602 | 3 | 4 | 5 | | V-1 | Gm4791 |
| 10507 | 3 | 4 | 5 | | | V-1 | Gm12505 | | | 10603 | 3 | 4 | 5 | | V-1 | Gm4827 |
| 10508 | 3 | 4 | 5 | | | V-1 | Gm12522 | | | 10604 | 3 | 4 | 5 | | V-1 | Gm4847 |
| 10509 | 3 | 4 | 5 | | | V-1 | Gm12669 | | | 10605 | 3 | 4 | 5 | | V-1 | Gm4922 |
| 10510 | 3 | 4 | 5 | | | V-1 | Gm12992 | | | 10606 | 3 | 4 | 5 | | V-1 | Gm4961 |
| 10511 | 3 | 4 | 5 | | | V-1 | Gm13157 | | | 10607 | 3 | 4 | 5 | | V-1 | Gm4971 |
| 10512 | 3 | 4 | 5 | | | V-1 | Gm13177 | | | 10608 | 3 | 4 | 5 | | V-1 | Gm4981 |
| 10513 | 3 | 4 | 5 | | | V-1 | Gm13222 | | | 10609 | 3 | 4 | 5 | | V-1 | Gm5089 |
| 10514 | 3 | 4 | 5 | | | V-1 | Gm13271 | | | 10610 | 3 | 4 | 5 | | V-1 | Gm5095 |
| 10515 | 3 | 4 | 5 | | | V-1 | Gm13305 | | | 10611 | 3 | 4 | 5 | | V-1 | Gm5108 |
| 10516 | 3 | 4 | 5 | | | V-1 | Gm13375 | | | 10612 | 3 | 4 | 5 | | V-1 | Gm5127 |
| 10517 | 3 | 4 | 5 | | | V-1 | Gm13749 | | | 10613 | 3 | 4 | 5 | | V-1 | Gm5166 |
| 10518 | 3 | 4 | 5 | | | V-1 | Gm13871 | | | 10614 | 3 | 4 | 5 | | V-1 | Gm5177 |
| 10519 | 3 | 4 | 5 | | | V-1 | Gm13939 | | | 10615 | 3 | 4 | 5 | | V-1 | Gm527 |
| 10520 | 3 | 4 | 5 | | | V-1 | Gm14005 | | | 10616 | 3 | 4 | 5 | | V-1 | Gm5414 |
| 10521 | 3 | 4 | 5 | | | V-1 | Gm14015 | | | 10617 | 3 | 4 | 5 | | V-1 | Gm5420 |

Fig. 30 - 57

| | | | | | | | | | | | | | | | | | |
|---|---|---|---|---|---|---|---|---|---|---|---|---|---|---|---|---|---|
| 10618 | 3 | 4 | 5 | | | V-1 | Gm5431 | | | 10714 | 3 | 4 | 5 | | | V-1 | Gpha2 | 170589 | 4-May-15 |
| 10619 | 3 | 4 | 5 | | | V-1 | Gm5434 | | | 10715 | 3 | 4 | 5 | | | V-1 | Gphb5 | 122876 | 4-May-15 |
| 10620 | 3 | 4 | 5 | | | V-1 | Gm5485 | | | 10716 | 3 | 4 | 5 | | | V-1 | Gpkow | 27238 | 4-May-15 |
| 10621 | 3 | 4 | 5 | | | V-1 | Gm5523 | | | 10717 | 3 | 4 | 5 | | | V-1 | Gpm6a | 2823 | 4-May-15 |
| 10622 | 3 | 4 | 5 | | | V-1 | Gm5535 | | | 10718 | 3 | 4 | 5 | | | V-1 | Gpn1 | 31321 | 4-May-15 |
| 10623 | 3 | 4 | 5 | | | V-1 | Gm5577 | | | 10719 | 3 | 4 | 5 | | | V-1 | Gpr111 | 222611 | 4-May-15 |
| 10624 | 3 | 4 | 5 | | | V-1 | Gm5592 | | | 10720 | 3 | 4 | 5 | | | V-1 | Gpr115 | 221393 | 12-May-15 |
| 10625 | 3 | 4 | 5 | | | V-1 | Gm5634 | | | 10721 | 3 | 4 | 5 | | | V-1 | Gpr119 | 139760 | 4-May-15 |
| 10626 | 3 | 4 | 5 | | | V-1 | Gm5662 | | | 10722 | 3 | 4 | 5 | | | V-1 | Gpr125 | 166647 | 14-May-15 |
| 10627 | 3 | 4 | 5 | | | V-1 | Gm5766 | | | 10723 | 3 | 4 | 5 | | | V-1 | Gpr137 | 56834 | 12-May-15 |
| 10628 | 3 | 4 | 5 | | | V-1 | Gm5779 | | | 10724 | 3 | 4 | 5 | | | V-1 | Gpr137c | 283554 | 4-May-15 |
| 10629 | 3 | 4 | 5 | | | V-1 | Gm5833 | | | 10725 | 3 | 4 | 5 | | | V-1 | Gpr139 | 124274 | 12-May-15 |
| 10630 | 3 | 4 | 5 | | | V-1 | Gm6042 | | | 10726 | 3 | 4 | 5 | | | V-1 | Gpr142 | 350383 | 4-May-15 |
| 10631 | 3 | 4 | 5 | | | V-1 | Gm6313 | | | 10727 | 3 | 4 | 5 | | | V-1 | Gpr150 | 285601 | 4-May-15 |
| 10632 | 3 | 4 | 5 | | | V-1 | Gm6402 | | | 10728 | 3 | 4 | 5 | | | V-1 | Gpr155 | 151556 | 4-May-15 |
| 10633 | 3 | 4 | 5 | | | V-1 | Gm6498 | | | 10729 | 3 | 4 | 5 | | | V-1 | Gpr161 | 23432 | 12-May-15 |
| 10634 | 3 | 4 | 5 | | | V-1 | Gm6537 | | | 10730 | 3 | 4 | 5 | | | V-1 | Gpr162 | 27239 | 4-May-15 |
| 10635 | 3 | 4 | 5 | | | V-1 | Gm6559 | | | 10731 | 3 | 4 | 5 | | | V-1 | Gpr165 | | |
| 10636 | 3 | 4 | 5 | | | V-1 | Gm6578 | | | 10732 | 3 | 4 | 5 | | | V-1 | Gpr173 | 54328 | 12-May-15 |
| 10637 | 3 | 4 | 5 | | | V-1 | Gm6623 | | | 10733 | 3 | 4 | 5 | | | V-1 | Gpr179 | 440435 | 4-May-15 |
| 10638 | 3 | 4 | 5 | | | V-1 | Gm6639 | | | 10734 | 3 | 4 | 5 | | | V-1 | Gpr180 | 160897 | 31-May-15 |
| 10639 | 3 | 4 | 5 | | | V-1 | Gm6696 | | | 10735 | 3 | 4 | 5 | | | V-1 | Gpr183 | 1880 | 4-May-15 |
| 10640 | 3 | 4 | 5 | | | V-1 | Gm6793 | | | 10736 | 3 | 4 | 5 | | | V-1 | Gpr19 | 2842 | 4-May-15 |
| 10641 | 3 | 4 | 5 | | | V-1 | Gm6812 | | | 10737 | 3 | 4 | 5 | | | V-1 | Gpr31b | | |
| 10642 | 3 | 4 | 5 | | | V-1 | Gm6927 | | | 10738 | 3 | 4 | 5 | | | V-1 | Gpr37 | 2861 | 28-May-15 |
| 10643 | 3 | 4 | 5 | | | V-1 | Gm7056 | | | 10739 | 3 | 4 | 5 | | | V-1 | Gpr4 | 2828 | 4-May-15 |
| 10644 | 3 | 4 | 5 | | | V-1 | Gm7104 | | | 10740 | 3 | 4 | 5 | | | V-1 | Gpr6 | 2830 | 4-May-15 |
| 10645 | 3 | 4 | 5 | | | V-1 | Gm7244 | | | 10741 | 3 | 4 | 5 | | | V-1 | Gpr68 | 8111 | 4-May-15 |
| 10646 | 3 | 4 | 5 | | | V-1 | Gm7257 | | | 10742 | 3 | 4 | 5 | | | V-1 | Gpr84 | 53831 | 4-May-15 |
| 10647 | 3 | 4 | 5 | | | V-1 | Gm7616 | | | 10743 | 3 | 4 | 5 | | | V-1 | Gpr98 | 84059 | 23-May-15 |
| 10648 | 3 | 4 | 5 | | | V-1 | Gm7714 | | | 10744 | 3 | 4 | 5 | | | V-1 | Gprc5b | 51704 | 12-May-15 |
| 10649 | 3 | 4 | 5 | | | V-1 | Gm7788 | | | 10745 | 3 | 4 | 5 | | | V-1 | Gps1 | 2873 | 4-May-15 |
| 10650 | 3 | 4 | 5 | | | V-1 | Gm7854 | | | 10746 | 3 | 4 | 5 | | | V-1 | Gpx4 | 2879 | 10-May-15 |
| 10651 | 3 | 4 | 5 | | | V-1 | Gm7904 | | | 10747 | 3 | 4 | 5 | | | V-1 | Gpx7 | 2882 | 4-May-15 |
| 10652 | 3 | 4 | 5 | | | V-1 | Gm7978 | | | 10748 | 3 | 4 | 5 | | | V-1 | Gpx8 | 493869 | 12-May-15 |
| 10653 | 3 | 4 | 5 | | | V-1 | Gm8234 | | | 10749 | 3 | 4 | 5 | | | V-1 | Gramd1a | 57655 | 12-May-15 |
| 10654 | 3 | 4 | 5 | | | V-1 | Gm8267 | | | 10750 | 3 | 4 | 5 | | | V-1 | Gramd1c | 54762 | 4-May-15 |
| 10655 | 3 | 4 | 5 | | | V-1 | Gm829 | | | 10751 | 3 | 4 | 5 | | | V-1 | Grap | 10750 | 4-May-15 |
| 10656 | 3 | 4 | 5 | | | V-1 | Gm839 | | | 10752 | 3 | 4 | 5 | | | V-1 | Grb2 | 2885 | 31-May-15 |
| 10657 | 3 | 4 | 5 | | | V-1 | Gm853 | | | 10753 | 3 | 4 | 5 | | | V-1 | Grcc10 | 113246 | 12-May-15 |
| 10658 | 3 | 4 | 5 | | | V-1 | Gm8615 | | | 10754 | 3 | 4 | 5 | | | V-1 | Greb1l | 80000 | 4-May-15 |
| 10659 | 3 | 4 | 5 | | | V-1 | Gm8677 | | | 10755 | 3 | 4 | 5 | | | V-1 | Grhl1 | 29841 | 28-May-15 |
| 10660 | 3 | 4 | 5 | | | V-1 | Gm8817 | | | 10756 | 3 | 4 | 5 | | | V-1 | Grhl3 | 57822 | 4-May-15 |
| 10661 | 3 | 4 | 5 | | | V-1 | Gm8994 | | | 10757 | 3 | 4 | 5 | | | V-1 | Grhpr | 9380 | 31-May-15 |
| 10662 | 3 | 4 | 5 | | | V-1 | Gm906 | | | 10758 | 3 | 4 | 5 | | | V-1 | Gria4 | 2893 | 12-May-15 |
| 10663 | 3 | 4 | 5 | | | V-1 | Gm9376 | | | 10759 | 3 | 4 | 5 | | | V-1 | Grik1 | 2897 | 31-May-15 |
| 10664 | 3 | 4 | 5 | | | V-1 | Gm9758 | | | 10760 | 3 | 4 | 5 | | | V-1 | Grin2d | 2906 | 4-May-15 |
| 10665 | 3 | 4 | 5 | | | V-1 | Gm9839 | | | 10761 | 3 | 4 | 5 | | | V-1 | Grinl | 23426 | 7-Jun-15 |
| 10666 | 3 | 4 | 5 | | | V-1 | Gm9866 | | | 10762 | 3 | 4 | 5 | | | V-1 | Grk6 | 2870 | 12-May-15 |
| 10667 | 3 | 4 | 5 | | | V-1 | Gm9899 | | | 10763 | 3 | 4 | 5 | | | V-1 | Grm7 | 2917 | 12-May-15 |
| 10668 | 3 | 4 | 5 | | | V-1 | Gm996 | | | 10764 | 3 | 4 | 5 | | | V-1 | Grpel1 | 80273 | 4-May-15 |
| 10669 | 3 | 4 | 5 | | | V-1 | Gm9994 | | | 10765 | 3 | 4 | 5 | | | V-1 | Grrp1 | 79927 | 4-May-15 |
| 10670 | 3 | 4 | 5 | | | V-1 | Gmcl1 | 64396 | 4-May-15 | 10766 | 3 | 4 | 5 | | | V-1 | Grsf1 | 2926 | 31-May-15 |
| 10671 | 3 | 4 | 5 | | | V-1 | Gmeb1 | 10691 | 4-May-15 | 10767 | 3 | 4 | 5 | | | V-1 | Grxcr1 | 389207 | 4-May-15 |
| 10672 | 3 | 4 | 5 | | | V-1 | Gmip | 51291 | 28-May-15 | 10768 | 3 | 4 | 5 | | | V-1 | Gsc | 145258 | 4-May-15 |
| 10673 | 3 | 4 | 5 | | | V-1 | Gml | 2765 | 4-May-15 | 10769 | 3 | 4 | 5 | | | V-1 | Gsdma2 | | |
| 10674 | 3 | 4 | 5 | | | V-1 | Gmppa | 29926 | 4-May-15 | 10770 | 3 | 4 | 5 | | | V-1 | Gsdmc4 | | |
| 10675 | 3 | 4 | 5 | | | V-1 | Gna12 | 2768 | 4-May-15 | 10771 | 3 | 4 | 5 | | | V-1 | Gsk3a | 2931 | 28-May-15 |
| 10676 | 3 | 4 | 5 | | | V-1 | Gna15 | 2769 | 4-May-15 | 10772 | 3 | 4 | 5 | | | V-1 | Gspt1 | 2935 | 4-May-15 |
| 10677 | 3 | 4 | 5 | | | V-1 | Gnai1 | 2770 | 12-May-15 | 10773 | 3 | 4 | 5 | | | V-1 | Gss | 2937 | 16-Jun-15 |
| 10678 | 3 | 4 | 5 | | | V-1 | Gnai2 | 2771 | 12-May-15 | 10774 | 3 | 4 | 5 | | | V-1 | Gsta4 | 2941 | 12-May-15 |
| 10679 | 3 | 4 | 5 | | | V-1 | Gnal | 2774 | 12-May-15 | 10775 | 3 | 4 | 5 | | | V-1 | Gsrk1 | 373156 | 4-May-15 |
| 10680 | 3 | 4 | 5 | | | V-1 | Gnaq | 2776 | 4-May-15 | 10776 | 3 | 4 | 5 | | | V-1 | Gstm2 | 2946 | 17-May-15 |
| 10681 | 3 | 4 | 5 | | | V-1 | Gnat3 | 346562 | 4-May-15 | 10777 | 3 | 4 | 5 | | | V-1 | Gstm3 | 2947 | 12-May-15 |
| 10682 | 3 | 4 | 5 | | | V-1 | Gnaz | 2781 | 4-May-15 | 10778 | 3 | 4 | 5 | | | V-1 | Gstm4 | 2948 | 12-May-15 |
| 10683 | 3 | 4 | 5 | | | V-1 | Gnb4 | 59345 | 4-May-15 | 10779 | 3 | 4 | 5 | | | V-1 | Gsto2 | 119391 | 12-May-15 |
| 10684 | 3 | 4 | 5 | | | V-1 | Gnb5 | 10681 | 4-May-15 | 10780 | 3 | 4 | 5 | | | V-1 | Gstt4 | 25774 | 4-May-15 |
| 10685 | 3 | 4 | 5 | | | V-1 | Gne | 10020 | 23-May-15 | 10781 | 3 | 4 | 5 | | | V-1 | Gsx1 | 219409 | 28-May-15 |
| 10686 | 3 | 4 | 5 | | | V-1 | Gng10 | 2790 | 4-May-15 | 10782 | 3 | 4 | 5 | | | V-1 | Gtf2h1 | 2965 | 4-May-15 |
| 10687 | 3 | 4 | 5 | | | V-1 | Gng11 | 2791 | 4-May-15 | 10783 | 3 | 4 | 5 | | | V-1 | Gtf2h2 | 2966 | 4-May-15 |
| 10688 | 3 | 4 | 5 | | | V-1 | Gng12 | 55970 | 4-May-15 | 10784 | 3 | 4 | 5 | | | V-1 | Gtf2ird2 | 84163 | 4-May-15 |
| 10689 | 3 | 4 | 5 | | | V-1 | Gng2 | 54331 | 12-May-15 | 10785 | 3 | 4 | 5 | | | V-1 | Gtf3c5 | 9328 | 4-May-15 |
| 10690 | 3 | 4 | 5 | | | V-1 | Gng3 | 2785 | 4-May-15 | 10786 | 3 | 4 | 5 | | | V-1 | Gtsf1 | 121355 | 4-May-15 |
| 10691 | 3 | 4 | 5 | | | V-1 | Gng5 | 2787 | 12-May-15 | 10787 | 3 | 4 | 5 | | | V-1 | Guca2b | 2981 | 4-May-15 |
| 10692 | 3 | 4 | 5 | | | V-1 | Gng7 | 2788 | 4-May-15 | 10788 | 3 | 4 | 5 | | | V-1 | Gucy1a2 | 2977 | 4-May-15 |
| 10693 | 3 | 4 | 5 | | | V-1 | Gngt1 | 2792 | 3-May-15 | 10789 | 3 | 4 | 5 | | | V-1 | Gucy1b2 | 2974 | 4-May-15 |
| 10694 | 3 | 4 | 5 | | | V-1 | Gnl1 | 2794 | 12-May-15 | 10790 | 3 | 4 | 5 | | | V-1 | Gucy2c | 2984 | 4-May-15 |
| 10695 | 3 | 4 | 5 | | | V-1 | Gnl3l | 54552 | 4-May-15 | 10791 | 3 | 4 | 5 | | | V-1 | Gucy2d | 3000 | 31-May-15 |
| 10696 | 3 | 4 | 5 | | | V-1 | Gnpat | 8443 | 12-May-15 | 10792 | 3 | 4 | 5 | | | V-1 | Gxylt1 | 283464 | 4-May-15 |
| 10697 | 3 | 4 | 5 | | | V-1 | Gnpnat1 | 64841 | 4-May-15 | 10793 | 3 | 4 | 5 | | | V-1 | Gyg | 2992 | 12-May-15 |
| 10698 | 3 | 4 | 5 | | | V-1 | Gnrhr | 2798 | 23-May-15 | 10794 | 3 | 4 | 5 | | | V-1 | Gyk | | |
| 10699 | 3 | 4 | 5 | | | V-1 | Golgb1 | 2804 | 4-May-15 | 10795 | 3 | 4 | 5 | | | V-1 | Gykl1 | | |
| 10700 | 3 | 4 | 5 | | | V-1 | Golph3 | 64083 | 12-May-15 | 10796 | 3 | 4 | 5 | | | V-1 | Gys1 | 2997 | 12-May-15 |
| 10701 | 3 | 4 | 5 | | | V-1 | Golt1b | 51026 | 4-May-15 | 10797 | 3 | 4 | 5 | | | V-1 | Gzf1 | 64412 | 4-May-15 |
| 10702 | 3 | 4 | 5 | | | V-1 | Gon4l | 54856 | 12-May-15 | 10798 | 3 | 4 | 5 | | | V-1 | Gzmb | 3002 | 31-May-15 |
| 10703 | 3 | 4 | 5 | | | V-1 | Got1l1 | 137362 | 4-May-15 | 10799 | 3 | 4 | 5 | | | V-1 | Gzmd | | |
| 10704 | 3 | 4 | 5 | | | V-1 | Gp1ba | 2811 | 12-May-15 | 10800 | 3 | 4 | 5 | | | V-1 | H1f0 | 3005 | 4-May-15 |
| 10705 | 3 | 4 | 5 | | | V-1 | Gp6 | 51026 | 4-May-15 | 10801 | 3 | 4 | 5 | | | V-1 | H2afb1 | 474382 | 4-May-15 |
| 10706 | 3 | 4 | 5 | | | V-1 | Gpa33 | 10223 | 4-May-15 | 10802 | 3 | 4 | 5 | | | V-1 | H2afj | 55766 | 7-Jun-15 |
| 10707 | 3 | 4 | 5 | | | V-1 | Gpank1 | 7918 | 4-May-15 | 10803 | 3 | 4 | 5 | | | V-1 | H2afy | 9555 | 12-May-15 |
| 10708 | 3 | 4 | 5 | | | V-1 | Gpatch11 | 253635 | 4-May-15 | 10804 | 3 | 4 | 5 | | | V-1 | H2afv2 | 55506 | 4-May-15 |
| 10709 | 3 | 4 | 5 | | | V-1 | Gpatch8 | 23131 | 4-May-15 | 10805 | 3 | 4 | 5 | | | V-1 | H2bfm | 286436 | 4-May-15 |
| 10710 | 3 | 4 | 5 | | | V-1 | Gpc5 | 2262 | 24-May-15 | 10806 | 3 | 4 | 5 | | | V-1 | H2-Eb2 | | |
| 10711 | 3 | 4 | 5 | | | V-1 | Gpd1l | 23171 | 4-May-15 | 10807 | 3 | 4 | 5 | | | V-1 | H2-Ke2 | 10471 | 4-May-15 |
| 10712 | 3 | 4 | 5 | | | V-1 | Gpd2 | 2820 | 12-May-15 | 10808 | 3 | 4 | 5 | | | V-1 | H2-M1 | | |
| 10713 | 3 | 4 | 5 | | | V-1 | Gper1 | 2852 | 31-May-15 | 10809 | 3 | 4 | 5 | | | V-1 | H2-M10.2 | | |

Fig. 30 - 58

| | | | | | | | | | | | | | | | |
|---|---|---|---|---|---|---|---|---|---|---|---|---|---|---|---|
| 10810 | 3 | 4 | 5 | | V-1 | H2-M5 | | | 10906 | 3 | 4 | 5 | | V-1 | Hist2h2be | 8349 | 4-May-15 |
| 10811 | 3 | 4 | 5 | | V-1 | H2-M9 | | | 10907 | 3 | 4 | 5 | | V-1 | Hist3h2a | 92815 | 4-May-15 |
| 10812 | 3 | 4 | 5 | | V-1 | H2-T10 | | | 10908 | 3 | 4 | 5 | | V-1 | Hivep1 | 3096 | 12-May-15 |
| 10813 | 3 | 4 | 5 | | V-1 | H2-T23 | | | 10909 | 3 | 4 | 5 | | V-1 | Hjurp | 55355 | 17-May-15 |
| 10814 | 3 | 4 | 5 | | V-1 | H2-T24 | | | 10910 | 3 | 4 | 5 | | V-1 | Hk1 | 3098 | 7-Jun-15 |
| 10815 | 3 | 4 | 5 | | V-1 | H2-T3 | | | 10911 | 3 | 4 | 5 | | V-1 | Hk1os | | |
| 10816 | 3 | 4 | 5 | | V-1 | H3f3a | 3020 | 12-May-15 | 10912 | 3 | 4 | 5 | | V-1 | Hkdc1 | 80201 | 4-May-15 |
| 10817 | 3 | 4 | 5 | | V-1 | H3f3b | 3021 | 4-May-15 | 10913 | 3 | 4 | 5 | | V-1 | Hlcs | 3141 | 4-May-15 |
| 10818 | 3 | 4 | 5 | | V-1 | H60c | | | 10914 | 3 | 4 | 5 | | V-1 | Hltf | 6596 | 4-May-15 |
| 10819 | 3 | 4 | 5 | | V-1 | Habp4 | 22927 | 12-May-15 | 10915 | 3 | 4 | 5 | | V-1 | Hmbox1 | 79618 | 4-May-15 |
| 10820 | 3 | 4 | 5 | | V-1 | Hacl1 | 26061 | 7-Jun-15 | 10916 | 3 | 4 | 5 | | V-1 | Hmces | 56941 | 4-May-15 |
| 10821 | 3 | 4 | 5 | | V-1 | Hadh | 3033 | 7-Jun-15 | 10917 | 3 | 4 | 5 | | V-1 | Hmg20a | 10363 | 12-May-15 |
| 10822 | 3 | 4 | 5 | | V-1 | Hadhb | 3032 | 4-May-15 | 10918 | 3 | 4 | 5 | | V-1 | Hmga2 | 8091 | 31-May-15 |
| 10823 | 3 | 4 | 5 | | V-1 | Haghl | 84264 | 21-May-15 | 10919 | 3 | 4 | 5 | | V-1 | Hmgb1 | 3146 | 7-Jun-15 |
| 10824 | 3 | 4 | 5 | | V-1 | Hao1 | 54363 | 12-May-15 | 10920 | 3 | 4 | 5 | | V-1 | Hmgb4 | 127540 | 4-May-15 |
| 10825 | 3 | 4 | 5 | | V-1 | Hapln1 | 1404 | 28-May-15 | 10921 | 3 | 4 | 5 | | V-1 | Hmgn1 | 3150 | 4-May-15 |
| 10826 | 3 | 4 | 5 | | V-1 | Hapln4 | 404037 | 4-May-15 | 10922 | 3 | 4 | 5 | | V-1 | Hmgn5 | 79366 | 4-May-15 |
| 10827 | 3 | 4 | 5 | | V-1 | Harbi1 | 283254 | 4-May-15 | 10923 | 3 | 4 | 5 | | V-1 | Hmgxb3 | 22993 | 4-May-15 |
| 10828 | 3 | 4 | 5 | | V-1 | Hars2 | 23438 | 7-Jun-15 | 10924 | 3 | 4 | 5 | | V-1 | Hmox2 | 3163 | 4-May-15 |
| 10829 | 3 | 4 | 5 | | V-1 | Has2 | 3037 | 14-May-15 | 10925 | 3 | 4 | 5 | | V-1 | Hn1l | 90861 | 7-Jun-15 |
| 10830 | 3 | 4 | 5 | | V-1 | Has2os | | | 10926 | 3 | 4 | 5 | | V-1 | Hnrnpa0 | 10949 | 4-May-15 |
| 10831 | 3 | 4 | 5 | | V-1 | Hat1 | 8520 | 17-May-15 | 10927 | 3 | 4 | 5 | | V-1 | Hnrnpa1 | 3178 | 23-May-15 |
| 10832 | 3 | 4 | 5 | | V-1 | Haus1 | 115106 | 4-May-15 | 10928 | 3 | 4 | 5 | | V-1 | Hook2 | 29911 | 4-May-15 |
| 10833 | 3 | 4 | 5 | | V-1 | Haus4 | 54930 | 4-May-15 | 10929 | 3 | 4 | 5 | | V-1 | Hormad1 | 84072 | 4-May-15 |
| 10834 | 3 | 4 | 5 | | V-1 | Haus5 | 23354 | 4-May-15 | 10930 | 3 | 4 | 5 | | V-1 | Hoxa4 | 3201 | 12-May-15 |
| 10835 | 3 | 4 | 5 | | V-1 | Haus7 | 55559 | 4-May-15 | 10931 | 3 | 4 | 5 | | V-1 | Hoxa5 | 3202 | 28-May-15 |
| 10836 | 3 | 4 | 5 | | V-1 | Hba-x | | | 10932 | 3 | 4 | 5 | | V-1 | Hoxa6 | 3203 | 4-May-15 |
| 10837 | 3 | 4 | 5 | | V-1 | Hbb-bh1 | | | 10933 | 3 | 4 | 5 | | V-1 | Hoxa7 | 3204 | 28-May-15 |
| 10838 | 3 | 4 | 5 | | V-1 | Hbb-y | | | 10934 | 3 | 4 | 5 | | V-1 | Hoxb3 | 3213 | 12-May-15 |
| 10839 | 3 | 4 | 5 | | V-1 | Hbp1 | 26959 | 4-May-15 | 10935 | 3 | 4 | 5 | | V-1 | Hoxb4 | 3214 | 4-May-15 |
| 10840 | 3 | 4 | 5 | | V-1 | Hbs1l | 10767 | 4-May-15 | 10936 | 3 | 4 | 5 | | V-1 | Hoxb5 | 3215 | 28-May-15 |
| 10841 | 3 | 4 | 5 | | V-1 | Hccs | 3052 | 23-May-15 | 10937 | 3 | 4 | 5 | | V-1 | Hoxc5 | 3222 | 4-May-15 |
| 10842 | 3 | 4 | 5 | | V-1 | Hcn1 | 348980 | 4-May-15 | 10938 | 3 | 4 | 5 | | V-1 | Hoxd11 | 3237 | 12-May-15 |
| 10843 | 3 | 4 | 5 | | V-1 | Hdac1 | 3065 | 28-May-15 | 10939 | 3 | 4 | 5 | | V-1 | Hoxd3os1 | | |
| 10844 | 3 | 4 | 5 | | V-1 | Hdac10 | 83933 | 28-May-15 | 10940 | 3 | 4 | 5 | | V-1 | Hp1bp3 | 50809 | 12-May-15 |
| 10845 | 3 | 4 | 5 | | V-1 | Hdac2 | 3066 | 28-May-15 | 10941 | 3 | 4 | 5 | | V-1 | Hpn | 3249 | 12-May-15 |
| 10846 | 3 | 4 | 5 | | V-1 | Hdac8 | 55869 | 28-May-15 | 10942 | 3 | 4 | 5 | | V-1 | Hprt | 3251 | 23-May-15 |
| 10847 | 3 | 4 | 5 | | V-1 | Hddc2 | 51020 | 4-May-15 | 10943 | 3 | 4 | 5 | | V-1 | Hps3 | 84343 | 23-May-15 |
| 10848 | 3 | 4 | 5 | | V-1 | Hddc3 | 374659 | 4-May-15 | 10944 | 3 | 4 | 5 | | V-1 | Hras | 3265 | 2-Jun-15 |
| 10849 | 3 | 4 | 5 | | V-1 | Hdgfl1 | 154150 | 12-May-15 | 10945 | 3 | 4 | 5 | | V-1 | Hrct1 | 646962 | 4-May-15 |
| 10850 | 3 | 4 | 5 | | V-1 | Hdlbp | 3069 | 12-May-15 | 10946 | 3 | 4 | 5 | | V-1 | Hrg | 3273 | 7-Jun-15 |
| 10851 | 3 | 4 | 5 | | V-1 | Heatr2 | 54919 | 7-Jun-15 | 10947 | 3 | 4 | 5 | | V-1 | Hrh1 | 3269 | 4-May-15 |
| 10852 | 3 | 4 | 5 | | V-1 | Heca | 51696 | 4-May-15 | 10948 | 3 | 4 | 5 | | V-1 | Hrh4 | 59340 | 4-May-15 |
| 10853 | 3 | 4 | 5 | | V-1 | Hectd2 | 143279 | 12-May-15 | 10949 | 3 | 4 | 5 | | V-1 | Hrsp12 | 10247 | 4-May-15 |
| 10854 | 3 | 4 | 5 | | V-1 | Heg1 | 57493 | 12-May-15 | 10950 | 3 | 4 | 5 | | V-1 | Hs3st2 | 9956 | 4-May-15 |
| 10855 | 3 | 4 | 5 | | V-1 | Helb | 92797 | 4-May-15 | 10951 | 3 | 4 | 5 | | V-1 | Hs3st4 | 9951 | 4-May-15 |
| 10856 | 3 | 4 | 5 | | V-1 | Helq | 113510 | 4-May-15 | 10952 | 3 | 4 | 5 | | V-1 | Hs6st1 | 9394 | 14-May-15 |
| 10857 | 3 | 4 | 5 | | V-1 | Hemk1 | 51409 | 4-May-15 | 10953 | 3 | 4 | 5 | | V-1 | Hs6st2 | 90161 | 4-May-15 |
| 10858 | 3 | 4 | 5 | | V-1 | Hepacam2 | 253012 | 4-May-15 | 10954 | 3 | 4 | 5 | | V-1 | Hs6st3 | 266722 | 4-May-15 |
| 10859 | 3 | 4 | 5 | | V-1 | Heph | 9843 | 4-May-15 | 10955 | 3 | 4 | 5 | | V-1 | Hscb | 150274 | 4-May-15 |
| 10860 | 3 | 4 | 5 | | V-1 | Hephl1 | 341208 | 4-May-15 | 10956 | 3 | 4 | 5 | | V-1 | Hsd11b2 | 3291 | 12-May-15 |
| 10861 | 3 | 4 | 5 | | V-1 | Herpud2 | 64224 | 4-May-15 | 10957 | 3 | 4 | 5 | | V-1 | Hsd17b1 | 3292 | 4-May-15 |
| 10862 | 3 | 4 | 5 | | V-1 | Hes1 | 3280 | 7-Jun-15 | 10958 | 3 | 4 | 5 | | V-1 | Hsd17b14 | 51171 | 4-May-15 |
| 10863 | 3 | 4 | 5 | | V-1 | Hexdc | 284004 | 4-May-15 | 10959 | 3 | 4 | 5 | | V-1 | Hsd17b3 | 3293 | 4-May-15 |
| 10864 | 3 | 4 | 5 | | V-1 | Hey1 | 26508 | 4-May-15 | 10960 | 3 | 4 | 5 | | V-1 | Hsd3b4 | | |
| 10865 | 3 | 4 | 5 | | V-1 | Hfe | 3077 | 23-May-15 | 10961 | 3 | 4 | 5 | | V-1 | Hsd3b7 | 80270 | 4-May-15 |
| 10866 | 3 | 4 | 5 | | V-1 | Hfm1 | 164045 | 4-May-15 | 10962 | 3 | 4 | 5 | | V-1 | Hsdl1 | 83693 | 4-May-15 |
| 10867 | 3 | 4 | 5 | | V-1 | Hgsnat | 138050 | 4-May-15 | 10963 | 3 | 4 | 5 | | V-1 | Hsp90ab1 | 3326 | 21-May-15 |
| 10868 | 3 | 4 | 5 | | V-1 | Hhipl2 | 79802 | 4-May-15 | 10964 | 3 | 4 | 5 | | V-1 | Hspa13 | 6782 | 4-May-15 |
| 10869 | 3 | 4 | 5 | | V-1 | Hif1a | 3091 | 31-May-15 | 10965 | 3 | 4 | 5 | | V-1 | Hspa14 | 51182 | 4-May-15 |
| 10870 | 3 | 4 | 5 | | V-1 | Hif1an | 55662 | 4-May-15 | 10966 | 3 | 4 | 5 | | V-1 | Hspa2 | 3306 | 4-May-15 |
| 10871 | 3 | 4 | 5 | | V-1 | Higd1a | 25994 | 4-May-15 | 10967 | 3 | 4 | 5 | | V-1 | Hspa4 | 3308 | 7-Jun-15 |
| 10872 | 3 | 4 | 5 | | V-1 | Higd1c | 613227 | 4-May-15 | 10968 | 3 | 4 | 5 | | V-1 | Hspa5 | 3309 | 31-May-15 |
| 10873 | 3 | 4 | 5 | | V-1 | Hip1r | 9026 | 4-May-15 | 10969 | 3 | 4 | 5 | | V-1 | Hspa8 | 3312 | 4-May-15 |
| 10874 | 3 | 4 | 5 | | V-1 | Hipk2 | 28996 | 31-May-15 | 10970 | 3 | 4 | 5 | | V-1 | Hspa9 | 3313 | 31-May-15 |
| 10875 | 3 | 4 | 5 | | V-1 | Hipk3 | 10114 | 4-May-15 | 10971 | 3 | 4 | 5 | | V-1 | Hspb11 | 51668 | 4-May-15 |
| 10876 | 3 | 4 | 5 | | V-1 | Hist1h1a | 3024 | 4-May-15 | 10972 | 3 | 4 | 5 | | V-1 | Hspb3 | 8988 | 4-May-15 |
| 10877 | 3 | 4 | 5 | | V-1 | Hist1h1t | 3010 | 4-May-15 | 10973 | 3 | 4 | 5 | | V-1 | Hspb8 | 26353 | 23-May-15 |
| 10878 | 3 | 4 | 5 | | V-1 | Hist1h2ab | 8335 | 4-May-15 | 10974 | 3 | 4 | 5 | | V-1 | Hspb9 | 94086 | 4-May-15 |
| 10879 | 3 | 4 | 5 | | V-1 | Hist1h2ad | 3013 | 4-May-15 | 10975 | 3 | 4 | 5 | | V-1 | Hspbap1 | 79663 | 7-Jun-15 |
| 10880 | 3 | 4 | 5 | | V-1 | Hist1h2ae | 3012 | 14-May-15 | 10976 | 3 | 4 | 5 | | V-1 | Hsph1 | 10808 | 12-May-15 |
| 10881 | 3 | 4 | 5 | | V-1 | Hist1h2ah | 85235 | 4-May-15 | 10977 | 3 | 4 | 5 | | V-1 | Htatip2 | 10553 | 31-May-15 |
| 10882 | 3 | 4 | 5 | | V-1 | Hist1h2ai | 8329 | 4-May-15 | 10978 | 3 | 4 | 5 | | V-1 | Htr1d | 3352 | 24-May-15 |
| 10883 | 3 | 4 | 5 | | V-1 | Hist1h2ak | 8330 | 4-May-15 | 10979 | 3 | 4 | 5 | | V-1 | Htr2c | 3358 | 31-May-15 |
| 10884 | 3 | 4 | 5 | | V-1 | Hist1h2an | | | 10980 | 3 | 4 | 5 | | V-1 | Htr6 | 3362 | 4-May-15 |
| 10885 | 3 | 4 | 5 | | V-1 | Hist1h2ap | | | 10981 | 3 | 4 | 5 | | V-1 | Htt | 3064 | 7-Jun-15 |
| 10886 | 3 | 4 | 5 | | V-1 | Hist1h2bb | 3018 | 4-May-15 | 10982 | 3 | 4 | 5 | | V-1 | Hus1 | 3364 | 4-May-15 |
| 10887 | 3 | 4 | 5 | | V-1 | Hist1h2bc | 8347 | 12-May-15 | 10983 | 3 | 4 | 5 | | V-1 | Hyal4 | 23553 | 4-May-15 |
| 10888 | 3 | 4 | 5 | | V-1 | Hist1h2be | 8344 | 4-May-15 | 10984 | 3 | 4 | 5 | | V-1 | Hykk | 123688 | 4-May-15 |
| 10889 | 3 | 4 | 5 | | V-1 | Hist1h2bh | 8345 | 4-May-15 | 10985 | 3 | 4 | 5 | | V-1 | Hyou1 | 10525 | 31-May-15 |
| 10890 | 3 | 4 | 5 | | V-1 | Hist1h2bj | 8970 | 4-May-15 | 10986 | 3 | 4 | 5 | | V-1 | Hypk | 25764 | 4-May-15 |
| 10891 | 3 | 4 | 5 | | V-1 | Hist1h2bk | 85236 | 4-May-15 | 10987 | 3 | 4 | 5 | | V-1 | I830077J02Rik | | |
| 10892 | 3 | 4 | 5 | | V-1 | Hist1h2bm | 8342 | 4-May-15 | 10988 | 3 | 4 | 5 | | V-1 | Iah1 | 285148 | 14-May-15 |
| 10893 | 3 | 4 | 5 | | V-1 | Hist1h2bn | 8341 | 4-May-15 | 10989 | 3 | 4 | 5 | | V-1 | Iars | 3376 | 4-May-15 |
| 10894 | 3 | 4 | 5 | | V-1 | Hist1h2bp | | | 10990 | 3 | 4 | 5 | | V-1 | Ibtk | 25998 | 4-May-15 |
| 10895 | 3 | 4 | 5 | | V-1 | Hist1h2bq | | | 10991 | 3 | 4 | 5 | | V-1 | Ica1 | 3382 | 12-May-15 |
| 10896 | 3 | 4 | 5 | | V-1 | Hist1h3a | 8350 | 4-May-15 | 10992 | 3 | 4 | 5 | | V-1 | Ica1l | 130026 | 4-May-15 |
| 10897 | 3 | 4 | 5 | | V-1 | Hist1h3d | 8351 | 4-May-15 | 10993 | 3 | 4 | 5 | | V-1 | Icam2 | 3384 | 12-May-15 |
| 10898 | 3 | 4 | 5 | | V-1 | Hist1h3f | 8968 | 4-May-15 | 10994 | 3 | 4 | 5 | | V-1 | Icam5 | 7087 | 4-May-15 |
| 10899 | 3 | 4 | 5 | | V-1 | Hist1h3h | 8357 | 4-May-15 | 10995 | 3 | 4 | 5 | | V-1 | Ict1 | 3396 | 4-May-15 |
| 10900 | 3 | 4 | 5 | | V-1 | Hist1h3i | 8354 | 4-May-15 | 10996 | 3 | 4 | 5 | | V-1 | Id2 | 3398 | 4-May-15 |
| 10901 | 3 | 4 | 5 | | V-1 | Hist1h4a | 8359 | 2-Jun-15 | 10997 | 3 | 4 | 5 | | V-1 | Id3 | 3399 | 21-May-15 |
| 10902 | 3 | 4 | 5 | | V-1 | Hist1h4d | 8360 | 1-Jun-15 | 10998 | 3 | 4 | 5 | | V-1 | Id4 | 3400 | 24-May-15 |
| 10903 | 3 | 4 | 5 | | V-1 | Hist1h4i | 8294 | 2-Jun-15 | 10999 | 3 | 4 | 5 | | V-1 | Ide | 3416 | 4-May-15 |
| 10904 | 3 | 4 | 5 | | V-1 | Hist1h4n | | | 11000 | 3 | 4 | 5 | | V-1 | Idi2 | 91734 | 12-May-15 |
| 10905 | 3 | 4 | 5 | | V-1 | Hist2h2aa1 | | | 11001 | 3 | 4 | 5 | | V-1 | Ids | 3423 | 23-May-15 |

Fig. 30 - 59

| | | | | | | | | | | | | | | | | |
|---|---|---|---|---|---|---|---|---|---|---|---|---|---|---|---|---|
| 11002 | 3 | 4 | 5 | | | V-1 | Ier3ip1 | 51124 | 4-May-15 | 11098 | 3 | 4 | 5 | | V-1 | Irx2 | 153572 | 4-May-15 |
| 11003 | 3 | 4 | 5 | | | V-1 | Ierf5l | 389792 | 4-May-15 | 11099 | 3 | 4 | 5 | | V-1 | Irx4 | 50805 | 4-May-15 |
| 11004 | 3 | 4 | 5 | | | V-1 | Iffo1 | 25900 | 4-May-15 | 11100 | 3 | 4 | 5 | | V-1 | Isca2 | 122961 | 31-May-15 |
| 11005 | 3 | 4 | 5 | | | V-1 | Ifi205 | | | 11101 | 3 | 4 | 5 | | V-1 | Isg20l2 | 81875 | 4-May-15 |
| 11006 | 3 | 4 | 5 | | | V-1 | Ifi35 | 3430 | 12-May-15 | 11102 | 3 | 4 | 5 | | V-1 | Isl2 | 64843 | 4-May-15 |
| 11007 | 3 | 4 | 5 | | | V-1 | Ifih1 | 64135 | 17-May-15 | 11103 | 3 | 4 | 5 | | V-1 | Ism2 | 145501 | 4-May-15 |
| 11008 | 3 | 4 | 5 | | | V-1 | Ifit2 | 3433 | 12-May-15 | 11104 | 3 | 4 | 5 | | V-1 | Itch | 83737 | 4-May-15 |
| 11009 | 3 | 4 | 5 | | | V-1 | Ifitm10 | 402778 | 4-May-15 | 11105 | 3 | 4 | 5 | | V-1 | Itga10 | 8515 | 12-May-15 |
| 11010 | 3 | 4 | 5 | | | V-1 | Ifitm3 | 10410 | 31-May-15 | 11106 | 3 | 4 | 5 | | V-1 | Itga2 | 3673 | 12-May-15 |
| 11011 | 3 | 4 | 5 | | | V-1 | Ifitm5 | 387733 | 4-May-15 | 11107 | 3 | 4 | 5 | | V-1 | Itga3 | 3675 | 30-May-15 |
| 11012 | 3 | 4 | 5 | | | V-1 | Ifitm7 | | | 11108 | 3 | 4 | 5 | | V-1 | Itga7 | 3679 | 23-May-15 |
| 11013 | 3 | 4 | 5 | | | V-1 | Ifitd1 | 160492 | 12-May-15 | 11109 | 3 | 4 | 5 | | V-1 | Itga8 | 8516 | 4-May-15 |
| 11014 | 3 | 4 | 5 | | | V-1 | Ifngr2 | 3460 | 24-May-15 | 11110 | 3 | 4 | 5 | | V-1 | Itgad | 3681 | 12-May-15 |
| 11015 | 3 | 4 | 5 | | | V-1 | Ifnk | 56832 | 4-May-15 | 11111 | 3 | 4 | 5 | | V-1 | Itgav | 3685 | 31-May-15 |
| 11016 | 3 | 4 | 5 | | | V-1 | Ifnz | | | 11112 | 3 | 4 | 5 | | V-1 | Itgb1 | 3688 | 31-May-15 |
| 11017 | 3 | 4 | 5 | | | V-1 | Ift122 | 55764 | 12-May-15 | 11113 | 3 | 4 | 5 | | V-1 | Itgb1bp1 | 9270 | 8-May-15 |
| 11018 | 3 | 4 | 5 | | | V-1 | Ift140 | 9742 | 4-May-15 | 11114 | 3 | 4 | 5 | | V-1 | Itgb2l | | |
| 11019 | 3 | 4 | 5 | | | V-1 | Igf1r | 3480 | 7-Jun-15 | 11115 | 3 | 4 | 5 | | V-1 | Itgb8 | 3696 | 31-May-15 |
| 11020 | 3 | 4 | 5 | | | V-1 | Igf2bp1 | 10642 | 1-Jun-15 | 11116 | 3 | 4 | 5 | | V-1 | Itih1 | 3697 | 4-May-15 |
| 11021 | 3 | 4 | 5 | | | V-1 | Igf2bp3 | 10643 | 4-May-15 | 11117 | 3 | 4 | 5 | | V-1 | Itih3 | 3699 | 4-May-15 |
| 11022 | 3 | 4 | 5 | | | V-1 | Igfbp4 | 3487 | 4-May-15 | 11118 | 3 | 4 | 5 | | V-1 | Itih5 | 80760 | 17-May-15 |
| 11023 | 3 | 4 | 5 | | | V-1 | Igfbpl1 | 347252 | 4-May-15 | 11119 | 3 | 4 | 5 | | V-1 | Itm2c | 81618 | 4-May-15 |
| 11024 | 3 | 4 | 5 | | | V-1 | Ighmbp2 | 3508 | 23-May-15 | 11120 | 3 | 4 | 5 | | V-1 | Itpa | 3704 | 31-May-15 |
| 11025 | 3 | 4 | 5 | | | V-1 | Iglon5 | 402665 | 4-May-15 | 11121 | 3 | 4 | 5 | | V-1 | Itpkb | 3707 | 4-May-15 |
| 11026 | 3 | 4 | 5 | | | V-1 | Igsf3 | 3321 | 4-May-15 | 11122 | 3 | 4 | 5 | | V-1 | Itpkc | 80271 | 31-May-15 |
| 11027 | 3 | 4 | 5 | | | V-1 | Igsf8 | 93185 | 4-May-15 | 11123 | 3 | 4 | 5 | | V-1 | Itpr1 | 3708 | 4-May-15 |
| 11028 | 3 | 4 | 5 | | | V-1 | Igsf9b | 22997 | 4-May-15 | 11124 | 3 | 4 | 5 | | V-1 | Itpripl1 | 150771 | 4-May-15 |
| 11029 | 3 | 4 | 5 | | | V-1 | Ik | 3550 | 7-Jun-15 | 11125 | 3 | 4 | 5 | | V-1 | Itpripl2 | 162073 | 4-May-15 |
| 11030 | 3 | 4 | 5 | | | V-1 | Ikbkap | 8518 | 23-May-15 | 11126 | 3 | 4 | 5 | | V-1 | Itsn1 | 6453 | 14-May-15 |
| 11031 | 3 | 4 | 5 | | | V-1 | Ikbkg | 8517 | 23-May-15 | 11127 | 3 | 4 | 5 | | V-1 | Itsn2 | 50618 | 4-May-15 |
| 11032 | 3 | 4 | 5 | | | V-1 | Ikzf2 | 22807 | 10-May-15 | 11128 | 3 | 4 | 5 | | V-1 | Ivns1abp | 10625 | 4-May-15 |
| 11033 | 3 | 4 | 5 | | | V-1 | Ikzf4 | 64375 | 4-May-15 | 11129 | 3 | 4 | 5 | | V-1 | Jade1 | 79960 | 4-May-15 |
| 11034 | 3 | 4 | 5 | | | V-1 | Ikzf5 | 64376 | 2-Jun-15 | 11130 | 3 | 4 | 5 | | V-1 | Jag1 | 182 | 31-May-15 |
| 11035 | 3 | 4 | 5 | | | V-1 | Il10rb | 3588 | 12-May-15 | 11131 | 3 | 4 | 5 | | V-1 | Jagn1 | 84522 | 4-May-15 |
| 11036 | 3 | 4 | 5 | | | V-1 | Il11ra1 | | | 11132 | 3 | 4 | 5 | | V-1 | Jakmip2 | 9832 | 4-May-15 |
| 11037 | 3 | 4 | 5 | | | V-1 | Il12b | 3593 | 23-May-15 | 11133 | 3 | 4 | 5 | | V-1 | Jarid2 | 3720 | 31-May-15 |
| 11038 | 3 | 4 | 5 | | | V-1 | Il12rb2 | 3595 | 4-May-15 | 11134 | 3 | 4 | 5 | | V-1 | Jkamp | 51528 | 4-May-15 |
| 11039 | 3 | 4 | 5 | | | V-1 | Il13 | 3596 | 4-May-15 | 11135 | 3 | 4 | 5 | | V-1 | Jmjd7-pla2g4b | 8681 | 4-May-15 |
| 11040 | 3 | 4 | 5 | | | V-1 | Il13ra2 | 3598 | 12-May-15 | 11136 | 3 | 4 | 5 | | V-1 | Jmjd8 | 339123 | 21-May-15 |
| 11041 | 3 | 4 | 5 | | | V-1 | Il15 | 3600 | 17-May-15 | 11137 | 3 | 4 | 5 | | V-1 | Jph1 | 56704 | 17-May-15 |
| 11042 | 3 | 4 | 5 | | | V-1 | Il15ra | 3601 | 4-May-15 | 11138 | 3 | 4 | 5 | | V-1 | Jph3 | 57338 | 23-May-15 |
| 11043 | 3 | 4 | 5 | | | V-1 | Il17a | 3605 | 7-Jun-15 | 11139 | 3 | 4 | 5 | | V-1 | Jtb | 10899 | 4-May-15 |
| 11044 | 3 | 4 | 5 | | | V-1 | Il17rb | 55540 | 4-May-15 | 11140 | 3 | 4 | 5 | | V-1 | Jund | 3727 | 4-May-15 |
| 11045 | 3 | 4 | 5 | | | V-1 | Il18bp | 10068 | 3-May-15 | 11141 | 3 | 4 | 5 | | V-1 | Jup | 3728 | 22-May-15 |
| 11046 | 3 | 4 | 5 | | | V-1 | Il19 | 29949 | 4-May-15 | 11142 | 3 | 4 | 5 | | V-1 | Kank2 | 25959 | 4-May-15 |
| 11047 | 3 | 4 | 5 | | | V-1 | Il1bos | | | 11143 | 3 | 4 | 5 | | V-1 | Kank4 | 163782 | 4-May-15 |
| 11048 | 3 | 4 | 5 | | | V-1 | Il1f6 | 27179 | 4-May-15 | 11144 | 3 | 4 | 5 | | V-1 | Kansl2 | 54934 | 12-May-15 |
| 11049 | 3 | 4 | 5 | | | V-1 | Il1rap | 3556 | 12-May-15 | 11145 | 3 | 4 | 5 | | V-1 | Kars | 3735 | 4-May-15 |
| 11050 | 3 | 4 | 5 | | | V-1 | Il1rapl1 | 11141 | 23-May-15 | 11146 | 3 | 4 | 5 | | V-1 | Katna1 | 11104 | 4-May-15 |
| 11051 | 3 | 4 | 5 | | | V-1 | Il1rl2 | 8808 | 4-May-15 | 11147 | 3 | 4 | 5 | | V-1 | Katnal2 | 83473 | 4-May-15 |
| 11052 | 3 | 4 | 5 | | | V-1 | Il2 | 3558 | 12-May-15 | 11148 | 3 | 4 | 5 | | V-1 | Kazald1 | 81621 | 4-May-15 |
| 11053 | 3 | 4 | 5 | | | V-1 | Il21 | 59067 | 7-Jun-15 | 11149 | 3 | 4 | 5 | | V-1 | Kazn | 23254 | 2-Jun-15 |
| 11054 | 3 | 4 | 5 | | | V-1 | Il22 | 50616 | 7-Jun-15 | 11150 | 3 | 4 | 5 | | V-1 | Kbtbd12 | 166348 | 4-May-15 |
| 11055 | 3 | 4 | 5 | | | V-1 | Il23a | 51561 | 17-May-15 | 11151 | 3 | 4 | 5 | | V-1 | Kcmf1 | 56888 | 4-May-15 |
| 11056 | 3 | 4 | 5 | | | V-1 | Il27ra | 9466 | 4-May-15 | 11152 | 3 | 4 | 5 | | V-1 | Kcna10 | 3744 | 4-May-15 |
| 11057 | 3 | 4 | 5 | | | V-1 | Il2rb | 3560 | 12-May-15 | 11153 | 3 | 4 | 5 | | V-1 | Kcna4 | 3739 | 12-May-15 |
| 11058 | 3 | 4 | 5 | | | V-1 | Il3 | 3562 | 12-May-15 | 11154 | 3 | 4 | 5 | | V-1 | Kcna6 | 3742 | 4-May-15 |
| 11059 | 3 | 4 | 5 | | | V-1 | Il4 | 3565 | 31-May-15 | 11155 | 3 | 4 | 5 | | V-1 | Kcnab3 | 9196 | 4-May-15 |
| 11060 | 3 | 4 | 5 | | | V-1 | Il4i1 | 259307 | 4-May-15 | 11156 | 3 | 4 | 5 | | V-1 | Kcng1 | 3755 | 3-May-15 |
| 11061 | 3 | 4 | 5 | | | V-1 | Il5 | 3567 | 28-May-15 | 11157 | 3 | 4 | 5 | | V-1 | Kcnh1 | 3756 | 17-May-15 |
| 11062 | 3 | 4 | 5 | | | V-1 | Il6st | 3572 | 12-May-15 | 11158 | 3 | 4 | 5 | | V-1 | Kcnh4 | 23415 | 4-May-15 |
| 11063 | 3 | 4 | 5 | | | V-1 | Il9 | 3578 | 7-Jun-15 | 11159 | 3 | 4 | 5 | | V-1 | Kcnip1 | 30820 | 4-May-15 |
| 11064 | 3 | 4 | 5 | | | V-1 | Ildr2 | 387597 | 12-May-15 | 11160 | 3 | 4 | 5 | | V-1 | Kcnip4 | 80333 | 4-May-15 |
| 11065 | 3 | 4 | 5 | | | V-1 | Ilf2 | 3608 | 4-May-15 | 11161 | 3 | 4 | 5 | | V-1 | Kcnj11 | 3767 | 31-May-15 |
| 11066 | 3 | 4 | 5 | | | V-1 | Immt | 10989 | 4-May-15 | 11162 | 3 | 4 | 5 | | V-1 | Kcnj13 | 3769 | 24-May-15 |
| 11067 | 3 | 4 | 5 | | | V-1 | Impad1 | 54928 | 4-May-15 | 11163 | 3 | 4 | 5 | | V-1 | Kcnj6 | 3763 | 4-May-15 |
| 11068 | 3 | 4 | 5 | | | V-1 | Impdh2 | 3615 | 31-May-15 | 11164 | 3 | 4 | 5 | | V-1 | Kcnj9 | 3765 | 12-May-15 |
| 11069 | 3 | 4 | 5 | | | V-1 | Inf2 | 64423 | 4-May-15 | 11165 | 3 | 4 | 5 | | V-1 | Kcnk10 | 54207 | 4-May-15 |
| 11070 | 3 | 4 | 5 | | | V-1 | Ing1 | 3621 | 17-May-15 | 11166 | 3 | 4 | 5 | | V-1 | Kcnk15 | 60598 | 4-May-15 |
| 11071 | 3 | 4 | 5 | | | V-1 | Inhbc | 3626 | 4-May-15 | 11167 | 3 | 4 | 5 | | V-1 | Kcnk4 | 50801 | 12-May-15 |
| 11072 | 3 | 4 | 5 | | | V-1 | Ino80 | 54617 | 4-May-15 | 11168 | 3 | 4 | 5 | | V-1 | Kcnk7 | 10089 | 4-May-15 |
| 11073 | 3 | 4 | 5 | | | V-1 | Ino80dos | | | 11169 | 3 | 4 | 5 | | V-1 | Kcnmb1 | 3779 | 4-May-15 |
| 11074 | 3 | 4 | 5 | | | V-1 | Inpp5e | 56623 | 23-May-15 | 11170 | 3 | 4 | 5 | | V-1 | Kcnmb4os1 | | |
| 11075 | 3 | 4 | 5 | | | V-1 | Inpp5k | 51763 | 4-May-15 | 11171 | 3 | 4 | 5 | | V-1 | Kcnn3 | 3782 | 12-May-15 |
| 11076 | 3 | 4 | 5 | | | V-1 | Insl3 | 3640 | 4-May-15 | 11172 | 3 | 4 | 5 | | V-1 | Kcnq1ot1 | 10984 | 22-May-15 |
| 11077 | 3 | 4 | 5 | | | V-1 | Insl5 | 10022 | 4-May-15 | 11173 | 3 | 4 | 5 | | V-1 | Kcnu1 | 157855 | 4-May-15 |
| 11078 | 3 | 4 | 5 | | | V-1 | Insm1 | 3642 | 4-May-15 | 11174 | 3 | 4 | 5 | | V-1 | Kctd1 | 284252 | 4-May-15 |
| 11079 | 3 | 4 | 5 | | | V-1 | Ints12 | 57117 | 4-May-15 | 11175 | 3 | 4 | 5 | | V-1 | Kctd12b | | |
| 11080 | 3 | 4 | 5 | | | V-1 | Ints8 | 55656 | 4-May-15 | 11176 | 3 | 4 | 5 | | V-1 | Kctd16 | 57528 | 4-May-15 |
| 11081 | 3 | 4 | 5 | | | V-1 | Ipmk | 253430 | 4-May-15 | 11177 | 3 | 4 | 5 | | V-1 | Kctd18 | 130535 | 4-May-15 |
| 11082 | 3 | 4 | 5 | | | V-1 | Ipo11 | 51194 | 4-May-15 | 11178 | 3 | 4 | 5 | | V-1 | Kctd8 | 386617 | 4-May-15 |
| 11083 | 3 | 4 | 5 | | | V-1 | Ipo4 | 79711 | 4-May-15 | 11179 | 3 | 4 | 5 | | V-1 | Kdelr1 | 10945 | 4-May-15 |
| 11084 | 3 | 4 | 5 | | | V-1 | Iqce | 23288 | 4-May-15 | 11180 | 3 | 4 | 5 | | V-1 | Kdelr3 | 11015 | 4-May-15 |
| 11085 | 3 | 4 | 5 | | | V-1 | Iqch | 64799 | 7-Jun-15 | 11181 | 3 | 4 | 5 | | V-1 | Kdm1a | 23028 | 10-May-15 |
| 11086 | 3 | 4 | 5 | | | V-1 | Iqsec1 | 9922 | 12-May-15 | 11182 | 3 | 4 | 5 | | V-1 | Kdsr | 2531 | 4-May-15 |
| 11087 | 3 | 4 | 5 | | | V-1 | Iqsec3 | 440073 | 4-May-15 | 11183 | 3 | 4 | 5 | | V-1 | Keap1 | 9817 | 31-May-15 |
| 11088 | 3 | 4 | 5 | | | V-1 | Irak2 | 3656 | 4-May-15 | 11184 | 3 | 4 | 5 | | V-1 | Kera | 11081 | 4-May-15 |
| 11089 | 3 | 4 | 5 | | | V-1 | Irak4 | 51135 | 3-May-15 | 11185 | 3 | 4 | 5 | | V-1 | Khk | 3795 | 3-May-15 |
| 11090 | 3 | 4 | 5 | | | V-1 | Ireb2 | 3658 | 12-May-15 | 11186 | 3 | 4 | 5 | | V-1 | Kif12 | 113220 | 4-May-15 |
| 11091 | 3 | 4 | 5 | | | V-1 | Irf2 | 3660 | 31-May-15 | 11187 | 3 | 4 | 5 | | V-1 | Kif13b | 23303 | 4-May-15 |
| 11092 | 3 | 4 | 5 | | | V-1 | Irf2bpl | 64207 | 12-May-15 | 11188 | 3 | 4 | 5 | | V-1 | Kif16b | 55614 | 4-May-15 |
| 11093 | 3 | 4 | 5 | | | V-1 | Irf9 | 10379 | 4-May-15 | 11189 | 3 | 4 | 5 | | V-1 | Kif17 | 57576 | 4-May-15 |
| 11094 | 3 | 4 | 5 | | | V-1 | Irgc1 | 56269 | 4-May-15 | 11190 | 3 | 4 | 5 | | V-1 | Kif19a | 124602 | 4-May-15 |
| 11095 | 3 | 4 | 5 | | | V-1 | Irgq | 126298 | 4-May-15 | 11191 | 3 | 4 | 5 | | V-1 | Kif1a | 547 | 23-May-15 |
| 11096 | 3 | 4 | 5 | | | V-1 | Irs3 | | | 11192 | 3 | 4 | 5 | | V-1 | Kif21a | 55605 | 23-May-15 |
| 11097 | 3 | 4 | 5 | | | V-1 | Irs4 | 8471 | 14-May-15 | 11193 | 3 | 4 | 5 | | V-1 | Kif26a | 26153 | 4-May-15 |

Fig. 30 - 60

| | | | | | | | | | | | | | | | | | |
|---|---|---|---|---|---|---|---|---|---|---|---|---|---|---|---|---|---|
| 11194 | 3 | 4 | 5 | | | V-1 | Kif27 | 55582 | 4-May-15 | 11290 | 3 | 4 | 5 | | | V-1 | Lct | 3938 | 12-May-15 |
| 11195 | 3 | 4 | 5 | | | V-1 | Kif3a | 11127 | 4-May-15 | 11291 | 3 | 4 | 5 | | | V-1 | Ldb1 | 8861 | 7-Jun-15 |
| 11196 | 3 | 4 | 5 | | | V-1 | Kif4-ps | | | 11292 | 3 | 4 | 5 | | | V-1 | Ldha | 3939 | 17-May-15 |
| 11197 | 3 | 4 | 5 | | | V-1 | Kifc2 | 90990 | 4-May-15 | 11293 | 3 | 4 | 5 | | | V-1 | Ldhal6b | 92483 | 12-May-15 |
| 11198 | 3 | 4 | 5 | | | V-1 | Kin | 22944 | 4-May-15 | 11294 | 3 | 4 | 5 | | | V-1 | Ldlrad1 | 388633 | 4-May-15 |
| 11199 | 3 | 4 | 5 | | | V-1 | Kirrel2 | 84063 | 4-May-15 | 11295 | 3 | 4 | 5 | | | V-1 | Ldlrad2 | 401944 | 4-May-15 |
| 11200 | 3 | 4 | 5 | | | V-1 | Kirrel3 | 84623 | 4-May-15 | 11296 | 3 | 4 | 5 | | | V-1 | Ldlrap1 | 26119 | 12-May-15 |
| 11201 | 3 | 4 | 5 | | | V-1 | Kitl | 4254 | 24-May-15 | 11297 | 3 | 4 | 5 | | | V-1 | Leap2 | 116842 | 4-May-15 |
| 11202 | 3 | 4 | 5 | | | V-1 | Kiz | 55857 | 21-May-15 | 11298 | 3 | 4 | 5 | | | V-1 | Lect1 | 11061 | 4-May-15 |
| 11203 | 3 | 4 | 5 | | | V-1 | Klc1 | 3831 | 12-May-15 | 11299 | 3 | 4 | 5 | | | V-1 | Lect2 | 3950 | 17-May-15 |
| 11204 | 3 | 4 | 5 | | | V-1 | Klc4 | 89953 | 4-May-15 | 11300 | 3 | 4 | 5 | | | V-1 | Lefty2 | 7044 | 4-May-15 |
| 11205 | 3 | 4 | 5 | | | V-1 | Klf11 | 8462 | 4-May-15 | 11301 | 3 | 4 | 5 | | | V-1 | Leo1 | 123169 | 4-May-15 |
| 11206 | 3 | 4 | 5 | | | V-1 | Klf12 | 11278 | 2-Jun-15 | 11302 | 3 | 4 | 5 | | | V-1 | Lepre1 | 64175 | 4-May-15 |
| 11207 | 3 | 4 | 5 | | | V-1 | Klf14 | 136259 | 4-May-15 | 11303 | 3 | 4 | 5 | | | V-1 | Leprel1 | 55214 | 4-May-15 |
| 11208 | 3 | 4 | 5 | | | V-1 | Klf16 | 83855 | 4-May-15 | 11304 | 3 | 4 | 5 | | | V-1 | Leprot | 54741 | 4-May-15 |
| 11209 | 3 | 4 | 5 | | | V-1 | Klf17 | 128209 | 24-May-15 | 11305 | 3 | 4 | 5 | | | V-1 | Lgals12 | 85329 | 4-May-15 |
| 11210 | 3 | 4 | 5 | | | V-1 | Klf3 | 51274 | 2-Jun-15 | 11306 | 3 | 4 | 5 | | | V-1 | Lgals2 | 3957 | 7-Jun-15 |
| 11211 | 3 | 4 | 5 | | | V-1 | Klf4 | 9314 | 31-May-15 | 11307 | 3 | 4 | 5 | | | V-1 | Lgals8 | 3964 | 17-May-15 |
| 11212 | 3 | 4 | 5 | | | V-1 | Klf7 | 8609 | 4-May-15 | 11308 | 3 | 4 | 5 | | | V-1 | Lgi1 | 9211 | 1-Jun-15 |
| 11213 | 3 | 4 | 5 | | | V-1 | Klf9 | 687 | 31-May-15 | 11309 | 3 | 4 | 5 | | | V-1 | Lgi4 | 163175 | 4-May-15 |
| 11214 | 3 | 4 | 5 | | | V-1 | Klhdc7b | 113730 | 4-May-15 | 11310 | 3 | 4 | 5 | | | V-1 | Lgr4 | 55366 | 12-May-15 |
| 11215 | 3 | 4 | 5 | | | V-1 | Klhdc8b | 200942 | 4-May-15 | 11311 | 3 | 4 | 5 | | | V-1 | Lgr6 | 59352 | 4-May-15 |
| 11216 | 3 | 4 | 5 | | | V-1 | Klhl13 | 90293 | 4-May-15 | 11312 | 3 | 4 | 5 | | | V-1 | Lhcgr | 3973 | 12-May-15 |
| 11217 | 3 | 4 | 5 | | | V-1 | Klhl5 | 80311 | 12-May-15 | 11313 | 3 | 4 | 5 | | | V-1 | Lhfpl1 | 340596 | 4-May-15 |
| 11218 | 3 | 4 | 5 | | | V-1 | Klhl20 | 27252 | 4-May-15 | 11314 | 3 | 4 | 5 | | | V-1 | Lhfpl3 | 375612 | 4-May-15 |
| 11219 | 3 | 4 | 5 | | | V-1 | Klhl24 | 54800 | 4-May-15 | 11315 | 3 | 4 | 5 | | | V-1 | Lhx3 | 8022 | 12-May-15 |
| 11220 | 3 | 4 | 5 | | | V-1 | Klhl26 | 55295 | 4-May-15 | 11316 | 3 | 4 | 5 | | | V-1 | Lhx8 | 431707 | 4-May-15 |
| 11221 | 3 | 4 | 5 | | | V-1 | Klhl31 | 401265 | 4-May-15 | 11317 | 3 | 4 | 5 | | | V-1 | Lig3 | 3980 | 16-Jun-15 |
| 11222 | 3 | 4 | 5 | | | V-1 | Klhl35 | 283212 | 7-Jun-15 | 11318 | 3 | 4 | 5 | | | V-1 | Lilra5 | 353514 | 4-May-15 |
| 11223 | 3 | 4 | 5 | | | V-1 | Klhl4 | 56062 | 4-May-15 | 11319 | 3 | 4 | 5 | | | V-1 | Lim2 | 3982 | 4-May-15 |
| 11224 | 3 | 4 | 5 | | | V-1 | Klhl42 | 57542 | 4-May-15 | 11320 | 3 | 4 | 5 | | | V-1 | Lime1 | 54923 | 4-May-15 |
| 11225 | 3 | 4 | 5 | | | V-1 | Klhl8 | 57563 | 12-May-15 | 11321 | 3 | 4 | 5 | | | V-1 | Lin28a | 79727 | 4-May-15 |
| 11226 | 3 | 4 | 5 | | | V-1 | Klk12 | 43849 | 4-May-15 | 11322 | 3 | 4 | 5 | | | V-1 | Lin7a | 8825 | 4-May-15 |
| 11227 | 3 | 4 | 5 | | | V-1 | Klk15 | 55554 | 12-May-15 | 11323 | 3 | 4 | 5 | | | V-1 | Lincrna-cox2 | | |
| 11228 | 3 | 4 | 5 | | | V-1 | Klk1b16 | | | 11324 | 3 | 4 | 5 | | | V-1 | Lingo2 | 158038 | 4-May-15 |
| 11229 | 3 | 4 | 5 | | | V-1 | Klk1b22 | | | 11325 | 3 | 4 | 5 | | | V-1 | Lingo4 | 339398 | 4-May-15 |
| 11230 | 3 | 4 | 5 | | | V-1 | Klk4 | 9622 | 7-Jun-15 | 11326 | 3 | 4 | 5 | | | V-1 | Lipc | 3990 | 24-May-15 |
| 11231 | 3 | 4 | 5 | | | V-1 | Klra13-ps | | | 11327 | 3 | 4 | 5 | | | V-1 | Lipf | 8513 | 4-May-15 |
| 11232 | 3 | 4 | 5 | | | V-1 | Klra15 | | | 11328 | 3 | 4 | 5 | | | V-1 | Liph | 200879 | 13-Jun-15 |
| 11233 | 3 | 4 | 5 | | | V-1 | Klra18 | | | 11329 | 3 | 4 | 5 | | | V-1 | Lipk | 643414 | 4-May-15 |
| 11234 | 3 | 4 | 5 | | | V-1 | Klra22 | | | 11330 | 3 | 4 | 5 | | | V-1 | Lipo1 | | |
| 11235 | 3 | 4 | 5 | | | V-1 | Klra3 | | | 11331 | 3 | 4 | 5 | | | V-1 | Lix1 | 167410 | 21-May-15 |
| 11236 | 3 | 4 | 5 | | | V-1 | Klra33 | | | 11332 | 3 | 4 | 5 | | | V-1 | Lix1l | 128077 | 12-May-15 |
| 11237 | 3 | 4 | 5 | | | V-1 | Klra4 | | | 11333 | 3 | 4 | 5 | | | V-1 | Llph | 84298 | 4-May-15 |
| 11238 | 3 | 4 | 5 | | | V-1 | Klra6 | | | 11334 | 3 | 4 | 5 | | | V-1 | Lman2 | 10960 | 4-May-15 |
| 11239 | 3 | 4 | 5 | | | V-1 | Klrb1 | 3820 | 4-May-15 | 11335 | 3 | 4 | 5 | | | V-1 | Lman2l | 81562 | 17-May-15 |
| 11240 | 3 | 4 | 5 | | | V-1 | Klrb1b | | | 11336 | 3 | 4 | 5 | | | V-1 | Lmf1 | 64788 | 14-May-15 |
| 11241 | 3 | 4 | 5 | | | V-1 | Klrb1c | | | 11337 | 3 | 4 | 5 | | | V-1 | Lmnb2 | 84823 | 4-May-15 |
| 11242 | 3 | 4 | 5 | | | V-1 | Klrb1-ps1 | | | 11338 | 3 | 4 | 5 | | | V-1 | Lmo1 | 4004 | 17-May-15 |
| 11243 | 3 | 4 | 5 | | | V-1 | Klrc3 | 3823 | 12-May-15 | 11339 | 3 | 4 | 5 | | | V-1 | Lmo3 | 55885 | 12-May-15 |
| 11244 | 3 | 4 | 5 | | | V-1 | Klrd1 | 3824 | 12-May-15 | 11340 | 3 | 4 | 5 | | | V-1 | Lnx2 | 222484 | 4-May-15 |
| 11245 | 3 | 4 | 5 | | | V-1 | Klrg1 | 10219 | 4-May-15 | 11341 | 3 | 4 | 5 | | | V-1 | LOC100040786 | | |
| 11246 | 3 | 4 | 5 | | | V-1 | Kmt2a | 4297 | 31-May-15 | 11342 | 3 | 4 | 5 | | | V-1 | LOC100502896 | | |
| 11247 | 3 | 4 | 5 | | | V-1 | Kmt2b | 9757 | 4-May-15 | 11343 | 3 | 4 | 5 | | | V-1 | LOC100504039 | | |
| 11248 | 3 | 4 | 5 | | | V-1 | Kpna1 | 3836 | 12-May-15 | 11344 | 3 | 4 | 5 | | | V-1 | LOC100504608 | | |
| 11249 | 3 | 4 | 5 | | | V-1 | Kpna3 | 3839 | 4-May-15 | 11345 | 3 | 4 | 5 | | | V-1 | LOC100504703 | | |
| 11250 | 3 | 4 | 5 | | | V-1 | Kptn | 11133 | 4-May-15 | 11346 | 3 | 4 | 5 | | | V-1 | LOC100505025 | | |
| 11251 | 3 | 4 | 5 | | | V-1 | Krt16 | 3868 | 23-May-15 | 11347 | 3 | 4 | 5 | | | V-1 | LOC100861978 | | |
| 11252 | 3 | 4 | 5 | | | V-1 | Krt2 | 3849 | 4-May-15 | 11348 | 3 | 4 | 5 | | | V-1 | LOC100862015 | | |
| 11253 | 3 | 4 | 5 | | | V-1 | Krt222 | 125113 | 4-May-15 | 11349 | 3 | 4 | 5 | | | V-1 | LOC101056136 | | |
| 11254 | 3 | 4 | 5 | | | V-1 | Krt24 | 192666 | 4-May-15 | 11350 | 3 | 4 | 5 | | | V-1 | LOC102632423 | | |
| 11255 | 3 | 4 | 5 | | | V-1 | Krt6a | 3853 | 28-May-15 | 11351 | 3 | 4 | 5 | | | V-1 | LOC102634101 | | |
| 11256 | 3 | 4 | 5 | | | V-1 | Krt77 | 374454 | 4-May-15 | 11352 | 3 | 4 | 5 | | | V-1 | LOC102636514 | | |
| 11257 | 3 | 4 | 5 | | | V-1 | Krt9 | 3857 | 4-May-15 | 11353 | 3 | 4 | 5 | | | V-1 | LOC666331 | | |
| 11258 | 3 | 4 | 5 | | | V-1 | Krtap3-3 | 85293 | 4-May-15 | 11354 | 3 | 4 | 5 | | | V-1 | Loxhd1 | 125336 | 23-May-15 |
| 11259 | 3 | 4 | 5 | | | V-1 | Krtcap3 | 200634 | 4-May-15 | 11355 | 3 | 4 | 5 | | | V-1 | Lpar1 | 1902 | 4-May-15 |
| 11260 | 3 | 4 | 5 | | | V-1 | Ksr1 | 8844 | 4-May-15 | 11356 | 3 | 4 | 5 | | | V-1 | Lpar2 | 9170 | 12-May-15 |
| 11261 | 3 | 4 | 5 | | | V-1 | Ktn2 | 112970 | 4-May-15 | 11357 | 3 | 4 | 5 | | | V-1 | Lpcat1 | 79888 | 4-May-15 |
| 11262 | 3 | 4 | 5 | | | V-1 | L1cam | 3897 | 23-May-15 | 11358 | 3 | 4 | 5 | | | V-1 | Lpcat2b | | |
| 11263 | 3 | 4 | 5 | | | V-1 | L3mbtl1 | 26013 | 4-May-15 | 11359 | 3 | 4 | 5 | | | V-1 | Lpcat4 | 254531 | 7-Jun-15 |
| 11264 | 3 | 4 | 5 | | | V-1 | Lage3 | 8270 | 4-May-15 | 11360 | 3 | 4 | 5 | | | V-1 | Lpgat1 | 9926 | 4-May-15 |
| 11265 | 3 | 4 | 5 | | | V-1 | Lalba | 3906 | 4-May-15 | 11361 | 3 | 4 | 5 | | | V-1 | Lphn3 | 23284 | 4-May-15 |
| 11266 | 3 | 4 | 5 | | | V-1 | Lama2 | 3908 | 23-May-15 | 11362 | 3 | 4 | 5 | | | V-1 | Lpp | 4026 | 12-May-15 |
| 11267 | 3 | 4 | 5 | | | V-1 | Lama3 | 3909 | 7-Jun-15 | 11363 | 3 | 4 | 5 | | | V-1 | Lrba | 987 | 7-Jun-15 |
| 11268 | 3 | 4 | 5 | | | V-1 | Lama5 | 3911 | 12-May-15 | 11364 | 3 | 4 | 5 | | | V-1 | Lrfn1 | 57622 | 12-May-15 |
| 11269 | 3 | 4 | 5 | | | V-1 | Lamb1 | 3912 | 12-May-15 | 11365 | 3 | 4 | 5 | | | V-1 | Lrfn4 | 78999 | 4-May-15 |
| 11270 | 3 | 4 | 5 | | | V-1 | Lamb2 | 3913 | 7-Jun-15 | 11366 | 3 | 4 | 5 | | | V-1 | Lrguk | 136332 | 12-May-15 |
| 11271 | 3 | 4 | 5 | | | V-1 | Lamc1 | 3915 | 12-May-15 | 11367 | 3 | 4 | 5 | | | V-1 | Lrig1 | 26018 | 4-May-15 |
| 11272 | 3 | 4 | 5 | | | V-1 | Lamc3 | 10319 | 4-May-15 | 11368 | 3 | 4 | 5 | | | V-1 | Lrig2 | 9860 | 7-Jun-15 |
| 11273 | 3 | 4 | 5 | | | V-1 | Lamp5 | 24141 | 4-May-15 | 11369 | 3 | 4 | 5 | | | V-1 | Lrit1 | 26103 | 12-May-15 |
| 11274 | 3 | 4 | 5 | | | V-1 | Lamtor5 | 10542 | 17-May-15 | 11370 | 3 | 4 | 5 | | | V-1 | Lrit2 | 340745 | 4-May-15 |
| 11275 | 3 | 4 | 5 | | | V-1 | Lancl3 | 347404 | 4-May-15 | 11371 | 3 | 4 | 5 | | | V-1 | Lrp10 | 26020 | 4-May-15 |
| 11276 | 3 | 4 | 5 | | | V-1 | Lao1 | | | 11372 | 3 | 4 | 5 | | | V-1 | Lrp1b | 53353 | 12-May-15 |
| 11277 | 3 | 4 | 5 | | | V-1 | Large | 9215 | 23-May-15 | 11373 | 3 | 4 | 5 | | | V-1 | Lrp2bp | 55805 | 7-Jun-15 |
| 11278 | 3 | 4 | 5 | | | V-1 | Larp4 | 113251 | 3-May-15 | 11374 | 3 | 4 | 5 | | | V-1 | Lrp4 | 4038 | 7-Jun-15 |
| 11279 | 3 | 4 | 5 | | | V-1 | Lars | 51520 | 4-May-15 | 11375 | 3 | 4 | 5 | | | V-1 | Lrp5 | 4041 | 23-May-15 |
| 11280 | 3 | 4 | 5 | | | V-1 | Lars2 | 81887 | 4-May-15 | 11376 | 3 | 4 | 5 | | | V-1 | Lrpap1 | 4043 | 12-May-15 |
| 11281 | 3 | 4 | 5 | | | V-1 | Lats1 | 9113 | 24-May-15 | 11377 | 3 | 4 | 5 | | | V-1 | Lrrc1 | 55227 | 4-May-15 |
| 11282 | 3 | 4 | 5 | | | V-1 | Lbh | 81606 | 7-Jun-15 | 11378 | 3 | 4 | 5 | | | V-1 | Lrrc10 | 376132 | 4-May-15 |
| 11283 | 3 | 4 | 5 | | | V-1 | Lbx1 | 10660 | 4-May-15 | 11379 | 3 | 4 | 5 | | | V-1 | Lrrc16b | 90668 | 12-May-15 |
| 11284 | 3 | 4 | 5 | | | V-1 | Lce1m | | | 11380 | 3 | 4 | 5 | | | V-1 | Lrrc27 | 80313 | 5-Jun-15 |
| 11285 | 3 | 4 | 5 | | | V-1 | Lce6a | 448835 | 4-May-15 | 11381 | 3 | 4 | 5 | | | V-1 | Lrrc3 | 81543 | 4-May-15 |
| 11286 | 3 | 4 | 5 | | | V-1 | Lcn11 | | | 11382 | 3 | 4 | 5 | | | V-1 | Lrrc32 | 2615 | 20-May-15 |
| 11287 | 3 | 4 | 5 | | | V-1 | Lcn3 | | | 11383 | 3 | 4 | 5 | | | V-1 | Lrrc34 | 151827 | 4-May-15 |
| 11288 | 3 | 4 | 5 | | | V-1 | Lcor | 84458 | 4-May-15 | 11384 | 3 | 4 | 5 | | | V-1 | Lrrc47 | 57470 | 4-May-15 |
| 11289 | 3 | 4 | 5 | | | V-1 | Lrp2 | 3937 | 4-May-15 | 11385 | 3 | 4 | 5 | | | V-1 | Lrrc51 | 220074 | 23-May-15 |

Fig. 30 - 61

| | | | | | | | | | | | | | | | | | |
|---|---|---|---|---|---|---|---|---|---|---|---|---|---|---|---|---|---|
| 11386 | 3 | 4 | 5 | | | V-1 | Lrrc59 | 55379 | 4-May-15 | 11480 | 3 | 4 | 5 | | | V-1 | Mapk8 | 5599 | 7-May-15 |
| 11387 | 3 | 4 | 5 | | | V-1 | Lrrc6 | 23639 | 7-Jun-15 | 11481 | 3 | 4 | 5 | | | V-1 | Mapre1 | 22919 | 31-May-15 |
| 11388 | 3 | 4 | 5 | | | V-1 | Lrrc69 | 100130742 | 12-May-15 | 11482 | 3 | 4 | 5 | | | V-1 | March10 | 162333 | 4-May-15 |
| | | | | | | | | | | 11483 | 3 | 4 | 5 | | | V-1 | March4 | 57574 | 4-May-15 |
| 11389 | 3 | 4 | 5 | | | V-1 | Lrrc72 | 100506049 | 4-May-15 | 11484 | 3 | 4 | 5 | | | V-1 | March6 | 10299 | 4-May-15 |
| 11390 | 3 | 4 | 5 | | | V-1 | Lrrc74 | 145497 | 4-May-15 | 11485 | 3 | 4 | 5 | | | V-1 | March9 | 92979 | 4-May-15 |
| 11391 | 3 | 4 | 5 | | | V-1 | Lrrc75b | 388886 | 4-May-15 | 11486 | 3 | 4 | 5 | | | V-1 | Marf1 | 9665 | 4-May-15 |
| 11392 | 3 | 4 | 5 | | | V-1 | Lrrc8a | 56262 | 1-Jun-15 | 11487 | 3 | 4 | 5 | | | V-1 | Mark2 | 2011 | 21-May-15 |
| 11393 | 3 | 4 | 5 | | | V-1 | Lrrc8b | 23507 | 4-May-15 | 11488 | 3 | 4 | 5 | | | V-1 | Marveld1 | 83742 | 4-May-15 |
| 11394 | 3 | 4 | 5 | | | V-1 | Lrrc8d | 55144 | 4-May-15 | 11489 | 3 | 4 | 5 | | | V-1 | Mas1 | 4142 | 4-May-15 |
| 11395 | 3 | 4 | 5 | | | V-1 | Lrrcc1 | 85444 | 4-May-15 | 11490 | 3 | 4 | 5 | | | V-1 | Mast1 | 22983 | 7-Jun-15 |
| 11396 | 3 | 4 | 5 | | | V-1 | Lrrd1 | 401387 | 4-May-15 | 11491 | 3 | 4 | 5 | | | V-1 | Mast4 | 375449 | 12-May-15 |
| 11397 | 3 | 4 | 5 | | | V-1 | Lrrfip2 | 9209 | 4-May-15 | 11492 | 3 | 4 | 5 | | | V-1 | Mat1a | 4143 | 12-May-15 |
| 11398 | 3 | 4 | 5 | | | V-1 | Lrrn2 | 10446 | 4-May-15 | 11493 | 3 | 4 | 5 | | | V-1 | Mat2a | 4144 | 12-May-15 |
| 11399 | 3 | 4 | 5 | | | V-1 | Lrrn3 | 54674 | 4-May-15 | 11494 | 3 | 4 | 5 | | | V-1 | Matn3 | 4148 | 23-May-15 |
| 11400 | 3 | 4 | 5 | | | V-1 | Lrrtm1 | 347730 | 17-May-15 | 11495 | 3 | 4 | 5 | | | V-1 | Matr3 | 9782 | 10-May-15 |
| 11401 | 3 | 4 | 5 | | | V-1 | Lsm3 | 27258 | 4-May-15 | 11496 | 3 | 4 | 5 | | | V-1 | Mb21d1 | 115004 | 4-May-15 |
| 11402 | 3 | 4 | 5 | | | V-1 | Lsm4 | 25804 | 28-May-15 | 11497 | 3 | 4 | 5 | | | V-1 | Mbd2 | 8932 | 7-Jun-15 |
| 11403 | 3 | 4 | 5 | | | V-1 | Lsm6 | 11157 | 4-May-15 | 11498 | 3 | 4 | 5 | | | V-1 | Mbd5 | 55777 | 31-May-15 |
| 11404 | 3 | 4 | 5 | | | V-1 | Lsm7 | 51690 | 4-May-15 | 11499 | 3 | 4 | 5 | | | V-1 | Mboat4 | 619373 | 12-May-15 |
| 11405 | 3 | 4 | 5 | | | V-1 | Lsm8 | 51691 | 4-May-15 | 11500 | 3 | 4 | 5 | | | V-1 | Mcat | 27349 | 4-May-15 |
| 11406 | 3 | 4 | 5 | | | V-1 | Lta | 4049 | 12-May-15 | 11501 | 3 | 4 | 5 | | | V-1 | Mccc1 | 56922 | 23-May-15 |
| 11407 | 3 | 4 | 5 | | | V-1 | Lta4h | 4048 | 12-May-15 | 11502 | 3 | 4 | 5 | | | V-1 | Mcf2 | 4168 | 4-May-15 |
| 11408 | 3 | 4 | 5 | | | V-1 | Ltb4r2 | 56413 | 4-May-15 | 11503 | 3 | 4 | 5 | | | V-1 | Mcfd2 | 90411 | 1-Jun-15 |
| 11409 | 3 | 4 | 5 | | | V-1 | Ltbp1 | 4052 | 12-May-15 | 11504 | 3 | 4 | 5 | | | V-1 | Mcm3ap | 8888 | 12-May-15 |
| 11410 | 3 | 4 | 5 | | | V-1 | Ltbp4 | 8425 | 12-May-15 | 11505 | 3 | 4 | 5 | | | V-1 | Mcm8 | 84515 | 4-May-15 |
| 11411 | 3 | 4 | 5 | | | V-1 | Ltbr | 4055 | 12-May-15 | 11506 | 3 | 4 | 5 | | | V-1 | Mcm9 | 254394 | 4-May-15 |
| 11412 | 3 | 4 | 5 | | | V-1 | Ltk | 4058 | 4-May-15 | 11507 | 3 | 4 | 5 | | | V-1 | Mcpt1 | 1375 | 4-May-15 |
| 11413 | 3 | 4 | 5 | | | V-1 | Ltn1 | 26046 | 23-May-15 | 11508 | 3 | 4 | 5 | | | V-1 | Mcpt2 | | |
| 11414 | 3 | 4 | 5 | | | V-1 | Lurap1 | 541468 | 4-May-15 | 11509 | 3 | 4 | 5 | | | V-1 | Mcpt9 | | |
| 11415 | 3 | 4 | 5 | | | V-1 | Luzp1 | 7798 | 4-May-15 | 11510 | 3 | 4 | 5 | | | V-1 | Mcrs1 | 10445 | 12-May-15 |
| 11416 | 3 | 4 | 5 | | | V-1 | Ly6c1 | | | 11511 | 3 | 4 | 5 | | | V-1 | Mctp2 | 55784 | 4-May-15 |
| 11417 | 3 | 4 | 5 | | | V-1 | Ly6e | 4061 | 4-May-15 | 11512 | 3 | 4 | 5 | | | V-1 | Mcts1 | 28985 | 4-May-15 |
| 11418 | 3 | 4 | 5 | | | V-1 | Ly6f | | | 11513 | 3 | 4 | 5 | | | V-1 | Mdfic | 29969 | 4-May-15 |
| 11419 | 3 | 4 | 5 | | | V-1 | Ly6g6c | 80740 | 4-May-15 | 11514 | 3 | 4 | 5 | | | V-1 | Mdga1 | 266727 | 4-May-15 |
| 11420 | 3 | 4 | 5 | | | V-1 | Ly6g6e | 79136 | 4-May-15 | 11515 | 3 | 4 | 5 | | | V-1 | Mdm1 | 56890 | 12-May-15 |
| 11421 | 3 | 4 | 5 | | | V-1 | Ly6g6f | 259215 | 4-May-15 | 11516 | 3 | 4 | 5 | | | V-1 | Mdp1 | 145553 | 7-Jun-15 |
| 11422 | 3 | 4 | 5 | | | V-1 | Ly6k | 54742 | 4-May-15 | 11517 | 3 | 4 | 5 | | | V-1 | Me3 | 10873 | 12-May-15 |
| 11423 | 3 | 4 | 5 | | | V-1 | Ly96 | 23643 | 31-May-15 | 11518 | 3 | 4 | 5 | | | V-1 | Med16 | 10025 | 12-May-15 |
| 11424 | 3 | 4 | 5 | | | V-1 | Lyar | 55646 | 4-May-15 | 11519 | 3 | 4 | 5 | | | V-1 | Med27 | 9442 | 4-May-15 |
| 11425 | 3 | 4 | 5 | | | V-1 | Lyg1 | 129530 | 4-May-15 | 11520 | 3 | 4 | 5 | | | V-1 | Med28 | 80306 | 4-May-15 |
| 11426 | 3 | 4 | 5 | | | V-1 | Lynx1 | 66004 | 4-May-15 | 11521 | 3 | 4 | 5 | | | V-1 | Med4 | 29079 | 31-May-15 |
| 11427 | 3 | 4 | 5 | | | V-1 | Lypd4 | 147719 | 12-May-15 | 11522 | 3 | 4 | 5 | | | V-1 | Med7 | 9443 | 4-May-15 |
| 11428 | 3 | 4 | 5 | | | V-1 | Lypd6 | 130574 | 4-May-15 | 11523 | 3 | 4 | 5 | | | V-1 | Mef2a | 4205 | 17-May-15 |
| 11429 | 3 | 4 | 5 | | | V-1 | Lypla1 | 10434 | 4-May-15 | 11524 | 3 | 4 | 5 | | | V-1 | Mef2d | 4209 | 28-May-15 |
| 11430 | 3 | 4 | 5 | | | V-1 | Lyrm1 | 57149 | 12-May-15 | 11525 | 3 | 4 | 5 | | | V-1 | Megf10 | 84466 | 7-Jun-15 |
| 11431 | 3 | 4 | 5 | | | V-1 | Lyrm7os | | | 11526 | 3 | 4 | 5 | | | V-1 | Megf8 | 1954 | 4-May-15 |
| 11432 | 3 | 4 | 5 | | | V-1 | Lyzl1 | 84569 | 4-May-15 | 11527 | 3 | 4 | 5 | | | V-1 | Megf9 | 1955 | 4-May-15 |
| 11433 | 3 | 4 | 5 | | | V-1 | M6pr | 4074 | 7-Jun-15 | 11528 | 3 | 4 | 5 | | | V-1 | Mei1 | 150365 | 12-May-15 |
| 11434 | 3 | 4 | 5 | | | V-1 | Macrod2 | 140733 | 3-May-15 | 11529 | 3 | 4 | 5 | | | V-1 | Meis3 | 56917 | 7-Jun-15 |
| 11435 | 3 | 4 | 5 | | | V-1 | Mad2l1bp | 9587 | 4-May-15 | 11530 | 3 | 4 | 5 | | | V-1 | Men1 | 4221 | 23-May-15 |
| 11436 | 3 | 4 | 5 | | | V-1 | Madd | 8567 | 7-Jun-15 | 11531 | 3 | 4 | 5 | | | V-1 | Mep1a | 4224 | 12-May-15 |
| 11437 | 3 | 4 | 5 | | | V-1 | Maea | 10296 | 12-May-15 | 11532 | 3 | 4 | 5 | | | V-1 | Mesdc1 | 59274 | 4-May-15 |
| 11438 | 3 | 4 | 5 | | | V-1 | Maf1 | 84232 | 4-May-15 | 11533 | 3 | 4 | 5 | | | V-1 | Mesdc2 | 23184 | 4-May-15 |
| 11439 | 3 | 4 | 5 | | | V-1 | Mafg | 4097 | 2-Jun-15 | 11534 | 3 | 4 | 5 | | | V-1 | Metap1 | 23173 | 4-May-15 |
| 11440 | 3 | 4 | 5 | | | V-1 | Mag | 4099 | 4-May-15 | 11535 | 3 | 4 | 5 | | | V-1 | Metrn | 79006 | 4-May-15 |
| 11441 | 3 | 4 | 5 | | | V-1 | Magea1 | 4100 | 4-May-15 | 11536 | 3 | 4 | 5 | | | V-1 | Mettl10 | 399818 | 4-May-15 |
| 11442 | 3 | 4 | 5 | | | V-1 | Mageb16 | 139604 | 4-May-15 | 11537 | 3 | 4 | 5 | | | V-1 | Mettl21a | 151194 | 23-May-15 |
| 11443 | 3 | 4 | 5 | | | V-1 | Magel2 | 54551 | 23-May-15 | 11538 | 3 | 4 | 5 | | | V-1 | Mettl7a2Higd1c | | |
| 11444 | 3 | 4 | 5 | | | V-1 | Magi2 | 9863 | 10-May-15 | 11539 | 3 | 4 | 5 | | | V-1 | Mettl9 | 51108 | 21-May-15 |
| 11445 | 3 | 4 | 5 | | | V-1 | Magt1 | 84061 | 23-May-15 | 11540 | 3 | 4 | 5 | | | V-1 | Mex3c | 51320 | 28-May-15 |
| 11446 | 3 | 4 | 5 | | | V-1 | Mal1 | 7851 | 4-May-15 | 11541 | 3 | 4 | 5 | | | V-1 | Mfap3 | 4238 | 4-May-15 |
| 11447 | 3 | 4 | 5 | | | V-1 | Malsu1 | 115416 | 12-May-15 | 11542 | 3 | 4 | 5 | | | V-1 | Mff | 56947 | 4-May-15 |
| 11448 | 3 | 4 | 5 | | | V-1 | Mamdc2 | 256691 | 4-May-15 | 11543 | 3 | 4 | 5 | | | V-1 | Mfhas1 | 9258 | 4-May-15 |
| 11449 | 3 | 4 | 5 | | | V-1 | Mamdc4 | 158056 | 4-May-15 | 11544 | 3 | 4 | 5 | | | V-1 | Mfi2 | 4241 | 4-May-15 |
| 11450 | 3 | 4 | 5 | | | V-1 | Mamld1 | 10046 | 23-May-15 | 11545 | 3 | 4 | 5 | | | V-1 | Mfsd1 | 64747 | 4-May-15 |
| 11451 | 3 | 4 | 5 | | | V-1 | Mamstr | 284358 | 4-May-15 | 11546 | 3 | 4 | 5 | | | V-1 | Mfsd10 | 10227 | 4-May-15 |
| 11452 | 3 | 4 | 5 | | | V-1 | Man1a2 | 10905 | 12-May-15 | 11547 | 3 | 4 | 5 | | | V-1 | Mfsd11 | 79157 | 4-May-15 |
| 11453 | 3 | 4 | 5 | | | V-1 | Man2a1 | 4124 | 4-May-15 | 11548 | 3 | 4 | 5 | | | V-1 | Mfsd2b | 388931 | 4-May-15 |
| 11454 | 3 | 4 | 5 | | | V-1 | Man2a2 | 4122 | 12-May-15 | 11549 | 3 | 4 | 5 | | | V-1 | Mfsd3 | 113655 | 4-May-15 |
| 11455 | 3 | 4 | 5 | | | V-1 | Man2b2 | 23324 | 12-May-15 | 11550 | 3 | 4 | 5 | | | V-1 | Mfsd7b | 28982 | 4-May-15 |
| 11456 | 3 | 4 | 5 | | | V-1 | Manr | | | 11551 | 3 | 4 | 5 | | | V-1 | Mfsd7c | 55640 | 4-May-15 |
| 11457 | 3 | 4 | 5 | | | V-1 | Map10 | 54627 | 4-May-15 | 11552 | 3 | 4 | 5 | | | V-1 | Mga | 23269 | 7-Jun-15 |
| 11458 | 3 | 4 | 5 | | | V-1 | Map1lc3a | 84557 | 21-May-15 | 11553 | 3 | 4 | 5 | | | V-1 | Mgam | 8972 | 12-May-15 |
| 11459 | 3 | 4 | 5 | | | V-1 | Map2k2 | 5605 | 7-Jun-15 | 11554 | 3 | 4 | 5 | | | V-1 | Mgat4b | 11282 | 4-May-15 |
| 11460 | 3 | 4 | 5 | | | V-1 | Map2k3os | | | 11555 | 3 | 4 | 5 | | | V-1 | Mgea5 | 10724 | 7-Jun-15 |
| 11461 | 3 | 4 | 5 | | | V-1 | Map2k4 | 6416 | 12-May-15 | 11556 | 3 | 4 | 5 | | | V-1 | Mgme1 | 92667 | 4-May-15 |
| 11462 | 3 | 4 | 5 | | | V-1 | Map3k10 | 4294 | 4-May-15 | 11557 | 3 | 4 | 5 | | | V-1 | Mgmt | 4255 | 17-May-15 |
| 11463 | 3 | 4 | 5 | | | V-1 | Map3k15 | 389840 | 21-May-15 | 11558 | 3 | 4 | 5 | | | V-1 | Mgrn1 | 23295 | 4-May-15 |
| 11464 | 3 | 4 | 5 | | | V-1 | Map3k2 | 10746 | 4-May-15 | 11559 | 3 | 4 | 5 | | | V-1 | Mia2 | 117153 | 7-Jun-15 |
| 11465 | 3 | 4 | 5 | | | V-1 | Map3k7 | 6885 | 12-May-15 | 11560 | 3 | 4 | 5 | | | V-1 | Mia3 | 375056 | 4-May-15 |
| 11466 | 3 | 4 | 5 | | | V-1 | Map3k9 | 4293 | 4-May-15 | 11561 | 3 | 4 | 5 | | | V-1 | Mical2 | 9645 | 12-May-15 |
| 11467 | 3 | 4 | 5 | | | V-1 | Map4 | 4134 | 4-May-15 | 11562 | 3 | 4 | 5 | | | V-1 | Mical3 | 57553 | 23-May-15 |
| 11468 | 3 | 4 | 5 | | | V-1 | Map4k2 | 5871 | 3-May-15 | 11563 | 3 | 4 | 5 | | | V-1 | Micalcl | 84953 | 4-May-15 |
| 11469 | 3 | 4 | 5 | | | V-1 | Map4k3 | 8491 | 12-May-15 | 11564 | 3 | 4 | 5 | | | V-1 | Micu1 | 10367 | 4-May-15 |
| 11470 | 3 | 4 | 5 | | | V-1 | Map4k5 | 11183 | 4-May-15 | 11565 | 3 | 4 | 5 | | | V-1 | Mid2 | 13043 | 4-May-15 |
| 11471 | 3 | 4 | 5 | | | V-1 | Map6d1 | 79929 | 4-May-15 | 11566 | 3 | 4 | 5 | | | V-1 | Mief1 | 54471 | 12-May-15 |
| 11472 | 3 | 4 | 5 | | | V-1 | Map7d1 | 55700 | 4-May-15 | 11567 | 3 | 4 | 5 | | | V-1 | Mier1 | 57708 | 12-May-15 |
| 11473 | 3 | 4 | 5 | | | V-1 | Map9 | 79884 | 4-May-15 | 11568 | 3 | 4 | 5 | | | V-1 | Mif | 4282 | 4-May-15 |
| 11474 | 3 | 4 | 5 | | | V-1 | Mapk1 | 5594 | 7-Jun-15 | 11569 | 3 | 4 | 5 | | | V-1 | Mif4gd | 57409 | 3-May-15 |
| 11475 | 3 | 4 | 5 | | | V-1 | Mapk12 | 6300 | 12-May-15 | 11570 | 3 | 4 | 5 | | | V-1 | Mill1 | | |
| 11476 | 3 | 4 | 5 | | | V-1 | Mapk14 | 1432 | 31-May-15 | 11571 | 3 | 4 | 5 | | | V-1 | Mina | 84864 | 12-May-15 |
| 11477 | 3 | 4 | 5 | | | V-1 | Mapk1ip1 | | | 11572 | 3 | 4 | 5 | | | V-1 | Mios | 54468 | 29-May-15 |
| 11478 | 3 | 4 | 5 | | | V-1 | Mapk1ip1l | 93487 | 4-May-15 | 11573 | 3 | 4 | 5 | | | V-1 | Mir101a | | |
| | | | | | | | | | | 11574 | 3 | 4 | 5 | | | V-1 | Mir105 | | |
| 11479 | 3 | 4 | 5 | | | V-1 | Mapk7 | 5598 | 4-May-15 | 11575 | 3 | 4 | 5 | | | V-1 | Mir1187 | | |

Fig. 30 - 62

| | | | | | | | | | | | | | | | | |
|---|---|---|---|---|---|---|---|---|---|---|---|---|---|---|---|---|
| 11576 | 3 | 4 | 5 | | | V-1 | Mir1195 | | | 11668 | 3 | 4 | 5 | | | V-1 | Mir6896 | | |
| 11577 | 3 | 4 | 5 | | | V-1 | Mir122a | 406906 | 7-Jun-15 | 11669 | 3 | 4 | 5 | | | V-1 | Mir6903 | | |
| 11578 | 3 | 4 | 5 | | | V-1 | Mir124a-1 | | | 11670 | 3 | 4 | 5 | | | V-1 | Mir691 | | |
| 11579 | 3 | 4 | 5 | | | V-1 | Mir1264 | 100302251 | 4-May-15 | 11671 | 3 | 4 | 5 | | | V-1 | Mir6923 | | |
| | | | | | | | | | | 11672 | 3 | 4 | 5 | | | V-1 | Mir6932 | | |
| 11580 | 3 | 4 | 5 | | | V-1 | Mir1298 | 100302153 | 4-May-15 | 11673 | 3 | 4 | 5 | | | V-1 | Mir694 | | |
| 11581 | 3 | 4 | 5 | | | V-1 | Mir136 | 406927 | 24-May-15 | 11674 | 3 | 4 | 5 | | | V-1 | Mir6978 | | |
| 11582 | 3 | 4 | 5 | | | V-1 | Mir143hg | 728264 | 12-May-15 | 11675 | 3 | 4 | 5 | | | V-1 | Mir7002 | | |
| 11583 | 3 | 4 | 5 | | | V-1 | Mir148b | 442892 | 21-May-15 | 11676 | 3 | 4 | 5 | | | V-1 | Mir7008 | | |
| 11584 | 3 | 4 | 5 | | | V-1 | Mir15b | 406949 | 21-May-15 | 11677 | 3 | 4 | 5 | | | V-1 | Mir7029 | | |
| 11585 | 3 | 4 | 5 | | | V-1 | Mir182 | 406958 | 7-Jun-15 | 11678 | 3 | 4 | 5 | | | V-1 | Mir7040 | | |
| 11586 | 3 | 4 | 5 | | | V-1 | Mir184 | 406960 | 21-May-15 | 11679 | 3 | 4 | 5 | | | V-1 | Mir7047 | | |
| 11587 | 3 | 4 | 5 | | | V-1 | Mir188 | 406964 | 21-May-15 | 11680 | 3 | 4 | 5 | | | V-1 | Mir706 | | |
| 11588 | 3 | 4 | 5 | | | V-1 | Mir190b | 100126346 | 21-May-15 | 11681 | 3 | 4 | 5 | | | V-1 | Mir7084 | | |
| | | | | | | | | | | 11682 | 3 | 4 | 5 | | | V-1 | Mir710 | | |
| 11589 | 3 | 4 | 5 | | | V-1 | Mir1912 | 100302144 | 21-May-15 | 11683 | 3 | 4 | 5 | | | V-1 | Mir7119 | | |
| | | | | | | | | | | 11684 | 3 | 4 | 5 | | | V-1 | Mir718 | 100313781 | 4-May-15 |
| 11590 | 3 | 4 | 5 | | | V-1 | Mir1951 | | | 11685 | 3 | 4 | 5 | | | V-1 | Mir7212 | | |
| 11591 | 3 | 4 | 5 | | | V-1 | Mir1962 | | | 11686 | 3 | 4 | 5 | | | V-1 | Mir7217 | | |
| 11592 | 3 | 4 | 5 | | | V-1 | Mir196a-2 | | | 11687 | 3 | 4 | 5 | | | V-1 | Mir7222 | | |
| 11593 | 3 | 4 | 5 | | | V-1 | Mir1971 | | | 11688 | 3 | 4 | 5 | | | V-1 | Mir7224 | | |
| 11594 | 3 | 4 | 5 | | | V-1 | Mir1982 | | | 11689 | 3 | 4 | 5 | | | V-1 | Mir7228 | | |
| 11595 | 3 | 4 | 5 | | | V-1 | Mir19b-2 | | | 11690 | 3 | 4 | 5 | | | V-1 | Mir7234 | | |
| 11596 | 3 | 4 | 5 | | | V-1 | Mir201 | | | 11691 | 3 | 4 | 5 | | | V-1 | Mir7238 | | |
| 11597 | 3 | 4 | 5 | | | V-1 | Mir204 | 406987 | 31-May-15 | 11692 | 3 | 4 | 5 | | | V-1 | Mir7243 | | |
| 11598 | 3 | 4 | 5 | | | V-1 | Mir20b | 574032 | 7-Jun-15 | 11693 | 3 | 4 | 5 | | | V-1 | Mir7648 | | |
| 11599 | 3 | 4 | 5 | | | V-1 | Mir2136 | | | 11694 | 3 | 4 | 5 | | | V-1 | Mir7652 | | |
| 11600 | 3 | 4 | 5 | | | V-1 | Mir216a | 406998 | 21-May-15 | 11695 | 3 | 4 | 5 | | | V-1 | Mir7654 | | |
| 11601 | 3 | 4 | 5 | | | V-1 | Mir21b | | | 11696 | 3 | 4 | 5 | | | V-1 | Mir7657 | | |
| 11602 | 3 | 4 | 5 | | | V-1 | Mir22hg | 84981 | 12-May-15 | 11697 | 3 | 4 | 5 | | | V-1 | Mir7659 | | |
| 11603 | 3 | 4 | 5 | | | V-1 | Mir28b | | | 11698 | 3 | 4 | 5 | | | V-1 | Mir7668 | | |
| 11604 | 3 | 4 | 5 | | | V-1 | Mir300 | 100126297 | 4-May-15 | 11699 | 3 | 4 | 5 | | | V-1 | Mir7671 | | |
| 11605 | 3 | 4 | 5 | | | V-1 | Mir3059 | | | 11700 | 3 | 4 | 5 | | | V-1 | Mir7680 | | |
| | | | | | | | | | | 11701 | 3 | 4 | 5 | | | V-1 | Mir7684 | | |
| 11606 | 3 | 4 | 5 | | | V-1 | Mir3064 | 100616387 | 4-May-15 | 11702 | 3 | 4 | 5 | | | V-1 | Mir7b | | |
| 11607 | 3 | 4 | 5 | | | V-1 | Mir3078 | | | 11703 | 3 | 4 | 5 | | | V-1 | Mir8112 | | |
| 11608 | 3 | 4 | 5 | | | V-1 | Mir3083 | | | 11704 | 3 | 4 | 5 | | | V-1 | Mir8115 | | |
| 11609 | 3 | 4 | 5 | | | V-1 | Mir3085 | | | 11705 | 3 | 4 | 5 | | | V-1 | Mir871 | | |
| 11610 | 3 | 4 | 5 | | | V-1 | Mir3088 | | | 11706 | 3 | 4 | 5 | | | V-1 | Mir876 | 100126310 | 21-May-15 |
| 11611 | 3 | 4 | 5 | | | V-1 | Mir3106 | | | 11707 | 3 | 4 | 5 | | | V-1 | Mir878 | | |
| 11612 | 3 | 4 | 5 | | | V-1 | Mir326 | 442900 | 21-May-15 | 11708 | 3 | 4 | 5 | | | V-1 | Mir883b | | |
| 11613 | 3 | 4 | 5 | | | V-1 | Mir33 | 407039 | 21-May-15 | 11709 | 3 | 4 | 5 | | | V-1 | Mira | | |
| 11614 | 3 | 4 | 5 | | | V-1 | Mir340 | 442908 | 21-May-15 | 11710 | 3 | 4 | 5 | | | V-1 | Mirlet7bhg | 400931 | 12-May-15 |
| 11615 | 3 | 4 | 5 | | | V-1 | Mir344h-2 | | | 11711 | 3 | 4 | 5 | | | V-1 | Mirlet7f-2 | | |
| 11616 | 3 | 4 | 5 | | | V-1 | Mir346 | 442911 | 21-May-15 | 11712 | 3 | 4 | 5 | | | V-1 | Mirlet7j | | |
| 11617 | 3 | 4 | 5 | | | V-1 | Mir3475 | | | 11713 | 3 | 4 | 5 | | | V-1 | Mis18a | 54069 | 12-May-15 |
| 11618 | 3 | 4 | 5 | | | V-1 | Mir3544 | | | 11714 | 3 | 4 | 5 | | | V-1 | Mitd1 | 129531 | 12-May-15 |
| 11619 | 3 | 4 | 5 | | | V-1 | Mir362 | 574030 | 21-May-15 | 11715 | 3 | 4 | 5 | | | V-1 | Mkks | 8195 | 23-May-15 |
| 11620 | 3 | 4 | 5 | | | V-1 | Mir375 | 494324 | 31-May-15 | 11716 | 3 | 4 | 5 | | | V-1 | Mkl2 | 57496 | 21-May-15 |
| 11621 | 3 | 4 | 5 | | | V-1 | Mir376b | 574435 | 21-May-15 | 11717 | 3 | 4 | 5 | | | V-1 | Mknk1 | 8569 | 4-May-15 |
| 11622 | 3 | 4 | 5 | | | V-1 | Mir379 | 494328 | 21-May-15 | 11718 | 3 | 4 | 5 | | | V-1 | Mkrn2 | 23609 | 23-May-15 |
| 11623 | 3 | 4 | 5 | | | V-1 | Mir383 | 494332 | 21-May-15 | 11719 | 3 | 4 | 5 | | | V-1 | Mlc1 | 23209 | 31-May-15 |
| 11624 | 3 | 4 | 5 | | | V-1 | Mir3967 | | | 11720 | 3 | 4 | 5 | | | V-1 | Mlf2 | 8079 | 4-May-15 |
| 11625 | 3 | 4 | 5 | | | V-1 | Mir3969 | | | 11721 | 3 | 4 | 5 | | | V-1 | Mlkt1 | 4298 | 21-May-15 |
| 11626 | 3 | 4 | 5 | | | V-1 | Mir411 | 693121 | 21-May-15 | 11722 | 3 | 4 | 5 | | | V-1 | Mlkt3 | 4300 | 12-May-15 |
| 11627 | 3 | 4 | 5 | | | V-1 | Mir448 | 554212 | 4-May-15 | 11723 | 3 | 4 | 5 | | | V-1 | Mlst8 | 64223 | 4-May-15 |
| 11628 | 3 | 4 | 5 | | | V-1 | Mir455 | 619556 | 21-May-15 | 11724 | 3 | 4 | 5 | | | V-1 | Mlycd | 23417 | 4-May-15 |
| 11629 | 3 | 4 | 5 | | | V-1 | Mir466g | | | 11725 | 3 | 4 | 5 | | | V-1 | Mmaa | 166785 | 7-Jun-15 |
| 11630 | 3 | 4 | 5 | | | V-1 | Mir466o | | | 11726 | 3 | 4 | 5 | | | V-1 | Mmel1 | 79258 | 4-May-15 |
| 11631 | 3 | 4 | 5 | | | V-1 | Mir467a-2 | | | 11727 | 3 | 4 | 5 | | | V-1 | Mmp10 | 4319 | 12-May-15 |
| 11632 | 3 | 4 | 5 | | | V-1 | Mir488 | 574441 | 21-May-15 | 11728 | 3 | 4 | 5 | | | V-1 | Mmp13 | 4322 | 24-May-15 |
| 11633 | 3 | 4 | 5 | | | V-1 | Mir494 | 574452 | 7-Jun-15 | 11729 | 3 | 4 | 5 | | | V-1 | Mmp15 | 4324 | 31-May-15 |
| 11634 | 3 | 4 | 5 | | | V-1 | Mir5101 | | | 11730 | 3 | 4 | 5 | | | V-1 | Mmp16 | 4325 | 17-May-15 |
| 11635 | 3 | 4 | 5 | | | V-1 | Mir5108 | | | 11731 | 3 | 4 | 5 | | | V-1 | Mmp1a | | |
| 11636 | 3 | 4 | 5 | | | V-1 | Mir5124b | | | 11732 | 3 | 4 | 5 | | | V-1 | Mmp20 | 9313 | 4-May-15 |
| 11637 | 3 | 4 | 5 | | | V-1 | Mir5130 | | | 11733 | 3 | 4 | 5 | | | V-1 | Mmp27 | 64066 | 4-May-15 |
| 11638 | 3 | 4 | 5 | | | V-1 | Mir532 | 693124 | 21-May-15 | 11734 | 3 | 4 | 5 | | | V-1 | Mmp28 | 79148 | 12-May-15 |
| 11639 | 3 | 4 | 5 | | | V-1 | Mir551b | 693136 | 21-May-15 | 11735 | 3 | 4 | 5 | | | V-1 | Mmrn1 | 22915 | 4-May-15 |
| 11640 | 3 | 4 | 5 | | | V-1 | Mir5616 | | | 11736 | 3 | 4 | 5 | | | V-1 | Mmrn2 | 79812 | 4-May-15 |
| 11641 | 3 | 4 | 5 | | | V-1 | Mir5624 | | | 11737 | 3 | 4 | 5 | | | V-1 | Mn1 | 4330 | 12-May-15 |
| 11642 | 3 | 4 | 5 | | | V-1 | Mir5626 | | | 11738 | 3 | 4 | 5 | | | V-1 | Mnat1 | 4331 | 1-Jun-15 |
| 11643 | 3 | 4 | 5 | | | V-1 | Mir574 | 693159 | 21-May-15 | 11739 | 3 | 4 | 5 | | | V-1 | Mnd1-ps | | |
| 11644 | 3 | 4 | 5 | | | V-1 | Mir6237 | | | 11740 | 3 | 4 | 5 | | | V-1 | Mnt | 4335 | 12-May-15 |
| 11645 | 3 | 4 | 5 | | | V-1 | Mir6335 | | | 11741 | 3 | 4 | 5 | | | V-1 | Mob1a | 55233 | 4-May-15 |
| 11646 | 3 | 4 | 5 | | | V-1 | Mir6343 | | | 11742 | 3 | 4 | 5 | | | V-1 | Mob3b | 79817 | 4-May-15 |
| 11647 | 3 | 4 | 5 | | | V-1 | Mir6348 | | | 11743 | 3 | 4 | 5 | | | V-1 | Mocs1 | 4337 | 12-May-15 |
| 11648 | 3 | 4 | 5 | | | V-1 | Mir6364 | | | 11744 | 3 | 4 | 5 | | | V-1 | Mocs2 | 4338 | 4-May-15 |
| 11649 | 3 | 4 | 5 | | | V-1 | Mir6367 | | | 11745 | 3 | 4 | 5 | | | V-1 | Mogat1 | 116255 | 4-May-15 |
| 11650 | 3 | 4 | 5 | | | V-1 | Mir6370 | | | 11746 | 3 | 4 | 5 | | | V-1 | Mogat2 | 80168 | 4-May-15 |
| 11651 | 3 | 4 | 5 | | | V-1 | Mir6373 | | | 11747 | 3 | 4 | 5 | | | V-1 | Mok | 5891 | 4-May-15 |
| 11652 | 3 | 4 | 5 | | | V-1 | Mir6384 | | | 11748 | 3 | 4 | 5 | | | V-1 | Morn1 | 79906 | 12-May-15 |
| 11653 | 3 | 4 | 5 | | | V-1 | Mir6388 | | | 11749 | 3 | 4 | 5 | | | V-1 | Mospd3 | 64598 | 4-May-15 |
| 11654 | 3 | 4 | 5 | | | V-1 | Mir6398 | | | 11750 | 3 | 4 | 5 | | | V-1 | Moxd2 | 100289017 | 4-May-15 |
| 11655 | 3 | 4 | 5 | | | V-1 | Mir6401 | | | 11751 | 3 | 4 | 5 | | | V-1 | Mpg | 4350 | 12-May-15 |
| 11656 | 3 | 4 | 5 | | | V-1 | Mir6408 | | | 11752 | 3 | 4 | 5 | | | V-1 | Mphosph10 | 10199 | 4-May-15 |
| 11657 | 3 | 4 | 5 | | | V-1 | Mir6414 | | | 11753 | 3 | 4 | 5 | | | V-1 | Mphosph6 | 10200 | 4-May-15 |
| 11658 | 3 | 4 | 5 | | | V-1 | Mir6416 | | | 11754 | 3 | 4 | 5 | | | V-1 | Mpp1 | 4354 | 7-Jun-15 |
| 11659 | 3 | 4 | 5 | | | V-1 | Mir6419 | | | 11755 | 3 | 4 | 5 | | | V-1 | Mpp4 | 58538 | 7-Jun-15 |
| 11660 | 3 | 4 | 5 | | | V-1 | Mir653 | 724023 | 21-May-15 | 11756 | 3 | 4 | 5 | | | V-1 | Mpped1 | 758 | 4-May-15 |
| 11661 | 3 | 4 | 5 | | | V-1 | Mir654 | 724024 | 21-May-15 | 11757 | 3 | 4 | 5 | | | V-1 | Mprip | 23164 | 12-May-15 |
| 11662 | 3 | 4 | 5 | | | V-1 | Mir66 | | | 11758 | 3 | 4 | 5 | | | V-1 | Mptx1 | 649458 | 4-May-15 |
| 11663 | 3 | 4 | 5 | | | V-1 | Mir669g | | | 11759 | 3 | 4 | 5 | | | V-1 | Mpzl3 | 196264 | 4-May-15 |
| 11664 | 3 | 4 | 5 | | | V-1 | Mir669j | | | 11760 | 3 | 4 | 5 | | | V-1 | Mr1 | 3140 | 7-Jun-15 |
| 11665 | 3 | 4 | 5 | | | V-1 | Mir6715 | | | 11761 | 3 | 4 | 5 | | | V-1 | Mras | 22808 | 4-May-15 |
| 11666 | 3 | 4 | 5 | | | V-1 | Mir673 | | | | | | | | | | | | |
| 11667 | 3 | 4 | 5 | | | V-1 | Mir684-1 | | | | | | | | | | | | |

Fig. 30 - 63

| | | | | | | | | | | | | | | | | | |
|---|---|---|---|---|---|---|---|---|---|---|---|---|---|---|---|---|---|
| 11762 | 3 | 4 | 5 | | | V-1 | Mrc1 | 4360 | 12-May-15 | 11858 | 3 | 4 | 5 | | | V-1 | Naif1 | 203245 | 4-May-15 |
| 11763 | 3 | 4 | 5 | | | V-1 | Mre11a | 4361 | 12-May-15 | 11859 | 3 | 4 | 5 | | | V-1 | Naip6 | | |
| 11764 | 3 | 4 | 5 | | | V-1 | Mrfap1 | 93621 | 4-May-15 | 11860 | 3 | 4 | 5 | | | V-1 | Naip7 | | |
| 11765 | 3 | 4 | 5 | | | V-1 | Mrgpra2b | | | 11861 | 3 | 4 | 5 | | | V-1 | Nalcn | 259232 | 17-May-15 |
| 11766 | 3 | 4 | 5 | | | V-1 | Mrgpra3 | | | 11862 | 3 | 4 | 5 | | | V-1 | Nanos2 | 339345 | 4-May-15 |
| 11767 | 3 | 4 | 5 | | | V-1 | Mrgpra9 | | | 11863 | 3 | 4 | 5 | | | V-1 | Nanp | 140838 | 4-May-15 |
| 11768 | 3 | 4 | 5 | | | V-1 | Mrgprf | 116535 | 4-May-15 | 11864 | 3 | 4 | 5 | | | V-1 | Nap1l1 | 4673 | 12-May-15 |
| 11769 | 3 | 4 | 5 | | | V-1 | Mrgprx1 | 259249 | 4-May-15 | 11865 | 3 | 4 | 5 | | | V-1 | Napa | 8775 | 7-Jun-15 |
| 11770 | 3 | 4 | 5 | | | V-1 | Mro | 83876 | 4-May-15 | 11866 | 3 | 4 | 5 | | | V-1 | Napb | 63908 | 7-Jun-15 |
| 11771 | 3 | 4 | 5 | | | V-1 | Mrpl22 | 29093 | 7-Jun-15 | 11867 | 3 | 4 | 5 | | | V-1 | Napepld | 222236 | 12-May-15 |
| 11772 | 3 | 4 | 5 | | | V-1 | Mrpl34 | 64981 | 4-May-15 | 11868 | 3 | 4 | 5 | | | V-1 | Napg | 8774 | 4-May-15 |
| 11773 | 3 | 4 | 5 | | | V-1 | Mrps2 | 51116 | 28-May-15 | 11869 | 3 | 4 | 5 | | | V-1 | Narf | 26502 | n-2015 |
| 11774 | 3 | 4 | 5 | | | V-1 | Mrto4 | 51154 | 4-May-15 | 11870 | 3 | 4 | 5 | | | V-1 | Narfl | 64428 | 12-May-15 |
| 11775 | 3 | 4 | 5 | | | V-1 | Ms4a10 | 341116 | 4-May-15 | 11871 | 3 | 4 | 5 | | | V-1 | Nat1 | 9 | 7-Jun-15 |
| 11776 | 3 | 4 | 5 | | | V-1 | Ms4a5 | 64232 | 4-May-15 | 11872 | 3 | 4 | 5 | | | V-1 | Nat2 | 10 | 16-Jun-15 |
| 11777 | 3 | 4 | 5 | | | V-1 | Msantd1 | 345222 | 4-May-15 | 11873 | 3 | 4 | 5 | | | V-1 | Nat8l | 339983 | 4-May-15 |
| 11778 | 3 | 4 | 5 | | | V-1 | Msc | 9242 | 7-Jun-15 | 11874 | 3 | 4 | 5 | | | V-1 | Nat9 | 26151 | 20-May-15 |
| 11779 | 3 | 4 | 5 | | | V-1 | Msgn1 | 343930 | 28-May-15 | 11875 | 3 | 4 | 5 | | | V-1 | Nav3 | 89795 | 12-May-15 |
| 11780 | 3 | 4 | 5 | | | V-1 | Msh6 | 2956 | 23-May-15 | 11876 | 3 | 4 | 5 | | | V-1 | Nbas | 51594 | 29-May-15 |
| 11781 | 3 | 4 | 5 | | | V-1 | Msi1 | 4440 | 1-Jun-15 | 11877 | 3 | 4 | 5 | | | V-1 | Nbeal1 | 65065 | 4-May-15 |
| 11782 | 3 | 4 | 5 | | | V-1 | Msi2 | 339287 | 7-Jun-15 | 11878 | 3 | 4 | 5 | | | V-1 | Nbn | 4683 | 7-Jun-15 |
| 11783 | 3 | 4 | 5 | | | V-1 | Mslnl | 401827 | 4-May-15 | 11879 | 3 | 4 | 5 | | | V-1 | Ncam2 | 4685 | 7-Jun-15 |
| 11784 | 3 | 4 | 5 | | | V-1 | Msmp | 692094 | 4-May-15 | 11880 | 3 | 4 | 5 | | | V-1 | Ncapd3 | 23310 | 4-May-15 |
| 11785 | 3 | 4 | 5 | | | V-1 | Msra | 4482 | 12-May-15 | 11881 | 3 | 4 | 5 | | | V-1 | Ncaph2 | 29781 | 4-May-15 |
| 11786 | 3 | 4 | 5 | | | V-1 | Msr1 | 4485 | 16-Jun-15 | 11882 | 3 | 4 | 5 | | | V-1 | Ncdn | 23154 | 12-May-15 |
| 11787 | 3 | 4 | 5 | | | V-1 | Msto1 | 55154 | 4-May-15 | 11883 | 3 | 4 | 5 | | | V-1 | Nck1 | 4690 | 1-Jun-15 |
| 11788 | 3 | 4 | 5 | | | V-1 | Msx1os | | | 11884 | 3 | 4 | 5 | | | V-1 | Nckipsd | 51517 | 4-May-15 |
| 11789 | 3 | 4 | 5 | | | V-1 | Mta1 | 9112 | 17-May-15 | 11885 | 3 | 4 | 5 | | | V-1 | Ncl | 4691 | 13-Jun-15 |
| 11790 | 3 | 4 | 5 | | | V-1 | Mta3 | 57504 | 4-May-15 | 11886 | 3 | 4 | 5 | | | V-1 | Ncoa5 | 57727 | 4-May-15 |
| 11791 | 3 | 4 | 5 | | | V-1 | Mtap7d3 | | | 11887 | 3 | 4 | 5 | | | V-1 | Ncor1 | 9611 | 4-May-15 |
| 11792 | 3 | 4 | 5 | | | V-1 | Mtch1 | 23787 | 14-May-15 | 11888 | 3 | 4 | 5 | | | V-1 | Ncs1 | 23413 | 12-May-15 |
| 11793 | 3 | 4 | 5 | | | V-1 | Mtf1 | 4520 | 7-Jun-15 | 11889 | 3 | 4 | 5 | | | V-1 | Ncstn | 23385 | 12-May-15 |
| 11794 | 3 | 4 | 5 | | | V-1 | Mtfmt | 123263 | 4-May-15 | 11890 | 3 | 4 | 5 | | | V-1 | Nctc1 | | |
| 11795 | 3 | 4 | 5 | | | V-1 | Mtfr1l | 56181 | 4-May-15 | 11891 | 3 | 4 | 5 | | | V-1 | Nde1 | 54820 | 4-May-15 |
| 11796 | 3 | 4 | 5 | | | V-1 | Mtg1 | 92170 | 4-May-15 | 11892 | 3 | 4 | 5 | | | V-1 | Ndel1 | 81565 | 2-Jun-15 |
| 11797 | 3 | 4 | 5 | | | V-1 | Mthfd2l | 441024 | 4-May-15 | 11893 | 3 | 4 | 5 | | | V-1 | Ndnf | 79625 | 4-May-15 |
| 11798 | 3 | 4 | 5 | | | V-1 | Mthfs | 10588 | 12-May-15 | 11894 | 3 | 4 | 5 | | | V-1 | Ndrg2 | 57447 | 4-May-15 |
| 11799 | 3 | 4 | 5 | | | V-1 | Mthfsd | 64779 | 4-May-15 | 11895 | 3 | 4 | 5 | | | V-1 | Ndrg3 | 57446 | 4-May-15 |
| 11800 | 3 | 4 | 5 | | | V-1 | Mtmr12 | 54545 | 12-May-15 | 11896 | 3 | 4 | 5 | | | V-1 | Ndst1 | 3340 | 4-May-15 |
| 11801 | 3 | 4 | 5 | | | V-1 | Mtr | 4548 | 23-May-15 | 11897 | 3 | 4 | 5 | | | V-1 | Ndst4 | 64579 | 4-May-15 |
| 11802 | 3 | 4 | 5 | | | V-1 | Mtrf1l | 54516 | 4-May-15 | 11898 | 3 | 4 | 5 | | | V-1 | Ndufa5 | 4698 | 12-May-15 |
| 11803 | 3 | 4 | 5 | | | V-1 | Mtx1 | 4580 | 4-May-15 | 11899 | 3 | 4 | 5 | | | V-1 | Ndufaf6 | 137682 | 23-May-15 |
| 11804 | 3 | 4 | 5 | | | V-1 | Muc19 | 283463 | 12-May-15 | 11900 | 3 | 4 | 5 | | | V-1 | Ndufs6 | 4726 | 4-May-15 |
| 11805 | 3 | 4 | 5 | | | V-1 | Muc4 | 4585 | 12-May-15 | 11901 | 3 | 4 | 5 | | | V-1 | Neb | 4703 | 23-May-15 |
| 11806 | 3 | 4 | 5 | | | V-1 | Muc6 | 4588 | 12-May-15 | 11902 | 3 | 4 | 5 | | | V-1 | Necab1 | 64168 | 4-May-15 |
| 11807 | 3 | 4 | 5 | | | V-1 | Mug1 | | | 11903 | 3 | 4 | 5 | | | V-1 | Nedd1 | 121441 | 4-May-15 |
| 11808 | 3 | 4 | 5 | | | V-1 | Mup21 | | | 11904 | 3 | 4 | 5 | | | V-1 | Nedd8 | 4738 | 4-May-15 |
| 11809 | 3 | 4 | 5 | | | V-1 | Musk | 4593 | 7-Jun-15 | 11905 | 3 | 4 | 5 | | | V-1 | Nefh | 4744 | 23-May-15 |
| 11810 | 3 | 4 | 5 | | | V-1 | Mut | 4594 | 23-May-15 | 11906 | 3 | 4 | 5 | | | V-1 | Neil2 | 252969 | 4-May-15 |
| 11811 | 3 | 4 | 5 | | | V-1 | Mvb12a | 93343 | 4-May-15 | 11907 | 3 | 4 | 5 | | | V-1 | Nek1 | 4750 | 4-May-15 |
| 11812 | 3 | 4 | 5 | | | V-1 | Mvp | 9961 | 7-Jun-15 | 11908 | 3 | 4 | 5 | | | V-1 | Nek3 | 4752 | 4-May-15 |
| 11813 | 3 | 4 | 5 | | | V-1 | Mxd4 | 10608 | 4-May-15 | 11909 | 3 | 4 | 5 | | | V-1 | Nek7 | 140609 | 4-May-15 |
| 11814 | 3 | 4 | 5 | | | V-1 | Mxi1 | 4601 | 4-May-15 | 11910 | 3 | 4 | 5 | | | V-1 | Nelfb | 25920 | 4-May-15 |
| 11815 | 3 | 4 | 5 | | | V-1 | Myadm | 91663 | 21-May-15 | 11911 | 3 | 4 | 5 | | | V-1 | Nell1 | 4745 | 12-May-15 |
| 11816 | 3 | 4 | 5 | | | V-1 | Myadml2 | 255275 | 4-May-15 | 11912 | 3 | 4 | 5 | | | V-1 | Nemf | 9147 | 12-May-15 |
| 11817 | 3 | 4 | 5 | | | V-1 | Mybbp1a | 10514 | 4-May-15 | 11913 | 3 | 4 | 5 | | | V-1 | Nespas | 149775 | 12-May-15 |
| 11818 | 3 | 4 | 5 | | | V-1 | Mycbp | 26292 | 4-May-15 | 11914 | 3 | 4 | 5 | | | V-1 | Neto1 | 81832 | 4-May-15 |
| 11819 | 3 | 4 | 5 | | | V-1 | Mycl | 4610 | 21-May-15 | 11915 | 3 | 4 | 5 | | | V-1 | Neu1 | 4758 | 7-Jun-15 |
| 11820 | 3 | 4 | 5 | | | V-1 | Mycs | | | 11916 | 3 | 4 | 5 | | | V-1 | Neu2 | 4759 | 4-May-15 |
| 11821 | 3 | 4 | 5 | | | V-1 | Myd88 | 4615 | 4-May-15 | 11917 | 3 | 4 | 5 | | | V-1 | Neu4 | 129807 | 4-May-15 |
| 11822 | 3 | 4 | 5 | | | V-1 | Myef2 | 50804 | 4-May-15 | 11918 | 3 | 4 | 5 | | | V-1 | Neurl1b | 54492 | 21-May-15 |
| 11823 | 3 | 4 | 5 | | | V-1 | Myeov2 | 150678 | 4-May-15 | 11919 | 3 | 4 | 5 | | | V-1 | Neurl4 | 84461 | 4-May-15 |
| 11824 | 3 | 4 | 5 | | | V-1 | Myh31 | 4629 | 28-May-15 | 11920 | 3 | 4 | 5 | | | V-1 | Neurog3 | 50674 | 28-May-15 |
| 11825 | 3 | 4 | 5 | | | V-1 | Myh13 | 8735 | 4-May-15 | 11921 | 3 | 4 | 5 | | | V-1 | Nf1 | 4763 | 23-May-15 |
| 11826 | 3 | 4 | 5 | | | V-1 | Myh15 | 22989 | 12-May-15 | 11922 | 3 | 4 | 5 | | | V-1 | Nfasc | 23114 | 4-May-15 |
| 11827 | 3 | 4 | 5 | | | V-1 | Myh3 | 4621 | 12-May-15 | 11923 | 3 | 4 | 5 | | | V-1 | Nfat5 | 10725 | 12-May-15 |
| 11828 | 3 | 4 | 5 | | | V-1 | Myl12a | 10627 | 12-May-15 | 11924 | 3 | 4 | 5 | | | V-1 | Nfe2l1 | 4779 | 4-May-15 |
| 11829 | 3 | 4 | 5 | | | V-1 | Myl6 | 4637 | 4-May-15 | 11925 | 3 | 4 | 5 | | | V-1 | Nfia | 4774 | 2-Jun-15 |
| 11830 | 3 | 4 | 5 | | | V-1 | Myl6b | 140465 | 4-May-15 | 11926 | 3 | 4 | 5 | | | V-1 | Nfib | 4781 | 28-May-15 |
| 11831 | 3 | 4 | 5 | | | V-1 | Myl9 | 10398 | 4-May-15 | 11927 | 3 | 4 | 5 | | | V-1 | Nfix | 4784 | 17-May-15 |
| 11832 | 3 | 4 | 5 | | | V-1 | Mylip | 29116 | 4-May-15 | 11928 | 3 | 4 | 5 | | | V-1 | Nfkbia | 4792 | 31-May-15 |
| 11833 | 3 | 4 | 5 | | | V-1 | Mylk2 | 85366 | 23-May-15 | 11929 | 3 | 4 | 5 | | | V-1 | Nfkbib | 4793 | 31-May-15 |
| 11834 | 3 | 4 | 5 | | | V-1 | Mynn | 55892 | 12-May-15 | 11930 | 3 | 4 | 5 | | | V-1 | Nfkbil1 | 4795 | 12-May-15 |
| 11835 | 3 | 4 | 5 | | | V-1 | Myo19 | 80179 | 12-May-15 | 11931 | 3 | 4 | 5 | | | V-1 | Nfrkb | 4798 | 4-May-15 |
| 11836 | 3 | 4 | 5 | | | V-1 | Myo1c | 4641 | 7-Jun-15 | 11932 | 3 | 4 | 5 | | | V-1 | Nfx1 | 4799 | 4-May-15 |
| 11837 | 3 | 4 | 5 | | | V-1 | Myo1e | 4643 | 12-May-15 | 11933 | 3 | 4 | 5 | | | V-1 | Nfyb | 4801 | 4-May-15 |
| 11838 | 3 | 4 | 5 | | | V-1 | Myo1h | 283446 | 4-May-15 | 11934 | 3 | 4 | 5 | | | V-1 | Ngly1 | 55768 | 12-May-15 |
| 11839 | 3 | 4 | 5 | | | V-1 | Myo5b | 4645 | 4-May-15 | 11935 | 3 | 4 | 5 | | | V-1 | Ngrn | 51335 | 4-May-15 |
| 11840 | 3 | 4 | 5 | | | V-1 | Myo5c | 55930 | 4-May-15 | 11936 | 3 | 4 | 5 | | | V-1 | Nhp2 | 55651 | 31-May-15 |
| 11841 | 3 | 4 | 5 | | | V-1 | Myo7b | 4648 | 4-May-15 | 11937 | 3 | 4 | 5 | | | V-1 | Nhp2l1 | 4809 | 2-Jun-15 |
| 11842 | 3 | 4 | 5 | | | V-1 | Myocd | 93649 | 31-May-15 | 11938 | 3 | 4 | 5 | | | V-1 | Nhsl2 | 340527 | 12-May-15 |
| 11843 | 3 | 4 | 5 | | | V-1 | Myom3 | 127294 | 4-May-15 | 11939 | 3 | 4 | 5 | | | V-1 | Nid2 | 22795 | 12-May-15 |
| 11844 | 3 | 4 | 5 | | | V-1 | Myoz3 | 91977 | 4-May-15 | 11940 | 3 | 4 | 5 | | | V-1 | Nif3l1 | 60491 | 3-May-15 |
| 11845 | 3 | 4 | 5 | | | V-1 | Mypop | 339344 | 4-May-15 | 11941 | 3 | 4 | 5 | | | V-1 | Ninj1 | 4814 | 18-May-15 |
| 11846 | 3 | 4 | 5 | | | V-1 | Myrfl | 196446 | 12-May-15 | 11942 | 3 | 4 | 5 | | | V-1 | Ninj2 | 4815 | 12-May-15 |
| 11847 | 3 | 4 | 5 | | | V-1 | Mysm1 | 114803 | 4-May-15 | 11943 | 3 | 4 | 5 | | | V-1 | Nip7 | 51388 | 4-May-15 |
| 11848 | 3 | 4 | 5 | | | V-1 | Mzf1 | 7593 | 7-Jun-15 | 11944 | 3 | 4 | 5 | | | V-1 | Nipa2 | 81614 | 7-Jun-15 |
| 11849 | 3 | 4 | 5 | | | V-1 | N4bp2l1 | 90634 | 4-May-15 | 11945 | 3 | 4 | 5 | | | V-1 | Nipal3 | 57185 | 4-May-15 |
| 11850 | 3 | 4 | 5 | | | V-1 | N4bp2l2 | 10443 | 4-May-15 | 11946 | 3 | 4 | 5 | | | V-1 | Nkain2 | 154215 | 4-May-15 |
| 11851 | 3 | 4 | 5 | | | V-1 | N6amt1 | 29104 | 4-May-15 | 11947 | 3 | 4 | 5 | | | V-1 | Nkap | 79576 | 4-May-15 |
| 11852 | 3 | 4 | 5 | | | V-1 | Naa30 | 122830 | 4-May-15 | 11948 | 3 | 4 | 5 | | | V-1 | Nkg7 | 4818 | 4-May-15 |
| 11853 | 3 | 4 | 5 | | | V-1 | Naaladl1 | 10004 | 4-May-15 | 11949 | 3 | 4 | 5 | | | V-1 | Nkiras1 | 28512 | 4-May-15 |
| 11854 | 3 | 4 | 5 | | | V-1 | Nabp2 | 79035 | 4-May-15 | 11950 | 3 | 4 | 5 | | | V-1 | Nktr | 4820 | 4-May-15 |
| 11855 | 3 | 4 | 5 | | | V-1 | Nadsyn1 | 55191 | 12-May-15 | 11951 | 3 | 4 | 5 | | | V-1 | Nkx2-2 | 4821 | 17-May-15 |
| 11856 | 3 | 4 | 5 | | | V-1 | Nagk | 55577 | 4-May-15 | 11952 | 3 | 4 | 5 | | | V-1 | Nlgn1 | 22871 | 28-May-15 |
| 11857 | 3 | 4 | 5 | | | V-1 | Nagpa | 51172 | 4-May-15 | 11953 | 3 | 4 | 5 | | | V-1 | Nlgn3 | 54413 | 28-May-15 |

Fig. 30 - 64

| | | | | | | | | | | | | | | | | |
|---|---|---|---|---|---|---|---|---|---|---|---|---|---|---|---|---|
| 11954 | 3 | 4 | 5 | | | V-1 | Nlrp10 | 338322 | 4-May-15 | 12050 | 3 | 4 | 5 | | | V-1 | Nup43 | 348995 | 4-May-15 |
| 11955 | 3 | 4 | 5 | | | V-1 | Nlrp1c-ps | | | 12051 | 3 | 4 | 5 | | | V-1 | Nup50 | 10762 | 4-May-15 |
| 11956 | 3 | 4 | 5 | | | V-1 | Nlrp4a | | | 12052 | 3 | 4 | 5 | | | V-1 | Nup62cl | 54830 | 4-May-15 |
| 11957 | 3 | 4 | 5 | | | V-1 | Nlrp9c | | | 12053 | 3 | 4 | 5 | | | V-1 | Nup85 | 79902 | 4-May-15 |
| 11958 | 3 | 4 | 5 | | | V-1 | Nmbr | 4829 | 4-May-15 | 12054 | 3 | 4 | 5 | | | V-1 | Nup98 | 4928 | 4-May-15 |
| 11959 | 3 | 4 | 5 | | | V-1 | Nmd3 | 51068 | 4-May-15 | 12055 | 3 | 4 | 5 | | | V-1 | Nupl1 | 9818 | 4-May-15 |
| 11960 | 3 | 4 | 5 | | | V-1 | Nme2 | 4831 | 31-May-15 | 12056 | 3 | 4 | 5 | | | V-1 | Nus1 | 116150 | 28-May-15 |
| 11961 | 3 | 4 | 5 | | | V-1 | Nme6 | 10201 | 21-May-15 | 12057 | 3 | 4 | 5 | | | V-1 | Nutf2 | 10204 | 12-May-15 |
| 11962 | 3 | 4 | 5 | | | V-1 | Nme7 | 29922 | 12-May-15 | 12058 | 3 | 4 | 5 | | | V-1 | Nutf2-ps1 | | |
| 11963 | 3 | 4 | 5 | | | V-1 | Nmi | 9111 | 7-Jun-15 | 12059 | 3 | 4 | 5 | | | V-1 | Nutm1 | 256646 | 4-May-15 |
| 11964 | 3 | 4 | 5 | | | V-1 | Nmrk1 | 54981 | 4-May-15 | 12060 | 3 | 4 | 5 | | | V-1 | Nwd2 | 57495 | 4-May-15 |
| 11965 | 3 | 4 | 5 | | | V-1 | Nms | 129521 | 4-May-15 | 12061 | 3 | 4 | 5 | | | V-1 | Nxf7 | | |
| 11966 | 3 | 4 | 5 | | | V-1 | Nmu | 10874 | 12-May-15 | 12062 | 3 | 4 | 5 | | | V-1 | Nxnl2 | 192046 | 4-May-15 |
| 11967 | 3 | 4 | 5 | | | V-1 | Nmur2 | 56923 | 4-May-15 | 12063 | 3 | 4 | 5 | | | V-1 | Nxph1 | 30010 | 4-May-15 |
| 11968 | 3 | 4 | 5 | | | V-1 | Nod2 | 64127 | 31-May-15 | 12064 | 3 | 4 | 5 | | | V-1 | Nxph3 | 11248 | 12-May-15 |
| 11969 | 3 | 4 | 5 | | | V-1 | Nodal | 4838 | 23-May-15 | 12065 | 3 | 4 | 5 | | | V-1 | Nxt1 | 29107 | 4-May-15 |
| 11970 | 3 | 4 | 5 | | | V-1 | Nol10 | 79954 | 4-May-15 | 12066 | 3 | 4 | 5 | | | V-1 | Nxt2 | 55916 | 4-May-15 |
| 11971 | 3 | 4 | 5 | | | V-1 | Nol3 | 8996 | 24-May-15 | 12067 | 3 | 4 | 5 | | | V-1 | Oard1 | 221443 | 4-May-15 |
| 11972 | 3 | 4 | 5 | | | V-1 | Nolc1 | 9221 | 12-May-15 | 12068 | 3 | 4 | 5 | | | V-1 | Oas1c | | |
| 11973 | 3 | 4 | 5 | | | V-1 | Nop2 | 4839 | 12-May-15 | 12069 | 3 | 4 | 5 | | | V-1 | Oas1d | | |
| 11974 | 3 | 4 | 5 | | | V-1 | Nop56 | 10528 | 22-May-15 | 12070 | 3 | 4 | 5 | | | V-1 | Oas1h | | |
| 11975 | 3 | 4 | 5 | | | V-1 | Nop9 | 161424 | 7-Jun-15 | 12071 | 3 | 4 | 5 | | | V-1 | Oat | 4942 | 12-May-15 |
| 11976 | 3 | 4 | 5 | | | V-1 | Nos2 | 4843 | 7-Jun-15 | 12072 | 3 | 4 | 5 | | | V-1 | Oaz1-ps | | |
| 11977 | 3 | 4 | 5 | | | V-1 | Nos3 | 4846 | 7-Jun-15 | 12073 | 3 | 4 | 5 | | | V-1 | Obfc1 | 79991 | 12-May-15 |
| 11978 | 3 | 4 | 5 | | | V-1 | Nosip | 51070 | 4-May-15 | 12074 | 3 | 4 | 5 | | | V-1 | Obox1 | | |
| 11979 | 3 | 4 | 5 | | | V-1 | Notch1 | 4853 | 31-May-15 | 12075 | 3 | 4 | 5 | | | V-1 | Obsl1 | 23363 | 23-May-15 |
| 11980 | 3 | 4 | 5 | | | V-1 | Noto | 344022 | 4-May-15 | 12076 | 3 | 4 | 5 | | | V-1 | Oc90 | 729330 | 4-May-15 |
| 11981 | 3 | 4 | 5 | | | V-1 | Nova1 | 4857 | 4-May-15 | 12077 | 3 | 4 | 5 | | | V-1 | Ociad1 | 54940 | 4-May-15 |
| 11982 | 3 | 4 | 5 | | | V-1 | Noxa1 | 10811 | 26-May-15 | 12078 | 3 | 4 | 5 | | | V-1 | Ocm | 654231 | 4-May-15 |
| 11983 | 3 | 4 | 5 | | | V-1 | Npas1 | 4861 | 28-May-15 | 12079 | 3 | 4 | 5 | | | V-1 | Ocrl | 4952 | 23-May-15 |
| 11984 | 3 | 4 | 5 | | | V-1 | Npas3 | 64067 | 28-May-15 | 12080 | 3 | 4 | 5 | | | V-1 | Odam | 54959 | 4-May-15 |
| 11985 | 3 | 4 | 5 | | | V-1 | Npat | 4863 | 4-May-15 | 12081 | 3 | 4 | 5 | | | V-1 | Odf2 | 4957 | 7-Jun-15 |
| 11986 | 3 | 4 | 5 | | | V-1 | Npc1l1 | 29881 | 17-May-15 | 12082 | 3 | 4 | 5 | | | V-1 | Odf4 | 146852 | 4-May-15 |
| 11987 | 3 | 4 | 5 | | | V-1 | Npcd | | | 12083 | 3 | 4 | 5 | | | V-1 | Ogt | 8473 | 17-May-15 |
| 11988 | 3 | 4 | 5 | | | V-1 | Npepl1 | 79716 | 4-May-15 | 12084 | 3 | 4 | 5 | | | V-1 | Olt1 | 131177 | 4-May-15 |
| 11989 | 3 | 4 | 5 | | | V-1 | Npffr1 | 64106 | 4-May-15 | 12085 | 3 | 4 | 5 | | | V-1 | Olfm2 | 93145 | 12-May-15 |
| 11990 | 3 | 4 | 5 | | | V-1 | Nploc4 | 55666 | 28-May-15 | 12086 | 3 | 4 | 5 | | | V-1 | Olfml1 | 283298 | 4-May-15 |
| 11991 | 3 | 4 | 5 | | | V-1 | Npm1 | 4869 | 17-May-15 | 12087 | 3 | 4 | 5 | | | V-1 | Olfml2b | 25903 | 4-May-15 |
| 11992 | 3 | 4 | 5 | | | V-1 | Npm2 | 10361 | 4-May-15 | 12088 | 3 | 4 | 5 | | | V-1 | Olfr1 | 4991 | 4-May-15 |
| 11993 | 3 | 4 | 5 | | | V-1 | Npm3-ps1 | | | 12089 | 3 | 4 | 5 | | | V-1 | Olfr1339 | | |
| 11994 | 3 | 4 | 5 | | | V-1 | Nppc | 4880 | 21-May-15 | 12090 | 3 | 4 | 5 | | | V-1 | Olfr1344 | | |
| 11995 | 3 | 4 | 5 | | | V-1 | Npr2 | 4882 | 7-Jun-15 | 12091 | 3 | 4 | 5 | | | V-1 | Olfr1373 | | |
| 11996 | 3 | 4 | 5 | | | V-1 | Nprl2 | 10641 | 29-May-15 | 12092 | 3 | 4 | 5 | | | V-1 | Olfr165 | | |
| 11997 | 3 | 4 | 5 | | | V-1 | Nptn | 27020 | 4-May-15 | 12093 | 3 | 4 | 5 | | | V-1 | Olfr420 | | |
| 11998 | 3 | 4 | 5 | | | V-1 | Nptx2 | 4885 | 12-May-15 | 12094 | 3 | 4 | 5 | | | V-1 | Olfr544 | | |
| 11999 | 3 | 4 | 5 | | | V-1 | Npy2r | 4887 | 12-May-15 | 12095 | 3 | 4 | 5 | | | V-1 | Olfr551 | | |
| 12000 | 3 | 4 | 5 | | | V-1 | Nqo2 | 4835 | 28-May-15 | 12096 | 3 | 4 | 5 | | | V-1 | Olfr780 | | |
| 12001 | 3 | 4 | 5 | | | V-1 | Nr1h4 | 9971 | 31-May-15 | 12097 | 3 | 4 | 5 | | | V-1 | Olfr980 | | |
| 12002 | 3 | 4 | 5 | | | V-1 | Nr2c1 | 7181 | 4-May-15 | 12098 | 3 | 4 | 5 | | | V-1 | Olfr992 | | |
| 12003 | 3 | 4 | 5 | | | V-1 | Nr2e1 | 7101 | 4-May-15 | 12099 | 3 | 4 | 5 | | | V-1 | Omg | 4974 | 4-May-15 |
| 12004 | 3 | 4 | 5 | | | V-1 | Nr2f2 | 7026 | 7-Jun-15 | 12100 | 3 | 4 | 5 | | | V-1 | Omt2a | | |
| 12005 | 3 | 4 | 5 | | | V-1 | Nr2f6 | 2063 | 4-May-15 | 12101 | 3 | 4 | 5 | | | V-1 | Oosp3 | | |
| 12006 | 3 | 4 | 5 | | | V-1 | Nr4a2 | 4929 | 31-May-15 | 12102 | 3 | 4 | 5 | | | V-1 | Oplah | 26873 | 4-May-15 |
| 12007 | 3 | 4 | 5 | | | V-1 | Nr5a1 | 2516 | 12-May-15 | 12103 | 3 | 4 | 5 | | | V-1 | Optn | 10133 | 23-May-15 |
| 12008 | 3 | 4 | 5 | | | V-1 | Nrarp | 441478 | 12-May-15 | 12104 | 3 | 4 | 5 | | | V-1 | Orai1 | 84876 | 21-May-15 |
| 12009 | 3 | 4 | 5 | | | V-1 | Nras | 4893 | 24-May-15 | 12105 | 3 | 4 | 5 | | | V-1 | Orai3 | 93129 | 4-May-15 |
| 12010 | 3 | 4 | 5 | | | V-1 | Nrbf2 | 29982 | 4-May-15 | 12106 | 3 | 4 | 5 | | | V-1 | Orc2 | 4999 | 7-Jun-15 |
| 12011 | 3 | 4 | 5 | | | V-1 | Nrcam | 4897 | 4-May-15 | 12107 | 3 | 4 | 5 | | | V-1 | Orc3 | 23595 | 4-May-15 |
| 12012 | 3 | 4 | 5 | | | V-1 | Nrd1 | 4898 | 12-May-15 | 12108 | 3 | 4 | 5 | | | V-1 | Orm3 | | |
| 12013 | 3 | 4 | 5 | | | V-1 | Nrf1 | 4899 | 7-Jun-15 | 12109 | 3 | 4 | 5 | | | V-1 | Ormdl1 | 94101 | 4-May-15 |
| 12014 | 3 | 4 | 5 | | | V-1 | Nrg2 | 9542 | 12-May-15 | 12110 | 3 | 4 | 5 | | | V-1 | Ormdl3 | 94103 | 4-May-15 |
| 12015 | 3 | 4 | 5 | | | V-1 | Nrip1 | 8204 | 3-May-15 | 12111 | 3 | 4 | 5 | | | V-1 | Osbpl11 | 114885 | 4-May-15 |
| 12016 | 3 | 4 | 5 | | | V-1 | Nrk | 203447 | 12-May-15 | 12112 | 3 | 4 | 5 | | | V-1 | Osbpl1a | 114876 | 4-May-15 |
| 12017 | 3 | 4 | 5 | | | V-1 | Nrn1 | 51299 | 4-May-15 | 12113 | 3 | 4 | 5 | | | V-1 | Osbpl8 | 114882 | 12-May-15 |
| 12018 | 3 | 4 | 5 | | | V-1 | Nron | 641373 | 4-May-15 | 12114 | 3 | 4 | 5 | | | V-1 | Oscp1 | 127700 | 4-May-15 |
| 12019 | 3 | 4 | 5 | | | V-1 | Nrsn1 | 140767 | 12-May-15 | 12115 | 3 | 4 | 5 | | | V-1 | Osgin2 | 734 | 4-May-15 |
| 12020 | 3 | 4 | 5 | | | V-1 | Nrxn1 | 9378 | 4-May-15 | 12116 | 3 | 4 | 5 | | | V-1 | Osmr | 9180 | 23-May-15 |
| 12021 | 3 | 4 | 5 | | | V-1 | Nsf | 4905 | 28-May-15 | 12117 | 3 | 4 | 5 | | | V-1 | Osr1 | 130497 | 7-Jun-15 |
| 12022 | 3 | 4 | 5 | | | V-1 | Nsg1 | 27065 | 4-May-15 | 12118 | 3 | 4 | 5 | | | V-1 | Osr2 | 116039 | 4-May-15 |
| 12023 | 3 | 4 | 5 | | | V-1 | Nsmaf | 8439 | 4-May-15 | 12119 | 3 | 4 | 5 | | | V-1 | Ost4 | 100128731 | 4-May-15 |
| 12024 | 3 | 4 | 5 | | | V-1 | Nsun2 | 54888 | 4-May-15 | 12120 | 3 | 4 | 5 | | | V-1 | Ostm1 | 28962 | 4-May-15 |
| 12025 | 3 | 4 | 5 | | | V-1 | Nt5c1a | 84618 | 4-May-15 | 12121 | 3 | 4 | 5 | | | V-1 | Otog | 340990 | 7-Jun-15 |
| 12026 | 3 | 4 | 5 | | | V-1 | Nt5c3b | 115024 | 10-May-15 | 12122 | 3 | 4 | 5 | | | V-1 | Otop2 | 92736 | 4-May-15 |
| 12027 | 3 | 4 | 5 | | | V-1 | Nt5m | 56953 | 4-May-15 | 12123 | 3 | 4 | 5 | | | V-1 | Otub1 | 55611 | 4-May-15 |
| 12028 | 3 | 4 | 5 | | | V-1 | Ntmt1 | 28989 | 4-May-15 | 12124 | 3 | 4 | 5 | | | V-1 | Otud3 | 23252 | 4-May-15 |
| 12029 | 3 | 4 | 5 | | | V-1 | Ntn3 | 4917 | 12-May-15 | 12125 | 3 | 4 | 5 | | | V-1 | Otx1 | 5013 | 30-May-15 |
| 12030 | 3 | 4 | 5 | | | V-1 | Ntn5 | 126147 | 4-May-15 | 12126 | 3 | 4 | 5 | | | V-1 | Ovol1 | 5017 | 4-May-15 |
| 12031 | 3 | 4 | 5 | | | V-1 | Ntrk3 | 4916 | 12-May-15 | 12127 | 3 | 4 | 5 | | | V-1 | Oxct2a | | |
| 12032 | 3 | 4 | 5 | | | V-1 | Ntsr1 | 4923 | 4-May-15 | 12128 | 3 | 4 | 5 | | | V-1 | P2rx4 | 5025 | 12-May-15 |
| 12033 | 3 | 4 | 5 | | | V-1 | Nub1 | 51667 | 4-May-15 | 12129 | 3 | 4 | 5 | | | V-1 | P2ry12 | 64805 | 17-May-15 |
| 12034 | 3 | 4 | 5 | | | V-1 | Nucks1 | 64710 | 4-May-15 | 12130 | 3 | 4 | 5 | | | V-1 | P2ry13 | 53829 | 21-May-15 |
| 12035 | 3 | 4 | 5 | | | V-1 | Nudc | 10726 | 4-May-15 | 12131 | 3 | 4 | 5 | | | V-1 | P2ry14 | 9934 | 4-May-15 |
| 12036 | 3 | 4 | 5 | | | V-1 | Nudcd2 | 134492 | 4-May-15 | 12132 | 3 | 4 | 5 | | | V-1 | P2ry2 | 5029 | 17-May-15 |
| 12037 | 3 | 4 | 5 | | | V-1 | Nudt11 | 55190 | 4-May-15 | 12133 | 3 | 4 | 5 | | | V-1 | P2ry4 | 5030 | 21-May-15 |
| 12038 | 3 | 4 | 5 | | | V-1 | Nudt2 | 318 | 12-May-15 | 12134 | 3 | 4 | 5 | | | V-1 | P4ha1 | 5033 | 12-May-15 |
| 12039 | 3 | 4 | 5 | | | V-1 | Nudt22 | 84304 | 4-May-15 | 12135 | 3 | 4 | 5 | | | V-1 | P4ha2 | 8974 | 4-May-15 |
| 12040 | 3 | 4 | 5 | | | V-1 | Nudt5 | 11164 | 21-May-15 | 12136 | 3 | 4 | 5 | | | V-1 | P4hb | 5034 | 17-May-15 |
| 12041 | 3 | 4 | 5 | | | V-1 | Nudt8 | 254552 | 4-May-15 | 12137 | 3 | 4 | 5 | | | V-1 | P4htm | 54681 | 12-May-15 |
| 12042 | 3 | 4 | 5 | | | V-1 | Nudt9 | 53343 | 4-May-15 | 12138 | 3 | 4 | 5 | | | V-1 | Pabpc1 | 26986 | 12-May-15 |
| 12043 | 3 | 4 | 5 | | | V-1 | Nufip1 | 26747 | 4-May-15 | 12139 | 3 | 4 | 5 | | | V-1 | Pabpc1l | 80336 | 4-May-15 |
| 12044 | 3 | 4 | 5 | | | V-1 | Numa1 | 4926 | 21-May-15 | 12140 | 3 | 4 | 5 | | | V-1 | Pabpc4l | 132430 | 12-May-15 |
| 12045 | 3 | 4 | 5 | | | V-1 | Nup107 | 57122 | 4-May-15 | 12141 | 3 | 4 | 5 | | | V-1 | Pacsin2 | 11252 | 4-May-15 |
| 12046 | 3 | 4 | 5 | | | V-1 | Nup133 | 55746 | 4-May-15 | 12142 | 3 | 4 | 5 | | | V-1 | Padi6 | 353238 | 4-May-15 |
| 12047 | 3 | 4 | 5 | | | V-1 | Nup160 | 23279 | 4-May-15 | 12143 | 3 | 4 | 5 | | | V-1 | Pafah2 | 5051 | 4-May-15 |
| 12048 | 3 | 4 | 5 | | | V-1 | Nup210l | 91181 | 21-May-15 | 12144 | 3 | 4 | 5 | | | V-1 | Pagr1a | | |
| 12049 | 3 | 4 | 5 | | | V-1 | Nup37 | 79023 | 2-Jun-15 | | | | | | | | | | |

Fig. 30 - 65

| | | | | | | | | | | | | | | | | |
|---|---|---|---|---|---|---|---|---|---|---|---|---|---|---|---|---|
| 12145 | 3 | 4 | 5 | | | V-1 | Pak1ip1 | 55003 | 4-May-15 | 12240 | 3 | 4 | 5 | | | V-1 | Pef2 | | |
| 12146 | 3 | 4 | 5 | | | V-1 | Pak6 | 56924 | 4-May-15 | 12241 | 3 | 4 | 5 | | | V-1 | Pex11b | 8799 | 4-May-15 |
| 12147 | 3 | 4 | 5 | | | V-1 | Pak7 | 57144 | 17-May-15 | 12242 | 3 | 4 | 5 | | | V-1 | Pfas | 5198 | 21-May-15 |
| 12148 | 3 | 4 | 5 | | | V-1 | Pald1 | 27143 | 4-May-15 | 12243 | 3 | 4 | 5 | | | V-1 | Pfdn1 | 5201 | 4-May-15 |
| 12149 | 3 | 4 | 5 | | | V-1 | Palld | 23022 | 31-May-15 | 12244 | 3 | 4 | 5 | | | V-1 | Pfkfb4 | 5210 | 12-May-15 |
| 12150 | 3 | 4 | 5 | | | V-1 | Palm2 | 114299 | 4-May-15 | 12245 | 3 | 4 | 5 | | | V-1 | Pfkl | 5211 | 4-May-15 |
| 12151 | 3 | 4 | 5 | | | V-1 | Palmd | 54873 | 4-May-15 | 12246 | 3 | 4 | 5 | | | V-1 | Pfn1 | 5216 | 7-Jun-15 |
| 12152 | 3 | 4 | 5 | | | V-1 | Pam16 | 51025 | 28-May-15 | 12247 | 3 | 4 | 5 | | | V-1 | Pfn3 | 345456 | 4-May-15 |
| 12153 | 3 | 4 | 5 | | | V-1 | Pan2 | 9324 | 7-Jun-15 | 12248 | 3 | 4 | 5 | | | V-1 | Pfpl | | |
| 12154 | 3 | 4 | 5 | | | V-1 | Pank2 | 80025 | 28-May-15 | 12249 | 3 | 4 | 5 | | | V-1 | Pgam1 | 5223 | 7-Jun-15 |
| 12155 | 3 | 4 | 5 | | | V-1 | Panx2 | 56666 | 4-May-15 | 12250 | 3 | 4 | 5 | | | V-1 | Pgam5 | 192111 | 24-May-15 |
| 12156 | 3 | 4 | 5 | | | V-1 | Panx3 | 116337 | 4-May-15 | 12251 | 3 | 4 | 5 | | | V-1 | Pgap3 | 93210 | 12-May-15 |
| 12157 | 3 | 4 | 5 | | | V-1 | Papd4 | 167153 | 4-May-15 | 12252 | 3 | 4 | 5 | | | V-1 | Pgbd1 | 84547 | 4-May-15 |
| 12158 | 3 | 4 | 5 | | | V-1 | Paqr3 | 152559 | 4-May-15 | 12253 | 3 | 4 | 5 | | | V-1 | Pgd | 5226 | 7-Jun-15 |
| 12159 | 3 | 4 | 5 | | | V-1 | Paqr4 | 124222 | 4-May-15 | 12254 | 3 | 4 | 5 | | | V-1 | Pggt1b | 5229 | 4-May-15 |
| 12160 | 3 | 4 | 5 | | | V-1 | Paqr7 | 164091 | 4-May-15 | 12255 | 3 | 4 | 5 | | | V-1 | Pglyrp2 | 114770 | 4-May-15 |
| 12161 | 3 | 4 | 5 | | | V-1 | Pard3 | 56288 | 4-May-15 | 12256 | 3 | 4 | 5 | | | V-1 | Pgm2 | 55276 | 4-May-15 |
| 12162 | 3 | 4 | 5 | | | V-1 | Pard6g | 84552 | 12-May-15 | 12257 | 3 | 4 | 5 | | | V-1 | Pgp | 283871 | 7-Jun-15 |
| 12163 | 3 | 4 | 5 | | | V-1 | Parp10 | 84875 | 4-May-15 | 12258 | 3 | 4 | 5 | | | V-1 | Pgpep1 | 54858 | 12-May-15 |
| 12164 | 3 | 4 | 5 | | | V-1 | Parp14 | 54625 | 4-May-15 | 12259 | 3 | 4 | 5 | | | V-1 | Pgr | 5241 | 24-May-15 |
| 12165 | 3 | 4 | 5 | | | V-1 | Parp2 | 10038 | 17-May-15 | 12260 | 3 | 4 | 5 | | | V-1 | Pgrmc2 | 10424 | 4-May-15 |
| 12166 | 3 | 4 | 5 | | | V-1 | Parp9 | 83666 | 4-May-15 | 12261 | 3 | 4 | 5 | | | V-1 | Phactr1 | 221692 | 4-May-15 |
| 12167 | 3 | 4 | 5 | | | V-1 | Pars2 | 25973 | 4-May-15 | 12262 | 3 | 4 | 5 | | | V-1 | Phactr2 | 9749 | 4-May-15 |
| 12168 | 3 | 4 | 5 | | | V-1 | Parvb | 29780 | 4-May-15 | 12263 | 3 | 4 | 5 | | | V-1 | Phax | 51808 | 4-May-15 |
| 12169 | 3 | 4 | 5 | | | V-1 | Paupar | 103157000 | 4-May-15 | 12264 | 3 | 4 | 5 | | | V-1 | Phf11d | | |
| 12170 | 3 | 4 | 5 | | | V-1 | Pax1 | 5075 | 4-May-15 | 12265 | 3 | 4 | 5 | | | V-1 | Phf12 | 57649 | 12-May-15 |
| 12171 | 3 | 4 | 5 | | | V-1 | Pax3 | 5077 | 23-May-15 | 12266 | 3 | 4 | 5 | | | V-1 | Phf2 | 5253 | 7-Jun-15 |
| 12172 | 3 | 4 | 5 | | | V-1 | Pax6 | 5080 | 23-May-15 | 12267 | 3 | 4 | 5 | | | V-1 | Phf7 | 51533 | 4-May-15 |
| 12173 | 3 | 4 | 5 | | | V-1 | Pax9 | 5083 | 28-May-15 | 12268 | 3 | 4 | 5 | | | V-1 | Phf8 | 23133 | 4-May-15 |
| 12174 | 3 | 4 | 5 | | | V-1 | Pbdc1 | 51260 | 12-May-15 | 12269 | 3 | 4 | 5 | | | V-1 | Phka1 | 5255 | 4-May-15 |
| 12175 | 3 | 4 | 5 | | | V-1 | Pbld1 | | | 12270 | 3 | 4 | 5 | | | V-1 | Phka2 | 5256 | 23-May-15 |
| 12176 | 3 | 4 | 5 | | | V-1 | Pbp2 | | | 12271 | 3 | 4 | 5 | | | V-1 | Phkg2 | 5261 | 4-May-15 |
| 12177 | 3 | 4 | 5 | | | V-1 | Pbxip1 | 57326 | 4-May-15 | 12272 | 3 | 4 | 5 | | | V-1 | Phlda2 | 7262 | 4-May-15 |
| 12178 | 3 | 4 | 5 | | | V-1 | Pcbp4 | 57060 | 4-May-15 | 12273 | 3 | 4 | 5 | | | V-1 | Phldb1 | 23187 | 29-May-15 |
| 12179 | 3 | 4 | 5 | | | V-1 | Pcdh15 | 65217 | 23-May-15 | 12274 | 3 | 4 | 5 | | | V-1 | Phldb3 | 653583 | 4-May-15 |
| 12180 | 3 | 4 | 5 | | | V-1 | Pcdh19 | 57526 | 7-Jun-15 | 12275 | 3 | 4 | 5 | | | V-1 | Phlpp2 | 23035 | 4-May-15 |
| 12181 | 3 | 4 | 5 | | | V-1 | Pcdhb10 | 56126 | 12-May-15 | 12276 | 3 | 4 | 5 | | | V-1 | Phospho2 | 493911 | 4-May-15 |
| 12182 | 3 | 4 | 5 | | | V-1 | Pcdhb3 | 56132 | 4-May-15 | 12277 | 3 | 4 | 5 | | | V-1 | Phf1os | | |
| 12183 | 3 | 4 | 5 | | | V-1 | Pcdhgb5 | 56101 | 4-May-15 | 12278 | 3 | 4 | 5 | | | V-1 | Phxr4 | | |
| 12184 | 3 | 4 | 5 | | | V-1 | Pcdhgb7 | 56099 | 4-May-15 | 12279 | 3 | 4 | 5 | | | V-1 | Phyhd1 | 254295 | 4-May-15 |
| 12185 | 3 | 4 | 5 | | | V-1 | Pcdhgc4 | 56098 | 12-May-15 | 12280 | 3 | 4 | 5 | | | V-1 | Phyhipl | 84457 | 4-May-15 |
| 12186 | 3 | 4 | 5 | | | V-1 | Pced1a | 64773 | 4-May-15 | 12281 | 3 | 4 | 5 | | | V-1 | Pi4k2a | 55361 | 28-May-15 |
| 12187 | 3 | 4 | 5 | | | V-1 | Pcf11 | 51585 | 4-May-15 | 12282 | 3 | 4 | 5 | | | V-1 | Pi4ka | 5297 | 4-May-15 |
| 12188 | 3 | 4 | 5 | | | V-1 | Pcgf1 | 84759 | 4-May-15 | 12283 | 3 | 4 | 5 | | | V-1 | Pias1 | 8554 | 4-May-15 |
| 12189 | 3 | 4 | 5 | | | V-1 | Pcgf3 | 10336 | 2-Jun-15 | 12284 | 3 | 4 | 5 | | | V-1 | Pick1 | 9463 | 4-May-15 |
| 12190 | 3 | 4 | 5 | | | V-1 | Pcgf6 | 84108 | 4-May-15 | 12285 | 3 | 4 | 5 | | | V-1 | Piezo1 | 9780 | 10-May-15 |
| 12191 | 3 | 4 | 5 | | | V-1 | Pck2 | 5106 | 12-May-15 | 12286 | 3 | 4 | 5 | | | V-1 | Piga | 5277 | 12-May-15 |
| 12192 | 3 | 4 | 5 | | | V-1 | Pclo | 27445 | 4-May-15 | 12287 | 3 | 4 | 5 | | | V-1 | Pigb | 9488 | 23-May-15 |
| 12193 | 3 | 4 | 5 | | | V-1 | Pcnp | 57092 | 4-May-15 | 12288 | 3 | 4 | 5 | | | V-1 | Pigg | 54872 | 4-May-15 |
| 12194 | 3 | 4 | 5 | | | V-1 | Pcp2 | 126006 | 7-Jun-15 | 12289 | 3 | 4 | 5 | | | V-1 | Pigo | 84720 | 4-May-15 |
| 12195 | 3 | 4 | 5 | | | V-1 | Pcsk1 | 5122 | 4-May-15 | 12290 | 3 | 4 | 5 | | | V-1 | Pigs | 94005 | 4-May-15 |
| 12196 | 3 | 4 | 5 | | | V-1 | Pcsk2 | 5126 | 12-May-15 | 12291 | 3 | 4 | 5 | | | V-1 | Pigw | 284098 | 4-May-15 |
| 12197 | 3 | 4 | 5 | | | V-1 | Pcsk6 | 5046 | 4-May-15 | 12292 | 3 | 4 | 5 | | | V-1 | Pigx | 54965 | 4-May-15 |
| 12198 | 3 | 4 | 5 | | | V-1 | Pcsk7 | 9159 | 4-May-15 | 12293 | 3 | 4 | 5 | | | V-1 | Pih1d1 | 55011 | 4-May-15 |
| 12199 | 3 | 4 | 5 | | | V-1 | Pcx | | | 12294 | 3 | 4 | 5 | | | V-1 | Pik3c2a | 5286 | 24-May-15 |
| 12200 | 3 | 4 | 5 | | | V-1 | Pcyox1 | 51449 | 4-May-15 | 12295 | 3 | 4 | 5 | | | V-1 | Pik3r1 | 5295 | 28-May-15 |
| 12201 | 3 | 4 | 5 | | | V-1 | Pcyt1a | 5130 | 4-May-15 | 12296 | 3 | 4 | 5 | | | V-1 | Pik3r2 | 5296 | 28-May-15 |
| 12202 | 3 | 4 | 5 | | | V-1 | Pcyt2 | 5833 | 21-May-15 | 12297 | 3 | 4 | 5 | | | V-1 | Pik3r4 | 30849 | 3-May-15 |
| 12203 | 3 | 4 | 5 | | | V-1 | Pdcd10 | 11235 | 23-May-15 | 12298 | 3 | 4 | 5 | | | V-1 | Pik3r6 | 146850 | 4-May-15 |
| 12204 | 3 | 4 | 5 | | | V-1 | Pdcd5 | 9141 | 4-May-15 | 12299 | 3 | 4 | 5 | | | V-1 | Pikfyve | 200576 | 12-May-15 |
| 12205 | 3 | 4 | 5 | | | V-1 | Pde10a | 10846 | 4-May-15 | 12300 | 3 | 4 | 5 | | | V-1 | Pilrb1 | | |
| 12206 | 3 | 4 | 5 | | | V-1 | Pde12 | 201626 | 12-May-15 | 12301 | 3 | 4 | 5 | | | V-1 | Pim2 | 11040 | 4-May-15 |
| 12207 | 3 | 4 | 5 | | | V-1 | Pde1c | 5137 | 4-May-15 | 12302 | 3 | 4 | 5 | | | V-1 | Pim3 | 415116 | 4-May-15 |
| 12208 | 3 | 4 | 5 | | | V-1 | Pde3a | 5139 | 31-May-15 | 12303 | 3 | 4 | 5 | | | V-1 | Pin1 | 5300 | 7-Jun-15 |
| 12209 | 3 | 4 | 5 | | | V-1 | Pde4d | 5144 | 2-Jun-15 | 12304 | 3 | 4 | 5 | | | V-1 | Pip | 5304 | 7-Jun-15 |
| 12210 | 3 | 4 | 5 | | | V-1 | Pde4dip | 9659 | 12-May-15 | 12305 | 3 | 4 | 5 | | | V-1 | Pip4k2b | 8396 | 4-May-15 |
| 12211 | 3 | 4 | 5 | | | V-1 | Pde6a | 5145 | 23-May-15 | 12306 | 3 | 4 | 5 | | | V-1 | Pip5k1a | 8394 | 4-May-15 |
| 12212 | 3 | 4 | 5 | | | V-1 | Pde8a | 5151 | 4-May-15 | 12307 | 3 | 4 | 5 | | | V-1 | Pip5k1c | 23396 | 4-May-15 |
| 12213 | 3 | 4 | 5 | | | V-1 | Pdf | 64146 | 24-May-15 | 12308 | 3 | 4 | 5 | | | V-1 | Pisd | 23761 | 7-Jun-15 |
| 12214 | 3 | 4 | 5 | | | V-1 | Pdgfd | 80310 | 4-May-15 | 12309 | 3 | 4 | 5 | | | V-1 | Pisd-ps2 | | |
| 12215 | 3 | 4 | 5 | | | V-1 | Pdgfrb | 5159 | 23-May-15 | 12310 | 3 | 4 | 5 | | | V-1 | Pithd1 | 57095 | 4-May-15 |
| 12216 | 3 | 4 | 5 | | | V-1 | Pdha1 | 5160 | 21-May-15 | 12311 | 3 | 4 | 5 | | | V-1 | Pitpna | 5306 | 21-May-15 |
| 12217 | 3 | 4 | 5 | | | V-1 | Pdia6 | 10130 | 4-May-15 | 12312 | 3 | 4 | 5 | | | V-1 | Pitpnm2 | 57605 | 12-May-15 |
| 12218 | 3 | 4 | 5 | | | V-1 | Pdik1l | 149420 | 4-May-15 | 12313 | 3 | 4 | 5 | | | V-1 | Pitx1 | 5307 | 28-May-15 |
| 12219 | 3 | 4 | 5 | | | V-1 | Pdk2 | 5164 | 4-May-15 | 12314 | 3 | 4 | 5 | | | V-1 | Piwi1 | 9271 | 4-May-15 |
| 12220 | 3 | 4 | 5 | | | V-1 | Pdlim1 | 9124 | 21-May-15 | 12315 | 3 | 4 | 5 | | | V-1 | Pja2 | 9867 | 4-May-15 |
| 12221 | 3 | 4 | 5 | | | V-1 | Pdlim3 | 27295 | 4-May-15 | 12316 | 3 | 4 | 5 | | | V-1 | Pkd1l2 | 114780 | 12-May-15 |
| 12222 | 3 | 4 | 5 | | | V-1 | Pdlim4 | 8572 | 4-May-15 | 12317 | 3 | 4 | 5 | | | V-1 | Pkd2l1 | 9033 | 12-May-15 |
| 12223 | 3 | 4 | 5 | | | V-1 | Pdlim5 | 10611 | 12-May-15 | 12318 | 3 | 4 | 5 | | | V-1 | Pkia | 5569 | 4-May-15 |
| 12224 | 3 | 4 | 5 | | | V-1 | Pdp1 | 54704 | 7-Jun-15 | 12319 | 3 | 4 | 5 | | | V-1 | Pkib | 5570 | 4-May-15 |
| 12225 | 3 | 4 | 5 | | | V-1 | Pdpr | 55066 | 4-May-15 | 12320 | 3 | 4 | 5 | | | V-1 | Pkig | 11142 | 4-May-15 |
| 12226 | 3 | 4 | 5 | | | V-1 | Pdrg1 | 81572 | 12-May-15 | 12321 | 3 | 4 | 5 | | | V-1 | Pkn1 | 5585 | 4-May-15 |
| 12227 | 3 | 4 | 5 | | | V-1 | Pdss1 | 23590 | 4-May-15 | 12322 | 3 | 4 | 5 | | | V-1 | Pkp1 | 5317 | 4-May-15 |
| 12228 | 3 | 4 | 5 | | | V-1 | Pdss2 | 57107 | 31-May-15 | 12323 | 3 | 4 | 5 | | | V-1 | Pla1a | 51365 | 12-May-15 |
| 12229 | 3 | 4 | 5 | | | V-1 | Pdxk | 8566 | 4-May-15 | 12324 | 3 | 4 | 5 | | | V-1 | Pla2g10 | 8399 | 12-May-15 |
| 12230 | 3 | 4 | 5 | | | V-1 | Pdyn | 5173 | 23-May-15 | 12325 | 3 | 4 | 5 | | | V-1 | Pla2g12a | 81579 | 4-May-15 |
| 12231 | 3 | 4 | 5 | | | V-1 | Pdzd9 | 255762 | 4-May-15 | 12326 | 3 | 4 | 5 | | | V-1 | Pla2g12b | 84647 | 4-May-15 |
| 12232 | 3 | 4 | 5 | | | V-1 | Pdzrn3 | 23024 | 12-May-15 | 12327 | 3 | 4 | 5 | | | V-1 | Pla2g16 | 11145 | 4-May-15 |
| 12233 | 3 | 4 | 5 | | | V-1 | Pdzrn4 | 29951 | 4-May-15 | 12328 | 3 | 4 | 5 | | | V-1 | Pla2g2d | 26279 | 4-May-15 |
| 12234 | 3 | 4 | 5 | | | V-1 | Pebp4 | 157310 | 4-May-15 | 12329 | 3 | 4 | 5 | | | V-1 | Pla2g4a | 5321 | 12-May-15 |
| 12235 | 3 | 4 | 5 | | | V-1 | Peg12 | | | 12330 | 3 | 4 | 5 | | | V-1 | Pla2g4b | 100137049 | 4-May-15 |
| 12236 | 3 | 4 | 5 | | | V-1 | Pell1 | 57162 | 12-May-15 | 12331 | 3 | 4 | 5 | | | V-1 | Pla2g4d | 283748 | 4-May-15 |
| 12237 | 3 | 4 | 5 | | | V-1 | Pelp1 | 27043 | 12-May-15 | 12332 | 3 | 4 | 5 | | | V-1 | Pla2g6 | 8398 | 4-May-15 |
| 12238 | 3 | 4 | 5 | | | V-1 | Peo1 | 56652 | 23-May-15 | 12333 | 3 | 4 | 5 | | | V-1 | Pla2r1 | 22925 | 24-May-15 |
| 12239 | 3 | 4 | 5 | | | V-1 | Pes1 | 23481 | 7-Jun-15 | 12334 | 3 | 4 | 5 | | | V-1 | Plaa | 9373 | 4-May-15 |

Fig. 30 - 66

| | | | | | | | | | | | | | | | |
|---|---|---|---|---|---|---|---|---|---|---|---|---|---|---|---|
| 12335 | 3 | 4 | 5 | | | V-1 | Plac8l1 | 153770 | 4-May-15 | 12431 | 3 | 4 | 5 | | | V-1 | Ppm1a | 5494 | 4-May-15 |
| 12336 | 3 | 4 | 5 | | | V-1 | Plag1 | 5324 | 28-May-15 | 12432 | 3 | 4 | 5 | | | V-1 | Ppm1f | 9647 | 4-May-15 |
| 12337 | 3 | 4 | 5 | | | V-1 | Plagl2 | 5326 | 31-May-15 | 12433 | 3 | 4 | 5 | | | V-1 | Ppm1k | 152926 | 4-May-15 |
| 12338 | 3 | 4 | 5 | | | V-1 | Plar | 5327 | 29-May-15 | 12434 | 3 | 4 | 5 | | | V-1 | Ppp1ca | 5499 | 12-May-15 |
| 12339 | 3 | 4 | 5 | | | V-1 | Plau | 5328 | 24-May-15 | 12435 | 3 | 4 | 5 | | | V-1 | Ppp1cc | 5501 | 21-May-15 |
| 12340 | 3 | 4 | 5 | | | V-1 | Plb1 | 151056 | 4-May-15 | 12436 | 3 | 4 | 5 | | | V-1 | Ppp1r11 | 6992 | 12-May-15 |
| 12341 | 3 | 4 | 5 | | | V-1 | Plbd2 | 196463 | 12-May-15 | 12437 | 3 | 4 | 5 | | | V-1 | Ppp1r12c | 54776 | 4-May-15 |
| 12342 | 3 | 4 | 5 | | | V-1 | Plcb2 | 5330 | 4-May-15 | 12438 | 3 | 4 | 5 | | | V-1 | Ppp1r14b | 26472 | 12-May-15 |
| 12343 | 3 | 4 | 5 | | | V-1 | Plcb3 | 5331 | 4-May-15 | 12439 | 3 | 4 | 5 | | | V-1 | Ppp1r14c | 81706 | 4-May-15 |
| 12344 | 3 | 4 | 5 | | | V-1 | Plch1 | 23007 | 4-May-15 | 12440 | 3 | 4 | 5 | | | V-1 | Ppp1r15b | 84919 | 4-May-15 |
| 12345 | 3 | 4 | 5 | | | V-1 | Plcxd1 | 55344 | 4-May-15 | 12441 | 3 | 4 | 5 | | | V-1 | Ppp1r16a | 84988 | 4-May-15 |
| 12346 | 3 | 4 | 5 | | | V-1 | Plcxd3 | 345557 | 4-May-15 | 12442 | 3 | 4 | 5 | | | V-1 | Ppp1r17 | 10842 | 4-May-15 |
| 12347 | 3 | 4 | 5 | | | V-1 | Pld2 | 5338 | 31-May-15 | 12443 | 3 | 4 | 5 | | | V-1 | Ppp1r1a | 5502 | 4-May-15 |
| 12348 | 3 | 4 | 5 | | | V-1 | Pld5 | 200150 | 4-May-15 | 12444 | 3 | 4 | 5 | | | V-1 | Ppp1r1c | 151242 | 12-May-15 |
| 12349 | 3 | 4 | 5 | | | V-1 | Plekha1 | 59338 | 17-May-15 | 12445 | 3 | 4 | 5 | | | V-1 | Ppp1r2-ps3 | | |
| 12350 | 3 | 4 | 5 | | | V-1 | Plekha5 | 54477 | 12-May-15 | 12446 | 3 | 4 | 5 | | | V-1 | Ppp1r3d | 5509 | 4-May-15 |
| 12351 | 3 | 4 | 5 | | | V-1 | Plekhb2 | 55041 | 12-May-15 | 12447 | 3 | 4 | 5 | | | V-1 | Ppp2r3a | 5523 | 4-May-15 |
| 12352 | 3 | 4 | 5 | | | V-1 | Plekhd1os | | | 12448 | 3 | 4 | 5 | | | V-1 | Ppp2r5a | 5525 | 4-May-15 |
| 12353 | 3 | 4 | 5 | | | V-1 | Plekhf2 | 79666 | 4-May-15 | 12449 | 3 | 4 | 5 | | | V-1 | Ppp2r5c | 5527 | 4-May-15 |
| 12354 | 3 | 4 | 5 | | | V-1 | Plekhg1 | 57480 | 4-May-15 | 12450 | 3 | 4 | 5 | | | V-1 | Ppp3r1 | 5534 | 4-May-15 |
| 12355 | 3 | 4 | 5 | | | V-1 | Plekhg2 | 64857 | 4-May-15 | 12451 | 3 | 4 | 5 | | | V-1 | Ppp4c | 5531 | 1-Jun-15 |
| 12356 | 3 | 4 | 5 | | | V-1 | Plekhg5 | 57449 | 4-May-15 | 12452 | 3 | 4 | 5 | | | V-1 | Ppt1 | 5538 | 23-May-15 |
| 12357 | 3 | 4 | 5 | | | V-1 | Plekhh3 | 79990 | 4-May-15 | 12453 | 3 | 4 | 5 | | | V-1 | Pqbp1 | 10084 | 4-May-15 |
| 12358 | 3 | 4 | 5 | | | V-1 | Plekho1 | 51177 | 12-May-15 | 12454 | 3 | 4 | 5 | | | V-1 | Pqlc3 | 130814 | 4-May-15 |
| 12359 | 3 | 4 | 5 | | | V-1 | Plekho2 | 80301 | 12-May-15 | 12455 | 3 | 4 | 5 | | | V-1 | Pradc1 | 84279 | 4-May-15 |
| 12360 | 3 | 4 | 5 | | | V-1 | Plekhs1 | 79949 | 30-Apr-15 | 12456 | 3 | 4 | 5 | | | V-1 | Prame | 23532 | 12-May-15 |
| 12361 | 3 | 4 | 5 | | | V-1 | Plin2 | 123 | 4-May-15 | 12457 | 3 | 4 | 5 | | | V-1 | Prb1 | 5542 | 7-Jun-15 |
| 12362 | 3 | 4 | 5 | | | V-1 | Plin3 | 10226 | 4-May-15 | 12458 | 3 | 4 | 5 | | | V-1 | Prcc | 5546 | 4-May-15 |
| 12363 | 3 | 4 | 5 | | | V-1 | Plk5 | 126520 | 4-May-15 | 12459 | 3 | 4 | 5 | | | V-1 | Prdm1 | 639 | 24-May-15 |
| 12364 | 3 | 4 | 5 | | | V-1 | Plod1 | 5351 | 23-May-15 | 12460 | 3 | 4 | 5 | | | V-1 | Prdm10 | 56980 | 4-May-15 |
| 12365 | 3 | 4 | 5 | | | V-1 | Plod3 | 8985 | 4-May-15 | 12461 | 3 | 4 | 5 | | | V-1 | Prdm6 | 93166 | 12-May-15 |
| 12366 | 3 | 4 | 5 | | | V-1 | Plrg1 | 5356 | 4-May-15 | 12462 | 3 | 4 | 5 | | | V-1 | Prdx1 | 5052 | 4-May-15 |
| 12367 | 3 | 4 | 5 | | | V-1 | Plscr1 | 5359 | 28-May-15 | 12463 | 3 | 4 | 5 | | | V-1 | Prdx3 | 10935 | 4-May-15 |
| 12368 | 3 | 4 | 5 | | | V-1 | Plscr5 | 389158 | 12-May-15 | 12464 | 3 | 4 | 5 | | | V-1 | Prdx4 | 10549 | 4-May-15 |
| 12369 | 3 | 4 | 5 | | | V-1 | Plxdc1 | 57125 | 4-May-15 | 12465 | 3 | 4 | 5 | | | V-1 | Prdx5 | 25824 | 4-May-15 |
| 12370 | 3 | 4 | 5 | | | V-1 | Plxna1 | 5361 | 4-May-15 | 12466 | 3 | 4 | 5 | | | V-1 | Prep | 5550 | 7-Jun-15 |
| 12371 | 3 | 4 | 5 | | | V-1 | Plxna3 | 55558 | 12-May-15 | 12467 | 3 | 4 | 5 | | | V-1 | Prex2 | 80243 | 4-May-15 |
| 12372 | 3 | 4 | 5 | | | V-1 | Plxna4 | 91584 | 4-May-15 | 12468 | 3 | 4 | 5 | | | V-1 | Prh1 | 5554 | 31-May-15 |
| 12373 | 3 | 4 | 5 | | | V-1 | Plxnb3 | 5365 | 4-May-15 | 12469 | 3 | 4 | 5 | | | V-1 | Prickle4 | 29964 | 4-May-15 |
| 12374 | 3 | 4 | 5 | | | V-1 | Plxnd1 | 23129 | 4-May-15 | 12470 | 3 | 4 | 5 | | | V-1 | Prima1 | 145270 | 4-May-15 |
| 12375 | 3 | 4 | 5 | | | V-1 | Pm20d2 | 135293 | 4-May-15 | 12471 | 3 | 4 | 5 | | | V-1 | Prkaa1 | 5562 | 31-May-15 |
| 12376 | 3 | 4 | 5 | | | V-1 | Pmel | 6490 | 12-May-15 | 12472 | 3 | 4 | 5 | | | V-1 | Prkaca | 5566 | 7-Jun-15 |
| 12377 | 3 | 4 | 5 | | | V-1 | Pmfbp1 | 83449 | 4-May-15 | 12473 | 3 | 4 | 5 | | | V-1 | Prkca | 5578 | 31-May-15 |
| 12378 | 3 | 4 | 5 | | | V-1 | Pmm1 | 5372 | 4-May-15 | 12474 | 3 | 4 | 5 | | | V-1 | Prkcdbp | 112464 | 4-May-15 |
| 12379 | 3 | 4 | 5 | | | V-1 | Pmpca | 23203 | 4-May-15 | 12475 | 3 | 4 | 5 | | | V-1 | Prkce | 5581 | 16-May-15 |
| 12380 | 3 | 4 | 5 | | | V-1 | Pmpcb | 9512 | 4-May-15 | 12476 | 3 | 4 | 5 | | | V-1 | Prkcg | 5582 | 23-May-15 |
| 12381 | 3 | 4 | 5 | | | V-1 | Pnck | 139728 | 4-May-15 | 12477 | 3 | 4 | 5 | | | V-1 | Prkci | 5584 | 17-May-15 |
| 12382 | 3 | 4 | 5 | | | V-1 | Pnma1 | 9240 | 17-May-15 | 12478 | 3 | 4 | 5 | | | V-1 | Prkcq | 5588 | 3-May-15 |
| 12383 | 3 | 4 | 5 | | | V-1 | Pnn | 5411 | 4-May-15 | 12479 | 3 | 4 | 5 | | | V-1 | Prkd1 | 5587 | 4-May-15 |
| 12384 | 3 | 4 | 5 | | | V-1 | Pnoc | 5368 | 12-May-15 | 12480 | 3 | 4 | 5 | | | V-1 | Prkd3 | 23683 | 17-May-15 |
| 12385 | 3 | 4 | 5 | | | V-1 | Pnpla1 | 285848 | 7-Jun-15 | 12481 | 3 | 4 | 5 | | | V-1 | Prl2a1 | | |
| 12386 | 3 | 4 | 5 | | | V-1 | Pnpla5 | 150379 | 4-May-15 | 12482 | 3 | 4 | 5 | | | V-1 | Prl3a1 | | |
| 12387 | 3 | 4 | 5 | | | V-1 | Pnpt1 | 87178 | 4-May-15 | 12483 | 3 | 4 | 5 | | | V-1 | Prm3 | 58531 | 12-May-15 |
| 12388 | 3 | 4 | 5 | | | V-1 | Pnrc2 | 55629 | 12-May-15 | 12484 | 3 | 4 | 5 | | | V-1 | Prmt10 | 90826 | 4-May-15 |
| 12389 | 3 | 4 | 5 | | | V-1 | Poc1b | 282809 | 12-May-15 | 12485 | 3 | 4 | 5 | | | V-1 | Prmt3 | 10196 | 4-May-15 |
| 12390 | 3 | 4 | 5 | | | V-1 | Podnl1 | 79883 | 4-May-15 | 12486 | 3 | 4 | 5 | | | V-1 | Prnp | 5621 | 23-May-15 |
| 12391 | 3 | 4 | 5 | | | V-1 | Pof1b | 79983 | 12-May-15 | 12487 | 3 | 4 | 5 | | | V-1 | Proc | 5624 | 31-May-15 |
| 12392 | 3 | 4 | 5 | | | V-1 | Poglut1 | 56983 | 4-May-15 | 12488 | 3 | 4 | 5 | | | V-1 | Prodh2 | 58510 | 7-Jun-15 |
| 12393 | 3 | 4 | 5 | | | V-1 | Pola2 | 23649 | 4-May-15 | 12489 | 3 | 4 | 5 | | | V-1 | Prokr2 | 128674 | 23-May-15 |
| 12394 | 3 | 4 | 5 | | | V-1 | Polb | 5423 | 7-Jun-15 | 12490 | 3 | 4 | 5 | | | V-1 | Prop1 | 5626 | 23-May-15 |
| 12395 | 3 | 4 | 5 | | | V-1 | Pold2 | 5425 | 12-May-15 | 12491 | 3 | 4 | 5 | | | V-1 | Prosc | 11212 | 4-May-15 |
| 12396 | 3 | 4 | 5 | | | V-1 | Poldip2 | 26073 | 12-May-15 | 12492 | 3 | 4 | 5 | | | V-1 | Prox1 | 5629 | 4-May-15 |
| 12397 | 3 | 4 | 5 | | | V-1 | Pole2 | 5427 | 12-May-15 | 12493 | 3 | 4 | 5 | | | V-1 | Prp2 | | |
| 12398 | 3 | 4 | 5 | | | V-1 | Pole3 | 54107 | 4-May-15 | 12494 | 3 | 4 | 5 | | | V-1 | Prps1l1 | 221823 | 4-May-15 |
| 12399 | 3 | 4 | 5 | | | V-1 | Pole4 | 56655 | 4-May-15 | 12495 | 3 | 4 | 5 | | | V-1 | Prpsap2 | 5636 | 4-May-15 |
| 12400 | 3 | 4 | 5 | | | V-1 | Poli | 11201 | 4-May-15 | 12496 | 3 | 4 | 5 | | | V-1 | Prr12 | 57479 | 4-May-15 |
| 12401 | 3 | 4 | 5 | | | V-1 | Polk | 51426 | 7-Jun-15 | 12497 | 3 | 4 | 5 | | | V-1 | Prr14 | 78994 | 4-May-15 |
| 12402 | 3 | 4 | 5 | | | V-1 | Poln | 353497 | 4-May-15 | 12498 | 3 | 4 | 5 | | | V-1 | Prr16 | 51334 | 12-May-15 |
| 12403 | 3 | 4 | 5 | | | V-1 | Polr1a | 25885 | 4-Jun-15 | 12499 | 3 | 4 | 5 | | | V-1 | Prr3 | 80742 | 7-Jun-15 |
| 12404 | 3 | 4 | 5 | | | V-1 | Polr2i | 5438 | 28-May-15 | 12500 | 3 | 4 | 5 | | | V-1 | Prr5l | 79899 | 4-May-15 |
| 12405 | 3 | 4 | 5 | | | V-1 | Polr3k | 51728 | 28-May-15 | 12501 | 3 | 4 | 5 | | | V-1 | Prr7 | 80758 | 4-May-15 |
| 12406 | 3 | 4 | 5 | | | V-1 | Pomgnt1 | 55624 | 23-May-15 | 12502 | 3 | 4 | 5 | | | V-1 | Prr9 | 574414 | 4-May-15 |
| 12407 | 3 | 4 | 5 | | | V-1 | Pon2 | 5445 | 31-May-15 | 12503 | 3 | 4 | 5 | | | V-1 | Prrg2 | 5639 | 4-May-15 |
| 12408 | 3 | 4 | 5 | | | V-1 | Pop1 | 10940 | 7-Jun-15 | 12504 | 3 | 4 | 5 | | | V-1 | Prrg4 | 79056 | 4-May-15 |
| 12409 | 3 | 4 | 5 | | | V-1 | Pop4 | 10775 | 4-May-15 | 12505 | 3 | 4 | 5 | | | V-1 | Prrt2 | 112476 | 31-May-15 |
| 12410 | 3 | 4 | 5 | | | V-1 | Pop5 | 51367 | 4-May-15 | 12506 | 3 | 4 | 5 | | | V-1 | Prrx1 | 5396 | 23-May-15 |
| 12411 | 3 | 4 | 5 | | | V-1 | Popdc3 | 64208 | 4-May-15 | 12507 | 3 | 4 | 5 | | | V-1 | Prrxl1 | 644163 | 4-May-15 |
| 12412 | 3 | 4 | 5 | | | V-1 | Porcn | 64840 | 23-May-15 | 12508 | 3 | 4 | 5 | | | V-1 | Prss16 | 10279 | 4-May-15 |
| 12413 | 3 | 4 | 5 | | | V-1 | Pot1a | | | 12509 | 3 | 4 | 5 | | | V-1 | Prss21 | 10942 | 10-May-15 |
| 12414 | 3 | 4 | 5 | | | V-1 | Pou2f1 | 5451 | 28-May-15 | 12510 | 3 | 4 | 5 | | | V-1 | Prss27 | 83886 | 4-May-15 |
| 12415 | 3 | 4 | 5 | | | V-1 | Pou2f3 | 25833 | 28-May-15 | 12511 | 3 | 4 | 5 | | | V-1 | Prss30 | | |
| 12416 | 3 | 4 | 5 | | | V-1 | Pou3f4 | 5456 | 23-May-15 | 12512 | 3 | 4 | 5 | | | V-1 | Prss35 | 167681 | 4-May-15 |
| 12417 | 3 | 4 | 5 | | | V-1 | Pou5f2 | 134187 | 4-May-15 | 12513 | 3 | 4 | 5 | | | V-1 | Prss51 | 346670 | 17-Mar-15 |
| 12418 | 3 | 4 | 5 | | | V-1 | Ppa2 | 27068 | 12-May-15 | 12514 | 3 | 4 | 5 | | | V-1 | Prtg | 283659 | 4-May-15 |
| 12419 | 3 | 4 | 5 | | | V-1 | Ppap2a | 8611 | 4-May-15 | 12515 | 3 | 4 | 5 | | | V-1 | Prune | 58497 | 12-May-15 |
| 12420 | 3 | 4 | 5 | | | V-1 | Ppap2b | 8613 | 21-May-15 | 12516 | 3 | 4 | 5 | | | V-1 | Prx | 57716 | 7-Jun-15 |
| 12421 | 3 | 4 | 5 | | | V-1 | Ppapdc1a | 196051 | 4-May-15 | 12517 | 3 | 4 | 5 | | | V-1 | Psca | 8000 | 4-May-15 |
| 12422 | 3 | 4 | 5 | | | V-1 | Ppcdc | 60490 | 12-May-15 | 12518 | 3 | 4 | 5 | | | V-1 | Psd | 5662 | 7-Jun-15 |
| 12423 | 3 | 4 | 5 | | | V-1 | Ppfia2 | 8499 | 4-May-15 | 12519 | 3 | 4 | 5 | | | V-1 | Psd2 | 84249 | 4-May-15 |
| 12424 | 3 | 4 | 5 | | | V-1 | Ppfibp1 | 8496 | 4-May-15 | 12520 | 3 | 4 | 5 | | | V-1 | Psen1 | 5663 | 31-May-15 |
| 12425 | 3 | 4 | 5 | | | V-1 | Ppib | 5479 | 12-May-15 | 12521 | 3 | 4 | 5 | | | V-1 | Psenen | 55851 | 31-May-15 |
| 12426 | 3 | 4 | 5 | | | V-1 | Ppid | 5481 | 17-May-15 | 12522 | 3 | 4 | 5 | | | V-1 | Psma2 | 5683 | 4-May-15 |
| 12427 | 3 | 4 | 5 | | | V-1 | Ppifos | | | 12523 | 3 | 4 | 5 | | | V-1 | Psma6 | 5687 | 4-May-15 |
| 12428 | 3 | 4 | 5 | | | V-1 | Ppil2 | 23759 | 12-May-15 | 12524 | 3 | 4 | 5 | | | V-1 | Psmc1 | 5700 | 21-May-15 |
| 12429 | 3 | 4 | 5 | | | V-1 | Ppil4 | 85313 | 4-May-15 | 12525 | 3 | 4 | 5 | | | V-1 | Psmc4 | 5704 | 4-May-15 |
| 12430 | 3 | 4 | 5 | | | V-1 | Ppip5k1 | 9677 | 4-May-15 | 12526 | 3 | 4 | 5 | | | V-1 | Psmc5 | 5705 | 4-May-15 |

Fig. 30 - 67

| | | | | | | | | | | | | | | | |
|---|---|---|---|---|---|---|---|---|---|---|---|---|---|---|---|
| 12527 | 3 | 4 | 5 | | | V-1 | Psmd11 | 5717 | 4-May-15 | 12622 | 3 | 4 | 5 | | | V-1 | Rad1 | 5810 | 7-Jun-15 |
| 12528 | 3 | 4 | 5 | | | V-1 | Psmd12 | 5718 | 2-Jun-15 | 12623 | 3 | 4 | 5 | | | V-1 | Rad21 | 5885 | 31-May-15 |
| 12529 | 3 | 4 | 5 | | | V-1 | Psmd5 | 5711 | 4-May-15 | 12624 | 3 | 4 | 5 | | | V-1 | Rad21l | 642636 | 4-May-15 |
| 12530 | 3 | 4 | 5 | | | V-1 | Psme1 | 5720 | 4-May-15 | 12625 | 3 | 4 | 5 | | | V-1 | Rad23b | 5887 | 4-May-15 |
| 12531 | 3 | 4 | 5 | | | V-1 | Psme4 | 23198 | 4-May-15 | 12626 | 3 | 4 | 5 | | | V-1 | Rad51ap2 | 729475 | 4-May-15 |
| 12532 | 3 | 4 | 5 | | | V-1 | Psmg1 | 8624 | 4-May-15 | 12627 | 3 | 4 | 5 | | | V-1 | Rad51c | 5889 | 23-May-15 |
| 12533 | 3 | 4 | 5 | | | V-1 | Psors1c2 | 170680 | 12-May-15 | 12628 | 3 | 4 | 5 | | | V-1 | Rad51d | 5892 | 4-May-15 |
| 12534 | 3 | 4 | 5 | | | V-1 | Psph | 5723 | 4-May-15 | 12629 | 3 | 4 | 5 | | | V-1 | Rad52 | 5893 | 12-May-15 |
| 12535 | 3 | 4 | 5 | | | V-1 | Pspn | 5623 | 12-May-15 | 12630 | 3 | 4 | 5 | | | V-1 | Rad9a | 5883 | 17-May-15 |
| 12536 | 3 | 4 | 5 | | | V-1 | Pstk | 118672 | 12-May-15 | 12631 | 3 | 4 | 5 | | | V-1 | Rad9b | 144715 | 4-May-15 |
| 12537 | 3 | 4 | 5 | | | V-1 | Ptbp2 | 58155 | 2-Jun-15 | 12632 | 3 | 4 | 5 | | | V-1 | Radil | 55698 | 4-May-15 |
| 12538 | 3 | 4 | 5 | | | V-1 | Ptcd1 | 26024 | 17-May-15 | 12633 | 3 | 4 | 5 | | | V-1 | Rae1 | 8480 | 12-May-15 |
| 12539 | 3 | 4 | 5 | | | V-1 | Pten | 5728 | 2-Jun-15 | 12634 | 3 | 4 | 5 | | | V-1 | Raf1 | 5894 | 23-May-15 |
| 12540 | 3 | 4 | 5 | | | V-1 | Ptgdr2 | 11251 | 4-May-15 | 12635 | 3 | 4 | 5 | | | V-1 | Rai3 | 10743 | 16-Jun-15 |
| 12541 | 3 | 4 | 5 | | | V-1 | Ptger1 | 5731 | 4-May-15 | 12636 | 3 | 4 | 5 | | | V-1 | Rai4 | 5898 | 4-May-15 |
| 12542 | 3 | 4 | 5 | | | V-1 | Ptges | 9536 | 12-May-15 | 12637 | 3 | 4 | 5 | | | V-1 | Ralbp1 | 10928 | 7-Jun-15 |
| 12543 | 3 | 4 | 5 | | | V-1 | Ptges2 | 80142 | 4-May-15 | 12638 | 3 | 4 | 5 | | | V-1 | Ralganb | 57148 | 4-May-15 |
| 12544 | 3 | 4 | 5 | | | V-1 | Ptgir | 5739 | 4-May-15 | 12639 | 3 | 4 | 5 | | | V-1 | Raly | 22913 | 12-May-15 |
| 12545 | 3 | 4 | 5 | | | V-1 | Ptgr2 | 145482 | 4-May-15 | 12640 | 3 | 4 | 5 | | | V-1 | Ramp2 | 10266 | 4-May-15 |
| 12546 | 3 | 4 | 5 | | | V-1 | Ptgs2os | | | 12641 | 3 | 4 | 5 | | | V-1 | Ran | 5901 | 23-May-15 |
| 12547 | 3 | 4 | 5 | | | V-1 | Pth2 | 113091 | 4-May-15 | 12642 | 3 | 4 | 5 | | | V-1 | Ranbp1 | 5902 | 1-Jun-15 |
| 12548 | 3 | 4 | 5 | | | V-1 | Ptk6 | 5753 | 12-May-15 | 12643 | 3 | 4 | 5 | | | V-1 | Ranbp17 | 64901 | 12-May-15 |
| 12549 | 3 | 4 | 5 | | | V-1 | Ptma | 5757 | 7-Jun-15 | 12644 | 3 | 4 | 5 | | | V-1 | Rangap1 | 5905 | 4-May-15 |
| 12550 | 3 | 4 | 5 | | | V-1 | Ptms | 5763 | 4-May-15 | 12645 | 3 | 4 | 5 | | | V-1 | Rangrf | 29098 | 4-May-15 |
| 12551 | 3 | 4 | 5 | | | V-1 | Ptov1 | 53635 | 17-May-15 | 12646 | 3 | 4 | 5 | | | V-1 | Rap1gap2 | 23108 | 4-May-15 |
| 12552 | 3 | 4 | 5 | | | V-1 | Ptp4a2 | 8073 | 12-May-15 | 12647 | 3 | 4 | 5 | | | V-1 | Rap2c | 57826 | 4-May-15 |
| 12553 | 3 | 4 | 5 | | | V-1 | Ptpdc1 | 138639 | 12-May-15 | 12648 | 3 | 4 | 5 | | | V-1 | Rapgef6 | 51735 | 12-May-15 |
| 12554 | 3 | 4 | 5 | | | V-1 | Ptplb | 201562 | 4-May-15 | 12649 | 3 | 4 | 5 | | | V-1 | Raph1 | 65059 | 4-May-15 |
| 12555 | 3 | 4 | 5 | | | V-1 | Ptpmt1 | 114971 | 4-May-15 | 12650 | 3 | 4 | 5 | | | V-1 | Rapsn | 5913 | 12-May-15 |
| 12556 | 3 | 4 | 5 | | | V-1 | Ptpn11 | 5781 | 31-May-15 | 12651 | 3 | 4 | 5 | | | V-1 | Rarb | 5915 | 12-May-15 |
| 12557 | 3 | 4 | 5 | | | V-1 | Ptpn13 | 5783 | 12-May-15 | 12652 | 3 | 4 | 5 | | | V-1 | Rars | 5917 | 4-May-15 |
| 12558 | 3 | 4 | 5 | | | V-1 | Ptpn14 | 5784 | 14-May-15 | 12653 | 3 | 4 | 5 | | | V-1 | Rasal1 | 8437 | 4-May-15 |
| 12559 | 3 | 4 | 5 | | | V-1 | Ptpn2 | 5771 | 24-May-15 | 12654 | 3 | 4 | 5 | | | V-1 | Rasgef1a | 221002 | 4-May-15 |
| 12560 | 3 | 4 | 5 | | | V-1 | Ptpn20 | 26095 | 14-May-15 | 12655 | 3 | 4 | 5 | | | V-1 | Rasgef1c | 255426 | 4-May-15 |
| 12561 | 3 | 4 | 5 | | | V-1 | Ptpn23 | 25930 | 4-May-15 | 12656 | 3 | 4 | 5 | | | V-1 | Rasgrf2 | 5924 | 4-May-15 |
| 12562 | 3 | 4 | 5 | | | V-1 | Ptpn9 | 5780 | 4-May-15 | 12657 | 3 | 4 | 5 | | | V-1 | Rasgrp4 | 115727 | 12-May-15 |
| 12563 | 3 | 4 | 5 | | | V-1 | Ptpra | 5786 | 17-May-15 | 12658 | 3 | 4 | 5 | | | V-1 | Rasip1 | 54922 | 4-May-15 |
| 12564 | 3 | 4 | 5 | | | V-1 | Ptprd | 5789 | 4-May-15 | 12659 | 3 | 4 | 5 | | | V-1 | Rasl10b | 91608 | 4-May-15 |
| 12565 | 3 | 4 | 5 | | | V-1 | Ptprg | 5793 | 12-May-15 | 12660 | 3 | 4 | 5 | | | V-1 | Rasl2-9 | | |
| 12566 | 3 | 4 | 5 | | | V-1 | Ptprk | 5796 | 12-May-15 | 12661 | 3 | 4 | 5 | | | V-1 | Rassf10 | 644943 | 4-May-15 |
| 12567 | 3 | 4 | 5 | | | V-1 | Ptprn | 5798 | 4-May-15 | 12662 | 3 | 4 | 5 | | | V-1 | Rassf3 | 283349 | 7-Jun-15 |
| 12568 | 3 | 4 | 5 | | | V-1 | Ptprq | 374462 | 4-May-15 | 12663 | 3 | 4 | 5 | | | V-1 | Rassf7 | 8045 | 4-May-15 |
| 12569 | 3 | 4 | 5 | | | V-1 | Ptprs | 5802 | 12-May-15 | 12664 | 3 | 4 | 5 | | | V-1 | Raver1 | 125950 | 4-May-15 |
| 12570 | 3 | 4 | 5 | | | V-1 | Ptprz1 | 5803 | 17-May-15 | 12665 | 3 | 4 | 5 | | | V-1 | Rb1cc1 | 9821 | 23-May-15 |
| 12571 | 3 | 4 | 5 | | | V-1 | Ptrh2 | 51651 | 21-May-15 | 12666 | 3 | 4 | 5 | | | V-1 | Rbbp8ni | 140893 | 4-May-15 |
| 12572 | 3 | 4 | 5 | | | V-1 | Pttg1ip | 754 | 12-May-15 | 12667 | 3 | 4 | 5 | | | V-1 | Rbfa | 79863 | 4-May-15 |
| 12573 | 3 | 4 | 5 | | | V-1 | Ptx4 | 390667 | 4-May-15 | 12668 | 3 | 4 | 5 | | | V-1 | Rbl1 | 5933 | 4-May-15 |
| 12574 | 3 | 4 | 5 | | | V-1 | Pus7l | 83448 | 4-May-15 | 12669 | 3 | 4 | 5 | | | V-1 | Rbl2 | 5934 | 4-May-15 |
| 12575 | 3 | 4 | 5 | | | V-1 | Pusl1 | 126789 | 23-May-15 | 12670 | 3 | 4 | 5 | | | V-1 | Rbm12 | 10137 | 4-May-15 |
| 12576 | 3 | 4 | 5 | | | V-1 | Pvrl2 | 5819 | 12-May-15 | 12671 | 3 | 4 | 5 | | | V-1 | Rbm12b | | |
| 12577 | 3 | 4 | 5 | | | V-1 | Pvrl3 | 25945 | 4-May-15 | 12672 | 3 | 4 | 5 | | | V-1 | Rbm14-rbm4 | 100526 737 | 4-May-15 |
| 12578 | 3 | 4 | 5 | | | V-1 | Pvrl | 5820 | 17-May-15 | 12673 | 3 | 4 | 5 | | | V-1 | Rbm15 | 64783 | 4-May-15 |
| 12579 | 3 | 4 | 5 | | | V-1 | Pxdn | 7837 | 4-May-15 | 12674 | 3 | 4 | 5 | | | V-1 | Rbm15b | 29890 | 4-May-15 |
| 12580 | 3 | 4 | 5 | | | V-1 | Pxk | 54899 | 17-May-15 | 12675 | 3 | 4 | 5 | | | V-1 | Rbm25 | 58517 | 12-May-15 |
| 12581 | 3 | 4 | 5 | | | V-1 | Pxmp4 | 11264 | 29-May-15 | 12676 | 3 | 4 | 5 | | | V-1 | Rbm3ly | | |
| 12582 | 3 | 4 | 5 | | | V-1 | Pxt1 | 222659 | 4-May-15 | 12677 | 3 | 4 | 5 | | | V-1 | Rbm39 | 9584 | 4-May-15 |
| 12583 | 3 | 4 | 5 | | | V-1 | Pycr1 | 5831 | 12-May-15 | 12678 | 3 | 4 | 5 | | | V-1 | Rbm41 | 55285 | 4-May-15 |
| 12584 | 3 | 4 | 5 | | | V-1 | Pycr2 | 29920 | 4-May-15 | 12679 | 3 | 4 | 5 | | | V-1 | Rbm44 | 375316 | 4-May-15 |
| 12585 | 3 | 4 | 5 | | | V-1 | Pycrl | 65263 | 4-May-15 | 12680 | 3 | 4 | 5 | | | V-1 | Rbm48 | 84060 | 4-May-15 |
| 12586 | 3 | 4 | 5 | | | V-1 | Pydc4 | | | 12681 | 3 | 4 | 5 | | | V-1 | Rbmx | 27316 | 12-May-15 |
| 12587 | 3 | 4 | 5 | | | V-1 | Pygo1 | 26108 | 4-May-15 | 12682 | 3 | 4 | 5 | | | V-1 | Rbmxl2 | 27288 | 4-May-15 |
| 12588 | 3 | 4 | 5 | | | V-1 | Pygo2 | 90780 | 4-May-15 | 12683 | 3 | 4 | 5 | | | V-1 | Rbp3 | 5949 | 7-Jun-15 |
| 12589 | 3 | 4 | 5 | | | V-1 | Pyroxd1 | 79912 | 4-May-15 | 12684 | 3 | 4 | 5 | | | V-1 | Rbpj | 3516 | 12-May-15 |
| 12590 | 3 | 4 | 5 | | | V-1 | Pyurf | 100996 939 | 4-May-15 | 12685 | 3 | 4 | 5 | | | V-1 | Rbx1 | 9978 | 2-Jun-15 |
| 12591 | 3 | 4 | 5 | | | V-1 | Pzp | 5858 | 12-May-15 | 12686 | 3 | 4 | 5 | | | V-1 | Rc3h2 | 54542 | 4-May-15 |
| 12592 | 3 | 4 | 5 | | | V-1 | Qpct1 | 54814 | 4-May-15 | 12687 | 3 | 4 | 5 | | | V-1 | Rcan3 | 11123 | 12-May-15 |
| 12593 | 3 | 4 | 5 | | | V-1 | Qrfp | 347148 | 4-May-15 | 12688 | 3 | 4 | 5 | | | V-1 | Rcc2 | 55920 | 12-May-15 |
| 12594 | 3 | 4 | 5 | | | V-1 | Qser1 | 79832 | 4-May-15 | 12689 | 3 | 4 | 5 | | | V-1 | Rccd1 | 91433 | 4-May-15 |
| 12595 | 3 | 4 | 5 | | | V-1 | Qtrt1 | 81890 | 4-May-15 | 12690 | 3 | 4 | 5 | | | V-1 | Rcn1 | 5954 | 13-Jun-15 |
| 12596 | 3 | 4 | 5 | | | V-1 | Rab11fip2 | 22841 | 4-May-15 | 12691 | 3 | 4 | 5 | | | V-1 | Rcn3 | 57333 | 7-Jun-15 |
| 12597 | 3 | 4 | 5 | | | V-1 | Rab11fip4os1 | | | 12692 | 3 | 4 | 5 | | | V-1 | Rcor1 | 23186 | 7-Jun-15 |
| 12598 | 3 | 4 | 5 | | | V-1 | Rab14 | 51552 | 4-May-15 | 12693 | 3 | 4 | 5 | | | V-1 | Rcor3 | 55758 | 14-May-15 |
| 12599 | 3 | 4 | 5 | | | V-1 | Rab1b | 81876 | 21-May-15 | 12694 | 3 | 4 | 5 | | | V-1 | Rcvrn | 5957 | 4-May-15 |
| 12600 | 3 | 4 | 5 | | | V-1 | Rab21 | 23011 | 4-May-15 | 12695 | 3 | 4 | 5 | | | V-1 | Rdh1 | 5959 | 4-May-15 |
| 12601 | 3 | 4 | 5 | | | V-1 | Rab24 | 53917 | 21-May-15 | 12696 | 3 | 4 | 5 | | | V-1 | Rdh10 | 157506 | 31-May-15 |
| 12602 | 3 | 4 | 5 | | | V-1 | Rab26 | 25837 | 12-May-15 | 12697 | 3 | 4 | 5 | | | V-1 | Rdh13 | 112724 | 4-May-15 |
| 12603 | 3 | 4 | 5 | | | V-1 | Rab27b | 5874 | 4-May-15 | 12698 | 3 | 4 | 5 | | | V-1 | Rdm1 | 201299 | 4-May-15 |
| 12604 | 3 | 4 | 5 | | | V-1 | Rab33a | 9363 | 21-May-15 | 12699 | 3 | 4 | 5 | | | V-1 | Rdx | 5962 | 3-Jun-15 |
| 12605 | 3 | 4 | 5 | | | V-1 | Rab33b | 83452 | 21-May-15 | 12700 | 3 | 4 | 5 | | | V-1 | Recql | 5965 | 4-May-15 |
| 12606 | 3 | 4 | 5 | | | V-1 | Rab35 | 11021 | 23-May-15 | 12701 | 3 | 4 | 5 | | | V-1 | Recql5 | 9400 | 21-May-15 |
| 12607 | 3 | 4 | 5 | | | V-1 | Rab38 | 23682 | 4-May-15 | 12702 | 3 | 4 | 5 | | | V-1 | Reep1 | 65055 | 4-May-15 |
| 12608 | 3 | 4 | 5 | | | V-1 | Rab39b | 116442 | 4-May-15 | 12703 | 3 | 4 | 5 | | | V-1 | Reep3 | 221035 | 4-May-15 |
| 12609 | 3 | 4 | 5 | | | V-1 | Rab3d | 9545 | 4-May-15 | 12704 | 3 | 4 | 5 | | | V-1 | Reep5 | 7905 | 12-May-15 |
| 12610 | 3 | 4 | 5 | | | V-1 | Rab3ip | 117177 | 4-May-15 | 12705 | 3 | 4 | 5 | | | V-1 | Reg4 | 83998 | 4-May-15 |
| 12611 | 3 | 4 | 5 | | | V-1 | Rab40b | 10966 | 4-May-15 | 12706 | 3 | 4 | 5 | | | V-1 | Rela | 5970 | 29-May-15 |
| 12612 | 3 | 4 | 5 | | | V-1 | Rab40c | 57799 | 4-May-15 | 12707 | 3 | 4 | 5 | | | V-1 | Rell2 | 285613 | 4-May-15 |
| 12613 | 3 | 4 | 5 | | | V-1 | Rab43 | 339122 | 4-May-15 | 12708 | 3 | 4 | 5 | | | V-1 | Rem2 | 161253 | 4-May-15 |
| 12614 | 3 | 4 | 5 | | | V-1 | Rab4a | 5867 | 21-May-15 | 12709 | 3 | 4 | 5 | | | V-1 | Ren | | |
| 12615 | 3 | 4 | 5 | | | V-1 | Rab5a | 5868 | 31-May-15 | 12710 | 3 | 4 | 5 | | | V-1 | Rep15 | 387849 | 28-May-15 |
| 12616 | 3 | 4 | 5 | | | V-1 | Rab7 | 7879 | 7-Jun-15 | 12711 | 3 | 4 | 5 | | | V-1 | Rer1 | 13079 | 20-May-15 |
| 12617 | 3 | 4 | 5 | | | V-1 | Rab8a | 4218 | 4-May-15 | 12712 | 3 | 4 | 5 | | | V-1 | Rergl | 79785 | 4-May-15 |
| 12618 | 3 | 4 | 5 | | | V-1 | Rab9 | 9367 | 29-May-15 | 12713 | 3 | 4 | 5 | | | V-1 | Rest | 5978 | 28-May-15 |
| 12619 | 3 | 4 | 5 | | | V-1 | Rabepk | 10244 | 4-May-15 | 12714 | 3 | 4 | 5 | | | V-1 | Rev1 | 51455 | 23-May-15 |
| 12620 | 3 | 4 | 5 | | | V-1 | Rabif | 5877 | 4-May-15 | 12715 | 3 | 4 | 5 | | | V-1 | Rfesd | 317673 | 4-May-15 |
| 12621 | 3 | 4 | 5 | | | V-1 | Rac3 | 5881 | 7-Jun-15 | 12716 | 3 | 4 | 5 | | | V-1 | Rfk | 55312 | 4-May-15 |

Fig. 30 - 68

| | | | | | | | | | | | | | | | | |
|---|---|---|---|---|---|---|---|---|---|---|---|---|---|---|---|---|
| 12717 | 3 | 4 | 5 | | | V-1 | Rftn2 | 130132 | 12-May-15 | 12813 | 3 | 4 | 5 | | | V-1 | Rpl36al | 6166 | 12-May-15 |
| 12718 | 3 | 4 | 5 | | | V-1 | Rfx1 | 5989 | 28-May-15 | 12814 | 3 | 4 | 5 | | | V-1 | Rpl37a | 6168 | 4-May-15 |
| 12719 | 3 | 4 | 5 | | | V-1 | Rfx3 | 5991 | 28-May-15 | 12815 | 3 | 4 | 5 | | | V-1 | Rpl39l | 116832 | 4-May-15 |
| 12720 | 3 | 4 | 5 | | | V-1 | Rfx8 | 731220 | 4-May-15 | 12816 | 3 | 4 | 5 | | | V-1 | Rpl4 | 6124 | 4-May-15 |
| 12721 | 3 | 4 | 5 | | | V-1 | Rfxap | 5994 | 4-May-15 | 12817 | 3 | 4 | 5 | | | V-1 | Rpl41 | 6171 | 12-May-15 |
| 12722 | 3 | 4 | 5 | | | V-1 | Rgl1 | 23179 | 7-Jun-15 | 12818 | 3 | 4 | 5 | | | V-1 | Rpl8 | 6132 | 4-May-15 |
| 12723 | 3 | 4 | 5 | | | V-1 | Rgl2 | 5863 | 4-May-15 | 12819 | 3 | 4 | 5 | | | V-1 | Rpip1 | 6176 | 12-May-15 |
| 12724 | 3 | 4 | 5 | | | V-1 | Rgma | 56963 | 12-May-15 | 12820 | 3 | 4 | 5 | | | V-1 | Rplp2-ps1 | | |
| 12725 | 3 | 4 | 5 | | | V-1 | Rgp1 | 9827 | un-2015 | 12821 | 3 | 4 | 5 | | | V-1 | Rpn1 | 6184 | 7-Jun-15 |
| 12726 | 3 | 4 | 5 | | | V-1 | Rgs12 | 6002 | 21-May-15 | 12822 | 3 | 4 | 5 | | | V-1 | Rpn2 | 6185 | 7-Jun-15 |
| 12727 | 3 | 4 | 5 | | | V-1 | Rgs17 | 26575 | 4-May-15 | 12823 | 3 | 4 | 5 | | | V-1 | Rpp21 | 79897 | 4-May-15 |
| 12728 | 3 | 4 | 5 | | | V-1 | Rgs20 | 8601 | 4-May-15 | 12824 | 3 | 4 | 5 | | | V-1 | Rprd1b | 58460 | 1-Jun-15 |
| 12729 | 3 | 4 | 5 | | | V-1 | Rgs9bp | 388531 | 4-May-15 | 12825 | 3 | 4 | 5 | | | V-1 | Rps12 | 6206 | 7-Jun-15 |
| 12730 | 3 | 4 | 5 | | | V-1 | Rhbdd1 | 84236 | 29-May-15 | 12826 | 3 | 4 | 5 | | | V-1 | Rps14 | 6208 | 2-Jun-15 |
| 12731 | 3 | 4 | 5 | | | V-1 | Rheb | 6009 | 7-Jun-15 | 12827 | 3 | 4 | 5 | | | V-1 | Rps15a-ps4 | | |
| 12732 | 3 | 4 | 5 | | | V-1 | Rho | 6010 | 7-Jun-15 | 12828 | 3 | 4 | 5 | | | V-1 | Rps15a-ps6 | | |
| 12733 | 3 | 4 | 5 | | | V-1 | Rhobtb2 | 23221 | 21-May-15 | 12829 | 3 | 4 | 5 | | | V-1 | Rps21 | 6227 | 21-May-15 |
| 12734 | 3 | 4 | 5 | | | V-1 | Rhoc | 389 | 3-May-15 | 12830 | 3 | 4 | 5 | | | V-1 | Rps23 | 6228 | 12-May-15 |
| 12735 | 3 | 4 | 5 | | | V-1 | Rhod | 29984 | 4-May-15 | 12831 | 3 | 4 | 5 | | | V-1 | Rps24 | 6229 | 23-May-15 |
| 12736 | 3 | 4 | 5 | | | V-1 | Rhof | 54509 | 23-May-15 | 12832 | 3 | 4 | 5 | | | V-1 | Rps25 | 6230 | 4-May-15 |
| 12737 | 3 | 4 | 5 | | | V-1 | Rhoq | 23433 | 4-May-15 | 12833 | 3 | 4 | 5 | | | V-1 | Rps27a | 6233 | 17-May-15 |
| 12738 | 3 | 4 | 5 | | | V-1 | Rhot1 | 55288 | 23-May-15 | 12834 | 3 | 4 | 5 | | | V-1 | Rps27l | 51065 | 4-May-15 |
| 12739 | 3 | 4 | 5 | | | V-1 | Rhov | 171177 | 4-May-15 | 12835 | 3 | 4 | 5 | | | V-1 | Rps29 | 6235 | 4-May-15 |
| 12740 | 3 | 4 | 5 | | | V-1 | Rhox1 | | | 12836 | 3 | 4 | 5 | | | V-1 | Rps3 | 6188 | 4-May-15 |
| 12741 | 3 | 4 | 5 | | | V-1 | Rhox4b | | | 12837 | 3 | 4 | 5 | | | V-1 | Rps4l | 128580 | 4-May-15 |
| 12742 | 3 | 4 | 5 | | | V-1 | Rhpn2 | 85415 | 4-May-15 | 12838 | 3 | 4 | 5 | | | V-1 | Rps4x | 6191 | 12-May-15 |
| 12743 | 3 | 4 | 5 | | | V-1 | Rian | 79104 | 12-May-15 | 12839 | 3 | 4 | 5 | | | V-1 | Rps6ka2 | 6196 | 21-May-15 |
| 12744 | 3 | 4 | 5 | | | V-1 | Ribc1 | 158787 | 4-May-15 | 12840 | 3 | 4 | 5 | | | V-1 | Rps6ka6 | 27330 | 4-May-15 |
| 12745 | 3 | 4 | 5 | | | V-1 | Rilp | 83547 | 7-Jun-15 | 12841 | 3 | 4 | 5 | | | V-1 | Rps8 | 6202 | 4-May-15 |
| 12746 | 3 | 4 | 5 | | | V-1 | Rilpl1 | 353116 | 4-May-15 | 12842 | 3 | 4 | 5 | | | V-1 | Rptor | 57521 | 17-May-15 |
| 12747 | 3 | 4 | 5 | | | V-1 | Rin2 | 54453 | 14-May-15 | 12843 | 3 | 4 | 5 | | | V-1 | Rraga | 10670 | 29-May-15 |
| 12748 | 3 | 4 | 5 | | | V-1 | Ring1 | 6015 | 4-May-15 | 12844 | 3 | 4 | 5 | | | V-1 | Rragc | 64121 | 31-May-15 |
| 12749 | 3 | 4 | 5 | | | V-1 | Rinl | 126432 | 4-May-15 | 12845 | 3 | 4 | 5 | | | V-1 | Rras | 6237 | 12-May-15 |
| 12750 | 3 | 4 | 5 | | | V-1 | Rint1 | 60561 | 29-May-15 | 12846 | 3 | 4 | 5 | | | V-1 | Rrbp1 | 6238 | 4-May-15 |
| 12751 | 3 | 4 | 5 | | | V-1 | Riok3 | 8780 | 4-May-15 | 12847 | 3 | 4 | 5 | | | V-1 | Rrm2b | 50484 | 17-May-15 |
| 12752 | 3 | 4 | 5 | | | V-1 | Ripply1 | 92129 | 4-May-15 | 12848 | 3 | 4 | 5 | | | V-1 | Rrp15 | 51018 | 4-May-15 |
| 12753 | 3 | 4 | 5 | | | V-1 | Rit2 | 6014 | 4-May-15 | 12849 | 3 | 4 | 5 | | | V-1 | Rrp1b | 23076 | 4-May-15 |
| 12754 | 3 | 4 | 5 | | | V-1 | Rlim | 51132 | 4-May-15 | 12850 | 3 | 4 | 5 | | | V-1 | Rrp36 | 88745 | 4-May-15 |
| 12755 | 3 | 4 | 5 | | | V-1 | Rmdn1 | 51115 | 12-May-15 | 12851 | 3 | 4 | 5 | | | V-1 | Rs1 | 6247 | 24-May-15 |
| 12756 | 3 | 4 | 5 | | | V-1 | Rmnd1 | 55005 | 4-May-15 | 12852 | 3 | 4 | 5 | | | V-1 | Rsbn1 | 54665 | 4-May-15 |
| 12757 | 3 | 4 | 5 | | | V-1 | Rmnd5a | 64795 | 4-May-15 | 12853 | 3 | 4 | 5 | | | V-1 | Rsf1 | 51773 | 31-May-15 |
| 12758 | 3 | 4 | 5 | | | V-1 | Rmst | 196475 | 4-May-15 | 12854 | 3 | 4 | 5 | | | V-1 | Rsph3a | | |
| 12759 | 3 | 4 | 5 | | | V-1 | Rnase6 | 6039 | 4-May-15 | 12855 | 3 | 4 | 5 | | | V-1 | Rsph3b | | |
| 12760 | 3 | 4 | 5 | | | V-1 | Rnaseh1 | 246243 | 7-Jun-15 | 12856 | 3 | 4 | 5 | | | V-1 | Rspo2 | 340419 | 4-May-15 |
| 12761 | 3 | 4 | 5 | | | V-1 | Rnaseh2c | 84153 | 23-May-15 | 12857 | 3 | 4 | 5 | | | V-1 | Rtn3 | 10313 | 12-May-15 |
| 12762 | 3 | 4 | 5 | | | V-1 | Rnaset2a | | | 12858 | 3 | 4 | 5 | | | V-1 | Rtn4rl1 | 146760 | 4-May-15 |
| 12763 | 3 | 4 | 5 | | | V-1 | Rnd2 | 8153 | 4-May-15 | 12859 | 3 | 4 | 5 | | | V-1 | Rtp1 | 132112 | 9-May-15 |
| 12764 | 3 | 4 | 5 | | | V-1 | Rnf10 | 9921 | 4-May-15 | 12860 | 3 | 4 | 5 | | | V-1 | Rttn | 25914 | 4-May-15 |
| 12765 | 3 | 4 | 5 | | | V-1 | Rnf103 | 7844 | 4-May-15 | 12861 | 3 | 4 | 5 | | | V-1 | Rufy1 | 80230 | 4-May-15 |
| 12766 | 3 | 4 | 5 | | | V-1 | Rnf11 | 26994 | 2-Jun-15 | 12862 | 3 | 4 | 5 | | | V-1 | Rundc1 | 146923 | 12-May-15 |
| 12767 | 3 | 4 | 5 | | | V-1 | Rnf111 | 54778 | 4-May-15 | 12863 | 3 | 4 | 5 | | | V-1 | Runx1t1 | 862 | 21-May-15 |
| 12768 | 3 | 4 | 5 | | | V-1 | Rnf114 | 55905 | 4-May-15 | 12864 | 3 | 4 | 5 | | | V-1 | Rusc1 | 23623 | 4-May-15 |
| 12769 | 3 | 4 | 5 | | | V-1 | Rnf121 | 55298 | 4-May-15 | 12865 | 3 | 4 | 5 | | | V-1 | Ruvbl1 | 8607 | 17-May-15 |
| 12770 | 3 | 4 | 5 | | | V-1 | Rnf123 | 63891 | 4-May-15 | 12866 | 3 | 4 | 5 | | | V-1 | Rwdd1 | 51389 | 4-May-15 |
| 12771 | 3 | 4 | 5 | | | V-1 | Rnf125 | 54941 | 23-May-15 | 12867 | 3 | 4 | 5 | | | V-1 | Rwdd2b | 10069 | 4-May-15 |
| 12772 | 3 | 4 | 5 | | | V-1 | Rnf126 | 55658 | 4-May-15 | 12868 | 3 | 4 | 5 | | | V-1 | Rwdd3 | 25950 | 4-May-15 |
| 12773 | 3 | 4 | 5 | | | V-1 | Rnf13 | 11342 | 1-Jun-15 | 12869 | 3 | 4 | 5 | | | V-1 | Rwdd4a | 201965 | 12-May-15 |
| 12774 | 3 | 4 | 5 | | | V-1 | Rnf144b | 255488 | 4-May-15 | 12870 | 3 | 4 | 5 | | | V-1 | Rxfp2 | 122042 | 4-May-15 |
| 12775 | 3 | 4 | 5 | | | V-1 | Rnf150 | 57484 | 4-May-15 | 12871 | 3 | 4 | 5 | | | V-1 | Rybp | 23429 | 2-Jun-15 |
| 12776 | 3 | 4 | 5 | | | V-1 | Rnf151 | 146310 | 4-May-15 | 12872 | 3 | 4 | 5 | | | V-1 | Ryr1 | 6261 | 24-May-15 |
| 12777 | 3 | 4 | 5 | | | V-1 | Rnf165 | 494470 | 1-Jun-15 | 12873 | 3 | 4 | 5 | | | V-1 | Ryr2 | 6262 | 23-May-15 |
| 12778 | 3 | 4 | 5 | | | V-1 | Rnf181 | 51255 | 23-May-15 | 12874 | 3 | 4 | 5 | | | V-1 | S100a1 | 6271 | 4-May-15 |
| 12779 | 3 | 4 | 5 | | | V-1 | Rnf185 | 91445 | 28-May-15 | 12875 | 3 | 4 | 5 | | | V-1 | S100a13 | 6284 | 12-May-15 |
| 12780 | 3 | 4 | 5 | | | V-1 | Rnf187 | 149603 | 12-May-15 | 12876 | 3 | 4 | 5 | | | V-1 | S100a16 | 140576 | 7-Jun-15 |
| 12781 | 3 | 4 | 5 | | | V-1 | Rnf19b | 127544 | 23-May-15 | 12877 | 3 | 4 | 5 | | | V-1 | S100a3 | 6274 | 4-May-15 |
| 12782 | 3 | 4 | 5 | | | V-1 | Rnf2 | 6045 | 2-Jun-15 | 12878 | 3 | 4 | 5 | | | V-1 | S100g | 795 | 4-May-15 |
| 12783 | 3 | 4 | 5 | | | V-1 | Rnf214 | 257160 | 4-May-15 | 12879 | 3 | 4 | 5 | | | V-1 | S100pbp | 64766 | 4-May-15 |
| 12784 | 3 | 4 | 5 | | | V-1 | Rnf219 | 79596 | 4-May-15 | 12880 | 3 | 4 | 5 | | | V-1 | S1pr3 | 1903 | 4-May-15 |
| 12785 | 3 | 4 | 5 | | | V-1 | Rnf25 | 64320 | 4-May-15 | 12881 | 3 | 4 | 5 | | | V-1 | Saa4 | 6291 | 7-Jun-15 |
| 12786 | 3 | 4 | 5 | | | V-1 | Rnf31 | 55072 | 4-May-15 | 12882 | 3 | 4 | 5 | | | V-1 | Safb | 6294 | 4-May-15 |
| 12787 | 3 | 4 | 5 | | | V-1 | Rnf34 | 80196 | 12-May-15 | 12883 | 3 | 4 | 5 | | | V-1 | Sall2 | 6297 | 21-May-15 |
| 12788 | 3 | 4 | 5 | | | V-1 | Rngtt | 8732 | 12-May-15 | 12884 | 3 | 4 | 5 | | | V-1 | Sall3 | 27164 | 4-May-15 |
| 12789 | 3 | 4 | 5 | | | V-1 | Rnls | 55328 | 12-May-15 | 12885 | 3 | 4 | 5 | | | V-1 | Samd12 | 401474 | 4-May-15 |
| 12790 | 3 | 4 | 5 | | | V-1 | Robo1 | 6091 | 17-May-15 | 12886 | 3 | 4 | 5 | | | V-1 | Samd15 | 161394 | 4-May-15 |
| 12791 | 3 | 4 | 5 | | | V-1 | Robo2 | 6092 | 12-May-15 | 12887 | 3 | 4 | 5 | | | V-1 | Samd4 | 23034 | 4-May-15 |
| 12792 | 3 | 4 | 5 | | | V-1 | Rock1 | 6093 | 31-May-15 | 12888 | 3 | 4 | 5 | | | V-1 | Samd7 | 344658 | 12-May-15 |
| 12793 | 3 | 4 | 5 | | | V-1 | Rora | 6095 | 12-May-15 | 12889 | 3 | 4 | 5 | | | V-1 | Samhd1 | 25939 | 23-May-15 |
| 12794 | 3 | 4 | 5 | | | V-1 | Rp1 | 6101 | 23-May-15 | 12890 | 3 | 4 | 5 | | | V-1 | Samm50 | 25813 | 4-May-15 |
| 12795 | 3 | 4 | 5 | | | V-1 | Rpa1 | 6117 | 7-Jun-15 | 12891 | 3 | 4 | 5 | | | V-1 | Samt1 | | |
| 12796 | 3 | 4 | 5 | | | V-1 | Rpain | 84268 | 4-May-15 | 12892 | 3 | 4 | 5 | | | V-1 | Sap18 | 10284 | 4-May-15 |
| 12797 | 3 | 4 | 5 | | | V-1 | Rpgr | 6103 | 23-May-15 | 12893 | 3 | 4 | 5 | | | V-1 | Sap30bp | 29115 | 12-May-15 |
| 12798 | 3 | 4 | 5 | | | V-1 | Rph3a | 22895 | 4-May-15 | 12894 | 3 | 4 | 5 | | | V-1 | Sap30l | 79685 | 4-May-15 |
| 12799 | 3 | 4 | 5 | | | V-1 | Rpl10 | 6134 | 7-Jun-15 | 12895 | 3 | 4 | 5 | | | V-1 | Sar1a | 56681 | 3-May-15 |
| 12800 | 3 | 4 | 5 | | | V-1 | Rpl10a | 4736 | 25-May-15 | 12896 | 3 | 4 | 5 | | | V-1 | Sarm1 | 23098 | 12-May-15 |
| 12801 | 3 | 4 | 5 | | | V-1 | Rpl13 | 6137 | 7-Jun-15 | 12897 | 3 | 4 | 5 | | | V-1 | Sart1 | 9092 | 12-May-15 |
| 12802 | 3 | 4 | 5 | | | V-1 | Rpl14 | 9045 | 12-May-15 | 12898 | 3 | 4 | 5 | | | V-1 | Sat2 | 112483 | 13-Jun-15 |
| 12803 | 3 | 4 | 5 | | | V-1 | Rpl21 | 6144 | 7-Jun-15 | 12899 | 3 | 4 | 5 | | | V-1 | Satb1 | 6304 | 26-May-15 |
| 12804 | 3 | 4 | 5 | | | V-1 | Rpl22 | 6146 | 4-May-15 | 12900 | 3 | 4 | 5 | | | V-1 | Sbp | | |
| 12805 | 3 | 4 | 5 | | | V-1 | Rpl27 | 6155 | 21-May-15 | 12901 | 3 | 4 | 5 | | | V-1 | Sbspon | 157869 | 4-May-15 |
| 12806 | 3 | 4 | 5 | | | V-1 | Rpl29 | 6159 | 4-May-15 | 12902 | 3 | 4 | 5 | | | V-1 | Scaf1 | 58506 | 4-May-15 |
| 12807 | 3 | 4 | 5 | | | V-1 | Rpl30 | 6156 | 4-May-15 | 12903 | 3 | 4 | 5 | | | V-1 | Scand1 | 51282 | 28-May-15 |
| 12808 | 3 | 4 | 5 | | | V-1 | Rpl31 | 6160 | 4-May-15 | 12904 | 3 | 4 | 5 | | | V-1 | Scarb1 | 949 | 24-May-15 |
| 12809 | 3 | 4 | 5 | | | V-1 | Rpl34-ps1 | | | 12905 | 3 | 4 | 5 | | | V-1 | Scarb2 | 950 | 17-May-15 |
| 12810 | 3 | 4 | 5 | | | V-1 | Rpl35 | 11224 | 4-May-15 | 12906 | 3 | 4 | 5 | | | V-1 | Sccpdh | 51097 | 4-May-15 |
| 12811 | 3 | 4 | 5 | | | V-1 | Rpl35a | 6165 | 2-Jun-15 | 12907 | 3 | 4 | 5 | | | V-1 | Scd2 | 79966 | 4-May-15 |
| 12812 | 3 | 4 | 5 | | | V-1 | Rpl36 | 25873 | 12-May-15 | 12908 | 3 | 4 | 5 | | | V-1 | Scd3 | | |

Fig. 30 - 69

| | | | | | | | | | | | | | | | | |
|---|---|---|---|---|---|---|---|---|---|---|---|---|---|---|---|---|
| 12909 | 3 | 4 | 5 | | V-1 | Scei | 8796 | 4-May-15 | 13005 | 3 | 4 | 5 | | V-1 | Sgcg | 6445 | 23-May-15 |
| 12910 | 3 | 4 | 5 | | V-1 | Scfd1 | 23256 | 21-May-15 | 13006 | 3 | 4 | 5 | | V-1 | Sgk2 | 10130 | 7-Jun-15 |
| 12911 | 3 | 4 | 5 | | V-1 | Scgb1b19 | | | 13007 | 3 | 4 | 5 | | V-1 | Sgk3 | 23678 | 4-May-15 |
| 12912 | 3 | 4 | 5 | | V-1 | Scgb1b20 | | | 13008 | 3 | 4 | 5 | | V-1 | Sgms1 | 259230 | 12-May-15 |
| 12913 | 3 | 4 | 5 | | V-1 | Scgb2b12 | | | 13009 | 3 | 4 | 5 | | V-1 | Sgms2 | 166929 | 4-May-15 |
| 12914 | 3 | 4 | 5 | | V-1 | Scgb2b24 | | | 13010 | 3 | 4 | 5 | | V-1 | Sgpl1 | 8879 | 4-May-15 |
| 12915 | 3 | 4 | 5 | | V-1 | Scimp | 388325 | 4-May-15 | 13011 | 3 | 4 | 5 | | V-1 | Sgpp2 | 130367 | 4-May-15 |
| 12916 | 3 | 4 | 5 | | V-1 | Scin | 85477 | 4-May-15 | 13012 | 3 | 4 | 5 | | V-1 | Sgsm1 | 129049 | 4-May-15 |
| 12917 | 3 | 4 | 5 | | V-1 | Scn11a | 11280 | 12-May-15 | 13013 | 3 | 4 | 5 | | V-1 | Sgsm2 | 9905 | 4-May-15 |
| 12918 | 3 | 4 | 5 | | V-1 | Scn1b | 6324 | 23-May-15 | 13014 | 3 | 4 | 5 | | V-1 | Sh2b3 | 10019 | 21-May-15 |
| 12919 | 3 | 4 | 5 | | V-1 | Scn2a1 | 6326 | 17-May-15 | 13015 | 3 | 4 | 5 | | V-1 | Sh2d4b | 387694 | 4-May-15 |
| 12920 | 3 | 4 | 5 | | V-1 | Scn5a | 6331 | 31-May-15 | 13016 | 3 | 4 | 5 | | V-1 | Sh2d7 | 646292 | 4-May-15 |
| 12921 | 3 | 4 | 5 | | V-1 | Scn7a | 6332 | 31-May-15 | 13017 | 3 | 4 | 5 | | V-1 | Sh3bgrl | 6451 | 4-May-15 |
| 12922 | 3 | 4 | 5 | | V-1 | Scn8a | 6334 | 21-May-15 | 13018 | 3 | 4 | 5 | | V-1 | Sh3bp1 | 23616 | 7-Jun-15 |
| 12923 | 3 | 4 | 5 | | V-1 | Scn9a | 6335 | 24-May-15 | 13019 | 3 | 4 | 5 | | V-1 | Sh3bp4 | 23677 | 4-May-15 |
| 12924 | 3 | 4 | 5 | | V-1 | Scnn1b | 6338 | 12-May-15 | 13020 | 3 | 4 | 5 | | V-1 | Sh3bp5l | 80851 | 4-May-15 |
| 12925 | 3 | 4 | 5 | | V-1 | Sco1 | 6341 | 12-May-15 | 13021 | 3 | 4 | 5 | | V-1 | Sh3d21 | 79729 | 4-May-15 |
| 12926 | 3 | 4 | 5 | | V-1 | Scoc | 60592 | 4-May-15 | 13022 | 3 | 4 | 5 | | V-1 | Sh3gl1 | 6455 | 14-May-15 |
| 12927 | 3 | 4 | 5 | | V-1 | Scp2 | 6342 | 7-Jun-15 | 13023 | 3 | 4 | 5 | | V-1 | Sh3glb1 | 51100 | 21-May-15 |
| 12928 | 3 | 4 | 5 | | V-1 | Scpep1os | | | 13024 | 3 | 4 | 5 | | V-1 | Sh3rf1 | 57630 | 23-May-15 |
| 12929 | 3 | 4 | 5 | | V-1 | Scrib | 23513 | 4-May-15 | 13025 | 3 | 4 | 5 | | V-1 | Sh3rf3 | 344558 | 4-May-15 |
| 12930 | 3 | 4 | 5 | | V-1 | Scrt1 | 83482 | 4-May-15 | 13026 | 3 | 4 | 5 | | V-1 | Sh3tc1 | 54436 | 4-May-15 |
| 12931 | 3 | 4 | 5 | | V-1 | Sctr | 6344 | 4-May-15 | 13027 | 3 | 4 | 5 | | V-1 | Shank3 | 85358 | 23-May-15 |
| 12932 | 3 | 4 | 5 | | V-1 | Scube1 | 80274 | 4-May-15 | 13028 | 3 | 4 | 5 | | V-1 | Sharpin | 81858 | 21-May-15 |
| 12933 | 3 | 4 | 5 | | V-1 | Scyl1 | 57410 | 7-Jun-15 | 13029 | 3 | 4 | 5 | | V-1 | Shbg | 6462 | 4-May-15 |
| 12934 | 3 | 4 | 5 | | V-1 | Sdc2 | 6383 | 31-May-15 | 13030 | 3 | 4 | 5 | | V-1 | Shc3 | 53358 | 12-May-15 |
| 12935 | 3 | 4 | 5 | | V-1 | Sdcbp | 6386 | 10-May-15 | 13031 | 3 | 4 | 5 | | V-1 | Shc4 | 399694 | 4-May-15 |
| 12936 | 3 | 4 | 5 | | V-1 | Sdccag3 | 10807 | 4-May-15 | 13032 | 3 | 4 | 5 | | V-1 | Shcbp1l | 81626 | 12-May-15 |
| 12937 | 3 | 4 | 5 | | V-1 | Sdf4 | 51150 | 4-May-15 | 13033 | 3 | 4 | 5 | | V-1 | Shfm1 | 7979 | 21-May-15 |
| 12938 | 3 | 4 | 5 | | V-1 | Sdr16c5 | 195814 | 4-May-15 | 13034 | 3 | 4 | 5 | | V-1 | Shisa5 | 51246 | 12-May-15 |
| 12939 | 3 | 4 | 5 | | V-1 | Sebox | 645832 | 12-May-15 | 13035 | 3 | 4 | 5 | | V-1 | Shisa6 | 388336 | 14-May-15 |
| 12940 | 3 | 4 | 5 | | V-1 | Sec13 | 6396 | 29-May-15 | 13036 | 3 | 4 | 5 | | V-1 | Shoc2 | 8036 | 3-Jun-15 |
| 12941 | 3 | 4 | 5 | | V-1 | Sec22a | 26984 | 4-May-15 | 13037 | 3 | 4 | 5 | | V-1 | Shroom4 | 57477 | 4-May-15 |
| 12942 | 3 | 4 | 5 | | V-1 | Sec24b | 10427 | 4-May-15 | 13038 | 3 | 4 | 5 | | V-1 | Siah1b | | |
| 12943 | 3 | 4 | 5 | | V-1 | Sec61a1 | 29927 | 12-May-15 | 13039 | 3 | 4 | 5 | | V-1 | Siah2 | 6478 | 24-May-15 |
| 12944 | 3 | 4 | 5 | | V-1 | Sec61a2 | 55176 | 4-May-15 | 13040 | 3 | 4 | 5 | | V-1 | Siah3 | 283514 | 28-May-15 |
| 12945 | 3 | 4 | 5 | | V-1 | Sec61g | 23480 | 4-May-15 | 13041 | 3 | 4 | 5 | | V-1 | Sidt2 | 51092 | 4-May-15 |
| 12946 | 3 | 4 | 5 | | V-1 | Sec62 | 7095 | 12-May-15 | 13042 | 3 | 4 | 5 | | V-1 | Siglec15 | 284266 | 4-May-15 |
| 12947 | 3 | 4 | 5 | | V-1 | Secisbp2l | 9728 | 4-May-15 | 13043 | 3 | 4 | 5 | | V-1 | Siglech | | |
| 12948 | 3 | 4 | 5 | | V-1 | Sehll | 81929 | 29-May-15 | 13044 | 3 | 4 | 5 | | V-1 | Sigmar1 | 10280 | 23-May-15 |
| 12949 | 3 | 4 | 5 | | V-1 | Selk | 58515 | 4-May-15 | 13045 | 3 | 4 | 5 | | V-1 | Sik2 | 23235 | 4-May-15 |
| 12950 | 3 | 4 | 5 | | V-1 | Selm | 140606 | 4-May-15 | 13046 | 3 | 4 | 5 | | V-1 | Sik3 | 23387 | 24-May-15 |
| 12951 | 3 | 4 | 5 | | V-1 | Selo | 83642 | 4-May-15 | 13047 | 3 | 4 | 5 | | V-1 | Sim2 | 6493 | 28-May-15 |
| 12952 | 3 | 4 | 5 | | V-1 | Selt | 51714 | 4-May-15 | 13048 | 3 | 4 | 5 | | V-1 | Simc1 | 375484 | 21-May-15 |
| 12953 | 3 | 4 | 5 | | V-1 | Sema3b | 7869 | 12-May-15 | 13049 | 3 | 4 | 5 | | V-1 | Sin3a | 25942 | 4-May-15 |
| 12954 | 3 | 4 | 5 | | V-1 | Sema3c | 10512 | 31-May-15 | 13050 | 3 | 4 | 5 | | V-1 | Sipa1 | 6494 | 12-May-15 |
| 12955 | 3 | 4 | 5 | | V-1 | Sema3e | 9723 | 23-May-15 | 13051 | 3 | 4 | 5 | | V-1 | Sirt1 | 23411 | 31-May-15 |
| 12956 | 3 | 4 | 5 | | V-1 | Sema3g | 56920 | 4-May-15 | 13052 | 3 | 4 | 5 | | V-1 | Sirt4 | 23409 | 31-May-15 |
| 12957 | 3 | 4 | 5 | | V-1 | Sema4a | 64218 | 23-May-15 | 13053 | 3 | 4 | 5 | | V-1 | Siva1 | 10572 | 31-May-15 |
| 12958 | 3 | 4 | 5 | | V-1 | Sema4c | 54910 | 4-May-15 | 13054 | 3 | 4 | 5 | | V-1 | Six1 | 6495 | 31-May-15 |
| 12959 | 3 | 4 | 5 | | V-1 | Sema4d | 10507 | 4-May-15 | 13055 | 3 | 4 | 5 | | V-1 | Six2 | 10736 | 4-May-15 |
| 12960 | 3 | 4 | 5 | | V-1 | Sema4f | 10505 | 4-May-15 | 13056 | 3 | 4 | 5 | | V-1 | Skap2 | 8935 | 4-May-15 |
| 12961 | 3 | 4 | 5 | | V-1 | Sema4g | 57715 | 4-May-15 | 13057 | 3 | 4 | 5 | | V-1 | Ski | 6497 | 23-May-15 |
| 12962 | 3 | 4 | 5 | | V-1 | Sema5b | 54437 | 4-May-15 | 13058 | 3 | 4 | 5 | | V-1 | Skint2 | | |
| 12963 | 3 | 4 | 5 | | V-1 | Sema6a | 57556 | 12-May-15 | 13059 | 3 | 4 | 5 | | V-1 | Skint5 | | |
| 12964 | 3 | 4 | 5 | | V-1 | Senp1 | 29843 | 4-May-15 | 13060 | 3 | 4 | 5 | | V-1 | Skint8 | | |
| 12965 | 3 | 4 | 5 | | V-1 | Sepp1 | 6414 | 3-May-15 | 13061 | 3 | 4 | 5 | | V-1 | Sla2 | 84174 | 4-May-15 |
| 12966 | 3 | 4 | 5 | | V-1 | Sepsecs | 51091 | 4-May-15 | 13062 | 3 | 4 | 5 | | V-1 | Slain1os | | |
| 12967 | 3 | 4 | 5 | | V-1 | Sept10 | 151011 | 4-May-15 | 13063 | 3 | 4 | 5 | | V-1 | Slc10a1 | 6554 | 17-May-15 |
| 12968 | 3 | 4 | 5 | | V-1 | Sept12 | 124404 | 12-May-15 | 13064 | 3 | 4 | 5 | | V-1 | Slc10a3 | 8273 | 4-May-15 |
| 12969 | 3 | 4 | 5 | | V-1 | Sept7 | 989 | 4-May-15 | 13065 | 3 | 4 | 5 | | V-1 | Slc10a4 | 201780 | 4-May-15 |
| 12970 | 3 | 4 | 5 | | V-1 | Sept9 | 10801 | 23-May-15 | 13066 | 3 | 4 | 5 | | V-1 | Slc10a7 | 84068 | 4-May-15 |
| 12971 | 3 | 4 | 5 | | V-1 | Sepw1 | 6415 | 12-May-15 | 13067 | 3 | 4 | 5 | | V-1 | Slc11a2 | 4891 | 12-May-15 |
| 12972 | 3 | 4 | 5 | | V-1 | Serbp1 | 26135 | 4-May-15 | 13068 | 3 | 4 | 5 | | V-1 | Slc12a1 | 6557 | 12-May-15 |
| 12973 | 3 | 4 | 5 | | V-1 | Serinc3 | 10955 | 12-May-15 | 13069 | 3 | 4 | 5 | | V-1 | Slc12a4 | 6560 | 4-May-15 |
| 12974 | 3 | 4 | 5 | | V-1 | Serinc4 | 619189 | 14-May-15 | 13070 | 3 | 4 | 5 | | V-1 | Slc12a7 | 10723 | 4-May-15 |
| 12975 | 3 | 4 | 5 | | V-1 | Serp2 | 387923 | 21-May-15 | 13071 | 3 | 4 | 5 | | V-1 | Slc15a1 | 6564 | 12-May-15 |
| 12976 | 3 | 4 | 5 | | V-1 | Serpina3b | | | 13072 | 3 | 4 | 5 | | V-1 | Slc15a4 | 121260 | 12-May-15 |
| 12977 | 3 | 4 | 5 | | V-1 | Serpinb10 | 5273 | 28-May-15 | 13073 | 3 | 4 | 5 | | V-1 | Slc16a12 | 387700 | 4-May-15 |
| 12978 | 3 | 4 | 5 | | V-1 | Serpinb13 | 5275 | 12-May-15 | 13074 | 3 | 4 | 5 | | V-1 | Slc16a4 | 9122 | 4-May-15 |
| 12979 | 3 | 4 | 5 | | V-1 | Serpinb1b | | | 13075 | 3 | 4 | 5 | | V-1 | Slc16a8 | 23539 | 4-May-15 |
| 12980 | 3 | 4 | 5 | | V-1 | Serpinb3b | | | 13076 | 3 | 4 | 5 | | V-1 | Slc17a1 | 6568 | 12-May-15 |
| 12981 | 3 | 4 | 5 | | V-1 | Serpinb3d | | | 13077 | 3 | 4 | 5 | | V-1 | Slc17a6 | 57084 | 12-May-15 |
| 12982 | 3 | 4 | 5 | | V-1 | Serpinb6c | | | 13078 | 3 | 4 | 5 | | V-1 | Slc18a1 | 6570 | 3-May-15 |
| 12983 | 3 | 4 | 5 | | V-1 | Serpinb6e | | | 13079 | 3 | 4 | 5 | | V-1 | Slc18a2 | 6571 | 4-May-15 |
| 12984 | 3 | 4 | 5 | | V-1 | Serpinb8 | 5271 | 4-May-15 | 13080 | 3 | 4 | 5 | | V-1 | Slc19a1 | 6573 | 12-May-15 |
| 12985 | 3 | 4 | 5 | | V-1 | Serpinb9 | 5272 | 4-May-15 | 13081 | 3 | 4 | 5 | | V-1 | Slc19a3 | 80704 | 4-May-15 |
| 12986 | 3 | 4 | 5 | | V-1 | Serpinb9c | | | 13082 | 3 | 4 | 5 | | V-1 | Slc1a2 | 6506 | 21-May-15 |
| 12987 | 3 | 4 | 5 | | V-1 | Serpine3 | 647174 | 4-May-15 | 13083 | 3 | 4 | 5 | | V-1 | Slc1a4 | 6509 | 28-May-15 |
| 12988 | 3 | 4 | 5 | | V-1 | Serpinh1 | 871 | 3-May-15 | 13084 | 3 | 4 | 5 | | V-1 | Slc1a6 | 6511 | 4-May-15 |
| 12989 | 3 | 4 | 5 | | V-1 | Sertad3 | 29946 | 4-May-15 | 13085 | 3 | 4 | 5 | | V-1 | Slc20a2 | 6575 | 23-May-15 |
| 12990 | 3 | 4 | 5 | | V-1 | Sertm1 | 400120 | 4-May-15 | 13086 | 3 | 4 | 5 | | V-1 | Slc22a18 | 5002 | 23-May-15 |
| 12991 | 3 | 4 | 5 | | V-1 | Sesn2 | 83667 | 4-May-15 | 13087 | 3 | 4 | 5 | | V-1 | Slc22a26 | | |
| 12992 | 3 | 4 | 5 | | V-1 | Sesn3 | 143686 | 4-May-15 | 13088 | 3 | 4 | 5 | | V-1 | Slc22a30 | | |
| 12993 | 3 | 4 | 5 | | V-1 | Set | 6418 | 3-May-15 | 13089 | 3 | 4 | 5 | | V-1 | Slc22a5 | 6584 | 23-May-15 |
| 12994 | 3 | 4 | 5 | | V-1 | Setd1a | 9739 | 24-May-15 | 13090 | 3 | 4 | 5 | | V-1 | Slc22a6 | 9356 | 4-May-15 |
| 12995 | 3 | 4 | 5 | | V-1 | Setd5 | 55209 | 4-May-15 | 13091 | 3 | 4 | 5 | | V-1 | Slc24a4 | 123041 | 4-May-15 |
| 12996 | 3 | 4 | 5 | | V-1 | Setmar | 6419 | 21-May-15 | 13092 | 3 | 4 | 5 | | V-1 | Slc25a1 | 6576 | 17-May-15 |
| 12997 | 3 | 4 | 5 | | V-1 | Setx | 23064 | 23-May-15 | 13093 | 3 | 4 | 5 | | V-1 | Slc25a10 | 1468 | 4-May-15 |
| 12998 | 3 | 4 | 5 | | V-1 | Sf3a1 | 10291 | 4-May-15 | 13094 | 3 | 4 | 5 | | V-1 | Slc25a11 | 8402 | 4-May-15 |
| 12999 | 3 | 4 | 5 | | V-1 | Sfpq | 6421 | 7-Jun-15 | 13095 | 3 | 4 | 5 | | V-1 | Slc25a16 | 8034 | 4-May-15 |
| 13000 | 3 | 4 | 5 | | V-1 | Sfswap | 6433 | 12-May-15 | 13096 | 3 | 4 | 5 | | V-1 | Slc25a22 | 79751 | 4-May-15 |
| 13001 | 3 | 4 | 5 | | V-1 | Sfxn1 | 94081 | 4-May-15 | 13097 | 3 | 4 | 5 | | V-1 | Slc25a23 | 79085 | 4-May-15 |
| 13002 | 3 | 4 | 5 | | V-1 | Sfxn4 | 119559 | 4-May-15 | 13098 | 3 | 4 | 5 | | V-1 | Slc25a26 | 115286 | 4-May-15 |
| 13003 | 3 | 4 | 5 | | V-1 | Sgcb | 6443 | 23-May-15 | 13099 | 3 | 4 | 5 | | V-1 | Slc25a28 | 81894 | 12-May-15 |
| 13004 | 3 | 4 | 5 | | V-1 | Sgce | 8910 | 23-May-15 | 13100 | 3 | 4 | 5 | | V-1 | Slc25a31 | 83447 | 4-May-15 |

Fig. 30 - 70

| | | | | | | | | | | | | | | | | | | |
|---|---|---|---|---|---|---|---|---|---|---|---|---|---|---|---|---|---|---|
| 13101 | 3 | 4 | 5 | | | V-1 | Slc25a35 | 399512 | 21-May-15 | 13197 | 3 | 4 | 5 | | | V-1 | Smim4 | 440957 | 4-May-15 |
| 13102 | 3 | 4 | 5 | | | V-1 | Slc25a36 | 55186 | 4-May-15 | 13198 | 3 | 4 | 5 | | | V-1 | Smim6 | 100130933 | 4-May-15 |
| 13103 | 3 | 4 | 5 | | | V-1 | Slc25a40 | 55972 | 4-May-15 | 13199 | 3 | 4 | 5 | | | V-1 | Smim7 | 79086 | 4-May-15 |
| 13104 | 3 | 4 | 5 | | | V-1 | Slc25a43 | 203427 | 4-May-15 | 13200 | 3 | 4 | 5 | | | V-1 | Smoc2 | 64094 | 4-May-15 |
| 13105 | 3 | 4 | 5 | | | V-1 | Slc25a46 | 91137 | 3-Jun-15 | 13201 | 3 | 4 | 5 | | | V-1 | Smok2a | | |
| 13106 | 3 | 4 | 5 | | | V-1 | Slc25a48 | 153328 | 4-May-15 | 13202 | 3 | 4 | 5 | | | V-1 | Smok2b | | |
| 13107 | 3 | 4 | 5 | | | V-1 | Slc25a5 | 292 | 6-May-15 | 13203 | 3 | 4 | 5 | | | V-1 | Smok3a | | |
| 13108 | 3 | 4 | 5 | | | V-1 | Slc25a53 | 401612 | 4-May-15 | 13204 | 3 | 4 | 5 | | | V-1 | Smpd1 | 6609 | 23-May-15 |
| 13109 | 3 | 4 | 5 | | | V-1 | Slc25a54 | | | 13205 | 3 | 4 | 5 | | | V-1 | Smpd4 | 55627 | 12-May-15 |
| 13110 | 3 | 4 | 5 | | | V-1 | Slc26a11 | 284129 | 4-May-15 | 13206 | 3 | 4 | 5 | | | V-1 | Smpd5 | 392275 | 4-May-15 |
| 13111 | 3 | 4 | 5 | | | V-1 | Slc26a2 | 1836 | 23-May-15 | 13207 | 3 | 4 | 5 | | | V-1 | Smr2 | | |
| 13112 | 3 | 4 | 5 | | | V-1 | Slc26a5 | 375611 | 4-May-15 | 13208 | 3 | 4 | 5 | | | V-1 | Smtn | 6525 | 4-May-15 |
| 13113 | 3 | 4 | 5 | | | V-1 | Slc27a3 | 11000 | 4-May-15 | 13209 | 3 | 4 | 5 | | | V-1 | Smu1 | 55234 | 4-May-15 |
| 13114 | 3 | 4 | 5 | | | V-1 | Slc27a4 | 10999 | 17-May-15 | 13210 | 3 | 4 | 5 | | | V-1 | Snai2 | 6591 | 1-Jun-15 |
| 13115 | 3 | 4 | 5 | | | V-1 | Slc28a3 | 64078 | 4-May-15 | 13211 | 3 | 4 | 5 | | | V-1 | Snap47 | 116841 | 21-May-15 |
| 13116 | 3 | 4 | 5 | | | V-1 | Slc29a2 | 3177 | 4-May-15 | 13212 | 3 | 4 | 5 | | | V-1 | Snapc1 | 6617 | 4-May-15 |
| 13117 | 3 | 4 | 5 | | | V-1 | Slc29a4 | 222962 | 4-May-15 | 13213 | 3 | 4 | 5 | | | V-1 | Sncaip | 9627 | 31-May-15 |
| 13118 | 3 | 4 | 5 | | | V-1 | Slc2a4rg-ps | | | 13214 | 3 | 4 | 5 | | | V-1 | Sncb | 6620 | 4-May-15 |
| 13119 | 3 | 4 | 5 | | | V-1 | Slc2a6 | 11182 | 4-May-15 | 13215 | 3 | 4 | 5 | | | V-1 | Snd1 | 27044 | 31-May-15 |
| 13120 | 3 | 4 | 5 | | | V-1 | Slc2a7 | 155184 | 4-May-15 | 13216 | 3 | 4 | 5 | | | V-1 | Snf8 | 11267 | 21-May-15 |
| 13121 | 3 | 4 | 5 | | | V-1 | Slc30a7 | 148867 | 4-May-15 | 13217 | 3 | 4 | 5 | | | V-1 | Snhg10 | 283596 | 12-May-15 |
| 13122 | 3 | 4 | 5 | | | V-1 | Slc31a1 | 1317 | 17-May-15 | 13218 | 3 | 4 | 5 | | | V-1 | Snhg18 | 100505806 | 4-May-15 |
| 13123 | 3 | 4 | 5 | | | V-1 | Slc32a1 | 140679 | 4-May-15 | 13219 | 3 | 4 | 5 | | | V-1 | Snhg7 | 84973 | 12-May-15 |
| 13124 | 3 | 4 | 5 | | | V-1 | Slc34a3 | 142680 | 12-May-15 | 13220 | 3 | 4 | 5 | | | V-1 | Snhg8 | 100093630 | 12-May-15 |
| 13125 | 3 | 4 | 5 | | | V-1 | Slc35c2 | 51006 | 4-May-15 | 13221 | 3 | 4 | 5 | | | V-1 | Snip1 | 79753 | 4-May-15 |
| 13126 | 3 | 4 | 5 | | | V-1 | Slc35d3 | 340146 | 4-May-15 | 13222 | 3 | 4 | 5 | | | V-1 | Snora81 | 677847 | 4-May-15 |
| 13127 | 3 | 4 | 5 | | | V-1 | Slc35e3 | 55508 | 4-May-15 | 13223 | 3 | 4 | 5 | | | V-1 | Snrk | 54861 | 4-May-15 |
| 13128 | 3 | 4 | 5 | | | V-1 | Slc35f1 | 222553 | 4-May-15 | 13224 | 3 | 4 | 5 | | | V-1 | Snrnp200 | 23020 | 23-May-15 |
| 13129 | 3 | 4 | 5 | | | V-1 | Slc35f6 | 54978 | 4-May-15 | 13225 | 3 | 4 | 5 | | | V-1 | Snrnp27 | 11017 | 4-May-15 |
| 13130 | 3 | 4 | 5 | | | V-1 | Slc35g2 | 80723 | 4-May-15 | 13226 | 3 | 4 | 5 | | | V-1 | Snrnp48 | 154007 | 4-May-15 |
| 13131 | 3 | 4 | 5 | | | V-1 | Slc35g3 | 146861 | 4-May-15 | 13227 | 3 | 4 | 5 | | | V-1 | Snrpd2 | 6633 | 4-May-15 |
| 13132 | 3 | 4 | 5 | | | V-1 | Slc36a3 | 285641 | 4-May-15 | 13228 | 3 | 4 | 5 | | | V-1 | Snrpd3 | 6634 | 4-May-15 |
| 13133 | 3 | 4 | 5 | | | V-1 | Slc37a3 | 84255 | 4-May-15 | 13229 | 3 | 4 | 5 | | | V-1 | Snrpf | 6636 | 28-May-15 |
| 13134 | 3 | 4 | 5 | | | V-1 | Slc38a10 | 124565 | 12-May-15 | 13230 | 3 | 4 | 5 | | | V-1 | Snrpg | 6637 | 4-May-15 |
| 13135 | 3 | 4 | 5 | | | V-1 | Slc38a6 | 145389 | 4-May-15 | 13231 | 3 | 4 | 5 | | | V-1 | Snrpn | 6638 | 23-May-15 |
| 13136 | 3 | 4 | 5 | | | V-1 | Slc38a7 | 55238 | 12-May-15 | 13232 | 3 | 4 | 5 | | | V-1 | Sntg1 | 54212 | 28-May-15 |
| 13137 | 3 | 4 | 5 | | | V-1 | Slc39a11 | 201266 | 4-May-15 | 13233 | 3 | 4 | 5 | | | V-1 | Snupn | 10073 | 4-May-15 |
| 13138 | 3 | 4 | 5 | | | V-1 | Slc39a12 | 221074 | 4-May-15 | 13234 | 3 | 4 | 5 | | | V-1 | Snx11 | 29916 | 21-May-15 |
| 13139 | 3 | 4 | 5 | | | V-1 | Slc39a2 | 29986 | 4-May-15 | 13235 | 3 | 4 | 5 | | | V-1 | Snx16 | 64089 | 4-May-15 |
| 13140 | 3 | 4 | 5 | | | V-1 | Slc39a7 | 7922 | 4-May-15 | 13236 | 3 | 4 | 5 | | | V-1 | Snx19 | 399979 | 12-May-15 |
| 13141 | 3 | 4 | 5 | | | V-1 | Slc39a9 | 55334 | 12-May-15 | 13237 | 3 | 4 | 5 | | | V-1 | Snx21 | 90203 | 4-May-15 |
| 13142 | 3 | 4 | 5 | | | V-1 | Slc3a2 | 6520 | 12-May-15 | 13238 | 3 | 4 | 5 | | | V-1 | Snx24 | 28966 | 4-May-15 |
| 13143 | 3 | 4 | 5 | | | V-1 | Slc40a1 | 30061 | 28-May-15 | 13239 | 3 | 4 | 5 | | | V-1 | Snx25 | 83891 | 4-May-15 |
| 13144 | 3 | 4 | 5 | | | V-1 | Slc43a2 | 124935 | 21-May-15 | 13240 | 3 | 4 | 5 | | | V-1 | Snx4 | 8723 | 4-May-15 |
| 13145 | 3 | 4 | 5 | | | V-1 | Slc44a1 | 23446 | 4-May-15 | 13241 | 3 | 4 | 5 | | | V-1 | Snx6 | 58533 | 4-May-15 |
| 13146 | 3 | 4 | 5 | | | V-1 | Slc44a3 | 126969 | 4-May-15 | 13242 | 3 | 4 | 5 | | | V-1 | Snx7 | 51375 | 4-May-15 |
| 13147 | 3 | 4 | 5 | | | V-1 | Slc44a4 | 80736 | 4-May-15 | 13243 | 3 | 4 | 5 | | | V-1 | Snx8 | 29886 | 4-May-15 |
| 13148 | 3 | 4 | 5 | | | V-1 | Slc45a4 | 57210 | 4-May-15 | 13244 | 3 | 4 | 5 | | | V-1 | Snx9 | 51429 | 4-May-15 |
| 13149 | 3 | 4 | 5 | | | V-1 | Slc46a3 | 283537 | 12-May-15 | 13245 | 3 | 4 | 5 | | | V-1 | Sobp | 55084 | 4-May-15 |
| 13150 | 3 | 4 | 5 | | | V-1 | Slc47a2 | 146802 | 4-May-15 | 13246 | 3 | 4 | 5 | | | V-1 | Socs4 | 122809 | 7-Jun-15 |
| 13151 | 3 | 4 | 5 | | | V-1 | Slc4a10 | 57282 | 4-May-15 | 13247 | 3 | 4 | 5 | | | V-1 | Soga1 | 140710 | 12-May-15 |
| 13152 | 3 | 4 | 5 | | | V-1 | Slc4a1ap | 22950 | 4-May-15 | 13248 | 3 | 4 | 5 | | | V-1 | Soga3 | 387104 | 4-May-15 |
| 13153 | 3 | 4 | 5 | | | V-1 | Slc4a5 | 57835 | 4-May-15 | 13249 | 3 | 4 | 5 | | | V-1 | Sorbs2 | 8470 | 20-May-15 |
| 13154 | 3 | 4 | 5 | | | V-1 | Slc52a2 | 79581 | 4-May-15 | 13250 | 3 | 4 | 5 | | | V-1 | Sorbs2os | | |
| 13155 | 3 | 4 | 5 | | | V-1 | Slc5a1 | 6523 | 12-May-15 | 13251 | 3 | 4 | 5 | | | V-1 | Sorbs3 | 10174 | 4-May-15 |
| 13156 | 3 | 4 | 5 | | | V-1 | Slc5a2 | 6524 | 20-May-15 | 13252 | 3 | 4 | 5 | | | V-1 | Sorcs1 | 114815 | 4-May-15 |
| 13157 | 3 | 4 | 5 | | | V-1 | Slc5a4a | | | 13253 | 3 | 4 | 5 | | | V-1 | Sorcs3 | 22986 | 4-May-15 |
| 13158 | 3 | 4 | 5 | | | V-1 | Slc5a7 | 60482 | 12-May-15 | 13254 | 3 | 4 | 5 | | | V-1 | Sort1 | 6272 | 31-May-15 |
| 13159 | 3 | 4 | 5 | | | V-1 | Slc6a1 | 6529 | 28-May-15 | 13255 | 3 | 4 | 5 | | | V-1 | Sostdc1 | 25928 | 4-May-15 |
| 13160 | 3 | 4 | 5 | | | V-1 | Slc6a14 | 11254 | 4-May-15 | 13256 | 3 | 4 | 5 | | | V-1 | Sowahb | 345079 | 4-May-15 |
| 13161 | 3 | 4 | 5 | | | V-1 | Slc6a18 | 348932 | 4-May-15 | 13257 | 3 | 4 | 5 | | | V-1 | Sowahd | 347454 | 4-May-15 |
| 13162 | 3 | 4 | 5 | | | V-1 | Slc6a20b | | | 13258 | 3 | 4 | 5 | | | V-1 | Sox11 | 6664 | 28-May-15 |
| 13163 | 3 | 4 | 5 | | | V-1 | Slc6a3 | 6531 | 24-May-15 | 13259 | 3 | 4 | 5 | | | V-1 | Sox14 | 8403 | 4-May-15 |
| 13164 | 3 | 4 | 5 | | | V-1 | Slc6a5 | 9152 | 7-Jun-15 | 13260 | 3 | 4 | 5 | | | V-1 | Sox21 | 11166 | 28-May-15 |
| 13165 | 3 | 4 | 5 | | | V-1 | Slc6a7 | 6534 | 4-May-15 | 13261 | 3 | 4 | 5 | | | V-1 | Sox5 | 6660 | 12-May-15 |
| 13166 | 3 | 4 | 5 | | | V-1 | Slc7a12 | | | 13262 | 3 | 4 | 5 | | | V-1 | Sox7 | 83595 | 4-May-15 |
| 13167 | 3 | 4 | 5 | | | V-1 | Slc7a3 | 84889 | 4-May-15 | 13263 | 3 | 4 | 5 | | | V-1 | Sox8 | 30812 | 4-May-15 |
| 13168 | 3 | 4 | 5 | | | V-1 | Slc7a6 | 9057 | 4-May-15 | 13264 | 3 | 4 | 5 | | | V-1 | Sp1 | 6667 | 13-Jun-15 |
| 13169 | 3 | 4 | 5 | | | V-1 | Slc7a6os | 84138 | 4-May-15 | 13265 | 3 | 4 | 5 | | | V-1 | Sp110 | 3431 | 7-Jun-15 |
| 13170 | 3 | 4 | 5 | | | V-1 | Slc8a2 | 6543 | 4-May-15 | 13266 | 3 | 4 | 5 | | | V-1 | Sp140 | 11262 | 4-May-15 |
| 13171 | 3 | 4 | 5 | | | V-1 | Slc9a1 | 6548 | 4-May-15 | 13267 | 3 | 4 | 5 | | | V-1 | Sp3 | 6670 | 16-Jun-15 |
| 13172 | 3 | 4 | 5 | | | V-1 | Slc9a4 | 389015 | 4-May-15 | 13268 | 3 | 4 | 5 | | | V-1 | Sp7 | 121340 | 17-May-15 |
| 13173 | 3 | 4 | 5 | | | V-1 | Slc9a8 | 23315 | 4-May-15 | 13269 | 3 | 4 | 5 | | | V-1 | Spaca7 | 122258 | 4-May-15 |
| 13174 | 3 | 4 | 5 | | | V-1 | Slc9b1 | 150159 | 31-May-15 | 13270 | 3 | 4 | 5 | | | V-1 | Sparcl1 | 8404 | 12-May-15 |
| 13175 | 3 | 4 | 5 | | | V-1 | Slco1a6 | | | 13271 | 3 | 4 | 5 | | | V-1 | Spast | 6683 | 31-May-15 |
| 13176 | 3 | 4 | 5 | | | V-1 | Slco2b1 | 11309 | 12-May-15 | 13272 | 3 | 4 | 5 | | | V-1 | Spata13 | 221178 | 4-May-15 |
| 13177 | 3 | 4 | 5 | | | V-1 | Slfn10-ps | | | 13273 | 3 | 4 | 5 | | | V-1 | Spata19 | 219938 | 4-May-15 |
| 13178 | 3 | 4 | 5 | | | V-1 | Slfn3 | 55106 | 4-May-15 | 13274 | 3 | 4 | 5 | | | V-1 | Spata24 | 202051 | 4-May-15 |
| 13179 | 3 | 4 | 5 | | | V-1 | Slfnl1 | 200172 | 4-May-15 | 13275 | 3 | 4 | 5 | | | V-1 | Spata25 | 128497 | 4-May-15 |
| 13180 | 3 | 4 | 5 | | | V-1 | Slitrk1 | 114798 | 23-May-15 | 13276 | 3 | 4 | 5 | | | V-1 | Spata31 | | |
| 13181 | 3 | 4 | 5 | | | V-1 | Slitrk5 | 26050 | 4-May-15 | 13277 | 3 | 4 | 5 | | | V-1 | Spata5l1 | 79029 | 4-May-15 |
| 13182 | 3 | 4 | 5 | | | V-1 | Slmo2 | 51012 | 4-May-15 | 13278 | 3 | 4 | 5 | | | V-1 | Spata6 | 54558 | 4-May-15 |
| 13183 | 3 | 4 | 5 | | | V-1 | Sltm | 79811 | 4-May-15 | 13279 | 3 | 4 | 5 | | | V-1 | Spata7 | 55812 | 23-May-15 |
| 13184 | 3 | 4 | 5 | | | V-1 | Smad2 | 4087 | 24-May-15 | 13280 | 3 | 4 | 5 | | | V-1 | Spats2l | 26010 | 4-May-15 |
| 13185 | 3 | 4 | 5 | | | V-1 | Smap1 | 60682 | 7-Jun-15 | 13281 | 3 | 4 | 5 | | | V-1 | Spcs1 | 28972 | 4-May-15 |
| 13186 | 3 | 4 | 5 | | | V-1 | Smarca1 | 6594 | 2-Jun-15 | 13282 | 3 | 4 | 5 | | | V-1 | Spcs3 | 60559 | 4-May-15 |
| 13187 | 3 | 4 | 5 | | | V-1 | Smarca5 | 8467 | 4-May-15 | 13283 | 3 | 4 | 5 | | | V-1 | Spdya | 245711 | 4-May-15 |
| 13188 | 3 | 4 | 5 | | | V-1 | Smarcc2 | 6601 | 4-May-15 | 13284 | 3 | 4 | 5 | | | V-1 | Specc1l | 23384 | 28-May-15 |
| 13189 | 3 | 4 | 5 | | | V-1 | Smarcd2 | 6603 | 4-May-15 | 13285 | 3 | 4 | 5 | | | V-1 | Spef2 | 79925 | 4-May-15 |
| 13190 | 3 | 4 | 5 | | | V-1 | Smarce1 | 6605 | 12-May-15 | 13286 | 3 | 4 | 5 | | | V-1 | Spg21 | 51324 | 4-May-15 |
| 13191 | 3 | 4 | 5 | | | V-1 | Smc2os | | | 13287 | 3 | 4 | 5 | | | V-1 | Sphk2 | 56848 | 4-May-15 |
| 13192 | 3 | 4 | 5 | | | V-1 | Smc3 | 9126 | 23-May-15 | 13288 | 3 | 4 | 5 | | | V-1 | Spic | 121599 | 28-May-15 |
| 13193 | 3 | 4 | 5 | | | V-1 | Smc5 | 23137 | 4-May-15 | 13289 | 3 | 4 | 5 | | | V-1 | Spin1 | 10927 | 7-Jun-15 |
| 13194 | 3 | 4 | 5 | | | V-1 | Smcr8 | 140775 | 4-May-15 | 13290 | 3 | 4 | 5 | | | V-1 | Spink13 | 153218 | 4-May-15 |
| 13195 | 3 | 4 | 5 | | | V-1 | Smim11 | 54065 | 4-May-15 | | | | | | | | | | |
| 13196 | 3 | 4 | 5 | | | V-1 | Smim23 | 644994 | 21-May-15 | | | | | | | | | | |

Fig. 30 - 71

| | | | | | | | | | | | | | | | | | |
|---|---|---|---|---|---|---|---|---|---|---|---|---|---|---|---|---|---|
| 13291 | 3 | 4 | 5 | | | V-1 | Spink14 | 408187 | 21-May-15 | 13387 | 3 | 4 | 5 | | | V-1 | Stk33 | 66975 | 12-May-15 |
| 13292 | 3 | 4 | 5 | | | V-1 | Spink4 | 27290 | 4-May-15 | 13388 | 3 | 4 | 5 | | | V-1 | Stk39 | 27347 | 4-May-15 |
| 13293 | 3 | 4 | 5 | | | V-1 | Spink6 | 404203 | 4-May-15 | 13389 | 3 | 4 | 5 | | | V-1 | Stmn1-rs1 | | |
| 13294 | 3 | 4 | 5 | | | V-1 | Spink7 | 84651 | 12-May-15 | 13390 | 3 | 4 | 5 | | | V-1 | Stmn3 | 50861 | 12-May-15 |
| 13295 | 3 | 4 | 5 | | | V-1 | Spint3 | 10816 | 7-Jun-15 | 13391 | 3 | 4 | 5 | | | V-1 | Stoml1 | 9399 | 12-May-15 |
| 13296 | 3 | 4 | 5 | | | V-1 | Spire2 | 84501 | 24-May-15 | 13392 | 3 | 4 | 5 | | | V-1 | Ston2 | 85439 | 12-May-15 |
| 13297 | 3 | 4 | 5 | | | V-1 | Spn-ps | | | 13393 | 3 | 4 | 5 | | | V-1 | Stradb | 55437 | 4-May-15 |
| 13298 | 3 | 4 | 5 | | | V-1 | Spns3 | 201305 | 4-May-15 | 13394 | 3 | 4 | 5 | | | V-1 | Strap | 11171 | 7-Jun-15 |
| 13299 | 3 | 4 | 5 | | | V-1 | Spo11 | 23626 | 31-May-15 | 13395 | 3 | 4 | 5 | | | V-1 | Strc | 161497 | 23-May-15 |
| 13300 | 3 | 4 | 5 | | | V-1 | Spock2 | 9806 | 12-May-15 | 13396 | 3 | 4 | 5 | | | V-1 | Strn | 6801 | 4-May-15 |
| 13301 | 3 | 4 | 5 | | | V-1 | Spock3 | 50859 | 12-May-15 | 13397 | 3 | 4 | 5 | | | V-1 | Stt3b | 201595 | 4-May-15 |
| 13302 | 3 | 4 | 5 | | | V-1 | Spon1 | 10418 | 4-May-15 | 13398 | 3 | 4 | 5 | | | V-1 | Stub1 | 10273 | 12-May-15 |
| 13303 | 3 | 4 | 5 | | | V-1 | Spop | 8405 | 17-May-15 | 13399 | 3 | 4 | 5 | | | V-1 | Stx12 | 23673 | 4-May-15 |
| 13304 | 3 | 4 | 5 | | | V-1 | Spopl | 339745 | 4-May-15 | 13400 | 3 | 4 | 5 | | | V-1 | Stx1b | 112755 | 12-May-15 |
| 13305 | 3 | 4 | 5 | | | V-1 | Spp2 | 6694 | 4-May-15 | 13401 | 3 | 4 | 5 | | | V-1 | Stx3 | 6809 | 3-May-15 |
| 13306 | 3 | 4 | 5 | | | V-1 | Sppl2c | 162540 | 12-May-15 | 13402 | 3 | 4 | 5 | | | V-1 | Stxbp2 | 6813 | 22-May-15 |
| 13307 | 3 | 4 | 5 | | | V-1 | Spred2 | 200734 | 2-Jun-15 | 13403 | 3 | 4 | 5 | | | V-1 | Stxbp3a | | |
| 13308 | 3 | 4 | 5 | | | V-1 | Sprn | 503542 | 4-May-15 | 13404 | 3 | 4 | 5 | | | V-1 | Stxbp5 | 134957 | 4-May-15 |
| 13309 | 3 | 4 | 5 | | | V-1 | Sprr2d | 6703 | 4-May-15 | 13405 | 3 | 4 | 5 | | | V-1 | Suco | 51430 | 4-May-15 |
| 13310 | 3 | 4 | 5 | | | V-1 | Sprr2g | 6706 | 4-May-15 | 13406 | 3 | 4 | 5 | | | V-1 | Suds3 | 64426 | 4-May-15 |
| 13311 | 3 | 4 | 5 | | | V-1 | Sprtn | 83932 | 12-May-15 | 13407 | 3 | 4 | 5 | | | V-1 | Sulf2 | 55959 | 4-May-15 |
| 13312 | 3 | 4 | 5 | | | V-1 | Spry1 | 10252 | 4-May-15 | 13408 | 3 | 4 | 5 | | | V-1 | Sult1a1 | 6817 | 31-May-15 |
| 13313 | 3 | 4 | 5 | | | V-1 | Spry2 | 10253 | 17-May-15 | 13409 | 3 | 4 | 5 | | | V-1 | Sult1b1 | 27284 | 4-May-15 |
| 13314 | 3 | 4 | 5 | | | V-1 | Spryd4 | 283377 | 4-May-15 | 13410 | 3 | 4 | 5 | | | V-1 | Sult2a1 | 6822 | 7-Jun-15 |
| 13315 | 3 | 4 | 5 | | | V-1 | Spsb2 | 84727 | 4-May-15 | 13411 | 3 | 4 | 5 | | | V-1 | Sult3a1 | | |
| 13316 | 3 | 4 | 5 | | | V-1 | Spsb3 | 90864 | 4-May-15 | 13412 | 3 | 4 | 5 | | | V-1 | Sult6b1 | 391365 | 4-May-15 |
| 13317 | 3 | 4 | 5 | | | V-1 | Spt1 | 10558 | 23-May-15 | 13413 | 3 | 4 | 5 | | | V-1 | Supt16 | | |
| 13318 | 3 | 4 | 5 | | | V-1 | Sptan1 | 6709 | 4-May-15 | 13414 | 3 | 4 | 5 | | | V-1 | Susd5 | 26032 | 4-May-15 |
| 13319 | 3 | 4 | 5 | | | V-1 | Sptbn1 | 6711 | 4-May-15 | 13415 | 3 | 4 | 5 | | | V-1 | Suv420h1 | 51111 | 12-May-15 |
| 13320 | 3 | 4 | 5 | | | V-1 | Sptbn4 | 57731 | 4-May-15 | 13416 | 3 | 4 | 5 | | | V-1 | Suz12 | 23512 | 4-May-15 |
| 13321 | 3 | 4 | 5 | | | V-1 | Sptlc3 | 55304 | 4-May-15 | 13417 | 3 | 4 | 5 | | | V-1 | Sv2a | 9900 | 12-May-15 |
| 13322 | 3 | 4 | 5 | | | V-1 | Sptv2d1 | 144108 | 4-May-15 | 13418 | 3 | 4 | 5 | | | V-1 | Svil | 6840 | 12-May-15 |
| 13323 | 3 | 4 | 5 | | | V-1 | Spz1 | 84654 | 4-May-15 | 13419 | 3 | 4 | 5 | | | V-1 | Svop | 55530 | 4-May-15 |
| 13324 | 3 | 4 | 5 | | | V-1 | Sqrdl | 58472 | 4-May-15 | 13420 | 3 | 4 | 5 | | | V-1 | Swap70 | 23075 | 4-May-15 |
| 13325 | 3 | 4 | 5 | | | V-1 | Sqstm1 | 8878 | 24-May-15 | 13421 | 3 | 4 | 5 | | | V-1 | Swi5 | 375757 | 4-May-15 |
| 13326 | 3 | 4 | 5 | | | V-1 | Srcin1 | 80725 | 4-May-15 | 13422 | 3 | 4 | 5 | | | V-1 | Syce1l | 100130958 | 4-May-15 |
| 13327 | 3 | 4 | 5 | | | V-1 | Srd5a3 | 79644 | 23-May-15 | 13423 | 3 | 4 | 5 | | | V-1 | Syce3 | 644186 | 4-May-15 |
| 13328 | 3 | 4 | 5 | | | V-1 | Srebf2 | 6721 | 17-May-15 | 13424 | 3 | 4 | 5 | | | V-1 | Synpl | 6847 | 4-May-15 |
| 13329 | 3 | 4 | 5 | | | V-1 | Srek1 | 140890 | 3-Jun-15 | 13425 | 3 | 4 | 5 | | | V-1 | Sympk | 8189 | 4-May-15 |
| 13330 | 3 | 4 | 5 | | | V-1 | Srgap2 | 23380 | 7-Jun-15 | 13426 | 3 | 4 | 5 | | | V-1 | Syn3 | 8224 | 4-May-15 |
| 13331 | 3 | 4 | 5 | | | V-1 | Sri | 6717 | 31-May-15 | 13427 | 3 | 4 | 5 | | | V-1 | Syna | | |
| 13332 | 3 | 4 | 5 | | | V-1 | Srms | 6725 | 4-May-15 | 13428 | 3 | 4 | 5 | | | V-1 | Syne2 | 23224 | 4-May-15 |
| 13333 | 3 | 4 | 5 | | | V-1 | Srpk1 | 6732 | 17-May-15 | 13429 | 3 | 4 | 5 | | | V-1 | Syngap1 | 8831 | 3-Jun-15 |
| 13334 | 3 | 4 | 5 | | | V-1 | Srpr | 6734 | 4-May-15 | 13430 | 3 | 4 | 5 | | | V-1 | Syngr2 | 9144 | 4-May-15 |
| 13335 | 3 | 4 | 5 | | | V-1 | Srr | 63826 | 4-May-15 | 13431 | 3 | 4 | 5 | | | V-1 | Synj2bp | 55333 | 4-May-15 |
| 13336 | 3 | 4 | 5 | | | V-1 | Srrm4os | | | 13432 | 3 | 4 | 5 | | | V-1 | Synpo2 | 171024 | 4-May-15 |
| 13337 | 3 | 4 | 5 | | | V-1 | Srsf11 | 9295 | 4-May-15 | 13433 | 3 | 4 | 5 | | | V-1 | Synrg | 11276 | 4-May-15 |
| 13338 | 3 | 4 | 5 | | | V-1 | Srsf4 | 6429 | 4-May-15 | 13434 | 3 | 4 | 5 | | | V-1 | Syt10 | 341359 | 4-May-15 |
| 13339 | 3 | 4 | 5 | | | V-1 | Srsf9 | 8683 | 31-May-15 | 13435 | 3 | 4 | 5 | | | V-1 | Syt13 | 57586 | 4-May-15 |
| 13340 | 3 | 4 | 5 | | | V-1 | Srv | 6736 | 28-May-15 | 13436 | 3 | 4 | 5 | | | V-1 | Syt14 | 255928 | 12-May-15 |
| 13341 | 3 | 4 | 5 | | | V-1 | Ssb | 6741 | 21-May-15 | 13437 | 3 | 4 | 5 | | | V-1 | Syt16 | 83851 | 21-May-15 |
| 13342 | 3 | 4 | 5 | | | V-1 | Ssbp4 | 170463 | 12-May-15 | 13438 | 3 | 4 | 5 | | | V-1 | Syt3 | 84258 | 4-May-15 |
| 13343 | 3 | 4 | 5 | | | V-1 | Ssfa2 | 6744 | 4-May-15 | 13439 | 3 | 4 | 5 | | | V-1 | Syt7 | 9066 | 4-May-15 |
| 13344 | 3 | 4 | 5 | | | V-1 | Ssh2 | 85464 | 12-May-15 | 13440 | 3 | 4 | 5 | | | V-1 | Sytl2 | 54843 | 12-May-15 |
| 13345 | 3 | 4 | 5 | | | V-1 | Ssmem1 | 136263 | 4-May-15 | 13441 | 3 | 4 | 5 | | | V-1 | Sytl3 | 94120 | 4-May-15 |
| 13346 | 3 | 4 | 5 | | | V-1 | Sspo | 23145 | 4-May-15 | 13442 | 3 | 4 | 5 | | | V-1 | Sytl5 | 94122 | 21-May-15 |
| 13347 | 3 | 4 | 5 | | | V-1 | Ssrp1 | 6749 | 24-May-15 | 13443 | 3 | 4 | 5 | | | V-1 | Szrd1 | 26099 | 4-May-15 |
| 13348 | 3 | 4 | 5 | | | V-1 | Sstr1 | 6751 | 4-May-15 | 13444 | 3 | 4 | 5 | | | V-1 | Tab3 | 257397 | 4-May-15 |
| 13349 | 3 | 4 | 5 | | | V-1 | Sstr3 | 6753 | 24-May-15 | 13445 | 3 | 4 | 5 | | | V-1 | Tac1 | 6863 | 4-May-15 |
| 13350 | 3 | 4 | 5 | | | V-1 | Sstr5 | 6755 | 12-May-15 | 13446 | 3 | 4 | 5 | | | V-1 | Tac4 | 255061 | 7-Jun-15 |
| 13351 | 3 | 4 | 5 | | | V-1 | Ssu72 | 29101 | 4-May-15 | 13447 | 3 | 4 | 5 | | | V-1 | Taco1 | 51204 | 4-May-15 |
| 13352 | 3 | 4 | 5 | | | V-1 | Ssx9 | 280660 | 4-May-15 | 13448 | 3 | 4 | 5 | | | V-1 | Tacr2 | 6865 | 12-May-15 |
| 13353 | 3 | 4 | 5 | | | V-1 | St18 | 9705 | 12-May-15 | 13449 | 3 | 4 | 5 | | | V-1 | Tada1 | 117143 | 7-Jun-15 |
| 13354 | 3 | 4 | 5 | | | V-1 | St3gal2 | 6483 | 12-May-15 | 13450 | 3 | 4 | 5 | | | V-1 | Taf2 | 6873 | 12-May-15 |
| 13355 | 3 | 4 | 5 | | | V-1 | St3gal3 | 6487 | 4-May-15 | 13451 | 3 | 4 | 5 | | | V-1 | Taf7l | 54457 | 12-May-15 |
| 13356 | 3 | 4 | 5 | | | V-1 | St3gal6 | 10402 | 4-May-15 | 13452 | 3 | 4 | 5 | | | V-1 | Taf9b | 51616 | 4-May-15 |
| 13357 | 3 | 4 | 5 | | | V-1 | St6gal2 | 84620 | 24-May-15 | 13453 | 3 | 4 | 5 | | | V-1 | Tagln3 | 29114 | 4-May-15 |
| 13358 | 3 | 4 | 5 | | | V-1 | St6galnac3 | 256435 | 4-May-15 | 13454 | 3 | 4 | 5 | | | V-1 | Tal2 | 6887 | 28-May-15 |
| 13359 | 3 | 4 | 5 | | | V-1 | St6galnac4 | 27090 | 4-May-15 | 13455 | 3 | 4 | 5 | | | V-1 | Tango2 | 128989 | 4-May-15 |
| 13360 | 3 | 4 | 5 | | | V-1 | St6galnac5 | 81849 | 4-May-15 | 13456 | 3 | 4 | 5 | | | V-1 | Tango6 | 79613 | 12-May-15 |
| 13361 | 3 | 4 | 5 | | | V-1 | St6galnac6 | 30815 | 4-May-15 | 13457 | 3 | 4 | 5 | | | V-1 | Tarbp2 | 6895 | 12-May-15 |
| 13362 | 3 | 4 | 5 | | | V-1 | St7 | 7982 | 7-Jun-15 | 13458 | 3 | 4 | 5 | | | V-1 | Tars | 6897 | 4-May-15 |
| 13363 | 3 | 4 | 5 | | | V-1 | St7l | 54879 | 21-May-15 | 13459 | 3 | 4 | 5 | | | V-1 | Tars2 | 80222 | 4-May-15 |
| 13364 | 3 | 4 | 5 | | | V-1 | Stab2 | 55576 | 12-May-15 | 13460 | 3 | 4 | 5 | | | V-1 | Tas1r1 | 80835 | 4-May-15 |
| 13365 | 3 | 4 | 5 | | | V-1 | Stac3 | 246329 | 4-May-15 | 13461 | 3 | 4 | 5 | | | V-1 | Tatdn1 | 83940 | 4-May-15 |
| 13366 | 3 | 4 | 5 | | | V-1 | Stamos | | | 13462 | 3 | 4 | 5 | | | V-1 | Tatdn2 | 9797 | 12-May-15 |
| 13367 | 3 | 4 | 5 | | | V-1 | Stap2 | 55620 | 4-May-15 | 13463 | 3 | 4 | 5 | | | V-1 | Tbc1d10a | 83874 | 4-May-15 |
| 13368 | 3 | 4 | 5 | | | V-1 | Star | 6770 | 7-Jun-15 | 13464 | 3 | 4 | 5 | | | V-1 | Tbc1d12 | 23232 | 4-May-15 |
| 13369 | 3 | 4 | 5 | | | V-1 | Stard10 | 10809 | 12-May-15 | 13465 | 3 | 4 | 5 | | | V-1 | Tbc1d17 | 79735 | 21-May-15 |
| 13370 | 3 | 4 | 5 | | | V-1 | Stard13 | 90627 | 17-May-15 | 13466 | 3 | 4 | 5 | | | V-1 | Tbc1d20 | 128637 | 4-May-15 |
| 13371 | 3 | 4 | 5 | | | V-1 | Stard3 | 10948 | 4-May-15 | 13467 | 3 | 4 | 5 | | | V-1 | Tbc1d23 | 55773 | 4-May-15 |
| 13372 | 3 | 4 | 5 | | | V-1 | Stard4 | 134429 | 12-May-15 | 13468 | 3 | 4 | 5 | | | V-1 | Tbc1d25 | 4943 | 21-May-15 |
| 13373 | 3 | 4 | 5 | | | V-1 | Stat1 | 6772 | 31-May-15 | 13469 | 3 | 4 | 5 | | | V-1 | Tbc1d32 | 221322 | 4-May-15 |
| 13374 | 3 | 4 | 5 | | | V-1 | Stat2 | 6773 | 28-May-15 | 13470 | 3 | 4 | 5 | | | V-1 | Tbc1d8b | 54885 | 12-May-15 |
| 13375 | 3 | 4 | 5 | | | V-1 | Stat3 | 6774 | 31-May-15 | 13471 | 3 | 4 | 5 | | | V-1 | Tbc1d9b | 23061 | 12-May-15 |
| 13376 | 3 | 4 | 5 | | | V-1 | Stat5a | 6776 | 31-May-15 | 13472 | 3 | 4 | 5 | | | V-1 | Tbcc | 6903 | 4-May-15 |
| 13377 | 3 | 4 | 5 | | | V-1 | Stat5b | 6777 | 24-May-15 | 13473 | 3 | 4 | 5 | | | V-1 | Tbcd | 6904 | 4-May-15 |
| 13378 | 3 | 4 | 5 | | | V-1 | Stat6 | 6778 | 24-May-15 | 13474 | 3 | 4 | 5 | | | V-1 | Tbcel | 219899 | 4-May-15 |
| 13379 | 3 | 4 | 5 | | | V-1 | Stc2 | 8614 | 4-May-15 | 13475 | 3 | 4 | 5 | | | V-1 | Tbck | 93627 | 4-May-15 |
| 13380 | 3 | 4 | 5 | | | V-1 | Steap2 | 261729 | 4-May-15 | 13476 | 3 | 4 | 5 | | | V-1 | Tbkbp1 | 9755 | 4-May-15 |
| 13381 | 3 | 4 | 5 | | | V-1 | Stfa3 | | | 13477 | 3 | 4 | 5 | | | V-1 | Tbx2 | 6909 | 12-May-15 |
| 13382 | 3 | 4 | 5 | | | V-1 | Stim1 | 6786 | 31-May-15 | 13478 | 3 | 4 | 5 | | | V-1 | Tbx20 | 57057 | 12-May-15 |
| 13383 | 3 | 4 | 5 | | | V-1 | Stk10 | 6793 | 4-May-15 | 13479 | 3 | 4 | 5 | | | V-1 | Tbx4 | 9496 | 4-May-15 |
| 13384 | 3 | 4 | 5 | | | V-1 | Stk11 | 6794 | 24-May-15 | 13480 | 3 | 4 | 5 | | | V-1 | Tbxa2r | 6915 | 31-May-15 |
| 13385 | 3 | 4 | 5 | | | V-1 | Stk19 | 8859 | 12-May-15 | 13481 | 3 | 4 | 5 | | | V-1 | Tbxas1 | 6916 | 12-May-15 |
| 13386 | 3 | 4 | 5 | | | V-1 | Stk31 | 56164 | 4-May-15 | | | | | | | | | | |

Fig. 30 - 72

| | | | | | | | | | | | | | | | | | |
|---|---|---|---|---|---|---|---|---|---|---|---|---|---|---|---|---|---|
| 13482 | 3 | 4 | 5 | | | V-1 | Tc2n | 123036 | 4-May-15 | 13577 | 3 | 4 | 5 | | | V-1 | Tmcc1 | 23023 | 4-May-15 |
| 13483 | 3 | 4 | 5 | | | V-1 | Tcea1 | 6917 | 4-May-15 | 13578 | 3 | 4 | 5 | | | V-1 | Tmcc3 | 57458 | 4-May-15 |
| 13484 | 3 | 4 | 5 | | | V-1 | Tcea2 | 6919 | 12-May-15 | 13579 | 3 | 4 | 5 | | | V-1 | Tmed2 | 10959 | 4-May-15 |
| 13485 | 3 | 4 | 5 | | | V-1 | Tcea3 | 6920 | 4-May-15 | 13580 | 3 | 4 | 5 | | | V-1 | Tmed4 | 222068 | 12-May-15 |
| 13486 | 3 | 4 | 5 | | | V-1 | Tceal1 | 9338 | 4-May-15 | 13581 | 3 | 4 | 5 | | | V-1 | Tmed5 | 50999 | 4-May-15 |
| 13487 | 3 | 4 | 5 | | | V-1 | Tceal3 | 85012 | 4-May-15 | 13582 | 3 | 4 | 5 | | | V-1 | Tmed7 | 51014 | 4-May-15 |
| 13488 | 3 | 4 | 5 | | | V-1 | Tceanc | 170082 | 4-May-15 | 13583 | 3 | 4 | 5 | | | V-1 | Tmeff2 | 23671 | 12-May-15 |
| 13489 | 3 | 4 | 5 | | | V-1 | Tcf20 | 6942 | 4-May-15 | 13584 | 3 | 4 | 5 | | | V-1 | Tmem101 | 84336 | 4-May-15 |
| 13490 | 3 | 4 | 5 | | | V-1 | Tcf23 | 150921 | 4-May-15 | 13585 | 3 | 4 | 5 | | | V-1 | Tmem104 | 54868 | 4-May-15 |
| 13491 | 3 | 4 | 5 | | | V-1 | Tcf24 | 100129654 | 4-May-15 | 13586 | 3 | 4 | 5 | | | V-1 | Tmem106b | 54664 | 17-May-15 |
| 13492 | 3 | 4 | 5 | | | V-1 | Tcf25 | 22980 | 31-May-15 | 13587 | 3 | 4 | 5 | | | V-1 | Tmem108 | 66000 | 4-May-15 |
| 13493 | 3 | 4 | 5 | | | V-1 | Tcf4 | 6925 | 7-Jun-15 | 13588 | 3 | 4 | 5 | | | V-1 | Tmem109 | 79073 | 4-May-15 |
| 13494 | 3 | 4 | 5 | | | V-1 | Tcf7l1 | 83439 | 4-May-15 | 13589 | 3 | 4 | 5 | | | V-1 | Tmem117 | 84216 | 4-May-15 |
| 13495 | 3 | 4 | 5 | | | V-1 | Tchp | 84260 | 12-May-15 | 13590 | 3 | 4 | 5 | | | V-1 | Tmem120a | 83862 | 4-May-15 |
| 13496 | 3 | 4 | 5 | | | V-1 | Tcl1 | 8115 | 7-Jun-15 | 13591 | 3 | 4 | 5 | | | V-1 | Tmem121 | 80757 | 4-May-15 |
| 13497 | 3 | 4 | 5 | | | V-1 | Tcp1 | 6950 | 17-May-15 | 13592 | 3 | 4 | 5 | | | V-1 | Tmem126a | 84233 | 4-May-15 |
| 13498 | 3 | 4 | 5 | | | V-1 | Tcstv1 | | | 13593 | 3 | 4 | 5 | | | V-1 | Tmem132c | 92293 | 4-May-15 |
| 13499 | 3 | 4 | 5 | | | V-1 | Tcte1 | 202500 | 4-May-15 | 13594 | 3 | 4 | 5 | | | V-1 | Tmem134 | 80194 | 4-May-15 |
| 13500 | 3 | 4 | 5 | | | V-1 | Tctex1d1 | 200132 | 12-May-15 | 13595 | 3 | 4 | 5 | | | V-1 | Tmem138 | 51524 | 23-May-15 |
| 13501 | 3 | 4 | 5 | | | V-1 | Tctn1 | 79600 | 23-May-15 | 13596 | 3 | 4 | 5 | | | V-1 | Tmem140 | 55281 | 4-May-15 |
| 13502 | 3 | 4 | 5 | | | V-1 | Tdgf1 | 6997 | 13-Jun-15 | 13597 | 3 | 4 | 5 | | | V-1 | Tmem141 | 85014 | 4-May-15 |
| 13503 | 3 | 4 | 5 | | | V-1 | Tdp2 | 51567 | 3-May-15 | 13598 | 3 | 4 | 5 | | | V-1 | Tmem143 | 55260 | 12-May-15 |
| 13504 | 3 | 4 | 5 | | | V-1 | Tdrd6 | 221400 | 4-May-15 | 13599 | 3 | 4 | 5 | | | V-1 | Tmem145 | 284339 | 4-May-15 |
| 13505 | 3 | 4 | 5 | | | V-1 | Tead1 | 7003 | 4-May-15 | 13600 | 3 | 4 | 5 | | | V-1 | Tmem150a | 129303 | 4-May-15 |
| 13506 | 3 | 4 | 5 | | | V-1 | Tead3 | 7005 | 4-May-15 | 13601 | 3 | 4 | 5 | | | V-1 | Tmem150cos | | |
| 13507 | 3 | 4 | 5 | | | V-1 | Tecpr1 | 25851 | 21-May-15 | 13602 | 3 | 4 | 5 | | | V-1 | Tmem159 | 57146 | 12-May-15 |
| 13508 | 3 | 4 | 5 | | | V-1 | Tekt2 | 27285 | 12-May-15 | 13603 | 3 | 4 | 5 | | | V-1 | Tmem160 | 54958 | 4-May-15 |
| 13509 | 3 | 4 | 5 | | | V-1 | Tekt5 | 146279 | 4-May-15 | 13604 | 3 | 4 | 5 | | | V-1 | Tmem164 | 84187 | 12-May-15 |
| 13510 | 3 | 4 | 5 | | | V-1 | Tenc1 | 23371 | 17-May-15 | 13605 | 3 | 4 | 5 | | | V-1 | Tmem167b | 56900 | 4-May-15 |
| 13511 | 3 | 4 | 5 | | | V-1 | Tenm1 | 10178 | 12-May-15 | 13606 | 3 | 4 | 5 | | | V-1 | Tmem17 | 200728 | 4-May-15 |
| 13512 | 3 | 4 | 5 | | | V-1 | Tenm4 | 26011 | 12-May-15 | 13607 | 3 | 4 | 5 | | | V-1 | Tmem174 | 134288 | 4-May-15 |
| 13513 | 3 | 4 | 5 | | | V-1 | Tep1 | 7011 | 7-Jun-15 | 13608 | 3 | 4 | 5 | | | V-1 | Tmem176b | 28959 | 4-May-15 |
| 13514 | 3 | 4 | 5 | | | V-1 | Terf1 | 7013 | 4-May-15 | 13609 | 3 | 4 | 5 | | | V-1 | Tmem177 | 80775 | 12-May-15 |
| 13515 | 3 | 4 | 5 | | | V-1 | Tesc | | | 13610 | 3 | 4 | 5 | | | V-1 | Tmem179b | 374395 | 4-May-15 |
| 13516 | 3 | 4 | 5 | | | V-1 | Tesk1 | 7016 | 4-May-15 | 13611 | 3 | 4 | 5 | | | V-1 | Tmem183a | 92703 | 4-May-15 |
| 13517 | 3 | 4 | 5 | | | V-1 | Tet1 | 80312 | 31-May-15 | 13612 | 3 | 4 | 5 | | | V-1 | Tmem184b | 25829 | 21-May-15 |
| 13518 | 3 | 4 | 5 | | | V-1 | Tex16 | | | 13613 | 3 | 4 | 5 | | | V-1 | Tmem194b | 100131211 | 28-May-15 |
| 13519 | 3 | 4 | 5 | | | V-1 | Tex33 | 339669 | 4-May-15 | 13614 | 3 | 4 | 5 | | | V-1 | Tmem200a | 114801 | 4-May-15 |
| 13520 | 3 | 4 | 5 | | | V-1 | Tfap2c | 7022 | 4-May-15 | 13615 | 3 | 4 | 5 | | | V-1 | Tmem200c | 645369 | 4-May-15 |
| 13521 | 3 | 4 | 5 | | | V-1 | Tfdp1 | 7027 | 2-Jun-15 | 13616 | 3 | 4 | 5 | | | V-1 | Tmem203 | 94107 | 28-May-15 |
| 13522 | 3 | 4 | 5 | | | V-1 | Tfe3 | 7030 | 28-May-15 | 13617 | 3 | 4 | 5 | | | V-1 | Tmem205 | 374882 | 4-May-15 |
| 13523 | 3 | 4 | 5 | | | V-1 | Tff1 | 7031 | 12-May-15 | 13618 | 3 | 4 | 5 | | | V-1 | Tmem214 | 54867 | 4-May-15 |
| 13524 | 3 | 4 | 5 | | | V-1 | Tfg | 10342 | 17-May-15 | 13619 | 3 | 4 | 5 | | | V-1 | Tmem217 | 221468 | 4-May-15 |
| 13525 | 3 | 4 | 5 | | | V-1 | Tfpt | 29844 | 4-May-15 | 13620 | 3 | 4 | 5 | | | V-1 | Tmem222 | 84065 | 4-May-15 |
| 13526 | 3 | 4 | 5 | | | V-1 | Tg | 7038 | 31-May-15 | 13621 | 3 | 4 | 5 | | | V-1 | Tmem230 | 29058 | 4-May-15 |
| 13527 | 3 | 4 | 5 | | | V-1 | Tgfb1i1 | 7041 | 4-May-15 | 13622 | 3 | 4 | 5 | | | V-1 | Tmem238 | 385564 | 4-May-15 |
| 13528 | 3 | 4 | 5 | | | V-1 | Tgfbr1 | 7046 | 24-May-15 | 13623 | 3 | 4 | 5 | | | V-1 | Tmem245 | 23731 | 4-May-15 |
| 13529 | 3 | 4 | 5 | | | V-1 | Tgfbr2 | 7048 | 23-May-15 | 13624 | 3 | 4 | 5 | | | V-1 | Tmem246 | 84302 | 12-May-15 |
| 13530 | 3 | 4 | 5 | | | V-1 | Tgif2 | 60436 | 4-May-15 | 13625 | 3 | 4 | 5 | | | V-1 | Tmem253 | 643382 | 4-May-15 |
| 13531 | 3 | 4 | 5 | | | V-1 | Tgm2 | 7052 | 12-May-15 | 13626 | 3 | 4 | 5 | | | V-1 | Tmem255b | 348013 | 4-May-15 |
| 13532 | 3 | 4 | 5 | | | V-1 | Tgm4 | 7047 | 21-May-15 | 13627 | 3 | 4 | 5 | | | V-1 | Tmem258 | 746 | 4-May-15 |
| 13533 | 3 | 4 | 5 | | | V-1 | Tgs1 | 96764 | 7-Jun-15 | 13628 | 3 | 4 | 5 | | | V-1 | Tmem259 | 91304 | 4-May-15 |
| 13534 | 3 | 4 | 5 | | | V-1 | Th | 7054 | 23-May-15 | 13629 | 3 | 4 | 5 | | | V-1 | Tmem260 | 54916 | 4-May-15 |
| 13535 | 3 | 4 | 5 | | | V-1 | Thap3 | 90326 | 4-May-15 | 13630 | 3 | 4 | 5 | | | V-1 | Tmem30a | 55754 | 3-May-15 |
| 13536 | 3 | 4 | 5 | | | V-1 | Thap7 | 80764 | 4-May-15 | 13631 | 3 | 4 | 5 | | | V-1 | Tmem30c | 644444 | 4-May-15 |
| 13537 | 3 | 4 | 5 | | | V-1 | Theg | 51298 | 4-May-15 | 13632 | 3 | 4 | 5 | | | V-1 | Tmem38b | 55151 | 4-May-15 |
| 13538 | 3 | 4 | 5 | | | V-1 | Themis3 | | | 13633 | 3 | 4 | 5 | | | V-1 | Tmem39b | 55116 | 28-May-15 |
| 13539 | 3 | 4 | 5 | | | V-1 | Thnsl1 | 79896 | 4-May-15 | 13634 | 3 | 4 | 5 | | | V-1 | Tmem41a | 90407 | 4-May-15 |
| 13540 | 3 | 4 | 5 | | | V-1 | Thoc1 | 9984 | 4-May-15 | 13635 | 3 | 4 | 5 | | | V-1 | Tmem44 | 93109 | 4-May-15 |
| 13541 | 3 | 4 | 5 | | | V-1 | Thoc7 | 80145 | 4-May-15 | 13636 | 3 | 4 | 5 | | | V-1 | Tmem52b | 120939 | 4-May-15 |
| 13542 | 3 | 4 | 5 | | | V-1 | Thra | 7067 | 12-May-15 | 13637 | 3 | 4 | 5 | | | V-1 | Tmem57 | 55219 | 4-May-15 |
| 13543 | 3 | 4 | 5 | | | V-1 | Thsd1 | 55901 | 4-May-15 | 13638 | 3 | 4 | 5 | | | V-1 | Tmem65 | 157378 | 12-May-15 |
| 13544 | 3 | 4 | 5 | | | V-1 | Thsd7b | 80731 | 4-May-15 | 13639 | 3 | 4 | 5 | | | V-1 | Tmem74 | 157753 | 21-May-15 |
| 13545 | 3 | 4 | 5 | | | V-1 | Thyn1 | 29087 | 4-May-15 | 13640 | 3 | 4 | 5 | | | V-1 | Tmem8 | 58986 | 4-May-15 |
| 13546 | 3 | 4 | 5 | | | V-1 | Tia1 | 7072 | 4-May-15 | 13641 | 3 | 4 | 5 | | | V-1 | Tmem80 | 283232 | 4-May-15 |
| 13547 | 3 | 4 | 5 | | | V-1 | Tiaf1 | 7073 | 2-Jun-15 | 13642 | 3 | 4 | 5 | | | V-1 | Tmem87a | 25963 | 4-May-15 |
| 13548 | 3 | 4 | 5 | | | V-1 | Tiam2 | 26230 | 4-May-15 | 13643 | 3 | 4 | 5 | | | V-1 | Tmem89 | 440955 | 4-May-15 |
| 13549 | 3 | 4 | 5 | | | V-1 | Ticam1 | 148022 | 17-May-15 | 13644 | 3 | 4 | 5 | | | V-1 | Tmem92 | 162461 | 7-Jun-15 |
| 13550 | 3 | 4 | 5 | | | V-1 | Tie1 | 7075 | 4-May-15 | 13645 | 3 | 4 | 5 | | | V-1 | Tmem9b | 56674 | 12-May-15 |
| 13551 | 3 | 4 | 5 | | | V-1 | Tigd2 | 166815 | 4-May-15 | 13646 | 3 | 4 | 5 | | | V-1 | Tmie | 55217 | 4-May-15 |
| 13552 | 3 | 4 | 5 | | | V-1 | Tigd4 | 201798 | 4-May-15 | 13647 | 3 | 4 | 5 | | | V-1 | Tmod2 | 29767 | 12-May-15 |
| 13553 | 3 | 4 | 5 | | | V-1 | Timd2 | | | 13648 | 3 | 4 | 5 | | | V-1 | Tmppe | 643853 | 4-May-15 |
| 13554 | 3 | 4 | 5 | | | V-1 | Timeless | 8914 | 3-May-15 | 13649 | 3 | 4 | 5 | | | V-1 | Tmprss12 | 283471 | 4-May-15 |
| 13555 | 3 | 4 | 5 | | | V-1 | Timm10 | 26519 | 21-May-15 | 13650 | 3 | 4 | 5 | | | V-1 | Tmprss4 | 56649 | 12-May-15 |
| 13556 | 3 | 4 | 5 | | | V-1 | Timm8a2 | | | 13651 | 3 | 4 | 5 | | | V-1 | Tmsb15b2 | | |
| 13557 | 3 | 4 | 5 | | | V-1 | Timp3 | 7078 | 12-May-15 | 13652 | 3 | 4 | 5 | | | V-1 | Tmtc1 | 83857 | 4-May-15 |
| 13558 | 3 | 4 | 5 | | | V-1 | Tinf2 | 26277 | 23-May-15 | 13653 | 3 | 4 | 5 | | | V-1 | Tmtc2 | 160335 | 4-May-15 |
| 13559 | 3 | 4 | 5 | | | V-1 | Tipr | 261726 | 31-May-15 | 13654 | 3 | 4 | 5 | | | V-1 | Tmtc3 | 160418 | 4-May-15 |
| 13560 | 3 | 4 | 5 | | | V-1 | Tjp2 | 9414 | 12-May-15 | 13655 | 3 | 4 | 5 | | | V-1 | Tmtc4 | 84899 | 4-May-15 |
| 13561 | 3 | 4 | 5 | | | V-1 | Tk2 | 7084 | 23-May-15 | 13656 | 3 | 4 | 5 | | | V-1 | Tnf | 7124 | 31-May-15 |
| 13562 | 3 | 4 | 5 | | | V-1 | Tktl1 | 8277 | 4-May-15 | 13657 | 3 | 4 | 5 | | | V-1 | Tnfaip1 | 7126 | 4-May-15 |
| 13563 | 3 | 4 | 5 | | | V-1 | Tle3 | 7090 | 21-May-15 | 13658 | 3 | 4 | 5 | | | V-1 | Tnfaip8l1 | 126282 | 12-May-15 |
| 13564 | 3 | 4 | 5 | | | V-1 | Tle4 | 7091 | 31-May-15 | 13659 | 3 | 4 | 5 | | | V-1 | Tnfaip8l3 | 388121 | 3-May-15 |
| 13565 | 3 | 4 | 5 | | | V-1 | Tlk1 | 9874 | 4-May-15 | 13660 | 3 | 4 | 5 | | | V-1 | Tnfrsf11a | 8792 | 31-May-15 |
| 13566 | 3 | 4 | 5 | | | V-1 | Tln2 | 83660 | 4-May-15 | 13661 | 3 | 4 | 5 | | | V-1 | Tnfrsf14 | 8764 | 10-May-15 |
| 13567 | 3 | 4 | 5 | | | V-1 | Tlr11 | | | 13662 | 3 | 4 | 5 | | | V-1 | Tnfrsf17 | 608 | 4-May-15 |
| 13568 | 3 | 4 | 5 | | | V-1 | Tlr3 | 7098 | 31-May-15 | 13663 | 3 | 4 | 5 | | | V-1 | Tnfrsf1a | 7132 | 14-May-15 |
| 13569 | 3 | 4 | 5 | | | V-1 | Tlr5 | 7100 | 17-May-15 | 13664 | 3 | 4 | 5 | | | V-1 | Tnfrsf21 | 27242 | 4-May-15 |
| 13570 | 3 | 4 | 5 | | | V-1 | Tlr6 | 10333 | 17-May-15 | 13665 | 3 | 4 | 5 | | | V-1 | Tnfrsf4 | 7293 | 4-May-15 |
| 13571 | 3 | 4 | 5 | | | V-1 | Tlx1 | 3195 | 4-May-15 | 13666 | 3 | 4 | 5 | | | V-1 | Tnfsf12 | 8742 | 4-May-15 |
| 13572 | 3 | 4 | 5 | | | V-1 | Tm4sf20 | 79853 | 12-May-15 | 13667 | 3 | 4 | 5 | | | V-1 | Tnfsf15 | 9966 | 12-May-15 |
| 13573 | 3 | 4 | 5 | | | V-1 | Tm7sf3 | 51768 | 12-May-15 | 13668 | 3 | 4 | 5 | | | V-1 | Tnip1 | 10318 | 21-May-15 |
| 13574 | 3 | 4 | 5 | | | V-1 | Tma7 | 51372 | 4-May-15 | 13669 | 3 | 4 | 5 | | | V-1 | Tnk2 | 10188 | 21-May-15 |
| 13575 | 3 | 4 | 5 | | | V-1 | Tmbim4 | 51643 | 4-May-15 | 13670 | 3 | 4 | 5 | | | V-1 | Tnks | 8658 | 4-May-15 |
| 13576 | 3 | 4 | 5 | | | V-1 | Tmc6 | 11322 | 4-May-15 | 13671 | 3 | 4 | 5 | | | V-1 | Tnni1 | 7135 | 12-May-15 |

Fig. 30 - 73

| | | | | | | | | | | | | | | | | |
|---|---|---|---|---|---|---|---|---|---|---|---|---|---|---|---|---|
| 13672 | 3 | 4 | 5 | | | V-1 | Tnpo1 | 3842 | 4-May-15 | 13768 | 3 | 4 | 5 | | V-1 | Tstd3 | 100130890 | 12-May-15 |
| 13673 | 3 | 4 | 5 | | | V-1 | Tns4 | 84951 | 12-May-15 | 13769 | 3 | 4 | 5 | | V-1 | Ttc25 | 83538 | 4-May-15 |
| 13674 | 3 | 4 | 5 | | | V-1 | Tob1 | 10140 | 4-May-15 | 13770 | 3 | 4 | 5 | | V-1 | Ttc39b | 158219 | 4-May-15 |
| 13675 | 3 | 4 | 5 | | | V-1 | Toe1 | 114034 | 4-May-15 | 13771 | 3 | 4 | 5 | | V-1 | Ttc7b | 145567 | 4-May-15 |
| 13676 | 3 | 4 | 5 | | | V-1 | Tom1l2 | 146691 | 4-May-15 | 13772 | 3 | 4 | 5 | | V-1 | Ttc9b | 148014 | 4-May-15 |
| 13677 | 3 | 4 | 5 | | | V-1 | Tomm7 | 54543 | 4-May-15 | 13773 | 3 | 4 | 5 | | V-1 | Tti1 | 9675 | 12-May-15 |
| 13678 | 3 | 4 | 5 | | | V-1 | Tonsl | 4796 | 4-May-15 | 13774 | 3 | 4 | 5 | | V-1 | Ttl | 150465 | 7-Jun-15 |
| 13679 | 3 | 4 | 5 | | | V-1 | Top1 | 7150 | 12-May-15 | 13775 | 3 | 4 | 5 | | V-1 | Ttll2 | 23170 | 4-May-15 |
| 13680 | 3 | 4 | 5 | | | V-1 | Top2b | 7155 | 17-May-15 | 13776 | 3 | 4 | 5 | | V-1 | Ttll3 | 440307 | 4-May-15 |
| 13681 | 3 | 4 | 5 | | | V-1 | Topors | 10210 | 23-May-15 | 13777 | 3 | 4 | 5 | | V-1 | Ttll4 | 9654 | 21-May-15 |
| 13682 | 3 | 4 | 5 | | | V-1 | Tor4a | 54863 | 4-May-15 | 13778 | 3 | 4 | 5 | | V-1 | Ttll5 | 23093 | 7-Jun-15 |
| 13683 | 3 | 4 | 5 | | | V-1 | Tox4 | 9878 | 4-May-15 | 13779 | 3 | 4 | 5 | | V-1 | Ttll8 | 164714 | 4-May-15 |
| 13684 | 3 | 4 | 5 | | | V-1 | Tpbpa | | | 13780 | 3 | 4 | 5 | | V-1 | Ttpal | 79183 | 4-May-15 |
| 13685 | 3 | 4 | 5 | | | V-1 | Tpcn2 | 219931 | 29-May-15 | 13781 | 3 | 4 | 5 | | V-1 | Ttr | 7276 | 31-May-15 |
| 13686 | 3 | 4 | 5 | | | V-1 | Tpd52l2 | 7165 | 4-May-15 | 13782 | 3 | 4 | 5 | | V-1 | Ttyh2 | 94015 | 12-May-15 |
| 13687 | 3 | 4 | 5 | | | V-1 | Tph2 | 121278 | 7-Jun-15 | 13783 | 3 | 4 | 5 | | V-1 | Tub | 7275 | 28-May-15 |
| 13688 | 3 | 4 | 5 | | | V-1 | Tpm2 | 7169 | 2-Jun-15 | 13784 | 3 | 4 | 5 | | V-1 | Tuba3a | | |
| 13689 | 3 | 4 | 5 | | | V-1 | Tpmt | 7172 | 12-May-15 | 13785 | 3 | 4 | 5 | | V-1 | Tubal3 | 79861 | 7-Jun-15 |
| 13690 | 3 | 4 | 5 | | | V-1 | Tpr | 7175 | 17-May-15 | 13786 | 3 | 4 | 5 | | V-1 | Tubd1 | 51174 | 4-May-15 |
| 13691 | 3 | 4 | 5 | | | V-1 | Tpsg1 | 25823 | 12-May-15 | 13787 | 3 | 4 | 5 | | V-1 | Tubg1 | 7283 | 31-May-15 |
| 13692 | 3 | 4 | 5 | | | V-1 | Tra2a | 29896 | 2-Jun-15 | 13788 | 3 | 4 | 5 | | V-1 | Tug1 | 55000 | 12-May-15 |
| 13693 | 3 | 4 | 5 | | | V-1 | Tra2b | 6434 | 17-May-15 | 13789 | 3 | 4 | 5 | | V-1 | Tusc2 | 11334 | 4-May-15 |
| 13694 | 3 | 4 | 5 | | | V-1 | Trabd | 80305 | 4-May-15 | 13790 | 3 | 4 | 5 | | V-1 | Tuft1 | 64852 | 4-May-15 |
| 13695 | 3 | 4 | 5 | | | V-1 | Trabd2b | 388630 | 4-May-15 | 13791 | 3 | 4 | 5 | | V-1 | Tvp23b | 51030 | 4-May-15 |
| 13696 | 3 | 4 | 5 | | | V-1 | Traf2 | 7186 | 7-Jun-15 | 13792 | 3 | 4 | 5 | | V-1 | Twist2 | 117581 | 4-May-15 |
| 13697 | 3 | 4 | 5 | | | V-1 | Traf4 | 9618 | 21-May-15 | 13793 | 3 | 4 | 5 | | V-1 | Twistnb | 221830 | 12-May-15 |
| 13698 | 3 | 4 | 5 | | | V-1 | Traf6 | 7189 | 23-May-15 | 13794 | 3 | 4 | 5 | | V-1 | Txlna | 200081 | 28-May-15 |
| 13699 | 3 | 4 | 5 | | | V-1 | Trafd1 | 10906 | 12-May-15 | 13795 | 3 | 4 | 5 | | V-1 | Txlng | 55787 | 4-May-15 |
| 13700 | 3 | 4 | 5 | | | V-1 | Trak1 | 22906 | 4-May-15 | 13796 | 3 | 4 | 5 | | V-1 | Txndc17 | 84817 | 4-May-15 |
| 13701 | 3 | 4 | 5 | | | V-1 | Tram1 | 23471 | 7-Jun-15 | 13797 | 3 | 4 | 5 | | V-1 | Txndc5 | 81567 | 31-May-15 |
| 13702 | 3 | 4 | 5 | | | V-1 | Trap1 | 10131 | 7-Jun-15 | 13798 | 3 | 4 | 5 | | V-1 | Txndc8 | 255220 | 4-May-15 |
| 13703 | 3 | 4 | 5 | | | V-1 | Trappc9 | 83696 | 4-May-15 | 13799 | 3 | 4 | 5 | | V-1 | Txnl1 | 9352 | 12-May-15 |
| 13704 | 3 | 4 | 5 | | | V-1 | Tratl | 50852 | 4-May-15 | 13800 | 3 | 4 | 5 | | V-1 | Txnl4a | 10907 | 2-Jun-15 |
| 13705 | 3 | 4 | 5 | | | V-1 | Trcg1 | | | 13801 | 3 | 4 | 5 | | V-1 | Txnrd3 | 114112 | 12-May-15 |
| 13706 | 3 | 4 | 5 | | | V-1 | Trem3 | | | 13802 | 3 | 4 | 5 | | V-1 | Tyk2 | 7297 | 4-May-15 |
| 13707 | 3 | 4 | 5 | | | V-1 | Trerf1 | 55809 | 28-May-15 | 13803 | 3 | 4 | 5 | | V-1 | Tyr | 7299 | 7-Jun-15 |
| 13708 | 3 | 4 | 5 | | | V-1 | Trex1 | 11277 | 23-May-15 | 13804 | 3 | 4 | 5 | | V-1 | Tyrp1 | 7306 | 7-Jun-15 |
| 13709 | 3 | 4 | 5 | | | V-1 | Trh | 7200 | 4-May-15 | 13805 | 3 | 4 | 5 | | V-1 | U2af1l4 | 199746 | 7-Jun-15 |
| 13710 | 3 | 4 | 5 | | | V-1 | Trhr | 7201 | 12-May-15 | 13806 | 3 | 4 | 5 | | V-1 | Uaca | 55075 | 4-May-15 |
| 13711 | 3 | 4 | 5 | | | V-1 | Trim11 | 81559 | 4-May-15 | 13807 | 3 | 4 | 5 | | V-1 | Uba1 | 7317 | 31-May-15 |
| 13712 | 3 | 4 | 5 | | | V-1 | Trim13 | 10206 | 4-May-15 | 13808 | 3 | 4 | 5 | | V-1 | Ubac2 | 337867 | 3-May-15 |
| 13713 | 3 | 4 | 5 | | | V-1 | Trim15 | 89870 | 7-Jun-15 | 13809 | 3 | 4 | 5 | | V-1 | Ubap1 | 51271 | 12-May-15 |
| 13714 | 3 | 4 | 5 | | | V-1 | Trim21 | 6737 | 24-May-15 | 13810 | 3 | 4 | 5 | | V-1 | Ubb | 7314 | 29-May-15 |
| 13715 | 3 | 4 | 5 | | | V-1 | Trim25 | 7706 | 4-May-15 | 13811 | 3 | 4 | 5 | | V-1 | Ube2a | 7319 | 2-Jun-15 |
| 13716 | 3 | 4 | 5 | | | V-1 | Trim26 | 7726 | 4-May-15 | 13812 | 3 | 4 | 5 | | V-1 | Ube2cbp | 90025 | 4-May-15 |
| 13717 | 3 | 4 | 5 | | | V-1 | Trim28 | 10155 | 4-May-15 | 13813 | 3 | 4 | 5 | | V-1 | Ube2f | 140739 | 2-Jun-15 |
| 13718 | 3 | 4 | 5 | | | V-1 | Trim3 | 10612 | 17-May-15 | 13814 | 3 | 4 | 5 | | V-1 | Ube2h | 7328 | 4-May-15 |
| 13719 | 3 | 4 | 5 | | | V-1 | Trim30e-ps1 | | | 13815 | 3 | 4 | 5 | | V-1 | Ube2j2 | 118424 | 29-May-15 |
| 13720 | 3 | 4 | 5 | | | V-1 | Trim34b | | | 13816 | 3 | 4 | 5 | | V-1 | Ube2m | 9040 | 4-May-15 |
| 13721 | 3 | 4 | 5 | | | V-1 | Trim35 | 23087 | 12-May-15 | 13817 | 3 | 4 | 5 | | V-1 | Ube2q1 | 55585 | 4-May-15 |
| 13722 | 3 | 4 | 5 | | | V-1 | Trim37 | 4591 | 4-May-15 | 13818 | 3 | 4 | 5 | | V-1 | Ube2r2 | 54926 | 12-May-15 |
| 13723 | 3 | 4 | 5 | | | V-1 | Trim50 | 135892 | 4-May-15 | 13819 | 3 | 4 | 5 | | V-1 | Ube2u | 148581 | 4-May-15 |
| 13724 | 3 | 4 | 5 | | | V-1 | Trim52 | 84851 | 12-May-15 | 13820 | 3 | 4 | 5 | | V-1 | Ube3a | 7337 | 23-May-15 |
| 13725 | 3 | 4 | 5 | | | V-1 | Trim55 | 84675 | 12-May-15 | 13821 | 3 | 4 | 5 | | V-1 | Ube4b | 10277 | 4-May-15 |
| 13726 | 3 | 4 | 5 | | | V-1 | Trim60 | 166655 | 4-May-15 | 13822 | 3 | 4 | 5 | | V-1 | Ubfd1 | 56061 | 12-May-15 |
| 13727 | 3 | 4 | 5 | | | V-1 | Trim65 | 201292 | 12-May-15 | 13823 | 3 | 4 | 5 | | V-1 | Ubiad1 | 29914 | 23-May-15 |
| 13728 | 3 | 4 | 5 | | | V-1 | Trim69 | 140691 | 12-May-15 | 13824 | 3 | 4 | 5 | | V-1 | Ubqln2 | 29978 | 23-May-15 |
| 13729 | 3 | 4 | 5 | | | V-1 | Trim75 | 391714 | 4-May-15 | 13825 | 3 | 4 | 5 | | V-1 | Ubr5 | 51366 | 12-May-15 |
| 13730 | 3 | 4 | 5 | | | V-1 | Trip4 | 9325 | 4-May-15 | 13826 | 3 | 4 | 5 | | V-1 | Ubtd2 | 92181 | 4-May-15 |
| 13731 | 3 | 4 | 5 | | | V-1 | Trmt1 | 55621 | 7-Jun-15 | 13827 | 3 | 4 | 5 | | V-1 | Ubtf | 7343 | 12-May-15 |
| 13732 | 3 | 4 | 5 | | | V-1 | Trmt10b | 158234 | 23-May-15 | 13828 | 3 | 4 | 5 | | V-1 | Ubxn6 | 80700 | 4-May-15 |
| 13733 | 3 | 4 | 5 | | | V-1 | Trmt61a | 115708 | 4-May-15 | 13829 | 3 | 4 | 5 | | V-1 | Uchl1os | | |
| 13734 | 3 | 4 | 5 | | | V-1 | Trmt61b | 55006 | 4-May-15 | 13830 | 3 | 4 | 5 | | V-1 | Uchl5 | 51377 | 4-May-15 |
| 13735 | 3 | 4 | 5 | | | V-1 | Trnu | 55687 | 23-May-15 | 13831 | 3 | 4 | 5 | | V-1 | Uck1 | 83549 | 13-Jun-15 |
| 13736 | 3 | 4 | 5 | | | V-1 | Trnt1 | 51095 | 7-Jun-15 | 13832 | 3 | 4 | 5 | | V-1 | Uckl1 | 54963 | 4-May-15 |
| 13737 | 3 | 4 | 5 | | | V-1 | Trove2 | 6738 | 4-May-15 | 13833 | 3 | 4 | 5 | | V-1 | Ucma | 221044 | 4-May-15 |
| 13738 | 3 | 4 | 5 | | | V-1 | Trp53bp1 | | | 13834 | 3 | 4 | 5 | | V-1 | Ucn | 7349 | 4-May-15 |
| 13739 | 3 | 4 | 5 | | | V-1 | Trp53i13 | | | 13835 | 3 | 4 | 5 | | V-1 | Ucn2 | 90226 | 7-Jun-15 |
| 13740 | 3 | 4 | 5 | | | V-1 | Trp53rk | | | 13836 | 3 | 4 | 5 | | V-1 | Ucn3 | 114131 | 7-Jun-15 |
| 13741 | 3 | 4 | 5 | | | V-1 | Trp73 | | | 13837 | 3 | 4 | 5 | | V-1 | Uevld | 55293 | 4-May-15 |
| 13742 | 3 | 4 | 5 | | | V-1 | Trpc4ap | 26133 | 12-May-15 | 13838 | 3 | 4 | 5 | | V-1 | Uggt1 | 56886 | 4-May-15 |
| 13743 | 3 | 4 | 5 | | | V-1 | Trpc6 | 7225 | 24-May-15 | 13839 | 3 | 4 | 5 | | V-1 | Uggt2 | 55757 | 4-May-15 |
| 13744 | 3 | 4 | 5 | | | V-1 | Trpc7 | 57113 | 7-Jun-15 | 13840 | 3 | 4 | 5 | | V-1 | Ugt1a9 | 54600 | 28-May-15 |
| 13745 | 3 | 4 | 5 | | | V-1 | Trpm4 | 54795 | 12-May-15 | 13841 | 3 | 4 | 5 | | V-1 | Ugt2b35 | | |
| 13746 | 3 | 4 | 5 | | | V-1 | Trpt1 | 83707 | 4-May-15 | 13842 | 3 | 4 | 5 | | V-1 | Uhmk1 | 127933 | 4-May-15 |
| 13747 | 3 | 4 | 5 | | | V-1 | Trpv3 | 162514 | 7-Jun-15 | 13843 | 3 | 4 | 5 | | V-1 | Uhrf1bp1 | 54887 | 4-May-15 |
| 13748 | 3 | 4 | 5 | | | V-1 | Trrap | 8295 | 4-May-15 | 13844 | 3 | 4 | 5 | | V-1 | Uhrf2 | 115426 | 4-May-15 |
| 13749 | 3 | 4 | 5 | | | V-1 | Tsacc | 128229 | 21-May-15 | 13845 | 3 | 4 | 5 | | V-1 | Uimc1 | 51720 | 4-May-15 |
| 13750 | 3 | 4 | 5 | | | V-1 | Tsc2 | 7249 | 12-May-15 | 13846 | 3 | 4 | 5 | | V-1 | Ulk1 | 8408 | 24-May-15 |
| 13751 | 3 | 4 | 5 | | | V-1 | Tsc22d2 | 9819 | 4-May-15 | 13847 | 3 | 4 | 5 | | V-1 | Ulk2 | 9706 | 21-May-15 |
| 13752 | 3 | 4 | 5 | | | V-1 | Tsc22d4 | 81628 | 12-May-15 | 13848 | 3 | 4 | 5 | | V-1 | Unc119 | 9094 | 4-May-15 |
| 13753 | 3 | 4 | 5 | | | V-1 | Tsga8 | | | 13849 | 3 | 4 | 5 | | V-1 | Unc119b | 84747 | 4-May-15 |
| 13754 | 3 | 4 | 5 | | | V-1 | Tshz1 | 10194 | 12-May-15 | 13850 | 3 | 4 | 5 | | V-1 | Unc50 | 25972 | 4-May-15 |
| 13755 | 3 | 4 | 5 | | | V-1 | Tshz3 | 57616 | 4-May-15 | 13851 | 3 | 4 | 5 | | V-1 | Unc5c | 8633 | 4-May-15 |
| 13756 | 3 | 4 | 5 | | | V-1 | Tspan14 | 81619 | 12-May-15 | 13852 | 3 | 4 | 5 | | V-1 | Unc5d | 137970 | 4-May-15 |
| 13757 | 3 | 4 | 5 | | | V-1 | Tspan17 | 26262 | 4-May-15 | 13853 | 3 | 4 | 5 | | V-1 | Uncx | 340260 | 21-May-15 |
| 13758 | 3 | 4 | 5 | | | V-1 | Tspan2 | 10100 | 21-May-15 | 13854 | 3 | 4 | 5 | | V-1 | Unk | 85451 | 21-May-15 |
| 13759 | 3 | 4 | 5 | | | V-1 | Tspan7 | 7102 | 23-May-15 | 13855 | 3 | 4 | 5 | | V-1 | Upk2 | 7379 | 4-May-15 |
| 13760 | 3 | 4 | 5 | | | V-1 | Tspear | 54084 | 7-Jun-15 | 13856 | 3 | 4 | 5 | | V-1 | Upk3a | 7380 | 4-May-15 |
| 13761 | 3 | 4 | 5 | | | V-1 | Tspyl1 | 7259 | 4-May-15 | 13857 | 3 | 4 | 5 | | V-1 | Uprt | 139596 | 12-May-15 |
| 13762 | 3 | 4 | 5 | | | V-1 | Tspyl4 | 23270 | 12-May-15 | 13858 | 3 | 4 | 5 | | V-1 | Urb1 | 9875 | 12-May-15 |
| 13763 | 3 | 4 | 5 | | | V-1 | Tsr2 | 90121 | 4-May-15 | 13859 | 3 | 4 | 5 | | V-1 | Ush1 | 79650 | 23-May-15 |
| 13764 | 3 | 4 | 5 | | | V-1 | Tssc4 | 10078 | 12-May-15 | 13860 | 3 | 4 | 5 | | V-1 | Ush2a | 7399 | 23-May-15 |
| 13765 | 3 | 4 | 5 | | | V-1 | Tssk5 | 283629 | 12-May-15 | 13861 | 3 | 4 | 5 | | V-1 | Usmg5 | 84833 | 4-May-15 |
| 13766 | 3 | 4 | 5 | | | V-1 | Tsta3 | 7264 | 4-May-15 | 13862 | 3 | 4 | 5 | | V-1 | Usp10 | 9100 | 7-Jun-15 |
| 13767 | 3 | 4 | 5 | | | V-1 | Tstd2 | 158427 | 4-May-15 | | | | | | | | | |

Fig. 30 - 74

| | | | | | | | | | | | | | | | | |
|---|---|---|---|---|---|---|---|---|---|---|---|---|---|---|---|---|
| 13863 | 3 | 4 | 5 | | | V-1 | Usp15 | 9958 | 2-Jun-15 | 13959 | 3 | 4 | 5 | | V-1 | Xkr8 | 55113 | 4-May-15 |
| 13864 | 3 | 4 | 5 | | | V-1 | Usp16 | 10600 | 7-Jun-15 | 13960 | 3 | 4 | 5 | | V-1 | Xkr9 | 389668 | 4-May-15 |
| 13865 | 3 | 4 | 5 | | | V-1 | Usp19 | 10869 | 28-May-15 | 13961 | 3 | 4 | 5 | | V-1 | Xlr4a | | |
| 13866 | 3 | 4 | 5 | | | V-1 | Usp21 | 27005 | 7-Jun-15 | 13962 | 3 | 4 | 5 | | V-1 | Xlr5a | | |
| 13867 | 3 | 4 | 5 | | | V-1 | Usp30 | 84749 | 12-May-15 | 13963 | 3 | 4 | 5 | | V-1 | Xpnpep2 | 7512 | 4-May-15 |
| 13868 | 3 | 4 | 5 | | | V-1 | Usp33 | 23032 | 21-May-15 | 13964 | 3 | 4 | 5 | | V-1 | Xpot | 11260 | 4-May-15 |
| 13869 | 3 | 4 | 5 | | | V-1 | Usp36 | 57602 | 12-May-15 | 13965 | 3 | 4 | 5 | | V-1 | Xrcc3 | 7517 | 22-May-15 |
| 13870 | 3 | 4 | 5 | | | V-1 | Usp47 | 55031 | 4-May-15 | 13966 | 3 | 4 | 5 | | V-1 | Xrcc4 | 7518 | 17-May-15 |
| 13871 | 3 | 4 | 5 | | | V-1 | Usp5 | 8078 | 29-May-15 | 13967 | 3 | 4 | 5 | | V-1 | Xrcc6bp1 | 91419 | 4-May-15 |
| 13872 | 3 | 4 | 5 | | | V-1 | Usp6nl | 9712 | 12-May-15 | 13968 | 3 | 4 | 5 | | V-1 | Xrn2 | 22803 | 4-May-15 |
| 13873 | 3 | 4 | 5 | | | V-1 | Usp8 | 9101 | 4-May-15 | 13969 | 3 | 4 | 5 | | V-1 | Xxylt1 | 152002 | 12-May-15 |
| 13874 | 3 | 4 | 5 | | | V-1 | Utf1 | 8433 | | 13970 | 3 | 4 | 5 | | V-1 | Xylt2 | 64132 | 31-May-15 |
| 13875 | 3 | 4 | 5 | | | V-1 | Utp15 | 84135 | 4-May-15 | 13971 | 3 | 4 | 5 | | V-1 | Yae1d1 | 57002 | 12-May-15 |
| 13876 | 3 | 4 | 5 | | | V-1 | Utp20 | 27340 | 4-May-15 | 13972 | 3 | 4 | 5 | | V-1 | Ydjc | 150223 | 4-May-15 |
| 13877 | 3 | 4 | 5 | | | V-1 | Uts2r | 2837 | 4-May-15 | 13973 | 3 | 4 | 5 | | V-1 | Yeats2 | 55689 | 4-May-15 |
| 13878 | 3 | 4 | 5 | | | V-1 | V1ra8 | | | 13974 | 3 | 4 | 5 | | V-1 | Yipf3 | 25844 | 4-May-15 |
| 13879 | 3 | 4 | 5 | | | V-1 | Vangl2 | 57216 | 4-May-15 | 13975 | 3 | 4 | 5 | | V-1 | Ykt6 | 10652 | 23-May-15 |
| 13880 | 3 | 4 | 5 | | | V-1 | Vasn | 114990 | 4-May-15 | 13976 | 3 | 4 | 5 | | V-1 | Ypel1 | 29799 | 2-Jun-15 |
| 13881 | 3 | 4 | 5 | | | V-1 | Vasp | 7408 | 17-May-15 | 13977 | 3 | 4 | 5 | | V-1 | Ypel3 | 83719 | 4-May-15 |
| 13882 | 3 | 4 | 5 | | | V-1 | Vat1 | 10493 | 13-Jun-15 | 13978 | 3 | 4 | 5 | | V-1 | Ypel5 | 51646 | 12-May-15 |
| 13883 | 3 | 4 | 5 | | | V-1 | Vaultrc5 | | | 13979 | 3 | 4 | 5 | | V-1 | Ythdc1 | 91746 | 12-May-15 |
| 13884 | 3 | 4 | 5 | | | V-1 | Vav2 | 7410 | 4-May-15 | 13980 | 3 | 4 | 5 | | V-1 | Ywhaq | 10971 | 31-May-15 |
| 13885 | 3 | 4 | 5 | | | V-1 | Vax1 | 11023 | 23-May-15 | 13981 | 3 | 4 | 5 | | V-1 | Yy1 | 7528 | 17-May-15 |
| 13886 | 3 | 4 | 5 | | | V-1 | Vcl | 7414 | 28-May-15 | 13982 | 3 | 4 | 5 | | V-1 | Zadh2 | 284273 | 12-May-15 |
| 13887 | 3 | 4 | 5 | | | V-1 | Vcp | 7415 | 29-May-15 | 13983 | 3 | 4 | 5 | | V-1 | Zan | 7455 | 12-May-15 |
| 13888 | 3 | 4 | 5 | | | V-1 | Vegfa | 7422 | 31-May-15 | 13984 | 3 | 4 | 5 | | V-1 | Zbed5 | 58486 | 4-May-15 |
| 13889 | 3 | 4 | 5 | | | V-1 | Vegfb | 7423 | 12-May-15 | 13985 | 3 | 4 | 5 | | V-1 | Zbtb1 | 22890 | 4-May-15 |
| 13890 | 3 | 4 | 5 | | | V-1 | Veph1 | 79674 | 4-May-15 | 13986 | 3 | 4 | 5 | | V-1 | Zbtb14 | 7541 | 1-Jun-15 |
| 13891 | 3 | 4 | 5 | | | V-1 | Vezf1 | 7716 | 4-May-15 | 13987 | 3 | 4 | 5 | | V-1 | Zbtb17 | 7709 | 3-May-15 |
| 13892 | 3 | 4 | 5 | | | V-1 | Vgll4 | 9686 | 12-May-15 | 13988 | 3 | 4 | 5 | | V-1 | Zbtb21 | 49854 | 28-May-15 |
| 13893 | 3 | 4 | 5 | | | V-1 | Vhl | 7428 | 31-May-15 | 13989 | 3 | 4 | 5 | | V-1 | Zbtb22 | 9278 | 4-May-15 |
| 13894 | 3 | 4 | 5 | | | V-1 | Vimp | 55829 | 29-May-15 | 13990 | 3 | 4 | 5 | | V-1 | Zbtb26 | 57684 | 2-Jun-15 |
| 13895 | 3 | 4 | 5 | | | V-1 | Vipr2 | 7434 | 12-May-15 | 13991 | 3 | 4 | 5 | | V-1 | Zbtb33 | 10009 | 12-May-15 |
| 13896 | 3 | 4 | 5 | | | V-1 | Vit | 5212 | 4-May-15 | 13992 | 3 | 4 | 5 | | V-1 | Zbtb38 | 253461 | 12-May-15 |
| 13897 | 3 | 4 | 5 | | | V-1 | Vkorc1 | 79001 | 17-May-15 | 13993 | 3 | 4 | 5 | | V-1 | Zbtb48 | 3104 | 4-May-15 |
| 13898 | 3 | 4 | 5 | | | V-1 | Vkorc1l1 | 154807 | 4-May-15 | 13994 | 3 | 4 | 5 | | V-1 | Zbtb8a | 653121 | 12-May-15 |
| 13899 | 3 | 4 | 5 | | | V-1 | Vma21 | 203547 | 7-Jun-15 | 13995 | 3 | 4 | 5 | | V-1 | Zbtb8b | 728116 | 4-May-15 |
| 13900 | 3 | 4 | 5 | | | V-1 | Vmn2r97 | | | 13996 | 3 | 4 | 5 | | V-1 | Zbtb8os | 339487 | 4-May-15 |
| 13901 | 3 | 4 | 5 | | | V-1 | Vmo1 | 284013 | 4-May-15 | 13997 | 3 | 4 | 5 | | V-1 | Zc2hc1a | 51101 | 4-May-15 |
| 13902 | 3 | 4 | 5 | | | V-1 | Vprbp | 9730 | 4-May-15 | 13998 | 3 | 4 | 5 | | V-1 | Zc3h10 | 84872 | 12-May-15 |
| 13903 | 3 | 4 | 5 | | | V-1 | Vps11 | 55823 | 12-May-15 | 13999 | 3 | 4 | 5 | | V-1 | Zc3h12b | 340554 | 4-May-15 |
| 13904 | 3 | 4 | 5 | | | V-1 | Vps13d | 55187 | 12-May-15 | 14000 | 3 | 4 | 5 | | V-1 | Zc3h13 | 23091 | 12-May-15 |
| 13905 | 3 | 4 | 5 | | | V-1 | Vps37c | 55048 | 4-May-15 | 14001 | 3 | 4 | 5 | | V-1 | Zc3hav1l | 92092 | 21-May-15 |
| 13906 | 3 | 4 | 5 | | | V-1 | Vps37d | 155382 | 4-May-15 | 14002 | 3 | 4 | 5 | | V-1 | Zc3hc1 | 51530 | 4-May-15 |
| 13907 | 3 | 4 | 5 | | | V-1 | Vrk2 | 7444 | 4-May-15 | 14003 | 3 | 4 | 5 | | V-1 | Zcchc10 | 54819 | 12-May-15 |
| 13908 | 3 | 4 | 5 | | | V-1 | Vrk3 | 51231 | 21-May-15 | 14004 | 3 | 4 | 5 | | V-1 | Zcchc12 | 170261 | 4-May-15 |
| 13909 | 3 | 4 | 5 | | | V-1 | Vsig10 | 54621 | 4-May-15 | 14005 | 3 | 4 | 5 | | V-1 | Zcchc2 | 54877 | 4-May-15 |
| 13910 | 3 | 4 | 5 | | | V-1 | Vsig10l | 147645 | 4-May-15 | 14006 | 3 | 4 | 5 | | V-1 | Zcchc24 | 219654 | 4-May-15 |
| 13911 | 3 | 4 | 5 | | | V-1 | Vsx1 | 30813 | 12-May-15 | 14007 | 3 | 4 | 5 | | V-1 | Zcchc3 | 85364 | 4-May-15 |
| 13912 | 3 | 4 | 5 | | | V-1 | Vsx2 | 338917 | 7-Jun-15 | 14008 | 3 | 4 | 5 | | V-1 | Zcchc4 | 29063 | 4-May-15 |
| 13913 | 3 | 4 | 5 | | | V-1 | Vwa1 | 64856 | 4-May-15 | 14009 | 3 | 4 | 5 | | V-1 | Zdbf2 | 57683 | 4-May-15 |
| 13914 | 3 | 4 | 5 | | | V-1 | Vwa5a | 4013 | 4-May-15 | 14010 | 3 | 4 | 5 | | V-1 | Zdhhc13 | 54503 | 12-May-15 |
| 13915 | 3 | 4 | 5 | | | V-1 | Wac | 51322 | 12-May-15 | 14011 | 3 | 4 | 5 | | V-1 | Zdhhc14 | 79683 | 4-May-15 |
| 13916 | 3 | 4 | 5 | | | V-1 | Wars2 | 10352 | 12-May-15 | 14012 | 3 | 4 | 5 | | V-1 | Zdhhc15 | 158866 | 23-May-15 |
| 13917 | 3 | 4 | 5 | | | V-1 | Wbscr16 | 81554 | 4-May-15 | 14013 | 3 | 4 | 5 | | V-1 | Zdhhc16 | 84287 | 4-May-15 |
| 13918 | 3 | 4 | 5 | | | V-1 | Wbscr22 | 114049 | 4-May-15 | 14014 | 3 | 4 | 5 | | V-1 | Zdhhc20 | 253832 | 12-May-15 |
| 13919 | 3 | 4 | 5 | | | V-1 | Wbscr27 | 155368 | 3-May-15 | 14015 | 3 | 4 | 5 | | V-1 | Zdhhc21 | 340481 | 4-May-15 |
| 13920 | 3 | 4 | 5 | | | V-1 | Wbscr28 | 135886 | 4-May-15 | 14016 | 3 | 4 | 5 | | V-1 | Zdhhc22 | 283576 | 4-May-15 |
| 13921 | 3 | 4 | 5 | | | V-1 | Wdfy2 | 115825 | 12-May-15 | 14017 | 3 | 4 | 5 | | V-1 | Zdhhc24 | 254359 | 4-May-15 |
| 13922 | 3 | 4 | 5 | | | V-1 | Wdpcp | 51057 | 23-May-15 | 14018 | 3 | 4 | 5 | | V-1 | Zer1 | 10444 | 4-May-15 |
| 13923 | 3 | 4 | 5 | | | V-1 | Wdr11 | 55717 | 7-Jun-15 | 14019 | 3 | 4 | 5 | | V-1 | Zfand2b | 130617 | 4-May-15 |
| 13924 | 3 | 4 | 5 | | | V-1 | Wdr26 | 80232 | 21-May-15 | 14020 | 3 | 4 | 5 | | V-1 | Zfand5 | 7763 | 4-May-15 |
| 13925 | 3 | 4 | 5 | | | V-1 | Wdr44 | 54521 | 4-May-15 | 14021 | 3 | 4 | 5 | | V-1 | Zfand6 | 54469 | 4-May-15 |
| 13926 | 3 | 4 | 5 | | | V-1 | Wdr6 | 11180 | 4-May-15 | 14022 | 3 | 4 | 5 | | V-1 | Zfa-ps | | |
| 13927 | 3 | 4 | 5 | | | V-1 | Wdr77 | 79084 | 4-May-15 | 14023 | 3 | 4 | 5 | | V-1 | Zfp105 | 7584 | 12-May-15 |
| 13928 | 3 | 4 | 5 | | | V-1 | Wdr91 | 29062 | 12-May-15 | 14024 | 3 | 4 | 5 | | V-1 | Zfp111 | | |
| 13929 | 3 | 4 | 5 | | | V-1 | Wdsub1 | 151525 | 12-May-15 | 14025 | 3 | 4 | 5 | | V-1 | Zfp131 | | |
| 13930 | 3 | 4 | 5 | | | V-1 | Wee2 | 494551 | 7-Jun-15 | 14026 | 3 | 4 | 5 | | V-1 | Zfp191 | 7572 | 12-May-15 |
| 13931 | 3 | 4 | 5 | | | V-1 | Wfdc15a | | | 14027 | 3 | 4 | 5 | | V-1 | Zfp276 | 92822 | 4-May-15 |
| 13932 | 3 | 4 | 5 | | | V-1 | Wfdc18 | | | 14028 | 3 | 4 | 5 | | V-1 | Zfp280d | | |
| 13933 | 3 | 4 | 5 | | | V-1 | Wfdc3 | 140686 | 4-May-15 | 14029 | 3 | 4 | 5 | | V-1 | Zfp3 | 124961 | 4-May-15 |
| 13934 | 3 | 4 | 5 | | | V-1 | Wfikkn1 | 117166 | 4-May-15 | 14030 | 3 | 4 | 5 | | V-1 | Zfp300 | | |
| 13935 | 3 | 4 | 5 | | | V-1 | Wfs1 | 7466 | 31-May-15 | 14031 | 3 | 4 | 5 | | V-1 | Zfp317 | | |
| 13936 | 3 | 4 | 5 | | | V-1 | Whamm | 123720 | 4-May-15 | 14032 | 3 | 4 | 5 | | V-1 | Zfp334 | | |
| 13937 | 3 | 4 | 5 | | | V-1 | Whsc1 | 7468 | 23-May-15 | 14033 | 3 | 4 | 5 | | V-1 | Zfp354c | | |
| 13938 | 3 | 4 | 5 | | | V-1 | Whsc1l1 | 54904 | 7-Jun-15 | 14034 | 3 | 4 | 5 | | V-1 | Zfp358 | | |
| 13939 | 3 | 4 | 5 | | | V-1 | Wipf2 | 147179 | 10-May-15 | 14035 | 3 | 4 | 5 | | V-1 | Zfp362 | | |
| 13940 | 3 | 4 | 5 | | | V-1 | Wipi2 | 26100 | 21-May-15 | 14036 | 3 | 4 | 5 | | V-1 | Zfp369 | | |
| 13941 | 3 | 4 | 5 | | | V-1 | Wisp3 | 8838 | 4-May-15 | 14037 | 3 | 4 | 5 | | V-1 | Zfp36l3 | | |
| 13942 | 3 | 4 | 5 | | | V-1 | Wnt16 | 51384 | 7-Jun-15 | 14038 | 3 | 4 | 5 | | V-1 | Zfp382 | | |
| 13943 | 3 | 4 | 5 | | | V-1 | Wnt3 | 7473 | 23-May-15 | 14039 | 3 | 4 | 5 | | V-1 | Zfp383 | | |
| 13944 | 3 | 4 | 5 | | | V-1 | Wnt5a | 7474 | 31-May-15 | 14040 | 3 | 4 | 5 | | V-1 | Zfp389 | | |
| 13945 | 3 | 4 | 5 | | | V-1 | Wnt6 | 7475 | 4-May-15 | 14041 | 3 | 4 | 5 | | V-1 | Zfp397 | | |
| 13946 | 3 | 4 | 5 | | | V-1 | Wnt7a | 7476 | 4-May-15 | 14042 | 3 | 4 | 5 | | V-1 | Zfp407 | | |
| 13947 | 3 | 4 | 5 | | | V-1 | Wnt7b | 7477 | 4-May-15 | 14043 | 3 | 4 | 5 | | V-1 | Zfp426 | | |
| 13948 | 3 | 4 | 5 | | | V-1 | Wnt9a | 7483 | 4-May-15 | 14044 | 3 | 4 | 5 | | V-1 | Zfp429 | | |
| 13949 | 3 | 4 | 5 | | | V-1 | Wnip1 | 56897 | 4-May-15 | 14045 | 3 | 4 | 5 | | V-1 | Zfp444 | | |
| 13950 | 3 | 4 | 5 | | | V-1 | Wsb2 | 55884 | 2-Jun-15 | 14046 | 3 | 4 | 5 | | V-1 | Zfp446 | | |
| 13951 | 3 | 4 | 5 | | | V-1 | Wt1os | | | 14047 | 3 | 4 | 5 | | V-1 | Zfp462 | 58499 | 4-May-15 |
| 13952 | 3 | 4 | 5 | | | V-1 | Wwc2 | 80014 | 4-May-15 | 14048 | 3 | 4 | 5 | | V-1 | Zfp467 | 168544 | 4-May-15 |
| 13953 | 3 | 4 | 5 | | | V-1 | Xab2 | 56949 | 4-May-15 | 14049 | 3 | 4 | 5 | | V-1 | Zfp493 | | |
| 13954 | 3 | 4 | 5 | | | V-1 | Xbp1 | 7494 | 7-Jun-15 | 14050 | 3 | 4 | 5 | | V-1 | Zfp507 | | |
| 13955 | 3 | 4 | 5 | | | V-1 | Xcl1 | 6375 | 4-May-15 | 14051 | 3 | 4 | 5 | | V-1 | Zfp512 | | |
| 13956 | 3 | 4 | 5 | | | V-1 | Xiap | 331 | 23-May-15 | 14052 | 3 | 4 | 5 | | V-1 | Zfp523 | 7629 | 4-May-15 |
| 13957 | 3 | 4 | 5 | | | V-1 | Xist | 7503 | 7-Jun-15 | 14053 | 3 | 4 | 5 | | V-1 | Zfp558 | | |
| 13958 | 3 | 4 | 5 | | | V-1 | Xkr4 | 114786 | 4-May-15 | 14054 | 3 | 4 | 5 | | V-1 | Zfp57 | 346171 | 22-May-15 |

Fig. 30 - 75

| | | | | | | | | | | | | | | | | | | |
|---|---|---|---|---|---|---|---|---|---|---|---|---|---|---|---|---|---|---|
| 14055 | 3 | 4 | 5 | | | V-1 | Zfp572 | | | 14149 | 3 | 4 | | | | IV-2 | 4921524J17Rik | | |
| 14056 | 3 | 4 | 5 | | | V-1 | Zfp583 | | | 14150 | 3 | 4 | | | | IV-2 | 4922502N22Rik | | |
| 14057 | 3 | 4 | 5 | | | V-1 | Zfp595 | | | 14151 | 3 | 4 | | | | IV-2 | 4930402K13Rik | | |
| 14058 | 3 | 4 | 5 | | | V-1 | Zfp609 | | | 14152 | 3 | 4 | | | | IV-2 | 4930413M19Rik | | |
| 14059 | 3 | 4 | 5 | | | V-1 | Zfp616 | | | 14153 | 3 | 4 | | | | IV-2 | 4930417O22Rik | | |
| 14060 | 3 | 4 | 5 | | | V-1 | Zfp618 | | | 14154 | 3 | 4 | | | | IV-2 | 4930428O21Rik | | |
| 14061 | 3 | 4 | 5 | | | V-1 | Zfp619 | | | 14155 | 3 | 4 | | | | IV-2 | 4930430D24Rik | | |
| 14062 | 3 | 4 | 5 | | | V-1 | Zfp628 | 89887 | 4-May-15 | 14156 | 3 | 4 | | | | IV-2 | 4930447K03Rik | | |
| 14063 | 3 | 4 | 5 | | | V-1 | Zfp641 | | | 14157 | 3 | 4 | | | | IV-2 | 4930448H16Rik | | |
| 14064 | 3 | 4 | 5 | | | V-1 | Zfp65 | | | 14158 | 3 | 4 | | | | IV-2 | 4930452A19Rik | | |
| 14065 | 3 | 4 | 5 | | | V-1 | Zfp663 | | | 14159 | 3 | 4 | | | | IV-2 | 4930465K10Rik | | |
| 14066 | 3 | 4 | 5 | | | V-1 | Zfp691 | 51058 | 4-May-15 | 14160 | 3 | 4 | | | | IV-2 | 4930467K11Rik | | |
| 14067 | 3 | 4 | 5 | | | V-1 | Zfp7 | | | 14161 | 3 | 4 | | | | IV-2 | 4930474G06Rik | | |
| 14068 | 3 | 4 | 5 | | | V-1 | Zfp704 | | | 14162 | 3 | 4 | | | | IV-2 | 4930479D17Rik | | |
| 14069 | 3 | 4 | 5 | | | V-1 | Zfp707 | | | 14163 | 3 | 4 | | | | IV-2 | 4930488L21Rik | | |
| 14070 | 3 | 4 | 5 | | | V-1 | Zfp758 | | | 14164 | 3 | 4 | | | | IV-2 | 4930500J02Rik | | |
| 14071 | 3 | 4 | 5 | | | V-1 | Zfp763 | | | 14165 | 3 | 4 | | | | IV-2 | 4930503H13Rik | | |
| 14072 | 3 | 4 | 5 | | | V-1 | Zfp799 | | | 14166 | 3 | 4 | | | | IV-2 | 4930515G01Rik | | |
| 14073 | 3 | 4 | 5 | | | V-1 | Zfp809 | | | 14167 | 3 | 4 | | | | IV-2 | 4930515L03Rik | | |
| 14074 | 3 | 4 | 5 | | | V-1 | Zfp819 | | | 14168 | 3 | 4 | | | | IV-2 | 4930519D14Rik | | |
| 14075 | 3 | 4 | 5 | | | V-1 | Zfp831 | | | 14169 | 3 | 4 | | | | IV-2 | 4930524N10Rik | | |
| 14076 | 3 | 4 | 5 | | | V-1 | Zfp839 | | | 14170 | 3 | 4 | | | | IV-2 | 4930528A17Rik | | |
| 14077 | 3 | 4 | 5 | | | V-1 | Zfp84 | | | 14171 | 3 | 4 | | | | IV-2 | 4930545H06Rik | | |
| 14078 | 3 | 4 | 5 | | | V-1 | Zfp85os | | | 14172 | 3 | 4 | | | | IV-2 | 4930545L23Rik | | |
| 14079 | 3 | 4 | 5 | | | V-1 | Zfp865 | | | 14173 | 3 | 4 | | | | IV-2 | 4930549C01Rik | | |
| 14080 | 3 | 4 | 5 | | | V-1 | Zfp869 | | | 14174 | 3 | 4 | | | | IV-2 | 4930553E22Rik | | |
| 14081 | 3 | 4 | 5 | | | V-1 | Zfp871 | | | 14175 | 3 | 4 | | | | IV-2 | 4930556J02Rik | | |
| 14082 | 3 | 4 | 5 | | | V-1 | Zfp873 | | | 14176 | 3 | 4 | | | | IV-2 | 4930557A04Rik | | |
| 14083 | 3 | 4 | 5 | | | V-1 | Zfp879 | | | 14177 | 3 | 4 | | | | IV-2 | 4930562F07Rik | | |
| 14084 | 3 | 4 | 5 | | | V-1 | Zfp90 | 146198 | 20-May-15 | 14178 | 3 | 4 | | | | IV-2 | 4930563E22Rik | | |
| 14085 | 3 | 4 | 5 | | | V-1 | Zfp938 | | | 14179 | 3 | 4 | | | | IV-2 | 4930567H17Rik | | |
| 14086 | 3 | 4 | 5 | | | V-1 | Zfp941 | | | 14180 | 3 | 4 | | | | IV-2 | 4930568D16Rik | | |
| 14087 | 3 | 4 | 5 | | | V-1 | Zfp951 | | | 14181 | 3 | 4 | | | | IV-2 | 4930595M18Rik | | |
| 14088 | 3 | 4 | 5 | | | V-1 | Zfp952 | | | 14182 | 3 | 4 | | | | IV-2 | 4930596I21Rik | | |
| 14089 | 3 | 4 | 5 | | | V-1 | Zfp964 | | | 14183 | 3 | 4 | | | | IV-2 | 4931429P17Rik | | |
| 14090 | 3 | 4 | 5 | | | V-1 | Zfpm2 | 23414 | 4-May-15 | 14184 | 3 | 4 | | | | IV-2 | 4931440L10Rik | | |
| 14091 | 3 | 4 | 5 | | | V-1 | Zfx | 7543 | 31-May-15 | 14185 | 3 | 4 | | | | IV-2 | 4933400B14Rik | | |
| 14092 | 3 | 4 | 5 | | | V-1 | Zfyve16 | 9765 | 4-May-15 | 14186 | 3 | 4 | | | | IV-2 | 4933400L20Rik | | |
| 14093 | 3 | 4 | 5 | | | V-1 | Zfyve26 | 23503 | 4-May-15 | 14187 | 3 | 4 | | | | IV-2 | 4933401H06Rik | | |
| 14094 | 3 | 4 | 5 | | | V-1 | Zfyve9 | 9372 | 24-May-15 | 14188 | 3 | 4 | | | | IV-2 | 4933402D24Rik | | |
| 14095 | 3 | 4 | 5 | | | V-1 | Zglp1 | 100125288 | 4-May-15 | 14189 | 3 | 4 | | | | IV-2 | 4933402J10Rik | | |
| 14096 | 3 | 4 | 5 | | | V-1 | Zhx1 | 11244 | 4-May-15 | 14190 | 3 | 4 | | | | IV-2 | 4933406I18Rik | | |
| 14097 | 3 | 4 | 5 | | | V-1 | Zic1 | 7545 | 2-Jun-15 | 14191 | 3 | 4 | | | | IV-2 | 4933416E03Rik | | |
| 14098 | 3 | 4 | 5 | | | V-1 | Zim3 | 114026 | 12-May-15 | 14192 | 3 | 4 | | | | IV-2 | 4933427E11Rik | | |
| 14099 | 3 | 4 | 5 | | | V-1 | Zmynd11 | 10771 | 4-May-15 | 14193 | 3 | 4 | | | | IV-2 | 4933427G17Rik | | |
| 14100 | 3 | 4 | 5 | | | V-1 | Zmynd19 | 116225 | 2-Jun-15 | 14194 | 3 | 4 | | | | IV-2 | 4933432I03Rik | | |
| 14101 | 3 | 4 | 5 | | | V-1 | Zmynd8 | 23613 | 12-May-15 | 14195 | 3 | 4 | | | | IV-2 | 4933433G19Rik | | |
| 14102 | 3 | 4 | 5 | | | V-1 | Znf512b | 57473 | 4-May-15 | 14196 | 3 | 4 | | | | IV-2 | 4933438B17Rik | | |
| 14103 | 3 | 4 | 5 | | | V-1 | Znrd1 | 30834 | 12-May-15 | 14197 | 3 | 4 | | | | IV-2 | 5330411J11Rik | | |
| 14104 | 3 | 4 | 5 | | | V-1 | Znrf1 | 84937 | 23-May-15 | 14198 | 3 | 4 | | | | IV-2 | 5430419D17Rik | | |
| 14105 | 3 | 4 | 5 | | | V-1 | Zrsr1 | 7310 | 4-May-15 | 14199 | 3 | 4 | | | | IV-2 | 5730403I07Rik | | |
| 14106 | 3 | 4 | 5 | | | V-1 | Zrsr2 | 8233 | 4-May-15 | 14200 | 3 | 4 | | | | IV-2 | 5730440C07Rik | | |
| 14107 | 3 | 4 | 5 | | | V-1 | Zscan2 | 54993 | 12-May-15 | 14201 | 3 | 4 | | | | IV-2 | 6030466F02Rik | | |
| 14108 | 3 | 4 | 5 | | | V-1 | Zscan22 | 342945 | 4-May-15 | 14202 | 3 | 4 | | | | IV-2 | 6430503K07Rik | | |
| 14109 | 3 | 4 | 5 | | | V-1 | Zscan25 | 221785 | 4-May-15 | 14203 | 3 | 4 | | | | IV-2 | 6430531B16Rik | | |
| 14110 | 3 | 4 | 5 | | | V-1 | Zswim5 | 57643 | 4-May-15 | 14204 | 3 | 4 | | | | IV-2 | 6530411M01Rik | | |
| 14111 | 3 | 4 | 5 | | | V-1 | Zw10 | 9183 | 29-May-15 | 14205 | 3 | 4 | | | | IV-2 | 7420426K07Rik | | |
| 14112 | 3 | 4 | 5 | | | V-1 | Zxda | 7789 | 4-May-15 | 14206 | 3 | 4 | | | | IV-2 | 8030442B05Rik | | |
| 14113 | 3 | 4 | 5 | | | V-1 | Zyg11b | 79699 | 2-Jun-15 | 14207 | 3 | 4 | | | | IV-2 | 8030443G20Rik | | |
| 14114 | 3 | 4 | 5 | | | V-1 | Zzef1 | 23140 | 12-May-15 | 14208 | 3 | 4 | | | | IV-2 | 8430426J06Rik | | |
| 14115 | 3 | 4 | | | | IV-2 | 1110032A03Rik | | | 14209 | 3 | 4 | | | | IV-2 | 8430437L04Rik | | |
| 14116 | 3 | 4 | | | | IV-2 | 1110057K04Rik | | | 14210 | 3 | 4 | | | | IV-2 | 9030025P20Rik | | |
| 14117 | 3 | 4 | | | | IV-2 | 1700001J03Rik | | | 14211 | 3 | 4 | | | | IV-2 | 9130023H24Rik | | |
| 14118 | 3 | 4 | | | | IV-2 | 1700001K23Rik | | | 14212 | 3 | 4 | | | | IV-2 | 9230112J17Rik | | |
| 14119 | 3 | 4 | | | | IV-2 | 1700003D09Rik | | | 14213 | 3 | 4 | | | | IV-2 | 9330188P03Rik | | |
| 14120 | 3 | 4 | | | | IV-2 | 1700018A04Rik | | | 14214 | 3 | 4 | | | | IV-2 | 9430008C03Rik | | |
| 14121 | 3 | 4 | | | | IV-2 | 1700020A23Rik | | | 14215 | 3 | 4 | | | | IV-2 | 9430020K01Rik | | |
| 14122 | 3 | 4 | | | | IV-2 | 1700024P16Rik | | | 14216 | 3 | 4 | | | | IV-2 | 9430060I03Rik | | |
| 14123 | 3 | 4 | | | | IV-2 | 1700025F24Rik | | | 14217 | 3 | 4 | | | | IV-2 | 9430069I07Rik | | |
| 14124 | 3 | 4 | | | | IV-2 | 1700026D08Rik | | | 14218 | 3 | 4 | | | | IV-2 | 9530053A07Rik | | |
| 14125 | 3 | 4 | | | | IV-2 | 1700030L20Rik | | | 14219 | 3 | 4 | | | | IV-2 | 9530059O14Rik | | |
| 14126 | 3 | 4 | | | | IV-2 | 1700034H15Rik | | | 14220 | 3 | 4 | | | | IV-2 | 9530082F21Rik | | |
| 14127 | 3 | 4 | | | | IV-2 | 1700049L16Rik | | | 14221 | 3 | 4 | | | | IV-2 | A1cf | 29974 | 4-May-15 |
| 14128 | 3 | 4 | | | | IV-2 | 1700061F12Rik | | | 14222 | 3 | 4 | | | | IV-2 | A230046K03Rik | | |
| 14129 | 3 | 4 | | | | IV-2 | 1700063D05Rik | | | 14223 | 3 | 4 | | | | IV-2 | A230073K19Rik | | |
| 14130 | 3 | 4 | | | | IV-2 | 1700065J11Rik | | | 14224 | 3 | 4 | | | | IV-2 | A530006G24Rik | | |
| 14131 | 3 | 4 | | | | IV-2 | 1700065O20Rik | | | 14225 | 3 | 4 | | | | IV-2 | A530013C23Rik | | |
| 14132 | 3 | 4 | | | | IV-2 | 1700066B19Rik | | | 14226 | 3 | 4 | | | | IV-2 | A630012P03Rik | | |
| 14133 | 3 | 4 | | | | IV-2 | 1700066N21Rik | | | 14227 | 3 | 4 | | | | IV-2 | A630073D07Rik | | |
| 14134 | 3 | 4 | | | | IV-2 | 2010111I01Rik | | | 14228 | 3 | 4 | | | | IV-2 | A730008H23Rik | | |
| 14135 | 3 | 4 | | | | IV-2 | 2210018M11Rik | | | 14229 | 3 | 4 | | | | IV-2 | A730098P11Rik | | |
| 14136 | 3 | 4 | | | | IV-2 | 2310034C09Rik | | | 14230 | 3 | 4 | | | | IV-2 | A830009L08Rik | | |
| 14137 | 3 | 4 | | | | IV-2 | 2310061I04Rik | | | 14231 | 3 | 4 | | | | IV-2 | A930013F10Rik | | |
| 14138 | 3 | 4 | | | | IV-2 | 2310067B10Rik | | | 14232 | 3 | 4 | | | | IV-2 | A930018P22Rik | | |
| 14139 | 3 | 4 | | | | IV-2 | 2410004B01Rik | | | 14233 | 3 | 4 | | | | IV-2 | Aamdc | 28971 | 4-May-15 |
| 14140 | 3 | 4 | | | | IV-2 | 2410015M20Rik | | | 14234 | 3 | 4 | | | | IV-2 | Agfg2 | 3268 | 4-May-15 |
| 14141 | 3 | 4 | | | | IV-2 | 2410127L17Rik | | | 14235 | 3 | 4 | | | | IV-2 | AI854703 | | |
| 14142 | 3 | 4 | | | | IV-2 | 2410141O09Rik | | | 14236 | 3 | 4 | | | | IV-2 | Asz1 | 136991 | 4-May-15 |
| 14143 | 3 | 4 | | | | IV-2 | 3000002C10Rik | | | 14237 | 3 | 4 | | | | IV-2 | AU019990 | | |
| 14144 | 3 | 4 | | | | IV-2 | 3110021A11Rik | | | 14238 | 3 | 4 | | | | IV-2 | Azin1 | 51582 | 4-May-15 |
| 14145 | 3 | 4 | | | | IV-2 | 3110040N11Rik | | | 14239 | 3 | 4 | | | | IV-2 | B020018J22Rik | | |
| 14146 | 3 | 4 | | | | IV-2 | 4921513I03Rik | | | 14240 | 3 | 4 | | | | IV-2 | B230118H07Rik | | |
| 14147 | 3 | 4 | | | | IV-2 | 4921515E04Rik | | | 14241 | 3 | 4 | | | | IV-2 | B230206H07Rik | | |
| 14148 | 3 | 4 | | | | IV-2 | 4921517D22Rik | | | 14242 | 3 | 4 | | | | IV-2 | Baat | 570 | 4-May-15 |

Fig. 30 - 76

| | | | | | | | | | | | | | | | |
|---|---|---|---|---|---|---|---|---|---|---|---|---|---|---|---|
| 14243 | 3 | 4 | | | | IV-2 | Bazla | 11177 | 4-May-15 | 14339 | 3 | 4 | | IV-2 | Gm10440 |
| 14244 | 3 | 4 | | | | IV-2 | Bbs2 | 583 | 23-May-15 | 14340 | 3 | 4 | | IV-2 | Gm10471 |
| 14245 | 3 | 4 | | | | IV-2 | BC020402 | | | 14341 | 3 | 4 | | IV-2 | Gm10486 |
| 14246 | 3 | 4 | | | | IV-2 | BC030499 | | | 14342 | 3 | 4 | | IV-2 | Gm10487 |
| 14247 | 3 | 4 | | | | IV-2 | BC061195 | | | 14343 | 3 | 4 | | IV-2 | Gm10512 |
| 14248 | 3 | 4 | | | | IV-2 | Bpnt1 | 10380 | 4-May-15 | 14344 | 3 | 4 | | IV-2 | Gm10516 |
| 14249 | 3 | 4 | | | | IV-2 | Bptf | 2186 | 4-May-15 | 14345 | 3 | 4 | | IV-2 | Gm10549 |
| 14250 | 3 | 4 | | | | IV-2 | Brap | 8315 | 7-Jun-15 | 14346 | 3 | 4 | | IV-2 | Gm10653 |
| 14251 | 3 | 4 | | | | IV-2 | Bud13 | 84811 | 12-May-15 | 14347 | 3 | 4 | | IV-2 | Gm10658 |
| 14252 | 3 | 4 | | | | IV-2 | Bud31 | 8896 | 4-May-15 | 14348 | 3 | 4 | | IV-2 | Gm10697 |
| 14253 | 3 | 4 | | | | IV-2 | C030046E11Rik | | | 14349 | 3 | 4 | | IV-2 | Gm10731 |
| 14254 | 3 | 4 | | | | IV-2 | C2cd2l | 9854 | 4-May-15 | 14350 | 3 | 4 | | IV-2 | Gm10767 |
| 14255 | 3 | 4 | | | | IV-2 | C330024D21Rik | | | 14351 | 3 | 4 | | IV-2 | Gm10782 |
| 14256 | 3 | 4 | | | | IV-2 | C430049B03Rik | | | 14352 | 3 | 4 | | IV-2 | Gm10787 |
| 14257 | 3 | 4 | | | | IV-2 | C8a | 731 | 12-May-15 | 14353 | 3 | 4 | | IV-2 | Gm10845 |
| 14258 | 3 | 4 | | | | IV-2 | Cacna1c | 775 | 23-May-15 | 14354 | 3 | 4 | | IV-2 | Gm11413 |
| 14259 | 3 | 4 | | | | IV-2 | Calm2 | 805 | 12-May-15 | 14355 | 3 | 4 | | IV-2 | Gm11426 |
| 14260 | 3 | 4 | | | | IV-2 | Capn8 | 388743 | 4-May-15 | 14356 | 3 | 4 | | IV-2 | Gm11545 |
| 14261 | 3 | 4 | | | | IV-2 | Cdipt | 10423 | 4-May-15 | 14357 | 3 | 4 | | IV-2 | Gm11548 |
| 14262 | 3 | 4 | | | | IV-2 | Ceacam12 | | | 14358 | 3 | 4 | | IV-2 | Gm12295 |
| 14263 | 3 | 4 | | | | IV-2 | Ceacam13 | | | 14359 | 3 | 4 | | IV-2 | Gm12942 |
| 14264 | 3 | 4 | | | | IV-2 | Ceacam19 | 56971 | 4-May-15 | 14360 | 3 | 4 | | IV-2 | Gm13119 |
| 14265 | 3 | 4 | | | | IV-2 | Ceacam3 | 1084 | 4-May-15 | 14361 | 3 | 4 | | IV-2 | Gm13124 |
| 14266 | 3 | 4 | | | | IV-2 | Ceacam5 | 1048 | 21-May-15 | 14362 | 3 | 4 | | IV-2 | Gm13125 |
| 14267 | 3 | 4 | | | | IV-2 | Cebpz | 10153 | 7-Jun-15 | 14363 | 3 | 4 | | IV-2 | Gm13128 |
| 14268 | 3 | 4 | | | | IV-2 | Cers4 | 79603 | 4-May-15 | 14364 | 3 | 4 | | IV-2 | Gm13178 |
| 14269 | 3 | 4 | | | | IV-2 | Cetn3 | 1070 | 12-May-15 | 14365 | 3 | 4 | | IV-2 | Gm13283 |
| 14270 | 3 | 4 | | | | IV-2 | Chml | 1122 | 4-May-15 | 14366 | 3 | 4 | | IV-2 | Gm13285 |
| 14271 | 3 | 4 | | | | IV-2 | Chmp2b | 25978 | 23-May-15 | 14367 | 3 | 4 | | IV-2 | Gm13288 |
| 14272 | 3 | 4 | | | | IV-2 | Chrna9 | 55584 | 12-May-15 | 14368 | 3 | 4 | | IV-2 | Gm13290 |
| 14273 | 3 | 4 | | | | IV-2 | Chst15 | 51363 | 12-May-15 | 14369 | 3 | 4 | | IV-2 | Gm13293 |
| 14274 | 3 | 4 | | | | IV-2 | Cltb | 1212 | 4-May-15 | 14370 | 3 | 4 | | IV-2 | Gm13580 |
| 14275 | 3 | 4 | | | | IV-2 | Cnih2 | 254263 | 4-May-15 | 14371 | 3 | 4 | | IV-2 | Gm13582 |
| 14276 | 3 | 4 | | | | IV-2 | Cryba2 | 1412 | 3-May-15 | 14372 | 3 | 4 | | IV-2 | Gm13769 |
| 14277 | 3 | 4 | | | | IV-2 | Cryl1 | 51084 | 4-May-15 | 14373 | 3 | 4 | | IV-2 | Gm13807 |
| 14278 | 3 | 4 | | | | IV-2 | Cs | 1431 | 4-May-15 | 14374 | 3 | 4 | | IV-2 | Gm14139 |
| 14279 | 3 | 4 | | | | IV-2 | Csmd2 | 114784 | 4-May-15 | 14375 | 3 | 4 | | IV-2 | Gm14204 |
| 14280 | 3 | 4 | | | | IV-2 | Csnk1a1 | 1452 | 4-May-15 | 14376 | 3 | 4 | | IV-2 | Gm14207 |
| 14281 | 3 | 4 | | | | IV-2 | Ctcf | 10664 | 12-May-15 | 14377 | 3 | 4 | | IV-2 | Gm14479 |
| 14282 | 3 | 4 | | | | IV-2 | Cttnbp2nl | 55917 | 4-May-15 | 14378 | 3 | 4 | | IV-2 | Gm14483 |
| 14283 | 3 | 4 | | | | IV-2 | Cyp21a1 | | | 14379 | 3 | 4 | | IV-2 | Gm14525 |
| 14284 | 3 | 4 | | | | IV-2 | Cyp2c66 | | | 14380 | 3 | 4 | | IV-2 | Gm14781 |
| 14285 | 3 | 4 | | | | IV-2 | Cyp4f14 | | | 14381 | 3 | 4 | | IV-2 | Gm14812 |
| 14286 | 3 | 4 | | | | IV-2 | D030047H15Rik | | | 14382 | 3 | 4 | | IV-2 | Gm14819 |
| 14287 | 3 | 4 | | | | IV-2 | D030056L22Rik | | | 14383 | 3 | 4 | | IV-2 | Gm14851 |
| 14288 | 3 | 4 | | | | IV-2 | D130009I18Rik | | | 14384 | 3 | 4 | | IV-2 | Gm14858 |
| 14289 | 3 | 4 | | | | IV-2 | D17Wsu104e | | | 14385 | 3 | 4 | | IV-2 | Gm15008 |
| 14290 | 3 | 4 | | | | IV-2 | Dcaf13 | 25879 | 4-May-15 | 14386 | 3 | 4 | | IV-2 | Gm15097 |
| 14291 | 3 | 4 | | | | IV-2 | Dennd1b | 163486 | 12-May-15 | 14387 | 3 | 4 | | IV-2 | Gm15328 |
| 14292 | 3 | 4 | | | | IV-2 | Dmap1 | 55929 | 4-May-15 | 14388 | 3 | 4 | | IV-2 | Gm16046 |
| 14293 | 3 | 4 | | | | IV-2 | Dmrt1 | 1761 | 4-May-15 | 14389 | 3 | 4 | | IV-2 | Gm16336 |
| 14294 | 3 | 4 | | | | IV-2 | Dmxl2 | 23312 | 31-May-15 | 14390 | 3 | 4 | | IV-2 | Gm16381 |
| 14295 | 3 | 4 | | | | IV-2 | Dnttip2 | 30836 | 4-May-15 | 14391 | 3 | 4 | | IV-2 | Gm16390 |
| 14296 | 3 | 4 | | | | IV-2 | Dpf1 | 8193 | 2-Jun-15 | 14392 | 3 | 4 | | IV-2 | Gm16404 |
| 14297 | 3 | 4 | | | | IV-2 | Drp2 | 1821 | 7-Jun-15 | 14393 | 3 | 4 | | IV-2 | Gm16432 |
| 14298 | 3 | 4 | | | | IV-2 | Dsg1b | | | 14394 | 3 | 4 | | IV-2 | Gm16532 |
| 14299 | 3 | 4 | | | | IV-2 | Dus4l | 11062 | 4-May-15 | 14395 | 3 | 4 | | IV-2 | Gm16548 |
| 14300 | 3 | 4 | | | | IV-2 | Dync2li1 | 51626 | 4-May-15 | 14396 | 3 | 4 | | IV-2 | Gm16982 |
| 14301 | 3 | 4 | | | | IV-2 | E130310I04Rik | | | 14397 | 3 | 4 | | IV-2 | Gm17644 |
| 14302 | 3 | 4 | | | | IV-2 | E330034G19Rik | | | 14398 | 3 | 4 | | IV-2 | Gm17751 |
| 14303 | 3 | 4 | | | | IV-2 | E530001F21Rik | | | 14399 | 3 | 4 | | IV-2 | Gm17769 |
| 14304 | 3 | 4 | | | | IV-2 | Eif4g1 | 1981 | 29-May-15 | 14400 | 3 | 4 | | IV-2 | Gm1821 |
| 14305 | 3 | 4 | | | | IV-2 | Engase | 64772 | 4-May-15 | 14401 | 3 | 4 | | IV-2 | Gm19303 |
| 14306 | 3 | 4 | | | | IV-2 | Entpd4 | 9583 | 21-May-15 | 14402 | 3 | 4 | | IV-2 | Gm1943 |
| 14307 | 3 | 4 | | | | IV-2 | Epha6 | 285220 | 4-May-15 | 14403 | 3 | 4 | | IV-2 | Gm19589 |
| 14308 | 3 | 4 | | | | IV-2 | Eps8 | 2059 | 4-May-15 | 14404 | 3 | 4 | | IV-2 | Gm1965 |
| 14309 | 3 | 4 | | | | IV-2 | Esp31 | | | 14405 | 3 | 4 | | IV-2 | Gm20172 |
| 14310 | 3 | 4 | | | | IV-2 | Esp34 | | | 14406 | 3 | 4 | | IV-2 | Gm20199 |
| 14311 | 3 | 4 | | | | IV-2 | Esp36 | | | 14407 | 3 | 4 | | IV-2 | Gm20300 |
| 14312 | 3 | 4 | | | | IV-2 | Esp38 | | | 14408 | 3 | 4 | | IV-2 | Gm20753 |
| 14313 | 3 | 4 | | | | IV-2 | Esp4 | | | 14409 | 3 | 4 | | IV-2 | Gm20806 |
| 14314 | 3 | 4 | | | | IV-2 | Esp5 | | | 14410 | 3 | 4 | | IV-2 | Gm20809 |
| 14315 | 3 | 4 | | | | IV-2 | Esp6 | | | 14411 | 3 | 4 | | IV-2 | Gm20815 |
| 14316 | 3 | 4 | | | | IV-2 | Esp6-esp5 | | | 14412 | 3 | 4 | | IV-2 | Gm20822 |
| 14317 | 3 | 4 | | | | IV-2 | Esp8 | | | 14413 | 3 | 4 | | IV-2 | Gm20823 |
| 14318 | 3 | 4 | | | | IV-2 | Esr1 | 2099 | 31-May-15 | 14414 | 3 | 4 | | IV-2 | Gm20826 |
| 14319 | 3 | 4 | | | | IV-2 | F9 | 2158 | 23-May-15 | 14415 | 3 | 4 | | IV-2 | Gm20857 |
| 14320 | 3 | 4 | | | | IV-2 | Fam161a | 84140 | 23-May-15 | 14416 | 3 | 4 | | IV-2 | Gm21284 |
| 14321 | 3 | 4 | | | | IV-2 | Fbxw2 | 26190 | 4-May-15 | 14417 | 3 | 4 | | IV-2 | Gm21312 |
| 14322 | 3 | 4 | | | | IV-2 | Fbxw20 | | | 14418 | 3 | 4 | | IV-2 | Gm21319 |
| 14323 | 3 | 4 | | | | IV-2 | Fbxw21 | | | 14419 | 3 | 4 | | IV-2 | Gm2381 |
| 14324 | 3 | 4 | | | | IV-2 | Fbxw22 | | | 14420 | 3 | 4 | | IV-2 | Gm3264 |
| 14325 | 3 | 4 | | | | IV-2 | Fbxw5 | 54461 | 4-May-15 | 14421 | 3 | 4 | | IV-2 | Gm3404 |
| 14326 | 3 | 4 | | | | IV-2 | Fbxw7 | 55294 | 12-May-15 | 14422 | 3 | 4 | | IV-2 | Gm3604 |
| 14327 | 3 | 4 | | | | IV-2 | Fbxw8 | 26259 | 4-May-15 | 14423 | 3 | 4 | | IV-2 | Gm362 |
| 14328 | 3 | 4 | | | | IV-2 | Fbxw9 | 84261 | 4-May-15 | 14424 | 3 | 4 | | IV-2 | Gm4201 |
| 14329 | 3 | 4 | | | | IV-2 | Fes | 2242 | 12-May-15 | 14425 | 3 | 4 | | IV-2 | Gm4224 |
| 14330 | 3 | 4 | | | | IV-2 | Foxl2 | 668 | 28-May-15 | 14426 | 3 | 4 | | IV-2 | Gm4251 |
| 14331 | 3 | 4 | | | | IV-2 | G6pc3 | 92579 | 4-May-15 | 14427 | 3 | 4 | | IV-2 | Gm4262 |
| 14332 | 3 | 4 | | | | IV-2 | Gapdh | 2597 | 7-Jun-15 | 14428 | 3 | 4 | | IV-2 | Gm4285 |
| 14333 | 3 | 4 | | | | IV-2 | Gdap2 | 54834 | 12-May-15 | 14429 | 3 | 4 | | IV-2 | Gm4371 |
| 14334 | 3 | 4 | | | | IV-2 | Gemin6 | 79833 | 4-May-15 | 14430 | 3 | 4 | | IV-2 | Gm438 |
| 14335 | 3 | 4 | | | | IV-2 | Gkn1 | 56287 | 4-May-15 | 14431 | 3 | 4 | | IV-2 | Gm44 |
| 14336 | 3 | 4 | | | | IV-2 | Gm10373 | | | 14432 | 3 | 4 | | IV-2 | Gm4461 |
| 14337 | 3 | 4 | | | | IV-2 | Gm10408 | | | 14433 | 3 | 4 | | IV-2 | Gm4532 |
| 14338 | 3 | 4 | | | | IV-2 | Gm10416 | | | 14434 | 3 | 4 | | IV-2 | Gm4710 |

Fig. 30 - 77

| | | | | | | | | | | | | | | | | |
|---|---|---|---|---|---|---|---|---|---|---|---|---|---|---|---|---|
| 14435 | 3 | 4 | | | | IV-2 | Gm4890 | | | 14531 | 3 | 4 | | | IV-2 | Mir380 | 494329 | 21-May-15 |
| 14436 | 3 | 4 | | | | IV-2 | Gm4894 | | | 14532 | 3 | 4 | | | IV-2 | Mir467a-4 | | |
| 14437 | 3 | 4 | | | | IV-2 | Gm4925 | | | 14533 | 3 | 4 | | | IV-2 | Mir467a-8 | | |
| 14438 | 3 | 4 | | | | IV-2 | Gm4944 | | | 14534 | 3 | 4 | | | IV-2 | Mir467d | | |
| 14439 | 3 | 4 | | | | IV-2 | Gm4951 | | | 14535 | 3 | 4 | | | IV-2 | Mir471 | | |
| 14440 | 3 | 4 | | | | IV-2 | Gm5065 | | | 14536 | 3 | 4 | | | IV-2 | Mir6240 | | |
| 14441 | 3 | 4 | | | | IV-2 | Gm5069 | | | 14537 | 3 | 4 | | | IV-2 | Mir669a-5 | | |
| 14442 | 3 | 4 | | | | IV-2 | Gm5091 | | | 14538 | 3 | 4 | | | IV-2 | Mir669a-9 | | |
| 14443 | 3 | 4 | | | | IV-2 | Gm5124 | | | 14539 | 3 | 4 | | | IV-2 | Mir669b | | |
| 14444 | 3 | 4 | | | | IV-2 | Gm5142 | | | 14540 | 3 | 4 | | | IV-2 | Mir669p-1 | | |
| 14445 | 3 | 4 | | | | IV-2 | Gm5477 | | | 14541 | 3 | 4 | | | IV-2 | Mir7213 | | |
| 14446 | 3 | 4 | | | | IV-2 | Gm5726 | | | 14542 | 3 | 4 | | | IV-2 | Mrgprb1 | | |
| 14447 | 3 | 4 | | | | IV-2 | Gm5796 | | | 14543 | 3 | 4 | | | IV-2 | Muc1 | 118430 | 4-May-15 |
| 14448 | 3 | 4 | | | | IV-2 | Gm5891 | | | 14544 | 3 | 4 | | | IV-2 | Mut1 | 79594 | 23-May-15 |
| 14449 | 3 | 4 | | | | IV-2 | Gm5916 | | | 14545 | 3 | 4 | | | IV-2 | Napjl2 | 4674 | 12-May-15 |
| 14450 | 3 | 4 | | | | IV-2 | Gm5925 | | | 14546 | 3 | 4 | | | IV-2 | Nf2 | 4771 | 1-Jun-15 |
| 14451 | 3 | 4 | | | | IV-2 | Gm5934 | | | 14547 | 3 | 4 | | | IV-2 | Nkx2-5 | 1482 | 31-May-15 |
| 14452 | 3 | 4 | | | | IV-2 | Gm5941 | | | 14548 | 3 | 4 | | | IV-2 | Nkx3-1 | 4824 | 12-May-15 |
| 14453 | 3 | 4 | | | | IV-2 | Gm6194 | | | 14549 | 3 | 4 | | | IV-2 | Nkx3-2 | 579 | 4-May-15 |
| 14454 | 3 | 4 | | | | IV-2 | Gm6225 | | | 14550 | 3 | 4 | | | IV-2 | Nlgn2 | 57555 | 28-May-15 |
| 14455 | 3 | 4 | | | | IV-2 | Gm6260 | | | 14551 | 3 | 4 | | | IV-2 | Nlrp4f | | |
| 14456 | 3 | 4 | | | | IV-2 | Gm6370 | | | 14552 | 3 | 4 | | | IV-2 | Nlrp4g | | |
| 14457 | 3 | 4 | | | | IV-2 | Gm6484 | | | 14553 | 3 | 4 | | | IV-2 | Nlrp9b | | |
| 14458 | 3 | 4 | | | | IV-2 | Gm6602 | | | 14554 | 3 | 4 | | | IV-2 | Nlrx1 | 79671 | 4-May-15 |
| 14459 | 3 | 4 | | | | IV-2 | Gm6938 | | | 14555 | 3 | 4 | | | IV-2 | Npepps | 9520 | 4-May-15 |
| 14460 | 3 | 4 | | | | IV-2 | Gm6984 | | | 14556 | 3 | 4 | | | IV-2 | Npsr1 | 387129 | 31-May-15 |
| 14461 | 3 | 4 | | | | IV-2 | Gm7073 | | | 14557 | 3 | 4 | | | IV-2 | Nr2e3 | 10002 | 23-May-15 |
| 14462 | 3 | 4 | | | | IV-2 | Gm715 | | | 14558 | 3 | 4 | | | IV-2 | Obscn | 84033 | 28-May-15 |
| 14463 | 3 | 4 | | | | IV-2 | Gm7367 | | | 14559 | 3 | 4 | | | IV-2 | Oce1 | 79629 | 4-May-15 |
| 14464 | 3 | 4 | | | | IV-2 | Gm7444 | | | 14560 | 3 | 4 | | | IV-2 | Olfr1009 | | |
| 14465 | 3 | 4 | | | | IV-2 | Gm7977 | | | 14561 | 3 | 4 | | | IV-2 | Olfr101 | | |
| 14466 | 3 | 4 | | | | IV-2 | Gm8298 | | | 14562 | 3 | 4 | | | IV-2 | Olfr1010 | | |
| 14467 | 3 | 4 | | | | IV-2 | Gm8580 | | | 14563 | 3 | 4 | | | IV-2 | Olfr1012 | | |
| 14468 | 3 | 4 | | | | IV-2 | Gm8882 | | | 14564 | 3 | 4 | | | IV-2 | Olfr1013 | | |
| 14469 | 3 | 4 | | | | IV-2 | Gm8884 | | | 14565 | 3 | 4 | | | IV-2 | Olfr1014 | | |
| 14470 | 3 | 4 | | | | IV-2 | Gm9513 | | | 14566 | 3 | 4 | | | IV-2 | Olfr1016 | | |
| 14471 | 3 | 4 | | | | IV-2 | Gm9696 | | | 14567 | 3 | 4 | | | IV-2 | Olfr1018 | | |
| 14472 | 3 | 4 | | | | IV-2 | Gm9961 | | | 14568 | 3 | 4 | | | IV-2 | Olfr1019 | | |
| 14473 | 3 | 4 | | | | IV-2 | Golga7 | 57125 | 4-May-15 | 14569 | 3 | 4 | | | IV-2 | Olfr102 | | |
| 14474 | 3 | 4 | | | | IV-2 | Gpr152 | 390212 | 4-May-15 | 14570 | 3 | 4 | | | IV-2 | Olfr1020 | | |
| 14475 | 3 | 4 | | | | IV-2 | Gpr153 | 387509 | 4-May-15 | 14571 | 3 | 4 | | | IV-2 | Olfr1022 | | |
| 14476 | 3 | 4 | | | | IV-2 | Gpr160 | 26996 | 4-May-15 | 14572 | 3 | 4 | | | IV-2 | Olfr1023 | | |
| 14477 | 3 | 4 | | | | IV-2 | Gpsm1 | 26086 | 4-May-15 | 14573 | 3 | 4 | | | IV-2 | Olfr1024 | | |
| 14478 | 3 | 4 | | | | IV-2 | Grifin | 402635 | 3-May-15 | 14574 | 3 | 4 | | | IV-2 | Olfr1026 | | |
| 14479 | 3 | 4 | | | | IV-2 | Grin2a | 2903 | 31-May-15 | 14575 | 3 | 4 | | | IV-2 | Olfr1028 | | |
| 14480 | 3 | 4 | | | | IV-2 | Grm4 | 2914 | 7-Jun-15 | 14576 | 3 | 4 | | | IV-2 | Olfr1029 | | |
| 14481 | 3 | 4 | | | | IV-2 | Gsdma3 | | | 14577 | 3 | 4 | | | IV-2 | Olfr103 | | |
| 14482 | 3 | 4 | | | | IV-2 | Gtf2b | 2959 | 4-May-15 | 14578 | 3 | 4 | | | IV-2 | Olfr1030 | | |
| 14483 | 3 | 4 | | | | IV-2 | Gulp1 | 51454 | 12-May-15 | 14579 | 3 | 4 | | | IV-2 | Olfr1031 | | |
| 14484 | 3 | 4 | | | | IV-2 | H13 | 81502 | 23-May-15 | 14580 | 3 | 4 | | | IV-2 | Olfr1032 | | |
| 14485 | 3 | 4 | | | | IV-2 | H2-M11 | | | 14581 | 3 | 4 | | | IV-2 | Olfr1033 | | |
| 14486 | 3 | 4 | | | | IV-2 | Hapln3 | 145864 | 12-May-15 | 14582 | 3 | 4 | | | IV-2 | Olfr1034 | | |
| 14487 | 3 | 4 | | | | IV-2 | Hnrnpab | 3182 | 4-May-15 | 14583 | 3 | 4 | | | IV-2 | Olfr1036 | | |
| 14488 | 3 | 4 | | | | IV-2 | Hoxa2 | 3199 | 12-May-15 | 14584 | 3 | 4 | | | IV-2 | Olfr1037 | | |
| 14489 | 3 | 4 | | | | IV-2 | Hoxd10 | 3236 | 12-May-15 | 14585 | 3 | 4 | | | IV-2 | Olfr1038-ps | | |
| 14490 | 3 | 4 | | | | IV-2 | Htr3a | 3359 | 12-May-15 | 14586 | 3 | 4 | | | IV-2 | Olfr1039 | | |
| 14491 | 3 | 4 | | | | IV-2 | Iars2 | 55699 | 12-May-15 | 14587 | 3 | 4 | | | IV-2 | Olfr1040 | | |
| 14492 | 3 | 4 | | | | IV-2 | Ifna2 | 3440 | 3-May-15 | 14588 | 3 | 4 | | | IV-2 | Olfr1042 | | |
| 14493 | 3 | 4 | | | | IV-2 | Ifna4 | 3441 | 4-May-15 | 14589 | 3 | 4 | | | IV-2 | Olfr1043 | | |
| 14494 | 3 | 4 | | | | IV-2 | Ifna5 | 3442 | 4-May-15 | 14590 | 3 | 4 | | | IV-2 | Olfr1044 | | |
| 14495 | 3 | 4 | | | | IV-2 | Ifna6 | 3443 | 4-May-15 | 14591 | 3 | 4 | | | IV-2 | Olfr1156 | | |
| 14496 | 3 | 4 | | | | IV-2 | Ifna7 | 3444 | 4-May-15 | 14592 | 3 | 4 | | | IV-2 | Olfr1164 | | |
| 14497 | 3 | 4 | | | | IV-2 | Ifna9 | | | 14593 | 3 | 4 | | | IV-2 | Olfr1179 | | |
| 14498 | 3 | 4 | | | | IV-2 | Ifnab | | | 14594 | 3 | 4 | | | IV-2 | Olfr119 | | |
| 14499 | 3 | 4 | | | | IV-2 | Ifnar1 | 3454 | 12-May-15 | 14595 | 3 | 4 | | | IV-2 | Olfr1208 | | |
| 14500 | 3 | 4 | | | | IV-2 | Ifnar2 | 3455 | 12-May-15 | 14596 | 3 | 4 | | | IV-2 | Olfr1301 | | |
| 14501 | 3 | 4 | | | | IV-2 | Ifnb1 | 3456 | 31-May-15 | 14597 | 3 | 4 | | | IV-2 | Olfr131 | | |
| 14502 | 3 | 4 | | | | IV-2 | Ifne | 338376 | 4-May-15 | 14598 | 3 | 4 | | | IV-2 | Olfr1321 | | |
| 14503 | 3 | 4 | | | | IV-2 | Ifng | 3458 | 31-May-15 | 14599 | 3 | 4 | | | IV-2 | Olfr1340 | | |
| 14504 | 3 | 4 | | | | IV-2 | Ifngr1 | 3459 | 12-May-15 | 14600 | 3 | 4 | | | IV-2 | Olfr1387 | | |
| 14505 | 3 | 4 | | | | IV-2 | Ifnl3 | 282617 | 7-Jun-15 | 14601 | 3 | 4 | | | IV-2 | Olfr1388 | | |
| 14506 | 3 | 4 | | | | IV-2 | Ifnlr1 | 163702 | 4-May-15 | 14602 | 3 | 4 | | | IV-2 | Olfr1419 | | |
| 14507 | 3 | 4 | | | | IV-2 | Il1f8 | 27177 | 4-May-15 | 14603 | 3 | 4 | | | IV-2 | Olfr1431 | | |
| 14508 | 3 | 4 | | | | IV-2 | Il31 | 386653 | 7-Jun-15 | 14604 | 3 | 4 | | | IV-2 | Olfr1445 | | |
| 14509 | 3 | 4 | | | | IV-2 | Ilkap | 80895 | 7-Jun-15 | 14605 | 3 | 4 | | | IV-2 | Olfr1448 | | |
| 14510 | 3 | 4 | | | | IV-2 | Ints3 | 65123 | 12-May-15 | 14606 | 3 | 4 | | | IV-2 | Olfr1461 | | |
| 14511 | 3 | 4 | | | | IV-2 | Iqcf3 | 401067 | 4-May-15 | 14607 | 3 | 4 | | | IV-2 | Olfr183 | | |
| 14512 | 3 | 4 | | | | IV-2 | Kcne1 | 3753 | 23-May-15 | 14608 | 3 | 4 | | | IV-2 | Olfr195 | | |
| 14513 | 3 | 4 | | | | IV-2 | Kcnk9 | 51305 | 4-May-15 | 14609 | 3 | 4 | | | IV-2 | Olfr206 | | |
| 14514 | 3 | 4 | | | | IV-2 | Kcns2 | 3788 | 4-May-15 | 14610 | 3 | 4 | | | IV-2 | Olfr24 | | |
| 14515 | 3 | 4 | | | | IV-2 | Khsrp | 8570 | 31-May-15 | 14611 | 3 | 4 | | | IV-2 | Olfr25 | | |
| 14516 | 3 | 4 | | | | IV-2 | Kiss1r | 84634 | 7-Jun-15 | 14612 | 3 | 4 | | | IV-2 | Olfr263 | | |
| 14517 | 3 | 4 | | | | IV-2 | Klrc2 | 3822 | 12-May-15 | 14613 | 3 | 4 | | | IV-2 | Olfr267 | | |
| 14518 | 3 | 4 | | | | IV-2 | Ktn1 | 3895 | 4-May-15 | 14614 | 3 | 4 | | | IV-2 | Olfr283 | | |
| 14519 | 3 | 4 | | | | IV-2 | Lhfpl4 | 375323 | 4-May-15 | 14615 | 3 | 4 | | | IV-2 | Olfr286 | | |
| 14520 | 3 | 4 | | | | IV-2 | LOC100861615 | | | 14616 | 3 | 4 | | | IV-2 | Olfr298 | | |
| 14521 | 3 | 4 | | | | IV-2 | Magea8 | 4107 | 12-May-15 | 14617 | 3 | 4 | | | IV-2 | Olfr329-ps | | |
| 14522 | 3 | 4 | | | | IV-2 | Mageb16-ps1 | | | 14618 | 3 | 4 | | | IV-2 | Olfr350 | | |
| 14523 | 3 | 4 | | | | IV-2 | Mageb18 | 286514 | 4-May-15 | 14619 | 3 | 4 | | | IV-2 | Olfr354 | | |
| 14524 | 3 | 4 | | | | IV-2 | Mageb2 | 4113 | 4-May-15 | 14620 | 3 | 4 | | | IV-2 | Olfr356 | | |
| 14525 | 3 | 4 | | | | IV-2 | Mageb4 | 4115 | 4-May-15 | 14621 | 3 | 4 | | | IV-2 | Olfr412 | | |
| 14526 | 3 | 4 | | | | IV-2 | Maged1 | 9500 | 4-May-15 | 14622 | 3 | 4 | | | IV-2 | Olfr48 | | |
| 14527 | 3 | 4 | | | | IV-2 | Mageh1 | 28986 | 4-May-15 | 14623 | 3 | 4 | | | IV-2 | Olfr480 | | |
| 14528 | 3 | 4 | | | | IV-2 | Mblac1 | 255374 | 4-May-15 | 14624 | 3 | 4 | | | IV-2 | Olfr570 | | |
| 14529 | 3 | 4 | | | | IV-2 | Mir216c | | | 14625 | 3 | 4 | | | IV-2 | Olfr597 | | |
| 14530 | 3 | 4 | | | | IV-2 | Mir299b | | | 14626 | 3 | 4 | | | IV-2 | Olfr605 | | |

Fig. 30 - 78

| | | | | | | | | |
|---|---|---|---|---|---|---|---|---|
| 14627 | 3 | 4 | | | IV-2 | Olfr645 | | |
| 14628 | 3 | 4 | | | IV-2 | Olfr681 | | |
| 14629 | 3 | 4 | | | IV-2 | Olfr782 | | |
| 14630 | 3 | 4 | | | IV-2 | Olfr784 | | |
| 14631 | 3 | 4 | | | IV-2 | Olfr805 | | |
| 14632 | 3 | 4 | | | IV-2 | Olfr808 | | |
| 14633 | 3 | 4 | | | IV-2 | Olfr824 | | |
| 14634 | 3 | 4 | | | IV-2 | Olfr919 | | |
| 14635 | 3 | 4 | | | IV-2 | Olfr92 | | |
| 14636 | 3 | 4 | | | IV-2 | Olfr971 | | |
| 14637 | 3 | 4 | | | IV-2 | Olfr972 | | |
| 14638 | 3 | 4 | | | IV-2 | Olfr987 | | |
| 14639 | 3 | 4 | | | IV-2 | Otop1 | 133060 | 4-May-15 |
| 14640 | 3 | 4 | | | IV-2 | Otos | 150677 | 4-May-15 |
| 14641 | 3 | 4 | | | IV-2 | Otp | 23440 | 4-May-15 |
| 14642 | 3 | 4 | | | IV-2 | Ott | 64783 | 4-May-15 |
| 14643 | 3 | 4 | | | IV-2 | Oxa1l | 5018 | 4-May-15 |
| 14644 | 3 | 4 | | | IV-2 | Pacs1 | 55690 | 4-May-15 |
| 14645 | 3 | 4 | | | IV-2 | Pax4 | 5078 | 4-May-15 |
| 14646 | 3 | 4 | | | IV-2 | Paxbp1 | 94104 | 12-May-15 |
| 14647 | 3 | 4 | | | IV-2 | Pcdhb12 | 56124 | 4-May-15 |
| 14648 | 3 | 4 | | | IV-2 | Pdgfa | 5154 | 31-May-15 |
| 14649 | 3 | 4 | | | IV-2 | Pip4k2c | 79837 | 4-May-15 |
| 14650 | 3 | 4 | | | IV-2 | Ppa1 | 5464 | 4-May-15 |
| 14651 | 3 | 4 | | | IV-2 | Ppp2ca | 5515 | 17-May-15 |
| 14652 | 3 | 4 | | | IV-2 | Pramel5 | | |
| 14653 | 3 | 4 | | | IV-2 | Pramel7 | | |
| 14654 | 3 | 4 | | | IV-2 | Prcp | 5547 | 4-May-15 |
| 14655 | 3 | 4 | | | IV-2 | Prl3b1 | | |
| 14656 | 3 | 4 | | | IV-2 | Prl3c1 | | |
| 14657 | 3 | 4 | | | IV-2 | Prl3d1 | | |
| 14658 | 3 | 4 | | | IV-2 | Prl3d2 | | |
| 14659 | 3 | 4 | | | IV-2 | Prl3d3 | | |
| 14660 | 3 | 4 | | | IV-2 | Prl5a1 | | |
| 14661 | 3 | 4 | | | IV-2 | Prl6a1 | | |
| 14662 | 3 | 4 | | | IV-2 | Prl7a2 | | |
| 14663 | 3 | 4 | | | IV-2 | Prl7b1 | | |
| 14664 | 3 | 4 | | | IV-2 | Prl7c1 | | |
| 14665 | 3 | 4 | | | IV-2 | Prl7d1 | | |
| 14666 | 3 | 4 | | | IV-2 | Prl8a1 | | |
| 14667 | 3 | 4 | | | IV-2 | Prl8a2 | | |
| 14668 | 3 | 4 | | | IV-2 | Prl8a6 | | |
| 14669 | 3 | 4 | | | IV-2 | Prl8a8 | | |
| 14670 | 3 | 4 | | | IV-2 | Prl8a9 | | |
| 14671 | 3 | 4 | | | IV-2 | Prlh | 51052 | 4-May-15 |
| 14672 | 3 | 4 | | | IV-2 | Prlhr | 2834 | 4-May-15 |
| 14673 | 3 | 4 | | | IV-2 | Prlr | 5618 | 7-Jun-15 |
| 14674 | 3 | 4 | | | IV-2 | Prmt1 | 3276 | 12-May-15 |
| 14675 | 3 | 4 | | | IV-2 | Prmt2 | 3275 | 4-May-15 |
| 14676 | 3 | 4 | | | IV-2 | Prpf39 | 55015 | 4-May-15 |
| 14677 | 3 | 4 | | | IV-2 | Prss39 | | |
| 14678 | 3 | 4 | | | IV-2 | Prss44 | 729756 | 17-Mar-15 |
| 14679 | 3 | 4 | | | IV-2 | Prss45 | 377047 | 4-May-15 |
| 14680 | 3 | 4 | | | IV-2 | Psg26 | | |
| 14681 | 3 | 4 | | | IV-2 | Psg29 | | |
| 14682 | 3 | 4 | | | IV-2 | Psg-ps1 | | |
| 14683 | 3 | 4 | | | IV-2 | Psip1 | 11168 | 21-May-15 |
| 14684 | 3 | 4 | | | IV-2 | Pskh1 | 5681 | 12-May-15 |
| 14685 | 3 | 4 | | | IV-2 | Psma1 | 5682 | 4-May-15 |
| 14686 | 3 | 4 | | | IV-2 | Psma5 | 5686 | 12-May-15 |
| 14687 | 3 | 4 | | | IV-2 | Ptf1a | 256297 | 28-May-15 |
| 14688 | 3 | 4 | | | IV-2 | Ptrhd1 | 391356 | 4-May-15 |
| 14689 | 3 | 4 | | | IV-2 | Rhox2c | | |
| 14690 | 3 | 4 | | | IV-2 | Rhox2d | | |
| 14691 | 3 | 4 | | | IV-2 | Rhox2f | | |
| 14692 | 3 | 4 | | | IV-2 | Rhox2h | | |
| 14693 | 3 | 4 | | | IV-2 | Rhox3a | | |
| 14694 | 3 | 4 | | | IV-2 | Rhox3c | | |
| 14695 | 3 | 4 | | | IV-2 | Rhox3e | | |
| 14696 | 3 | 4 | | | IV-2 | Rhox3g | | |
| 14697 | 3 | 4 | | | IV-2 | Rhox3h | | |
| 14698 | 3 | 4 | | | IV-2 | Rhox4a | | |
| 14699 | 3 | 4 | | | IV-2 | Rhox9 | | |
| 14700 | 3 | 4 | | | IV-2 | Ribc2 | 26150 | 4-May-15 |
| 14701 | 3 | 4 | | | IV-2 | Ric3 | 79608 | 14-May-15 |
| 14702 | 3 | 4 | | | IV-2 | Ric8 | 60626 | 7-Jun-15 |
| 14703 | 3 | 4 | | | IV-2 | Rpap1 | 26015 | 4-May-15 |
| 14704 | 3 | 4 | | | IV-2 | Rps13 | 6207 | 12-May-15 |
| 14705 | 3 | 4 | | | IV-2 | Rsg1 | 79363 | 4-May-15 |
| 14706 | 3 | 4 | | | IV-2 | Rufy2 | 55680 | 1-Jun-15 |
| 14707 | 3 | 4 | | | IV-2 | Safb2 | 9667 | 4-May-15 |
| 14708 | 3 | 4 | | | IV-2 | Scgb1b30 | | |
| 14709 | 3 | 4 | | | IV-2 | Scgb2b17 | | |
| 14710 | 3 | 4 | | | IV-2 | Scgb2b19 | | |
| 14711 | 3 | 4 | | | IV-2 | Scgb2b2 | 284402 | 4-May-15 |
| 14712 | 3 | 4 | | | IV-2 | Scgb2b20 | | |
| 14713 | 3 | 4 | | | IV-2 | Scgb2b26 | | |
| 14714 | 3 | 4 | | | IV-2 | Scgb2b27 | | |
| 14715 | 3 | 4 | | | IV-2 | Scgb2b7 | | |
| 14716 | 3 | 4 | | | IV-2 | Sclt1 | 132320 | 12-May-15 |
| 14717 | 3 | 4 | | | IV-2 | Six4 | 51804 | 4-May-15 |
| 14718 | 3 | 4 | | | IV-2 | Slc27a1 | 376497 | 4-May-15 |
| 14719 | 3 | 4 | | | IV-2 | Slc37a4 | 2542 | 28-May-15 |
| 14720 | 3 | 4 | | | IV-2 | Slc38a8 | 146167 | 4-May-15 |
| 14721 | 3 | 4 | | | IV-2 | Slc5a8 | 160728 | 4-May-15 |
| 14722 | 3 | 4 | | | IV-2 | Slc6a19 | 340024 | 4-May-15 |
| 14723 | 3 | 4 | | | IV-2 | Slmap | 7871 | 12-May-15 |
| 14724 | 3 | 4 | | | IV-2 | Smim18 | 100507341 | 4-May-15 |
| 14725 | 3 | 4 | | | IV-2 | Smurf1 | 57154 | 31-May-15 |
| 14726 | 3 | 4 | | | IV-2 | Spaca5 | 389852 | 4-May-15 |
| 14727 | 3 | 4 | | | IV-2 | Spaca6 | 147650 | 3-May-15 |
| 14728 | 3 | 4 | | | IV-2 | Spata31d1d | | |
| 14729 | 3 | 4 | | | IV-2 | Speer4b | | |
| 14730 | 3 | 4 | | | IV-2 | Spry3 | 10251 | 12-May-15 |
| 14731 | 3 | 4 | | | IV-2 | Ssxb1 | | |
| 14732 | 3 | 4 | | | IV-2 | Sult2a4 | | |
| 14733 | 3 | 4 | | | IV-2 | Sult4a1 | 25830 | 4-May-15 |
| 14734 | 3 | 4 | | | IV-2 | Sumo2 | 6613 | 24-May-15 |
| 14735 | 3 | 4 | | | IV-2 | Svop1 | 136306 | 4-May-15 |
| 14736 | 3 | 4 | | | IV-2 | Swsap1 | 126074 | 4-May-15 |
| 14737 | 3 | 4 | | | IV-2 | Swt1 | 54823 | 4-May-15 |
| 14738 | 3 | 4 | | | IV-2 | Taar6 | 319100 | 4-May-15 |
| 14739 | 3 | 4 | | | IV-2 | Taar7b | | |
| 14740 | 3 | 4 | | | IV-2 | Taar7d | | |
| 14741 | 3 | 4 | | | IV-2 | Taar7e | | |
| 14742 | 3 | 4 | | | IV-2 | Taar7f | | |
| 14743 | 3 | 4 | | | IV-2 | Taar8a | | |
| 14744 | 3 | 4 | | | IV-2 | Taar8b | | |
| 14745 | 3 | 4 | | | IV-2 | Taar8c | | |
| 14746 | 3 | 4 | | | IV-2 | Taar9 | 134860 | 4-May-15 |
| 14747 | 3 | 4 | | | IV-2 | Tab1 | 10454 | 4-May-15 |
| 14748 | 3 | 4 | | | IV-2 | Tab2 | 23118 | 12-May-15 |
| 14749 | 3 | 4 | | | IV-2 | Tacc1 | 6867 | 4-May-15 |
| 14750 | 3 | 4 | | | IV-2 | Tacc3 | 6870 | 12-May-15 |
| 14751 | 3 | 4 | | | IV-2 | Tas2r107 | | |
| 14752 | 3 | 4 | | | IV-2 | Tas2r109 | | |
| 14753 | 3 | 4 | | | IV-2 | Tas2r110 | | |
| 14754 | 3 | 4 | | | IV-2 | Tas2r113 | | |
| 14755 | 3 | 4 | | | IV-2 | Tas2r114 | | |
| 14756 | 3 | 4 | | | IV-2 | Tas2r115 | | |
| 14757 | 3 | 4 | | | IV-2 | Tas2r116 | | |
| 14758 | 3 | 4 | | | IV-2 | Tas2r117 | | |
| 14759 | 3 | 4 | | | IV-2 | Tas2r118 | | |
| 14760 | 3 | 4 | | | IV-2 | Tas2r119 | | |
| 14761 | 3 | 4 | | | IV-2 | Tas2r120 | | |
| 14762 | 3 | 4 | | | IV-2 | Tas2r121 | | |
| 14763 | 3 | 4 | | | IV-2 | Tas2r122 | | |
| 14764 | 3 | 4 | | | IV-2 | Tas2r123 | | |
| 14765 | 3 | 4 | | | IV-2 | Tas2r124 | | |
| 14766 | 3 | 4 | | | IV-2 | Tas2r125 | | |
| 14767 | 3 | 4 | | | IV-2 | Tas2r126 | | |
| 14768 | 3 | 4 | | | IV-2 | Tas2r129 | | |
| 14769 | 3 | 4 | | | IV-2 | Tas2r130 | | |
| 14770 | 3 | 4 | | | IV-2 | Tas2r131 | | |
| 14771 | 3 | 4 | | | IV-2 | Tas2r134 | | |
| 14772 | 3 | 4 | | | IV-2 | Tas2r135 | | |
| 14773 | 3 | 4 | | | IV-2 | Tas2r136 | | |
| 14774 | 3 | 4 | | | IV-2 | Tas2r137 | | |
| 14775 | 3 | 4 | | | IV-2 | Tas2r138 | | |
| 14776 | 3 | 4 | | | IV-2 | Tas2r139 | | |
| 14777 | 3 | 4 | | | IV-2 | Tas2r140 | | |
| 14778 | 3 | 4 | | | IV-2 | Tas2r143 | | |
| 14779 | 3 | 4 | | | IV-2 | Tas2r144 | | |
| 14780 | 3 | 4 | | | IV-2 | Tasp1 | 55617 | 4-May-15 |
| 14781 | 3 | 4 | | | IV-2 | Tcp10a | 6953 | 4-May-15 |
| 14782 | 3 | 4 | | | IV-2 | Tcp10b | | |
| 14783 | 3 | 4 | | | IV-2 | Tdpoz3 | | |
| 14784 | 3 | 4 | | | IV-2 | Tdrd7 | 23424 | 4-May-15 |
| 14785 | 3 | 4 | | | IV-2 | Tdrd9 | 122402 | 4-May-15 |
| 14786 | 3 | 4 | | | IV-2 | Tex264 | 51368 | 4-May-15 |
| 14787 | 3 | 4 | | | IV-2 | Tm9sf1 | 10548 | 21-May-15 |
| 14788 | 3 | 4 | | | IV-2 | Tmem161a | 54929 | 4-May-15 |
| 14789 | 3 | 4 | | | IV-2 | Tmprss6 | 164656 | 4-May-15 |
| 14790 | 3 | 4 | | | IV-2 | Tmprss9 | 360200 | 4-May-15 |
| 14791 | 3 | 4 | | | IV-2 | Tnip3 | 79931 | 12-May-15 |
| 14792 | 3 | 4 | | | IV-2 | Trim45 | 80263 | 4-May-15 |
| 14793 | 3 | 4 | | | IV-2 | Trip10 | 9322 | 4-May-15 |
| 14794 | 3 | 4 | | | IV-2 | Tusc3 | 7991 | 23-May-15 |
| 14795 | 3 | 4 | | | IV-2 | Ugt8a | | |
| 14796 | 3 | 4 | | | IV-2 | Usp22 | 23326 | 21-May-15 |
| 14797 | 3 | 4 | | | IV-2 | Usp24 | 23358 | 4-May-15 |
| 14798 | 3 | 4 | | | IV-2 | Vamp4 | 8674 | 4-May-15 |
| 14799 | 3 | 4 | | | IV-2 | Vamp7 | 6845 | 21-May-15 |
| 14800 | 3 | 4 | | | IV-2 | Vmn1r111 | | |
| 14801 | 3 | 4 | | | IV-2 | Vmn1r112 | | |
| 14802 | 3 | 4 | | | IV-2 | Vmn1r113 | | |
| 14803 | 3 | 4 | | | IV-2 | Vmn1r114 | | |
| 14804 | 3 | 4 | | | IV-2 | Vmn1r115 | | |
| 14805 | 3 | 4 | | | IV-2 | Vmn1r116 | | |
| 14806 | 3 | 4 | | | IV-2 | Vmn1r117 | | |
| 14807 | 3 | 4 | | | IV-2 | Vmn1r118 | | |
| 14808 | 3 | 4 | | | IV-2 | Vmn1r119 | | |
| 14809 | 3 | 4 | | | IV-2 | Vmn1r12 | | |
| 14810 | 3 | 4 | | | IV-2 | Vmn1r120 | | |
| 14811 | 3 | 4 | | | IV-2 | Vmn1r121 | | |
| 14812 | 3 | 4 | | | IV-2 | Vmn1r122 | | |
| 14813 | 3 | 4 | | | IV-2 | Vmn1r123 | | |
| 14814 | 3 | 4 | | | IV-2 | Vmn1r124 | | |
| 14815 | 3 | 4 | | | IV-2 | Vmn1r125 | | |
| 14816 | 3 | 4 | | | IV-2 | Vmn1r126 | | |
| 14817 | 3 | 4 | | | IV-2 | Vmn1r127 | | |

Fig. 30 - 79

| | | | | | | | | | | | | | | | |
|---|---|---|---|---|---|---|---|---|---|---|---|---|---|---|---|
| 14818 | 3 | 4 | | | | IV-2 | Vmn1r128 | | | 14912 | 3 | 4 | | IV-1 | 1700011M02Rik |
| 14819 | 3 | 4 | | | | IV-2 | Vmn1r129 | | | 14913 | 3 | 4 | | IV-1 | 1700012A03Rik |
| 14820 | 3 | 4 | | | | IV-2 | Vmn1r13 | | | 14914 | 3 | 4 | | IV-1 | 1700012L04Rik |
| 14821 | 3 | 4 | | | | IV-2 | Vmn1r130 | | | 14915 | 3 | 4 | | IV-1 | 1700012P22Rik |
| 14822 | 3 | 4 | | | | IV-2 | Vmn1r131 | | | 14916 | 3 | 4 | | IV-1 | 1700013H16Rik |
| 14823 | 3 | 4 | | | | IV-2 | Vmn1r132 | | | 14917 | 3 | 4 | | IV-1 | 1700015E13Rik |
| 14824 | 3 | 4 | | | | IV-2 | Vmn1r135 | | | 14918 | 3 | 4 | | IV-1 | 1700015F17Rik |
| 14825 | 3 | 4 | | | | IV-2 | Vmn1r138 | | | 14919 | 3 | 4 | | IV-1 | 1700015G11Rik |
| 14826 | 3 | 4 | | | | IV-2 | Vmn1r139 | | | 14920 | 3 | 4 | | IV-1 | 1700016C15Rik |
| 14827 | 3 | 4 | | | | IV-2 | Vmn1r14 | | | 14921 | 3 | 4 | | IV-1 | 1700016G22Rik |
| 14828 | 3 | 4 | | | | IV-2 | Vmn1r142 | | | 14922 | 3 | 4 | | IV-1 | 1700016H13Rik |
| 14829 | 3 | 4 | | | | IV-2 | Vmn1r143 | | | 14923 | 3 | 4 | | IV-1 | 1700016L21Rik |
| 14830 | 3 | 4 | | | | IV-2 | Vmn1r148 | | | 14924 | 3 | 4 | | IV-1 | 1700016P04Rik |
| 14831 | 3 | 4 | | | | IV-2 | Vmn1r15 | | | 14925 | 3 | 4 | | IV-1 | 1700017B05Rik |
| 14832 | 3 | 4 | | | | IV-2 | Vmn1r218 | | | 14926 | 3 | 4 | | IV-1 | 1700017G19Rik |
| 14833 | 3 | 4 | | | | IV-2 | Vmn2r19 | | | 14927 | 3 | 4 | | IV-1 | 1700017I07Rik |
| 14834 | 3 | 4 | | | | IV-2 | Vmn2r61 | | | 14928 | 3 | 4 | | IV-1 | 1700017N19Rik |
| 14835 | 3 | 4 | | | | IV-2 | Vmn2r65 | | | 14929 | 3 | 4 | | IV-1 | 1700018B24Rik |
| 14836 | 3 | 4 | | | | IV-2 | Vmn2r-ps60 | | | 14930 | 3 | 4 | | IV-1 | 1700018C11Rik |
| 14837 | 3 | 4 | | | | IV-2 | vmp1 | 81671 | 21-May-15 | 14931 | 3 | 4 | | IV-1 | 1700018F24Rik |
| 14838 | 3 | 4 | | | | IV-2 | Vtcn1 | 79679 | 24-May-15 | 14932 | 3 | 4 | | IV-1 | 1700019B03Rik |
| 14839 | 3 | 4 | | | | IV-2 | Wapal | 23063 | 4-May-15 | 14933 | 3 | 4 | | IV-1 | 1700019B21Rik |
| 14840 | 3 | 4 | | | | IV-2 | Wasf3 | 10810 | 12-May-15 | 14934 | 3 | 4 | | IV-1 | 1700020D05Rik |
| 14841 | 3 | 4 | | | | IV-2 | Wfdc1 | 58189 | 4-May-15 | 14935 | 3 | 4 | | IV-1 | 1700020G17Rik |
| 14842 | 3 | 4 | | | | IV-2 | Xpnpep1 | 7511 | 12-May-15 | 14936 | 3 | 4 | | IV-1 | 1700020I14Rik |
| 14843 | 3 | 4 | | | | IV-2 | Zfp365 | | | 14937 | 3 | 4 | | IV-1 | 1700020N01Rik |
| 14844 | 3 | 4 | | | | IV-2 | Zpld1 | 131368 | 4-May-15 | 14938 | 3 | 4 | | IV-1 | 1700020N15Rik |
| 14845 | 3 | 4 | | | | IV-2 | Zranb1 | 54764 | 2-Jun-15 | 14939 | 3 | 4 | | IV-1 | 1700020N18Rik |
| 14846 | 3 | 4 | | | | IV-2 | Zswim1 | 90204 | 4-May-15 | 14940 | 3 | 4 | | IV-1 | 1700021K19Rik |
| 14847 | 3 | 4 | | | | IV-2 | Zswim2 | 151112 | 4-May-15 | 14941 | 3 | 4 | | IV-1 | 1700022A21Rik |
| 14848 | 3 | 4 | | | | IV-2 | Zswim3 | 140831 | 4-May-15 | 14942 | 3 | 4 | | IV-1 | 1700022A22Rik |
| 14849 | 3 | 4 | | | | IV-2 | Zswim4 | 65249 | 4-May-15 | 14943 | 3 | 4 | | IV-1 | 1700022E09Rik |
| 14850 | 3 | 4 | | | | IV-2 | Zswim7 | 125150 | 4-May-15 | 14944 | 3 | 4 | | IV-1 | 1700022H16Rik |
| 14851 | 3 | 4 | | | | IV-1 | 0610010K14Rik | | | 14945 | 3 | 4 | | IV-1 | 1700022I11Rik |
| 14852 | 3 | 4 | | | | IV-1 | 0610011F06Rik | | | 14946 | 3 | 4 | | IV-1 | 1700023C21Rik |
| 14853 | 3 | 4 | | | | IV-1 | 0610012G03Rik | | | 14947 | 3 | 4 | | IV-1 | 1700023E05Rik |
| 14854 | 3 | 4 | | | | IV-1 | 0610030E20Rik | | | 14948 | 3 | 4 | | IV-1 | 1700023F02Rik |
| 14855 | 3 | 4 | | | | IV-1 | 0610031J06Rik | | | 14949 | 3 | 4 | | IV-1 | 1700023L04Rik |
| 14856 | 3 | 4 | | | | IV-1 | 0610031O16Rik | | | 14950 | 3 | 4 | | IV-1 | 1700025C18Rik |
| 14857 | 3 | 4 | | | | IV-1 | 0610038B21Rik | | | 14951 | 3 | 4 | | IV-1 | 1700025F22Rik |
| 14858 | 3 | 4 | | | | IV-1 | 1010001N08Rik | | | 14952 | 3 | 4 | | IV-1 | 1700025G04Rik |
| 14859 | 3 | 4 | | | | IV-1 | 1110004F10Rik | | | 14953 | 3 | 4 | | IV-1 | 1700025M24Rik |
| 14860 | 3 | 4 | | | | IV-1 | 1110006O24Rik | | | 14954 | 3 | 4 | | IV-1 | 1700026F02Rik |
| 14861 | 3 | 4 | | | | IV-1 | 1110008F13Rik | | | 14955 | 3 | 4 | | IV-1 | 1700027H10Rik |
| 14862 | 3 | 4 | | | | IV-1 | 1110008L16Rik | | | 14956 | 3 | 4 | | IV-1 | 1700027I24Rik |
| 14863 | 3 | 4 | | | | IV-1 | 1110008P14Rik | | | 14957 | 3 | 4 | | IV-1 | 1700028E10Rik |
| 14864 | 3 | 4 | | | | IV-1 | 1110012L19Rik | | | 14958 | 3 | 4 | | IV-1 | 1700028M03Rik |
| 14865 | 3 | 4 | | | | IV-1 | 1110015O18Rik | | | 14959 | 3 | 4 | | IV-1 | 1700029B22Rik |
| 14866 | 3 | 4 | | | | IV-1 | 1110028F18Rik | | | 14960 | 3 | 4 | | IV-1 | 1700029J07Rik |
| 14867 | 3 | 4 | | | | IV-1 | 1110037F02Rik | | | 14961 | 3 | 4 | | IV-1 | 1700029N11Rik |
| 14868 | 3 | 4 | | | | IV-1 | 1110058L19Rik | | | 14962 | 3 | 4 | | IV-1 | 1700029P13Rik |
| 14869 | 3 | 4 | | | | IV-1 | 1110059G10Rik | | | 14963 | 3 | 4 | | IV-1 | 1700030A11Rik |
| 14870 | 3 | 4 | | | | IV-1 | 1110065P20Rik | | | 14964 | 3 | 4 | | IV-1 | 1700030C10Rik |
| 14871 | 3 | 4 | | | | IV-1 | 1190005I06Rik | | | 14965 | 3 | 4 | | IV-1 | 1700030F04Rik |
| 14872 | 3 | 4 | | | | IV-1 | 1300002E11Rik | | | 14966 | 3 | 4 | | IV-1 | 1700030F18Rik |
| 14873 | 3 | 4 | | | | IV-1 | 1500015A07Rik | | | 14967 | 3 | 4 | | IV-1 | 1700030J22Rik |
| 14874 | 3 | 4 | | | | IV-1 | 1600010M07Rik | | | 14968 | 3 | 4 | | IV-1 | 1700030K09Rik |
| 14875 | 3 | 4 | | | | IV-1 | 1600015I10Rik | | | 14969 | 3 | 4 | | IV-1 | 1700030M09Rik |
| 14876 | 3 | 4 | | | | IV-1 | 1600020E01Rik | | | 14970 | 3 | 4 | | IV-1 | 1700030N03Rik |
| 14877 | 3 | 4 | | | | IV-1 | 1600025M17Rik | | | 14971 | 3 | 4 | | IV-1 | 1700031A10Rik |
| 14878 | 3 | 4 | | | | IV-1 | 1600027J07Rik | | | 14972 | 3 | 4 | | IV-1 | 1700031F05Rik |
| 14879 | 3 | 4 | | | | IV-1 | 1700001F09Rik | | | 14973 | 3 | 4 | | IV-1 | 1700031M16Rik |
| 14880 | 3 | 4 | | | | IV-1 | 1700001L17Rik | | | 14974 | 3 | 4 | | IV-1 | 1700031P21Rik |
| 14881 | 3 | 4 | | | | IV-1 | 1700001J11Rik | | | 14975 | 3 | 4 | | IV-1 | 1700034E13Rik |
| 14882 | 3 | 4 | | | | IV-1 | 1700001K19Rik | | | 14976 | 3 | 4 | | IV-1 | 1700034F02Rik |
| 14883 | 3 | 4 | | | | IV-1 | 1700001O22Rik | | | 14977 | 3 | 4 | | IV-1 | 1700034G24Rik |
| 14884 | 3 | 4 | | | | IV-1 | 1700003C15Rik | | | 14978 | 3 | 4 | | IV-1 | 1700034I23Rik |
| 14885 | 3 | 4 | | | | IV-1 | 1700003E16Rik | | | 14979 | 3 | 4 | | IV-1 | 1700034I05Rik |
| 14886 | 3 | 4 | | | | IV-1 | 1700003G13Rik | | | 14980 | 3 | 4 | | IV-1 | 1700034K08Rik |
| 14887 | 3 | 4 | | | | IV-1 | 1700003G18Rik | | | 14981 | 3 | 4 | | IV-1 | 1700034O15Rik |
| 14888 | 3 | 4 | | | | IV-1 | 1700003L19Rik | | | 14982 | 3 | 4 | | IV-1 | 1700034P13Rik |
| 14889 | 3 | 4 | | | | IV-1 | 1700003P14Rik | | | 14983 | 3 | 4 | | IV-1 | 1700036G14Rik |
| 14890 | 3 | 4 | | | | IV-1 | 1700006E09Rik | | | 14984 | 3 | 4 | | IV-1 | 1700037C18Rik |
| 14891 | 3 | 4 | | | | IV-1 | 1700006F04Rik | | | 14985 | 3 | 4 | | IV-1 | 1700041M19Rik |
| 14892 | 3 | 4 | | | | IV-1 | 1700006H21Rik | | | 14986 | 3 | 4 | | IV-1 | 1700042B14Rik |
| 14893 | 3 | 4 | | | | IV-1 | 1700007F19Rik | | | 14987 | 3 | 4 | | IV-1 | 1700042G07Rik |
| 14894 | 3 | 4 | | | | IV-1 | 1700007G11Rik | | | 14988 | 3 | 4 | | IV-1 | 1700042G15Rik |
| 14895 | 3 | 4 | | | | IV-1 | 1700007J10Rik | | | 14989 | 3 | 4 | | IV-1 | 1700042O10Rik |
| 14896 | 3 | 4 | | | | IV-1 | 1700007K09Rik | | | 14990 | 3 | 4 | | IV-1 | 1700044C05Rik |
| 14897 | 3 | 4 | | | | IV-1 | 1700008F21Rik | | | 14991 | 3 | 4 | | IV-1 | 1700044K03Rik |
| 14898 | 3 | 4 | | | | IV-1 | 1700008I05Rik | | | 14992 | 3 | 4 | | IV-1 | 1700047A11Rik |
| 14899 | 3 | 4 | | | | IV-1 | 1700008J07Rik | | | 14993 | 3 | 4 | | IV-1 | 1700047E10Rik |
| 14900 | 3 | 4 | | | | IV-1 | 1700008K24Rik | | | 14994 | 3 | 4 | | IV-1 | 1700047L14Rik |
| 14901 | 3 | 4 | | | | IV-1 | 1700008O03Rik | | | 14995 | 3 | 4 | | IV-1 | 1700047M11Rik |
| 14902 | 3 | 4 | | | | IV-1 | 1700008P02Rik | | | 14996 | 3 | 4 | | IV-1 | 1700049G17Rik |
| 14903 | 3 | 4 | | | | IV-1 | 1700009C05Rik | | | 14997 | 3 | 4 | | IV-1 | 1700051A21Rik |
| 14904 | 3 | 4 | | | | IV-1 | 1700009J07Rik | | | 14998 | 3 | 4 | | IV-1 | 1700052I22Rik |
| 14905 | 3 | 4 | | | | IV-1 | 1700009N14Rik | | | 14999 | 3 | 4 | | IV-1 | 1700052K11Rik |
| 14906 | 3 | 4 | | | | IV-1 | 1700010D01Rik | | | 15000 | 3 | 4 | | IV-1 | 1700054K19Rik |
| 14907 | 3 | 4 | | | | IV-1 | 1700010I02Rik | | | 15001 | 3 | 4 | | IV-1 | 1700054M17Rik |
| 14908 | 3 | 4 | | | | IV-1 | 1700010K23Rik | | | | | | | | |
| 14909 | 3 | 4 | | | | IV-1 | 1700011B04Rik | | | | | | | | |
| 14910 | 3 | 4 | | | | IV-1 | 1700011E24Rik | | | | | | | | |
| 14911 | 3 | 4 | | | | IV-1 | 1700011L22Rik | | | | | | | | |

Fig. 30 - 80

| | | | | | | | | | | | | | | | | |
|---|---|---|---|---|---|---|---|---|---|---|---|---|---|---|---|---|
| 15002 | 3 | 4 | | | | | IV-1 | 1700055C04Rik | | 15094 | 3 | 4 | | | IV-1 | 2310009A05Rik |
| 15003 | 3 | 4 | | | | | IV-1 | 1700055N04Rik | | 15095 | 3 | 4 | | | IV-1 | 2310022B05Rik |
| 15004 | 3 | 4 | | | | | IV-1 | 1700056E22Rik | | 15096 | 3 | 4 | | | IV-1 | 2310030G06Rik |
| 15005 | 3 | 4 | | | | | IV-1 | 1700057G04Rik | | 15097 | 3 | 4 | | | IV-1 | 2310034G01Rik |
| 15006 | 3 | 4 | | | | | IV-1 | 1700057H15Rik | | 15098 | 3 | 4 | | | IV-1 | 2310036O22Rik |
| 15007 | 3 | 4 | | | | | IV-1 | 1700060C16Rik | | 15099 | 3 | 4 | | | IV-1 | 2310039H08Rik |
| 15008 | 3 | 4 | | | | | IV-1 | 1700060C20Rik | | 15100 | 3 | 4 | | | IV-1 | 2310043O21Rik |
| 15009 | 3 | 4 | | | | | IV-1 | 1700061G19Rik | | 15101 | 3 | 4 | | | IV-1 | 2310045N01Rik |
| 15010 | 3 | 4 | | | | | IV-1 | 1700063O14Rik | | 15102 | 3 | 4 | | | IV-1 | 2310047M10Rik |
| 15011 | 3 | 4 | | | | | IV-1 | 1700064J06Rik | | 15103 | 3 | 4 | | | IV-1 | 2310050C09Rik |
| 15012 | 3 | 4 | | | | | IV-1 | 1700064M15Rik | | 15104 | 3 | 4 | | | IV-1 | 2310057J18Rik |
| 15013 | 3 | 4 | | | | | IV-1 | 1700065D16Rik | | 15105 | 3 | 4 | | | IV-1 | 2310081J21Rik |
| 15014 | 3 | 4 | | | | | IV-1 | 1700065I16Rik | | 15106 | 3 | 4 | | | IV-1 | 2410002F23Rik |
| 15015 | 3 | 4 | | | | | IV-1 | 1700065J18Rik | | 15107 | 3 | 4 | | | IV-1 | 2410004N09Rik |
| 15016 | 3 | 4 | | | | | IV-1 | 1700066B17Rik | | 15108 | 3 | 4 | | | IV-1 | 2410012E07Rik |
| 15017 | 3 | 4 | | | | | IV-1 | 1700066M21Rik | | 15109 | 3 | 4 | | | IV-1 | 2410012M07Rik |
| 15018 | 3 | 4 | | | | | IV-1 | 1700067K01Rik | | 15110 | 3 | 4 | | | IV-1 | 2410016O06Rik |
| 15019 | 3 | 4 | | | | | IV-1 | 1700069L16Rik | | 15111 | 3 | 4 | | | IV-1 | 2410089E03Rik |
| 15020 | 3 | 4 | | | | | IV-1 | 1700069P05Rik | | 15112 | 3 | 4 | | | IV-1 | 2410114N07Rik |
| 15021 | 3 | 4 | | | | | IV-1 | 1700071K01Rik | | 15113 | 3 | 4 | | | IV-1 | 2410124H12Rik |
| 15022 | 3 | 4 | | | | | IV-1 | 1700072O05Rik | | 15114 | 3 | 4 | | | IV-1 | 2410131K14Rik |
| 15023 | 3 | 4 | | | | | IV-1 | 1700073E17Rik | | 15115 | 3 | 4 | | | IV-1 | 2410137M14Rik |
| 15024 | 3 | 4 | | | | | IV-1 | 1700074H08Rik | | 15116 | 3 | 4 | | | IV-1 | 2500004C02Rik |
| 15025 | 3 | 4 | | | | | IV-1 | 1700080E11Rik | | 15117 | 3 | 4 | | | IV-1 | 2510009E07Rik |
| 15026 | 3 | 4 | | | | | IV-1 | 1700080N15Rik | | 15118 | 3 | 4 | | | IV-1 | 2510039O18Rik |
| 15027 | 3 | 4 | | | | | IV-1 | 1700080O16Rik | | 15119 | 3 | 4 | | | IV-1 | 2510049H12Rik |
| 15028 | 3 | 4 | | | | | IV-1 | 1700081H04Rik | | 15120 | 3 | 4 | | | IV-1 | 2610001J05Rik |
| 15029 | 3 | 4 | | | | | IV-1 | 1700084C01Rik | | 15121 | 3 | 4 | | | IV-1 | 2610002J02Rik |
| 15030 | 3 | 4 | | | | | IV-1 | 1700084E18Rik | | 15122 | 3 | 4 | | | IV-1 | 2610008E11Rik |
| 15031 | 3 | 4 | | | | | IV-1 | 1700084J12Rik | | 15123 | 3 | 4 | | | IV-1 | 2610015P09Rik |
| 15032 | 3 | 4 | | | | | IV-1 | 1700086L19Rik | | 15124 | 3 | 4 | | | IV-1 | 2610020H08Rik |
| 15033 | 3 | 4 | | | | | IV-1 | 1700092K14Rik | | 15125 | 3 | 4 | | | IV-1 | 2610034M16Rik |
| 15034 | 3 | 4 | | | | | IV-1 | 1700094M24Rik | | 15126 | 3 | 4 | | | IV-1 | 2610035D17Rik |
| 15035 | 3 | 4 | | | | | IV-1 | 1700096J18Rik | | 15127 | 3 | 4 | | | IV-1 | 2610035F20Rik |
| 15036 | 3 | 4 | | | | | IV-1 | 1700096K18Rik | | 15128 | 3 | 4 | | | IV-1 | 2610037D02Rik |
| 15037 | 3 | 4 | | | | | IV-1 | 1700102H20Rik | | 15129 | 3 | 4 | | | IV-1 | 2610203C20Rik |
| 15038 | 3 | 4 | | | | | IV-1 | 1700105P06Rik | | 15130 | 3 | 4 | | | IV-1 | 2700046G09Rik |
| 15039 | 3 | 4 | | | | | IV-1 | 1700106J16Rik | | 15131 | 3 | 4 | | | IV-1 | 2700054A10Rik |
| 15040 | 3 | 4 | | | | | IV-1 | 1700108F19Rik | | 15132 | 3 | 4 | | | IV-1 | 2700062C07Rik |
| 15041 | 3 | 4 | | | | | IV-1 | 1700108J01Rik | | 15133 | 3 | 4 | | | IV-1 | 2700070H01Rik |
| 15042 | 3 | 4 | | | | | IV-1 | 1700109G14Rik | | 15134 | 3 | 4 | | | IV-1 | 2700081O15Rik |
| 15043 | 3 | 4 | | | | | IV-1 | 1700109G15Rik | | 15135 | 3 | 4 | | | IV-1 | 2700089J24Rik |
| 15044 | 3 | 4 | | | | | IV-1 | 1700109K24Rik | | 15136 | 3 | 4 | | | IV-1 | 2810002D19Rik |
| 15045 | 3 | 4 | | | | | IV-1 | 1700110C19Rik | | 15137 | 3 | 4 | | | IV-1 | 2810004N23Rik |
| 15046 | 3 | 4 | | | | | IV-1 | 1700110I01Rik | | 15138 | 3 | 4 | | | IV-1 | 2810021J22Rik |
| 15047 | 3 | 4 | | | | | IV-1 | 1700110K17Rik | | 15139 | 3 | 4 | | | IV-1 | 2810029C07Rik |
| 15048 | 3 | 4 | | | | | IV-1 | 1700112E06Rik | | 15140 | 3 | 4 | | | IV-1 | 2810047C21Rik |
| 15049 | 3 | 4 | | | | | IV-1 | 1700112J05Rik | | 15141 | 3 | 4 | | | IV-1 | 2810055G20Rik |
| 15050 | 3 | 4 | | | | | IV-1 | 1700113A16Rik | | 15142 | 3 | 4 | | | IV-1 | 2810403A07Rik |
| 15051 | 3 | 4 | | | | | IV-1 | 1700113H08Rik | | 15143 | 3 | 4 | | | IV-1 | 2810403D21Rik |
| 15052 | 3 | 4 | | | | | IV-1 | 1700119H24Rik | | 15144 | 3 | 4 | | | IV-1 | 2810405F15Rik |
| 15053 | 3 | 4 | | | | | IV-1 | 1700121N20Rik | | 15145 | 3 | 4 | | | IV-1 | 2810454H06Rik |
| 15054 | 3 | 4 | | | | | IV-1 | 1700122O11Rik | | 15146 | 3 | 4 | | | IV-1 | 2900026A02Rik |
| 15055 | 3 | 4 | | | | | IV-1 | 1700123I01Rik | | 15147 | 3 | 4 | | | IV-1 | 2900052N01Rik |
| 15056 | 3 | 4 | | | | | IV-1 | 1700123K08Rik | | 15148 | 3 | 4 | | | IV-1 | 2900056M20Rik |
| 15057 | 3 | 4 | | | | | IV-1 | 1700123L14Rik | | 15149 | 3 | 4 | | | IV-1 | 2900057B20Rik |
| 15058 | 3 | 4 | | | | | IV-1 | 1700123M08Rik | | 15150 | 3 | 4 | | | IV-1 | 2900060B14Rik |
| 15059 | 3 | 4 | | | | | IV-1 | 1700123O20Rik | | 15151 | 3 | 4 | | | IV-1 | 2900076A07Rik |
| 15060 | 3 | 4 | | | | | IV-1 | 1700123O21Rik | | 15152 | 3 | 4 | | | IV-1 | 3010026O09Rik |
| 15061 | 3 | 4 | | | | | IV-1 | 1700124I16Rik | | 15153 | 3 | 4 | | | IV-1 | 3110001I22Rik |
| 15062 | 3 | 4 | | | | | IV-1 | 1700125H03Rik | | 15154 | 3 | 4 | | | IV-1 | 3110015C05Rik |
| 15063 | 3 | 4 | | | | | IV-1 | 1700125H20Rik | | 15155 | 3 | 4 | | | IV-1 | 3110021N24Rik |
| 15064 | 3 | 4 | | | | | IV-1 | 1700126B18Rik | | 15156 | 3 | 4 | | | IV-1 | 3110039I08Rik |
| 15065 | 3 | 4 | | | | | IV-1 | 1700129C05Rik | | 15157 | 3 | 4 | | | IV-1 | 3110039M20Rik |
| 15066 | 3 | 4 | | | | | IV-1 | 1810006J02Rik | | 15158 | 3 | 4 | | | IV-1 | 3110043O21Rik |
| 15067 | 3 | 4 | | | | | IV-1 | 1810007C17Rik | | 15159 | 3 | 4 | | | IV-1 | 3110052M02Rik |
| 15068 | 3 | 4 | | | | | IV-1 | 1810026B05Rik | | 15160 | 3 | 4 | | | IV-1 | 3110056K07Rik |
| 15069 | 3 | 4 | | | | | IV-1 | 1810026J23Rik | | 15161 | 3 | 4 | | | IV-1 | 3110099E03Rik |
| 15070 | 3 | 4 | | | | | IV-1 | 1810030O07Rik | | 15162 | 3 | 4 | | | IV-1 | 3200001D21Rik |
| 15071 | 3 | 4 | | | | | IV-1 | 1810032O08Rik | | 15163 | 3 | 4 | | | IV-1 | 3300002I08Rik |
| 15072 | 3 | 4 | | | | | IV-1 | 1810041L15Rik | | 15164 | 3 | 4 | | | IV-1 | 3830403N18Rik |
| 15073 | 3 | 4 | | | | | IV-1 | 1810043H04Rik | | 15165 | 3 | 4 | | | IV-1 | 3830408C21Rik |
| 15074 | 3 | 4 | | | | | IV-1 | 1810062G17Rik | | 15166 | 3 | 4 | | | IV-1 | 3930402G23Rik |
| 15075 | 3 | 4 | | | | | IV-1 | 2010002M12Rik | | 15167 | 3 | 4 | | | IV-1 | 4632415L05Rik |
| 15076 | 3 | 4 | | | | | IV-1 | 2010010A06Rik | | 15168 | 3 | 4 | | | IV-1 | 4732471J01Rik |
| 15077 | 3 | 4 | | | | | IV-1 | 2010310C07Rik | | 15169 | 3 | 4 | | | IV-1 | 4732491K20Rik |
| 15078 | 3 | 4 | | | | | IV-1 | 2010315B03Rik | | 15170 | 3 | 4 | | | IV-1 | 4831440E17Rik |
| 15079 | 3 | 4 | | | | | IV-1 | 2210015D19Rik | | 15171 | 3 | 4 | | | IV-1 | 4833420G17Rik |
| 15080 | 3 | 4 | | | | | IV-1 | 2210016F16Rik | | 15172 | 3 | 4 | | | IV-1 | 4833422C13Rik |
| 15081 | 3 | 4 | | | | | IV-1 | 2210016L21Rik | | 15173 | 3 | 4 | | | IV-1 | 4833424O15Rik |
| 15082 | 3 | 4 | | | | | IV-1 | 2210019I11Rik | | 15174 | 3 | 4 | | | IV-1 | 4833427F10Rik |
| 15083 | 3 | 4 | | | | | IV-1 | 2210039B01Rik | | 15175 | 3 | 4 | | | IV-1 | 4833439L19Rik |
| 15084 | 3 | 4 | | | | | IV-1 | 2210408I21Rik | | 15176 | 3 | 4 | | | IV-1 | 4921501E09Rik |
| 15085 | 3 | 4 | | | | | IV-1 | 2210409D07Rik | | 15177 | 3 | 4 | | | IV-1 | 4921504A21Rik |
| 15086 | 3 | 4 | | | | | IV-1 | 2210416O15Rik | | 15178 | 3 | 4 | | | IV-1 | 4921506M07Rik |
| 15087 | 3 | 4 | | | | | IV-1 | 2210417A02Rik | | 15179 | 3 | 4 | | | IV-1 | 4921507L20Rik |
| 15088 | 3 | 4 | | | | | IV-1 | 2210420H20Rik | | 15180 | 3 | 4 | | | IV-1 | 4921509C19Rik |
| 15089 | 3 | 4 | | | | | IV-1 | 2300002M23Rik | | 15181 | 3 | 4 | | | IV-1 | 4921511C10Rik |
| 15090 | 3 | 4 | | | | | IV-1 | 2300005B03Rik | | 15182 | 3 | 4 | | | IV-1 | 4921511C20Rik |
| 15091 | 3 | 4 | | | | | IV-1 | 2310005A03Rik | | 15183 | 3 | 4 | | | IV-1 | 4921511H03Rik |
| 15092 | 3 | 4 | | | | | IV-1 | 2310005E17Rik | | | | | | | | |
| 15093 | 3 | 4 | | | | | IV-1 | 2310005G13Rik | | | | | | | | |

Fig. 30 - 81

| | | | | | | | | | | | | | | |
|---|---|---|---|---|---|---|---|---|---|---|---|---|---|---|
| 15184 | 3 | 4 | | | | IV-1 | 4921511J17Rik | | | 15276 | 3 | 4 | | | | IV-1 | 4930502A04Rik | | |
| 15185 | 3 | 4 | | | | IV-1 | 4921524L21Rik | | | 15277 | 3 | 4 | | | | IV-1 | 4930502E09Rik | | |
| 15186 | 3 | 4 | | | | IV-1 | 4921525O09Rik | | | 15278 | 3 | 4 | | | | IV-1 | 4930505A04Rik | | |
| 15187 | 3 | 4 | | | | IV-1 | 4921530L21Rik | | | 15279 | 3 | 4 | | | | IV-1 | 4930505G20Rik | | |
| 15188 | 3 | 4 | | | | IV-1 | 4921531C22Rik | | | 15280 | 3 | 4 | | | | IV-1 | 4930507D10Rik | | |
| 15189 | 3 | 4 | | | | IV-1 | 4921533J20Rik | | | 15281 | 3 | 4 | | | | IV-1 | 4930509E16Rik | | |
| 15190 | 3 | 4 | | | | IV-1 | 4921536K21Rik | | | 15282 | 3 | 4 | | | | IV-1 | 4930509J09Rik | | |
| 15191 | 3 | 4 | | | | IV-1 | 4922502H24Rik | | | 15283 | 3 | 4 | | | | IV-1 | 4930509K18Rik | | |
| 15192 | 3 | 4 | | | | IV-1 | 4930401C15Rik | | | 15284 | 3 | 4 | | | | IV-1 | 4930511A02Rik | | |
| 15193 | 3 | 4 | | | | IV-1 | 4930401O10Rik | | | 15285 | 3 | 4 | | | | IV-1 | 4930511M06Rik | | |
| 15194 | 3 | 4 | | | | IV-1 | 4930402F11Rik | | | 15286 | 3 | 4 | | | | IV-1 | 4930512B01Rik | | |
| 15195 | 3 | 4 | | | | IV-1 | 4930404H J1Rik | | | 15287 | 3 | 4 | | | | IV-1 | 4930513D17Rik | | |
| 15196 | 3 | 4 | | | | IV-1 | 4930404I05Rik | | | 15288 | 3 | 4 | | | | IV-1 | 4930513N10Rik | | |
| 15197 | 3 | 4 | | | | IV-1 | 4930405A21Rik | | | 15289 | 3 | 4 | | | | IV-1 | 4930515B02Rik | | |
| 15198 | 3 | 4 | | | | IV-1 | 4930406D18Rik | | | 15290 | 3 | 4 | | | | IV-1 | 4930515G16Rik | | |
| 15199 | 3 | 4 | | | | IV-1 | 4930407I10Rik | | | 15291 | 3 | 4 | | | | IV-1 | 4930515L19Rik | | |
| 15200 | 3 | 4 | | | | IV-1 | 4930412B13Rik | | | 15292 | 3 | 4 | | | | IV-1 | 4930518P08Rik | | |
| 15201 | 3 | 4 | | | | IV-1 | 4930412C18Rik | | | 15293 | 3 | 4 | | | | IV-1 | 4930519F09Rik | | |
| 15202 | 3 | 4 | | | | IV-1 | 4930412D23Rik | | | 15294 | 3 | 4 | | | | IV-1 | 4930519F24Rik | | |
| 15203 | 3 | 4 | | | | IV-1 | 4930414L22Rik | | | 15295 | 3 | 4 | | | | IV-1 | 4930519G04Rik | | |
| 15204 | 3 | 4 | | | | IV-1 | 4930414N06Rik | | | 15296 | 3 | 4 | | | | IV-1 | 4930520O04Rik | | |
| 15205 | 3 | 4 | | | | IV-1 | 4930415F15Rik | | | 15297 | 3 | 4 | | | | IV-1 | 4930520P13Rik | | |
| 15206 | 3 | 4 | | | | IV-1 | 4930415L06Rik | | | 15298 | 3 | 4 | | | | IV-1 | 4930522H14Rik | | |
| 15207 | 3 | 4 | | | | IV-1 | 4930415O20Rik | | | 15299 | 3 | 4 | | | | IV-1 | 4930522O17Rik | | |
| 15208 | 3 | 4 | | | | IV-1 | 4930419G24Rik | | | 15300 | 3 | 4 | | | | IV-1 | 4930523C07Rik | | |
| 15209 | 3 | 4 | | | | IV-1 | 4930423M02Rik | | | 15301 | 3 | 4 | | | | IV-1 | 4930524B15Rik | | |
| 15210 | 3 | 4 | | | | IV-1 | 4930425K10Rik | | | 15302 | 3 | 4 | | | | IV-1 | 4930524C18Rik | | |
| 15211 | 3 | 4 | | | | IV-1 | 4930425O10Rik | | | 15303 | 3 | 4 | | | | IV-1 | 4930525G20Rik | | |
| 15212 | 3 | 4 | | | | IV-1 | 4930428E07Rik | | | 15304 | 3 | 4 | | | | IV-1 | 4930525M21Rik | | |
| 15213 | 3 | 4 | | | | IV-1 | 4930428G15Rik | | | 15305 | 3 | 4 | | | | IV-1 | 4930526L06Rik | | |
| 15214 | 3 | 4 | | | | IV-1 | 4930429B21Rik | | | 15306 | 3 | 4 | | | | IV-1 | 4930527F14Rik | | |
| 15215 | 3 | 4 | | | | IV-1 | 4930429D17Rik | | | 15307 | 3 | 4 | | | | IV-1 | 4930527G23Rik | | |
| 15216 | 3 | 4 | | | | IV-1 | 4930429F11Rik | | | 15308 | 3 | 4 | | | | IV-1 | 4930528D03Rik | | |
| 15217 | 3 | 4 | | | | IV-1 | 4930429F24Rik | | | 15309 | 3 | 4 | | | | IV-1 | 4930528P14Rik | | |
| 15218 | 3 | 4 | | | | IV-1 | 4930430J02Rik | | | 15310 | 3 | 4 | | | | IV-1 | 4930529K09Rik | | |
| 15219 | 3 | 4 | | | | IV-1 | 4930431F12Rik | | | 15311 | 3 | 4 | | | | IV-1 | 4930533P14Rik | | |
| 15220 | 3 | 4 | | | | IV-1 | 4930431P03Rik | | | 15312 | 3 | 4 | | | | IV-1 | 4930538K18Rik | | |
| 15221 | 3 | 4 | | | | IV-1 | 4930432K21Rik | | | 15313 | 3 | 4 | | | | IV-1 | 4930539C22Rik | | |
| 15222 | 3 | 4 | | | | IV-1 | 4930432M17Rik | | | 15314 | 3 | 4 | | | | IV-1 | 4930539E08Rik | | |
| 15223 | 3 | 4 | | | | IV-1 | 4930433B08Rik | | | 15315 | 3 | 4 | | | | IV-1 | 4930539N22Rik | | |
| 15224 | 3 | 4 | | | | IV-1 | 4930433I11Rik | | | 15316 | 3 | 4 | | | | IV-1 | 4930543E12Rik | | |
| 15225 | 3 | 4 | | | | IV-1 | 4930433N12Rik | | | 15317 | 3 | 4 | | | | IV-1 | 4930545E07Rik | | |
| 15226 | 3 | 4 | | | | IV-1 | 4930434J06Rik | | | 15318 | 3 | 4 | | | | IV-1 | 4930546C10Rik | | |
| 15227 | 3 | 4 | | | | IV-1 | 4930435E12Rik | | | 15319 | 3 | 4 | | | | IV-1 | 4930546K05Rik | | |
| 15228 | 3 | 4 | | | | IV-1 | 4930438E09Rik | | | 15320 | 3 | 4 | | | | IV-1 | 4930547E08Rik | | |
| 15229 | 3 | 4 | | | | IV-1 | 4930442J19Rik | | | 15321 | 3 | 4 | | | | IV-1 | 4930547E14Rik | | |
| 15230 | 3 | 4 | | | | IV-1 | 4930442L01Rik | | | 15322 | 3 | 4 | | | | IV-1 | 4930548G14Rik | | |
| 15231 | 3 | 4 | | | | IV-1 | 4930444F02Rik | | | 15323 | 3 | 4 | | | | IV-1 | 4930548H24Rik | | |
| 15232 | 3 | 4 | | | | IV-1 | 4930444G20Rik | | | 15324 | 3 | 4 | | | | IV-1 | 4930548J01Rik | | |
| 15233 | 3 | 4 | | | | IV-1 | 4930444M15Rik | | | 15325 | 3 | 4 | | | | IV-1 | 4930549G23Rik | | |
| 15234 | 3 | 4 | | | | IV-1 | 4930444P10Rik | | | 15326 | 3 | 4 | | | | IV-1 | 4930550L24Rik | | |
| 15235 | 3 | 4 | | | | IV-1 | 4930447A16Rik | | | 15327 | 3 | 4 | | | | IV-1 | 4930552N02Rik | | |
| 15236 | 3 | 4 | | | | IV-1 | 4930448C13Rik | | | 15328 | 3 | 4 | | | | IV-1 | 4930554C24Rik | | |
| 15237 | 3 | 4 | | | | IV-1 | 4930448F12Rik | | | 15329 | 3 | 4 | | | | IV-1 | 4930555B11Rik | | |
| 15238 | 3 | 4 | | | | IV-1 | 4930448I06Rik | | | 15330 | 3 | 4 | | | | IV-1 | 4930555G01Rik | | |
| 15239 | 3 | 4 | | | | IV-1 | 4930448I18Rik | | | 15331 | 3 | 4 | | | | IV-1 | 4930556C24Rik | | |
| 15240 | 3 | 4 | | | | IV-1 | 4930448K20Rik | | | 15332 | 3 | 4 | | | | IV-1 | 4930556G01Rik | | |
| 15241 | 3 | 4 | | | | IV-1 | 4930449E01Rik | | | 15333 | 3 | 4 | | | | IV-1 | 4930557J02Rik | | |
| 15242 | 3 | 4 | | | | IV-1 | 4930452B06Rik | | | 15334 | 3 | 4 | | | | IV-1 | 4930558C23Rik | | |
| 15243 | 3 | 4 | | | | IV-1 | 4930452G13Rik | | | 15335 | 3 | 4 | | | | IV-1 | 4930558G05Rik | | |
| 15244 | 3 | 4 | | | | IV-1 | 4930452N14Rik | | | 15336 | 3 | 4 | | | | IV-1 | 4930558J18Rik | | |
| 15245 | 3 | 4 | | | | IV-1 | 4930453H23Rik | | | 15337 | 3 | 4 | | | | IV-1 | 4930563E18Rik | | |
| 15246 | 3 | 4 | | | | IV-1 | 4930453L07Rik | | | 15338 | 3 | 4 | | | | IV-1 | 4930563F08Rik | | |
| 15247 | 3 | 4 | | | | IV-1 | 4930453N24Rik | | | 15339 | 3 | 4 | | | | IV-1 | 4930563M20Rik | | |
| 15248 | 3 | 4 | | | | IV-1 | 4930455B14Rik | | | 15340 | 3 | 4 | | | | IV-1 | 4930564D02Rik | | |
| 15249 | 3 | 4 | | | | IV-1 | 4930455C13Rik | | | 15341 | 3 | 4 | | | | IV-1 | 4930565N06Rik | | |
| 15250 | 3 | 4 | | | | IV-1 | 4930455H04Rik | | | 15342 | 3 | 4 | | | | IV-1 | 4930567H12Rik | | |
| 15251 | 3 | 4 | | | | IV-1 | 4930455J16Rik | | | 15343 | 3 | 4 | | | | IV-1 | 4930567J20Rik | | |
| 15252 | 3 | 4 | | | | IV-1 | 4930456L15Rik | | | 15344 | 3 | 4 | | | | IV-1 | 4930567K20Rik | | |
| 15253 | 3 | 4 | | | | IV-1 | 4930459C07Rik | | | 15345 | 3 | 4 | | | | IV-1 | 4930568E12Rik | | |
| 15254 | 3 | 4 | | | | IV-1 | 4930459L07Rik | | | 15346 | 3 | 4 | | | | IV-1 | 4930570G19Rik | | |
| 15255 | 3 | 4 | | | | IV-1 | 4930467E23Rik | | | 15347 | 3 | 4 | | | | IV-1 | 4930571K23Rik | | |
| 15256 | 3 | 4 | | | | IV-1 | 4930468A15Rik | | | 15348 | 3 | 4 | | | | IV-1 | 4930571O06Rik | | |
| 15257 | 3 | 4 | | | | IV-1 | 4930470H14Rik | | | 15349 | 3 | 4 | | | | IV-1 | 4930572K03Rik | | |
| 15258 | 3 | 4 | | | | IV-1 | 4930470P17Rik | | | 15350 | 3 | 4 | | | | IV-1 | 4930572O03Rik | | |
| 15259 | 3 | 4 | | | | IV-1 | 4930471C04Rik | | | 15351 | 3 | 4 | | | | IV-1 | 4930578C19Rik | 79742 | 4-May-15 |
| 15260 | 3 | 4 | | | | IV-1 | 4930471G03Rik | | | 15352 | 3 | 4 | | | | IV-1 | 4930578I06Rik | | |
| 15261 | 3 | 4 | | | | IV-1 | 4930471M09Rik | | | 15353 | 3 | 4 | | | | IV-1 | 4930579F01Rik | | |
| 15262 | 3 | 4 | | | | IV-1 | 4930474H20Rik | | | 15354 | 3 | 4 | | | | IV-1 | 4930579G18Rik | | |
| 15263 | 3 | 4 | | | | IV-1 | 4930474M22Rik | | | 15355 | 3 | 4 | | | | IV-1 | 4930583K01Rik | | |
| 15264 | 3 | 4 | | | | IV-1 | 4930474N05Rik | | | 15356 | 3 | 4 | | | | IV-1 | 4930583P06Rik | | |
| 15265 | 3 | 4 | | | | IV-1 | 4930474N09Rik | | | 15357 | 3 | 4 | | | | IV-1 | 4930584F24Rik | | |
| 15266 | 3 | 4 | | | | IV-1 | 4930478L05Rik | | | 15358 | 3 | 4 | | | | IV-1 | 4930590J08Rik | | |
| 15267 | 3 | 4 | | | | IV-1 | 4930478P22Rik | | | 15359 | 3 | 4 | | | | IV-1 | 4930590L20Rik | | |
| 15268 | 3 | 4 | | | | IV-1 | 4930480G23Rik | | | 15360 | 3 | 4 | | | | IV-1 | 4930591A17Rik | | |
| 15269 | 3 | 4 | | | | IV-1 | 4930480M12Rik | | | 15361 | 3 | 4 | | | | IV-1 | 4930592A05Rik | | |
| 15270 | 3 | 4 | | | | IV-1 | 4930483J18Rik | | | 15362 | 3 | 4 | | | | IV-1 | 4930592I03Rik | | |
| 15271 | 3 | 4 | | | | IV-1 | 4930486F22Rik | | | 15363 | 3 | 4 | | | | IV-1 | 4930593A02Rik | | |
| 15272 | 3 | 4 | | | | IV-1 | 4930487H11Rik | | | 15364 | 3 | 4 | | | | IV-1 | 4930593C16Rik | | |
| 15273 | 3 | 4 | | | | IV-1 | 4930488B22Rik | | | 15365 | 3 | 4 | | | | IV-1 | 4930594C11Rik | | |
| 15274 | 3 | 4 | | | | IV-1 | 4930500F04Rik | | | 15366 | 3 | 4 | | | | IV-1 | 4930596D02Rik | | |
| 15275 | 3 | 4 | | | | IV-1 | 4930500L23Rik | | | 15367 | 3 | 4 | | | | IV-1 | 4930597G03Rik | | |
| | | | | | | | | | | 15368 | 3 | 4 | | | | IV-1 | 4930598F16Rik | | |
| | | | | | | | | | | 15369 | 3 | 4 | | | | IV-1 | 4930599N23Rik | | |

Fig. 30 - 82

| | | | | | | | |
|---|---|---|---|---|---|---|---|
| 15370 | 3 | 4 | | | | IV-1 | 4931402G19Rik |
| 15371 | 3 | 4 | | | | IV-1 | 4931403E22Rik |
| 15372 | 3 | 4 | | | | IV-1 | 4931406B18Rik |
| 15373 | 3 | 4 | | | | IV-1 | 4931406C07Rik |
| 15374 | 3 | 4 | | | | IV-1 | 4931406H21Rik |
| 15375 | 3 | 4 | | | | IV-1 | 4931412M21 |
| 15376 | 3 | 4 | | | | IV-1 | 4931414P19Rik |
| 15377 | 3 | 4 | | | | IV-1 | 4931417E11Rik |
| 15378 | 3 | 4 | | | | IV-1 | 4931419H13Rik |
| 15379 | 3 | 4 | | | | IV-1 | 4931420L22Rik |
| 15380 | 3 | 4 | | | | IV-1 | 4931423N10Rik |
| 15381 | 3 | 4 | | | | IV-1 | 4931428F04Rik |
| 15382 | 3 | 4 | | | | IV-1 | 4931430N09Rik |
| 15383 | 3 | 4 | | | | IV-1 | 4931431B13Rik |
| 15384 | 3 | 4 | | | | IV-1 | 4931440F15Rik |
| 15385 | 3 | 4 | | | | IV-1 | 4931440P22Rik |
| 15386 | 3 | 4 | | | | IV-1 | 4932412D23Rik |
| 15387 | 3 | 4 | | | | IV-1 | 4932413F04Rik |
| 15388 | 3 | 4 | | | | IV-1 | 4932414J04Rik |
| 15389 | 3 | 4 | | | | IV-1 | 4932414N04Rik |
| 15390 | 3 | 4 | | | | IV-1 | 4932415M13Rik |
| 15391 | 3 | 4 | | | | IV-1 | 4932416H05Rik |
| 15392 | 3 | 4 | | | | IV-1 | 4932416K20Rik |
| 15393 | 3 | 4 | | | | IV-1 | 4932435O22Rik |
| 15394 | 3 | 4 | | | | IV-1 | 4932438A13Rik |
| 15395 | 3 | 4 | | | | IV-1 | 4932443I19Rik |
| 15396 | 3 | 4 | | | | IV-1 | 4933400C23Rik |
| 15397 | 3 | 4 | | | | IV-1 | 4933400F21Rik |
| 15398 | 3 | 4 | | | | IV-1 | 4933401B06Rik |
| 15399 | 3 | 4 | | | | IV-1 | 4933401D09Rik |
| 15400 | 3 | 4 | | | | IV-1 | 4933402E13Rik |
| 15401 | 3 | 4 | | | | IV-1 | 4933402J07Rik |
| 15402 | 3 | 4 | | | | IV-1 | 4933402J15Rik |
| 15403 | 3 | 4 | | | | IV-1 | 4933402N03Rik |
| 15404 | 3 | 4 | | | | IV-1 | 4933402N22Rik |
| 15405 | 3 | 4 | | | | IV-1 | 4933402P03Rik |
| 15406 | 3 | 4 | | | | IV-1 | 4933403O08Rik |
| 15407 | 3 | 4 | | | | IV-1 | 4933404G15Rik |
| 15408 | 3 | 4 | | | | IV-1 | 4933405E24Rik |
| 15409 | 3 | 4 | | | | IV-1 | 4933405L10Rik |
| 15410 | 3 | 4 | | | | IV-1 | 4933405O20Rik |
| 15411 | 3 | 4 | | | | IV-1 | 4933406C10Rik |
| 15412 | 3 | 4 | | | | IV-1 | 4933406F09Rik |
| 15413 | 3 | 4 | | | | IV-1 | 4933406G16Rik |
| 15414 | 3 | 4 | | | | IV-1 | 4933406J10Rik |
| 15415 | 3 | 4 | | | | IV-1 | 4933406K04Rik |
| 15416 | 3 | 4 | | | | IV-1 | 4933406M09Rik |
| 15417 | 3 | 4 | | | | IV-1 | 4933407E24Rik |
| 15418 | 3 | 4 | | | | IV-1 | 4933407G14Rik |
| 15419 | 3 | 4 | | | | IV-1 | 4933407I05Rik |
| 15420 | 3 | 4 | | | | IV-1 | 4933407K13Rik |
| 15421 | 3 | 4 | | | | IV-1 | 4933408B17Rik |
| 15422 | 3 | 4 | | | | IV-1 | 4933408N05Rik |
| 15423 | 3 | 4 | | | | IV-1 | 4933411G06Rik |
| 15424 | 3 | 4 | | | | IV-1 | 4933411G11Rik |
| 15425 | 3 | 4 | | | | IV-1 | 4933411K16Rik |
| 15426 | 3 | 4 | | | | IV-1 | 4933412O06Rik |
| 15427 | 3 | 4 | | | | IV-1 | 4933413J09Rik |
| 15428 | 3 | 4 | | | | IV-1 | 4933413L06Rik |
| 15429 | 3 | 4 | | | | IV-1 | 4933415F23Rik |
| 15430 | 3 | 4 | | | | IV-1 | 4933416C03Rik |
| 15431 | 3 | 4 | | | | IV-1 | 4933416I08Rik |
| 15432 | 3 | 4 | | | | IV-1 | 4933416M07Rik |
| 15433 | 3 | 4 | | | | IV-1 | 4933417A18Rik |
| 15434 | 3 | 4 | | | | IV-1 | 4933417D19Rik |
| 15435 | 3 | 4 | | | | IV-1 | 4933417E11Rik |
| 15436 | 3 | 4 | | | | IV-1 | 4933417G07Rik |
| 15437 | 3 | 4 | | | | IV-1 | 4933421I07Rik |
| 15438 | 3 | 4 | | | | IV-1 | 4933421O10Rik |
| 15439 | 3 | 4 | | | | IV-1 | 4933424G06Rik |
| 15440 | 3 | 4 | | | | IV-1 | 4933425B07Rik |
| 15441 | 3 | 4 | | | | IV-1 | 4933425L06Rik |
| 15442 | 3 | 4 | | | | IV-1 | 4933426M11Rik |
| 15443 | 3 | 4 | | | | IV-1 | 4933427D14Rik |
| 15444 | 3 | 4 | | | | IV-1 | 4933427E13Rik |
| 15445 | 3 | 4 | | | | IV-1 | 4933428G20Rik |
| 15446 | 3 | 4 | | | | IV-1 | 4933429K18Rik |
| 15447 | 3 | 4 | | | | IV-1 | 4933429O19Rik |
| 15448 | 3 | 4 | | | | IV-1 | 4933430H16Rik |
| 15449 | 3 | 4 | | | | IV-1 | 4933430I17Rik |
| 15450 | 3 | 4 | | | | IV-1 | 4933430M04Rik |
| 15451 | 3 | 4 | | | | IV-1 | 4933430N04Rik |
| 15452 | 3 | 4 | | | | IV-1 | 4933431E20Rik |
| 15453 | 3 | 4 | | | | IV-1 | 4933432G23Rik |
| 15454 | 3 | 4 | | | | IV-1 | 4933432J09Rik |
| 15455 | 3 | 4 | | | | IV-1 | 4933432K03Rik |
| 15456 | 3 | 4 | | | | IV-1 | 4933433F19Rik |
| 15457 | 3 | 4 | | | | IV-1 | 4933433G08Rik |
| 15458 | 3 | 4 | | | | IV-1 | 4933434I20Rik |
| 15459 | 3 | 4 | | | | IV-1 | 4933436H12Rik |
| 15460 | 3 | 4 | | | | IV-1 | 4933440M02Rik |
| 15461 | 3 | 4 | | | | IV-1 | 5031410I06Rik |
| 15462 | 3 | 4 | | | | IV-1 | 5031425F14Rik |
| 15463 | 3 | 4 | | | | IV-1 | 5031426D15Rik |
| 15464 | 3 | 4 | | | | IV-1 | 5031434C07Rik |
| 15465 | 3 | 4 | | | | IV-1 | 5330413P13Rik |
| 15466 | 3 | 4 | | | | IV-1 | 5330439B14Rik |
| 15467 | 3 | 4 | | | | IV-1 | 5430402E10Rik |
| 15468 | 3 | 4 | | | | IV-1 | 5430402O13Rik |
| 15469 | 3 | 4 | | | | IV-1 | 5430403N17Rik |
| 15470 | 3 | 4 | | | | IV-1 | 5430405H02Rik |
| 15471 | 3 | 4 | | | | IV-1 | 5430421F17Rik |
| 15472 | 3 | 4 | | | | IV-1 | 5430434I15Rik |
| 15473 | 3 | 4 | | | | IV-1 | 5430440P10Rik |
| 15474 | 3 | 4 | | | | IV-1 | 5530400C23Rik |
| 15475 | 3 | 4 | | | | IV-1 | 5530401A14Rik |
| 15476 | 3 | 4 | | | | IV-1 | 5730405O15Rik |
| 15477 | 3 | 4 | | | | IV-1 | 5730455P16Rik |
| 15478 | 3 | 4 | | | | IV-1 | 5730457N03Rik |
| 15479 | 3 | 4 | | | | IV-1 | 5730480H06Rik |
| 15480 | 3 | 4 | | | | IV-1 | 5730488B01Rik |
| 15481 | 3 | 4 | | | | IV-1 | 5830418P13Rik |
| 15482 | 3 | 4 | | | | IV-1 | 5830432E09Rik |
| 15483 | 3 | 4 | | | | IV-1 | 5930403L14Rik |
| 15484 | 3 | 4 | | | | IV-1 | 6030407O03Rik |
| 15485 | 3 | 4 | | | | IV-1 | 6030408B16Rik |
| 15486 | 3 | 4 | | | | IV-1 | 6030443J06Rik |
| 15487 | 3 | 4 | | | | IV-1 | 6030458C11Rik |
| 15488 | 3 | 4 | | | | IV-1 | 6030498E09Rik |
| 15489 | 3 | 4 | | | | IV-1 | 6330403A02Rik |
| 15490 | 3 | 4 | | | | IV-1 | 6330408A02Rik |
| 15491 | 3 | 4 | | | | IV-1 | 6330415B21Rik |
| 15492 | 3 | 4 | | | | IV-1 | 6330416G13Rik |
| 15493 | 3 | 4 | | | | IV-1 | 6430411K18Rik |
| 15494 | 3 | 4 | | | | IV-1 | 6430562O15Rik |
| 15495 | 3 | 4 | | | | IV-1 | 6530402F15Rik |
| 15496 | 3 | 4 | | | | IV-1 | 7420461P10Rik |
| 15497 | 3 | 4 | | | | IV-1 | 7420701I03Rik |
| 15498 | 3 | 4 | | | | IV-1 | 7530416G11Rik |
| 15499 | 3 | 4 | | | | IV-1 | 7630403G23Rik |
| 15500 | 3 | 4 | | | | IV-1 | 8030411F24Rik |
| 15501 | 3 | 4 | | | | IV-1 | 8030423J24Rik |
| 15502 | 3 | 4 | | | | IV-1 | 8430431K14Rik |
| 15503 | 3 | 4 | | | | IV-1 | 8430436N08Rik |
| 15504 | 3 | 4 | | | | IV-1 | 9030204H09Rik |
| 15505 | 3 | 4 | | | | IV-1 | 9030404E10Rik |
| 15506 | 3 | 4 | | | | IV-1 | 9030624J02Rik |
| 15507 | 3 | 4 | | | | IV-1 | 9130015A21Rik |
| 15508 | 3 | 4 | | | | IV-1 | 9130015L21Rik |
| 15509 | 3 | 4 | | | | IV-1 | 9130019P16Rik |
| 15510 | 3 | 4 | | | | IV-1 | 9130204L05Rik |
| 15511 | 3 | 4 | | | | IV-1 | 9130221H12Rik |
| 15512 | 3 | 4 | | | | IV-1 | 9130227L01Rik |
| 15513 | 3 | 4 | | | | IV-1 | 9130409I23Rik |
| 15514 | 3 | 4 | | | | IV-1 | 9230102O04Rik |
| 15515 | 3 | 4 | | | | IV-1 | 9230110C19Rik |
| 15516 | 3 | 4 | | | | IV-1 | 9330020H09Rik |
| 15517 | 3 | 4 | | | | IV-1 | 9330117O12Rik |
| 15518 | 3 | 4 | | | | IV-1 | 9330159F19Rik |
| 15519 | 3 | 4 | | | | IV-1 | 9330178D15Rik |
| 15520 | 3 | 4 | | | | IV-1 | 9330179D12Rik |
| 15521 | 3 | 4 | | | | IV-1 | 9330182L06Rik |
| 15522 | 3 | 4 | | | | IV-1 | 9330182O14Rik |
| 15523 | 3 | 4 | | | | IV-1 | 9430007A20Rik |
| 15524 | 3 | 4 | | | | IV-1 | 9430015G10Rik |
| 15525 | 3 | 4 | | | | IV-1 | 9430016H08Rik |
| 15526 | 3 | 4 | | | | IV-1 | 9430019H16Rik |
| 15527 | 3 | 4 | | | | IV-1 | 9430037G07Rik |
| 15528 | 3 | 4 | | | | IV-1 | 9430038I01Rik |
| 15529 | 3 | 4 | | | | IV-1 | 9430076C15Rik |
| 15530 | 3 | 4 | | | | IV-1 | 9530026F06Rik |
| 15531 | 3 | 4 | | | | IV-1 | 9530026P05Rik |
| 15532 | 3 | 4 | | | | IV-1 | 9530036O11Rik |
| 15533 | 3 | 4 | | | | IV-1 | 9530051G07Rik |
| 15534 | 3 | 4 | | | | IV-1 | 9530052E02Rik |
| 15535 | 3 | 4 | | | | IV-1 | 9530068E07Rik |
| 15536 | 3 | 4 | | | | IV-1 | 9630028B13Rik |
| 15537 | 3 | 4 | | | | IV-1 | 9630028H03Rik |
| 15538 | 3 | 4 | | | | IV-1 | 9630033F20Rik |
| 15539 | 3 | 4 | | | | IV-1 | 9830166K06Rik |
| 15540 | 3 | 4 | | | | IV-1 | 9930021J03Rik |
| 15541 | 3 | 4 | | | | IV-1 | 9930104L06Rik |
| 15542 | 3 | 4 | | | | IV-1 | 9930111H07Rik |
| 15543 | 3 | 4 | | | | IV-1 | 9930111J21Rik |
| 15544 | 3 | 4 | | | | IV-1 | A1bg | 1 | 4-May-15 |
| 15545 | 3 | 4 | | | | IV-1 | A230009B12Rik |
| 15546 | 3 | 4 | | | | IV-1 | A230020J21Rik |
| 15547 | 3 | 4 | | | | IV-1 | A230028O05Rik |
| 15548 | 3 | 4 | | | | IV-1 | A230065H16Rik |
| 15549 | 3 | 4 | | | | IV-1 | A230072C01Rik |
| 15550 | 3 | 4 | | | | IV-1 | A230072E10Rik |
| 15551 | 3 | 4 | | | | IV-1 | A230077H06Rik |
| 15552 | 3 | 4 | | | | IV-1 | A230103J11Rik |
| 15553 | 3 | 4 | | | | IV-1 | A230108P19Rik |
| 15554 | 3 | 4 | | | | IV-1 | A330010I07Rik |
| 15555 | 3 | 4 | | | | IV-1 | A330048O09Rik |
| 15556 | 3 | 4 | | | | IV-1 | A330076H08Rik |

Fig. 30 - 83

| | | | | | | | | | |
|---|---|---|---|---|---|---|---|---|---|
| 15557 | 3 | 4 | | | | IV-1 | A330093E20Rik | | |
| 15558 | 3 | 4 | | | | IV-1 | A330102H10Rik | | |
| 15559 | 3 | 4 | | | | IV-1 | A3galt2 | 127550 | 4-May-15 |
| 15560 | 3 | 4 | | | | IV-1 | A430005L14Rik | | |
| 15561 | 3 | 4 | | | | IV-1 | A430090L17Rik | | |
| 15562 | 3 | 4 | | | | IV-1 | A430093F15Rik | | |
| 15563 | 3 | 4 | | | | IV-1 | A430105I19Rik | | |
| 15564 | 3 | 4 | | | | IV-1 | A530050N04Rik | | |
| 15565 | 3 | 4 | | | | IV-1 | A530053G22Rik | | |
| 15566 | 3 | 4 | | | | IV-1 | A530088E08Rik | | |
| 15567 | 3 | 4 | | | | IV-1 | A630010A05Rik | | |
| 15568 | 3 | 4 | | | | IV-1 | A630023A22Rik | | |
| 15569 | 3 | 4 | | | | IV-1 | A630075F10Rik | | |
| 15570 | 3 | 4 | | | | IV-1 | A730020E08Rik | | |
| 15571 | 3 | 4 | | | | IV-1 | A730046J19Rik | | |
| 15572 | 3 | 4 | | | | IV-1 | A730056A06Rik | | |
| 15573 | 3 | 4 | | | | IV-1 | A730085K08Rik | | |
| 15574 | 3 | 4 | | | | IV-1 | A730090N16Rik | | |
| 15575 | 3 | 4 | | | | IV-1 | A830019L24Rik | | |
| 15576 | 3 | 4 | | | | IV-1 | A830052D11Rik | | |
| 15577 | 3 | 4 | | | | IV-1 | A830082K12Rik | | |
| 15578 | 3 | 4 | | | | IV-1 | A830082N09Rik | | |
| 15579 | 3 | 4 | | | | IV-1 | A930001A20Rik | | |
| 15580 | 3 | 4 | | | | IV-1 | A930004D18Rik | | |
| 15581 | 3 | 4 | | | | IV-1 | A930009A15Rik | | |
| 15582 | 3 | 4 | | | | IV-1 | A930011G23Rik | | |
| 15583 | 3 | 4 | | | | IV-1 | A930011O12Rik | | |
| 15584 | 3 | 4 | | | | IV-1 | A930012L18Rik | | |
| 15585 | 3 | 4 | | | | IV-1 | A930019D19Rik | | |
| 15586 | 3 | 4 | | | | IV-1 | A930024E05Rik | | |
| 15587 | 3 | 4 | | | | IV-1 | AA536875 | | |
| 15588 | 3 | 4 | | | | IV-1 | AA543186 | | |
| 15589 | 3 | 4 | | | | IV-1 | AA545401 | | |
| 15590 | 3 | 4 | | | | IV-1 | AA545190 | | |
| 15591 | 3 | 4 | | | | IV-1 | AA619741 | | |
| 15592 | 3 | 4 | | | | IV-1 | AA792892 | | |
| 15593 | 3 | 4 | | | | IV-1 | Aaas | 8086 | 12-May-15 |
| 15594 | 3 | 4 | | | | IV-1 | Aadacl3 | 126767 | 12-May-15 |
| 15595 | 3 | 4 | | | | IV-1 | Aadat | 51166 | 4-May-15 |
| 15596 | 3 | 4 | | | | IV-1 | Aagab | 79719 | 17-May-15 |
| 15597 | 3 | 4 | | | | IV-1 | Aak1 | 22848 | 31-May-15 |
| 15598 | 3 | 4 | | | | IV-1 | Aanat | 15 | 12-May-15 |
| 15599 | 3 | 4 | | | | IV-1 | Aar2 | 25980 | 4-May-15 |
| 15600 | 3 | 4 | | | | IV-1 | Aard | 441376 | 4-May-15 |
| 15601 | 3 | 4 | | | | IV-1 | Aars | 16 | 31-May-15 |
| 15602 | 3 | 4 | | | | IV-1 | Aars2 | 57505 | 4-May-15 |
| 15603 | 3 | 4 | | | | IV-1 | Aasdhppt | 60496 | 4-May-15 |
| 15604 | 3 | 4 | | | | IV-1 | Abca13 | 154664 | 12-May-15 |
| 15605 | 3 | 4 | | | | IV-1 | Abca15 | | |
| 15606 | 3 | 4 | | | | IV-1 | Abca16 | | |
| 15607 | 3 | 4 | | | | IV-1 | Abca17 | 650665 | 12-May-15 |
| 15608 | 3 | 4 | | | | IV-1 | Abcc10 | 89845 | 4-May-15 |
| 15609 | 3 | 4 | | | | IV-1 | Abcc2 | 1244 | 17-May-15 |
| 15610 | 3 | 4 | | | | IV-1 | Abcc6 | 368 | 23-May-15 |
| 15611 | 3 | 4 | | | | IV-1 | Abcc8 | 6833 | 24-May-15 |
| 15612 | 3 | 4 | | | | IV-1 | Abce1 | 6059 | 21-May-15 |
| 15613 | 3 | 4 | | | | IV-1 | Abcf1 | 23 | 21-May-15 |
| 15614 | 3 | 4 | | | | IV-1 | Abcf2 | 10061 | 12-May-15 |
| 15615 | 3 | 4 | | | | IV-1 | Abcf3 | 55324 | 4-May-15 |
| 15616 | 3 | 4 | | | | IV-1 | Abcg8 | 64241 | 23-May-15 |
| 15617 | 3 | 4 | | | | IV-1 | Abhd11 | 83451 | 4-May-15 |
| 15618 | 3 | 4 | | | | IV-1 | Abhd12b | 145447 | 4-May-15 |
| 15619 | 3 | 4 | | | | IV-1 | Abhd13 | 84945 | 4-May-15 |
| 15620 | 3 | 4 | | | | IV-1 | Abhd14a | 25864 | 4-May-15 |
| 15621 | 3 | 4 | | | | IV-1 | Abhd14b | 84836 | 4-May-15 |
| 15622 | 3 | 4 | | | | IV-1 | Abhd15 | 116236 | 4-May-15 |
| 15623 | 3 | 4 | | | | IV-1 | Abhd16b | 140701 | 4-May-15 |
| 15624 | 3 | 4 | | | | IV-1 | Abhd17a | 81926 | 4-May-15 |
| 15625 | 3 | 4 | | | | IV-1 | Abhd17b | 51104 | 4-May-15 |
| 15626 | 3 | 4 | | | | IV-1 | Abhd5 | 51099 | 12-May-15 |
| 15627 | 3 | 4 | | | | IV-1 | Abi1 | 10006 | 12-May-15 |
| 15628 | 3 | 4 | | | | IV-1 | Abi2 | 10152 | 12-May-15 |
| 15629 | 3 | 4 | | | | IV-1 | Abi3 | 51225 | 4-May-15 |
| 15630 | 3 | 4 | | | | IV-1 | Abl2 | 27 | 12-May-15 |
| 15631 | 3 | 4 | | | | IV-1 | Ablim1 | 3983 | 12-May-15 |
| 15632 | 3 | 4 | | | | IV-1 | Abtb1 | 80325 | 4-May-15 |
| 15633 | 3 | 4 | | | | IV-1 | Acad9 | 28976 | 4-May-15 |
| 15634 | 3 | 4 | | | | IV-1 | Acadl | 33 | 4-May-15 |
| 15635 | 3 | 4 | | | | IV-1 | Acadvl | 37 | 23-May-15 |
| 15636 | 3 | 4 | | | | IV-1 | Acap3 | 116983 | 4-May-15 |
| 15637 | 3 | 4 | | | | IV-1 | Acat1 | 38 | 7-Jun-15 |
| 15638 | 3 | 4 | | | | IV-1 | Acbd4 | 79777 | 4-May-15 |
| 15639 | 3 | 4 | | | | IV-1 | Acbd6 | 84320 | 14-May-15 |
| 15640 | 3 | 4 | | | | IV-1 | Acd | 65057 | 4-May-15 |
| 15641 | 3 | 4 | | | | IV-1 | Aco2 | 50 | 12-May-15 |
| 15642 | 3 | 4 | | | | IV-1 | Acot13 | 55856 | 24-May-15 |
| 15643 | 3 | 4 | | | | IV-1 | Acot9 | 23597 | 4-May-15 |
| 15644 | 3 | 4 | | | | IV-1 | Acox2 | 8309 | 4-May-15 |
| 15645 | 3 | 4 | | | | IV-1 | Acox3 | 8310 | 4-May-15 |
| 15646 | 3 | 4 | | | | IV-1 | Acr | 49 | 12-May-15 |
| 15647 | 3 | 4 | | | | IV-1 | Acrbp | 84519 | 4-May-15 |
| 15648 | 3 | 4 | | | | IV-1 | Acsf2 | 80221 | 4-May-15 |
| 15649 | 3 | 4 | | | | IV-1 | Actl11 | | |
| 15650 | 3 | 4 | | | | IV-1 | Actl6a | 86 | 3-May-15 |
| 15651 | 3 | 4 | | | | IV-1 | Actl6b | 51412 | 1-Jun-15 |
| 15652 | 3 | 4 | | | | IV-1 | Actl7a | 10881 | 4-May-15 |
| 15653 | 3 | 4 | | | | IV-1 | Actl7b | 10880 | 12-May-15 |
| 15654 | 3 | 4 | | | | IV-1 | Actl9 | 284382 | 4-May-15 |
| 15655 | 3 | 4 | | | | IV-1 | Actr1a | 10121 | 4-May-15 |
| 15656 | 3 | 4 | | | | IV-1 | Actr1b | 10120 | 4-May-15 |
| 15657 | 3 | 4 | | | | IV-1 | Actr2 | 10097 | 4-May-15 |
| 15658 | 3 | 4 | | | | IV-1 | Actr3 | 10096 | 4-May-15 |
| 15659 | 3 | 4 | | | | IV-1 | Actr6 | 64431 | 4-May-15 |
| 15660 | 3 | 4 | | | | IV-1 | Actr8 | 93973 | 4-May-15 |
| 15661 | 3 | 4 | | | | IV-1 | Actrt1 | 139741 | 28-May-15 |
| 15662 | 3 | 4 | | | | IV-1 | Actrt2 | 140625 | 4-May-15 |
| 15663 | 3 | 4 | | | | IV-1 | Actrt3 | 84517 | 4-May-15 |
| 15664 | 3 | 4 | | | | IV-1 | Acvr1 | 90 | 12-May-15 |
| 15665 | 3 | 4 | | | | IV-1 | Adad2 | 161931 | 4-May-15 |
| 15666 | 3 | 4 | | | | IV-1 | Adat | 161823 | 4-May-15 |
| 15667 | 3 | 4 | | | | IV-1 | Adam10 | 102 | 24-May-15 |
| 15668 | 3 | 4 | | | | IV-1 | Adam18 | 8749 | May-15 |
| 15669 | 3 | 4 | | | | IV-1 | Adam1b | 100420505 | 4-May-15 |
| 15670 | 3 | 4 | | | | IV-1 | Adam2 | 2515 | 4-May-15 |
| 15671 | 3 | 4 | | | | IV-1 | Adam20 | 8748 | 4-May-15 |
| 15672 | 3 | 4 | | | | IV-1 | Adam21 | 8747 | 4-May-15 |
| 15673 | 3 | 4 | | | | IV-1 | Adam22 | 53616 | 4-May-15 |
| 15674 | 3 | 4 | | | | IV-1 | Adam25 | | |
| 15675 | 3 | 4 | | | | IV-1 | Adam26a | | |
| 15676 | 3 | 4 | | | | IV-1 | Adam26b | | |
| 15677 | 3 | 4 | | | | IV-1 | Adam3 | 1587 | 4-May-15 |
| 15678 | 3 | 4 | | | | IV-1 | Adam30 | 11085 | 4-May-15 |
| 15679 | 3 | 4 | | | | IV-1 | Adam32 | 203102 | 4-May-15 |
| 15680 | 3 | 4 | | | | IV-1 | Adam39 | | |
| 15681 | 3 | 4 | | | | IV-1 | Adam4 | | |
| 15682 | 3 | 4 | | | | IV-1 | Adam5 | 255926 | 4-May-15 |
| 15683 | 3 | 4 | | | | IV-1 | Adam6a | | |
| 15684 | 3 | 4 | | | | IV-1 | Adamts14 | 140766 | 10-May-15 |
| 15685 | 3 | 4 | | | | IV-1 | Adamts17 | 170691 | 17-May-15 |
| 15686 | 3 | 4 | | | | IV-1 | Adamts19 | 171019 | 4-May-15 |
| 15687 | 3 | 4 | | | | IV-1 | Adat1 | 23536 | 4-May-15 |
| 15688 | 3 | 4 | | | | IV-1 | Adat2 | 134637 | 23-May-15 |
| 15689 | 3 | 4 | | | | IV-1 | Adck2 | 90956 | 4-May-15 |
| 15690 | 3 | 4 | | | | IV-1 | Adck5 | 203054 | 4-May-15 |
| 15691 | 3 | 4 | | | | IV-1 | Adcy2 | 108 | 4-May-15 |
| 15692 | 3 | 4 | | | | IV-1 | Adgb | 79747 | 4-May-15 |
| 15693 | 3 | 4 | | | | IV-1 | Adh6a | | |
| 15694 | 3 | 4 | | | | IV-1 | Adipor2 | 79602 | 31-May-15 |
| 15695 | 3 | 4 | | | | IV-1 | Adnp2 | 22850 | 4-May-15 |
| 15696 | 3 | 4 | | | | IV-1 | Ado | 84890 | 4-May-15 |
| 15697 | 3 | 4 | | | | IV-1 | Adpgk | 83440 | 14-May-15 |
| 15698 | 3 | 4 | | | | IV-1 | Adprm | 56985 | 4-May-15 |
| 15699 | 3 | 4 | | | | IV-1 | Adra2c | 152 | 4-May-15 |
| 15700 | 3 | 4 | | | | IV-1 | Adsl | 158 | 12-May-15 |
| 15701 | 3 | 4 | | | | IV-1 | Afap1 | 60312 | 4-May-15 |
| 15702 | 3 | 4 | | | | IV-1 | Afap1l1 | 134265 | 4-May-15 |
| 15703 | 3 | 4 | | | | IV-1 | Afg3l1 | 172 | 12-May-15 |
| 15704 | 3 | 4 | | | | IV-1 | Afg3l2 | 10939 | 23-May-15 |
| 15705 | 3 | 4 | | | | IV-1 | Afm | 173 | 4-May-15 |
| 15706 | 3 | 4 | | | | IV-1 | Aftph | 54812 | 4-May-15 |
| 15707 | 3 | 4 | | | | IV-1 | Aga | 175 | 12-May-15 |
| 15708 | 3 | 4 | | | | IV-1 | Agbl1 | 123624 | 23-May-15 |
| 15709 | 3 | 4 | | | | IV-1 | Agbl3 | 340351 | 4-May-15 |
| 15710 | 3 | 4 | | | | IV-1 | Agbl4 | 84871 | 4-May-15 |
| 15711 | 3 | 4 | | | | IV-1 | Agbl5 | 60509 | 4-May-15 |
| 15712 | 3 | 4 | | | | IV-1 | Agk | 55750 | 4-May-15 |
| 15713 | 3 | 4 | | | | IV-1 | Agl | 178 | 23-May-15 |
| 15714 | 3 | 4 | | | | IV-1 | Ago2 | 27161 | 28-May-15 |
| 15715 | 3 | 4 | | | | IV-1 | Ago3 | 192669 | 4-May-15 |
| 15716 | 3 | 4 | | | | IV-1 | Ago4 | 192670 | 4-May-15 |
| 15717 | 3 | 4 | | | | IV-1 | Agpat1 | 10554 | 4-May-15 |
| 15718 | 3 | 4 | | | | IV-1 | Agpat2 | 10555 | 23-May-15 |
| 15719 | 3 | 4 | | | | IV-1 | Agpat4 | 56895 | 4-May-15 |
| 15720 | 3 | 4 | | | | IV-1 | Agpat6 | 137964 | 4-May-15 |
| 15721 | 3 | 4 | | | | IV-1 | Agtrap | 57085 | 4-May-15 |
| 15722 | 3 | 4 | | | | IV-1 | Agxt2 | 64902 | 12-May-15 |
| 15723 | 3 | 4 | | | | IV-1 | Ahcy | 191 | 12-May-15 |
| 15724 | 3 | 4 | | | | IV-1 | Ahcyl2 | 23382 | 3-May-15 |
| 15725 | 3 | 4 | | | | IV-1 | Ahi1 | 54806 | 23-May-15 |
| 15726 | 3 | 4 | | | | IV-1 | Ahnak | 79026 | 4-May-15 |
| 15727 | 3 | 4 | | | | IV-1 | Ahsa1 | 10598 | 4-May-15 |
| 15728 | 3 | 4 | | | | IV-1 | Ahsa2 | 130872 | 4-May-15 |
| 15729 | 3 | 4 | | | | IV-1 | Ahsg | 197 | 12-May-15 |
| 15730 | 3 | 4 | | | | IV-1 | AI115009 | | |
| 15731 | 3 | 4 | | | | IV-1 | AI450353 | | |
| 15732 | 3 | 4 | | | | IV-1 | AI463170 | | |
| 15733 | 3 | 4 | | | | IV-1 | AI597479 | | |
| 15734 | 3 | 4 | | | | IV-1 | AI606473 | | |
| 15735 | 3 | 4 | | | | IV-1 | AI837181 | | |
| 15736 | 3 | 4 | | | | IV-1 | AI847159 | | |
| 15737 | 3 | 4 | | | | IV-1 | AI987944 | | |
| 15738 | 3 | 4 | | | | IV-1 | Aig1 | 51390 | 12-May-15 |
| 15739 | 3 | 4 | | | | IV-1 | Aim2 | 9447 | 17-May-15 |
| 15740 | 3 | 4 | | | | IV-1 | Aimp2 | 7965 | 4-May-15 |
| 15741 | 3 | 4 | | | | IV-1 | Aipl1 | 23386 | 23-May-15 |
| 15742 | 3 | 4 | | | | IV-1 | Aire | 326 | 28-May-15 |
| 15743 | 3 | 4 | | | | IV-1 | Ajuba | 84962 | 4-May-15 |
| 15744 | 3 | 4 | | | | IV-1 | Ak6 | 102157402 | 4-May-15 |
| 15745 | 3 | 4 | | | | IV-1 | Akap11 | 11215 | 4-May-15 |
| 15746 | 3 | 4 | | | | IV-1 | Akap17b | | |

Fig. 30 - 84

| | | | | | | | | | | | | | | | |
|---|---|---|---|---|---|---|---|---|---|---|---|---|---|---|---|
| 15747 | 3 | 4 | | | | IV-1 | Akap8l | 26993 | 12-May-15 | 15841 | 3 | 4 | | IV-1 | Ap3m1 | 26985 | 4-May-15 |
| 15748 | 3 | 4 | | | | IV-1 | Akap9 | 10142 | 29-May-15 | 15842 | 3 | 4 | | IV-1 | Ap3s1 | 1176 | 4-May-15 |
| 15749 | 3 | 4 | | | | IV-1 | Akip1 | 56672 | 4-May-15 | 15843 | 3 | 4 | | IV-1 | Ap4b1 | 10717 | 12-May-15 |
| 15750 | 3 | 4 | | | | IV-1 | Akirin1 | 79647 | 4-May-15 | 15844 | 3 | 4 | | IV-1 | Ap4e1 | 23431 | 12-May-15 |
| 15751 | 3 | 4 | | | | IV-1 | Akirin2 | 55122 | 4-May-15 | 15845 | 3 | 4 | | IV-1 | Ap4m1 | 9179 | 4-May-15 |
| 15752 | 3 | 4 | | | | IV-1 | Akp3 | | | 15846 | 3 | 4 | | IV-1 | Ap4s1 | 11154 | 4-May-15 |
| 15753 | 3 | 4 | | | | IV-1 | Akr1a1 | 10327 | 12-May-15 | 15847 | 3 | 4 | | IV-1 | Ap5m1 | 55745 | 4-May-15 |
| 15754 | 3 | 4 | | | | IV-1 | Akr1b10 | 57016 | 4-May-15 | 15848 | 3 | 4 | | IV-1 | Ap5s1 | 55317 | 4-May-15 |
| 15755 | 3 | 4 | | | | IV-1 | Akr1c13 | | | 15849 | 3 | 4 | | IV-1 | Ap5z1 | 9907 | 4-May-15 |
| 15756 | 3 | 4 | | | | IV-1 | Akr1c21 | | | 15850 | 3 | 4 | | IV-1 | Apaf1 | 317 | 12-May-15 |
| 15757 | 3 | 4 | | | | IV-1 | Akr1cl | | | 15851 | 3 | 4 | | IV-1 | Apba2 | 321 | 12-May-15 |
| 15758 | 3 | 4 | | | | IV-1 | Akr1d1 | 6718 | 4-May-15 | 15852 | 3 | 4 | | IV-1 | Apba3 | 9546 | 4-May-15 |
| 15759 | 3 | 4 | | | | IV-1 | Akt1s1 | 84335 | 4-May-15 | 15853 | 3 | 4 | | IV-1 | Apc | 324 | 7-Jun-15 |
| 15760 | 3 | 4 | | | | IV-1 | Akt2 | 208 | 17-May-15 | 15854 | 3 | 4 | | IV-1 | Apc2 | 10297 | 7-Jun-15 |
| 15761 | 3 | 4 | | | | IV-1 | Akt3 | 10000 | 17-May-15 | 15855 | 3 | 4 | | IV-1 | Aph1b | 83464 | 4-May-15 |
| 15762 | 3 | 4 | | | | IV-1 | Aldh18a1 | 5832 | 23-May-15 | 15856 | 3 | 4 | | IV-1 | Aph1c | | |
| 15763 | 3 | 4 | | | | IV-1 | Aldh8a1 | 64577 | 23-May-15 | 15857 | 3 | 4 | | IV-1 | Apip | 51074 | 4-May-15 |
| 15764 | 3 | 4 | | | | IV-1 | Aldh9a1 | 223 | 23-May-15 | 15858 | 3 | 4 | | IV-1 | Apmap | 57136 | 4-May-15 |
| 15765 | 3 | 4 | | | | IV-1 | Aldoa | 226 | 4-May-15 | 15859 | 3 | 4 | | IV-1 | Apoo | 79135 | 4-May-15 |
| 15766 | 3 | 4 | | | | IV-1 | Alg11 | 440138 | 23-May-15 | 15860 | 3 | 4 | | IV-1 | Appl2 | 55198 | 7-Jun-15 |
| 15767 | 3 | 4 | | | | IV-1 | Alg12 | 79087 | 23-May-15 | 15861 | 3 | 4 | | IV-1 | Aprt | 353 | 23-May-15 |
| 15768 | 3 | 4 | | | | IV-1 | Alg14 | 199857 | 5-May-15 | 15862 | 3 | 4 | | IV-1 | Ar | 367 | 7-Jun-15 |
| 15769 | 3 | 4 | | | | IV-1 | Alg2 | 85365 | 13-Jun-15 | 15863 | 3 | 4 | | IV-1 | Arap1 | 116985 | 4-May-15 |
| 15770 | 3 | 4 | | | | IV-1 | Alg5 | 29880 | 4-May-15 | 15864 | 3 | 4 | | IV-1 | Arf3 | 377 | 4-May-15 |
| 15771 | 3 | 4 | | | | IV-1 | Alg6 | 29929 | 23-May-15 | 15865 | 3 | 4 | | IV-1 | Arf4 | 378 | 31-May-15 |
| 15772 | 3 | 4 | | | | IV-1 | Alk | 238 | 26-May-15 | 15866 | 3 | 4 | | IV-1 | Arf5 | 381 | 23-May-15 |
| 15773 | 3 | 4 | | | | IV-1 | Alkbh1 | 8846 | 4-May-15 | 15867 | 3 | 4 | | IV-1 | Arfgap3 | 26286 | 4-May-15 |
| 15774 | 3 | 4 | | | | IV-1 | Alkbh2 | 121642 | 12-May-15 | 15868 | 3 | 4 | | IV-1 | Arfgef2 | 10564 | 4-May-15 |
| 15775 | 3 | 4 | | | | IV-1 | Alkbh4 | 54784 | 4-May-15 | 15869 | 3 | 4 | | IV-1 | Arfip1 | 27236 | 4-May-15 |
| 15776 | 3 | 4 | | | | IV-1 | Alkbh7 | 84266 | 4-May-15 | 15870 | 3 | 4 | | IV-1 | Arfip2 | 23647 | 4-May-15 |
| 15777 | 3 | 4 | | | | IV-1 | Allc | 55821 | 20-May-15 | 15871 | 3 | 4 | | IV-1 | Arfrp1 | 10139 | 23-May-15 |
| 15778 | 3 | 4 | | | | IV-1 | Aloxe3 | 59344 | 23-May-15 | 15872 | 3 | 4 | | IV-1 | Arhgap1 | 392 | 4-May-15 |
| 15779 | 3 | 4 | | | | IV-1 | Alpk1 | 80216 | 28-May-15 | 15873 | 3 | 4 | | IV-1 | Arhgap10 | 79658 | 7-Jun-15 |
| 15780 | 3 | 4 | | | | IV-1 | Als2cr11 | 151254 | 4-May-15 | 15874 | 3 | 4 | | IV-1 | Arhgap17 | 55114 | 4-May-15 |
| 15781 | 3 | 4 | | | | IV-1 | Alx3 | 257 | 12-May-15 | 15875 | 3 | 4 | | IV-1 | Arhgap18 | 93663 | 4-May-15 |
| 15782 | 3 | 4 | | | | IV-1 | Alx4 | 60529 | 23-May-15 | 15876 | 3 | 4 | | IV-1 | Arhgap29 | 9411 | 24-May-15 |
| 15783 | 3 | 4 | | | | IV-1 | Amacr | 23600 | 12-May-15 | 15877 | 3 | 4 | | IV-1 | Arhgap35 | 2909 | 17-May-15 |
| 15784 | 3 | 4 | | | | IV-1 | Ambp | 259 | 12-May-15 | 15878 | 3 | 4 | | IV-1 | Arhgap36 | 158763 | 4-May-15 |
| 15785 | 3 | 4 | | | | IV-1 | Ambra1 | 55626 | 21-May-15 | 15879 | 3 | 4 | | IV-1 | Arhgap39 | 80728 | 21-May-15 |
| 15786 | 3 | 4 | | | | IV-1 | Amer1 | 139285 | 4-May-15 | 15880 | 3 | 4 | | IV-1 | Arhgap42 | 143872 | 4-May-15 |
| 15787 | 3 | 4 | | | | IV-1 | Amer3 | 205147 | 4-May-15 | 15881 | 3 | 4 | | IV-1 | Arhgap6 | 395 | 4-May-15 |
| 15788 | 3 | 4 | | | | IV-1 | Amfr | 267 | 29-May-15 | 15882 | 3 | 4 | | IV-1 | Arhgef10 | 9639 | 12-May-15 |
| 15789 | 3 | 4 | | | | IV-1 | Amh | 268 | 17-May-15 | 15883 | 3 | 4 | | IV-1 | Arhgef10l | 55160 | 4-May-15 |
| 15790 | 3 | 4 | | | | IV-1 | Amigo2 | 347902 | 4-May-15 | 15884 | 3 | 4 | | IV-1 | Arhgef12 | 23365 | 12-May-15 |
| 15791 | 3 | 4 | | | | IV-1 | Amotl2 | 51421 | 4-May-15 | 15885 | 3 | 4 | | IV-1 | Arhgef3 | 50650 | 4-May-15 |
| 15792 | 3 | 4 | | | | IV-1 | Ampd2 | 271 | 12-May-15 | 15886 | 3 | 4 | | IV-1 | Arhgef6 | 9459 | 4-May-15 |
| 15793 | 3 | 4 | | | | IV-1 | Anapc1 | 64682 | 12-May-15 | 15887 | 3 | 4 | | IV-1 | Arhgef9 | 23229 | 23-May-15 |
| 15794 | 3 | 4 | | | | IV-1 | Anapc4 | 29945 | 4-May-15 | 15888 | 3 | 4 | | IV-1 | Arid1b | 57492 | 12-May-15 |
| 15795 | 3 | 4 | | | | IV-1 | Anapc5 | 51433 | 4-May-15 | 15889 | 3 | 4 | | IV-1 | Arid2 | 196528 | 4-May-15 |
| 15796 | 3 | 4 | | | | IV-1 | Anapc7 | 51434 | 4-May-15 | 15890 | 3 | 4 | | IV-1 | Arid3a | 1820 | 28-May-15 |
| 15797 | 3 | 4 | | | | IV-1 | Ang6 | | | 15891 | 3 | 4 | | IV-1 | Arid3c | 138715 | 4-May-15 |
| 15798 | 3 | 4 | | | | IV-1 | Angel1 | 23357 | 29-May-15 | 15892 | 3 | 4 | | IV-1 | Arid4a | 5926 | 4-May-15 |
| 15799 | 3 | 4 | | | | IV-1 | Angel2 | 90806 | 12-May-15 | 15893 | 3 | 4 | | IV-1 | Arid4b | 51742 | 4-May-15 |
| 15800 | 3 | 4 | | | | IV-1 | Angpt1 | 284 | 17-May-15 | 15894 | 3 | 4 | | IV-1 | Arih2 | 10425 | 4-May-15 |
| 15801 | 3 | 4 | | | | IV-1 | Ankdd1b | 728780 | 4-May-15 | 15895 | 3 | 4 | | IV-1 | Arl1 | 400 | 7-Jun-15 |
| 15802 | 3 | 4 | | | | IV-1 | Ankfy1 | 51479 | 4-May-15 | 15896 | 3 | 4 | | IV-1 | Arl10 | 285598 | 4-May-15 |
| 15803 | 3 | 4 | | | | IV-1 | Ankhd1 | 54882 | 3-May-15 | 15897 | 3 | 4 | | IV-1 | Arl13b | 200894 | 23-May-15 |
| 15804 | 3 | 4 | | | | IV-1 | Ankmy1 | 51281 | 21-May-15 | 15898 | 3 | 4 | | IV-1 | Arl14 | 80117 | 4-May-15 |
| 15805 | 3 | 4 | | | | IV-1 | Ankmy2 | 57037 | 4-May-15 | 15899 | 3 | 4 | | IV-1 | Arl14ep | 120534 | 4-May-15 |
| 15806 | 3 | 4 | | | | IV-1 | Ankrd11 | 29123 | 12-May-15 | 15900 | 3 | 4 | | IV-1 | Arl14epl | 644100 | 4-May-15 |
| 15807 | 3 | 4 | | | | IV-1 | Ankrd12 | 23253 | 21-May-15 | 15901 | 3 | 4 | | IV-1 | Arl15 | 54622 | 4-May-15 |
| 15808 | 3 | 4 | | | | IV-1 | Ankrd13a | 88455 | 12-May-15 | 15902 | 3 | 4 | | IV-1 | Arl16 | 339231 | 4-May-15 |
| 15809 | 3 | 4 | | | | IV-1 | Ankrd13b | 124930 | 4-May-15 | 15903 | 3 | 4 | | IV-1 | Arl2 | 402 | 4-May-15 |
| 15810 | 3 | 4 | | | | IV-1 | Ankrd13c | 81573 | 4-May-15 | 15904 | 3 | 4 | | IV-1 | Arl4a | 10124 | 4-May-15 |
| 15811 | 3 | 4 | | | | IV-1 | Ankrd13d | 338692 | 4-May-15 | 15905 | 3 | 4 | | IV-1 | Arl6ip1 | 23204 | 4-May-15 |
| 15812 | 3 | 4 | | | | IV-1 | Ankrd17 | 26057 | 4-May-15 | 15906 | 3 | 4 | | IV-1 | Arl6ip5 | 10550 | 12-May-15 |
| 15813 | 3 | 4 | | | | IV-1 | Ankrd27 | 84079 | 4-May-15 | 15907 | 3 | 4 | | IV-1 | Arl6ip6 | 151188 | 4-May-15 |
| 15814 | 3 | 4 | | | | IV-1 | Ankrd34c | 390616 | 4-May-15 | 15908 | 3 | 4 | | IV-1 | Arl9 | 132946 | 4-May-15 |
| 15815 | 3 | 4 | | | | IV-1 | Ankrd35 | 148741 | 4-May-15 | 15909 | 3 | 4 | | IV-1 | Armc1 | 55156 | 4-May-15 |
| 15816 | 3 | 4 | | | | IV-1 | Ankrd40 | 91369 | 21-May-15 | 15910 | 3 | 4 | | IV-1 | Armc10 | 83787 | 4-May-15 |
| 15817 | 3 | 4 | | | | IV-1 | Ankrd42 | 338699 | 12-May-15 | 15911 | 3 | 4 | | IV-1 | Armc4 | 55130 | 28-May-15 |
| 15818 | 3 | 4 | | | | IV-1 | Ankrd44 | 91526 | 4-May-15 | 15912 | 3 | 4 | | IV-1 | Armc5 | 79798 | 4-May-15 |
| 15819 | 3 | 4 | | | | IV-1 | Ankrd49 | 54851 | 4-May-15 | 15913 | 3 | 4 | | IV-1 | Armc6 | 93436 | 4-May-15 |
| 15820 | 3 | 4 | | | | IV-1 | Ankrd52 | 283373 | 4-May-15 | 15914 | 3 | 4 | | IV-1 | Armc9 | 80210 | 12-May-15 |
| 15821 | 3 | 4 | | | | IV-1 | Ankrd53 | 79998 | 4-May-15 | 15915 | 3 | 4 | | IV-1 | Arnt | 405 | 7-Jun-15 |
| 15822 | 3 | 4 | | | | IV-1 | Ankrd54 | 129138 | 4-May-15 | 15916 | 3 | 4 | | IV-1 | Arpc1b | 10095 | 4-May-15 |
| 15823 | 3 | 4 | | | | IV-1 | Ankrd61 | 100330 846 | 4-May-15 | 15917 | 3 | 4 | | IV-1 | Arpc3 | 10094 | 12-May-15 |
| | | | | | | | | | | 15918 | 3 | 4 | | IV-1 | Arpc4 | 10093 | 4-May-15 |
| 15824 | 3 | 4 | | | | IV-1 | Ankrd63 | 100131 244 | 4-May-15 | 15919 | 3 | 4 | | IV-1 | Arpc5 | 10092 | 4-May-15 |
| 15825 | 3 | 4 | | | | IV-1 | Ankub1 | 389161 | 4-May-15 | 15920 | 3 | 4 | | IV-1 | Arpp21 | 10777 | 4-May-15 |
| 15826 | 3 | 4 | | | | IV-1 | Ankzf1 | 55139 | 4-May-15 | 15921 | 3 | 4 | | IV-1 | Arrb1 | 408 | 17-May-15 |
| 15827 | 3 | 4 | | | | IV-1 | Ano8 | 57719 | 4-May-15 | 15922 | 3 | 4 | | IV-1 | Arsa | 410 | 23-May-15 |
| 15828 | 3 | 4 | | | | IV-1 | Anp32b | 10541 | 4-May-15 | 15923 | 3 | 4 | | IV-1 | Asah2 | 56624 | 4-May-15 |
| 15829 | 3 | 4 | | | | IV-1 | Antxrl | 195977 | 4-May-15 | 15924 | 3 | 4 | | IV-1 | Asap1 | 50807 | 12-May-15 |
| 15830 | 3 | 4 | | | | IV-1 | Anxa11 | 311 | 10-May-15 | 15925 | 3 | 4 | | IV-1 | Asb17 | 127247 | 4-May-15 |
| 15831 | 3 | 4 | | | | IV-1 | Anxa13 | 312 | 4-May-15 | 15926 | 3 | 4 | | IV-1 | Asb4 | 51666 | 4-May-15 |
| 15832 | 3 | 4 | | | | IV-1 | Anxa7 | 310 | 4-May-15 | 15927 | 3 | 4 | | IV-1 | Asb7 | 140460 | 4-May-15 |
| 15833 | 3 | 4 | | | | IV-1 | Ap1g1 | 164 | 4-May-15 | 15928 | 3 | 4 | | IV-1 | Asb8 | 140461 | 4-May-15 |
| 15834 | 3 | 4 | | | | IV-1 | Ap1g2 | 8906 | 12-May-15 | 15929 | 3 | 4 | | IV-1 | Asb9 | 140462 | 3-May-15 |
| 15835 | 3 | 4 | | | | IV-1 | Ap1m1 | 8907 | 4-May-15 | 15930 | 3 | 4 | | IV-1 | Ascc1 | 51008 | 12-May-15 |
| 15836 | 3 | 4 | | | | IV-1 | Ap2a2 | 161 | 4-May-15 | 15931 | 3 | 4 | | IV-1 | Ascc2 | 84164 | 4-May-15 |
| 15837 | 3 | 4 | | | | IV-1 | Ap2b1 | 163 | 4-May-15 | 15932 | 3 | 4 | | IV-1 | Ascc3 | 10973 | 4-May-15 |
| 15838 | 3 | 4 | | | | IV-1 | Ap2m1 | 1173 | 4-May-15 | 15933 | 3 | 4 | | IV-1 | Ascl1 | 429 | 23-May-15 |
| 15839 | 3 | 4 | | | | IV-1 | Ap2s1 | 1175 | 12-May-15 | 15934 | 3 | 4 | | IV-1 | Ascl4 | 121549 | 4-May-15 |
| 15840 | 3 | 4 | | | | IV-1 | Ap3b1 | 8546 | 23-May-15 | 15935 | 3 | 4 | | IV-1 | Ascl5 | 647219 | 4-May-15 |
| | | | | | | | | | | 15936 | 3 | 4 | | IV-1 | Asf1a | 25842 | 4-May-15 |

Fig. 30 - 85

| | | | | | | | | | |
|---|---|---|---|---|---|---|---|---|---|
| 15937 | 3 | 4 | | | | IV-1 | Asgr2 | 433 | 12-May-15 |
| 15938 | 3 | 4 | | | | IV-1 | Ash1l | 55870 | 4-May-15 |
| 15939 | 3 | 4 | | | | IV-1 | Asic1 | 41 | 4-May-15 |
| 15940 | 3 | 4 | | | | IV-1 | Asic2 | 40 | 12-May-15 |
| 15941 | 3 | 4 | | | | IV-1 | Asic3 | 9311 | 4-May-15 |
| 15942 | 3 | 4 | | | | IV-1 | Asic4 | 55515 | 12-May-15 |
| 15943 | 3 | 4 | | | | IV-1 | Asic5 | 51802 | 4-May-15 |
| 15944 | 3 | 4 | | | | IV-1 | Asrgl1 | 80150 | 12-May-15 |
| 15945 | 3 | 4 | | | | IV-1 | Astl | 431705 | 4-May-15 |
| 15946 | 3 | 4 | | | | IV-1 | Astn1 | 460 | 4-May-15 |
| 15947 | 3 | 4 | | | | IV-1 | Astn2 | 23245 | 4-May-15 |
| 15948 | 3 | 4 | | | | IV-1 | Asun | 55726 | 4-May-15 |
| 15949 | 3 | 4 | | | | IV-1 | Asxl2 | 55252 | 4-May-15 |
| 15950 | 3 | 4 | | | | IV-1 | Asxl3 | 80816 | 4-May-15 |
| 15951 | 3 | 4 | | | | IV-1 | Atad1 | 84896 | 4-May-15 |
| 15952 | 3 | 4 | | | | IV-1 | Atad3a | 55210 | 4-May-15 |
| 15953 | 3 | 4 | | | | IV-1 | Atad3aos | | |
| 15954 | 3 | 4 | | | | IV-1 | Atf1 | 466 | 7-Jun-15 |
| 15955 | 3 | 4 | | | | IV-1 | Atf2 | 1386 | 7-Jun-15 |
| 15956 | 3 | 4 | | | | IV-1 | Atf6b | 1388 | 4-May-15 |
| 15957 | 3 | 4 | | | | IV-1 | Atf7ip2 | 80063 | 4-May-15 |
| 15958 | 3 | 4 | | | | IV-1 | Atg10 | 83734 | 4-May-15 |
| 15959 | 3 | 4 | | | | IV-1 | Atg13 | 9776 | 28-May-15 |
| 15960 | 3 | 4 | | | | IV-1 | Atg14 | 22863 | 28-May-15 |
| 15961 | 3 | 4 | | | | IV-1 | Atg16l1 | 55054 | 21-May-15 |
| 15962 | 3 | 4 | | | | IV-1 | Atg16l2 | 89849 | 21-May-15 |
| 15963 | 3 | 4 | | | | IV-1 | Atg2b | 55102 | 21-May-15 |
| 15964 | 3 | 4 | | | | IV-1 | Atg3 | 64422 | 23-May-15 |
| 15965 | 3 | 4 | | | | IV-1 | Atg7 | 10533 | 4-May-15 |
| 15966 | 3 | 4 | | | | IV-1 | Atg9a | 79065 | 21-May-15 |
| 15967 | 3 | 4 | | | | IV-1 | Athl1 | 80162 | 12-May-15 |
| 15968 | 3 | 4 | | | | IV-1 | Atl1 | 51062 | 7-Jun-15 |
| 15969 | 3 | 4 | | | | IV-1 | Atl3 | 25923 | 4-May-15 |
| 15970 | 3 | 4 | | | | IV-1 | Atm | 472 | 31-May-15 |
| 15971 | 3 | 4 | | | | IV-1 | Atmin | 23300 | 4-May-15 |
| 15972 | 3 | 4 | | | | IV-1 | Atn1 | 1822 | 23-May-15 |
| 15973 | 3 | 4 | | | | IV-1 | Atoh7 | 220202 | 23-May-15 |
| 15974 | 3 | 4 | | | | IV-1 | Atoh8 | 84913 | 3-May-15 |
| 15975 | 3 | 4 | | | | IV-1 | Atp11c | 286410 | 4-May-15 |
| 15976 | 3 | 4 | | | | IV-1 | Atp12a | 479 | 4-May-15 |
| 15977 | 3 | 4 | | | | IV-1 | Atp13a1 | 57130 | 4-May-15 |
| 15978 | 3 | 4 | | | | IV-1 | Atp13a2 | 23400 | 23-May-15 |
| 15979 | 3 | 4 | | | | IV-1 | Atp1a1 | 476 | 7-Jun-15 |
| 15980 | 3 | 4 | | | | IV-1 | Atp2b2 | 491 | 7-Jun-15 |
| 15981 | 3 | 4 | | | | IV-1 | Atp2c2 | 9914 | 4-May-15 |
| 15982 | 3 | 4 | | | | IV-1 | Atp5a1 | 498 | 12-May-15 |
| 15983 | 3 | 4 | | | | IV-1 | Atp5e | 514 | 4-May-15 |
| 15984 | 3 | 4 | | | | IV-1 | Atp5g3 | 518 | 4-May-15 |
| 15985 | 3 | 4 | | | | IV-1 | Atp5o | 539 | 23-May-15 |
| 15986 | 3 | 4 | | | | IV-1 | Atp6ap1l | 92270 | 4-May-15 |
| 15987 | 3 | 4 | | | | IV-1 | Atp6v0a2 | 23545 | 23-May-15 |
| 15988 | 3 | 4 | | | | IV-1 | Atp6v0c | 527 | 4-May-15 |
| 15989 | 3 | 4 | | | | IV-1 | Atp6v0e2 | 155066 | 4-May-15 |
| 15990 | 3 | 4 | | | | IV-1 | Atp6v1c1 | 528 | 2-Jun-15 |
| 15991 | 3 | 4 | | | | IV-1 | Atp6v1e1 | 529 | 4-May-15 |
| 15992 | 3 | 4 | | | | IV-1 | Atp6v1e2 | 90423 | 4-May-15 |
| 15993 | 3 | 4 | | | | IV-1 | Atp6v1f | 9296 | 4-May-15 |
| 15994 | 3 | 4 | | | | IV-1 | Atp6v1g1 | 9550 | 4-May-15 |
| 15995 | 3 | 4 | | | | IV-1 | Atp8b1 | 5205 | 23-May-15 |
| 15996 | 3 | 4 | | | | IV-1 | Atp9a | 10079 | 4-May-15 |
| 15997 | 3 | 4 | | | | IV-1 | Atp9b | 374868 | 12-May-15 |
| 15998 | 3 | 4 | | | | IV-1 | Atpaf1 | 64756 | 4-May-15 |
| 15999 | 3 | 4 | | | | IV-1 | Atraid | 51374 | 4-May-15 |
| 16000 | 3 | 4 | | | | IV-1 | Atrip | 84126 | 4-May-15 |
| 16001 | 3 | 4 | | | | IV-1 | Atrn | 8455 | 12-May-15 |
| 16002 | 3 | 4 | | | | IV-1 | Atrnl1 | 26033 | 4-May-15 |
| 16003 | 3 | 4 | | | | IV-1 | Atrx | 546 | 23-May-15 |
| 16004 | 3 | 4 | | | | IV-1 | Atxn2 | 6311 | 23-May-15 |
| 16005 | 3 | 4 | | | | IV-1 | Atxn3 | 4287 | 7-Jun-15 |
| 16006 | 3 | 4 | | | | IV-1 | Atxn7 | 6314 | 23-May-15 |
| 16007 | 3 | 4 | | | | IV-1 | Atxn7l1 | 222255 | 12-May-15 |
| 16008 | 3 | 4 | | | | IV-1 | Atxn7l2 | 127002 | 4-May-15 |
| 16009 | 3 | 4 | | | | IV-1 | Atxn7l3b | 552889 | 12-May-15 |
| 16010 | 3 | 4 | | | | IV-1 | AU015228 | | |
| 16011 | 3 | 4 | | | | IV-1 | AU016765 | | |
| 16012 | 3 | 4 | | | | IV-1 | AU018091 | | |
| 16013 | 3 | 4 | | | | IV-1 | AU018829 | | |
| 16014 | 3 | 4 | | | | IV-1 | AU019823 | | |
| 16015 | 3 | 4 | | | | IV-1 | AU021063 | | |
| 16016 | 3 | 4 | | | | IV-1 | AU022751 | | |
| 16017 | 3 | 4 | | | | IV-1 | AU022754 | | |
| 16018 | 3 | 4 | | | | IV-1 | AU022793 | | |
| 16019 | 3 | 4 | | | | IV-1 | AU040320 | | |
| 16020 | 3 | 4 | | | | IV-1 | Auts2 | 26053 | 7-Jun-15 |
| 16021 | 3 | 4 | | | | IV-1 | Aven | 57099 | 4-May-15 |
| 16022 | 3 | 4 | | | | IV-1 | Avp | 551 | 7-Jun-15 |
| 16023 | 3 | 4 | | | | IV-1 | Avpr2 | 554 | 23-May-15 |
| 16024 | 3 | 4 | | | | IV-1 | AW011738 | | |
| 16025 | 3 | 4 | | | | IV-1 | AW495222 | | |
| 16026 | 3 | 4 | | | | IV-1 | AW551984 | | |
| 16027 | 3 | 4 | | | | IV-1 | AW554918 | | |
| 16028 | 3 | 4 | | | | IV-1 | AW822252 | | |
| 16029 | 3 | 4 | | | | IV-1 | Awat2 | 158835 | 4-May-15 |
| 16030 | 3 | 4 | | | | IV-1 | Axin1 | 8312 | 4-May-15 |
| 16031 | 3 | 4 | | | | IV-1 | Axin2 | 8313 | 4-May-15 |
| 16032 | 3 | 4 | | | | IV-1 | AY358078 | | |
| 16033 | 3 | 4 | | | | IV-1 | AY512931 | | |
| 16034 | 3 | 4 | | | | IV-1 | AY761184 | | |
| 16035 | 3 | 4 | | | | IV-1 | B020004J07Rik | | |
| 16036 | 3 | 4 | | | | IV-1 | B020014A21Rik | | |
| 16037 | 3 | 4 | | | | IV-1 | B020031M17Rik | | |
| 16038 | 3 | 4 | | | | IV-1 | B130006D01Rik | | |
| 16039 | 3 | 4 | | | | IV-1 | B130024G19Rik | | |
| 16040 | 3 | 4 | | | | IV-1 | B230214G05Rik | | |
| 16041 | 3 | 4 | | | | IV-1 | B230216G23Rik | | |
| 16042 | 3 | 4 | | | | IV-1 | B230216N24Rik | | |
| 16043 | 3 | 4 | | | | IV-1 | B230217C12Rik | | |
| 16044 | 3 | 4 | | | | IV-1 | B230323A14Rik | | |
| 16045 | 3 | 4 | | | | IV-1 | B3galt1 | 8708 | 21-May-15 |
| 16046 | 3 | 4 | | | | IV-1 | B3galt5 | 10317 | 23-May-15 |
| 16047 | 3 | 4 | | | | IV-1 | B3galt6 | 126792 | 4-May-15 |
| 16048 | 3 | 4 | | | | IV-1 | B3gat1 | 27087 | 12-May-15 |
| 16049 | 3 | 4 | | | | IV-1 | B3gat2 | 135152 | 12-May-15 |
| 16050 | 3 | 4 | | | | IV-1 | B3gat3 | 26229 | 23-May-15 |
| 16051 | 3 | 4 | | | | IV-1 | B3glct | 145173 | 23-May-15 |
| 16052 | 3 | 4 | | | | IV-1 | B3gnt7 | 93010 | 4-May-15 |
| 16053 | 3 | 4 | | | | IV-1 | B4galt1 | 2683 | 23-May-15 |
| 16054 | 3 | 4 | | | | IV-1 | B4galt2 | 8704 | 4-May-15 |
| 16055 | 3 | 4 | | | | IV-1 | B630005N14Rik | | |
| 16056 | 3 | 4 | | | | IV-1 | B630019K06Rik | | |
| 16057 | 3 | 4 | | | | IV-1 | B830017H08Rik | | |
| 16058 | 3 | 4 | | | | IV-1 | B930003M22Rik | | |
| 16059 | 3 | 4 | | | | IV-1 | B930018H19Rik | | |
| 16060 | 3 | 4 | | | | IV-1 | B930025P03Rik | | |
| 16061 | 3 | 4 | | | | IV-1 | B930041F14Rik | | |
| 16062 | 3 | 4 | | | | IV-1 | B930092H01Rik | | |
| 16063 | 3 | 4 | | | | IV-1 | B9d1 | 27077 | 4-May-15 |
| 16064 | 3 | 4 | | | | IV-1 | Babam1 | 29086 | 4-May-15 |
| 16065 | 3 | 4 | | | | IV-1 | Bace1 | 23621 | 17-May-15 |
| 16066 | 3 | 4 | | | | IV-1 | Bace2 | 25825 | 12-May-15 |
| 16067 | 3 | 4 | | | | IV-1 | Bag1 | 573 | 17-May-15 |
| 16068 | 3 | 4 | | | | IV-1 | Bag6 | 7917 | 29-May-15 |
| 16069 | 3 | 4 | | | | IV-1 | Bai1 | 575 | 4-May-15 |
| 16070 | 3 | 4 | | | | IV-1 | Bai2 | 576 | 4-May-15 |
| 16071 | 3 | 4 | | | | IV-1 | Baiap2 | 10458 | 12-May-15 |
| 16072 | 3 | 4 | | | | IV-1 | Bambi | 25805 | 4-May-15 |
| 16073 | 3 | 4 | | | | IV-1 | Banf2 | 140836 | 4-May-15 |
| 16074 | 3 | 4 | | | | IV-1 | Barhl2 | 343472 | 28-May-15 |
| 16075 | 3 | 4 | | | | IV-1 | Barx1 | 56033 | 4-May-15 |
| 16076 | 3 | 4 | | | | IV-1 | Barx2 | 8538 | 28-May-15 |
| 16077 | 3 | 4 | | | | IV-1 | Baz2a | 11176 | 4-May-15 |
| 16078 | 3 | 4 | | | | IV-1 | Baz2b | 29994 | 12-May-15 |
| 16079 | 3 | 4 | | | | IV-1 | BB014433 | | |
| 16080 | 3 | 4 | | | | IV-1 | BB283400 | | |
| 16081 | 3 | 4 | | | | IV-1 | BB287469 | | |
| 16082 | 3 | 4 | | | | IV-1 | BB557941 | | |
| 16083 | 3 | 4 | | | | IV-1 | Bbs10 | 79738 | 23-May-15 |
| 16084 | 3 | 4 | | | | IV-1 | Bbs12 | 166379 | 23-May-15 |
| 16085 | 3 | 4 | | | | IV-1 | Bbs5 | 129880 | 23-May-15 |
| 16086 | 3 | 4 | | | | IV-1 | BC003965 | | |
| 16087 | 3 | 4 | | | | IV-1 | BC004004 | | |
| 16088 | 3 | 4 | | | | IV-1 | BC005764 | | |
| 16089 | 3 | 4 | | | | IV-1 | BC016579 | | |
| 16090 | 3 | 4 | | | | IV-1 | BC017158 | | |
| 16091 | 3 | 4 | | | | IV-1 | BC017643 | | |
| 16092 | 3 | 4 | | | | IV-1 | BC024978 | | |
| 16093 | 3 | 4 | | | | IV-1 | BC025920 | | |
| 16094 | 3 | 4 | | | | IV-1 | BC027072 | | |
| 16095 | 3 | 4 | | | | IV-1 | BC027231 | | |
| 16096 | 3 | 4 | | | | IV-1 | BC030336 | | |
| 16097 | 3 | 4 | | | | IV-1 | BC030500 | | |
| 16098 | 3 | 4 | | | | IV-1 | BC031361 | | |
| 16099 | 3 | 4 | | | | IV-1 | BC039966 | | |
| 16100 | 3 | 4 | | | | IV-1 | BC048403 | | |
| 16101 | 3 | 4 | | | | IV-1 | BC048502 | | |
| 16102 | 3 | 4 | | | | IV-1 | BC048507 | | |
| 16103 | 3 | 4 | | | | IV-1 | BC048602 | | |
| 16104 | 3 | 4 | | | | IV-1 | BC048609 | | |
| 16105 | 3 | 4 | | | | IV-1 | BC049635 | | |
| 16106 | 3 | 4 | | | | IV-1 | BC049715 | | |
| 16107 | 3 | 4 | | | | IV-1 | BC049730 | | |
| 16108 | 3 | 4 | | | | IV-1 | BC051019 | | |
| 16109 | 3 | 4 | | | | IV-1 | BC051665 | | |
| 16110 | 3 | 4 | | | | IV-1 | BC052040 | | |
| 16111 | 3 | 4 | | | | IV-1 | BC053393 | | |
| 16112 | 3 | 4 | | | | IV-1 | BC053749 | | |
| 16113 | 3 | 4 | | | | IV-1 | BC061194 | | |
| 16114 | 3 | 4 | | | | IV-1 | BC068157 | | |
| 16115 | 3 | 4 | | | | IV-1 | BC068281 | | |
| 16116 | 3 | 4 | | | | IV-1 | BC080695 | | |
| 16117 | 3 | 4 | | | | IV-1 | BC089597 | | |
| 16118 | 3 | 4 | | | | IV-1 | BC117090 | | |
| 16119 | 3 | 4 | | | | IV-1 | Bcap29 | 55973 | 4-May-15 |
| 16120 | 3 | 4 | | | | IV-1 | Bcas2 | 10286 | 4-May-15 |
| 16121 | 3 | 4 | | | | IV-1 | Bcas3 | 54828 | 12-May-15 |
| 16122 | 3 | 4 | | | | IV-1 | Bcas3os1 | | |
| 16123 | 3 | 4 | | | | IV-1 | Bcas3os2 | | |
| 16124 | 3 | 4 | | | | IV-1 | Bcdin3d | 144233 | 4-May-15 |
| 16125 | 3 | 4 | | | | IV-1 | Bcl10 | 8915 | 12-May-15 |
| 16126 | 3 | 4 | | | | IV-1 | Bcl2 | 596 | 31-May-15 |

Fig. 30 - 86

| | | | | | | | | | | | | | | | | | | |
|---|---|---|---|---|---|---|---|---|---|---|---|---|---|---|---|---|---|---|
| 16127 | 3 | 4 | | | | IV-1 | Bcl7c | 9274 | 4-May-15 | 16223 | 3 | 4 | | | | IV-1 | C130030K03Rik | | |
| 16128 | 3 | 4 | | | | IV-1 | Bcl9 | 607 | 4-May-15 | 16224 | 3 | 4 | | | | IV-1 | C130046K22Rik | | |
| 16129 | 3 | 4 | | | | IV-1 | Bclaf1 | 9774 | 4-May-15 | 16225 | 3 | 4 | | | | IV-1 | C130060K24Rik | | |
| 16130 | 3 | 4 | | | | IV-1 | Bcor | 54880 | 23-May-15 | 16226 | 3 | 4 | | | | IV-1 | C130071C03Rik | | |
| 16131 | 3 | 4 | | | | IV-1 | Bdnf | 627 | 7-Jun-15 | 16227 | 3 | 4 | | | | IV-1 | C130074G19Rik | | |
| 16132 | 3 | 4 | | | | IV-1 | Bean1 | 146227 | 23-May-15 | 16228 | 3 | 4 | | | | IV-1 | C130080G10Rik | | |
| 16133 | 3 | 4 | | | | IV-1 | Becn2 | 441925 | 4-May-15 | 16229 | 3 | 4 | | | | IV-1 | C1ql2 | 165257 | 4-May-15 |
| 16134 | 3 | 4 | | | | IV-1 | Begain | 57596 | 4-May-15 | 16230 | 3 | 4 | | | | IV-1 | C1ql3 | 389941 | 4-May-15 |
| 16135 | 3 | 4 | | | | IV-1 | Best2 | 54831 | 4-May-15 | 16231 | 3 | 4 | | | | IV-1 | C1ql4 | 338761 | 4-May-15 |
| 16136 | 3 | 4 | | | | IV-1 | Best3 | 144453 | 4-May-15 | 16232 | 3 | 4 | | | | IV-1 | C1qtnf1 | 114897 | 4-May-15 |
| 16137 | 3 | 4 | | | | IV-1 | Bet1l | 51272 | 4-May-15 | 16233 | 3 | 4 | | | | IV-1 | C230024C17Rik | | |
| 16138 | 3 | 4 | | | | IV-1 | Bfar | 51283 | 4-May-15 | 16234 | 3 | 4 | | | | IV-1 | C230029M16 | | |
| 16139 | 3 | 4 | | | | IV-1 | Bhlhe22 | 27319 | 4-May-15 | 16235 | 3 | 4 | | | | IV-1 | C230091D08Rik | | |
| 16140 | 3 | 4 | | | | IV-1 | Bhlhe23 | 128408 | 4-May-15 | 16236 | 3 | 4 | | | | IV-1 | C2cd4a | 145741 | 4-May-15 |
| 16141 | 3 | 4 | | | | IV-1 | Bicc1 | 80114 | 4-May-15 | 16237 | 3 | 4 | | | | IV-1 | C2cd4b | 388125 | 4-May-15 |
| 16142 | 3 | 4 | | | | IV-1 | Birc2 | 329 | 24-May-15 | 16238 | 3 | 4 | | | | IV-1 | C2cd4c | 126567 | 4-May-15 |
| 16143 | 3 | 4 | | | | IV-1 | Birc3 | 330 | 24-May-15 | 16239 | 3 | 4 | | | | IV-1 | C330007P06Rik | | |
| 16144 | 3 | 4 | | | | IV-1 | Birc7 | 79444 | 23-May-15 | 16240 | 3 | 4 | | | | IV-1 | C330022C24Rik | | |
| 16145 | 3 | 4 | | | | IV-1 | Bivm | 54841 | 4-May-15 | 16241 | 3 | 4 | | | | IV-1 | C330024C12Rik | | |
| 16146 | 3 | 4 | | | | IV-1 | Blcap | 10904 | 4-May-15 | 16242 | 3 | 4 | | | | IV-1 | C430002N11Rik | | |
| 16147 | 3 | 4 | | | | IV-1 | Bloc1s2 | 282991 | 4-May-15 | 16243 | 3 | 4 | | | | IV-1 | C630031E19Rik | | |
| 16148 | 3 | 4 | | | | IV-1 | Bloc1s3 | 388552 | 23-May-15 | 16244 | 3 | 4 | | | | IV-1 | C630043F03Rik | | |
| 16149 | 3 | 4 | | | | IV-1 | Bloc1s4 | 55330 | 4-May-15 | 16245 | 3 | 4 | | | | IV-1 | C730027H18Rik | | |
| 16150 | 3 | 4 | | | | IV-1 | Bloc1s5 | 63915 | 4-May-15 | 16246 | 3 | 4 | | | | IV-1 | C86187 | | |
| 16151 | 3 | 4 | | | | IV-1 | Bloc1s6 | 26258 | 23-May-15 | 16247 | 3 | 4 | | | | IV-1 | C86695 | | |
| 16152 | 3 | 4 | | | | IV-1 | Blvra | 644 | 4-May-15 | 16248 | 3 | 4 | | | | IV-1 | C87198 | | |
| 16153 | 3 | 4 | | | | IV-1 | Bmp1 | 649 | 12-May-15 | 16249 | 3 | 4 | | | | IV-1 | C87436 | | |
| 16154 | 3 | 4 | | | | IV-1 | Bmp6 | 654 | 17-May-15 | 16250 | 3 | 4 | | | | IV-1 | C87499 | | |
| 16155 | 3 | 4 | | | | IV-1 | Bmp8b | 656 | 4-May-15 | 16251 | 3 | 4 | | | | IV-1 | C87977 | | |
| 16156 | 3 | 4 | | | | IV-1 | Bmper | 168667 | 4-May-15 | 16252 | 3 | 4 | | | | IV-1 | Cab39 | 51719 | 4-May-15 |
| 16157 | 3 | 4 | | | | IV-1 | Bms1 | 9790 | 4-May-15 | 16253 | 3 | 4 | | | | IV-1 | Cab39l | 81617 | 4-May-15 |
| 16158 | 3 | 4 | | | | IV-1 | Bmx | 660 | 4-May-15 | 16254 | 3 | 4 | | | | IV-1 | Cabin1 | 23523 | 21-May-15 |
| 16159 | 3 | 4 | | | | IV-1 | Bnip2 | 663 | 4-May-15 | 16255 | 3 | 4 | | | | IV-1 | Cables1 | 91768 | 4-May-15 |
| 16160 | 3 | 4 | | | | IV-1 | Bnip3 | 664 | 12-May-15 | 16256 | 3 | 4 | | | | IV-1 | Cabp7 | 164633 | 4-May-15 |
| 16161 | 3 | 4 | | | | IV-1 | Bod1l | 259282 | 4-May-15 | 16257 | 3 | 4 | | | | IV-1 | Cabs1 | 85438 | 4-May-15 |
| 16162 | 3 | 4 | | | | IV-1 | Bok | 666 | 4-May-15 | 16258 | 3 | 4 | | | | IV-1 | Cabyr | 26256 | 12-May-15 |
| 16163 | 3 | 4 | | | | IV-1 | Bola2 | 552900 | 7-Jun-15 | 16259 | 3 | 4 | | | | IV-1 | Cacng3 | 10368 | 4-May-15 |
| 16164 | 3 | 4 | | | | IV-1 | Bop1 | 23246 | 4-May-15 | 16260 | 3 | 4 | | | | IV-1 | Cacng4 | 27092 | 4-May-15 |
| 16165 | 3 | 4 | | | | IV-1 | Bpi | 671 | 4-May-15 | 16261 | 3 | 4 | | | | IV-1 | Cacng5 | 27091 | 4-May-15 |
| 16166 | 3 | 4 | | | | IV-1 | Bpifa3 | 128861 | 4-May-15 | 16262 | 3 | 4 | | | | IV-1 | Cacng6 | 59285 | 4-May-15 |
| 16167 | 3 | 4 | | | | IV-1 | Bpifa5 | | | 16263 | 3 | 4 | | | | IV-1 | Cactin | 58509 | 4-May-15 |
| 16168 | 3 | 4 | | | | IV-1 | Bpifa6 | | | 16264 | 3 | 4 | | | | IV-1 | Cacul1 | 143384 | 4-May-15 |
| 16169 | 3 | 4 | | | | IV-1 | Bpifb3 | 359710 | 26-May-15 | 16265 | 3 | 4 | | | | IV-1 | Cacybp | 27101 | 26-May-15 |
| 16170 | 3 | 4 | | | | IV-1 | Bpifb4 | 149954 | 4-May-15 | 16266 | 3 | 4 | | | | IV-1 | Cadps2 | 93664 | 12-May-15 |
| 16171 | 3 | 4 | | | | IV-1 | Bpifb6 | | | 16267 | 3 | 4 | | | | IV-1 | Cage1 | 285782 | 4-May-15 |
| 16172 | 3 | 4 | | | | IV-1 | Bpifc | 254240 | 4-May-15 | 16268 | 3 | 4 | | | | IV-1 | Calb1 | 793 | 4-May-15 |
| 16173 | 3 | 4 | | | | IV-1 | Braf | 673 | 7-Jun-15 | 16269 | 3 | 4 | | | | IV-1 | Calb2 | 794 | 17-May-15 |
| 16174 | 3 | 4 | | | | IV-1 | Brd1 | 23774 | 12-May-15 | 16270 | 3 | 4 | | | | IV-1 | Calca | 796 | 17-May-15 |
| 16175 | 3 | 4 | | | | IV-1 | Brd2 | 6046 | 12-May-15 | 16271 | 3 | 4 | | | | IV-1 | Calcoco1 | 57658 | 29-May-15 |
| 16176 | 3 | 4 | | | | IV-1 | Brd3 | 8019 | 4-May-15 | 16272 | 3 | 4 | | | | IV-1 | Calcoco2 | 10241 | 12-May-15 |
| 16177 | 3 | 4 | | | | IV-1 | Brd4 | 23476 | 24-May-15 | 16273 | 3 | 4 | | | | IV-1 | Calcr | 799 | 31-May-15 |
| 16178 | 3 | 4 | | | | IV-1 | Brd7 | 29117 | 4-May-15 | 16274 | 3 | 4 | | | | IV-1 | Calcrl | 10203 | 4-May-15 |
| 16179 | 3 | 4 | | | | IV-1 | Brd8 | 10902 | 12-May-15 | 16275 | 3 | 4 | | | | IV-1 | Calhm2 | 51063 | 12-May-15 |
| 16180 | 3 | 4 | | | | IV-1 | Brd9 | 65980 | 4-May-15 | 16276 | 3 | 4 | | | | IV-1 | Calr3 | 125972 | 4-May-15 |
| 16181 | 3 | 4 | | | | IV-1 | Bre | 9577 | 12-May-15 | 16277 | 3 | 4 | | | | IV-1 | Calr4 | | |
| 16182 | 3 | 4 | | | | IV-1 | Brf1 | 2972 | 7-Jun-15 | 16278 | 3 | 4 | | | | IV-1 | Calu | 813 | 2-Jun-15 |
| 16183 | 3 | 4 | | | | IV-1 | Brf2 | 55290 | 7-Jun-15 | 16279 | 3 | 4 | | | | IV-1 | Caly | 50632 | 20-May-15 |
| 16184 | 3 | 4 | | | | IV-1 | Bri3 | 25798 | 7-Jun-15 | 16280 | 3 | 4 | | | | IV-1 | Camk1 | 8536 | 7-Jun-15 |
| 16185 | 3 | 4 | | | | IV-1 | Brinp1 | 1620 | 4-May-15 | 16281 | 3 | 4 | | | | IV-1 | Caml | 819 | 4-May-15 |
| 16186 | 3 | 4 | | | | IV-1 | Brinp3 | 339479 | 4-May-15 | 16282 | 3 | 4 | | | | IV-1 | Camta2 | 23125 | 4-May-15 |
| 16187 | 3 | 4 | | | | IV-1 | Brip1 | 83990 | 7-Jun-15 | 16283 | 3 | 4 | | | | IV-1 | Cand1 | 55832 | 4-May-15 |
| 16188 | 3 | 4 | | | | IV-1 | Brk1 | 55845 | 4-May-15 | 16284 | 3 | 4 | | | | IV-1 | Cand2 | 23066 | 4-May-15 |
| 16189 | 3 | 4 | | | | IV-1 | Brms1 | 25855 | 7-Jun-15 | 16285 | 3 | 4 | | | | IV-1 | Canx | 821 | 17-May-15 |
| 16190 | 3 | 4 | | | | IV-1 | Brms1l | 84312 | 4-May-15 | 16286 | 3 | 4 | | | | IV-1 | Cap1 | 10487 | 7-Jun-15 |
| 16191 | 3 | 4 | | | | IV-1 | Brox | 148362 | 4-May-15 | 16287 | 3 | 4 | | | | IV-1 | Capn10 | 11132 | 23-May-15 |
| 16192 | 3 | 4 | | | | IV-1 | Brpf1 | 7862 | 7-Jun-15 | 16288 | 3 | 4 | | | | IV-1 | Capn12 | 147968 | 4-May-15 |
| 16193 | 3 | 4 | | | | IV-1 | Brsk1 | 84446 | 4-May-15 | 16289 | 3 | 4 | | | | IV-1 | Capn15 | 6650 | 12-May-15 |
| 16194 | 3 | 4 | | | | IV-1 | Brwd1 | 54014 | 12-May-15 | 16290 | 3 | 4 | | | | IV-1 | Capn2 | 824 | 12-May-15 |
| 16195 | 3 | 4 | | | | IV-1 | Brwd3 | 254065 | 4-May-15 | 16291 | 3 | 4 | | | | IV-1 | Capns1 | 826 | 4-May-15 |
| 16196 | 3 | 4 | | | | IV-1 | Bsdc1 | 55108 | 4-May-15 | 16292 | 3 | 4 | | | | IV-1 | Capns2 | 84290 | 4-May-15 |
| 16197 | 3 | 4 | | | | IV-1 | Btaf1 | 9044 | 4-May-15 | 16293 | 3 | 4 | | | | IV-1 | Caprin2 | 65981 | 12-May-15 |
| 16198 | 3 | 4 | | | | IV-1 | Btbd1 | 53339 | 4-May-15 | 16294 | 3 | 4 | | | | IV-1 | Capza3 | 93661 | 4-May-15 |
| 16199 | 3 | 4 | | | | IV-1 | Btbd10 | 84280 | 12-May-15 | 16295 | 3 | 4 | | | | IV-1 | Capzb | 832 | 4-May-15 |
| 16200 | 3 | 4 | | | | IV-1 | Btbd16 | 118663 | 4-May-15 | 16296 | 3 | 4 | | | | IV-1 | Car11 | | |
| 16201 | 3 | 4 | | | | IV-1 | Btbd17 | 388419 | 4-May-15 | 16297 | 3 | 4 | | | | IV-1 | Card6 | 84674 | 12-May-15 |
| 16202 | 3 | 4 | | | | IV-1 | Btbd18 | 643376 | 4-May-15 | 16298 | 3 | 4 | | | | IV-1 | Carm1 | 10498 | 3-May-15 |
| 16203 | 3 | 4 | | | | IV-1 | Btbd19 | 149478 | 4-May-15 | 16299 | 3 | 4 | | | | IV-1 | Cars2 | 79587 | 4-May-15 |
| 16204 | 3 | 4 | | | | IV-1 | Btbd3 | 22903 | 4-May-15 | 16300 | 3 | 4 | | | | IV-1 | Casc3 | 22794 | 4-May-15 |
| 16205 | 3 | 4 | | | | IV-1 | Btbd8 | 284697 | 4-May-15 | 16301 | 3 | 4 | | | | IV-1 | Cask | 8573 | 4-May-15 |
| 16206 | 3 | 4 | | | | IV-1 | Btf3 | 689 | 7-Jun-15 | 16302 | 3 | 4 | | | | IV-1 | Caskin1 | 57524 | 4-May-15 |
| 16207 | 3 | 4 | | | | IV-1 | Btf3l4 | 91408 | 4-May-15 | 16303 | 3 | 4 | | | | IV-1 | Caskin2 | 57513 | 4-May-15 |
| 16208 | 3 | 4 | | | | IV-1 | Btnl1 | | | 16304 | 3 | 4 | | | | IV-1 | Casp7 | 840 | 12-May-15 |
| 16209 | 3 | 4 | | | | IV-1 | Btnl5-ps | | | 16305 | 3 | 4 | | | | IV-1 | Casp9 | 842 | 4-May-15 |
| 16210 | 3 | 4 | | | | IV-1 | Btnl6 | | | 16306 | 3 | 4 | | | | IV-1 | Casz1 | 54897 | 4-May-15 |
| 16211 | 3 | 4 | | | | IV-1 | Bves | 11149 | 4-May-15 | 16307 | 3 | 4 | | | | IV-1 | Cat | 847 | 7-Jun-15 |
| 16212 | 3 | 4 | | | | IV-1 | Bysl | 705 | 21-May-15 | 16308 | 3 | 4 | | | | IV-1 | Catsper2 | 117155 | 23-May-15 |
| 16213 | 3 | 4 | | | | IV-1 | Bzw2 | 28969 | 4-May-15 | 16309 | 3 | 4 | | | | IV-1 | Catsper3 | 347732 | 4-May-15 |
| 16214 | 3 | 4 | | | | IV-1 | C030013G03Rik | | | 16310 | 3 | 4 | | | | IV-1 | Catsper4 | 378807 | 4-May-15 |
| 16215 | 3 | 4 | | | | IV-1 | C030016D13Rik | | | 16311 | 3 | 4 | | | | IV-1 | Catsperd | 257062 | 4-May-15 |
| 16216 | 3 | 4 | | | | IV-1 | C030018K13Rik | | | 16312 | 3 | 4 | | | | IV-1 | Catsperg1 | | |
| 16217 | 3 | 4 | | | | IV-1 | C030023E24Rik | | | 16313 | 3 | 4 | | | | IV-1 | Catsperg2 | | |
| 16218 | 3 | 4 | | | | IV-1 | C030029H02Rik | | | 16314 | 3 | 4 | | | | IV-1 | Cav1 | 857 | 31-May-15 |
| 16219 | 3 | 4 | | | | IV-1 | C030034I22Rik | | | 16315 | 3 | 4 | | | | IV-1 | Cbfa2t3 | 863 | 4-May-15 |
| 16220 | 3 | 4 | | | | IV-1 | C030037D09Rik | | | 16316 | 3 | 4 | | | | IV-1 | Cbfb | 865 | 7-Jun-15 |
| 16221 | 3 | 4 | | | | IV-1 | C130021I20Rik | | | 16317 | 3 | 4 | | | | IV-1 | Cbll1 | 79872 | 12-May-15 |
| 16222 | 3 | 4 | | | | IV-1 | C130026I21Rik | | | 16318 | 3 | 4 | | | | IV-1 | Cbln1 | 869 | 4-May-15 |

Fig. 30 - 87

| | | | | | | | | | | | |
|---|---|---|---|---|---|---|---|---|---|---|---|
| 16319 | 3 | 4 | | | | IV-1 | Cbln2 | 147381 | 4-May-15 | 16414 | 3 | 4 | | | | IV-1 | Cd164l2 | 388611 | 4-May-15 |
| 16320 | 3 | 4 | | | | IV-1 | Cbln3 | 643866 | 4-May-15 | 16415 | 3 | 4 | | | | IV-1 | Cd200r3 | | |
| 16321 | 3 | 4 | | | | IV-1 | Cbln4 | 140689 | 4-May-15 | 16416 | 3 | 4 | | | | IV-1 | Cd47 | 961 | 31-May-15 |
| 16322 | 3 | 4 | | | | IV-1 | Cbr1 | 873 | 4-May-15 | 16417 | 3 | 4 | | | | IV-1 | Cdan1 | 146059 | 23-May-15 |
| 16323 | 3 | 4 | | | | IV-1 | Cbx1 | 10951 | 4-May-15 | 16418 | 3 | 4 | | | | IV-1 | Cdc123 | 8872 | 4-May-15 |
| 16324 | 3 | 4 | | | | IV-1 | Cbx2 | 84733 | 4-May-15 | 16419 | 3 | 4 | | | | IV-1 | Cdc14a | 8556 | 4-May-15 |
| 16325 | 3 | 4 | | | | IV-1 | Cbx7 | 23492 | 21-May-15 | 16420 | 3 | 4 | | | | IV-1 | Cdc23 | 8697 | 4-May-15 |
| 16326 | 3 | 4 | | | | IV-1 | Cby1 | 25776 | 4-May-15 | 16421 | 3 | 4 | | | | IV-1 | Cdc25a | 993 | 31-May-15 |
| 16327 | 3 | 4 | | | | IV-1 | Cc2d1a | 54862 | 31-May-15 | 16422 | 3 | 4 | | | | IV-1 | Cdc27 | 996 | 31-May-15 |
| 16328 | 3 | 4 | | | | IV-1 | Cc2d1b | 200014 | 28-May-15 | 16423 | 3 | 4 | | | | IV-1 | Cdc34 | 997 | 4-May-15 |
| 16329 | 3 | 4 | | | | IV-1 | Cc2d2a | 57545 | 12-May-15 | 16424 | 3 | 4 | | | | IV-1 | Cdc37 | 11140 | 17-May-15 |
| 16330 | 3 | 4 | | | | IV-1 | Ccar2 | 57805 | 29-May-15 | 16425 | 3 | 4 | | | | IV-1 | Cdc37l1 | 55664 | 4-May-15 |
| 16331 | 3 | 4 | | | | IV-1 | Ccdc102a | 92922 | 12-May-15 | 16426 | 3 | 4 | | | | IV-1 | Cdc42 | 998 | 23-May-15 |
| 16332 | 3 | 4 | | | | IV-1 | Ccdc104 | 112942 | 4-May-15 | 16427 | 3 | 4 | | | | IV-1 | Cdc42bpa | 8476 | 4-May-15 |
| 16333 | 3 | 4 | | | | IV-1 | Ccdc105 | 126402 | 4-May-15 | 16428 | 3 | 4 | | | | IV-1 | Cdc42bpb | 9578 | 4-May-15 |
| 16334 | 3 | 4 | | | | IV-1 | Ccdc106 | 29903 | 4-May-15 | 16429 | 3 | 4 | | | | IV-1 | Cdc42bpg | 55561 | 4-May-15 |
| 16335 | 3 | 4 | | | | IV-1 | Ccdc107 | 203260 | 4-May-15 | 16430 | 3 | 4 | | | | IV-1 | Cdh13 | 1012 | 17-May-15 |
| 16336 | 3 | 4 | | | | IV-1 | Ccdc110 | 256309 | 4-May-15 | 16431 | 3 | 4 | | | | IV-1 | Cdh22 | 64405 | 4-May-15 |
| 16337 | 3 | 4 | | | | IV-1 | Ccdc112 | 153733 | 12-May-15 | 16432 | 3 | 4 | | | | IV-1 | Cdh23 | 64072 | 23-May-15 |
| 16338 | 3 | 4 | | | | IV-1 | Ccdc117 | 150275 | 4-May-15 | 16433 | 3 | 4 | | | | IV-1 | Cdh24 | 64403 | 7-Jun-15 |
| 16339 | 3 | 4 | | | | IV-1 | Ccdc12 | 151903 | 4-May-15 | 16434 | 3 | 4 | | | | IV-1 | Cdh7 | 1005 | 7-Jun-15 |
| 16340 | 3 | 4 | | | | IV-1 | Ccdc121 | 79635 | 4-May-15 | 16435 | 3 | 4 | | | | IV-1 | Cdh8 | 1006 | 12-May-15 |
| 16341 | 3 | 4 | | | | IV-1 | Ccdc125 | 202243 | 4-May-15 | 16436 | 3 | 4 | | | | IV-1 | Cdh9 | 1007 | 4-May-15 |
| 16342 | 3 | 4 | | | | IV-1 | Ccdc127 | 133957 | 4-May-15 | 16437 | 3 | 4 | | | | IV-1 | Cdhr1 | 92211 | 4-May-15 |
| 16343 | 3 | 4 | | | | IV-1 | Ccdc129 | 223075 | 4-May-15 | 16438 | 3 | 4 | | | | IV-1 | Cdk11b | 984 | 12-May-15 |
| 16344 | 3 | 4 | | | | IV-1 | Ccdc130 | 81576 | 14-May-15 | 16439 | 3 | 4 | | | | IV-1 | Cdk12 | 51755 | 21-May-15 |
| 16345 | 3 | 4 | | | | IV-1 | Ccdc132 | 55610 | 29-May-15 | 16440 | 3 | 4 | | | | IV-1 | Cdk13 | 8621 | 4-May-15 |
| 16346 | 3 | 4 | | | | IV-1 | Ccdc134 | 79879 | 12-May-15 | 16441 | 3 | 4 | | | | IV-1 | Cdk16 | 5127 | 31-May-15 |
| 16347 | 3 | 4 | | | | IV-1 | Ccdc138 | 165055 | 12-May-15 | 16442 | 3 | 4 | | | | IV-1 | Cdk17 | 5128 | 4-May-15 |
| 16348 | 3 | 4 | | | | IV-1 | Ccdc14 | 64770 | 12-May-15 | 16443 | 3 | 4 | | | | IV-1 | Cdk18 | 5129 | 4-May-15 |
| 16349 | 3 | 4 | | | | IV-1 | Ccdc144b | 284047 | 4-May-15 | 16444 | 3 | 4 | | | | IV-1 | Cdk2 | 1017 | 12-May-15 |
| 16350 | 3 | 4 | | | | IV-1 | Ccdc146 | 57639 | 4-May-15 | 16445 | 3 | 4 | | | | IV-1 | Cdk2ap2 | 10263 | 4-May-15 |
| 16351 | 3 | 4 | | | | IV-1 | Ccdc151 | 115948 | 28-May-15 | 16446 | 3 | 4 | | | | IV-1 | Cdk3-ps | | |
| 16352 | 3 | 4 | | | | IV-1 | Ccdc155 | 147872 | 14-May-15 | 16447 | 3 | 4 | | | | IV-1 | Cdk5 | 1020 | 27-May-15 |
| 16353 | 3 | 4 | | | | IV-1 | Ccdc157 | 550631 | 4-May-15 | 16448 | 3 | 4 | | | | IV-1 | Cdk5r1 | 8851 | 4-May-15 |
| 16354 | 3 | 4 | | | | IV-1 | Ccdc166 | 100130274 | 4-May-15 | 16449 | 3 | 4 | | | | IV-1 | Cdk5rap1 | 51654 | 4-May-15 |
| 16355 | 3 | 4 | | | | IV-1 | Ccdc167 | 154467 | 4-May-15 | 16450 | 3 | 4 | | | | IV-1 | Cdk5rap3 | 80279 | 12-May-15 |
| 16356 | 3 | 4 | | | | IV-1 | Ccdc169 | 728591 | 12-May-15 | 16451 | 3 | 4 | | | | IV-1 | Cdk6 | 1021 | 17-May-15 |
| 16357 | 3 | 4 | | | | IV-1 | Ccdc173 | 129881 | 4-May-15 | 16452 | 3 | 4 | | | | IV-1 | Cdk8 | 1024 | 17-May-15 |
| 16358 | 3 | 4 | | | | IV-1 | Ccdc175 | 729665 | 4-May-15 | 16453 | 3 | 4 | | | | IV-1 | Cdk9 | 1025 | 4-May-15 |
| 16359 | 3 | 4 | | | | IV-1 | Ccdc176 | 80127 | 4-May-15 | 16454 | 3 | 4 | | | | IV-1 | Cdkal1 | 54903 | 31-May-15 |
| 16360 | 3 | 4 | | | | IV-1 | Ccdc178 | 374864 | 12-May-15 | 16455 | 3 | 4 | | | | IV-1 | Cdkl1 | 8814 | 21-May-15 |
| 16361 | 3 | 4 | | | | IV-1 | Ccdc23 | 374969 | 4-May-15 | 16456 | 3 | 4 | | | | IV-1 | Cdkn2aipnl | 91368 | 4-May-15 |
| 16362 | 3 | 4 | | | | IV-1 | Ccdc27 | 148870 | 4-May-15 | 16457 | 3 | 4 | | | | IV-1 | Cdr1 | 1038 | 4-May-15 |
| 16363 | 3 | 4 | | | | IV-1 | Ccdc28a | 25901 | 4-May-15 | 16458 | 3 | 4 | | | | IV-1 | Cdsn | 1041 | 30-May-15 |
| 16364 | 3 | 4 | | | | IV-1 | Ccdc3 | 83643 | 12-May-15 | 16459 | 3 | 4 | | | | IV-1 | Cdx1 | 1044 | 28-May-15 |
| 16365 | 3 | 4 | | | | IV-1 | Ccdc33 | 80125 | 12-May-15 | 16460 | 3 | 4 | | | | IV-1 | Cdx2 | 1045 | 31-May-15 |
| 16366 | 3 | 4 | | | | IV-1 | Ccdc36 | 339834 | 4-May-15 | 16461 | 3 | 4 | | | | IV-1 | Cdx4 | 1046 | 28-May-15 |
| 16367 | 3 | 4 | | | | IV-1 | Ccdc37 | 348807 | 4-May-15 | 16462 | 3 | 4 | | | | IV-1 | Cdyl | 9425 | 4-May-15 |
| 16368 | 3 | 4 | | | | IV-1 | Ccdc47 | 57003 | 4-May-15 | 16463 | 3 | 4 | | | | IV-1 | Cdyl2 | 124359 | 4-May-15 |
| 16369 | 3 | 4 | | | | IV-1 | Ccdc50 | 152137 | 23-May-15 | 16464 | 3 | 4 | | | | IV-1 | Ceacam14 | | |
| 16370 | 3 | 4 | | | | IV-1 | Ccdc51 | 79714 | 4-May-15 | 16465 | 3 | 4 | | | | IV-1 | Ceacam15 | | |
| 16371 | 3 | 4 | | | | IV-1 | Ccdc54 | 84692 | 4-May-15 | 16466 | 3 | 4 | | | | IV-1 | Ceacam9 | | |
| 16372 | 3 | 4 | | | | IV-1 | Ccdc55 | 84081 | 4-May-15 | 16467 | 3 | 4 | | | | IV-1 | Ceacam-ps1 | | |
| 16373 | 3 | 4 | | | | IV-1 | Ccdc59 | 29080 | 4-May-15 | 16468 | 3 | 4 | | | | IV-1 | Cebpzos | 100505876 | 12-May-15 |
| 16374 | 3 | 4 | | | | IV-1 | Ccdc61 | 729440 | 4-May-15 | 16469 | 3 | 4 | | | | IV-1 | Celf6 | 60677 | 4-May-15 |
| 16375 | 3 | 4 | | | | IV-1 | Ccdc62 | 84660 | 4-May-15 | 16470 | 3 | 4 | | | | IV-1 | Celrr | | |
| 16376 | 3 | 4 | | | | IV-1 | Ccdc63 | 160762 | 12-May-15 | 16471 | 3 | 4 | | | | IV-1 | Celsr3 | 1951 | 12-May-15 |
| 16377 | 3 | 4 | | | | IV-1 | Ccdc70 | 83446 | 4-May-15 | 16472 | 3 | 4 | | | | IV-1 | Cenpc1 | 1060 | 4-May-15 |
| 16378 | 3 | 4 | | | | IV-1 | Ccdc71 | 64925 | 12-May-15 | 16473 | 3 | 4 | | | | IV-1 | Cep112 | 201134 | 12-May-15 |
| 16379 | 3 | 4 | | | | IV-1 | Ccdc71l | 168455 | 4-May-15 | 16474 | 3 | 4 | | | | IV-1 | Cep164 | 22897 | 31-May-15 |
| 16380 | 3 | 4 | | | | IV-1 | Ccdc8 | 83987 | 23-May-15 | 16475 | 3 | 4 | | | | IV-1 | Cep170 | 9859 | 12-May-15 |
| 16381 | 3 | 4 | | | | IV-1 | Ccdc84 | 338657 | 4-May-15 | 16476 | 3 | 4 | | | | IV-1 | Cep192 | 55125 | 4-May-15 |
| 16382 | 3 | 4 | | | | IV-1 | Ccdc85c | 317762 | 4-May-15 | 16477 | 3 | 4 | | | | IV-1 | Cep41 | 95681 | 23-May-15 |
| 16383 | 3 | 4 | | | | IV-1 | Ccdc88a | 55704 | 31-May-15 | 16478 | 3 | 4 | | | | IV-1 | Cep57l1 | 285753 | 12-May-15 |
| 16384 | 3 | 4 | | | | IV-1 | Ccdc9 | 26093 | 4-May-15 | 16479 | 3 | 4 | | | | IV-1 | Cep68 | 23177 | 7-Jun-15 |
| 16385 | 3 | 4 | | | | IV-1 | Ccdc90b | 60492 | 4-May-15 | 16480 | 3 | 4 | | | | IV-1 | Cep70 | 80321 | 4-May-15 |
| 16386 | 3 | 4 | | | | IV-1 | Ccdc91 | 55297 | 4-May-15 | 16481 | 3 | 4 | | | | IV-1 | Cep83 | 51134 | 12-May-15 |
| 16387 | 3 | 4 | | | | IV-1 | Ccdc92 | 80212 | 21-May-15 | 16482 | 3 | 4 | | | | IV-1 | Cep83os | | |
| 16388 | 3 | 4 | | | | IV-1 | Ccdc94 | 55702 | 4-May-15 | 16483 | 3 | 4 | | | | IV-1 | Cep97 | 79598 | 4-May-15 |
| 16389 | 3 | 4 | | | | IV-1 | Ccdc96 | 257236 | 28-May-15 | 16484 | 3 | 4 | | | | IV-1 | Cer1 | 9350 | 4-May-15 |
| 16390 | 3 | 4 | | | | IV-1 | Ccer1 | 196477 | 4-May-15 | 16485 | 3 | 4 | | | | IV-1 | Cers3 | 204219 | 4-May-15 |
| 16391 | 3 | 4 | | | | IV-1 | Cchcr1 | 54535 | 12-May-15 | 16486 | 3 | 4 | | | | IV-1 | Ces1b | | |
| 16392 | 3 | 4 | | | | IV-1 | Cci1 | 6346 | 4-May-15 | 16487 | 3 | 4 | | | | IV-1 | Cetn4 | | |
| 16393 | 3 | 4 | | | | IV-1 | Ccnc | 892 | 17-May-15 | 16488 | 3 | 4 | | | | IV-1 | Cfhr2 | 3080 | 4-May-15 |
| 16394 | 3 | 4 | | | | IV-1 | Ccnd3 | 896 | 12-May-15 | 16489 | 3 | 4 | | | | IV-1 | Cflar | 8837 | 31-May-15 |
| 16395 | 3 | 4 | | | | IV-1 | Ccnj | 54619 | 4-May-15 | 16490 | 3 | 4 | | | | IV-1 | Cfp | 5199 | 17-May-15 |
| 16396 | 3 | 4 | | | | IV-1 | Ccnjl | 57018 | 7-Jun-15 | 16491 | 3 | 4 | | | | IV-1 | Chat | 1103 | 23-May-15 |
| 16397 | 3 | 4 | | | | IV-1 | Ccny | 219771 | 4-May-15 | 16492 | 3 | 4 | | | | IV-1 | Chchd1 | 118487 | 4-May-15 |
| 16398 | 3 | 4 | | | | IV-1 | Ccnyl1 | 151195 | 4-May-15 | 16493 | 3 | 4 | | | | IV-1 | Chchd6 | 84303 | 2-Jun-15 |
| 16399 | 3 | 4 | | | | IV-1 | Ccp110 | 9738 | 31-May-15 | 16494 | 3 | 4 | | | | IV-1 | Chchd7 | 79145 | 4-May-15 |
| 16400 | 3 | 4 | | | | IV-1 | Ccpg1os | | | 16495 | 3 | 4 | | | | IV-1 | Chd1l | 9557 | 12-May-15 |
| 16401 | 3 | 4 | | | | IV-1 | Ccser2 | 54462 | 4-May-15 | 16496 | 3 | 4 | | | | IV-1 | Chd2 | 1106 | 7-Jun-15 |
| 16402 | 3 | 4 | | | | IV-1 | Cct2 | 10576 | 17-May-15 | 16497 | 3 | 4 | | | | IV-1 | Chd3 | 1107 | 4-May-15 |
| 16403 | 3 | 4 | | | | IV-1 | Cct3 | 7203 | 4-May-15 | 16498 | 3 | 4 | | | | IV-1 | Chd3os | | |
| 16404 | 3 | 4 | | | | IV-1 | Cct4 | 10575 | 4-May-15 | 16499 | 3 | 4 | | | | IV-1 | Chd4 | 1108 | 12-May-15 |
| 16405 | 3 | 4 | | | | IV-1 | Cct5 | 22948 | 2-Jun-15 | 16500 | 3 | 4 | | | | IV-1 | Chd5 | 26038 | 7-Jun-15 |
| 16406 | 3 | 4 | | | | IV-1 | Cct6a | 908 | 4-May-15 | 16501 | 3 | 4 | | | | IV-1 | Chd6 | 84181 | 4-May-15 |
| 16407 | 3 | 4 | | | | IV-1 | Cct6b | 10693 | 4-May-15 | 16502 | 3 | 4 | | | | IV-1 | Chd7 | 55636 | 23-May-15 |
| 16408 | 3 | 4 | | | | IV-1 | Cct7 | 10574 | 4-May-15 | 16503 | 3 | 4 | | | | IV-1 | Chd9 | 80205 | 12-May-15 |
| 16409 | 3 | 4 | | | | IV-1 | Cct8 | 10694 | 12-May-15 | 16504 | 3 | 4 | | | | IV-1 | Chdh | 55349 | 21-May-15 |
| 16410 | 3 | 4 | | | | IV-1 | Cct8l1 | 155100 | 4-May-15 | 16505 | 3 | 4 | | | | IV-1 | Chfr | 55743 | 23-May-15 |
| 16411 | 3 | 4 | | | | IV-1 | Ccz1 | 51622 | 4-May-15 | 16506 | 3 | 4 | | | | IV-1 | Chid1 | 66005 | 4-May-15 |
| 16412 | 3 | 4 | | | | IV-1 | Cd160 | 11126 | 31-May-15 | 16507 | 3 | 4 | | | | IV-1 | ChkbCpt1b | 386593 | 4-May-15 |
| 16413 | 3 | 4 | | | | IV-1 | Cd164 | 8763 | 12-May-15 | 16508 | 3 | 4 | | | | IV-1 | Chmp1a | 5119 | 4-May-15 |

Fig. 30 - 88

| | | | | | | | | | | | | | | |
|---|---|---|---|---|---|---|---|---|---|---|---|---|---|---|
| 16509 | 3 | 4 | | | | IV-1 | Chmp1b | 57132 | 4-May-15 | 16605 | 3 | 4 | | | | IV-1 | Cntnap5b | | |
| 16510 | 3 | 4 | | | | IV-1 | Chmp2a | 27243 | 4-May-15 | 16606 | 3 | 4 | | | | IV-1 | Cntnap5c | | |
| 16511 | 3 | 4 | | | | IV-1 | Chmp3 | 51652 | 4-May-15 | 16607 | 3 | 4 | | | | IV-1 | Coa4 | 51287 | 4-May-15 |
| 16512 | 3 | 4 | | | | IV-1 | Chmp4b | 128866 | 7-Jun-15 | 16608 | 3 | 4 | | | | IV-1 | Coa5 | 493753 | 4-May-15 |
| 16513 | 3 | 4 | | | | IV-1 | Chmp4c | 92423 | 4-May-15 | 16609 | 3 | 4 | | | | IV-1 | Coa6 | 388753 | 21-May-15 |
| 16514 | 3 | 4 | | | | IV-1 | Chmp5 | 51510 | 31-May-15 | 16610 | 3 | 4 | | | | IV-1 | Coa7 | 65260 | 4-May-15 |
| 16515 | 3 | 4 | | | | IV-1 | Chmp6 | 79643 | 3-May-15 | 16611 | 3 | 4 | | | | IV-1 | Cog2 | 22796 | 4-May-15 |
| 16516 | 3 | 4 | | | | IV-1 | Chmp7 | 91782 | 4-May-15 | 16612 | 3 | 4 | | | | IV-1 | Cog3 | 83548 | 4-May-15 |
| 16517 | 3 | 4 | | | | IV-1 | Chn1 | 1123 | 23-May-15 | 16613 | 3 | 4 | | | | IV-1 | Cog4 | 25839 | 23-May-15 |
| 16518 | 3 | 4 | | | | IV-1 | Chn1os3 | | | 16614 | 3 | 4 | | | | IV-1 | Cog5 | 10466 | 23-May-15 |
| 16519 | 3 | 4 | | | | IV-1 | Chn2 | 1124 | 12-May-15 | 16615 | 3 | 4 | | | | IV-1 | Cog6 | 57511 | 4-May-15 |
| 16520 | 3 | 4 | | | | IV-1 | Chordc1 | 26973 | 4-May-15 | 16616 | 3 | 4 | | | | IV-1 | Cog7 | 91949 | 23-May-15 |
| 16521 | 3 | 4 | | | | IV-1 | Chp1 | 11261 | 7-Jun-15 | 16617 | 3 | 4 | | | | IV-1 | Cog8 | 84342 | 23-May-15 |
| 16522 | 3 | 4 | | | | IV-1 | Chrm2 | 1129 | 4-May-15 | 16618 | 3 | 4 | | | | IV-1 | Coil | 8161 | 4-May-15 |
| 16523 | 3 | 4 | | | | IV-1 | Chrna1 | 1134 | 23-May-15 | 16619 | 3 | 4 | | | | IV-1 | Col26a1 | 136227 | 4-May-15 |
| 16524 | 3 | 4 | | | | IV-1 | Chrna10 | 57053 | 4-May-15 | 16620 | 3 | 4 | | | | IV-1 | Col4a4 | 1286 | 23-May-15 |
| 16525 | 3 | 4 | | | | IV-1 | Chrna3 | 1136 | 12-May-15 | 16621 | 3 | 4 | | | | IV-1 | Col9a2 | 1298 | 23-May-15 |
| 16526 | 3 | 4 | | | | IV-1 | Chrna6 | 8973 | 12-May-15 | 16622 | 3 | 4 | | | | IV-1 | Col9a3 | 1299 | 23-May-15 |
| 16527 | 3 | 4 | | | | IV-1 | Chrnb3 | 1142 | 12-May-15 | 16623 | 3 | 4 | | | | IV-1 | Colec10 | 10584 | 4-May-15 |
| 16528 | 3 | 4 | | | | IV-1 | Chrnb4 | 1143 | 12-May-15 | 16624 | 3 | 4 | | | | IV-1 | Commd10 | 51397 | 12-May-15 |
| 16529 | 3 | 4 | | | | IV-1 | Chrne | 1145 | 23-May-15 | 16625 | 3 | 4 | | | | IV-1 | Commd3 | 23412 | 4-May-15 |
| 16530 | 3 | 4 | | | | IV-1 | Chst14 | 113389 | 4-May-15 | 16626 | 3 | 4 | | | | IV-1 | Commd4 | 54939 | 4-May-15 |
| 16531 | 3 | 4 | | | | IV-1 | Chst7 | 56548 | 12-May-15 | 16627 | 3 | 4 | | | | IV-1 | Commd5 | 28991 | 14-May-15 |
| 16532 | 3 | 4 | | | | IV-1 | Chsy1 | 22856 | 4-May-15 | 16628 | 3 | 4 | | | | IV-1 | Commd7 | 149951 | 4-May-15 |
| 16533 | 3 | 4 | | | | IV-1 | Chtop | 26097 | 4-May-15 | 16629 | 3 | 4 | | | | IV-1 | Commd8 | 54951 | 4-May-15 |
| 16534 | 3 | 4 | | | | IV-1 | Chuk | 1147 | 4-May-15 | 16630 | 3 | 4 | | | | IV-1 | Commd9 | 29099 | 12-May-15 |
| 16535 | 3 | 4 | | | | IV-1 | Churc1 | 91612 | 4-May-15 | 16631 | 3 | 4 | | | | IV-1 | Cnpb1 | 1315 | 4-May-15 |
| 16536 | 3 | 4 | | | | IV-1 | Ciao1 | 9391 | 4-May-15 | 16632 | 3 | 4 | | | | IV-1 | Cnpb2 | 9276 | 12-May-15 |
| 16537 | 3 | 4 | | | | IV-1 | Cib2 | 10518 | 4-May-15 | 16633 | 3 | 4 | | | | IV-1 | Cnpe | 11316 | 4-May-15 |
| 16538 | 3 | 4 | | | | IV-1 | Cic | 23152 | 17-May-15 | 16634 | 3 | 4 | | | | IV-1 | Cnpg1 | 22820 | 4-May-15 |
| 16539 | 3 | 4 | | | | IV-1 | Cipc | 85457 | 4-May-15 | 16635 | 3 | 4 | | | | IV-1 | Cnpg2 | 26958 | 12-May-15 |
| 16540 | 3 | 4 | | | | IV-1 | Cir1 | 9541 | 7-Jun-15 | 16636 | 3 | 4 | | | | IV-1 | Cnprs | 55352 | 4-May-15 |
| 16541 | 3 | 4 | | | | IV-1 | Cirbp | 1153 | 17-May-15 | 16637 | 3 | 4 | | | | IV-1 | Cops3 | 8533 | 4-May-15 |
| 16542 | 3 | 4 | | | | IV-1 | Cisd1 | 55847 | 4-May-15 | 16638 | 3 | 4 | | | | IV-1 | Cops4 | 51138 | 4-May-15 |
| 16543 | 3 | 4 | | | | IV-1 | Cisd3 | 284106 | 4-May-15 | 16639 | 3 | 4 | | | | IV-1 | Cops5 | 10987 | 4-May-15 |
| 16544 | 3 | 4 | | | | IV-1 | CK137956 | | | 16640 | 3 | 4 | | | | IV-1 | Cops6 | 10980 | 4-May-15 |
| 16545 | 3 | 4 | | | | IV-1 | Clasp2 | 23122 | 28-May-15 | 16641 | 3 | 4 | | | | IV-1 | Cops7a | 50813 | 4-May-15 |
| 16546 | 3 | 4 | | | | IV-1 | Clasrp | 11129 | 12-May-15 | 16642 | 3 | 4 | | | | IV-1 | Cops7b | 64708 | 21-May-15 |
| 16547 | 3 | 4 | | | | IV-1 | Clca5 | | | 16643 | 3 | 4 | | | | IV-1 | Cops8 | 10920 | 4-May-15 |
| 16548 | 3 | 4 | | | | IV-1 | Clcc1 | 23155 | 4-May-15 | 16644 | 3 | 4 | | | | IV-1 | Copz1 | 22818 | 12-May-15 |
| 16549 | 3 | 4 | | | | IV-1 | Clcnka | 1187 | 4-May-15 | 16645 | 3 | 4 | | | | IV-1 | Copz2 | 51226 | 4-May-15 |
| 16550 | 3 | 4 | | | | IV-1 | Cldn17 | 26285 | 4-May-15 | 16646 | 3 | 4 | | | | IV-1 | Coq5 | 84274 | 21-May-15 |
| 16551 | 3 | 4 | | | | IV-1 | Cldn26 | | | 16647 | 3 | 4 | | | | IV-1 | Coro1c | 23603 | 4-May-15 |
| 16552 | 3 | 4 | | | | IV-1 | Clec10a | 10462 | 4-May-15 | 16648 | 3 | 4 | | | | IV-1 | Cox17 | 10063 | 4-May-15 |
| 16553 | 3 | 4 | | | | IV-1 | Clec14a | 161198 | 4-May-15 | 16649 | 3 | 4 | | | | IV-1 | Cox18 | 285521 | 4-May-15 |
| 16554 | 3 | 4 | | | | IV-1 | Clec18a | 348174 | 4-May-15 | 16650 | 3 | 4 | | | | IV-1 | Cox19 | 90639 | 4-May-15 |
| 16555 | 3 | 4 | | | | IV-1 | Clec2e | | | 16651 | 3 | 4 | | | | IV-1 | Cox4i1 | 1327 | 4-May-15 |
| 16556 | 3 | 4 | | | | IV-1 | Clk2 | 1196 | 7-Jun-15 | 16652 | 3 | 4 | | | | IV-1 | Cox7b | 1349 | 15-May-15 |
| 16557 | 3 | 4 | | | | IV-1 | Clk3 | 1198 | 4-May-15 | 16653 | 3 | 4 | | | | IV-1 | Cox7c | 1350 | 12-May-15 |
| 16558 | 3 | 4 | | | | IV-1 | Clk4 | 57396 | 12-May-15 | 16654 | 3 | 4 | | | | IV-1 | Cpa5 | 93979 | 4-May-15 |
| 16559 | 3 | 4 | | | | IV-1 | Cln5 | 1203 | 23-May-15 | 16655 | 3 | 4 | | | | IV-1 | Cpa6 | 57094 | 16-Jun-15 |
| 16560 | 3 | 4 | | | | IV-1 | Cln6 | 54982 | 23-May-15 | 16656 | 3 | 4 | | | | IV-1 | Cpe | 1363 | 12-May-15 |
| 16561 | 3 | 4 | | | | IV-1 | Clns1a | 1207 | 12-May-15 | 16657 | 3 | 4 | | | | IV-1 | Cplx1 | 10815 | 4-May-15 |
| 16562 | 3 | 4 | | | | IV-1 | Clock | 9575 | 12-May-15 | 16658 | 3 | 4 | | | | IV-1 | Cplx4 | 339302 | 4-May-15 |
| 16563 | 3 | 4 | | | | IV-1 | Clpb | 81570 | 31-May-15 | 16659 | 3 | 4 | | | | IV-1 | Cpne1 | 8904 | 3-May-15 |
| 16564 | 3 | 4 | | | | IV-1 | Clpp | 8192 | 4-May-15 | 16660 | 3 | 4 | | | | IV-1 | Cpne4 | 131034 | 4-May-15 |
| 16565 | 3 | 4 | | | | IV-1 | Clptm1l | 81037 | 17-May-15 | 16661 | 3 | 4 | | | | IV-1 | Cpq | 10404 | 4-May-15 |
| 16566 | 3 | 4 | | | | IV-1 | Clrn2 | 645104 | 4-May-15 | 16662 | 3 | 4 | | | | IV-1 | Cpsf2 | 53981 | 4-May-15 |
| 16567 | 3 | 4 | | | | IV-1 | Cltc | 1213 | 31-May-15 | 16663 | 3 | 4 | | | | IV-1 | Cpsf3l | 54973 | 4-May-15 |
| 16568 | 3 | 4 | | | | IV-1 | Cluh | 23277 | 12-May-15 | 16664 | 3 | 4 | | | | IV-1 | Cpsf4 | 10898 | 4-May-15 |
| 16569 | 3 | 4 | | | | IV-1 | Clvs2 | 134829 | 4-May-15 | 16665 | 3 | 4 | | | | IV-1 | Cpsf4l | 642843 | 4-May-15 |
| 16570 | 3 | 4 | | | | IV-1 | Cmtm2a | | | 16666 | 3 | 4 | | | | IV-1 | Cpsf7 | 79869 | 4-May-15 |
| 16571 | 3 | 4 | | | | IV-1 | Cmtm2b | | | 16667 | 3 | 4 | | | | IV-1 | Cpt1a | 1374 | 23-May-15 |
| 16572 | 3 | 4 | | | | IV-1 | Cmtm3 | 123920 | 4-May-15 | 16668 | 3 | 4 | | | | IV-1 | Cpxcr1 | 53336 | 4-May-15 |
| 16573 | 3 | 4 | | | | IV-1 | Cmtm6 | 54918 | 4-May-15 | 16669 | 3 | 4 | | | | IV-1 | Cr1l | 1379 | 4-May-15 |
| 16574 | 3 | 4 | | | | IV-1 | Cmtr2 | 55783 | 12-May-15 | 16670 | 3 | 4 | | | | IV-1 | Crat | 1384 | 12-May-15 |
| 16575 | 3 | 4 | | | | IV-1 | Cnbp | 7555 | 23-May-15 | 16671 | 3 | 4 | | | | IV-1 | Crb2 | 286204 | 12-May-15 |
| 16576 | 3 | 4 | | | | IV-1 | Cndp1 | 84735 | 4-May-15 | 16672 | 3 | 4 | | | | IV-1 | Crb3 | 92359 | 4-May-15 |
| 16577 | 3 | 4 | | | | IV-1 | Cnga3 | 1261 | 31-May-15 | 16673 | 3 | 4 | | | | IV-1 | Crcp | 27297 | 4-May-15 |
| 16578 | 3 | 4 | | | | IV-1 | Cnga4 | 1262 | 4-May-15 | 16674 | 3 | 4 | | | | IV-1 | Creb3 | 10488 | 7-Jun-15 |
| 16579 | 3 | 4 | | | | IV-1 | Cngb1 | 1258 | 23-May-15 | 16675 | 3 | 4 | | | | IV-1 | Creb5 | 9586 | 21-May-15 |
| 16580 | 3 | 4 | | | | IV-1 | Cngb3 | 54714 | 23-May-15 | 16676 | 3 | 4 | | | | IV-1 | Crebl2 | 1389 | 5-May-15 |
| 16581 | 3 | 4 | | | | IV-1 | Cnih1 | 10175 | 4-May-15 | 16677 | 3 | 4 | | | | IV-1 | Crebrf | 153222 | 4-May-15 |
| 16582 | 3 | 4 | | | | IV-1 | Cnih3 | 149111 | 4-May-15 | 16678 | 3 | 4 | | | | IV-1 | Crebzf | 58487 | 4-May-15 |
| 16583 | 3 | 4 | | | | IV-1 | Cnih4 | 29097 | 21-May-15 | 16679 | 3 | 4 | | | | IV-1 | Creg1 | 8804 | 4-May-15 |
| 16584 | 3 | 4 | | | | IV-1 | Cnnm4 | 26504 | 12-May-15 | 16680 | 3 | 4 | | | | IV-1 | Crk | 1399 | 29-May-15 |
| 16585 | 3 | 4 | | | | IV-1 | Cnot1 | 23019 | 21-May-15 | 16681 | 3 | 4 | | | | IV-1 | Crtc2 | 200186 | 4-May-15 |
| 16586 | 3 | 4 | | | | IV-1 | Cnot10 | 25904 | 21-May-15 | 16682 | 3 | 4 | | | | IV-1 | Crtc3 | 64784 | 12-May-15 |
| 16587 | 3 | 4 | | | | IV-1 | Cnot11 | 55571 | 4-May-15 | 16683 | 3 | 4 | | | | IV-1 | Crx | 1406 | 28-May-15 |
| 16588 | 3 | 4 | | | | IV-1 | Cnot2 | 4848 | 28-May-15 | 16684 | 3 | 4 | | | | IV-1 | Crxos | | |
| 16589 | 3 | 4 | | | | IV-1 | Cnot3 | 4849 | 4-May-15 | 16685 | 3 | 4 | | | | IV-1 | Crygc | 1420 | 4-May-15 |
| 16590 | 3 | 4 | | | | IV-1 | Cnot4 | 4850 | 3-Jun-15 | 16686 | 3 | 4 | | | | IV-1 | Crygd | 1421 | 4-May-15 |
| 16591 | 3 | 4 | | | | IV-1 | Cnot6 | 57472 | 4-May-15 | 16687 | 3 | 4 | | | | IV-1 | Crygf | | |
| 16592 | 3 | 4 | | | | IV-1 | Cnot6l | 246175 | 3-Jun-15 | 16688 | 3 | 4 | | | | IV-1 | Crygn | 155051 | 21-May-15 |
| 16593 | 3 | 4 | | | | IV-1 | Cnot7 | 29883 | 16-May-15 | 16689 | 3 | 4 | | | | IV-1 | Cse1l | 1434 | 12-May-15 |
| 16594 | 3 | 4 | | | | IV-1 | Cnot8 | 9337 | 2-Jun-15 | 16690 | 3 | 4 | | | | IV-1 | Csf1 | 1435 | 12-May-15 |
| 16595 | 3 | 4 | | | | IV-1 | Cnp | 1267 | 7-Jun-15 | 16691 | 3 | 4 | | | | IV-1 | Csf2ra | 1438 | 4-May-15 |
| 16596 | 3 | 4 | | | | IV-1 | Cnpy1 | 285888 | 4-May-15 | 16692 | 3 | 4 | | | | IV-1 | Csk | 1445 | 3-May-15 |
| 16597 | 3 | 4 | | | | IV-1 | Cnpy2 | 10330 | 4-May-15 | 16693 | 3 | 4 | | | | IV-1 | Csmd2os | | |
| 16598 | 3 | 4 | | | | IV-1 | Cnpy3 | 10695 | 4-May-15 | 16694 | 3 | 4 | | | | IV-1 | Csmd3 | 114788 | 4-May-15 |
| 16599 | 3 | 4 | | | | IV-1 | Cnpy4 | 245812 | 4-May-15 | 16695 | 3 | 4 | | | | IV-1 | Csn1s1 | 1446 | 12-May-15 |
| 16600 | 3 | 4 | | | | IV-1 | Cntn3 | 5067 | 4-May-15 | 16696 | 3 | 4 | | | | IV-1 | Csn1s2a | 286828 | 4-May-15 |
| 16601 | 3 | 4 | | | | IV-1 | Cntn4 | 152330 | 4-May-15 | 16697 | 3 | 4 | | | | IV-1 | Csn1s2b | 100337616 | 4-May-15 |
| 16602 | 3 | 4 | | | | IV-1 | Cntnap1 | 8506 | 12-May-15 | 16698 | 3 | 4 | | | | IV-1 | Csn2 | 1447 | 7-Jun-15 |
| 16603 | 3 | 4 | | | | IV-1 | Cntnap4 | 85445 | 4-May-15 | 16699 | 3 | 4 | | | | IV-1 | Csn3 | 1448 | 7-Jun-15 |
| 16604 | 3 | 4 | | | | IV-1 | Cntnap5a | | | | | | | | | | | | |

Fig. 30 - 89

| | | | | | | | | | | | | |
|---|---|---|---|---|---|---|---|---|---|---|---|---|
| 16700 | 3 | 4 | | | | IV-1 | Csnk1d | 1453 | 29-May-15 | | | |
| 16701 | 3 | 4 | | | | IV-1 | Csnk1g1 | 53944 | 21-May-15 | | | |
| 16702 | 3 | 4 | | | | IV-1 | Csnk1g3 | 1456 | 4-May-15 | | | |
| 16703 | 3 | 4 | | | | IV-1 | Csnk2a1 | 1457 | 7-Jun-15 | | | |
| 16704 | 3 | 4 | | | | IV-1 | Csnk2a2 | 1459 | 2-Jun-15 | | | |
| 16705 | 3 | 4 | | | | IV-1 | Csnk2b | 1460 | 21-May-15 | | | |
| 16706 | 3 | 4 | | | | IV-1 | Csnka2ip | | | | | |
| 16707 | 3 | 4 | | | | IV-1 | Csrnp3 | 80034 | 28-May-15 | | | |
| 16708 | 3 | 4 | | | | IV-1 | Csrp1 | 1465 | 12-May-15 | | | |
| 16709 | 3 | 4 | | | | IV-1 | Cst3 | 1471 | 24-May-15 | | | |
| 16710 | 3 | 4 | | | | IV-1 | Cstad | | | | | |
| 16711 | 3 | 4 | | | | IV-1 | Cstf2 | 1478 | 12-May-15 | | | |
| 16712 | 3 | 4 | | | | IV-1 | Cstf2t | 23283 | 4-May-15 | | | |
| 16713 | 3 | 4 | | | | IV-1 | Cstf3 | 1479 | 4-May-15 | | | |
| 16714 | 3 | 4 | | | | IV-1 | Ctag2 | 30848 | 4-May-15 | | | |
| 16715 | 3 | 4 | | | | IV-1 | Ctage5 | 4253 | 4-May-15 | | | |
| 16716 | 3 | 4 | | | | IV-1 | Ctbp1 | 1487 | 4-May-15 | | | |
| 16717 | 3 | 4 | | | | IV-1 | Ctbp2 | 1488 | 12-May-15 | | | |
| 16718 | 3 | 4 | | | | IV-1 | Ctbs | 1486 | 12-May-15 | | | |
| 16719 | 3 | 4 | | | | IV-1 | Ctc1 | 80169 | 22-May-15 | | | |
| 16720 | 3 | 4 | | | | IV-1 | Ctdp1 | 9150 | 4-May-15 | | | |
| 16721 | 3 | 4 | | | | IV-1 | Ctdsp2 | 10106 | 12-May-15 | | | |
| 16722 | 3 | 4 | | | | IV-1 | Ctdspl | 10217 | 4-May-15 | | | |
| 16723 | 3 | 4 | | | | IV-1 | Ctf1 | 1489 | 12-May-15 | | | |
| 16724 | 3 | 4 | | | | IV-1 | Ctnnbip1 | 56998 | 14-May-15 | | | |
| 16725 | 3 | 4 | | | | IV-1 | Ctnnd1 | 1500 | 3-May-15 | | | |
| 16726 | 3 | 4 | | | | IV-1 | Ctnnd2 | 1501 | 29-May-15 | | | |
| 16727 | 3 | 4 | | | | IV-1 | Cts6 | | | | | |
| 16728 | 3 | 4 | | | | IV-1 | Cts7 | | | | | |
| 16729 | 3 | 4 | | | | IV-1 | Cts8 | | | | | |
| 16730 | 3 | 4 | | | | IV-1 | Cts8-ps | | | | | |
| 16731 | 3 | 4 | | | | IV-1 | Ctsa | 5476 | 12-May-15 | | | |
| 16732 | 3 | 4 | | | | IV-1 | Ctsm | | | | | |
| 16733 | 3 | 4 | | | | IV-1 | Ctso | 1519 | 7-Jun-15 | | | |
| 16734 | 3 | 4 | | | | IV-1 | Ctsq | | | | | |
| 16735 | 3 | 4 | | | | IV-1 | Ctsr | | | | | |
| 16736 | 3 | 4 | | | | IV-1 | Ctxn1 | 404217 | 4-May-15 | | | |
| 16737 | 3 | 4 | | | | IV-1 | Cuedc1 | 404093 | 12-May-15 | | | |
| 16738 | 3 | 4 | | | | IV-1 | Cuedc2 | 79004 | 4-May-15 | | | |
| 16739 | 3 | 4 | | | | IV-1 | Cul1 | 8454 | 24-May-15 | | | |
| 16740 | 3 | 4 | | | | IV-1 | Cul2 | 8453 | 12-May-15 | | | |
| 16741 | 3 | 4 | | | | IV-1 | Cul3 | 8452 | 4-May-15 | | | |
| 16742 | 3 | 4 | | | | IV-1 | Cul4a | 8451 | 21-May-15 | | | |
| 16743 | 3 | 4 | | | | IV-1 | Cul5 | 8065 | 4-May-15 | | | |
| 16744 | 3 | 4 | | | | IV-1 | Cul7 | 9820 | 23-May-15 | | | |
| 16745 | 3 | 4 | | | | IV-1 | Cuta | 51596 | 12-May-15 | | | |
| 16746 | 3 | 4 | | | | IV-1 | Cutal | | | | | |
| 16747 | 3 | 4 | | | | IV-1 | Cwc27 | 10283 | 21-May-15 | | | |
| 16748 | 3 | 4 | | | | IV-1 | Cwf19l1 | 55280 | 4-May-15 | | | |
| 16749 | 3 | 4 | | | | IV-1 | Cwh43 | 80157 | 4-May-15 | | | |
| 16750 | 3 | 4 | | | | IV-1 | Cxxc1b | 26071 | 4-May-15 | | | |
| 16751 | 3 | 4 | | | | IV-1 | Cxxc1c | 441518 | 4-May-15 | | | |
| 16752 | 3 | 4 | | | | IV-1 | Cxxc1 | 30827 | 4-May-15 | | | |
| 16753 | 3 | 4 | | | | IV-1 | Cxxc4 | 80319 | 4-May-15 | | | |
| 16754 | 3 | 4 | | | | IV-1 | Cyb561d1 | 284613 | 4-May-15 | | | |
| 16755 | 3 | 4 | | | | IV-1 | Cyb561d2 | 11068 | 4-May-15 | | | |
| 16756 | 3 | 4 | | | | IV-1 | Cyb5b | 80777 | 4-May-15 | | | |
| 16757 | 3 | 4 | | | | IV-1 | Cyb5d1 | 124637 | 4-May-15 | | | |
| 16758 | 3 | 4 | | | | IV-1 | Cyb5d2 | 124936 | 4-May-15 | | | |
| 16759 | 3 | 4 | | | | IV-1 | Cyfip1 | 23191 | 17-May-15 | | | |
| 16760 | 3 | 4 | | | | IV-1 | Cylc1 | 1538 | 4-May-15 | | | |
| 16761 | 3 | 4 | | | | IV-1 | Cylc2 | 1539 | 4-May-15 | | | |
| 16762 | 3 | 4 | | | | IV-1 | Cyld | 1540 | 12-May-15 | | | |
| 16763 | 3 | 4 | | | | IV-1 | Cym | | | | | |
| 16764 | 3 | 4 | | | | IV-1 | Cyp11a1 | 1583 | 12-May-15 | | | |
| 16765 | 3 | 4 | | | | IV-1 | Cyp11b2 | 1585 | 24-May-15 | | | |
| 16766 | 3 | 4 | | | | IV-1 | Cyp17a1 | 1586 | 24-May-15 | | | |
| 16767 | 3 | 4 | | | | IV-1 | Cyp27a1 | 1593 | 24-May-15 | | | |
| 16768 | 3 | 4 | | | | IV-1 | Cyp2c37 | | | | | |
| 16769 | 3 | 4 | | | | IV-1 | Cyp2c67 | | | | | |
| 16770 | 3 | 4 | | | | IV-1 | Cyp2c69 | | | | | |
| 16771 | 3 | 4 | | | | IV-1 | Cyp2j12 | | | | | |
| 16772 | 3 | 4 | | | | IV-1 | Cyp2j13 | | | | | |
| 16773 | 3 | 4 | | | | IV-1 | Cyp2j5 | | | | | |
| 16774 | 3 | 4 | | | | IV-1 | Cyp2j6 | | | | | |
| 16775 | 3 | 4 | | | | IV-1 | Cyp2j9 | | | | | |
| 16776 | 3 | 4 | | | | IV-1 | Cyp3a41a | | | | | |
| 16777 | 3 | 4 | | | | IV-1 | Cyp3a41b | | | | | |
| 16778 | 3 | 4 | | | | IV-1 | Cyp3a44 | | | | | |
| 16779 | 3 | 4 | | | | IV-1 | Cyp3a57 | | | | | |
| 16780 | 3 | 4 | | | | IV-1 | Cyp3a59 | | | | | |
| 16781 | 3 | 4 | | | | IV-1 | Cyp4a30b | | | | | |
| 16782 | 3 | 4 | | | | IV-1 | Cyp4f15 | | | | | |
| 16783 | 3 | 4 | | | | IV-1 | Cyp4f43-ps | | | | | |
| 16784 | 3 | 4 | | | | IV-1 | Cyp4v3 | | | | | |
| 16785 | 3 | 4 | | | | IV-1 | Cypt10 | | | | | |
| 16786 | 3 | 4 | | | | IV-1 | Cypt12 | | | | | |
| 16787 | 3 | 4 | | | | IV-1 | Cypt15 | | | | | |
| 16788 | 3 | 4 | | | | IV-1 | Cypt2 | | | | | |
| 16789 | 3 | 4 | | | | IV-1 | Cypt3 | | | | | |
| 16790 | 3 | 4 | | | | IV-1 | Cypt4 | | | | | |
| 16791 | 3 | 4 | | | | IV-1 | Cypt7 | | | | | |
| 16792 | 3 | 4 | | | | IV-1 | Cyth3 | 9265 | 4-May-15 | | | |
| 16793 | 3 | 4 | | | | IV-1 | D030024E09Rik | | | | | |
| 16794 | 3 | 4 | | | | IV-1 | D030025E07Rik | | | | | |
| 16795 | 3 | 4 | | | | IV-1 | D030025P21Rik | | | | | |
| 16796 | 3 | 4 | | | | IV-1 | D030028A08Rik | | | |
| 16797 | 3 | 4 | | | | IV-1 | D030045P18Rik | | | |
| 16798 | 3 | 4 | | | | IV-1 | D11Wsu47e | | | |
| 16799 | 3 | 4 | | | | IV-1 | D130017N08Rik | | | |
| 16800 | 3 | 4 | | | | IV-1 | D130020L05Rik | | | |
| 16801 | 3 | 4 | | | | IV-1 | D130043K22Rik | | | |
| 16802 | 3 | 4 | | | | IV-1 | D16Ertd472e | | | |
| 16803 | 3 | 4 | | | | IV-1 | D16Ertd519e | | | |
| 16804 | 3 | 4 | | | | IV-1 | D17Ertd648e | | | |
| 16805 | 3 | 4 | | | | IV-1 | D17H6S53E | | | |
| 16806 | 3 | 4 | | | | IV-1 | D17Wsu92e | | | |
| 16807 | 3 | 4 | | | | IV-1 | D1Ertd622e | | | |
| 16808 | 3 | 4 | | | | IV-1 | D230025D16Rik | | | |
| 16809 | 3 | 4 | | | | IV-1 | D2hgdh | 728294 | 4-May-15 |
| 16810 | 3 | 4 | | | | IV-1 | D330050G23Rik | | | |
| 16811 | 3 | 4 | | | | IV-1 | D3Bwg0562e | | | |
| 16812 | 3 | 4 | | | | IV-1 | D3Ertd254e | | | |
| 16813 | 3 | 4 | | | | IV-1 | D3Ertd751e | | | |
| 16814 | 3 | 4 | | | | IV-1 | D4Ertd617e | | | |
| 16815 | 3 | 4 | | | | IV-1 | D530049I02Rik | | | |
| 16816 | 3 | 4 | | | | IV-1 | D5Ertd577e | | | |
| 16817 | 3 | 4 | | | | IV-1 | D5Ertd579e | | | |
| 16818 | 3 | 4 | | | | IV-1 | D630032N06Rik | | | |
| 16819 | 3 | 4 | | | | IV-1 | D630045J12Rik | | | |
| 16820 | 3 | 4 | | | | IV-1 | D6Ertd474e | | | |
| 16821 | 3 | 4 | | | | IV-1 | D6Ertd527e | | | |
| 16822 | 3 | 4 | | | | IV-1 | D6Wsu163e | | | |
| 16823 | 3 | 4 | | | | IV-1 | D730001G18Rik | | | |
| 16824 | 3 | 4 | | | | IV-1 | D730045A05Rik | | | |
| 16825 | 3 | 4 | | | | IV-1 | D7Ertd143e | | | |
| 16826 | 3 | 4 | | | | IV-1 | D7Ertd443e | | | |
| 16827 | 3 | 4 | | | | IV-1 | D830031N03Rik | | | |
| 16828 | 3 | 4 | | | | IV-1 | D830032E09Rik | | | |
| 16829 | 3 | 4 | | | | IV-1 | D8Ertd82e | | | |
| 16830 | 3 | 4 | | | | IV-1 | D930007P13Rik | | | |
| 16831 | 3 | 4 | | | | IV-1 | D930028M14Rik | | | |
| 16832 | 3 | 4 | | | | IV-1 | D930032P07Rik | | | |
| 16833 | 3 | 4 | | | | IV-1 | Daam2 | 23500 | 14-May-15 |
| 16834 | 3 | 4 | | | | IV-1 | Dact1 | 51339 | 3-May-15 |
| 16835 | 3 | 4 | | | | IV-1 | Dag1a | 747 | 4-May-15 |
| 16836 | 3 | 4 | | | | IV-1 | Dars2 | 55157 | 23-May-15 |
| 16837 | 3 | 4 | | | | IV-1 | Daxx | 1616 | 17-May-15 |
| 16838 | 3 | 4 | | | | IV-1 | Dazap1 | 26528 | 2-Jun-15 |
| 16839 | 3 | 4 | | | | IV-1 | Dazap2 | 9802 | 12-May-15 |
| 16840 | 3 | 4 | | | | IV-1 | Dazl | 1618 | 12-May-15 |
| 16841 | 3 | 4 | | | | IV-1 | Dbhos | | | |
| 16842 | 3 | 4 | | | | IV-1 | Dbi | 1622 | 7-Jun-15 |
| 16843 | 3 | 4 | | | | IV-1 | Dbnl | 28988 | 4-May-15 |
| 16844 | 3 | 4 | | | | IV-1 | Dbr1 | 51163 | 4-May-15 |
| 16845 | 3 | 4 | | | | IV-1 | Dbx2 | 440097 | 4-May-15 |
| 16846 | 3 | 4 | | | | IV-1 | Dcaf10 | 79269 | 4-May-15 |
| 16847 | 3 | 4 | | | | IV-1 | Dcaf11 | 80344 | 12-May-15 |
| 16848 | 3 | 4 | | | | IV-1 | Dcaf15 | 90379 | 4-May-15 |
| 16849 | 3 | 4 | | | | IV-1 | Dcaf17 | 80067 | 23-May-15 |
| 16850 | 3 | 4 | | | | IV-1 | Dcaf4 | 26094 | 21-May-15 |
| 16851 | 3 | 4 | | | | IV-1 | Dcaf6 | 55827 | 4-May-15 |
| 16852 | 3 | 4 | | | | IV-1 | Dcaf8 | 50717 | 4-May-15 |
| 16853 | 3 | 4 | | | | IV-1 | Dcakd | 79877 | 4-May-15 |
| 16854 | 3 | 4 | | | | IV-1 | Dcbld2 | 131566 | 4-May-15 |
| 16855 | 3 | 4 | | | | IV-1 | Dcc | 1630 | 17-May-15 |
| 16856 | 3 | 4 | | | | IV-1 | Dchs1 | 8642 | 4-May-15 |
| 16857 | 3 | 4 | | | | IV-1 | Dcp1b | 196513 | 23-May-15 |
| 16858 | 3 | 4 | | | | IV-1 | Dcp2 | 167227 | 4-May-15 |
| 16859 | 3 | 4 | | | | IV-1 | Dcpp1 | | | |
| 16860 | 3 | 4 | | | | IV-1 | Dcpp3 | | | |
| 16861 | 3 | 4 | | | | IV-1 | Dcps | 28960 | 4-May-15 |
| 16862 | 3 | 4 | | | | IV-1 | Dcst1 | 149095 | 4-May-15 |
| 16863 | 3 | 4 | | | | IV-1 | Dctn2 | 10540 | 29-May-15 |
| 16864 | 3 | 4 | | | | IV-1 | Dctn3 | 11258 | 4-May-15 |
| 16865 | 3 | 4 | | | | IV-1 | Dctn4 | 51164 | 4-May-15 |
| 16866 | 3 | 4 | | | | IV-1 | Dctn5 | 84516 | 4-May-15 |
| 16867 | 3 | 4 | | | | IV-1 | Dctn6 | 10671 | 4-May-15 |
| 16868 | 3 | 4 | | | | IV-1 | Dcun1d2 | 55208 | 4-May-15 |
| 16869 | 3 | 4 | | | | IV-1 | Dcxr | 51181 | 4-May-15 |
| 16870 | 3 | 4 | | | | IV-1 | Ddb2 | 1643 | 23-May-15 |
| 16871 | 3 | 4 | | | | IV-1 | Ddhd2 | 23259 | 4-May-15 |
| 16872 | 3 | 4 | | | | IV-1 | Ddi1 | 414301 | 4-May-15 |
| 16873 | 3 | 4 | | | | IV-1 | Ddi2 | 84301 | 4-May-15 |
| 16874 | 3 | 4 | | | | IV-1 | Ddo | 8528 | 4-May-15 |
| 16875 | 3 | 4 | | | | IV-1 | Ddr1 | 780 | 4-May-15 |
| 16876 | 3 | 4 | | | | IV-1 | Ddt | 1652 | 4-May-15 |
| 16877 | 3 | 4 | | | | IV-1 | Ddx10 | 1662 | 4-May-15 |
| 16878 | 3 | 4 | | | | IV-1 | Ddx11 | 1663 | 21-May-15 |
| 16879 | 3 | 4 | | | | IV-1 | Ddx18 | 8886 | 4-May-15 |
| 16880 | 3 | 4 | | | | IV-1 | Ddx19a | 55308 | 4-May-15 |
| 16881 | 3 | 4 | | | | IV-1 | Ddx19b | 11269 | 4-May-15 |
| 16882 | 3 | 4 | | | | IV-1 | Ddx20 | 11218 | 28-May-15 |
| 16883 | 3 | 4 | | | | IV-1 | Ddx21 | 9188 | 7-Jun-15 |
| 16884 | 3 | 4 | | | | IV-1 | Ddx24 | 57062 | 4-May-15 |
| 16885 | 3 | 4 | | | | IV-1 | Ddx25 | 29118 | 12-May-15 |
| 16886 | 3 | 4 | | | | IV-1 | Ddx26b | 203522 | 4-May-15 |
| 16887 | 3 | 4 | | | | IV-1 | Ddx28 | 55794 | 4-May-15 |
| 16888 | 3 | 4 | | | | IV-1 | Ddx31 | 64794 | 7-Jun-15 |
| 16889 | 3 | 4 | | | | IV-1 | Ddx39 | 10212 | 4-May-15 |
| 16890 | 3 | 4 | | | | IV-1 | Ddx3x | 1654 | 12-May-15 |

Fig. 30 - 90

| | | | | | | | | | | | | | | | | |
|---|---|---|---|---|---|---|---|---|---|---|---|---|---|---|---|---|
| 16891 | 3 | 4 | | | | IV-1 | Ddx3y | 8653 | 23-May-15 | 16986 | 3 | 4 | | | IV-1 | Dmrtc1c2 | | |
| 16892 | 3 | 4 | | | | IV-1 | Ddx4 | 54514 | 4-May-15 | 16987 | 3 | 4 | | | IV-1 | Dmrtc2 | 63946 | 4-May-15 |
| 16893 | 3 | 4 | | | | IV-1 | Ddx41 | 51428 | 4-May-15 | 16988 | 3 | 4 | | | IV-1 | Dmtf1 | 9988 | 4-May-15 |
| 16894 | 3 | 4 | | | | IV-1 | Ddx42 | 11325 | 4-May-15 | 16989 | 3 | 4 | | | IV-1 | Dmxl1 | 1657 | 4-May-15 |
| 16895 | 3 | 4 | | | | IV-1 | Ddx43 | 55510 | 17-May-15 | 16990 | 3 | 4 | | | IV-1 | Dnaaf2 | 55172 | 28-May-15 |
| 16896 | 3 | 4 | | | | IV-1 | Ddx46 | 9879 | 3-May-15 | 16991 | 3 | 4 | | | IV-1 | Dnah10 | 196385 | 4-May-15 |
| 16897 | 3 | 4 | | | | IV-1 | Ddx47 | 51202 | 4-May-15 | 16992 | 3 | 4 | | | IV-1 | Dnah2 | 146754 | 12-May-15 |
| 16898 | 3 | 4 | | | | IV-1 | Ddx49 | 54555 | 4-May-15 | 16993 | 3 | 4 | | | IV-1 | Dnah7b | | |
| 16899 | 3 | 4 | | | | IV-1 | Ddx5 | 1655 | 4-May-15 | 16994 | 3 | 4 | | | IV-1 | Dnajc2 | | |
| 16900 | 3 | 4 | | | | IV-1 | Ddx50 | 79009 | 4-May-15 | 16995 | 3 | 4 | | | IV-1 | Dnaja2 | 10294 | 4-May-15 |
| 16901 | 3 | 4 | | | | IV-1 | Ddx51 | 317781 | 4-May-15 | 16996 | 3 | 4 | | | IV-1 | Dnajb12 | 54788 | 12-May-15 |
| 16902 | 3 | 4 | | | | IV-1 | Ddx52 | 11056 | 4-May-15 | 16997 | 3 | 4 | | | IV-1 | Dnajb6 | 10049 | 23-May-15 |
| 16903 | 3 | 4 | | | | IV-1 | Ddx54 | 79039 | 4-May-15 | 16998 | 3 | 4 | | | IV-1 | Dnajb7 | 150353 | 4-May-15 |
| 16904 | 3 | 4 | | | | IV-1 | Ddx55 | 57696 | 4-May-15 | 16999 | 3 | 4 | | | IV-1 | Dnajb8 | 165721 | 4-May-15 |
| 16905 | 3 | 4 | | | | IV-1 | Ddx56 | 54606 | 4-May-15 | 17000 | 3 | 4 | | | IV-1 | Dnajb9 | 4189 | 4-May-15 |
| 16906 | 3 | 4 | | | | IV-1 | Ddx58 | 23586 | 24-May-15 | 17001 | 3 | 4 | | | IV-1 | Dnajc13 | 23317 | 23-May-15 |
| 16907 | 3 | 4 | | | | IV-1 | Ddx6 | 1656 | 4-May-15 | 17002 | 3 | 4 | | | IV-1 | Dnajc14 | 85406 | 4-May-15 |
| 16908 | 3 | 4 | | | | IV-1 | Dear1 | 55223 | 4-May-15 | 17003 | 3 | 4 | | | IV-1 | Dnajc15 | 29103 | 21-May-15 |
| 16909 | 3 | 4 | | | | IV-1 | Dedd | 9191 | 4-May-15 | 17004 | 3 | 4 | | | IV-1 | Dnajc17 | 55192 | 4-May-15 |
| 16910 | 3 | 4 | | | | IV-1 | Dedd2 | 162989 | 4-May-15 | 17005 | 3 | 4 | | | IV-1 | Dnajc19 | 131118 | 4-May-15 |
| 16911 | 3 | 4 | | | | IV-1 | Defa17 | | | 17006 | 3 | 4 | | | IV-1 | Dnajc25 | 548645 | 4-May-15 |
| 16912 | 3 | 4 | | | | IV-1 | Defa21 | | | 17007 | 3 | 4 | | | IV-1 | Dnajc27 | 51277 | 4-May-15 |
| 16913 | 3 | 4 | | | | IV-1 | Defa23 | | | 17008 | 3 | 4 | | | IV-1 | Dnajc30 | 84277 | 4-May-15 |
| 16914 | 3 | 4 | | | | IV-1 | Defa25 | | | 17009 | 3 | 4 | | | IV-1 | Dnajc4 | 3338 | 21-May-15 |
| 16915 | 3 | 4 | | | | IV-1 | Defa26 | | | 17010 | 3 | 4 | | | IV-1 | Dnajc5 | 80331 | 12-May-15 |
| 16916 | 3 | 4 | | | | IV-1 | Defa3 | 1668 | 4-May-15 | 17011 | 3 | 4 | | | IV-1 | Dnajc5b | 85479 | 4-May-15 |
| 16917 | 3 | 4 | | | | IV-1 | Defa6 | 1671 | 4-May-15 | 17012 | 3 | 4 | | | IV-1 | Dnajc5g | 285126 | 14-May-15 |
| 16918 | 3 | 4 | | | | IV-1 | Defa-ps1 | | | 17013 | 3 | 4 | | | IV-1 | Dnajc6 | 9829 | 12-May-15 |
| 16919 | 3 | 4 | | | | IV-1 | Defa-rs1 | | | 17014 | 3 | 4 | | | IV-1 | Dnajc8 | 22826 | 4-May-15 |
| 16920 | 3 | 4 | | | | IV-1 | Degs1 | 8560 | 12-May-15 | 17015 | 3 | 4 | | | IV-1 | Dnal4 | 10126 | 4-May-15 |
| 16921 | 3 | 4 | | | | IV-1 | Dennd5a | 23258 | 4-May-15 | 17016 | 3 | 4 | | | IV-1 | Dnase2b | 58511 | 4-May-15 |
| 16922 | 3 | 4 | | | | IV-1 | Dennd6b | 414918 | 4-May-15 | 17017 | 3 | 4 | | | IV-1 | Dnm1 | 1759 | 21-May-15 |
| 16923 | 3 | 4 | | | | IV-1 | Denr | 8562 | 4-May-15 | 17018 | 3 | 4 | | | IV-1 | Dnm2 | 1785 | 23-May-15 |
| 16924 | 3 | 4 | | | | IV-1 | Derl2 | 51009 | 12-May-15 | 17019 | 3 | 4 | | | IV-1 | Dnm3 | 26052 | 12-May-15 |
| 16925 | 3 | 4 | | | | IV-1 | Dexi | 28955 | 4-May-15 | 17020 | 3 | 4 | | | IV-1 | Dnmt3aos | | |
| 16926 | 3 | 4 | | | | IV-1 | Dffa | 1676 | 4-May-15 | 17021 | 3 | 4 | | | IV-1 | Dnmt3b | 1789 | 24-May-15 |
| 16927 | 3 | 4 | | | | IV-1 | Dffb | 1677 | 12-May-15 | 17022 | 3 | 4 | | | IV-1 | Dnpep | 23549 | 4-May-15 |
| 16928 | 3 | 4 | | | | IV-1 | Dgat1 | 8694 | 4-May-15 | 17023 | 3 | 4 | | | IV-1 | Dock4 | 9732 | 4-May-15 |
| 16929 | 3 | 4 | | | | IV-1 | Dgcr14 | 8220 | 23-May-15 | 17024 | 3 | 4 | | | IV-1 | Dock7 | 85440 | 4-May-15 |
| 16930 | 3 | 4 | | | | IV-1 | Dgcr2 | 9993 | 7-Jun-15 | 17025 | 3 | 4 | | | IV-1 | Dock8 | 81704 | 4-May-15 |
| 16931 | 3 | 4 | | | | IV-1 | Dgcr6 | 8214 | 7-Jun-15 | 17026 | 3 | 4 | | | IV-1 | Dok5 | 55816 | 4-May-15 |
| 16932 | 3 | 4 | | | | IV-1 | Dgcr8 | 54487 | 23-May-15 | 17027 | 3 | 4 | | | IV-1 | Donson | 29980 | 4-May-15 |
| 16933 | 3 | 4 | | | | IV-1 | Dgka | 1606 | 12-May-15 | 17028 | 3 | 4 | | | IV-1 | Dopey2 | 9980 | 4-May-15 |
| 16934 | 3 | 4 | | | | IV-1 | Dgkd | 8527 | 4-May-15 | 17029 | 3 | 4 | | | IV-1 | Dos | 255057 | 4-May-15 |
| 16935 | 3 | 4 | | | | IV-1 | Dgkk | 139189 | 12-May-15 | 17030 | 3 | 4 | | | IV-1 | Dot1l | 84444 | 4-May-15 |
| 16936 | 3 | 4 | | | | IV-1 | Dgkq | 1609 | 21-May-15 | 17031 | 3 | 4 | | | IV-1 | Doxl2 | | |
| 16937 | 3 | 4 | | | | IV-1 | Dgkz | 8525 | 4-May-15 | 17032 | 3 | 4 | | | IV-1 | Dpagt1 | 1798 | 23-May-15 |
| 16938 | 3 | 4 | | | | IV-1 | Dguok | 1716 | 23-May-15 | 17033 | 3 | 4 | | | IV-1 | Dpcd | 25911 | 4-May-15 |
| 16939 | 3 | 4 | | | | IV-1 | Dhcr24 | 1718 | 12-May-15 | 17034 | 3 | 4 | | | IV-1 | Dpcr1 | 135656 | 4-May-15 |
| 16940 | 3 | 4 | | | | IV-1 | Dhrs1 | 115817 | 12-May-15 | 17035 | 3 | 4 | | | IV-1 | Dpf2 | 5977 | 2-Jun-15 |
| 16941 | 3 | 4 | | | | IV-1 | Dhrs3 | 9249 | 21-May-15 | 17036 | 3 | 4 | | | IV-1 | Dph2 | 1802 | 4-May-15 |
| 16942 | 3 | 4 | | | | IV-1 | Dhtkd1 | 55526 | 4-May-15 | 17037 | 3 | 4 | | | IV-1 | Dph3 | 285383 | 4-May-15 |
| 16943 | 3 | 4 | | | | IV-1 | Dhx16 | 8449 | 4-May-15 | 17038 | 3 | 4 | | | IV-1 | Dpm1 | 8813 | 4-May-15 |
| 16944 | 3 | 4 | | | | IV-1 | Dhx29 | 54505 | 4-May-15 | 17039 | 3 | 4 | | | IV-1 | Dpm2 | 8818 | 23-May-15 |
| 16945 | 3 | 4 | | | | IV-1 | Dhx30 | 22907 | 4-May-15 | 17040 | 3 | 4 | | | IV-1 | Dpm3 | 54344 | 4-May-15 |
| 16946 | 3 | 4 | | | | IV-1 | Dhx32 | 55760 | 4-May-15 | 17041 | 3 | 4 | | | IV-1 | Dpp10 | 57628 | 4-May-15 |
| 16947 | 3 | 4 | | | | IV-1 | Dhx33 | 56919 | 4-May-15 | 17042 | 3 | 4 | | | IV-1 | Dpp3 | 10072 | 12-May-15 |
| 16948 | 3 | 4 | | | | IV-1 | Dhx34 | 9704 | 4-May-15 | 17043 | 3 | 4 | | | IV-1 | Dpp4 | 1803 | 17-May-15 |
| 16949 | 3 | 4 | | | | IV-1 | Dhx35 | 60625 | 4-May-15 | 17044 | 3 | 4 | | | IV-1 | Dpp7 | 29952 | 4-May-15 |
| 16950 | 3 | 4 | | | | IV-1 | Dhx36 | 170506 | 21-May-15 | 17045 | 3 | 4 | | | IV-1 | Dpp9 | 91039 | 4-May-15 |
| 16951 | 3 | 4 | | | | IV-1 | Dhx37 | 57647 | 4-May-15 | 17046 | 3 | 4 | | | IV-1 | Dppa1 | | |
| 16952 | 3 | 4 | | | | IV-1 | Dhx38 | 9785 | 4-May-15 | 17047 | 3 | 4 | | | IV-1 | Dppa2 | 151871 | 4-May-15 |
| 16953 | 3 | 4 | | | | IV-1 | Dhx40 | 79665 | 12-May-15 | 17048 | 3 | 4 | | | IV-1 | Dppa3 | 359787 | 4-May-15 |
| 16954 | 3 | 4 | | | | IV-1 | Dhx57 | 90957 | 12-May-15 | 17049 | 3 | 4 | | | IV-1 | Dppa4 | 55211 | 4-May-15 |
| 16955 | 3 | 4 | | | | IV-1 | Dhx9 | 1660 | 4-May-15 | 17050 | 3 | 4 | | | IV-1 | Dppa5a | | |
| 16956 | 3 | 4 | | | | IV-1 | Diablo | 56616 | 17-May-15 | 17051 | 3 | 4 | | | IV-1 | Dpt | 1805 | 4-May-15 |
| 16957 | 3 | 4 | | | | IV-1 | Diap1 | | | 17052 | 3 | 4 | | | IV-1 | Dpyd | 1806 | 31-May-15 |
| 16958 | 3 | 4 | | | | IV-1 | Diap2 | | | 17053 | 3 | 4 | | | IV-1 | Dpysl2 | 1808 | 4-May-15 |
| 16959 | 3 | 4 | | | | IV-1 | Dido1 | 11083 | 4-May-15 | 17054 | 3 | 4 | | | IV-1 | Drap1 | 10589 | 4-May-15 |
| 16960 | 3 | 4 | | | | IV-1 | Dimt1 | 27292 | 4-May-15 | 17055 | 3 | 4 | | | IV-1 | Draxin | 374946 | 4-May-15 |
| 16961 | 3 | 4 | | | | IV-1 | Dip2b | 57609 | 4-May-15 | 17056 | 3 | 4 | | | IV-1 | Drd3 | 1814 | 17-May-15 |
| 16962 | 3 | 4 | | | | IV-1 | Diras1 | 148252 | 4-May-15 | 17057 | 3 | 4 | | | IV-1 | Drd4 | 1815 | 29-May-15 |
| 16963 | 3 | 4 | | | | IV-1 | Dis3 | 22894 | 17-May-15 | 17058 | 3 | 4 | | | IV-1 | Dreh | | |
| 16964 | 3 | 4 | | | | IV-1 | Disc1 | 27185 | 31-May-15 | 17059 | 3 | 4 | | | IV-1 | Drg1 | 4733 | 7-Jun-15 |
| 16965 | 3 | 4 | | | | IV-1 | Disp1 | 84976 | 12-May-15 | 17060 | 3 | 4 | | | IV-1 | Drg2 | 1819 | 4-May-15 |
| 16966 | 3 | 4 | | | | IV-1 | Dkk2 | 27123 | 4-May-15 | 17061 | 3 | 4 | | | IV-1 | Drosha | 29102 | 4-May-15 |
| 16967 | 3 | 4 | | | | IV-1 | Dlg2 | 1740 | 7-Jun-15 | 17062 | 3 | 4 | | | IV-1 | Dsc1 | 1823 | 7-Jun-15 |
| 16968 | 3 | 4 | | | | IV-1 | Dlgap1 | 9229 | 17-May-15 | 17063 | 3 | 4 | | | IV-1 | Dscaml1 | 57453 | 4-May-15 |
| 16969 | 3 | 4 | | | | IV-1 | Dlgap3 | 58512 | 4-May-15 | 17064 | 3 | 4 | | | IV-1 | Dsg4 | 147409 | 4-May-15 |
| 16970 | 3 | 4 | | | | IV-1 | Dlgap4 | 22839 | 4-May-15 | 17065 | 3 | 4 | | | IV-1 | Dst | 667 | 12-May-15 |
| 16971 | 3 | 4 | | | | IV-1 | Dlk2 | 65989 | 4-May-15 | 17066 | 3 | 4 | | | IV-1 | Dstyk | 25778 | 4-May-15 |
| 16972 | 3 | 4 | | | | IV-1 | Dll4 | 54567 | 4-May-15 | 17067 | 3 | 4 | | | IV-1 | Dtd1 | 92675 | 4-May-15 |
| 16973 | 3 | 4 | | | | IV-1 | Dlx1as | | | 17068 | 3 | 4 | | | IV-1 | Dtd2 | 112487 | 4-May-15 |
| 16974 | 3 | 4 | | | | IV-1 | Dlx2 | 1746 | 4-May-15 | 17069 | 3 | 4 | | | IV-1 | Dthd1 | 403124 | 4-May-15 |
| 16975 | 3 | 4 | | | | IV-1 | Dlx3 | 1747 | 28-May-15 | 17070 | 3 | 4 | | | IV-1 | Dtwd1 | 56986 | 14-May-15 |
| 16976 | 3 | 4 | | | | IV-1 | Dlx4 | 1748 | 4-May-15 | 17071 | 3 | 4 | | | IV-1 | Dtx3l | 151636 | 12-May-15 |
| 16977 | 3 | 4 | | | | IV-1 | Dlx6 | 1750 | 4-May-15 | 17072 | 3 | 4 | | | IV-1 | Duoxa1 | 90527 | 20-May-15 |
| 16978 | 3 | 4 | | | | IV-1 | Dlx6as2 | 100873931 | 1-Feb-15 | 17073 | 3 | 4 | | | IV-1 | Dupd1 | 338599 | 4-May-15 |
| 16979 | 3 | 4 | | | | IV-1 | Dlx6os1 | | | 17074 | 3 | 4 | | | IV-1 | Dus1l | 64118 | 4-May-15 |
| 16980 | 3 | 4 | | | | IV-1 | Dmc1 | 11144 | 7-Jun-15 | 17075 | 3 | 4 | | | IV-1 | Dus2 | 54920 | 4-May-15 |
| 16981 | 3 | 4 | | | | IV-1 | Dmd | 1756 | 24-May-15 | 17076 | 3 | 4 | | | IV-1 | Dus3l | 56931 | 4-May-15 |
| 16982 | 3 | 4 | | | | IV-1 | Dmrt2 | 10655 | 4-May-15 | 17077 | 3 | 4 | | | IV-1 | Dusp12 | 11266 | 4-May-15 |
| 16983 | 3 | 4 | | | | IV-1 | Dmrta1 | 63951 | 4-May-15 | 17078 | 3 | 4 | | | IV-1 | Dusp13 | 51207 | 4-May-15 |
| 16984 | 3 | 4 | | | | IV-1 | Dmrta2 | 63950 | 4-May-15 | 17079 | 3 | 4 | | | IV-1 | Dusp14 | 11072 | 4-May-15 |
| 16985 | 3 | 4 | | | | IV-1 | Dmrtc1c1 | | | 17080 | 3 | 4 | | | IV-1 | Dusp16 | 80824 | 4-May-15 |
| | | | | | | | | | | 17081 | 3 | 4 | | | IV-1 | Dusp22 | 56940 | 4-May-15 |

Fig. 30 - 91

| | | | | | | | | |
|---|---|---|---|---|---|---|---|---|
| 17082 | 3 | 4 | IV-1 | Dusp23 | 54935 | 7-Jun-15 |
| 17083 | 3 | 4 | IV-1 | Duxbl1 | | |
| 17084 | 3 | 4 | IV-1 | Duxbl2 | | |
| 17085 | 3 | 4 | IV-1 | Duxbl3 | | |
| 17086 | 3 | 4 | IV-1 | Dvl1 | 1855 | 7-Jun-15 |
| 17087 | 3 | 4 | IV-1 | Dvl2 | 1856 | 3-May-15 |
| 17088 | 3 | 4 | IV-1 | DXBay18 | | |
| 17089 | 3 | 4 | IV-1 | Dydc1 | 143241 | 4-May-15 |
| 17090 | 3 | 4 | IV-1 | Dynap | 284254 | 12-May-15 |
| 17091 | 3 | 4 | IV-1 | Dync1h1 | 1778 | 23-May-15 |
| 17092 | 3 | 4 | IV-1 | Dync1i2 | 1781 | 1-Jun-15 |
| 17093 | 3 | 4 | IV-1 | Dync1li1 | 51143 | 4-May-15 |
| 17094 | 3 | 4 | IV-1 | Dync1li2 | 1783 | 4-May-15 |
| 17095 | 3 | 4 | IV-1 | Dync2h1 | 79659 | 23-May-15 |
| 17096 | 3 | 4 | IV-1 | Dyrk1a | 1859 | 12-May-15 |
| 17097 | 3 | 4 | IV-1 | Dyrk1b | 9149 | 4-May-15 |
| 17098 | 3 | 4 | IV-1 | Dyrk2 | 8445 | 12-May-15 |
| 17099 | 3 | 4 | IV-1 | Dysf | 8291 | 31-May-15 |
| 17100 | 3 | 4 | IV-1 | Dyx1c1 | 161582 | 4-May-15 |
| 17101 | 3 | 4 | IV-1 | Dzank1 | 55184 | 28-May-15 |
| 17102 | 3 | 4 | IV-1 | E030002O03Rik | | |
| 17103 | 3 | 4 | IV-1 | E030024N20Rik | | |
| 17104 | 3 | 4 | IV-1 | E030025P04Rik | | |
| 17105 | 3 | 4 | IV-1 | E130008D07Rik | | |
| 17106 | 3 | 4 | IV-1 | E130012A19Rik | | |
| 17107 | 3 | 4 | IV-1 | E130102H24Rik | | |
| 17108 | 3 | 4 | IV-1 | E130304I02Rik | | |
| 17109 | 3 | 4 | IV-1 | E130307A14Rik | | |
| 17110 | 3 | 4 | IV-1 | E130309D02Rik | | |
| 17111 | 3 | 4 | IV-1 | E230016M11Rik | | |
| 17112 | 3 | 4 | IV-1 | E230019M04Rik | | |
| 17113 | 3 | 4 | IV-1 | E230025N22Rik | | |
| 17114 | 3 | 4 | IV-1 | E230029C05Rik | | |
| 17115 | 3 | 4 | IV-1 | E2f6 | 1876 | 4-May-15 |
| 17116 | 3 | 4 | IV-1 | E330017A01Rik | | |
| 17117 | 3 | 4 | IV-1 | E330017L17Rik | | |
| 17118 | 3 | 4 | IV-1 | E330023G01Rik | | |
| 17119 | 3 | 4 | IV-1 | E330038O04Rik | | |
| 17120 | 3 | 4 | IV-1 | E530011L22Rik | | |
| 17121 | 3 | 4 | IV-1 | Eaf1 | 85403 | 7-Jun-15 |
| 17122 | 3 | 4 | IV-1 | Ebp | 10682 | 7-Jun-15 |
| 17123 | 3 | 4 | IV-1 | Ebpl | 84650 | 4-May-15 |
| 17124 | 3 | 4 | IV-1 | Ecd | 11339 | 7-Jun-15 |
| 17125 | 3 | 4 | IV-1 | Ece1 | 1889 | 12-May-15 |
| 17126 | 3 | 4 | IV-1 | Ece2 | 9718 | 4-May-15 |
| 17127 | 3 | 4 | IV-1 | Eda | 1896 | 24-May-15 |
| 17128 | 3 | 4 | IV-1 | Edc4 | 23644 | 4-May-15 |
| 17129 | 3 | 4 | IV-1 | Edf1 | 8721 | 4-May-15 |
| 17130 | 3 | 4 | IV-1 | Edil3 | 10085 | 4-May-15 |
| 17131 | 3 | 4 | IV-1 | Edn1 | 1906 | 24-May-15 |
| 17132 | 3 | 4 | IV-1 | Eea1 | 8411 | 4-May-15 |
| 17133 | 3 | 4 | IV-1 | Eed | 8726 | 2-Jun-15 |
| 17134 | 3 | 4 | IV-1 | Eef1a1 | 1915 | 24-May-15 |
| 17135 | 3 | 4 | IV-1 | Eef1d | 1936 | 4-May-15 |
| 17136 | 3 | 4 | IV-1 | Eef1e1 | 9521 | 4-May-15 |
| 17137 | 3 | 4 | IV-1 | Eef2 | 1938 | 23-May-15 |
| 17138 | 3 | 4 | IV-1 | Eef2k | 29904 | 4-May-15 |
| 17139 | 3 | 4 | IV-1 | Eepd1 | 80820 | 4-May-15 |
| 17140 | 3 | 4 | IV-1 | Efcab14 | 9813 | 4-May-15 |
| 17141 | 3 | 4 | IV-1 | Efcab2 | 84288 | 4-May-15 |
| 17142 | 3 | 4 | IV-1 | Efcab4a | 283229 | 4-May-15 |
| 17143 | 3 | 4 | IV-1 | Efcab4b | 84766 | 4-May-15 |
| 17144 | 3 | 4 | IV-1 | Efcab6 | 64800 | 4-May-15 |
| 17145 | 3 | 4 | IV-1 | Efcab8 | 388795 | 4-May-15 |
| 17146 | 3 | 4 | IV-1 | Efnb1 | 1947 | 12-May-15 |
| 17147 | 3 | 4 | IV-1 | Eftud2 | 9343 | 23-May-15 |
| 17148 | 3 | 4 | IV-1 | Egfl6 | 25975 | 4-May-15 |
| 17149 | 3 | 4 | IV-1 | Egflam | 133584 | 4-May-15 |
| 17150 | 3 | 4 | IV-1 | Egln3 | 112399 | 12-May-15 |
| 17151 | 3 | 4 | IV-1 | Ehbp1l1 | 254102 | 12-May-15 |
| 17152 | 3 | 4 | IV-1 | Ehmt2 | 10919 | 4-May-15 |
| 17153 | 3 | 4 | IV-1 | Ei24 | 9538 | 21-May-15 |
| 17154 | 3 | 4 | IV-1 | Eid1 | 23741 | 4-May-15 |
| 17155 | 3 | 4 | IV-1 | Eid2 | 163126 | 4-May-15 |
| 17156 | 3 | 4 | IV-1 | Eif1ax | 1964 | 4-May-15 |
| 17157 | 3 | 4 | IV-1 | Eif2a | 83939 | 7-Jun-15 |
| 17158 | 3 | 4 | IV-1 | Eif2b1 | 1967 | 23-May-15 |
| 17159 | 3 | 4 | IV-1 | Eif2b2 | 8892 | 23-May-15 |
| 17160 | 3 | 4 | IV-1 | Eif2b3 | 8891 | 23-May-15 |
| 17161 | 3 | 4 | IV-1 | Eif2b4 | 8890 | 23-May-15 |
| 17162 | 3 | 4 | IV-1 | Eif2b5 | 8893 | 23-May-15 |
| 17163 | 3 | 4 | IV-1 | Eif2d | 1939 | 21-May-15 |
| 17164 | 3 | 4 | IV-1 | Eif2s1 | 1965 | 28-May-15 |
| 17165 | 3 | 4 | IV-1 | Eif2s2 | 8894 | 4-May-15 |
| 17166 | 3 | 4 | IV-1 | Eif2s3x | | |
| 17167 | 3 | 4 | IV-1 | Eif2s3y | | |
| 17168 | 3 | 4 | IV-1 | Eif3a | 8661 | 13-Jun-15 |
| 17169 | 3 | 4 | IV-1 | Eif3b | 8662 | 12-May-15 |
| 17170 | 3 | 4 | IV-1 | Eif3c | 8663 | 4-May-15 |
| 17171 | 3 | 4 | IV-1 | Eif3d | 8664 | 4-May-15 |
| 17172 | 3 | 4 | IV-1 | Eif3e | 3646 | 4-May-15 |
| 17173 | 3 | 4 | IV-1 | Eif3f | 8665 | 4-May-15 |
| 17174 | 3 | 4 | IV-1 | Eif3g | 8666 | 12-May-15 |
| 17175 | 3 | 4 | IV-1 | Eif3h | 8667 | 12-May-15 |
| 17176 | 3 | 4 | IV-1 | Eif3i | 8668 | 4-May-15 |
| 17177 | 3 | 4 | IV-1 | Eif3l | 51386 | 4-May-15 |
| 17178 | 3 | 4 | IV-1 | Eif3m | 10480 | 12-May-15 |
| 17179 | 3 | 4 | IV-1 | Eif4a1 | 1973 | 17-May-15 |
| 17180 | 3 | 4 | IV-1 | Eif4a3 | 9775 | 4-May-15 |
| 17181 | 3 | 4 | IV-1 | Eif4h | 1975 | 17-May-15 |
| 17182 | 3 | 4 | IV-1 | Eif4e | 1977 | 31-May-15 |
| 17183 | 3 | 4 | IV-1 | Eif4e2 | 9470 | 31-May-15 |
| 17184 | 3 | 4 | IV-1 | Eif4e3 | 317649 | 4-May-15 |
| 17185 | 3 | 4 | IV-1 | Eif4ebp3 | 8637 | 4-May-15 |
| 17186 | 3 | 4 | IV-1 | Eif4g2 | 1982 | 4-May-15 |
| 17187 | 3 | 4 | IV-1 | Eif4g3 | 8672 | 4-May-15 |
| 17188 | 3 | 4 | IV-1 | Eif4h | 7458 | 12-May-15 |
| 17189 | 3 | 4 | IV-1 | Eif5 | 1983 | 4-May-15 |
| 17190 | 3 | 4 | IV-1 | Eif5a2 | 56648 | 4-May-15 |
| 17191 | 3 | 4 | IV-1 | Eif5b | 9669 | 12-May-15 |
| 17192 | 3 | 4 | IV-1 | Eif6 | 3692 | 12-May-15 |
| 17193 | 3 | 4 | IV-1 | Elac2 | 60528 | 4-May-15 |
| 17194 | 3 | 4 | IV-1 | Elavl2 | 1993 | 4-May-15 |
| 17195 | 3 | 4 | IV-1 | Elavl3 | 1995 | 2-Jun-15 |
| 17196 | 3 | 4 | IV-1 | Elk3 | 2004 | 7-Jun-15 |
| 17197 | 3 | 4 | IV-1 | Elk4 | 2005 | 28-May-15 |
| 17198 | 3 | 4 | IV-1 | Elmo2 | 63916 | 4-May-15 |
| 17199 | 3 | 4 | IV-1 | Elmod3 | 84173 | 4-May-15 |
| 17200 | 3 | 4 | IV-1 | Elmsan1 | 91748 | 9-May-15 |
| 17201 | 3 | 4 | IV-1 | Elovl1 | 64834 | 4-May-15 |
| 17202 | 3 | 4 | IV-1 | Elovl5 | 60481 | 21-May-15 |
| 17203 | 3 | 4 | IV-1 | Elp3 | 55140 | 4-May-15 |
| 17204 | 3 | 4 | IV-1 | Elp4 | 26610 | 23-May-15 |
| 17205 | 3 | 4 | IV-1 | Elp5 | 23587 | 4-May-15 |
| 17206 | 3 | 4 | IV-1 | Elp6 | 54859 | 4-May-15 |
| 17207 | 3 | 4 | IV-1 | Emc10 | 284361 | 4-May-15 |
| 17208 | 3 | 4 | IV-1 | Emc2 | 9694 | 12-May-15 |
| 17209 | 3 | 4 | IV-1 | Emc3 | 55831 | 21-May-15 |
| 17210 | 3 | 4 | IV-1 | Emc4 | 51234 | 4-May-15 |
| 17211 | 3 | 4 | IV-1 | Emc6 | 83460 | 21-May-15 |
| 17212 | 3 | 4 | IV-1 | Emc7 | 56851 | 4-May-15 |
| 17213 | 3 | 4 | IV-1 | Emc8 | 10328 | 4-May-15 |
| 17214 | 3 | 4 | IV-1 | Emc9 | 51016 | 4-May-15 |
| 17215 | 3 | 4 | IV-1 | Eml1 | 2009 | 12-May-15 |
| 17216 | 3 | 4 | IV-1 | Eml3 | 256364 | 12-May-15 |
| 17217 | 3 | 4 | IV-1 | Eml4 | 27436 | 17-May-15 |
| 17218 | 3 | 4 | IV-1 | Eml6 | 400954 | 12-May-15 |
| 17219 | 3 | 4 | IV-1 | En2 | 2020 | 4-May-15 |
| 17220 | 3 | 4 | IV-1 | Enah | 55740 | 31-May-15 |
| 17221 | 3 | 4 | IV-1 | Enc1 | 8507 | 4-May-15 |
| 17222 | 3 | 4 | IV-1 | Eng | 2022 | 23-May-15 |
| 17223 | 3 | 4 | IV-1 | Enho | 375704 | 4-May-15 |
| 17224 | 3 | 4 | IV-1 | Enox1 | 55068 | 4-May-15 |
| 17225 | 3 | 4 | IV-1 | Enox2 | 10495 | 17-May-15 |
| 17226 | 3 | 4 | IV-1 | Enpp4 | 22875 | 4-May-15 |
| 17227 | 3 | 4 | IV-1 | Ensa | 2029 | 4-May-15 |
| 17228 | 3 | 4 | IV-1 | Enthd1 | 150350 | 4-May-15 |
| 17229 | 3 | 4 | IV-1 | Enthd2 | 146705 | 4-May-15 |
| 17230 | 3 | 4 | IV-1 | Entpd1 | 953 | 12-May-15 |
| 17231 | 3 | 4 | IV-1 | Entpd5 | 957 | 12-May-15 |
| 17232 | 3 | 4 | IV-1 | Eogt | 285203 | 4-May-15 |
| 17233 | 3 | 4 | IV-1 | Ep400 | 57634 | 4-May-15 |
| 17234 | 3 | 4 | IV-1 | Epas1 | 2034 | 17-May-15 |
| 17235 | 3 | 4 | IV-1 | Epc2 | 26122 | 4-May-15 |
| 17236 | 3 | 4 | IV-1 | Epgn | 255324 | 4-May-15 |
| 17237 | 3 | 4 | IV-1 | Epha1 | 2041 | 12-May-15 |
| 17238 | 3 | 4 | IV-1 | Epha4 | 2043 | 12-May-15 |
| 17239 | 3 | 4 | IV-1 | Epm2a | 7957 | 13-Jun-15 |
| 17240 | 3 | 4 | IV-1 | Epn1 | 29924 | 3-May-15 |
| 17241 | 3 | 4 | IV-1 | Epn2 | 22905 | 3-May-15 |
| 17242 | 3 | 4 | IV-1 | Eps15 | 2060 | 12-May-15 |
| 17243 | 3 | 4 | IV-1 | Eps15l1 | 58513 | 3-May-15 |
| 17244 | 3 | 4 | IV-1 | Eral1 | 26284 | 4-May-15 |
| 17245 | 3 | 4 | IV-1 | Erap1 | 51752 | 21-May-15 |
| 17246 | 3 | 4 | IV-1 | Eras | 3266 | 10-May-15 |
| 17247 | 3 | 4 | IV-1 | Erbb2 | 2064 | 31-May-15 |
| 17248 | 3 | 4 | IV-1 | Ercc1 | 23085 | 12-May-15 |
| 17249 | 3 | 4 | IV-1 | Ercc2 | 26059 | 12-May-15 |
| 17250 | 3 | 4 | IV-1 | Ercc3 | 2071 | 4-Jun-15 |
| 17251 | 3 | 4 | IV-1 | Ercc4 | 2072 | 23-May-15 |
| 17252 | 3 | 4 | IV-1 | Ercc5 | 2073 | 23-May-15 |
| 17253 | 3 | 4 | IV-1 | Ercc6 | 2074 | 23-May-15 |
| 17254 | 3 | 4 | IV-1 | Ercc8 | 1161 | 23-May-15 |
| 17255 | 3 | 4 | IV-1 | Erg | 2078 | 31-May-15 |
| 17256 | 3 | 4 | IV-1 | Ergic2 | 51290 | 4-May-15 |
| 17257 | 3 | 4 | IV-1 | Ergic3 | 51614 | 2-Jun-15 |
| 17258 | 3 | 4 | IV-1 | Erh | 2079 | 4-May-15 |
| 17259 | 3 | 4 | IV-1 | Erich1 | 157697 | 14-May-15 |
| 17260 | 3 | 4 | IV-1 | Erich2 | 285141 | 12-May-15 |
| 17261 | 3 | 4 | IV-1 | Erich6 | 131831 | 12-May-15 |
| 17262 | 3 | 4 | IV-1 | Ermn | 57471 | 14-May-15 |
| 17263 | 3 | 4 | IV-1 | Ermp1 | 79956 | 4-May-15 |
| 17264 | 3 | 4 | IV-1 | Erp44 | 23071 | 4-May-15 |
| 17265 | 3 | 4 | IV-1 | Esam | 90952 | 4-May-15 |
| 17266 | 3 | 4 | IV-1 | Esf1 | 51575 | 4-May-15 |
| 17267 | 3 | 4 | IV-1 | Esp15 | | |
| 17268 | 3 | 4 | IV-1 | Esp16 | | |
| 17269 | 3 | 4 | IV-1 | Esp18 | | |
| 17270 | 3 | 4 | IV-1 | Esp23 | | |
| 17271 | 3 | 4 | IV-1 | Esp24 | | |

Fig. 30 - 92

| | | | | | | | | | | | | | | | |
|---|---|---|---|---|---|---|---|---|---|---|---|---|---|---|---|
| 17272 | 3 | 4 | | | | IV-1 | Esp3 | | | 17366 | 3 | 4 | | IV-1 | Fam19a1 | 407738 | 4-May-15 |
| 17273 | 3 | 4 | | | | IV-1 | Esyt1 | 23344 | 4-May-15 | 17367 | 3 | 4 | | IV-1 | Fam19a2 | 338811 | 21-May-15 |
| 17274 | 3 | 4 | | | | IV-1 | Esyt3 | 83850 | 4-May-15 | 17368 | 3 | 4 | | IV-1 | Fam19a3 | 284467 | 4-May-15 |
| 17275 | 3 | 4 | | | | IV-1 | Etd | | | 17369 | 3 | 4 | | IV-1 | Fam19a4 | 151647 | 4-May-15 |
| 17276 | 3 | 4 | | | | IV-1 | Etf1 | 2107 | 2-Jun-15 | 17370 | 3 | 4 | | IV-1 | Fam203a | 51236 | 4-May-15 |
| 17277 | 3 | 4 | | | | IV-1 | Etfa | 2108 | 21-May-15 | 17371 | 3 | 4 | | IV-1 | Fam208a | 23272 | 4-May-15 |
| 17278 | 3 | 4 | | | | IV-1 | Etnk2 | 55224 | 12-May-15 | 17372 | 3 | 4 | | IV-1 | Fam208b | 54906 | 4-May-15 |
| 17279 | 3 | 4 | | | | IV-1 | Etohi1 | | | 17373 | 3 | 4 | | IV-1 | Fam209 | | |
| 17280 | 3 | 4 | | | | IV-1 | Evx2 | 344191 | 4-May-15 | 17374 | 3 | 4 | | IV-1 | Fam210a | 125228 | 12-May-15 |
| 17281 | 3 | 4 | | | | IV-1 | Ewsr1 | 2130 | 21-May-15 | 17375 | 3 | 4 | | IV-1 | Fam212b | 55924 | 4-May-15 |
| 17282 | 3 | 4 | | | | IV-1 | Exd1 | 161829 | 4-May-15 | 17376 | 3 | 4 | | IV-1 | Fam217b | 63939 | 4-May-15 |
| 17283 | 3 | 4 | | | | IV-1 | Exd2 | 55218 | 4-May-15 | 17377 | 3 | 4 | | IV-1 | Fam220a | 84792 | 4-May-15 |
| 17284 | 3 | 4 | | | | IV-1 | Exoc2 | 55770 | 3-May-15 | 17378 | 3 | 4 | | IV-1 | Fam222a | 84915 | 4-May-15 |
| 17285 | 3 | 4 | | | | IV-1 | Exoc3 | 11336 | 4-May-15 | 17379 | 3 | 4 | | IV-1 | Fam227a | 646851 | 4-May-15 |
| 17286 | 3 | 4 | | | | IV-1 | Exoc3l | 283849 | 4-May-15 | 17380 | 3 | 4 | | IV-1 | Fam227b | 196951 | 4-May-15 |
| 17287 | 3 | 4 | | | | IV-1 | Exoc5 | 10640 | 4-May-15 | 17381 | 3 | 4 | | IV-1 | Fam229b | 619208 | 4-May-15 |
| 17288 | 3 | 4 | | | | IV-1 | Exoc6 | 54536 | 4-May-15 | 17382 | 3 | 4 | | IV-1 | Fam3b | 54097 | 12-May-15 |
| 17289 | 3 | 4 | | | | IV-1 | Exoc6b | 23233 | 4-May-15 | 17383 | 3 | 4 | | IV-1 | Fam45a | 404636 | 4-May-15 |
| 17290 | 3 | 4 | | | | IV-1 | Exoc7 | 23265 | 3-May-15 | 17384 | 3 | 4 | | IV-1 | Fam50b | 26240 | 4-May-15 |
| 17291 | 3 | 4 | | | | IV-1 | Exoc8 | 149371 | 4-May-15 | 17385 | 3 | 4 | | IV-1 | Fam53a | 152877 | 21-May-15 |
| 17292 | 3 | 4 | | | | IV-1 | Exog | 9941 | 3-May-15 | 17386 | 3 | 4 | | IV-1 | Fam53b | 9679 | 4-May-15 |
| 17293 | 3 | 4 | | | | IV-1 | Exosc1 | 51013 | 2-Jun-15 | 17387 | 3 | 4 | | IV-1 | Fam57a | 79850 | 4-May-15 |
| 17294 | 3 | 4 | | | | IV-1 | Exosc10 | 5394 | 12-May-15 | 17388 | 3 | 4 | | IV-1 | Fam60a | 58516 | 12-May-15 |
| 17295 | 3 | 4 | | | | IV-1 | Exosc2 | 23404 | 20-May-15 | 17389 | 3 | 4 | | IV-1 | Fam63b | 54629 | 4-May-15 |
| 17296 | 3 | 4 | | | | IV-1 | Exosc4 | 54512 | 4-May-15 | 17390 | 3 | 4 | | IV-1 | Fam71a | 149647 | 12-May-15 |
| 17297 | 3 | 4 | | | | IV-1 | Exosc5 | 56915 | 4-May-15 | 17391 | 3 | 4 | | IV-1 | Fam71f1 | 84691 | 4-May-15 |
| 17298 | 3 | 4 | | | | IV-1 | Exosc6 | 118460 | 23-May-15 | 17392 | 3 | 4 | | IV-1 | Fam73b | 84895 | 4-May-15 |
| 17299 | 3 | 4 | | | | IV-1 | Exosc8 | 11340 | 4-May-15 | 17393 | 3 | 4 | | IV-1 | Fam76a | 199870 | 4-May-15 |
| 17300 | 3 | 4 | | | | IV-1 | Exosc9 | 5393 | 4-May-15 | 17394 | 3 | 4 | | IV-1 | Fam76b | 143684 | 4-May-15 |
| 17301 | 3 | 4 | | | | IV-1 | Exph5 | 23086 | 12-May-15 | 17395 | 3 | 4 | | IV-1 | Fam83g | 644815 | 4-May-15 |
| 17302 | 3 | 4 | | | | IV-1 | Ext2 | 2132 | 7-Jun-15 | 17396 | 3 | 4 | | IV-1 | Fam92a | | |
| 17303 | 3 | 4 | | | | IV-1 | Extl1 | 2134 | 12-May-15 | 17397 | 3 | 4 | | IV-1 | Fam98a | 25940 | 4-May-15 |
| 17304 | 3 | 4 | | | | IV-1 | Extl3 | 2137 | 4-May-15 | 17398 | 3 | 4 | | IV-1 | Fam98b | 283742 | 4-May-15 |
| 17305 | 3 | 4 | | | | IV-1 | Eya1 | 2138 | 23-May-15 | 17399 | 3 | 4 | | IV-1 | Fam98c | 147965 | 4-May-15 |
| 17306 | 3 | 4 | | | | IV-1 | Eya4 | 2070 | 23-May-15 | 17400 | 3 | 4 | | IV-1 | Fan1 | 22909 | 7-Jun-15 |
| 17307 | 3 | 4 | | | | IV-1 | Ezh1 | 2145 | 13-Jun-15 | 17401 | 3 | 4 | | IV-1 | Fance | 2178 | 23-May-15 |
| 17308 | 3 | 4 | | | | IV-1 | F11r | 50848 | 4-May-15 | 17402 | 3 | 4 | | IV-1 | Fancf | 2188 | 28-May-15 |
| 17309 | 3 | 4 | | | | IV-1 | F12 | 2161 | 31-May-15 | 17403 | 3 | 4 | | IV-1 | Fancg | 2189 | 23-May-15 |
| 17310 | 3 | 4 | | | | IV-1 | F13a1 | 2162 | 23-May-15 | 17404 | 3 | 4 | | IV-1 | Fancm | 57697 | 23-May-15 |
| 17311 | 3 | 4 | | | | IV-1 | F2 | 2147 | 31-May-15 | 17405 | 3 | 4 | | IV-1 | Fars2 | 10667 | 21-May-15 |
| 17312 | 3 | 4 | | | | IV-1 | F2rl3 | 9002 | 17-May-15 | 17406 | 3 | 4 | | IV-1 | Farsb | 10056 | 4-May-15 |
| 17313 | 3 | 4 | | | | IV-1 | F630111L10Rik | | | 17407 | 3 | 4 | | IV-1 | Fastkd5 | 60493 | 4-May-15 |
| 17314 | 3 | 4 | | | | IV-1 | F630206G17Rik | | | 17408 | 3 | 4 | | IV-1 | Fat3 | 120114 | 4-May-15 |
| 17315 | 3 | 4 | | | | IV-1 | F730043M19Rik | | | 17409 | 3 | 4 | | IV-1 | Fat4 | 79633 | 4-May-15 |
| 17316 | 3 | 4 | | | | IV-1 | F8a | 8263 | 4-May-15 | 17410 | 3 | 4 | | IV-1 | Fau | 2197 | 12-May-15 |
| 17317 | 3 | 4 | | | | IV-1 | F930015N05Rik | | | 17411 | 3 | 4 | | IV-1 | Fbrsl1 | 57666 | 4-May-15 |
| 17318 | 3 | 4 | | | | IV-1 | Fa2h | 79152 | 31-May-15 | 17412 | 3 | 4 | | IV-1 | Fbxl12 | 54850 | 20-May-15 |
| 17319 | 3 | 4 | | | | IV-1 | Fabp2 | 2169 | 17-May-15 | 17413 | 3 | 4 | | IV-1 | Fbxl13 | 222235 | 4-May-15 |
| 17320 | 3 | 4 | | | | IV-1 | Fads2 | 9415 | 4-May-15 | 17414 | 3 | 4 | | IV-1 | Fbxl14 | 144699 | 2-Jun-15 |
| 17321 | 3 | 4 | | | | IV-1 | Faf2 | 23197 | 12-May-15 | 17415 | 3 | 4 | | IV-1 | Fbxl15 | 79176 | 4-May-15 |
| 17322 | 3 | 4 | | | | IV-1 | Fah | 2184 | 7-Jun-15 | 17416 | 3 | 4 | | IV-1 | Fbxl16 | 146330 | 4-May-15 |
| 17323 | 3 | 4 | | | | IV-1 | Fam104a | 84923 | 4-May-15 | 17417 | 3 | 4 | | IV-1 | Fbxl18 | 80028 | 4-May-15 |
| 17324 | 3 | 4 | | | | IV-1 | Fam115a | 9747 | 4-May-15 | 17418 | 3 | 4 | | IV-1 | Fbxl19 | 54620 | 4-May-15 |
| 17325 | 3 | 4 | | | | IV-1 | Fam118b | 79607 | 4-May-15 | 17419 | 3 | 4 | | IV-1 | Fbxl21 | 26223 | 4-May-15 |
| 17326 | 3 | 4 | | | | IV-1 | Fam120a | 23196 | 4-May-15 | 17420 | 3 | 4 | | IV-1 | Fbxl4 | 26235 | 4-May-15 |
| 17327 | 3 | 4 | | | | IV-1 | Fam120aos | 158293 | 4-May-15 | 17421 | 3 | 4 | | IV-1 | Fbxl5 | 26234 | 4-May-15 |
| 17328 | 3 | 4 | | | | IV-1 | Fam120b | 84498 | 12-May-15 | 17422 | 3 | 4 | | IV-1 | Fbxl6 | 26233 | 4-May-15 |
| 17329 | 3 | 4 | | | | IV-1 | Fam120c | 54954 | 4-May-15 | 17423 | 3 | 4 | | IV-1 | Fbxo10 | 26267 | 4-May-15 |
| 17330 | 3 | 4 | | | | IV-1 | Fam122a | 116224 | 4-May-15 | 17424 | 3 | 4 | | IV-1 | Fbxo15 | 201456 | 4-May-15 |
| 17331 | 3 | 4 | | | | IV-1 | Fam122b | 159090 | 12-May-15 | 17425 | 3 | 4 | | IV-1 | Fbxo16 | 157574 | 4-May-15 |
| 17332 | 3 | 4 | | | | IV-1 | Fam122c | 159091 | 12-May-15 | 17426 | 3 | 4 | | IV-1 | Fbxo17 | 115290 | 4-May-15 |
| 17333 | 3 | 4 | | | | IV-1 | Fam124a | 220108 | 4-May-15 | 17427 | 3 | 4 | | IV-1 | Fbxo24 | 26261 | 4-May-15 |
| 17334 | 3 | 4 | | | | IV-1 | Fam131c | 348487 | 4-May-15 | 17428 | 3 | 4 | | IV-1 | Fbxo25 | 26260 | 4-May-15 |
| 17335 | 3 | 4 | | | | IV-1 | Fam134a | 79137 | 4-May-15 | 17429 | 3 | 4 | | IV-1 | Fbxo27 | 126433 | 4-May-15 |
| 17336 | 3 | 4 | | | | IV-1 | Fam135a | 57579 | 4-May-15 | 17430 | 3 | 4 | | IV-1 | Fbxo28 | 23219 | 4-May-15 |
| 17337 | 3 | 4 | | | | IV-1 | Fam135b | 51059 | 14-May-15 | 17431 | 3 | 4 | | IV-1 | Fbxo3 | 26273 | 31-May-15 |
| 17338 | 3 | 4 | | | | IV-1 | Fam136a | 84908 | 4-May-15 | 17432 | 3 | 4 | | IV-1 | Fbxo39 | 162517 | 4-May-15 |
| 17339 | 3 | 4 | | | | IV-1 | Fam150a | 389658 | 4-May-15 | 17433 | 3 | 4 | | IV-1 | Fbxo4 | 26272 | 4-May-15 |
| 17340 | 3 | 4 | | | | IV-1 | Fam151b | 167555 | 4-May-15 | 17434 | 3 | 4 | | IV-1 | Fbxo42 | 54455 | 4-May-15 |
| 17341 | 3 | 4 | | | | IV-1 | Fam154a | 158297 | 4-May-15 | 17435 | 3 | 4 | | IV-1 | Fbxo46 | 23403 | 4-May-15 |
| 17342 | 3 | 4 | | | | IV-1 | Fam154b | 283726 | 4-May-15 | 17436 | 3 | 4 | | IV-1 | Fbxo47 | 494188 | 4-May-15 |
| 17343 | 3 | 4 | | | | IV-1 | Fam159a | 348378 | 4-May-15 | 17437 | 3 | 4 | | IV-1 | Fbxo48 | 554251 | 4-May-15 |
| 17344 | 3 | 4 | | | | IV-1 | Fam159b | 100132936 | 4-May-15 | 17438 | 3 | 4 | | IV-1 | Fbxo7 | 25793 | 23-May-15 |
| 17345 | 3 | 4 | | | | IV-1 | Fam160a1 | 729830 | 4-May-15 | 17439 | 3 | 4 | | IV-1 | Fbxo9 | 26268 | 4-May-15 |
| 17346 | 3 | 4 | | | | IV-1 | Fam160b1 | 57700 | 4-May-15 | 17440 | 3 | 4 | | IV-1 | Fbxw13 | | |
| 17347 | 3 | 4 | | | | IV-1 | Fam160b2 | 64760 | 4-May-15 | 17441 | 3 | 4 | | IV-1 | Fbxw14 | | |
| 17348 | 3 | 4 | | | | IV-1 | Fam162b | 221303 | 4-May-15 | 17442 | 3 | 4 | | IV-1 | Fbxw15 | | |
| 17349 | 3 | 4 | | | | IV-1 | Fam166a | 401565 | 4-May-15 | 17443 | 3 | 4 | | IV-1 | Fbxw16 | | |
| 17350 | 3 | 4 | | | | IV-1 | Fam168b | 130074 | 21-May-15 | 17444 | 3 | 4 | | IV-1 | Fbxw17 | | |
| 17351 | 3 | 4 | | | | IV-1 | Fam170b | 170370 | 4-May-15 | 17445 | 3 | 4 | | IV-1 | Fbxw19 | | |
| 17352 | 3 | 4 | | | | IV-1 | Fam171a1 | 221061 | 12-May-15 | 17446 | 3 | 4 | | IV-1 | Fbxw24 | | |
| 17353 | 3 | 4 | | | | IV-1 | Fam173a | 65990 | 21-May-15 | 17447 | 3 | 4 | | IV-1 | Fbxw26 | | |
| 17354 | 3 | 4 | | | | IV-1 | Fam173b | 134145 | 4-May-15 | 17448 | 3 | 4 | | IV-1 | Fbxw28 | | |
| 17355 | 3 | 4 | | | | IV-1 | Fam174a | 345757 | 4-May-15 | 17449 | 3 | 4 | | IV-1 | Fbxw4 | 6468 | 4-May-15 |
| 17356 | 3 | 4 | | | | IV-1 | Fam175b | 23172 | 4-May-15 | 17450 | 3 | 4 | | IV-1 | Fcgbp | 8857 | 4-May-15 |
| 17357 | 3 | 4 | | | | IV-1 | Fam178a | 55719 | 12-May-15 | 17451 | 3 | 4 | | IV-1 | Fchsd1 | 89848 | 4-May-15 |
| 17358 | 3 | 4 | | | | IV-1 | Fam187a | 100528020 | 7-Dec-14 | 17452 | 3 | 4 | | IV-1 | Fdxacb1 | 91893 | 4-May-15 |
| 17359 | 3 | 4 | | | | IV-1 | Fam188b | 84182 | 4-May-15 | 17453 | 3 | 4 | | IV-1 | Fdxr | 2232 | 4-May-15 |
| 17360 | 3 | 4 | | | | IV-1 | Fam189a2 | 9413 | 4-May-15 | 17454 | 3 | 4 | | IV-1 | Fer1l4 | 80307 | 4-May-15 |
| 17361 | 3 | 4 | | | | IV-1 | Fam193a | 8603 | 4-May-15 | 17455 | 3 | 4 | | IV-1 | Fer1l5 | 90342 | 12-May-15 |
| 17362 | 3 | 4 | | | | IV-1 | Fam193b | 54540 | 4-May-15 | 17456 | 3 | 4 | | IV-1 | Ferd3l | 222894 | 4-May-15 |
| 17363 | 3 | 4 | | | | IV-1 | Fam195a | 84331 | 4-May-15 | 17457 | 3 | 4 | | IV-1 | Fez1 | 9638 | 7-Jun-15 |
| 17364 | 3 | 4 | | | | IV-1 | Fam196a | 642938 | 4-May-15 | 17458 | 3 | 4 | | IV-1 | Fez2 | 9637 | 21-May-15 |
| 17365 | 3 | 4 | | | | IV-1 | Fam196b | 100131 | 4-May-15 | 17459 | 3 | 4 | | IV-1 | Fezf1 | 389549 | 4-May-15 |
| | | | | | | | | | | 17460 | 3 | 4 | | IV-1 | Fezf2 | 55079 | 4-May-15 |

Fig. 30 - 93

| | | | | | | | | | | | | | | | | | | |
|---|---|---|---|---|---|---|---|---|---|---|---|---|---|---|---|---|---|---|
| 17461 | 3 | 4 | | | | IV-1 | Fgd6 | 55785 | 4-May-15 | 17555 | 3 | 4 | | | | IV-1 | Gabarap | 11337 | 24-May-15 |
| 17462 | 3 | 4 | | | | IV-1 | Fgf16 | 8823 | 4-May-15 | 17556 | 3 | 4 | | | | IV-1 | Gabarapl1 | 23710 | 21-May-15 |
| 17463 | 3 | 4 | | | | IV-1 | Fgf4 | 2249 | 4-May-15 | 17557 | 3 | 4 | | | | IV-1 | Gabbr1 | 2550 | 7-Jun-15 |
| 17464 | 3 | 4 | | | | IV-1 | Fgf5 | 2250 | 12-May-15 | 17558 | 3 | 4 | | | | IV-1 | Gabbr2 | 9568 | 4-May-15 |
| 17465 | 3 | 4 | | | | IV-1 | Fgf9 | 2254 | 4-May-15 | 17559 | 3 | 4 | | | | IV-1 | Gabpa | 2551 | 12-May-15 |
| 17466 | 3 | 4 | | | | IV-1 | Fgfr1op2 | 26127 | 4-May-15 | 17560 | 3 | 4 | | | | IV-1 | Gabpb1 | 2553 | 7-Jun-15 |
| 17467 | 3 | 4 | | | | IV-1 | Fhadlos1 | | | 17561 | 3 | 4 | | | | IV-1 | Gabra1 | 2554 | 3-May-15 |
| 17468 | 3 | 4 | | | | IV-1 | Fhod1 | 29109 | 4-May-15 | 17562 | 3 | 4 | | | | IV-1 | Gabra2 | 2555 | 4-May-15 |
| 17469 | 3 | 4 | | | | IV-1 | Fhod3 | 80206 | 7-Jun-15 | 17563 | 3 | 4 | | | | IV-1 | Gabra3 | 2556 | 12-May-15 |
| 17470 | 3 | 4 | | | | IV-1 | Ficd | 11153 | 4-May-15 | 17564 | 3 | 4 | | | | IV-1 | Gabra6 | 2559 | 4-May-15 |
| 17471 | 3 | 4 | | | | IV-1 | Fig4 | 9896 | 23-May-15 | 17565 | 3 | 4 | | | | IV-1 | Gabrb3 | 2562 | 4-May-15 |
| 17472 | 3 | 4 | | | | IV-1 | Filip1 | 27145 | 4-May-15 | 17566 | 3 | 4 | | | | IV-1 | Gabrd | 2563 | 4-May-15 |
| 17473 | 3 | 4 | | | | IV-1 | Firre | 286467 | 22-May-15 | 17567 | 3 | 4 | | | | IV-1 | Gabre | 2564 | 12-May-15 |
| 17474 | 3 | 4 | | | | IV-1 | Fkbp1a | 2280 | 12-May-15 | 17568 | 3 | 4 | | | | IV-1 | Gabrg1 | 2565 | 4-May-15 |
| 17475 | 3 | 4 | | | | IV-1 | Fkbp3 | 2287 | 4-May-15 | 17569 | 3 | 4 | | | | IV-1 | Gabrg2 | 2566 | 2-Jun-15 |
| 17476 | 3 | 4 | | | | IV-1 | Fkbp7 | 51661 | 4-May-15 | 17570 | 3 | 4 | | | | IV-1 | Gabrg3 | 2567 | 12-May-15 |
| 17477 | 3 | 4 | | | | IV-1 | Fkbp8 | 23770 | 12-May-15 | 17571 | 3 | 4 | | | | IV-1 | Gabrr1 | 2569 | 4-May-15 |
| 17478 | 3 | 4 | | | | IV-1 | Fkbp9 | 11328 | 4-May-15 | 17572 | 3 | 4 | | | | IV-1 | Gad1 | 2571 | 24-May-15 |
| 17479 | 3 | 4 | | | | IV-1 | Fkbpl | 63943 | 25-May-15 | 17573 | 3 | 4 | | | | IV-1 | Gad2 | 2572 | 24-May-15 |
| 17480 | 3 | 4 | | | | IV-1 | Fkrp | 79147 | 23-May-15 | 17574 | 3 | 4 | | | | IV-1 | Gadl1 | 339896 | 4-May-15 |
| 17481 | 3 | 4 | | | | IV-1 | Fktn | 2218 | 23-May-15 | 17575 | 3 | 4 | | | | IV-1 | Gak | 2580 | 31-May-15 |
| 17482 | 3 | 4 | | | | IV-1 | Flad1 | 80308 | 4-May-15 | 17576 | 3 | 4 | | | | IV-1 | Galm | 130589 | 12-May-15 |
| 17483 | 3 | 4 | | | | IV-1 | Flna | 2316 | 28-May-15 | 17577 | 3 | 4 | | | | IV-1 | Galnt10 | 55568 | 4-May-15 |
| 17484 | 3 | 4 | | | | IV-1 | Flot2 | 2319 | 3-May-15 | 17578 | 3 | 4 | | | | IV-1 | Galnt3 | 2591 | 4-May-15 |
| 17485 | 3 | 4 | | | | IV-1 | Flrt1 | 23769 | 12-May-15 | 17579 | 3 | 4 | | | | IV-1 | Galnt5 | 11227 | 4-May-15 |
| 17486 | 3 | 4 | | | | IV-1 | Flrt2 | 23768 | 4-May-15 | 17580 | 3 | 4 | | | | IV-1 | Galnt6 | 11226 | 4-May-15 |
| 17487 | 3 | 4 | | | | IV-1 | Fmn2 | 56776 | 24-May-15 | 17581 | 3 | 4 | | | | IV-1 | Galntl6 | 442117 | 4-May-15 |
| 17488 | 3 | 4 | | | | IV-1 | Fmo9 | | | 17582 | 3 | 4 | | | | IV-1 | Galr1 | 2587 | 12-May-15 |
| 17489 | 3 | 4 | | | | IV-1 | Fnbp1l | 54874 | 4-May-15 | 17583 | 3 | 4 | | | | IV-1 | Galr2 | 8811 | 4-May-15 |
| 17490 | 3 | 4 | | | | IV-1 | Fnbp4 | 23360 | 21-May-15 | 17584 | 3 | 4 | | | | IV-1 | Galr3 | 8484 | 12-May-15 |
| 17491 | 3 | 4 | | | | IV-1 | Fndc3b | 64778 | 4-May-15 | 17585 | 3 | 4 | | | | IV-1 | Galt | 2592 | 7-Jun-15 |
| 17492 | 3 | 4 | | | | IV-1 | Fndc4 | 64838 | 4-May-15 | 17586 | 3 | 4 | | | | IV-1 | Ganc | 2595 | 12-May-15 |
| 17493 | 3 | 4 | | | | IV-1 | Folh1 | 2346 | 14-May-15 | 17587 | 3 | 4 | | | | IV-1 | Gapdhs | 26330 | 12-May-15 |
| 17494 | 3 | 4 | | | | IV-1 | Foxa3 | 3171 | 28-May-15 | 17588 | 3 | 4 | | | | IV-1 | Gar1 | 54433 | 7-Jun-15 |
| 17495 | 3 | 4 | | | | IV-1 | Foxd2 | 2306 | 28-May-15 | 17589 | 3 | 4 | | | | IV-1 | Garnl3 | 84253 | 14-May-15 |
| 17496 | 3 | 4 | | | | IV-1 | Foxe3 | 2301 | 12-May-15 | 17590 | 3 | 4 | | | | IV-1 | Gars | 2617 | 7-Jun-15 |
| 17497 | 3 | 4 | | | | IV-1 | Foxf1 | 2294 | 28-May-15 | 17591 | 3 | 4 | | | | IV-1 | Gart | 2618 | 4-May-15 |
| 17498 | 3 | 4 | | | | IV-1 | Foxh1 | 8928 | 23-May-15 | 17592 | 3 | 4 | | | | IV-1 | Gast | 2520 | 12-May-15 |
| 17499 | 3 | 4 | | | | IV-1 | Foxi3 | 344167 | 12-May-15 | 17593 | 3 | 4 | | | | IV-1 | Gata6 | 2627 | 24-May-15 |
| 17500 | 3 | 4 | | | | IV-1 | Foxj3 | 22887 | 28-May-15 | 17594 | 3 | 4 | | | | IV-1 | Gatad2a | 54815 | 12-May-15 |
| 17501 | 3 | 4 | | | | IV-1 | Foxk1 | 221937 | 4-May-15 | 17595 | 3 | 4 | | | | IV-1 | Gatc | 283459 | 23-May-15 |
| 17502 | 3 | 4 | | | | IV-1 | Foxk2 | 3607 | 28-May-15 | 17596 | 3 | 4 | | | | IV-1 | Gbas | 2631 | 4-May-15 |
| 17503 | 3 | 4 | | | | IV-1 | Foxl1 | 2300 | 28-May-15 | 17597 | 3 | 4 | | | | IV-1 | Gbgt1 | 26301 | 12-May-15 |
| 17504 | 3 | 4 | | | | IV-1 | Foxl2os | | | 17598 | 3 | 4 | | | | IV-1 | Gcc2 | 9648 | 4-May-15 |
| 17505 | 3 | 4 | | | | IV-1 | Foxn2 | 3344 | 4-May-15 | 17599 | 3 | 4 | | | | IV-1 | Gcg | 2641 | 17-May-15 |
| 17506 | 3 | 4 | | | | IV-1 | Foxn4 | 121643 | 4-May-15 | 17600 | 3 | 4 | | | | IV-1 | Gcm2 | 9247 | 12-May-15 |
| 17507 | 3 | 4 | | | | IV-1 | Foxo6 | 100132074 | 28-May-15 | 17601 | 3 | 4 | | | | IV-1 | Gcnt1l | 10985 | 12-May-15 |
| | | | | | | | | | | 17602 | 3 | 4 | | | | IV-1 | Gcnt4 | 51301 | 4-May-15 |
| 17508 | 3 | 4 | | | | IV-1 | Foxp2 | 93986 | 3-May-15 | 17603 | 3 | 4 | | | | IV-1 | Gcnt7 | 140687 | 4-May-15 |
| 17509 | 3 | 4 | | | | IV-1 | Foxp4 | 116113 | 4-May-15 | 17604 | 3 | 4 | | | | IV-1 | Gde1 | 51573 | 4-May-15 |
| 17510 | 3 | 4 | | | | IV-1 | Foxr2 | 139628 | 28-May-15 | 17605 | 3 | 4 | | | | IV-1 | Gdf3 | 9573 | 4-May-15 |
| 17511 | 3 | 4 | | | | IV-1 | Foxred1 | 55572 | 23-May-15 | 17606 | 3 | 4 | | | | IV-1 | Gdi2 | 2665 | 4-May-15 |
| 17512 | 3 | 4 | | | | IV-1 | Fpr-rs3 | | | 17607 | 3 | 4 | | | | IV-1 | Gdnf | 2668 | 23-May-15 |
| 17513 | 3 | 4 | | | | IV-1 | Fpr-rs4 | | | 17608 | 3 | 4 | | | | IV-1 | Gdpd1 | 284161 | 4-May-15 |
| 17514 | 3 | 4 | | | | IV-1 | Fpr-rs6 | | | 17609 | 3 | 4 | | | | IV-1 | Gdpd5 | 81546 | 4-May-15 |
| 17515 | 3 | 4 | | | | IV-1 | Fra10ac1 | 118924 | 12-May-15 | 17610 | 3 | 4 | | | | IV-1 | Gemin4 | 50628 | 4-May-15 |
| 17516 | 3 | 4 | | | | IV-1 | Fras1 | 80144 | 12-May-15 | 17611 | 3 | 4 | | | | IV-1 | Gemin5 | 25929 | 12-May-15 |
| 17517 | 3 | 4 | | | | IV-1 | Frat1 | 10023 | 4-May-15 | 17612 | 3 | 4 | | | | IV-1 | Gemin8 | 54960 | 4-May-15 |
| 17518 | 3 | 4 | | | | IV-1 | Frat2 | 23401 | 4-May-15 | 17613 | 3 | 4 | | | | IV-1 | Gfy | 100507003 | 4-May-15 |
| 17519 | 3 | 4 | | | | IV-1 | Frg1 | 2483 | 23-May-15 | | | | | | | | | | |
| 17520 | 3 | 4 | | | | IV-1 | Frmd3 | 257019 | 4-May-15 | 17614 | 3 | 4 | | | | IV-1 | Gga1 | 26088 | 21-May-15 |
| 17521 | 3 | 4 | | | | IV-1 | Frmd4a | 55691 | 14-May-15 | 17615 | 3 | 4 | | | | IV-1 | Gga2 | 23062 | 4-May-15 |
| 17522 | 3 | 4 | | | | IV-1 | Frmd7 | 90147 | 23-May-15 | 17616 | 3 | 4 | | | | IV-1 | Gga3 | 23163 | 12-May-15 |
| 17523 | 3 | 4 | | | | IV-1 | Frmd8 | 83786 | 12-May-15 | 17617 | 3 | 4 | | | | IV-1 | Ggact | 87769 | 4-May-15 |
| 17524 | 3 | 4 | | | | IV-1 | Frmpd3 | 84443 | 4-May-15 | 17618 | 3 | 4 | | | | IV-1 | Ggct | 79017 | 4-May-15 |
| 17525 | 3 | 4 | | | | IV-1 | Frs2 | 10818 | 4-May-15 | 17619 | 3 | 4 | | | | IV-1 | Ggnbp1 | 449520 | 4-May-15 |
| 17526 | 3 | 4 | | | | IV-1 | Frs3 | 10817 | 3-May-15 | 17620 | 3 | 4 | | | | IV-1 | Ggps1 | 9453 | 4-May-15 |
| 17527 | 3 | 4 | | | | IV-1 | Fscb | 84075 | 4-May-15 | 17621 | 3 | 4 | | | | IV-1 | Ggt7 | 2686 | 4-May-15 |
| 17528 | 3 | 4 | | | | IV-1 | Fsd1 | 79187 | 4-May-15 | 17622 | 3 | 4 | | | | IV-1 | Ghitm | 27069 | 4-May-15 |
| 17529 | 3 | 4 | | | | IV-1 | Fsd1l | 83856 | 12-May-15 | 17623 | 3 | 4 | | | | IV-1 | Ghr | 2690 | 24-May-15 |
| 17530 | 3 | 4 | | | | IV-1 | Fshr | 2492 | 24-May-15 | 17624 | 3 | 4 | | | | IV-1 | Gid4 | 79018 | 12-May-15 |
| 17531 | 3 | 4 | | | | IV-1 | Fsip1 | 161835 | 4-May-15 | 17625 | 3 | 4 | | | | IV-1 | Gigyf1 | 64599 | 4-May-15 |
| 17532 | 3 | 4 | | | | IV-1 | Fstl5 | 56884 | 4-May-15 | 17626 | 3 | 4 | | | | IV-1 | Gigyf2 | 26058 | 23-May-15 |
| 17533 | 3 | 4 | | | | IV-1 | Fthl17 | 53940 | 4-May-15 | 17627 | 3 | 4 | | | | IV-1 | Git1 | 28964 | 12-May-15 |
| 17534 | 3 | 4 | | | | IV-1 | Fto | 79068 | 4-May-15 | 17628 | 3 | 4 | | | | IV-1 | Git2 | 9815 | 31-May-15 |
| 17535 | 3 | 4 | | | | IV-1 | Ftsj1 | 24140 | 23-May-15 | 17629 | 3 | 4 | | | | IV-1 | Gja3 | 2700 | 4-May-15 |
| 17536 | 3 | 4 | | | | IV-1 | Ftsj3 | 117246 | 4-May-15 | 17630 | 3 | 4 | | | | IV-1 | Gja4 | 2701 | 12-May-15 |
| 17537 | 3 | 4 | | | | IV-1 | Ftx | 100302692 | 22-May-15 | 17631 | 3 | 4 | | | | IV-1 | Gja8 | 2703 | 12-May-15 |
| | | | | | | | | | | 17632 | 3 | 4 | | | | IV-1 | Gjc3 | 349149 | 20-May-15 |
| 17538 | 3 | 4 | | | | IV-1 | Fubp3 | 8939 | 28-May-15 | 17633 | 3 | 4 | | | | IV-1 | Gjd2 | 57369 | 12-May-15 |
| 17539 | 3 | 4 | | | | IV-1 | Fuca1 | 2517 | 21-May-15 | 17634 | 3 | 4 | | | | IV-1 | Gjd4 | 219770 | 4-May-15 |
| 17540 | 3 | 4 | | | | IV-1 | Fuom | 282969 | 12-May-15 | 17635 | 3 | 4 | | | | IV-1 | Gje1 | 100126572 | 4-May-15 |
| 17541 | 3 | 4 | | | | IV-1 | Fus | 2521 | 31-May-15 | | | | | | | | | | |
| 17542 | 3 | 4 | | | | IV-1 | Fut11 | 170384 | 23-May-15 | 17636 | 3 | 4 | | | | IV-1 | Gk2 | 2712 | 12-May-15 |
| 17543 | 3 | 4 | | | | IV-1 | Fut7 | 2529 | 4-May-15 | 17637 | 3 | 4 | | | | IV-1 | Gkap1 | 80318 | 12-May-15 |
| 17544 | 3 | 4 | | | | IV-1 | Fuz | 80199 | 4-May-15 | 17638 | 3 | 4 | | | | IV-1 | Gldnos | | |
| 17545 | 3 | 4 | | | | IV-1 | Fxr2 | 9513 | 12-May-15 | 17639 | 3 | 4 | | | | IV-1 | Gle1 | 2733 | 4-May-15 |
| 17546 | 3 | 4 | | | | IV-1 | G3bp2 | 9908 | 31-May-15 | 17640 | 3 | 4 | | | | IV-1 | Glg1 | 2734 | 4-May-15 |
| 17547 | 3 | 4 | | | | IV-1 | G630055G22Rik | | | 17641 | 3 | 4 | | | | IV-1 | Glipr1l2 | 144321 | 4-May-15 |
| 17548 | 3 | 4 | | | | IV-1 | G630071F17Rik | | | 17642 | 3 | 4 | | | | IV-1 | Glis2 | 84662 | 28-May-15 |
| 17549 | 3 | 4 | | | | IV-1 | G630090E17Rik | | | 17643 | 3 | 4 | | | | IV-1 | Glo1 | 2739 | 17-May-15 |
| 17550 | 3 | 4 | | | | IV-1 | G6b | 80739 | 4-May-15 | 17644 | 3 | 4 | | | | IV-1 | Glod5 | 392465 | 4-May-15 |
| 17551 | 3 | 4 | | | | IV-1 | G6pc | 2538 | 23-May-15 | 17645 | 3 | 4 | | | | IV-1 | Glra1 | 2741 | 23-May-15 |
| 17552 | 3 | 4 | | | | IV-1 | G6pd2 | | | 17646 | 3 | 4 | | | | IV-1 | Glra2 | 2742 | 4-May-15 |
| 17553 | 3 | 4 | | | | IV-1 | Gaa | 2548 | 23-May-15 | 17647 | 3 | 4 | | | | IV-1 | Glra3 | 8001 | 12-May-15 |
| 17554 | 3 | 4 | | | | IV-1 | Gab1 | 2549 | 7-Jun-15 | 17648 | 3 | 4 | | | | IV-1 | Glra4 | 441509 | 4-May-15 |

Fig. 30 - 94

| | | | | | | | | | | | | | | |
|---|---|---|---|---|---|---|---|---|---|---|---|---|---|---|
| 17649 | 3 | 4 | | | IV-1 | Glrx3 | 10539 | 4-May-15 | 17745 | 3 | 4 | | IV-1 | Gm13544 | | |
| 17650 | 3 | 4 | | | IV-1 | Glt8d1 | 55830 | 23-May-15 | 17746 | 3 | 4 | | IV-1 | Gm13546 | | |
| 17651 | 3 | 4 | | | IV-1 | Glt8d2 | 83468 | 23-May-15 | 17747 | 3 | 4 | | IV-1 | Gm136 | | |
| 17652 | 3 | 4 | | | IV-1 | Gltscr1 | 29998 | 21-May-15 | 17748 | 3 | 4 | | IV-1 | Gm13629 | | |
| 17653 | 3 | 4 | | | IV-1 | Gltscr2 | 29997 | 4-May-15 | 17749 | 3 | 4 | | IV-1 | Gm13752 | | |
| 17654 | 3 | 4 | | | IV-1 | Glud1 | 2746 | 7-Jun-15 | 17750 | 3 | 4 | | IV-1 | Gm13826 | | |
| 17655 | 3 | 4 | | | IV-1 | Gm10007 | | | 17751 | 3 | 4 | | IV-1 | Gm14023 | | |
| 17656 | 3 | 4 | | | IV-1 | Gm10046 | | | 17752 | 3 | 4 | | IV-1 | Gm14057 | | |
| 17657 | 3 | 4 | | | IV-1 | Gm10052 | | | 17753 | 3 | 4 | | IV-1 | Gm14124 | | |
| 17658 | 3 | 4 | | | IV-1 | Gm10069 | | | 17754 | 3 | 4 | | IV-1 | Gm14137 | | |
| 17659 | 3 | 4 | | | IV-1 | Gm10094 | | | 17755 | 3 | 4 | | IV-1 | Gm14169 | | |
| 17660 | 3 | 4 | | | IV-1 | Gm10096 | | | 17756 | 3 | 4 | | IV-1 | Gm14325 | | |
| 17661 | 3 | 4 | | | IV-1 | Gm10125 | | | 17757 | 3 | 4 | | IV-1 | Gm14326 | | |
| 17662 | 3 | 4 | | | IV-1 | Gm10324 | | | 17758 | 3 | 4 | | IV-1 | Gm14327 | | |
| 17663 | 3 | 4 | | | IV-1 | Gm10364 | | | 17759 | 3 | 4 | | IV-1 | Gm14345 | | |
| 17664 | 3 | 4 | | | IV-1 | Gm10375 | | | 17760 | 3 | 4 | | IV-1 | Gm14346 | | |
| 17665 | 3 | 4 | | | IV-1 | Gm10390 | | | 17761 | 3 | 4 | | IV-1 | Gm14347 | | |
| 17666 | 3 | 4 | | | IV-1 | Gm10400 | | | 17762 | 3 | 4 | | IV-1 | Gm14351 | | |
| 17667 | 3 | 4 | | | IV-1 | Gm10406 | | | 17763 | 3 | 4 | | IV-1 | Gm14459 | | |
| 17668 | 3 | 4 | | | IV-1 | Gm10409 | | | 17764 | 3 | 4 | | IV-1 | Gm14474 | | |
| 17669 | 3 | 4 | | | IV-1 | Gm10432 | | | 17765 | 3 | 4 | | IV-1 | Gm14475 | | |
| 17670 | 3 | 4 | | | IV-1 | Gm10433 | | | 17766 | 3 | 4 | | IV-1 | Gm14477 | | |
| 17671 | 3 | 4 | | | IV-1 | Gm10436 | | | 17767 | 3 | 4 | | IV-1 | Gm14478 | | |
| 17672 | 3 | 4 | | | IV-1 | Gm10439 | | | 17768 | 3 | 4 | | IV-1 | Gm14482 | | |
| 17673 | 3 | 4 | | | IV-1 | Gm10445 | | | 17769 | 3 | 4 | | IV-1 | Gm14484 | | |
| 17674 | 3 | 4 | | | IV-1 | Gm10474 | | | 17770 | 3 | 4 | | IV-1 | Gm14496 | | |
| 17675 | 3 | 4 | | | IV-1 | Gm10488 | | | 17771 | 3 | 4 | | IV-1 | Gm14499 | | |
| 17676 | 3 | 4 | | | IV-1 | Gm10494 | | | 17772 | 3 | 4 | | IV-1 | Gm14501 | | |
| 17677 | 3 | 4 | | | IV-1 | Gm10510 | | | 17773 | 3 | 4 | | IV-1 | Gm14511 | | |
| 17678 | 3 | 4 | | | IV-1 | Gm10536 | | | 17774 | 3 | 4 | | IV-1 | Gm14635 | | |
| 17679 | 3 | 4 | | | IV-1 | Gm10538 | | | 17775 | 3 | 4 | | IV-1 | Gm14692 | | |
| 17680 | 3 | 4 | | | IV-1 | Gm10548 | | | 17776 | 3 | 4 | | IV-1 | Gm14718 | | |
| 17681 | 3 | 4 | | | IV-1 | Gm10556 | | | 17777 | 3 | 4 | | IV-1 | Gm14725 | | |
| 17682 | 3 | 4 | | | IV-1 | Gm10560 | | | 17778 | 3 | 4 | | IV-1 | Gm14743 | | |
| 17683 | 3 | 4 | | | IV-1 | Gm10637 | | | 17779 | 3 | 4 | | IV-1 | Gm14744 | | |
| 17684 | 3 | 4 | | | IV-1 | Gm10665 | | | 17780 | 3 | 4 | | IV-1 | Gm14850 | | |
| 17685 | 3 | 4 | | | IV-1 | Gm10670 | | | 17781 | 3 | 4 | | IV-1 | Gm14920 | | |
| 17686 | 3 | 4 | | | IV-1 | Gm10677 | | | 17782 | 3 | 4 | | IV-1 | Gm15023 | | |
| 17687 | 3 | 4 | | | IV-1 | Gm10696 | | | 17783 | 3 | 4 | | IV-1 | Gm15055 | | |
| 17688 | 3 | 4 | | | IV-1 | Gm10754 | | | 17784 | 3 | 4 | | IV-1 | Gm15093 | | |
| 17689 | 3 | 4 | | | IV-1 | Gm10785 | | | 17785 | 3 | 4 | | IV-1 | Gm15104 | | |
| 17690 | 3 | 4 | | | IV-1 | Gm10790 | | | 17786 | 3 | 4 | | IV-1 | Gm15107 | | |
| 17691 | 3 | 4 | | | IV-1 | Gm10791 | | | 17787 | 3 | 4 | | IV-1 | Gm15114 | | |
| 17692 | 3 | 4 | | | IV-1 | Gm10804 | | | 17788 | 3 | 4 | | IV-1 | Gm15127 | | |
| 17693 | 3 | 4 | | | IV-1 | Gm10823 | | | 17789 | 3 | 4 | | IV-1 | Gm15133 | | |
| 17694 | 3 | 4 | | | IV-1 | Gm10825 | | | 17790 | 3 | 4 | | IV-1 | Gm15284 | | |
| 17695 | 3 | 4 | | | IV-1 | Gm10863 | | | 17791 | 3 | 4 | | IV-1 | Gm15293 | | |
| 17696 | 3 | 4 | | | IV-1 | Gm11166 | | | 17792 | 3 | 4 | | IV-1 | Gm15299 | | |
| 17697 | 3 | 4 | | | IV-1 | Gm11190 | | | 17793 | 3 | 4 | | IV-1 | Gm15315 | | |
| 17698 | 3 | 4 | | | IV-1 | Gm11201 | | | 17794 | 3 | 4 | | IV-1 | Gm15319 | | |
| 17699 | 3 | 4 | | | IV-1 | Gm11213 | | | 17795 | 3 | 4 | | IV-1 | Gm15348 | | |
| 17700 | 3 | 4 | | | IV-1 | Gm1123 | | | 17796 | 3 | 4 | | IV-1 | Gm15413 | | |
| 17701 | 3 | 4 | | | IV-1 | Gm11237 | | | 17797 | 3 | 4 | | IV-1 | Gm15417 | | |
| 17702 | 3 | 4 | | | IV-1 | Gm11240 | | | 17798 | 3 | 4 | | IV-1 | Gm15455 | | |
| 17703 | 3 | 4 | | | IV-1 | Gm1141 | | | 17799 | 3 | 4 | | IV-1 | Gm15471 | | |
| 17704 | 3 | 4 | | | IV-1 | Gm11517 | | | 17800 | 3 | 4 | | IV-1 | Gm1553 | | |
| 17705 | 3 | 4 | | | IV-1 | Gm11544 | | | 17801 | 3 | 4 | | IV-1 | Gm15545 | | |
| 17706 | 3 | 4 | | | IV-1 | Gm11757 | | | 17802 | 3 | 4 | | IV-1 | Gm15645 | | |
| 17707 | 3 | 4 | | | IV-1 | Gm11762 | | | 17803 | 3 | 4 | | IV-1 | Gm15760 | | |
| 17708 | 3 | 4 | | | IV-1 | Gm11780 | | | 17804 | 3 | 4 | | IV-1 | Gm15772 | | |
| 17709 | 3 | 4 | | | IV-1 | Gm11981 | | | 17805 | 3 | 4 | | IV-1 | Gm15880 | | |
| 17710 | 3 | 4 | | | IV-1 | Gm11985 | | | 17806 | 3 | 4 | | IV-1 | Gm15881 | | |
| 17711 | 3 | 4 | | | IV-1 | Gm12070 | | | 17807 | 3 | 4 | | IV-1 | Gm15910 | | |
| 17712 | 3 | 4 | | | IV-1 | Gm12130 | | | 17808 | 3 | 4 | | IV-1 | Gm16023 | | |
| 17713 | 3 | 4 | | | IV-1 | Gm12159 | | | 17809 | 3 | 4 | | IV-1 | Gm16039 | | |
| 17714 | 3 | 4 | | | IV-1 | Gm12169 | | | 17810 | 3 | 4 | | IV-1 | Gm16130 | | |
| 17715 | 3 | 4 | | | IV-1 | Gm12171 | | | 17811 | 3 | 4 | | IV-1 | Gm16291 | | |
| 17716 | 3 | 4 | | | IV-1 | Gm12338 | | | 17812 | 3 | 4 | | IV-1 | Gm16294 | | |
| 17717 | 3 | 4 | | | IV-1 | Gm12530 | | | 17813 | 3 | 4 | | IV-1 | Gm1631 | | |
| 17718 | 3 | 4 | | | IV-1 | Gm12603 | | | 17814 | 3 | 4 | | IV-1 | Gm16325 | | |
| 17719 | 3 | 4 | | | IV-1 | Gm12657 | | | 17815 | 3 | 4 | | IV-1 | Gm16367 | | |
| 17720 | 3 | 4 | | | IV-1 | Gm12695 | | | 17816 | 3 | 4 | | IV-1 | Gm16430 | | |
| 17721 | 3 | 4 | | | IV-1 | Gm12794 | | | 17817 | 3 | 4 | | IV-1 | Gm16445 | | |
| 17722 | 3 | 4 | | | IV-1 | Gm12886 | | | 17818 | 3 | 4 | | IV-1 | Gm16451 | | |
| 17723 | 3 | 4 | | | IV-1 | Gm12887 | | | 17819 | 3 | 4 | | IV-1 | Gm1647 | | |
| 17724 | 3 | 4 | | | IV-1 | Gm13032 | | | 17820 | 3 | 4 | | IV-1 | Gm16501 | | |
| 17725 | 3 | 4 | | | IV-1 | Gm13034 | | | 17821 | 3 | 4 | | IV-1 | Gm16515 | | |
| 17726 | 3 | 4 | | | IV-1 | Gm13040 | | | 17822 | 3 | 4 | | IV-1 | Gm1653 | | |
| 17727 | 3 | 4 | | | IV-1 | Gm13043 | | | 17823 | 3 | 4 | | IV-1 | Gm16701 | | |
| 17728 | 3 | 4 | | | IV-1 | Gm13051 | | | 17824 | 3 | 4 | | IV-1 | Gm16702 | | |
| 17729 | 3 | 4 | | | IV-1 | Gm13078 | | | 17825 | 3 | 4 | | IV-1 | Gm16712 | | |
| 17730 | 3 | 4 | | | IV-1 | Gm13083 | | | 17826 | 3 | 4 | | IV-1 | Gm16833 | | |
| 17731 | 3 | 4 | | | IV-1 | Gm13084 | | | 17827 | 3 | 4 | | IV-1 | Gm16845 | | |
| 17732 | 3 | 4 | | | IV-1 | Gm13193 | | | 17828 | 3 | 4 | | IV-1 | Gm16863 | | |
| 17733 | 3 | 4 | | | IV-1 | Gm13238 | | | 17829 | 3 | 4 | | IV-1 | Gm16863 | | |
| 17734 | 3 | 4 | | | IV-1 | Gm13242 | | | 17830 | 3 | 4 | | IV-1 | Gm17066 | | |
| 17735 | 3 | 4 | | | IV-1 | Gm13272 | | | 17831 | 3 | 4 | | IV-1 | Gm1720 | | |
| 17736 | 3 | 4 | | | IV-1 | Gm13276 | | | 17832 | 3 | 4 | | IV-1 | Gm17660 | | |
| 17737 | 3 | 4 | | | IV-1 | Gm13277 | | | 17833 | 3 | 4 | | IV-1 | Gm17677 | | |
| 17738 | 3 | 4 | | | IV-1 | Gm13278 | | | 17834 | 3 | 4 | | IV-1 | Gm17689 | | |
| 17739 | 3 | 4 | | | IV-1 | Gm13279 | | | 17835 | 3 | 4 | | IV-1 | Gm17801 | | |
| 17740 | 3 | 4 | | | IV-1 | Gm13483 | | | 17836 | 3 | 4 | | IV-1 | Gm17821 | | |
| 17741 | 3 | 4 | | | IV-1 | Gm13490 | | | 17837 | 3 | 4 | | IV-1 | Gm17830 | | |
| 17742 | 3 | 4 | | | IV-1 | Gm13497 | | | 17838 | 3 | 4 | | IV-1 | Gm18409 | | |
| 17743 | 3 | 4 | | | IV-1 | Gm13498 | | | 17839 | 3 | 4 | | IV-1 | Gm19345 | | |
| 17744 | 3 | 4 | | | IV-1 | Gm13539 | | | 17840 | 3 | 4 | | IV-1 | Gm19510 | | |

Fig. 30 - 95

| | | | | | | | | | | | | | |
|---|---|---|---|---|---|---|---|---|---|---|---|---|---|
| 17841 | 3 | 4 | | | | IV-1 | Gm19619 | 17937 | 3 | 4 | | IV-1 | Gm4884 |
| 17842 | 3 | 4 | | | | IV-1 | Gm19689 | 17938 | 3 | 4 | | IV-1 | Gm4926 |
| 17843 | 3 | 4 | | | | IV-1 | Gm19705 | 17939 | 3 | 4 | | IV-1 | Gm4937 |
| 17844 | 3 | 4 | | | | IV-1 | Gm19784 | 17940 | 3 | 4 | | IV-1 | Gm4975 |
| 17845 | 3 | 4 | | | | IV-1 | Gm1979 | 17941 | 3 | 4 | | IV-1 | Gm4984 |
| 17846 | 3 | 4 | | | | IV-1 | Gm1993 | 17942 | 3 | 4 | | IV-1 | Gm5 |
| 17847 | 3 | 4 | | | | IV-1 | Gm1995 | 17943 | 3 | 4 | | IV-1 | Gm5039 |
| 17848 | 3 | 4 | | | | IV-1 | Gm20063 | 17944 | 3 | 4 | | IV-1 | Gm5071 |
| 17849 | 3 | 4 | | | | IV-1 | Gm20098 | 17945 | 3 | 4 | | IV-1 | Gm5082 |
| 17850 | 3 | 4 | | | | IV-1 | Gm2011 | 17946 | 3 | 4 | | IV-1 | Gm5084 |
| 17851 | 3 | 4 | | | | IV-1 | Gm2012 | 17947 | 3 | 4 | | IV-1 | Gm5086 |
| 17852 | 3 | 4 | | | | IV-1 | Gm20125 | 17948 | 3 | 4 | | IV-1 | Gm5111 |
| 17853 | 3 | 4 | | | | IV-1 | Gm20139 | 17949 | 3 | 4 | | IV-1 | Gm5122 |
| 17854 | 3 | 4 | | | | IV-1 | Gm2016 | 17950 | 3 | 4 | | IV-1 | Gm5128 |
| 17855 | 3 | 4 | | | | IV-1 | Gm20187 | 17951 | 3 | 4 | | IV-1 | Gm5129 |
| 17856 | 3 | 4 | | | | IV-1 | Gm2022 | 17952 | 3 | 4 | | IV-1 | Gm5132 |
| 17857 | 3 | 4 | | | | IV-1 | Gm20356 | 17953 | 3 | 4 | | IV-1 | Gm5134 |
| 17858 | 3 | 4 | | | | IV-1 | Gm20362 | 17954 | 3 | 4 | | IV-1 | Gm5141 |
| 17859 | 3 | 4 | | | | IV-1 | Gm2042 | 17955 | 3 | 4 | | IV-1 | Gm5148 |
| 17860 | 3 | 4 | | | | IV-1 | Gm20594 | 17956 | 3 | 4 | | IV-1 | Gm5168 |
| 17861 | 3 | 4 | | | | IV-1 | Gm20611 | 17957 | 3 | 4 | | IV-1 | Gm5169 |
| 17862 | 3 | 4 | | | | IV-1 | Gm20736 | 17958 | 3 | 4 | | IV-1 | Gm5176 |
| 17863 | 3 | 4 | | | | IV-1 | Gm20738 | 17959 | 3 | 4 | | IV-1 | Gm5294 |
| 17864 | 3 | 4 | | | | IV-1 | Gm20741 | 17960 | 3 | 4 | | IV-1 | Gm5346 |
| 17865 | 3 | 4 | | | | IV-1 | Gm20745 | 17961 | 3 | 4 | | IV-1 | Gm5382 |
| 17866 | 3 | 4 | | | | IV-1 | Gm20747 | 17962 | 3 | 4 | | IV-1 | Gm5415 |
| 17867 | 3 | 4 | | | | IV-1 | Gm20752 | 17963 | 3 | 4 | | IV-1 | Gm5441 |
| 17868 | 3 | 4 | | | | IV-1 | Gm20755 | 17964 | 3 | 4 | | IV-1 | Gm5458 |
| 17869 | 3 | 4 | | | | IV-1 | Gm20756 | 17965 | 3 | 4 | | IV-1 | Gm5460 |
| 17870 | 3 | 4 | | | | IV-1 | Gm20758 | 17966 | 3 | 4 | | IV-1 | Gm5464 |
| 17871 | 3 | 4 | | | | IV-1 | Gm20765 | 17967 | 3 | 4 | | IV-1 | Gm5468 |
| 17872 | 3 | 4 | | | | IV-1 | Gm20816 | 17968 | 3 | 4 | | IV-1 | Gm5475 |
| 17873 | 3 | 4 | | | | IV-1 | Gm20854 | 17969 | 3 | 4 | | IV-1 | Gm5476 |
| 17874 | 3 | 4 | | | | IV-1 | Gm20865 | 17970 | 3 | 4 | | IV-1 | Gm5478 |
| 17875 | 3 | 4 | | | | IV-1 | Gm20867 | 17971 | 3 | 4 | | IV-1 | Gm5538 |
| 17876 | 3 | 4 | | | | IV-1 | Gm2087 | 17972 | 3 | 4 | | IV-1 | Gm5595 |
| 17877 | 3 | 4 | | | | IV-1 | Gm20877 | 17973 | 3 | 4 | | IV-1 | Gm5607 |
| 17878 | 3 | 4 | | | | IV-1 | Gm21002 | 17974 | 3 | 4 | | IV-1 | Gm561 |
| 17879 | 3 | 4 | | | | IV-1 | Gm21057 | 17975 | 3 | 4 | | IV-1 | Gm5617 |
| 17880 | 3 | 4 | | | | IV-1 | Gm21119 | 17976 | 3 | 4 | | IV-1 | Gm5635 |
| 17881 | 3 | 4 | | | | IV-1 | Gm2115 | 17977 | 3 | 4 | | IV-1 | Gm5640 |
| 17882 | 3 | 4 | | | | IV-1 | Gm21269 | 17978 | 3 | 4 | | IV-1 | Gm5643 |
| 17883 | 3 | 4 | | | | IV-1 | Gm21276 | 17979 | 3 | 4 | | IV-1 | Gm5712 |
| 17884 | 3 | 4 | | | | IV-1 | Gm21283 | 17980 | 3 | 4 | | IV-1 | Gm572 |
| 17885 | 3 | 4 | | | | IV-1 | Gm21293 | 17981 | 3 | 4 | | IV-1 | Gm5728 |
| 17886 | 3 | 4 | | | | IV-1 | Gm21304 | 17982 | 3 | 4 | | IV-1 | Gm5800 |
| 17887 | 3 | 4 | | | | IV-1 | Gm21498 | 17983 | 3 | 4 | | IV-1 | Gm5801 |
| 17888 | 3 | 4 | | | | IV-1 | Gm21944 | 17984 | 3 | 4 | | IV-1 | Gm5803 |
| 17889 | 3 | 4 | | | | IV-1 | Gm21949 | 17985 | 3 | 4 | | IV-1 | Gm5860 |
| 17890 | 3 | 4 | | | | IV-1 | Gm2382 | 17986 | 3 | 4 | | IV-1 | Gm5868 |
| 17891 | 3 | 4 | | | | IV-1 | Gm2447 | 17987 | 3 | 4 | | IV-1 | Gm5878 |
| 17892 | 3 | 4 | | | | IV-1 | Gm2516 | 17988 | 3 | 4 | | IV-1 | Gm5885 |
| 17893 | 3 | 4 | | | | IV-1 | Gm2518 | 17989 | 3 | 4 | | IV-1 | Gm5886 |
| 17894 | 3 | 4 | | | | IV-1 | Gm2762 | 17990 | 3 | 4 | | IV-1 | Gm5893 |
| 17895 | 3 | 4 | | | | IV-1 | Gm2799 | 17991 | 3 | 4 | | IV-1 | Gm590 |
| 17896 | 3 | 4 | | | | IV-1 | Gm2927 | 17992 | 3 | 4 | | IV-1 | Gm5901 |
| 17897 | 3 | 4 | | | | IV-1 | Gm3020 | 17993 | 3 | 4 | | IV-1 | Gm5936 |
| 17898 | 3 | 4 | | | | IV-1 | Gm3086 | 17994 | 3 | 4 | | IV-1 | Gm5938 |
| 17899 | 3 | 4 | | | | IV-1 | Gm3143 | 17995 | 3 | 4 | | IV-1 | Gm597 |
| 17900 | 3 | 4 | | | | IV-1 | Gm3259 | 17996 | 3 | 4 | | IV-1 | Gm6026 |
| 17901 | 3 | 4 | | | | IV-1 | Gm3279 | 17997 | 3 | 4 | | IV-1 | Gm6034 |
| 17902 | 3 | 4 | | | | IV-1 | Gm3383 | 17998 | 3 | 4 | | IV-1 | Gm608 |
| 17903 | 3 | 4 | | | | IV-1 | Gm3414 | 17999 | 3 | 4 | | IV-1 | Gm6083 |
| 17904 | 3 | 4 | | | | IV-1 | Gm3415 | 18000 | 3 | 4 | | IV-1 | Gm609 |
| 17905 | 3 | 4 | | | | IV-1 | Gm3417 | 18001 | 3 | 4 | | IV-1 | Gm6116 |
| 17906 | 3 | 4 | | | | IV-1 | Gm3434 | 18002 | 3 | 4 | | IV-1 | Gm6121 |
| 17907 | 3 | 4 | | | | IV-1 | Gm3435 | 18003 | 3 | 4 | | IV-1 | Gm614 |
| 17908 | 3 | 4 | | | | IV-1 | Gm3448 | 18004 | 3 | 4 | | IV-1 | Gm6150 |
| 17909 | 3 | 4 | | | | IV-1 | Gm3500 | 18005 | 3 | 4 | | IV-1 | Gm6164 |
| 17910 | 3 | 4 | | | | IV-1 | Gm364 | 18006 | 3 | 4 | | IV-1 | Gm6249 |
| 17911 | 3 | 4 | | | | IV-1 | Gm3706 | 18007 | 3 | 4 | | IV-1 | Gm6251 |
| 17912 | 3 | 4 | | | | IV-1 | Gm4013 | 18008 | 3 | 4 | | IV-1 | Gm6268 |
| 17913 | 3 | 4 | | | | IV-1 | Gm4027 | 18009 | 3 | 4 | | IV-1 | Gm6277 |
| 17914 | 3 | 4 | | | | IV-1 | Gm4133 | 18010 | 3 | 4 | | IV-1 | Gm6297 |
| 17915 | 3 | 4 | | | | IV-1 | Gm4141 | 18011 | 3 | 4 | | IV-1 | Gm6300 |
| 17916 | 3 | 4 | | | | IV-1 | Gm4175 | 18012 | 3 | 4 | | IV-1 | Gm6329 |
| 17917 | 3 | 4 | | | | IV-1 | Gm4177 | 18013 | 3 | 4 | | IV-1 | Gm6367 |
| 17918 | 3 | 4 | | | | IV-1 | Gm4214 | 18014 | 3 | 4 | | IV-1 | Gm6377 |
| 17919 | 3 | 4 | | | | IV-1 | Gm4216 | 18015 | 3 | 4 | | IV-1 | Gm6406 |
| 17920 | 3 | 4 | | | | IV-1 | Gm4302 | 18016 | 3 | 4 | | IV-1 | Gm6455 |
| 17921 | 3 | 4 | | | | IV-1 | Gm4303 | 18017 | 3 | 4 | | IV-1 | Gm6460 |
| 17922 | 3 | 4 | | | | IV-1 | Gm4349 | 18018 | 3 | 4 | | IV-1 | Gm648 |
| 17923 | 3 | 4 | | | | IV-1 | Gm4432 | 18019 | 3 | 4 | | IV-1 | Gm6525 |
| 17924 | 3 | 4 | | | | IV-1 | Gm4498 | 18020 | 3 | 4 | | IV-1 | Gm6548 |
| 17925 | 3 | 4 | | | | IV-1 | Gm4567 | 18021 | 3 | 4 | | IV-1 | Gm6567 |
| 17926 | 3 | 4 | | | | IV-1 | Gm4598 | 18022 | 3 | 4 | | IV-1 | Gm6568 |
| 17927 | 3 | 4 | | | | IV-1 | Gm4719 | 18023 | 3 | 4 | | IV-1 | Gm6583 |
| 17928 | 3 | 4 | | | | IV-1 | Gm4736 | 18024 | 3 | 4 | | IV-1 | Gm6588 |
| 17929 | 3 | 4 | | | | IV-1 | Gm4794 | 18025 | 3 | 4 | | IV-1 | Gm6592 |
| 17930 | 3 | 4 | | | | IV-1 | Gm4814 | 18026 | 3 | 4 | | IV-1 | Gm6607 |
| 17931 | 3 | 4 | | | | IV-1 | Gm4832 | 18027 | 3 | 4 | | IV-1 | Gm6634 |
| 17932 | 3 | 4 | | | | IV-1 | Gm4836 | 18028 | 3 | 4 | | IV-1 | Gm6710 |
| 17933 | 3 | 4 | | | | IV-1 | Gm4850 | 18029 | 3 | 4 | | IV-1 | Gm6763 |
| 17934 | 3 | 4 | | | | IV-1 | Gm4861 | 18030 | 3 | 4 | | IV-1 | Gm6787 |
| 17935 | 3 | 4 | | | | IV-1 | Gm4871 | 18031 | 3 | 4 | | IV-1 | Gm6815 |
| 17936 | 3 | 4 | | | | IV-1 | Gm4872 | 18032 | 3 | 4 | | IV-1 | Gm684 |

Fig. 30 - 96

| | | | | | | | | | | | | | | | | |
|---|---|---|---|---|---|---|---|---|---|---|---|---|---|---|---|---|
| 18033 | 3 | 4 | | | | IV-1 | Gm6880 | | | 18129 | 3 | 4 | | | IV-1 | Gpbp1 | 65056 | 4-May-15 |
| 18034 | 3 | 4 | | | | IV-1 | Gm6890 | | | 18130 | 3 | 4 | | | IV-1 | Gpbp1l1 | 60313 | 4-May-15 |
| 18035 | 3 | 4 | | | | IV-1 | Gm6902 | | | 18131 | 3 | 4 | | | IV-1 | Gpc1 | 2817 | 3-May-15 |
| 18036 | 3 | 4 | | | | IV-1 | Gm6936 | | | 18132 | 3 | 4 | | | IV-1 | Gphn | 10243 | 23-May-15 |
| 18037 | 3 | 4 | | | | IV-1 | Gm694 | | | 18133 | 3 | 4 | | | IV-1 | Gpi1 | 9091 | 4-May-15 |
| 18038 | 3 | 4 | | | | IV-1 | Gm6981 | | | 18134 | 3 | 4 | | | IV-1 | Gpn2 | 54707 | 4-May-15 |
| 18039 | 3 | 4 | | | | IV-1 | Gm7008 | | | 18135 | 3 | 4 | | | IV-1 | Gpn3 | 51184 | 4-May-15 |
| 18040 | 3 | 4 | | | | IV-1 | Gm7102 | | | 18136 | 3 | 4 | | | IV-1 | Gpr107 | 57720 | 12-May-15 |
| 18041 | 3 | 4 | | | | IV-1 | Gm7157 | | | 18137 | 3 | 4 | | | IV-1 | Gpr108 | 56927 | 4-May-15 |
| 18042 | 3 | 4 | | | | IV-1 | Gm7168 | | | 18138 | 3 | 4 | | | IV-1 | Gpr113 | 165082 | 4-May-15 |
| 18043 | 3 | 4 | | | | IV-1 | Gm7173 | | | 18139 | 3 | 4 | | | IV-1 | Gpr114 | 221188 | 12-May-15 |
| 18044 | 3 | 4 | | | | IV-1 | Gm7271 | | | 18140 | 3 | 4 | | | IV-1 | Gpr116 | 221395 | 4-May-15 |
| 18045 | 3 | 4 | | | | IV-1 | Gm732 | | | 18141 | 3 | 4 | | | IV-1 | Gpr12 | 2835 | 4-May-15 |
| 18046 | 3 | 4 | | | | IV-1 | Gm7457 | | | 18142 | 3 | 4 | | | IV-1 | Gpr123 | 84435 | 12-May-15 |
| 18047 | 3 | 4 | | | | IV-1 | Gm7534 | | | 18143 | 3 | 4 | | | IV-1 | Gpr124 | 25960 | 4-May-15 |
| 18048 | 3 | 4 | | | | IV-1 | Gm7538 | | | 18144 | 3 | 4 | | | IV-1 | Gpr126 | 57211 | 4-May-15 |
| 18049 | 3 | 4 | | | | IV-1 | Gm7550 | | | 18145 | 3 | 4 | | | IV-1 | Gpr128 | 84873 | 21-May-15 |
| 18050 | 3 | 4 | | | | IV-1 | Gm765 | | | 18146 | 3 | 4 | | | IV-1 | Gpr141 | 353345 | 14-May-15 |
| 18051 | 3 | 4 | | | | IV-1 | Gm7861 | | | 18147 | 3 | 4 | | | IV-1 | Gpr143 | 4935 | 23-May-15 |
| 18052 | 3 | 4 | | | | IV-1 | Gm805 | | | 18148 | 3 | 4 | | | IV-1 | Gpr146 | 115330 | 12-May-15 |
| 18053 | 3 | 4 | | | | IV-1 | Gm806 | | | 18149 | 3 | 4 | | | IV-1 | Gpr151 | 134391 | 4-May-15 |
| 18054 | 3 | 4 | | | | IV-1 | Gm8096 | | | 18150 | 3 | 4 | | | IV-1 | Gpr157 | 80045 | 12-May-15 |
| 18055 | 3 | 4 | | | | IV-1 | Gm815 | | | 18151 | 3 | 4 | | | IV-1 | Gpr17 | 2840 | 10-May-15 |
| 18056 | 3 | 4 | | | | IV-1 | Gm8179 | | | 18152 | 3 | 4 | | | IV-1 | Gpr174 | 84636 | 4-May-15 |
| 18057 | 3 | 4 | | | | IV-1 | Gm833 | | | 18153 | 3 | 4 | | | IV-1 | Gpr20 | 2843 | 21-May-15 |
| 18058 | 3 | 4 | | | | IV-1 | Gm8363 | | | 18154 | 3 | 4 | | | IV-1 | Gpr21 | 2844 | 4-May-15 |
| 18059 | 3 | 4 | | | | IV-1 | Gm8693 | | | 18155 | 3 | 4 | | | IV-1 | Gpr26 | 2849 | 7-Jun-15 |
| 18060 | 3 | 4 | | | | IV-1 | Gm8709 | | | 18156 | 3 | 4 | | | IV-1 | Gpr27 | 2850 | 4-May-15 |
| 18061 | 3 | 4 | | | | IV-1 | Gm8720 | | | 18157 | 3 | 4 | | | IV-1 | Gpr3 | 2827 | 4-May-15 |
| 18062 | 3 | 4 | | | | IV-1 | Gm8765 | | | 18158 | 3 | 4 | | | IV-1 | Gpr33 | 2856 | 2-Jun-15 |
| 18063 | 3 | 4 | | | | IV-1 | Gm8773 | | | 18159 | 3 | 4 | | | IV-1 | Gpr45 | 11250 | 4-May-15 |
| 18064 | 3 | 4 | | | | IV-1 | Gm8787 | | | 18160 | 3 | 4 | | | IV-1 | Gpr50 | 9248 | 21-May-15 |
| 18065 | 3 | 4 | | | | IV-1 | Gm8883 | | | 18161 | 3 | 4 | | | IV-1 | Gpr52 | 9293 | 4-May-15 |
| 18066 | 3 | 4 | | | | IV-1 | Gm9 | | | 18162 | 3 | 4 | | | IV-1 | Gpr61 | 83873 | 4-May-15 |
| 18067 | 3 | 4 | | | | IV-1 | Gm904 | | | 18163 | 3 | 4 | | | IV-1 | Gpr62 | 118442 | 12-May-15 |
| 18068 | 3 | 4 | | | | IV-1 | Gm9047 | | | 18164 | 3 | 4 | | | IV-1 | Gpr63 | 81491 | 4-May-15 |
| 18069 | 3 | 4 | | | | IV-1 | Gm9054 | | | 18165 | 3 | 4 | | | IV-1 | Gpr87 | 53836 | 4-May-15 |
| 18070 | 3 | 4 | | | | IV-1 | Gm9079 | | | 18166 | 3 | 4 | | | IV-1 | Gpr88 | 54112 | 4-May-15 |
| 18071 | 3 | 4 | | | | IV-1 | Gm9112 | | | 18167 | 3 | 4 | | | IV-1 | Gprasp1 | 9737 | 4-May-15 |
| 18072 | 3 | 4 | | | | IV-1 | Gm9125 | | | 18168 | 3 | 4 | | | IV-1 | Gprasp2 | 114928 | 4-May-15 |
| 18073 | 3 | 4 | | | | IV-1 | Gm9159 | | | 18169 | 3 | 4 | | | IV-1 | Gprin2 | 9721 | 4-May-15 |
| 18074 | 3 | 4 | | | | IV-1 | Gm9199 | | | 18170 | 3 | 4 | | | IV-1 | Gps2 | 2874 | 4-May-15 |
| 18075 | 3 | 4 | | | | IV-1 | Gm9268 | | | 18171 | 3 | 4 | | | IV-1 | Grid1 | 2894 | 4-May-15 |
| 18076 | 3 | 4 | | | | IV-1 | Gm94 | | | 18172 | 3 | 4 | | | IV-1 | Grid2 | 2895 | 4-May-15 |
| 18077 | 3 | 4 | | | | IV-1 | Gm9573 | | | 18173 | 3 | 4 | | | IV-1 | Grid2ip | 392862 | 4-May-15 |
| 18078 | 3 | 4 | | | | IV-1 | Gm960 | | | 18174 | 3 | 4 | | | IV-1 | Grik2 | 2898 | 7-Jun-15 |
| 18079 | 3 | 4 | | | | IV-1 | Gm973 | | | 18175 | 3 | 4 | | | IV-1 | Grik3 | 2899 | 4-May-15 |
| 18080 | 3 | 4 | | | | IV-1 | Gm9776 | | | 18176 | 3 | 4 | | | IV-1 | Grik4 | 2900 | 4-May-15 |
| 18081 | 3 | 4 | | | | IV-1 | Gm9871 | | | 18177 | 3 | 4 | | | IV-1 | Grin1 | 2902 | 7-Jun-15 |
| 18082 | 3 | 4 | | | | IV-1 | Gm9926 | | | 18178 | 3 | 4 | | | IV-1 | Grin1os | | |
| 18083 | 3 | 4 | | | | IV-1 | Gm9958 | | | 18179 | 3 | 4 | | | IV-1 | Grin2b | 2904 | 17-May-15 |
| 18084 | 3 | 4 | | | | IV-1 | Gm9962 | | | 18180 | 3 | 4 | | | IV-1 | Grin3a | 116443 | 4-May-15 |
| 18085 | 3 | 4 | | | | IV-1 | Gm9992 | | | 18181 | 3 | 4 | | | IV-1 | Grin3b | 116444 | 4-May-15 |
| 18086 | 3 | 4 | | | | IV-1 | Gm9999 | | | 18182 | 3 | 4 | | | IV-1 | Grina | 2907 | 4-May-15 |
| 18087 | 3 | 4 | | | | IV-1 | Gmcl1 | 64395 | 4-May-15 | 18183 | 3 | 4 | | | IV-1 | Grip1os2 | | |
| 18088 | 3 | 4 | | | | IV-1 | Gmeb2 | 26205 | 4-May-15 | 18184 | 3 | 4 | | | IV-1 | Grip2 | 80852 | 4-May-15 |
| 18089 | 3 | 4 | | | | IV-1 | Gmfb | 2764 | 4-May-15 | 18185 | 3 | 4 | | | IV-1 | Grk1 | 6011 | 12-May-15 |
| 18090 | 3 | 4 | | | | IV-1 | Gmnc | 647309 | 4-May-15 | 18186 | 3 | 4 | | | IV-1 | Grk4 | 2868 | 12-May-15 |
| 18091 | 3 | 4 | | | | IV-1 | Gmppb | 29925 | 4-May-15 | 18187 | 3 | 4 | | | IV-1 | Grm3 | 2913 | 4-May-15 |
| 18092 | 3 | 4 | | | | IV-1 | Gmps | 8833 | 4-May-15 | 18188 | 3 | 4 | | | IV-1 | Grm5 | 2915 | 7-Jun-15 |
| 18093 | 3 | 4 | | | | IV-1 | Gna11 | 2767 | 4-May-15 | 18189 | 3 | 4 | | | IV-1 | Grm6 | 2916 | 4-May-15 |
| 18094 | 3 | 4 | | | | IV-1 | Gna13 | 10672 | 17-May-15 | 18190 | 3 | 4 | | | IV-1 | Grpr | 2925 | 17-May-15 |
| 18095 | 3 | 4 | | | | IV-1 | Gnai3 | 2773 | 12-May-15 | 18191 | 3 | 4 | | | IV-1 | Grxcr2 | 643226 | 4-May-15 |
| 18096 | 3 | 4 | | | | IV-1 | Gnas | 2778 | 23-May-15 | 18192 | 3 | 4 | | | IV-1 | Gsc2 | 2928 | 4-May-15 |
| 18097 | 3 | 4 | | | | IV-1 | Gnat1 | 2779 | 21-May-15 | 18193 | 3 | 4 | | | IV-1 | Gsdma | 284110 | 4-May-15 |
| 18098 | 3 | 4 | | | | IV-1 | Gnb1l | 54584 | 4-May-15 | 18194 | 3 | 4 | | | IV-1 | Gsdmc | 56169 | 4-May-15 |
| 18099 | 3 | 4 | | | | IV-1 | Gnb2 | 2783 | 4-May-15 | 18195 | 3 | 4 | | | IV-1 | Gsdmcl1 | | |
| 18100 | 3 | 4 | | | | IV-1 | Gnb2l1 | 10399 | 31-May-15 | 18196 | 3 | 4 | | | IV-1 | Gsdmcl2 | | |
| 18101 | 3 | 4 | | | | IV-1 | Gng13 | 51764 | 4-May-15 | 18197 | 3 | 4 | | | IV-1 | Gsdmcl-ps | | |
| 18102 | 3 | 4 | | | | IV-1 | Gnl2 | 29889 | 4-May-15 | 18198 | 3 | 4 | | | IV-1 | Gsdmd | 79792 | 4-May-15 |
| 18103 | 3 | 4 | | | | IV-1 | Gnpda1 | 10007 | 12-May-15 | 18199 | 3 | 4 | | | IV-1 | Gse1 | 23199 | 21-May-15 |
| 18104 | 3 | 4 | | | | IV-1 | Gnptab | 79158 | 23-May-15 | 18200 | 3 | 4 | | | IV-1 | Gsk3b | 2932 | 31-May-15 |
| 18105 | 3 | 4 | | | | IV-1 | Gns | 2799 | 4-May-15 | 18201 | 3 | 4 | | | IV-1 | Gskip | 51527 | 4-May-15 |
| 18106 | 3 | 4 | | | | IV-1 | Golga1 | 2800 | 4-May-15 | 18202 | 3 | 4 | | | IV-1 | Gstt1 | 2954 | 12-May-15 |
| 18107 | 3 | 4 | | | | IV-1 | Golga2 | 2801 | 4-May-15 | 18203 | 3 | 4 | | | IV-1 | Gsx2 | 170825 | 12-May-15 |
| 18108 | 3 | 4 | | | | IV-1 | Golga3 | 2802 | 4-May-15 | 18204 | 3 | 4 | | | IV-1 | Gt(ROSA)26Sor | | |
| 18109 | 3 | 4 | | | | IV-1 | Golga4 | 2803 | 4-May-15 | 18205 | 3 | 4 | | | IV-1 | Gtdc1 | 79712 | 21-May-15 |
| 18110 | 3 | 4 | | | | IV-1 | Golga5 | 9950 | 7-Jun-15 | 18206 | 3 | 4 | | | IV-1 | Gtf2a1 | 2957 | 4-May-15 |
| 18111 | 3 | 4 | | | | IV-1 | Golga7b | 401647 | 4-May-15 | 18207 | 3 | 4 | | | IV-1 | Gtf2a1l | 11036 | 4-May-15 |
| 18112 | 3 | 4 | | | | IV-1 | Golim4 | 27333 | 12-May-15 | 18208 | 3 | 4 | | | IV-1 | Gtf2a2 | 2958 | 2-Jun-15 |
| 18113 | 3 | 4 | | | | IV-1 | Golm1 | 51280 | 17-May-15 | 18209 | 3 | 4 | | | IV-1 | Gtf2e1 | 2960 | 4-May-15 |
| 18114 | 3 | 4 | | | | IV-1 | Golph3l | 55204 | 4-May-15 | 18210 | 3 | 4 | | | IV-1 | Gtf2e2 | 2961 | 31-May-15 |
| 18115 | 3 | 4 | | | | IV-1 | Gopc | 57120 | 24-May-15 | 18211 | 3 | 4 | | | IV-1 | Gtf2f1 | 2962 | 4-May-15 |
| 18116 | 3 | 4 | | | | IV-1 | Gorab | 92344 | 4-May-15 | 18212 | 3 | 4 | | | IV-1 | Gtf2f2 | 2963 | 4-May-15 |
| 18117 | 3 | 4 | | | | IV-1 | Gorasp1 | 64689 | 4-May-15 | 18213 | 3 | 4 | | | IV-1 | Gtf2h3 | 2967 | 4-May-15 |
| 18118 | 3 | 4 | | | | IV-1 | Gosr1 | 9527 | 4-May-15 | 18214 | 3 | 4 | | | IV-1 | Gtf2h4 | 2968 | 4-May-15 |
| 18119 | 3 | 4 | | | | IV-1 | Gosr2 | 9570 | 4-May-15 | 18215 | 3 | 4 | | | IV-1 | Gtf2i | 2969 | 7-Jun-15 |
| 18120 | 3 | 4 | | | | IV-1 | Gpaa1 | 8733 | 4-May-15 | 18216 | 3 | 4 | | | IV-1 | Gtf2ird1 | 9569 | 28-May-15 |
| 18121 | 3 | 4 | | | | IV-1 | Gpalpp1 | 55425 | 12-May-15 | 18217 | 3 | 4 | | | IV-1 | Gtf3c1 | 2975 | 4-May-15 |
| 18122 | 3 | 4 | | | | IV-1 | Gpat2 | 150763 | 4-May-15 | 18218 | 3 | 4 | | | IV-1 | Gtf3c2 | 2976 | 4-May-15 |
| 18123 | 3 | 4 | | | | IV-1 | Gpatch1 | 55094 | 4-May-15 | 18219 | 3 | 4 | | | IV-1 | Gtf3c3 | 9330 | 4-May-15 |
| 18124 | 3 | 4 | | | | IV-1 | Gpatch2 | 55105 | 4-May-15 | 18220 | 3 | 4 | | | IV-1 | Gtf3c4 | 9329 | 4-May-15 |
| 18125 | 3 | 4 | | | | IV-1 | Gpatch2l | 55668 | 12-May-15 | 18221 | 3 | 4 | | | IV-1 | Gtf3c6 | 112495 | 4-May-15 |
| 18126 | 3 | 4 | | | | IV-1 | Gpatch3 | 63906 | 4-May-15 | 18222 | 3 | 4 | | | IV-1 | Gtl3 | 29105 | 4-May-15 |
| 18127 | 3 | 4 | | | | IV-1 | Gpatch4 | 54865 | 4-May-15 | 18223 | 3 | 4 | | | IV-1 | Gtpbp1 | 9567 | 4-May-15 |
| 18128 | 3 | 4 | | | | IV-1 | Gpbar1 | 151306 | 4-May-15 | 18224 | 3 | 4 | | | IV-1 | Gtpbp10 | 85865 | 4-May-15 |

Fig. 30 - 97

| | | | | | | | | | | | | | | | | | |
|---|---|---|---|---|---|---|---|---|---|---|---|---|---|---|---|---|---|
| 18225 | 3 | 4 | | | | IV-1 | Gtpbp2 | 54676 | 2-Jun-15 | 18321 | 3 | 4 | | | IV-1 | Hmx1 | 3166 | 12-May-15 |
| 18226 | 3 | 4 | | | | IV-1 | Gtpbp3 | 84705 | 4-May-15 | 18322 | 3 | 4 | | | IV-1 | Hmx2 | 3167 | 4-May-15 |
| 18227 | 3 | 4 | | | | IV-1 | Gtpbp4 | 23560 | 4-May-15 | 18323 | 3 | 4 | | | IV-1 | Hmx3 | 340784 | 4-May-15 |
| 18228 | 3 | 4 | | | | IV-1 | Gtpbp8 | 29083 | 4-May-15 | 18324 | 3 | 4 | | | IV-1 | Hn1 | 51155 | 7-Jun-15 |
| 18229 | 3 | 4 | | | | IV-1 | Gtsf1l | 149699 | 4-May-15 | 18325 | 3 | 4 | | | IV-1 | Hnf4g | 3174 | 12-May-15 |
| 18230 | 3 | 4 | | | | IV-1 | Guca1a | 2978 | 31-May-15 | 18326 | 3 | 4 | | | IV-1 | Hnmt | 3176 | 12-May-15 |
| 18231 | 3 | 4 | | | | IV-1 | Gucd1 | 83606 | 4-May-15 | 18327 | 3 | 4 | | | IV-1 | Hnrnpa2b1 | 3181 | 31-May-15 |
| 18232 | 3 | 4 | | | | IV-1 | Gucy1a3 | 2982 | 12-May-15 | 18328 | 3 | 4 | | | IV-1 | Hnrnpa3 | 220988 | 4-May-15 |
| 18233 | 3 | 4 | | | | IV-1 | Gucy1b3 | 2983 | 12-May-15 | 18329 | 3 | 4 | | | IV-1 | Hnrnpc | 3183 | 4-May-15 |
| 18234 | 3 | 4 | | | | IV-1 | Gucy2e | 390226 | 4-May-15 | 18330 | 3 | 4 | | | IV-1 | Hnrnpd | 3184 | 2-Jun-15 |
| 18235 | 3 | 4 | | | | IV-1 | Gucy2f | 2986 | 4-May-15 | 18331 | 3 | 4 | | | IV-1 | Hnrnpdl | 9987 | 4-May-15 |
| 18236 | 3 | 4 | | | | IV-1 | Gucy2g | 390003 | 4-May-15 | 18332 | 3 | 4 | | | IV-1 | Hnrnpf | 3185 | 4-May-15 |
| 18237 | 3 | 4 | | | | IV-1 | Guf1 | 60558 | 4-May-15 | 18333 | 3 | 4 | | | IV-1 | Hnrnph1 | 3187 | 4-May-15 |
| 18238 | 3 | 4 | | | | IV-1 | Guk1 | 2987 | 4-May-15 | 18334 | 3 | 4 | | | IV-1 | Hnrnph2 | 3188 | 4-May-15 |
| 18239 | 3 | 4 | | | | IV-1 | Gulo | 2989 | 12-May-15 | 18335 | 3 | 4 | | | IV-1 | Hnrnph3 | 3189 | 4-May-15 |
| 18240 | 3 | 4 | | | | IV-1 | Gzme | | | 18336 | 3 | 4 | | | IV-1 | Hnrnpl | 3191 | 1-Jun-15 |
| 18241 | 3 | 4 | | | | IV-1 | Gzmf | | | 18337 | 3 | 4 | | | IV-1 | Hnrnpll | 92906 | 12-May-15 |
| 18242 | 3 | 4 | | | | IV-1 | Gzmg | | | 18338 | 3 | 4 | | | IV-1 | Hnrnpm | 4670 | 3-Jun-15 |
| 18243 | 3 | 4 | | | | IV-1 | Gzmk | 3003 | 4-May-15 | 18339 | 3 | 4 | | | IV-1 | Hnrnpr | 10236 | 2-Jun-15 |
| 18244 | 3 | 4 | | | | IV-1 | H1foo | 132243 | 12-May-15 | 18340 | 3 | 4 | | | IV-1 | Hnrnpu | 3192 | 4-May-15 |
| 18245 | 3 | 4 | | | | IV-1 | H2afb2 | 474381 | 4-May-15 | 18341 | 3 | 4 | | | IV-1 | Hnrnpul1 | 11100 | 12-May-15 |
| 18246 | 3 | 4 | | | | IV-1 | H2afb3 | 83740 | 4-May-15 | 18342 | 3 | 4 | | | IV-1 | Hnrnpul2 | 221092 | 12-May-15 |
| 18247 | 3 | 4 | | | | IV-1 | H2afy3 | | | 18343 | 3 | 4 | | | IV-1 | Hoga1 | 112817 | 12-May-15 |
| 18248 | 3 | 4 | | | | IV-1 | H2-Ke6 | 7923 | 4-May-15 | 18344 | 3 | 4 | | | IV-1 | Homer2 | 9455 | 14-May-15 |
| 18249 | 3 | 4 | | | | IV-1 | H2-M10.1 | | | 18345 | 3 | 4 | | | IV-1 | Homez | 57594 | 12-May-15 |
| 18250 | 3 | 4 | | | | IV-1 | H2-M10.5 | | | 18346 | 3 | 4 | | | IV-1 | Hormad2 | 150280 | 4-May-15 |
| 18251 | 3 | 4 | | | | IV-1 | H2-M10.6 | | | 18347 | 3 | 4 | | | IV-1 | Hotair | 100124700 | 31-May-15 |
| 18252 | 3 | 4 | | | | IV-1 | H6pd | 9563 | 13-May-15 | 18348 | 3 | 4 | | | IV-1 | Hottip | 100316868 | 12-May-15 |
| 18253 | 3 | 4 | | | | IV-1 | Hace1 | 57531 | 12-May-15 | 18349 | 3 | 4 | | | IV-1 | Hoxa1 | 3198 | 7-Jun-15 |
| 18254 | 3 | 4 | | | | IV-1 | Hao2 | 51179 | 12-May-15 | 18350 | 3 | 4 | | | IV-1 | Hoxa10 | 3206 | 28-May-15 |
| 18255 | 3 | 4 | | | | IV-1 | Hars | 3035 | 12-May-15 | 18351 | 3 | 4 | | | IV-1 | Hoxa11 | 3207 | 4-May-15 |
| 18256 | 3 | 4 | | | | IV-1 | Has3 | 3038 | 4-May-15 | 18352 | 3 | 4 | | | IV-1 | Hoxa1os | | |
| 18257 | 3 | 4 | | | | IV-1 | Haus2 | 55142 | 4-May-15 | 18353 | 3 | 4 | | | IV-1 | Hoxa13 | 3209 | 23-May-15 |
| 18258 | 3 | 4 | | | | IV-1 | Haus6 | 54801 | 4-May-15 | 18354 | 3 | 4 | | | IV-1 | Hoxa3 | 3200 | 21-May-15 |
| 18259 | 3 | 4 | | | | IV-1 | Haus8 | 93323 | 4-May-15 | 18355 | 3 | 4 | | | IV-1 | Hoxa9 | 3205 | 31-May-15 |
| 18260 | 3 | 4 | | | | IV-1 | Hcfc1r1 | 54385 | 12-May-15 | 18356 | 3 | 4 | | | IV-1 | Hoxb1 | 3211 | 7-Jun-15 |
| 18261 | 3 | 4 | | | | IV-1 | Hcfc2 | 29915 | 4-May-15 | 18357 | 3 | 4 | | | IV-1 | Hoxb13 | 10481 | 31-May-15 |
| 18262 | 3 | 4 | | | | IV-1 | Hcn2 | 610 | 12-May-15 | 18358 | 3 | 4 | | | IV-1 | Hoxb2 | 3212 | 4-May-15 |
| 18263 | 3 | 4 | | | | IV-1 | Hcrtr2 | 3062 | 16-Jun-15 | 18359 | 3 | 4 | | | IV-1 | Hoxc11 | 3227 | 28-May-15 |
| 18264 | 3 | 4 | | | | IV-1 | Hdac3 | 8841 | 31-May-15 | 18360 | 3 | 4 | | | IV-1 | Hoxc12 | 3228 | 4-May-15 |
| 18265 | 3 | 4 | | | | IV-1 | Hdac4 | 9759 | 28-May-15 | 18361 | 3 | 4 | | | IV-1 | Hoxc13 | 3229 | 7-Jun-15 |
| 18266 | 3 | 4 | | | | IV-1 | Hdgf | 3068 | 17-May-15 | 18362 | 3 | 4 | | | IV-1 | Hoxc4 | 3221 | 4-May-15 |
| 18267 | 3 | 4 | | | | IV-1 | Hdgfrp2 | 84717 | 30-May-15 | 18363 | 3 | 4 | | | IV-1 | Hoxc9 | 3225 | 4-May-15 |
| 18268 | 3 | 4 | | | | IV-1 | Hdgfrp3 | 50810 | 4-May-15 | 18364 | 3 | 4 | | | IV-1 | Hoxd1 | 3231 | 12-May-15 |
| 18269 | 3 | 4 | | | | IV-1 | Hdhd1a | 8226 | 28-May-15 | 18365 | 3 | 4 | | | IV-1 | Hoxd12 | 3238 | 4-May-15 |
| 18270 | 3 | 4 | | | | IV-1 | Hdhd2 | 84064 | 12-May-15 | 18366 | 3 | 4 | | | IV-1 | Hoxd13 | 3239 | 4-May-15 |
| 18271 | 3 | 4 | | | | IV-1 | Hdx | 139324 | 4-May-15 | 18367 | 3 | 4 | | | IV-1 | Hps4 | 89781 | 23-May-15 |
| 18272 | 3 | 4 | | | | IV-1 | Heatr1 | 55127 | 21-May-15 | 18368 | 3 | 4 | | | IV-1 | Hps6 | 79803 | 23-May-15 |
| 18273 | 3 | 4 | | | | IV-1 | Heatr3 | 55027 | 4-May-15 | 18369 | 3 | 4 | | | IV-1 | Hrh2 | 3274 | 4-May-15 |
| 18274 | 3 | 4 | | | | IV-1 | Heatr5a | 25938 | 4-May-15 | 18370 | 3 | 4 | | | IV-1 | Hrk | 8739 | 4-May-15 |
| 18275 | 3 | 4 | | | | IV-1 | Heatr5b | 54497 | 12-May-15 | 18371 | 3 | 4 | | | IV-1 | Hrnr | 388697 | 17-May-15 |
| 18276 | 3 | 4 | | | | IV-1 | Heatr6 | 63867 | 4-May-15 | 18372 | 3 | 4 | | | IV-1 | Hs2st1 | 9653 | 4-May-15 |
| 18277 | 3 | 4 | | | | IV-1 | Heatr9 | 256957 | 4-May-15 | 18373 | 3 | 4 | | | IV-1 | Hsbp1l1 | 440498 | 4-May-15 |
| 18278 | 3 | 4 | | | | IV-1 | Hebp1 | 50865 | 4-May-15 | 18374 | 3 | 4 | | | IV-1 | Hsd17b10 | 3028 | 4-May-15 |
| 18279 | 3 | 4 | | | | IV-1 | Hectd1 | 25831 | 12-May-15 | 18375 | 3 | 4 | | | IV-1 | Hsd17b7 | 51478 | 7-Jun-15 |
| 18280 | 3 | 4 | | | | IV-1 | Hectd3 | 79654 | 4-May-15 | 18376 | 3 | 4 | | | IV-1 | Hsdl2 | 84263 | 4-May-15 |
| 18281 | 3 | 4 | | | | IV-1 | Hecw1 | 23072 | 4-May-15 | 18377 | 3 | 4 | | | IV-1 | Hsf2 | 3298 | 12-May-15 |
| 18282 | 3 | 4 | | | | IV-1 | Hecw2 | 57520 | 12-May-15 | 18378 | 3 | 4 | | | IV-1 | Hsf2bp | 11077 | 28-May-15 |
| 18283 | 3 | 4 | | | | IV-1 | Helt | 391723 | 4-May-15 | 18379 | 3 | 4 | | | IV-1 | Hsf3 | | |
| 18284 | 3 | 4 | | | | IV-1 | Helz | 9931 | 23-May-15 | 18380 | 3 | 4 | | | IV-1 | Hsfy2 | 159119 | 4-May-15 |
| 18285 | 3 | 4 | | | | IV-1 | Helz2 | 85441 | 12-May-15 | 18381 | 3 | 4 | | | IV-1 | Hsp90b1 | 7184 | 10-May-15 |
| 18286 | 3 | 4 | | | | IV-1 | Henmt1 | 113802 | 4-May-15 | 18382 | 3 | 4 | | | IV-1 | Hspa4l | 22824 | 4-May-15 |
| 18287 | 3 | 4 | | | | IV-1 | Herc1 | 8925 | 12-May-15 | 18383 | 3 | 4 | | | IV-1 | Hspb2 | 3316 | 4-May-15 |
| 18288 | 3 | 4 | | | | IV-1 | Herc2 | 8924 | 23-May-15 | 18384 | 3 | 4 | | | IV-1 | Hspb1 | 23640 | 4-May-15 |
| 18289 | 3 | 4 | | | | IV-1 | Herc3 | 8916 | 4-May-15 | 18385 | 3 | 4 | | | IV-1 | Hspd1 | 3329 | 17-May-15 |
| 18290 | 3 | 4 | | | | IV-1 | Herc6 | 55008 | 4-May-15 | 18386 | 3 | 4 | | | IV-1 | Htr1a | 3350 | 17-May-15 |
| 18291 | 3 | 4 | | | | IV-1 | Hes5 | 388585 | 4-May-15 | 18387 | 3 | 4 | | | IV-1 | Htr1b | 3351 | 24-May-15 |
| 18292 | 3 | 4 | | | | IV-1 | Hes6 | 55502 | 24-May-15 | 18388 | 3 | 4 | | | IV-1 | Htr1f | 3355 | 4-May-15 |
| 18293 | 3 | 4 | | | | IV-1 | Hesx1 | 8820 | 4-May-15 | 18389 | 3 | 4 | | | IV-1 | Htr2a | 3356 | 7-Jun-15 |
| 18294 | 3 | 4 | | | | IV-1 | Hexa | 3073 | 23-May-15 | 18390 | 3 | 4 | | | IV-1 | Htr3b | 9177 | 12-May-15 |
| 18295 | 3 | 4 | | | | IV-1 | Hexim1 | 10614 | 4-May-15 | 18391 | 3 | 4 | | | IV-1 | Htr4 | 3360 | 21-May-15 |
| 18296 | 3 | 4 | | | | IV-1 | Hexim2 | 124790 | 12-May-15 | 18392 | 3 | 4 | | | IV-1 | Htr5a | 3361 | 12-May-15 |
| 18297 | 3 | 4 | | | | IV-1 | Hey1 | 23462 | 28-May-15 | 18393 | 3 | 4 | | | IV-1 | Htr5b | 645694 | 4-May-15 |
| 18298 | 3 | 4 | | | | IV-1 | Hgd | 3081 | 23-May-15 | 18394 | 3 | 4 | | | IV-1 | Htr7 | 3363 | 4-May-15 |
| 18299 | 3 | 4 | | | | IV-1 | Hhat | 55733 | 4-May-15 | 18395 | 3 | 4 | | | IV-1 | Htra1 | 5654 | 23-May-15 |
| 18300 | 3 | 4 | | | | IV-1 | Hhla1 | 10086 | 4-May-15 | 18396 | 3 | 4 | | | IV-1 | Hus1b | 135458 | 4-May-15 |
| 18301 | 3 | 4 | | | | IV-1 | Hiat1 | 64645 | 12-May-15 | 18397 | 3 | 4 | | | IV-1 | Huwe1 | 10075 | 12-May-15 |
| 18302 | 3 | 4 | | | | IV-1 | Hiatl1 | 84641 | 4-May-15 | 18398 | 3 | 4 | | | IV-1 | Hyal3 | 8372 | 7-Jun-15 |
| 18303 | 3 | 4 | | | | IV-1 | Hibadh | 11112 | 12-May-15 | 18399 | 3 | 4 | | | IV-1 | Hyal5 | 6677 | 12-May-15 |
| 18304 | 3 | 4 | | | | IV-1 | Hid1 | 283987 | 12-May-15 | 18400 | 3 | 4 | | | IV-1 | Hyal6 | 26062 | 12-May-15 |
| 18305 | 3 | 4 | | | | IV-1 | Higd2a | 192286 | 4-May-15 | 18401 | 3 | 4 | | | IV-1 | Hydin | 54768 | 23-May-15 |
| 18306 | 3 | 4 | | | | IV-1 | Hint1 | 3094 | 7-Jun-15 | 18402 | 3 | 4 | | | IV-1 | Hyi | 81888 | 4-May-15 |
| 18307 | 3 | 4 | | | | IV-1 | Hint2 | 84681 | 12-May-15 | 18403 | 3 | 4 | | | IV-1 | I730028E13Rik | | |
| 18308 | 3 | 4 | | | | IV-1 | Hipk3 | 204851 | 4-May-15 | 18404 | 3 | 4 | | | IV-1 | I730030J21Rik | | |
| 18309 | 3 | 4 | | | | IV-1 | Hipk4 | 147746 | 4-May-15 | 18405 | 3 | 4 | | | IV-1 | Ick | 22858 | 4-May-15 |
| 18310 | 3 | 4 | | | | IV-1 | Hira | 7290 | 4-May-15 | 18406 | 3 | 4 | | | IV-1 | Icmt | 23463 | 4-May-15 |
| 18311 | 3 | 4 | | | | IV-1 | Hirip3 | 8479 | 4-May-15 | 18407 | 3 | 4 | | | IV-1 | Icos | 29851 | 17-May-15 |
| 18312 | 3 | 4 | | | | IV-1 | Hist1h1b | 3009 | 4-May-15 | 18408 | 3 | 4 | | | IV-1 | Id1 | 3397 | 31-May-15 |
| 18313 | 3 | 4 | | | | IV-1 | Hist2h2aa | 221613 | 4-May-15 | 18409 | 3 | 4 | | | IV-1 | Idh1 | 3417 | 7-Jun-15 |
| 18314 | 3 | 4 | | | | IV-1 | Hivep2 | 3097 | 12-May-15 | 18410 | 3 | 4 | | | IV-1 | Idnk | 414328 | 4-May-15 |
| 18315 | 3 | 4 | | | | IV-1 | Hlx | 3142 | 4-May-15 | 18411 | 3 | 4 | | | IV-1 | Idua | 3425 | 23-May-15 |
| 18316 | 3 | 4 | | | | IV-1 | Hmg20b | 10362 | 4-May-15 | 18412 | 3 | 4 | | | IV-1 | Ifna11 | | |
| 18317 | 3 | 4 | | | | IV-1 | Hmga1 | 3159 | 12-May-15 | 18413 | 3 | 4 | | | IV-1 | Ifna12 | | |
| 18318 | 3 | 4 | | | | IV-1 | Hmgcl | 3155 | 23-May-15 | 18414 | 3 | 4 | | | IV-1 | Ifna13 | 3447 | 4-May-15 |
| 18319 | 3 | 4 | | | | IV-1 | Hmgcll1 | 54511 | 4-May-15 | | | | | | | | | |
| 18320 | 3 | 4 | | | | IV-1 | Hmgxb4 | 10042 | 4-May-15 | | | | | | | | | |

Fig. 30 - 98

| | | | | | | | | | | | | | | | | |
|---|---|---|---|---|---|---|---|---|---|---|---|---|---|---|---|---|
| 18415 | 3 | 4 | | | | IV-1 | Ifna14 | 3448 | 12-May-15 | 18510 | 3 | 4 | | | IV-1 | Iqcf5 | 389124 | 4-May-15 |
| 18416 | 3 | 4 | | | | IV-1 | Ifna15 | | | 18511 | 3 | 4 | | | IV-1 | Iqcf6 | 440956 | 4-May-15 |
| 18417 | 3 | 4 | | | | IV-1 | Ifna16 | 3449 | 12-May-15 | 18512 | 3 | 4 | | | IV-1 | Iqcj | 654502 | 4-May-15 |
| 18418 | 3 | 4 | | | | IV-1 | Ifnl2 | 282616 | 4-May-15 | 18513 | 3 | 4 | | | IV-1 | Iqck | 124152 | 4-May-15 |
| 18419 | 3 | 4 | | | | IV-1 | Ift20 | 90410 | 29-May-15 | 18514 | 3 | 4 | | | IV-1 | Iqub | 154865 | 4-May-15 |
| 18420 | 3 | 4 | | | | IV-1 | Ift22 | 64792 | 12-May-15 | 18515 | 3 | 4 | | | IV-1 | Irak1 | 3654 | 12-May-15 |
| 18421 | 3 | 4 | | | | IV-1 | Ift27 | 11020 | 4-May-15 | 18516 | 3 | 4 | | | IV-1 | Irf1 | 3659 | 12-May-15 |
| 18422 | 3 | 4 | | | | IV-1 | Ift46 | 56912 | 12-May-15 | 18517 | 3 | 4 | | | IV-1 | Irf2bp1 | 26145 | 4-May-15 |
| 18423 | 3 | 4 | | | | IV-1 | Ift52 | 51098 | 12-May-15 | 18518 | 3 | 4 | | | IV-1 | Irf3 | 3661 | 7-Jun-15 |
| 18424 | 3 | 4 | | | | IV-1 | Ift57 | 55081 | 4-May-15 | 18519 | 3 | 4 | | | IV-1 | Irgm1 | 345611 | 21-May-15 |
| 18425 | 3 | 4 | | | | IV-1 | Ift74 | 80173 | 4-May-15 | 18520 | 3 | 4 | | | IV-1 | Irs1 | 3667 | 17-May-15 |
| 18426 | 3 | 4 | | | | IV-1 | Igbp1 | 3476 | 4-May-15 | 18521 | 3 | 4 | | | IV-1 | Iscu | 23479 | 23-May-15 |
| 18427 | 3 | 4 | | | | IV-1 | Igbp1b | | | 18522 | 3 | 4 | | | IV-1 | Isl1 | 3670 | 4-May-15 |
| 18428 | 3 | 4 | | | | IV-1 | Igdcc3 | 9543 | 4-May-15 | 18523 | 3 | 4 | | | IV-1 | Isoc1 | 51015 | 4-May-15 |
| 18429 | 3 | 4 | | | | IV-1 | Igdcc4 | 57722 | 4-May-15 | 18524 | 3 | 4 | | | IV-1 | Isoc2a | | |
| 18430 | 3 | 4 | | | | IV-1 | Igf2r | 3482 | 21-May-15 | 18525 | 3 | 4 | | | IV-1 | Ist1 | 9798 | 7-Jun-15 |
| 18431 | 3 | 4 | | | | IV-1 | Igfl3 | 388555 | 4-May-15 | 18526 | 3 | 4 | | | IV-1 | Isx | 91464 | 4-May-15 |
| 18432 | 3 | 4 | | | | IV-1 | Igflr1 | 79713 | 4-May-15 | 18527 | 3 | 4 | | | IV-1 | Isy1 | 57461 | 12-May-15 |
| 18433 | 3 | 4 | | | | IV-1 | Igfn1 | 91156 | 4-May-15 | 18528 | 3 | 4 | | | IV-1 | Itfg1 | 81533 | 12-May-15 |
| 18434 | 3 | 4 | | | | IV-1 | Igip | 492311 | 4-May-15 | 18529 | 3 | 4 | | | IV-1 | Itfg2 | 55846 | 4-May-15 |
| 18435 | 3 | 4 | | | | IV-1 | Igsf1 | 3547 | 4-May-15 | 18530 | 3 | 4 | | | IV-1 | Itgai | 3683 | 12-May-15 |
| 18436 | 3 | 4 | | | | IV-1 | Ikbip | 121457 | 4-May-15 | 18531 | 3 | 4 | | | IV-1 | Itih2 | 3698 | 4-May-15 |
| 18437 | 3 | 4 | | | | IV-1 | Ikbkb | 3551 | 31-May-15 | 18532 | 3 | 4 | | | IV-1 | Itpk1 | 3705 | 4-May-15 |
| 18438 | 3 | 4 | | | | IV-1 | Ikbke | 9641 | 12-May-15 | 18533 | 3 | 4 | | | IV-1 | Itpka | 3706 | 4-May-15 |
| 18439 | 3 | 4 | | | | IV-1 | Il10 | 3586 | 31-May-15 | 18534 | 3 | 4 | | | IV-1 | Itpr2 | 3709 | 21-May-15 |
| 18440 | 3 | 4 | | | | IV-1 | Il12rb1 | 3594 | 4-May-15 | 18535 | 3 | 4 | | | IV-1 | Itpr3 | 3710 | 12-May-15 |
| 18441 | 3 | 4 | | | | IV-1 | Il17c | 27189 | 12-May-15 | 18536 | 3 | 4 | | | IV-1 | Ivd | 3712 | 23-May-15 |
| 18442 | 3 | 4 | | | | IV-1 | Il17d | 53342 | 4-May-15 | 18537 | 3 | 4 | | | IV-1 | Izumo2 | 126123 | 4-May-15 |
| 18443 | 3 | 4 | | | | IV-1 | Il17f | 112744 | 4-May-15 | 18538 | 3 | 4 | | | IV-1 | Izumo3 | 100129669 | 4-May-15 |
| 18444 | 3 | 4 | | | | IV-1 | Il17rd | 54756 | 4-May-15 | 18539 | 3 | 4 | | | IV-1 | Jak1 | 3716 | 31-May-15 |
| 18445 | 3 | 4 | | | | IV-1 | Il1a | 3552 | 31-May-15 | 18540 | 3 | 4 | | | IV-1 | Jak2 | 3717 | 7-Jun-15 |
| 18446 | 3 | 4 | | | | IV-1 | Il1f10 | 84639 | 4-May-15 | 18541 | 3 | 4 | | | IV-1 | Jakmip3 | 282973 | 4-May-15 |
| 18447 | 3 | 4 | | | | IV-1 | Il1f5 | 26525 | 7-Jun-15 | 18542 | 3 | 4 | | | IV-1 | Jam2 | 58494 | 7-Jun-15 |
| 18448 | 3 | 4 | | | | IV-1 | Il1rapl2 | 26280 | 12-May-15 | 18543 | 3 | 4 | | | IV-1 | Jam3 | 83700 | 4-May-15 |
| 18449 | 3 | 4 | | | | IV-1 | Il20 | 50604 | 4-May-15 | 18544 | 3 | 4 | | | IV-1 | Jazf1 | 221895 | 4-May-15 |
| 18450 | 3 | 4 | | | | IV-1 | Il20ra | 53832 | 12-May-15 | 18545 | 3 | 4 | | | IV-1 | Jmjd1c | 221037 | 4-May-15 |
| 18451 | 3 | 4 | | | | IV-1 | Il20rb | 53833 | 4-May-15 | 18546 | 3 | 4 | | | IV-1 | Jmjd4 | 65094 | 12-May-15 |
| 18452 | 3 | 4 | | | | IV-1 | Il21r | 50615 | 4-May-15 | 18547 | 3 | 4 | | | IV-1 | Jmjd6 | 23210 | 4-May-15 |
| 18453 | 3 | 4 | | | | IV-1 | Il25 | 64806 | 7-Jun-15 | 18548 | 3 | 4 | | | IV-1 | Jmy | 133746 | 4-May-15 |
| 18454 | 3 | 4 | | | | IV-1 | Il27 | 246778 | 4-May-15 | 18549 | 3 | 4 | | | IV-1 | Josd1 | 9929 | 12-May-15 |
| 18455 | 3 | 4 | | | | IV-1 | Il31ra | 133396 | 7-Jun-15 | 18550 | 3 | 4 | | | IV-1 | Jpx | 554203 | 22-May-15 |
| 18456 | 3 | 4 | | | | IV-1 | Il7 | 3574 | 17-May-15 | 18551 | 3 | 4 | | | IV-1 | Jrk | 8629 | 4-May-15 |
| 18457 | 3 | 4 | | | | IV-1 | Ilf3 | 3609 | 12-May-15 | 18552 | 3 | 4 | | | IV-1 | Jrkl | 8690 | 4-May-15 |
| 18458 | 3 | 4 | | | | IV-1 | Ilk | 3611 | 4-May-15 | 18553 | 3 | 4 | | | IV-1 | Jsrp1 | 126306 | 4-May-15 |
| 18459 | 3 | 4 | | | | IV-1 | Iltifb | | | 18554 | 3 | 4 | | | IV-1 | Jun | 3725 | 31-May-15 |
| 18460 | 3 | 4 | | | | IV-1 | Ilvbl | 10994 | 4-May-15 | 18555 | 3 | 4 | | | IV-1 | Kank1 | 23189 | 12-May-15 |
| 18461 | 3 | 4 | | | | IV-1 | Immp1l | 196294 | 23-May-15 | 18556 | 3 | 4 | | | IV-1 | Kank3 | 256949 | 12-May-15 |
| 18462 | 3 | 4 | | | | IV-1 | Immp2l | 83943 | 23-May-15 | 18557 | 3 | 4 | | | IV-1 | Kansl1 | 284058 | 23-May-15 |
| 18463 | 3 | 4 | | | | IV-1 | Imp4 | 92856 | 7-Jun-15 | 18558 | 3 | 4 | | | IV-1 | Kansl3 | 55683 | 4-May-15 |
| 18464 | 3 | 4 | | | | IV-1 | Impa1 | 3612 | 12-May-15 | 18559 | 3 | 4 | | | IV-1 | Kat2a | 2648 | 17-May-15 |
| 18465 | 3 | 4 | | | | IV-1 | Impg1 | 3617 | 12-May-15 | 18560 | 3 | 4 | | | IV-1 | Kat2b | 8850 | 4-May-15 |
| 18466 | 3 | 4 | | | | IV-1 | Impg2 | 50939 | 23-May-15 | 18561 | 3 | 4 | | | IV-1 | Kat5 | 10524 | 31-May-15 |
| 18467 | 3 | 4 | | | | IV-1 | Ina | 9118 | 17-May-15 | 18562 | 3 | 4 | | | IV-1 | Kat6a | 7994 | 3-Jun-15 |
| 18468 | 3 | 4 | | | | IV-1 | Inadl | 10207 | 4-May-15 | 18563 | 3 | 4 | | | IV-1 | Kat6b | 23522 | 4-May-15 |
| 18469 | 3 | 4 | | | | IV-1 | Ing2 | 3622 | 7-Jun-15 | 18564 | 3 | 4 | | | IV-1 | Kat7 | 11143 | 24-May-15 |
| 18470 | 3 | 4 | | | | IV-1 | Ing3 | 54556 | 4-May-15 | 18565 | 3 | 4 | | | IV-1 | Katnal1 | 84056 | 4-May-15 |
| 18471 | 3 | 4 | | | | IV-1 | Ing4 | 51147 | 2-Jun-15 | 18566 | 3 | 4 | | | IV-1 | Katnb1 | 10300 | 12-May-15 |
| 18472 | 3 | 4 | | | | IV-1 | Ing5 | 84289 | 4-May-15 | 18567 | 3 | 4 | | | IV-1 | Katnbl1 | 79768 | 4-May-15 |
| 18473 | 3 | 4 | | | | IV-1 | Ino80b | 83444 | 4-May-15 | 18568 | 3 | 4 | | | IV-1 | Kbtbd11 | 9920 | 4-May-15 |
| 18474 | 3 | 4 | | | | IV-1 | Ino80c | 125476 | 12-May-15 | 18569 | 3 | 4 | | | IV-1 | Kbtbd3 | 143879 | 4-May-15 |
| 18475 | 3 | 4 | | | | IV-1 | Ino80d | 54891 | 12-May-15 | 18570 | 3 | 4 | | | IV-1 | Kbtbd7 | 84078 | 4-May-15 |
| 18476 | 3 | 4 | | | | IV-1 | Ino80e | 283899 | 12-May-15 | 18571 | 3 | 4 | | | IV-1 | Kbtbd8 | 84541 | 4-May-15 |
| 18477 | 3 | 4 | | | | IV-1 | Inpp1 | 3628 | 12-May-15 | 18572 | 3 | 4 | | | IV-1 | Kcna2 | 3737 | 22-May-15 |
| 18478 | 3 | 4 | | | | IV-1 | Inpp4a | 3631 | 12-May-15 | 18573 | 3 | 4 | | | IV-1 | Kcna7 | 3743 | 4-May-15 |
| 18479 | 3 | 4 | | | | IV-1 | Inpp4b | 8821 | 4-May-15 | 18574 | 3 | 4 | | | IV-1 | Kcnc1 | 3746 | 4-May-15 |
| 18480 | 3 | 4 | | | | IV-1 | Inpp5a | 3632 | 4-May-15 | 18575 | 3 | 4 | | | IV-1 | Kcnc3 | 3748 | 23-May-15 |
| 18481 | 3 | 4 | | | | IV-1 | Inpp5b | 3633 | 16-May-15 | 18576 | 3 | 4 | | | IV-1 | Kcne1l | 23630 | 4-May-15 |
| 18482 | 3 | 4 | | | | IV-1 | Inpp5f | 22876 | 16-Jun-15 | 18577 | 3 | 4 | | | IV-1 | Kcng2 | 26251 | 12-May-15 |
| 18483 | 3 | 4 | | | | IV-1 | Inppl1 | 3636 | 17-May-15 | 18578 | 3 | 4 | | | IV-1 | Kcng3 | 170850 | 4-May-15 |
| 18484 | 3 | 4 | | | | IV-1 | Ins1 | 2305 | 31-May-15 | 18579 | 3 | 4 | | | IV-1 | Kcnh5 | 27133 | 2-Jun-15 |
| 18485 | 3 | 4 | | | | IV-1 | Insm2 | 84684 | 21-May-15 | 18580 | 3 | 4 | | | IV-1 | Kcnh6 | 81033 | 4-May-15 |
| 18486 | 3 | 4 | | | | IV-1 | Insr | 3643 | 17-May-15 | 18581 | 3 | 4 | | | IV-1 | Kcnh7 | 90134 | 4-May-15 |
| 18487 | 3 | 4 | | | | IV-1 | Insrr | 3645 | 4-May-15 | 18582 | 3 | 4 | | | IV-1 | Kcnj1 | 3758 | 4-May-15 |
| 18488 | 3 | 4 | | | | IV-1 | Ints1 | 26173 | 4-May-15 | 18583 | 3 | 4 | | | IV-1 | Kcnj10 | 3766 | 23-May-15 |
| 18489 | 3 | 4 | | | | IV-1 | Ints10 | 55174 | 4-May-15 | 18584 | 3 | 4 | | | IV-1 | Kcnj14 | 3770 | 4-May-15 |
| 18490 | 3 | 4 | | | | IV-1 | Ints2 | 57508 | 4-May-15 | 18585 | 3 | 4 | | | IV-1 | Kcnj8 | 3764 | 4-May-15 |
| 18491 | 3 | 4 | | | | IV-1 | Ints4 | 92105 | 4-May-15 | 18586 | 3 | 4 | | | IV-1 | Kcnk12 | 56660 | 4-May-15 |
| 18492 | 3 | 4 | | | | IV-1 | Ints5 | 80789 | 4-May-15 | 18587 | 3 | 4 | | | IV-1 | Kcnk16 | 83795 | 4-May-15 |
| 18493 | 3 | 4 | | | | IV-1 | Ints6 | 26512 | 12-May-15 | 18588 | 3 | 4 | | | IV-1 | Kcnk18 | 338567 | 4-May-15 |
| 18494 | 3 | 4 | | | | IV-1 | Ints7 | 25896 | 4-May-15 | 18589 | 3 | 4 | | | IV-1 | Kcnk2 | 3776 | 4-May-15 |
| 18495 | 3 | 4 | | | | IV-1 | Ints9 | 55756 | 4-May-15 | 18590 | 3 | 4 | | | IV-1 | Kcnma1 | 3778 | 14-May-15 |
| 18496 | 3 | 4 | | | | IV-1 | Intu | 27152 | 12-May-15 | 18591 | 3 | 4 | | | IV-1 | Kcnmb3 | 27094 | 4-May-15 |
| 18497 | 3 | 4 | | | | IV-1 | Ip6k1 | 9807 | 12-May-15 | 18592 | 3 | 4 | | | IV-1 | Kcnq2 | 3785 | 23-May-15 |
| 18498 | 3 | 4 | | | | IV-1 | Ipo13 | 9670 | 4-May-15 | 18593 | 3 | 4 | | | IV-1 | Kcnq3 | 3786 | 23-May-15 |
| 18499 | 3 | 4 | | | | IV-1 | Ipo5 | 3843 | 12-May-15 | 18594 | 3 | 4 | | | IV-1 | Kcnrg | 283518 | 4-May-15 |
| 18500 | 3 | 4 | | | | IV-1 | Ipo7 | 10527 | 4-May-15 | 18595 | 3 | 4 | | | IV-1 | Kcns3 | 3790 | 12-May-15 |
| 18501 | 3 | 4 | | | | IV-1 | Ipo8 | 10526 | 4-May-15 | 18596 | 3 | 4 | | | IV-1 | Kcnt2 | 343450 | 4-May-15 |
| 18502 | 3 | 4 | | | | IV-1 | Ipo9 | 55705 | 4-May-15 | 18597 | 3 | 4 | | | IV-1 | Kcnv1 | 27012 | 1-Jun-15 |
| 18503 | 3 | 4 | | | | IV-1 | Ipp | 3652 | 4-May-15 | 18598 | 3 | 4 | | | IV-1 | Kctd10 | 83892 | 4-May-15 |
| 18504 | 3 | 4 | | | | IV-1 | Ippk | 64768 | 28-May-15 | 18599 | 3 | 4 | | | IV-1 | Kctd14 | 65987 | 4-May-15 |
| 18505 | 3 | 4 | | | | IV-1 | Ipw | 3653 | 23-May-15 | 18600 | 3 | 4 | | | IV-1 | Kctd17 | 79734 | 27-May-15 |
| 18506 | 3 | 4 | | | | IV-1 | Iqcb1 | 9657 | 4-May-15 | 18601 | 3 | 4 | | | IV-1 | Kctd19 | 146212 | 4-May-15 |
| 18507 | 3 | 4 | | | | IV-1 | Iqcc | 55721 | 4-May-15 | 18602 | 3 | 4 | | | IV-1 | Kctd2 | 23510 | 4-May-15 |
| 18508 | 3 | 4 | | | | IV-1 | Iqcf1 | 132141 | 4-May-15 | 18603 | 3 | 4 | | | IV-1 | Kctd21 | 283219 | 4-May-15 |
| 18509 | 3 | 4 | | | | IV-1 | Iqcf4 | 100506840 | 4-May-15 | 18604 | 3 | 4 | | | IV-1 | Kctd3 | 51133 | 12-May-15 |

Fig. 30 - 99

| | | | | | | | | | | | | | | |
|---|---|---|---|---|---|---|---|---|---|---|---|---|---|---|
| 18605 | 3 | 4 | | | | IV-1 | Kctd4 | 386618 | 4-May-15 | 18701 | 3 | 4 | | | | IV-1 | L2hgdh | 79944 | 4-May-15 |
| 18606 | 3 | 4 | | | | IV-1 | Kctd5 | 54442 | 4-May-15 | 18702 | 3 | 4 | | | | IV-1 | L3mbtl2 | 83746 | 21-May-15 |
| 18607 | 3 | 4 | | | | IV-1 | Kctd6 | 200845 | 2-Jun-15 | 18703 | 3 | 4 | | | | IV-1 | L3mbtl3 | 84456 | 4-May-15 |
| 18608 | 3 | 4 | | | | IV-1 | Kctd7 | 154881 | 4-May-15 | 18704 | 3 | 4 | | | | IV-1 | L3mbtl4 | 91133 | 14-May-15 |
| 18609 | 3 | 4 | | | | IV-1 | Kctd9 | 54793 | 4-May-15 | 18705 | 3 | 4 | | | | IV-1 | l7Rn6 | 51501 | 4-May-15 |
| 18610 | 3 | 4 | | | | IV-1 | Kdelc1 | 79070 | 4-May-15 | 18706 | 3 | 4 | | | | IV-1 | Lacc1 | 144811 | 4-May-15 |
| 18611 | 3 | 4 | | | | IV-1 | Kdelc2 | 143888 | 4-May-15 | 18707 | 3 | 4 | | | | IV-1 | Lactb2 | 51110 | 4-May-15 |
| 18612 | 3 | 4 | | | | IV-1 | Kdelr2 | 11014 | 4-May-15 | 18708 | 3 | 4 | | | | IV-1 | Lamp2 | 3920 | 12-May-15 |
| 18613 | 3 | 4 | | | | IV-1 | Kdm1b | 221656 | 31-May-15 | 18709 | 3 | 4 | | | | IV-1 | Lamtor1 | 55004 | 4-May-15 |
| 18614 | 3 | 4 | | | | IV-1 | Kdm2b | 84678 | 17-May-15 | 18710 | 3 | 4 | | | | IV-1 | Lamtor2 | 28956 | 4-May-15 |
| 18615 | 3 | 4 | | | | IV-1 | Kdm3a | 55818 | 3-May-15 | 18711 | 3 | 4 | | | | IV-1 | Lamtor3 | 8649 | 4-May-15 |
| 18616 | 3 | 4 | | | | IV-1 | Kdm3b | 51780 | 4-May-15 | 18712 | 3 | 4 | | | | IV-1 | Lamtor4 | 389541 | 4-May-15 |
| 18617 | 3 | 4 | | | | IV-1 | Kdm4a | 9682 | 12-May-15 | 18713 | 3 | 4 | | | | IV-1 | Lancl1 | 10314 | 12-May-15 |
| 18618 | 3 | 4 | | | | IV-1 | Kdm4b | 23030 | 24-May-15 | 18714 | 3 | 4 | | | | IV-1 | Lancl2 | 55915 | 12-May-15 |
| 18619 | 3 | 4 | | | | IV-1 | Kdm4c | 23081 | 17-May-15 | 18715 | 3 | 4 | | | | IV-1 | Lap3 | 51056 | 7-Jun-15 |
| 18620 | 3 | 4 | | | | IV-1 | Kdm4d | 55693 | 4-May-15 | 18716 | 3 | 4 | | | | IV-1 | Laptm4a | 9741 | 4-May-15 |
| 18621 | 3 | 4 | | | | IV-1 | Kdm5a | 5927 | 4-May-15 | 18717 | 3 | 4 | | | | IV-1 | Larp1 | 23367 | 4-May-15 |
| 18622 | 3 | 4 | | | | IV-1 | Kdm5b | 10765 | 12-May-15 | 18718 | 3 | 4 | | | | IV-1 | Larp1b | 55132 | 28-May-15 |
| 18623 | 3 | 4 | | | | IV-1 | Kdm5c | 8242 | 23-May-15 | 18719 | 3 | 4 | | | | IV-1 | Larp4b | 23185 | 24-May-15 |
| 18624 | 3 | 4 | | | | IV-1 | Kdm5d | 8284 | 23-May-15 | 18720 | 3 | 4 | | | | IV-1 | Larp6 | 55323 | 4-May-15 |
| 18625 | 3 | 4 | | | | IV-1 | Kdm6a | 7403 | 23-May-15 | 18721 | 3 | 4 | | | | IV-1 | Larp7 | 51574 | 17-May-15 |
| 18626 | 3 | 4 | | | | IV-1 | Kdm6b | 23135 | 4-May-15 | 18722 | 3 | 4 | | | | IV-1 | Lasp1 | 3927 | 7-Jun-15 |
| 18627 | 3 | 4 | | | | IV-1 | Kdm7a | 80853 | 23-May-15 | 18723 | 3 | 4 | | | | IV-1 | Lar | 27040 | 7-Jun-15 |
| 18628 | 3 | 4 | | | | IV-1 | Khdc1a | | | 18724 | 3 | 4 | | | | IV-1 | Lats2 | 26524 | 4-May-15 |
| 18629 | 3 | 4 | | | | IV-1 | Khdc1b | | | 18725 | 3 | 4 | | | | IV-1 | Lax1 | 54900 | 4-May-15 |
| 18630 | 3 | 4 | | | | IV-1 | Khdc1c | | | 18726 | 3 | 4 | | | | IV-1 | Lck | 3932 | 4-May-15 |
| 18631 | 3 | 4 | | | | IV-1 | Khdc3 | | | 18727 | 3 | 4 | | | | IV-1 | Lcmt2 | 9836 | 4-May-15 |
| 18632 | 3 | 4 | | | | IV-1 | Khdrbs1 | 10657 | 31-May-15 | 18728 | 3 | 4 | | | | IV-1 | Lcn4 | | |
| 18633 | 3 | 4 | | | | IV-1 | Khdrbs2 | 202559 | 12-May-15 | 18729 | 3 | 4 | | | | IV-1 | Lcorl | 254251 | 4-May-15 |
| 18634 | 3 | 4 | | | | IV-1 | Khdrbs3 | 10656 | 12-May-15 | 18730 | 3 | 4 | | | | IV-1 | Ldoc1 | 23641 | 21-May-15 |
| 18635 | 3 | 4 | | | | IV-1 | Kidins220 | 57498 | 4-May-15 | 18731 | 3 | 4 | | | | IV-1 | Ldoc1l | 84247 | 4-May-15 |
| 18636 | 3 | 4 | | | | IV-1 | Kif1b | 23095 | 23-May-15 | 18732 | 3 | 4 | | | | IV-1 | Lekr1 | 389170 | 4-May-15 |
| 18637 | 3 | 4 | | | | IV-1 | Kif2b | 84643 | 12-May-15 | 18733 | 3 | 4 | | | | IV-1 | Lelp1 | 149018 | 4-May-15 |
| 18638 | 3 | 4 | | | | IV-1 | Kif3b | 9371 | 4-May-15 | 18734 | 3 | 4 | | | | IV-1 | Lemd1 | 93273 | 4-May-15 |
| 18639 | 3 | 4 | | | | IV-1 | Kif3c | 3797 | 4-May-15 | 18735 | 3 | 4 | | | | IV-1 | Lemd3 | 23592 | 12-May-15 |
| 18640 | 3 | 4 | | | | IV-1 | Kif5a | 3798 | 10-May-15 | 18736 | 3 | 4 | | | | IV-1 | Leng8 | 114823 | 4-May-15 |
| 18641 | 3 | 4 | | | | IV-1 | Kif5b | 3799 | 4-May-15 | 18737 | 3 | 4 | | | | IV-1 | Leng9 | 94059 | 28-May-15 |
| 18642 | 3 | 4 | | | | IV-1 | Kif5c | 3800 | 4-May-15 | 18738 | 3 | 4 | | | | IV-1 | Leprot1 | 23484 | 4-May-15 |
| 18643 | 3 | 4 | | | | IV-1 | Kif6 | 221458 | 4-May-15 | 18739 | 3 | 4 | | | | IV-1 | Letm1 | 3954 | 17-May-15 |
| 18644 | 3 | 4 | | | | IV-1 | Kif7 | 374654 | 23-May-15 | 18740 | 3 | 4 | | | | IV-1 | Lgi2 | 55203 | 12-May-15 |
| 18645 | 3 | 4 | | | | IV-1 | Kir3dl1 | 3811 | 12-May-15 | 18741 | 3 | 4 | | | | IV-1 | Lhfpl5 | 222662 | 23-May-15 |
| 18646 | 3 | 4 | | | | IV-1 | Kir3dl2 | 3812 | 12-May-15 | 18742 | 3 | 4 | | | | IV-1 | Lhx1os | | |
| 18647 | 3 | 4 | | | | IV-1 | Kirrel | 55243 | 4-May-15 | 18743 | 3 | 4 | | | | IV-1 | Lhx4 | 89884 | 4-May-15 |
| 18648 | 3 | 4 | | | | IV-1 | Kis2 | | | 18744 | 3 | 4 | | | | IV-1 | Lhx5 | 64211 | 4-May-15 |
| 18649 | 3 | 4 | | | | IV-1 | Kiss1 | 3814 | 7-Jun-15 | 18745 | 3 | 4 | | | | IV-1 | Lhx6 | 26468 | 4-May-15 |
| 18650 | 3 | 4 | | | | IV-1 | Klc2 | 64837 | 7-Jun-15 | 18746 | 3 | 4 | | | | IV-1 | Lhx9 | 56956 | 12-May-15 |
| 18651 | 3 | 4 | | | | IV-1 | Klf13 | 51621 | 4-May-15 | 18747 | 3 | 4 | | | | IV-1 | Lias | 11019 | 4-May-15 |
| 18652 | 3 | 4 | | | | IV-1 | Klhdc2 | 23588 | 4-May-15 | 18748 | 3 | 4 | | | | IV-1 | Lig4 | 3981 | 4-May-15 |
| 18653 | 3 | 4 | | | | IV-1 | Klhdc3 | 116138 | 12-May-15 | 18749 | 3 | 4 | | | | IV-1 | Lima1 | 51474 | 12-May-15 |
| 18654 | 3 | 4 | | | | IV-1 | Klhdc9 | 126823 | 21-May-15 | 18750 | 3 | 4 | | | | IV-1 | Limd2 | 80774 | 4-May-15 |
| 18655 | 3 | 4 | | | | IV-1 | Klhl1 | 57626 | 4-May-15 | 18751 | 3 | 4 | | | | IV-1 | Limk1 | 3984 | 4-May-15 |
| 18656 | 3 | 4 | | | | IV-1 | Klhl10 | 317719 | 7-Jun-15 | 18752 | 3 | 4 | | | | IV-1 | Limk2 | 3985 | 12-May-15 |
| 18657 | 3 | 4 | | | | IV-1 | Klhl11 | 55175 | 2-Jun-15 | 18753 | 3 | 4 | | | | IV-1 | Lims1 | 3987 | 24-May-15 |
| 18658 | 3 | 4 | | | | IV-1 | Klhl17 | 339451 | 4-May-15 | 18754 | 3 | 4 | | | | IV-1 | Lin28b | 389421 | 4-May-15 |
| 18659 | 3 | 4 | | | | IV-1 | Klhl18 | 23276 | 4-May-15 | 18755 | 3 | 4 | | | | IV-1 | Lin37 | 55957 | 4-May-15 |
| 18660 | 3 | 4 | | | | IV-1 | Klhl21 | 9903 | 4-May-15 | 18756 | 3 | 4 | | | | IV-1 | Lin52 | 91750 | 4-May-15 |
| 18661 | 3 | 4 | | | | IV-1 | Klhl28 | 54813 | 12-May-15 | 18757 | 3 | 4 | | | | IV-1 | Lin54 | 132630 | 1-Jun-15 |
| 18662 | 3 | 4 | | | | IV-1 | Klhl30 | 377007 | 4-May-15 | 18758 | 3 | 4 | | | | IV-1 | Lin9 | 286826 | 4-May-15 |
| 18663 | 3 | 4 | | | | IV-1 | Klhl36 | 79786 | 12-May-15 | 18759 | 3 | 4 | | | | IV-1 | Lipm | 340654 | 4-May-15 |
| 18664 | 3 | 4 | | | | IV-1 | Klhl5 | 51088 | 12-May-15 | 18760 | 3 | 4 | | | | IV-1 | Lkaaear1 | 198437 | 4-May-15 |
| 18665 | 3 | 4 | | | | IV-1 | Klhl9 | 55958 | 4-May-15 | 18761 | 3 | 4 | | | | IV-1 | Llgl1 | 3996 | 4-May-15 |
| 18666 | 3 | 4 | | | | IV-1 | Klk13 | 26085 | 4-May-15 | 18762 | 3 | 4 | | | | IV-1 | Llgl2 | 3993 | 31-May-15 |
| 18667 | 3 | 4 | | | | IV-1 | Klk1b1 | | | 18763 | 3 | 4 | | | | IV-1 | Lman1 | 3998 | 12-May-15 |
| 18668 | 3 | 4 | | | | IV-1 | Klk5 | 25818 | 4-May-15 | 18764 | 3 | 4 | | | | IV-1 | Lmbr1l | 55716 | 4-May-15 |
| 18669 | 3 | 4 | | | | IV-1 | Klk6 | 5653 | 7-Jun-15 | 18765 | 3 | 4 | | | | IV-1 | Lmbrd1 | 55788 | 23-May-15 |
| 18670 | 3 | 4 | | | | IV-1 | Klk8 | 11202 | 4-May-15 | 18766 | 3 | 4 | | | | IV-1 | Lmbrd2 | 92255 | 4-May-15 |
| 18671 | 3 | 4 | | | | IV-1 | Klkb1 | 3818 | 4-May-15 | 18767 | 3 | 4 | | | | IV-1 | Lmf2 | 91289 | 4-May-15 |
| 18672 | 3 | 4 | | | | IV-1 | Klra19 | | | 18768 | 3 | 4 | | | | IV-1 | Lmln | 89782 | 4-May-15 |
| 18673 | 3 | 4 | | | | IV-1 | Klrb1f | | | 18769 | 3 | 4 | | | | IV-1 | Lmo4 | 8543 | 7-Jun-15 |
| 18674 | 3 | 4 | | | | IV-1 | Klrc1 | 3821 | 12-May-15 | 18770 | 3 | 4 | | | | IV-1 | Lmtk3 | 114783 | 4-May-15 |
| 18675 | 3 | 4 | | | | IV-1 | Klri1 | | | 18771 | 3 | 4 | | | | IV-1 | Lmx1a | 4009 | 3-May-15 |
| 18676 | 3 | 4 | | | | IV-1 | Klri2 | | | 18772 | 3 | 4 | | | | IV-1 | Lmx1b | 4010 | 23-May-15 |
| 18677 | 3 | 4 | | | | IV-1 | Kmt2c | 58508 | 4-May-15 | 18773 | 3 | 4 | | | | IV-1 | Lnp | 80856 | 13-Jun-15 |
| 18678 | 3 | 4 | | | | IV-1 | Kmt2d | 8085 | 23-May-15 | 18774 | 3 | 4 | | | | IV-1 | Lnpep | 4012 | 12-May-15 |
| 18679 | 3 | 4 | | | | IV-1 | Kmt2e | 55904 | 4-May-15 | 18775 | 3 | 4 | | | | IV-1 | LOC100043315 | | |
| 18680 | 3 | 4 | | | | IV-1 | Kncn | 148930 | 4-May-15 | 18776 | 3 | 4 | | | | IV-1 | LOC100503280 | | |
| 18681 | 3 | 4 | | | | IV-1 | Kng2 | | | 18777 | 3 | 4 | | | | IV-1 | LOC100862268 | | |
| 18682 | 3 | 4 | | | | IV-1 | Knop1 | 400506 | 4-May-15 | 18778 | 3 | 4 | | | | IV-1 | LOC101055709 | | |
| 18683 | 3 | 4 | | | | IV-1 | Kpna4 | 3840 | 4-May-15 | 18779 | 3 | 4 | | | | IV-1 | LOC101055863 | | |
| 18684 | 3 | 4 | | | | IV-1 | Kpna6 | 23633 | 4-May-15 | 18780 | 3 | 4 | | | | IV-1 | LOC101056043 | | |
| 18685 | 3 | 4 | | | | IV-1 | Kpna7 | 402569 | 7-Jun-15 | 18781 | 3 | 4 | | | | IV-1 | LOC101243624 | | |
| 18686 | 3 | 4 | | | | IV-1 | Kpnb1 | 3837 | 4-May-15 | 18782 | 3 | 4 | | | | IV-1 | LOC101669761 | | |
| 18687 | 3 | 4 | | | | IV-1 | Kras | 3845 | 7-Jun-15 | 18783 | 3 | 4 | | | | IV-1 | LOC102631757 | | |
| 18688 | 3 | 4 | | | | IV-1 | Krba1 | 84626 | 12-May-15 | 18784 | 3 | 4 | | | | IV-1 | LOC102633085 | | |
| 18689 | 3 | 4 | | | | IV-1 | Krcc1 | 51315 | 21-May-15 | 18785 | 3 | 4 | | | | IV-1 | LOC102634401 | | |
| 18690 | 3 | 4 | | | | IV-1 | Kremen1 | 83999 | 21-May-15 | 18786 | 3 | 4 | | | | IV-1 | LOC102634431 | | |
| 18691 | 3 | 4 | | | | IV-1 | Kremen2 | 79412 | 4-May-15 | 18787 | 3 | 4 | | | | IV-1 | LOC102634753 | | |
| 18692 | 3 | 4 | | | | IV-1 | Kri1 | 65095 | 4-May-15 | 18788 | 3 | 4 | | | | IV-1 | LOC102635087 | | |
| 18693 | 3 | 4 | | | | IV-1 | Krit1 | 889 | 31-May-15 | 18789 | 3 | 4 | | | | IV-1 | LOC171588 | | |
| 18694 | 3 | 4 | | | | IV-1 | Krr1 | 11103 | 4-May-15 | 18790 | 3 | 4 | | | | IV-1 | LOC381967 | | |
| 18695 | 3 | 4 | | | | IV-1 | Krt1 | 3848 | 24-May-15 | 18791 | 3 | 4 | | | | IV-1 | Loh12cr1 | 118426 | 4-May-15 |
| 18696 | 3 | 4 | | | | IV-1 | Krt10 | 3858 | 4-May-15 | 18792 | 3 | 4 | | | | IV-1 | Lonp1 | 9361 | 23-May-15 |
| 18697 | 3 | 4 | | | | IV-1 | Krt20 | 54474 | 4-May-15 | 18793 | 3 | 4 | | | | IV-1 | Lonp2 | 83752 | 23-May-15 |
| 18698 | 3 | 4 | | | | IV-1 | Krt75 | 9119 | 4-May-15 | 18794 | 3 | 4 | | | | IV-1 | Lpar3 | 23566 | 4-May-15 |
| 18699 | 3 | 4 | | | | IV-1 | Krtcap2 | 200185 | 4-May-15 | 18795 | 3 | 4 | | | | IV-1 | Lpar5 | 57121 | 4-May-15 |
| 18700 | 3 | 4 | | | | IV-1 | Kxd1 | 79036 | 4-May-15 | 18796 | 3 | 4 | | | | IV-1 | Lpcat3 | 10162 | 12-May-15 |

Fig. 30 - 100

| | | | | | | | | | | | | | | | | |
|---|---|---|---|---|---|---|---|---|---|---|---|---|---|---|---|---|
| 18797 | 3 | 4 | | | | IV-1 | Lphn1 | 22859 | 4-May-15 | 18890 | 3 | 4 | | | IV-1 | Man2c1os | | |
| 18798 | 3 | 4 | | | | IV-1 | Lrch1 | 23143 | 4-May-15 | 18891 | 3 | 4 | | | IV-1 | Manba | 4126 | 4-May-15 |
| 18799 | 3 | 4 | | | | IV-1 | Lrch2 | 57631 | 4-May-15 | 18892 | 3 | 4 | | | IV-1 | Manba1 | 63905 | 4-May-15 |
| 18800 | 3 | 4 | | | | IV-1 | Lrch3 | 84859 | 4-May-15 | 18893 | 3 | 4 | | | IV-1 | Manea | 79694 | 4-May-15 |
| 18801 | 3 | 4 | | | | IV-1 | Lrch4 | 4034 | 4-May-15 | 18894 | 3 | 4 | | | IV-1 | Manea1 | 149175 | 4-May-15 |
| 18802 | 3 | 4 | | | | IV-1 | Lrfn2 | 57497 | 4-May-15 | 18895 | 3 | 4 | | | IV-1 | Mansc1 | 54682 | 4-May-15 |
| 18803 | 3 | 4 | | | | IV-1 | Lrfn5 | 145581 | 4-May-15 | 18896 | 3 | 4 | | | IV-1 | Maoa | 4128 | 31-May-15 |
| 18804 | 3 | 4 | | | | IV-1 | Lrif1 | 55791 | 4-May-15 | 18897 | 3 | 4 | | | IV-1 | Map1s | 55201 | 21-May-15 |
| 18805 | 3 | 4 | | | | IV-1 | Lrit3 | 345193 | 7-Jun-15 | 18898 | 3 | 4 | | | IV-1 | Map2 | 4133 | 7-Jun-15 |
| 18806 | 3 | 4 | | | | IV-1 | Lrp11 | 84918 | 29-May-15 | 18899 | 3 | 4 | | | IV-1 | Map2k1 | 5604 | 28-May-15 |
| 18807 | 3 | 4 | | | | IV-1 | Lrp6 | 4040 | 4-May-15 | 18900 | 3 | 4 | | | IV-1 | Map2k3 | 5606 | 4-May-15 |
| 18808 | 3 | 4 | | | | IV-1 | Lrppre | 10128 | 7-Jun-15 | 18901 | 3 | 4 | | | IV-1 | Map2k5 | 5607 | 3-May-15 |
| 18809 | 3 | 4 | | | | IV-1 | Lrrc2 | 79442 | 4-May-15 | 18902 | 3 | 4 | | | IV-1 | Map3k1 | 4214 | 4-May-15 |
| 18810 | 3 | 4 | | | | IV-1 | Lrrc28 | 123355 | 4-May-15 | 18903 | 3 | 4 | | | IV-1 | Map3k11 | 4296 | 4-May-15 |
| 18811 | 3 | 4 | | | | IV-1 | Lrrc29 | 26231 | 4-May-15 | 18904 | 3 | 4 | | | IV-1 | Map3k12 | 7786 | 28-May-15 |
| 18812 | 3 | 4 | | | | IV-1 | Lrrc40 | 55631 | 4-May-15 | 18905 | 3 | 4 | | | IV-1 | Map3k13 | 9175 | 12-May-15 |
| 18813 | 3 | 4 | | | | IV-1 | Lrrc41 | 10489 | 12-May-15 | 18906 | 3 | 4 | | | IV-1 | Map3k3 | 4215 | 24-May-15 |
| 18814 | 3 | 4 | | | | IV-1 | Lrrc42 | 115353 | 4-May-15 | 18907 | 3 | 4 | | | IV-1 | Map3k4 | 4216 | 4-May-15 |
| 18815 | 3 | 4 | | | | IV-1 | Lrrc43 | 254050 | 4-May-15 | 18908 | 3 | 4 | | | IV-1 | Map3k5 | 4217 | 7-Jun-15 |
| 18816 | 3 | 4 | | | | IV-1 | Lrrc45 | 201255 | 4-May-15 | 18909 | 3 | 4 | | | IV-1 | Map7 | 9053 | 4-May-15 |
| 18817 | 3 | 4 | | | | IV-1 | Lrrc57 | 255252 | 4-May-15 | 18910 | 3 | 4 | | | IV-1 | Mapk3 | 5595 | 7-Jun-15 |
| 18818 | 3 | 4 | | | | IV-1 | Lrrc61 | 65999 | 4-May-15 | 18911 | 3 | 4 | | | IV-1 | Mapk8ip1 | 9479 | 4-May-15 |
| 18819 | 3 | 4 | | | | IV-1 | Lrrc66 | 339977 | 4-May-15 | 18912 | 3 | 4 | | | IV-1 | Mapk8ip3 | 23162 | 4-May-15 |
| 18820 | 3 | 4 | | | | IV-1 | Lrrc7 | 57554 | 14-May-15 | 18913 | 3 | 4 | | | IV-1 | Mapk9 | 5601 | 4-May-15 |
| 18821 | 3 | 4 | | | | IV-1 | Lrrc73 | 221424 | 2-Jun-15 | 18914 | 3 | 4 | | | IV-1 | Mapkapk2 | 9261 | 3-May-15 |
| 18822 | 3 | 4 | | | | IV-1 | Lrrc75a | 388341 | 4-May-15 | 18915 | 3 | 4 | | | IV-1 | Mapkapk3 | 7867 | 4-May-15 |
| 18823 | 3 | 4 | | | | IV-1 | Lrrfip1 | 9208 | 4-May-15 | 18916 | 3 | 4 | | | IV-1 | Mapkbp1 | 23005 | 4-May-15 |
| 18824 | 3 | 4 | | | | IV-1 | Lrriq1 | 84125 | 4-May-15 | 18917 | 3 | 4 | | | IV-1 | Mapre2 | 10982 | 12-May-15 |
| 18825 | 3 | 4 | | | | IV-1 | Lrriq3 | 127255 | 4-May-15 | 18918 | 3 | 4 | | | IV-1 | March11 | 441061 | 4-May-15 |
| 18826 | 3 | 4 | | | | IV-1 | Lrriq4 | 344657 | 4-May-15 | 18919 | 3 | 4 | | | IV-1 | March5 | 54708 | 31-May-15 |
| 18827 | 3 | 4 | | | | IV-1 | Lrrk1 | 79705 | 4-May-15 | 18920 | 3 | 4 | | | IV-1 | March7 | 64844 | 23-May-15 |
| 18828 | 3 | 4 | | | | IV-1 | Lrrtm2 | 26045 | 2-Jun-15 | 18921 | 3 | 4 | | | IV-1 | Mark1 | 4139 | 4-May-15 |
| 18829 | 3 | 4 | | | | IV-1 | Lrrtm3 | 347731 | 1-Jun-15 | 18922 | 3 | 4 | | | IV-1 | Mark3 | 4140 | 4-May-15 |
| 18830 | 3 | 4 | | | | IV-1 | Lrrtm4 | 80059 | 4-May-15 | 18923 | 3 | 4 | | | IV-1 | Mark4 | 57787 | 4-May-15 |
| 18831 | 3 | 4 | | | | IV-1 | Lrsam1 | 90678 | 7-Jun-15 | 18924 | 3 | 4 | | | IV-1 | Mars | 4141 | 7-Jun-15 |
| 18832 | 3 | 4 | | | | IV-1 | Lsamp | 4045 | 21-May-15 | 18925 | 3 | 4 | | | IV-1 | Mars2 | 92935 | 4-May-15 |
| 18833 | 3 | 4 | | | | IV-1 | Lsg1 | 55341 | 23-May-15 | 18926 | 3 | 4 | | | IV-1 | Mast2 | 23139 | 4-May-15 |
| 18834 | 3 | 4 | | | | IV-1 | Lsm1 | 27257 | 4-May-15 | 18927 | 3 | 4 | | | IV-1 | Mast3 | 23031 | 4-May-15 |
| 18835 | 3 | 4 | | | | IV-1 | Lsm10 | 84967 | 4-May-15 | 18928 | 3 | 4 | | | IV-1 | Matk | 4145 | 12-May-15 |
| 18836 | 3 | 4 | | | | IV-1 | Lsm11 | 134353 | 4-May-15 | 18929 | 3 | 4 | | | IV-1 | Matn2 | 4147 | 14-May-15 |
| 18837 | 3 | 4 | | | | IV-1 | Lsm12 | 124801 | 21-May-15 | 18930 | 3 | 4 | | | IV-1 | Mau2 | 23383 | 4-May-15 |
| 18838 | 3 | 4 | | | | IV-1 | Lsm14a | 26065 | 4-May-15 | 18931 | 3 | 4 | | | IV-1 | Mavs | 57506 | 24-May-15 |
| 18839 | 3 | 4 | | | | IV-1 | Lsm14b | 149986 | 4-May-15 | 18932 | 3 | 4 | | | IV-1 | Maz | 4150 | 4-May-15 |
| 18840 | 3 | 4 | | | | IV-1 | Lsm2 | 57819 | 4-May-15 | 18933 | 3 | 4 | | | IV-1 | Mb21d2 | 151963 | 4-May-15 |
| 18841 | 3 | 4 | | | | IV-1 | Ltc4s | 4056 | 4-May-15 | 18934 | 3 | 4 | | | IV-1 | Mbd3 | 53615 | 7-Jun-15 |
| 18842 | 3 | 4 | | | | IV-1 | Ltv1 | 84946 | 12-May-15 | 18935 | 3 | 4 | | | IV-1 | Mbd3l1 | 85509 | 4-May-15 |
| 18843 | 3 | 4 | | | | IV-1 | Luc7l | 55692 | 21-May-15 | 18936 | 3 | 4 | | | IV-1 | Mbd3l2 | 125997 | 21-May-15 |
| 18844 | 3 | 4 | | | | IV-1 | Luc7l2 | 51631 | 4-May-15 | 18937 | 3 | 4 | | | IV-1 | Mbd6 | 114785 | 31-May-15 |
| 18845 | 3 | 4 | | | | IV-1 | Luzp2 | 338645 | 4-May-15 | 18938 | 3 | 4 | | | IV-1 | Mbip | 51562 | 12-May-15 |
| 18846 | 3 | 4 | | | | IV-1 | Luzp4 | 51213 | 4-May-15 | 18939 | 3 | 4 | | | IV-1 | Mbl1 | | |
| 18847 | 3 | 4 | | | | IV-1 | Lyg2 | 254773 | 4-May-15 | 18940 | 3 | 4 | | | IV-1 | Mbnl2 | 10150 | 12-May-15 |
| 18848 | 3 | 4 | | | | IV-1 | Lypd6b | 130576 | 4-May-15 | 18941 | 3 | 4 | | | IV-1 | Mboat7 | 79143 | 4-May-15 |
| 18849 | 3 | 4 | | | | IV-1 | Lypla2 | 11313 | 4-May-15 | 18942 | 3 | 4 | | | IV-1 | Mbp | 4155 | 7-Jun-15 |
| 18850 | 3 | 4 | | | | IV-1 | Lyplal1 | 127018 | 4-May-15 | 18943 | 3 | 4 | | | IV-1 | Mbtps1 | 8720 | 17-May-15 |
| 18851 | 3 | 4 | | | | IV-1 | Lyrm2 | 57226 | 4-May-15 | 18944 | 3 | 4 | | | IV-1 | Mbtps2 | 51360 | 4-May-15 |
| 18852 | 3 | 4 | | | | IV-1 | Lyrm4 | 57128 | 12-May-15 | 18945 | 3 | 4 | | | IV-1 | Mc1r | 4157 | 7-Jun-15 |
| 18853 | 3 | 4 | | | | IV-1 | Lyrm9 | 201229 | 4-May-15 | 18946 | 3 | 4 | | | IV-1 | Mc2r | 4158 | 12-May-15 |
| 18854 | 3 | 4 | | | | IV-1 | Lysmd2 | 256586 | 4-May-15 | 18947 | 3 | 4 | | | IV-1 | Mc3r | 4159 | 24-May-15 |
| 18855 | 3 | 4 | | | | IV-1 | Lysmd3 | 116068 | 4-May-15 | 18948 | 3 | 4 | | | IV-1 | Mc4r | 4160 | 31-May-15 |
| 18856 | 3 | 4 | | | | IV-1 | Lysmd4 | 145748 | 4-May-15 | 18949 | 3 | 4 | | | IV-1 | Mchr1 | 2847 | 12-May-15 |
| 18857 | 3 | 4 | | | | IV-1 | Lyzl4 | 131375 | 12-May-15 | 18950 | 3 | 4 | | | IV-1 | Mcl1 | 4170 | 7-Jun-15 |
| 18858 | 3 | 4 | | | | IV-1 | Lyzl4os | | | 18951 | 3 | 4 | | | IV-1 | Mcmbp | 79892 | 4-May-15 |
| 18859 | 3 | 4 | | | | IV-1 | Lyzl6 | 57151 | 4-May-15 | 18952 | 3 | 4 | | | IV-1 | Mcmdc2 | 157777 | 4-May-15 |
| 18860 | 3 | 4 | | | | IV-1 | Lzic | 84328 | 12-May-15 | 18953 | 3 | 4 | | | IV-1 | Mcoln1 | 57192 | 7-Jun-15 |
| 18861 | 3 | 4 | | | | IV-1 | Lztfl1 | 54585 | 4-May-15 | 18954 | 3 | 4 | | | IV-1 | Mcpt-ps1 | | |
| 18862 | 3 | 4 | | | | IV-1 | Lztr1 | 8216 | 12-May-15 | 18955 | 3 | 4 | | | IV-1 | Mcts2 | 100101490 | 4-May-15 |
| 18863 | 3 | 4 | | | | IV-1 | Lzts1 | 11178 | 4-May-15 | 18956 | 3 | 4 | | | IV-1 | Mcur1 | 63933 | 4-May-15 |
| 18864 | 3 | 4 | | | | IV-1 | Lzts2 | 84445 | 4-May-15 | 18957 | 3 | 4 | | | IV-1 | Mdc1 | 9656 | 4-May-15 |
| 18865 | 3 | 4 | | | | IV-1 | Lzts3 | 9762 | 4-May-15 | 18958 | 3 | 4 | | | IV-1 | Mdh1 | 4190 | 28-May-15 |
| 18866 | 3 | 4 | | | | IV-1 | Mab21l2 | 10586 | 4-May-15 | 18959 | 3 | 4 | | | IV-1 | Mdh2 | 4191 | 4-May-15 |
| 18867 | 3 | 4 | | | | IV-1 | Mab21l3 | 126868 | 4-May-15 | 18960 | 3 | 4 | | | IV-1 | Mdn1 | 23195 | 21-May-15 |
| 18868 | 3 | 4 | | | | IV-1 | Macc1 | 346389 | 17-May-15 | 18961 | 3 | 4 | | | IV-1 | Me1 | 4199 | 7-Jun-15 |
| 18869 | 3 | 4 | | | | IV-1 | Macf1 | 23499 | 12-May-15 | 18962 | 3 | 4 | | | IV-1 | Meaf6 | 64769 | 2-Jun-15 |
| 18870 | 3 | 4 | | | | IV-1 | Macrod1 | 28992 | 12-May-15 | 18963 | 3 | 4 | | | IV-1 | Mecom | 2122 | 4-May-15 |
| 18871 | 3 | 4 | | | | IV-1 | Mael | 84944 | 4-May-15 | 18964 | 3 | 4 | | | IV-1 | Mecp2 | 4204 | 23-May-15 |
| 18872 | 3 | 4 | | | | IV-1 | Maf | 4094 | 12-May-15 | 18965 | 3 | 4 | | | IV-1 | Mecr | 51102 | 4-May-15 |
| 18873 | 3 | 4 | | | | IV-1 | Mafa | 389692 | 7-Jun-15 | 18966 | 3 | 4 | | | IV-1 | Med10 | 84246 | 4-May-15 |
| 18874 | 3 | 4 | | | | IV-1 | Magea10 | 4109 | 4-May-15 | 18967 | 3 | 4 | | | IV-1 | Med11 | 400569 | 28-May-15 |
| 18875 | 3 | 4 | | | | IV-1 | Magea2 | 4101 | 7-Jun-15 | 18968 | 3 | 4 | | | IV-1 | Med12 | 9968 | 4-May-15 |
| 18876 | 3 | 4 | | | | IV-1 | Magea3 | 4102 | 31-May-15 | 18969 | 3 | 4 | | | IV-1 | Med12l | 116931 | 28-May-15 |
| 18877 | 3 | 4 | | | | IV-1 | Magea4 | 4103 | 7-Jun-15 | 18970 | 3 | 4 | | | IV-1 | Med13l | 23389 | 28-May-15 |
| 18878 | 3 | 4 | | | | IV-1 | Magea5 | 4104 | 4-May-15 | 18971 | 3 | 4 | | | IV-1 | Med14 | 9282 | 21-May-15 |
| 18879 | 3 | 4 | | | | IV-1 | Magea6 | 4105 | 7-Jun-15 | 18972 | 3 | 4 | | | IV-1 | Med15 | 51586 | 12-May-15 |
| 18880 | 3 | 4 | | | | IV-1 | Mageb1 | 4112 | 12-May-15 | 18973 | 3 | 4 | | | IV-1 | Med17 | 9440 | 4-May-15 |
| 18881 | 3 | 4 | | | | IV-1 | Mageb5 | 347541 | 4-May-15 | 18974 | 3 | 4 | | | IV-1 | Med18 | 54797 | 4-May-15 |
| 18882 | 3 | 4 | | | | IV-1 | Magee2 | 139599 | 4-May-15 | 18975 | 3 | 4 | | | IV-1 | Med19 | 219541 | 28-May-15 |
| 18883 | 3 | 4 | | | | IV-1 | Mak | 4117 | 7-Jun-15 | 18976 | 3 | 4 | | | IV-1 | Med20 | 9477 | 2-Jun-15 |
| 18884 | 3 | 4 | | | | IV-1 | Mak16 | 84549 | 4-May-15 | 18977 | 3 | 4 | | | IV-1 | Med21 | 9412 | 4-May-15 |
| 18885 | 3 | 4 | | | | IV-1 | Mami1 | 9794 | 4-May-15 | 18978 | 3 | 4 | | | IV-1 | Med22 | 6837 | 28-May-15 |
| 18886 | 3 | 4 | | | | IV-1 | Mami2 | 84441 | 4-May-15 | 18979 | 3 | 4 | | | IV-1 | Med23 | 9439 | 21-May-15 |
| 18887 | 3 | 4 | | | | IV-1 | Mami3 | 55534 | 4-May-15 | 18980 | 3 | 4 | | | IV-1 | Med24 | 9862 | 7-Jun-15 |
| 18888 | 3 | 4 | | | | IV-1 | Man1b1 | 11253 | 17-May-15 | 18981 | 3 | 4 | | | IV-1 | Med25 | 81857 | 7-Jun-15 |
| 18889 | 3 | 4 | | | | IV-1 | Man1c1 | 57134 | 4-May-15 | 18982 | 3 | 4 | | | IV-1 | Med29 | 55588 | 4-May-15 |
| | | | | | | | | | | 18983 | 3 | 4 | | | IV-1 | Med30 | 90390 | 4-May-15 |
| | | | | | | | | | | 18984 | 3 | 4 | | | IV-1 | Med31 | 51003 | 2-Jun-15 |

Fig. 30 - 101

| | | | | | | | | | |
|---|---|---|---|---|---|---|---|---|---|
| 18985 | 3 | 4 | | | | IV-1 | Med6 | 10003 | 4-May-15 |
| 18986 | 3 | 4 | | | | IV-1 | Med8 | 112950 | 12-May-15 |
| 18987 | 3 | 4 | | | | IV-1 | Med9 | 55090 | 28-May-15 |
| 18988 | 3 | 4 | | | | IV-1 | Med9os | | |
| 18989 | 3 | 4 | | | | IV-1 | Megf13 | 84465 | 4-May-15 |
| 18990 | 3 | 4 | | | | IV-1 | Mei4 | 101928601 | 4-May-15 |
| 18991 | 3 | 4 | | | | IV-1 | Meis1 | 4211 | 4-May-15 |
| 18992 | 3 | 4 | | | | IV-1 | Mepce | 56257 | 4-May-15 |
| 18993 | 3 | 4 | | | | IV-1 | Mepe | 56955 | 12-May-15 |
| 18994 | 3 | 4 | | | | IV-1 | Mesp1 | 55897 | 28-May-15 |
| 18995 | 3 | 4 | | | | IV-1 | Mesp2 | 145873 | 23-May-15 |
| 18996 | 3 | 4 | | | | IV-1 | Mettl1 | 4234 | 4-May-15 |
| 18997 | 3 | 4 | | | | IV-1 | Mettl1b | 149281 | 4-May-15 |
| 18998 | 3 | 4 | | | | IV-1 | Mettl14 | 57721 | 4-May-15 |
| 18999 | 3 | 4 | | | | IV-1 | Mettl15 | 196074 | 4-May-15 |
| 19000 | 3 | 4 | | | | IV-1 | Mettl17 | 64745 | 4-May-15 |
| 19001 | 3 | 4 | | | | IV-1 | Mettl18 | 92342 | 4-May-15 |
| 19002 | 3 | 4 | | | | IV-1 | Mettl2 | 339175 | 7-Jun-15 |
| 19003 | 3 | 4 | | | | IV-1 | Mettl21c | 196541 | 4-May-15 |
| 19004 | 3 | 4 | | | | IV-1 | Mettl23 | 124512 | 12-May-15 |
| 19005 | 3 | 4 | | | | IV-1 | Mettl25 | 84190 | 4-May-15 |
| 19006 | 3 | 4 | | | | IV-1 | Mettl3 | 56339 | 29-May-15 |
| 19007 | 3 | 4 | | | | IV-1 | Mettl4 | 64863 | 12-May-15 |
| 19008 | 3 | 4 | | | | IV-1 | Mettl5 | 29081 | 4-May-15 |
| 19009 | 3 | 4 | | | | IV-1 | Mettl6 | 131965 | 12-May-15 |
| 19010 | 3 | 4 | | | | IV-1 | Mex3d | 399664 | 4-May-15 |
| 19011 | 3 | 4 | | | | IV-1 | Mfap1a | | |
| 19012 | 3 | 4 | | | | IV-1 | Mfap1b | | |
| 19013 | 3 | 4 | | | | IV-1 | Mfap3l | 9848 | 12-May-15 |
| 19014 | 3 | 4 | | | | IV-1 | Mfn1 | 55669 | 24-May-15 |
| 19015 | 3 | 4 | | | | IV-1 | Mfsd5 | 84975 | 4-May-15 |
| 19016 | 3 | 4 | | | | IV-1 | Mfsd6 | 54842 | 4-May-15 |
| 19017 | 3 | 4 | | | | IV-1 | Mfsd6l | 162387 | 4-May-15 |
| 19018 | 3 | 4 | | | | IV-1 | Mfsd7a | | |
| 19019 | 3 | 4 | | | | IV-1 | Mgat1 | 4245 | 7-Jun-15 |
| 19020 | 3 | 4 | | | | IV-1 | Mgat2 | 4247 | 23-May-15 |
| 19021 | 3 | 4 | | | | IV-1 | Mgat3 | 4248 | 7-Jun-15 |
| 19022 | 3 | 4 | | | | IV-1 | Mgat4c | 25834 | 12-May-15 |
| 19023 | 3 | 4 | | | | IV-1 | Mgat5 | 4249 | 4-May-15 |
| 19024 | 3 | 4 | | | | IV-1 | Mgat5b | 146664 | 12-May-15 |
| 19025 | 3 | 4 | | | | IV-1 | Mgl2 | | |
| 19026 | 3 | 4 | | | | IV-1 | Miat | 440823 | 12-May-15 |
| 19027 | 3 | 4 | | | | IV-1 | Mib1 | 57534 | 7-Jun-15 |
| 19028 | 3 | 4 | | | | IV-1 | Mib2 | 142678 | 4-May-15 |
| 19029 | 3 | 4 | | | | IV-1 | Mical1 | 64780 | 12-May-15 |
| 19030 | 3 | 4 | | | | IV-1 | Micall1 | 85377 | 4-May-15 |
| 19031 | 3 | 4 | | | | IV-1 | Micu2 | 221154 | 4-May-15 |
| 19032 | 3 | 4 | | | | IV-1 | Micu3 | 286097 | 4-May-15 |
| 19033 | 3 | 4 | | | | IV-1 | Midn | 90007 | 4-May-15 |
| 19034 | 3 | 4 | | | | IV-1 | Mief2 | 125170 | 12-May-15 |
| 19035 | 3 | 4 | | | | IV-1 | Mier2 | 54531 | 4-May-15 |
| 19036 | 3 | 4 | | | | IV-1 | Mier3 | 166968 | 12-May-15 |
| 19037 | 3 | 4 | | | | IV-1 | Miip | 60672 | 4-May-15 |
| 19038 | 3 | 4 | | | | IV-1 | Mink1 | 50488 | 4-May-15 |
| 19039 | 3 | 4 | | | | IV-1 | Minos1 | 440574 | 7-Jun-15 |
| 19040 | 3 | 4 | | | | IV-1 | Miox | 55586 | 4-May-15 |
| 19041 | 3 | 4 | | | | IV-1 | Mipep | 4285 | 12-May-15 |
| 19042 | 3 | 4 | | | | IV-1 | Mir106a | 406899 | 21-May-15 |
| 19043 | 3 | 4 | | | | IV-1 | Mir129b | | |
| 19044 | 3 | 4 | | | | IV-1 | Mir183 | 406959 | 7-Jun-15 |
| 19045 | 3 | 4 | | | | IV-1 | Mir1952 | | |
| 19046 | 3 | 4 | | | | IV-1 | Mir1963 | | |
| 19047 | 3 | 4 | | | | IV-1 | Mir21 | 406991 | 7-Jun-15 |
| 19048 | 3 | 4 | | | | IV-1 | Mir216b | 100126319 | 21-May-15 |
| 19049 | 3 | 4 | | | | IV-1 | Mir21c | | |
| 19050 | 3 | 4 | | | | IV-1 | Mir297a-3 | | |
| 19051 | 3 | 4 | | | | IV-1 | Mir297b | | |
| 19052 | 3 | 4 | | | | IV-1 | Mir297c | | |
| 19053 | 3 | 4 | | | | IV-1 | Mir376c | 442913 | 21-May-15 |
| 19054 | 3 | 4 | | | | IV-1 | Mir465b-2 | | |
| 19055 | 3 | 4 | | | | IV-1 | Mir465c-1 | | |
| 19056 | 3 | 4 | | | | IV-1 | Mir465d | | |
| 19057 | 3 | 4 | | | | IV-1 | Mir467a-3 | | |
| 19058 | 3 | 4 | | | | IV-1 | Mir467a-5 | | |
| 19059 | 3 | 4 | | | | IV-1 | Mir467b | | |
| 19060 | 3 | 4 | | | | IV-1 | Mir495 | 574453 | 21-May-15 |
| 19061 | 3 | 4 | | | | IV-1 | Mir497b | | |
| 19062 | 3 | 4 | | | | IV-1 | Mir511 | 574445 | 21-May-15 |
| 19063 | 3 | 4 | | | | IV-1 | Mir5131 | | |
| 19064 | 3 | 4 | | | | IV-1 | Mir5615-1 | | |
| 19065 | 3 | 4 | | | | IV-1 | Mir5627 | | |
| 19066 | 3 | 4 | | | | IV-1 | Mir582 | 693167 | 5-May-15 |
| 19067 | 3 | 4 | | | | IV-1 | Mir598 | 693183 | 21-May-15 |
| 19068 | 3 | 4 | | | | IV-1 | Mir6241 | | |
| 19069 | 3 | 4 | | | | IV-1 | Mir6344 | | |
| 19070 | 3 | 4 | | | | IV-1 | Mir6349 | | |
| 19071 | 3 | 4 | | | | IV-1 | Mir6350 | | |
| 19072 | 3 | 4 | | | | IV-1 | Mir6378 | | |
| 19073 | 3 | 4 | | | | IV-1 | Mir6402 | | |
| 19074 | 3 | 4 | | | | IV-1 | Mir6412 | | |
| 19075 | 3 | 4 | | | | IV-1 | Mir6420 | | |
| 19076 | 3 | 4 | | | | IV-1 | Mir6540 | | |
| 19077 | 3 | 4 | | | | IV-1 | Mir669a-11 | | |
| 19078 | 3 | 4 | | | | IV-1 | Mir669a-12 | | |
| 19079 | 3 | 4 | | | | IV-1 | Mir669a-4 | | |
| 19080 | 3 | 4 | | | | IV-1 | Mir669m-2 | | |
| 19081 | 3 | 4 | | | | IV-1 | Mir669p-2 | | |
| 19082 | 3 | 4 | | | | IV-1 | Mir7218 | | |
| 19083 | 3 | 4 | | | | IV-1 | Mir7239 | | |
| 19084 | 3 | 4 | | | | IV-1 | Mir741 | | |
| 19085 | 3 | 4 | | | | IV-1 | Mir7669 | | |
| 19086 | 3 | 4 | | | | IV-1 | Mir767 | 768215 | 21-May-15 |
| 19087 | 3 | 4 | | | | IV-1 | Mir7672 | | |
| 19088 | 3 | 4 | | | | IV-1 | Mir7685 | | |
| 19089 | 3 | 4 | | | | IV-1 | Mir879 | | |
| 19090 | 3 | 4 | | | | IV-1 | Mir880 | | |
| 19091 | 3 | 4 | | | | IV-1 | Mir881 | | |
| 19092 | 3 | 4 | | | | IV-1 | Mir882 | | |
| 19093 | 3 | 4 | | | | IV-1 | Mir98 | 407054 | 21-May-15 |
| 19094 | 3 | 4 | | | | IV-1 | Mirlet7k | | |
| 19095 | 3 | 4 | | | | IV-1 | Mis12 | 79003 | 4-May-15 |
| 19096 | 3 | 4 | | | | IV-1 | Mitf | 4286 | 31-May-15 |
| 19097 | 3 | 4 | | | | IV-1 | Mkln1 | 4289 | 4-May-15 |
| 19098 | 3 | 4 | | | | IV-1 | Mkln1os | | |
| 19099 | 3 | 4 | | | | IV-1 | Mknk2 | 2872 | 4-May-15 |
| 19100 | 3 | 4 | | | | IV-1 | Mkrn3 | 7681 | 23-May-15 |
| 19101 | 3 | 4 | | | | IV-1 | Mks1 | 54903 | 23-May-15 |
| 19102 | 3 | 4 | | | | IV-1 | Mkx | 283078 | 4-May-15 |
| 19103 | 3 | 4 | | | | IV-1 | Mlec | 9761 | 12-May-15 |
| 19104 | 3 | 4 | | | | IV-1 | Mlh1 | 4292 | 7-Jun-15 |
| 19105 | 3 | 4 | | | | IV-1 | Mlh3 | 27030 | 4-May-15 |
| 19106 | 3 | 4 | | | | IV-1 | Mlip | 90523 | 4-May-15 |
| 19107 | 3 | 4 | | | | IV-1 | Mllt10 | 8028 | 4-May-15 |
| 19108 | 3 | 4 | | | | IV-1 | Mllt11 | 10962 | 4-May-15 |
| 19109 | 3 | 4 | | | | IV-1 | Mllt4 | 4301 | 21-May-15 |
| 19110 | 3 | 4 | | | | IV-1 | Mllt6 | 4302 | 4-May-15 |
| 19111 | 3 | 4 | | | | IV-1 | Mlx | 6945 | 4-May-15 |
| 19112 | 3 | 4 | | | | IV-1 | Mmd | 23531 | 4-May-15 |
| 19113 | 3 | 4 | | | | IV-1 | Mmgt1 | 93380 | 4-May-15 |
| 19114 | 3 | 4 | | | | IV-1 | Mmgt2 | | |
| 19115 | 3 | 4 | | | | IV-1 | Mmp17 | 4326 | 4-May-15 |
| 19116 | 3 | 4 | | | | IV-1 | Mmp1b | | |
| 19117 | 3 | 4 | | | | IV-1 | Mmp21 | 118856 | 17-May-15 |
| 19118 | 3 | 4 | | | | IV-1 | Mnx1 | 3110 | 12-May-15 |
| 19119 | 3 | 4 | | | | IV-1 | Moap1 | 64112 | 4-May-15 |
| 19120 | 3 | 4 | | | | IV-1 | Mob1b | 92597 | 4-May-15 |
| 19121 | 3 | 4 | | | | IV-1 | Mob2 | 81532 | 4-May-15 |
| 19122 | 3 | 4 | | | | IV-1 | Mob4 | 25843 | 4-May-15 |
| 19123 | 3 | 4 | | | | IV-1 | Mobp | 4336 | 4-May-15 |
| 19124 | 3 | 4 | | | | IV-1 | Mocos | 55034 | 4-May-15 |
| 19125 | 3 | 4 | | | | IV-1 | Mocs3 | 27304 | 24-May-15 |
| 19126 | 3 | 4 | | | | IV-1 | Mon1b | 22879 | 4-May-15 |
| 19127 | 3 | 4 | | | | IV-1 | Mon2 | 23041 | 4-May-15 |
| 19128 | 3 | 4 | | | | IV-1 | Morc2b | | |
| 19129 | 3 | 4 | | | | IV-1 | Morc3 | 23515 | 4-May-15 |
| 19130 | 3 | 4 | | | | IV-1 | Morf4l1 | 10933 | 4-May-15 |
| 19131 | 3 | 4 | | | | IV-1 | Mospd1 | 56180 | 12-May-15 |
| 19132 | 3 | 4 | | | | IV-1 | Mospd2 | 158747 | 4-May-15 |
| 19133 | 3 | 4 | | | | IV-1 | Mov10 | 4343 | 4-May-15 |
| 19134 | 3 | 4 | | | | IV-1 | Mpc1 | 51660 | 7-Jun-15 |
| 19135 | 3 | 4 | | | | IV-1 | Mpc2 | 25874 | 12-May-15 |
| 19136 | 3 | 4 | | | | IV-1 | Mpdz | 8777 | 7-Jun-15 |
| 19137 | 3 | 4 | | | | IV-1 | Mphosph8 | 54737 | 17-May-15 |
| 19138 | 3 | 4 | | | | IV-1 | Mphosph9 | 10198 | 4-May-15 |
| 19139 | 3 | 4 | | | | IV-1 | Mpi | 4351 | 7-Jun-15 |
| 19140 | 3 | 4 | | | | IV-1 | Mpi | 4352 | 3-May-15 |
| 19141 | 3 | 4 | | | | IV-1 | Mpnd | 84954 | 4-May-15 |
| 19142 | 3 | 4 | | | | IV-1 | Mpp6 | 51678 | 7-Jun-15 |
| 19143 | 3 | 4 | | | | IV-1 | Mpp7 | 143098 | 7-Jun-15 |
| 19144 | 3 | 4 | | | | IV-1 | Mppe1 | 65258 | 4-May-15 |
| 19145 | 3 | 4 | | | | IV-1 | Mpped2 | 744 | 4-May-15 |
| 19146 | 3 | 4 | | | | IV-1 | Mpst | 4357 | 7-Jun-15 |
| 19147 | 3 | 4 | | | | IV-1 | Mptx2 | | |
| 19148 | 3 | 4 | | | | IV-1 | Mpv17 | 4358 | 23-May-15 |
| 19149 | 3 | 4 | | | | IV-1 | Mrgbp | 55257 | 4-May-15 |
| 19150 | 3 | 4 | | | | IV-1 | Mrgpra1 | | |
| 19151 | 3 | 4 | | | | IV-1 | Mrgpra4 | | |
| 19152 | 3 | 4 | | | | IV-1 | Mrgpra6 | | |
| 19153 | 3 | 4 | | | | IV-1 | Mrgprb2 | | |
| 19154 | 3 | 4 | | | | IV-1 | Mrgprb3 | | |
| 19155 | 3 | 4 | | | | IV-1 | Mrgprb4 | | |
| 19156 | 3 | 4 | | | | IV-1 | Mrgprb5 | | |
| 19157 | 3 | 4 | | | | IV-1 | Mrgprb8 | | |
| 19158 | 3 | 4 | | | | IV-1 | Mrgprd | 116512 | 4-May-15 |
| 19159 | 3 | 4 | | | | IV-1 | Mrgpre | 116534 | 12-May-15 |
| 19160 | 3 | 4 | | | | IV-1 | Mrgprx2 | 117194 | 12-May-15 |
| 19161 | 3 | 4 | | | | IV-1 | Mrl1 | 84245 | 4-May-15 |
| 19162 | 3 | 4 | | | | IV-1 | Mrm1 | 79922 | 4-May-15 |
| 19163 | 3 | 4 | | | | IV-1 | Mroh1 | 727957 | 4-May-15 |
| 19164 | 3 | 4 | | | | IV-1 | Mroh2a | 339766 | 4-May-15 |
| 19165 | 3 | 4 | | | | IV-1 | Mroh2b | 133558 | 4-May-15 |
| 19166 | 3 | 4 | | | | IV-1 | Mroh4 | | |
| 19167 | 3 | 4 | | | | IV-1 | Mroh5 | 389690 | 4-May-15 |
| 19168 | 3 | 4 | | | | IV-1 | Mroh6 | 642475 | 4-May-15 |
| 19169 | 3 | 4 | | | | IV-1 | Mroh7 | 374977 | 4-May-15 |
| 19170 | 3 | 4 | | | | IV-1 | Mroh8 | 140699 | 12-May-15 |
| 19171 | 3 | 4 | | | | IV-1 | Mroh9 | 80133 | 4-May-15 |
| 19172 | 3 | 4 | | | | IV-1 | Mrpl1 | 65008 | 4-May-15 |
| 19173 | 3 | 4 | | | | IV-1 | Mrpl11 | 65003 | 12-May-15 |
| 19174 | 3 | 4 | | | | IV-1 | Mrpl12 | 6182 | 4-May-15 |

Fig. 30 - 102

| | | | | | | | | | | | | | | |
|---|---|---|---|---|---|---|---|---|---|---|---|---|---|---|
| 19175 | 3 | 4 | | | | IV-1 | Mrpl14 | 64928 | 7-Jun-15 | 19271 | 3 | 4 | | | | IV-1 | Myo10 | 4651 | 31-May-15 |
| 19176 | 3 | 4 | | | | IV-1 | Mrpl18 | 29074 | 7-Jun-15 | 19272 | 3 | 4 | | | | IV-1 | Myo15 | 51168 | 23-May-15 |
| 19177 | 3 | 4 | | | | IV-1 | Mrpl21 | 219927 | 4-May-15 | 19273 | 3 | 4 | | | | IV-1 | Myo16 | 23026 | 4-May-15 |
| 19178 | 3 | 4 | | | | IV-1 | Mrpl24 | 79590 | 4-May-15 | 19274 | 3 | 4 | | | | IV-1 | Myo18a | 399687 | 4-May-15 |
| 19179 | 3 | 4 | | | | IV-1 | Mrpl27 | 51264 | 7-Jun-15 | 19275 | 3 | 4 | | | | IV-1 | Myo18b | 84700 | 4-May-15 |
| 19180 | 3 | 4 | | | | IV-1 | Mrpl28 | 10573 | 7-Jun-15 | 19276 | 3 | 4 | | | | IV-1 | Myo1a | 4640 | 23-May-15 |
| 19181 | 3 | 4 | | | | IV-1 | Mrpl33 | 9553 | 4-May-15 | 19277 | 3 | 4 | | | | IV-1 | Myo1b | 4430 | 4-May-15 |
| 19182 | 3 | 4 | | | | IV-1 | Mrpl37 | 51253 | 4-May-15 | 19278 | 3 | 4 | | | | IV-1 | Myo3a | 53904 | 23-May-15 |
| 19183 | 3 | 4 | | | | IV-1 | Mrpl39 | 54148 | 12-May-15 | 19279 | 3 | 4 | | | | IV-1 | Myo6 | 4646 | 23-May-15 |
| 19184 | 3 | 4 | | | | IV-1 | Mrpl41 | 64975 | 4-May-15 | 19280 | 3 | 4 | | | | IV-1 | Myo9b | 4650 | 4-May-15 |
| 19185 | 3 | 4 | | | | IV-1 | Mrpl44 | 65080 | 21-May-15 | 19281 | 3 | 4 | | | | IV-1 | Mypn | 84665 | 12-May-15 |
| 19186 | 3 | 4 | | | | IV-1 | Mrpl48 | 51642 | 4-May-15 | 19282 | 3 | 4 | | | | IV-1 | Myrf | 745 | 12-May-15 |
| 19187 | 3 | 4 | | | | IV-1 | Mrpl49 | 740 | 4-May-15 | 19283 | 3 | 4 | | | | IV-1 | Myt1 | 4661 | 7-Jun-15 |
| 19188 | 3 | 4 | | | | IV-1 | Mrpl50 | 54534 | 14-May-15 | 19284 | 3 | 4 | | | | IV-1 | Myt1l | 23040 | 12-May-15 |
| 19189 | 3 | 4 | | | | IV-1 | Mrpl53 | 116540 | 4-May-15 | 19285 | 3 | 4 | | | | IV-1 | Mzt1 | 440145 | 4-May-15 |
| 19190 | 3 | 4 | | | | IV-1 | Mrpl54 | 116541 | 21-May-15 | 19286 | 3 | 4 | | | | IV-1 | Mzt2 | | |
| 19191 | 3 | 4 | | | | IV-1 | Mrpl55 | 128308 | 4-May-15 | 19287 | 3 | 4 | | | | IV-1 | N28178 | | |
| 19192 | 3 | 4 | | | | IV-1 | Mrpl57 | 78988 | 28-May-15 | 19288 | 3 | 4 | | | | IV-1 | N4bp1 | 9683 | 4-May-15 |
| 19193 | 3 | 4 | | | | IV-1 | Mrpl9 | 65005 | 4-May-15 | 19289 | 3 | 4 | | | | IV-1 | N4bp3 | 23138 | 4-May-15 |
| 19194 | 3 | 4 | | | | IV-1 | Mrps11 | 64963 | 28-May-15 | 19290 | 3 | 4 | | | | IV-1 | N6amt2 | 221143 | 4-May-15 |
| 19195 | 3 | 4 | | | | IV-1 | Mrps12 | 6183 | 7-Jun-15 | 19291 | 3 | 4 | | | | IV-1 | Naa10 | 8260 | 23-May-15 |
| 19196 | 3 | 4 | | | | IV-1 | Mrps14 | 63931 | 12-May-15 | 19292 | 3 | 4 | | | | IV-1 | Naa11 | 84779 | 4-May-15 |
| 19197 | 3 | 4 | | | | IV-1 | Mrps16 | 51021 | 28-May-15 | 19293 | 3 | 4 | | | | IV-1 | Naa15 | 80155 | 4-May-15 |
| 19198 | 3 | 4 | | | | IV-1 | Mrps17 | 51373 | 28-May-15 | 19294 | 3 | 4 | | | | IV-1 | Naa16 | 79612 | 12-May-15 |
| 19199 | 3 | 4 | | | | IV-1 | Mrps18a | 55168 | 28-May-15 | 19295 | 3 | 4 | | | | IV-1 | Naa20 | 51126 | 4-May-15 |
| 19200 | 3 | 4 | | | | IV-1 | Mrps21 | 54460 | 28-May-15 | 19296 | 3 | 4 | | | | IV-1 | Naa25 | 80018 | 4-May-15 |
| 19201 | 3 | 4 | | | | IV-1 | Mrps22 | 56945 | 4-May-15 | 19297 | 3 | 4 | | | | IV-1 | Naa35 | 60560 | 4-May-15 |
| 19202 | 3 | 4 | | | | IV-1 | Mrps24 | 64951 | 28-May-15 | 19298 | 3 | 4 | | | | IV-1 | Naa38 | 84316 | 7-Jun-15 |
| 19203 | 3 | 4 | | | | IV-1 | Mrps26 | 64949 | 4-May-15 | 19299 | 3 | 4 | | | | IV-1 | Naa40 | 79829 | 4-May-15 |
| 19204 | 3 | 4 | | | | IV-1 | Mrps27 | 23107 | 4-May-15 | 19300 | 3 | 4 | | | | IV-1 | Naa50 | 80218 | 2-Jun-15 |
| 19205 | 3 | 4 | | | | IV-1 | Mrps34 | 65993 | 21-May-15 | 19301 | 3 | 4 | | | | IV-1 | Naa60 | 79903 | 4-May-15 |
| 19206 | 3 | 4 | | | | IV-1 | Mrps35 | 60488 | 7-Jun-15 | 19302 | 3 | 4 | | | | IV-1 | Nab1 | 4664 | 4-May-15 |
| 19207 | 3 | 4 | | | | IV-1 | Mrps6 | 64968 | 28-May-15 | 19303 | 3 | 4 | | | | IV-1 | Nab2 | 4665 | 24-May-15 |
| 19208 | 3 | 4 | | | | IV-1 | Mrps7 | 51081 | 28-May-15 | 19304 | 3 | 4 | | | | IV-1 | Naca | 4666 | 3-May-15 |
| 19209 | 3 | 4 | | | | IV-1 | Mrps9 | 64965 | 4-May-15 | 19305 | 3 | 4 | | | | IV-1 | Nacad | 23148 | 4-May-15 |
| 19210 | 3 | 4 | | | | IV-1 | Ms4a13 | 503497 | 12-May-15 | 19306 | 3 | 4 | | | | IV-1 | Nacc1 | 112939 | 4-May-15 |
| 19211 | 3 | 4 | | | | IV-1 | Ms4a15 | 219995 | 4-May-15 | 19307 | 3 | 4 | | | | IV-1 | Nacc2 | 138151 | 28-May-15 |
| 19212 | 3 | 4 | | | | IV-1 | Ms4a18 | 728588 | 4-May-15 | 19308 | 3 | 4 | | | | IV-1 | Nadk | 65220 | 4-May-15 |
| 19213 | 3 | 4 | | | | IV-1 | Ms4a2 | 2206 | 7-Jun-15 | 19309 | 3 | 4 | | | | IV-1 | Nae1 | 8883 | 12-May-15 |
| 19214 | 3 | 4 | | | | IV-1 | Msantd2 | 79684 | 12-May-15 | 19310 | 3 | 4 | | | | IV-1 | Naf1 | 92345 | 16-Jun-15 |
| 19215 | 3 | 4 | | | | IV-1 | Msantd3 | 91283 | 4-May-15 | 19311 | 3 | 4 | | | | IV-1 | Naga | 4668 | 4-May-15 |
| 19216 | 3 | 4 | | | | IV-1 | Msh2 | 4436 | 23-May-15 | 19312 | 3 | 4 | | | | IV-1 | Naglu | 4669 | 4-May-15 |
| 19217 | 3 | 4 | | | | IV-1 | Msh3 | 4437 | 4-May-15 | 19313 | 3 | 4 | | | | IV-1 | Naip1 | | |
| 19218 | 3 | 4 | | | | IV-1 | Msh4 | 4438 | 4-May-15 | 19314 | 3 | 4 | | | | IV-1 | Nanos1 | 340719 | 4-May-15 |
| 19219 | 3 | 4 | | | | IV-1 | Msi2 | 124540 | 17-May-15 | 19315 | 3 | 4 | | | | IV-1 | Nap1l3 | 4675 | 12-May-15 |
| 19220 | 3 | 4 | | | | IV-1 | Msl2 | 55167 | 4-May-15 | 19316 | 3 | 4 | | | | IV-1 | Nap1l4 | 4676 | 12-May-15 |
| 19221 | 3 | 4 | | | | IV-1 | Msl3 | 10943 | 4-May-15 | 19317 | 3 | 4 | | | | IV-1 | Nap1l5 | 266812 | 4-May-15 |
| 19222 | 3 | 4 | | | | IV-1 | Msl3l2 | 151507 | 4-May-15 | 19318 | 3 | 4 | | | | IV-1 | Naprt1 | 93100 | 4-May-15 |
| 19223 | 3 | 4 | | | | IV-1 | Msmb | 4477 | 12-May-15 | 19319 | 3 | 4 | | | | IV-1 | Narg2 | 79664 | 4-May-15 |
| 19224 | 3 | 4 | | | | IV-1 | Msrb1 | 51734 | 12-May-15 | 19320 | 3 | 4 | | | | IV-1 | Nars | 4677 | 4-May-15 |
| 19225 | 3 | 4 | | | | IV-1 | Msx1 | 4487 | 17-May-15 | 19321 | 3 | 4 | | | | IV-1 | Nars2 | 79731 | 3-May-15 |
| 19226 | 3 | 4 | | | | IV-1 | Msx2 | 4488 | 23-May-15 | 19322 | 3 | 4 | | | | IV-1 | Nat10 | 55226 | 4-May-15 |
| 19227 | 3 | 4 | | | | IV-1 | Mtag2 | 84677 | 4-May-15 | 19323 | 3 | 4 | | | | IV-1 | Nat14 | 57106 | 23-May-15 |
| 19228 | 3 | 4 | | | | IV-1 | Mtap | 4507 | 12-May-15 | 19324 | 3 | 4 | | | | IV-1 | Nat3 | | |
| 19229 | 3 | 4 | | | | IV-1 | Mtbp | 27085 | 4-May-15 | 19325 | 3 | 4 | | | | IV-1 | Nat6 | 24142 | 7-Jun-15 |
| 19230 | 3 | 4 | | | | IV-1 | Mtch2 | 23788 | 4-May-15 | 19326 | 3 | 4 | | | | IV-1 | Nav1 | 89796 | 4-May-15 |
| 19231 | 3 | 4 | | | | IV-1 | Mtcl1 | 23255 | 12-May-15 | 19327 | 3 | 4 | | | | IV-1 | Nbea | 26960 | 4-May-15 |
| 19232 | 3 | 4 | | | | IV-1 | Mtdh | 92140 | 17-May-15 | 19328 | 3 | 4 | | | | IV-1 | Nbr1 | 4077 | 24-May-15 |
| 19233 | 3 | 4 | | | | IV-1 | Mterf1a | | | 19329 | 3 | 4 | | | | IV-1 | Ncald | 83988 | 4-May-15 |
| 19234 | 3 | 4 | | | | IV-1 | Mterf1b | | | 19330 | 3 | 4 | | | | IV-1 | Ncan | 1463 | 4-May-15 |
| 19235 | 3 | 4 | | | | IV-1 | Mterfd2 | 130916 | 4-May-15 | 19331 | 3 | 4 | | | | IV-1 | Ncbp1 | 4686 | 4-May-15 |
| 19236 | 3 | 4 | | | | IV-1 | Mtf2 | 22823 | 4-May-15 | 19332 | 3 | 4 | | | | IV-1 | Ncbp2 | 22916 | 2-Jun-15 |
| 19237 | 3 | 4 | | | | IV-1 | Mtif2 | 4528 | 12-May-15 | 19333 | 3 | 4 | | | | IV-1 | Nceh1 | 57552 | 12-May-15 |
| 19238 | 3 | 4 | | | | IV-1 | Mtif3 | 219402 | 4-May-15 | 19334 | 3 | 4 | | | | IV-1 | Nck2 | 8440 | 4-May-15 |
| 19239 | 3 | 4 | | | | IV-1 | Mtmr1 | 8776 | 12-May-15 | 19335 | 3 | 4 | | | | IV-1 | Nckap1 | 10787 | 4-May-15 |
| 19240 | 3 | 4 | | | | IV-1 | Mtmr10 | 54893 | 4-May-15 | 19336 | 3 | 4 | | | | IV-1 | Ncln | 56926 | 3-May-15 |
| 19241 | 3 | 4 | | | | IV-1 | Mtmr11 | 10903 | 17-May-15 | 19337 | 3 | 4 | | | | IV-1 | Ncoa2 | 10499 | 17-May-15 |
| 19242 | 3 | 4 | | | | IV-1 | Mtmr14 | 64419 | 4-May-15 | 19338 | 3 | 4 | | | | IV-1 | Ncoa3 | 8202 | 17-May-15 |
| 19243 | 3 | 4 | | | | IV-1 | Mtmr2 | 8898 | 4-May-15 | 19339 | 3 | 4 | | | | IV-1 | Ncoa4 | 8031 | 4-May-15 |
| 19244 | 3 | 4 | | | | IV-1 | Mtmr3 | 8897 | 24-May-15 | 19340 | 3 | 4 | | | | IV-1 | Ncoa6 | 23054 | 4-May-15 |
| 19245 | 3 | 4 | | | | IV-1 | Mtmr4 | 9110 | 24-May-15 | 19341 | 3 | 4 | | | | IV-1 | Ncoa7 | 135112 | 4-May-15 |
| 19246 | 3 | 4 | | | | IV-1 | Mtmr6 | 9107 | 4-May-15 | 19342 | 3 | 4 | | | | IV-1 | Ncor2 | 9612 | 4-May-15 |
| 19247 | 3 | 4 | | | | IV-1 | Mtmr7 | 9108 | 12-May-15 | 19343 | 3 | 4 | | | | IV-1 | Ndc1 | 55706 | 4-May-15 |
| 19248 | 3 | 4 | | | | IV-1 | Mtnr1a | 4543 | 4-May-15 | 19344 | 3 | 4 | | | | IV-1 | Ndfip1 | 80762 | 31-May-15 |
| 19249 | 3 | 4 | | | | IV-1 | Mtnr1b | 4544 | 21-May-15 | 19345 | 3 | 4 | | | | IV-1 | Ndfip2 | 54602 | 4-May-15 |
| 19250 | 3 | 4 | | | | IV-1 | Mto1 | 25821 | 12-May-15 | 19346 | 3 | 4 | | | | IV-1 | Ndnl2 | 56160 | 4-May-15 |
| 19251 | 3 | 4 | | | | IV-1 | Mtor | 2475 | 31-May-15 | 19347 | 3 | 4 | | | | IV-1 | Ndp | 4693 | 23-May-15 |
| 19252 | 3 | 4 | | | | IV-1 | Mtpap | 55149 | 4-May-15 | 19348 | 3 | 4 | | | | IV-1 | Ndst2 | 8509 | 4-May-15 |
| 19253 | 3 | 4 | | | | IV-1 | Mtpn | 136319 | 4-May-15 | 19349 | 3 | 4 | | | | IV-1 | Ndst3 | 9348 | 4-May-15 |
| 19254 | 3 | 4 | | | | IV-1 | Mtrr | 4552 | 23-May-15 | 19350 | 3 | 4 | | | | IV-1 | Ndufa4 | 4694 | 3-May-15 |
| 19255 | 3 | 4 | | | | IV-1 | Mtss1 | 9788 | 3-May-15 | 19351 | 3 | 4 | | | | IV-1 | Ndufa10 | 4705 | 23-May-15 |
| 19256 | 3 | 4 | | | | IV-1 | Mttp | 4547 | 7-Jun-15 | 19352 | 3 | 4 | | | | IV-1 | Ndufa12 | 55967 | 23-May-15 |
| 19257 | 3 | 4 | | | | IV-1 | Mturn | 222166 | 4-May-15 | 19353 | 3 | 4 | | | | IV-1 | Ndufa3 | 4696 | 4-May-15 |
| 19258 | 3 | 4 | | | | IV-1 | Mtx2 | 10651 | 4-May-15 | 19354 | 3 | 4 | | | | IV-1 | Ndufaf4 | 29078 | 4-May-15 |
| 19259 | 3 | 4 | | | | IV-1 | Muc5ac | 4586 | 7-Jun-15 | 19355 | 3 | 4 | | | | IV-1 | Ndufb10 | 4716 | 12-May-15 |
| 19260 | 3 | 4 | | | | IV-1 | Mug2 | | | 19356 | 3 | 4 | | | | IV-1 | Ndufb2 | 4708 | 12-May-15 |
| 19261 | 3 | 4 | | | | IV-1 | Mug-ps1 | | | 19357 | 3 | 4 | | | | IV-1 | Ndufb6 | 4712 | 4-May-15 |
| 19262 | 3 | 4 | | | | IV-1 | Mup4 | | | 19358 | 3 | 4 | | | | IV-1 | Ndufb7 | 4713 | 4-May-15 |
| 19263 | 3 | 4 | | | | IV-1 | Mvb12b | 89853 | 12-May-15 | 19359 | 3 | 4 | | | | IV-1 | Ndufs1 | 4719 | 4-May-15 |
| 19264 | 3 | 4 | | | | IV-1 | Mycbp2 | 23077 | 4-May-15 | 19360 | 3 | 4 | | | | IV-1 | Necab2 | 54550 | 12-May-15 |
| 19265 | 3 | 4 | | | | IV-1 | Mycbpap | 84073 | 4-May-15 | 19361 | 3 | 4 | | | | IV-1 | Necab3 | 63941 | 4-May-15 |
| 19266 | 3 | 4 | | | | IV-1 | Myct1 | 80177 | 4-May-15 | 19362 | 3 | 4 | | | | IV-1 | Necap1 | 25977 | 4-May-15 |
| 19267 | 3 | 4 | | | | IV-1 | Myf5 | 4617 | 28-May-15 | 19363 | 3 | 4 | | | | IV-1 | Necap2 | 55707 | 4-May-15 |
| 19268 | 3 | 4 | | | | IV-1 | Myf6 | 4618 | 28-May-15 | 19364 | 3 | 4 | | | | IV-1 | Nedd4 | 4734 | 4-May-15 |
| 19269 | 3 | 4 | | | | IV-1 | Myg1 | 60314 | 4-May-15 | 19365 | 3 | 4 | | | | IV-1 | Nedd4l | 23327 | 17-May-15 |
| 19270 | 3 | 4 | | | | IV-1 | Mylk | 4638 | 28-May-15 | 19366 | 3 | 4 | | | | IV-1 | Nefl | 4747 | 23-May-15 |

Fig. 30 - 103

| | | | | | | | | | | | | | | | | |
|---|---|---|---|---|---|---|---|---|---|---|---|---|---|---|---|---|
| 19367 | 3 | 4 | | | | IV-1 | Nefm | 4741 | 28-May-15 | 19463 | 3 | 4 | | | IV-1 | Nova2 | 4858 | 4-May-15 |
| 19368 | 3 | 4 | | | | IV-1 | Negr1 | 257194 | 4-May-15 | 19464 | 3 | 4 | | | IV-1 | Nox1 | 27035 | 10-May-15 |
| 19369 | 3 | 4 | | | | IV-1 | Nek10 | 152110 | 12-May-15 | 19465 | 3 | 4 | | | IV-1 | Nox3 | 50508 | 3-May-15 |
| 19370 | 3 | 4 | | | | IV-1 | Nek11 | 79858 | 28-May-15 | 19466 | 3 | 4 | | | IV-1 | Noxred1 | 122945 | 4-May-15 |
| 19371 | 3 | 4 | | | | IV-1 | Nek4 | 6787 | 4-May-15 | 19467 | 3 | 4 | | | IV-1 | Npas4 | 266743 | 28-May-15 |
| 19372 | 3 | 4 | | | | IV-1 | Nek5 | 341676 | 4-May-15 | 19468 | 3 | 4 | | | IV-1 | Npb | 256933 | 4-May-15 |
| 19373 | 3 | 4 | | | | IV-1 | Nek8 | 284086 | 7-Jun-15 | 19469 | 3 | 4 | | | IV-1 | Npbwr1 | 2831 | 4-May-15 |
| 19374 | 3 | 4 | | | | IV-1 | Nek9 | 91754 | 4-May-15 | 19470 | 3 | 4 | | | IV-1 | Npc1 | 4864 | 7-Jun-15 |
| 19375 | 3 | 4 | | | | IV-1 | Nelfa | 7469 | 4-May-15 | 19471 | 3 | 4 | | | IV-1 | Npdc1 | 56654 | 4-May-15 |
| 19376 | 3 | 4 | | | | IV-1 | Nelfcd | 51497 | 4-May-15 | 19472 | 3 | 4 | | | IV-1 | Npffr2 | 10886 | 4-May-15 |
| 19377 | 3 | 4 | | | | IV-1 | Nelfe | 7936 | 12-May-15 | 19473 | 3 | 4 | | | IV-1 | Nphp1 | 4867 | 23-May-15 |
| 19378 | 3 | 4 | | | | IV-1 | Nellios | | | 19474 | 3 | 4 | | | IV-1 | Nphp3 | 27031 | 12-May-15 |
| 19379 | 3 | 4 | | | | IV-1 | Nell2 | 4753 | 12-May-15 | 19475 | 3 | 4 | | | IV-1 | Nphp4 | 261734 | 17-May-15 |
| 19380 | 3 | 4 | | | | IV-1 | Nenf | 29937 | 4-May-15 | 19476 | 3 | 4 | | | IV-1 | Nphs1 | 4868 | 4-May-15 |
| 19381 | 3 | 4 | | | | IV-1 | Neo1 | 4756 | 4-May-15 | 19477 | 3 | 4 | | | IV-1 | Nphs1os | | |
| 19382 | 3 | 4 | | | | IV-1 | Neto2 | 81831 | 4-May-15 | 19478 | 3 | 4 | | | IV-1 | Npm3 | 10360 | 4-May-15 |
| 19383 | 3 | 4 | | | | IV-1 | Neurl1a | | | 19479 | 3 | 4 | | | IV-1 | Npr1 | 4881 | 24-May-15 |
| 19384 | 3 | 4 | | | | IV-1 | Neurod1 | 4760 | 28-May-15 | 19480 | 3 | 4 | | | IV-1 | Nps | 594857 | 4-May-15 |
| 19385 | 3 | 4 | | | | IV-1 | Neurod2 | 4761 | 28-May-15 | 19481 | 3 | 4 | | | IV-1 | Nptxr | 23467 | 4-May-15 |
| 19386 | 3 | 4 | | | | IV-1 | Neurod4 | 58158 | 7-Jun-15 | 19482 | 3 | 4 | | | IV-1 | Npvf | 64111 | 4-May-15 |
| 19387 | 3 | 4 | | | | IV-1 | Neurod6 | 63974 | 4-May-15 | 19483 | 3 | 4 | | | IV-1 | Npw | 283869 | 12-May-15 |
| 19388 | 3 | 4 | | | | IV-1 | Neurog1 | 4762 | 12-May-15 | 19484 | 3 | 4 | | | IV-1 | Npy4r | 5540 | 4-May-15 |
| 19389 | 3 | 4 | | | | IV-1 | Neurog2 | 63973 | 4-May-15 | 19485 | 3 | 4 | | | IV-1 | Npy5r | 4889 | 4-May-15 |
| 19390 | 3 | 4 | | | | IV-1 | Nfam1 | 150372 | 4-May-15 | 19486 | 3 | 4 | | | IV-1 | Npy6r | 4888 | 4-May-15 |
| 19391 | 3 | 4 | | | | IV-1 | Nfatc1 | 4772 | 31-May-15 | 19487 | 3 | 4 | | | IV-1 | Nr0b2 | 8431 | 24-May-15 |
| 19392 | 3 | 4 | | | | IV-1 | Nfatc2 | 4773 | 28-May-15 | 19488 | 3 | 4 | | | IV-1 | Nr1h3 | 10062 | 31-May-15 |
| 19393 | 3 | 4 | | | | IV-1 | Nfatc2ip | 84901 | 4-May-15 | 19489 | 3 | 4 | | | IV-1 | Nr1i2 | 8856 | 24-May-15 |
| 19394 | 3 | 4 | | | | IV-1 | Nfatc3 | 4775 | 24-May-15 | 19490 | 3 | 4 | | | IV-1 | Nr2c2 | 7182 | 31-May-15 |
| 19395 | 3 | 4 | | | | IV-1 | Nfatc4 | 4776 | 24-May-15 | 19491 | 3 | 4 | | | IV-1 | Nr2c2ap | 126382 | 4-May-15 |
| 19396 | 3 | 4 | | | | IV-1 | Nfe2l2 | 4780 | 31-May-15 | 19492 | 3 | 4 | | | IV-1 | Nr2f1 | 7025 | 7-Jun-15 |
| 19397 | 3 | 4 | | | | IV-1 | Nfic | 4782 | 17-May-15 | 19493 | 3 | 4 | | | IV-1 | Nr3c1 | 2908 | 31-May-15 |
| 19398 | 3 | 4 | | | | IV-1 | Nfkb1 | 4790 | 28-May-15 | 19494 | 3 | 4 | | | IV-1 | Nr5a2 | 2494 | 12-May-15 |
| 19399 | 3 | 4 | | | | IV-1 | Nfkb2 | 4791 | 28-May-15 | 19495 | 3 | 4 | | | IV-1 | Nr6a1 | 2649 | 4-May-15 |
| 19400 | 3 | 4 | | | | IV-1 | Nfs1 | 9054 | 4-May-15 | 19496 | 3 | 4 | | | IV-1 | Nradd | | |
| 19401 | 3 | 4 | | | | IV-1 | Nfx1 | 152518 | 12-May-15 | 19497 | 3 | 4 | | | IV-1 | Nrbp1 | 29959 | 4-May-15 |
| 19402 | 3 | 4 | | | | IV-1 | Nfya | 4800 | 4-May-15 | 19498 | 3 | 4 | | | IV-1 | Nrbp2 | 340371 | 4-May-15 |
| 19403 | 3 | 4 | | | | IV-1 | Nfyc | 4802 | 21-May-15 | 19499 | 3 | 4 | | | IV-1 | Nrde2 | 55051 | 4-May-15 |
| 19404 | 3 | 4 | | | | IV-1 | Ngb | 58157 | 7-Jun-15 | 19500 | 3 | 4 | | | IV-1 | Nrg3os | | |
| 19405 | 3 | 4 | | | | IV-1 | Nhlh2 | 4808 | 28-May-15 | 19501 | 3 | 4 | | | IV-1 | Nrip2 | 83714 | 4-May-15 |
| 19406 | 3 | 4 | | | | IV-1 | Nhlrc1 | 378884 | 23-May-15 | 19502 | 3 | 4 | | | IV-1 | Nrl | 4901 | 23-May-15 |
| 19407 | 3 | 4 | | | | IV-1 | Nhs | 4810 | 17-May-15 | 19503 | 3 | 4 | | | IV-1 | Nrp1 | 8829 | 7-Jun-15 |
| 19408 | 3 | 4 | | | | IV-1 | Nicn3 | 84276 | 4-May-15 | 19504 | 3 | 4 | | | IV-1 | Nrp2 | 8828 | 7-Jun-15 |
| 19409 | 3 | 4 | | | | IV-1 | Nifk | 84365 | 4-May-15 | 19505 | 3 | 4 | | | IV-1 | Nrsn2 | 80023 | 4-May-15 |
| 19410 | 3 | 4 | | | | IV-1 | Nipsnap1 | 8508 | 17-May-15 | 19506 | 3 | 4 | | | IV-1 | Nrtn | 4902 | 23-May-15 |
| 19411 | 3 | 4 | | | | IV-1 | Nipsnap3b | 55335 | 12-May-15 | 19507 | 3 | 4 | | | IV-1 | Nrxn2 | 9379 | 4-May-15 |
| 19412 | 3 | 4 | | | | IV-1 | Nisch | 11188 | 17-May-15 | 19508 | 3 | 4 | | | IV-1 | Nsa2 | 10412 | 4-May-15 |
| 19413 | 3 | 4 | | | | IV-1 | Nit1 | 4817 | 4-May-15 | 19509 | 3 | 4 | | | IV-1 | Nsd1 | 64324 | 23-May-15 |
| 19414 | 3 | 4 | | | | IV-1 | Nit2 | 56954 | 12-May-15 | 19510 | 3 | 4 | | | IV-1 | Nsg2 | | |
| 19415 | 3 | 4 | | | | IV-1 | Nkain3 | 286183 | 4-May-15 | 19511 | 3 | 4 | | | IV-1 | Nsmce1 | 197370 | 23-May-15 |
| 19416 | 3 | 4 | | | | IV-1 | Nkpd1 | 284353 | 4-May-15 | 19512 | 3 | 4 | | | IV-1 | Nsmce2 | 286053 | 17-May-15 |
| 19417 | 3 | 4 | | | | IV-1 | Nkrf | 55922 | 4-May-15 | 19513 | 3 | 4 | | | IV-1 | Nsmce4a | 54780 | 4-May-15 |
| 19418 | 3 | 4 | | | | IV-1 | Nkx1-1 | 54729 | 4-May-15 | 19514 | 3 | 4 | | | IV-1 | Nsun3 | 63899 | 4-May-15 |
| 19419 | 3 | 4 | | | | IV-1 | Nkx1-2 | 390010 | 4-May-15 | 19515 | 3 | 4 | | | IV-1 | Nsun4 | 387338 | 4-May-15 |
| 19420 | 3 | 4 | | | | IV-1 | Nkx2-2os | | | 19516 | 3 | 4 | | | IV-1 | Nsun6 | 221078 | 12-May-15 |
| 19421 | 3 | 4 | | | | IV-1 | Nkx2-3 | 159296 | 4-May-15 | 19517 | 3 | 4 | | | IV-1 | Nsun7 | 79730 | 4-May-15 |
| 19422 | 3 | 4 | | | | IV-1 | Nkx2-4 | 644524 | 4-May-15 | 19518 | 3 | 4 | | | IV-1 | Nt5c | 30833 | 4-May-15 |
| 19423 | 3 | 4 | | | | IV-1 | Nkx2-9 | 26257 | 12-May-15 | 19519 | 3 | 4 | | | IV-1 | Nt5c2 | 22978 | 2-Jun-15 |
| 19424 | 3 | 4 | | | | IV-1 | Nle1 | 54475 | 4-May-15 | 19520 | 3 | 4 | | | IV-1 | Nt5dc2 | 64943 | 4-May-15 |
| 19425 | 3 | 4 | | | | IV-1 | Nlk | 51701 | 7-Jun-15 | 19521 | 3 | 4 | | | IV-1 | Ntan1 | 123803 | 4-May-15 |
| 19426 | 3 | 4 | | | | IV-1 | Nln | 57486 | 4-May-15 | 19522 | 3 | 4 | | | IV-1 | Ntm | 50863 | 2-Jun-15 |
| 19427 | 3 | 4 | | | | IV-1 | Nlrp12 | 91662 | 4-May-15 | 19523 | 3 | 4 | | | IV-1 | Ntn4 | 59277 | 7-Jun-15 |
| 19428 | 3 | 4 | | | | IV-1 | Nlrp14 | 338323 | 4-May-15 | 19524 | 3 | 4 | | | IV-1 | Ntng1 | 22854 | 7-Jun-15 |
| 19429 | 3 | 4 | | | | IV-1 | Nlrp1a | | | 19525 | 3 | 4 | | | IV-1 | Ntng2 | 84628 | 4-May-15 |
| 19430 | 3 | 4 | | | | IV-1 | Nlrp1b | | | 19526 | 3 | 4 | | | IV-1 | Nubp1 | 4682 | 10-Jun-15 |
| 19431 | 3 | 4 | | | | IV-1 | Nlrp2 | 55655 | 28-May-15 | 19527 | 3 | 4 | | | IV-1 | Nubp2 | 10101 | 4-May-15 |
| 19432 | 3 | 4 | | | | IV-1 | Nlrp4b | | | 19528 | 3 | 4 | | | IV-1 | Nubpl | 80224 | 4-May-15 |
| 19433 | 3 | 4 | | | | IV-1 | Nlrp4c | | | 19529 | 3 | 4 | | | IV-1 | Nudcd1 | 84955 | 12-May-15 |
| 19434 | 3 | 4 | | | | IV-1 | Nlrp4e | | | 19530 | 3 | 4 | | | IV-1 | Nudcd3 | 23386 | 4-May-15 |
| 19435 | 3 | 4 | | | | IV-1 | Nlrp5 | 126206 | 4-May-15 | 19531 | 3 | 4 | | | IV-1 | Nudt1 | 4521 | 31-May-15 |
| 19436 | 3 | 4 | | | | IV-1 | Nme3 | 4832 | 12-May-15 | 19532 | 3 | 4 | | | IV-1 | Nudt14 | 256281 | 4-May-15 |
| 19437 | 3 | 4 | | | | IV-1 | Nme8 | 51314 | 28-May-15 | 19533 | 3 | 4 | | | IV-1 | Nudt16l1 | 84309 | 4-May-15 |
| 19438 | 3 | 4 | | | | IV-1 | Nmnat1 | 64802 | 23-May-15 | 19534 | 3 | 4 | | | IV-1 | Nudt21 | 11051 | 4-May-15 |
| 19439 | 3 | 4 | | | | IV-1 | Nmt1 | 4836 | 4-May-15 | 19535 | 3 | 4 | | | IV-1 | Nudt3 | 11165 | 4-May-15 |
| 19440 | 3 | 4 | | | | IV-1 | Nmt2 | 9397 | 12-May-15 | 19536 | 3 | 4 | | | IV-1 | Nudt6 | 11162 | 12-May-15 |
| 19441 | 3 | 4 | | | | IV-1 | Nmur1 | 10316 | 12-May-15 | 19537 | 3 | 4 | | | IV-1 | Nufip2 | 57532 | 4-May-15 |
| 19442 | 3 | 4 | | | | IV-1 | Nobox | 135935 | 28-May-15 | 19538 | 3 | 4 | | | IV-1 | Nuggc | 389643 | 4-May-15 |
| 19443 | 3 | 4 | | | | IV-1 | Noc3l | 64318 | 4-May-15 | 19539 | 3 | 4 | | | IV-1 | Numb | 8650 | 4-May-15 |
| 19444 | 3 | 4 | | | | IV-1 | Noc4l | 79050 | 12-May-15 | 19540 | 3 | 4 | | | IV-1 | Numbl | 9253 | 12-May-15 |
| 19445 | 3 | 4 | | | | IV-1 | Nod1 | 10392 | 29-May-15 | 19541 | 3 | 4 | | | IV-1 | Nup153 | 9972 | 4-May-15 |
| 19446 | 3 | 4 | | | | IV-1 | Nog | 9241 | 13-May-15 | 19542 | 3 | 4 | | | IV-1 | Nup155 | 9631 | 4-May-15 |
| 19447 | 3 | 4 | | | | IV-1 | Nol11 | 25926 | 4-May-15 | 19543 | 3 | 4 | | | IV-1 | Nup188 | 23511 | 4-May-15 |
| 19448 | 3 | 4 | | | | IV-1 | Nol12 | 79159 | 12-May-15 | 19544 | 3 | 4 | | | IV-1 | Nup205 | 23165 | 12-May-15 |
| 19449 | 3 | 4 | | | | IV-1 | Nol6 | 65083 | 4-May-15 | 19545 | 3 | 4 | | | IV-1 | Nup214 | 8021 | 12-May-15 |
| 19450 | 3 | 4 | | | | IV-1 | Nol7 | 51406 | 4-May-15 | 19546 | 3 | 4 | | | IV-1 | Nup35 | 129401 | 4-May-15 |
| 19451 | 3 | 4 | | | | IV-1 | Nol8 | 55035 | 4-May-15 | 19547 | 3 | 4 | | | IV-1 | Nup54 | 53371 | 4-May-15 |
| 19452 | 3 | 4 | | | | IV-1 | Nol9 | 79707 | 4-May-15 | 19548 | 3 | 4 | | | IV-1 | Nup62 | 23636 | 4-May-15 |
| 19453 | 3 | 4 | | | | IV-1 | Nom1 | 64434 | 4-May-15 | 19549 | 3 | 4 | | | IV-1 | Nup62-il1 | | |
| 19454 | 3 | 4 | | | | IV-1 | Nomo1 | 23420 | 4-May-15 | 19550 | 3 | 4 | | | IV-1 | Nup88 | 4927 | 4-May-15 |
| 19455 | 3 | 4 | | | | IV-1 | Nono | 4841 | 1-Jun-15 | 19551 | 3 | 4 | | | IV-1 | Nup93 | 9688 | 28-May-15 |
| 19456 | 3 | 4 | | | | IV-1 | Nop10 | 55505 | 31-May-15 | 19552 | 3 | 4 | | | IV-1 | Nupl2 | 11097 | 12-May-15 |
| 19457 | 3 | 4 | | | | IV-1 | Nop14 | 8602 | 12-May-15 | 19553 | 3 | 4 | | | IV-1 | Nvl | 4931 | 4-May-15 |
| 19458 | 3 | 4 | | | | IV-1 | Nop16 | 51491 | 12-May-15 | 19554 | 3 | 4 | | | IV-1 | Nxf1 | 10482 | 1-Jun-15 |
| 19459 | 3 | 4 | | | | IV-1 | Nos1 | 4842 | 7-Jun-15 | 19555 | 3 | 4 | | | IV-1 | Nxf2 | 56001 | 14-May-15 |
| 19460 | 3 | 4 | | | | IV-1 | Nos1ap | 9722 | 1-Jun-15 | 19556 | 3 | 4 | | | IV-1 | Nxn | 64359 | 4-May-15 |
| 19461 | 3 | 4 | | | | IV-1 | Nostrin | 115677 | 4-May-15 | 19557 | 3 | 4 | | | IV-1 | Nxph2 | 11249 | 4-May-15 |
| 19462 | 3 | 4 | | | | IV-1 | Notch2 | 4853 | 23-May-15 | 19558 | 3 | 4 | | | IV-1 | Nyap1 | 222950 | 4-May-15 |

Fig. 30 - 104

| | | | | | | | | | |
|---|---|---|---|---|---|---|---|---|---|
| 19559 | 3 | 4 | | | IV-1 | Nynrin | 57523 | 4-May-15 |
| 19560 | 3 | 4 | | | IV-1 | Nyx | 60506 | 23-May-15 |
| 19561 | 3 | 4 | | | IV-1 | Oacyl | | |
| 19562 | 3 | 4 | | | IV-1 | Oas1e | | |
| 19563 | 3 | 4 | | | IV-1 | Oas1f | | |
| 19564 | 3 | 4 | | | IV-1 | Oaz2 | 4947 | 4-May-15 |
| 19565 | 3 | 4 | | | IV-1 | Obox2 | | |
| 19566 | 3 | 4 | | | IV-1 | Obox3 | | |
| 19567 | 3 | 4 | | | IV-1 | Obox5 | | |
| 19568 | 3 | 4 | | | IV-1 | Obox6 | | |
| 19569 | 3 | 4 | | | IV-1 | Obp1a | | |
| 19570 | 3 | 4 | | | IV-1 | Obp2a | 29991 | 12-May-15 |
| 19571 | 3 | 4 | | | IV-1 | Oca2 | 4948 | 23-May-15 |
| 19572 | 3 | 4 | | | IV-1 | Odf3 | 113746 | 4-May-15 |
| 19573 | 3 | 4 | | | IV-1 | Ofcc1 | 266553 | 7-Jun-15 |
| 19574 | 3 | 4 | | | IV-1 | Ofd1 | 8481 | 31-May-15 |
| 19575 | 3 | 4 | | | IV-1 | Ogdh | 4967 | 12-May-15 |
| 19576 | 3 | 4 | | | IV-1 | Ogfod2 | 79676 | 23-May-15 |
| 19577 | 3 | 4 | | | IV-1 | Ogfod3 | 79701 | 4-May-15 |
| 19578 | 3 | 4 | | | IV-1 | Ogfr | 11054 | 4-May-15 |
| 19579 | 3 | 4 | | | IV-1 | Ogfrl1 | 79627 | 12-May-15 |
| 19580 | 3 | 4 | | | IV-1 | Ogg1 | 4968 | 4-May-15 |
| 19581 | 3 | 4 | | | IV-1 | Olah | 55301 | 4-May-15 |
| 19582 | 3 | 4 | | | IV-1 | Olfm1 | 10439 | 4-May-15 |
| 19583 | 3 | 4 | | | IV-1 | Olfr10 | | |
| 19584 | 3 | 4 | | | IV-1 | Olfr100 | | |
| 19585 | 3 | 4 | | | IV-1 | Olfr1000 | | |
| 19586 | 3 | 4 | | | IV-1 | Olfr1002 | | |
| 19587 | 3 | 4 | | | IV-1 | Olfr1006 | | |
| 19588 | 3 | 4 | | | IV-1 | Olfr1008 | | |
| 19589 | 3 | 4 | | | IV-1 | Olfr1118 | | |
| 19590 | 3 | 4 | | | IV-1 | Olfr1128 | | |
| 19591 | 3 | 4 | | | IV-1 | Olfr1136 | | |
| 19592 | 3 | 4 | | | IV-1 | Olfr1151 | | |
| 19593 | 3 | 4 | | | IV-1 | Olfr1167 | | |
| 19594 | 3 | 4 | | | IV-1 | Olfr1276 | | |
| 19595 | 3 | 4 | | | IV-1 | Olfr1287 | | |
| 19596 | 3 | 4 | | | IV-1 | Olfr1306 | | |
| 19597 | 3 | 4 | | | IV-1 | Olfr1346 | | |
| 19598 | 3 | 4 | | | IV-1 | Olfr1350 | | |
| 19599 | 3 | 4 | | | IV-1 | Olfr1351 | | |
| 19600 | 3 | 4 | | | IV-1 | Olfr1381 | | |
| 19601 | 3 | 4 | | | IV-1 | Olfr1382 | | |
| 19602 | 3 | 4 | | | IV-1 | Olfr139 | | |
| 19603 | 3 | 4 | | | IV-1 | Olfr1390 | | |
| 19604 | 3 | 4 | | | IV-1 | Olfr1410 | | |
| 19605 | 3 | 4 | | | IV-1 | Olfr142 | | |
| 19606 | 3 | 4 | | | IV-1 | Olfr143 | | |
| 19607 | 3 | 4 | | | IV-1 | Olfr1450 | | |
| 19608 | 3 | 4 | | | IV-1 | Olfr1500 | | |
| 19609 | 3 | 4 | | | IV-1 | Olfr1513 | | |
| 19610 | 3 | 4 | | | IV-1 | Olfr170 | | |
| 19611 | 3 | 4 | | | IV-1 | Olfr196 | | |
| 19612 | 3 | 4 | | | IV-1 | Olfr20 | | |
| 19613 | 3 | 4 | | | IV-1 | Olfr205 | | |
| 19614 | 3 | 4 | | | IV-1 | Olfr222 | | |
| 19615 | 3 | 4 | | | IV-1 | Olfr225 | | |
| 19616 | 3 | 4 | | | IV-1 | Olfr243 | | |
| 19617 | 3 | 4 | | | IV-1 | Olfr297 | | |
| 19618 | 3 | 4 | | | IV-1 | Olfr314 | | |
| 19619 | 3 | 4 | | | IV-1 | Olfr367-ps | | |
| 19620 | 3 | 4 | | | IV-1 | Olfr373 | | |
| 19621 | 3 | 4 | | | IV-1 | Olfr43 | | |
| 19622 | 3 | 4 | | | IV-1 | Olfr444 | | |
| 19623 | 3 | 4 | | | IV-1 | Olfr446 | | |
| 19624 | 3 | 4 | | | IV-1 | Olfr557 | | |
| 19625 | 3 | 4 | | | IV-1 | Olfr568 | | |
| 19626 | 3 | 4 | | | IV-1 | Olfr703 | | |
| 19627 | 3 | 4 | | | IV-1 | Olfr71 | | |
| 19628 | 3 | 4 | | | IV-1 | Olfr74 | | |
| 19629 | 3 | 4 | | | IV-1 | Olfr740 | | |
| 19630 | 3 | 4 | | | IV-1 | Olfr770 | | |
| 19631 | 3 | 4 | | | IV-1 | Olfr788 | | |
| 19632 | 3 | 4 | | | IV-1 | Olfr798 | | |
| 19633 | 3 | 4 | | | IV-1 | Olfr883 | | |
| 19634 | 3 | 4 | | | IV-1 | Olfr884 | | |
| 19635 | 3 | 4 | | | IV-1 | Olfr930 | | |
| 19636 | 3 | 4 | | | IV-1 | Olfr95 | | |
| 19637 | 3 | 4 | | | IV-1 | Olfr986 | | |
| 19638 | 3 | 4 | | | IV-1 | Olig1 | 116448 | 4-May-15 |
| 19639 | 3 | 4 | | | IV-1 | Omp | 4975 | 4-May-15 |
| 19640 | 3 | 4 | | | IV-1 | Omt2b | | |
| 19641 | 3 | 4 | | | IV-1 | Oog1 | | |
| 19642 | 3 | 4 | | | IV-1 | Oog4 | | |
| 19643 | 3 | 4 | | | IV-1 | Oosp1 | 255649 | 4-May-15 |
| 19644 | 3 | 4 | | | IV-1 | Ophn1 | 4983 | 12-May-15 |
| 19645 | 3 | 4 | | | IV-1 | Opn1sw | 611 | 12-May-15 |
| 19646 | 3 | 4 | | | IV-1 | Opn3 | 23596 | 12-May-15 |
| 19647 | 3 | 4 | | | IV-1 | Oprd1 | 4985 | 4-May-15 |
| 19648 | 3 | 4 | | | IV-1 | Oprk1 | 4986 | 12-May-15 |
| 19649 | 3 | 4 | | | IV-1 | Oprl1 | 4987 | 4-May-15 |
| 19650 | 3 | 4 | | | IV-1 | Oprm1 | 4988 | 31-May-15 |
| 19651 | 3 | 4 | | | IV-1 | Oraov1 | 220064 | 4-May-15 |
| 19652 | 3 | 4 | | | IV-1 | Orc4 | 5000 | 4-May-15 |
| 19653 | 3 | 4 | | | IV-1 | Orc5 | 5001 | 4-May-15 |
| 19654 | 3 | 4 | | | IV-1 | Orc6 | 23594 | 4-May-15 |
| 19655 | 3 | 4 | | | IV-1 | Os9 | 10956 | 3-May-15 |
| 19656 | 3 | 4 | | | IV-1 | Osbp | 5007 | 28-May-15 |
| 19657 | 3 | 4 | | | IV-1 | Osbp2 | 23762 | 12-May-15 |
| 19658 | 3 | 4 | | | IV-1 | Osbpl2 | 9885 | 22-May-15 |
| 19659 | 3 | 4 | | | IV-1 | Osbpl9 | 114883 | 12-May-15 |
| 19660 | 3 | 4 | | | IV-1 | Oscar | 126014 | 17-May-15 |
| 19661 | 3 | 4 | | | IV-1 | Oser1 | 51526 | 4-May-15 |
| 19662 | 3 | 4 | | | IV-1 | Osgep | 55644 | 4-May-15 |
| 19663 | 3 | 4 | | | IV-1 | Osgepl1 | 64172 | 4-May-15 |
| 19664 | 3 | 4 | | | IV-1 | Ostc | 58505 | 4-May-15 |
| 19665 | 3 | 4 | | | IV-1 | Ostf1 | 26578 | 4-May-15 |
| 19666 | 3 | 4 | | | IV-1 | Otoa | 146183 | 23-May-15 |
| 19667 | 3 | 4 | | | IV-1 | Otogl | 283310 | 7-Jun-15 |
| 19668 | 3 | 4 | | | IV-1 | Otol1 | 131149 | 4-May-15 |
| 19669 | 3 | 4 | | | IV-1 | Otop3 | 347741 | 4-May-15 |
| 19670 | 3 | 4 | | | IV-1 | Otor | 56914 | 12-May-15 |
| 19671 | 3 | 4 | | | IV-1 | Otud5 | 55593 | 4-May-15 |
| 19672 | 3 | 4 | | | IV-1 | Otud6a | 139562 | 4-May-15 |
| 19673 | 3 | 4 | | | IV-1 | Otud6b | 51633 | 4-May-15 |
| 19674 | 3 | 4 | | | IV-1 | Otud7a | 161725 | 4-May-15 |
| 19675 | 3 | 4 | | | IV-1 | Otud7b | 56957 | 17-May-15 |
| 19676 | 3 | 4 | | | IV-1 | Otulin | 90268 | 4-May-15 |
| 19677 | 3 | 4 | | | IV-1 | Otx2 | 5015 | 28-May-15 |
| 19678 | 3 | 4 | | | IV-1 | Otx2os1 | 100309464 | 21-May-15 |
| 19679 | 3 | 4 | | | IV-1 | Ovca2 | 124641 | 4-May-15 |
| 19680 | 3 | 4 | | | IV-1 | Ovol2 | 58495 | 4-May-15 |
| 19681 | 3 | 4 | | | IV-1 | Oxct2b | | |
| 19682 | 3 | 4 | | | IV-1 | Oxgr1 | 27199 | 4-May-15 |
| 19683 | 3 | 4 | | | IV-1 | Oxsm | 54995 | 4-May-15 |
| 19684 | 3 | 4 | | | IV-1 | Oxt | 5020 | 4-May-15 |
| 19685 | 3 | 4 | | | IV-1 | Oxtr | 5021 | 31-May-15 |
| 19686 | 3 | 4 | | | IV-1 | Pabpc2 | 26986 | 12-May-15 |
| 19687 | 3 | 4 | | | IV-1 | Pabpc5 | 140886 | 4-May-15 |
| 19688 | 3 | 4 | | | IV-1 | Pabpc6 | | |
| 19689 | 3 | 4 | | | IV-1 | Pabpn1 | 8106 | 23-May-15 |
| 19690 | 3 | 4 | | | IV-1 | Pabpn1l | 390748 | 4-May-15 |
| 19691 | 3 | 4 | | | IV-1 | Pacs2 | 23241 | 21-May-15 |
| 19692 | 3 | 4 | | | IV-1 | Pacsin1 | 29993 | 4-May-15 |
| 19693 | 3 | 4 | | | IV-1 | Pacsin3 | 29763 | 4-May-15 |
| 19694 | 3 | 4 | | | IV-1 | Padi1 | 29943 | 4-May-15 |
| 19695 | 3 | 4 | | | IV-1 | Paf1 | 54623 | 7-Jun-15 |
| 19696 | 3 | 4 | | | IV-1 | Pafah1b1 | 5048 | 23-May-15 |
| 19697 | 3 | 4 | | | IV-1 | Pafah1b2 | 5049 | 2-Jun-15 |
| 19698 | 3 | 4 | | | IV-1 | Paip1 | 10605 | 12-May-15 |
| 19699 | 3 | 4 | | | IV-1 | Paip2 | 51247 | 4-May-15 |
| 19700 | 3 | 4 | | | IV-1 | Paip2b | 400961 | 4-May-15 |
| 19701 | 3 | 4 | | | IV-1 | Pak2 | 5062 | 7-Jun-15 |
| 19702 | 3 | 4 | | | IV-1 | Pak3 | 5063 | 7-Jun-15 |
| 19703 | 3 | 4 | | | IV-1 | Pak4 | 10298 | 4-May-15 |
| 19704 | 3 | 4 | | | IV-1 | Palb2 | 79728 | 24-May-15 |
| 19705 | 3 | 4 | | | IV-1 | Palm3 | 342979 | 4-May-15 |
| 19706 | 3 | 4 | | | IV-1 | Pan3 | 255967 | 7-Jun-15 |
| 19707 | 3 | 4 | | | IV-1 | Pank1 | 53354 | 4-May-15 |
| 19708 | 3 | 4 | | | IV-1 | Pank3 | 79646 | 4-May-15 |
| 19709 | 3 | 4 | | | IV-1 | Paox | 196743 | 4-May-15 |
| 19710 | 3 | 4 | | | IV-1 | Papd5 | 64282 | 4-May-15 |
| 19711 | 3 | 4 | | | IV-1 | Papd7 | 11044 | 4-May-15 |
| 19712 | 3 | 4 | | | IV-1 | Papln | 89932 | 4-May-15 |
| 19713 | 3 | 4 | | | IV-1 | Papolb | 56903 | 4-May-15 |
| 19714 | 3 | 4 | | | IV-1 | Papolg | 64895 | 4-May-15 |
| 19715 | 3 | 4 | | | IV-1 | Pappa | 5069 | 17-May-15 |
| 19716 | 3 | 4 | | | IV-1 | Pard6a | 50855 | 4-May-15 |
| 19717 | 3 | 4 | | | IV-1 | Park2 | 5071 | 31-May-15 |
| 19718 | 3 | 4 | | | IV-1 | Park7 | 11315 | 31-May-15 |
| 19719 | 3 | 4 | | | IV-1 | Parl | 55486 | 24-May-15 |
| 19720 | 3 | 4 | | | IV-1 | Parm1 | 25849 | 4-May-15 |
| 19721 | 3 | 4 | | | IV-1 | Parp1 | 142 | 31-May-15 |
| 19722 | 3 | 4 | | | IV-1 | Parp11 | 57097 | 2-Jun-15 |
| 19723 | 3 | 4 | | | IV-1 | Parp3 | 10039 | 4-May-15 |
| 19724 | 3 | 4 | | | IV-1 | Parp4 | 143 | 4-May-15 |
| 19725 | 3 | 4 | | | IV-1 | Parp6 | 56965 | 12-May-15 |
| 19726 | 3 | 4 | | | IV-1 | Parp8 | 79668 | 12-May-15 |
| 19727 | 3 | 4 | | | IV-1 | Patl2 | 197135 | 12-May-15 |
| 19728 | 3 | 4 | | | IV-1 | Patz1 | 23598 | 4-May-15 |
| 19729 | 3 | 4 | | | IV-1 | Pawr | 5074 | 24-May-15 |
| 19730 | 3 | 4 | | | IV-1 | Pax6os1 | | |
| 19731 | 3 | 4 | | | IV-1 | Pax7 | 5081 | 12-May-15 |
| 19732 | 3 | 4 | | | IV-1 | Paxip1 | 22976 | 31-May-15 |
| 19733 | 3 | 4 | | | IV-1 | Pbrm1 | 55193 | 4-May-15 |
| 19734 | 3 | 4 | | | IV-1 | Pbsn | | |
| 19735 | 3 | 4 | | | IV-1 | Pbx1 | 5087 | 28-May-15 |
| 19736 | 3 | 4 | | | IV-1 | Pbx2 | 5089 | 7-Jun-15 |
| 19737 | 3 | 4 | | | IV-1 | Pbx3 | 5090 | 17-May-15 |
| 19738 | 3 | 4 | | | IV-1 | Pcbp2 | 5094 | 4-May-15 |
| 19739 | 3 | 4 | | | IV-1 | Pcbp3 | 54039 | 4-May-15 |
| 19740 | 3 | 4 | | | IV-1 | Pcca | 5095 | 23-May-15 |
| 19741 | 3 | 4 | | | IV-1 | Pcdh11x | 27328 | 12-May-15 |
| 19742 | 3 | 4 | | | IV-1 | Pcdh12 | 51294 | 4-May-15 |
| 19743 | 3 | 4 | | | IV-1 | Pcdh17 | 27253 | 4-May-15 |
| 19744 | 3 | 4 | | | IV-1 | Pcdh20 | 64881 | 4-May-15 |
| 19745 | 3 | 4 | | | IV-1 | Pcdh7 | 5099 | 4-May-15 |
| 19746 | 3 | 4 | | | IV-1 | Pcdh8 | 5100 | 18-May-15 |
| 19747 | 3 | 4 | | | IV-1 | Pcdh9 | 5101 | 4-May-15 |
| 19748 | 3 | 4 | | | IV-1 | Pcdha1 | 56147 | 4-May-15 |
| 19749 | 3 | 4 | | | IV-1 | Pcdha10 | 56139 | 4-May-15 |

Fig. 30 - 105

| | | | | | | | | | | | | | | | | | |
|---|---|---|---|---|---|---|---|---|---|---|---|---|---|---|---|---|---|
| 19750 | 3 | 4 | | | | | IV-1 | Pcdha11 | 56138 | 4-May-15 | 19846 | 3 | 4 | | | IV-1 | Pet100 | 100131801 | 4-May-15 |
| 19751 | 3 | 4 | | | | | IV-1 | Pcdha12 | 56137 | 4-May-15 | 19847 | 3 | 4 | | | IV-1 | Pet112 | 5188 | 23-May-15 |
| 19752 | 3 | 4 | | | | | IV-1 | Pcdha2 | 56146 | 4-May-15 | 19848 | 3 | 4 | | | IV-1 | Pex1 | 5189 | 13-Jun-15 |
| 19753 | 3 | 4 | | | | | IV-1 | Pcdha3 | 56145 | 4-May-15 | 19849 | 3 | 4 | | | IV-1 | Pex10 | 5192 | 4-May-15 |
| 19754 | 3 | 4 | | | | | IV-1 | Pcdha4 | 56144 | 4-May-15 | 19850 | 3 | 4 | | | IV-1 | Pex11g | 92960 | 12-May-15 |
| 19755 | 3 | 4 | | | | | IV-1 | Pcdha4-g | | | 19851 | 3 | 4 | | | IV-1 | Pex12 | 5193 | 23-May-15 |
| 19756 | 3 | 4 | | | | | IV-1 | Pcdha5 | 56143 | 4-May-15 | 19852 | 3 | 4 | | | IV-1 | Pex13 | 5194 | 28-May-15 |
| 19757 | 3 | 4 | | | | | IV-1 | Pcdha6 | 56142 | 4-May-15 | 19853 | 3 | 4 | | | IV-1 | Pex14 | 5195 | 4-May-15 |
| 19758 | 3 | 4 | | | | | IV-1 | Pcdha7 | 56141 | 4-May-15 | 19854 | 3 | 4 | | | IV-1 | Pex16 | 9409 | 23-May-15 |
| 19759 | 3 | 4 | | | | | IV-1 | Pcdha8 | 56140 | 4-May-15 | 19855 | 3 | 4 | | | IV-1 | Pex19 | 5824 | 4-May-15 |
| 19760 | 3 | 4 | | | | | IV-1 | Pcdha9 | 9752 | 4-May-15 | 19856 | 3 | 4 | | | IV-1 | Pex2 | 5828 | 17-May-15 |
| 19761 | 3 | 4 | | | | | IV-1 | Pcdhac1 | 56135 | 4-May-15 | 19857 | 3 | 4 | | | IV-1 | Pex5 | 5830 | 23-May-15 |
| 19762 | 3 | 4 | | | | | IV-1 | Pcdhb11 | 56125 | 4-May-15 | 19858 | 3 | 4 | | | IV-1 | Pex5l | 51555 | 3-Jun-15 |
| 19763 | 3 | 4 | | | | | IV-1 | Pcdhb13 | 56123 | 4-May-15 | 19859 | 3 | 4 | | | IV-1 | Pex6 | 5190 | 23-May-15 |
| 19764 | 3 | 4 | | | | | IV-1 | Pcdhb14 | 56122 | 12-May-15 | 19860 | 3 | 4 | | | IV-1 | Pex7 | 5191 | 23-May-15 |
| 19765 | 3 | 4 | | | | | IV-1 | Pcdhb15 | 56121 | 4-May-15 | 19861 | 3 | 4 | | | IV-1 | Pfdn2 | 5202 | 4-May-15 |
| 19766 | 3 | 4 | | | | | IV-1 | Pcdhb16 | 57717 | 12-May-15 | 19862 | 3 | 4 | | | IV-1 | Pfdn4 | 5203 | 4-May-15 |
| 19767 | 3 | 4 | | | | | IV-1 | Pcdhb17 | 54661 | 12-May-15 | 19863 | 3 | 4 | | | IV-1 | Pfdn5 | 5204 | 4-May-15 |
| 19768 | 3 | 4 | | | | | IV-1 | Pcdhb18 | 54660 | 4-May-15 | 19864 | 3 | 4 | | | IV-1 | Pfn2 | 5217 | 4-May-15 |
| 19769 | 3 | 4 | | | | | IV-1 | Pcdhb19 | 84054 | 4-May-15 | 19865 | 3 | 4 | | | IV-1 | Pgbd5 | 79605 | 4-May-15 |
| 19770 | 3 | 4 | | | | | IV-1 | Pcdhb2 | 56133 | 12-May-15 | 19866 | 3 | 4 | | | IV-1 | Pgc | 5225 | 12-May-15 |
| 19771 | 3 | 4 | | | | | IV-1 | Pcdhb20 | | | 19867 | 3 | 4 | | | IV-1 | Pgk1 | 5230 | 12-May-15 |
| 19772 | 3 | 4 | | | | | IV-1 | Pcdhb21 | | | 19868 | 3 | 4 | | | IV-1 | Pgk2 | 5232 | 28-May-15 |
| 19773 | 3 | 4 | | | | | IV-1 | Pcdhb22 | | | 19869 | 3 | 4 | | | IV-1 | Pglyrp4 | 57115 | 4-May-15 |
| 19774 | 3 | 4 | | | | | IV-1 | Pcdhb4 | 56131 | 12-May-15 | 19870 | 3 | 4 | | | IV-1 | Pgm3 | 5238 | 4-May-15 |
| 19775 | 3 | 4 | | | | | IV-1 | Pcdhb5 | 26167 | 4-May-15 | 19871 | 3 | 4 | | | IV-1 | Pgm5 | 5239 | 17-May-15 |
| 19776 | 3 | 4 | | | | | IV-1 | Pcdhb6 | 56130 | 21-May-15 | 19872 | 3 | 4 | | | IV-1 | Pgs1 | 9489 | 4-May-15 |
| 19777 | 3 | 4 | | | | | IV-1 | Pcdhb7 | 56129 | 4-May-15 | 19873 | 3 | 4 | | | IV-1 | Phactr3 | 116154 | 4-May-15 |
| 19778 | 3 | 4 | | | | | IV-1 | Pcdhb8 | 56128 | 4-May-15 | 19874 | 3 | 4 | | | IV-1 | Phactr4 | 65979 | 4-May-15 |
| 19779 | 3 | 4 | | | | | IV-1 | Pcdhb9 | 56127 | 4-May-15 | 19875 | 3 | 4 | | | IV-1 | Phb | 5245 | 23-May-15 |
| 19780 | 3 | 4 | | | | | IV-1 | Pcdhga1 | 56114 | 4-May-15 | 19876 | 3 | 4 | | | IV-1 | Phc1 | 1911 | 4-May-15 |
| 19781 | 3 | 4 | | | | | IV-1 | Pcdhga10 | 56106 | 4-May-15 | 19877 | 3 | 4 | | | IV-1 | Phc2 | 1912 | 14-May-15 |
| 19782 | 3 | 4 | | | | | IV-1 | Pcdhga11 | 56105 | 4-May-15 | 19878 | 3 | 4 | | | IV-1 | Phc3 | 80012 | 12-May-15 |
| 19783 | 3 | 4 | | | | | IV-1 | Pcdhga2 | 56113 | 4-May-15 | 19879 | 3 | 4 | | | IV-1 | Phex | 5251 | 23-May-15 |
| 19784 | 3 | 4 | | | | | IV-1 | Pcdhga4 | 56111 | 4-May-15 | 19880 | 3 | 4 | | | IV-1 | Phf1 | 5252 | 4-May-15 |
| 19785 | 3 | 4 | | | | | IV-1 | Pcdhga6 | 56109 | 4-May-15 | 19881 | 3 | 4 | | | IV-1 | Phf10 | 55274 | 4-May-15 |
| 19786 | 3 | 4 | | | | | IV-1 | Pcdhga7 | 56108 | 4-May-15 | 19882 | 3 | 4 | | | IV-1 | Phf13 | 148479 | 4-May-15 |
| 19787 | 3 | 4 | | | | | IV-1 | Pcdhga8 | 9708 | 4-May-15 | 19883 | 3 | 4 | | | IV-1 | Phf14 | 9678 | 12-May-15 |
| 19788 | 3 | 4 | | | | | IV-1 | Pcdhga9 | 56107 | 4-May-15 | 19884 | 3 | 4 | | | IV-1 | Phf20 | 51230 | 12-May-15 |
| 19789 | 3 | 4 | | | | | IV-1 | Pcdhgb1 | 56104 | 4-May-15 | 19885 | 3 | 4 | | | IV-1 | Phf20l1 | 51105 | 4-May-15 |
| 19790 | 3 | 4 | | | | | IV-1 | Pcdhgb2 | 56103 | 4-May-15 | 19886 | 3 | 4 | | | IV-1 | Phf21a | 51317 | 4-May-15 |
| 19791 | 3 | 4 | | | | | IV-1 | Pcdhgb4 | 8641 | 4-May-15 | 19887 | 3 | 4 | | | IV-1 | Phf21b | 112885 | 4-May-15 |
| 19792 | 3 | 4 | | | | | IV-1 | Pcdhgb6 | 56100 | 4-May-15 | 19888 | 3 | 4 | | | IV-1 | Phf23 | 79142 | 4-May-15 |
| 19793 | 3 | 4 | | | | | IV-1 | Pcdhgb8 | | | 19889 | 3 | 4 | | | IV-1 | Phf3 | 23469 | 12-May-15 |
| 19794 | 3 | 4 | | | | | IV-1 | Pcdhgc3 | 5098 | 4-May-15 | 19890 | 3 | 4 | | | IV-1 | Phf5a | 84844 | 4-May-15 |
| 19795 | 3 | 4 | | | | | IV-1 | Pcdhgc5 | 56097 | 4-May-15 | 19891 | 3 | 4 | | | IV-1 | Phkb | 5257 | 23-May-15 |
| 19796 | 3 | 4 | | | | | IV-1 | Pcgf2 | 7703 | 4-May-15 | 19892 | 3 | 4 | | | IV-1 | Phlpp1 | 23239 | 4-May-15 |
| 19797 | 3 | 4 | | | | | IV-1 | Pcgf5 | 84333 | 2-Jun-15 | 19893 | 3 | 4 | | | IV-1 | Phox2a | 401 | 23-May-15 |
| 19798 | 3 | 4 | | | | | IV-1 | Pcid2 | 55795 | 4-May-15 | 19894 | 3 | 4 | | | IV-1 | Phox2b | 8929 | 28-May-15 |
| 19799 | 3 | 4 | | | | | IV-1 | Pcif1 | 63935 | 4-May-15 | 19895 | 3 | 4 | | | IV-1 | Phpt1 | 29085 | 4-May-15 |
| 19800 | 3 | 4 | | | | | IV-1 | Pcm1 | 5108 | 7-Jun-15 | 19896 | 3 | 4 | | | IV-1 | Phtf1 | 10745 | 4-May-15 |
| 19801 | 3 | 4 | | | | | IV-1 | Pcmt1 | 5110 | 4-May-15 | 19897 | 3 | 4 | | | IV-1 | Phtf2 | 57157 | 4-May-15 |
| 19802 | 3 | 4 | | | | | IV-1 | Pcmtd1 | 115294 | 4-May-15 | 19898 | 3 | 4 | | | IV-1 | Phyh | 5264 | 23-May-15 |
| 19803 | 3 | 4 | | | | | IV-1 | Pcmtd2 | 55251 | 4-May-15 | 19899 | 3 | 4 | | | IV-1 | Phykpl | 85007 | 4-May-15 |
| 19804 | 3 | 4 | | | | | IV-1 | Pcnt | 5116 | 4-May-15 | 19900 | 3 | 4 | | | IV-1 | Pi4kb | 5298 | 4-May-15 |
| 19805 | 3 | 4 | | | | | IV-1 | Pcnxl2 | 80003 | 4-May-15 | 19901 | 3 | 4 | | | IV-1 | Pias2 | 9063 | 4-May-15 |
| 19806 | 3 | 4 | | | | | IV-1 | Pcnxl3 | 399909 | 4-May-15 | 19902 | 3 | 4 | | | IV-1 | Pias3 | 10401 | 4-May-15 |
| 19807 | 3 | 4 | | | | | IV-1 | Pcnxl4 | 64430 | 4-May-15 | 19903 | 3 | 4 | | | IV-1 | Pias4 | 51588 | 4-May-15 |
| 19808 | 3 | 4 | | | | | IV-1 | Pcsk1n | 27344 | 4-May-15 | 19904 | 3 | 4 | | | IV-1 | Pibf1 | 10464 | 4-May-15 |
| 19809 | 3 | 4 | | | | | IV-1 | Pcsk2os1 | | | 19905 | 3 | 4 | | | IV-1 | Pigc | 5279 | 4-May-15 |
| 19810 | 3 | 4 | | | | | IV-1 | Pcsk2os2 | | | 19906 | 3 | 4 | | | IV-1 | Pigf | 5281 | 12-May-15 |
| 19811 | 3 | 4 | | | | | IV-1 | Pcyox1l | 78991 | 4-May-15 | 19907 | 3 | 4 | | | IV-1 | Pigh | 5283 | 12-May-15 |
| 19812 | 3 | 4 | | | | | IV-1 | Pdc | 5132 | 7-Jun-15 | 19908 | 3 | 4 | | | IV-1 | Pigl | 9487 | 4-May-15 |
| 19813 | 3 | 4 | | | | | IV-1 | Pdcd11 | 22984 | 4-May-15 | 19909 | 3 | 4 | | | IV-1 | Pigm | 93183 | 31-May-15 |
| 19814 | 3 | 4 | | | | | IV-1 | Pdcd1lg2 | 80380 | 4-May-15 | 19910 | 3 | 4 | | | IV-1 | Pign | 23556 | 31-May-15 |
| 19815 | 3 | 4 | | | | | IV-1 | Pdcd2 | 5134 | 4-May-15 | 19911 | 3 | 4 | | | IV-1 | Pigu | 128869 | 21-May-15 |
| 19816 | 3 | 4 | | | | | IV-1 | Pdcd2l | 84306 | 4-May-15 | 19912 | 3 | 4 | | | IV-1 | Pigyl | | |
| 19817 | 3 | 4 | | | | | IV-1 | Pdcd6 | 10016 | 4-May-15 | 19913 | 3 | 4 | | | IV-1 | Pik3cb | 5291 | 31-May-15 |
| 19818 | 3 | 4 | | | | | IV-1 | Pdcd6ip | 10015 | 3-May-15 | 19914 | 3 | 4 | | | IV-1 | Pik3r3 | 8503 | 28-May-15 |
| 19819 | 3 | 4 | | | | | IV-1 | Pdcd7 | 10081 | 4-May-15 | 19915 | 3 | 4 | | | IV-1 | Pin1rt1 | | |
| 19820 | 3 | 4 | | | | | IV-1 | Pdcl | 5082 | 3-May-15 | 19916 | 3 | 4 | | | IV-1 | Pinx1 | 54984 | 31-May-15 |
| 19821 | 3 | 4 | | | | | IV-1 | Pdcl2 | 132954 | 4-May-15 | 19917 | 3 | 4 | | | IV-1 | Pip4k2a | 5305 | 4-May-15 |
| 19822 | 3 | 4 | | | | | IV-1 | Pdcl3 | 79031 | 4-May-15 | 19918 | 3 | 4 | | | IV-1 | Pip5k1 | 138429 | 4-May-15 |
| 19823 | 3 | 4 | | | | | IV-1 | Pddc1 | 347862 | 12-May-15 | 19919 | 3 | 4 | | | IV-1 | Pitpnb | 23760 | 4-May-15 |
| 19824 | 3 | 4 | | | | | IV-1 | Pde1a | 5136 | 14-May-15 | 19920 | 3 | 4 | | | IV-1 | Pitpnc1 | 26207 | 4-May-15 |
| 19825 | 3 | 4 | | | | | IV-1 | Pde6c | 5146 | 23-May-15 | 19921 | 3 | 4 | | | IV-1 | Pitpnm1 | 9600 | 4-May-15 |
| 19826 | 3 | 4 | | | | | IV-1 | Pde6d | 5147 | 12-May-15 | 19922 | 3 | 4 | | | IV-1 | Pitpnm2os1 | | |
| 19827 | 3 | 4 | | | | | IV-1 | Pde6h | 5149 | 23-May-15 | 19923 | 3 | 4 | | | IV-1 | Pitpnm3 | 83394 | 4-May-15 |
| 19828 | 3 | 4 | | | | | IV-1 | Pdgfb | 5155 | 31-May-15 | 19924 | 3 | 4 | | | IV-1 | Piwil2 | 55124 | 4-May-15 |
| 19829 | 3 | 4 | | | | | IV-1 | Pdhb | 5162 | 4-May-15 | 19925 | 3 | 4 | | | IV-1 | Pkd1 | 5310 | 31-May-15 |
| 19830 | 3 | 4 | | | | | IV-1 | Pdlim7 | 9260 | 24-May-15 | 19926 | 3 | 4 | | | IV-1 | Pkd1l3 | 342372 | 4-May-15 |
| 19831 | 3 | 4 | | | | | IV-1 | Pds5b | 23047 | 4-May-15 | 19927 | 3 | 4 | | | IV-1 | Pkd2 | 5311 | 7-Jun-15 |
| 19832 | 3 | 4 | | | | | IV-1 | Pdxdc1 | 23042 | 23-May-15 | 19928 | 3 | 4 | | | IV-1 | Pkd2l2 | 27039 | 12-May-15 |
| 19833 | 3 | 4 | | | | | IV-1 | Pdxp | 57026 | 4-May-15 | 19929 | 3 | 4 | | | IV-1 | Pkn2 | 5586 | 4-May-15 |
| 19834 | 3 | 4 | | | | | IV-1 | Pdzd11 | 51248 | 4-May-15 | 19930 | 3 | 4 | | | IV-1 | Pkn3 | 29941 | 21-May-15 |
| 19835 | 3 | 4 | | | | | IV-1 | Pdzd2 | 23037 | 12-May-15 | 19931 | 3 | 4 | | | IV-1 | Pknox1 | 5316 | 4-May-15 |
| 19836 | 3 | 4 | | | | | IV-1 | Pea15b | | | 19932 | 3 | 4 | | | IV-1 | Pknox2 | 63876 | 4-May-15 |
| 19837 | 3 | 4 | | | | | IV-1 | Peak1 | 79834 | 4-May-15 | 19933 | 3 | 4 | | | IV-1 | Pkp2 | 5318 | 23-May-15 |
| 19838 | 3 | 4 | | | | | IV-1 | Pear1 | 375033 | 4-May-15 | 19934 | 3 | 4 | | | IV-1 | Pkp3 | 11187 | 4-May-15 |
| 19839 | 3 | 4 | | | | | IV-1 | Pecam1 | 5175 | 17-May-15 | 19935 | 3 | 4 | | | IV-1 | Pkp4 | 8502 | 4-May-15 |
| 19840 | 3 | 4 | | | | | IV-1 | Pecr | 55825 | 4-May-15 | 19936 | 3 | 4 | | | IV-1 | Pla2g10os | | |
| 19841 | 3 | 4 | | | | | IV-1 | Peg10 | 23089 | 4-May-15 | 19937 | 3 | 4 | | | IV-1 | Plagl1 | 5325 | 28-May-15 |
| 19842 | 3 | 4 | | | | | IV-1 | Peg13 | | | 19938 | 3 | 4 | | | IV-1 | Plbd1 | 79887 | 4-May-15 |
| 19843 | 3 | 4 | | | | | IV-1 | Peli2 | 57161 | 4-May-15 | 19939 | 3 | 4 | | | IV-1 | Plcb4 | 5332 | 12-May-15 |
| 19844 | 3 | 4 | | | | | IV-1 | Peli3 | 246330 | 3-May-15 | 19940 | 3 | 4 | | | IV-1 | Plch2 | 9651 | 4-May-15 |
| 19845 | 3 | 4 | | | | | IV-1 | Pelo | 53918 | 4-May-15 | | | | | | | | | |

Fig. 30 - 106

| | | | | | | | | | | | | | | | |
|---|---|---|---|---|---|---|---|---|---|---|---|---|---|---|---|
| 19941 | 3 | 4 | | | | IV-1 | Plxnd2 | 257068 | 4-May-15 | 20037 | 3 | 4 | | IV-1 | Ppih | 10465 | 12-May-15 |
| 19942 | 3 | 4 | | | | IV-1 | Plcz1 | 89869 | 4-May-15 | 20038 | 3 | 4 | | IV-1 | Ppil3 | 53938 | 4-May-15 |
| 19943 | 3 | 4 | | | | IV-1 | Pld1 | 5337 | 13-Jun-15 | 20039 | 3 | 4 | | IV-1 | Ppm1b | 5495 | 31-May-15 |
| 19944 | 3 | 4 | | | | IV-1 | Pld6 | 201164 | 29-May-15 | 20040 | 3 | 4 | | IV-1 | Ppm1d | 8493 | 31-May-15 |
| 19945 | 3 | 4 | | | | IV-1 | Plec | 5339 | 23-May-15 | 20041 | 3 | 4 | | IV-1 | Ppm1g | 5496 | 4-May-15 |
| 19946 | 3 | 4 | | | | IV-1 | Plekhg3 | 26030 | 21-May-15 | 20042 | 3 | 4 | | IV-1 | Ppm1h | 57460 | 4-May-15 |
| 19947 | 3 | 4 | | | | IV-1 | Plekhg4 | 25894 | 17-May-15 | 20043 | 3 | 4 | | IV-1 | Ppm1j | 333926 | 12-May-15 |
| 19948 | 3 | 4 | | | | IV-1 | Plekhm1 | 9842 | 12-May-15 | 20044 | 3 | 4 | | IV-1 | Ppm1n | 147699 | 4-May-15 |
| 19949 | 3 | 4 | | | | IV-1 | Plekhm2 | 23207 | 29-May-15 | 20045 | 3 | 4 | | IV-1 | Ppp1cb | 5500 | 4-May-15 |
| 19950 | 3 | 4 | | | | IV-1 | Plekhm3 | 389072 | 21-May-15 | 20046 | 3 | 4 | | IV-1 | Ppp1r12a | 4659 | 12-May-15 |
| 19951 | 3 | 4 | | | | IV-1 | Plscr4 | 57088 | 4-May-15 | 20047 | 3 | 4 | | IV-1 | Ppp1r12b | 4660 | 14-May-15 |
| 19952 | 3 | 4 | | | | IV-1 | Plxna4os1 | | | 20048 | 3 | 4 | | IV-1 | Ppp1r13b | 23368 | 17-May-15 |
| 19953 | 3 | 4 | | | | IV-1 | Pnis2 | | | 20049 | 3 | 4 | | IV-1 | Ppp1r14d | 54866 | 4-May-15 |
| 19954 | 3 | 4 | | | | IV-1 | Pnm2 | 5373 | 23-May-15 | 20050 | 3 | 4 | | IV-1 | Ppp1r16b | 26051 | 12-May-15 |
| 19955 | 3 | 4 | | | | IV-1 | Pnp2 | 5375 | 4-May-15 | 20051 | 3 | 4 | | IV-1 | Ppp1r2 | 5504 | 12-May-15 |
| 19956 | 3 | 4 | | | | IV-1 | Pnkd | 25953 | 23-May-15 | 20052 | 3 | 4 | | IV-1 | Ppp1r21 | 129285 | 4-May-15 |
| 19957 | 3 | 4 | | | | IV-1 | Pnkp | 11284 | 17-May-15 | 20053 | 3 | 4 | | IV-1 | Ppp1r26 | 9858 | 4-May-15 |
| 19958 | 3 | 4 | | | | IV-1 | Pnldc1 | 154197 | 4-May-15 | 20054 | 3 | 4 | | IV-1 | Ppp1r27 | 116729 | 4-May-15 |
| 19959 | 3 | 4 | | | | IV-1 | Pnma2 | 10687 | 4-May-15 | 20055 | 3 | 4 | | IV-1 | Ppp1r2-ps9 | | |
| 19960 | 3 | 4 | | | | IV-1 | Pnma3 | 29944 | 4-May-15 | 20056 | 3 | 4 | | IV-1 | Ppp1r3f | 89801 | 4-May-15 |
| 19961 | 3 | 4 | | | | IV-1 | Pnma5 | 114824 | 12-May-15 | 20057 | 3 | 4 | | IV-1 | Ppp1r3g | 648791 | 4-May-15 |
| 19962 | 3 | 4 | | | | IV-1 | Pnmal1 | 55228 | 4-May-15 | 20058 | 3 | 4 | | IV-1 | Ppp1r42 | 286187 | 4-May-15 |
| 19963 | 3 | 4 | | | | IV-1 | Pnmal2 | 57469 | 4-May-15 | 20059 | 3 | 4 | | IV-1 | Ppp1r7 | 5510 | 12-May-15 |
| 19964 | 3 | 4 | | | | IV-1 | Pno1 | 56902 | 12-May-15 | 20060 | 3 | 4 | | IV-1 | Ppp1r8 | 5511 | 4-May-15 |
| 19965 | 3 | 4 | | | | IV-1 | Pnp | 4860 | 7-Jun-15 | 20061 | 3 | 4 | | IV-1 | Ppp1r9a | 55607 | 12-May-15 |
| 19966 | 3 | 4 | | | | IV-1 | Pnpla6 | 10908 | 12-May-15 | 20062 | 3 | 4 | | IV-1 | Ppp2cb | 5516 | 4-May-15 |
| 19967 | 3 | 4 | | | | IV-1 | Pnpla7 | 375775 | 4-Jun-15 | 20063 | 3 | 4 | | IV-1 | Ppp2r1a | 5518 | 23-May-15 |
| 19968 | 3 | 4 | | | | IV-1 | Pnpla8 | 50640 | 31-May-15 | 20064 | 3 | 4 | | IV-1 | Ppp2r1b | 5519 | 12-May-15 |
| 19969 | 3 | 4 | | | | IV-1 | Pnpo | 55163 | 2-Jun-15 | 20065 | 3 | 4 | | IV-1 | Ppp2r2a | 5520 | 4-May-15 |
| 19970 | 3 | 4 | | | | IV-1 | Poc1a | 25886 | 4-May-15 | 20066 | 3 | 4 | | IV-1 | Ppp2r2d | 55844 | 4-May-15 |
| 19971 | 3 | 4 | | | | IV-1 | Poc5 | 134359 | 17-May-15 | 20067 | 3 | 4 | | IV-1 | Ppp2r3d | | |
| 19972 | 3 | 4 | | | | IV-1 | Podn | 127435 | 4-May-15 | 20068 | 3 | 4 | | IV-1 | Ppp2r4 | 5524 | 12-May-15 |
| 19973 | 3 | 4 | | | | IV-1 | Podxl | 5420 | 12-May-15 | 20069 | 3 | 4 | | IV-1 | Ppp2r5d | 5528 | 23-May-15 |
| 19974 | 3 | 4 | | | | IV-1 | Pofut1 | 23509 | 17-May-15 | 20070 | 3 | 4 | | IV-1 | Ppp2r5e | 5529 | 4-May-15 |
| 19975 | 3 | 4 | | | | IV-1 | Pofut2 | 23275 | 12-May-15 | 20071 | 3 | 4 | | IV-1 | Ppp3ca | 5530 | 17-May-15 |
| 19976 | 3 | 4 | | | | IV-1 | Pogk | 57645 | 4-May-15 | 20072 | 3 | 4 | | IV-1 | Ppp3cb | 5532 | 4-May-15 |
| 19977 | 3 | 4 | | | | IV-1 | Pogz | 23126 | 23-May-15 | 20073 | 3 | 4 | | IV-1 | Ppp3r2 | 5535 | 4-May-15 |
| 19978 | 3 | 4 | | | | IV-1 | Pold4 | 57804 | 7-Jun-15 | 20074 | 3 | 4 | | IV-1 | Ppp4r1 | 9989 | 4-May-15 |
| 19979 | 3 | 4 | | | | IV-1 | Poldip3 | 84271 | 4-May-15 | 20075 | 3 | 4 | | IV-1 | Ppp4r1l-ps | | |
| 19980 | 3 | 4 | | | | IV-1 | Polg | 5428 | 23-May-15 | 20076 | 3 | 4 | | IV-1 | Ppp4r2 | 151987 | 4-May-15 |
| 19981 | 3 | 4 | | | | IV-1 | Polg2 | 11232 | 12-May-15 | 20077 | 3 | 4 | | IV-1 | Ppp4r4 | 57718 | 4-May-15 |
| 19982 | 3 | 4 | | | | IV-1 | Polh | 5429 | 7-Jun-15 | 20078 | 3 | 4 | | IV-1 | Ppp5c | 5536 | 4-May-15 |
| 19983 | 3 | 4 | | | | IV-1 | Polm | 27434 | 4-May-15 | 20079 | 3 | 4 | | IV-1 | Ppp6c | 5537 | 4-May-15 |
| 19984 | 3 | 4 | | | | IV-1 | Polr1b | 84172 | 4-May-15 | 20080 | 3 | 4 | | IV-1 | Ppp6r1 | 22870 | 4-May-15 |
| 19985 | 3 | 4 | | | | IV-1 | Polr1c | 9533 | 7-Jun-15 | 20081 | 3 | 4 | | IV-1 | Ppp6r2 | 9701 | 4-May-15 |
| 19986 | 3 | 4 | | | | IV-1 | Polr1d | 51082 | 24-May-15 | 20082 | 3 | 4 | | IV-1 | Ppp6r3 | 55291 | 4-May-15 |
| 19987 | 3 | 4 | | | | IV-1 | Polr1e | 64425 | 4-May-15 | 20083 | 3 | 4 | | IV-1 | Ppt2 | 9374 | 4-May-15 |
| 19988 | 3 | 4 | | | | IV-1 | Polr2a | 5430 | 17-May-15 | 20084 | 3 | 4 | | IV-1 | Pptc7 | 160760 | 4-May-15 |
| 19989 | 3 | 4 | | | | IV-1 | Polr2b | 5431 | 12-May-15 | 20085 | 3 | 4 | | IV-1 | Pqlc1 | 80148 | 4-May-15 |
| 19990 | 3 | 4 | | | | IV-1 | Polr2c | 5432 | 12-May-15 | 20086 | 3 | 4 | | IV-1 | Praf2 | 11230 | 12-May-15 |
| 19991 | 3 | 4 | | | | IV-1 | Polr2d | 5433 | 4-May-15 | 20087 | 3 | 4 | | IV-1 | Pramef12 | 390999 | 4-May-15 |
| 19992 | 3 | 4 | | | | IV-1 | Polr2e | 5434 | 4-May-15 | 20088 | 3 | 4 | | IV-1 | Pramef17 | 391004 | 4-May-15 |
| 19993 | 3 | 4 | | | | IV-1 | Polr2f | 5435 | 12-May-15 | 20089 | 3 | 4 | | IV-1 | Pramef25 | 441873 | 4-May-15 |
| 19994 | 3 | 4 | | | | IV-1 | Polr2j | 5439 | 4-May-15 | 20090 | 3 | 4 | | IV-1 | Pramef6 | 440561 | 4-May-15 |
| 19995 | 3 | 4 | | | | IV-1 | Polr2k | 5440 | 4-May-15 | 20091 | 3 | 4 | | IV-1 | Pramef8 | 391002 | 4-May-15 |
| 19996 | 3 | 4 | | | | IV-1 | Polr2m | 81488 | 4-May-15 | 20092 | 3 | 4 | | IV-1 | Pramel1 | | |
| 19997 | 3 | 4 | | | | IV-1 | Polr3a | 11128 | 23-May-15 | 20093 | 3 | 4 | | IV-1 | Pramel3 | | |
| 19998 | 3 | 4 | | | | IV-1 | Polr3b | 55703 | 2-Jun-15 | 20094 | 3 | 4 | | IV-1 | Pramel4 | | |
| 19999 | 3 | 4 | | | | IV-1 | Polr3c | 10623 | 12-May-15 | 20095 | 3 | 4 | | IV-1 | Pramel6 | | |
| 20000 | 3 | 4 | | | | IV-1 | Polr3d | 661 | 21-May-15 | 20096 | 3 | 4 | | IV-1 | Prap1 | 118471 | 12-May-15 |
| 20001 | 3 | 4 | | | | IV-1 | Polr3e | 55718 | 4-May-15 | 20097 | 3 | 4 | | IV-1 | Prdm11 | 56981 | 13-May-15 |
| 20002 | 3 | 4 | | | | IV-1 | Polr3f | 10621 | 4-May-15 | 20098 | 3 | 4 | | IV-1 | Prdm12 | 59335 | 28-May-15 |
| 20003 | 3 | 4 | | | | IV-1 | Polr3g | 10622 | 12-May-15 | 20099 | 3 | 4 | | IV-1 | Prdm13 | 59336 | 28-May-15 |
| 20004 | 3 | 4 | | | | IV-1 | Polr3gl | 84265 | 4-May-15 | 20100 | 3 | 4 | | IV-1 | Prdm14 | 63978 | 4-May-15 |
| 20005 | 3 | 4 | | | | IV-1 | Polr3h | 171568 | 4-May-15 | 20101 | 3 | 4 | | IV-1 | Prdm15 | 63977 | 21-May-15 |
| 20006 | 3 | 4 | | | | IV-1 | Polrmt | 5442 | 4-May-15 | 20102 | 3 | 4 | | IV-1 | Prdm16 | 63976 | 4-May-15 |
| 20007 | 3 | 4 | | | | IV-1 | Pom121l12 | 285877 | 4-May-15 | 20103 | 3 | 4 | | IV-1 | Prdm4 | 11108 | 4-May-15 |
| 20008 | 3 | 4 | | | | IV-1 | Pom121l2 | 94026 | 4-May-15 | 20104 | 3 | 4 | | IV-1 | Prdx6 | 9588 | 7-Jun-15 |
| 20009 | 3 | 4 | | | | IV-1 | Pomgnt2 | 84892 | 4-May-15 | 20105 | 3 | 4 | | IV-1 | Prelid1 | 27166 | 4-May-15 |
| 20010 | 3 | 4 | | | | IV-1 | Pomt1 | 10585 | 23-May-15 | 20106 | 3 | 4 | | IV-1 | Prickle3 | 4007 | 12-May-15 |
| 20011 | 3 | 4 | | | | IV-1 | Pomt2 | 29954 | 23-May-15 | 20107 | 3 | 4 | | IV-1 | Prkaa2 | 5563 | 4-May-15 |
| 20012 | 3 | 4 | | | | IV-1 | Pon3 | 5446 | 4-May-15 | 20108 | 3 | 4 | | IV-1 | Prkab2 | 5565 | 12-May-15 |
| 20013 | 3 | 4 | | | | IV-1 | Pop7 | 10248 | 4-May-15 | 20109 | 3 | 4 | | IV-1 | Prkacb | 5567 | 12-May-15 |
| 20014 | 3 | 4 | | | | IV-1 | Pot1b | | | 20110 | 3 | 4 | | IV-1 | Prkag1 | 5571 | 31-May-15 |
| 20015 | 3 | 4 | | | | IV-1 | Poteg | 404785 | 4-May-15 | 20111 | 3 | 4 | | IV-1 | Prkag2 | 51422 | 31-May-15 |
| 20016 | 3 | 4 | | | | IV-1 | Pou1f1 | 5449 | 4-May-15 | 20112 | 3 | 4 | | IV-1 | Prkag2os1 | | |
| 20017 | 3 | 4 | | | | IV-1 | Pou3f2 | 5454 | 4-May-15 | 20113 | 3 | 4 | | IV-1 | Prkag3 | 53632 | 12-May-15 |
| 20018 | 3 | 4 | | | | IV-1 | Pou4f1 | 5457 | 28-May-15 | 20114 | 3 | 4 | | IV-1 | Prkar1b | 5575 | 4-May-15 |
| 20019 | 3 | 4 | | | | IV-1 | Pou4f2 | 5458 | 28-May-15 | 20115 | 3 | 4 | | IV-1 | Prkcsh | 5589 | 12-May-15 |
| 20020 | 3 | 4 | | | | IV-1 | Pou4f3 | 5459 | 28-May-15 | 20116 | 3 | 4 | | IV-1 | Prkcz | 5590 | 4-May-15 |
| 20021 | 3 | 4 | | | | IV-1 | Pou5f1 | 5460 | 24-May-15 | 20117 | 3 | 4 | | IV-1 | Prkdc | 5591 | 12-May-15 |
| 20022 | 3 | 4 | | | | IV-1 | Pou6f1 | 5463 | 4-May-15 | 20118 | 3 | 4 | | IV-1 | Prkg1 | 5592 | 28-May-15 |
| 20023 | 3 | 4 | | | | IV-1 | Pou6f2 | 11281 | 4-May-15 | 20119 | 3 | 4 | | IV-1 | Prkrip1 | 79706 | 4-May-15 |
| 20024 | 3 | 4 | | | | IV-1 | Pp2d1 | 151649 | 4-May-15 | 20120 | 3 | 4 | | IV-1 | Prkrir | 5612 | 4-May-15 |
| 20025 | 3 | 4 | | | | IV-1 | Ppapdc1b | 84513 | 4-May-15 | 20121 | 3 | 4 | | IV-1 | Prkx | 5613 | 4-May-15 |
| 20026 | 3 | 4 | | | | IV-1 | Ppapdc2 | 403313 | 23-May-15 | 20122 | 3 | 4 | | IV-1 | Prl2b1 | | |
| 20027 | 3 | 4 | | | | IV-1 | Ppapdc3 | 84814 | 4-May-15 | 20123 | 3 | 4 | | IV-1 | Prl2c1 | | |
| 20028 | 3 | 4 | | | | IV-1 | Ppcs | 79717 | 4-May-15 | 20124 | 3 | 4 | | IV-1 | Prl2c2 | | |
| 20029 | 3 | 4 | | | | IV-1 | Ppdpf | 79144 | 12-May-15 | 20125 | 3 | 4 | | IV-1 | Prl2c3 | | |
| 20030 | 3 | 4 | | | | IV-1 | Ppef1 | 5475 | 4-May-15 | 20126 | 3 | 4 | | IV-1 | Prl2c4 | | |
| 20031 | 3 | 4 | | | | IV-1 | Ppef2 | 5470 | 4-May-15 | 20127 | 3 | 4 | | IV-1 | Prl2c5 | | |
| 20032 | 3 | 4 | | | | IV-1 | Ppfia1 | 8500 | 4-May-15 | 20128 | 3 | 4 | | IV-1 | Prl4a1 | | |
| 20033 | 3 | 4 | | | | IV-1 | Ppfia3 | 8541 | 4-May-15 | 20129 | 3 | 4 | | IV-1 | Prl7a1 | | |
| 20034 | 3 | 4 | | | | IV-1 | Ppia | 5478 | 12-May-15 | 20130 | 3 | 4 | | IV-1 | Prmt5 | 10419 | 4-May-15 |
| 20035 | 3 | 4 | | | | IV-1 | Ppie | 10450 | 3-Jun-15 | 20131 | 3 | 4 | | IV-1 | Prmt6 | 55170 | 4-May-15 |
| 20036 | 3 | 4 | | | | IV-1 | Ppif | 10105 | 4-May-15 | 20132 | 3 | 4 | | IV-1 | Prmt7 | 54496 | 4-May-15 |

Fig. 30 - 107

| | | | | | | | | | | | | | | | | | | |
|---|---|---|---|---|---|---|---|---|---|---|---|---|---|---|---|---|---|---|
| 20133 | 3 | 4 | | | | IV-1 | Prmt8 | 56341 | 4-May-15 | 20228 | 3 | 4 | | | | IV-1 | Ptchd2 | 57540 | 12-May-15 |
| 20134 | 3 | 4 | | | | IV-1 | Prn | 64428 | 12-May-15 | 20229 | 3 | 4 | | | | IV-1 | Ptchd3 | 374308 | 12-May-15 |
| 20135 | 3 | 4 | | | | IV-1 | Prnd | 23627 | 12-May-15 | 20230 | 3 | 4 | | | | IV-1 | Ptchd4 | 442213 | 4-May-15 |
| 20136 | 3 | 4 | | | | IV-1 | Prob1 | 389333 | 4-May-15 | 20231 | 3 | 4 | | | | IV-1 | Ptdss1 | 9791 | 4-May-15 |
| 20137 | 3 | 4 | | | | IV-1 | Proca1 | 147011 | 4-May-15 | 20232 | 3 | 4 | | | | IV-1 | Pter | 9317 | 4-May-15 |
| 20138 | 3 | 4 | | | | IV-1 | Prol1 | 58503 | 4-May-15 | 20233 | 3 | 4 | | | | IV-1 | Ptges3l | 100885848 | 4-May-15 |
| 20139 | 3 | 4 | | | | IV-1 | Prorsd1 | | | 20234 | 3 | 4 | | | | IV-1 | Pth2r | 5746 | 4-May-15 |
| 20140 | 3 | 4 | | | | IV-1 | Pros1 | 5627 | 12-May-15 | 20235 | 3 | 4 | | | | IV-1 | Pthlh | 5744 | 12-May-15 |
| 20141 | 3 | 4 | | | | IV-1 | Proser1 | 80209 | 4-May-15 | 20236 | 3 | 4 | | | | IV-1 | Ptk2 | 5747 | 31-May-15 |
| 20142 | 3 | 4 | | | | IV-1 | Proser2 | 254427 | 4-May-15 | 20237 | 3 | 4 | | | | IV-1 | Ptpla | 9200 | 12-May-15 |
| 20143 | 3 | 4 | | | | IV-1 | Prpf18 | 8559 | 12-May-15 | 20238 | 3 | 4 | | | | IV-1 | Ptplad2 | 401494 | 1-Jun-15 |
| 20144 | 3 | 4 | | | | IV-1 | Prpf19 | 27339 | 4-May-15 | 20239 | 3 | 4 | | | | IV-1 | Ptpn1 | 5770 | 17-May-15 |
| 20145 | 3 | 4 | | | | IV-1 | Prpf3 | 9129 | 23-May-15 | 20240 | 3 | 4 | | | | IV-1 | Ptpn12 | 5782 | 4-May-15 |
| 20146 | 3 | 4 | | | | IV-1 | Prpf31 | 26121 | 23-May-15 | 20241 | 3 | 4 | | | | IV-1 | Ptpn21 | 11099 | 4-May-15 |
| 20147 | 3 | 4 | | | | IV-1 | Prpf38a | 84950 | 4-May-15 | 20242 | 3 | 4 | | | | IV-1 | Ptprb | 5787 | 12-May-15 |
| 20148 | 3 | 4 | | | | IV-1 | Prpf38b | 55119 | 4-May-15 | 20243 | 3 | 4 | | | | IV-1 | Ptpre | 5791 | 4-May-15 |
| 20149 | 3 | 4 | | | | IV-1 | Prpf4 | 9128 | 4-May-15 | 20244 | 3 | 4 | | | | IV-1 | Ptprh | 5794 | 12-May-15 |
| 20150 | 3 | 4 | | | | IV-1 | Prpf40a | 55660 | 4-May-15 | 20245 | 3 | 4 | | | | IV-1 | Ptprj | 5795 | 12-May-15 |
| 20151 | 3 | 4 | | | | IV-1 | Prpf40b | 25766 | 4-May-15 | 20246 | 3 | 4 | | | | IV-1 | Ptprm | 5797 | 4-May-15 |
| 20152 | 3 | 4 | | | | IV-1 | Prpf4b | 8899 | 4-May-15 | 20247 | 3 | 4 | | | | IV-1 | Ptprtos | | |
| 20153 | 3 | 4 | | | | IV-1 | Prpf6 | 24148 | 23-May-15 | 20248 | 3 | 4 | | | | IV-1 | Ptpru | 10076 | 12-May-15 |
| 20154 | 3 | 4 | | | | IV-1 | Prpf8 | 10594 | 23-May-15 | 20249 | 3 | 4 | | | | IV-1 | Ptrf | 284119 | 3-May-15 |
| 20155 | 3 | 4 | | | | IV-1 | Prph | 5630 | 7-Jun-15 | 20250 | 3 | 4 | | | | IV-1 | Pts | 5805 | 12-May-15 |
| 20156 | 3 | 4 | | | | IV-1 | Prph2 | 5961 | 23-May-15 | 20251 | 3 | 4 | | | | IV-1 | Puf60 | 22827 | 2-Jun-15 |
| 20157 | 3 | 4 | | | | IV-1 | Prpmp5 | | | 20252 | 3 | 4 | | | | IV-1 | Pum1 | 9698 | 29-May-15 |
| 20158 | 3 | 4 | | | | IV-1 | Prps1 | 5631 | 7-Jun-15 | 20253 | 3 | 4 | | | | IV-1 | Pum2 | 23369 | 29-May-15 |
| 20159 | 3 | 4 | | | | IV-1 | Prps1l3 | | | 20254 | 3 | 4 | | | | IV-1 | Pura | 5813 | 28-May-15 |
| 20160 | 3 | 4 | | | | IV-1 | Prr13 | 54458 | 4-May-15 | 20255 | 3 | 4 | | | | IV-1 | Purb | 5814 | 4-May-15 |
| 20161 | 3 | 4 | | | | IV-1 | Prr14l | 253143 | 4-May-15 | 20256 | 3 | 4 | | | | IV-1 | Purg | 29942 | 4-May-15 |
| 20162 | 3 | 4 | | | | IV-1 | Prr22 | 163154 | 4-May-15 | 20257 | 3 | 4 | | | | IV-1 | Pus1 | 80324 | 4-May-15 |
| 20163 | 3 | 4 | | | | IV-1 | Prr23a | 729627 | 4-May-15 | 20258 | 3 | 4 | | | | IV-1 | Pus10 | 150962 | 12-May-15 |
| 20164 | 3 | 4 | | | | IV-1 | Prr24 | 255783 | 4-May-15 | 20259 | 3 | 4 | | | | IV-1 | Pus3 | 83480 | 4-May-15 |
| 20165 | 3 | 4 | | | | IV-1 | Prrc2a | 7916 | 12-May-15 | 20260 | 3 | 4 | | | | IV-1 | Pus7 | 54517 | 12-May-15 |
| 20166 | 3 | 4 | | | | IV-1 | Prrc2b | 84726 | 4-May-15 | 20261 | 3 | 4 | | | | IV-1 | Pwp1 | 13137 | 4-May-15 |
| 20167 | 3 | 4 | | | | IV-1 | Prrc2c | 23215 | 4-May-15 | 20262 | 3 | 4 | | | | IV-1 | Pwp2 | 5822 | 4-May-15 |
| 20168 | 3 | 4 | | | | IV-1 | Prss28 | | | 20263 | 3 | 4 | | | | IV-1 | Pwwp2a | 114825 | 4-May-15 |
| 20169 | 3 | 4 | | | | IV-1 | Prss36 | 146547 | 4-May-15 | 20264 | 3 | 4 | | | | IV-1 | Pwwp2b | 170394 | 12-May-15 |
| 20170 | 3 | 4 | | | | IV-1 | Prss38 | 339501 | 4-May-15 | 20265 | 3 | 4 | | | | IV-1 | Pyroxd2 | 84795 | 4-May-15 |
| 20171 | 3 | 4 | | | | IV-1 | Prss40 | | | 20266 | 3 | 4 | | | | IV-1 | Qars | 5859 | 7-Jun-15 |
| 20172 | 3 | 4 | | | | IV-1 | Prss41 | 360226 | 4-May-15 | 20267 | 3 | 4 | | | | IV-1 | Qdpr | 5860 | 12-May-15 |
| 20173 | 3 | 4 | | | | IV-1 | Prss42 | 339906 | 4-May-15 | 20268 | 3 | 4 | | | | IV-1 | Qk | 9444 | 28-May-15 |
| 20174 | 3 | 4 | | | | IV-1 | Prss43 | 100288960 | 4-May-15 | 20269 | 3 | 4 | | | | IV-1 | Qpct | 25797 | 4-May-15 |
| 20175 | 3 | 4 | | | | IV-1 | Prss48 | 345062 | 4-May-15 | 20270 | 3 | 4 | | | | IV-1 | Qprt | 23475 | 21-May-15 |
| 20176 | 3 | 4 | | | | IV-1 | Prss50 | 29122 | 4-May-15 | 20271 | 3 | 4 | | | | IV-1 | Qrfpr | 84109 | 4-May-15 |
| 20177 | 3 | 4 | | | | IV-1 | Prss52 | | | 20272 | 3 | 4 | | | | IV-1 | Qrich1 | 54870 | 12-May-15 |
| 20178 | 3 | 4 | | | | IV-1 | Prss53 | 339105 | 4-May-15 | 20273 | 3 | 4 | | | | IV-1 | Qrich2 | 84074 | 4-May-15 |
| 20179 | 3 | 4 | | | | IV-1 | Prss55 | 203074 | 4-May-15 | 20274 | 3 | 4 | | | | IV-1 | Qrsl1 | 55278 | 4-May-15 |
| 20180 | 3 | 4 | | | | IV-1 | Prune2 | 158471 | 12-May-15 | 20275 | 3 | 4 | | | | IV-1 | Qscox1 | 5768 | 4-May-15 |
| 20181 | 3 | 4 | | | | IV-1 | Psap1 | 768239 | 4-May-15 | 20276 | 3 | 4 | | | | IV-1 | Qtrtd1 | 79691 | 4-May-15 |
| 20182 | 3 | 4 | | | | IV-1 | Psd3 | 23362 | 4-May-15 | 20277 | 3 | 4 | | | | IV-1 | R3hcc1 | 203069 | 12-May-15 |
| 20183 | 3 | 4 | | | | IV-1 | Psen2 | 5664 | 31-May-15 | 20278 | 3 | 4 | | | | IV-1 | R3hcc1l | 27291 | 4-May-15 |
| 20184 | 3 | 4 | | | | IV-1 | Psg16 | | | 20279 | 3 | 4 | | | | IV-1 | R3hdm1 | 23518 | 4-May-15 |
| 20185 | 3 | 4 | | | | IV-1 | Psg17 | | | 20280 | 3 | 4 | | | | IV-1 | R3hdm2 | 22864 | 21-May-15 |
| 20186 | 3 | 4 | | | | IV-1 | Psg18 | | | 20281 | 3 | 4 | | | | IV-1 | R3hdm4 | 91300 | 4-May-15 |
| 20187 | 3 | 4 | | | | IV-1 | Psg19 | | | 20282 | 3 | 4 | | | | IV-1 | R3hdml | 140902 | 4-May-15 |
| 20188 | 3 | 4 | | | | IV-1 | Psg20 | | | 20283 | 3 | 4 | | | | IV-1 | Rab1 | 5861 | 7-Jun-15 |
| 20189 | 3 | 4 | | | | IV-1 | Psg21 | | | 20284 | 3 | 4 | | | | IV-1 | Rab10 | 10890 | 4-May-15 |
| 20190 | 3 | 4 | | | | IV-1 | Psg22 | | | 20285 | 3 | 4 | | | | IV-1 | Rab10os | | |
| 20191 | 3 | 4 | | | | IV-1 | Psg23 | | | 20286 | 3 | 4 | | | | IV-1 | Rab11a | 8766 | 29-May-15 |
| 20192 | 3 | 4 | | | | IV-1 | Psg25 | | | 20287 | 3 | 4 | | | | IV-1 | Rab11b | 9230 | 7-Jun-15 |
| 20193 | 3 | 4 | | | | IV-1 | Psg27 | | | 20288 | 3 | 4 | | | | IV-1 | Rab11fip3 | 9727 | 21-May-15 |
| 20194 | 3 | 4 | | | | IV-1 | Psma3 | 5684 | 4-May-15 | 20289 | 3 | 4 | | | | IV-1 | Rab11fip4os2 | | |
| 20195 | 3 | 4 | | | | IV-1 | Psma4 | 5685 | 4-May-15 | 20290 | 3 | 4 | | | | IV-1 | Rab11fip5 | 26056 | 4-May-15 |
| 20196 | 3 | 4 | | | | IV-1 | Psma7 | 5688 | 12-May-15 | 20291 | 3 | 4 | | | | IV-1 | Rab12 | 201475 | 21-May-15 |
| 20197 | 3 | 4 | | | | IV-1 | Psmb10 | 5699 | 4-May-15 | 20292 | 3 | 4 | | | | IV-1 | Rab13 | 5872 | 3-May-15 |
| 20198 | 3 | 4 | | | | IV-1 | Psmb11 | 122706 | 4-May-15 | 20293 | 3 | 4 | | | | IV-1 | Rab20 | 55647 | 4-May-15 |
| 20199 | 3 | 4 | | | | IV-1 | Psmb3 | 5691 | 4-May-15 | 20294 | 3 | 4 | | | | IV-1 | Rab22a | 57403 | 4-May-15 |
| 20200 | 3 | 4 | | | | IV-1 | Psmb4 | 5692 | 3-May-15 | 20295 | 3 | 4 | | | | IV-1 | Rab23 | 51715 | 21-May-15 |
| 20201 | 3 | 4 | | | | IV-1 | Psmb5 | 5693 | 4-May-15 | 20296 | 3 | 4 | | | | IV-1 | Rab2a | 5862 | 21-May-15 |
| 20202 | 3 | 4 | | | | IV-1 | Psmb6 | 5694 | 4-May-15 | 20297 | 3 | 4 | | | | IV-1 | Rab2b | 84932 | 4-May-15 |
| 20203 | 3 | 4 | | | | IV-1 | Psmb7 | 5695 | 21-May-15 | 20298 | 3 | 4 | | | | IV-1 | Rab30 | 27314 | 4-May-15 |
| 20204 | 3 | 4 | | | | IV-1 | Psmc2 | 5701 | 4-May-15 | 20299 | 3 | 4 | | | | IV-1 | Rab34 | 83873 | 4-May-15 |
| 20205 | 3 | 4 | | | | IV-1 | Psmc3 | 5702 | 4-May-15 | 20300 | 3 | 4 | | | | IV-1 | Rab3a | 5864 | 4-May-15 |
| 20206 | 3 | 4 | | | | IV-1 | Psmc6 | 5706 | 4-May-15 | 20301 | 3 | 4 | | | | IV-1 | Rab3c | 115827 | 12-May-15 |
| 20207 | 3 | 4 | | | | IV-1 | Psmd1 | 5707 | 4-May-15 | 20302 | 3 | 4 | | | | IV-1 | Rab3gap2 | 25782 | 4-May-15 |
| 20208 | 3 | 4 | | | | IV-1 | Psmd10 | 5716 | 4-May-15 | 20303 | 3 | 4 | | | | IV-1 | Rab42 | 115273 | 4-May-15 |
| 20209 | 3 | 4 | | | | IV-1 | Psmd13 | 5719 | 4-May-15 | 20304 | 3 | 4 | | | | IV-1 | Rab4b | 53916 | 23-May-15 |
| 20210 | 3 | 4 | | | | IV-1 | Psmd14 | 10213 | 12-May-15 | 20305 | 3 | 4 | | | | IV-1 | Rab5b | 5869 | 2-Jun-15 |
| 20211 | 3 | 4 | | | | IV-1 | Psmd2 | 5708 | 4-May-15 | 20306 | 3 | 4 | | | | IV-1 | Rab5c | 5878 | 4-May-15 |
| 20212 | 3 | 4 | | | | IV-1 | Psmd3 | 5709 | 3-May-15 | 20307 | 3 | 4 | | | | IV-1 | Rab6a | 5870 | 29-May-15 |
| 20213 | 3 | 4 | | | | IV-1 | Psmd4 | 5710 | 4-May-15 | 20308 | 3 | 4 | | | | IV-1 | Rab7l1 | 8934 | 4-May-15 |
| 20214 | 3 | 4 | | | | IV-1 | Psmd6 | 9861 | 4-May-15 | 20309 | 3 | 4 | | | | IV-1 | Rab9b | 51209 | 4-May-15 |
| 20215 | 3 | 4 | | | | IV-1 | Psmd7 | 5713 | 4-May-15 | 20310 | 3 | 4 | | | | IV-1 | Rabep1 | 9135 | 4-May-15 |
| 20216 | 3 | 4 | | | | IV-1 | Psmd8 | 5714 | 4-May-15 | 20311 | 3 | 4 | | | | IV-1 | Rabep2 | 79874 | 4-May-15 |
| 20217 | 3 | 4 | | | | IV-1 | Psmd9 | 5715 | 4-May-15 | 20312 | 3 | 4 | | | | IV-1 | Rabgap1 | 23637 | 4-May-15 |
| 20218 | 3 | 4 | | | | IV-1 | Psme2b | | | 20313 | 3 | 4 | | | | IV-1 | Rabgap1l | 9910 | 3-May-15 |
| 20219 | 3 | 4 | | | | IV-1 | Psme3 | 10197 | 24-May-15 | 20314 | 3 | 4 | | | | IV-1 | Rabgef1 | 27342 | 31-May-15 |
| 20220 | 3 | 4 | | | | IV-1 | Psmf1 | 9491 | 4-May-15 | 20315 | 3 | 4 | | | | IV-1 | Rabggta | 5875 | 12-May-15 |
| 20221 | 3 | 4 | | | | IV-1 | Psmg2 | 56984 | 4-May-15 | 20316 | 3 | 4 | | | | IV-1 | Rabggtb | 5876 | 4-May-15 |
| 20222 | 3 | 4 | | | | IV-1 | Psmg3 | 84262 | 4-May-15 | 20317 | 3 | 4 | | | | IV-1 | Rabl2 | | |
| 20223 | 3 | 4 | | | | IV-1 | Psmg4 | 389362 | 4-May-15 | 20318 | 3 | 4 | | | | IV-1 | Rabl3 | 285282 | 4-May-15 |
| 20224 | 3 | 4 | | | | IV-1 | Pspc1 | 55269 | 4-May-15 | 20319 | 3 | 4 | | | | IV-1 | Rabl6 | 55684 | 4-May-15 |
| 20225 | 3 | 4 | | | | IV-1 | Ptbp3 | 9991 | 1-Jun-15 | 20320 | 3 | 4 | | | | IV-1 | Rac1 | 5879 | 7-Jun-15 |
| 20226 | 3 | 4 | | | | IV-1 | Ptcd2 | 79810 | 4-May-15 | 20321 | 3 | 4 | | | | IV-1 | Rad17 | 5884 | 12-May-15 |
| 20227 | 3 | 4 | | | | IV-1 | Ptcd3 | 55037 | 4-May-15 | 20322 | 3 | 4 | | | | IV-1 | Rad50 | 10111 | 4-May-15 |

Fig. 30 - 108

| | | | | | | | | | | | | | | |
|---|---|---|---|---|---|---|---|---|---|---|---|---|---|---|
| 20323 | 3 | 4 | | | | IV-1 | Raet1a | | | 20419 | 3 | 4 | | | | IV-1 | Rgs21 | 431704 | 4-May-15 |
| 20324 | 3 | 4 | | | | IV-1 | Ralb | 5899 | 21-May-15 | 20420 | 3 | 4 | | | | IV-1 | Rgsl1 | 353299 | 4-May-15 |
| 20325 | 3 | 4 | | | | IV-1 | Ralgapa1 | 253959 | 12-May-15 | 20421 | 3 | 4 | | | | IV-1 | Rhbdd2 | 57414 | 4-May-15 |
| 20326 | 3 | 4 | | | | IV-1 | Ralgapa2 | 57186 | 4-May-15 | 20422 | 3 | 4 | | | | IV-1 | Rhbdl1 | 9028 | 4-May-15 |
| 20327 | 3 | 4 | | | | IV-1 | Ralgds | 5900 | 12-May-15 | 20423 | 3 | 4 | | | | IV-1 | Rhebl3 | 121268 | 12-May-15 |
| 20328 | 3 | 4 | | | | IV-1 | Ralgps2 | 55103 | 4-May-15 | 20424 | 3 | 4 | | | | IV-1 | Rhoa | 387 | 31-May-15 |
| 20329 | 3 | 4 | | | | IV-1 | Ralyl | 138046 | 2-Jun-15 | 20425 | 3 | 4 | | | | IV-1 | Rhob | 388 | 12-May-15 |
| 20330 | 3 | 4 | | | | IV-1 | Ramp1 | 10267 | 21-May-15 | 20426 | 3 | 4 | | | | IV-1 | Rhobtb3 | 22836 | 4-May-15 |
| 20331 | 3 | 4 | | | | IV-1 | Ranbp2 | 5903 | 23-May-15 | 20427 | 3 | 4 | | | | IV-1 | Rhog | 391 | 4-May-15 |
| 20332 | 3 | 4 | | | | IV-1 | Ranbp3 | 8498 | 4-May-15 | 20428 | 3 | 4 | | | | IV-1 | Rhot2 | 89941 | 4-May-15 |
| 20333 | 3 | 4 | | | | IV-1 | Ranbp3l | 202151 | 28-May-15 | 20429 | 3 | 4 | | | | IV-1 | Rhox10 | | |
| 20334 | 3 | 4 | | | | IV-1 | Ranbp6 | 26953 | 12-May-15 | 20430 | 3 | 4 | | | | IV-1 | Rhox11 | | |
| 20335 | 3 | 4 | | | | IV-1 | Ranbp9 | 10048 | 4-May-15 | 20431 | 3 | 4 | | | | IV-1 | Rhox12 | | |
| 20336 | 3 | 4 | | | | IV-1 | Rap1a | 5906 | 10-May-15 | 20432 | 3 | 4 | | | | IV-1 | Rhox13 | | |
| 20337 | 3 | 4 | | | | IV-1 | Rap1b | 5908 | 21-May-15 | 20433 | 3 | 4 | | | | IV-1 | Rhox2a | | |
| 20338 | 3 | 4 | | | | IV-1 | Rap2a | 5911 | 12-May-15 | 20434 | 3 | 4 | | | | IV-1 | Rhox2b | | |
| 20339 | 3 | 4 | | | | IV-1 | Rapgef1 | 2889 | 12-May-15 | 20435 | 3 | 4 | | | | IV-1 | Rhox2e | | |
| 20340 | 3 | 4 | | | | IV-1 | Rapgef2 | 9693 | 4-May-15 | 20436 | 3 | 4 | | | | IV-1 | Rhox2g | | |
| 20341 | 3 | 4 | | | | IV-1 | Rapgef3 | 10411 | 31-May-15 | 20437 | 3 | 4 | | | | IV-1 | Rhox4c | | |
| 20342 | 3 | 4 | | | | IV-1 | Rars2 | 57038 | 4-May-15 | 20438 | 3 | 4 | | | | IV-1 | Rhox4d | | |
| 20343 | 3 | 4 | | | | IV-1 | Rasa1 | 5921 | 7-Jun-15 | 20439 | 3 | 4 | | | | IV-1 | Rhox4e | | |
| 20344 | 3 | 4 | | | | IV-1 | Rasa2 | 5922 | 4-May-15 | 20440 | 3 | 4 | | | | IV-1 | Rhox4f | | |
| 20345 | 3 | 4 | | | | IV-1 | Rasa3 | 22821 | 12-May-15 | 20441 | 3 | 4 | | | | IV-1 | Rhox4g | | |
| 20346 | 3 | 4 | | | | IV-1 | Rasal2 | 9462 | 4-May-15 | 20442 | 3 | 4 | | | | IV-1 | Rhox6 | | |
| 20347 | 3 | 4 | | | | IV-1 | Rassf2 | 9770 | 28-May-15 | 20443 | 3 | 4 | | | | IV-1 | Rhox7 | | |
| 20348 | 3 | 4 | | | | IV-1 | Raver1-fdxll | | | 20444 | 3 | 4 | | | | IV-1 | Rhox8 | | |
| 20349 | 3 | 4 | | | | IV-1 | Raver2 | 55225 | 4-May-15 | 20445 | 3 | 4 | | | | IV-1 | Ric8b | 55188 | 4-May-15 |
| 20350 | 3 | 4 | | | | IV-1 | Rb1 | 5925 | 7-Jun-15 | 20446 | 3 | 4 | | | | IV-1 | Rif1 | 55183 | 7-Jun-15 |
| 20351 | 3 | 4 | | | | IV-1 | Rbak | 57786 | 12-May-15 | 20447 | 3 | 4 | | | | IV-1 | Riiad1 | 284485 | 4-May-15 |
| 20352 | 3 | 4 | | | | IV-1 | Rbakdn | 389458 | 4-May-15 | 20448 | 3 | 4 | | | | IV-1 | Rimbp2 | 23504 | 4-May-15 |
| 20353 | 3 | 4 | | | | IV-1 | Rbbp5 | 5929 | 4-May-15 | 20449 | 3 | 4 | | | | IV-1 | Rimkla | 284716 | 4-May-15 |
| 20354 | 3 | 4 | | | | IV-1 | Rbbp6 | 5930 | 12-May-15 | 20450 | 3 | 4 | | | | IV-1 | Rimklb | 57494 | 12-May-15 |
| 20355 | 3 | 4 | | | | IV-1 | Rbbp7 | 5931 | 4-May-15 | 20451 | 3 | 4 | | | | IV-1 | Rims1 | 22999 | 12-May-15 |
| 20356 | 3 | 4 | | | | IV-1 | Rbbp8 | 5932 | 17-May-15 | 20452 | 3 | 4 | | | | IV-1 | Rims2 | 9699 | 12-May-15 |
| 20357 | 3 | 4 | | | | IV-1 | Rbbp9 | 10741 | 4-May-15 | 20453 | 3 | 4 | | | | IV-1 | Rims3 | 9783 | 28-May-15 |
| 20358 | 3 | 4 | | | | IV-1 | Rbfox3 | 146713 | 4-May-15 | 20454 | 3 | 4 | | | | IV-1 | Riok1 | 83732 | 4-May-15 |
| 20359 | 3 | 4 | | | | IV-1 | Rbm17 | 84991 | 21-May-15 | 20455 | 3 | 4 | | | | IV-1 | Riok2 | 55781 | 4-May-15 |
| 20360 | 3 | 4 | | | | IV-1 | Rbm18 | 92400 | 4-May-15 | 20456 | 3 | 4 | | | | IV-1 | Ripk1 | 8737 | 4-May-15 |
| 20361 | 3 | 4 | | | | IV-1 | Rbm19 | 9904 | 4-May-15 | 20457 | 3 | 4 | | | | IV-1 | Ripk2 | 8767 | 29-May-15 |
| 20362 | 3 | 4 | | | | IV-1 | Rbm20 | 282996 | 23-May-15 | 20458 | 3 | 4 | | | | IV-1 | Ripply2 | 134701 | 12-May-15 |
| 20363 | 3 | 4 | | | | IV-1 | Rbm24 | 221662 | 4-May-15 | 20459 | 3 | 4 | | | | IV-1 | Ripply3 | 53820 | 4-May-15 |
| 20364 | 3 | 4 | | | | IV-1 | Rbm26 | 64062 | 4-May-15 | 20460 | 3 | 4 | | | | IV-1 | Rita1 | 84934 | 4-May-15 |
| 20365 | 3 | 4 | | | | IV-1 | Rbm27 | 54439 | 4-May-15 | 20461 | 3 | 4 | | | | IV-1 | Rin1 | 6013 | 4-May-15 |
| 20366 | 3 | 4 | | | | IV-1 | Rbm28 | 55131 | 12-May-15 | 20462 | 3 | 4 | | | | IV-1 | Rin3 | 117579 | 4-May-15 |
| 20367 | 3 | 4 | | | | IV-1 | Rbm33 | 155435 | 4-May-15 | 20463 | 3 | 4 | | | | IV-1 | Rmdn2 | 151393 | 4-May-15 |
| 20368 | 3 | 4 | | | | IV-1 | Rbm3os | | | 20464 | 3 | 4 | | | | IV-1 | Rmi1 | 80010 | 4-May-15 |
| 20369 | 3 | 4 | | | | IV-1 | Rbm4 | 5936 | 17-May-15 | 20465 | 3 | 4 | | | | IV-1 | Rmnd5b | 64777 | 4-May-15 |
| 20370 | 3 | 4 | | | | IV-1 | Rbm42 | 79171 | 4-May-15 | 20466 | 3 | 4 | | | | IV-1 | Rnaseh2a | 10535 | 23-May-15 |
| 20371 | 3 | 4 | | | | IV-1 | Rbm45 | 129831 | 4-May-15 | 20467 | 3 | 4 | | | | IV-1 | Rnaseh2b | 79621 | 23-May-15 |
| 20372 | 3 | 4 | | | | IV-1 | Rbm46 | 166863 | 4-May-15 | 20468 | 3 | 4 | | | | IV-1 | Rnasek | 440400 | 21-May-15 |
| 20373 | 3 | 4 | | | | IV-1 | Rbm47 | 54502 | 21-May-15 | 20469 | 3 | 4 | | | | IV-1 | Rnd3 | 390 | 12-May-15 |
| 20374 | 3 | 4 | | | | IV-1 | Rbm4b | 83759 | 4-May-15 | 20470 | 3 | 4 | | | | IV-1 | Rnf112 | 7732 | 4-May-15 |
| 20375 | 3 | 4 | | | | IV-1 | Rbm5 | 10181 | 4-May-15 | 20471 | 3 | 4 | | | | IV-1 | Rnf113a1 | | |
| 20376 | 3 | 4 | | | | IV-1 | Rbm6 | 10180 | 4-May-15 | 20472 | 3 | 4 | | | | IV-1 | Rnf113a2 | | |
| 20377 | 3 | 4 | | | | IV-1 | Rbm7 | 10179 | 4-May-15 | 20473 | 3 | 4 | | | | IV-1 | Rnf122 | 79845 | 4-May-15 |
| 20378 | 3 | 4 | | | | IV-1 | Rbm8a | 9939 | 23-May-15 | 20474 | 3 | 4 | | | | IV-1 | Rnf130 | 55819 | 2-Jun-15 |
| 20379 | 3 | 4 | | | | IV-1 | Rbms1 | 5937 | 4-May-15 | 20475 | 3 | 4 | | | | IV-1 | Rnf133 | 168433 | 4-May-15 |
| 20380 | 3 | 4 | | | | IV-1 | Rbms2 | 5939 | 4-May-15 | 20476 | 3 | 4 | | | | IV-1 | Rnf135 | 84282 | 4-May-15 |
| 20381 | 3 | 4 | | | | IV-1 | Rbmx2 | 51634 | 4-May-15 | 20477 | 3 | 4 | | | | IV-1 | Rnf138 | 51444 | 4-May-15 |
| 20382 | 3 | 4 | | | | IV-1 | Rbmxl1 | 494115 | 4-May-15 | 20478 | 3 | 4 | | | | IV-1 | Rnf138rt1 | | |
| 20383 | 3 | 4 | | | | IV-1 | Rbmy | 5940 | 23-May-15 | 20479 | 3 | 4 | | | | IV-1 | Rnf139 | 11236 | 4-May-15 |
| 20384 | 3 | 4 | | | | IV-1 | Rc3h1 | 149041 | 4-May-15 | 20480 | 3 | 4 | | | | IV-1 | Rnf14 | 9604 | 4-May-15 |
| 20385 | 3 | 4 | | | | IV-1 | Rcbtb1 | 55233 | 4-May-15 | 20481 | 3 | 4 | | | | IV-1 | Rnf141 | 50862 | 1-Jun-15 |
| 20386 | 3 | 4 | | | | IV-1 | Rcbtb2 | 1102 | 4-May-15 | 20482 | 3 | 4 | | | | IV-1 | Rnf146 | 81847 | 4-Jun-15 |
| 20387 | 3 | 4 | | | | IV-1 | Rce1 | 9986 | 4-May-15 | 20483 | 3 | 4 | | | | IV-1 | Rnf148 | 378925 | 4-May-15 |
| 20388 | 3 | 4 | | | | IV-1 | Rcl1 | 10171 | 1-Jun-15 | 20484 | 3 | 4 | | | | IV-1 | Rnf152 | 220441 | 4-May-15 |
| 20389 | 3 | 4 | | | | IV-1 | Rd3 | 343035 | 23-May-15 | 20485 | 3 | 4 | | | | IV-1 | Rnf166 | 115992 | 4-May-15 |
| 20390 | 3 | 4 | | | | IV-1 | Rdh14 | 57665 | 4-May-15 | 20486 | 3 | 4 | | | | IV-1 | Rnf168 | 165918 | 23-May-15 |
| 20391 | 3 | 4 | | | | IV-1 | Rdh8 | 50700 | 21-May-15 | 20487 | 3 | 4 | | | | IV-1 | Rnf169 | 254225 | 4-May-15 |
| 20392 | 3 | 4 | | | | IV-1 | Rdh9 | | | 20488 | 3 | 4 | | | | IV-1 | Rnf170 | 81790 | 23-May-15 |
| 20393 | 3 | 4 | | | | IV-1 | Rec8 | 9985 | 4-May-15 | 20489 | 3 | 4 | | | | IV-1 | Rnf182 | 221687 | 4-May-15 |
| 20394 | 3 | 4 | | | | IV-1 | Reck | 8434 | 31-May-15 | 20490 | 3 | 4 | | | | IV-1 | Rnf183 | 138065 | 4-May-15 |
| 20395 | 3 | 4 | | | | IV-1 | Reep4 | 80346 | 4-May-15 | 20491 | 3 | 4 | | | | IV-1 | Rnf19a | 25897 | 12-May-15 |
| 20396 | 3 | 4 | | | | IV-1 | Rei | 5966 | 28-May-15 | 20492 | 3 | 4 | | | | IV-1 | Rnf20 | 56254 | 2-Jun-15 |
| 20397 | 3 | 4 | | | | IV-1 | Relb | 5971 | 28-May-15 | 20493 | 3 | 4 | | | | IV-1 | Rnf215 | 200312 | 4-May-15 |
| 20398 | 3 | 4 | | | | IV-1 | Repin1 | 29803 | 17-May-15 | 20494 | 3 | 4 | | | | IV-1 | Rnf216 | 54476 | 4-May-15 |
| 20399 | 3 | 4 | | | | IV-1 | Reps1 | 85021 | 4-May-15 | 20495 | 3 | 4 | | | | IV-1 | Rnf217 | 154214 | 4-May-15 |
| 20400 | 3 | 4 | | | | IV-1 | Reps2 | 9185 | 4-May-15 | 20496 | 3 | 4 | | | | IV-1 | Rnf220 | 55182 | 4-May-15 |
| 20401 | 3 | 4 | | | | IV-1 | Rere | 473 | 12-May-15 | 20497 | 3 | 4 | | | | IV-1 | Rnf222 | 643904 | 12-May-15 |
| 20402 | 3 | 4 | | | | IV-1 | Rexo2 | 25996 | 4-May-15 | 20498 | 3 | 4 | | | | IV-1 | Rnf223 | 401934 | 4-May-15 |
| 20403 | 3 | 4 | | | | IV-1 | Rexo4 | 57109 | 4-May-15 | 20499 | 3 | 4 | | | | IV-1 | Rnf24 | 11237 | 2-Jun-15 |
| 20404 | 3 | 4 | | | | IV-1 | Rfc1 | 5981 | 7-Jun-15 | 20500 | 3 | 4 | | | | IV-1 | Rnf26 | 79102 | 4-May-15 |
| 20405 | 3 | 4 | | | | IV-1 | Rfng | 5986 | 4-May-15 | 20501 | 3 | 4 | | | | IV-1 | Rnf32 | 140545 | 21-May-15 |
| 20406 | 3 | 4 | | | | IV-1 | Rfpl3s | 10737 | 4-May-15 | 20502 | 3 | 4 | | | | IV-1 | Rnf38 | 152006 | 2-Jun-15 |
| 20407 | 3 | 4 | | | | IV-1 | Rfpl4 | 342931 | 24-May-15 | 20503 | 3 | 4 | | | | IV-1 | Rnf39 | 80352 | 4-May-15 |
| 20408 | 3 | 4 | | | | IV-1 | Rfpl4b | 442247 | 4-May-15 | 20504 | 3 | 4 | | | | IV-1 | Rnf40 | 9810 | 4-May-15 |
| 20409 | 3 | 4 | | | | IV-1 | Rft1 | 91869 | 13-Jun-15 | 20505 | 3 | 4 | | | | IV-1 | Rnf41 | 10193 | 2-Jun-15 |
| 20410 | 3 | 4 | | | | IV-1 | Rfwd3 | 55159 | 28-May-15 | 20506 | 3 | 4 | | | | IV-1 | Rnf5 | 6048 | 2-Jun-15 |
| 20411 | 3 | 4 | | | | IV-1 | Rfx5 | 5993 | 4-May-15 | 20507 | 3 | 4 | | | | IV-1 | Rnf6 | 6049 | 4-May-15 |
| 20412 | 3 | 4 | | | | IV-1 | Rfx6 | 222546 | 28-May-15 | 20508 | 3 | 4 | | | | IV-1 | Rnf7 | 9616 | 2-Jun-15 |
| 20413 | 3 | 4 | | | | IV-1 | Rfx7 | 64864 | 4-May-15 | 20509 | 3 | 4 | | | | IV-1 | Rnf8 | 9025 | 4-May-15 |
| 20414 | 3 | 4 | | | | IV-1 | Rfxank | 8625 | 4-May-15 | 20510 | 3 | 4 | | | | IV-1 | Rnft1 | 51136 | 4-May-15 |
| 20415 | 3 | 4 | | | | IV-1 | Rgag1 | 57529 | 4-May-15 | 20511 | 3 | 4 | | | | IV-1 | Rnft2 | 84900 | 12-May-15 |
| 20416 | 3 | 4 | | | | IV-1 | Rgag4 | 340526 | 4-May-15 | 20512 | 3 | 4 | | | | IV-1 | Rnh1 | 6050 | 12-May-15 |
| 20417 | 3 | 4 | | | | IV-1 | Rgl3 | 57139 | 4-May-15 | 20513 | 3 | 4 | | | | IV-1 | Rnmtl1 | 55178 | 4-May-15 |
| 20418 | 3 | 4 | | | | IV-1 | Rgr | 5995 | 7-Jun-15 | 20514 | 3 | 4 | | | | IV-1 | Rnpep | 6051 | 4-May-15 |

Fig. 30 - 109

| | | | | | | | | | | | | | | | | |
|---|---|---|---|---|---|---|---|---|---|---|---|---|---|---|---|---|
| 20515 | 3 | 4 | | | | IV-1 | Rnpepl1 | 57140 | 4-May-15 | 20611 | 3 | 4 | | | IV-1 | Rsrc1 | 51319 | 4-May-15 |
| 20516 | 3 | 4 | | | | IV-1 | Rnps1 | 10921 | 12-May-15 | 20612 | 3 | 4 | | | IV-1 | Rsrc2 | 65137 | 4-May-15 |
| 20517 | 3 | 4 | | | | IV-1 | Robo3 | 64221 | 4-May-15 | 20613 | 3 | 4 | | | IV-1 | Rsrp1 | 57035 | 4-May-15 |
| 20518 | 3 | 4 | | | | IV-1 | Rock2 | 9475 | 31-May-15 | 20614 | 3 | 4 | | | IV-1 | Rsu1 | 6251 | 1-Jun-15 |
| 20519 | 3 | 4 | | | | IV-1 | Rogdi | 79643 | 12-May-15 | 20615 | 3 | 4 | | | IV-1 | Rtbdn | 83546 | 10-May-15 |
| 20520 | 3 | 4 | | | | IV-1 | Rom1 | 6094 | 23-May-15 | 20616 | 3 | 4 | | | IV-1 | Rtca | 8634 | 12-May-15 |
| 20521 | 3 | 4 | | | | IV-1 | Ropn1 | 54763 | 31-May-15 | 20617 | 3 | 4 | | | IV-1 | Rtcb | 51493 | 4-May-15 |
| 20522 | 3 | 4 | | | | IV-1 | Ropn1l | 83853 | 4-May-15 | 20618 | 3 | 4 | | | IV-1 | Rtdr1 | 27156 | 9-May-15 |
| 20523 | 3 | 4 | | | | IV-1 | Rp1l1 | 94137 | 12-May-15 | 20619 | 3 | 4 | | | IV-1 | Rtf1 | 23168 | 4-May-15 |
| 20524 | 3 | 4 | | | | IV-1 | Rp2h | | | 20620 | 3 | 4 | | | IV-1 | Rtfdc1 | 51507 | 4-May-15 |
| 20525 | 3 | 4 | | | | IV-1 | Rp9 | 6100 | 23-May-15 | 20621 | 3 | 4 | | | IV-1 | Rtkn | 6242 | 12-May-15 |
| 20526 | 3 | 4 | | | | IV-1 | Rpap2 | 79871 | 4-May-15 | 20622 | 3 | 4 | | | IV-1 | Rtp2 | 344892 | 9-May-15 |
| 20527 | 3 | 4 | | | | IV-1 | Rpe | 6120 | 4-May-15 | 20623 | 3 | 4 | | | IV-1 | Rufy3 | 22902 | 7-Jun-15 |
| 20528 | 3 | 4 | | | | IV-1 | Rpe65 | 6121 | 23-May-15 | 20624 | 3 | 4 | | | IV-1 | Rusc2 | 9853 | 4-May-15 |
| 20529 | 3 | 4 | | | | IV-1 | Rpf1 | 80135 | 7-Jun-15 | 20625 | 3 | 4 | | | IV-1 | Ruvbl2 | 10856 | 17-May-15 |
| 20530 | 3 | 4 | | | | IV-1 | Rpf2 | 84154 | 4-May-15 | 20626 | 3 | 4 | | | IV-1 | Rwdd2a | 112611 | 4-May-15 |
| 20531 | 3 | 4 | | | | IV-1 | Rpgrip1 | 57096 | 12-May-15 | 20627 | 3 | 4 | | | IV-1 | Rxfp3 | 51289 | 4-May-15 |
| 20532 | 3 | 4 | | | | IV-1 | Rpgrip1l | 23322 | 23-May-15 | 20628 | 3 | 4 | | | IV-1 | Rxfp4 | 339403 | 4-May-15 |
| 20533 | 3 | 4 | | | | IV-1 | Rph3al | 9501 | 4-May-15 | 20629 | 3 | 4 | | | IV-1 | Rxra | 6256 | 4-May-15 |
| 20534 | 3 | 4 | | | | IV-1 | Rpia | 22934 | 4-May-15 | 20630 | 3 | 4 | | | IV-1 | Rxrb | 6257 | 4-May-15 |
| 20535 | 3 | 4 | | | | IV-1 | Rpl10l | 140801 | 4-May-15 | 20631 | 3 | 4 | | | IV-1 | Ryk | 6259 | 21-May-15 |
| 20536 | 3 | 4 | | | | IV-1 | Rpl12 | 6136 | 12-May-15 | 20632 | 3 | 4 | | | IV-1 | S100z | 170591 | 4-May-15 |
| 20537 | 3 | 4 | | | | IV-1 | Rpl13a | 23521 | 4-May-15 | 20633 | 3 | 4 | | | IV-1 | Sac3d1 | 29901 | 4-May-15 |
| 20538 | 3 | 4 | | | | IV-1 | Rpl14-ps1 | | | 20634 | 3 | 4 | | | IV-1 | Sacm1l | 22908 | 23-May-15 |
| 20539 | 3 | 4 | | | | IV-1 | Rpl15 | 6138 | 12-May-15 | 20635 | 3 | 4 | | | IV-1 | Sag | 6295 | 7-Jun-15 |
| 20540 | 3 | 4 | | | | IV-1 | Rpl17 | 6139 | 7-Jun-15 | 20636 | 3 | 4 | | | IV-1 | Sall4 | 57167 | 23-May-15 |
| 20541 | 3 | 4 | | | | IV-1 | Rpl18 | 6141 | 21-May-15 | 20637 | 3 | 4 | | | IV-1 | Samd1 | 90378 | 4-May-15 |
| 20542 | 3 | 4 | | | | IV-1 | Rpl18a | 6142 | 12-May-15 | 20638 | 3 | 4 | | | IV-1 | Samd3 | 154075 | 7-Jun-15 |
| 20543 | 3 | 4 | | | | IV-1 | Rpl19 | 6143 | 21-May-15 | 20639 | 3 | 4 | | | IV-1 | Samd4b | 55095 | 12-May-15 |
| 20544 | 3 | 4 | | | | IV-1 | Rpl22l1 | 200916 | 4-May-15 | 20640 | 3 | 4 | | | IV-1 | Samd8 | 142891 | 4-May-15 |
| 20545 | 3 | 4 | | | | IV-1 | Rpl23 | 9349 | 7-Jun-15 | 20641 | 3 | 4 | | | IV-1 | Samt2 | | |
| 20546 | 3 | 4 | | | | IV-1 | Rpl23a | 6147 | 12-May-15 | 20642 | 3 | 4 | | | IV-1 | Samt3 | | |
| 20547 | 3 | 4 | | | | IV-1 | Rpl24 | 6152 | 7-Jun-15 | 20643 | 3 | 4 | | | IV-1 | Samt4 | | |
| 20548 | 3 | 4 | | | | IV-1 | Rpl28 | 6158 | 3-May-15 | 20644 | 3 | 4 | | | IV-1 | Sap130 | 79595 | 7-Jun-15 |
| 20549 | 3 | 4 | | | | IV-1 | Rpl3 | 6122 | 31-May-15 | 20645 | 3 | 4 | | | IV-1 | Sar1b | 51128 | 4-May-15 |
| 20550 | 3 | 4 | | | | IV-1 | Rpl31-ps12 | | | 20646 | 3 | 4 | | | IV-1 | Sardh | 1757 | 12-May-15 |
| 20551 | 3 | 4 | | | | IV-1 | Rpl32 | 6161 | 4-May-15 | 20647 | 3 | 4 | | | IV-1 | Sarnp | 84324 | 4-May-15 |
| 20552 | 3 | 4 | | | | IV-1 | Rpl34 | 6164 | 4-May-15 | 20648 | 3 | 4 | | | IV-1 | Sars | 6301 | 7-Jun-15 |
| 20553 | 3 | 4 | | | | IV-1 | Rpl36a | 6173 | 7-Jun-15 | 20649 | 3 | 4 | | | IV-1 | Sars2 | 54938 | 4-May-15 |
| 20554 | 3 | 4 | | | | IV-1 | Rpl37 | 6167 | 4-May-15 | 20650 | 3 | 4 | | | IV-1 | Sart3 | 9733 | 12-May-15 |
| 20555 | 3 | 4 | | | | IV-1 | Rpl38 | 6169 | 12-May-15 | 20651 | 3 | 4 | | | IV-1 | Sash1 | 23328 | 12-May-15 |
| 20556 | 3 | 4 | | | | IV-1 | Rpl39 | 6170 | 12-May-15 | 20652 | 3 | 4 | | | IV-1 | Satl1 | 340562 | 4-May-15 |
| 20557 | 3 | 4 | | | | IV-1 | Rpl5 | 6125 | 23-May-15 | 20653 | 3 | 4 | | | IV-1 | Sav1 | 60485 | 4-May-15 |
| 20558 | 3 | 4 | | | | IV-1 | Rpl6 | 6128 | 12-May-15 | 20654 | 3 | 4 | | | IV-1 | Saysd1 | 55776 | 12-May-15 |
| 20559 | 3 | 4 | | | | IV-1 | Rpl7 | 6129 | 5-May-15 | 20655 | 3 | 4 | | | IV-1 | Sbds | 51119 | 23-May-15 |
| 20560 | 3 | 4 | | | | IV-1 | Rpl7a | 6130 | 7-Jun-15 | 20656 | 3 | 4 | | | IV-1 | Sbf1 | 6305 | 23-May-15 |
| 20561 | 3 | 4 | | | | IV-1 | Rpl7l1 | 285855 | 12-May-15 | 20657 | 3 | 4 | | | IV-1 | Sbf2 | 81846 | 23-May-15 |
| 20562 | 3 | 4 | | | | IV-1 | Rpl9 | 6133 | 4-May-15 | 20658 | 3 | 4 | | | IV-1 | Sbpl | | |
| 20563 | 3 | 4 | | | | IV-1 | Rplp0 | 6175 | 4-May-15 | 20659 | 3 | 4 | | | IV-1 | Scaf11 | 9169 | 12-May-15 |
| 20564 | 3 | 4 | | | | IV-1 | Rplp2 | 6181 | 12-May-15 | 20660 | 3 | 4 | | | IV-1 | Scaf4 | 57466 | 12-May-15 |
| 20565 | 3 | 4 | | | | IV-1 | Rpp14 | 11102 | 4-May-15 | 20661 | 3 | 4 | | | IV-1 | Scaf8 | 22828 | 4-May-15 |
| 20566 | 3 | 4 | | | | IV-1 | Rpp30 | 10556 | 4-May-15 | 20662 | 3 | 4 | | | IV-1 | Scai | 286205 | 4-May-15 |
| 20567 | 3 | 4 | | | | IV-1 | Rpp38 | 10557 | 4-May-15 | 20663 | 3 | 4 | | | IV-1 | Scamp1 | 9522 | 12-May-15 |
| 20568 | 3 | 4 | | | | IV-1 | Rpp40 | 10799 | 12-May-15 | 20664 | 3 | 4 | | | IV-1 | Scamp2 | 10066 | 4-May-15 |
| 20569 | 3 | 4 | | | | IV-1 | Rprd2 | 23248 | 4-May-15 | 20665 | 3 | 4 | | | IV-1 | Scamp3 | 10067 | 4-May-15 |
| 20570 | 3 | 4 | | | | IV-1 | Rprl1 | | | 20666 | 3 | 4 | | | IV-1 | Scamp4 | 113178 | 4-May-15 |
| 20571 | 3 | 4 | | | | IV-1 | Rprl2 | | | 20667 | 3 | 4 | | | IV-1 | Scap | 22937 | 7-Jun-15 |
| 20572 | 3 | 4 | | | | IV-1 | Rps15 | 6209 | 12-May-15 | 20668 | 3 | 4 | | | IV-1 | Scaper | 49855 | 4-May-15 |
| 20573 | 3 | 4 | | | | IV-1 | Rps15a | 6210 | 4-May-15 | 20669 | 3 | 4 | | | IV-1 | Scarf1 | 8578 | 4-May-15 |
| 20574 | 3 | 4 | | | | IV-1 | Rps18 | 6222 | 7-Jun-15 | 20670 | 3 | 4 | | | IV-1 | Scfd2 | 152579 | 4-May-15 |
| 20575 | 3 | 4 | | | | IV-1 | Rps19bp1 | 91582 | 4-May-15 | 20671 | 3 | 4 | | | IV-1 | Scg2 | 7857 | 7-Jun-15 |
| 20576 | 3 | 4 | | | | IV-1 | Rps19-ps3 | | | 20672 | 3 | 4 | | | IV-1 | Scg3 | 29106 | 7-Jun-15 |
| 20577 | 3 | 4 | | | | IV-1 | Rps27rt | | | 20673 | 3 | 4 | | | IV-1 | Scgb1b24 | | |
| 20578 | 3 | 4 | | | | IV-1 | Rps3a1 | | | 20674 | 3 | 4 | | | IV-1 | Scgb1b27 | | |
| 20579 | 3 | 4 | | | | IV-1 | Rps5 | 6193 | 12-May-15 | 20675 | 3 | 4 | | | IV-1 | Scgb1b29 | | |
| 20580 | 3 | 4 | | | | IV-1 | Rps6 | 6194 | 4-May-15 | 20676 | 3 | 4 | | | IV-1 | Scgb1b3 | | |
| 20581 | 3 | 4 | | | | IV-1 | Rps6ka1 | 6195 | 17-May-15 | 20677 | 3 | 4 | | | IV-1 | Scgb1b7 | | |
| 20582 | 3 | 4 | | | | IV-1 | Rps6ka3 | 6197 | 23-May-15 | 20678 | 3 | 4 | | | IV-1 | Scgb2b15 | | |
| 20583 | 3 | 4 | | | | IV-1 | Rps6ka4 | 8986 | 4-May-15 | 20679 | 3 | 4 | | | IV-1 | Scly | 51540 | 4-May-15 |
| 20584 | 3 | 4 | | | | IV-1 | Rps6ka5 | 9252 | 4-May-15 | 20680 | 3 | 4 | | | IV-1 | Scmh1 | 22955 | 4-May-15 |
| 20585 | 3 | 4 | | | | IV-1 | Rps6kb1 | 6198 | 3-May-15 | 20681 | 3 | 4 | | | IV-1 | Scml2 | 10389 | 31-May-15 |
| 20586 | 3 | 4 | | | | IV-1 | Rps6kb2 | 6199 | 4-May-15 | 20682 | 3 | 4 | | | IV-1 | Scn1a | 6323 | 22-May-15 |
| 20587 | 3 | 4 | | | | IV-1 | Rps6kc1 | 26750 | 21-May-15 | 20683 | 3 | 4 | | | IV-1 | Scn2b | 6327 | 12-May-15 |
| 20588 | 3 | 4 | | | | IV-1 | Rps6kl1 | 83694 | 12-May-15 | 20684 | 3 | 4 | | | IV-1 | Scn3b | 55800 | 23-May-15 |
| 20589 | 3 | 4 | | | | IV-1 | Rps9 | 6203 | 4-May-15 | 20685 | 3 | 4 | | | IV-1 | Scnm1 | 79005 | 4-May-15 |
| 20590 | 3 | 4 | | | | IV-1 | Rpsa | 3921 | 21-May-15 | 20686 | 3 | 4 | | | IV-1 | Scnn1g | 6340 | 17-May-15 |
| 20591 | 3 | 4 | | | | IV-1 | Rptoros | | | 20687 | 3 | 4 | | | IV-1 | Scpep1 | 59342 | 4-May-15 |
| 20592 | 3 | 4 | | | | IV-1 | Rpusd2 | 27079 | 4-May-15 | 20688 | 3 | 4 | | | IV-1 | Scrg1 | 13341 | 4-May-15 |
| 20593 | 3 | 4 | | | | IV-1 | Rpusd3 | 285367 | 4-May-15 | 20689 | 3 | 4 | | | IV-1 | Scrt2 | 85508 | 4-May-15 |
| 20594 | 3 | 4 | | | | IV-1 | Rreb1 | 6239 | 7-Jun-15 | 20690 | 3 | 4 | | | IV-1 | Scyl2 | 55681 | 4-May-15 |
| 20595 | 3 | 4 | | | | IV-1 | Rrh | 10692 | 4-May-15 | 20691 | 3 | 4 | | | IV-1 | Scyl3 | 57147 | 7-Jun-15 |
| 20596 | 3 | 4 | | | | IV-1 | Rrn3 | 54700 | 4-May-15 | 20692 | 3 | 4 | | | IV-1 | Sdad1 | 55153 | 4-May-15 |
| 20597 | 3 | 4 | | | | IV-1 | Rrnad1 | 51093 | 4-May-15 | 20693 | 3 | 4 | | | IV-1 | Sdc3 | 9672 | 4-May-15 |
| 20598 | 3 | 4 | | | | IV-1 | Rrp1 | 8568 | 7-Jun-15 | 20694 | 3 | 4 | | | IV-1 | Sdccag8 | 10806 | 23-May-15 |
| 20599 | 3 | 4 | | | | IV-1 | Rrp7a | 27341 | 4-May-15 | 20695 | 3 | 4 | | | IV-1 | Sde2 | 163859 | 4-May-15 |
| 20600 | 3 | 4 | | | | IV-1 | Rrp8 | 23378 | 28-May-15 | 20696 | 3 | 4 | | | IV-1 | Sdf2 | 6388 | 4-May-15 |
| 20601 | 3 | 4 | | | | IV-1 | Rrp9 | 9136 | 4-May-15 | 20697 | 3 | 4 | | | IV-1 | Sdha | 6389 | 23-May-15 |
| 20602 | 3 | 4 | | | | IV-1 | Rsad1 | 55316 | 4-May-15 | 20698 | 3 | 4 | | | IV-1 | Sdhaf2 | 54949 | 23-May-15 |
| 20603 | 3 | 4 | | | | IV-1 | Rsbn1l | 222194 | 4-May-15 | 20699 | 3 | 4 | | | IV-1 | Sdhb | 6390 | 4-May-15 |
| 20604 | 3 | 4 | | | | IV-1 | Rsc1a1 | 6248 | 4-May-15 | 20700 | 3 | 4 | | | IV-1 | Sdk2 | 54549 | 4-May-15 |
| 20605 | 3 | 4 | | | | IV-1 | Rsl1 | | | 20701 | 3 | 4 | | | IV-1 | Sdr16c6 | 442388 | 4-May-15 |
| 20606 | 3 | 4 | | | | IV-1 | Rsl1d1 | 26156 | 4-May-15 | 20702 | 3 | 4 | | | IV-1 | Sdr39u1 | 56948 | 21-May-15 |
| 20607 | 3 | 4 | | | | IV-1 | Rsl24d1 | 51187 | 4-May-15 | 20703 | 3 | 4 | | | IV-1 | Sec1 | 653677 | 4-May-15 |
| 20608 | 3 | 4 | | | | IV-1 | Rslcan18 | | | 20704 | 3 | 4 | | | IV-1 | Sec14l3 | 6397 | 31-May-15 |
| 20609 | 3 | 4 | | | | IV-1 | Rspo3 | 84870 | 4-May-15 | 20705 | 3 | 4 | | | IV-1 | Sec16b | 89866 | 3-May-15 |
| 20610 | 3 | 4 | | | | IV-1 | Rsprv1 | 89970 | 20-May-15 | 20706 | 3 | 4 | | | IV-1 | Sec22b | 9554 | 4-May-15 |

Fig. 30 - 110

| | | | | | | | | | | | | | | | | |
|---|---|---|---|---|---|---|---|---|---|---|---|---|---|---|---|---|
| 20707 | 3 | 4 | | | | IV-1 | Sec22c | 9117 | 4-May-15 | 20803 | 3 | 4 | | | IV-1 | Sipa1l3 | 23094 | 4-May-15 |
| 20708 | 3 | 4 | | | | IV-1 | Sec23b | 10483 | 4-May-15 | 20804 | 3 | 4 | | | IV-1 | Sirt2 | 22933 | 17-May-15 |
| 20709 | 3 | 4 | | | | IV-1 | Sec24a | 10802 | 4-May-15 | 20805 | 3 | 4 | | | IV-1 | Sirt3 | 23410 | 31-May-15 |
| 20710 | 3 | 4 | | | | IV-1 | Sec24c | 9632 | 12-May-15 | 20806 | 3 | 4 | | | IV-1 | Sirt7 | 51547 | 23-May-15 |
| 20711 | 3 | 4 | | | | IV-1 | Sec24d | 9871 | 17-May-15 | 20807 | 3 | 4 | | | IV-1 | Sis | 5155 | 7-Jun-15 |
| 20712 | 3 | 4 | | | | IV-1 | Sec31a | 22872 | 10-May-15 | 20808 | 3 | 4 | | | IV-1 | Six3 | 6496 | 22-May-15 |
| 20713 | 3 | 4 | | | | IV-1 | Sec63 | 11231 | 4-May-15 | 20809 | 3 | 4 | | | IV-1 | Six3os1 | | |
| 20714 | 3 | 4 | | | | IV-1 | Secisbp2 | 79048 | 4-May-15 | 20810 | 3 | 4 | | | IV-1 | Six6 | 4990 | 28-May-15 |
| 20715 | 3 | 4 | | | | IV-1 | Sel1l | 6400 | 12-May-15 | 20811 | 3 | 4 | | | IV-1 | Skida1 | 387640 | 4-May-15 |
| 20716 | 3 | 4 | | | | IV-1 | Sellll2 | 80343 | 4-May-15 | 20812 | 3 | 4 | | | IV-1 | Skint11 | | |
| 20717 | 3 | 4 | | | | IV-1 | Sema3a | 10371 | 17-May-15 | 20813 | 3 | 4 | | | IV-1 | Skint6 | | |
| 20718 | 3 | 4 | | | | IV-1 | Senp2 | 59343 | 7-Jun-15 | 20814 | 3 | 4 | | | IV-1 | Skint7 | | |
| 20719 | 3 | 4 | | | | IV-1 | Senp3 | 26168 | 4-May-15 | 20815 | 3 | 4 | | | IV-1 | Skint9 | | |
| 20720 | 3 | 4 | | | | IV-1 | Senp5 | 205564 | 12-May-15 | 20816 | 3 | 4 | | | IV-1 | Skiv2l | 6499 | 12-May-15 |
| 20721 | 3 | 4 | | | | IV-1 | Senp6 | 26054 | 12-May-15 | 20817 | 3 | 4 | | | IV-1 | Skiv2l2 | 23517 | 21-May-15 |
| 20722 | 3 | 4 | | | | IV-1 | Senp7 | 57337 | 4-May-15 | 20818 | 3 | 4 | | | IV-1 | Skor1 | 390598 | 4-May-15 |
| 20723 | 3 | 4 | | | | IV-1 | Senp8 | 123228 | 4-May-15 | 20819 | 3 | 4 | | | IV-1 | Skor2 | 652991 | 21-May-15 |
| 20724 | 3 | 4 | | | | IV-1 | Sephs1 | 22929 | 2-Jun-15 | 20820 | 3 | 4 | | | IV-1 | Skp1a | 6500 | 4-May-15 |
| 20725 | 3 | 4 | | | | IV-1 | Sephs2 | 22928 | 4-May-15 | 20821 | 3 | 4 | | | IV-1 | Slain1 | 122060 | 4-May-15 |
| 20726 | 3 | 4 | | | | IV-1 | Sepn1 | 57190 | 23-May-15 | 20822 | 3 | 4 | | | IV-1 | Slain2 | 57606 | 4-May-15 |
| 20727 | 3 | 4 | | | | IV-1 | Sept11 | 55752 | 12-May-15 | 20823 | 3 | 4 | | | IV-1 | Slamf1 | 6504 | 12-May-15 |
| 20728 | 3 | 4 | | | | IV-1 | Sept14 | 346288 | 4-May-15 | 20824 | 3 | 4 | | | IV-1 | Slc10a2 | 6555 | 12-May-15 |
| 20729 | 3 | 4 | | | | IV-1 | Sept15 | | | 20825 | 3 | 4 | | | IV-1 | Slc10a5 | 347051 | 4-May-15 |
| 20730 | 3 | 4 | | | | IV-1 | Sept2 | 4735 | 7-Jun-15 | 20826 | 3 | 4 | | | IV-1 | Slc12a6 | 9990 | 23-May-15 |
| 20731 | 3 | 4 | | | | IV-1 | Serac1 | 84947 | 23-May-15 | 20827 | 3 | 4 | | | IV-1 | Slc12a8 | 84561 | 1-Jun-15 |
| 20732 | 3 | 4 | | | | IV-1 | Serf1 | 8293 | 4-May-15 | 20828 | 3 | 4 | | | IV-1 | Slc12a9 | 56996 | 4-May-15 |
| 20733 | 3 | 4 | | | | IV-1 | Serf2 | 10169 | 4-May-15 | 20829 | 3 | 4 | | | IV-1 | Slc13a1 | 6561 | 4-May-15 |
| 20734 | 3 | 4 | | | | IV-1 | Sergef | 26297 | 4-May-15 | 20830 | 3 | 4 | | | IV-1 | Slc14a1 | 6563 | 21-May-15 |
| 20735 | 3 | 4 | | | | IV-1 | Serhl | 94009 | 4-May-15 | 20831 | 3 | 4 | | | IV-1 | Slc16a9 | 220963 | 4-May-15 |
| 20736 | 3 | 4 | | | | IV-1 | Serinc2 | 347735 | 4-May-15 | 20832 | 3 | 4 | | | IV-1 | Slc17a5 | 26503 | 23-May-15 |
| 20737 | 3 | 4 | | | | IV-1 | Serinc5 | 256987 | 28-May-15 | 20833 | 3 | 4 | | | IV-1 | Slc17a7 | 57030 | 4-May-15 |
| 20738 | 3 | 4 | | | | IV-1 | Serpinb6a | | | 20834 | 3 | 4 | | | IV-1 | Slc18a3 | 6572 | 4-May-15 |
| 20739 | 3 | 4 | | | | IV-1 | Serpinb6d | | | 20835 | 3 | 4 | | | IV-1 | Slc18b1 | 116843 | 4-May-15 |
| 20740 | 3 | 4 | | | | IV-1 | Serpinb7 | 8710 | 4-May-15 | 20836 | 3 | 4 | | | IV-1 | Slc1a7 | 6512 | 4-May-15 |
| 20741 | 3 | 4 | | | | IV-1 | Serpinb9d | | | 20837 | 3 | 4 | | | IV-1 | Slc20a1 | 6574 | 4-May-15 |
| 20742 | 3 | 4 | | | | IV-1 | Serpinb9e | | | 20838 | 3 | 4 | | | IV-1 | Slc22a13 | 9390 | 4-May-15 |
| 20743 | 3 | 4 | | | | IV-1 | Serpinb9f | | | 20839 | 3 | 4 | | | IV-1 | Slc22a13b-ps | | |
| 20744 | 3 | 4 | | | | IV-1 | Sestd1 | 91404 | 4-May-15 | 20840 | 3 | 4 | | | IV-1 | Slc22a16 | 85413 | 4-May-15 |
| 20745 | 3 | 4 | | | | IV-1 | Setd1b | 23067 | 4-May-15 | 20841 | 3 | 4 | | | IV-1 | Slc22a17 | 51310 | 1-Jun-15 |
| 20746 | 3 | 4 | | | | IV-1 | Setd2 | 29072 | 31-May-15 | 20842 | 3 | 4 | | | IV-1 | Slc22a2 | 6582 | 4-May-15 |
| 20747 | 3 | 4 | | | | IV-1 | Setd3 | 84193 | 4-May-15 | 20843 | 3 | 4 | | | IV-1 | Slc22a21 | | |
| 20748 | 3 | 4 | | | | IV-1 | Setd4 | 54093 | 4-May-15 | 20844 | 3 | 4 | | | IV-1 | Slc22a22 | | |
| 20749 | 3 | 4 | | | | IV-1 | Setd6 | 79918 | 4-May-15 | 20845 | 3 | 4 | | | IV-1 | Slc22a27 | | |
| 20750 | 3 | 4 | | | | IV-1 | Setd7 | 80854 | 12-May-15 | 20846 | 3 | 4 | | | IV-1 | Slc23a1 | 9963 | 7-Jun-15 |
| 20751 | 3 | 4 | | | | IV-1 | Setd8 | 387893 | 4-May-15 | 20847 | 3 | 4 | | | IV-1 | Slc23a3 | 151295 | 4-May-15 |
| 20752 | 3 | 4 | | | | IV-1 | Sez6 | 124925 | 4-May-15 | 20848 | 3 | 4 | | | IV-1 | Slc24a1 | 9187 | 4-May-15 |
| 20753 | 3 | 4 | | | | IV-1 | Sez6l | 23544 | 12-May-15 | 20849 | 3 | 4 | | | IV-1 | Slc24a2 | 25769 | 4-May-15 |
| 20754 | 3 | 4 | | | | IV-1 | Sez6l2 | 26470 | 4-May-15 | 20850 | 3 | 4 | | | IV-1 | Slc24a3 | 57419 | 4-May-15 |
| 20755 | 3 | 4 | | | | IV-1 | Sf3a2 | 8175 | 4-May-15 | 20851 | 3 | 4 | | | IV-1 | Slc25a17 | 10478 | 4-May-15 |
| 20756 | 3 | 4 | | | | IV-1 | Sf3a3 | 10946 | 4-May-15 | 20852 | 3 | 4 | | | IV-1 | Slc25a18 | 83733 | 12-May-15 |
| 20757 | 3 | 4 | | | | IV-1 | Sf3b1 | 23451 | 16-Jun-15 | 20853 | 3 | 4 | | | IV-1 | Slc25a19 | 60386 | 23-May-15 |
| 20758 | 3 | 4 | | | | IV-1 | Sf3b2 | 10992 | 12-May-15 | 20854 | 3 | 4 | | | IV-1 | Slc25a20 | 788 | 12-May-15 |
| 20759 | 3 | 4 | | | | IV-1 | Sf3b3 | 23450 | 4-May-15 | 20855 | 3 | 4 | | | IV-1 | Slc25a24 | 29957 | 4-May-15 |
| 20760 | 3 | 4 | | | | IV-1 | Sf3b4 | 10262 | 1-Jun-15 | 20856 | 3 | 4 | | | IV-1 | Slc25a32 | 81034 | 4-May-15 |
| 20761 | 3 | 4 | | | | IV-1 | Sf3b5 | 83443 | 4-May-15 | 20857 | 3 | 4 | | | IV-1 | Slc25a41 | 284427 | 4-May-15 |
| 20762 | 3 | 4 | | | | IV-1 | Sf3b6 | 51639 | 4-May-15 | 20858 | 3 | 4 | | | IV-1 | Slc25a42 | 284439 | 4-May-15 |
| 20763 | 3 | 4 | | | | IV-1 | Sfmbt2 | 57713 | 4-May-15 | 20859 | 3 | 4 | | | IV-1 | Slc26a6 | 65010 | 4-May-15 |
| 20764 | 3 | 4 | | | | IV-1 | Sfr1 | 119392 | 4-May-15 | 20860 | 3 | 4 | | | IV-1 | Slc26a9 | 115019 | 4-May-15 |
| 20765 | 3 | 4 | | | | IV-1 | Sft2d1 | 113402 | 4-May-15 | 20861 | 3 | 4 | | | IV-1 | Slc27a5 | 10998 | 4-May-15 |
| 20766 | 3 | 4 | | | | IV-1 | Sft2d2 | 375035 | 4-May-15 | 20862 | 3 | 4 | | | IV-1 | Slc28a2 | 9153 | 4-May-15 |
| 20767 | 3 | 4 | | | | IV-1 | Sft2d3 | 84826 | 4-May-15 | 20863 | 3 | 4 | | | IV-1 | Slc29a1 | 2030 | 17-May-15 |
| 20768 | 3 | 4 | | | | IV-1 | Sfxn2 | 118980 | 4-May-15 | 20864 | 3 | 4 | | | IV-1 | Slc2a8 | 29988 | 4-May-15 |
| 20769 | 3 | 4 | | | | IV-1 | Sgca | 6442 | 12-May-15 | 20865 | 3 | 4 | | | IV-1 | Slc30a6 | 55676 | 4-May-15 |
| 20770 | 3 | 4 | | | | IV-1 | Sgip1 | 84251 | 12-May-15 | 20866 | 3 | 4 | | | IV-1 | Slc30a8 | 169026 | 31-May-15 |
| 20771 | 3 | 4 | | | | IV-1 | Sgsh | 6448 | 17-May-15 | 20867 | 3 | 4 | | | IV-1 | Slc30a9 | 10463 | 4-May-15 |
| 20772 | 3 | 4 | | | | IV-1 | Sgsm3 | 27352 | 4-May-15 | 20868 | 3 | 4 | | | IV-1 | Slc33a1 | 9197 | 4-May-15 |
| 20773 | 3 | 4 | | | | IV-1 | Sgta | 6449 | 28-May-15 | 20869 | 3 | 4 | | | IV-1 | Slc34a1 | 6569 | 24-May-15 |
| 20774 | 3 | 4 | | | | IV-1 | Sgtb | 54557 | 14-May-15 | 20870 | 3 | 4 | | | IV-1 | Slc35a1 | 10559 | 23-May-15 |
| 20775 | 3 | 4 | | | | IV-1 | Sh2b1 | 25970 | 21-May-15 | 20871 | 3 | 4 | | | IV-1 | Slc35a2 | 7355 | 4-May-15 |
| 20776 | 3 | 4 | | | | IV-1 | Sh2d1a | 4068 | 23-May-15 | 20872 | 3 | 4 | | | IV-1 | Slc35a3 | 23443 | 4-May-15 |
| 20777 | 3 | 4 | | | | IV-1 | Sh2d1b1 | | | 20873 | 3 | 4 | | | IV-1 | Slc35a4 | 113829 | 4-May-15 |
| 20778 | 3 | 4 | | | | IV-1 | Sh2d1b2 | | | 20874 | 3 | 4 | | | IV-1 | Slc35a5 | 55032 | 4-May-15 |
| 20779 | 3 | 4 | | | | IV-1 | Sh2d2a | 9047 | 4-May-15 | 20875 | 3 | 4 | | | IV-1 | Slc35b1 | 10237 | 21-May-15 |
| 20780 | 3 | 4 | | | | IV-1 | Sh2d3c | 10044 | 12-May-15 | 20876 | 3 | 4 | | | IV-1 | Slc35b2 | 347734 | 4-May-15 |
| 20781 | 3 | 4 | | | | IV-1 | Sh3d19 | 152503 | 4-May-15 | 20877 | 3 | 4 | | | IV-1 | Slc35b3 | 51000 | 28-May-15 |
| 20782 | 3 | 4 | | | | IV-1 | Sh3glb2 | 56904 | 4-May-15 | 20878 | 3 | 4 | | | IV-1 | Slc35b4 | 84912 | 4-May-15 |
| 20783 | 3 | 4 | | | | IV-1 | Sh3kbp1 | 30011 | 4-May-15 | 20879 | 3 | 4 | | | IV-1 | Slc35c1 | 55343 | 28-May-15 |
| 20784 | 3 | 4 | | | | IV-1 | Shc1 | 6464 | 31-May-15 | 20880 | 3 | 4 | | | IV-1 | Slc35d1 | 23169 | 12-May-15 |
| 20785 | 3 | 4 | | | | IV-1 | Shc2 | 25759 | 4-May-15 | 20881 | 3 | 4 | | | IV-1 | Slc35d2 | 11046 | 4-May-15 |
| 20786 | 3 | 4 | | | | IV-1 | Shd | 56961 | 4-May-15 | 20882 | 3 | 4 | | | IV-1 | Slc35e1 | 79939 | 4-May-15 |
| 20787 | 3 | 4 | | | | IV-1 | Shf | 90525 | 21-May-15 | 20883 | 3 | 4 | | | IV-1 | Slc35e2 | 9906 | 7-Jun-15 |
| 20788 | 3 | 4 | | | | IV-1 | Shisa9 | 729993 | 12-May-15 | 20884 | 3 | 4 | | | IV-1 | Slc35e4 | 339665 | 4-May-15 |
| 20789 | 3 | 4 | | | | IV-1 | Shkbp1 | 92799 | 4-May-15 | 20885 | 3 | 4 | | | IV-1 | Slc35f5 | 80255 | 4-May-15 |
| 20790 | 3 | 4 | | | | IV-1 | Shmt1 | 6470 | 12-May-15 | 20886 | 3 | 4 | | | IV-1 | Slc36a1 | 206358 | 12-May-15 |
| 20791 | 3 | 4 | | | | IV-1 | Shox2 | 6474 | 17-May-15 | 20887 | 3 | 4 | | | IV-1 | Slc36a4 | 120103 | 28-May-15 |
| 20792 | 3 | 4 | | | | IV-1 | Shpk | 23729 | 4-May-15 | 20888 | 3 | 4 | | | IV-1 | Slc38a11 | 151258 | 4-May-15 |
| 20793 | 3 | 4 | | | | IV-1 | Shq1 | 55164 | 3-May-15 | 20889 | 3 | 4 | | | IV-1 | Slc38a9 | 153129 | 14-May-15 |
| 20794 | 3 | 4 | | | | IV-1 | Shroom1 | 134549 | 12-May-15 | 20890 | 3 | 4 | | | IV-1 | Slc39a1 | 27173 | 17-May-15 |
| 20795 | 3 | 4 | | | | IV-1 | Siae | 54414 | 4-May-15 | 20891 | 3 | 4 | | | IV-1 | Slc39a10 | 57181 | 4-May-15 |
| 20796 | 3 | 4 | | | | IV-1 | Sidt1 | 54847 | 12-May-15 | 20892 | 3 | 4 | | | IV-1 | Slc39a13 | 91252 | 17-May-15 |
| 20797 | 3 | 4 | | | | IV-1 | Sigirr | 59307 | 24-May-15 | 20893 | 3 | 4 | | | IV-1 | Slc39a3 | 29985 | 4-May-15 |
| 20798 | 3 | 4 | | | | IV-1 | Sike1 | 80143 | 4-May-15 | 20894 | 3 | 4 | | | IV-1 | Slc39a4 | 55630 | 10-May-15 |
| 20799 | 3 | 4 | | | | IV-1 | Sil1 | 64374 | 23-May-15 | 20895 | 3 | 4 | | | IV-1 | Slc3a1 | 6519 | 12-May-15 |
| 20800 | 3 | 4 | | | | IV-1 | Sim1 | 6492 | 28-May-15 | 20896 | 3 | 4 | | | IV-1 | Slc45a1 | 50651 | 4-May-15 |
| 20801 | 3 | 4 | | | | IV-1 | Sipa1l1 | 26037 | 4-May-15 | 20897 | 3 | 4 | | | IV-1 | Slc45a2 | 51151 | 23-May-15 |
| 20802 | 3 | 4 | | | | IV-1 | Sipa1l2 | 57568 | 4-May-15 | 20898 | 3 | 4 | | | IV-1 | Slc46a1 | 113235 | 23-May-15 |

Fig. 30 - 111

| | | | | | | | | | | | | | | | | |
|---|---|---|---|---|---|---|---|---|---|---|---|---|---|---|---|---|
| 20899 | 3 | 4 | | | | IV-1 | Slc48a1 | 55652 | 4-May-15 | 20994 | 3 | 4 | | | IV-1 | Sntg2 | 54221 | 4-May-15 |
| 20900 | 3 | 4 | | | | IV-1 | Slc4a2 | 6522 | 21-May-15 | 20995 | 3 | 4 | | | IV-1 | Snurf | 8926 | 7-Jun-15 |
| 20901 | 3 | 4 | | | | IV-1 | Slc4a3 | 6508 | 12-May-15 | 20996 | 3 | 4 | | | IV-1 | Snw1 | 22938 | 4-May-15 |
| 20902 | 3 | 4 | | | | IV-1 | Slc50a1 | 55974 | 4-May-15 | 20997 | 3 | 4 | | | IV-1 | Snx1 | 6642 | 21-May-15 |
| 20903 | 3 | 4 | | | | IV-1 | Slc5a11 | 115584 | 4-May-15 | 20998 | 3 | 4 | | | IV-1 | Snx10 | 29887 | 4-May-15 |
| 20904 | 3 | 4 | | | | IV-1 | Slc5a12 | 159963 | 4-May-15 | 20999 | 3 | 4 | | | IV-1 | Snx12 | 29934 | 2-Jun-15 |
| 20905 | 3 | 4 | | | | IV-1 | Slc5a4b | | | 21000 | 3 | 4 | | | IV-1 | Snx13 | 23161 | 12-May-15 |
| 20906 | 3 | 4 | | | | IV-1 | Slc5a5 | 6528 | 12-May-15 | 21001 | 3 | 4 | | | IV-1 | Snx14 | 57231 | 29-May-15 |
| 20907 | 3 | 4 | | | | IV-1 | Slc6a11 | 6538 | 4-May-15 | 21002 | 3 | 4 | | | IV-1 | Snx15 | 29907 | 4-May-15 |
| 20908 | 3 | 4 | | | | IV-1 | Slc6a2 | 6530 | 12-May-15 | 21003 | 3 | 4 | | | IV-1 | Snx17 | 9784 | 4-May-15 |
| 20909 | 3 | 4 | | | | IV-1 | Slc6a6 | 6533 | 12-May-15 | 21004 | 3 | 4 | | | IV-1 | Snx18 | 112574 | 4-May-15 |
| 20910 | 3 | 4 | | | | IV-1 | Slc7a13 | 157724 | 4-May-15 | 21005 | 3 | 4 | | | IV-1 | Snx2 | 6643 | 4-May-15 |
| 20911 | 3 | 4 | | | | IV-1 | Slc7a14 | 57709 | 4-May-15 | 21006 | 3 | 4 | | | IV-1 | Snx27 | 81609 | 4-May-15 |
| 20912 | 3 | 4 | | | | IV-1 | Slc7a7 | 9056 | 23-May-15 | 21007 | 3 | 4 | | | IV-1 | Snx29 | 92017 | 4-May-15 |
| 20913 | 3 | 4 | | | | IV-1 | Slc8a1 | 6547 | 12-May-15 | 21008 | 3 | 4 | | | IV-1 | Snx3 | 8724 | 2-Jun-15 |
| 20914 | 3 | 4 | | | | IV-1 | Slc9a5 | 6553 | 4-May-15 | 21009 | 3 | 4 | | | IV-1 | Snx30 | 401548 | 4-May-15 |
| 20915 | 3 | 4 | | | | IV-1 | Slc9b2 | 133308 | 4-May-15 | 21010 | 3 | 4 | | | IV-1 | Snx31 | 169166 | 4-May-15 |
| 20916 | 3 | 4 | | | | IV-1 | Slc9c1 | 285335 | 4-May-15 | 21011 | 3 | 4 | | | IV-1 | Snx33 | 257364 | 12-May-15 |
| 20917 | 3 | 4 | | | | IV-1 | Slco1a1 | | | 21012 | 3 | 4 | | | IV-1 | Socs5 | 9655 | 12-May-15 |
| 20918 | 3 | 4 | | | | IV-1 | Slco1c1 | 53919 | 4-May-15 | 21013 | 3 | 4 | | | IV-1 | Socs6 | 9306 | 4-May-15 |
| 20919 | 3 | 4 | | | | IV-1 | Slco6c1 | | | 21014 | 3 | 4 | | | IV-1 | Socs7 | 30837 | 7-Jun-15 |
| 20920 | 3 | 4 | | | | IV-1 | Slco6d1 | | | 21015 | 3 | 4 | | | IV-1 | Sod1 | 6647 | 31-May-15 |
| 20921 | 3 | 4 | | | | IV-1 | Slirp | 81892 | 4-May-15 | 21016 | 3 | 4 | | | IV-1 | Sohlh1 | 402381 | 4-May-15 |
| 20922 | 3 | 4 | | | | IV-1 | Slitrk2 | 84631 | 4-May-15 | 21017 | 3 | 4 | | | IV-1 | Sohlh2 | 54937 | 4-May-15 |
| 20923 | 3 | 4 | | | | IV-1 | Slitrk3 | 22865 | 4-May-15 | 21018 | 3 | 4 | | | IV-1 | Son | 6651 | 12-May-15 |
| 20924 | 3 | 4 | | | | IV-1 | Slitrk4 | 139065 | 4-May-15 | 21019 | 3 | 4 | | | IV-1 | Sorbs1 | 10580 | 12-May-15 |
| 20925 | 3 | 4 | | | | IV-1 | Slu7 | 10569 | 4-May-15 | 21020 | 3 | 4 | | | IV-1 | Sord | 6652 | 12-May-15 |
| 20926 | 3 | 4 | | | | IV-1 | Six1b | 79008 | 4-May-15 | 21021 | 3 | 4 | | | IV-1 | Sos2 | 6655 | 4-May-15 |
| 20927 | 3 | 4 | | | | IV-1 | Six4 | 84464 | 23-May-15 | 21022 | 3 | 4 | | | IV-1 | Sox1 | 6656 | 4-May-15 |
| 20928 | 3 | 4 | | | | IV-1 | Six4ip | 128710 | 4-May-15 | 21023 | 3 | 4 | | | IV-1 | Sox10 | 6663 | 31-May-15 |
| 20929 | 3 | 4 | | | | IV-1 | Sixl1 | | | 21024 | 3 | 4 | | | IV-1 | Sox15 | 6665 | 12-May-15 |
| 20930 | 3 | 4 | | | | IV-1 | Sly | 54440 | 4-May-15 | 21025 | 3 | 4 | | | IV-1 | Sox17 | 64321 | 31-May-15 |
| 20931 | 3 | 4 | | | | IV-1 | Smad1 | 4086 | 7-Jun-15 | 21026 | 3 | 4 | | | IV-1 | Sox2ot | 347689 | 12-May-15 |
| 20932 | 3 | 4 | | | | IV-1 | Smad3 | 4088 | 24-May-15 | 21027 | 3 | 4 | | | IV-1 | Sox30 | 11063 | 28-May-15 |
| 20933 | 3 | 4 | | | | IV-1 | Smad5 | 4090 | 12-May-15 | 21028 | 3 | 4 | | | IV-1 | Sp2 | 6668 | 7-Jun-15 |
| 20934 | 3 | 4 | | | | IV-1 | Smarca2 | 6595 | 4-May-15 | 21029 | 3 | 4 | | | IV-1 | Sp3os | | |
| 20935 | 3 | 4 | | | | IV-1 | Smarca5-ps | | | 21030 | 3 | 4 | | | IV-1 | Sp4 | 6671 | 28-May-15 |
| 20936 | 3 | 4 | | | | IV-1 | Smarcad1 | 56916 | 4-May-15 | 21031 | 3 | 4 | | | IV-1 | Sp5 | 389058 | 4-May-15 |
| 20937 | 3 | 4 | | | | IV-1 | Smarcal1 | 50485 | 23-May-15 | 21032 | 3 | 4 | | | IV-1 | Sp8 | 221833 | 4-May-15 |
| 20938 | 3 | 4 | | | | IV-1 | Smarcb1 | 6598 | 12-May-15 | 21033 | 3 | 4 | | | IV-1 | Sp9 | 100131390 | 4-May-15 |
| 20939 | 3 | 4 | | | | IV-1 | Smarcc1 | 6599 | 4-May-15 | 21034 | 3 | 4 | | | IV-1 | Spaca4 | 171169 | 4-May-15 |
| 20940 | 3 | 4 | | | | IV-1 | Smarcd1 | 6602 | 4-May-15 | 21035 | 3 | 4 | | | IV-1 | Spag1 | 6674 | 26-May-15 |
| 20941 | 3 | 4 | | | | IV-1 | Smc1a | 8243 | 23-May-15 | 21036 | 3 | 4 | | | IV-1 | Spag4 | 6676 | 4-May-15 |
| 20942 | 3 | 4 | | | | IV-1 | Smc1b | 27127 | 4-May-15 | 21037 | 3 | 4 | | | IV-1 | Spam1 | 6677 | 12-May-15 |
| 20943 | 3 | 4 | | | | IV-1 | Smc6 | 79677 | 4-May-15 | 21038 | 3 | 4 | | | IV-1 | Spata1 | 100505741 | 4-May-15 |
| 20944 | 3 | 4 | | | | IV-1 | Smchd1 | 23347 | 23-May-15 | 21039 | 3 | 4 | | | IV-1 | Spata17 | 128153 | 4-May-15 |
| 20945 | 3 | 4 | | | | IV-1 | Smco3 | 440087 | 4-May-15 | 21040 | 3 | 4 | | | IV-1 | Spata20 | 64847 | 4-May-15 |
| 20946 | 3 | 4 | | | | IV-1 | Smco4 | 56935 | 4-May-15 | 21041 | 3 | 4 | | | IV-1 | Spata21 | 374955 | 4-May-15 |
| 20947 | 3 | 4 | | | | IV-1 | Smdt1 | 91689 | 4-May-15 | 21042 | 3 | 4 | | | IV-1 | Spata22 | 84690 | 4-May-15 |
| 20948 | 3 | 4 | | | | IV-1 | Smek1 | 55671 | 1-Jun-15 | 21043 | 3 | 4 | | | IV-1 | Spata2l | 124044 | 4-May-15 |
| 20949 | 3 | 4 | | | | IV-1 | Smek2 | 57223 | 4-May-15 | 21044 | 3 | 4 | | | IV-1 | Spata31d1a | | |
| 20950 | 3 | 4 | | | | IV-1 | Smg1 | 23049 | 4-May-15 | 21045 | 3 | 4 | | | IV-1 | Spata31d1b | | |
| 20951 | 3 | 4 | | | | IV-1 | Smg5 | 23381 | 12-May-15 | 21046 | 3 | 4 | | | IV-1 | Spata31d1c | | |
| 20952 | 3 | 4 | | | | IV-1 | Smg6 | 23293 | 4-May-15 | 21047 | 3 | 4 | | | IV-1 | Spata32 | 124783 | 21-May-15 |
| 20953 | 3 | 4 | | | | IV-1 | Smg7 | 9887 | 4-May-15 | 21048 | 3 | 4 | | | IV-1 | Spata5 | 166378 | 4-May-15 |
| 20954 | 3 | 4 | | | | IV-1 | Smg8 | 55181 | 4-May-15 | 21049 | 3 | 4 | | | IV-1 | Spatc1 | 375686 | 4-May-15 |
| 20955 | 3 | 4 | | | | IV-1 | Smg9 | 56006 | 4-May-15 | 21050 | 3 | 4 | | | IV-1 | Spatc1l | 84221 | 4-May-15 |
| 20956 | 3 | 4 | | | | IV-1 | Smgc | | | 21051 | 3 | 4 | | | IV-1 | Spats1 | 221409 | 4-May-15 |
| 20957 | 3 | 4 | | | | IV-1 | Smim1 | 388588 | 12-May-15 | 21052 | 3 | 4 | | | IV-1 | Spdyb | | |
| 20958 | 3 | 4 | | | | IV-1 | Smim12 | 113444 | 4-May-15 | 21053 | 3 | 4 | | | IV-1 | Speer1-ps1 | | |
| 20959 | 3 | 4 | | | | IV-1 | Smim13 | 221710 | 12-May-15 | 21054 | 3 | 4 | | | IV-1 | Speer2 | | |
| 20960 | 3 | 4 | | | | IV-1 | Smim14 | 201895 | 4-May-15 | 21055 | 3 | 4 | | | IV-1 | Speer3 | | |
| 20961 | 3 | 4 | | | | IV-1 | Smim15 | 643155 | 4-May-15 | 21056 | 3 | 4 | | | IV-1 | Speer4a | | |
| 20962 | 3 | 4 | | | | IV-1 | Smim19 | 114926 | 4-May-15 | 21057 | 3 | 4 | | | IV-1 | Speer4c | | |
| 20963 | 3 | 4 | | | | IV-1 | Smim20 | 389203 | 4-May-15 | 21058 | 3 | 4 | | | IV-1 | Speer4d | | |
| 20964 | 3 | 4 | | | | IV-1 | Smim8 | 57150 | 4-May-15 | 21059 | 3 | 4 | | | IV-1 | Speer4e | | |
| 20965 | 3 | 4 | | | | IV-1 | Smlr1 | 100507203 | 4-May-15 | 21060 | 3 | 4 | | | IV-1 | Speer4f | | |
| 20966 | 3 | 4 | | | | IV-1 | Smn1 | 6606 | 23-May-15 | 21061 | 3 | 4 | | | IV-1 | Speer5-ps1 | | |
| 20967 | 3 | 4 | | | | IV-1 | Smndc1 | 10285 | 23-May-15 | 21062 | 3 | 4 | | | IV-1 | Speer6-ps1 | | |
| 20968 | 3 | 4 | | | | IV-1 | Smo | 6608 | 7-Jun-15 | 21063 | 3 | 4 | | | IV-1 | Speer7-ps1 | | |
| 20969 | 3 | 4 | | | | IV-1 | Smok3b | | | 21064 | 3 | 4 | | | IV-1 | Speer8-ps1 | | |
| 20970 | 3 | 4 | | | | IV-1 | Smok4a | | | 21065 | 3 | 4 | | | IV-1 | Speer9-ps1 | | |
| 20971 | 3 | 4 | | | | IV-1 | Smpd2 | 6610 | 4-May-15 | 21066 | 3 | 4 | | | IV-1 | Spef1 | 25876 | 4-May-15 |
| 20972 | 3 | 4 | | | | IV-1 | Smr3a | 26952 | 4-May-15 | 21067 | 3 | 4 | | | IV-1 | Spen | 23013 | 13-Jun-15 |
| 20973 | 3 | 4 | | | | IV-1 | Sms | 6611 | 13-Jun-15 | 21068 | 3 | 4 | | | IV-1 | Spert | 220082 | 4-May-15 |
| 20974 | 3 | 4 | | | | IV-1 | Smtnl1 | 219537 | 4-May-15 | 21069 | 3 | 4 | | | IV-1 | Spesp1 | 246777 | 4-May-15 |
| 20975 | 3 | 4 | | | | IV-1 | Smug1 | 23583 | 4-May-15 | 21070 | 3 | 4 | | | IV-1 | Spg11 | 80208 | 4-May-15 |
| 20976 | 3 | 4 | | | | IV-1 | Smurf2 | 64750 | 23-May-15 | 21071 | 3 | 4 | | | IV-1 | Spg20 | 23111 | 23-May-15 |
| 20977 | 3 | 4 | | | | IV-1 | Smyd1 | 150792 | 4-May-15 | 21072 | 3 | 4 | | | IV-1 | Spg7 | 6687 | 23-May-15 |
| 20978 | 3 | 4 | | | | IV-1 | Smyd4 | 114826 | 4-May-15 | 21073 | 3 | 4 | | | IV-1 | Sphkap | 80309 | 12-May-15 |
| 20979 | 3 | 4 | | | | IV-1 | Snap29 | 9342 | 28-May-15 | 21074 | 3 | 4 | | | IV-1 | Spidr | 23514 | 12-May-15 |
| 20980 | 3 | 4 | | | | IV-1 | Snapc2 | 6618 | 4-May-15 | 21075 | 3 | 4 | | | IV-1 | Spns1 | 83985 | 4-May-15 |
| 20981 | 3 | 4 | | | | IV-1 | Snapc3 | 6619 | 4-May-15 | 21076 | 3 | 4 | | | IV-1 | Sppl3 | 121665 | 29-May-15 |
| 20982 | 3 | 4 | | | | IV-1 | Snapc4 | 6621 | 4-May-15 | 21077 | 3 | 4 | | | IV-1 | Spr | 6697 | 7-Jun-15 |
| 20983 | 3 | 4 | | | | IV-1 | Snapc5 | 10302 | 21-May-15 | 21078 | 3 | 4 | | | IV-1 | Spred1 | 161742 | 23-May-15 |
| 20984 | 3 | 4 | | | | IV-1 | Snapin | 23557 | 21-May-15 | 21079 | 3 | 4 | | | IV-1 | Sprr2e | 6704 | 4-May-15 |
| 20985 | 3 | 4 | | | | IV-1 | Snrnp35 | 11066 | 4-May-15 | 21080 | 3 | 4 | | | IV-1 | Sprr2h | | |
| 20986 | 3 | 4 | | | | IV-1 | Snrnp40 | 9410 | 4-May-15 | 21081 | 3 | 4 | | | IV-1 | Sprr2i | | |
| 20987 | 3 | 4 | | | | IV-1 | Snrnp70 | 6625 | 12-May-15 | 21082 | 3 | 4 | | | IV-1 | Sprr2j-ps | | |
| 20988 | 3 | 4 | | | | IV-1 | Snrpa | 6626 | 12-May-15 | 21083 | 3 | 4 | | | IV-1 | Sprr2k | | |
| 20989 | 3 | 4 | | | | IV-1 | Snrpa1 | 6627 | 2-Jun-15 | 21084 | 3 | 4 | | | IV-1 | Sprtn2 | 6712 | 23-May-15 |
| 20990 | 3 | 4 | | | | IV-1 | Snrpb | 6628 | 28-May-15 | 21085 | 3 | 4 | | | IV-1 | Sptbc1 | 10558 | 23-May-15 |
| 20991 | 3 | 4 | | | | IV-1 | Snrpb2 | 6629 | 4-May-15 | 21086 | 3 | 4 | | | IV-1 | Sptlc2 | 9517 | 4-May-15 |
| 20992 | 3 | 4 | | | | IV-1 | Snrpd1 | 6632 | 7-Jun-15 | 21087 | 3 | 4 | | | IV-1 | Sptssa | 171546 | 4-May-15 |
| 20993 | 3 | 4 | | | | IV-1 | Sntb1 | 6641 | 4-May-15 | | | | | | | | | |

Fig. 30 - 112

| | | | | | | | | | | | | | | |
|---|---|---|---|---|---|---|---|---|---|---|---|---|---|---|
| 21088 | 3 | 4 | | | | IV-1 | Sptssb | 165679 | 4-May-15 | 21184 | 3 | 4 | | | | IV-1 | Strn4 | 29888 | 12-May-15 |
| 21089 | 3 | 4 | | | | IV-1 | Sra1 | 10011 | 7-Jun-15 | 21185 | 3 | 4 | | | | IV-1 | Stt3a | 3703 | 4-May-15 |
| 21090 | 3 | 4 | | | | IV-1 | Srbd1 | 55133 | 4-May-15 | 21186 | 3 | 4 | | | | IV-1 | Stx16 | 8675 | 4-May-15 |
| 21091 | 3 | 4 | | | | IV-1 | Srcrb4d | 136853 | 12-May-15 | 21187 | 3 | 4 | | | | IV-1 | Stx17 | 55014 | 21-May-15 |
| 21092 | 3 | 4 | | | | IV-1 | Srebf1 | 6720 | 24-May-15 | 21188 | 3 | 4 | | | | IV-1 | Stx18 | 53407 | 4-May-15 |
| 21093 | 3 | 4 | | | | IV-1 | Srek1ip1 | 285672 | 12-May-15 | 21189 | 3 | 4 | | | | IV-1 | Stx19 | 415117 | 4-May-15 |
| 21094 | 3 | 4 | | | | IV-1 | Srf | 6722 | 4-May-15 | 21190 | 3 | 4 | | | | IV-1 | Stx1a | 6804 | 4-May-15 |
| 21095 | 3 | 4 | | | | IV-1 | Srgap3 | 9901 | 7-Jun-15 | 21191 | 3 | 4 | | | | IV-1 | Stx4a | 6810 | 4-May-15 |
| 21096 | 3 | 4 | | | | IV-1 | Srl | 6345 | 4-May-15 | 21192 | 3 | 4 | | | | IV-1 | Stx5a | 6811 | 4-May-15 |
| 21097 | 3 | 4 | | | | IV-1 | Srp19 | 6728 | 4-May-15 | 21193 | 3 | 4 | | | | IV-1 | Stx6 | 10228 | 12-May-15 |
| 21098 | 3 | 4 | | | | IV-1 | Srp54a | | | 21194 | 3 | 4 | | | | IV-1 | Stx7 | 8417 | 4-May-15 |
| 21099 | 3 | 4 | | | | IV-1 | Srp54b | | | 21195 | 3 | 4 | | | | IV-1 | Stx8 | 9482 | 10-May-15 |
| 21100 | 3 | 4 | | | | IV-1 | Srp54c | | | 21196 | 3 | 4 | | | | IV-1 | Stxbp1 | 6812 | 26-May-15 |
| 21101 | 3 | 4 | | | | IV-1 | Srp68 | 6730 | 4-May-15 | 21197 | 3 | 4 | | | | IV-1 | Stxbp3b | | |
| 21102 | 3 | 4 | | | | IV-1 | Srp72 | 6731 | 12-May-15 | 21198 | 3 | 4 | | | | IV-1 | Stxbp4 | 252983 | 4-May-15 |
| 21103 | 3 | 4 | | | | IV-1 | Srp9 | 6726 | 12-May-15 | 21199 | 3 | 4 | | | | IV-1 | Stxbp5l | 9515 | 12-May-15 |
| 21104 | 3 | 4 | | | | IV-1 | Srpk2 | 6733 | 4-May-15 | 21200 | 3 | 4 | | | | IV-1 | Stxbp6 | 29091 | 12-May-15 |
| 21105 | 3 | 4 | | | | IV-1 | Srprb | 58477 | 21-May-15 | 21201 | 3 | 4 | | | | IV-1 | Styx | 6815 | 4-May-15 |
| 21106 | 3 | 4 | | | | IV-1 | Srrd | 402055 | 4-May-15 | 21202 | 3 | 4 | | | | IV-1 | Styxl1 | 51657 | 12-May-15 |
| 21107 | 3 | 4 | | | | IV-1 | Srrm1 | 10250 | 4-May-15 | 21203 | 3 | 4 | | | | IV-1 | Sub1 | 10923 | 28-May-15 |
| 21108 | 3 | 4 | | | | IV-1 | Srrm2 | 23524 | 3-Jun-15 | 21204 | 3 | 4 | | | | IV-1 | Sucla2 | 8803 | 23-May-15 |
| 21109 | 3 | 4 | | | | IV-1 | Srrm3 | 222183 | 4-May-15 | 21205 | 3 | 4 | | | | IV-1 | Sufu | 51684 | 23-May-15 |
| 21110 | 3 | 4 | | | | IV-1 | Srrt | 51593 | 4-May-15 | 21206 | 3 | 4 | | | | IV-1 | Sugp2 | 10147 | 4-May-15 |
| 21111 | 3 | 4 | | | | IV-1 | Srsf1 | 6426 | 4-May-15 | 21207 | 3 | 4 | | | | IV-1 | Sugt1 | 10910 | 28-May-15 |
| 21112 | 3 | 4 | | | | IV-1 | Srsf10 | 10772 | 1-Jun-15 | 21208 | 3 | 4 | | | | IV-1 | Sult1c1 | 6819 | 7-Jun-15 |
| 21113 | 3 | 4 | | | | IV-1 | Srsf12 | 135295 | 4-May-15 | 21209 | 3 | 4 | | | | IV-1 | Sult2a2 | | |
| 21114 | 3 | 4 | | | | IV-1 | Srsf2 | 6427 | 31-May-15 | 21210 | 3 | 4 | | | | IV-1 | Sult2a3 | | |
| 21115 | 3 | 4 | | | | IV-1 | Srsf3 | 6428 | 21-May-15 | 21211 | 3 | 4 | | | | IV-1 | Sult2a5 | | |
| 21116 | 3 | 4 | | | | IV-1 | Srsf5 | 6430 | 1-Jun-15 | 21212 | 3 | 4 | | | | IV-1 | Sult2a6 | | |
| 21117 | 3 | 4 | | | | IV-1 | Srsf6 | 6431 | 21-May-15 | 21213 | 3 | 4 | | | | IV-1 | Sult2a7 | | |
| 21118 | 3 | 4 | | | | IV-1 | Srsf7 | 6432 | 1-Jun-15 | 21214 | 3 | 4 | | | | IV-1 | Sumf1 | 285362 | 4-May-15 |
| 21119 | 3 | 4 | | | | IV-1 | Srxn1 | 140809 | 4-May-15 | 21215 | 3 | 4 | | | | IV-1 | Sumf2 | 25870 | 4-May-15 |
| 21120 | 3 | 4 | | | | IV-1 | Ss18 | 6760 | 12-May-15 | 21216 | 3 | 4 | | | | IV-1 | Sumo1 | 7341 | 17-May-15 |
| 21121 | 3 | 4 | | | | IV-1 | Ssbp1 | 6742 | 14-May-15 | 21217 | 3 | 4 | | | | IV-1 | Sumo3 | 6612 | 7-Jun-15 |
| 21122 | 3 | 4 | | | | IV-1 | Ssbp2 | 23635 | 12-May-15 | 21218 | 3 | 4 | | | | IV-1 | Sun1 | 23353 | 4-May-15 |
| 21123 | 3 | 4 | | | | IV-1 | Ssh1 | 54434 | 24-May-15 | 21219 | 3 | 4 | | | | IV-1 | Sun2 | 25777 | 17-May-15 |
| 21124 | 3 | 4 | | | | IV-1 | Ssh3 | 54961 | 12-May-15 | 21220 | 3 | 4 | | | | IV-1 | Sun3 | 256979 | 4-May-15 |
| 21125 | 3 | 4 | | | | IV-1 | Ssna1 | 8636 | 4-May-15 | 21221 | 3 | 4 | | | | IV-1 | Sun5 | 140732 | 4-May-15 |
| 21126 | 3 | 4 | | | | IV-1 | Sspn | 8082 | 14-May-15 | 21222 | 3 | 4 | | | | IV-1 | Supt20 | | |
| 21127 | 3 | 4 | | | | IV-1 | Ssr1 | 6745 | 12-May-15 | 21223 | 3 | 4 | | | | IV-1 | Supt3 | | |
| 21128 | 3 | 4 | | | | IV-1 | Ssr3 | 6747 | 21-May-15 | 21224 | 3 | 4 | | | | IV-1 | Supt4a | | |
| 21129 | 3 | 4 | | | | IV-1 | Ssr4 | 6748 | 23-May-15 | 21225 | 3 | 4 | | | | IV-1 | Supt5 | | |
| 21130 | 3 | 4 | | | | IV-1 | Sssca1 | 10534 | 12-May-15 | 21226 | 3 | 4 | | | | IV-1 | Supt6 | | |
| 21131 | 3 | 4 | | | | IV-1 | Sst | 6750 | 17-May-15 | 21227 | 3 | 4 | | | | IV-1 | Supt7l | 9913 | 4-May-15 |
| 21132 | 3 | 4 | | | | IV-1 | Sstr2 | 6752 | 24-May-15 | 21228 | 3 | 4 | | | | IV-1 | Supv3l1 | 6832 | 4-May-15 |
| 21133 | 3 | 4 | | | | IV-1 | Ssty1 | | | 21229 | 3 | 4 | | | | IV-1 | Surf2 | 6835 | 4-May-15 |
| 21134 | 3 | 4 | | | | IV-1 | Ssty2 | | | 21230 | 3 | 4 | | | | IV-1 | Surf4 | 6836 | 4-May-15 |
| 21135 | 3 | 4 | | | | IV-1 | Ssu2 | 51066 | 21-May-15 | 21231 | 3 | 4 | | | | IV-1 | Surf6 | 6838 | 31-May-15 |
| 21136 | 3 | 4 | | | | IV-1 | Ssx2ip | 117178 | 4-May-15 | 21232 | 3 | 4 | | | | IV-1 | Suv420h2 | 84787 | 4-May-15 |
| 21137 | 3 | 4 | | | | IV-1 | Ssxb10 | | | 21233 | 3 | 4 | | | | IV-1 | Sv2c | 22987 | 4-May-15 |
| 21138 | 3 | 4 | | | | IV-1 | Ssxb2 | | | 21234 | 3 | 4 | | | | IV-1 | Sval2 | | |
| 21139 | 3 | 4 | | | | IV-1 | Ssxb3 | | | 21235 | 3 | 4 | | | | IV-1 | Sval3 | | |
| 21140 | 3 | 4 | | | | IV-1 | Ssxb5 | | | 21236 | 3 | 4 | | | | IV-1 | Syap1 | 94056 | 4-May-15 |
| 21141 | 3 | 4 | | | | IV-1 | Ssxb6 | | | 21237 | 3 | 4 | | | | IV-1 | Svcp1-ps1 | | |
| 21142 | 3 | 4 | | | | IV-1 | Ssxb8 | | | 21238 | 3 | 4 | | | | IV-1 | Sycp2 | 10388 | 4-May-15 |
| 21143 | 3 | 4 | | | | IV-1 | Ssxb9 | | | 21239 | 3 | 4 | | | | IV-1 | Sycp3 | 50511 | 4-May-15 |
| 21144 | 3 | 4 | | | | IV-1 | St13 | 6767 | 4-May-15 | 21240 | 3 | 4 | | | | IV-1 | Syn1 | 6853 | 7-Jun-15 |
| 21145 | 3 | 4 | | | | IV-1 | St3gal1 | 6482 | 12-May-15 | 21241 | 3 | 4 | | | | IV-1 | Syn2 | 6854 | 4-May-15 |
| 21146 | 3 | 4 | | | | IV-1 | St8sia3os | | | 21242 | 3 | 4 | | | | IV-1 | Synb | | |
| 21147 | 3 | 4 | | | | IV-1 | St8sia4 | 7903 | 4-May-15 | 21243 | 3 | 4 | | | | IV-1 | Sync | 81493 | 4-May-15 |
| 21148 | 3 | 4 | | | | IV-1 | Stac | 6769 | 12-May-15 | 21244 | 3 | 4 | | | | IV-1 | Syncrip | 10492 | 1-Jun-15 |
| 21149 | 3 | 4 | | | | IV-1 | Stag1 | 10274 | 16-Jun-15 | 21245 | 3 | 4 | | | | IV-1 | Syndig1 | 79953 | 4-May-15 |
| 21150 | 3 | 4 | | | | IV-1 | Stag2 | 10735 | 21-May-15 | 21246 | 3 | 4 | | | | IV-1 | Syngr3 | 9143 | 4-May-15 |
| 21151 | 3 | 4 | | | | IV-1 | Stag3 | 10734 | 4-May-15 | 21247 | 3 | 4 | | | | IV-1 | Syngr4 | 23546 | 4-May-15 |
| 21152 | 3 | 4 | | | | IV-1 | Stam2 | 10254 | 4-May-15 | 21248 | 3 | 4 | | | | IV-1 | Synj1 | 8867 | 12-May-15 |
| 21153 | 3 | 4 | | | | IV-1 | Stambp | 10617 | 23-May-15 | 21249 | 3 | 4 | | | | IV-1 | Synj2 | 8871 | 4-May-15 |
| 21154 | 3 | 4 | | | | IV-1 | Stard6 | 147323 | 4-May-15 | 21250 | 3 | 4 | | | | IV-1 | Synm | 23336 | 4-May-15 |
| 21155 | 3 | 4 | | | | IV-1 | Stard7 | 56910 | 4-May-15 | 21251 | 3 | 4 | | | | IV-1 | Syp | 6855 | 4-May-15 |
| 21156 | 3 | 4 | | | | IV-1 | Stau1 | 6780 | 4-May-15 | 21252 | 3 | 4 | | | | IV-1 | Sypl2 | 284612 | 4-May-15 |
| 21157 | 3 | 4 | | | | IV-1 | Stau2 | 27067 | 4-May-15 | 21253 | 3 | 4 | | | | IV-1 | Syt1 | 6857 | 12-May-15 |
| 21158 | 3 | 4 | | | | IV-1 | Stim2 | 57620 | 10-May-15 | 21254 | 3 | 4 | | | | IV-1 | Syt17 | 51760 | 12-May-15 |
| 21159 | 3 | 4 | | | | IV-1 | Stip1 | 10963 | 7-Jun-15 | 21255 | 3 | 4 | | | | IV-1 | Syt5 | 6861 | 4-May-15 |
| 21160 | 3 | 4 | | | | IV-1 | Stk11ip | 114790 | 1-Jun-15 | 21256 | 3 | 4 | | | | IV-1 | Syt9 | 143425 | 4-May-15 |
| 21161 | 3 | 4 | | | | IV-1 | Stk16 | 8576 | 28-May-15 | 21257 | 3 | 4 | | | | IV-1 | Syvn1 | 84447 | 29-May-15 |
| 21162 | 3 | 4 | | | | IV-1 | Stk17b | 9262 | 4-May-15 | 21258 | 3 | 4 | | | | IV-1 | Szt2 | 23334 | 12-May-15 |
| 21163 | 3 | 4 | | | | IV-1 | Stk24 | 8428 | 12-May-15 | 21259 | 3 | 4 | | | | IV-1 | T | 6862 | 4-May-15 |
| 21164 | 3 | 4 | | | | IV-1 | Stk25 | 10494 | 4-May-15 | 21260 | 3 | 4 | | | | IV-1 | T2 | | |
| 21165 | 3 | 4 | | | | IV-1 | Stk3 | 6788 | 7-Jun-15 | 21261 | 3 | 4 | | | | IV-1 | Taar2 | 9287 | 7-Jun-15 |
| 21166 | 3 | 4 | | | | IV-1 | Stk32a | 202374 | 28-May-15 | 21262 | 3 | 4 | | | | IV-1 | Taar3 | 9288 | 4-May-15 |
| 21167 | 3 | 4 | | | | IV-1 | Stk32b | 55351 | 14-May-15 | 21263 | 3 | 4 | | | | IV-1 | Taar4 | | |
| 21168 | 3 | 4 | | | | IV-1 | Stk32c | 282974 | 4-May-15 | 21264 | 3 | 4 | | | | IV-1 | Taar5 | 9038 | 4-May-15 |
| 21169 | 3 | 4 | | | | IV-1 | Stk38 | 23012 | 4-May-15 | 21265 | 3 | 4 | | | | IV-1 | Taar7a | | |
| 21170 | 3 | 4 | | | | IV-1 | Stk40 | 83931 | 4-May-15 | 21266 | 3 | 4 | | | | IV-1 | Tacc2 | 10579 | 12-May-15 |
| 21171 | 3 | 4 | | | | IV-1 | Stmn4 | 81551 | 4-May-15 | 21267 | 3 | 4 | | | | IV-1 | Tada2a | 6871 | 1-Jun-15 |
| 21172 | 3 | 4 | | | | IV-1 | Stoml2 | 30968 | 4-May-15 | 21268 | 3 | 4 | | | | IV-1 | Tada2b | 93624 | 4-May-15 |
| 21173 | 3 | 4 | | | | IV-1 | Stoml3 | 161003 | 4-May-15 | 21269 | 3 | 4 | | | | IV-1 | Tada3 | 10474 | 4-May-15 |
| 21174 | 3 | 4 | | | | IV-1 | Stox2 | 56977 | 4-May-15 | 21270 | 3 | 4 | | | | IV-1 | Taf1 | 6872 | 23-May-15 |
| 21175 | 3 | 4 | | | | IV-1 | Stpg1 | 90529 | 4-May-15 | 21271 | 3 | 4 | | | | IV-1 | Taf10 | 6881 | 4-May-15 |
| 21176 | 3 | 4 | | | | IV-1 | Stpg2 | 285555 | 12-May-15 | 21272 | 3 | 4 | | | | IV-1 | Taf11 | 6882 | 4-May-15 |
| 21177 | 3 | 4 | | | | IV-1 | Stra13 | 201254 | 7-Jun-15 | 21273 | 3 | 4 | | | | IV-1 | Taf12 | 6883 | 4-May-15 |
| 21178 | 3 | 4 | | | | IV-1 | Stra6 | 64220 | 4-May-15 | 21274 | 3 | 4 | | | | IV-1 | Taf13 | 6884 | 4-May-15 |
| 21179 | 3 | 4 | | | | IV-1 | Strada | 92335 | 4-May-15 | 21275 | 3 | 4 | | | | IV-1 | Taf15 | 8148 | 4-May-15 |
| 21180 | 3 | 4 | | | | IV-1 | Strbp | 55342 | 4-May-15 | 21276 | 3 | 4 | | | | IV-1 | Taf1a | 9015 | 4-May-15 |
| 21181 | 3 | 4 | | | | IV-1 | Strip1 | 85369 | 4-May-15 | 21277 | 3 | 4 | | | | IV-1 | Taf1b | 9014 | 4-May-15 |
| 21182 | 3 | 4 | | | | IV-1 | Strip2 | 57464 | 4-May-15 | 21278 | 3 | 4 | | | | IV-1 | Taf1c | 9013 | 4-May-15 |
| 21183 | 3 | 4 | | | | IV-1 | Strn3 | 29966 | 4-May-15 | 21279 | 3 | 4 | | | | IV-1 | Taf1d | 79101 | 12-May-15 |

Fig. 30 - 113

| | | | | | | | | | | | | | | | |
|---|---|---|---|---|---|---|---|---|---|---|---|---|---|---|---|
| 21280 | 3 | 4 | | | | IV-1 | Taf3 | 83860 | 4-May-15 | 21376 | 3 | 4 | | IV-1 | Terf2ip | 54386 | 4-May-15 |
| 21281 | 3 | 4 | | | | IV-1 | Taf4a | 6874 | 12-May-15 | 21377 | 3 | 4 | | IV-1 | Tesk2 | 10420 | 4-May-15 |
| 21282 | 3 | 4 | | | | IV-1 | Taf4b | 6875 | 16-Jun-15 | 21378 | 3 | 4 | | IV-1 | Tet3 | 200424 | 10-May-15 |
| 21283 | 3 | 4 | | | | IV-1 | Taf5 | 6877 | 12-May-15 | 21379 | 3 | 4 | | IV-1 | Tex10 | 54881 | 4-May-15 |
| 21284 | 3 | 4 | | | | IV-1 | Taf5l | 27097 | 4-May-15 | 21380 | 3 | 4 | | IV-1 | Tex101 | 83639 | 4-May-15 |
| 21285 | 3 | 4 | | | | IV-1 | Taf6 | 6878 | 12-May-15 | 21381 | 3 | 4 | | IV-1 | Tex11 | 56159 | 4-May-15 |
| 21286 | 3 | 4 | | | | IV-1 | Taf6l | 10629 | 4-May-15 | 21382 | 3 | 4 | | IV-1 | Tex13 | | |
| 21287 | 3 | 4 | | | | IV-1 | Taf8 | 129685 | 4-May-15 | 21383 | 3 | 4 | | IV-1 | Tex13a | 56157 | 21-May-15 |
| 21288 | 3 | 4 | | | | IV-1 | Taf9 | 6880 | 4-May-15 | 21384 | 3 | 4 | | IV-1 | Tex14 | 56155 | 4-May-15 |
| 21289 | 3 | 4 | | | | IV-1 | Tagap | 117289 | 4-May-15 | 21385 | 3 | 4 | | IV-1 | Tex19.1 | | |
| 21290 | 3 | 4 | | | | IV-1 | Taldo1 | 6888 | 12-May-15 | 21386 | 3 | 4 | | IV-1 | Tex19.2 | | |
| 21291 | 3 | 4 | | | | IV-1 | Tamm41 | 132001 | 4-May-15 | 21387 | 3 | 4 | | IV-1 | Tex2 | 55852 | 4-May-15 |
| 21292 | 3 | 4 | | | | IV-1 | Tanc1 | 85461 | 4-May-15 | 21388 | 3 | 4 | | IV-1 | Tex21 | | |
| 21293 | 3 | 4 | | | | IV-1 | Tanc2 | 26115 | 4-May-15 | 21389 | 3 | 4 | | IV-1 | Tex22 | 647310 | 4-May-15 |
| 21294 | 3 | 4 | | | | IV-1 | Taok1 | 57551 | 4-May-15 | 21390 | 3 | 4 | | IV-1 | Tex24 | | |
| 21295 | 3 | 4 | | | | IV-1 | Taok2 | 9344 | 4-May-15 | 21391 | 3 | 4 | | IV-1 | Tex26 | 122046 | 4-May-15 |
| 21296 | 3 | 4 | | | | IV-1 | Taok3 | 51347 | 12-May-15 | 21392 | 3 | 4 | | IV-1 | Tex261 | 113419 | 4-May-15 |
| 21297 | 3 | 4 | | | | IV-1 | Tapbpl | 55080 | 4-May-15 | 21393 | 3 | 4 | | IV-1 | Tex28 | 1527 | 4-May-15 |
| 21298 | 3 | 4 | | | | IV-1 | Tardbp | 23435 | 31-May-15 | 21394 | 3 | 4 | | IV-1 | Tex29 | 121793 | 4-May-15 |
| 21299 | 3 | 4 | | | | IV-1 | Tas1r2 | 80834 | 7-Jun-15 | 21395 | 3 | 4 | | IV-1 | Tex35 | 84066 | 4-May-15 |
| 21300 | 3 | 4 | | | | IV-1 | Tas1r3 | 83756 | 4-May-15 | 21396 | 3 | 4 | | IV-1 | Tex36 | 387718 | 4-May-15 |
| 21301 | 3 | 4 | | | | IV-1 | Tas2r102 | | | 21397 | 3 | 4 | | IV-1 | Tex37 | 200523 | 20-May-15 |
| 21302 | 3 | 4 | | | | IV-1 | Tas2r103 | | | 21398 | 3 | 4 | | IV-1 | Tex38 | 374973 | 28-May-15 |
| 21303 | 3 | 4 | | | | IV-1 | Tas2r104 | | | 21399 | 3 | 4 | | IV-1 | Tex9 | 374618 | 4-May-15 |
| 21304 | 3 | 4 | | | | IV-1 | Tas2r105 | | | 21400 | 3 | 4 | | IV-1 | Tfap2d | 83741 | 4-May-15 |
| 21305 | 3 | 4 | | | | IV-1 | Tas2r106 | | | 21401 | 3 | 4 | | IV-1 | Tfap2e | 339488 | 28-May-15 |
| 21306 | 3 | 4 | | | | IV-1 | Tas2r108 | | | 21402 | 3 | 4 | | IV-1 | Tfap4 | 7023 | 28-May-15 |
| 21307 | 3 | 4 | | | | IV-1 | Taz | 6901 | 7-Jun-15 | 21403 | 3 | 4 | | IV-1 | Tfeb | 7942 | 28-May-15 |
| 21308 | 3 | 4 | | | | IV-1 | Tbata | 219793 | 12-May-15 | 21404 | 3 | 4 | | IV-1 | Tfip11 | 24144 | 4-May-15 |
| 21309 | 3 | 4 | | | | IV-1 | Tbc1d13 | 54662 | 4-May-15 | 21405 | 3 | 4 | | IV-1 | Tgds | 23483 | 4-May-15 |
| 21310 | 3 | 4 | | | | IV-1 | Tbc1d14 | 57533 | 21-May-15 | 21406 | 3 | 4 | | IV-1 | Tgfa | 7039 | 12-May-15 |
| 21311 | 3 | 4 | | | | IV-1 | Tbc1d15 | 64786 | 4-May-15 | 21407 | 3 | 4 | | IV-1 | Tgfbr3 | 7049 | 12-May-15 |
| 21312 | 3 | 4 | | | | IV-1 | Tbc1d19 | 55296 | 4-May-15 | 21408 | 3 | 4 | | IV-1 | Tgif2lx1 | | |
| 21313 | 3 | 4 | | | | IV-1 | Tbc1d2 | 55357 | 4-May-15 | 21409 | 3 | 4 | | IV-1 | Tgm5 | 9333 | 4-May-15 |
| 21314 | 3 | 4 | | | | IV-1 | Tbc1d21 | 161514 | 12-May-15 | 21410 | 3 | 4 | | IV-1 | Tgm6 | 343641 | 23-May-15 |
| 21315 | 3 | 4 | | | | IV-1 | Tbc1d22a | 25771 | 12-May-15 | 21411 | 3 | 4 | | IV-1 | Tgm7 | 116179 | 12-May-15 |
| 21316 | 3 | 4 | | | | IV-1 | Tbc1d22b | 55633 | 4-May-15 | 21412 | 3 | 4 | | IV-1 | Tgoln1 | | |
| 21317 | 3 | 4 | | | | IV-1 | Tbc1d24 | 57465 | 4-May-15 | 21413 | 3 | 4 | | IV-1 | Tha1 | | |
| 21318 | 3 | 4 | | | | IV-1 | Tbc1d2b | 23102 | 4-May-15 | 21414 | 3 | 4 | | IV-1 | Thap1 | 55145 | 17-May-15 |
| 21319 | 3 | 4 | | | | IV-1 | Tbc1d30 | 23329 | 4-May-15 | 21415 | 3 | 4 | | IV-1 | Thap11 | 57215 | 12-May-15 |
| 21320 | 3 | 4 | | | | IV-1 | Tbc1d7 | 51256 | 4-May-15 | 21416 | 3 | 4 | | IV-1 | Thap2 | 83591 | 4-May-15 |
| 21321 | 3 | 4 | | | | IV-1 | Tbca | 6902 | 12-May-15 | 21417 | 3 | 4 | | IV-1 | Thap4 | 51078 | 4-May-15 |
| 21322 | 3 | 4 | | | | IV-1 | Tbcb | 1155 | 10-May-15 | 21418 | 3 | 4 | | IV-1 | Thap6 | 152815 | 4-May-15 |
| 21323 | 3 | 4 | | | | IV-1 | Tbccd1 | 55171 | 4-May-15 | 21419 | 3 | 4 | | IV-1 | Them4 | 117145 | 4-May-15 |
| 21324 | 3 | 4 | | | | IV-1 | Tbce | 6905 | 4-May-15 | 21420 | 3 | 4 | | IV-1 | Thg1l | 54974 | 4-May-15 |
| 21325 | 3 | 4 | | | | IV-1 | Tbk1 | 29110 | 4-May-15 | 21421 | 3 | 4 | | IV-1 | Thnsl2 | 55258 | 4-May-15 |
| 21326 | 3 | 4 | | | | IV-1 | Tbl1x | 6907 | 4-May-15 | 21422 | 3 | 4 | | IV-1 | Thoc2 | 57187 | 4-May-15 |
| 21327 | 3 | 4 | | | | IV-1 | Tbl1xr1 | 79718 | 12-May-15 | 21423 | 3 | 4 | | IV-1 | Thoc3 | 84321 | 4-May-15 |
| 21328 | 3 | 4 | | | | IV-1 | Tbl2 | 26608 | 4-May-15 | 21424 | 3 | 4 | | IV-1 | Thoc5 | 8563 | 4-May-15 |
| 21329 | 3 | 4 | | | | IV-1 | Tbl3 | 10607 | 4-May-15 | 21425 | 3 | 4 | | IV-1 | Thop1 | 7064 | 12-May-15 |
| 21330 | 3 | 4 | | | | IV-1 | Tbp | 6908 | 31-May-15 | 21426 | 3 | 4 | | IV-1 | Thpo | 7066 | 12-May-15 |
| 21331 | 3 | 4 | | | | IV-1 | Tbpl1 | 9519 | 4-May-15 | 21427 | 3 | 4 | | IV-1 | Thrap3 | 9967 | 12-May-15 |
| 21332 | 3 | 4 | | | | IV-1 | Tbpl2 | 387332 | 7-Jun-15 | 21428 | 3 | 4 | | IV-1 | Thrb | 7068 | 14-May-15 |
| 21333 | 3 | 4 | | | | IV-1 | Tbr1 | 10716 | 12-May-15 | 21429 | 3 | 4 | | IV-1 | Thsd4 | 79875 | 4-May-15 |
| 21334 | 3 | 4 | | | | IV-1 | Tbrg1 | 84897 | 4-May-15 | 21430 | 3 | 4 | | IV-1 | Thsd7a | 221981 | 4-May-15 |
| 21335 | 3 | 4 | | | | IV-1 | Tbrg3 | | | 21431 | 3 | 4 | | IV-1 | Thtpa | 79178 | 4-May-15 |
| 21336 | 3 | 4 | | | | IV-1 | Tbrg4 | 9238 | 4-May-15 | 21432 | 3 | 4 | | IV-1 | Thumpd1 | 55623 | 4-May-15 |
| 21337 | 3 | 4 | | | | IV-1 | Tbx18 | 9096 | 4-May-15 | 21433 | 3 | 4 | | IV-1 | Thumpd2 | 80745 | 12-May-15 |
| 21338 | 3 | 4 | | | | IV-1 | Tbx19 | 9095 | 4-May-15 | 21434 | 3 | 4 | | IV-1 | Thumpd3 | 25917 | 12-May-15 |
| 21339 | 3 | 4 | | | | IV-1 | Tbx21 | 30009 | 4-May-15 | 21435 | 3 | 4 | | IV-1 | Ticam2 | 353376 | 4-May-15 |
| 21340 | 3 | 4 | | | | IV-1 | Tceal7 | 56849 | 4-May-15 | 21436 | 3 | 4 | | IV-1 | Tigd5 | 84948 | 4-May-15 |
| 21341 | 3 | 4 | | | | IV-1 | Tceal8 | 90843 | 4-May-15 | 21437 | 3 | 4 | | IV-1 | Timm10b | 26515 | 4-May-15 |
| 21342 | 3 | 4 | | | | IV-1 | Tceanc2 | 127428 | 4-May-15 | 21438 | 3 | 4 | | IV-1 | Timm13 | 26517 | 4-May-15 |
| 21343 | 3 | 4 | | | | IV-1 | Tceb1 | 6921 | 4-May-15 | 21439 | 3 | 4 | | IV-1 | Timm17a | 10440 | 4-May-15 |
| 21344 | 3 | 4 | | | | IV-1 | Tceb2 | 6923 | 2-Jun-15 | 21440 | 3 | 4 | | IV-1 | Timm17b | 10245 | 4-May-15 |
| 21345 | 3 | 4 | | | | IV-1 | Tceb3 | 6924 | 4-May-15 | 21441 | 3 | 4 | | IV-1 | Timm21 | 29090 | 4-May-15 |
| 21346 | 3 | 4 | | | | IV-1 | Tcerg1 | 10915 | 4-May-15 | 21442 | 3 | 4 | | IV-1 | Timm23 | 100287932 | 7-Jun-15 |
| 21347 | 3 | 4 | | | | IV-1 | Tcf21 | 6943 | 28-May-15 | 21443 | 3 | 4 | | IV-1 | Timm8a1 | | |
| 21348 | 3 | 4 | | | | IV-1 | Tcfl5 | 10732 | 24-May-15 | 21444 | 3 | 4 | | IV-1 | Timm8b | 26521 | 4-May-15 |
| 21349 | 3 | 4 | | | | IV-1 | Tc1b1 | | | 21445 | 3 | 4 | | IV-1 | Timm9 | 26520 | 12-May-15 |
| 21350 | 3 | 4 | | | | IV-1 | Tc1b2 | | | 21446 | 3 | 4 | | IV-1 | Timmdc1 | 51300 | 4-May-15 |
| 21351 | 3 | 4 | | | | IV-1 | Tc1b3 | | | 21447 | 3 | 4 | | IV-1 | Tirap | 114609 | 12-May-15 |
| 21352 | 3 | 4 | | | | IV-1 | Tc1b4 | | | 21448 | 3 | 4 | | IV-1 | Tjap1 | 93643 | 4-May-15 |
| 21353 | 3 | 4 | | | | IV-1 | Tc1b5 | | | 21449 | 3 | 4 | | IV-1 | Tjp1 | 7082 | 31-May-15 |
| 21354 | 3 | 4 | | | | IV-1 | Tcn2 | 6948 | 4-May-15 | 21450 | 3 | 4 | | IV-1 | Tkt | 7086 | 7-Jun-15 |
| 21355 | 3 | 4 | | | | IV-1 | Tcp10c | | | 21451 | 3 | 4 | | IV-1 | Tktl2 | 84076 | 4-May-15 |
| 21356 | 3 | 4 | | | | IV-1 | Tcp11 | 6954 | 4-May-15 | 21452 | 3 | 4 | | IV-1 | Tle1 | 7088 | 4-May-15 |
| 21357 | 3 | 4 | | | | IV-1 | Tcp11l1 | 55346 | 4-May-15 | 21453 | 3 | 4 | | IV-1 | Tlk2 | 11011 | 4-May-15 |
| 21358 | 3 | 4 | | | | IV-1 | Tcte3 | 6991 | 12-May-15 | 21454 | 3 | 4 | | IV-1 | Tll1 | 7092 | 4-May-15 |
| 21359 | 3 | 4 | | | | IV-1 | Tctn2 | 79867 | 23-May-15 | 21455 | 3 | 4 | | IV-1 | Tln1 | 7094 | 12-May-15 |
| 21360 | 3 | 4 | | | | IV-1 | Tctn3 | 26123 | 23-May-15 | 21456 | 3 | 4 | | IV-1 | Tlr4 | 7099 | 31-May-15 |
| 21361 | 3 | 4 | | | | IV-1 | Tdg | 6996 | 12-May-15 | 21457 | 3 | 4 | | IV-1 | Tm2d1 | 83941 | 4-May-15 |
| 21362 | 3 | 4 | | | | IV-1 | Tdh | 157739 | 7-Jun-15 | 21458 | 3 | 4 | | IV-1 | Tm2d2 | 83877 | 4-May-15 |
| 21363 | 3 | 4 | | | | IV-1 | Tdpoz2 | | | 21459 | 3 | 4 | | IV-1 | Tm2d3 | 80213 | 12-May-15 |
| 21364 | 3 | 4 | | | | IV-1 | Tdpoz4 | | | 21460 | 3 | 4 | | IV-1 | Tm4sf1 | 4071 | 4-May-15 |
| 21365 | 3 | 4 | | | | IV-1 | Tdpoz5 | | | 21461 | 3 | 4 | | IV-1 | Tm4sf4 | 7104 | 4-May-15 |
| 21366 | 3 | 4 | | | | IV-1 | Tdrd1 | 56165 | 4-May-15 | 21462 | 3 | 4 | | IV-1 | Tm9sf2 | 9375 | 4-May-15 |
| 21367 | 3 | 4 | | | | IV-1 | Tdrd12 | 91646 | 4-May-15 | 21463 | 3 | 4 | | IV-1 | Tm9sf3 | 56889 | 4-May-15 |
| 21368 | 3 | 4 | | | | IV-1 | Tdrkh | 11022 | 4-May-15 | 21464 | 3 | 4 | | IV-1 | Tm9sf4 | 9777 | 4-May-15 |
| 21369 | 3 | 4 | | | | IV-1 | Tecpr2 | 9895 | 4-May-15 | 21465 | 3 | 4 | | IV-1 | Tma16 | 55319 | 4-May-15 |
| 21370 | 3 | 4 | | | | IV-1 | Tectb | 6975 | 4-May-15 | 21466 | 3 | 4 | | IV-1 | Tmbim1 | 64114 | 4-May-15 |
| 21371 | 3 | 4 | | | | IV-1 | Telo2 | 9894 | 4-May-15 | 21467 | 3 | 4 | | IV-1 | Tmbim6 | 7009 | 31-May-15 |
| 21372 | 3 | 4 | | | | IV-1 | Tenm2 | 57451 | 12-May-15 | 21468 | 3 | 4 | | IV-1 | Tmbim7 | | |
| 21373 | 3 | 4 | | | | IV-1 | Tepp | 374739 | 4-May-15 | 21469 | 3 | 4 | | IV-1 | Tmc1 | 117531 | 23-May-15 |
| 21374 | 3 | 4 | | | | IV-1 | Terc | 7012 | 24-May-15 | 21470 | 3 | 4 | | IV-1 | Tmc2 | 117532 | 4-May-15 |
| 21375 | 3 | 4 | | | | IV-1 | Terf2 | 7014 | 4-May-15 | | | | | | | | |

Fig. 30 - 114

| | | | | | | | | | | | | | | | | |
|---|---|---|---|---|---|---|---|---|---|---|---|---|---|---|---|---|
| 21471 | 3 | 4 | | | | IV-1 | Tmc3 | 342125 | 4-May-15 | 21563 | 3 | 4 | | | IV-1 | Tmem60 | 85025 | 21-May-15 |
| 21472 | 3 | 4 | | | | IV-1 | Tmc4 | 147798 | 21-May-15 | 21564 | 3 | 4 | | | IV-1 | Tmem62 | 80023 | 4-May-15 |
| 21473 | 3 | 4 | | | | IV-1 | Tmco1 | 54499 | 4-May-15 | 21565 | 3 | 4 | | | IV-1 | Tmem63a | 9725 | 12-May-15 |
| 21474 | 3 | 4 | | | | IV-1 | Tmco2 | 127391 | 4-May-15 | 21566 | 3 | 4 | | | IV-1 | Tmem63b | 55362 | 4-May-15 |
| 21475 | 3 | 4 | | | | IV-1 | Tmco4 | 255104 | 4-May-15 | 21567 | 3 | 4 | | | IV-1 | Tmem63c | 57156 | 4-May-15 |
| 21476 | 3 | 4 | | | | IV-1 | Tmco5 | 145942 | 12-May-15 | 21568 | 3 | 4 | | | IV-1 | Tmem67 | 91147 | 23-May-15 |
| 21477 | 3 | 4 | | | | IV-1 | Tmco5b | 100652857 | 4-May-15 | 21569 | 3 | 4 | | | IV-1 | Tmem68 | 137695 | 4-May-15 |
| 21478 | 3 | 4 | | | | IV-1 | Tmco6 | 55374 | 4-May-15 | 21570 | 3 | 4 | | | IV-1 | Tmem69 | 51249 | 4-May-15 |
| 21479 | 3 | 4 | | | | IV-1 | Tmed1 | 11018 | 4-May-15 | 21571 | 3 | 4 | | | IV-1 | Tmem74b | 55321 | 12-May-15 |
| 21480 | 3 | 4 | | | | IV-1 | Tmed10 | 10972 | 12-May-15 | 21572 | 3 | 4 | | | IV-1 | Tmem81 | 388730 | 4-May-15 |
| 21481 | 3 | 4 | | | | IV-1 | Tmed3 | 23423 | 4-May-15 | 21573 | 3 | 4 | | | IV-1 | Tmem82 | 385595 | 4-May-15 |
| 21482 | 3 | 4 | | | | IV-1 | Tmed8 | 283578 | 12-May-15 | 21574 | 3 | 4 | | | IV-1 | Tmem88 | 92162 | 4-May-15 |
| 21483 | 3 | 4 | | | | IV-1 | Tmed9 | 54732 | 4-May-15 | 21575 | 3 | 4 | | | IV-1 | Tmem8b | 51754 | 4-May-15 |
| 21484 | 3 | 4 | | | | IV-1 | Tmeff1 | 8577 | 4-May-15 | 21576 | 3 | 4 | | | IV-1 | Tmem95 | 339168 | 4-May-15 |
| 21485 | 3 | 4 | | | | IV-1 | Tmem106c | 79022 | 4-May-15 | 21577 | 3 | 4 | | | IV-1 | Tmem97 | 27346 | 31-May-15 |
| 21486 | 3 | 4 | | | | IV-1 | Tmem107 | 84314 | 12-May-15 | 21578 | 3 | 4 | | | IV-1 | Tmevpg1 | 100885789 | 1-May-15 |
| 21487 | 3 | 4 | | | | IV-1 | Tmem11 | 8834 | 4-May-15 | 21579 | 3 | 4 | | | IV-1 | Tmf1 | 7110 | 4-May-15 |
| 21488 | 3 | 4 | | | | IV-1 | Tmem110 | 375346 | 4-May-15 | 21580 | 3 | 4 | | | IV-1 | Tmie | 259236 | 23-May-15 |
| 21489 | 3 | 4 | | | | IV-1 | Tmem115 | 11070 | 4-May-15 | 21581 | 3 | 4 | | | IV-1 | Tmod3 | 29766 | 4-May-15 |
| 21490 | 3 | 4 | | | | IV-1 | Tmem116 | 89894 | 4-May-15 | 21582 | 3 | 4 | | | IV-1 | Tmprss11c | | |
| 21491 | 3 | 4 | | | | IV-1 | Tmem123 | 114908 | 7-Jun-15 | 21583 | 3 | 4 | | | IV-1 | Tmprss11d | 9407 | 4-May-15 |
| 21492 | 3 | 4 | | | | IV-1 | Tmem126b | 55863 | 4-May-15 | 21584 | 3 | 4 | | | IV-1 | Tmprss11e | 28983 | 4-May-15 |
| 21493 | 3 | 4 | | | | IV-1 | Tmem127 | 55654 | 23-May-15 | 21585 | 3 | 4 | | | IV-1 | Tmprss11f | 389208 | 4-May-15 |
| 21494 | 3 | 4 | | | | IV-1 | Tmem128 | 85013 | 12-May-15 | 21586 | 3 | 4 | | | IV-1 | Tmprss11g | | |
| 21495 | 3 | 4 | | | | IV-1 | Tmem129 | 92305 | 23-May-15 | 21587 | 3 | 4 | | | IV-1 | Tmprss7 | 344805 | 12-May-15 |
| 21496 | 3 | 4 | | | | IV-1 | Tmem130 | 222865 | 4-May-15 | 21588 | 3 | 4 | | | IV-1 | Tmub2 | 79089 | 4-May-15 |
| 21497 | 3 | 4 | | | | IV-1 | Tmem131 | 23505 | 4-May-15 | 21589 | 3 | 4 | | | IV-1 | Tmx1 | 81542 | 4-May-15 |
| 21498 | 3 | 4 | | | | IV-1 | Tmem132a | 54972 | 4-May-15 | 21590 | 3 | 4 | | | IV-1 | Tmx2 | 51075 | 4-May-15 |
| 21499 | 3 | 4 | | | | IV-1 | Tmem132cos | | | 21591 | 3 | 4 | | | IV-1 | Tmx4 | 56255 | 4-May-15 |
| 21500 | 3 | 4 | | | | IV-1 | Tmem132d | 121256 | 4-May-15 | 21592 | 3 | 4 | | | IV-1 | Tnfrsf10b | 8795 | 17-May-15 |
| 21501 | 3 | 4 | | | | IV-1 | Tmem135 | 65084 | 15-May-15 | 21593 | 3 | 4 | | | IV-1 | Tnfrsf8 | 943 | 4-May-15 |
| 21502 | 3 | 4 | | | | IV-1 | Tmem147 | 10430 | 4-May-15 | 21594 | 3 | 4 | | | IV-1 | Tnfsf12Tnfsf13 | 407977 | 4-May-15 |
| 21503 | 3 | 4 | | | | IV-1 | Tmem150b | 284417 | 4-May-15 | 21595 | 3 | 4 | | | IV-1 | Tnfsf13 | 8741 | 17-May-15 |
| 21504 | 3 | 4 | | | | IV-1 | Tmem151a | 256472 | 4-May-15 | 21596 | 3 | 4 | | | IV-1 | Tnfsf4 | 7292 | 4-May-15 |
| 21505 | 3 | 4 | | | | IV-1 | Tmem161b | 153396 | 4-May-15 | 21597 | 3 | 4 | | | IV-1 | Tnip2 | 79155 | 4-May-15 |
| 21506 | 3 | 4 | | | | IV-1 | Tmem163 | 81615 | 4-May-15 | 21598 | 3 | 4 | | | IV-1 | Tnks1bp1 | 85456 | 4-May-15 |
| 21507 | 3 | 4 | | | | IV-1 | Tmem165 | 55858 | 23-May-15 | 21599 | 3 | 4 | | | IV-1 | Tnks2 | 80351 | 12-May-15 |
| 21508 | 3 | 4 | | | | IV-1 | Tmem167 | 153339 | 4-May-15 | 21600 | 3 | 4 | | | IV-1 | Tnmd | 64102 | 4-May-15 |
| 21509 | 3 | 4 | | | | IV-1 | Tmem168 | 64418 | 4-May-15 | 21601 | 3 | 4 | | | IV-1 | Tnpo2 | 30000 | 12-May-15 |
| 21510 | 3 | 4 | | | | IV-1 | Tmem169 | 92691 | 4-May-15 | 21602 | 3 | 4 | | | IV-1 | Tnpo3 | 23534 | 4-May-15 |
| 21511 | 3 | 4 | | | | IV-1 | Tmem170 | 124491 | 12-May-15 | 21603 | 3 | 4 | | | IV-1 | Tnr | 7143 | 4-May-15 |
| 21512 | 3 | 4 | | | | IV-1 | Tmem170b | 100113407 | 4-May-15 | 21604 | 3 | 4 | | | IV-1 | Tnrc18 | 84629 | 7-Jun-15 |
| 21513 | 3 | 4 | | | | IV-1 | Tmem171 | 134285 | 4-May-15 | 21605 | 3 | 4 | | | IV-1 | Tnrc6a | 27327 | 4-May-15 |
| 21514 | 3 | 4 | | | | IV-1 | Tmem175 | 84286 | 12-May-15 | 21606 | 3 | 4 | | | IV-1 | Tnrc6b | 23112 | 4-May-15 |
| 21515 | 3 | 4 | | | | IV-1 | Tmem178b | 100507421 | 4-May-15 | 21607 | 3 | 4 | | | IV-1 | Tnrc6c | 57690 | 12-May-15 |
| 21516 | 3 | 4 | | | | IV-1 | Tmem18 | 129787 | 4-May-15 | 21608 | 3 | 4 | | | IV-1 | Tns1 | 7145 | 12-May-15 |
| 21517 | 3 | 4 | | | | IV-1 | Tmem180 | 79847 | 21-May-15 | 21609 | 3 | 4 | | | IV-1 | Tollip | 54472 | 4-May-15 |
| 21518 | 3 | 4 | | | | IV-1 | Tmem184a | 202915 | 4-May-15 | 21610 | 3 | 4 | | | IV-1 | Tom1 | 10043 | 4-May-15 |
| 21519 | 3 | 4 | | | | IV-1 | Tmem185b | 79134 | 12-May-15 | 21611 | 3 | 4 | | | IV-1 | Tom1l1 | 10040 | 4-May-15 |
| 21520 | 3 | 4 | | | | IV-1 | Tmem186 | 25880 | 4-May-15 | 21612 | 3 | 4 | | | IV-1 | Tomm20 | 9804 | 12-May-15 |
| 21521 | 3 | 4 | | | | IV-1 | Tmem19 | 55266 | 4-May-15 | 21613 | 3 | 4 | | | IV-1 | Tomm20l | 387990 | 4-May-15 |
| 21522 | 3 | 4 | | | | IV-1 | Tmem191c | 645426 | 20-May-15 | 21614 | 3 | 4 | | | IV-1 | Tomm34 | 10953 | 4-May-15 |
| 21523 | 3 | 4 | | | | IV-1 | Tmem192 | 201931 | 4-May-15 | 21615 | 3 | 4 | | | IV-1 | Tomm40 | 10452 | 12-May-15 |
| 21524 | 3 | 4 | | | | IV-1 | Tmem194 | 23306 | 28-May-15 | 21616 | 3 | 4 | | | IV-1 | Tomm6os | | |
| 21525 | 3 | 4 | | | | IV-1 | Tmem198 | 130612 | 12-May-15 | 21617 | 3 | 4 | | | IV-1 | Tomm70a | 9868 | 24-May-15 |
| 21526 | 3 | 4 | | | | IV-1 | Tmem199 | 147007 | 4-May-15 | 21618 | 3 | 4 | | | IV-1 | Tomt | | |
| 21527 | 3 | 4 | | | | IV-1 | Tmem2 | 23670 | 4-May-15 | 21619 | 3 | 4 | | | IV-1 | Top1mt | 116447 | 14-May-15 |
| 21528 | 3 | 4 | | | | IV-1 | Tmem201 | 199953 | 4-May-15 | 21620 | 3 | 4 | | | IV-1 | Top3a | 7156 | 4-May-15 |
| 21529 | 3 | 4 | | | | IV-1 | Tmem207 | 131920 | 4-May-15 | 21621 | 3 | 4 | | | IV-1 | Top3b | 8940 | 4-May-15 |
| 21530 | 3 | 4 | | | | IV-1 | Tmem208 | 29100 | 4-May-15 | 21622 | 3 | 4 | | | IV-1 | Topaz1 | 375337 | 4-May-15 |
| 21531 | 3 | 4 | | | | IV-1 | Tmem209 | 84928 | 21-May-15 | 21623 | 3 | 4 | | | IV-1 | Topbp1 | 11073 | 4-May-15 |
| 21532 | 3 | 4 | | | | IV-1 | Tmem210 | 100505993 | 4-May-15 | 21624 | 3 | 4 | | | IV-1 | Toporsl | | |
| | | | | | | | | | | 21625 | 3 | 4 | | | IV-1 | Toporsos | | |
| 21533 | 3 | 4 | | | | IV-1 | Tmem211 | 255349 | 4-May-15 | 21626 | 3 | 4 | | | IV-1 | Tor1a | 1861 | 23-May-15 |
| 21534 | 3 | 4 | | | | IV-1 | Tmem215 | 401498 | 4-May-15 | 21627 | 3 | 4 | | | IV-1 | Tor1aip1 | 26092 | 4-May-15 |
| 21535 | 3 | 4 | | | | IV-1 | Tmem216 | 51259 | 23-May-15 | 21628 | 3 | 4 | | | IV-1 | Tor1aip2 | 163590 | 12-May-15 |
| 21536 | 3 | 4 | | | | IV-1 | Tmem220 | 388335 | 4-May-15 | 21629 | 3 | 4 | | | IV-1 | Tor1b | 27348 | 4-May-15 |
| 21537 | 3 | 4 | | | | IV-1 | Tmem223 | 79064 | 4-May-15 | 21630 | 3 | 4 | | | IV-1 | Tor2a | 27433 | 31-May-15 |
| 21538 | 3 | 4 | | | | IV-1 | Tmem225 | 338661 | 4-May-15 | 21631 | 3 | 4 | | | IV-1 | Tox | 9760 | 31-May-15 |
| 21539 | 3 | 4 | | | | IV-1 | Tmem229a | 730130 | 12-May-15 | 21632 | 3 | 4 | | | IV-1 | Tox2 | 84969 | 4-May-15 |
| 21540 | 3 | 4 | | | | IV-1 | Tmem229b | 161145 | 4-May-15 | 21633 | 3 | 4 | | | IV-1 | Tpbpb | | |
| 21541 | 3 | 4 | | | | IV-1 | Tmem231 | 79583 | 23-May-15 | 21634 | 3 | 4 | | | IV-1 | Tpcn1 | 53373 | 12-May-15 |
| 21542 | 3 | 4 | | | | IV-1 | Tmem235 | 283999 | 4-May-15 | 21635 | 3 | 4 | | | IV-1 | Tpgs1 | 93978 | 12-May-15 |
| 21543 | 3 | 4 | | | | IV-1 | Tmem236 | 653567 | 4-May-15 | 21636 | 3 | 4 | | | IV-1 | Tph1 | 7166 | 3-May-15 |
| 21544 | 3 | 4 | | | | IV-1 | Tmem237 | 65062 | 23-May-15 | 21637 | 3 | 4 | | | IV-1 | Tpi1 | 7167 | 4-May-15 |
| 21545 | 3 | 4 | | | | IV-1 | Tmem239 | 100288797 | 4-May-15 | 21638 | 3 | 4 | | | IV-1 | Tpk1 | 27010 | 4-May-15 |
| 21546 | 3 | 4 | | | | IV-1 | Tmem240 | 339453 | 23-May-15 | 21639 | 3 | 4 | | | IV-1 | Tpm1 | 7168 | 31-May-15 |
| 21547 | 3 | 4 | | | | IV-1 | Tmem241 | 85019 | 4-May-15 | 21640 | 3 | 4 | | | IV-1 | Tpp1 | 1200 | 7-Jun-15 |
| 21548 | 3 | 4 | | | | IV-1 | Tmem242 | 729515 | 4-May-15 | 21641 | 3 | 4 | | | IV-1 | Tpp2 | 7174 | 4-May-15 |
| 21549 | 3 | 4 | | | | IV-1 | Tmem248 | 55069 | 4-May-15 | 21642 | 3 | 4 | | | IV-1 | Tpp | 11076 | 4-May-15 |
| 21550 | 3 | 4 | | | | IV-1 | Tmem254a | | | 21643 | 3 | 4 | | | IV-1 | Tpra1 | 131601 | 4-May-15 |
| 21551 | 3 | 4 | | | | IV-1 | Tmem263 | 90488 | 4-May-15 | 21644 | 3 | 4 | | | IV-1 | Tprg | | |
| 21552 | 3 | 4 | | | | IV-1 | Tmem33 | 55161 | 1-Jun-15 | 21645 | 3 | 4 | | | IV-1 | Tprgl | | |
| 21553 | 3 | 4 | | | | IV-1 | Tmem39a | 55254 | 28-May-15 | 21646 | 3 | 4 | | | IV-1 | Tprkb | 51002 | 4-May-15 |
| 21554 | 3 | 4 | | | | IV-1 | Tmem42 | 131616 | 4-May-15 | 21647 | 3 | 4 | | | IV-1 | Tpst1 | 8460 | 21-May-15 |
| 21555 | 3 | 4 | | | | IV-1 | Tmem43 | 79188 | 23-May-15 | 21648 | 3 | 4 | | | IV-1 | Tpst2 | 8459 | 21-May-15 |
| 21556 | 3 | 4 | | | | IV-1 | Tmem50a | 23585 | 4-May-15 | 21649 | 3 | 4 | | | IV-1 | Tpt1 | 7178 | 4-May-15 |
| 21557 | 3 | 4 | | | | IV-1 | Tmem50b | 757 | 4-May-15 | 21650 | 3 | 4 | | | IV-1 | Tpte | 7179 | 12-May-15 |
| 21558 | 3 | 4 | | | | IV-1 | Tmem53 | 79639 | 4-May-15 | 21651 | 3 | 4 | | | IV-1 | Traf3 | 7187 | 29-May-15 |
| 21559 | 3 | 4 | | | | IV-1 | Tmem55a | 55529 | 4-May-15 | 21652 | 3 | 4 | | | IV-1 | Traf3ip1 | 26146 | 4-May-15 |
| 21560 | 3 | 4 | | | | IV-1 | Tmem55b | 90809 | 4-May-15 | 21653 | 3 | 4 | | | IV-1 | Traf3ip2 | 10758 | 13-May-15 |
| 21561 | 3 | 4 | | | | IV-1 | Tmem59 | 9528 | 4-May-15 | 21654 | 3 | 4 | | | IV-1 | Traf5 | 7188 | 4-May-15 |
| 21562 | 3 | 4 | | | | IV-1 | Tmem59l | 25789 | 4-May-15 | 21655 | 3 | 4 | | | IV-1 | Traf7 | 84231 | 4-May-15 |
| | | | | | | | | | | 21656 | 3 | 4 | | | IV-1 | Tram2 | 9697 | 21-May-15 |
| | | | | | | | | | | 21657 | 3 | 4 | | | IV-1 | Trap1a | | |

Fig. 30 - 115

| | | | | | | | | | | | | | | | | | |
|---|---|---|---|---|---|---|---|---|---|---|---|---|---|---|---|---|---|
| 21658 | 3 | 4 | | | | IV-1 | Trappc1 | 58485 | 4-May-15 | 21753 | 3 | 4 | | | | IV-1 | Tspyl3 | 128854 | 4-May-15 |
| 21659 | 3 | 4 | | | | IV-1 | Trappc10 | 7109 | 4-May-15 | 21754 | 3 | 4 | | | | IV-1 | Tspy-ps | | |
| 21660 | 3 | 4 | | | | IV-1 | Trappc11 | 60684 | 12-May-15 | 21755 | 3 | 4 | | | | IV-1 | Tsr1 | 55720 | 12-May-15 |
| 21661 | 3 | 4 | | | | IV-1 | Trappc12 | 51112 | 14-May-15 | 21756 | 3 | 4 | | | | IV-1 | Tsr3 | 115939 | 4-May-15 |
| 21662 | 3 | 4 | | | | IV-1 | Trappc13 | 80006 | 4-May-15 | 21757 | 3 | 4 | | | | IV-1 | Tssc1 | 7260 | 4-May-15 |
| 21663 | 3 | 4 | | | | IV-1 | Trappc2 | 6399 | 23-May-15 | 21758 | 3 | 4 | | | | IV-1 | Tssk1 | 83942 | 7-Jun-15 |
| 21664 | 3 | 4 | | | | IV-1 | Trappc2l | 51693 | 4-May-15 | 21759 | 3 | 4 | | | | IV-1 | Tssk2 | 23617 | 4-May-15 |
| 21665 | 3 | 4 | | | | IV-1 | Trappc3l | 100128327 | 7-Jun-15 | 21760 | 3 | 4 | | | | IV-1 | Tssk3 | 81629 | 4-May-15 |
| 21666 | 3 | 4 | | | | IV-1 | Trappc4 | 51399 | 4-May-15 | 21761 | 3 | 4 | | | | IV-1 | Tssk4 | 283629 | 7-Jun-15 |
| 21667 | 3 | 4 | | | | IV-1 | Trappc5 | 126003 | 4-May-15 | 21762 | 3 | 4 | | | | IV-1 | Ttbk1 | 84630 | 12-May-15 |
| 21668 | 3 | 4 | | | | IV-1 | Trappc6a | 79090 | 4-May-15 | 21763 | 3 | 4 | | | | IV-1 | Ttbk2 | 146057 | 31-May-15 |
| 21669 | 3 | 4 | | | | IV-1 | Trappc6b | 122553 | 4-May-15 | 21764 | 3 | 4 | | | | IV-1 | Ttc1 | 7265 | 4-May-15 |
| 21670 | 3 | 4 | | | | IV-1 | Trappc8 | 22878 | 21-May-15 | 21765 | 3 | 4 | | | | IV-1 | Ttc12 | 54970 | 12-May-15 |
| 21671 | 3 | 4 | | | | IV-1 | Trdmt1 | 1787 | 12-May-15 | 21766 | 3 | 4 | | | | IV-1 | Ttc14 | 151613 | 4-May-15 |
| 21672 | 3 | 4 | | | | IV-1 | Trdn | 10345 | 23-May-15 | 21767 | 3 | 4 | | | | IV-1 | Ttc16 | 158248 | 4-May-15 |
| 21673 | 3 | 4 | | | | IV-1 | Trhde | 29953 | 4-May-15 | 21768 | 3 | 4 | | | | IV-1 | Ttc17 | 55761 | 12-May-15 |
| 21674 | 3 | 4 | | | | IV-1 | Trhr2 | | | 21769 | 3 | 4 | | | | IV-1 | Ttc18 | 118491 | 4-May-15 |
| 21675 | 3 | 4 | | | | IV-1 | Triap1 | 51499 | 4-May-15 | 21770 | 3 | 4 | | | | IV-1 | Ttc24 | 164118 | 4-May-15 |
| 21676 | 3 | 4 | | | | IV-1 | Trib1 | 10221 | 4-May-15 | 21771 | 3 | 4 | | | | IV-1 | Ttc26 | 79989 | 12-May-15 |
| 21677 | 3 | 4 | | | | IV-1 | Trim12a | | | 21772 | 3 | 4 | | | | IV-1 | Ttc28 | 23331 | 12-May-15 |
| 21678 | 3 | 4 | | | | IV-1 | Trim12c | | | 21773 | 3 | 4 | | | | IV-1 | Ttc29 | 83894 | 4-May-15 |
| 21679 | 3 | 4 | | | | IV-1 | Trim23 | 373 | 2-Jun-15 | 21774 | 3 | 4 | | | | IV-1 | Ttc3 | 7267 | 12-May-15 |
| 21680 | 3 | 4 | | | | IV-1 | Trim24 | 8805 | 4-May-15 | 21775 | 3 | 4 | | | | IV-1 | Ttc30a1 | | |
| 21681 | 3 | 4 | | | | IV-1 | Trim27 | 5987 | 2-Jun-15 | 21776 | 3 | 4 | | | | IV-1 | Ttc38 | 55020 | 4-May-15 |
| 21682 | 3 | 4 | | | | IV-1 | Trim29 | 23650 | 12-May-15 | 21777 | 3 | 4 | | | | IV-1 | Ttc4 | 7268 | 4-May-15 |
| 21683 | 3 | 4 | | | | IV-1 | Trim31 | 11074 | 7-Jun-15 | 21778 | 3 | 4 | | | | IV-1 | Ttc5 | 91875 | 4-May-15 |
| 21684 | 3 | 4 | | | | IV-1 | Trim32 | 22954 | 23-May-15 | 21779 | 3 | 4 | | | | IV-1 | Ttc7 | 57217 | 12-May-15 |
| 21685 | 3 | 4 | | | | IV-1 | Trim34a | | | 21780 | 3 | 4 | | | | IV-1 | Ttc8 | 123016 | 23-May-15 |
| 21686 | 3 | 4 | | | | IV-1 | Trim40 | 135644 | 7-Jun-15 | 21781 | 3 | 4 | | | | IV-1 | Ttc9c | 283237 | 4-May-15 |
| 21687 | 3 | 4 | | | | IV-1 | Trim41 | 90933 | 4-May-15 | 21782 | 3 | 4 | | | | IV-1 | Ttf1 | 7270 | 7-Jun-15 |
| 21688 | 3 | 4 | | | | IV-1 | Trim42 | 287035 | 4-May-15 | 21783 | 3 | 4 | | | | IV-1 | Ttf2 | 8458 | 7-Jun-15 |
| 21689 | 3 | 4 | | | | IV-1 | Trim43a | 129868 | 4-May-15 | 21784 | 3 | 4 | | | | IV-1 | Ttll2 | 80185 | 4-May-15 |
| 21690 | 3 | 4 | | | | IV-1 | Trim43b | 653192 | 4-May-15 | 21785 | 3 | 4 | | | | IV-1 | Ttll2 | 83887 | 4-May-15 |
| 21691 | 3 | 4 | | | | IV-1 | Trim43c | | | 21786 | 3 | 4 | | | | IV-1 | Ttll7 | 79739 | 4-May-15 |
| 21692 | 3 | 4 | | | | IV-1 | Trim44 | 54765 | 4-May-15 | 21787 | 3 | 4 | | | | IV-1 | Ttll9 | 164395 | 4-May-15 |
| 21693 | 3 | 4 | | | | IV-1 | Trim46 | 80128 | 4-May-15 | 21788 | 3 | 4 | | | | IV-1 | Tuba3b | | |
| 21694 | 3 | 4 | | | | IV-1 | Trim61 | 391712 | 4-May-15 | 21789 | 3 | 4 | | | | IV-1 | Tube1 | 51175 | 4-May-15 |
| 21695 | 3 | 4 | | | | IV-1 | Trim62 | 55223 | 4-May-15 | 21790 | 3 | 4 | | | | IV-1 | Tubg2 | 27175 | 14-May-15 |
| 21696 | 3 | 4 | | | | IV-1 | Trim66 | 9866 | 4-May-15 | 21791 | 3 | 4 | | | | IV-1 | Tubgcp2 | 10844 | 4-May-15 |
| 21697 | 3 | 4 | | | | IV-1 | Trim67 | 440730 | 12-May-15 | 21792 | 3 | 4 | | | | IV-1 | Tubgcp3 | 10426 | 4-May-15 |
| 21698 | 3 | 4 | | | | IV-1 | Trim7 | 81786 | 4-May-15 | 21793 | 3 | 4 | | | | IV-1 | Tubgcp4 | 27229 | 30-May-15 |
| 21699 | 3 | 4 | | | | IV-1 | Trim8 | 81603 | 4-May-15 | 21794 | 3 | 4 | | | | IV-1 | Tubgcp5 | 114791 | 4-May-15 |
| 21700 | 3 | 4 | | | | IV-1 | Trim9 | 114088 | 4-May-15 | 21795 | 3 | 4 | | | | IV-1 | Tubgcp6 | 85378 | 4-May-15 |
| 21701 | 3 | 4 | | | | IV-1 | Triml1 | 339976 | 4-May-15 | 21796 | 3 | 4 | | | | IV-1 | Tufm | 7284 | 4-May-15 |
| 21702 | 3 | 4 | | | | IV-1 | Triml2 | 205860 | 7-Jun-15 | 21797 | 3 | 4 | | | | IV-1 | Tulp1 | 7287 | 31-May-15 |
| 21703 | 3 | 4 | | | | IV-1 | Trio | 7204 | 12-May-15 | 21798 | 3 | 4 | | | | IV-1 | Tulp2 | 7288 | 28-May-15 |
| 21704 | 3 | 4 | | | | IV-1 | Triobp | 11078 | 23-May-15 | 21799 | 3 | 4 | | | | IV-1 | Tulp3 | 7289 | 28-May-15 |
| 21705 | 3 | 4 | | | | IV-1 | Trip12 | 9320 | 23-May-15 | 21800 | 3 | 4 | | | | IV-1 | Tulp4 | 56995 | 28-May-15 |
| 21706 | 3 | 4 | | | | IV-1 | Trip6 | 7205 | 12-May-15 | 21801 | 3 | 4 | | | | IV-1 | Tunar | 100507043 | 16-May-15 |
| 21707 | 3 | 4 | | | | IV-1 | Triqk | 286144 | 4-May-15 | 21802 | 3 | 4 | | | | IV-1 | Tusc1 | 286319 | 4-May-15 |
| 21708 | 3 | 4 | | | | IV-1 | Trmt10a | 93587 | 4-May-15 | 21803 | 3 | 4 | | | | IV-1 | Tvp23a | 780776 | 4-May-15 |
| 21709 | 3 | 4 | | | | IV-1 | Trmt10c | 54931 | 4-May-15 | 21804 | 3 | 4 | | | | IV-1 | Twf1 | 5756 | 3-May-15 |
| 21710 | 3 | 4 | | | | IV-1 | Trmt11 | 60487 | 4-May-15 | 21805 | 3 | 4 | | | | IV-1 | Twf2 | 11344 | 3-May-15 |
| 21711 | 3 | 4 | | | | IV-1 | Trmt112 | 51504 | 4-May-15 | 21806 | 3 | 4 | | | | IV-1 | Twsg1 | 57045 | 4-May-15 |
| 21712 | 3 | 4 | | | | IV-1 | Trmt12 | 55039 | 4-May-15 | 21807 | 3 | 4 | | | | IV-1 | Txk | 7294 | 28-May-15 |
| 21713 | 3 | 4 | | | | IV-1 | Trmt13 | 54482 | 4-May-15 | 21808 | 3 | 4 | | | | IV-1 | Txlnb | 167838 | 12-May-15 |
| 21714 | 3 | 4 | | | | IV-1 | Trmt1l | 81627 | 4-May-15 | 21809 | 3 | 4 | | | | IV-1 | Txn1 | | |
| 21715 | 3 | 4 | | | | IV-1 | Trmt2a | 27037 | 4-May-15 | 21810 | 3 | 4 | | | | IV-1 | Txn2 | 25828 | 12-May-15 |
| 21716 | 3 | 4 | | | | IV-1 | Trmt2b | 79979 | 4-May-15 | 21811 | 3 | 4 | | | | IV-1 | Txndc12 | 51060 | 4-May-15 |
| 21717 | 3 | 4 | | | | IV-1 | Trmt44 | 152992 | 12-May-15 | 21812 | 3 | 4 | | | | IV-1 | Txndc15 | 79770 | 4-May-15 |
| 21718 | 3 | 4 | | | | IV-1 | Trmt5 | 57570 | 4-May-15 | 21813 | 3 | 4 | | | | IV-1 | Txndc16 | 57544 | 4-May-15 |
| 21719 | 3 | 4 | | | | IV-1 | Trnau1ap | 54952 | 4-May-15 | 21814 | 3 | 4 | | | | IV-1 | Txndc2 | 84203 | 12-May-15 |
| 21720 | 3 | 4 | | | | IV-1 | Trnp1 | 388610 | 4-May-15 | 21815 | 3 | 4 | | | | IV-1 | Txndc9 | 10190 | 4-May-15 |
| 21721 | 3 | 4 | | | | IV-1 | Tro | 7216 | 4-May-15 | 21816 | 3 | 4 | | | | IV-1 | Txnl4b | 54957 | 4-May-15 |
| 21722 | 3 | 4 | | | | IV-1 | Trp53 | 7157 | 31-May-15 | 21817 | 3 | 4 | | | | IV-1 | Tyro3 | 7301 | 4-May-15 |
| 21723 | 3 | 4 | | | | IV-1 | Trp53bp2 | | | 21818 | 3 | 4 | | | | IV-1 | Tysnd1 | 219743 | 21-May-15 |
| 21724 | 3 | 4 | | | | IV-1 | Trp53tg5 | | | 21819 | 3 | 4 | | | | IV-1 | Tyw1 | 55253 | 4-May-15 |
| 21725 | 3 | 4 | | | | IV-1 | Trpc1 | 7220 | 10-May-15 | 21820 | 3 | 4 | | | | IV-1 | Tyw3 | 127253 | 4-May-15 |
| 21726 | 3 | 4 | | | | IV-1 | Trpc3 | 7222 | 10-May-15 | 21821 | 3 | 4 | | | | IV-1 | U2af1 | 7307 | 2-Jun-15 |
| 21727 | 3 | 4 | | | | IV-1 | Trpc4 | 7223 | 12-May-15 | 21822 | 3 | 4 | | | | IV-1 | U2af2 | 11338 | 21-May-15 |
| 21728 | 3 | 4 | | | | IV-1 | Trpc5 | 7224 | 4-May-15 | 21823 | 3 | 4 | | | | IV-1 | U2surp | 23350 | 4-May-15 |
| 21729 | 3 | 4 | | | | IV-1 | Trpd52l3 | | | 21824 | 3 | 4 | | | | IV-1 | U90926 | | |
| 21730 | 3 | 4 | | | | IV-1 | Trpm1 | 4308 | 12-May-15 | 21825 | 3 | 4 | | | | IV-1 | Uba1y | | |
| 21731 | 3 | 4 | | | | IV-1 | Trpm2 | 7226 | 7-Jun-15 | 21826 | 3 | 4 | | | | IV-1 | Uba2 | 10054 | 23-May-15 |
| 21732 | 3 | 4 | | | | IV-1 | Trpm8 | 79054 | 24-May-15 | 21827 | 3 | 4 | | | | IV-1 | Uba3 | 9039 | 23-May-15 |
| 21733 | 3 | 4 | | | | IV-1 | Trps1 | 7227 | 4-May-15 | 21828 | 3 | 4 | | | | IV-1 | Uba5 | 79876 | 4-May-15 |
| 21734 | 3 | 4 | | | | IV-1 | Trpv1 | 7442 | 17-May-15 | 21829 | 3 | 4 | | | | IV-1 | Uba52 | 7311 | 1-Jun-15 |
| 21735 | 3 | 4 | | | | IV-1 | Trpv4 | 59341 | 23-May-15 | 21830 | 3 | 4 | | | | IV-1 | Uba6 | 55236 | 4-May-15 |
| 21736 | 3 | 4 | | | | IV-1 | Trub1 | 142940 | 12-May-15 | 21831 | 3 | 4 | | | | IV-1 | Uba7 | 7318 | 4-May-15 |
| 21737 | 3 | 4 | | | | IV-1 | Tsen15 | 116461 | 4-May-15 | 21832 | 3 | 4 | | | | IV-1 | Ubald1 | 124402 | 4-May-15 |
| 21738 | 3 | 4 | | | | IV-1 | Tsen2 | 80746 | 23-May-15 | 21833 | 3 | 4 | | | | IV-1 | Ubap1l | 390595 | 4-May-15 |
| 21739 | 3 | 4 | | | | IV-1 | Tsen34 | 79042 | 23-May-15 | 21834 | 3 | 4 | | | | IV-1 | Ubap2 | 55833 | 4-May-15 |
| 21740 | 3 | 4 | | | | IV-1 | Tsen54 | 283989 | 23-May-15 | 21835 | 3 | 4 | | | | IV-1 | Ubap2l | 9898 | 4-May-15 |
| 21741 | 3 | 4 | | | | IV-1 | Tsfm | 10102 | 4-May-15 | 21836 | 3 | 4 | | | | IV-1 | Ubc | 7316 | 7-Jun-15 |
| 21742 | 3 | 4 | | | | IV-1 | Tsga10 | 80705 | 21-May-15 | 21837 | 3 | 4 | | | | IV-1 | Ube2b | 7320 | 12-May-15 |
| 21743 | 3 | 4 | | | | IV-1 | Tshb | 7252 | 31-May-15 | 21838 | 3 | 4 | | | | IV-1 | Ube2d1 | 7321 | 31-May-15 |
| 21744 | 3 | 4 | | | | IV-1 | Tsix | 9383 | 12-May-15 | 21839 | 3 | 4 | | | | IV-1 | Ube2d2a | | |
| 21745 | 3 | 4 | | | | IV-1 | Tsks | 60385 | 4-May-15 | 21840 | 3 | 4 | | | | IV-1 | Ube2d2b | | |
| 21746 | 3 | 4 | | | | IV-1 | Tsnax | 7257 | 12-May-15 | 21841 | 3 | 4 | | | | IV-1 | Ube2d3 | 7323 | 4-May-15 |
| 21747 | 3 | 4 | | | | IV-1 | Tsnaxip1 | 55815 | 4-May-15 | 21842 | 3 | 4 | | | | IV-1 | Ube2dnl1 | | |
| 21748 | 3 | 4 | | | | IV-1 | Tspan2os | | | 21843 | 3 | 4 | | | | IV-1 | Ube2dnl2 | | |
| 21749 | 3 | 4 | | | | IV-1 | Tspan3 | 10099 | 4-May-15 | 21844 | 3 | 4 | | | | IV-1 | Ube2e1 | 7324 | 4-May-15 |
| 21750 | 3 | 4 | | | | IV-1 | Tspan31 | 6302 | 20-May-15 | 21845 | 3 | 4 | | | | IV-1 | Ube2e2 | 7325 | 4-May-15 |
| 21751 | 3 | 4 | | | | IV-1 | Tspo | 706 | 12-May-15 | 21846 | 3 | 4 | | | | IV-1 | Ube2g1 | 7326 | 29-May-15 |
| 21752 | 3 | 4 | | | | IV-1 | Tspyl2 | 64061 | 4-May-15 | 21847 | 3 | 4 | | | | IV-1 | Ube2g2 | 7327 | 12-May-15 |

Fig. 30 - 116

| | | | | | | | | | | | | | | | |
|---|---|---|---|---|---|---|---|---|---|---|---|---|---|---|---|
| 21848 | 3 | 4 | | | | IV-1 | Ube2j | 7329 | 17-May-15 | 21943 | 3 | 4 | | IV-1 | Usp26 | 83844 | 4-May-15 |
| 21849 | 3 | 4 | | | | IV-1 | Ube2j1 | 51465 | 3-May-15 | 21944 | 3 | 4 | | IV-1 | Usp27x | 389856 | 4-May-15 |
| 21850 | 3 | 4 | | | | IV-1 | Ube2k | 3093 | 2-Jun-15 | 21945 | 3 | 4 | | IV-1 | Usp28 | 57646 | 12-May-15 |
| 21851 | 3 | 4 | | | | IV-1 | Ube2l3 | 7332 | 3-May-15 | 21946 | 3 | 4 | | IV-1 | Usp3 | 9960 | 4-May-15 |
| 21852 | 3 | 4 | | | | IV-1 | Ube2n | 7334 | 4-May-15 | 21947 | 3 | 4 | | IV-1 | Usp31 | 57478 | 7-Jun-15 |
| 21853 | 3 | 4 | | | | IV-1 | Ube2o | 63893 | 4-May-15 | 21948 | 3 | 4 | | IV-1 | Usp34 | 9736 | 4-May-15 |
| 21854 | 3 | 4 | | | | IV-1 | Ube2q2 | 92912 | 12-May-15 | 21949 | 3 | 4 | | IV-1 | Usp35 | 57558 | 4-May-15 |
| 21855 | 3 | 4 | | | | IV-1 | Ube2ql1 | 134111 | 4-May-15 | 21950 | 3 | 4 | | IV-1 | Usp37 | 57695 | 4-May-15 |
| 21856 | 3 | 4 | | | | IV-1 | Ube2v1 | 7335 | 2-Jun-15 | 21951 | 3 | 4 | | IV-1 | Usp38 | 84640 | 12-May-15 |
| 21857 | 3 | 4 | | | | IV-1 | Ube2v2 | 7336 | 4-May-15 | 21952 | 3 | 4 | | IV-1 | Usp39 | 10713 | 4-May-15 |
| 21858 | 3 | 4 | | | | IV-1 | Ube2w | 55284 | 4-May-15 | 21953 | 3 | 4 | | IV-1 | Usp4 | 7375 | 12-May-15 |
| 21859 | 3 | 4 | | | | IV-1 | Ube2z | 65264 | 4-May-15 | 21954 | 3 | 4 | | IV-1 | Usp40 | 55230 | 12-May-15 |
| 21860 | 3 | 4 | | | | IV-1 | Ube3b | 89910 | 4-May-15 | 21955 | 3 | 4 | | IV-1 | Usp42 | 84132 | 12-May-15 |
| 21861 | 3 | 4 | | | | IV-1 | Ube3c | 9690 | 4-May-15 | 21956 | 3 | 4 | | IV-1 | Usp43 | 124739 | 4-May-15 |
| 21862 | 3 | 4 | | | | IV-1 | Ubl3 | 5412 | 4-May-15 | 21957 | 3 | 4 | | IV-1 | Usp44 | 84101 | 4-May-15 |
| 21863 | 3 | 4 | | | | IV-1 | Ubl4 | 8266 | 29-May-15 | 21958 | 3 | 4 | | IV-1 | Usp46 | 64854 | 4-May-15 |
| 21864 | 3 | 4 | | | | IV-1 | Ubl4b | 164153 | 4-May-15 | 21959 | 3 | 4 | | IV-1 | Usp48 | 84196 | 4-May-15 |
| 21865 | 3 | 4 | | | | IV-1 | Ubl5 | 59286 | 7-Jun-15 | 21960 | 3 | 4 | | IV-1 | Usp50 | 373509 | 12-May-15 |
| 21866 | 3 | 4 | | | | IV-1 | Ubl7 | 84993 | 12-May-15 | 21961 | 3 | 4 | | IV-1 | Usp51 | 158880 | 4-May-15 |
| 21867 | 3 | 4 | | | | IV-1 | Ublcp1 | 134510 | 28-May-15 | 21962 | 3 | 4 | | IV-1 | Usp7 | 7874 | 31-May-15 |
| 21868 | 3 | 4 | | | | IV-1 | Ubn1 | 29855 | 12-May-15 | 21963 | 3 | 4 | | IV-1 | Usp9x | 8239 | 4-May-15 |
| 21869 | 3 | 4 | | | | IV-1 | Ubn2 | 254048 | 4-May-15 | 21964 | 3 | 4 | | IV-1 | Usp9y | 8287 | 23-May-15 |
| 21870 | 3 | 4 | | | | IV-1 | Ubox5 | 22888 | 4-May-15 | 21965 | 3 | 4 | | IV-1 | Uspl | 10208 | 23-May-15 |
| 21871 | 3 | 4 | | | | IV-1 | Ubp1 | 7342 | 4-May-15 | 21966 | 3 | 4 | | IV-1 | Ust | 10090 | 4-May-15 |
| 21872 | 3 | 4 | | | | IV-1 | Ubqln1 | 29979 | 21-May-15 | 21967 | 3 | 4 | | IV-1 | Utp11l | 51118 | 4-May-15 |
| 21873 | 3 | 4 | | | | IV-1 | Ubqln3 | 50613 | 4-May-15 | 21968 | 3 | 4 | | IV-1 | Utp18 | 51096 | 4-May-15 |
| 21874 | 3 | 4 | | | | IV-1 | Ubqln4 | 56893 | 21-May-15 | 21969 | 3 | 4 | | IV-1 | Utp23 | 84294 | 4-May-15 |
| 21875 | 3 | 4 | | | | IV-1 | Ubqlnl | 143630 | 4-May-15 | 21970 | 3 | 4 | | IV-1 | Utp3 | 57050 | 4-May-15 |
| 21876 | 3 | 4 | | | | IV-1 | Ubr1 | 197131 | 12-May-15 | 21971 | 3 | 4 | | IV-1 | Utp6 | 55843 | 4-May-15 |
| 21877 | 3 | 4 | | | | IV-1 | Ubr2 | 23304 | 4-May-15 | 21972 | 3 | 4 | | IV-1 | Utrn | 7402 | 12-May-15 |
| 21878 | 3 | 4 | | | | IV-1 | Ubr4 | 23352 | 12-May-15 | 21973 | 3 | 4 | | IV-1 | Uts2 | 10911 | 17-May-15 |
| 21879 | 3 | 4 | | | | IV-1 | Ubr7 | 55148 | 4-May-15 | 21974 | 3 | 4 | | IV-1 | Uvrag | 7405 | 7-Jun-15 |
| 21880 | 3 | 4 | | | | IV-1 | Ubtd1 | 80019 | 28-May-15 | 21975 | 3 | 4 | | IV-1 | Uxs1 | 80146 | 12-May-15 |
| 21881 | 3 | 4 | | | | IV-1 | Ubtfl1 | 642623 | 4-May-15 | 21976 | 3 | 4 | | IV-1 | Uxt | 8409 | 4-May-15 |
| 21882 | 3 | 4 | | | | IV-1 | Ubxn1 | 51035 | 31-May-15 | 21977 | 3 | 4 | | IV-1 | V1rd18 | | |
| 21883 | 3 | 4 | | | | IV-1 | Ubxn2b | 137886 | 21-May-15 | 21978 | 3 | 4 | | IV-1 | V1rd19 | | |
| 21884 | 3 | 4 | | | | IV-1 | Ubxn4 | 23190 | 4-May-15 | 21979 | 3 | 4 | | IV-1 | Vac14 | 55697 | 4-May-15 |
| 21885 | 3 | 4 | | | | IV-1 | Ubxn7 | 26043 | 4-May-15 | 21980 | 3 | 4 | | IV-1 | Vamp3 | 9341 | 4-May-15 |
| 21886 | 3 | 4 | | | | IV-1 | Ubxn8 | 7993 | 4-May-15 | 21981 | 3 | 4 | | IV-1 | Vamp5 | 10791 | 4-May-15 |
| 21887 | 3 | 4 | | | | IV-1 | Uchl3 | 7347 | 12-May-15 | 21982 | 3 | 4 | | IV-1 | Vamp8 | 8673 | 28-May-15 |
| 21888 | 3 | 4 | | | | IV-1 | Ufc1 | 51506 | 12-May-15 | 21983 | 3 | 4 | | IV-1 | Vapa | 9218 | 4-May-15 |
| 21889 | 3 | 4 | | | | IV-1 | Ufd1l | 7353 | 28-May-15 | 21984 | 3 | 4 | | IV-1 | Vapb | 9217 | 23-May-15 |
| 21890 | 3 | 4 | | | | IV-1 | Ufl1 | 23376 | 23-May-15 | 21985 | 3 | 4 | | IV-1 | Vars | 7407 | 21-May-15 |
| 21891 | 3 | 4 | | | | IV-1 | Ufm1 | 51569 | 4-May-15 | 21986 | 3 | 4 | | IV-1 | Vav3 | 10451 | 4-May-15 |
| 21892 | 3 | 4 | | | | IV-1 | Ufsp1 | 402682 | 4-May-15 | 21987 | 3 | 4 | | IV-1 | Vax2 | 25806 | 4-May-15 |
| 21893 | 3 | 4 | | | | IV-1 | Ufsp2 | 55325 | 4-May-15 | 21988 | 3 | 4 | | IV-1 | Vax2os | | |
| 21894 | 3 | 4 | | | | IV-1 | Ugcg | 7357 | 4-May-15 | 21989 | 3 | 4 | | IV-1 | Vbp1 | 7411 | 1-Jun-15 |
| 21895 | 3 | 4 | | | | IV-1 | Ugdh | 7358 | 12-May-15 | 21990 | 3 | 4 | | IV-1 | Vcam1 | 7412 | 17-May-15 |
| 21896 | 3 | 4 | | | | IV-1 | Ugp2 | 7360 | 4-May-15 | 21991 | 3 | 4 | | IV-1 | Vcpip1 | 80124 | 4-May-15 |
| 21897 | 3 | 4 | | | | IV-1 | Ugt1a1 | 54658 | 28-May-15 | 21992 | 3 | 4 | | IV-1 | Vcpkmt | 79609 | 4-May-15 |
| 21898 | 3 | 4 | | | | IV-1 | Ugt1a10 | 54575 | 28-May-15 | 21993 | 3 | 4 | | IV-1 | Vdac1 | 7416 | 12-May-15 |
| 21899 | 3 | 4 | | | | IV-1 | Ugt1a2 | | | 21994 | 3 | 4 | | IV-1 | Vdac3 | 7419 | 7-Jun-15 |
| 21900 | 3 | 4 | | | | IV-1 | Ugt2a1 | 10941 | 12-May-15 | 21995 | 3 | 4 | | IV-1 | Vezt | 55591 | 4-May-15 |
| 21901 | 3 | 4 | | | | IV-1 | Ugt2a2 | 574537 | 12-May-15 | 21996 | 3 | 4 | | IV-1 | Vgf | 7425 | 4-May-15 |
| 21902 | 3 | 4 | | | | IV-1 | Ugt2a3 | 79799 | 28-May-15 | 21997 | 3 | 4 | | IV-1 | Vgll1 | 51442 | 7-Jun-15 |
| 21903 | 3 | 4 | | | | IV-1 | Ugt2b37 | | | 21998 | 3 | 4 | | IV-1 | Vip | 7432 | 7-Jun-15 |
| 21904 | 3 | 4 | | | | IV-1 | Uhrf1bp1l | 23074 | 4-May-15 | 21999 | 3 | 4 | | IV-1 | Vipas39 | 63894 | 4-May-15 |
| 21905 | 3 | 4 | | | | IV-1 | Ulk3 | 25989 | 21-May-15 | 22000 | 3 | 4 | | IV-1 | Vmac | 400673 | 4-May-15 |
| 21906 | 3 | 4 | | | | IV-1 | Ulk4 | 54986 | 4-May-15 | 22001 | 3 | 4 | | IV-1 | Vmn1r10 | | |
| 21907 | 3 | 4 | | | | IV-1 | Umodl1 | 89766 | 4-May-15 | 22002 | 3 | 4 | | IV-1 | Vmn1r100 | | |
| 21908 | 3 | 4 | | | | IV-1 | Umps | 7372 | 12-May-15 | 22003 | 3 | 4 | | IV-1 | Vmn1r101 | | |
| 21909 | 3 | 4 | | | | IV-1 | Unc13a | 23025 | 17-May-15 | 22004 | 3 | 4 | | IV-1 | Vmn1r103 | | |
| 21910 | 3 | 4 | | | | IV-1 | Unc13b | 10497 | 4-May-15 | 22005 | 3 | 4 | | IV-1 | Vmn1r104 | | |
| 21911 | 3 | 4 | | | | IV-1 | Unc13c | 440279 | 12-May-15 | 22006 | 3 | 4 | | IV-1 | Vmn1r11 | | |
| 21912 | 3 | 4 | | | | IV-1 | Unc13d | 201294 | 23-May-15 | 22007 | 3 | 4 | | IV-1 | Vmn1r189 | | |
| 21913 | 3 | 4 | | | | IV-1 | Unc45a | 55898 | 4-May-15 | 22008 | 3 | 4 | | IV-1 | Vmn1r230 | | |
| 21914 | 3 | 4 | | | | IV-1 | Unc5a | 90249 | 4-May-15 | 22009 | 3 | 4 | | IV-1 | Vmn1r47 | | |
| 21915 | 3 | 4 | | | | IV-1 | Unc79 | 57578 | 4-May-15 | 22010 | 3 | 4 | | IV-1 | Vmn2r46 | | |
| 21916 | 3 | 4 | | | | IV-1 | Unc80 | 285175 | 4-May-15 | 22011 | 3 | 4 | | IV-1 | Vmn2r56 | | |
| 21917 | 3 | 4 | | | | IV-1 | Unkl | 64718 | 4-May-15 | 22012 | 3 | 4 | | IV-1 | Vmn2r67 | | |
| 21918 | 3 | 4 | | | | IV-1 | Upf1 | 5976 | 2-Jun-15 | 22013 | 3 | 4 | | IV-1 | Vmn2r74 | | |
| 21919 | 3 | 4 | | | | IV-1 | Upf2 | 26019 | 12-May-15 | 22014 | 3 | 4 | | IV-1 | Vmn2r76 | | |
| 21920 | 3 | 4 | | | | IV-1 | Upf3a | 65110 | 4-May-15 | 22015 | 3 | 4 | | IV-1 | Vmn2r-ps54 | | |
| 21921 | 3 | 4 | | | | IV-1 | Upf3b | 65109 | 23-May-15 | 22016 | 3 | 4 | | IV-1 | Vps13a | 23230 | 23-May-15 |
| 21922 | 3 | 4 | | | | IV-1 | Uqcr10 | 29796 | 4-May-15 | 22017 | 3 | 4 | | IV-1 | Vps13c | 54832 | 4-May-15 |
| 21923 | 3 | 4 | | | | IV-1 | Uqcrq | 27089 | 4-May-15 | 22018 | 3 | 4 | | IV-1 | Vps16 | 64601 | 21-May-15 |
| 21924 | 3 | 4 | | | | IV-1 | Urah | 100130015 | 4-May-15 | 22019 | 3 | 4 | | IV-1 | Vps18 | 57617 | 4-May-15 |
| 21925 | 3 | 4 | | | | IV-1 | Urb2 | 9816 | 4-May-15 | 22020 | 3 | 4 | | IV-1 | Vps25 | 84313 | 4-May-15 |
| 21926 | 3 | 4 | | | | IV-1 | Urgcp | 55665 | 12-May-15 | 22021 | 3 | 4 | | IV-1 | Vps26a | 9559 | 4-May-15 |
| 21927 | 3 | 4 | | | | IV-1 | Uri1 | 8725 | 24-May-15 | 22022 | 3 | 4 | | IV-1 | Vps26b | 112936 | 4-May-15 |
| 21928 | 3 | 4 | | | | IV-1 | Urm1 | 81605 | 24-May-15 | 22023 | 3 | 4 | | IV-1 | Vps28 | 51160 | 4-May-15 |
| 21929 | 3 | 4 | | | | IV-1 | Use1 | 55850 | 7-Jun-15 | 22024 | 3 | 4 | | IV-1 | Vps29 | 51699 | 4-May-15 |
| 21930 | 3 | 4 | | | | IV-1 | Usf1 | 7391 | 4-May-15 | 22025 | 3 | 4 | | IV-1 | Vps33a | 65082 | 4-May-15 |
| 21931 | 3 | 4 | | | | IV-1 | Usf2 | 7392 | 17-May-15 | 22026 | 3 | 4 | | IV-1 | Vps33b | 26276 | 4-May-15 |
| 21932 | 3 | 4 | | | | IV-1 | Usp1 | 7398 | 4-May-15 | 22027 | 3 | 4 | | IV-1 | Vps36 | 51028 | 4-May-15 |
| 21933 | 3 | 4 | | | | IV-1 | Usp11 | 8237 | 21-May-15 | 22028 | 3 | 4 | | IV-1 | Vps37a | 137492 | 4-May-15 |
| 21934 | 3 | 4 | | | | IV-1 | Usp12 | 219333 | 7-Jun-15 | 22029 | 3 | 4 | | IV-1 | Vps37b | 79720 | 4-May-15 |
| 21935 | 3 | 4 | | | | IV-1 | Usp13 | 8975 | 29-May-15 | 22030 | 3 | 4 | | IV-1 | Vps39 | 23339 | 21-May-15 |
| 21936 | 3 | 4 | | | | IV-1 | Usp14 | 9097 | 4-May-15 | 22031 | 3 | 4 | | IV-1 | Vps41 | 27072 | 7-Jun-15 |
| 21937 | 3 | 4 | | | | IV-1 | Usp17la | | | 22032 | 3 | 4 | | IV-1 | Vps45 | 11311 | 4-May-15 |
| 21938 | 3 | 4 | | | | IV-1 | Usp17lb | | | 22033 | 3 | 4 | | IV-1 | Vps4a | 27183 | 4-May-15 |
| 21939 | 3 | 4 | | | | IV-1 | Usp17lc | | | 22034 | 3 | 4 | | IV-1 | Vps4b | 9525 | 31-May-15 |
| 21940 | 3 | 4 | | | | IV-1 | Usp17ld | | | 22035 | 3 | 4 | | IV-1 | Vps51 | 738 | 29-May-15 |
| 21941 | 3 | 4 | | | | IV-1 | Usp17le | | | 22036 | 3 | 4 | | IV-1 | Vps52 | 6293 | 29-May-15 |
| 21942 | 3 | 4 | | | | IV-1 | Usp25 | 29761 | 12-May-15 | 22037 | 3 | 4 | | IV-1 | Vps53 | 55275 | 29-May-15 |
| | | | | | | | | | | 22038 | 3 | 4 | | IV-1 | Vps54 | 51542 | 29-May-15 |

Fig. 30 - 117

| | | | | | | | | | | | | | | |
|---|---|---|---|---|---|---|---|---|---|---|---|---|---|---|
| 22039 | 3 | 4 | | | | IV-1 | Vps72 | 6944 | 4-May-15 | 22135 | 3 | 4 | | | | IV-1 | Kntrpc | | |
| 22040 | 3 | 4 | | | | IV-1 | Vps8 | 23355 | 21-May-15 | 22136 | 3 | 4 | | | | IV-1 | Xpa | 7507 | 23-May-15 |
| 22041 | 3 | 4 | | | | IV-1 | Vps9d1 | 9605 | 4-May-15 | 22137 | 3 | 4 | | | | IV-1 | Xpc | 7508 | 23-May-15 |
| 22042 | 3 | 4 | | | | IV-1 | Vrk1 | 7443 | 4-May-15 | 22138 | 3 | 4 | | | | IV-1 | Xpnpep3 | 63929 | 4-May-15 |
| 22043 | 3 | 4 | | | | IV-1 | Vrtn | 55237 | 4-May-15 | 22139 | 3 | 4 | | | | IV-1 | Xpo4 | 64328 | 4-May-15 |
| 22044 | 3 | 4 | | | | IV-1 | Vsig1 | 340547 | 4-May-15 | 22140 | 3 | 4 | | | | IV-1 | Xpo5 | 57510 | 4-May-15 |
| 22045 | 3 | 4 | | | | IV-1 | Vstm4 | 196740 | 4-May-15 | 22141 | 3 | 4 | | | | IV-1 | Xpo6 | 23214 | 4-May-15 |
| 22046 | 3 | 4 | | | | IV-1 | Vta1 | 51534 | 31-May-15 | 22142 | 3 | 4 | | | | IV-1 | Xpr1 | 9213 | 4-May-15 |
| 22047 | 3 | 4 | | | | IV-1 | Vwa5b1 | 127731 | 4-May-15 | 22143 | 3 | 4 | | | | IV-1 | Xrcc1 | 7515 | 31-May-15 |
| 22048 | 3 | 4 | | | | IV-1 | Vwa5b2 | 90113 | 4-May-15 | 22144 | 3 | 4 | | | | IV-1 | Xrcc5 | 7520 | 23-May-15 |
| 22049 | 3 | 4 | | | | IV-1 | Vwa7 | 80737 | 4-May-15 | 22145 | 3 | 4 | | | | IV-1 | Xrn1 | 54464 | 4-May-15 |
| 22050 | 3 | 4 | | | | IV-1 | Vwa8 | 23078 | 4-May-15 | 22146 | 3 | 4 | | | | IV-1 | Yaf2 | 10138 | 4-May-15 |
| 22051 | 3 | 4 | | | | IV-1 | Vwc2 | 375567 | 4-May-15 | 22147 | 3 | 4 | | | | IV-1 | Yars | 8565 | 17-May-15 |
| 22052 | 3 | 4 | | | | IV-1 | Vwc2l | 402117 | 2-Jun-15 | 22148 | 3 | 4 | | | | IV-1 | Yars2 | 51067 | 4-May-15 |
| 22053 | 3 | 4 | | | | IV-1 | Vwce | 220001 | 4-May-15 | 22149 | 3 | 4 | | | | IV-1 | Yeats4 | 8089 | 4-May-15 |
| 22054 | 3 | 4 | | | | IV-1 | Vwf | 7450 | 31-May-15 | 22150 | 3 | 4 | | | | IV-1 | Yes1 | 7525 | 12-May-15 |
| 22055 | 3 | 4 | | | | IV-1 | Wap | | | 22151 | 3 | 4 | | | | IV-1 | Yif1a | 10897 | 12-May-15 |
| 22056 | 3 | 4 | | | | IV-1 | Wasl | 8976 | 4-May-15 | 22152 | 3 | 4 | | | | IV-1 | Yif1b | 90522 | 4-May-15 |
| 22057 | 3 | 4 | | | | IV-1 | Wbp1 | 23559 | 7-Jun-15 | 22153 | 3 | 4 | | | | IV-1 | Yipf1 | 54432 | 28-May-15 |
| 22058 | 3 | 4 | | | | IV-1 | Wbp11 | 51729 | 3-May-15 | 22154 | 3 | 4 | | | | IV-1 | Yipf2 | 78992 | 4-May-15 |
| 22059 | 3 | 4 | | | | IV-1 | Wbp1l | 54838 | 4-May-15 | 22155 | 3 | 4 | | | | IV-1 | Yipf4 | 84272 | 4-May-15 |
| 22060 | 3 | 4 | | | | IV-1 | Wbp2 | 23558 | 12-May-15 | 22156 | 3 | 4 | | | | IV-1 | Yipf6 | 286451 | 4-May-15 |
| 22061 | 3 | 4 | | | | IV-1 | Wbp2nl | 164684 | 12-May-15 | 22157 | 3 | 4 | | | | IV-1 | Ylpm1 | 56252 | 12-May-15 |
| 22062 | 3 | 4 | | | | IV-1 | Wbp4 | 11193 | 4-May-15 | 22158 | 3 | 4 | | | | IV-1 | Yme1l1 | 10730 | 12-May-15 |
| 22063 | 3 | 4 | | | | IV-1 | Wbp5 | 51186 | 4-May-15 | 22159 | 3 | 4 | | | | IV-1 | Yod1 | 55432 | 29-May-15 |
| 22064 | 3 | 4 | | | | IV-1 | Wbscr17 | 64409 | 4-May-15 | 22160 | 3 | 4 | | | | IV-1 | Yrdc | 79693 | 4-May-15 |
| 22065 | 3 | 4 | | | | IV-1 | Wdfy3 | 23001 | 21-May-15 | 22161 | 3 | 4 | | | | IV-1 | Ythdc2 | 64848 | 4-May-15 |
| 22066 | 3 | 4 | | | | IV-1 | Wdr12 | 55759 | 4-May-15 | 22162 | 3 | 4 | | | | IV-1 | Ythdf1 | 54915 | 12-May-15 |
| 22067 | 3 | 4 | | | | IV-1 | Wdr13 | 64743 | 20-May-15 | 22163 | 3 | 4 | | | | IV-1 | Ythdf2 | 51441 | 4-May-15 |
| 22068 | 3 | 4 | | | | IV-1 | Wdr18 | 57418 | 4-May-15 | 22164 | 3 | 4 | | | | IV-1 | Ythdf3 | 253943 | 4-May-15 |
| 22069 | 3 | 4 | | | | IV-1 | Wdr19 | 57728 | 4-May-15 | 22165 | 3 | 4 | | | | IV-1 | Ywhab | 7529 | 4-May-15 |
| 22070 | 3 | 4 | | | | IV-1 | Wdr20rt | | | 22166 | 3 | 4 | | | | IV-1 | Ywhag | 7532 | 4-May-15 |
| 22071 | 3 | 4 | | | | IV-1 | Wdr24 | 84219 | 29-May-15 | 22167 | 3 | 4 | | | | IV-1 | Ywhah | 7533 | 12-May-15 |
| 22072 | 3 | 4 | | | | IV-1 | Wdr27 | 253769 | 4-May-15 | 22168 | 3 | 4 | | | | IV-1 | Ywhaz | 7534 | 31-May-15 |
| 22073 | 3 | 4 | | | | IV-1 | Wdr3 | 10885 | 12-May-15 | 22169 | 3 | 4 | | | | IV-1 | Yy2 | 404281 | 4-May-15 |
| 22074 | 3 | 4 | | | | IV-1 | Wdr31 | 114987 | 4-May-15 | 22170 | 3 | 4 | | | | IV-1 | Zak | 51776 | 4-May-15 |
| 22075 | 3 | 4 | | | | IV-1 | Wdr34 | 89891 | 4-May-15 | 22171 | 3 | 4 | | | | IV-1 | Zap70 | 7535 | 23-May-15 |
| 22076 | 3 | 4 | | | | IV-1 | Wdr35 | 57539 | 28-May-15 | 22172 | 3 | 4 | | | | IV-1 | Zar1 | 326340 | 4-May-15 |
| 22077 | 3 | 4 | | | | IV-1 | Wdr36 | 134430 | 4-May-15 | 22173 | 3 | 4 | | | | IV-1 | Zar1l | 646799 | 4-May-15 |
| 22078 | 3 | 4 | | | | IV-1 | Wdr37 | 22884 | 4-May-15 | 22174 | 3 | 4 | | | | IV-1 | Zbbx | 79740 | 4-May-15 |
| 22079 | 3 | 4 | | | | IV-1 | Wdr4 | 10785 | 4-May-15 | 22175 | 3 | 4 | | | | IV-1 | Zbed3 | 84327 | 4-May-15 |
| 22080 | 3 | 4 | | | | IV-1 | Wdr41 | 55255 | 4-May-15 | 22176 | 3 | 4 | | | | IV-1 | Zbed6 | 100381270 | 4-May-15 |
| 22081 | 3 | 4 | | | | IV-1 | Wdr43 | 23160 | 4-May-15 | 22177 | 3 | 4 | | | | IV-1 | Zbtb10 | 65986 | 4-May-15 |
| 22082 | 3 | 4 | | | | IV-1 | Wdr45 | 11152 | 23-May-15 | 22178 | 3 | 4 | | | | IV-1 | Zbtb11 | 27107 | 12-May-15 |
| 22083 | 3 | 4 | | | | IV-1 | Wdr45b | 56270 | 21-May-15 | 22179 | 3 | 4 | | | | IV-1 | Zbtb12 | 221527 | 4-May-15 |
| 22084 | 3 | 4 | | | | IV-1 | Wdr46 | 9277 | 4-May-15 | 22180 | 3 | 4 | | | | IV-1 | Zbtb18 | 10472 | 4-May-15 |
| 22085 | 3 | 4 | | | | IV-1 | Wdr48 | 57599 | 12-May-15 | 22181 | 3 | 4 | | | | IV-1 | Zbtb2 | 57621 | 3-May-15 |
| 22086 | 3 | 4 | | | | IV-1 | Wdr5 | 11091 | 4-May-15 | 22182 | 3 | 4 | | | | IV-1 | Zbtb20 | 26137 | 4-May-15 |
| 22087 | 3 | 4 | | | | IV-1 | Wdr54 | 84058 | 4-May-15 | 22183 | 3 | 4 | | | | IV-1 | Zbtb24 | 9841 | 4-May-15 |
| 22088 | 3 | 4 | | | | IV-1 | Wdr59 | 79726 | 29-May-15 | 22184 | 3 | 4 | | | | IV-1 | Zbtb25 | 7597 | 28-May-15 |
| 22089 | 3 | 4 | | | | IV-1 | Wdr5b | 54554 | 4-May-15 | 22185 | 3 | 4 | | | | IV-1 | Zbtb3 | 79842 | 4-May-15 |
| 22090 | 3 | 4 | | | | IV-1 | Wdr60 | 55112 | 4-May-15 | 22186 | 3 | 4 | | | | IV-1 | Zbtb34 | 403341 | 1-Jun-15 |
| 22091 | 3 | 4 | | | | IV-1 | Wdr61 | 80349 | 12-May-15 | 22187 | 3 | 4 | | | | IV-1 | Zbtb37 | 84614 | 4-May-15 |
| 22092 | 3 | 4 | | | | IV-1 | Wdr62 | 284403 | 23-May-15 | 22188 | 3 | 4 | | | | IV-1 | Zbtb39 | 9880 | 4-May-15 |
| 22093 | 3 | 4 | | | | IV-1 | Wdr65 | 149465 | 12-May-15 | 22189 | 3 | 4 | | | | IV-1 | Zbtb4 | 57659 | 4-May-15 |
| 22094 | 3 | 4 | | | | IV-1 | Wdr7 | 23335 | 4-May-15 | 22190 | 3 | 4 | | | | IV-1 | Zbtb40 | 9923 | 4-May-15 |
| 22095 | 3 | 4 | | | | IV-1 | Wdr70 | 55100 | 4-May-15 | 22191 | 3 | 4 | | | | IV-1 | Zbtb41 | 360023 | 4-May-15 |
| 22096 | 3 | 4 | | | | IV-1 | Wdr72 | 256764 | 4-May-15 | 22192 | 3 | 4 | | | | IV-1 | Zbtb42 | 100128927 | 4-May-15 |
| 22097 | 3 | 4 | | | | IV-1 | Wdr73 | 84942 | 20-May-15 | 22193 | 3 | 4 | | | | IV-1 | Zbtb43 | 23099 | 4-May-15 |
| 22098 | 3 | 4 | | | | IV-1 | Wdr74 | 54663 | 12-May-15 | 22194 | 3 | 4 | | | | IV-1 | Zbtb44 | 29068 | 4-May-15 |
| 22099 | 3 | 4 | | | | IV-1 | Wdr75 | 84128 | 3-May-15 | 22195 | 3 | 4 | | | | IV-1 | Zbtb45 | 84878 | 12-May-15 |
| 22100 | 3 | 4 | | | | IV-1 | Wdr76 | 79968 | 4-May-15 | 22196 | 3 | 4 | | | | IV-1 | Zbtb46 | 140685 | 28-May-15 |
| 22101 | 3 | 4 | | | | IV-1 | Wdr81 | 124997 | 4-May-15 | 22197 | 3 | 4 | | | | IV-1 | Zbtb49 | 166793 | 28-May-15 |
| 22102 | 3 | 4 | | | | IV-1 | Wdr82 | 80335 | 10-Jun-15 | 22198 | 3 | 4 | | | | IV-1 | Zbtb5 | 9925 | 4-May-15 |
| 22103 | 3 | 4 | | | | IV-1 | Wdr83 | 84292 | 4-May-15 | 22199 | 3 | 4 | | | | IV-1 | Zbtb6 | 10773 | 4-May-15 |
| 22104 | 3 | 4 | | | | IV-1 | Wdr83os | 51398 | 4-May-15 | 22200 | 3 | 4 | | | | IV-1 | Zbtb7a | 51341 | 4-May-15 |
| 22105 | 3 | 4 | | | | IV-1 | Wdr86 | 349136 | 21-May-15 | 22201 | 3 | 4 | | | | IV-1 | Zbtb7b | 51043 | 4-May-15 |
| 22106 | 3 | 4 | | | | IV-1 | Wdr90 | 197335 | 4-May-15 | 22202 | 3 | 4 | | | | IV-1 | Zbtb9 | 221504 | 4-May-15 |
| 22107 | 3 | 4 | | | | IV-1 | Wdr92 | 116143 | 4-May-15 | 22203 | 3 | 4 | | | | IV-1 | Zbtbd6 | | |
| 22108 | 3 | 4 | | | | IV-1 | Wdr93 | 56964 | 4-May-15 | 22204 | 3 | 4 | | | | IV-1 | Zc2hc1b | 153918 | 4-May-15 |
| 22109 | 3 | 4 | | | | IV-1 | Wdytw1 | 55093 | 23-May-15 | 22205 | 3 | 4 | | | | IV-1 | Zc3h11a | 9877 | 4-May-15 |
| 22110 | 3 | 4 | | | | IV-1 | Wfdc5 | 149708 | 4-May-15 | 22206 | 3 | 4 | | | | IV-1 | Zc3h12a | 80149 | 4-May-15 |
| 22111 | 3 | 4 | | | | IV-1 | Wibg | 84305 | 4-May-15 | 22207 | 3 | 4 | | | | IV-1 | Zc3h12c | 85463 | 4-May-15 |
| 22112 | 3 | 4 | | | | IV-1 | Wls | 79971 | 17-May-15 | 22208 | 3 | 4 | | | | IV-1 | Zc3h14 | 79882 | 4-May-15 |
| 22113 | 3 | 4 | | | | IV-1 | Wnk1 | 65125 | 31-May-15 | 22209 | 3 | 4 | | | | IV-1 | Zc3h15 | 55854 | 12-May-15 |
| 22114 | 3 | 4 | | | | IV-1 | Wnk4 | 65266 | 23-May-15 | 22210 | 3 | 4 | | | | IV-1 | Zc3h18 | 124245 | 7-Jun-15 |
| 22115 | 3 | 4 | | | | IV-1 | Wnt1 | 7471 | 17-May-15 | 22211 | 3 | 4 | | | | IV-1 | Zc3h3 | 23144 | 21-May-15 |
| 22116 | 3 | 4 | | | | IV-1 | Wnt10a | 80326 | 4-May-15 | 22212 | 3 | 4 | | | | IV-1 | Zc3h4 | 23211 | 4-May-15 |
| 22117 | 3 | 4 | | | | IV-1 | Wnt10b | 7480 | 4-May-15 | 22213 | 3 | 4 | | | | IV-1 | Zc3h7b | 23264 | 4-May-15 |
| 22118 | 3 | 4 | | | | IV-1 | Wrap53 | 55135 | 23-May-15 | 22214 | 3 | 4 | | | | IV-1 | Zc3h8 | 84524 | 4-May-15 |
| 22119 | 3 | 4 | | | | IV-1 | Wrb | 7485 | 4-May-15 | 22215 | 3 | 4 | | | | IV-1 | Zc4h2 | 55906 | 4-May-15 |
| 22120 | 3 | 4 | | | | IV-1 | Wrn | 7486 | 23-May-15 | 22216 | 3 | 4 | | | | IV-1 | Zcchc11 | 23318 | 4-May-15 |
| 22121 | 3 | 4 | | | | IV-1 | Wsb1 | 26118 | 14-May-15 | 22217 | 3 | 4 | | | | IV-1 | Zcchc13 | 389874 | 4-May-15 |
| 22122 | 3 | 4 | | | | IV-1 | Wsnd1 | 23302 | 4-May-15 | 22218 | 3 | 4 | | | | IV-1 | Zcchc14 | 23174 | 4-May-15 |
| 22123 | 3 | 4 | | | | IV-1 | Wtap | 9589 | 4-May-15 | 22219 | 3 | 4 | | | | IV-1 | Zcchc16 | 340595 | 4-May-15 |
| 22124 | 3 | 4 | | | | IV-1 | Wtip | 126374 | 4-May-15 | 22220 | 3 | 4 | | | | IV-1 | Zcchc17 | 51538 | 28-May-15 |
| 22125 | 3 | 4 | | | | IV-1 | Wwox | 51741 | 12-May-15 | 22221 | 3 | 4 | | | | IV-1 | Zcchc7 | 84186 | 4-May-15 |
| 22126 | 3 | 4 | | | | IV-1 | Wwp1 | 11059 | 4-May-15 | 22222 | 3 | 4 | | | | IV-1 | Zcchc8 | 55596 | 27-May-15 |
| 22127 | 3 | 4 | | | | IV-1 | Wwp2 | 11060 | 23-May-15 | 22223 | 3 | 4 | | | | IV-1 | Zcchc9 | 84240 | 4-May-15 |
| 22128 | 3 | 4 | | | | IV-1 | Wwtr1 | 25937 | 4-May-15 | 22224 | 3 | 4 | | | | IV-1 | Zcrb1 | 85437 | 4-May-15 |
| 22129 | 3 | 4 | | | | IV-1 | Xkr5 | 389610 | 4-May-15 | 22225 | 3 | 4 | | | | IV-1 | Zcwpw1 | 55063 | 4-May-15 |
| 22130 | 3 | 4 | | | | IV-1 | Xkr6 | 286046 | 4-May-15 | 22226 | 3 | 4 | | | | IV-1 | Zdhhc1 | 29800 | 4-May-15 |
| 22131 | 3 | 4 | | | | IV-1 | Xkr7 | 343702 | 4-May-15 | 22227 | 3 | 4 | | | | IV-1 | Zdhhc11 | 79844 | 14-May-15 |
| 22132 | 3 | 4 | | | | IV-1 | Xlr5b | | | 22228 | 3 | 4 | | | | IV-1 | Zdhhc12 | 84885 | 4-May-15 |
| 22133 | 3 | 4 | | | | IV-1 | Xlr5c | | | | | | | | | | | | |
| 22134 | 3 | 4 | | | | IV-1 | Xndc1 | | | | | | | | | | | | |

Fig. 30 - 118

| | | | | | | | | | | | | | | | | | |
|---|---|---|---|---|---|---|---|---|---|---|---|---|---|---|---|---|---|
| 22229 | 3 | 4 | | | | IV-1 | Zdhhc17 | 23390 | 1-Jun-15 | 22325 | 3 | 4 | | | | IV-1 | Zfp398 | | |
| 22230 | 3 | 4 | | | | IV-1 | Zdhhc18 | 84243 | 4-May-15 | 22326 | 3 | 4 | | | | IV-1 | Zfp40 | | |
| 22231 | 3 | 4 | | | | IV-1 | Zdhhc19 | 131540 | 4-May-15 | 22327 | 3 | 4 | | | | IV-1 | Zfp408 | | |
| 22232 | 3 | 4 | | | | IV-1 | Zdhhc2 | 51201 | 4-May-15 | 22328 | 3 | 4 | | | | IV-1 | Zfp41 | 286128 | 12-May-15 |
| 22233 | 3 | 4 | | | | IV-1 | Zdhhc23 | 254887 | 4-May-15 | 22329 | 3 | 4 | | | | IV-1 | Zfp410 | | |
| 22234 | 3 | 4 | | | | IV-1 | Zdhhc25 | | | 22330 | 3 | 4 | | | | IV-1 | Zfp414 | 84330 | 4-May-15 |
| 22235 | 3 | 4 | | | | IV-1 | Zdhhc3 | 51304 | 4-May-15 | 22331 | 3 | 4 | | | | IV-1 | Zfp418 | | |
| 22236 | 3 | 4 | | | | IV-1 | Zdhhc4 | 55146 | 4-May-15 | 22332 | 3 | 4 | | | | IV-1 | Zfp42 | 132625 | 12-May-15 |
| 22237 | 3 | 4 | | | | IV-1 | Zdhhc5 | 25921 | 4-May-15 | 22333 | 3 | 4 | | | | IV-1 | Zfp420 | | |
| 22238 | 3 | 4 | | | | IV-1 | Zdhhc6 | 64429 | 12-May-15 | 22334 | 3 | 4 | | | | IV-1 | Zfp422 | 7570 | 4-May-15 |
| 22239 | 3 | 4 | | | | IV-1 | Zdhhc7 | 55625 | 4-May-15 | 22335 | 3 | 4 | | | | IV-1 | Zfp423 | 23090 | 20-May-15 |
| 22240 | 3 | 4 | | | | IV-1 | Zdhhc8 | 29801 | 3-Jun-15 | 22336 | 3 | 4 | | | | IV-1 | Zfp428 | 126299 | 4-May-15 |
| 22241 | 3 | 4 | | | | IV-1 | Zdhhc9 | 51114 | 4-May-15 | 22337 | 3 | 4 | | | | IV-1 | Zfp433 | | |
| 22242 | 3 | 4 | | | | IV-1 | Zeb1 | 6935 | 31-May-15 | 22338 | 3 | 4 | | | | IV-1 | Zfp438 | | |
| 22243 | 3 | 4 | | | | IV-1 | Zeb2 | 9839 | 31-May-15 | 22339 | 3 | 4 | | | | IV-1 | Zfp442 | | |
| 22244 | 3 | 4 | | | | IV-1 | Zf12 | | | 22340 | 3 | 4 | | | | IV-1 | Zfp445 | | |
| 22245 | 3 | 4 | | | | IV-1 | Zfand1 | 79752 | 4-May-15 | 22341 | 3 | 4 | | | | IV-1 | Zfp449 | | |
| 22246 | 3 | 4 | | | | IV-1 | Zfand3 | 60685 | 4-May-15 | 22342 | 3 | 4 | | | | IV-1 | Zfp454 | | |
| 22247 | 3 | 4 | | | | IV-1 | Zfat | 57623 | 28-May-15 | 22343 | 3 | 4 | | | | IV-1 | Zfp455 | | |
| 22248 | 3 | 4 | | | | IV-1 | Zfc3h1 | 196441 | 4-May-15 | 22344 | 3 | 4 | | | | IV-1 | Zfp456 | | |
| 22249 | 3 | 4 | | | | IV-1 | Zfhx2 | 85446 | 4-May-15 | 22345 | 3 | 4 | | | | IV-1 | Zfp457 | | |
| 22250 | 3 | 4 | | | | IV-1 | Zfhx3 | 463 | 12-May-15 | 22346 | 3 | 4 | | | | IV-1 | Zfp458 | | |
| 22251 | 3 | 4 | | | | IV-1 | Zfhx4 | 79776 | 12-May-15 | 22347 | 3 | 4 | | | | IV-1 | Zfp459 | | |
| 22252 | 3 | 4 | | | | IV-1 | Zfml | 27332 | 4-May-15 | 22348 | 3 | 4 | | | | IV-1 | Zfp46 | 80818 | 4-May-15 |
| 22253 | 3 | 4 | | | | IV-1 | Zfp1 | 162239 | 12-May-15 | 22349 | 3 | 4 | | | | IV-1 | Zfp473 | | |
| 22254 | 3 | 4 | | | | IV-1 | Zfp106 | 64397 | 12-May-15 | 22350 | 3 | 4 | | | | IV-1 | Zfp51 | | |
| 22255 | 3 | 4 | | | | IV-1 | Zfp108 | | | 22351 | 3 | 4 | | | | IV-1 | Zfp511 | | |
| 22256 | 3 | 4 | | | | IV-1 | Zfp11 | | | 22352 | 3 | 4 | | | | IV-1 | Zfp513 | | |
| 22257 | 3 | 4 | | | | IV-1 | Zfp110 | | | 22353 | 3 | 4 | | | | IV-1 | Zfp516 | | |
| 22258 | 3 | 4 | | | | IV-1 | Zfp112 | 7771 | 4-May-15 | 22354 | 3 | 4 | | | | IV-1 | Zfp518a | | |
| 22259 | 3 | 4 | | | | IV-1 | Zfp114 | | | 22355 | 3 | 4 | | | | IV-1 | Zfp518b | | |
| 22260 | 3 | 4 | | | | IV-1 | Zfp119a | | | 22356 | 3 | 4 | | | | IV-1 | Zfp52 | | |
| 22261 | 3 | 4 | | | | IV-1 | Zfp119b | | | 22357 | 3 | 4 | | | | IV-1 | Zfp521 | | |
| 22262 | 3 | 4 | | | | IV-1 | Zfp12 | | | 22358 | 3 | 4 | | | | IV-1 | Zfp524 | | |
| 22263 | 3 | 4 | | | | IV-1 | Zfp120 | | | 22359 | 3 | 4 | | | | IV-1 | Zfp526 | | |
| 22264 | 3 | 4 | | | | IV-1 | Zfp128 | 7554 | 4-May-15 | 22360 | 3 | 4 | | | | IV-1 | Zfp53 | | |
| 22265 | 3 | 4 | | | | IV-1 | Zfp143 | | | 22361 | 3 | 4 | | | | IV-1 | Zfp532 | | |
| 22266 | 3 | 4 | | | | IV-1 | Zfp146 | | | 22362 | 3 | 4 | | | | IV-1 | Zfp54 | | |
| 22267 | 3 | 4 | | | | IV-1 | Zfp148 | 7707 | 2-Jun-15 | 22363 | 3 | 4 | | | | IV-1 | Zfp541 | | |
| 22268 | 3 | 4 | | | | IV-1 | Zfp169 | | | 22364 | 3 | 4 | | | | IV-1 | Zfp551 | | |
| 22269 | 3 | 4 | | | | IV-1 | Zfp174 | | | 22365 | 3 | 4 | | | | IV-1 | Zfp553 | | |
| 22270 | 3 | 4 | | | | IV-1 | Zfp180 | | | 22366 | 3 | 4 | | | | IV-1 | Zfp560 | | |
| 22271 | 3 | 4 | | | | IV-1 | Zfp182 | 7569 | 4-May-15 | 22367 | 3 | 4 | | | | IV-1 | Zfp563 | | |
| 22272 | 3 | 4 | | | | IV-1 | Zfp184 | | | 22368 | 3 | 4 | | | | IV-1 | Zfp566 | | |
| 22273 | 3 | 4 | | | | IV-1 | Zfp2 | 80108 | 4-May-15 | 22369 | 3 | 4 | | | | IV-1 | Zfp574 | | |
| 22274 | 3 | 4 | | | | IV-1 | Zfp207 | | | 22370 | 3 | 4 | | | | IV-1 | Zfp575 | | |
| 22275 | 3 | 4 | | | | IV-1 | Zfp212 | | | 22371 | 3 | 4 | | | | IV-1 | Zfp579 | | |
| 22276 | 3 | 4 | | | | IV-1 | Zfp213 | | | 22372 | 3 | 4 | | | | IV-1 | Zfp58 | | |
| 22277 | 3 | 4 | | | | IV-1 | Zfp217 | | | 22373 | 3 | 4 | | | | IV-1 | Zfp580 | | |
| 22278 | 3 | 4 | | | | IV-1 | Zfp219 | 51222 | 4-May-15 | 22374 | 3 | 4 | | | | IV-1 | Zfp59 | | |
| 22279 | 3 | 4 | | | | IV-1 | Zfp229 | | | 22375 | 3 | 4 | | | | IV-1 | Zfp592 | | |
| 22280 | 3 | 4 | | | | IV-1 | Zfp235 | | | 22376 | 3 | 4 | | | | IV-1 | Zfp593 | | |
| 22281 | 3 | 4 | | | | IV-1 | Zfp236 | | | 22377 | 3 | 4 | | | | IV-1 | Zfp597 | | |
| 22282 | 3 | 4 | | | | IV-1 | Zfp239 | | | 22378 | 3 | 4 | | | | IV-1 | Zfp598 | | |
| 22283 | 3 | 4 | | | | IV-1 | Zfp248 | | | 22379 | 3 | 4 | | | | IV-1 | Zfp599 | | |
| 22284 | 3 | 4 | | | | IV-1 | Zfp251 | | | 22380 | 3 | 4 | | | | IV-1 | Zfp60 | | |
| 22285 | 3 | 4 | | | | IV-1 | Zfp26 | 50862 | 1-Jun-15 | 22381 | 3 | 4 | | | | IV-1 | Zfp600 | | |
| 22286 | 3 | 4 | | | | IV-1 | Zfp260 | 339324 | 4-May-15 | 22382 | 3 | 4 | | | | IV-1 | Zfp607 | | |
| 22287 | 3 | 4 | | | | IV-1 | Zfp263 | | | 22383 | 3 | 4 | | | | IV-1 | Zfp608 | | |
| 22288 | 3 | 4 | | | | IV-1 | Zfp266 | | | 22384 | 3 | 4 | | | | IV-1 | Zfp61 | | |
| 22289 | 3 | 4 | | | | IV-1 | Zfp27 | | | 22385 | 3 | 4 | | | | IV-1 | Zfp617 | | |
| 22290 | 3 | 4 | | | | IV-1 | Zfp273 | | | 22386 | 3 | 4 | | | | IV-1 | Zfp62 | 643836 | 4-May-15 |
| 22291 | 3 | 4 | | | | IV-1 | Zfp275 | | | 22387 | 3 | 4 | | | | IV-1 | Zfp622 | | |
| 22292 | 3 | 4 | | | | IV-1 | Zfp277 | | | 22388 | 3 | 4 | | | | IV-1 | Zfp623 | | |
| 22293 | 3 | 4 | | | | IV-1 | Zfp28 | 140612 | 12-May-15 | 22389 | 3 | 4 | | | | IV-1 | Zfp629 | | |
| 22294 | 3 | 4 | | | | IV-1 | Zfp280b | | | 22390 | 3 | 4 | | | | IV-1 | Zfp637 | | |
| 22295 | 3 | 4 | | | | IV-1 | Zfp280c | | | 22391 | 3 | 4 | | | | IV-1 | Zfp639 | | |
| 22296 | 3 | 4 | | | | IV-1 | Zfp281 | | | 22392 | 3 | 4 | | | | IV-1 | Zfp64 | 55734 | 4-May-15 |
| 22297 | 3 | 4 | | | | IV-1 | Zfp282 | | | 22393 | 3 | 4 | | | | IV-1 | Zfp644 | | |
| 22298 | 3 | 4 | | | | IV-1 | Zfp286 | | | 22394 | 3 | 4 | | | | IV-1 | Zfp651 | | |
| 22299 | 3 | 4 | | | | IV-1 | Zfp287 | | | 22395 | 3 | 4 | | | | IV-1 | Zfp652os | | |
| 22300 | 3 | 4 | | | | IV-1 | Zfp292 | 23036 | 28-May-15 | 22396 | 3 | 4 | | | | IV-1 | Zfp654 | | |
| 22301 | 3 | 4 | | | | IV-1 | Zfp296 | 162979 | 4-May-15 | 22397 | 3 | 4 | | | | IV-1 | Zfp655 | | |
| 22302 | 3 | 4 | | | | IV-1 | Zfp316 | | | 22398 | 3 | 4 | | | | IV-1 | Zfp658 | | |
| 22303 | 3 | 4 | | | | IV-1 | Zfp318 | 24149 | 4-May-15 | 22399 | 3 | 4 | | | | IV-1 | Zfp661 | 7549 | 12-May-15 |
| 22304 | 3 | 4 | | | | IV-1 | Zfp319 | 57567 | 4-May-15 | 22400 | 3 | 4 | | | | IV-1 | Zfp663 | | |
| 22305 | 3 | 4 | | | | IV-1 | Zfp322a | | | 22401 | 3 | 4 | | | | IV-1 | Zfp664 | | |
| 22306 | 3 | 4 | | | | IV-1 | Zfp324 | | | 22402 | 3 | 4 | | | | IV-1 | Zfp667 | | |
| 22307 | 3 | 4 | | | | IV-1 | Zfp329 | | | 22403 | 3 | 4 | | | | IV-1 | Zfp672 | | |
| 22308 | 3 | 4 | | | | IV-1 | Zfp330 | | | 22404 | 3 | 4 | | | | IV-1 | Zfp677 | | |
| 22309 | 3 | 4 | | | | IV-1 | Zfp335 | | | 22405 | 3 | 4 | | | | IV-1 | Zfp68 | | |
| 22310 | 3 | 4 | | | | IV-1 | Zfp341 | | | 22406 | 3 | 4 | | | | IV-1 | Zfp687 | | |
| 22311 | 3 | 4 | | | | IV-1 | Zfp345 | | | 22407 | 3 | 4 | | | | IV-1 | Zfp688 | | |
| 22312 | 3 | 4 | | | | IV-1 | Zfp346 | 23967 | 21-May-15 | 22408 | 3 | 4 | | | | IV-1 | Zfp689 | | |
| 22313 | 3 | 4 | | | | IV-1 | Zfp35 | | | 22409 | 3 | 4 | | | | IV-1 | Zfp703 | | |
| 22314 | 3 | 4 | | | | IV-1 | Zfp352 | | | 22410 | 3 | 4 | | | | IV-1 | Zfp706 | | |
| 22315 | 3 | 4 | | | | IV-1 | Zfp354a | | | 22411 | 3 | 4 | | | | IV-1 | Zfp708 | | |
| 22316 | 3 | 4 | | | | IV-1 | Zfp354b | | | 22412 | 3 | 4 | | | | IV-1 | Zfp709 | | |
| 22317 | 3 | 4 | | | | IV-1 | Zfp36l1 | 677 | 4-May-15 | 22413 | 3 | 4 | | | | IV-1 | Zfp710 | | |
| 22318 | 3 | 4 | | | | IV-1 | Zfp36l2 | 678 | 4-May-15 | 22414 | 3 | 4 | | | | IV-1 | Zfp712 | | |
| 22319 | 3 | 4 | | | | IV-1 | Zfp37 | 7539 | 4-May-15 | 22415 | 3 | 4 | | | | IV-1 | Zfp715 | | |
| 22320 | 3 | 4 | | | | IV-1 | Zfp384 | | | 22416 | 3 | 4 | | | | IV-1 | Zfp719 | | |
| 22321 | 3 | 4 | | | | IV-1 | Zfp385a | | | 22417 | 3 | 4 | | | | IV-1 | Zfp72 | | |
| 22322 | 3 | 4 | | | | IV-1 | Zfp385b | | | 22418 | 3 | 4 | | | | IV-1 | Zfp735 | | |
| 22323 | 3 | 4 | | | | IV-1 | Zfp386 | | | 22419 | 3 | 4 | | | | IV-1 | Zfp738 | | |
| 22324 | 3 | 4 | | | | IV-1 | Zfp39 | | | 22420 | 3 | 4 | | | | IV-1 | Zfp74 | | |

Fig. 30 - 119

| | | | | | | | | | | | |
|---|---|---|---|---|---|---|---|---|---|---|---|
| 22421 | 3 | 4 | | | | IV-1 | Zfp740 | 283337 | 4-May-15 |
| 22422 | 3 | 4 | | | | IV-1 | Zfp746 | | |
| 22423 | 3 | 4 | | | | IV-1 | Zfp747 | | |
| 22424 | 3 | 4 | | | | IV-1 | Zfp748 | | |
| 22425 | 3 | 4 | | | | IV-1 | Zfp759 | | |
| 22426 | 3 | 4 | | | | IV-1 | Zfp768 | | |
| 22427 | 3 | 4 | | | | IV-1 | Zfp770 | | |
| 22428 | 3 | 4 | | | | IV-1 | Zfp772 | | |
| 22429 | 3 | 4 | | | | IV-1 | Zfp773 | | |
| 22430 | 3 | 4 | | | | IV-1 | Zfp775 | | |
| 22431 | 3 | 4 | | | | IV-1 | Zfp777 | | |
| 22432 | 3 | 4 | | | | IV-1 | Zfp78 | | |
| 22433 | 3 | 4 | | | | IV-1 | Zfp780b | | |
| 22434 | 3 | 4 | | | | IV-1 | Zfp781 | | |
| 22435 | 3 | 4 | | | | IV-1 | Zfp783 | | |
| 22436 | 3 | 4 | | | | IV-1 | Zfp786 | | |
| 22437 | 3 | 4 | | | | IV-1 | Zfp787 | | |
| 22438 | 3 | 4 | | | | IV-1 | Zfp788 | | |
| 22439 | 3 | 4 | | | | IV-1 | Zfp790 | | |
| 22440 | 3 | 4 | | | | IV-1 | Zfp804a | | |
| 22441 | 3 | 4 | | | | IV-1 | Zfp804b | | |
| 22442 | 3 | 4 | | | | IV-1 | Zfp808 | | |
| 22443 | 3 | 4 | | | | IV-1 | Zfp81 | | |
| 22444 | 3 | 4 | | | | IV-1 | Zfp810 | | |
| 22445 | 3 | 4 | | | | IV-1 | Zfp811 | | |
| 22446 | 3 | 4 | | | | IV-1 | Zfp82 | 284406 | 4-May-15 |
| 22447 | 3 | 4 | | | | IV-1 | Zfp820 | | |
| 22448 | 3 | 4 | | | | IV-1 | Zfp825 | | |
| 22449 | 3 | 4 | | | | IV-1 | Zfp827 | | |
| 22450 | 3 | 4 | | | | IV-1 | Zfp846 | | |
| 22451 | 3 | 4 | | | | IV-1 | Zfp85 | | |
| 22452 | 3 | 4 | | | | IV-1 | Zfp850 | | |
| 22453 | 3 | 4 | | | | IV-1 | Zfp862-ps | | |
| 22454 | 3 | 4 | | | | IV-1 | Zfp866 | | |
| 22455 | 3 | 4 | | | | IV-1 | Zfp867 | | |
| 22456 | 3 | 4 | | | | IV-1 | Zfp868 | | |
| 22457 | 3 | 4 | | | | IV-1 | Zfp87 | | |
| 22458 | 3 | 4 | | | | IV-1 | Zfp872 | | |
| 22459 | 3 | 4 | | | | IV-1 | Zfp874a | | |
| 22460 | 3 | 4 | | | | IV-1 | Zfp874b | | |
| 22461 | 3 | 4 | | | | IV-1 | Zfp882 | | |
| 22462 | 3 | 4 | | | | IV-1 | Zfp9 | 219749 | 4-May-15 |
| 22463 | 3 | 4 | | | | IV-1 | Zfp91 | 80829 | 4-May-15 |
| 22464 | 3 | 4 | | | | IV-1 | Zfp91Cntf | 386607 | 7-Jun-15 |
| 22465 | 3 | 4 | | | | IV-1 | Zfp92 | 139735 | 4-May-15 |
| 22466 | 3 | 4 | | | | IV-1 | Zfp93 | 9330 | 12-May-15 |
| 22467 | 3 | 4 | | | | IV-1 | Zfp930 | | |
| 22468 | 3 | 4 | | | | IV-1 | Zfp931 | | |
| 22469 | 3 | 4 | | | | IV-1 | Zfp932 | | |
| 22470 | 3 | 4 | | | | IV-1 | Zfp933 | | |
| 22471 | 3 | 4 | | | | IV-1 | Zfp934 | | |
| 22472 | 3 | 4 | | | | IV-1 | Zfp935 | | |
| 22473 | 3 | 4 | | | | IV-1 | Zfp936 | | |
| 22474 | 3 | 4 | | | | IV-1 | Zfp937 | | |
| 22475 | 3 | 4 | | | | IV-1 | Zfp939 | | |
| 22476 | 3 | 4 | | | | IV-1 | Zfp940 | | |
| 22477 | 3 | 4 | | | | IV-1 | Zfp942 | | |
| 22478 | 3 | 4 | | | | IV-1 | Zfp943 | | |
| 22479 | 3 | 4 | | | | IV-1 | Zfp944 | | |
| 22480 | 3 | 4 | | | | IV-1 | Zfp945 | | |
| 22481 | 3 | 4 | | | | IV-1 | Zfp946 | | |
| 22482 | 3 | 4 | | | | IV-1 | Zfp947 | | |
| 22483 | 3 | 4 | | | | IV-1 | Zfp953 | | |
| 22484 | 3 | 4 | | | | IV-1 | Zfp954 | | |
| 22485 | 3 | 4 | | | | IV-1 | Zfp955a | | |
| 22486 | 3 | 4 | | | | IV-1 | Zfp955b | | |
| 22487 | 3 | 4 | | | | IV-1 | Zfp956 | | |
| 22488 | 3 | 4 | | | | IV-1 | Zfp958 | | |
| 22489 | 3 | 4 | | | | IV-1 | Zfp959 | | |
| 22490 | 3 | 4 | | | | IV-1 | Zfp960 | | |
| 22491 | 3 | 4 | | | | IV-1 | Zfp963 | | |
| 22492 | 3 | 4 | | | | IV-1 | Zfp97 | | |
| 22493 | 3 | 4 | | | | IV-1 | Zfr2 | 23217 | 4-May-15 |
| 22494 | 3 | 4 | | | | IV-1 | Zfy1 | | |
| 22495 | 3 | 4 | | | | IV-1 | Zfy2 | | |
| 22496 | 3 | 4 | | | | IV-1 | Zfyve1 | 53349 | 21-May-15 |
| 22497 | 3 | 4 | | | | IV-1 | Zfyve19 | 84936 | 21-May-15 |
| 22498 | 3 | 4 | | | | IV-1 | Zfyve20 | 64145 | 12-May-15 |
| 22499 | 3 | 4 | | | | IV-1 | Zfyve27 | 118813 | 12-May-15 |
| 22500 | 3 | 4 | | | | IV-1 | Zhx2 | 22882 | 31-May-15 |
| 22501 | 3 | 4 | | | | IV-1 | Zhx3 | 23051 | 4-May-15 |
| 22502 | 3 | 4 | | | | IV-1 | Zic2 | 7546 | 2-Jun-15 |
| 22503 | 3 | 4 | | | | IV-1 | Zic3 | 7547 | 28-May-15 |
| 22504 | 3 | 4 | | | | IV-1 | Zic4 | 84107 | 4-May-15 |
| 22505 | 3 | 4 | | | | IV-1 | Zic5 | 85416 | 4-May-15 |
| 22506 | 3 | 4 | | | | IV-1 | Zik1 | 284307 | 4-May-15 |
| 22507 | 3 | 4 | | | | IV-1 | Zkscan1 | 7586 | 4-May-15 |
| 22508 | 3 | 4 | | | | IV-1 | Zkscan14 | 84124 | 21-May-15 |
| 22509 | 3 | 4 | | | | IV-1 | Zkscan16 | 158399 | 4-May-15 |
| 22510 | 3 | 4 | | | | IV-1 | Zkscan17 | 84838 | 28-May-15 |
| 22511 | 3 | 4 | | | | IV-1 | Zkscan2 | 342357 | 28-May-15 |
| 22512 | 3 | 4 | | | | IV-1 | Zkscan3 | 80317 | 4-May-15 |
| 22513 | 3 | 4 | | | | IV-1 | Zkscan4 | 387032 | 20-May-15 |
| 22514 | 3 | 4 | | | | IV-1 | Zkscan5 | 23660 | 12-May-15 |
| 22515 | 3 | 4 | | | | IV-1 | Zkscan6 | 7566 | 28-May-15 |
| 22516 | 3 | 4 | | | | IV-1 | Zkscan7 | 55888 | 4-May-15 |
| 22517 | 3 | 4 | | | | IV-1 | Zmat1 | 84460 | 4-May-15 |
| 22518 | 3 | 4 | | | | IV-1 | Zmat3 | 64393 | 4-May-15 |
| 22519 | 3 | 4 | | | | IV-1 | Zmat4 | 79698 | 2-Jun-15 |
| 22520 | 3 | 4 | | | | IV-1 | Zmat5 | 55954 | 2-Jun-15 |
| 22521 | 3 | 4 | | | | IV-1 | Zmiz1 | 57178 | 17-May-15 |
| 22522 | 3 | 4 | | | | IV-1 | Zmiz2 | 83637 | 4-May-15 |
| 22523 | 3 | 4 | | | | IV-1 | Zmpste24 | 10269 | 4-May-15 |
| 22524 | 3 | 4 | | | | IV-1 | Zmym1 | 79830 | 20-May-15 |
| 22525 | 3 | 4 | | | | IV-1 | Zmym2 | 7750 | 12-May-15 |
| 22526 | 3 | 4 | | | | IV-1 | Zmym3 | 9203 | 12-May-15 |
| 22527 | 3 | 4 | | | | IV-1 | Zmym4 | 9202 | 4-May-15 |
| 22528 | 3 | 4 | | | | IV-1 | Zmym5 | 9205 | 4-May-15 |
| 22529 | 3 | 4 | | | | IV-1 | Zmym6 | 9204 | 12-May-15 |
| 22530 | 3 | 4 | | | | IV-1 | Zmynd12 | 84217 | 4-May-15 |
| 22531 | 3 | 4 | | | | IV-1 | Znfx1 | 57169 | 4-May-15 |
| 22532 | 3 | 4 | | | | IV-1 | Znhit1 | 10467 | 4-May-15 |
| 22533 | 3 | 4 | | | | IV-1 | Znhit3 | 9326 | 4-May-15 |
| 22534 | 3 | 4 | | | | IV-1 | Znhit6 | 54680 | 4-May-15 |
| 22535 | 3 | 4 | | | | IV-1 | Znrd1as | 80862 | 12-May-15 |
| 22536 | 3 | 4 | | | | IV-1 | Znrf2 | 223082 | 23-May-15 |
| 22537 | 3 | 4 | | | | IV-1 | Znrf3 | 84133 | 23-May-15 |
| 22538 | 3 | 4 | | | | IV-1 | Zp1 | 22917 | 12-May-15 |
| 22539 | 3 | 4 | | | | IV-1 | Zp2 | 7783 | 4-May-15 |
| 22540 | 3 | 4 | | | | IV-1 | Zp3 | 7784 | 7-Jun-15 |
| 22541 | 3 | 4 | | | | IV-1 | Zp3r | | |
| 22542 | 3 | 4 | | | | IV-1 | Zp4-ps | | |
| 22543 | 3 | 4 | | | | IV-1 | Zpbp | 11055 | 4-May-15 |
| 22544 | 3 | 4 | | | | IV-1 | Zpbp2 | 124626 | 4-May-15 |
| 22545 | 3 | 4 | | | | IV-1 | Zpr1 | 8882 | 12-May-15 |
| 22546 | 3 | 4 | | | | IV-1 | Zranb2 | 9406 | 2-Jun-15 |
| 22547 | 3 | 4 | | | | IV-1 | Zscan10 | 84891 | 4-May-15 |
| 22548 | 3 | 4 | | | | IV-1 | Zscan12 | 9753 | 4-May-15 |
| 22549 | 3 | 4 | | | | IV-1 | Zscan26 | 7741 | 12-May-15 |
| 22550 | 3 | 4 | | | | IV-1 | Zscan29 | 146050 | 28-May-15 |
| 22551 | 3 | 4 | | | | IV-1 | Zscan4a | | |
| 22552 | 3 | 4 | | | | IV-1 | Zscan4b | | |
| 22553 | 3 | 4 | | | | IV-1 | Zscan4c | | |
| 22554 | 3 | 4 | | | | IV-1 | Zscan4d | | |
| 22555 | 3 | 4 | | | | IV-1 | Zscan4e | | |
| 22556 | 3 | 4 | | | | IV-1 | Zscan4f | | |
| 22557 | 3 | 4 | | | | IV-1 | Zscan5b | 342933 | 28-May-15 |
| 22558 | 3 | 4 | | | | IV-1 | Zswim6 | 57688 | 4-May-15 |
| 22559 | 3 | 4 | | | | IV-1 | Zufsp | 221302 | 4-May-15 |
| 22560 | 3 | 4 | | | | IV-1 | Zxdb | 158586 | 4-May-15 |
| 22561 | 3 | 4 | | | | IV-1 | Zxdc | 79364 | 4-May-15 |
| 22562 | 3 | 4 | | | | IV-1 | Zyx | 7791 | 4-May-15 |
| 22563 | 3 | 4 | | | | IV-1 | Zzz3 | 26009 | 21-May-15 |
| 22564 | 3 | | | | | | 1700065L07Rik | | |
| 22565 | 3 | | | | | | 1700092C02Rik | | |
| 22566 | 3 | | | | | | 2310007B03Rik | | |
| 22567 | 3 | | | | | | 2410021H03Rik | | |
| 22568 | 3 | | | | | | 2510003E04Rik | | |
| 22569 | 3 | | | | | | 2610044O15Rik | | |
| 22570 | 3 | | | | | | 2810471M01Rik | | |
| 22571 | 3 | | | | | | 4922502D21Rik | | |
| 22572 | 3 | | | | | | 4930430F08Rik | | |
| 22573 | 3 | | | | | | 4930440C22Rik | | |
| 22574 | 3 | | | | | | 4930455F16Rik | | |
| 22575 | 3 | | | | | | 4930486I03Rik | | |
| 22576 | 3 | | | | | | 4930502E18Rik | | |
| 22577 | 3 | | | | | | 4930503E24Rik | | |
| 22578 | 3 | | | | | | 4930519H02Rik | | |
| 22579 | 3 | | | | | | 4930544M13Rik | | |
| 22580 | 3 | | | | | | 4930552P12Rik | | |
| 22581 | 3 | | | | | | 4930565D16Rik | | |
| 22582 | 3 | | | | | | 4933402C06Rik | | |
| 22583 | 3 | | | | | | 4933409G03Rik | | |
| 22584 | 3 | | | | | | 4933433C11Rik | | |
| 22585 | 3 | | | | | | 4933433G15Rik | | |
| 22586 | 3 | | | | | | 4933440I02Rik | | |
| 22587 | 3 | | | | | | 5430401F13Rik | | |
| 22588 | 3 | | | | | | 5530601H04Rik | | |
| 22589 | 3 | | | | | | 5730412P04Rik | | |
| 22590 | 3 | | | | | | 6230400D17Rik | | |
| 22591 | 3 | | | | | | 8030423F21Rik | | |
| 22592 | 3 | | | | | | 8030462N17Rik | | |
| 22593 | 3 | | | | | | 8430422H06Rik | | |
| 22594 | 3 | | | | | | 8430423G03Rik | | |
| 22595 | 3 | | | | | | 9030625G05Rik | | |
| 22596 | 3 | | | | | | 9130019O22Rik | | |
| 22597 | 3 | | | | | | 9130221F21Rik | | |
| 22598 | 3 | | | | | | 9230102K24Rik | | |
| 22599 | 3 | | | | | | 9230116N13Rik | | |
| 22600 | 3 | | | | | | 9430018G01Rik | | |
| 22601 | 3 | | | | | | 9630033A20Rik | | |
| 22602 | 3 | | | | | | A230050P20Rik | | |
| 22603 | 3 | | | | | | A530072M11Rik | | |
| 22604 | 3 | | | | | | A730006G06Rik | | |
| 22605 | 3 | | | | | | A730082K24Rik | | |
| 22606 | 3 | | | | | | A830010M20Rik | | |
| 22607 | 3 | | | | | | Bad | 572 | 4-May-15 |
| 22608 | 3 | | | | | | BC089491 | | |

Fig. 30 - 120

| | | | | | | | | | | | | | | | |
|---|---|---|---|---|---|---|---|---|---|---|---|---|---|---|---|
| 22609 | 3 | | | | | Bpifb9a | | | 22704 | 3 | | | | | Olfr1048 |
| 22610 | 3 | | | | | C2cd2 | 25966 | 4-May-15 | 22705 | 3 | | | | | Olfr1049 |
| 22611 | 3 | | | | | Cryge | | | 22706 | 3 | | | | | Olfr1051 |
| 22612 | 3 | | | | | Csnk1e | 1454 | 4-May-15 | 22707 | 3 | | | | | Olfr1052 |
| 22613 | 3 | | | | | Csnk1g2 | 1455 | 4-May-15 | 22708 | 3 | | | | | Olfr1053 |
| 22614 | 3 | | | | | D830005E20Rik | | | 22709 | 3 | | | | | Olfr1054 |
| 22615 | 3 | | | | | Defb6 | | | 22710 | 3 | | | | | Olfr1055 |
| 22616 | 3 | | | | | Dxo | 1797 | 12-May-15 | 22711 | 3 | | | | | Olfr1056 |
| 22617 | 3 | | | | | E4f1 | 1877 | 23-May-15 | 22712 | 3 | | | | | Olfr1057 |
| 22618 | 3 | | | | | Gcdh | 2639 | 31-May-15 | 22713 | 3 | | | | | Olfr1058 |
| 22619 | 3 | | | | | Gm10415 | | | 22714 | 3 | | | | | Olfr1061 |
| 22620 | 3 | | | | | Gm1045 | | | 22715 | 3 | | | | | Olfr1062 |
| 22621 | 3 | | | | | Gm10509 | | | 22716 | 3 | | | | | Olfr1065 |
| 22622 | 3 | | | | | Gm10584 | | | 22717 | 3 | | | | | Olfr1066 |
| 22623 | 3 | | | | | Gm10635 | | | 22718 | 3 | | | | | Olfr107 |
| 22624 | 3 | | | | | Gm10636 | | | 22719 | 3 | | | | | Olfr1076 |
| 22625 | 3 | | | | | Gm10714 | | | 22720 | 3 | | | | | Olfr1077-ps1 |
| 22626 | 3 | | | | | Gm10745 | | | 22721 | 3 | | | | | Olfr1079 |
| 22627 | 3 | | | | | Gm10768 | | | 22722 | 3 | | | | | Olfr108 |
| 22628 | 3 | | | | | Gm11487 | | | 22723 | 3 | | | | | Olfr1080 |
| 22629 | 3 | | | | | Gm11538 | | | 22724 | 3 | | | | | Olfr1082 |
| 22630 | 3 | | | | | Gm11541 | | | 22725 | 3 | | | | | Olfr1084 |
| 22631 | 3 | | | | | Gm11992 | | | 22726 | 3 | | | | | Olfr1085 |
| 22632 | 3 | | | | | Gm12060 | | | 22727 | 3 | | | | | Olfr1086 |
| 22633 | 3 | | | | | Gm12633 | | | 22728 | 3 | | | | | Olfr1087 |
| 22634 | 3 | | | | | Gm12709 | | | 22729 | 3 | | | | | Olfr1089 |
| 22635 | 3 | | | | | Gm12888 | | | 22730 | 3 | | | | | Olfr109 |
| 22636 | 3 | | | | | Gm13031 | | | 22731 | 3 | | | | | Olfr1090 |
| 22637 | 3 | | | | | Gm13088 | | | 22732 | 3 | | | | | Olfr1093 |
| 22638 | 3 | | | | | Gm13102 | | | 22733 | 3 | | | | | Olfr1094 |
| 22639 | 3 | | | | | Gm13275 | | | 22734 | 3 | | | | | Olfr1095 |
| 22640 | 3 | | | | | Gm13286 | | | 22735 | 3 | | | | | Olfr1097 |
| 22641 | 3 | | | | | Gm13944 | | | 22736 | 3 | | | | | Olfr1098 |
| 22642 | 3 | | | | | Gm14391 | | | 22737 | 3 | | | | | Olfr1099 |
| 22643 | 3 | | | | | Gm14685 | | | 22738 | 3 | | | | | Olfr11 |
| 22644 | 3 | | | | | Gm1527 | | | 22739 | 3 | | | | | Olfr110 |
| 22645 | 3 | | | | | Gm16157 | | | 22740 | 3 | | | | | Olfr1100 |
| 22646 | 3 | | | | | Gm16386 | | | 22741 | 3 | | | | | Olfr1101 |
| 22647 | 3 | | | | | Gm16897 | | | 22742 | 3 | | | | | Olfr1102 |
| 22648 | 3 | | | | | Gm18853 | | | 22743 | 3 | | | | | Olfr1104 |
| 22649 | 3 | | | | | Gm19990 | | | 22744 | 3 | | | | | Olfr1105 |
| 22650 | 3 | | | | | Gm2027 | | | 22745 | 3 | | | | | Olfr1106 |
| 22651 | 3 | | | | | Gm2030 | | | 22746 | 3 | | | | | Olfr1107 |
| 22652 | 3 | | | | | Gm20735 | | | 22747 | 3 | | | | | Olfr1109 |
| 22653 | 3 | | | | | Gm20751 | | | 22748 | 3 | | | | | Olfr111 |
| 22654 | 3 | | | | | Gm20754 | | | 22749 | 3 | | | | | Olfr1110 |
| 22655 | 3 | | | | | Gm20757 | | | 22750 | 3 | | | | | Olfr1111 |
| 22656 | 3 | | | | | Gm20759 | | | 22751 | 3 | | | | | Olfr1112 |
| 22657 | 3 | | | | | Gm21704 | | | 22752 | 3 | | | | | Olfr1113 |
| 22658 | 3 | | | | | Gm2176 | | | 22753 | 3 | | | | | Olfr1115 |
| 22659 | 3 | | | | | Gm21943 | | | 22754 | 3 | | | | | Olfr1116-ps |
| 22660 | 3 | | | | | Gm3219 | | | 22755 | 3 | | | | | Olfr112 |
| 22661 | 3 | | | | | Gm3409 | | | 22756 | 3 | | | | | Olfr1120 |
| 22662 | 3 | | | | | Gm4278 | | | 22757 | 3 | | | | | Olfr1121 |
| 22663 | 3 | | | | | Gm428 | | | 22758 | 3 | | | | | Olfr1122 |
| 22664 | 3 | | | | | Gm4305 | | | 22759 | 3 | | | | | Olfr1123 |
| 22665 | 3 | | | | | Gm4745 | | | 22760 | 3 | | | | | Olfr1124 |
| 22666 | 3 | | | | | Gm4776 | | | 22761 | 3 | | | | | Olfr1126 |
| 22667 | 3 | | | | | Gm4787 | | | 22762 | 3 | | | | | Olfr1129 |
| 22668 | 3 | | | | | Gm4792 | | | 22763 | 3 | | | | | Olfr113 |
| 22669 | 3 | | | | | Gm4858 | | | 22764 | 3 | | | | | Olfr1130 |
| 22670 | 3 | | | | | Gm4906 | | | 22765 | 3 | | | | | Olfr1131 |
| 22671 | 3 | | | | | Gm4907 | | | 22766 | 3 | | | | | Olfr1132 |
| 22672 | 3 | | | | | Gm5072 | | | 22767 | 3 | | | | | Olfr1133 |
| 22673 | 3 | | | | | Gm5083 | | | 22768 | 3 | | | | | Olfr1134 |
| 22674 | 3 | | | | | Gm5347 | | | 22769 | 3 | | | | | Olfr1135 |
| 22675 | 3 | | | | | Gm5795 | | | 22770 | 3 | | | | | Olfr1137 |
| 22676 | 3 | | | | | Gm5935 | | | 22771 | 3 | | | | | Olfr1138 |
| 22677 | 3 | | | | | Gm595 | | | 22772 | 3 | | | | | Olfr114 |
| 22678 | 3 | | | | | Gm6086 | | | 22773 | 3 | | | | | Olfr1140 |
| 22679 | 3 | | | | | Gm6213 | | | 22774 | 3 | | | | | Olfr1141 |
| 22680 | 3 | | | | | Gm6289 | | | 22775 | 3 | | | | | Olfr1143 |
| 22681 | 3 | | | | | Gm6408 | | | 22776 | 3 | | | | | Olfr1145 |
| 22682 | 3 | | | | | Gm711 | | | 22777 | 3 | | | | | Olfr1148 |
| 22683 | 3 | | | | | Gm7849 | | | 22778 | 3 | | | | | Olfr115 |
| 22684 | 3 | | | | | Gm8300 | | | 22779 | 3 | | | | | Olfr1152 |
| 22685 | 3 | | | | | Gm884 | | | 22780 | 3 | | | | | Olfr1153 |
| 22686 | 3 | | | | | Gm9767 | | | 22781 | 3 | | | | | Olfr1154 |
| 22687 | 3 | | | | | Klrg2 | 346689 | 4-May-15 | 22782 | 3 | | | | | Olfr1155 |
| 22688 | 3 | | | | | Mir463 | | | 22783 | 3 | | | | | Olfr1157 |
| 22689 | 3 | | | | | Mir465 | | | 22784 | 3 | | | | | Olfr1158 |
| 22690 | 3 | | | | | Mir465c-2 | | | 22785 | 3 | | | | | Olfr116 |
| 22691 | 3 | | | | | Mir466 | 100423038 | 4-May-15 | 22786 | 3 | | | | | Olfr1160 |
| | | | | | | | | | 22787 | 3 | | | | | Olfr1161 |
| 22692 | 3 | | | | | Mir467a-1 | | | 22788 | 3 | | | | | Olfr1162 |
| 22693 | 3 | | | | | Mir467a-9 | | | 22789 | 3 | | | | | Olfr1163 |
| 22694 | 3 | | | | | Mir483 | 619552 | 24-May-15 | 22790 | 3 | | | | | Olfr1166 |
| 22695 | 3 | | | | | Mir592 | 693177 | 21-May-15 | 22791 | 3 | | | | | Olfr1168 |
| 22696 | 3 | | | | | Mir6380 | | | 22792 | 3 | | | | | Olfr117 |
| 22697 | 3 | | | | | Mir742 | | | 22793 | 3 | | | | | Olfr1170 |
| 22698 | 3 | | | | | Nlrp5-ps | | | 22794 | 3 | | | | | Olfr1173 |
| 22699 | 3 | | | | | Nob1 | 28987 | 17-May-15 | 22795 | 3 | | | | | Olfr1176 |
| 22700 | 3 | | | | | Olfr1015 | | | 22796 | 3 | | | | | Olfr1178 |
| 22701 | 3 | | | | | Olfr1045 | | | 22797 | 3 | | | | | Olfr118 |
| 22702 | 3 | | | | | Olfr1046 | | | 22798 | 3 | | | | | Olfr1180 |
| 22703 | 3 | | | | | Olfr1047 | | | 22799 | 3 | | | | | Olfr1181 |

Fig. 30 - 121

| | | | |
|---|---|---|---|
| 22800 | 3 | Olfr1182 | |
| 22801 | 3 | Olfr1183 | |
| 22802 | 3 | Olfr1184 | |
| 22803 | 3 | Olfr1186 | |
| 22804 | 3 | Olfr1188 | |
| 22805 | 3 | Olfr1189 | |
| 22806 | 3 | Olfr1193 | |
| 22807 | 3 | Olfr1195 | |
| 22808 | 3 | Olfr1196 | |
| 22809 | 3 | Olfr1197 | |
| 22810 | 3 | Olfr1198 | |
| 22811 | 3 | Olfr1199 | |
| 22812 | 3 | Olfr12 | |
| 22813 | 3 | Olfr120 | |
| 22814 | 3 | Olfr1200 | |
| 22815 | 3 | Olfr1201 | |
| 22816 | 3 | Olfr1202 | |
| 22817 | 3 | Olfr1204 | |
| 22818 | 3 | Olfr1205 | |
| 22819 | 3 | Olfr1206 | |
| 22820 | 3 | Olfr1209 | |
| 22821 | 3 | Olfr121 | |
| 22822 | 3 | Olfr1211 | |
| 22823 | 3 | Olfr1212 | |
| 22824 | 3 | Olfr1213 | |
| 22825 | 3 | Olfr1214 | |
| 22826 | 3 | Olfr1215 | |
| 22827 | 3 | Olfr1216 | |
| 22828 | 3 | Olfr1217 | |
| 22829 | 3 | Olfr1218 | |
| 22830 | 3 | Olfr1219 | |
| 22831 | 3 | Olfr122 | |
| 22832 | 3 | Olfr1220 | |
| 22833 | 3 | Olfr1221 | |
| 22834 | 3 | Olfr1222 | |
| 22835 | 3 | Olfr1223 | |
| 22836 | 3 | Olfr1225 | |
| 22837 | 3 | Olfr1226 | |
| 22838 | 3 | Olfr1228 | |
| 22839 | 3 | Olfr1229 | |
| 22840 | 3 | Olfr123 | |
| 22841 | 3 | Olfr1230 | |
| 22842 | 3 | Olfr1231 | |
| 22843 | 3 | Olfr1232 | |
| 22844 | 3 | Olfr1233 | |
| 22845 | 3 | Olfr1234 | |
| 22846 | 3 | Olfr1238 | |
| 22847 | 3 | Olfr1239 | |
| 22848 | 3 | Olfr124 | |
| 22849 | 3 | Olfr1240 | |
| 22850 | 3 | Olfr1241 | |
| 22851 | 3 | Olfr1242 | |
| 22852 | 3 | Olfr1243 | |
| 22853 | 3 | Olfr1245 | |
| 22854 | 3 | Olfr1246 | |
| 22855 | 3 | Olfr1247 | |
| 22856 | 3 | Olfr1248 | |
| 22857 | 3 | Olfr1249 | |
| 22858 | 3 | Olfr125 | |
| 22859 | 3 | Olfr1250 | |
| 22860 | 3 | Olfr1251 | |
| 22861 | 3 | Olfr1252 | |
| 22862 | 3 | Olfr1253 | |
| 22863 | 3 | Olfr1254 | |
| 22864 | 3 | Olfr1255 | |
| 22865 | 3 | Olfr1256 | |
| 22866 | 3 | Olfr1257 | |
| 22867 | 3 | Olfr1258 | |
| 22868 | 3 | Olfr1259 | |
| 22869 | 3 | Olfr126 | |
| 22870 | 3 | Olfr1260 | |
| 22871 | 3 | Olfr1261 | |
| 22872 | 3 | Olfr1262 | |
| 22873 | 3 | Olfr1263 | |
| 22874 | 3 | Olfr1264 | |
| 22875 | 3 | Olfr1265 | |
| 22876 | 3 | Olfr1269 | |
| 22877 | 3 | Olfr127 | |
| 22878 | 3 | Olfr1270 | |
| 22879 | 3 | Olfr1271 | |
| 22880 | 3 | Olfr1272 | |
| 22881 | 3 | Olfr1273-ps | |
| 22882 | 3 | Olfr1274-ps | |
| 22883 | 3 | Olfr1275 | |
| 22884 | 3 | Olfr1277 | |
| 22885 | 3 | Olfr1278 | |
| 22886 | 3 | Olfr1279 | |
| 22887 | 3 | Olfr128 | |
| 22888 | 3 | Olfr1280 | |
| 22889 | 3 | Olfr1281 | |
| 22890 | 3 | Olfr1282 | |
| 22891 | 3 | Olfr1283 | |
| 22892 | 3 | Olfr1284 | |
| 22893 | 3 | Olfr1286 | |
| 22894 | 3 | Olfr1288 | |
| 22895 | 3 | Olfr1289 | |
| 22896 | 3 | Olfr129 | |
| 22897 | 3 | Olfr1290 | |
| 22898 | 3 | Olfr1294 | |
| 22899 | 3 | Olfr1295 | |
| 22900 | 3 | Olfr1297 | |
| 22901 | 3 | Olfr1298 | |
| 22902 | 3 | Olfr1299 | |
| 22903 | 3 | Olfr13 | |
| 22904 | 3 | Olfr130 | |
| 22905 | 3 | Olfr1300-ps1 | |
| 22906 | 3 | Olfr1302 | |
| 22907 | 3 | Olfr1303 | |
| 22908 | 3 | Olfr1305 | |
| 22909 | 3 | Olfr1307 | |
| 22910 | 3 | Olfr1308 | |
| 22911 | 3 | Olfr1309 | |
| 22912 | 3 | Olfr1310 | |
| 22913 | 3 | Olfr1311 | |
| 22914 | 3 | Olfr1312 | |
| 22915 | 3 | Olfr1313 | |
| 22916 | 3 | Olfr1314 | |
| 22917 | 3 | Olfr1316 | |
| 22918 | 3 | Olfr1317 | |
| 22919 | 3 | Olfr1318 | |
| 22920 | 3 | Olfr132 | |
| 22921 | 3 | Olfr1320 | |
| 22922 | 3 | Olfr1322 | |
| 22923 | 3 | Olfr1323 | |
| 22924 | 3 | Olfr1324 | |
| 22925 | 3 | Olfr1325 | |
| 22926 | 3 | Olfr1328 | |
| 22927 | 3 | Olfr1329 | |
| 22928 | 3 | Olfr133 | |
| 22929 | 3 | Olfr1330 | |
| 22930 | 3 | Olfr1331 | |
| 22931 | 3 | Olfr1333 | |
| 22932 | 3 | Olfr1335 | |
| 22933 | 3 | Olfr1336 | |
| 22934 | 3 | Olfr1337 | |
| 22935 | 3 | Olfr134 | |
| 22936 | 3 | Olfr1341 | |
| 22937 | 3 | Olfr1347 | |
| 22938 | 3 | Olfr1348 | |
| 22939 | 3 | Olfr1349 | |
| 22940 | 3 | Olfr135 | |
| 22941 | 3 | Olfr1352 | |
| 22942 | 3 | Olfr1353 | |
| 22943 | 3 | Olfr1354 | |
| 22944 | 3 | Olfr1355 | |
| 22945 | 3 | Olfr1356 | |
| 22946 | 3 | Olfr1357 | |
| 22947 | 3 | Olfr1359 | |
| 22948 | 3 | Olfr136 | |
| 22949 | 3 | Olfr1360 | |
| 22950 | 3 | Olfr1361 | |
| 22951 | 3 | Olfr1362 | |
| 22952 | 3 | Olfr1364 | |
| 22953 | 3 | Olfr1366 | |
| 22954 | 3 | Olfr1367 | |
| 22955 | 3 | Olfr1368 | |
| 22956 | 3 | Olfr137 | |
| 22957 | 3 | Olfr1370 | |
| 22958 | 3 | Olfr1371 | |
| 22959 | 3 | Olfr1372-ps1 | |
| 22960 | 3 | Olfr1377 | |
| 22961 | 3 | Olfr1378 | |
| 22962 | 3 | Olfr138 | |
| 22963 | 3 | Olfr1380 | |
| 22964 | 3 | Olfr1383 | |
| 22965 | 3 | Olfr1384 | |
| 22966 | 3 | Olfr1385 | |
| 22967 | 3 | Olfr1386 | |
| 22968 | 3 | Olfr1389 | |
| 22969 | 3 | Olfr1391 | |
| 22970 | 3 | Olfr1392 | |
| 22971 | 3 | Olfr1393 | |
| 22972 | 3 | Olfr1394 | |
| 22973 | 3 | Olfr1395 | |
| 22974 | 3 | Olfr1402 | |
| 22975 | 3 | Olfr1404 | |
| 22976 | 3 | Olfr1406 | |
| 22977 | 3 | Olfr1408 | |
| 22978 | 3 | Olfr141 | |
| 22979 | 3 | Olfr1411 | |
| 22980 | 3 | Olfr1412 | |
| 22981 | 3 | Olfr1413 | |
| 22982 | 3 | Olfr1414 | |
| 22983 | 3 | Olfr1415 | |
| 22984 | 3 | Olfr1416 | |
| 22985 | 3 | Olfr1417 | |
| 22986 | 3 | Olfr1418 | |
| 22987 | 3 | Olfr1420 | |
| 22988 | 3 | Olfr1423 | |
| 22989 | 3 | Olfr1424 | |
| 22990 | 3 | Olfr1425 | |
| 22991 | 3 | Olfr1426 | |

Fig. 30 - 122

| | | | | | | | | | | | | | | | | | | | | |
|---|---|---|---|---|---|---|---|---|---|---|---|---|---|---|---|---|---|---|---|---|
| 22992 | 3 | | | | | Olfr1427 | | | | | 23088 | 3 | | | | | Olfr198 | | | |
| 22993 | 3 | | | | | Olfr1428 | | | | | 23089 | 3 | | | | | Olfr199 | | | |
| 22994 | 3 | | | | | Olfr1433 | | | | | 23090 | 3 | | | | | Olfr2 | | 7932 | 4-May-15 |
| 22995 | 3 | | | | | Olfr1434 | | | | | 23091 | 3 | | | | | Olfr201 | | | |
| 22996 | 3 | | | | | Olfr1436 | | | | | 23092 | 3 | | | | | Olfr202 | | | |
| 22997 | 3 | | | | | Olfr1437 | | | | | 23093 | 3 | | | | | Olfr203 | | | |
| 22998 | 3 | | | | | Olfr1440 | | | | | 23094 | 3 | | | | | Olfr204 | | | |
| 22999 | 3 | | | | | Olfr1441 | | | | | 23095 | 3 | | | | | Olfr207 | | | |
| 23000 | 3 | | | | | Olfr1442 | | | | | 23096 | 3 | | | | | Olfr211 | | | |
| 23001 | 3 | | | | | Olfr1443 | | | | | 23097 | 3 | | | | | Olfr212 | | | |
| 23002 | 3 | | | | | Olfr1444 | | | | | 23098 | 3 | | | | | Olfr213 | | | |
| 23003 | 3 | | | | | Olfr1446 | | | | | 23099 | 3 | | | | | Olfr214 | | | |
| 23004 | 3 | | | | | Olfr1447 | | | | | 23100 | 3 | | | | | Olfr215 | | | |
| 23005 | 3 | | | | | Olfr1449 | | | | | 23101 | 3 | | | | | Olfr218 | | | |
| 23006 | 3 | | | | | Olfr145 | | | | | 23102 | 3 | | | | | Olfr220 | | | |
| 23007 | 3 | | | | | Olfr1451 | | | | | 23103 | 3 | | | | | Olfr221 | | | |
| 23008 | 3 | | | | | Olfr1453 | | | | | 23104 | 3 | | | | | Olfr223 | | | |
| 23009 | 3 | | | | | Olfr1454 | | | | | 23105 | 3 | | | | | Olfr224 | | | |
| 23010 | 3 | | | | | Olfr1457 | | | | | 23106 | 3 | | | | | Olfr228 | | | |
| 23011 | 3 | | | | | Olfr1459 | | | | | 23107 | 3 | | | | | Olfr229 | | | |
| 23012 | 3 | | | | | Olfr146 | | | | | 23108 | 3 | | | | | Olfr23 | | | |
| 23013 | 3 | | | | | Olfr1462 | | | | | 23109 | 3 | | | | | Olfr231 | | | |
| 23014 | 3 | | | | | Olfr1463 | | | | | 23110 | 3 | | | | | Olfr235 | | | |
| 23015 | 3 | | | | | Olfr1465 | | | | | 23111 | 3 | | | | | Olfr237-ps1 | | | |
| 23016 | 3 | | | | | Olfr1466 | | | | | 23112 | 3 | | | | | Olfr239 | | | |
| 23017 | 3 | | | | | Olfr1467 | | | | | 23113 | 3 | | | | | Olfr242 | | | |
| 23018 | 3 | | | | | Olfr1469 | | | | | 23114 | 3 | | | | | Olfr247 | | | |
| 23019 | 3 | | | | | Olfr147 | | | | | 23115 | 3 | | | | | Olfr248 | | | |
| 23020 | 3 | | | | | Olfr1471 | | | | | 23116 | 3 | | | | | Olfr251 | | | |
| 23021 | 3 | | | | | Olfr1472 | | | | | 23117 | 3 | | | | | Olfr259 | | | |
| 23022 | 3 | | | | | Olfr1474 | | | | | 23118 | 3 | | | | | Olfr26 | | | |
| 23023 | 3 | | | | | Olfr1475 | | | | | 23119 | 3 | | | | | Olfr262 | | | |
| 23024 | 3 | | | | | Olfr1477 | | | | | 23120 | 3 | | | | | Olfr266 | | | |
| 23025 | 3 | | | | | Olfr148 | | | | | 23121 | 3 | | | | | Olfr27 | | | |
| 23026 | 3 | | | | | Olfr1480 | | | | | 23122 | 3 | | | | | Olfr270 | | | |
| 23027 | 3 | | | | | Olfr1484 | | | | | 23123 | 3 | | | | | Olfr272 | | | |
| 23028 | 3 | | | | | Olfr1487 | | | | | 23124 | 3 | | | | | Olfr273 | | | |
| 23029 | 3 | | | | | Olfr1489 | | | | | 23125 | 3 | | | | | Olfr275 | | | |
| 23030 | 3 | | | | | Olfr149 | | | | | 23126 | 3 | | | | | Olfr279 | | | |
| 23031 | 3 | | | | | Olfr1490 | | | | | 23127 | 3 | | | | | Olfr281 | | | |
| 23032 | 3 | | | | | Olfr1491 | | | | | 23128 | 3 | | | | | Olfr282 | | | |
| 23033 | 3 | | | | | Olfr1494 | | | | | 23129 | 3 | | | | | Olfr284 | | | |
| 23034 | 3 | | | | | Olfr1495 | | | | | 23130 | 3 | | | | | Olfr285 | | | |
| 23035 | 3 | | | | | Olfr1496 | | | | | 23131 | 3 | | | | | Olfr287 | | | |
| 23036 | 3 | | | | | Olfr1497 | | | | | 23132 | 3 | | | | | Olfr288 | | | |
| 23037 | 3 | | | | | Olfr1499 | | | | | 23133 | 3 | | | | | Olfr290 | | | |
| 23038 | 3 | | | | | Olfr15 | | | | | 23134 | 3 | | | | | Olfr291 | | | |
| 23039 | 3 | | | | | Olfr150 | | | | | 23135 | 3 | | | | | Olfr292 | | | |
| 23040 | 3 | | | | | Olfr1501 | | | | | 23136 | 3 | | | | | Olfr293 | | | |
| 23041 | 3 | | | | | Olfr1502 | | | | | 23137 | 3 | | | | | Olfr294 | | | |
| 23042 | 3 | | | | | Olfr1504 | | | | | 23138 | 3 | | | | | Olfr295 | | | |
| 23043 | 3 | | | | | Olfr1505 | | | | | 23139 | 3 | | | | | Olfr299 | | | |
| 23044 | 3 | | | | | Olfr1507 | | | | | 23140 | 3 | | | | | Olfr29-ps1 | | | |
| 23045 | 3 | | | | | Olfr1508 | | | | | 23141 | 3 | | | | | Olfr3 | | | |
| 23046 | 3 | | | | | Olfr1509 | | | | | 23142 | 3 | | | | | Olfr30 | | | |
| 23047 | 3 | | | | | Olfr151 | | | | | 23143 | 3 | | | | | Olfr301 | | | |
| 23048 | 3 | | | | | Olfr1510 | | | | | 23144 | 3 | | | | | Olfr303 | | | |
| 23049 | 3 | | | | | Olfr1511 | | | | | 23145 | 3 | | | | | Olfr304 | | | |
| 23050 | 3 | | | | | Olfr1512 | | | | | 23146 | 3 | | | | | Olfr305 | | | |
| 23051 | 3 | | | | | Olfr152 | | | | | 23147 | 3 | | | | | Olfr307 | | | |
| 23052 | 3 | | | | | Olfr153 | | | | | 23148 | 3 | | | | | Olfr308 | | | |
| 23053 | 3 | | | | | Olfr1532-ps1 | | | | | 23149 | 3 | | | | | Olfr309 | | | |
| 23054 | 3 | | | | | Olfr1535 | | | | | 23150 | 3 | | | | | Olfr31 | | | |
| 23055 | 3 | | | | | Olfr1537 | | | | | 23151 | 3 | | | | | Olfr311 | | | |
| 23056 | 3 | | | | | Olfr154 | | | | | 23152 | 3 | | | | | Olfr312 | | | |
| 23057 | 3 | | | | | Olfr155 | | | | | 23153 | 3 | | | | | Olfr313 | | | |
| 23058 | 3 | | | | | Olfr156 | | | | | 23154 | 3 | | | | | Olfr315 | | | |
| 23059 | 3 | | | | | Olfr157 | | | | | 23155 | 3 | | | | | Olfr316 | | | |
| 23060 | 3 | | | | | Olfr159 | | | | | 23156 | 3 | | | | | Olfr317 | | | |
| 23061 | 3 | | | | | Olfr16 | | | | | 23157 | 3 | | | | | Olfr318 | | | |
| 23062 | 3 | | | | | Olfr160 | | | | | 23158 | 3 | | | | | Olfr319 | | | |
| 23063 | 3 | | | | | Olfr161 | | | | | 23159 | 3 | | | | | Olfr32 | | | |
| 23064 | 3 | | | | | Olfr164 | | | | | 23160 | 3 | | | | | Olfr320 | | | |
| 23065 | 3 | | | | | Olfr166 | | | | | 23161 | 3 | | | | | Olfr322 | | | |
| 23066 | 3 | | | | | Olfr167 | | | | | 23162 | 3 | | | | | Olfr323 | | | |
| 23067 | 3 | | | | | Olfr168 | | | | | 23163 | 3 | | | | | Olfr324 | | | |
| 23068 | 3 | | | | | Olfr169 | | | | | 23164 | 3 | | | | | Olfr325 | | | |
| 23069 | 3 | | | | | Olfr17 | | | | | 23165 | 3 | | | | | Olfr328 | | | |
| 23070 | 3 | | | | | Olfr171 | | | | | 23166 | 3 | | | | | Olfr33 | | | |
| 23071 | 3 | | | | | Olfr172 | | | | | 23167 | 3 | | | | | Olfr330 | | | |
| 23072 | 3 | | | | | Olfr173 | | | | | 23168 | 3 | | | | | Olfr331 | | | |
| 23073 | 3 | | | | | Olfr175-ps1 | | | | | 23169 | 3 | | | | | Olfr332 | | | |
| 23074 | 3 | | | | | Olfr176 | | | | | 23170 | 3 | | | | | Olfr338 | | | |
| 23075 | 3 | | | | | Olfr177 | | | | | 23171 | 3 | | | | | Olfr339 | | | |
| 23076 | 3 | | | | | Olfr178 | | | | | 23172 | 3 | | | | | Olfr340 | | | |
| 23077 | 3 | | | | | Olfr18 | | | | | 23173 | 3 | | | | | Olfr341 | | | |
| 23078 | 3 | | | | | Olfr180 | | | | | 23174 | 3 | | | | | Olfr342 | | | |
| 23079 | 3 | | | | | Olfr181 | | | | | 23175 | 3 | | | | | Olfr344 | | | |
| 23080 | 3 | | | | | Olfr186 | | | | | 23176 | 3 | | | | | Olfr345 | | | |
| 23081 | 3 | | | | | Olfr187 | | | | | 23177 | 3 | | | | | Olfr346 | | | |
| 23082 | 3 | | | | | Olfr19 | | | | | 23178 | 3 | | | | | Olfr347 | | | |
| 23083 | 3 | | | | | Olfr191 | | | | | 23179 | 3 | | | | | Olfr348 | | | |
| 23084 | 3 | | | | | Olfr192 | | | | | 23180 | 3 | | | | | Olfr351 | | | |
| 23085 | 3 | | | | | Olfr193 | | | | | 23181 | 3 | | | | | Olfr352 | | | |
| 23086 | 3 | | | | | Olfr194 | | | | | 23182 | 3 | | | | | Olfr353 | | | |
| 23087 | 3 | | | | | Olfr197 | | | | | 23183 | 3 | | | | | Olfr355 | | | |

Fig. 30 - 123

| | | | | | | | | | | | | | | | | | | | | |
|---|---|---|---|---|---|---|---|---|---|---|---|---|---|---|---|---|---|---|---|---|
| 23184 | 3 | | | | | Olfr357 | | | 23280 | 3 | | | | | Olfr493 | | |
| 23185 | 3 | | | | | Olfr358 | | | 23281 | 3 | | | | | Olfr494 | | |
| 23186 | 3 | | | | | Olfr360 | | | 23282 | 3 | | | | | Olfr495 | | |
| 23187 | 3 | | | | | Olfr361 | | | 23283 | 3 | | | | | Olfr497 | | |
| 23188 | 3 | | | | | Olfr362 | | | 23284 | 3 | | | | | Olfr498 | | |
| 23189 | 3 | | | | | Olfr365 | | | 23285 | 3 | | | | | Olfr5 | | |
| 23190 | 3 | | | | | Olfr366 | | | 23286 | 3 | | | | | Olfr50 | | |
| 23191 | 3 | | | | | Olfr368 | | | 23287 | 3 | | | | | Olfr502 | | |
| 23192 | 3 | | | | | Olfr370 | | | 23288 | 3 | | | | | Olfr503 | | |
| 23193 | 3 | | | | | Olfr371 | | | 23289 | 3 | | | | | Olfr504 | | |
| 23194 | 3 | | | | | Olfr372 | | | 23290 | 3 | | | | | Olfr506 | | |
| 23195 | 3 | | | | | Olfr374 | | | 23291 | 3 | | | | | Olfr507 | | |
| 23196 | 3 | | | | | Olfr376 | | | 23292 | 3 | | | | | Olfr508 | | |
| 23197 | 3 | | | | | Olfr378 | | | 23293 | 3 | | | | | Olfr509 | | |
| 23198 | 3 | | | | | Olfr38 | | | 23294 | 3 | | | | | Olfr51 | | |
| 23199 | 3 | | | | | Olfr380 | | | 23295 | 3 | | | | | Olfr510 | | |
| 23200 | 3 | | | | | Olfr381 | | | 23296 | 3 | | | | | Olfr512 | | |
| 23201 | 3 | | | | | Olfr382 | | | 23297 | 3 | | | | | Olfr513 | | |
| 23202 | 3 | | | | | Olfr384 | | | 23298 | 3 | | | | | Olfr514 | | |
| 23203 | 3 | | | | | Olfr385 | | | 23299 | 3 | | | | | Olfr516 | | |
| 23204 | 3 | | | | | Olfr389 | | | 23300 | 3 | | | | | Olfr517 | | |
| 23205 | 3 | | | | | Olfr39 | | | 23301 | 3 | | | | | Olfr518 | | |
| 23206 | 3 | | | | | Olfr390 | | | 23302 | 3 | | | | | Olfr519 | | |
| 23207 | 3 | | | | | Olfr391-ps | | | 23303 | 3 | | | | | Olfr52 | | |
| 23208 | 3 | | | | | Olfr392 | | | 23304 | 3 | | | | | Olfr520 | | |
| 23209 | 3 | | | | | Olfr393 | | | 23305 | 3 | | | | | Olfr521 | | |
| 23210 | 3 | | | | | Olfr394 | | | 23306 | 3 | | | | | Olfr522 | | |
| 23211 | 3 | | | | | Olfr395 | | | 23307 | 3 | | | | | Olfr523 | | |
| 23212 | 3 | | | | | Olfr397 | | | 23308 | 3 | | | | | Olfr525 | | |
| 23213 | 3 | | | | | Olfr398 | | | 23309 | 3 | | | | | Olfr527 | | |
| 23214 | 3 | | | | | Olfr399 | | | 23310 | 3 | | | | | Olfr53 | | |
| 23215 | 3 | | | | | Olfr401 | | | 23311 | 3 | | | | | Olfr530 | | |
| 23216 | 3 | | | | | Olfr402 | | | 23312 | 3 | | | | | Olfr531 | | |
| 23217 | 3 | | | | | Olfr403 | | | 23313 | 3 | | | | | Olfr532 | | |
| 23218 | 3 | | | | | Olfr406 | | | 23314 | 3 | | | | | Olfr533 | | |
| 23219 | 3 | | | | | Olfr410 | | | 23315 | 3 | | | | | Olfr535 | | |
| 23220 | 3 | | | | | Olfr411 | | | 23316 | 3 | | | | | Olfr536 | | |
| 23221 | 3 | | | | | Olfr414 | | | 23317 | 3 | | | | | Olfr538 | | |
| 23222 | 3 | | | | | Olfr417 | | | 23318 | 3 | | | | | Olfr539 | | |
| 23223 | 3 | | | | | Olfr418-ps1 | | | 23319 | 3 | | | | | Olfr54 | | |
| 23224 | 3 | | | | | Olfr419 | | | 23320 | 3 | | | | | Olfr541 | | |
| 23225 | 3 | | | | | Olfr421-ps1 | | | 23321 | 3 | | | | | Olfr543 | | |
| 23226 | 3 | | | | | Olfr424 | | | 23322 | 3 | | | | | Olfr545 | | |
| 23227 | 3 | | | | | Olfr426 | | | 23323 | 3 | | | | | Olfr547 | | |
| 23228 | 3 | | | | | Olfr427 | | | 23324 | 3 | | | | | Olfr549 | | |
| 23229 | 3 | | | | | Olfr429 | | | 23325 | 3 | | | | | Olfr55 | | |
| 23230 | 3 | | | | | Olfr430 | | | 23326 | 3 | | | | | Olfr550 | | |
| 23231 | 3 | | | | | Olfr432 | | | 23327 | 3 | | | | | Olfr552 | | |
| 23232 | 3 | | | | | Olfr433 | | | 23328 | 3 | | | | | Olfr553 | | |
| 23233 | 3 | | | | | Olfr434 | | | 23329 | 3 | | | | | Olfr554 | | |
| 23234 | 3 | | | | | Olfr435 | | | 23330 | 3 | | | | | Olfr555 | | |
| 23235 | 3 | | | | | Olfr437 | | | 23331 | 3 | | | | | Olfr556 | | |
| 23236 | 3 | | | | | Olfr44 | | | 23332 | 3 | | | | | Olfr558 | | |
| 23237 | 3 | | | | | Olfr441 | | | 23333 | 3 | | | | | Olfr559 | | |
| 23238 | 3 | | | | | Olfr447 | | | 23334 | 3 | | | | | Olfr56 | | |
| 23239 | 3 | | | | | Olfr448 | | | 23335 | 3 | | | | | Olfr560 | | |
| 23240 | 3 | | | | | Olfr449 | | | 23336 | 3 | | | | | Olfr561 | | |
| 23241 | 3 | | | | | Olfr45 | | | 23337 | 3 | | | | | Olfr564 | | |
| 23242 | 3 | | | | | Olfr450 | | | 23338 | 3 | | | | | Olfr566 | | |
| 23243 | 3 | | | | | Olfr452 | | | 23339 | 3 | | | | | Olfr569 | | |
| 23244 | 3 | | | | | Olfr453 | | | 23340 | 3 | | | | | Olfr57 | | |
| 23245 | 3 | | | | | Olfr455 | | | 23341 | 3 | | | | | Olfr571 | | |
| 23246 | 3 | | | | | Olfr456 | | | 23342 | 3 | | | | | Olfr572 | | |
| 23247 | 3 | | | | | Olfr457 | | | 23343 | 3 | | | | | Olfr574 | | |
| 23248 | 3 | | | | | Olfr458 | | | 23344 | 3 | | | | | Olfr575 | | |
| 23249 | 3 | | | | | Olfr459 | | | 23345 | 3 | | | | | Olfr576 | | |
| 23250 | 3 | | | | | Olfr46 | | | 23346 | 3 | | | | | Olfr577 | | |
| 23251 | 3 | | | | | Olfr460 | | | 23347 | 3 | | | | | Olfr578 | | |
| 23252 | 3 | | | | | Olfr461 | | | 23348 | 3 | | | | | Olfr58 | | |
| 23253 | 3 | | | | | Olfr462 | | | 23349 | 3 | | | | | Olfr582 | | |
| 23254 | 3 | | | | | Olfr463 | | | 23350 | 3 | | | | | Olfr583 | | |
| 23255 | 3 | | | | | Olfr464 | | | 23351 | 3 | | | | | Olfr584 | | |
| 23256 | 3 | | | | | Olfr466 | | | 23352 | 3 | | | | | Olfr585 | | |
| 23257 | 3 | | | | | Olfr467 | | | 23353 | 3 | | | | | Olfr586 | | |
| 23258 | 3 | | | | | Olfr469 | | | 23354 | 3 | | | | | Olfr589 | | |
| 23259 | 3 | | | | | Olfr47 | | | 23355 | 3 | | | | | Olfr59 | | |
| 23260 | 3 | | | | | Olfr470 | | | 23356 | 3 | | | | | Olfr591 | | |
| 23261 | 3 | | | | | Olfr472 | | | 23357 | 3 | | | | | Olfr592 | | |
| 23262 | 3 | | | | | Olfr473 | | | 23358 | 3 | | | | | Olfr593 | | |
| 23263 | 3 | | | | | Olfr474 | | | 23359 | 3 | | | | | Olfr594 | | |
| 23264 | 3 | | | | | Olfr476 | | | 23360 | 3 | | | | | Olfr596 | | |
| 23265 | 3 | | | | | Olfr477 | | | 23361 | 3 | | | | | Olfr598 | | |
| 23266 | 3 | | | | | Olfr478 | | | 23362 | 3 | | | | | Olfr599 | | |
| 23267 | 3 | | | | | Olfr479 | | | 23363 | 3 | | | | | Olfr6 | | |
| 23268 | 3 | | | | | Olfr481 | | | 23364 | 3 | | | | | Olfr60 | | |
| 23269 | 3 | | | | | Olfr482 | | | 23365 | 3 | | | | | Olfr600 | | |
| 23270 | 3 | | | | | Olfr483 | | | 23366 | 3 | | | | | Olfr601 | | |
| 23271 | 3 | | | | | Olfr484 | | | 23367 | 3 | | | | | Olfr603 | | |
| 23272 | 3 | | | | | Olfr485 | | | 23368 | 3 | | | | | Olfr606 | | |
| 23273 | 3 | | | | | Olfr486 | | | 23369 | 3 | | | | | Olfr608 | | |
| 23274 | 3 | | | | | Olfr487 | | | 23370 | 3 | | | | | Olfr609 | | |
| 23275 | 3 | | | | | Olfr488 | | | 23371 | 3 | | | | | Olfr61 | | |
| 23276 | 3 | | | | | Olfr49 | | | 23372 | 3 | | | | | Olfr610 | | |
| 23277 | 3 | | | | | Olfr490 | | | 23373 | 3 | | | | | Olfr611 | | |
| 23278 | 3 | | | | | Olfr491 | | | 23374 | 3 | | | | | Olfr612 | | |
| 23279 | 3 | | | | | Olfr492 | | | 23375 | 3 | | | | | Olfr613 | | |

Fig. 30 - 124

| | | | | | | | | | | | | | | |
|---|---|---|---|---|---|---|---|---|---|---|---|---|---|---|
| 23376 | 3 | | | | | Olfr615 | | | | 23472 | 3 | | | Olfr73 |
| 23377 | 3 | | | | | Olfr616 | | | | 23473 | 3 | | | Olfr730 |
| 23378 | 3 | | | | | Olfr617 | | | | 23474 | 3 | | | Olfr731 |
| 23379 | 3 | | | | | Olfr618 | | | | 23475 | 3 | | | Olfr732 |
| 23380 | 3 | | | | | Olfr619 | | | | 23476 | 3 | | | Olfr733 |
| 23381 | 3 | | | | | Olfr62 | | | | 23477 | 3 | | | Olfr734 |
| 23382 | 3 | | | | | Olfr620 | | | | 23478 | 3 | | | Olfr735 |
| 23383 | 3 | | | | | Olfr622 | | | | 23479 | 3 | | | Olfr736 |
| 23384 | 3 | | | | | Olfr623 | | | | 23480 | 3 | | | Olfr738 |
| 23385 | 3 | | | | | Olfr624 | | | | 23481 | 3 | | | Olfr739 |
| 23386 | 3 | | | | | Olfr628 | | | | 23482 | 3 | | | Olfr741 |
| 23387 | 3 | | | | | Olfr629 | | | | 23483 | 3 | | | Olfr742 |
| 23388 | 3 | | | | | Olfr63 | | | | 23484 | 3 | | | Olfr743 |
| 23389 | 3 | | | | | Olfr630 | | | | 23485 | 3 | | | Olfr744 |
| 23390 | 3 | | | | | Olfr631 | | | | 23486 | 3 | | | Olfr745 |
| 23391 | 3 | | | | | Olfr632 | | | | 23487 | 3 | | | Olfr746 |
| 23392 | 3 | | | | | Olfr633 | | | | 23488 | 3 | | | Olfr747 |
| 23393 | 3 | | | | | Olfr635 | | | | 23489 | 3 | | | Olfr748 |
| 23394 | 3 | | | | | Olfr638 | | | | 23490 | 3 | | | Olfr749 |
| 23395 | 3 | | | | | Olfr639 | | | | 23491 | 3 | | | Olfr750 |
| 23396 | 3 | | | | | Olfr64 | | | | 23492 | 3 | | | Olfr76 |
| 23397 | 3 | | | | | Olfr640 | | | | 23493 | 3 | | | Olfr761 |
| 23398 | 3 | | | | | Olfr641 | | | | 23494 | 3 | | | Olfr763 |
| 23399 | 3 | | | | | Olfr642 | | | | 23495 | 3 | | | Olfr765 |
| 23400 | 3 | | | | | Olfr643 | | | | 23496 | 3 | | | Olfr767 |
| 23401 | 3 | | | | | Olfr644 | | | | 23497 | 3 | | | Olfr768 |
| 23402 | 3 | | | | | Olfr646 | | | | 23498 | 3 | | | Olfr769 |
| 23403 | 3 | | | | | Olfr648 | | | | 23499 | 3 | | | Olfr77 |
| 23404 | 3 | | | | | Olfr649 | | | | 23500 | 3 | | | Olfr771 |
| 23405 | 3 | | | | | Olfr65 | | | | 23501 | 3 | | | Olfr772 |
| 23406 | 3 | | | | | Olfr651 | | | | 23502 | 3 | | | Olfr773 |
| 23407 | 3 | | | | | Olfr652 | | | | 23503 | 3 | | | Olfr774 |
| 23408 | 3 | | | | | Olfr653 | | | | 23504 | 3 | | | Olfr775 |
| 23409 | 3 | | | | | Olfr654 | | | | 23505 | 3 | | | Olfr776 |
| 23410 | 3 | | | | | Olfr655 | | | | 23506 | 3 | | | Olfr777 |
| 23411 | 3 | | | | | Olfr656 | | | | 23507 | 3 | | | Olfr78 |
| 23412 | 3 | | | | | Olfr657 | | | | 23508 | 3 | | | Olfr781 |
| 23413 | 3 | | | | | Olfr658 | | | | 23509 | 3 | | | Olfr786 |
| 23414 | 3 | | | | | Olfr659 | | | | 23510 | 3 | | | Olfr787 |
| 23415 | 3 | | | | | Olfr66 | | | | 23511 | 3 | | | Olfr790 |
| 23416 | 3 | | | | | Olfr661 | | | | 23512 | 3 | | | Olfr791 |
| 23417 | 3 | | | | | Olfr663 | | | | 23513 | 3 | | | Olfr792 |
| 23418 | 3 | | | | | Olfr665 | | | | 23514 | 3 | | | Olfr794 |
| 23419 | 3 | | | | | Olfr666 | | | | 23515 | 3 | | | Olfr796 |
| 23420 | 3 | | | | | Olfr667 | | | | 23516 | 3 | | | Olfr799 |
| 23421 | 3 | | | | | Olfr668 | | | | 23517 | 3 | | | Olfr8 |
| 23422 | 3 | | | | | Olfr669 | | | | 23518 | 3 | | | Olfr800 |
| 23423 | 3 | | | | | Olfr67 | | | | 23519 | 3 | | | Olfr801 |
| 23424 | 3 | | | | | Olfr670 | | | | 23520 | 3 | | | Olfr802 |
| 23425 | 3 | | | | | Olfr671 | | | | 23521 | 3 | | | Olfr803 |
| 23426 | 3 | | | | | Olfr672 | | | | 23522 | 3 | | | Olfr804 |
| 23427 | 3 | | | | | Olfr675 | | | | 23523 | 3 | | | Olfr806 |
| 23428 | 3 | | | | | Olfr676 | | | | 23524 | 3 | | | Olfr807 |
| 23429 | 3 | | | | | Olfr677 | | | | 23525 | 3 | | | Olfr809 |
| 23430 | 3 | | | | | Olfr678 | | | | 23526 | 3 | | | Olfr810 |
| 23431 | 3 | | | | | Olfr679 | | | | 23527 | 3 | | | Olfr811 |
| 23432 | 3 | | | | | Olfr68 | | | | 23528 | 3 | | | Olfr812 |
| 23433 | 3 | | | | | Olfr683 | | | | 23529 | 3 | | | Olfr813 |
| 23434 | 3 | | | | | Olfr684 | | | | 23530 | 3 | | | Olfr814 |
| 23435 | 3 | | | | | Olfr685 | | | | 23531 | 3 | | | Olfr815 |
| 23436 | 3 | | | | | Olfr686 | | | | 23532 | 3 | | | Olfr816 |
| 23437 | 3 | | | | | Olfr688 | | | | 23533 | 3 | | | Olfr818 |
| 23438 | 3 | | | | | Olfr689 | | | | 23534 | 3 | | | Olfr819 |
| 23439 | 3 | | | | | Olfr69 | | | | 23535 | 3 | | | Olfr820 |
| 23440 | 3 | | | | | Olfr690 | | | | 23536 | 3 | | | Olfr821 |
| 23441 | 3 | | | | | Olfr691 | | | | 23537 | 3 | | | Olfr822 |
| 23442 | 3 | | | | | Olfr692 | | | | 23538 | 3 | | | Olfr823 |
| 23443 | 3 | | | | | Olfr693 | | | | 23539 | 3 | | | Olfr825 |
| 23444 | 3 | | | | | Olfr694 | | | | 23540 | 3 | | | Olfr826 |
| 23445 | 3 | | | | | Olfr695 | | | | 23541 | 3 | | | Olfr827 |
| 23446 | 3 | | | | | Olfr697 | | | | 23542 | 3 | | | Olfr828 |
| 23447 | 3 | | | | | Olfr698 | | | | 23543 | 3 | | | Olfr829 |
| 23448 | 3 | | | | | Olfr699 | | | | 23544 | 3 | | | Olfr830 |
| 23449 | 3 | | | | | Olfr70 | | | | 23545 | 3 | | | Olfr832 |
| 23450 | 3 | | | | | Olfr700 | | | | 23546 | 3 | | | Olfr834 |
| 23451 | 3 | | | | | Olfr701 | | | | 23547 | 3 | | | Olfr835 |
| 23452 | 3 | | | | | Olfr702 | | | | 23548 | 3 | | | Olfr836 |
| 23453 | 3 | | | | | Olfr704 | | | | 23549 | 3 | | | Olfr837 |
| 23454 | 3 | | | | | Olfr705 | | | | 23550 | 3 | | | Olfr843 |
| 23455 | 3 | | | | | Olfr706 | | | | 23551 | 3 | | | Olfr845 |
| 23456 | 3 | | | | | Olfr707 | | | | 23552 | 3 | | | Olfr846 |
| 23457 | 3 | | | | | Olfr710 | | | | 23553 | 3 | | | Olfr847 |
| 23458 | 3 | | | | | Olfr711 | | | | 23554 | 3 | | | Olfr849 |
| 23459 | 3 | | | | | Olfr713 | | | | 23555 | 3 | | | Olfr850 |
| 23460 | 3 | | | | | Olfr714 | | | | 23556 | 3 | | | Olfr851 |
| 23461 | 3 | | | | | Olfr715 | | | | 23557 | 3 | | | Olfr853 |
| 23462 | 3 | | | | | Olfr716 | | | | 23558 | 3 | | | Olfr854 |
| 23463 | 3 | | | | | Olfr720 | | | | 23559 | 3 | | | Olfr855 |
| 23464 | 3 | | | | | Olfr722 | | | | 23560 | 3 | | | Olfr856-ps1 |
| 23465 | 3 | | | | | Olfr723 | | | | 23561 | 3 | | | Olfr857 |
| 23466 | 3 | | | | | Olfr724 | | | | 23562 | 3 | | | Olfr859 |
| 23467 | 3 | | | | | Olfr725 | | | | 23563 | 3 | | | Olfr860 |
| 23468 | 3 | | | | | Olfr726 | | | | 23564 | 3 | | | Olfr862 |
| 23469 | 3 | | | | | Olfr727 | | | | 23565 | 3 | | | Olfr866 |
| 23470 | 3 | | | | | Olfr728 | | | | 23566 | 3 | | | Olfr867 |
| 23471 | 3 | | | | | Olfr729 | | | | 23567 | 3 | | | Olfr868 |

Fig. 30 - 125

| | | | | | | | | | | | | | | | | | |
|---|---|---|---|---|---|---|---|---|---|---|---|---|---|---|---|---|---|
| 23568 | 3 | | | | | | Olfr869 | | | 23664 | 3 | | | | | Ooep | | |
| 23569 | 3 | | | | | | Olfr870 | | | 23665 | 3 | | | | | Oog2 | 441161 | 4-May-15 |
| 23570 | 3 | | | | | | Olfr871 | | | 23666 | 3 | | | | | Oog3 | | |
| 23571 | 3 | | | | | | Olfr872 | | | 23667 | 3 | | | | | Oosp2 | 219990 | 4-May-15 |
| 23572 | 3 | | | | | | Olfr873 | | | 23668 | 3 | | | | | Opa1 | 4976 | 7-Jun-15 |
| 23573 | 3 | | | | | | Olfr874 | | | 23669 | 3 | | | | | Opcml | 4978 | 4-May-15 |
| 23574 | 3 | | | | | | Olfr875 | | | 23670 | 3 | | | | | Psg28 | | |
| 23575 | 3 | | | | | | Olfr876 | | | 23671 | 3 | | | | | Tatdn3 | 128387 | 4-May-15 |
| 23576 | 3 | | | | | | Olfr877 | | | 23672 | 3 | | | | | Tax1bp3 | 30851 | 1-Jun-15 |
| 23577 | 3 | | | | | | Olfr878 | | | 23673 | 3 | | | | | Tdrd3 | 81550 | 4-May-15 |
| 23578 | 3 | | | | | | Olfr881 | | | 23674 | 3 | | | | | Vmn1r151 | | |
| 23579 | 3 | | | | | | Olfr885 | | | 23675 | 3 | | | | | Vmn1r152 | | |
| 23580 | 3 | | | | | | Olfr887 | | | 23676 | 3 | | | | | Vmn1r155 | | |
| 23581 | 3 | | | | | | Olfr888 | | | 23677 | 3 | | | | | Vmn1r157 | | |
| 23582 | 3 | | | | | | Olfr889 | | | 23678 | 3 | | | | | Vmn1r158 | | |
| 23583 | 3 | | | | | | Olfr890 | | | 23679 | 3 | | | | | Vmn1r159 | | |
| 23584 | 3 | | | | | | Olfr891 | | | 23680 | 3 | | | | | Vmn1r16 | | |
| 23585 | 3 | | | | | | Olfr893 | | | 23681 | 3 | | | | | Vmn1r160 | | |
| 23586 | 3 | | | | | | Olfr894 | | | 23682 | 3 | | | | | Vmn1r163 | | |
| 23587 | 3 | | | | | | Olfr895 | | | 23683 | 3 | | | | | Vmn1r165 | | |
| 23588 | 3 | | | | | | Olfr898 | | | 23684 | 3 | | | | | Vmn1r166 | | |
| 23589 | 3 | | | | | | Olfr899 | | | 23685 | 3 | | | | | Vmn1r167 | | |
| 23590 | 3 | | | | | | Olfr9 | | | 23686 | 3 | | | | | Vmn1r168 | | |
| 23591 | 3 | | | | | | Olfr90 | | | 23687 | 3 | | | | | Vmn1r169 | | |
| 23592 | 3 | | | | | | Olfr901 | | | 23688 | 3 | | | | | Vmn1r17 | | |
| 23593 | 3 | | | | | | Olfr902 | | | 23689 | 3 | | | | | Vmn1r170 | | |
| 23594 | 3 | | | | | | Olfr904 | | | 23690 | 3 | | | | | Vmn1r171 | | |
| 23595 | 3 | | | | | | Olfr905 | | | 23691 | 3 | | | | | Vmn1r172 | | |
| 23596 | 3 | | | | | | Olfr906 | | | 23692 | 3 | | | | | Vmn1r173 | | |
| 23597 | 3 | | | | | | Olfr907 | | | 23693 | 3 | | | | | Vmn1r174 | | |
| 23598 | 3 | | | | | | Olfr908 | | | 23694 | 3 | | | | | Vmn1r175 | | |
| 23599 | 3 | | | | | | Olfr91 | | | 23695 | 3 | | | | | Vmn1r176 | | |
| 23600 | 3 | | | | | | Olfr910 | | | 23696 | 3 | | | | | Vmn1r177 | | |
| 23601 | 3 | | | | | | Olfr911-ps1 | | | 23697 | 3 | | | | | Vmn1r178 | | |
| 23602 | 3 | | | | | | Olfr912 | | | 23698 | 3 | | | | | Vmn1r179 | | |
| 23603 | 3 | | | | | | Olfr913 | | | 23699 | 3 | | | | | Vmn1r18 | | |
| 23604 | 3 | | | | | | Olfr914 | | | 23700 | 3 | | | | | Vmn1r180 | | |
| 23605 | 3 | | | | | | Olfr915 | | | 23701 | 3 | | | | | Vmn1r181 | | |
| 23606 | 3 | | | | | | Olfr916 | | | 23702 | 3 | | | | | Vmn1r183 | | |
| 23607 | 3 | | | | | | Olfr917 | | | 23703 | 3 | | | | | Vmn1r184 | | |
| 23608 | 3 | | | | | | Olfr918 | | | 23704 | 3 | | | | | Vmn1r185 | | |
| 23609 | 3 | | | | | | Olfr920 | | | 23705 | 3 | | | | | Vmn1r186 | | |
| 23610 | 3 | | | | | | Olfr921 | | | 23706 | 3 | | | | | Vmn1r187 | | |
| 23611 | 3 | | | | | | Olfr922 | | | 23707 | 3 | | | | | Vmn1r188 | | |
| 23612 | 3 | | | | | | Olfr923 | | | 23708 | 3 | | | | | Vmn1r19 | | |
| 23613 | 3 | | | | | | Olfr924 | | | 23709 | 3 | | | | | Vmn1r191 | | |
| 23614 | 3 | | | | | | Olfr926 | | | 23710 | 3 | | | | | Vmn1r192 | | |
| 23615 | 3 | | | | | | Olfr93 | | | 23711 | 3 | | | | | Vmn1r193 | | |
| 23616 | 3 | | | | | | Olfr933 | | | 23712 | 3 | | | | | Vmn1r194 | | |
| 23617 | 3 | | | | | | Olfr934 | | | 23713 | 3 | | | | | Vmn1r195 | | |
| 23618 | 3 | | | | | | Olfr935 | | | 23714 | 3 | | | | | Vmn1r196 | | |
| 23619 | 3 | | | | | | Olfr936 | | | 23715 | 3 | | | | | Vmn1r197 | | |
| 23620 | 3 | | | | | | Olfr937 | | | 23716 | 3 | | | | | Vmn1r198 | | |
| 23621 | 3 | | | | | | Olfr938 | | | 23717 | 3 | | | | | Vmn1r199 | | |
| 23622 | 3 | | | | | | Olfr94 | | | 23718 | 3 | | | | | Vmn1r2 | | |
| 23623 | 3 | | | | | | Olfr943 | | | 23719 | 3 | | | | | Vmn1r20 | | |
| 23624 | 3 | | | | | | Olfr944 | | | 23720 | 3 | | | | | Vmn1r200 | | |
| 23625 | 3 | | | | | | Olfr945 | | | 23721 | 3 | | | | | Vmn1r201 | | |
| 23626 | 3 | | | | | | Olfr947-ps1 | | | 23722 | 3 | | | | | Vmn1r202 | | |
| 23627 | 3 | | | | | | Olfr948 | | | 23723 | 3 | | | | | Vmn1r203 | | |
| 23628 | 3 | | | | | | Olfr951 | | | 23724 | 3 | | | | | Vmn1r204 | | |
| 23629 | 3 | | | | | | Olfr952 | | | 23725 | 3 | | | | | Vmn1r205 | | |
| 23630 | 3 | | | | | | Olfr954 | | | 23726 | 3 | | | | | Vmn1r206 | | |
| 23631 | 3 | | | | | | Olfr955 | | | 23727 | 3 | | | | | Vmn1r207-ps | | |
| 23632 | 3 | | | | | | Olfr957 | | | 23728 | 3 | | | | | Vmn1r208 | | |
| 23633 | 3 | | | | | | Olfr958 | | | 23729 | 3 | | | | | Vmn1r209 | | |
| 23634 | 3 | | | | | | Olfr959 | | | 23730 | 3 | | | | | Vmn1r21 | | |
| 23635 | 3 | | | | | | Olfr96 | | | 23731 | 3 | | | | | Vmn1r210 | | |
| 23636 | 3 | | | | | | Olfr960 | | | 23732 | 3 | | | | | Vmn1r211 | | |
| 23637 | 3 | | | | | | Olfr961 | | | 23733 | 3 | | | | | Vmn1r212 | | |
| 23638 | 3 | | | | | | Olfr963 | | | 23734 | 3 | | | | | Vmn1r213 | | |
| 23639 | 3 | | | | | | Olfr965 | | | 23735 | 3 | | | | | Vmn1r214 | | |
| 23640 | 3 | | | | | | Olfr967 | | | 23736 | 3 | | | | | Vmn1r215 | | |
| 23641 | 3 | | | | | | Olfr968 | | | 23737 | 3 | | | | | Vmn1r216 | | |
| 23642 | 3 | | | | | | Olfr969 | | | 23738 | 3 | | | | | Vmn1r217 | | |
| 23643 | 3 | | | | | | Olfr97 | | | 23739 | 3 | | | | | Vmn1r219 | | |
| 23644 | 3 | | | | | | Olfr970 | | | 23740 | 3 | | | | | Vmn1r22 | | |
| 23645 | 3 | | | | | | Olfr974 | | | 23741 | 3 | | | | | Vmn1r220 | | |
| 23646 | 3 | | | | | | Olfr975 | | | 23742 | 3 | | | | | Vmn1r221 | | |
| 23647 | 3 | | | | | | Olfr976 | | | 23743 | 3 | | | | | Vmn1r222 | | |
| 23648 | 3 | | | | | | Olfr978 | | | 23744 | 3 | | | | | Vmn1r223 | | |
| 23649 | 3 | | | | | | Olfr979 | | | 23745 | 3 | | | | | Vmn1r224 | | |
| 23650 | 3 | | | | | | Olfr98 | | | 23746 | 3 | | | | | Vmn1r225 | | |
| 23651 | 3 | | | | | | Olfr981 | | | 23747 | 3 | | | | | Vmn1r226 | | |
| 23652 | 3 | | | | | | Olfr982 | | | 23748 | 3 | | | | | Vmn1r227 | | |
| 23653 | 3 | | | | | | Olfr983 | | | 23749 | 3 | | | | | Vmn1r228 | | |
| 23654 | 3 | | | | | | Olfr984 | | | 23750 | 3 | | | | | Vmn1r229 | | |
| 23655 | 3 | | | | | | Olfr985 | | | 23751 | 3 | | | | | Vmn1r23 | | |
| 23656 | 3 | | | | | | Olfr988 | | | 23752 | 3 | | | | | Vmn1r231 | | |
| 23657 | 3 | | | | | | Olfr99 | | | 23753 | 3 | | | | | Vmn1r232 | | |
| 23658 | 3 | | | | | | Olfr993 | | | 23754 | 3 | | | | | Vmn1r233 | | |
| 23659 | 3 | | | | | | Olfr994 | | | 23755 | 3 | | | | | Vmn1r234 | | |
| 23660 | 3 | | | | | | Olfr995 | | | 23756 | 3 | | | | | Vmn1r235 | | |
| 23661 | 3 | | | | | | Olfr996 | | | 23757 | 3 | | | | | Vmn1r236 | | |
| 23662 | 3 | | | | | | Olfr998 | | | 23758 | 3 | | | | | Vmn1r237 | | |
| 23663 | 3 | | | | | | Oma1 | 115209 | 3-May-15 | 23759 | 3 | | | | | Vmn1r238 | | |

Fig. 30 - 126

| | | | | | | | |
|---|---|---|---|---|---|---|---|
| 23760 | 3 | | | | | Vmn1r24 | |
| 23761 | 3 | | | | | Vmn1r25 | |
| 23762 | 3 | | | | | Vmn1r26 | |
| 23763 | 3 | | | | | Vmn1r27 | |
| 23764 | 3 | | | | | Vmn1r28 | |
| 23765 | 3 | | | | | Vmn1r29 | |
| 23766 | 3 | | | | | Vmn1r3 | |
| 23767 | 3 | | | | | Vmn1r30 | |
| 23768 | 3 | | | | | Vmn1r31 | |
| 23769 | 3 | | | | | Vmn1r32 | |
| 23770 | 3 | | | | | Vmn1r33 | |
| 23771 | 3 | | | | | Vmn1r34 | |
| 23772 | 3 | | | | | Vmn1r35 | |
| 23773 | 3 | | | | | Vmn1r36 | |
| 23774 | 3 | | | | | Vmn1r37 | |
| 23775 | 3 | | | | | Vmn1r38 | |
| 23776 | 3 | | | | | Vmn1r39 | |
| 23777 | 3 | | | | | Vmn1r4 | |
| 23778 | 3 | | | | | Vmn1r40 | |
| 23779 | 3 | | | | | Vmn1r41 | |
| 23780 | 3 | | | | | Vmn1r42 | |
| 23781 | 3 | | | | | Vmn1r43 | |
| 23782 | 3 | | | | | Vmn1r44 | |
| 23783 | 3 | | | | | Vmn1r45 | |
| 23784 | 3 | | | | | Vmn1r46 | |
| 23785 | 3 | | | | | Vmn1r48 | |
| 23786 | 3 | | | | | Vmn1r49 | |
| 23787 | 3 | | | | | Vmn1r5 | |
| 23788 | 3 | | | | | Vmn1r50 | |
| 23789 | 3 | | | | | Vmn1r51 | |
| 23790 | 3 | | | | | Vmn1r52 | |
| 23791 | 3 | | | | | Vmn1r53 | |
| 23792 | 3 | | | | | Vmn1r54 | |
| 23793 | 3 | | | | | Vmn1r55 | |
| 23794 | 3 | | | | | Vmn1r56 | |
| 23795 | 3 | | | | | Vmn1r57 | |
| 23796 | 3 | | | | | Vmn1r58 | |
| 23797 | 3 | | | | | Vmn1r59 | |
| 23798 | 3 | | | | | Vmn1r6 | |
| 23799 | 3 | | | | | Vmn1r60 | |
| 23800 | 3 | | | | | Vmn1r61 | |
| 23801 | 3 | | | | | Vmn1r62 | |
| 23802 | 3 | | | | | Vmn1r63 | |
| 23803 | 3 | | | | | Vmn1r64 | |
| 23804 | 3 | | | | | Vmn1r65 | |
| 23805 | 3 | | | | | Vmn1r66 | |
| 23806 | 3 | | | | | Vmn1r67 | |
| 23807 | 3 | | | | | Vmn1r68 | |
| 23808 | 3 | | | | | Vmn1r69 | |
| 23809 | 3 | | | | | Vmn1r7 | |
| 23810 | 3 | | | | | Vmn1r70 | |
| 23811 | 3 | | | | | Vmn1r71 | |
| 23812 | 3 | | | | | Vmn1r72 | |
| 23813 | 3 | | | | | Vmn1r73 | |
| 23814 | 3 | | | | | Vmn1r74 | |
| 23815 | 3 | | | | | Vmn1r75 | |
| 23816 | 3 | | | | | Vmn1r76 | |
| 23817 | 3 | | | | | Vmn1r77 | |
| 23818 | 3 | | | | | Vmn1r78 | |
| 23819 | 3 | | | | | Vmn1r79 | |
| 23820 | 3 | | | | | Vmn1r8 | |
| 23821 | 3 | | | | | Vmn1r80 | |
| 23822 | 3 | | | | | Vmn1r81 | |
| 23823 | 3 | | | | | Vmn1r82 | |
| 23824 | 3 | | | | | Vmn1r83 | |
| 23825 | 3 | | | | | Vmn1r84 | |
| 23826 | 3 | | | | | Vmn1r85 | |
| 23827 | 3 | | | | | Vmn1r86 | |
| 23828 | 3 | | | | | Vmn1r87 | |
| 23829 | 3 | | | | | Vmn1r88 | |
| 23830 | 3 | | | | | Vmn1r89 | |
| 23831 | 3 | | | | | Vmn1r9 | |
| 23832 | 3 | | | | | Vmn1r90 | |
| 23833 | 3 | | | | | Vmn1r91 | |
| 23834 | 3 | | | | | Vmn1r93 | |
| 23835 | 3 | | | | | Vmn1r94 | |
| 23836 | 3 | | | | | Vmn1r-ps103 | |
| 23837 | 3 | | | | | Vmn1r-ps79 | |
| 23838 | 3 | | | | | Vmn2r1 | |
| 23839 | 3 | | | | | Vmn2r10 | |
| 23840 | 3 | | | | | Vmn2r100 | |
| 23841 | 3 | | | | | Vmn2r101 | |
| 23842 | 3 | | | | | Vmn2r102 | |
| 23843 | 3 | | | | | Vmn2r103 | |
| 23844 | 3 | | | | | Vmn2r104 | |
| 23845 | 3 | | | | | Vmn2r105 | |
| 23846 | 3 | | | | | Vmn2r106 | |
| 23847 | 3 | | | | | Vmn2r107 | |
| 23848 | 3 | | | | | Vmn2r108 | |
| 23849 | 3 | | | | | Vmn2r109 | |
| 23850 | 3 | | | | | Vmn2r11 | |
| 23851 | 3 | | | | | Vmn2r110 | |
| 23852 | 3 | | | | | Vmn2r111 | |
| 23853 | 3 | | | | | Vmn2r112 | |
| 23854 | 3 | | | | | Vmn2r113 | |
| 23855 | 3 | | | | | Vmn2r114 | |
| 23856 | 3 | | | | | Vmn2r115 | |
| 23857 | 3 | | | | | Vmn2r116 | |
| 23858 | 3 | | | | | Vmn2r117 | |
| 23859 | 3 | | | | | Vmn2r118 | |
| 23860 | 3 | | | | | Vmn2r12 | |
| 23861 | 3 | | | | | Vmn2r120 | |
| 23862 | 3 | | | | | Vmn2r121 | |
| 23863 | 3 | | | | | Vmn2r123 | |
| 23864 | 3 | | | | | Vmn2r124 | |
| 23865 | 3 | | | | | Vmn2r13 | |
| 23866 | 3 | | | | | Vmn2r14 | |
| 23867 | 3 | | | | | Vmn2r15 | |
| 23868 | 3 | | | | | Vmn2r16 | |
| 23869 | 3 | | | | | Vmn2r17 | |
| 23870 | 3 | | | | | Vmn2r18 | |
| 23871 | 3 | | | | | Vmn2r2 | |
| 23872 | 3 | | | | | Vmn2r20 | |
| 23873 | 3 | | | | | Vmn2r21 | |
| 23874 | 3 | | | | | Vmn2r22 | |
| 23875 | 3 | | | | | Vmn2r23 | |
| 23876 | 3 | | | | | Vmn2r24 | |
| 23877 | 3 | | | | | Vmn2r25 | |
| 23878 | 3 | | | | | Vmn2r26 | |
| 23879 | 3 | | | | | Vmn2r28 | |
| 23880 | 3 | | | | | Vmn2r30 | |
| 23881 | 3 | | | | | Vmn2r31 | |
| 23882 | 3 | | | | | Vmn2r32 | |
| 23883 | 3 | | | | | Vmn2r33 | |
| 23884 | 3 | | | | | Vmn2r34 | |
| 23885 | 3 | | | | | Vmn2r35 | |
| 23886 | 3 | | | | | Vmn2r36 | |
| 23887 | 3 | | | | | Vmn2r37 | |
| 23888 | 3 | | | | | Vmn2r38 | |
| 23889 | 3 | | | | | Vmn2r39 | |
| 23890 | 3 | | | | | Vmn2r4 | |
| 23891 | 3 | | | | | Vmn2r40 | |
| 23892 | 3 | | | | | Vmn2r41 | |
| 23893 | 3 | | | | | Vmn2r42 | |
| 23894 | 3 | | | | | Vmn2r43 | |
| 23895 | 3 | | | | | Vmn2r44 | |
| 23896 | 3 | | | | | Vmn2r45 | |
| 23897 | 3 | | | | | Vmn2r47 | |
| 23898 | 3 | | | | | Vmn2r48 | |
| 23899 | 3 | | | | | Vmn2r49 | |
| 23900 | 3 | | | | | Vmn2r5 | |
| 23901 | 3 | | | | | Vmn2r50 | |
| 23902 | 3 | | | | | Vmn2r51 | |
| 23903 | 3 | | | | | Vmn2r52 | |
| 23904 | 3 | | | | | Vmn2r53 | |
| 23905 | 3 | | | | | Vmn2r54 | |
| 23906 | 3 | | | | | Vmn2r55 | |
| 23907 | 3 | | | | | Vmn2r57 | |
| 23908 | 3 | | | | | Vmn2r58 | |
| 23909 | 3 | | | | | Vmn2r59 | |
| 23910 | 3 | | | | | Vmn2r6 | |
| 23911 | 3 | | | | | Vmn2r60 | |
| 23912 | 3 | | | | | Vmn2r62 | |
| 23913 | 3 | | | | | Vmn2r63 | |
| 23914 | 3 | | | | | Vmn2r66 | |
| 23915 | 3 | | | | | Vmn2r68 | |
| 23916 | 3 | | | | | Vmn2r69 | |
| 23917 | 3 | | | | | Vmn2r7 | |
| 23918 | 3 | | | | | Vmn2r70 | |
| 23919 | 3 | | | | | Vmn2r71 | |
| 23920 | 3 | | | | | Vmn2r72 | |
| 23921 | 3 | | | | | Vmn2r73 | |
| 23922 | 3 | | | | | Vmn2r75 | |
| 23923 | 3 | | | | | Vmn2r77 | |
| 23924 | 3 | | | | | Vmn2r78 | |
| 23925 | 3 | | | | | Vmn2r79 | |
| 23926 | 3 | | | | | Vmn2r8 | |
| 23927 | 3 | | | | | Vmn2r80 | |
| 23928 | 3 | | | | | Vmn2r81 | |
| 23929 | 3 | | | | | Vmn2r82 | |
| 23930 | 3 | | | | | Vmn2r83 | |
| 23931 | 3 | | | | | Vmn2r84 | |
| 23932 | 3 | | | | | Vmn2r86 | |
| 23933 | 3 | | | | | Vmn2r87 | |
| 23934 | 3 | | | | | Vmn2r88 | |
| 23935 | 3 | | | | | Vmn2r89 | |
| 23936 | 3 | | | | | Vmn2r9 | |
| 23937 | 3 | | | | | Vmn2r90 | |
| 23938 | 3 | | | | | Vmn2r91 | |
| 23939 | 3 | | | | | Vmn2r92 | |
| 23940 | 3 | | | | | Vmn2r93 | |
| 23941 | 3 | | | | | Vmn2r94 | |
| 23942 | 3 | | | | | Vmn2r95 | |
| 23943 | 3 | | | | | Vmn2r98 | |
| 23944 | 3 | | | | | Vmn2r99 | |
| 23945 | 3 | | | | | Vmn2r-ps11 | |
| 23946 | 3 | | | | | Vmn2r-ps129 | |
| 23947 | 3 | | | | | Vmn2r-ps159 | |

Fig. 31-1

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| 1110017D15Rik | 1.00 | 1.00 | 1.00 | 1.00 | 1.00 | 1.00 | 1.00 | 1.00 | 1.00 |
| 1700001C02Rik | 1.00 | 1.00 | 1.00 | 1.00 | 1.00 | 1.00 | 1.00 | 1.00 | 1.00 |
| 1700007K13Rik | 1.00 | 1.00 | 1.00 | 1.00 | 1.00 | 1.00 | 1.00 | 1.00 | 1.00 |
| 1700009P17Rik | 1.00 | 1.00 | 1.19 | 1.48 | 0.86 | 0.71 | 1.00 | 1.00 | 1.00 |
| 1700024G13Rik | 1.00 | 1.00 | 1.00 | 1.00 | 1.00 | 1.00 | 1.00 | 1.00 | 1.00 |
| 1810007D17Rik | 1.00 | 1.00 | 1.00 | 1.00 | 1.00 | 1.00 | 1.00 | 1.00 | 1.00 |
| 1810065E05Rik | 1.00 | 1.00 | 1.00 | 1.00 | 1.00 | 1.00 | 1.00 | 1.00 | 1.00 |
| 2210010C04Rik | 1.00 | 1.00 | 1.00 | 1.00 | 1.00 | 1.00 | 1.00 | 1.53 | 1.00 |
| 2310007L24Rik | 0.98 | 0.81 | 0.86 | 1.00 | 1.00 | 1.00 | 1.00 | 1.00 | 1.00 |
| 2410004P03Rik | 1.00 | 1.00 | 1.00 | 1.00 | 1.00 | 1.00 | 1.00 | 1.00 | 1.00 |
| 2610305D13Rik | 1.44 | 0.24 | 0.59 | 1.20 | 0.32 | 0.56 | 1.00 | 1.00 | 1.00 |
| 2610507I01Rik | 1.00 | 2.42 | 1.00 | 1.00 | 2.10 | 1.00 | 1.00 | 1.98 | 1.00 |
| 4930401O12Rik | 1.00 | 1.00 | 1.00 | 1.00 | 1.00 | 1.00 | 1.00 | 1.00 | 1.00 |
| AF357426 | 1.00 | 1.00 | 1.00 | 1.00 | 1.00 | 1.00 | 1.00 | 1.00 | 1.00 |
| Aldob | 0.46 | 0.95 | 0.36 | 1.14 | 0.85 | 0.99 | 1.18 | 0.76 | 0.88 |
| Alox15 | 1.00 | 1.00 | 1.61 | 1.00 | 1.00 | 0.90 | 1.00 | 1.00 | 1.00 |
| Amy1 | 0.39 | 0.31 | 0.45 | 1.56 | 0.60 | 0.65 | 1.22 | 1.16 | 0.81 |
| Amy2a2 | 1.00 | 1.00 | 1.00 | 1.00 | 1.00 | 1.00 | 1.00 | 1.00 | 1.00 |
| Amy2a4 | 1.00 | 1.00 | 1.00 | 1.00 | 1.00 | 1.00 | 1.00 | 1.00 | 1.00 |
| Amy2b | 1.00 | 1.00 | 1.00 | 1.00 | 1.00 | 1.00 | 1.02 | 2.81 | 0.75 |
| Anapc11 | 0.83 | 0.94 | 0.86 | 0.97 | 0.95 | 0.98 | 0.91 | 1.07 | 0.98 |
| Apol7b | 1.00 | 1.00 | 1.00 | 1.00 | 1.00 | 1.00 | 0.93 | 1.28 | 0.56 |
| Aqp12 | 1.00 | 1.00 | 1.00 | 1.00 | 1.00 | 1.00 | 1.00 | 1.00 | 1.00 |
| Arhgdig | 1.98 | 1.10 | 1.10 | 0.91 | 1.34 | 1.00 | 1.00 | 1.00 | 1.00 |
| Atp6v0c-ps2 | 1.87 | 1.65 | 0.90 | 0.06 | 1.72 | 1.72 | 1.00 | 0.81 | 1.15 |
| Bdh2 | 1.00 | 1.02 | 1.01 | 1.04 | 0.87 | 0.92 | 0.69 | 0.73 | 0.87 |
| Bglap | 1.00 | 1.00 | 1.00 | 1.00 | 1.00 | 1.00 | 1.00 | 1.00 | 1.00 |
| Bglap2 | 1.00 | 1.00 | 1.00 | 1.00 | 1.00 | 1.19 | 1.00 | 1.00 | 1.00 |
| Bmp10 | 0.04 | 0.67 | 1.78 | 1.00 | 1.00 | 1.00 | 1.20 | 0.80 | 1.11 |
| Camk2b | 0.71 | 0.68 | 0.74 | 1.00 | 1.00 | 1.00 | 0.10 | 0.93 | 0.76 |
| Carns1 | 0.79 | 0.84 | 0.76 | 1.00 | 1.00 | 1.00 | 1.00 | 1.18 | 1.00 |
| Ccdc108 | 1.00 | 1.00 | 1.00 | 1.00 | 1.00 | 1.00 | 1.00 | 1.00 | 1.00 |
| Ccdc153 | 1.00 | 1.00 | 1.00 | 1.00 | 1.00 | 1.00 | 1.00 | 1.00 | 1.00 |
| Cckar | 1.00 | 1.00 | 1.00 | 0.99 | 0.79 | 1.14 | 1.00 | 1.00 | 1.00 |
| Ccl28 | 1.00 | 1.00 | 1.00 | 1.04 | 0.88 | 1.67 | 1.00 | 1.00 | 1.00 |
| Cd5l | 1.00 | 1.27 | 1.00 | 1.00 | 1.00 | 1.00 | 0.92 | 1.98 | 0.81 |
| Cda | 1.46 | 3.00 | 2.83 | 1.23 | 0.81 | 0.84 | 0.58 | 2.54 | 1.74 |
| Cdhr5 | 1.00 | 1.00 | 1.00 | 1.07 | 0.85 | 1.01 | 0.99 | 1.01 | 0.98 |
| Cel | 1.00 | 1.00 | 1.00 | 1.00 | 1.00 | 1.00 | 1.00 | 1.46 | 1.00 |
| Cela1 | 1.03 | 1.27 | 1.64 | 0.69 | 0.72 | 1.19 | 0.43 | 0.91 | 1.29 |
| Cela3b | 1.00 | 1.00 | 1.00 | 1.00 | 1.00 | 1.00 | 1.00 | 1.66 | 1.00 |
| Celsr1 | 0.66 | 0.79 | 0.62 | 0.96 | 1.06 | 0.90 | 0.79 | 2.18 | 0.99 |
| Chac1 | 2.13 | 1.32 | 1.20 | 0.19 | 1.23 | 1.00 | 0.98 | 1.25 | 0.40 |
| Ciart | 1.13 | 0.11 | 0.50 | 0.94 | 0.36 | 0.71 | 3.36 | 0.21 | 0.45 |
| Cidea | 0.84 | 0.80 | 0.93 | 0.68 | 0.14 | 0.50 | 1.00 | 1.00 | 1.00 |
| Cideb | 0.41 | 0.80 | 0.90 | 0.97 | 0.82 | 1.07 | 1.01 | 0.88 | 0.99 |
| Cish | 0.60 | 0.69 | 0.71 | 0.31 | 1.14 | 0.87 | 0.24 | 1.03 | 0.76 |
| Cldn10 | 1.00 | 1.00 | 1.41 | 0.88 | 1.13 | 1.31 | 1.00 | 1.00 | 1.00 |
| Clec3a | 0.86 | 0.51 | 1.94 | 1.00 | 1.00 | 1.00 | 1.00 | 1.00 | 1.00 |
| Clps | 1.00 | 1.00 | 1.00 | 1.00 | 1.00 | 1.00 | 1.00 | 3.82 | 1.00 |
| Cpa1 | 1.00 | 1.00 | 1.00 | 1.00 | 1.00 | 1.00 | 1.00 | 1.97 | 1.00 |
| Cpa2 | 1.00 | 1.00 | 1.00 | 1.00 | 1.00 | 1.00 | 1.00 | 1.00 | 1.00 |
| Cpb1 | 1.00 | 1.00 | 1.00 | 1.00 | 1.00 | 1.00 | 1.00 | 1.77 | 1.00 |
| Crabp1 | 1.00 | 1.00 | 1.00 | 1.00 | 1.00 | 1.00 | 1.00 | 1.00 | 1.00 |
| Crtac1 | 1.00 | 1.00 | 1.00 | 1.00 | 1.00 | 1.00 | 1.00 | 1.00 | 1.00 |
| Cryab | 1.71 | 0.71 | 0.90 | 1.14 | 1.16 | 1.06 | 1.15 | 0.85 | 1.07 |
| Ctrc | 1.00 | 1.00 | 1.00 | 1.00 | 1.00 | 1.00 | 1.00 | 1.25 | 1.00 |
| Ctrcos | 1.00 | 1.00 | 1.00 | 1.00 | 1.00 | 1.00 | 1.00 | 1.00 | 1.00 |
| Ctrl | 1.00 | 1.00 | 1.00 | 1.00 | 1.00 | 1.00 | 1.00 | 1.72 | 1.00 |
| Ctsg | 1.00 | 1.00 | 1.00 | 1.00 | 1.00 | 1.00 | 1.00 | 1.90 | 1.00 |
| Cwc22 | 0.09 | 0.40 | 1.50 | 0.10 | 0.44 | 1.42 | 0.10 | 0.41 | 1.40 |
| Cxcl11 | 1.00 | 1.00 | 1.00 | 1.00 | 1.00 | 1.00 | 0.80 | 1.00 | 1.19 |
| Cyp2b9 | 1.00 | 1.00 | 1.00 | 1.00 | 1.00 | 1.00 | 3.62 | 0.92 | 0.16 |
| Cyp2d12 | 1.00 | 1.00 | 1.00 | 3.10 | 0.06 | 0.87 | 1.04 | 0.67 | 1.00 |

Fig. 31-2

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| 1110017D15Rik | 0.80 | 0.75 | 0.91 | 1.00 | 1.00 | 1.00 | 1.00 | 1.00 | 1.00 |
| 1700001C02Rik | 0.78 | 0.75 | 0.77 | 1.00 | 1.00 | 1.00 | 1.00 | 1.00 | 1.00 |
| 1700007K13Rik | 0.88 | 0.76 | 1.01 | 1.00 | 1.00 | 1.00 | 1.00 | 1.00 | 1.00 |
| 1700009P17Rik | 0.81 | 0.87 | 0.91 | 1.00 | 1.00 | 1.00 | 0.96 | 1.46 | 1.74 |
| 1700024G13Rik | 0.65 | 0.77 | 0.87 | 1.00 | 1.00 | 1.00 | 1.00 | 1.00 | 1.00 |
| 1810007D17Rik | 1.00 | 1.00 | 1.00 | 1.00 | 1.00 | 1.00 | 1.00 | 1.00 | 1.00 |
| 1810065E05Rik | 1.00 | 1.00 | 1.00 | 1.00 | 1.00 | 1.00 | 1.00 | 1.00 | 1.00 |
| 2210010C04Rik | 1.00 | 1.00 | 1.00 | 1.00 | 1.00 | 1.00 | 1.45 | 0.07 | 0.00 |
| 2310007L24Rik | 0.88 | 1.01 | 1.40 | 0.77 | 0.86 | 1.34 | 1.00 | 1.00 | 1.00 |
| 2410004P03Rik | 0.78 | 0.76 | 1.00 | 1.00 | 1.00 | 1.00 | 1.00 | 1.00 | 1.00 |
| 2610305D13Rik | 0.88 | 0.18 | 0.36 | 1.09 | 0.39 | 0.91 | 1.02 | 1.11 | 0.37 |
| 2610507I01Rik | 0.77 | 3.29 | 0.97 | 1.00 | 1.94 | 1.00 | 1.06 | 0.97 | 1.16 |
| 4930401O12Rik | 1.00 | 1.00 | 1.00 | 1.00 | 1.00 | 1.00 | 1.00 | 1.00 | 1.00 |
| AF357426 | 1.00 | 1.00 | 1.00 | 1.00 | 1.00 | 1.00 | 1.00 | 1.00 | 1.00 |
| Aldob | 1.00 | 1.00 | 1.00 | 1.00 | 1.00 | 1.00 | 1.00 | 1.00 | 1.00 |
| Alox15 | 2.05 | 1.26 | 0.52 | 1.00 | 0.99 | 1.00 | 0.91 | 0.53 | 0.85 |
| Amy1 | 0.88 | 0.68 | 0.69 | 0.80 | 0.93 | 0.68 | 0.72 | 0.29 | 0.02 |
| Amy2a2 | 1.00 | 1.00 | 1.00 | 1.00 | 1.00 | 1.00 | 1.16 | 0.20 | 0.31 |
| Amy2a4 | 1.00 | 1.00 | 1.00 | 1.00 | 1.00 | 1.00 | 1.21 | 0.11 | 0.15 |
| Amy2b | 1.00 | 1.00 | 1.00 | 1.00 | 1.00 | 0.92 | 1.24 | 0.09 | 0.00 |
| Anapc11 | 0.89 | 0.91 | 1.00 | 0.87 | 0.93 | 0.99 | 0.89 | 0.99 | 1.11 |
| Apol7b | 1.00 | 1.00 | 1.00 | 1.00 | 1.00 | 1.00 | 0.79 | 0.78 | 3.01 |
| Aqp12 | 1.00 | 1.00 | 1.00 | 1.00 | 1.00 | 1.00 | 1.27 | 0.10 | 0.14 |
| Arhgdig | 0.85 | 0.92 | 0.86 | 1.03 | 1.00 | 1.00 | 1.91 | 0.18 | 0.32 |
| Atp6v0c-ps2 | 1.70 | 0.64 | 1.35 | 0.37 | 1.00 | 0.92 | 0.87 | 1.00 | 0.90 |
| Bdh2 | 0.98 | 1.00 | 1.00 | 0.97 | 0.81 | 1.04 | 0.68 | 1.00 | 1.00 |
| Bglap | 1.00 | 1.00 | 1.00 | 1.00 | 0.12 | 0.44 | 1.00 | 1.00 | 1.00 |
| Bglap2 | 1.00 | 1.00 | 1.00 | 1.00 | 0.20 | 0.55 | 0.99 | 1.00 | 1.00 |
| Bmp10 | 1.00 | 1.00 | 1.00 | 1.00 | 1.00 | 1.00 | 1.00 | 1.00 | 1.00 |
| Camk2b | 1.00 | 1.00 | 1.00 | 1.05 | 1.14 | 0.92 | 1.00 | 1.00 | 1.00 |
| Carns1 | 0.54 | 2.99 | 0.66 | 0.53 | 1.32 | 0.67 | 0.75 | 1.29 | 0.19 |
| Ccdc108 | 0.82 | 0.79 | 0.83 | 1.00 | 1.00 | 1.00 | 1.00 | 1.00 | 1.00 |
| Ccdc153 | 0.83 | 0.89 | 0.90 | 1.00 | 1.00 | 1.00 | 1.00 | 1.00 | 1.00 |
| Cckar | 0.86 | 0.60 | 1.10 | 1.00 | 1.00 | 1.00 | 1.69 | 0.14 | 0.20 |
| Ccl28 | 1.00 | 1.00 | 1.00 | 1.00 | 1.00 | 1.00 | 1.00 | 1.00 | 1.00 |
| Cd5l | 2.02 | 0.37 | 1.38 | 1.00 | 1.00 | 1.00 | 0.91 | 0.96 | 0.64 |
| Cda | 1.39 | 0.86 | 0.55 | 0.66 | 1.03 | 2.04 | 1.00 | 1.00 | 1.00 |
| Cdhr5 | 1.00 | 1.00 | 1.00 | 1.00 | 1.00 | 1.00 | 1.00 | 1.00 | 1.00 |
| Cel | 1.00 | 1.00 | 1.00 | 1.00 | 1.00 | 1.00 | 1.12 | 0.08 | 0.00 |
| Cela1 | 1.33 | 1.04 | 0.81 | 1.00 | 1.00 | 1.00 | 1.31 | 0.07 | 0.01 |
| Cela3b | 1.00 | 1.00 | 1.00 | 1.00 | 1.00 | 1.00 | 1.43 | 0.08 | 0.00 |
| Celsr1 | 0.98 | 0.99 | 1.16 | 1.00 | 1.00 | 1.00 | 1.12 | 1.17 | 0.76 |
| Chac1 | 0.82 | 1.05 | 1.44 | 1.27 | 1.15 | 0.47 | 0.99 | 1.15 | 0.67 |
| Ciart | 1.29 | 0.64 | 0.68 | 0.99 | 0.18 | 1.25 | 1.95 | 0.72 | 0.52 |
| Cidea | 0.81 | 1.08 | 0.63 | 1.48 | 1.34 | 0.81 | 1.00 | 1.00 | 1.00 |
| Cideb | 1.00 | 1.00 | 1.00 | 1.00 | 1.00 | 1.00 | 1.00 | 1.00 | 1.00 |
| Cish | 0.86 | 1.42 | 1.16 | 0.12 | 1.00 | 0.84 | 1.00 | 1.12 | 0.56 |
| Cldn10 | 1.10 | 0.66 | 1.02 | 1.09 | 1.00 | 1.00 | 1.45 | 0.49 | 0.67 |
| Clec3a | 1.00 | 1.00 | 1.00 | 1.00 | 0.12 | 0.18 | 1.00 | 1.00 | 1.00 |
| Clps | 1.00 | 1.00 | 1.00 | 1.00 | 1.00 | 1.00 | 1.10 | 0.07 | 0.00 |
| Cpa1 | 1.00 | 1.00 | 1.00 | 1.00 | 1.00 | 1.00 | 1.32 | 0.08 | 0.00 |
| Cpa2 | 1.00 | 1.00 | 1.00 | 1.00 | 1.00 | 1.00 | 1.36 | 0.08 | 0.00 |
| Cpb1 | 1.00 | 1.00 | 1.00 | 1.00 | 1.00 | 1.00 | 1.40 | 0.07 | 0.00 |
| Crabp1 | 1.00 | 1.00 | 1.00 | 1.00 | 1.00 | 1.00 | 1.00 | 1.00 | 1.00 |
| Crtac1 | 1.00 | 1.00 | 1.00 | 1.00 | 1.00 | 1.00 | 1.00 | 1.00 | 1.00 |
| Cryab | 0.99 | 0.76 | 0.92 | 0.87 | 0.92 | 1.17 | 0.64 | 0.73 | 1.00 |
| Ctrc | 1.00 | 1.00 | 1.00 | 1.00 | 1.00 | 1.00 | 1.08 | 0.08 | 0.00 |
| Ctrcos | 1.00 | 1.00 | 1.00 | 1.00 | 1.00 | 1.00 | 1.30 | 1.00 | 1.00 |
| Ctrl | 1.03 | 1.02 | 1.00 | 1.00 | 1.00 | 1.00 | 1.17 | 0.06 | 0.00 |
| Ctsg | 1.00 | 2.30 | 1.00 | 1.00 | 0.39 | 0.85 | 0.20 | 1.30 | 2.20 |
| Cwc22 | 0.08 | 0.53 | 1.47 | 0.11 | 0.42 | 1.44 | 0.09 | 0.57 | 1.54 |
| Cxcl11 | 1.00 | 1.00 | 1.00 | 1.00 | 1.00 | 1.00 | 1.00 | 1.00 | 1.00 |
| Cyp2b9 | 1.23 | 0.63 | 0.73 | 1.00 | 1.00 | 1.00 | 1.00 | 1.00 | 1.00 |
| Cyp2d12 | 1.00 | 1.00 | 1.00 | 1.00 | 1.00 | 1.00 | 1.00 | 1.00 | 1.00 |

Fig. 31-3

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| 1110017D15Rik | 1.03 | 1.05 | 0.94 | 0.32 | 0.10 | 1.00 | 1.02 | 1.04 | 1.01 |
| 1700001C02Rik | 1.00 | 1.00 | 1.00 | 0.45 | 0.18 | 1.00 | 1.06 | 1.18 | 1.09 |
| 1700007K13Rik | 1.03 | 0.84 | 1.22 | 0.50 | 0.15 | 1.00 | 1.19 | 1.13 | 1.03 |
| 1700009P17Rik | 0.90 | 1.22 | 0.99 | 0.55 | 0.13 | 1.00 | 1.02 | 1.19 | 1.04 |
| 1700024G13Rik | 1.01 | 1.21 | 1.06 | 0.48 | 0.19 | 1.00 | 1.13 | 1.11 | 1.10 |
| 1810007D17Rik | 1.00 | 1.00 | 1.00 | 1.00 | 1.00 | 1.00 | 1.00 | 1.00 | 1.00 |
| 1810065E05Rik | 1.00 | 1.00 | 1.00 | 1.00 | 0.10 | 1.00 | 1.00 | 1.00 | 1.00 |
| 2210010C04Rik | 1.00 | 1.00 | 1.00 | 1.00 | 1.00 | 1.00 | 1.00 | 1.00 | 1.00 |
| 2310007L24Rik | 1.00 | 1.00 | 1.00 | 0.51 | 0.17 | 1.00 | 1.00 | 1.00 | 1.00 |
| 2410004P03Rik | 0.91 | 0.99 | 1.11 | 0.51 | 0.20 | 1.00 | 1.00 | 1.00 | 1.00 |
| 2610305D13Rik | 1.00 | 1.00 | 1.00 | 1.68 | 0.19 | 0.36 | 1.17 | 0.82 | 1.00 |
| 2610507I01Rik | 0.90 | 2.89 | 1.01 | 0.87 | 4.27 | 1.03 | 1.00 | 1.00 | 1.00 |
| 4930401O12Rik | 1.00 | 1.00 | 1.00 | 1.00 | 1.00 | 1.00 | 0.16 | 1.20 | 0.44 |
| AF357426 | 0.00 | 1.00 | 3.70 | 1.00 | 1.00 | 1.00 | 1.00 | 1.00 | 1.00 |
| Aldob | 0.79 | 1.09 | 0.51 | 0.74 | 0.13 | 1.38 | 1.00 | 1.00 | 1.00 |
| Alox15 | 1.00 | 1.00 | 1.00 | 3.08 | 0.47 | 0.12 | 1.00 | 1.00 | 1.00 |
| Amy1 | 1.18 | 0.71 | 0.86 | 1.20 | 0.80 | 0.89 | 1.21 | 0.76 | 1.05 |
| Amy2a2 | 1.00 | 1.00 | 1.00 | 1.00 | 1.00 | 1.00 | 1.00 | 1.00 | 1.00 |
| Amy2a4 | 1.00 | 1.00 | 1.00 | 1.00 | 1.00 | 1.00 | 1.00 | 1.00 | 1.00 |
| Amy2b | 1.00 | 1.00 | 1.00 | 1.09 | 1.27 | 0.83 | 1.05 | 1.00 | 1.00 |
| Anapc11 | 0.96 | 0.94 | 1.03 | 0.94 | 0.99 | 0.92 | 0.93 | 0.93 | 0.97 |
| Apol7b | 1.00 | 1.00 | 1.00 | 1.00 | 1.00 | 1.00 | 0.75 | 1.04 | 0.80 |
| Aqp12 | 1.00 | 1.00 | 1.00 | 1.00 | 1.00 | 1.00 | 1.00 | 1.00 | 1.00 |
| Arhgdig | 0.87 | 1.07 | 0.85 | 0.87 | 0.54 | 1.00 | 1.07 | 0.96 | 1.23 |
| Atp6v0c-ps2 | 0.72 | 1.00 | 1.25 | 1.00 | 1.00 | 1.00 | 1.00 | 1.00 | 1.49 |
| Bdh2 | 0.99 | 1.01 | 1.00 | 0.77 | 0.78 | 0.92 | 0.94 | 0.99 | 0.92 |
| Bglap | 1.00 | 1.00 | 1.00 | 1.00 | 1.31 | 1.00 | 1.00 | 1.00 | 1.00 |
| Bglap2 | 1.00 | 1.00 | 1.00 | 1.00 | 3.54 | 1.00 | 1.00 | 1.00 | 1.00 |
| Bmp10 | 1.00 | 1.00 | 1.45 | 1.00 | 1.00 | 1.00 | 1.00 | 1.00 | 1.00 |
| Camk2b | 1.00 | 0.99 | 0.95 | 1.00 | 0.96 | 1.00 | 1.04 | 1.00 | 0.98 |
| Carns1 | 1.31 | 1.02 | 0.97 | 0.94 | 0.88 | 0.78 | 0.85 | 0.85 | 0.89 |
| Ccdc108 | 1.08 | 1.17 | 1.06 | 0.40 | 0.13 | 1.00 | 1.03 | 1.01 | 1.03 |
| Ccdc153 | 0.76 | 1.46 | 1.01 | 0.35 | 0.08 | 1.00 | 1.00 | 1.00 | 1.00 |
| Cckar | 1.00 | 1.00 | 1.00 | 1.00 | 1.00 | 1.00 | 1.00 | 1.00 | 1.00 |
| Ccl28 | 1.00 | 1.00 | 1.00 | 0.43 | 0.10 | 1.00 | 0.74 | 0.86 | 1.00 |
| Cd5l | 1.00 | 1.00 | 1.00 | 1.86 | 0.54 | 0.06 | 0.51 | 1.84 | 0.66 |
| Cda | 0.99 | 0.96 | 0.79 | 0.42 | 0.18 | 1.00 | 1.00 | 1.00 | 1.00 |
| Cdhr5 | 1.00 | 1.00 | 1.00 | 0.45 | 0.14 | 1.00 | 0.71 | 0.89 | 0.91 |
| Cel | 1.00 | 1.00 | 1.00 | 1.00 | 1.00 | 1.00 | 1.00 | 1.00 | 1.00 |
| Cela1 | 0.83 | 1.07 | 1.10 | 0.89 | 0.98 | 1.14 | 1.00 | 1.00 | 1.00 |
| Cela3b | 1.00 | 1.00 | 1.00 | 1.00 | 1.00 | 1.00 | 1.00 | 1.00 | 1.00 |
| Celsr1 | 1.00 | 1.19 | 1.00 | 0.44 | 0.16 | 1.00 | 1.00 | 1.00 | 1.00 |
| Chac1 | 0.94 | 0.93 | 0.96 | 1.44 | 0.97 | 0.63 | 1.18 | 1.01 | 0.81 |
| Ciart | 1.12 | 0.84 | 0.57 | 1.11 | 0.27 | 0.76 | 1.01 | 1.00 | 0.90 |
| Cidea | 1.02 | 1.11 | 1.35 | 0.27 | 0.67 | 0.64 | 0.77 | 0.93 | 0.96 |
| Cideb | 0.73 | 0.67 | 1.17 | 0.40 | 0.11 | 1.00 | 1.00 | 1.00 | 1.00 |
| Cish | 1.17 | 1.49 | 0.89 | 0.07 | 1.46 | 3.38 | 1.03 | 1.05 | 1.05 |
| Cldn10 | 0.93 | 0.93 | 1.05 | 0.59 | 0.20 | 0.62 | 0.86 | 1.01 | 1.00 |
| Clec3a | 1.00 | 1.00 | 1.00 | 1.00 | 1.00 | 1.00 | 1.00 | 1.00 | 1.00 |
| Clps | 1.00 | 1.00 | 1.00 | 1.00 | 1.00 | 1.00 | 1.15 | 0.97 | 1.02 |
| Cpa1 | 1.00 | 1.00 | 1.00 | 1.00 | 1.00 | 1.00 | 1.00 | 1.00 | 1.00 |
| Cpa2 | 1.17 | 1.01 | 0.98 | 1.02 | 1.00 | 1.00 | 1.00 | 1.00 | 0.97 |
| Cpb1 | 1.00 | 1.00 | 1.00 | 1.00 | 1.00 | 1.00 | 1.00 | 1.00 | 1.00 |
| Crabp1 | 0.83 | 0.82 | 0.91 | 0.21 | 0.11 | 1.00 | 1.15 | 1.00 | 1.00 |
| Crtac1 | 0.95 | 1.03 | 0.92 | 2.00 | 0.17 | 0.49 | 0.79 | 0.96 | 1.09 |
| Cryab | 0.89 | 0.71 | 1.20 | 1.00 | 0.83 | 0.86 | 1.02 | 1.39 | 0.76 |
| Ctrc | 1.00 | 1.00 | 1.00 | 1.00 | 1.00 | 1.00 | 2.53 | 0.51 | 1.05 |
| Ctrcos | 1.00 | 1.00 | 1.00 | 1.00 | 1.00 | 1.00 | 1.00 | 1.00 | 1.00 |
| Ctrl | 1.00 | 1.00 | 1.00 | 1.00 | 1.00 | 1.00 | 1.00 | 1.00 | 1.00 |
| Ctsg | 1.00 | 1.00 | 1.00 | 1.00 | 1.00 | 1.00 | 1.00 | 1.00 | 1.00 |
| Cwc22 | 0.08 | 0.39 | 1.69 | 0.10 | 0.37 | 1.70 | 0.10 | 0.43 | 1.19 |
| Cxcl11 | 1.00 | 1.00 | 1.00 | 1.00 | 1.00 | 1.00 | 1.00 | 1.00 | 1.00 |
| Cyp2b9 | 1.00 | 1.00 | 1.00 | 1.00 | 1.00 | 1.00 | 1.00 | 1.00 | 1.00 |
| Cyp2d12 | 1.00 | 1.00 | 1.00 | 1.00 | 1.00 | 1.00 | 1.00 | 1.00 | 1.00 |

Fig. 31- 4

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| 1110017D15Rik | 1.57 | 3.23 | 1.01 | 1.00 | 1.00 | 1.00 | 1.00 | 1.00 | 1.00 | 1.00 | 1.00 | 1.00 |
| 1700001C02Rik | 1.00 | 1.54 | 1.00 | 1.00 | 1.00 | 1.00 | 1.00 | 1.00 | 1.00 | 1.00 | 1.00 | 1.00 |
| 1700007K13Rik | 1.68 | 2.49 | 1.00 | 1.00 | 1.00 | 1.00 | 1.00 | 1.00 | 1.00 | 1.00 | 1.00 | 1.00 |
| 1700009P17Rik | 1.29 | 2.01 | 0.83 | 0.69 | 0.88 | 1.00 | 1.00 | 1.00 | 1.00 | 1.00 | 1.00 | 1.00 |
| 1700024G13Rik | 1.00 | 2.50 | 1.00 | 1.00 | 1.00 | 1.00 | 1.00 | 1.00 | 1.00 | 1.00 | 1.00 | 1.00 |
| 1810007D17Rik | 1.00 | 1.00 | 1.00 | 1.00 | 1.00 | 1.00 | 1.00 | 0.17 | 0.17 | 1.00 | 1.00 | 1.00 |
| 1810065E05Rik | 1.00 | 1.00 | 1.00 | 1.00 | 1.00 | 1.00 | 1.00 | 1.00 | 1.00 | 1.00 | 1.00 | 1.00 |
| 2210010C04Rik | 0.49 | 1.00 | 0.46 | 1.00 | 1.00 | 1.00 | 0.89 | 0.99 | 1.08 | 1.00 | 1.00 | 1.00 |
| 2310007L24Rik | 0.96 | 0.83 | 0.45 | 1.00 | 1.00 | 1.00 | 1.00 | 1.00 | 1.00 | 1.00 | 1.00 | 1.00 |
| 2410004P03Rik | 1.04 | 2.63 | 1.00 | 1.00 | 1.00 | 1.00 | 1.00 | 1.00 | 1.00 | 1.00 | 1.00 | 1.00 |
| 2610305D13Rik | 2.82 | 1.05 | 0.30 | 3.06 | 0.95 | 0.52 | 1.00 | 1.00 | 1.00 | 1.86 | 2.21 | 2.58 |
| 2610507I01Rik | 0.39 | 1.03 | 0.36 | 0.16 | 0.89 | 0.16 | 1.00 | 1.00 | 1.00 | 1.69 | 0.31 | 1.91 |
| 4930401O12Rik | 1.00 | 1.00 | 1.00 | 1.00 | 1.00 | 1.00 | 1.00 | 1.00 | 1.00 | 1.00 | 1.00 | 1.00 |
| AF357426 | 1.00 | 0.03 | 1.00 | 1.00 | 1.00 | 1.00 | 1.00 | 1.00 | 1.00 | 1.00 | 0.88 | 0.79 |
| Aldob | 2.07 | 1.00 | 1.00 | 1.00 | 1.00 | 1.00 | 1.00 | 0.62 | 1.02 | 1.00 | 1.00 | 1.00 |
| Alox15 | 1.72 | 0.87 | 1.46 | 1.18 | 0.82 | 0.67 | 1.00 | 1.00 | 1.00 | 1.00 | 0.95 | 0.96 |
| Amy1 | 2.13 | 1.14 | 1.59 | 1.00 | 1.00 | 1.00 | 0.63 | 1.17 | 2.67 | 1.45 | 1.00 | 1.00 |
| Amy2a2 | 1.00 | 1.00 | 1.00 | 1.00 | 1.00 | 1.00 | 0.73 | 0.97 | 0.85 | 1.00 | 1.22 | 1.01 |
| Amy2a4 | 1.00 | 1.00 | 1.00 | 1.00 | 1.00 | 1.00 | 0.74 | 0.98 | 0.86 | 1.00 | 0.93 | 1.09 |
| Amy2b | 0.45 | 1.00 | 0.12 | 1.00 | 1.00 | 1.00 | 0.75 | 1.19 | 1.14 | 1.00 | 1.03 | 0.95 |
| Anapc11 | 0.95 | 0.97 | 0.98 | 0.92 | 1.01 | 1.13 | 1.00 | 1.00 | 1.00 | 1.01 | 1.00 | 0.19 |
| Apol7b | 3.27 | 0.05 | 3.28 | 1.06 | 1.00 | 1.00 | 1.00 | 1.00 | 1.00 | 1.00 | 1.03 | 1.15 |
| Aqp12 | 1.00 | 1.00 | 1.00 | 1.00 | 1.00 | 1.00 | 0.86 | 1.00 | 1.17 | 1.00 | 1.00 | 1.00 |
| Arhgdig | 1.00 | 1.58 | 1.00 | 1.00 | 1.00 | 1.00 | 1.10 | 0.86 | 1.05 | 1.00 | 1.36 | 0.93 |
| Atp6v0c-ps2 | 0.66 | 1.00 | 1.00 | 2.06 | 1.00 | 0.69 | 1.00 | 1.00 | 1.00 | 1.00 | 1.00 | 1.00 |
| Bdh2 | 1.00 | 1.00 | 1.00 | 1.00 | 1.00 | 1.00 | 2.20 | 0.13 | 0.78 | 0.87 | 1.04 | 1.25 |
| Bglap | 1.15 | 1.18 | 0.94 | 1.00 | 0.77 | 1.00 | 1.00 | 1.00 | 1.00 | 1.00 | 2.02 | 1.43 |
| Bglap2 | 1.35 | 1.72 | 1.00 | 1.00 | 1.00 | 1.00 | 1.00 | 0.44 | 1.01 | 0.78 | 0.96 | 0.93 |
| Bmp10 | 1.00 | 4.91 | 1.00 | 1.00 | 1.00 | 1.00 | 1.00 | 1.00 | 1.00 | 1.00 | 1.00 | 1.00 |
| Camk2b | 1.00 | 1.00 | 1.00 | 1.00 | 1.00 | 1.00 | 1.00 | 1.00 | 1.00 | 1.28 | 0.89 | 1.07 |
| Carns1 | 3.72 | 0.77 | 0.88 | 2.78 | 0.61 | 1.07 | 1.00 | 1.00 | 1.00 | 1.11 | 1.13 | 1.06 |
| Ccdc108 | 1.00 | 1.89 | 1.00 | 1.00 | 1.00 | 1.00 | 1.00 | 1.00 | 1.00 | 1.00 | 1.00 | 1.00 |
| Ccdc153 | 1.19 | 0.84 | 0.58 | 1.00 | 1.00 | 1.00 | 1.00 | 1.00 | 1.00 | 1.00 | 1.00 | 1.00 |
| Cckar | 1.00 | 1.00 | 1.00 | 1.00 | 1.00 | 1.00 | 1.04 | 0.98 | 1.05 | 1.00 | 1.00 | 1.00 |
| Ccl28 | 1.00 | 1.00 | 1.00 | 1.00 | 1.00 | 1.00 | 1.00 | 1.00 | 1.00 | 1.03 | 1.00 | 1.17 |
| Cd5l | 1.59 | 1.63 | 0.73 | 1.18 | 1.12 | 1.51 | 1.00 | 1.00 | 1.00 | 1.00 | 1.00 | 1.00 |
| Cda | 1.00 | 1.00 | 1.00 | 1.00 | 1.00 | 1.00 | 1.00 | 1.00 | 1.00 | 1.00 | 1.00 | 1.00 |
| Cdhr5 | 1.33 | 0.82 | 1.15 | 1.00 | 1.00 | 1.00 | 1.00 | 1.00 | 1.00 | 1.00 | 1.00 | 1.00 |
| Cel | 0.41 | 1.00 | 0.39 | 1.00 | 1.00 | 1.00 | 0.85 | 0.98 | 1.05 | 1.00 | 1.00 | 1.00 |
| Cela1 | 0.63 | 0.93 | 0.15 | 0.87 | 1.07 | 1.18 | 0.92 | 0.85 | 1.05 | 1.10 | 1.00 | 2.78 |
| Cela3b | 0.60 | 1.00 | 0.57 | 1.00 | 1.00 | 1.00 | 0.84 | 0.97 | 0.94 | 1.00 | 1.00 | 1.00 |
| Celsr1 | 0.73 | 1.08 | 0.86 | 0.70 | 1.19 | 0.86 | 1.03 | 1.04 | 1.14 | 1.04 | 0.80 | 1.01 |
| Chac1 | 1.00 | 1.16 | 1.00 | 0.85 | 1.48 | 1.18 | 1.08 | 0.56 | 0.49 | 0.65 | 0.72 | 1.10 |
| Ciart | 0.96 | 1.26 | 0.97 | 1.00 | 1.00 | 1.00 | 0.77 | 0.76 | 1.00 | 0.98 | 1.03 | 1.00 |
| Cidea | 0.94 | 0.89 | 2.65 | 1.00 | 1.00 | 1.00 | 1.00 | 1.00 | 1.00 | 0.95 | 0.97 | 0.98 |
| Cideb | 1.00 | 1.00 | 1.00 | 1.00 | 1.00 | 1.00 | 1.00 | 1.00 | 1.00 | 1.00 | 1.00 | 1.00 |
| Cish | 1.30 | 1.01 | 1.41 | 0.75 | 1.49 | 1.09 | 0.61 | 1.60 | 2.58 | 0.92 | 1.08 | 1.09 |
| Cldn10 | 0.56 | 1.71 | 1.54 | 0.87 | 0.75 | 1.40 | 1.09 | 0.96 | 1.05 | 0.87 | 1.00 | 1.00 |
| Clec3a | 1.00 | 1.00 | 1.00 | 1.00 | 1.00 | 1.00 | 1.00 | 1.00 | 1.00 | 1.15 | 0.82 | 0.99 |
| Clps | 0.30 | 1.00 | 0.14 | 1.00 | 1.00 | 1.00 | 0.72 | 0.87 | 1.03 | 1.00 | 1.00 | 1.00 |
| Cpa1 | 0.43 | 1.00 | 0.35 | 1.00 | 1.00 | 1.00 | 0.86 | 1.00 | 1.07 | 1.00 | 1.00 | 1.00 |
| Cpa2 | 0.82 | 1.00 | 0.58 | 1.00 | 1.00 | 1.00 | 0.92 | 0.87 | 0.98 | 1.00 | 1.15 | 0.98 |
| Cpb1 | 0.51 | 1.00 | 0.39 | 1.00 | 1.00 | 1.00 | 0.85 | 1.29 | 1.00 | 1.00 | 1.00 | 1.00 |
| Crabp1 | 1.39 | 0.82 | 1.28 | 1.00 | 1.00 | 1.00 | 1.00 | 1.00 | 1.00 | 0.79 | 1.04 | 1.02 |
| Crtac1 | 1.00 | 1.00 | 1.00 | 1.19 | 1.89 | 1.02 | 1.00 | 1.00 | 1.00 | 1.00 | 1.00 | 1.00 |
| Cryab | 1.69 | 2.82 | 1.90 | 0.94 | 1.00 | 0.97 | 0.77 | 0.10 | 0.28 | 1.04 | 1.00 | 1.00 |
| Ctrc | 0.64 | 1.00 | 0.62 | 1.00 | 1.00 | 1.00 | 0.75 | 1.20 | 1.21 | 1.00 | 1.00 | 1.00 |
| Ctrcos | 1.00 | 1.00 | 1.00 | 1.00 | 1.00 | 1.00 | 2.22 | 0.18 | 1.76 | 1.00 | 1.00 | 1.00 |
| Ctrl | 0.45 | 1.02 | 0.46 | 1.00 | 1.00 | 1.00 | 0.86 | 0.89 | 1.02 | 1.00 | 1.00 | 1.00 |
| Ctsg | 1.09 | 1.00 | 1.00 | 0.92 | 1.03 | 0.97 | 1.00 | 1.00 | 1.00 | 0.69 | 1.02 | 0.89 |
| Cwc22 | 1.28 | 3.13 | 1.33 | 1.36 | 3.13 | 1.18 | 1.42 | 3.25 | 1.26 | 1.44 | 1.04 | 1.02 |
| Cxcl11 | 0.66 | 0.10 | 0.58 | 1.00 | 1.00 | 1.00 | 1.00 | 1.00 | 1.00 | 1.00 | 1.09 | 1.00 |
| Cyp2b9 | 1.00 | 1.00 | 1.00 | 1.00 | 1.00 | 1.00 | 1.00 | 1.00 | 1.00 | 1.00 | 0.76 | 1.00 |
| Cyp2d12 | 1.00 | 1.00 | 1.00 | 1.00 | 1.00 | 1.00 | 1.00 | 1.00 | 1.00 | 1.00 | 1.00 | 1.00 |

Fig. 31-5

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Cyp2d9 | 1.00 | 1.00 | 1.00 | 3.82 | 0.85 | 0.95 | 1.04 | 0.65 | 0.98 |
| Cypt8 | 1.00 | 1.00 | 1.00 | 1.00 | 1.00 | 1.00 | 1.00 | 1.00 | 1.00 |
| Dao | 1.00 | 1.00 | 1.00 | 0.97 | 0.88 | 1.04 | 1.00 | 1.00 | 1.00 |
| Dbp | 0.45 | 0.12 | 0.44 | 0.59 | 0.18 | 0.80 | 0.24 | 0.15 | 0.63 |
| Dcdc2a | 1.00 | 1.00 | 1.00 | 1.02 | 1.63 | 1.25 | 1.00 | 1.00 | 1.00 |
| Dmbt1 | 1.00 | 1.00 | 1.00 | 1.00 | 1.00 | 1.00 | 1.12 | 1.00 | 1.00 |
| Dnajc22 | 1.00 | 1.00 | 1.00 | 0.91 | 0.90 | 1.14 | 0.99 | 0.83 | 0.91 |
| Dnali1 | 1.00 | 1.00 | 1.00 | 1.00 | 1.00 | 1.00 | 1.00 | 1.00 | 1.00 |
| Dydc2 | 1.00 | 1.00 | 1.00 | 0.93 | 0.84 | 1.00 | 1.00 | 1.00 | 1.00 |
| Dynlrb2 | 1.00 | 1.00 | 1.00 | 1.00 | 1.00 | 1.00 | 1.00 | 1.00 | 1.00 |
| Ear3 | 1.00 | 1.00 | 1.21 | 1.00 | 1.00 | 1.00 | 1.01 | 1.46 | 0.50 |
| Eif3j2 | 1.08 | 0.83 | 0.96 | 0.78 | 0.81 | 1.06 | 0.88 | 1.32 | 1.16 |
| Elane | 1.00 | 1.01 | 1.00 | 1.00 | 1.00 | 1.00 | 1.00 | 3.54 | 1.00 |
| Erp27 | 1.00 | 1.00 | 1.00 | 1.00 | 1.00 | 1.00 | 0.64 | 0.58 | 0.87 |
| F5 | 1.00 | 0.97 | 1.52 | 1.00 | 0.83 | 1.00 | 1.32 | 0.88 | 0.84 |
| Fabp5 | 1.34 | 2.44 | 1.09 | 1.42 | 1.11 | 0.91 | 0.17 | 1.08 | 1.43 |
| Fam166b | 1.00 | 1.00 | 1.00 | 1.00 | 1.00 | 1.00 | 1.00 | 1.00 | 1.00 |
| Fam167a | 1.00 | 1.00 | 1.00 | 1.00 | 1.00 | 1.00 | 1.00 | 1.13 | 1.00 |
| Fam183b | 0.81 | 0.93 | 1.05 | 1.00 | 1.00 | 1.00 | 1.00 | 1.00 | 1.00 |
| Fam213b | 0.67 | 0.73 | 0.70 | 0.18 | 1.20 | 1.01 | 0.44 | 1.05 | 1.06 |
| Fbp1 | 1.00 | 1.00 | 1.00 | 1.03 | 0.77 | 0.97 | 0.91 | 0.65 | 0.98 |
| Fbp2 | 1.20 | 0.66 | 0.48 | 1.19 | 0.97 | 0.92 | 1.00 | 1.00 | 1.00 |
| Fcer2a | 1.00 | 1.00 | 1.39 | 1.00 | 1.00 | 1.00 | 1.00 | 1.00 | 1.00 |
| Fermt1 | 1.00 | 1.00 | 1.00 | 0.97 | 1.02 | 1.12 | 1.00 | 1.00 | 1.00 |
| Fgfr4 | 1.00 | 1.00 | 1.00 | 0.96 | 0.86 | 0.96 | 0.89 | 0.93 | 0.83 |
| Fndc7 | 1.00 | 1.00 | 1.00 | 1.00 | 1.00 | 1.00 | 1.00 | 1.00 | 1.00 |
| Foxj1 | 1.00 | 1.00 | 1.00 | 1.00 | 1.00 | 1.00 | 1.00 | 1.00 | 1.00 |
| Ggta1 | 1.09 | 1.35 | 1.16 | 1.02 | 1.02 | 1.10 | 0.91 | 1.23 | 0.98 |
| Gipc2 | 1.33 | 0.76 | 1.28 | 0.96 | 0.96 | 0.96 | 1.00 | 1.00 | 1.00 |
| Gm10334 | 1.00 | 1.00 | 1.00 | 1.00 | 1.00 | 1.00 | 1.00 | 1.00 | 1.00 |
| Gm11549 | 1.00 | 1.00 | 1.00 | 1.00 | 1.00 | 1.00 | 1.00 | 1.00 | 1.00 |
| Gm12185 | 1.00 | 1.00 | 1.00 | 1.00 | 1.00 | 1.00 | 1.00 | 1.00 | 1.00 |
| Gm13011 | 1.00 | 1.00 | 1.00 | 1.00 | 1.00 | 1.00 | 1.00 | 1.00 | 1.00 |
| Gm21637 | 1.00 | 1.00 | 1.00 | 1.00 | 1.00 | 1.00 | 1.00 | 1.00 | 1.00 |
| Gm5409 | 1.00 | 1.00 | 1.00 | 1.00 | 1.00 | 1.00 | 1.00 | 1.00 | 1.00 |
| Gm5771 | 1.00 | 1.00 | 1.00 | 1.00 | 1.00 | 1.00 | 1.00 | 1.00 | 1.00 |
| Gp2 | 1.00 | 1.00 | 1.00 | 1.24 | 0.98 | 0.87 | 1.00 | 1.00 | 1.00 |
| Guca2a | 1.00 | 1.00 | 1.00 | 0.63 | 1.56 | 0.93 | 1.00 | 1.00 | 1.00 |
| Haao | 1.00 | 1.00 | 1.00 | 1.06 | 0.79 | 0.99 | 0.86 | 0.80 | 0.92 |
| Hal | 1.51 | 3.54 | 1.57 | 1.00 | 1.00 | 1.00 | 0.82 | 0.98 | 1.55 |
| Hamp2 | 0.28 | 0.65 | 1.47 | 1.00 | 1.00 | 1.00 | 1.07 | 0.53 | 1.28 |
| Hdc | 2.15 | 0.85 | 1.21 | 0.80 | 2.91 | 1.81 | 1.15 | 0.71 | 0.60 |
| Hlf | 0.48 | 0.20 | 0.32 | 1.02 | 0.63 | 0.92 | 0.93 | 0.50 | 0.90 |
| Hmgcr | 1.75 | 1.30 | 1.24 | 0.57 | 0.84 | 0.97 | 1.35 | 1.08 | 0.19 |
| Hnf4a | 1.00 | 1.00 | 1.00 | 1.09 | 1.00 | 1.13 | 1.32 | 0.94 | 1.12 |
| Igfals | 1.00 | 1.00 | 0.99 | 0.72 | 0.67 | 0.91 | 0.69 | 0.65 | 1.01 |
| Igsf11 | 1.02 | 1.00 | 1.00 | 0.72 | 0.93 | 1.36 | 0.77 | 1.12 | 1.22 |
| Ihh | 1.00 | 1.00 | 1.00 | 0.83 | 1.00 | 1.62 | 0.55 | 0.61 | 1.06 |
| Iqcg | 1.00 | 0.27 | 3.42 | 0.84 | 0.58 | 1.76 | 1.00 | 0.71 | 1.25 |
| Iyd | 1.00 | 1.00 | 1.00 | 1.11 | 0.70 | 1.03 | 1.10 | 0.87 | 0.88 |
| Klk1 | 1.00 | 1.00 | 1.00 | 0.75 | 0.67 | 0.69 | 1.00 | 1.00 | 1.00 |
| Klk1b11 | 1.00 | 1.00 | 1.00 | 0.77 | 0.74 | 0.64 | 1.00 | 1.00 | 1.00 |
| Klk1b21 | 1.00 | 1.00 | 1.00 | 0.73 | 0.65 | 0.69 | 1.00 | 1.00 | 1.00 |
| Klk1b3 | 1.00 | 1.00 | 1.00 | 0.70 | 0.73 | 0.68 | 1.00 | 1.00 | 1.00 |
| Klk1b4 | 1.00 | 1.00 | 1.00 | 0.75 | 0.66 | 0.68 | 0.88 | 1.18 | 1.02 |
| Klk1b5 | 1.00 | 1.00 | 1.00 | 0.74 | 0.66 | 0.67 | 1.00 | 1.00 | 1.00 |
| Krt12 | 1.00 | 1.00 | 1.00 | 1.00 | 1.00 | 1.00 | 1.00 | 1.00 | 1.00 |
| LOC100048884 | 1.00 | 1.00 | 1.00 | 1.00 | 1.00 | 1.00 | 0.53 | 0.55 | 1.22 |
| Lrrc23 | 1.00 | 1.00 | 1.05 | 1.00 | 1.00 | 1.00 | 1.00 | 1.00 | 1.00 |
| Ltf | 1.00 | 3.08 | 2.31 | 1.00 | 1.19 | 1.00 | 1.00 | 3.71 | 1.00 |
| Ly6d | 1.15 | 1.25 | 2.31 | 0.83 | 1.46 | 1.53 | 0.95 | 1.35 | 1.00 |
| Lyve1 | 1.32 | 0.60 | 1.49 | 1.00 | 1.00 | 1.03 | 1.67 | 2.56 | 0.20 |
| Mapk15 | 1.00 | 1.00 | 1.00 | 0.89 | 0.98 | 0.90 | 1.17 | 1.25 | 1.00 |
| Mcpt8 | 1.00 | 1.00 | 1.00 | 1.00 | 1.00 | 1.00 | 1.00 | 1.27 | 1.00 |

Fig. 31-6

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Cyp2d9 | 1.00 | 1.00 | 1.00 | 1.00 | 1.00 | 1.00 | 1.00 | 1.00 | 1.00 |
| Cypt8 | 1.00 | 1.00 | 1.00 | 1.00 | 1.00 | 1.00 | 1.00 | 1.00 | 1.00 |
| Dao | 1.00 | 1.00 | 1.00 | 1.00 | 1.00 | 1.00 | 1.00 | 1.00 | 1.00 |
| Dbp | 0.37 | 0.09 | 0.50 | 0.28 | 0.13 | 0.63 | 1.00 | 0.31 | 0.65 |
| Dcdc2a | 0.96 | 1.00 | 1.08 | 1.00 | 1.00 | 1.00 | 1.00 | 1.00 | 1.00 |
| Dmbt1 | 1.00 | 1.00 | 1.00 | 1.00 | 1.00 | 1.00 | 1.81 | 0.06 | 0.01 |
| Dnajc22 | 1.00 | 1.00 | 1.00 | 1.00 | 1.00 | 1.00 | 1.00 | 1.00 | 1.00 |
| Dnali1 | 0.90 | 0.77 | 0.89 | 1.00 | 1.00 | 1.00 | 1.00 | 1.00 | 1.00 |
| Dydc2 | 0.84 | 0.81 | 0.78 | 1.00 | 1.00 | 1.00 | 1.00 | 1.00 | 1.00 |
| Dynlrb2 | 0.89 | 0.74 | 0.80 | 1.00 | 1.00 | 1.00 | 1.00 | 1.00 | 1.00 |
| Ear3 | 0.86 | 0.97 | 1.16 | 1.21 | 0.66 | 1.00 | 1.05 | 0.57 | 1.82 |
| Eif3j2 | 1.19 | 1.16 | 0.95 | 1.07 | 1.41 | 0.69 | 1.22 | 1.25 | 1.11 |
| Elane | 0.61 | 2.74 | 1.26 | 1.00 | 0.14 | 0.35 | 0.23 | 1.34 | 2.02 |
| Erp27 | 1.00 | 1.34 | 1.00 | 1.00 | 1.00 | 1.00 | 1.43 | 0.16 | 0.25 |
| F5 | 1.03 | 0.82 | 0.63 | 1.00 | 1.00 | 1.00 | 0.73 | 0.59 | 0.63 |
| Fabp5 | 1.05 | 1.23 | 0.95 | 0.82 | 1.34 | 1.15 | 1.07 | 1.47 | 0.85 |
| Fam166b | 0.88 | 0.80 | 0.93 | 1.00 | 1.00 | 1.00 | 1.00 | 1.00 | 1.00 |
| Fam167a | 1.30 | 0.84 | 0.86 | 1.00 | 1.00 | 0.93 | 0.77 | 0.85 | 1.09 |
| Fam183b | 0.79 | 0.74 | 0.88 | 1.00 | 1.00 | 0.89 | 1.00 | 1.00 | 1.00 |
| Fam213b | 0.87 | 0.88 | 0.90 | 0.84 | 0.94 | 1.14 | 0.91 | 0.95 | 0.93 |
| Fbp1 | 0.72 | 1.13 | 1.00 | 1.00 | 1.00 | 1.00 | 1.00 | 1.00 | 1.00 |
| Fbp2 | 1.17 | 1.05 | 2.11 | 1.17 | 1.26 | 0.79 | 1.21 | 1.00 | 1.00 |
| Fcer2a | 0.18 | 0.65 | 1.27 | 1.00 | 1.00 | 1.00 | 0.71 | 0.69 | 0.98 |
| Fermt1 | 0.81 | 0.82 | 1.00 | 1.00 | 1.00 | 1.00 | 1.00 | 1.00 | 1.00 |
| Fgfr4 | 0.53 | 0.49 | 0.92 | 0.97 | 1.00 | 1.00 | 1.13 | 0.54 | 0.88 |
| Fndc7 | 0.75 | 1.04 | 0.99 | 1.00 | 1.00 | 1.00 | 1.11 | 0.98 | 1.03 |
| Foxj1 | 1.05 | 0.90 | 1.03 | 1.00 | 1.00 | 1.00 | 1.00 | 1.00 | 1.00 |
| Ggta1 | 1.05 | 1.04 | 1.11 | 1.11 | 0.95 | 1.10 | 1.22 | 0.99 | 0.93 |
| Gipc2 | 0.94 | 0.80 | 0.92 | 1.00 | 1.00 | 1.00 | 1.00 | 1.00 | 1.00 |
| Gm10334 | 1.00 | 1.00 | 1.00 | 1.00 | 1.00 | 1.00 | 1.88 | 0.08 | 0.05 |
| Gm11549 | 1.00 | 1.00 | 1.00 | 1.00 | 1.00 | 1.00 | 1.00 | 1.00 | 1.00 |
| Gm12185 | 0.91 | 0.89 | 0.87 | 1.00 | 1.00 | 1.00 | 1.04 | 1.18 | 0.72 |
| Gm13011 | 1.00 | 1.00 | 1.00 | 1.00 | 1.00 | 1.00 | 1.40 | 0.08 | 0.01 |
| Gm21637 | 1.00 | 1.00 | 1.00 | 1.00 | 1.00 | 1.00 | 1.00 | 1.00 | 1.00 |
| Gm5409 | 1.00 | 1.00 | 1.00 | 1.00 | 1.00 | 1.00 | 1.87 | 0.09 | 0.02 |
| Gm5771 | 1.00 | 1.00 | 1.00 | 1.00 | 1.00 | 1.00 | 1.87 | 0.09 | 0.02 |
| Gp2 | 1.52 | 0.98 | 2.21 | 1.00 | 1.00 | 1.00 | 1.59 | 0.08 | 0.03 |
| Guca2a | 1.00 | 1.00 | 1.00 | 1.00 | 1.00 | 1.00 | 1.00 | 1.00 | 1.00 |
| Haao | 0.37 | 0.96 | 0.79 | 1.00 | 1.00 | 1.00 | 1.03 | 0.81 | 0.71 |
| Hal | 2.28 | 1.19 | 1.12 | 1.11 | 0.94 | 0.86 | 1.00 | 1.00 | 0.89 |
| Hamp2 | 1.33 | 0.85 | 1.26 | 1.00 | 1.00 | 1.00 | 0.66 | 0.18 | 0.26 |
| Hdc | 1.04 | 0.93 | 1.43 | 1.00 | 1.00 | 1.00 | 0.74 | 0.95 | 0.88 |
| Hlf | 0.59 | 0.12 | 0.39 | 0.77 | 0.44 | 0.55 | 2.05 | 0.68 | 0.62 |
| Hmgcr | 1.24 | 1.33 | 1.24 | 0.97 | 0.84 | 1.00 | 0.87 | 1.11 | 1.01 |
| Hnf4a | 1.00 | 1.00 | 1.00 | 1.00 | 1.00 | 1.00 | 1.00 | 1.00 | 1.00 |
| Igfals | 1.00 | 1.00 | 1.00 | 0.68 | 0.89 | 1.13 | 1.00 | 1.00 | 1.00 |
| Igsf11 | 1.00 | 1.00 | 1.00 | 1.00 | 1.00 | 1.00 | 1.06 | 1.00 | 1.00 |
| Ihh | 1.00 | 1.00 | 1.00 | 1.00 | 1.00 | 1.00 | 1.00 | 1.00 | 1.00 |
| Iqcg | 0.79 | 0.74 | 1.16 | 0.91 | 0.26 | 2.66 | 1.00 | 1.11 | 4.46 |
| Iyd | 1.08 | 1.01 | 0.96 | 1.00 | 1.00 | 1.00 | 1.00 | 1.00 | 1.00 |
| Klk1 | 0.80 | 1.17 | 1.39 | 1.00 | 1.00 | 1.00 | 1.80 | 0.09 | 0.04 |
| Klk1b11 | 1.00 | 1.00 | 1.00 | 1.00 | 1.00 | 1.00 | 1.77 | 0.19 | 0.32 |
| Klk1b21 | 1.00 | 1.00 | 1.00 | 1.00 | 1.00 | 1.00 | 1.70 | 0.16 | 0.25 |
| Klk1b3 | 1.00 | 1.00 | 1.00 | 1.00 | 1.00 | 1.00 | 2.07 | 0.11 | 0.14 |
| Klk1b4 | 1.00 | 1.00 | 1.00 | 1.00 | 1.00 | 1.00 | 1.94 | 0.10 | 0.12 |
| Klk1b5 | 1.00 | 1.00 | 1.00 | 1.00 | 1.00 | 1.00 | 1.73 | 0.10 | 0.04 |
| Krt12 | 1.00 | 1.00 | 1.00 | 1.00 | 1.00 | 1.00 | 1.00 | 1.00 | 1.00 |
| LOC100048884 | 1.00 | 1.00 | 1.00 | 0.13 | 1.79 | 1.20 | 1.00 | 1.00 | 1.00 |
| Lrrc23 | 0.85 | 0.95 | 0.88 | 1.00 | 1.00 | 1.00 | 1.00 | 1.00 | 0.89 |
| Ltf | 0.69 | 3.48 | 1.00 | 1.00 | 0.13 | 0.30 | 0.25 | 1.47 | 2.08 |
| Ly6d | 0.38 | 1.93 | 0.66 | 1.00 | 1.00 | 1.00 | 0.78 | 1.10 | 0.75 |
| Lyve1 | 2.37 | 1.36 | 2.16 | 1.37 | 0.83 | 1.29 | 3.74 | 0.90 | 0.80 |
| Mapk15 | 0.94 | 0.78 | 0.90 | 1.00 | 1.00 | 1.00 | 1.00 | 1.00 | 1.00 |
| Mcpt8 | 0.88 | 2.07 | 1.00 | 1.00 | 1.00 | 1.00 | 0.16 | 1.34 | 1.36 |

Fig. 31-7

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Cyp2d9 | 1.00 | 1.00 | 1.00 | 0.91 | 0.20 | 1.00 | 1.00 | 1.00 | 1.00 |
| Cypt8 | 1.00 | 1.00 | 1.00 | 1.00 | 1.00 | 1.00 | 1.95 | 3.04 | 0.15 |
| Dao | 1.10 | 1.11 | 1.15 | 0.37 | 0.09 | 1.00 | 1.00 | 1.00 | 1.00 |
| Dbp | 0.81 | 0.80 | 0.70 | 0.46 | 0.15 | 0.68 | 0.80 | 0.78 | 1.03 |
| Dcdc2a | 0.87 | 0.84 | 1.13 | 0.39 | 0.07 | 1.00 | 1.11 | 1.15 | 1.02 |
| Dmbt1 | 1.00 | 1.00 | 1.00 | 1.00 | 0.16 | 1.00 | 1.00 | 1.00 | 1.00 |
| Dnajc22 | 1.00 | 1.00 | 1.00 | 0.38 | 0.11 | 1.00 | 0.74 | 0.80 | 0.92 |
| Dnali1 | 0.95 | 0.89 | 1.22 | 0.43 | 0.20 | 1.00 | 1.06 | 1.00 | 1.06 |
| Dydc2 | 0.99 | 1.05 | 0.80 | 0.46 | 0.17 | 1.00 | 0.96 | 1.08 | 0.94 |
| Dynlrb2 | 0.85 | 0.78 | 0.91 | 0.32 | 0.09 | 1.00 | 1.01 | 1.10 | 1.01 |
| Ear3 | 1.00 | 1.00 | 1.00 | 0.80 | 0.62 | 0.52 | 1.00 | 1.00 | 1.00 |
| Eif3j2 | 0.98 | 0.99 | 1.94 | 1.11 | 1.16 | 1.07 | 1.33 | 0.18 | 1.00 |
| Elane | 1.00 | 1.00 | 1.00 | 1.73 | 0.94 | 1.54 | 1.00 | 1.00 | 1.00 |
| Erp27 | 1.00 | 1.00 | 1.00 | 1.00 | 1.00 | 1.00 | 1.00 | 1.00 | 1.00 |
| F5 | 1.03 | 1.14 | 1.24 | 2.35 | 0.40 | 0.10 | 0.89 | 1.06 | 0.94 |
| Fabp5 | 0.96 | 0.96 | 0.97 | 1.77 | 0.90 | 1.42 | 0.87 | 0.81 | 0.82 |
| Fam166b | 0.99 | 1.03 | 1.08 | 0.52 | 0.13 | 1.00 | 1.17 | 1.20 | 1.39 |
| Fam167a | 1.03 | 1.05 | 1.04 | 0.43 | 0.15 | 1.00 | 1.09 | 1.18 | 1.04 |
| Fam183b | 0.78 | 0.97 | 0.96 | 0.65 | 0.15 | 1.39 | 0.99 | 1.08 | 0.98 |
| Fam213b | 0.97 | 0.94 | 0.97 | 0.78 | 0.81 | 1.18 | 1.09 | 0.89 | 0.85 |
| Fbp1 | 1.00 | 1.00 | 1.00 | 0.79 | 0.19 | 1.05 | 0.98 | 1.00 | 1.06 |
| Fbp2 | 1.00 | 1.00 | 1.00 | 0.64 | 0.09 | 0.95 | 0.97 | 1.00 | 1.00 |
| Fcer2a | 1.00 | 1.00 | 1.00 | 1.00 | 1.00 | 1.00 | 1.00 | 1.00 | 1.00 |
| Fermt1 | 1.00 | 1.00 | 1.00 | 0.42 | 0.16 | 1.00 | 1.00 | 1.00 | 1.00 |
| Fgfr4 | 1.00 | 1.00 | 1.00 | 0.46 | 0.10 | 1.00 | 0.97 | 0.80 | 0.81 |
| Fndc7 | 1.00 | 1.00 | 1.00 | 0.56 | 0.14 | 1.00 | 1.00 | 1.00 | 1.00 |
| Foxj1 | 0.74 | 0.94 | 1.10 | 0.36 | 0.08 | 1.00 | 0.95 | 1.23 | 1.15 |
| Ggta1 | 0.99 | 1.36 | 1.10 | 1.24 | 0.88 | 1.16 | 1.00 | 1.00 | 1.00 |
| Gipc2 | 0.85 | 0.96 | 1.01 | 0.41 | 0.15 | 1.00 | 0.80 | 1.13 | 0.95 |
| Gm10334 | 1.00 | 1.00 | 1.00 | 1.00 | 1.00 | 1.00 | 1.00 | 1.00 | 1.00 |
| Gm11549 | 1.10 | 1.02 | 0.95 | 1.00 | 1.00 | 1.00 | 1.00 | 1.00 | 1.00 |
| Gm12185 | 1.00 | 1.00 | 1.00 | 1.00 | 1.00 | 1.00 | 1.00 | 1.00 | 1.00 |
| Gm13011 | 1.00 | 1.00 | 1.00 | 1.00 | 1.00 | 1.00 | 1.00 | 1.00 | 1.00 |
| Gm21637 | 1.00 | 1.00 | 1.00 | 1.00 | 1.00 | 1.00 | 1.00 | 1.00 | 0.10 |
| Gm5409 | 1.00 | 1.00 | 1.00 | 1.00 | 1.00 | 1.00 | 1.00 | 1.00 | 1.00 |
| Gm5771 | 1.00 | 1.00 | 1.00 | 1.00 | 1.00 | 1.00 | 1.00 | 1.00 | 1.00 |
| Gp2 | 1.00 | 1.00 | 1.00 | 1.00 | 1.00 | 1.00 | 1.00 | 1.00 | 1.00 |
| Guca2a | 1.00 | 1.00 | 1.00 | 1.00 | 0.19 | 1.00 | 1.00 | 1.00 | 1.06 |
| Haao | 1.00 | 1.00 | 1.00 | 0.44 | 0.18 | 0.79 | 1.00 | 1.00 | 1.00 |
| Hal | 1.00 | 1.00 | 1.00 | 1.69 | 1.75 | 0.59 | 0.93 | 1.09 | 1.00 |
| Hamp2 | 1.00 | 1.00 | 1.00 | 1.00 | 1.00 | 1.00 | 1.00 | 1.00 | 1.00 |
| Hdc | 0.78 | 0.92 | 1.11 | 1.88 | 0.17 | 0.72 | 0.95 | 1.03 | 0.98 |
| Hlf | 0.99 | 1.04 | 0.92 | 0.56 | 0.64 | 0.36 | 1.00 | 1.00 | 1.00 |
| Hmgcr | 1.06 | 0.99 | 0.93 | 1.05 | 1.93 | 1.20 | 1.02 | 1.02 | 1.02 |
| Hnf4a | 1.00 | 1.00 | 1.00 | 0.42 | 0.10 | 1.00 | 1.00 | 1.00 | 1.00 |
| Igfals | 1.00 | 1.00 | 1.00 | 0.17 | 1.17 | 1.13 | 1.02 | 1.08 | 1.07 |
| Igsf11 | 1.19 | 0.99 | 1.01 | 0.73 | 0.18 | 1.00 | 1.12 | 1.06 | 1.13 |
| Ihh | 1.00 | 1.00 | 1.00 | 0.51 | 0.20 | 1.00 | 1.00 | 1.00 | 1.00 |
| Iqcg | 0.75 | 0.58 | 1.95 | 0.57 | 0.23 | 1.41 | 1.09 | 0.99 | 1.01 |
| Iyd | 1.00 | 1.00 | 1.00 | 0.44 | 0.11 | 1.00 | 1.00 | 1.00 | 1.00 |
| Klk1 | 1.00 | 1.00 | 1.00 | 1.00 | 0.38 | 1.00 | 1.45 | 0.67 | 1.02 |
| Klk1b11 | 1.00 | 1.00 | 1.00 | 1.00 | 1.00 | 1.00 | 1.00 | 1.00 | 1.00 |
| Klk1b21 | 1.00 | 1.00 | 1.00 | 1.00 | 1.00 | 1.00 | 0.62 | 0.31 | 1.42 |
| Klk1b3 | 1.00 | 1.00 | 1.00 | 1.00 | 1.00 | 1.00 | 1.23 | 0.62 | 1.08 |
| Klk1b4 | 1.00 | 1.00 | 1.00 | 1.00 | 1.00 | 1.00 | 1.33 | 0.73 | 1.16 |
| Klk1b5 | 1.00 | 1.00 | 1.00 | 1.00 | 1.93 | 1.00 | 1.11 | 0.73 | 0.90 |
| Krt12 | 0.14 | 0.93 | 0.40 | 1.00 | 1.00 | 1.00 | 1.00 | 1.00 | 1.00 |
| LOC100048884 | 1.00 | 1.00 | 1.00 | 1.00 | 1.00 | 1.00 | 1.00 | 1.00 | 1.00 |
| Lrrc23 | 0.98 | 0.98 | 1.30 | 0.41 | 0.17 | 1.00 | 1.12 | 1.03 | 1.06 |
| Ltf | 1.00 | 1.04 | 1.00 | 1.00 | 0.35 | 1.00 | 1.00 | 1.00 | 1.30 |
| Ly6d | 1.00 | 1.12 | 1.00 | 1.05 | 1.50 | 0.16 | 0.69 | 2.22 | 0.98 |
| Lyve1 | 1.10 | 1.10 | 1.00 | 1.95 | 1.21 | 0.53 | 1.00 | 1.00 | 1.00 |
| Mapk15 | 1.00 | 1.00 | 1.00 | 0.50 | 0.12 | 1.00 | 0.90 | 1.00 | 1.00 |
| Mcpt8 | 1.00 | 1.00 | 1.00 | 1.00 | 1.00 | 1.00 | 1.00 | 1.00 | 1.00 |

Fig. 31- 8

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Cyp2d9 | 1.00 | 1.00 | 1.00 | 1.00 | 1.00 | 1.00 | 1.00 | 1.00 | 1.00 | 1.00 | 1.00 | 0.65 |
| Cypt8 | 1.00 | 1.00 | 1.00 | 1.00 | 1.00 | 1.00 | 1.00 | 1.00 | 1.00 | 1.00 | 0.98 | 0.85 |
| Dao | 1.00 | 1.00 | 1.00 | 1.00 | 1.00 | 1.00 | 1.00 | 1.00 | 1.00 | 1.00 | 0.94 | 0.87 |
| Dbp | 1.25 | 1.06 | 0.65 | 1.31 | 0.66 | 0.84 | 0.36 | 0.50 | 0.19 | 0.81 | 0.65 | 0.84 |
| Dcdc2a | 1.00 | 1.00 | 1.00 | 1.00 | 1.00 | 1.00 | 1.00 | 1.00 | 1.00 | 1.00 | 0.98 | 1.01 |
| Dmbt1 | 1.00 | 1.00 | 1.00 | 1.00 | 1.00 | 1.00 | 0.85 | 1.18 | 1.01 | 1.00 | 1.00 | 1.00 |
| Dnajc22 | 1.00 | 1.00 | 1.00 | 1.00 | 1.00 | 1.00 | 0.77 | 0.70 | 1.16 | 1.00 | 1.19 | 0.82 |
| Dnali1 | 1.00 | 2.62 | 1.00 | 1.00 | 1.00 | 1.00 | 1.00 | 1.00 | 1.00 | 1.00 | 0.99 | 0.95 |
| Dydc2 | 1.21 | 1.31 | 1.00 | 1.00 | 1.00 | 1.00 | 1.00 | 1.00 | 1.00 | 1.00 | 0.85 | 0.95 |
| Dynlrb2 | 1.78 | 3.55 | 1.00 | 1.00 | 1.00 | 1.00 | 1.00 | 1.00 | 1.00 | 1.00 | 0.92 | 0.86 |
| Ear3 | 2.02 | 2.62 | 0.85 | 1.03 | 0.14 | 0.66 | 1.00 | 1.00 | 1.00 | 1.00 | 1.39 | 1.00 |
| Eif3j2 | 0.99 | 0.95 | 0.99 | 0.71 | 1.82 | 1.33 | 1.18 | 1.32 | 1.04 | 1.10 | 1.10 | 1.06 |
| Elane | 0.78 | 1.61 | 1.00 | 0.86 | 0.95 | 0.93 | 1.00 | 1.00 | 1.00 | 1.00 | 1.00 | 1.00 |
| Erp27 | 1.03 | 1.19 | 1.01 | 1.26 | 1.17 | 0.76 | 0.83 | 1.09 | 1.08 | 1.00 | 1.00 | 1.00 |
| F5 | 1.00 | 0.97 | 1.00 | 1.23 | 1.00 | 1.04 | 1.00 | 1.00 | 1.00 | 1.00 | 1.32 | 1.44 |
| Fabp5 | 0.71 | 0.86 | 1.08 | 0.88 | 1.09 | 1.09 | 0.57 | 1.28 | 0.86 | 0.97 | 0.81 | 1.04 |
| Fam166b | 1.00 | 1.67 | 1.00 | 1.00 | 1.00 | 1.00 | 1.00 | 1.00 | 1.00 | 1.00 | 0.90 | 0.84 |
| Fam167a | 0.89 | 0.85 | 1.24 | 1.00 | 0.84 | 1.00 | 1.00 | 1.00 | 1.00 | 0.91 | 1.00 | 1.00 |
| Fam183b | 1.62 | 3.36 | 1.00 | 1.00 | 1.00 | 1.00 | 1.00 | 1.00 | 1.00 | 1.00 | 1.00 | 1.00 |
| Fam213b | 0.95 | 0.79 | 0.73 | 1.19 | 0.90 | 1.09 | 0.95 | 0.86 | 1.07 | 0.87 | 1.02 | 1.08 |
| Fbp1 | 1.01 | 1.48 | 1.55 | 1.50 | 1.57 | 0.71 | 1.00 | 1.00 | 1.00 | 0.61 | 0.95 | 1.26 |
| Fbp2 | 1.07 | 1.41 | 1.00 | 1.00 | 1.00 | 1.00 | 2.21 | 1.95 | 0.78 | 1.20 | 1.17 | 0.98 |
| Fcer2a | 2.17 | 2.83 | 2.42 | 1.19 | 1.10 | 0.94 | 1.00 | 0.95 | 0.97 | 0.99 | 0.78 | 0.69 |
| Fermt1 | 1.25 | 0.76 | 1.01 | 1.00 | 1.00 | 1.00 | 1.00 | 1.04 | 1.00 | 1.02 | 0.97 | 1.07 |
| Fgfr4 | 1.00 | 1.00 | 1.00 | 1.00 | 1.00 | 1.00 | 1.00 | 1.00 | 1.00 | 1.12 | 0.93 | 0.98 |
| Fndc7 | 1.42 | 0.83 | 1.13 | 1.00 | 1.00 | 1.00 | 1.00 | 1.00 | 1.00 | 1.00 | 1.00 | 1.00 |
| Foxj1 | 2.00 | 2.16 | 1.28 | 1.00 | 1.00 | 1.00 | 1.00 | 1.00 | 1.00 | 1.00 | 1.05 | 0.93 |
| Ggta1 | 0.91 | 1.33 | 1.08 | 1.03 | 1.39 | 1.01 | 1.04 | 0.13 | 1.21 | 1.00 | 1.00 | 1.00 |
| Gipc2 | 1.16 | 0.83 | 0.70 | 1.00 | 1.00 | 1.00 | 1.00 | 1.00 | 1.00 | 0.75 | 1.00 | 1.00 |
| Gm10334 | 1.00 | 1.00 | 1.00 | 1.00 | 1.00 | 1.00 | 0.86 | 1.01 | 0.92 | 1.00 | 1.01 | 1.00 |
| Gm11549 | 1.00 | 1.00 | 1.00 | 1.00 | 1.00 | 1.00 | 1.00 | 1.00 | 1.00 | 1.00 | 0.20 | 0.79 |
| Gm12185 | 1.18 | 1.84 | 1.38 | 1.00 | 1.31 | 1.00 | 1.00 | 1.00 | 1.00 | 1.00 | 0.50 | 0.05 |
| Gm13011 | 1.00 | 1.00 | 1.00 | 1.00 | 1.00 | 1.00 | 0.85 | 0.97 | 0.92 | 1.00 | 1.00 | 1.00 |
| Gm21637 | 1.00 | 1.00 | 1.00 | 1.00 | 1.00 | 1.00 | 1.00 | 1.00 | 1.00 | 1.00 | 1.00 | 1.00 |
| Gm5409 | 1.00 | 1.00 | 1.00 | 1.00 | 1.00 | 1.00 | 0.84 | 1.04 | 0.99 | 1.00 | 1.00 | 1.00 |
| Gm5771 | 1.00 | 1.00 | 1.00 | 1.00 | 1.00 | 1.00 | 0.86 | 1.10 | 0.98 | 1.00 | 0.79 | 1.10 |
| Gp2 | 2.29 | 1.23 | 0.66 | 1.00 | 1.00 | 1.00 | 1.04 | 1.21 | 1.07 | 1.00 | 1.53 | 1.06 |
| Guca2a | 1.00 | 1.00 | 1.00 | 1.00 | 1.00 | 1.00 | 1.00 | 1.00 | 1.00 | 0.58 | 1.00 | 1.00 |
| Haao | 1.82 | 2.60 | 1.98 | 1.05 | 0.87 | 1.19 | 1.00 | 1.00 | 1.00 | 1.00 | 1.00 | 1.00 |
| Hal | 1.34 | 2.37 | 1.91 | 1.06 | 1.49 | 0.87 | 1.00 | 1.00 | 1.00 | 1.01 | 0.19 | 1.00 |
| Hamp2 | 0.92 | 1.30 | 1.03 | 1.00 | 1.00 | 1.00 | 1.39 | 0.59 | 1.46 | 1.00 | 1.00 | 1.00 |
| Hdc | 0.99 | 1.45 | 1.06 | 1.11 | 1.27 | 1.37 | 1.00 | 1.00 | 1.00 | 1.27 | 1.11 | 1.00 |
| Hlf | 1.01 | 1.06 | 1.00 | 0.98 | 1.21 | 0.82 | 1.00 | 1.00 | 1.00 | 1.00 | 1.19 | 1.11 |
| Hmgcr | 0.83 | 0.80 | 0.89 | 0.97 | 1.00 | 0.86 | 1.00 | 1.00 | 1.00 | 0.94 | 1.10 | 1.09 |
| Hnf4a | 1.00 | 1.00 | 1.00 | 1.00 | 1.00 | 1.00 | 0.77 | 1.22 | 1.13 | 1.00 | 1.00 | 1.00 |
| Igfals | 1.18 | 0.92 | 1.09 | 1.00 | 1.00 | 1.00 | 1.00 | 0.19 | 1.00 | 1.00 | 1.00 | 1.00 |
| Igsf11 | 1.00 | 1.00 | 1.00 | 1.00 | 1.00 | 1.00 | 1.13 | 0.90 | 0.99 | 1.20 | 1.00 | 1.00 |
| Ihh | 1.00 | 1.00 | 1.00 | 1.00 | 1.00 | 1.00 | 1.00 | 1.00 | 1.00 | 1.00 | 1.33 | 1.68 |
| Iqcg | 1.00 | 0.18 | 0.20 | 1.00 | 0.30 | 0.42 | 1.00 | 1.00 | 1.00 | 0.80 | 1.00 | 1.00 |
| Iyd | 1.00 | 1.00 | 1.00 | 1.00 | 1.00 | 1.00 | 1.00 | 0.86 | 0.77 | 1.00 | 1.00 | 1.00 |
| Klk1 | 1.32 | 1.05 | 0.90 | 1.32 | 0.46 | 1.19 | 0.93 | 1.24 | 0.99 | 1.00 | 0.91 | 0.94 |
| Klk1b11 | 1.91 | 0.92 | 0.91 | 1.00 | 1.00 | 1.00 | 1.08 | 1.16 | 0.87 | 1.00 | 1.00 | 1.00 |
| Klk1b21 | 1.01 | 0.98 | 0.81 | 1.00 | 1.00 | 1.00 | 0.97 | 1.26 | 0.98 | 1.00 | 1.00 | 1.00 |
| Klk1b3 | 1.38 | 1.09 | 0.93 | 1.00 | 1.00 | 1.00 | 0.98 | 1.19 | 0.99 | 1.00 | 1.00 | 1.00 |
| Klk1b4 | 1.31 | 1.11 | 0.54 | 1.00 | 1.00 | 1.00 | 1.03 | 1.19 | 1.00 | 1.00 | 1.00 | 1.00 |
| Klk1b5 | 1.38 | 0.87 | 0.84 | 1.15 | 0.83 | 1.00 | 0.94 | 1.18 | 0.99 | 1.00 | 1.00 | 1.00 |
| Krt12 | 1.00 | 1.00 | 1.00 | 1.00 | 1.00 | 1.00 | 1.00 | 1.00 | 1.00 | 1.00 | 1.00 | 1.00 |
| LOC100048884 | 1.00 | 1.00 | 1.00 | 1.00 | 1.00 | 1.00 | 1.00 | 1.00 | 1.00 | 1.00 | 1.01 | 0.98 |
| Lrrc23 | 1.12 | 1.35 | 0.94 | 1.00 | 1.00 | 1.00 | 1.00 | 1.00 | 1.00 | 1.00 | 1.03 | 0.96 |
| Ltf | 0.94 | 3.91 | 0.80 | 1.03 | 1.13 | 0.99 | 1.00 | 1.00 | 1.00 | 1.00 | 1.04 | 0.96 |
| Ly6d | 0.95 | 0.96 | 0.82 | 0.95 | 0.45 | 1.08 | 1.12 | 0.51 | 0.72 | 0.88 | 1.00 | 1.00 |
| Lyve1 | 1.74 | 3.15 | 4.96 | 1.00 | 0.71 | 0.92 | 1.10 | 1.19 | 1.01 | 1.39 | 1.17 | 1.01 |
| Mapk15 | 1.21 | 1.80 | 1.00 | 1.00 | 1.00 | 1.00 | 1.00 | 1.00 | 1.00 | 1.00 | 0.99 | 1.04 |
| Mcpt8 | 1.00 | 1.00 | 1.00 | 1.43 | 1.23 | 0.66 | 1.00 | 1.00 | 1.00 | 1.00 | 1.00 | 1.00 |

Fig. 31-9

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mettl7b | 1.00 | 1.00 | 1.00 | 0.82 | 0.74 | 1.18 | 0.75 | 0.76 | 1.06 |
| Mid1 | 1.04 | 1.65 | 1.69 | 0.88 | 0.86 | 1.07 | 1.28 | 1.27 | 1.52 |
| Mir101c | 1.00 | 1.00 | 1.00 | 1.00 | 1.00 | 1.00 | 1.00 | 1.00 | 1.00 |
| Mir128-2 | 1.00 | 1.00 | 1.00 | 1.00 | 1.00 | 1.00 | 1.00 | 1.00 | 1.00 |
| Mir1291 | 1.38 | 0.89 | 1.34 | 0.92 | 1.02 | 1.10 | 4.34 | 1.94 | 1.02 |
| Mir129-1 | 1.00 | 1.00 | 1.00 | 1.00 | 1.00 | 1.00 | 1.00 | 1.00 | 1.00 |
| Mir130b | 1.00 | 1.00 | 1.00 | 1.00 | 1.00 | 1.00 | 1.00 | 1.00 | 1.00 |
| Mir135b | 1.00 | 1.00 | 1.00 | 1.00 | 1.00 | 1.00 | 1.00 | 1.00 | 1.00 |
| Mir137 | 1.00 | 1.00 | 1.00 | 1.00 | 1.00 | 1.00 | 1.00 | 1.00 | 1.00 |
| Mir145b | 1.00 | 1.00 | 1.00 | 1.00 | 1.00 | 1.00 | 1.00 | 1.00 | 1.00 |
| Mir152 | 1.00 | 1.00 | 1.00 | 1.00 | 1.00 | 1.00 | 1.00 | 1.00 | 1.00 |
| Mir16-2 | 1.00 | 1.00 | 1.00 | 1.00 | 1.00 | 1.00 | 1.00 | 1.00 | 1.00 |
| Mir1896 | 0.02 | 1.00 | 1.00 | 1.00 | 1.00 | 1.00 | 1.00 | 1.00 | 1.00 |
| Mir18b | 1.00 | 1.00 | 1.00 | 1.00 | 0.03 | 0.07 | 1.00 | 1.00 | 1.00 |
| Mir1903 | 1.00 | 1.00 | 1.00 | 1.00 | 1.00 | 1.00 | 1.00 | 1.00 | 1.00 |
| Mir1947 | 1.00 | 1.00 | 1.00 | 0.08 | 1.00 | 0.08 | 0.07 | 1.00 | 1.00 |
| Mir195b | 1.00 | 1.00 | 1.00 | 1.00 | 1.00 | 1.00 | 1.00 | 1.00 | 1.00 |
| Mir196a-1 | 1.00 | 1.00 | 1.00 | 1.32 | 1.06 | 0.67 | 1.00 | 1.00 | 1.00 |
| Mir1a-1 | 1.00 | 1.00 | 1.00 | 1.00 | 1.00 | 0.05 | 1.00 | 1.00 | 1.00 |
| Mir1b | 1.00 | 0.17 | 0.30 | 1.00 | 1.00 | 1.00 | 0.25 | 0.28 | 1.00 |
| Mir208a | 1.00 | 0.01 | 1.00 | 1.00 | 1.00 | 1.00 | 1.00 | 1.00 | 1.00 |
| Mir2137 | 1.00 | 0.03 | 1.00 | 1.00 | 1.00 | 1.00 | 1.00 | 1.00 | 1.00 |
| Mir218-1 | 1.00 | 1.00 | 1.00 | 1.00 | 1.00 | 4.36 | 1.00 | 1.00 | 1.00 |
| Mir219b | 1.00 | 1.00 | 1.00 | 1.00 | 1.00 | 1.00 | 1.00 | 1.00 | 1.00 |
| Mir223 | 1.00 | 0.28 | 1.00 | 1.00 | 1.00 | 0.30 | 0.36 | 1.00 | 1.00 |
| Mir296 | 1.00 | 1.00 | 1.00 | 1.00 | 1.00 | 1.00 | 1.00 | 1.00 | 1.00 |
| Mir298 | 1.00 | 1.00 | 1.00 | 1.00 | 1.00 | 1.00 | 1.00 | 1.00 | 1.00 |
| Mir29b-1 | 1.00 | 1.00 | 1.00 | 1.00 | 1.00 | 1.00 | 1.00 | 1.00 | 1.00 |
| Mir3070b | 1.00 | 1.00 | 1.00 | 1.00 | 1.00 | 1.00 | 1.00 | 1.00 | 1.00 |
| Mir3073b | 1.00 | 1.00 | 1.00 | 1.00 | 1.00 | 1.00 | 1.00 | 1.00 | 1.00 |
| Mir3099 | 1.00 | 1.00 | 1.00 | 1.00 | 1.00 | 1.00 | 1.00 | 1.00 | 1.00 |
| Mir30c-1 | 1.00 | 1.00 | 1.00 | 1.00 | 1.00 | 1.00 | 1.00 | 1.00 | 1.00 |
| Mir31 | 1.00 | 1.00 | 1.00 | 1.00 | 1.00 | 1.00 | 0.18 | 0.17 | 1.00 |
| Mir3101 | 1.24 | 1.74 | 1.69 | 2.36 | 0.98 | 2.30 | 0.02 | 1.12 | 0.61 |
| Mir3108 | 1.00 | 1.00 | 1.00 | 1.00 | 1.00 | 1.00 | 1.00 | 1.00 | 1.00 |
| Mir3110 | 1.00 | 1.00 | 1.00 | 1.00 | 1.00 | 1.00 | 1.00 | 1.00 | 1.00 |
| Mir341 | 1.00 | 1.00 | 1.00 | 1.00 | 1.00 | 1.00 | 0.12 | 1.00 | 1.00 |
| Mir344 | 1.00 | 1.00 | 1.00 | 1.00 | 1.00 | 1.00 | 1.00 | 1.00 | 1.00 |
| Mir344-2 | 1.00 | 1.00 | 1.00 | 1.00 | 1.00 | 1.00 | 1.00 | 1.00 | 1.00 |
| Mir344b | 1.00 | 1.00 | 1.00 | 1.00 | 1.00 | 1.00 | 1.00 | 1.00 | 1.00 |
| Mir344d-2 | 1.00 | 1.00 | 1.00 | 1.00 | 1.16 | 1.00 | 1.00 | 1.00 | 1.00 |
| Mir344e | 1.00 | 1.00 | 1.00 | 1.00 | 1.00 | 1.00 | 1.00 | 1.00 | 1.00 |
| Mir344f | 1.00 | 1.00 | 1.00 | 1.00 | 1.00 | 1.00 | 1.00 | 1.00 | 1.00 |
| Mir370 | 1.00 | 1.00 | 1.00 | 1.00 | 1.00 | 1.00 | 1.00 | 1.00 | 1.00 |
| Mir384 | 1.00 | 1.00 | 1.00 | 1.00 | 1.00 | 1.00 | 1.00 | 1.00 | 1.00 |
| Mir449a | 1.00 | 1.00 | 1.00 | 1.00 | 1.00 | 1.00 | 1.00 | 1.00 | 1.00 |
| Mir450-1 | 1.00 | 1.00 | 1.00 | 1.00 | 1.00 | 1.00 | 1.00 | 1.00 | 1.00 |
| Mir452 | 0.07 | 1.00 | 1.00 | 1.00 | 1.00 | 1.00 | 1.00 | 1.00 | 1.00 |
| Mir468 | 1.00 | 1.00 | 1.00 | 1.00 | 1.00 | 1.00 | 1.00 | 1.00 | 1.00 |
| Mir500 | 1.00 | 1.00 | 1.00 | 1.00 | 1.00 | 1.00 | 1.00 | 1.00 | 1.00 |
| Mir504 | 1.00 | 1.00 | 1.00 | 1.00 | 1.00 | 1.00 | 1.00 | 1.00 | 1.00 |
| Mir509 | 1.00 | 1.00 | 1.00 | 1.00 | 1.00 | 1.00 | 1.00 | 1.00 | 1.00 |
| Mir5122 | 1.00 | 1.00 | 1.42 | 1.00 | 0.08 | 1.00 | 1.00 | 1.00 | 0.16 |
| Mir539 | 1.00 | 1.00 | 1.00 | 1.00 | 1.00 | 1.00 | 1.00 | 1.00 | 1.00 |
| Mir542 | 1.00 | 1.00 | 1.00 | 1.00 | 1.00 | 1.00 | 1.00 | 1.00 | 1.00 |
| Mir543 | 1.00 | 1.00 | 1.00 | 1.00 | 1.00 | 1.00 | 1.00 | 1.00 | 1.00 |
| Mir615 | 1.00 | 1.00 | 1.00 | 0.10 | 1.00 | 1.00 | 1.00 | 1.00 | 1.00 |
| Mir6345 | 1.00 | 0.90 | 1.00 | 1.00 | 1.00 | 1.00 | 1.00 | 1.00 | 1.00 |
| Mir6351 | 1.00 | 1.00 | 1.00 | 1.00 | 1.00 | 1.00 | 1.00 | 1.00 | 1.00 |
| Mir6353 | 1.00 | 1.00 | 1.00 | 1.00 | 1.00 | 1.00 | 1.00 | 1.00 | 0.20 |
| Mir6361 | 1.00 | 1.00 | 1.00 | 1.00 | 1.00 | 1.00 | 1.00 | 1.00 | 1.00 |
| Mir6374 | 1.00 | 1.00 | 1.00 | 1.00 | 1.00 | 1.00 | 1.00 | 1.00 | 1.00 |
| Mir6375 | 1.00 | 1.00 | 1.00 | 0.07 | 1.00 | 1.00 | 1.00 | 1.00 | 1.00 |
| Mir6381 | 1.00 | 1.00 | 1.00 | 1.00 | 1.00 | 1.00 | 1.00 | 1.00 | 1.00 |

Fig. 31-10

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mettl7b | 1.00 | 1.00 | 1.00 | 1.00 | 1.00 | 1.00 | 1.00 | 1.00 | 1.00 |
| Mid1 | 1.08 | 1.27 | 1.30 | 1.15 | 0.97 | 1.18 | 0.58 | 1.52 | 0.82 |
| Mir101c | 1.00 | 1.00 | 1.00 | 1.00 | 1.00 | 1.00 | 1.00 | 1.00 | 1.00 |
| Mir128-2 | 1.00 | 1.00 | 1.00 | 1.00 | 1.00 | 1.00 | 1.00 | 1.00 | 1.00 |
| Mir1291 | 1.36 | 1.32 | 1.52 | 1.68 | 0.75 | 1.13 | 2.05 | 0.87 | 1.15 |
| Mir129-1 | 1.00 | 1.00 | 1.00 | 1.00 | 1.00 | 1.00 | 1.00 | 1.00 | 1.00 |
| Mir130b | 1.00 | 1.00 | 1.00 | 1.00 | 1.00 | 1.00 | 1.00 | 1.00 | 1.00 |
| Mir135b | 1.00 | 1.00 | 1.00 | 1.00 | 1.00 | 1.00 | 1.00 | 1.00 | 1.00 |
| Mir137 | 1.00 | 1.00 | 1.00 | 1.00 | 1.00 | 1.00 | 1.00 | 1.00 | 1.00 |
| Mir145b | 1.00 | 1.00 | 0.06 | 1.00 | 1.00 | 1.00 | 1.00 | 1.00 | 1.00 |
| Mir152 | 1.00 | 1.00 | 1.00 | 1.00 | 1.00 | 1.00 | 1.00 | 1.00 | 1.00 |
| Mir16-2 | 1.00 | 1.00 | 0.16 | 1.00 | 1.00 | 1.00 | 1.00 | 1.00 | 1.00 |
| Mir1896 | 1.00 | 1.00 | 1.00 | 1.00 | 1.00 | 1.00 | 1.00 | 1.00 | 1.00 |
| Mir18b | 1.00 | 1.00 | 1.00 | 1.00 | 1.00 | 1.00 | 1.00 | 1.00 | 1.00 |
| Mir1903 | 1.00 | 1.00 | 1.00 | 1.00 | 1.00 | 1.00 | 1.00 | 1.00 | 1.00 |
| Mir1947 | 1.00 | 1.00 | 1.00 | 1.00 | 1.00 | 1.00 | 1.00 | 0.06 | 1.00 |
| Mir195b | 1.00 | 1.00 | 1.00 | 1.00 | 1.00 | 1.00 | 1.00 | 1.00 | 1.00 |
| Mir196a-1 | 1.00 | 0.21 | 1.00 | 1.00 | 1.00 | 1.00 | 1.01 | 0.12 | 1.59 |
| Mir1a-1 | 1.00 | 1.00 | 1.00 | 0.03 | 0.03 | 0.03 | 1.00 | 1.00 | 1.00 |
| Mir1b | 1.00 | 1.00 | 1.00 | 0.35 | 1.00 | 1.00 | 1.00 | 4.13 | 1.00 |
| Mir208a | 1.00 | 1.00 | 0.09 | 1.00 | 1.00 | 1.00 | 1.00 | 1.00 | 1.00 |
| Mir2137 | 1.00 | 0.03 | 1.00 | 1.00 | 1.00 | 1.00 | 1.00 | 1.00 | 1.00 |
| Mir218-1 | 1.00 | 0.27 | 1.00 | 1.00 | 1.00 | 1.00 | 1.00 | 1.00 | 1.00 |
| Mir219b | 1.00 | 1.00 | 0.03 | 1.00 | 1.00 | 1.00 | 1.00 | 1.00 | 1.00 |
| Mir223 | 0.27 | 1.02 | 2.11 | 0.59 | 1.00 | 1.00 | 1.00 | 1.00 | 1.00 |
| Mir296 | 1.00 | 1.00 | 1.00 | 1.00 | 1.00 | 1.00 | 1.00 | 1.00 | 1.00 |
| Mir298 | 1.00 | 1.00 | 1.00 | 1.00 | 1.00 | 1.00 | 1.00 | 1.00 | 1.00 |
| Mir29b-1 | 1.00 | 0.05 | 1.00 | 1.00 | 1.00 | 1.00 | 1.00 | 1.00 | 1.00 |
| Mir3070b | 1.00 | 1.00 | 1.00 | 1.00 | 1.00 | 1.00 | 1.00 | 1.00 | 1.00 |
| Mir3073b | 1.00 | 1.00 | 1.00 | 1.00 | 1.00 | 1.00 | 1.00 | 1.00 | 1.00 |
| Mir3099 | 1.00 | 1.00 | 1.00 | 1.00 | 1.00 | 1.00 | 1.00 | 1.00 | 1.00 |
| Mir30c-1 | 1.00 | 1.00 | 1.00 | 1.00 | 1.00 | 1.00 | 0.08 | 1.00 | 1.00 |
| Mir31 | 0.23 | 1.00 | 1.00 | 1.00 | 1.00 | 1.00 | 1.00 | 1.00 | 1.00 |
| Mir3101 | 0.83 | 1.54 | 0.96 | 0.10 | 3.85 | 1.77 | 1.06 | 0.82 | 1.17 |
| Mir3108 | 1.00 | 1.00 | 1.00 | 1.00 | 1.00 | 1.00 | 1.00 | 1.00 | 1.00 |
| Mir3110 | 1.00 | 1.00 | 1.00 | 1.00 | 1.00 | 1.00 | 1.00 | 1.00 | 1.00 |
| Mir341 | 1.00 | 1.00 | 1.00 | 1.00 | 1.00 | 1.00 | 1.00 | 1.00 | 1.00 |
| Mir344 | 1.00 | 1.00 | 0.16 | 1.00 | 1.00 | 1.00 | 1.00 | 1.00 | 1.00 |
| Mir344-2 | 1.01 | 1.00 | 0.08 | 1.00 | 1.00 | 1.00 | 1.00 | 1.00 | 1.00 |
| Mir344b | 1.00 | 1.00 | 1.00 | 1.00 | 1.00 | 1.00 | 1.00 | 1.00 | 1.00 |
| Mir344d-2 | 1.00 | 0.08 | 1.00 | 1.00 | 1.00 | 1.00 | 1.00 | 1.00 | 1.00 |
| Mir344e | 1.00 | 1.00 | 0.03 | 1.00 | 1.00 | 1.00 | 1.00 | 1.00 | 1.00 |
| Mir344f | 1.00 | 0.04 | 1.00 | 1.00 | 1.00 | 1.00 | 1.00 | 1.00 | 1.00 |
| Mir370 | 1.00 | 1.00 | 1.00 | 0.07 | 1.00 | 1.00 | 1.00 | 1.00 | 1.00 |
| Mir384 | 1.00 | 1.00 | 1.00 | 1.00 | 1.00 | 1.00 | 1.00 | 1.00 | 1.00 |
| Mir449a | 1.00 | 1.00 | 1.00 | 1.00 | 1.00 | 1.18 | 1.00 | 1.00 | 1.00 |
| Mir450-1 | 1.00 | 1.00 | 1.00 | 1.00 | 1.00 | 1.00 | 1.00 | 1.00 | 1.00 |
| Mir452 | 1.00 | 1.00 | 1.00 | 1.00 | 1.00 | 1.00 | 1.00 | 1.00 | 1.00 |
| Mir468 | 1.00 | 1.00 | 1.00 | 1.00 | 1.00 | 0.06 | 1.00 | 1.00 | 1.00 |
| Mir500 | 1.00 | 1.00 | 1.00 | 1.00 | 1.00 | 1.00 | 1.00 | 1.00 | 1.00 |
| Mir504 | 1.00 | 1.00 | 1.00 | 1.00 | 0.07 | 1.00 | 1.00 | 1.00 | 1.00 |
| Mir509 | 1.00 | 1.00 | 1.00 | 1.00 | 1.00 | 1.00 | 1.00 | 1.00 | 1.00 |
| Mir5122 | 0.26 | 1.00 | 1.00 | 1.00 | 1.00 | 1.00 | 1.00 | 1.00 | 1.00 |
| Mir539 | 1.00 | 1.00 | 1.00 | 1.00 | 1.00 | 1.00 | 1.00 | 1.00 | 1.00 |
| Mir542 | 0.10 | 1.00 | 1.00 | 1.00 | 1.00 | 1.00 | 1.00 | 1.00 | 1.00 |
| Mir543 | 1.00 | 1.00 | 1.00 | 1.00 | 1.00 | 1.00 | 1.00 | 1.00 | 1.00 |
| Mir615 | 1.00 | 1.00 | 1.00 | 0.13 | 1.00 | 0.11 | 1.00 | 1.00 | 1.00 |
| Mir6345 | 0.44 | 0.14 | 1.11 | 1.00 | 1.00 | 1.00 | 0.31 | 3.85 | 1.00 |
| Mir6351 | 1.00 | 1.00 | 1.00 | 1.00 | 1.00 | 1.00 | 1.00 | 1.00 | 1.00 |
| Mir6353 | 1.00 | 1.00 | 1.00 | 1.00 | 1.00 | 1.00 | 1.00 | 1.00 | 1.00 |
| Mir6361 | 1.00 | 1.00 | 1.00 | 1.00 | 1.00 | 1.00 | 1.00 | 1.00 | 1.00 |
| Mir6374 | 1.00 | 4.48 | 1.00 | 1.00 | 1.00 | 1.00 | 1.00 | 1.00 | 1.00 |
| Mir6375 | 1.00 | 1.00 | 1.00 | 1.00 | 1.00 | 1.00 | 1.00 | 1.00 | 1.00 |
| Mir6381 | 1.00 | 1.00 | 1.00 | 1.00 | 1.00 | 1.00 | 1.00 | 1.00 | 1.00 |

Fig. 31-11

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mettl7b | 1.00 | 1.00 | 1.00 | 0.37 | 0.18 | 1.31 | 0.96 | 1.00 | 1.00 |
| Mid1 | 0.87 | 1.39 | 1.15 | 0.99 | 0.94 | 1.17 | 0.62 | 1.33 | 1.00 |
| Mir101c | 1.00 | 1.00 | 1.00 | 1.00 | 1.00 | 1.00 | 0.06 | 1.00 | 1.00 |
| Mir128-2 | 1.00 | 1.00 | 1.00 | 1.00 | 1.00 | 1.00 | 1.00 | 1.00 | 1.00 |
| Mir1291 | 1.80 | 0.69 | 0.92 | 0.40 | 1.23 | 0.70 | 1.48 | 1.93 | 3.66 |
| Mir129-1 | 1.00 | 0.03 | 1.00 | 1.00 | 1.00 | 1.00 | 1.00 | 1.00 | 1.00 |
| Mir130b | 1.00 | 1.00 | 1.00 | 1.00 | 1.00 | 1.00 | 1.00 | 0.09 | 1.12 |
| Mir135b | 1.00 | 0.97 | 1.00 | 1.00 | 1.00 | 1.00 | 2.04 | 0.16 | 1.01 |
| Mir137 | 1.00 | 0.03 | 1.00 | 1.00 | 1.00 | 1.00 | 1.00 | 1.00 | 1.00 |
| Mir145b | 1.00 | 1.00 | 1.00 | 1.00 | 1.00 | 1.00 | 1.00 | 1.00 | 1.00 |
| Mir152 | 1.00 | 1.00 | 1.00 | 1.00 | 1.00 | 1.00 | 1.00 | 1.00 | 1.00 |
| Mir16-2 | 1.00 | 1.00 | 1.00 | 1.00 | 1.00 | 1.00 | 1.00 | 1.00 | 0.16 |
| Mir1896 | 1.00 | 1.00 | 1.00 | 1.00 | 1.00 | 1.00 | 1.00 | 1.26 | 2.59 |
| Mir18b | 1.00 | 1.00 | 1.00 | 1.00 | 1.00 | 1.00 | 1.00 | 1.00 | 1.00 |
| Mir1903 | 0.03 | 1.00 | 1.00 | 1.00 | 1.00 | 1.00 | 1.00 | 1.00 | 1.00 |
| Mir1947 | 1.00 | 1.00 | 0.09 | 1.00 | 1.00 | 1.00 | 1.11 | 0.09 | 1.00 |
| Mir195b | 1.00 | 1.00 | 1.00 | 1.00 | 1.00 | 1.00 | 1.00 | 1.00 | 1.00 |
| Mir196a-1 | 1.00 | 1.00 | 1.00 | 0.23 | 0.75 | 1.00 | 0.30 | 0.92 | 1.86 |
| Mir1a-1 | 1.00 | 1.00 | 1.00 | 1.00 | 1.00 | 1.00 | 1.00 | 1.00 | 1.00 |
| Mir1b | 3.91 | 1.00 | 1.00 | 1.00 | 1.00 | 1.00 | 1.00 | 1.00 | 1.00 |
| Mir208a | 2.00 | 2.00 | 2.10 | 1.00 | 1.00 | 1.00 | 1.00 | 1.00 | 1.00 |
| Mir2137 | 1.00 | 1.00 | 1.00 | 1.00 | 1.00 | 1.00 | 1.00 | 1.00 | 0.04 |
| Mir218-1 | 0.20 | 1.00 | 0.14 | 1.00 | 1.00 | 1.00 | 1.00 | 1.00 | 1.00 |
| Mir219b | 0.34 | 0.60 | 2.39 | 1.00 | 1.00 | 1.00 | 1.00 | 1.00 | 1.00 |
| Mir223 | 1.00 | 3.62 | 1.00 | 2.17 | 0.13 | 1.00 | 0.26 | 1.00 | 1.00 |
| Mir296 | 1.00 | 1.00 | 1.00 | 1.00 | 1.00 | 1.00 | 1.00 | 0.07 | 1.00 |
| Mir298 | 1.00 | 1.00 | 1.00 | 0.06 | 1.00 | 1.00 | 1.00 | 1.00 | 1.00 |
| Mir29b-1 | 1.00 | 1.00 | 1.00 | 1.00 | 1.00 | 1.00 | 1.00 | 1.00 | 1.00 |
| Mir3070b | 0.67 | 0.74 | 0.35 | 1.00 | 1.00 | 1.00 | 1.00 | 1.00 | 1.00 |
| Mir3073b | 1.00 | 1.00 | 1.00 | 1.00 | 1.00 | 1.00 | 0.07 | 1.00 | 1.00 |
| Mir3099 | 0.05 | 1.00 | 1.00 | 1.00 | 1.00 | 1.00 | 1.00 | 1.00 | 1.00 |
| Mir30c-1 | 1.00 | 1.00 | 1.00 | 1.00 | 1.00 | 1.00 | 1.00 | 1.00 | 1.00 |
| Mir31 | 0.18 | 1.00 | 4.76 | 1.00 | 1.00 | 1.00 | 1.00 | 1.00 | 1.00 |
| Mir3101 | 0.70 | 0.59 | 0.30 | 1.46 | 0.79 | 0.71 | 0.61 | 0.88 | 1.35 |
| Mir3108 | 1.00 | 1.00 | 1.00 | 1.00 | 1.00 | 1.00 | 0.08 | 0.04 | 1.12 |
| Mir3110 | 1.00 | 1.00 | 0.06 | 1.00 | 1.00 | 1.00 | 1.00 | 1.00 | 1.00 |
| Mir341 | 1.09 | 3.15 | 1.47 | 1.00 | 0.13 | 1.00 | 1.00 | 1.00 | 1.00 |
| Mir344 | 1.00 | 1.00 | 1.00 | 1.00 | 1.00 | 1.00 | 0.15 | 1.00 | 1.00 |
| Mir344-2 | 0.41 | 0.87 | 0.93 | 1.00 | 1.00 | 1.00 | 1.00 | 1.00 | 1.00 |
| Mir344b | 1.00 | 1.00 | 1.00 | 1.00 | 1.00 | 1.00 | 1.10 | 0.01 | 0.69 |
| Mir344d-2 | 1.00 | 1.00 | 0.02 | 1.00 | 1.00 | 1.00 | 4.16 | 0.02 | 2.60 |
| Mir344e | 1.00 | 1.00 | 1.00 | 1.00 | 1.00 | 1.00 | 1.00 | 1.00 | 1.00 |
| Mir344f | 1.00 | 1.00 | 1.00 | 1.00 | 1.00 | 1.00 | 1.00 | 1.00 | 1.00 |
| Mir370 | 1.00 | 1.00 | 1.00 | 1.00 | 1.00 | 1.00 | 1.00 | 1.00 | 1.00 |
| Mir384 | 0.83 | 1.79 | 0.15 | 1.00 | 1.00 | 1.00 | 1.00 | 1.00 | 1.00 |
| Mir449a | 1.00 | 1.00 | 1.00 | 1.00 | 1.00 | 1.00 | 1.00 | 1.00 | 1.00 |
| Mir450-1 | 1.00 | 1.00 | 1.00 | 1.00 | 1.00 | 1.00 | 0.13 | 1.00 | 1.00 |
| Mir452 | 1.00 | 1.00 | 1.00 | 1.00 | 1.00 | 1.00 | 1.00 | 1.00 | 1.00 |
| Mir468 | 1.00 | 1.00 | 1.00 | 1.00 | 1.00 | 1.00 | 0.81 | 0.96 | 0.81 |
| Mir500 | 1.00 | 1.00 | 1.00 | 1.00 | 1.00 | 1.00 | 1.00 | 1.00 | 1.00 |
| Mir504 | 1.00 | 1.00 | 1.00 | 1.00 | 1.00 | 1.00 | 1.00 | 1.00 | 1.00 |
| Mir509 | 1.00 | 1.00 | 1.00 | 1.00 | 1.00 | 1.00 | 1.00 | 0.06 | 1.00 |
| Mir5122 | 1.00 | 1.00 | 1.00 | 1.00 | 1.00 | 1.00 | 1.00 | 1.00 | 1.00 |
| Mir539 | 1.00 | 1.00 | 1.00 | 1.00 | 1.00 | 1.00 | 0.06 | 1.00 | 1.99 |
| Mir542 | 1.00 | 1.00 | 1.00 | 1.00 | 1.00 | 1.00 | 0.10 | 0.10 | 0.11 |
| Mir543 | 1.00 | 1.00 | 1.00 | 1.00 | 1.00 | 1.00 | 1.00 | 1.00 | 1.00 |
| Mir615 | 1.00 | 1.00 | 1.00 | 0.46 | 1.00 | 0.99 | 1.00 | 1.00 | 1.00 |
| Mir6345 | 1.00 | 0.33 | 1.81 | 1.00 | 1.00 | 1.00 | 1.00 | 1.00 | 0.43 |
| Mir6351 | 1.00 | 0.13 | 1.00 | 1.00 | 1.00 | 1.00 | 1.00 | 1.00 | 1.00 |
| Mir6353 | 1.00 | 1.00 | 1.00 | 1.00 | 1.00 | 1.00 | 1.00 | 1.00 | 1.00 |
| Mir6361 | 1.00 | 1.00 | 1.00 | 1.00 | 1.00 | 1.00 | 1.00 | 1.00 | 1.00 |
| Mir6374 | 1.00 | 1.00 | 1.00 | 1.00 | 1.00 | 1.00 | 4.71 | 1.00 | 0.13 |
| Mir6375 | 1.00 | 1.00 | 0.14 | 1.00 | 1.00 | 1.00 | 0.15 | 1.00 | 1.00 |
| Mir6381 | 1.00 | 1.00 | 1.00 | 1.00 | 1.00 | 1.00 | 0.11 | 1.00 | 1.00 |

Fig. 31- 12

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mettl7b | 1.00 | 1.00 | 1.00 | 1.00 | 1.00 | 1.00 | 1.00 | 1.00 | 1.00 | 0.73 | 1.07 | 1.00 |
| Mid1 | 0.56 | 0.22 | 1.39 | 0.33 | 0.19 | 1.48 | 0.81 | 0.47 | 1.00 | 1.16 | 1.09 | 0.97 |
| Mir101c | 1.00 | 1.00 | 1.00 | 1.00 | 1.00 | 1.00 | 1.00 | 1.00 | 1.00 | 1.00 | 1.00 | 1.00 |
| Mir128-2 | 1.00 | 1.00 | 0.05 | 1.00 | 1.00 | 1.00 | 1.00 | 1.00 | 1.00 | 1.00 | 1.00 | 1.00 |
| Mir1291 | 0.76 | 0.97 | 1.06 | 1.24 | 0.92 | 0.56 | 2.47 | 0.24 | 0.85 | 1.00 | 1.00 | 0.08 |
| Mir129-1 | 1.00 | 1.00 | 1.00 | 1.00 | 1.00 | 1.00 | 1.00 | 1.00 | 1.00 | 1.00 | 1.00 | 1.00 |
| Mir130b | 1.00 | 1.03 | 0.02 | 1.00 | 1.00 | 0.09 | 1.00 | 1.00 | 1.00 | 1.00 | 1.00 | 1.00 |
| Mir135b | 1.00 | 1.00 | 1.00 | 1.00 | 1.00 | 1.00 | 1.00 | 1.00 | 1.00 | 1.00 | 1.00 | 1.00 |
| Mir137 | 1.00 | 1.00 | 1.00 | 1.00 | 1.00 | 1.00 | 1.00 | 1.00 | 1.00 | 1.00 | 1.00 | 1.00 |
| Mir145b | 1.00 | 1.00 | 1.00 | 1.00 | 1.00 | 1.00 | 1.00 | 1.00 | 1.00 | 1.00 | 1.00 | 1.00 |
| Mir152 | 1.00 | 1.00 | 0.04 | 1.00 | 1.00 | 1.00 | 1.00 | 1.00 | 1.00 | 1.00 | 1.00 | 1.00 |
| Mir16-2 | 1.00 | 1.00 | 1.00 | 1.00 | 0.14 | 1.00 | 1.00 | 1.00 | 1.00 | 1.00 | 1.00 | 1.00 |
| Mir1896 | 1.00 | 1.00 | 1.00 | 1.00 | 1.00 | 1.26 | 1.00 | 1.00 | 1.00 | 1.00 | 1.00 | 1.00 |
| Mir18b | 1.00 | 1.00 | 1.00 | 1.00 | 1.00 | 1.00 | 1.00 | 1.00 | 1.00 | 1.00 | 1.00 | 1.00 |
| Mir1903 | 1.00 | 1.00 | 1.00 | 1.00 | 1.00 | 1.00 | 1.00 | 1.00 | 1.00 | 1.00 | 1.00 | 1.00 |
| Mir1947 | 1.00 | 1.00 | 1.00 | 1.00 | 0.10 | 1.00 | 1.00 | 1.00 | 1.00 | 1.00 | 1.00 | 1.00 |
| Mir195b | 1.00 | 0.13 | 1.00 | 1.00 | 1.00 | 1.00 | 1.00 | 1.00 | 1.00 | 1.00 | 1.00 | 1.00 |
| Mir196a-1 | 1.00 | 0.88 | 0.16 | 1.00 | 1.00 | 1.00 | 1.00 | 1.00 | 1.00 | 1.00 | 1.00 | 1.00 |
| Mir1a-1 | 1.00 | 1.00 | 1.00 | 1.00 | 1.00 | 1.00 | 1.00 | 1.00 | 1.00 | 1.00 | 1.00 | 1.00 |
| Mir1b | 1.00 | 3.03 | 1.00 | 0.32 | 1.00 | 1.00 | 1.00 | 1.00 | 1.00 | 1.00 | 1.00 | 1.00 |
| Mir208a | 1.00 | 1.00 | 1.00 | 1.00 | 1.00 | 1.00 | 1.00 | 1.00 | 1.00 | 1.00 | 1.00 | 1.00 |
| Mir2137 | 1.00 | 1.00 | 1.00 | 1.00 | 1.00 | 1.00 | 1.00 | 1.00 | 1.00 | 1.00 | 1.00 | 1.00 |
| Mir218-1 | 1.00 | 1.00 | 1.00 | 1.00 | 1.00 | 1.00 | 1.00 | 1.00 | 1.00 | 1.00 | 1.00 | 1.00 |
| Mir219b | 1.00 | 1.00 | 1.00 | 1.00 | 1.00 | 1.00 | 1.00 | 1.00 | 1.00 | 1.00 | 1.00 | 1.00 |
| Mir223 | 0.13 | 0.13 | 1.00 | 1.00 | 1.00 | 1.00 | 1.00 | 1.00 | 1.00 | 1.00 | 0.97 | 1.06 |
| Mir296 | 1.00 | 1.00 | 1.00 | 1.00 | 1.00 | 1.00 | 1.00 | 1.00 | 1.00 | 1.00 | 1.00 | 1.00 |
| Mir298 | 1.00 | 1.00 | 0.07 | 1.00 | 1.00 | 1.00 | 1.00 | 1.00 | 1.00 | 1.00 | 1.00 | 1.00 |
| Mir29b-1 | 1.00 | 1.00 | 1.00 | 1.00 | 1.00 | 1.00 | 1.00 | 1.00 | 1.00 | 1.00 | 1.00 | 1.00 |
| Mir3070b | 0.10 | 1.00 | 1.00 | 1.00 | 1.00 | 1.00 | 1.00 | 1.00 | 1.00 | 1.00 | 1.00 | 1.00 |
| Mir3073b | 1.00 | 1.00 | 1.00 | 1.00 | 1.00 | 1.00 | 1.00 | 1.00 | 1.00 | 1.00 | 1.00 | 1.00 |
| Mir3099 | 1.00 | 1.00 | 1.00 | 1.00 | 1.00 | 1.00 | 1.00 | 1.00 | 1.00 | 1.00 | 1.00 | 1.00 |
| Mir30c-1 | 0.10 | 1.00 | 1.00 | 1.00 | 1.00 | 1.00 | 1.00 | 1.00 | 1.00 | 1.00 | 1.00 | 1.00 |
| Mir31 | 1.00 | 1.00 | 1.00 | 1.00 | 1.00 | 1.00 | 1.00 | 1.00 | 1.00 | 1.00 | 1.00 | 1.00 |
| Mir3101 | 1.23 | 0.82 | 0.93 | 1.37 | 1.11 | 1.25 | 0.37 | 0.66 | 0.55 | 1.00 | 1.00 | 1.00 |
| Mir3108 | 1.00 | 1.00 | 1.00 | 1.00 | 1.00 | 1.00 | 1.00 | 1.00 | 1.00 | 1.00 | 1.00 | 1.00 |
| Mir3110 | 1.00 | 1.00 | 1.00 | 1.00 | 1.00 | 1.00 | 1.00 | 1.00 | 1.00 | 1.00 | 1.00 | 1.00 |
| Mir341 | 1.00 | 1.00 | 1.00 | 1.00 | 1.00 | 1.00 | 1.00 | 1.00 | 1.00 | 1.00 | 1.00 | 1.00 |
| Mir344 | 1.00 | 1.00 | 1.00 | 1.00 | 1.00 | 1.00 | 1.00 | 1.00 | 1.00 | 1.00 | 1.00 | 1.00 |
| Mir344-2 | 1.00 | 1.00 | 1.00 | 1.00 | 1.00 | 1.00 | 1.00 | 1.00 | 1.00 | 1.00 | 1.00 | 1.00 |
| Mir344b | 1.00 | 1.00 | 1.00 | 1.00 | 1.00 | 1.00 | 1.00 | 1.00 | 1.00 | 1.00 | 1.00 | 1.00 |
| Mir344d-2 | 1.00 | 1.00 | 1.00 | 1.00 | 1.00 | 1.00 | 1.00 | 1.00 | 1.00 | 1.00 | 1.00 | 1.00 |
| Mir344e | 1.00 | 1.00 | 1.00 | 1.00 | 1.00 | 1.00 | 1.00 | 1.00 | 1.00 | 1.00 | 1.00 | 1.00 |
| Mir344f | 1.00 | 1.00 | 1.00 | 1.00 | 1.00 | 1.00 | 1.00 | 1.00 | 1.00 | 1.00 | 1.00 | 1.00 |
| Mir370 | 1.00 | 1.00 | 1.00 | 1.00 | 1.00 | 1.00 | 1.00 | 1.00 | 1.00 | 1.00 | 1.00 | 1.00 |
| Mir384 | 1.00 | 1.00 | 1.00 | 1.00 | 1.00 | 1.00 | 1.00 | 1.00 | 1.00 | 1.00 | 1.00 | 1.00 |
| Mir449a | 1.00 | 0.11 | 1.00 | 1.00 | 1.00 | 1.00 | 1.00 | 1.00 | 1.00 | 1.00 | 1.00 | 1.00 |
| Mir450-1 | 1.00 | 1.00 | 1.00 | 1.00 | 1.00 | 1.00 | 1.00 | 1.00 | 1.00 | 1.00 | 1.00 | 1.00 |
| Mir452 | 1.00 | 1.00 | 1.00 | 1.00 | 1.00 | 1.00 | 1.00 | 1.00 | 1.00 | 1.00 | 1.00 | 1.00 |
| Mir468 | 1.00 | 1.00 | 1.00 | 1.00 | 1.00 | 1.00 | 1.00 | 1.00 | 1.00 | 1.00 | 1.00 | 1.00 |
| Mir500 | 1.00 | 1.00 | 1.00 | 1.00 | 1.00 | 0.14 | 1.00 | 1.00 | 1.00 | 1.00 | 1.00 | 1.00 |
| Mir504 | 1.00 | 1.00 | 1.00 | 1.00 | 1.00 | 1.00 | 1.00 | 1.00 | 1.00 | 1.00 | 1.00 | 1.00 |
| Mir509 | 1.00 | 1.00 | 1.00 | 1.00 | 1.00 | 1.00 | 1.00 | 1.00 | 1.00 | 1.00 | 1.00 | 1.00 |
| Mir5122 | 1.00 | 1.00 | 1.00 | 1.00 | 1.00 | 1.00 | 1.00 | 1.00 | 2.07 | 1.00 | 1.00 | 1.00 |
| Mir539 | 1.00 | 1.00 | 1.00 | 1.00 | 1.00 | 1.00 | 1.00 | 1.00 | 1.00 | 1.00 | 1.00 | 1.00 |
| Mir542 | 1.00 | 1.00 | 1.00 | 0.11 | 1.00 | 1.00 | 1.00 | 1.00 | 1.00 | 1.00 | 1.00 | 1.00 |
| Mir543 | 0.05 | 1.00 | 1.00 | 1.00 | 1.00 | 1.00 | 1.00 | 1.00 | 1.00 | 1.00 | 1.00 | 1.00 |
| Mir615 | 1.00 | 1.00 | 1.00 | 1.00 | 1.00 | 1.00 | 1.00 | 1.00 | 1.00 | 1.00 | 1.00 | 1.00 |
| Mir6345 | 1.16 | 0.34 | 0.19 | 1.00 | 1.00 | 0.26 | 1.00 | 0.41 | 0.52 | 1.00 | 1.00 | 1.00 |
| Mir6351 | 1.00 | 1.00 | 1.00 | 1.00 | 1.00 | 1.00 | 1.00 | 1.00 | 1.00 | 1.00 | 1.00 | 1.00 |
| Mir6353 | 1.00 | 1.00 | 1.00 | 1.00 | 1.00 | 1.00 | 1.00 | 1.00 | 1.00 | 1.00 | 1.00 | 1.00 |
| Mir6361 | 1.00 | 0.16 | 1.00 | 1.00 | 1.00 | 1.00 | 1.00 | 1.00 | 1.00 | 1.00 | 1.00 | 1.00 |
| Mir6374 | 1.00 | 1.00 | 1.00 | 1.00 | 1.00 | 1.00 | 1.00 | 1.00 | 1.00 | 1.00 | 1.00 | 1.00 |
| Mir6375 | 1.00 | 1.00 | 1.00 | 1.00 | 1.00 | 1.00 | 1.00 | 1.00 | 1.00 | 1.00 | 1.00 | 1.00 |
| Mir6381 | 1.00 | 1.00 | 1.00 | 1.00 | 1.00 | 1.00 | 1.00 | 1.00 | 1.00 | 1.00 | 1.00 | 1.00 |

Fig. 31-13

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir6385 | 3.01 | 0.43 | 2.10 | 1.19 | 3.24 | 0.29 | 0.17 | 4.21 | 1.00 |
| Mir6393 | 1.00 | 1.00 | 1.00 | 0.12 | 1.00 | 1.00 | 1.00 | 1.00 | 1.00 |
| Mir6394 | 1.00 | 1.00 | 1.00 | 1.00 | 1.00 | 1.00 | 1.00 | 1.00 | 1.00 |
| Mir6409 | 1.00 | 1.00 | 1.00 | 1.00 | 1.00 | 1.00 | 1.00 | 0.10 | 1.00 |
| Mir6410 | 1.00 | 1.00 | 1.00 | 1.00 | 1.00 | 1.00 | 1.00 | 1.00 | 1.00 |
| Mir6516 | 1.37 | 1.73 | 0.70 | 0.95 | 1.00 | 0.64 | 1.97 | 0.55 | 4.01 |
| Mir668 | 1.00 | 1.00 | 1.00 | 1.00 | 1.00 | 1.00 | 1.00 | 1.00 | 0.02 |
| Mir669a-2 | 1.00 | 1.00 | 1.00 | 1.00 | 1.00 | 1.00 | 1.00 | 1.00 | 1.00 |
| Mir670 | 1.00 | 1.00 | 1.00 | 1.00 | 1.00 | 1.00 | 1.00 | 1.00 | 1.00 |
| Mir677 | 1.04 | 0.71 | 1.29 | 1.79 | 0.61 | 1.24 | 2.42 | 0.23 | 0.41 |
| Mir680-3 | 1.00 | 1.00 | 1.00 | 1.00 | 1.00 | 1.00 | 1.00 | 1.00 | 1.00 |
| Mir683-1 | 1.00 | 1.00 | 1.00 | 1.00 | 0.19 | 4.66 | 1.00 | 1.00 | 1.00 |
| Mir6899 | 1.00 | 1.00 | 1.00 | 1.00 | 1.00 | 1.00 | 1.00 | 1.00 | 1.00 |
| Mir6901 | 0.02 | 1.00 | 1.00 | 1.00 | 1.00 | 1.00 | 1.00 | 1.00 | 1.00 |
| Mir6906 | 1.00 | 1.00 | 1.00 | 1.00 | 1.00 | 1.00 | 1.00 | 1.00 | 1.00 |
| Mir693 | 1.00 | 1.00 | 1.00 | 1.00 | 1.00 | 1.00 | 1.00 | 1.00 | 1.00 |
| Mir6949 | 1.00 | 1.00 | 1.00 | 1.00 | 1.00 | 1.00 | 1.00 | 1.00 | 1.00 |
| Mir695 | 1.00 | 1.00 | 1.00 | 1.00 | 1.00 | 1.00 | 1.00 | 1.00 | 1.00 |
| Mir6952 | 1.00 | 0.02 | 1.00 | 1.00 | 1.00 | 1.00 | 1.00 | 1.00 | 1.00 |
| Mir6955 | 3.37 | 0.85 | 0.75 | 0.97 | 2.26 | 0.61 | 1.04 | 0.39 | 0.47 |
| Mir6956 | 1.00 | 1.00 | 1.00 | 1.00 | 1.00 | 1.00 | 1.00 | 1.00 | 1.00 |
| Mir6965 | 1.00 | 1.00 | 1.00 | 1.00 | 1.00 | 1.00 | 1.00 | 1.00 | 1.00 |
| Mir6971 | 1.00 | 1.00 | 1.00 | 1.00 | 1.00 | 1.00 | 1.00 | 1.00 | 1.00 |
| Mir698 | 1.00 | 1.00 | 1.00 | 1.00 | 0.20 | 1.00 | 1.00 | 1.00 | 1.00 |
| Mir6983 | 1.00 | 1.00 | 1.00 | 1.00 | 1.00 | 1.00 | 1.00 | 1.00 | 1.00 |
| Mir6987 | 1.00 | 1.00 | 1.00 | 1.00 | 1.00 | 1.00 | 1.00 | 1.00 | 1.00 |
| Mir7038 | 1.00 | 1.00 | 1.00 | 1.00 | 1.00 | 1.00 | 1.00 | 1.00 | 1.00 |
| Mir705 | 1.00 | 1.00 | 1.00 | 1.00 | 1.00 | 1.00 | 1.00 | 1.00 | 1.00 |
| Mir7055 | 1.00 | 1.00 | 1.00 | 1.00 | 1.00 | 1.00 | 1.00 | 1.00 | 1.00 |
| Mir7056 | 1.00 | 1.00 | 1.00 | 1.00 | 1.00 | 1.00 | 1.00 | 1.00 | 1.00 |
| Mir7060 | 2.85 | 0.27 | 2.08 | 1.25 | 3.56 | 0.69 | 1.47 | 2.98 | 2.32 |
| Mir7065 | 1.00 | 1.00 | 1.00 | 1.00 | 0.01 | 1.00 | 1.00 | 1.00 | 1.00 |
| Mir7076 | 1.00 | 1.00 | 1.00 | 1.00 | 1.00 | 1.00 | 1.00 | 1.00 | 1.00 |
| Mir7094-1 | 1.00 | 1.00 | 1.00 | 1.00 | 1.00 | 1.00 | 1.00 | 1.00 | 1.00 |
| Mir7094-2 | 1.00 | 1.00 | 1.00 | 1.00 | 1.00 | 1.00 | 1.00 | 1.00 | 1.00 |
| Mir7-2 | 1.00 | 1.00 | 1.00 | 1.00 | 1.00 | 1.00 | 1.00 | 1.00 | 1.00 |
| Mir721 | 1.00 | 1.00 | 1.00 | 1.00 | 1.00 | 1.00 | 1.00 | 1.00 | 1.00 |
| Mir7235 | 1.00 | 1.00 | 1.00 | 1.00 | 1.00 | 1.00 | 1.00 | 1.00 | 1.00 |
| Mir743 | 1.00 | 1.00 | 1.00 | 1.00 | 1.00 | 1.00 | 1.00 | 1.00 | 1.00 |
| Mir7667 | 1.00 | 1.00 | 1.00 | 1.00 | 1.00 | 1.00 | 1.00 | 1.00 | 1.00 |
| Mir770 | 1.00 | 1.00 | 1.00 | 1.00 | 1.00 | 1.00 | 1.00 | 1.00 | 1.00 |
| Mir8091 | 1.58 | 1.02 | 0.56 | 0.59 | 0.92 | 2.32 | 0.52 | 0.51 | 1.01 |
| Mir8101 | 1.00 | 1.00 | 1.00 | 0.21 | 1.00 | 1.00 | 1.00 | 1.00 | 1.00 |
| Mir8109 | 1.00 | 1.00 | 1.00 | 1.00 | 1.00 | 1.00 | 1.00 | 1.00 | 1.00 |
| Mir8110 | 1.00 | 1.00 | 1.00 | 1.00 | 1.00 | 1.00 | 1.00 | 1.00 | 1.00 |
| Mir9-3 | 1.00 | 1.00 | 1.00 | 1.00 | 1.00 | 1.00 | 1.00 | 1.00 | 1.00 |
| Mirlet7a-2 | 1.00 | 1.00 | 1.00 | 1.00 | 1.00 | 1.00 | 1.00 | 1.00 | 1.00 |
| Mmd2 | 1.00 | 1.00 | 1.00 | 1.00 | 1.00 | 1.00 | 0.67 | 1.63 | 1.29 |
| Mmp7 | 1.00 | 1.00 | 1.00 | 1.00 | 1.00 | 1.00 | 1.00 | 1.00 | 1.00 |
| Mpo | 1.00 | 1.15 | 1.00 | 1.00 | 1.00 | 1.00 | 1.00 | 4.01 | 1.00 |
| Mrs2 | 0.83 | 0.58 | 0.91 | 0.82 | 0.77 | 1.10 | 0.95 | 0.90 | 1.20 |
| Ms4a1 | 1.00 | 1.00 | 1.49 | 1.00 | 1.00 | 1.00 | 1.00 | 1.00 | 1.00 |
| Mt3 | 0.72 | 0.64 | 2.05 | 0.58 | 0.74 | 0.88 | 1.00 | 1.00 | 1.00 |
| Mup1 | 1.00 | 1.00 | 1.00 | 1.00 | 1.00 | 1.00 | 0.48 | 0.53 | 1.18 |
| Mup10 | 1.00 | 1.00 | 1.00 | 1.00 | 1.00 | 1.00 | 0.50 | 0.55 | 1.17 |
| Mup11 | 1.00 | 1.00 | 1.00 | 1.00 | 1.00 | 1.00 | 0.53 | 0.56 | 1.18 |
| Mup12 | 1.00 | 1.00 | 1.00 | 1.00 | 1.00 | 1.00 | 0.48 | 0.53 | 1.17 |
| Mup13 | 1.00 | 1.00 | 1.00 | 1.00 | 1.00 | 1.00 | 0.50 | 0.55 | 1.21 |
| Mup14 | 1.00 | 1.00 | 1.00 | 1.00 | 1.00 | 1.00 | 0.48 | 0.56 | 1.22 |
| Mup15 | 1.00 | 1.00 | 1.00 | 1.00 | 1.00 | 1.00 | 0.48 | 0.52 | 1.16 |
| Mup16 | 1.00 | 1.00 | 1.00 | 1.00 | 1.00 | 1.00 | 0.48 | 0.54 | 1.23 |
| Mup17 | 1.00 | 1.00 | 1.00 | 1.00 | 1.00 | 1.00 | 0.47 | 0.52 | 1.23 |
| Mup19 | 1.00 | 1.00 | 1.00 | 1.00 | 1.00 | 1.00 | 0.50 | 0.54 | 1.20 |
| Mup2 | 1.00 | 1.00 | 1.00 | 1.00 | 1.00 | 1.00 | 0.52 | 0.55 | 1.20 |

Fig. 31-14

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir6385 | 1.44 | 4.53 | 0.43 | 0.08 | 3.64 | 0.19 | 0.96 | 1.23 | 1.06 |
| Mir6393 | 1.00 | 1.00 | 1.00 | 1.00 | 1.00 | 1.00 | 1.00 | 1.00 | 1.00 |
| Mir6394 | 1.00 | 1.00 | 1.00 | 1.00 | 1.00 | 1.00 | 1.00 | 1.00 | 1.00 |
| Mir6409 | 1.00 | 1.00 | 3.32 | 1.00 | 1.00 | 0.14 | 1.00 | 0.05 | 1.00 |
| Mir6410 | 1.00 | 1.00 | 1.00 | 1.00 | 1.00 | 1.00 | 1.00 | 1.00 | 0.14 |
| Mir6516 | 1.28 | 0.77 | 0.68 | 0.49 | 2.80 | 1.26 | 1.15 | 0.98 | 1.31 |
| Mir668 | 1.00 | 1.00 | 1.00 | 1.00 | 1.00 | 1.00 | 1.00 | 1.00 | 1.00 |
| Mir669a-2 | 1.00 | 1.00 | 1.00 | 1.00 | 1.00 | 1.00 | 1.00 | 1.00 | 1.00 |
| Mir670 | 1.00 | 1.00 | 1.00 | 0.18 | 1.00 | 1.00 | 1.00 | 1.00 | 1.00 |
| Mir677 | 0.88 | 0.50 | 0.86 | 1.04 | 0.70 | 0.74 | 0.94 | 1.31 | 1.35 |
| Mir680-3 | 1.00 | 1.00 | 1.00 | 1.00 | 1.00 | 1.00 | 1.00 | 1.00 | 1.00 |
| Mir683-1 | 1.00 | 1.00 | 1.00 | 1.00 | 4.05 | 1.00 | 1.00 | 1.00 | 1.00 |
| Mir6899 | 1.00 | 1.00 | 1.00 | 1.00 | 1.00 | 1.00 | 1.00 | 1.00 | 1.00 |
| Mir6901 | 1.00 | 0.03 | 1.00 | 1.00 | 1.00 | 1.00 | 1.00 | 1.00 | 1.00 |
| Mir6906 | 1.00 | 1.00 | 1.00 | 1.00 | 1.00 | 1.00 | 1.00 | 1.00 | 1.00 |
| Mir693 | 1.00 | 1.00 | 1.00 | 1.00 | 1.00 | 1.00 | 1.00 | 1.00 | 1.00 |
| Mir6949 | 1.00 | 1.00 | 1.00 | 1.00 | 1.00 | 1.00 | 0.02 | 1.00 | 1.00 |
| Mir695 | 1.00 | 3.80 | 1.00 | 1.00 | 1.00 | 1.00 | 1.00 | 1.00 | 4.84 |
| Mir6952 | 1.00 | 1.00 | 1.00 | 1.00 | 1.00 | 1.00 | 0.01 | 1.00 | 1.00 |
| Mir6955 | 1.30 | 1.27 | 0.97 | 0.61 | 0.67 | 0.90 | 1.09 | 1.29 | 1.45 |
| Mir6956 | 1.00 | 1.00 | 1.00 | 1.00 | 1.00 | 1.00 | 1.00 | 1.00 | 1.00 |
| Mir6965 | 1.00 | 1.00 | 1.00 | 1.00 | 1.00 | 1.00 | 1.00 | 0.01 | 1.00 |
| Mir6971 | 1.00 | 1.00 | 1.00 | 1.00 | 1.00 | 1.00 | 1.00 | 1.00 | 1.00 |
| Mir698 | 1.00 | 1.00 | 1.00 | 1.00 | 1.00 | 1.00 | 1.00 | 1.00 | 1.00 |
| Mir6983 | 1.00 | 1.00 | 1.00 | 1.00 | 1.00 | 1.00 | 1.00 | 1.00 | 1.00 |
| Mir6987 | 1.00 | 1.00 | 1.00 | 1.00 | 0.05 | 1.00 | 0.01 | 1.00 | 1.00 |
| Mir7038 | 1.00 | 1.00 | 1.00 | 1.00 | 1.00 | 1.00 | 1.00 | 1.00 | 1.00 |
| Mir705 | 1.00 | 1.00 | 1.00 | 1.00 | 1.00 | 1.00 | 0.26 | 1.00 | 1.00 |
| Mir7055 | 1.00 | 1.00 | 1.00 | 1.00 | 1.00 | 1.00 | 1.00 | 1.00 | 1.00 |
| Mir7056 | 1.00 | 1.00 | 1.00 | 1.00 | 1.00 | 1.00 | 1.00 | 1.00 | 1.00 |
| Mir7060 | 1.20 | 0.96 | 0.64 | 0.69 | 0.41 | 0.47 | 1.35 | 1.21 | 1.33 |
| Mir7065 | 1.00 | 0.02 | 1.00 | 1.00 | 1.00 | 1.00 | 1.00 | 1.00 | 1.00 |
| Mir7076 | 1.00 | 1.00 | 1.00 | 1.00 | 1.00 | 1.00 | 0.02 | 0.01 | 1.00 |
| Mir7094-1 | 1.00 | 1.00 | 1.00 | 1.00 | 1.00 | 1.00 | 1.00 | 1.00 | 0.01 |
| Mir7094-2 | 1.00 | 1.00 | 1.00 | 1.00 | 1.00 | 1.00 | 1.00 | 1.00 | 0.01 |
| Mir7-2 | 1.00 | 1.00 | 1.00 | 1.00 | 1.00 | 1.00 | 1.00 | 1.00 | 1.00 |
| Mir721 | 1.00 | 1.00 | 1.00 | 1.00 | 1.00 | 1.00 | 1.00 | 1.00 | 1.00 |
| Mir7235 | 1.00 | 1.00 | 1.00 | 1.00 | 1.00 | 1.00 | 1.00 | 1.00 | 1.00 |
| Mir743 | 1.00 | 1.00 | 1.00 | 1.00 | 1.00 | 1.00 | 1.00 | 1.00 | 1.00 |
| Mir7667 | 1.00 | 1.00 | 1.00 | 1.00 | 1.00 | 1.00 | 1.00 | 1.00 | 1.00 |
| Mir770 | 1.00 | 1.00 | 1.00 | 1.00 | 1.00 | 1.00 | 1.00 | 1.00 | 1.00 |
| Mir8091 | 1.62 | 0.82 | 1.01 | 0.33 | 3.05 | 0.51 | 0.62 | 0.96 | 0.87 |
| Mir8101 | 1.00 | 1.00 | 1.00 | 1.00 | 1.00 | 1.00 | 1.00 | 1.00 | 1.00 |
| Mir8109 | 1.00 | 1.00 | 1.00 | 1.00 | 1.00 | 1.00 | 1.00 | 1.00 | 1.00 |
| Mir8110 | 1.00 | 1.00 | 1.00 | 1.00 | 1.00 | 1.00 | 1.00 | 1.00 | 1.00 |
| Mir9-3 | 1.00 | 1.00 | 1.00 | 1.00 | 1.00 | 1.00 | 1.00 | 1.00 | 1.00 |
| Mirlet7a-2 | 1.00 | 1.00 | 1.00 | 1.00 | 1.00 | 1.00 | 1.00 | 1.00 | 1.00 |
| Mmd2 | 1.00 | 1.00 | 1.00 | 1.00 | 1.00 | 1.00 | 1.00 | 1.00 | 1.00 |
| Mmp7 | 1.00 | 1.00 | 1.00 | 1.00 | 1.00 | 1.00 | 1.00 | 1.00 | 1.00 |
| Mpo | 0.55 | 3.89 | 1.17 | 1.00 | 0.15 | 0.43 | 0.24 | 1.22 | 1.99 |
| Mrs2 | 1.07 | 0.77 | 1.06 | 0.80 | 0.84 | 1.03 | 0.97 | 0.92 | 1.05 |
| Ms4a1 | 0.25 | 1.06 | 0.70 | 1.00 | 1.00 | 1.00 | 0.90 | 0.92 | 0.88 |
| Mt3 | 2.09 | 2.45 | 1.33 | 0.50 | 0.88 | 1.41 | 1.00 | 1.00 | 1.00 |
| Mup1 | 1.00 | 1.00 | 1.00 | 0.13 | 2.00 | 1.29 | 1.00 | 1.00 | 1.00 |
| Mup10 | 1.00 | 1.00 | 1.00 | 0.11 | 1.68 | 1.45 | 1.00 | 1.00 | 1.00 |
| Mup11 | 1.00 | 1.00 | 1.00 | 0.13 | 2.34 | 1.43 | 1.00 | 1.00 | 1.00 |
| Mup12 | 1.00 | 1.00 | 1.00 | 0.14 | 2.17 | 1.18 | 1.00 | 1.00 | 1.00 |
| Mup13 | 1.00 | 1.00 | 1.00 | 0.13 | 1.66 | 1.37 | 1.00 | 1.00 | 1.00 |
| Mup14 | 1.00 | 1.00 | 1.00 | 0.15 | 2.21 | 1.22 | 1.00 | 1.00 | 1.00 |
| Mup15 | 1.00 | 1.00 | 1.00 | 0.17 | 2.11 | 1.10 | 1.00 | 1.00 | 1.00 |
| Mup16 | 1.00 | 1.00 | 1.00 | 0.14 | 1.73 | 1.19 | 1.00 | 1.00 | 1.00 |
| Mup17 | 1.00 | 1.00 | 1.00 | 0.10 | 1.74 | 1.20 | 1.00 | 1.00 | 1.00 |
| Mup19 | 1.00 | 1.00 | 1.00 | 0.11 | 1.83 | 1.30 | 1.00 | 1.00 | 1.00 |
| Mup2 | 1.00 | 1.00 | 1.00 | 0.14 | 1.82 | 1.00 | 1.00 | 1.00 | 1.00 |

Fig. 31-15

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir6385 | 0.17 | 0.18 | 0.56 | 1.66 | 0.84 | 0.31 | 1.00 | 0.20 | 4.87 |
| Mir6393 | 1.00 | 1.00 | 1.00 | 1.00 | 1.00 | 1.00 | 1.00 | 1.00 | 1.00 |
| Mir6394 | 1.00 | 1.00 | 1.00 | 1.00 | 1.00 | 1.00 | 0.18 | 1.00 | 1.00 |
| Mir6409 | 1.00 | 1.00 | 1.00 | 0.09 | 1.00 | 0.19 | 0.04 | 0.30 | 1.00 |
| Mir6410 | 1.00 | 1.00 | 1.00 | 1.00 | 1.00 | 1.00 | 1.00 | 0.21 | 1.00 |
| Mir6516 | 0.36 | 2.20 | 0.64 | 0.21 | 1.83 | 1.39 | 0.82 | 0.67 | 0.62 |
| Mir668 | 0.01 | 0.01 | 0.02 | 1.00 | 1.00 | 1.00 | 1.00 | 1.00 | 0.04 |
| Mir669a-2 | 1.00 | 1.00 | 1.00 | 1.00 | 1.00 | 1.00 | 1.00 | 0.15 | 1.00 |
| Mir670 | 0.75 | 1.00 | 0.09 | 1.00 | 1.00 | 1.00 | 1.11 | 0.39 | 0.64 |
| Mir677 | 3.80 | 1.97 | 0.83 | 1.96 | 1.65 | 2.31 | 2.19 | 0.69 | 1.39 |
| Mir680-3 | 1.00 | 1.00 | 1.00 | 1.00 | 1.00 | 1.00 | 1.00 | 1.00 | 1.00 |
| Mir683-1 | 1.00 | 1.00 | 1.00 | 1.00 | 1.00 | 1.00 | 0.73 | 0.79 | 1.54 |
| Mir6899 | 1.00 | 1.00 | 1.00 | 1.00 | 1.00 | 1.00 | 1.00 | 1.00 | 1.00 |
| Mir6901 | 1.00 | 1.00 | 1.00 | 1.00 | 1.00 | 1.00 | 1.00 | 1.00 | 1.00 |
| Mir6906 | 1.00 | 1.00 | 1.00 | 1.00 | 1.00 | 1.00 | 1.00 | 1.00 | 0.02 |
| Mir693 | 1.00 | 1.00 | 1.00 | 1.00 | 1.00 | 1.00 | 1.00 | 0.12 | 1.00 |
| Mir6949 | 1.00 | 1.00 | 1.00 | 1.00 | 1.00 | 1.00 | 1.00 | 1.00 | 1.00 |
| Mir695 | 1.00 | 0.19 | 1.00 | 1.00 | 1.00 | 1.00 | 1.00 | 1.00 | 1.00 |
| Mir6952 | 1.00 | 1.00 | 1.00 | 1.00 | 1.00 | 1.00 | 1.00 | 1.00 | 1.00 |
| Mir6955 | 1.01 | 0.77 | 1.04 | 0.74 | 1.38 | 1.87 | 0.03 | 1.69 | 0.76 |
| Mir6956 | 1.00 | 1.00 | 1.00 | 1.00 | 1.00 | 1.00 | 1.00 | 1.00 | 1.00 |
| Mir6965 | 1.00 | 1.00 | 1.00 | 1.00 | 1.00 | 1.00 | 1.00 | 1.00 | 1.00 |
| Mir6971 | 1.00 | 1.00 | 1.00 | 1.00 | 1.00 | 1.00 | 1.00 | 0.03 | 1.00 |
| Mir698 | 1.00 | 1.00 | 1.00 | 1.00 | 1.00 | 1.00 | 0.09 | 3.95 | 1.00 |
| Mir6983 | 1.00 | 1.00 | 1.00 | 1.00 | 1.00 | 1.00 | 1.00 | 1.00 | 1.00 |
| Mir6987 | 1.00 | 1.00 | 1.00 | 1.00 | 1.00 | 1.00 | 1.00 | 1.00 | 1.00 |
| Mir7038 | 1.00 | 1.00 | 1.00 | 1.00 | 0.03 | 1.00 | 1.00 | 1.00 | 1.00 |
| Mir705 | 1.00 | 1.00 | 1.00 | 1.00 | 0.16 | 1.00 | 1.00 | 1.00 | 1.00 |
| Mir7055 | 0.00 | 1.00 | 1.00 | 1.00 | 1.00 | 1.00 | 1.00 | 1.00 | 1.00 |
| Mir7056 | 1.00 | 1.00 | 1.00 | 1.00 | 1.00 | 1.00 | 1.00 | 1.00 | 1.00 |
| Mir7060 | 0.65 | 0.43 | 2.65 | 1.34 | 0.31 | 2.99 | 0.14 | 0.90 | 0.73 |
| Mir7065 | 1.00 | 1.00 | 1.00 | 1.00 | 1.00 | 1.00 | 1.00 | 1.00 | 1.14 |
| Mir7076 | 1.00 | 1.00 | 1.00 | 1.00 | 1.00 | 1.00 | 1.00 | 1.00 | 1.00 |
| Mir7094-1 | 1.00 | 1.00 | 1.00 | 1.00 | 1.00 | 1.00 | 1.00 | 1.00 | 1.00 |
| Mir7094-2 | 1.00 | 1.00 | 1.00 | 1.00 | 1.00 | 1.00 | 1.00 | 1.00 | 1.00 |
| Mir7-2 | 1.00 | 1.00 | 1.00 | 1.00 | 1.00 | 1.00 | 1.00 | 0.15 | 1.00 |
| Mir721 | 1.00 | 1.00 | 0.10 | 1.00 | 1.00 | 1.00 | 1.00 | 1.00 | 1.00 |
| Mir7235 | 1.00 | 1.00 | 1.00 | 1.00 | 1.00 | 1.00 | 1.00 | 1.00 | 1.00 |
| Mir743 | 1.00 | 1.00 | 1.00 | 1.00 | 1.00 | 1.00 | 0.02 | 1.00 | 0.98 |
| Mir7667 | 1.00 | 1.00 | 1.00 | 1.00 | 1.00 | 1.00 | 0.01 | 0.89 | 3.04 |
| Mir770 | 1.00 | 1.00 | 1.00 | 1.00 | 1.00 | 1.00 | 1.00 | 1.00 | 1.00 |
| Mir8091 | 1.84 | 1.39 | 0.74 | 1.39 | 0.68 | 0.92 | 3.24 | 0.33 | 1.53 |
| Mir8101 | 1.00 | 1.00 | 1.00 | 1.00 | 1.00 | 1.00 | 1.00 | 1.00 | 1.00 |
| Mir8109 | 0.14 | 4.01 | 3.55 | 1.00 | 1.00 | 1.00 | 1.00 | 1.00 | 1.00 |
| Mir8110 | 1.00 | 1.00 | 1.00 | 1.00 | 1.00 | 1.00 | 1.00 | 1.00 | 1.00 |
| Mir9-3 | 1.00 | 1.00 | 1.00 | 1.00 | 1.00 | 1.00 | 0.12 | 0.12 | 1.00 |
| Mirlet7a-2 | 1.00 | 1.00 | 1.00 | 1.00 | 1.00 | 1.00 | 0.16 | 1.00 | 1.00 |
| Mmd2 | 1.01 | 0.97 | 0.98 | 0.49 | 0.11 | 0.96 | 0.80 | 0.88 | 1.09 |
| Mmp7 | 1.00 | 1.00 | 1.00 | 0.31 | 0.13 | 1.00 | 0.75 | 1.00 | 1.00 |
| Mpo | 1.00 | 1.00 | 1.00 | 1.00 | 1.00 | 1.00 | 1.00 | 1.00 | 1.00 |
| Mrs2 | 0.86 | 0.70 | 1.06 | 0.97 | 0.94 | 1.27 | 0.82 | 0.14 | 1.09 |
| Ms4a1 | 1.00 | 1.00 | 1.00 | 0.89 | 1.24 | 0.12 | 1.00 | 1.00 | 1.00 |
| Mt3 | 0.88 | 0.78 | 0.98 | 0.22 | 0.14 | 1.00 | 0.64 | 0.44 | 1.44 |
| Mup1 | 1.00 | 1.00 | 1.00 | 1.00 | 1.00 | 1.00 | 1.00 | 1.00 | 1.19 |
| Mup10 | 1.00 | 1.00 | 1.00 | 1.00 | 1.00 | 1.00 | 0.98 | 1.00 | 1.00 |
| Mup11 | 1.00 | 1.00 | 1.00 | 1.00 | 1.00 | 1.00 | 1.00 | 1.00 | 1.00 |
| Mup12 | 1.00 | 1.00 | 1.00 | 1.00 | 1.00 | 1.00 | 0.90 | 1.00 | 1.13 |
| Mup13 | 1.00 | 1.00 | 1.00 | 1.00 | 1.00 | 1.00 | 1.00 | 1.00 | 1.00 |
| Mup14 | 1.00 | 1.00 | 1.00 | 1.00 | 1.00 | 1.00 | 1.00 | 1.00 | 1.09 |
| Mup15 | 1.00 | 1.00 | 1.00 | 1.00 | 1.00 | 1.00 | 0.75 | 1.00 | 1.60 |
| Mup16 | 1.00 | 1.00 | 1.00 | 1.00 | 1.00 | 1.00 | 1.00 | 1.00 | 1.13 |
| Mup17 | 1.00 | 1.00 | 1.00 | 1.00 | 1.00 | 1.00 | 1.00 | 1.00 | 1.00 |
| Mup19 | 1.00 | 1.00 | 1.00 | 1.00 | 1.00 | 1.00 | 1.00 | 1.00 | 1.00 |
| Mup2 | 1.00 | 1.00 | 1.00 | 1.00 | 1.00 | 1.00 | 1.00 | 1.00 | 1.22 |

Fig. 31-16

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir6385 | 1.52 | 1.68 | 0.83 | 0.94 | 1.06 | 0.89 | 0.09 | 0.09 | 0.10 | 1.00 | 1.00 | 1.00 |
| Mir6393 | 1.00 | 1.00 | 1.00 | 1.00 | 1.00 | 1.00 | 1.00 | 1.00 | 1.00 | 1.00 | 1.00 | 1.00 |
| Mir6394 | 1.00 | 1.00 | 1.00 | 1.00 | 1.00 | 1.00 | 1.00 | 1.00 | 1.00 | 1.00 | 1.00 | 1.00 |
| Mir6409 | 1.16 | 1.46 | 2.47 | 0.22 | 0.21 | 0.08 | 1.00 | 1.00 | 1.00 | 1.00 | 1.00 | 1.00 |
| Mir6410 | 1.00 | 1.00 | 1.00 | 1.00 | 1.00 | 1.00 | 1.00 | 1.00 | 1.00 | 1.00 | 1.00 | 1.00 |
| Mir6516 | 0.49 | 1.39 | 0.75 | 1.00 | 1.27 | 0.32 | 0.62 | 0.85 | 0.17 | 1.00 | 1.00 | 1.00 |
| Mir668 | 1.00 | 1.00 | 1.00 | 1.00 | 1.00 | 1.00 | 1.00 | 1.00 | 1.00 | 1.00 | 1.00 | 1.00 |
| Mir669a-2 | 1.00 | 1.00 | 1.00 | 1.00 | 1.00 | 1.00 | 1.00 | 1.00 | 1.00 | 1.00 | 1.00 | 1.00 |
| Mir670 | 1.00 | 1.00 | 1.00 | 1.00 | 1.00 | 1.00 | 1.00 | 1.00 | 1.00 | 1.00 | 1.00 | 1.00 |
| Mir677 | 0.72 | 0.91 | 0.77 | 0.81 | 1.18 | 0.72 | 0.42 | 0.04 | 0.02 | 1.00 | 1.00 | 1.00 |
| Mir680-3 | 1.00 | 1.00 | 1.00 | 1.00 | 1.00 | 1.00 | 1.00 | 1.00 | 1.00 | 1.00 | 0.82 | 0.00 |
| Mir683-1 | 1.00 | 1.00 | 1.00 | 1.00 | 1.00 | 1.00 | 1.00 | 1.00 | 1.00 | 1.00 | 1.00 | 1.00 |
| Mir6899 | 1.00 | 1.00 | 0.02 | 1.00 | 1.00 | 1.00 | 1.00 | 1.00 | 1.00 | 1.00 | 1.00 | 1.00 |
| Mir6901 | 0.02 | 1.00 | 1.00 | 1.00 | 1.00 | 1.00 | 1.00 | 1.00 | 1.00 | 1.00 | 1.00 | 1.00 |
| Mir6906 | 1.00 | 0.02 | 1.00 | 1.00 | 1.00 | 1.00 | 1.00 | 1.00 | 1.00 | 1.00 | 1.00 | 1.00 |
| Mir693 | 1.00 | 1.00 | 1.00 | 1.00 | 1.00 | 1.00 | 1.00 | 1.00 | 1.00 | 1.00 | 1.00 | 1.00 |
| Mir6949 | 1.00 | 1.00 | 1.00 | 1.00 | 1.00 | 1.00 | 1.00 | 1.00 | 1.00 | 1.00 | 1.00 | 1.00 |
| Mir695 | 1.00 | 0.20 | 0.20 | 1.00 | 1.00 | 1.00 | 1.00 | 1.00 | 1.00 | 1.00 | 1.00 | 1.00 |
| Mir6952 | 1.00 | 1.00 | 1.00 | 1.00 | 1.00 | 1.00 | 1.00 | 1.00 | 1.00 | 1.00 | 1.00 | 1.00 |
| Mir6955 | 1.22 | 0.91 | 0.57 | 1.66 | 0.59 | 1.00 | 0.77 | 0.54 | 0.02 | 1.00 | 1.00 | 1.00 |
| Mir6956 | 1.00 | 0.02 | 1.00 | 1.00 | 1.00 | 1.00 | 1.00 | 1.00 | 1.00 | 1.00 | 1.00 | 1.00 |
| Mir6965 | 1.00 | 1.00 | 1.00 | 0.03 | 1.00 | 0.01 | 1.00 | 1.00 | 1.00 | 1.00 | 1.00 | 1.00 |
| Mir6971 | 1.00 | 1.00 | 1.00 | 1.00 | 1.00 | 1.00 | 1.00 | 1.00 | 1.00 | 1.00 | 1.00 | 1.00 |
| Mir698 | 1.00 | 1.00 | 1.00 | 1.00 | 1.00 | 1.00 | 1.00 | 1.00 | 1.00 | 1.00 | 1.00 | 1.00 |
| Mir6983 | 1.00 | 1.00 | 1.00 | 1.00 | 0.03 | 1.00 | 1.00 | 1.00 | 1.00 | 1.00 | 1.00 | 1.00 |
| Mir6987 | 1.00 | 1.00 | 1.00 | 1.00 | 1.00 | 1.00 | 1.00 | 1.00 | 1.00 | 1.00 | 1.00 | 1.00 |
| Mir7038 | 1.00 | 1.00 | 1.00 | 1.00 | 1.00 | 1.00 | 1.00 | 1.00 | 1.00 | 1.00 | 1.00 | 1.00 |
| Mir705 | 1.00 | 1.00 | 1.00 | 1.00 | 1.00 | 1.00 | 1.00 | 1.00 | 1.96 | 1.00 | 1.00 | 1.00 |
| Mir7055 | 1.00 | 1.00 | 1.00 | 1.00 | 1.00 | 1.00 | 1.00 | 1.00 | 1.00 | 1.00 | 1.00 | 1.00 |
| Mir7056 | 1.00 | 0.02 | 1.00 | 1.00 | 1.00 | 1.00 | 1.00 | 1.00 | 1.00 | 1.00 | 1.00 | 1.00 |
| Mir7060 | 0.50 | 0.69 | 0.76 | 1.71 | 1.11 | 1.14 | 1.56 | 1.00 | 1.93 | 1.00 | 1.00 | 1.00 |
| Mir7065 | 1.00 | 1.00 | 1.00 | 1.00 | 0.02 | 1.00 | 1.00 | 1.00 | 1.00 | 1.00 | 1.00 | 1.00 |
| Mir7076 | 1.00 | 1.00 | 1.00 | 1.00 | 1.00 | 1.00 | 2.54 | 0.00 | 0.00 | 1.00 | 1.00 | 1.00 |
| Mir7094-1 | 1.00 | 1.00 | 1.00 | 1.00 | 1.00 | 1.00 | 1.00 | 1.00 | 1.00 | 1.00 | 1.00 | 1.00 |
| Mir7094-2 | 1.00 | 1.00 | 1.00 | 1.00 | 1.00 | 1.00 | 1.00 | 1.00 | 1.00 | 1.00 | 1.00 | 1.00 |
| Mir7-2 | 1.00 | 1.00 | 1.00 | 1.00 | 1.00 | 1.00 | 1.00 | 1.00 | 1.00 | 1.00 | 1.00 | 1.00 |
| Mir721 | 1.00 | 1.00 | 1.00 | 1.00 | 1.00 | 1.00 | 1.00 | 1.00 | 1.00 | 1.00 | 1.00 | 1.00 |
| Mir7235 | 1.00 | 0.01 | 1.00 | 1.00 | 1.00 | 1.00 | 1.00 | 1.00 | 1.00 | 1.00 | 1.00 | 1.00 |
| Mir743 | 1.00 | 1.00 | 1.00 | 1.00 | 1.00 | 1.00 | 1.00 | 1.00 | 1.00 | 1.00 | 1.00 | 1.00 |
| Mir7667 | 1.00 | 1.00 | 1.00 | 1.00 | 1.00 | 1.00 | 1.00 | 1.00 | 1.00 | 1.00 | 1.00 | 1.00 |
| Mir770 | 0.13 | 1.00 | 1.00 | 1.00 | 1.00 | 1.00 | 2.64 | 1.00 | 1.00 | 1.00 | 1.00 | 1.00 |
| Mir8091 | 0.81 | 1.25 | 0.86 | 1.91 | 0.58 | 0.93 | 1.44 | 0.97 | 0.58 | 1.00 | 0.19 | 0.26 |
| Mir8101 | 1.00 | 1.00 | 1.00 | 1.00 | 1.00 | 1.00 | 1.00 | 1.00 | 1.00 | 1.00 | 0.01 | 1.00 |
| Mir8109 | 1.00 | 1.00 | 1.00 | 1.00 | 1.00 | 1.00 | 1.00 | 1.00 | 1.00 | 1.00 | 1.00 | 1.00 |
| Mir8110 | 1.00 | 1.00 | 1.00 | 1.00 | 1.00 | 1.00 | 1.00 | 1.00 | 1.00 | 1.00 | 1.63 | 0.07 |
| Mir9-3 | 1.00 | 1.00 | 1.00 | 1.00 | 1.00 | 1.00 | 1.00 | 1.00 | 1.00 | 1.00 | 1.00 | 1.00 |
| Mirlet7a-2 | 1.00 | 1.00 | 1.00 | 1.00 | 1.00 | 1.00 | 1.00 | 1.00 | 1.00 | 1.00 | 0.74 | 0.97 |
| Mmd2 | 1.00 | 1.00 | 1.00 | 1.00 | 1.00 | 1.00 | 1.00 | 1.00 | 1.00 | 1.00 | 1.00 | 1.00 |
| Mmp7 | 1.74 | 0.89 | 1.17 | 1.00 | 1.00 | 1.00 | 1.00 | 1.00 | 1.00 | 1.00 | 1.05 | 0.92 |
| Mpo | 0.85 | 2.31 | 1.00 | 0.89 | 1.11 | 0.93 | 1.00 | 1.00 | 1.00 | 0.80 | 1.15 | 0.99 |
| Mrs2 | 1.06 | 1.36 | 0.94 | 1.00 | 1.60 | 0.98 | 1.14 | 1.34 | 0.99 | 1.22 | 1.44 | 0.84 |
| Ms4a1 | 2.37 | 3.86 | 2.78 | 1.07 | 0.71 | 0.83 | 1.00 | 0.89 | 0.89 | 1.00 | 1.00 | 1.00 |
| Mt3 | 1.29 | 0.94 | 1.39 | 1.00 | 1.00 | 1.00 | 1.00 | 1.00 | 1.00 | 1.00 | 1.02 | 1.04 |
| Mup1 | 0.89 | 1.00 | 1.00 | 1.00 | 1.00 | 1.00 | 1.00 | 1.00 | 1.00 | 1.00 | 0.25 | 1.00 |
| Mup10 | 0.83 | 1.00 | 1.00 | 1.00 | 1.00 | 1.00 | 1.00 | 1.00 | 1.00 | 1.00 | 0.37 | 1.00 |
| Mup11 | 1.00 | 1.00 | 1.00 | 1.00 | 1.00 | 1.00 | 1.00 | 1.00 | 1.00 | 1.00 | 0.30 | 1.00 |
| Mup12 | 0.96 | 1.00 | 1.00 | 1.00 | 1.00 | 1.00 | 1.00 | 1.00 | 1.00 | 1.00 | 0.43 | 1.00 |
| Mup13 | 1.00 | 1.00 | 1.00 | 1.00 | 1.00 | 1.00 | 1.00 | 1.00 | 1.00 | 1.00 | 0.45 | 1.00 |
| Mup14 | 0.99 | 1.00 | 1.00 | 1.00 | 1.00 | 1.00 | 1.00 | 1.00 | 1.00 | 1.00 | 0.36 | 1.00 |
| Mup15 | 0.61 | 1.00 | 1.00 | 1.00 | 1.00 | 1.00 | 1.00 | 1.00 | 1.00 | 1.00 | 0.33 | 1.00 |
| Mup16 | 1.00 | 1.00 | 1.00 | 1.00 | 1.00 | 1.00 | 1.00 | 1.00 | 1.00 | 1.00 | 0.40 | 1.00 |
| Mup17 | 1.00 | 1.00 | 1.00 | 1.00 | 1.00 | 1.00 | 1.00 | 1.00 | 1.00 | 1.00 | 0.32 | 1.00 |
| Mup19 | 0.86 | 1.00 | 1.00 | 1.00 | 1.00 | 1.00 | 1.00 | 1.00 | 1.00 | 1.00 | 0.24 | 1.00 |
| Mup2 | 0.56 | 1.00 | 1.00 | 1.00 | 1.00 | 1.00 | 1.00 | 1.00 | 1.00 | 0.95 | 1.00 | 1.00 |

Fig. 31-17

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mup7 | 1.00 | 1.00 | 1.00 | 1.00 | 1.00 | 1.00 | 0.43 | 0.54 | 1.37 |
| Mup8 | 1.00 | 1.00 | 1.00 | 1.00 | 1.00 | 1.00 | 0.51 | 0.55 | 1.17 |
| Mup9 | 1.00 | 1.00 | 1.00 | 1.00 | 1.00 | 1.00 | 0.47 | 0.54 | 1.21 |
| Nlrp6 | 1.00 | 1.00 | 1.00 | 1.15 | 0.95 | 1.04 | 1.05 | 0.95 | 0.98 |
| Nme5 | 0.86 | 0.71 | 0.94 | 0.75 | 1.11 | 0.91 | 1.00 | 1.00 | 1.00 |
| Notum | 1.00 | 1.00 | 1.00 | 0.89 | 0.62 | 1.03 | 0.80 | 0.78 | 1.35 |
| Nrep | 1.25 | 2.28 | 1.25 | 0.61 | 1.11 | 1.10 | 0.14 | 0.49 | 0.56 |
| Oaz1 | 0.95 | 0.86 | 0.80 | 1.05 | 1.00 | 1.00 | 1.05 | 0.78 | 1.01 |
| Odf3b | 1.00 | 1.00 | 1.00 | 1.00 | 1.00 | 1.00 | 0.67 | 0.70 | 1.59 |
| Padi4 | 1.00 | 1.32 | 1.36 | 1.71 | 1.24 | 1.57 | 1.00 | 1.23 | 1.00 |
| Pate4 | 1.00 | 1.00 | 1.00 | 1.00 | 1.00 | 1.00 | 1.00 | 1.00 | 1.00 |
| Pdia2 | 1.00 | 1.00 | 1.00 | 1.00 | 1.00 | 1.00 | 1.00 | 1.00 | 1.00 |
| Pet117 | 1.11 | 0.17 | 0.30 | 1.58 | 0.63 | 0.59 | 2.00 | 0.61 | 0.61 |
| Pglyrp1 | 3.14 | 1.77 | 1.76 | 1.00 | 1.45 | 1.00 | 1.00 | 2.84 | 1.00 |
| Pipox | 0.96 | 1.00 | 0.96 | 1.20 | 0.85 | 0.88 | 1.13 | 0.84 | 0.83 |
| Pklr | 1.00 | 1.00 | 1.00 | 1.04 | 0.79 | 0.94 | 0.82 | 0.80 | 0.63 |
| Pla2g1b | 1.00 | 1.00 | 1.00 | 1.00 | 1.00 | 1.00 | 1.00 | 1.00 | 1.00 |
| Plet1 | 1.02 | 0.93 | 2.35 | 0.85 | 1.10 | 0.92 | 1.00 | 0.87 | 1.00 |
| Pnlip | 1.00 | 1.00 | 1.00 | 1.00 | 1.00 | 1.00 | 1.00 | 3.31 | 1.00 |
| Pnliprp1 | 1.00 | 1.00 | 1.00 | 1.00 | 1.00 | 1.00 | 1.00 | 1.27 | 1.00 |
| Pnliprp2 | 1.00 | 1.00 | 1.00 | 1.00 | 1.00 | 1.00 | 1.00 | 1.00 | 1.00 |
| Ppil6 | 0.95 | 0.88 | 1.00 | 1.01 | 0.96 | 1.06 | 1.00 | 1.00 | 1.00 |
| Ppp1r1b | 1.51 | 0.48 | 0.40 | 0.85 | 0.99 | 1.02 | 1.22 | 1.43 | 0.98 |
| Prg4 | 3.39 | 1.27 | 3.14 | 1.00 | 1.00 | 0.73 | 0.82 | 1.08 | 0.83 |
| Prm1 | 1.00 | 1.00 | 1.00 | 1.00 | 1.00 | 1.00 | 1.00 | 1.00 | 1.00 |
| Prm2 | 1.00 | 1.00 | 1.00 | 1.00 | 1.00 | 1.00 | 1.00 | 1.00 | 1.00 |
| Prss1 | 1.00 | 1.00 | 1.00 | 1.00 | 1.00 | 1.00 | 1.00 | 1.00 | 1.00 |
| Prss2 | 1.00 | 1.00 | 1.00 | 1.00 | 1.00 | 1.00 | 1.00 | 2.59 | 1.00 |
| Prss3 | 1.00 | 1.00 | 1.00 | 1.00 | 1.00 | 1.00 | 1.00 | 1.00 | 1.00 |
| Prss34 | 1.00 | 1.00 | 1.00 | 1.00 | 1.00 | 1.00 | 1.00 | 1.05 | 1.00 |
| Ptprr | 1.05 | 1.03 | 1.02 | 1.00 | 1.50 | 0.20 | 1.00 | 1.00 | 1.00 |
| Rap1gap | 0.69 | 0.64 | 0.82 | 1.11 | 0.91 | 0.77 | 0.57 | 1.70 | 0.85 |
| Rdh16 | 1.00 | 1.00 | 1.00 | 1.13 | 0.79 | 0.68 | 1.61 | 0.63 | 0.64 |
| Reg1 | 1.00 | 1.00 | 1.00 | 1.00 | 1.00 | 1.00 | 1.00 | 1.07 | 1.00 |
| Reg3a | 0.58 | 1.00 | 1.00 | 1.00 | 1.00 | 1.00 | 1.00 | 1.00 | 1.00 |
| Reg3b | 0.77 | 1.00 | 1.00 | 1.00 | 1.00 | 1.00 | 0.56 | 1.00 | 1.00 |
| Reg3d | 1.00 | 1.00 | 1.00 | 1.00 | 1.00 | 1.00 | 1.00 | 1.00 | 1.00 |
| Retnlb | 1.00 | 1.00 | 1.00 | 1.00 | 1.00 | 1.00 | 1.00 | 1.00 | 1.00 |
| Rnase1 | 0.51 | 0.97 | 0.52 | 1.23 | 1.45 | 0.82 | 1.00 | 1.55 | 1.00 |
| Rnase2a | 1.00 | 1.00 | 1.17 | 1.00 | 1.00 | 1.00 | 1.00 | 1.00 | 1.00 |
| Rnase2b | 1.00 | 1.00 | 1.00 | 1.00 | 1.00 | 1.00 | 1.00 | 1.00 | 1.00 |
| Rsph4a | 1.00 | 1.00 | 1.00 | 1.00 | 1.00 | 1.00 | 1.00 | 1.00 | 1.00 |
| Saa1 | 1.00 | 1.00 | 1.00 | 1.00 | 1.00 | 1.00 | 1.09 | 2.35 | 0.36 |
| Sap25 | 1.35 | 1.26 | 1.49 | 0.92 | 1.08 | 1.09 | 0.69 | 1.33 | 1.18 |
| Scarna2 | 1.00 | 0.02 | 0.92 | 1.00 | 1.00 | 1.00 | 1.00 | 1.00 | 1.00 |
| Scarna3a | 2.67 | 0.11 | 1.36 | 0.63 | 1.00 | 1.10 | 1.00 | 4.52 | 0.21 |
| Serpina9 | 1.00 | 1.00 | 1.00 | 1.00 | 1.00 | 1.00 | 0.16 | 0.41 | 1.78 |
| Serpini2 | 1.00 | 1.00 | 1.00 | 1.00 | 1.00 | 1.00 | 1.00 | 1.00 | 1.00 |
| Siglece | 1.14 | 1.00 | 1.00 | 1.00 | 1.00 | 1.00 | 0.86 | 0.86 | 1.00 |
| Slc30a3 | 1.00 | 1.00 | 1.00 | 1.00 | 1.00 | 1.00 | 1.00 | 1.00 | 1.00 |
| Slc39a5 | 1.00 | 1.00 | 1.00 | 1.00 | 0.57 | 0.92 | 1.00 | 1.00 | 1.00 |
| Slc7a9 | 1.00 | 1.00 | 1.00 | 1.16 | 0.94 | 0.73 | 1.00 | 1.00 | 1.00 |
| Slc9a3 | 1.00 | 1.00 | 1.00 | 1.10 | 0.68 | 1.13 | 1.00 | 1.00 | 1.00 |
| Slc9a3r2 | 1.09 | 0.74 | 0.79 | 1.15 | 1.13 | 0.93 | 1.03 | 0.86 | 0.99 |
| Slfn5os | 0.68 | 0.61 | 0.94 | 1.11 | 0.82 | 1.00 | 1.00 | 1.00 | 1.00 |
| Slurp1 | 1.00 | 0.74 | 1.13 | 1.00 | 1.00 | 1.00 | 1.00 | 1.00 | 1.00 |
| Snai3 | 0.42 | 0.51 | 0.19 | 1.00 | 1.00 | 1.00 | 1.00 | 1.00 | 1.00 |
| Snora3 | 3.12 | 1.03 | 0.16 | 2.15 | 0.66 | 2.36 | 1.85 | 0.74 | 0.26 |
| Snora30 | 0.87 | 0.67 | 0.69 | 0.49 | 0.46 | 0.58 | 0.82 | 0.29 | 1.12 |
| Snora31 | 2.04 | 0.92 | 2.71 | 2.09 | 1.91 | 1.44 | 3.32 | 0.39 | 3.07 |
| Snora65 | 1.99 | 0.92 | 1.33 | 0.57 | 1.08 | 1.75 | 0.53 | 1.49 | 1.08 |
| Snora70 | 1.86 | 1.63 | 0.86 | 1.46 | 1.56 | 0.37 | 1.24 | 1.13 | 1.48 |
| Snord116l2 | 1.00 | 1.00 | 1.00 | 1.00 | 1.00 | 1.00 | 1.00 | 1.00 | 1.00 |
| Snord15b | 0.59 | 0.88 | 2.25 | 1.28 | 0.23 | 0.61 | 0.74 | 0.31 | 0.99 |

Fig. 31-18

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mup7 | 1.00 | 1.00 | 1.00 | 0.14 | 2.00 | 1.39 | 1.00 | 1.00 | 1.00 |
| Mup8 | 1.00 | 1.00 | 1.00 | 0.14 | 1.71 | 1.25 | 1.00 | 1.00 | 1.00 |
| Mup9 | 1.00 | 1.00 | 1.00 | 0.09 | 1.42 | 1.41 | 1.00 | 1.00 | 1.00 |
| Nlrp6 | 1.00 | 1.00 | 1.00 | 1.00 | 1.00 | 1.00 | 0.72 | 1.00 | 1.00 |
| Nme5 | 0.87 | 0.95 | 0.87 | 1.00 | 1.00 | 1.00 | 1.00 | 1.00 | 1.00 |
| Notum | 0.61 | 0.60 | 0.78 | 1.00 | 1.00 | 1.00 | 1.00 | 1.00 | 1.00 |
| Nrep | 0.72 | 0.82 | 0.86 | 0.55 | 0.64 | 0.83 | 0.83 | 0.60 | 1.13 |
| Oaz1 | 0.96 | 1.21 | 0.85 | 1.00 | 0.89 | 1.06 | 0.77 | 1.20 | 1.41 |
| Odf3b | 0.75 | 0.85 | 0.88 | 1.00 | 1.00 | 1.00 | 1.00 | 1.03 | 1.00 |
| Padi4 | 1.77 | 1.00 | 1.12 | 1.00 | 1.16 | 1.69 | 1.56 | 0.84 | 1.18 |
| Pate4 | 1.00 | 1.00 | 1.00 | 0.18 | 1.00 | 1.00 | 1.00 | 1.00 | 1.00 |
| Pdia2 | 1.00 | 1.00 | 1.19 | 1.00 | 1.00 | 1.00 | 1.24 | 0.14 | 0.07 |
| Pet117 | 0.84 | 0.75 | 2.97 | 0.67 | 0.79 | 0.44 | 0.69 | 1.06 | 2.33 |
| Pglyrp1 | 0.70 | 1.71 | 0.74 | 1.00 | 0.47 | 0.50 | 0.47 | 1.21 | 0.91 |
| Pipox | 1.00 | 1.00 | 1.00 | 1.00 | 1.00 | 1.00 | 1.00 | 1.00 | 1.00 |
| Pklr | 1.00 | 1.00 | 1.00 | 1.00 | 1.00 | 1.00 | 0.46 | 1.22 | 2.51 |
| Pla2g1b | 0.90 | 1.01 | 0.78 | 1.00 | 1.00 | 1.00 | 1.18 | 0.07 | 0.01 |
| Plet1 | 1.19 | 1.00 | 1.34 | 1.00 | 1.00 | 1.00 | 1.00 | 1.00 | 1.00 |
| Pnlip | 1.00 | 1.00 | 1.00 | 1.00 | 1.00 | 1.00 | 1.25 | 0.08 | 0.00 |
| Pnliprp1 | 1.00 | 0.78 | 0.83 | 1.00 | 1.00 | 1.00 | 1.52 | 0.08 | 0.00 |
| Pnliprp2 | 1.00 | 1.00 | 1.00 | 1.00 | 1.00 | 1.00 | 1.50 | 0.08 | 0.01 |
| Ppil6 | 0.83 | 0.72 | 0.92 | 1.00 | 1.00 | 1.00 | 1.00 | 1.00 | 1.00 |
| Ppp1r1b | 0.80 | 0.77 | 1.13 | 1.00 | 1.00 | 1.00 | 1.28 | 1.00 | 1.00 |
| Prg4 | 1.99 | 0.66 | 1.56 | 1.15 | 0.62 | 0.25 | 0.78 | 0.46 | 0.77 |
| Prm1 | 1.00 | 1.56 | 1.00 | 1.00 | 0.61 | 0.06 | 0.89 | 1.00 | 1.00 |
| Prm2 | 1.00 | 1.00 | 1.00 | 1.00 | 1.00 | 0.09 | 1.00 | 1.00 | 1.00 |
| Prss1 | 1.00 | 1.00 | 1.00 | 1.00 | 1.00 | 1.00 | 1.83 | 0.09 | 0.01 |
| Prss2 | 1.00 | 1.00 | 1.00 | 1.00 | 1.00 | 1.00 | 1.44 | 0.07 | 0.00 |
| Prss3 | 1.00 | 1.00 | 1.00 | 1.00 | 1.00 | 1.00 | 1.81 | 0.08 | 0.02 |
| Prss34 | 1.00 | 1.35 | 1.00 | 1.00 | 1.00 | 1.00 | 0.13 | 1.50 | 1.38 |
| Ptprr | 1.12 | 0.93 | 0.77 | 1.00 | 1.00 | 1.00 | 1.00 | 1.00 | 1.00 |
| Rap1gap | 1.56 | 0.58 | 0.76 | 0.60 | 1.07 | 1.14 | 1.54 | 0.60 | 0.82 |
| Rdh16 | 1.00 | 1.00 | 1.00 | 1.00 | 1.00 | 1.00 | 1.00 | 1.00 | 1.00 |
| Reg1 | 1.00 | 1.00 | 1.00 | 1.00 | 1.00 | 1.00 | 1.22 | 0.04 | 0.00 |
| Reg3a | 1.00 | 1.00 | 1.00 | 1.00 | 1.00 | 1.00 | 0.94 | 0.02 | 0.62 |
| Reg3b | 1.00 | 1.00 | 1.00 | 1.00 | 1.00 | 1.00 | 1.24 | 0.01 | 0.04 |
| Reg3d | 1.00 | 1.00 | 1.00 | 1.00 | 1.00 | 1.00 | 1.48 | 0.03 | 0.18 |
| Retnlb | 1.00 | 1.00 | 1.00 | 1.00 | 1.00 | 1.00 | 1.00 | 1.00 | 1.00 |
| Rnase1 | 1.00 | 1.00 | 1.00 | 1.00 | 1.00 | 1.00 | 1.04 | 0.07 | 0.00 |
| Rnase2a | 1.00 | 1.00 | 3.37 | 1.00 | 1.00 | 2.98 | 1.00 | 1.25 | 1.09 |
| Rnase2b | 1.00 | 1.00 | 1.00 | 1.00 | 1.00 | 1.00 | 1.00 | 1.00 | 1.00 |
| Rsph4a | 0.86 | 0.55 | 0.89 | 1.00 | 1.00 | 1.00 | 1.00 | 1.00 | 1.00 |
| Saa1 | 1.71 | 0.75 | 1.35 | 1.06 | 1.00 | 1.00 | 1.00 | 1.00 | 1.00 |
| Sap25 | 0.64 | 1.19 | 0.88 | 1.53 | 1.43 | 0.95 | 1.11 | 0.91 | 0.79 |
| Scarna2 | 1.00 | 1.00 | 1.00 | 1.00 | 0.02 | 1.00 | 0.01 | 1.00 | 1.00 |
| Scarna3a | 2.60 | 1.83 | 1.33 | 0.53 | 1.71 | 0.36 | 0.76 | 1.06 | 1.83 |
| Serpina9 | 1.00 | 1.00 | 1.00 | 1.00 | 1.00 | 1.00 | 1.00 | 1.00 | 1.00 |
| Serpini2 | 1.00 | 1.00 | 1.00 | 1.00 | 1.00 | 1.00 | 1.84 | 0.10 | 0.05 |
| Siglece | 0.44 | 0.77 | 1.04 | 1.00 | 1.00 | 1.00 | 0.19 | 0.45 | 0.83 |
| Slc30a3 | 1.00 | 1.00 | 1.00 | 1.00 | 1.00 | 1.00 | 1.00 | 1.00 | 1.00 |
| Slc39a5 | 1.00 | 1.00 | 1.00 | 1.00 | 1.00 | 1.00 | 1.74 | 0.19 | 0.29 |
| Slc7a9 | 1.00 | 1.00 | 1.00 | 1.00 | 1.00 | 1.00 | 1.00 | 1.00 | 1.00 |
| Slc9a3 | 1.00 | 1.00 | 1.00 | 1.00 | 1.00 | 1.00 | 1.00 | 1.00 | 1.00 |
| Slc9a3r2 | 1.00 | 0.58 | 0.84 | 1.03 | 0.78 | 1.36 | 1.20 | 0.56 | 0.91 |
| Slfn5os | 1.36 | 0.62 | 0.46 | 0.85 | 1.14 | 1.26 | 1.00 | 1.00 | 1.00 |
| Slurp1 | 0.43 | 0.11 | 0.90 | 1.00 | 0.97 | 1.00 | 1.00 | 1.00 | 1.00 |
| Snai3 | 1.00 | 1.00 | 1.00 | 0.90 | 0.39 | 0.63 | 1.18 | 1.05 | 1.00 |
| Snora3 | 1.03 | 1.07 | 1.47 | 2.95 | 0.33 | 2.99 | 1.40 | 0.91 | 1.73 |
| Snora30 | 1.17 | 2.79 | 1.46 | 1.35 | 0.79 | 1.42 | 1.36 | 0.99 | 0.55 |
| Snora31 | 1.13 | 1.71 | 0.85 | 1.09 | 1.42 | 1.24 | 1.47 | 1.19 | 0.99 |
| Snora65 | 1.34 | 1.63 | 1.43 | 0.81 | 1.47 | 0.78 | 1.00 | 1.19 | 1.13 |
| Snora70 | 1.23 | 1.45 | 1.07 | 3.05 | 1.11 | 0.76 | 0.85 | 0.88 | 0.93 |
| Snord116l2 | 1.00 | 1.00 | 1.00 | 1.00 | 1.00 | 1.00 | 1.00 | 1.00 | 1.00 |
| Snord15b | 0.37 | 1.23 | 1.10 | 0.82 | 2.94 | 3.37 | 1.11 | 1.70 | 0.86 |

Fig. 31-19

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mup7 | 1.00 | 1.00 | 1.00 | 1.00 | 1.00 | 1.00 | 1.00 | 1.00 | 1.00 |
| Mup8 | 1.00 | 1.00 | 1.00 | 1.00 | 1.00 | 1.00 | 1.00 | 1.00 | 1.00 |
| Mup9 | 1.00 | 1.00 | 1.00 | 1.00 | 1.00 | 1.00 | 0.96 | 1.00 | 1.17 |
| Nlrp6 | 1.00 | 1.00 | 1.00 | 0.58 | 0.17 | 1.00 | 1.00 | 1.00 | 1.00 |
| Nme5 | 0.98 | 1.12 | 0.93 | 0.50 | 0.19 | 1.00 | 1.09 | 1.12 | 1.06 |
| Notum | 0.79 | 0.82 | 1.19 | 0.41 | 0.12 | 1.00 | 1.00 | 1.00 | 1.00 |
| Nrep | 1.03 | 0.91 | 1.19 | 0.41 | 0.88 | 0.96 | 0.97 | 0.93 | 1.10 |
| Oaz1 | 1.12 | 1.12 | 0.87 | 1.06 | 1.09 | 0.99 | 0.92 | 1.01 | 0.95 |
| Odf3b | 1.07 | 1.09 | 1.06 | 0.45 | 0.17 | 1.00 | 0.89 | 1.15 | 0.99 |
| Padi4 | 1.43 | 1.45 | 1.53 | 2.31 | 2.29 | 0.57 | 1.00 | 1.00 | 1.00 |
| Pate4 | 1.00 | 1.00 | 1.00 | 1.00 | 1.48 | 1.00 | 1.00 | 1.00 | 1.00 |
| Pdia2 | 1.00 | 1.00 | 1.00 | 1.00 | 1.00 | 1.00 | 1.00 | 1.00 | 1.00 |
| Pet117 | 0.73 | 3.27 | 1.27 | 0.45 | 0.85 | 1.28 | 0.76 | 1.17 | 0.57 |
| Pglyrp1 | 2.10 | 1.04 | 1.06 | 1.80 | 1.01 | 0.19 | 1.00 | 1.00 | 1.00 |
| Pipox | 0.91 | 0.88 | 0.77 | 0.38 | 0.09 | 1.00 | 1.00 | 1.00 | 1.00 |
| Pklr | 1.00 | 1.00 | 1.00 | 0.56 | 0.17 | 1.00 | 1.00 | 1.00 | 1.00 |
| Pla2g1b | 1.00 | 1.00 | 1.00 | 1.00 | 1.00 | 1.00 | 1.00 | 1.00 | 0.97 |
| Plet1 | 1.00 | 1.00 | 1.00 | 0.41 | 0.12 | 1.00 | 1.00 | 1.00 | 1.00 |
| Pnlip | 1.00 | 1.00 | 1.00 | 1.00 | 1.00 | 1.00 | 1.00 | 1.00 | 1.00 |
| Pnliprp1 | 1.00 | 1.00 | 1.00 | 1.00 | 1.00 | 1.00 | 1.24 | 1.00 | 1.00 |
| Pnliprp2 | 1.00 | 1.00 | 1.00 | 1.00 | 1.00 | 1.00 | 1.00 | 1.00 | 1.00 |
| Ppil6 | 1.04 | 0.97 | 1.13 | 0.58 | 0.19 | 1.01 | 1.03 | 1.12 | 1.08 |
| Ppp1r1b | 1.02 | 0.99 | 0.98 | 0.27 | 0.10 | 1.00 | 0.83 | 1.00 | 1.00 |
| Prg4 | 2.12 | 1.74 | 0.95 | 2.40 | 0.36 | 0.13 | 1.00 | 1.00 | 1.00 |
| Prm1 | 0.84 | 1.00 | 1.00 | 1.00 | 2.60 | 1.00 | 0.97 | 0.93 | 1.05 |
| Prm2 | 1.00 | 1.00 | 1.00 | 1.00 | 3.76 | 1.00 | 1.11 | 1.03 | 1.06 |
| Prss1 | 1.00 | 1.00 | 1.00 | 1.00 | 1.00 | 1.00 | 1.00 | 1.00 | 1.00 |
| Prss2 | 1.00 | 1.00 | 1.00 | 1.00 | 1.00 | 1.00 | 1.00 | 1.00 | 1.00 |
| Prss3 | 1.00 | 1.00 | 1.00 | 1.00 | 1.00 | 1.00 | 1.00 | 1.00 | 1.00 |
| Prss34 | 1.00 | 1.00 | 1.00 | 1.00 | 1.00 | 1.00 | 1.00 | 1.00 | 1.00 |
| Ptprr | 1.00 | 1.08 | 1.04 | 1.53 | 0.87 | 0.91 | 1.00 | 1.00 | 1.00 |
| Rap1gap | 0.97 | 0.96 | 0.95 | 0.86 | 0.20 | 1.00 | 1.08 | 0.81 | 0.98 |
| Rdh16 | 1.00 | 1.00 | 1.00 | 0.58 | 0.11 | 1.00 | 1.00 | 1.00 | 1.00 |
| Reg1 | 1.00 | 1.00 | 1.00 | 1.00 | 1.00 | 1.00 | 1.00 | 1.00 | 1.00 |
| Reg3a | 1.00 | 1.00 | 1.00 | 1.00 | 1.00 | 1.00 | 1.00 | 1.00 | 1.00 |
| Reg3b | 1.00 | 1.00 | 1.00 | 1.00 | 0.01 | 1.00 | 1.00 | 1.00 | 1.00 |
| Reg3d | 1.00 | 1.00 | 1.00 | 1.00 | 1.00 | 1.00 | 1.00 | 1.00 | 1.00 |
| Retnlb | 1.00 | 1.00 | 1.00 | 1.00 | 0.13 | 1.00 | 1.00 | 1.00 | 1.00 |
| Rnase1 | 0.86 | 0.74 | 0.98 | 1.00 | 1.00 | 1.00 | 1.00 | 1.00 | 1.00 |
| Rnase2a | 1.00 | 1.00 | 1.00 | 2.70 | 1.54 | 0.67 | 1.00 | 1.00 | 1.00 |
| Rnase2b | 1.00 | 1.00 | 1.00 | 1.00 | 1.00 | 1.00 | 1.00 | 1.00 | 1.00 |
| Rsph4a | 0.92 | 1.05 | 1.16 | 0.45 | 0.16 | 1.00 | 1.00 | 1.00 | 1.00 |
| Saa1 | 1.00 | 1.00 | 1.00 | 3.56 | 0.16 | 1.00 | 0.68 | 0.84 | 1.15 |
| Sap25 | 1.39 | 1.17 | 1.14 | 1.03 | 1.12 | 0.99 | 0.71 | 1.26 | 0.98 |
| Scarna2 | 1.00 | 1.00 | 1.00 | 1.00 | 1.00 | 1.00 | 1.00 | 1.00 | 1.00 |
| Scarna3a | 1.17 | 0.94 | 0.65 | 3.29 | 2.07 | 0.38 | 2.02 | 0.17 | 0.32 |
| Serpina9 | 0.94 | 1.07 | 1.01 | 1.00 | 1.00 | 1.00 | 1.06 | 1.00 | 1.00 |
| Serpini2 | 1.00 | 1.00 | 1.00 | 1.00 | 1.00 | 1.00 | 1.55 | 0.99 | 1.06 |
| Siglece | 1.00 | 1.00 | 1.00 | 1.00 | 1.72 | 1.00 | 0.95 | 1.08 | 0.92 |
| Slc30a3 | 1.06 | 0.94 | 0.85 | 0.42 | 0.16 | 1.00 | 1.05 | 1.04 | 1.06 |
| Slc39a5 | 1.00 | 1.00 | 1.00 | 1.00 | 1.00 | 1.00 | 1.00 | 1.00 | 1.00 |
| Slc7a9 | 1.00 | 1.00 | 1.00 | 0.47 | 0.09 | 1.00 | 1.00 | 1.00 | 1.00 |
| Slc9a3 | 1.00 | 1.00 | 1.00 | 0.47 | 0.14 | 1.00 | 1.00 | 1.00 | 1.00 |
| Slc9a3r2 | 1.16 | 0.89 | 1.06 | 1.64 | 0.92 | 1.43 | 1.01 | 0.76 | 0.95 |
| Slfn5os | 1.00 | 1.00 | 1.00 | 1.70 | 0.59 | 0.73 | 4.40 | 0.69 | 0.14 |
| Slurp1 | 1.00 | 1.00 | 1.00 | 1.00 | 1.00 | 1.00 | 1.00 | 1.00 | 1.00 |
| Snai3 | 1.00 | 1.00 | 1.00 | 1.00 | 1.00 | 1.00 | 0.96 | 0.83 | 1.19 |
| Snora3 | 1.61 | 0.15 | 1.55 | 0.48 | 1.26 | 2.25 | 0.73 | 0.90 | 1.29 |
| Snora30 | 0.98 | 0.45 | 0.42 | 1.33 | 0.46 | 1.70 | 1.09 | 0.92 | 0.09 |
| Snora31 | 1.23 | 0.83 | 0.78 | 0.75 | 2.07 | 0.51 | 1.29 | 0.98 | 0.74 |
| Snora65 | 1.25 | 1.21 | 1.07 | 1.23 | 1.37 | 1.53 | 0.66 | 0.75 | 0.74 |
| Snora70 | 0.92 | 1.63 | 0.81 | 1.16 | 1.69 | 1.29 | 1.83 | 0.89 | 1.03 |
| Snord116l2 | 0.04 | 0.97 | 1.00 | 1.00 | 1.00 | 1.00 | 1.00 | 1.00 | 1.00 |
| Snord15b | 0.31 | 0.30 | 2.08 | 0.63 | 1.07 | 2.36 | 1.36 | 0.90 | 0.60 |

Fig. 31- 20

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mup7 | 1.00 | 1.00 | 1.00 | 1.00 | 1.00 | 1.00 | 1.00 | 1.00 | 1.00 | 1.00 | 0.31 | 1.00 |
| Mup8 | 0.90 | 1.00 | 1.00 | 1.00 | 1.00 | 1.00 | 1.00 | 1.00 | 1.00 | 1.00 | 1.07 | 1.02 |
| Mup9 | 0.89 | 1.00 | 1.00 | 1.00 | 1.00 | 1.00 | 1.00 | 1.00 | 1.00 | 1.00 | 0.90 | 0.81 |
| Nlrp6 | 1.00 | 1.00 | 1.00 | 1.00 | 1.00 | 1.00 | 1.00 | 1.00 | 1.00 | 1.00 | 1.00 | 1.00 |
| Nme5 | 1.05 | 2.39 | 1.00 | 1.00 | 1.00 | 1.00 | 1.00 | 1.00 | 1.00 | 1.00 | 0.79 | 1.00 |
| Notum | 1.00 | 1.00 | 1.00 | 1.00 | 0.41 | 1.00 | 1.00 | 1.00 | 1.00 | 1.10 | 1.11 | 1.10 |
| Nrep | 1.09 | 0.75 | 1.29 | 1.00 | 1.00 | 1.00 | 0.84 | 0.58 | 0.94 | 0.88 | 1.00 | 1.00 |
| Oaz1 | 0.86 | 0.91 | 0.97 | 1.14 | 0.92 | 0.98 | 0.98 | 0.67 | 1.29 | 0.93 | 0.10 | 2.26 |
| Odf3b | 0.80 | 1.55 | 0.71 | 1.00 | 1.00 | 1.00 | 1.00 | 1.00 | 1.00 | 1.00 | 1.00 | 1.00 |
| Padi4 | 0.28 | 0.74 | 0.18 | 1.46 | 1.08 | 1.18 | 1.00 | 1.00 | 1.00 | 0.39 | 0.93 | 0.92 |
| Pate4 | 1.00 | 1.00 | 1.00 | 1.00 | 1.00 | 1.00 | 1.00 | 1.00 | 1.00 | 1.00 | 1.00 | 1.00 |
| Pdia2 | 1.00 | 1.00 | 1.00 | 0.67 | 0.77 | 1.04 | 0.86 | 1.01 | 1.14 | 1.00 | 1.18 | 0.98 |
| Pet117 | 0.38 | 0.69 | 0.83 | 0.59 | 0.59 | 1.07 | 1.00 | 1.45 | 1.00 | 1.33 | 1.03 | 1.11 |
| Pglyrp1 | 1.42 | 2.22 | 1.18 | 0.96 | 1.10 | 0.97 | 0.73 | 2.46 | 0.16 | 1.03 | 1.00 | 1.00 |
| Pipox | 0.73 | 0.93 | 0.83 | 1.00 | 1.00 | 1.00 | 1.00 | 0.90 | 1.00 | 1.00 | 1.37 | 1.07 |
| Pklr | 1.00 | 1.00 | 1.00 | 0.93 | 0.82 | 0.90 | 0.80 | 1.04 | 1.00 | 1.00 | 1.20 | 1.21 |
| Pla2g1b | 1.17 | 1.00 | 0.96 | 1.00 | 1.00 | 1.00 | 0.95 | 0.81 | 1.04 | 1.03 | 1.00 | 1.00 |
| Plet1 | 1.46 | 1.24 | 0.92 | 1.00 | 1.00 | 1.00 | 1.00 | 0.69 | 0.87 | 1.06 | 1.00 | 1.00 |
| Pnlip | 0.23 | 1.00 | 0.10 | 1.00 | 1.00 | 1.00 | 1.05 | 1.11 | 1.55 | 1.00 | 1.00 | 1.00 |
| Pnliprp1 | 0.53 | 1.00 | 0.52 | 1.00 | 1.00 | 1.00 | 0.78 | 1.13 | 0.85 | 1.00 | 1.00 | 1.00 |
| Pnliprp2 | 1.00 | 1.00 | 1.00 | 1.00 | 1.00 | 1.00 | 0.95 | 1.03 | 1.18 | 1.00 | 1.00 | 1.00 |
| Ppil6 | 1.16 | 1.99 | 1.00 | 1.00 | 1.00 | 1.00 | 1.00 | 1.00 | 1.00 | 0.96 | 1.09 | 1.08 |
| Ppp1r1b | 0.69 | 0.42 | 0.53 | 1.00 | 1.00 | 1.00 | 1.34 | 1.11 | 0.76 | 1.16 | 1.05 | 1.09 |
| Prg4 | 1.41 | 2.00 | 1.44 | 1.00 | 1.00 | 1.00 | 1.00 | 0.98 | 1.00 | 1.83 | 0.96 | 0.93 |
| Prm1 | 0.93 | 0.75 | 0.90 | 1.00 | 0.87 | 1.00 | 1.00 | 1.00 | 1.00 | 1.00 | 1.00 | 1.00 |
| Prm2 | 1.00 | 1.00 | 1.00 | 1.00 | 1.00 | 1.00 | 1.00 | 1.00 | 1.00 | 0.87 | 0.89 | 0.82 |
| Prss1 | 1.00 | 1.00 | 1.00 | 1.00 | 1.00 | 1.00 | 0.87 | 1.06 | 0.97 | 1.00 | 1.00 | 1.00 |
| Prss2 | 0.34 | 0.80 | 0.30 | 1.00 | 1.00 | 1.00 | 0.75 | 1.07 | 1.06 | 0.68 | 0.49 | 0.92 |
| Prss3 | 1.00 | 1.00 | 1.00 | 1.00 | 1.00 | 1.00 | 0.86 | 0.96 | 0.91 | 1.00 | 1.00 | 1.00 |
| Prss34 | 1.00 | 1.00 | 1.00 | 1.41 | 0.86 | 0.71 | 1.00 | 1.00 | 1.00 | 1.00 | 1.29 | 1.19 |
| Ptprr | 1.00 | 1.00 | 1.00 | 1.00 | 1.00 | 1.00 | 1.00 | 1.00 | 1.00 | 1.00 | 1.00 | 1.00 |
| Rap1gap | 1.17 | 1.09 | 0.92 | 0.92 | 1.09 | 1.80 | 1.14 | 0.96 | 1.00 | 0.98 | 0.98 | 1.04 |
| Rdh16 | 1.00 | 1.00 | 1.00 | 1.00 | 1.00 | 1.00 | 1.00 | 1.00 | 1.00 | 0.86 | 0.81 | 0.78 |
| Reg1 | 0.61 | 0.88 | 0.77 | 1.00 | 1.00 | 1.00 | 0.68 | 1.58 | 1.16 | 1.13 | 1.00 | 1.00 |
| Reg3a | 1.00 | 1.00 | 1.00 | 1.00 | 1.00 | 1.00 | 0.90 | 3.72 | 0.66 | 1.00 | 1.00 | 1.00 |
| Reg3b | 2.13 | 0.70 | 1.64 | 1.00 | 1.00 | 1.00 | 0.60 | 3.05 | 1.51 | 0.95 | 1.00 | 1.00 |
| Reg3d | 1.00 | 1.00 | 1.00 | 1.00 | 1.00 | 1.00 | 0.97 | 1.65 | 1.01 | 1.00 | 1.00 | 1.00 |
| Retnlb | 1.00 | 1.00 | 1.00 | 1.00 | 1.00 | 1.00 | 1.00 | 1.00 | 1.00 | 1.00 | 1.27 | 0.96 |
| Rnase1 | 0.90 | 0.48 | 0.42 | 1.00 | 1.00 | 1.00 | 0.75 | 0.77 | 1.04 | 0.86 | 1.00 | 1.00 |
| Rnase2a | 1.78 | 0.32 | 2.16 | 1.62 | 0.20 | 0.12 | 1.00 | 1.00 | 1.00 | 1.42 | 0.98 | 1.00 |
| Rnase2b | 0.88 | 1.00 | 1.00 | 1.20 | 0.06 | 1.00 | 1.07 | 1.38 | 0.47 | 0.63 | 1.48 | 0.80 |
| Rsph4a | 1.00 | 1.31 | 1.00 | 1.00 | 1.00 | 1.00 | 1.00 | 1.00 | 1.00 | 1.00 | 1.08 | 1.16 |
| Saa1 | 1.13 | 1.73 | 1.15 | 1.00 | 1.00 | 1.00 | 1.00 | 0.89 | 1.00 | 1.00 | 1.00 | 1.00 |
| Sap25 | 0.80 | 1.03 | 0.87 | 1.06 | 0.93 | 1.00 | 0.79 | 0.57 | 1.11 | 0.19 | 0.91 | 1.04 |
| Scarna2 | 1.20 | 1.04 | 1.00 | 1.00 | 0.02 | 1.00 | 1.00 | 0.01 | 1.00 | 1.00 | 1.00 | 1.00 |
| Scarna3a | 0.59 | 0.90 | 0.20 | 3.66 | 1.47 | 1.17 | 1.00 | 3.01 | 1.00 | 1.00 | 1.00 | 1.00 |
| Serpina9 | 1.00 | 1.21 | 1.00 | 1.00 | 1.00 | 1.00 | 1.00 | 1.00 | 1.00 | 1.00 | 1.11 | 1.31 |
| Serpini2 | 1.00 | 1.00 | 1.00 | 1.00 | 1.00 | 1.00 | 0.85 | 1.43 | 1.07 | 1.00 | 0.89 | 1.02 |
| Siglece | 1.23 | 1.01 | 1.04 | 1.55 | 1.08 | 0.98 | 1.00 | 1.00 | 1.00 | 1.00 | 1.00 | 0.79 |
| Slc30a3 | 1.00 | 1.00 | 1.00 | 1.00 | 1.00 | 1.00 | 1.00 | 1.00 | 1.00 | 1.00 | 0.98 | 0.99 |
| Slc39a5 | 1.00 | 1.00 | 1.00 | 1.00 | 1.00 | 1.00 | 1.01 | 1.02 | 1.03 | 1.00 | 0.94 | 0.99 |
| Slc7a9 | 1.00 | 1.00 | 1.00 | 1.00 | 1.00 | 1.00 | 1.00 | 1.00 | 1.00 | 1.00 | 1.00 | 1.00 |
| Slc9a3 | 1.00 | 1.00 | 1.00 | 1.00 | 1.00 | 1.00 | 1.00 | 1.00 | 1.00 | 1.02 | 1.16 | 1.15 |
| Slc9a3r2 | 1.29 | 1.25 | 1.63 | 1.45 | 0.10 | 0.94 | 1.10 | 0.95 | 1.08 | 1.15 | 1.07 | 1.01 |
| Slfn5os | 1.02 | 1.02 | 1.00 | 1.00 | 1.00 | 1.00 | 1.00 | 1.00 | 1.00 | 1.00 | 1.26 | 1.08 |
| Slurp1 | 0.88 | 1.46 | 1.00 | 1.00 | 1.00 | 1.00 | 1.00 | 1.00 | 1.00 | 0.91 | 1.00 | 0.91 |
| Snai3 | 0.83 | 0.56 | 0.80 | 1.00 | 1.00 | 1.00 | 1.00 | 1.00 | 1.00 | 1.00 | 1.00 | 1.00 |
| Snora3 | 0.95 | 1.43 | 0.61 | 0.97 | 1.00 | 0.96 | 0.56 | 0.30 | 0.82 | 0.03 | 0.82 | 1.00 |
| Snora30 | 3.10 | 0.70 | 0.17 | 1.02 | 3.67 | 0.86 | 1.00 | 1.09 | 1.08 | 1.00 | 1.00 | 1.00 |
| Snora31 | 0.86 | 0.84 | 0.84 | 1.21 | 1.08 | 1.00 | 0.93 | 1.28 | 0.63 | 1.00 | 1.00 | 0.09 |
| Snora65 | 0.90 | 1.07 | 0.90 | 0.92 | 0.97 | 1.06 | 0.84 | 0.53 | 1.12 | 1.00 | 0.08 | 2.20 |
| Snora70 | 1.10 | 1.05 | 1.09 | 1.06 | 1.14 | 0.63 | 1.53 | 0.95 | 1.01 | 0.80 | 0.05 | 1.00 |
| Snord116l2 | 1.00 | 1.00 | 1.00 | 1.00 | 1.00 | 1.00 | 1.00 | 1.00 | 1.00 | 1.00 | 1.00 | 1.00 |
| Snord15b | 0.86 | 1.33 | 1.19 | 1.40 | 0.67 | 1.13 | 1.34 | 0.13 | 1.51 | 1.00 | 1.00 | 0.80 |

Fig. 31-21

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Snord33 | 5.00 | 1.44 | 1.60 | 0.39 | 1.52 | 0.04 | 1.50 | 1.44 | 2.15 |
| Snord35a | 1.96 | 0.98 | 2.14 | 1.42 | 1.12 | 0.88 | 0.60 | 0.03 | 1.17 |
| Snord43 | 1.00 | 1.00 | 1.00 | 1.00 | 1.00 | 1.00 | 1.00 | 1.00 | 1.00 |
| Sntn | 1.00 | 1.00 | 1.00 | 1.00 | 1.00 | 1.00 | 1.00 | 1.00 | 1.00 |
| Sorcs2 | 1.12 | 1.58 | 1.37 | 1.00 | 1.00 | 1.00 | 1.00 | 1.00 | 1.00 |
| Spink3 | 1.00 | 1.00 | 1.00 | 0.94 | 0.91 | 1.15 | 1.00 | 1.00 | 1.00 |
| Stbd1 | 2.50 | 1.79 | 1.44 | 0.99 | 0.96 | 1.13 | 1.09 | 0.65 | 0.70 |
| Sult5a1 | 0.65 | 1.25 | 1.70 | 1.17 | 1.00 | 1.00 | 0.11 | 0.50 | 0.77 |
| Svs2 | 1.00 | 1.00 | 1.00 | 1.00 | 1.00 | 1.00 | 1.00 | 1.00 | 1.00 |
| Svs4 | 1.00 | 1.00 | 1.00 | 1.00 | 1.00 | 1.00 | 1.00 | 1.00 | 1.00 |
| Svs6 | 1.00 | 1.00 | 1.00 | 1.00 | 1.00 | 1.00 | 1.00 | 1.00 | 1.00 |
| Sycn | 1.00 | 1.00 | 1.00 | 0.44 | 2.39 | 1.00 | 1.00 | 1.59 | 1.00 |
| Tcerg1l | 1.00 | 1.00 | 1.00 | 1.00 | 1.00 | 1.00 | 1.00 | 1.00 | 1.00 |
| Tctex1d4 | 1.00 | 1.00 | 1.00 | 1.00 | 1.00 | 1.00 | 1.00 | 1.00 | 1.00 |
| Tekt1 | 1.00 | 1.00 | 1.00 | 1.00 | 1.00 | 1.00 | 1.00 | 1.00 | 1.00 |
| Tesc | 1.25 | 0.57 | 0.58 | 0.44 | 1.22 | 0.95 | 1.00 | 1.00 | 1.00 |
| Tff3 | 1.00 | 1.00 | 1.00 | 1.00 | 1.00 | 1.00 | 0.94 | 2.38 | 0.19 |
| Tmed6 | 1.00 | 1.00 | 1.00 | 0.68 | 0.95 | 0.99 | 1.11 | 1.00 | 1.62 |
| Tmem212 | 1.00 | 1.00 | 1.00 | 1.00 | 1.00 | 1.00 | 1.00 | 1.00 | 1.00 |
| Tnp1 | 1.00 | 1.00 | 1.00 | 1.00 | 1.00 | 1.00 | 1.00 | 1.00 | 1.00 |
| Tnp2 | 1.00 | 1.00 | 1.00 | 1.00 | 1.00 | 1.00 | 1.00 | 1.00 | 1.00 |
| Try10 | 1.00 | 1.00 | 1.00 | 1.00 | 1.00 | 1.00 | 1.00 | 1.00 | 1.00 |
| Try4 | 1.00 | 1.00 | 1.00 | 1.00 | 1.00 | 1.00 | 1.00 | 1.82 | 1.00 |
| Try5 | 1.00 | 1.00 | 1.00 | 1.00 | 1.00 | 1.00 | 1.00 | 1.68 | 1.00 |
| Ubash3a | 1.00 | 1.00 | 1.00 | 1.00 | 1.00 | 1.00 | 1.00 | 1.19 | 1.00 |
| Vil1 | 1.00 | 1.00 | 1.00 | 1.02 | 0.83 | 1.03 | 1.00 | 1.00 | 1.00 |
| Vmn2r29 | 1.00 | 1.00 | 1.00 | 1.00 | 1.00 | 1.00 | 1.00 | 1.00 | 1.00 |
| Wdr52 | 1.00 | 1.00 | 1.00 | 1.00 | 1.00 | 1.00 | 1.00 | 1.00 | 1.00 |
| Zg16 | 1.00 | 1.00 | 1.00 | 1.00 | 1.00 | 1.00 | 1.00 | 1.61 | 1.00 |
| 1190002F15Rik | 1.00 | 1.94 | 1.00 | 0.99 | 1.00 | 1.00 | 1.00 | 2.10 | 1.00 |
| 1500011B03Rik | 1.21 | 1.62 | 1.09 | 1.17 | 1.05 | 0.95 | 1.66 | 1.66 | 0.90 |
| 1500015O10Rik | 0.95 | 4.28 | 9.27 | 1.28 | 0.91 | 0.93 | 1.00 | 1.00 | 1.00 |
| 1700018G05Rik | 1.00 | 1.00 | 1.00 | 1.00 | 1.00 | 1.00 | 1.00 | 1.00 | 1.00 |
| 1700027J07Rik | 1.00 | 1.35 | 1.00 | 1.00 | 1.00 | 1.00 | 1.00 | 2.81 | 1.00 |
| 1700049E15Rik | 1.00 | 1.00 | 1.00 | 1.00 | 1.00 | 1.00 | 1.00 | 1.00 | 1.00 |
| 1700095A21Rik | 1.00 | 1.00 | 1.00 | 1.00 | 1.00 | 1.00 | 1.00 | 1.00 | 1.00 |
| 1700097N02Rik | 1.00 | 1.79 | 1.00 | 1.00 | 1.00 | 1.00 | 1.00 | 5.02 | 1.00 |
| 1700120C14Rik | 0.97 | 1.25 | 0.86 | 1.10 | 1.38 | 1.00 | 1.00 | 1.00 | 1.00 |
| 1810009J06Rik | 1.00 | 1.00 | 1.00 | 1.00 | 1.00 | 1.00 | 1.00 | 1.00 | 1.00 |
| 1810019D21Rik | 1.00 | 1.00 | 1.00 | 1.30 | 0.99 | 1.14 | 1.05 | 0.66 | 1.02 |
| 2010109A12Rik | 1.00 | 1.00 | 1.00 | 1.00 | 1.00 | 1.00 | 1.00 | 1.00 | 1.00 |
| 2310002J15Rik | 1.00 | 1.00 | 1.00 | 1.00 | 0.98 | 1.00 | 1.00 | 1.00 | 1.00 |
| 2700099C18Rik | 1.00 | 1.12 | 1.00 | 1.00 | 1.00 | 1.00 | 1.00 | 1.06 | 1.00 |
| 2810417H13Rik | 1.00 | 1.84 | 1.00 | 1.00 | 1.00 | 1.00 | 1.00 | 4.21 | 1.00 |
| 4931429I11Rik | 1.00 | 1.16 | 1.00 | 1.00 | 1.00 | 1.00 | 1.00 | 2.00 | 1.00 |
| 5033403H07Rik | 1.00 | 1.00 | 1.00 | 1.00 | 1.00 | 1.00 | 1.06 | 0.85 | 1.19 |
| 8430408G22Rik | 2.36 | 0.88 | 0.58 | 1.61 | 1.58 | 0.44 | 0.61 | 1.27 | 0.66 |
| 9130230L23Rik | 1.00 | 1.00 | 1.00 | 1.00 | 1.00 | 1.00 | 1.00 | 1.00 | 1.00 |
| 9230104L09Rik | 1.00 | 1.00 | 1.00 | 1.00 | 1.00 | 1.00 | 1.00 | 1.00 | 1.00 |
| AA467197 | 6.10 | 1.53 | 1.00 | 1.15 | 1.00 | 1.00 | 1.00 | 1.00 | 1.00 |
| Aass | 1.19 | 1.88 | 1.54 | 1.13 | 0.68 | 0.92 | 1.06 | 0.72 | 1.03 |
| Acnat2 | 1.00 | 1.00 | 1.00 | 2.25 | 1.59 | 1.16 | 1.74 | 5.49 | 1.05 |
| Acta1 | 1.33 | 1.15 | 1.87 | 0.94 | 0.98 | 1.25 | 1.00 | 1.13 | 1.00 |
| Actc1 | 1.21 | 0.61 | 0.91 | 1.00 | 1.00 | 1.00 | 1.00 | 1.00 | 1.00 |
| Actn2 | 1.01 | 0.72 | 0.84 | 1.00 | 1.00 | 1.00 | 1.00 | 1.00 | 1.00 |
| Adam7 | 1.00 | 1.00 | 1.00 | 1.00 | 1.00 | 1.00 | 1.00 | 1.00 | 1.00 |
| Adam8 | 4.26 | 10.26 | 1.38 | 1.00 | 1.00 | 1.00 | 1.00 | 1.00 | 1.00 |
| Adamts4 | 20.35 | 5.38 | 1.33 | 1.00 | 1.00 | 1.00 | 1.00 | 1.00 | 1.00 |
| Adamts8 | 7.84 | 8.57 | 16.46 | 0.81 | 1.00 | 1.00 | 1.00 | 1.00 | 1.00 |
| Adamtsl2 | 0.92 | 5.21 | 5.14 | 1.10 | 1.07 | 0.98 | 1.28 | 1.03 | 1.16 |
| Adh7 | 1.00 | 1.00 | 1.00 | 1.07 | 1.23 | 1.64 | 0.90 | 0.61 | 0.77 |
| Adipoq | 0.79 | 0.52 | 10.29 | 0.75 | 0.22 | 0.83 | 1.00 | 1.00 | 1.00 |
| AF251705 | 1.12 | 5.24 | 2.78 | 0.87 | 1.34 | 0.77 | 0.83 | 1.78 | 0.81 |
| AF357355 | 0.04 | 1.00 | 1.00 | 1.00 | 1.00 | 1.00 | 1.00 | 1.00 | 1.00 |

Fig. 31-22

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Snord33 | 2.48 | 1.55 | 0.82 | 0.02 | 1.02 | 2.60 | 1.16 | 0.94 | 1.92 |
| Snord35a | 0.57 | 4.75 | 2.54 | 0.34 | 4.72 | 0.55 | 0.90 | 1.28 | 1.19 |
| Snord43 | 1.00 | 1.00 | 1.00 | 1.00 | 1.00 | 1.00 | 1.00 | 1.00 | 1.00 |
| Sntn | 0.84 | 0.80 | 0.69 | 1.00 | 1.00 | 1.00 | 1.00 | 1.00 | 1.00 |
| Sorcs2 | 1.48 | 1.06 | 0.96 | 1.00 | 1.00 | 1.00 | 1.00 | 1.00 | 1.00 |
| Spink3 | 1.00 | 1.00 | 1.00 | 0.35 | 1.00 | 1.00 | 1.35 | 0.08 | 0.02 |
| Stbd1 | 1.03 | 0.99 | 1.04 | 0.86 | 1.02 | 1.51 | 1.17 | 0.84 | 0.79 |
| Sult5a1 | 1.02 | 0.82 | 0.93 | 1.38 | 1.13 | 1.15 | 1.00 | 1.00 | 1.00 |
| Svs2 | 1.00 | 1.00 | 1.00 | 0.06 | 2.28 | 1.00 | 1.00 | 1.00 | 1.00 |
| Svs4 | 1.00 | 1.00 | 1.00 | 0.03 | 4.96 | 1.00 | 1.00 | 1.00 | 1.00 |
| Svs6 | 1.00 | 1.00 | 1.00 | 0.06 | 2.35 | 1.00 | 1.00 | 1.00 | 1.00 |
| Sycn | 1.00 | 1.00 | 1.00 | 1.00 | 1.00 | 1.00 | 1.48 | 0.08 | 0.00 |
| Tcerg1l | 1.00 | 1.00 | 1.00 | 1.00 | 1.00 | 1.00 | 1.00 | 1.00 | 1.00 |
| Tctex1d4 | 0.78 | 0.77 | 0.80 | 1.00 | 1.00 | 1.00 | 1.00 | 1.00 | 1.00 |
| Tekt1 | 0.87 | 0.81 | 0.88 | 2.11 | 1.22 | 0.81 | 1.00 | 1.00 | 1.00 |
| Tesc | 1.67 | 0.64 | 0.82 | 1.00 | 0.92 | 0.94 | 0.86 | 0.78 | 0.72 |
| Tff3 | 1.00 | 1.00 | 1.00 | 1.00 | 1.00 | 1.00 | 1.00 | 1.00 | 1.00 |
| Tmed6 | 0.84 | 0.96 | 0.89 | 1.00 | 1.00 | 1.00 | 1.35 | 0.10 | 0.10 |
| Tmem212 | 0.93 | 1.05 | 0.76 | 1.00 | 1.00 | 1.00 | 1.00 | 1.00 | 1.00 |
| Tnp1 | 1.00 | 1.00 | 1.00 | 1.00 | 0.94 | 0.06 | 1.00 | 1.00 | 1.00 |
| Tnp2 | 1.00 | 1.00 | 1.00 | 1.00 | 0.98 | 0.09 | 1.00 | 1.00 | 1.00 |
| Try10 | 1.00 | 1.00 | 1.00 | 1.00 | 1.00 | 1.00 | 1.57 | 0.08 | 0.01 |
| Try4 | 1.00 | 1.00 | 1.00 | 1.00 | 1.00 | 1.00 | 1.81 | 0.08 | 0.00 |
| Try5 | 1.00 | 1.00 | 1.00 | 1.00 | 1.00 | 1.00 | 2.06 | 0.08 | 0.00 |
| Ubash3a | 1.00 | 3.17 | 1.00 | 1.00 | 1.00 | 1.00 | 1.15 | 1.25 | 1.22 |
| Vil1 | 1.00 | 1.00 | 1.00 | 1.00 | 1.00 | 1.00 | 1.00 | 1.00 | 1.00 |
| Vmn2r29 | 1.00 | 1.00 | 1.00 | 1.00 | 1.00 | 1.00 | 1.00 | 1.00 | 1.00 |
| Wdr52 | 0.87 | 0.71 | 0.90 | 1.00 | 1.00 | 1.00 | 1.00 | 1.00 | 1.00 |
| Zg16 | 1.00 | 1.00 | 1.00 | 1.00 | 1.00 | 1.00 | 1.25 | 0.07 | 0.00 |
| 1190002F15Rik | 1.46 | 11.31 | 0.95 | 1.00 | 1.00 | 1.00 | 1.22 | 1.26 | 3.46 |
| 1500011B03Rik | 1.18 | 1.40 | 0.97 | 1.22 | 1.04 | 1.20 | 1.10 | 1.17 | 0.82 |
| 1500015O10Rik | 0.93 | 2.30 | 1.41 | 1.33 | 0.54 | 0.54 | 1.58 | 0.41 | 0.89 |
| 1700018G05Rik | 1.00 | 1.00 | 1.00 | 1.00 | 1.00 | 1.00 | 1.00 | 1.00 | 1.00 |
| 1700027J07Rik | 1.00 | 16.18 | 1.00 | 1.14 | 0.98 | 1.00 | 1.65 | 0.50 | 0.65 |
| 1700049E15Rik | 1.00 | 1.00 | 1.00 | 1.00 | 1.00 | 1.00 | 1.00 | 1.00 | 1.00 |
| 1700095A21Rik | 1.00 | 1.00 | 1.00 | 1.00 | 1.00 | 1.00 | 1.00 | 1.00 | 1.00 |
| 1700097N02Rik | 1.32 | 20.43 | 1.45 | 1.00 | 1.00 | 1.00 | 1.94 | 0.98 | 1.38 |
| 1700120C14Rik | 0.91 | 1.38 | 1.19 | 0.80 | 1.10 | 0.98 | 1.08 | 1.27 | 1.26 |
| 1810009J06Rik | 1.00 | 1.00 | 1.00 | 1.00 | 1.00 | 1.00 | 1.05 | 1.00 | 1.00 |
| 1810019D21Rik | 1.20 | 0.92 | 1.14 | 1.00 | 1.00 | 1.00 | 1.68 | 0.88 | 1.00 |
| 2010109A12Rik | 1.00 | 1.00 | 1.00 | 1.00 | 1.00 | 1.00 | 1.00 | 1.14 | 1.00 |
| 2310002J15Rik | 1.00 | 1.00 | 1.00 | 1.00 | 1.00 | 1.00 | 1.00 | 1.00 | 1.00 |
| 2700099C18Rik | 1.38 | 5.53 | 0.92 | 1.00 | 1.00 | 1.00 | 0.81 | 1.27 | 1.14 |
| 2810417H13Rik | 2.12 | 14.55 | 1.00 | 1.00 | 1.00 | 1.00 | 0.67 | 1.50 | 2.12 |
| 4931429I11Rik | 0.72 | 11.79 | 0.98 | 1.00 | 1.00 | 1.00 | 0.85 | 0.53 | 1.11 |
| 5033403H07Rik | 1.10 | 0.53 | 0.77 | 1.00 | 1.00 | 1.00 | 1.00 | 1.00 | 1.00 |
| 8430408G22Rik | 0.90 | 0.62 | 0.73 | 6.17 | 12.88 | 0.86 | 1.07 | 0.71 | 1.19 |
| 9130230L23Rik | 0.72 | 0.81 | 0.94 | 1.00 | 1.00 | 1.00 | 1.00 | 1.00 | 1.00 |
| 9230104L09Rik | 0.53 | 0.94 | 1.51 | 1.00 | 1.00 | 1.00 | 1.00 | 1.00 | 1.00 |
| AA467197 | 1.36 | 2.31 | 0.87 | 1.00 | 1.00 | 1.00 | 0.59 | 1.21 | 1.16 |
| Aass | 0.61 | 7.94 | 1.15 | 1.00 | 1.00 | 1.00 | 0.82 | 18.24 | 1.58 |
| Acnat2 | 1.00 | 1.00 | 1.00 | 1.00 | 1.00 | 1.00 | 1.00 | 1.00 | 1.00 |
| Acta1 | 2.04 | 1.84 | 1.65 | 0.96 | 1.07 | 1.01 | 0.92 | 0.92 | 1.11 |
| Actc1 | 1.02 | 0.91 | 1.48 | 0.84 | 0.38 | 0.35 | 1.00 | 1.00 | 1.00 |
| Actn2 | 0.98 | 1.08 | 1.27 | 1.02 | 0.80 | 1.03 | 1.07 | 0.86 | 0.94 |
| Adam7 | 1.00 | 1.00 | 1.00 | 1.00 | 1.00 | 1.00 | 1.00 | 1.00 | 1.00 |
| Adam8 | 1.35 | 1.03 | 1.06 | 1.00 | 0.98 | 1.00 | 0.80 | 1.03 | 0.94 |
| Adamts4 | 2.84 | 1.10 | 1.00 | 1.00 | 1.00 | 1.00 | 1.00 | 1.00 | 1.00 |
| Adamts8 | 1.03 | 0.77 | 1.09 | 0.78 | 1.52 | 1.00 | 1.00 | 1.00 | 1.00 |
| Adamtsl2 | 1.09 | 0.95 | 0.92 | 1.39 | 0.66 | 1.19 | 1.90 | 0.59 | 0.70 |
| Adh7 | 0.93 | 0.53 | 0.40 | 1.00 | 1.00 | 1.00 | 1.00 | 1.00 | 1.00 |
| Adipoq | 0.44 | 1.53 | 0.34 | 0.81 | 1.75 | 1.66 | 3.53 | 0.62 | 1.24 |
| AF251705 | 0.81 | 1.27 | 1.18 | 0.94 | 1.00 | 1.00 | 0.92 | 0.93 | 0.92 |
| AF357355 | 0.05 | 1.00 | 1.00 | 1.00 | 1.00 | 1.00 | 1.00 | 1.00 | 1.00 |

Fig. 31- 23

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Snord33 | 0.34 | 0.75 | 0.69 | 1.09 | 0.51 | 0.43 | 0.88 | 1.81 | 1.27 |
| Snord35a | 0.41 | 0.76 | 1.05 | 1.06 | 1.07 | 2.33 | 0.83 | 0.84 | 1.33 |
| Snord43 | 1.00 | 1.00 | 1.00 | 1.00 | 1.00 | 1.00 | 1.00 | 1.00 | 1.00 |
| Sntn | 1.00 | 1.00 | 1.00 | 0.55 | 0.15 | 1.00 | 1.00 | 1.00 | 1.00 |
| Sorcs2 | 1.00 | 1.01 | 0.96 | 0.37 | 0.18 | 0.85 | 1.05 | 0.96 | 0.89 |
| Spink3 | 1.00 | 1.00 | 0.72 | 1.00 | 1.00 | 1.00 | 1.00 | 1.00 | 1.00 |
| Stbd1 | 0.99 | 1.00 | 1.00 | 0.55 | 0.20 | 0.88 | 1.03 | 0.91 | 0.79 |
| Sult5a1 | 1.00 | 1.00 | 1.00 | 0.92 | 1.61 | 0.95 | 1.35 | 1.00 | 1.02 |
| Svs2 | 1.00 | 1.00 | 1.00 | 1.00 | 1.00 | 1.00 | 1.00 | 1.00 | 1.00 |
| Svs4 | 1.00 | 1.00 | 1.00 | 1.00 | 1.00 | 1.00 | 1.01 | 1.07 | 1.26 |
| Svs6 | 1.00 | 1.00 | 1.00 | 1.00 | 1.00 | 1.00 | 1.00 | 1.00 | 1.00 |
| Sycn | 1.00 | 1.00 | 1.00 | 1.00 | 1.00 | 1.00 | 1.00 | 1.00 | 1.00 |
| Tcerg1l | 1.00 | 0.99 | 1.04 | 0.11 | 1.00 | 1.00 | 0.92 | 1.02 | 1.17 |
| Tctex1d4 | 1.00 | 1.00 | 1.00 | 0.40 | 0.14 | 1.00 | 1.00 | 1.00 | 1.00 |
| Tekt1 | 0.89 | 1.03 | 1.28 | 0.45 | 0.18 | 1.00 | 1.10 | 1.07 | 0.96 |
| Tesc | 0.90 | 0.96 | 0.99 | 0.54 | 0.12 | 0.88 | 0.69 | 0.74 | 1.28 |
| Tff3 | 1.00 | 1.00 | 1.00 | 1.00 | 0.34 | 1.00 | 1.00 | 1.00 | 1.00 |
| Tmed6 | 1.00 | 1.00 | 1.00 | 0.59 | 3.11 | 1.00 | 0.97 | 1.01 | 0.78 |
| Tmem212 | 0.84 | 1.22 | 0.93 | 0.27 | 0.09 | 1.00 | 1.00 | 1.00 | 1.00 |
| Tnp1 | 1.00 | 1.00 | 1.00 | 1.00 | 2.17 | 1.00 | 0.95 | 0.95 | 0.99 |
| Tnp2 | 1.00 | 1.00 | 1.00 | 1.00 | 2.45 | 1.00 | 0.95 | 0.94 | 1.01 |
| Try10 | 1.00 | 1.00 | 1.00 | 1.00 | 1.00 | 1.00 | 1.00 | 1.00 | 1.00 |
| Try4 | 1.00 | 1.00 | 1.00 | 1.00 | 1.00 | 1.00 | 0.72 | 1.01 | 1.11 |
| Try5 | 1.00 | 1.00 | 1.00 | 1.00 | 1.00 | 1.00 | 0.92 | 0.78 | 0.86 |
| Ubash3a | 1.00 | 1.00 | 1.00 | 1.00 | 1.00 | 1.00 | 0.36 | 0.15 | 0.15 |
| Vil1 | 1.00 | 1.00 | 1.00 | 0.53 | 0.16 | 1.00 | 1.00 | 1.00 | 1.00 |
| Vmn2r29 | 1.00 | 1.00 | 1.00 | 1.00 | 1.00 | 1.00 | 1.00 | 1.00 | 1.00 |
| Wdr52 | 0.95 | 1.13 | 1.02 | 0.48 | 0.16 | 1.00 | 0.92 | 0.82 | 1.15 |
| Zg16 | 1.00 | 1.00 | 1.00 | 1.00 | 0.15 | 1.00 | 1.00 | 1.00 | 1.00 |
| 1190002F15Rik | 1.00 | 1.07 | 1.00 | 1.00 | 1.16 | 1.00 | 1.00 | 1.00 | 1.00 |
| 1500011B03Rik | 1.02 | 1.03 | 0.95 | 0.98 | 5.66 | 1.05 | 0.84 | 0.79 | 1.05 |
| 1500015O10Rik | 0.85 | 1.29 | 1.23 | 1.57 | 0.98 | 0.82 | 0.92 | 0.84 | 0.93 |
| 1700018G05Rik | 1.10 | 0.97 | 1.00 | 1.00 | 13.38 | 1.00 | 0.91 | 1.03 | 0.99 |
| 1700027J07Rik | 1.00 | 1.30 | 1.00 | 1.00 | 1.00 | 1.00 | 1.00 | 1.00 | 1.00 |
| 1700049E15Rik | 1.00 | 1.00 | 1.00 | 1.00 | 1.00 | 1.00 | 1.09 | 5.01 | 2.13 |
| 1700095A21Rik | 1.00 | 1.00 | 1.00 | 1.00 | 1.00 | 1.00 | 8.20 | 0.65 | 0.96 |
| 1700097N02Rik | 1.00 | 2.11 | 1.00 | 1.00 | 1.00 | 1.00 | 1.44 | 0.76 | 1.66 |
| 1700120C14Rik | 1.00 | 0.78 | 1.07 | 0.77 | 6.57 | 1.00 | 0.97 | 0.85 | 0.71 |
| 1810009J06Rik | 1.00 | 1.00 | 1.00 | 1.00 | 1.00 | 1.00 | 1.00 | 1.00 | 1.00 |
| 1810019D21Rik | 1.00 | 1.00 | 1.00 | 1.00 | 15.09 | 1.00 | 1.00 | 1.00 | 1.00 |
| 2010109A12Rik | 1.00 | 1.00 | 1.00 | 1.00 | 1.26 | 1.00 | 11.66 | 2.01 | 10.74 |
| 2310002J15Rik | 1.00 | 1.00 | 1.00 | 1.00 | 1.00 | 1.00 | 1.44 | 0.95 | 1.23 |
| 2700099C18Rik | 1.00 | 1.00 | 1.00 | 1.00 | 1.25 | 1.00 | 0.99 | 1.02 | 0.74 |
| 2810417H13Rik | 1.00 | 1.92 | 1.00 | 1.00 | 1.02 | 1.00 | 0.97 | 0.90 | 1.00 |
| 4931429I11Rik | 1.08 | 1.73 | 1.49 | 1.00 | 0.94 | 1.00 | 1.16 | 1.11 | 0.98 |
| 5033403H07Rik | 1.00 | 1.00 | 1.00 | 1.00 | 15.11 | 1.00 | 0.88 | 0.97 | 0.68 |
| 8430408G22Rik | 3.28 | 0.93 | 1.20 | 3.33 | 2.46 | 0.38 | 1.00 | 1.00 | 1.00 |
| 9130230L23Rik | 1.00 | 1.00 | 1.00 | 1.00 | 9.83 | 1.00 | 1.00 | 1.00 | 1.00 |
| 9230104L09Rik | 1.00 | 1.00 | 1.00 | 1.00 | 6.06 | 1.21 | 1.53 | 1.17 | 1.85 |
| AA467197 | 1.00 | 1.00 | 1.00 | 1.79 | 0.76 | 1.85 | 1.03 | 0.98 | 1.01 |
| Aass | 1.12 | 2.05 | 1.30 | 0.85 | 8.06 | 1.17 | 0.74 | 1.51 | 1.13 |
| Acnat2 | 1.00 | 1.00 | 1.00 | 1.00 | 1.00 | 1.00 | 1.00 | 1.00 | 1.00 |
| Acta1 | 0.88 | 1.06 | 0.94 | 0.64 | 1.11 | 0.73 | 0.91 | 1.10 | 0.93 |
| Actc1 | 1.00 | 1.00 | 2.05 | 1.00 | 1.00 | 1.00 | 0.93 | 1.02 | 1.00 |
| Actn2 | 0.90 | 1.07 | 1.04 | 1.00 | 1.00 | 1.00 | 3.75 | 0.92 | 1.16 |
| Adam7 | 1.00 | 1.00 | 1.00 | 1.00 | 43.90 | 1.00 | 1.00 | 1.00 | 1.47 |
| Adam8 | 1.06 | 0.99 | 1.14 | 2.15 | 1.82 | 0.40 | 0.93 | 1.13 | 0.71 |
| Adamts4 | 0.98 | 0.92 | 1.11 | 4.43 | 1.43 | 2.25 | 1.00 | 1.00 | 1.00 |
| Adamts8 | 0.96 | 0.99 | 1.06 | 1.00 | 1.00 | 1.00 | 1.00 | 1.00 | 1.00 |
| Adamtsl2 | 0.91 | 0.94 | 0.78 | 1.05 | 0.75 | 1.08 | 1.00 | 1.00 | 1.00 |
| Adh7 | 1.00 | 1.00 | 1.00 | 1.00 | 7.08 | 1.00 | 1.12 | 1.23 | 1.03 |
| Adipoq | 1.00 | 1.00 | 1.00 | 0.91 | 0.81 | 1.09 | 0.84 | 1.19 | 1.01 |
| AF251705 | 0.97 | 1.10 | 0.88 | 1.33 | 1.52 | 0.74 | 1.00 | 1.00 | 1.00 |
| AF357355 | 1.00 | 1.00 | 0.04 | 1.00 | 1.00 | 28.53 | 1.00 | 1.00 | 1.00 |

Fig. 31- 24

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Snord33 | 0.94 | 0.77 | 0.91 | 0.44 | 1.78 | 0.92 | 2.07 | 0.27 | 0.86 | 1.00 | 1.00 | 1.00 |
| Snord35a | 1.02 | 0.67 | 0.90 | 2.07 | 1.48 | 0.74 | 4.27 | 0.30 | 1.73 | 1.00 | 1.00 | 1.00 |
| Snord43 | 1.00 | 1.00 | 1.00 | 1.00 | 0.01 | 1.00 | 1.00 | 1.00 | 1.00 | 1.00 | 1.00 | 1.00 |
| Sntn | 1.00 | 1.58 | 1.00 | 1.00 | 1.00 | 1.00 | 1.00 | 1.00 | 1.00 | 1.00 | 1.00 | 1.00 |
| Sorcs2 | 1.05 | 1.48 | 1.29 | 1.00 | 1.00 | 1.00 | 1.00 | 1.00 | 1.00 | 0.84 | 1.09 | 1.02 |
| Spink3 | 1.77 | 0.62 | 0.94 | 1.00 | 1.00 | 1.00 | 0.73 | 0.80 | 1.09 | 1.00 | 1.11 | 1.06 |
| Stbd1 | 0.87 | 1.32 | 1.40 | 1.00 | 1.00 | 1.00 | 0.81 | 1.00 | 1.00 | 1.33 | 1.00 | 1.32 |
| Sult5a1 | 1.17 | 1.17 | 1.22 | 1.00 | 1.00 | 1.00 | 1.00 | 1.00 | 1.00 | 1.20 | 1.07 | 0.97 |
| Svs2 | 1.00 | 1.00 | 1.00 | 1.00 | 1.00 | 1.00 | 1.00 | 1.00 | 1.00 | 1.00 | 1.00 | 1.00 |
| Svs4 | 1.02 | 1.00 | 1.00 | 1.00 | 1.00 | 1.00 | 1.00 | 1.00 | 1.00 | 1.00 | 1.00 | 1.00 |
| Svs6 | 1.00 | 1.00 | 1.00 | 1.00 | 1.00 | 1.00 | 1.00 | 1.00 | 1.00 | 1.00 | 1.10 | 0.85 |
| Sycn | 0.65 | 1.00 | 0.38 | 1.00 | 1.00 | 1.00 | 0.61 | 0.69 | 1.07 | 1.76 | 1.00 | 1.00 |
| Tcerg1l | 1.00 | 1.00 | 1.00 | 1.00 | 1.00 | 1.00 | 1.00 | 1.00 | 1.00 | 1.00 | 0.91 | 1.00 |
| Tctex1d4 | 1.00 | 2.41 | 1.00 | 1.00 | 1.00 | 1.00 | 1.00 | 1.00 | 1.00 | 1.00 | 1.35 | 0.69 |
| Tekt1 | 1.00 | 1.58 | 1.00 | 1.00 | 1.00 | 1.00 | 1.00 | 1.00 | 1.00 | 1.00 | 1.00 | 1.00 |
| Tesc | 0.82 | 1.16 | 0.95 | 0.95 | 0.62 | 1.48 | 1.00 | 1.00 | 1.00 | 0.71 | 0.97 | 1.14 |
| Tff3 | 2.05 | 0.58 | 1.06 | 1.00 | 1.00 | 1.00 | 1.00 | 0.57 | 1.00 | 1.00 | 0.81 | 1.06 |
| Tmed6 | 1.00 | 1.00 | 1.00 | 1.00 | 1.00 | 1.00 | 0.81 | 1.00 | 1.10 | 1.00 | 0.93 | 0.98 |
| Tmem212 | 1.29 | 4.08 | 1.00 | 1.00 | 1.00 | 1.00 | 1.00 | 1.00 | 1.00 | 1.00 | 1.03 | 1.14 |
| Tnp1 | 1.00 | 1.00 | 1.00 | 1.00 | 1.00 | 1.00 | 1.00 | 1.00 | 1.00 | 1.00 | 0.86 | 1.09 |
| Tnp2 | 1.08 | 1.00 | 1.00 | 1.00 | 1.00 | 1.00 | 1.00 | 1.00 | 1.00 | 1.05 | 0.95 | 0.96 |
| Try10 | 1.00 | 1.00 | 1.00 | 1.00 | 1.00 | 1.00 | 0.84 | 0.95 | 0.99 | 1.00 | 1.00 | 1.38 |
| Try4 | 0.39 | 1.00 | 0.35 | 1.00 | 1.00 | 1.00 | 0.87 | 0.99 | 0.95 | 0.92 | 1.57 | 1.66 |
| Try5 | 0.51 | 1.00 | 0.46 | 1.00 | 1.00 | 1.00 | 0.89 | 1.21 | 0.97 | 0.62 | 0.91 | 0.95 |
| Ubash3a | 0.79 | 0.69 | 1.05 | 0.92 | 0.74 | 1.09 | 1.00 | 1.00 | 1.00 | 1.00 | 0.84 | 1.05 |
| Vil1 | 1.18 | 1.00 | 1.00 | 1.00 | 1.00 | 1.00 | 1.00 | 1.00 | 1.00 | 1.00 | 0.97 | 0.92 |
| Vmn2r29 | 1.00 | 0.15 | 1.00 | 1.00 | 0.64 | 1.00 | 1.00 | 1.00 | 1.00 | 1.00 | 1.00 | 1.00 |
| Wdr52 | 1.00 | 1.16 | 1.00 | 1.00 | 1.00 | 1.00 | 1.00 | 1.00 | 1.00 | 1.00 | 1.34 | 1.00 |
| Zg16 | 0.77 | 1.00 | 0.37 | 0.82 | 1.00 | 1.46 | 0.84 | 0.81 | 1.08 | 1.13 | 0.93 | 0.85 |
| 1190002F15Rik | 0.41 | 0.66 | 0.91 | 1.18 | 0.86 | 1.25 | 1.00 | 1.00 | 1.00 | 0.85 | 0.89 | 1.15 |
| 1500011B03Rik | 1.04 | 0.98 | 0.86 | 1.13 | 0.90 | 0.94 | 1.21 | 0.85 | 0.84 | 0.89 | 1.02 | 1.01 |
| 1500015O10Rik | 1.00 | 1.90 | 1.10 | 1.00 | 1.00 | 1.00 | 1.00 | 1.00 | 1.00 | 0.98 | 0.90 | 1.14 |
| 1700018G05Rik | 1.00 | 1.00 | 1.00 | 1.00 | 1.00 | 1.00 | 1.00 | 1.00 | 1.00 | 1.00 | 1.00 | 1.00 |
| 1700027J07Rik | 1.00 | 1.00 | 1.00 | 1.07 | 0.48 | 0.61 | 1.00 | 1.00 | 1.00 | 1.00 | 1.00 | 1.00 |
| 1700049E15Rik | 1.00 | 1.00 | 1.00 | 1.00 | 1.00 | 1.00 | 1.00 | 1.00 | 1.00 | 1.00 | 1.00 | 1.00 |
| 1700095A21Rik | 1.00 | 1.00 | 1.00 | 1.00 | 1.00 | 1.00 | 1.00 | 1.00 | 1.00 | 1.00 | 1.00 | 1.00 |
| 1700097N02Rik | 1.05 | 1.73 | 0.68 | 1.04 | 1.75 | 0.98 | 1.00 | 1.00 | 1.00 | 0.82 | 1.32 | 1.48 |
| 1700120C14Rik | 1.11 | 0.75 | 0.45 | 0.91 | 0.68 | 1.27 | 1.00 | 1.00 | 1.00 | 1.05 | 1.00 | 1.00 |
| 1810009J06Rik | 1.00 | 1.00 | 1.00 | 1.00 | 1.00 | 1.00 | 5.43 | 0.97 | 1.12 | 1.00 | 1.00 | 1.00 |
| 1810019D21Rik | 1.40 | 0.82 | 0.69 | 1.00 | 1.00 | 1.00 | 0.81 | 0.89 | 1.12 | 0.87 | 1.08 | 0.83 |
| 2010109A12Rik | 1.43 | 1.00 | 0.84 | 1.00 | 1.01 | 1.00 | 1.00 | 1.00 | 1.00 | 1.00 | 1.00 | 1.00 |
| 2310002J15Rik | 1.00 | 5.67 | 1.00 | 1.00 | 1.00 | 1.00 | 1.00 | 1.00 | 1.00 | 0.94 | 0.88 | 1.06 |
| 2700099C18Rik | 0.47 | 0.72 | 0.89 | 1.00 | 0.97 | 0.88 | 1.00 | 1.00 | 1.00 | 0.98 | 1.29 | 1.05 |
| 2810417H13Rik | 0.37 | 0.64 | 1.00 | 0.86 | 0.94 | 0.94 | 1.00 | 1.00 | 1.00 | 0.71 | 1.36 | 1.26 |
| 4931429I11Rik | 1.00 | 2.29 | 1.39 | 0.92 | 0.55 | 0.67 | 1.00 | 1.00 | 1.00 | 1.00 | 1.00 | 1.00 |
| 5033403H07Rik | 1.00 | 1.00 | 1.00 | 1.00 | 1.00 | 1.00 | 1.00 | 1.00 | 1.00 | 1.00 | 1.00 | 1.00 |
| 8430408G22Rik | 2.94 | 2.19 | 3.80 | 0.71 | 1.77 | 1.85 | 1.62 | 1.03 | 1.02 | 1.70 | 1.35 | 1.35 |
| 9130230L23Rik | 1.00 | 1.00 | 1.00 | 1.00 | 1.00 | 1.00 | 1.00 | 1.00 | 1.00 | 0.89 | 1.11 | 1.00 |
| 9230104L09Rik | 1.00 | 1.00 | 1.00 | 1.00 | 1.00 | 1.00 | 1.00 | 1.00 | 1.00 | 1.00 | 1.00 | 1.00 |
| AA467197 | 1.19 | 1.11 | 0.71 | 1.13 | 0.98 | 0.96 | 1.00 | 1.00 | 1.00 | 1.00 | 1.00 | 1.00 |
| Aass | 0.09 | 24.62 | 1.31 | 0.15 | 7.40 | 0.94 | 0.88 | 1.04 | 0.99 | 1.39 | 1.13 | 0.85 |
| Acnat2 | 1.00 | 1.00 | 1.00 | 1.00 | 1.00 | 1.00 | 1.00 | 1.00 | 1.00 | 1.00 | 1.00 | 1.00 |
| Acta1 | 0.97 | 10.26 | 1.17 | 1.03 | 1.15 | 1.12 | 1.68 | 1.00 | 1.00 | 1.43 | 1.06 | 1.14 |
| Actc1 | 11.53 | 4.40 | 5.87 | 1.00 | 1.00 | 1.00 | 1.00 | 1.00 | 1.00 | 1.15 | 1.10 | 1.00 |
| Actn2 | 2.60 | 5.67 | 3.65 | 1.00 | 1.00 | 1.00 | 1.00 | 1.00 | 1.00 | 0.99 | 0.88 | 1.17 |
| Adam7 | 1.00 | 1.00 | 1.00 | 1.00 | 1.00 | 1.00 | 1.00 | 1.00 | 1.00 | 1.00 | 1.00 | 1.00 |
| Adam8 | 1.06 | 1.40 | 1.18 | 1.08 | 1.14 | 1.13 | 1.00 | 1.00 | 1.00 | 1.11 | 1.00 | 1.00 |
| Adamts4 | 1.07 | 0.87 | 1.00 | 1.00 | 1.00 | 1.00 | 1.00 | 1.00 | 1.00 | 1.00 | 1.00 | 1.00 |
| Adamts8 | 1.00 | 1.09 | 1.00 | 1.00 | 1.00 | 1.00 | 1.00 | 1.00 | 1.00 | 1.00 | 1.00 | 1.00 |
| Adamtsl2 | 0.82 | 1.00 | 0.61 | 1.00 | 1.00 | 1.00 | 1.00 | 1.00 | 1.00 | 1.00 | 0.84 | 0.91 |
| Adh7 | 1.00 | 3.57 | 1.00 | 1.00 | 1.00 | 1.00 | 1.00 | 1.00 | 1.00 | 1.10 | 1.00 | 1.00 |
| Adipoq | 2.08 | 1.37 | 2.48 | 1.58 | 0.40 | 1.63 | 0.70 | 0.77 | 0.80 | 0.82 | 1.00 | 1.00 |
| AF251705 | 1.26 | 1.05 | 1.00 | 1.35 | 0.73 | 1.02 | 1.00 | 1.00 | 1.00 | 0.68 | 0.99 | 1.01 |
| AF357355 | 1.00 | 1.00 | 1.00 | 1.00 | 1.00 | 1.00 | 1.00 | 1.00 | 1.00 | 1.00 | 1.00 | 1.00 |

Fig. 31-25

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| AF357399 | 1.29 | 0.91 | 0.54 | 2.31 | 7.66 | 1.01 | 1.70 | 0.96 | 0.37 |
| AF357425 | 1.00 | 1.00 | 1.00 | 1.00 | 1.00 | 1.00 | 1.00 | 1.00 | 1.00 |
| Ager | 1.94 | 1.00 | 18.05 | 1.00 | 1.00 | 1.00 | 1.00 | 1.00 | 1.00 |
| Agr2 | 1.00 | 1.00 | 1.00 | 1.00 | 1.00 | 1.00 | 1.00 | 1.00 | 1.00 |
| Alas2 | 0.64 | 1.26 | 4.01 | 1.29 | 6.82 | 1.43 | 0.32 | 0.71 | 0.19 |
| Aldh3a1 | 1.00 | 1.00 | 1.00 | 1.00 | 1.00 | 1.04 | 1.00 | 1.00 | 1.00 |
| Alpl | 1.09 | 0.79 | 1.05 | 1.07 | 0.71 | 0.85 | 0.72 | 1.60 | 0.97 |
| Alppl2 | 1.00 | 1.00 | 1.00 | 1.00 | 1.00 | 1.00 | 1.00 | 1.00 | 1.00 |
| Amd1 | 2.20 | 0.44 | 0.41 | 1.00 | 1.00 | 1.00 | 0.64 | 0.85 | 0.69 |
| Amy2a5 | 1.00 | 1.00 | 1.00 | 1.00 | 1.00 | 1.00 | 1.16 | 7.35 | 0.79 |
| Angptl4 | 5.23 | 1.71 | 5.13 | 4.36 | 1.41 | 0.98 | 4.01 | 1.14 | 0.65 |
| Angptl7 | 0.85 | 3.89 | 5.96 | 1.64 | 0.73 | 0.98 | 1.00 | 1.00 | 1.00 |
| Ankef1 | 1.00 | 1.00 | 1.00 | 1.00 | 1.00 | 1.00 | 1.00 | 1.00 | 1.00 |
| Ankrd1 | 2.05 | 1.80 | 2.85 | 1.00 | 1.00 | 1.00 | 1.00 | 1.00 | 1.00 |
| Ankrd2 | 6.08 | 1.84 | 1.03 | 1.00 | 1.00 | 1.00 | 1.00 | 1.00 | 1.00 |
| Ap1s2 | 1.09 | 1.32 | 1.12 | 1.03 | 1.29 | 1.02 | 1.05 | 2.13 | 0.99 |
| Ap3b2 | 1.00 | 1.00 | 1.00 | 1.00 | 1.00 | 1.00 | 1.00 | 1.00 | 1.00 |
| Apitd1 | 1.17 | 1.20 | 1.10 | 0.92 | 1.01 | 1.00 | 1.00 | 2.81 | 1.00 |
| Apln | 8.02 | 1.43 | 0.87 | 0.62 | 1.10 | 1.05 | 1.00 | 1.00 | 1.00 |
| Apobec1 | 1.21 | 6.11 | 1.92 | 0.85 | 1.58 | 1.07 | 0.83 | 1.87 | 0.85 |
| Apobec2 | 1.06 | 0.69 | 0.74 | 4.60 | 0.91 | 3.31 | 1.00 | 1.00 | 1.00 |
| Apol11a | 1.00 | 1.00 | 1.00 | 1.00 | 1.00 | 1.00 | 1.00 | 1.00 | 1.00 |
| Apol11b | 1.00 | 1.00 | 1.02 | 1.00 | 1.00 | 1.00 | 1.00 | 1.00 | 1.00 |
| Apol7c | 1.00 | 1.00 | 1.00 | 1.00 | 1.00 | 1.00 | 0.93 | 1.29 | 0.57 |
| Apol8 | 1.00 | 1.00 | 1.00 | 1.00 | 1.00 | 1.00 | 1.00 | 1.00 | 1.00 |
| Apold1 | 5.09 | 1.77 | 1.11 | 1.27 | 1.80 | 1.00 | 1.00 | 1.00 | 1.00 |
| Aqp6 | 1.00 | 1.00 | 1.00 | 0.83 | 1.13 | 0.71 | 1.00 | 1.00 | 1.00 |
| Arg1 | 5.80 | 1.13 | 1.00 | 1.00 | 1.00 | 1.00 | 1.31 | 1.04 | 0.77 |
| Arhgdib | 1.35 | 1.85 | 1.74 | 0.85 | 1.40 | 0.91 | 0.65 | 5.76 | 1.00 |
| Arntl | 0.81 | 4.58 | 5.89 | 1.36 | 6.54 | 2.86 | 0.92 | 7.91 | 2.95 |
| Arrdc2 | 1.04 | 1.04 | 0.39 | 1.54 | 1.55 | 0.82 | 2.01 | 1.65 | 0.49 |
| Arrdc3 | 1.46 | 1.23 | 0.75 | 1.27 | 0.90 | 1.01 | 0.63 | 0.63 | 1.66 |
| Asb11 | 0.77 | 0.67 | 0.64 | 1.25 | 1.16 | 0.88 | 1.00 | 1.00 | 1.00 |
| Asf1b | 1.09 | 1.58 | 1.39 | 1.00 | 1.00 | 1.00 | 1.00 | 4.79 | 1.00 |
| Aspm | 1.00 | 1.27 | 1.00 | 1.00 | 1.00 | 1.00 | 1.00 | 1.25 | 1.00 |
| Atf3 | 5.55 | 1.16 | 4.20 | 0.93 | 1.06 | 0.88 | 1.06 | 1.25 | 1.00 |
| Atp2a1 | 1.00 | 1.00 | 1.00 | 1.00 | 1.00 | 1.00 | 1.00 | 1.00 | 1.00 |
| Atp2b3 | 1.00 | 1.00 | 1.00 | 1.00 | 1.00 | 1.00 | 1.00 | 1.00 | 1.00 |
| Atp6v0d2 | 1.00 | 8.83 | 1.15 | 0.75 | 1.03 | 0.93 | 1.00 | 1.22 | 1.00 |
| Atp6v1g3 | 1.00 | 1.00 | 1.00 | 0.84 | 1.06 | 0.86 | 1.00 | 1.00 | 1.00 |
| AU015791 | 1.00 | 1.17 | 1.00 | 1.00 | 1.00 | 1.00 | 1.00 | 1.00 | 1.00 |
| AU040972 | 1.00 | 1.00 | 1.25 | 1.00 | 1.00 | 1.00 | 1.00 | 1.00 | 1.00 |
| Aurkb | 1.26 | 2.50 | 1.00 | 1.00 | 1.01 | 1.00 | 1.00 | 3.26 | 1.00 |
| AW549542 | 0.80 | 0.96 | 0.44 | 1.08 | 1.00 | 1.00 | 0.81 | 0.56 | 0.89 |
| AY761185 | 1.00 | 1.00 | 1.00 | 0.87 | 1.00 | 1.00 | 1.00 | 1.00 | 1.00 |
| Azgp1 | 1.00 | 1.00 | 1.00 | 54.18 | 1.30 | 42.64 | 1.16 | 0.97 | 0.98 |
| Basp1 | 3.93 | 5.25 | 1.99 | 0.81 | 1.00 | 1.06 | 1.00 | 1.15 | 1.00 |
| BC018473 | 1.00 | 1.00 | 1.00 | 1.00 | 1.00 | 6.13 | 1.00 | 1.00 | 1.00 |
| BC035044 | 1.00 | 1.28 | 1.00 | 1.00 | 1.00 | 1.00 | 1.00 | 2.66 | 1.00 |
| BC048679 | 1.00 | 1.00 | 1.00 | 1.00 | 1.00 | 1.00 | 1.00 | 1.00 | 1.00 |
| BC094916 | 1.00 | 1.35 | 1.00 | 1.00 | 1.00 | 1.00 | 1.00 | 2.43 | 1.00 |
| Bcl11a | 0.89 | 1.12 | 0.80 | 1.00 | 1.00 | 1.00 | 1.00 | 2.03 | 1.00 |
| Bcl2l15 | 1.25 | 1.00 | 1.00 | 1.78 | 1.73 | 1.01 | 1.01 | 1.00 | 1.00 |
| Bglap3 | 1.00 | 1.00 | 1.00 | 1.70 | 0.47 | 3.27 | 0.85 | 1.00 | 1.03 |
| Birc5 | 1.65 | 2.72 | 1.28 | 0.92 | 1.04 | 1.11 | 1.01 | 5.91 | 1.00 |
| Blnk | 0.72 | 3.95 | 1.04 | 0.96 | 0.91 | 0.77 | 1.00 | 4.03 | 1.03 |
| Bpifa1 | 1.00 | 1.00 | 26.49 | 1.00 | 1.00 | 1.00 | 1.00 | 1.00 | 1.00 |
| Bpifb1 | 1.00 | 1.00 | 3.43 | 1.00 | 1.00 | 1.00 | 1.00 | 1.00 | 1.00 |
| Bsph1 | 1.00 | 1.00 | 1.00 | 1.00 | 1.00 | 1.00 | 1.00 | 1.00 | 1.00 |
| Bub1b | 1.00 | 2.29 | 1.00 | 1.00 | 1.00 | 1.00 | 1.00 | 2.65 | 1.00 |
| C1qa | 1.03 | 1.75 | 1.48 | 1.13 | 1.29 | 0.95 | 0.96 | 1.72 | 0.86 |
| C1qtnf3 | 1.00 | 19.10 | 1.00 | 1.04 | 0.70 | 1.00 | 1.00 | 1.00 | 1.00 |
| C330027C09Rik | 1.02 | 1.82 | 1.00 | 1.00 | 1.00 | 1.00 | 1.00 | 1.85 | 1.00 |
| C4bp | 1.00 | 1.00 | 1.00 | 1.00 | 1.00 | 1.00 | 1.08 | 1.02 | 0.83 |

Fig. 31-26

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| AF357399 | 0.89 | 1.04 | 1.83 | 0.07 | 0.98 | 1.36 | 1.67 | 0.88 | 2.29 |
| AF357425 | 24.34 | 1.00 | 1.00 | 1.00 | 1.00 | 1.00 | 1.00 | 1.00 | 36.58 |
| Ager | 1.01 | 0.71 | 0.83 | 1.00 | 1.00 | 1.00 | 1.24 | 1.25 | 1.01 |
| Agr2 | 3.01 | 1.05 | 0.62 | 1.00 | 1.00 | 1.00 | 1.00 | 1.00 | 1.00 |
| Alas2 | 0.78 | 0.97 | 0.75 | 2.12 | 1.70 | 1.07 | 0.62 | 1.08 | 2.69 |
| Aldh3a1 | 1.03 | 0.75 | 1.05 | 1.00 | 1.00 | 1.00 | 1.00 | 1.00 | 0.99 |
| Alpl | 0.90 | 7.81 | 0.96 | 0.67 | 0.62 | 1.08 | 0.57 | 2.14 | 1.05 |
| Alppl2 | 1.00 | 1.00 | 1.00 | 1.00 | 1.00 | 1.00 | 1.00 | 1.00 | 1.00 |
| Amd1 | 1.00 | 1.00 | 1.00 | 0.86 | 0.26 | 1.91 | 1.00 | 1.00 | 1.00 |
| Amy2a5 | 1.00 | 1.00 | 1.00 | 1.01 | 1.00 | 0.97 | 1.48 | 0.05 | 0.00 |
| Angptl4 | 4.59 | 1.22 | 0.89 | 2.25 | 2.18 | 2.53 | 2.76 | 1.04 | 1.63 |
| Angptl7 | 1.77 | 0.13 | 0.43 | 2.15 | 0.65 | 0.77 | 1.10 | 0.70 | 0.74 |
| Ankef1 | 1.00 | 1.00 | 1.00 | 1.00 | 1.04 | 1.00 | 1.00 | 1.00 | 1.00 |
| Ankrd1 | 1.60 | 2.12 | 2.47 | 0.91 | 1.18 | 1.16 | 1.00 | 1.00 | 1.00 |
| Ankrd2 | 1.00 | 1.00 | 1.00 | 1.22 | 0.47 | 1.18 | 0.96 | 0.95 | 1.05 |
| Ap1s2 | 0.94 | 1.28 | 1.02 | 0.83 | 1.05 | 1.02 | 1.24 | 0.99 | 0.82 |
| Ap3b2 | 1.00 | 1.00 | 1.00 | 1.00 | 1.00 | 1.00 | 1.00 | 1.00 | 1.00 |
| Apitd1 | 1.48 | 9.34 | 0.80 | 1.00 | 1.00 | 1.00 | 0.96 | 1.23 | 0.95 |
| Apln | 1.16 | 1.01 | 0.97 | 1.00 | 0.83 | 1.00 | 1.00 | 1.00 | 1.00 |
| Apobec1 | 0.91 | 3.93 | 1.21 | 0.90 | 1.27 | 1.30 | 1.51 | 1.21 | 0.77 |
| Apobec2 | 0.66 | 0.87 | 1.00 | 0.62 | 0.70 | 0.87 | 1.12 | 1.00 | 1.09 |
| Apol11a | 1.00 | 1.00 | 1.00 | 1.00 | 1.00 | 1.00 | 2.00 | 2.93 | 6.83 |
| Apol11b | 1.00 | 1.00 | 1.00 | 1.00 | 1.00 | 1.00 | 1.41 | 3.00 | 5.59 |
| Apol7c | 1.00 | 1.00 | 1.00 | 1.00 | 1.00 | 1.00 | 1.00 | 1.00 | 9.24 |
| Apol8 | 1.00 | 1.00 | 1.00 | 1.00 | 1.00 | 1.00 | 1.54 | 1.77 | 5.14 |
| Apold1 | 1.21 | 1.84 | 1.06 | 1.55 | 2.41 | 0.82 | 0.98 | 0.97 | 0.86 |
| Aqp6 | 1.00 | 1.00 | 1.00 | 1.00 | 1.00 | 1.00 | 1.00 | 1.00 | 1.00 |
| Arg1 | 9.90 | 0.56 | 0.77 | 1.00 | 1.00 | 1.00 | 1.00 | 1.00 | 1.00 |
| Arhgdib | 0.83 | 2.47 | 0.94 | 0.81 | 0.74 | 0.92 | 0.83 | 0.96 | 0.83 |
| Arntl | 1.29 | 9.17 | 3.38 | 1.49 | 2.48 | 2.65 | 1.05 | 1.16 | 0.99 |
| Arrdc2 | 1.32 | 1.10 | 0.62 | 5.14 | 3.09 | 0.17 | 1.22 | 0.93 | 1.69 |
| Arrdc3 | 1.31 | 0.88 | 0.78 | 5.48 | 2.86 | 0.43 | 1.08 | 0.87 | 1.16 |
| Asb11 | 0.91 | 1.05 | 1.27 | 1.51 | 1.06 | 0.95 | 1.58 | 1.00 | 1.00 |
| Asf1b | 2.05 | 7.01 | 0.96 | 1.00 | 1.00 | 1.00 | 0.96 | 1.39 | 2.76 |
| Aspm | 1.00 | 6.27 | 1.00 | 1.00 | 1.00 | 1.00 | 1.08 | 1.49 | 2.97 |
| Atf3 | 1.58 | 2.07 | 1.68 | 0.97 | 1.75 | 3.01 | 0.91 | 1.03 | 0.71 |
| Atp2a1 | 0.87 | 1.00 | 1.00 | 1.10 | 0.98 | 0.88 | 1.03 | 0.78 | 0.89 |
| Atp2b3 | 1.00 | 1.00 | 1.00 | 1.03 | 1.36 | 0.90 | 1.00 | 1.00 | 1.00 |
| Atp6v0d2 | 1.31 | 1.40 | 1.10 | 1.00 | 1.00 | 1.00 | 1.00 | 1.00 | 1.00 |
| Atp6v1g3 | 1.00 | 1.00 | 1.00 | 1.00 | 1.00 | 1.00 | 1.00 | 1.00 | 1.00 |
| AU015791 | 1.00 | 1.00 | 1.00 | 1.00 | 1.00 | 1.00 | 1.00 | 1.00 | 1.00 |
| AU040972 | 1.15 | 1.18 | 1.24 | 1.00 | 1.00 | 1.00 | 1.00 | 1.00 | 1.00 |
| Aurkb | 1.79 | 7.50 | 0.95 | 1.00 | 1.00 | 1.00 | 0.83 | 1.44 | 2.40 |
| AW549542 | 1.15 | 0.68 | 0.51 | 1.11 | 1.00 | 0.98 | 1.00 | 1.00 | 1.00 |
| AY761185 | 1.00 | 1.00 | 1.00 | 1.00 | 1.00 | 1.00 | 1.00 | 1.00 | 1.00 |
| Azgp1 | 2.15 | 1.00 | 1.00 | 1.00 | 1.00 | 1.00 | 1.00 | 1.00 | 1.00 |
| Basp1 | 1.18 | 1.05 | 1.42 | 0.98 | 1.32 | 1.35 | 0.75 | 1.20 | 1.04 |
| BC018473 | 1.00 | 1.00 | 5.32 | 1.00 | 1.00 | 1.00 | 1.00 | 1.00 | 11.56 |
| BC035044 | 1.00 | 11.91 | 0.90 | 1.00 | 1.00 | 1.00 | 0.80 | 0.85 | 1.07 |
| BC048679 | 1.00 | 1.00 | 1.00 | 1.93 | 1.44 | 0.75 | 1.00 | 1.00 | 1.00 |
| BC094916 | 0.96 | 15.59 | 0.79 | 1.00 | 1.00 | 1.00 | 1.09 | 1.05 | 0.72 |
| Bcl11a | 0.52 | 6.34 | 0.91 | 1.00 | 1.00 | 1.00 | 0.91 | 1.07 | 0.96 |
| Bcl2l15 | 1.16 | 1.19 | 1.00 | 1.00 | 1.00 | 1.00 | 2.73 | 1.96 | 1.41 |
| Bglap3 | 1.00 | 1.00 | 1.00 | 1.00 | 0.47 | 1.00 | 1.00 | 1.00 | 1.00 |
| Birc5 | 1.77 | 10.41 | 1.22 | 1.00 | 0.72 | 1.00 | 1.00 | 1.41 | 3.53 |
| Blnk | 0.51 | 9.64 | 0.79 | 1.00 | 1.52 | 1.00 | 1.01 | 1.04 | 0.93 |
| Bpifa1 | 0.15 | 0.21 | 0.29 | 1.00 | 1.00 | 1.00 | 1.00 | 1.00 | 1.00 |
| Bpifb1 | 0.83 | 2.65 | 1.01 | 1.00 | 1.00 | 1.00 | 1.00 | 1.00 | 1.00 |
| Bsph1 | 1.00 | 1.00 | 1.00 | 1.00 | 1.00 | 1.00 | 1.00 | 1.00 | 1.00 |
| Bub1b | 1.89 | 8.05 | 1.06 | 1.00 | 1.00 | 1.00 | 0.75 | 1.29 | 2.57 |
| C1qa | 1.19 | 1.21 | 1.09 | 0.97 | 0.95 | 1.11 | 1.01 | 0.90 | 0.93 |
| C1qtnf3 | 1.00 | 1.50 | 1.00 | 0.61 | 0.76 | 0.56 | 1.00 | 1.00 | 1.00 |
| C330027C09Rik | 1.50 | 7.37 | 1.06 | 1.00 | 1.00 | 1.00 | 0.94 | 1.50 | 2.67 |
| C4bp | 1.00 | 1.00 | 1.00 | 1.00 | 1.00 | 1.00 | 1.00 | 1.00 | 1.00 |

Fig. 31-27

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| AF357399 | 0.88 | 3.82 | 66.62 | 0.56 | 6.34 | 0.81 | 1.65 | 1.63 | 1.01 |
| AF357425 | 0.30 | 1.02 | 2.14 | 1.00 | 1.00 | 1.00 | 1.00 | 1.00 | 1.00 |
| Ager | 1.00 | 1.00 | 1.00 | 1.27 | 1.19 | 1.08 | 1.00 | 1.00 | 1.00 |
| Agr2 | 1.00 | 1.00 | 1.00 | 1.00 | 6.49 | 1.00 | 1.00 | 1.00 | 1.00 |
| Alas2 | 0.83 | 3.11 | 1.23 | 1.42 | 3.28 | 1.16 | 1.23 | 1.12 | 1.22 |
| Aldh3a1 | 1.00 | 1.00 | 1.00 | 1.00 | 1.41 | 1.00 | 1.00 | 0.96 | 1.00 |
| Alpl | 0.78 | 1.27 | 0.95 | 1.21 | 7.06 | 1.04 | 0.91 | 0.99 | 0.95 |
| Alppl2 | 1.00 | 1.00 | 1.00 | 1.00 | 5.57 | 1.00 | 1.03 | 1.07 | 0.96 |
| Amd1 | 0.16 | 1.00 | 0.36 | 1.00 | 1.00 | 0.19 | 5.83 | 0.55 | 0.82 |
| Amy2a5 | 1.00 | 1.00 | 1.00 | 1.24 | 1.73 | 0.87 | 1.18 | 0.71 | 0.94 |
| Angptl4 | 1.61 | 1.61 | 1.05 | 2.29 | 0.92 | 1.35 | 1.28 | 0.67 | 1.03 |
| Angptl7 | 1.00 | 1.00 | 1.00 | 0.65 | 0.83 | 1.09 | 0.67 | 0.76 | 0.78 |
| Ankef1 | 1.00 | 1.00 | 1.00 | 1.02 | 0.67 | 2.23 | 0.98 | 1.06 | 0.98 |
| Ankrd1 | 1.00 | 1.00 | 1.53 | 1.00 | 1.00 | 1.00 | 1.00 | 1.00 | 1.00 |
| Ankrd2 | 1.00 | 1.00 | 1.00 | 1.00 | 1.00 | 1.00 | 0.91 | 1.00 | 1.00 |
| Ap1s2 | 1.02 | 0.94 | 1.02 | 0.84 | 15.04 | 0.77 | 0.95 | 1.09 | 1.02 |
| Ap3b2 | 0.95 | 0.96 | 1.02 | 1.00 | 15.76 | 1.00 | 1.00 | 1.00 | 1.00 |
| Apitd1 | 1.21 | 1.33 | 0.95 | 1.00 | 0.71 | 0.84 | 1.00 | 0.92 | 0.95 |
| Apln | 0.75 | 0.80 | 1.34 | 1.22 | 0.82 | 1.48 | 0.55 | 1.15 | 1.86 |
| Apobec1 | 1.00 | 2.75 | 1.00 | 1.41 | 1.43 | 0.62 | 1.00 | 1.00 | 1.00 |
| Apobec2 | 1.00 | 1.00 | 1.00 | 1.00 | 1.00 | 1.00 | 0.91 | 0.84 | 0.96 |
| Apol11a | 1.00 | 1.00 | 1.00 | 1.00 | 1.00 | 1.00 | 1.00 | 1.00 | 1.00 |
| Apol11b | 1.00 | 1.00 | 1.00 | 1.00 | 1.00 | 1.00 | 1.00 | 1.00 | 1.00 |
| Apol7c | 1.00 | 1.00 | 1.00 | 1.00 | 1.00 | 1.00 | 1.00 | 0.99 | 1.22 |
| Apol8 | 1.06 | 0.95 | 0.91 | 1.00 | 1.00 | 1.00 | 1.00 | 1.00 | 1.00 |
| Apold1 | 1.90 | 2.44 | 0.80 | 4.32 | 2.70 | 1.86 | 1.00 | 1.00 | 1.00 |
| Aqp6 | 1.15 | 0.77 | 1.12 | 1.00 | 7.14 | 1.00 | 1.00 | 1.00 | 1.00 |
| Arg1 | 1.00 | 1.00 | 1.00 | 29.03 | 0.96 | 0.16 | 1.00 | 1.00 | 1.00 |
| Arhgdib | 0.82 | 1.88 | 1.05 | 1.12 | 0.99 | 0.59 | 0.81 | 0.77 | 1.08 |
| Arntl | 0.96 | 1.05 | 1.26 | 1.02 | 3.28 | 2.91 | 1.01 | 1.12 | 1.02 |
| Arrdc2 | 2.99 | 1.75 | 0.54 | 1.53 | 1.41 | 0.89 | 0.81 | 1.10 | 1.03 |
| Arrdc3 | 1.23 | 1.17 | 0.90 | 1.86 | 1.67 | 0.66 | 0.97 | 0.94 | 0.96 |
| Asb11 | 1.04 | 1.23 | 0.85 | 0.75 | 8.04 | 1.00 | 1.00 | 1.00 | 1.00 |
| Asf1b | 1.00 | 2.12 | 1.00 | 1.01 | 1.19 | 0.80 | 1.05 | 0.97 | 1.03 |
| Aspm | 1.00 | 1.00 | 1.00 | 1.00 | 1.00 | 1.00 | 1.13 | 1.10 | 1.09 |
| Atf3 | 1.00 | 1.03 | 1.00 | 1.51 | 2.02 | 0.63 | 1.00 | 1.00 | 1.00 |
| Atp2a1 | 1.00 | 1.00 | 1.00 | 1.00 | 1.00 | 0.79 | 1.00 | 1.00 | 1.00 |
| Atp2b3 | 1.01 | 1.02 | 1.01 | 1.00 | 10.91 | 1.00 | 1.11 | 0.97 | 1.02 |
| Atp6v0d2 | 1.00 | 1.00 | 1.00 | 2.02 | 6.54 | 0.76 | 1.00 | 1.00 | 1.00 |
| Atp6v1g3 | 1.00 | 1.00 | 1.00 | 1.00 | 6.07 | 1.00 | 1.00 | 1.00 | 1.00 |
| AU015791 | 1.00 | 1.00 | 1.00 | 1.00 | 6.01 | 1.00 | 1.00 | 1.00 | 1.00 |
| AU040972 | 1.00 | 1.00 | 1.00 | 1.00 | 1.00 | 1.00 | 1.00 | 1.00 | 1.00 |
| Aurkb | 1.00 | 1.51 | 1.00 | 1.00 | 0.88 | 0.76 | 1.00 | 0.99 | 0.98 |
| AW549542 | 1.06 | 1.02 | 1.00 | 1.02 | 5.10 | 0.84 | 1.00 | 1.00 | 1.00 |
| AY761185 | 1.00 | 1.00 | 1.00 | 1.00 | 73.75 | 1.00 | 1.00 | 1.00 | 1.21 |
| Azgp1 | 1.00 | 1.00 | 1.00 | 1.00 | 1.00 | 1.00 | 1.00 | 1.00 | 1.00 |
| Basp1 | 0.92 | 1.07 | 0.97 | 1.12 | 9.92 | 0.58 | 0.94 | 0.93 | 0.91 |
| BC018473 | 1.00 | 1.00 | 1.00 | 1.00 | 0.38 | 1.10 | 1.00 | 1.00 | 1.00 |
| BC035044 | 1.00 | 1.46 | 1.00 | 1.00 | 1.22 | 0.93 | 1.00 | 1.00 | 1.00 |
| BC048679 | 1.00 | 1.00 | 1.00 | 1.00 | 25.26 | 1.00 | 0.91 | 1.00 | 1.03 |
| BC094916 | 1.00 | 1.52 | 1.00 | 1.00 | 1.00 | 1.00 | 1.00 | 1.00 | 1.00 |
| Bcl11a | 1.01 | 1.00 | 0.96 | 1.00 | 1.00 | 0.88 | 1.05 | 1.14 | 0.92 |
| Bcl2l15 | 0.97 | 0.96 | 1.13 | 1.00 | 31.92 | 1.00 | 1.17 | 0.83 | 1.19 |
| Bglap3 | 1.00 | 1.00 | 1.00 | 1.00 | 10.34 | 1.00 | 1.00 | 1.00 | 1.00 |
| Birc5 | 1.00 | 2.99 | 0.97 | 1.00 | 0.93 | 0.76 | 1.09 | 0.99 | 0.95 |
| Blnk | 0.90 | 2.22 | 1.05 | 0.94 | 1.13 | 0.54 | 0.88 | 1.00 | 0.87 |
| Bpifa1 | 1.00 | 1.00 | 1.00 | 1.00 | 1.00 | 1.00 | 1.00 | 1.00 | 1.00 |
| Bpifb1 | 1.00 | 1.00 | 1.00 | 1.00 | 1.00 | 1.00 | 1.00 | 1.00 | 1.00 |
| Bsph1 | 1.00 | 1.00 | 1.00 | 1.00 | 41.91 | 1.00 | 1.00 | 1.00 | 1.00 |
| Bub1b | 1.00 | 1.30 | 1.00 | 1.00 | 1.00 | 1.00 | 1.10 | 0.93 | 1.01 |
| C1qa | 1.13 | 1.08 | 0.89 | 1.27 | 1.03 | 0.72 | 1.00 | 1.00 | 0.98 |
| C1qtnf3 | 1.00 | 1.00 | 1.00 | 0.72 | 0.80 | 0.83 | 1.02 | 0.94 | 1.17 |
| C330027C09Rik | 1.05 | 1.48 | 1.03 | 1.00 | 1.00 | 1.00 | 1.08 | 1.06 | 1.06 |
| C4bp | 1.00 | 1.00 | 1.00 | 1.00 | 154.29 | 1.00 | 1.00 | 1.00 | 1.00 |

Fig. 31- 28

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| AF357399 | 0.99 | 0.78 | 0.76 | 0.76 | 1.03 | 0.92 | 1.32 | 0.09 | 2.13 | 1.00 | 1.14 | 1.06 |
| AF357425 | 1.00 | 1.00 | 1.00 | 1.00 | 1.00 | 1.00 | 1.00 | 1.00 | 1.00 | 1.00 | 1.13 | 0.99 |
| Ager | 1.20 | 0.91 | 0.84 | 1.51 | 1.06 | 0.74 | 1.00 | 1.00 | 1.00 | 1.11 | 1.17 | 0.77 |
| Agr2 | 1.00 | 6.05 | 1.00 | 1.00 | 1.00 | 1.00 | 0.94 | 1.00 | 1.00 | 1.00 | 1.07 | 1.00 |
| Alas2 | 1.12 | 1.67 | 2.27 | 1.31 | 1.06 | 1.34 | 1.20 | 0.62 | 0.74 | 0.95 | 1.00 | 1.00 |
| Aldh3a1 | 1.18 | 10.43 | 1.33 | 1.00 | 1.00 | 1.00 | 1.00 | 1.00 | 1.00 | 1.10 | 1.00 | 0.94 |
| Alpl | 1.06 | 1.58 | 1.61 | 1.00 | 0.89 | 0.67 | 1.00 | 1.00 | 1.00 | 0.87 | 1.13 | 1.03 |
| Alppl2 | 1.00 | 1.00 | 1.00 | 1.00 | 1.00 | 1.00 | 1.00 | 1.00 | 1.00 | 1.00 | 0.78 | 0.76 |
| Amd1 | 0.39 | 1.00 | 0.48 | 0.21 | 1.00 | 0.29 | 1.00 | 1.00 | 1.00 | 1.00 | 1.42 | 0.79 |
| Amy2a5 | 0.06 | 1.00 | 0.04 | 1.00 | 1.00 | 1.00 | 0.88 | 1.18 | 0.91 | 0.78 | 1.04 | 1.01 |
| Angptl4 | 1.43 | 1.65 | 2.53 | 0.87 | 0.92 | 1.42 | 1.58 | 1.00 | 1.14 | 1.27 | 1.09 | 1.37 |
| Angptl7 | 1.21 | 1.05 | 1.33 | 1.22 | 0.98 | 0.98 | 1.00 | 1.00 | 1.00 | 1.52 | 0.99 | 1.07 |
| Ankef1 | 1.00 | 1.00 | 1.16 | 1.00 | 1.00 | 1.00 | 1.00 | 1.00 | 1.00 | 1.00 | 1.00 | 5.37 |
| Ankrd1 | 4.43 | 8.58 | 5.92 | 1.00 | 1.00 | 1.00 | 1.00 | 1.00 | 1.00 | 0.94 | 0.97 | 0.91 |
| Ankrd2 | 1.00 | 1.00 | 1.00 | 1.00 | 1.00 | 1.00 | 1.00 | 1.00 | 1.00 | 1.74 | 1.01 | 1.01 |
| Ap1s2 | 0.94 | 0.99 | 0.98 | 1.24 | 1.04 | 0.88 | 1.00 | 1.00 | 1.00 | 1.18 | 0.80 | 0.91 |
| Ap3b2 | 1.00 | 1.00 | 1.00 | 1.00 | 1.00 | 1.00 | 1.00 | 1.00 | 1.00 | 1.00 | 0.97 | 0.95 |
| Apitd1 | 0.75 | 0.80 | 0.86 | 0.91 | 0.82 | 0.91 | 1.00 | 1.00 | 1.00 | 0.80 | 0.90 | 1.00 |
| Apln | 1.03 | 1.22 | 0.89 | 1.00 | 1.00 | 1.00 | 1.00 | 1.00 | 1.00 | 0.95 | 1.00 | 1.00 |
| Apobec1 | 1.02 | 1.78 | 1.31 | 1.10 | 1.21 | 1.21 | 1.00 | 1.00 | 1.00 | 1.23 | 0.90 | 0.87 |
| Apobec2 | 1.52 | 6.48 | 1.75 | 1.00 | 1.00 | 1.00 | 1.00 | 1.00 | 1.00 | 1.16 | 1.00 | 0.93 |
| Apol11a | 1.00 | 1.00 | 1.00 | 1.18 | 1.42 | 1.14 | 1.00 | 1.00 | 1.00 | 1.00 | 1.08 | 0.83 |
| Apol11b | 1.11 | 1.56 | 0.93 | 1.14 | 1.79 | 1.06 | 1.00 | 1.00 | 1.00 | 1.00 | 1.00 | 1.00 |
| Apol7c | 3.64 | 0.14 | 1.00 | 1.00 | 1.00 | 1.00 | 1.00 | 1.00 | 1.00 | 1.00 | 0.95 | 0.94 |
| Apol8 | 1.00 | 1.00 | 1.00 | 1.01 | 0.68 | 1.07 | 1.00 | 1.00 | 1.00 | 0.76 | 1.08 | 1.09 |
| Apold1 | 0.99 | 1.54 | 1.00 | 1.00 | 1.00 | 1.00 | 1.00 | 1.00 | 1.00 | 1.11 | 1.00 | 0.93 |
| Aqp6 | 1.00 | 1.00 | 1.00 | 1.00 | 1.00 | 1.00 | 1.00 | 1.00 | 1.00 | 1.00 | 0.42 | 1.00 |
| Arg1 | 0.98 | 6.39 | 1.00 | 1.00 | 1.00 | 1.00 | 1.00 | 1.00 | 1.00 | 0.69 | 1.19 | 1.18 |
| Arhgdib | 0.84 | 0.99 | 0.95 | 1.06 | 1.10 | 1.02 | 1.09 | 0.46 | 0.53 | 1.07 | 0.95 | 0.92 |
| Arntl | 0.92 | 0.79 | 0.81 | 0.94 | 0.60 | 0.86 | 0.86 | 1.39 | 2.19 | 0.99 | 1.18 | 0.82 |
| Arrdc2 | 0.87 | 1.28 | 0.82 | 1.52 | 0.75 | 1.55 | 1.16 | 1.14 | 1.33 | 1.08 | 1.18 | 1.07 |
| Arrdc3 | 1.30 | 1.04 | 1.05 | 1.24 | 0.97 | 1.05 | 0.96 | 1.20 | 0.78 | 1.21 | 1.06 | 1.06 |
| Asb11 | 1.15 | 1.22 | 1.00 | 1.00 | 1.00 | 1.00 | 1.19 | 0.87 | 1.70 | 1.00 | 1.08 | 1.01 |
| Asf1b | 0.45 | 0.68 | 0.98 | 0.96 | 1.02 | 1.15 | 1.00 | 1.00 | 1.00 | 0.69 | 1.00 | 1.00 |
| Aspm | 0.37 | 0.72 | 0.93 | 1.09 | 1.18 | 1.00 | 1.00 | 1.00 | 1.00 | 1.00 | 1.08 | 0.92 |
| Atf3 | 0.95 | 1.68 | 1.54 | 1.00 | 1.43 | 1.26 | 1.00 | 1.00 | 1.00 | 0.90 | 0.79 | 0.67 |
| Atp2a1 | 1.21 | 8.65 | 1.06 | 1.00 | 0.89 | 1.00 | 1.00 | 1.00 | 1.00 | 1.66 | 1.12 | 1.08 |
| Atp2b3 | 1.00 | 1.00 | 1.00 | 1.00 | 1.00 | 1.00 | 1.00 | 1.00 | 1.00 | 1.00 | 1.10 | 0.98 |
| Atp6v0d2 | 0.72 | 1.04 | 1.15 | 1.00 | 1.00 | 0.82 | 1.00 | 1.00 | 1.00 | 1.34 | 0.93 | 0.97 |
| Atp6v1g3 | 1.00 | 1.00 | 1.00 | 1.00 | 1.00 | 1.00 | 1.00 | 1.00 | 1.00 | 1.00 | 1.00 | 0.79 |
| AU015791 | 1.71 | 1.00 | 0.70 | 1.00 | 1.00 | 1.00 | 1.00 | 1.00 | 1.00 | 1.00 | 0.83 | 1.06 |
| AU040972 | 1.05 | 17.36 | 1.00 | 1.00 | 1.00 | 1.00 | 1.00 | 1.00 | 1.00 | 1.00 | 0.88 | 0.88 |
| Aurkb | 0.42 | 0.69 | 1.00 | 0.89 | 1.01 | 1.09 | 1.00 | 1.00 | 1.00 | 0.75 | 1.20 | 0.95 |
| AW549542 | 1.00 | 1.00 | 1.00 | 1.00 | 1.00 | 1.00 | 1.00 | 1.00 | 1.00 | 1.00 | 1.00 | 1.00 |
| AY761185 | 1.46 | 1.10 | 1.23 | 1.00 | 1.00 | 1.00 | 1.00 | 1.00 | 1.00 | 1.00 | 1.00 | 1.00 |
| Azgp1 | 1.00 | 1.00 | 1.00 | 1.00 | 1.00 | 1.00 | 1.00 | 1.00 | 1.00 | 1.00 | 1.03 | 0.98 |
| Basp1 | 1.03 | 1.30 | 1.26 | 1.09 | 1.24 | 0.75 | 1.00 | 1.00 | 1.00 | 1.01 | 1.07 | 1.24 |
| BC018473 | 1.00 | 0.04 | 5.12 | 4.12 | 0.03 | 3.83 | 1.00 | 1.00 | 1.00 | 1.00 | 1.00 | 1.00 |
| BC035044 | 0.77 | 0.82 | 0.90 | 1.08 | 0.87 | 0.82 | 1.00 | 1.00 | 1.00 | 1.00 | 0.92 | 1.06 |
| BC048679 | 1.00 | 1.00 | 1.00 | 1.00 | 1.00 | 1.00 | 1.00 | 1.00 | 1.00 | 1.00 | 1.00 | 1.00 |
| BC094916 | 1.25 | 2.13 | 1.12 | 1.04 | 1.08 | 0.84 | 1.00 | 1.00 | 1.00 | 1.00 | 0.96 | 0.94 |
| Bcl11a | 1.40 | 2.29 | 1.87 | 0.97 | 0.83 | 0.93 | 1.00 | 1.00 | 1.00 | 1.04 | 1.05 | 1.00 |
| Bcl2l15 | 0.93 | 0.90 | 0.88 | 1.33 | 1.20 | 1.15 | 1.00 | 1.00 | 1.00 | 0.89 | 0.99 | 0.98 |
| Bglap3 | 0.60 | 3.10 | 1.00 | 1.00 | 1.00 | 1.00 | 0.67 | 0.32 | 0.57 | 0.88 | 1.14 | 1.05 |
| Birc5 | 0.41 | 0.73 | 0.92 | 1.00 | 1.00 | 1.08 | 1.00 | 1.00 | 1.00 | 0.75 | 0.94 | 1.02 |
| Blnk | 1.42 | 2.16 | 1.92 | 1.09 | 0.50 | 0.80 | 1.00 | 1.00 | 1.00 | 0.94 | 0.70 | 0.94 |
| Bpifa1 | 1.31 | 13.73 | 0.50 | 1.00 | 1.00 | 1.00 | 1.00 | 1.00 | 1.00 | 1.00 | 1.00 | 1.00 |
| Bpifb1 | 1.00 | 41.93 | 1.00 | 1.00 | 1.00 | 1.00 | 1.00 | 1.00 | 1.00 | 1.00 | 1.00 | 1.00 |
| Bsph1 | 1.00 | 1.00 | 1.00 | 1.00 | 1.00 | 1.00 | 1.00 | 1.00 | 1.00 | 1.00 | 1.00 | 1.00 |
| Bub1b | 0.35 | 0.62 | 0.99 | 0.86 | 0.99 | 1.02 | 1.00 | 1.00 | 1.00 | 0.60 | 0.93 | 1.01 |
| C1qa | 1.12 | 1.40 | 1.11 | 1.21 | 0.93 | 1.25 | 0.45 | 4.26 | 10.37 | 1.34 | 0.94 | 0.89 |
| C1qtnf3 | 1.00 | 1.14 | 1.00 | 1.00 | 1.00 | 1.00 | 1.00 | 1.00 | 1.00 | 1.13 | 0.66 | 0.87 |
| C330027C09Rik | 0.42 | 0.65 | 0.91 | 0.96 | 1.00 | 0.95 | 1.00 | 1.00 | 1.00 | 0.92 | 1.00 | 1.00 |
| C4bp | 1.00 | 1.00 | 1.00 | 1.00 | 1.00 | 1.00 | 1.00 | 1.00 | 1.00 | 1.00 | 1.00 | 1.00 |

Fig. 31-29

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| C730036E19Rik | 1.00 | 1.00 | 1.00 | 2.79 | 1.17 | 0.75 | 5.63 | 1.04 | 1.31 |
| Cacna1e | 1.00 | 1.00 | 1.00 | 1.00 | 1.00 | 1.00 | 1.00 | 1.00 | 1.00 |
| Cadm1 | 1.32 | 5.12 | 1.91 | 0.90 | 1.00 | 1.15 | 1.00 | 1.32 | 0.76 |
| Camp | 1.00 | 5.30 | 1.34 | 1.00 | 1.68 | 1.00 | 1.00 | 8.83 | 1.00 |
| Capn3 | 0.69 | 0.56 | 0.47 | 1.00 | 1.00 | 1.00 | 1.00 | 1.00 | 1.00 |
| Car12 | 1.00 | 1.00 | 1.00 | 0.73 | 0.74 | 0.88 | 1.00 | 1.00 | 1.00 |
| Car3 | 0.80 | 0.48 | 8.85 | 0.65 | 0.27 | 1.08 | 0.53 | 0.78 | 1.13 |
| Ccl4 | 4.22 | 2.93 | 1.00 | 1.00 | 1.00 | 1.00 | 1.00 | 1.00 | 1.00 |
| Ccl5 | 0.99 | 5.18 | 4.47 | 0.98 | 1.01 | 0.44 | 0.94 | 2.53 | 0.78 |
| Ccl8 | 1.08 | 0.70 | 4.27 | 1.47 | 1.00 | 0.51 | 1.00 | 1.00 | 1.00 |
| Ccna2 | 1.54 | 2.90 | 1.10 | 1.17 | 1.60 | 1.16 | 1.00 | 4.56 | 1.00 |
| Ccnb1 | 1.00 | 2.08 | 1.00 | 1.00 | 1.00 | 1.00 | 1.00 | 1.48 | 1.00 |
| Ccnb2 | 1.08 | 2.89 | 1.08 | 1.05 | 1.24 | 1.01 | 1.00 | 3.58 | 1.00 |
| Ccnf | 1.00 | 1.46 | 1.00 | 1.00 | 1.00 | 1.00 | 1.34 | 1.37 | 0.69 |
| Ccno | 1.00 | 1.00 | 1.00 | 1.00 | 1.00 | 1.00 | 1.00 | 1.00 | 1.00 |
| Cd177 | 1.49 | 1.29 | 1.00 | 1.00 | 1.00 | 1.00 | 1.00 | 1.43 | 1.00 |
| Cd180 | 0.85 | 5.03 | 1.39 | 1.00 | 1.19 | 0.98 | 1.00 | 1.27 | 1.00 |
| Cd19 | 1.00 | 5.33 | 1.58 | 1.00 | 2.46 | 1.00 | 1.00 | 13.22 | 1.00 |
| Cd24a | 1.69 | 3.99 | 4.76 | 1.02 | 1.19 | 1.10 | 1.00 | 27.67 | 1.00 |
| Cd300lf | 5.78 | 6.24 | 1.01 | 1.00 | 1.00 | 1.00 | 1.01 | 1.87 | 1.00 |
| Cd37 | 1.37 | 2.89 | 2.21 | 0.94 | 2.41 | 0.81 | 1.00 | 7.62 | 0.84 |
| Cd52 | 1.67 | 4.50 | 4.55 | 0.69 | 2.16 | 0.98 | 0.43 | 7.58 | 1.03 |
| Cd69 | 1.00 | 1.51 | 1.00 | 1.00 | 1.00 | 1.00 | 1.00 | 2.15 | 1.00 |
| Cd72 | 0.90 | 7.94 | 1.72 | 0.61 | 2.96 | 0.80 | 1.00 | 4.25 | 1.00 |
| Cd79a | 1.00 | 7.53 | 2.82 | 1.00 | 3.31 | 0.99 | 1.00 | 21.42 | 1.00 |
| Cd79b | 0.98 | 9.33 | 2.88 | 0.98 | 4.43 | 0.99 | 1.00 | 20.71 | 1.00 |
| Cdc45 | 1.35 | 1.26 | 0.89 | 1.62 | 1.35 | 0.91 | 1.00 | 2.01 | 1.00 |
| Cdca3 | 1.10 | 2.98 | 1.00 | 1.01 | 1.05 | 1.10 | 1.00 | 3.31 | 1.00 |
| Cdca5 | 1.00 | 1.28 | 1.00 | 1.00 | 1.00 | 1.00 | 1.00 | 1.72 | 1.00 |
| Cdca8 | 1.46 | 2.67 | 1.00 | 0.99 | 1.17 | 1.03 | 1.00 | 3.21 | 1.00 |
| Cdk1 | 1.31 | 2.79 | 1.00 | 1.00 | 1.19 | 1.00 | 1.00 | 2.56 | 1.00 |
| Cdkn1a | 2.38 | 2.58 | 1.62 | 1.83 | 3.87 | 1.61 | 6.45 | 25.59 | 3.61 |
| Cdkn2a | 1.00 | 1.11 | 1.00 | 1.00 | 1.00 | 1.00 | 1.00 | 1.30 | 1.00 |
| Cebpd | 2.20 | 2.54 | 1.23 | 1.68 | 2.03 | 0.67 | 2.52 | 2.50 | 0.44 |
| Cela2a | 1.00 | 1.00 | 1.00 | 1.00 | 1.00 | 1.00 | 1.00 | 5.68 | 1.00 |
| Cemip | 1.00 | 5.86 | 1.00 | 1.00 | 1.00 | 1.00 | 1.00 | 1.00 | 1.00 |
| Cenpa | 0.62 | 0.71 | 0.83 | 1.00 | 1.14 | 1.00 | 0.66 | 2.68 | 0.90 |
| Cenpe | 1.00 | 1.38 | 1.00 | 1.00 | 1.00 | 1.00 | 1.00 | 1.25 | 1.00 |
| Cenpf | 1.25 | 0.81 | 0.36 | 1.00 | 1.00 | 1.00 | 1.00 | 1.21 | 1.00 |
| Cenph | 1.00 | 1.00 | 1.00 | 1.00 | 1.00 | 1.00 | 1.00 | 1.26 | 1.00 |
| Cenpn | 1.09 | 1.62 | 1.00 | 1.02 | 1.02 | 1.00 | 1.00 | 1.72 | 1.00 |
| Cep55 | 1.00 | 2.46 | 1.00 | 1.00 | 1.00 | 1.00 | 1.00 | 2.07 | 1.00 |
| Ces5a | 1.00 | 1.00 | 1.00 | 1.00 | 1.00 | 1.00 | 1.00 | 1.00 | 1.00 |
| Cfd | 0.96 | 0.62 | 11.45 | 0.64 | 0.23 | 1.22 | 1.00 | 1.00 | 0.83 |
| Ch25h | 7.16 | 2.70 | 1.41 | 1.25 | 1.32 | 1.00 | 1.00 | 1.00 | 1.00 |
| Chad | 0.70 | 1.41 | 10.89 | 1.00 | 1.00 | 1.00 | 1.00 | 0.66 | 2.04 |
| Chil1 | 3.80 | 0.77 | 9.85 | 1.00 | 1.00 | 1.00 | 1.00 | 1.16 | 1.00 |
| Chil3 | 5.05 | 1.89 | 4.41 | 1.00 | 1.00 | 0.59 | 1.00 | 2.66 | 1.00 |
| Chil4 | 2.18 | 1.00 | 1.14 | 1.00 | 1.00 | 1.00 | 1.00 | 1.00 | 1.00 |
| Cidec | 0.76 | 0.49 | 7.16 | 0.71 | 0.20 | 0.90 | 1.57 | 0.57 | 1.08 |
| Cilp | 0.82 | 6.27 | 11.16 | 1.00 | 1.00 | 1.00 | 1.00 | 1.00 | 1.00 |
| Cited1 | 1.32 | 1.00 | 1.00 | 1.00 | 1.00 | 1.00 | 1.00 | 1.00 | 1.00 |
| Ckap2 | 1.00 | 2.83 | 1.00 | 1.00 | 1.00 | 1.00 | 1.00 | 1.75 | 1.00 |
| Ckap2l | 1.03 | 2.45 | 1.00 | 1.00 | 1.00 | 1.00 | 1.00 | 2.06 | 1.00 |
| Ckm | 0.79 | 0.52 | 0.67 | 1.00 | 1.00 | 1.00 | 1.00 | 1.00 | 1.00 |
| Cks2 | 1.50 | 3.02 | 0.95 | 0.77 | 0.82 | 1.06 | 0.83 | 1.48 | 1.02 |
| Clca3 | 1.00 | 1.00 | 1.00 | 1.00 | 1.00 | 1.00 | 1.00 | 1.00 | 1.00 |
| Cldn18 | 1.00 | 1.00 | 5.88 | 1.00 | 1.00 | 1.00 | 1.00 | 1.00 | 1.00 |
| Cldn3 | 1.00 | 0.80 | 2.57 | 1.16 | 1.01 | 1.13 | 0.75 | 0.89 | 1.09 |
| Cldn4 | 1.00 | 1.00 | 1.00 | 0.90 | 0.76 | 0.94 | 1.00 | 1.00 | 1.00 |
| Cldn8 | 1.00 | 1.00 | 1.00 | 1.07 | 1.43 | 1.07 | 1.00 | 1.00 | 1.00 |
| Clec4e | 3.85 | 1.00 | 1.00 | 1.00 | 1.00 | 1.00 | 1.00 | 1.00 | 1.00 |
| Clpsl2 | 1.00 | 1.00 | 1.00 | 1.00 | 1.00 | 1.00 | 1.00 | 1.00 | 1.00 |
| Clu | 0.84 | 2.68 | 1.41 | 0.98 | 0.84 | 1.17 | 1.04 | 0.84 | 1.06 |

Fig. 31-30

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| C730036E19Rik | 1.00 | 1.00 | 1.00 | 1.00 | 1.00 | 1.00 | 1.00 | 1.00 | 1.00 |
| Cacna1e | 1.00 | 5.39 | 1.00 | 1.00 | 1.00 | 1.00 | 2.36 | 0.74 | 0.50 |
| Cadm1 | 0.87 | 0.70 | 0.84 | 0.70 | 1.18 | 0.81 | 0.98 | 0.78 | 1.13 |
| Camp | 0.42 | 13.17 | 2.68 | 1.00 | 0.07 | 0.10 | 0.28 | 1.55 | 2.36 |
| Capn3 | 1.00 | 1.00 | 1.00 | 0.97 | 1.12 | 0.85 | 0.97 | 1.00 | 0.85 |
| Car12 | 1.00 | 1.00 | 1.00 | 1.00 | 1.00 | 1.00 | 1.00 | 1.00 | 0.99 |
| Car3 | 0.47 | 1.48 | 0.36 | 0.88 | 1.45 | 0.94 | 2.92 | 0.61 | 1.20 |
| Ccl4 | 1.78 | 0.85 | 1.00 | 1.00 | 1.00 | 1.00 | 0.86 | 2.09 | 0.80 |
| Ccl5 | 0.71 | 1.36 | 0.95 | 1.00 | 1.33 | 1.00 | 0.86 | 1.29 | 0.85 |
| Ccl8 | 0.97 | 1.71 | 1.08 | 2.02 | 0.18 | 0.42 | 1.00 | 5.77 | 0.81 |
| Ccna2 | 2.00 | 7.82 | 1.12 | 1.00 | 0.81 | 0.97 | 0.99 | 1.26 | 3.07 |
| Ccnb1 | 1.79 | 6.83 | 1.00 | 1.00 | 1.00 | 1.00 | 0.89 | 1.51 | 3.15 |
| Ccnb2 | 1.84 | 8.25 | 1.08 | 1.00 | 1.00 | 1.00 | 0.94 | 1.34 | 3.48 |
| Ccnf | 1.55 | 6.71 | 1.06 | 1.00 | 1.00 | 1.00 | 1.11 | 1.37 | 3.11 |
| Ccno | 1.24 | 1.39 | 1.16 | 1.00 | 1.00 | 1.00 | 1.00 | 1.00 | 1.00 |
| Cd177 | 0.57 | 1.23 | 5.08 | 1.00 | 0.46 | 0.88 | 0.31 | 1.15 | 1.75 |
| Cd180 | 0.40 | 1.11 | 0.89 | 1.00 | 1.00 | 1.00 | 0.73 | 0.79 | 0.89 |
| Cd19 | 0.24 | 16.71 | 0.78 | 1.00 | 1.94 | 1.00 | 0.98 | 0.80 | 0.87 |
| Cd24a | 0.90 | 2.44 | 1.10 | 0.79 | 1.10 | 1.38 | 1.03 | 1.33 | 3.33 |
| Cd300lf | 1.10 | 1.20 | 1.20 | 1.00 | 1.00 | 1.00 | 0.99 | 1.04 | 0.82 |
| Cd37 | 0.44 | 4.17 | 0.78 | 0.88 | 0.90 | 0.90 | 0.90 | 0.89 | 0.78 |
| Cd52 | 0.51 | 3.05 | 0.91 | 0.47 | 0.81 | 0.86 | 0.85 | 0.98 | 0.81 |
| Cd69 | 0.77 | 25.07 | 1.00 | 1.00 | 1.00 | 1.00 | 1.30 | 1.62 | 0.58 |
| Cd72 | 0.40 | 4.44 | 1.02 | 1.00 | 1.00 | 1.00 | 1.28 | 1.04 | 0.75 |
| Cd79a | 0.25 | 13.16 | 0.75 | 1.00 | 2.46 | 1.00 | 1.04 | 0.90 | 0.75 |
| Cd79b | 0.36 | 11.67 | 0.78 | 1.00 | 3.41 | 1.00 | 0.93 | 0.84 | 0.81 |
| Cdc45 | 1.78 | 5.67 | 1.13 | 1.07 | 0.90 | 1.10 | 0.63 | 1.33 | 2.60 |
| Cdca3 | 1.84 | 6.85 | 0.86 | 1.00 | 0.92 | 0.91 | 1.08 | 1.11 | 3.22 |
| Cdca5 | 1.93 | 6.48 | 1.00 | 1.00 | 1.00 | 1.00 | 0.76 | 1.52 | 2.61 |
| Cdca8 | 1.60 | 7.44 | 1.00 | 1.00 | 0.92 | 1.00 | 0.82 | 1.34 | 2.89 |
| Cdk1 | 2.37 | 7.45 | 1.05 | 1.00 | 1.00 | 1.00 | 0.94 | 1.45 | 3.17 |
| Cdkn1a | 3.16 | 2.36 | 1.21 | 2.06 | 4.53 | 1.27 | 1.19 | 1.40 | 0.67 |
| Cdkn2a | 0.64 | 5.55 | 1.40 | 0.89 | 0.96 | 0.91 | 0.50 | 2.52 | 0.73 |
| Cebpd | 2.06 | 1.71 | 0.86 | 7.11 | 4.13 | 0.34 | 1.71 | 1.36 | 0.89 |
| Cela2a | 1.00 | 1.00 | 1.00 | 1.00 | 1.00 | 1.00 | 1.12 | 0.08 | 0.00 |
| Cemip | 1.00 | 2.61 | 1.00 | 1.00 | 1.00 | 1.00 | 1.12 | 0.75 | 0.94 |
| Cenpa | 0.91 | 5.47 | 1.10 | 0.94 | 0.76 | 0.82 | 0.90 | 1.30 | 2.34 |
| Cenpe | 1.00 | 5.22 | 1.00 | 1.00 | 1.00 | 1.00 | 0.98 | 1.37 | 3.15 |
| Cenpf | 1.06 | 5.60 | 1.00 | 1.00 | 1.00 | 1.00 | 1.23 | 1.41 | 3.73 |
| Cenph | 1.47 | 5.38 | 1.00 | 1.00 | 1.00 | 1.00 | 0.64 | 1.37 | 3.02 |
| Cenpn | 1.52 | 6.41 | 1.00 | 1.00 | 1.00 | 1.00 | 0.83 | 1.31 | 2.65 |
| Cep55 | 1.73 | 7.61 | 0.92 | 1.00 | 1.00 | 1.00 | 0.48 | 1.72 | 0.91 |
| Ces5a | 1.00 | 1.00 | 1.00 | 1.00 | 1.00 | 1.00 | 1.00 | 1.00 | 1.00 |
| Cfd | 0.60 | 1.74 | 0.48 | 0.67 | 1.94 | 1.70 | 2.59 | 0.52 | 1.66 |
| Ch25h | 1.33 | 1.60 | 1.31 | 1.00 | 1.00 | 1.00 | 1.95 | 0.86 | 0.78 |
| Chad | 0.95 | 1.09 | 1.12 | 0.88 | 0.67 | 0.89 | 1.58 | 1.06 | 1.27 |
| Chil1 | 0.50 | 1.00 | 1.45 | 1.00 | 0.57 | 0.20 | 0.88 | 0.88 | 1.59 |
| Chil3 | 0.98 | 1.21 | 0.87 | 1.00 | 0.20 | 0.26 | 0.49 | 1.65 | 1.36 |
| Chil4 | 0.97 | 1.23 | 0.86 | 1.00 | 0.89 | 1.00 | 0.53 | 1.53 | 1.33 |
| Cidec | 0.78 | 0.90 | 0.60 | 0.76 | 1.68 | 1.40 | 2.57 | 0.77 | 1.15 |
| Cilp | 1.00 | 2.52 | 1.00 | 1.06 | 1.15 | 1.47 | 1.02 | 0.60 | 0.85 |
| Cited1 | 1.00 | 1.00 | 1.00 | 1.00 | 1.00 | 1.00 | 1.00 | 1.00 | 1.00 |
| Ckap2 | 1.89 | 8.15 | 1.00 | 1.00 | 1.00 | 1.00 | 1.15 | 1.52 | 2.90 |
| Ckap2l | 1.61 | 5.59 | 1.06 | 1.00 | 1.00 | 1.00 | 0.86 | 1.44 | 2.34 |
| Ckm | 0.79 | 0.94 | 1.22 | 1.02 | 1.03 | 0.92 | 1.00 | 1.00 | 1.07 |
| Cks2 | 1.29 | 5.69 | 1.09 | 1.00 | 1.00 | 1.00 | 0.80 | 1.48 | 2.77 |
| Clca3 | 1.00 | 2.65 | 0.11 | 1.00 | 1.00 | 1.00 | 1.00 | 1.00 | 1.00 |
| Cldn18 | 1.23 | 0.70 | 1.03 | 1.00 | 1.00 | 1.00 | 1.00 | 1.00 | 1.00 |
| Cldn3 | 1.18 | 0.80 | 1.01 | 1.00 | 1.00 | 1.00 | 1.82 | 0.76 | 1.00 |
| Cldn4 | 0.89 | 0.76 | 1.14 | 1.00 | 1.00 | 1.00 | 1.00 | 1.00 | 1.00 |
| Cldn8 | 0.94 | 0.72 | 0.73 | 1.00 | 1.00 | 1.00 | 1.25 | 1.00 | 1.00 |
| Clec4e | 1.76 | 1.47 | 1.59 | 1.00 | 1.00 | 1.00 | 0.71 | 1.45 | 0.94 |
| Clpsl2 | 1.00 | 1.00 | 1.00 | 1.00 | 1.00 | 1.00 | 1.00 | 1.00 | 1.00 |
| Clu | 0.78 | 1.11 | 1.14 | 0.67 | 0.84 | 1.15 | 1.03 | 0.65 | 0.93 |

Fig. 31-31

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| C730036E19Rik | 1.00 | 1.00 | 1.00 | 1.00 | 1.00 | 1.00 | 1.00 | 1.00 | 1.00 |
| Cacna1e | 1.13 | 1.05 | 1.00 | 1.66 | 1.00 | 0.42 | 0.66 | 1.14 | 1.04 |
| Cadm1 | 0.95 | 0.94 | 1.02 | 0.64 | 1.25 | 0.65 | 1.05 | 1.07 | 1.04 |
| Camp | 1.00 | 1.65 | 1.00 | 1.00 | 1.93 | 1.00 | 1.00 | 1.00 | 1.00 |
| Capn3 | 1.06 | 1.23 | 0.85 | 1.00 | 10.67 | 1.00 | 0.98 | 1.00 | 1.00 |
| Car12 | 0.90 | 0.78 | 1.14 | 1.00 | 5.83 | 1.00 | 1.00 | 1.00 | 1.00 |
| Car3 | 1.00 | 1.00 | 1.00 | 0.76 | 0.68 | 1.21 | 0.22 | 0.84 | 0.78 |
| Ccl4 | 1.00 | 1.00 | 1.00 | 5.65 | 1.00 | 1.00 | 1.00 | 1.00 | 1.00 |
| Ccl5 | 1.00 | 1.39 | 1.00 | 1.10 | 0.78 | 0.75 | 1.11 | 0.73 | 0.71 |
| Ccl8 | 1.00 | 1.00 | 1.00 | 1.20 | 0.86 | 0.46 | 1.30 | 1.17 | 0.42 |
| Ccna2 | 1.08 | 2.81 | 1.00 | 0.95 | 0.88 | 0.73 | 1.24 | 1.15 | 1.04 |
| Ccnb1 | 1.00 | 1.04 | 1.00 | 1.00 | 1.00 | 1.00 | 1.21 | 1.11 | 0.96 |
| Ccnb2 | 1.00 | 2.10 | 1.00 | 1.00 | 0.83 | 0.76 | 1.11 | 1.03 | 1.03 |
| Ccnf | 0.97 | 1.22 | 1.03 | 1.00 | 1.39 | 1.00 | 1.25 | 1.10 | 1.12 |
| Ccno | 1.00 | 1.00 | 1.00 | 0.97 | 7.22 | 1.00 | 0.93 | 1.17 | 1.01 |
| Cd177 | 1.00 | 1.00 | 1.00 | 1.00 | 0.69 | 0.53 | 0.72 | 1.12 | 1.19 |
| Cd180 | 0.93 | 1.00 | 0.84 | 0.66 | 1.47 | 0.51 | 1.00 | 1.00 | 1.00 |
| Cd19 | 1.00 | 6.38 | 1.00 | 1.00 | 3.32 | 0.17 | 1.00 | 1.00 | 1.00 |
| Cd24a | 0.97 | 1.97 | 1.07 | 0.85 | 1.44 | 0.44 | 1.32 | 0.90 | 0.65 |
| Cd300lf | 1.00 | 1.12 | 1.00 | 3.68 | 0.99 | 0.84 | 1.00 | 1.00 | 1.00 |
| Cd37 | 0.83 | 2.97 | 0.89 | 1.07 | 1.05 | 0.45 | 0.81 | 1.22 | 0.93 |
| Cd52 | 0.98 | 4.76 | 1.14 | 1.07 | 2.04 | 0.49 | 1.79 | 0.93 | 1.48 |
| Cd69 | 1.00 | 1.11 | 1.00 | 1.00 | 1.00 | 1.00 | 1.00 | 1.00 | 1.00 |
| Cd72 | 1.00 | 1.14 | 1.00 | 1.00 | 1.31 | 0.76 | 1.00 | 1.00 | 1.00 |
| Cd79a | 1.00 | 10.70 | 1.00 | 0.80 | 3.01 | 0.09 | 1.00 | 1.00 | 1.00 |
| Cd79b | 1.00 | 9.16 | 1.00 | 0.71 | 3.24 | 0.12 | 1.00 | 1.00 | 1.00 |
| Cdc45 | 1.00 | 1.18 | 1.00 | 1.03 | 0.67 | 1.04 | 1.11 | 1.22 | 1.01 |
| Cdca3 | 1.00 | 1.42 | 1.00 | 1.07 | 0.93 | 0.85 | 1.11 | 1.04 | 1.05 |
| Cdca5 | 1.00 | 1.00 | 1.00 | 1.00 | 1.00 | 1.00 | 1.01 | 1.02 | 0.94 |
| Cdca8 | 1.00 | 1.80 | 1.00 | 1.00 | 0.90 | 0.87 | 0.97 | 0.92 | 0.99 |
| Cdk1 | 1.00 | 1.07 | 1.00 | 0.95 | 1.02 | 0.82 | 1.06 | 0.94 | 0.96 |
| Cdkn1a | 3.03 | 1.43 | 1.22 | 2.88 | 2.76 | 1.31 | 0.86 | 0.91 | 0.85 |
| Cdkn2a | 1.00 | 1.00 | 1.00 | 1.00 | 1.00 | 1.00 | 0.83 | 0.90 | 1.01 |
| Cebpd | 1.52 | 1.75 | 0.84 | 1.84 | 1.63 | 0.66 | 0.95 | 0.97 | 0.94 |
| Cela2a | 1.00 | 1.00 | 1.00 | 1.00 | 1.00 | 1.00 | 1.00 | 1.00 | 1.00 |
| Cemip | 0.97 | 1.01 | 1.01 | 1.00 | 2.61 | 1.00 | 1.10 | 1.10 | 1.02 |
| Cenpa | 1.03 | 1.91 | 1.04 | 1.35 | 1.07 | 0.92 | 1.08 | 0.97 | 0.84 |
| Cenpe | 1.00 | 1.00 | 1.00 | 1.00 | 1.00 | 1.00 | 1.24 | 1.00 | 1.10 |
| Cenpf | 1.00 | 1.00 | 1.00 | 1.00 | 1.00 | 1.00 | 1.25 | 1.08 | 1.20 |
| Cenph | 1.00 | 1.00 | 1.00 | 1.00 | 1.02 | 1.00 | 1.01 | 1.14 | 1.08 |
| Cenpn | 1.00 | 1.31 | 0.95 | 0.96 | 1.26 | 1.00 | 1.06 | 1.02 | 1.00 |
| Cep55 | 1.00 | 1.11 | 1.00 | 1.00 | 1.00 | 1.00 | 1.07 | 0.99 | 1.00 |
| Ces5a | 1.00 | 1.00 | 1.00 | 1.00 | 9.98 | 1.00 | 1.00 | 1.00 | 1.76 |
| Cfd | 1.00 | 1.00 | 1.00 | 0.77 | 0.92 | 1.37 | 0.21 | 0.87 | 0.65 |
| Ch25h | 1.14 | 1.41 | 1.00 | 1.00 | 1.44 | 1.00 | 1.00 | 1.00 | 1.00 |
| Chad | 1.00 | 1.00 | 1.00 | 0.40 | 0.36 | 1.00 | 1.00 | 1.00 | 1.00 |
| Chil1 | 0.89 | 0.81 | 0.97 | 4.69 | 1.15 | 0.22 | 1.00 | 1.00 | 1.00 |
| Chil3 | 1.00 | 1.00 | 1.00 | 2.88 | 1.10 | 0.01 | 0.79 | 0.84 | 0.63 |
| Chil4 | 1.00 | 1.00 | 1.00 | 1.00 | 1.00 | 0.08 | 1.00 | 1.00 | 1.00 |
| Cidec | 1.00 | 1.00 | 1.00 | 0.94 | 0.83 | 1.31 | 0.45 | 1.00 | 1.00 |
| Cilp | 1.00 | 1.00 | 1.00 | 0.87 | 0.59 | 1.12 | 0.72 | 1.04 | 1.00 |
| Cited1 | 1.22 | 1.07 | 0.98 | 1.00 | 34.32 | 1.00 | 1.00 | 0.94 | 0.89 |
| Ckap2 | 1.00 | 1.11 | 1.00 | 1.00 | 1.00 | 1.00 | 0.98 | 1.02 | 0.96 |
| Ckap2l | 1.00 | 1.25 | 1.00 | 1.00 | 1.00 | 1.00 | 1.18 | 1.03 | 1.03 |
| Ckm | 1.00 | 1.00 | 1.00 | 3.00 | 1.00 | 0.48 | 1.00 | 1.00 | 1.00 |
| Cks2 | 0.95 | 2.14 | 1.00 | 1.71 | 1.66 | 0.54 | 0.91 | 1.00 | 0.99 |
| Clca3 | 1.00 | 1.00 | 1.00 | 1.00 | 0.67 | 1.00 | 1.00 | 1.00 | 1.00 |
| Cldn18 | 1.00 | 1.00 | 1.00 | 1.00 | 1.00 | 1.00 | 1.00 | 1.00 | 1.00 |
| Cldn3 | 1.00 | 1.00 | 1.00 | 0.71 | 8.40 | 0.50 | 0.97 | 0.99 | 1.01 |
| Cldn4 | 1.00 | 1.00 | 1.00 | 1.00 | 7.17 | 1.00 | 1.00 | 1.00 | 1.00 |
| Cldn8 | 1.00 | 1.00 | 1.00 | 1.00 | 10.45 | 1.00 | 1.00 | 1.00 | 1.00 |
| Clec4e | 1.00 | 1.00 | 1.00 | 1.64 | 1.00 | 0.95 | 1.00 | 1.00 | 1.00 |
| Clpsl2 | 1.00 | 1.00 | 1.00 | 1.00 | 78.93 | 1.00 | 1.00 | 1.00 | 1.00 |
| Clu | 1.03 | 1.02 | 1.07 | 1.05 | 38.58 | 0.68 | 0.93 | 0.94 | 1.01 |

Fig. 31- 32

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| C730036E19Rik | 1.00 | 1.00 | 1.00 | 1.00 | 1.00 | 1.00 | 1.00 | 1.00 | 1.00 | 1.00 | 0.98 | 1.04 |
| Cacna1e | 1.15 | 0.48 | 0.59 | 0.93 | 0.72 | 0.71 | 1.00 | 1.00 | 1.00 | 1.58 | 0.92 | 1.00 |
| Cadm1 | 0.99 | 1.20 | 1.10 | 1.01 | 0.79 | 1.20 | 1.00 | 1.00 | 1.00 | 1.12 | 1.15 | 1.01 |
| Camp | 1.19 | 3.08 | 0.85 | 0.96 | 1.01 | 1.00 | 1.16 | 1.00 | 1.00 | 1.00 | 1.00 | 1.27 |
| Capn3 | 0.95 | 0.88 | 0.53 | 1.00 | 1.00 | 1.00 | 1.00 | 1.00 | 1.00 | 1.00 | 1.00 | 1.00 |
| Car12 | 0.87 | 1.32 | 0.89 | 1.00 | 1.00 | 1.00 | 1.00 | 1.00 | 1.00 | 0.70 | 1.01 | 1.15 |
| Car3 | 1.84 | 1.62 | 2.61 | 1.70 | 0.74 | 1.93 | 0.77 | 0.89 | 0.76 | 0.97 | 1.11 | 0.84 |
| Ccl4 | 0.68 | 1.58 | 1.22 | 1.50 | 1.19 | 1.00 | 1.00 | 1.00 | 1.00 | 1.00 | 1.00 | 1.00 |
| Ccl5 | 1.17 | 2.32 | 1.38 | 1.11 | 1.79 | 0.99 | 0.64 | 0.22 | 0.34 | 1.00 | 1.00 | 1.00 |
| Ccl8 | 0.97 | 3.88 | 1.83 | 1.00 | 1.20 | 1.00 | 1.00 | 2.86 | 1.00 | 0.69 | 1.28 | 0.59 |
| Ccna2 | 0.39 | 0.68 | 0.96 | 1.02 | 1.17 | 1.08 | 1.00 | 1.00 | 1.00 | 0.82 | 1.35 | 1.18 |
| Ccnb1 | 0.35 | 0.72 | 0.92 | 0.96 | 1.03 | 1.06 | 1.00 | 1.00 | 1.00 | 0.80 | 1.14 | 0.98 |
| Ccnb2 | 0.31 | 0.61 | 0.90 | 1.02 | 0.90 | 1.07 | 1.00 | 1.00 | 1.00 | 1.05 | 1.18 | 0.97 |
| Ccnf | 0.38 | 0.69 | 0.98 | 0.88 | 0.96 | 1.08 | 1.00 | 1.00 | 1.00 | 0.86 | 1.00 | 0.94 |
| Ccno | 1.23 | 0.80 | 1.10 | 1.06 | 1.22 | 1.14 | 1.00 | 1.00 | 1.00 | 1.00 | 1.00 | 1.00 |
| Cd177 | 1.89 | 2.30 | 1.00 | 1.03 | 1.27 | 1.26 | 1.00 | 1.00 | 1.00 | 1.00 | 1.00 | 1.00 |
| Cd180 | 1.33 | 2.44 | 1.61 | 1.05 | 1.35 | 0.78 | 1.00 | 1.00 | 1.00 | 1.28 | 1.56 | 0.93 |
| Cd19 | 2.60 | 3.34 | 2.51 | 1.03 | 0.43 | 0.79 | 1.00 | 0.89 | 0.85 | 1.00 | 1.00 | 1.00 |
| Cd24a | 0.98 | 0.90 | 0.97 | 1.19 | 0.79 | 1.11 | 0.97 | 1.00 | 1.04 | 0.90 | 1.21 | 1.14 |
| Cd300lf | 1.11 | 1.65 | 1.20 | 0.91 | 1.30 | 1.05 | 1.00 | 1.00 | 1.00 | 1.00 | 1.00 | 1.00 |
| Cd37 | 0.94 | 1.94 | 1.19 | 0.99 | 0.89 | 0.88 | 0.93 | 0.67 | 0.63 | 0.89 | 0.99 | 0.79 |
| Cd52 | 0.91 | 1.49 | 1.00 | 1.09 | 1.03 | 1.07 | 0.98 | 0.43 | 0.25 | 0.97 | 1.13 | 1.03 |
| Cd69 | 0.90 | 0.79 | 1.31 | 0.81 | 0.75 | 1.67 | 1.00 | 1.00 | 1.00 | 1.00 | 1.00 | 1.00 |
| Cd72 | 1.64 | 2.95 | 1.91 | 1.16 | 0.48 | 0.75 | 1.00 | 1.00 | 1.00 | 1.00 | 1.18 | 0.90 |
| Cd79a | 2.79 | 3.73 | 2.49 | 1.06 | 0.54 | 0.85 | 1.04 | 0.67 | 0.53 | 1.00 | 1.00 | 1.00 |
| Cd79b | 2.13 | 3.07 | 2.10 | 1.08 | 0.49 | 0.86 | 1.53 | 0.51 | 0.53 | 1.00 | 1.00 | 1.00 |
| Cdc45 | 0.50 | 0.63 | 0.87 | 0.91 | 1.03 | 1.04 | 1.00 | 1.00 | 1.00 | 0.95 | 0.82 | 0.84 |
| Cdca3 | 0.36 | 0.79 | 0.86 | 0.86 | 1.11 | 1.06 | 1.00 | 1.00 | 1.00 | 0.84 | 1.40 | 1.06 |
| Cdca5 | 0.42 | 0.71 | 0.96 | 0.92 | 0.99 | 1.00 | 1.00 | 1.00 | 1.00 | 1.11 | 1.25 | 1.09 |
| Cdca8 | 0.40 | 0.69 | 0.95 | 0.96 | 0.93 | 1.03 | 1.00 | 1.00 | 1.00 | 0.85 | 1.16 | 0.98 |
| Cdk1 | 0.45 | 0.67 | 0.88 | 1.04 | 0.91 | 1.07 | 1.00 | 1.00 | 1.00 | 0.80 | 1.26 | 0.92 |
| Cdkn1a | 1.19 | 0.92 | 1.18 | 0.99 | 1.06 | 0.90 | 0.97 | 2.54 | 2.84 | 1.11 | 0.95 | 1.09 |
| Cdkn2a | 1.27 | 1.47 | 1.14 | 1.00 | 1.00 | 1.00 | 1.00 | 1.00 | 1.00 | 1.00 | 1.00 | 1.00 |
| Cebpd | 1.34 | 1.61 | 2.66 | 1.07 | 1.04 | 1.24 | 0.91 | 1.01 | 1.33 | 1.46 | 0.87 | 0.93 |
| Cela2a | 0.23 | 1.00 | 0.12 | 1.00 | 1.00 | 1.00 | 0.94 | 0.98 | 1.14 | 1.00 | 1.00 | 1.02 |
| Cemip | 1.10 | 1.03 | 1.00 | 1.00 | 1.00 | 1.00 | 1.00 | 1.00 | 1.00 | 1.00 | 1.00 | 1.01 |
| Cenpa | 0.52 | 0.70 | 0.85 | 1.02 | 0.81 | 1.09 | 1.00 | 1.00 | 1.00 | 0.92 | 1.12 | 0.86 |
| Cenpe | 0.36 | 0.59 | 0.90 | 1.04 | 0.95 | 0.91 | 1.00 | 1.00 | 1.00 | 1.00 | 1.27 | 1.00 |
| Cenpf | 0.33 | 0.58 | 0.94 | 1.05 | 0.90 | 1.00 | 1.00 | 1.00 | 1.00 | 0.84 | 1.16 | 0.97 |
| Cenph | 0.65 | 0.68 | 0.85 | 0.92 | 0.93 | 0.98 | 1.00 | 1.00 | 1.00 | 0.96 | 1.21 | 0.67 |
| Cenpn | 0.58 | 0.71 | 0.88 | 0.96 | 0.85 | 0.92 | 1.00 | 1.00 | 1.00 | 0.91 | 1.05 | 1.04 |
| Cep55 | 0.47 | 0.79 | 0.93 | 0.93 | 1.14 | 0.88 | 1.00 | 1.00 | 1.00 | 0.97 | 1.42 | 1.00 |
| Ces5a | 1.00 | 1.00 | 1.00 | 1.00 | 1.00 | 1.00 | 1.00 | 1.00 | 1.00 | 1.00 | 1.00 | 1.00 |
| Cfd | 2.37 | 2.33 | 3.24 | 1.00 | 1.00 | 1.00 | 0.75 | 1.07 | 1.14 | 0.91 | 1.04 | 0.72 |
| Ch25h | 0.85 | 1.57 | 2.16 | 1.00 | 1.00 | 1.00 | 1.00 | 1.00 | 1.00 | 1.00 | 1.00 | 1.00 |
| Chad | 1.62 | 5.68 | 1.51 | 1.00 | 1.00 | 1.00 | 1.04 | 1.05 | 1.00 | 1.17 | 0.88 | 0.90 |
| Chil1 | 0.59 | 1.70 | 1.16 | 1.05 | 0.74 | 1.03 | 1.00 | 1.00 | 1.00 | 1.02 | 1.20 | 1.48 |
| Chil3 | 2.34 | 3.18 | 0.75 | 1.20 | 0.85 | 0.85 | 1.00 | 1.00 | 1.00 | 1.00 | 1.00 | 1.00 |
| Chil4 | 1.47 | 5.39 | 0.64 | 1.21 | 0.84 | 0.86 | 1.00 | 1.00 | 1.00 | 0.89 | 1.00 | 1.00 |
| Cidec | 1.76 | 1.46 | 2.32 | 1.00 | 1.00 | 1.00 | 0.79 | 1.00 | 0.78 | 0.88 | 0.96 | 0.64 |
| Cilp | 1.73 | 1.04 | 1.59 | 1.00 | 1.00 | 1.00 | 1.00 | 1.00 | 1.00 | 1.15 | 0.81 | 1.05 |
| Cited1 | 1.00 | 1.00 | 1.00 | 1.00 | 1.00 | 1.00 | 1.00 | 1.00 | 1.00 | 1.00 | 1.09 | 1.00 |
| Ckap2 | 0.42 | 0.69 | 0.88 | 1.10 | 1.04 | 1.05 | 1.00 | 1.00 | 1.00 | 0.83 | 1.21 | 0.88 |
| Ckap2l | 0.38 | 0.67 | 0.88 | 0.98 | 0.99 | 0.99 | 1.00 | 1.00 | 1.00 | 1.04 | 1.17 | 0.99 |
| Ckm | 5.89 | 13.73 | 4.55 | 6.86 | 1.00 | 3.47 | 1.52 | 1.00 | 1.00 | 1.56 | 0.97 | 0.99 |
| Cks2 | 0.50 | 0.66 | 0.93 | 1.03 | 0.88 | 1.01 | 1.00 | 1.00 | 1.00 | 0.67 | 0.99 | 1.02 |
| Clca3 | 1.00 | 11.85 | 1.00 | 1.00 | 1.00 | 1.00 | 1.00 | 0.62 | 1.00 | 0.57 | 1.00 | 1.00 |
| Cldn18 | 1.00 | 1.00 | 1.00 | 1.00 | 1.00 | 1.00 | 1.00 | 1.00 | 1.00 | 1.00 | 1.00 | 1.01 |
| Cldn3 | 1.54 | 1.76 | 1.06 | 1.00 | 1.00 | 1.00 | 0.95 | 1.12 | 1.07 | 0.78 | 0.91 | 0.98 |
| Cldn4 | 1.10 | 0.75 | 0.79 | 1.00 | 1.00 | 1.00 | 1.00 | 1.00 | 1.00 | 1.05 | 0.87 | 0.92 |
| Cldn8 | 1.00 | 1.09 | 1.00 | 1.00 | 1.00 | 1.00 | 0.96 | 0.89 | 1.13 | 0.84 | 1.00 | 1.00 |
| Clec4e | 0.48 | 5.05 | 1.00 | 0.96 | 1.48 | 1.31 | 1.00 | 1.00 | 1.00 | 1.00 | 1.00 | 1.00 |
| Clpsl2 | 1.00 | 1.00 | 1.00 | 1.00 | 1.00 | 1.00 | 1.00 | 1.00 | 1.00 | 1.00 | 1.04 | 1.01 |
| Clu | 1.39 | 1.89 | 2.12 | 1.05 | 0.68 | 1.49 | 1.16 | 0.90 | 1.23 | 1.07 | 1.07 | 0.81 |

Fig. 31- 33

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Cmtm7 | 1.18 | 1.86 | 1.43 | 0.75 | 2.00 | 1.07 | 0.91 | 6.89 | 1.02 |
| Cnfn | 1.00 | 1.00 | 1.00 | 1.00 | 1.00 | 1.00 | 1.00 | 1.00 | 1.00 |
| Cnksr2 | 1.00 | 1.00 | 1.00 | 1.00 | 1.00 | 1.00 | 1.00 | 1.00 | 1.00 |
| Col11a1 | 1.00 | 10.03 | 1.40 | 1.00 | 1.00 | 1.00 | 1.00 | 1.00 | 1.00 |
| Col12a1 | 1.68 | 6.88 | 1.74 | 1.01 | 1.25 | 1.26 | 1.00 | 1.00 | 1.00 |
| Col6a5 | 0.87 | 1.16 | 6.68 | 1.00 | 1.00 | 1.00 | 1.00 | 1.00 | 1.00 |
| Col8a1 | 1.96 | 8.08 | 3.34 | 1.33 | 1.31 | 1.12 | 1.00 | 1.00 | 1.00 |
| Col8a2 | 1.00 | 14.14 | 5.83 | 1.00 | 1.00 | 1.00 | 1.00 | 1.00 | 1.00 |
| Comp | 0.67 | 6.82 | 23.85 | 1.00 | 1.00 | 1.00 | 1.00 | 1.00 | 1.00 |
| Coro1a | 1.84 | 2.53 | 3.28 | 0.73 | 1.60 | 0.91 | 0.54 | 10.04 | 1.20 |
| Cpb2 | 1.00 | 1.00 | 1.00 | 7.90 | 0.47 | 0.22 | 0.81 | 1.08 | 1.02 |
| Cplx2 | 1.08 | 2.16 | 1.08 | 0.96 | 1.31 | 0.89 | 1.00 | 5.47 | 1.00 |
| Cpn1 | 1.00 | 1.00 | 1.00 | 1.00 | 3.50 | 1.00 | 1.04 | 0.88 | 0.93 |
| Cpne5 | 0.49 | 1.30 | 0.69 | 1.00 | 1.00 | 1.00 | 1.00 | 1.00 | 1.00 |
| Cr2 | 1.00 | 1.00 | 1.00 | 1.00 | 1.00 | 1.00 | 1.00 | 1.00 | 1.00 |
| Crct1 | 1.00 | 1.00 | 1.00 | 1.00 | 1.00 | 1.00 | 1.00 | 1.00 | 1.00 |
| Crhbp | 1.00 | 1.00 | 1.00 | 1.00 | 1.00 | 1.00 | 1.00 | 2.25 | 1.00 |
| Crisp4 | 1.00 | 1.00 | 1.00 | 1.00 | 1.00 | 1.00 | 1.00 | 1.00 | 1.00 |
| Crlf1 | 3.28 | 8.23 | 9.07 | 1.00 | 1.00 | 1.00 | 1.00 | 1.00 | 1.00 |
| Crtam | 1.00 | 1.00 | 1.00 | 1.00 | 1.00 | 1.08 | 1.00 | 1.00 | 1.00 |
| Cryba4 | 0.65 | 0.22 | 0.59 | 1.00 | 1.00 | 1.00 | 1.00 | 1.00 | 1.00 |
| Csrp3 | 1.47 | 0.78 | 0.78 | 1.00 | 1.00 | 1.00 | 1.02 | 1.14 | 1.07 |
| Cst11 | 1.00 | 1.00 | 1.00 | 1.00 | 1.00 | 1.00 | 1.00 | 1.00 | 1.00 |
| Ctgf | 7.12 | 4.22 | 3.47 | 2.27 | 1.36 | 0.85 | 3.82 | 1.93 | 0.54 |
| Ctrb1 | 1.00 | 1.00 | 1.00 | 1.00 | 1.00 | 1.00 | 1.00 | 6.84 | 1.00 |
| Ctse | 2.06 | 1.34 | 1.50 | 1.25 | 1.01 | 1.05 | 3.12 | 0.60 | 1.11 |
| Ctss | 1.64 | 5.69 | 2.12 | 0.94 | 1.67 | 0.74 | 0.94 | 1.89 | 0.80 |
| Cuzd1 | 0.85 | 0.95 | 1.00 | 1.00 | 1.00 | 1.00 | 1.00 | 1.00 | 1.00 |
| Cxcl13 | 0.24 | 1.19 | 2.84 | 1.00 | 1.00 | 1.00 | 0.67 | 1.59 | 1.06 |
| Cxcl15 | 1.33 | 1.00 | 13.27 | 1.00 | 1.00 | 1.00 | 1.00 | 1.00 | 1.00 |
| Cxcl17 | 1.00 | 1.00 | 1.71 | 1.00 | 1.00 | 1.00 | 1.00 | 1.00 | 1.00 |
| Cxcl2 | 10.39 | 1.00 | 1.00 | 1.00 | 1.00 | 1.00 | 1.00 | 1.00 | 1.00 |
| Cxcl3 | 9.89 | 1.00 | 1.00 | 1.00 | 1.00 | 1.00 | 1.00 | 1.00 | 1.00 |
| Cxcr2 | 6.34 | 1.59 | 1.00 | 1.00 | 1.00 | 1.00 | 1.00 | 1.00 | 1.00 |
| Cxcr4 | 1.82 | 2.95 | 1.16 | 1.27 | 1.80 | 0.95 | 1.00 | 10.74 | 1.00 |
| Cxcr5 | 1.00 | 1.00 | 1.00 | 1.00 | 1.00 | 1.00 | 1.00 | 1.52 | 1.00 |
| Cxcr6 | 8.53 | 2.05 | 1.40 | 1.00 | 1.00 | 0.91 | 1.00 | 1.00 | 1.00 |
| Cyb561 | 1.25 | 1.23 | 1.64 | 0.77 | 0.96 | 1.21 | 0.42 | 1.09 | 1.56 |
| Cyp2a5 | 1.00 | 1.00 | 3.17 | 1.71 | 0.46 | 0.85 | 5.28 | 0.23 | 0.37 |
| Cyp2e1 | 0.53 | 0.32 | 5.49 | 1.44 | 0.73 | 1.05 | 1.32 | 0.61 | 0.76 |
| Cyp2f2 | 1.00 | 1.00 | 13.35 | 2.62 | 1.03 | 0.40 | 0.62 | 0.55 | 1.59 |
| Cyp46a1 | 1.00 | 1.00 | 1.00 | 0.91 | 1.00 | 0.99 | 5.70 | 0.73 | 0.07 |
| Cyp4a10 | 1.00 | 1.00 | 1.00 | 2.12 | 1.76 | 1.12 | 3.98 | 7.05 | 0.36 |
| Cyp4a14 | 1.00 | 1.00 | 1.00 | 3.65 | 2.68 | 0.94 | 11.04 | 4.50 | 0.13 |
| D730048I06Rik | 1.00 | 1.00 | 1.00 | 1.00 | 1.00 | 1.00 | 1.00 | 1.00 | 1.00 |
| Dck | 1.52 | 2.13 | 1.12 | 1.04 | 1.33 | 1.09 | 0.72 | 4.95 | 0.76 |
| Ddit4 | 2.45 | 2.43 | 0.33 | 1.78 | 2.38 | 0.89 | 1.46 | 3.20 | 0.69 |
| Defb1 | 1.00 | 1.00 | 1.00 | 1.02 | 1.13 | 1.23 | 1.00 | 1.00 | 1.00 |
| Defb10 | 1.00 | 1.00 | 1.00 | 1.00 | 1.00 | 1.00 | 1.00 | 1.00 | 1.00 |
| Defb12 | 1.00 | 1.00 | 1.00 | 1.00 | 1.00 | 1.00 | 1.00 | 1.00 | 1.00 |
| Defb13 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 |
| Defb19 | 1.00 | 1.00 | 1.00 | 0.94 | 0.57 | 1.37 | 1.00 | 1.00 | 1.00 |
| Defb2 | 1.00 | 1.00 | 1.00 | 1.01 | 0.93 | 1.05 | 1.00 | 1.00 | 1.00 |
| Defb20 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 |
| Defb23 | 1.00 | 1.00 | 1.00 | 1.00 | 1.00 | 1.00 | 1.00 | 1.00 | 1.00 |
| Defb25 | 1.00 | 1.00 | 1.00 | 1.00 | 1.00 | 1.00 | 1.00 | 1.00 | 1.00 |
| Defb26 | 1.00 | 1.00 | 1.00 | 1.00 | 1.00 | 1.00 | 1.00 | 1.00 | 1.00 |
| Defb28 | 1.00 | 1.00 | 1.00 | 1.00 | 1.00 | 1.00 | 1.00 | 1.00 | 1.00 |
| Defb29 | 1.00 | 1.00 | 1.00 | 1.05 | 1.11 | 1.15 | 1.00 | 1.00 | 1.00 |
| Defb30 | 1.00 | 1.00 | 1.00 | 1.00 | 1.00 | 1.00 | 1.00 | 1.00 | 1.00 |
| Defb35 | 1.00 | 1.00 | 1.00 | 1.00 | 1.00 | 1.00 | 1.00 | 1.00 | 1.00 |

Fig. 31- 34

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Cmtm7 | 0.88 | 4.56 | 1.18 | 0.87 | 1.28 | 1.31 | 0.90 | 0.98 | 0.88 |
| Cnfn | 1.00 | 1.00 | 1.00 | 1.00 | 1.00 | 1.00 | 1.00 | 1.00 | 1.00 |
| Cnksr2 | 1.00 | 1.00 | 1.00 | 1.00 | 1.00 | 1.00 | 1.00 | 1.00 | 1.00 |
| Col11a1 | 1.00 | 1.00 | 1.00 | 1.00 | 0.76 | 1.00 | 1.00 | 1.00 | 1.00 |
| Col12a1 | 1.00 | 1.36 | 0.82 | 1.33 | 0.68 | 0.81 | 1.46 | 0.90 | 0.86 |
| Col6a5 | 0.65 | 0.79 | 1.13 | 1.00 | 1.00 | 1.00 | 1.13 | 1.00 | 0.83 |
| Col8a1 | 1.78 | 1.88 | 1.06 | 0.91 | 0.72 | 0.97 | 1.00 | 1.00 | 1.00 |
| Col8a2 | 0.73 | 0.71 | 0.89 | 1.07 | 0.96 | 1.00 | 0.92 | 0.71 | 0.92 |
| Comp | 1.00 | 1.00 | 1.00 | 1.15 | 0.53 | 0.55 | 1.00 | 1.00 | 1.00 |
| Coro1a | 0.64 | 2.53 | 0.99 | 0.73 | 0.81 | 1.13 | 0.89 | 0.96 | 0.80 |
| Cpb2 | 1.00 | 1.00 | 1.00 | 1.00 | 1.00 | 1.00 | 1.00 | 1.00 | 1.00 |
| Cplx2 | 0.78 | 7.51 | 0.79 | 1.00 | 1.10 | 1.00 | 0.92 | 0.76 | 0.86 |
| Cpn1 | 0.82 | 0.94 | 1.12 | 1.00 | 1.00 | 1.00 | 1.24 | 0.61 | 0.90 |
| Cpne5 | 0.76 | 0.78 | 1.12 | 1.00 | 1.00 | 1.00 | 1.00 | 1.00 | 0.81 |
| Cr2 | 0.81 | 0.91 | 0.63 | 1.00 | 1.00 | 1.00 | 0.84 | 0.71 | 1.04 |
| Crct1 | 1.00 | 1.00 | 1.00 | 1.00 | 1.00 | 1.00 | 1.00 | 1.00 | 1.00 |
| Crhbp | 1.00 | 7.31 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 |
| Crlf1 | 1.78 | 1.16 | 0.79 | 1.16 | 0.89 | 1.05 | 1.26 | 1.00 | 1.00 |
| Crtam | 1.00 | 1.00 | 1.00 | 1.00 | 1.00 | 1.00 | 0.99 | 1.09 | 0.79 |
| Cryba4 | 1.00 | 1.00 | 1.00 | 1.00 | 1.00 | 1.00 | 0.89 | 1.23 | 1.00 |
| Csrp3 | 0.96 | 0.95 | 1.23 | 1.40 | 0.34 | 1.24 | 1.00 | 1.00 | 1.00 |
| Cst11 | 1.00 | 1.00 | 1.00 | 1.00 | 1.00 | 1.00 | 1.00 | 1.00 | 1.00 |
| Ctgf | 3.11 | 1.30 | 1.01 | 1.96 | 1.07 | 0.58 | 1.80 | 1.06 | 0.86 |
| Ctrb1 | 1.00 | 1.00 | 1.00 | 1.00 | 1.00 | 1.00 | 1.59 | 0.07 | 0.00 |
| Ctse | 1.91 | 0.96 | 1.21 | 1.00 | 0.52 | 1.00 | 2.41 | 1.12 | 2.44 |
| Ctss | 1.02 | 1.50 | 0.94 | 0.85 | 0.98 | 1.27 | 0.95 | 0.92 | 0.80 |
| Cuzd1 | 1.00 | 1.00 | 1.00 | 0.89 | 1.39 | 1.05 | 1.14 | 0.11 | 0.04 |
| Cxcl13 | 1.46 | 1.24 | 0.81 | 1.62 | 2.01 | 0.60 | 0.83 | 0.54 | 1.52 |
| Cxcl15 | 1.10 | 1.43 | 1.69 | 1.00 | 1.00 | 1.00 | 1.00 | 1.00 | 1.00 |
| Cxcl17 | 1.69 | 1.15 | 1.14 | 1.00 | 1.00 | 1.00 | 1.00 | 1.00 | 1.00 |
| Cxcl2 | 3.94 | 1.17 | 1.00 | 1.00 | 1.00 | 1.00 | 1.00 | 1.00 | 1.00 |
| Cxcl3 | 3.96 | 1.00 | 1.00 | 1.00 | 1.00 | 1.00 | 1.00 | 1.00 | 1.00 |
| Cxcr2 | 1.03 | 0.98 | 1.17 | 1.00 | 0.98 | 1.00 | 0.73 | 1.11 | 1.55 |
| Cxcr4 | 0.89 | 4.12 | 0.95 | 1.18 | 1.38 | 1.22 | 1.59 | 1.50 | 0.70 |
| Cxcr5 | 0.32 | 5.72 | 0.82 | 1.00 | 1.00 | 1.00 | 1.00 | 0.95 | 0.81 |
| Cxcr6 | 0.73 | 0.87 | 1.68 | 1.00 | 1.00 | 1.00 | 1.20 | 0.50 | 1.76 |
| Cyb561 | 1.07 | 0.81 | 0.95 | 0.81 | 0.81 | 1.23 | 1.63 | 0.88 | 1.05 |
| Cyp2a5 | 0.40 | 0.24 | 0.58 | 1.00 | 1.00 | 1.00 | 1.00 | 1.00 | 1.00 |
| Cyp2e1 | 0.46 | 0.69 | 0.48 | 0.96 | 1.14 | 1.60 | 4.01 | 0.35 | 1.25 |
| Cyp2f2 | 0.95 | 0.59 | 0.75 | 1.44 | 0.92 | 0.52 | 1.00 | 1.00 | 1.00 |
| Cyp46a1 | 1.00 | 1.00 | 1.00 | 1.00 | 1.00 | 1.00 | 0.93 | 1.00 | 0.92 |
| Cyp4a10 | 1.00 | 1.00 | 1.00 | 1.00 | 1.00 | 1.00 | 1.00 | 1.00 | 1.00 |
| Cyp4a14 | 1.00 | 1.00 | 1.00 | 1.00 | 1.00 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 |
| Dck | 1.16 | 6.26 | 0.99 | 0.86 | 1.06 | 0.96 | 1.16 | 1.32 | 1.72 |
| Ddit4 | 1.74 | 1.84 | 0.58 | 18.19 | 8.39 | 0.32 | 2.23 | 1.71 | 0.45 |
| Defb1 | 1.00 | 1.00 | 1.00 | 1.00 | 1.00 | 1.00 | 1.00 | 1.00 | 1.00 |
| Defb10 | 1.00 | 1.00 | 1.00 | 1.00 | 1.00 | 1.00 | 1.00 | 1.00 | 1.00 |
| Defb12 | 1.00 | 1.00 | 1.00 | 1.00 | 1.00 | 1.00 | 1.00 | 1.00 | 1.00 |
| Defb13 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 |
| Defb19 | 1.00 | 1.00 | 1.00 | 1.00 | 1.00 | 0.88 | 1.00 | 1.00 | 1.00 |
| Defb2 | 1.00 | 1.00 | 1.00 | 1.00 | 1.00 | 1.00 | 1.00 | 1.00 | 1.00 |
| Defb20 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 |
| Defb23 | 0.99 | 1.00 | 1.50 | 1.00 | 1.00 | 1.00 | 1.00 | 1.00 | 1.00 |
| Defb25 | 1.00 | 1.00 | 1.00 | 1.00 | 1.00 | 1.00 | 1.00 | 1.00 | 1.00 |
| Defb26 | 1.00 | 1.00 | 1.00 | 1.00 | 1.00 | 1.00 | 1.00 | 1.00 | 1.00 |
| Defb28 | 1.00 | 1.00 | 1.00 | 1.00 | 1.00 | 1.00 | 1.00 | 1.00 | 1.00 |
| Defb29 | 1.00 | 1.00 | 1.00 | 1.00 | 1.00 | 1.00 | 1.00 | 1.00 | 1.00 |
| Defb30 | 1.00 | 1.00 | 1.00 | 1.00 | 1.00 | 1.00 | 1.00 | 1.00 | 1.00 |
| Defb35 | 1.00 | 1.00 | 1.00 | 1.00 | 1.00 | 1.00 | 1.00 | 1.00 | 1.00 |

Fig. 31-35

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Cmtm7 | 0.69 | 3.45 | 0.89 | 1.25 | 2.14 | 0.89 | 0.64 | 1.04 | 1.06 |
| Cnfn | 1.00 | 1.00 | 1.00 | 1.00 | 1.00 | 1.00 | 1.00 | 1.00 | 1.00 |
| Cnksr2 | 1.05 | 1.06 | 0.96 | 1.00 | 7.29 | 1.00 | 1.00 | 1.00 | 1.00 |
| Col11a1 | 1.12 | 0.99 | 0.97 | 1.00 | 1.00 | 1.00 | 1.00 | 1.00 | 1.00 |
| Col12a1 | 1.03 | 1.55 | 1.03 | 1.70 | 2.21 | 0.65 | 0.80 | 0.90 | 1.00 |
| Col6a5 | 1.00 | 1.00 | 1.00 | 0.83 | 1.38 | 0.75 | 0.66 | 1.08 | 0.92 |
| Col8a1 | 1.11 | 1.06 | 1.00 | 1.08 | 1.06 | 0.75 | 1.00 | 1.00 | 1.00 |
| Col8a2 | 1.00 | 1.16 | 1.09 | 0.61 | 0.59 | 1.14 | 1.00 | 1.00 | 1.00 |
| Comp | 1.00 | 0.90 | 1.00 | 1.00 | 0.84 | 1.13 | 1.06 | 1.01 | 1.07 |
| Coro1a | 0.96 | 1.20 | 0.91 | 1.09 | 0.95 | 0.80 | 1.00 | 0.97 | 1.00 |
| Cpb2 | 1.00 | 1.00 | 1.00 | 1.00 | 1.00 | 1.00 | 1.00 | 1.00 | 1.00 |
| Cplx2 | 0.95 | 1.00 | 1.00 | 0.89 | 1.31 | 0.78 | 1.00 | 1.00 | 1.00 |
| Cpn1 | 1.00 | 1.00 | 1.00 | 1.00 | 9.71 | 1.00 | 1.00 | 3.88 | 1.00 |
| Cpne5 | 1.01 | 1.01 | 0.94 | 1.00 | 10.34 | 1.00 | 0.77 | 1.10 | 0.74 |
| Cr2 | 1.00 | 1.00 | 1.00 | 1.00 | 1.00 | 1.00 | 1.00 | 1.00 | 1.00 |
| Crct1 | 1.00 | 1.00 | 1.00 | 1.00 | 1.00 | 1.00 | 1.00 | 1.00 | 1.00 |
| Crhbp | 0.84 | 1.13 | 0.98 | 1.00 | 1.00 | 1.00 | 1.00 | 1.00 | 1.00 |
| Crisp4 | 1.00 | 1.00 | 1.00 | 1.00 | 43.53 | 1.00 | 1.00 | 1.00 | 1.00 |
| Crlf1 | 1.02 | 1.04 | 0.93 | 1.00 | 0.69 | 1.10 | 1.14 | 0.99 | 1.05 |
| Crtam | 1.17 | 0.89 | 1.10 | 1.00 | 1.00 | 1.00 | 5.32 | 1.60 | 0.22 |
| Cryba4 | 1.00 | 1.00 | 1.00 | 1.00 | 26.93 | 1.00 | 1.00 | 1.00 | 1.00 |
| Csrp3 | 1.00 | 1.00 | 1.00 | 1.00 | 1.00 | 1.00 | 1.00 | 1.00 | 1.00 |
| Cst11 | 1.00 | 1.00 | 1.00 | 1.00 | 7.64 | 1.00 | 1.00 | 1.00 | 1.00 |
| Ctgf | 1.62 | 1.15 | 0.90 | 4.15 | 1.22 | 0.61 | 1.35 | 1.00 | 0.90 |
| Ctrb1 | 1.00 | 1.00 | 1.00 | 1.00 | 1.00 | 1.00 | 1.00 | 1.00 | 1.00 |
| Ctse | 1.00 | 1.00 | 1.00 | 2.54 | 0.89 | 0.40 | 1.00 | 1.00 | 1.00 |
| Ctss | 0.91 | 1.19 | 0.78 | 1.35 | 1.31 | 0.59 | 0.94 | 0.85 | 0.89 |
| Cuzd1 | 1.00 | 1.00 | 1.00 | 0.31 | 6.60 | 1.00 | 0.98 | 1.20 | 1.38 |
| Cxcl13 | 1.00 | 1.00 | 1.00 | 2.74 | 1.52 | 0.32 | 1.00 | 1.00 | 1.00 |
| Cxcl15 | 1.00 | 1.00 | 1.00 | 1.00 | 1.00 | 1.00 | 1.00 | 1.00 | 1.00 |
| Cxcl17 | 1.00 | 1.00 | 1.00 | 1.00 | 1.00 | 1.00 | 1.00 | 1.00 | 1.00 |
| Cxcl2 | 1.00 | 1.00 | 1.00 | 12.02 | 1.00 | 1.00 | 1.00 | 1.00 | 1.00 |
| Cxcl3 | 1.00 | 1.00 | 1.00 | 6.62 | 1.00 | 1.00 | 1.00 | 1.00 | 1.00 |
| Cxcr2 | 1.00 | 1.00 | 1.00 | 4.26 | 1.00 | 1.00 | 1.00 | 1.00 | 1.00 |
| Cxcr4 | 0.89 | 3.51 | 1.00 | 1.55 | 1.21 | 0.41 | 0.93 | 0.95 | 0.87 |
| Cxcr5 | 1.00 | 1.00 | 1.00 | 1.00 | 1.15 | 0.25 | 1.00 | 0.76 | 1.14 |
| Cxcr6 | 1.00 | 1.00 | 1.00 | 1.00 | 0.93 | 1.09 | 1.00 | 1.00 | 1.00 |
| Cyb561 | 0.91 | 0.97 | 1.03 | 0.65 | 10.45 | 1.78 | 1.05 | 1.07 | 1.10 |
| Cyp2a5 | 1.00 | 1.00 | 1.00 | 1.00 | 1.00 | 1.00 | 1.00 | 1.00 | 1.00 |
| Cyp2e1 | 1.00 | 1.00 | 0.98 | 1.07 | 0.73 | 1.64 | 0.26 | 1.13 | 0.87 |
| Cyp2f2 | 1.00 | 1.00 | 1.00 | 0.57 | 0.70 | 0.98 | 0.48 | 0.75 | 1.90 |
| Cyp46a1 | 0.92 | 1.01 | 1.26 | 1.00 | 1.00 | 1.00 | 1.38 | 1.14 | 0.86 |
| Cyp4a10 | 1.00 | 1.00 | 1.00 | 1.00 | 1.00 | 1.00 | 1.00 | 1.00 | 1.00 |
| Cyp4a14 | 1.00 | 1.00 | 1.00 | 1.00 | 1.00 | 1.00 | 1.00 | 1.00 | 1.00 |
| D730048I06Rik | 1.00 | 1.00 | 1.00 | 1.00 | 224.96 | 1.00 | 1.00 | 1.00 | 1.00 |
| Dck | 0.99 | 1.30 | 0.95 | 0.88 | 1.12 | 0.93 | 1.00 | 1.00 | 0.97 |
| Ddit4 | 1.75 | 1.37 | 0.72 | 1.80 | 1.90 | 0.56 | 1.02 | 0.98 | 0.98 |
| Defb1 | 1.00 | 1.00 | 1.00 | 1.00 | 13.93 | 1.00 | 1.00 | 1.00 | 1.00 |
| Defb10 | 1.00 | 1.00 | 1.00 | 1.00 | 9.20 | 1.00 | 1.00 | 1.00 | 1.00 |
| Defb12 | 1.00 | 1.00 | 1.00 | 1.00 | 250.54 | 1.00 | 1.00 | 1.00 | 1.00 |
| Defb13 | 1.00 | 1.00 | 1.00 | 1.00 | 54.72 | 1.00 | 1.10 | 0.93 | 0.99 |
| Defb15 | 1.00 | 1.00 | 1.00 | 1.00 | 286.50 | 1.00 | 1.00 | 1.01 | 1.00 |
| Defb18 | 1.00 | 1.00 | 1.00 | 1.00 | 251.95 | 1.00 | 1.00 | 1.00 | 1.00 |
| Defb19 | 1.00 | 1.00 | 1.00 | 1.00 | 61.72 | 1.00 | 0.89 | 0.90 | 1.02 |
| Defb2 | 1.00 | 1.00 | 1.00 | 1.00 | 7.40 | 1.00 | 1.00 | 1.00 | 0.89 |
| Defb20 | 1.00 | 1.00 | 1.00 | 1.00 | 55.31 | 1.00 | 1.00 | 1.00 | 1.00 |
| Defb21 | 1.00 | 1.00 | 1.00 | 1.00 | 596.19 | 1.00 | 0.91 | 0.79 | 0.76 |
| Defb23 | 1.00 | 1.00 | 1.00 | 1.00 | 255.58 | 1.00 | 1.19 | 0.93 | 1.27 |
| Defb25 | 1.00 | 1.00 | 1.00 | 0.83 | 9.41 | 1.00 | 1.00 | 1.00 | 1.00 |
| Defb26 | 1.00 | 1.00 | 1.00 | 1.00 | 7.04 | 1.00 | 1.00 | 1.00 | 1.00 |
| Defb28 | 1.00 | 1.00 | 1.00 | 1.00 | 5.45 | 1.00 | 1.35 | 1.36 | 1.41 |
| Defb29 | 1.00 | 1.00 | 1.00 | 0.57 | 42.72 | 1.00 | 1.00 | 1.00 | 1.00 |
| Defb30 | 1.00 | 1.00 | 1.00 | 1.00 | 1010.11 | 1.00 | 0.80 | 1.00 | 0.77 |
| Defb35 | 1.00 | 1.00 | 1.00 | 1.00 | 45.71 | 1.00 | 1.00 | 1.00 | 1.00 |

Fig. 31- 36

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Cmtm7 | 0.89 | 0.84 | 0.78 | 0.93 | 1.00 | 0.93 | 1.13 | 0.95 | 1.09 | 0.99 | 1.20 | 1.05 |
| Cnfn | 1.06 | 12.67 | 1.37 | 1.00 | 1.00 | 1.00 | 1.00 | 1.00 | 1.00 | 1.15 | 1.00 | 1.00 |
| Cnksr2 | 1.00 | 1.00 | 1.00 | 1.00 | 1.00 | 1.00 | 1.00 | 1.00 | 1.00 | 1.00 | 1.01 | 1.02 |
| Col11a1 | 1.00 | 1.00 | 1.00 | 1.00 | 1.00 | 1.00 | 1.00 | 1.00 | 1.00 | 0.81 | 0.88 | 0.93 |
| Col12a1 | 1.27 | 0.89 | 1.12 | 1.00 | 1.00 | 1.00 | 1.00 | 1.00 | 1.00 | 0.82 | 1.00 | 1.00 |
| Col6a5 | 1.14 | 1.64 | 1.66 | 1.00 | 1.00 | 1.00 | 1.00 | 1.00 | 1.05 | 1.00 | 0.99 | 0.99 |
| Col8a1 | 1.20 | 0.88 | 1.09 | 1.00 | 1.00 | 1.00 | 1.00 | 1.00 | 1.00 | 1.12 | 1.07 | 1.05 |
| Col8a2 | 1.00 | 0.76 | 1.00 | 1.00 | 1.00 | 1.00 | 1.00 | 1.00 | 1.00 | 0.96 | 0.93 | 1.00 |
| Comp | 1.36 | 2.01 | 0.86 | 1.00 | 1.00 | 1.00 | 1.00 | 1.00 | 1.00 | 0.97 | 0.91 | 0.99 |
| Coro1a | 0.81 | 0.90 | 0.89 | 1.10 | 1.00 | 1.03 | 0.91 | 0.49 | 0.49 | 1.08 | 0.92 | 0.88 |
| Cpb2 | 1.00 | 1.00 | 1.00 | 1.00 | 1.00 | 1.00 | 1.00 | 1.00 | 1.00 | 1.00 | 1.02 | 1.01 |
| Cplx2 | 1.27 | 1.03 | 1.20 | 0.89 | 0.38 | 0.67 | 1.00 | 1.00 | 1.00 | 0.98 | 1.00 | 1.00 |
| Cpn1 | 1.00 | 1.00 | 1.00 | 1.00 | 1.00 | 1.00 | 0.78 | 0.95 | 1.09 | 1.00 | 1.00 | 1.00 |
| Cpne5 | 1.00 | 0.85 | 1.15 | 1.00 | 1.00 | 1.00 | 1.00 | 1.00 | 1.00 | 0.66 | 1.00 | 1.00 |
| Cr2 | 3.78 | 5.18 | 4.17 | 1.42 | 1.68 | 1.26 | 1.00 | 1.00 | 1.00 | 1.00 | 1.05 | 0.94 |
| Crct1 | 1.12 | 7.24 | 1.02 | 1.00 | 1.00 | 1.00 | 1.00 | 1.00 | 1.00 | 0.94 | 1.06 | 1.11 |
| Crhbp | 1.00 | 1.07 | 0.84 | 1.00 | 1.00 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 | 1.00 | 1.19 | 1.10 |
| Crlf1 | 1.00 | 1.02 | 1.00 | 1.00 | 1.00 | 1.00 | 0.95 | 0.80 | 0.92 | 0.93 | 0.82 | 0.98 |
| Crtam | 0.93 | 1.33 | 1.25 | 1.00 | 1.00 | 1.00 | 1.00 | 1.00 | 1.00 | 1.00 | 0.86 | 0.97 |
| Cryba4 | 1.09 | 1.07 | 1.00 | 1.08 | 1.17 | 0.96 | 1.00 | 1.00 | 1.00 | 0.56 | 1.00 | 1.00 |
| Csrp3 | 4.80 | 5.97 | 3.93 | 1.43 | 1.14 | 1.02 | 1.00 | 1.00 | 1.00 | 1.11 | 1.00 | 1.00 |
| Cst11 | 1.00 | 1.00 | 1.00 | 1.00 | 1.00 | 1.00 | 1.00 | 1.00 | 1.00 | 1.00 | 1.00 | 1.00 |
| Ctgf | 2.02 | 1.83 | 2.66 | 1.00 | 1.00 | 1.00 | 1.00 | 0.95 | 1.03 | 1.27 | 1.02 | 0.97 |
| Ctrb1 | 0.29 | 0.71 | 0.07 | 1.00 | 1.00 | 1.00 | 0.89 | 1.00 | 0.99 | 1.02 | 1.00 | 1.00 |
| Ctse | 6.76 | 0.28 | 0.59 | 1.76 | 0.51 | 1.04 | 1.00 | 0.80 | 1.00 | 0.79 | 0.94 | 0.91 |
| Ctss | 1.22 | 1.95 | 1.33 | 1.16 | 1.81 | 1.16 | 0.88 | 0.79 | 0.65 | 1.02 | 1.00 | 0.99 |
| Cuzd1 | 1.00 | 1.00 | 1.00 | 1.00 | 1.00 | 1.00 | 0.96 | 1.25 | 1.30 | 1.00 | 1.38 | 0.90 |
| Cxcl13 | 1.94 | 5.89 | 5.98 | 1.00 | 1.00 | 1.00 | 0.90 | 1.64 | 0.80 | 1.64 | 0.97 | 1.23 |
| Cxcl15 | 1.00 | 1.18 | 1.00 | 1.00 | 1.00 | 1.00 | 1.00 | 1.00 | 1.00 | 1.00 | 1.03 | 0.93 |
| Cxcl17 | 2.20 | 5.02 | 0.93 | 1.00 | 1.00 | 1.00 | 1.00 | 1.00 | 1.00 | 1.00 | 1.00 | 1.00 |
| Cxcl2 | 0.59 | 0.70 | 0.94 | 1.00 | 1.00 | 1.00 | 1.00 | 1.00 | 1.00 | 2.04 | 1.00 | 1.00 |
| Cxcl3 | 0.73 | 0.96 | 0.99 | 1.00 | 1.00 | 1.00 | 1.00 | 1.00 | 1.00 | 1.00 | 1.00 | 1.00 |
| Cxcr2 | 1.37 | 2.27 | 2.99 | 1.04 | 1.23 | 1.06 | 1.00 | 1.00 | 1.00 | 0.94 | 1.10 | 0.71 |
| Cxcr4 | 0.87 | 0.85 | 0.91 | 1.19 | 0.87 | 1.06 | 0.94 | 0.71 | 1.00 | 1.21 | 1.00 | 1.00 |
| Cxcr5 | 2.60 | 4.45 | 3.18 | 1.08 | 1.30 | 1.02 | 1.00 | 1.00 | 1.00 | 1.00 | 1.90 | 0.96 |
| Cxcr6 | 0.98 | 0.78 | 1.02 | 0.94 | 1.07 | 0.76 | 1.00 | 1.00 | 1.00 | 0.78 | 1.03 | 1.04 |
| Cyb561 | 1.03 | 1.36 | 1.29 | 1.00 | 1.00 | 1.00 | 1.20 | 1.15 | 0.92 | 1.05 | 0.91 | 0.93 |
| Cyp2a5 | 2.15 | 2.27 | 0.63 | 1.00 | 1.00 | 1.00 | 1.00 | 1.00 | 1.00 | 1.00 | 1.00 | 1.00 |
| Cyp2e1 | 2.65 | 1.81 | 2.19 | 1.00 | 1.00 | 1.00 | 0.82 | 0.88 | 1.29 | 1.53 | 0.89 | 1.01 |
| Cyp2f2 | 0.86 | 6.79 | 1.02 | 1.00 | 1.00 | 1.00 | 1.00 | 1.00 | 1.00 | 1.27 | 1.00 | 1.00 |
| Cyp46a1 | 1.00 | 1.00 | 1.00 | 1.00 | 1.00 | 1.00 | 1.00 | 1.00 | 1.00 | 0.81 | 1.00 | 1.00 |
| Cyp4a10 | 1.00 | 1.00 | 1.00 | 1.00 | 1.00 | 1.00 | 1.00 | 1.00 | 1.00 | 1.00 | 1.00 | 1.00 |
| Cyp4a14 | 1.00 | 1.00 | 1.00 | 1.00 | 1.00 | 1.00 | 1.00 | 1.00 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 | 1.00 | 1.00 | 1.00 |
| Dck | 0.82 | 0.71 | 0.84 | 1.10 | 1.04 | 1.04 | 1.00 | 1.00 | 1.00 | 0.83 | 1.00 | 1.00 |
| Ddit4 | 1.06 | 1.19 | 2.06 | 1.67 | 1.50 | 2.83 | 1.69 | 0.86 | 1.71 | 2.00 | 1.00 | 1.00 |
| Defb1 | 1.89 | 1.08 | 1.36 | 1.00 | 1.00 | 1.00 | 1.00 | 1.00 | 1.00 | 1.14 | 1.00 | 1.00 |
| Defb10 | 1.00 | 1.00 | 1.00 | 1.00 | 1.00 | 1.00 | 1.00 | 1.00 | 1.00 | 1.00 | 1.00 | 1.00 |
| Defb12 | 1.00 | 1.00 | 1.00 | 1.00 | 1.00 | 1.00 | 1.00 | 1.00 | 1.00 | 1.00 | 1.20 | 1.15 |
| Defb13 | 1.00 | 1.00 | 1.00 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 | 1.00 | 1.00 | 1.00 |
| Defb19 | 1.34 | 1.04 | 0.99 | 1.00 | 1.00 | 1.00 | 1.00 | 1.00 | 1.00 | 1.00 | 1.34 | 1.00 |
| Defb2 | 1.00 | 1.00 | 1.00 | 1.00 | 1.00 | 1.00 | 1.00 | 1.00 | 1.00 | 1.27 | 1.00 | 1.00 |
| Defb20 | 1.00 | 1.00 | 1.00 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 | 1.00 | 1.00 | 1.00 |
| Defb23 | 1.00 | 1.00 | 1.00 | 1.00 | 1.00 | 1.00 | 1.00 | 1.00 | 1.00 | 1.00 | 1.00 | 1.00 |
| Defb25 | 1.10 | 1.00 | 1.00 | 1.00 | 1.00 | 1.00 | 1.00 | 1.00 | 1.00 | 1.00 | 1.00 | 1.00 |
| Defb26 | 1.00 | 1.00 | 1.00 | 1.00 | 1.00 | 1.00 | 1.00 | 1.00 | 1.00 | 1.00 | 1.00 | 1.00 |
| Defb28 | 1.00 | 1.00 | 1.00 | 1.00 | 1.00 | 1.00 | 1.00 | 1.00 | 1.00 | 1.00 | 1.00 | 1.00 |
| Defb29 | 1.00 | 1.00 | 1.00 | 1.00 | 1.00 | 1.00 | 1.00 | 1.00 | 1.00 | 1.00 | 0.81 | 1.00 |
| Defb30 | 1.00 | 1.00 | 1.00 | 1.00 | 1.00 | 1.00 | 1.00 | 1.00 | 1.00 | 1.00 | 1.00 | 1.00 |
| Defb35 | 1.00 | 1.00 | 1.00 | 1.00 | 1.00 | 1.00 | 1.00 | 1.00 | 1.00 | 1.00 | 1.00 | 1.00 |

Fig. 31- 37

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Defb39 | 1.00 | 1.00 | 1.00 | 0.88 | 1.00 | 1.00 | 1.00 | 1.00 | 1.00 |
| Defb4 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 |
| Defb42 | 1.00 | 1.00 | 1.00 | 0.86 | 2.43 | 1.52 | 1.00 | 1.00 | 1.00 |
| Defb45 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 |
| Depdc7 | 1.07 | 1.29 | 1.27 | 1.15 | 0.75 | 1.02 | 0.62 | 0.69 | 1.18 |
| Derl3 | 1.72 | 1.00 | 1.00 | 1.03 | 0.75 | 1.18 | 1.04 | 0.86 | 2.87 |
| Dio1 | 1.00 | 1.00 | 1.00 | 1.25 | 1.48 | 0.82 | 5.16 | 1.11 | 0.78 |
| Dio2 | 1.32 | 5.37 | 3.53 | 1.00 | 1.00 | 1.00 | 1.00 | 1.00 | 1.00 |
| Dlgap5 | 1.00 | 1.22 | 1.00 | 1.00 | 1.00 | 1.00 | 1.00 | 1.52 | 1.00 |
| Dmrtc1a | 1.00 | 1.00 | 1.00 | 1.00 | 1.00 | 1.00 | 1.00 | 1.00 | 1.00 |
| Dnase1l2 | 1.09 | 1.16 | 0.98 | 0.96 | 1.04 | 1.11 | 1.00 | 1.00 | 1.00 |
| DQ267100 | 1.00 | 22.50 | 1.00 | 1.00 | 1.00 | 1.00 | 1.00 | 1.00 | 1.00 |
| DQ267101 | 1.00 | 1.00 | 1.00 | 1.00 | 1.00 | 1.00 | 1.00 | 1.00 | 1.00 |
| DQ267102 | 1.00 | 1.00 | 1.00 | 1.00 | 1.00 | 1.00 | 1.00 | 1.00 | 1.00 |
| Dtl | 1.02 | 1.07 | 1.00 | 1.00 | 1.00 | 1.00 | 1.00 | 1.58 | 1.00 |
| Dusp2 | 1.51 | 1.87 | 1.00 | 1.00 | 1.08 | 1.00 | 1.00 | 2.28 | 1.00 |
| E2f8 | 1.12 | 1.53 | 1.00 | 1.00 | 1.00 | 1.00 | 0.84 | 1.59 | 1.50 |
| E330020D12Rik | 1.00 | 1.00 | 1.00 | 1.00 | 1.00 | 1.00 | 1.00 | 1.08 | 1.00 |
| Ear7 | 1.00 | 1.00 | 1.00 | 1.00 | 1.09 | 1.00 | 1.00 | 1.95 | 1.00 |
| Ebf1 | 1.03 | 1.28 | 1.08 | 1.17 | 1.55 | 1.08 | 1.00 | 3.19 | 1.00 |
| Eddm3b | 1.00 | 1.00 | 1.00 | 1.44 | 1.02 | 1.00 | 1.00 | 1.00 | 1.00 |
| Eef1a2 | 0.76 | 0.64 | 0.72 | 1.00 | 1.00 | 1.00 | 1.00 | 1.00 | 1.00 |
| Egr2 | 3.62 | 2.86 | 1.52 | 1.00 | 1.00 | 1.00 | 1.00 | 1.00 | 1.00 |
| Eif3j1 | 1.00 | 1.00 | 1.00 | 3.59 | 3.87 | 1.00 | 1.06 | 0.26 | 1.00 |
| Eln | 1.28 | 6.17 | 3.97 | 1.14 | 1.05 | 1.36 | 1.00 | 1.01 | 1.00 |
| Elovl2 | 1.00 | 1.00 | 1.00 | 0.85 | 0.93 | 1.14 | 0.99 | 0.74 | 1.05 |
| Elovl3 | 1.00 | 1.00 | 1.00 | 1.00 | 1.00 | 1.00 | 0.38 | 0.81 | 7.59 |
| Enpp1 | 1.52 | 2.52 | 2.31 | 1.18 | 1.00 | 0.80 | 1.25 | 1.20 | 0.70 |
| Esco2 | 1.00 | 1.01 | 1.00 | 1.00 | 1.00 | 1.00 | 1.00 | 1.74 | 1.00 |
| Esrp2 | 1.00 | 1.00 | 1.00 | 0.99 | 0.77 | 1.24 | 0.96 | 0.89 | 1.14 |
| Ezh2 | 1.25 | 1.88 | 1.03 | 1.02 | 1.17 | 1.05 | 1.05 | 4.54 | 0.92 |
| F10 | 5.15 | 0.99 | 1.00 | 1.00 | 1.00 | 1.00 | 1.05 | 0.87 | 0.86 |
| Faim2 | 1.00 | 1.00 | 1.00 | 1.00 | 1.00 | 1.00 | 1.00 | 1.00 | 1.00 |
| Fam101a | 1.00 | 1.00 | 1.00 | 0.97 | 1.41 | 1.02 | 1.00 | 1.00 | 1.00 |
| Fam129c | 1.37 | 4.85 | 1.25 | 1.00 | 2.28 | 1.09 | 1.00 | 7.16 | 1.00 |
| Fam64a | 1.00 | 2.94 | 1.00 | 1.00 | 1.00 | 1.00 | 1.00 | 1.93 | 1.00 |
| Fam84a | 1.00 | 1.00 | 1.00 | 1.34 | 1.25 | 0.87 | 0.92 | 1.00 | 1.00 |
| Fcgr4 | 3.14 | 4.98 | 1.38 | 1.00 | 2.03 | 0.90 | 1.22 | 2.39 | 0.69 |
| Fcho1 | 1.00 | 1.12 | 1.00 | 1.00 | 1.00 | 1.00 | 1.00 | 2.11 | 1.00 |
| Fcrla | 1.41 | 2.03 | 1.00 | 1.00 | 1.04 | 1.00 | 1.00 | 2.26 | 1.00 |
| Fetub | 0.83 | 1.00 | 1.52 | 1.00 | 1.01 | 1.00 | 1.14 | 1.00 | 0.75 |
| Ffar1 | 1.00 | 1.00 | 1.00 | 1.00 | 1.00 | 1.00 | 1.00 | 1.00 | 1.00 |
| Fggy | 0.70 | 1.15 | 1.00 | 0.99 | 0.74 | 0.88 | 0.89 | 0.81 | 0.87 |
| Fignl1 | 1.34 | 1.49 | 1.00 | 1.00 | 1.00 | 1.00 | 1.00 | 1.82 | 1.00 |
| Fmod | 0.62 | 4.94 | 6.94 | 0.99 | 0.96 | 0.67 | 1.00 | 1.00 | 1.00 |
| Fos | 7.13 | 3.25 | 5.16 | 1.22 | 0.94 | 1.00 | 1.24 | 1.78 | 0.81 |
| Foxi1 | 1.00 | 1.00 | 1.00 | 1.52 | 0.95 | 0.95 | 1.00 | 1.00 | 1.00 |
| Foxm1 | 1.28 | 2.34 | 1.00 | 1.00 | 1.11 | 1.00 | 1.00 | 2.46 | 1.00 |
| Fut1 | 1.00 | 1.00 | 1.00 | 1.00 | 1.00 | 1.00 | 1.00 | 1.00 | 1.00 |
| Gal3st4 | 1.00 | 1.10 | 1.00 | 1.00 | 1.00 | 1.00 | 1.00 | 1.00 | 1.00 |
| Galnt12 | 1.00 | 1.11 | 1.00 | 1.00 | 1.01 | 1.00 | 1.00 | 1.00 | 1.00 |
| Gbp2b | 1.00 | 1.00 | 1.07 | 1.00 | 1.00 | 1.00 | 0.97 | 1.27 | 0.73 |
| Gc | 1.00 | 1.00 | 1.00 | 1.31 | 0.44 | 0.45 | 1.01 | 1.04 | 0.94 |
| Gdf15 | 9.95 | 2.92 | 34.55 | 0.72 | 1.10 | 1.06 | 1.14 | 0.97 | 0.77 |
| Gdf6 | 1.56 | 5.87 | 2.18 | 1.00 | 1.00 | 1.00 | 1.00 | 1.00 | 1.00 |
| Gdpd3 | 8.91 | 1.20 | 20.68 | 4.00 | 1.11 | 3.73 | 3.40 | 1.00 | 4.47 |
| Gfra1 | 0.71 | 1.21 | 0.61 | 1.73 | 0.23 | 0.43 | 1.45 | 0.72 | 1.00 |
| Gh | 1.00 | 1.00 | 1.00 | 1.00 | 1.00 | 1.00 | 1.00 | 1.00 | 1.00 |
| Gldc | 1.00 | 1.00 | 1.00 | 1.06 | 0.64 | 0.96 | 1.26 | 1.19 | 1.55 |
| Glycam1 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 |

Fig. 31-38

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Defb39 | 1.00 | 1.00 | 1.00 | 1.00 | 1.00 | 1.00 | 1.00 | 1.00 | 1.00 |
| Defb4 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 |
| Defb42 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 |
| Depdc7 | 1.34 | 1.46 | 1.12 | 1.72 | 0.99 | 1.16 | 1.06 | 0.83 | 1.04 |
| Derl3 | 0.64 | 0.59 | 0.84 | 1.00 | 1.00 | 1.00 | 0.64 | 1.37 | 0.71 |
| Dio1 | 1.00 | 1.00 | 1.00 | 1.00 | 1.00 | 1.00 | 1.00 | 1.00 | 1.00 |
| Dio2 | 1.05 | 3.25 | 1.57 | 1.00 | 1.00 | 1.00 | 1.00 | 1.00 | 1.00 |
| Dlgap5 | 1.27 | 6.72 | 1.00 | 1.00 | 1.00 | 1.00 | 1.05 | 1.41 | 3.09 |
| Dmrtc1a | 1.00 | 1.00 | 1.00 | 1.00 | 1.00 | 1.00 | 1.00 | 1.00 | 1.00 |
| Dnase1l2 | 1.16 | 1.11 | 1.27 | 1.17 | 1.00 | 0.81 | 1.69 | 0.99 | 1.30 |
| DQ267100 | 1.00 | 0.05 | 0.05 | 1.00 | 1.00 | 1.00 | 1.00 | 1.00 | 1.00 |
| DQ267101 | 1.00 | 1.00 | 1.00 | 1.00 | 1.00 | 1.00 | 1.00 | 1.00 | 1.00 |
| DQ267102 | 1.00 | 0.05 | 1.00 | 1.00 | 1.00 | 1.00 | 1.00 | 1.00 | 1.00 |
| Dtl | 1.54 | 5.07 | 1.00 | 1.00 | 1.00 | 1.00 | 0.64 | 1.30 | 2.82 |
| Dusp2 | 0.66 | 11.55 | 0.69 | 1.05 | 0.81 | 1.00 | 1.26 | 1.20 | 0.60 |
| E2f8 | 1.51 | 6.11 | 1.00 | 1.00 | 1.00 | 1.00 | 1.00 | 1.37 | 3.21 |
| E330020D12Rik | 1.00 | 5.05 | 1.00 | 1.00 | 1.00 | 1.00 | 2.41 | 0.85 | 0.94 |
| Ear7 | 1.00 | 6.83 | 1.00 | 1.00 | 0.67 | 1.00 | 1.06 | 1.65 | 0.82 |
| Ebf1 | 0.87 | 7.29 | 0.92 | 1.12 | 1.22 | 1.18 | 1.02 | 0.85 | 0.83 |
| Eddm3b | 1.00 | 1.00 | 1.00 | 1.00 | 1.00 | 1.00 | 1.00 | 1.00 | 1.00 |
| Eef1a2 | 0.59 | 1.05 | 1.17 | 0.95 | 0.94 | 1.12 | 1.00 | 1.00 | 1.00 |
| Egr2 | 0.97 | 1.04 | 1.42 | 1.00 | 1.00 | 1.00 | 0.93 | 1.29 | 0.64 |
| Eif3j1 | 1.00 | 1.00 | 2.30 | 1.86 | 0.62 | 9.76 | 0.23 | 4.89 | 6.49 |
| Eln | 1.70 | 3.39 | 2.25 | 1.06 | 0.81 | 1.60 | 0.97 | 1.08 | 1.26 |
| Elovl2 | 1.00 | 1.00 | 1.00 | 1.00 | 1.00 | 1.00 | 1.00 | 1.00 | 1.00 |
| Elovl3 | 1.00 | 1.00 | 1.00 | 1.00 | 1.00 | 1.00 | 1.00 | 1.00 | 1.00 |
| Enpp1 | 1.15 | 1.12 | 0.99 | 0.99 | 0.79 | 0.46 | 0.99 | 1.12 | 0.83 |
| Esco2 | 1.34 | 6.60 | 1.00 | 1.00 | 1.00 | 1.00 | 1.14 | 1.52 | 3.27 |
| Esrp2 | 1.16 | 0.76 | 1.26 | 1.00 | 1.00 | 1.00 | 1.72 | 0.94 | 1.00 |
| Ezh2 | 1.25 | 6.90 | 1.03 | 0.89 | 1.21 | 0.84 | 0.82 | 1.37 | 1.85 |
| F10 | 1.75 | 1.00 | 1.58 | 1.00 | 1.00 | 1.00 | 0.62 | 0.68 | 0.72 |
| Faim2 | 0.76 | 0.33 | 0.81 | 1.00 | 1.00 | 1.00 | 1.00 | 1.00 | 1.00 |
| Fam101a | 0.47 | 1.39 | 1.63 | 1.00 | 1.00 | 1.00 | 1.00 | 1.00 | 1.00 |
| Fam129c | 1.22 | 30.64 | 1.07 | 1.00 | 2.02 | 0.96 | 0.98 | 0.69 | 0.73 |
| Fam64a | 1.32 | 10.49 | 1.00 | 1.00 | 1.00 | 1.00 | 0.53 | 1.25 | 0.78 |
| Fam84a | 0.86 | 0.82 | 0.84 | 1.00 | 1.00 | 1.00 | 1.35 | 1.06 | 0.77 |
| Fcgr4 | 0.99 | 2.42 | 0.84 | 1.00 | 1.00 | 1.00 | 1.21 | 1.94 | 0.98 |
| Fcho1 | 0.56 | 7.11 | 0.85 | 1.00 | 1.00 | 1.00 | 0.88 | 1.12 | 1.27 |
| Fcrla | 0.37 | 7.03 | 0.93 | 1.00 | 1.00 | 1.00 | 0.97 | 0.81 | 0.88 |
| Fetub | 1.15 | 0.96 | 0.79 | 1.00 | 1.00 | 1.00 | 1.00 | 1.00 | 1.00 |
| Ffar1 | 1.00 | 1.00 | 0.84 | 1.00 | 1.00 | 1.00 | 0.98 | 1.03 | 0.92 |
| Fggy | 0.92 | 1.07 | 1.00 | 0.81 | 1.22 | 1.00 | 0.80 | 1.04 | 1.00 |
| Fignl1 | 1.79 | 6.10 | 1.00 | 1.00 | 1.00 | 1.00 | 0.79 | 1.15 | 2.62 |
| Fmod | 0.39 | 1.12 | 0.73 | 1.21 | 0.95 | 1.00 | 0.57 | 0.95 | 0.44 |
| Fos | 2.02 | 0.59 | 2.60 | 1.97 | 3.46 | 0.77 | 1.59 | 1.57 | 0.97 |
| Foxi1 | 1.00 | 1.00 | 1.00 | 1.00 | 1.00 | 1.00 | 1.00 | 1.00 | 1.00 |
| Foxm1 | 1.77 | 5.65 | 0.93 | 1.00 | 1.00 | 1.00 | 1.03 | 1.47 | 2.22 |
| Fut1 | 1.00 | 1.00 | 1.00 | 1.00 | 1.00 | 1.00 | 0.95 | 0.98 | 1.00 |
| Gal3st4 | 1.00 | 1.00 | 1.00 | 1.00 | 1.00 | 1.00 | 1.00 | 1.00 | 1.00 |
| Galnt12 | 0.79 | 1.96 | 0.89 | 1.00 | 1.00 | 1.00 | 1.06 | 0.97 | 0.88 |
| Gbp2b | 0.81 | 0.99 | 1.23 | 1.00 | 1.00 | 1.00 | 1.02 | 0.71 | 0.84 |
| Gc | 1.00 | 1.00 | 1.00 | 1.00 | 1.00 | 1.00 | 1.00 | 1.00 | 1.00 |
| Gdf15 | 2.75 | 1.34 | 1.87 | 1.00 | 1.00 | 1.00 | 0.57 | 1.38 | 0.93 |
| Gdf6 | 1.00 | 1.75 | 0.84 | 1.00 | 1.00 | 1.00 | 0.28 | 0.76 | 2.14 |
| Gdpd3 | 6.06 | 1.18 | 9.76 | 8.85 | 0.97 | 12.54 | 11.79 | 0.86 | 13.63 |
| Gfra1 | 0.96 | 1.58 | 0.95 | 1.37 | 0.94 | 1.11 | 1.00 | 1.00 | 1.00 |
| Gh | 1.00 | 1.43 | 1.00 | 1.00 | 1.00 | 1.00 | 1.00 | 1.00 | 1.00 |
| Gldc | 1.00 | 10.76 | 1.00 | 1.00 | 1.00 | 1.00 | 1.00 | 1.00 | 1.00 |
| Glycam1 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 |

Fig. 31- 39

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Defb39 | 1.00 | 1.00 | 1.00 | 1.00 | 364.89 | 1.00 | 1.00 | 1.00 | 0.97 |
| Defb4 | 1.00 | 1.00 | 1.00 | 1.00 | 1.00 | 1.00 | 1.00 | 1.00 | 1.00 |
| Defb41 | 1.00 | 1.00 | 1.00 | 1.00 | 67.82 | 1.00 | 0.95 | 0.69 | 0.85 |
| Defb42 | 1.00 | 1.00 | 1.00 | 1.00 | 276.09 | 1.00 | 1.05 | 1.23 | 1.00 |
| Defb45 | 1.00 | 1.00 | 1.00 | 1.00 | 104.46 | 1.00 | 0.81 | 1.09 | 1.03 |
| Defb47 | 1.00 | 1.00 | 1.00 | 1.00 | 16.90 | 1.00 | 1.00 | 0.98 | 1.00 |
| Defb48 | 1.00 | 1.00 | 1.00 | 1.00 | 20.41 | 1.00 | 1.00 | 1.00 | 1.00 |
| Depdc7 | 1.05 | 0.92 | 1.31 | 0.92 | 6.98 | 1.33 | 1.10 | 0.93 | 0.82 |
| Derl3 | 0.57 | 0.68 | 1.33 | 0.82 | 13.18 | 0.73 | 0.87 | 1.01 | 0.85 |
| Dio1 | 1.00 | 1.00 | 1.00 | 1.00 | 0.82 | 1.00 | 1.06 | 1.10 | 0.98 |
| Dio2 | 1.42 | 0.75 | 1.05 | 1.00 | 1.00 | 1.00 | 1.09 | 1.06 | 0.82 |
| Dlgap5 | 1.00 | 1.00 | 1.00 | 1.00 | 1.00 | 1.00 | 1.02 | 0.90 | 1.06 |
| Dmrtc1a | 0.90 | 1.15 | 0.96 | 1.00 | 7.93 | 1.00 | 0.91 | 0.99 | 0.97 |
| Dnase1l2 | 1.31 | 0.96 | 1.11 | 1.01 | 10.07 | 0.93 | 1.03 | 0.77 | 1.14 |
| DQ267100 | 0.54 | 1.72 | 0.87 | 1.00 | 1.00 | 1.00 | 1.00 | 0.04 | 1.00 |
| DQ267101 | 1.00 | 1.00 | 56.12 | 1.00 | 1.00 | 1.00 | 1.00 | 1.00 | 1.00 |
| DQ267102 | 1.00 | 3.00 | 0.51 | 1.00 | 1.00 | 28.53 | 1.00 | 1.00 | 1.00 |
| Dtl | 0.78 | 1.61 | 0.85 | 1.00 | 1.00 | 1.00 | 1.01 | 0.94 | 0.99 |
| Dusp2 | 1.00 | 1.74 | 1.00 | 1.00 | 1.51 | 1.00 | 0.96 | 1.04 | 0.80 |
| E2f8 | 1.00 | 1.10 | 1.00 | 1.00 | 1.00 | 1.00 | 1.04 | 1.02 | 1.04 |
| E330020D12Rik | 1.00 | 1.00 | 1.00 | 1.00 | 1.00 | 1.00 | 1.00 | 1.00 | 1.00 |
| Ear7 | 1.00 | 1.00 | 1.00 | 1.00 | 1.00 | 1.00 | 1.00 | 1.00 | 1.00 |
| Ebf1 | 1.07 | 1.22 | 0.93 | 1.06 | 0.92 | 0.84 | 1.00 | 1.00 | 1.00 |
| Eddm3b | 1.00 | 1.00 | 1.00 | 0.59 | 17.72 | 1.00 | 1.00 | 1.00 | 1.00 |
| Eef1a2 | 0.96 | 0.95 | 1.06 | 1.00 | 1.00 | 1.00 | 1.00 | 1.00 | 1.00 |
| Egr2 | 2.80 | 1.33 | 1.22 | 0.84 | 16.99 | 0.70 | 1.00 | 1.00 | 1.00 |
| Eif3j1 | 0.90 | 1.00 | 0.20 | 1.00 | 1.00 | 1.00 | 0.87 | 1.82 | 0.97 |
| Eln | 1.19 | 0.78 | 1.00 | 1.49 | 0.98 | 1.31 | 1.03 | 0.90 | 0.90 |
| Elovl2 | 0.95 | 0.97 | 0.99 | 1.00 | 5.37 | 1.00 | 1.03 | 1.00 | 0.96 |
| Elovl3 | 1.00 | 1.00 | 1.00 | 1.00 | 1.00 | 1.00 | 1.00 | 1.00 | 1.00 |
| Enpp1 | 0.82 | 0.98 | 0.99 | 1.12 | 43.88 | 0.73 | 1.00 | 1.00 | 1.00 |
| Esco2 | 1.00 | 1.00 | 1.00 | 1.00 | 1.00 | 1.00 | 0.99 | 1.08 | 0.96 |
| Esrp2 | 1.00 | 1.00 | 1.00 | 1.00 | 9.87 | 1.00 | 1.00 | 1.00 | 1.00 |
| Ezh2 | 1.06 | 1.71 | 0.91 | 1.14 | 0.90 | 0.83 | 1.03 | 1.01 | 0.98 |
| F10 | 1.00 | 1.00 | 1.00 | 3.13 | 0.67 | 0.17 | 1.00 | 1.00 | 1.00 |
| Faim2 | 0.96 | 0.96 | 1.02 | 1.00 | 6.93 | 1.00 | 1.00 | 1.00 | 1.00 |
| Fam101a | 1.00 | 1.00 | 1.00 | 1.00 | 5.23 | 1.00 | 1.00 | 1.00 | 1.00 |
| Fam129c | 1.23 | 2.80 | 1.14 | 1.31 | 2.21 | 0.95 | 0.94 | 1.11 | 0.98 |
| Fam64a | 1.00 | 1.24 | 1.00 | 1.00 | 1.00 | 0.84 | 1.00 | 1.00 | 1.00 |
| Fam84a | 1.07 | 0.96 | 0.97 | 0.56 | 5.13 | 0.68 | 1.20 | 1.05 | 1.00 |
| Fcgr4 | 1.00 | 1.00 | 1.00 | 1.88 | 1.41 | 0.52 | 1.00 | 1.00 | 1.00 |
| Fcho1 | 1.06 | 1.07 | 0.98 | 1.00 | 1.20 | 0.90 | 1.00 | 1.00 | 1.00 |
| Fcrla | 1.00 | 1.00 | 1.00 | 1.00 | 1.39 | 0.31 | 1.17 | 0.88 | 0.88 |
| Fetub | 1.00 | 1.00 | 1.00 | 1.00 | 1.54 | 1.00 | 1.21 | 1.33 | 1.42 |
| Ffar1 | 1.00 | 1.00 | 1.00 | 1.00 | 1.00 | 1.00 | 1.00 | 1.00 | 1.00 |
| Fggy | 0.88 | 1.03 | 1.00 | 0.73 | 0.63 | 0.49 | 0.88 | 1.11 | 0.85 |
| Fignl1 | 1.00 | 1.22 | 1.00 | 1.00 | 1.00 | 1.00 | 1.02 | 0.97 | 1.02 |
| Fmod | 0.93 | 1.20 | 1.05 | 0.79 | 1.03 | 0.46 | 0.62 | 0.80 | 0.64 |
| Fos | 3.86 | 1.43 | 1.10 | 2.29 | 1.67 | 0.51 | 1.00 | 1.00 | 1.00 |
| Foxi1 | 1.00 | 1.00 | 1.00 | 1.00 | 6.53 | 1.00 | 1.00 | 1.00 | 1.00 |
| Foxm1 | 1.00 | 1.52 | 1.00 | 1.00 | 0.99 | 0.95 | 1.25 | 1.05 | 1.02 |
| Fut1 | 1.00 | 1.00 | 1.00 | 1.00 | 9.42 | 1.00 | 1.19 | 1.18 | 0.93 |
| Gal3st4 | 0.79 | 1.13 | 0.98 | 1.00 | 23.44 | 1.00 | 1.00 | 1.00 | 1.00 |
| Galnt12 | 1.00 | 1.00 | 1.00 | 0.79 | 11.34 | 0.74 | 0.96 | 0.93 | 0.98 |
| Gbp2b | 1.00 | 1.00 | 1.00 | 1.02 | 0.88 | 0.66 | 1.00 | 1.00 | 1.00 |
| Gc | 1.00 | 1.00 | 1.00 | 1.00 | 7.82 | 1.00 | 1.00 | 1.00 | 1.00 |
| Gdf15 | 1.00 | 1.00 | 1.00 | 1.09 | 1.11 | 1.00 | 1.00 | 1.00 | 1.00 |
| Gdf6 | 1.00 | 1.00 | 1.00 | 1.00 | 1.00 | 1.00 | 1.00 | 1.00 | 1.00 |
| Gdpd3 | 2.56 | 1.15 | 3.85 | 13.40 | 1.51 | 21.65 | 1.11 | 1.00 | 1.09 |
| Gfra1 | 0.89 | 1.10 | 1.03 | 1.00 | 31.06 | 1.00 | 0.94 | 1.27 | 1.03 |
| Gh | 6.43 | 243.04 | 1.00 | 1.00 | 1.00 | 1.00 | 1.00 | 1.00 | 1.00 |
| Gldc | 1.02 | 1.19 | 1.04 | 1.00 | 7.45 | 1.00 | 1.11 | 0.88 | 1.09 |
| Glycam1 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 157.77 | 1.00 | 1.00 | 1.00 | 1.00 |

Fig. 31- 40

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Defb39 | 1.00 | 1.00 | 1.00 | 1.00 | 1.00 | 1.00 | 1.00 | 1.00 | 1.00 | 1.00 | 1.00 | 1.00 |
| Defb4 | 1.00 | 11.22 | 1.00 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 | 1.00 | 1.00 | 1.00 |
| Defb42 | 0.91 | 0.92 | 0.83 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Depdc7 | 1.14 | 1.13 | 1.29 | 0.95 | 1.08 | 0.90 | 1.30 | 1.29 | 0.85 | 1.25 | 1.34 | 1.07 |
| Derl3 | 0.88 | 1.77 | 1.95 | 0.75 | 0.59 | 0.87 | 0.61 | 0.92 | 0.95 | 1.00 | 1.07 | 1.05 |
| Dio1 | 1.36 | 0.86 | 1.04 | 1.00 | 1.00 | 1.00 | 1.00 | 1.02 | 1.00 | 1.00 | 1.03 | 1.01 |
| Dio2 | 1.12 | 1.00 | 1.07 | 0.85 | 0.91 | 0.82 | 1.00 | 1.00 | 1.00 | 1.00 | 1.00 | 1.02 |
| Dlgap5 | 0.39 | 0.63 | 0.86 | 1.03 | 0.90 | 1.05 | 1.00 | 1.00 | 1.00 | 1.00 | 1.00 | 1.00 |
| Dmrtc1a | 1.00 | 0.90 | 1.00 | 1.00 | 1.00 | 1.00 | 1.00 | 1.00 | 1.00 | 1.00 | 1.00 | 1.00 |
| Dnase1l2 | 0.92 | 1.31 | 1.14 | 0.89 | 1.04 | 1.26 | 1.00 | 1.00 | 1.00 | 1.00 | 1.00 | 1.00 |
| DQ267100 | 1.00 | 1.00 | 1.00 | 1.00 | 1.00 | 1.00 | 1.00 | 1.00 | 1.00 | 1.00 | 1.23 | 1.01 |
| DQ267101 | 1.00 | 1.00 | 1.00 | 1.00 | 1.00 | 1.00 | 1.00 | 1.00 | 1.00 | 1.00 | 1.04 | 0.94 |
| DQ267102 | 1.00 | 1.00 | 1.00 | 1.00 | 1.00 | 1.00 | 1.00 | 1.00 | 1.00 | 1.00 | 1.25 | 1.18 |
| Dtl | 0.64 | 0.64 | 0.75 | 0.88 | 0.88 | 0.89 | 1.00 | 1.00 | 1.00 | 0.75 | 1.61 | 1.01 |
| Dusp2 | 0.99 | 0.94 | 1.01 | 1.02 | 0.61 | 0.80 | 0.97 | 0.87 | 1.00 | 0.77 | 0.70 | 0.78 |
| E2f8 | 0.39 | 0.57 | 0.98 | 0.92 | 1.00 | 1.03 | 1.00 | 1.00 | 1.00 | 0.89 | 0.68 | 1.19 |
| E330020D12Rik | 0.81 | 1.14 | 0.94 | 1.54 | 1.07 | 0.94 | 1.00 | 1.00 | 1.00 | 1.00 | 1.00 | 1.00 |
| Ear7 | 1.00 | 1.00 | 1.00 | 0.94 | 0.54 | 0.70 | 1.00 | 1.00 | 1.00 | 1.00 | 1.00 | 1.00 |
| Ebf1 | 1.46 | 1.86 | 2.35 | 0.89 | 0.56 | 0.71 | 1.00 | 1.00 | 1.00 | 0.92 | 1.35 | 1.08 |
| Eddm3b | 1.00 | 1.00 | 1.00 | 1.00 | 1.00 | 1.00 | 1.00 | 1.00 | 1.00 | 1.00 | 1.00 | 1.00 |
| Eef1a2 | 2.34 | 5.97 | 3.21 | 1.00 | 1.00 | 1.00 | 1.00 | 1.00 | 1.00 | 1.41 | 1.00 | 0.97 |
| Egr2 | 0.85 | 0.84 | 0.97 | 1.00 | 1.00 | 1.00 | 1.00 | 1.00 | 1.00 | 0.97 | 1.02 | 0.95 |
| Eif3j1 | 1.00 | 1.00 | 1.00 | 2.66 | 0.18 | 0.25 | 1.00 | 1.00 | 1.00 | 1.00 | 1.00 | 1.00 |
| Eln | 1.78 | 1.26 | 2.03 | 1.00 | 1.00 | 1.00 | 0.97 | 0.73 | 0.82 | 0.97 | 1.20 | 0.94 |
| Elovl2 | 1.00 | 1.00 | 1.00 | 1.00 | 1.00 | 1.00 | 1.00 | 1.00 | 1.00 | 1.00 | 1.00 | 1.00 |
| Elovl3 | 1.00 | 1.00 | 1.00 | 1.00 | 1.00 | 1.00 | 1.00 | 1.00 | 1.00 | 0.83 | 0.98 | 1.10 |
| Enpp1 | 1.24 | 1.62 | 1.56 | 1.01 | 0.95 | 1.02 | 1.10 | 1.11 | 1.00 | 0.71 | 1.04 | 0.70 |
| Esco2 | 0.36 | 0.65 | 0.98 | 0.93 | 1.07 | 1.07 | 1.00 | 1.00 | 1.00 | 0.86 | 1.61 | 0.98 |
| Esrp2 | 1.63 | 1.06 | 0.53 | 1.00 | 1.00 | 1.00 | 0.94 | 1.23 | 1.21 | 0.95 | 0.95 | 0.99 |
| Ezh2 | 0.72 | 0.63 | 0.89 | 0.93 | 0.85 | 0.92 | 0.93 | 0.85 | 1.00 | 1.23 | 0.94 | 1.03 |
| F10 | 0.86 | 3.82 | 1.00 | 1.08 | 2.21 | 1.23 | 1.00 | 1.00 | 1.00 | 1.00 | 1.00 | 1.00 |
| Faim2 | 1.00 | 1.00 | 1.00 | 1.00 | 1.00 | 1.00 | 1.00 | 1.00 | 1.00 | 1.14 | 1.00 | 1.00 |
| Fam101a | 1.00 | 1.00 | 1.00 | 1.00 | 1.00 | 1.00 | 1.00 | 1.00 | 1.00 | 1.01 | 0.99 | 1.00 |
| Fam129c | 1.59 | 0.89 | 1.17 | 1.38 | 0.30 | 0.90 | 1.00 | 1.00 | 1.00 | 0.77 | 1.18 | 1.02 |
| Fam64a | 0.36 | 0.60 | 0.96 | 1.01 | 0.87 | 0.83 | 1.00 | 1.00 | 1.00 | 0.94 | 1.07 | 0.88 |
| Fam84a | 0.95 | 1.36 | 1.03 | 1.00 | 1.00 | 1.00 | 1.00 | 1.00 | 1.00 | 1.01 | 1.00 | 0.99 |
| Fcgr4 | 1.02 | 8.17 | 1.37 | 1.19 | 1.32 | 1.08 | 1.00 | 1.00 | 1.00 | 1.00 | 1.03 | 0.90 |
| Fcho1 | 0.99 | 0.79 | 0.87 | 0.99 | 0.83 | 0.98 | 1.00 | 1.00 | 1.00 | 1.05 | 1.21 | 1.02 |
| Fcrla | 1.62 | 2.41 | 1.79 | 0.95 | 0.41 | 0.73 | 1.00 | 1.00 | 1.00 | 1.00 | 1.00 | 1.00 |
| Fetub | 1.32 | 6.12 | 1.00 | 1.00 | 1.00 | 1.00 | 1.21 | 1.89 | 0.51 | 1.16 | 1.00 | 1.00 |
| Ffar1 | 1.24 | 6.17 | 4.08 | 1.24 | 1.29 | 1.10 | 1.00 | 1.00 | 1.00 | 1.00 | 0.92 | 1.01 |
| Fggy | 1.10 | 5.20 | 0.95 | 1.14 | 2.53 | 1.00 | 1.04 | 1.04 | 1.00 | 1.00 | 1.00 | 1.00 |
| Fignl1 | 0.41 | 0.70 | 0.90 | 0.81 | 0.95 | 0.97 | 1.00 | 1.00 | 1.00 | 0.73 | 0.84 | 1.12 |
| Fmod | 1.18 | 2.40 | 2.75 | 1.00 | 1.00 | 1.00 | 1.05 | 1.82 | 1.54 | 0.99 | 1.22 | 1.05 |
| Fos | 1.12 | 1.28 | 1.02 | 1.06 | 2.10 | 1.22 | 1.00 | 1.00 | 1.00 | 0.41 | 1.19 | 0.98 |
| Foxi1 | 1.00 | 1.00 | 1.00 | 1.00 | 1.00 | 1.00 | 1.00 | 1.00 | 1.00 | 1.00 | 1.00 | 1.00 |
| Foxm1 | 0.42 | 0.64 | 1.00 | 0.94 | 1.01 | 1.11 | 1.00 | 1.00 | 1.00 | 0.96 | 0.91 | 1.10 |
| Fut1 | 0.85 | 0.86 | 1.46 | 1.00 | 1.00 | 1.00 | 0.72 | 0.98 | 0.84 | 0.81 | 1.05 | 0.89 |
| Gal3st4 | 1.26 | 0.81 | 0.90 | 1.13 | 1.02 | 0.75 | 1.00 | 1.00 | 1.00 | 0.98 | 0.96 | 1.05 |
| Galnt12 | 0.85 | 0.95 | 0.85 | 0.84 | 1.00 | 1.05 | 1.00 | 1.00 | 1.00 | 1.21 | 1.00 | 1.00 |
| Gbp2b | 1.86 | 5.09 | 0.90 | 1.00 | 1.26 | 1.00 | 1.00 | 1.00 | 1.00 | 1.00 | 1.15 | 1.10 |
| Gc | 1.00 | 1.00 | 1.00 | 1.00 | 1.00 | 1.00 | 1.00 | 0.96 | 1.00 | 1.00 | 1.00 | 1.00 |
| Gdf15 | 1.11 | 1.34 | 1.14 | 1.00 | 1.00 | 1.00 | 1.00 | 1.00 | 1.00 | 1.00 | 1.00 | 1.00 |
| Gdf6 | 1.00 | 1.00 | 1.00 | 1.00 | 1.00 | 1.00 | 1.00 | 1.00 | 1.00 | 1.00 | 1.00 | 1.00 |
| Gdpd3 | 1.22 | 1.05 | 4.35 | 0.97 | 0.86 | 5.30 | 1.00 | 1.00 | 1.00 | 0.87 | 1.00 | 1.00 |
| Gfra1 | 0.42 | 0.19 | 0.67 | 1.02 | 0.53 | 0.93 | 0.72 | 1.00 | 1.00 | 1.18 | 1.12 | 1.03 |
| Gh | 1.03 | 1.00 | 1.00 | 1.00 | 0.89 | 1.11 | 1.00 | 1.00 | 1.00 | 1.00 | 0.91 | 0.96 |
| Gldc | 1.00 | 1.00 | 1.00 | 1.00 | 1.00 | 1.00 | 1.00 | 1.00 | 1.00 | 0.92 | 1.16 | 1.06 |
| Glycam1 | 6.34 | 0.64 | 2.62 | 1.00 | 1.00 | 1.00 | 0.88 | 0.53 | 0.67 | 1.00 | 0.89 | 0.96 |
| Gm1110 | 1.00 | 1.00 | 1.00 | 1.00 | 1.00 | 1.00 | 1.00 | 1.00 | 1.00 | 1.00 | 1.03 | 1.05 |

Fig. 31-41

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Gm11346 | 1.00 | 1.00 | 1.00 | 1.00 | 1.00 | 1.00 | 1.00 | 1.00 | 1.00 |
| Gm12191 | 1.66 | 0.90 | 0.38 | 1.85 | 0.99 | 0.38 | 1.64 | 1.24 | 0.30 |
| Gm12238 | 1.00 | 0.32 | 4.98 | 1.00 | 1.00 | 1.00 | 3.32 | 1.00 | 1.00 |
| Gm15056 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 |
| Gm1987 | 0.13 | 1.00 | 1.00 | 1.00 | 1.00 | 1.00 | 1.00 | 1.00 | 1.00 |
| Gm2083 | 1.00 | 1.00 | 1.00 | 1.00 | 1.00 | 1.00 | 0.80 | 2.25 | 223.66 |
| Gm266 | 1.69 | 1.12 | 1.07 | 0.60 | 1.01 | 1.95 | 1.00 | 1.23 | 1.00 |
| Gm2663 | 1.00 | 1.00 | 1.00 | 1.00 | 1.00 | 1.00 | 1.00 | 1.00 | 1.00 |
| Gm4759 | 1.00 | 1.01 | 1.00 | 1.00 | 1.00 | 1.00 | 1.00 | 1.44 | 1.00 |
| Gm4846 | 1.00 | 1.00 | 1.00 | 1.00 | 1.00 | 1.00 | 1.00 | 1.00 | 1.00 |
| Gm4952 | 1.00 | 1.00 | 1.00 | 0.88 | 0.61 | 5.32 | 1.59 | 1.03 | 0.81 |
| Gm5483 | 10.70 | 1.00 | 1.00 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 |
| Gm6642 | 1.00 | 1.00 | 1.00 | 0.83 | 1.19 | 1.00 | 1.00 | 1.00 | 1.00 |
| Gm6792 | 1.00 | 1.00 | 1.00 | 1.00 | 1.00 | 1.00 | 1.00 | 1.00 | 1.00 |
| Gm7325 | 1.00 | 1.00 | 1.00 | 0.93 | 0.99 | 0.89 | 1.00 | 1.00 | 1.00 |
| Gm7334 | 1.15 | 1.00 | 0.98 | 1.46 | 1.08 | 0.99 | 1.34 | 1.04 | 1.00 |
| Gm933 | 1.00 | 1.00 | 1.00 | 1.00 | 1.00 | 1.00 | 1.00 | 1.00 | 1.00 |
| Gpc2 | 1.00 | 1.07 | 1.00 | 1.00 | 1.00 | 1.00 | 1.00 | 1.00 | 1.00 |
| Gpnmb | 0.74 | 38.19 | 3.62 | 1.00 | 1.00 | 1.00 | 1.00 | 1.00 | 1.00 |
| Gpr35 | 5.39 | 2.68 | 1.00 | 1.00 | 1.00 | 1.00 | 1.00 | 1.00 | 1.00 |
| Gpr82 | 1.00 | 1.00 | 1.00 | 1.00 | 1.00 | 1.00 | 1.00 | 1.00 | 1.00 |
| Gprc5a | 5.15 | 1.57 | 5.85 | 1.55 | 1.78 | 1.02 | 1.00 | 1.00 | 1.00 |
| Gpx5 | 1.00 | 1.00 | 1.00 | 1.00 | 1.00 | 1.00 | 1.00 | 1.00 | 1.00 |
| Grhl2 | 1.00 | 1.00 | 0.95 | 1.08 | 1.22 | 0.83 | 1.00 | 1.00 | 1.00 |
| Gtse1 | 1.00 | 1.85 | 1.00 | 1.00 | 1.00 | 1.00 | 1.00 | 4.08 | 1.00 |
| Gvin1 | 1.22 | 2.86 | 1.04 | 1.00 | 1.00 | 1.00 | 1.00 | 1.18 | 1.00 |
| H2-Ea-ps | 1.58 | 3.06 | 2.82 | 0.89 | 1.59 | 0.72 | 1.13 | 1.00 | 1.00 |
| H2-Eb1 | 1.36 | 2.20 | 2.62 | 0.78 | 1.48 | 1.11 | 0.70 | 1.00 | 0.69 |
| H2-M2 | 1.00 | 1.00 | 1.00 | 1.00 | 1.00 | 0.75 | 1.00 | 1.00 | 0.78 |
| Havcr1 | 1.00 | 1.00 | 1.00 | 0.44 | 5.36 | 0.50 | 1.08 | 0.65 | 1.20 |
| Hba-a1 | 0.60 | 1.12 | 5.24 | 1.20 | 6.24 | 2.14 | 0.85 | 3.26 | 1.05 |
| Hba-a2 | 0.48 | 1.92 | 5.40 | 1.33 | 7.00 | 1.67 | 1.10 | 2.50 | 1.15 |
| Hbb-b1 | 0.61 | 1.14 | 4.65 | 1.29 | 6.23 | 1.92 | 0.91 | 2.77 | 0.94 |
| Hbb-bh2 | 1.00 | 1.00 | 1.00 | 1.00 | 1.00 | 1.00 | 1.00 | 1.00 | 1.00 |
| Hbb-bs | 0.51 | 1.49 | 3.97 | 1.32 | 7.52 | 1.39 | 0.93 | 3.54 | 1.20 |
| Hbb-bt | 0.56 | 1.12 | 4.86 | 1.17 | 6.25 | 1.80 | 0.85 | 2.80 | 0.99 |
| Hmgb2 | 1.22 | 1.91 | 0.88 | 1.00 | 1.08 | 1.10 | 1.00 | 5.59 | 1.00 |
| Hmgcs2 | 0.98 | 1.18 | 1.03 | 5.59 | 3.22 | 1.00 | 1.41 | 0.75 | 1.02 |
| Hmmr | 1.00 | 2.37 | 1.00 | 1.00 | 1.00 | 1.00 | 1.00 | 1.77 | 1.00 |
| Hp | 2.39 | 0.54 | 8.61 | 0.80 | 0.36 | 5.73 | 1.11 | 2.19 | 0.91 |
| Hspa1a | 16.31 | 0.75 | 2.30 | 1.63 | 1.89 | 0.72 | 1.81 | 0.95 | 0.85 |
| Hspa1b | 14.89 | 0.78 | 2.34 | 1.73 | 1.91 | 0.72 | 1.67 | 0.97 | 0.85 |
| Ido1 | 1.00 | 1.00 | 1.00 | 1.00 | 1.00 | 1.00 | 1.00 | 1.00 | 1.00 |
| Ifi27l2a | 1.12 | 3.00 | 2.22 | 0.60 | 0.80 | 1.12 | 0.70 | 6.27 | 0.19 |
| Igfbp1 | 1.00 | 1.00 | 1.00 | 1.22 | 1.37 | 1.08 | 6.50 | 4.80 | 0.40 |
| Igj | 1.00 | 1.23 | 11.00 | 0.63 | 2.11 | 5.22 | 1.00 | 2.40 | 1.00 |
| Igll1 | 1.00 | 6.80 | 1.00 | 1.00 | 3.15 | 1.00 | 1.00 | 28.54 | 1.00 |
| Ikzf3 | 1.00 | 1.81 | 1.00 | 1.00 | 1.06 | 1.00 | 1.00 | 2.97 | 1.00 |
| Il12a | 1.00 | 1.00 | 1.00 | 1.00 | 1.00 | 1.00 | 1.00 | 1.28 | 1.00 |
| Il1b | 5.80 | 1.36 | 2.97 | 0.95 | 1.70 | 1.00 | 1.70 | 2.17 | 2.22 |
| Il1r2 | 16.88 | 1.00 | 1.00 | 1.00 | 1.00 | 1.00 | 1.00 | 1.00 | 1.00 |
| Il1rn | 7.48 | 3.25 | 1.00 | 1.00 | 1.00 | 1.00 | 1.00 | 1.10 | 1.00 |
| Il22ra2 | 1.00 | 1.00 | 1.00 | 1.00 | 1.00 | 1.00 | 1.00 | 1.00 | 1.00 |
| Il2ra | 1.00 | 1.04 | 1.00 | 1.00 | 1.00 | 1.00 | 1.00 | 1.36 | 1.00 |
| Il6 | 7.24 | 2.44 | 1.00 | 1.00 | 1.00 | 1.00 | 1.00 | 1.00 | 1.00 |
| Il7r | 1.00 | 6.71 | 1.06 | 1.00 | 1.62 | 1.00 | 1.00 | 5.46 | 1.00 |
| Inha | 0.76 | 0.83 | 0.71 | 1.08 | 1.00 | 1.08 | 1.00 | 1.00 | 1.00 |
| Inhbb | 10.60 | 2.07 | 2.83 | 1.38 | 1.05 | 1.00 | 1.34 | 1.00 | 0.94 |
| Inpp5d | 2.00 | 2.31 | 1.51 | 1.41 | 1.57 | 0.83 | 1.08 | 5.03 | 1.03 |
| Irf4 | 1.00 | 3.28 | 1.00 | 1.00 | 1.96 | 1.00 | 1.00 | 6.41 | 1.00 |

Fig. 31- 42

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Gm11346 | 0.61 | 1.00 | 0.72 | 1.00 | 1.00 | 1.00 | 0.76 | 0.58 | 0.85 |
| Gm12191 | 1.53 | 1.65 | 0.46 | 1.88 | 1.08 | 0.41 | 1.81 | 1.75 | 0.36 |
| Gm12238 | 1.00 | 6.57 | 1.00 | 0.14 | 5.08 | 2.85 | 3.44 | 0.72 | 0.40 |
| Gm15056 | 0.83 | 1.00 | 1.00 | 1.00 | 1.00 | 1.00 | 0.97 | 4.06 | 0.30 |
| Gm15386 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 |
| Gm1987 | 0.12 | 0.66 | 1.00 | 1.00 | 1.00 | 1.00 | 0.03 | 1.01 | 0.88 |
| Gm2083 | 1.00 | 1.00 | 1.00 | 1.00 | 1.00 | 1.00 | 1.00 | 1.00 | 1.00 |
| Gm266 | 1.00 | 4.72 | 1.00 | 1.00 | 1.00 | 1.00 | 0.87 | 1.00 | 1.00 |
| Gm2663 | 1.00 | 1.00 | 1.00 | 1.00 | 1.00 | 1.00 | 1.31 | 1.00 | 1.00 |
| Gm4759 | 0.78 | 5.22 | 0.85 | 1.00 | 1.00 | 1.00 | 1.20 | 1.10 | 0.76 |
| Gm4846 | 1.00 | 1.00 | 1.00 | 1.00 | 1.00 | 1.00 | 1.00 | 1.00 | 1.00 |
| Gm4952 | 1.00 | 1.00 | 1.00 | 1.00 | 1.00 | 1.00 | 1.00 | 1.00 | 1.00 |
| Gm5483 | 1.29 | 1.06 | 0.44 | 1.00 | 0.80 | 1.00 | 0.70 | 1.03 | 1.08 |
| Gm5531 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 |
| Gm6642 | 1.00 | 1.00 | 1.00 | 1.00 | 1.00 | 1.00 | 0.84 | 0.93 | 1.00 |
| Gm6792 | 1.00 | 1.00 | 1.00 | 1.00 | 1.00 | 1.00 | 1.00 | 1.00 | 1.00 |
| Gm7325 | 1.00 | 1.00 | 1.00 | 0.82 | 1.00 | 1.00 | 1.00 | 1.00 | 1.00 |
| Gm7334 | 1.12 | 0.87 | 0.90 | 0.76 | 0.91 | 1.22 | 1.06 | 1.24 | 1.16 |
| Gm933 | 1.00 | 1.00 | 1.00 | 1.00 | 1.00 | 1.00 | 1.00 | 1.00 | 1.00 |
| Gpc2 | 0.60 | 1.22 | 1.03 | 1.00 | 1.00 | 1.00 | 0.72 | 1.07 | 0.86 |
| Gpnmb | 1.37 | 1.82 | 1.03 | 1.08 | 1.62 | 1.55 | 1.09 | 1.35 | 0.59 |
| Gpr35 | 1.07 | 1.55 | 1.35 | 1.00 | 1.00 | 1.00 | 1.27 | 0.99 | 0.85 |
| Gpr82 | 1.00 | 1.00 | 1.00 | 1.00 | 1.00 | 1.00 | 1.25 | 1.00 | 0.96 |
| Gprc5a | 0.95 | 0.71 | 0.95 | 1.00 | 1.56 | 1.00 | 1.00 | 1.00 | 1.00 |
| Gpx5 | 1.00 | 1.00 | 1.00 | 1.00 | 1.00 | 1.00 | 1.00 | 1.00 | 1.00 |
| Grhl2 | 1.00 | 0.70 | 0.92 | 1.00 | 1.00 | 1.00 | 1.00 | 1.00 | 1.00 |
| Gtse1 | 1.50 | 14.39 | 1.00 | 1.00 | 1.00 | 1.00 | 0.85 | 1.43 | 2.82 |
| Gvin1 | 1.84 | 1.28 | 0.76 | 1.00 | 1.01 | 1.00 | 0.58 | 0.45 | 0.52 |
| H2-Ea-ps | 0.68 | 1.01 | 0.96 | 0.90 | 1.12 | 1.00 | 1.08 | 2.92 | 0.71 |
| H2-Eb1 | 0.67 | 1.00 | 1.36 | 0.72 | 1.08 | 1.17 | 1.03 | 6.55 | 0.84 |
| H2-M2 | 0.93 | 2.24 | 0.68 | 1.00 | 1.00 | 1.00 | 1.24 | 1.33 | 0.35 |
| Havcr1 | 1.00 | 1.00 | 1.00 | 1.00 | 1.00 | 1.00 | 1.64 | 0.72 | 1.20 |
| Hba-a1 | 0.75 | 0.92 | 0.86 | 1.97 | 1.67 | 1.40 | 0.55 | 1.04 | 3.01 |
| Hba-a2 | 0.59 | 0.90 | 0.88 | 1.89 | 1.06 | 2.86 | 0.51 | 0.99 | 2.46 |
| Hbb-b1 | 0.77 | 0.98 | 0.82 | 2.06 | 1.62 | 1.33 | 0.57 | 1.05 | 2.81 |
| Hbb-bh2 | 1.00 | 1.00 | 1.00 | 1.00 | 1.00 | 1.00 | 1.00 | 1.00 | 1.00 |
| Hbb-bs | 0.64 | 0.68 | 0.77 | 2.02 | 1.88 | 3.03 | 0.60 | 1.12 | 2.43 |
| Hbb-bt | 0.72 | 0.94 | 0.85 | 1.91 | 1.60 | 1.34 | 0.53 | 1.05 | 2.83 |
| Hmgb2 | 1.22 | 8.19 | 0.99 | 1.00 | 1.03 | 0.97 | 0.86 | 1.60 | 2.33 |
| Hmgcs2 | 1.18 | 0.81 | 0.95 | 1.51 | 1.34 | 1.73 | 2.08 | 0.52 | 1.08 |
| Hmmr | 1.70 | 6.51 | 1.00 | 1.00 | 1.00 | 1.00 | 0.96 | 1.43 | 3.94 |
| Hp | 1.08 | 0.77 | 1.04 | 0.99 | 1.82 | 2.28 | 0.59 | 1.22 | 1.94 |
| Hspa1a | 2.28 | 1.75 | 0.69 | 1.23 | 1.17 | 2.45 | 1.93 | 2.06 | 0.80 |
| Hspa1b | 2.26 | 1.91 | 0.73 | 1.33 | 1.15 | 2.28 | 2.13 | 1.97 | 0.74 |
| Ido1 | 1.00 | 1.00 | 1.00 | 1.00 | 1.00 | 1.00 | 1.00 | 1.00 | 1.00 |
| Ifi27l2a | 0.89 | 6.66 | 0.38 | 0.73 | 1.68 | 1.85 | 0.91 | 1.80 | 0.37 |
| Igfbp1 | 1.00 | 1.00 | 1.00 | 1.00 | 1.00 | 1.00 | 1.00 | 1.00 | 1.00 |
| Igj | 1.34 | 1.16 | 1.55 | 1.00 | 1.00 | 1.00 | 0.80 | 1.67 | 1.72 |
| Igll1 | 1.00 | 159.64 | 1.00 | 1.00 | 1.98 | 1.00 | 1.00 | 1.00 | 0.53 |
| Ikzf3 | 0.44 | 5.69 | 0.99 | 1.00 | 1.00 | 1.00 | 0.85 | 0.93 | 0.93 |
| Il12a | 0.53 | 8.65 | 0.88 | 0.57 | 1.00 | 0.73 | 0.85 | 1.21 | 0.57 |
| Il1b | 1.00 | 0.93 | 1.48 | 1.00 | 1.00 | 1.00 | 1.08 | 1.22 | 1.37 |
| Il1r2 | 3.67 | 1.78 | 0.98 | 1.05 | 0.51 | 1.26 | 1.98 | 2.73 | 1.02 |
| Il1rn | 1.73 | 1.19 | 1.26 | 1.00 | 1.00 | 1.00 | 0.70 | 1.03 | 1.02 |
| Il22ra2 | 1.10 | 1.00 | 1.00 | 1.00 | 1.00 | 1.00 | 0.85 | 0.88 | 0.67 |
| Il2ra | 1.00 | 7.78 | 0.95 | 1.00 | 1.00 | 1.00 | 1.15 | 1.00 | 0.68 |
| Il6 | 1.04 | 1.31 | 1.00 | 1.00 | 1.00 | 1.00 | 1.00 | 1.00 | 1.00 |
| Il7r | 1.01 | 12.22 | 0.66 | 1.00 | 1.30 | 1.00 | 1.79 | 1.65 | 0.53 |
| Inha | 0.81 | 0.69 | 0.93 | 1.08 | 1.44 | 1.01 | 1.66 | 1.00 | 1.02 |
| Inhbb | 1.46 | 1.34 | 2.06 | 1.11 | 1.17 | 1.00 | 2.09 | 1.21 | 0.82 |
| Inpp5d | 1.43 | 2.03 | 0.79 | 1.35 | 1.05 | 0.84 | 1.31 | 1.09 | 0.81 |
| Irf4 | 0.57 | 25.94 | 1.11 | 1.05 | 1.83 | 0.88 | 0.84 | 1.18 | 0.91 |

Fig. 31-43

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Gm11346 | 1.00 | 1.00 | 1.00 | 1.00 | 1.00 | 1.00 | 1.00 | 1.00 | 1.00 |
| Gm12191 | 2.06 | 1.20 | 0.45 | 1.85 | 1.70 | 0.36 | 0.91 | 9.81 | 0.25 |
| Gm12238 | 0.31 | 0.31 | 4.68 | 1.00 | 1.00 | 2.64 | 1.00 | 2.47 | 1.01 |
| Gm15056 | 1.00 | 1.00 | 1.00 | 1.00 | 25.95 | 1.00 | 1.00 | 1.00 | 1.00 |
| Gm15386 | 1.00 | 1.00 | 1.00 | 1.00 | 316.50 | 1.00 | 1.33 | 0.90 | 0.72 |
| Gm17727 | 1.00 | 1.00 | 1.00 | 1.00 | 22.60 | 1.00 | 1.00 | 1.00 | 1.00 |
| Gm1987 | 1.00 | 1.00 | 1.00 | 1.00 | 8.07 | 0.15 | 1.17 | 0.96 | 1.00 |
| Gm2083 | 1.00 | 1.00 | 1.00 | 1.00 | 1.00 | 1.00 | 1.00 | 1.00 | 1.00 |
| Gm266 | 0.93 | 1.22 | 1.79 | 0.75 | 5.13 | 1.00 | 0.91 | 0.97 | 1.05 |
| Gm2663 | 1.00 | 1.00 | 1.00 | 1.00 | 1.00 | 1.00 | 1.00 | 1.00 | 1.00 |
| Gm4759 | 1.00 | 1.00 | 1.00 | 1.00 | 1.00 | 1.00 | 1.00 | 1.00 | 1.00 |
| Gm4846 | 1.00 | 1.00 | 1.00 | 1.00 | 6.62 | 1.00 | 1.06 | 0.93 | 1.00 |
| Gm4952 | 1.00 | 1.00 | 1.00 | 1.00 | 1.00 | 1.00 | 1.00 | 1.00 | 1.00 |
| Gm5483 | 1.00 | 1.00 | 1.00 | 3.51 | 1.00 | 1.00 | 1.00 | 1.00 | 1.00 |
| Gm5531 | 1.00 | 1.00 | 1.00 | 1.00 | 73.22 | 1.00 | 1.00 | 1.00 | 1.00 |
| Gm6040 | 1.00 | 1.00 | 1.00 | 1.00 | 49.61 | 1.00 | 1.00 | 1.00 | 1.00 |
| Gm6642 | 1.11 | 1.13 | 0.98 | 0.91 | 1.20 | 1.00 | 1.00 | 1.00 | 1.00 |
| Gm6792 | 1.00 | 1.00 | 1.00 | 1.00 | 1411.19 | 1.00 | 1.00 | 1.00 | 1.00 |
| Gm7325 | 1.00 | 1.00 | 1.00 | 1.00 | 1.00 | 1.00 | 0.85 | 1.06 | 1.06 |
| Gm7334 | 1.15 | 1.23 | 0.96 | 0.94 | 5.32 | 0.88 | 1.15 | 0.94 | 0.94 |
| Gm933 | 1.00 | 1.00 | 1.00 | 1.00 | 6.42 | 1.00 | 1.00 | 1.00 | 1.00 |
| Gpc2 | 0.79 | 1.01 | 1.21 | 0.66 | 6.20 | 0.99 | 1.06 | 1.06 | 0.97 |
| Gpnmb | 1.00 | 1.00 | 1.00 | 1.36 | 5.76 | 0.65 | 1.00 | 1.00 | 1.00 |
| Gpr35 | 1.00 | 1.00 | 1.00 | 1.87 | 0.99 | 0.73 | 1.00 | 1.00 | 1.00 |
| Gpr82 | 1.00 | 1.00 | 1.00 | 1.00 | 5.67 | 1.00 | 1.00 | 1.00 | 1.00 |
| Gprc5a | 1.00 | 1.00 | 1.00 | 2.85 | 1.39 | 1.12 | 1.00 | 1.00 | 1.00 |
| Gpx5 | 1.00 | 1.00 | 1.00 | 1.00 | 1875.09 | 1.00 | 1.15 | 1.00 | 1.00 |
| Grhl2 | 1.00 | 1.00 | 1.00 | 1.00 | 7.17 | 1.00 | 1.24 | 0.69 | 1.06 |
| Gtse1 | 1.00 | 2.10 | 1.00 | 1.00 | 1.00 | 1.00 | 1.02 | 0.96 | 0.94 |
| Gvin1 | 1.00 | 1.00 | 1.00 | 1.42 | 1.04 | 0.75 | 1.00 | 1.00 | 1.00 |
| H2-Ea-ps | 1.00 | 1.00 | 1.00 | 1.13 | 0.82 | 0.45 | 0.95 | 1.00 | 1.00 |
| H2-Eb1 | 1.00 | 1.00 | 1.00 | 0.99 | 0.65 | 0.81 | 0.81 | 1.06 | 0.75 |
| H2-M2 | 1.00 | 1.00 | 1.00 | 1.00 | 1.00 | 0.90 | 1.00 | 1.00 | 1.00 |
| Havcr1 | 1.00 | 1.00 | 1.00 | 1.00 | 1.00 | 1.00 | 1.00 | 1.00 | 1.00 |
| Hba-a1 | 0.73 | 3.04 | 1.55 | 1.41 | 3.04 | 1.46 | 1.06 | 7.57 | 1.77 |
| Hba-a2 | 0.89 | 2.43 | 1.29 | 1.34 | 3.07 | 1.30 | 1.00 | 1.00 | 1.00 |
| Hbb-b1 | 0.79 | 3.03 | 1.43 | 1.40 | 3.14 | 1.27 | 0.85 | 7.12 | 1.72 |
| Hbb-bh2 | 1.00 | 1.00 | 1.00 | 1.00 | 1.00 | 1.00 | 1.00 | 1.00 | 1.00 |
| Hbb-bs | 0.61 | 2.35 | 1.19 | 1.56 | 2.86 | 1.38 | 1.00 | 1.00 | 1.00 |
| Hbb-bt | 0.72 | 2.96 | 1.42 | 1.31 | 3.12 | 1.33 | 0.88 | 7.23 | 1.50 |
| Hmgb2 | 1.00 | 2.75 | 1.00 | 1.01 | 1.52 | 0.87 | 1.03 | 1.17 | 1.01 |
| Hmgcs2 | 1.67 | 1.54 | 1.21 | 2.21 | 1.18 | 0.94 | 1.23 | 0.79 | 0.89 |
| Hmmr | 1.00 | 1.03 | 1.00 | 1.00 | 1.00 | 1.00 | 1.15 | 1.04 | 1.02 |
| Hp | 1.00 | 1.00 | 1.00 | 1.30 | 0.85 | 1.46 | 0.25 | 1.46 | 1.00 |
| Hspa1a | 0.85 | 1.06 | 1.20 | 0.89 | 2.74 | 1.19 | 1.03 | 1.01 | 1.03 |
| Hspa1b | 0.91 | 1.02 | 1.17 | 0.85 | 2.66 | 1.09 | 1.00 | 1.00 | 1.04 |
| Ido1 | 0.79 | 1.00 | 1.07 | 1.00 | 147.26 | 1.00 | 1.00 | 1.00 | 1.00 |
| Ifi27l2a | 1.21 | 5.03 | 0.78 | 1.00 | 0.83 | 1.52 | 0.43 | 2.29 | 0.62 |
| Igfbp1 | 1.00 | 1.00 | 1.00 | 0.99 | 0.37 | 1.00 | 1.00 | 1.00 | 1.00 |
| Igj | 1.00 | 1.00 | 1.00 | 1.14 | 2.14 | 0.30 | 1.00 | 1.00 | 1.00 |
| Igll1 | 1.00 | 12.77 | 1.00 | 1.00 | 3.70 | 1.00 | 1.00 | 1.00 | 1.00 |
| Ikzf3 | 1.00 | 1.66 | 1.00 | 1.00 | 1.35 | 0.33 | 1.00 | 1.00 | 1.00 |
| Il12a | 1.00 | 1.19 | 1.00 | 1.00 | 1.00 | 1.00 | 1.00 | 1.00 | 1.00 |
| Il1b | 1.00 | 1.00 | 1.00 | 7.64 | 1.00 | 1.02 | 0.82 | 0.97 | 1.11 |
| Il1r2 | 1.00 | 1.00 | 1.00 | 3.72 | 1.00 | 1.00 | 1.00 | 1.00 | 1.00 |
| Il1rn | 1.00 | 1.00 | 1.00 | 4.26 | 2.05 | 0.67 | 1.00 | 1.00 | 1.00 |
| Il22ra2 | 1.00 | 1.00 | 1.00 | 1.00 | 1.00 | 1.00 | 1.00 | 1.00 | 1.00 |
| Il2ra | 1.00 | 1.00 | 1.00 | 0.83 | 0.98 | 0.63 | 1.00 | 1.00 | 1.00 |
| Il6 | 1.00 | 1.00 | 1.00 | 1.00 | 1.00 | 1.00 | 1.00 | 1.00 | 1.00 |
| Il7r | 1.00 | 3.62 | 1.00 | 1.52 | 2.79 | 0.64 | 1.00 | 1.00 | 1.00 |
| Inha | 0.91 | 0.99 | 1.04 | 0.79 | 5.70 | 0.86 | 0.83 | 0.89 | 1.01 |
| Inhbb | 0.86 | 0.90 | 1.12 | 1.00 | 0.61 | 0.90 | 0.95 | 1.01 | 0.97 |
| Inpp5d | 1.05 | 1.73 | 0.92 | 1.76 | 1.03 | 0.63 | 1.36 | 0.92 | 1.09 |
| Irf4 | 1.00 | 2.58 | 1.00 | 1.05 | 1.39 | 0.50 | 1.00 | 1.00 | 1.00 |

Fig. 31- 44

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Gm11346 | 1.27 | 6.99 | 1.60 | 1.46 | 1.95 | 1.39 | 1.00 | 1.00 | 1.00 | 1.00 | 1.00 | 1.00 |
| Gm12191 | 2.32 | 0.57 | 1.66 | 3.39 | 0.47 | 1.72 | 1.45 | 0.62 | 1.82 | 0.38 | 1.00 | 1.00 |
| Gm12238 | 1.00 | 1.72 | 1.56 | 0.33 | 0.96 | 1.72 | 1.00 | 1.00 | 1.00 | 0.04 | 1.00 | 1.00 |
| Gm15056 | 0.53 | 7.96 | 1.65 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 | 1.00 | 1.00 | 1.00 |
| Gm1987 | 1.31 | 0.84 | 1.00 | 1.00 | 1.00 | 1.00 | 1.00 | 1.00 | 1.00 | 1.00 | 1.00 | 1.00 |
| Gm2083 | 1.00 | 1.00 | 1.00 | 1.00 | 1.00 | 1.00 | 1.00 | 1.00 | 1.00 | 1.00 | 1.00 | 1.00 |
| Gm266 | 1.17 | 1.28 | 1.36 | 1.00 | 1.00 | 1.00 | 1.00 | 1.00 | 1.00 | 0.92 | 1.00 | 1.00 |
| Gm2663 | 1.00 | 1.00 | 1.00 | 1.00 | 1.00 | 1.00 | 6.35 | 0.96 | 0.99 | 1.00 | 1.00 | 1.00 |
| Gm4759 | 0.87 | 1.13 | 1.20 | 0.89 | 1.32 | 0.97 | 1.00 | 1.00 | 1.00 | 1.00 | 1.00 | 1.00 |
| Gm4846 | 1.00 | 1.00 | 1.00 | 1.00 | 1.00 | 1.00 | 1.00 | 1.00 | 1.00 | 1.00 | 1.00 | 1.00 |
| Gm4952 | 1.00 | 1.00 | 1.00 | 1.00 | 1.00 | 1.00 | 1.00 | 1.00 | 1.00 | 1.00 | 1.00 | 1.00 |
| Gm5483 | 0.99 | 1.00 | 1.00 | 1.54 | 1.03 | 0.80 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 | 1.00 | 1.00 | 1.00 |
| Gm6642 | 1.00 | 1.00 | 1.20 | 1.00 | 1.00 | 1.00 | 1.00 | 1.00 | 1.00 | 1.00 | 6.20 | 3.52 |
| Gm6792 | 1.00 | 1.00 | 1.00 | 1.00 | 1.00 | 1.00 | 1.00 | 1.00 | 1.00 | 1.00 | 1.00 | 1.00 |
| Gm7325 | 1.00 | 1.00 | 1.00 | 1.00 | 1.00 | 1.00 | 1.00 | 1.00 | 1.00 | 1.42 | 2.37 | 5.23 |
| Gm7334 | 0.97 | 0.75 | 1.02 | 0.96 | 0.66 | 0.96 | 1.03 | 1.38 | 1.27 | 1.67 | 1.00 | 1.00 |
| Gm933 | 1.00 | 1.00 | 1.00 | 1.00 | 1.00 | 1.00 | 1.00 | 1.00 | 1.00 | 1.00 | 1.00 | 1.00 |
| Gpc2 | 1.00 | 0.71 | 0.57 | 1.16 | 0.93 | 0.85 | 1.00 | 1.00 | 1.00 | 0.81 | 1.07 | 1.03 |
| Gpnmb | 0.80 | 1.22 | 1.96 | 1.00 | 1.53 | 0.67 | 1.00 | 1.00 | 1.00 | 1.04 | 1.16 | 1.20 |
| Gpr35 | 0.94 | 1.90 | 1.53 | 1.03 | 2.43 | 1.16 | 1.00 | 1.00 | 1.00 | 0.88 | 1.16 | 0.71 |
| Gpr82 | 1.00 | 1.00 | 1.00 | 1.00 | 1.00 | 1.00 | 1.00 | 1.00 | 1.00 | 1.00 | 1.00 | 1.00 |
| Gprc5a | 1.22 | 1.18 | 1.32 | 1.00 | 1.00 | 1.00 | 1.00 | 1.00 | 1.00 | 1.01 | 1.09 | 0.94 |
| Gpx5 | 1.00 | 1.00 | 1.00 | 1.00 | 1.00 | 1.00 | 1.00 | 1.00 | 1.00 | 1.00 | 1.00 | 1.00 |
| Grhl2 | 1.41 | 0.83 | 1.07 | 1.00 | 1.00 | 1.00 | 0.90 | 1.07 | 1.11 | 1.03 | 0.97 | 1.07 |
| Gtse1 | 0.43 | 0.64 | 0.89 | 0.88 | 0.84 | 0.89 | 1.00 | 1.00 | 1.00 | 1.02 | 1.00 | 1.00 |
| Gvin1 | 0.93 | 1.98 | 0.40 | 0.50 | 6.02 | 1.04 | 1.00 | 1.00 | 1.00 | 1.00 | 0.98 | 1.08 |
| H2-Ea-ps | 21.11 | 0.73 | 2.11 | 10.09 | 0.75 | 1.66 | 1.00 | 0.46 | 0.63 | 0.67 | 1.00 | 1.00 |
| H2-Eb1 | 0.41 | 2.27 | 4.79 | 0.29 | 1.30 | 3.77 | 0.27 | 1.13 | 1.35 | 1.00 | 1.00 | 1.00 |
| H2-M2 | 1.04 | 1.29 | 0.79 | 0.73 | 6.11 | 5.15 | 1.00 | 1.00 | 1.00 | 0.86 | 0.96 | 0.72 |
| Havcr1 | 1.18 | 1.36 | 1.73 | 0.84 | 0.62 | 0.93 | 1.00 | 1.00 | 1.00 | 1.00 | 1.09 | 0.96 |
| Hba-a1 | 1.25 | 1.64 | 2.48 | 1.44 | 0.98 | 1.28 | 1.39 | 0.53 | 0.75 | 0.97 | 0.14 | 0.05 |
| Hba-a2 | 1.38 | 1.49 | 2.85 | 1.40 | 0.93 | 1.69 | 1.78 | 0.65 | 0.83 | 0.06 | 1.00 | 1.00 |
| Hbb-b1 | 1.17 | 1.60 | 2.51 | 1.49 | 0.93 | 1.43 | 1.31 | 0.58 | 0.77 | 1.18 | 1.00 | 1.00 |
| Hbb-bh2 | 1.00 | 1.00 | 1.00 | 1.00 | 1.00 | 1.00 | 1.00 | 1.00 | 1.00 | 1.00 | 10.97 | 0.18 |
| Hbb-bs | 1.94 | 1.36 | 4.74 | 1.57 | 0.84 | 1.61 | 2.19 | 0.44 | 0.66 | 1.00 | 1.02 | 2.06 |
| Hbb-bt | 1.19 | 1.67 | 2.56 | 1.43 | 0.95 | 1.37 | 1.39 | 0.56 | 0.74 | 1.10 | 1.00 | 1.00 |
| Hmgb2 | 0.38 | 0.68 | 0.94 | 1.02 | 1.03 | 1.07 | 1.00 | 1.00 | 1.00 | 0.78 | 1.04 | 1.00 |
| Hmgcs2 | 1.50 | 1.72 | 1.99 | 1.00 | 1.00 | 1.00 | 1.99 | 2.25 | 10.58 | 1.21 | 1.06 | 1.02 |
| Hmmr | 0.38 | 0.64 | 0.89 | 0.93 | 0.91 | 1.28 | 1.00 | 1.00 | 1.00 | 0.92 | 1.16 | 1.00 |
| Hp | 1.28 | 2.40 | 4.05 | 0.97 | 1.39 | 1.38 | 1.05 | 1.02 | 1.42 | 1.00 | 1.13 | 1.00 |
| Hspa1a | 1.40 | 0.62 | 1.40 | 1.00 | 0.81 | 1.00 | 1.00 | 1.00 | 1.00 | 0.94 | 0.76 | 1.02 |
| Hspa1b | 1.40 | 0.66 | 1.43 | 1.00 | 0.81 | 1.00 | 1.00 | 1.00 | 1.00 | 0.95 | 0.59 | 0.72 |
| Ido1 | 1.00 | 1.00 | 1.00 | 1.00 | 1.00 | 1.00 | 1.00 | 1.00 | 1.00 | 1.00 | 1.00 | 1.00 |
| Ifi27l2a | 1.39 | 1.57 | 1.46 | 0.93 | 2.71 | 0.89 | 0.58 | 1.17 | 0.69 | 0.96 | 1.00 | 1.00 |
| Igfbp1 | 1.00 | 1.00 | 1.00 | 1.00 | 1.00 | 1.00 | 1.00 | 1.00 | 1.00 | 1.00 | 0.92 | 1.11 |
| Igj | 1.36 | 1.37 | 1.54 | 1.04 | 0.70 | 1.29 | 1.25 | 1.09 | 0.57 | 1.00 | 1.00 | 1.00 |
| Igll1 | 1.00 | 1.00 | 1.00 | 0.90 | 0.56 | 0.61 | 1.00 | 1.00 | 1.00 | 1.00 | 1.07 | 1.02 |
| Ikzf3 | 0.77 | 0.83 | 0.80 | 1.01 | 0.60 | 0.78 | 1.00 | 1.00 | 1.00 | 1.00 | 1.19 | 0.94 |
| Il12a | 1.09 | 1.55 | 1.29 | 0.92 | 0.56 | 0.97 | 1.00 | 1.00 | 1.00 | 1.00 | 1.00 | 1.00 |
| Il1b | 0.50 | 1.93 | 1.64 | 1.14 | 1.43 | 1.15 | 1.00 | 1.00 | 1.00 | 1.41 | 1.25 | 0.46 |
| Il1r2 | 1.04 | 0.81 | 1.02 | 0.75 | 1.45 | 1.50 | 1.00 | 1.00 | 1.00 | 1.21 | 1.09 | 1.03 |
| Il1rn | 0.70 | 1.64 | 1.25 | 1.10 | 0.73 | 1.07 | 1.00 | 1.00 | 1.00 | 0.86 | 1.00 | 1.00 |
| Il22ra2 | 1.00 | 2.02 | 6.29 | 1.00 | 1.00 | 1.00 | 1.00 | 1.00 | 1.00 | 1.19 | 1.00 | 1.00 |
| Il2ra | 0.96 | 1.06 | 0.89 | 0.98 | 0.31 | 0.74 | 1.00 | 1.00 | 1.00 | 1.00 | 1.18 | 0.94 |
| Il6 | 0.76 | 1.00 | 1.00 | 1.05 | 1.36 | 1.00 | 1.00 | 1.00 | 1.00 | 1.00 | 0.79 | 0.86 |
| Il7r | 0.85 | 0.82 | 1.25 | 1.12 | 0.60 | 1.02 | 1.00 | 1.00 | 1.00 | 1.36 | 1.00 | 1.00 |
| Inha | 1.42 | 0.98 | 0.88 | 1.00 | 1.00 | 1.00 | 0.90 | 1.47 | 0.89 | 0.92 | 1.00 | 1.00 |
| Inhbb | 1.22 | 0.97 | 0.94 | 1.00 | 1.00 | 1.00 | 1.00 | 1.00 | 1.00 | 1.00 | 1.00 | 1.00 |
| Inpp5d | 0.93 | 1.18 | 1.07 | 1.02 | 1.08 | 0.95 | 1.00 | 1.00 | 1.00 | 1.04 | 1.06 | 1.07 |
| Irf4 | 1.09 | 1.73 | 1.85 | 0.99 | 0.55 | 0.81 | 1.00 | 1.00 | 1.00 | 1.01 | 1.00 | 0.91 |

Fig. 31- 45

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Irg1 | 1.76 | 1.00 | 1.00 | 1.00 | 1.00 | 1.00 | 1.00 | 1.00 | 1.00 |
| Isg20 | 0.71 | 1.28 | 2.53 | 0.75 | 2.22 | 1.06 | 1.01 | 1.72 | 1.01 |
| Ism1 | 0.97 | 3.79 | 6.06 | 1.00 | 1.00 | 1.00 | 1.00 | 1.00 | 1.00 |
| Itih4 | 1.03 | 1.83 | 2.95 | 1.00 | 1.00 | 1.00 | 1.17 | 1.14 | 0.89 |
| Itln1 | 1.00 | 1.00 | 1.00 | 1.00 | 1.00 | 1.00 | 1.00 | 1.00 | 1.00 |
| Jakmip1 | 1.00 | 1.00 | 1.00 | 1.00 | 1.00 | 1.00 | 1.00 | 1.40 | 1.00 |
| Kap | 1.00 | 1.00 | 1.00 | 1.11 | 0.86 | 1.12 | 1.00 | 1.00 | 1.00 |
| Kcnc4 | 1.00 | 1.00 | 1.00 | 1.00 | 1.00 | 1.00 | 1.00 | 1.00 | 1.00 |
| Kcnh3 | 1.00 | 1.00 | 1.00 | 1.00 | 1.00 | 1.00 | 1.00 | 1.00 | 1.00 |
| Kcnmb4 | 1.00 | 1.00 | 1.00 | 1.00 | 1.00 | 1.00 | 1.00 | 1.00 | 1.00 |
| Kif11 | 1.00 | 2.01 | 1.00 | 1.00 | 1.00 | 1.00 | 1.00 | 2.45 | 1.00 |
| Kif15 | 1.00 | 1.04 | 1.00 | 1.00 | 1.00 | 1.00 | 1.00 | 1.45 | 1.00 |
| Kif18b | 1.00 | 1.23 | 1.00 | 1.00 | 1.00 | 1.00 | 1.00 | 1.49 | 1.00 |
| Kif22 | 1.21 | 3.00 | 1.00 | 1.00 | 1.00 | 1.00 | 1.00 | 2.78 | 1.00 |
| Kif2c | 1.00 | 1.61 | 1.00 | 1.00 | 1.00 | 1.00 | 1.00 | 1.26 | 1.00 |
| Kifc1 | 1.00 | 2.11 | 1.00 | 1.00 | 1.00 | 1.00 | 1.00 | 1.71 | 1.00 |
| Kifc5b | 1.00 | 1.64 | 1.00 | 1.00 | 1.00 | 1.00 | 1.00 | 1.26 | 1.00 |
| Klhl23 | 0.64 | 0.55 | 0.71 | 1.00 | 1.00 | 1.00 | 1.00 | 1.00 | 1.00 |
| Klhl34 | 0.67 | 0.41 | 0.79 | 1.00 | 1.00 | 1.00 | 1.00 | 1.00 | 1.00 |
| Klhl6 | 1.47 | 2.52 | 1.56 | 1.12 | 1.27 | 0.86 | 0.95 | 8.22 | 1.11 |
| Knstrn | 1.00 | 2.31 | 1.00 | 1.00 | 1.00 | 1.00 | 1.00 | 1.51 | 1.00 |
| Krt13 | 1.00 | 1.00 | 1.00 | 1.00 | 1.00 | 1.00 | 1.00 | 1.00 | 1.00 |
| Krt14 | 1.75 | 0.60 | 1.13 | 1.00 | 1.00 | 1.00 | 1.00 | 1.00 | 1.00 |
| Krt15 | 1.00 | 1.00 | 1.24 | 1.13 | 1.13 | 1.49 | 1.00 | 1.00 | 1.00 |
| Krt18 | 2.93 | 1.22 | 8.63 | 0.77 | 0.88 | 1.13 | 0.75 | 1.14 | 1.42 |
| Krt4 | 1.00 | 1.00 | 1.00 | 1.00 | 1.00 | 1.00 | 1.00 | 1.00 | 1.00 |
| Krt5 | 1.93 | 1.00 | 1.00 | 1.00 | 1.40 | 1.41 | 1.00 | 1.00 | 1.00 |
| Krt78 | 1.00 | 1.00 | 1.00 | 1.00 | 1.00 | 1.00 | 1.00 | 1.00 | 1.00 |
| Laptm5 | 1.62 | 2.79 | 2.03 | 0.79 | 1.61 | 0.90 | 0.88 | 2.65 | 0.98 |
| Lars2 | 0.86 | 0.78 | 0.76 | 0.91 | 0.87 | 1.42 | 1.23 | 0.35 | 0.96 |
| Lce1a1 | 1.00 | 1.00 | 1.00 | 1.00 | 1.00 | 1.00 | 1.00 | 1.00 | 1.00 |
| Lce1a2 | 1.00 | 1.00 | 1.00 | 1.00 | 1.00 | 1.00 | 1.00 | 1.00 | 1.00 |
| Lce1b | 1.00 | 1.00 | 1.00 | 1.00 | 1.00 | 1.00 | 1.00 | 1.00 | 1.00 |
| Lce1d | 1.00 | 1.00 | 1.00 | 1.00 | 1.00 | 1.00 | 1.00 | 1.00 | 1.00 |
| Lce3a | 1.00 | 1.00 | 1.00 | 1.00 | 1.00 | 1.00 | 1.00 | 1.00 | 1.00 |
| Lce3b | 1.00 | 1.00 | 1.00 | 1.00 | 1.00 | 1.00 | 1.00 | 1.00 | 1.00 |
| Lce3c | 1.00 | 1.00 | 1.00 | 1.00 | 1.00 | 1.00 | 1.00 | 1.00 | 1.00 |
| Lce3d | 1.00 | 1.00 | 1.00 | 1.00 | 1.00 | 1.00 | 1.00 | 1.00 | 1.00 |
| Lce3e | 1.00 | 1.00 | 1.00 | 1.00 | 1.00 | 1.00 | 1.00 | 1.00 | 1.00 |
| Lce3f | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 |
| Lcn2 | 1.13 | 1.86 | 2.17 | 1.27 | 1.76 | 0.97 | 0.66 | 9.08 | 0.50 |
| Lcn5 | 1.00 | 1.00 | 1.00 | 0.46 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 |
| Ldb3 | 0.83 | 0.55 | 0.71 | 1.00 | 1.00 | 1.00 | 1.00 | 1.00 | 1.00 |
| Lef1 | 1.00 | 1.61 | 1.00 | 1.00 | 1.08 | 1.00 | 1.00 | 3.52 | 1.00 |
| Lgals3 | 2.53 | 11.45 | 3.29 | 0.65 | 0.94 | 0.98 | 1.16 | 2.56 | 1.05 |
| Lgr5 | 1.00 | 1.00 | 1.00 | 1.00 | 1.00 | 1.00 | 0.88 | 1.47 | 1.06 |
| Lingo1 | 1.00 | 1.00 | 1.00 | 1.00 | 1.00 | 1.00 | 1.00 | 1.00 | 1.00 |
| Lipg | 1.00 | 1.00 | 1.00 | 1.03 | 0.99 | 0.99 | 0.71 | 0.45 | 0.71 |
| Lmnb1 | 1.85 | 1.95 | 1.19 | 0.95 | 1.20 | 0.95 | 0.70 | 4.79 | 1.10 |
| LOC547349 | 1.56 | 1.73 | 1.26 | 0.83 | 1.00 | 1.65 | 1.00 | 1.00 | 5.44 |
| Lor | 1.00 | 1.00 | 1.00 | 1.00 | 1.00 | 1.00 | 1.00 | 1.00 | 1.00 |
| Lox | 3.30 | 5.88 | 5.56 | 2.25 | 1.86 | 1.82 | 1.00 | 1.00 | 1.00 |
| Loxl3 | 1.29 | 5.26 | 3.90 | 0.82 | 1.00 | 1.04 | 1.00 | 1.00 | 1.00 |
| Lpin1 | 0.54 | 0.55 | 0.74 | 1.45 | 0.84 | 0.83 | 8.17 | 0.92 | 0.29 |
| Lrcol1 | 1.00 | 1.00 | 1.00 | 1.00 | 1.00 | 1.00 | 1.00 | 1.00 | 1.00 |
| Lrmp | 1.88 | 2.98 | 1.18 | 1.00 | 1.59 | 0.87 | 1.24 | 9.61 | 0.81 |
| Ltbp2 | 2.51 | 13.15 | 13.91 | 1.00 | 1.00 | 1.00 | 1.00 | 1.00 | 1.00 |
| Ly6g5b | 1.00 | 1.00 | 1.00 | 1.00 | 1.00 | 1.00 | 1.00 | 1.00 | 1.00 |
| Ly6g5c | 1.00 | 1.00 | 1.00 | 1.00 | 1.00 | 1.00 | 1.00 | 1.00 | 1.00 |
| Ly9 | 0.87 | 5.16 | 1.20 | 1.00 | 1.00 | 1.00 | 1.00 | 2.29 | 1.01 |

Fig. 31- 46

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Irg1 | 1.17 | 1.00 | 1.00 | 1.00 | 1.00 | 1.00 | 1.00 | 1.00 | 1.00 |
| Isg20 | 0.75 | 0.88 | 0.98 | 1.05 | 1.15 | 0.94 | 0.74 | 1.25 | 2.62 |
| Ism1 | 1.21 | 0.83 | 1.03 | 1.00 | 0.91 | 1.00 | 1.00 | 1.00 | 1.00 |
| Itih4 | 1.88 | 1.00 | 1.69 | 1.00 | 1.00 | 1.00 | 0.81 | 0.76 | 1.00 |
| Itln1 | 0.77 | 1.49 | 0.16 | 1.00 | 1.00 | 1.00 | 1.09 | 0.77 | 0.92 |
| Jakmip1 | 0.93 | 6.58 | 0.84 | 1.00 | 1.00 | 1.00 | 1.08 | 0.92 | 0.88 |
| Kap | 1.00 | 1.00 | 1.00 | 1.00 | 1.00 | 1.00 | 1.00 | 1.00 | 1.00 |
| Kcnc4 | 1.00 | 1.00 | 1.00 | 0.97 | 1.48 | 0.85 | 1.00 | 1.00 | 1.00 |
| Kcnh3 | 0.68 | 0.72 | 0.90 | 1.00 | 1.00 | 1.00 | 1.30 | 1.00 | 1.00 |
| Kcnmb4 | 0.79 | 0.79 | 0.86 | 1.00 | 1.00 | 1.00 | 1.29 | 1.20 | 1.15 |
| Kif11 | 1.86 | 8.14 | 1.05 | 1.00 | 1.00 | 1.00 | 1.01 | 1.53 | 3.15 |
| Kif15 | 1.26 | 6.22 | 1.00 | 1.00 | 1.00 | 1.00 | 0.74 | 1.26 | 2.79 |
| Kif18b | 1.14 | 6.27 | 1.00 | 1.00 | 1.00 | 1.00 | 1.06 | 1.47 | 3.33 |
| Kif22 | 1.45 | 7.65 | 1.32 | 1.00 | 0.96 | 1.00 | 0.94 | 1.46 | 2.97 |
| Kif2c | 1.50 | 5.35 | 1.00 | 1.00 | 1.00 | 1.00 | 0.89 | 1.53 | 2.63 |
| Kifc1 | 1.50 | 6.06 | 0.92 | 1.00 | 1.00 | 1.00 | 0.99 | 1.39 | 2.89 |
| Kifc5b | 1.39 | 5.36 | 1.00 | 1.00 | 1.00 | 1.00 | 1.00 | 1.43 | 2.49 |
| Klhl23 | 0.85 | 0.82 | 1.34 | 0.53 | 0.77 | 1.05 | 0.70 | 1.15 | 1.69 |
| Klhl34 | 1.00 | 1.00 | 1.00 | 1.05 | 0.49 | 1.04 | 1.00 | 1.00 | 1.00 |
| Klhl6 | 1.20 | 10.23 | 0.94 | 0.87 | 1.50 | 1.12 | 1.28 | 1.04 | 0.74 |
| Knstrn | 1.43 | 5.26 | 1.08 | 1.00 | 1.00 | 1.00 | 0.76 | 1.28 | 2.26 |
| Krt13 | 1.00 | 1.00 | 1.00 | 1.00 | 1.00 | 1.00 | 1.00 | 1.00 | 1.00 |
| Krt14 | 1.58 | 0.35 | 1.00 | 1.00 | 1.00 | 1.00 | 1.00 | 1.00 | 1.00 |
| Krt15 | 1.00 | 0.93 | 1.00 | 1.00 | 1.00 | 1.00 | 1.00 | 1.00 | 1.00 |
| Krt18 | 1.20 | 0.83 | 1.64 | 0.84 | 1.00 | 1.00 | 1.96 | 0.25 | 0.36 |
| Krt4 | 1.00 | 1.00 | 1.00 | 1.00 | 1.00 | 1.00 | 1.00 | 1.00 | 1.00 |
| Krt5 | 1.00 | 1.00 | 0.94 | 1.00 | 1.00 | 1.00 | 1.00 | 1.00 | 1.00 |
| Krt78 | 1.00 | 1.00 | 1.00 | 1.00 | 1.00 | 1.00 | 1.00 | 1.00 | 1.00 |
| Laptm5 | 0.91 | 1.60 | 1.12 | 0.92 | 0.92 | 1.12 | 1.04 | 0.96 | 0.79 |
| Lars2 | 1.30 | 1.03 | 0.82 | 1.10 | 0.77 | 2.38 | 1.00 | 1.25 | 1.13 |
| Lce1a1 | 1.00 | 1.00 | 1.00 | 1.00 | 1.00 | 1.00 | 1.00 | 1.00 | 1.00 |
| Lce1a2 | 1.00 | 1.00 | 1.00 | 1.00 | 1.00 | 1.00 | 1.00 | 1.00 | 1.00 |
| Lce1b | 1.00 | 1.00 | 1.00 | 1.00 | 1.00 | 1.00 | 1.00 | 1.00 | 1.00 |
| Lce1d | 1.00 | 1.00 | 1.00 | 1.00 | 1.00 | 1.00 | 1.00 | 1.00 | 1.00 |
| Lce3a | 1.00 | 1.00 | 1.00 | 1.00 | 1.00 | 1.00 | 1.00 | 1.00 | 1.00 |
| Lce3b | 1.00 | 1.00 | 1.00 | 1.00 | 1.00 | 1.00 | 1.00 | 1.00 | 1.00 |
| Lce3c | 1.00 | 1.00 | 1.00 | 1.00 | 1.00 | 1.00 | 1.00 | 1.00 | 1.00 |
| Lce3d | 1.00 | 1.00 | 1.00 | 1.00 | 1.00 | 1.00 | 1.00 | 1.00 | 1.00 |
| Lce3e | 1.00 | 1.00 | 1.00 | 1.00 | 1.00 | 1.00 | 1.00 | 1.00 | 1.00 |
| Lce3f | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 |
| Lcn2 | 1.83 | 1.69 | 1.73 | 2.41 | 0.25 | 0.36 | 0.37 | 1.55 | 2.36 |
| Lcn5 | 1.00 | 1.00 | 1.00 | 1.00 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 |
| Ldb3 | 0.78 | 0.71 | 1.15 | 1.09 | 0.93 | 0.95 | 1.00 | 1.00 | 0.98 |
| Lef1 | 0.75 | 6.82 | 0.86 | 1.00 | 1.00 | 1.00 | 1.18 | 1.18 | 0.83 |
| Lgals3 | 1.40 | 1.22 | 1.42 | 1.17 | 0.88 | 0.93 | 0.83 | 0.94 | 0.91 |
| Lgr5 | 1.00 | 9.15 | 1.00 | 1.00 | 1.00 | 1.00 | 1.00 | 1.00 | 1.00 |
| Lingo1 | 1.00 | 0.82 | 0.99 | 1.00 | 1.00 | 1.00 | 0.76 | 0.77 | 0.79 |
| Lipg | 0.94 | 0.73 | 1.21 | 1.00 | 1.00 | 1.00 | 1.07 | 1.66 | 0.78 |
| Lmnb1 | 1.34 | 5.22 | 1.23 | 1.11 | 1.35 | 0.72 | 0.84 | 1.26 | 1.93 |
| LOC547349 | 0.87 | 1.22 | 0.84 | 1.64 | 0.72 | 0.55 | 0.72 | 1.54 | 1.00 |
| Lor | 1.00 | 1.00 | 1.00 | 1.00 | 1.00 | 1.00 | 1.00 | 1.00 | 1.00 |
| Lox | 2.38 | 2.03 | 2.24 | 1.82 | 1.37 | 1.36 | 2.19 | 1.32 | 1.03 |
| Loxl3 | 0.91 | 1.08 | 0.97 | 1.14 | 0.96 | 1.02 | 0.80 | 0.95 | 0.91 |
| Lpin1 | 1.44 | 0.75 | 0.87 | 1.42 | 0.94 | 1.14 | 1.19 | 0.87 | 0.99 |
| Lrcol1 | 1.00 | 1.00 | 1.00 | 1.00 | 1.00 | 1.00 | 1.00 | 1.00 | 1.00 |
| Lrmp | 0.87 | 11.45 | 0.79 | 1.11 | 1.22 | 0.95 | 1.05 | 0.95 | 0.76 |
| Ltbp2 | 1.01 | 1.09 | 1.25 | 1.00 | 1.00 | 1.00 | 0.80 | 0.95 | 0.98 |
| Ly6g5b | 1.00 | 1.03 | 1.13 | 1.00 | 1.00 | 1.00 | 0.70 | 0.98 | 1.05 |
| Ly6g5c | 1.00 | 1.00 | 1.00 | 1.00 | 1.00 | 1.00 | 1.00 | 1.00 | 1.00 |
| Ly9 | 0.56 | 2.40 | 1.04 | 1.00 | 1.00 | 1.00 | 1.07 | 0.99 | 0.87 |

Fig. 31- 47

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Irg1 | 1.00 | 1.00 | 1.00 | 1.62 | 1.00 | 1.00 | 1.00 | 1.00 | 1.00 |
| Isg20 | 1.00 | 1.55 | 1.00 | 1.35 | 7.35 | 1.02 | 0.88 | 1.05 | 1.02 |
| Ism1 | 1.10 | 0.98 | 0.91 | 1.37 | 3.69 | 1.54 | 1.00 | 1.00 | 1.00 |
| Itih4 | 1.00 | 1.00 | 1.00 | 1.00 | 1.00 | 1.00 | 1.00 | 1.00 | 1.00 |
| Itln1 | 1.00 | 1.00 | 1.00 | 1.00 | 1.00 | 1.00 | 1.00 | 1.00 | 1.00 |
| Jakmip1 | 0.95 | 1.00 | 0.91 | 1.00 | 2.86 | 1.00 | 1.02 | 0.86 | 1.07 |
| Kap | 0.19 | 1.00 | 0.25 | 1.44 | 3.09 | 12.46 | 1.00 | 1.00 | 1.00 |
| Kcnc4 | 0.95 | 1.00 | 0.97 | 1.00 | 6.17 | 1.00 | 1.00 | 1.00 | 1.00 |
| Kcnh3 | 1.04 | 1.02 | 0.83 | 1.00 | 18.64 | 1.00 | 1.00 | 1.00 | 1.00 |
| Kcnmb4 | 0.95 | 1.05 | 0.94 | 1.00 | 6.35 | 1.00 | 1.04 | 1.07 | 1.02 |
| Kif11 | 1.00 | 1.31 | 1.00 | 1.00 | 1.00 | 1.00 | 0.97 | 1.03 | 0.99 |
| Kif15 | 1.00 | 1.00 | 1.00 | 1.00 | 1.00 | 1.00 | 0.87 | 0.96 | 0.96 |
| Kif18b | 1.00 | 1.00 | 1.00 | 1.00 | 1.00 | 1.00 | 1.27 | 1.13 | 1.11 |
| Kif22 | 0.97 | 1.16 | 1.26 | 1.00 | 1.10 | 0.89 | 1.08 | 1.10 | 0.99 |
| Kif2c | 1.00 | 1.00 | 1.00 | 1.00 | 1.00 | 1.00 | 1.03 | 1.00 | 0.99 |
| Kifc1 | 0.81 | 1.29 | 1.33 | 1.00 | 0.92 | 1.00 | 1.09 | 1.07 | 0.98 |
| Kifc5b | 0.94 | 1.10 | 1.20 | 1.00 | 1.01 | 1.00 | 1.09 | 1.06 | 1.03 |
| Klhl23 | 0.92 | 0.98 | 0.99 | 0.93 | 5.62 | 1.00 | 0.86 | 0.90 | 0.95 |
| Klhl34 | 1.10 | 1.07 | 1.05 | 1.00 | 6.36 | 1.00 | 1.00 | 1.00 | 1.00 |
| Klhl6 | 1.00 | 4.25 | 1.00 | 1.26 | 1.38 | 0.60 | 1.00 | 1.00 | 1.00 |
| Knstrn | 1.00 | 1.00 | 1.00 | 1.00 | 1.01 | 1.00 | 1.03 | 1.00 | 1.00 |
| Krt13 | 1.00 | 1.00 | 1.00 | 1.00 | 1.00 | 1.00 | 1.00 | 1.00 | 1.00 |
| Krt14 | 1.00 | 1.00 | 1.00 | 1.00 | 10.56 | 1.00 | 1.00 | 1.00 | 1.00 |
| Krt15 | 1.00 | 1.00 | 1.00 | 1.00 | 11.18 | 1.00 | 1.00 | 1.00 | 1.06 |
| Krt18 | 1.17 | 0.84 | 1.34 | 0.79 | 2.27 | 0.57 | 1.00 | 1.00 | 1.07 |
| Krt4 | 1.00 | 1.00 | 1.00 | 1.00 | 1.00 | 1.00 | 1.00 | 1.00 | 1.00 |
| Krt5 | 1.00 | 1.00 | 1.00 | 1.00 | 11.77 | 1.00 | 1.00 | 1.00 | 1.00 |
| Krt78 | 1.00 | 1.00 | 1.00 | 1.00 | 1.00 | 1.00 | 1.00 | 1.00 | 1.00 |
| Laptm5 | 0.90 | 1.29 | 0.97 | 1.30 | 1.02 | 0.56 | 0.83 | 0.87 | 1.00 |
| Lars2 | 0.91 | 1.02 | 0.75 | 1.07 | 7.12 | 1.27 | 0.58 | 1.19 | 1.02 |
| Lce1a1 | 1.00 | 1.00 | 1.00 | 1.00 | 1.00 | 1.00 | 1.00 | 1.00 | 1.00 |
| Lce1a2 | 1.00 | 1.00 | 1.00 | 1.00 | 1.00 | 1.00 | 1.00 | 1.00 | 1.00 |
| Lce1b | 1.00 | 1.00 | 1.00 | 1.00 | 1.00 | 1.00 | 1.00 | 1.00 | 1.00 |
| Lce1d | 1.00 | 1.00 | 1.00 | 1.00 | 1.00 | 1.00 | 1.00 | 1.00 | 1.00 |
| Lce3a | 1.00 | 1.00 | 1.00 | 1.00 | 1.00 | 1.00 | 1.00 | 1.00 | 1.00 |
| Lce3b | 1.00 | 1.00 | 1.00 | 1.00 | 1.00 | 1.00 | 1.00 | 1.00 | 1.00 |
| Lce3c | 1.00 | 1.00 | 1.00 | 1.00 | 1.00 | 1.00 | 1.00 | 1.00 | 1.00 |
| Lce3d | 1.00 | 1.00 | 1.00 | 1.00 | 1.00 | 1.00 | 1.00 | 1.00 | 1.00 |
| Lce3e | 1.00 | 1.00 | 1.00 | 1.00 | 1.00 | 1.00 | 1.00 | 1.00 | 1.00 |
| Lce3f | 1.00 | 1.00 | 1.00 | 1.00 | 1.00 | 1.00 | 1.00 | 1.00 | 1.00 |
| Lcn12 | 1.00 | 1.00 | 1.00 | 1.00 | 38.12 | 1.00 | 1.00 | 1.00 | 1.00 |
| Lcn2 | 2.47 | 1.86 | 1.34 | 1.73 | 0.72 | 0.48 | 0.73 | 1.25 | 1.50 |
| Lcn5 | 1.00 | 1.00 | 1.00 | 1.00 | 5998.39 | 1.00 | 1.00 | 1.00 | 1.00 |
| Lcn6 | 1.00 | 1.00 | 1.00 | 1.00 | 15.51 | 1.00 | 1.00 | 1.00 | 1.00 |
| Lcn8 | 1.00 | 1.00 | 1.00 | 1.00 | 16.29 | 1.00 | 1.00 | 1.00 | 1.00 |
| Lcn9 | 1.00 | 1.00 | 1.00 | 1.00 | 7.34 | 1.00 | 1.00 | 1.00 | 1.00 |
| Ldb3 | 0.71 | 1.14 | 1.07 | 1.05 | 0.66 | 1.44 | 1.00 | 1.00 | 1.00 |
| Lef1 | 0.76 | 1.32 | 1.05 | 1.00 | 1.90 | 1.00 | 1.00 | 0.96 | 0.99 |
| Lgals3 | 1.00 | 1.39 | 1.00 | 1.66 | 1.74 | 0.65 | 1.00 | 1.00 | 1.00 |
| Lgr5 | 1.03 | 1.06 | 1.10 | 1.00 | 1.00 | 1.00 | 0.94 | 1.08 | 0.91 |
| Lingo1 | 0.96 | 1.00 | 0.92 | 1.00 | 16.23 | 1.00 | 1.06 | 0.93 | 1.00 |
| Lipg | 1.13 | 1.26 | 1.30 | 1.49 | 21.03 | 1.02 | 0.73 | 0.76 | 1.14 |
| Lmnb1 | 0.95 | 1.85 | 1.04 | 1.16 | 1.18 | 0.85 | 1.02 | 1.02 | 0.94 |
| LOC547349 | 1.00 | 1.00 | 1.00 | 1.72 | 1.00 | 1.15 | 1.20 | 1.80 | 1.59 |
| Lor | 0.87 | 1.05 | 1.18 | 1.00 | 1.00 | 1.00 | 1.00 | 1.00 | 1.00 |
| Lox | 1.00 | 1.00 | 1.00 | 2.27 | 1.26 | 1.23 | 1.00 | 1.00 | 1.00 |
| Loxl3 | 0.86 | 0.96 | 0.99 | 0.96 | 0.94 | 0.89 | 1.00 | 1.00 | 1.00 |
| Lpin1 | 1.13 | 1.00 | 1.01 | 2.05 | 0.93 | 0.75 | 1.08 | 1.01 | 1.03 |
| Lrcol1 | 1.00 | 1.00 | 1.00 | 1.00 | 112.61 | 1.00 | 0.93 | 1.00 | 1.11 |
| Lrmp | 1.00 | 3.90 | 1.00 | 1.47 | 1.28 | 0.52 | 1.00 | 1.05 | 0.86 |
| Ltbp2 | 1.05 | 1.07 | 1.43 | 0.79 | 1.54 | 1.07 | 0.88 | 1.02 | 0.93 |
| Ly6g5b | 1.00 | 1.00 | 1.00 | 1.00 | 5.06 | 1.00 | 1.00 | 1.00 | 1.00 |
| Ly6g5c | 1.00 | 1.00 | 1.00 | 1.00 | 11.49 | 1.00 | 1.00 | 1.00 | 1.00 |
| Ly9 | 1.00 | 1.00 | 1.00 | 1.03 | 1.67 | 0.59 | 0.85 | 0.85 | 0.99 |

Fig. 31- 48

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Irg1 | 0.42 | 5.56 | 1.00 | 0.47 | 3.69 | 1.23 | 1.00 | 1.00 | 1.00 | 1.00 | 1.00 | 1.00 |
| Isg20 | 1.00 | 0.91 | 0.73 | 1.03 | 1.08 | 1.38 | 0.85 | 1.35 | 1.22 | 1.42 | 1.11 | 1.10 |
| Ism1 | 1.29 | 1.65 | 1.00 | 1.00 | 1.00 | 1.00 | 1.00 | 1.00 | 1.00 | 1.19 | 1.00 | 1.00 |
| Itih4 | 0.55 | 2.24 | 1.13 | 1.00 | 1.00 | 1.00 | 0.60 | 5.43 | 1.38 | 1.00 | 1.03 | 1.04 |
| Itln1 | 1.34 | 13.73 | 1.00 | 1.00 | 0.94 | 0.77 | 0.33 | 1.28 | 1.00 | 0.87 | 1.03 | 1.18 |
| Jakmip1 | 0.79 | 0.75 | 0.80 | 0.96 | 0.51 | 0.80 | 1.00 | 1.00 | 1.00 | 1.00 | 1.00 | 1.00 |
| Kap | 1.00 | 1.00 | 1.00 | 1.00 | 1.00 | 1.00 | 1.00 | 1.00 | 1.00 | 1.00 | 0.94 | 0.79 |
| Kcnc4 | 1.00 | 1.00 | 1.00 | 1.00 | 1.00 | 1.00 | 1.00 | 1.00 | 1.00 | 1.40 | 1.00 | 1.00 |
| Kcnh3 | 0.88 | 0.82 | 0.58 | 1.00 | 1.00 | 1.00 | 1.00 | 1.00 | 1.00 | 1.00 | 1.00 | 1.00 |
| Kcnmb4 | 0.72 | 0.63 | 0.81 | 1.00 | 1.00 | 1.00 | 1.00 | 1.00 | 1.00 | 0.70 | 1.00 | 1.00 |
| Kif11 | 0.34 | 0.63 | 0.92 | 0.99 | 1.03 | 1.07 | 1.00 | 1.00 | 1.00 | 1.08 | 1.00 | 1.00 |
| Kif15 | 0.39 | 0.59 | 0.96 | 0.92 | 0.97 | 0.98 | 1.00 | 1.00 | 1.00 | 1.00 | 1.01 | 0.99 |
| Kif18b | 0.35 | 0.67 | 0.92 | 1.02 | 0.98 | 1.02 | 1.00 | 1.00 | 1.00 | 0.85 | 1.00 | 1.00 |
| Kif22 | 0.52 | 0.69 | 0.92 | 1.03 | 0.95 | 1.03 | 1.00 | 1.00 | 1.00 | 0.83 | 0.98 | 0.87 |
| Kif2c | 0.40 | 0.72 | 0.88 | 1.04 | 1.06 | 1.00 | 1.00 | 1.00 | 1.00 | 0.83 | 1.28 | 1.01 |
| Kifc1 | 0.50 | 0.70 | 0.87 | 1.11 | 0.99 | 1.05 | 1.00 | 1.00 | 1.00 | 0.75 | 0.96 | 1.13 |
| Kifc5b | 0.59 | 0.71 | 0.82 | 1.10 | 0.95 | 1.01 | 1.00 | 1.00 | 1.00 | 0.90 | 1.12 | 1.00 |
| Klhl23 | 0.79 | 0.77 | 0.81 | 1.02 | 0.97 | 1.21 | 1.00 | 1.00 | 1.00 | 0.97 | 0.98 | 0.94 |
| Klhl34 | 1.00 | 1.00 | 1.00 | 1.00 | 1.00 | 1.00 | 1.00 | 1.00 | 1.00 | 1.00 | 0.66 | 1.05 |
| Klhl6 | 0.92 | 0.87 | 0.94 | 1.01 | 0.87 | 1.00 | 1.00 | 1.00 | 1.00 | 1.13 | 1.01 | 1.08 |
| Knstrn | 0.41 | 0.69 | 0.87 | 0.98 | 0.98 | 1.01 | 1.00 | 1.00 | 1.00 | 0.92 | 1.00 | 1.00 |
| Krt13 | 1.52 | 268.30 | 1.00 | 1.00 | 1.00 | 1.00 | 1.00 | 1.00 | 1.00 | 1.00 | 1.08 | 1.06 |
| Krt14 | 1.12 | 0.88 | 0.98 | 1.00 | 1.00 | 1.00 | 1.00 | 1.00 | 1.00 | 0.81 | 0.89 | 1.05 |
| Krt15 | 1.30 | 3.87 | 0.60 | 1.00 | 1.00 | 1.00 | 1.00 | 1.00 | 1.00 | 0.92 | 1.27 | 1.00 |
| Krt18 | 0.98 | 0.73 | 0.75 | 0.87 | 0.77 | 0.62 | 1.15 | 0.93 | 0.93 | 1.00 | 0.82 | 0.81 |
| Krt4 | 1.13 | 113.94 | 1.00 | 1.00 | 1.00 | 1.00 | 1.00 | 1.00 | 1.00 | 1.05 | 0.71 | 0.84 |
| Krt5 | 1.08 | 0.88 | 0.97 | 1.00 | 1.00 | 1.00 | 1.00 | 1.00 | 1.00 | 0.78 | 0.83 | 1.08 |
| Krt78 | 1.10 | 5.95 | 1.01 | 1.00 | 1.00 | 1.00 | 1.00 | 1.00 | 1.00 | 0.97 | 0.89 | 0.97 |
| Laptm5 | 0.90 | 1.01 | 1.03 | 1.07 | 1.09 | 1.07 | 1.03 | 0.56 | 0.49 | 1.09 | 5.38 | 2.70 |
| Lars2 | 2.92 | 0.96 | 1.21 | 0.40 | 0.85 | 1.07 | 0.65 | 1.16 | 0.86 | 1.03 | 1.03 | 1.17 |
| Lce1a1 | 0.78 | 7.37 | 1.00 | 1.00 | 1.00 | 1.00 | 1.00 | 1.00 | 1.00 | 1.02 | 1.00 | 1.00 |
| Lce1a2 | 1.00 | 6.09 | 1.00 | 1.00 | 1.00 | 1.00 | 1.00 | 1.00 | 1.00 | 0.97 | 0.98 | 1.02 |
| Lce1b | 0.98 | 6.04 | 1.00 | 1.00 | 1.00 | 1.00 | 1.00 | 1.00 | 1.00 | 0.99 | 1.02 | 0.96 |
| Lce1d | 0.90 | 6.50 | 1.00 | 1.00 | 1.00 | 1.00 | 1.00 | 1.00 | 1.00 | 1.01 | 0.98 | 1.04 |
| Lce3a | 1.00 | 18.64 | 1.00 | 1.00 | 1.00 | 1.00 | 1.00 | 1.00 | 1.00 | 1.95 | 0.91 | 0.94 |
| Lce3b | 1.00 | 13.98 | 1.00 | 1.00 | 1.00 | 1.00 | 1.00 | 1.00 | 1.00 | 3.34 | 0.95 | 0.99 |
| Lce3c | 1.00 | 15.23 | 1.00 | 1.00 | 1.00 | 1.00 | 1.00 | 1.00 | 1.00 | 2.05 | 1.12 | 1.07 |
| Lce3d | 1.00 | 7.70 | 1.00 | 1.00 | 1.00 | 1.00 | 1.00 | 1.00 | 1.00 | 4.22 | 1.13 | 1.08 |
| Lce3e | 1.00 | 12.05 | 1.00 | 1.00 | 1.00 | 1.00 | 1.00 | 1.00 | 1.00 | 3.76 | 0.95 | 1.02 |
| Lce3f | 1.00 | 13.85 | 1.00 | 1.00 | 1.00 | 1.00 | 1.00 | 1.00 | 1.00 | 3.75 | 0.94 | 0.96 |
| Lcn12 | 1.00 | 1.00 | 1.00 | 1.00 | 1.00 | 1.00 | 1.00 | 1.00 | 1.00 | 1.00 | 1.00 | 1.05 |
| Lcn2 | 1.16 | 2.51 | 1.19 | 0.96 | 1.25 | 1.13 | 1.15 | 0.98 | 1.00 | 1.51 | 0.89 | 0.93 |
| Lcn5 | 1.00 | 1.00 | 1.00 | 1.00 | 1.00 | 1.00 | 1.00 | 1.00 | 1.00 | 1.00 | 1.08 | 0.90 |
| Lcn6 | 1.00 | 1.00 | 1.00 | 1.00 | 1.00 | 1.00 | 1.00 | 1.00 | 1.00 | 1.00 | 0.90 | 0.86 |
| Lcn8 | 1.00 | 1.00 | 1.00 | 1.00 | 1.00 | 1.00 | 1.00 | 1.00 | 1.00 | 1.00 | 1.04 | 1.00 |
| Lcn9 | 1.00 | 1.00 | 1.00 | 1.00 | 1.00 | 1.00 | 1.00 | 1.00 | 1.00 | 1.00 | 0.89 | 1.00 |
| Ldb3 | 2.08 | 5.28 | 3.28 | 1.00 | 1.00 | 1.00 | 1.00 | 1.00 | 1.00 | 1.36 | 1.05 | 1.15 |
| Lef1 | 0.78 | 0.75 | 0.95 | 1.08 | 0.75 | 0.74 | 1.00 | 1.00 | 1.00 | 0.89 | 0.90 | 0.87 |
| Lgals3 | 1.07 | 1.23 | 1.12 | 1.18 | 1.26 | 1.09 | 0.99 | 0.80 | 1.00 | 0.95 | 1.01 | 1.00 |
| Lgr5 | 1.00 | 1.00 | 1.00 | 1.04 | 0.66 | 0.73 | 1.00 | 1.00 | 1.00 | 0.77 | 1.18 | 1.00 |
| Lingo1 | 1.00 | 1.36 | 1.00 | 1.00 | 1.00 | 1.00 | 1.00 | 1.00 | 1.00 | 0.81 | 1.00 | 1.21 |
| Lipg | 1.60 | 1.73 | 4.82 | 0.11 | 1.63 | 1.00 | 1.00 | 1.00 | 1.00 | 0.83 | 1.00 | 1.00 |
| Lmnb1 | 0.62 | 0.64 | 0.88 | 0.88 | 1.06 | 1.01 | 0.99 | 0.92 | 1.00 | 0.72 | 1.00 | 1.00 |
| LOC547349 | 1.21 | 1.01 | 0.26 | 1.55 | 1.39 | 1.27 | 0.99 | 0.74 | 1.00 | 1.15 | 0.78 | 1.18 |
| Lor | 1.11 | 33.94 | 1.01 | 1.00 | 1.00 | 1.00 | 1.00 | 1.00 | 1.00 | 0.90 | 1.00 | 1.00 |
| Lox | 1.29 | 1.42 | 2.12 | 1.00 | 1.00 | 1.00 | 1.00 | 1.00 | 1.00 | 1.38 | 0.92 | 1.03 |
| Loxl3 | 1.28 | 1.16 | 1.25 | 1.04 | 1.01 | 1.04 | 1.00 | 1.00 | 1.00 | 1.23 | 0.96 | 1.07 |
| Lpin1 | 1.05 | 1.16 | 1.56 | 1.03 | 1.00 | 1.05 | 0.96 | 0.99 | 1.47 | 1.22 | 0.84 | 0.95 |
| Lrcol1 | 1.00 | 1.00 | 1.00 | 1.00 | 1.00 | 1.00 | 1.00 | 1.00 | 1.00 | 1.00 | 1.00 | 1.00 |
| Lrmp | 1.06 | 0.76 | 0.72 | 1.00 | 0.65 | 0.86 | 0.85 | 0.80 | 1.11 | 1.14 | 0.92 | 1.03 |
| Ltbp2 | 1.11 | 1.00 | 1.61 | 1.00 | 1.00 | 1.00 | 1.00 | 1.00 | 1.00 | 0.92 | 0.85 | 0.88 |
| Ly6g5b | 1.13 | 0.55 | 0.57 | 1.44 | 0.87 | 0.63 | 1.00 | 1.00 | 1.00 | 0.91 | 1.04 | 1.07 |
| Ly6g5c | 1.00 | 1.00 | 1.00 | 1.00 | 1.00 | 1.00 | 1.00 | 1.00 | 1.00 | 1.00 | 0.54 | 1.28 |
| Ly9 | 0.79 | 1.22 | 1.03 | 0.94 | 0.98 | 0.90 | 1.00 | 1.00 | 1.00 | 1.17 | 1.03 | 0.77 |

Fig. 31- 49

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mal | 0.90 | 0.60 | 0.94 | 1.05 | 1.06 | 0.94 | 1.00 | 1.00 | 1.00 |
| Man1a | 1.09 | 1.16 | 1.23 | 1.01 | 0.87 | 0.97 | 1.15 | 0.86 | 0.91 |
| Marco | 1.00 | 0.91 | 1.42 | 1.00 | 1.00 | 1.00 | 0.37 | 3.34 | 2.77 |
| Matn4 | 1.00 | 5.84 | 2.21 | 1.00 | 0.97 | 1.00 | 1.00 | 1.00 | 1.00 |
| Mb | 0.67 | 0.58 | 0.72 | 1.00 | 1.00 | 1.00 | 1.00 | 1.00 | 1.00 |
| Mbnl3 | 1.00 | 1.00 | 1.00 | 1.00 | 1.00 | 1.00 | 1.00 | 1.00 | 1.00 |
| Mboat2 | 1.16 | 0.63 | 0.56 | 1.23 | 1.09 | 0.75 | 1.00 | 1.00 | 1.00 |
| Mfap4 | 0.68 | 4.00 | 6.78 | 1.02 | 0.95 | 1.51 | 1.11 | 0.88 | 1.02 |
| Mfrp | 1.00 | 1.00 | 1.00 | 0.87 | 1.38 | 1.00 | 1.00 | 1.00 | 1.00 |
| Mfsd2a | 1.00 | 1.00 | 1.00 | 0.62 | 1.02 | 1.45 | 18.46 | 0.80 | 0.30 |
| Mir100 | 1.00 | 1.00 | 1.00 | 1.00 | 1.00 | 1.00 | 1.00 | 1.00 | 1.00 |
| Mir101b | 1.00 | 1.00 | 1.00 | 1.00 | 1.00 | 1.00 | 1.00 | 1.00 | 1.00 |
| Mir103-2 | 0.08 | 10.06 | 1.00 | 1.76 | 0.07 | 0.52 | 14.27 | 1.00 | 0.12 |
| Mir106b | 1.00 | 1.00 | 1.00 | 42.07 | 1.00 | 1.98 | 1.00 | 19.53 | 18.02 |
| Mir107 | 1.00 | 1.00 | 1.00 | 1.00 | 1.00 | 1.00 | 1.00 | 1.00 | 1.00 |
| Mir10a | 1.00 | 1.00 | 1.00 | 5.98 | 0.79 | 0.23 | 1.00 | 1.00 | 1.00 |
| Mir10b | 1.00 | 1.00 | 1.00 | 0.02 | 0.02 | 1.00 | 1.00 | 1.00 | 1.00 |
| Mir1190 | 1.00 | 1.00 | 1.00 | 1.00 | 1.00 | 1.00 | 1.00 | 1.00 | 1.00 |
| Mir1191b | 1.00 | 1.00 | 66.21 | 1.00 | 1.00 | 1.00 | 1.00 | 1.00 | 1.00 |
| Mir1192 | 0.27 | 0.34 | 0.93 | 0.85 | 2.09 | 1.54 | 0.38 | 0.88 | 2.75 |
| Mir1199 | 0.39 | 2.37 | 1.00 | 2.40 | 0.93 | 2.45 | 1.17 | 1.00 | 1.00 |
| Mir1224 | 0.08 | 1.00 | 1.00 | 1.00 | 1.00 | 1.00 | 1.00 | 1.00 | 1.00 |
| Mir1231 | 1.00 | 0.46 | 0.06 | 1.00 | 1.00 | 1.00 | 1.00 | 1.00 | 1.00 |
| Mir1247 | 1.00 | 1.70 | 25.39 | 0.03 | 1.15 | 1.03 | 1.00 | 0.06 | 0.97 |
| Mir1249 | 1.79 | 0.86 | 2.55 | 0.89 | 1.91 | 2.04 | 8.26 | 0.86 | 1.74 |
| Mir124a-3 | 1.00 | 1.00 | 1.00 | 1.00 | 1.00 | 1.00 | 1.00 | 1.00 | 1.00 |
| Mir1251 | 1.00 | 1.00 | 1.00 | 1.00 | 1.00 | 1.00 | 1.00 | 1.00 | 1.00 |
| Mir1258 | 1.00 | 1.00 | 0.92 | 1.00 | 1.00 | 0.52 | 0.17 | 0.01 | 1.00 |
| Mir125a | 1.00 | 0.45 | 1.00 | 51.44 | 1.14 | 1.00 | 1.00 | 1.00 | 1.00 |
| Mir125b-1 | 1.00 | 1.00 | 1.00 | 1.00 | 1.00 | 1.00 | 1.00 | 1.00 | 1.00 |
| Mir125b-2 | 1.00 | 1.00 | 1.00 | 1.00 | 1.00 | 1.00 | 1.00 | 1.00 | 1.00 |
| Mir126 | 1.31 | 0.23 | 2.56 | 0.03 | 3.19 | 0.30 | 1.00 | 1.00 | 0.47 |
| Mir126b | 0.01 | 84.82 | 0.00 | 1.00 | 73.53 | 0.01 | 1.00 | 140.31 | 1.00 |
| Mir127 | 1.00 | 1.00 | 1.00 | 1.00 | 1.00 | 1.00 | 1.00 | 1.00 | 1.00 |
| Mir129-2 | 1.00 | 1.00 | 1.00 | 1.00 | 1.00 | 1.00 | 1.00 | 1.00 | 1.00 |
| Mir1306 | 0.34 | 0.31 | 15.87 | 1.10 | 0.13 | 0.63 | 0.20 | 37.50 | 3.48 |
| Mir130a | 1.00 | 1.00 | 1.00 | 1.00 | 1.00 | 1.00 | 1.00 | 1.00 | 1.00 |
| Mir130c | 0.10 | 148.98 | 0.05 | 82.44 | 0.06 | 1.00 | 0.06 | 28.60 | 3.11 |
| Mir132 | 1.00 | 1.00 | 1.00 | 1.00 | 1.00 | 1.00 | 1.00 | 1.00 | 1.00 |
| Mir133a-1 | 1.45 | 1.28 | 0.58 | 1.00 | 1.00 | 1.00 | 1.00 | 1.00 | 1.00 |
| Mir133a-2 | 0.46 | 0.29 | 0.30 | 1.00 | 6.96 | 5.55 | 1.00 | 1.00 | 1.00 |
| Mir133c | 1.00 | 1.00 | 1.00 | 1.00 | 1.00 | 1.00 | 1.00 | 0.05 | 1.00 |
| Mir134 | 1.00 | 22.50 | 1.00 | 1.00 | 1.00 | 1.00 | 1.00 | 1.00 | 1.00 |
| Mir135a-1 | 2.38 | 1.00 | 1.15 | 1.20 | 0.93 | 2.22 | 0.62 | 0.86 | 0.70 |
| Mir135a-2 | 1.00 | 1.00 | 1.00 | 1.00 | 1.00 | 1.00 | 1.00 | 1.00 | 1.00 |
| Mir138-1 | 1.00 | 1.00 | 1.00 | 1.00 | 1.00 | 1.00 | 1.00 | 1.00 | 1.00 |
| Mir140 | 1.00 | 1.00 | 1.00 | 1.00 | 1.00 | 1.00 | 1.00 | 1.00 | 1.00 |
| Mir141 | 1.00 | 1.00 | 1.00 | 1.00 | 1.00 | 1.00 | 1.00 | 1.00 | 1.00 |
| Mir142 | 1.00 | 46.96 | 1.00 | 1.00 | 1.00 | 1.00 | 1.00 | 1.00 | 1.00 |
| Mir142b | 4.61 | 2.25 | 1.65 | 5.05 | 3.05 | 0.56 | 1.00 | 0.23 | 1.00 |
| Mir143 | 0.87 | 1.00 | 1.00 | 1.00 | 1.00 | 1.00 | 1.00 | 1.00 | 1.00 |
| Mir144 | 1.00 | 1.00 | 1.00 | 1.00 | 1.00 | 1.00 | 1.00 | 1.00 | 1.00 |
| Mir145 | 1.76 | 1.46 | 1.18 | 1.00 | 1.00 | 0.03 | 1.00 | 1.00 | 1.00 |
| Mir146 | 1.00 | 1.00 | 1.00 | 1.00 | 1.00 | 0.02 | 1.00 | 1.00 | 1.00 |
| Mir147 | 14.52 | 0.18 | 1.00 | 1.00 | 0.05 | 0.29 | 1.00 | 1.00 | 1.00 |
| Mir149 | 1.00 | 1.00 | 1.00 | 1.00 | 1.00 | 1.00 | 1.00 | 1.00 | 1.00 |
| Mir150 | 1.00 | 1.00 | 1.00 | 1.00 | 1.00 | 1.00 | 1.00 | 1.00 | 1.00 |
| Mir154 | 1.00 | 1.00 | 1.00 | 1.00 | 1.00 | 1.00 | 1.00 | 1.00 | 1.00 |
| Mir155 | 1.00 | 1.00 | 1.00 | 1.00 | 1.00 | 1.00 | 1.00 | 1.00 | 1.00 |
| Mir15a | 12.44 | 1.00 | 1.00 | 1.00 | 18.23 | 0.08 | 1.00 | 1.00 | 1.00 |
| Mir16-1 | 1.00 | 7.81 | 1.00 | 1.18 | 1.00 | 1.00 | 1.00 | 1.00 | 1.00 |
| Mir1668 | 1.63 | 0.51 | 3.31 | 1.17 | 17.22 | 0.12 | 5.58 | 1.84 | 5.78 |
| Mir17 | 1.00 | 1.00 | 1.00 | 1.38 | 1.13 | 13.05 | 1.00 | 1.00 | 1.00 |
| Mir18 | 1.00 | 1.00 | 1.00 | 8.98 | 18.62 | 1.00 | 8.50 | 1.00 | 1.00 |

Fig. 31- 50

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mal | 1.31 | 0.91 | 1.48 | 1.06 | 0.99 | 1.01 | 1.32 | 0.71 | 0.96 |
| Man1a | 1.05 | 1.46 | 1.17 | 1.03 | 1.00 | 1.03 | 1.05 | 0.98 | 0.72 |
| Marco | 1.56 | 0.89 | 4.04 | 1.00 | 1.00 | 1.00 | 1.38 | 0.42 | 1.52 |
| Matn4 | 0.95 | 0.71 | 0.98 | 0.96 | 0.68 | 0.97 | 1.46 | 0.90 | 1.00 |
| Mb | 0.46 | 1.57 | 2.34 | 0.75 | 0.94 | 0.91 | 1.00 | 1.00 | 1.00 |
| Mbnl3 | 1.04 | 1.77 | 0.87 | 1.00 | 1.00 | 1.00 | 0.88 | 0.86 | 1.17 |
| Mboat2 | 1.03 | 0.87 | 0.90 | 1.00 | 1.00 | 1.00 | 0.93 | 1.12 | 2.83 |
| Mfap4 | 1.00 | 0.69 | 1.38 | 0.79 | 0.90 | 1.20 | 0.95 | 0.91 | 0.98 |
| Mfrp | 1.00 | 1.00 | 1.00 | 1.00 | 1.00 | 1.00 | 1.00 | 1.00 | 1.00 |
| Mfsd2a | 3.14 | 1.66 | 2.66 | 1.00 | 1.00 | 1.00 | 1.00 | 1.00 | 1.00 |
| Mir100 | 1.00 | 1.00 | 1.00 | 1.00 | 1.00 | 1.00 | 19.54 | 1.00 | 1.00 |
| Mir101b | 5.73 | 1.00 | 1.00 | 1.00 | 1.00 | 1.00 | 1.00 | 1.00 | 1.00 |
| Mir103-2 | 0.43 | 0.21 | 5.31 | 1.00 | 0.10 | 0.09 | 41.22 | 0.06 | 0.94 |
| Mir106b | 0.09 | 1.10 | 1.00 | 1.00 | 0.04 | 1.00 | 1.00 | 1.00 | 1.00 |
| Mir107 | 1.00 | 1.00 | 1.00 | 1.00 | 1.00 | 1.00 | 1.00 | 1.00 | 1.00 |
| Mir10a | 0.44 | 1.84 | 2.01 | 0.25 | 1.00 | 1.00 | 1.00 | 1.00 | 1.00 |
| Mir10b | 1.00 | 1.00 | 1.00 | 1.00 | 1.00 | 1.00 | 1.00 | 1.00 | 1.00 |
| Mir1190 | 1.00 | 1.00 | 1.00 | 1.00 | 1.00 | 1.00 | 1.00 | 1.00 | 1.00 |
| Mir1191b | 1.00 | 0.02 | 1.00 | 1.00 | 1.00 | 1.00 | 1.00 | 1.00 | 119.91 |
| Mir1192 | 2.08 | 5.23 | 0.26 | 0.10 | 0.34 | 2.87 | 1.00 | 1.00 | 3.36 |
| Mir1199 | 0.43 | 0.49 | 0.73 | 1.00 | 5.64 | 21.52 | 2.87 | 1.00 | 1.00 |
| Mir1224 | 1.00 | 0.50 | 1.00 | 1.00 | 1.00 | 1.00 | 1.00 | 1.00 | 1.00 |
| Mir1231 | 0.09 | 0.09 | 0.08 | 1.00 | 1.00 | 1.00 | 1.00 | 1.00 | 0.42 |
| Mir1247 | 0.05 | 0.03 | 1.08 | 0.04 | 1.00 | 1.00 | 1.00 | 1.00 | 0.05 |
| Mir1249 | 2.38 | 3.10 | 0.55 | 3.73 | 0.28 | 0.48 | 0.77 | 0.56 | 0.98 |
| Mir124a-3 | 1.00 | 1.00 | 1.00 | 1.00 | 1.00 | 1.00 | 1.00 | 1.00 | 1.00 |
| Mir1251 | 1.00 | 1.00 | 1.00 | 1.00 | 1.00 | 1.00 | 1.00 | 1.00 | 1.00 |
| Mir1258 | 48.68 | 1.00 | 1.00 | 1.00 | 1.00 | 1.00 | 105.64 | 1.00 | 1.00 |
| Mir125a | 0.78 | 1.10 | 1.07 | 1.00 | 0.04 | 1.00 | 1.00 | 1.00 | 1.00 |
| Mir125b-1 | 1.00 | 1.00 | 1.00 | 1.00 | 1.00 | 1.00 | 1.00 | 1.00 | 1.00 |
| Mir125b-2 | 1.00 | 1.00 | 1.00 | 1.00 | 1.00 | 1.00 | 1.00 | 1.00 | 1.00 |
| Mir126 | 0.66 | 0.51 | 1.02 | 0.02 | 0.05 | 0.40 | 0.32 | 2.20 | 0.21 |
| Mir126b | 0.25 | 23.12 | 84.86 | 72.02 | 0.02 | 0.63 | 1.00 | 1.00 | 119.91 |
| Mir127 | 1.00 | 1.00 | 1.00 | 1.00 | 0.05 | 1.00 | 1.00 | 1.00 | 1.00 |
| Mir129-2 | 1.00 | 1.00 | 1.00 | 1.00 | 1.00 | 1.00 | 1.00 | 1.00 | 1.00 |
| Mir1306 | 1.01 | 0.09 | 3.90 | 35.42 | 0.31 | 2.21 | 0.77 | 1.63 | 1.44 |
| Mir130a | 1.00 | 1.00 | 1.00 | 1.00 | 1.00 | 1.00 | 69.25 | 0.52 | 1.00 |
| Mir130c | 0.23 | 0.06 | 2.82 | 0.44 | 0.65 | 0.32 | 1.24 | 23.06 | 0.01 |
| Mir132 | 1.00 | 0.04 | 1.00 | 1.00 | 1.00 | 1.00 | 1.00 | 1.00 | 47.10 |
| Mir133a-1 | 1.00 | 1.00 | 27.47 | 0.42 | 2.38 | 0.73 | 1.00 | 57.74 | 1.00 |
| Mir133a-2 | 1.00 | 20.28 | 0.23 | 1.55 | 2.03 | 0.16 | 1.00 | 7.40 | 11.94 |
| Mir133c | 1.00 | 13.39 | 1.00 | 1.00 | 0.08 | 1.00 | 1.00 | 1.00 | 1.00 |
| Mir134 | 1.00 | 1.00 | 1.00 | 1.00 | 1.00 | 1.00 | 1.00 | 1.00 | 1.00 |
| Mir135a-1 | 0.17 | 29.42 | 1.12 | 1.00 | 1.73 | 4.78 | 0.04 | 4.54 | 2.29 |
| Mir135a-2 | 1.00 | 1.00 | 1.00 | 1.00 | 1.00 | 1.00 | 1.00 | 1.00 | 1.00 |
| Mir138-1 | 1.00 | 1.00 | 1.00 | 1.00 | 1.00 | 1.00 | 1.00 | 1.00 | 1.00 |
| Mir140 | 0.02 | 0.98 | 22.53 | 0.04 | 22.83 | 1.00 | 1.00 | 0.02 | 1.00 |
| Mir141 | 1.00 | 1.00 | 1.00 | 1.00 | 1.00 | 1.00 | 1.00 | 1.00 | 1.00 |
| Mir142 | 1.00 | 1.00 | 1.00 | 1.00 | 1.00 | 1.00 | 1.00 | 1.00 | 1.00 |
| Mir142b | 0.70 | 1.08 | 0.89 | 0.15 | 0.16 | 1.00 | 0.63 | 1.16 | 0.45 |
| Mir143 | 0.03 | 0.37 | 0.03 | 129.20 | 0.03 | 1.00 | 1.00 | 81.86 | 1.00 |
| Mir144 | 1.00 | 1.00 | 1.00 | 1.00 | 1.00 | 1.00 | 0.19 | 5.81 | 1.10 |
| Mir145 | 0.69 | 0.25 | 1.22 | 0.56 | 1.32 | 0.45 | 0.46 | 49.18 | 2.18 |
| Mir146 | 1.00 | 30.17 | 67.68 | 1.00 | 1.00 | 1.00 | 120.34 | 1.00 | 1.00 |
| Mir147 | 0.43 | 0.75 | 1.00 | 1.00 | 1.00 | 1.00 | 1.00 | 1.00 | 0.09 |
| Mir149 | 1.00 | 1.00 | 1.00 | 1.00 | 1.00 | 1.00 | 1.00 | 1.00 | 1.00 |
| Mir150 | 1.00 | 1.00 | 1.00 | 1.00 | 1.00 | 1.00 | 1.00 | 67.48 | 1.00 |
| Mir154 | 1.00 | 28.02 | 1.00 | 1.00 | 1.00 | 1.00 | 1.00 | 1.00 | 1.00 |
| Mir155 | 1.00 | 1.00 | 1.00 | 1.00 | 1.00 | 1.00 | 1.00 | 1.00 | 1.00 |
| Mir15a | 1.00 | 1.00 | 0.10 | 20.64 | 1.00 | 1.00 | 1.00 | 20.01 | 0.06 |
| Mir16-1 | 1.00 | 1.00 | 1.00 | 1.00 | 1.00 | 1.00 | 0.09 | 1.00 | 9.69 |
| Mir1668 | 0.72 | 1.61 | 1.48 | 0.12 | 1.00 | 0.85 | 1.40 | 0.36 | 0.84 |
| Mir17 | 1.00 | 1.00 | 1.00 | 1.00 | 1.00 | 1.00 | 1.00 | 0.06 | 0.82 |
| Mir18 | 1.00 | 5.92 | 6.24 | 1.00 | 1.00 | 1.00 | 1.00 | 0.10 | 1.00 |

Fig. 31-51

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mal | 1.20 | 0.99 | 0.94 | 0.82 | 8.45 | 1.00 | 1.38 | 0.93 | 1.09 |
| Man1a | 1.00 | 1.13 | 1.02 | 1.29 | 6.94 | 0.78 | 1.00 | 1.00 | 1.00 |
| Marco | 1.00 | 1.00 | 1.00 | 0.74 | 0.82 | 1.02 | 1.00 | 1.00 | 1.00 |
| Matn4 | 0.97 | 0.94 | 1.07 | 0.74 | 1.49 | 0.50 | 1.00 | 1.00 | 1.00 |
| Mb | 1.00 | 1.00 | 2.38 | 0.97 | 1.35 | 0.76 | 1.00 | 1.00 | 1.00 |
| Mbnl3 | 1.00 | 1.00 | 1.00 | 1.00 | 20.60 | 1.00 | 1.00 | 1.00 | 1.00 |
| Mboat2 | 1.13 | 0.92 | 0.94 | 1.00 | 6.47 | 0.76 | 0.90 | 1.04 | 0.94 |
| Mfap4 | 0.79 | 0.95 | 1.15 | 0.66 | 0.98 | 1.48 | 0.88 | 0.93 | 0.82 |
| Mfrp | 0.87 | 1.14 | 1.91 | 1.00 | 8.65 | 1.00 | 1.00 | 1.00 | 1.00 |
| Mfsd2a | 1.47 | 0.90 | 0.84 | 1.00 | 2.98 | 1.00 | 0.82 | 0.95 | 0.89 |
| Mir100 | 1.00 | 1.00 | 0.06 | 1.00 | 1.00 | 1.00 | 1.00 | 0.91 | 12.09 |
| Mir101b | 1.00 | 1.00 | 1.00 | 1.00 | 1.00 | 1.00 | 1.00 | 1.00 | 1.00 |
| Mir103-2 | 0.46 | 42.25 | 0.55 | 45.29 | 42.33 | 0.29 | 0.05 | 0.89 | 18.20 |
| Mir106b | 1.03 | 1.00 | 1.07 | 1.00 | 0.06 | 0.07 | 0.09 | 1.68 | 1.00 |
| Mir107 | 15.91 | 1.00 | 1.00 | 1.00 | 1.00 | 1.00 | 1.00 | 1.00 | 1.00 |
| Mir10a | 1.00 | 1.00 | 1.00 | 0.19 | 19.41 | 0.24 | 0.25 | 3.59 | 1.00 |
| Mir10b | 1.00 | 1.00 | 1.00 | 1.00 | 1.00 | 1.00 | 1.00 | 0.04 | 1.00 |
| Mir1190 | 1.00 | 1.00 | 1.00 | 1.00 | 1.00 | 1.00 | 1.00 | 0.16 | 1.00 |
| Mir1191b | 1.00 | 1.00 | 1.00 | 1.00 | 1.00 | 1.00 | 61.37 | 1.00 | 1.00 |
| Mir1192 | 8.88 | 3.49 | 1.06 | 0.12 | 1.00 | 2.05 | 0.34 | 0.92 | 0.35 |
| Mir1199 | 1.00 | 0.18 | 1.00 | 0.13 | 0.22 | 1.00 | 1.00 | 1.00 | 1.00 |
| Mir1224 | 0.90 | 44.64 | 0.22 | 1.00 | 1.00 | 1.00 | 1.00 | 1.00 | 1.00 |
| Mir1231 | 1.00 | 0.05 | 1.00 | 1.32 | 0.55 | 13.91 | 1.00 | 1.00 | 1.00 |
| Mir1247 | 1.00 | 1.00 | 1.00 | 1.00 | 1.01 | 0.04 | 1.00 | 0.89 | 1.00 |
| Mir1249 | 0.88 | 1.22 | 0.89 | 1.02 | 0.96 | 0.27 | 1.09 | 2.26 | 1.05 |
| Mir124a-3 | 48.78 | 1.00 | 1.00 | 1.00 | 1.00 | 1.00 | 1.00 | 22.87 | 0.04 |
| Mir1251 | 18.90 | 0.06 | 1.00 | 1.00 | 1.00 | 1.00 | 1.00 | 1.00 | 1.00 |
| Mir1258 | 302.63 | 1.00 | 1.00 | 1.00 | 1.00 | 81.90 | 51.30 | 41.90 | 1.00 |
| Mir125a | 3.15 | 2.00 | 0.03 | 125.53 | 1.97 | 0.71 | 7.45 | 0.86 | 1.05 |
| Mir125b-1 | 1.00 | 1.00 | 20.02 | 1.00 | 1.00 | 1.00 | 1.00 | 1.00 | 1.00 |
| Mir125b-2 | 84.09 | 1.00 | 1.00 | 1.00 | 1.00 | 1.00 | 1.00 | 1.00 | 1.00 |
| Mir126 | 101.28 | 1.02 | 49.82 | 1.11 | 0.11 | 4.38 | 20.40 | 1.00 | 1.00 |
| Mir126b | 1.00 | 1.00 | 1.00 | 1.00 | 1.00 | 1.00 | 1.00 | 1.00 | 1.00 |
| Mir127 | 1.00 | 1.00 | 12.95 | 1.00 | 1.00 | 1.00 | 1.00 | 1.00 | 1.00 |
| Mir129-2 | 1.00 | 1.00 | 9.13 | 1.00 | 1.00 | 1.00 | 1.00 | 1.00 | 1.00 |
| Mir1306 | 1.61 | 0.03 | 1.25 | 117.97 | 1.80 | 1.52 | 4.12 | 0.01 | 77.27 |
| Mir130a | 1.00 | 1.00 | 1.00 | 1.00 | 1.00 | 1.00 | 0.03 | 1.00 | 1.00 |
| Mir130c | 1.00 | 0.84 | 2.25 | 39.32 | 8.02 | 2.73 | 0.41 | 0.09 | 0.63 |
| Mir132 | 1.75 | 0.01 | 0.25 | 1.00 | 1.00 | 1.00 | 1.00 | 28.31 | 0.02 |
| Mir133a-1 | 1.00 | 1.00 | 1.00 | 1.00 | 1.00 | 1.00 | 1.00 | 1.00 | 1.00 |
| Mir133a-2 | 1.00 | 1.00 | 1.00 | 1.00 | 1.00 | 1.00 | 1.00 | 1.00 | 1.00 |
| Mir133c | 1.00 | 1.00 | 1.00 | 1.00 | 1.00 | 1.00 | 1.00 | 1.00 | 1.00 |
| Mir134 | 1.00 | 0.01 | 0.37 | 1.00 | 1.00 | 1.00 | 1.00 | 1.00 | 1.00 |
| Mir135a-1 | 22.27 | 0.12 | 10.61 | 1.00 | 0.01 | 0.25 | 0.91 | 8.35 | 1.56 |
| Mir135a-2 | 6.57 | 1.00 | 1.00 | 1.00 | 1.00 | 1.00 | 1.00 | 1.00 | 1.00 |
| Mir138-1 | 1.00 | 0.13 | 6.60 | 1.00 | 1.00 | 1.00 | 6.25 | 0.17 | 1.00 |
| Mir140 | 1.00 | 0.02 | 1.00 | 1.00 | 47.59 | 1.00 | 0.36 | 1.00 | 0.02 |
| Mir141 | 1.00 | 1.00 | 1.00 | 0.02 | 1.00 | 1.00 | 1.00 | 1.00 | 1.00 |
| Mir142 | 1.00 | 1.00 | 1.00 | 25.86 | 0.03 | 1.00 | 1.00 | 1.00 | 1.00 |
| Mir142b | 1.00 | 0.23 | 3.77 | 1.15 | 0.92 | 1.20 | 1.10 | 0.35 | 0.98 |
| Mir143 | 1.00 | 1.00 | 1.00 | 0.01 | 0.33 | 0.94 | 0.03 | 1.00 | 1.00 |
| Mir144 | 1.00 | 1.00 | 1.00 | 1.00 | 1.00 | 1.00 | 1.00 | 1.00 | 1.00 |
| Mir145 | 40.27 | 0.02 | 1.00 | 4.28 | 0.77 | 0.85 | 0.01 | 60.31 | 1.01 |
| Mir146 | 1.00 | 1.00 | 1.00 | 1.00 | 1.00 | 1.00 | 1.00 | 1.00 | 1.00 |
| Mir147 | 1.00 | 39.49 | 1.00 | 1.00 | 27.96 | 1.00 | 1.00 | 1.00 | 1.00 |
| Mir149 | 1.00 | 1.00 | 1.00 | 1.00 | 1.00 | 1.00 | 1.00 | 26.25 | 1.00 |
| Mir150 | 1.00 | 1.00 | 1.00 | 1.00 | 1.00 | 1.00 | 1.00 | 1.00 | 1.00 |
| Mir154 | 1.75 | 67.67 | 0.36 | 1.00 | 1.00 | 1.00 | 1.00 | 1.00 | 1.00 |
| Mir155 | 1.00 | 1.00 | 0.02 | 1.00 | 1.00 | 1.00 | 1.00 | 1.00 | 1.00 |
| Mir15a | 1.00 | 1.00 | 1.00 | 0.07 | 1.00 | 1.00 | 1.00 | 1.00 | 1.00 |
| Mir16-1 | 1.00 | 10.16 | 1.00 | 1.00 | 1.00 | 0.14 | 1.00 | 1.00 | 1.00 |
| Mir1668 | 0.97 | 0.06 | 1.00 | 1.32 | 1.31 | 1.51 | 0.55 | 3.99 | 0.23 |
| Mir17 | 1.00 | 1.00 | 1.00 | 1.00 | 1.00 | 1.00 | 1.00 | 1.00 | 1.00 |
| Mir18 | 1.00 | 1.00 | 1.00 | 9.11 | 8.14 | 1.00 | 6.91 | 1.00 | 1.00 |

Fig. 31- 52

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mal | 1.74 | 1.27 | 1.00 | 1.00 | 1.00 | 1.00 | 1.00 | 1.00 | 1.00 | 0.88 | 1.02 | 1.03 |
| Man1a | 0.94 | 1.38 | 1.28 | 1.05 | 1.07 | 0.96 | 0.96 | 1.19 | 1.13 | 1.22 | 1.05 | 1.04 |
| Marco | 7.46 | 2.64 | 2.64 | 2.01 | 1.00 | 1.21 | 1.00 | 0.55 | 0.71 | 1.00 | 1.07 | 0.95 |
| Matn4 | 1.00 | 1.14 | 1.00 | 1.00 | 1.00 | 1.00 | 1.07 | 0.89 | 1.01 | 0.89 | 0.95 | 0.97 |
| Mb | 14.83 | 6.79 | 7.03 | 1.00 | 1.00 | 1.00 | 1.00 | 1.00 | 1.00 | 1.18 | 0.99 | 1.07 |
| Mbnl3 | 0.78 | 0.63 | 0.84 | 1.00 | 1.03 | 0.84 | 1.00 | 1.00 | 1.00 | 0.92 | 0.98 | 1.00 |
| Mboat2 | 1.00 | 1.00 | 1.00 | 1.12 | 0.94 | 1.07 | 1.00 | 1.00 | 1.00 | 0.98 | 1.13 | 1.06 |
| Mfap4 | 3.07 | 0.88 | 2.32 | 1.00 | 1.00 | 1.00 | 1.00 | 1.00 | 1.00 | 0.96 | 0.98 | 1.02 |
| Mfrp | 1.00 | 1.00 | 1.00 | 1.00 | 1.00 | 1.00 | 1.00 | 1.00 | 1.00 | 1.00 | 0.98 | 1.06 |
| Mfsd2a | 1.00 | 1.17 | 1.00 | 1.00 | 1.00 | 1.00 | 1.00 | 1.00 | 1.00 | 0.95 | 0.90 | 0.98 |
| Mir100 | 1.00 | 1.00 | 1.00 | 1.00 | 1.00 | 1.00 | 1.00 | 1.00 | 1.00 | 1.00 | 1.00 | 1.00 |
| Mir101b | 0.13 | 1.00 | 1.00 | 1.00 | 1.00 | 1.00 | 1.00 | 1.00 | 1.00 | 1.00 | 1.00 | 1.00 |
| Mir103-2 | 0.05 | 0.48 | 1.00 | 1.00 | 9.19 | 1.00 | 1.00 | 1.00 | 1.00 | 1.00 | 1.00 | 1.00 |
| Mir106b | 2.83 | 1.00 | 1.00 | 0.08 | 1.00 | 1.00 | 0.11 | 1.00 | 1.00 | 1.00 | 1.00 | 1.00 |
| Mir107 | 1.00 | 1.00 | 1.00 | 1.00 | 1.00 | 1.00 | 1.00 | 1.00 | 1.00 | 1.00 | 1.00 | 1.00 |
| Mir10a | 1.00 | 1.00 | 4.64 | 1.00 | 4.23 | 1.00 | 1.00 | 1.00 | 1.00 | 1.00 | 1.00 | 1.00 |
| Mir10b | 30.28 | 0.04 | 1.00 | 1.00 | 1.00 | 1.00 | 1.00 | 1.00 | 1.00 | 1.00 | 1.00 | 1.00 |
| Mir1190 | 1.00 | 1.00 | 7.66 | 1.00 | 1.00 | 1.00 | 1.00 | 1.00 | 1.00 | 1.00 | 1.00 | 1.00 |
| Mir1191b | 1.00 | 1.00 | 1.00 | 0.02 | 1.00 | 1.00 | 1.00 | 1.00 | 1.00 | 1.00 | 1.00 | 1.00 |
| Mir1192 | 0.94 | 1.00 | 0.29 | 0.36 | 1.00 | 1.00 | 1.00 | 0.40 | 1.50 | 1.00 | 1.00 | 1.00 |
| Mir1199 | 2.96 | 2.28 | 0.44 | 1.00 | 2.99 | 1.00 | 1.23 | 1.70 | 1.00 | 1.00 | 1.00 | 1.00 |
| Mir1224 | 1.00 | 1.00 | 1.00 | 1.00 | 1.00 | 11.90 | 1.00 | 1.00 | 1.00 | 1.00 | 1.00 | 1.00 |
| Mir1231 | 1.00 | 1.00 | 1.00 | 1.00 | 22.67 | 1.00 | 1.00 | 12.81 | 1.00 | 1.00 | 1.00 | 1.00 |
| Mir1247 | 1.00 | 1.00 | 1.00 | 1.00 | 1.00 | 1.00 | 1.00 | 1.00 | 1.00 | 1.00 | 1.00 | 1.00 |
| Mir1249 | 1.80 | 0.98 | 0.88 | 14.27 | 1.03 | 0.62 | 4.05 | 1.00 | 0.17 | 1.00 | 1.00 | 1.00 |
| Mir124a-3 | 1.00 | 1.00 | 1.00 | 1.00 | 1.00 | 1.00 | 1.00 | 1.00 | 1.00 | 1.00 | 1.00 | 1.00 |
| Mir1251 | 1.00 | 1.00 | 1.00 | 1.00 | 1.00 | 1.00 | 1.00 | 1.00 | 1.00 | 1.00 | 1.00 | 1.00 |
| Mir1258 | 0.01 | 57.19 | 0.01 | 1.00 | 1.00 | 1.00 | 1.00 | 42.20 | 0.02 | 1.00 | 1.00 | 1.00 |
| Mir125a | 1.00 | 0.46 | 1.00 | 1.00 | 1.00 | 1.00 | 1.00 | 1.00 | 1.00 | 1.00 | 1.00 | 1.00 |
| Mir125b-1 | 1.00 | 0.47 | 1.00 | 1.00 | 1.00 | 1.00 | 1.00 | 1.00 | 1.00 | 1.00 | 1.00 | 1.00 |
| Mir125b-2 | 1.00 | 1.00 | 1.00 | 1.00 | 1.00 | 1.00 | 1.00 | 1.00 | 1.00 | 1.00 | 1.00 | 1.00 |
| Mir126 | 0.53 | 1.00 | 1.00 | 1.00 | 1.00 | 1.00 | 1.00 | 1.00 | 1.00 | 1.00 | 1.00 | 1.00 |
| Mir126b | 0.01 | 1.53 | 1.04 | 1.00 | 1.00 | 1.00 | 36.88 | 1.29 | 62.83 | 1.00 | 1.00 | 1.00 |
| Mir127 | 1.00 | 1.00 | 1.00 | 1.00 | 1.00 | 1.00 | 1.00 | 1.00 | 1.00 | 1.00 | 1.00 | 1.00 |
| Mir129-2 | 1.00 | 1.00 | 1.00 | 1.00 | 1.00 | 1.00 | 1.00 | 1.00 | 1.00 | 1.00 | 1.00 | 1.00 |
| Mir1306 | 47.70 | 0.14 | 1.32 | 1.13 | 2.30 | 2.00 | 1.13 | 42.74 | 0.22 | 1.00 | 1.00 | 1.00 |
| Mir130a | 1.00 | 1.00 | 1.00 | 1.00 | 35.28 | 0.02 | 1.00 | 1.00 | 1.00 | 1.00 | 1.00 | 1.00 |
| Mir130c | 12.97 | 0.14 | 0.43 | 1.00 | 22.37 | 18.27 | 1.00 | 2.56 | 8.53 | 1.00 | 1.00 | 1.00 |
| Mir132 | 1.00 | 1.00 | 1.01 | 1.00 | 1.00 | 1.00 | 1.00 | 1.00 | 1.00 | 1.00 | 1.00 | 1.00 |
| Mir133a-1 | 34.30 | 26.71 | 1.00 | 1.00 | 1.00 | 1.00 | 1.00 | 1.00 | 1.00 | 1.00 | 1.00 | 1.00 |
| Mir133a-2 | 1.00 | 5.99 | 1.00 | 0.85 | 0.07 | 0.67 | 1.00 | 1.00 | 1.00 | 1.00 | 1.00 | 1.00 |
| Mir133c | 1.00 | 1.00 | 1.00 | 1.00 | 1.00 | 1.00 | 1.00 | 1.00 | 1.00 | 1.00 | 1.00 | 1.00 |
| Mir134 | 1.00 | 1.00 | 1.00 | 1.00 | 1.00 | 1.00 | 1.00 | 1.00 | 1.00 | 1.00 | 1.00 | 1.00 |
| Mir135a-1 | 2.15 | 0.47 | 0.47 | 0.69 | 0.30 | 1.74 | 0.08 | 1.00 | 0.15 | 1.00 | 1.00 | 1.00 |
| Mir135a-2 | 1.00 | 1.00 | 1.00 | 1.00 | 1.00 | 1.00 | 1.00 | 1.00 | 1.00 | 1.00 | 1.00 | 1.00 |
| Mir138-1 | 1.00 | 1.00 | 1.00 | 1.00 | 1.00 | 1.00 | 1.00 | 1.00 | 1.00 | 1.00 | 1.00 | 1.00 |
| Mir140 | 0.01 | 0.01 | 1.00 | 1.00 | 1.00 | 2.06 | 15.25 | 1.00 | 22.08 | 1.00 | 1.00 | 1.00 |
| Mir141 | 23.59 | 1.00 | 1.00 | 1.00 | 1.00 | 1.00 | 1.00 | 1.00 | 1.00 | 1.00 | 16.59 | 1.00 |
| Mir142 | 1.00 | 1.00 | 1.00 | 1.00 | 1.00 | 1.00 | 1.00 | 1.00 | 1.00 | 1.00 | 1.00 | 1.00 |
| Mir142b | 1.38 | 0.74 | 0.62 | 1.45 | 0.83 | 0.85 | 1.23 | 0.34 | 0.38 | 1.00 | 1.16 | 0.73 |
| Mir143 | 85.61 | 37.95 | 4.17 | 1.00 | 1.00 | 1.00 | 1.00 | 1.00 | 1.00 | 1.00 | 1.00 | 1.00 |
| Mir144 | 1.00 | 1.00 | 1.00 | 0.51 | 0.26 | 0.01 | 1.00 | 1.00 | 1.00 | 1.00 | 1.00 | 1.00 |
| Mir145 | 0.94 | 0.62 | 0.85 | 1.00 | 1.00 | 1.00 | 1.00 | 1.00 | 1.00 | 1.00 | 1.00 | 1.00 |
| Mir146 | 37.17 | 1.00 | 1.00 | 1.00 | 32.83 | 1.00 | 1.00 | 1.00 | 1.00 | 1.00 | 1.00 | 1.00 |
| Mir147 | 1.00 | 1.00 | 1.00 | 1.00 | 1.00 | 1.00 | 7.89 | 1.00 | 1.00 | 1.00 | 1.00 | 1.00 |
| Mir149 | 1.00 | 1.00 | 1.00 | 1.00 | 1.00 | 1.00 | 1.00 | 1.00 | 1.00 | 1.00 | 1.00 | 1.00 |
| Mir150 | 1.00 | 1.00 | 1.00 | 1.00 | 1.00 | 1.00 | 1.00 | 1.00 | 1.00 | 1.00 | 1.00 | 1.00 |
| Mir154 | 1.00 | 1.00 | 1.00 | 1.00 | 1.00 | 1.00 | 1.00 | 1.00 | 1.00 | 1.00 | 1.00 | 1.00 |
| Mir155 | 42.12 | 1.00 | 1.00 | 1.00 | 1.00 | 1.00 | 1.00 | 1.00 | 1.00 | 1.00 | 1.00 | 1.00 |
| Mir15a | 0.08 | 1.00 | 1.00 | 0.10 | 0.99 | 23.36 | 1.00 | 1.00 | 1.00 | 1.00 | 1.00 | 1.00 |
| Mir16-1 | 1.00 | 1.00 | 9.35 | 0.13 | 1.00 | 1.00 | 1.00 | 1.00 | 1.00 | 1.00 | 1.00 | 1.00 |
| Mir1668 | 0.86 | 0.97 | 0.95 | 0.83 | 1.11 | 0.40 | 1.00 | 0.23 | 1.00 | 1.00 | 1.13 | 1.16 |
| Mir17 | 0.08 | 1.00 | 1.00 | 1.00 | 1.00 | 1.00 | 1.00 | 1.00 | 1.00 | 1.00 | 1.00 | 1.00 |
| Mir18 | 0.14 | 0.88 | 0.13 | 1.00 | 1.00 | 1.00 | 1.00 | 1.00 | 0.16 | 1.00 | 1.00 | 1.00 |

Fig. 31-53

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir181a-1 | 1.00 | 1.00 | 1.00 | 1.00 | 1.00 | 1.00 | 1.00 | 1.00 | 1.00 |
| Mir181a-2 | 1.00 | 1.00 | 1.00 | 1.00 | 1.00 | 1.00 | 1.00 | 1.00 | 1.00 |
| Mir181b-1 | 1.00 | 0.06 | 1.00 | 1.00 | 1.00 | 0.06 | 1.00 | 1.00 | 1.00 |
| Mir181b-2 | 0.08 | 1.00 | 1.00 | 14.63 | 1.00 | 1.00 | 1.00 | 1.00 | 1.00 |
| Mir181c | 1.00 | 1.00 | 1.00 | 1.00 | 1.00 | 1.00 | 1.00 | 1.00 | 1.00 |
| Mir181d | 1.00 | 1.00 | 1.00 | 1.00 | 1.00 | 1.00 | 1.00 | 1.00 | 1.00 |
| Mir1839 | 0.51 | 0.69 | 0.79 | 0.95 | 0.01 | 3.54 | 1.76 | 1.98 | 60.48 |
| Mir1843 | 1.00 | 1.00 | 1.00 | 1.00 | 1.00 | 1.00 | 1.00 | 1.00 | 1.00 |
| Mir1843b | 52.46 | 0.07 | 7.28 | 1.00 | 1.00 | 1.00 | 1.00 | 1.00 | 1.00 |
| Mir185 | 1.00 | 1.00 | 1.00 | 1.00 | 1.00 | 1.00 | 1.00 | 1.00 | 1.00 |
| Mir186 | 0.58 | 0.60 | 0.74 | 0.43 | 1.14 | 0.01 | 0.03 | 39.76 | 0.02 |
| Mir187 | 1.00 | 1.00 | 1.00 | 1.00 | 1.00 | 1.00 | 1.00 | 1.00 | 1.00 |
| Mir1892 | 1.00 | 14.93 | 1.00 | 275.82 | 0.01 | 0.04 | 7.64 | 1.29 | 111.00 |
| Mir1893 | 1.00 | 0.03 | 0.04 | 0.02 | 0.03 | 1.00 | 0.02 | 1.00 | 0.09 |
| Mir1894 | 26.61 | 0.44 | 0.06 | 0.43 | 1.15 | 0.71 | 2.07 | 0.03 | 2.54 |
| Mir1895 | 0.04 | 0.08 | 0.02 | 1.00 | 1.00 | 1.00 | 1.00 | 1.00 | 1.00 |
| Mir1897 | 1.00 | 1.00 | 1.00 | 11.71 | 1.00 | 1.00 | 1.00 | 1.00 | 1.00 |
| Mir1898 | 1.65 | 0.87 | 12.74 | 2.19 | 1.00 | 0.01 | 0.03 | 1.00 | 1.00 |
| Mir1899 | 1.00 | 1.00 | 1.00 | 1.00 | 1.00 | 1.00 | 1.00 | 1.00 | 1.00 |
| Mir1900 | 1.00 | 1.00 | 1.00 | 1.00 | 1.00 | 1.00 | 1.00 | 1.00 | 1.00 |
| Mir1901 | 55.31 | 0.09 | 0.75 | 1.00 | 3.57 | 1.38 | 5.36 | 0.94 | 1.00 |
| Mir1902 | 0.01 | 0.49 | 0.25 | 0.34 | 1.48 | 0.50 | 0.93 | 0.02 | 1.08 |
| Mir1904 | 1.00 | 1.00 | 1.00 | 1.00 | 1.00 | 1.00 | 1.00 | 1.00 | 1.00 |
| Mir1905 | 0.12 | 1.32 | 2.08 | 0.09 | 31.41 | 0.29 | 14.23 | 1.00 | 1.00 |
| Mir1906-1 | 1.00 | 1.00 | 1.00 | 1.00 | 1.00 | 0.35 | 0.15 | 15.05 | 0.03 |
| Mir1906-2 | 0.98 | 1.37 | 1.96 | 1.00 | 0.59 | 16.37 | 0.49 | 0.21 | 0.73 |
| Mir1907 | 1.00 | 1.00 | 9.26 | 0.04 | 25.25 | 1.04 | 1.00 | 0.09 | 1.00 |
| Mir191 | 1.00 | 0.05 | 1.00 | 1.00 | 0.03 | 1.00 | 1.00 | 1.00 | 1.00 |
| Mir192 | 1.00 | 1.00 | 1.00 | 0.40 | 2.20 | 1.01 | 1.00 | 13.57 | 0.08 |
| Mir1929 | 15.26 | 1.00 | 1.76 | 0.10 | 11.25 | 1.00 | 0.05 | 1.05 | 1.00 |
| Mir193 | 1.00 | 1.00 | 1.00 | 1.00 | 0.02 | 1.00 | 1.00 | 1.00 | 1.00 |
| Mir1930 | 23.14 | 21.59 | 0.95 | 16.35 | 1.00 | 0.08 | 0.07 | 42.20 | 0.06 |
| Mir1932 | 1.70 | 0.05 | 0.87 | 0.09 | 0.05 | 1.00 | 1.00 | 9.71 | 1.00 |
| Mir1933 | 1.00 | 1.00 | 1.00 | 1.00 | 1.00 | 1.00 | 1.00 | 1.00 | 1.00 |
| Mir1934 | 13.05 | 1.00 | 1.00 | 1.00 | 1.00 | 1.00 | 1.00 | 1.00 | 17.05 |
| Mir1936 | 1.00 | 1.00 | 1.00 | 1.00 | 1.00 | 1.00 | 1.00 | 1.00 | 1.00 |
| Mir1938 | 3.17 | 0.15 | 0.48 | 1.00 | 1.00 | 0.16 | 1.00 | 6.35 | 0.12 |
| Mir193b | 1.00 | 1.00 | 1.00 | 1.00 | 1.00 | 1.00 | 1.00 | 1.00 | 1.00 |
| Mir1940 | 1.00 | 1.56 | 5.30 | 1.41 | 0.06 | 2.03 | 1.68 | 0.15 | 6.43 |
| Mir1941 | 1.00 | 1.00 | 1.00 | 1.00 | 1.00 | 0.07 | 1.00 | 1.00 | 1.00 |
| Mir194-1 | 1.00 | 59.31 | 32.42 | 0.02 | 1.00 | 1.00 | 1.00 | 0.82 | 0.03 |
| Mir1942 | 90.36 | 1.00 | 1.00 | 1.00 | 1.00 | 1.00 | 1.00 | 0.01 | 1.00 |
| Mir194-2 | 1.00 | 1.00 | 1.00 | 0.04 | 0.04 | 2.05 | 0.92 | 0.86 | 1.00 |
| Mir1943 | 0.50 | 1.20 | 0.82 | 1.97 | 2.30 | 0.27 | 0.52 | 0.56 | 0.02 |
| Mir1945 | 2.51 | 15.69 | 1.00 | 0.66 | 0.04 | 1.05 | 4.16 | 0.86 | 22.79 |
| Mir1948 | 1.00 | 1.00 | 1.00 | 1.00 | 0.07 | 1.00 | 0.02 | 0.33 | 0.60 |
| Mir1949 | 4.92 | 96.37 | 1.76 | 1.00 | 1.00 | 1.00 | 1.00 | 73.84 | 1.00 |
| Mir195 | 1.00 | 1.00 | 1.00 | 1.00 | 1.00 | 1.00 | 1.00 | 1.00 | 1.00 |
| Mir1953 | 1.00 | 1.00 | 0.10 | 14.46 | 1.00 | 0.10 | 1.00 | 1.00 | 1.00 |
| Mir1955 | 1.00 | 1.00 | 1.00 | 1.00 | 1.00 | 1.00 | 1.00 | 1.00 | 0.20 |
| Mir1956 | 1.00 | 35.76 | 1.00 | 0.02 | 1.00 | 1.00 | 1.00 | 1.00 | 1.00 |
| Mir1957b | 2.13 | 1.07 | 1.58 | 1.35 | 0.28 | 8.69 | 0.08 | 3.73 | 1.00 |
| Mir1960 | 0.05 | 1.00 | 1.00 | 1.00 | 1.00 | 1.00 | 1.00 | 1.00 | 1.00 |
| Mir1964 | 0.04 | 22.74 | 0.04 | 0.07 | 1.00 | 0.04 | 1.00 | 1.00 | 16.42 |
| Mir1966 | 1.14 | 0.71 | 1.04 | 0.60 | 1.50 | 1.65 | 10.85 | 1.00 | 3.19 |
| Mir1967 | 1.00 | 1.00 | 1.00 | 1.00 | 1.00 | 1.00 | 1.00 | 1.00 | 1.00 |
| Mir1968 | 1.00 | 0.03 | 1.00 | 0.01 | 0.17 | 0.34 | 1.04 | 1.00 | 0.49 |
| Mir1969 | 1.00 | 1.00 | 1.00 | 1.00 | 1.00 | 1.00 | 1.00 | 1.00 | 1.00 |
| Mir196b | 1.00 | 1.00 | 1.00 | 0.84 | 1.01 | 1.07 | 1.00 | 1.00 | 1.00 |
| Mir1981 | 0.06 | 12.76 | 13.01 | 0.53 | 1.14 | 1.01 | 0.32 | 0.42 | 0.03 |
| Mir199a-1 | 0.83 | 74.57 | 0.92 | 0.03 | 1.16 | 65.22 | 1.00 | 0.03 | 1.00 |
| Mir199b | 1.00 | 1.00 | 1.00 | 1.00 | 1.00 | 1.00 | 1.00 | 1.00 | 1.00 |
| Mir19a | 1.00 | 1.00 | 1.00 | 1.00 | 1.00 | 1.01 | 1.00 | 1.00 | 1.00 |
| Mir19b-1 | 10.18 | 1.00 | 1.00 | 16.05 | 0.07 | 1.00 | 1.00 | 1.00 | 1.00 |

Fig. 31- 54

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir181a-1 | 1.00 | 1.00 | 0.11 | 1.00 | 1.00 | 1.00 | 1.00 | 17.11 | 1.00 |
| Mir181a-2 | 1.00 | 1.00 | 1.00 | 1.00 | 1.00 | 1.00 | 1.00 | 1.00 | 1.00 |
| Mir181b-1 | 1.00 | 0.08 | 1.00 | 1.00 | 1.00 | 1.00 | 1.00 | 1.00 | 1.00 |
| Mir181b-2 | 1.00 | 1.00 | 1.00 | 1.00 | 1.00 | 1.00 | 1.00 | 1.00 | 1.00 |
| Mir181c | 0.13 | 1.00 | 1.00 | 1.00 | 1.00 | 1.00 | 1.00 | 1.00 | 1.00 |
| Mir181d | 0.05 | 1.00 | 1.00 | 1.00 | 1.00 | 1.00 | 1.00 | 1.00 | 1.00 |
| Mir1839 | 0.68 | 3.09 | 0.69 | 0.65 | 1.03 | 1.13 | 1.10 | 0.94 | 1.35 |
| Mir1843 | 30.31 | 1.00 | 1.00 | 1.00 | 1.00 | 1.00 | 1.00 | 1.00 | 1.00 |
| Mir1843b | 1.00 | 1.00 | 40.84 | 1.00 | 1.00 | 1.00 | 1.00 | 1.00 | 1.00 |
| Mir185 | 1.00 | 33.85 | 1.00 | 1.00 | 1.00 | 1.00 | 0.02 | 1.00 | 1.00 |
| Mir186 | 0.73 | 0.42 | 1.25 | 1.91 | 1.00 | 1.37 | 0.91 | 1.08 | 1.72 |
| Mir187 | 1.00 | 0.02 | 1.00 | 1.00 | 1.00 | 1.00 | 1.00 | 1.00 | 1.00 |
| Mir1892 | 1.00 | 1.00 | 1.00 | 0.52 | 0.01 | 159.05 | 2.04 | 0.36 | 74.57 |
| Mir1893 | 1.00 | 1.60 | 1.64 | 1.00 | 1.00 | 0.01 | 18.99 | 1.00 | 8.80 |
| Mir1894 | 0.51 | 1.98 | 0.45 | 0.03 | 0.99 | 1.00 | 1.20 | 0.70 | 1.64 |
| Mir1895 | 1.00 | 0.17 | 0.70 | 1.00 | 0.04 | 0.15 | 11.60 | 1.00 | 0.04 |
| Mir1897 | 1.00 | 1.00 | 1.00 | 1.00 | 1.00 | 1.00 | 1.00 | 1.00 | 1.00 |
| Mir1898 | 1.32 | 2.08 | 0.43 | 4.97 | 4.80 | 22.88 | 0.83 | 9.38 | 15.49 |
| Mir1899 | 1.00 | 1.00 | 1.00 | 1.00 | 1.00 | 1.00 | 1.00 | 1.00 | 1.00 |
| Mir1900 | 1.00 | 0.07 | 1.00 | 1.00 | 1.00 | 1.00 | 47.04 | 1.07 | 1.76 |
| Mir1901 | 1.41 | 34.18 | 0.02 | 0.01 | 1.23 | 42.44 | 0.17 | 0.47 | 1.98 |
| Mir1902 | 0.31 | 68.64 | 0.08 | 1.86 | 0.97 | 0.70 | 0.61 | 0.03 | 2.07 |
| Mir1904 | 1.00 | 1.00 | 1.00 | 1.00 | 0.08 | 1.00 | 1.00 | 22.55 | 1.00 |
| Mir1905 | 0.28 | 17.57 | 8.68 | 0.05 | 1.00 | 1.24 | 24.90 | 0.08 | 24.56 |
| Mir1906-1 | 1.00 | 1.00 | 1.00 | 1.00 | 1.00 | 1.00 | 18.62 | 1.00 | 0.37 |
| Mir1906-2 | 0.89 | 0.74 | 1.09 | 1.86 | 1.14 | 0.66 | 1.58 | 0.45 | 0.92 |
| Mir1907 | 1.00 | 8.39 | 0.13 | 1.00 | 8.05 | 1.00 | 11.56 | 1.00 | 1.09 |
| Mir191 | 1.00 | 1.00 | 1.00 | 1.00 | 1.00 | 1.00 | 0.03 | 1.00 | 1.00 |
| Mir192 | 1.00 | 1.00 | 1.00 | 1.00 | 1.00 | 1.00 | 1.00 | 1.00 | 1.00 |
| Mir1929 | 1.02 | 32.28 | 1.94 | 1.00 | 0.14 | 1.00 | 10.85 | 0.30 | 9.69 |
| Mir193 | 1.00 | 1.00 | 1.00 | 1.00 | 1.00 | 1.00 | 1.00 | 1.00 | 1.00 |
| Mir1930 | 1.00 | 3.19 | 0.72 | 10.57 | 1.00 | 10.46 | 0.03 | 0.06 | 53.91 |
| Mir1932 | 0.69 | 2.13 | 0.54 | 1.00 | 1.02 | 1.00 | 0.95 | 0.35 | 10.27 |
| Mir1933 | 1.00 | 1.00 | 1.00 | 1.11 | 1.00 | 9.28 | 1.00 | 1.00 | 1.00 |
| Mir1934 | 1.00 | 1.00 | 1.00 | 1.00 | 11.61 | 1.00 | 1.01 | 1.00 | 42.86 |
| Mir1936 | 1.00 | 1.00 | 1.00 | 1.00 | 1.00 | 1.00 | 1.00 | 12.86 | 1.00 |
| Mir1938 | 1.91 | 1.87 | 0.07 | 1.00 | 1.04 | 0.17 | 1.00 | 1.10 | 6.70 |
| Mir193b | 1.00 | 1.00 | 1.00 | 1.00 | 1.00 | 1.00 | 1.00 | 1.00 | 1.00 |
| Mir1940 | 0.97 | 0.51 | 0.94 | 5.72 | 1.00 | 1.00 | 15.87 | 1.30 | 1.47 |
| Mir1941 | 0.09 | 1.00 | 1.00 | 1.00 | 1.00 | 1.00 | 1.00 | 1.00 | 15.85 |
| Mir194-1 | 1.03 | 1.10 | 0.01 | 1.00 | 27.99 | 1.00 | 52.71 | 1.19 | 43.16 |
| Mir1942 | 1.00 | 1.00 | 1.00 | 1.00 | 1.00 | 1.00 | 1.00 | 1.00 | 1.00 |
| Mir194-2 | 1.00 | 1.00 | 1.00 | 1.00 | 1.00 | 1.00 | 1.00 | 1.00 | 1.00 |
| Mir1943 | 0.52 | 0.45 | 0.67 | 1.05 | 0.30 | 1.25 | 1.65 | 0.28 | 0.80 |
| Mir1945 | 0.07 | 0.04 | 0.04 | 1.00 | 0.34 | 1.00 | 1.00 | 1.00 | 1.00 |
| Mir1948 | 1.00 | 1.00 | 1.00 | 1.00 | 1.00 | 1.00 | 1.00 | 1.00 | 1.00 |
| Mir1949 | 45.07 | 0.98 | 45.55 | 22.93 | 0.04 | 44.87 | 2.54 | 3.28 | 178.20 |
| Mir195 | 6.42 | 1.00 | 0.15 | 1.00 | 1.00 | 1.00 | 1.00 | 1.00 | 1.00 |
| Mir1953 | 0.13 | 1.00 | 1.00 | 1.00 | 1.00 | 1.00 | 1.00 | 1.00 | 1.00 |
| Mir1955 | 1.00 | 1.00 | 1.00 | 1.00 | 0.17 | 5.83 | 1.00 | 1.00 | 1.00 |
| Mir1956 | 1.00 | 1.00 | 0.03 | 1.00 | 1.00 | 1.00 | 1.00 | 1.00 | 0.02 |
| Mir1957b | 5.73 | 1.83 | 0.24 | 5.34 | 0.66 | 0.64 | 3.68 | 0.09 | 1.10 |
| Mir1960 | 1.00 | 1.00 | 1.00 | 1.00 | 1.00 | 1.00 | 1.00 | 1.00 | 38.53 |
| Mir1964 | 1.02 | 1.01 | 0.03 | 13.44 | 0.09 | 1.00 | 1.00 | 1.11 | 1.01 |
| Mir1966 | 0.63 | 1.03 | 0.88 | 32.82 | 0.86 | 33.62 | 0.75 | 0.78 | 0.95 |
| Mir1967 | 1.00 | 10.82 | 1.00 | 1.00 | 1.00 | 1.00 | 1.00 | 1.00 | 0.05 |
| Mir1968 | 26.05 | 0.49 | 0.02 | 1.00 | 1.00 | 1.00 | 1.00 | 1.00 | 1.00 |
| Mir1969 | 1.00 | 1.00 | 1.00 | 1.00 | 6.83 | 1.00 | 1.00 | 1.00 | 1.00 |
| Mir196b | 1.00 | 1.00 | 1.00 | 0.10 | 0.26 | 0.47 | 15.97 | 1.00 | 1.00 |
| Mir1981 | 1.00 | 2.08 | 0.72 | 1.00 | 11.59 | 1.00 | 4.32 | 1.00 | 0.93 |
| Mir199a-1 | 1.45 | 0.99 | 0.02 | 0.32 | 0.99 | 24.21 | 2.01 | 0.30 | 1.13 |
| Mir199b | 1.00 | 1.00 | 3.88 | 1.00 | 1.00 | 1.00 | 1.00 | 1.00 | 1.00 |
| Mir19a | 1.00 | 1.00 | 1.00 | 1.00 | 1.00 | 1.00 | 1.00 | 44.18 | 1.00 |
| Mir19b-1 | 25.40 | 1.00 | 0.04 | 1.00 | 1.00 | 1.00 | 13.38 | 17.11 | 0.09 |

Fig. 31- 55

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir181a-1 | 1.00 | 1.00 | 1.00 | 1.00 | 1.00 | 1.00 | 1.11 | 0.11 | 1.00 |
| Mir181a-2 | 1.00 | 1.00 | 1.00 | 1.00 | 28.99 | 1.00 | 1.00 | 0.06 | 1.00 |
| Mir181b-1 | 0.04 | 1.00 | 1.00 | 1.00 | 1.00 | 15.54 | 1.00 | 1.00 | 0.98 |
| Mir181b-2 | 1.00 | 1.00 | 1.00 | 1.00 | 1.00 | 1.00 | 1.00 | 1.00 | 0.11 |
| Mir181c | 1.00 | 0.08 | 18.82 | 0.09 | 1.00 | 1.00 | 1.13 | 0.11 | 1.09 |
| Mir181d | 1.00 | 0.96 | 1.00 | 1.00 | 1.00 | 1.00 | 21.66 | 19.13 | 1.00 |
| Mir1839 | 0.39 | 1.24 | 0.27 | 0.52 | 1.12 | 1.16 | 2.14 | 0.56 | 0.21 |
| Mir1843 | 1.00 | 1.00 | 1.00 | 0.02 | 1.00 | 1.00 | 1.00 | 1.00 | 28.43 |
| Mir1843b | 1.00 | 1.00 | 1.00 | 14.63 | 1.00 | 0.03 | 1.00 | 1.00 | 1.00 |
| Mir185 | 0.01 | 1.00 | 1.00 | 1.00 | 1.00 | 1.00 | 1.00 | 1.00 | 1.00 |
| Mir186 | 0.44 | 1.32 | 1.34 | 1.15 | 1.04 | 0.53 | 1.09 | 0.29 | 0.56 |
| Mir187 | 1.00 | 1.00 | 1.00 | 1.00 | 1.00 | 1.00 | 1.00 | 41.54 | 1.00 |
| Mir1892 | 0.72 | 1.08 | 294.70 | 0.24 | 21.99 | 0.29 | 54.80 | 1.00 | 44.85 |
| Mir1893 | 1.00 | 1.00 | 1.00 | 1.00 | 0.06 | 4.95 | 0.06 | 10.37 | 1.00 |
| Mir1894 | 0.04 | 0.02 | 3.06 | 0.62 | 2.00 | 5.97 | 0.33 | 0.57 | 0.51 |
| Mir1895 | 2.05 | 0.02 | 0.03 | 0.03 | 38.20 | 0.60 | 1.00 | 0.08 | 1.00 |
| Mir1897 | 1.00 | 1.00 | 1.00 | 1.00 | 1.00 | 1.00 | 0.09 | 16.32 | 1.00 |
| Mir1898 | 1.78 | 0.67 | 0.38 | 0.56 | 4.48 | 0.12 | 0.91 | 2.39 | 0.89 |
| Mir1899 | 1.00 | 1.00 | 1.00 | 1.00 | 1.00 | 1.00 | 6.99 | 16.09 | 1.05 |
| Mir1900 | 1.07 | 1.64 | 0.75 | 1.00 | 1.00 | 1.00 | 0.07 | 1.00 | 1.00 |
| Mir1901 | 0.01 | 0.13 | 0.39 | 0.42 | 1.98 | 15.31 | 1.00 | 0.07 | 8.27 |
| Mir1902 | 50.77 | 1.52 | 0.70 | 1.17 | 2.78 | 0.10 | 1.00 | 1.00 | 1.00 |
| Mir1904 | 1.00 | 1.00 | 1.00 | 1.00 | 1.00 | 1.00 | 1.00 | 1.00 | 1.00 |
| Mir1905 | 0.89 | 1.00 | 3.49 | 0.30 | 4.82 | 2.71 | 2.31 | 1.69 | 0.53 |
| Mir1906-1 | 0.00 | 0.00 | 1.00 | 0.01 | 13.79 | 1.00 | 1.00 | 1.00 | 1.00 |
| Mir1906-2 | 1.02 | 1.05 | 1.17 | 0.77 | 0.47 | 0.50 | 0.47 | 1.10 | 0.85 |
| Mir1907 | 0.90 | 0.09 | 1.00 | 13.33 | 1.00 | 8.69 | 1.00 | 1.00 | 1.00 |
| Mir191 | 0.90 | 0.50 | 45.17 | 0.03 | 33.81 | 1.00 | 0.75 | 15.78 | 2.15 |
| Mir192 | 1.00 | 1.00 | 1.00 | 0.09 | 1.00 | 1.00 | 1.00 | 0.11 | 1.00 |
| Mir1929 | 1.00 | 1.00 | 0.13 | 11.47 | 0.10 | 7.58 | 1.00 | 6.89 | 1.00 |
| Mir193 | 1.00 | 1.00 | 1.00 | 1.00 | 62.84 | 0.02 | 1.00 | 1.00 | 1.00 |
| Mir1930 | 1.18 | 16.44 | 1.04 | 1.00 | 0.35 | 0.08 | 1.09 | 18.35 | 20.04 |
| Mir1932 | 0.07 | 1.00 | 1.00 | 0.57 | 1.18 | 3.10 | 0.55 | 15.07 | 0.04 |
| Mir1933 | 1.00 | 1.00 | 1.00 | 1.00 | 13.60 | 1.00 | 1.00 | 1.00 | 1.00 |
| Mir1934 | 1.00 | 17.25 | 1.00 | 1.91 | 16.04 | 1.00 | 1.07 | 1.00 | 0.50 |
| Mir1936 | 1.00 | 1.00 | 1.00 | 1.00 | 1.00 | 1.00 | 1.00 | 6.89 | 1.00 |
| Mir1938 | 1.00 | 7.42 | 0.09 | 0.05 | 0.56 | 15.78 | 1.25 | 1.00 | 1.03 |
| Mir193b | 25.99 | 1.00 | 1.00 | 1.00 | 1.00 | 1.00 | 1.00 | 0.85 | 25.88 |
| Mir1940 | 0.48 | 2.47 | 11.30 | 2.38 | 1.31 | 2.43 | 1.94 | 0.54 | 17.75 |
| Mir1941 | 1.00 | 1.00 | 1.00 | 1.00 | 1.00 | 1.00 | 1.00 | 1.00 | 0.09 |
| Mir194-1 | 1.00 | 60.79 | 1.00 | 69.82 | 112.40 | 74.78 | 29.92 | 1.00 | 1.00 |
| Mir1942 | 1.00 | 1.00 | 1.00 | 1.00 | 1.00 | 1.00 | 1.00 | 1.00 | 1.00 |
| Mir194-2 | 33.16 | 1.00 | 1.00 | 1.00 | 1.00 | 1.00 | 0.11 | 0.10 | 0.11 |
| Mir1943 | 2.18 | 1.31 | 0.59 | 0.65 | 0.81 | 0.57 | 0.05 | 0.84 | 17.69 |
| Mir1945 | 21.27 | 1.00 | 18.79 | 24.98 | 49.68 | 1.02 | 1.19 | 1.79 | 0.92 |
| Mir1948 | 1.00 | 1.00 | 1.00 | 1.00 | 1.00 | 1.00 | 21.00 | 9.68 | 11.08 |
| Mir1949 | 1.00 | 1.00 | 1.00 | 1.00 | 1.08 | 87.87 | 0.04 | 0.04 | 0.05 |
| Mir195 | 8.56 | 1.00 | 1.00 | 1.00 | 0.12 | 1.00 | 1.00 | 1.00 | 1.00 |
| Mir1953 | 1.00 | 1.00 | 1.00 | 1.00 | 1.00 | 1.00 | 1.00 | 1.00 | 7.98 |
| Mir1955 | 1.00 | 1.00 | 1.00 | 1.00 | 1.00 | 1.00 | 1.00 | 5.32 | 1.00 |
| Mir1956 | 1.00 | 76.69 | 0.02 | 1.00 | 1.00 | 0.02 | 0.86 | 0.95 | 1.26 |
| Mir1957b | 0.39 | 0.98 | 0.06 | 0.28 | 0.52 | 0.22 | 0.17 | 1.00 | 0.75 |
| Mir1960 | 27.85 | 1.00 | 1.00 | 24.98 | 1.00 | 1.00 | 1.00 | 1.00 | 1.00 |
| Mir1964 | 20.08 | 0.03 | 0.08 | 0.07 | 47.12 | 1.00 | 0.09 | 1.00 | 1.00 |
| Mir1966 | 1.48 | 3.49 | 1.63 | 2.41 | 3.00 | 0.47 | 1.10 | 0.85 | 0.39 |
| Mir1967 | 1.00 | 1.00 | 1.00 | 1.00 | 0.06 | 1.00 | 1.00 | 11.15 | 12.19 |
| Mir1968 | 0.02 | 0.02 | 1.00 | 0.02 | 0.01 | 0.03 | 0.02 | 1.00 | 0.04 |
| Mir1969 | 1.17 | 18.65 | 1.00 | 1.00 | 1.00 | 1.00 | 0.15 | 1.00 | 1.00 |
| Mir196b | 1.00 | 1.00 | 1.00 | 1.00 | 0.03 | 1.00 | 1.00 | 1.00 | 1.00 |
| Mir1981 | 1.18 | 18.57 | 1.00 | 57.87 | 1.62 | 1.02 | 0.57 | 0.90 | 1.55 |
| Mir199a-1 | 1.04 | 0.02 | 1.03 | 3.24 | 182.84 | 0.66 | 0.04 | 0.91 | 21.25 |
| Mir199b | 0.29 | 0.41 | 19.07 | 1.00 | 5.23 | 1.00 | 1.00 | 1.00 | 1.00 |
| Mir19a | 1.00 | 1.00 | 1.00 | 0.03 | 35.32 | 13.84 | 1.00 | 1.00 | 1.00 |
| Mir19b-1 | 1.00 | 1.00 | 1.00 | 1.00 | 0.60 | 10.06 | 0.11 | 0.11 | 8.70 |

Fig. 31- 56

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir181a-1 | 1.57 | 0.56 | 0.16 | 1.00 | 1.00 | 1.00 | 1.00 | 1.00 | 1.00 | 1.00 | 1.00 | 1.00 |
| Mir181a-2 | 1.00 | 1.00 | 1.00 | 1.00 | 1.00 | 1.00 | 1.00 | 1.00 | 1.00 | 1.00 | 1.00 | 1.00 |
| Mir181b-1 | 0.78 | 1.03 | 0.44 | 1.00 | 1.00 | 1.00 | 1.00 | 1.00 | 1.00 | 1.00 | 1.00 | 1.00 |
| Mir181b-2 | 1.00 | 1.00 | 0.08 | 1.00 | 1.00 | 1.00 | 1.00 | 1.00 | 1.00 | 1.00 | 1.00 | 1.00 |
| Mir181c | 1.06 | 8.94 | 1.01 | 1.00 | 1.00 | 1.00 | 1.00 | 1.00 | 1.00 | 1.00 | 1.00 | 1.00 |
| Mir181d | 0.04 | 0.02 | 1.01 | 24.65 | 1.00 | 1.00 | 1.00 | 1.00 | 1.00 | 1.00 | 1.00 | 1.00 |
| Mir1839 | 0.51 | 0.98 | 0.83 | 1.20 | 0.41 | 0.50 | 1.81 | 0.45 | 0.02 | 1.00 | 1.00 | 1.00 |
| Mir1843 | 1.00 | 1.00 | 1.00 | 1.00 | 1.00 | 1.00 | 1.00 | 1.00 | 1.00 | 1.00 | 1.00 | 1.00 |
| Mir1843b | 1.68 | 0.04 | 38.27 | 1.00 | 0.06 | 1.00 | 1.00 | 1.00 | 1.00 | 1.00 | 1.00 | 1.00 |
| Mir185 | 1.00 | 1.00 | 1.00 | 1.00 | 1.00 | 1.00 | 1.00 | 1.00 | 1.00 | 1.00 | 1.00 | 1.00 |
| Mir186 | 0.43 | 0.70 | 0.59 | 3.34 | 1.46 | 1.10 | 1.41 | 19.41 | 0.52 | 1.00 | 1.00 | 1.00 |
| Mir187 | 1.00 | 1.00 | 1.00 | 1.00 | 1.00 | 1.00 | 1.00 | 1.00 | 1.00 | 1.00 | 1.00 | 1.00 |
| Mir1892 | 0.73 | 0.41 | 0.88 | 1.70 | 0.41 | 1.00 | 0.01 | 32.34 | 9.01 | 1.00 | 1.00 | 1.00 |
| Mir1893 | 1.00 | 1.00 | 79.53 | 1.99 | 10.16 | 0.14 | 0.18 | 1.00 | 1.59 | 1.00 | 1.00 | 1.00 |
| Mir1894 | 0.77 | 3.55 | 2.11 | 1.09 | 0.48 | 2.19 | 23.05 | 0.35 | 0.54 | 1.00 | 1.00 | 1.00 |
| Mir1895 | 0.08 | 1.52 | 0.07 | 1.00 | 1.00 | 1.00 | 3.85 | 0.47 | 0.43 | 1.00 | 1.00 | 1.00 |
| Mir1897 | 1.00 | 1.00 | 1.00 | 1.00 | 1.00 | 1.00 | 1.00 | 1.00 | 1.00 | 1.00 | 1.00 | 1.00 |
| Mir1898 | 1.98 | 1.06 | 2.01 | 0.55 | 0.96 | 0.85 | 0.82 | 11.64 | 1.00 | 1.00 | 1.00 | 1.00 |
| Mir1899 | 1.00 | 1.00 | 1.00 | 1.00 | 1.00 | 1.00 | 1.00 | 1.00 | 1.00 | 1.00 | 1.00 | 1.00 |
| Mir1900 | 16.91 | 1.00 | 1.00 | 17.66 | 13.46 | 0.01 | 1.00 | 1.00 | 1.00 | 1.00 | 1.00 | 1.00 |
| Mir1901 | 0.14 | 11.83 | 0.02 | 23.02 | 0.57 | 6.01 | 47.77 | 48.04 | 0.03 | 1.00 | 1.00 | 1.00 |
| Mir1902 | 108.69 | 0.90 | 2.01 | 1.72 | 0.09 | 59.69 | 31.68 | 0.66 | 0.09 | 1.00 | 1.00 | 1.00 |
| Mir1904 | 1.00 | 1.00 | 1.00 | 1.00 | 1.00 | 1.00 | 1.00 | 1.00 | 1.00 | 1.00 | 1.00 | 1.00 |
| Mir1905 | 1.00 | 2.12 | 0.70 | 13.27 | 0.67 | 0.29 | 1.00 | 0.43 | 0.56 | 1.00 | 1.00 | 1.00 |
| Mir1906-1 | 0.13 | 1.00 | 25.74 | 1.78 | 1.00 | 1.00 | 1.00 | 0.27 | 7.26 | 1.00 | 1.00 | 1.00 |
| Mir1906-2 | 0.02 | 0.99 | 3.15 | 15.94 | 0.08 | 15.43 | 0.51 | 0.21 | 3.54 | 1.00 | 1.00 | 1.00 |
| Mir1907 | 0.11 | 10.11 | 10.66 | 0.58 | 1.40 | 1.98 | 1.00 | 1.00 | 1.00 | 1.00 | 1.00 | 1.00 |
| Mir191 | 1.00 | 1.00 | 23.04 | 36.84 | 1.00 | 1.00 | 1.00 | 1.00 | 0.05 | 1.00 | 1.00 | 1.00 |
| Mir192 | 10.09 | 1.00 | 1.00 | 1.00 | 1.00 | 1.00 | 1.00 | 1.00 | 1.00 | 1.00 | 1.00 | 1.00 |
| Mir1929 | 1.16 | 1.00 | 1.01 | 2.92 | 0.92 | 15.18 | 9.20 | 1.00 | 1.00 | 1.00 | 1.00 | 1.00 |
| Mir193 | 1.00 | 1.00 | 1.00 | 1.00 | 1.00 | 1.00 | 1.00 | 1.00 | 1.00 | 1.00 | 1.00 | 1.00 |
| Mir1930 | 1.37 | 0.12 | 2.51 | 1.15 | 20.22 | 1.00 | 0.42 | 0.58 | 1.00 | 1.00 | 1.00 | 1.00 |
| Mir1932 | 0.78 | 0.11 | 39.05 | 0.56 | 0.52 | 0.59 | 5.68 | 0.15 | 1.00 | 1.00 | 1.00 | 1.00 |
| Mir1933 | 1.00 | 1.00 | 1.00 | 0.10 | 1.00 | 1.00 | 1.00 | 1.00 | 1.00 | 1.00 | 1.00 | 1.00 |
| Mir1934 | 1.01 | 1.11 | 27.10 | 24.53 | 1.79 | 13.16 | 1.00 | 1.00 | 1.00 | 1.00 | 1.00 | 1.00 |
| Mir1936 | 1.00 | 1.00 | 1.00 | 0.15 | 1.00 | 1.00 | 1.00 | 1.00 | 1.00 | 1.00 | 1.00 | 1.00 |
| Mir1938 | 0.08 | 1.00 | 1.00 | 0.51 | 0.17 | 11.39 | 0.77 | 1.00 | 0.92 | 1.00 | 1.00 | 1.00 |
| Mir193b | 1.00 | 1.00 | 1.00 | 1.00 | 1.00 | 1.00 | 1.00 | 1.00 | 1.00 | 1.00 | 1.00 | 1.00 |
| Mir1940 | 1.37 | 1.53 | 0.28 | 0.25 | 0.19 | 14.49 | 0.46 | 5.10 | 1.00 | 1.00 | 1.00 | 1.00 |
| Mir1941 | 1.00 | 1.00 | 1.00 | 1.00 | 11.69 | 12.46 | 1.00 | 1.00 | 1.00 | 1.00 | 1.00 | 1.00 |
| Mir194-1 | 1.00 | 1.08 | 1.01 | 1.00 | 1.00 | 1.00 | 1.00 | 1.00 | 1.00 | 1.00 | 1.00 | 1.00 |
| Mir1942 | 1.00 | 1.00 | 1.00 | 1.00 | 1.00 | 1.00 | 1.00 | 1.00 | 1.00 | 1.00 | 1.00 | 1.00 |
| Mir194-2 | 1.00 | 1.00 | 1.00 | 1.00 | 1.00 | 1.00 | 1.00 | 1.00 | 0.10 | 1.00 | 1.00 | 1.00 |
| Mir1943 | 1.19 | 1.35 | 0.43 | 1.11 | 1.17 | 0.44 | 12.77 | 1.00 | 18.12 | 1.00 | 1.00 | 1.00 |
| Mir1945 | 0.03 | 0.87 | 0.03 | 1.00 | 0.03 | 1.00 | 1.00 | 1.00 | 1.00 | 1.00 | 1.00 | 1.00 |
| Mir1948 | 1.00 | 1.00 | 1.00 | 1.00 | 1.00 | 1.00 | 1.00 | 1.00 | 1.00 | 1.00 | 1.00 | 1.00 |
| Mir1949 | 0.40 | 0.36 | 1.56 | 0.78 | 0.61 | 0.55 | 0.06 | 1.00 | 1.00 | 1.00 | 1.00 | 1.00 |
| Mir195 | 1.00 | 1.00 | 1.00 | 1.00 | 1.00 | 1.00 | 1.00 | 1.00 | 1.00 | 1.00 | 1.00 | 1.00 |
| Mir1953 | 0.05 | 1.00 | 1.00 | 0.98 | 1.00 | 18.19 | 1.00 | 1.00 | 1.00 | 1.00 | 1.00 | 1.00 |
| Mir1955 | 1.00 | 1.00 | 1.00 | 1.00 | 1.00 | 1.00 | 1.00 | 1.00 | 1.00 | 1.00 | 1.00 | 1.00 |
| Mir1956 | 0.03 | 0.03 | 1.00 | 1.00 | 0.92 | 1.00 | 1.00 | 1.00 | 1.00 | 1.00 | 1.00 | 1.00 |
| Mir1957b | 0.78 | 0.48 | 0.63 | 0.15 | 0.06 | 1.00 | 0.38 | 1.00 | 1.00 | 1.00 | 1.00 | 1.00 |
| Mir1960 | 0.06 | 1.00 | 1.00 | 1.00 | 0.92 | 0.06 | 1.00 | 1.00 | 1.00 | 1.00 | 1.00 | 1.00 |
| Mir1964 | 0.07 | 0.94 | 0.04 | 1.00 | 0.47 | 1.02 | 1.00 | 1.00 | 1.00 | 1.00 | 1.00 | 1.00 |
| Mir1966 | 0.89 | 1.04 | 0.80 | 0.06 | 0.21 | 0.74 | 1.36 | 1.00 | 1.16 | 1.00 | 1.00 | 1.00 |
| Mir1967 | 0.54 | 0.07 | 0.07 | 1.00 | 1.00 | 1.00 | 1.00 | 1.00 | 1.00 | 1.00 | 1.00 | 1.00 |
| Mir1968 | 1.00 | 1.00 | 34.83 | 1.00 | 1.00 | 1.00 | 1.00 | 0.96 | 75.93 | 1.00 | 1.00 | 1.00 |
| Mir1969 | 0.13 | 1.00 | 1.00 | 1.00 | 1.00 | 1.00 | 1.00 | 1.00 | 1.00 | 1.00 | 1.00 | 1.00 |
| Mir196b | 0.09 | 1.00 | 1.00 | 1.15 | 0.10 | 11.90 | 1.00 | 1.00 | 1.00 | 1.00 | 1.00 | 1.00 |
| Mir1981 | 0.85 | 0.36 | 0.52 | 4.72 | 0.03 | 13.12 | 8.03 | 21.05 | 10.73 | 1.00 | 1.00 | 1.00 |
| Mir199a-1 | 0.33 | 0.57 | 0.73 | 0.66 | 0.92 | 3.28 | 0.03 | 1.00 | 1.00 | 1.00 | 1.00 | 1.00 |
| Mir199b | 1.00 | 1.00 | 1.00 | 1.00 | 1.00 | 1.00 | 1.00 | 1.00 | 1.00 | 1.00 | 1.00 | 1.00 |
| Mir19a | 0.08 | 1.00 | 15.71 | 1.00 | 1.00 | 1.00 | 1.00 | 1.00 | 1.00 | 1.00 | 1.00 | 1.00 |
| Mir19b-1 | 0.61 | 0.05 | 0.22 | 1.00 | 1.00 | 1.00 | 1.00 | 1.00 | 1.00 | 1.00 | 1.00 | 1.00 |

Fig. 31- 57

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir200a | 1.00 | 0.10 | 1.00 | 13.75 | 1.00 | 1.00 | 1.00 | 1.00 | 1.00 |
| Mir200b | 1.00 | 1.00 | 1.00 | 1.00 | 1.00 | 1.00 | 1.00 | 1.00 | 1.00 |
| Mir200c | 1.00 | 1.00 | 1.00 | 1.00 | 1.00 | 1.00 | 1.00 | 1.00 | 1.00 |
| Mir202 | 1.00 | 1.00 | 1.00 | 1.00 | 1.00 | 1.00 | 1.00 | 1.00 | 1.00 |
| Mir203 | 1.00 | 1.00 | 1.00 | 1.00 | 1.00 | 1.00 | 1.00 | 1.00 | 1.00 |
| Mir205 | 1.00 | 1.00 | 1.00 | 1.00 | 1.00 | 1.00 | 1.00 | 1.00 | 1.00 |
| Mir206 | 1.00 | 1.00 | 1.00 | 1.00 | 1.00 | 1.00 | 1.00 | 1.00 | 1.00 |
| Mir207 | 1.00 | 1.00 | 1.00 | 21.01 | 0.03 | 0.06 | 1.00 | 0.02 | 1.00 |
| Mir208b | 0.38 | 0.30 | 0.52 | 1.00 | 1.00 | 1.00 | 1.00 | 1.00 | 1.00 |
| Mir20a | 9.01 | 1.00 | 1.00 | 1.04 | 6.21 | 1.04 | 5.58 | 1.00 | 1.00 |
| Mir210 | 1.00 | 4.10 | 1.00 | 5.21 | 1.00 | 1.00 | 1.00 | 1.00 | 1.00 |
| Mir211 | 1.00 | 1.00 | 1.00 | 1.00 | 1.00 | 1.00 | 1.00 | 1.00 | 1.00 |
| Mir212 | 1.00 | 1.00 | 1.00 | 1.00 | 1.00 | 1.00 | 1.00 | 1.00 | 1.00 |
| Mir2139 | 1.00 | 2.92 | 1.00 | 1.00 | 1.00 | 1.00 | 1.00 | 1.00 | 1.00 |
| Mir214 | 0.51 | 11.61 | 8.24 | 1.00 | 1.68 | 4.31 | 1.00 | 1.00 | 3.14 |
| Mir215 | 1.00 | 0.06 | 7.57 | 1.00 | 5.41 | 1.00 | 4.88 | 0.87 | 1.00 |
| Mir217 | 1.00 | 1.00 | 1.00 | 1.00 | 1.00 | 1.00 | 1.00 | 1.00 | 1.00 |
| Mir218-2 | 1.00 | 1.00 | 1.00 | 1.00 | 1.00 | 1.00 | 1.00 | 1.00 | 1.00 |
| Mir219-1 | 1.00 | 1.00 | 1.00 | 1.00 | 1.00 | 0.23 | 1.00 | 1.00 | 1.00 |
| Mir219-2 | 1.00 | 6.68 | 1.00 | 1.00 | 1.00 | 1.00 | 1.00 | 1.00 | 1.00 |
| Mir219c | 1.00 | 1.00 | 1.00 | 1.00 | 1.00 | 1.00 | 1.00 | 1.00 | 1.00 |
| Mir22 | 0.48 | 0.74 | 31.37 | 134.76 | 0.43 | 0.80 | 1.00 | 0.03 | 0.02 |
| Mir221 | 1.00 | 7.21 | 0.12 | 1.18 | 1.00 | 1.00 | 17.23 | 7.77 | 1.00 |
| Mir222 | 1.00 | 1.00 | 1.00 | 1.00 | 1.00 | 1.00 | 1.00 | 1.00 | 1.00 |
| Mir224 | 1.00 | 1.00 | 1.00 | 21.28 | 1.00 | 1.00 | 1.00 | 1.00 | 1.00 |
| Mir23a | 36.97 | 1.00 | 1.00 | 29.08 | 1.00 | 1.00 | 1.00 | 1.00 | 1.00 |
| Mir23b | 1.00 | 1.00 | 1.00 | 1.00 | 1.00 | 1.00 | 1.00 | 1.00 | 1.00 |
| Mir24-1 | 33.57 | 0.03 | 1.00 | 1.00 | 1.00 | 1.00 | 5.70 | 0.03 | 1.00 |
| Mir24-2 | 4.76 | 1.00 | 8.71 | 1.03 | 1.00 | 1.00 | 1.00 | 1.00 | 1.00 |
| Mir25 | 47.02 | 0.65 | 1.35 | 0.90 | 1.43 | 0.69 | 29.84 | 1.78 | 1.00 |
| Mir26a-1 | 1.00 | 1.00 | 1.00 | 0.10 | 0.09 | 1.00 | 1.00 | 1.00 | 1.00 |
| Mir26a-2 | 1.00 | 1.00 | 1.00 | 1.00 | 0.06 | 1.00 | 1.00 | 1.00 | 1.00 |
| Mir26b | 11.16 | 11.05 | 1.00 | 1.00 | 0.07 | 0.04 | 1.00 | 1.00 | 0.11 |
| Mir27a | 0.87 | 1.00 | 1.00 | 0.04 | 1.00 | 1.00 | 1.00 | 0.07 | 1.00 |
| Mir27b | 1.00 | 1.00 | 1.00 | 1.00 | 1.00 | 1.00 | 1.00 | 1.00 | 1.00 |
| Mir290 | 1.00 | 1.00 | 1.00 | 1.00 | 1.00 | 1.00 | 16.72 | 4.71 | 0.05 |
| Mir290b | 1.00 | 1.00 | 1.00 | 1.00 | 1.00 | 1.00 | 1.04 | 40.48 | 248.09 |
| Mir291a | 0.09 | 1.00 | 1.00 | 1.00 | 1.00 | 1.00 | 1.00 | 1.00 | 5.46 |
| Mir291b | 1.00 | 12.02 | 1.00 | 1.00 | 1.00 | 1.00 | 32.70 | 1.72 | 19.21 |
| Mir292 | 1.00 | 1.00 | 1.00 | 1.00 | 1.00 | 1.00 | 0.13 | 25.86 | 1.58 |
| Mir292b | 1.00 | 39.94 | 1.00 | 1.00 | 1.00 | 1.00 | 1.00 | 1.00 | 1.00 |
| Mir293 | 4.91 | 1.00 | 1.00 | 1.00 | 1.00 | 1.00 | 0.06 | 1.00 | 12.76 |
| Mir294 | 4.07 | 1.00 | 1.00 | 1.00 | 1.00 | 1.00 | 1.00 | 1.00 | 0.34 |
| Mir295 | 1.00 | 1.00 | 1.00 | 1.00 | 1.00 | 1.00 | 0.01 | 0.01 | 14.71 |
| Mir29a | 10.35 | 1.00 | 1.00 | 1.00 | 1.00 | 1.00 | 1.00 | 1.00 | 1.00 |
| Mir29b-2 | 1.00 | 0.07 | 1.00 | 1.00 | 27.17 | 18.15 | 0.76 | 17.14 | 17.89 |
| Mir29c | 1.51 | 0.98 | 0.65 | 1.62 | 1.22 | 0.35 | 0.72 | 0.06 | 1.96 |
| Mir301 | 1.00 | 1.00 | 1.00 | 0.07 | 1.00 | 1.00 | 1.00 | 1.00 | 1.00 |
| Mir301b | 1.00 | 1.00 | 1.00 | 1.00 | 1.00 | 1.00 | 1.00 | 1.00 | 1.00 |
| Mir302a | 1.00 | 1.00 | 1.00 | 1.00 | 1.00 | 1.00 | 1.00 | 1.00 | 1.00 |
| Mir302b | 1.00 | 1.00 | 0.05 | 1.00 | 0.03 | 1.00 | 1.00 | 1.00 | 1.00 |
| Mir302c | 1.00 | 1.00 | 1.00 | 1.00 | 1.00 | 1.00 | 1.00 | 1.00 | 1.00 |
| Mir302d | 1.00 | 1.00 | 1.00 | 1.00 | 1.00 | 0.02 | 1.00 | 1.00 | 1.00 |
| Mir3057 | 0.67 | 0.84 | 2.70 | 1.72 | 0.91 | 1.17 | 2.21 | 0.86 | 0.94 |
| Mir3058 | 1.78 | 0.44 | 0.63 | 2.09 | 1.43 | 0.56 | 0.56 | 0.43 | 0.15 |
| Mir3060 | 1.46 | 1.15 | 0.64 | 1.16 | 0.81 | 0.57 | 1.72 | 0.42 | 1.00 |
| Mir3061 | 1.07 | 0.58 | 1.07 | 2.42 | 2.29 | 1.41 | 2.59 | 1.30 | 0.68 |
| Mir3062 | 1.00 | 8.84 | 0.10 | 1.00 | 0.58 | 1.53 | 6.31 | 0.17 | 1.00 |
| Mir3063 | 1.00 | 1.00 | 1.00 | 0.64 | 2.71 | 1.00 | 1.00 | 1.00 | 1.00 |
| Mir3065 | 1.00 | 1.00 | 1.00 | 1.00 | 1.00 | 1.00 | 1.00 | 1.00 | 1.00 |
| Mir3066 | 1.00 | 1.00 | 1.00 | 1.00 | 1.00 | 1.00 | 1.00 | 1.00 | 1.00 |
| Mir3067 | 1.00 | 1.00 | 1.00 | 1.00 | 1.00 | 1.00 | 0.92 | 3.07 | 0.11 |
| Mir3068 | 0.87 | 1.00 | 15.17 | 1.00 | 0.02 | 1.00 | 21.03 | 0.86 | 1.00 |
| Mir3069 | 0.88 | 0.03 | 0.02 | 1.00 | 1.00 | 2.33 | 1.00 | 1.00 | 1.00 |

Fig. 31- 58

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir200a | 1.00 | 1.00 | 1.00 | 1.00 | 1.00 | 1.00 | 1.00 | 1.00 | 1.00 |
| Mir200b | 1.00 | 1.00 | 1.00 | 1.00 | 1.00 | 1.00 | 1.00 | 1.00 | 1.00 |
| Mir200c | 1.00 | 1.00 | 1.00 | 1.00 | 1.00 | 1.00 | 1.00 | 1.00 | 1.00 |
| Mir202 | 1.00 | 1.10 | 1.00 | 24.58 | 1.00 | 1.00 | 1.00 | 1.00 | 29.11 |
| Mir203 | 1.00 | 1.00 | 1.00 | 1.00 | 1.00 | 1.00 | 1.00 | 1.00 | 1.00 |
| Mir205 | 1.00 | 1.00 | 1.00 | 1.00 | 1.00 | 1.00 | 1.00 | 1.00 | 1.00 |
| Mir206 | 1.00 | 1.00 | 1.00 | 1.00 | 1.00 | 18.80 | 1.00 | 1.00 | 1.00 |
| Mir207 | 1.00 | 1.00 | 1.81 | 13.04 | 1.00 | 14.32 | 1.00 | 1.06 | 0.02 |
| Mir208b | 0.37 | 0.81 | 0.91 | 1.00 | 1.00 | 1.00 | 1.00 | 1.00 | 1.00 |
| Mir20a | 0.25 | 1.00 | 0.14 | 1.00 | 1.00 | 1.00 | 11.95 | 1.00 | 1.00 |
| Mir210 | 0.39 | 3.69 | 4.11 | 1.00 | 1.00 | 1.00 | 1.00 | 1.00 | 1.00 |
| Mir211 | 1.00 | 1.00 | 1.00 | 1.00 | 1.00 | 1.00 | 1.00 | 1.00 | 1.00 |
| Mir212 | 1.00 | 0.14 | 1.00 | 1.00 | 1.00 | 1.00 | 1.00 | 1.00 | 1.00 |
| Mir2139 | 1.00 | 1.00 | 1.00 | 1.00 | 1.00 | 1.00 | 1.00 | 1.00 | 1.00 |
| Mir214 | 0.79 | 2.23 | 0.08 | 7.25 | 6.80 | 1.00 | 5.73 | 16.24 | 0.27 |
| Mir215 | 3.59 | 3.58 | 1.00 | 0.24 | 3.99 | 3.79 | 0.36 | 11.17 | 1.55 |
| Mir217 | 1.00 | 1.00 | 1.00 | 1.00 | 1.00 | 1.00 | 1.00 | 1.00 | 1.00 |
| Mir218-2 | 1.00 | 1.00 | 1.00 | 1.00 | 1.00 | 1.00 | 1.00 | 1.00 | 1.00 |
| Mir219-1 | 3.70 | 0.14 | 0.27 | 1.00 | 1.00 | 1.00 | 1.00 | 1.00 | 0.18 |
| Mir219-2 | 1.00 | 1.00 | 1.00 | 1.00 | 1.00 | 1.00 | 1.00 | 1.00 | 1.00 |
| Mir219c | 1.00 | 1.00 | 1.00 | 1.00 | 1.00 | 1.00 | 1.00 | 1.00 | 1.00 |
| Mir22 | 0.08 | 0.09 | 0.07 | 4.51 | 2.56 | 0.37 | 4.01 | 2.21 | 1.00 |
| Mir221 | 0.96 | 0.06 | 12.38 | 1.00 | 6.57 | 1.00 | 1.00 | 1.00 | 1.00 |
| Mir222 | 1.00 | 1.00 | 0.08 | 1.00 | 1.00 | 1.00 | 1.00 | 1.00 | 1.00 |
| Mir224 | 0.09 | 1.00 | 1.00 | 11.64 | 1.00 | 1.00 | 1.00 | 1.00 | 1.00 |
| Mir23a | 3.01 | 0.56 | 2.24 | 1.00 | 1.00 | 1.00 | 1.00 | 1.00 | 73.45 |
| Mir23b | 1.00 | 1.00 | 1.00 | 1.00 | 1.00 | 1.00 | 1.00 | 1.00 | 1.00 |
| Mir24-1 | 1.00 | 0.72 | 0.01 | 1.00 | 1.00 | 0.02 | 1.00 | 1.00 | 1.00 |
| Mir24-2 | 1.26 | 4.04 | 1.13 | 1.00 | 1.00 | 1.00 | 0.99 | 1.00 | 19.22 |
| Mir25 | 1.41 | 2.82 | 0.73 | 1.19 | 0.99 | 1.00 | 1.10 | 0.99 | 1.17 |
| Mir26a-1 | 1.00 | 14.54 | 0.37 | 1.00 | 1.00 | 1.00 | 1.00 | 1.00 | 1.00 |
| Mir26a-2 | 1.00 | 1.00 | 1.00 | 1.00 | 1.00 | 1.00 | 1.00 | 1.00 | 1.00 |
| Mir26b | 0.10 | 18.25 | 2.21 | 1.00 | 1.00 | 0.09 | 1.01 | 0.06 | 3.31 |
| Mir27a | 0.42 | 0.45 | 1.87 | 0.11 | 1.00 | 0.09 | 0.32 | 1.09 | 0.04 |
| Mir27b | 1.00 | 1.00 | 1.00 | 8.46 | 1.00 | 1.00 | 6.09 | 1.00 | 1.00 |
| Mir290 | 1.00 | 1.00 | 1.14 | 1.00 | 1.00 | 1.00 | 1.00 | 1.00 | 1.00 |
| Mir290b | 1.00 | 54.69 | 1.00 | 1.00 | 1.00 | 1.00 | 1.00 | 1.00 | 1.00 |
| Mir291a | 1.00 | 1.00 | 9.81 | 1.00 | 1.00 | 1.00 | 9.84 | 8.95 | 1.00 |
| Mir291b | 8.98 | 1.00 | 1.00 | 1.00 | 1.00 | 1.00 | 1.00 | 0.08 | 1.00 |
| Mir292 | 0.10 | 10.01 | 1.00 | 1.00 | 1.00 | 1.00 | 0.05 | 1.00 | 1.00 |
| Mir292b | 39.91 | 1.00 | 1.00 | 1.00 | 1.00 | 1.00 | 0.04 | 1.00 | 1.00 |
| Mir293 | 1.00 | 1.00 | 1.00 | 1.00 | 1.00 | 1.00 | 1.00 | 0.09 | 16.38 |
| Mir294 | 0.14 | 0.29 | 4.52 | 1.00 | 1.00 | 1.00 | 1.00 | 1.00 | 0.06 |
| Mir295 | 1.00 | 1.00 | 0.05 | 1.00 | 1.00 | 1.00 | 2.77 | 1.00 | 0.03 |
| Mir29a | 1.00 | 1.00 | 1.00 | 1.00 | 1.00 | 1.00 | 0.84 | 1.00 | 1.00 |
| Mir29b-2 | 0.09 | 29.88 | 0.05 | 2.96 | 1.26 | 0.26 | 1.47 | 1.75 | 0.03 |
| Mir29c | 1.34 | 0.60 | 1.19 | 83.17 | 0.02 | 0.55 | 1.02 | 2.31 | 0.43 |
| Mir301 | 0.11 | 1.00 | 1.00 | 1.00 | 1.00 | 1.00 | 1.00 | 1.00 | 1.00 |
| Mir301b | 1.00 | 1.00 | 1.00 | 1.00 | 1.00 | 1.00 | 1.00 | 1.00 | 1.00 |
| Mir302a | 1.00 | 1.00 | 1.00 | 1.00 | 1.00 | 1.00 | 1.00 | 47.82 | 0.01 |
| Mir302b | 1.00 | 16.62 | 0.06 | 1.00 | 1.00 | 1.00 | 1.00 | 1.00 | 1.00 |
| Mir302c | 1.00 | 1.00 | 1.00 | 1.00 | 1.00 | 1.00 | 48.44 | 1.00 | 1.00 |
| Mir302d | 1.00 | 1.00 | 1.00 | 1.00 | 1.00 | 1.00 | 57.53 | 1.00 | 51.17 |
| Mir3057 | 1.35 | 3.00 | 1.97 | 16.15 | 0.51 | 0.37 | 0.79 | 2.13 | 0.72 |
| Mir3058 | 0.36 | 2.40 | 2.08 | 1.18 | 0.05 | 1.37 | 32.45 | 0.20 | 2.83 |
| Mir3060 | 1.15 | 0.58 | 0.65 | 0.39 | 43.30 | 3.24 | 1.49 | 0.85 | 1.08 |
| Mir3061 | 0.23 | 0.69 | 1.30 | 0.82 | 1.49 | 0.86 | 0.75 | 1.21 | 0.66 |
| Mir3062 | 11.75 | 0.12 | 2.75 | 9.15 | 4.82 | 0.98 | 0.84 | 2.32 | 2.80 |
| Mir3063 | 1.00 | 0.54 | 0.04 | 1.00 | 1.00 | 1.00 | 1.00 | 1.00 | 1.00 |
| Mir3065 | 0.06 | 1.00 | 1.00 | 1.00 | 1.00 | 1.00 | 1.00 | 1.00 | 0.07 |
| Mir3066 | 1.00 | 1.00 | 1.00 | 1.00 | 1.00 | 1.00 | 1.00 | 1.00 | 1.00 |
| Mir3067 | 1.00 | 1.00 | 0.10 | 1.00 | 1.00 | 0.09 | 1.00 | 1.00 | 1.00 |
| Mir3068 | 49.44 | 0.04 | 1.00 | 1.00 | 0.04 | 1.00 | 20.74 | 0.04 | 0.94 |
| Mir3069 | 20.44 | 16.52 | 62.03 | 0.01 | 1.00 | 1.00 | 1.00 | 1.00 | 1.80 |

Fig. 31-59

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir200a | 1.00 | 1.00 | 1.00 | 1.00 | 1.00 | 1.00 | 0.75 | 3.47 | 1.13 |
| Mir200b | 1.00 | 1.00 | 1.00 | 1.00 | 1.00 | 1.00 | 1.00 | 0.04 | 21.25 |
| Mir200c | 1.00 | 1.00 | 1.00 | 1.00 | 52.28 | 1.00 | 1.00 | 0.04 | 0.04 |
| Mir202 | 1.00 | 1.00 | 1.00 | 1.00 | 0.03 | 1.00 | 0.37 | 0.24 | 21.45 |
| Mir203 | 1.00 | 1.00 | 1.00 | 1.00 | 1.00 | 1.00 | 1.00 | 1.00 | 1.00 |
| Mir205 | 1.00 | 1.00 | 1.00 | 1.00 | 1.00 | 1.00 | 1.00 | 1.00 | 1.00 |
| Mir206 | 1.00 | 1.00 | 1.00 | 1.00 | 1.00 | 1.00 | 1.00 | 1.00 | 1.00 |
| Mir207 | 30.40 | 1.00 | 0.04 | 0.05 | 0.02 | 41.33 | 0.37 | 0.03 | 106.21 |
| Mir208b | 1.08 | 1.50 | 1.72 | 1.00 | 1.00 | 1.00 | 0.07 | 26.22 | 0.07 |
| Mir20a | 1.00 | 1.00 | 1.00 | 6.32 | 1.00 | 1.00 | 1.00 | 4.21 | 1.00 |
| Mir210 | 0.17 | 1.00 | 1.00 | 1.00 | 9.95 | 1.00 | 1.00 | 10.51 | 1.01 |
| Mir211 | 1.00 | 5.78 | 1.00 | 1.00 | 1.00 | 1.00 | 1.00 | 1.00 | 1.00 |
| Mir212 | 2.00 | 1.18 | 0.69 | 1.00 | 1.00 | 1.00 | 2.07 | 0.91 | 1.41 |
| Mir2139 | 1.53 | 5.65 | 1.00 | 1.00 | 1.00 | 1.00 | 1.00 | 1.00 | 1.00 |
| Mir214 | 1.00 | 1.00 | 1.33 | 1.08 | 1.90 | 4.48 | 1.00 | 0.16 | 1.27 |
| Mir215 | 0.08 | 0.21 | 2.77 | 0.69 | 1.05 | 1.69 | 2.05 | 1.00 | 0.14 |
| Mir217 | 1.00 | 1.00 | 1.00 | 1.00 | 1.00 | 1.00 | 1.00 | 1.00 | 1.00 |
| Mir218-2 | 9.25 | 1.00 | 0.24 | 9.88 | 1.00 | 1.00 | 0.25 | 1.00 | 1.00 |
| Mir219-1 | 9.25 | 1.00 | 1.00 | 1.00 | 0.96 | 7.13 | 1.00 | 0.90 | 1.12 |
| Mir219-2 | 0.47 | 1.30 | 0.70 | 1.00 | 1.00 | 1.00 | 1.00 | 1.00 | 1.00 |
| Mir219c | 1.00 | 1.00 | 1.00 | 1.00 | 0.01 | 1.00 | 51.30 | 1.00 | 1.00 |
| Mir22 | 0.05 | 0.81 | 0.02 | 0.91 | 22.17 | 1.00 | 11.82 | 0.10 | 0.63 |
| Mir221 | 0.04 | 1.00 | 21.37 | 0.13 | 0.11 | 1.81 | 1.00 | 1.00 | 1.00 |
| Mir222 | 1.00 | 1.00 | 1.00 | 1.00 | 1.00 | 1.00 | 1.00 | 1.00 | 1.00 |
| Mir224 | 1.00 | 1.00 | 1.00 | 1.00 | 1.00 | 0.08 | 1.00 | 1.00 | 1.00 |
| Mir23a | 1.00 | 0.03 | 1.00 | 31.13 | 0.01 | 0.54 | 35.57 | 1.00 | 1.00 |
| Mir23b | 1.00 | 1.00 | 1.00 | 1.00 | 1.00 | 1.00 | 14.26 | 1.00 | 1.00 |
| Mir24-1 | 1.00 | 1.00 | 1.00 | 1.00 | 1.00 | 1.00 | 4.15 | 1.00 | 1.00 |
| Mir24-2 | 5.00 | 0.17 | 1.00 | 1.26 | 10.03 | 2.09 | 1.00 | 1.00 | 1.00 |
| Mir25 | 83.16 | 0.75 | 1.51 | 1.72 | 1.26 | 1.54 | 1.09 | 0.49 | 1.55 |
| Mir26a-1 | 0.90 | 11.80 | 1.00 | 0.03 | 1.16 | 0.04 | 0.07 | 1.00 | 1.00 |
| Mir26a-2 | 1.00 | 1.00 | 1.00 | 1.00 | 1.00 | 1.00 | 1.00 | 10.14 | 1.00 |
| Mir26b | 0.07 | 1.00 | 1.00 | 1.00 | 1.00 | 1.00 | 1.07 | 1.00 | 0.59 |
| Mir27a | 1.00 | 13.85 | 0.09 | 1.39 | 0.49 | 0.42 | 0.11 | 0.11 | 0.11 |
| Mir27b | 1.00 | 1.00 | 1.00 | 11.16 | 1.00 | 3.74 | 1.00 | 1.00 | 14.08 |
| Mir290 | 1.00 | 1.00 | 1.00 | 19.75 | 1.00 | 1.00 | 1.00 | 1.00 | 1.00 |
| Mir290b | 1.00 | 1.00 | 1.00 | 1.00 | 1.00 | 1.00 | 1.00 | 1.00 | 1.00 |
| Mir291a | 1.00 | 1.00 | 1.00 | 1.00 | 1.00 | 1.00 | 1.00 | 1.00 | 1.00 |
| Mir291b | 1.00 | 1.00 | 1.00 | 1.00 | 1.00 | 1.00 | 1.00 | 12.97 | 1.00 |
| Mir292 | 1.00 | 1.00 | 1.00 | 0.06 | 1.00 | 1.00 | 1.00 | 1.00 | 1.00 |
| Mir292b | 1.00 | 1.00 | 1.00 | 1.00 | 1.00 | 1.00 | 1.00 | 1.00 | 1.00 |
| Mir293 | 1.00 | 1.00 | 1.00 | 1.00 | 1.00 | 1.00 | 0.09 | 1.00 | 10.12 |
| Mir294 | 1.00 | 1.00 | 1.00 | 1.00 | 1.00 | 1.00 | 9.95 | 1.00 | 0.05 |
| Mir295 | 1.00 | 1.00 | 1.00 | 1.00 | 1.00 | 1.00 | 0.05 | 1.00 | 1.00 |
| Mir29a | 1.00 | 1.00 | 1.00 | 1.00 | 1.00 | 1.00 | 1.00 | 1.00 | 1.00 |
| Mir29b-2 | 1.00 | 1.00 | 40.80 | 1.00 | 1.30 | 1.00 | 1.29 | 0.68 | 1.00 |
| Mir29c | 2.02 | 0.99 | 0.86 | 2.00 | 2.63 | 0.62 | 0.46 | 3.72 | 0.30 |
| Mir301 | 1.00 | 1.00 | 1.00 | 15.12 | 0.08 | 0.10 | 0.10 | 1.00 | 1.00 |
| Mir301b | 1.00 | 1.00 | 7.16 | 1.00 | 1.00 | 1.00 | 1.00 | 1.00 | 0.53 |
| Mir302a | 1.00 | 1.00 | 1.00 | 1.00 | 1.00 | 1.00 | 1.00 | 1.00 | 1.00 |
| Mir302b | 1.00 | 1.00 | 1.00 | 1.00 | 1.00 | 1.00 | 1.00 | 1.00 | 1.00 |
| Mir302c | 48.78 | 1.00 | 1.00 | 1.00 | 0.02 | 1.00 | 1.00 | 1.00 | 1.00 |
| Mir302d | 1.00 | 1.00 | 0.02 | 1.00 | 1.00 | 1.00 | 0.03 | 1.00 | 1.00 |
| Mir3057 | 2.58 | 0.97 | 1.00 | 0.98 | 0.52 | 0.43 | 1.11 | 7.47 | 1.03 |
| Mir3058 | 0.94 | 32.25 | 1.00 | 1.86 | 1.00 | 0.74 | 0.13 | 0.12 | 1.18 |
| Mir3060 | 2.39 | 0.53 | 0.48 | 0.82 | 1.48 | 1.15 | 1.00 | 0.43 | 1.98 |
| Mir3061 | 0.82 | 0.67 | 0.90 | 0.31 | 0.53 | 0.14 | 0.05 | 5.05 | 2.00 |
| Mir3062 | 0.14 | 0.06 | 2.81 | 12.01 | 1.08 | 0.56 | 5.03 | 3.14 | 0.41 |
| Mir3063 | 1.00 | 1.00 | 1.00 | 1.00 | 1.00 | 1.00 | 1.17 | 0.74 | 0.66 |
| Mir3065 | 0.74 | 1.00 | 1.00 | 0.07 | 1.00 | 0.48 | 0.11 | 0.10 | 1.00 |
| Mir3066 | 1.00 | 1.00 | 1.00 | 1.00 | 1.00 | 1.00 | 1.00 | 1.00 | 11.62 |
| Mir3067 | 1.00 | 1.00 | 1.00 | 34.57 | 1.62 | 1.31 | 1.00 | 0.89 | 1.00 |
| Mir3068 | 1.00 | 1.02 | 1.00 | 0.04 | 1.00 | 15.67 | 1.00 | 1.78 | 14.17 |
| Mir3069 | 0.01 | 0.02 | 1.23 | 1.00 | 1.00 | 81.01 | 1.00 | 1.00 | 23.94 |

Fig. 31- 60

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir200a | 1.00 | 1.00 | 1.00 | 1.00 | 1.00 | 1.00 | 1.00 | 1.00 | 1.00 | 1.00 | 1.00 | 1.00 |
| Mir200b | 1.00 | 1.00 | 0.03 | 1.00 | 1.00 | 1.00 | 1.00 | 1.00 | 1.00 | 1.00 | 1.00 | 1.00 |
| Mir200c | 1.00 | 49.57 | 1.00 | 1.00 | 1.00 | 1.00 | 1.00 | 1.00 | 1.00 | 1.00 | 1.00 | 1.00 |
| Mir202 | 1.06 | 1.00 | 28.39 | 1.00 | 1.00 | 1.00 | 1.00 | 1.00 | 1.00 | 1.00 | 1.00 | 1.00 |
| Mir203 | 1.00 | 1.00 | 20.36 | 1.00 | 1.00 | 1.00 | 1.00 | 1.00 | 1.00 | 1.00 | 1.00 | 1.00 |
| Mir205 | 0.03 | 57.39 | 34.83 | 1.00 | 1.00 | 1.00 | 1.00 | 1.00 | 1.00 | 1.00 | 1.00 | 1.00 |
| Mir206 | 1.00 | 1.00 | 1.00 | 1.00 | 1.00 | 1.00 | 1.00 | 1.00 | 1.00 | 1.00 | 1.00 | 1.00 |
| Mir207 | 0.09 | 29.20 | 1.00 | 2.29 | 1.00 | 17.95 | 6.92 | 1.00 | 12.61 | 1.00 | 1.00 | 1.00 |
| Mir208b | 1.00 | 0.56 | 20.75 | 1.00 | 1.00 | 1.00 | 1.00 | 1.00 | 1.00 | 1.00 | 1.00 | 1.00 |
| Mir20a | 5.84 | 0.91 | 1.00 | 0.21 | 0.12 | 0.24 | 3.15 | 1.00 | 3.86 | 1.00 | 1.00 | 1.00 |
| Mir210 | 1.00 | 4.23 | 0.12 | 1.00 | 1.00 | 1.00 | 1.00 | 1.00 | 1.00 | 1.00 | 1.00 | 1.00 |
| Mir211 | 1.00 | 1.00 | 1.00 | 1.00 | 1.00 | 1.00 | 1.00 | 1.00 | 1.00 | 1.00 | 1.00 | 1.00 |
| Mir212 | 18.07 | 1.00 | 1.00 | 1.00 | 1.00 | 1.00 | 1.00 | 1.00 | 1.00 | 1.00 | 1.00 | 1.00 |
| Mir2139 | 1.00 | 1.00 | 1.00 | 1.00 | 1.00 | 1.00 | 1.00 | 0.13 | 1.00 | 1.00 | 1.00 | 1.00 |
| Mir214 | 16.57 | 5.92 | 1.30 | 0.23 | 0.24 | 1.00 | 2.25 | 1.44 | 0.44 | 1.00 | 1.00 | 1.00 |
| Mir215 | 1.00 | 1.96 | 1.00 | 1.00 | 0.24 | 0.13 | 1.00 | 1.00 | 1.00 | 1.00 | 1.00 | 1.00 |
| Mir217 | 1.00 | 1.00 | 1.00 | 1.00 | 1.00 | 1.00 | 1.00 | 0.24 | 7.02 | 1.00 | 1.00 | 1.00 |
| Mir218-2 | 1.00 | 4.94 | 1.00 | 1.00 | 1.00 | 1.00 | 1.00 | 1.00 | 1.00 | 1.00 | 1.00 | 1.00 |
| Mir219-1 | 8.97 | 1.00 | 1.00 | 1.00 | 1.00 | 1.00 | 0.30 | 1.00 | 1.00 | 1.00 | 1.00 | 1.00 |
| Mir219-2 | 1.00 | 1.00 | 1.00 | 1.00 | 1.00 | 1.00 | 1.00 | 1.00 | 1.00 | 1.00 | 1.00 | 1.00 |
| Mir219c | 1.00 | 1.00 | 0.01 | 1.00 | 1.00 | 1.00 | 1.00 | 1.00 | 1.00 | 1.00 | 1.00 | 1.00 |
| Mir22 | 1.00 | 1.00 | 0.99 | 0.39 | 0.10 | 2.50 | 1.00 | 1.00 | 1.62 | 1.00 | 1.00 | 1.00 |
| Mir221 | 0.61 | 1.00 | 7.97 | 1.00 | 1.00 | 7.22 | 1.00 | 1.00 | 1.00 | 1.00 | 1.00 | 1.00 |
| Mir222 | 16.06 | 1.00 | 1.00 | 1.00 | 1.00 | 1.00 | 1.00 | 1.00 | 1.00 | 1.00 | 1.00 | 1.00 |
| Mir224 | 1.00 | 1.00 | 1.00 | 1.00 | 1.00 | 1.00 | 1.00 | 1.00 | 1.00 | 1.00 | 1.00 | 1.00 |
| Mir23a | 0.05 | 1.00 | 1.00 | 0.06 | 1.94 | 0.03 | 10.94 | 1.00 | 1.00 | 1.00 | 1.00 | 1.00 |
| Mir23b | 1.00 | 1.00 | 1.00 | 1.00 | 1.00 | 1.00 | 1.00 | 1.00 | 1.00 | 1.00 | 1.00 | 0.03 |
| Mir24-1 | 1.00 | 1.00 | 1.00 | 1.00 | 1.00 | 1.00 | 2.45 | 1.00 | 1.00 | 1.00 | 1.00 | 1.00 |
| Mir24-2 | 1.00 | 0.19 | 0.11 | 0.13 | 0.22 | 0.13 | 1.00 | 1.00 | 1.00 | 1.00 | 1.00 | 1.00 |
| Mir25 | 0.84 | 0.89 | 1.33 | 1.32 | 0.71 | 0.56 | 7.02 | 11.11 | 1.00 | 1.00 | 1.00 | 1.00 |
| Mir26a-1 | 9.68 | 0.10 | 1.00 | 1.00 | 1.00 | 1.00 | 1.00 | 1.00 | 1.00 | 1.00 | 1.00 | 1.00 |
| Mir26a-2 | 1.00 | 1.00 | 1.00 | 1.00 | 1.00 | 1.00 | 1.00 | 1.00 | 1.00 | 1.00 | 1.00 | 1.00 |
| Mir26b | 0.61 | 0.88 | 0.53 | 34.33 | 0.03 | 0.03 | 1.00 | 1.00 | 1.00 | 1.00 | 1.00 | 1.00 |
| Mir27a | 1.91 | 9.74 | 12.24 | 0.26 | 0.32 | 0.77 | 1.00 | 1.00 | 1.00 | 1.00 | 1.00 | 1.00 |
| Mir27b | 1.00 | 1.00 | 1.00 | 1.00 | 1.00 | 1.00 | 1.00 | 1.00 | 1.00 | 1.00 | 1.00 | 1.00 |
| Mir290 | 1.00 | 1.00 | 1.00 | 1.00 | 0.04 | 1.07 | 1.00 | 1.00 | 1.00 | 1.00 | 1.00 | 1.00 |
| Mir290b | 1.00 | 1.00 | 1.00 | 0.02 | 1.10 | 1.00 | 1.00 | 1.00 | 1.00 | 1.00 | 1.00 | 1.00 |
| Mir291a | 1.00 | 1.00 | 1.00 | 1.00 | 18.63 | 1.00 | 1.00 | 1.00 | 1.00 | 1.00 | 1.00 | 1.00 |
| Mir291b | 1.00 | 1.00 | 1.00 | 39.12 | 0.10 | 1.00 | 1.00 | 1.00 | 1.00 | 1.00 | 1.00 | 1.00 |
| Mir292 | 1.00 | 1.00 | 1.00 | 8.28 | 1.00 | 1.00 | 1.00 | 1.00 | 1.00 | 1.00 | 1.00 | 1.00 |
| Mir292b | 39.35 | 1.00 | 1.00 | 1.00 | 1.00 | 1.00 | 1.00 | 1.00 | 1.00 | 1.00 | 1.00 | 1.00 |
| Mir293 | 1.00 | 1.51 | 1.00 | 1.00 | 0.25 | 1.00 | 1.00 | 1.00 | 1.00 | 1.00 | 1.00 | 1.00 |
| Mir294 | 1.00 | 1.00 | 1.00 | 1.00 | 1.00 | 1.00 | 1.00 | 1.00 | 1.00 | 1.00 | 1.00 | 1.00 |
| Mir295 | 1.00 | 1.00 | 1.00 | 1.00 | 0.29 | 1.00 | 1.00 | 1.00 | 1.00 | 1.00 | 1.00 | 1.00 |
| Mir29a | 1.00 | 1.00 | 1.00 | 1.00 | 0.11 | 1.00 | 1.00 | 1.00 | 1.00 | 1.00 | 1.00 | 1.00 |
| Mir29b-2 | 0.32 | 1.21 | 0.01 | 2.63 | 0.12 | 0.39 | 3.55 | 1.00 | 1.00 | 1.00 | 1.00 | 1.00 |
| Mir29c | 0.55 | 0.36 | 0.53 | 0.57 | 7.37 | 0.12 | 0.53 | 1.96 | 0.57 | 1.00 | 1.00 | 1.00 |
| Mir301 | 11.50 | 0.04 | 0.04 | 1.00 | 1.00 | 1.00 | 1.00 | 1.00 | 1.00 | 1.00 | 1.00 | 1.00 |
| Mir301b | 0.94 | 1.00 | 0.13 | 1.00 | 1.00 | 1.00 | 1.00 | 1.00 | 1.00 | 1.00 | 1.00 | 1.00 |
| Mir302a | 0.03 | 1.00 | 1.00 | 1.00 | 1.00 | 0.04 | 1.00 | 1.00 | 1.00 | 1.00 | 1.00 | 1.00 |
| Mir302b | 43.78 | 1.00 | 0.04 | 1.00 | 0.05 | 1.00 | 1.00 | 1.00 | 1.00 | 1.00 | 1.00 | 1.00 |
| Mir302c | 1.00 | 0.03 | 1.00 | 1.00 | 1.00 | 1.00 | 1.00 | 1.00 | 1.00 | 1.00 | 1.00 | 1.00 |
| Mir302d | 1.00 | 1.00 | 1.00 | 36.22 | 1.00 | 1.00 | 1.00 | 1.00 | 1.00 | 1.00 | 1.00 | 1.00 |
| Mir3057 | 1.15 | 1.30 | 1.02 | 3.93 | 6.42 | 8.55 | 1.33 | 1.13 | 7.02 | 1.00 | 1.00 | 1.00 |
| Mir3058 | 18.76 | 1.94 | 0.66 | 0.55 | 0.74 | 0.92 | 14.66 | 1.00 | 7.05 | 1.00 | 1.00 | 1.00 |
| Mir3060 | 1.20 | 1.72 | 0.62 | 0.22 | 0.94 | 0.62 | 1.15 | 0.04 | 2.96 | 1.00 | 1.00 | 1.00 |
| Mir3061 | 3.89 | 2.01 | 1.22 | 1.56 | 0.98 | 1.14 | 1.64 | 0.04 | 1.07 | 1.00 | 1.00 | 1.00 |
| Mir3062 | 1.25 | 0.51 | 0.99 | 1.30 | 0.63 | 1.13 | 3.23 | 4.93 | 0.22 | 1.00 | 1.00 | 1.00 |
| Mir3063 | 9.95 | 1.00 | 1.00 | 1.00 | 1.00 | 1.00 | 1.00 | 1.00 | 1.00 | 1.00 | 1.00 | 1.00 |
| Mir3065 | 1.00 | 1.00 | 1.00 | 1.00 | 1.00 | 1.00 | 17.26 | 25.39 | 0.04 | 1.00 | 1.00 | 1.00 |
| Mir3066 | 1.00 | 1.00 | 1.00 | 1.00 | 1.00 | 1.00 | 1.00 | 1.00 | 1.00 | 1.00 | 1.00 | 1.00 |
| Mir3067 | 1.00 | 1.00 | 14.17 | 1.00 | 1.00 | 1.00 | 1.00 | 1.00 | 0.12 | 1.00 | 1.00 | 1.00 |
| Mir3068 | 1.06 | 1.85 | 33.71 | 0.98 | 0.34 | 0.28 | 1.00 | 0.09 | 0.05 | 1.00 | 1.00 | 1.00 |
| Mir3069 | 1.00 | 0.11 | 59.25 | 30.65 | 1.00 | 0.04 | 0.04 | 0.05 | 1.00 | 1.00 | 1.00 | 1.00 |

Fig. 31-61

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir3070a | 1.00 | 1.00 | 1.00 | 1.00 | 1.00 | 1.00 | 1.00 | 1.00 | 1.00 |
| Mir3071 | 1.00 | 1.00 | 1.00 | 1.00 | 1.00 | 1.00 | 1.00 | 1.00 | 1.00 |
| Mir3072 | 1.00 | 12.15 | 12.39 | 1.00 | 1.00 | 1.00 | 1.00 | 1.00 | 0.06 |
| Mir3073 | 1.00 | 1.00 | 1.00 | 1.00 | 1.00 | 12.80 | 1.00 | 1.00 | 1.00 |
| Mir3074-1 | 0.16 | 0.04 | 0.57 | 4.82 | 0.43 | 0.73 | 0.54 | 0.24 | 0.30 |
| Mir3074-2 | 1.00 | 1.00 | 1.00 | 1.00 | 1.00 | 1.00 | 1.00 | 1.00 | 1.00 |
| Mir3075 | 1.00 | 1.00 | 1.00 | 1.00 | 1.00 | 1.00 | 1.00 | 1.00 | 1.00 |
| Mir3076 | 1.00 | 1.00 | 1.00 | 1.00 | 1.00 | 1.00 | 1.00 | 1.00 | 1.00 |
| Mir3077 | 1.00 | 1.00 | 39.38 | 1.00 | 1.00 | 1.00 | 1.00 | 1.00 | 1.00 |
| Mir3081 | 1.00 | 1.00 | 1.00 | 1.00 | 1.00 | 1.00 | 1.00 | 1.00 | 1.00 |
| Mir3082 | 0.01 | 1.00 | 108.35 | 1.00 | 1.00 | 1.00 | 1.00 | 1.00 | 1.00 |
| Mir3084 | 1.00 | 1.00 | 1.00 | 1.00 | 1.00 | 1.00 | 1.00 | 1.00 | 0.04 |
| Mir3086 | 1.00 | 1.00 | 1.00 | 1.00 | 1.00 | 0.09 | 1.00 | 1.00 | 1.00 |
| Mir3087 | 1.00 | 1.00 | 1.00 | 1.00 | 1.00 | 1.00 | 1.00 | 1.00 | 1.00 |
| Mir3089 | 1.00 | 1.00 | 1.00 | 1.00 | 1.00 | 13.05 | 1.00 | 1.00 | 1.00 |
| Mir3091 | 0.85 | 0.17 | 0.46 | 2.07 | 0.58 | 2.06 | 0.73 | 20.91 | 25.86 |
| Mir3092 | 1.00 | 0.13 | 1.00 | 1.00 | 1.00 | 1.00 | 1.00 | 1.00 | 1.00 |
| Mir3094 | 1.00 | 1.00 | 1.00 | 1.00 | 1.00 | 1.00 | 1.00 | 1.00 | 1.00 |
| Mir3095 | 1.00 | 0.09 | 1.00 | 1.00 | 1.00 | 1.00 | 1.00 | 1.00 | 1.00 |
| Mir3097 | 1.00 | 1.00 | 1.00 | 1.00 | 1.00 | 0.02 | 1.00 | 1.00 | 1.00 |
| Mir30b | 1.00 | 1.00 | 1.00 | 1.00 | 0.12 | 1.01 | 1.00 | 1.00 | 1.00 |
| Mir30c-2 | 11.70 | 0.08 | 0.08 | 0.06 | 1.12 | 0.04 | 1.00 | 1.00 | 15.55 |
| Mir30d | 1.00 | 1.00 | 13.38 | 0.29 | 1.15 | 1.04 | 16.73 | 0.05 | 1.00 |
| Mir30f | 1.00 | 1.00 | 1.00 | 1.00 | 0.09 | 1.00 | 1.00 | 1.00 | 1.00 |
| Mir3100 | 0.57 | 0.43 | 1.06 | 1.00 | 256.89 | 52.17 | 55.95 | 113.20 | 0.97 |
| Mir3102 | 1.64 | 0.45 | 1.00 | 0.06 | 1.12 | 1.86 | 0.17 | 1.00 | 1.00 |
| Mir3103 | 1.00 | 1.00 | 1.00 | 1.00 | 1.00 | 1.00 | 1.00 | 1.00 | 1.00 |
| Mir3104 | 1.00 | 1.00 | 1.00 | 1.00 | 1.00 | 1.00 | 1.00 | 1.00 | 1.00 |
| Mir3107 | 1.00 | 1.00 | 1.00 | 1.00 | 1.00 | 1.00 | 1.00 | 1.00 | 1.00 |
| Mir3109 | 1.00 | 1.00 | 1.00 | 1.00 | 1.00 | 1.00 | 1.00 | 1.00 | 1.00 |
| Mir3112 | 0.06 | 0.04 | 1.00 | 0.10 | 1.00 | 0.10 | 0.23 | 0.21 | 1.00 |
| Mir32 | 1.00 | 25.19 | 1.00 | 1.00 | 1.00 | 1.00 | 1.00 | 1.00 | 1.00 |
| Mir320 | 1.00 | 1.00 | 1.00 | 0.06 | 1.00 | 1.00 | 17.67 | 1.00 | 1.00 |
| Mir324 | 1.03 | 0.40 | 0.60 | 1.11 | 0.76 | 0.36 | 0.92 | 1.67 | 35.21 |
| Mir328 | 6.75 | 1.00 | 6.99 | 1.92 | 1.17 | 1.94 | 1.00 | 1.74 | 1.00 |
| Mir329 | 1.00 | 1.00 | 1.00 | 1.00 | 1.00 | 1.00 | 1.00 | 1.00 | 1.00 |
| Mir330 | 0.31 | 0.14 | 0.07 | 1.00 | 1.14 | 0.15 | 1.00 | 1.00 | 1.00 |
| Mir331 | 0.12 | 2.38 | 26.47 | 1.36 | 2.22 | 7.61 | 0.06 | 0.87 | 1.00 |
| Mir335 | 1.00 | 1.00 | 1.00 | 1.00 | 1.00 | 1.00 | 1.00 | 1.00 | 1.00 |
| Mir337 | 1.00 | 1.00 | 1.00 | 1.00 | 1.00 | 1.00 | 1.00 | 1.00 | 1.00 |
| Mir338 | 1.00 | 1.00 | 1.00 | 1.00 | 1.00 | 1.00 | 1.00 | 0.13 | 1.00 |
| Mir339 | 0.89 | 6.63 | 2.47 | 1.15 | 0.11 | 0.07 | 0.02 | 1.05 | 9.14 |
| Mir343 | 3.64 | 3.44 | 0.24 | 0.73 | 0.98 | 1.71 | 0.92 | 44.15 | 53.20 |
| Mir344c | 1.00 | 1.00 | 1.00 | 1.00 | 1.00 | 1.00 | 1.00 | 1.00 | 1.00 |
| Mir344d-1 | 1.00 | 1.00 | 1.00 | 46.99 | 0.02 | 2.01 | 1.00 | 1.00 | 1.00 |
| Mir344d-3 | 1.00 | 1.00 | 1.00 | 1.00 | 1.00 | 1.00 | 1.00 | 1.00 | 1.00 |
| Mir344g | 1.00 | 1.00 | 1.00 | 0.03 | 1.00 | 1.00 | 1.00 | 1.00 | 1.00 |
| Mir344i | 1.00 | 1.00 | 1.00 | 1.00 | 1.00 | 1.00 | 1.00 | 1.00 | 1.00 |
| Mir345 | 1.00 | 0.45 | 1.00 | 10.36 | 0.11 | 1.00 | 1.00 | 1.00 | 1.00 |
| Mir3471-1 | 1.00 | 5.98 | 1.00 | 1.00 | 1.00 | 1.00 | 1.00 | 1.00 | 1.00 |
| Mir3473 | 1.00 | 1.00 | 1.00 | 1.00 | 1.00 | 1.00 | 1.00 | 1.00 | 1.00 |
| Mir3473c | 1.00 | 12.79 | 1.00 | 1.00 | 1.00 | 1.00 | 1.00 | 1.00 | 1.00 |
| Mir3473d | 1.00 | 1.00 | 0.92 | 1.00 | 1.00 | 0.07 | 1.00 | 15.44 | 0.02 |
| Mir3473e | 0.47 | 0.85 | 8.45 | 5.21 | 1.13 | 1.90 | 14.15 | 0.20 | 3.16 |
| Mir3473g | 7.84 | 6.57 | 0.91 | 2.13 | 4.74 | 2.35 | 0.42 | 0.63 | 0.15 |
| Mir3474 | 1.00 | 1.00 | 1.00 | 1.00 | 1.00 | 1.00 | 1.00 | 1.00 | 1.00 |
| Mir34a | 1.00 | 1.00 | 5.67 | 1.00 | 0.15 | 1.00 | 1.00 | 1.00 | 1.00 |
| Mir34c | 1.00 | 1.00 | 1.00 | 1.00 | 1.00 | 1.00 | 1.00 | 1.00 | 1.00 |
| Mir350 | 1.00 | 0.15 | 1.00 | 1.00 | 1.00 | 1.00 | 1.00 | 1.00 | 1.00 |
| Mir351 | 0.07 | 0.55 | 1.00 | 2.54 | 8.06 | 1.00 | 1.00 | 0.26 | 1.00 |
| Mir3547 | 1.00 | 1.00 | 1.00 | 1.00 | 1.00 | 1.00 | 1.00 | 1.00 | 1.00 |
| Mir3569 | 0.01 | 1.00 | 1.00 | 1.00 | 1.00 | 1.00 | 1.00 | 1.00 | 1.00 |
| Mir3572 | 1.00 | 10.06 | 1.00 | 1.19 | 1.15 | 0.09 | 1.09 | 1.00 | 0.97 |
| Mir3620 | 1.00 | 0.02 | 1.00 | 1.00 | 1.00 | 1.00 | 1.00 | 1.00 | 1.00 |

Fig. 31- 62

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir3070a | 1.00 | 1.00 | 1.00 | 1.00 | 1.00 | 1.00 | 1.00 | 1.00 | 1.00 |
| Mir3071 | 1.00 | 1.00 | 1.00 | 1.00 | 1.00 | 1.00 | 1.00 | 1.00 | 1.00 |
| Mir3072 | 1.00 | 1.00 | 0.58 | 1.00 | 32.76 | 1.00 | 1.00 | 1.00 | 1.00 |
| Mir3073 | 1.00 | 1.00 | 1.00 | 1.00 | 1.00 | 1.00 | 1.00 | 1.00 | 1.00 |
| Mir3074-1 | 0.26 | 0.02 | 1.00 | 1.00 | 0.42 | 1.00 | 0.23 | 17.53 | 24.53 |
| Mir3074-2 | 1.00 | 1.09 | 24.85 | 1.00 | 11.61 | 1.00 | 16.49 | 19.02 | 0.04 |
| Mir3075 | 9.42 | 1.00 | 1.00 | 1.00 | 1.00 | 1.00 | 1.00 | 1.00 | 1.00 |
| Mir3076 | 1.00 | 1.00 | 0.01 | 1.00 | 1.00 | 1.00 | 1.00 | 1.00 | 0.01 |
| Mir3077 | 1.00 | 1.00 | 1.00 | 1.00 | 1.00 | 1.00 | 1.00 | 1.00 | 61.58 |
| Mir3081 | 1.00 | 1.00 | 10.39 | 1.00 | 1.00 | 1.00 | 1.00 | 1.00 | 1.00 |
| Mir3082 | 0.01 | 263.35 | 1.33 | 236.67 | 0.02 | 0.03 | 19.99 | 0.16 | 715.24 |
| Mir3084 | 1.00 | 1.00 | 1.00 | 1.00 | 1.00 | 1.00 | 1.00 | 1.00 | 51.17 |
| Mir3086 | 1.00 | 1.00 | 9.63 | 1.00 | 1.00 | 1.00 | 1.00 | 1.00 | 1.00 |
| Mir3087 | 1.00 | 75.17 | 1.00 | 1.00 | 1.00 | 1.00 | 1.00 | 1.00 | 1.00 |
| Mir3089 | 1.00 | 1.00 | 1.00 | 1.00 | 1.00 | 1.00 | 1.00 | 1.00 | 1.00 |
| Mir3091 | 0.69 | 0.03 | 0.01 | 0.61 | 0.02 | 1.68 | 2.90 | 1.09 | 0.50 |
| Mir3092 | 1.00 | 1.00 | 1.00 | 1.00 | 6.64 | 1.00 | 1.00 | 1.00 | 1.00 |
| Mir3094 | 1.00 | 1.00 | 1.00 | 1.00 | 1.00 | 1.00 | 1.00 | 1.00 | 1.00 |
| Mir3095 | 1.00 | 1.00 | 1.00 | 1.00 | 1.00 | 1.00 | 1.00 | 1.00 | 1.00 |
| Mir3097 | 0.02 | 1.04 | 0.76 | 1.00 | 27.99 | 1.00 | 52.71 | 62.83 | 0.01 |
| Mir30b | 0.16 | 1.00 | 1.00 | 1.00 | 1.00 | 1.00 | 1.00 | 1.00 | 1.00 |
| Mir30c-2 | 1.37 | 28.47 | 0.02 | 1.00 | 10.53 | 1.00 | 1.00 | 1.00 | 1.00 |
| Mir30d | 0.09 | 23.70 | 1.01 | 1.00 | 1.00 | 1.00 | 0.05 | 1.00 | 1.00 |
| Mir30f | 1.00 | 1.00 | 1.00 | 1.00 | 1.00 | 1.00 | 1.00 | 1.00 | 1.00 |
| Mir3100 | 0.48 | 0.94 | 1.26 | 1.34 | 3.47 | 0.90 | 58.34 | 0.02 | 1.71 |
| Mir3102 | 0.22 | 1.76 | 1.61 | 0.19 | 0.21 | 1.00 | 0.84 | 0.07 | 11.94 |
| Mir3103 | 1.00 | 1.00 | 1.00 | 1.00 | 1.00 | 1.00 | 1.00 | 1.00 | 1.00 |
| Mir3104 | 1.00 | 1.00 | 1.00 | 1.00 | 1.00 | 1.00 | 1.00 | 1.00 | 1.00 |
| Mir3107 | 1.00 | 1.00 | 1.00 | 1.00 | 1.00 | 1.00 | 0.84 | 1.00 | 11.12 |
| Mir3109 | 1.00 | 9.15 | 1.00 | 1.00 | 1.00 | 8.72 | 13.72 | 0.07 | 1.00 |
| Mir3112 | 0.07 | 1.00 | 13.50 | 1.00 | 1.00 | 5.88 | 4.64 | 0.07 | 1.00 |
| Mir32 | 1.00 | 0.05 | 24.02 | 1.00 | 1.00 | 1.00 | 1.00 | 1.00 | 1.00 |
| Mir320 | 1.00 | 12.10 | 1.00 | 1.00 | 11.59 | 0.07 | 0.05 | 0.05 | 1.00 |
| Mir324 | 0.77 | 1.49 | 0.47 | 0.17 | 0.41 | 1.58 | 0.29 | 0.27 | 0.93 |
| Mir328 | 16.18 | 10.90 | 1.07 | 1.00 | 1.00 | 1.00 | 2.22 | 0.31 | 3.28 |
| Mir329 | 1.00 | 1.00 | 1.00 | 1.00 | 1.00 | 1.00 | 1.00 | 1.00 | 1.00 |
| Mir330 | 2.09 | 0.64 | 1.06 | 1.00 | 0.17 | 0.16 | 0.94 | 9.35 | 7.84 |
| Mir331 | 2.06 | 0.40 | 1.09 | 0.98 | 0.16 | 3.71 | 0.47 | 1.00 | 0.50 |
| Mir335 | 5.52 | 1.00 | 1.00 | 5.89 | 1.00 | 1.00 | 0.12 | 0.11 | 1.00 |
| Mir337 | 1.00 | 1.00 | 1.00 | 1.00 | 1.00 | 1.00 | 1.00 | 1.00 | 1.00 |
| Mir338 | 1.00 | 1.00 | 0.17 | 1.00 | 1.00 | 1.00 | 8.77 | 1.00 | 1.00 |
| Mir339 | 0.28 | 0.44 | 0.22 | 1.00 | 17.79 | 0.92 | 0.94 | 3.45 | 2.39 |
| Mir343 | 0.66 | 3.68 | 1.67 | 1.00 | 1.52 | 0.64 | 2.64 | 1.75 | 1.22 |
| Mir344c | 1.00 | 1.00 | 1.00 | 1.00 | 1.00 | 1.00 | 1.00 | 1.00 | 1.00 |
| Mir344d-1 | 1.00 | 1.00 | 1.00 | 1.00 | 1.00 | 1.00 | 1.00 | 1.00 | 1.00 |
| Mir344d-3 | 1.00 | 1.00 | 1.00 | 1.00 | 1.00 | 1.00 | 1.00 | 1.00 | 1.00 |
| Mir344g | 0.22 | 0.02 | 0.36 | 1.00 | 1.00 | 21.27 | 38.24 | 1.00 | 1.00 |
| Mir344i | 1.09 | 1.95 | 2.18 | 1.00 | 1.00 | 1.00 | 1.00 | 1.00 | 1.00 |
| Mir345 | 1.01 | 0.51 | 1.00 | 0.15 | 1.00 | 6.68 | 0.11 | 11.27 | 1.00 |
| Mir3471-1 | 1.00 | 1.00 | 1.00 | 1.00 | 1.00 | 1.00 | 1.00 | 1.00 | 1.00 |
| Mir3473 | 0.07 | 1.00 | 1.00 | 1.00 | 1.00 | 1.00 | 1.00 | 1.00 | 1.00 |
| Mir3473c | 22.58 | 4.74 | 3.20 | 1.00 | 1.00 | 0.07 | 0.57 | 0.50 | 0.77 |
| Mir3473d | 0.05 | 0.09 | 1.00 | 1.00 | 1.00 | 1.00 | 18.44 | 1.00 | 0.02 |
| Mir3473e | 1.08 | 4.08 | 1.18 | 0.22 | 0.99 | 7.31 | 0.06 | 0.03 | 3.79 |
| Mir3473g | 0.58 | 2.72 | 0.72 | 0.98 | 3.17 | 4.80 | 0.37 | 7.41 | 0.21 |
| Mir3474 | 1.00 | 0.98 | 0.02 | 1.00 | 61.89 | 1.00 | 124.88 | 1.00 | 1.00 |
| Mir34a | 5.08 | 0.21 | 1.00 | 1.00 | 1.00 | 1.00 | 1.00 | 1.00 | 0.13 |
| Mir34c | 1.00 | 1.00 | 1.00 | 1.00 | 1.00 | 1.00 | 1.00 | 1.00 | 1.00 |
| Mir350 | 1.00 | 1.00 | 1.00 | 1.00 | 1.00 | 1.00 | 1.00 | 0.11 | 1.00 |
| Mir351 | 1.40 | 1.00 | 1.00 | 1.00 | 1.00 | 1.00 | 1.00 | 0.07 | 1.00 |
| Mir3547 | 1.00 | 1.00 | 1.00 | 1.00 | 1.00 | 1.00 | 1.00 | 1.00 | 1.00 |
| Mir3569 | 1.00 | 0.02 | 1.00 | 1.00 | 1.00 | 1.00 | 1.00 | 1.00 | 1.00 |
| Mir3572 | 0.11 | 68.70 | 10.07 | 1.00 | 0.10 | 1.00 | 1.34 | 0.89 | 0.51 |
| Mir3620 | 1.00 | 0.02 | 1.00 | 1.00 | 1.00 | 1.00 | 1.00 | 1.00 | 0.01 |

Fig. 31- 63

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir3070a | 8.27 | 1.00 | 27.90 | 1.00 | 12.89 | 1.00 | 9.26 | 1.00 | 1.00 |
| Mir3071 | 1.00 | 11.92 | 1.00 | 1.00 | 1.00 | 1.00 | 1.00 | 1.00 | 1.00 |
| Mir3072 | 0.97 | 0.87 | 0.85 | 0.02 | 0.52 | 1.00 | 1.11 | 28.88 | 1.97 |
| Mir3073 | 1.00 | 1.00 | 1.00 | 1.00 | 1.00 | 1.00 | 0.04 | 1.00 | 0.04 |
| Mir3074-1 | 0.10 | 0.94 | 1.88 | 0.71 | 0.42 | 21.50 | 0.61 | 6.81 | 1.00 |
| Mir3074-2 | 0.05 | 17.25 | 1.00 | 0.36 | 0.07 | 1.00 | 1.00 | 10.62 | 1.00 |
| Mir3075 | 1.00 | 1.00 | 1.00 | 1.00 | 1.00 | 11.75 | 1.00 | 1.00 | 1.00 |
| Mir3076 | 1.00 | 1.00 | 1.00 | 1.00 | 1.00 | 1.00 | 1.00 | 1.00 | 1.00 |
| Mir3077 | 1.00 | 1.00 | 1.00 | 1.00 | 1.00 | 1.00 | 0.03 | 1.00 | 1.00 |
| Mir3081 | 1.00 | 1.00 | 1.00 | 1.00 | 1.00 | 1.00 | 11.45 | 9.43 | 1.00 |
| Mir3082 | 0.01 | 1.00 | 1.00 | 1.00 | 133.03 | 1.00 | 1.00 | 1.00 | 1.00 |
| Mir3084 | 0.01 | 0.01 | 38.96 | 1.00 | 1.00 | 41.20 | 1.00 | 1.00 | 1.00 |
| Mir3086 | 1.00 | 1.00 | 1.00 | 1.00 | 1.00 | 1.00 | 1.00 | 1.00 | 0.98 |
| Mir3087 | 1.00 | 1.00 | 0.01 | 1.00 | 1.00 | 1.00 | 1.00 | 1.00 | 1.00 |
| Mir3089 | 1.00 | 1.00 | 1.00 | 1.00 | 1.00 | 1.00 | 11.45 | 1.00 | 1.00 |
| Mir3091 | 1.34 | 1.36 | 1.36 | 0.69 | 78.78 | 4.19 | 2.85 | 0.63 | 1.05 |
| Mir3092 | 1.00 | 1.00 | 1.00 | 1.00 | 9.15 | 0.16 | 1.00 | 5.72 | 0.16 |
| Mir3094 | 1.00 | 1.00 | 1.00 | 1.00 | 1.00 | 1.00 | 1.00 | 1.00 | 36.42 |
| Mir3095 | 1.00 | 1.00 | 1.00 | 1.00 | 1.00 | 1.00 | 0.06 | 1.00 | 1.00 |
| Mir3097 | 1.00 | 61.56 | 42.51 | 1.00 | 1.00 | 37.64 | 1.00 | 26.40 | 1.00 |
| Mir30b | 10.12 | 0.12 | 1.00 | 0.13 | 1.00 | 1.00 | 1.00 | 1.00 | 1.00 |
| Mir30c-2 | 18.90 | 16.24 | 1.00 | 54.79 | 0.03 | 1.84 | 1.00 | 1.00 | 1.00 |
| Mir30d | 16.34 | 1.97 | 0.07 | 1.65 | 33.62 | 0.94 | 1.00 | 1.00 | 1.00 |
| Mir30f | 0.08 | 1.00 | 1.00 | 1.00 | 1.00 | 1.00 | 1.00 | 1.00 | 1.00 |
| Mir3100 | 221.69 | 76.69 | 1.01 | 0.00 | 0.77 | 1.89 | 0.73 | 1.55 | 1.13 |
| Mir3102 | 6.01 | 17.35 | 1.72 | 0.38 | 0.18 | 4.88 | 0.21 | 4.33 | 4.56 |
| Mir3103 | 1.00 | 0.02 | 1.00 | 1.00 | 63.89 | 1.00 | 1.00 | 1.00 | 1.00 |
| Mir3104 | 85.84 | 96.62 | 1.00 | 1.00 | 1.00 | 1.00 | 1.00 | 1.00 | 1.00 |
| Mir3107 | 10.44 | 1.00 | 17.76 | 1.00 | 1.00 | 8.69 | 1.00 | 1.00 | 1.00 |
| Mir3109 | 1.00 | 1.00 | 1.00 | 0.07 | 13.60 | 10.08 | 1.00 | 0.44 | 2.11 |
| Mir3112 | 16.21 | 7.79 | 0.04 | 1.00 | 0.05 | 1.00 | 1.00 | 1.00 | 1.00 |
| Mir32 | 1.00 | 1.00 | 1.00 | 1.00 | 1.00 | 1.00 | 1.00 | 1.00 | 1.00 |
| Mir320 | 0.97 | 18.57 | 29.09 | 1.00 | 0.03 | 1.00 | 12.60 | 1.88 | 1.09 |
| Mir324 | 7.13 | 0.84 | 0.69 | 2.03 | 1.32 | 1.00 | 9.26 | 7.56 | 15.84 |
| Mir328 | 1.00 | 0.12 | 6.70 | 0.06 | 1.00 | 0.94 | 1.00 | 1.00 | 1.00 |
| Mir329 | 1.00 | 8.34 | 1.07 | 1.00 | 1.00 | 1.00 | 1.00 | 1.00 | 1.00 |
| Mir330 | 15.40 | 0.52 | 6.43 | 0.07 | 0.70 | 6.44 | 0.92 | 0.45 | 0.26 |
| Mir331 | 1.59 | 0.69 | 0.92 | 0.63 | 0.13 | 18.81 | 0.09 | 0.08 | 1.00 |
| Mir335 | 0.05 | 7.99 | 1.00 | 0.83 | 0.14 | 1.04 | 1.00 | 1.00 | 1.00 |
| Mir337 | 1.17 | 8.44 | 1.00 | 1.00 | 1.00 | 1.00 | 1.00 | 0.15 | 1.00 |
| Mir338 | 1.00 | 15.66 | 1.00 | 1.00 | 0.07 | 1.00 | 1.08 | 1.00 | 1.00 |
| Mir339 | 0.75 | 0.52 | 0.72 | 0.98 | 4.07 | 0.77 | 0.06 | 1.70 | 1.91 |
| Mir343 | 1.48 | 0.50 | 1.26 | 2.94 | 2.38 | 1.07 | 1.38 | 2.71 | 0.52 |
| Mir344c | 1.00 | 1.00 | 1.00 | 1.00 | 1.00 | 1.00 | 0.13 | 6.68 | 1.00 |
| Mir344d-1 | 1.00 | 1.00 | 1.00 | 1.00 | 1.00 | 1.00 | 1.00 | 1.00 | 0.04 |
| Mir344d-3 | 0.05 | 1.00 | 1.00 | 1.00 | 1.00 | 1.00 | 0.37 | 66.47 | 0.71 |
| Mir344g | 0.90 | 1.00 | 0.42 | 1.00 | 0.03 | 1.00 | 0.05 | 1.00 | 1.00 |
| Mir344i | 11.56 | 1.00 | 0.10 | 1.00 | 1.00 | 1.00 | 1.00 | 0.11 | 1.00 |
| Mir345 | 1.00 | 0.13 | 1.35 | 9.11 | 2.10 | 0.16 | 1.00 | 1.00 | 1.00 |
| Mir3471-1 | 1.00 | 1.00 | 1.00 | 1.00 | 1.00 | 0.19 | 1.00 | 4.95 | 1.00 |
| Mir3473 | 1.00 | 23.89 | 1.00 | 1.00 | 1.00 | 1.00 | 1.00 | 1.00 | 1.00 |
| Mir3473c | 1.00 | 0.05 | 0.56 | 1.00 | 20.52 | 1.00 | 1.00 | 1.00 | 1.00 |
| Mir3473d | 17.41 | 0.05 | 1.08 | 0.06 | 18.17 | 1.94 | 0.77 | 0.77 | 1.26 |
| Mir3473e | 1.00 | 5.00 | 1.04 | 0.81 | 2.57 | 2.60 | 0.25 | 0.50 | 4.56 |
| Mir3473g | 1.34 | 1.01 | 0.69 | 1.00 | 0.46 | 0.53 | 4.96 | 1.89 | 2.39 |
| Mir3474 | 1.00 | 1.00 | 1.00 | 1.00 | 1.00 | 1.00 | 1.00 | 54.08 | 1.00 |
| Mir34a | 1.00 | 1.00 | 1.00 | 0.17 | 1.00 | 0.49 | 0.10 | 1.00 | 1.00 |
| Mir34c | 1.00 | 1.00 | 1.00 | 1.00 | 1.00 | 1.00 | 1.00 | 0.23 | 31.49 |
| Mir350 | 1.00 | 1.00 | 1.00 | 1.00 | 0.15 | 1.00 | 0.60 | 3.37 | 11.48 |
| Mir351 | 5.38 | 1.00 | 1.00 | 0.17 | 1.00 | 0.45 | 1.00 | 1.08 | 1.00 |
| Mir3547 | 1.00 | 1.00 | 0.10 | 1.00 | 1.00 | 1.00 | 1.00 | 1.00 | 1.00 |
| Mir3569 | 1.00 | 1.00 | 1.00 | 1.00 | 1.00 | 1.00 | 1.00 | 50.10 | 1.00 |
| Mir3572 | 0.03 | 1.00 | 1.00 | 30.67 | 1.00 | 1.00 | 0.11 | 1.00 | 1.00 |
| Mir3620 | 1.00 | 1.00 | 1.00 | 1.00 | 133.49 | 1.00 | 1.00 | 1.00 | 1.00 |

Fig. 31- 64

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir3070a | 1.00 | 1.00 | 1.00 | 1.00 | 1.00 | 1.00 | 1.00 | 1.00 | 1.00 | 1.00 | 1.00 | 1.00 |
| Mir3071 | 1.00 | 1.00 | 1.00 | 1.00 | 1.00 | 1.00 | 1.00 | 1.00 | 1.00 | 1.00 | 1.00 | 1.00 |
| Mir3072 | 1.00 | 1.00 | 1.00 | 1.00 | 1.00 | 1.00 | 0.75 | 1.00 | 1.00 | 1.00 | 1.00 | 1.00 |
| Mir3073 | 1.00 | 1.00 | 1.00 | 1.00 | 1.00 | 1.00 | 1.00 | 1.00 | 1.00 | 1.00 | 1.00 | 1.00 |
| Mir3074-1 | 22.00 | 7.70 | 0.11 | 1.00 | 1.00 | 1.00 | 0.15 | 0.17 | 0.39 | 1.00 | 1.00 | 1.00 |
| Mir3074-2 | 0.58 | 22.83 | 1.00 | 1.00 | 0.99 | 1.00 | 1.00 | 1.00 | 1.00 | 1.00 | 1.00 | 1.00 |
| Mir3075 | 1.00 | 1.00 | 1.00 | 1.00 | 1.00 | 1.00 | 1.00 | 1.00 | 1.00 | 1.00 | 1.00 | 1.00 |
| Mir3076 | 1.00 | 57.19 | 1.00 | 57.13 | 0.02 | 1.00 | 1.00 | 1.00 | 1.00 | 1.00 | 1.00 | 1.00 |
| Mir3077 | 1.00 | 1.00 | 1.00 | 41.77 | 0.03 | 1.00 | 1.00 | 1.00 | 1.00 | 1.00 | 1.00 | 1.00 |
| Mir3081 | 1.00 | 1.00 | 1.00 | 1.00 | 1.00 | 1.00 | 1.00 | 1.00 | 1.00 | 1.00 | 1.00 | 1.00 |
| Mir3082 | 1.16 | 0.42 | 2.53 | 0.36 | 56.77 | 0.65 | 1.00 | 0.10 | 1.00 | 1.00 | 1.00 | 1.00 |
| Mir3084 | 1.00 | 1.00 | 0.03 | 0.02 | 0.03 | 1.00 | 1.00 | 1.00 | 1.00 | 1.00 | 1.00 | 1.00 |
| Mir3086 | 1.00 | 1.00 | 1.00 | 1.00 | 1.00 | 1.00 | 1.00 | 1.00 | 1.00 | 1.00 | 1.00 | 1.00 |
| Mir3087 | 1.00 | 1.00 | 1.00 | 1.00 | 1.00 | 1.00 | 1.00 | 1.00 | 1.00 | 1.00 | 1.00 | 1.00 |
| Mir3089 | 1.00 | 1.00 | 1.00 | 1.00 | 1.00 | 1.00 | 1.00 | 1.00 | 1.00 | 1.00 | 1.00 | 1.00 |
| Mir3091 | 1.91 | 0.88 | 0.63 | 1.07 | 0.89 | 0.14 | 1.06 | 0.07 | 15.04 | 1.00 | 1.00 | 1.00 |
| Mir3092 | 1.00 | 1.00 | 1.00 | 1.00 | 1.00 | 0.17 | 1.00 | 1.00 | 1.00 | 1.00 | 1.00 | 1.00 |
| Mir3094 | 1.00 | 0.94 | 1.00 | 1.00 | 1.00 | 1.00 | 1.00 | 1.00 | 1.00 | 1.00 | 1.00 | 1.00 |
| Mir3095 | 1.00 | 9.74 | 1.09 | 1.00 | 1.00 | 1.00 | 1.00 | 1.00 | 1.00 | 1.00 | 1.00 | 1.00 |
| Mir3097 | 68.02 | 1.11 | 1.98 | 1.00 | 1.00 | 0.03 | 1.00 | 1.00 | 1.00 | 1.00 | 1.00 | 1.00 |
| Mir30b | 1.00 | 1.00 | 1.00 | 1.00 | 1.00 | 1.00 | 1.00 | 1.00 | 1.00 | 1.00 | 1.00 | 1.00 |
| Mir30c-2 | 0.07 | 1.00 | 1.00 | 1.00 | 1.00 | 1.00 | 1.00 | 11.11 | 1.00 | 1.00 | 1.00 | 1.00 |
| Mir30d | 1.00 | 1.00 | 0.07 | 12.32 | 1.00 | 1.00 | 0.11 | 0.09 | 1.00 | 1.00 | 1.00 | 1.00 |
| Mir30f | 1.00 | 1.00 | 1.00 | 1.00 | 1.00 | 8.20 | 1.00 | 1.00 | 1.00 | 1.00 | 1.00 | 1.00 |
| Mir3100 | 1.00 | 2.90 | 0.21 | 0.03 | 1.00 | 0.03 | 1.00 | 1.00 | 1.00 | 1.00 | 1.00 | 1.00 |
| Mir3102 | 10.98 | 5.99 | 0.10 | 1.00 | 1.00 | 1.00 | 1.00 | 1.00 | 1.00 | 1.00 | 1.00 | 1.00 |
| Mir3103 | 1.00 | 1.00 | 1.00 | 1.00 | 1.00 | 1.00 | 1.00 | 1.00 | 1.00 | 1.00 | 1.00 | 1.00 |
| Mir3104 | 1.00 | 1.00 | 1.00 | 1.00 | 1.00 | 1.00 | 0.03 | 0.03 | 1.00 | 1.00 | 1.00 | 1.00 |
| Mir3107 | 1.00 | 1.00 | 1.00 | 0.26 | 1.00 | 1.00 | 1.00 | 1.00 | 1.00 | 1.00 | 1.00 | 1.00 |
| Mir3109 | 0.09 | 0.10 | 0.56 | 1.00 | 9.34 | 1.00 | 1.00 | 1.00 | 1.00 | 1.00 | 1.00 | 1.00 |
| Mir3112 | 1.00 | 1.00 | 2.12 | 3.02 | 0.06 | 1.00 | 1.00 | 1.00 | 1.00 | 1.00 | 1.00 | 1.00 |
| Mir32 | 1.00 | 1.00 | 1.00 | 1.00 | 1.00 | 1.00 | 1.00 | 1.00 | 1.00 | 1.00 | 1.00 | 1.00 |
| Mir320 | 13.84 | 0.08 | 2.05 | 1.00 | 1.00 | 1.00 | 1.00 | 1.00 | 1.00 | 1.00 | 1.00 | 1.00 |
| Mir324 | 0.22 | 1.89 | 0.96 | 5.90 | 4.62 | 1.14 | 0.08 | 1.00 | 7.70 | 1.00 | 1.00 | 1.00 |
| Mir328 | 0.02 | 0.60 | 0.62 | 1.12 | 5.91 | 0.58 | 0.81 | 1.00 | 0.21 | 1.00 | 1.00 | 1.00 |
| Mir329 | 1.00 | 1.00 | 1.00 | 1.00 | 1.00 | 1.00 | 1.00 | 1.00 | 1.00 | 1.00 | 1.00 | 1.00 |
| Mir330 | 1.00 | 1.81 | 7.08 | 1.66 | 10.90 | 1.77 | 4.21 | 1.00 | 1.00 | 1.00 | 1.00 | 1.00 |
| Mir331 | 0.54 | 0.04 | 1.01 | 1.00 | 0.08 | 0.17 | 0.76 | 1.00 | 0.56 | 1.00 | 1.00 | 1.00 |
| Mir335 | 1.00 | 1.00 | 1.00 | 2.26 | 0.16 | 1.00 | 1.00 | 1.00 | 1.00 | 1.00 | 1.00 | 1.00 |
| Mir337 | 1.00 | 1.00 | 1.00 | 1.00 | 1.00 | 1.00 | 1.00 | 1.00 | 1.00 | 1.00 | 1.00 | 1.00 |
| Mir338 | 1.00 | 1.00 | 1.00 | 0.16 | 1.00 | 1.00 | 1.00 | 0.17 | 1.00 | 1.00 | 1.00 | 1.00 |
| Mir339 | 0.79 | 1.81 | 0.71 | 0.08 | 18.20 | 2.19 | 1.00 | 1.00 | 1.00 | 1.00 | 1.00 | 1.00 |
| Mir343 | 2.19 | 0.74 | 1.15 | 0.72 | 1.23 | 0.35 | 0.85 | 3.44 | 1.80 | 1.00 | 1.00 | 1.00 |
| Mir344c | 1.00 | 1.00 | 1.00 | 1.00 | 1.00 | 1.00 | 1.00 | 1.00 | 1.00 | 1.00 | 1.00 | 1.00 |
| Mir344d-1 | 1.00 | 1.00 | 1.00 | 1.00 | 1.00 | 1.00 | 1.00 | 1.00 | 1.00 | 1.00 | 1.00 | 1.00 |
| Mir344d-3 | 1.00 | 1.00 | 1.00 | 1.00 | 1.00 | 1.00 | 1.00 | 1.00 | 1.00 | 1.00 | 1.00 | 1.00 |
| Mir344g | 25.05 | 1.00 | 1.00 | 1.00 | 1.00 | 1.00 | 13.74 | 1.00 | 1.00 | 1.00 | 1.00 | 1.00 |
| Mir344i | 1.00 | 1.00 | 1.00 | 1.00 | 1.00 | 1.00 | 1.00 | 1.00 | 1.00 | 1.00 | 1.00 | 1.00 |
| Mir345 | 8.59 | 1.00 | 1.09 | 1.00 | 1.00 | 1.00 | 4.35 | 1.00 | 1.00 | 1.00 | 1.00 | 1.00 |
| Mir3471-1 | 1.00 | 1.00 | 1.00 | 1.00 | 1.00 | 0.17 | 1.00 | 1.00 | 1.00 | 1.00 | 1.00 | 1.00 |
| Mir3473 | 0.06 | 1.00 | 1.00 | 1.00 | 1.00 | 1.00 | 1.00 | 1.00 | 1.00 | 1.00 | 1.00 | 1.00 |
| Mir3473c | 0.38 | 1.98 | 77.86 | 0.98 | 23.45 | 1.00 | 1.00 | 1.00 | 1.00 | 1.00 | 1.00 | 1.00 |
| Mir3473d | 1.00 | 0.07 | 15.33 | 1.00 | 1.00 | 13.83 | 1.00 | 1.00 | 1.00 | 1.00 | 1.00 | 1.00 |
| Mir3473e | 3.86 | 0.08 | 3.83 | 1.14 | 0.52 | 0.83 | 2.79 | 0.26 | 1.00 | 1.00 | 1.00 | 1.00 |
| Mir3473g | 1.06 | 1.04 | 3.25 | 4.04 | 0.33 | 1.60 | 1.00 | 1.00 | 0.61 | 1.00 | 1.00 | 1.00 |
| Mir3474 | 1.05 | 1.00 | 0.01 | 1.00 | 1.00 | 1.00 | 1.00 | 1.00 | 1.00 | 1.00 | 1.00 | 1.00 |
| Mir34a | 0.17 | 5.47 | 0.08 | 1.00 | 1.00 | 1.00 | 1.00 | 1.00 | 1.00 | 1.00 | 1.00 | 1.00 |
| Mir34c | 1.00 | 1.00 | 1.00 | 1.00 | 1.00 | 1.00 | 1.00 | 1.00 | 1.00 | 1.00 | 1.00 | 1.00 |
| Mir350 | 1.00 | 1.00 | 1.00 | 0.16 | 1.00 | 1.00 | 1.00 | 1.00 | 1.00 | 1.00 | 1.00 | 1.00 |
| Mir351 | 1.99 | 0.55 | 6.17 | 0.18 | 0.86 | 5.78 | 1.00 | 1.00 | 1.00 | 1.00 | 1.00 | 1.00 |
| Mir3547 | 10.53 | 1.00 | 1.00 | 1.00 | 1.00 | 1.00 | 1.00 | 1.00 | 1.00 | 1.00 | 1.00 | 1.00 |
| Mir3569 | 0.02 | 68.00 | 1.00 | 1.00 | 1.00 | 1.00 | 1.00 | 1.00 | 1.00 | 1.00 | 1.00 | 1.00 |
| Mir3572 | 0.38 | 0.70 | 0.99 | 12.00 | 1.02 | 2.26 | 0.13 | 1.00 | 1.00 | 1.00 | 1.00 | 1.00 |
| Mir3620 | 1.00 | 0.02 | 1.00 | 0.85 | 2.03 | 2.24 | 1.00 | 1.00 | 1.00 | 1.00 | 1.00 | 1.00 |

Fig. 31-65

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir363 | 1.00 | 1.00 | 1.00 | 29.08 | 0.03 | 1.00 | 1.00 | 22.33 | 1.00 |
| Mir365-1 | 0.08 | 9.62 | 1.00 | 1.00 | 1.00 | 1.00 | 1.00 | 1.00 | 1.00 |
| Mir365-2 | 7.38 | 3.86 | 1.00 | 4.45 | 0.57 | 0.61 | 0.12 | 0.80 | 0.53 |
| Mir367 | 1.00 | 1.00 | 1.00 | 1.00 | 1.00 | 23.31 | 1.00 | 1.00 | 1.00 |
| Mir369 | 1.00 | 1.00 | 1.00 | 1.00 | 1.00 | 1.00 | 1.00 | 1.00 | 1.00 |
| Mir374 | 0.12 | 6.89 | 2.47 | 0.64 | 2.28 | 2.02 | 0.10 | 1.00 | 1.00 |
| Mir374c | 1.00 | 1.00 | 1.00 | 1.00 | 1.00 | 1.00 | 1.00 | 1.00 | 1.00 |
| Mir376a | 1.00 | 1.00 | 1.00 | 1.00 | 1.00 | 1.00 | 1.00 | 1.00 | 1.00 |
| Mir377 | 1.00 | 1.00 | 1.00 | 1.00 | 0.02 | 1.00 | 1.00 | 1.00 | 1.00 |
| Mir378b | 1.12 | 1.14 | 0.50 | 44.51 | 0.05 | 0.28 | 10.13 | 1.68 | 1.00 |
| Mir381 | 1.00 | 1.00 | 1.00 | 1.00 | 1.00 | 1.00 | 1.00 | 1.00 | 1.00 |
| Mir382 | 1.00 | 1.00 | 1.00 | 1.00 | 1.00 | 1.00 | 1.00 | 1.00 | 0.04 |
| Mir3960 | 0.76 | 2.15 | 1.51 | 0.29 | 1.15 | 0.69 | 1.68 | 0.47 | 5.78 |
| Mir3966 | 1.00 | 1.00 | 1.00 | 1.00 | 1.00 | 1.00 | 1.00 | 1.00 | 1.00 |
| Mir3968 | 1.00 | 5.19 | 1.00 | 1.00 | 1.00 | 0.16 | 0.66 | 0.42 | 2.01 |
| Mir3971 | 1.00 | 1.00 | 1.00 | 1.00 | 0.06 | 0.07 | 1.00 | 1.00 | 1.00 |
| Mir409 | 1.00 | 1.00 | 0.06 | 1.00 | 1.00 | 1.00 | 1.00 | 1.00 | 1.00 |
| Mir410 | 1.00 | 1.00 | 3.89 | 1.00 | 1.00 | 1.00 | 15.09 | 12.53 | 1.00 |
| Mir412 | 1.00 | 1.00 | 14.80 | 1.00 | 1.00 | 1.00 | 1.00 | 1.00 | 1.00 |
| Mir421 | 0.87 | 0.03 | 0.95 | 0.41 | 0.02 | 0.05 | 1.00 | 1.00 | 1.00 |
| Mir423 | 1.00 | 4.23 | 1.00 | 1.00 | 1.00 | 1.00 | 1.00 | 1.00 | 1.00 |
| Mir425 | 0.08 | 0.86 | 32.92 | 1.85 | 0.39 | 1.07 | 14.23 | 0.07 | 0.04 |
| Mir429 | 1.00 | 1.00 | 1.00 | 1.00 | 1.00 | 1.00 | 1.00 | 1.00 | 1.00 |
| Mir431 | 1.00 | 1.00 | 1.00 | 1.00 | 1.00 | 1.00 | 1.00 | 1.00 | 1.00 |
| Mir432 | 1.00 | 1.00 | 1.00 | 1.00 | 1.00 | 1.00 | 1.00 | 1.00 | 1.00 |
| Mir433 | 1.00 | 4.75 | 1.00 | 6.09 | 1.00 | 1.00 | 1.00 | 1.00 | 1.00 |
| Mir434 | 1.00 | 1.00 | 1.00 | 1.00 | 1.00 | 1.00 | 1.00 | 1.00 | 1.00 |
| Mir450b | 1.00 | 1.00 | 1.00 | 1.00 | 1.00 | 1.00 | 1.00 | 1.00 | 1.00 |
| Mir451 | 1.00 | 1.00 | 1.00 | 1.00 | 1.00 | 1.00 | 1.00 | 1.00 | 1.00 |
| Mir453 | 1.00 | 1.72 | 1.00 | 1.00 | 1.00 | 1.00 | 1.00 | 1.00 | 1.00 |
| Mir4660 | 1.00 | 1.00 | 1.00 | 1.00 | 1.00 | 1.00 | 1.00 | 1.00 | 1.00 |
| Mir466i | 1.32 | 1.31 | 0.59 | 0.56 | 0.29 | 0.33 | 1.57 | 3.19 | 8.21 |
| Mir467a-10 | 1.00 | 1.00 | 1.00 | 1.00 | 1.00 | 1.00 | 1.00 | 1.00 | 1.00 |
| Mir467f | 9.29 | 3.09 | 6.21 | 0.82 | 2.29 | 0.25 | 0.28 | 0.61 | 3.83 |
| Mir484 | 1.00 | 1.00 | 0.03 | 1.00 | 1.00 | 1.00 | 1.00 | 1.00 | 1.00 |
| Mir485 | 1.00 | 0.04 | 1.00 | 1.00 | 1.00 | 1.00 | 29.39 | 1.00 | 1.00 |
| Mir486 | 2.05 | 0.38 | 0.19 | 0.34 | 1.00 | 1.00 | 1.00 | 1.00 | 1.00 |
| Mir487b | 1.00 | 1.00 | 1.00 | 1.00 | 1.00 | 1.00 | 1.00 | 1.00 | 1.00 |
| Mir490 | 1.00 | 1.00 | 12.14 | 1.00 | 1.00 | 1.00 | 1.00 | 1.00 | 1.00 |
| Mir491 | 1.00 | 1.00 | 1.00 | 1.00 | 1.00 | 1.00 | 1.00 | 1.00 | 1.00 |
| Mir493 | 1.00 | 1.00 | 1.00 | 1.00 | 1.00 | 1.00 | 1.00 | 1.00 | 1.00 |
| Mir496 | 1.00 | 1.00 | 1.00 | 1.00 | 1.00 | 1.00 | 1.00 | 1.00 | 1.00 |
| Mir499 | 15.99 | 14.88 | 1.00 | 1.00 | 1.00 | 1.00 | 1.00 | 1.00 | 1.00 |
| Mir5046 | 1.00 | 1.00 | 1.00 | 1.00 | 1.00 | 1.00 | 0.03 | 0.04 | 1.00 |
| Mir505 | 1.00 | 1.00 | 1.00 | 1.00 | 1.00 | 1.00 | 1.00 | 1.00 | 1.00 |
| Mir5098 | 1.00 | 1.00 | 1.00 | 1.00 | 1.00 | 1.00 | 1.00 | 1.00 | 1.00 |
| Mir5100 | 0.02 | 0.02 | 1.00 | 89.39 | 1.00 | 1.00 | 1.00 | 53.49 | 66.34 |
| Mir5103 | 1.00 | 0.46 | 1.00 | 1.00 | 1.00 | 18.01 | 1.00 | 1.00 | 1.00 |
| Mir5104 | 1.00 | 7.16 | 1.00 | 1.00 | 1.00 | 1.00 | 1.00 | 8.11 | 1.00 |
| Mir5106 | 1.00 | 1.00 | 1.00 | 1.00 | 1.00 | 1.00 | 1.00 | 1.00 | 1.00 |
| Mir5107 | 0.87 | 79.63 | 4.05 | 3.61 | 1.14 | 0.67 | 12.23 | 41.25 | 1.00 |
| Mir5112 | 1.00 | 1.00 | 1.00 | 1.00 | 1.00 | 1.00 | 1.00 | 1.00 | 1.00 |
| Mir5113 | 0.15 | 1.00 | 1.06 | 15.60 | 1.00 | 1.00 | 1.00 | 1.00 | 0.12 |
| Mir5114 | 1.00 | 1.00 | 1.00 | 1.00 | 1.00 | 1.00 | 1.00 | 1.00 | 1.00 |
| Mir5116 | 0.00 | 490.66 | 0.20 | 28.19 | 1.00 | 1.00 | 0.01 | 1.00 | 16.22 |
| Mir5119 | 0.88 | 1.00 | 73.09 | 1.00 | 1.00 | 1.00 | 1.00 | 1.00 | 147.59 |
| Mir5121 | 139.35 | 55.61 | 5.47 | 1.00 | 144.46 | 0.51 | 1.04 | 2.58 | 1.48 |
| Mir5123 | 13.05 | 0.91 | 1.00 | 1.00 | 1.00 | 1.00 | 1.00 | 1.00 | 1.00 |
| Mir5126 | 1.00 | 1.00 | 1.00 | 1.00 | 1.00 | 1.00 | 1.00 | 1.00 | 1.00 |
| Mir5127 | 1.00 | 1.00 | 1.00 | 1.00 | 1.00 | 1.00 | 1.00 | 1.00 | 1.00 |
| Mir5128 | 1.00 | 1.00 | 1.00 | 1.00 | 1.00 | 1.00 | 1.00 | 1.00 | 1.00 |
| Mir5129 | 1.00 | 1.00 | 16.00 | 1.00 | 1.00 | 1.00 | 1.00 | 1.00 | 1.00 |
| Mir5132 | 1.64 | 0.65 | 24.78 | 45.97 | 0.02 | 2.02 | 0.48 | 1.00 | 0.02 |
| Mir5133 | 0.99 | 0.62 | 1.57 | 0.90 | 1.14 | 0.38 | 1.19 | 2.71 | 3.06 |

Fig. 31-66

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir363 | 1.00 | 15.68 | 1.00 | 1.00 | 1.00 | 1.00 | 0.48 | 61.19 | 0.82 |
| Mir365-1 | 1.00 | 1.00 | 1.00 | 1.91 | 0.99 | 0.10 | 1.00 | 1.00 | 1.00 |
| Mir365-2 | 1.90 | 1.79 | 0.63 | 0.25 | 0.10 | 0.25 | 0.19 | 1.00 | 0.19 |
| Mir367 | 1.00 | 1.00 | 1.00 | 1.00 | 1.00 | 1.00 | 0.04 | 1.00 | 1.00 |
| Mir369 | 1.00 | 1.00 | 1.00 | 1.00 | 0.07 | 1.00 | 1.00 | 1.00 | 19.93 |
| Mir374 | 0.58 | 3.99 | 0.03 | 0.92 | 1.91 | 6.53 | 0.72 | 1.35 | 6.89 |
| Mir374c | 1.00 | 1.00 | 184.84 | 1.00 | 1.00 | 1.00 | 1.00 | 1.00 | 1.00 |
| Mir376a | 1.00 | 1.00 | 1.00 | 1.00 | 1.00 | 1.00 | 1.00 | 1.00 | 1.00 |
| Mir377 | 0.04 | 1.00 | 1.00 | 1.00 | 1.00 | 1.00 | 1.00 | 1.00 | 1.00 |
| Mir378b | 0.37 | 0.46 | 0.73 | 0.98 | 0.99 | 1.63 | 0.27 | 1.78 | 1.40 |
| Mir381 | 1.00 | 1.00 | 1.00 | 1.00 | 1.00 | 1.00 | 1.00 | 1.00 | 1.00 |
| Mir382 | 1.00 | 14.82 | 1.00 | 1.00 | 1.00 | 1.00 | 1.00 | 1.00 | 1.00 |
| Mir3960 | 0.47 | 1.14 | 1.01 | 0.66 | 0.63 | 0.51 | 1.73 | 0.00 | 0.59 |
| Mir3966 | 1.00 | 1.00 | 10.55 | 1.00 | 1.00 | 1.00 | 1.00 | 1.00 | 1.00 |
| Mir3968 | 0.19 | 1.00 | 1.00 | 1.00 | 5.72 | 1.00 | 1.00 | 1.00 | 0.15 |
| Mir3971 | 1.00 | 1.00 | 10.90 | 1.00 | 1.00 | 1.00 | 1.00 | 1.00 | 15.85 |
| Mir409 | 1.00 | 1.00 | 1.00 | 0.07 | 1.00 | 1.00 | 1.00 | 1.00 | 1.00 |
| Mir410 | 1.00 | 1.00 | 1.00 | 0.10 | 0.14 | 5.89 | 0.10 | 10.70 | 1.00 |
| Mir412 | 0.08 | 0.08 | 1.00 | 1.00 | 1.00 | 1.00 | 0.94 | 1.00 | 1.00 |
| Mir421 | 0.16 | 1.93 | 15.68 | 19.40 | 2.06 | 1.00 | 2.90 | 0.01 | 1.00 |
| Mir423 | 0.27 | 1.00 | 0.25 | 0.93 | 1.00 | 1.00 | 1.00 | 0.16 | 1.00 |
| Mir425 | 1.33 | 1.60 | 1.25 | 1.00 | 1.00 | 0.08 | 2.27 | 1.32 | 0.14 |
| Mir429 | 20.21 | 0.10 | 1.00 | 1.00 | 1.00 | 1.00 | 1.00 | 1.00 | 1.00 |
| Mir431 | 1.00 | 1.00 | 1.00 | 1.00 | 7.38 | 1.00 | 1.00 | 1.00 | 1.00 |
| Mir432 | 1.00 | 1.00 | 1.00 | 1.00 | 1.00 | 1.00 | 1.00 | 1.00 | 1.00 |
| Mir433 | 1.00 | 1.00 | 1.00 | 0.38 | 1.25 | 1.00 | 1.00 | 1.00 | 1.00 |
| Mir434 | 1.00 | 1.00 | 1.00 | 1.00 | 1.00 | 1.00 | 1.00 | 10.91 | 1.00 |
| Mir450b | 0.05 | 10.82 | 1.00 | 1.00 | 1.00 | 1.00 | 0.05 | 1.00 | 1.00 |
| Mir451 | 1.00 | 21.01 | 1.00 | 1.00 | 1.00 | 1.00 | 0.54 | 3.33 | 2.49 |
| Mir453 | 1.00 | 0.09 | 1.00 | 1.00 | 1.00 | 1.00 | 17.43 | 1.00 | 1.00 |
| Mir4660 | 1.00 | 1.00 | 1.00 | 1.00 | 1.00 | 1.00 | 1.00 | 1.00 | 1.00 |
| Mir466i | 2.09 | 0.61 | 1.52 | 2.04 | 1.52 | 2.18 | 0.99 | 1.94 | 1.20 |
| Mir467a-10 | 1.00 | 1.00 | 1.00 | 1.00 | 1.00 | 1.00 | 1.00 | 21.13 | 1.00 |
| Mir467f | 0.24 | 0.81 | 0.48 | 2.97 | 1.04 | 0.18 | 2.20 | 2.12 | 1.15 |
| Mir484 | 0.04 | 1.00 | 1.00 | 1.00 | 1.00 | 1.00 | 1.00 | 1.00 | 1.00 |
| Mir485 | 1.00 | 1.00 | 1.01 | 1.00 | 1.00 | 1.00 | 1.00 | 0.03 | 1.00 |
| Mir486 | 2.43 | 1.00 | 0.44 | 0.12 | 1.56 | 0.73 | 8.91 | 1.31 | 1.00 |
| Mir487b | 1.00 | 1.00 | 1.00 | 1.00 | 1.00 | 1.00 | 1.00 | 1.00 | 1.00 |
| Mir490 | 1.00 | 1.00 | 1.00 | 1.00 | 1.00 | 1.00 | 1.00 | 1.00 | 1.00 |
| Mir491 | 9.57 | 1.00 | 1.00 | 1.00 | 1.00 | 1.00 | 1.00 | 1.00 | 1.00 |
| Mir493 | 1.00 | 1.00 | 1.00 | 1.00 | 1.00 | 1.00 | 1.00 | 1.00 | 1.00 |
| Mir496 | 1.00 | 1.00 | 1.00 | 1.00 | 1.00 | 1.00 | 1.00 | 1.00 | 1.00 |
| Mir499 | 1.00 | 1.00 | 1.00 | 1.00 | 1.00 | 1.00 | 1.00 | 1.00 | 1.00 |
| Mir5046 | 1.00 | 1.00 | 1.00 | 0.03 | 1.00 | 0.12 | 1.00 | 1.00 | 1.00 |
| Mir505 | 1.00 | 0.13 | 1.00 | 1.00 | 1.00 | 1.00 | 1.00 | 1.00 | 1.00 |
| Mir5098 | 1.00 | 1.00 | 1.00 | 1.00 | 1.00 | 1.00 | 1.00 | 1.00 | 0.05 |
| Mir5100 | 1.00 | 0.03 | 0.03 | 1.00 | 1.05 | 1.00 | 1.00 | 1.00 | 1.00 |
| Mir5103 | 1.00 | 3.63 | 0.04 | 16.46 | 1.00 | 0.07 | 42.10 | 23.93 | 1.01 |
| Mir5104 | 1.00 | 1.00 | 1.00 | 1.00 | 1.00 | 1.00 | 1.00 | 1.00 | 8.57 |
| Mir5106 | 0.06 | 1.00 | 1.00 | 1.00 | 1.00 | 1.00 | 1.00 | 1.00 | 1.00 |
| Mir5107 | 1.11 | 1.02 | 1.15 | 1.00 | 0.99 | 0.90 | 1.27 | 1.18 | 0.81 |
| Mir5112 | 1.00 | 1.00 | 0.02 | 1.00 | 1.00 | 1.00 | 1.00 | 1.00 | 1.00 |
| Mir5113 | 0.04 | 0.96 | 31.05 | 2.83 | 1.00 | 2.85 | 1.00 | 1.00 | 1.00 |
| Mir5114 | 1.00 | 1.00 | 1.00 | 1.00 | 1.00 | 7.73 | 1.00 | 1.00 | 1.00 |
| Mir5116 | 31.27 | 0.01 | 0.81 | 99.79 | 1.00 | 0.73 | 1.00 | 1.00 | 21.34 |
| Mir5119 | 0.96 | 0.02 | 0.56 | 79.51 | 68.32 | 1.00 | 307.68 | 0.01 | 125.99 |
| Mir5121 | 1.68 | 1.91 | 1.91 | 1.81 | 1.05 | 35.61 | 1.67 | 0.94 | 0.89 |
| Mir5123 | 1.00 | 1.00 | 0.10 | 1.00 | 1.00 | 1.00 | 1.00 | 21.13 | 14.62 |
| Mir5126 | 1.00 | 1.00 | 1.00 | 1.00 | 1.00 | 1.00 | 1.00 | 1.00 | 1.00 |
| Mir5127 | 1.00 | 1.00 | 1.00 | 1.00 | 1.00 | 1.00 | 1.00 | 1.00 | 1.00 |
| Mir5128 | 1.00 | 1.00 | 11.06 | 1.00 | 1.00 | 1.00 | 1.00 | 1.00 | 1.00 |
| Mir5129 | 1.00 | 1.00 | 1.00 | 1.00 | 1.00 | 1.00 | 1.00 | 1.00 | 1.00 |
| Mir5132 | 1.02 | 1.35 | 3.26 | 2.13 | 1.05 | 0.90 | 1.35 | 1.10 | 0.26 |
| Mir5133 | 1.34 | 0.90 | 1.80 | 0.53 | 1.53 | 1.87 | 2.35 | 0.79 | 1.14 |

Fig. 31-67

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir363 | 1.00 | 1.00 | 1.00 | 1.00 | 1.00 | 1.00 | 1.00 | 1.00 | 1.00 |
| Mir365-1 | 1.18 | 26.86 | 0.05 | 1.00 | 12.73 | 1.00 | 0.11 | 0.10 | 2.97 |
| Mir365-2 | 1.00 | 1.00 | 1.00 | 0.87 | 0.47 | 1.16 | 1.00 | 6.00 | 1.00 |
| Mir367 | 1.00 | 1.00 | 1.00 | 1.00 | 1.00 | 1.00 | 1.08 | 14.91 | 17.58 |
| Mir369 | 2.94 | 1.95 | 0.60 | 1.00 | 1.00 | 1.00 | 1.00 | 1.00 | 0.08 |
| Mir374 | 0.71 | 0.82 | 0.79 | 18.97 | 1.46 | 0.75 | 13.86 | 5.94 | 0.16 |
| Mir374c | 1.00 | 1.00 | 1.00 | 1.00 | 1.00 | 1.00 | 1.00 | 1.00 | 1.00 |
| Mir376a | 0.02 | 1.00 | 38.96 | 1.00 | 1.00 | 1.00 | 1.00 | 1.00 | 1.00 |
| Mir377 | 1.00 | 0.67 | 2.52 | 1.00 | 1.00 | 1.00 | 1.00 | 1.00 | 1.00 |
| Mir378b | 0.53 | 0.63 | 1.05 | 0.05 | 2.31 | 1.14 | 0.19 | 0.92 | 2.17 |
| Mir381 | 1.00 | 1.00 | 1.00 | 1.00 | 1.00 | 1.00 | 1.00 | 1.00 | 15.77 |
| Mir382 | 0.54 | 0.33 | 58.78 | 1.00 | 1.00 | 1.00 | 1.00 | 1.00 | 1.00 |
| Mir3960 | 0.36 | 1.60 | 1.02 | 0.38 | 0.83 | 9.32 | 1.43 | 0.64 | 1.52 |
| Mir3966 | 1.00 | 1.00 | 1.00 | 17.54 | 1.00 | 11.75 | 1.00 | 1.00 | 1.00 |
| Mir3968 | 1.00 | 1.00 | 1.00 | 1.00 | 1.00 | 1.00 | 1.48 | 0.93 | 3.82 |
| Mir3971 | 1.00 | 0.06 | 1.00 | 1.00 | 1.00 | 1.00 | 1.00 | 1.00 | 1.00 |
| Mir409 | 4.95 | 0.84 | 1.06 | 1.00 | 1.00 | 1.00 | 1.00 | 25.40 | 1.00 |
| Mir410 | 1.00 | 1.00 | 1.00 | 1.00 | 1.00 | 1.00 | 1.00 | 3.84 | 1.00 |
| Mir412 | 0.31 | 1.14 | 1.77 | 0.06 | 1.00 | 1.00 | 1.00 | 1.00 | 0.08 |
| Mir421 | 0.77 | 0.91 | 0.50 | 1.00 | 0.80 | 1.00 | 1.00 | 1.00 | 0.07 |
| Mir423 | 0.16 | 1.00 | 1.00 | 5.39 | 0.22 | 1.00 | 1.00 | 3.95 | 0.25 |
| Mir425 | 1.11 | 3.59 | 1.06 | 0.56 | 74.23 | 0.18 | 0.77 | 2.13 | 0.93 |
| Mir429 | 1.00 | 1.00 | 1.00 | 1.00 | 18.11 | 1.00 | 0.09 | 0.85 | 1.12 |
| Mir431 | 0.72 | 0.57 | 2.12 | 1.00 | 1.00 | 1.00 | 1.00 | 6.69 | 1.00 |
| Mir432 | 1.00 | 1.00 | 9.85 | 1.00 | 1.00 | 1.00 | 1.00 | 1.00 | 1.00 |
| Mir433 | 2.18 | 0.24 | 1.83 | 1.00 | 1.00 | 1.00 | 1.00 | 1.00 | 1.00 |
| Mir434 | 1.00 | 5.42 | 1.00 | 1.00 | 1.00 | 1.00 | 1.00 | 1.00 | 1.00 |
| Mir450b | 1.00 | 1.00 | 1.00 | 1.00 | 1.00 | 1.00 | 1.00 | 10.36 | 1.00 |
| Mir451 | 1.00 | 1.00 | 1.00 | 1.00 | 1.00 | 1.00 | 0.05 | 1.00 | 1.00 |
| Mir453 | 1.21 | 0.49 | 1.04 | 1.00 | 0.06 | 0.08 | 2.18 | 2.48 | 0.03 |
| Mir4660 | 1.00 | 1.00 | 1.00 | 1.00 | 1.00 | 1.00 | 1.00 | 1.00 | 1.00 |
| Mir466i | 0.43 | 0.96 | 0.57 | 0.32 | 0.09 | 0.39 | 3.18 | 0.84 | 0.73 |
| Mir467a-10 | 1.00 | 1.00 | 1.00 | 1.00 | 1.00 | 1.00 | 1.00 | 1.00 | 10.44 |
| Mir467f | 3.20 | 0.16 | 0.59 | 0.79 | 1.53 | 1.08 | 1.00 | 9.07 | 1.08 |
| Mir484 | 1.00 | 1.00 | 1.00 | 1.00 | 1.00 | 1.00 | 59.21 | 1.00 | 25.91 |
| Mir485 | 0.82 | 0.03 | 2.10 | 1.00 | 1.00 | 1.00 | 0.05 | 1.00 | 1.99 |
| Mir486 | 0.12 | 0.92 | 0.50 | 1.00 | 2.72 | 1.00 | 1.00 | 1.00 | 2.57 |
| Mir487b | 1.00 | 1.00 | 1.00 | 1.00 | 1.00 | 1.00 | 1.00 | 11.15 | 1.00 |
| Mir490 | 1.00 | 1.00 | 1.00 | 1.00 | 1.00 | 1.00 | 1.00 | 1.00 | 1.00 |
| Mir491 | 3.15 | 14.47 | 0.51 | 1.00 | 1.00 | 1.00 | 1.00 | 1.00 | 1.00 |
| Mir493 | 1.00 | 1.02 | 0.08 | 1.00 | 1.00 | 1.00 | 0.55 | 20.76 | 4.92 |
| Mir496 | 1.00 | 22.30 | 50.28 | 1.00 | 1.00 | 1.00 | 1.00 | 1.00 | 1.00 |
| Mir499 | 1.00 | 1.00 | 17.66 | 1.00 | 1.00 | 1.00 | 1.00 | 1.00 | 1.00 |
| Mir5046 | 1.00 | 1.00 | 1.00 | 1.00 | 1.00 | 1.00 | 1.00 | 1.00 | 1.00 |
| Mir505 | 1.00 | 1.00 | 1.00 | 1.00 | 1.00 | 1.00 | 8.88 | 1.00 | 1.00 |
| Mir5098 | 1.00 | 1.00 | 1.00 | 1.00 | 1.00 | 1.00 | 1.00 | 0.09 | 1.00 |
| Mir5100 | 1.00 | 1.00 | 1.00 | 1.00 | 0.00 | 0.50 | 1.10 | 1.82 | 36.42 |
| Mir5103 | 0.04 | 0.02 | 16.47 | 50.63 | 1.00 | 1.00 | 2.09 | 1.00 | 1.00 |
| Mir5104 | 1.00 | 1.00 | 1.00 | 1.00 | 1.00 | 1.00 | 1.00 | 1.00 | 1.00 |
| Mir5106 | 1.00 | 34.89 | 1.00 | 1.00 | 36.66 | 1.00 | 1.00 | 1.00 | 1.00 |
| Mir5107 | 1.00 | 1.00 | 1.00 | 0.21 | 0.34 | 0.82 | 1.00 | 1.00 | 1.00 |
| Mir5112 | 1.00 | 1.00 | 81.71 | 1.00 | 1.00 | 1.00 | 102.23 | 130.82 | 0.02 |
| Mir5113 | 1.00 | 1.00 | 1.00 | 0.14 | 0.28 | 1.00 | 1.00 | 1.00 | 6.35 |
| Mir5114 | 1.00 | 1.00 | 1.00 | 1.00 | 1.00 | 1.00 | 1.00 | 1.00 | 1.00 |
| Mir5116 | 1.00 | 1.00 | 0.02 | 1.00 | 1.00 | 0.01 | 1.00 | 102.89 | 0.57 |
| Mir5119 | 1.00 | 1.00 | 1.08 | 1.00 | 1.00 | 1.00 | 0.02 | 109.67 | 1.00 |
| Mir5121 | 28.63 | 32.18 | 67.50 | 1.10 | 0.02 | 0.95 | 1.08 | 2.73 | 0.42 |
| Mir5123 | 1.00 | 1.00 | 0.08 | 1.00 | 1.00 | 1.00 | 1.00 | 1.00 | 11.62 |
| Mir5126 | 1.00 | 1.00 | 1.00 | 1.00 | 1.00 | 1.00 | 1.00 | 1.00 | 1.00 |
| Mir5127 | 1.00 | 1.00 | 1.00 | 1.00 | 1.00 | 1.00 | 23.31 | 1.00 | 1.00 |
| Mir5128 | 1.00 | 1.00 | 1.00 | 1.00 | 1.00 | 1.00 | 11.59 | 0.05 | 1.00 |
| Mir5129 | 1.00 | 1.00 | 1.00 | 1.00 | 1.00 | 1.00 | 1.00 | 1.00 | 1.00 |
| Mir5132 | 0.02 | 0.02 | 0.37 | 0.01 | 1.45 | 3.38 | 1.00 | 20.33 | 1.00 |
| Mir5133 | 0.57 | 0.53 | 0.63 | 0.55 | 1.37 | 1.11 | 0.92 | 0.72 | 2.11 |

Fig. 31- 68

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir363 | 0.45 | 0.43 | 0.82 | 1.00 | 1.00 | 1.00 | 1.00 | 1.00 | 1.00 | 1.00 | 1.00 | 1.00 |
| Mir365-1 | 1.00 | 1.00 | 1.00 | 1.00 | 1.00 | 1.00 | 1.00 | 1.00 | 1.00 | 1.00 | 1.00 | 1.00 |
| Mir365-2 | 4.46 | 1.00 | 0.23 | 1.00 | 0.25 | 1.00 | 1.00 | 9.65 | 1.00 | 59.90 | 1.00 | 1.00 |
| Mir367 | 1.00 | 0.05 | 1.00 | 1.00 | 1.00 | 1.00 | 1.00 | 1.00 | 1.00 | 1.00 | 1.00 | 1.00 |
| Mir369 | 1.00 | 1.00 | 0.06 | 1.00 | 1.00 | 1.00 | 0.08 | 1.00 | 1.00 | 1.00 | 1.00 | 1.00 |
| Mir374 | 0.26 | 0.40 | 0.84 | 3.82 | 1.00 | 0.08 | 1.00 | 1.00 | 1.00 | 1.00 | 1.00 | 1.00 |
| Mir374c | 1.00 | 1.00 | 149.55 | 1.00 | 1.00 | 1.00 | 1.00 | 1.00 | 1.00 | 1.00 | 1.00 | 1.00 |
| Mir376a | 1.00 | 1.00 | 1.00 | 1.00 | 1.00 | 1.00 | 1.00 | 1.00 | 1.00 | 1.00 | 1.00 | 1.00 |
| Mir377 | 1.00 | 1.00 | 34.83 | 1.00 | 1.00 | 1.00 | 1.00 | 1.00 | 1.00 | 1.00 | 1.00 | 1.00 |
| Mir378b | 1.07 | 0.73 | 0.21 | 1.32 | 1.02 | 0.61 | 1.00 | 1.09 | 6.73 | 1.00 | 1.00 | 1.00 |
| Mir381 | 1.00 | 1.00 | 1.00 | 1.00 | 1.00 | 1.00 | 1.00 | 1.00 | 1.00 | 1.00 | 1.00 | 1.00 |
| Mir382 | 1.00 | 1.00 | 1.00 | 1.00 | 1.00 | 1.00 | 1.00 | 1.00 | 1.00 | 1.00 | 1.00 | 1.00 |
| Mir3960 | 1.25 | 0.53 | 0.80 | 0.99 | 0.66 | 1.16 | 0.27 | 1.12 | 0.98 | 1.00 | 1.00 | 1.00 |
| Mir3966 | 1.00 | 12.57 | 1.00 | 1.00 | 1.00 | 1.00 | 1.00 | 1.00 | 1.00 | 1.00 | 1.00 | 1.00 |
| Mir3968 | 2.12 | 0.23 | 1.00 | 1.00 | 1.00 | 1.00 | 1.00 | 1.00 | 1.00 | 1.00 | 1.00 | 1.00 |
| Mir3971 | 1.84 | 1.00 | 13.80 | 1.00 | 1.00 | 1.00 | 1.00 | 1.00 | 1.00 | 1.00 | 1.00 | 1.00 |
| Mir409 | 1.00 | 14.19 | 1.00 | 1.00 | 1.00 | 1.00 | 1.00 | 1.00 | 1.00 | 1.00 | 1.00 | 1.00 |
| Mir410 | 1.00 | 1.00 | 1.00 | 1.00 | 1.00 | 1.00 | 0.10 | 1.00 | 1.00 | 1.00 | 1.00 | 1.00 |
| Mir412 | 1.00 | 1.00 | 0.06 | 1.00 | 1.00 | 1.00 | 1.00 | 1.00 | 1.00 | 1.00 | 1.00 | 1.00 |
| Mir421 | 0.75 | 0.67 | 1.03 | 0.03 | 0.26 | 19.40 | 0.07 | 1.00 | 14.97 | 1.00 | 1.00 | 1.00 |
| Mir423 | 1.99 | 1.00 | 1.00 | 1.00 | 1.00 | 0.23 | 1.00 | 3.88 | 1.00 | 1.00 | 1.00 | 1.00 |
| Mir425 | 1.19 | 1.09 | 1.50 | 1.83 | 0.38 | 0.41 | 0.85 | 0.10 | 17.51 | 1.00 | 1.00 | 1.00 |
| Mir429 | 0.04 | 0.92 | 1.00 | 1.00 | 1.00 | 1.00 | 1.00 | 1.00 | 1.00 | 1.00 | 1.00 | 1.00 |
| Mir431 | 0.27 | 1.00 | 1.00 | 1.00 | 1.00 | 1.00 | 1.00 | 1.00 | 1.00 | 1.00 | 1.00 | 1.00 |
| Mir432 | 1.00 | 1.00 | 1.00 | 1.00 | 1.00 | 1.00 | 1.00 | 1.00 | 1.00 | 1.00 | 1.00 | 1.00 |
| Mir433 | 1.00 | 1.00 | 1.00 | 1.00 | 1.00 | 1.00 | 1.00 | 1.00 | 1.00 | 1.00 | 1.00 | 1.00 |
| Mir434 | 8.09 | 1.00 | 1.00 | 1.00 | 1.00 | 1.00 | 1.00 | 1.00 | 1.00 | 1.00 | 1.00 | 1.00 |
| Mir450b | 1.00 | 1.00 | 1.00 | 0.09 | 1.00 | 1.00 | 1.00 | 1.00 | 1.00 | 1.00 | 1.00 | 1.00 |
| Mir451 | 1.00 | 1.00 | 1.00 | 0.85 | 1.21 | 1.91 | 1.00 | 0.06 | 1.00 | 1.00 | 1.00 | 1.00 |
| Mir453 | 1.00 | 1.00 | 1.00 | 1.00 | 1.00 | 1.00 | 1.00 | 1.00 | 1.00 | 1.00 | 1.00 | 1.00 |
| Mir466o | 1.00 | 1.00 | 1.00 | 1.00 | 1.00 | 1.00 | 1.00 | 1.00 | 1.00 | 1.00 | 1.00 | 20.12 |
| Mir466i | 0.97 | 0.96 | 2.05 | 0.82 | 0.97 | 0.60 | 1.00 | 0.97 | 0.93 | 1.00 | 1.00 | 1.00 |
| Mir467a-10 | 1.00 | 1.00 | 1.00 | 1.00 | 1.00 | 1.00 | 1.00 | 1.00 | 1.00 | 1.00 | 1.00 | 1.00 |
| Mir467f | 0.47 | 1.28 | 0.81 | 0.17 | 2.92 | 6.11 | 2.23 | 1.00 | 0.24 | 1.00 | 1.00 | 1.00 |
| Mir484 | 1.00 | 1.00 | 1.00 | 1.00 | 1.00 | 1.00 | 1.00 | 0.05 | 1.00 | 1.00 | 6.67 | 1.00 |
| Mir485 | 25.18 | 1.00 | 1.00 | 1.00 | 1.00 | 1.00 | 1.00 | 1.00 | 1.00 | 1.00 | 1.00 | 1.00 |
| Mir486 | 1.00 | 1.00 | 1.00 | 1.55 | 0.75 | 0.66 | 1.00 | 1.00 | 1.00 | 1.00 | 1.00 | 1.00 |
| Mir487b | 1.00 | 1.00 | 1.00 | 1.00 | 1.00 | 1.00 | 1.00 | 1.00 | 1.00 | 1.00 | 1.00 | 1.00 |
| Mir490 | 1.00 | 1.00 | 1.00 | 1.00 | 1.00 | 1.00 | 1.00 | 1.00 | 1.00 | 1.00 | 1.00 | 1.00 |
| Mir491 | 0.09 | 1.00 | 0.08 | 1.00 | 1.00 | 1.00 | 1.00 | 1.00 | 1.00 | 1.00 | 1.00 | 1.00 |
| Mir493 | 1.00 | 1.00 | 1.00 | 1.00 | 1.00 | 1.00 | 1.00 | 1.00 | 1.00 | 1.00 | 1.00 | 1.00 |
| Mir496 | 1.00 | 1.00 | 1.00 | 1.00 | 1.00 | 1.00 | 1.00 | 1.00 | 1.00 | 1.00 | 1.00 | 1.00 |
| Mir499 | 1.00 | 1.00 | 1.00 | 1.00 | 1.00 | 1.00 | 1.00 | 1.00 | 1.00 | 1.00 | 1.00 | 1.00 |
| Mir5046 | 1.00 | 1.00 | 1.00 | 1.00 | 1.00 | 1.00 | 1.00 | 0.03 | 12.10 | 1.00 | 1.00 | 1.00 |
| Mir505 | 1.00 | 1.00 | 1.00 | 1.00 | 1.00 | 1.00 | 1.00 | 1.00 | 1.00 | 1.00 | 1.00 | 1.00 |
| Mir5098 | 13.84 | 1.00 | 14.54 | 1.00 | 0.08 | 13.12 | 1.00 | 1.00 | 1.00 | 1.00 | 1.00 | 1.00 |
| Mir5100 | 90.08 | 35.23 | 1.00 | 1.00 | 1.00 | 43.23 | 1.00 | 0.04 | 35.31 | 1.00 | 1.00 | 1.00 |
| Mir5103 | 1.10 | 0.03 | 0.34 | 1.00 | 0.01 | 1.15 | 1.00 | 1.00 | 1.00 | 1.00 | 1.00 | 1.00 |
| Mir5104 | 8.24 | 1.00 | 1.00 | 1.00 | 1.00 | 1.00 | 1.00 | 1.00 | 1.00 | 1.00 | 1.00 | 1.00 |
| Mir5106 | 1.00 | 1.00 | 1.00 | 1.00 | 1.00 | 1.00 | 1.00 | 1.00 | 1.00 | 1.00 | 1.00 | 1.00 |
| Mir5107 | 1.60 | 1.65 | 2.07 | 1.02 | 0.86 | 0.87 | 0.72 | 0.31 | 0.74 | 1.00 | 1.00 | 1.00 |
| Mir5112 | 1.00 | 1.00 | 1.00 | 1.00 | 1.00 | 1.00 | 1.00 | 1.00 | 1.00 | 1.00 | 1.00 | 1.00 |
| Mir5113 | 57.02 | 4.66 | 33.15 | 1.00 | 1.00 | 1.00 | 0.36 | 67.88 | 0.05 | 1.00 | 1.00 | 1.00 |
| Mir5114 | 1.00 | 1.00 | 1.00 | 1.00 | 1.00 | 92.53 | 1.00 | 1.00 | 172.90 | 1.00 | 1.00 | 1.00 |
| Mir5116 | 0.77 | 178.79 | 1.00 | 1.84 | 1.19 | 1.00 | 38.82 | 1.00 | 1.00 | 1.00 | 1.00 | 1.00 |
| Mir5119 | 0.00 | 1.04 | 0.01 | 0.02 | 1.00 | 1.00 | 1.00 | 1.00 | 1.00 | 1.00 | 1.00 | 1.00 |
| Mir5121 | 0.69 | 1.01 | 1.06 | 0.39 | 1.70 | 1.14 | 4.90 | 0.72 | 1.17 | 1.00 | 1.00 | 1.00 |
| Mir5123 | 1.00 | 1.00 | 1.00 | 0.04 | 1.00 | 1.00 | 1.00 | 1.00 | 1.00 | 1.00 | 1.00 | 1.00 |
| Mir5126 | 19.36 | 1.00 | 1.00 | 1.00 | 1.00 | 1.00 | 1.00 | 1.00 | 1.00 | 1.00 | 1.00 | 1.00 |
| Mir5127 | 1.00 | 1.00 | 1.00 | 1.00 | 1.00 | 1.00 | 1.00 | 1.00 | 1.00 | 1.00 | 1.00 | 1.00 |
| Mir5128 | 1.00 | 1.00 | 1.00 | 1.00 | 1.00 | 1.00 | 1.00 | 1.00 | 1.00 | 1.00 | 1.00 | 1.00 |
| Mir5129 | 1.00 | 1.00 | 1.00 | 1.00 | 1.00 | 1.00 | 1.00 | 1.00 | 1.00 | 1.00 | 1.00 | 1.00 |
| Mir5132 | 0.04 | 1.87 | 0.01 | 0.48 | 0.20 | 0.81 | 2.79 | 1.00 | 0.37 | 1.00 | 1.00 | 1.00 |
| Mir5133 | 1.90 | 1.74 | 0.79 | 0.77 | 56.32 | 0.75 | 0.38 | 1.28 | 0.22 | 1.00 | 1.00 | 1.00 |

Fig. 31- 69

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir5134 | 1.00 | 1.00 | 1.00 | 1.00 | 1.00 | 1.00 | 1.00 | 1.00 | 1.00 |
| Mir5135 | 1.00 | 0.06 | 1.00 | 1.00 | 1.00 | 1.00 | 1.00 | 23.25 | 1.00 |
| Mir5136 | 1.00 | 1.00 | 1.00 | 1.00 | 1.00 | 1.00 | 8.38 | 1.00 | 1.00 |
| Mir540 | 1.00 | 1.00 | 1.00 | 1.00 | 1.00 | 1.00 | 1.00 | 1.00 | 1.00 |
| Mir541 | 1.00 | 1.00 | 1.00 | 1.00 | 13.07 | 1.00 | 1.00 | 1.00 | 1.00 |
| Mir547 | 1.00 | 1.00 | 1.00 | 1.00 | 1.00 | 1.00 | 1.00 | 1.00 | 1.00 |
| Mir5615-2 | 1.00 | 1.00 | 1.00 | 1.00 | 1.00 | 1.00 | 1.00 | 1.00 | 1.00 |
| Mir5617 | 1.00 | 1.00 | 1.00 | 1.00 | 1.00 | 1.00 | 1.00 | 1.00 | 0.01 |
| Mir5618 | 1.00 | 1.00 | 1.00 | 1.00 | 1.00 | 1.00 | 1.00 | 1.00 | 1.00 |
| Mir5619 | 1.00 | 49.35 | 1.00 | 1.00 | 1.00 | 1.00 | 1.00 | 1.00 | 1.00 |
| Mir5620 | 1.00 | 1.00 | 81.05 | 235.24 | 1.00 | 1.00 | 1.00 | 1.00 | 1.00 |
| Mir5621 | 1.00 | 1.00 | 0.02 | 0.01 | 108.79 | 1.00 | 1.00 | 59.02 | 1.00 |
| Mir5622 | 1.00 | 1.00 | 1.00 | 1.00 | 1.00 | 1.00 | 1.00 | 1.00 | 1.00 |
| Mir5623 | 1.00 | 25.19 | 1.00 | 1.00 | 1.00 | 1.00 | 1.00 | 31.93 | 1.00 |
| Mir5625 | 0.92 | 0.06 | 16.07 | 1.00 | 1.00 | 0.06 | 1.00 | 1.00 | 1.00 |
| Mir568 | 0.64 | 0.61 | 0.55 | 1.62 | 0.70 | 0.87 | 1.22 | 0.66 | 0.75 |
| Mir5709 | 1.00 | 0.10 | 1.00 | 1.00 | 1.00 | 10.10 | 1.00 | 1.00 | 1.00 |
| Mir5710 | 1.00 | 1.00 | 0.03 | 1.00 | 0.02 | 1.00 | 1.00 | 1.00 | 1.00 |
| Mir599 | 1.00 | 1.00 | 1.00 | 0.08 | 0.08 | 1.00 | 1.00 | 1.00 | 1.00 |
| Mir6236 | 1.12 | 0.83 | 0.72 | 0.78 | 0.92 | 1.68 | 1.32 | 0.30 | 1.04 |
| Mir6244 | 0.93 | 0.45 | 1.00 | 1.27 | 1.03 | 0.16 | 7.27 | 0.35 | 0.03 |
| Mir6337 | 1.00 | 1.00 | 1.00 | 1.00 | 1.00 | 1.00 | 1.00 | 1.00 | 1.00 |
| Mir6338 | 0.84 | 0.87 | 4.50 | 6.19 | 5.81 | 0.13 | 1.00 | 1.00 | 1.00 |
| Mir6340 | 0.68 | 0.79 | 1.33 | 0.54 | 1.37 | 1.32 | 3.13 | 0.49 | 0.96 |
| Mir6356 | 1.00 | 1.00 | 1.00 | 1.00 | 1.00 | 1.00 | 1.00 | 1.00 | 1.00 |
| Mir6357 | 3.64 | 10.86 | 1.22 | 0.74 | 0.51 | 0.79 | 0.79 | 0.95 | 0.93 |
| Mir6358 | 1.00 | 1.00 | 1.00 | 1.00 | 1.00 | 1.00 | 1.00 | 1.00 | 1.00 |
| Mir6359 | 0.04 | 0.08 | 0.13 | 0.11 | 43.09 | 1.00 | 0.15 | 0.68 | 1.00 |
| Mir6363 | 0.06 | 0.26 | 29.26 | 0.94 | 1.00 | 0.82 | 0.26 | 4.00 | 0.15 |
| Mir6365 | 6.18 | 1.00 | 1.00 | 1.00 | 1.00 | 6.21 | 1.00 | 1.00 | 1.00 |
| Mir6366 | 1.00 | 1.00 | 1.00 | 1.00 | 1.00 | 1.00 | 1.00 | 1.00 | 1.00 |
| Mir6368 | 1.00 | 1.00 | 1.00 | 1.00 | 1.00 | 1.00 | 1.00 | 1.00 | 1.00 |
| Mir6386 | 0.90 | 0.87 | 0.86 | 0.31 | 0.31 | 1.04 | 0.06 | 1.05 | 0.13 |
| Mir6387 | 4.88 | 11.99 | 4.65 | 1.35 | 0.04 | 0.28 | 5.39 | 13.25 | 1.00 |
| Mir6389 | 1.00 | 1.00 | 1.00 | 1.00 | 1.00 | 1.00 | 1.00 | 1.00 | 1.00 |
| Mir6391 | 1.00 | 1.00 | 1.00 | 1.00 | 1.00 | 1.00 | 1.00 | 1.00 | 1.00 |
| Mir6392 | 1.40 | 1.00 | 0.95 | 6.42 | 0.10 | 1.00 | 1.00 | 1.00 | 1.00 |
| Mir6395 | 0.03 | 1.68 | 0.11 | 0.10 | 1.00 | 9.18 | 0.36 | 1.00 | 31.87 |
| Mir6396 | 1.00 | 0.22 | 0.50 | 0.23 | 1.00 | 1.04 | 1.00 | 1.00 | 1.00 |
| Mir6397 | 8.37 | 1.00 | 1.00 | 23.27 | 0.60 | 0.04 | 1.14 | 0.46 | 1.00 |
| Mir6399 | 1.00 | 1.00 | 1.00 | 1.00 | 1.00 | 0.08 | 1.00 | 1.00 | 0.97 |
| Mir6400 | 1.00 | 1.00 | 1.00 | 1.00 | 0.09 | 1.00 | 1.00 | 1.00 | 1.00 |
| Mir6403 | 6.43 | 0.48 | 0.55 | 0.13 | 0.11 | 1.82 | 1.00 | 1.00 | 1.00 |
| Mir6404 | 1.00 | 1.00 | 1.00 | 1.00 | 1.00 | 1.00 | 1.00 | 1.00 | 1.00 |
| Mir6405 | 1.00 | 1.00 | 1.00 | 3.38 | 1.00 | 0.35 | 1.00 | 1.00 | 1.00 |
| Mir6406 | 0.33 | 0.16 | 0.48 | 1.20 | 4.01 | 3.22 | 1.00 | 0.27 | 1.00 |
| Mir6407 | 0.08 | 1.00 | 0.15 | 7.28 | 1.00 | 1.00 | 1.00 | 1.00 | 1.00 |
| Mir6415 | 1.00 | 1.00 | 1.00 | 1.00 | 1.00 | 1.00 | 1.00 | 1.00 | 0.93 |
| Mir6417 | 1.00 | 1.00 | 1.00 | 1.19 | 4.58 | 1.00 | 1.00 | 1.00 | 1.00 |
| Mir6418 | 3.73 | 0.82 | 1.64 | 5.05 | 2.03 | 1.12 | 4.29 | 0.23 | 4.27 |
| Mir6481 | 0.33 | 2.28 | 1.00 | 0.10 | 0.07 | 0.51 | 9.92 | 1.83 | 5.39 |
| Mir6537 | 1.00 | 1.00 | 1.00 | 1.00 | 1.00 | 1.00 | 1.00 | 1.00 | 1.00 |
| Mir6538 | 1.00 | 0.21 | 1.00 | 0.20 | 1.00 | 1.00 | 1.00 | 1.00 | 1.00 |
| Mir6546 | 1.00 | 0.02 | 1.00 | 1.00 | 1.00 | 1.00 | 1.00 | 1.00 | 1.00 |
| Mir664 | 1.00 | 1.00 | 1.00 | 46.99 | 1.00 | 35.27 | 1.00 | 1.00 | 1.00 |
| Mir665 | 1.00 | 1.00 | 0.06 | 1.00 | 1.00 | 1.00 | 1.00 | 1.00 | 1.00 |
| Mir667 | 1.00 | 1.00 | 1.00 | 1.00 | 1.00 | 1.00 | 1.00 | 1.00 | 1.00 |
| Mir671 | 9.55 | 0.07 | 5.82 | 0.29 | 1.00 | 23.35 | 1.00 | 0.43 | 2.79 |
| Mir672 | 1.00 | 1.00 | 1.00 | 1.00 | 1.00 | 1.00 | 1.00 | 1.00 | 1.00 |
| Mir674 | 0.14 | 1.00 | 1.00 | 1.00 | 1.00 | 0.16 | 7.62 | 1.00 | 1.00 |
| Mir675 | 5.03 | 2.44 | 0.48 | 1.00 | 1.00 | 1.00 | 1.00 | 1.00 | 1.00 |
| Mir676 | 1.00 | 1.00 | 1.00 | 1.00 | 1.00 | 1.00 | 1.00 | 1.00 | 1.00 |
| Mir6769b | 1.00 | 1.00 | 1.00 | 1.00 | 1.00 | 1.00 | 1.00 | 1.00 | 1.00 |
| Mir678 | 6.53 | 0.44 | 0.06 | 0.09 | 0.67 | 0.03 | 25.49 | 0.90 | 1.00 |

Fig. 31-70

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir5134 | 1.00 | 1.00 | 1.00 | 1.00 | 1.00 | 1.00 | 1.00 | 1.00 | 1.00 |
| Mir5135 | 0.08 | 1.00 | 1.00 | 1.00 | 0.07 | 1.00 | 0.45 | 26.61 | 1.00 |
| Mir5136 | 1.00 | 1.00 | 1.00 | 1.00 | 1.00 | 1.00 | 1.00 | 30.99 | 1.00 |
| Mir540 | 1.00 | 1.00 | 1.00 | 1.00 | 1.00 | 1.00 | 1.00 | 1.00 | 1.00 |
| Mir541 | 1.00 | 1.00 | 0.13 | 1.00 | 8.05 | 1.00 | 1.00 | 1.00 | 1.00 |
| Mir547 | 1.00 | 1.00 | 1.00 | 1.00 | 1.00 | 1.00 | 1.00 | 1.00 | 1.00 |
| Mir5615-2 | 1.00 | 1.00 | 1.00 | 1.00 | 1.00 | 1.00 | 1.00 | 1.00 | 1.00 |
| Mir5617 | 1.00 | 1.00 | 1.00 | 1.00 | 1.00 | 1.00 | 1.00 | 1.00 | 136.96 |
| Mir5618 | 1.00 | 1.00 | 0.01 | 1.00 | 1.00 | 1.00 | 1.00 | 1.00 | 1.00 |
| Mir5619 | 1.00 | 1.00 | 1.00 | 44.89 | 1.00 | 0.02 | 1.00 | 1.00 | 1.00 |
| Mir5620 | 1.00 | 1.00 | 0.02 | 72.23 | 1.00 | 1.00 | 1.00 | 1.00 | 0.01 |
| Mir5621 | 1.00 | 1.00 | 39.83 | 1.00 | 1.00 | 0.02 | 1.00 | 1.00 | 0.02 |
| Mir5622 | 1.00 | 1.00 | 1.00 | 1.00 | 1.00 | 1.00 | 1.00 | 1.00 | 1.00 |
| Mir5623 | 1.00 | 1.00 | 1.00 | 1.00 | 1.00 | 1.00 | 1.00 | 1.00 | 1.00 |
| Mir5625 | 1.00 | 1.00 | 13.80 | 1.00 | 1.00 | 1.00 | 1.00 | 1.00 | 1.00 |
| Mir568 | 0.56 | 0.66 | 0.92 | 1.25 | 0.84 | 1.28 | 1.23 | 0.34 | 2.72 |
| Mir5709 | 1.00 | 1.00 | 1.00 | 1.00 | 1.00 | 1.00 | 1.00 | 1.00 | 1.00 |
| Mir5710 | 24.34 | 1.00 | 0.04 | 1.00 | 1.00 | 1.00 | 1.00 | 1.00 | 1.00 |
| Mir599 | 1.00 | 1.00 | 1.00 | 1.00 | 1.00 | 1.00 | 1.00 | 1.00 | 1.00 |
| Mir6236 | 1.64 | 1.04 | 0.81 | 1.29 | 0.69 | 3.14 | 1.33 | 1.34 | 1.06 |
| Mir6244 | 0.98 | 38.88 | 0.77 | 0.30 | 1.13 | 0.98 | 0.74 | 0.70 | 3.84 |
| Mir6337 | 1.00 | 1.00 | 1.00 | 1.00 | 1.00 | 1.00 | 1.00 | 1.00 | 1.00 |
| Mir6338 | 0.27 | 7.10 | 4.24 | 0.96 | 3.25 | 1.04 | 1.00 | 1.00 | 1.00 |
| Mir6340 | 2.00 | 1.35 | 1.32 | 1.13 | 0.79 | 0.79 | 0.48 | 0.90 | 1.43 |
| Mir6356 | 1.00 | 1.00 | 1.00 | 1.00 | 1.00 | 1.00 | 1.00 | 7.98 | 6.70 |
| Mir6357 | 0.90 | 1.04 | 0.23 | 0.86 | 3.94 | 0.42 | 1.52 | 1.14 | 0.79 |
| Mir6358 | 1.00 | 0.20 | 1.00 | 1.00 | 1.00 | 1.00 | 1.00 | 1.00 | 1.00 |
| Mir6359 | 3.86 | 1.00 | 30.26 | 1.00 | 4.91 | 1.00 | 1.23 | 0.05 | 8.50 |
| Mir6363 | 0.70 | 1.84 | 0.23 | 5.16 | 8.79 | 1.57 | 1.32 | 0.25 | 1.35 |
| Mir6365 | 1.00 | 1.00 | 0.19 | 1.00 | 0.19 | 5.56 | 1.00 | 1.00 | 1.00 |
| Mir6366 | 1.00 | 1.00 | 1.00 | 1.00 | 1.00 | 1.00 | 1.00 | 1.00 | 1.00 |
| Mir6368 | 1.00 | 1.00 | 1.00 | 1.00 | 1.00 | 1.00 | 1.00 | 1.00 | 1.00 |
| Mir6386 | 0.68 | 0.59 | 1.54 | 1.00 | 0.08 | 0.52 | 0.23 | 1.61 | 0.25 |
| Mir6387 | 0.29 | 2.41 | 1.04 | 0.12 | 0.13 | 1.00 | 0.94 | 0.62 | 3.82 |
| Mir6389 | 1.00 | 1.00 | 1.00 | 1.00 | 1.00 | 1.00 | 1.00 | 1.00 | 1.00 |
| Mir6391 | 1.00 | 1.00 | 1.00 | 1.00 | 4.98 | 4.72 | 1.00 | 0.13 | 6.22 |
| Mir6392 | 0.26 | 1.00 | 11.12 | 0.98 | 12.39 | 0.98 | 1.00 | 1.00 | 1.00 |
| Mir6395 | 0.92 | 0.68 | 1.44 | 0.12 | 14.82 | 0.98 | 1.29 | 2.17 | 0.94 |
| Mir6396 | 1.00 | 3.58 | 1.12 | 1.00 | 0.99 | 1.00 | 1.00 | 1.00 | 1.00 |
| Mir6397 | 1.00 | 0.15 | 1.00 | 1.00 | 7.47 | 1.00 | 0.09 | 1.00 | 1.00 |
| Mir6399 | 1.00 | 9.82 | 0.10 | 1.00 | 1.00 | 1.00 | 16.84 | 1.00 | 27.87 |
| Mir6400 | 1.00 | 1.00 | 1.00 | 1.00 | 1.00 | 1.00 | 1.00 | 0.08 | 1.00 |
| Mir6403 | 4.13 | 0.35 | 0.19 | 1.00 | 0.42 | 1.00 | 0.92 | 1.04 | 14.11 |
| Mir6404 | 1.00 | 1.00 | 1.00 | 1.00 | 1.00 | 1.00 | 1.00 | 1.00 | 1.00 |
| Mir6405 | 1.00 | 1.00 | 1.00 | 1.00 | 1.00 | 1.00 | 1.00 | 1.00 | 1.00 |
| Mir6406 | 0.53 | 3.07 | 5.02 | 0.31 | 1.00 | 1.00 | 1.00 | 1.00 | 1.00 |
| Mir6407 | 1.00 | 1.00 | 0.19 | 1.00 | 1.00 | 1.00 | 1.00 | 9.19 | 1.00 |
| Mir6415 | 1.00 | 1.00 | 1.00 | 1.00 | 1.00 | 1.00 | 1.00 | 0.12 | 6.70 |
| Mir6417 | 1.00 | 1.00 | 1.00 | 1.00 | 1.00 | 0.98 | 0.22 | 4.93 | 0.26 |
| Mir6418 | 1.21 | 1.78 | 1.07 | 0.29 | 1.04 | 6.24 | 2.82 | 1.10 | 0.96 |
| Mir6481 | 2.03 | 1.04 | 0.06 | 1.00 | 1.96 | 4.02 | 1.22 | 2.12 | 0.48 |
| Mir6537 | 1.00 | 4.08 | 1.00 | 1.00 | 1.00 | 1.00 | 1.00 | 0.17 | 0.90 |
| Mir6538 | 0.28 | 1.00 | 1.00 | 1.00 | 1.00 | 1.00 | 1.00 | 1.00 | 1.00 |
| Mir6546 | 0.02 | 42.92 | 1.00 | 1.00 | 1.00 | 1.00 | 1.00 | 1.00 | 1.00 |
| Mir664 | 1.00 | 1.00 | 1.00 | 1.00 | 1.00 | 0.04 | 1.00 | 1.00 | 1.00 |
| Mir665 | 1.00 | 1.00 | 1.00 | 1.00 | 1.00 | 1.00 | 1.00 | 1.00 | 1.00 |
| Mir667 | 1.00 | 1.00 | 1.00 | 1.00 | 1.00 | 1.00 | 1.00 | 1.00 | 1.00 |
| Mir671 | 0.49 | 1.00 | 1.25 | 0.45 | 3.14 | 13.64 | 0.05 | 2.54 | 1.61 |
| Mir672 | 1.00 | 0.19 | 2.05 | 1.00 | 1.00 | 1.00 | 1.00 | 1.00 | 1.00 |
| Mir674 | 1.00 | 1.00 | 1.00 | 1.00 | 1.00 | 1.00 | 1.00 | 1.00 | 1.00 |
| Mir675 | 1.05 | 9.96 | 0.05 | 0.70 | 0.79 | 1.03 | 0.06 | 1.00 | 1.00 |
| Mir676 | 1.00 | 1.00 | 1.00 | 1.00 | 1.00 | 1.00 | 1.00 | 1.00 | 1.00 |
| Mir6769b | 1.00 | 1.00 | 1.00 | 1.00 | 1.00 | 1.00 | 1.00 | 1.00 | 1.00 |
| Mir678 | 0.73 | 129.39 | 4.14 | 0.03 | 2.61 | 1.00 | 9.39 | 0.01 | 29.54 |

Fig. 31-71

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir5134 | 1.00 | 1.00 | 1.00 | 1.00 | 1.00 | 1.00 | 1.00 | 1.00 | 1.00 |
| Mir5135 | 1.00 | 1.00 | 1.00 | 1.00 | 20.73 | 1.00 | 1.00 | 1.00 | 0.08 |
| Mir5136 | 1.00 | 1.00 | 1.00 | 1.00 | 1.00 | 1.00 | 0.06 | 1.00 | 39.78 |
| Mir540 | 1.00 | 0.01 | 0.01 | 1.00 | 1.00 | 1.00 | 1.00 | 1.00 | 1.00 |
| Mir541 | 1.13 | 0.74 | 0.92 | 1.00 | 2.12 | 0.12 | 1.00 | 7.25 | 1.00 |
| Mir547 | 1.00 | 1.00 | 1.00 | 1.00 | 1.00 | 1.00 | 15.43 | 0.96 | 1.00 |
| Mir5615-2 | 172.50 | 1.00 | 1.00 | 1.00 | 0.01 | 1.00 | 1.00 | 1.00 | 44.37 |
| Mir5617 | 1.00 | 1.00 | 1.00 | 1.00 | 1.00 | 1.00 | 1.00 | 1.00 | 1.00 |
| Mir5618 | 1.00 | 1.00 | 1.00 | 1.00 | 1.00 | 1.00 | 131.78 | 0.01 | 1.00 |
| Mir5619 | 1.00 | 1.00 | 1.00 | 1.00 | 1.00 | 1.00 | 1.00 | 1.00 | 1.00 |
| Mir5620 | 1.00 | 1.00 | 1.00 | 1.00 | 1.00 | 1.00 | 0.66 | 3.74 | 1.01 |
| Mir5621 | 85.84 | 1.00 | 58.23 | 1.00 | 1.00 | 1.00 | 40.12 | 1.00 | 1.00 |
| Mir5622 | 1.00 | 1.00 | 1.00 | 1.00 | 1.00 | 1.00 | 1.00 | 1.00 | 1.00 |
| Mir5623 | 1.00 | 1.00 | 1.00 | 1.00 | 47.59 | 1.00 | 0.04 | 1.00 | 1.00 |
| Mir5625 | 0.04 | 1.00 | 1.00 | 1.00 | 1.00 | 1.00 | 1.00 | 12.70 | 1.00 |
| Mir568 | 0.79 | 0.99 | 0.99 | 0.82 | 1.19 | 1.41 | 0.19 | 1.50 | 0.81 |
| Mir5709 | 1.00 | 1.00 | 1.00 | 1.00 | 1.00 | 1.00 | 1.00 | 1.00 | 1.00 |
| Mir5710 | 44.23 | 1.00 | 1.00 | 1.00 | 0.01 | 1.00 | 0.02 | 0.01 | 1.06 |
| Mir599 | 1.00 | 1.00 | 1.00 | 1.00 | 1.00 | 1.00 | 1.00 | 1.00 | 1.00 |
| Mir6236 | 0.85 | 1.16 | 0.58 | 1.32 | 18.91 | 1.38 | 0.62 | 1.40 | 1.02 |
| Mir6244 | 1.35 | 53.46 | 1.00 | 2.76 | 1.06 | 1.18 | 0.48 | 1.63 | 5.70 |
| Mir6337 | 1.00 | 1.00 | 1.00 | 6.26 | 1.00 | 0.23 | 1.45 | 1.78 | 1.41 |
| Mir6338 | 1.00 | 1.00 | 1.00 | 1.00 | 1.00 | 1.00 | 0.25 | 1.00 | 1.00 |
| Mir6340 | 1.51 | 0.70 | 1.81 | 0.57 | 0.63 | 1.03 | 0.85 | 0.91 | 0.93 |
| Mir6356 | 1.00 | 1.00 | 1.00 | 1.00 | 1.00 | 1.00 | 5.62 | 1.00 | 5.39 |
| Mir6357 | 1.24 | 1.27 | 0.45 | 0.44 | 0.41 | 1.13 | 1.84 | 1.15 | 2.00 |
| Mir6358 | 1.00 | 1.00 | 0.18 | 1.00 | 1.00 | 1.00 | 5.82 | 1.00 | 1.00 |
| Mir6359 | 0.08 | 1.00 | 0.07 | 0.29 | 0.10 | 17.38 | 23.56 | 1.00 | 1.00 |
| Mir6363 | 1.34 | 0.31 | 0.51 | 3.99 | 1.02 | 0.70 | 0.24 | 2.26 | 0.17 |
| Mir6365 | 0.14 | 1.00 | 5.71 | 1.00 | 1.00 | 0.36 | 0.30 | 1.37 | 2.94 |
| Mir6366 | 1.00 | 1.00 | 1.00 | 1.00 | 1.00 | 1.00 | 12.75 | 1.00 | 1.00 |
| Mir6368 | 1.00 | 1.00 | 1.00 | 1.00 | 1.00 | 1.00 | 1.00 | 1.00 | 1.00 |
| Mir6386 | 1.00 | 0.15 | 0.37 | 2.51 | 0.22 | 0.67 | 1.00 | 4.63 | 1.00 |
| Mir6387 | 4.82 | 1.00 | 0.23 | 1.00 | 1.00 | 1.78 | 1.00 | 1.00 | 1.00 |
| Mir6389 | 1.00 | 1.00 | 5.50 | 1.00 | 1.00 | 1.00 | 1.00 | 1.00 | 1.00 |
| Mir6391 | 1.00 | 1.00 | 1.00 | 1.00 | 1.00 | 1.00 | 1.00 | 1.00 | 1.00 |
| Mir6392 | 0.67 | 1.17 | 0.52 | 0.22 | 1.28 | 1.25 | 1.00 | 1.00 | 1.00 |
| Mir6395 | 19.29 | 1.00 | 0.55 | 2.35 | 0.96 | 16.03 | 8.52 | 0.12 | 8.16 |
| Mir6396 | 1.00 | 1.00 | 1.00 | 1.00 | 1.00 | 1.00 | 0.26 | 6.21 | 0.27 |
| Mir6397 | 1.18 | 0.96 | 0.13 | 0.11 | 20.57 | 1.82 | 1.00 | 1.00 | 1.00 |
| Mir6399 | 0.97 | 1.00 | 1.00 | 1.00 | 1.00 | 1.00 | 0.10 | 0.09 | 1.09 |
| Mir6400 | 1.00 | 1.00 | 8.32 | 1.00 | 1.00 | 1.00 | 1.00 | 1.00 | 1.00 |
| Mir6403 | 0.63 | 0.14 | 2.72 | 2.48 | 1.40 | 0.29 | 0.23 | 2.33 | 1.01 |
| Mir6404 | 1.00 | 1.00 | 1.00 | 1.00 | 1.00 | 1.00 | 7.55 | 0.08 | 0.08 |
| Mir6405 | 1.00 | 1.00 | 1.00 | 1.00 | 9.10 | 1.00 | 0.36 | 0.35 | 1.00 |
| Mir6406 | 3.27 | 1.00 | 0.18 | 0.31 | 2.93 | 0.36 | 0.34 | 1.00 | 1.00 |
| Mir6407 | 8.14 | 1.00 | 0.06 | 1.00 | 7.37 | 1.00 | 1.00 | 1.00 | 0.19 |
| Mir6415 | 1.00 | 2.75 | 5.94 | 1.00 | 1.00 | 1.00 | 1.00 | 1.00 | 1.00 |
| Mir6417 | 1.00 | 1.00 | 3.66 | 1.00 | 1.00 | 1.00 | 1.00 | 1.00 | 3.50 |
| Mir6418 | 1.00 | 0.97 | 0.69 | 0.09 | 0.07 | 5.95 | 6.91 | 0.35 | 1.01 |
| Mir6481 | 0.10 | 1.00 | 0.38 | 0.22 | 0.22 | 0.26 | 1.00 | 0.86 | 0.25 |
| Mir6537 | 1.00 | 0.19 | 8.35 | 1.00 | 1.00 | 1.00 | 1.94 | 0.24 | 1.08 |
| Mir6538 | 5.76 | 1.00 | 1.00 | 5.67 | 0.22 | 0.24 | 1.04 | 0.52 | 1.04 |
| Mir6546 | 1.00 | 1.00 | 1.00 | 1.00 | 1.00 | 1.00 | 0.73 | 0.67 | 3.16 |
| Mir664 | 1.00 | 1.00 | 1.00 | 1.00 | 1.00 | 1.00 | 1.00 | 1.00 | 1.00 |
| Mir665 | 1.00 | 9.69 | 0.13 | 1.00 | 0.12 | 1.00 | 1.00 | 1.00 | 1.00 |
| Mir667 | 1.00 | 1.00 | 8.32 | 1.00 | 1.00 | 1.00 | 1.00 | 1.00 | 1.00 |
| Mir671 | 1.00 | 0.50 | 0.32 | 1.00 | 1.00 | 1.00 | 0.18 | 1.98 | 8.41 |
| Mir672 | 1.00 | 1.00 | 1.00 | 1.00 | 1.00 | 1.00 | 5.97 | 1.00 | 1.00 |
| Mir674 | 0.50 | 13.75 | 17.12 | 0.62 | 1.00 | 1.00 | 5.97 | 1.00 | 1.00 |
| Mir675 | 1.00 | 0.30 | 1.00 | 0.06 | 3.25 | 9.86 | 0.12 | 0.11 | 1.00 |
| Mir676 | 1.00 | 1.00 | 1.00 | 1.00 | 1.00 | 1.00 | 1.00 | 1.00 | 1.00 |
| Mir6769b | 172.50 | 1.00 | 174.99 | 1.00 | 155.18 | 1.00 | 51.30 | 0.47 | 44.37 |
| Mir678 | 0.10 | 0.32 | 0.02 | 1.00 | 1.00 | 1.00 | 0.09 | 13.19 | 1.00 |

Fig. 31- 72

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir5134 | 1.00 | 0.06 | 1.00 | 1.00 | 0.95 | 16.33 | 1.00 | 1.00 | 1.00 | 1.00 | 1.00 | 1.00 |
| Mir5135 | 1.05 | 0.07 | 1.00 | 0.07 | 0.02 | 15.43 | 1.00 | 1.00 | 0.07 | 1.00 | 1.00 | 1.00 |
| Mir5136 | 1.00 | 1.00 | 1.00 | 1.00 | 1.00 | 1.00 | 1.00 | 1.00 | 1.00 | 1.00 | 1.00 | 1.00 |
| Mir540 | 1.00 | 33.86 | 1.00 | 1.00 | 1.00 | 1.00 | 1.00 | 1.00 | 1.00 | 1.00 | 1.00 | 1.00 |
| Mir541 | 1.00 | 1.00 | 1.00 | 1.00 | 1.00 | 1.00 | 1.00 | 1.00 | 1.00 | 1.00 | 1.00 | 1.00 |
| Mir547 | 1.00 | 1.00 | 1.00 | 1.00 | 1.00 | 1.00 | 1.00 | 1.00 | 1.00 | 1.00 | 1.00 | 1.00 |
| Mir5615-2 | 1.00 | 1.00 | 1.00 | 1.00 | 1.00 | 1.00 | 1.00 | 1.00 | 1.00 | 1.00 | 1.00 | 1.00 |
| Mir5617 | 1.00 | 1.00 | 1.00 | 1.00 | 1.00 | 1.00 | 1.00 | 1.00 | 1.00 | 1.00 | 1.00 | 1.00 |
| Mir5618 | 1.00 | 1.00 | 442.54 | 1.00 | 0.01 | 1.00 | 1.00 | 1.00 | 1.00 | 1.00 | 1.00 | 1.00 |
| Mir5619 | 1.00 | 1.00 | 1.00 | 1.00 | 1.00 | 1.00 | 1.00 | 1.00 | 1.00 | 1.00 | 1.00 | 1.00 |
| Mir5620 | 1.20 | 1.00 | 117.55 | 69.42 | 1.00 | 0.01 | 1.00 | 1.00 | 1.00 | 1.00 | 1.00 | 1.00 |
| Mir5621 | 0.02 | 45.06 | 56.76 | 0.03 | 1.00 | 0.02 | 1.00 | 1.00 | 1.00 | 1.00 | 1.00 | 1.00 |
| Mir5622 | 1.00 | 1.00 | 75.45 | 1.00 | 1.00 | 1.00 | 1.00 | 1.00 | 1.00 | 1.00 | 1.00 | 1.00 |
| Mir5623 | 1.00 | 27.88 | 1.00 | 1.00 | 0.99 | 1.00 | 1.00 | 1.00 | 1.00 | 1.00 | 1.00 | 1.00 |
| Mir5625 | 1.00 | 1.00 | 1.00 | 0.04 | 1.00 | 1.00 | 1.00 | 1.00 | 1.00 | 1.00 | 1.00 | 1.00 |
| Mir568 | 0.80 | 0.77 | 0.62 | 1.13 | 41.30 | 1.18 | 20.86 | 0.11 | 1.03 | 1.00 | 1.00 | 1.00 |
| Mir5709 | 10.09 | 1.00 | 1.00 | 1.00 | 1.00 | 1.00 | 1.00 | 1.00 | 1.00 | 1.00 | 1.00 | 1.00 |
| Mir5710 | 1.00 | 1.00 | 1.00 | 0.04 | 1.00 | 57.77 | 1.00 | 1.00 | 1.00 | 1.00 | 1.00 | 1.00 |
| Mir599 | 1.00 | 1.00 | 1.00 | 9.39 | 1.00 | 1.00 | 1.00 | 1.00 | 1.00 | 1.00 | 0.54 | 2.73 |
| Mir6236 | 4.28 | 0.88 | 1.20 | 0.30 | 0.68 | 1.08 | 0.68 | 0.87 | 0.87 | 1.32 | 1.00 | 1.00 |
| Mir6244 | 0.67 | 1.52 | 0.34 | 0.49 | 0.53 | 0.85 | 0.84 | 2.57 | 2.56 | 1.00 | 1.00 | 1.00 |
| Mir6337 | 1.00 | 1.00 | 1.00 | 1.00 | 1.00 | 1.00 | 1.00 | 1.00 | 1.00 | 1.00 | 1.00 | 1.00 |
| Mir6338 | 1.00 | 1.00 | 1.00 | 1.00 | 1.00 | 1.00 | 1.00 | 1.00 | 1.00 | 1.00 | 1.00 | 1.00 |
| Mir6340 | 1.33 | 0.75 | 0.96 | 1.00 | 0.59 | 1.25 | 0.42 | 13.01 | 0.86 | 1.00 | 1.00 | 1.00 |
| Mir6356 | 1.00 | 1.00 | 1.00 | 1.00 | 1.00 | 1.00 | 1.00 | 1.00 | 1.00 | 1.00 | 1.00 | 1.00 |
| Mir6357 | 0.60 | 1.80 | 0.61 | 1.05 | 5.13 | 1.05 | 0.54 | 0.06 | 0.78 | 1.00 | 1.00 | 1.00 |
| Mir6358 | 0.08 | 1.00 | 1.00 | 1.00 | 1.00 | 1.00 | 1.00 | 1.00 | 1.00 | 1.00 | 1.00 | 1.00 |
| Mir6359 | 1.00 | 11.52 | 0.06 | 21.41 | 6.59 | 0.27 | 1.00 | 1.00 | 1.00 | 1.00 | 1.00 | 1.00 |
| Mir6363 | 0.02 | 0.09 | 2.51 | 2.20 | 0.55 | 0.94 | 3.53 | 5.68 | 3.64 | 1.00 | 1.00 | 1.00 |
| Mir6365 | 1.00 | 0.50 | 1.00 | 1.00 | 1.00 | 1.00 | 1.00 | 1.00 | 1.00 | 1.00 | 1.00 | 1.00 |
| Mir6366 | 1.00 | 1.00 | 1.00 | 1.00 | 1.00 | 1.00 | 1.00 | 1.00 | 1.00 | 1.00 | 1.00 | 1.00 |
| Mir6368 | 1.00 | 8.95 | 1.00 | 1.00 | 1.00 | 1.00 | 1.00 | 1.00 | 1.00 | 1.00 | 1.00 | 1.00 |
| Mir6386 | 7.10 | 2.72 | 2.01 | 1.32 | 0.54 | 3.16 | 1.00 | 0.25 | 1.00 | 1.00 | 1.00 | 1.00 |
| Mir6387 | 0.53 | 0.06 | 0.77 | 0.92 | 0.06 | 1.22 | 1.00 | 1.00 | 1.00 | 1.00 | 1.00 | 1.00 |
| Mir6389 | 1.00 | 1.00 | 1.00 | 1.00 | 1.00 | 1.00 | 1.00 | 1.00 | 1.00 | 1.00 | 1.00 | 1.00 |
| Mir6391 | 1.00 | 5.99 | 1.00 | 1.00 | 1.00 | 1.00 | 1.00 | 1.00 | 1.00 | 1.00 | 1.00 | 1.00 |
| Mir6392 | 2.64 | 0.71 | 1.90 | 1.00 | 1.00 | 1.00 | 1.00 | 1.00 | 1.00 | 1.00 | 1.00 | 1.00 |
| Mir6395 | 1.08 | 0.52 | 0.48 | 1.30 | 0.89 | 0.63 | 0.16 | 1.00 | 1.00 | 1.00 | 1.00 | 1.00 |
| Mir6396 | 2.92 | 0.58 | 0.70 | 1.00 | 1.00 | 4.09 | 1.00 | 1.00 | 1.00 | 1.00 | 1.00 | 1.00 |
| Mir6397 | 1.00 | 8.95 | 9.35 | 1.00 | 0.48 | 0.13 | 1.00 | 1.00 | 1.00 | 1.00 | 1.00 | 1.00 |
| Mir6399 | 1.19 | 1.00 | 13.12 | 1.00 | 1.00 | 23.36 | 1.00 | 9.82 | 1.00 | 1.00 | 1.00 | 1.00 |
| Mir6400 | 1.00 | 1.00 | 1.00 | 1.00 | 1.00 | 8.63 | 1.00 | 1.00 | 1.00 | 1.00 | 1.00 | 1.00 |
| Mir6403 | 0.07 | 0.99 | 2.08 | 0.49 | 0.94 | 1.12 | 1.00 | 2.55 | 0.31 | 1.00 | 1.00 | 1.00 |
| Mir6404 | 1.00 | 1.00 | 1.00 | 1.00 | 1.00 | 1.00 | 1.00 | 1.00 | 1.00 | 1.00 | 1.00 | 1.00 |
| Mir6405 | 1.00 | 1.00 | 1.00 | 1.00 | 1.00 | 1.00 | 1.00 | 1.00 | 1.00 | 1.00 | 1.00 | 1.00 |
| Mir6406 | 6.62 | 3.19 | 1.02 | 1.00 | 1.00 | 1.00 | 0.39 | 0.54 | 0.93 | 1.00 | 1.00 | 1.00 |
| Mir6407 | 1.00 | 1.00 | 0.15 | 1.00 | 1.00 | 1.00 | 1.00 | 1.00 | 1.00 | 1.00 | 1.00 | 1.00 |
| Mir6415 | 6.59 | 0.15 | 6.56 | 1.00 | 1.00 | 1.00 | 1.00 | 1.00 | 1.00 | 1.00 | 1.00 | 1.00 |
| Mir6417 | 0.26 | 1.00 | 7.00 | 1.00 | 1.00 | 1.19 | 2.37 | 1.00 | 1.00 | 1.00 | 1.00 | 1.00 |
| Mir6418 | 0.50 | 0.33 | 0.61 | 0.79 | 1.03 | 0.74 | 0.42 | 6.02 | 1.00 | 1.00 | 1.00 | 1.00 |
| Mir6481 | 2.61 | 0.34 | 0.37 | 1.13 | 4.37 | 1.17 | 1.00 | 0.29 | 1.00 | 1.00 | 1.00 | 1.00 |
| Mir6537 | 1.00 | 1.00 | 4.98 | 1.00 | 3.85 | 1.00 | 1.00 | 1.00 | 1.00 | 1.00 | 1.00 | 1.00 |
| Mir6538 | 1.00 | 1.00 | 1.00 | 1.00 | 1.00 | 1.00 | 1.00 | 1.00 | 1.00 | 1.00 | 1.00 | 1.00 |
| Mir6546 | 1.00 | 1.00 | 1.00 | 41.25 | 1.00 | 1.00 | 1.00 | 1.00 | 1.00 | 1.00 | 1.00 | 1.00 |
| Mir664 | 1.00 | 1.00 | 1.00 | 1.00 | 1.00 | 1.00 | 1.00 | 1.00 | 1.00 | 1.00 | 1.00 | 1.00 |
| Mir665 | 1.00 | 1.00 | 1.00 | 1.00 | 1.00 | 1.00 | 1.00 | 1.00 | 1.00 | 1.00 | 1.00 | 1.00 |
| Mir667 | 1.00 | 1.00 | 1.00 | 1.00 | 1.00 | 1.00 | 1.00 | 1.00 | 0.14 | 1.00 | 1.00 | 1.00 |
| Mir671 | 1.00 | 4.95 | 7.52 | 8.46 | 23.10 | 1.00 | 7.76 | 0.74 | 0.07 | 1.00 | 1.00 | 1.00 |
| Mir672 | 1.00 | 1.00 | 1.00 | 1.00 | 1.00 | 1.00 | 1.00 | 1.00 | 1.00 | 1.00 | 1.00 | 1.00 |
| Mir674 | 1.08 | 1.00 | 0.15 | 1.00 | 1.00 | 1.00 | 1.00 | 1.00 | 0.19 | 1.00 | 1.00 | 1.00 |
| Mir675 | 1.29 | 4.44 | 0.05 | 1.00 | 1.00 | 1.00 | 1.00 | 1.00 | 1.00 | 1.00 | 1.00 | 1.00 |
| Mir676 | 1.00 | 1.00 | 1.00 | 1.00 | 1.00 | 1.00 | 5.91 | 1.00 | 1.00 | 1.00 | 1.00 | 1.00 |
| Mir6769b | 1.00 | 57.19 | 1.00 | 1.00 | 1.00 | 1.00 | 1.00 | 0.02 | 1.00 | 1.00 | 1.00 | 1.00 |
| Mir678 | 0.78 | 1.00 | 62.12 | 0.06 | 15.75 | 0.06 | 0.71 | 1.88 | 1.00 | 1.00 | 1.00 | 1.00 |

Fig. 31-73

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir679 | 1.00 | 19.66 | 1.00 | 1.00 | 1.00 | 1.00 | 1.00 | 1.00 | 1.00 |
| Mir680-1 | 1.00 | 1.00 | 1.00 | 1.00 | 1.00 | 1.00 | 1.00 | 1.00 | 1.00 |
| Mir680-2 | 0.48 | 1.53 | 0.34 | 5.98 | 1.00 | 1.00 | 1.00 | 4.44 | 0.18 |
| Mir681 | 1.00 | 1.00 | 1.00 | 0.42 | 1.01 | 1.03 | 1.00 | 1.00 | 1.00 |
| Mir682 | 1.16 | 1.14 | 0.89 | 1.02 | 1.18 | 1.01 | 1.00 | 1.20 | 1.14 |
| Mir686 | 1.00 | 0.95 | 0.55 | 1.90 | 0.42 | 1.33 | 0.75 | 1.00 | 1.01 |
| Mir687 | 1.00 | 1.00 | 1.00 | 12.50 | 13.89 | 1.00 | 1.00 | 1.00 | 12.53 |
| Mir688 | 0.04 | 1.00 | 0.05 | 0.04 | 33.74 | 1.00 | 1.00 | 1.00 | 1.00 |
| Mir6897 | 1.00 | 1.00 | 47.59 | 1.00 | 1.00 | 1.00 | 1.00 | 1.00 | 1.00 |
| Mir6898 | 1.00 | 1.00 | 1.00 | 1.00 | 1.00 | 1.00 | 1.00 | 1.00 | 23.35 |
| Mir6900 | 1.00 | 1.00 | 1.00 | 1.00 | 1.00 | 1.00 | 1.00 | 1.00 | 1.00 |
| Mir6902 | 1.00 | 1.00 | 1.00 | 1.00 | 1.00 | 1.00 | 1.00 | 72.02 | 1.00 |
| Mir6904 | 0.03 | 1.66 | 1.00 | 1.00 | 0.58 | 84.23 | 46.82 | 0.02 | 1.00 |
| Mir6905 | 1.00 | 0.02 | 26.43 | 1.00 | 1.00 | 32.53 | 1.00 | 0.01 | 0.04 |
| Mir6907 | 0.93 | 1.74 | 1.00 | 1.19 | 0.02 | 0.03 | 1.00 | 29.59 | 0.05 |
| Mir6908 | 1.00 | 1.00 | 1.00 | 1.00 | 0.58 | 1.00 | 1.00 | 1.00 | 1.00 |
| Mir6909 | 1.00 | 1.00 | 1.00 | 1.00 | 0.01 | 3.04 | 0.01 | 1.00 | 1.00 |
| Mir6910 | 0.01 | 0.90 | 1.00 | 1.00 | 76.18 | 1.00 | 54.03 | 1.00 | 1.00 |
| Mir6911 | 1.00 | 1.00 | 54.69 | 1.00 | 0.02 | 1.00 | 1.00 | 1.00 | 1.00 |
| Mir6912 | 1.00 | 25.19 | 51.12 | 1.00 | 1.00 | 1.00 | 1.00 | 1.00 | 1.00 |
| Mir6913 | 1.00 | 31.61 | 67.71 | 1.00 | 1.00 | 1.00 | 1.00 | 59.82 | 1.00 |
| Mir6914 | 1.00 | 1.00 | 1.00 | 1.00 | 1.00 | 1.00 | 1.00 | 1.00 | 41.17 |
| Mir6915 | 0.46 | 0.44 | 0.90 | 0.65 | 56.45 | 0.03 | 39.67 | 1.00 | 1.00 |
| Mir6916 | 0.83 | 0.00 | 0.01 | 1.00 | 1.00 | 1.00 | 1.00 | 0.01 | 0.93 |
| Mir6917 | 1.00 | 1.00 | 1.00 | 1.00 | 1.00 | 1.00 | 1.00 | 1.00 | 0.02 |
| Mir6918 | 1.00 | 1.00 | 1.00 | 0.01 | 0.00 | 1.00 | 1.00 | 1.00 | 1.00 |
| Mir6919 | 0.88 | 87.51 | 0.02 | 1.00 | 1.00 | 1.00 | 1.00 | 65.41 | 1.00 |
| Mir6920 | 1.00 | 1.00 | 0.04 | 1.00 | 1.00 | 1.00 | 35.93 | 0.03 | 70.90 |
| Mir6921 | 0.06 | 0.90 | 29.11 | 0.57 | 1.00 | 1.01 | 0.60 | 1.79 | 1.13 |
| Mir692-1 | 1.00 | 4.42 | 0.21 | 0.05 | 1.00 | 1.00 | 0.10 | 0.55 | 0.87 |
| Mir6922 | 33.55 | 31.61 | 0.89 | 1.00 | 1.00 | 1.00 | 0.48 | 0.02 | 0.89 |
| Mir6924 | 1.00 | 1.00 | 1.00 | 1.00 | 1.00 | 1.00 | 0.01 | 0.01 | 1.00 |
| Mir6925 | 75.36 | 0.85 | 0.95 | 43.07 | 51.38 | 0.03 | 1.00 | 0.86 | 0.02 |
| Mir6926 | 1.00 | 27.43 | 1.00 | 1.00 | 1.00 | 1.00 | 1.00 | 1.00 | 1.00 |
| Mir6927 | 0.87 | 1.00 | 47.87 | 1.00 | 46.94 | 1.00 | 1.00 | 29.59 | 1.00 |
| Mir6928 | 1.00 | 1.00 | 1.00 | 50.01 | 1.00 | 32.53 | 1.00 | 1.00 | 1.00 |
| Mir6929 | 0.54 | 0.45 | 0.92 | 1.00 | 1.00 | 43.37 | 1.00 | 1.00 | 1.00 |
| Mir6930 | 1.00 | 1.00 | 1.00 | 1.00 | 61.76 | 38.37 | 0.02 | 1.00 | 92.33 |
| Mir6931 | 0.17 | 0.73 | 0.50 | 1.00 | 1.00 | 1.00 | 1.00 | 1.00 | 1.00 |
| Mir6933 | 1.00 | 1.00 | 1.00 | 1.00 | 1.00 | 1.00 | 1.00 | 1.00 | 1.00 |
| Mir6934 | 1.00 | 1.00 | 1.00 | 1.00 | 1.00 | 1.00 | 1.00 | 1.00 | 1.00 |
| Mir6935 | 2.66 | 1.18 | 0.75 | 0.37 | 0.01 | 1.00 | 1.00 | 1.00 | 1.00 |
| Mir6936 | 100.18 | 1.00 | 101.14 | 1.00 | 1.00 | 1.00 | 1.00 | 0.00 | 0.01 |
| Mir6937 | 1.00 | 0.02 | 1.72 | 69.09 | 85.26 | 3.11 | 1.00 | 65.52 | 0.02 |
| Mir6938 | 1.00 | 1.00 | 1.00 | 0.01 | 1.00 | 1.00 | 67.86 | 1.00 | 73.21 |
| Mir6939 | 0.02 | 35.21 | 0.02 | 29.08 | 66.21 | 22.51 | 51.70 | 1.00 | 1.00 |
| Mir6940 | 1.00 | 1.00 | 1.00 | 1.00 | 1.00 | 1.00 | 1.00 | 1.00 | 1.00 |
| Mir6941 | 63.55 | 0.01 | 1.00 | 1.00 | 1.00 | 1.00 | 1.00 | 1.00 | 1.00 |
| Mir6942 | 1.69 | 0.25 | 0.30 | 0.01 | 4.59 | 0.51 | 1.04 | 0.78 | 1.00 |
| Mir6943 | 35.76 | 1.00 | 1.00 | 0.02 | 1.00 | 1.00 | 1.00 | 1.00 | 1.00 |
| Mir6944 | 13.44 | 1.00 | 0.12 | 1.00 | 1.00 | 1.00 | 1.00 | 1.00 | 1.00 |
| Mir6945 | 1.77 | 0.02 | 87.15 | 1.00 | 1.00 | 1.00 | 1.00 | 1.00 | 1.00 |
| Mir6946 | 1.00 | 1.70 | 0.95 | 1.16 | 166.97 | 1.00 | 0.03 | 34.91 | 41.17 |
| Mir6947 | 1.00 | 1.00 | 1.00 | 1.00 | 1.00 | 50.35 | 1.00 | 1.00 | 0.02 |
| Mir6948 | 0.02 | 0.86 | 93.02 | 305.12 | 4.50 | 1.00 | 1.10 | 0.29 | 1.00 |
| Mir6950 | 1.00 | 1.00 | 21.89 | 1.00 | 1.00 | 1.00 | 1.00 | 1.00 | 1.00 |
| Mir6951 | 1.00 | 1.00 | 1.00 | 1.00 | 1.00 | 1.00 | 1.00 | 0.04 | 26.58 |
| Mir6953 | 146.82 | 1.28 | 0.92 | 0.99 | 1.13 | 114.98 | 1.00 | 50.37 | 0.47 |
| Mir6954 | 0.41 | 0.34 | 3.66 | 0.01 | 1.00 | 1.04 | 1.00 | 1.00 | 1.70 |
| Mir6958 | 0.68 | 1.15 | 0.19 | 0.02 | 1.15 | 0.04 | 1.10 | 34.37 | 31.68 |
| Mir6959 | 1.00 | 1.00 | 1.00 | 29.08 | 1.00 | 1.00 | 1.00 | 1.00 | 1.00 |
| Mir6960 | 1.00 | 1.00 | 1.00 | 1.00 | 1.00 | 1.00 | 1.00 | 1.00 | 1.00 |
| Mir6961 | 1.00 | 29.42 | 1.00 | 1.00 | 1.00 | 1.00 | 1.00 | 1.00 | 1.00 |
| Mir6962 | 1.00 | 1.00 | 1.00 | 1.00 | 1.00 | 1.00 | 1.00 | 1.00 | 1.00 |

Fig. 31-74

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir679 | 1.00 | 1.00 | 1.00 | 1.00 | 1.00 | 1.00 | 1.00 | 1.00 | 1.00 |
| Mir680-1 | 1.00 | 1.00 | 1.00 | 1.00 | 1.00 | 1.00 | 1.00 | 1.00 | 0.17 |
| Mir680-2 | 0.51 | 2.13 | 0.44 | 0.93 | 1.00 | 1.00 | 0.18 | 6.61 | 2.51 |
| Mir681 | 0.55 | 0.27 | 0.26 | 1.00 | 1.00 | 1.00 | 1.77 | 0.18 | 1.09 |
| Mir682 | 1.12 | 1.34 | 1.00 | 1.06 | 1.16 | 1.05 | 0.89 | 1.15 | 0.94 |
| Mir686 | 1.23 | 1.75 | 1.11 | 1.65 | 0.85 | 1.50 | 0.39 | 0.63 | 0.56 |
| Mir687 | 22.65 | 22.95 | 0.12 | 8.43 | 0.12 | 1.00 | 13.06 | 0.74 | 0.82 |
| Mir688 | 1.03 | 1.00 | 1.00 | 0.05 | 1.00 | 1.00 | 1.00 | 1.00 | 1.00 |
| Mir6897 | 1.00 | 1.00 | 1.00 | 1.00 | 0.02 | 1.00 | 1.00 | 0.01 | 1.00 |
| Mir6898 | 1.00 | 1.00 | 0.07 | 18.34 | 1.00 | 1.00 | 1.00 | 1.00 | 0.05 |
| Mir6900 | 1.00 | 1.00 | 1.00 | 1.00 | 1.00 | 1.00 | 1.00 | 1.00 | 1.00 |
| Mir6902 | 1.00 | 0.03 | 1.00 | 1.00 | 1.00 | 1.00 | 1.00 | 1.00 | 1.00 |
| Mir6904 | 26.20 | 0.66 | 0.56 | 1.00 | 0.04 | 1.00 | 157.13 | 0.39 | 0.90 |
| Mir6905 | 1.02 | 3.11 | 0.54 | 45.37 | 45.87 | 0.04 | 0.01 | 272.12 | 2.08 |
| Mir6907 | 2.87 | 2.98 | 21.13 | 1.00 | 42.95 | 0.04 | 1.01 | 0.52 | 0.46 |
| Mir6908 | 1.00 | 35.24 | 39.83 | 0.03 | 37.84 | 0.02 | 1.00 | 1.00 | 62.54 |
| Mir6909 | 0.02 | 38.23 | 1.00 | 1.00 | 1.00 | 1.00 | 1.00 | 1.00 | 1.00 |
| Mir6910 | 0.02 | 0.37 | 0.02 | 1.00 | 1.00 | 1.00 | 1.00 | 1.13 | 0.65 |
| Mir6911 | 1.00 | 0.98 | 0.04 | 1.00 | 1.00 | 1.00 | 1.00 | 1.00 | 1.06 |
| Mir6912 | 0.04 | 1.94 | 0.04 | 1.00 | 1.00 | 24.21 | 2.93 | 0.40 | 67.13 |
| Mir6913 | 55.80 | 1.94 | 0.03 | 1.00 | 0.03 | 1.00 | 1.01 | 1.00 | 0.50 |
| Mir6914 | 1.00 | 1.00 | 1.00 | 1.00 | 1.00 | 1.00 | 1.00 | 1.00 | 0.82 |
| Mir6915 | 1.03 | 1.58 | 2.15 | 0.48 | 2.00 | 6.42 | 0.70 | 0.75 | 0.55 |
| Mir6916 | 0.01 | 151.89 | 0.01 | 6.02 | 0.76 | 0.19 | 0.01 | 1.00 | 67.95 |
| Mir6917 | 1.00 | 1.00 | 1.00 | 1.00 | 1.00 | 1.00 | 1.00 | 1.00 | 1.00 |
| Mir6918 | 1.00 | 1.00 | 57.96 | 1.00 | 1.00 | 1.00 | 1.00 | 0.01 | 1.00 |
| Mir6919 | 1.00 | 0.01 | 2.12 | 1.00 | 0.02 | 1.00 | 1.00 | 90.74 | 1.00 |
| Mir6920 | 0.05 | 0.50 | 0.05 | 1.00 | 1.00 | 0.04 | 1.01 | 0.02 | 0.01 |
| Mir6921 | 0.48 | 3.01 | 0.60 | 0.08 | 2.04 | 0.90 | 1.90 | 3.03 | 1.99 |
| Mir692-1 | 0.55 | 1.09 | 0.40 | 4.06 | 1.00 | 1.00 | 1.00 | 1.07 | 5.22 |
| Mir6922 | 0.42 | 0.98 | 1.08 | 1.00 | 1.00 | 0.92 | 1.00 | 1.00 | 1.00 |
| Mir6924 | 0.26 | 2.02 | 4.28 | 46.34 | 1.00 | 1.00 | 0.95 | 0.27 | 0.94 |
| Mir6925 | 1.04 | 1.00 | 1.08 | 1.08 | 0.36 | 24.21 | 41.27 | 0.02 | 1.10 |
| Mir6926 | 1.00 | 1.00 | 1.00 | 1.00 | 1.00 | 1.00 | 1.00 | 1.00 | 0.02 |
| Mir6927 | 0.03 | 19.95 | 0.57 | 1.00 | 1.00 | 0.04 | 0.01 | 85.50 | 1.36 |
| Mir6928 | 1.00 | 1.00 | 24.02 | 1.00 | 1.00 | 1.00 | 82.04 | 0.02 | 33.81 |
| Mir6929 | 51.90 | 29.25 | 27.62 | 0.09 | 0.82 | 0.43 | 52.71 | 62.83 | 1.00 |
| Mir6930 | 1.00 | 1.00 | 27.47 | 1.00 | 0.04 | 1.00 | 1.00 | 1.00 | 1.00 |
| Mir6931 | 16.70 | 18.62 | 17.59 | 1.00 | 0.06 | 17.71 | 1.00 | 1.00 | 1.00 |
| Mir6933 | 1.00 | 1.00 | 1.00 | 1.00 | 1.00 | 1.00 | 1.00 | 1.00 | 17.73 |
| Mir6934 | 1.00 | 1.00 | 1.00 | 1.00 | 1.00 | 1.00 | 1.00 | 1.00 | 1.00 |
| Mir6935 | 2.43 | 0.59 | 2.41 | 1.52 | 1.02 | 0.96 | 0.74 | 1.35 | 0.77 |
| Mir6936 | 0.99 | 1.00 | 88.50 | 2.17 | 1.00 | 0.01 | 224.66 | 2.21 | 1.00 |
| Mir6937 | 0.03 | 0.56 | 1.00 | 1.00 | 32.40 | 0.44 | 1.00 | 75.12 | 0.02 |
| Mir6938 | 1.00 | 69.97 | 37.33 | 0.03 | 1.00 | 1.00 | 0.01 | 81.86 | 1.00 |
| Mir6939 | 47.82 | 1.02 | 17.69 | 1.00 | 0.99 | 1.00 | 2.20 | 0.26 | 2.17 |
| Mir6940 | 21.38 | 1.00 | 1.00 | 1.00 | 1.00 | 1.00 | 1.00 | 1.00 | 1.00 |
| Mir6941 | 2.10 | 0.01 | 0.34 | 1.00 | 1.00 | 1.00 | 1.00 | 1.00 | 1.00 |
| Mir6942 | 1.09 | 1.95 | 44.08 | 0.02 | 1.00 | 47.42 | 1.01 | 1.07 | 0.64 |
| Mir6943 | 1.00 | 28.08 | 31.65 | 1.00 | 1.00 | 1.00 | 1.01 | 0.02 | 0.02 |
| Mir6944 | 1.00 | 1.00 | 1.00 | 1.00 | 1.00 | 1.00 | 1.00 | 1.00 | 1.00 |
| Mir6945 | 1.09 | 2.03 | 0.04 | 0.87 | 0.58 | 0.70 | 0.02 | 1.00 | 2.08 |
| Mir6946 | 48.18 | 2.99 | 2.23 | 24.50 | 0.04 | 25.87 | 0.01 | 0.01 | 0.63 |
| Mir6947 | 1.00 | 0.03 | 0.03 | 0.03 | 1.00 | 1.00 | 1.00 | 0.02 | 1.00 |
| Mir6948 | 0.50 | 0.69 | 1.05 | 50.30 | 0.50 | 0.02 | 0.93 | 0.47 | 0.76 |
| Mir6950 | 1.00 | 1.00 | 1.00 | 1.00 | 1.00 | 1.00 | 1.00 | 1.00 | 0.03 |
| Mir6951 | 31.54 | 0.06 | 1.00 | 1.00 | 1.00 | 16.71 | 0.02 | 1.04 | 23.64 |
| Mir6953 | 0.21 | 1.03 | 1.14 | 0.92 | 79.57 | 0.92 | 1.82 | 1.55 | 2.66 |
| Mir6954 | 0.51 | 0.33 | 2.70 | 1.20 | 0.33 | 51.77 | 97.80 | 113.17 | 0.01 |
| Mir6958 | 18.88 | 1.25 | 1.12 | 0.30 | 0.54 | 59.18 | 1.22 | 2.37 | 0.96 |
| Mir6959 | 1.00 | 1.00 | 17.69 | 1.00 | 1.00 | 1.00 | 1.00 | 0.02 | 1.00 |
| Mir6960 | 1.00 | 1.00 | 1.00 | 1.00 | 1.00 | 1.00 | 94.35 | 1.00 | 1.00 |
| Mir6961 | 1.00 | 1.00 | 1.00 | 1.00 | 1.00 | 1.00 | 1.00 | 0.02 | 1.00 |
| Mir6962 | 37.76 | 1.00 | 0.03 | 46.34 | 1.00 | 1.00 | 1.00 | 1.00 | 1.00 |

Fig. 31-75

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir679 | 1.00 | 1.00 | 70.32 | 1.00 | 1.00 | 1.00 | 1.00 | 1.00 | 1.00 |
| Mir680-1 | 1.00 | 1.00 | 1.00 | 5.39 | 1.00 | 1.00 | 1.00 | 1.00 | 1.00 |
| Mir680-2 | 4.49 | 1.00 | 1.00 | 0.23 | 0.22 | 1.00 | 0.78 | 2.23 | 1.07 |
| Mir681 | 0.99 | 0.96 | 0.24 | 1.00 | 1.00 | 1.00 | 4.34 | 0.86 | 6.94 |
| Mir682 | 1.00 | 1.19 | 0.87 | 1.11 | 1.33 | 0.73 | 1.03 | 0.93 | 1.10 |
| Mir686 | 0.21 | 0.39 | 1.90 | 1.58 | 0.54 | 3.34 | 0.25 | 0.19 | 0.41 |
| Mir687 | 1.00 | 0.08 | 1.00 | 0.05 | 0.34 | 9.12 | 1.00 | 0.11 | 1.00 |
| Mir688 | 0.03 | 1.00 | 0.02 | 1.15 | 1.08 | 21.36 | 1.00 | 14.91 | 1.00 |
| Mir6897 | 1.00 | 1.00 | 1.00 | 1.00 | 1.00 | 1.00 | 1.00 | 1.00 | 1.00 |
| Mir6898 | 1.00 | 1.00 | 1.00 | 1.00 | 1.00 | 1.00 | 4.21 | 4.27 | 46.24 |
| Mir6900 | 1.00 | 1.00 | 1.00 | 1.00 | 1.00 | 1.00 | 1.00 | 45.21 | 1.00 |
| Mir6902 | 1.00 | 0.01 | 1.00 | 1.00 | 1.00 | 1.00 | 1.00 | 0.03 | 32.16 |
| Mir6904 | 1.07 | 0.24 | 11.21 | 1.00 | 190.66 | 1.00 | 0.01 | 2.69 | 79.25 |
| Mir6905 | 80.04 | 1.00 | 1.00 | 1.00 | 42.07 | 30.85 | 0.73 | 0.13 | 0.32 |
| Mir6907 | 0.54 | 1.00 | 1.00 | 43.29 | 0.96 | 1.00 | 1.09 | 76.39 | 2.99 |
| Mir6908 | 0.90 | 1.00 | 58.23 | 0.01 | 0.01 | 1.00 | 1.00 | 35.37 | 1.00 |
| Mir6909 | 1.00 | 1.00 | 1.00 | 1.00 | 1.00 | 61.60 | 1.00 | 1.00 | 1.00 |
| Mir6910 | 1.00 | 1.00 | 1.00 | 1.00 | 0.02 | 1.00 | 1.00 | 0.96 | 0.04 |
| Mir6911 | 0.02 | 50.38 | 1.00 | 1.00 | 1.00 | 1.00 | 0.02 | 1.71 | 0.98 |
| Mir6912 | 40.27 | 0.02 | 30.78 | 1.00 | 1.00 | 1.00 | 2.18 | 1.00 | 1.01 |
| Mir6913 | 1.00 | 1.00 | 1.00 | 77.73 | 1.00 | 1.00 | 0.55 | 0.45 | 1.00 |
| Mir6914 | 0.02 | 0.02 | 1.00 | 1.00 | 1.00 | 1.00 | 1.00 | 1.00 | 0.04 |
| Mir6915 | 1.63 | 0.97 | 1.02 | 108.18 | 3.13 | 0.51 | 1.10 | 0.48 | 0.04 |
| Mir6916 | 1.00 | 1.00 | 2.07 | 0.01 | 89.70 | 110.16 | 0.01 | 1.73 | 0.50 |
| Mir6917 | 1.00 | 1.00 | 1.00 | 1.00 | 1.00 | 1.00 | 1.00 | 1.00 | 1.00 |
| Mir6918 | 1.00 | 1.00 | 1.00 | 1.00 | 1.00 | 1.00 | 0.01 | 1.00 | 59.31 |
| Mir6919 | 1.00 | 1.00 | 1.00 | 1.00 | 115.94 | 61.60 | 1.00 | 38.28 | 1.00 |
| Mir6920 | 84.09 | 1.00 | 0.04 | 0.03 | 1.00 | 1.00 | 1.00 | 0.04 | 1.00 |
| Mir6921 | 41.87 | 1.00 | 0.06 | 0.45 | 0.43 | 1.85 | 13.92 | 11.43 | 0.04 |
| Mir692-1 | 1.00 | 1.00 | 1.00 | 1.00 | 1.00 | 4.30 | 4.42 | 0.13 | 3.89 |
| Mir6922 | 1.00 | 135.20 | 1.00 | 0.01 | 1.00 | 0.73 | 0.03 | 1.00 | 1.00 |
| Mir6924 | 1.00 | 1.00 | 1.00 | 1.00 | 1.00 | 1.00 | 0.03 | 0.01 | 1.00 |
| Mir6925 | 0.02 | 1.00 | 1.00 | 0.31 | 2.02 | 3.25 | 1.00 | 1.00 | 1.00 |
| Mir6926 | 1.00 | 1.00 | 1.00 | 1.00 | 1.00 | 1.00 | 27.95 | 22.87 | 0.02 |
| Mir6927 | 1.00 | 0.02 | 1.07 | 1.00 | 0.53 | 0.02 | 1.00 | 1.00 | 0.05 |
| Mir6928 | 0.54 | 90.15 | 1.61 | 1.33 | 1.00 | 0.02 | 0.02 | 1.00 | 64.71 |
| Mir6929 | 54.03 | 61.56 | 0.01 | 0.02 | 0.01 | 1.08 | 1.62 | 0.29 | 5.42 |
| Mir6930 | 1.00 | 1.00 | 1.00 | 1.00 | 1.00 | 1.00 | 1.00 | 1.00 | 1.00 |
| Mir6931 | 0.01 | 0.03 | 1.00 | 1.00 | 1.00 | 1.00 | 1.00 | 1.00 | 1.00 |
| Mir6933 | 1.00 | 1.00 | 1.00 | 1.00 | 1.00 | 1.00 | 1.00 | 11.71 | 1.00 |
| Mir6934 | 1.00 | 1.00 | 1.00 | 1.00 | 1.00 | 1.00 | 1.00 | 1.00 | 1.00 |
| Mir6935 | 1.00 | 86.33 | 0.02 | 89.21 | 256.87 | 1.14 | 0.01 | 3.64 | 102.49 |
| Mir6936 | 1.00 | 1.00 | 198.26 | 1.00 | 1.00 | 188.33 | 1.12 | 1.00 | 0.98 |
| Mir6937 | 1.00 | 1.00 | 47.64 | 0.02 | 1.00 | 0.02 | 1.00 | 0.01 | 0.03 |
| Mir6938 | 1.00 | 97.84 | 0.01 | 1.00 | 1.00 | 1.00 | 0.03 | 1.00 | 1.01 |
| Mir6939 | 34.71 | 1.00 | 1.98 | 0.03 | 0.02 | 1.80 | 1.00 | 1.00 | 1.00 |
| Mir6940 | 92.13 | 1.00 | 0.03 | 1.00 | 1.00 | 1.00 | 1.00 | 0.04 | 1.00 |
| Mir6941 | 1.00 | 1.00 | 1.00 | 1.00 | 1.00 | 0.01 | 1.00 | 1.00 | 1.00 |
| Mir6942 | 1.00 | 2.01 | 0.50 | 132.89 | 0.01 | 2.21 | 0.74 | 0.91 | 0.02 |
| Mir6943 | 60.14 | 1.00 | 1.00 | 70.81 | 1.00 | 1.00 | 1.00 | 1.00 | 0.04 |
| Mir6944 | 1.00 | 17.07 | 1.00 | 1.00 | 16.29 | 0.06 | 1.00 | 5.72 | 0.54 |
| Mir6945 | 0.93 | 0.34 | 1.53 | 0.01 | 0.01 | 0.03 | 0.04 | 0.04 | 1.00 |
| Mir6946 | 1.00 | 1.00 | 0.02 | 0.02 | 3.13 | 33.45 | 0.04 | 0.96 | 1.00 |
| Mir6947 | 1.00 | 1.00 | 1.00 | 1.00 | 1.00 | 1.00 | 34.91 | 1.00 | 0.03 |
| Mir6948 | 1.18 | 0.00 | 1.00 | 1.00 | 3.28 | 0.02 | 0.01 | 4.42 | 1.07 |
| Mir6950 | 1.00 | 35.33 | 1.00 | 40.04 | 68.07 | 1.00 | 1.00 | 1.00 | 1.00 |
| Mir6951 | 26.48 | 1.00 | 21.31 | 1.00 | 1.00 | 1.00 | 1.00 | 0.89 | 0.03 |
| Mir6953 | 48.78 | 0.33 | 0.65 | 0.42 | 1.64 | 1.96 | 0.16 | 2.35 | 0.53 |
| Mir6954 | 131.13 | 149.49 | 0.00 | 1.00 | 1.00 | 1.00 | 1.00 | 0.01 | 1.00 |
| Mir6958 | 1.64 | 0.77 | 1.11 | 0.03 | 0.02 | 0.54 | 0.77 | 1.16 | 1.40 |
| Mir6959 | 1.00 | 1.00 | 0.05 | 1.00 | 1.00 | 1.00 | 1.00 | 1.00 | 1.00 |
| Mir6960 | 1.00 | 1.00 | 1.00 | 1.00 | 1.00 | 1.00 | 1.00 | 0.02 | 1.00 |
| Mir6961 | 1.00 | 1.00 | 1.00 | 1.00 | 1.00 | 1.00 | 1.00 | 1.00 | 1.00 |
| Mir6962 | 1.00 | 1.00 | 58.23 | 1.00 | 101.55 | 1.00 | 1.00 | 0.03 | 38.78 |

Fig. 31-76

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir679 | 1.00 | 1.00 | 1.00 | 1.00 | 1.00 | 1.00 | 1.00 | 1.00 | 1.00 | 1.00 | 1.00 | 1.00 |
| Mir680-1 | 1.00 | 1.00 | 1.00 | 1.00 | 1.00 | 1.00 | 1.00 | 1.00 | 1.00 | 1.00 | 1.00 | 1.00 |
| Mir680-2 | 2.64 | 2.49 | 0.34 | 0.23 | 4.23 | 0.24 | 1.00 | 1.00 | 3.52 | 1.00 | 1.00 | 1.00 |
| Mir681 | 0.94 | 9.37 | 4.98 | 1.12 | 1.00 | 23.20 | 1.00 | 1.00 | 1.00 | 1.00 | 1.00 | 1.00 |
| Mir682 | 1.06 | 1.14 | 0.97 | 1.04 | 0.91 | 1.23 | 0.88 | 1.11 | 0.93 | 6319 | 1.00 | 1.00 |
| Mir686 | 14.56 | 0.09 | 0.64 | 1.06 | 1.31 | 0.83 | 2.02 | 1.24 | 1.68 | 1.00 | 1.00 | 1.00 |
| Mir687 | 0.10 | 0.04 | 0.96 | 0.58 | 0.47 | 1.21 | 1.00 | 1.00 | 0.15 | 1.00 | 1.00 | 1.00 |
| Mir688 | 1.00 | 1.00 | 1.00 | 1.00 | 1.00 | 1.00 | 1.00 | 1.00 | 1.00 | 1.00 | 1.00 | 1.00 |
| Mir6897 | 52.70 | 1.00 | 1.00 | 1.00 | 1.00 | 0.02 | 1.00 | 1.00 | 1.00 | 1.00 | 1.00 | 1.00 |
| Mir6898 | 0.06 | 0.06 | 0.49 | 15.84 | 14.19 | 1.00 | 1.00 | 1.00 | 1.00 | 1.00 | 1.00 | 1.00 |
| Mir6900 | 1.00 | 1.00 | 1.00 | 1.00 | 1.00 | 1.00 | 1.00 | 1.00 | 1.00 | 1.00 | 1.00 | 1.00 |
| Mir6902 | 1.00 | 1.00 | 95.56 | 41.77 | 1.00 | 1.00 | 1.00 | 1.00 | 1.00 | 1.00 | 1.00 | 1.00 |
| Mir6904 | 1.49 | 0.94 | 0.66 | 0.02 | 0.93 | 1.07 | 1.00 | 1.00 | 0.03 | 1.00 | 1.00 | 1.00 |
| Mir6905 | 85.49 | 1.00 | 0.66 | 1.00 | 1.00 | 2.33 | 1.00 | 1.00 | 1.00 | 1.00 | 1.00 | 1.00 |
| Mir6907 | 1.31 | 0.56 | 0.31 | 1.00 | 0.05 | 1.02 | 0.06 | 1.00 | 1.00 | 1.00 | 1.00 | 1.00 |
| Mir6908 | 1.00 | 0.01 | 1.00 | 1.00 | 1.00 | 1.00 | 1.00 | 1.00 | 1.00 | 1.00 | 1.00 | 1.00 |
| Mir6909 | 1.20 | 40.97 | 1.00 | 1.00 | 1.00 | 0.02 | 1.00 | 1.00 | 1.00 | 1.00 | 1.00 | 1.00 |
| Mir6910 | 0.86 | 1.00 | 0.67 | 0.01 | 0.99 | 0.28 | 1.00 | 1.00 | 1.00 | 1.00 | 1.00 | 1.00 |
| Mir6911 | 0.02 | 117.28 | 1.01 | 1.13 | 0.04 | 1.22 | 1.00 | 1.00 | 1.00 | 1.00 | 1.00 | 1.00 |
| Mir6912 | 0.04 | 23.51 | 0.51 | 1.00 | 23.54 | 0.04 | 1.00 | 1.00 | 1.00 | 1.00 | 1.00 | 1.00 |
| Mir6913 | 1.06 | 1.04 | 0.02 | 30.76 | 1.00 | 2.14 | 1.00 | 0.04 | 0.03 | 1.00 | 1.00 | 1.00 |
| Mir6914 | 1.00 | 1.00 | 1.00 | 1.00 | 1.00 | 1.00 | 1.00 | 1.00 | 1.00 | 1.00 | 1.00 | 1.00 |
| Mir6915 | 2.61 | 1.39 | 1.33 | 1.49 | 1.75 | 0.04 | 30.77 | 1.09 | 1.17 | 1.00 | 1.00 | 1.00 |
| Mir6916 | 1.38 | 1.08 | 0.25 | 0.01 | 38.01 | 49.93 | 1.00 | 1.00 | 1.00 | 1.00 | 1.00 | 1.00 |
| Mir6917 | 1.00 | 1.00 | 1.00 | 1.00 | 1.00 | 1.00 | 27.38 | 1.00 | 1.00 | 1.00 | 1.00 | 1.00 |
| Mir6918 | 73.67 | 0.02 | 1.00 | 1.00 | 1.00 | 1.00 | 1.00 | 1.00 | 1.00 | 1.00 | 1.00 | 1.00 |
| Mir6919 | 0.57 | 1.00 | 0.02 | 48.61 | 0.01 | 0.62 | 1.00 | 1.00 | 1.00 | 1.00 | 1.00 | 1.00 |
| Mir6920 | 0.01 | 0.04 | 1.01 | 0.04 | 22.14 | 1.00 | 1.00 | 1.00 | 1.00 | 1.00 | 1.00 | 1.00 |
| Mir6921 | 1.88 | 0.76 | 1.85 | 2.27 | 1.35 | 0.73 | 0.46 | 0.08 | 1.00 | 1.00 | 1.00 | 1.00 |
| Mir692-1 | 0.19 | 1.00 | 1.00 | 1.30 | 0.23 | 4.58 | 1.00 | 1.12 | 1.00 | 1.00 | 1.00 | 1.00 |
| Mir6922 | 1.55 | 0.03 | 3.14 | 0.02 | 0.03 | 38.75 | 37.69 | 26.81 | 1.00 | 1.00 | 1.00 | 1.00 |
| Mir6924 | 0.96 | 1.15 | 1.02 | 1.00 | 1.21 | 2.89 | 1.00 | 0.03 | 1.00 | 1.00 | 1.00 | 1.00 |
| Mir6925 | 0.34 | 0.87 | 0.34 | 1.00 | 23.54 | 0.02 | 1.00 | 1.00 | 1.00 | 1.00 | 1.00 | 1.00 |
| Mir6926 | 0.03 | 1.00 | 1.00 | 1.00 | 1.00 | 1.00 | 1.00 | 1.00 | 1.00 | 1.00 | 1.00 | 1.00 |
| Mir6927 | 0.52 | 0.04 | 0.99 | 1.00 | 1.00 | 1.00 | 1.00 | 1.00 | 20.70 | 1.00 | 1.00 | 1.00 |
| Mir6928 | 30.17 | 0.04 | 0.03 | 27.84 | 2.79 | 0.02 | 1.00 | 1.00 | 1.00 | 1.00 | 1.00 | 1.00 |
| Mir6929 | 1.19 | 28.54 | 0.03 | 1.00 | 1.00 | 1.00 | 1.00 | 1.00 | 1.00 | 1.00 | 1.00 | 1.00 |
| Mir6930 | 1.00 | 1.00 | 1.00 | 2.42 | 1.00 | 1.00 | 1.00 | 1.00 | 1.00 | 1.00 | 1.00 | 1.00 |
| Mir6931 | 2.36 | 0.01 | 0.66 | 0.06 | 1.00 | 1.00 | 1.00 | 1.00 | 1.00 | 1.00 | 1.00 | 1.00 |
| Mir6933 | 1.00 | 1.00 | 15.33 | 1.00 | 1.00 | 1.00 | 1.00 | 1.00 | 1.00 | 1.00 | 1.00 | 1.00 |
| Mir6934 | 1.00 | 40.97 | 1.00 | 1.00 | 1.00 | 1.00 | 1.00 | 1.00 | 1.00 | 1.00 | 1.00 | 1.00 |
| Mir6935 | 1.13 | 0.92 | 1.66 | 0.43 | 1.17 | 1.43 | 0.04 | 1.00 | 0.03 | 1.00 | 1.00 | 1.00 |
| Mir6936 | 1.59 | 0.70 | 1.01 | 2.31 | 0.15 | 0.01 | 54.33 | 1.00 | 1.00 | 1.00 | 1.00 | 1.00 |
| Mir6937 | 83.75 | 65.04 | 0.02 | 1.00 | 1.00 | 1.00 | 0.04 | 32.67 | 64.11 | 1.00 | 1.00 | 1.00 |
| Mir6938 | 48.80 | 0.02 | 0.02 | 1.00 | 1.00 | 1.00 | 1.00 | 1.00 | 1.00 | 1.00 | 1.00 | 1.00 |
| Mir6939 | 1.10 | 0.74 | 0.62 | 2.30 | 3.77 | 0.52 | 0.07 | 34.47 | 1.00 | 1.00 | 1.00 | 1.00 |
| Mir6940 | 1.00 | 1.00 | 1.00 | 1.00 | 1.00 | 1.00 | 1.00 | 1.00 | 1.00 | 1.00 | 1.00 | 1.00 |
| Mir6941 | 0.02 | 0.02 | 0.01 | 1.00 | 1.00 | 1.00 | 1.00 | 1.00 | 1.00 | 1.00 | 1.00 | 1.00 |
| Mir6942 | 2.11 | 139.89 | 0.54 | 1.10 | 1.92 | 1.66 | 1.00 | 1.00 | 1.00 | 1.00 | 1.00 | 1.00 |
| Mir6943 | 0.34 | 0.56 | 1.09 | 1.00 | 1.76 | 0.01 | 1.00 | 1.00 | 0.04 | 1.00 | 1.00 | 1.00 |
| Mir6944 | 1.00 | 1.00 | 1.00 | 1.00 | 1.00 | 1.00 | 1.00 | 1.00 | 1.00 | 1.00 | 1.00 | 1.00 |
| Mir6945 | 34.30 | 62.87 | 1.98 | 0.02 | 0.93 | 1.22 | 1.00 | 1.00 | 1.00 | 1.00 | 1.00 | 1.00 |
| Mir6946 | 0.55 | 1.02 | 1.42 | 0.02 | 0.34 | 1.52 | 1.00 | 0.03 | 0.92 | 1.00 | 1.00 | 1.00 |
| Mir6947 | 0.03 | 1.00 | 1.00 | 1.00 | 0.03 | 1.00 | 1.00 | 1.00 | 1.00 | 1.00 | 1.00 | 1.00 |
| Mir6948 | 1.01 | 1.38 | 1.03 | 0.36 | 0.29 | 0.73 | 1.00 | 71.36 | 0.01 | 1.00 | 1.00 | 1.00 |
| Mir6950 | 0.04 | 1.00 | 1.00 | 1.00 | 1.00 | 1.00 | 1.00 | 1.00 | 1.00 | 1.00 | 1.00 | 1.00 |
| Mir6951 | 0.05 | 1.00 | 0.04 | 0.35 | 1.02 | 0.02 | 0.04 | 1.00 | 1.00 | 1.00 | 1.00 | 1.00 |
| Mir6953 | 0.44 | 1.00 | 2.07 | 0.84 | 0.95 | 1.04 | 0.81 | 1.00 | 25.52 | 1.00 | 1.00 | 1.00 |
| Mir6954 | 1.00 | 2.96 | 1.04 | 0.02 | 1.00 | 0.02 | 1.00 | 0.01 | 0.02 | 1.00 | 1.00 | 1.00 |
| Mir6958 | 1.07 | 1.01 | 0.59 | 84.02 | 0.02 | 0.86 | 0.39 | 3.07 | 0.91 | 1.00 | 1.00 | 1.00 |
| Mir6959 | 0.05 | 1.00 | 1.00 | 0.06 | 1.00 | 1.00 | 1.00 | 1.00 | 1.00 | 1.00 | 1.00 | 1.00 |
| Mir6960 | 1.05 | 1.73 | 0.96 | 1.16 | 0.50 | 0.01 | 1.00 | 1.00 | 1.00 | 1.00 | 1.00 | 1.00 |
| Mir6961 | 1.00 | 1.00 | 1.00 | 0.04 | 1.00 | 35.81 | 1.00 | 1.00 | 1.00 | 1.00 | 1.00 | 1.00 |
| Mir6962 | 1.00 | 1.00 | 1.00 | 38.20 | 1.00 | 1.00 | 1.00 | 1.00 | 1.00 | 1.00 | 1.00 | 1.00 |

Fig. 31-77

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir6963 | 70.60 | 1.70 | 2.72 | 1.00 | 1.00 | 1.00 | 33.98 | 1.00 | 1.00 |
| Mir6964 | 1.00 | 1.00 | 1.00 | 1.00 | 1.00 | 1.00 | 1.00 | 1.00 | 1.00 |
| Mir6966 | 0.85 | 0.86 | 0.04 | 0.02 | 42.80 | 0.04 | 33.39 | 1.05 | 32.75 |
| Mir6968 | 1.00 | 1.00 | 1.00 | 0.02 | 0.02 | 1.00 | 1.00 | 1.00 | 1.00 |
| Mir6969 | 1.00 | 1.00 | 1.00 | 1.00 | 1.00 | 1.00 | 1.00 | 1.00 | 1.00 |
| Mir697 | 0.89 | 1.54 | 1.80 | 21.16 | 2.08 | 1.01 | 0.17 | 0.80 | 1.85 |
| Mir6970 | 0.86 | 2.23 | 1.38 | 0.40 | 5.72 | 1.02 | 49.51 | 0.86 | 0.02 |
| Mir6972 | 0.87 | 0.90 | 2.78 | 1.39 | 288.05 | 1.01 | 1.70 | 1.83 | 0.93 |
| Mir6973a | 1.00 | 1.00 | 16.45 | 0.05 | 1.00 | 18.50 | 1.00 | 0.05 | 1.00 |
| Mir6973b | 1.65 | 0.35 | 1.81 | 24.07 | 0.05 | 1.00 | 1.00 | 1.00 | 1.00 |
| Mir6974 | 1.00 | 1.00 | 1.00 | 1.00 | 1.00 | 1.00 | 1.00 | 1.00 | 1.00 |
| Mir6975 | 1.00 | 49.35 | 1.00 | 1.00 | 1.00 | 1.00 | 1.00 | 1.00 | 1.00 |
| Mir6976 | 0.01 | 1.00 | 1.85 | 0.01 | 0.01 | 1.00 | 1.00 | 1.00 | 1.00 |
| Mir6977 | 1.00 | 1.00 | 0.02 | 1.00 | 1.00 | 1.00 | 1.00 | 1.00 | 1.00 |
| Mir6979 | 1.00 | 1.00 | 81.05 | 1.00 | 1.00 | 1.00 | 1.00 | 184.61 | 0.01 |
| Mir6980 | 59.65 | 59.03 | 1.00 | 1.00 | 1.00 | 1.00 | 1.00 | 1.00 | 1.00 |
| Mir6981 | 0.37 | 0.57 | 0.65 | 0.63 | 3.13 | 5.34 | 1.00 | 0.21 | 0.11 |
| Mir6984 | 1.00 | 1.00 | 1.00 | 1.00 | 1.00 | 1.00 | 1.04 | 72.02 | 1.00 |
| Mir6985 | 1.00 | 1.00 | 1.00 | 1.00 | 1.00 | 1.00 | 1.00 | 1.00 | 1.00 |
| Mir6986 | 69.88 | 1.00 | 66.21 | 1.00 | 1.00 | 1.00 | 1.10 | 1.00 | 1.00 |
| Mir6988 | 0.01 | 169.90 | 1.00 | 1.00 | 1.00 | 0.01 | 1.00 | 1.00 | 3.46 |
| Mir6989 | 0.88 | 1.15 | 2.26 | 0.01 | 0.01 | 1.04 | 1.00 | 48.68 | 1.00 |
| Mir6991 | 4.38 | 2.89 | 0.30 | 1.00 | 0.01 | 0.02 | 38.99 | 74.39 | 0.02 |
| Mir6993 | 36.14 | 1.00 | 0.45 | 1.00 | 1.00 | 1.00 | 0.37 | 0.02 | 0.45 |
| Mir6994 | 1.00 | 1.00 | 1.00 | 1.00 | 1.00 | 1.00 | 1.00 | 1.00 | 1.00 |
| Mir6995 | 1.00 | 1.00 | 1.00 | 1.00 | 1.00 | 1.00 | 1.00 | 1.00 | 1.00 |
| Mir6996 | 1.00 | 1.00 | 1.00 | 1.00 | 1.00 | 1.00 | 1.00 | 1.00 | 1.00 |
| Mir6997 | 25.41 | 22.50 | 1.00 | 1.00 | 1.00 | 1.00 | 1.00 | 0.03 | 1.00 |
| Mir6998 | 39.01 | 36.76 | 39.38 | 1.00 | 0.01 | 1.00 | 1.00 | 1.06 | 1.00 |
| Mir6999 | 0.51 | 0.55 | 1.07 | 0.01 | 1.00 | 1.00 | 0.01 | 1.00 | 1.00 |
| Mir700 | 0.90 | 1.00 | 1.00 | 0.67 | 0.58 | 68.93 | 39.93 | 1.00 | 1.00 |
| Mir7000 | 1.00 | 0.02 | 1.00 | 1.00 | 1.00 | 1.00 | 1.00 | 1.00 | 1.00 |
| Mir7001 | 0.03 | 14.88 | 1.00 | 5.44 | 2.01 | 0.81 | 39.30 | 0.05 | 0.05 |
| Mir7003 | 1.00 | 1.00 | 1.00 | 1.00 | 1.00 | 1.00 | 1.00 | 1.00 | 1.00 |
| Mir7004 | 39.01 | 0.02 | 1.00 | 1.00 | 95.99 | 1.00 | 1.00 | 1.00 | 66.34 |
| Mir7005 | 0.88 | 0.76 | 0.89 | 0.35 | 0.45 | 0.78 | 1.00 | 0.02 | 1.00 |
| Mir7006 | 57.41 | 0.03 | 1.00 | 1.00 | 0.02 | 36.54 | 0.01 | 0.02 | 1.69 |
| Mir7007 | 1.00 | 1.00 | 51.12 | 1.00 | 1.00 | 1.00 | 1.00 | 1.00 | 1.00 |
| Mir7009 | 39.01 | 1.00 | 1.00 | 1.00 | 1.00 | 1.00 | 1.00 | 1.00 | 1.00 |
| Mir7010 | 1.00 | 1.00 | 1.00 | 1.00 | 1.00 | 1.00 | 1.00 | 0.01 | 1.00 |
| Mir7011 | 42.53 | 0.04 | 1.00 | 171.72 | 0.01 | 0.41 | 31.06 | 0.03 | 1.23 |
| Mir7012 | 1.00 | 1.00 | 39.38 | 1.00 | 1.00 | 1.00 | 1.00 | 1.00 | 1.00 |
| Mir7013 | 0.35 | 1.73 | 0.68 | 0.37 | 126.89 | 0.04 | 63.94 | 0.02 | 0.03 |
| Mir7014 | 83.95 | 0.85 | 0.02 | 0.01 | 1.00 | 124.34 | 1.00 | 1.00 | 73.21 |
| Mir7015 | 1.00 | 1.00 | 1.00 | 1.00 | 95.99 | 1.00 | 1.00 | 1.00 | 1.00 |
| Mir7016 | 1.00 | 1.00 | 1.00 | 0.57 | 1.15 | 139.89 | 1.00 | 1.00 | 1.00 |
| Mir7017 | 1.00 | 1.00 | 1.00 | 1.00 | 1.00 | 71.02 | 1.00 | 1.00 | 1.00 |
| Mir7018 | 0.07 | 1.00 | 0.08 | 1.00 | 1.00 | 1.00 | 1.00 | 1.00 | 1.00 |
| Mir7019 | 53.89 | 0.29 | 0.02 | 2.08 | 2.30 | 1.05 | 1.04 | 34.53 | 1.76 |
| Mir702 | 4.73 | 7.96 | 4.50 | 1.00 | 10.58 | 4.51 | 1.00 | 1.00 | 0.30 |
| Mir7020 | 1.00 | 0.04 | 1.00 | 50.01 | 0.02 | 0.02 | 1.00 | 1.00 | 1.00 |
| Mir7021 | 1.00 | 1.00 | 1.00 | 1.00 | 1.00 | 1.00 | 1.00 | 1.00 | 1.00 |
| Mir7022 | 1.00 | 1.00 | 1.00 | 1.00 | 1.00 | 1.00 | 1.00 | 1.00 | 176.31 |
| Mir7023 | 1.00 | 1.00 | 1.00 | 1.00 | 1.00 | 1.00 | 1.00 | 53.49 | 1.00 |
| Mir7024 | 45.82 | 0.01 | 0.02 | 1.21 | 124.21 | 68.54 | 3.21 | 1.00 | 1.00 |
| Mir7025 | 0.01 | 0.90 | 1.71 | 31.29 | 1.00 | 0.04 | 28.98 | 1.00 | 1.00 |
| Mir7026 | 0.65 | 88.23 | 0.46 | 0.01 | 68.99 | 0.41 | 46.82 | 0.41 | 3.38 |
| Mir7027 | 1.17 | 0.44 | 1.08 | 2.41 | 3.36 | 2.99 | 0.51 | 0.03 | 0.03 |
| Mir7028 | 39.01 | 1.79 | 0.01 | 0.43 | 1.00 | 2.04 | 65.04 | 1.06 | 1.00 |
| Mir7030 | 54.45 | 51.29 | 112.62 | 1.00 | 0.01 | 0.01 | 1.00 | 0.01 | 1.00 |
| Mir7031 | 0.93 | 0.02 | 0.48 | 80.28 | 0.01 | 50.35 | 0.02 | 1.00 | 1.00 |
| Mir7032 | 1.00 | 1.00 | 1.00 | 1.00 | 1.00 | 1.00 | 1.00 | 17.36 | 1.00 |
| Mir7033 | 14.42 | 1.00 | 13.68 | 1.00 | 1.00 | 1.00 | 1.00 | 1.00 | 1.00 |
| Mir7034 | 1.00 | 1.00 | 1.00 | 0.58 | 18.23 | 0.08 | 0.06 | 0.06 | 0.93 |

Fig. 31-78

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir6963 | 0.96 | 2.99 | 44.55 | 1.00 | 0.99 | 22.70 | 1.00 | 40.94 | 1.00 |
| Mir6964 | 1.00 | 55.86 | 56.25 | 0.02 | 1.00 | 1.00 | 1.00 | 0.01 | 1.00 |
| Mir6966 | 1.52 | 1.53 | 21.15 | 39.90 | 21.17 | 0.04 | 0.48 | 3.41 | 1.89 |
| Mir6968 | 1.90 | 1.00 | 0.02 | 1.00 | 1.00 | 27.69 | 1.00 | 0.02 | 0.02 |
| Mir6969 | 1.00 | 1.00 | 1.00 | 1.00 | 1.00 | 1.00 | 188.19 | 0.01 | 0.01 |
| Mir697 | 0.60 | 0.67 | 1.06 | 0.98 | 1.92 | 2.35 | 1.29 | 0.58 | 1.61 |
| Mir6970 | 0.71 | 3.13 | 1.09 | 61.37 | 1.00 | 0.90 | 1.97 | 1.00 | 1.01 |
| Mir6972 | 64.94 | 0.56 | 0.37 | 0.03 | 1.00 | 0.01 | 1.00 | 82.58 | 2.01 |
| Mir6973a | 0.02 | 3.39 | 0.97 | 1.00 | 1.00 | 1.00 | 0.87 | 1.14 | 0.88 |
| Mir6973b | 0.09 | 0.08 | 49.43 | 1.92 | 1.00 | 0.90 | 1.86 | 2.19 | 18.78 |
| Mir6974 | 2.02 | 10.30 | 0.09 | 1.00 | 11.04 | 10.97 | 0.30 | 1.41 | 1.09 |
| Mir6975 | 1.00 | 1.00 | 1.00 | 1.00 | 1.00 | 1.00 | 1.00 | 0.01 | 1.00 |
| Mir6976 | 0.26 | 0.56 | 79.15 | 1.00 | 39.85 | 1.00 | 1.00 | 0.52 | 3.18 |
| Mir6977 | 1.00 | 0.03 | 1.00 | 1.00 | 1.00 | 1.00 | 69.25 | 1.00 | 1.00 |
| Mir6979 | 0.01 | 1.00 | 1.07 | 1.00 | 1.00 | 1.00 | 1.00 | 1.00 | 1.00 |
| Mir6980 | 0.02 | 0.50 | 2.01 | 1.00 | 1.00 | 1.00 | 1.00 | 1.00 | 1.00 |
| Mir6981 | 0.95 | 0.99 | 1.14 | 0.69 | 0.24 | 11.88 | 1.53 | 1.00 | 2.87 |
| Mir6984 | 1.00 | 1.00 | 1.00 | 1.00 | 1.00 | 1.00 | 1.00 | 1.00 | 1.00 |
| Mir6985 | 1.00 | 41.60 | 44.08 | 1.00 | 1.00 | 44.39 | 1.00 | 1.00 | 1.00 |
| Mir6986 | 0.01 | 0.01 | 57.96 | 1.00 | 119.65 | 62.35 | 1.00 | 1.00 | 110.32 |
| Mir6988 | 0.02 | 1.35 | 4.07 | 1.00 | 1.00 | 0.02 | 0.94 | 1.61 | 290.94 |
| Mir6989 | 1.18 | 1.06 | 0.86 | 1.12 | 1.05 | 1.00 | 0.94 | 0.72 | 0.56 |
| Mir6991 | 1.03 | 1.75 | 4.85 | 27.92 | 0.01 | 1.94 | 41.60 | 1.00 | 0.03 |
| Mir6993 | 2.09 | 1.00 | 0.01 | 1.00 | 1.00 | 1.00 | 0.01 | 0.01 | 0.02 |
| Mir6994 | 1.00 | 1.00 | 1.00 | 1.00 | 1.00 | 1.00 | 62.69 | 1.00 | 1.00 |
| Mir6995 | 0.05 | 0.05 | 0.05 | 0.04 | 0.05 | 0.04 | 1.00 | 1.00 | 1.00 |
| Mir6996 | 1.00 | 1.00 | 1.00 | 1.00 | 1.00 | 1.00 | 1.00 | 1.00 | 0.01 |
| Mir6997 | 1.00 | 1.00 | 1.00 | 1.00 | 1.00 | 1.00 | 1.00 | 1.00 | 1.00 |
| Mir6998 | 0.03 | 0.98 | 1.00 | 1.00 | 0.03 | 34.74 | 64.12 | 1.00 | 1.00 |
| Mir6999 | 1.91 | 2.00 | 2.04 | 1.65 | 2.30 | 1.62 | 0.34 | 0.80 | 1.18 |
| Mir700 | 40.00 | 2.86 | 20.01 | 1.00 | 0.06 | 1.00 | 1.00 | 42.36 | 0.06 |
| Mir7000 | 1.00 | 1.00 | 1.00 | 1.00 | 1.00 | 1.00 | 1.00 | 1.00 | 1.00 |
| Mir7001 | 14.32 | 0.81 | 1.82 | 1.12 | 14.20 | 1.00 | 1.85 | 5.17 | 0.41 |
| Mir7003 | 1.00 | 1.00 | 1.00 | 1.00 | 1.00 | 1.00 | 1.00 | 1.00 | 51.17 |
| Mir7004 | 0.03 | 36.55 | 1.00 | 0.03 | 1.00 | 1.00 | 1.00 | 1.00 | 1.00 |
| Mir7005 | 0.96 | 0.41 | 1.44 | 1.08 | 1.36 | 0.67 | 0.01 | 0.02 | 1.00 |
| Mir7006 | 48.18 | 0.49 | 0.38 | 1.00 | 0.04 | 0.84 | 1.01 | 1.00 | 1.63 |
| Mir7007 | 0.88 | 3.20 | 2.21 | 1.00 | 45.87 | 24.21 | 1.00 | 1.00 | 1.00 |
| Mir7009 | 34.89 | 0.03 | 1.00 | 1.00 | 1.00 | 1.00 | 1.00 | 1.00 | 1.00 |
| Mir7010 | 1.00 | 35.24 | 1.00 | 1.00 | 1.00 | 1.00 | 1.00 | 0.01 | 0.02 |
| Mir7011 | 1.02 | 1.00 | 36.84 | 1.12 | 18.92 | 1.00 | 1.00 | 1.00 | 0.02 |
| Mir7012 | 1.00 | 0.98 | 34.50 | 35.12 | 0.99 | 0.02 | 1.00 | 1.00 | 1.01 |
| Mir7013 | 0.69 | 1.03 | 1.61 | 0.30 | 0.05 | 0.46 | 0.92 | 2.09 | 0.82 |
| Mir7014 | 2.90 | 0.01 | 0.01 | 46.34 | 39.85 | 0.02 | 1.00 | 1.00 | 0.00 |
| Mir7015 | 1.00 | 1.00 | 34.50 | 1.00 | 1.00 | 1.00 | 1.00 | 0.01 | 0.02 |
| Mir7016 | 1.00 | 0.03 | 1.00 | 1.00 | 1.00 | 1.00 | 1.00 | 1.00 | 1.00 |
| Mir7017 | 1.00 | 38.23 | 1.00 | 41.25 | 1.00 | 1.00 | 168.92 | 1.00 | 1.00 |
| Mir7018 | 1.00 | 1.00 | 1.00 | 1.00 | 1.00 | 9.98 | 1.00 | 1.00 | 1.00 |
| Mir7019 | 1.03 | 67.17 | 1.05 | 1.12 | 0.04 | 24.23 | 0.94 | 1.00 | 0.02 |
| Mir702 | 1.08 | 0.98 | 1.06 | 1.00 | 1.00 | 0.21 | 1.59 | 1.91 | 1.00 |
| Mir7020 | 1.00 | 1.00 | 1.00 | 1.00 | 0.04 | 1.00 | 1.00 | 1.00 | 1.00 |
| Mir7021 | 1.00 | 35.24 | 1.00 | 1.00 | 1.00 | 1.00 | 1.00 | 1.00 | 1.00 |
| Mir7022 | 1.00 | 1.00 | 0.02 | 0.01 | 1.00 | 1.00 | 1.00 | 1.00 | 1.00 |
| Mir7023 | 34.89 | 1.00 | 1.00 | 1.00 | 0.03 | 1.00 | 1.00 | 0.58 | 0.89 |
| Mir7024 | 38.42 | 189.16 | 0.56 | 1.00 | 1.00 | 0.02 | 1.00 | 1.20 | 293.25 |
| Mir7025 | 2.00 | 68.48 | 0.36 | 21.77 | 17.83 | 17.71 | 30.83 | 1.00 | 1.00 |
| Mir7026 | 1.21 | 1.25 | 0.94 | 28.12 | 1.52 | 0.45 | 2.52 | 0.73 | 0.70 |
| Mir7027 | 0.63 | 1.78 | 3.79 | 24.58 | 0.02 | 0.60 | 5.94 | 1.99 | 3.83 |
| Mir7028 | 1.05 | 1.10 | 9.30 | 76.94 | 34.97 | 34.74 | 0.83 | 155.76 | 0.01 |
| Mir7030 | 1.03 | 3.04 | 0.56 | 1.00 | 1.00 | 1.00 | 299.74 | 0.38 | 1.30 |
| Mir7031 | 1.07 | 1.48 | 1.63 | 32.54 | 0.53 | 1.00 | 1.94 | 0.01 | 106.60 |
| Mir7032 | 13.47 | 1.00 | 1.00 | 1.00 | 1.00 | 1.00 | 1.00 | 1.00 | 19.93 |
| Mir7033 | 1.00 | 1.00 | 1.00 | 1.00 | 1.00 | 1.00 | 1.00 | 1.00 | 16.34 |
| Mir7034 | 0.56 | 1.00 | 1.00 | 1.00 | 0.09 | 0.08 | 1.01 | 1.00 | 15.02 |

Fig. 31-79

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir6963 | 1.00 | 1.00 | 1.00 | 1.00 | 1.00 | 1.00 | 1.00 | 1.00 | 1.00 |
| Mir6964 | 1.00 | 1.00 | 1.00 | 1.00 | 1.00 | 1.00 | 1.00 | 1.00 | 1.00 |
| Mir6966 | 1.00 | 1.00 | 0.26 | 86.59 | 1.00 | 1.00 | 21.92 | 34.99 | 1.00 |
| Mir6968 | 64.07 | 54.88 | 1.00 | 1.00 | 1.00 | 1.00 | 0.02 | 0.89 | 0.04 |
| Mir6969 | 1.00 | 1.00 | 1.00 | 1.00 | 1.00 | 1.00 | 1.00 | 1.00 | 1.00 |
| Mir697 | 0.82 | 0.85 | 2.12 | 1.20 | 3.74 | 1.30 | 2.91 | 1.83 | 3.08 |
| Mir6970 | 1.69 | 1.00 | 0.01 | 3.25 | 1.91 | 0.20 | 0.95 | 1.83 | 0.73 |
| Mir6972 | 1.00 | 1.00 | 0.02 | 1.00 | 1.00 | 1.56 | 0.90 | 0.72 | 1.90 |
| Mir6973a | 1.00 | 24.19 | 1.00 | 1.00 | 2.00 | 1.00 | 1.10 | 0.85 | 26.29 |
| Mir6973b | 1.10 | 0.92 | 0.34 | 0.87 | 80.59 | 1.02 | 0.94 | 0.91 | 1.35 |
| Mir6974 | 1.00 | 1.00 | 1.07 | 0.07 | 1.00 | 1.00 | 12.01 | 1.00 | 1.00 |
| Mir6975 | 1.00 | 1.00 | 1.00 | 1.00 | 1.00 | 1.00 | 1.00 | 1.00 | 1.00 |
| Mir6976 | 1.07 | 1.00 | 1.00 | 1.00 | 1.00 | 55.33 | 6.41 | 0.01 | 2.66 |
| Mir6977 | 1.00 | 1.00 | 1.00 | 1.00 | 1.00 | 1.00 | 0.03 | 30.49 | 1.00 |
| Mir6979 | 1.00 | 1.00 | 1.00 | 1.00 | 1.00 | 1.00 | 1.00 | 60.81 | 0.02 |
| Mir6980 | 1.00 | 1.00 | 1.00 | 1.00 | 1.00 | 1.00 | 1.00 | 1.00 | 1.00 |
| Mir6981 | 0.12 | 0.24 | 3.77 | 1.58 | 0.50 | 2.32 | 1.00 | 0.17 | 6.69 |
| Mir6984 | 1.00 | 1.00 | 1.00 | 1.00 | 89.61 | 1.00 | 1.00 | 1.00 | 1.00 |
| Mir6985 | 1.00 | 1.00 | 1.00 | 1.00 | 0.01 | 68.95 | 1.00 | 0.89 | 40.77 |
| Mir6986 | 1.00 | 206.62 | 1.00 | 1.09 | 1.08 | 416.47 | 123.73 | 0.02 | 59.31 |
| Mir6988 | 1.00 | 1.00 | 1.00 | 1.00 | 1.00 | 1.00 | 0.01 | 0.86 | 0.01 |
| Mir6989 | 67.30 | 1.00 | 94.77 | 79.24 | 2.16 | 92.01 | 0.03 | 1.00 | 1.01 |
| Mir6991 | 1.13 | 226.23 | 1.36 | 0.34 | 0.23 | 1.47 | 24.74 | 1.00 | 0.02 |
| Mir6993 | 67.30 | 0.01 | 51.14 | 87.00 | 158.69 | 1.00 | 0.01 | 0.03 | 66.19 |
| Mir6994 | 1.00 | 1.00 | 1.00 | 1.00 | 1.00 | 1.00 | 1.00 | 1.00 | 1.09 |
| Mir6995 | 1.00 | 1.00 | 1.00 | 0.02 | 2.96 | 82.61 | 1.00 | 0.04 | 1.00 |
| Mir6996 | 1.00 | 1.00 | 1.00 | 132.89 | 1.00 | 1.00 | 1.00 | 1.00 | 1.00 |
| Mir6997 | 1.00 | 1.00 | 1.00 | 1.00 | 1.00 | 1.00 | 1.00 | 1.00 | 22.27 |
| Mir6998 | 1.00 | 1.02 | 1.08 | 1.00 | 1.00 | 0.02 | 1.00 | 32.76 | 0.03 |
| Mir6999 | 0.90 | 1.00 | 77.92 | 1.00 | 1.00 | 1.00 | 47.13 | 0.01 | 1.01 |
| Mir700 | 0.67 | 131.63 | 1.16 | 25.56 | 0.35 | 0.50 | 1.00 | 1.00 | 0.04 |
| Mir7000 | 0.01 | 1.00 | 0.02 | 1.00 | 1.00 | 1.00 | 0.03 | 1.00 | 34.72 |
| Mir7001 | 1.00 | 43.89 | 1.00 | 0.05 | 1.49 | 0.06 | 1.43 | 1.19 | 12.73 |
| Mir7003 | 1.00 | 1.00 | 1.00 | 1.00 | 1.00 | 1.00 | 1.00 | 28.31 | 1.00 |
| Mir7004 | 1.00 | 85.26 | 1.00 | 1.00 | 1.00 | 0.94 | 1.00 | 1.00 | 1.00 |
| Mir7005 | 58.08 | 1.00 | 0.03 | 1.27 | 0.66 | 5.39 | 1.00 | 23.09 | 0.04 |
| Mir7006 | 0.74 | 50.38 | 0.02 | 0.02 | 1.19 | 31.73 | 0.41 | 0.27 | 3.82 |
| Mir7007 | 1.00 | 1.00 | 1.00 | 1.15 | 3.91 | 0.21 | 1.00 | 20.08 | 1.00 |
| Mir7009 | 1.00 | 1.00 | 1.00 | 89.21 | 1.00 | 1.00 | 1.00 | 1.00 | 1.00 |
| Mir7010 | 0.01 | 1.00 | 1.00 | 1.00 | 1.00 | 1.00 | 1.00 | 1.00 | 1.00 |
| Mir7011 | 1.00 | 35.33 | 1.00 | 1.10 | 1.00 | 0.12 | 0.44 | 3.41 | 1.43 |
| Mir7012 | 174.34 | 1.00 | 0.02 | 1.00 | 1.00 | 1.00 | 1.00 | 1.00 | 1.00 |
| Mir7013 | 0.84 | 3.98 | 2.14 | 0.81 | 1.07 | 0.43 | 2.93 | 4.36 | 1.08 |
| Mir7014 | 1.00 | 1.00 | 1.00 | 332.01 | 190.25 | 55.33 | 0.03 | 35.37 | 2.00 |
| Mir7015 | 99.59 | 1.00 | 1.00 | 1.00 | 1.00 | 1.00 | 1.00 | 1.00 | 1.00 |
| Mir7016 | 1.00 | 1.00 | 1.00 | 1.00 | 1.00 | 1.00 | 0.05 | 1.00 | 1.00 |
| Mir7017 | 1.00 | 1.00 | 1.00 | 0.01 | 1.00 | 1.00 | 1.00 | 1.00 | 1.00 |
| Mir7018 | 1.00 | 1.00 | 1.00 | 1.00 | 14.25 | 1.00 | 11.06 | 1.00 | 0.11 |
| Mir7019 | 0.02 | 0.48 | 0.03 | 1.00 | 1.05 | 1.42 | 0.04 | 0.91 | 0.51 |
| Mir702 | 4.65 | 9.85 | 0.39 | 5.88 | 0.22 | 4.10 | 0.24 | 1.00 | 1.08 |
| Mir7020 | 80.04 | 0.02 | 33.03 | 1.00 | 1.00 | 1.00 | 1.00 | 1.00 | 1.00 |
| Mir7021 | 1.00 | 1.00 | 1.00 | 1.00 | 1.00 | 1.00 | 1.00 | 1.00 | 1.00 |
| Mir7022 | 1.00 | 1.00 | 1.00 | 1.00 | 1.00 | 1.00 | 47.13 | 1.00 | 1.56 |
| Mir7023 | 1.00 | 1.00 | 1.00 | 0.01 | 1.00 | 1.00 | 1.00 | 1.00 | 1.00 |
| Mir7024 | 1.00 | 1.00 | 1.00 | 1.00 | 0.00 | 1.00 | 86.38 | 38.28 | 1.00 |
| Mir7025 | 1.00 | 1.00 | 1.00 | 1.09 | 1.00 | 1.00 | 1.00 | 1.00 | 1.00 |
| Mir7026 | 0.21 | 5.01 | 0.01 | 126.71 | 63.89 | 0.96 | 1.45 | 1.85 | 0.28 |
| Mir7027 | 0.01 | 37.94 | 4.15 | 1.69 | 39.86 | 0.01 | 1.11 | 0.96 | 0.39 |
| Mir7028 | 99.59 | 85.26 | 1.00 | 0.01 | 0.01 | 0.58 | 1.09 | 0.91 | 67.08 |
| Mir7030 | 131.13 | 1.00 | 0.01 | 0.99 | 0.01 | 0.01 | 51.92 | 0.89 | 1.00 |
| Mir7031 | 1.00 | 76.69 | 1.00 | 0.02 | 1.00 | 2.16 | 2.73 | 0.45 | 1.83 |
| Mir7032 | 1.00 | 1.00 | 1.00 | 1.00 | 23.42 | 1.00 | 14.65 | 1.00 | 1.00 |
| Mir7033 | 1.00 | 1.00 | 1.00 | 1.00 | 1.00 | 1.00 | 0.04 | 0.85 | 11.50 |
| Mir7034 | 1.00 | 1.00 | 1.00 | 1.74 | 1.06 | 1.68 | 1.00 | 9.43 | 1.14 |

Fig. 31-80

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir6963 | 28.37 | 1.00 | 0.04 | 0.04 | 1.00 | 1.02 | 1.00 | 1.00 | 0.03 | 1.00 | 1.00 | 1.00 |
| Mir6964 | 1.00 | 52.41 | 1.00 | 1.00 | 1.00 | 0.02 | 1.00 | 1.00 | 1.00 | 1.00 | 1.00 | 1.00 |
| Mir6966 | 26.71 | 0.01 | 0.41 | 65.07 | 0.67 | 3.05 | 1.00 | 71.65 | 0.03 | 1.00 | 1.00 | 1.00 |
| Mir6968 | 3.15 | 1.11 | 69.16 | 0.04 | 26.75 | 1.02 | 1.00 | 1.00 | 1.00 | 1.00 | 1.00 | 1.00 |
| Mir6969 | 1.00 | 1.00 | 1.00 | 1.00 | 1.00 | 1.00 | 1.20 | 0.76 | 0.76 | 1.00 | 1.00 | 1.00 |
| Mir697 | 0.71 | 0.65 | 0.41 | 1.36 | 0.34 | 2.42 | 0.29 | 0.60 | 1.59 | 1.00 | 1.00 | 1.00 |
| Mir6970 | 0.71 | 0.97 | 1.50 | 0.59 | 1.39 | 0.90 | 0.77 | 1.44 | 2.32 | 1.00 | 1.00 | 1.00 |
| Mir6972 | 90.08 | 0.01 | 1.03 | 1.33 | 1.91 | 45.74 | 1.00 | 1.00 | 35.31 | 1.00 | 1.00 | 1.00 |
| Mir6973a | 0.90 | 1.25 | 1.19 | 0.95 | 3.50 | 1.23 | 0.82 | 0.09 | 1.00 | 1.00 | 1.00 | 1.00 |
| Mir6973b | 2.68 | 0.38 | 2.61 | 13.58 | 1.00 | 14.60 | 1.00 | 1.00 | 0.91 | 1.00 | 1.00 | 1.00 |
| Mir6974 | 0.91 | 1.09 | 3.09 | 13.78 | 1.00 | 0.09 | 1.00 | 1.00 | 1.00 | 1.00 | 1.00 | 1.00 |
| Mir6975 | 1.00 | 1.00 | 0.02 | 1.00 | 39.88 | 1.00 | 1.00 | 1.00 | 1.00 | 1.00 | 1.00 | 1.00 |
| Mir6976 | 0.53 | 1.05 | 1.98 | 119.91 | 1.00 | 1.00 | 1.00 | 0.03 | 1.00 | 1.00 | 1.00 | 1.00 |
| Mir6977 | 1.00 | 1.00 | 1.00 | 1.00 | 1.00 | 1.00 | 1.00 | 1.00 | 1.00 | 1.00 | 1.00 | 1.00 |
| Mir6979 | 0.72 | 0.48 | 1.00 | 0.01 | 1.40 | 0.01 | 1.00 | 1.00 | 1.00 | 1.00 | 1.00 | 1.00 |
| Mir6980 | 1.00 | 1.00 | 1.00 | 0.02 | 1.00 | 1.02 | 1.00 | 1.00 | 1.00 | 1.00 | 1.00 | 1.00 |
| Mir6981 | 2.10 | 0.10 | 0.09 | 0.87 | 0.90 | 0.37 | 0.35 | 1.00 | 0.30 | 1.00 | 1.00 | 1.00 |
| Mir6984 | 84.25 | 1.00 | 1.00 | 1.00 | 0.03 | 1.00 | 1.00 | 1.00 | 1.00 | 1.00 | 1.00 | 1.00 |
| Mir6985 | 1.00 | 0.02 | 1.00 | 0.03 | 1.00 | 1.00 | 1.00 | 1.00 | 1.00 | 1.00 | 1.00 | 1.00 |
| Mir6986 | 0.40 | 68.00 | 0.01 | 57.61 | 57.32 | 1.22 | 1.00 | 0.02 | 1.00 | 1.00 | 1.00 | 1.00 |
| Mir6988 | 1.62 | 0.87 | 0.77 | 237.35 | 2.83 | 1.16 | 33.79 | 0.57 | 56.42 | 1.00 | 1.00 | 1.00 |
| Mir6989 | 1.14 | 1.35 | 0.45 | 1.07 | 0.91 | 1.37 | 1.00 | 1.00 | 0.04 | 1.00 | 1.00 | 1.00 |
| Mir6991 | 1.91 | 0.58 | 0.96 | 2.42 | 0.92 | 27.12 | 15.39 | 1.00 | 1.00 | 1.00 | 1.00 | 1.00 |
| Mir6993 | 78.30 | 3.60 | 0.01 | 1.16 | 0.03 | 0.03 | 1.00 | 1.00 | 1.00 | 1.00 | 1.00 | 1.00 |
| Mir6994 | 1.00 | 1.00 | 1.00 | 1.00 | 1.00 | 1.00 | 1.00 | 1.00 | 1.00 | 1.00 | 1.00 | 1.00 |
| Mir6995 | 25.05 | 1.00 | 30.38 | 1.00 | 1.00 | 1.00 | 1.00 | 1.00 | 1.00 | 1.00 | 1.00 | 1.00 |
| Mir6996 | 1.00 | 1.00 | 0.02 | 0.03 | 0.02 | 1.00 | 1.00 | 1.00 | 1.00 | 1.00 | 1.00 | 1.00 |
| Mir6997 | 1.00 | 1.00 | 1.00 | 1.00 | 1.00 | 1.00 | 1.00 | 1.00 | 1.00 | 1.00 | 1.00 | 1.00 |
| Mir6998 | 123.71 | 0.87 | 0.50 | 76.23 | 0.03 | 1.00 | 21.79 | 1.00 | 0.03 | 1.00 | 1.00 | 75.93 |
| Mir6999 | 0.93 | 0.94 | 0.81 | 1.05 | 1.46 | 1.33 | 1.00 | 0.65 | 1.00 | 1.00 | 1.00 | 1.00 |
| Mir700 | 0.81 | 0.79 | 0.02 | 0.02 | 4.13 | 48.55 | 0.51 | 1.00 | 1.00 | 1.00 | 1.00 | 1.00 |
| Mir7000 | 1.00 | 1.00 | 1.00 | 1.00 | 1.00 | 1.00 | 1.00 | 1.00 | 1.00 | 1.00 | 1.00 | 1.00 |
| Mir7001 | 4.07 | 0.26 | 1.20 | 0.60 | 1.65 | 0.75 | 9.30 | 0.96 | 1.79 | 1.00 | 1.00 | 1.00 |
| Mir7003 | 1.00 | 1.00 | 1.00 | 1.00 | 1.00 | 1.00 | 1.00 | 1.00 | 1.00 | 1.00 | 1.00 | 1.00 |
| Mir7004 | 0.03 | 1.00 | 1.00 | 1.00 | 1.00 | 1.00 | 1.00 | 1.00 | 1.00 | 1.00 | 1.00 | 1.00 |
| Mir7005 | 28.38 | 0.94 | 1.00 | 1.00 | 1.00 | 1.00 | 15.54 | 24.96 | 1.00 | 1.00 | 1.00 | 1.00 |
| Mir7006 | 178.57 | 1.57 | 0.63 | 6.57 | 0.46 | 0.28 | 1.00 | 1.00 | 0.04 | 1.00 | 1.00 | 1.00 |
| Mir7007 | 1.00 | 23.51 | 0.03 | 23.66 | 21.16 | 2.33 | 0.05 | 1.00 | 1.00 | 1.00 | 1.00 | 1.00 |
| Mir7009 | 1.00 | 1.00 | 1.00 | 41.77 | 1.00 | 1.00 | 1.00 | 1.00 | 1.00 | 1.00 | 1.00 | 1.00 |
| Mir7010 | 1.00 | 1.00 | 1.00 | 1.00 | 1.00 | 1.00 | 1.00 | 1.00 | 1.00 | 1.00 | 1.00 | 1.00 |
| Mir7011 | 0.57 | 0.94 | 76.22 | 0.03 | 0.50 | 1.22 | 1.00 | 19.58 | 1.00 | 1.00 | 1.00 | 1.00 |
| Mir7012 | 0.50 | 2.22 | 52.00 | 0.03 | 1.00 | 0.58 | 21.79 | 0.04 | 1.00 | 1.00 | 1.00 | 1.00 |
| Mir7013 | 0.79 | 0.69 | 0.89 | 0.82 | 1.81 | 1.13 | 0.75 | 2.01 | 0.05 | 1.00 | 1.00 | 1.00 |
| Mir7014 | 0.94 | 3.72 | 1.98 | 45.01 | 0.95 | 1.00 | 0.85 | 1.00 | 1.00 | 1.00 | 1.00 | 1.00 |
| Mir7015 | 0.01 | 0.01 | 1.00 | 1.00 | 1.00 | 1.08 | 1.00 | 1.00 | 1.00 | 1.00 | 1.00 | 1.00 |
| Mir7016 | 1.00 | 1.00 | 0.04 | 1.00 | 1.00 | 1.00 | 1.00 | 1.00 | 1.00 | 1.00 | 1.00 | 1.00 |
| Mir7017 | 46.50 | 1.00 | 1.00 | 1.00 | 1.00 | 54.68 | 1.00 | 1.00 | 1.00 | 1.00 | 1.00 | 1.00 |
| Mir7018 | 1.00 | 1.00 | 1.00 | 1.00 | 1.00 | 1.00 | 1.00 | 1.00 | 1.00 | 1.00 | 1.00 | 1.00 |
| Mir7019 | 0.72 | 3.86 | 0.64 | 0.04 | 46.61 | 1.08 | 1.00 | 1.00 | 1.00 | 1.00 | 1.00 | 1.00 |
| Mir702 | 1.00 | 9.68 | 1.00 | 0.14 | 1.71 | 0.10 | 1.00 | 0.29 | 3.63 | 1.00 | 1.00 | 1.00 |
| Mir7020 | 0.53 | 1.00 | 30.10 | 1.00 | 1.00 | 1.00 | 1.00 | 1.00 | 1.00 | 1.00 | 1.00 | 1.00 |
| Mir7021 | 1.00 | 1.00 | 1.00 | 1.00 | 1.00 | 1.00 | 1.00 | 1.00 | 1.00 | 1.00 | 1.00 | 1.00 |
| Mir7022 | 0.01 | 44.35 | 1.00 | 0.03 | 1.00 | 1.00 | 1.00 | 1.00 | 1.00 | 1.00 | 1.00 | 1.00 |
| Mir7023 | 2.90 | 0.01 | 1.00 | 0.33 | 0.98 | 1.00 | 1.00 | 1.00 | 1.00 | 1.00 | 1.00 | 1.00 |
| Mir7024 | 1.12 | 0.40 | 1.98 | 0.78 | 0.48 | 2.36 | 1.00 | 0.03 | 1.00 | 1.00 | 1.00 | 1.00 |
| Mir7025 | 1.00 | 1.00 | 1.00 | 1.00 | 1.00 | 1.00 | 1.00 | 1.00 | 1.00 | 1.00 | 1.00 | 1.00 |
| Mir7026 | 1.42 | 2.52 | 1.52 | 1.48 | 0.01 | 0.84 | 0.02 | 0.04 | 0.03 | 1.00 | 1.00 | 1.00 |
| Mir7027 | 1.23 | 1.01 | 2.14 | 0.99 | 1.53 | 2.03 | 12.96 | 55.83 | 1.08 | 1.00 | 1.00 | 1.00 |
| Mir7028 | 1.12 | 0.67 | 0.20 | 1.16 | 0.03 | 0.01 | 1.00 | 0.04 | 1.00 | 1.00 | 1.00 | 1.00 |
| Mir7030 | 0.44 | 0.24 | 3.90 | 2.45 | 1.02 | 0.70 | 29.71 | 1.00 | 1.00 | 1.00 | 1.00 | 1.00 |
| Mir7031 | 0.03 | 1.88 | 95.07 | 1.00 | 2.92 | 1.02 | 1.00 | 1.00 | 1.00 | 1.00 | 1.00 | 1.00 |
| Mir7032 | 1.00 | 2.75 | 1.00 | 16.77 | 1.00 | 0.07 | 1.00 | 1.00 | 1.00 | 1.00 | 1.00 | 1.00 |
| Mir7033 | 1.00 | 25.19 | 1.00 | 1.00 | 12.87 | 1.00 | 1.00 | 1.00 | 1.00 | 1.00 | 1.00 | 1.00 |
| Mir7034 | 1.00 | 1.11 | 0.36 | 2.21 | 11.16 | 1.00 | 1.00 | 9.82 | 1.00 | 1.00 | 1.00 | 1.00 |

Fig. 31-81

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir7035 | 1.73 | 4.94 | 0.93 | 21.28 | 0.05 | 1.00 | 1.00 | 14.60 | 1.00 |
| Mir7036 | 0.62 | 1.07 | 0.77 | 2.17 | 4.49 | 2.08 | 1.00 | 2.34 | 0.01 |
| Mir7036b | 89.45 | 0.02 | 1.00 | 0.01 | 108.79 | 0.01 | 0.01 | 0.01 | 73.21 |
| Mir7037 | 73.62 | 0.90 | 1.00 | 2.24 | 1.00 | 1.00 | 1.00 | 1.00 | 1.00 |
| Mir7039 | 1.00 | 1.00 | 1.00 | 1.00 | 1.00 | 1.00 | 1.00 | 12.43 | 1.00 |
| Mir704 | 1.00 | 1.00 | 1.00 | 1.00 | 1.00 | 0.05 | 1.82 | 1.06 | 1.76 |
| Mir7041 | 1.00 | 0.01 | 1.00 | 1.00 | 1.00 | 1.00 | 1.00 | 1.00 | 1.00 |
| Mir7042 | 1.00 | 1.00 | 1.00 | 1.00 | 1.00 | 111.83 | 1.00 | 1.00 | 1.00 |
| Mir7043 | 1.00 | 23.99 | 1.00 | 1.00 | 1.00 | 1.00 | 1.00 | 1.00 | 1.00 |
| Mir7044 | 1.00 | 1.00 | 1.00 | 1.00 | 1.00 | 1.00 | 1.00 | 1.00 | 1.00 |
| Mir7045 | 0.99 | 0.99 | 0.73 | 0.79 | 1.37 | 0.52 | 0.55 | 0.01 | 0.02 |
| Mir7046 | 0.88 | 1.00 | 1.00 | 124.21 | 76.81 | 45.83 | 0.44 | 1.00 | 0.02 |
| Mir7048 | 1.00 | 1.00 | 66.21 | 1.00 | 1.00 | 1.00 | 1.00 | 1.00 | 1.00 |
| Mir7049 | 1.00 | 1.00 | 1.00 | 1.00 | 1.00 | 1.00 | 1.00 | 1.00 | 1.00 |
| Mir7050 | 115.64 | 5.32 | 0.02 | 1.00 | 1.00 | 1.00 | 1.00 | 1.00 | 0.02 |
| Mir7051 | 1.16 | 0.43 | 0.02 | 1.62 | 1.31 | 2.05 | 3.52 | 1.72 | 0.62 |
| Mir7052 | 0.74 | 0.86 | 0.90 | 0.00 | 1.70 | 201.23 | 0.63 | 0.41 | 0.86 |
| Mir7053 | 22.44 | 39.74 | 1.00 | 1.00 | 1.00 | 26.83 | 1.00 | 1.00 | 1.00 |
| Mir7054 | 1.78 | 1.00 | 47.59 | 0.01 | 1.00 | 1.00 | 1.00 | 1.00 | 1.00 |
| Mir7058 | 36.97 | 18.54 | 1.00 | 1.00 | 1.00 | 23.31 | 27.08 | 29.96 | 1.00 |
| Mir7059 | 118.80 | 0.90 | 1.00 | 1.00 | 1.15 | 1.00 | 1.00 | 1.00 | 0.01 |
| Mir7061 | 0.03 | 1.00 | 1.00 | 1.00 | 1.15 | 0.01 | 1.00 | 1.00 | 1.00 |
| Mir7062 | 35.73 | 1.00 | 34.84 | 1.00 | 1.00 | 1.00 | 1.00 | 1.00 | 1.00 |
| Mir7063 | 24.69 | 1.00 | 0.05 | 1.21 | 0.39 | 0.11 | 2.14 | 9.27 | 11.40 |
| Mir7064 | 1.00 | 1.00 | 1.00 | 1.00 | 1.00 | 1.00 | 1.00 | 1.00 | 1.00 |
| Mir7066 | 1.00 | 1.00 | 1.00 | 1.00 | 1.00 | 1.00 | 1.00 | 1.00 | 1.00 |
| Mir7067 | 2.57 | 124.35 | 0.89 | 185.18 | 108.79 | 0.02 | 0.01 | 1.00 | 1.00 |
| Mir7068 | 0.04 | 1.67 | 20.05 | 0.01 | 0.03 | 0.52 | 55.39 | 32.06 | 1.00 |
| Mir7069 | 2.23 | 0.88 | 0.89 | 112.69 | 0.01 | 1.01 | 0.01 | 1.00 | 0.01 |
| Mir707 | 67.96 | 1.00 | 0.02 | 0.01 | 0.54 | 0.21 | 1.00 | 0.29 | 1.00 |
| Mir7070 | 10.66 | 1.00 | 0.47 | 1.00 | 1.00 | 2.04 | 1.00 | 1.94 | 0.97 |
| Mir7071 | 1.00 | 1.00 | 28.24 | 1.00 | 1.00 | 0.03 | 1.00 | 1.00 | 1.00 |
| Mir7072 | 1.00 | 1.00 | 1.00 | 1.00 | 1.00 | 1.00 | 1.00 | 1.00 | 1.00 |
| Mir7073 | 1.00 | 1.00 | 1.00 | 1.00 | 1.00 | 1.00 | 1.00 | 1.00 | 1.00 |
| Mir7074 | 1.00 | 1.00 | 1.00 | 1.00 | 1.00 | 1.00 | 1.00 | 79.48 | 1.00 |
| Mir7075 | 1.00 | 0.07 | 0.95 | 18.37 | 1.00 | 14.57 | 1.00 | 1.00 | 1.00 |
| Mir7077 | 1.00 | 1.00 | 1.00 | 1.00 | 1.00 | 1.00 | 1.00 | 1.00 | 1.00 |
| Mir7078 | 1.00 | 0.02 | 40.52 | 1.00 | 0.01 | 1.00 | 1.00 | 1.00 | 1.00 |
| Mir7079 | 1.73 | 103.09 | 0.62 | 0.56 | 0.58 | 3.02 | 1.77 | 1.11 | 0.01 |
| Mir708 | 1.00 | 1.00 | 1.00 | 1.00 | 1.00 | 0.22 | 1.00 | 1.00 | 1.00 |
| Mir7080 | 1.00 | 59.31 | 0.95 | 0.02 | 1.00 | 0.02 | 1.00 | 1.00 | 1.00 |
| Mir7081 | 1.00 | 1.00 | 1.00 | 1.00 | 1.00 | 1.00 | 1.00 | 1.00 | 1.00 |
| Mir7082 | 0.66 | 0.11 | 0.95 | 1.76 | 1.13 | 1.28 | 0.53 | 0.09 | 1.65 |
| Mir7083 | 0.02 | 0.01 | 1.00 | 125.50 | 1.00 | 1.00 | 1.00 | 0.01 | 1.00 |
| Mir7085 | 1.00 | 1.00 | 0.03 | 1.00 | 2.25 | 1.00 | 2.06 | 2.87 | 0.59 |
| Mir7086 | 1.00 | 1.00 | 1.00 | 1.00 | 1.00 | 1.00 | 1.00 | 1.00 | 1.00 |
| Mir7087 | 1.68 | 0.04 | 1.36 | 1.68 | 2.24 | 0.69 | 0.33 | 147.68 | 0.86 |
| Mir7088 | 1.00 | 0.09 | 1.00 | 30.57 | 1.00 | 1.00 | 14.27 | 0.86 | 0.03 |
| Mir7089 | 1.00 | 1.00 | 30.23 | 1.00 | 1.00 | 77.11 | 1.00 | 1.00 | 44.66 |
| Mir709 | 1.00 | 9.64 | 1.00 | 1.00 | 1.00 | 1.00 | 1.00 | 10.69 | 1.00 |
| Mir7090 | 1.00 | 0.02 | 1.00 | 1.00 | 1.00 | 1.00 | 1.00 | 1.00 | 0.02 |
| Mir7091 | 0.64 | 1.36 | 2.15 | 1.29 | 0.38 | 0.26 | 19.90 | 2.81 | 0.08 |
| Mir7092 | 1.00 | 1.00 | 0.03 | 1.00 | 1.00 | 1.00 | 1.00 | 1.00 | 1.00 |
| Mir7093 | 0.15 | 5.52 | 6.04 | 0.08 | 0.14 | 0.37 | 1.03 | 0.13 | 1.00 |
| Mir711 | 10.35 | 0.50 | 1.71 | 1.00 | 1.00 | 15.09 | 1.00 | 1.00 | 1.00 |
| Mir7115 | 2.23 | 1.23 | 6.05 | 76.93 | 1.15 | 1.01 | 0.67 | 1.51 | 0.63 |
| Mir7117 | 0.47 | 0.26 | 0.93 | 1.00 | 0.01 | 1.00 | 1.00 | 1.00 | 1.00 |
| Mir7118 | 1.00 | 1.00 | 1.00 | 1.00 | 1.00 | 1.00 | 88.60 | 1.00 | 1.00 |
| Mir713 | 1.00 | 1.00 | 1.00 | 1.00 | 1.00 | 1.00 | 1.00 | 1.00 | 1.00 |
| Mir719 | 0.73 | 0.56 | 0.47 | 2.81 | 1.86 | 1.47 | 1.81 | 0.20 | 0.60 |
| Mir7210 | 1.00 | 1.00 | 1.00 | 1.00 | 1.00 | 1.00 | 1.00 | 1.00 | 1.00 |
| Mir7211 | 1.36 | 0.02 | 0.01 | 1.00 | 1.00 | 1.00 | 1.00 | 79.48 | 0.02 |
| Mir7214 | 1.00 | 1.00 | 1.00 | 1.00 | 1.00 | 1.00 | 1.00 | 1.00 | 1.00 |
| Mir7215 | 1.00 | 1.00 | 1.00 | 1.00 | 1.00 | 1.00 | 1.00 | 1.00 | 1.00 |

Fig. 31-82

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir7035 | 1.02 | 0.99 | 2.67 | 0.66 | 1.01 | 0.94 | 3.44 | 0.56 | 0.86 |
| Mir7036 | 0.81 | 1.23 | 0.45 | 1.09 | 2.57 | 3.31 | 2.23 | 2.79 | 1.94 |
| Mir7036b | 1.02 | 112.84 | 0.71 | 0.92 | 1.00 | 37.59 | 0.71 | 1.08 | 0.80 |
| Mir7037 | 61.64 | 0.66 | 0.57 | 39.65 | 1.00 | 1.00 | 1.00 | 0.60 | 0.01 |
| Mir7039 | 1.00 | 10.48 | 1.00 | 1.00 | 1.00 | 1.00 | 1.00 | 1.00 | 1.00 |
| Mir704 | 0.07 | 42.24 | 1.08 | 1.00 | 15.82 | 14.94 | 1.89 | 0.79 | 7.16 |
| Mir7041 | 0.00 | 1.00 | 0.00 | 1.00 | 1.00 | 1.00 | 1.00 | 1.00 | 1.00 |
| Mir7042 | 1.00 | 1.00 | 1.00 | 1.00 | 1.00 | 62.35 | 1.00 | 1.00 | 119.91 |
| Mir7043 | 1.00 | 0.05 | 1.00 | 1.00 | 1.00 | 1.00 | 1.00 | 1.00 | 1.00 |
| Mir7044 | 2.60 | 0.14 | 0.53 | 1.00 | 1.00 | 1.00 | 1.00 | 1.00 | 1.00 |
| Mir7045 | 3.71 | 2.50 | 1.61 | 1.15 | 3.75 | 2.28 | 1.28 | 1.90 | 0.50 |
| Mir7046 | 3.16 | 0.56 | 1.09 | 161.77 | 0.03 | 1.87 | 162.58 | 1.09 | 0.55 |
| Mir7048 | 1.00 | 0.98 | 57.96 | 1.00 | 1.00 | 1.00 | 1.01 | 2.26 | 0.55 |
| Mir7049 | 0.00 | 0.25 | 1.08 | 1.00 | 0.02 | 51.77 | 1.00 | 1.00 | 0.01 |
| Mir7050 | 0.80 | 1.76 | 3.29 | 0.02 | 1.00 | 0.02 | 0.46 | 0.92 | 0.48 |
| Mir7051 | 1.93 | 0.20 | 0.39 | 41.12 | 2.07 | 1.47 | 0.45 | 1.07 | 1.33 |
| Mir7052 | 0.46 | 0.80 | 2.56 | 5.32 | 0.25 | 1.82 | 1.17 | 1.21 | 1.91 |
| Mir7053 | 1.00 | 17.64 | 1.00 | 1.00 | 1.00 | 1.00 | 0.01 | 3.41 | 108.73 |
| Mir7054 | 40.97 | 1.00 | 3.13 | 1.00 | 0.02 | 0.02 | 1.00 | 90.74 | 0.01 |
| Mir7058 | 0.73 | 1.58 | 0.72 | 1.00 | 1.00 | 0.06 | 3.06 | 1.74 | 1.49 |
| Mir7059 | 0.48 | 0.50 | 1.00 | 1.00 | 1.00 | 1.00 | 1.87 | 2.10 | 0.01 |
| Mir7061 | 0.22 | 0.28 | 2.70 | 1.00 | 26.11 | 0.04 | 2.86 | 57.74 | 0.01 |
| Mir7062 | 30.01 | 1.00 | 1.00 | 1.00 | 1.00 | 1.00 | 0.02 | 0.02 | 0.02 |
| Mir7063 | 1.55 | 1.48 | 1.61 | 0.07 | 8.10 | 1.00 | 0.52 | 6.17 | 4.88 |
| Mir7064 | 1.00 | 1.00 | 1.00 | 1.00 | 1.00 | 1.00 | 1.00 | 30.50 | 1.00 |
| Mir7066 | 1.00 | 1.00 | 1.00 | 1.00 | 1.00 | 1.00 | 1.00 | 1.00 | 1.00 |
| Mir7067 | 1.02 | 0.64 | 1.50 | 1.00 | 37.84 | 0.01 | 0.25 | 0.01 | 1.29 |
| Mir7068 | 3.01 | 0.74 | 1.64 | 0.92 | 0.99 | 1.00 | 3.56 | 0.59 | 0.54 |
| Mir7069 | 0.50 | 0.99 | 0.52 | 0.02 | 1.00 | 40.79 | 0.65 | 2.26 | 2.51 |
| Mir707 | 1.00 | 44.41 | 0.73 | 87.95 | 37.88 | 0.36 | 0.37 | 111.89 | 1.34 |
| Mir7070 | 3.94 | 1.99 | 1.14 | 0.10 | 1.00 | 1.00 | 1.89 | 1.00 | 12.48 |
| Mir7071 | 1.00 | 22.72 | 1.00 | 1.00 | 24.39 | 24.23 | 1.00 | 1.00 | 1.00 |
| Mir7072 | 1.00 | 51.00 | 1.00 | 1.00 | 1.00 | 1.00 | 105.64 | 113.17 | 1.00 |
| Mir7073 | 1.00 | 1.00 | 1.00 | 1.00 | 1.00 | 1.00 | 1.00 | 1.00 | 1.00 |
| Mir7074 | 1.00 | 1.00 | 1.00 | 1.00 | 1.00 | 1.00 | 1.00 | 1.00 | 1.00 |
| Mir7075 | 1.00 | 1.99 | 12.18 | 1.00 | 0.09 | 1.00 | 0.05 | 1.11 | 0.47 |
| Mir7077 | 1.00 | 1.00 | 68.27 | 1.00 | 1.00 | 1.00 | 1.00 | 1.00 | 1.00 |
| Mir7078 | 69.28 | 0.56 | 68.49 | 1.00 | 1.00 | 1.00 | 69.25 | 0.01 | 169.02 |
| Mir7079 | 0.84 | 2.21 | 2.41 | 0.96 | 0.50 | 0.01 | 2.07 | 1.93 | 1.05 |
| Mir708 | 1.00 | 1.00 | 1.00 | 1.00 | 1.00 | 1.00 | 1.00 | 1.00 | 1.00 |
| Mir7080 | 1.00 | 1.00 | 54.73 | 28.12 | 1.00 | 1.00 | 1.00 | 1.07 | 1.00 |
| Mir7081 | 0.07 | 15.68 | 16.60 | 1.00 | 16.82 | 1.00 | 0.04 | 1.00 | 1.00 |
| Mir7082 | 1.53 | 7.62 | 3.26 | 23.89 | 0.13 | 2.06 | 1.40 | 2.65 | 0.71 |
| Mir7083 | 0.02 | 95.41 | 1.08 | 49.00 | 1.00 | 1.00 | 1.00 | 1.00 | 1.00 |
| Mir7085 | 30.01 | 28.02 | 1.00 | 1.00 | 0.03 | 29.88 | 53.28 | 0.58 | 1.01 |
| Mir7086 | 1.00 | 30.17 | 65.05 | 1.00 | 1.00 | 1.00 | 58.34 | 0.50 | 1.10 |
| Mir7087 | 1.53 | 2.02 | 1.34 | 49.85 | 1.02 | 0.84 | 2.44 | 0.52 | 0.69 |
| Mir7088 | 1.02 | 0.06 | 19.65 | 1.00 | 1.00 | 1.00 | 0.73 | 2.28 | 0.47 |
| Mir7089 | 26.05 | 0.98 | 0.02 | 1.00 | 1.00 | 1.00 | 1.36 | 0.58 | 0.51 |
| Mir709 | 1.00 | 1.00 | 0.12 | 1.00 | 1.00 | 1.00 | 13.72 | 1.00 | 1.00 |
| Mir7090 | 1.00 | 42.92 | 1.00 | 1.00 | 1.00 | 1.00 | 1.00 | 0.99 | 0.89 |
| Mir7091 | 0.78 | 1.55 | 0.90 | 0.88 | 1.71 | 1.69 | 1.07 | 1.51 | 2.05 |
| Mir7092 | 1.00 | 0.04 | 27.47 | 1.00 | 1.00 | 1.00 | 1.00 | 1.00 | 39.67 |
| Mir7093 | 1.90 | 1.88 | 1.63 | 1.87 | 2.75 | 5.24 | 0.07 | 9.19 | 4.82 |
| Mir711 | 1.00 | 1.00 | 1.00 | 1.00 | 12.99 | 1.00 | 1.00 | 0.05 | 1.00 |
| Mir7115 | 1.12 | 1.84 | 1.32 | 0.59 | 0.77 | 0.92 | 1.05 | 0.09 | 0.60 |
| Mir7117 | 32.32 | 1.00 | 34.09 | 2.91 | 0.41 | 1.21 | 0.01 | 0.02 | 1.00 |
| Mir7118 | 1.00 | 1.00 | 1.00 | 1.00 | 1.00 | 1.00 | 1.00 | 1.00 | 1.00 |
| Mir713 | 1.00 | 1.00 | 1.00 | 1.00 | 1.00 | 1.00 | 1.00 | 1.00 | 1.00 |
| Mir719 | 1.00 | 0.93 | 0.66 | 1.62 | 1.11 | 1.16 | 0.82 | 2.17 | 0.37 |
| Mir7210 | 1.00 | 1.00 | 1.00 | 1.00 | 1.00 | 1.00 | 1.00 | 1.00 | 1.00 |
| Mir7211 | 0.01 | 0.51 | 0.32 | 38.01 | 39.85 | 76.74 | 1.79 | 0.01 | 0.02 |
| Mir7214 | 1.00 | 1.00 | 1.00 | 1.00 | 1.00 | 1.00 | 1.00 | 1.00 | 1.00 |
| Mir7215 | 1.00 | 1.00 | 1.00 | 1.00 | 1.00 | 1.00 | 1.00 | 1.00 | 1.00 |

Fig. 31-83

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir7035 | 0.74 | 0.02 | 0.04 | 0.36 | 1.36 | 0.99 | 1.00 | 1.00 | 1.00 |
| Mir7036 | 0.53 | 0.72 | 0.90 | 0.27 | 1.40 | 1.09 | 0.55 | 1.38 | 1.21 |
| Mir7036b | 0.38 | 0.01 | 0.02 | 101.10 | 101.55 | 112.04 | 1.00 | 32.79 | 1.00 |
| Mir7037 | 0.01 | 0.00 | 51.14 | 0.02 | 1.08 | 0.02 | 1.00 | 28.20 | 29.86 |
| Mir7039 | 1.00 | 15.51 | 1.00 | 1.00 | 1.00 | 1.00 | 1.00 | 1.00 | 1.18 |
| Mir704 | 1.00 | 1.00 | 1.00 | 0.61 | 79.82 | 1.03 | 16.47 | 1.00 | 16.25 |
| Mir7041 | 1.00 | 1.00 | 1.00 | 1.00 | 1.00 | 1.00 | 1.00 | 1.00 | 1.00 |
| Mir7042 | 1.00 | 1.00 | 1.00 | 1.00 | 1.00 | 1.00 | 1.00 | 1.00 | 1.00 |
| Mir7043 | 1.00 | 1.00 | 1.00 | 1.00 | 1.00 | 1.00 | 1.00 | 1.00 | 1.00 |
| Mir7044 | 1.18 | 0.50 | 28.31 | 1.00 | 1.00 | 1.00 | 1.00 | 1.00 | 1.00 |
| Mir7045 | 1.87 | 1.97 | 1.03 | 1.14 | 3.53 | 1.47 | 0.55 | 2.30 | 3.83 |
| Mir7046 | 1.93 | 272.60 | 0.02 | 0.01 | 132.96 | 0.51 | 1.00 | 51.99 | 1.13 |
| Mir7048 | 1.00 | 1.00 | 1.00 | 1.00 | 1.00 | 1.00 | 1.00 | 1.00 | 0.02 |
| Mir7049 | 1.00 | 1.00 | 1.00 | 1.00 | 1.00 | 1.00 | 1.00 | 1.00 | 0.02 |
| Mir7050 | 0.01 | 149.49 | 0.01 | 1.00 | 1.00 | 1.00 | 1.00 | 1.00 | 1.01 |
| Mir7051 | 1.00 | 0.03 | 0.04 | 1.00 | 1.14 | 1.72 | 1.00 | 33.74 | 0.06 |
| Mir7052 | 0.71 | 1.49 | 0.46 | 0.02 | 0.01 | 0.02 | 0.44 | 1.37 | 0.60 |
| Mir7053 | 1.00 | 1.00 | 1.00 | 1.00 | 1.00 | 1.00 | 0.05 | 1.00 | 1.00 |
| Mir7054 | 1.00 | 0.01 | 0.02 | 0.01 | 1.00 | 125.58 | 43.43 | 1.00 | 0.03 |
| Mir7058 | 1.00 | 1.00 | 1.00 | 1.00 | 0.04 | 0.05 | 18.39 | 1.00 | 1.00 |
| Mir7059 | 0.01 | 1.00 | 1.00 | 0.01 | 1.00 | 1.00 | 1.09 | 0.02 | 1.00 |
| Mir7061 | 0.90 | 0.97 | 74.26 | 1.00 | 114.84 | 0.51 | 0.01 | 1.00 | 50.24 |
| Mir7062 | 1.00 | 1.00 | 1.00 | 1.00 | 1.00 | 1.00 | 1.00 | 26.25 | 1.00 |
| Mir7063 | 21.77 | 0.96 | 2.90 | 1.99 | 1.18 | 1.00 | 1.92 | 1.48 | 0.51 |
| Mir7064 | 0.08 | 1.00 | 1.00 | 1.00 | 0.09 | 1.00 | 9.26 | 1.00 | 1.00 |
| Mir7066 | 1.00 | 1.00 | 58.23 | 1.00 | 1.00 | 1.00 | 1.00 | 1.00 | 1.00 |
| Mir7067 | 0.74 | 1.00 | 1.00 | 1.00 | 1.00 | 2.84 | 40.60 | 0.03 | 34.72 |
| Mir7068 | 0.74 | 0.34 | 22.83 | 1.74 | 0.70 | 0.99 | 0.37 | 15.78 | 3.05 |
| Mir7069 | 1.00 | 0.00 | 0.77 | 0.01 | 115.94 | 61.60 | 1.38 | 1.77 | 1.99 |
| Mir707 | 0.52 | 0.32 | 28.83 | 4.07 | 47.46 | 0.01 | 35.68 | 0.13 | 52.42 |
| Mir7070 | 1.00 | 1.00 | 0.35 | 16.56 | 13.46 | 1.00 | 1.11 | 16.71 | 10.11 |
| Mir7071 | 1.00 | 1.00 | 1.00 | 1.00 | 1.00 | 1.00 | 1.00 | 1.00 | 0.04 |
| Mir7072 | 1.00 | 1.00 | 1.00 | 1.00 | 1.00 | 1.00 | 1.00 | 1.00 | 1.00 |
| Mir7073 | 1.00 | 1.00 | 1.00 | 1.00 | 1.00 | 1.00 | 1.00 | 1.00 | 1.00 |
| Mir7074 | 1.00 | 1.00 | 1.00 | 1.00 | 1.00 | 1.00 | 1.00 | 1.00 | 1.00 |
| Mir7075 | 1.00 | 1.00 | 0.04 | 37.85 | 1.98 | 1.08 | 1.00 | 0.91 | 0.09 |
| Mir7077 | 1.00 | 1.00 | 0.01 | 1.00 | 1.00 | 1.00 | 1.00 | 1.00 | 1.00 |
| Mir7078 | 1.00 | 0.01 | 1.00 | 1.00 | 79.16 | 1.00 | 1.00 | 1.00 | 0.03 |
| Mir7079 | 1.78 | 0.96 | 0.50 | 1.15 | 0.80 | 0.35 | 0.55 | 1.00 | 0.67 |
| Mir708 | 4.65 | 1.00 | 1.00 | 1.89 | 15.25 | 1.94 | 1.00 | 1.00 | 1.00 |
| Mir7080 | 3.85 | 3.81 | 0.63 | 1.00 | 1.00 | 0.02 | 1.00 | 1.21 | 28.93 |
| Mir7081 | 1.00 | 1.00 | 1.00 | 1.00 | 1.00 | 1.00 | 1.00 | 0.03 | 15.77 |
| Mir7082 | 47.42 | 2.01 | 0.62 | 0.63 | 1.07 | 16.17 | 0.59 | 1.38 | 0.29 |
| Mir7083 | 1.00 | 1.00 | 1.00 | 1.00 | 1.00 | 1.00 | 1.00 | 1.00 | 1.00 |
| Mir7085 | 1.00 | 1.00 | 0.02 | 77.73 | 1.00 | 43.45 | 1.00 | 1.00 | 31.08 |
| Mir7086 | 1.00 | 1.00 | 1.00 | 79.24 | 1.00 | 45.27 | 1.00 | 1.00 | 1.00 |
| Mir7087 | 40.27 | 2.00 | 2.97 | 0.01 | 1.64 | 2.15 | 0.37 | 21.65 | 0.50 |
| Mir7088 | 0.03 | 1.00 | 11.91 | 1.00 | 44.55 | 1.00 | 1.00 | 1.00 | 1.00 |
| Mir7089 | 0.02 | 0.02 | 1.00 | 1.00 | 0.01 | 1.00 | 55.24 | 0.89 | 27.08 |
| Mir709 | 0.06 | 0.08 | 0.10 | 1.00 | 1.00 | 1.00 | 1.00 | 7.88 | 0.06 |
| Mir7090 | 1.00 | 1.00 | 1.00 | 1.00 | 1.00 | 1.00 | 1.00 | 1.00 | 0.03 |
| Mir7091 | 1.00 | 1.98 | 1.00 | 0.84 | 2.52 | 0.16 | 14.65 | 0.04 | 1.00 |
| Mir7092 | 1.00 | 1.00 | 1.00 | 1.00 | 50.96 | 1.00 | 1.00 | 1.00 | 1.00 |
| Mir7093 | 1.48 | 0.65 | 1.99 | 2.29 | 3.03 | 0.17 | 1.00 | 0.85 | 1.00 |
| Mir711 | 1.00 | 1.00 | 1.00 | 1.00 | 1.00 | 1.00 | 1.00 | 0.06 | 1.00 |
| Mir7115 | 0.40 | 7.03 | 1.03 | 1.44 | 0.78 | 0.19 | 37.16 | 0.03 | 32.16 |
| Mir7117 | 1.00 | 1.00 | 1.00 | 1.00 | 1.00 | 1.00 | 1.00 | 1.00 | 1.00 |
| Mir7118 | 1.00 | 1.00 | 1.00 | 1.00 | 1.00 | 1.00 | 1.00 | 1.00 | 1.00 |
| Mir713 | 1.00 | 1.00 | 1.00 | 1.00 | 1.00 | 1.00 | 4.61 | 4.08 | 1.00 |
| Mir719 | 0.92 | 0.83 | 1.12 | 1.75 | 0.60 | 1.06 | 1.03 | 1.27 | 0.94 |
| Mir7210 | 1.00 | 1.00 | 1.00 | 1.00 | 1.00 | 1.00 | 184.23 | 0.91 | 158.63 |
| Mir7211 | 112.87 | 0.01 | 0.02 | 101.10 | 1.05 | 0.71 | 40.12 | 0.03 | 1.00 |
| Mir7214 | 1.00 | 1.00 | 1.00 | 1.00 | 1.00 | 1.00 | 0.41 | 2.35 | 0.80 |
| Mir7215 | 1.00 | 1.00 | 1.00 | 1.00 | 1.00 | 1.00 | 0.01 | 107.48 | 0.98 |

Fig. 31- 84

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir7035 | 2.57 | 2.51 | 2.99 | 0.08 | 2.74 | 1.08 | 1.00 | 1.00 | 10.73 | 1.00 | 1.00 | 1.00 |
| Mir7036 | 0.88 | 0.75 | 0.82 | 0.18 | 0.74 | 0.82 | 2.12 | 60.42 | 0.46 | 1.00 | 1.00 | 1.00 |
| Mir7036b | 0.46 | 1.02 | 0.69 | 4.88 | 0.93 | 1.05 | 23.45 | 0.03 | 0.02 | 1.00 | 1.00 | 1.00 |
| Mir7037 | 0.39 | 0.97 | 2.91 | 1.16 | 65.15 | 0.01 | 20.28 | 1.00 | 1.00 | 1.00 | 1.00 | 1.00 |
| Mir7039 | 13.59 | 1.00 | 13.48 | 1.00 | 1.00 | 0.09 | 1.00 | 1.00 | 1.00 | 1.00 | 1.00 | 1.00 |
| Mir704 | 0.33 | 0.54 | 0.51 | 0.06 | 0.06 | 17.30 | 9.84 | 1.28 | 1.00 | 1.00 | 1.00 | 1.00 |
| Mir7041 | 119.70 | 1.00 | 1.00 | 1.00 | 105.57 | 1.00 | 1.00 | 1.00 | 1.00 | 1.00 | 1.00 | 1.00 |
| Mir7042 | 0.02 | 1.00 | 1.00 | 1.00 | 1.00 | 1.00 | 1.00 | 1.00 | 1.00 | 1.00 | 1.00 | 1.00 |
| Mir7043 | 1.00 | 27.88 | 1.00 | 1.00 | 1.00 | 1.00 | 1.00 | 1.00 | 1.00 | 1.00 | 1.00 | 1.00 |
| Mir7044 | 1.00 | 1.00 | 1.00 | 41.42 | 1.00 | 1.00 | 1.00 | 1.00 | 1.00 | 1.00 | 1.00 | 1.00 |
| Mir7045 | 0.46 | 0.30 | 0.70 | 1.06 | 71.14 | 0.00 | 0.82 | 0.41 | 0.02 | 1.00 | 1.00 | 1.00 |
| Mir7046 | 0.86 | 0.85 | 0.83 | 61.01 | 0.01 | 1.02 | 18.92 | 26.81 | 0.59 | 1.00 | 1.00 | 1.00 |
| Mir7048 | 1.05 | 1.11 | 86.03 | 114.73 | 2.73 | 0.01 | 1.00 | 1.00 | 1.00 | 1.00 | 1.00 | 1.00 |
| Mir7049 | 0.02 | 0.01 | 0.36 | 1.00 | 1.00 | 0.02 | 1.00 | 1.00 | 1.00 | 1.00 | 1.00 | 1.00 |
| Mir7050 | 0.67 | 0.61 | 2.07 | 2.70 | 1.28 | 0.68 | 31.06 | 1.00 | 1.00 | 1.00 | 1.00 | 1.00 |
| Mir7051 | 0.47 | 0.99 | 1.01 | 1.15 | 0.64 | 46.31 | 1.00 | 1.00 | 1.00 | 1.00 | 1.00 | 1.00 |
| Mir7052 | 1.06 | 0.99 | 0.62 | 1.59 | 0.95 | 0.36 | 2.20 | 2.25 | 0.04 | 1.00 | 1.00 | 1.00 |
| Mir7053 | 0.60 | 0.94 | 1.03 | 2.09 | 2.02 | 2.05 | 1.00 | 1.00 | 1.00 | 1.00 | 1.00 | 1.00 |
| Mir7054 | 0.33 | 0.46 | 1.99 | 0.01 | 1.00 | 1.00 | 1.00 | 1.00 | 0.02 | 1.00 | 1.00 | 1.00 |
| Mir7058 | 0.73 | 0.87 | 0.93 | 1.22 | 0.91 | 2.95 | 0.26 | 1.00 | 15.98 | 1.00 | 1.00 | 1.00 |
| Mir7059 | 1.05 | 0.01 | 1.00 | 0.60 | 1.68 | 0.33 | 1.00 | 1.00 | 1.00 | 1.00 | 1.00 | 1.00 |
| Mir7061 | 6.78 | 0.02 | 0.03 | 0.63 | 1.00 | 33.18 | 1.00 | 1.00 | 1.00 | 1.00 | 1.00 | 1.00 |
| Mir7062 | 0.77 | 0.91 | 2.18 | 0.42 | 1.84 | 0.37 | 1.00 | 1.00 | 1.00 | 1.00 | 1.00 | 1.00 |
| Mir7063 | 0.62 | 24.66 | 0.55 | 0.51 | 2.22 | 1.69 | 1.00 | 1.00 | 7.02 | 1.00 | 1.00 | 1.00 |
| Mir7064 | 1.00 | 1.00 | 1.00 | 1.00 | 1.00 | 1.00 | 1.00 | 1.00 | 1.00 | 1.00 | 1.00 | 1.00 |
| Mir7066 | 1.00 | 1.00 | 1.00 | 1.00 | 1.00 | 1.00 | 1.00 | 1.00 | 1.00 | 1.00 | 1.00 | 1.00 |
| Mir7067 | 0.69 | 3.90 | 0.80 | 0.78 | 0.63 | 0.76 | 70.99 | 0.03 | 0.01 | 1.00 | 1.00 | 1.00 |
| Mir7068 | 0.97 | 0.41 | 1.13 | 0.60 | 1.23 | 1.81 | 1.00 | 18.49 | 1.00 | 1.00 | 1.00 | 1.00 |
| Mir7069 | 0.88 | 0.64 | 1.24 | 2.04 | 5.85 | 2.03 | 1.00 | 2.40 | 1.00 | 1.00 | 1.00 | 1.00 |
| Mir707 | 9.67 | 51.19 | 1.32 | 43.77 | 0.14 | 1.62 | 1.49 | 0.04 | 5.37 | 1.00 | 1.00 | 1.00 |
| Mir7070 | 1.92 | 3.02 | 1.03 | 1.00 | 1.00 | 1.00 | 1.00 | 1.00 | 1.00 | 1.00 | 1.00 | 1.00 |
| Mir7071 | 1.00 | 1.00 | 1.00 | 1.00 | 1.00 | 1.00 | 1.00 | 1.00 | 1.00 | 1.00 | 1.00 | 1.00 |
| Mir7072 | 0.94 | 57.19 | 69.67 | 1.00 | 1.00 | 1.00 | 1.00 | 1.00 | 1.00 | 1.00 | 1.00 | 1.00 |
| Mir7073 | 1.00 | 0.02 | 1.00 | 41.77 | 1.00 | 1.00 | 1.00 | 1.00 | 1.00 | 1.00 | 1.00 | 1.00 |
| Mir7074 | 1.00 | 0.01 | 1.00 | 1.00 | 1.00 | 1.00 | 0.03 | 37.83 | 1.00 | 1.00 | 1.00 | 1.00 |
| Mir7075 | 4.10 | 1.64 | 1.03 | 24.14 | 24.02 | 3.45 | 1.00 | 1.00 | 1.00 | 1.00 | 1.00 | 1.00 |
| Mir7077 | 1.00 | 1.00 | 1.00 | 1.00 | 1.00 | 1.00 | 1.00 | 1.00 | 1.00 | 1.00 | 1.00 | 1.00 |
| Mir7078 | 1.06 | 1.38 | 0.01 | 0.02 | 2.03 | 1.00 | 0.03 | 0.04 | 1.00 | 1.00 | 1.00 | 1.00 |
| Mir7079 | 1.78 | 1.04 | 1.13 | 1.54 | 1.87 | 1.53 | 0.43 | 1.18 | 0.36 | 1.00 | 1.00 | 1.00 |
| Mir708 | 1.00 | 1.00 | 1.00 | 1.00 | 1.00 | 1.00 | 1.00 | 1.00 | 1.00 | 1.00 | 1.00 | 1.00 |
| Mir7080 | 0.03 | 0.03 | 1.00 | 1.00 | 0.03 | 1.00 | 1.00 | 1.00 | 1.00 | 1.00 | 1.00 | 1.00 |
| Mir7081 | 1.00 | 17.54 | 44.05 | 0.02 | 0.06 | 2.04 | 1.00 | 1.00 | 1.00 | 1.00 | 1.00 | 1.00 |
| Mir7082 | 0.57 | 1.08 | 1.08 | 0.69 | 6.18 | 0.28 | 1.00 | 1.00 | 6.73 | 1.00 | 1.00 | 1.00 |
| Mir7083 | 0.02 | 1.00 | 1.00 | 1.00 | 1.00 | 1.00 | 1.00 | 1.00 | 1.00 | 1.00 | 1.00 | 1.00 |
| Mir7085 | 68.80 | 0.50 | 1.64 | 36.22 | 1.00 | 0.55 | 1.00 | 1.00 | 1.00 | 1.00 | 1.00 | 1.00 |
| Mir7086 | 1.00 | 70.67 | 2.07 | 70.85 | 0.46 | 42.04 | 21.20 | 1.00 | 1.00 | 1.00 | 1.00 | 1.00 |
| Mir7087 | 0.96 | 0.82 | 1.31 | 0.67 | 0.58 | 3.05 | 0.03 | 23.43 | 22.18 | 1.00 | 1.00 | 1.00 |
| Mir7088 | 3.29 | 0.94 | 0.81 | 0.03 | 1.00 | 5.86 | 6.71 | 1.00 | 1.00 | 1.00 | 1.00 | 1.00 |
| Mir7089 | 0.33 | 0.30 | 0.52 | 0.33 | 1.90 | 62.24 | 0.05 | 1.00 | 1.00 | 1.00 | 1.00 | 1.00 |
| Mir709 | 1.00 | 0.48 | 0.09 | 1.00 | 1.00 | 1.00 | 1.00 | 1.00 | 1.00 | 1.00 | 1.00 | 1.00 |
| Mir7090 | 150.40 | 1.00 | 1.92 | 1.00 | 1.00 | 0.62 | 1.00 | 1.00 | 1.00 | 1.00 | 1.00 | 1.00 |
| Mir7091 | 1.79 | 0.69 | 1.49 | 1.33 | 1.13 | 1.14 | 0.72 | 1.09 | 1.05 | 1.00 | 1.00 | 1.00 |
| Mir7092 | 1.00 | 1.00 | 1.00 | 1.00 | 1.00 | 1.00 | 1.00 | 1.00 | 1.00 | 1.00 | 1.00 | 1.00 |
| Mir7093 | 1.58 | 0.37 | 1.16 | 0.10 | 0.55 | 1.14 | 1.38 | 0.27 | 0.24 | 1.00 | 1.00 | 1.00 |
| Mir711 | 1.00 | 1.00 | 1.00 | 1.00 | 1.00 | 1.00 | 1.00 | 23.18 | 0.11 | 1.00 | 1.00 | 1.00 |
| Mir7115 | 1.50 | 0.83 | 1.72 | 1.44 | 1.19 | 1.83 | 0.49 | 0.79 | 69.45 | 1.00 | 1.00 | 1.00 |
| Mir7117 | 1.00 | 0.03 | 1.00 | 1.00 | 1.00 | 1.00 | 1.00 | 1.00 | 1.00 | 1.00 | 1.00 | 1.00 |
| Mir7118 | 1.00 | 1.00 | 1.00 | 1.00 | 83.31 | 1.00 | 1.00 | 1.00 | 1.00 | 1.00 | 1.00 | 1.00 |
| Mir713 | 5.04 | 1.00 | 1.00 | 1.00 | 1.00 | 1.00 | 1.00 | 1.00 | 1.00 | 1.00 | 1.00 | 1.00 |
| Mir719 | 1.50 | 0.72 | 1.83 | 0.85 | 1.15 | 0.91 | 5.31 | 0.18 | 1.35 | 1.00 | 1.00 | 1.00 |
| Mir7210 | 1.00 | 1.00 | 1.00 | 1.00 | 1.00 | 1.00 | 1.00 | 1.00 | 1.00 | 1.00 | 1.00 | 1.00 |
| Mir7211 | 48.80 | 1.46 | 0.02 | 1.00 | 1.00 | 1.00 | 1.00 | 1.00 | 1.00 | 1.00 | 1.00 | 1.00 |
| Mir7214 | 1.00 | 44.35 | 1.00 | 1.00 | 1.00 | 1.00 | 1.00 | 1.00 | 1.00 | 1.00 | 1.00 | 1.00 |
| Mir7215 | 1.00 | 1.00 | 1.00 | 1.00 | 1.00 | 1.00 | 1.00 | 1.00 | 1.00 | 1.00 | 1.00 | 1.00 |

Fig. 31-85

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir7216 | 1.00 | 1.00 | 1.00 | 1.00 | 1.00 | 1.00 | 1.00 | 1.00 | 1.00 |
| Mir7220 | 1.00 | 1.00 | 1.00 | 1.00 | 1.00 | 1.00 | 1.00 | 1.00 | 1.00 |
| Mir7221 | 1.00 | 1.00 | 1.00 | 1.00 | 1.00 | 1.00 | 1.00 | 1.00 | 1.00 |
| Mir7223 | 1.00 | 1.00 | 1.00 | 1.00 | 1.00 | 1.00 | 1.00 | 1.00 | 1.00 |
| Mir7225 | 1.00 | 1.00 | 1.00 | 1.00 | 1.00 | 1.00 | 1.00 | 1.00 | 1.00 |
| Mir7226 | 1.00 | 1.00 | 1.00 | 1.00 | 1.00 | 1.00 | 1.00 | 1.00 | 1.00 |
| Mir7227 | 1.00 | 1.00 | 1.00 | 1.00 | 1.00 | 1.00 | 1.00 | 1.00 | 1.00 |
| Mir7231 | 1.00 | 1.00 | 0.02 | 1.00 | 1.00 | 1.00 | 1.00 | 1.00 | 1.00 |
| Mir7232 | 1.00 | 1.00 | 1.00 | 1.00 | 1.00 | 1.00 | 1.00 | 1.00 | 1.00 |
| Mir7236 | 1.00 | 1.00 | 1.00 | 1.00 | 1.00 | 1.00 | 1.00 | 81.54 | 1.00 |
| Mir7237 | 86.20 | 41.78 | 1.00 | 100.08 | 0.01 | 61.56 | 1.00 | 1.00 | 1.00 |
| Mir7240 | 1.00 | 1.00 | 1.00 | 1.00 | 234.64 | 1.00 | 1.00 | 104.10 | 1.00 |
| Mir7241 | 1.00 | 1.00 | 1.00 | 1.00 | 1.00 | 1.00 | 1.00 | 1.00 | 1.00 |
| Mir7242 | 1.00 | 1.00 | 1.00 | 1.00 | 1.00 | 1.00 | 1.00 | 1.00 | 1.00 |
| Mir744 | 1.00 | 0.08 | 1.00 | 1.00 | 1.00 | 6.25 | 1.00 | 8.39 | 1.00 |
| Mir7578 | 13.71 | 1.00 | 1.00 | 0.06 | 1.00 | 1.00 | 17.67 | 14.60 | 1.00 |
| Mir758 | 1.00 | 1.00 | 1.00 | 1.00 | 1.00 | 1.00 | 1.00 | 1.00 | 1.00 |
| Mir759 | 1.00 | 1.00 | 1.00 | 1.00 | 1.00 | 1.00 | 1.00 | 1.00 | 1.00 |
| Mir760 | 1.00 | 3.17 | 1.00 | 3.90 | 4.14 | 3.41 | 4.00 | 1.00 | 1.00 |
| Mir761 | 55.50 | 0.87 | 0.89 | 1.00 | 0.04 | 1.00 | 1.00 | 1.00 | 1.00 |
| Mir762 | 0.27 | 9.59 | 0.22 | 0.43 | 2.90 | 1.00 | 1.00 | 1.00 | 12.06 |
| Mir7646 | 1.00 | 67.53 | 1.00 | 1.00 | 1.00 | 1.00 | 1.00 | 0.01 | 1.00 |
| Mir7647 | 1.00 | 1.00 | 1.00 | 1.00 | 1.00 | 1.00 | 1.00 | 1.00 | 1.00 |
| Mir7649 | 0.01 | 0.74 | 1.00 | 1.00 | 1.00 | 1.00 | 1.00 | 1.00 | 1.00 |
| Mir7650 | 5.95 | 0.43 | 0.93 | 2.25 | 1.13 | 0.01 | 0.01 | 0.00 | 1.00 |
| Mir7653 | 1.00 | 1.00 | 1.00 | 1.00 | 1.00 | 1.00 | 1.00 | 1.00 | 33.49 |
| Mir7655 | 0.01 | 1.00 | 1.00 | 1.00 | 1.00 | 1.00 | 1.00 | 1.00 | 1.00 |
| Mir7656 | 1.00 | 1.00 | 1.00 | 1.00 | 1.00 | 1.00 | 1.00 | 1.00 | 1.00 |
| Mir7658 | 1.00 | 0.20 | 1.00 | 1.00 | 1.00 | 1.00 | 1.00 | 1.00 | 1.00 |
| Mir7661 | 1.00 | 1.00 | 1.00 | 1.00 | 143.01 | 1.00 | 1.00 | 1.00 | 1.00 |
| Mir7662 | 1.00 | 0.02 | 1.00 | 1.00 | 1.00 | 1.00 | 1.00 | 1.00 | 1.00 |
| Mir7663 | 1.00 | 1.00 | 1.00 | 1.00 | 1.00 | 1.00 | 1.00 | 1.00 | 1.00 |
| Mir7665 | 1.00 | 1.00 | 1.00 | 1.00 | 1.00 | 1.00 | 1.00 | 1.00 | 1.00 |
| Mir7666 | 1.00 | 1.00 | 0.01 | 1.00 | 1.00 | 1.00 | 1.00 | 1.00 | 1.00 |
| Mir7670 | 1.00 | 1.00 | 0.63 | 1.00 | 1.00 | 1.00 | 14.73 | 1.00 | 1.00 |
| Mir7673 | 79.56 | 1.69 | 0.01 | 1.39 | 96.78 | 1.53 | 65.04 | 72.02 | 0.01 |
| Mir7674 | 0.71 | 0.53 | 0.40 | 1.00 | 109.68 | 1.00 | 1.00 | 1.00 | 1.00 |
| Mir7675 | 1.00 | 1.00 | 1.00 | 1.00 | 1.00 | 1.00 | 1.00 | 1.00 | 1.00 |
| Mir7676-1 | 1.00 | 0.28 | 1.00 | 0.01 | 1.00 | 1.00 | 35.10 | 1.20 | 1.00 |
| Mir7676-2 | 0.57 | 35.59 | 2.00 | 0.02 | 1.00 | 0.65 | 0.04 | 0.01 | 64.35 |
| Mir7677 | 1.00 | 1.00 | 1.00 | 1.00 | 1.00 | 1.00 | 1.00 | 1.00 | 1.00 |
| Mir7678 | 0.04 | 1.00 | 1.00 | 1.00 | 1.00 | 1.00 | 1.00 | 1.00 | 1.00 |
| Mir7679 | 1.00 | 1.00 | 1.00 | 1.00 | 1.00 | 1.00 | 1.00 | 1.00 | 1.00 |
| Mir7681 | 1.00 | 1.00 | 1.00 | 1.00 | 1.00 | 1.00 | 1.00 | 1.00 | 1.00 |
| Mir7682 | 1.00 | 1.00 | 1.00 | 1.00 | 1.00 | 1.00 | 1.00 | 1.00 | 1.00 |
| Mir7683 | 1.00 | 1.00 | 1.00 | 1.00 | 1.00 | 1.00 | 1.00 | 1.00 | 1.00 |
| Mir7686 | 1.00 | 1.00 | 0.01 | 1.00 | 1.00 | 1.00 | 1.00 | 1.00 | 1.00 |
| Mir7687 | 59.65 | 0.01 | 1.00 | 1.00 | 1.00 | 1.00 | 1.00 | 1.00 | 1.00 |
| Mir802 | 1.00 | 1.00 | 1.00 | 1.00 | 1.00 | 1.00 | 1.00 | 1.00 | 1.00 |
| Mir804 | 1.00 | 1.00 | 1.00 | 1.00 | 1.00 | 1.00 | 1.00 | 1.00 | 1.00 |
| Mir8092 | 1.00 | 1.00 | 1.00 | 1.00 | 1.00 | 1.00 | 1.00 | 0.08 | 3.10 |
| Mir8093 | 0.91 | 1.40 | 2.06 | 1.24 | 1.14 | 0.65 | 0.78 | 2.32 | 3.21 |
| Mir8096 | 2.72 | 0.52 | 1.00 | 1.00 | 1.00 | 1.00 | 1.00 | 1.00 | 1.00 |
| Mir8097 | 3.94 | 0.90 | 0.45 | 0.18 | 1.29 | 0.06 | 1.00 | 0.04 | 10.15 |
| Mir8098 | 0.82 | 2.32 | 0.82 | 2.47 | 0.56 | 1.71 | 3.13 | 1.67 | 1.38 |
| Mir8099-2 | 0.96 | 1.26 | 1.54 | 0.65 | 0.68 | 1.25 | 1.86 | 0.75 | 1.13 |
| Mir8102 | 1.00 | 1.00 | 2.10 | 1.04 | 1.00 | 0.50 | 1.00 | 1.00 | 1.00 |
| Mir8103 | 13.33 | 4.71 | 0.47 | 2.32 | 0.07 | 0.21 | 1.00 | 1.00 | 1.00 |
| Mir8104 | 1.68 | 1.09 | 0.07 | 10.16 | 1.85 | 1.09 | 1.87 | 1.00 | 1.00 |
| Mir8105 | 1.00 | 1.00 | 1.00 | 1.00 | 1.00 | 1.04 | 12.29 | 1.00 | 1.00 |
| Mir8107 | 1.00 | 1.00 | 1.00 | 1.00 | 1.00 | 1.00 | 1.00 | 1.00 | 1.00 |
| Mir8108 | 6.21 | 2.11 | 1.80 | 0.83 | 0.29 | 0.69 | 0.89 | 0.80 | 2.12 |
| Mir8113 | 2.60 | 0.35 | 1.69 | 2.43 | 8.41 | 1.01 | 2.91 | 0.87 | 1.00 |
| Mir8114 | 1.00 | 11.86 | 0.12 | 1.00 | 1.00 | 1.00 | 1.00 | 1.00 | 1.00 |

Fig. 31-86

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir7216 | 1.00 | 1.00 | 1.00 | 1.00 | 1.00 | 1.00 | 1.00 | 57.25 | 1.00 |
| Mir7220 | 1.00 | 1.00 | 1.00 | 0.02 | 1.00 | 1.00 | 1.00 | 1.00 | 1.00 |
| Mir7221 | 1.00 | 1.00 | 1.00 | 1.00 | 20.11 | 1.00 | 1.00 | 1.00 | 1.00 |
| Mir7223 | 1.00 | 1.00 | 1.00 | 1.00 | 1.00 | 1.00 | 0.02 | 1.00 | 1.00 |
| Mir7225 | 1.00 | 1.00 | 1.00 | 1.00 | 1.00 | 1.00 | 0.00 | 1.00 | 1.00 |
| Mir7226 | 45.64 | 1.06 | 1.00 | 1.00 | 1.00 | 1.00 | 1.00 | 1.00 | 1.00 |
| Mir7227 | 1.00 | 1.00 | 1.00 | 1.00 | 1.00 | 1.00 | 1.00 | 1.00 | 1.00 |
| Mir7231 | 1.02 | 0.02 | 1.00 | 44.89 | 1.00 | 1.83 | 261.05 | 0.01 | 1.01 |
| Mir7232 | 1.00 | 1.00 | 1.00 | 1.00 | 1.00 | 1.00 | 1.00 | 1.00 | 1.00 |
| Mir7236 | 1.00 | 1.00 | 0.02 | 1.00 | 0.02 | 1.00 | 1.00 | 1.00 | 1.00 |
| Mir7237 | 1.96 | 3.15 | 37.33 | 1.00 | 37.84 | 1.00 | 2.02 | 0.58 | 0.02 |
| Mir7240 | 1.91 | 1.00 | 1.00 | 72.02 | 1.00 | 1.00 | 0.01 | 0.01 | 1.70 |
| Mir7241 | 1.00 | 1.00 | 1.00 | 1.00 | 1.00 | 1.00 | 1.00 | 1.00 | 1.00 |
| Mir7242 | 1.00 | 1.00 | 1.00 | 1.00 | 1.00 | 1.00 | 1.00 | 1.00 | 1.00 |
| Mir744 | 1.00 | 9.80 | 1.00 | 0.18 | 5.72 | 1.00 | 8.09 | 1.00 | 1.00 |
| Mir7578 | 1.89 | 1.04 | 1.00 | 1.00 | 1.00 | 1.00 | 0.94 | 1.00 | 46.15 |
| Mir758 | 1.00 | 1.00 | 1.00 | 1.00 | 1.00 | 1.00 | 1.00 | 1.00 | 1.00 |
| Mir759 | 1.00 | 1.00 | 1.00 | 1.00 | 1.00 | 1.00 | 1.00 | 1.00 | 1.00 |
| Mir760 | 0.40 | 0.59 | 0.61 | 1.00 | 0.33 | 1.00 | 1.00 | 1.00 | 1.00 |
| Mir761 | 0.20 | 1.47 | 1.04 | 72.15 | 1.36 | 2.89 | 0.04 | 1.00 | 0.04 |
| Mir762 | 266.50 | 0.86 | 0.97 | 2.14 | 0.94 | 0.36 | 0.41 | 1.81 | 2.57 |
| Mir7646 | 180.86 | 1.00 | 127.73 | 1.00 | 83.66 | 1.00 | 1.00 | 1.00 | 1.00 |
| Mir7647 | 1.00 | 55.86 | 1.00 | 1.00 | 56.29 | 1.00 | 1.00 | 1.00 | 1.00 |
| Mir7649 | 0.37 | 9.04 | 1.71 | 1.00 | 1.00 | 1.00 | 0.93 | 1.09 | 1.26 |
| Mir7650 | 3.19 | 2.00 | 1.37 | 0.98 | 167.87 | 1.00 | 0.51 | 1.55 | 4.22 |
| Mir7653 | 1.00 | 1.00 | 1.00 | 4.75 | 1.00 | 1.00 | 1.00 | 0.02 | 1.00 |
| Mir7655 | 1.00 | 1.00 | 1.00 | 1.00 | 1.00 | 1.00 | 1.00 | 1.00 | 1.00 |
| Mir7656 | 40.97 | 1.00 | 1.00 | 1.00 | 1.00 | 1.00 | 1.00 | 1.00 | 1.00 |
| Mir7658 | 1.00 | 1.00 | 1.00 | 1.68 | 0.02 | 1.00 | 1.00 | 1.00 | 1.00 |
| Mir7661 | 0.02 | 1.00 | 1.00 | 1.00 | 1.00 | 1.00 | 1.00 | 1.00 | 1.00 |
| Mir7662 | 0.96 | 0.01 | 87.67 | 1.00 | 44.69 | 1.00 | 0.90 | 1.00 | 0.01 |
| Mir7663 | 1.00 | 41.60 | 1.00 | 1.00 | 1.00 | 1.00 | 1.00 | 1.00 | 1.00 |
| Mir7665 | 35.41 | 0.03 | 1.00 | 1.00 | 1.00 | 1.00 | 1.00 | 1.00 | 1.00 |
| Mir7666 | 0.01 | 1.00 | 1.00 | 1.00 | 1.98 | 1.00 | 191.06 | 1.00 | 1.00 |
| Mir7670 | 1.00 | 1.00 | 1.00 | 1.00 | 20.46 | 1.00 | 1.00 | 1.00 | 1.00 |
| Mir7673 | 0.35 | 32.56 | 0.02 | 35.12 | 0.99 | 0.84 | 69.25 | 147.85 | 1.70 |
| Mir7674 | 0.54 | 473.14 | 4.05 | 0.30 | 1.01 | 0.58 | 76.42 | 2.20 | 0.85 |
| Mir7675 | 1.00 | 1.00 | 1.00 | 1.00 | 1.00 | 1.00 | 1.00 | 1.00 | 1.00 |
| Mir7676-1 | 1.00 | 1.00 | 1.00 | 1.00 | 0.53 | 1.00 | 1.00 | 1.00 | 1.00 |
| Mir7676-2 | 0.01 | 2.86 | 0.01 | 0.40 | 0.01 | 25.61 | 1.00 | 0.36 | 1.00 |
| Mir7677 | 27.93 | 1.00 | 1.00 | 1.00 | 1.00 | 1.00 | 1.00 | 62.83 | 1.00 |
| Mir7678 | 20.05 | 1.00 | 2.04 | 1.00 | 1.00 | 1.00 | 0.01 | 85.50 | 0.03 |
| Mir7679 | 1.00 | 1.00 | 1.00 | 1.00 | 1.00 | 1.00 | 1.00 | 1.00 | 1.00 |
| Mir7681 | 1.00 | 21.01 | 1.00 | 20.20 | 1.00 | 1.00 | 1.00 | 1.00 | 1.00 |
| Mir7682 | 1.00 | 1.00 | 1.00 | 1.00 | 1.00 | 1.00 | 1.00 | 1.00 | 1.00 |
| Mir7683 | 1.00 | 41.60 | 44.08 | 1.00 | 1.00 | 1.00 | 1.00 | 1.00 | 160.06 |
| Mir7686 | 1.00 | 67.80 | 1.00 | 1.00 | 1.00 | 1.00 | 154.09 | 1.00 | 1.00 |
| Mir7687 | 1.00 | 1.00 | 1.00 | 1.00 | 1.00 | 1.00 | 1.00 | 1.00 | 1.00 |
| Mir802 | 1.00 | 1.00 | 1.00 | 1.00 | 1.00 | 1.00 | 1.00 | 1.00 | 1.00 |
| Mir804 | 1.00 | 1.00 | 0.16 | 1.00 | 1.00 | 1.00 | 1.00 | 1.00 | 1.00 |
| Mir8092 | 1.00 | 1.00 | 1.00 | 1.00 | 1.00 | 9.70 | 1.00 | 1.00 | 13.07 |
| Mir8093 | 0.70 | 0.33 | 1.00 | 0.98 | 0.28 | 0.47 | 1.20 | 1.16 | 8.97 |
| Mir8096 | 1.00 | 1.00 | 0.41 | 1.00 | 4.08 | 1.00 | 3.39 | 6.70 | 0.49 |
| Mir8097 | 0.34 | 43.11 | 0.35 | 0.90 | 1.53 | 6.11 | 1.04 | 1.82 | 1.07 |
| Mir8098 | 0.96 | 0.07 | 0.55 | 1.05 | 3.59 | 1.69 | 0.61 | 2.55 | 0.58 |
| Mir8099-2 | 0.70 | 0.85 | 1.60 | 0.67 | 0.81 | 1.46 | 0.59 | 1.97 | 1.19 |
| Mir8102 | 1.83 | 1.82 | 0.55 | 1.00 | 1.00 | 2.01 | 3.93 | 1.00 | 0.11 |
| Mir8103 | 1.29 | 0.81 | 1.31 | 8.15 | 1.00 | 0.11 | 0.95 | 0.71 | 1.61 |
| Mir8104 | 0.04 | 1.74 | 12.42 | 1.00 | 9.83 | 3.30 | 0.95 | 1.00 | 1.01 |
| Mir8105 | 1.00 | 0.13 | 1.00 | 1.00 | 1.00 | 1.00 | 12.13 | 1.00 | 0.08 |
| Mir8107 | 1.00 | 0.33 | 0.32 | 1.00 | 1.00 | 1.00 | 1.00 | 1.00 | 1.00 |
| Mir8108 | 1.69 | 0.24 | 0.70 | 0.10 | 1.87 | 5.34 | 4.14 | 0.33 | 2.35 |
| Mir8113 | 4.01 | 1.80 | 0.81 | 0.39 | 2.48 | 0.40 | 1.16 | 1.34 | 0.88 |
| Mir8114 | 1.00 | 0.20 | 0.20 | 1.65 | 0.04 | 1.00 | 1.00 | 0.11 | 1.00 |

Fig. 31-87

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir7216 | 1.00 | 1.00 | 1.00 | 1.00 | 1.00 | 1.00 | 0.37 | 0.69 | 1.06 |
| Mir7220 | 267.48 | 0.52 | 0.00 | 1.00 | 1.00 | 1.00 | 1.00 | 1.00 | 1.00 |
| Mir7221 | 1.00 | 1.00 | 1.00 | 1.00 | 1.00 | 1.00 | 0.56 | 0.92 | 1.06 |
| Mir7223 | 1.00 | 1.00 | 1.00 | 1.00 | 1.00 | 1.00 | 0.57 | 0.67 | 1.90 |
| Mir7225 | 1.00 | 1.00 | 1.00 | 1.00 | 1.00 | 1.00 | 0.23 | 0.79 | 2.08 |
| Mir7226 | 1.00 | 1.00 | 1.00 | 1.00 | 1.00 | 1.00 | 1.00 | 1.00 | 1.00 |
| Mir7227 | 1.00 | 1.00 | 1.00 | 1.00 | 1.00 | 1.00 | 1.00 | 0.02 | 1.00 |
| Mir7231 | 1.00 | 0.01 | 1.00 | 1.00 | 1.00 | 1.00 | 1.00 | 1.00 | 1.00 |
| Mir7232 | 74.58 | 32.18 | 1.00 | 1.00 | 1.00 | 1.00 | 0.93 | 1.26 | 1.04 |
| Mir7236 | 1.00 | 149.49 | 1.00 | 1.00 | 1.00 | 1.00 | 1.00 | 1.00 | 1.00 |
| Mir7237 | 1.00 | 1.00 | 0.02 | 1.00 | 1.00 | 0.99 | 0.03 | 35.37 | 1.00 |
| Mir7240 | 1.00 | 1.00 | 105.76 | 1.00 | 1.00 | 1.00 | 1.00 | 1.00 | 1.00 |
| Mir7241 | 1.00 | 1.00 | 1.00 | 1.00 | 1.00 | 1.00 | 0.01 | 1.00 | 32.16 |
| Mir7242 | 1.00 | 1.00 | 1.00 | 1.00 | 1.00 | 1.00 | 14.65 | 0.91 | 4.22 |
| Mir744 | 1.74 | 0.53 | 2.89 | 1.00 | 1.00 | 1.00 | 1.00 | 1.00 | 1.00 |
| Mir7578 | 1.00 | 18.57 | 0.04 | 0.05 | 17.06 | 13.84 | 0.03 | 11.15 | 1.49 |
| Mir758 | 1.00 | 0.05 | 1.00 | 1.00 | 18.17 | 1.00 | 1.00 | 1.00 | 1.00 |
| Mir759 | 1.00 | 1.00 | 1.00 | 1.00 | 1.00 | 1.00 | 6.41 | 2.44 | 2.15 |
| Mir760 | 0.87 | 2.80 | 1.39 | 1.00 | 13.18 | 3.16 | 1.00 | 0.62 | 0.57 |
| Mir761 | 1.00 | 1.00 | 21.65 | 1.00 | 1.00 | 1.00 | 0.85 | 1.36 | 0.93 |
| Mir762 | 0.06 | 105.09 | 0.01 | 0.90 | 0.03 | 0.31 | 1.13 | 1.43 | 0.80 |
| Mir7646 | 1.00 | 1.00 | 1.00 | 1.00 | 1.00 | 1.00 | 0.66 | 0.00 | 0.01 |
| Mir7647 | 1.00 | 1.00 | 92.61 | 1.00 | 1.00 | 1.00 | 1.10 | 0.96 | 101.58 |
| Mir7649 | 1.00 | 1.00 | 1.00 | 1.00 | 1.00 | 1.00 | 1.00 | 1.00 | 1.00 |
| Mir7650 | 0.01 | 173.52 | 1.08 | 0.01 | 1.05 | 179.81 | 0.56 | 5.13 | 0.01 |
| Mir7653 | 1.00 | 1.00 | 1.00 | 1.00 | 1.00 | 1.00 | 1.00 | 1.00 | 1.00 |
| Mir7655 | 1.00 | 1.00 | 1.00 | 1.00 | 1.00 | 1.00 | 0.56 | 157.67 | 0.56 |
| Mir7656 | 1.00 | 1.00 | 1.00 | 1.00 | 1.00 | 1.00 | 1.00 | 1.00 | 1.00 |
| Mir7658 | 1.00 | 1.00 | 1.00 | 1.00 | 1.00 | 1.00 | 1.00 | 11.56 | 0.01 |
| Mir7661 | 1.00 | 1.00 | 1.00 | 1.00 | 1.00 | 1.00 | 1.00 | 1.00 | 1.00 |
| Mir7662 | 1.00 | 127.00 | 1.00 | 132.89 | 0.01 | 0.01 | 0.02 | 1.00 | 1.00 |
| Mir7663 | 0.01 | 1.00 | 1.00 | 1.00 | 1.00 | 1.00 | 0.02 | 41.54 | 46.06 |
| Mir7665 | 1.00 | 97.84 | 1.00 | 1.00 | 1.00 | 1.00 | 1.00 | 1.00 | 0.03 |
| Mir7666 | 1.00 | 1.00 | 1.00 | 1.00 | 1.00 | 1.00 | 83.62 | 1.33 | 0.81 |
| Mir7670 | 1.00 | 1.00 | 1.00 | 1.00 | 1.00 | 1.00 | 1.00 | 1.00 | 1.00 |
| Mir7673 | 0.97 | 0.01 | 3.12 | 2.53 | 157.81 | 0.02 | 0.55 | 1.72 | 67.08 |
| Mir7674 | 85.84 | 195.17 | 0.02 | 1.00 | 1.00 | 1.00 | 0.82 | 1.50 | 0.53 |
| Mir7675 | 1.00 | 1.00 | 1.00 | 1.00 | 1.00 | 1.00 | 1.00 | 1.00 | 1.00 |
| Mir7676-1 | 1.00 | 1.00 | 1.00 | 1.00 | 1.00 | 1.00 | 1.00 | 1.00 | 1.00 |
| Mir7676-2 | 0.01 | 1.00 | 1.00 | 0.23 | 1.00 | 1.00 | 1.00 | 28.27 | 1.00 |
| Mir7677 | 1.00 | 1.00 | 1.00 | 1.00 | 1.00 | 1.00 | 1.00 | 1.00 | 25.91 |
| Mir7678 | 1.00 | 41.90 | 1.00 | 0.03 | 76.38 | 56.56 | 1.00 | 1.00 | 1.00 |
| Mir7679 | 1.00 | 1.00 | 1.00 | 1.00 | 1.00 | 0.02 | 1.00 | 1.00 | 1.00 |
| Mir7681 | 1.00 | 1.00 | 1.00 | 1.00 | 1.00 | 1.00 | 1.00 | 1.00 | 1.00 |
| Mir7682 | 1.00 | 1.00 | 1.00 | 1.00 | 1.00 | 1.00 | 0.02 | 1.00 | 53.07 |
| Mir7683 | 1.00 | 1.00 | 1.00 | 1.00 | 1.00 | 1.00 | 0.02 | 79.04 | 1.01 |
| Mir7686 | 1.00 | 1.00 | 130.80 | 1.00 | 1.00 | 1.00 | 0.61 | 1.42 | 1.23 |
| Mir7687 | 1.00 | 1.00 | 1.00 | 1.00 | 1.00 | 1.00 | 56.02 | 1.00 | 1.00 |
| Mir802 | 1.00 | 1.00 | 1.00 | 1.00 | 1.00 | 1.00 | 1.00 | 5.92 | 1.00 |
| Mir804 | 1.00 | 1.00 | 0.14 | 10.43 | 18.66 | 1.00 | 1.36 | 0.15 | 0.69 |
| Mir8092 | 1.00 | 1.00 | 0.10 | 1.00 | 1.00 | 1.00 | 1.00 | 1.00 | 1.00 |
| Mir8093 | 0.37 | 1.00 | 1.00 | 1.62 | 0.92 | 0.40 | 1.42 | 1.88 | 2.12 |
| Mir8096 | 1.00 | 1.00 | 1.00 | 1.00 | 1.00 | 1.00 | 0.59 | 1.00 | 1.00 |
| Mir8097 | 0.34 | 4.76 | 2.20 | 1.35 | 0.08 | 1.53 | 1.00 | 1.00 | 1.00 |
| Mir8098 | 2.23 | 0.49 | 0.23 | 0.57 | 0.20 | 0.51 | 0.22 | 0.89 | 0.79 |
| Mir8099-2 | 1.27 | 0.74 | 1.21 | 1.18 | 0.93 | 1.95 | 0.87 | 0.92 | 1.83 |
| Mir8102 | 1.38 | 0.32 | 0.35 | 0.29 | 1.90 | 2.82 | 1.06 | 0.93 | 0.78 |
| Mir8103 | 0.55 | 1.30 | 0.53 | 1.25 | 2.72 | 0.13 | 0.57 | 1.64 | 0.35 |
| Mir8104 | 0.04 | 0.30 | 0.54 | 1.00 | 0.05 | 4.88 | 1.00 | 1.00 | 1.00 |
| Mir8105 | 1.00 | 0.97 | 1.00 | 1.00 | 1.00 | 9.60 | 0.88 | 0.59 | 1.04 |
| Mir8107 | 1.00 | 1.00 | 1.00 | 1.00 | 4.14 | 1.00 | 0.31 | 1.00 | 1.00 |
| Mir8108 | 1.20 | 0.39 | 0.61 | 0.33 | 1.77 | 1.04 | 4.33 | 0.03 | 0.93 |
| Mir8113 | 0.21 | 0.97 | 1.00 | 0.79 | 1.60 | 0.27 | 1.09 | 0.79 | 0.86 |
| Mir8114 | 6.51 | 1.00 | 1.00 | 1.00 | 0.99 | 1.00 | 0.52 | 0.62 | 1.48 |

Fig. 31-88

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir7216 | 1.00 | 1.00 | 1.00 | 1.00 | 1.00 | 1.00 | 1.00 | 1.00 | 1.00 | 1.00 | 1.00 | 1.00 |
| Mir7220 | 1.00 | 1.00 | 1.00 | 1.00 | 1.00 | 1.00 | 1.00 | 1.00 | 1.00 | 1.00 | 1.00 | 1.00 |
| Mir7221 | 1.00 | 1.00 | 1.00 | 1.00 | 1.00 | 1.00 | 1.00 | 1.00 | 1.00 | 1.00 | 1.00 | 1.00 |
| Mir7223 | 1.00 | 1.00 | 35.01 | 1.00 | 1.00 | 1.00 | 1.00 | 1.00 | 1.00 | 1.00 | 1.00 | 1.00 |
| Mir7225 | 1.00 | 1.00 | 1.00 | 58.60 | 1.00 | 92.62 | 1.00 | 0.02 | 1.00 | 1.00 | 1.00 | 1.00 |
| Mir7226 | 1.00 | 1.00 | 1.00 | 1.00 | 1.00 | 1.00 | 1.00 | 1.00 | 1.00 | 1.00 | 1.00 | 1.00 |
| Mir7227 | 59.49 | 1.00 | 1.00 | 1.00 | 1.00 | 1.00 | 1.00 | 1.00 | 1.00 | 1.00 | 1.00 | 1.00 |
| Mir7231 | 0.02 | 52.68 | 68.35 | 52.62 | 0.92 | 1.00 | 1.00 | 1.00 | 1.00 | 1.00 | 1.00 | 1.00 |
| Mir7232 | 1.00 | 1.00 | 1.00 | 1.00 | 1.00 | 1.00 | 1.00 | 1.00 | 1.00 | 1.00 | 1.00 | 1.00 |
| Mir7236 | 1.00 | 1.00 | 1.00 | 1.00 | 1.00 | 1.00 | 1.00 | 1.00 | 1.00 | 1.00 | 1.00 | 1.00 |
| Mir7237 | 0.01 | 0.01 | 0.75 | 0.01 | 0.01 | 1.00 | 1.00 | 0.03 | 1.00 | 1.00 | 1.00 | 1.00 |
| Mir7240 | 1.37 | 1.30 | 1.09 | 1.56 | 0.88 | 0.28 | 1.00 | 1.00 | 1.00 | 1.00 | 1.00 | 1.00 |
| Mir7241 | 1.00 | 1.00 | 1.00 | 1.00 | 1.00 | 1.00 | 1.00 | 1.00 | 0.03 | 1.00 | 1.00 | 1.00 |
| Mir7242 | 1.00 | 1.00 | 1.00 | 1.00 | 1.00 | 1.00 | 1.00 | 1.00 | 1.00 | 1.00 | 1.00 | 1.00 |
| Mir744 | 1.00 | 1.00 | 1.00 | 1.00 | 1.00 | 1.00 | 1.00 | 1.00 | 1.00 | 1.00 | 1.00 | 1.00 |
| Mir7578 | 1.05 | 0.65 | 0.07 | 0.08 | 0.45 | 0.56 | 1.00 | 1.00 | 1.00 | 1.00 | 1.00 | 1.00 |
| Mir758 | 1.00 | 1.00 | 1.00 | 1.00 | 1.00 | 1.00 | 1.00 | 1.00 | 1.00 | 1.00 | 1.00 | 1.00 |
| Mir759 | 1.00 | 1.00 | 1.00 | 1.00 | 1.00 | 1.00 | 1.00 | 1.00 | 1.00 | 1.00 | 1.00 | 1.00 |
| Mir760 | 1.00 | 0.62 | 0.28 | 1.00 | 1.00 | 1.00 | 2.20 | 0.33 | 0.42 | 1.00 | 1.00 | 1.00 |
| Mir761 | 1.44 | 2.67 | 3.91 | 0.02 | 3.32 | 2.28 | 21.16 | 0.27 | 0.08 | 1.00 | 1.00 | 1.00 |
| Mir762 | 270.43 | 0.01 | 0.04 | 3.53 | 0.59 | 0.27 | 63.61 | 0.63 | 0.03 | 1.00 | 1.00 | 1.00 |
| Mir7646 | 1.00 | 1.00 | 1.00 | 1.00 | 1.00 | 1.00 | 1.00 | 1.00 | 1.00 | 1.00 | 1.00 | 1.00 |
| Mir7647 | 1.00 | 1.11 | 1.00 | 0.02 | 52.50 | 1.00 | 1.00 | 1.00 | 1.00 | 1.00 | 1.00 | 1.00 |
| Mir7649 | 7.92 | 3.92 | 1.34 | 0.69 | 1.46 | 1.60 | 29.43 | 0.01 | 1.00 | 1.00 | 1.00 | 1.00 |
| Mir7650 | 2.07 | 3.95 | 0.50 | 0.64 | 2.93 | 1.45 | 1.43 | 1.00 | 0.02 | 1.00 | 1.00 | 1.00 |
| Mir7653 | 1.00 | 9.55 | 1.00 | 1.00 | 0.03 | 0.04 | 33.73 | 0.02 | 0.50 | 1.00 | 1.00 | 1.00 |
| Mir7655 | 1.00 | 1.00 | 1.00 | 0.02 | 1.00 | 1.00 | 1.00 | 1.00 | 1.00 | 1.00 | 1.00 | 1.00 |
| Mir7656 | 0.01 | 48.66 | 1.04 | 0.03 | 1.00 | 54.68 | 1.00 | 1.00 | 1.00 | 1.00 | 1.00 | 1.00 |
| Mir7658 | 1.00 | 1.00 | 1.00 | 1.00 | 1.00 | 1.00 | 1.00 | 22.44 | 1.00 | 1.00 | 1.00 | 1.00 |
| Mir7661 | 1.00 | 1.00 | 1.00 | 1.00 | 1.00 | 1.00 | 1.00 | 1.00 | 1.00 | 1.00 | 1.00 | 1.00 |
| Mir7662 | 1.00 | 44.35 | 68.35 | 1.00 | 1.00 | 1.00 | 1.00 | 1.00 | 1.00 | 1.00 | 1.00 | 1.00 |
| Mir7663 | 1.00 | 1.00 | 68.35 | 1.00 | 39.88 | 0.02 | 1.00 | 1.00 | 1.00 | 1.00 | 1.00 | 1.00 |
| Mir7665 | 1.00 | 37.95 | 1.00 | 1.00 | 1.00 | 1.00 | 1.00 | 1.00 | 1.00 | 1.00 | 1.00 | 1.00 |
| Mir7666 | 0.01 | 0.01 | 1.00 | 90.40 | 1.00 | 1.00 | 1.00 | 1.00 | 1.00 | 1.00 | 1.00 | 1.00 |
| Mir7670 | 1.00 | 1.00 | 1.00 | 1.00 | 1.00 | 1.00 | 1.00 | 1.00 | 1.00 | 1.00 | 1.00 | 1.00 |
| Mir7673 | 1.00 | 0.56 | 0.02 | 0.01 | 0.46 | 0.39 | 1.00 | 1.00 | 1.00 | 1.00 | 1.00 | 1.00 |
| Mir7674 | 0.79 | 0.73 | 0.82 | 4.05 | 0.95 | 2.02 | 1.00 | 1.00 | 1.00 | 1.00 | 1.00 | 1.00 |
| Mir7675 | 1.00 | 1.00 | 1.00 | 57.61 | 1.00 | 1.00 | 1.00 | 1.00 | 1.00 | 1.00 | 1.00 | 1.00 |
| Mir7676-1 | 1.00 | 1.00 | 1.00 | 1.00 | 1.00 | 1.00 | 1.40 | 1.00 | 1.00 | 1.00 | 1.00 | 1.00 |
| Mir7676-2 | 1.00 | 1.00 | 1.00 | 0.54 | 1.83 | 0.00 | 19.58 | 1.00 | 26.22 | 1.00 | 1.00 | 1.00 |
| Mir7677 | 1.00 | 1.00 | 1.00 | 1.00 | 1.00 | 1.00 | 1.00 | 1.00 | 1.00 | 1.00 | 1.00 | 1.00 |
| Mir7678 | 1.00 | 86.92 | 1.00 | 1.35 | 1.12 | 0.98 | 1.00 | 1.00 | 20.70 | 1.00 | 1.00 | 1.00 |
| Mir7679 | 97.10 | 0.87 | 113.03 | 0.03 | 0.01 | 1.08 | 1.00 | 1.00 | 1.00 | 1.00 | 1.00 | 1.00 |
| Mir7681 | 1.00 | 1.00 | 1.00 | 1.00 | 1.00 | 0.05 | 1.00 | 1.00 | 1.00 | 1.00 | 1.00 | 1.00 |
| Mir7682 | 1.00 | 1.00 | 1.00 | 1.00 | 1.00 | 1.00 | 1.00 | 1.00 | 1.00 | 1.00 | 1.00 | 1.00 |
| Mir7683 | 1.00 | 1.00 | 1.00 | 0.02 | 0.02 | 0.02 | 1.00 | 1.00 | 1.00 | 1.00 | 1.00 | 1.00 |
| Mir7686 | 1.00 | 1.00 | 104.34 | 1.00 | 1.00 | 1.00 | 1.00 | 1.00 | 1.00 | 1.00 | 1.00 | 1.00 |
| Mir7687 | 1.00 | 1.00 | 1.00 | 1.00 | 1.00 | 1.00 | 1.00 | 1.00 | 1.00 | 1.00 | 1.00 | 1.00 |
| Mir802 | 1.00 | 1.00 | 1.00 | 1.00 | 1.00 | 1.00 | 0.43 | 0.19 | 0.56 | 1.00 | 7.86 | 1.00 |
| Mir804 | 1.00 | 1.00 | 1.00 | 1.00 | 1.00 | 1.00 | 1.00 | 1.00 | 1.00 | 1.00 | 1.00 | 1.00 |
| Mir8092 | 1.00 | 14.11 | 1.00 | 1.00 | 15.05 | 1.00 | 1.00 | 1.00 | 1.00 | 1.00 | 0.80 | 2.88 |
| Mir8093 | 1.18 | 0.29 | 0.71 | 0.29 | 0.45 | 2.02 | 0.19 | 1.48 | 2.43 | 8.93 | 1.00 | 1.00 |
| Mir8096 | 3.60 | 0.39 | 0.75 | 0.41 | 1.00 | 0.43 | 1.00 | 1.00 | 1.00 | 1.00 | 1.00 | 1.00 |
| Mir8097 | 1.66 | 0.40 | 2.03 | 39.53 | 0.43 | 0.18 | 0.82 | 7.14 | 0.94 | 1.00 | 7.06 | 2.11 |
| Mir8098 | 0.86 | 2.15 | 0.30 | 1.53 | 1.07 | 7.08 | 1.02 | 8.27 | 2.71 | 1.00 | 1.00 | 1.00 |
| Mir8099-2 | 0.93 | 1.13 | 0.92 | 0.77 | 1.69 | 1.17 | 1.18 | 0.67 | 0.80 | 16.12 | 1.00 | 1.00 |
| Mir8102 | 0.46 | 1.35 | 0.46 | 5.30 | 0.28 | 0.46 | 1.00 | 1.00 | 1.00 | 1.00 | 124.20 | 1.00 |
| Mir8103 | 0.51 | 0.42 | 0.59 | 1.67 | 7.93 | 1.47 | 0.10 | 1.00 | 1.00 | 1.00 | 1.00 | 1.00 |
| Mir8104 | 0.06 | 0.80 | 0.20 | 0.18 | 3.61 | 1.80 | 10.25 | 2.53 | 1.59 | 1.00 | 1.00 | 1.00 |
| Mir8105 | 1.05 | 0.65 | 0.26 | 1.32 | 1.00 | 0.57 | 1.00 | 1.00 | 1.00 | 1.00 | 1.00 | 1.00 |
| Mir8107 | 7.22 | 4.02 | 0.15 | 0.71 | 0.29 | 3.59 | 1.00 | 1.00 | 1.00 | 1.00 | 1.00 | 1.00 |
| Mir8108 | 0.81 | 0.82 | 1.18 | 0.66 | 3.03 | 1.22 | 9.78 | 0.72 | 0.36 | 1.00 | 1.00 | 1.00 |
| Mir8113 | 0.79 | 0.75 | 0.63 | 1.75 | 0.93 | 0.37 | 0.85 | 1.00 | 0.53 | 1.00 | 1.00 | 1.00 |
| Mir8114 | 1.00 | 0.15 | 0.13 | 0.03 | 7.00 | 0.16 | 1.00 | 1.00 | 4.46 | 1.00 | 1.00 | 1.00 |

Fig. 31- 89

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Mir8116 | 6.75 | 0.59 | 1.19 | 2.41 | 1.12 | 0.46 | 2.97 | 1.67 | 0.07 |
| Mir8118 | 1.00 | 1.00 | 1.00 | 1.00 | 1.00 | 0.40 | 1.00 | 1.00 | 1.00 |
| Mir8120 | 1.00 | 1.00 | 2.10 | 1.04 | 0.45 | 1.00 | 1.00 | 1.00 | 1.00 |
| Mir872 | 1.00 | 1.00 | 1.00 | 1.00 | 1.00 | 1.00 | 1.00 | 1.00 | 1.00 |
| Mir873 | 1.00 | 1.00 | 1.00 | 1.00 | 1.00 | 1.00 | 1.00 | 1.00 | 1.00 |
| Mir874 | 1.00 | 1.00 | 1.00 | 4.43 | 0.04 | 0.02 | 1.00 | 1.00 | 1.00 |
| Mir875 | 1.00 | 1.00 | 1.00 | 1.00 | 1.00 | 1.00 | 0.04 | 1.00 | 1.00 |
| Mir877 | 11.16 | 1.00 | 1.00 | 1.19 | 1.00 | 1.00 | 0.07 | 0.06 | 1.00 |
| Mir883a | 1.00 | 1.00 | 1.00 | 1.00 | 1.00 | 1.00 | 1.00 | 1.00 | 1.00 |
| Mir9-1 | 1.00 | 1.00 | 1.00 | 1.00 | 1.00 | 1.00 | 1.00 | 1.00 | 1.00 |
| Mir92-1 | 0.21 | 1.00 | 1.00 | 1.00 | 1.00 | 14.39 | 1.00 | 1.00 | 16.05 |
| Mir92-2 | 1.00 | 1.00 | 1.00 | 0.09 | 1.00 | 1.08 | 1.00 | 1.00 | 1.00 |
| Mir92b | 1.00 | 1.00 | 12.39 | 1.00 | 1.00 | 1.00 | 1.00 | 1.00 | 1.00 |
| Mir93 | 1.00 | 1.00 | 1.00 | 1.00 | 14.53 | 10.97 | 12.91 | 1.00 | 1.00 |
| Mir99a | 1.73 | 1.00 | 74.56 | 1.00 | 1.00 | 50.35 | 1.00 | 1.00 | 0.02 |
| Mir99b | 1.00 | 1.00 | 1.00 | 1.38 | 1.00 | 1.00 | 1.00 | 1.00 | 1.00 |
| Mirlet7a-1 | 1.00 | 1.00 | 1.00 | 0.06 | 1.00 | 1.01 | 1.00 | 1.00 | 1.00 |
| Mirlet7b | 7.39 | 4.22 | 1.00 | 33.74 | 4.58 | 0.07 | 1.00 | 0.05 | 7.39 |
| Mirlet7c-1 | 1.00 | 1.00 | 1.00 | 1.00 | 10.81 | 8.29 | 1.00 | 1.00 | 1.00 |
| Mirlet7c-2 | 1.00 | 3.58 | 1.00 | 1.00 | 1.00 | 0.22 | 1.00 | 1.00 | 1.00 |
| Mirlet7d | 1.03 | 1.00 | 0.36 | 0.66 | 2.26 | 0.46 | 4.85 | 12.14 | 0.79 |
| Mirlet7e | 2.68 | 1.00 | 0.89 | 10.29 | 0.10 | 0.37 | 1.00 | 11.27 | 1.00 |
| Mirlet7f-1 | 1.00 | 1.00 | 1.00 | 1.00 | 13.89 | 10.10 | 1.00 | 13.57 | 1.00 |
| Mirlet7g | 1.00 | 1.00 | 1.00 | 0.08 | 0.08 | 1.00 | 1.00 | 1.00 | 1.00 |
| Mirlet7i | 0.08 | 0.31 | 1.00 | 0.08 | 17.19 | 12.80 | 1.00 | 1.00 | 1.00 |
| Mki67 | 1.25 | 2.76 | 1.30 | 1.00 | 1.70 | 1.00 | 1.00 | 7.00 | 1.00 |
| Mmp12 | 1.57 | 18.78 | 1.00 | 0.94 | 1.03 | 1.08 | 1.00 | 1.00 | 1.00 |
| Mpeg1 | 1.50 | 10.79 | 2.16 | 0.94 | 1.95 | 0.80 | 0.74 | 2.43 | 1.41 |
| Ms4a7 | 0.93 | 9.24 | 1.55 | 1.00 | 1.00 | 1.00 | 1.00 | 1.00 | 1.00 |
| Mt4 | 1.00 | 1.00 | 1.00 | 1.00 | 1.00 | 1.00 | 1.00 | 1.00 | 1.00 |
| Muc15 | 1.00 | 1.26 | 1.00 | 1.00 | 1.00 | 1.00 | 1.00 | 1.00 | 1.00 |
| Muc5b | 1.00 | 1.00 | 1.00 | 1.00 | 1.00 | 1.00 | 1.00 | 1.00 | 1.00 |
| Mxd3 | 1.02 | 2.27 | 1.00 | 1.00 | 1.00 | 1.00 | 1.00 | 1.19 | 1.00 |
| Myb | 1.00 | 3.31 | 1.00 | 1.00 | 1.55 | 1.00 | 1.00 | 6.16 | 1.00 |
| Myh1 | 0.56 | 0.60 | 0.74 | 1.00 | 1.00 | 1.00 | 1.00 | 1.00 | 1.00 |
| Myh6 | 0.54 | 0.54 | 0.65 | 1.00 | 1.00 | 1.00 | 1.00 | 1.00 | 1.00 |
| Myh8 | 0.75 | 0.90 | 0.86 | 1.00 | 1.00 | 1.00 | 1.00 | 1.00 | 1.00 |
| Myl1 | 0.84 | 1.97 | 1.41 | 1.00 | 1.00 | 1.00 | 1.00 | 1.00 | 1.00 |
| Myl10 | 1.00 | 1.00 | 1.00 | 1.00 | 1.00 | 1.00 | 1.00 | 2.66 | 1.00 |
| Myl3 | 0.81 | 0.52 | 0.59 | 1.00 | 1.00 | 1.00 | 1.00 | 1.00 | 1.00 |
| Myl4 | 0.78 | 1.33 | 1.45 | 1.24 | 1.08 | 0.97 | 1.00 | 1.01 | 1.00 |
| Myl7 | 0.55 | 0.88 | 1.09 | 0.83 | 1.00 | 1.00 | 1.00 | 1.00 | 1.00 |
| Myo3b | 1.00 | 1.00 | 1.00 | 1.27 | 1.16 | 1.00 | 1.00 | 1.00 | 1.00 |
| Mzb1 | 0.96 | 3.55 | 2.60 | 0.79 | 2.51 | 2.18 | 1.00 | 19.18 | 1.00 |
| Napsa | 3.26 | 4.08 | 5.52 | 1.13 | 0.99 | 0.95 | 1.00 | 4.09 | 1.00 |
| Ncapg | 1.00 | 1.23 | 1.00 | 1.00 | 1.00 | 1.00 | 1.00 | 1.86 | 0.89 |
| Ndc80 | 1.00 | 1.33 | 1.00 | 1.00 | 1.00 | 1.00 | 1.00 | 1.57 | 1.00 |
| Neil3 | 1.00 | 1.37 | 1.00 | 1.00 | 1.00 | 1.00 | 1.00 | 1.73 | 1.00 |
| Nfe2l3 | 1.00 | 1.00 | 1.00 | 1.00 | 1.00 | 1.00 | 1.00 | 1.00 | 1.11 |
| Ngp | 1.07 | 6.64 | 2.20 | 1.00 | 2.54 | 1.00 | 1.00 | 14.31 | 1.00 |
| Nipal2 | 1.00 | 1.00 | 1.00 | 5.17 | 4.90 | 1.22 | 1.00 | 1.00 | 1.00 |
| Nmrk2 | 15.94 | 2.79 | 3.65 | 1.00 | 1.00 | 1.00 | 1.00 | 1.00 | 1.00 |
| Nov | 0.95 | 1.54 | 1.81 | 1.00 | 1.00 | 1.00 | 1.00 | 3.07 | 1.00 |
| Nox4 | 1.12 | 4.18 | 5.57 | 1.11 | 0.74 | 0.65 | 1.25 | 0.61 | 0.77 |
| Nppa | 1.13 | 3.58 | 4.16 | 1.00 | 1.00 | 1.00 | 1.00 | 1.00 | 1.00 |
| Nppb | 5.78 | 2.31 | 6.52 | 1.00 | 1.00 | 1.00 | 1.00 | 1.00 | 1.00 |
| Nptx1 | 1.00 | 1.00 | 1.00 | 1.00 | 1.00 | 1.00 | 1.00 | 1.00 | 1.00 |
| Npy | 1.92 | 2.38 | 1.79 | 12.05 | 15.33 | 2.15 | 1.00 | 1.00 | 1.00 |
| Nr4a1 | 9.10 | 1.27 | 1.96 | 2.14 | 1.95 | 0.75 | 1.00 | 1.76 | 1.18 |
| Nr4a3 | 1.18 | 0.32 | 2.81 | 1.00 | 1.30 | 1.00 | 1.00 | 1.00 | 1.00 |
| Nuf2 | 1.00 | 2.25 | 1.00 | 1.00 | 1.00 | 1.00 | 1.00 | 1.66 | 1.00 |
| Nupr1 | 1.89 | 2.55 | 5.40 | 1.11 | 1.16 | 0.89 | 1.19 | 1.32 | 1.00 |
| Nusap1 | 1.00 | 2.34 | 1.00 | 1.00 | 1.22 | 1.00 | 1.00 | 2.99 | 1.00 |
| Nxf3 | 1.00 | 1.00 | 1.00 | 1.00 | 1.00 | 1.00 | 1.00 | 1.00 | 1.00 |

Fig. 31-90

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Mir8116 | 0.45 | 1.88 | 0.60 | 0.30 | 0.80 | 0.47 | 0.96 | 1.29 | 1.92 |
| Mir8118 | 1.00 | 1.00 | 1.00 | 1.00 | 1.00 | 1.00 | 1.00 | 3.42 | 1.00 |
| Mir8120 | 0.53 | 0.54 | 2.42 | 1.00 | 1.00 | 1.00 | 1.00 | 1.00 | 1.00 |
| Mir872 | 1.00 | 1.00 | 1.00 | 1.00 | 1.00 | 1.00 | 1.00 | 1.00 | 1.00 |
| Mir873 | 1.00 | 1.00 | 1.00 | 1.00 | 1.00 | 1.00 | 1.00 | 1.00 | 1.00 |
| Mir874 | 1.00 | 1.00 | 1.00 | 15.96 | 1.00 | 1.00 | 1.00 | 1.00 | 1.00 |
| Mir875 | 14.21 | 0.04 | 1.00 | 1.00 | 1.00 | 1.00 | 1.00 | 1.00 | 1.00 |
| Mir877 | 2.01 | 1.00 | 0.28 | 1.00 | 0.10 | 1.00 | 0.06 | 1.00 | 1.10 |
| Mir883a | 1.00 | 1.00 | 1.00 | 1.00 | 1.00 | 1.00 | 1.00 | 1.00 | 1.00 |
| Mir9-1 | 1.00 | 1.00 | 1.00 | 1.00 | 1.00 | 1.00 | 1.00 | 1.00 | 1.00 |
| Mir92-1 | 0.53 | 1.00 | 1.00 | 1.00 | 1.00 | 1.00 | 1.00 | 1.00 | 1.00 |
| Mir92-2 | 1.00 | 1.00 | 1.00 | 1.00 | 1.00 | 1.00 | 1.00 | 1.00 | 9.80 |
| Mir92b | 1.00 | 1.00 | 1.00 | 1.00 | 1.00 | 1.00 | 1.00 | 1.00 | 1.00 |
| Mir93 | 1.00 | 1.00 | 1.00 | 1.00 | 1.00 | 18.06 | 0.07 | 16.28 | 11.30 |
| Mir99a | 1.00 | 2.05 | 67.68 | 0.01 | 32.40 | 1.00 | 1.00 | 1.00 | 1.00 |
| Mir99b | 1.03 | 1.06 | 1.00 | 1.00 | 1.00 | 1.00 | 1.00 | 1.00 | 0.02 |
| Mirlet7a-1 | 6.82 | 1.00 | 0.15 | 6.86 | 1.00 | 1.00 | 0.09 | 1.00 | 1.00 |
| Mirlet7b | 15.95 | 0.11 | 11.69 | 1.00 | 0.32 | 1.00 | 0.02 | 1.00 | 12.01 |
| Mirlet7c-1 | 1.00 | 1.00 | 1.00 | 0.13 | 1.00 | 1.00 | 1.00 | 1.00 | 1.00 |
| Mirlet7c-2 | 5.58 | 1.00 | 9.77 | 1.99 | 1.00 | 1.00 | 12.16 | 1.00 | 4.12 |
| Mirlet7d | 0.47 | 0.42 | 0.34 | 0.58 | 1.01 | 0.92 | 1.50 | 0.74 | 0.96 |
| Mirlet7e | 0.47 | 1.04 | 0.86 | 1.00 | 1.00 | 7.52 | 1.00 | 1.00 | 1.00 |
| Mirlet7f-1 | 8.38 | 0.03 | 0.12 | 1.00 | 1.00 | 8.34 | 1.00 | 1.00 | 0.08 |
| Mirlet7g | 0.96 | 1.00 | 1.00 | 1.00 | 1.00 | 1.00 | 1.00 | 1.00 | 23.98 |
| Mirlet7i | 1.37 | 0.69 | 3.10 | 1.00 | 1.00 | 1.00 | 4.61 | 2.35 | 0.69 |
| Mki67 | 1.89 | 8.05 | 1.22 | 1.00 | 0.61 | 0.83 | 1.11 | 1.41 | 3.50 |
| Mmp12 | 1.23 | 1.43 | 2.29 | 1.00 | 1.00 | 1.00 | 1.59 | 0.63 | 0.80 |
| Mpeg1 | 0.93 | 1.49 | 1.07 | 0.64 | 1.84 | 1.51 | 0.92 | 0.91 | 0.93 |
| Ms4a7 | 1.03 | 1.62 | 1.16 | 0.94 | 0.83 | 0.65 | 0.70 | 1.33 | 0.58 |
| Mt4 | 1.00 | 1.00 | 1.00 | 1.00 | 1.00 | 1.00 | 1.00 | 1.00 | 1.00 |
| Muc15 | 1.00 | 1.00 | 1.00 | 1.00 | 1.00 | 1.00 | 1.00 | 1.00 | 1.00 |
| Muc5b | 1.62 | 0.75 | 1.48 | 1.00 | 1.00 | 1.00 | 1.00 | 1.00 | 1.00 |
| Mxd3 | 1.81 | 5.96 | 0.96 | 1.00 | 1.00 | 1.00 | 1.19 | 1.34 | 3.28 |
| Myb | 0.92 | 10.17 | 0.89 | 1.00 | 1.32 | 1.00 | 0.66 | 1.11 | 1.28 |
| Myh1 | 1.00 | 1.00 | 1.00 | 0.90 | 1.10 | 0.88 | 1.00 | 1.00 | 1.00 |
| Myh6 | 0.60 | 0.84 | 1.06 | 1.34 | 1.27 | 1.00 | 1.00 | 1.00 | 1.00 |
| Myh8 | 1.00 | 1.00 | 1.00 | 1.05 | 0.95 | 0.88 | 1.00 | 1.00 | 1.00 |
| Myl1 | 1.26 | 4.29 | 1.77 | 0.95 | 0.88 | 1.02 | 1.00 | 1.00 | 1.00 |
| Myl10 | 1.00 | 6.71 | 1.00 | 0.74 | 1.22 | 0.74 | 1.00 | 1.00 | 1.00 |
| Myl3 | 0.50 | 1.72 | 0.69 | 1.46 | 1.07 | 1.05 | 1.00 | 1.00 | 1.00 |
| Myl4 | 0.80 | 0.97 | 1.17 | 0.32 | 1.36 | 1.68 | 0.79 | 1.10 | 1.12 |
| Myl7 | 0.59 | 0.90 | 1.14 | 1.00 | 1.00 | 1.00 | 1.00 | 1.00 | 1.00 |
| Myo3b | 1.00 | 1.00 | 1.00 | 1.00 | 1.00 | 1.00 | 1.00 | 1.00 | 1.00 |
| Mzb1 | 0.58 | 19.21 | 0.85 | 1.10 | 1.73 | 1.00 | 0.81 | 1.51 | 1.02 |
| Napsa | 1.29 | 1.17 | 1.06 | 1.00 | 0.93 | 1.00 | 1.19 | 0.93 | 0.65 |
| Ncapg | 1.69 | 7.55 | 1.00 | 1.00 | 1.00 | 1.00 | 0.88 | 1.43 | 2.96 |
| Ndc80 | 1.62 | 8.42 | 1.00 | 1.00 | 1.00 | 1.00 | 1.00 | 1.38 | 2.53 |
| Neil3 | 1.17 | 7.79 | 1.00 | 1.00 | 1.00 | 1.00 | 1.14 | 1.39 | 3.16 |
| Nfe2l3 | 0.67 | 0.59 | 1.32 | 1.00 | 1.00 | 1.00 | 1.00 | 1.00 | 1.09 |
| Ngp | 0.52 | 18.43 | 2.44 | 1.00 | 0.07 | 0.07 | 0.29 | 1.52 | 2.26 |
| Nipal2 | 1.24 | 1.11 | 0.74 | 1.00 | 1.00 | 1.00 | 1.33 | 1.00 | 1.00 |
| Nmrk2 | 2.51 | 1.08 | 1.00 | 0.14 | 0.63 | 2.14 | 1.00 | 1.00 | 1.00 |
| Nov | 1.10 | 6.51 | 1.89 | 1.42 | 0.63 | 1.09 | 1.00 | 1.00 | 1.00 |
| Nox4 | 1.00 | 0.64 | 1.01 | 1.55 | 1.09 | 1.19 | 1.00 | 1.00 | 1.00 |
| Nppa | 1.48 | 28.68 | 14.14 | 1.00 | 2.10 | 1.00 | 1.00 | 1.00 | 1.00 |
| Nppb | 1.96 | 10.58 | 4.12 | 1.00 | 1.00 | 1.00 | 1.00 | 1.00 | 1.00 |
| Nptx1 | 1.12 | 1.06 | 1.01 | 1.00 | 1.00 | 1.00 | 1.00 | 1.00 | 1.00 |
| Npy | 2.63 | 1.30 | 0.69 | 1.00 | 1.00 | 1.00 | 22.07 | 4.62 | 0.84 |
| Nr4a1 | 1.02 | 1.52 | 1.41 | 1.15 | 0.61 | 0.97 | 0.93 | 0.83 | 0.82 |
| Nr4a3 | 2.13 | 0.96 | 3.58 | 0.70 | 0.18 | 7.49 | 1.02 | 1.24 | 0.93 |
| Nuf2 | 1.63 | 7.19 | 1.00 | 1.00 | 1.00 | 1.00 | 0.86 | 1.37 | 3.10 |
| Nupr1 | 0.97 | 0.88 | 1.39 | 1.29 | 0.83 | 1.01 | 1.85 | 0.27 | 0.16 |
| Nusap1 | 1.39 | 7.99 | 0.94 | 1.00 | 0.96 | 1.00 | 1.15 | 1.44 | 3.57 |
| Nxf3 | 1.00 | 1.00 | 1.00 | 1.00 | 1.00 | 1.00 | 1.00 | 1.00 | 1.00 |

Fig. 31- 91

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Mir8116 | 0.42 | 0.04 | 1.56 | 1.87 | 0.87 | 3.16 | 6.73 | 0.91 | 1.09 |
| Mir8118 | 1.00 | 1.00 | 0.41 | 1.00 | 1.00 | 1.00 | 1.00 | 1.00 | 1.00 |
| Mir8120 | 0.26 | 0.43 | 0.52 | 0.21 | 4.13 | 0.46 | 2.08 | 0.93 | 1.00 |
| Mir872 | 1.00 | 1.00 | 1.00 | 1.00 | 1.00 | 1.00 | 0.08 | 1.00 | 11.50 |
| Mir873 | 1.00 | 25.97 | 18.67 | 1.00 | 1.00 | 1.00 | 1.00 | 1.00 | 1.00 |
| Mir874 | 1.00 | 27.94 | 0.05 | 1.00 | 1.00 | 0.06 | 1.00 | 0.06 | 1.00 |
| Mir875 | 1.00 | 24.19 | 1.00 | 1.00 | 1.00 | 1.00 | 1.00 | 12.67 | 1.00 |
| Mir877 | 0.05 | 1.96 | 1.00 | 1.00 | 0.02 | 21.81 | 11.06 | 2.67 | 0.11 |
| Mir883a | 1.00 | 1.00 | 1.00 | 1.00 | 1.00 | 1.00 | 17.40 | 1.00 | 0.07 |
| Mir9-1 | 1.21 | 0.50 | 1.96 | 1.00 | 1.00 | 1.00 | 17.82 | 1.00 | 0.07 |
| Mir92-1 | 16.66 | 1.00 | 1.00 | 1.00 | 1.32 | 1.00 | 1.00 | 1.00 | 1.00 |
| Mir92-2 | 1.00 | 1.00 | 1.00 | 1.00 | 1.00 | 1.00 | 1.00 | 1.00 | 1.00 |
| Mir92b | 1.00 | 1.00 | 1.00 | 1.00 | 1.00 | 1.00 | 2.07 | 1.00 | 1.00 |
| Mir93 | 0.95 | 0.52 | 1.39 | 0.09 | 1.00 | 1.00 | 1.00 | 0.11 | 0.12 |
| Mir99a | 1.00 | 1.00 | 51.14 | 1.00 | 70.32 | 1.00 | 1.11 | 1.00 | 1.00 |
| Mir99b | 1.00 | 0.02 | 0.03 | 1.00 | 1.00 | 1.62 | 2.12 | 1.00 | 2.11 |
| Mirlet7a-1 | 0.94 | 1.00 | 14.75 | 1.20 | 0.12 | 7.25 | 7.55 | 1.00 | 1.00 |
| Mirlet7b | 2.70 | 1.00 | 0.03 | 1.00 | 1.00 | 1.83 | 1.00 | 1.00 | 1.00 |
| Mirlet7c-1 | 1.00 | 1.00 | 1.00 | 0.06 | 1.00 | 0.13 | 1.00 | 1.00 | 1.00 |
| Mirlet7c-2 | 0.83 | 1.00 | 1.00 | 1.00 | 0.04 | 0.88 | 0.29 | 1.00 | 4.62 |
| Mirlet7d | 1.23 | 1.21 | 0.88 | 1.41 | 2.98 | 0.97 | 0.63 | 0.54 | 1.02 |
| Mirlet7e | 1.98 | 1.50 | 0.52 | 2.06 | 1.32 | 0.70 | 1.11 | 0.90 | 0.71 |
| Mirlet7f-1 | 0.97 | 0.08 | 1.54 | 0.04 | 46.65 | 0.04 | 1.00 | 1.00 | 7.98 |
| Mirlet7g | 1.00 | 1.00 | 10.05 | 1.20 | 1.00 | 1.00 | 1.00 | 1.00 | 1.00 |
| Mirlet7i | 1.00 | 0.51 | 1.00 | 17.54 | 44.91 | 1.00 | 1.00 | 0.49 | 0.04 |
| Mki67 | 1.00 | 2.98 | 1.00 | 0.99 | 0.85 | 0.75 | 1.05 | 1.08 | 1.03 |
| Mmp12 | 1.00 | 1.00 | 1.00 | 1.48 | 3.47 | 0.23 | 1.00 | 1.00 | 1.00 |
| Mpeg1 | 1.02 | 2.26 | 1.03 | 1.68 | 2.47 | 0.58 | 1.01 | 1.58 | 0.93 |
| Ms4a7 | 1.00 | 1.00 | 1.00 | 1.38 | 1.51 | 0.65 | 1.02 | 1.00 | 1.00 |
| Mt4 | 1.00 | 1.00 | 1.00 | 1.00 | 1.00 | 1.00 | 1.18 | 1.15 | 1.00 |
| Muc15 | 1.00 | 1.00 | 1.00 | 1.00 | 164.78 | 1.00 | 1.06 | 0.82 | 1.06 |
| Muc5b | 1.00 | 1.00 | 1.00 | 1.00 | 65.00 | 1.00 | 1.00 | 1.00 | 1.00 |
| Mxd3 | 1.00 | 1.32 | 1.00 | 1.00 | 1.00 | 1.00 | 1.11 | 0.79 | 1.04 |
| Myb | 1.00 | 3.33 | 1.00 | 0.76 | 0.67 | 1.00 | 1.00 | 1.00 | 1.00 |
| Myh1 | 1.00 | 1.00 | 1.00 | 1.00 | 1.00 | 1.00 | 1.00 | 1.00 | 1.00 |
| Myh6 | 0.88 | 0.87 | 1.75 | 1.00 | 1.00 | 1.00 | 0.63 | 0.66 | 0.98 |
| Myh8 | 1.00 | 1.00 | 1.00 | 1.00 | 1.00 | 1.00 | 1.00 | 1.00 | 1.00 |
| Myl1 | 0.90 | 1.00 | 1.14 | 0.86 | 0.62 | 1.29 | 1.00 | 1.00 | 1.00 |
| Myl10 | 1.00 | 2.28 | 1.00 | 0.92 | 1.00 | 1.00 | 0.93 | 0.97 | 0.93 |
| Myl3 | 1.00 | 1.00 | 1.00 | 1.00 | 1.00 | 1.00 | 1.00 | 1.00 | 1.00 |
| Myl4 | 0.63 | 1.05 | 1.54 | 1.84 | 0.95 | 1.06 | 1.10 | 1.08 | 0.94 |
| Myl7 | 1.00 | 1.00 | 1.96 | 1.16 | 0.70 | 1.00 | 1.00 | 1.00 | 1.00 |
| Myo3b | 1.00 | 1.00 | 1.00 | 1.00 | 6.00 | 1.00 | 1.00 | 1.00 | 1.00 |
| Mzb1 | 1.00 | 8.48 | 1.00 | 1.00 | 2.58 | 0.22 | 0.95 | 1.00 | 1.00 |
| Napsa | 1.00 | 1.99 | 1.00 | 0.84 | 0.45 | 0.27 | 1.05 | 1.04 | 1.00 |
| Ncapg | 1.00 | 1.06 | 1.00 | 1.00 | 1.00 | 1.00 | 1.06 | 1.00 | 0.98 |
| Ndc80 | 1.00 | 1.00 | 1.00 | 1.00 | 1.00 | 1.00 | 1.00 | 0.93 | 0.93 |
| Neil3 | 1.00 | 1.00 | 1.00 | 1.00 | 1.00 | 1.00 | 1.13 | 0.85 | 1.03 |
| Nfe2l3 | 0.89 | 0.82 | 1.12 | 0.88 | 8.38 | 0.75 | 0.91 | 0.99 | 1.00 |
| Ngp | 1.00 | 2.13 | 1.11 | 1.00 | 3.69 | 1.00 | 1.00 | 1.00 | 1.00 |
| Nipal2 | 1.23 | 1.19 | 0.91 | 1.00 | 2.24 | 1.00 | 1.00 | 1.00 | 1.00 |
| Nmrk2 | 1.00 | 1.00 | 1.00 | 1.00 | 1.00 | 1.00 | 1.18 | 1.00 | 0.99 |
| Nov | 0.94 | 1.29 | 0.87 | 1.62 | 0.82 | 0.72 | 1.00 | 1.00 | 1.00 |
| Nox4 | 1.00 | 1.00 | 1.00 | 1.80 | 1.08 | 0.86 | 1.00 | 1.00 | 1.00 |
| Nppa | 1.00 | 1.09 | 12.19 | 1.00 | 1.00 | 1.00 | 1.00 | 1.00 | 1.00 |
| Nppb | 1.00 | 1.00 | 1.00 | 1.00 | 1.00 | 1.00 | 1.00 | 1.00 | 1.00 |
| Nptx1 | 1.04 | 0.96 | 1.04 | 1.00 | 8.04 | 1.00 | 1.00 | 1.00 | 1.00 |
| Npy | 1.05 | 0.88 | 1.04 | 1.00 | 0.84 | 1.00 | 1.00 | 1.00 | 1.08 |
| Nr4a1 | 2.30 | 1.19 | 1.11 | 1.84 | 1.62 | 1.21 | 0.89 | 1.12 | 0.91 |
| Nr4a3 | 1.66 | 1.24 | 1.15 | 3.17 | 1.24 | 1.18 | 0.71 | 0.91 | 0.95 |
| Nuf2 | 1.00 | 1.16 | 1.00 | 1.00 | 1.00 | 1.00 | 1.16 | 0.91 | 1.13 |
| Nupr1 | 0.99 | 1.05 | 1.24 | 1.10 | 1.13 | 0.87 | 0.85 | 0.80 | 1.32 |
| Nusap1 | 1.00 | 1.84 | 0.96 | 1.00 | 0.92 | 0.94 | 1.13 | 0.89 | 0.99 |
| Nxf3 | 1.00 | 1.00 | 1.00 | 1.00 | 30.47 | 1.00 | 0.99 | 0.90 | 0.93 |

Fig. 31- 92

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Mir8116 | 0.90 | 0.74 | 0.75 | 1.26 | 0.60 | 1.13 | 4.19 | 1.00 | 1.00 | 1.00 | 1.00 | 1.00 |
| Mir8118 | 5.18 | 1.00 | 1.00 | 1.00 | 1.00 | 1.00 | 1.00 | 1.00 | 1.00 | 1.00 | 1.00 | 1.00 |
| Mir8120 | 7.84 | 1.00 | 0.57 | 1.00 | 1.00 | 1.00 | 1.00 | 1.00 | 1.00 | 1.00 | 1.00 | 1.00 |
| Mir872 | 1.00 | 1.00 | 1.00 | 1.00 | 1.00 | 1.00 | 1.00 | 1.00 | 1.00 | 1.00 | 1.00 | 1.00 |
| Mir873 | 1.00 | 1.00 | 1.00 | 1.00 | 1.00 | 1.00 | 1.00 | 1.00 | 1.00 | 1.00 | 1.00 | 1.00 |
| Mir874 | 1.00 | 0.05 | 1.00 | 1.00 | 1.00 | 1.00 | 1.00 | 1.00 | 1.00 | 1.00 | 1.00 | 1.00 |
| Mir875 | 1.00 | 1.00 | 1.00 | 1.00 | 1.00 | 1.00 | 1.00 | 1.00 | 1.00 | 1.00 | 1.00 | 1.00 |
| Mir877 | 0.72 | 1.36 | 0.26 | 0.66 | 0.91 | 11.90 | 0.12 | 10.61 | 0.13 | 1.00 | 1.00 | 1.00 |
| Mir883a | 1.00 | 1.00 | 1.00 | 1.00 | 1.00 | 1.00 | 1.00 | 1.00 | 1.00 | 1.00 | 1.00 | 1.00 |
| Mir9-1 | 1.00 | 1.00 | 1.00 | 1.00 | 1.00 | 1.00 | 1.00 | 1.00 | 1.00 | 1.00 | 1.00 | 1.00 |
| Mir92-1 | 1.00 | 1.00 | 1.00 | 1.00 | 1.00 | 1.00 | 1.00 | 1.00 | 0.73 | 1.00 | 1.00 | 1.00 |
| Mir92-2 | 1.39 | 0.37 | 1.71 | 1.00 | 7.44 | 1.00 | 1.00 | 1.00 | 1.00 | 1.00 | 1.00 | 1.00 |
| Mir92b | 1.00 | 1.00 | 1.00 | 1.00 | 1.00 | 1.00 | 1.00 | 1.00 | 1.00 | 1.00 | 1.00 | 1.00 |
| Mir93 | 1.06 | 0.94 | 0.96 | 1.00 | 1.00 | 0.10 | 1.00 | 1.00 | 1.00 | 1.00 | 1.00 | 1.00 |
| Mir99a | 42.12 | 1.00 | 1.04 | 1.00 | 1.00 | 1.00 | 1.00 | 1.00 | 1.00 | 1.00 | 1.00 | 1.00 |
| Mir99b | 1.00 | 27.88 | 30.10 | 1.00 | 1.00 | 1.00 | 1.00 | 1.00 | 1.00 | 1.00 | 1.00 | 1.00 |
| Mirlet7a-1 | 1.00 | 0.12 | 1.00 | 0.13 | 1.00 | 1.00 | 4.87 | 1.00 | 1.00 | 1.00 | 1.00 | 1.00 |
| Mirlet7b | 1.00 | 0.19 | 3.45 | 1.00 | 1.00 | 7.27 | 1.00 | 0.11 | 1.00 | 1.00 | 1.00 | 1.00 |
| Mirlet7c-1 | 1.00 | 1.00 | 1.00 | 1.00 | 1.00 | 1.00 | 1.00 | 1.00 | 1.00 | 1.00 | 1.00 | 1.00 |
| Mirlet7c-2 | 0.20 | 1.00 | 1.00 | 1.00 | 1.00 | 0.44 | 1.00 | 1.00 | 0.15 | 1.00 | 1.00 | 1.00 |
| Mirlet7d | 1.29 | 1.09 | 0.69 | 3.00 | 0.92 | 0.30 | 0.86 | 0.12 | 0.51 | 1.00 | 1.00 | 1.00 |
| Mirlet7e | 4.47 | 0.33 | 1.09 | 1.00 | 1.00 | 1.00 | 1.00 | 0.17 | 1.00 | 1.00 | 1.00 | 1.00 |
| Mirlet7f-1 | 1.15 | 1.00 | 11.15 | 9.00 | 1.00 | 1.00 | 5.67 | 1.00 | 1.00 | 1.00 | 1.00 | 1.00 |
| Mirlet7g | 1.00 | 1.00 | 1.00 | 1.00 | 1.00 | 1.00 | 1.00 | 1.00 | 1.00 | 1.00 | 1.00 | 1.00 |
| Mirlet7i | 0.66 | 1.87 | 0.50 | 0.09 | 9.61 | 0.10 | 1.00 | 1.28 | 1.00 | 1.00 | 1.00 | 1.00 |
| Mki67 | 0.35 | 0.67 | 1.05 | 1.07 | 1.07 | 1.10 | 1.00 | 1.00 | 1.00 | 0.91 | 0.98 | 1.11 |
| Mmp12 | 0.58 | 0.56 | 0.95 | 1.00 | 1.00 | 1.00 | 1.00 | 1.00 | 1.00 | 1.00 | 0.83 | 0.88 |
| Mpeg1 | 1.01 | 1.60 | 1.31 | 1.14 | 1.28 | 1.05 | 0.78 | 0.72 | 0.71 | 1.21 | 1.03 | 1.00 |
| Ms4a7 | 1.00 | 1.21 | 1.07 | 1.00 | 1.00 | 0.91 | 1.00 | 1.00 | 1.00 | 0.84 | 1.00 | 1.00 |
| Mt4 | 1.42 | 22.59 | 0.62 | 1.00 | 1.00 | 1.00 | 1.00 | 1.00 | 1.00 | 0.78 | 1.00 | 0.89 |
| Muc15 | 1.01 | 0.84 | 1.00 | 1.00 | 1.00 | 1.00 | 1.00 | 1.00 | 1.00 | 0.99 | 1.00 | 1.00 |
| Muc5b | 1.00 | 3.87 | 1.00 | 1.00 | 1.00 | 1.00 | 1.00 | 1.00 | 1.00 | 1.00 | 0.97 | 1.00 |
| Mxd3 | 0.33 | 0.66 | 0.93 | 1.07 | 0.90 | 1.14 | 1.00 | 1.00 | 1.00 | 0.72 | 0.97 | 0.95 |
| Myb | 0.94 | 0.71 | 0.64 | 1.00 | 0.76 | 0.83 | 1.00 | 1.00 | 1.00 | 0.79 | 1.23 | 1.27 |
| Myh1 | 1.00 | 10.92 | 1.00 | 1.00 | 1.00 | 1.00 | 1.00 | 1.00 | 1.00 | 1.41 | 0.99 | 0.86 |
| Myh6 | 12.78 | 4.34 | 5.80 | 1.00 | 1.00 | 1.00 | 1.00 | 1.00 | 1.00 | 1.00 | 1.00 | 1.00 |
| Myh8 | 1.00 | 14.29 | 1.00 | 1.00 | 1.00 | 1.00 | 1.00 | 1.00 | 1.00 | 1.36 | 1.00 | 0.86 |
| Myl1 | 2.05 | 11.17 | 4.20 | 1.00 | 1.00 | 1.00 | 1.00 | 1.00 | 1.00 | 1.55 | 1.06 | 1.02 |
| Myl10 | 1.04 | 1.00 | 0.88 | 1.39 | 0.90 | 0.93 | 1.00 | 1.00 | 1.00 | 1.00 | 1.03 | 0.98 |
| Myl3 | 1.39 | 16.87 | 1.00 | 1.00 | 1.00 | 1.00 | 1.00 | 1.00 | 1.00 | 1.00 | 0.96 | 0.87 |
| Myl4 | 9.58 | 4.10 | 3.97 | 0.77 | 0.41 | 0.77 | 1.00 | 1.00 | 1.00 | 1.34 | 1.19 | 0.98 |
| Myl7 | 6.64 | 2.34 | 3.25 | 1.00 | 1.00 | 1.00 | 1.00 | 1.00 | 1.00 | 1.00 | 0.99 | 0.93 |
| Myo3b | 1.09 | 0.92 | 1.00 | 1.00 | 1.00 | 1.00 | 1.00 | 1.00 | 1.00 | 1.00 | 0.92 | 0.93 |
| Mzb1 | 1.49 | 2.88 | 2.34 | 1.05 | 0.43 | 0.80 | 1.00 | 0.94 | 0.92 | 1.00 | 1.16 | 1.20 |
| Napsa | 1.36 | 2.50 | 1.47 | 1.03 | 1.21 | 1.02 | 1.00 | 1.00 | 1.00 | 1.35 | 1.05 | 1.08 |
| Ncapg | 0.37 | 0.63 | 0.89 | 0.96 | 0.96 | 0.97 | 1.00 | 1.00 | 1.00 | 1.00 | 1.21 | 1.12 |
| Ndc80 | 0.42 | 0.53 | 0.83 | 1.02 | 0.94 | 1.04 | 1.00 | 1.00 | 1.00 | 1.00 | 0.92 | 1.01 |
| Neil3 | 0.36 | 0.63 | 0.98 | 1.03 | 0.83 | 1.02 | 1.00 | 1.00 | 1.00 | 0.95 | 1.00 | 1.00 |
| Nfe2l3 | 0.99 | 1.00 | 1.11 | 1.00 | 1.00 | 1.00 | 1.00 | 1.00 | 1.00 | 0.89 | 1.09 | 0.96 |
| Ngp | 1.05 | 4.21 | 1.22 | 1.04 | 1.01 | 1.06 | 1.00 | 0.98 | 1.00 | 1.00 | 1.42 | 1.03 |
| Nipal2 | 1.20 | 0.93 | 1.00 | 1.00 | 1.00 | 1.00 | 1.17 | 1.07 | 0.98 | 1.04 | 0.96 | 0.97 |
| Nmrk2 | 1.00 | 1.00 | 1.00 | 1.00 | 1.00 | 1.00 | 1.00 | 1.00 | 1.00 | 1.25 | 1.01 | 0.93 |
| Nov | 1.44 | 0.76 | 1.68 | 1.00 | 1.00 | 1.00 | 1.00 | 1.00 | 1.00 | 0.97 | 1.00 | 1.00 |
| Nox4 | 1.19 | 1.13 | 1.10 | 1.00 | 1.00 | 1.00 | 1.00 | 1.00 | 1.00 | 0.90 | 0.96 | 1.15 |
| Nppa | 4.70 | 116.93 | 7.81 | 1.00 | 1.00 | 1.00 | 1.00 | 1.00 | 1.00 | 1.00 | 1.00 | 1.00 |
| Nppb | 1.00 | 5.46 | 1.00 | 1.00 | 1.00 | 1.00 | 1.00 | 1.00 | 1.00 | 1.00 | 0.88 | 0.96 |
| Nptx1 | 1.00 | 1.00 | 1.00 | 1.00 | 1.00 | 1.00 | 1.00 | 1.00 | 1.00 | 1.13 | 0.66 | 0.86 |
| Npy | 1.00 | 1.00 | 1.00 | 1.29 | 4.07 | 0.54 | 1.00 | 1.00 | 1.00 | 1.01 | 1.00 | 1.00 |
| Nr4a1 | 0.81 | 0.95 | 0.92 | 1.15 | 1.25 | 0.94 | 1.86 | 1.00 | 1.00 | 1.07 | 0.53 | 1.00 |
| Nr4a3 | 0.78 | 0.96 | 1.26 | 1.00 | 1.00 | 1.00 | 1.00 | 1.00 | 1.00 | 1.12 | 1.00 | 1.00 |
| Nuf2 | 0.43 | 0.66 | 0.91 | 1.02 | 0.98 | 1.06 | 1.00 | 1.00 | 1.00 | 0.81 | 1.16 | 1.03 |
| Nupr1 | 1.41 | 1.24 | 1.72 | 0.83 | 2.04 | 1.34 | 1.71 | 1.17 | 0.96 | 0.93 | 1.03 | 1.14 |
| Nusap1 | 0.35 | 0.67 | 0.98 | 1.09 | 0.91 | 1.16 | 1.00 | 1.00 | 1.00 | 0.79 | 0.97 | 2.95 |
| Nxf3 | 1.00 | 1.00 | 1.00 | 1.00 | 1.00 | 1.00 | 1.00 | 1.00 | 1.00 | 1.00 | 1.05 | 1.06 |

Fig. 31-93

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Nxpe2 | 1.00 | 1.00 | 1.00 | 1.00 | 1.00 | 1.00 | 1.41 | 1.08 | 0.66 |
| Nxpe5 | 1.27 | 1.76 | 2.69 | 1.00 | 1.00 | 1.00 | 1.00 | 1.00 | 1.00 |
| Oas2 | 1.21 | 2.30 | 0.78 | 1.00 | 1.72 | 0.99 | 1.00 | 2.12 | 0.98 |
| Odf1 | 1.00 | 1.00 | 1.00 | 1.00 | 1.00 | 1.00 | 1.00 | 1.00 | 1.00 |
| Otof | 1.00 | 1.00 | 1.00 | 1.00 | 1.00 | 1.00 | 1.00 | 1.00 | 1.00 |
| Otud1 | 5.05 | 1.70 | 0.86 | 1.15 | 1.07 | 0.91 | 1.15 | 1.15 | 0.66 |
| Ovch2 | 1.00 | 1.00 | 1.00 | 1.00 | 1.00 | 1.00 | 1.00 | 1.00 | 1.00 |
| P2rx2 | 1.00 | 1.00 | 1.00 | 1.00 | 1.00 | 1.00 | 1.00 | 1.00 | 1.00 |
| Pate2 | 1.00 | 1.00 | 1.00 | 1.00 | 1.00 | 1.00 | 1.00 | 1.00 | 1.00 |
| Pax2 | 1.00 | 1.00 | 1.00 | 1.02 | 1.04 | 0.94 | 1.00 | 1.00 | 1.00 |
| Pax5 | 1.00 | 1.87 | 1.00 | 1.00 | 1.06 | 1.00 | 1.00 | 4.74 | 1.00 |
| Pbk | 1.09 | 2.41 | 1.00 | 1.00 | 1.12 | 1.00 | 1.00 | 1.77 | 1.00 |
| Pck1 | 1.00 | 1.21 | 7.04 | 2.20 | 0.77 | 0.94 | 2.42 | 1.06 | 0.55 |
| Pctp | 0.85 | 0.94 | 0.75 | 1.07 | 0.78 | 0.96 | 1.90 | 1.53 | 0.21 |
| Pde2a | 1.07 | 1.03 | 0.92 | 1.21 | 1.22 | 0.95 | 1.00 | 2.96 | 0.86 |
| Pdk4 | 1.17 | 0.81 | 1.93 | 2.38 | 1.47 | 1.02 | 1.30 | 1.38 | 1.03 |
| Pemt | 1.01 | 1.33 | 1.35 | 0.95 | 1.06 | 1.37 | 0.95 | 1.00 | 0.81 |
| Pga5 | 1.00 | 1.00 | 1.00 | 1.00 | 1.00 | 1.00 | 1.00 | 1.00 | 1.00 |
| Pgf | 5.60 | 0.81 | 0.86 | 1.00 | 1.00 | 1.00 | 1.00 | 1.09 | 1.00 |
| Phgdh | 1.75 | 1.66 | 1.20 | 0.66 | 0.88 | 0.89 | 1.00 | 3.46 | 1.00 |
| Pip5k1b | 0.75 | 0.84 | 1.05 | 0.87 | 0.91 | 0.87 | 1.00 | 1.00 | 1.00 |
| Pisd-ps1 | 1.00 | 0.25 | 0.34 | 1.32 | 8.54 | 0.43 | 0.69 | 1.31 | 0.16 |
| Plac8 | 3.50 | 3.91 | 3.65 | 0.91 | 1.70 | 0.89 | 0.93 | 6.25 | 0.76 |
| Plaur | 9.32 | 2.14 | 1.74 | 1.65 | 1.54 | 0.79 | 1.00 | 1.30 | 1.00 |
| Plin1 | 0.87 | 0.53 | 7.74 | 0.65 | 0.27 | 0.94 | 1.00 | 1.00 | 1.00 |
| Plin4 | 1.16 | 0.60 | 0.75 | 1.27 | 0.31 | 1.16 | 5.75 | 1.00 | 0.69 |
| Pln | 0.71 | 0.54 | 0.58 | 1.00 | 1.19 | 1.00 | 1.00 | 1.00 | 1.00 |
| Pomc | 1.00 | 1.00 | 1.00 | 1.00 | 1.00 | 1.00 | 1.00 | 1.00 | 1.00 |
| Pou2af1 | 1.00 | 3.89 | 1.10 | 1.00 | 2.14 | 1.00 | 1.00 | 13.80 | 1.00 |
| Pou3f3os | 1.00 | 1.00 | 1.00 | 1.20 | 1.14 | 0.74 | 1.00 | 1.00 | 1.00 |
| Ppbp | 0.97 | 0.84 | 3.56 | 1.00 | 1.00 | 1.00 | 1.00 | 5.82 | 1.00 |
| Ppm1e | 1.35 | 1.41 | 1.28 | 0.69 | 1.59 | 1.35 | 1.00 | 1.13 | 1.00 |
| Prelid2 | 1.10 | 1.01 | 0.80 | 1.25 | 1.02 | 1.15 | 1.32 | 2.54 | 0.88 |
| Prg2 | 1.00 | 1.34 | 1.00 | 1.00 | 1.66 | 1.00 | 1.00 | 8.86 | 1.00 |
| Prkcb | 1.19 | 2.71 | 1.00 | 1.00 | 1.00 | 1.00 | 1.00 | 2.57 | 1.00 |
| Prl | 1.00 | 1.00 | 1.00 | 1.00 | 1.00 | 1.00 | 1.00 | 1.00 | 1.00 |
| Prokr1 | 1.00 | 1.00 | 1.00 | 1.00 | 1.00 | 1.00 | 1.00 | 1.00 | 1.00 |
| Prom2 | 1.00 | 1.00 | 1.00 | 0.86 | 0.98 | 1.10 | 1.00 | 1.04 | 1.00 |
| Prr11 | 1.00 | 1.75 | 1.00 | 1.00 | 1.00 | 1.00 | 1.00 | 1.28 | 1.00 |
| Prss22 | 1.00 | 1.00 | 4.01 | 1.00 | 1.00 | 3.79 | 1.00 | 1.00 | 1.46 |
| Prtn3 | 1.00 | 1.26 | 1.01 | 1.00 | 1.00 | 1.00 | 1.01 | 16.43 | 1.00 |
| Psrc1 | 1.00 | 1.89 | 1.00 | 1.00 | 1.00 | 1.00 | 1.00 | 1.11 | 1.00 |
| Pstpip1 | 1.92 | 1.86 | 1.33 | 1.00 | 1.00 | 1.00 | 1.00 | 1.01 | 1.00 |
| Ptgr1 | 1.03 | 1.81 | 1.46 | 1.35 | 0.83 | 0.85 | 0.45 | 5.31 | 1.29 |
| Ptgs2 | 6.11 | 1.69 | 2.52 | 1.00 | 1.00 | 0.99 | 1.00 | 1.00 | 1.00 |
| Ptn | 0.86 | 5.08 | 2.96 | 1.00 | 1.23 | 1.00 | 1.00 | 1.00 | 1.00 |
| Ptpn5 | 1.00 | 1.00 | 1.00 | 1.22 | 1.05 | 1.47 | 1.00 | 1.00 | 1.00 |
| Ptprcap | 1.21 | 3.93 | 2.20 | 0.94 | 2.86 | 0.78 | 1.00 | 14.35 | 1.00 |
| Ptx3 | 3.22 | 2.18 | 1.50 | 1.00 | 1.00 | 1.00 | 1.00 | 1.00 | 1.00 |
| Pygm | 0.69 | 0.54 | 0.69 | 0.70 | 1.65 | 0.94 | 1.00 | 1.00 | 1.00 |
| Pyhin1 | 1.07 | 1.48 | 1.00 | 1.00 | 1.00 | 1.00 | 1.00 | 1.86 | 1.00 |
| Rac2 | 1.88 | 2.63 | 2.87 | 0.68 | 1.96 | 0.85 | 0.82 | 5.30 | 0.98 |
| Rad51 | 1.11 | 1.33 | 1.00 | 1.00 | 1.00 | 1.00 | 1.00 | 1.68 | 1.00 |
| Rag1 | 1.09 | 2.18 | 1.00 | 1.00 | 1.13 | 1.00 | 1.00 | 2.27 | 1.00 |
| Ramp3 | 1.04 | 0.95 | 0.79 | 0.75 | 1.07 | 0.93 | 1.00 | 1.00 | 1.00 |
| Rasgrf1 | 1.00 | 1.00 | 1.00 | 1.00 | 1.00 | 1.00 | 1.00 | 1.00 | 1.00 |
| Rasl10a | 0.31 | 0.48 | 0.42 | 1.00 | 1.00 | 1.00 | 1.00 | 1.00 | 1.00 |
| Rbm11 | 1.00 | 1.00 | 1.00 | 1.09 | 0.73 | 0.95 | 1.00 | 1.00 | 1.00 |
| Reg2 | 1.00 | 1.00 | 1.00 | 1.00 | 1.00 | 1.00 | 1.00 | 1.00 | 1.00 |
| Reg3g | 1.00 | 1.00 | 5.47 | 1.00 | 1.00 | 1.00 | 0.74 | 1.00 | 1.00 |
| Retn | 1.05 | 0.67 | 6.23 | 0.73 | 0.32 | 1.24 | 1.00 | 1.00 | 1.00 |
| Retnla | 0.90 | 0.66 | 1.68 | 1.59 | 0.41 | 0.52 | 1.00 | 1.00 | 0.57 |
| Retnlg | 3.53 | 4.42 | 1.96 | 1.16 | 2.22 | 1.00 | 1.00 | 6.65 | 1.00 |
| Rgs16 | 5.48 | 2.11 | 1.49 | 1.00 | 1.00 | 1.00 | 3.12 | 1.07 | 0.07 |

Fig. 31-94

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Nxpe2 | 1.00 | 1.00 | 1.00 | 1.00 | 1.00 | 1.00 | 1.16 | 1.26 | 3.56 |
| Nxpe5 | 2.20 | 1.31 | 1.25 | 0.74 | 1.24 | 1.15 | 0.93 | 0.96 | 1.58 |
| Oas2 | 0.90 | 4.87 | 0.42 | 0.87 | 1.59 | 0.88 | 0.96 | 3.41 | 0.23 |
| Odf1 | 1.00 | 1.00 | 1.00 | 1.00 | 1.00 | 0.71 | 1.00 | 1.00 | 1.00 |
| Otof | 1.00 | 1.00 | 1.00 | 1.00 | 1.00 | 1.00 | 1.00 | 1.00 | 1.00 |
| Otud1 | 1.20 | 1.03 | 0.86 | 2.48 | 2.53 | 0.64 | 1.13 | 1.07 | 0.92 |
| Ovch2 | 1.00 | 1.00 | 1.00 | 1.00 | 1.00 | 1.00 | 1.00 | 1.00 | 1.00 |
| P2rx2 | 1.00 | 1.00 | 1.00 | 1.00 | 1.00 | 1.00 | 1.00 | 1.00 | 1.00 |
| Pate2 | 1.00 | 1.00 | 1.00 | 1.00 | 1.00 | 1.00 | 1.00 | 1.00 | 1.00 |
| Pax2 | 1.00 | 1.00 | 1.00 | 1.00 | 1.00 | 1.00 | 1.00 | 1.00 | 1.00 |
| Pax5 | 0.35 | 19.29 | 0.76 | 1.00 | 1.00 | 1.00 | 0.92 | 0.78 | 0.86 |
| Pbk | 2.02 | 7.28 | 1.00 | 1.00 | 1.00 | 1.00 | 0.89 | 1.31 | 2.63 |
| Pck1 | 0.88 | 1.36 | 0.20 | 1.91 | 2.20 | 0.99 | 4.01 | 1.02 | 0.81 |
| Pctp | 1.22 | 1.10 | 0.93 | 0.92 | 1.11 | 1.04 | 1.00 | 0.80 | 0.95 |
| Pde2a | 1.00 | 12.00 | 0.97 | 1.32 | 1.10 | 1.05 | 1.07 | 0.97 | 0.70 |
| Pdk4 | 3.62 | 1.86 | 1.08 | 4.20 | 1.63 | 2.26 | 7.50 | 1.66 | 0.40 |
| Pemt | 1.11 | 0.97 | 1.03 | 1.32 | 1.09 | 0.97 | 0.69 | 0.82 | 0.83 |
| Pga5 | 1.00 | 1.00 | 1.00 | 1.00 | 1.00 | 1.00 | 1.00 | 1.00 | 1.00 |
| Pgf | 1.50 | 2.28 | 1.47 | 2.25 | 0.77 | 1.13 | 1.50 | 0.90 | 1.00 |
| Phgdh | 1.13 | 5.34 | 0.95 | 1.18 | 1.25 | 1.04 | 1.07 | 1.29 | 0.71 |
| Pip5k1b | 1.20 | 0.90 | 1.34 | 1.00 | 1.00 | 1.00 | 1.03 | 1.34 | 2.14 |
| Pisd-ps1 | 0.38 | 0.25 | 0.57 | 0.33 | 0.52 | 2.94 | 1.06 | 1.49 | 0.55 |
| Plac8 | 0.69 | 5.93 | 1.26 | 1.13 | 0.99 | 0.64 | 0.72 | 0.95 | 0.84 |
| Plaur | 1.71 | 1.26 | 0.95 | 1.00 | 0.94 | 0.92 | 1.01 | 0.88 | 0.89 |
| Plin1 | 0.60 | 1.22 | 0.42 | 0.87 | 1.79 | 1.60 | 2.48 | 0.94 | 1.17 |
| Plin4 | 1.04 | 0.79 | 0.74 | 1.74 | 1.04 | 0.85 | 3.21 | 0.95 | 0.87 |
| Pln | 0.33 | 0.83 | 1.20 | 1.15 | 1.33 | 1.57 | 1.00 | 1.00 | 1.00 |
| Pomc | 1.00 | 1.00 | 1.00 | 1.00 | 1.00 | 1.00 | 1.00 | 1.00 | 1.00 |
| Pou2af1 | 0.32 | 17.18 | 0.67 | 1.00 | 1.47 | 1.00 | 0.75 | 1.32 | 0.70 |
| Pou3f3os | 1.00 | 1.00 | 1.00 | 1.00 | 1.00 | 1.00 | 1.00 | 1.00 | 1.00 |
| Ppbp | 0.82 | 0.95 | 0.78 | 1.00 | 0.18 | 0.26 | 0.65 | 0.73 | 0.66 |
| Ppm1e | 1.00 | 6.13 | 1.00 | 1.00 | 1.00 | 1.00 | 0.99 | 0.80 | 0.86 |
| Prelid2 | 1.08 | 7.33 | 0.79 | 1.00 | 1.00 | 1.00 | 1.37 | 1.04 | 0.77 |
| Prg2 | 1.00 | 38.36 | 0.98 | 1.00 | 0.10 | 1.00 | 0.57 | 1.67 | 0.52 |
| Prkcb | 0.59 | 6.08 | 0.80 | 1.00 | 1.04 | 1.00 | 1.03 | 0.85 | 0.69 |
| Prl | 1.00 | 1.00 | 1.00 | 1.00 | 1.00 | 1.00 | 1.00 | 1.00 | 1.00 |
| Prokr1 | 1.00 | 1.00 | 1.00 | 1.00 | 0.97 | 1.00 | 1.92 | 2.01 | 1.77 |
| Prom2 | 0.94 | 1.00 | 0.81 | 1.00 | 1.00 | 1.00 | 1.53 | 1.00 | 1.00 |
| Prr11 | 1.27 | 5.45 | 1.00 | 1.00 | 1.00 | 1.00 | 0.92 | 1.56 | 2.93 |
| Prss22 | 1.00 | 1.00 | 7.59 | 1.00 | 1.00 | 3.76 | 1.00 | 1.00 | 23.40 |
| Prtn3 | 0.62 | 2.59 | 1.25 | 1.00 | 0.24 | 0.42 | 0.18 | 1.50 | 2.43 |
| Psrc1 | 0.95 | 5.59 | 1.00 | 1.00 | 1.00 | 1.00 | 0.67 | 1.18 | 2.24 |
| Pstpip1 | 0.71 | 1.43 | 1.06 | 1.00 | 1.00 | 1.00 | 0.91 | 0.97 | 0.87 |
| Ptgr1 | 1.23 | 3.21 | 1.02 | 0.88 | 0.86 | 1.03 | 0.58 | 1.07 | 1.06 |
| Ptgs2 | 1.33 | 1.25 | 1.39 | 1.00 | 1.00 | 1.00 | 1.00 | 1.00 | 1.00 |
| Ptn | 1.00 | 1.20 | 1.00 | 1.00 | 0.93 | 1.00 | 1.00 | 1.00 | 1.00 |
| Ptpn5 | 1.00 | 1.00 | 1.00 | 1.00 | 1.00 | 1.00 | 1.00 | 1.00 | 1.00 |
| Ptprcap | 0.46 | 9.83 | 0.82 | 1.00 | 1.39 | 1.00 | 1.03 | 1.01 | 0.74 |
| Ptx3 | 1.67 | 1.29 | 1.16 | 0.47 | 0.83 | 1.12 | 1.00 | 1.00 | 1.00 |
| Pygm | 0.75 | 0.70 | 1.24 | 1.12 | 0.93 | 0.95 | 0.98 | 0.74 | 0.82 |
| Pyhin1 | 0.68 | 11.22 | 0.94 | 1.00 | 1.00 | 1.00 | 1.10 | 0.90 | 0.75 |
| Rac2 | 0.74 | 2.59 | 1.00 | 0.89 | 0.85 | 0.73 | 0.90 | 1.00 | 0.81 |
| Rad51 | 1.90 | 5.19 | 1.00 | 1.00 | 1.00 | 1.00 | 0.70 | 1.19 | 2.31 |
| Rag1 | 1.00 | 20.23 | 1.00 | 1.00 | 1.00 | 1.00 | 1.00 | 1.00 | 1.00 |
| Ramp3 | 1.00 | 0.75 | 0.91 | 0.69 | 0.82 | 1.51 | 0.76 | 0.71 | 1.54 |
| Rasgrf1 | 1.00 | 1.00 | 0.78 | 1.00 | 1.00 | 1.00 | 1.00 | 1.00 | 1.00 |
| Rasl10a | 0.93 | 0.90 | 0.93 | 1.00 | 1.00 | 1.00 | 1.01 | 0.62 | 0.63 |
| Rbm11 | 1.00 | 1.00 | 1.00 | 1.00 | 1.00 | 1.00 | 1.00 | 1.00 | 1.00 |
| Reg2 | 1.00 | 1.00 | 1.00 | 1.00 | 1.00 | 1.00 | 1.60 | 0.00 | 0.03 |
| Reg3g | 2.84 | 1.57 | 0.95 | 1.00 | 1.00 | 1.00 | 3.96 | 0.22 | 1.00 |
| Retn | 0.77 | 1.19 | 0.71 | 0.84 | 2.19 | 1.77 | 2.52 | 0.71 | 1.17 |
| Retnla | 3.06 | 2.46 | 1.07 | 1.02 | 1.08 | 1.14 | 2.21 | 1.35 | 0.18 |
| Retnlg | 1.05 | 2.24 | 0.84 | 1.00 | 0.29 | 0.37 | 0.63 | 1.54 | 1.21 |
| Rgs16 | 1.12 | 1.22 | 1.00 | 1.00 | 1.00 | 1.00 | 1.03 | 1.42 | 0.59 |

Fig. 31-95

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Nxpe2 | 1.00 | 1.00 | 1.00 | 1.00 | 16.44 | 1.00 | 1.00 | 1.00 | 1.00 |
| Nxpe5 | 1.00 | 1.00 | 1.00 | 1.02 | 5.58 | 1.69 | 1.00 | 1.00 | 1.00 |
| Oas2 | 1.00 | 1.00 | 1.00 | 0.98 | 1.81 | 0.41 | 1.00 | 1.00 | 1.00 |
| Odf1 | 1.00 | 1.00 | 1.00 | 1.00 | 11.53 | 1.00 | 1.00 | 1.07 | 1.03 |
| Otof | 0.95 | 0.95 | 0.85 | 1.00 | 6.10 | 1.00 | 1.00 | 1.00 | 1.00 |
| Otud1 | 1.04 | 1.14 | 1.09 | 1.03 | 0.97 | 0.93 | 0.97 | 1.00 | 0.93 |
| Ovch2 | 1.00 | 1.00 | 1.00 | 1.00 | 5.45 | 1.00 | 1.00 | 1.00 | 1.00 |
| P2rx2 | 1.00 | 1.00 | 1.00 | 1.00 | 12.62 | 1.00 | 0.92 | 1.03 | 0.83 |
| Pate2 | 1.00 | 1.00 | 1.00 | 1.00 | 9.65 | 1.00 | 1.00 | 1.00 | 1.11 |
| Pax2 | 1.16 | 0.94 | 0.96 | 1.00 | 10.17 | 1.00 | 0.90 | 1.17 | 1.00 |
| Pax5 | 1.00 | 2.56 | 1.00 | 1.00 | 1.32 | 0.53 | 0.90 | 1.19 | 0.94 |
| Pbk | 1.00 | 1.06 | 1.00 | 1.00 | 1.00 | 1.00 | 1.01 | 0.96 | 1.00 |
| Pck1 | 1.00 | 1.00 | 1.00 | 2.38 | 0.40 | 0.86 | 1.00 | 1.00 | 1.00 |
| Pctp | 1.00 | 1.01 | 1.05 | 1.15 | 7.34 | 0.94 | 1.34 | 1.06 | 1.01 |
| Pde2a | 0.92 | 1.07 | 0.99 | 1.42 | 0.87 | 0.80 | 1.19 | 0.92 | 0.96 |
| Pdk4 | 3.65 | 1.57 | 0.66 | 4.25 | 1.64 | 1.24 | 1.18 | 0.71 | 1.06 |
| Pemt | 0.93 | 1.15 | 0.94 | 0.92 | 7.63 | 1.27 | 1.05 | 1.04 | 0.98 |
| Pga5 | 1.00 | 1.00 | 1.00 | 1.00 | 1.00 | 1.00 | 0.54 | 0.18 | 11.77 |
| Pgf | 0.89 | 1.08 | 0.93 | 0.88 | 2.84 | 1.03 | 1.70 | 0.65 | 1.32 |
| Phgdh | 1.04 | 1.14 | 0.90 | 1.07 | 1.26 | 0.97 | 0.84 | 1.00 | 0.88 |
| Pip5k1b | 0.96 | 0.89 | 1.08 | 0.79 | 6.74 | 1.00 | 0.92 | 0.79 | 0.99 |
| Pisd-ps1 | 0.45 | 0.95 | 0.61 | 0.87 | 2.93 | 0.61 | 1.00 | 1.00 | 1.61 |
| Plac8 | 1.00 | 8.27 | 1.00 | 0.99 | 15.33 | 0.19 | 0.93 | 1.55 | 0.86 |
| Plaur | 1.00 | 1.00 | 1.00 | 2.45 | 1.18 | 0.61 | 1.00 | 1.00 | 1.00 |
| Plin1 | 1.00 | 1.00 | 1.00 | 0.90 | 0.72 | 1.29 | 0.73 | 0.57 | 1.00 |
| Plin4 | 2.99 | 1.06 | 0.81 | 1.19 | 0.53 | 1.01 | 0.63 | 1.00 | 1.00 |
| Pln | 1.00 | 1.00 | 1.13 | 0.97 | 0.97 | 0.89 | 0.96 | 1.29 | 1.09 |
| Pomc | 26.99 | 1.87 | 0.97 | 1.00 | 1.35 | 1.00 | 0.95 | 1.03 | 1.09 |
| Pou2af1 | 1.00 | 6.45 | 1.00 | 1.00 | 2.30 | 0.23 | 1.00 | 1.00 | 1.00 |
| Pou3f3os | 1.14 | 0.98 | 0.97 | 1.00 | 7.20 | 1.00 | 1.32 | 1.17 | 0.95 |
| Ppbp | 1.00 | 1.00 | 1.00 | 3.47 | 1.17 | 0.93 | 1.00 | 1.00 | 1.00 |
| Ppm1e | 1.00 | 0.99 | 0.99 | 1.00 | 1.00 | 1.00 | 1.00 | 1.00 | 1.07 |
| Prelid2 | 1.00 | 1.54 | 1.00 | 1.48 | 1.16 | 0.77 | 1.04 | 1.00 | 1.00 |
| Prg2 | 1.00 | 1.12 | 1.00 | 1.00 | 1.80 | 1.00 | 0.99 | 1.00 | 1.00 |
| Prkcb | 1.09 | 1.04 | 1.02 | 0.98 | 1.25 | 0.55 | 1.06 | 0.92 | 1.06 |
| Prl | 1.00 | 13.04 | 1.00 | 1.00 | 1.00 | 1.00 | 1.00 | 1.00 | 1.00 |
| Prokr1 | 1.00 | 1.00 | 1.00 | 0.86 | 5.73 | 1.70 | 1.00 | 1.00 | 1.00 |
| Prom2 | 1.00 | 1.00 | 1.00 | 0.55 | 6.55 | 1.00 | 1.00 | 1.00 | 1.26 |
| Prr11 | 1.00 | 1.00 | 1.00 | 1.00 | 1.00 | 1.00 | 1.22 | 1.18 | 1.06 |
| Prss22 | 1.00 | 1.00 | 5.98 | 1.00 | 1.00 | 2.98 | 1.00 | 1.00 | 1.00 |
| Prtn3 | 0.87 | 1.25 | 0.97 | 1.15 | 0.66 | 0.95 | 1.00 | 1.00 | 1.00 |
| Psrc1 | 1.03 | 1.08 | 0.94 | 1.00 | 1.00 | 1.00 | 1.00 | 1.00 | 1.00 |
| Pstpip1 | 1.00 | 1.08 | 1.05 | 1.06 | 5.06 | 0.57 | 0.72 | 1.22 | 0.88 |
| Ptgr1 | 1.00 | 2.82 | 1.00 | 0.68 | 1.06 | 0.69 | 1.02 | 0.82 | 0.97 |
| Ptgs2 | 1.46 | 1.06 | 1.14 | 1.00 | 1.07 | 1.00 | 1.00 | 1.00 | 1.00 |
| Ptn | 0.94 | 0.92 | 1.01 | 1.00 | 0.44 | 1.00 | 1.00 | 1.00 | 1.00 |
| Ptpn5 | 0.92 | 0.94 | 1.03 | 1.00 | 9.95 | 1.00 | 1.00 | 1.00 | 1.00 |
| Ptprcap | 1.00 | 6.18 | 1.00 | 0.89 | 1.89 | 0.40 | 1.00 | 1.00 | 1.00 |
| Ptx3 | 1.00 | 1.00 | 1.00 | 6.32 | 1.26 | 1.29 | 1.00 | 1.00 | 1.00 |
| Pygm | 0.96 | 1.07 | 0.99 | 0.92 | 0.96 | 0.90 | 0.98 | 0.85 | 0.88 |
| Pyhin1 | 1.00 | 1.15 | 1.00 | 1.00 | 1.05 | 0.90 | 0.89 | 1.08 | 0.86 |
| Rac2 | 1.00 | 2.94 | 1.00 | 1.17 | 1.24 | 0.48 | 0.99 | 1.13 | 0.97 |
| Rad51 | 1.00 | 1.20 | 1.00 | 1.00 | 1.03 | 1.00 | 1.03 | 1.04 | 0.90 |
| Rag1 | 1.00 | 2.23 | 1.00 | 1.00 | 1.29 | 1.00 | 1.00 | 1.56 | 1.59 |
| Ramp3 | 0.92 | 0.98 | 0.93 | 0.67 | 14.57 | 0.96 | 1.14 | 0.99 | 0.90 |
| Rasgrf1 | 1.01 | 1.02 | 0.96 | 1.00 | 5.88 | 1.00 | 0.81 | 1.05 | 0.88 |
| Rasl10a | 0.97 | 1.23 | 0.94 | 0.73 | 7.03 | 1.00 | 1.49 | 1.15 | 1.29 |
| Rbm11 | 0.90 | 1.09 | 0.90 | 0.95 | 13.10 | 1.00 | 1.12 | 0.86 | 1.04 |
| Reg2 | 1.00 | 1.00 | 1.00 | 1.00 | 1.00 | 1.00 | 1.00 | 1.00 | 1.00 |
| Reg3g | 1.00 | 1.00 | 1.00 | 1.00 | 0.06 | 1.00 | 1.00 | 1.00 | 1.00 |
| Retn | 1.00 | 1.03 | 0.98 | 0.68 | 0.73 | 1.47 | 0.62 | 1.36 | 1.22 |
| Retnla | 1.00 | 1.00 | 1.00 | 1.34 | 1.21 | 0.40 | 0.56 | 1.00 | 0.64 |
| Retnlg | 1.00 | 1.03 | 1.00 | 4.20 | 2.64 | 0.28 | 1.00 | 1.00 | 1.00 |
| Rgs16 | 0.88 | 0.88 | 1.05 | 1.08 | 1.06 | 1.63 | 1.00 | 1.00 | 1.00 |

Fig. 31- 96

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Nxpe2 | 1.23 | 0.90 | 1.00 | 1.12 | 0.84 | 1.08 | 1.00 | 1.00 | 1.00 | 1.00 | 1.00 | 1.00 |
| Nxpe5 | 1.04 | 2.43 | 1.31 | 1.06 | 2.29 | 1.31 | 1.00 | 1.00 | 1.00 | 0.88 | 1.00 | 1.00 |
| Oas2 | 1.34 | 1.77 | 1.25 | 0.79 | 5.85 | 0.65 | 1.00 | 1.00 | 1.00 | 0.90 | 1.00 | 1.00 |
| Odf1 | 1.00 | 1.00 | 1.00 | 1.00 | 1.00 | 1.00 | 1.00 | 1.00 | 1.00 | 1.00 | 1.01 | 0.93 |
| Otof | 1.00 | 1.00 | 1.00 | 1.00 | 1.00 | 1.00 | 1.00 | 1.00 | 1.00 | 1.00 | 1.00 | 1.00 |
| Otud1 | 1.03 | 0.91 | 1.05 | 1.09 | 0.68 | 1.01 | 0.96 | 1.00 | 1.00 | 1.01 | 1.10 | 1.10 |
| Ovch2 | 1.00 | 1.00 | 1.00 | 1.00 | 1.00 | 1.00 | 1.00 | 1.00 | 1.00 | 1.00 | 1.07 | 0.95 |
| P2rx2 | 1.00 | 1.00 | 1.00 | 1.00 | 1.00 | 1.00 | 1.00 | 1.00 | 1.00 | 1.15 | 0.94 | 0.94 |
| Pate2 | 1.00 | 1.00 | 1.00 | 1.00 | 1.00 | 1.00 | 1.00 | 1.00 | 1.00 | 1.00 | 1.00 | 1.07 |
| Pax2 | 1.00 | 1.00 | 1.00 | 1.00 | 1.00 | 1.00 | 1.00 | 1.00 | 1.00 | 1.00 | 1.00 | 1.00 |
| Pax5 | 3.52 | 3.78 | 3.12 | 1.13 | 0.47 | 0.79 | 1.00 | 1.00 | 1.00 | 1.00 | 1.00 | 1.00 |
| Pbk | 0.36 | 0.64 | 0.91 | 0.90 | 0.92 | 1.12 | 1.00 | 1.00 | 1.00 | 0.69 | 1.23 | 0.96 |
| Pck1 | 1.83 | 1.78 | 2.85 | 1.00 | 1.00 | 1.00 | 0.94 | 0.87 | 1.00 | 0.62 | 1.00 | 1.00 |
| Pctp | 0.82 | 1.05 | 0.93 | 0.91 | 0.92 | 0.79 | 1.00 | 1.00 | 0.97 | 1.17 | 0.98 | 0.99 |
| Pde2a | 1.47 | 1.65 | 1.58 | 1.20 | 0.99 | 0.92 | 0.98 | 0.85 | 0.97 | 1.13 | 1.12 | 0.93 |
| Pdk4 | 1.31 | 1.96 | 4.34 | 1.00 | 1.00 | 1.00 | 1.31 | 1.78 | 2.00 | 2.04 | 0.84 | 1.05 |
| Pemt | 0.97 | 0.96 | 0.83 | 0.87 | 0.93 | 1.05 | 0.99 | 1.00 | 1.00 | 0.84 | 1.04 | 0.96 |
| Pga5 | 1.00 | 1.00 | 1.00 | 1.00 | 1.00 | 1.00 | 1.00 | 1.00 | 1.00 | 1.00 | 0.98 | 1.06 |
| Pgf | 1.18 | 1.27 | 1.54 | 1.00 | 1.00 | 1.00 | 1.30 | 0.29 | 1.32 | 0.80 | 1.02 | 0.93 |
| Phgdh | 0.81 | 0.69 | 1.39 | 0.72 | 0.96 | 1.11 | 0.79 | 0.82 | 1.61 | 0.89 | 1.06 | 1.01 |
| Pip5k1b | 1.18 | 0.77 | 0.85 | 1.17 | 0.96 | 1.15 | 1.00 | 1.00 | 1.11 | 0.69 | 1.00 | 1.00 |
| Pisd-ps1 | 0.93 | 0.30 | 2.33 | 0.69 | 1.66 | 0.49 | 1.33 | 0.71 | 0.56 | 1.34 | 1.04 | 0.84 |
| Plac8 | 1.10 | 1.78 | 1.12 | 0.94 | 1.38 | 1.01 | 0.71 | 0.78 | 0.92 | 0.54 | 0.30 | 1.17 |
| Plaur | 1.19 | 2.44 | 2.12 | 1.08 | 1.27 | 1.10 | 1.00 | 1.00 | 1.00 | 1.19 | 0.90 | 0.94 |
| Plin1 | 1.88 | 1.29 | 2.14 | 1.00 | 1.00 | 1.00 | 1.00 | 0.82 | 0.88 | 0.58 | 1.07 | 0.97 |
| Plin4 | 1.84 | 1.53 | 2.07 | 1.00 | 1.00 | 1.00 | 0.89 | 0.90 | 1.16 | 1.18 | 1.17 | 1.06 |
| Pln | 3.56 | 5.24 | 5.36 | 1.00 | 1.00 | 1.00 | 1.00 | 1.00 | 1.00 | 1.00 | 1.18 | 0.90 |
| Pomc | 1.25 | 0.79 | 0.83 | 1.00 | 1.00 | 1.00 | 1.00 | 1.00 | 1.00 | 1.00 | 0.83 | 1.06 |
| Pou2af1 | 1.91 | 3.24 | 2.60 | 1.18 | 0.50 | 0.79 | 1.00 | 1.00 | 1.00 | 1.00 | 1.00 | 1.00 |
| Pou3f3os | 1.00 | 1.00 | 1.00 | 1.00 | 1.00 | 1.00 | 1.00 | 1.00 | 1.00 | 1.00 | 1.08 | 0.90 |
| Ppbp | 1.31 | 1.16 | 1.00 | 1.00 | 0.80 | 1.85 | 1.68 | 1.00 | 1.00 | 1.00 | 0.89 | 0.88 |
| Ppm1e | 0.79 | 0.61 | 0.70 | 1.03 | 0.46 | 0.69 | 1.00 | 1.00 | 1.00 | 1.00 | 0.94 | 0.99 |
| Prelid2 | 0.73 | 1.24 | 1.12 | 0.83 | 0.90 | 0.97 | 1.02 | 0.85 | 0.71 | 1.00 | 0.98 | 0.98 |
| Prg2 | 0.92 | 1.15 | 1.39 | 1.14 | 0.47 | 0.59 | 1.00 | 1.00 | 1.00 | 1.00 | 1.97 | 0.85 |
| Prkcb | 0.73 | 0.73 | 0.75 | 1.00 | 0.93 | 0.86 | 1.00 | 1.00 | 1.00 | 1.34 | 0.99 | 1.07 |
| Prl | 1.00 | 1.00 | 1.00 | 1.00 | 1.00 | 1.00 | 1.00 | 1.00 | 1.00 | 1.00 | 1.00 | 1.00 |
| Prokr1 | 1.00 | 1.00 | 1.00 | 1.42 | 1.11 | 1.25 | 1.00 | 1.00 | 1.00 | 1.00 | 1.00 | 1.00 |
| Prom2 | 1.35 | 0.84 | 1.13 | 1.00 | 1.00 | 1.00 | 0.98 | 1.13 | 0.66 | 0.89 | 1.22 | 1.26 |
| Prr11 | 0.42 | 0.67 | 1.00 | 0.93 | 1.05 | 0.96 | 1.00 | 1.00 | 1.00 | 1.10 | 1.16 | 1.07 |
| Prss22 | 1.27 | 0.11 | 1.16 | 1.00 | 0.18 | 1.00 | 1.00 | 1.00 | 1.00 | 0.85 | 0.81 | 1.20 |
| Prtn3 | 1.27 | 2.44 | 1.11 | 0.79 | 1.28 | 1.01 | 1.00 | 1.00 | 1.00 | 1.00 | 0.96 | 1.30 |
| Psrc1 | 0.49 | 0.53 | 0.94 | 0.86 | 0.62 | 0.89 | 1.00 | 1.00 | 1.00 | 0.73 | 0.94 | 0.73 |
| Pstpip1 | 0.88 | 0.86 | 0.76 | 1.06 | 1.10 | 1.04 | 1.00 | 1.00 | 1.00 | 0.61 | 1.15 | 0.96 |
| Ptgr1 | 0.81 | 0.98 | 0.88 | 1.04 | 0.87 | 0.94 | 1.00 | 1.00 | 1.00 | 0.93 | 1.10 | 1.05 |
| Ptgs2 | 1.31 | 0.89 | 0.87 | 1.00 | 1.00 | 1.00 | 1.00 | 1.00 | 1.00 | 1.00 | 1.00 | 1.00 |
| Ptn | 1.17 | 0.89 | 1.25 | 1.00 | 1.00 | 1.00 | 1.00 | 1.00 | 1.00 | 0.88 | 1.12 | 1.08 |
| Ptpn5 | 1.00 | 1.00 | 0.93 | 1.00 | 1.00 | 1.00 | 1.00 | 1.00 | 1.00 | 1.00 | 1.26 | 0.98 |
| Ptprcap | 0.84 | 0.93 | 0.84 | 1.01 | 0.60 | 0.94 | 0.67 | 0.58 | 0.59 | 1.20 | 0.89 | 0.96 |
| Ptx3 | 0.63 | 0.76 | 1.04 | 1.00 | 1.00 | 1.00 | 1.00 | 1.00 | 1.00 | 1.28 | 1.00 | 0.96 |
| Pygm | 1.37 | 5.41 | 1.62 | 1.38 | 1.04 | 0.80 | 1.00 | 1.00 | 1.00 | 1.55 | 1.06 | 1.09 |
| Pyhin1 | 1.28 | 1.64 | 1.16 | 1.08 | 1.06 | 0.86 | 1.00 | 1.00 | 1.00 | 1.00 | 0.89 | 1.03 |
| Rac2 | 0.87 | 1.03 | 1.01 | 1.05 | 1.04 | 1.03 | 0.95 | 0.62 | 0.73 | 1.10 | 1.39 | 1.04 |
| Rad51 | 0.52 | 0.69 | 0.91 | 0.87 | 0.97 | 0.93 | 1.00 | 1.00 | 1.00 | 0.99 | 1.00 | 1.00 |
| Rag1 | 0.92 | 0.72 | 0.70 | 1.22 | 0.52 | 0.92 | 1.00 | 1.00 | 1.00 | 1.00 | 0.83 | 1.01 |
| Ramp3 | 0.91 | 0.91 | 0.99 | 1.00 | 1.00 | 1.00 | 1.00 | 1.00 | 1.00 | 1.44 | 1.12 | 0.95 |
| Rasgrf1 | 1.00 | 1.00 | 1.00 | 1.00 | 1.00 | 1.00 | 1.00 | 1.00 | 1.00 | 1.00 | 1.06 | 1.10 |
| Rasl10a | 1.07 | 0.97 | 0.97 | 1.04 | 0.71 | 1.15 | 1.00 | 1.00 | 1.00 | 1.35 | 1.14 | 1.41 |
| Rbm11 | 1.00 | 1.00 | 1.00 | 1.00 | 1.00 | 1.00 | 1.00 | 1.00 | 1.00 | 1.00 | 1.24 | 0.99 |
| Reg2 | 1.00 | 1.00 | 1.00 | 1.00 | 1.00 | 1.00 | 1.41 | 7.20 | 1.24 | 1.00 | 1.00 | 1.00 |
| Reg3g | 1.41 | 15.79 | 1.25 | 1.00 | 1.00 | 1.00 | 0.51 | 2.99 | 1.00 | 0.97 | 0.88 | 0.97 |
| Retn | 3.59 | 1.52 | 2.98 | 1.00 | 0.77 | 1.00 | 1.00 | 0.93 | 0.98 | 0.52 | 1.00 | 1.00 |
| Retnla | 1.80 | 3.90 | 5.61 | 1.48 | 1.09 | 1.17 | 1.16 | 2.28 | 2.33 | 0.98 | 1.00 | 1.00 |
| Retnlg | 1.60 | 1.42 | 1.87 | 1.44 | 1.15 | 1.19 | 1.00 | 1.00 | 1.00 | 1.00 | 0.92 | 1.12 |
| Rgs16 | 1.37 | 1.12 | 0.87 | 1.00 | 1.00 | 1.00 | 1.00 | 1.00 | 1.00 | 0.82 | 1.24 | 0.99 |

Fig. 31- 97

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Rhbg | 1.00 | 1.00 | 1.00 | 0.72 | 0.88 | 0.85 | 0.69 | 1.16 | 0.94 |
| Rhcg | 1.00 | 1.00 | 1.00 | 0.94 | 0.94 | 0.73 | 1.00 | 1.00 | 1.00 |
| Rhoh | 1.00 | 1.10 | 1.00 | 1.00 | 1.00 | 1.00 | 1.00 | 1.55 | 1.00 |
| Rhpn1 | 1.00 | 1.00 | 1.00 | 0.90 | 1.10 | 1.39 | 1.00 | 1.00 | 1.00 |
| Rn45s | 1.01 | 0.98 | 1.05 | 0.89 | 1.16 | 1.45 | 1.25 | 0.34 | 1.22 |
| Rnase11 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.00 |
| Rnase13 | 1.00 | 1.00 | 1.00 | 1.00 | 1.00 | 1.00 | 1.00 | 1.00 | 1.29 |
| Rnase9 | 1.00 | 1.00 | 1.00 | 0.99 | 1.00 | 1.00 | 1.00 | 1.00 | 1.00 |
| Rnf149 | 1.69 | 2.39 | 1.51 | 0.86 | 0.96 | 1.02 | 0.91 | 1.01 | 0.99 |
| Rnu11 | 0.19 | 0.19 | 0.20 | 1.00 | 1.00 | 1.00 | 1.00 | 1.00 | 1.00 |
| Rnu73b | 0.87 | 1.79 | 0.31 | 0.27 | 92.50 | 0.26 | 1.01 | 3.44 | 1.87 |
| Ros1 | 1.00 | 1.00 | 1.00 | 1.00 | 1.00 | 1.00 | 1.00 | 1.00 | 1.00 |
| Rps27 | 1.41 | 1.32 | 1.55 | 1.34 | 0.95 | 0.88 | 1.21 | 0.64 | 0.77 |
| Rptn | 1.00 | 1.00 | 1.00 | 1.00 | 1.00 | 1.00 | 1.00 | 1.00 | 1.00 |
| Rrm2 | 1.54 | 1.85 | 1.29 | 1.14 | 0.83 | 1.03 | 1.00 | 4.15 | 0.90 |
| Rsph1 | 0.70 | 0.76 | 0.76 | 0.85 | 0.79 | 0.73 | 1.00 | 1.42 | 1.00 |
| S100a8 | 2.74 | 3.92 | 3.94 | 0.56 | 7.30 | 1.32 | 0.57 | 26.13 | 0.93 |
| S100a9 | 2.68 | 3.76 | 3.49 | 0.64 | 6.52 | 1.25 | 0.58 | 25.23 | 1.42 |
| S100b | 0.95 | 1.11 | 1.60 | 1.00 | 1.00 | 1.00 | 1.00 | 1.00 | 1.00 |
| Saa3 | 2.28 | 0.68 | 6.20 | 0.61 | 1.00 | 1.00 | 0.78 | 3.59 | 0.62 |
| Scarna10 | 1.00 | 1.00 | 24.09 | 1.00 | 1.00 | 1.00 | 1.00 | 0.03 | 1.00 |
| Scarna17 | 0.01 | 1.69 | 1.00 | 0.01 | 1.00 | 1.00 | 75.21 | 65.41 | 1.00 |
| Scarna3b | 1.00 | 0.89 | 9.88 | 1.00 | 3.57 | 1.00 | 0.27 | 0.28 | 1.00 |
| Scarna8 | 0.25 | 1.00 | 1.00 | 0.26 | 0.26 | 5.92 | 1.00 | 1.00 | 1.00 |
| Scarna9 | 1.00 | 1.00 | 1.00 | 1.00 | 1.00 | 1.00 | 1.00 | 1.00 | 1.00 |
| Scgb1a1 | 0.16 | 1.00 | 561.83 | 1.00 | 1.00 | 1.00 | 1.00 | 1.00 | 1.00 |
| Scgb3a1 | 2.02 | 1.05 | 12.57 | 1.00 | 1.00 | 1.00 | 1.00 | 1.00 | 1.00 |
| Scgb3a2 | 1.00 | 1.00 | 16.77 | 1.00 | 1.00 | 1.00 | 1.00 | 1.00 | 1.00 |
| Scn4b | 0.27 | 0.47 | 0.60 | 0.97 | 0.94 | 0.76 | 1.00 | 3.06 | 1.00 |
| Scx | 1.15 | 1.98 | 1.54 | 0.76 | 1.46 | 0.88 | 1.00 | 1.00 | 1.00 |
| Sec14l3 | 1.00 | 1.00 | 7.57 | 1.35 | 0.83 | 0.93 | 1.00 | 1.00 | 1.00 |
| Serpina1f | 1.00 | 1.00 | 1.00 | 1.30 | 1.52 | 0.99 | 1.00 | 1.00 | 1.00 |
| Serpinb12 | 1.00 | 1.00 | 1.00 | 1.00 | 1.00 | 1.00 | 1.00 | 1.00 | 1.00 |
| Serpinb1c | 0.75 | 6.47 | 1.82 | 1.00 | 1.00 | 1.00 | 1.00 | 1.00 | 1.00 |
| Serpinb2 | 3.69 | 0.33 | 1.00 | 1.00 | 1.00 | 1.00 | 1.00 | 1.00 | 1.00 |
| Serpine1 | 10.17 | 2.23 | 2.12 | 1.53 | 0.97 | 0.87 | 1.00 | 1.00 | 1.00 |
| Serpinf2 | 1.00 | 1.00 | 1.00 | 1.03 | 0.75 | 1.21 | 0.95 | 1.09 | 1.10 |
| Sfrp2 | 0.26 | 7.69 | 14.74 | 0.68 | 2.41 | 1.37 | 1.00 | 1.00 | 1.00 |
| Sftpa1 | 1.77 | 1.00 | 23.59 | 1.00 | 1.00 | 1.00 | 3.59 | 1.00 | 0.65 |
| Sftpb | 5.55 | 1.00 | 44.18 | 1.00 | 1.00 | 1.00 | 1.00 | 1.00 | 1.00 |
| Sftpc | 11.39 | 1.00 | 361.67 | 1.00 | 1.00 | 1.00 | 1.00 | 1.00 | 1.00 |
| Sftpd | 1.38 | 1.00 | 9.93 | 1.00 | 1.00 | 1.00 | 1.00 | 1.00 | 1.00 |
| Sh2d5 | 6.76 | 1.00 | 1.00 | 1.00 | 1.00 | 1.00 | 1.00 | 1.00 | 1.00 |
| Sh3gl3 | 1.00 | 1.00 | 1.00 | 1.00 | 1.00 | 1.00 | 1.00 | 1.00 | 1.00 |
| Siglecg | 1.00 | 2.31 | 1.00 | 1.00 | 1.28 | 1.00 | 1.00 | 4.02 | 1.00 |
| Slamf6 | 1.00 | 1.60 | 1.00 | 1.00 | 1.00 | 1.00 | 1.00 | 3.46 | 1.00 |
| Slamf7 | 1.00 | 2.21 | 1.00 | 1.00 | 1.27 | 1.00 | 1.00 | 3.38 | 1.00 |
| Slc15a2 | 0.34 | 0.46 | 0.41 | 0.57 | 0.68 | 0.65 | 0.63 | 0.89 | 0.57 |
| Slc16a3 | 9.86 | 1.90 | 2.27 | 1.00 | 1.01 | 1.00 | 1.00 | 1.00 | 1.00 |
| Slc17a9 | 1.00 | 1.49 | 1.03 | 1.00 | 1.00 | 1.00 | 0.59 | 0.92 | 1.23 |
| Slc1a5 | 1.08 | 1.18 | 2.02 | 0.85 | 0.78 | 0.74 | 1.00 | 5.12 | 1.00 |
| Slc34a2 | 1.04 | 1.00 | 12.29 | 0.85 | 0.86 | 1.34 | 1.00 | 1.00 | 1.14 |
| Slc38a5 | 1.00 | 0.95 | 1.56 | 1.00 | 1.00 | 1.00 | 1.00 | 1.00 | 1.00 |
| Slc41a2 | 2.21 | 2.02 | 2.00 | 0.90 | 0.91 | 1.14 | 0.84 | 1.39 | 1.53 |
| Slc46a2 | 1.00 | 1.00 | 1.00 | 1.00 | 1.00 | 1.00 | 1.00 | 1.00 | 1.00 |
| Slc9a2 | 0.90 | 0.43 | 1.08 | 0.92 | 0.92 | 0.79 | 1.00 | 1.00 | 1.00 |
| Slco4a1 | 1.00 | 1.00 | 1.00 | 1.76 | 1.26 | 0.86 | 1.00 | 1.16 | 1.00 |
| Slfn1 | 10.12 | 2.28 | 1.03 | 1.00 | 1.00 | 1.00 | 1.00 | 1.00 | 1.00 |
| Slfn2 | 3.10 | 2.49 | 1.25 | 1.25 | 2.16 | 0.79 | 0.94 | 5.24 | 0.81 |
| Slfn4 | 14.75 | 2.64 | 1.00 | 1.00 | 1.00 | 1.00 | 1.00 | 1.24 | 1.00 |
| Slit1 | 1.00 | 1.00 | 1.00 | 1.00 | 1.00 | 1.00 | 1.00 | 1.00 | 1.00 |
| Slmo1 | 1.00 | 1.00 | 1.00 | 1.00 | 1.00 | 1.00 | 1.00 | 1.00 | 1.00 |
| Sln | 0.65 | 1.17 | 1.44 | 1.00 | 1.00 | 1.00 | 1.00 | 1.00 | 1.00 |

Fig. 31- 98

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Rhbg | 0.59 | 0.70 | 0.84 | 1.00 | 1.00 | 1.00 | 1.00 | 1.00 | 1.00 |
| Rhcg | 1.00 | 1.00 | 1.00 | 1.00 | 1.00 | 1.00 | 1.00 | 1.00 | 1.00 |
| Rhoh | 0.64 | 6.28 | 0.83 | 1.00 | 1.00 | 1.00 | 0.96 | 0.97 | 0.81 |
| Rhpn1 | 0.94 | 1.00 | 1.14 | 1.00 | 1.00 | 1.00 | 1.00 | 1.00 | 1.00 |
| Rn45s | 1.18 | 0.84 | 0.82 | 0.99 | 0.71 | 4.26 | 0.93 | 1.25 | 1.12 |
| Rnase11 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 0.77 | 1.00 | 1.02 |
| Rnase13 | 1.00 | 1.00 | 1.00 | 1.70 | 1.87 | 0.70 | 1.00 | 1.00 | 1.00 |
| Rnase9 | 1.00 | 1.00 | 1.00 | 1.00 | 1.00 | 1.00 | 1.00 | 1.00 | 1.00 |
| Rnf149 | 0.96 | 1.05 | 1.18 | 0.79 | 1.08 | 1.00 | 0.80 | 1.02 | 1.03 |
| Rnu11 | 1.00 | 0.25 | 7.75 | 1.00 | 0.24 | 1.00 | 0.17 | 0.16 | 1.00 |
| Rnu73b | 0.58 | 1.26 | 1.79 | 1.12 | 1.05 | 0.86 | 0.47 | 0.53 | 1.61 |
| Ros1 | 1.00 | 0.91 | 0.92 | 1.00 | 1.00 | 1.00 | 1.00 | 1.00 | 1.00 |
| Rps27 | 1.16 | 1.39 | 0.98 | 1.21 | 1.05 | 0.63 | 1.43 | 0.74 | 0.88 |
| Rptn | 1.00 | 0.83 | 0.99 | 1.00 | 1.00 | 1.00 | 1.00 | 1.00 | 1.00 |
| Rrm2 | 2.11 | 6.68 | 0.99 | 1.24 | 0.57 | 0.85 | 0.99 | 1.33 | 3.27 |
| Rsph1 | 0.66 | 0.75 | 0.59 | 0.66 | 0.42 | 0.45 | 0.59 | 0.93 | 0.43 |
| S100a8 | 0.63 | 2.97 | 1.60 | 1.40 | 0.10 | 0.03 | 0.36 | 1.84 | 2.16 |
| S100a9 | 0.61 | 2.67 | 1.37 | 1.08 | 0.11 | 0.03 | 0.37 | 1.68 | 1.99 |
| S100b | 1.00 | 1.30 | 1.00 | 1.11 | 2.03 | 1.06 | 1.00 | 1.00 | 1.00 |
| Saa3 | 1.48 | 0.67 | 8.38 | 0.94 | 1.00 | 1.00 | 0.22 | 0.62 | 0.87 |
| Scarna10 | 1.00 | 22.37 | 1.00 | 1.00 | 1.00 | 1.00 | 35.43 | 1.07 | 34.03 |
| Scarna17 | 0.03 | 38.23 | 40.51 | 1.00 | 1.00 | 1.00 | 0.01 | 1.19 | 0.01 |
| Scarna3b | 0.38 | 0.39 | 2.64 | 1.00 | 1.00 | 2.66 | 0.15 | 0.09 | 0.90 |
| Scarna8 | 1.02 | 0.52 | 4.40 | 1.00 | 1.00 | 1.00 | 0.93 | 1.67 | 1.19 |
| Scarna9 | 1.00 | 1.00 | 1.00 | 1.00 | 1.00 | 1.00 | 1.00 | 1.00 | 1.00 |
| Scgb1a1 | 0.98 | 0.71 | 0.82 | 1.00 | 1.00 | 1.00 | 1.00 | 1.00 | 1.00 |
| Scgb3a1 | 0.99 | 1.43 | 0.85 | 1.05 | 1.00 | 1.00 | 1.00 | 1.00 | 1.00 |
| Scgb3a2 | 0.81 | 0.87 | 0.79 | 1.00 | 1.00 | 1.00 | 1.00 | 1.00 | 1.00 |
| Scn4b | 1.00 | 18.54 | 1.11 | 0.77 | 1.05 | 0.79 | 1.50 | 1.00 | 1.76 |
| Scx | 0.68 | 0.92 | 1.04 | 0.62 | 1.35 | 1.11 | 1.11 | 0.87 | 1.22 |
| Sec14l3 | 0.99 | 0.60 | 0.74 | 1.00 | 1.00 | 1.00 | 1.00 | 1.00 | 1.00 |
| Serpina1f | 1.00 | 1.00 | 1.00 | 1.00 | 1.00 | 1.00 | 1.00 | 1.00 | 1.00 |
| Serpinb12 | 1.00 | 1.00 | 1.00 | 1.00 | 1.00 | 1.00 | 1.00 | 1.00 | 1.00 |
| Serpinb1c | 1.00 | 1.05 | 1.00 | 1.45 | 0.95 | 1.65 | 0.95 | 0.96 | 0.90 |
| Serpinb2 | 5.58 | 0.84 | 1.00 | 1.00 | 1.00 | 1.00 | 0.72 | 0.67 | 0.70 |
| Serpine1 | 5.17 | 1.64 | 1.30 | 7.80 | 0.76 | 0.42 | 1.28 | 1.22 | 0.61 |
| Serpinf2 | 1.00 | 1.00 | 1.00 | 1.00 | 1.00 | 1.00 | 1.00 | 1.00 | 1.00 |
| Sfrp2 | 0.31 | 1.73 | 1.38 | 0.45 | 1.12 | 1.31 | 1.00 | 1.00 | 1.00 |
| Sftpa1 | 1.12 | 0.81 | 0.87 | 1.00 | 1.00 | 1.00 | 1.00 | 1.00 | 1.00 |
| Sftpb | 1.23 | 0.84 | 1.01 | 1.00 | 1.00 | 1.00 | 1.00 | 1.00 | 1.00 |
| Sftpc | 1.05 | 0.81 | 1.03 | 1.00 | 1.00 | 1.00 | 1.00 | 1.00 | 1.00 |
| Sftpd | 1.60 | 0.93 | 1.02 | 1.00 | 1.00 | 1.00 | 1.00 | 1.00 | 1.00 |
| Sh2d5 | 1.00 | 3.70 | 1.00 | 1.00 | 1.00 | 1.00 | 0.77 | 1.33 | 1.75 |
| Sh3gl3 | 1.00 | 1.00 | 1.00 | 1.00 | 1.00 | 1.00 | 1.34 | 0.99 | 1.00 |
| Siglecg | 0.29 | 10.36 | 0.71 | 1.00 | 1.11 | 1.00 | 1.09 | 0.81 | 0.87 |
| Slamf6 | 0.63 | 8.49 | 0.64 | 1.00 | 1.00 | 1.00 | 1.06 | 1.08 | 0.68 |
| Slamf7 | 0.63 | 17.31 | 0.86 | 1.00 | 1.00 | 1.00 | 0.92 | 1.02 | 0.80 |
| Slc15a2 | 0.87 | 1.13 | 0.64 | 0.28 | 0.63 | 0.32 | 0.19 | 0.40 | 0.30 |
| Slc16a3 | 1.13 | 1.11 | 1.08 | 1.17 | 0.94 | 1.08 | 1.03 | 1.15 | 0.96 |
| Slc17a9 | 0.90 | 1.99 | 0.94 | 1.00 | 1.00 | 1.00 | 1.17 | 1.14 | 0.76 |
| Slc1a5 | 0.92 | 0.91 | 0.87 | 0.81 | 1.09 | 1.13 | 1.25 | 1.22 | 1.46 |
| Slc34a2 | 1.20 | 0.82 | 1.15 | 1.00 | 1.00 | 1.00 | 1.00 | 1.00 | 1.00 |
| Slc38a5 | 0.72 | 0.62 | 1.10 | 1.00 | 1.00 | 1.00 | 0.71 | 1.24 | 2.97 |
| Slc41a2 | 1.43 | 1.00 | 1.08 | 1.00 | 1.00 | 1.00 | 1.14 | 0.82 | 0.94 |
| Slc46a2 | 1.00 | 1.00 | 1.00 | 1.00 | 1.00 | 1.00 | 1.00 | 1.00 | 1.00 |
| Slc9a2 | 0.99 | 1.18 | 1.00 | 0.90 | 0.80 | 1.66 | 1.00 | 1.00 | 1.00 |
| Slco4a1 | 0.74 | 5.16 | 1.33 | 1.00 | 1.00 | 1.00 | 0.63 | 1.17 | 0.93 |
| Slfn1 | 1.04 | 1.73 | 0.79 | 1.00 | 1.00 | 1.00 | 1.12 | 1.56 | 0.67 |
| Slfn2 | 1.12 | 3.07 | 0.78 | 1.04 | 1.39 | 0.98 | 0.97 | 1.28 | 0.68 |
| Slfn4 | 0.68 | 3.25 | 0.65 | 1.00 | 0.95 | 1.00 | 0.44 | 1.95 | 1.01 |
| Slit1 | 1.00 | 1.00 | 1.00 | 1.00 | 1.00 | 1.00 | 1.00 | 1.00 | 1.00 |
| Slmo1 | 1.00 | 1.00 | 1.00 | 1.00 | 1.00 | 1.00 | 1.00 | 1.00 | 1.00 |
| Sln | 0.66 | 1.36 | 1.18 | 0.90 | 2.06 | 0.85 | 1.00 | 1.00 | 1.00 |

Fig. 31-99

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Rhbg | 1.00 | 1.00 | 1.00 | 1.00 | 6.26 | 1.00 | 0.98 | 0.48 | 0.88 |
| Rhcg | 1.00 | 1.00 | 1.00 | 1.00 | 102.43 | 1.00 | 1.09 | 0.90 | 1.03 |
| Rhoh | 1.00 | 1.05 | 1.00 | 1.00 | 1.00 | 1.00 | 1.00 | 1.00 | 1.00 |
| Rhpn1 | 0.96 | 1.01 | 1.06 | 1.00 | 12.22 | 1.00 | 1.16 | 1.05 | 1.21 |
| Rn45s | 0.83 | 1.04 | 0.84 | 1.13 | 5.04 | 1.33 | 0.63 | 1.30 | 1.08 |
| Rnase11 | 1.00 | 1.00 | 1.00 | 1.00 | 5.02 | 1.00 | 1.00 | 1.00 | 1.00 |
| Rnase12 | 1.00 | 1.00 | 1.00 | 1.00 | 17.48 | 1.00 | 1.00 | 1.00 | 1.53 |
| Rnase13 | 1.00 | 1.00 | 1.00 | 1.00 | 167.24 | 1.00 | 1.00 | 1.00 | 1.00 |
| Rnase9 | 1.00 | 1.00 | 1.00 | 1.00 | 96.19 | 1.00 | 1.00 | 1.00 | 1.21 |
| Rnf149 | 0.97 | 1.01 | 0.99 | 0.91 | 6.37 | 1.05 | 0.84 | 0.95 | 1.06 |
| Rnu11 | 1.00 | 1.00 | 1.00 | 6.09 | 0.21 | 1.00 | 4.56 | 10.47 | 0.25 |
| Rnu73b | 36.80 | 0.02 | 1.02 | 0.79 | 0.60 | 0.70 | 0.02 | 0.02 | 1.01 |
| Ros1 | 1.00 | 1.00 | 1.00 | 1.00 | 8.25 | 1.00 | 1.00 | 1.00 | 1.00 |
| Rps27 | 1.02 | 1.34 | 0.64 | 1.29 | 1.41 | 1.25 | 7.53 | 0.78 | 1.12 |
| Rptn | 1.00 | 1.00 | 1.00 | 1.00 | 1.00 | 1.00 | 0.92 | 1.00 | 1.00 |
| Rrm2 | 1.00 | 2.61 | 1.00 | 1.05 | 1.14 | 0.76 | 1.09 | 1.07 | 0.98 |
| Rsph1 | 0.75 | 0.63 | 0.61 | 0.34 | 0.19 | 0.64 | 0.81 | 0.63 | 0.65 |
| S100a8 | 1.13 | 2.59 | 2.67 | 3.03 | 6.50 | 1.86 | 1.00 | 1.00 | 1.00 |
| S100a9 | 0.67 | 2.98 | 1.94 | 3.34 | 7.52 | 1.60 | 1.00 | 1.00 | 1.00 |
| S100b | 1.04 | 0.96 | 1.04 | 1.00 | 5.72 | 0.70 | 1.00 | 0.93 | 1.00 |
| Saa3 | 1.00 | 1.00 | 1.00 | 4.53 | 0.65 | 0.28 | 1.00 | 1.00 | 1.00 |
| Scarna10 | 1.00 | 1.00 | 1.00 | 1.00 | 0.03 | 1.00 | 0.05 | 0.04 | 0.02 |
| Scarna17 | 1.00 | 111.70 | 1.00 | 1.00 | 0.01 | 0.02 | 0.03 | 35.48 | 1.00 |
| Scarna3b | 0.26 | 3.26 | 2.92 | 0.30 | 3.03 | 0.23 | 0.37 | 1.67 | 4.52 |
| Scarna8 | 0.22 | 1.00 | 1.06 | 1.00 | 0.44 | 1.12 | 0.64 | 1.00 | 0.38 |
| Scarna9 | 1.00 | 1.00 | 1.00 | 1.00 | 1.00 | 1.00 | 1.00 | 562.26 | 1.00 |
| Scgb1a1 | 1.00 | 1.00 | 1.00 | 1.68 | 0.94 | 1.13 | 1.00 | 1.00 | 1.00 |
| Scgb3a1 | 1.08 | 1.00 | 1.00 | 1.00 | 1.00 | 1.00 | 1.00 | 1.00 | 1.00 |
| Scgb3a2 | 1.00 | 1.00 | 1.00 | 1.00 | 1.00 | 1.00 | 1.00 | 1.00 | 1.00 |
| Scn4b | 0.97 | 0.91 | 1.05 | 0.96 | 1.25 | 0.76 | 1.00 | 1.00 | 1.00 |
| Scx | 1.08 | 1.26 | 0.83 | 1.00 | 5.62 | 1.00 | 0.93 | 0.91 | 1.29 |
| Sec14l3 | 1.00 | 1.00 | 1.00 | 1.00 | 1.00 | 1.00 | 1.00 | 1.00 | 1.00 |
| Serpina1f | 1.00 | 1.00 | 1.00 | 1.00 | 27.36 | 1.00 | 1.00 | 1.00 | 1.03 |
| Serpinb12 | 1.00 | 1.00 | 1.00 | 1.00 | 1.00 | 1.00 | 1.00 | 1.00 | 1.00 |
| Serpinb1c | 1.00 | 1.00 | 1.00 | 1.00 | 1.00 | 1.00 | 1.00 | 1.00 | 1.00 |
| Serpinb2 | 1.00 | 1.00 | 1.00 | 3.29 | 0.72 | 0.17 | 1.00 | 1.00 | 1.00 |
| Serpine1 | 1.00 | 1.00 | 1.00 | 2.93 | 0.28 | 0.51 | 1.00 | 1.00 | 1.00 |
| Serpinf2 | 1.00 | 1.00 | 1.00 | 1.00 | 6.09 | 1.00 | 1.00 | 1.00 | 1.00 |
| Sfrp2 | 0.83 | 0.97 | 0.93 | 0.77 | 2.00 | 0.72 | 1.00 | 1.00 | 1.00 |
| Sftpa1 | 1.00 | 1.00 | 1.00 | 1.00 | 1.00 | 1.00 | 1.00 | 1.00 | 1.00 |
| Sftpb | 1.00 | 1.00 | 1.00 | 1.00 | 1.00 | 1.00 | 0.80 | 0.76 | 1.25 |
| Sftpc | 0.87 | 0.92 | 1.00 | 1.00 | 1.00 | 1.00 | 1.00 | 1.00 | 1.00 |
| Sftpd | 1.00 | 1.00 | 1.00 | 1.00 | 1.00 | 1.00 | 1.00 | 1.00 | 1.00 |
| Sh2d5 | 1.02 | 0.96 | 0.93 | 1.00 | 1.00 | 1.00 | 1.00 | 1.00 | 1.00 |
| Sh3gl3 | 1.03 | 1.05 | 0.97 | 1.00 | 6.02 | 1.00 | 1.04 | 1.03 | 1.03 |
| Siglecg | 1.00 | 2.60 | 1.00 | 1.00 | 1.81 | 0.23 | 1.00 | 1.00 | 1.00 |
| Slamf6 | 1.00 | 1.90 | 1.00 | 1.00 | 1.17 | 0.74 | 1.00 | 1.00 | 1.00 |
| Slamf7 | 1.00 | 1.68 | 1.00 | 1.00 | 1.27 | 1.00 | 1.07 | 1.05 | 1.08 |
| Slc15a2 | 0.94 | 0.78 | 0.89 | 0.39 | 0.90 | 0.40 | 1.00 | 1.00 | 1.00 |
| Slc16a3 | 0.87 | 1.17 | 1.11 | 2.61 | 1.36 | 0.60 | 0.90 | 1.07 | 0.92 |
| Slc17a9 | 1.00 | 1.00 | 1.00 | 1.07 | 5.60 | 0.71 | 0.99 | 0.99 | 0.95 |
| Slc1a5 | 1.23 | 2.36 | 1.00 | 0.76 | 0.55 | 0.94 | 0.76 | 1.24 | 0.97 |
| Slc34a2 | 1.00 | 1.00 | 1.00 | 1.00 | 8.19 | 1.00 | 1.07 | 0.95 | 1.03 |
| Slc38a5 | 1.03 | 1.30 | 1.43 | 0.63 | 44.44 | 1.42 | 0.95 | 0.76 | 0.89 |
| Slc41a2 | 0.97 | 1.02 | 1.00 | 1.43 | 5.35 | 0.85 | 1.00 | 0.95 | 1.01 |
| Slc46a2 | 1.00 | 1.00 | 1.00 | 1.00 | 6.89 | 1.00 | 1.00 | 1.00 | 1.00 |
| Slc9a2 | 0.98 | 1.10 | 0.90 | 1.00 | 8.05 | 1.00 | 1.08 | 0.89 | 0.96 |
| Slco4a1 | 1.13 | 1.19 | 0.70 | 1.00 | 3.68 | 1.00 | 1.00 | 1.00 | 1.00 |
| Slfn1 | 1.00 | 1.00 | 1.00 | 2.49 | 1.32 | 0.74 | 1.00 | 1.00 | 1.00 |
| Slfn2 | 1.00 | 3.61 | 1.06 | 1.63 | 1.53 | 0.63 | 1.00 | 1.00 | 1.00 |
| Slfn4 | 1.00 | 1.00 | 1.00 | 3.39 | 1.08 | 0.38 | 1.00 | 1.00 | 1.00 |
| Slit1 | 0.95 | 1.06 | 0.95 | 1.00 | 5.44 | 1.00 | 1.00 | 1.00 | 1.00 |
| Slmo1 | 1.28 | 1.11 | 0.98 | 1.00 | 5.23 | 1.00 | 1.22 | 0.92 | 1.11 |
| Sln | 1.16 | 0.94 | 2.51 | 1.00 | 1.00 | 1.00 | 1.02 | 0.99 | 1.10 |

Fig. 31- 100

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Rhbg | 1.03 | 1.12 | 1.00 | 1.00 | 1.00 | 1.00 | 1.00 | 1.00 | 1.00 | 0.85 | 1.00 | 1.00 |
| Rhcg | 1.00 | 1.00 | 1.00 | 1.00 | 1.00 | 1.00 | 1.00 | 1.00 | 1.00 | 1.00 | 1.06 | 1.21 |
| Rhoh | 0.86 | 0.80 | 0.84 | 1.12 | 0.66 | 0.93 | 1.00 | 1.00 | 1.00 | 1.00 | 1.02 | 1.11 |
| Rhpn1 | 1.00 | 1.00 | 1.00 | 1.00 | 1.00 | 1.00 | 1.00 | 1.00 | 1.00 | 1.00 | 1.44 | 1.09 |
| Rn45s | 3.63 | 1.12 | 1.21 | 0.39 | 0.96 | 1.10 | 0.67 | 1.09 | 1.01 | 0.98 | 1.00 | 1.00 |
| Rnase11 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.05 | 1.00 | 1.00 | 1.00 | 1.00 | 0.59 | 1.00 | 1.00 |
| Rnase13 | 1.00 | 1.00 | 1.00 | 1.00 | 1.00 | 1.00 | 1.00 | 1.00 | 1.00 | 1.00 | 1.24 | 0.91 |
| Rnase9 | 1.00 | 1.00 | 1.00 | 1.00 | 1.00 | 1.00 | 1.00 | 1.00 | 1.00 | 1.00 | 0.94 | 0.70 |
| Rnf149 | 0.99 | 1.07 | 1.05 | 1.10 | 1.18 | 1.02 | 0.93 | 1.23 | 1.01 | 0.90 | 1.00 | 1.00 |
| Rnu11 | 1.00 | 5.25 | 1.00 | 4.52 | 7.68 | 4.50 | 1.00 | 1.00 | 1.00 | 1.00 | 1.00 | 1.00 |
| Rnu73b | 0.60 | 0.65 | 1.10 | 0.84 | 1.02 | 1.12 | 0.21 | 2.58 | 0.66 | 1.00 | 1.08 | 1.03 |
| Ros1 | 1.00 | 1.00 | 1.00 | 1.00 | 1.00 | 1.00 | 1.00 | 1.00 | 1.00 | 1.00 | 1.00 | 1.00 |
| Rps27 | 1.05 | 1.04 | 1.08 | 0.88 | 1.11 | 0.92 | 1.45 | 1.00 | 1.00 | 0.98 | 1.08 | 0.92 |
| Rptn | 0.95 | 7.39 | 1.29 | 1.00 | 1.00 | 1.00 | 1.00 | 1.00 | 1.00 | 0.84 | 1.00 | 1.00 |
| Rrm2 | 0.40 | 0.57 | 0.92 | 0.94 | 0.90 | 0.99 | 1.00 | 0.97 | 0.99 | 0.98 | 1.03 | 1.05 |
| Rsph1 | 2.73 | 5.62 | 0.66 | 1.18 | 0.98 | 0.72 | 1.00 | 1.00 | 1.00 | 1.00 | 1.15 | 0.80 |
| S100a8 | 1.14 | 3.68 | 1.34 | 1.14 | 1.05 | 1.10 | 1.66 | 0.57 | 1.00 | 4.51 | 1.05 | 0.83 |
| S100a9 | 1.05 | 3.00 | 1.42 | 1.07 | 1.00 | 1.08 | 1.88 | 0.53 | 0.99 | 3.14 | 1.00 | 1.00 |
| S100b | 1.00 | 0.82 | 2.04 | 1.00 | 1.00 | 1.00 | 1.00 | 1.00 | 1.00 | 0.93 | 1.25 | 0.90 |
| Saa3 | 0.77 | 4.10 | 1.21 | 1.15 | 11.48 | 1.18 | 4.89 | 1.00 | 1.00 | 1.00 | 1.10 | 0.91 |
| Scarna10 | 0.04 | 22.11 | 1.00 | 0.05 | 1.00 | 0.02 | 1.00 | 1.00 | 1.00 | 1.00 | 1.00 | 1.00 |
| Scarna17 | 1.00 | 81.45 | 57.42 | 0.02 | 36.85 | 0.02 | 25.31 | 1.00 | 0.02 | 1.00 | 1.00 | 1.00 |
| Scarna3b | 0.94 | 1.00 | 0.59 | 0.38 | 1.00 | 0.36 | 1.00 | 1.00 | 1.00 | 1.00 | 1.00 | 25.61 |
| Scarna8 | 0.06 | 1.03 | 0.51 | 4.14 | 0.98 | 0.74 | 1.00 | 1.00 | 1.00 | 1.00 | 0.96 | 0.91 |
| Scarna9 | 618.36 | 1.00 | 1.00 | 1.00 | 1.00 | 1.00 | 1.00 | 1.00 | 1.00 | 1.00 | 1.11 | 1.08 |
| Scgb1a1 | 1.89 | 245.78 | 0.93 | 1.00 | 1.00 | 1.00 | 1.00 | 1.00 | 1.00 | 0.76 | 1.00 | 1.00 |
| Scgb3a1 | 1.68 | 131.23 | 0.97 | 1.00 | 1.00 | 1.00 | 1.00 | 1.00 | 1.00 | 1.00 | 1.00 | 1.00 |
| Scgb3a2 | 1.00 | 266.63 | 1.05 | 1.00 | 1.00 | 1.00 | 1.00 | 1.00 | 1.00 | 1.00 | 1.16 | 0.94 |
| Scn4b | 1.02 | 0.84 | 0.63 | 1.00 | 1.01 | 0.63 | 1.37 | 0.50 | 0.94 | 1.29 | 1.41 | 1.12 |
| Scx | 1.48 | 0.90 | 1.05 | 1.00 | 1.00 | 1.00 | 1.00 | 0.99 | 0.84 | 0.77 | 0.92 | 1.03 |
| Sec14l3 | 1.00 | 13.43 | 1.00 | 1.00 | 1.00 | 1.00 | 1.00 | 1.00 | 1.00 | 1.00 | 1.00 | 1.00 |
| Serpina1f | 1.00 | 1.00 | 1.00 | 1.00 | 1.00 | 1.00 | 1.00 | 1.00 | 1.00 | 1.00 | 1.36 | 1.23 |
| Serpinb12 | 1.02 | 10.15 | 1.14 | 1.00 | 1.00 | 1.00 | 1.00 | 1.00 | 1.00 | 0.72 | 1.07 | 0.97 |
| Serpinb1c | 1.11 | 1.81 | 1.07 | 1.00 | 1.17 | 1.01 | 1.01 | 1.14 | 1.02 | 1.00 | 1.21 | 1.42 |
| Serpinb2 | 0.47 | 1.07 | 0.99 | 1.12 | 0.97 | 0.75 | 1.00 | 1.00 | 1.00 | 0.91 | 1.11 | 1.10 |
| Serpine1 | 1.00 | 1.27 | 1.63 | 1.00 | 1.00 | 1.00 | 1.00 | 1.00 | 1.00 | 1.02 | 1.00 | 1.00 |
| Serpinf2 | 1.00 | 1.00 | 1.00 | 1.00 | 1.00 | 1.00 | 1.00 | 1.00 | 1.00 | 1.00 | 0.99 | 1.08 |
| Sfrp2 | 2.28 | 0.87 | 1.52 | 1.00 | 1.00 | 1.00 | 1.00 | 1.00 | 1.00 | 0.82 | 1.05 | 1.06 |
| Sftpa1 | 1.00 | 1.33 | 1.00 | 1.00 | 1.00 | 1.00 | 1.00 | 1.00 | 1.00 | 1.00 | 1.00 | 1.00 |
| Sftpb | 1.00 | 1.00 | 1.00 | 1.00 | 0.65 | 1.28 | 1.00 | 1.00 | 1.00 | 1.00 | 1.00 | 1.00 |
| Sftpc | 1.02 | 1.72 | 1.00 | 1.00 | 1.00 | 1.00 | 1.00 | 1.00 | 1.00 | 1.00 | 1.17 | 0.92 |
| Sftpd | 1.17 | 1.67 | 0.80 | 1.00 | 1.00 | 1.00 | 1.00 | 1.00 | 1.00 | 1.00 | 0.78 | 1.09 |
| Sh2d5 | 0.98 | 1.18 | 0.93 | 0.93 | 0.88 | 0.96 | 1.00 | 1.00 | 1.00 | 1.60 | 0.89 | 0.85 |
| Sh3gl3 | 1.00 | 1.06 | 1.45 | 1.00 | 1.00 | 1.00 | 1.00 | 1.00 | 1.00 | 1.00 | 1.06 | 1.05 |
| Siglecg | 2.29 | 3.20 | 1.95 | 1.11 | 0.55 | 0.77 | 1.00 | 1.00 | 1.00 | 1.00 | 1.01 | 1.09 |
| Slamf6 | 0.94 | 1.12 | 0.88 | 1.01 | 0.58 | 0.75 | 1.00 | 1.00 | 1.00 | 1.00 | 1.00 | 1.00 |
| Slamf7 | 1.06 | 1.84 | 1.31 | 1.00 | 0.59 | 0.72 | 1.00 | 1.00 | 1.00 | 1.00 | 1.41 | 1.10 |
| Slc15a2 | 0.91 | 7.69 | 0.31 | 1.12 | 2.42 | 0.47 | 0.89 | 1.37 | 0.65 | 0.69 | 0.96 | 0.99 |
| Slc16a3 | 0.97 | 1.95 | 1.28 | 1.08 | 1.23 | 1.14 | 1.00 | 1.00 | 1.00 | 1.27 | 1.10 | 1.00 |
| Slc17a9 | 1.40 | 1.78 | 1.46 | 1.17 | 1.08 | 0.99 | 0.83 | 1.20 | 1.12 | 0.97 | 1.28 | 1.02 |
| Slc1a5 | 1.57 | 1.03 | 1.27 | 1.11 | 0.75 | 1.05 | 1.11 | 1.02 | 0.93 | 1.09 | 1.00 | 1.00 |
| Slc34a2 | 0.94 | 0.84 | 1.00 | 1.00 | 1.00 | 1.00 | 1.00 | 1.00 | 1.00 | 0.92 | 0.99 | 1.04 |
| Slc38a5 | 1.00 | 1.00 | 1.00 | 1.09 | 0.72 | 1.13 | 0.66 | 0.92 | 0.99 | 1.00 | 0.95 | 0.96 |
| Slc41a2 | 1.10 | 1.69 | 2.00 | 1.07 | 1.00 | 1.08 | 1.00 | 1.00 | 1.00 | 1.04 | 0.97 | 1.17 |
| Slc46a2 | 0.86 | 0.76 | 0.80 | 1.00 | 1.00 | 1.00 | 1.00 | 1.00 | 1.00 | 1.03 | 1.00 | 1.00 |
| Slc9a2 | 1.24 | 0.98 | 1.03 | 1.00 | 1.00 | 1.00 | 1.00 | 1.00 | 1.00 | 1.00 | 1.04 | 1.03 |
| Slco4a1 | 1.05 | 0.86 | 0.89 | 1.06 | 0.96 | 0.82 | 1.00 | 1.05 | 0.88 | 1.10 | 1.00 | 1.00 |
| Slfn1 | 1.16 | 1.54 | 1.13 | 1.20 | 1.44 | 1.17 | 1.00 | 1.00 | 1.00 | 1.00 | 1.00 | 1.00 |
| Slfn2 | 1.08 | 1.34 | 1.02 | 1.17 | 1.39 | 1.21 | 0.78 | 0.92 | 0.92 | 1.29 | 1.00 | 1.00 |
| Slfn4 | 0.65 | 1.74 | 1.05 | 0.87 | 1.94 | 1.13 | 1.00 | 1.00 | 1.00 | 1.27 | 1.00 | 1.00 |
| Slit1 | 1.00 | 1.00 | 1.00 | 1.00 | 1.00 | 1.00 | 1.00 | 1.00 | 1.00 | 1.00 | 0.83 | 0.90 |
| Slmo1 | 1.00 | 1.00 | 1.00 | 1.00 | 1.00 | 1.00 | 1.00 | 1.00 | 1.00 | 1.04 | 0.95 | 1.07 |
| Sln | 9.85 | 5.62 | 4.98 | 1.00 | 1.00 | 1.00 | 1.00 | 1.00 | 1.00 | 1.04 | 1.09 | 1.11 |

Fig. 31-101

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Slpi | 3.84 | 0.70 | 10.32 | 0.83 | 1.02 | 2.26 | 1.33 | 1.20 | 0.87 |
| Smcp | 1.00 | 1.00 | 1.00 | 0.62 | 0.77 | 1.65 | 1.00 | 1.00 | 1.00 |
| Smpx | 1.32 | 0.90 | 0.85 | 0.89 | 1.00 | 1.00 | 1.00 | 1.00 | 1.00 |
| Snn | 0.85 | 1.09 | 0.72 | 0.95 | 1.22 | 0.93 | 1.00 | 7.69 | 1.00 |
| Snora15 | 1.57 | 0.52 | 6.40 | 0.49 | 0.86 | 0.68 | 1.08 | 0.07 | 1.13 |
| Snora16a | 1.22 | 1.63 | 1.29 | 0.31 | 0.62 | 2.94 | 0.62 | 0.67 | 1.48 |
| Snora19 | 0.01 | 1.00 | 1.00 | 1.00 | 1.00 | 1.00 | 1.00 | 1.00 | 1.00 |
| Snora20 | 49.87 | 0.86 | 1.00 | 0.01 | 0.01 | 0.01 | 0.56 | 535.17 | 1.00 |
| Snora21 | 9.06 | 0.60 | 6.66 | 0.80 | 0.21 | 0.39 | 5.12 | 0.92 | 1.58 |
| Snora24 | 0.51 | 1.00 | 1.00 | 1.00 | 1.00 | 1.00 | 1.00 | 1.00 | 1.00 |
| Snora26 | 0.46 | 1.00 | 2.95 | 2.86 | 2.97 | 1.00 | 0.50 | 1.32 | 3.25 |
| Snora2b | 1.88 | 0.85 | 2.90 | 1.76 | 1.68 | 2.24 | 8.69 | 1.92 | 0.64 |
| Snora33 | 1.70 | 1.39 | 1.40 | 0.71 | 0.94 | 2.05 | 0.78 | 4.49 | 6.06 |
| Snora35 | 1.00 | 1.00 | 1.00 | 1.00 | 1.00 | 1.00 | 1.00 | 1.00 | 1.00 |
| Snora36b | 1.00 | 7.00 | 1.00 | 1.04 | 1.00 | 1.00 | 1.00 | 1.00 | 1.00 |
| Snora41 | 2.36 | 1.52 | 1.27 | 1.17 | 4.36 | 0.23 | 0.79 | 1.69 | 0.71 |
| Snora44 | 0.87 | 0.57 | 0.50 | 2.45 | 1.28 | 1.49 | 0.78 | 1.02 | 0.66 |
| Snora47 | 0.31 | 0.34 | 0.55 | 0.73 | 0.95 | 0.25 | 0.33 | 1.00 | 1.59 |
| Snora52 | 2.05 | 0.66 | 0.90 | 1.10 | 1.14 | 0.85 | 1.23 | 1.73 | 0.75 |
| Snora5c | 1.44 | 0.26 | 1.04 | 0.08 | 1.71 | 1.02 | 0.67 | 0.92 | 3.54 |
| Snora61 | 0.71 | 3.02 | 0.63 | 1.18 | 2.30 | 0.69 | 3.16 | 1.55 | 0.22 |
| Snora62 | 1.64 | 1.15 | 0.33 | 2.88 | 0.35 | 0.92 | 0.47 | 1.20 | 0.77 |
| Snora64 | 1.78 | 1.29 | 0.71 | 0.44 | 1.75 | 1.26 | 0.85 | 0.93 | 1.75 |
| Snora68 | 1.85 | 2.23 | 2.09 | 0.20 | 0.46 | 0.89 | 0.98 | 0.55 | 0.69 |
| Snora69 | 1.55 | 7.54 | 0.28 | 3.58 | 1.12 | 0.62 | 0.16 | 1.00 | 0.90 |
| Snora75 | 1.81 | 0.61 | 0.90 | 5.04 | 1.90 | 2.05 | 1.66 | 1.30 | 1.35 |
| Snord100 | 3.76 | 1.05 | 1.55 | 1.21 | 0.01 | 0.68 | 2.68 | 2.58 | 3.42 |
| Snord11 | 1.00 | 1.00 | 1.00 | 1.00 | 1.00 | 1.00 | 143.04 | 1.00 | 1.00 |
| Snord110 | 1.00 | 1.00 | 0.46 | 1.00 | 1.00 | 1.00 | 1.00 | 0.01 | 1.00 |
| Snord111 | 1.00 | 1.00 | 1.00 | 1.00 | 1.00 | 1.00 | 1.00 | 1.00 | 1.00 |
| Snord116 | 1.00 | 1.00 | 1.00 | 1.00 | 1.00 | 1.00 | 1.00 | 1.00 | 1.00 |
| Snord116l1 | 1.00 | 1.00 | 1.00 | 1.00 | 1.00 | 1.00 | 1.00 | 1.00 | 1.00 |
| Snord12 | 2.82 | 0.78 | 0.70 | 0.88 | 3.44 | 1.52 | 0.71 | 1.31 | 1.77 |
| Snord123 | 1.72 | 0.88 | 0.44 | 2.02 | 2.82 | 0.31 | 25.31 | 14.25 | 1.00 |
| Snord16a | 11.86 | 3.84 | 0.62 | 1.61 | 1.37 | 2.99 | 1.97 | 5.49 | 1.01 |
| Snord19 | 0.87 | 0.28 | 0.00 | 1.00 | 1.00 | 1.00 | 1.00 | 1.00 | 1.00 |
| Snord1a | 36.47 | 0.58 | 1.00 | 1.00 | 0.33 | 1.00 | 1.06 | 1.00 | 1.00 |
| Snord1b | 0.05 | 0.03 | 0.92 | 58.11 | 1.90 | 0.05 | 1.00 | 1.06 | 23.35 |
| Snord1c | 0.05 | 1.00 | 1.00 | 1.19 | 0.01 | 18.50 | 1.00 | 1.00 | 43.37 |
| Snord23 | 0.14 | 0.85 | 0.95 | 0.82 | 0.24 | 6.50 | 1.00 | 8.73 | 0.05 |
| Snord34 | 169.61 | 1.66 | 0.48 | 1.00 | 1.15 | 0.53 | 2.64 | 0.02 | 3.51 |
| Snord35b | 0.97 | 1.58 | 2.37 | 44.70 | 10.93 | 2.01 | 0.49 | 2.52 | 0.60 |
| Snord37 | 1.14 | 1.21 | 0.90 | 1.00 | 1.00 | 1.00 | 1.00 | 1.00 | 1.00 |
| Snord38a | 59.65 | 0.01 | 1.00 | 1.00 | 1.00 | 1.00 | 0.01 | 123.75 | 109.63 |
| Snord42a | 873.18 | 0.83 | 0.00 | 1.00 | 1.00 | 1.00 | 1.00 | 1.00 | 1.00 |
| Snord42b | 95.31 | 1.00 | 0.01 | 1.00 | 1.00 | 1.00 | 1.00 | 1.00 | 1.00 |
| Snord45b | 1.00 | 771.24 | 0.00 | 1.00 | 1.00 | 1.00 | 1.00 | 1.00 | 1.00 |
| Snord45c | 1.00 | 0.59 | 0.67 | 105.38 | 102.14 | 82.40 | 0.02 | 0.91 | 0.61 |
| Snord49a | 45.82 | 45.34 | 0.01 | 1.21 | 1.00 | 0.01 | 79.55 | 1.06 | 1.00 |
| Snord49b | 44.98 | 0.01 | 1.00 | 1.19 | 108.79 | 1.00 | 1.00 | 79.48 | 1.00 |
| Snord4a | 0.39 | 0.32 | 0.37 | 1.21 | 1.14 | 1.03 | 4.24 | 0.29 | 0.65 |
| Snord52 | 2.70 | 1.73 | 244.10 | 1.00 | 0.00 | 0.01 | 1.00 | 0.78 | 109.63 |
| Snord53 | 29.11 | 27.43 | 0.92 | 110.19 | 62.27 | 77.11 | 1.04 | 1.00 | 1.00 |
| Snord55 | 1.75 | 2.54 | 0.95 | 0.01 | 52.92 | 0.02 | 1.00 | 0.79 | 1.18 |
| Snord57 | 3.32 | 39.78 | 0.92 | 1.00 | 1.00 | 1.00 | 138.63 | 1.00 | 73.21 |
| Snord58b | 1.41 | 178.08 | 1.00 | 1.00 | 1.00 | 1.00 | 1.00 | 1.00 | 1.00 |
| Snord61 | 1.00 | 1.00 | 1.00 | 1.00 | 1.00 | 1.00 | 1.00 | 1.00 | 1.00 |
| Snord64 | 1371.98 | 1.00 | 335.73 | 1.00 | 1.00 | 1.00 | 1.00 | 1.00 | 1.00 |
| Snord65 | 72.40 | 0.01 | 1.00 | 1.00 | 1.00 | 1.00 | 1.00 | 160.27 | 0.60 |
| Snord66 | 0.88 | 1.00 | 131.92 | 1.22 | 234.64 | 115.88 | 0.92 | 0.82 | 1.70 |
| Snord67 | 1.00 | 1.00 | 1.00 | 1.00 | 9.00 | 1.00 | 7.83 | 0.87 | 1.00 |
| Snord68 | 1.00 | 217.16 | 1.00 | 1.00 | 1.00 | 1.00 | 1.00 | 1.00 | 1.00 |
| Snord69 | 1.00 | 0.43 | 0.00 | 0.00 | 1.00 | 97.93 | 222.95 | 0.86 | 0.02 |
| Snord7 | 0.06 | 1.00 | 0.32 | 1.47 | 0.21 | 1.00 | 13.46 | 3.64 | 0.12 |

Fig. 31-102

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Slpi | 1.16 | 0.52 | 1.37 | 1.00 | 0.53 | 1.00 | 0.68 | 3.04 | 1.13 |
| Smcp | 1.00 | 1.00 | 1.00 | 1.00 | 1.00 | 0.35 | 1.00 | 1.00 | 1.00 |
| Smpx | 1.57 | 1.61 | 1.07 | 0.83 | 0.84 | 1.00 | 1.00 | 1.00 | 1.00 |
| Snn | 0.85 | 2.19 | 0.90 | 0.81 | 1.69 | 1.06 | 0.86 | 0.94 | 0.67 |
| Snora15 | 1.27 | 3.49 | 0.53 | 0.11 | 0.39 | 1.01 | 0.91 | 0.88 | 0.77 |
| Snora16a | 1.02 | 1.28 | 1.15 | 0.85 | 1.43 | 2.03 | 0.88 | 1.20 | 1.22 |
| Snora19 | 83.90 | 216.33 | 145.63 | 1.00 | 1.00 | 1.00 | 242.72 | 1.00 | 1.00 |
| Snora20 | 0.01 | 1.35 | 0.02 | 1.00 | 1.00 | 0.92 | 1.00 | 1.11 | 2.11 |
| Snora21 | 0.11 | 1.71 | 0.54 | 1.65 | 1.87 | 0.12 | 1.90 | 1.06 | 0.54 |
| Snora24 | 1.00 | 1.00 | 1.00 | 1.00 | 1.00 | 1.00 | 1.00 | 1.00 | 1.00 |
| Snora26 | 1.00 | 1.00 | 1.00 | 1.00 | 1.00 | 1.00 | 1.00 | 0.21 | 1.00 |
| Snora2b | 2.25 | 1.63 | 2.00 | 1.01 | 0.59 | 1.54 | 1.66 | 0.61 | 0.49 |
| Snora33 | 1.22 | 2.31 | 1.67 | 1.63 | 0.83 | 1.25 | 1.01 | 1.19 | 1.29 |
| Snora35 | 1.00 | 1.00 | 1.00 | 1.00 | 1.00 | 1.00 | 1.00 | 1.00 | 1.00 |
| Snora36b | 1.08 | 6.25 | 3.55 | 1.00 | 3.59 | 0.24 | 1.00 | 1.00 | 4.58 |
| Snora41 | 1.08 | 1.76 | 1.37 | 1.50 | 0.83 | 1.65 | 1.22 | 1.43 | 1.45 |
| Snora44 | 1.52 | 1.91 | 1.33 | 2.95 | 1.85 | 0.67 | 1.01 | 1.17 | 1.00 |
| Snora47 | 1.25 | 0.17 | 1.14 | 0.64 | 2.66 | 1.00 | 4.60 | 0.76 | 3.59 |
| Snora52 | 1.80 | 2.20 | 1.10 | 2.02 | 1.78 | 2.44 | 1.30 | 0.88 | 1.22 |
| Snora5c | 1.23 | 2.09 | 0.43 | 1.35 | 0.75 | 1.50 | 1.32 | 0.86 | 1.12 |
| Snora61 | 0.68 | 1.33 | 0.99 | 1.24 | 0.34 | 1.54 | 0.86 | 1.60 | 1.17 |
| Snora62 | 1.02 | 17.06 | 0.86 | 0.38 | 2.53 | 0.23 | 0.52 | 0.23 | 0.55 |
| Snora64 | 0.79 | 1.15 | 1.00 | 0.64 | 1.74 | 1.44 | 1.26 | 1.44 | 0.96 |
| Snora68 | 1.77 | 2.26 | 1.47 | 0.76 | 1.37 | 0.95 | 0.74 | 0.93 | 1.31 |
| Snora69 | 3.49 | 3.39 | 0.27 | 1.70 | 0.14 | 7.05 | 1.04 | 0.80 | 0.53 |
| Snora75 | 1.67 | 2.13 | 1.40 | 1.13 | 1.90 | 0.88 | 1.99 | 1.19 | 0.88 |
| Snord100 | 0.40 | 1.11 | 1.78 | 0.19 | 4.04 | 0.72 | 1.30 | 0.90 | 0.92 |
| Snord11 | 1.00 | 1.00 | 1.00 | 1.00 | 1.00 | 1.00 | 1.00 | 1.07 | 1.00 |
| Snord110 | 0.02 | 104.61 | 1.14 | 1.00 | 1.00 | 1.00 | 0.00 | 0.28 | 1.00 |
| Snord111 | 1.00 | 32.56 | 1.07 | 0.03 | 0.03 | 34.74 | 1.00 | 1.00 | 1.00 |
| Snord116 | 1.00 | 1.00 | 1.00 | 1.00 | 1.00 | 8.00 | 1.00 | 1.00 | 1.00 |
| Snord116l1 | 1.00 | 1.00 | 1.00 | 1.00 | 1.00 | 1.00 | 1.00 | 1.00 | 1.00 |
| Snord12 | 0.97 | 1.61 | 0.87 | 3.01 | 0.45 | 6.57 | 0.86 | 1.06 | 1.32 |
| Snord123 | 0.59 | 0.84 | 0.77 | 8.81 | 0.37 | 17.00 | 1.12 | 0.18 | 2.41 |
| Snord16a | 1.94 | 2.04 | 1.17 | 6.12 | 2.56 | 37.32 | 0.79 | 1.19 | 1.34 |
| Snord19 | 0.99 | 249.47 | 1.08 | 0.98 | 1.05 | 89.12 | 1.00 | 1.00 | 1.00 |
| Snord1a | 6.44 | 22.34 | 24.70 | 7.17 | 1.00 | 1.00 | 1.00 | 0.44 | 1.00 |
| Snord1b | 0.52 | 2.87 | 0.12 | 32.44 | 1.00 | 0.06 | 5.03 | 0.42 | 4.15 |
| Snord1c | 1.00 | 13.28 | 1.06 | 1.00 | 0.07 | 1.00 | 1.00 | 1.00 | 79.38 |
| Snord23 | 0.63 | 1.93 | 1.00 | 24.17 | 5.93 | 0.09 | 1.34 | 0.67 | 0.88 |
| Snord34 | 0.88 | 1.44 | 0.92 | 59.93 | 0.03 | 0.94 | 1.76 | 2.00 | 1.72 |
| Snord35b | 0.52 | 1.40 | 1.12 | 0.87 | 0.34 | 0.57 | 1.26 | 0.99 | 0.78 |
| Snord37 | 1.06 | 1.92 | 0.69 | 347.98 | 1.05 | 0.91 | 0.00 | 1.20 | 1.00 |
| Snord38a | 0.36 | 2.92 | 52.72 | 53.68 | 1.00 | 1.00 | 0.97 | 268.43 | 1.63 |
| Snord42a | 0.00 | 766.76 | 1.08 | 1.00 | 1.00 | 0.00 | 1.00 | 1.00 | 1.00 |
| Snord42b | 2.05 | 0.98 | 3.25 | 80.46 | 0.00 | 0.01 | 0.00 | 0.00 | 0.01 |
| Snord45b | 366.03 | 0.49 | 3.09 | 1.00 | 1.00 | 1.00 | 1.00 | 1.00 | 1.00 |
| Snord45c | 123.20 | 279.22 | 0.54 | 97.29 | 84.60 | 1.00 | 0.48 | 0.07 | 0.12 |
| Snord49a | 0.80 | 2.08 | 0.64 | 1.00 | 0.02 | 43.57 | 0.18 | 2.09 | 0.60 |
| Snord49b | 0.35 | 8.96 | 4.28 | 38.01 | 0.03 | 37.59 | 0.83 | 0.85 | 0.16 |
| Snord4a | 1.08 | 1.05 | 0.84 | 1.19 | 1.00 | 67.05 | 0.89 | 1.23 | 1.89 |
| Snord52 | 1.04 | 2.75 | 1.11 | 53.69 | 0.50 | 0.98 | 0.49 | 1.67 | 0.61 |
| Snord53 | 0.96 | 71.95 | 5.22 | 26.22 | 1.00 | 0.04 | 1.56 | 114.98 | 1.40 |
| Snord55 | 39.40 | 1.01 | 1.35 | 2.10 | 0.04 | 28.24 | 0.52 | 1.54 | 2.64 |
| Snord57 | 0.34 | 360.30 | 1.46 | 1.95 | 79.21 | 0.92 | 2.21 | 0.68 | 2.13 |
| Snord58b | 0.48 | 1.22 | 1.05 | 160.43 | 80.11 | 0.01 | 1.27 | 0.72 | 1.51 |
| Snord61 | 1.00 | 1.00 | 1.00 | 1.00 | 1.00 | 1.00 | 1.00 | 1.00 | 1.00 |
| Snord64 | 278.31 | 1.00 | 293.62 | 0.00 | 594.89 | 295.70 | 1.00 | 1.00 | 1.00 |
| Snord65 | 1.02 | 6.83 | 63.98 | 1.00 | 1.00 | 0.01 | 0.00 | 0.27 | 3.40 |
| Snord66 | 0.50 | 108.88 | 180.15 | 1.00 | 1.05 | 2.93 | 0.83 | 0.01 | 0.99 |
| Snord67 | 5.86 | 5.49 | 1.00 | 1.00 | 1.00 | 1.00 | 1.00 | 0.06 | 1.00 |
| Snord68 | 0.00 | 1.00 | 0.00 | 0.00 | 1.00 | 1.00 | 1.00 | 1.00 | 1.00 |
| Snord69 | 10.57 | 1.26 | 2.15 | 4.31 | 106.38 | 1.00 | 2.18 | 2.70 | 1.85 |
| Snord7 | 0.52 | 2.37 | 12.47 | 4.71 | 1.00 | 0.32 | 1.40 | 12.99 | 23.41 |

Fig. 31-103

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Slpi | 1.00 | 1.00 | 1.00 | 1.18 | 2.04 | 0.38 | 0.68 | 1.33 | 0.58 |
| Smcp | 1.00 | 1.00 | 1.00 | 1.00 | 7.59 | 1.00 | 1.01 | 1.09 | 1.03 |
| Smpx | 0.98 | 0.79 | 1.21 | 1.00 | 1.00 | 1.00 | 1.02 | 1.02 | 0.98 |
| Snn | 1.01 | 1.06 | 0.91 | 0.87 | 1.02 | 0.91 | 0.94 | 1.14 | 1.00 |
| Snora15 | 1.00 | 7.77 | 0.39 | 1.17 | 0.96 | 1.21 | 1.85 | 0.86 | 0.59 |
| Snora16a | 1.66 | 1.18 | 1.22 | 1.13 | 0.85 | 0.94 | 2.20 | 1.43 | 6.29 |
| Snora19 | 1.00 | 1.00 | 1.00 | 1.00 | 1.00 | 1.00 | 1.00 | 1.00 | 1.00 |
| Snora20 | 1.00 | 127.00 | 77.92 | 145.93 | 1.08 | 0.01 | 1.10 | 117.04 | 5.60 |
| Snora21 | 0.78 | 0.40 | 1.03 | 4.11 | 2.57 | 2.57 | 1.78 | 1.37 | 0.69 |
| Snora24 | 1.00 | 1.00 | 1.00 | 1.00 | 1.00 | 1.00 | 1.00 | 1.00 | 1.00 |
| Snora26 | 2.69 | 1.00 | 2.16 | 5.50 | 1.00 | 1.00 | 1.00 | 1.00 | 1.00 |
| Snora2b | 1.86 | 0.77 | 1.72 | 4.80 | 0.31 | 0.99 | 1.73 | 3.38 | 2.08 |
| Snora33 | 1.35 | 1.22 | 0.90 | 1.38 | 1.08 | 1.27 | 0.92 | 1.10 | 1.92 |
| Snora35 | 1.00 | 1.00 | 1.00 | 1.00 | 1.00 | 1.00 | 1.00 | 1.00 | 1.00 |
| Snora36b | 1.00 | 4.56 | 1.00 | 1.00 | 8.93 | 0.30 | 1.00 | 1.00 | 1.00 |
| Snora41 | 0.51 | 0.67 | 1.18 | 0.58 | 2.19 | 1.49 | 4.01 | 1.21 | 0.81 |
| Snora44 | 0.43 | 4.98 | 0.90 | 1.27 | 1.48 | 1.53 | 0.30 | 8.43 | 1.04 |
| Snora47 | 0.17 | 1.38 | 5.61 | 4.28 | 1.83 | 1.45 | 0.95 | 8.95 | 0.25 |
| Snora52 | 0.91 | 1.56 | 1.00 | 0.73 | 1.36 | 1.28 | 0.89 | 1.65 | 0.27 |
| Snora5c | 1.83 | 1.73 | 1.45 | 1.44 | 5.68 | 0.23 | 5.76 | 1.76 | 0.19 |
| Snora61 | 0.94 | 1.00 | 0.62 | 6.12 | 0.14 | 0.76 | 0.65 | 0.93 | 0.55 |
| Snora62 | 0.16 | 2.93 | 3.39 | 6.01 | 2.48 | 0.41 | 1.65 | 2.26 | 1.58 |
| Snora64 | 1.09 | 2.22 | 0.84 | 1.92 | 1.85 | 1.35 | 1.09 | 1.28 | 1.23 |
| Snora68 | 1.37 | 2.46 | 0.44 | 2.15 | 2.52 | 1.17 | 0.29 | 0.30 | 1.08 |
| Snora69 | 1.17 | 1.88 | 1.72 | 0.87 | 3.31 | 0.85 | 3.07 | 0.33 | 1.00 |
| Snora75 | 0.87 | 1.19 | 1.41 | 2.41 | 0.73 | 1.09 | 1.47 | 0.48 | 0.84 |
| Snord100 | 0.97 | 0.01 | 3.63 | 1.21 | 0.55 | 2.41 | 0.73 | 5.37 | 1.08 |
| Snord11 | 1.00 | 1.00 | 1.00 | 1.00 | 1.00 | 1.00 | 0.03 | 1.00 | 0.01 |
| Snord110 | 1.00 | 173.52 | 1.00 | 1.00 | 1.00 | 1.00 | 1.00 | 49.36 | 0.02 |
| Snord111 | 1.00 | 1.00 | 1.00 | 1.00 | 1.00 | 1.00 | 1.00 | 1.00 | 0.03 |
| Snord116 | 0.97 | 0.26 | 1.00 | 1.00 | 1.00 | 1.00 | 1.00 | 1.00 | 8.50 |
| Snord116l1 | 1.00 | 1.00 | 9.77 | 1.00 | 1.00 | 1.00 | 1.00 | 1.00 | 1.00 |
| Snord12 | 1.49 | 0.51 | 0.47 | 2.75 | 2.43 | 2.18 | 0.73 | 0.66 | 2.00 |
| Snord123 | 1.18 | 1.00 | 1.00 | 1.71 | 1.49 | 1.23 | 1.00 | 0.85 | 0.06 |
| Snord16a | 4.25 | 1.37 | 0.21 | 4.14 | 1.10 | 1.11 | 2.03 | 0.90 | 0.39 |
| Snord19 | 1.00 | 1.00 | 1.00 | 1.00 | 1.00 | 1.00 | 93.36 | 1.00 | 167.52 |
| Snord1a | 1.00 | 0.44 | 1.00 | 16.25 | 13.63 | 15.00 | 1.00 | 40.92 | 11.26 |
| Snord1b | 0.04 | 25.65 | 0.03 | 1.00 | 1.71 | 0.77 | 0.07 | 0.01 | 0.26 |
| Snord1c | 21.28 | 24.19 | 1.00 | 0.04 | 1.00 | 17.56 | 2.14 | 13.64 | 0.34 |
| Snord23 | 2.58 | 0.50 | 0.39 | 15.70 | 1.45 | 5.89 | 0.18 | 0.85 | 6.49 |
| Snord34 | 1.00 | 0.98 | 1.08 | 1.10 | 0.02 | 0.52 | 0.01 | 0.94 | 0.64 |
| Snord35b | 1.06 | 0.31 | 1.13 | 1.04 | 1.17 | 0.48 | 0.27 | 0.78 | 2.02 |
| Snord37 | 1.00 | 1.00 | 1.00 | 1.00 | 1.00 | 1.00 | 0.88 | 0.01 | 286.91 |
| Snord38a | 1.00 | 1.00 | 1.00 | 1.00 | 1.00 | 1.08 | 1.00 | 45.74 | 1.00 |
| Snord42a | 1.00 | 1.00 | 1.00 | 1.00 | 1.00 | 1.00 | 1.00 | 1.75 | 295.83 |
| Snord42b | 1.00 | 1.00 | 0.01 | 1.00 | 1.00 | 1.00 | 1.09 | 1.33 | 0.01 |
| Snord45b | 1.00 | 1.00 | 1.00 | 1.00 | 1.00 | 1.00 | 342.46 | 1.00 | 1.00 |
| Snord45c | 13.63 | 136.36 | 0.01 | 0.01 | 7.95 | 204.48 | 0.04 | 1.00 | 1.00 |
| Snord49a | 0.01 | 1.00 | 0.02 | 1.00 | 1.00 | 61.60 | 0.55 | 1.33 | 0.98 |
| Snord49b | 0.00 | 1.00 | 1.00 | 111.01 | 190.25 | 1.00 | 0.03 | 2.56 | 1.04 |
| Snord4a | 1.10 | 1.00 | 1.88 | 1.79 | 0.44 | 0.66 | 0.12 | 0.47 | 1.33 |
| Snord52 | 0.53 | 1.00 | 1.00 | 1.00 | 0.54 | 87.99 | 0.01 | 0.87 | 48.50 |
| Snord53 | 1.00 | 1.00 | 38.96 | 114.32 | 1.00 | 0.99 | 1.10 | 1.00 | 1.00 |
| Snord55 | 0.82 | 2.39 | 0.02 | 0.66 | 1.64 | 1.08 | 1.00 | 0.91 | 0.08 |
| Snord57 | 1.07 | 97.84 | 0.72 | 0.60 | 202.60 | 3.82 | 40.60 | 0.03 | 1.00 |
| Snord58b | 1.00 | 1.00 | 1.00 | 1.00 | 1.00 | 166.85 | 0.01 | 0.45 | 0.01 |
| Snord61 | 1.00 | 1.00 | 1.00 | 1.00 | 1.00 | 1.00 | 1.00 | 1.00 | 1.00 |
| Snord64 | 1.00 | 1.00 | 1.00 | 1.00 | 1.00 | 1.00 | 1.00 | 1.00 | 1.00 |
| Snord65 | 1.00 | 1.00 | 1.00 | 1.00 | 1.00 | 1.00 | 1.09 | 59.46 | 0.01 |
| Snord66 | 1.00 | 1.00 | 1.00 | 216.23 | 191.78 | 1.00 | 0.02 | 1.84 | 53.07 |
| Snord67 | 1.00 | 1.00 | 1.00 | 1.00 | 1.00 | 1.00 | 0.59 | 0.09 | 16.53 |
| Snord68 | 1.00 | 1.00 | 1.00 | 1.00 | 1.00 | 1.00 | 204.34 | 1.00 | 1.00 |
| Snord69 | 0.00 | 0.00 | 1.58 | 1.00 | 161.06 | 2.84 | 1.09 | 4.43 | 2.12 |
| Snord7 | 0.04 | 0.96 | 0.44 | 1.00 | 8.93 | 4.54 | 0.08 | 12.88 | 1.00 |

Fig. 31- 104

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Slpi | 1.13 | 21.45 | 20.41 | 1.21 | 1.00 | 1.04 | 1.44 | 1.36 | 1.72 | 2.40 | 1.15 | 0.94 |
| Smcp | 1.00 | 1.00 | 1.00 | 1.00 | 1.00 | 1.00 | 1.00 | 1.00 | 1.00 | 1.00 | 0.89 | 1.01 |
| Smpx | 1.80 | 5.22 | 2.58 | 1.00 | 1.00 | 1.00 | 1.00 | 1.00 | 1.00 | 1.31 | 1.00 | 1.00 |
| Snn | 1.16 | 1.22 | 1.00 | 1.10 | 0.51 | 0.74 | 0.91 | 0.91 | 0.75 | 0.92 | 1.62 | 0.98 |
| Snora15 | 1.72 | 1.06 | 1.66 | 6.71 | 0.70 | 3.95 | 2.46 | 0.31 | 1.00 | 1.00 | 10.82 | 1.00 |
| Snora16a | 0.83 | 0.97 | 0.96 | 1.26 | 1.26 | 0.97 | 8.58 | 1.47 | 0.70 | 9.41 | 1.00 | 1.00 |
| Snora19 | 1.00 | 0.01 | 1.00 | 2.57 | 1.00 | 1.00 | 1.00 | 1.00 | 1.00 | 1.00 | 1.00 | 1.00 |
| Snora20 | 1.05 | 2.22 | 1.99 | 96.28 | 0.02 | 60.11 | 0.71 | 1.00 | 1.00 | 1.00 | 1.00 | 1.00 |
| Snora21 | 1.09 | 0.87 | 0.71 | 1.09 | 2.30 | 1.15 | 0.66 | 0.91 | 2.18 | 1.00 | 1.00 | 1.00 |
| Snora24 | 1.00 | 1.00 | 1.00 | 6.56 | 1.00 | 1.00 | 0.35 | 1.00 | 1.00 | 1.00 | 1.00 | 1.00 |
| Snora26 | 1.00 | 0.42 | 0.97 | 0.24 | 3.40 | 1.00 | 0.42 | 1.00 | 2.05 | 1.00 | 1.00 | 1.00 |
| Snora2b | 0.51 | 1.83 | 0.66 | 0.31 | 0.60 | 1.27 | 1.00 | 1.00 | 1.00 | 59.91 | 1.00 | 0.01 |
| Snora33 | 0.70 | 1.12 | 1.23 | 1.34 | 1.98 | 0.96 | 1.50 | 2.34 | 4.86 | 1.00 | 1.00 | 1.00 |
| Snora35 | 1.00 | 1.00 | 1.00 | 1.00 | 1.00 | 1.00 | 1.00 | 1.00 | 1.00 | 1.00 | 20.04 | 0.03 |
| Snora36b | 1.00 | 1.10 | 0.24 | 0.29 | 1.00 | 1.19 | 1.00 | 1.00 | 1.00 | 1.00 | 0.49 | 3.84 |
| Snora41 | 0.92 | 1.13 | 1.12 | 0.98 | 0.59 | 0.92 | 1.74 | 0.80 | 0.84 | 53.46 | 1.00 | 1.00 |
| Snora44 | 1.46 | 0.70 | 0.62 | 0.70 | 1.18 | 0.67 | 0.61 | 1.19 | 2.17 | 1.00 | 0.41 | 1.99 |
| Snora47 | 0.32 | 0.19 | 0.76 | 1.00 | 5.00 | 0.61 | 4.19 | 0.27 | 2.29 | 1.00 | 1.00 | 1.00 |
| Snora52 | 1.26 | 0.90 | 0.99 | 0.85 | 1.13 | 0.79 | 0.84 | 0.75 | 0.43 | 10.49 | 1.00 | 1.00 |
| Snora5c | 1.13 | 2.08 | 0.55 | 1.21 | 0.51 | 1.33 | 0.82 | 2.16 | 1.02 | 1.00 | 1.00 | 1.00 |
| Snora61 | 0.28 | 1.08 | 1.23 | 1.08 | 1.48 | 1.13 | 0.79 | 1.12 | 1.17 | 1.00 | 0.82 | 4.60 |
| Snora62 | 0.29 | 1.07 | 2.37 | 0.34 | 2.49 | 2.29 | 1.11 | 0.74 | 3.36 | 1.00 | 0.54 | 0.76 |
| Snora64 | 0.86 | 0.95 | 1.52 | 0.87 | 0.67 | 1.33 | 1.04 | 0.63 | 2.47 | 35.59 | 1.00 | 1.00 |
| Snora68 | 0.92 | 1.08 | 0.84 | 1.03 | 0.71 | 0.84 | 1.13 | 0.77 | 1.72 | 1.00 | 5.70 | 2.07 |
| Snora69 | 1.06 | 0.94 | 0.94 | 0.45 | 2.63 | 1.74 | 0.74 | 3.75 | 4.04 | 0.03 | 0.91 | 1.00 |
| Snora75 | 1.35 | 1.08 | 1.35 | 1.36 | 0.38 | 0.74 | 1.32 | 1.11 | 0.63 | 1.00 | 1.00 | 1.00 |
| Snord100 | 1.18 | 1.28 | 0.79 | 1.31 | 0.80 | 1.75 | 0.37 | 3.24 | 0.72 | 1.00 | 1.00 | 1.00 |
| Snord11 | 48.80 | 0.01 | 0.96 | 1.06 | 1.00 | 1.00 | 1.00 | 1.00 | 1.00 | 1.00 | 1.00 | 1.00 |
| Snord110 | 0.01 | 1.47 | 1.09 | 2.26 | 0.02 | 142.03 | 33.79 | 0.02 | 1.00 | 1.00 | 1.00 | 1.00 |
| Snord111 | 0.03 | 41.82 | 52.00 | 41.77 | 0.01 | 0.03 | 1.00 | 1.00 | 1.00 | 1.00 | 1.00 | 1.00 |
| Snord116 | 1.00 | 1.00 | 1.00 | 1.00 | 1.00 | 1.00 | 1.00 | 1.00 | 1.00 | 1.00 | 1.00 | 1.00 |
| Snord116l1 | 1.00 | 1.00 | 1.00 | 1.00 | 1.00 | 1.00 | 1.00 | 1.00 | 1.00 | 1.00 | 1.00 | 1.00 |
| Snord12 | 0.89 | 1.16 | 0.72 | 1.06 | 0.69 | 0.90 | 0.40 | 0.21 | 0.40 | 1.00 | 1.00 | 1.00 |
| Snord123 | 3.28 | 3.56 | 22.85 | 1.00 | 1.00 | 1.00 | 0.66 | 2.00 | 0.65 | 1.00 | 3.11 | 1.84 |
| Snord16a | 1.02 | 0.78 | 0.79 | 1.58 | 1.12 | 1.30 | 1.42 | 2.30 | 0.89 | 1.00 | 1.00 | 1.00 |
| Snord19 | 0.58 | 2.76 | 0.98 | 268.76 | 243.90 | 1.19 | 0.02 | 1.00 | 0.01 | 1.00 | 1.00 | 1.00 |
| Snord1a | 0.02 | 1.00 | 67.45 | 1.00 | 1.00 | 1.00 | 1.00 | 1.00 | 6.73 | 1.00 | 1.00 | 1.00 |
| Snord1b | 0.58 | 0.67 | 3.92 | 3.68 | 0.02 | 1.83 | 1.00 | 1.00 | 1.00 | 1.00 | 1.00 | 1.00 |
| Snord1c | 1.00 | 1.04 | 0.66 | 31.70 | 1.00 | 0.59 | 1.00 | 1.00 | 1.00 | 1.00 | 3.26 | 6.38 |
| Snord23 | 0.31 | 2.60 | 0.67 | 4.49 | 0.92 | 0.83 | 0.77 | 0.21 | 1.00 | 1.00 | 1.00 | 1.00 |
| Snord34 | 1.97 | 0.69 | 0.81 | 1.01 | 0.85 | 0.32 | 1.42 | 1.20 | 58.71 | 1.00 | 1.00 | 1.00 |
| Snord35b | 0.86 | 1.58 | 1.15 | 1.13 | 0.68 | 1.24 | 0.75 | 0.34 | 1.79 | 1.00 | 1.00 | 1.00 |
| Snord37 | 1.04 | 0.38 | 0.41 | 1.44 | 0.48 | 0.57 | 115.23 | 0.57 | 0.52 | 1.00 | 1.00 | 1.00 |
| Snord38a | 125.94 | 0.02 | 4.06 | 0.02 | 0.44 | 1.22 | 1.00 | 0.02 | 1.00 | 1.00 | 1.00 | 1.00 |
| Snord42a | 0.56 | 1.04 | 1.00 | 0.00 | 0.33 | 1.00 | 1.00 | 1.00 | 1.00 | 1.00 | 1.00 | 1.00 |
| Snord42b | 1.20 | 1.74 | 1.37 | 0.43 | 219.45 | 0.01 | 1.00 | 1.00 | 0.01 | 1.00 | 1.00 | 1.00 |
| Snord45b | 0.47 | 0.75 | 1.00 | 1.24 | 289.89 | 1.00 | 1.45 | 0.00 | 1.00 | 1.00 | 1.00 | 1.00 |
| Snord45c | 7.74 | 1.22 | 0.26 | 0.16 | 1.96 | 1.43 | 2.37 | 1.00 | 1.00 | 1.00 | 1.00 | 1.00 |
| Snord49a | 1.12 | 0.59 | 2.02 | 1.14 | 1.43 | 1.05 | 1.02 | 0.34 | 0.33 | 1.00 | 1.00 | 1.00 |
| Snord49b | 0.54 | 0.36 | 1.29 | 1.80 | 0.67 | 0.67 | 4.08 | 2.98 | 1.00 | 1.00 | 1.00 | 1.00 |
| Snord4a | 2.74 | 1.74 | 0.92 | 0.74 | 0.66 | 1.58 | 1.41 | 0.02 | 1.54 | 1.00 | 1.00 | 1.00 |
| Snord52 | 2.21 | 0.99 | 0.73 | 0.69 | 1.87 | 0.54 | 1.00 | 0.02 | 1.00 | 1.00 | 1.00 | 1.00 |
| Snord53 | 0.94 | 0.01 | 0.36 | 0.57 | 0.01 | 0.01 | 0.02 | 0.05 | 1.00 | 1.00 | 1.00 | 1.00 |
| Snord55 | 1.35 | 1.75 | 1.77 | 2.35 | 0.58 | 0.69 | 1.20 | 0.03 | 1.17 | 1.00 | 1.00 | 1.00 |
| Snord57 | 0.42 | 0.99 | 1.09 | 0.33 | 0.67 | 0.75 | 0.85 | 0.03 | 1.00 | 1.00 | 1.00 | 1.00 |
| Snord58b | 1.10 | 1.46 | 2.05 | 1.53 | 1.26 | 2.01 | 3.41 | 148.86 | 179.14 | 1.00 | 1.00 | 1.00 |
| Snord61 | 1.00 | 40.97 | 1.00 | 1.00 | 1.00 | 1.00 | 1.00 | 1.00 | 1.00 | 1.00 | 1.00 | 1.00 |
| Snord64 | 1.00 | 1.00 | 1.00 | 1.00 | 1.00 | 1.00 | 1.00 | 1.00 | 1.00 | 1.00 | 1.00 | 1.00 |
| Snord65 | 1.01 | 1.06 | 2.55 | 1.44 | 0.50 | 0.00 | 0.36 | 1.00 | 1.00 | 1.00 | 1.00 | 1.00 |
| Snord66 | 0.77 | 0.67 | 0.01 | 2.66 | 0.02 | 3.04 | 2.43 | 50.16 | 0.01 | 1.00 | 1.00 | 1.00 |
| Snord67 | 7.08 | 0.05 | 7.63 | 0.08 | 6.30 | 0.18 | 1.00 | 1.00 | 0.17 | 1.00 | 1.00 | 1.00 |
| Snord68 | 0.01 | 0.45 | 0.00 | 210.76 | 0.01 | 1.00 | 1.00 | 1.00 | 1.00 | 1.00 | 1.00 | 1.00 |
| Snord69 | 0.74 | 0.50 | 0.85 | 0.49 | 3.46 | 0.24 | 0.64 | 0.18 | 0.01 | 1.00 | 1.00 | 1.00 |
| Snord7 | 13.83 | 0.04 | 47.11 | 2.92 | 1.00 | 5.39 | 6.03 | 0.28 | 0.89 | 1.00 | 1.00 | 1.00 |

Fig. 31-105

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Snord70 | 1.00 | 1.00 | 1.00 | 1.00 | 1.00 | 1.00 | 256.59 | 1.00 | 1.00 |
| Snord71 | 0.31 | 0.02 | 0.23 | 1.00 | 1.00 | 0.02 | 1.00 | 1.00 | 0.97 |
| Snord72 | 1.75 | 0.30 | 0.92 | 145.88 | 0.01 | 0.01 | 0.01 | 0.39 | 1.71 |
| Snord73a | 1.68 | 1.00 | 1.00 | 0.01 | 1.00 | 1.00 | 0.02 | 1.00 | 0.02 |
| Snord8 | 0.46 | 22.25 | 1.00 | 0.42 | 1.52 | 1.01 | 0.05 | 6.60 | 3.29 |
| Snord82 | 1.00 | 1.00 | 1.00 | 1.00 | 1.00 | 1.00 | 1.00 | 1.00 | 1.00 |
| Snord83b | 3.32 | 2.12 | 1.70 | 0.01 | 1.00 | 78.26 | 0.92 | 5.41 | 1.00 |
| Snord85 | 1.00 | 1.00 | 1.00 | 1.00 | 1.00 | 1.00 | 1.00 | 1.00 | 1.00 |
| Snord87 | 2.48 | 3.44 | 0.23 | 0.70 | 1.16 | 2.04 | 0.48 | 23.88 | 0.01 |
| Snord88a | 0.04 | 0.84 | 1.00 | 1.00 | 42.68 | 0.01 | 1.00 | 1.00 | 0.05 |
| Snord88c | 0.42 | 4.13 | 4.19 | 1.96 | 0.02 | 0.36 | 15.00 | 25.69 | 0.03 |
| Snord89 | 1.24 | 1.02 | 0.90 | 0.70 | 0.71 | 1.89 | 0.84 | 0.84 | 5.84 |
| Snord90 | 1.00 | 1.00 | 0.03 | 1.00 | 1.00 | 1.00 | 1.00 | 1.00 | 1.00 |
| Snord92 | 1.00 | 0.07 | 1.00 | 1.00 | 1.00 | 1.00 | 1.00 | 1.00 | 1.00 |
| Snord93 | 5.32 | 0.44 | 1276.50 | 1.00 | 1.00 | 1.00 | 1.00 | 1.00 | 1.00 |
| Snord95 | 0.87 | 110.48 | 0.15 | 51.44 | 1.15 | 2.03 | 45.51 | 2.10 | 3.42 |
| Snord99 | 80.28 | 225.83 | 1.00 | 1.00 | 1.00 | 155.17 | 0.52 | 0.82 | 3.51 |
| Spag11a | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 |
| Spag5 | 1.00 | 1.41 | 1.00 | 1.85 | 1.60 | 1.11 | 1.00 | 1.50 | 1.00 |
| Spata3 | 1.00 | 1.00 | 1.00 | 1.00 | 1.00 | 1.00 | 1.00 | 1.00 | 1.00 |
| Spdef | 1.00 | 1.84 | 1.00 | 1.00 | 1.50 | 1.00 | 1.00 | 1.00 | 1.00 |
| Sphk1 | 9.15 | 3.08 | 2.57 | 1.61 | 1.28 | 1.12 | 1.00 | 1.00 | 1.00 |
| Spib | 1.00 | 2.60 | 1.06 | 1.00 | 1.38 | 1.00 | 1.00 | 6.75 | 1.00 |
| Spin2c | 1.00 | 1.00 | 1.00 | 0.88 | 1.00 | 1.00 | 1.00 | 1.00 | 1.00 |
| Spink10 | 1.00 | 1.00 | 1.00 | 1.00 | 1.00 | 1.00 | 1.00 | 1.00 | 1.00 |
| Spink11 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 |
| Spink2 | 1.00 | 0.87 | 1.00 | 1.00 | 1.00 | 1.00 | 1.00 | 1.00 | 1.00 |
| Spink5 | 1.00 | 1.00 | 1.00 | 1.00 | 1.00 | 1.00 | 1.00 | 1.00 | 1.00 |
| Spink8 | 1.00 | 1.00 | 1.00 | 0.69 | 1.01 | 0.76 | 1.00 | 1.00 | 1.00 |
| Spinkl | 1.00 | 1.00 | 1.00 | 1.00 | 1.00 | 1.00 | 1.00 | 1.00 | 1.00 |
| Spint4 | 1.00 | 1.00 | 1.00 | 1.00 | 1.00 | 1.00 | 1.00 | 1.00 | 1.00 |
| Spint5 | 1.00 | 1.00 | 1.00 | 1.00 | 1.00 | 1.00 | 1.00 | 1.00 | 1.00 |
| Spp1 | 5.69 | 19.73 | 10.79 | 0.95 | 0.88 | 0.66 | 0.62 | 1.00 | 1.25 |
| Sprr1a | 1.12 | 18.52 | 13.02 | 1.24 | 2.24 | 1.26 | 1.00 | 1.00 | 1.00 |
| Sprr2f | 1.00 | 1.00 | 1.00 | 1.00 | 1.00 | 1.94 | 1.00 | 1.00 | 1.00 |
| Sprr3 | 1.00 | 1.00 | 1.00 | 1.00 | 1.00 | 1.00 | 1.00 | 1.00 | 1.00 |
| Ss18l1 | 0.92 | 1.05 | 1.01 | 1.06 | 1.19 | 1.02 | 1.16 | 0.92 | 0.95 |
| St6gal1 | 1.05 | 1.35 | 1.20 | 0.93 | 1.06 | 1.11 | 1.07 | 1.17 | 0.95 |
| St8sia5 | 1.00 | 1.00 | 1.00 | 1.00 | 1.00 | 1.00 | 1.00 | 1.00 | 1.00 |
| Stambpl1 | 1.45 | 2.26 | 1.13 | 1.00 | 1.47 | 1.00 | 1.00 | 4.99 | 1.00 |
| Stap1 | 1.00 | 2.18 | 1.03 | 0.75 | 1.04 | 0.87 | 1.00 | 1.00 | 0.82 |
| Stc1 | 4.49 | 2.01 | 1.00 | 1.94 | 1.69 | 1.01 | 1.00 | 1.00 | 1.00 |
| Steap4 | 0.74 | 0.98 | 1.35 | 0.75 | 0.73 | 1.41 | 1.13 | 1.06 | 1.37 |
| Stfa2l1 | 5.01 | 1.01 | 1.00 | 1.00 | 1.00 | 1.00 | 1.00 | 1.00 | 1.00 |
| Stmn1 | 0.75 | 1.08 | 0.85 | 1.20 | 0.98 | 0.90 | 1.73 | 5.70 | 1.17 |
| Sult2b1 | 1.00 | 1.00 | 1.00 | 0.90 | 1.00 | 1.00 | 1.00 | 1.00 | 1.00 |
| Susd1 | 1.00 | 1.45 | 1.01 | 1.33 | 1.29 | 0.60 | 1.40 | 1.50 | 0.59 |
| Svs5 | 1.00 | 1.00 | 1.00 | 1.00 | 1.00 | 1.00 | 1.00 | 1.00 | 1.00 |
| Syk | 1.27 | 1.40 | 0.98 | 0.87 | 2.30 | 1.04 | 0.74 | 6.11 | 0.92 |
| Syndig1l | 1.00 | 1.00 | 1.00 | 1.00 | 1.00 | 1.00 | 1.00 | 1.43 | 1.00 |
| Synpr | 1.00 | 1.00 | 1.00 | 1.31 | 1.00 | 6.32 | 1.00 | 1.00 | 1.00 |
| Sytl4 | 0.91 | 1.03 | 1.59 | 0.89 | 1.13 | 1.40 | 1.00 | 1.00 | 1.00 |
| Tacstd2 | 1.00 | 1.00 | 1.23 | 0.95 | 0.82 | 1.03 | 1.00 | 1.00 | 1.00 |
| Tcf7 | 2.59 | 0.73 | 2.02 | 1.00 | 1.00 | 1.00 | 0.86 | 0.86 | 0.91 |
| Tchh | 1.01 | 1.09 | 0.82 | 0.74 | 0.69 | 1.18 | 1.00 | 1.00 | 1.00 |
| Tdrd5 | 1.00 | 1.00 | 1.00 | 1.03 | 1.79 | 2.15 | 1.00 | 1.00 | 1.00 |
| Teddm1 | 1.00 | 1.00 | 1.00 | 1.00 | 1.00 | 1.00 | 1.00 | 1.00 | 1.00 |
| Tfap2a | 1.00 | 1.00 | 1.00 | 0.96 | 1.01 | 0.99 | 1.00 | 1.00 | 1.00 |
| Tfap2b | 1.00 | 1.00 | 1.00 | 1.15 | 1.12 | 0.87 | 1.00 | 1.00 | 1.00 |
| Tff2 | 1.00 | 1.00 | 1.00 | 1.00 | 1.00 | 1.00 | 1.00 | 1.00 | 1.00 |
| Tgm3 | 1.00 | 1.00 | 1.00 | 1.00 | 1.00 | 1.00 | 1.00 | 1.00 | 1.00 |
| Thbs1 | 7.02 | 4.28 | 7.07 | 1.03 | 1.13 | 1.19 | 1.00 | 1.39 | 1.00 |

Fig. 31-106

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Snord70 | 1.00 | 105.68 | 1.00 | 1.00 | 0.01 | 1.00 | 1.00 | 1.00 | 1.00 |
| Snord71 | 2.02 | 2.12 | 1.10 | 1.00 | 0.03 | 70.84 | 196.00 | 164.66 | 0.22 |
| Snord72 | 1.00 | 1.64 | 0.00 | 0.92 | 0.02 | 0.98 | 2.09 | 1.32 | 0.30 |
| Snord73a | 0.51 | 2.57 | 0.72 | 0.02 | 0.04 | 51.37 | 1.44 | 0.54 | 1.79 |
| Snord8 | 2.58 | 6.46 | 1.06 | 6.83 | 1.00 | 0.32 | 0.97 | 2.95 | 0.56 |
| Snord82 | 1.00 | 1.00 | 1.00 | 1.00 | 1.00 | 1.00 | 1.00 | 1.00 | 1.00 |
| Snord83b | 4.16 | 4.12 | 2.20 | 0.71 | 0.53 | 0.06 | 1.51 | 1.71 | 1.27 |
| Snord85 | 1.00 | 1.00 | 1.00 | 1.00 | 1.00 | 1.00 | 1.00 | 1.00 | 1.00 |
| Snord87 | 1.40 | 1.26 | 2.19 | 0.47 | 0.03 | 37.30 | 1.08 | 0.51 | 0.92 |
| Snord88a | 20.07 | 1.10 | 0.05 | 1.00 | 1.00 | 1.00 | 1.51 | 6.59 | 0.01 |
| Snord88c | 0.44 | 3.19 | 1.33 | 0.60 | 10.53 | 11.14 | 2.47 | 0.35 | 0.93 |
| Snord89 | 0.67 | 1.03 | 0.54 | 0.40 | 0.68 | 0.93 | 2.34 | 1.11 | 0.68 |
| Snord90 | 1.00 | 1.00 | 1.00 | 1.00 | 1.00 | 1.00 | 1.00 | 1.00 | 1.00 |
| Snord92 | 1.00 | 1.00 | 1.00 | 1.00 | 1.00 | 1.00 | 1.00 | 1.00 | 1.00 |
| Snord93 | 1.98 | 1.10 | 1.14 | 1.00 | 733.25 | 389.49 | 1.00 | 1.00 | 1.00 |
| Snord95 | 0.44 | 4.53 | 0.73 | 0.46 | 0.04 | 1.00 | 0.83 | 1.58 | 1.67 |
| Snord99 | 275.99 | 2.02 | 0.65 | 0.00 | 2.03 | 76.32 | 1.83 | 1.15 | 1.28 |
| Spag11a | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 |
| Spag5 | 1.50 | 6.55 | 1.00 | 0.55 | 0.71 | 0.64 | 0.98 | 1.39 | 3.09 |
| Spata3 | 1.00 | 1.00 | 1.00 | 1.00 | 1.00 | 0.88 | 1.00 | 1.00 | 1.00 |
| Spdef | 0.89 | 2.66 | 1.03 | 1.00 | 2.01 | 1.00 | 1.35 | 1.00 | 1.00 |
| Sphk1 | 2.08 | 1.06 | 0.84 | 1.00 | 1.06 | 1.00 | 0.80 | 1.19 | 2.43 |
| Spib | 0.34 | 10.00 | 0.80 | 1.00 | 1.05 | 1.00 | 0.98 | 0.86 | 0.77 |
| Spin2c | 1.00 | 1.00 | 0.97 | 1.00 | 1.00 | 1.00 | 1.01 | 1.00 | 0.96 |
| Spink10 | 1.00 | 1.00 | 1.00 | 1.00 | 1.00 | 1.00 | 1.00 | 1.00 | 1.00 |
| Spink11 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 |
| Spink2 | 1.04 | 0.58 | 1.00 | 1.00 | 1.00 | 0.68 | 1.00 | 1.00 | 1.00 |
| Spink5 | 1.00 | 1.00 | 0.92 | 1.00 | 1.00 | 1.00 | 1.00 | 1.00 | 1.00 |
| Spink8 | 1.00 | 1.00 | 1.00 | 1.00 | 1.00 | 1.00 | 1.00 | 1.00 | 1.00 |
| Spinkl | 1.00 | 1.00 | 1.00 | 0.29 | 1.08 | 1.00 | 1.00 | 1.00 | 1.00 |
| Spint4 | 1.00 | 1.00 | 1.00 | 1.00 | 1.00 | 1.00 | 1.00 | 1.00 | 1.00 |
| Spint5 | 1.00 | 1.00 | 1.00 | 1.00 | 1.00 | 1.00 | 1.00 | 1.00 | 1.00 |
| Spp1 | 3.13 | 1.40 | 1.15 | 0.74 | 0.11 | 0.16 | 1.25 | 0.39 | 0.52 |
| Sprr1a | 1.00 | 0.99 | 1.37 | 1.00 | 1.00 | 1.00 | 1.00 | 1.00 | 1.00 |
| Sprr2f | 1.00 | 1.00 | 1.00 | 1.00 | 1.00 | 1.00 | 1.00 | 1.00 | 1.00 |
| Sprr3 | 1.00 | 1.00 | 1.00 | 1.00 | 1.00 | 1.00 | 1.00 | 1.00 | 1.00 |
| Ss18l1 | 1.05 | 1.09 | 0.94 | 1.12 | 1.17 | 0.84 | 1.34 | 0.98 | 0.90 |
| St6gal1 | 0.87 | 0.97 | 1.13 | 1.03 | 0.85 | 1.07 | 0.98 | 1.00 | 0.84 |
| St8sia5 | 1.00 | 1.00 | 1.00 | 0.54 | 0.94 | 1.06 | 1.00 | 1.00 | 1.00 |
| Stambpl1 | 1.01 | 6.54 | 1.23 | 1.00 | 1.27 | 1.00 | 1.19 | 0.85 | 0.89 |
| Stap1 | 0.33 | 2.43 | 0.93 | 1.00 | 1.00 | 1.00 | 0.82 | 0.94 | 0.85 |
| Stc1 | 1.54 | 1.56 | 0.69 | 1.14 | 1.11 | 1.00 | 0.99 | 1.00 | 1.00 |
| Steap4 | 1.06 | 1.21 | 1.56 | 0.90 | 1.09 | 1.63 | 0.83 | 0.83 | 1.32 |
| Stfa2l1 | 1.06 | 1.11 | 1.05 | 1.00 | 1.00 | 1.00 | 0.92 | 1.71 | 1.09 |
| Stmn1 | 0.89 | 1.97 | 0.77 | 0.87 | 0.62 | 1.03 | 0.75 | 1.21 | 2.41 |
| Sult2b1 | 0.54 | 0.80 | 1.72 | 1.00 | 1.00 | 1.00 | 1.00 | 1.00 | 1.00 |
| Susd1 | 1.05 | 5.82 | 0.97 | 1.09 | 1.35 | 1.00 | 0.86 | 0.93 | 1.12 |
| Svs5 | 1.00 | 1.00 | 1.00 | 0.02 | 7.16 | 1.00 | 1.00 | 1.00 | 1.00 |
| Syk | 0.84 | 3.30 | 1.03 | 1.03 | 0.84 | 1.30 | 0.96 | 0.86 | 0.81 |
| Syndig1l | 1.00 | 5.27 | 1.00 | 1.00 | 1.00 | 1.00 | 1.00 | 1.00 | 1.00 |
| Synpr | 1.00 | 1.00 | 1.00 | 1.00 | 1.00 | 1.00 | 1.00 | 1.00 | 1.00 |
| Sytl4 | 0.83 | 0.89 | 0.86 | 1.00 | 1.00 | 1.00 | 0.72 | 0.67 | 0.76 |
| Tacstd2 | 0.72 | 1.02 | 1.11 | 1.00 | 1.00 | 1.00 | 0.93 | 0.91 | 1.19 |
| Tcf7 | 0.71 | 0.84 | 0.97 | 1.00 | 1.00 | 1.00 | 1.22 | 1.40 | 0.75 |
| Tchh | 0.83 | 0.61 | 1.10 | 1.00 | 1.00 | 1.00 | 1.00 | 1.00 | 1.00 |
| Tdrd5 | 0.94 | 1.00 | 1.03 | 1.00 | 1.00 | 1.00 | 1.00 | 1.00 | 1.00 |
| Teddm1 | 1.00 | 1.00 | 1.00 | 1.00 | 1.00 | 1.00 | 1.00 | 1.00 | 1.00 |
| Tfap2a | 1.00 | 1.00 | 1.00 | 1.00 | 1.00 | 1.00 | 1.00 | 1.00 | 1.00 |
| Tfap2b | 1.00 | 1.00 | 1.00 | 1.00 | 1.00 | 1.00 | 1.00 | 1.00 | 1.00 |
| Tff2 | 0.58 | 1.16 | 1.65 | 1.00 | 1.00 | 1.00 | 1.23 | 0.08 | 0.01 |
| Tgm3 | 1.00 | 1.00 | 1.00 | 1.00 | 1.00 | 1.00 | 1.00 | 1.00 | 1.00 |
| Thbs1 | 4.03 | 2.35 | 3.07 | 1.74 | 0.74 | 1.52 | 0.65 | 0.70 | 0.67 |

Fig. 31-107

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Snord70 | 1.00 | 1.00 | 1.00 | 1.00 | 1.00 | 1.00 | 1.00 | 1.00 | 1.00 |
| Snord71 | 99.59 | 86.33 | 1.00 | 97.95 | 0.01 | 1.00 | 0.00 | 2.77 | 0.65 |
| Snord72 | 0.90 | 1.00 | 87.75 | 1.00 | 546.63 | 2.22 | 0.02 | 86.11 | 1.00 |
| Snord73a | 1.00 | 1.02 | 0.03 | 57.41 | 0.64 | 1.60 | 1.08 | 0.04 | 0.51 |
| Snord8 | 1.00 | 14.98 | 0.06 | 7.98 | 1.64 | 0.59 | 2.57 | 0.37 | 0.70 |
| Snord82 | 1.00 | 1.00 | 1.00 | 1.00 | 1.00 | 1.00 | 1.00 | 24.66 | 1.00 |
| Snord83b | 2.19 | 1.48 | 0.44 | 0.19 | 76.22 | 0.54 | 1.08 | 54.52 | 0.98 |
| Snord85 | 1.00 | 1.00 | 1.00 | 1.00 | 1.00 | 1.00 | 34.91 | 1.00 | 1.00 |
| Snord87 | 2.35 | 1.00 | 3.09 | 0.89 | 1.31 | 0.51 | 1.08 | 0.29 | 0.51 |
| Snord88a | 44.27 | 0.03 | 81.51 | 1.00 | 143.59 | 1.00 | 0.54 | 17.74 | 1.00 |
| Snord88c | 0.32 | 1.82 | 1.02 | 34.57 | 1.14 | 4.31 | 11.59 | 0.92 | 0.04 |
| Snord89 | 2.47 | 0.28 | 0.61 | 1.19 | 2.84 | 0.59 | 0.63 | 0.91 | 1.73 |
| Snord90 | 1.00 | 1.00 | 1.00 | 1.00 | 1.00 | 1.00 | 1.00 | 1.00 | 24.21 |
| Snord92 | 1.00 | 1.00 | 1.00 | 1.00 | 1.00 | 1.00 | 1.00 | 1.00 | 11.62 |
| Snord93 | 1.00 | 1.00 | 1.00 | 1.00 | 1.00 | 1.00 | 1.12 | 0.00 | 2.26 |
| Snord95 | 0.02 | 110.63 | 0.01 | 0.01 | 0.01 | 1.01 | 1.00 | 0.48 | 50.24 |
| Snord99 | 1.00 | 1.00 | 1.00 | 1.00 | 1.00 | 1.00 | 0.01 | 0.89 | 1.00 |
| Spag11a | 1.00 | 1.00 | 1.00 | 1.00 | 353.13 | 1.00 | 1.00 | 1.00 | 1.00 |
| Spag11b | 1.00 | 1.00 | 1.00 | 1.00 | 320.27 | 1.00 | 1.00 | 1.00 | 1.00 |
| Spag5 | 1.26 | 1.09 | 1.06 | 1.00 | 1.00 | 1.00 | 0.99 | 0.98 | 0.94 |
| Spata3 | 1.00 | 1.00 | 1.00 | 1.00 | 7.45 | 1.00 | 1.11 | 0.95 | 1.06 |
| Spdef | 1.00 | 9.37 | 1.00 | 1.00 | 2.92 | 1.00 | 0.70 | 1.67 | 1.20 |
| Sphk1 | 0.95 | 1.13 | 0.91 | 1.30 | 1.06 | 1.64 | 0.82 | 1.05 | 0.87 |
| Spib | 1.00 | 3.45 | 1.00 | 1.01 | 2.00 | 0.25 | 1.00 | 1.00 | 1.00 |
| Spin2c | 1.08 | 1.14 | 0.98 | 1.00 | 6.45 | 1.00 | 1.00 | 1.00 | 1.00 |
| Spink10 | 0.73 | 1.04 | 1.00 | 1.00 | 5.91 | 1.00 | 1.00 | 1.00 | 1.00 |
| Spink11 | 1.00 | 1.00 | 1.00 | 1.00 | 1251.70 | 1.00 | 1.00 | 1.00 | 1.00 |
| Spink12 | 1.00 | 1.00 | 1.00 | 1.00 | 152.93 | 1.00 | 1.00 | 1.00 | 1.00 |
| Spink2 | 1.00 | 1.00 | 1.00 | 1.24 | 194.71 | 0.78 | 1.09 | 1.01 | 1.02 |
| Spink5 | 1.00 | 1.00 | 1.00 | 1.00 | 108.13 | 1.00 | 1.00 | 1.00 | 1.00 |
| Spink8 | 1.05 | 1.11 | 0.85 | 1.00 | 19.82 | 1.00 | 3.42 | 1.43 | 1.53 |
| Spinkl | 1.00 | 1.00 | 1.00 | 1.00 | 8.78 | 1.00 | 1.00 | 1.00 | 1.00 |
| Spint4 | 1.00 | 1.00 | 1.00 | 1.00 | 727.73 | 1.00 | 1.00 | 1.00 | 1.00 |
| Spint5 | 1.00 | 1.00 | 1.00 | 1.00 | 489.42 | 1.00 | 1.23 | 0.96 | 1.08 |
| Spp1 | 1.03 | 1.03 | 0.96 | 11.88 | 0.59 | 0.99 | 0.96 | 0.69 | 1.17 |
| Sprr1a | 1.00 | 1.00 | 1.00 | 1.00 | 1.00 | 1.00 | 1.00 | 1.00 | 1.00 |
| Sprr2f | 1.00 | 1.00 | 1.00 | 1.00 | 1.00 | 1.00 | 1.00 | 1.00 | 1.00 |
| Sprr3 | 1.00 | 1.00 | 1.00 | 1.00 | 1.00 | 1.00 | 1.00 | 1.00 | 1.00 |
| Ss18l1 | 1.04 | 1.02 | 0.91 | 0.97 | 5.94 | 1.21 | 0.95 | 0.96 | 1.04 |
| St6gal1 | 1.08 | 1.02 | 0.93 | 1.13 | 30.47 | 0.83 | 0.90 | 0.94 | 1.02 |
| St8sia5 | 0.99 | 0.99 | 1.06 | 1.00 | 8.55 | 1.00 | 0.97 | 0.92 | 0.79 |
| Stambpl1 | 1.02 | 1.31 | 0.97 | 1.31 | 0.91 | 1.14 | 1.02 | 1.14 | 1.00 |
| Stap1 | 1.00 | 1.00 | 1.00 | 0.87 | 9.26 | 0.65 | 1.13 | 0.88 | 0.90 |
| Stc1 | 1.27 | 1.06 | 0.96 | 2.13 | 6.42 | 0.88 | 1.00 | 1.00 | 1.00 |
| Steap4 | 1.00 | 1.22 | 1.00 | 0.58 | 0.71 | 1.39 | 0.74 | 0.92 | 1.19 |
| Stfa2l1 | 1.00 | 1.00 | 1.00 | 3.23 | 1.00 | 1.00 | 1.00 | 1.00 | 1.00 |
| Stmn1 | 0.94 | 0.95 | 1.08 | 0.89 | 0.63 | 0.58 | 1.01 | 0.96 | 1.04 |
| Sult2b1 | 0.89 | 1.01 | 1.14 | 1.00 | 5.34 | 1.00 | 1.18 | 1.04 | 0.66 |
| Susd1 | 0.87 | 1.41 | 0.85 | 1.81 | 1.66 | 0.85 | 1.00 | 1.04 | 1.02 |
| Svs5 | 1.00 | 1.00 | 1.00 | 1.00 | 1.00 | 1.00 | 1.10 | 1.15 | 1.02 |
| Syk | 1.00 | 3.68 | 1.00 | 1.53 | 4.34 | 0.63 | 0.88 | 0.89 | 1.00 |
| Syndig1l | 0.94 | 0.97 | 1.03 | 1.00 | 1.00 | 1.00 | 1.10 | 0.95 | 0.98 |
| Synpr | 0.99 | 0.98 | 0.96 | 1.00 | 1.00 | 1.00 | 1.00 | 1.00 | 1.00 |
| Sytl4 | 0.96 | 0.87 | 0.92 | 0.67 | 9.64 | 0.95 | 0.93 | 0.96 | 0.96 |
| Tacstd2 | 1.00 | 1.00 | 1.00 | 1.00 | 5.26 | 1.00 | 1.00 | 1.00 | 1.00 |
| Tcf7 | 1.00 | 0.92 | 1.04 | 0.55 | 13.47 | 1.00 | 1.04 | 1.04 | 0.97 |
| Tchh | 1.03 | 1.08 | 0.90 | 0.81 | 6.70 | 1.00 | 0.89 | 1.02 | 0.94 |
| Tdrd5 | 1.00 | 1.00 | 1.00 | 1.00 | 1.00 | 1.00 | 0.95 | 1.04 | 1.02 |
| Teddm1 | 1.00 | 1.00 | 1.00 | 1.00 | 13.41 | 1.00 | 1.00 | 1.00 | 1.00 |
| Tfap2a | 1.12 | 1.13 | 1.10 | 1.00 | 5.97 | 1.00 | 1.00 | 1.00 | 1.00 |
| Tfap2b | 1.09 | 1.05 | 1.11 | 1.00 | 22.80 | 1.00 | 1.00 | 1.00 | 1.00 |
| Tff2 | 1.00 | 1.00 | 1.00 | 1.00 | 1.00 | 1.00 | 1.00 | 1.00 | 1.00 |
| Tgm3 | 1.00 | 1.00 | 1.00 | 1.00 | 1.00 | 1.00 | 1.00 | 1.00 | 1.00 |
| Thbs1 | 1.26 | 1.00 | 1.00 | 5.51 | 2.08 | 0.75 | 0.95 | 0.90 | 0.92 |

Fig. 31-108

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Snord70 | 1.00 | 1.00 | 1.00 | 1.13 | 84.54 | 0.01 | 0.01 | 1.00 | 1.00 | 1.00 | 1.00 | 1.00 |
| Snord71 | 1.06 | 0.36 | 2.01 | 2.30 | 0.01 | 0.58 | 0.85 | 30.90 | 35.31 | 1.00 | 1.00 | 1.00 |
| Snord72 | 0.84 | 0.71 | 0.69 | 0.72 | 1.03 | 0.95 | 0.02 | 1.21 | 0.02 | 1.00 | 1.00 | 1.00 |
| Snord73a | 1.22 | 1.48 | 0.33 | 0.64 | 2.46 | 0.01 | 0.75 | 26.62 | 25.52 | 1.00 | 1.00 | 1.00 |
| Snord8 | 0.76 | 1.53 | 0.51 | 1.11 | 0.44 | 0.47 | 1.00 | 0.21 | 0.92 | 1.00 | 1.00 | 1.00 |
| Snord82 | 1.00 | 1.00 | 1.00 | 0.04 | 0.04 | 1.00 | 1.00 | 1.00 | 1.00 | 1.00 | 1.00 | 1.00 |
| Snord83b | 0.78 | 1.18 | 1.16 | 1.12 | 1.23 | 1.12 | 1.15 | 2.53 | 2.25 | 1.00 | 1.00 | 1.00 |
| Snord85 | 42.12 | 1.00 | 0.02 | 38.86 | 0.89 | 1.00 | 1.00 | 1.00 | 1.00 | 1.00 | 1.00 | 1.00 |
| Snord87 | 0.63 | 0.82 | 2.22 | 0.83 | 0.75 | 1.15 | 0.03 | 0.58 | 0.53 | 1.00 | 1.00 | 1.00 |
| Snord88a | 1.38 | 0.80 | 0.51 | 0.02 | 18.75 | 1.00 | 0.81 | 0.06 | 1.00 | 1.00 | 1.00 | 1.00 |
| Snord88c | 1.80 | 1.82 | 1.20 | 0.03 | 0.56 | 0.52 | 1.84 | 0.49 | 0.60 | 1.00 | 1.00 | 1.00 |
| Snord89 | 0.60 | 0.90 | 0.87 | 0.65 | 1.12 | 0.97 | 1.00 | 0.15 | 0.03 | 1.00 | 1.00 | 1.00 |
| Snord90 | 1.00 | 1.00 | 1.00 | 1.00 | 1.00 | 1.00 | 1.00 | 1.00 | 1.00 | 1.00 | 1.00 | 1.00 |
| Snord92 | 1.00 | 1.00 | 1.00 | 1.00 | 1.00 | 1.00 | 1.00 | 1.00 | 1.00 | 1.00 | 1.00 | 1.00 |
| Snord93 | 0.47 | 0.50 | 1.00 | 0.62 | 548.86 | 1.00 | 1.00 | 1.00 | 1.00 | 1.00 | 1.00 | 1.00 |
| Snord95 | 1.22 | 0.57 | 0.33 | 0.74 | 0.75 | 0.83 | 84.53 | 1.76 | 0.01 | 1.00 | 1.00 | 1.00 |
| Snord99 | 0.35 | 0.50 | 0.25 | 1.50 | 1.90 | 0.89 | 2.91 | 0.01 | 79.61 | 1.00 | 0.85 | 1.03 |
| Spag11a | 1.00 | 1.00 | 1.00 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 | 1.00 | 1.00 |
| Spag5 | 0.40 | 0.66 | 0.89 | 1.10 | 0.93 | 1.06 | 1.00 | 1.00 | 1.00 | 1.00 | 1.39 | 1.25 |
| Spata3 | 1.00 | 1.00 | 1.00 | 1.00 | 1.00 | 1.00 | 1.00 | 1.00 | 1.00 | 1.00 | 1.00 | 1.00 |
| Spdef | 1.00 | 1.00 | 1.00 | 1.00 | 1.00 | 1.00 | 0.82 | 0.97 | 1.09 | 3.20 | 1.23 | 1.00 |
| Sphk1 | 0.92 | 0.75 | 1.08 | 1.03 | 0.88 | 1.10 | 1.00 | 1.35 | 1.00 | 0.90 | 1.00 | 1.00 |
| Spib | 1.51 | 2.09 | 1.74 | 0.93 | 0.52 | 0.66 | 1.00 | 1.00 | 0.98 | 1.00 | 1.10 | 0.96 |
| Spin2c | 1.00 | 1.06 | 1.13 | 1.00 | 1.00 | 1.00 | 1.00 | 1.00 | 1.00 | 1.09 | 1.00 | 1.00 |
| Spink10 | 1.00 | 1.00 | 1.00 | 1.00 | 1.00 | 1.00 | 1.00 | 1.00 | 1.00 | 1.00 | 1.00 | 1.00 |
| Spink11 | 1.00 | 1.00 | 1.00 | 1.00 | 1.00 | 1.00 | 1.00 | 1.00 | 1.00 | 1.00 | 1.00 | 1.00 |
| Spink12 | 0.83 | 0.90 | 1.24 | 1.00 | 1.00 | 1.00 | 1.00 | 1.00 | 1.00 | 1.00 | 1.00 | 1.00 |
| Spink2 | 1.00 | 1.00 | 1.00 | 1.00 | 1.00 | 1.00 | 1.00 | 1.00 | 1.00 | 1.00 | 1.00 | 1.00 |
| Spink5 | 1.02 | 0.78 | 1.06 | 1.00 | 1.00 | 1.00 | 1.00 | 1.00 | 1.00 | 1.06 | 1.00 | 1.00 |
| Spink8 | 1.27 | 1.00 | 1.00 | 1.00 | 1.00 | 1.00 | 1.00 | 1.00 | 1.00 | 1.00 | 1.01 | 0.99 |
| Spinkl | 1.00 | 1.00 | 1.00 | 1.00 | 1.00 | 1.00 | 1.00 | 1.00 | 1.00 | 1.00 | 0.91 | 1.01 |
| Spint4 | 1.00 | 1.00 | 1.00 | 1.00 | 1.00 | 1.00 | 1.00 | 1.00 | 1.00 | 1.00 | 0.95 | 1.06 |
| Spint5 | 1.00 | 1.00 | 1.00 | 1.00 | 1.00 | 1.00 | 1.00 | 1.00 | 1.00 | 1.00 | 0.64 | 0.80 |
| Spp1 | 1.06 | 0.41 | 1.19 | 1.15 | 0.71 | 1.45 | 0.94 | 0.80 | 0.86 | 1.42 | 1.14 | 1.03 |
| Sprr1a | 1.10 | 0.90 | 0.77 | 1.00 | 1.00 | 1.00 | 1.00 | 1.00 | 1.00 | 0.80 | 1.94 | 1.13 |
| Sprr2f | 1.25 | 0.80 | 1.00 | 1.00 | 1.00 | 1.00 | 1.00 | 1.00 | 1.00 | 6.56 | 1.13 | 1.07 |
| Sprr3 | 1.00 | 35.78 | 1.00 | 1.00 | 1.00 | 1.00 | 1.00 | 1.00 | 1.00 | 1.00 | 0.73 | 0.90 |
| Ss18l1 | 0.89 | 0.86 | 0.89 | 1.14 | 0.82 | 0.97 | 1.00 | 1.00 | 1.00 | 1.08 | 1.09 | 0.99 |
| St6gal1 | 0.83 | 1.39 | 1.12 | 1.01 | 0.74 | 0.88 | 1.00 | 0.98 | 1.00 | 1.11 | 1.00 | 1.00 |
| St8sia5 | 1.00 | 1.00 | 1.00 | 1.00 | 1.00 | 1.00 | 1.00 | 1.00 | 1.00 | 1.00 | 0.96 | 0.82 |
| Stambpl1 | 0.69 | 1.01 | 1.04 | 0.97 | 0.91 | 0.89 | 0.93 | 0.95 | 0.94 | 0.87 | 1.00 | 1.00 |
| Stap1 | 0.87 | 0.87 | 0.94 | 1.06 | 0.90 | 1.01 | 1.00 | 1.00 | 1.00 | 1.00 | 0.88 | 1.11 |
| Stc1 | 0.98 | 0.97 | 1.06 | 1.00 | 1.00 | 1.00 | 1.00 | 1.00 | 1.00 | 1.64 | 1.00 | 1.00 |
| Steap4 | 1.03 | 1.90 | 2.20 | 0.69 | 7.69 | 1.33 | 1.05 | 1.57 | 1.01 | 1.03 | 1.37 | 1.00 |
| Stfa2l1 | 1.21 | 1.00 | 1.00 | 1.85 | 1.12 | 0.77 | 1.00 | 1.00 | 1.00 | 1.00 | 1.43 | 0.86 |
| Stmn1 | 0.54 | 0.67 | 0.94 | 0.97 | 0.93 | 0.96 | 0.91 | 0.83 | 1.00 | 0.63 | 1.15 | 0.98 |
| Sult2b1 | 1.08 | 1.17 | 0.76 | 1.00 | 1.00 | 1.00 | 1.00 | 1.00 | 1.00 | 0.81 | 1.00 | 1.00 |
| Susd1 | 0.95 | 0.84 | 0.95 | 1.04 | 0.86 | 0.91 | 1.00 | 1.00 | 1.00 | 1.00 | 1.18 | 0.95 |
| Svs5 | 1.00 | 1.00 | 1.00 | 1.00 | 1.00 | 1.00 | 1.00 | 1.00 | 1.00 | 1.00 | 1.12 | 0.98 |
| Syk | 1.14 | 1.90 | 1.60 | 1.02 | 0.93 | 1.01 | 0.96 | 0.85 | 1.00 | 0.91 | 1.00 | 1.00 |
| Syndig1l | 1.12 | 1.00 | 1.00 | 1.00 | 1.00 | 1.00 | 1.00 | 1.00 | 1.00 | 1.00 | 0.89 | 1.01 |
| Synpr | 0.37 | 1.38 | 0.26 | 1.00 | 1.00 | 1.00 | 1.00 | 1.00 | 1.00 | 1.00 | 1.08 | 0.71 |
| Sytl4 | 1.00 | 1.00 | 1.00 | 0.93 | 0.93 | 1.19 | 0.99 | 1.04 | 1.00 | 1.00 | 0.95 | 0.98 |
| Tacstd2 | 1.43 | 1.06 | 0.78 | 0.65 | 0.92 | 1.36 | 1.00 | 1.00 | 1.00 | 1.07 | 0.99 | 1.10 |
| Tcf7 | 0.79 | 0.72 | 0.92 | 1.24 | 1.76 | 1.43 | 0.96 | 0.72 | 0.62 | 0.89 | 1.24 | 0.98 |
| Tchh | 1.17 | 0.71 | 1.04 | 1.00 | 1.00 | 1.00 | 1.00 | 1.00 | 1.00 | 0.50 | 1.02 | 1.00 |
| Tdrd5 | 0.71 | 5.49 | 0.53 | 1.00 | 1.00 | 1.00 | 1.00 | 1.00 | 1.00 | 1.00 | 1.02 | 1.01 |
| Teddm1 | 1.00 | 1.00 | 1.00 | 1.00 | 1.00 | 1.00 | 1.00 | 1.00 | 1.00 | 1.00 | 0.90 | 1.01 |
| Tfap2a | 0.89 | 0.89 | 0.60 | 1.00 | 1.00 | 1.00 | 1.00 | 1.00 | 1.00 | 0.92 | 0.92 | 0.97 |
| Tfap2b | 1.00 | 1.00 | 1.00 | 1.00 | 1.00 | 1.00 | 1.00 | 1.00 | 1.00 | 0.92 | 1.00 | 1.00 |
| Tff2 | 1.11 | 7.01 | 1.00 | 1.00 | 1.00 | 1.00 | 0.64 | 0.80 | 1.17 | 1.00 | 1.10 | 0.91 |
| Tgm3 | 1.00 | 10.69 | 1.00 | 1.00 | 0.73 | 1.00 | 1.00 | 1.00 | 1.00 | 0.89 | 1.10 | 0.90 |
| Thbs1 | 1.39 | 1.69 | 1.51 | 0.85 | 0.80 | 1.03 | 0.86 | 1.00 | 1.01 | 1.12 | 0.85 | 1.02 |

Fig. 31- 109

| Gene Name | Heart | | | Kidney | | | Liver | | |
|---|---|---|---|---|---|---|---|---|---|
| | 1d | 1w | 8w | 1d | 1w | 8w | 1d | 1w | 8w |
| Them5 | 1.00 | 1.00 | 1.00 | 1.00 | 1.00 | 1.00 | 1.00 | 1.00 | 1.00 |
| Tifa | 1.24 | 2.94 | 1.48 | 0.81 | 1.05 | 1.39 | 0.59 | 1.98 | 1.21 |
| Timp1 | 4.50 | 1.81 | 6.28 | 1.00 | 1.00 | 1.15 | 1.00 | 1.00 | 1.00 |
| Tmem132e | 1.00 | 1.13 | 1.00 | 1.00 | 1.00 | 1.00 | 0.95 | 3.28 | 1.00 |
| Tmem150c | 0.64 | 0.49 | 0.65 | 0.99 | 1.17 | 1.02 | 1.00 | 1.00 | 1.00 |
| Tmem30b | 1.00 | 1.00 | 1.00 | 0.99 | 1.31 | 0.89 | 1.26 | 0.81 | 1.06 |
| Tmem51 | 0.66 | 1.78 | 1.30 | 0.74 | 0.88 | 1.06 | 0.49 | 0.86 | 1.33 |
| Tnc | 8.69 | 2.28 | 1.70 | 1.10 | 1.44 | 1.23 | 1.00 | 1.00 | 1.00 |
| Tnnc1 | 0.96 | 0.67 | 0.75 | 0.88 | 0.68 | 1.23 | 1.44 | 1.46 | 0.38 |
| Tnnc2 | 1.00 | 1.00 | 1.00 | 1.00 | 1.00 | 1.00 | 1.00 | 1.00 | 1.00 |
| Tnni2 | 1.48 | 1.90 | 1.36 | 1.00 | 1.00 | 1.00 | 1.00 | 1.00 | 1.00 |
| Tnni3 | 0.76 | 0.50 | 0.57 | 1.00 | 1.00 | 1.00 | 1.00 | 1.00 | 1.00 |
| Tnnt2 | 0.90 | 0.67 | 0.74 | 1.00 | 1.00 | 1.00 | 1.00 | 1.00 | 1.00 |
| Tnnt3 | 1.69 | 3.73 | 1.22 | 1.00 | 1.00 | 1.00 | 1.00 | 1.00 | 1.00 |
| Top2a | 1.51 | 2.74 | 1.25 | 1.00 | 1.45 | 1.00 | 1.00 | 6.82 | 1.00 |
| Tox3 | 1.40 | 1.01 | 0.75 | 1.66 | 1.36 | 0.98 | 1.00 | 1.00 | 1.00 |
| Tpsab1 | 0.56 | 1.19 | 1.00 | 1.00 | 1.00 | 1.00 | 1.00 | 1.00 | 1.00 |
| Tpx2 | 1.05 | 2.44 | 1.00 | 1.00 | 1.00 | 1.00 | 1.00 | 2.20 | 1.00 |
| Trank1 | 1.00 | 1.00 | 1.00 | 1.00 | 1.00 | 1.00 | 1.00 | 1.00 | 1.00 |
| Trem2 | 3.68 | 8.18 | 2.54 | 1.00 | 1.00 | 1.00 | 1.00 | 1.00 | 1.00 |
| Trpc5os | 1.00 | 1.00 | 1.00 | 1.00 | 1.00 | 1.00 | 1.00 | 1.00 | 1.00 |
| Trpm3 | 1.00 | 1.00 | 1.00 | 1.00 | 1.00 | 1.00 | 1.00 | 1.00 | 1.00 |
| Trpv6 | 1.00 | 1.00 | 1.00 | 1.00 | 0.93 | 1.00 | 1.00 | 1.00 | 1.00 |
| Tspan13 | 0.68 | 0.77 | 0.92 | 0.63 | 1.06 | 1.00 | 1.00 | 5.82 | 0.97 |
| Ube2c | 0.94 | 2.30 | 2.14 | 1.00 | 1.09 | 1.00 | 1.00 | 5.67 | 1.00 |
| Ubxn10 | 0.66 | 0.62 | 0.43 | 1.62 | 1.33 | 6.97 | 1.00 | 1.00 | 1.00 |
| Uchl1 | 0.50 | 5.09 | 3.12 | 0.37 | 1.67 | 0.96 | 1.00 | 1.72 | 1.00 |
| Ucp2 | 1.36 | 2.11 | 1.90 | 1.31 | 1.64 | 1.22 | 1.14 | 5.22 | 0.90 |
| Uhrf1 | 1.94 | 2.30 | 1.00 | 1.21 | 1.28 | 1.00 | 1.00 | 5.27 | 1.00 |
| Unc5cl | 1.00 | 1.00 | 1.00 | 1.00 | 1.00 | 1.00 | 1.00 | 1.00 | 1.00 |
| Upk1a | 1.05 | 1.00 | 1.00 | 0.94 | 1.19 | 1.13 | 1.00 | 1.00 | 1.00 |
| Vash2 | 1.00 | 1.00 | 1.00 | 1.00 | 1.00 | 1.00 | 1.00 | 1.00 | 1.00 |
| Vcan | 2.29 | 2.06 | 3.08 | 1.00 | 1.00 | 1.00 | 1.00 | 1.00 | 1.00 |
| Vgll2 | 1.00 | 1.00 | 4.02 | 1.00 | 1.00 | 1.00 | 1.00 | 1.00 | 1.00 |
| Vpreb1 | 1.00 | 8.76 | 1.00 | 1.10 | 4.52 | 1.00 | 1.00 | 37.57 | 1.00 |
| Vpreb2 | 1.00 | 8.79 | 1.00 | 1.00 | 5.91 | 1.00 | 1.00 | 44.48 | 1.00 |
| Vpreb3 | 1.00 | 12.28 | 1.00 | 1.00 | 4.73 | 1.00 | 1.00 | 36.20 | 1.00 |
| Wars | 1.01 | 0.84 | 1.01 | 0.86 | 0.92 | 1.07 | 0.98 | 1.06 | 1.31 |
| Wdfy4 | 1.57 | 3.47 | 1.32 | 1.00 | 1.43 | 1.00 | 1.00 | 5.14 | 1.00 |
| Wfdc10 | 1.00 | 1.00 | 1.00 | 1.00 | 1.00 | 1.00 | 1.00 | 1.00 | 1.00 |
| Wfdc11 | 1.00 | 1.00 | 1.00 | 1.00 | 1.00 | 1.00 | 1.00 | 1.00 | 1.00 |
| Wfdc13 | 1.00 | 1.00 | 1.00 | 1.00 | 1.00 | 1.00 | 1.00 | 1.00 | 1.00 |
| Wfdc2 | 1.22 | 1.00 | 14.44 | 0.87 | 0.92 | 0.86 | 0.98 | 0.57 | 1.27 |
| Wfdc6a | 1.00 | 1.00 | 1.00 | 1.00 | 1.00 | 1.00 | 1.00 | 1.00 | 1.00 |
| Wfdc6b | 1.00 | 1.00 | 1.00 | 1.00 | 1.00 | 1.00 | 1.00 | 1.00 | 1.00 |
| Wfdc8 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 |
| Wisp2 | 0.55 | 6.97 | 5.03 | 1.00 | 1.00 | 1.00 | 1.00 | 1.00 | 1.00 |
| Xkrx | 1.00 | 1.00 | 1.00 | 1.00 | 1.00 | 1.00 | 1.00 | 1.00 | 1.00 |
| Zbtb16 | 2.48 | 0.45 | 0.65 | 11.22 | 1.86 | 0.36 | 10.65 | 1.29 | 0.21 |
| Zfp648 | 1.00 | 1.00 | 1.00 | 1.45 | 1.10 | 1.18 | 1.00 | 1.00 | 1.00 |
| Zfp697 | 7.20 | 3.49 | 3.02 | 1.23 | 1.28 | 1.15 | 1.00 | 1.00 | 1.00 |
| Zim1 | 1.00 | 1.00 | 1.00 | 1.87 | 1.00 | 1.00 | 1.00 | 1.00 | 1.00 |

Fig. 31- 110

| Gene Name | Lung | | | Skeletal muscle | | | Spleen | | |
|---|---|---|---|---|---|---|---|---|---|
| | 1d | 1w | 8w | 1d | 1w | 8w | 1d | 1w | 8w |
| Them5 | 1.00 | 1.00 | 1.00 | 1.00 | 1.00 | 1.00 | 1.00 | 1.00 | 1.00 |
| Tifa | 0.89 | 10.71 | 1.35 | 0.86 | 1.62 | 1.05 | 0.94 | 1.17 | 1.37 |
| Timp1 | 2.61 | 1.33 | 1.39 | 0.65 | 0.77 | 0.26 | 0.99 | 0.85 | 0.84 |
| Tmem132e | 1.00 | 11.58 | 1.00 | 1.00 | 1.00 | 1.00 | 1.00 | 1.00 | 1.00 |
| Tmem150c | 0.74 | 1.11 | 0.77 | 1.00 | 1.00 | 1.00 | 0.89 | 1.03 | 0.66 |
| Tmem30b | 1.02 | 0.78 | 1.00 | 1.00 | 1.00 | 1.00 | 1.17 | 1.00 | 1.00 |
| Tmem51 | 0.87 | 0.99 | 1.11 | 1.00 | 1.00 | 1.00 | 0.80 | 0.78 | 0.93 |
| Tnc | 4.90 | 1.93 | 3.45 | 0.89 | 0.74 | 0.43 | 1.00 | 1.00 | 1.00 |
| Tnnc1 | 1.02 | 1.27 | 1.18 | 1.88 | 1.39 | 1.15 | 1.00 | 1.00 | 1.00 |
| Tnnc2 | 1.00 | 1.00 | 1.00 | 0.96 | 0.95 | 1.01 | 1.00 | 1.00 | 1.03 |
| Tnni2 | 0.97 | 1.11 | 0.69 | 1.08 | 0.99 | 0.97 | 0.90 | 0.61 | 0.89 |
| Tnni3 | 0.66 | 0.62 | 0.99 | 1.00 | 3.16 | 1.00 | 1.10 | 0.77 | 0.72 |
| Tnnt2 | 0.78 | 1.21 | 1.15 | 0.46 | 3.52 | 1.44 | 1.00 | 1.00 | 1.00 |
| Tnnt3 | 0.87 | 1.13 | 0.68 | 1.08 | 0.94 | 0.96 | 1.01 | 1.00 | 0.88 |
| Top2a | 2.08 | 8.81 | 1.12 | 1.00 | 0.86 | 1.00 | 0.91 | 1.38 | 2.87 |
| Tox3 | 0.74 | 0.66 | 1.10 | 1.00 | 1.00 | 1.00 | 1.00 | 1.00 | 1.00 |
| Tpsab1 | 1.01 | 1.00 | 1.00 | 0.54 | 0.94 | 1.08 | 2.64 | 1.00 | 1.00 |
| Tpx2 | 1.77 | 6.97 | 1.07 | 1.05 | 0.79 | 1.13 | 0.97 | 1.41 | 2.96 |
| Trank1 | 1.00 | 1.00 | 1.00 | 1.00 | 1.00 | 1.00 | 1.00 | 1.00 | 1.00 |
| Trem2 | 2.00 | 2.12 | 1.56 | 1.00 | 1.01 | 1.27 | 1.07 | 1.00 | 1.00 |
| Trpc5os | 1.00 | 1.00 | 1.00 | 1.00 | 1.00 | 1.00 | 1.00 | 1.00 | 1.00 |
| Trpm3 | 1.00 | 1.00 | 1.00 | 1.00 | 1.00 | 1.00 | 1.00 | 1.00 | 1.00 |
| Trpv6 | 1.10 | 0.75 | 0.72 | 1.00 | 1.00 | 1.00 | 1.00 | 1.00 | 1.00 |
| Tspan13 | 0.82 | 1.06 | 0.86 | 0.70 | 0.84 | 1.07 | 1.07 | 0.95 | 0.96 |
| Ube2c | 1.83 | 7.25 | 1.10 | 1.00 | 0.62 | 0.74 | 1.13 | 1.37 | 3.61 |
| Ubxn10 | 0.69 | 0.67 | 0.89 | 1.00 | 1.00 | 1.00 | 1.00 | 1.00 | 1.00 |
| Uchl1 | 0.30 | 9.32 | 1.32 | 0.31 | 1.20 | 1.40 | 1.00 | 1.00 | 1.00 |
| Ucp2 | 1.51 | 1.81 | 1.13 | 1.41 | 1.30 | 1.24 | 0.87 | 1.39 | 1.60 |
| Uhrf1 | 1.99 | 8.58 | 1.07 | 1.00 | 1.00 | 1.00 | 0.68 | 1.24 | 2.73 |
| Unc5cl | 1.00 | 1.00 | 1.00 | 1.00 | 1.00 | 1.00 | 1.98 | 1.51 | 6.13 |
| Upk1a | 1.39 | 0.55 | 1.05 | 1.00 | 1.00 | 1.00 | 1.00 | 1.00 | 1.00 |
| Vash2 | 1.00 | 1.00 | 1.00 | 0.91 | 1.15 | 0.62 | 0.94 | 1.00 | 1.00 |
| Vcan | 1.77 | 1.24 | 1.55 | 1.09 | 0.58 | 1.27 | 0.66 | 1.02 | 1.00 |
| Vgll2 | 1.00 | 1.00 | 1.00 | 1.06 | 0.88 | 1.09 | 1.00 | 1.00 | 1.00 |
| Vpreb1 | 1.00 | 253.68 | 0.83 | 1.00 | 2.56 | 1.00 | 1.00 | 1.00 | 0.34 |
| Vpreb2 | 1.00 | 307.31 | 0.91 | 1.00 | 3.02 | 1.00 | 1.00 | 1.00 | 0.43 |
| Vpreb3 | 0.63 | 11.53 | 0.51 | 1.00 | 3.60 | 1.00 | 1.30 | 1.07 | 0.77 |
| Wars | 0.97 | 0.82 | 1.02 | 0.89 | 0.93 | 1.12 | 0.88 | 1.05 | 0.92 |
| Wdfy4 | 0.83 | 5.72 | 0.81 | 1.00 | 1.17 | 1.00 | 0.91 | 0.87 | 0.85 |
| Wfdc10 | 0.80 | 0.80 | 1.06 | 1.00 | 1.00 | 1.00 | 1.00 | 1.00 | 1.00 |
| Wfdc11 | 1.00 | 1.00 | 1.00 | 1.00 | 1.00 | 1.00 | 1.00 | 1.00 | 1.00 |
| Wfdc13 | 1.00 | 1.00 | 1.00 | 1.00 | 1.00 | 1.00 | 1.00 | 1.00 | 1.00 |
| Wfdc2 | 0.98 | 0.73 | 0.84 | 1.00 | 1.00 | 1.00 | 1.00 | 1.00 | 1.00 |
| Wfdc6a | 0.74 | 0.51 | 0.69 | 1.00 | 1.00 | 1.00 | 1.00 | 1.00 | 1.00 |
| Wfdc6b | 0.83 | 0.56 | 1.35 | 1.00 | 1.00 | 1.00 | 1.00 | 1.00 | 1.00 |
| Wfdc8 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 |
| Wisp2 | 0.65 | 0.96 | 0.78 | 0.97 | 1.09 | 0.78 | 0.50 | 0.98 | 1.16 |
| Xkrx | 1.00 | 1.00 | 0.86 | 1.00 | 1.00 | 1.00 | 0.84 | 0.63 | 0.73 |
| Zbtb16 | 16.54 | 0.87 | 0.15 | 1.52 | 0.82 | 1.94 | 8.01 | 0.91 | 0.66 |
| Zfp648 | 1.00 | 1.00 | 1.00 | 1.00 | 1.00 | 1.00 | 1.00 | 1.00 | 1.00 |
| Zfp697 | 0.83 | 0.73 | 0.83 | 1.00 | 1.00 | 1.00 | 1.00 | 1.00 | 1.00 |
| Zim1 | 1.00 | 1.00 | 1.00 | 2.13 | 1.05 | 1.00 | 1.00 | 1.00 | 1.00 |

Fig. 31- 111

| Gene Name | Brain | | | Adipose tissue | | | Testis | | |
|---|---|---|---|---|---|---|---|---|---|
| | 1d | 1w | 8w | 1d | 1w | 8w | 1d | 1w | 8w |
| Them5 | 1.00 | 1.00 | 1.00 | 1.00 | 1.00 | 1.00 | 1.00 | 1.00 | 1.00 |
| Tifa | 1.01 | 1.99 | 0.96 | 0.98 | 1.00 | 0.77 | 0.80 | 0.92 | 0.92 |
| Timp1 | 1.39 | 1.35 | 1.00 | 5.73 | 0.89 | 0.35 | 0.83 | 0.83 | 1.08 |
| Tmem132e | 0.96 | 1.24 | 0.85 | 1.00 | 1.00 | 1.00 | 1.00 | 1.00 | 1.00 |
| Tmem150c | 1.00 | 0.94 | 0.96 | 0.63 | 10.09 | 1.00 | 1.03 | 1.50 | 0.93 |
| Tmem30b | 1.00 | 1.00 | 1.00 | 0.66 | 5.70 | 1.00 | 1.00 | 1.00 | 1.00 |
| Tmem51 | 0.80 | 1.10 | 1.03 | 0.68 | 7.45 | 0.81 | 0.85 | 0.86 | 1.02 |
| Tnc | 0.83 | 1.17 | 1.30 | 0.98 | 0.57 | 0.91 | 1.00 | 1.00 | 1.00 |
| Tnnc1 | 0.92 | 0.85 | 1.29 | 1.00 | 1.00 | 0.90 | 1.00 | 1.00 | 1.00 |
| Tnnc2 | 1.00 | 1.00 | 1.00 | 1.47 | 1.00 | 0.42 | 1.03 | 1.12 | 0.94 |
| Tnni2 | 1.00 | 1.00 | 1.00 | 2.32 | 1.00 | 0.46 | 1.00 | 1.00 | 1.00 |
| Tnni3 | 1.00 | 1.00 | 1.79 | 1.00 | 0.51 | 1.00 | 0.99 | 1.01 | 0.91 |
| Tnnt2 | 1.49 | 0.94 | 2.34 | 0.89 | 0.87 | 1.00 | 0.67 | 0.95 | 0.70 |
| Tnnt3 | 1.00 | 1.00 | 1.00 | 2.25 | 1.00 | 0.54 | 1.00 | 1.00 | 1.00 |
| Top2a | 1.00 | 2.88 | 1.00 | 1.00 | 0.82 | 0.73 | 1.07 | 1.00 | 1.04 |
| Tox3 | 1.02 | 0.94 | 0.87 | 1.00 | 11.66 | 1.00 | 1.00 | 1.00 | 1.00 |
| Tpsab1 | 1.00 | 1.00 | 1.00 | 0.86 | 1.05 | 1.05 | 1.00 | 1.00 | 1.00 |
| Tpx2 | 1.00 | 1.50 | 1.00 | 1.00 | 1.00 | 1.00 | 1.10 | 0.94 | 0.97 |
| Trank1 | 0.94 | 1.03 | 0.95 | 1.00 | 9.40 | 1.00 | 0.96 | 0.88 | 0.92 |
| Trem2 | 1.20 | 1.12 | 1.07 | 2.10 | 3.93 | 0.66 | 1.00 | 1.14 | 0.98 |
| Trpc5os | 1.00 | 1.00 | 1.00 | 1.00 | 8.21 | 1.00 | 0.88 | 0.87 | 1.00 |
| Trpm3 | 1.10 | 0.99 | 1.05 | 1.00 | 9.93 | 1.00 | 0.97 | 1.00 | 1.00 |
| Trpv6 | 0.99 | 0.86 | 1.08 | 1.00 | 10.81 | 1.00 | 1.00 | 1.00 | 1.00 |
| Tspan13 | 0.97 | 1.03 | 1.02 | 0.78 | 1.02 | 0.84 | 1.02 | 1.03 | 1.03 |
| Ube2c | 1.00 | 2.30 | 1.00 | 0.71 | 0.78 | 0.68 | 1.20 | 1.17 | 1.03 |
| Ubxn10 | 0.91 | 0.92 | 1.18 | 0.43 | 0.15 | 1.00 | 0.90 | 0.93 | 0.66 |
| Uchl1 | 0.91 | 1.03 | 0.96 | 0.52 | 0.74 | 0.41 | 0.83 | 0.93 | 0.90 |
| Ucp2 | 1.29 | 2.19 | 1.04 | 1.76 | 1.23 | 1.02 | 0.95 | 1.01 | 1.00 |
| Uhrf1 | 1.00 | 2.58 | 1.00 | 0.98 | 0.88 | 0.93 | 1.07 | 0.97 | 0.99 |
| Unc5cl | 1.00 | 1.00 | 1.00 | 0.42 | 0.16 | 1.00 | 1.00 | 1.00 | 1.00 |
| Upk1a | 1.00 | 1.00 | 1.00 | 1.00 | 8.83 | 1.00 | 1.00 | 1.00 | 1.00 |
| Vash2 | 1.07 | 0.96 | 0.87 | 1.00 | 10.48 | 1.00 | 1.12 | 1.16 | 1.04 |
| Vcan | 1.28 | 1.04 | 0.86 | 1.27 | 0.68 | 1.11 | 1.00 | 1.00 | 1.00 |
| Vgll2 | 1.00 | 1.00 | 1.00 | 1.00 | 1.00 | 1.00 | 13.41 | 5.16 | 12.54 |
| Vpreb1 | 1.00 | 19.75 | 1.00 | 1.00 | 4.40 | 1.00 | 1.00 | 1.00 | 1.00 |
| Vpreb2 | 1.00 | 22.02 | 1.00 | 1.00 | 4.63 | 1.00 | 1.00 | 1.00 | 1.00 |
| Vpreb3 | 1.00 | 18.37 | 1.00 | 1.00 | 6.29 | 1.00 | 0.77 | 0.90 | 0.98 |
| Wars | 0.91 | 0.93 | 1.03 | 1.06 | 5.21 | 1.06 | 1.00 | 0.92 | 1.03 |
| Wdfy4 | 1.00 | 2.63 | 1.00 | 1.21 | 1.56 | 0.39 | 1.62 | 1.28 | 0.82 |
| Wfdc10 | 1.00 | 1.00 | 1.00 | 1.00 | 17.28 | 1.00 | 1.00 | 0.93 | 0.93 |
| Wfdc11 | 1.00 | 1.00 | 1.00 | 1.00 | 29.44 | 1.00 | 1.00 | 1.00 | 1.00 |
| Wfdc13 | 1.00 | 1.00 | 1.00 | 1.00 | 8.64 | 1.00 | 1.00 | 1.00 | 1.58 |
| Wfdc2 | 0.84 | 1.23 | 0.91 | 0.43 | 0.55 | 1.00 | 1.00 | 1.00 | 1.00 |
| Wfdc6a | 1.00 | 1.00 | 1.00 | 1.00 | 5.61 | 1.00 | 0.84 | 0.93 | 0.99 |
| Wfdc6b | 1.00 | 1.00 | 1.00 | 1.00 | 21.88 | 1.00 | 0.82 | 1.09 | 0.89 |
| Wfdc8 | 1.00 | 1.00 | 1.00 | 1.00 | 79.20 | 1.00 | 0.80 | 0.97 | 1.07 |
| Wfdc9 | 1.00 | 1.00 | 1.00 | 1.00 | 43.06 | 1.00 | 0.86 | 1.44 | 0.72 |
| Wisp2 | 1.00 | 1.00 | 1.00 | 1.42 | 0.81 | 0.78 | 0.76 | 0.92 | 1.60 |
| Xkrx | 1.00 | 1.00 | 1.00 | 1.00 | 10.49 | 1.00 | 1.00 | 1.00 | 1.00 |
| Zbtb16 | 1.89 | 0.78 | 0.82 | 3.99 | 0.94 | 0.54 | 1.20 | 0.72 | 0.93 |
| Zfp648 | 1.00 | 1.00 | 1.00 | 1.00 | 16.54 | 1.00 | 1.00 | 1.00 | 1.00 |
| Zfp697 | 0.98 | 0.97 | 0.99 | 1.70 | 2.03 | 1.96 | 1.00 | 1.00 | 1.00 |
| Zim1 | 1.12 | 1.05 | 1.06 | 9.97 | 1.00 | 1.29 | 1.00 | 1.00 | 1.00 |

Fig. 31- 112

| Gene Name | Thymus | | | Bone marrow | | | Pancreas | | | Ear (skin) | | |
|---|---|---|---|---|---|---|---|---|---|---|---|---|
| | 1d | 1w | 8w | 1d | 1w | 8w | 1d | 1w | 8w | 1d | 1w | 8w |
| Them5 | 0.81 | 5.94 | 1.00 | 1.00 | 1.00 | 1.00 | 1.00 | 1.00 | 1.00 | 0.93 | 1.00 | 1.00 |
| Tifa | 1.20 | 1.93 | 1.67 | 1.09 | 0.73 | 0.87 | 0.81 | 0.83 | 1.03 | 1.13 | 1.08 | 0.95 |
| Timp1 | 0.62 | 1.01 | 1.29 | 1.00 | 1.00 | 1.00 | 1.00 | 1.00 | 1.00 | 0.84 | 1.06 | 0.97 |
| Tmem132e | 1.00 | 1.00 | 1.00 | 1.00 | 0.39 | 0.66 | 1.00 | 1.00 | 1.00 | 1.00 | 1.04 | 1.08 |
| Tmem150c | 0.98 | 0.77 | 1.15 | 1.00 | 1.00 | 1.00 | 1.00 | 1.00 | 1.00 | 1.00 | 1.00 | 1.00 |
| Tmem30b | 1.32 | 0.90 | 1.07 | 1.00 | 1.00 | 1.00 | 0.82 | 1.09 | 1.02 | 1.06 | 1.14 | 1.09 |
| Tmem51 | 1.19 | 1.42 | 1.20 | 1.09 | 1.53 | 1.69 | 0.87 | 0.89 | 0.94 | 0.88 | 1.00 | 1.17 |
| Tnc | 0.87 | 0.84 | 1.08 | 0.97 | 0.61 | 1.23 | 1.00 | 1.00 | 1.00 | 0.80 | 1.03 | 1.10 |
| Tnnc1 | 5.62 | 3.47 | 3.41 | 1.08 | 1.00 | 1.02 | 1.00 | 1.00 | 1.00 | 1.92 | 1.05 | 0.91 |
| Tnnc2 | 1.10 | 27.08 | 1.08 | 1.00 | 1.00 | 1.03 | 1.13 | 1.00 | 1.00 | 1.36 | 1.09 | 0.96 |
| Tnni2 | 0.94 | 12.46 | 0.96 | 1.11 | 0.75 | 0.96 | 1.09 | 1.00 | 1.00 | 1.37 | 1.00 | 1.00 |
| Tnni3 | 6.53 | 3.40 | 3.75 | 1.00 | 1.00 | 1.00 | 1.00 | 1.00 | 1.00 | 1.00 | 1.52 | 0.70 |
| Tnnt2 | 7.36 | 3.56 | 4.50 | 1.00 | 1.00 | 1.00 | 1.00 | 1.00 | 1.00 | 0.88 | 1.00 | 1.00 |
| Tnnt3 | 1.09 | 15.52 | 0.58 | 1.00 | 1.00 | 1.00 | 1.25 | 1.00 | 1.00 | 1.42 | 1.00 | 1.00 |
| Top2a | 0.35 | 0.64 | 0.95 | 0.94 | 1.05 | 1.05 | 1.00 | 1.00 | 1.00 | 0.98 | 0.88 | 0.91 |
| Tox3 | 1.69 | 1.36 | 0.70 | 1.00 | 1.00 | 1.00 | 1.00 | 1.00 | 1.00 | 1.00 | 0.92 | 0.97 |
| Tpsab1 | 2.78 | 5.08 | 2.34 | 1.00 | 1.00 | 1.00 | 1.00 | 1.00 | 1.00 | 1.03 | 1.23 | 1.41 |
| Tpx2 | 0.39 | 0.64 | 0.90 | 1.02 | 0.97 | 0.99 | 1.00 | 1.00 | 1.00 | 0.69 | 1.24 | 1.10 |
| Trank1 | 1.00 | 1.00 | 1.00 | 1.00 | 1.00 | 1.00 | 1.00 | 1.00 | 1.00 | 1.00 | 1.00 | 1.00 |
| Trem2 | 1.16 | 0.47 | 1.67 | 1.81 | 0.44 | 1.19 | 1.00 | 1.00 | 1.00 | 0.80 | 1.00 | 1.00 |
| Trpc5os | 1.00 | 1.00 | 1.00 | 1.00 | 1.00 | 1.00 | 1.00 | 1.00 | 1.00 | 1.00 | 1.00 | 1.00 |
| Trpm3 | 1.17 | 1.00 | 1.00 | 1.00 | 1.00 | 1.00 | 1.00 | 1.00 | 1.00 | 1.17 | 1.00 | 1.00 |
| Trpv6 | 0.73 | 0.63 | 0.75 | 1.00 | 1.00 | 1.00 | 0.84 | 0.71 | 0.73 | 1.00 | 0.78 | 0.98 |
| Tspan13 | 0.92 | 0.92 | 0.99 | 1.23 | 0.77 | 1.11 | 0.76 | 1.00 | 1.05 | 1.04 | 1.00 | 1.03 |
| Ube2c | 0.36 | 0.72 | 0.95 | 1.09 | 0.96 | 1.13 | 1.00 | 1.00 | 1.00 | 0.64 | 1.14 | 1.12 |
| Ubxn10 | 1.02 | 2.00 | 1.00 | 1.00 | 1.00 | 1.00 | 1.00 | 1.00 | 1.00 | 1.00 | 1.15 | 1.11 |
| Uchl1 | 0.91 | 1.19 | 0.96 | 1.36 | 0.59 | 0.77 | 1.00 | 1.00 | 1.00 | 1.00 | 0.76 | 0.74 |
| Ucp2 | 0.89 | 1.03 | 1.02 | 1.13 | 0.93 | 1.06 | 1.57 | 0.94 | 0.80 | 1.05 | 1.09 | 1.00 |
| Uhrf1 | 0.54 | 0.65 | 0.85 | 0.83 | 0.87 | 0.92 | 1.00 | 1.00 | 1.00 | 0.75 | 0.91 | 1.00 |
| Unc5cl | 1.04 | 0.61 | 0.29 | 1.59 | 0.56 | 0.78 | 1.00 | 1.00 | 1.00 | 1.00 | 1.00 | 1.00 |
| Upk1a | 0.95 | 1.11 | 1.35 | 1.00 | 1.00 | 1.00 | 1.00 | 1.00 | 1.00 | 1.43 | 1.00 | 1.00 |
| Vash2 | 1.13 | 0.96 | 0.77 | 1.00 | 1.00 | 1.00 | 1.00 | 1.00 | 1.00 | 1.07 | 1.07 | 0.98 |
| Vcan | 1.27 | 1.12 | 1.71 | 1.10 | 5.15 | 1.01 | 1.00 | 1.00 | 1.00 | 1.14 | 0.92 | 0.82 |
| Vgll2 | 1.00 | 1.00 | 1.00 | 1.00 | 1.00 | 1.00 | 1.00 | 1.00 | 1.00 | 1.28 | 0.80 | 0.90 |
| Vpreb1 | 0.89 | 0.89 | 1.13 | 0.89 | 0.61 | 0.62 | 1.00 | 1.00 | 1.00 | 1.00 | 1.00 | 1.00 |
| Vpreb2 | 0.71 | 1.00 | 1.17 | 1.06 | 0.67 | 0.64 | 1.00 | 1.00 | 1.00 | 1.00 | 0.97 | 0.94 |
| Vpreb3 | 2.09 | 2.79 | 4.00 | 0.95 | 0.44 | 0.76 | 1.00 | 1.00 | 1.00 | 1.00 | 1.14 | 1.05 |
| Wars | 0.93 | 1.20 | 0.97 | 0.86 | 1.08 | 1.04 | 0.99 | 0.97 | 0.83 | 0.87 | 1.14 | 1.13 |
| Wdfy4 | 1.17 | 1.80 | 1.42 | 0.96 | 0.97 | 0.90 | 1.00 | 1.00 | 1.00 | 1.00 | 0.89 | 0.75 |
| Wfdc10 | 1.00 | 1.00 | 1.00 | 1.00 | 1.00 | 1.00 | 1.00 | 1.00 | 1.00 | 1.00 | 1.50 | 1.27 |
| Wfdc11 | 1.00 | 1.00 | 1.00 | 1.00 | 1.00 | 1.00 | 1.00 | 1.00 | 1.00 | 1.00 | 1.00 | 1.00 |
| Wfdc13 | 1.00 | 1.00 | 1.00 | 1.00 | 1.00 | 1.00 | 1.00 | 1.00 | 1.00 | 1.00 | 1.00 | 1.00 |
| Wfdc2 | 1.89 | 3.09 | 0.79 | 1.00 | 1.00 | 1.00 | 1.00 | 1.00 | 1.00 | 0.60 | 0.96 | 1.08 |
| Wfdc6a | 1.00 | 1.00 | 1.00 | 1.00 | 1.00 | 1.00 | 1.00 | 1.00 | 1.00 | 1.00 | 1.00 | 1.00 |
| Wfdc6b | 1.00 | 1.00 | 1.00 | 1.00 | 1.00 | 1.00 | 1.00 | 1.00 | 1.00 | 1.00 | 1.00 | 1.00 |
| Wfdc8 | 1.00 | 1.00 | 1.00 | 1.00 | 1.00 | 1.00 | 1.00 | 1.00 | 1.00 | 1.00 | 0.75 | 0.84 |
| Wfdc9 | 1.00 | 1.00 | 1.00 | 1.00 | 1.00 | 1.00 | 1.00 | 1.00 | 1.00 | 1.00 | 0.82 | 0.90 |
| Wisp2 | 1.85 | 1.87 | 1.34 | 1.00 | 0.92 | 1.73 | 1.00 | 1.00 | 1.00 | 1.03 | 1.12 | 1.09 |
| Xkrx | 1.30 | 0.95 | 0.81 | 1.09 | 0.84 | 0.91 | 1.00 | 1.00 | 1.00 | 1.08 | 1.00 | 1.00 |
| Zbtb16 | 0.90 | 1.30 | 1.94 | 1.22 | 0.90 | 0.93 | 0.74 | 1.22 | 1.26 | 1.89 | 1.00 | 1.09 |
| Zfp648 | 1.00 | 1.00 | 1.00 | 1.00 | 1.00 | 1.00 | 1.00 | 1.00 | 1.00 | 1.16 | 0.98 | 1.03 |
| Zfp697 | 1.00 | 1.00 | 1.00 | 1.00 | 1.00 | 1.00 | 1.00 | 1.00 | 1.00 | 1.00 | 1.08 | 0.97 |
| Zim1 | 1.00 | 1.00 | 1.00 | 1.00 | 1.00 | 1.00 | 1.00 | 1.00 | 1.00 | 1.00 | 0.90 | 1.13 |

Fig. 32 - 1

| Gene | Heart | | | | | Brain | | | | | Lung | | | | |
|---|---|---|---|---|---|---|---|---|---|---|---|---|---|---|---|
| | 1 h | 6 h | 1 d | 1 w | 8 w | 1 h | 6 h | 1 d | 1 w | 8 w | 1 h | 6 h | 1 d | 1 w | 8 w |
| Adrb3 | | 0.69 | | | | | | | | | | | | | |
| Ager | | | | | | | 0.76 | | | | | 0.72 | | 0.49 | 0.83 |
| Aqp5 | | | 4.55 | | | | 1.58 | | | | | | | | |
| Alas2 | | 1.39 | | | | | | | 1.80 | | | | | | |
| Alb | | | | | | | | | | | | | | 0.50 | |
| Aldob | | | 0.27 | 0.32 | 0.37 | | | | 0.71 | | | | | | |
| Angptl4 | | 1.70 | 2.18 | 3.96 | | | 1.59 | 1.36 | 1.59 | | | | | | |
| Ano3 | 1.66 | 0.61 | 0.69 | 2.37 | | | | | | | | | | | |
| Arg1 | | | 3.12 | | | | | | | | | | | | |
| Arntl | | | | 3.18 | 3.02 | | 0.84 | 0.83 | | | | | | | 2.91 |
| Arrdc2 | | 0.47 | 0.70 | 0.40 | | | | | | | | | 1.38 | 0.55 | |
| Arrdc3 | | 1.28 | | 0.39 | | | 1.16 | | | | | 0.73 | | 0.78 | |
| Atp6v0d2 | | | 8.06 | | | | | | | | | | | | |
| Cebpd | 0.70 | | | 1.58 | 1.64 | | | | | | 0.46 | | | | |
| Ciart | | 0.59 | | 0.28 | 0.38 | | 1.42 | | 0.72 | 0.73 | | | | 0.41 | 0.72 |
| Cidea | | 0.66 | 0.67 | 0.31 | | | | | | | | | | | |
| Cwc22 | | | | | | | | | 1.75 | 0.31 | | | | | 1.57 |
| Dbp | | 0.61 | 0.31 | 0.31 | 0.24 | | 0.84 | | 0.65 | 0.44 | 0.44 | 0.58 | | 0.35 | 0.28 |
| Ddit4 | | 2.45 | | | | | 2.19 | | | | 1.43 | 1.94 | | | |
| Fabp4 | | 0.73 | 0.88 | 0.77 | | | | | | | | | | 1.44 | |
| Fabp5 | | 1.32 | | 2.41 | 0.63 | | 1.16 | | 0.74 | | | | | | |
| Foxo1 | | 0.66 | 0.66 | 0.29 | | | 1.14 | | | | | 0.76 | | 0.58 | |
| Fst | 2.01 | 2.10 | 1.52 | 4.02 | 4.51 | | 1.31 | 1.24 | | | | | | | |
| Ftcd | | | | | | | | | | | 1.52 | | | | |
| Gdpd3 | | | | 0.37 | | | | | 0.74 | | | | | 0.42 | |
| Gnmt | | 0.62 | 0.47 | 0.27 | 0.37 | | | | | | | | | 0.55 | |
| Gpnmb | | | | 24.7 | 3.83 | | | | | | | | | | |
| Hba-a | | | | | | | | | 2.12 | | | | | | |
| Hbb-b | | 1.38 | | | | | | | 1.86 | | | | | | |
| Hif3a | | 0.52 | | 0.60 | 0.49 | | | | | | 0.45 | 0.72 | | 0.50 | |
| Hlf | | | 0.47 | 0.32 | 0.41 | 1.34 | 1.36 | | 0.76 | | | | | 0.43 | 0.45 |
| Hmgcs2 | 1.56 | 0.59 | | 1.21 | | | 0.83 | 1.56 | 1.34 | | 1.55 | | | 0.47 | |
| Hpcal4 | | | | | | | | | | | | | 0.18 | 0.23 | 0.39 |
| Hpd | | | | | | | | | | | | | | | |
| Ky | 1.71 | | | 0.39 | 0.41 | | 1.43 | | | | 1.69 | | | | |
| Mmp12 | | 1.58 | 5.32 | 11.3 | | | | | | | | | | 1.72 | 1.60 |
| Nmrk2 | | 4.23 | 17.1 | 5.71 | 4.89 | | | | | | | | 248 | | |
| Nppa | | 1.33 | | 2.03 | 3.08 | | 0.79 | | | | | 0.54 | 3.42 | 8.23 | |
| Nppb | | 5.06 | 5.19 | 2.69 | 4.85 | | | | 0.48 | | | 3.15 | 47.8 | 19.5 | 4.81 |
| Pah | | | 0.51 | 0.36 | 0.64 | | | | | | | | | | |
| Pdk4 | 0.66 | 0.74 | | 0.55 | | | | | | | | | | 0.51 | |
| Plin4 | | 0.60 | 0.73 | 0.51 | 0.61 | | | | | | 0.68 | | | 0.57 | |
| Prm1 | | | | | | | | | | | | | | | |
| Scgb1a1 | | | | | | | | | | | | | | 0.50 | |
| Sftpc | | | | | | | | | | | | | | 0.55 | |
| Snap25 | | | | | | | | | 0.79 | | | | | | |
| Snph | | | 6.22 | 2.93 | | | 1.39 | 1.30 | | | | | | | |
| Spp1 | | 2.78 | 33.1 | 7.26 | | | | | 0.75 | | 1.70 | | | | |
| Sult5a1 | | | 0.50 | 0.39 | | | 1.39 | | 0.66 | | | | | 0.51 | |
| Thrsp | | 0.51 | 0.48 | 0.14 | 0.76 | | 0.76 | | 0.63 | | | | | 0.42 | |
| Tnnc2 | | | | | | | | | 0.55 | | | | | | 1.66 |
| Umod | | | | | | | | | | | | | | | |
| Vgll2 | | | | 0.25 | 3.42 | | | | | | | | | | 3.72 |
| Elovl3 | | | 1.55 | 0.49 | | | 0.70 | | | | | 0.67 | | | |
| Saa1 | | | | 0.44 | | | | | | | | | | | |
| Saa2 | | | | | | | | | | | | | | | |

Fig. 32 - 2

| Gene | Kidney | | | | | Adipose tissue | | | | | Liver | | | | |
|---|---|---|---|---|---|---|---|---|---|---|---|---|---|---|---|
| | 1 h | 6 h | 1 d | 1 w | 8 w | 1 h | 6 h | 1 d | 1 w | 8 w | 1 h | 6 h | 1 d | 1 w | 8 w |
| Adrb3 | | | | 0.42 | | | 0.49 | | | 1.75 | | | | | |
| Ager | | | | | | | | | | | | 0.67 | | | |
| Aqp5 | | | 1.62 | | | | | | | | | | | | |
| Alas2 | | | 2.88 | | | | | | 1.84 | | | | | | |
| Alb | | 0.68 | | | | | | | | | | | | 1.20 | |
| Aldob | 0.84 | 0.82 | | 0.66 | 0.72 | | | | 0.41 | | | 0.71 | | 0.65 | |
| Angptl4 | | 1.56 | 2.34 | 1.73 | | | | 1.44 | | 1.80 | | | | | |
| Ano3 | | | | | | | | | | | | | | | |
| Arg1 | | | | | | | | | | | | 0.68 | | 0.66 | 0.80 |
| Arntl | | | 3.35 | 2.98 | | | | | 2.60 | 2.32 | | | | 7.19 | 2.95 |
| Arrdc2 | | 2.03 | | | | | | | | | | | | 1.67 | |
| Arrdc3 | | | 1.58 | | | | | | | | | | | | |
| Atp6v0d2 | | | | | | | | | | | | | | | |
| Cebpd | | | | 0.48 | | 0.58 | | | | | | | | | 0.53 |
| Ciart | | | | | | | | | 0.48 | | | | | 0.33 | 0.51 |
| Cidea | | 2.60 | | | | | | | | | | | | | |
| Cwc22 | | | | 1.76 | | | | | 2.21 | | | | | | 1.71 |
| Dbp | 0.38 | 0.73 | 0.61 | 0.49 | 0.52 | | 0.53 | | 0.48 | 0.51 | | | | 0.27 | 0.35 |
| Ddit4 | | 3.19 | | | | | 1.44 | | | | | | | | |
| Fabp4 | | 1.62 | | | | | 0.72 | | 1.48 | | | | | | 1.35 |
| Fabp5 | 0.84 | | | | | | 0.64 | | | | | | 0.33 | | |
| Foxo1 | 0.79 | | | 0.70 | | | | | | | 0.84 | | | 0.65 | |
| Fst | | | 1.38 | | | | | 1.42 | | | | 0.64 | | 1.62 | |
| Ftcd | | | | | | | | | | | | 0.80 | | 0.67 | |
| Gdpd3 | | | 0.62 | | | | | | | | | | | 0.64 | |
| Gnmt | | | 1.47 | 0.59 | | | | | | | | 0.63 | | 0.62 | 0.75 |
| Gpnmb | | | 1.45 | 2.82 | | | | | | | | | 2.88 | 1.84 | |
| Hba-a | | | | 3.73 | | | | | 1.93 | | | 0.62 | | 2.52 | |
| Hbb-b | | | | 3.41 | | | | | 1.76 | | | | | 2.07 | |
| Hif3a | 0.68 | | | | | | 0.64 | | | | | | | | |
| Hlf | | | 1.29 | | | | | | 0.72 | 0.56 | | 1.54 | | 0.63 | |
| Hmgcs2 | | | | | | | | | | | | | | | |
| Hpcal4 | 0.69 | | | 0.65 | 0.75 | | | | | | | | | | |
| Hpd | | | 3.08 | 0.32 | | | | | | | | | | 0.60 | |
| Ky | | | | | | | | | | | | | | | |
| Mmp12 | | | | | | | 0.54 | | | | | | | | |
| Nmrk2 | | | | | | | | | | | | | | | |
| Nppa | | | | 0.33 | | | | | | | | | | | |
| Nppb | | | | | | | | | | | | | | | |
| Pah | | 0.80 | | 0.65 | | | | | | | | 0.67 | | 0.76 | |
| Pdk4 | 0.56 | | | | | | | | 1.66 | | | | | | |
| Plin4 | | 2.33 | | | | | 0.61 | | | | | 2.05 | | | |
| Prm1 | | | 2.43 | 0.50 | | | | | 0.42 | 1.50 | | | | | |
| Scgb1a1 | | | | | | | | | | | | | | | |
| Sftpc | | 2.58 | | | | | 2.42 | | | | | | | | |
| Snap25 | | | | | | | | | 0.43 | | | | | | |
| Snph | | | | | | | 2.80 | | | | | | | | |
| Spp1 | 0.83 | | | | | | | | 0.41 | | | | | | |
| Sult5a1 | 0.68 | | | | | | 1.71 | | | | | | | | |
| Thrsp | | | | | | | 0.45 | | | | | | | | 0.35 |
| Tnnc2 | | 1.88 | | | | | | | | | | | | | |
| Umod | | | | | | 0.27 | | | | | | | | | |
| Vgll2 | | | | | | | 1.56 | | | | | | | | |
| Elovl3 | | | | | | | | | | | | | | | 3.46 |
| Saa1 | | 5.42 | | | | | | | | | | | | | |
| Saa2 | | | | | | | | | | | | | 0.66 | | |

Fig. 32 - 3

| Gene | Skeletal muscle | | | | | Testis | | | | | Spleen | | | | |
|---|---|---|---|---|---|---|---|---|---|---|---|---|---|---|---|
| | 1h | 6h | 1d | 1w | 8w | 1h | 6h | 1d | 1w | 8w | 1h | 6h | 1d | 1w | 8w |
| Adrb3 | 1.74 | | | | | | | | | | | 0.53 | | | |
| Ager | | | | | | | | | | | | | | | |
| Aqp5 | | | | | | | | | | | | | | | |
| Alas2 | | 0.63 | | | | | | | | | | | | | |
| Alb | | | | | | | | | | | | | | | |
| Aldob | | | | | | | 0.68 | | | | | | | | |
| Angptl4 | 1.78 | 2.03 | | 1.64 | | | | | | | 1.30 | 1.67 | | 1.86 | |
| Ano3 | | | | | | | | 1.88 | | | | | | | |
| Arg1 | | | | | | | | | | | | | | | |
| Arntl | | 0.75 | | 2.05 | 1.89 | | | | | | | | | | |
| Arrdc2 | | | | | | | | 1.17 | | | | 1.40 | | 1.36 | |
| Arrdc3 | | | | | | | | 1.27 | | | | | | | |
| Atp6v0d2 | | | | | | | | | | | | 0.66 | | | |
| Cebpd | 0.67 | | | | | | | 1.58 | | | 0.53 | 0.72 | | | |
| Ciart | | | | | | | | | | | | | | 0.51 | 0.55 |
| Cidea | | | | | | | | | | | | | | | |
| Cwc22 | | | | 1.69 | | | | | | | | | | | 1.57 |
| Dbp | | 0.79 | | 0.50 | 0.43 | 0.71 | 0.66 | 0.59 | | | 0.55 | | | 0.46 | 0.38 |
| Ddit4 | | 1.73 | | | | | 2.30 | | | | | 1.86 | | | |
| Fabp4 | 1.34 | | | | | 0.12 | | | | | | | | | |
| Fabp5 | | | 0.73 | 0.66 | | | | | 0.59 | | | | | | |
| Foxo1 | | | | 1.87 | | 0.77 | | | | | | | | 0.46 | 0.69 |
| Fst | | 1.56 | | | | | | | | | | | | 0.44 | |
| Ftcd | | | | | | | 0.61 | | | | | | | | |
| Gdpd3 | | | | | | | | | | | | | | | |
| Gnmt | | | | | | | 0.66 | | 0.40 | | | | | | |
| Gpnmb | | | | | | | | | | | | | | | 0.59 |
| Hba-a | | 0.62 | | 2.10 | | | | | | | | | | | |
| Hbb-b | | 0.55 | | 1.70 | | | | | | | | | | | |
| Hif3a | | | | 1.66 | | | | 1.32 | | | | | | 1.94 | |
| Hlf | | | | 0.69 | 1.53 | | | | | | | 1.74 | 1.59 | 0.58 | |
| Hmgcs2 | | | | | | | | 0.66 | | | | | | 0.67 | |
| Hpcal4 | | | | | | | | | | | | | | | |
| Hpd | | | | | | | | | | | | | | | |
| Ky | | | | | | | | | | | | 2.44 | | | |
| Mmp12 | | | | | | | | | | | | | | | 0.68 |
| Nmrk2 | | | | | | | | | | | | | | | |
| Nppa | | | | | | | | | | | | 0.40 | | | |
| Nppb | | | | | | | | | | | | | | | |
| Pah | | | | | | | | | | | | | | | |
| Pdk4 | | | | | | | | | | | | | | 0.53 | |
| Plin4 | | | | | | | | | | | | | | | |
| Prm1 | | | | | | 1.49 | 1.83 | 2.07 | 1.54 | | | | | | |
| Scgb1a1 | | | | | | | | | | | | 1.70 | | | |
| Sftpc | | | | | | | 0.67 | | | | | | | | |
| Snap25 | | | | | | | | | | | | | | | |
| Snph | | | | | | | 2.75 | 6.98 | 5.70 | | | | | | |
| Spp1 | | 0.16 | | | | | 0.26 | | | | | | | | |
| Sult5a1 | | 0.76 | | | | | | | 0.73 | | | | | | |
| Thrsp | | | | 0.69 | | | | 0.54 | | | | | | 0.50 | |
| Tnnc2 | | | | | | | | | | | | | | | |
| Umod | | | | | | | | | 1.55 | | | | | | |
| Vgll2 | | | | | | | | | | | | | | | |
| Elovl3 | | | | | | | | | | | | 0.62 | | 1.97 | |
| Saa1 | | | | | | | | | | | | | | | |
| Saa2 | | | | | | | | | | | | 0.12 | | | |

Fig. 32 - 4

| Gene | Thymus | | | | | Bone marrow | | | | | Pancreas | | | | |
|---|---|---|---|---|---|---|---|---|---|---|---|---|---|---|---|
| | 1 h | 6 h | 1 d | 1 w | 8 w | 1 h | 6 h | 1 d | 1 w | 8 w | 1 h | 6 h | 1 d | 1 w | 8 w |
| Adrb3 | | | | 1.76 | | | | 0.67 | 0.36 | | | | | | |
| Ager | | | | 0.34 | 0.51 | | 0.77 | | | 0.69 | | | 0.16 | 5.19 | 0.29 |
| Aqp5 | | | | | | | | | | | | | | | |
| Alas2 | | | | | | | | | | | | 1.35 | | | |
| Alb | | | | | | | | | | | | | | | |
| Aldob | | | 1.68 | | | | | | | | | | | | |
| Angptl4 | | | | | | | 1.37 | | | | | 1.63 | | | |
| Ano3 | | | | | | | | | | | | | | | |
| Arg1 | | | | | | | | | | | | | | | |
| Arntl | | | 0.62 | 0.55 | | | 0.68 | 0.62 | 0.44 | | | | | 5.21 | |
| Arrdc2 | | | | | | | | | | | | 2.12 | | | |
| Arrdc3 | | | | | | | | | 0.67 | | | | | | |
| Atp6v0d2 | | | | | | | | | | | | | | | |
| Cebpd | 0.55 | | | 0.54 | 0.47 | 0.72 | 0.47 | | 0.64 | 0.61 | | | | | |
| Ciart | | | | | | | | | 0.77 | | | | | 0.45 | 0.35 |
| Cidea | | | | | | | | | | | | | | | |
| Cwc22 | | | 3.69 | | | | | | 2.79 | | | | | | |
| Dbp | | | 0.43 | 0.32 | | | | | 0.61 | | | | | | |
| Ddit4 | | 2.08 | | | | | | | | | | 3.81 | | | |
| Fabp4 | | 0.47 | | | | | | | 0.58 | | | 1.38 | | | |
| Fabp5 | | 0.82 | 0.54 | 0.65 | | | 0.75 | | 0.71 | | | 1.55 | | | |
| Foxo1 | | 0.82 | 0.62 | 0.62 | 0.61 | | | | 0.45 | 0.74 | | 0.72 | | | |
| Fst | | | | | | | | | | | | | | | |
| Ftcd | | | | | | | | | | | | | | | |
| Gdpd3 | | | 0.56 | | | | | | 0.67 | | | | | | |
| Gnmt | | | 0.51 | | | | 0.64 | | 0.52 | | | | | | |
| Gpnmb | | | | | | | | | | | | | | | |
| Hba-a | | | | | | | | | | | | 1.32 | | | |
| Hbb-b | | | | | | | 0.73 | | | | | 1.25 | | | |
| Hif3a | | | 0.59 | 0.64 | | | | | | | | | | | |
| Hlf | | | | | | | 1.32 | | | | | | | 0.56 | |
| Hmgcs2 | | | 1.38 | | | | 1.33 | | | | | | | | |
| Hpcal4 | | | | | | | | | | | | | | | |
| Hpd | | | | | | | | | | | | | | | |
| Ky | | | | | | | | | | | | | | | |
| Mmp12 | | | 0.58 | | | | | | | | | | | | |
| Nmrk2 | | | | | | | | | | | | | | | |
| Nppa | | | | | | | | | | | | | | | |
| Nppb | | | | | | | | | | | | | | | |
| Pah | | | | | | | | | | | | | | | |
| Pdk4 | | | | | | | | | | | | 2.37 | | | |
| Plin4 | | | | | | | | | | | | | | | |
| Prm1 | | | | | | | | | | | | | | | |
| Scgb1a1 | | | | | | | | | | | | | | | |
| Sftpc | | | | | | | 2.00 | | | | | 2.25 | | | |
| Snap25 | | | | | | | | | | | | | | | 0.27 |
| Snph | | | | | | | | | | | | | | | |
| Spp1 | 1.64 | | 0.53 | | | | 1.62 | 0.78 | | | | | | | |
| Sult5a1 | 0.75 | | | | | | | | | | | 1.54 | | | |
| Thrsp | | | | | | | | | 0.41 | | | | | | |
| Tnnc2 | 3.83 | | | | | | | | 1.49 | | | | | | |
| Umod | | | | | | | | | | | | | | | |
| Vgll2 | | | | 0.46 | | | | | 0.36 | | | | | | |
| Elovl3 | | | 0.47 | | | | | | 0.65 | 0.78 | | | | | |
| Saa1 | | | | | | | | | | | | | | | |
| Saa2 | | | | | | | | | | | | | | | |

Fig. 32 - 5

| Gene | Ear | | |
|---|---|---|---|
| | 1d | 1w | 8w |
| Adrb3 | | | |
| Ager | 0.64 | | |
| Aqp5 | | | |
| Alas2 | | | |
| Alb | | | |
| Aldob | | | |
| Angptl4 | | | |
| Ano3 | | | |
| Arg1 | 0.68 | | |
| Arntl | | 0.73 | |
| Arrdc2 | | | 1.38 |
| Arrdc3 | | | 0.87 |
| Atp6v0d2 | | | |
| Cebpd | | | |
| Ciart | | | |
| Cidea | | | |
| Cwc22 | | | |
| Dbp | 0.66 | | |
| Ddit4 | | | 2.17 |
| Fabp4 | 0.68 | | |
| Fabp5 | | | |
| Foxo1 | | 0.75 | |
| Fst | | | |
| Ftcd | | | |
| Gdpd3 | | | |
| Gnmt | 0.61 | 0.51 | |
| Gpnmb | | | |
| Hba-a | | | |
| Hbb-b | | | |
| Hif3a | | | |
| Hlf | | | |
| Hmgcs2 | | | |
| Hpcal4 | | | |
| Hpd | | | |
| Ky | | | |
| Mmp12 | | 1.96 | |
| Nmrk2 | | | |
| Nppa | | | |
| Nppb | | | |
| Pah | | | |
| Pdk4 | | 0.56 | |
| Plin4 | | | |
| Prm1 | | | |
| Scgb1a1 | | 0.68 | |
| Sftpc | | | |
| Snap25 | 0.55 | | |
| Snph | | | 1.98 |
| Spp1 | | | |
| Sult5a1 | 0.74 | | |
| Thrsp | | | |
| Tnnc2 | 1.63 | | |
| Umod | | | |
| Vgll2 | | | |
| Elovl3 | 0.76 | 0.79 | |
| Saa1 | | | |
| Saa2 | | | |

Fig. 33-1

| Metabolite | Plasma | | Skeletal muscle | | Brown fat | | Heart | | Lung | |
|---|---|---|---|---|---|---|---|---|---|---|
| | E | M | E | M | E | M | E | M | E | M |
| 2-Hydroxybutyric acid | 2.25 | 4.57 | 2.00 | 3.23 | 3.04 | 4.03 | 2.31 | 3.52 | 2.15 | 3.37 |
| 2-Oxoglutaric acid | 0.54 | 0.25 | N.A. | N.A. | N.A. | N.A. | N.A. | N.A. | N.A. | N.A. |
| 2-Oxoisovaleric acid | 1.22 | 1.06 | N.A. | N.A. | N.A. | N.A. | N.A. | N.A. | 1.13 | 0.74 |
| 2-Phosphoglyceric acid | N.A. | N.A. | N.A. | N.A. | 1< | 1< | 1.34 | 0.79 | 0.96 | 1.05 |
| 3-Hydroxybutyric acid | 0.55 | 0.81 | 0.58 | 1.01 | 0.74 | 1.02 | 0.71 | 1.18 | 0.67 | 0.96 |
| 3-Phosphoglyceric acid | 1.41 | 1.55 | 1< | <1 | 1.30 | 1.51 | 1.34 | 0.77 | 0.95 | 0.94 |
| 6-Phosphogluconic acid | N.A. | N.A. | 1.26 | 1.34 | 0.75 | 0.92 | 1.19 | 0.88 | 0.73 | 1.05 |
| ADP | 2.60 | 0.67 | 1.70 | 2.70 | 1.30 | 0.83 | 1.11 | 0.84 | 1.33 | 0.92 |
| AMP | 1.82 | 0.53 | 6.09 | 15.03 | 0.76 | 0.73 | 1.00 | 0.80 | 1.08 | 0.81 |
| ATP | 3.13 | 0.70 | 0.86 | 0.60 | 2.38 | 0.93 | 1.51 | 0.75 | 1.29 | 0.96 |
| Acetyl CoA_divalent | N.A. | N.A. | N.A. | N.A. | 1.15 | 2.34 | 1.31 | 1.27 | 1.21 | 1< |
| Adenine | N.A. | N.A. | 1.54 | 1.38 | 0.99 | 1.02 | 1.19 | 1.34 | 1.18 | 1.20 |
| Adenosine | 1.11 | 2.06 | 1.23 | 2.10 | 0.91 | 1.04 | 0.83 | 1.72 | 1.28 | 1.30 |
| Ala | 1.29 | 0.87 | 0.99 | 0.98 | 1.33 | 1.09 | 1.31 | 1.01 | 1.01 | 0.89 |
| Anthranilic acid | 3.58 | 4.51 | N.A. | N.A. | N.A. | N.A. | N.A. | N.A. | 1.96 | 2.99 |
| Arg | 1.24 | 1.12 | 1.28 | 1.27 | 1.76 | 1.71 | 1.25 | 1.39 | 0.95 | 1.07 |
| Asn | 1.33 | 1.47 | 1.29 | 1.66 | 1.95 | 2.08 | 1.46 | 1.57 | 1.29 | 1.33 |
| Asp | 1.42 | 0.90 | 0.79 | 1.13 | 2.10 | 1.87 | 1.50 | 1.40 | 0.73 | 0.75 |
| Betaine | 0.97 | 0.86 | 0.77 | 0.82 | 1.51 | 1.67 | 0.64 | 0.73 | 0.61 | 0.80 |
| Betaine aldehyde_+H2O | N.A. | N.A. | N.A. | N.A. | 1.01 | 1.14 | N.A. | N.A. | 0.74 | 1.45 |
| CDP | N.A. | N.A. | 2.93 | 2.56 | 1.80 | 0.66 | 0.99 | 1< | 1.69 | 0.75 |
| CMP | N.A. | N.A. | 1.21 | 1.34 | 0.95 | 0.82 | 1.04 | 0.78 | 1.08 | 0.87 |
| CTP | N.A. | N.A. | 1.03 | 0.72 | N.A. | N.A. | N.A. | N.A. | N.A. | N.A. |
| Carnosine | 1.13 | 1.49 | 1.65 | 1.62 | 1.94 | 4.11 | 1.11 | 1.48 | 1.11 | 1.41 |
| Choline | 1.13 | 0.60 | 1.90 | 2.46 | 1.39 | 1.43 | 1.30 | 1.28 | 1.00 | 1.55 |
| Citric acid | 0.64 | 0.59 | 0.80 | 0.90 | 1.32 | 0.81 | 0.69 | 0.81 | 0.86 | 0.90 |
| Citrulline | 0.99 | 0.83 | 1.14 | 1.13 | 1.09 | 0.84 | 1.00 | 0.97 | 1.04 | 0.89 |
| CoA_divalent | N.A. | N.A. | 1.03 | 0.92 | 0.90 | 0.82 | 0.96 | 1.04 | 0.95 | 0.87 |
| Creatine | 1.14 | 1.10 | 1.07 | 1.04 | 1.20 | 1.39 | 1.10 | 1.04 | 1.01 | 1.08 |
| Creatinine | 1.12 | 0.92 | 0.94 | 0.91 | 1.25 | 1.12 | 1.17 | 1.18 | 1.09 | 0.96 |
| Cys | N.A. | N.A. | 0.72 | 1.41 | 1.71 | 1.92 | N.A. | 1< | 1.32 | 1.32 |
| Cytidine | 1.78 | 1.11 | 1.17 | 1.43 | 1.58 | 1.29 | 1.06 | 1.25 | 1.16 | 1.37 |
| Cytosine | N.A. | N.A. | N.A. | N.A. | N.A. | N.A. | N.A. | N.A. | N.A. | N.A. |
| Dihydroxyacetone phosphate | N.A. | N.A. | 1< | <1 | 0.83 | 1.67 | 1< | 1.11 | 0.98 | 0.90 |
| Erythrose 4-phosphate | 1.15 | 3.30 | N.A. | N.A. | N.A. | N.A. | N.A. | N.A. | N.A. | N.A. |
| Fructose 1,6-diphosphate | N.A. | N.A. | 1.55 | 0.48 | N.A. | N.A. | 1< | 0.46 | 0.89 | 1.39 |
| Fructose 6-phosphate | N.A. | N.A. | 1.78 | 0.31 | 0.97 | 1.26 | 3.64 | 0.95 | 1.12 | 1.38 |
| Fumaric acid | <1 | <1 | 0.75 | 0.85 | 0.84 | 0.80 | 0.96 | 0.96 | 0.90 | 0.67 |
| GABA | N.A. | N.A. | 0.64 | 0.92 | 0.69 | 1.41 | 0.54 | 0.79 | 0.86 | 1.53 |
| GDP | 2.02 | 0.64 | 2.25 | 3.86 | 1.51 | 1.28 | 1.28 | 0.90 | 1.37 | 0.99 |
| GMP | 1< | <1 | 1.36 | 1.78 | 1.43 | 1.41 | 1.16 | 1.10 | 1.25 | 1.08 |
| GTP | N.A. | N.A. | 1.24 | 0.91 | 2.62 | 1.60 | 1.60 | 0.90 | 1.39 | 1.09 |
| Gln | 1.07 | 0.77 | 1.10 | 1.25 | 1.48 | 1.18 | 1.28 | 1.25 | 1.09 | 0.92 |
| Glu | 1.00 | 0.77 | 0.47 | 0.66 | 1.69 | 1.42 | 0.87 | 1.07 | 0.84 | 0.82 |
| Gluconic acid | 0.86 | 0.88 | N.A. | N.A. | 1.13 | 0.99 | 0.70 | 0.97 | 0.76 | 0.80 |
| Glucose 1-phosphate | N.A. | N.A. | 1.47 | 0.42 | 1.14 | 1.68 | 2.80 | 1.23 | 0.96 | 1.20 |
| Glucose 6-phosphate | 1.54 | 0.71 | 1.77 | 0.30 | 0.93 | 1.28 | 3.87 | 0.97 | 1.25 | 1.43 |
| Glutathione (GSH) | N.A. | N.A. | 0.77 | 0.67 | 1.01 | 1.10 | 0.86 | 0.94 | 1.06 | 0.95 |
| Glutathione (GSSG)_divalent | 0.19 | 0.04 | 0.93 | 0.99 | 0.94 | 0.99 | 0.90 | 0.89 | 0.95 | 0.97 |
| Gly | 0.83 | 0.75 | 0.98 | 1.04 | 1.25 | 1.18 | 0.91 | 0.85 | 1.17 | 1.18 |
| Glycerol 3-phosphate | 1.57 | 0.86 | 0.82 | 0.77 | 1.40 | 1.84 | 1.01 | 0.87 | 1.12 | 1.13 |
| Guanine | N.A. | N.A. | N.A. | N.A. | 1.38 | 1.08 | 1< | 1< | N.A. | N.A. |
| Guanosine | N.A. | N.A. | 1.11 | 2.01 | 1.89 | 2.06 | 0.94 | 1.60 | 1.50 | 1.75 |
| His | 1.47 | 1.29 | 1.22 | 1.37 | 1.86 | 1.70 | 1.01 | 1.07 | 1.34 | 1.21 |
| Homoserine | N.A. | N.A. | 0.97 | 1.29 | 1.24 | 1.00 | <1 | 1.16 | 0.94 | 0.89 |
| Hydroxyproline | 0.91 | 0.90 | 2.06 | 1.88 | 0.97 | 1.03 | 0.86 | 0.82 | 0.75 | 0.79 |
| Hypoxanthine | 1.24 | <1 | 1.10 | 1.50 | 1.45 | 2.22 | 0.96 | 0.96 | 0.94 | 1.92 |
| IMP | N.A. | N.A. | 0.91 | 1.02 | 1.23 | 1.40 | 0.91 | 1.01 | 1.43 | 1.40 |
| Ile | 1.30 | 1.32 | 1.19 | 1.27 | 2.05 | 1.90 | 1.10 | 1.23 | 1.03 | 1.29 |
| Inosine | N.A. | N.A. | 0.96 | 1.32 | 1.86 | 2.91 | 0.98 | 0.94 | 1.71 | 2.68 |
| Isocitric acid | 0.70 | 0.64 | N.A. | N.A. | N.A. | N.A. | N.A. | N.A. | <1 | <1 |
| Lactic acid | 1.38 | 0.75 | 0.98 | 0.86 | 1.47 | 1.11 | 1.33 | 0.86 | 0.90 | 0.68 |

Fig. 33- 2

| Metabolite | Thymus | | Kidney | | Liver | | Colon | | Stomach | | Adipose tissue | |
|---|---|---|---|---|---|---|---|---|---|---|---|---|
| | E | M | E | M | E | M | E | M | E | M | E | M |
| 2-Hydroxybutyric acid | 2.03 | 3.62 | 2.05 | 2.45 | 2.12 | 2.78 | 1.81 | 3.11 | 1.70 | 3.38 | 4.00 | 1< |
| 2-Oxoglutaric acid | N.A. | N.A. | N.A. | N.A. | N.A. | N.A. | N.A. | N.A. | N.A. | N.A. | N.A. | N.A. |
| 2-Oxoisovaleric acid | N.A. | N.A. | N.A. | N.A. | N.A. | N.A. | N.A. | N.A. | N.A. | N.A. | N.A. | N.A. |
| 2-Phosphoglyceric acid | 2.63 | 1.92 | 0.78 | <1 | N.A. | N.A. | N.A. | N.A. | N.A. | N.A. | N.A. | N.A. |
| 3-Hydroxybutyric acid | 0.65 | 1.18 | 0.54 | 0.93 | 0.85 | 1.26 | 0.55 | 1.06 | 0.48 | 1.03 | 1.08 | 2.11 |
| 3-Phosphoglyceric acid | 2.35 | 1.76 | 0.91 | 0.94 | 1.32 | 1.33 | 1.22 | <1 | N.A. | N.A. | 1.52 | 1.78 |
| 6-Phosphogluconic acid | 1.30 | 1.24 | 0.86 | 0.92 | 0.54 | 0.26 | 0.86 | 1< | 0.88 | 1.02 | 1.92 | 1< |
| ADP | 0.74 | 0.87 | 1.00 | 0.94 | 0.98 | 0.61 | 1.07 | 0.73 | 1.07 | 1.11 | 1.38 | 2.20 |
| AMP | 1.03 | 1.12 | 0.86 | 0.77 | 0.63 | 0.62 | 1.35 | 0.68 | 0.93 | 1.10 | 0.26 | 0.48 |
| ATP | 0.41 | 0.61 | 1.14 | 1.10 | 1.42 | 0.56 | 0.87 | 0.78 | 1.16 | 1.04 | 3.58 | 3.22 |
| Acetyl CoA_divalent | 1< | 1< | 1.18 | 1.44 | 0.98 | 0.49 | 0.89 | 1.03 | 1.03 | 0.82 | N.A. | N.A. |
| Adenine | 0.97 | 0.96 | 0.89 | 0.93 | 0.86 | 0.84 | 1.30 | 2.00 | 0.92 | 1.06 | 1< | 1< |
| Adenosine | 3.12 | 2.09 | 0.75 | 0.69 | 1.40 | 2.45 | 0.95 | 1.02 | 11.01 | 3.43 | 1.80 | 2.77 |
| Ala | 1.08 | 0.82 | 1.06 | 0.89 | 0.89 | 0.57 | 1.12 | 1.01 | 1.08 | 1.02 | 1.74 | 1.69 |
| Anthranilic acid | N.A. | N.A. | N.A. | N.A. | N.A. | 1< | N.A. | N.A. | N.A. | N.A. | N.A. | N.A. |
| Arg | 2.43 | 1.75 | 0.93 | 0.99 | 1.00 | 0.83 | 0.92 | 0.99 | 0.93 | 0.95 | 2.44 | 3.09 |
| Asn | 1.37 | 1.17 | 1.06 | 1.18 | 0.95 | 1.01 | 1.09 | 1.18 | 1.04 | 1.11 | 2.65 | 3.95 |
| Asp | 0.91 | 0.91 | 0.75 | 0.70 | 1.45 | 1.34 | 1.12 | 1.02 | 0.96 | 1.01 | 1.82 | 2.76 |
| Betaine | 0.68 | 0.72 | 1.01 | 1.06 | 0.88 | 1.59 | 0.90 | 0.89 | 0.78 | 1.05 | 1.82 | 3.37 |
| Betaine aldehyde_+H2O | 2.00 | 1.53 | 1.10 | 1.31 | 0.82 | 0.92 | 0.84 | 0.95 | 1.04 | 0.44 | 1.44 | 2.25 |
| CDP | 1.32 | 1.35 | 1.05 | 0.77 | 1.18 | 1< | 0.85 | 0.70 | 1.02 | 1.20 | N.A. | N.A. |
| CMP | 1.44 | 1.61 | 0.46 | 0.49 | 0.91 | 1.20 | 1.40 | 0.84 | 1.24 | 1.13 | 0.94 | 0.99 |
| CTP | 0.71 | 0.79 | 1.07 | 0.92 | N.A. | N.A. | 0.87 | 0.90 | N.A. | N.A. | N.A. | N.A. |
| Carnosine | 1.90 | 3.87 | 1.57 | 1.57 | 1.22 | 0.98 | 1.05 | 1.38 | 1.30 | 0.87 | 1< | 1< |
| Choline | 2.18 | 1.80 | 0.89 | 1.06 | 0.95 | 1.10 | 1.17 | 1.36 | 1.13 | 1.21 | 1.79 | 1.89 |
| Citric acid | 0.97 | 1.02 | 0.57 | 0.77 | 1.11 | 0.82 | 0.86 | 0.77 | 0.95 | 0.90 | 1.51 | 2.02 |
| Citrulline | 1.24 | 1.03 | 0.98 | 0.96 | 1.58 | 2.03 | 1.20 | 1.07 | 0.93 | 1.06 | 2.19 | 2.41 |
| CoA_divalent | <1 | <1 | 1.67 | 1.54 | 0.88 | 0.84 | 1.12 | 1.08 | 1.14 | 1.22 | N.A. | N.A. |
| Creatine | 0.98 | 1.16 | 0.99 | 1.08 | 1.49 | 1.40 | 0.96 | 1.08 | 1.04 | 1.07 | 1.64 | 3.03 |
| Creatinine | 1.35 | 1.29 | 0.80 | 0.63 | 1.18 | 1.25 | 1.03 | 0.98 | 1.34 | 1.46 | 2.58 | 3.37 |
| Cys | 1.15 | 1< | 1.37 | 1.45 | 0.63 | 0.75 | 0.89 | 1.29 | 0.73 | 1.69 | N.A. | N.A. |
| Cytidine | 1.35 | 1.28 | 0.61 | 0.74 | 1.76 | 1.50 | 1.20 | 1.27 | 1.28 | 1.31 | 3.37 | 4.10 |
| Cytosine | 2.03 | 1.37 | N.A. | N.A. | N.A. | N.A. | N.A. | N.A. | 1< | N.A. | N.A. | N.A. |
| Dihydroxyacetone phosphate | 2.54 | 1.66 | N.A. | N.A. | 0.52 | 0.35 | 0.92 | 0.92 | 1.11 | 0.61 | 4.01 | 2.04 |
| Erythrose 4-phosphate | N.A. | N.A. | N.A. | N.A. | N.A. | N.A. | N.A. | N.A. | N.A. | N.A. | N.A. | N.A. |
| Fructose 1,6-diphosphate | 1.35 | 1.76 | N.A. | N.A. | N.A. | N.A. | 1.37 | 0.65 | 1.02 | 0.69 | 5.38 | 4.42 |
| Fructose 6-phosphate | 3.43 | 3.11 | 0.84 | 0.82 | 1.03 | 0.35 | 0.92 | 0.94 | 1.03 | 0.78 | 5.40 | 4.24 |
| Fumaric acid | 0.93 | 1.03 | 1.04 | 0.99 | 1.45 | 0.83 | 1.01 | 0.99 | 1.08 | 0.99 | N.A. | N.A. |
| GABA | 1.04 | 1.28 | 0.85 | 0.80 | 1.25 | 1.30 | 0.84 | 0.83 | 0.79 | 1.03 | 1.08 | 3.18 |
| GDP | 0.83 | 0.93 | 1.04 | 0.99 | 1.14 | 0.87 | 0.93 | 0.90 | 1.25 | 1.34 | 1.28 | 1.69 |
| GMP | 1.04 | 1.18 | 0.69 | 0.55 | 0.75 | 0.82 | 1.44 | 0.62 | 0.97 | 1.15 | 0.69 | 0.91 |
| GTP | 0.44 | 0.59 | 1.30 | 1.17 | 1.64 | 0.66 | 0.76 | 0.88 | 1.28 | 1.33 | 1< | 1< |
| Gln | 1.32 | 0.98 | 0.85 | 0.68 | 0.81 | 0.74 | 1.08 | 1.11 | 1.22 | 1.18 | 2.47 | 2.85 |
| Glu | 0.85 | 0.86 | 0.91 | 0.88 | 1.32 | 1.40 | 1.12 | 1.11 | 1.10 | 1.15 | 1.77 | 3.24 |
| Gluconic acid | 1.59 | 1.31 | 0.75 | 0.86 | 1.40 | 1.59 | 0.92 | 1.00 | 1.06 | 1.02 | 1.62 | 2.70 |
| Glucose 1-phosphate | 1.55 | 1.63 | 0.47 | 0.53 | 0.68 | 0.35 | 0.90 | 0.87 | 0.87 | 0.68 | 2.99 | 3.31 |
| Glucose 6-phosphate | 2.07 | 2.51 | 0.83 | 0.81 | 1.05 | 0.22 | 1.03 | 1.01 | 0.85 | 0.77 | 5.62 | 6.10 |
| Glutathione (GSH) | 0.62 | 1< | N.A. | N.A. | 0.73 | 0.76 | 1.05 | 0.97 | 0.98 | 0.99 | N.A. | N.A. |
| Glutathione (GSSG)_divalent | 0.89 | 0.89 | N.A. | N.A. | 1.24 | 1.32 | 1.02 | 1.47 | 1.07 | 1.06 | 1.32 | 2.19 |
| Gly | 1.13 | 0.99 | 0.96 | 0.92 | 0.86 | 0.96 | 1.00 | 1.01 | 0.90 | 0.98 | 1.88 | 2.47 |
| Glycerol 3-phosphate | 0.81 | 0.86 | 0.86 | 1.09 | 1.08 | 0.57 | 1.21 | 1.37 | 1.12 | 1.16 | 1.63 | 1.36 |
| Guanine | 1.03 | 0.81 | 1.15 | 1.31 | 1.10 | 1.59 | 0.98 | 1.24 | 1.11 | 0.85 | N.A. | N.A. |
| Guanosine | 1.65 | 1.44 | 1.00 | 1.01 | 1.83 | 3.01 | 1.13 | 1.19 | 1.25 | 1.21 | 4.84 | 7.48 |
| His | 1.87 | 1.57 | 1.19 | 1.26 | 0.85 | 0.94 | 1.07 | 1.19 | 1.00 | 1.15 | 2.83 | 3.85 |
| Homoserine | 0.73 | 0.76 | 1.32 | 1.66 | 1.34 | 1.60 | 1.17 | 1.07 | 1.10 | 1.08 | N.A. | N.A. |
| Hydroxyproline | 0.51 | 0.54 | 0.67 | 0.81 | 1.15 | 1.29 | 0.81 | 0.91 | 0.81 | 0.93 | 1.95 | 2.98 |
| Hypoxanthine | 1.65 | 1.41 | 1.00 | 1.14 | 0.77 | 1.27 | 0.97 | 1.28 | 0.96 | 1.18 | 3.82 | 4.73 |
| IMP | 1.48 | 1.70 | 0.89 | 0.69 | 0.89 | 0.49 | 1.86 | 0.98 | 1.54 | 1.27 | 0.39 | 0.29 |
| Ile | 1.83 | 1.49 | 1.14 | 1.18 | 1.13 | 1.25 | 1.05 | 1.16 | 0.97 | 1.07 | 2.19 | 3.31 |
| Inosine | 1.86 | 1.57 | 1.05 | 1.27 | 1.07 | 1.42 | 1.13 | 1.31 | 1.12 | 1.23 | 3.93 | 6.52 |
| Isocitric acid | 1.03 | 0.98 | N.A. | N.A. | N.A. | N.A. | N.A. | N.A. | N.A. | N.A. | N.A. | N.A. |
| Lactic acid | 0.90 | 0.83 | 0.91 | 0.82 | 0.54 | 0.26 | 0.91 | 0.85 | 0.88 | 0.83 | 2.15 | 2.37 |

Fig. 33-3

| Metabolite | Testis | | Spleen | | Pancreas | | Brain | |
|---|---|---|---|---|---|---|---|---|
| | E | M | E | M | E | M | E | M |
| 2-Hydroxybutyric acid | 1.20 | 1.66 | 2.04 | 3.85 | 1.57 | 2.26 | 1.93 | 4.02 |
| 2-Oxoglutaric acid | N.A. | N.A. | N.A. | N.A. | N.A. | N.A. | N.A. | N.A. |
| 2-Oxoisovaleric acid | N.A. | N.A. | N.A. | N.A. | N.A. | N.A. | N.A. | N.A. |
| 2-Phosphoglyceric acid | N.A. | N.A. | N.A. | N.A. | N.A. | N.A. | N.A. | N.A. |
| 3-Hydroxybutyric acid | 0.37 | 0.51 | 0.59 | 0.87 | 0.88 | 1.51 | 0.62 | 0.99 |
| 3-Phosphoglyceric acid | 1.68 | 1.09 | 1.22 | 1.16 | N.A. | N.A. | 1< | 1< |
| 6-Phosphogluconic acid | 0.73 | 0.93 | 0.99 | 0.78 | 0.72 | 1.04 | 0.90 | 0.74 |
| ADP | 1.09 | 0.32 | 1.16 | 0.71 | 0.88 | 0.79 | 0.98 | 0.76 |
| AMP | 1.13 | 0.26 | 0.81 | 0.45 | 0.83 | 0.99 | 0.89 | 0.84 |
| ATP | 1.11 | 0.43 | 1.67 | 0.98 | 1.22 | 0.67 | 1.01 | 0.59 |
| Acetyl CoA_divalent | N.A. | N.A. | N.A. | N.A. | N.A. | N.A. | 1.72 | 1.07 |
| Adenine | 1.15 | 1.13 | 1.14 | 0.78 | 1.07 | 1.17 | 0.89 | 0.86 |
| Adenosine | 1.24 | 0.91 | 0.99 | 1.86 | 1.24 | 1.61 | 0.93 | 1.08 |
| Ala | 0.92 | 0.85 | 1.11 | 0.84 | 1.64 | 1.13 | 1.04 | 0.96 |
| Anthranilic acid | N.A. | N.A. | N.A. | N.A. | 3.01 | 3.26 | N.A. | N.A. |
| Arg | 0.66 | 0.72 | 1.19 | 1.05 | 1.09 | 0.93 | 0.88 | 0.95 |
| Asn | 1.08 | 1.29 | 1.28 | 1.12 | 1.11 | 0.99 | 0.99 | 1.02 |
| Asp | 1.14 | 1.20 | 1.00 | 1.04 | 0.98 | 1.13 | 0.98 | 0.99 |
| Betaine | 1.09 | 1.11 | 0.73 | 0.69 | 0.75 | 1.02 | 1.49 | 1.80 |
| Betaine aldehyde_+H2O | 0.77 | 0.96 | 0.91 | 1.23 | 1.03 | 1.24 | 1< | 0.88 |
| CDP | 1.35 | 1.13 | 1.53 | 1.05 | 1.39 | 0.89 | 0.74 | <1 |
| CMP | 1.13 | 0.56 | 1.10 | 0.81 | 1.50 | 1.32 | 0.96 | 1.17 |
| CTP | 1.03 | 1.26 | 1< | N.A. | 2.00 | N.A. | N.A. | N.A. |
| Carnosine | 0.98 | 1.08 | <1 | 1.37 | <1 | 1.81 | 1.34 | 0.95 |
| Choline | 1.00 | 1.12 | 1.20 | 1.09 | 0.88 | 1.02 | 1.00 | 1.15 |
| Citric acid | 0.89 | 0.71 | 1.05 | 0.94 | 0.51 | 0.39 | 1.12 | 1.06 |
| Citrulline | 0.96 | 0.76 | 0.94 | 0.79 | 1.17 | 1.08 | 0.88 | 0.86 |
| CoA_divalent | 1.01 | 1.04 | 1.14 | 0.94 | 0.81 | 1.07 | 0.97 | 1.05 |
| Creatine | 1.03 | 1.01 | 0.94 | 0.88 | 1.02 | 1.02 | 0.96 | 1.03 |
| Creatinine | 1.05 | 1.05 | 1.14 | 1.03 | 1.14 | 1.05 | 0.98 | 0.97 |
| Cys | 0.82 | 1.10 | 0.83 | 0.78 | 0.64 | 0.99 | 1.21 | 1.46 |
| Cytidine | 1.03 | 1.14 | 1.24 | 1.18 | 1.20 | 1.41 | 1.07 | 1.07 |
| Cytosine | N.A. | N.A. | N.A. | N.A. | 0.77 | 1.22 | N.A. | N.A. |
| Dihydroxyacetone phosphate | 1.00 | 0.56 | 1.34 | 1.24 | N.A. | N.A. | 0.77 | 0.71 |
| Erythrose 4-phosphate | N.A. | N.A. | N.A. | N.A. | N.A. | N.A. | N.A. | N.A. |
| Fructose 1,6-diphosphate | N.A. | N.A. | 1.31 | 1.27 | 1< | N.A. | N.A. | N.A. |
| Fructose 6-phosphate | 0.96 | 0.60 | 1.13 | 1.29 | 0.81 | 0.98 | 1.05 | 0.85 |
| Fumaric acid | 0.86 | 0.71 | 0.98 | 0.82 | 1.00 | 0.91 | 0.91 | 1.00 |
| GABA | 0.52 | 0.80 | 0.98 | 0.92 | 1.02 | 1.00 | 1.01 | 1.06 |
| GDP | 1.04 | 0.64 | 1.18 | 0.92 | 0.89 | 0.86 | 1.12 | 1.10 |
| GMP | 1.11 | 0.25 | 0.89 | 0.61 | 0.90 | 1.05 | 0.92 | 0.92 |
| GTP | 1.04 | 0.88 | 1.78 | 1.35 | 1.14 | 0.73 | 1.20 | 0.92 |
| Gln | 1.06 | 1.13 | 1.18 | 0.91 | 1.62 | 1.22 | 1.08 | 1.07 |
| Glu | 0.97 | 0.96 | 0.99 | 0.94 | 0.86 | 0.93 | 1.08 | 1.14 |
| Gluconic acid | 0.95 | 0.84 | 0.97 | 0.99 | 0.75 | 0.79 | 1< | 1< |
| Glucose 1-phosphate | 0.81 | 0.57 | 1.37 | 1.28 | 3.17 | 2.47 | 1.17 | 0.82 |
| Glucose 6-phosphate | 1.03 | 0.76 | 1.29 | 1.07 | 0.64 | 0.92 | 0.91 | 0.83 |
| Glutathione (GSH) | 1.00 | 0.99 | 0.93 | 0.93 | 0.52 | 0.37 | 0.96 | 1.04 |
| Glutathione (GSSG)_divalent | 0.94 | 0.91 | 0.97 | 0.82 | 0.81 | 0.17 | 1.08 | 0.98 |
| Gly | 1.11 | 1.12 | 1.10 | 0.99 | 0.92 | 0.95 | 1.00 | 1.05 |
| Glycerol 3-phosphate | 0.76 | 0.64 | 1.00 | 0.78 | 0.96 | 1.17 | 1.02 | 1.18 |
| Guanine | N.A. | N.A. | 1.01 | 1.21 | N.A. | N.A. | 0.96 | 0.87 |
| Guanosine | 1.03 | 1.07 | 1.21 | 1.52 | 1.49 | 1.94 | 1.30 | 1.50 |
| His | 1.01 | 1.09 | 1.06 | 0.94 | 1.91 | 1.61 | 0.94 | 1.02 |
| Homoserine | N.A. | 1< | 1< | 0.82 | N.A. | N.A. | 1.09 | 1.11 |
| Hydroxyproline | 1.17 | 1.22 | 0.89 | 0.77 | 0.77 | 0.71 | 1.28 | 1.33 |
| Hypoxanthine | 0.83 | 1.64 | 1.12 | 1.25 | 1.09 | 1.57 | 0.97 | 1.10 |
| IMP | 0.91 | 0.45 | 0.96 | 0.80 | 0.61 | 0.93 | 1.13 | 1.28 |
| Ile | 0.93 | 0.97 | 1.30 | 1.21 | 1.33 | 1.52 | 0.98 | 0.95 |
| Inosine | 0.76 | 1.25 | 1.22 | 1.35 | 1.44 | 1.84 | 1.24 | 1.39 |
| Isocitric acid | N.A. | N.A. | N.A. | N.A. | N.A. | N.A. | N.A. | N.A. |
| Lactic acid | 0.76 | 0.64 | 1.05 | 0.81 | 1.60 | 1.06 | 1.01 | 0.87 |

Fig. 33- 4

| Metabolite | Plasma | | Skeletal muscle | | Brown fat | | Heart | | Lung | |
|---|---|---|---|---|---|---|---|---|---|---|
| | E | M | E | M | E | M | E | M | E | M |
| Leu | 1.47 | 1.44 | 1.31 | 1.42 | 1.89 | 1.83 | 1.26 | 1.33 | 1.11 | 1.36 |
| Lys | 1.26 | 1.40 | 1.37 | 1.40 | 1.93 | 1.85 | 1.32 | 1.53 | 1.00 | 1.19 |
| Malic acid | 0.53 | 0.26 | 0.69 | 0.88 | 1.46 | 1.01 | 1.00 | 0.99 | 0.86 | 0.77 |
| Met | 1.41 | 1.56 | 1.12 | 1.24 | 1.75 | 1.91 | 1.02 | 1.18 | 1.10 | 1.76 |
| N,N-Dimethylglycine | 0.75 | 0.99 | 1.04 | 1.17 | 0.90 | 1.28 | 0.81 | 1.06 | 0.80 | 1.06 |
| NAD+ | N.A. | N.A. | 1.22 | 0.89 | 0.81 | 0.71 | 1.04 | 0.82 | 1.10 | 0.77 |
| NADP+ | N.A. | N.A. | 1.20 | 1.00 | 0.79 | 0.65 | 0.96 | 0.77 | 1.38 | 1.27 |
| Ornithine | 1.35 | 1.64 | 1.12 | 1.24 | 1.65 | 1.64 | 1.24 | 1.18 | 1.17 | 1.14 |
| PRPP | N.A. | N.A. | 1.14 | 0.89 | N.A. | N.A. | N.A. | N.A. | 1.24 | 1.01 |
| Phe | 1.26 | 1.15 | 1.16 | 1.20 | 1.70 | 1.81 | 1.16 | 1.16 | 1.09 | 1.20 |
| Phosphoenolpyruvic acid | N.A. | N.A. | N.A. | N.A. | 1.32 | 1.41 | 1.21 | 0.74 | 0.96 | 0.88 |
| Pro | 1.13 | 1.08 | 1.27 | 1.52 | 1.68 | 1.54 | 0.99 | 1.03 | 0.93 | 1.08 |
| Putrescine | 1.01 | 1< | 2.79 | 3.73 | 1.32 | 1.10 | 1.12 | 0.65 | 0.59 | 0.56 |
| Pyruvic acid | 2.16 | 0.83 | N.A. | N.A. | 1.46 | <1 | N.A. | N.A. | 0.93 | 0.72 |
| Ribose 5-phosphate | N.A. | N.A. | 1.06 | 1.40 | 0.83 | 1.24 | 0.92 | 0.73 | 1.02 | 1.29 |
| Ribulose 5-phosphate | 1.43 | 0.38 | 1.03 | 1.37 | 1.33 | 1.78 | 1.09 | 1.14 | 1.29 | 1.61 |
| S-Adenosylmethionine | N.A. | <1 | 0.89 | 0.93 | 0.75 | 0.88 | 1.19 | 1.11 | 0.92 | 0.96 |
| Sarcosine | 1.16 | 1.83 | 0.63 | 1.20 | 1.39 | 2.01 | 0.92 | 1< | 1.72 | 3.11 |
| Sedoheptulose 7-phosphate | N.A. | N.A. | N.A. | N.A. | 0.92 | 1.22 | 0.91 | 1.44 | 1.15 | 1.43 |
| Ser | 1.28 | 1.30 | 1.11 | 1.36 | 1.47 | 1.36 | 1.06 | 1.01 | 1.10 | 1.16 |
| Spermidine | 2.24 | 2.42 | 1.92 | 1.89 | 1.04 | 1.19 | 0.99 | 0.61 | 0.94 | 0.87 |
| Spermine | N.A. | N.A. | 1.05 | <1 | 1.24 | 1.57 | 1.21 | 0.70 | 1.15 | 1.08 |
| Succinic acid | 0.85 | <1 | 0.66 | 0.68 | 1.21 | 1.02 | 1.12 | 0.90 | 0.75 | 0.59 |
| Thr | 1.29 | 1.44 | 1.14 | 1.53 | 1.43 | 1.49 | 1.23 | 1.41 | 1.09 | 1.44 |
| Thymidine | 1.91 | 1.78 | N.A. | N.A. | N.A. | N.A. | N.A. | N.A. | N.A. | N.A. |
| Trp | 1.03 | 0.96 | 1.02 | 1.22 | 1.60 | 1.66 | 1.01 | 1.07 | 0.98 | 1.08 |
| Tyr | 1.08 | 1.13 | 1.09 | 1.13 | 1.61 | 1.79 | 0.99 | 1.06 | 1.18 | 1.14 |
| Tyramine | N.A. | N.A. | N.A. | N.A. | 1< | 1.20 | N.A. | N.A. | N.A. | N.A. |
| UDP | 1< | <1 | 2.04 | 2.42 | 2.47 | 0.99 | 1.00 | 0.63 | 1.63 | 0.77 |
| UMP | N.A. | N.A. | 1.00 | 1.18 | 1.06 | 1.07 | 1.09 | 0.61 | 1.10 | 0.86 |
| UTP | 1< | <1 | 0.99 | 0.62 | 4.15 | 1.18 | 1.05 | <1 | 0.88 | 0.70 |
| Uracil | 1.94 | 1.39 | N.A. | N.A. | 1.47 | 1.52 | 0.87 | 0.95 | 1.06 | 1.40 |
| Uridine | 1.49 | 0.98 | 1.24 | 1.31 | 1.40 | 1.41 | 1.18 | 1.25 | 1.22 | 1.54 |
| Val | 1.50 | 1.69 | 1.25 | 1.45 | 1.84 | 1.86 | 1.18 | 1.34 | 1.26 | 1.45 |
| cAMP | N.A. | N.A. | N.A. | N.A. | 1.11 | 1.22 | N.A. | N.A. | 1.34 | 0.93 |
| cGMP | N.A. | N.A. | N.A. | N.A. | N.A. | N.A. | N.A. | N.A. | N.A. | N.A. |
| cis-Aconitic acid | 0.68 | 0.55 | N.A. | N.A. | 1.50 | 0.86 | N.A. | N.A. | 0.75 | 0.70 |
| dATP | N.A. | N.A. | N.A. | N.A. | N.A. | N.A. | N.A. | N.A. | N.A. | N.A. |
| dCTP | N.A. | N.A. | N.A. | N.A. | N.A. | N.A. | N.A. | N.A. | N.A. | N.A. |
| dTDP | N.A. | N.A. | N.A. | N.A. | N.A. | N.A. | N.A. | N.A. | N.A. | N.A. |
| dTMP | N.A. | N.A. | N.A. | N.A. | 0.72 | <1 | N.A. | N.A. | N.A. | N.A. |
| dTTP | N.A. | N.A. | N.A. | N.A. | N.A. | N.A. | N.A. | N.A. | N.A. | N.A. |
| β-Ala | 1.64 | 1.08 | 2.25 | 2.23 | 2.82 | 2.83 | 1.94 | 2.01 | 2.27 | 1.93 |

1<: SAMR1 in SAMP8/SAMR1 is below the detection limit.
<1: SAMRP8 in SAMP8/SAMR1 is below the detection limit.

Fig. 33- 5

| Metabolite | Thymus | | Kidney | | Liver | | Colon | | Stomach | | Adipose tissue | |
|---|---|---|---|---|---|---|---|---|---|---|---|---|
| | E | M | E | M | E | M | E | M | E | M | E | M |
| Leu | 1.78 | 1.50 | 1.18 | 1.29 | 1.10 | 1.21 | 1.10 | 1.24 | 0.96 | 1.08 | 2.64 | 3.90 |
| Lys | 2.28 | 1.80 | 1.02 | 1.18 | 1.34 | 1.67 | 0.93 | 1.05 | 0.91 | 1.04 | 2.45 | 3.41 |
| Malic acid | 0.90 | 0.97 | 0.78 | 0.39 | 1.81 | 0.78 | 0.99 | 0.92 | 0.86 | 0.89 | 2.15 | 2.69 |
| Met | 1.57 | 1.52 | 1.13 | 1.30 | 1.08 | 1.62 | 1.06 | 1.24 | 0.86 | 1.16 | 2.28 | 3.71 |
| N,N-Dimethylglycine | 0.95 | 1.22 | 0.64 | 0.98 | 1.05 | 1.57 | 0.87 | 1.18 | 1.01 | 1.49 | 1.76 | 2.16 |
| NAD+ | 0.61 | 0.80 | 1.33 | 1.06 | 0.77 | 0.60 | 0.92 | 1.03 | 1.20 | 1.06 | 1.16 | 1.54 |
| NADP+ | 0.63 | 0.79 | 1.55 | 1.27 | 0.79 | 0.49 | 1.09 | 0.89 | 1.29 | 1.06 | 1.07 | 1< |
| Ornithine | 1.38 | 1.19 | 1.08 | 1.30 | 1.45 | 1.91 | 1.04 | 1.18 | 0.77 | 1.02 | 1.99 | 2.93 |
| PRPP | 0.54 | 0.65 | N.A. | N.A. | N.A. | N.A. | 0.83 | N.A. | 1.17 | 1.12 | N.A. | N.A. |
| Phe | 1.65 | 1.44 | 1.11 | 1.13 | 1.00 | 0.94 | 1.11 | 1.15 | 0.96 | 1.03 | 2.44 | 3.45 |
| Phosphoenolpyruvic acid | 1< | 1< | 0.83 | 0.89 | N.A. | N.A. | 1.37 | <1 | N.A. | N.A. | N.A. | N.A. |
| Pro | 1.30 | 1.15 | 0.97 | 1.03 | 1.08 | 1.13 | 1.04 | 1.02 | 0.99 | 1.07 | 2.54 | 3.39 |
| Putrescine | 2.25 | 1.43 | 0.97 | 0.87 | 1.40 | 0.84 | 0.83 | 0.78 | 0.80 | 0.79 | 1.75 | 1.51 |
| Pyruvic acid | N.A. | N.A. | N.A. | N.A. | 0.70 | 0.38 | 0.95 | 1.19 | 1.00 | 1.08 | N.A. | N.A. |
| Ribose 5-phosphate | 4.17 | 2.27 | 0.78 | 1.10 | 0.80 | 0.62 | 0.81 | 1.08 | 0.99 | 0.95 | 1.71 | 2.71 |
| Ribulose 5-phosphate | 2.39 | 1.64 | 1.07 | 1.38 | 1.20 | 1.27 | 1.03 | 1.07 | 0.80 | 0.97 | 2.84 | 3.98 |
| S-Adenosylmethionine | 0.94 | 0.93 | 0.93 | 0.91 | 0.40 | 0.26 | 1.00 | 1.08 | 1.11 | 1.16 | 1.53 | 3.10 |
| Sarcosine | 0.89 | 1.12 | 0.71 | 1.60 | 2.11 | 4.87 | 2.25 | 2.84 | 1.44 | 2.60 | 1< | N.A. |
| Sedoheptulose 7-phosphate | 1.88 | 1.60 | 0.79 | 0.97 | 1.18 | 1.22 | 1.28 | 1.33 | 1.16 | 1.39 | 2.58 | 2.62 |
| Ser | 1.08 | 0.91 | 1.05 | 1.17 | 1.00 | 1.09 | 0.94 | 1.06 | 0.97 | 1.01 | 2.21 | 3.31 |
| Spermidine | 0.70 | 0.72 | 1.28 | 1.39 | 1.93 | 1.39 | 1.05 | 0.88 | 0.96 | 1.29 | 2.49 | 3.53 |
| Spermine | <1 | <1 | 1.33 | 1.24 | 1.29 | 1.12 | 1.03 | 0.99 | 2.49 | 2.17 | 1< | 1< |
| Succinic acid | 0.43 | 0.60 | 0.81 | 0.69 | 0.76 | 0.54 | 0.97 | 0.98 | 0.82 | 0.92 | 0.98 | 1.36 |
| Thr | 1.28 | 1.33 | 1.16 | 1.36 | 1.04 | 1.26 | 1.05 | 1.40 | 1.11 | 1.35 | 2.42 | 4.06 |
| Thymidine | 3.14 | 1.93 | 0.98 | 1.27 | N.A. | N.A. | 1.18 | 1.30 | 1.02 | 1.35 | N.A. | N.A. |
| Trp | 1.64 | 1.33 | 1.02 | 1.08 | 0.94 | 0.95 | 0.95 | 1.11 | 0.85 | 0.98 | 2.09 | 3.04 |
| Tyr | 1.93 | 1.53 | 0.97 | 1.18 | 0.86 | 0.94 | 1.02 | 1.15 | 0.89 | 0.99 | 2.48 | 3.37 |
| Tyramine | N.A. | N.A. | N.A. | N.A. | N.A. | N.A. | N.A. | N.A. | <1 | <1 | N.A. | N.A. |
| UDP | 0.77 | 0.88 | 0.88 | 0.80 | 1.21 | 0.66 | 0.74 | 0.65 | 1.27 | 1.38 | N.A. | N.A. |
| UMP | 0.89 | 1.12 | 0.28 | 0.28 | 0.95 | 0.98 | 1.18 | 0.51 | 1.03 | 1.27 | 0.45 | 0.59 |
| UTP | 0.41 | 0.55 | 1.06 | 0.91 | 1.84 | 0.55 | 0.66 | 0.90 | 1.41 | 1.46 | N.A. | N.A. |
| Uracil | 1.39 | 1.11 | 0.83 | 0.96 | 1.31 | 1.38 | 1.25 | 1.44 | 1.01 | 1.03 | 1< | 1< |
| Uridine | 1.13 | 1.00 | 0.75 | 0.83 | 1.22 | 1.35 | 1.00 | 1.09 | 1.03 | 1.33 | 3.16 | 4.08 |
| Val | 1.73 | 1.57 | 1.15 | 1.32 | 1.21 | 1.34 | 1.17 | 1.35 | 1.07 | 1.25 | 2.58 | 3.60 |
| cAMP | 1.49 | 1.29 | N.A. | N.A. | N.A. | N.A. | 1.10 | 1.05 | N.A. | N.A. | N.A. | N.A. |
| cGMP | N.A. | N.A. | N.A. | N.A. | N.A. | N.A. | N.A. | N.A. | N.A. | N.A. | N.A. | N.A. |
| cis-Aconitic acid | 1.16 | 1.09 | N.A. | N.A. | N.A. | N.A. | 0.59 | 0.66 | 0.85 | 0.79 | N.A. | N.A. |
| dATP | 0.52 | 0.61 | N.A. | N.A. | N.A. | N.A. | N.A. | N.A. | N.A. | N.A. | N.A. | N.A. |
| dCTP | 0.53 | 0.64 | N.A. | N.A. | N.A. | N.A. | N.A. | N.A. | N.A. | N.A. | N.A. | N.A. |
| dTDP | 1.05 | 1.09 | N.A. | N.A. | N.A. | N.A. | N.A. | N.A. | N.A. | N.A. | N.A. | N.A. |
| dTMP | 1.40 | 1.29 | N.A. | N.A. | N.A. | N.A. | N.A. | N.A. | N.A. | N.A. | N.A. | N.A. |
| dTTP | 0.63 | 0.73 | N.A. | N.A. | N.A. | N.A. | N.A. | N.A. | N.A. | N.A. | N.A. | N.A. |
| β-Ala | 1.60 | 1.60 | 1.10 | 1.04 | 0.86 | 1.18 | 1.35 | 1.27 | 1.40 | 1.46 | 2.35 | 2.88 |

1<: SAMR1 in SAMP8/SAMR1 is below the detection limit.
<1: SAMRP8 in SAMP8/SAMR1 is below the detection limit.

Fig. 33- 6

| Metabolite | Testis | | Spleen | | Pancreas | | Brain | |
|---|---|---|---|---|---|---|---|---|
| | E | M | E | M | E | M | E | M |
| Leu | 1.02 | 1.06 | 1.22 | 1.13 | 1.29 | 1.34 | 1.01 | 1.05 |
| Lys | 0.82 | 1.00 | 1.16 | 1.07 | 0.98 | 1.05 | 0.82 | 0.86 |
| Malic acid | 0.71 | 0.48 | 0.92 | 0.85 | 0.93 | 0.96 | 0.95 | 0.92 |
| Met | 0.90 | 1.08 | 0.94 | 1.35 | 2.05 | 2.94 | 0.95 | 0.95 |
| N,N-Dimethylglycine | 0.86 | 0.94 | 0.84 | 0.96 | 0.72 | 0.92 | 1< | 1< |
| NAD+ | 1.05 | 0.74 | 1.09 | 0.79 | 1.06 | 0.95 | 1.05 | 0.88 |
| NADP+ | 1.00 | 0.83 | 0.72 | 0.51 | 0.91 | 0.86 | 1.10 | 0.83 |
| Ornithine | 1.09 | 0.90 | 0.93 | 1.04 | 0.92 | 1.03 | 0.81 | 0.85 |
| PRPP | 1.04 | 1.05 | 1.46 | 1.54 | 1.28 | 1.03 | 0.98 | 1.21 |
| Phe | 0.94 | 0.98 | 1.12 | 0.98 | 1.33 | 1.44 | 0.83 | 0.89 |
| Phosphoenolpyruvic acid | N.A. | N.A. | 1.15 | 1.16 | N.A. | N.A. | <1 | N.A. |
| Pro | 1.14 | 1.31 | 1.20 | 1.09 | 1.11 | 1.20 | 1.02 | 1.02 |
| Putrescine | 0.54 | 0.67 | 0.83 | 0.60 | 0.81 | 0.66 | 1.08 | 1.00 |
| Pyruvic acid | N.A. | N.A. | N.A. | N.A. | N.A. | N.A. | N.A. | N.A. |
| Ribose 5-phosphate | <1 | 1.81 | 3.07 | 1.27 | N.A. | N.A. | 0.92 | 1.17 |
| Ribulose 5-phosphate | 0.99 | 1.88 | 1.03 | 1.53 | 1.21 | 1.22 | 0.94 | 1.10 |
| S-Adenosylmethionine | 1.21 | 1.15 | 1.02 | 0.99 | 1.10 | 1.48 | 0.81 | 0.85 |
| Sarcosine | 0.89 | 0.98 | 1.15 | 1.43 | 1.35 | 4.34 | N.A. | N.A. |
| Sedoheptulose 7-phosphate | 0.91 | 1.09 | 0.98 | 1.30 | 0.93 | 1.49 | 1.04 | 1.42 |
| Ser | 1.16 | 1.21 | 1.10 | 0.99 | 0.87 | 0.89 | 1.03 | 1.09 |
| Spermidine | 0.85 | 0.98 | 1.16 | 0.81 | 1.06 | 2.12 | 1.01 | 1.00 |
| Spermine | 0.86 | 0.71 | 1.50 | 1.07 | 1.74 | 3.98 | 1.17 | 1.10 |
| Succinic acid | 0.72 | 0.67 | 0.67 | 0.59 | 0.98 | 1.09 | 0.98 | 1.04 |
| Thr | 1.05 | 1.36 | 1.24 | 1.19 | 1.32 | 1.78 | 1.03 | 1.27 |
| Thymidine | 0.91 | 1.09 | 2.34 | 1.91 | N.A. | N.A. | N.A. | N.A. |
| Trp | 0.80 | 0.93 | 1.06 | 1.05 | 1.30 | 1.50 | 0.73 | 0.81 |
| Tyr | 0.86 | 0.90 | 1.17 | 1.08 | 1.98 | 1.74 | 0.70 | 0.80 |
| Tyramine | N.A. | N.A. | N.A. | N.A. | N.A. | N.A. | N.A. | N.A. |
| UDP | 1.07 | 0.69 | 1.34 | 0.93 | 1.25 | 1.05 | 0.86 | 0.55 |
| UMP | 1.08 | 0.26 | 0.91 | 0.54 | 1.38 | 1.49 | 0.93 | 0.98 |
| UTP | 1.13 | 0.82 | 1.84 | 1.28 | 1.62 | 0.93 | N.A. | N.A. |
| Uracil | 1.02 | 1.08 | 1.14 | 1.26 | 1.33 | 1.62 | 1.05 | 1.07 |
| Uridine | 1.04 | 1.10 | 1.25 | 1.34 | 1.24 | 1.57 | 1.09 | 1.14 |
| Val | 1.04 | 1.12 | 1.28 | 1.25 | 1.54 | 1.80 | 0.98 | 1.02 |
| cAMP | N.A. | N.A. | 1.11 | 1.10 | N.A. | N.A. | N.A. | N.A. |
| cGMP | N.A. | N.A. | N.A. | N.A. | N.A. | N.A. | N.A. | 1.02 |
| cis-Aconitic acid | N.A. | N.A. | 1.14 | 0.76 | 0.65 | 0.44 | N.A. | 1< |
| dATP | N.A. | N.A. | N.A. | N.A. | N.A. | N.A. | N.A. | N.A. |
| dCTP | N.A. | N.A. | N.A. | N.A. | N.A. | N.A. | N.A. | N.A. |
| dTDP | N.A. | N.A. | N.A. | N.A. | N.A. | N.A. | N.A. | N.A. |
| dTMP | N.A. | N.A. | 1.15 | 0.58 | N.A. | N.A. | N.A. | N.A. |
| dTTP | N.A. | N.A. | N.A. | N.A. | N.A. | N.A. | N.A. | N.A. |
| β-Ala | 1.06 | 1.23 | 2.30 | 2.08 | 1.14 | 1.28 | 1.18 | 1.03 |

1<: SAMR1 in SAMP8/SAMR1 is below the detection limit.
<1: SAMRP8 in SAMP8/SAMR1 is below the detection limit.

Fig. 34 - 1

| Line No. | Group No. | | | | | Sub-Groups | Gene Name |
|---|---|---|---|---|---|---|---|
| 1 | 3 | 4 | 5 | 6 | 7 | VII-2 | 0610010B08Rik |
| 2 | 3 | 4 | 5 | 6 | 7 | VII-2 | 0610031O16Rik |
| 3 | 3 | 4 | 5 | 6 | 7 | VII-2 | 1110007C09Rik |
| 4 | 3 | 4 | 5 | 6 | 7 | VII-2 | 1500017E21Rik |
| 5 | 3 | 4 | 5 | 6 | 7 | VII-2 | 1600029D14Rik |
| 6 | 3 | 4 | 5 | 6 | 7 | VII-2 | 1700001C02Rik |
| 7 | 3 | 4 | 5 | 6 | 7 | VII-2 | 1700003C15Rik |
| 8 | 3 | 4 | 5 | 6 | 7 | VII-2 | 1700006A11Rik |
| 9 | 3 | 4 | 5 | 6 | 7 | VII-2 | 1700020L24Rik |
| 10 | 3 | 4 | 5 | 6 | 7 | VII-2 | 1700023L04Rik |
| 11 | 3 | 4 | 5 | 6 | 7 | VII-2 | 1700025K24Rik |
| 12 | 3 | 4 | 5 | 6 | 7 | VII-2 | 1700028B04Rik |
| 13 | 3 | 4 | 5 | 6 | 7 | VII-2 | 1700029P11Rik |
| 14 | 3 | 4 | 5 | 6 | 7 | VII-2 | 1700044K03Rik |
| 15 | 3 | 4 | 5 | 6 | 7 | VII-2 | 1700045H11Rik |
| 16 | 3 | 4 | 5 | 6 | 7 | VII-2 | 1700047G03Rik |
| 17 | 3 | 4 | 5 | 6 | 7 | VII-2 | 1700088E04Rik |
| 18 | 3 | 4 | 5 | 6 | 7 | VII-2 | 1700123I01Rik |
| 19 | 3 | 4 | 5 | 6 | 7 | VII-2 | 1810007D17Rik |
| 20 | 3 | 4 | 5 | 6 | 7 | VII-2 | 1810021B22Rik |
| 21 | 3 | 4 | 5 | 6 | 7 | VII-2 | 1810030O07Rik |
| 22 | 3 | 4 | 5 | 6 | 7 | VII-2 | 1810043H04Rik |
| 23 | 3 | 4 | 5 | 6 | 7 | VII-2 | 1810064F22Rik |
| 24 | 3 | 4 | 5 | 6 | 7 | VII-2 | 2010016I18Rik |
| 25 | 3 | 4 | 5 | 6 | 7 | VII-2 | 2310015A10Rik |
| 26 | 3 | 4 | 5 | 6 | 7 | VII-2 | 2410017I17Rik |
| 27 | 3 | 4 | 5 | 6 | 7 | VII-2 | 2510003E04Rik |
| 28 | 3 | 4 | 5 | 6 | 7 | VII-2 | 2610001J05Rik |
| 29 | 3 | 4 | 5 | 6 | 7 | VII-2 | 2610035D17Rik |
| 30 | 3 | 4 | 5 | 6 | 7 | VII-2 | 2610203C20Rik |
| 31 | 3 | 4 | 5 | 6 | 7 | VII-2 | 2610528J11Rik |
| 32 | 3 | 4 | 5 | 6 | 7 | VII-2 | 2810004N23Rik |
| 33 | 3 | 4 | 5 | 6 | 7 | VII-2 | 2810403A07Rik |
| 34 | 3 | 4 | 5 | 6 | 7 | VII-2 | 3010033K07Rik |
| 35 | 3 | 4 | 5 | 6 | 7 | VII-2 | 4732471J01Rik |
| 36 | 3 | 4 | 5 | 6 | 7 | VII-2 | 4921524J17Rik |
| 37 | 3 | 4 | 5 | 6 | 7 | VII-2 | 4921525O09Rik |
| 38 | 3 | 4 | 5 | 6 | 7 | VII-2 | 4930401O12Rik |
| 39 | 3 | 4 | 5 | 6 | 7 | VII-2 | 4930402H24Rik |
| 40 | 3 | 4 | 5 | 6 | 7 | VII-2 | 4930412O13Rik |
| 41 | 3 | 4 | 5 | 6 | 7 | VII-2 | 4930413G21Rik |
| 42 | 3 | 4 | 5 | 6 | 7 | VII-2 | 4930519F09Rik |
| 43 | 3 | 4 | 5 | 6 | 7 | VII-2 | 4930594C11Rik |
| 44 | 3 | 4 | 5 | 6 | 7 | VII-2 | 4933402N22Rik |
| 45 | 3 | 4 | 5 | 6 | 7 | VII-2 | 4933417G07Rik |
| 46 | 3 | 4 | 5 | 6 | 7 | VII-2 | 4933421I07Rik |
| 47 | 3 | 4 | 5 | 6 | 7 | VII-2 | 4933426M11Rik |
| 48 | 3 | 4 | 5 | 6 | 7 | VII-2 | 4933430N04Rik |
| 49 | 3 | 4 | 5 | 6 | 7 | VII-2 | 5730416F02Rik |
| 50 | 3 | 4 | 5 | 6 | 7 | VII-2 | 5830403L16Rik |
| 51 | 3 | 4 | 5 | 6 | 7 | VII-2 | 5830454E08Rik |
| 52 | 3 | 4 | 5 | 6 | 7 | VII-2 | 6430571L13Rik |
| 53 | 3 | 4 | 5 | 6 | 7 | VII-2 | 6430706D22Rik |
| 54 | 3 | 4 | 5 | 6 | 7 | VII-2 | 8430429K09Rik |
| 55 | 3 | 4 | 5 | 6 | 7 | VII-2 | 9130221H12Rik |
| 56 | 3 | 4 | 5 | 6 | 7 | VII-2 | 9230104L09Rik |
| 57 | 3 | 4 | 5 | 6 | 7 | VII-2 | 9330151L19Rik |
| 58 | 3 | 4 | 5 | 6 | 7 | VII-2 | 9330159F19Rik |
| 59 | 3 | 4 | 5 | 6 | 7 | VII-2 | 9530002B09Rik |
| 60 | 3 | 4 | 5 | 6 | 7 | VII-2 | 9530053A07Rik |
| 61 | 3 | 4 | 5 | 6 | 7 | VII-2 | 9630033F20Rik |
| 62 | 3 | 4 | 5 | 6 | 7 | VII-2 | A530016L24Rik |
| 63 | 3 | 4 | 5 | 6 | 7 | VII-2 | A530050N04Rik |
| 64 | 3 | 4 | 5 | 6 | 7 | VII-2 | A730008H23Rik |
| 65 | 3 | 4 | 5 | 6 | 7 | VII-2 | A930015D03Rik |
| 66 | 3 | 4 | 5 | 6 | 7 | VII-2 | AA465934 |
| 67 | 3 | 4 | 5 | 6 | 7 | VII-2 | AI597479 |
| 68 | 3 | 4 | 5 | 6 | 7 | VII-2 | AI607873 |
| 69 | 3 | 4 | 5 | 6 | 7 | VII-2 | AI747448 |
| 70 | 3 | 4 | 5 | 6 | 7 | VII-2 | AY074887 |
| 71 | 3 | 4 | 5 | 6 | 7 | VII-2 | Abat |
| 72 | 3 | 4 | 5 | 6 | 7 | VII-2 | Abca12 |
| 73 | 3 | 4 | 5 | 6 | 7 | VII-2 | Abca5 |
| 74 | 3 | 4 | 5 | 6 | 7 | VII-2 | Abcd1 |
| 75 | 3 | 4 | 5 | 6 | 7 | VII-2 | Abcd2 |
| 76 | 3 | 4 | 5 | 6 | 7 | VII-2 | Abcg4 |
| 77 | 3 | 4 | 5 | 6 | 7 | VII-2 | Abhd1 |
| 78 | 3 | 4 | 5 | 6 | 7 | VII-2 | Abhd2 |
| 79 | 3 | 4 | 5 | 6 | 7 | VII-2 | Abl1 |
| 80 | 3 | 4 | 5 | 6 | 7 | VII-2 | Abr |
| 81 | 3 | 4 | 5 | 6 | 7 | VII-2 | Acadm |
| 82 | 3 | 4 | 5 | 6 | 7 | VII-2 | Acap2 |
| 83 | 3 | 4 | 5 | 6 | 7 | VII-2 | Acbd3 |
| 84 | 3 | 4 | 5 | 6 | 7 | VII-2 | Accs |
| 85 | 3 | 4 | 5 | 6 | 7 | VII-2 | Ache |
| 86 | 3 | 4 | 5 | 6 | 7 | VII-2 | Ackr4 |
| 87 | 3 | 4 | 5 | 6 | 7 | VII-2 | Acp5 |
| 88 | 3 | 4 | 5 | 6 | 7 | VII-2 | Acsbg1 |
| 89 | 3 | 4 | 5 | 6 | 7 | VII-2 | Acsm3 |
| 90 | 3 | 4 | 5 | 6 | 7 | VII-2 | Actn2 |
| 91 | 3 | 4 | 5 | 6 | 7 | VII-2 | Acvr1b |
| 92 | 3 | 4 | 5 | 6 | 7 | VII-2 | Acvr1c |
| 93 | 3 | 4 | 5 | 6 | 7 | VII-2 | Acyp1 |
| 94 | 3 | 4 | 5 | 6 | 7 | VII-2 | Adam11 |
| 95 | 3 | 4 | 5 | 6 | 7 | VII-2 | Adam7 |
| 96 | 3 | 4 | 5 | 6 | 7 | VII-2 | Adam9 |
| 97 | 3 | 4 | 5 | 6 | 7 | VII-2 | Adap2 |
| 98 | 3 | 4 | 5 | 6 | 7 | VII-2 | Adc |
| 99 | 3 | 4 | 5 | 6 | 7 | VII-2 | Adcy6 |
| 100 | 3 | 4 | 5 | 6 | 7 | VII-2 | Adcy7 |
| 101 | 3 | 4 | 5 | 6 | 7 | VII-2 | Add2 |
| 102 | 3 | 4 | 5 | 6 | 7 | VII-2 | Adnp |
| 103 | 3 | 4 | 5 | 6 | 7 | VII-2 | Adnp2 |
| 104 | 3 | 4 | 5 | 6 | 7 | VII-2 | Adra1d |
| 105 | 3 | 4 | 5 | 6 | 7 | VII-2 | Adrb1 |
| 106 | 3 | 4 | 5 | 6 | 7 | VII-2 | Adrb3 |
| 107 | 3 | 4 | 5 | 6 | 7 | VII-2 | Adrbk2 |
| 108 | 3 | 4 | 5 | 6 | 7 | VII-2 | Aebp2 |
| 109 | 3 | 4 | 5 | 6 | 7 | VII-2 | Afap1l2 |
| 110 | 3 | 4 | 5 | 6 | 7 | VII-2 | Aga |
| 111 | 3 | 4 | 5 | 6 | 7 | VII-2 | Agfg2 |
| 112 | 3 | 4 | 5 | 6 | 7 | VII-2 | Agmo |
| 113 | 3 | 4 | 5 | 6 | 7 | VII-2 | Ago4 |
| 114 | 3 | 4 | 5 | 6 | 7 | VII-2 | Agpat2 |
| 115 | 3 | 4 | 5 | 6 | 7 | VII-2 | Ahcyl2 |
| 116 | 3 | 4 | 5 | 6 | 7 | VII-2 | Ahr |
| 117 | 3 | 4 | 5 | 6 | 7 | VII-2 | Aim |
| 118 | 3 | 4 | 5 | 6 | 7 | VII-2 | Ajuba |
| 119 | 3 | 4 | 5 | 6 | 7 | VII-2 | Ak1 |
| 120 | 3 | 4 | 5 | 6 | 7 | VII-2 | Ak4 |
| 121 | 3 | 4 | 5 | 6 | 7 | VII-2 | Akap10 |
| 122 | 3 | 4 | 5 | 6 | 7 | VII-2 | Akap2 |
| 123 | 3 | 4 | 5 | 6 | 7 | VII-2 | Akirin2 |
| 124 | 3 | 4 | 5 | 6 | 7 | VII-2 | Akr1b3 |
| 125 | 3 | 4 | 5 | 6 | 7 | VII-2 | Akr1b7 |
| 126 | 3 | 4 | 5 | 6 | 7 | VII-2 | Akr1c19 |
| 127 | 3 | 4 | 5 | 6 | 7 | VII-2 | Akr1c21 |
| 128 | 3 | 4 | 5 | 6 | 7 | VII-2 | Alas1 |
| 129 | 3 | 4 | 5 | 6 | 7 | VII-2 | Aldoart1 |
| 130 | 3 | 4 | 5 | 6 | 7 | VII-2 | Aldoart2 |
| 131 | 3 | 4 | 5 | 6 | 7 | VII-2 | Alg2 |
| 132 | 3 | 4 | 5 | 6 | 7 | VII-2 | Alox12 |
| 133 | 3 | 4 | 5 | 6 | 7 | VII-2 | Alox8 |
| 134 | 3 | 4 | 5 | 6 | 7 | VII-2 | Als2cl |
| 135 | 3 | 4 | 5 | 6 | 7 | VII-2 | Ammecr1 |
| 136 | 3 | 4 | 5 | 6 | 7 | VII-2 | Ammecr1l |
| 137 | 3 | 4 | 5 | 6 | 7 | VII-2 | Amotl2 |
| 138 | 3 | 4 | 5 | 6 | 7 | VII-2 | Angptl2 |
| 139 | 3 | 4 | 5 | 6 | 7 | VII-2 | Ankhd1 |
| 140 | 3 | 4 | 5 | 6 | 7 | VII-2 | Ankrd11 |
| 141 | 3 | 4 | 5 | 6 | 7 | VII-2 | Ankrd23 |
| 142 | 3 | 4 | 5 | 6 | 7 | VII-2 | Ankrd29 |
| 143 | 3 | 4 | 5 | 6 | 7 | VII-2 | Ankrd49 |
| 144 | 3 | 4 | 5 | 6 | 7 | VII-2 | Ankrd52 |
| 145 | 3 | 4 | 5 | 6 | 7 | VII-2 | Anln |
| 146 | 3 | 4 | 5 | 6 | 7 | VII-2 | Ano7 |
| 147 | 3 | 4 | 5 | 6 | 7 | VII-2 | Aox3 |
| 148 | 3 | 4 | 5 | 6 | 7 | VII-2 | Ap1ar |
| 149 | 3 | 4 | 5 | 6 | 7 | VII-2 | Apcdd1 |
| 150 | 3 | 4 | 5 | 6 | 7 | VII-2 | Aph1b |
| 151 | 3 | 4 | 5 | 6 | 7 | VII-2 | Apitd1 |
| 152 | 3 | 4 | 5 | 6 | 7 | VII-2 | Apmap |
| 153 | 3 | 4 | 5 | 6 | 7 | VII-2 | Apobec1 |
| 154 | 3 | 4 | 5 | 6 | 7 | VII-2 | Apol7a |
| 155 | 3 | 4 | 5 | 6 | 7 | VII-2 | Apol8 |
| 156 | 3 | 4 | 5 | 6 | 7 | VII-2 | Arap2 |
| 157 | 3 | 4 | 5 | 6 | 7 | VII-2 | Arfip1 |
| 158 | 3 | 4 | 5 | 6 | 7 | VII-2 | Arg1 |
| 159 | 3 | 4 | 5 | 6 | 7 | VII-2 | Arhgap24 |
| 160 | 3 | 4 | 5 | 6 | 7 | VII-2 | Arhgap29 |
| 161 | 3 | 4 | 5 | 6 | 7 | VII-2 | Arhgap30 |
| 162 | 3 | 4 | 5 | 6 | 7 | VII-2 | Arhgap31 |
| 163 | 3 | 4 | 5 | 6 | 7 | VII-2 | Arhgap40 |
| 164 | 3 | 4 | 5 | 6 | 7 | VII-2 | Arhgdig |
| 165 | 3 | 4 | 5 | 6 | 7 | VII-2 | Arhgef11 |
| 166 | 3 | 4 | 5 | 6 | 7 | VII-2 | Arhgef37 |
| 167 | 3 | 4 | 5 | 6 | 7 | VII-2 | Arid3b |
| 168 | 3 | 4 | 5 | 6 | 7 | VII-2 | Arl1 |
| 169 | 3 | 4 | 5 | 6 | 7 | VII-2 | Arl6ip5 |
| 170 | 3 | 4 | 5 | 6 | 7 | VII-2 | Arl6ip6 |
| 171 | 3 | 4 | 5 | 6 | 7 | VII-2 | Arl8a |
| 172 | 3 | 4 | 5 | 6 | 7 | VII-2 | Arl9 |
| 173 | 3 | 4 | 5 | 6 | 7 | VII-2 | Armcx1 |
| 174 | 3 | 4 | 5 | 6 | 7 | VII-2 | Armcx5 |
| 175 | 3 | 4 | 5 | 6 | 7 | VII-2 | Art4 |
| 176 | 3 | 4 | 5 | 6 | 7 | VII-2 | Arxes1 |
| 177 | 3 | 4 | 5 | 6 | 7 | VII-2 | Asap2 |
| 178 | 3 | 4 | 5 | 6 | 7 | VII-2 | Asb13 |
| 179 | 3 | 4 | 5 | 6 | 7 | VII-2 | Asb17os |
| 180 | 3 | 4 | 5 | 6 | 7 | VII-2 | Asf1b |
| 181 | 3 | 4 | 5 | 6 | 7 | VII-2 | Atad2b |
| 182 | 3 | 4 | 5 | 6 | 7 | VII-2 | Atg4a |
| 183 | 3 | 4 | 5 | 6 | 7 | VII-2 | Atg4c |
| 184 | 3 | 4 | 5 | 6 | 7 | VII-2 | Atn1 |
| 185 | 3 | 4 | 5 | 6 | 7 | VII-2 | Atp11b |
| 186 | 3 | 4 | 5 | 6 | 7 | VII-2 | Atp1b1 |
| 187 | 3 | 4 | 5 | 6 | 7 | VII-2 | Atp1b2 |
| 188 | 3 | 4 | 5 | 6 | 7 | VII-2 | Atp4b |
| 189 | 3 | 4 | 5 | 6 | 7 | VII-2 | Atp5j |
| 190 | 3 | 4 | 5 | 6 | 7 | VII-2 | Atp6v0d2 |

Fig. 34 - 2

| | | | | | | | |
|---|---|---|---|---|---|---|---|
| 191 | 3 | 4 | 5 | 6 | 7 | VII-2 | Atp6v1a |
| 192 | 3 | 4 | 5 | 6 | 7 | VII-2 | Atp6v1h |
| 193 | 3 | 4 | 5 | 6 | 7 | VII-2 | Atrx |
| 194 | 3 | 4 | 5 | 6 | 7 | VII-2 | Atxn1l |
| 195 | 3 | 4 | 5 | 6 | 7 | VII-2 | Atxn7l1 |
| 196 | 3 | 4 | 5 | 6 | 7 | VII-2 | Atxn7l3 |
| 197 | 3 | 4 | 5 | 6 | 7 | VII-2 | Atxn7l3b |
| 198 | 3 | 4 | 5 | 6 | 7 | VII-2 | Auh |
| 199 | 3 | 4 | 5 | 6 | 7 | VII-2 | Axin2 |
| 200 | 3 | 4 | 5 | 6 | 7 | VII-2 | B230206H07Rik |
| 201 | 3 | 4 | 5 | 6 | 7 | VII-2 | B230217O12Rik |
| 202 | 3 | 4 | 5 | 6 | 7 | VII-2 | B230219D22Rik |
| 203 | 3 | 4 | 5 | 6 | 7 | VII-2 | B3galnt2 |
| 204 | 3 | 4 | 5 | 6 | 7 | VII-2 | B3galt2 |
| 205 | 3 | 4 | 5 | 6 | 7 | VII-2 | B930041F14Rik |
| 206 | 3 | 4 | 5 | 6 | 7 | VII-2 | B9d1 |
| 207 | 3 | 4 | 5 | 6 | 7 | VII-2 | BC016579 |
| 208 | 3 | 4 | 5 | 6 | 7 | VII-2 | BC023829 |
| 209 | 3 | 4 | 5 | 6 | 7 | VII-2 | BC028528 |
| 210 | 3 | 4 | 5 | 6 | 7 | VII-2 | BC030336 |
| 211 | 3 | 4 | 5 | 6 | 7 | VII-2 | BC051537 |
| 212 | 3 | 4 | 5 | 6 | 7 | VII-2 | BC061195 |
| 213 | 3 | 4 | 5 | 6 | 7 | VII-2 | BC100530 |
| 214 | 3 | 4 | 5 | 6 | 7 | VII-2 | Bahd1 |
| 215 | 3 | 4 | 5 | 6 | 7 | VII-2 | Basp1 |
| 216 | 3 | 4 | 5 | 6 | 7 | VII-2 | Bcap29 |
| 217 | 3 | 4 | 5 | 6 | 7 | VII-2 | Bcl10 |
| 218 | 3 | 4 | 5 | 6 | 7 | VII-2 | Bcl2l2 |
| 219 | 3 | 4 | 5 | 6 | 7 | VII-2 | Bcl7a |
| 220 | 3 | 4 | 5 | 6 | 7 | VII-2 | Bcl9l |
| 221 | 3 | 4 | 5 | 6 | 7 | VII-2 | Bend6 |
| 222 | 3 | 4 | 5 | 6 | 7 | VII-2 | Bex4 |
| 223 | 3 | 4 | 5 | 6 | 7 | VII-2 | Bglap2 |
| 224 | 3 | 4 | 5 | 6 | 7 | VII-2 | Bmp10 |
| 225 | 3 | 4 | 5 | 6 | 7 | VII-2 | Bmp3 |
| 226 | 3 | 4 | 5 | 6 | 7 | VII-2 | Bmp6 |
| 227 | 3 | 4 | 5 | 6 | 7 | VII-2 | Bmpr1a |
| 228 | 3 | 4 | 5 | 6 | 7 | VII-2 | Bpifc |
| 229 | 3 | 4 | 5 | 6 | 7 | VII-2 | Brms1l |
| 230 | 3 | 4 | 5 | 6 | 7 | VII-2 | Brpf1 |
| 231 | 3 | 4 | 5 | 6 | 7 | VII-2 | Btbd10 |
| 232 | 3 | 4 | 5 | 6 | 7 | VII-2 | Btbd3 |
| 233 | 3 | 4 | 5 | 6 | 7 | VII-2 | Btnl9 |
| 234 | 3 | 4 | 5 | 6 | 7 | VII-2 | C030029H02Rik |
| 235 | 3 | 4 | 5 | 6 | 7 | VII-2 | C030046E11Rik |
| 236 | 3 | 4 | 5 | 6 | 7 | VII-2 | C1galt1c1 |
| 237 | 3 | 4 | 5 | 6 | 7 | VII-2 | C1s1 |
| 238 | 3 | 4 | 5 | 6 | 7 | VII-2 | C230091D08Rik |
| 239 | 3 | 4 | 5 | 6 | 7 | VII-2 | C2cd4d |
| 240 | 3 | 4 | 5 | 6 | 7 | VII-2 | C330022C24Rik |
| 241 | 3 | 4 | 5 | 6 | 7 | VII-2 | C4a |
| 242 | 3 | 4 | 5 | 6 | 7 | VII-2 | C6 |
| 243 | 3 | 4 | 5 | 6 | 7 | VII-2 | C730036E19Rik |
| 244 | 3 | 4 | 5 | 6 | 7 | VII-2 | C78339 |
| 245 | 3 | 4 | 5 | 6 | 7 | VII-2 | C920009B18Rik |
| 246 | 3 | 4 | 5 | 6 | 7 | VII-2 | Calm4 |
| 247 | 3 | 4 | 5 | 6 | 7 | VII-2 | Calml3 |
| 248 | 3 | 4 | 5 | 6 | 7 | VII-2 | Camk2n1 |
| 249 | 3 | 4 | 5 | 6 | 7 | VII-2 | Cap1 |
| 250 | 3 | 4 | 5 | 6 | 7 | VII-2 | Capg |
| 251 | 3 | 4 | 5 | 6 | 7 | VII-2 | Capn15 |
| 252 | 3 | 4 | 5 | 6 | 7 | VII-2 | Car1 |
| 253 | 3 | 4 | 5 | 6 | 7 | VII-2 | Car12 |
| 254 | 3 | 4 | 5 | 6 | 7 | VII-2 | Car2 |
| 255 | 3 | 4 | 5 | 6 | 7 | VII-2 | Car3 |
| 256 | 3 | 4 | 5 | 6 | 7 | VII-2 | Car7 |
| 257 | 3 | 4 | 5 | 6 | 7 | VII-2 | Caskin2 |
| 258 | 3 | 4 | 5 | 6 | 7 | VII-2 | Casp6 |
| 259 | 3 | 4 | 5 | 6 | 7 | VII-2 | Casp8 |
| 260 | 3 | 4 | 5 | 6 | 7 | VII-2 | Cav1 |
| 261 | 3 | 4 | 5 | 6 | 7 | VII-2 | Cbfb |
| 262 | 3 | 4 | 5 | 6 | 7 | VII-2 | Cbl |
| 263 | 3 | 4 | 5 | 6 | 7 | VII-2 | Cbx1 |
| 264 | 3 | 4 | 5 | 6 | 7 | VII-2 | Ccdc34 |
| 265 | 3 | 4 | 5 | 6 | 7 | VII-2 | Ccdc47 |
| 266 | 3 | 4 | 5 | 6 | 7 | VII-2 | Ccdc50 |
| 267 | 3 | 4 | 5 | 6 | 7 | VII-2 | Ccdc64 |
| 268 | 3 | 4 | 5 | 6 | 7 | VII-2 | Ccdc80 |
| 269 | 3 | 4 | 5 | 6 | 7 | VII-2 | Ccdc82 |
| 270 | 3 | 4 | 5 | 6 | 7 | VII-2 | Cckbr |
| 271 | 3 | 4 | 5 | 6 | 7 | VII-2 | Ccl20 |
| 272 | 3 | 4 | 5 | 6 | 7 | VII-2 | Ccl21a |
| 273 | 3 | 4 | 5 | 6 | 7 | VII-2 | Ccl21c |
| 274 | 3 | 4 | 5 | 6 | 7 | VII-2 | Ccnd2 |
| 275 | 3 | 4 | 5 | 6 | 7 | VII-2 | Ccne2 |
| 276 | 3 | 4 | 5 | 6 | 7 | VII-2 | Ccnt2 |
| 277 | 3 | 4 | 5 | 6 | 7 | VII-2 | Ccr4 |
| 278 | 3 | 4 | 5 | 6 | 7 | VII-2 | Ccr6 |
| 279 | 3 | 4 | 5 | 6 | 7 | VII-2 | Cd164 |
| 280 | 3 | 4 | 5 | 6 | 7 | VII-2 | Cd1d1 |
| 281 | 3 | 4 | 5 | 6 | 7 | VII-2 | Cd1d2 |
| 282 | 3 | 4 | 5 | 6 | 7 | VII-2 | Cd207 |
| 283 | 3 | 4 | 5 | 6 | 7 | VII-2 | Cd209f |
| 284 | 3 | 4 | 5 | 6 | 7 | VII-2 | Cd274 |
| 285 | 3 | 4 | 5 | 6 | 7 | VII-2 | Cd300ld |
| 286 | 3 | 4 | 5 | 6 | 7 | VII-2 | Cd300lh |

| | | | | | | | |
|---|---|---|---|---|---|---|---|
| 287 | 3 | 4 | 5 | 6 | 7 | VII-2 | Cd302 |
| 288 | 3 | 4 | 5 | 6 | 7 | VII-2 | Cd52 |
| 289 | 3 | 4 | 5 | 6 | 7 | VII-2 | Cdc14b |
| 290 | 3 | 4 | 5 | 6 | 7 | VII-2 | Cdc23 |
| 291 | 3 | 4 | 5 | 6 | 7 | VII-2 | Cdc40 |
| 292 | 3 | 4 | 5 | 6 | 7 | VII-2 | Cdc42bpg |
| 293 | 3 | 4 | 5 | 6 | 7 | VII-2 | Cdc42ep3 |
| 294 | 3 | 4 | 5 | 6 | 7 | VII-2 | Cdc6 |
| 295 | 3 | 4 | 5 | 6 | 7 | VII-2 | Cdcp1 |
| 296 | 3 | 4 | 5 | 6 | 7 | VII-2 | Cdh11 |
| 297 | 3 | 4 | 5 | 6 | 7 | VII-2 | Cdh13 |
| 298 | 3 | 4 | 5 | 6 | 7 | VII-2 | Cdh3 |
| 299 | 3 | 4 | 5 | 6 | 7 | VII-2 | Cdh5 |
| 300 | 3 | 4 | 5 | 6 | 7 | VII-2 | Cdk14 |
| 301 | 3 | 4 | 5 | 6 | 7 | VII-2 | Cdk5r1 |
| 302 | 3 | 4 | 5 | 6 | 7 | VII-2 | Cdkn2c |
| 303 | 3 | 4 | 5 | 6 | 7 | VII-2 | Ceacam1 |
| 304 | 3 | 4 | 5 | 6 | 7 | VII-2 | Ceacam10 |
| 305 | 3 | 4 | 5 | 6 | 7 | VII-2 | Cebpa |
| 306 | 3 | 4 | 5 | 6 | 7 | VII-2 | Cebpb |
| 307 | 3 | 4 | 5 | 6 | 7 | VII-2 | Cep170b |
| 308 | 3 | 4 | 5 | 6 | 7 | VII-2 | Cep68 |
| 309 | 3 | 4 | 5 | 6 | 7 | VII-2 | Ces1f |
| 310 | 3 | 4 | 5 | 6 | 7 | VII-2 | Ces5a |
| 311 | 3 | 4 | 5 | 6 | 7 | VII-2 | Cetn3 |
| 312 | 3 | 4 | 5 | 6 | 7 | VII-2 | Cflar |
| 313 | 3 | 4 | 5 | 6 | 7 | VII-2 | Chd3os |
| 314 | 3 | 4 | 5 | 6 | 7 | VII-2 | Chp1 |
| 315 | 3 | 4 | 5 | 6 | 7 | VII-2 | Chst14 |
| 316 | 3 | 4 | 5 | 6 | 7 | VII-2 | Chst15 |
| 317 | 3 | 4 | 5 | 6 | 7 | VII-2 | Chuk |
| 318 | 3 | 4 | 5 | 6 | 7 | VII-2 | Ciart |
| 319 | 3 | 4 | 5 | 6 | 7 | VII-2 | Cideb |
| 320 | 3 | 4 | 5 | 6 | 7 | VII-2 | Cish |
| 321 | 3 | 4 | 5 | 6 | 7 | VII-2 | Ckap2 |
| 322 | 3 | 4 | 5 | 6 | 7 | VII-2 | Cks2 |
| 323 | 3 | 4 | 5 | 6 | 7 | VII-2 | Clca5 |
| 324 | 3 | 4 | 5 | 6 | 7 | VII-2 | Clcf1 |
| 325 | 3 | 4 | 5 | 6 | 7 | VII-2 | Clcn3 |
| 326 | 3 | 4 | 5 | 6 | 7 | VII-2 | Cldn13 |
| 327 | 3 | 4 | 5 | 6 | 7 | VII-2 | Cldn23 |
| 328 | 3 | 4 | 5 | 6 | 7 | VII-2 | Cldn25 |
| 329 | 3 | 4 | 5 | 6 | 7 | VII-2 | Clec1a |
| 330 | 3 | 4 | 5 | 6 | 7 | VII-2 | Clec2g |
| 331 | 3 | 4 | 5 | 6 | 7 | VII-2 | Clgn |
| 332 | 3 | 4 | 5 | 6 | 7 | VII-2 | Cmbl |
| 333 | 3 | 4 | 5 | 6 | 7 | VII-2 | Cmpk1 |
| 334 | 3 | 4 | 5 | 6 | 7 | VII-2 | Cmtm6 |
| 335 | 3 | 4 | 5 | 6 | 7 | VII-2 | Cnnm4 |
| 336 | 3 | 4 | 5 | 6 | 7 | VII-2 | Cnot3 |
| 337 | 3 | 4 | 5 | 6 | 7 | VII-2 | Cntfr |
| 338 | 3 | 4 | 5 | 6 | 7 | VII-2 | Cog1 |
| 339 | 3 | 4 | 5 | 6 | 7 | VII-2 | Cog3 |
| 340 | 3 | 4 | 5 | 6 | 7 | VII-2 | Col13a1 |
| 341 | 3 | 4 | 5 | 6 | 7 | VII-2 | Col3a1 |
| 342 | 3 | 4 | 5 | 6 | 7 | VII-2 | Col4a3 |
| 343 | 3 | 4 | 5 | 6 | 7 | VII-2 | Col4a3bp |
| 344 | 3 | 4 | 5 | 6 | 7 | VII-2 | Coq2 |
| 345 | 3 | 4 | 5 | 6 | 7 | VII-2 | Cox15 |
| 346 | 3 | 4 | 5 | 6 | 7 | VII-2 | Cox6c |
| 347 | 3 | 4 | 5 | 6 | 7 | VII-2 | Cpeb4 |
| 348 | 3 | 4 | 5 | 6 | 7 | VII-2 | Cped1 |
| 349 | 3 | 4 | 5 | 6 | 7 | VII-2 | Cpn2 |
| 350 | 3 | 4 | 5 | 6 | 7 | VII-2 | Cpne1 |
| 351 | 3 | 4 | 5 | 6 | 7 | VII-2 | Cpne3 |
| 352 | 3 | 4 | 5 | 6 | 7 | VII-2 | Cpq |
| 353 | 3 | 4 | 5 | 6 | 7 | VII-2 | Cramp1l |
| 354 | 3 | 4 | 5 | 6 | 7 | VII-2 | Crebbp |
| 355 | 3 | 4 | 5 | 6 | 7 | VII-2 | Crebl2 |
| 356 | 3 | 4 | 5 | 6 | 7 | VII-2 | Crebrf |
| 357 | 3 | 4 | 5 | 6 | 7 | VII-2 | Crisp1 |
| 358 | 3 | 4 | 5 | 6 | 7 | VII-2 | Crk |
| 359 | 3 | 4 | 5 | 6 | 7 | VII-2 | Crlf3 |
| 360 | 3 | 4 | 5 | 6 | 7 | VII-2 | Crygc |
| 361 | 3 | 4 | 5 | 6 | 7 | VII-2 | Cryl1 |
| 362 | 3 | 4 | 5 | 6 | 7 | VII-2 | Csdc2 |
| 363 | 3 | 4 | 5 | 6 | 7 | VII-2 | Csf1 |
| 364 | 3 | 4 | 5 | 6 | 7 | VII-2 | Csl |
| 365 | 3 | 4 | 5 | 6 | 7 | VII-2 | Cst12 |
| 366 | 3 | 4 | 5 | 6 | 7 | VII-2 | Cthrc1 |
| 367 | 3 | 4 | 5 | 6 | 7 | VII-2 | Ctnnd1 |
| 368 | 3 | 4 | 5 | 6 | 7 | VII-2 | Ctse |
| 369 | 3 | 4 | 5 | 6 | 7 | VII-2 | Cul4a |
| 370 | 3 | 4 | 5 | 6 | 7 | VII-2 | Cwc22 |
| 371 | 3 | 4 | 5 | 6 | 7 | VII-2 | Cwf19l2 |
| 372 | 3 | 4 | 5 | 6 | 7 | VII-2 | Cxcl12 |
| 373 | 3 | 4 | 5 | 6 | 7 | VII-2 | Cxcl9 |
| 374 | 3 | 4 | 5 | 6 | 7 | VII-2 | Cxxc5 |
| 375 | 3 | 4 | 5 | 6 | 7 | VII-2 | Cyb5 |
| 376 | 3 | 4 | 5 | 6 | 7 | VII-2 | Cyb5r1 |
| 377 | 3 | 4 | 5 | 6 | 7 | VII-2 | Cyfip2 |
| 378 | 3 | 4 | 5 | 6 | 7 | VII-2 | Cyp1a1 |
| 379 | 3 | 4 | 5 | 6 | 7 | VII-2 | Cyp1a2 |
| 380 | 3 | 4 | 5 | 6 | 7 | VII-2 | Cyp2a22 |
| 381 | 3 | 4 | 5 | 6 | 7 | VII-2 | Cyp2a4 |
| 382 | 3 | 4 | 5 | 6 | 7 | VII-2 | Cyp2a5 |

Fig. 34 - 3

| | | | | | | | |
|---|---|---|---|---|---|---|---|
| 383 | 3 | 4 | 5 | 6 | 7 | VII-2 | Cyp2b9 |
| 384 | 3 | 4 | 5 | 6 | 7 | VII-2 | Cyp2c44 |
| 385 | 3 | 4 | 5 | 6 | 7 | VII-2 | Cypt9 |
| 386 | 3 | 4 | 5 | 6 | 7 | VII-2 | Cystm1 |
| 387 | 3 | 4 | 5 | 6 | 7 | VII-2 | Cyth3 |
| 388 | 3 | 4 | 5 | 6 | 7 | VII-2 | Cyyr1 |
| 389 | 3 | 4 | 5 | 6 | 7 | VII-2 | D030056L22Rik |
| 390 | 3 | 4 | 5 | 6 | 7 | VII-2 | D430019H16Rik |
| 391 | 3 | 4 | 5 | 6 | 7 | VII-2 | D930016D06Rik |
| 392 | 3 | 4 | 5 | 6 | 7 | VII-2 | Dag1 |
| 393 | 3 | 4 | 5 | 6 | 7 | VII-2 | Dagla |
| 394 | 3 | 4 | 5 | 6 | 7 | VII-2 | Dapk1 |
| 395 | 3 | 4 | 5 | 6 | 7 | VII-2 | Dbf4 |
| 396 | 3 | 4 | 5 | 6 | 7 | VII-2 | Dbp |
| 397 | 3 | 4 | 5 | 6 | 7 | VII-2 | Dbt |
| 398 | 3 | 4 | 5 | 6 | 7 | VII-2 | Dclk3 |
| 399 | 3 | 4 | 5 | 6 | 7 | VII-2 | Dcp1a |
| 400 | 3 | 4 | 5 | 6 | 7 | VII-2 | Ddb2 |
| 401 | 3 | 4 | 5 | 6 | 7 | VII-2 | Ddr1 |
| 402 | 3 | 4 | 5 | 6 | 7 | VII-2 | Ddx19b |
| 403 | 3 | 4 | 5 | 6 | 7 | VII-2 | Ddx20 |
| 404 | 3 | 4 | 5 | 6 | 7 | VII-2 | Ddx23 |
| 405 | 3 | 4 | 5 | 6 | 7 | VII-2 | Ddx26b |
| 406 | 3 | 4 | 5 | 6 | 7 | VII-2 | Ddx3x |
| 407 | 3 | 4 | 5 | 6 | 7 | VII-2 | Def8 |
| 408 | 3 | 4 | 5 | 6 | 7 | VII-2 | Defb38 |
| 409 | 3 | 4 | 5 | 6 | 7 | VII-2 | Defb43 |
| 410 | 3 | 4 | 5 | 6 | 7 | VII-2 | Defb48 |
| 411 | 3 | 4 | 5 | 6 | 7 | VII-2 | Defb50 |
| 412 | 3 | 4 | 5 | 6 | 7 | VII-2 | Defb8 |
| 413 | 3 | 4 | 5 | 6 | 7 | VII-2 | Dffa |
| 414 | 3 | 4 | 5 | 6 | 7 | VII-2 | Dgat2 |
| 415 | 3 | 4 | 5 | 6 | 7 | VII-2 | Dgkq |
| 416 | 3 | 4 | 5 | 6 | 7 | VII-2 | Dhdh |
| 417 | 3 | 4 | 5 | 6 | 7 | VII-2 | Dhrs1 |
| 418 | 3 | 4 | 5 | 6 | 7 | VII-2 | Dhrs9 |
| 419 | 3 | 4 | 5 | 6 | 7 | VII-2 | Diap1 |
| 420 | 3 | 4 | 5 | 6 | 7 | VII-2 | Dip2a |
| 421 | 3 | 4 | 5 | 6 | 7 | VII-2 | Diras2 |
| 422 | 3 | 4 | 5 | 6 | 7 | VII-2 | Disp1 |
| 423 | 3 | 4 | 5 | 6 | 7 | VII-2 | Dkk2 |
| 424 | 3 | 4 | 5 | 6 | 7 | VII-2 | Dlg2 |
| 425 | 3 | 4 | 5 | 6 | 7 | VII-2 | Dlg4 |
| 426 | 3 | 4 | 5 | 6 | 7 | VII-2 | Dlk1 |
| 427 | 3 | 4 | 5 | 6 | 7 | VII-2 | Dll1 |
| 428 | 3 | 4 | 5 | 6 | 7 | VII-2 | Dmtf1 |
| 429 | 3 | 4 | 5 | 6 | 7 | VII-2 | Dnajb3 |
| 430 | 3 | 4 | 5 | 6 | 7 | VII-2 | Dnajb9 |
| 431 | 3 | 4 | 5 | 6 | 7 | VII-2 | Dnmt1 |
| 432 | 3 | 4 | 5 | 6 | 7 | VII-2 | Dot1l |
| 433 | 3 | 4 | 5 | 6 | 7 | VII-2 | Dpcr1 |
| 434 | 3 | 4 | 5 | 6 | 7 | VII-2 | Dpp8 |
| 435 | 3 | 4 | 5 | 6 | 7 | VII-2 | Dpys |
| 436 | 3 | 4 | 5 | 6 | 7 | VII-2 | Dr1 |
| 437 | 3 | 4 | 5 | 6 | 7 | VII-2 | Dram1 |
| 438 | 3 | 4 | 5 | 6 | 7 | VII-2 | Dsc1 |
| 439 | 3 | 4 | 5 | 6 | 7 | VII-2 | Dsg1b |
| 440 | 3 | 4 | 5 | 6 | 7 | VII-2 | Dsg1c |
| 441 | 3 | 4 | 5 | 6 | 7 | VII-2 | Dsg3 |
| 442 | 3 | 4 | 5 | 6 | 7 | VII-2 | Dtd1 |
| 443 | 3 | 4 | 5 | 6 | 7 | VII-2 | Dtwd1 |
| 444 | 3 | 4 | 5 | 6 | 7 | VII-2 | Dusp5 |
| 445 | 3 | 4 | 5 | 6 | 7 | VII-2 | Dusp7 |
| 446 | 3 | 4 | 5 | 6 | 7 | VII-2 | Dvl3 |
| 447 | 3 | 4 | 5 | 6 | 7 | VII-2 | E030011O05Rik |
| 448 | 3 | 4 | 5 | 6 | 7 | VII-2 | E130006D01Rik |
| 449 | 3 | 4 | 5 | 6 | 7 | VII-2 | E2f6 |
| 450 | 3 | 4 | 5 | 6 | 7 | VII-2 | Eaf1 |
| 451 | 3 | 4 | 5 | 6 | 7 | VII-2 | Ear10 |
| 452 | 3 | 4 | 5 | 6 | 7 | VII-2 | Ebag9 |
| 453 | 3 | 4 | 5 | 6 | 7 | VII-2 | Ebf1 |
| 454 | 3 | 4 | 5 | 6 | 7 | VII-2 | Echdc1 |
| 455 | 3 | 4 | 5 | 6 | 7 | VII-2 | Eci3 |
| 456 | 3 | 4 | 5 | 6 | 7 | VII-2 | Efcab14 |
| 457 | 3 | 4 | 5 | 6 | 7 | VII-2 | Efna3 |
| 458 | 3 | 4 | 5 | 6 | 7 | VII-2 | Efnb2 |
| 459 | 3 | 4 | 5 | 6 | 7 | VII-2 | Efr3a |
| 460 | 3 | 4 | 5 | 6 | 7 | VII-2 | Egr2 |
| 461 | 3 | 4 | 5 | 6 | 7 | VII-2 | Ehd3 |
| 462 | 3 | 4 | 5 | 6 | 7 | VII-2 | Ehmt1 |
| 463 | 3 | 4 | 5 | 6 | 7 | VII-2 | Eif2a |
| 464 | 3 | 4 | 5 | 6 | 7 | VII-2 | Eif2ak3 |
| 465 | 3 | 4 | 5 | 6 | 7 | VII-2 | Eif3a |
| 466 | 3 | 4 | 5 | 6 | 7 | VII-2 | Eif3e |
| 467 | 3 | 4 | 5 | 6 | 7 | VII-2 | Eif4a3 |
| 468 | 3 | 4 | 5 | 6 | 7 | VII-2 | Eif4e3 |
| 469 | 3 | 4 | 5 | 6 | 7 | VII-2 | Eif4ebp2 |
| 470 | 3 | 4 | 5 | 6 | 7 | VII-2 | Elf1 |
| 471 | 3 | 4 | 5 | 6 | 7 | VII-2 | Elmo1 |
| 472 | 3 | 4 | 5 | 6 | 7 | VII-2 | Elmsan1 |
| 473 | 3 | 4 | 5 | 6 | 7 | VII-2 | Elovl5 |
| 474 | 3 | 4 | 5 | 6 | 7 | VII-2 | Elovl6 |
| 475 | 3 | 4 | 5 | 6 | 7 | VII-2 | Emp1 |
| 476 | 3 | 4 | 5 | 6 | 7 | VII-2 | Emp2 |
| 477 | 3 | 4 | 5 | 6 | 7 | VII-2 | Eno1 |
| 478 | 3 | 4 | 5 | 6 | 7 | VII-2 | Eogt |
| 479 | 3 | 4 | 5 | 6 | 7 | VII-2 | Epb4.1l2 |
| 480 | 3 | 4 | 5 | 6 | 7 | VII-2 | Epb4.2 |
| 481 | 3 | 4 | 5 | 6 | 7 | VII-2 | Ephb1 |
| 482 | 3 | 4 | 5 | 6 | 7 | VII-2 | Ephx1 |
| 483 | 3 | 4 | 5 | 6 | 7 | VII-2 | Eppin |
| 484 | 3 | 4 | 5 | 6 | 7 | VII-2 | Epyc |
| 485 | 3 | 4 | 5 | 6 | 7 | VII-2 | Eral1 |
| 486 | 3 | 4 | 5 | 6 | 7 | VII-2 | Erbb2ip |
| 487 | 3 | 4 | 5 | 6 | 7 | VII-2 | Erbb3 |
| 488 | 3 | 4 | 5 | 6 | 7 | VII-2 | Ercc6l2 |
| 489 | 3 | 4 | 5 | 6 | 7 | VII-2 | Erdr1 |
| 490 | 3 | 4 | 5 | 6 | 7 | VII-2 | Erg |
| 491 | 3 | 4 | 5 | 6 | 7 | VII-2 | Erich1 |
| 492 | 3 | 4 | 5 | 6 | 7 | VII-2 | Esrp2 |
| 493 | 3 | 4 | 5 | 6 | 7 | VII-2 | Esrrg |
| 494 | 3 | 4 | 5 | 6 | 7 | VII-2 | Etv3 |
| 495 | 3 | 4 | 5 | 6 | 7 | VII-2 | Etv6 |
| 496 | 3 | 4 | 5 | 6 | 7 | VII-2 | Evi2b |
| 497 | 3 | 4 | 5 | 6 | 7 | VII-2 | Evi5 |
| 498 | 3 | 4 | 5 | 6 | 7 | VII-2 | Exd2 |
| 499 | 3 | 4 | 5 | 6 | 7 | VII-2 | Exosc3 |
| 500 | 3 | 4 | 5 | 6 | 7 | VII-2 | Exosc9 |
| 501 | 3 | 4 | 5 | 6 | 7 | VII-2 | Extl2 |
| 502 | 3 | 4 | 5 | 6 | 7 | VII-2 | F13b |
| 503 | 3 | 4 | 5 | 6 | 7 | VII-2 | Fzd1 |
| 504 | 3 | 4 | 5 | 6 | 7 | VII-2 | Fabp1 |
| 505 | 3 | 4 | 5 | 6 | 7 | VII-2 | Fabp5 |
| 506 | 3 | 4 | 5 | 6 | 7 | VII-2 | Fabp7 |
| 507 | 3 | 4 | 5 | 6 | 7 | VII-2 | Fam102a |
| 508 | 3 | 4 | 5 | 6 | 7 | VII-2 | Fam103a1 |
| 509 | 3 | 4 | 5 | 6 | 7 | VII-2 | Fam107b |
| 510 | 3 | 4 | 5 | 6 | 7 | VII-2 | Fam117a |
| 511 | 3 | 4 | 5 | 6 | 7 | VII-2 | Fam122a |
| 512 | 3 | 4 | 5 | 6 | 7 | VII-2 | Fam122c |
| 513 | 3 | 4 | 5 | 6 | 7 | VII-2 | Fam129a |
| 514 | 3 | 4 | 5 | 6 | 7 | VII-2 | Fam131a |
| 515 | 3 | 4 | 5 | 6 | 7 | VII-2 | Fam135a |
| 516 | 3 | 4 | 5 | 6 | 7 | VII-2 | Fam167a |
| 517 | 3 | 4 | 5 | 6 | 7 | VII-2 | Fam173b |
| 518 | 3 | 4 | 5 | 6 | 7 | VII-2 | Fam204a |
| 519 | 3 | 4 | 5 | 6 | 7 | VII-2 | Fam20b |
| 520 | 3 | 4 | 5 | 6 | 7 | VII-2 | Fam219a |
| 521 | 3 | 4 | 5 | 6 | 7 | VII-2 | Fam26e |
| 522 | 3 | 4 | 5 | 6 | 7 | VII-2 | Fam43a |
| 523 | 3 | 4 | 5 | 6 | 7 | VII-2 | Fam57a |
| 524 | 3 | 4 | 5 | 6 | 7 | VII-2 | Fam60a |
| 525 | 3 | 4 | 5 | 6 | 7 | VII-2 | Fam65c |
| 526 | 3 | 4 | 5 | 6 | 7 | VII-2 | Fam78a |
| 527 | 3 | 4 | 5 | 6 | 7 | VII-2 | Fam83c |
| 528 | 3 | 4 | 5 | 6 | 7 | VII-2 | Fam84b |
| 529 | 3 | 4 | 5 | 6 | 7 | VII-2 | Far2 |
| 530 | 3 | 4 | 5 | 6 | 7 | VII-2 | Fastkd5 |
| 531 | 3 | 4 | 5 | 6 | 7 | VII-2 | Fat1 |
| 532 | 3 | 4 | 5 | 6 | 7 | VII-2 | Fbxl12 |
| 533 | 3 | 4 | 5 | 6 | 7 | VII-2 | Fbxl14 |
| 534 | 3 | 4 | 5 | 6 | 7 | VII-2 | Fbxl15 |
| 535 | 3 | 4 | 5 | 6 | 7 | VII-2 | Fbxl4 |
| 536 | 3 | 4 | 5 | 6 | 7 | VII-2 | Fbxo21 |
| 537 | 3 | 4 | 5 | 6 | 7 | VII-2 | Fbxo44 |
| 538 | 3 | 4 | 5 | 6 | 7 | VII-2 | Fbxo5 |
| 539 | 3 | 4 | 5 | 6 | 7 | VII-2 | Fcer2a |
| 540 | 3 | 4 | 5 | 6 | 7 | VII-2 | Fcho2 |
| 541 | 3 | 4 | 5 | 6 | 7 | VII-2 | Fchsd2 |
| 542 | 3 | 4 | 5 | 6 | 7 | VII-2 | Fermt1 |
| 543 | 3 | 4 | 5 | 6 | 7 | VII-2 | Fetub |
| 544 | 3 | 4 | 5 | 6 | 7 | VII-2 | Ffar1 |
| 545 | 3 | 4 | 5 | 6 | 7 | VII-2 | Ffar4 |
| 546 | 3 | 4 | 5 | 6 | 7 | VII-2 | Fgf22 |
| 547 | 3 | 4 | 5 | 6 | 7 | VII-2 | Fgfbp1 |
| 548 | 3 | 4 | 5 | 6 | 7 | VII-2 | Fgfrl1 |
| 549 | 3 | 4 | 5 | 6 | 7 | VII-2 | Fhdc1 |
| 550 | 3 | 4 | 5 | 6 | 7 | VII-2 | Fignl1 |
| 551 | 3 | 4 | 5 | 6 | 7 | VII-2 | Filip1l |
| 552 | 3 | 4 | 5 | 6 | 7 | VII-2 | Fkrp |
| 553 | 3 | 4 | 5 | 6 | 7 | VII-2 | Flg2 |
| 554 | 3 | 4 | 5 | 6 | 7 | VII-2 | Flt1 |
| 555 | 3 | 4 | 5 | 6 | 7 | VII-2 | Flywch1 |
| 556 | 3 | 4 | 5 | 6 | 7 | VII-2 | Fmr1 |
| 557 | 3 | 4 | 5 | 6 | 7 | VII-2 | Fn3krp |
| 558 | 3 | 4 | 5 | 6 | 7 | VII-2 | Fndc3b |
| 559 | 3 | 4 | 5 | 6 | 7 | VII-2 | Fosb |
| 560 | 3 | 4 | 5 | 6 | 7 | VII-2 | Foxf2 |
| 561 | 3 | 4 | 5 | 6 | 7 | VII-2 | Foxj3 |
| 562 | 3 | 4 | 5 | 6 | 7 | VII-2 | Foxk1 |
| 563 | 3 | 4 | 5 | 6 | 7 | VII-2 | Foxn2 |
| 564 | 3 | 4 | 5 | 6 | 7 | VII-2 | Foxq1 |
| 565 | 3 | 4 | 5 | 6 | 7 | VII-2 | Fpgt |
| 566 | 3 | 4 | 5 | 6 | 7 | VII-2 | Frmd4a |
| 567 | 3 | 4 | 5 | 6 | 7 | VII-2 | Frmd6 |
| 568 | 3 | 4 | 5 | 6 | 7 | VII-2 | Frs2 |
| 569 | 3 | 4 | 5 | 6 | 7 | VII-2 | Frs3 |
| 570 | 3 | 4 | 5 | 6 | 7 | VII-2 | Fstl1 |
| 571 | 3 | 4 | 5 | 6 | 7 | VII-2 | Fzd1 |
| 572 | 3 | 4 | 5 | 6 | 7 | VII-2 | Fzd4 |
| 573 | 3 | 4 | 5 | 6 | 7 | VII-2 | Fzd7 |
| 574 | 3 | 4 | 5 | 6 | 7 | VII-2 | G0s2 |

Fig. 34 - 4

| | | | | | | | |
|---|---|---|---|---|---|---|---|
| 575 | 3 | 4 | 5 | 6 | 7 | VII-2 | G6pd2 |
| 576 | 3 | 4 | 5 | 6 | 7 | VII-2 | Gabpa |
| 577 | 3 | 4 | 5 | 6 | 7 | VII-2 | Gabpb1 |
| 578 | 3 | 4 | 5 | 6 | 7 | VII-2 | Gadd45a |
| 579 | 3 | 4 | 5 | 6 | 7 | VII-2 | Gak |
| 580 | 3 | 4 | 5 | 6 | 7 | VII-2 | Gale |
| 581 | 3 | 4 | 5 | 6 | 7 | VII-2 | Galm |
| 582 | 3 | 4 | 5 | 6 | 7 | VII-2 | Galnt11 |
| 583 | 3 | 4 | 5 | 6 | 7 | VII-2 | Galnt15 |
| 584 | 3 | 4 | 5 | 6 | 7 | VII-2 | Galnt7 |
| 585 | 3 | 4 | 5 | 6 | 7 | VII-2 | Gamt |
| 586 | 3 | 4 | 5 | 6 | 7 | VII-2 | Gapvd1 |
| 587 | 3 | 4 | 5 | 6 | 7 | VII-2 | Gas5 |
| 588 | 3 | 4 | 5 | 6 | 7 | VII-2 | Gas7 |
| 589 | 3 | 4 | 5 | 6 | 7 | VII-2 | Gck |
| 590 | 3 | 4 | 5 | 6 | 7 | VII-2 | Gdf11 |
| 591 | 3 | 4 | 5 | 6 | 7 | VII-2 | Gfap |
| 592 | 3 | 4 | 5 | 6 | 7 | VII-2 | Gfod1 |
| 593 | 3 | 4 | 5 | 6 | 7 | VII-2 | Gh |
| 594 | 3 | 4 | 5 | 6 | 7 | VII-2 | Gimap4 |
| 595 | 3 | 4 | 5 | 6 | 7 | VII-2 | Gk5 |
| 596 | 3 | 4 | 5 | 6 | 7 | VII-2 | Gkn1 |
| 597 | 3 | 4 | 5 | 6 | 7 | VII-2 | Gkn2 |
| 598 | 3 | 4 | 5 | 6 | 7 | VII-2 | Gldc |
| 599 | 3 | 4 | 5 | 6 | 7 | VII-2 | Glt6d1 |
| 600 | 3 | 4 | 5 | 6 | 7 | VII-2 | Gltp |
| 601 | 3 | 4 | 5 | 6 | 7 | VII-2 | Gltscr1 |
| 602 | 3 | 4 | 5 | 6 | 7 | VII-2 | Gltscr1l |
| 603 | 3 | 4 | 5 | 6 | 7 | VII-2 | Gm10046 |
| 604 | 3 | 4 | 5 | 6 | 7 | VII-2 | Gm10058 |
| 605 | 3 | 4 | 5 | 6 | 7 | VII-2 | Gm10100 |
| 606 | 3 | 4 | 5 | 6 | 7 | VII-2 | Gm10142 |
| 607 | 3 | 4 | 5 | 6 | 7 | VII-2 | Gm10190 |
| 608 | 3 | 4 | 5 | 6 | 7 | VII-2 | Gm10272 |
| 609 | 3 | 4 | 5 | 6 | 7 | VII-2 | Gm10336 |
| 610 | 3 | 4 | 5 | 6 | 7 | VII-2 | Gm10413 |
| 611 | 3 | 4 | 5 | 6 | 7 | VII-2 | Gm10486 |
| 612 | 3 | 4 | 5 | 6 | 7 | VII-2 | Gm10768 |
| 613 | 3 | 4 | 5 | 6 | 7 | VII-2 | Gm11127 |
| 614 | 3 | 4 | 5 | 6 | 7 | VII-2 | Gm11559 |
| 615 | 3 | 4 | 5 | 6 | 7 | VII-2 | Gm11710 |
| 616 | 3 | 4 | 5 | 6 | 7 | VII-2 | Gm11937 |
| 617 | 3 | 4 | 5 | 6 | 7 | VII-2 | Gm11992 |
| 618 | 3 | 4 | 5 | 6 | 7 | VII-2 | Gm12070 |
| 619 | 3 | 4 | 5 | 6 | 7 | VII-2 | Gm12657 |
| 620 | 3 | 4 | 5 | 6 | 7 | VII-2 | Gm12888 |
| 621 | 3 | 4 | 5 | 6 | 7 | VII-2 | Gm13034 |
| 622 | 3 | 4 | 5 | 6 | 7 | VII-2 | Gm13124 |
| 623 | 3 | 4 | 5 | 6 | 7 | VII-2 | Gm13177 |
| 624 | 3 | 4 | 5 | 6 | 7 | VII-2 | Gm13304 |
| 625 | 3 | 4 | 5 | 6 | 7 | VII-2 | Gm13375 |
| 626 | 3 | 4 | 5 | 6 | 7 | VII-2 | Gm13498 |
| 627 | 3 | 4 | 5 | 6 | 7 | VII-2 | Gm13710 |
| 628 | 3 | 4 | 5 | 6 | 7 | VII-2 | Gm14308 |
| 629 | 3 | 4 | 5 | 6 | 7 | VII-2 | Gm14322 |
| 630 | 3 | 4 | 5 | 6 | 7 | VII-2 | Gm14346 |
| 631 | 3 | 4 | 5 | 6 | 7 | VII-2 | Gm14403 |
| 632 | 3 | 4 | 5 | 6 | 7 | VII-2 | Gm14420 |
| 633 | 3 | 4 | 5 | 6 | 7 | VII-2 | Gm14431 |
| 634 | 3 | 4 | 5 | 6 | 7 | VII-2 | Gm14436 |
| 635 | 3 | 4 | 5 | 6 | 7 | VII-2 | Gm14475 |
| 636 | 3 | 4 | 5 | 6 | 7 | VII-2 | Gm14476 |
| 637 | 3 | 4 | 5 | 6 | 7 | VII-2 | Gm14478 |
| 638 | 3 | 4 | 5 | 6 | 7 | VII-2 | Gm15104 |
| 639 | 3 | 4 | 5 | 6 | 7 | VII-2 | Gm15455 |
| 640 | 3 | 4 | 5 | 6 | 7 | VII-2 | Gm15987 |
| 641 | 3 | 4 | 5 | 6 | 7 | VII-2 | Gm16039 |
| 642 | 3 | 4 | 5 | 6 | 7 | VII-2 | Gm16675 |
| 643 | 3 | 4 | 5 | 6 | 7 | VII-2 | Gm19402 |
| 644 | 3 | 4 | 5 | 6 | 7 | VII-2 | Gm1987 |
| 645 | 3 | 4 | 5 | 6 | 7 | VII-2 | Gm20319 |
| 646 | 3 | 4 | 5 | 6 | 7 | VII-2 | Gm20594 |
| 647 | 3 | 4 | 5 | 6 | 7 | VII-2 | Gm20605 |
| 648 | 3 | 4 | 5 | 6 | 7 | VII-2 | Gm20748 |
| 649 | 3 | 4 | 5 | 6 | 7 | VII-2 | Gm20809 |
| 650 | 3 | 4 | 5 | 6 | 7 | VII-2 | Gm20815 |
| 651 | 3 | 4 | 5 | 6 | 7 | VII-2 | Gm21541 |
| 652 | 3 | 4 | 5 | 6 | 7 | VII-2 | Gm3086 |
| 653 | 3 | 4 | 5 | 6 | 7 | VII-2 | Gm3238 |
| 654 | 3 | 4 | 5 | 6 | 7 | VII-2 | Gm3402 |
| 655 | 3 | 4 | 5 | 6 | 7 | VII-2 | Gm3415 |
| 656 | 3 | 4 | 5 | 6 | 7 | VII-2 | Gm4559 |
| 657 | 3 | 4 | 5 | 6 | 7 | VII-2 | Gm4759 |
| 658 | 3 | 4 | 5 | 6 | 7 | VII-2 | Gm4836 |
| 659 | 3 | 4 | 5 | 6 | 7 | VII-2 | Gm5088 |
| 660 | 3 | 4 | 5 | 6 | 7 | VII-2 | Gm5538 |
| 661 | 3 | 4 | 5 | 6 | 7 | VII-2 | Gm5901 |
| 662 | 3 | 4 | 5 | 6 | 7 | VII-2 | Gm6194 |
| 663 | 3 | 4 | 5 | 6 | 7 | VII-2 | Gm6370 |
| 664 | 3 | 4 | 5 | 6 | 7 | VII-2 | Gm6402 |
| 665 | 3 | 4 | 5 | 6 | 7 | VII-2 | Gm6524 |
| 666 | 3 | 4 | 5 | 6 | 7 | VII-2 | Gm6548 |
| 667 | 3 | 4 | 5 | 6 | 7 | VII-2 | Gm6578 |
| 668 | 3 | 4 | 5 | 6 | 7 | VII-2 | Gm6623 |
| 669 | 3 | 4 | 5 | 6 | 7 | VII-2 | Gm6682 |
| 670 | 3 | 4 | 5 | 6 | 7 | VII-2 | Gm6710 |
| 671 | 3 | 4 | 5 | 6 | 7 | VII-2 | Gm7030 |
| 672 | 3 | 4 | 5 | 6 | 7 | VII-2 | Gm7073 |
| 673 | 3 | 4 | 5 | 6 | 7 | VII-2 | Gm7244 |
| 674 | 3 | 4 | 5 | 6 | 7 | VII-2 | Gm867 |
| 675 | 3 | 4 | 5 | 6 | 7 | VII-2 | Gm8898 |
| 676 | 3 | 4 | 5 | 6 | 7 | VII-2 | Gm94 |
| 677 | 3 | 4 | 5 | 6 | 7 | VII-2 | Gm9696 |
| 678 | 3 | 4 | 5 | 6 | 7 | VII-2 | Gmcl1i |
| 679 | 3 | 4 | 5 | 6 | 7 | VII-2 | Gna12 |
| 680 | 3 | 4 | 5 | 6 | 7 | VII-2 | Gnai1 |
| 681 | 3 | 4 | 5 | 6 | 7 | VII-2 | Gnai3 |
| 682 | 3 | 4 | 5 | 6 | 7 | VII-2 | Gng5 |
| 683 | 3 | 4 | 5 | 6 | 7 | VII-2 | Gnpda1 |
| 684 | 3 | 4 | 5 | 6 | 7 | VII-2 | Golga4 |
| 685 | 3 | 4 | 5 | 6 | 7 | VII-2 | Golga7 |
| 686 | 3 | 4 | 5 | 6 | 7 | VII-2 | Golim4 |
| 687 | 3 | 4 | 5 | 6 | 7 | VII-2 | Golph3l |
| 688 | 3 | 4 | 5 | 6 | 7 | VII-2 | Gpam |
| 689 | 3 | 4 | 5 | 6 | 7 | VII-2 | Gpatch2 |
| 690 | 3 | 4 | 5 | 6 | 7 | VII-2 | Gpatch2l |
| 691 | 3 | 4 | 5 | 6 | 7 | VII-2 | Gpatch8 |
| 692 | 3 | 4 | 5 | 6 | 7 | VII-2 | Gpd1 |
| 693 | 3 | 4 | 5 | 6 | 7 | VII-2 | Gpkow |
| 694 | 3 | 4 | 5 | 6 | 7 | VII-2 | Gpm6b |
| 695 | 3 | 4 | 5 | 6 | 7 | VII-2 | Gpn3 |
| 696 | 3 | 4 | 5 | 6 | 7 | VII-2 | Gpr116 |
| 697 | 3 | 4 | 5 | 6 | 7 | VII-2 | Gpr124 |
| 698 | 3 | 4 | 5 | 6 | 7 | VII-2 | Gpr135 |
| 699 | 3 | 4 | 5 | 6 | 7 | VII-2 | Gprasp1 |
| 700 | 3 | 4 | 5 | 6 | 7 | VII-2 | Gpt |
| 701 | 3 | 4 | 5 | 6 | 7 | VII-2 | Gpx5 |
| 702 | 3 | 4 | 5 | 6 | 7 | VII-2 | Gramd4 |
| 703 | 3 | 4 | 5 | 6 | 7 | VII-2 | Grem2 |
| 704 | 3 | 4 | 5 | 6 | 7 | VII-2 | Grhl2 |
| 705 | 3 | 4 | 5 | 6 | 7 | VII-2 | Grhl3 |
| 706 | 3 | 4 | 5 | 6 | 7 | VII-2 | Gsdmc2 |
| 707 | 3 | 4 | 5 | 6 | 7 | VII-2 | Gsta2 |
| 708 | 3 | 4 | 5 | 6 | 7 | VII-2 | Gstm3 |
| 709 | 3 | 4 | 5 | 6 | 7 | VII-2 | Gtf2ird1 |
| 710 | 3 | 4 | 5 | 6 | 7 | VII-2 | Gtpbp10 |
| 711 | 3 | 4 | 5 | 6 | 7 | VII-2 | Gucy1b3 |
| 712 | 3 | 4 | 5 | 6 | 7 | VII-2 | Gyk |
| 713 | 3 | 4 | 5 | 6 | 7 | VII-2 | H2-Aa |
| 714 | 3 | 4 | 5 | 6 | 7 | VII-2 | H2-Ab1 |
| 715 | 3 | 4 | 5 | 6 | 7 | VII-2 | H2-DMb2 |
| 716 | 3 | 4 | 5 | 6 | 7 | VII-2 | H2-Eb1 |
| 717 | 3 | 4 | 5 | 6 | 7 | VII-2 | H2-K1 |
| 718 | 3 | 4 | 5 | 6 | 7 | VII-2 | H2-M2 |
| 719 | 3 | 4 | 5 | 6 | 7 | VII-2 | H2-Q2 |
| 720 | 3 | 4 | 5 | 6 | 7 | VII-2 | H2-Q4 |
| 721 | 3 | 4 | 5 | 6 | 7 | VII-2 | H2-Q5 |
| 722 | 3 | 4 | 5 | 6 | 7 | VII-2 | H2-Q6 |
| 723 | 3 | 4 | 5 | 6 | 7 | VII-2 | H2-Q7 |
| 724 | 3 | 4 | 5 | 6 | 7 | VII-2 | H2-Q8 |
| 725 | 3 | 4 | 5 | 6 | 7 | VII-2 | H2-Q9 |
| 726 | 3 | 4 | 5 | 6 | 7 | VII-2 | H2-T24 |
| 727 | 3 | 4 | 5 | 6 | 7 | VII-2 | H2-T3 |
| 728 | 3 | 4 | 5 | 6 | 7 | VII-2 | Hace1 |
| 729 | 3 | 4 | 5 | 6 | 7 | VII-2 | Haus2 |
| 730 | 3 | 4 | 5 | 6 | 7 | VII-2 | Hcar1 |
| 731 | 3 | 4 | 5 | 6 | 7 | VII-2 | Hcar2 |
| 732 | 3 | 4 | 5 | 6 | 7 | VII-2 | Hccs |
| 733 | 3 | 4 | 5 | 6 | 7 | VII-2 | Hdac2 |
| 734 | 3 | 4 | 5 | 6 | 7 | VII-2 | Hdhd3 |
| 735 | 3 | 4 | 5 | 6 | 7 | VII-2 | Heca |
| 736 | 3 | 4 | 5 | 6 | 7 | VII-2 | Heg1 |
| 737 | 3 | 4 | 5 | 6 | 7 | VII-2 | Hemgn |
| 738 | 3 | 4 | 5 | 6 | 7 | VII-2 | Hephl1 |
| 739 | 3 | 4 | 5 | 6 | 7 | VII-2 | Herc3 |
| 740 | 3 | 4 | 5 | 6 | 7 | VII-2 | Hfe |
| 741 | 3 | 4 | 5 | 6 | 7 | VII-2 | Hibadh |
| 742 | 3 | 4 | 5 | 6 | 7 | VII-2 | Hipk1 |
| 743 | 3 | 4 | 5 | 6 | 7 | VII-2 | Hist1h1d |
| 744 | 3 | 4 | 5 | 6 | 7 | VII-2 | Hist1h1e |
| 745 | 3 | 4 | 5 | 6 | 7 | VII-2 | Hist1h2af |
| 746 | 3 | 4 | 5 | 6 | 7 | VII-2 | Hist1h2ag |
| 747 | 3 | 4 | 5 | 6 | 7 | VII-2 | Hist1h2ap |
| 748 | 3 | 4 | 5 | 6 | 7 | VII-2 | Hist1h2bk |
| 749 | 3 | 4 | 5 | 6 | 7 | VII-2 | Hist1h3c |
| 750 | 3 | 4 | 5 | 6 | 7 | VII-2 | Hist1h3e |
| 751 | 3 | 4 | 5 | 6 | 7 | VII-2 | Hist1h3i |
| 752 | 3 | 4 | 5 | 6 | 7 | VII-2 | Hist1h4d |
| 753 | 3 | 4 | 5 | 6 | 7 | VII-2 | Hist2h2bb |
| 754 | 3 | 4 | 5 | 6 | 7 | VII-2 | Hist2h3c2 |
| 755 | 3 | 4 | 5 | 6 | 7 | VII-2 | Hist2h4 |
| 756 | 3 | 4 | 5 | 6 | 7 | VII-2 | Hist3h2a |
| 757 | 3 | 4 | 5 | 6 | 7 | VII-2 | Hmgcs1 |
| 758 | 3 | 4 | 5 | 6 | 7 | VII-2 | Hn1l |
| 759 | 3 | 4 | 5 | 6 | 7 | VII-2 | Hnf4aos |
| 760 | 3 | 4 | 5 | 6 | 7 | VII-2 | Hnrnph1 |
| 761 | 3 | 4 | 5 | 6 | 7 | VII-2 | Hnrnph2 |
| 762 | 3 | 4 | 5 | 6 | 7 | VII-2 | Hnrnpu1 |
| 763 | 3 | 4 | 5 | 6 | 7 | VII-2 | Hook1 |
| 764 | 3 | 4 | 5 | 6 | 7 | VII-2 | Hoxa4 |
| 765 | 3 | 4 | 5 | 6 | 7 | VII-2 | Hoxc13 |
| 766 | 3 | 4 | 5 | 6 | 7 | VII-2 | Hpgds |

Fig. 34 - 5

| | | | | | | | |
|---|---|---|---|---|---|---|---|
| 767 | 3 | 4 | 5 | 6 | 7 | VII-2 | Hps3 |
| 768 | 3 | 4 | 5 | 6 | 7 | VII-2 | Hrc |
| 769 | 3 | 4 | 5 | 6 | 7 | VII-2 | Hs3st1 |
| 770 | 3 | 4 | 5 | 6 | 7 | VII-2 | Hsd17b6 |
| 771 | 3 | 4 | 5 | 6 | 7 | VII-2 | Hsd3b1 |
| 772 | 3 | 4 | 5 | 6 | 7 | VII-2 | Hsd3b2 |
| 773 | 3 | 4 | 5 | 6 | 7 | VII-2 | Hsd3b3 |
| 774 | 3 | 4 | 5 | 6 | 7 | VII-2 | Hsdl2 |
| 775 | 3 | 4 | 5 | 6 | 7 | VII-2 | Hspa12a |
| 776 | 3 | 4 | 5 | 6 | 7 | VII-2 | Hspb6 |
| 777 | 3 | 4 | 5 | 6 | 7 | VII-2 | Hyal1 |
| 778 | 3 | 4 | 5 | 6 | 7 | VII-2 | Hyou1 |
| 779 | 3 | 4 | 5 | 6 | 7 | VII-2 | Icam4 |
| 780 | 3 | 4 | 5 | 6 | 7 | VII-2 | Id2 |
| 781 | 3 | 4 | 5 | 6 | 7 | VII-2 | Id3 |
| 782 | 3 | 4 | 5 | 6 | 7 | VII-2 | Ier3 |
| 783 | 3 | 4 | 5 | 6 | 7 | VII-2 | Ifitm6 |
| 784 | 3 | 4 | 5 | 6 | 7 | VII-2 | Ift20 |
| 785 | 3 | 4 | 5 | 6 | 7 | VII-2 | Igfals |
| 786 | 3 | 4 | 5 | 6 | 7 | VII-2 | Igfbp5 |
| 787 | 3 | 4 | 5 | 6 | 7 | VII-2 | Igfbp7 |
| 788 | 3 | 4 | 5 | 6 | 7 | VII-2 | Igfbpl1 |
| 789 | 3 | 4 | 5 | 6 | 7 | VII-2 | Ikzf5 |
| 790 | 3 | 4 | 5 | 6 | 7 | VII-2 | Il10rb |
| 791 | 3 | 4 | 5 | 6 | 7 | VII-2 | Il15ra |
| 792 | 3 | 4 | 5 | 6 | 7 | VII-2 | Il1a |
| 793 | 3 | 4 | 5 | 6 | 7 | VII-2 | Il1f8 |
| 794 | 3 | 4 | 5 | 6 | 7 | VII-2 | Il1f9 |
| 795 | 3 | 4 | 5 | 6 | 7 | VII-2 | Il1r1 |
| 796 | 3 | 4 | 5 | 6 | 7 | VII-2 | Il1rap |
| 797 | 3 | 4 | 5 | 6 | 7 | VII-2 | Il1rl2 |
| 798 | 3 | 4 | 5 | 6 | 7 | VII-2 | Il1rn |
| 799 | 3 | 4 | 5 | 6 | 7 | VII-2 | Il20ra |
| 800 | 3 | 4 | 5 | 6 | 7 | VII-2 | Il33 |
| 801 | 3 | 4 | 5 | 6 | 7 | VII-2 | Impact |
| 802 | 3 | 4 | 5 | 6 | 7 | VII-2 | Impad1 |
| 803 | 3 | 4 | 5 | 6 | 7 | VII-2 | Ino80dos |
| 804 | 3 | 4 | 5 | 6 | 7 | VII-2 | Ints12 |
| 805 | 3 | 4 | 5 | 6 | 7 | VII-2 | Ipo7 |
| 806 | 3 | 4 | 5 | 6 | 7 | VII-2 | Ipw |
| 807 | 3 | 4 | 5 | 6 | 7 | VII-2 | Ireb2 |
| 808 | 3 | 4 | 5 | 6 | 7 | VII-2 | Irf2 |
| 809 | 3 | 4 | 5 | 6 | 7 | VII-2 | Isg20l2 |
| 810 | 3 | 4 | 5 | 6 | 7 | VII-2 | Isoc1 |
| 811 | 3 | 4 | 5 | 6 | 7 | VII-2 | Itgax |
| 812 | 3 | 4 | 5 | 6 | 7 | VII-2 | Itpkb |
| 813 | 3 | 4 | 5 | 6 | 7 | VII-2 | Iyd |
| 814 | 3 | 4 | 5 | 6 | 7 | VII-2 | Jade1 |
| 815 | 3 | 4 | 5 | 6 | 7 | VII-2 | Jag2 |
| 816 | 3 | 4 | 5 | 6 | 7 | VII-2 | Kank1 |
| 817 | 3 | 4 | 5 | 6 | 7 | VII-2 | Kansl1 |
| 818 | 3 | 4 | 5 | 6 | 7 | VII-2 | Kat6b |
| 819 | 3 | 4 | 5 | 6 | 7 | VII-2 | Kazald1 |
| 820 | 3 | 4 | 5 | 6 | 7 | VII-2 | Kcna3 |
| 821 | 3 | 4 | 5 | 6 | 7 | VII-2 | Kcnab2 |
| 822 | 3 | 4 | 5 | 6 | 7 | VII-2 | Kcnc3 |
| 823 | 3 | 4 | 5 | 6 | 7 | VII-2 | Kcne1l |
| 824 | 3 | 4 | 5 | 6 | 7 | VII-2 | Kcng2 |
| 825 | 3 | 4 | 5 | 6 | 7 | VII-2 | Kcnj14 |
| 826 | 3 | 4 | 5 | 6 | 7 | VII-2 | Kcnk2 |
| 827 | 3 | 4 | 5 | 6 | 7 | VII-2 | Kcnv1 |
| 828 | 3 | 4 | 5 | 6 | 7 | VII-2 | Kctd13 |
| 829 | 3 | 4 | 5 | 6 | 7 | VII-2 | Kctd5 |
| 830 | 3 | 4 | 5 | 6 | 7 | VII-2 | Kdelc2 |
| 831 | 3 | 4 | 5 | 6 | 7 | VII-2 | Kdm4a |
| 832 | 3 | 4 | 5 | 6 | 7 | VII-2 | Kdr |
| 833 | 3 | 4 | 5 | 6 | 7 | VII-2 | Keg1 |
| 834 | 3 | 4 | 5 | 6 | 7 | VII-2 | Kel |
| 835 | 3 | 4 | 5 | 6 | 7 | VII-2 | Khnyn |
| 836 | 3 | 4 | 5 | 6 | 7 | VII-2 | Kif13a |
| 837 | 3 | 4 | 5 | 6 | 7 | VII-2 | Kif21a |
| 838 | 3 | 4 | 5 | 6 | 7 | VII-2 | Kif3b |
| 839 | 3 | 4 | 5 | 6 | 7 | VII-2 | Kifc5b |
| 840 | 3 | 4 | 5 | 6 | 7 | VII-2 | Kirrel |
| 841 | 3 | 4 | 5 | 6 | 7 | VII-2 | Klf1 |
| 842 | 3 | 4 | 5 | 6 | 7 | VII-2 | Klf3 |
| 843 | 3 | 4 | 5 | 6 | 7 | VII-2 | Klf4 |
| 844 | 3 | 4 | 5 | 6 | 7 | VII-2 | Klf7 |
| 845 | 3 | 4 | 5 | 6 | 7 | VII-2 | Klf9 |
| 846 | 3 | 4 | 5 | 6 | 7 | VII-2 | Klhl20 |
| 847 | 3 | 4 | 5 | 6 | 7 | VII-2 | Klhl24 |
| 848 | 3 | 4 | 5 | 6 | 7 | VII-2 | Klhl9 |
| 849 | 3 | 4 | 5 | 6 | 7 | VII-2 | Klra22 |
| 850 | 3 | 4 | 5 | 6 | 7 | VII-2 | Klrd1 |
| 851 | 3 | 4 | 5 | 6 | 7 | VII-2 | Kmt2d |
| 852 | 3 | 4 | 5 | 6 | 7 | VII-2 | Kmt2e |
| 853 | 3 | 4 | 5 | 6 | 7 | VII-2 | Krcc1 |
| 854 | 3 | 4 | 5 | 6 | 7 | VII-2 | Kremen1 |
| 855 | 3 | 4 | 5 | 6 | 7 | VII-2 | Krt10 |
| 856 | 3 | 4 | 5 | 6 | 7 | VII-2 | Krt6b |
| 857 | 3 | 4 | 5 | 6 | 7 | VII-2 | Krt80 |
| 858 | 3 | 4 | 5 | 6 | 7 | VII-2 | Krt83 |
| 859 | 3 | 4 | 5 | 6 | 7 | VII-2 | Krtap16-3 |
| 860 | 3 | 4 | 5 | 6 | 7 | VII-2 | Krtap4-1 |
| 861 | 3 | 4 | 5 | 6 | 7 | VII-2 | Krtap4-16 |
| 862 | 3 | 4 | 5 | 6 | 7 | VII-2 | Krtap4-2 |
| 863 | 3 | 4 | 5 | 6 | 7 | VII-2 | Krtap4-8 |
| 864 | 3 | 4 | 5 | 6 | 7 | VII-2 | Krtap9-1 |
| 865 | 3 | 4 | 5 | 6 | 7 | VII-2 | Krtcap3 |
| 866 | 3 | 4 | 5 | 6 | 7 | VII-2 | Ky |
| 867 | 3 | 4 | 5 | 6 | 7 | VII-2 | L2hgdh |
| 868 | 3 | 4 | 5 | 6 | 7 | VII-2 | LOC100503496 |
| 869 | 3 | 4 | 5 | 6 | 7 | VII-2 | LOC106740 |
| 870 | 3 | 4 | 5 | 6 | 7 | VII-2 | Lacc1 |
| 871 | 3 | 4 | 5 | 6 | 7 | VII-2 | Lactb |
| 872 | 3 | 4 | 5 | 6 | 7 | VII-2 | Lactb2 |
| 873 | 3 | 4 | 5 | 6 | 7 | VII-2 | Larp4b |
| 874 | 3 | 4 | 5 | 6 | 7 | VII-2 | Lat2 |
| 875 | 3 | 4 | 5 | 6 | 7 | VII-2 | Lca5 |
| 876 | 3 | 4 | 5 | 6 | 7 | VII-2 | Ldlrad3 |
| 877 | 3 | 4 | 5 | 6 | 7 | VII-2 | Leap2 |
| 878 | 3 | 4 | 5 | 6 | 7 | VII-2 | Lefty1 |
| 879 | 3 | 4 | 5 | 6 | 7 | VII-2 | Lep |
| 880 | 3 | 4 | 5 | 6 | 7 | VII-2 | Lgals12 |
| 881 | 3 | 4 | 5 | 6 | 7 | VII-2 | Lgals2 |
| 882 | 3 | 4 | 5 | 6 | 7 | VII-2 | Lima1 |
| 883 | 3 | 4 | 5 | 6 | 7 | VII-2 | Lin52 |
| 884 | 3 | 4 | 5 | 6 | 7 | VII-2 | Lingo1 |
| 885 | 3 | 4 | 5 | 6 | 7 | VII-2 | Lipg |
| 886 | 3 | 4 | 5 | 6 | 7 | VII-2 | Lipo1 |
| 887 | 3 | 4 | 5 | 6 | 7 | VII-2 | Lix1l |
| 888 | 3 | 4 | 5 | 6 | 7 | VII-2 | Lnpep |
| 889 | 3 | 4 | 5 | 6 | 7 | VII-2 | Lonrf1 |
| 890 | 3 | 4 | 5 | 6 | 7 | VII-2 | Loxl1 |
| 891 | 3 | 4 | 5 | 6 | 7 | VII-2 | Lpar3 |
| 892 | 3 | 4 | 5 | 6 | 7 | VII-2 | Lpar5 |
| 893 | 3 | 4 | 5 | 6 | 7 | VII-2 | Lpcat1 |
| 894 | 3 | 4 | 5 | 6 | 7 | VII-2 | Lphn1 |
| 895 | 3 | 4 | 5 | 6 | 7 | VII-2 | Lrch1 |
| 896 | 3 | 4 | 5 | 6 | 7 | VII-2 | Lrch3 |
| 897 | 3 | 4 | 5 | 6 | 7 | VII-2 | Lrif1 |
| 898 | 3 | 4 | 5 | 6 | 7 | VII-2 | Lrig1 |
| 899 | 3 | 4 | 5 | 6 | 7 | VII-2 | Lrig3 |
| 900 | 3 | 4 | 5 | 6 | 7 | VII-2 | Lrp4 |
| 901 | 3 | 4 | 5 | 6 | 7 | VII-2 | Lrr1 |
| 902 | 3 | 4 | 5 | 6 | 7 | VII-2 | Lrrc16a |
| 903 | 3 | 4 | 5 | 6 | 7 | VII-2 | Lrrc17 |
| 904 | 3 | 4 | 5 | 6 | 7 | VII-2 | Lrrc38 |
| 905 | 3 | 4 | 5 | 6 | 7 | VII-2 | Lrrc3b |
| 906 | 3 | 4 | 5 | 6 | 7 | VII-2 | Lrrc40 |
| 907 | 3 | 4 | 5 | 6 | 7 | VII-2 | Lrrc52 |
| 908 | 3 | 4 | 5 | 6 | 7 | VII-2 | Lrrc57 |
| 909 | 3 | 4 | 5 | 6 | 7 | VII-2 | Lrrc58 |
| 910 | 3 | 4 | 5 | 6 | 7 | VII-2 | Lrrc8b |
| 911 | 3 | 4 | 5 | 6 | 7 | VII-2 | Lrrc8d |
| 912 | 3 | 4 | 5 | 6 | 7 | VII-2 | Ltbp2 |
| 913 | 3 | 4 | 5 | 6 | 7 | VII-2 | Ly6f |
| 914 | 3 | 4 | 5 | 6 | 7 | VII-2 | Ly6g5b |
| 915 | 3 | 4 | 5 | 6 | 7 | VII-2 | Ly6g6e |
| 916 | 3 | 4 | 5 | 6 | 7 | VII-2 | Ly75 |
| 917 | 3 | 4 | 5 | 6 | 7 | VII-2 | Lypd1 |
| 918 | 3 | 4 | 5 | 6 | 7 | VII-2 | Lypd5 |
| 919 | 3 | 4 | 5 | 6 | 7 | VII-2 | Mad2l1 |
| 920 | 3 | 4 | 5 | 6 | 7 | VII-2 | Maf |
| 921 | 3 | 4 | 5 | 6 | 7 | VII-2 | Magee1 |
| 922 | 3 | 4 | 5 | 6 | 7 | VII-2 | Magt1 |
| 923 | 3 | 4 | 5 | 6 | 7 | VII-2 | Mal |
| 924 | 3 | 4 | 5 | 6 | 7 | VII-2 | Mamdc2 |
| 925 | 3 | 4 | 5 | 6 | 7 | VII-2 | Maml1 |
| 926 | 3 | 4 | 5 | 6 | 7 | VII-2 | Maml3 |
| 927 | 3 | 4 | 5 | 6 | 7 | VII-2 | Man2b2 |
| 928 | 3 | 4 | 5 | 6 | 7 | VII-2 | Manscl |
| 929 | 3 | 4 | 5 | 6 | 7 | VII-2 | Map2k1 |
| 930 | 3 | 4 | 5 | 6 | 7 | VII-2 | Map2k3os |
| 931 | 3 | 4 | 5 | 6 | 7 | VII-2 | Map3k1 |
| 932 | 3 | 4 | 5 | 6 | 7 | VII-2 | Map3k3 |
| 933 | 3 | 4 | 5 | 6 | 7 | VII-2 | Map4k3 |
| 934 | 3 | 4 | 5 | 6 | 7 | VII-2 | Map7 |
| 935 | 3 | 4 | 5 | 6 | 7 | VII-2 | Mapk7 |
| 936 | 3 | 4 | 5 | 6 | 7 | VII-2 | Mapkapk3 |
| 937 | 3 | 4 | 5 | 6 | 7 | VII-2 | March3 |
| 938 | 3 | 4 | 5 | 6 | 7 | VII-2 | March8 |
| 939 | 3 | 4 | 5 | 6 | 7 | VII-2 | Marcksl1-ps4 |
| 940 | 3 | 4 | 5 | 6 | 7 | VII-2 | Mark4 |
| 941 | 3 | 4 | 5 | 6 | 7 | VII-2 | Mast4 |
| 942 | 3 | 4 | 5 | 6 | 7 | VII-2 | Mat2b |
| 943 | 3 | 4 | 5 | 6 | 7 | VII-2 | Mavs |
| 944 | 3 | 4 | 5 | 6 | 7 | VII-2 | Mbip |
| 945 | 3 | 4 | 5 | 6 | 7 | VII-2 | Mblac2 |
| 946 | 3 | 4 | 5 | 6 | 7 | VII-2 | Mcam |
| 947 | 3 | 4 | 5 | 6 | 7 | VII-2 | Mcm5 |
| 948 | 3 | 4 | 5 | 6 | 7 | VII-2 | Mdm4 |
| 949 | 3 | 4 | 5 | 6 | 7 | VII-2 | Med6 |
| 950 | 3 | 4 | 5 | 6 | 7 | VII-2 | Mef2c |
| 951 | 3 | 4 | 5 | 6 | 7 | VII-2 | Mef2d |
| 952 | 3 | 4 | 5 | 6 | 7 | VII-2 | Megf9 |
| 953 | 3 | 4 | 5 | 6 | 7 | VII-2 | Mep1a |
| 954 | 3 | 4 | 5 | 6 | 7 | VII-2 | Mertk |
| 955 | 3 | 4 | 5 | 6 | 7 | VII-2 | Mettl20 |
| 956 | 3 | 4 | 5 | 6 | 7 | VII-2 | Mex3c |
| 957 | 3 | 4 | 5 | 6 | 7 | VII-2 | Mfsd8 |
| 958 | 3 | 4 | 5 | 6 | 7 | VII-2 | Mgat5 |

Fig. 34 - 6

| | | | | | | | |
|---|---|---|---|---|---|---|---|
| 959 | 3 | 4 | 5 | 6 | 7 | VII-2 | Mia2 |
| 960 | 3 | 4 | 5 | 6 | 7 | VII-2 | Mical2 |
| 961 | 3 | 4 | 5 | 6 | 7 | VII-2 | Mid2 |
| 962 | 3 | 4 | 5 | 6 | 7 | VII-2 | Mier1 |
| 963 | 3 | 4 | 5 | 6 | 7 | VII-2 | Mir1199 |
| 964 | 3 | 4 | 5 | 6 | 7 | VII-2 | Mir215 |
| 965 | 3 | 4 | 5 | 6 | 7 | VII-2 | Mir3473g |
| 966 | 3 | 4 | 5 | 6 | 7 | VII-2 | Mir486 |
| 967 | 3 | 4 | 5 | 6 | 7 | VII-2 | Mir6345 |
| 968 | 3 | 4 | 5 | 6 | 7 | VII-2 | Mir6363 |
| 969 | 3 | 4 | 5 | 6 | 7 | VII-2 | Mir6386 |
| 970 | 3 | 4 | 5 | 6 | 7 | VII-2 | Mir6403 |
| 971 | 3 | 4 | 5 | 6 | 7 | VII-2 | Mir6516 |
| 972 | 3 | 4 | 5 | 6 | 7 | VII-2 | Mir683-2 |
| 973 | 3 | 4 | 5 | 6 | 7 | VII-2 | Mir6981 |
| 974 | 3 | 4 | 5 | 6 | 7 | VII-2 | Mir7060 |
| 975 | 3 | 4 | 5 | 6 | 7 | VII-2 | Mir8101 |
| 976 | 3 | 4 | 5 | 6 | 7 | VII-2 | Mir8103 |
| 977 | 3 | 4 | 5 | 6 | 7 | VII-2 | Mir8106 |
| 978 | 3 | 4 | 5 | 6 | 7 | VII-2 | Mir8116 |
| 979 | 3 | 4 | 5 | 6 | 7 | VII-2 | Mllt10 |
| 980 | 3 | 4 | 5 | 6 | 7 | VII-2 | Mllt4 |
| 981 | 3 | 4 | 5 | 6 | 7 | VII-2 | Mmab |
| 982 | 3 | 4 | 5 | 6 | 7 | VII-2 | Mmd |
| 983 | 3 | 4 | 5 | 6 | 7 | VII-2 | Mmp19 |
| 984 | 3 | 4 | 5 | 6 | 7 | VII-2 | Mmp28 |
| 985 | 3 | 4 | 5 | 6 | 7 | VII-2 | Mob1a |
| 986 | 3 | 4 | 5 | 6 | 7 | VII-2 | Morc3 |
| 987 | 3 | 4 | 5 | 6 | 7 | VII-2 | Morn2 |
| 988 | 3 | 4 | 5 | 6 | 7 | VII-2 | Mospd2 |
| 989 | 3 | 4 | 5 | 6 | 7 | VII-2 | Moxd1 |
| 990 | 3 | 4 | 5 | 6 | 7 | VII-2 | Mpzl3 |
| 991 | 3 | 4 | 5 | 6 | 7 | VII-2 | Mr1 |
| 992 | 3 | 4 | 5 | 6 | 7 | VII-2 | Mrgbp |
| 993 | 3 | 4 | 5 | 6 | 7 | VII-2 | Mrgprf |
| 994 | 3 | 4 | 5 | 6 | 7 | VII-2 | Mroh6 |
| 995 | 3 | 4 | 5 | 6 | 7 | VII-2 | Mrps2 |
| 996 | 3 | 4 | 5 | 6 | 7 | VII-2 | Mrrf |
| 997 | 3 | 4 | 5 | 6 | 7 | VII-2 | Msl2 |
| 998 | 3 | 4 | 5 | 6 | 7 | VII-2 | Msln |
| 999 | 3 | 4 | 5 | 6 | 7 | VII-2 | Msmp |
| 1000 | 3 | 4 | 5 | 6 | 7 | VII-2 | Msn |
| 1001 | 3 | 4 | 5 | 6 | 7 | VII-2 | Msx2 |
| 1002 | 3 | 4 | 5 | 6 | 7 | VII-2 | Mterf1a |
| 1003 | 3 | 4 | 5 | 6 | 7 | VII-2 | Mterfd3 |
| 1004 | 3 | 4 | 5 | 6 | 7 | VII-2 | Mthfs |
| 1005 | 3 | 4 | 5 | 6 | 7 | VII-2 | Mtm1 |
| 1006 | 3 | 4 | 5 | 6 | 7 | VII-2 | Mtmr9 |
| 1007 | 3 | 4 | 5 | 6 | 7 | VII-2 | Mtss1l |
| 1008 | 3 | 4 | 5 | 6 | 7 | VII-2 | Muc15 |
| 1009 | 3 | 4 | 5 | 6 | 7 | VII-2 | Mvb12b |
| 1010 | 3 | 4 | 5 | 6 | 7 | VII-2 | Mxd4 |
| 1011 | 3 | 4 | 5 | 6 | 7 | VII-2 | Mxi1 |
| 1012 | 3 | 4 | 5 | 6 | 7 | VII-2 | Myc |
| 1013 | 3 | 4 | 5 | 6 | 7 | VII-2 | Mylip |
| 1014 | 3 | 4 | 5 | 6 | 7 | VII-2 | Mylk |
| 1015 | 3 | 4 | 5 | 6 | 7 | VII-2 | Mylk4 |
| 1016 | 3 | 4 | 5 | 6 | 7 | VII-2 | Myo19 |
| 1017 | 3 | 4 | 5 | 6 | 7 | VII-2 | Mysm1 |
| 1018 | 3 | 4 | 5 | 6 | 7 | VII-2 | Mzt1 |
| 1019 | 3 | 4 | 5 | 6 | 7 | VII-2 | Naa40 |
| 1020 | 3 | 4 | 5 | 6 | 7 | VII-2 | Naa60 |
| 1021 | 3 | 4 | 5 | 6 | 7 | VII-2 | Nab2 |
| 1022 | 3 | 4 | 5 | 6 | 7 | VII-2 | Nabp1 |
| 1023 | 3 | 4 | 5 | 6 | 7 | VII-2 | Naf1 |
| 1024 | 3 | 4 | 5 | 6 | 7 | VII-2 | Nat2 |
| 1025 | 3 | 4 | 5 | 6 | 7 | VII-2 | Nbn |
| 1026 | 3 | 4 | 5 | 6 | 7 | VII-2 | Nck1 |
| 1027 | 3 | 4 | 5 | 6 | 7 | VII-2 | Ncoa4 |
| 1028 | 3 | 4 | 5 | 6 | 7 | VII-2 | Ncstn |
| 1029 | 3 | 4 | 5 | 6 | 7 | VII-2 | Ndel1 |
| 1030 | 3 | 4 | 5 | 6 | 7 | VII-2 | Ndst1 |
| 1031 | 3 | 4 | 5 | 6 | 7 | VII-2 | Ndufa12 |
| 1032 | 3 | 4 | 5 | 6 | 7 | VII-2 | Ndufaf3 |
| 1033 | 3 | 4 | 5 | 6 | 7 | VII-2 | Nebl |
| 1034 | 3 | 4 | 5 | 6 | 7 | VII-2 | Nedd4 |
| 1035 | 3 | 4 | 5 | 6 | 7 | VII-2 | Nedd9 |
| 1036 | 3 | 4 | 5 | 6 | 7 | VII-2 | Nek7 |
| 1037 | 3 | 4 | 5 | 6 | 7 | VII-2 | Nenf |
| 1038 | 3 | 4 | 5 | 6 | 7 | VII-2 | Nfat5 |
| 1039 | 3 | 4 | 5 | 6 | 7 | VII-2 | Nfe2l3 |
| 1040 | 3 | 4 | 5 | 6 | 7 | VII-2 | Nfkb1 |
| 1041 | 3 | 4 | 5 | 6 | 7 | VII-2 | Nfya |
| 1042 | 3 | 4 | 5 | 6 | 7 | VII-2 | Ngfr |
| 1043 | 3 | 4 | 5 | 6 | 7 | VII-2 | Nhsl1 |
| 1044 | 3 | 4 | 5 | 6 | 7 | VII-2 | Nid1 |
| 1045 | 3 | 4 | 5 | 6 | 7 | VII-2 | Nipal1 |
| 1046 | 3 | 4 | 5 | 6 | 7 | VII-2 | Nipal2 |
| 1047 | 3 | 4 | 5 | 6 | 7 | VII-2 | Nkain1 |
| 1048 | 3 | 4 | 5 | 6 | 7 | VII-2 | Nkx2-2 |
| 1049 | 3 | 4 | 5 | 6 | 7 | VII-2 | Nlgn2 |
| 1050 | 3 | 4 | 5 | 6 | 7 | VII-2 | Nlrp10 |
| 1051 | 3 | 4 | 5 | 6 | 7 | VII-2 | Nme6 |
| 1052 | 3 | 4 | 5 | 6 | 7 | VII-2 | Nmt1 |
| 1053 | 3 | 4 | 5 | 6 | 7 | VII-2 | Nnt |
| 1054 | 3 | 4 | 5 | 6 | 7 | VII-2 | Notch1 |
| 1055 | 3 | 4 | 5 | 6 | 7 | VII-2 | Notch3 |
| 1056 | 3 | 4 | 5 | 6 | 7 | VII-2 | Notum |
| 1057 | 3 | 4 | 5 | 6 | 7 | VII-2 | Npepps |
| 1058 | 3 | 4 | 5 | 6 | 7 | VII-2 | Npnt |
| 1059 | 3 | 4 | 5 | 6 | 7 | VII-2 | Npr3 |
| 1060 | 3 | 4 | 5 | 6 | 7 | VII-2 | Npw |
| 1061 | 3 | 4 | 5 | 6 | 7 | VII-2 | Npy1r |
| 1062 | 3 | 4 | 5 | 6 | 7 | VII-2 | Nr1d2 |
| 1063 | 3 | 4 | 5 | 6 | 7 | VII-2 | Nr1h5 |
| 1064 | 3 | 4 | 5 | 6 | 7 | VII-2 | Nr2c2 |
| 1065 | 3 | 4 | 5 | 6 | 7 | VII-2 | Nrbf2 |
| 1066 | 3 | 4 | 5 | 6 | 7 | VII-2 | Nrep |
| 1067 | 3 | 4 | 5 | 6 | 7 | VII-2 | Nrgn |
| 1068 | 3 | 4 | 5 | 6 | 7 | VII-2 | Nrip1 |
| 1069 | 3 | 4 | 5 | 6 | 7 | VII-2 | Nrn1 |
| 1070 | 3 | 4 | 5 | 6 | 7 | VII-2 | Nsd1 |
| 1071 | 3 | 4 | 5 | 6 | 7 | VII-2 | Nsdhl |
| 1072 | 3 | 4 | 5 | 6 | 7 | VII-2 | Nsg2 |
| 1073 | 3 | 4 | 5 | 6 | 7 | VII-2 | Nsun3 |
| 1074 | 3 | 4 | 5 | 6 | 7 | VII-2 | Ntn4 |
| 1075 | 3 | 4 | 5 | 6 | 7 | VII-2 | Nuak1 |
| 1076 | 3 | 4 | 5 | 6 | 7 | VII-2 | Nudt12 |
| 1077 | 3 | 4 | 5 | 6 | 7 | VII-2 | Nudt15 |
| 1078 | 3 | 4 | 5 | 6 | 7 | VII-2 | Nudt22 |
| 1079 | 3 | 4 | 5 | 6 | 7 | VII-2 | Nup153 |
| 1080 | 3 | 4 | 5 | 6 | 7 | VII-2 | Nupl2 |
| 1081 | 3 | 4 | 5 | 6 | 7 | VII-2 | Nutf2-ps1 |
| 1082 | 3 | 4 | 5 | 6 | 7 | VII-2 | OTTMUSG00000016609 |
| 1083 | 3 | 4 | 5 | 6 | 7 | VII-2 | Ocrl |
| 1084 | 3 | 4 | 5 | 6 | 7 | VII-2 | Olfr761 |
| 1085 | 3 | 4 | 5 | 6 | 7 | VII-2 | Olfr920 |
| 1086 | 3 | 4 | 5 | 6 | 7 | VII-2 | Opa3 |
| 1087 | 3 | 4 | 5 | 6 | 7 | VII-2 | Ormdl2 |
| 1088 | 3 | 4 | 5 | 6 | 7 | VII-2 | Osbpl5 |
| 1089 | 3 | 4 | 5 | 6 | 7 | VII-2 | Ost4 |
| 1090 | 3 | 4 | 5 | 6 | 7 | VII-2 | Ostn |
| 1091 | 3 | 4 | 5 | 6 | 7 | VII-2 | Oxtr |
| 1092 | 3 | 4 | 5 | 6 | 7 | VII-2 | P2ry1 |
| 1093 | 3 | 4 | 5 | 6 | 7 | VII-2 | Pacsin1 |
| 1094 | 3 | 4 | 5 | 6 | 7 | VII-2 | Pak1 |
| 1095 | 3 | 4 | 5 | 6 | 7 | VII-2 | Palmd |
| 1096 | 3 | 4 | 5 | 6 | 7 | VII-2 | Pank3 |
| 1097 | 3 | 4 | 5 | 6 | 7 | VII-2 | Paqr3 |
| 1098 | 3 | 4 | 5 | 6 | 7 | VII-2 | Paqr9 |
| 1099 | 3 | 4 | 5 | 6 | 7 | VII-2 | Pard6g |
| 1100 | 3 | 4 | 5 | 6 | 7 | VII-2 | Pate2 |
| 1101 | 3 | 4 | 5 | 6 | 7 | VII-2 | Pawr |
| 1102 | 3 | 4 | 5 | 6 | 7 | VII-2 | Pbsn |
| 1103 | 3 | 4 | 5 | 6 | 7 | VII-2 | Pcbp1 |
| 1104 | 3 | 4 | 5 | 6 | 7 | VII-2 | Pcdh1 |
| 1105 | 3 | 4 | 5 | 6 | 7 | VII-2 | Pcdh7 |
| 1106 | 3 | 4 | 5 | 6 | 7 | VII-2 | Pcdhga11 |
| 1107 | 3 | 4 | 5 | 6 | 7 | VII-2 | Pcid2 |
| 1108 | 3 | 4 | 5 | 6 | 7 | VII-2 | Pcp4l1 |
| 1109 | 3 | 4 | 5 | 6 | 7 | VII-2 | Pde12 |
| 1110 | 3 | 4 | 5 | 6 | 7 | VII-2 | Pde6g |
| 1111 | 3 | 4 | 5 | 6 | 7 | VII-2 | Pde8a |
| 1112 | 3 | 4 | 5 | 6 | 7 | VII-2 | Pdgfa |
| 1113 | 3 | 4 | 5 | 6 | 7 | VII-2 | Pdgfrl |
| 1114 | 3 | 4 | 5 | 6 | 7 | VII-2 | Pdia4 |
| 1115 | 3 | 4 | 5 | 6 | 7 | VII-2 | Pdpk1 |
| 1116 | 3 | 4 | 5 | 6 | 7 | VII-2 | Pdss2 |
| 1117 | 3 | 4 | 5 | 6 | 7 | VII-2 | Pdxp |
| 1118 | 3 | 4 | 5 | 6 | 7 | VII-2 | Pdzd2 |
| 1119 | 3 | 4 | 5 | 6 | 7 | VII-2 | Peak1 |
| 1120 | 3 | 4 | 5 | 6 | 7 | VII-2 | Per3 |
| 1121 | 3 | 4 | 5 | 6 | 7 | VII-2 | Perm1 |
| 1122 | 3 | 4 | 5 | 6 | 7 | VII-2 | Pex11a |
| 1123 | 3 | 4 | 5 | 6 | 7 | VII-2 | Pfdn4 |
| 1124 | 3 | 4 | 5 | 6 | 7 | VII-2 | Pfkfb2 |
| 1125 | 3 | 4 | 5 | 6 | 7 | VII-2 | Pfkl |
| 1126 | 3 | 4 | 5 | 6 | 7 | VII-2 | Pfn2 |
| 1127 | 3 | 4 | 5 | 6 | 7 | VII-2 | Pfn4 |
| 1128 | 3 | 4 | 5 | 6 | 7 | VII-2 | Phactr4 |
| 1129 | 3 | 4 | 5 | 6 | 7 | VII-2 | Phf12 |
| 1130 | 3 | 4 | 5 | 6 | 7 | VII-2 | Phf2 |
| 1131 | 3 | 4 | 5 | 6 | 7 | VII-2 | Phyhip |
| 1132 | 3 | 4 | 5 | 6 | 7 | VII-2 | Pi16 |
| 1133 | 3 | 4 | 5 | 6 | 7 | VII-2 | Piezo1 |
| 1134 | 3 | 4 | 5 | 6 | 7 | VII-2 | Pigg |
| 1135 | 3 | 4 | 5 | 6 | 7 | VII-2 | Pigh |
| 1136 | 3 | 4 | 5 | 6 | 7 | VII-2 | Pik3c2g |
| 1137 | 3 | 4 | 5 | 6 | 7 | VII-2 | Pik3r1 |
| 1138 | 3 | 4 | 5 | 6 | 7 | VII-2 | Pim1 |
| 1139 | 3 | 4 | 5 | 6 | 7 | VII-2 | Pin1rt1 |
| 1140 | 3 | 4 | 5 | 6 | 7 | VII-2 | Pip5k1a |
| 1141 | 3 | 4 | 5 | 6 | 7 | VII-2 | Pip5kl1 |
| 1142 | 3 | 4 | 5 | 6 | 7 | VII-2 | Pira4 |
| 1143 | 3 | 4 | 5 | 6 | 7 | VII-2 | Pirt |
| 1144 | 3 | 4 | 5 | 6 | 7 | VII-2 | Pkd1 |
| 1145 | 3 | 4 | 5 | 6 | 7 | VII-2 | Pkd2 |
| 1146 | 3 | 4 | 5 | 6 | 7 | VII-2 | Pkia |
| 1147 | 3 | 4 | 5 | 6 | 7 | VII-2 | Pla2g4a |
| 1148 | 3 | 4 | 5 | 6 | 7 | VII-2 | Plac9b |
| 1149 | 3 | 4 | 5 | 6 | 7 | VII-2 | Plagl1 |
| 1150 | 3 | 4 | 5 | 6 | 7 | VII-2 | Plau |

Fig. 34 - 7

| | | | | | | | |
|---|---|---|---|---|---|---|---|
| 1151 | 3 | 4 | 5 | 6 | 7 | VII-2 | Picg1 |
| 1152 | 3 | 4 | 5 | 6 | 7 | VII-2 | Picl2 |
| 1153 | 3 | 4 | 5 | 6 | 7 | VII-2 | Pietlos |
| 1154 | 3 | 4 | 5 | 6 | 7 | VII-2 | Pip2 |
| 1155 | 3 | 4 | 5 | 6 | 7 | VII-2 | Piscr1 |
| 1156 | 3 | 4 | 5 | 6 | 7 | VII-2 | Piscr2 |
| 1157 | 3 | 4 | 5 | 6 | 7 | VII-2 | Piscr4 |
| 1158 | 3 | 4 | 5 | 6 | 7 | VII-2 | Pitp |
| 1159 | 3 | 4 | 5 | 6 | 7 | VII-2 | Plxna1 |
| 1160 | 3 | 4 | 5 | 6 | 7 | VII-2 | Plxna2 |
| 1161 | 3 | 4 | 5 | 6 | 7 | VII-2 | Pm20d2 |
| 1162 | 3 | 4 | 5 | 6 | 7 | VII-2 | Pnisr |
| 1163 | 3 | 4 | 5 | 6 | 7 | VII-2 | Pnmal2 |
| 1164 | 3 | 4 | 5 | 6 | 7 | VII-2 | Pnp2 |
| 1165 | 3 | 4 | 5 | 6 | 7 | VII-2 | Pnpla5 |
| 1166 | 3 | 4 | 5 | 6 | 7 | VII-2 | Polh |
| 1167 | 3 | 4 | 5 | 6 | 7 | VII-2 | Polm |
| 1168 | 3 | 4 | 5 | 6 | 7 | VII-2 | Poln |
| 1169 | 3 | 4 | 5 | 6 | 7 | VII-2 | Polr2i |
| 1170 | 3 | 4 | 5 | 6 | 7 | VII-2 | Polr3g |
| 1171 | 3 | 4 | 5 | 6 | 7 | VII-2 | Polrmt |
| 1172 | 3 | 4 | 5 | 6 | 7 | VII-2 | Pom121 |
| 1173 | 3 | 4 | 5 | 6 | 7 | VII-2 | Pou2f3 |
| 1174 | 3 | 4 | 5 | 6 | 7 | VII-2 | Ppap2b |
| 1175 | 3 | 4 | 5 | 6 | 7 | VII-2 | Ppapdc1b |
| 1176 | 3 | 4 | 5 | 6 | 7 | VII-2 | Pparg |
| 1177 | 3 | 4 | 5 | 6 | 7 | VII-2 | Pphln1 |
| 1178 | 3 | 4 | 5 | 6 | 7 | VII-2 | Ppifos |
| 1179 | 3 | 4 | 5 | 6 | 7 | VII-2 | Ppp1r14c |
| 1180 | 3 | 4 | 5 | 6 | 7 | VII-2 | Ppp1r1a |
| 1181 | 3 | 4 | 5 | 6 | 7 | VII-2 | Ppp1r2-ps3 |
| 1182 | 3 | 4 | 5 | 6 | 7 | VII-2 | Ppp5c |
| 1183 | 3 | 4 | 5 | 6 | 7 | VII-2 | Ppwd1 |
| 1184 | 3 | 4 | 5 | 6 | 7 | VII-2 | Prcp |
| 1185 | 3 | 4 | 5 | 6 | 7 | VII-2 | Prdm1 |
| 1186 | 3 | 4 | 5 | 6 | 7 | VII-2 | Prdx3 |
| 1187 | 3 | 4 | 5 | 6 | 7 | VII-2 | Prdx6b |
| 1188 | 3 | 4 | 5 | 6 | 7 | VII-2 | Prep |
| 1189 | 3 | 4 | 5 | 6 | 7 | VII-2 | Prex2 |
| 1190 | 3 | 4 | 5 | 6 | 7 | VII-2 | Prkacb |
| 1191 | 3 | 4 | 5 | 6 | 7 | VII-2 | Prkar1b |
| 1192 | 3 | 4 | 5 | 6 | 7 | VII-2 | Prkar2a |
| 1193 | 3 | 4 | 5 | 6 | 7 | VII-2 | Prkcb |
| 1194 | 3 | 4 | 5 | 6 | 7 | VII-2 | Prkce |
| 1195 | 3 | 4 | 5 | 6 | 7 | VII-2 | Prkch |
| 1196 | 3 | 4 | 5 | 6 | 7 | VII-2 | Prkci |
| 1197 | 3 | 4 | 5 | 6 | 7 | VII-2 | Prkx |
| 1198 | 3 | 4 | 5 | 6 | 7 | VII-2 | Prom2 |
| 1199 | 3 | 4 | 5 | 6 | 7 | VII-2 | Prr32 |
| 1200 | 3 | 4 | 5 | 6 | 7 | VII-2 | Prrc2c |
| 1201 | 3 | 4 | 5 | 6 | 7 | VII-2 | Prrt2 |
| 1202 | 3 | 4 | 5 | 6 | 7 | VII-2 | Psd3 |
| 1203 | 3 | 4 | 5 | 6 | 7 | VII-2 | Psmb11 |
| 1204 | 3 | 4 | 5 | 6 | 7 | VII-2 | Pstpip2 |
| 1205 | 3 | 4 | 5 | 6 | 7 | VII-2 | Ptbp2 |
| 1206 | 3 | 4 | 5 | 6 | 7 | VII-2 | Ptch1 |
| 1207 | 3 | 4 | 5 | 6 | 7 | VII-2 | Ptger1 |
| 1208 | 3 | 4 | 5 | 6 | 7 | VII-2 | Ptger3 |
| 1209 | 3 | 4 | 5 | 6 | 7 | VII-2 | Ptgs2 |
| 1210 | 3 | 4 | 5 | 6 | 7 | VII-2 | Ptk7 |
| 1211 | 3 | 4 | 5 | 6 | 7 | VII-2 | Ptn |
| 1212 | 3 | 4 | 5 | 6 | 7 | VII-2 | Ptpn9 |
| 1213 | 3 | 4 | 5 | 6 | 7 | VII-2 | Ptprb |
| 1214 | 3 | 4 | 5 | 6 | 7 | VII-2 | Pura |
| 1215 | 3 | 4 | 5 | 6 | 7 | VII-2 | Pvrl4 |
| 1216 | 3 | 4 | 5 | 6 | 7 | VII-2 | Pxk |
| 1217 | 3 | 4 | 5 | 6 | 7 | VII-2 | Pxt1 |
| 1218 | 3 | 4 | 5 | 6 | 7 | VII-2 | Qpct |
| 1219 | 3 | 4 | 5 | 6 | 7 | VII-2 | Qtrtd1 |
| 1220 | 3 | 4 | 5 | 6 | 7 | VII-2 | Rab11fip2 |
| 1221 | 3 | 4 | 5 | 6 | 7 | VII-2 | Rab11fip4 |
| 1222 | 3 | 4 | 5 | 6 | 7 | VII-2 | Rab12 |
| 1223 | 3 | 4 | 5 | 6 | 7 | VII-2 | Rab20 |
| 1224 | 3 | 4 | 5 | 6 | 7 | VII-2 | Rab32 |
| 1225 | 3 | 4 | 5 | 6 | 7 | VII-2 | Rab5c |
| 1226 | 3 | 4 | 5 | 6 | 7 | VII-2 | Rad21 |
| 1227 | 3 | 4 | 5 | 6 | 7 | VII-2 | Raet1e |
| 1228 | 3 | 4 | 5 | 6 | 7 | VII-2 | Rai1 |
| 1229 | 3 | 4 | 5 | 6 | 7 | VII-2 | Rai14 |
| 1230 | 3 | 4 | 5 | 6 | 7 | VII-2 | Ranbp2 |
| 1231 | 3 | 4 | 5 | 6 | 7 | VII-2 | Rasgrp1 |
| 1232 | 3 | 4 | 5 | 6 | 7 | VII-2 | Rasgrp3 |
| 1233 | 3 | 4 | 5 | 6 | 7 | VII-2 | Rasl2-9 |
| 1234 | 3 | 4 | 5 | 6 | 7 | VII-2 | Rassf3 |
| 1235 | 3 | 4 | 5 | 6 | 7 | VII-2 | Rassf6 |
| 1236 | 3 | 4 | 5 | 6 | 7 | VII-2 | Rbbp9 |
| 1237 | 3 | 4 | 5 | 6 | 7 | VII-2 | Rbfox2 |
| 1238 | 3 | 4 | 5 | 6 | 7 | VII-2 | Rbl2 |
| 1239 | 3 | 4 | 5 | 6 | 7 | VII-2 | Rbm12 |
| 1240 | 3 | 4 | 5 | 6 | 7 | VII-2 | Rbm15b |
| 1241 | 3 | 4 | 5 | 6 | 7 | VII-2 | Rbms1 |
| 1242 | 3 | 4 | 5 | 6 | 7 | VII-2 | Rbmx2 |
| 1243 | 3 | 4 | 5 | 6 | 7 | VII-2 | Rcn2 |
| 1244 | 3 | 4 | 5 | 6 | 7 | VII-2 | Rcor1 |
| 1245 | 3 | 4 | 5 | 6 | 7 | VII-2 | Rdh10 |
| 1246 | 3 | 4 | 5 | 6 | 7 | VII-2 | Reck |
| 1247 | 3 | 4 | 5 | 6 | 7 | VII-2 | Reep3 |
| 1248 | 3 | 4 | 5 | 6 | 7 | VII-2 | Rere |
| 1249 | 3 | 4 | 5 | 6 | 7 | VII-2 | Rest |
| 1250 | 3 | 4 | 5 | 6 | 7 | VII-2 | Rfesd |
| 1251 | 3 | 4 | 5 | 6 | 7 | VII-2 | Rgmb |
| 1252 | 3 | 4 | 5 | 6 | 7 | VII-2 | Rgn |
| 1253 | 3 | 4 | 5 | 6 | 7 | VII-2 | Rgs20 |
| 1254 | 3 | 4 | 5 | 6 | 7 | VII-2 | Rgs4 |
| 1255 | 3 | 4 | 5 | 6 | 7 | VII-2 | Rhbdf2 |
| 1256 | 3 | 4 | 5 | 6 | 7 | VII-2 | Rhbdl1 |
| 1257 | 3 | 4 | 5 | 6 | 7 | VII-2 | Rhbdl2 |
| 1258 | 3 | 4 | 5 | 6 | 7 | VII-2 | Rhbdl3 |
| 1259 | 3 | 4 | 5 | 6 | 7 | VII-2 | Rhd |
| 1260 | 3 | 4 | 5 | 6 | 7 | VII-2 | Rheb |
| 1261 | 3 | 4 | 5 | 6 | 7 | VII-2 | Rian |
| 1262 | 3 | 4 | 5 | 6 | 7 | VII-2 | Rictor |
| 1263 | 3 | 4 | 5 | 6 | 7 | VII-2 | Rilpl2 |
| 1264 | 3 | 4 | 5 | 6 | 7 | VII-2 | Rin1 |
| 1265 | 3 | 4 | 5 | 6 | 7 | VII-2 | Ripk2 |
| 1266 | 3 | 4 | 5 | 6 | 7 | VII-2 | Ripply3 |
| 1267 | 3 | 4 | 5 | 6 | 7 | VII-2 | Rlf |
| 1268 | 3 | 4 | 5 | 6 | 7 | VII-2 | Rnase4 |
| 1269 | 3 | 4 | 5 | 6 | 7 | VII-2 | Rnase6 |
| 1270 | 3 | 4 | 5 | 6 | 7 | VII-2 | Rnase9 |
| 1271 | 3 | 4 | 5 | 6 | 7 | VII-2 | Rnd3 |
| 1272 | 3 | 4 | 5 | 6 | 7 | VII-2 | Rnf10 |
| 1273 | 3 | 4 | 5 | 6 | 7 | VII-2 | Rnf11 |
| 1274 | 3 | 4 | 5 | 6 | 7 | VII-2 | Rnf145 |
| 1275 | 3 | 4 | 5 | 6 | 7 | VII-2 | Rnf146 |
| 1276 | 3 | 4 | 5 | 6 | 7 | VII-2 | Rnf186 |
| 1277 | 3 | 4 | 5 | 6 | 7 | VII-2 | Rnf19b |
| 1278 | 3 | 4 | 5 | 6 | 7 | VII-2 | Rnf24 |
| 1279 | 3 | 4 | 5 | 6 | 7 | VII-2 | Rnf34 |
| 1280 | 3 | 4 | 5 | 6 | 7 | VII-2 | Rnf38 |
| 1281 | 3 | 4 | 5 | 6 | 7 | VII-2 | Rnf39 |
| 1282 | 3 | 4 | 5 | 6 | 7 | VII-2 | Rnf44 |
| 1283 | 3 | 4 | 5 | 6 | 7 | VII-2 | Rnft1 |
| 1284 | 3 | 4 | 5 | 6 | 7 | VII-2 | Rnu12 |
| 1285 | 3 | 4 | 5 | 6 | 7 | VII-2 | Rpa3 |
| 1286 | 3 | 4 | 5 | 6 | 7 | VII-2 | Rpl12 |
| 1287 | 3 | 4 | 5 | 6 | 7 | VII-2 | Rpl30 |
| 1288 | 3 | 4 | 5 | 6 | 7 | VII-2 | Rpl37 |
| 1289 | 3 | 4 | 5 | 6 | 7 | VII-2 | Rpp38 |
| 1290 | 3 | 4 | 5 | 6 | 7 | VII-2 | Rprd1b |
| 1291 | 3 | 4 | 5 | 6 | 7 | VII-2 | Rprd2 |
| 1292 | 3 | 4 | 5 | 6 | 7 | VII-2 | Rprl2 |
| 1293 | 3 | 4 | 5 | 6 | 7 | VII-2 | Rprml |
| 1294 | 3 | 4 | 5 | 6 | 7 | VII-2 | Rps10 |
| 1295 | 3 | 4 | 5 | 6 | 7 | VII-2 | Rps27 |
| 1296 | 3 | 4 | 5 | 6 | 7 | VII-2 | Rraga |
| 1297 | 3 | 4 | 5 | 6 | 7 | VII-2 | Rsu1 |
| 1298 | 3 | 4 | 5 | 6 | 7 | VII-2 | Rtp3 |
| 1299 | 3 | 4 | 5 | 6 | 7 | VII-2 | Rusc2 |
| 1300 | 3 | 4 | 5 | 6 | 7 | VII-2 | Ruvbl2 |
| 1301 | 3 | 4 | 5 | 6 | 7 | VII-2 | Rybp |
| 1302 | 3 | 4 | 5 | 6 | 7 | VII-2 | S1pr5 |
| 1303 | 3 | 4 | 5 | 6 | 7 | VII-2 | Samd14 |
| 1304 | 3 | 4 | 5 | 6 | 7 | VII-2 | Sap30 |
| 1305 | 3 | 4 | 5 | 6 | 7 | VII-2 | Sash1 |
| 1306 | 3 | 4 | 5 | 6 | 7 | VII-2 | Sbf2 |
| 1307 | 3 | 4 | 5 | 6 | 7 | VII-2 | Sbno2 |
| 1308 | 3 | 4 | 5 | 6 | 7 | VII-2 | Scaf4 |
| 1309 | 3 | 4 | 5 | 6 | 7 | VII-2 | Scara3 |
| 1310 | 3 | 4 | 5 | 6 | 7 | VII-2 | Scarna13 |
| 1311 | 3 | 4 | 5 | 6 | 7 | VII-2 | Scarna3a |
| 1312 | 3 | 4 | 5 | 6 | 7 | VII-2 | Scarna3b |
| 1313 | 3 | 4 | 5 | 6 | 7 | VII-2 | Scd1 |
| 1314 | 3 | 4 | 5 | 6 | 7 | VII-2 | Scd2 |
| 1315 | 3 | 4 | 5 | 6 | 7 | VII-2 | Scd4 |
| 1316 | 3 | 4 | 5 | 6 | 7 | VII-2 | Scg5 |
| 1317 | 3 | 4 | 5 | 6 | 7 | VII-2 | Scgb1b27 |
| 1318 | 3 | 4 | 5 | 6 | 7 | VII-2 | Scn2b |
| 1319 | 3 | 4 | 5 | 6 | 7 | VII-2 | Scn7a |
| 1320 | 3 | 4 | 5 | 6 | 7 | VII-2 | Sde2 |
| 1321 | 3 | 4 | 5 | 6 | 7 | VII-2 | Sdr16c6 |
| 1322 | 3 | 4 | 5 | 6 | 7 | VII-2 | Sdr9c7 |
| 1323 | 3 | 4 | 5 | 6 | 7 | VII-2 | Sec24d |
| 1324 | 3 | 4 | 5 | 6 | 7 | VII-2 | Secisbp2 |
| 1325 | 3 | 4 | 5 | 6 | 7 | VII-2 | Secisbp2l |
| 1326 | 3 | 4 | 5 | 6 | 7 | VII-2 | Sema3d |
| 1327 | 3 | 4 | 5 | 6 | 7 | VII-2 | Sema3g |
| 1328 | 3 | 4 | 5 | 6 | 7 | VII-2 | Sema4c |
| 1329 | 3 | 4 | 5 | 6 | 7 | VII-2 | Sema4d |
| 1330 | 3 | 4 | 5 | 6 | 7 | VII-2 | Senp5 |
| 1331 | 3 | 4 | 5 | 6 | 7 | VII-2 | Sept11 |
| 1332 | 3 | 4 | 5 | 6 | 7 | VII-2 | Sept3 |
| 1333 | 3 | 4 | 5 | 6 | 7 | VII-2 | Sept8 |
| 1334 | 3 | 4 | 5 | 6 | 7 | VII-2 | Serp1 |
| 1335 | 3 | 4 | 5 | 6 | 7 | VII-2 | Serpina1f |
| 1336 | 3 | 4 | 5 | 6 | 7 | VII-2 | Serpina3f |
| 1337 | 3 | 4 | 5 | 6 | 7 | VII-2 | Serpina3i |
| 1338 | 3 | 4 | 5 | 6 | 7 | VII-2 | Serpina3j |
| 1339 | 3 | 4 | 5 | 6 | 7 | VII-2 | Serpina7 |
| 1340 | 3 | 4 | 5 | 6 | 7 | VII-2 | Serpinb10 |
| 1341 | 3 | 4 | 5 | 6 | 7 | VII-2 | Serpinb2 |
| 1342 | 3 | 4 | 5 | 6 | 7 | VII-2 | Serpinb3a |

Fig. 34 - 8

| | | | | | | | |
|---|---|---|---|---|---|---|---|
| 1343 | 3 | 4 | 5 | 6 | 7 | VII-2 | Serpinb3b |
| 1344 | 3 | 4 | 5 | 6 | 7 | VII-2 | Serpini1 |
| 1345 | 3 | 4 | 5 | 6 | 7 | VII-2 | Sertad4 |
| 1346 | 3 | 4 | 5 | 6 | 7 | VII-2 | Sesn2 |
| 1347 | 3 | 4 | 5 | 6 | 7 | VII-2 | Setdb1 |
| 1348 | 3 | 4 | 5 | 6 | 7 | VII-2 | Sfrp2 |
| 1349 | 3 | 4 | 5 | 6 | 7 | VII-2 | Sfrp5 |
| 1350 | 3 | 4 | 5 | 6 | 7 | VII-2 | Sft2d1 |
| 1351 | 3 | 4 | 5 | 6 | 7 | VII-2 | Sgk2 |
| 1352 | 3 | 4 | 5 | 6 | 7 | VII-2 | Sgpl1 |
| 1353 | 3 | 4 | 5 | 6 | 7 | VII-2 | Sh2b1 |
| 1354 | 3 | 4 | 5 | 6 | 7 | VII-2 | Sh2d1a |
| 1355 | 3 | 4 | 5 | 6 | 7 | VII-2 | Sh3bp5 |
| 1356 | 3 | 4 | 5 | 6 | 7 | VII-2 | Sh3gl1 |
| 1357 | 3 | 4 | 5 | 6 | 7 | VII-2 | Shisa7 |
| 1358 | 3 | 4 | 5 | 6 | 7 | VII-2 | Shpk |
| 1359 | 3 | 4 | 5 | 6 | 7 | VII-2 | Sik2 |
| 1360 | 3 | 4 | 5 | 6 | 7 | VII-2 | Sik3 |
| 1361 | 3 | 4 | 5 | 6 | 7 | VII-2 | Sipa1l3 |
| 1362 | 3 | 4 | 5 | 6 | 7 | VII-2 | Six5 |
| 1363 | 3 | 4 | 5 | 6 | 7 | VII-2 | Skint10 |
| 1364 | 3 | 4 | 5 | 6 | 7 | VII-2 | Slamf6 |
| 1365 | 3 | 4 | 5 | 6 | 7 | VII-2 | Slc10a3 |
| 1366 | 3 | 4 | 5 | 6 | 7 | VII-2 | Slc16a1 |
| 1367 | 3 | 4 | 5 | 6 | 7 | VII-2 | Slc16a2 |
| 1368 | 3 | 4 | 5 | 6 | 7 | VII-2 | Slc16a6 |
| 1369 | 3 | 4 | 5 | 6 | 7 | VII-2 | Slc17a5 |
| 1370 | 3 | 4 | 5 | 6 | 7 | VII-2 | Slc18a2 |
| 1371 | 3 | 4 | 5 | 6 | 7 | VII-2 | Slc22a17 |
| 1372 | 3 | 4 | 5 | 6 | 7 | VII-2 | Slc24a3 |
| 1373 | 3 | 4 | 5 | 6 | 7 | VII-2 | Slc25a16 |
| 1374 | 3 | 4 | 5 | 6 | 7 | VII-2 | Slc25a24 |
| 1375 | 3 | 4 | 5 | 6 | 7 | VII-2 | Slc25a35 |
| 1376 | 3 | 4 | 5 | 6 | 7 | VII-2 | Slc25a36 |
| 1377 | 3 | 4 | 5 | 6 | 7 | VII-2 | Slc26a2 |
| 1378 | 3 | 4 | 5 | 6 | 7 | VII-2 | Slc27a6 |
| 1379 | 3 | 4 | 5 | 6 | 7 | VII-2 | Slc30a7 |
| 1380 | 3 | 4 | 5 | 6 | 7 | VII-2 | Slc35b4 |
| 1381 | 3 | 4 | 5 | 6 | 7 | VII-2 | Slc35d1 |
| 1382 | 3 | 4 | 5 | 6 | 7 | VII-2 | Slc35f2 |
| 1383 | 3 | 4 | 5 | 6 | 7 | VII-2 | Slc35f5 |
| 1384 | 3 | 4 | 5 | 6 | 7 | VII-2 | Slc35g1 |
| 1385 | 3 | 4 | 5 | 6 | 7 | VII-2 | Slc39a10 |
| 1386 | 3 | 4 | 5 | 6 | 7 | VII-2 | Slc40a1 |
| 1387 | 3 | 4 | 5 | 6 | 7 | VII-2 | Slc45a3 |
| 1388 | 3 | 4 | 5 | 6 | 7 | VII-2 | Slc6a13 |
| 1389 | 3 | 4 | 5 | 6 | 7 | VII-2 | Slc6a14 |
| 1390 | 3 | 4 | 5 | 6 | 7 | VII-2 | Slc6a19 |
| 1391 | 3 | 4 | 5 | 6 | 7 | VII-2 | Slc6a6 |
| 1392 | 3 | 4 | 5 | 6 | 7 | VII-2 | Slco4a1 |
| 1393 | 3 | 4 | 5 | 6 | 7 | VII-2 | Slfn3 |
| 1394 | 3 | 4 | 5 | 6 | 7 | VII-2 | Slfn9 |
| 1395 | 3 | 4 | 5 | 6 | 7 | VII-2 | Slitrk6 |
| 1396 | 3 | 4 | 5 | 6 | 7 | VII-2 | Sltm |
| 1397 | 3 | 4 | 5 | 6 | 7 | VII-2 | Smad3 |
| 1398 | 3 | 4 | 5 | 6 | 7 | VII-2 | Smad6 |
| 1399 | 3 | 4 | 5 | 6 | 7 | VII-2 | Smg1 |
| 1400 | 3 | 4 | 5 | 6 | 7 | VII-2 | Smim3 |
| 1401 | 3 | 4 | 5 | 6 | 7 | VII-2 | Snai2 |
| 1402 | 3 | 4 | 5 | 6 | 7 | VII-2 | Snai3 |
| 1403 | 3 | 4 | 5 | 6 | 7 | VII-2 | Snca |
| 1404 | 3 | 4 | 5 | 6 | 7 | VII-2 | Snn |
| 1405 | 3 | 4 | 5 | 6 | 7 | VII-2 | Snora24 |
| 1406 | 3 | 4 | 5 | 6 | 7 | VII-2 | Snora26 |
| 1407 | 3 | 4 | 5 | 6 | 7 | VII-2 | Snora68 |
| 1408 | 3 | 4 | 5 | 6 | 7 | VII-2 | Snord23 |
| 1409 | 3 | 4 | 5 | 6 | 7 | VII-2 | Snrnp48 |
| 1410 | 3 | 4 | 5 | 6 | 7 | VII-2 | Sntb1 |
| 1411 | 3 | 4 | 5 | 6 | 7 | VII-2 | Snx13 |
| 1412 | 3 | 4 | 5 | 6 | 7 | VII-2 | Snx18 |
| 1413 | 3 | 4 | 5 | 6 | 7 | VII-2 | Snx24 |
| 1414 | 3 | 4 | 5 | 6 | 7 | VII-2 | Socs3 |
| 1415 | 3 | 4 | 5 | 6 | 7 | VII-2 | Sorbs1 |
| 1416 | 3 | 4 | 5 | 6 | 7 | VII-2 | Sostdc1 |
| 1417 | 3 | 4 | 5 | 6 | 7 | VII-2 | Sox18 |
| 1418 | 3 | 4 | 5 | 6 | 7 | VII-2 | Sox21 |
| 1419 | 3 | 4 | 5 | 6 | 7 | VII-2 | Sox7 |
| 1420 | 3 | 4 | 5 | 6 | 7 | VII-2 | Sp1 |
| 1421 | 3 | 4 | 5 | 6 | 7 | VII-2 | Sp2 |
| 1422 | 3 | 4 | 5 | 6 | 7 | VII-2 | Sp3 |
| 1423 | 3 | 4 | 5 | 6 | 7 | VII-2 | Spag1 |
| 1424 | 3 | 4 | 5 | 6 | 7 | VII-2 | Spag11b |
| 1425 | 3 | 4 | 5 | 6 | 7 | VII-2 | Spag9 |
| 1426 | 3 | 4 | 5 | 6 | 7 | VII-2 | Spata2 |
| 1427 | 3 | 4 | 5 | 6 | 7 | VII-2 | Speer1-ps1 |
| 1428 | 3 | 4 | 5 | 6 | 7 | VII-2 | Spin1 |
| 1429 | 3 | 4 | 5 | 6 | 7 | VII-2 | Spin2d |
| 1430 | 3 | 4 | 5 | 6 | 7 | VII-2 | Spns3 |
| 1431 | 3 | 4 | 5 | 6 | 7 | VII-2 | Spred2 |
| 1432 | 3 | 4 | 5 | 6 | 7 | VII-2 | Sprr2a1 |
| 1433 | 3 | 4 | 5 | 6 | 7 | VII-2 | Sprr2a2 |
| 1434 | 3 | 4 | 5 | 6 | 7 | VII-2 | Sprr2b |
| 1435 | 3 | 4 | 5 | 6 | 7 | VII-2 | Sprr2e |
| 1436 | 3 | 4 | 5 | 6 | 7 | VII-2 | Sprr3 |
| 1437 | 3 | 4 | 5 | 6 | 7 | VII-2 | Sprr4 |
| 1438 | 3 | 4 | 5 | 6 | 7 | VII-2 | Sprtn |
| 1439 | 3 | 4 | 5 | 6 | 7 | VII-2 | Spry1 |
| 1440 | 3 | 4 | 5 | 6 | 7 | VII-2 | Spry2 |
| 1441 | 3 | 4 | 5 | 6 | 7 | VII-2 | Spry4 |
| 1442 | 3 | 4 | 5 | 6 | 7 | VII-2 | Spryd7 |
| 1443 | 3 | 4 | 5 | 6 | 7 | VII-2 | Spta1 |
| 1444 | 3 | 4 | 5 | 6 | 7 | VII-2 | Sptb |
| 1445 | 3 | 4 | 5 | 6 | 7 | VII-2 | Sptbn1 |
| 1446 | 3 | 4 | 5 | 6 | 7 | VII-2 | Sptssb |
| 1447 | 3 | 4 | 5 | 6 | 7 | VII-2 | Srd5a1 |
| 1448 | 3 | 4 | 5 | 6 | 7 | VII-2 | Srebf1 |
| 1449 | 3 | 4 | 5 | 6 | 7 | VII-2 | Srebf2 |
| 1450 | 3 | 4 | 5 | 6 | 7 | VII-2 | Srek1ip1 |
| 1451 | 3 | 4 | 5 | 6 | 7 | VII-2 | Srsf5 |
| 1452 | 3 | 4 | 5 | 6 | 7 | VII-2 | Ssbp1 |
| 1453 | 3 | 4 | 5 | 6 | 7 | VII-2 | Ssh3 |
| 1454 | 3 | 4 | 5 | 6 | 7 | VII-2 | St3gal5 |
| 1455 | 3 | 4 | 5 | 6 | 7 | VII-2 | St6galnac5 |
| 1456 | 3 | 4 | 5 | 6 | 7 | VII-2 | St8sia4 |
| 1457 | 3 | 4 | 5 | 6 | 7 | VII-2 | Stam |
| 1458 | 3 | 4 | 5 | 6 | 7 | VII-2 | Stard3nl |
| 1459 | 3 | 4 | 5 | 6 | 7 | VII-2 | Stat5b |
| 1460 | 3 | 4 | 5 | 6 | 7 | VII-2 | Steap3 |
| 1461 | 3 | 4 | 5 | 6 | 7 | VII-2 | Steap4 |
| 1462 | 3 | 4 | 5 | 6 | 7 | VII-2 | Stim1 |
| 1463 | 3 | 4 | 5 | 6 | 7 | VII-2 | Stk10 |
| 1464 | 3 | 4 | 5 | 6 | 7 | VII-2 | Strada |
| 1465 | 3 | 4 | 5 | 6 | 7 | VII-2 | Stradb |
| 1466 | 3 | 4 | 5 | 6 | 7 | VII-2 | Strn |
| 1467 | 3 | 4 | 5 | 6 | 7 | VII-2 | Stub1 |
| 1468 | 3 | 4 | 5 | 6 | 7 | VII-2 | Stxbp1 |
| 1469 | 3 | 4 | 5 | 6 | 7 | VII-2 | Stxbp3a |
| 1470 | 3 | 4 | 5 | 6 | 7 | VII-2 | Stxbp3b |
| 1471 | 3 | 4 | 5 | 6 | 7 | VII-2 | Styx |
| 1472 | 3 | 4 | 5 | 6 | 7 | VII-2 | Sucnr1 |
| 1473 | 3 | 4 | 5 | 6 | 7 | VII-2 | Sugct |
| 1474 | 3 | 4 | 5 | 6 | 7 | VII-2 | Susd3 |
| 1475 | 3 | 4 | 5 | 6 | 7 | VII-2 | Suz12 |
| 1476 | 3 | 4 | 5 | 6 | 7 | VII-2 | Sv2a |
| 1477 | 3 | 4 | 5 | 6 | 7 | VII-2 | Svep1 |
| 1478 | 3 | 4 | 5 | 6 | 7 | VII-2 | Sybu |
| 1479 | 3 | 4 | 5 | 6 | 7 | VII-2 | Synpo2 |
| 1480 | 3 | 4 | 5 | 6 | 7 | VII-2 | Syt11 |
| 1481 | 3 | 4 | 5 | 6 | 7 | VII-2 | Tacc1 |
| 1482 | 3 | 4 | 5 | 6 | 7 | VII-2 | Tada2b |
| 1483 | 3 | 4 | 5 | 6 | 7 | VII-2 | Taf1 |
| 1484 | 3 | 4 | 5 | 6 | 7 | VII-2 | Taf1d |
| 1485 | 3 | 4 | 5 | 6 | 7 | VII-2 | Taf2 |
| 1486 | 3 | 4 | 5 | 6 | 7 | VII-2 | Taf4a |
| 1487 | 3 | 4 | 5 | 6 | 7 | VII-2 | Taf5l |
| 1488 | 3 | 4 | 5 | 6 | 7 | VII-2 | Taf7 |
| 1489 | 3 | 4 | 5 | 6 | 7 | VII-2 | Tamm41 |
| 1490 | 3 | 4 | 5 | 6 | 7 | VII-2 | Tank |
| 1491 | 3 | 4 | 5 | 6 | 7 | VII-2 | Taok1 |
| 1492 | 3 | 4 | 5 | 6 | 7 | VII-2 | Tarbp2 |
| 1493 | 3 | 4 | 5 | 6 | 7 | VII-2 | Tbc1d20 |
| 1494 | 3 | 4 | 5 | 6 | 7 | VII-2 | Tbc1d21 |
| 1495 | 3 | 4 | 5 | 6 | 7 | VII-2 | Tbc1d23 |
| 1496 | 3 | 4 | 5 | 6 | 7 | VII-2 | Tbc1d25 |
| 1497 | 3 | 4 | 5 | 6 | 7 | VII-2 | Tbc1d7 |
| 1498 | 3 | 4 | 5 | 6 | 7 | VII-2 | Tbccd1 |
| 1499 | 3 | 4 | 5 | 6 | 7 | VII-2 | Tbcel |
| 1500 | 3 | 4 | 5 | 6 | 7 | VII-2 | Tbx21 |
| 1501 | 3 | 4 | 5 | 6 | 7 | VII-2 | Tcea3 |
| 1502 | 3 | 4 | 5 | 6 | 7 | VII-2 | Tceal3 |
| 1503 | 3 | 4 | 5 | 6 | 7 | VII-2 | Tcf12 |
| 1504 | 3 | 4 | 5 | 6 | 7 | VII-2 | Tcf21 |
| 1505 | 3 | 4 | 5 | 6 | 7 | VII-2 | Tcf24 |
| 1506 | 3 | 4 | 5 | 6 | 7 | VII-2 | Tcf7 |
| 1507 | 3 | 4 | 5 | 6 | 7 | VII-2 | Tead3 |
| 1508 | 3 | 4 | 5 | 6 | 7 | VII-2 | Tecpr1 |
| 1509 | 3 | 4 | 5 | 6 | 7 | VII-2 | Teddm1 |
| 1510 | 3 | 4 | 5 | 6 | 7 | VII-2 | Tefm |
| 1511 | 3 | 4 | 5 | 6 | 7 | VII-2 | Tenm4 |
| 1512 | 3 | 4 | 5 | 6 | 7 | VII-2 | Tet2 |
| 1513 | 3 | 4 | 5 | 6 | 7 | VII-2 | Tet3 |
| 1514 | 3 | 4 | 5 | 6 | 7 | VII-2 | Tex10 |
| 1515 | 3 | 4 | 5 | 6 | 7 | VII-2 | Tfap4 |
| 1516 | 3 | 4 | 5 | 6 | 7 | VII-2 | Tfb2m |
| 1517 | 3 | 4 | 5 | 6 | 7 | VII-2 | Tgfa |
| 1518 | 3 | 4 | 5 | 6 | 7 | VII-2 | Tgfb2 |
| 1519 | 3 | 4 | 5 | 6 | 7 | VII-2 | Tgif2lx2 |
| 1520 | 3 | 4 | 5 | 6 | 7 | VII-2 | Tgm4 |
| 1521 | 3 | 4 | 5 | 6 | 7 | VII-2 | Tgm7 |
| 1522 | 3 | 4 | 5 | 6 | 7 | VII-2 | Tgs1 |
| 1523 | 3 | 4 | 5 | 6 | 7 | VII-2 | Thbd |
| 1524 | 3 | 4 | 5 | 6 | 7 | VII-2 | Them6 |
| 1525 | 3 | 4 | 5 | 6 | 7 | VII-2 | Themis2 |
| 1526 | 3 | 4 | 5 | 6 | 7 | VII-2 | Thnsl2 |
| 1527 | 3 | 4 | 5 | 6 | 7 | VII-2 | Thoc2 |
| 1528 | 3 | 4 | 5 | 6 | 7 | VII-2 | Thra |
| 1529 | 3 | 4 | 5 | 6 | 7 | VII-2 | Thy1 |
| 1530 | 3 | 4 | 5 | 6 | 7 | VII-2 | Tifa |
| 1531 | 3 | 4 | 5 | 6 | 7 | VII-2 | Timm21 |
| 1532 | 3 | 4 | 5 | 6 | 7 | VII-2 | Timp3 |
| 1533 | 3 | 4 | 5 | 6 | 7 | VII-2 | Tiparp |
| 1534 | 3 | 4 | 5 | 6 | 7 | VII-2 | Tjp1 |

Fig. 34 - 9

| | | | | | | | |
|---|---|---|---|---|---|---|---|
| 1535 | 3 | 4 | 5 | 6 | 7 | VII-2 | Tk1 |
| 1536 | 3 | 4 | 5 | 6 | 7 | VII-2 | Tldc1 |
| 1537 | 3 | 4 | 5 | 6 | 7 | VII-2 | Tm4sf19 |
| 1538 | 3 | 4 | 5 | 6 | 7 | VII-2 | Tm6sf1 |
| 1539 | 3 | 4 | 5 | 6 | 7 | VII-2 | Tmeff1 |
| 1540 | 3 | 4 | 5 | 6 | 7 | VII-2 | Tmem123 |
| 1541 | 3 | 4 | 5 | 6 | 7 | VII-2 | Tmem161b |
| 1542 | 3 | 4 | 5 | 6 | 7 | VII-2 | Tmem170b |
| 1543 | 3 | 4 | 5 | 6 | 7 | VII-2 | Tmem171 |
| 1544 | 3 | 4 | 5 | 6 | 7 | VII-2 | Tmem181b-ps |
| 1545 | 3 | 4 | 5 | 6 | 7 | VII-2 | Tmem184c |
| 1546 | 3 | 4 | 5 | 6 | 7 | VII-2 | Tmem185b |
| 1547 | 3 | 4 | 5 | 6 | 7 | VII-2 | Tmem189 |
| 1548 | 3 | 4 | 5 | 6 | 7 | VII-2 | Tmem2 |
| 1549 | 3 | 4 | 5 | 6 | 7 | VII-2 | Tmem200b |
| 1550 | 3 | 4 | 5 | 6 | 7 | VII-2 | Tmem212 |
| 1551 | 3 | 4 | 5 | 6 | 7 | VII-2 | Tmem233 |
| 1552 | 3 | 4 | 5 | 6 | 7 | VII-2 | Tmem234 |
| 1553 | 3 | 4 | 5 | 6 | 7 | VII-2 | Tmem245 |
| 1554 | 3 | 4 | 5 | 6 | 7 | VII-2 | Tmem38b |
| 1555 | 3 | 4 | 5 | 6 | 7 | VII-2 | Tmem43 |
| 1556 | 3 | 4 | 5 | 6 | 7 | VII-2 | Tmtc3 |
| 1557 | 3 | 4 | 5 | 6 | 7 | VII-2 | Tnfrsf11b |
| 1558 | 3 | 4 | 5 | 6 | 7 | VII-2 | Tnfrsf14 |
| 1559 | 3 | 4 | 5 | 6 | 7 | VII-2 | Tnfrsf19 |
| 1560 | 3 | 4 | 5 | 6 | 7 | VII-2 | Tnfsf10 |
| 1561 | 3 | 4 | 5 | 6 | 7 | VII-2 | Tnk1 |
| 1562 | 3 | 4 | 5 | 6 | 7 | VII-2 | Tnks1bp1 |
| 1563 | 3 | 4 | 5 | 6 | 7 | VII-2 | Tnni3k |
| 1564 | 3 | 4 | 5 | 6 | 7 | VII-2 | Tns1 |
| 1565 | 3 | 4 | 5 | 6 | 7 | VII-2 | Tns3 |
| 1566 | 3 | 4 | 5 | 6 | 7 | VII-2 | Tom1l1 |
| 1567 | 3 | 4 | 5 | 6 | 7 | VII-2 | Top1 |
| 1568 | 3 | 4 | 5 | 6 | 7 | VII-2 | Topbp1 |
| 1569 | 3 | 4 | 5 | 6 | 7 | VII-2 | Tpm4 |
| 1570 | 3 | 4 | 5 | 6 | 7 | VII-2 | Trappc10 |
| 1571 | 3 | 4 | 5 | 6 | 7 | VII-2 | Trappc2 |
| 1572 | 3 | 4 | 5 | 6 | 7 | VII-2 | Trappc6b |
| 1573 | 3 | 4 | 5 | 6 | 7 | VII-2 | Trappc8 |
| 1574 | 3 | 4 | 5 | 6 | 7 | VII-2 | Trim10 |
| 1575 | 3 | 4 | 5 | 6 | 7 | VII-2 | Trim13 |
| 1576 | 3 | 4 | 5 | 6 | 7 | VII-2 | Trim56 |
| 1577 | 3 | 4 | 5 | 6 | 7 | VII-2 | Trim59 |
| 1578 | 3 | 4 | 5 | 6 | 7 | VII-2 | Trim8 |
| 1579 | 3 | 4 | 5 | 6 | 7 | VII-2 | Trmt10c |
| 1580 | 3 | 4 | 5 | 6 | 7 | VII-2 | Trmt61b |
| 1581 | 3 | 4 | 5 | 6 | 7 | VII-2 | Trp53 |
| 1582 | 3 | 4 | 5 | 6 | 7 | VII-2 | Trp53bp2 |
| 1583 | 3 | 4 | 5 | 6 | 7 | VII-2 | Trp63 |
| 1584 | 3 | 4 | 5 | 6 | 7 | VII-2 | Trpm7 |
| 1585 | 3 | 4 | 5 | 6 | 7 | VII-2 | Tsen2 |
| 1586 | 3 | 4 | 5 | 6 | 7 | VII-2 | Tshb |
| 1587 | 3 | 4 | 5 | 6 | 7 | VII-2 | Tshr |
| 1588 | 3 | 4 | 5 | 6 | 7 | VII-2 | Tshz1 |
| 1589 | 3 | 4 | 5 | 6 | 7 | VII-2 | Tshz2 |
| 1590 | 3 | 4 | 5 | 6 | 7 | VII-2 | Tspan18 |
| 1591 | 3 | 4 | 5 | 6 | 7 | VII-2 | Tspan4 |
| 1592 | 3 | 4 | 5 | 6 | 7 | VII-2 | Tspo2 |
| 1593 | 3 | 4 | 5 | 6 | 7 | VII-2 | Tspyl4 |
| 1594 | 3 | 4 | 5 | 6 | 7 | VII-2 | Tstd2 |
| 1595 | 3 | 4 | 5 | 6 | 7 | VII-2 | Ttc30b |
| 1596 | 3 | 4 | 5 | 6 | 7 | VII-2 | Tusc3 |
| 1597 | 3 | 4 | 5 | 6 | 7 | VII-2 | Twf1 |
| 1598 | 3 | 4 | 5 | 6 | 7 | VII-2 | Twist1 |
| 1599 | 3 | 4 | 5 | 6 | 7 | VII-2 | Txnip |
| 1600 | 3 | 4 | 5 | 6 | 7 | VII-2 | Tyrobp |
| 1601 | 3 | 4 | 5 | 6 | 7 | VII-2 | Tyrp1 |
| 1602 | 3 | 4 | 5 | 6 | 7 | VII-2 | U2surp |
| 1603 | 3 | 4 | 5 | 6 | 7 | VII-2 | Uap1l1 |
| 1604 | 3 | 4 | 5 | 6 | 7 | VII-2 | Ubb |
| 1605 | 3 | 4 | 5 | 6 | 7 | VII-2 | Ube2g1 |
| 1606 | 3 | 4 | 5 | 6 | 7 | VII-2 | Ube2w |
| 1607 | 3 | 4 | 5 | 6 | 7 | VII-2 | Ubiad1 |
| 1608 | 3 | 4 | 5 | 6 | 7 | VII-2 | Ubxn2a |
| 1609 | 3 | 4 | 5 | 6 | 7 | VII-2 | Ubxn7 |
| 1610 | 3 | 4 | 5 | 6 | 7 | VII-2 | Uckl1os |
| 1611 | 3 | 4 | 5 | 6 | 7 | VII-2 | Uevld |
| 1612 | 3 | 4 | 5 | 6 | 7 | VII-2 | Ugcg |
| 1613 | 3 | 4 | 5 | 6 | 7 | VII-2 | Ugt1a1 |
| 1614 | 3 | 4 | 5 | 6 | 7 | VII-2 | Ugt1a6a |
| 1615 | 3 | 4 | 5 | 6 | 7 | VII-2 | Ulk3 |
| 1616 | 3 | 4 | 5 | 6 | 7 | VII-2 | Unc5b |
| 1617 | 3 | 4 | 5 | 6 | 7 | VII-2 | Unkl |
| 1618 | 3 | 4 | 5 | 6 | 7 | VII-2 | Upf3b |
| 1619 | 3 | 4 | 5 | 6 | 7 | VII-2 | Upk3b |
| 1620 | 3 | 4 | 5 | 6 | 7 | VII-2 | Ush1c |
| 1621 | 3 | 4 | 5 | 6 | 7 | VII-2 | Usmg5 |
| 1622 | 3 | 4 | 5 | 6 | 7 | VII-2 | Usp12 |
| 1623 | 3 | 4 | 5 | 6 | 7 | VII-2 | Usp16 |
| 1624 | 3 | 4 | 5 | 6 | 7 | VII-2 | Usp22 |
| 1625 | 3 | 4 | 5 | 6 | 7 | VII-2 | Usp32 |
| 1626 | 3 | 4 | 5 | 6 | 7 | VII-2 | Usp53 |
| 1627 | 3 | 4 | 5 | 6 | 7 | VII-2 | Utrn |
| 1628 | 3 | 4 | 5 | 6 | 7 | VII-2 | Uts2 |
| 1629 | 3 | 4 | 5 | 6 | 7 | VII-2 | Uts2r |
| 1630 | 3 | 4 | 5 | 6 | 7 | VII-2 | Uvrag |
| 1631 | 3 | 4 | 5 | 6 | 7 | VII-2 | Vamp1 |
| 1632 | 3 | 4 | 5 | 6 | 7 | VII-2 | Vamp4 |
| 1633 | 3 | 4 | 5 | 6 | 7 | VII-2 | Vav3 |
| 1634 | 3 | 4 | 5 | 6 | 7 | VII-2 | Vcp |
| 1635 | 3 | 4 | 5 | 6 | 7 | VII-2 | Vpreb2 |
| 1636 | 3 | 4 | 5 | 6 | 7 | VII-2 | Vps37c |
| 1637 | 3 | 4 | 5 | 6 | 7 | VII-2 | Vstm2b |
| 1638 | 3 | 4 | 5 | 6 | 7 | VII-2 | Vwa1 |
| 1639 | 3 | 4 | 5 | 6 | 7 | VII-2 | Wasf2 |
| 1640 | 3 | 4 | 5 | 6 | 7 | VII-2 | Wasl |
| 1641 | 3 | 4 | 5 | 6 | 7 | VII-2 | Wdr20 |
| 1642 | 3 | 4 | 5 | 6 | 7 | VII-2 | Wdr26 |
| 1643 | 3 | 4 | 5 | 6 | 7 | VII-2 | Wdr47 |
| 1644 | 3 | 4 | 5 | 6 | 7 | VII-2 | Wdr5 |
| 1645 | 3 | 4 | 5 | 6 | 7 | VII-2 | Wdr8 |
| 1646 | 3 | 4 | 5 | 6 | 7 | VII-2 | Wee1 |
| 1647 | 3 | 4 | 5 | 6 | 7 | VII-2 | Wfdc16 |
| 1648 | 3 | 4 | 5 | 6 | 7 | VII-2 | Wfdc6a |
| 1649 | 3 | 4 | 5 | 6 | 7 | VII-2 | Wipi1 |
| 1650 | 3 | 4 | 5 | 6 | 7 | VII-2 | Wisp2 |
| 1651 | 3 | 4 | 5 | 6 | 7 | VII-2 | Wiz |
| 1652 | 3 | 4 | 5 | 6 | 7 | VII-2 | Wnt3 |
| 1653 | 3 | 4 | 5 | 6 | 7 | VII-2 | Wnt5a |
| 1654 | 3 | 4 | 5 | 6 | 7 | VII-2 | Wwc1 |
| 1655 | 3 | 4 | 5 | 6 | 7 | VII-2 | Xiap |
| 1656 | 3 | 4 | 5 | 6 | 7 | VII-2 | Xpr1 |
| 1657 | 3 | 4 | 5 | 6 | 7 | VII-2 | Xrcc3 |
| 1658 | 3 | 4 | 5 | 6 | 7 | VII-2 | Xrcc6bp1 |
| 1659 | 3 | 4 | 5 | 6 | 7 | VII-2 | Xxylt1 |
| 1660 | 3 | 4 | 5 | 6 | 7 | VII-2 | Yeats2 |
| 1661 | 3 | 4 | 5 | 6 | 7 | VII-2 | Yipf4 |
| 1662 | 3 | 4 | 5 | 6 | 7 | VII-2 | Ypel4 |
| 1663 | 3 | 4 | 5 | 6 | 7 | VII-2 | Zbed3 |
| 1664 | 3 | 4 | 5 | 6 | 7 | VII-2 | Zbed5 |
| 1665 | 3 | 4 | 5 | 6 | 7 | VII-2 | Zbed6 |
| 1666 | 3 | 4 | 5 | 6 | 7 | VII-2 | Zbtb1 |
| 1667 | 3 | 4 | 5 | 6 | 7 | VII-2 | Zbtb11 |
| 1668 | 3 | 4 | 5 | 6 | 7 | VII-2 | Zbtb12 |
| 1669 | 3 | 4 | 5 | 6 | 7 | VII-2 | Zbtb18 |
| 1670 | 3 | 4 | 5 | 6 | 7 | VII-2 | Zbtb20 |
| 1671 | 3 | 4 | 5 | 6 | 7 | VII-2 | Zbtb25 |
| 1672 | 3 | 4 | 5 | 6 | 7 | VII-2 | Zbtb33 |
| 1673 | 3 | 4 | 5 | 6 | 7 | VII-2 | Zbtb39 |
| 1674 | 3 | 4 | 5 | 6 | 7 | VII-2 | Zc3h11a |
| 1675 | 3 | 4 | 5 | 6 | 7 | VII-2 | Zc3h13 |
| 1676 | 3 | 4 | 5 | 6 | 7 | VII-2 | Zc3h4 |
| 1677 | 3 | 4 | 5 | 6 | 7 | VII-2 | Zc3h6 |
| 1678 | 3 | 4 | 5 | 6 | 7 | VII-2 | Zcchc14 |
| 1679 | 3 | 4 | 5 | 6 | 7 | VII-2 | Zcchc18 |
| 1680 | 3 | 4 | 5 | 6 | 7 | VII-2 | Zcchc2 |
| 1681 | 3 | 4 | 5 | 6 | 7 | VII-2 | Zcchc6 |
| 1682 | 3 | 4 | 5 | 6 | 7 | VII-2 | Zcchc9 |
| 1683 | 3 | 4 | 5 | 6 | 7 | VII-2 | Zdhhc16 |
| 1684 | 3 | 4 | 5 | 6 | 7 | VII-2 | Zdhhc21 |
| 1685 | 3 | 4 | 5 | 6 | 7 | VII-2 | Zfp146 |
| 1686 | 3 | 4 | 5 | 6 | 7 | VII-2 | Zfp160 |
| 1687 | 3 | 4 | 5 | 6 | 7 | VII-2 | Zfp217 |
| 1688 | 3 | 4 | 5 | 6 | 7 | VII-2 | Zfp219 |
| 1689 | 3 | 4 | 5 | 6 | 7 | VII-2 | Zfp266 |
| 1690 | 3 | 4 | 5 | 6 | 7 | VII-2 | Zfp280c |
| 1691 | 3 | 4 | 5 | 6 | 7 | VII-2 | Zfp280d |
| 1692 | 3 | 4 | 5 | 6 | 7 | VII-2 | Zfp367 |
| 1693 | 3 | 4 | 5 | 6 | 7 | VII-2 | Zfp36l2 |
| 1694 | 3 | 4 | 5 | 6 | 7 | VII-2 | Zfp395 |
| 1695 | 3 | 4 | 5 | 6 | 7 | VII-2 | Zfp423 |
| 1696 | 3 | 4 | 5 | 6 | 7 | VII-2 | Zfp46 |
| 1697 | 3 | 4 | 5 | 6 | 7 | VII-2 | Zfp51 |
| 1698 | 3 | 4 | 5 | 6 | 7 | VII-2 | Zfp516 |
| 1699 | 3 | 4 | 5 | 6 | 7 | VII-2 | Zfp553 |
| 1700 | 3 | 4 | 5 | 6 | 7 | VII-2 | Zfp58 |
| 1701 | 3 | 4 | 5 | 6 | 7 | VII-2 | Zfp646 |
| 1702 | 3 | 4 | 5 | 6 | 7 | VII-2 | Zfp710 |
| 1703 | 3 | 4 | 5 | 6 | 7 | VII-2 | Zfp715 |
| 1704 | 3 | 4 | 5 | 6 | 7 | VII-2 | Zfp740 |
| 1705 | 3 | 4 | 5 | 6 | 7 | VII-2 | Zfp746 |
| 1706 | 3 | 4 | 5 | 6 | 7 | VII-2 | Zfp758 |
| 1707 | 3 | 4 | 5 | 6 | 7 | VII-2 | Zfp770 |
| 1708 | 3 | 4 | 5 | 6 | 7 | VII-2 | Zfp866 |
| 1709 | 3 | 4 | 5 | 6 | 7 | VII-2 | Zfp871 |
| 1710 | 3 | 4 | 5 | 6 | 7 | VII-2 | Zfp942 |
| 1711 | 3 | 4 | 5 | 6 | 7 | VII-2 | Zfp943 |
| 1712 | 3 | 4 | 5 | 6 | 7 | VII-2 | Zfp948 |
| 1713 | 3 | 4 | 5 | 6 | 7 | VII-2 | Zfp955a |
| 1714 | 3 | 4 | 5 | 6 | 7 | VII-2 | Zfp955b |
| 1715 | 3 | 4 | 5 | 6 | 7 | VII-2 | Zfp961 |
| 1716 | 3 | 4 | 5 | 6 | 7 | VII-2 | Zfx |
| 1717 | 3 | 4 | 5 | 6 | 7 | VII-2 | Zfyve9 |
| 1718 | 3 | 4 | 5 | 6 | 7 | VII-2 | Zhx3 |
| 1719 | 3 | 4 | 5 | 6 | 7 | VII-2 | Zmat5 |
| 1720 | 3 | 4 | 5 | 6 | 7 | VII-2 | Zmiz1 |
| 1721 | 3 | 4 | 5 | 6 | 7 | VII-2 | Znf512b |
| 1722 | 3 | 4 | 5 | 6 | 7 | VII-2 | Znfx1 |
| 1723 | 3 | 4 | 5 | 6 | 7 | VII-2 | Zrsr1 |
| 1724 | 3 | 4 | 5 | 6 | 7 | VII-2 | Zscan25 |
| 1725 | 3 | 4 | 5 | 6 | 7 | VII-2 | Zscan26 |
| 1726 | 3 | 4 | 5 | 6 | 7 | VII-2 | l7Rn6 |

Fig. 34 - 10

| | | | | | | | |
|---|---|---|---|---|---|---|---|
| 1727 | 3 | 4 | 5 | 6 | 7 | VII-1 | 0610009L18Rik |
| 1728 | 3 | 4 | 5 | 6 | 7 | VII-1 | 0610010K14Rik |
| 1729 | 3 | 4 | 5 | 6 | 7 | VII-1 | 0610037L13Rik |
| 1730 | 3 | 4 | 5 | 6 | 7 | VII-1 | 0610040B10Rik |
| 1731 | 3 | 4 | 5 | 6 | 7 | VII-1 | 0610043K17Rik |
| 1732 | 3 | 4 | 5 | 6 | 7 | VII-1 | 1100001G20Rik |
| 1733 | 3 | 4 | 5 | 6 | 7 | VII-1 | 1100002L01Rik |
| 1734 | 3 | 4 | 5 | 6 | 7 | VII-1 | 1110004E09Rik |
| 1735 | 3 | 4 | 5 | 6 | 7 | VII-1 | 1110017D15Rik |
| 1736 | 3 | 4 | 5 | 6 | 7 | VII-1 | 1110020A21Rik |
| 1737 | 3 | 4 | 5 | 6 | 7 | VII-1 | 1110034G24Rik |
| 1738 | 3 | 4 | 5 | 6 | 7 | VII-1 | 1110038B12Rik |
| 1739 | 3 | 4 | 5 | 6 | 7 | VII-1 | 1110046J04Rik |
| 1740 | 3 | 4 | 5 | 6 | 7 | VII-1 | 1110054M08Rik |
| 1741 | 3 | 4 | 5 | 6 | 7 | VII-1 | 1110065P20Rik |
| 1742 | 3 | 4 | 5 | 6 | 7 | VII-1 | 1190002F15Rik |
| 1743 | 3 | 4 | 5 | 6 | 7 | VII-1 | 1190005J06Rik |
| 1744 | 3 | 4 | 5 | 6 | 7 | VII-1 | 1190007I07Rik |
| 1745 | 3 | 4 | 5 | 6 | 7 | VII-1 | 1300002E11Rik |
| 1746 | 3 | 4 | 5 | 6 | 7 | VII-1 | 1500009C09Rik |
| 1747 | 3 | 4 | 5 | 6 | 7 | VII-1 | 1500012F01Rik |
| 1748 | 3 | 4 | 5 | 6 | 7 | VII-1 | 1500015O10Rik |
| 1749 | 3 | 4 | 5 | 6 | 7 | VII-1 | 1600002K03Rik |
| 1750 | 3 | 4 | 5 | 6 | 7 | VII-1 | 1600014C23Rik |
| 1751 | 3 | 4 | 5 | 6 | 7 | VII-1 | 1600020E01Rik |
| 1752 | 3 | 4 | 5 | 6 | 7 | VII-1 | 1700001O22Rik |
| 1753 | 3 | 4 | 5 | 6 | 7 | VII-1 | 1700003E16Rik |
| 1754 | 3 | 4 | 5 | 6 | 7 | VII-1 | 1700003F12Rik |
| 1755 | 3 | 4 | 5 | 6 | 7 | VII-1 | 1700003G13Rik |
| 1756 | 3 | 4 | 5 | 6 | 7 | VII-1 | 1700007L15Rik |
| 1757 | 3 | 4 | 5 | 6 | 7 | VII-1 | 1700008K24Rik |
| 1758 | 3 | 4 | 5 | 6 | 7 | VII-1 | 1700009N14Rik |
| 1759 | 3 | 4 | 5 | 6 | 7 | VII-1 | 1700009P17Rik |
| 1760 | 3 | 4 | 5 | 6 | 7 | VII-1 | 1700012A03Rik |
| 1761 | 3 | 4 | 5 | 6 | 7 | VII-1 | 1700017B05Rik |
| 1762 | 3 | 4 | 5 | 6 | 7 | VII-1 | 1700025F24Rik |
| 1763 | 3 | 4 | 5 | 6 | 7 | VII-1 | 1700027A15Rik |
| 1764 | 3 | 4 | 5 | 6 | 7 | VII-1 | 1700029I15Rik |
| 1765 | 3 | 4 | 5 | 6 | 7 | VII-1 | 1700037C18Rik |
| 1766 | 3 | 4 | 5 | 6 | 7 | VII-1 | 1700047M11Rik |
| 1767 | 3 | 4 | 5 | 6 | 7 | VII-1 | 1700057H15Rik |
| 1768 | 3 | 4 | 5 | 6 | 7 | VII-1 | 1700084C01Rik |
| 1769 | 3 | 4 | 5 | 6 | 7 | VII-1 | 1700084E18Rik |
| 1770 | 3 | 4 | 5 | 6 | 7 | VII-1 | 1700101I11Rik |
| 1771 | 3 | 4 | 5 | 6 | 7 | VII-1 | 1700102H20Rik |
| 1772 | 3 | 4 | 5 | 6 | 7 | VII-1 | 1700112E06Rik |
| 1773 | 3 | 4 | 5 | 6 | 7 | VII-1 | 1700113A16Rik |
| 1774 | 3 | 4 | 5 | 6 | 7 | VII-1 | 1700121N20Rik |
| 1775 | 3 | 4 | 5 | 6 | 7 | VII-1 | 1700123L14Rik |
| 1776 | 3 | 4 | 5 | 6 | 7 | VII-1 | 1810009A15Rik |
| 1777 | 3 | 4 | 5 | 6 | 7 | VII-1 | 1810009J06Rik |
| 1778 | 3 | 4 | 5 | 6 | 7 | VII-1 | 1810010H24Rik |
| 1779 | 3 | 4 | 5 | 6 | 7 | VII-1 | 1810012K16Rik |
| 1780 | 3 | 4 | 5 | 6 | 7 | VII-1 | 1810022K09Rik |
| 1781 | 3 | 4 | 5 | 6 | 7 | VII-1 | 1810026B05Rik |
| 1782 | 3 | 4 | 5 | 6 | 7 | VII-1 | 1810032O08Rik |
| 1783 | 3 | 4 | 5 | 6 | 7 | VII-1 | 1810044D09Rik |
| 1784 | 3 | 4 | 5 | 6 | 7 | VII-1 | 1810053B23Rik |
| 1785 | 3 | 4 | 5 | 6 | 7 | VII-1 | 1810058I24Rik |
| 1786 | 3 | 4 | 5 | 6 | 7 | VII-1 | 2010005H15Rik |
| 1787 | 3 | 4 | 5 | 6 | 7 | VII-1 | 2010010A06Rik |
| 1788 | 3 | 4 | 5 | 6 | 7 | VII-1 | 2010107E04Rik |
| 1789 | 3 | 4 | 5 | 6 | 7 | VII-1 | 2010109I03Rik |
| 1790 | 3 | 4 | 5 | 6 | 7 | VII-1 | 2010300C02Rik |
| 1791 | 3 | 4 | 5 | 6 | 7 | VII-1 | 2010320M18Rik |
| 1792 | 3 | 4 | 5 | 6 | 7 | VII-1 | 2200002D01Rik |
| 1793 | 3 | 4 | 5 | 6 | 7 | VII-1 | 2210010C04Rik |
| 1794 | 3 | 4 | 5 | 6 | 7 | VII-1 | 2210011C24Rik |
| 1795 | 3 | 4 | 5 | 6 | 7 | VII-1 | 2210013O21Rik |
| 1796 | 3 | 4 | 5 | 6 | 7 | VII-1 | 2210407C18Rik |
| 1797 | 3 | 4 | 5 | 6 | 7 | VII-1 | 2210408F21Rik |
| 1798 | 3 | 4 | 5 | 6 | 7 | VII-1 | 2210409D07Rik |
| 1799 | 3 | 4 | 5 | 6 | 7 | VII-1 | 2310001H17Rik |
| 1800 | 3 | 4 | 5 | 6 | 7 | VII-1 | 2310002J15Rik |
| 1801 | 3 | 4 | 5 | 6 | 7 | VII-1 | 2310003H01Rik |
| 1802 | 3 | 4 | 5 | 6 | 7 | VII-1 | 2310010J17Rik |
| 1803 | 3 | 4 | 5 | 6 | 7 | VII-1 | 2310015B20Rik |
| 1804 | 3 | 4 | 5 | 6 | 7 | VII-1 | 2310034O05Rik |
| 1805 | 3 | 4 | 5 | 6 | 7 | VII-1 | 2310036O22Rik |
| 1806 | 3 | 4 | 5 | 6 | 7 | VII-1 | 2310045N01Rik |
| 1807 | 3 | 4 | 5 | 6 | 7 | VII-1 | 2310057J18Rik |
| 1808 | 3 | 4 | 5 | 6 | 7 | VII-1 | 2310057M21Rik |
| 1809 | 3 | 4 | 5 | 6 | 7 | VII-1 | 2310061I04Rik |
| 1810 | 3 | 4 | 5 | 6 | 7 | VII-1 | 2410004N09Rik |
| 1811 | 3 | 4 | 5 | 6 | 7 | VII-1 | 2410006H16Rik |
| 1812 | 3 | 4 | 5 | 6 | 7 | VII-1 | 2410015M20Rik |
| 1813 | 3 | 4 | 5 | 6 | 7 | VII-1 | 2410131K14Rik |
| 1814 | 3 | 4 | 5 | 6 | 7 | VII-1 | 2510049J12Rik |
| 1815 | 3 | 4 | 5 | 6 | 7 | VII-1 | 2610002J02Rik |
| 1816 | 3 | 4 | 5 | 6 | 7 | VII-1 | 2610016A17Rik |
| 1817 | 3 | 4 | 5 | 6 | 7 | VII-1 | 2610524H06Rik |
| 1818 | 3 | 4 | 5 | 6 | 7 | VII-1 | 2700060E02Rik |
| 1819 | 3 | 4 | 5 | 6 | 7 | VII-1 | 2810025M15Rik |
| 1820 | 3 | 4 | 5 | 6 | 7 | VII-1 | 2810405F15Rik |
| 1821 | 3 | 4 | 5 | 6 | 7 | VII-1 | 2810428I15Rik |
| 1822 | 3 | 4 | 5 | 6 | 7 | VII-1 | 2810474O19Rik |
| 1823 | 3 | 4 | 5 | 6 | 7 | VII-1 | 2900008C10Rik |
| 1824 | 3 | 4 | 5 | 6 | 7 | VII-1 | 2900009J06Rik |
| 1825 | 3 | 4 | 5 | 6 | 7 | VII-1 | 2900011O08Rik |
| 1826 | 3 | 4 | 5 | 6 | 7 | VII-1 | 2900079G21Rik |
| 1827 | 3 | 4 | 5 | 6 | 7 | VII-1 | 3010026O09Rik |
| 1828 | 3 | 4 | 5 | 6 | 7 | VII-1 | 3110009E18Rik |
| 1829 | 3 | 4 | 5 | 6 | 7 | VII-1 | 3110035E14Rik |
| 1830 | 3 | 4 | 5 | 6 | 7 | VII-1 | 3110040N11Rik |
| 1831 | 3 | 4 | 5 | 6 | 7 | VII-1 | 3110043O21Rik |
| 1832 | 3 | 4 | 5 | 6 | 7 | VII-1 | 3110079O15Rik |
| 1833 | 3 | 4 | 5 | 6 | 7 | VII-1 | 3300002I08Rik |
| 1834 | 3 | 4 | 5 | 6 | 7 | VII-1 | 3930402G23Rik |
| 1835 | 3 | 4 | 5 | 6 | 7 | VII-1 | 4833411C07Rik |
| 1836 | 3 | 4 | 5 | 6 | 7 | VII-1 | 4922502D21Rik |
| 1837 | 3 | 4 | 5 | 6 | 7 | VII-1 | 4930401C15Rik |
| 1838 | 3 | 4 | 5 | 6 | 7 | VII-1 | 4930404A05Rik |
| 1839 | 3 | 4 | 5 | 6 | 7 | VII-1 | 4930412C18Rik |
| 1840 | 3 | 4 | 5 | 6 | 7 | VII-1 | 4930413F20Rik |
| 1841 | 3 | 4 | 5 | 6 | 7 | VII-1 | 4930447K03Rik |
| 1842 | 3 | 4 | 5 | 6 | 7 | VII-1 | 4930481A15Rik |
| 1843 | 3 | 4 | 5 | 6 | 7 | VII-1 | 4930511M06Rik |
| 1844 | 3 | 4 | 5 | 6 | 7 | VII-1 | 4930523O13Rik |
| 1845 | 3 | 4 | 5 | 6 | 7 | VII-1 | 4930526I15Rik |
| 1846 | 3 | 4 | 5 | 6 | 7 | VII-1 | 4930529K09Rik |
| 1847 | 3 | 4 | 5 | 6 | 7 | VII-1 | 4930539J05Rik |
| 1848 | 3 | 4 | 5 | 6 | 7 | VII-1 | 4930593C16Rik |
| 1849 | 3 | 4 | 5 | 6 | 7 | VII-1 | 4931428L18Rik |
| 1850 | 3 | 4 | 5 | 6 | 7 | VII-1 | 4932414J04Rik |
| 1851 | 3 | 4 | 5 | 6 | 7 | VII-1 | 4932702P03Rik |
| 1852 | 3 | 4 | 5 | 6 | 7 | VII-1 | 4933402C06Rik |
| 1853 | 3 | 4 | 5 | 6 | 7 | VII-1 | 4933406K04Rik |
| 1854 | 3 | 4 | 5 | 6 | 7 | VII-1 | 4933407E24Rik |
| 1855 | 3 | 4 | 5 | 6 | 7 | VII-1 | 4933409K07Rik |
| 1856 | 3 | 4 | 5 | 6 | 7 | VII-1 | 4933411K16Rik |
| 1857 | 3 | 4 | 5 | 6 | 7 | VII-1 | 4933422A05Rik |
| 1858 | 3 | 4 | 5 | 6 | 7 | VII-1 | 4933439C10Rik |
| 1859 | 3 | 4 | 5 | 6 | 7 | VII-1 | 5031434O11Rik |
| 1860 | 3 | 4 | 5 | 6 | 7 | VII-1 | 5430405H02Rik |
| 1861 | 3 | 4 | 5 | 6 | 7 | VII-1 | 5430421N21Rik |
| 1862 | 3 | 4 | 5 | 6 | 7 | VII-1 | 5430425K12Rik |
| 1863 | 3 | 4 | 5 | 6 | 7 | VII-1 | 6030408B16Rik |
| 1864 | 3 | 4 | 5 | 6 | 7 | VII-1 | 6030419C18Rik |
| 1865 | 3 | 4 | 5 | 6 | 7 | VII-1 | 6330403K07Rik |
| 1866 | 3 | 4 | 5 | 6 | 7 | VII-1 | 6330418K02Rik |
| 1867 | 3 | 4 | 5 | 6 | 7 | VII-1 | 6430531B16Rik |
| 1868 | 3 | 4 | 5 | 6 | 7 | VII-1 | 6720468P15Rik |
| 1869 | 3 | 4 | 5 | 6 | 7 | VII-1 | 8430408G22Rik |
| 1870 | 3 | 4 | 5 | 6 | 7 | VII-1 | 9030025P20Rik |
| 1871 | 3 | 4 | 5 | 6 | 7 | VII-1 | 9130204L05Rik |
| 1872 | 3 | 4 | 5 | 6 | 7 | VII-1 | 9130401M01Rik |
| 1873 | 3 | 4 | 5 | 6 | 7 | VII-1 | 9130409I23Rik |
| 1874 | 3 | 4 | 5 | 6 | 7 | VII-1 | 9230102O04Rik |
| 1875 | 3 | 4 | 5 | 6 | 7 | VII-1 | 9230105E05Rik |
| 1876 | 3 | 4 | 5 | 6 | 7 | VII-1 | 9330020H09Rik |
| 1877 | 3 | 4 | 5 | 6 | 7 | VII-1 | 9430016H08Rik |
| 1878 | 3 | 4 | 5 | 6 | 7 | VII-1 | 9430037G07Rik |
| 1879 | 3 | 4 | 5 | 6 | 7 | VII-1 | A230065H16Rik |
| 1880 | 3 | 4 | 5 | 6 | 7 | VII-1 | A330021E22Rik |
| 1881 | 3 | 4 | 5 | 6 | 7 | VII-1 | A330069E16Rik |
| 1882 | 3 | 4 | 5 | 6 | 7 | VII-1 | A430005L14Rik |
| 1883 | 3 | 4 | 5 | 6 | 7 | VII-1 | A530013C23Rik |
| 1884 | 3 | 4 | 5 | 6 | 7 | VII-1 | A630023P12Rik |
| 1885 | 3 | 4 | 5 | 6 | 7 | VII-1 | A730020M07Rik |
| 1886 | 3 | 4 | 5 | 6 | 7 | VII-1 | A930001C03Rik |
| 1887 | 3 | 4 | 5 | 6 | 7 | VII-1 | A930011O12Rik |
| 1888 | 3 | 4 | 5 | 6 | 7 | VII-1 | AA467197 |
| 1889 | 3 | 4 | 5 | 6 | 7 | VII-1 | AI427809 |
| 1890 | 3 | 4 | 5 | 6 | 7 | VII-1 | AI462493 |
| 1891 | 3 | 4 | 5 | 6 | 7 | VII-1 | AI463170 |
| 1892 | 3 | 4 | 5 | 6 | 7 | VII-1 | AI507597 |
| 1893 | 3 | 4 | 5 | 6 | 7 | VII-1 | AI593442 |
| 1894 | 3 | 4 | 5 | 6 | 7 | VII-1 | AU021092 |
| 1895 | 3 | 4 | 5 | 6 | 7 | VII-1 | AU022252 |
| 1896 | 3 | 4 | 5 | 6 | 7 | VII-1 | AV039307 |
| 1897 | 3 | 4 | 5 | 6 | 7 | VII-1 | AW112010 |
| 1898 | 3 | 4 | 5 | 6 | 7 | VII-1 | AY761185 |
| 1899 | 3 | 4 | 5 | 6 | 7 | VII-1 | Aacs |
| 1900 | 3 | 4 | 5 | 6 | 7 | VII-1 | Aarsd1 |
| 1901 | 3 | 4 | 5 | 6 | 7 | VII-1 | Aatf |
| 1902 | 3 | 4 | 5 | 6 | 7 | VII-1 | Abca7 |
| 1903 | 3 | 4 | 5 | 6 | 7 | VII-1 | Abcb1a |
| 1904 | 3 | 4 | 5 | 6 | 7 | VII-1 | Abcb1b |
| 1905 | 3 | 4 | 5 | 6 | 7 | VII-1 | Abcb6 |
| 1906 | 3 | 4 | 5 | 6 | 7 | VII-1 | Abcd4 |
| 1907 | 3 | 4 | 5 | 6 | 7 | VII-1 | Abcf1 |
| 1908 | 3 | 4 | 5 | 6 | 7 | VII-1 | Abhd11os |
| 1909 | 3 | 4 | 5 | 6 | 7 | VII-1 | Abra |
| 1910 | 3 | 4 | 5 | 6 | 7 | VII-1 | Abracl |
| 1911 | 3 | 4 | 5 | 6 | 7 | VII-1 | Abtb1 |
| 1912 | 3 | 4 | 5 | 6 | 7 | VII-1 | Acaa1a |
| 1913 | 3 | 4 | 5 | 6 | 7 | VII-1 | Acadvl |
| 1914 | 3 | 4 | 5 | 6 | 7 | VII-1 | Acat3 |
| 1915 | 3 | 4 | 5 | 6 | 7 | VII-1 | Acbd4 |
| 1916 | 3 | 4 | 5 | 6 | 7 | VII-1 | Acmsd |
| 1917 | 3 | 4 | 5 | 6 | 7 | VII-1 | Acot1 |
| 1918 | 3 | 4 | 5 | 6 | 7 | VII-1 | Acot3 |

Fig. 34 - 11

| | | | | | | | |
|---|---|---|---|---|---|---|---|
| 1919 | 3 | 4 | 5 | 6 | 7 | VII-1 | Acot5 |
| 1920 | 3 | 4 | 5 | 6 | 7 | VII-1 | Acot7 |
| 1921 | 3 | 4 | 5 | 6 | 7 | VII-1 | Acoxl |
| 1922 | 3 | 4 | 5 | 6 | 7 | VII-1 | Acsf3 |
| 1923 | 3 | 4 | 5 | 6 | 7 | VII-1 | Acsm1 |
| 1924 | 3 | 4 | 5 | 6 | 7 | VII-1 | Acta1 |
| 1925 | 3 | 4 | 5 | 6 | 7 | VII-1 | Actb |
| 1926 | 3 | 4 | 5 | 6 | 7 | VII-1 | Actl7b |
| 1927 | 3 | 4 | 5 | 6 | 7 | VII-1 | Actn3 |
| 1928 | 3 | 4 | 5 | 6 | 7 | VII-1 | Actr5 |
| 1929 | 3 | 4 | 5 | 6 | 7 | VII-1 | Ada |
| 1930 | 3 | 4 | 5 | 6 | 7 | VII-1 | Adamtsl4 |
| 1931 | 3 | 4 | 5 | 6 | 7 | VII-1 | Adat2 |
| 1932 | 3 | 4 | 5 | 6 | 7 | VII-1 | Adck4 |
| 1933 | 3 | 4 | 5 | 6 | 7 | VII-1 | Adck5 |
| 1934 | 3 | 4 | 5 | 6 | 7 | VII-1 | Adcy1 |
| 1935 | 3 | 4 | 5 | 6 | 7 | VII-1 | Adh1 |
| 1936 | 3 | 4 | 5 | 6 | 7 | VII-1 | Adh6-ps1 |
| 1937 | 3 | 4 | 5 | 6 | 7 | VII-1 | Adh6a |
| 1938 | 3 | 4 | 5 | 6 | 7 | VII-1 | Adh7 |
| 1939 | 3 | 4 | 5 | 6 | 7 | VII-1 | Adig |
| 1940 | 3 | 4 | 5 | 6 | 7 | VII-1 | Adora1 |
| 1941 | 3 | 4 | 5 | 6 | 7 | VII-1 | Adrb2 |
| 1942 | 3 | 4 | 5 | 6 | 7 | VII-1 | Aes |
| 1943 | 3 | 4 | 5 | 6 | 7 | VII-1 | Ager |
| 1944 | 3 | 4 | 5 | 6 | 7 | VII-1 | Agrp |
| 1945 | 3 | 4 | 5 | 6 | 7 | VII-1 | Agt |
| 1946 | 3 | 4 | 5 | 6 | 7 | VII-1 | Ahsg |
| 1947 | 3 | 4 | 5 | 6 | 7 | VII-1 | Aif1 |
| 1948 | 3 | 4 | 5 | 6 | 7 | VII-1 | Aifm2 |
| 1949 | 3 | 4 | 5 | 6 | 7 | VII-1 | Aimp1 |
| 1950 | 3 | 4 | 5 | 6 | 7 | VII-1 | Aimp2 |
| 1951 | 3 | 4 | 5 | 6 | 7 | VII-1 | Ak6 |
| 1952 | 3 | 4 | 5 | 6 | 7 | VII-1 | Akap4 |
| 1953 | 3 | 4 | 5 | 6 | 7 | VII-1 | Akap8l |
| 1954 | 3 | 4 | 5 | 6 | 7 | VII-1 | Akip1 |
| 1955 | 3 | 4 | 5 | 6 | 7 | VII-1 | Akp3 |
| 1956 | 3 | 4 | 5 | 6 | 7 | VII-1 | Akr1b8 |
| 1957 | 3 | 4 | 5 | 6 | 7 | VII-1 | Akr7a5 |
| 1958 | 3 | 4 | 5 | 6 | 7 | VII-1 | Alb |
| 1959 | 3 | 4 | 5 | 6 | 7 | VII-1 | Aldh1a1 |
| 1960 | 3 | 4 | 5 | 6 | 7 | VII-1 | Aldh1l1 |
| 1961 | 3 | 4 | 5 | 6 | 7 | VII-1 | Aldh3a1 |
| 1962 | 3 | 4 | 5 | 6 | 7 | VII-1 | Aldh7a1 |
| 1963 | 3 | 4 | 5 | 6 | 7 | VII-1 | Aldob |
| 1964 | 3 | 4 | 5 | 6 | 7 | VII-1 | Aldoc |
| 1965 | 3 | 4 | 5 | 6 | 7 | VII-1 | Alg1 |
| 1966 | 3 | 4 | 5 | 6 | 7 | VII-1 | Alg3 |
| 1967 | 3 | 4 | 5 | 6 | 7 | VII-1 | Alkbh2 |
| 1968 | 3 | 4 | 5 | 6 | 7 | VII-1 | Alkbh3 |
| 1969 | 3 | 4 | 5 | 6 | 7 | VII-1 | Alkbh7 |
| 1970 | 3 | 4 | 5 | 6 | 7 | VII-1 | Als2cr12 |
| 1971 | 3 | 4 | 5 | 6 | 7 | VII-1 | Alyref |
| 1972 | 3 | 4 | 5 | 6 | 7 | VII-1 | Amd1 |
| 1973 | 3 | 4 | 5 | 6 | 7 | VII-1 | Amd2 |
| 1974 | 3 | 4 | 5 | 6 | 7 | VII-1 | Amdhd2 |
| 1975 | 3 | 4 | 5 | 6 | 7 | VII-1 | Amica1 |
| 1976 | 3 | 4 | 5 | 6 | 7 | VII-1 | Ampd3 |
| 1977 | 3 | 4 | 5 | 6 | 7 | VII-1 | Amph |
| 1978 | 3 | 4 | 5 | 6 | 7 | VII-1 | Amy2a5 |
| 1979 | 3 | 4 | 5 | 6 | 7 | VII-1 | Amy2b |
| 1980 | 3 | 4 | 5 | 6 | 7 | VII-1 | Anapc11 |
| 1981 | 3 | 4 | 5 | 6 | 7 | VII-1 | Anapc13 |
| 1982 | 3 | 4 | 5 | 6 | 7 | VII-1 | Anapc15 |
| 1983 | 3 | 4 | 5 | 6 | 7 | VII-1 | Anapc16 |
| 1984 | 3 | 4 | 5 | 6 | 7 | VII-1 | Anapc7 |
| 1985 | 3 | 4 | 5 | 6 | 7 | VII-1 | Ang4 |
| 1986 | 3 | 4 | 5 | 6 | 7 | VII-1 | Angptl4 |
| 1987 | 3 | 4 | 5 | 6 | 7 | VII-1 | Angptl7 |
| 1988 | 3 | 4 | 5 | 6 | 7 | VII-1 | Ank2 |
| 1989 | 3 | 4 | 5 | 6 | 7 | VII-1 | Ankrd1 |
| 1990 | 3 | 4 | 5 | 6 | 7 | VII-1 | Ankrd2 |
| 1991 | 3 | 4 | 5 | 6 | 7 | VII-1 | Ankrd33b |
| 1992 | 3 | 4 | 5 | 6 | 7 | VII-1 | Ankrd55 |
| 1993 | 3 | 4 | 5 | 6 | 7 | VII-1 | Anks1b |
| 1994 | 3 | 4 | 5 | 6 | 7 | VII-1 | Anks3 |
| 1995 | 3 | 4 | 5 | 6 | 7 | VII-1 | Anp32a |
| 1996 | 3 | 4 | 5 | 6 | 7 | VII-1 | Aoc2 |
| 1997 | 3 | 4 | 5 | 6 | 7 | VII-1 | Aox4 |
| 1998 | 3 | 4 | 5 | 6 | 7 | VII-1 | Ap1g2 |
| 1999 | 3 | 4 | 5 | 6 | 7 | VII-1 | Ap2s1 |
| 2000 | 3 | 4 | 5 | 6 | 7 | VII-1 | Ap5s1 |
| 2001 | 3 | 4 | 5 | 6 | 7 | VII-1 | Apbb1 |
| 2002 | 3 | 4 | 5 | 6 | 7 | VII-1 | Apeh |
| 2003 | 3 | 4 | 5 | 6 | 7 | VII-1 | Apex1 |
| 2004 | 3 | 4 | 5 | 6 | 7 | VII-1 | Apip |
| 2005 | 3 | 4 | 5 | 6 | 7 | VII-1 | Aplp1 |
| 2006 | 3 | 4 | 5 | 6 | 7 | VII-1 | Apoa1 |
| 2007 | 3 | 4 | 5 | 6 | 7 | VII-1 | Apoa1bp |
| 2008 | 3 | 4 | 5 | 6 | 7 | VII-1 | Apoa2 |
| 2009 | 3 | 4 | 5 | 6 | 7 | VII-1 | Apoa4 |
| 2010 | 3 | 4 | 5 | 6 | 7 | VII-1 | Apob |
| 2011 | 3 | 4 | 5 | 6 | 7 | VII-1 | Apoc1 |
| 2012 | 3 | 4 | 5 | 6 | 7 | VII-1 | Apoc2 |
| 2013 | 3 | 4 | 5 | 6 | 7 | VII-1 | Apoc3 |
| 2014 | 3 | 4 | 5 | 6 | 7 | VII-1 | Apoc4 |
| 2015 | 3 | 4 | 5 | 6 | 7 | VII-1 | Apod |
| 2016 | 3 | 4 | 5 | 6 | 7 | VII-1 | Apoe |
| 2017 | 3 | 4 | 5 | 6 | 7 | VII-1 | Apoh |
| 2018 | 3 | 4 | 5 | 6 | 7 | VII-1 | Apol9a |
| 2019 | 3 | 4 | 5 | 6 | 7 | VII-1 | Apol9b |
| 2020 | 3 | 4 | 5 | 6 | 7 | VII-1 | Aprt |
| 2021 | 3 | 4 | 5 | 6 | 7 | VII-1 | Aqp11 |
| 2022 | 3 | 4 | 5 | 6 | 7 | VII-1 | Arc |
| 2023 | 3 | 4 | 5 | 6 | 7 | VII-1 | Arhgap26 |
| 2024 | 3 | 4 | 5 | 6 | 7 | VII-1 | Arhgap42 |
| 2025 | 3 | 4 | 5 | 6 | 7 | VII-1 | Arhgap5 |
| 2026 | 3 | 4 | 5 | 6 | 7 | VII-1 | Arhgef9 |
| 2027 | 3 | 4 | 5 | 6 | 7 | VII-1 | Arid5a |
| 2028 | 3 | 4 | 5 | 6 | 7 | VII-1 | Arid5b |
| 2029 | 3 | 4 | 5 | 6 | 7 | VII-1 | Arl13b |
| 2030 | 3 | 4 | 5 | 6 | 7 | VII-1 | Arl2 |
| 2031 | 3 | 4 | 5 | 6 | 7 | VII-1 | Arl3 |
| 2032 | 3 | 4 | 5 | 6 | 7 | VII-1 | Arl4d |
| 2033 | 3 | 4 | 5 | 6 | 7 | VII-1 | Armc12 |
| 2034 | 3 | 4 | 5 | 6 | 7 | VII-1 | Armc3 |
| 2035 | 3 | 4 | 5 | 6 | 7 | VII-1 | Arntl |
| 2036 | 3 | 4 | 5 | 6 | 7 | VII-1 | Arpc3 |
| 2037 | 3 | 4 | 5 | 6 | 7 | VII-1 | Arpc4 |
| 2038 | 3 | 4 | 5 | 6 | 7 | VII-1 | Arpp21 |
| 2039 | 3 | 4 | 5 | 6 | 7 | VII-1 | Arrb2 |
| 2040 | 3 | 4 | 5 | 6 | 7 | VII-1 | Arrdc1 |
| 2041 | 3 | 4 | 5 | 6 | 7 | VII-1 | Arrdc2 |
| 2042 | 3 | 4 | 5 | 6 | 7 | VII-1 | Arrdc3 |
| 2043 | 3 | 4 | 5 | 6 | 7 | VII-1 | Arsi |
| 2044 | 3 | 4 | 5 | 6 | 7 | VII-1 | Art5 |
| 2045 | 3 | 4 | 5 | 6 | 7 | VII-1 | Arv1 |
| 2046 | 3 | 4 | 5 | 6 | 7 | VII-1 | Asb11 |
| 2047 | 3 | 4 | 5 | 6 | 7 | VII-1 | Asb2 |
| 2048 | 3 | 4 | 5 | 6 | 7 | VII-1 | Ascc1 |
| 2049 | 3 | 4 | 5 | 6 | 7 | VII-1 | Ascc2 |
| 2050 | 3 | 4 | 5 | 6 | 7 | VII-1 | Ascl3 |
| 2051 | 3 | 4 | 5 | 6 | 7 | VII-1 | Asgr1 |
| 2052 | 3 | 4 | 5 | 6 | 7 | VII-1 | Asl |
| 2053 | 3 | 4 | 5 | 6 | 7 | VII-1 | Aspg |
| 2054 | 3 | 4 | 5 | 6 | 7 | VII-1 | Asph |
| 2055 | 3 | 4 | 5 | 6 | 7 | VII-1 | Asphd1 |
| 2056 | 3 | 4 | 5 | 6 | 7 | VII-1 | Asphd2 |
| 2057 | 3 | 4 | 5 | 6 | 7 | VII-1 | Atf3 |
| 2058 | 3 | 4 | 5 | 6 | 7 | VII-1 | Atg101 |
| 2059 | 3 | 4 | 5 | 6 | 7 | VII-1 | Atox1 |
| 2060 | 3 | 4 | 5 | 6 | 7 | VII-1 | Atp13a1 |
| 2061 | 3 | 4 | 5 | 6 | 7 | VII-1 | Atp13a2 |
| 2062 | 3 | 4 | 5 | 6 | 7 | VII-1 | Atp1a2 |
| 2063 | 3 | 4 | 5 | 6 | 7 | VII-1 | Atp1a3 |
| 2064 | 3 | 4 | 5 | 6 | 7 | VII-1 | Atp2a1 |
| 2065 | 3 | 4 | 5 | 6 | 7 | VII-1 | Atp2a3 |
| 2066 | 3 | 4 | 5 | 6 | 7 | VII-1 | Atp2b2 |
| 2067 | 3 | 4 | 5 | 6 | 7 | VII-1 | Atp5d |
| 2068 | 3 | 4 | 5 | 6 | 7 | VII-1 | Atp5e |
| 2069 | 3 | 4 | 5 | 6 | 7 | VII-1 | Atp5g3 |
| 2070 | 3 | 4 | 5 | 6 | 7 | VII-1 | Atp5h |
| 2071 | 3 | 4 | 5 | 6 | 7 | VII-1 | Atp5j2 |
| 2072 | 3 | 4 | 5 | 6 | 7 | VII-1 | Atp5k |
| 2073 | 3 | 4 | 5 | 6 | 7 | VII-1 | Atp5l |
| 2074 | 3 | 4 | 5 | 6 | 7 | VII-1 | Atp5o |
| 2075 | 3 | 4 | 5 | 6 | 7 | VII-1 | Atp6v0h |
| 2076 | 3 | 4 | 5 | 6 | 7 | VII-1 | Atp6v0c |
| 2077 | 3 | 4 | 5 | 6 | 7 | VII-1 | Atp6v0c-ps2 |
| 2078 | 3 | 4 | 5 | 6 | 7 | VII-1 | Atp6v1e1 |
| 2079 | 3 | 4 | 5 | 6 | 7 | VII-1 | Atp6v1g2 |
| 2080 | 3 | 4 | 5 | 6 | 7 | VII-1 | Atp8b3 |
| 2081 | 3 | 4 | 5 | 6 | 7 | VII-1 | Atp9a |
| 2082 | 3 | 4 | 5 | 6 | 7 | VII-1 | Atp9b |
| 2083 | 3 | 4 | 5 | 6 | 7 | VII-1 | Atpif1 |
| 2084 | 3 | 4 | 5 | 6 | 7 | VII-1 | Atraid |
| 2085 | 3 | 4 | 5 | 6 | 7 | VII-1 | Aup1 |
| 2086 | 3 | 4 | 5 | 6 | 7 | VII-1 | Aurkaip1 |
| 2087 | 3 | 4 | 5 | 6 | 7 | VII-1 | Awat1 |
| 2088 | 3 | 4 | 5 | 6 | 7 | VII-1 | B330016D10Rik |
| 2089 | 3 | 4 | 5 | 6 | 7 | VII-1 | B3gat1 |
| 2090 | 3 | 4 | 5 | 6 | 7 | VII-1 | B3gnt9 |
| 2091 | 3 | 4 | 5 | 6 | 7 | VII-1 | B4galnt1 |
| 2092 | 3 | 4 | 5 | 6 | 7 | VII-1 | B4galt4 |
| 2093 | 3 | 4 | 5 | 6 | 7 | VII-1 | B9d2 |
| 2094 | 3 | 4 | 5 | 6 | 7 | VII-1 | BC004004 |
| 2095 | 3 | 4 | 5 | 6 | 7 | VII-1 | BC005537 |
| 2096 | 3 | 4 | 5 | 6 | 7 | VII-1 | BC005561 |
| 2097 | 3 | 4 | 5 | 6 | 7 | VII-1 | BC018473 |
| 2098 | 3 | 4 | 5 | 6 | 7 | VII-1 | BC021614 |
| 2099 | 3 | 4 | 5 | 6 | 7 | VII-1 | BC029214 |
| 2100 | 3 | 4 | 5 | 6 | 7 | VII-1 | BC048679 |
| 2101 | 3 | 4 | 5 | 6 | 7 | VII-1 | BC049730 |
| 2102 | 3 | 4 | 5 | 6 | 7 | VII-1 | BC051142 |
| 2103 | 3 | 4 | 5 | 6 | 7 | VII-1 | BC051226 |
| 2104 | 3 | 4 | 5 | 6 | 7 | VII-1 | BC064078 |
| 2105 | 3 | 4 | 5 | 6 | 7 | VII-1 | BC147527 |
| 2106 | 3 | 4 | 5 | 6 | 7 | VII-1 | Baalc |
| 2107 | 3 | 4 | 5 | 6 | 7 | VII-1 | Bag1 |
| 2108 | 3 | 4 | 5 | 6 | 7 | VII-1 | Bai1 |
| 2109 | 3 | 4 | 5 | 6 | 7 | VII-1 | Batf3 |
| 2110 | 3 | 4 | 5 | 6 | 7 | VII-1 | Bcan |

Fig. 34 - 12

| | | | | | | | |
|---|---|---|---|---|---|---|---|
| 2111 | 3 | 4 | 5 | 6 | 7 | VII-1 | Bcas1 |
| 2112 | 3 | 4 | 5 | 6 | 7 | VII-1 | Bcas2 |
| 2113 | 3 | 4 | 5 | 6 | 7 | VII-1 | Bcat2 |
| 2114 | 3 | 4 | 5 | 6 | 7 | VII-1 | Bckdhb |
| 2115 | 3 | 4 | 5 | 6 | 7 | VII-1 | Bckdk |
| 2116 | 3 | 4 | 5 | 6 | 7 | VII-1 | Bcl2a1b |
| 2117 | 3 | 4 | 5 | 6 | 7 | VII-1 | Bcl2l15 |
| 2118 | 3 | 4 | 5 | 6 | 7 | VII-1 | Bcl7c |
| 2119 | 3 | 4 | 5 | 6 | 7 | VII-1 | Bdh2 |
| 2120 | 3 | 4 | 5 | 6 | 7 | VII-1 | Best2 |
| 2121 | 3 | 4 | 5 | 6 | 7 | VII-1 | Bex1 |
| 2122 | 3 | 4 | 5 | 6 | 7 | VII-1 | Bex2 |
| 2123 | 3 | 4 | 5 | 6 | 7 | VII-1 | Bglap3 |
| 2124 | 3 | 4 | 5 | 6 | 7 | VII-1 | Bhlha9 |
| 2125 | 3 | 4 | 5 | 6 | 7 | VII-1 | Bid |
| 2126 | 3 | 4 | 5 | 6 | 7 | VII-1 | Bik |
| 2127 | 3 | 4 | 5 | 6 | 7 | VII-1 | Bin1 |
| 2128 | 3 | 4 | 5 | 6 | 7 | VII-1 | Bin3 |
| 2129 | 3 | 4 | 5 | 6 | 7 | VII-1 | Blnk |
| 2130 | 3 | 4 | 5 | 6 | 7 | VII-1 | Bloc1s1 |
| 2131 | 3 | 4 | 5 | 6 | 7 | VII-1 | Bloc1s2 |
| 2132 | 3 | 4 | 5 | 6 | 7 | VII-1 | Blvra |
| 2133 | 3 | 4 | 5 | 6 | 7 | VII-1 | Blvrb |
| 2134 | 3 | 4 | 5 | 6 | 7 | VII-1 | Bmyc |
| 2135 | 3 | 4 | 5 | 6 | 7 | VII-1 | Bnip1 |
| 2136 | 3 | 4 | 5 | 6 | 7 | VII-1 | Bola1 |
| 2137 | 3 | 4 | 5 | 6 | 7 | VII-1 | Bola2 |
| 2138 | 3 | 4 | 5 | 6 | 7 | VII-1 | Brinp1 |
| 2139 | 3 | 4 | 5 | 6 | 7 | VII-1 | Brms1 |
| 2140 | 3 | 4 | 5 | 6 | 7 | VII-1 | Brsk1 |
| 2141 | 3 | 4 | 5 | 6 | 7 | VII-1 | Bscl2 |
| 2142 | 3 | 4 | 5 | 6 | 7 | VII-1 | Bst2 |
| 2143 | 3 | 4 | 5 | 6 | 7 | VII-1 | Btg1 |
| 2144 | 3 | 4 | 5 | 6 | 7 | VII-1 | Btg2 |
| 2145 | 3 | 4 | 5 | 6 | 7 | VII-1 | Bud31 |
| 2146 | 3 | 4 | 5 | 6 | 7 | VII-1 | Bzw2 |
| 2147 | 3 | 4 | 5 | 6 | 7 | VII-1 | C130036L24Rik |
| 2148 | 3 | 4 | 5 | 6 | 7 | VII-1 | C1qa |
| 2149 | 3 | 4 | 5 | 6 | 7 | VII-1 | C1qb |
| 2150 | 3 | 4 | 5 | 6 | 7 | VII-1 | C1qc |
| 2151 | 3 | 4 | 5 | 6 | 7 | VII-1 | C1qtnf2 |
| 2152 | 3 | 4 | 5 | 6 | 7 | VII-1 | C1qtnf4 |
| 2153 | 3 | 4 | 5 | 6 | 7 | VII-1 | C2cd4a |
| 2154 | 3 | 4 | 5 | 6 | 7 | VII-1 | C2cd4b |
| 2155 | 3 | 4 | 5 | 6 | 7 | VII-1 | C3 |
| 2156 | 3 | 4 | 5 | 6 | 7 | VII-1 | C4b |
| 2157 | 3 | 4 | 5 | 6 | 7 | VII-1 | C4bp-ps1 |
| 2158 | 3 | 4 | 5 | 6 | 7 | VII-1 | C7 |
| 2159 | 3 | 4 | 5 | 6 | 7 | VII-1 | Caap1 |
| 2160 | 3 | 4 | 5 | 6 | 7 | VII-1 | Cab39l |
| 2161 | 3 | 4 | 5 | 6 | 7 | VII-1 | Cables1 |
| 2162 | 3 | 4 | 5 | 6 | 7 | VII-1 | Cacna1c |
| 2163 | 3 | 4 | 5 | 6 | 7 | VII-1 | Cacnb4 |
| 2164 | 3 | 4 | 5 | 6 | 7 | VII-1 | Cacng1 |
| 2165 | 3 | 4 | 5 | 6 | 7 | VII-1 | Cacng3 |
| 2166 | 3 | 4 | 5 | 6 | 7 | VII-1 | Cadm3 |
| 2167 | 3 | 4 | 5 | 6 | 7 | VII-1 | Calb1 |
| 2168 | 3 | 4 | 5 | 6 | 7 | VII-1 | Calb2 |
| 2169 | 3 | 4 | 5 | 6 | 7 | VII-1 | Calca |
| 2170 | 3 | 4 | 5 | 6 | 7 | VII-1 | Calml4 |
| 2171 | 3 | 4 | 5 | 6 | 7 | VII-1 | Calr |
| 2172 | 3 | 4 | 5 | 6 | 7 | VII-1 | Caly |
| 2173 | 3 | 4 | 5 | 6 | 7 | VII-1 | Camk1 |
| 2174 | 3 | 4 | 5 | 6 | 7 | VII-1 | Camk2a |
| 2175 | 3 | 4 | 5 | 6 | 7 | VII-1 | Camk2b |
| 2176 | 3 | 4 | 5 | 6 | 7 | VII-1 | Camk2n2 |
| 2177 | 3 | 4 | 5 | 6 | 7 | VII-1 | Camkv |
| 2178 | 3 | 4 | 5 | 6 | 7 | VII-1 | Camp |
| 2179 | 3 | 4 | 5 | 6 | 7 | VII-1 | Cand2 |
| 2180 | 3 | 4 | 5 | 6 | 7 | VII-1 | Cant1 |
| 2181 | 3 | 4 | 5 | 6 | 7 | VII-1 | Cap2 |
| 2182 | 3 | 4 | 5 | 6 | 7 | VII-1 | Capn10 |
| 2183 | 3 | 4 | 5 | 6 | 7 | VII-1 | Capn12 |
| 2184 | 3 | 4 | 5 | 6 | 7 | VII-1 | Capn8 |
| 2185 | 3 | 4 | 5 | 6 | 7 | VII-1 | Capn9 |
| 2186 | 3 | 4 | 5 | 6 | 7 | VII-1 | Car14 |
| 2187 | 3 | 4 | 5 | 6 | 7 | VII-1 | Car15 |
| 2188 | 3 | 4 | 5 | 6 | 7 | VII-1 | Car6 |
| 2189 | 3 | 4 | 5 | 6 | 7 | VII-1 | Carkd |
| 2190 | 3 | 4 | 5 | 6 | 7 | VII-1 | Carm1 |
| 2191 | 3 | 4 | 5 | 6 | 7 | VII-1 | Cars |
| 2192 | 3 | 4 | 5 | 6 | 7 | VII-1 | Cars2 |
| 2193 | 3 | 4 | 5 | 6 | 7 | VII-1 | Casp4 |
| 2194 | 3 | 4 | 5 | 6 | 7 | VII-1 | Cast |
| 2195 | 3 | 4 | 5 | 6 | 7 | VII-1 | Catsper4 |
| 2196 | 3 | 4 | 5 | 6 | 7 | VII-1 | Cav3 |
| 2197 | 3 | 4 | 5 | 6 | 7 | VII-1 | Cblb |
| 2198 | 3 | 4 | 5 | 6 | 7 | VII-1 | Cbln1 |
| 2199 | 3 | 4 | 5 | 6 | 7 | VII-1 | Cbln3 |
| 2200 | 3 | 4 | 5 | 6 | 7 | VII-1 | Cbr3 |
| 2201 | 3 | 4 | 5 | 6 | 7 | VII-1 | Cbs |
| 2202 | 3 | 4 | 5 | 6 | 7 | VII-1 | Cc2d1a |
| 2203 | 3 | 4 | 5 | 6 | 7 | VII-1 | Ccbl2 |
| 2204 | 3 | 4 | 5 | 6 | 7 | VII-1 | Ccdc101 |
| 2205 | 3 | 4 | 5 | 6 | 7 | VII-1 | Ccdc107 |
| 2206 | 3 | 4 | 5 | 6 | 7 | VII-1 | Ccdc113 |
| 2207 | 3 | 4 | 5 | 6 | 7 | VII-1 | Ccdc12 |
| 2208 | 3 | 4 | 5 | 6 | 7 | VII-1 | Ccdc124 |
| 2209 | 3 | 4 | 5 | 6 | 7 | VII-1 | Ccdc153 |
| 2210 | 3 | 4 | 5 | 6 | 7 | VII-1 | Ccdc163 |
| 2211 | 3 | 4 | 5 | 6 | 7 | VII-1 | Ccdc22 |
| 2212 | 3 | 4 | 5 | 6 | 7 | VII-1 | Ccdc23 |
| 2213 | 3 | 4 | 5 | 6 | 7 | VII-1 | Ccdc28b |
| 2214 | 3 | 4 | 5 | 6 | 7 | VII-1 | Ccdc37 |
| 2215 | 3 | 4 | 5 | 6 | 7 | VII-1 | Ccdc53 |
| 2216 | 3 | 4 | 5 | 6 | 7 | VII-1 | Ccdc59 |
| 2217 | 3 | 4 | 5 | 6 | 7 | VII-1 | Ccdc85b |
| 2218 | 3 | 4 | 5 | 6 | 7 | VII-1 | Ccdc9 |
| 2219 | 3 | 4 | 5 | 6 | 7 | VII-1 | Cck |
| 2220 | 3 | 4 | 5 | 6 | 7 | VII-1 | Ccl17 |
| 2221 | 3 | 4 | 5 | 6 | 7 | VII-1 | Ccl19 |
| 2222 | 3 | 4 | 5 | 6 | 7 | VII-1 | Ccl21b |
| 2223 | 3 | 4 | 5 | 6 | 7 | VII-1 | Ccl24 |
| 2224 | 3 | 4 | 5 | 6 | 7 | VII-1 | Ccl25 |
| 2225 | 3 | 4 | 5 | 6 | 7 | VII-1 | Ccl27a |
| 2226 | 3 | 4 | 5 | 6 | 7 | VII-1 | Ccl27b |
| 2227 | 3 | 4 | 5 | 6 | 7 | VII-1 | Ccl28 |
| 2228 | 3 | 4 | 5 | 6 | 7 | VII-1 | Ccl6 |
| 2229 | 3 | 4 | 5 | 6 | 7 | VII-1 | Ccl8 |
| 2230 | 3 | 4 | 5 | 6 | 7 | VII-1 | Ccl9 |
| 2231 | 3 | 4 | 5 | 6 | 7 | VII-1 | Ccm2 |
| 2232 | 3 | 4 | 5 | 6 | 7 | VII-1 | Ccrn4l |
| 2233 | 3 | 4 | 5 | 6 | 7 | VII-1 | Ccs |
| 2234 | 3 | 4 | 5 | 6 | 7 | VII-1 | Cct7 |
| 2235 | 3 | 4 | 5 | 6 | 7 | VII-1 | Cd14 |
| 2236 | 3 | 4 | 5 | 6 | 7 | VII-1 | Cd164l2 |
| 2237 | 3 | 4 | 5 | 6 | 7 | VII-1 | Cd177 |
| 2238 | 3 | 4 | 5 | 6 | 7 | VII-1 | Cd209d |
| 2239 | 3 | 4 | 5 | 6 | 7 | VII-1 | Cd320 |
| 2240 | 3 | 4 | 5 | 6 | 7 | VII-1 | Cd55 |
| 2241 | 3 | 4 | 5 | 6 | 7 | VII-1 | Cd5l |
| 2242 | 3 | 4 | 5 | 6 | 7 | VII-1 | Cd63 |
| 2243 | 3 | 4 | 5 | 6 | 7 | VII-1 | Cd72 |
| 2244 | 3 | 4 | 5 | 6 | 7 | VII-1 | Cd82 |
| 2245 | 3 | 4 | 5 | 6 | 7 | VII-1 | Cda |
| 2246 | 3 | 4 | 5 | 6 | 7 | VII-1 | Cdc26 |
| 2247 | 3 | 4 | 5 | 6 | 7 | VII-1 | Cdc34 |
| 2248 | 3 | 4 | 5 | 6 | 7 | VII-1 | Cdc37 |
| 2249 | 3 | 4 | 5 | 6 | 7 | VII-1 | Cdc42ep5 |
| 2250 | 3 | 4 | 5 | 6 | 7 | VII-1 | Cdh16 |
| 2251 | 3 | 4 | 5 | 6 | 7 | VII-1 | Cdk10 |
| 2252 | 3 | 4 | 5 | 6 | 7 | VII-1 | Cdk11b |
| 2253 | 3 | 4 | 5 | 6 | 7 | VII-1 | Cdk20 |
| 2254 | 3 | 4 | 5 | 6 | 7 | VII-1 | Cdk5r2 |
| 2255 | 3 | 4 | 5 | 6 | 7 | VII-1 | Cdk5rap3 |
| 2256 | 3 | 4 | 5 | 6 | 7 | VII-1 | Cdkn1a |
| 2257 | 3 | 4 | 5 | 6 | 7 | VII-1 | Cdo1 |
| 2258 | 3 | 4 | 5 | 6 | 7 | VII-1 | Cdpf1 |
| 2259 | 3 | 4 | 5 | 6 | 7 | VII-1 | Ceacam12 |
| 2260 | 3 | 4 | 5 | 6 | 7 | VII-1 | Cebpd |
| 2261 | 3 | 4 | 5 | 6 | 7 | VII-1 | Cebpe |
| 2262 | 3 | 4 | 5 | 6 | 7 | VII-1 | Cel |
| 2263 | 3 | 4 | 5 | 6 | 7 | VII-1 | Cela1 |
| 2264 | 3 | 4 | 5 | 6 | 7 | VII-1 | Cela2a |
| 2265 | 3 | 4 | 5 | 6 | 7 | VII-1 | Cela3b |
| 2266 | 3 | 4 | 5 | 6 | 7 | VII-1 | Celf4 |
| 2267 | 3 | 4 | 5 | 6 | 7 | VII-1 | Celf5 |
| 2268 | 3 | 4 | 5 | 6 | 7 | VII-1 | Cend1 |
| 2269 | 3 | 4 | 5 | 6 | 7 | VII-1 | Cenpo |
| 2270 | 3 | 4 | 5 | 6 | 7 | VII-1 | Cenpv |
| 2271 | 3 | 4 | 5 | 6 | 7 | VII-1 | Cep63 |
| 2272 | 3 | 4 | 5 | 6 | 7 | VII-1 | Cep89 |
| 2273 | 3 | 4 | 5 | 6 | 7 | VII-1 | Cers4 |
| 2274 | 3 | 4 | 5 | 6 | 7 | VII-1 | Ces1d |
| 2275 | 3 | 4 | 5 | 6 | 7 | VII-1 | Ces2h |
| 2276 | 3 | 4 | 5 | 6 | 7 | VII-1 | Cetn1 |
| 2277 | 3 | 4 | 5 | 6 | 7 | VII-1 | Cfb |
| 2278 | 3 | 4 | 5 | 6 | 7 | VII-1 | Cfd |
| 2279 | 3 | 4 | 5 | 6 | 7 | VII-1 | Cfdp1 |
| 2280 | 3 | 4 | 5 | 6 | 7 | VII-1 | Cfp |
| 2281 | 3 | 4 | 5 | 6 | 7 | VII-1 | Cgref1 |
| 2282 | 3 | 4 | 5 | 6 | 7 | VII-1 | Chac1 |
| 2283 | 3 | 4 | 5 | 6 | 7 | VII-1 | Chaf1b |
| 2284 | 3 | 4 | 5 | 6 | 7 | VII-1 | Chchd1 |
| 2285 | 3 | 4 | 5 | 6 | 7 | VII-1 | Chchd10 |
| 2286 | 3 | 4 | 5 | 6 | 7 | VII-1 | Chchd2 |
| 2287 | 3 | 4 | 5 | 6 | 7 | VII-1 | Chchd6 |
| 2288 | 3 | 4 | 5 | 6 | 7 | VII-1 | Chchd7 |
| 2289 | 3 | 4 | 5 | 6 | 7 | VII-1 | Chga |
| 2290 | 3 | 4 | 5 | 6 | 7 | VII-1 | Chgb |
| 2291 | 3 | 4 | 5 | 6 | 7 | VII-1 | Chia1 |
| 2292 | 3 | 4 | 5 | 6 | 7 | VII-1 | Chic2 |
| 2293 | 3 | 4 | 5 | 6 | 7 | VII-1 | Chil1 |
| 2294 | 3 | 4 | 5 | 6 | 7 | VII-1 | Chil3 |
| 2295 | 3 | 4 | 5 | 6 | 7 | VII-1 | Chil4 |
| 2296 | 3 | 4 | 5 | 6 | 7 | VII-1 | Chkb |
| 2297 | 3 | 4 | 5 | 6 | 7 | VII-1 | Chmp2a |
| 2298 | 3 | 4 | 5 | 6 | 7 | VII-1 | Chmp3 |
| 2299 | 3 | 4 | 5 | 6 | 7 | VII-1 | Chn1 |
| 2300 | 3 | 4 | 5 | 6 | 7 | VII-1 | Chrne |
| 2301 | 3 | 4 | 5 | 6 | 7 | VII-1 | Chst2 |
| 2302 | 3 | 4 | 5 | 6 | 7 | VII-1 | Churc1 |

Fig. 34 - 13

| | | | | | | | |
|---|---|---|---|---|---|---|---|
| 2303 | 3 | 4 | 5 | 6 | 7 | VII-1 | Cib1 |
| 2304 | 3 | 4 | 5 | 6 | 7 | VII-1 | Cib3 |
| 2305 | 3 | 4 | 5 | 6 | 7 | VII-1 | Cidea |
| 2306 | 3 | 4 | 5 | 6 | 7 | VII-1 | Cidec |
| 2307 | 3 | 4 | 5 | 6 | 7 | VII-1 | Cisd2 |
| 2308 | 3 | 4 | 5 | 6 | 7 | VII-1 | Cisd3 |
| 2309 | 3 | 4 | 5 | 6 | 7 | VII-1 | Cited1 |
| 2310 | 3 | 4 | 5 | 6 | 7 | VII-1 | Ckb |
| 2311 | 3 | 4 | 5 | 6 | 7 | VII-1 | Ckm |
| 2312 | 3 | 4 | 5 | 6 | 7 | VII-1 | Ckmt1 |
| 2313 | 3 | 4 | 5 | 6 | 7 | VII-1 | Clca3 |
| 2314 | 3 | 4 | 5 | 6 | 7 | VII-1 | Cldn10 |
| 2315 | 3 | 4 | 5 | 6 | 7 | VII-1 | Cldn11 |
| 2316 | 3 | 4 | 5 | 6 | 7 | VII-1 | Cldn15 |
| 2317 | 3 | 4 | 5 | 6 | 7 | VII-1 | Cldn3 |
| 2318 | 3 | 4 | 5 | 6 | 7 | VII-1 | Cldn5 |
| 2319 | 3 | 4 | 5 | 6 | 7 | VII-1 | Cldn7 |
| 2320 | 3 | 4 | 5 | 6 | 7 | VII-1 | Clec10a |
| 2321 | 3 | 4 | 5 | 6 | 7 | VII-1 | Clec12b |
| 2322 | 3 | 4 | 5 | 6 | 7 | VII-1 | Clec1b |
| 2323 | 3 | 4 | 5 | 6 | 7 | VII-1 | Clec2l |
| 2324 | 3 | 4 | 5 | 6 | 7 | VII-1 | Clec4d |
| 2325 | 3 | 4 | 5 | 6 | 7 | VII-1 | Clint1 |
| 2326 | 3 | 4 | 5 | 6 | 7 | VII-1 | Clpp |
| 2327 | 3 | 4 | 5 | 6 | 7 | VII-1 | Clps |
| 2328 | 3 | 4 | 5 | 6 | 7 | VII-1 | Clstn3 |
| 2329 | 3 | 4 | 5 | 6 | 7 | VII-1 | Cma1 |
| 2330 | 3 | 4 | 5 | 6 | 7 | VII-1 | Cmc1 |
| 2331 | 3 | 4 | 5 | 6 | 7 | VII-1 | Cmc2 |
| 2332 | 3 | 4 | 5 | 6 | 7 | VII-1 | Cmtm2b |
| 2333 | 3 | 4 | 5 | 6 | 7 | VII-1 | Cmtm7 |
| 2334 | 3 | 4 | 5 | 6 | 7 | VII-1 | Cnfn |
| 2335 | 3 | 4 | 5 | 6 | 7 | VII-1 | Cnih2 |
| 2336 | 3 | 4 | 5 | 6 | 7 | VII-1 | Cnksr3 |
| 2337 | 3 | 4 | 5 | 6 | 7 | VII-1 | Cnot10 |
| 2338 | 3 | 4 | 5 | 6 | 7 | VII-1 | Cnot11 |
| 2339 | 3 | 4 | 5 | 6 | 7 | VII-1 | Cntd1 |
| 2340 | 3 | 4 | 5 | 6 | 7 | VII-1 | Cntn1 |
| 2341 | 3 | 4 | 5 | 6 | 7 | VII-1 | Cntnap1 |
| 2342 | 3 | 4 | 5 | 6 | 7 | VII-1 | Cntrl |
| 2343 | 3 | 4 | 5 | 6 | 7 | VII-1 | Col7a1 |
| 2344 | 3 | 4 | 5 | 6 | 7 | VII-1 | Commd6 |
| 2345 | 3 | 4 | 5 | 6 | 7 | VII-1 | Comtd1 |
| 2346 | 3 | 4 | 5 | 6 | 7 | VII-1 | Cops3 |
| 2347 | 3 | 4 | 5 | 6 | 7 | VII-1 | Cops6 |
| 2348 | 3 | 4 | 5 | 6 | 7 | VII-1 | Copz1 |
| 2349 | 3 | 4 | 5 | 6 | 7 | VII-1 | Copz2 |
| 2350 | 3 | 4 | 5 | 6 | 7 | VII-1 | Coq6 |
| 2351 | 3 | 4 | 5 | 6 | 7 | VII-1 | Coro2b |
| 2352 | 3 | 4 | 5 | 6 | 7 | VII-1 | Coro6 |
| 2353 | 3 | 4 | 5 | 6 | 7 | VII-1 | Cort |
| 2354 | 3 | 4 | 5 | 6 | 7 | VII-1 | Cox17 |
| 2355 | 3 | 4 | 5 | 6 | 7 | VII-1 | Cox20 |
| 2356 | 3 | 4 | 5 | 6 | 7 | VII-1 | Cox4i1 |
| 2357 | 3 | 4 | 5 | 6 | 7 | VII-1 | Cox4i2 |
| 2358 | 3 | 4 | 5 | 6 | 7 | VII-1 | Cox5b |
| 2359 | 3 | 4 | 5 | 6 | 7 | VII-1 | Cox6a1 |
| 2360 | 3 | 4 | 5 | 6 | 7 | VII-1 | Cox6a2 |
| 2361 | 3 | 4 | 5 | 6 | 7 | VII-1 | Cox6b1 |
| 2362 | 3 | 4 | 5 | 6 | 7 | VII-1 | Cox6b2 |
| 2363 | 3 | 4 | 5 | 6 | 7 | VII-1 | Cox7a1 |
| 2364 | 3 | 4 | 5 | 6 | 7 | VII-1 | Cox7a2 |
| 2365 | 3 | 4 | 5 | 6 | 7 | VII-1 | Cox7b |
| 2366 | 3 | 4 | 5 | 6 | 7 | VII-1 | Cox7c |
| 2367 | 3 | 4 | 5 | 6 | 7 | VII-1 | Cox8b |
| 2368 | 3 | 4 | 5 | 6 | 7 | VII-1 | Cox8c |
| 2369 | 3 | 4 | 5 | 6 | 7 | VII-1 | Cpa1 |
| 2370 | 3 | 4 | 5 | 6 | 7 | VII-1 | Cpa2 |
| 2371 | 3 | 4 | 5 | 6 | 7 | VII-1 | Cpb1 |
| 2372 | 3 | 4 | 5 | 6 | 7 | VII-1 | Cpe |
| 2373 | 3 | 4 | 5 | 6 | 7 | VII-1 | Cplx1 |
| 2374 | 3 | 4 | 5 | 6 | 7 | VII-1 | Cplx2 |
| 2375 | 3 | 4 | 5 | 6 | 7 | VII-1 | Cpsf3l |
| 2376 | 3 | 4 | 5 | 6 | 7 | VII-1 | Cpsf4 |
| 2377 | 3 | 4 | 5 | 6 | 7 | VII-1 | Cpsf4l |
| 2378 | 3 | 4 | 5 | 6 | 7 | VII-1 | Cpt1c |
| 2379 | 3 | 4 | 5 | 6 | 7 | VII-1 | Cpxm1 |
| 2380 | 3 | 4 | 5 | 6 | 7 | VII-1 | Crabp1 |
| 2381 | 3 | 4 | 5 | 6 | 7 | VII-1 | Crip1 |
| 2382 | 3 | 4 | 5 | 6 | 7 | VII-1 | Crisp2 |
| 2383 | 3 | 4 | 5 | 6 | 7 | VII-1 | Crls1 |
| 2384 | 3 | 4 | 5 | 6 | 7 | VII-1 | Crmp1 |
| 2385 | 3 | 4 | 5 | 6 | 7 | VII-1 | Crnde |
| 2386 | 3 | 4 | 5 | 6 | 7 | VII-1 | Cryaa |
| 2387 | 3 | 4 | 5 | 6 | 7 | VII-1 | Cryba4 |
| 2388 | 3 | 4 | 5 | 6 | 7 | VII-1 | Crybb3 |
| 2389 | 3 | 4 | 5 | 6 | 7 | VII-1 | Crygn |
| 2390 | 3 | 4 | 5 | 6 | 7 | VII-1 | Crym |
| 2391 | 3 | 4 | 5 | 6 | 7 | VII-1 | Cspg5 |
| 2392 | 3 | 4 | 5 | 6 | 7 | VII-1 | Csrnp1 |
| 2393 | 3 | 4 | 5 | 6 | 7 | VII-1 | Csrp2 |
| 2394 | 3 | 4 | 5 | 6 | 7 | VII-1 | Csrp3 |
| 2395 | 3 | 4 | 5 | 6 | 7 | VII-1 | Cst3 |
| 2396 | 3 | 4 | 5 | 6 | 7 | VII-1 | Cst6 |
| 2397 | 3 | 4 | 5 | 6 | 7 | VII-1 | Csta1 |
| 2398 | 3 | 4 | 5 | 6 | 7 | VII-1 | Ctc1 |
| 2399 | 3 | 4 | 5 | 6 | 7 | VII-1 | Ctcflos |
| 2400 | 3 | 4 | 5 | 6 | 7 | VII-1 | Ctdnep1 |
| 2401 | 3 | 4 | 5 | 6 | 7 | VII-1 | Ctgf |
| 2402 | 3 | 4 | 5 | 6 | 7 | VII-1 | Ctla2a |
| 2403 | 3 | 4 | 5 | 6 | 7 | VII-1 | Ctla2b |
| 2404 | 3 | 4 | 5 | 6 | 7 | VII-1 | Ctrb1 |
| 2405 | 3 | 4 | 5 | 6 | 7 | VII-1 | Ctrc |
| 2406 | 3 | 4 | 5 | 6 | 7 | VII-1 | Ctrl |
| 2407 | 3 | 4 | 5 | 6 | 7 | VII-1 | Ctsa |
| 2408 | 3 | 4 | 5 | 6 | 7 | VII-1 | Ctsd |
| 2409 | 3 | 4 | 5 | 6 | 7 | VII-1 | Ctsg |
| 2410 | 3 | 4 | 5 | 6 | 7 | VII-1 | Ctsh |
| 2411 | 3 | 4 | 5 | 6 | 7 | VII-1 | Ctsl |
| 2412 | 3 | 4 | 5 | 6 | 7 | VII-1 | Ctsz |
| 2413 | 3 | 4 | 5 | 6 | 7 | VII-1 | Ctu2 |
| 2414 | 3 | 4 | 5 | 6 | 7 | VII-1 | Ctxn1 |
| 2415 | 3 | 4 | 5 | 6 | 7 | VII-1 | Ctxn3 |
| 2416 | 3 | 4 | 5 | 6 | 7 | VII-1 | Cuedc2 |
| 2417 | 3 | 4 | 5 | 6 | 7 | VII-1 | Cuta |
| 2418 | 3 | 4 | 5 | 6 | 7 | VII-1 | Cutc |
| 2419 | 3 | 4 | 5 | 6 | 7 | VII-1 | Cuzd1 |
| 2420 | 3 | 4 | 5 | 6 | 7 | VII-1 | Cx3cl1 |
| 2421 | 3 | 4 | 5 | 6 | 7 | VII-1 | Cxcl13 |
| 2422 | 3 | 4 | 5 | 6 | 7 | VII-1 | Cyb5rl |
| 2423 | 3 | 4 | 5 | 6 | 7 | VII-1 | Cyba |
| 2424 | 3 | 4 | 5 | 6 | 7 | VII-1 | Cyp17a1 |
| 2425 | 3 | 4 | 5 | 6 | 7 | VII-1 | Cyp1b1 |
| 2426 | 3 | 4 | 5 | 6 | 7 | VII-1 | Cyp24a1 |
| 2427 | 3 | 4 | 5 | 6 | 7 | VII-1 | Cyp26b1 |
| 2428 | 3 | 4 | 5 | 6 | 7 | VII-1 | Cyp27b1 |
| 2429 | 3 | 4 | 5 | 6 | 7 | VII-1 | Cyp2b10 |
| 2430 | 3 | 4 | 5 | 6 | 7 | VII-1 | Cyp2e1 |
| 2431 | 3 | 4 | 5 | 6 | 7 | VII-1 | Cyp2s1 |
| 2432 | 3 | 4 | 5 | 6 | 7 | VII-1 | Cyp4a10 |
| 2433 | 3 | 4 | 5 | 6 | 7 | VII-1 | Cyp4a14 |
| 2434 | 3 | 4 | 5 | 6 | 7 | VII-1 | Cyp4f13 |
| 2435 | 3 | 4 | 5 | 6 | 7 | VII-1 | Cyp4f15 |
| 2436 | 3 | 4 | 5 | 6 | 7 | VII-1 | Cyp51 |
| 2437 | 3 | 4 | 5 | 6 | 7 | VII-1 | Cypt2 |
| 2438 | 3 | 4 | 5 | 6 | 7 | VII-1 | Cys1 |
| 2439 | 3 | 4 | 5 | 6 | 7 | VII-1 | Cytl1 |
| 2440 | 3 | 4 | 5 | 6 | 7 | VII-1 | D17H6S53E |
| 2441 | 3 | 4 | 5 | 6 | 7 | VII-1 | D198wg1357e |
| 2442 | 3 | 4 | 5 | 6 | 7 | VII-1 | D230025D16Rik |
| 2443 | 3 | 4 | 5 | 6 | 7 | VII-1 | D2Wsu81e |
| 2444 | 3 | 4 | 5 | 6 | 7 | VII-1 | D330041H03Rik |
| 2445 | 3 | 4 | 5 | 6 | 7 | VII-1 | D330050I16Rik |
| 2446 | 3 | 4 | 5 | 6 | 7 | VII-1 | D3Bwg0562e |
| 2447 | 3 | 4 | 5 | 6 | 7 | VII-1 | D8Ertd738e |
| 2448 | 3 | 4 | 5 | 6 | 7 | VII-1 | Dancr |
| 2449 | 3 | 4 | 5 | 6 | 7 | VII-1 | Dao |
| 2450 | 3 | 4 | 5 | 6 | 7 | VII-1 | Dap3 |
| 2451 | 3 | 4 | 5 | 6 | 7 | VII-1 | Dapk3 |
| 2452 | 3 | 4 | 5 | 6 | 7 | VII-1 | Dapp1 |
| 2453 | 3 | 4 | 5 | 6 | 7 | VII-1 | Dbi |
| 2454 | 3 | 4 | 5 | 6 | 7 | VII-1 | Dbil5 |
| 2455 | 3 | 4 | 5 | 6 | 7 | VII-1 | Dclk1 |
| 2456 | 3 | 4 | 5 | 6 | 7 | VII-1 | Dcps |
| 2457 | 3 | 4 | 5 | 6 | 7 | VII-1 | Dctn2 |
| 2458 | 3 | 4 | 5 | 6 | 7 | VII-1 | Dctn3 |
| 2459 | 3 | 4 | 5 | 6 | 7 | VII-1 | Dctpp1 |
| 2460 | 3 | 4 | 5 | 6 | 7 | VII-1 | Dcun1d5 |
| 2461 | 3 | 4 | 5 | 6 | 7 | VII-1 | Dcxr |
| 2462 | 3 | 4 | 5 | 6 | 7 | VII-1 | Ddb1 |
| 2463 | 3 | 4 | 5 | 6 | 7 | VII-1 | Ddi2 |
| 2464 | 3 | 4 | 5 | 6 | 7 | VII-1 | Ddit3 |
| 2465 | 3 | 4 | 5 | 6 | 7 | VII-1 | Ddit4 |
| 2466 | 3 | 4 | 5 | 6 | 7 | VII-1 | Ddn |
| 2467 | 3 | 4 | 5 | 6 | 7 | VII-1 | Ddx47 |
| 2468 | 3 | 4 | 5 | 6 | 7 | VII-1 | Ddx49 |
| 2469 | 3 | 4 | 5 | 6 | 7 | VII-1 | Ddx56 |
| 2470 | 3 | 4 | 5 | 6 | 7 | VII-1 | Decr1 |
| 2471 | 3 | 4 | 5 | 6 | 7 | VII-1 | Dedd2 |
| 2472 | 3 | 4 | 5 | 6 | 7 | VII-1 | Defa-rs1 |
| 2473 | 3 | 4 | 5 | 6 | 7 | VII-1 | Defa-rs7 |
| 2474 | 3 | 4 | 5 | 6 | 7 | VII-1 | Defa17 |
| 2475 | 3 | 4 | 5 | 6 | 7 | VII-1 | Defa23 |
| 2476 | 3 | 4 | 5 | 6 | 7 | VII-1 | Defa24 |
| 2477 | 3 | 4 | 5 | 6 | 7 | VII-1 | Defa3 |
| 2478 | 3 | 4 | 5 | 6 | 7 | VII-1 | Defb1 |
| 2479 | 3 | 4 | 5 | 6 | 7 | VII-1 | Defb11 |
| 2480 | 3 | 4 | 5 | 6 | 7 | VII-1 | Defb14 |
| 2481 | 3 | 4 | 5 | 6 | 7 | VII-1 | Defb2 |
| 2482 | 3 | 4 | 5 | 6 | 7 | VII-1 | Defb22 |
| 2483 | 3 | 4 | 5 | 6 | 7 | VII-1 | Defb25 |
| 2484 | 3 | 4 | 5 | 6 | 7 | VII-1 | Defb28 |
| 2485 | 3 | 4 | 5 | 6 | 7 | VII-1 | Defb36 |
| 2486 | 3 | 4 | 5 | 6 | 7 | VII-1 | Defb37 |
| 2487 | 3 | 4 | 5 | 6 | 7 | VII-1 | Defb39 |
| 2488 | 3 | 4 | 5 | 6 | 7 | VII-1 | Defb40 |
| 2489 | 3 | 4 | 5 | 6 | 7 | VII-1 | Defb45 |
| 2490 | 3 | 4 | 5 | 6 | 7 | VII-1 | Defb6 |
| 2491 | 3 | 4 | 5 | 6 | 7 | VII-1 | Degs2 |
| 2492 | 3 | 4 | 5 | 6 | 7 | VII-1 | Dennd4a |
| 2493 | 3 | 4 | 5 | 6 | 7 | VII-1 | Deptor |
| 2494 | 3 | 4 | 5 | 6 | 7 | VII-1 | Derl2 |

Fig. 34 - 14

| | | | | | | | |
|---|---|---|---|---|---|---|---|
| 2495 | 3 | 4 | 5 | 6 | 7 | VII-1 | Derl3 |
| 2496 | 3 | 4 | 5 | 6 | 7 | VII-1 | Des |
| 2497 | 3 | 4 | 5 | 6 | 7 | VII-1 | Dgat1 |
| 2498 | 3 | 4 | 5 | 6 | 7 | VII-1 | Dhrs13 |
| 2499 | 3 | 4 | 5 | 6 | 7 | VII-1 | Dhrs7c |
| 2500 | 3 | 4 | 5 | 6 | 7 | VII-1 | Dhrsx |
| 2501 | 3 | 4 | 5 | 6 | 7 | VII-1 | Dhx58 |
| 2502 | 3 | 4 | 5 | 6 | 7 | VII-1 | Dio3os |
| 2503 | 3 | 4 | 5 | 6 | 7 | VII-1 | Diras1 |
| 2504 | 3 | 4 | 5 | 6 | 7 | VII-1 | Disp2 |
| 2505 | 3 | 4 | 5 | 6 | 7 | VII-1 | Dlgap1 |
| 2506 | 3 | 4 | 5 | 6 | 7 | VII-1 | Dlgap3 |
| 2507 | 3 | 4 | 5 | 6 | 7 | VII-1 | Dlgap4 |
| 2508 | 3 | 4 | 5 | 6 | 7 | VII-1 | Dmap1 |
| 2509 | 3 | 4 | 5 | 6 | 7 | VII-1 | Dmbt1 |
| 2510 | 3 | 4 | 5 | 6 | 7 | VII-1 | Dmkn |
| 2511 | 3 | 4 | 5 | 6 | 7 | VII-1 | Dnaaf1 |
| 2512 | 3 | 4 | 5 | 6 | 7 | VII-1 | Dnajb12 |
| 2513 | 3 | 4 | 5 | 6 | 7 | VII-1 | Dnajb14 |
| 2514 | 3 | 4 | 5 | 6 | 7 | VII-1 | Dnajb2 |
| 2515 | 3 | 4 | 5 | 6 | 7 | VII-1 | Dnajc11 |
| 2516 | 3 | 4 | 5 | 6 | 7 | VII-1 | Dnajc15 |
| 2517 | 3 | 4 | 5 | 6 | 7 | VII-1 | Dnajc17 |
| 2518 | 3 | 4 | 5 | 6 | 7 | VII-1 | Dnajc19 |
| 2519 | 3 | 4 | 5 | 6 | 7 | VII-1 | Dnajc22 |
| 2520 | 3 | 4 | 5 | 6 | 7 | VII-1 | Dnajc9 |
| 2521 | 3 | 4 | 5 | 6 | 7 | VII-1 | Dnase2a |
| 2522 | 3 | 4 | 5 | 6 | 7 | VII-1 | Dner |
| 2523 | 3 | 4 | 5 | 6 | 7 | VII-1 | Dnph1 |
| 2524 | 3 | 4 | 5 | 6 | 7 | VII-1 | Dnttip1 |
| 2525 | 3 | 4 | 5 | 6 | 7 | VII-1 | Doc2b |
| 2526 | 3 | 4 | 5 | 6 | 7 | VII-1 | Doc2g |
| 2527 | 3 | 4 | 5 | 6 | 7 | VII-1 | Dpagt1 |
| 2528 | 3 | 4 | 5 | 6 | 7 | VII-1 | Dpcd |
| 2529 | 3 | 4 | 5 | 6 | 7 | VII-1 | Dpep1 |
| 2530 | 3 | 4 | 5 | 6 | 7 | VII-1 | Dph1 |
| 2531 | 3 | 4 | 5 | 6 | 7 | VII-1 | Dph5 |
| 2532 | 3 | 4 | 5 | 6 | 7 | VII-1 | Dpm3 |
| 2533 | 3 | 4 | 5 | 6 | 7 | VII-1 | Dpp6 |
| 2534 | 3 | 4 | 5 | 6 | 7 | VII-1 | Dpp7 |
| 2535 | 3 | 4 | 5 | 6 | 7 | VII-1 | Dpy30 |
| 2536 | 3 | 4 | 5 | 6 | 7 | VII-1 | Drap1 |
| 2537 | 3 | 4 | 5 | 6 | 7 | VII-1 | Dreh |
| 2538 | 3 | 4 | 5 | 6 | 7 | VII-1 | Drosha |
| 2539 | 3 | 4 | 5 | 6 | 7 | VII-1 | Dtnb |
| 2540 | 3 | 4 | 5 | 6 | 7 | VII-1 | Dus1l |
| 2541 | 3 | 4 | 5 | 6 | 7 | VII-1 | Dus2 |
| 2542 | 3 | 4 | 5 | 6 | 7 | VII-1 | Dusp1 |
| 2543 | 3 | 4 | 5 | 6 | 7 | VII-1 | Dusp22 |
| 2544 | 3 | 4 | 5 | 6 | 7 | VII-1 | Dusp26 |
| 2545 | 3 | 4 | 5 | 6 | 7 | VII-1 | Dym |
| 2546 | 3 | 4 | 5 | 6 | 7 | VII-1 | Dync1h1 |
| 2547 | 3 | 4 | 5 | 6 | 7 | VII-1 | Dync1li1 |
| 2548 | 3 | 4 | 5 | 6 | 7 | VII-1 | Dynlrb1 |
| 2549 | 3 | 4 | 5 | 6 | 7 | VII-1 | Dynlt1c |
| 2550 | 3 | 4 | 5 | 6 | 7 | VII-1 | Dzank1 |
| 2551 | 3 | 4 | 5 | 6 | 7 | VII-1 | E030018B13Rik |
| 2552 | 3 | 4 | 5 | 6 | 7 | VII-1 | E030030I06Rik |
| 2553 | 3 | 4 | 5 | 6 | 7 | VII-1 | E030044B06Rik |
| 2554 | 3 | 4 | 5 | 6 | 7 | VII-1 | E130012A19Rik |
| 2555 | 3 | 4 | 5 | 6 | 7 | VII-1 | E130203H02Rik |
| 2556 | 3 | 4 | 5 | 6 | 7 | VII-1 | E230008N13Rik |
| 2557 | 3 | 4 | 5 | 6 | 7 | VII-1 | E530011L22Rik |
| 2558 | 3 | 4 | 5 | 6 | 7 | VII-1 | Eapp |
| 2559 | 3 | 4 | 5 | 6 | 7 | VII-1 | Ear1 |
| 2560 | 3 | 4 | 5 | 6 | 7 | VII-1 | Ear3 |
| 2561 | 3 | 4 | 5 | 6 | 7 | VII-1 | Ear6 |
| 2562 | 3 | 4 | 5 | 6 | 7 | VII-1 | Ebi3 |
| 2563 | 3 | 4 | 5 | 6 | 7 | VII-1 | Ebp |
| 2564 | 3 | 4 | 5 | 6 | 7 | VII-1 | Ebpl |
| 2565 | 3 | 4 | 5 | 6 | 7 | VII-1 | Echdc2 |
| 2566 | 3 | 4 | 5 | 6 | 7 | VII-1 | Eci2 |
| 2567 | 3 | 4 | 5 | 6 | 7 | VII-1 | Ecscr |
| 2568 | 3 | 4 | 5 | 6 | 7 | VII-1 | Eddm3b |
| 2569 | 3 | 4 | 5 | 6 | 7 | VII-1 | Edf1 |
| 2570 | 3 | 4 | 5 | 6 | 7 | VII-1 | Eef1a2 |
| 2571 | 3 | 4 | 5 | 6 | 7 | VII-1 | Eef1d |
| 2572 | 3 | 4 | 5 | 6 | 7 | VII-1 | Eef1g |
| 2573 | 3 | 4 | 5 | 6 | 7 | VII-1 | Efcab2 |
| 2574 | 3 | 4 | 5 | 6 | 7 | VII-1 | Efcab4a |
| 2575 | 3 | 4 | 5 | 6 | 7 | VII-1 | Efemp1 |
| 2576 | 3 | 4 | 5 | 6 | 7 | VII-1 | Efemp2 |
| 2577 | 3 | 4 | 5 | 6 | 7 | VII-1 | Egfbp2 |
| 2578 | 3 | 4 | 5 | 6 | 7 | VII-1 | Egfl7 |
| 2579 | 3 | 4 | 5 | 6 | 7 | VII-1 | Egln2 |
| 2580 | 3 | 4 | 5 | 6 | 7 | VII-1 | Egln3 |
| 2581 | 3 | 4 | 5 | 6 | 7 | VII-1 | Egr1 |
| 2582 | 3 | 4 | 5 | 6 | 7 | VII-1 | Ehhadh |
| 2583 | 3 | 4 | 5 | 6 | 7 | VII-1 | Eif2b2 |
| 2584 | 3 | 4 | 5 | 6 | 7 | VII-1 | Eif2b4 |
| 2585 | 3 | 4 | 5 | 6 | 7 | VII-1 | Eif3b |
| 2586 | 3 | 4 | 5 | 6 | 7 | VII-1 | Eif3d |
| 2587 | 3 | 4 | 5 | 6 | 7 | VII-1 | Eif3f |
| 2588 | 3 | 4 | 5 | 6 | 7 | VII-1 | Eif3h |
| 2589 | 3 | 4 | 5 | 6 | 7 | VII-1 | Eif3j1 |
| 2590 | 3 | 4 | 5 | 6 | 7 | VII-1 | Eif3j2 |

| | | | | | | | |
|---|---|---|---|---|---|---|---|
| 2591 | 3 | 4 | 5 | 6 | 7 | VII-1 | Eif3k |
| 2592 | 3 | 4 | 5 | 6 | 7 | VII-1 | Eif3m |
| 2593 | 3 | 4 | 5 | 6 | 7 | VII-1 | Eif4e2 |
| 2594 | 3 | 4 | 5 | 6 | 7 | VII-1 | Eif4ebp1 |
| 2595 | 3 | 4 | 5 | 6 | 7 | VII-1 | Eif4ebp3 |
| 2596 | 3 | 4 | 5 | 6 | 7 | VII-1 | Eif6 |
| 2597 | 3 | 4 | 5 | 6 | 7 | VII-1 | Elane |
| 2598 | 3 | 4 | 5 | 6 | 7 | VII-1 | Elavl3 |
| 2599 | 3 | 4 | 5 | 6 | 7 | VII-1 | Elk4 |
| 2600 | 3 | 4 | 5 | 6 | 7 | VII-1 | Elmod1 |
| 2601 | 3 | 4 | 5 | 6 | 7 | VII-1 | Elovl3 |
| 2602 | 3 | 4 | 5 | 6 | 7 | VII-1 | Elp6 |
| 2603 | 3 | 4 | 5 | 6 | 7 | VII-1 | Emc9 |
| 2604 | 3 | 4 | 5 | 6 | 7 | VII-1 | Emd |
| 2605 | 3 | 4 | 5 | 6 | 7 | VII-1 | Emp3 |
| 2606 | 3 | 4 | 5 | 6 | 7 | VII-1 | Endog |
| 2607 | 3 | 4 | 5 | 6 | 7 | VII-1 | Engase |
| 2608 | 3 | 4 | 5 | 6 | 7 | VII-1 | Enho |
| 2609 | 3 | 4 | 5 | 6 | 7 | VII-1 | Eno2 |
| 2610 | 3 | 4 | 5 | 6 | 7 | VII-1 | Eno3 |
| 2611 | 3 | 4 | 5 | 6 | 7 | VII-1 | Enpp1 |
| 2612 | 3 | 4 | 5 | 6 | 7 | VII-1 | Epdr1 |
| 2613 | 3 | 4 | 5 | 6 | 7 | VII-1 | Ephx2 |
| 2614 | 3 | 4 | 5 | 6 | 7 | VII-1 | Epn1 |
| 2615 | 3 | 4 | 5 | 6 | 7 | VII-1 | Eri3 |
| 2616 | 3 | 4 | 5 | 6 | 7 | VII-1 | Ern1 |
| 2617 | 3 | 4 | 5 | 6 | 7 | VII-1 | Ero1lb |
| 2618 | 3 | 4 | 5 | 6 | 7 | VII-1 | Erp27 |
| 2619 | 3 | 4 | 5 | 6 | 7 | VII-1 | Errfi1 |
| 2620 | 3 | 4 | 5 | 6 | 7 | VII-1 | Esd |
| 2621 | 3 | 4 | 5 | 6 | 7 | VII-1 | Esm1 |
| 2622 | 3 | 4 | 5 | 6 | 7 | VII-1 | Espn |
| 2623 | 3 | 4 | 5 | 6 | 7 | VII-1 | Etfb |
| 2624 | 3 | 4 | 5 | 6 | 7 | VII-1 | Etnppl |
| 2625 | 3 | 4 | 5 | 6 | 7 | VII-1 | Etohd2 |
| 2626 | 3 | 4 | 5 | 6 | 7 | VII-1 | Etohi1 |
| 2627 | 3 | 4 | 5 | 6 | 7 | VII-1 | Eva1a |
| 2628 | 3 | 4 | 5 | 6 | 7 | VII-1 | Eva1c |
| 2629 | 3 | 4 | 5 | 6 | 7 | VII-1 | Exoc7 |
| 2630 | 3 | 4 | 5 | 6 | 7 | VII-1 | Extl1 |
| 2631 | 3 | 4 | 5 | 6 | 7 | VII-1 | Ezh2 |
| 2632 | 3 | 4 | 5 | 6 | 7 | VII-1 | F13a1 |
| 2633 | 3 | 4 | 5 | 6 | 7 | VII-1 | F3 |
| 2634 | 3 | 4 | 5 | 6 | 7 | VII-1 | Fabp3 |
| 2635 | 3 | 4 | 5 | 6 | 7 | VII-1 | Fabp6 |
| 2636 | 3 | 4 | 5 | 6 | 7 | VII-1 | Fabp9 |
| 2637 | 3 | 4 | 5 | 6 | 7 | VII-1 | Fads2 |
| 2638 | 3 | 4 | 5 | 6 | 7 | VII-1 | Fads6 |
| 2639 | 3 | 4 | 5 | 6 | 7 | VII-1 | Faf1 |
| 2640 | 3 | 4 | 5 | 6 | 7 | VII-1 | Fah |
| 2641 | 3 | 4 | 5 | 6 | 7 | VII-1 | Fahd2a |
| 2642 | 3 | 4 | 5 | 6 | 7 | VII-1 | Faim2 |
| 2643 | 3 | 4 | 5 | 6 | 7 | VII-1 | Faim3 |
| 2644 | 3 | 4 | 5 | 6 | 7 | VII-1 | Fam107a |
| 2645 | 3 | 4 | 5 | 6 | 7 | VII-1 | Fam131b |
| 2646 | 3 | 4 | 5 | 6 | 7 | VII-1 | Fam132a |
| 2647 | 3 | 4 | 5 | 6 | 7 | VII-1 | Fam134b |
| 2648 | 3 | 4 | 5 | 6 | 7 | VII-1 | Fam151a |
| 2649 | 3 | 4 | 5 | 6 | 7 | VII-1 | Fam163b |
| 2650 | 3 | 4 | 5 | 6 | 7 | VII-1 | Fam167b |
| 2651 | 3 | 4 | 5 | 6 | 7 | VII-1 | Fam171b |
| 2652 | 3 | 4 | 5 | 6 | 7 | VII-1 | Fam173a |
| 2653 | 3 | 4 | 5 | 6 | 7 | VII-1 | Fam195a |
| 2654 | 3 | 4 | 5 | 6 | 7 | VII-1 | Fam195b |
| 2655 | 3 | 4 | 5 | 6 | 7 | VII-1 | Fam19a5 |
| 2656 | 3 | 4 | 5 | 6 | 7 | VII-1 | Fam21 |
| 2657 | 3 | 4 | 5 | 6 | 7 | VII-1 | Fam212a |
| 2658 | 3 | 4 | 5 | 6 | 7 | VII-1 | Fam213b |
| 2659 | 3 | 4 | 5 | 6 | 7 | VII-1 | Fam214a |
| 2660 | 3 | 4 | 5 | 6 | 7 | VII-1 | Fam219aos |
| 2661 | 3 | 4 | 5 | 6 | 7 | VII-1 | Fam222a |
| 2662 | 3 | 4 | 5 | 6 | 7 | VII-1 | Fam229a |
| 2663 | 3 | 4 | 5 | 6 | 7 | VII-1 | Fam229b |
| 2664 | 3 | 4 | 5 | 6 | 7 | VII-1 | Fam24a |
| 2665 | 3 | 4 | 5 | 6 | 7 | VII-1 | Fam25c |
| 2666 | 3 | 4 | 5 | 6 | 7 | VII-1 | Fam49a |
| 2667 | 3 | 4 | 5 | 6 | 7 | VII-1 | Fam53b |
| 2668 | 3 | 4 | 5 | 6 | 7 | VII-1 | Fam57b |
| 2669 | 3 | 4 | 5 | 6 | 7 | VII-1 | Fam69b |
| 2670 | 3 | 4 | 5 | 6 | 7 | VII-1 | Fam83a |
| 2671 | 3 | 4 | 5 | 6 | 7 | VII-1 | Fam92b |
| 2672 | 3 | 4 | 5 | 6 | 7 | VII-1 | Fam96b |
| 2673 | 3 | 4 | 5 | 6 | 7 | VII-1 | Fam98c |
| 2674 | 3 | 4 | 5 | 6 | 7 | VII-1 | Fasn |
| 2675 | 3 | 4 | 5 | 6 | 7 | VII-1 | Fau |
| 2676 | 3 | 4 | 5 | 6 | 7 | VII-1 | Fbll1 |
| 2677 | 3 | 4 | 5 | 6 | 7 | VII-1 | Fbxl16 |
| 2678 | 3 | 4 | 5 | 6 | 7 | VII-1 | Fbxl22 |
| 2679 | 3 | 4 | 5 | 6 | 7 | VII-1 | Fbxo31 |
| 2680 | 3 | 4 | 5 | 6 | 7 | VII-1 | Fbxo7 |
| 2681 | 3 | 4 | 5 | 6 | 7 | VII-1 | Fbxw4 |
| 2682 | 3 | 4 | 5 | 6 | 7 | VII-1 | Fbxw5 |
| 2683 | 3 | 4 | 5 | 6 | 7 | VII-1 | Fcer1g |
| 2684 | 3 | 4 | 5 | 6 | 7 | VII-1 | Fcf1 |
| 2685 | 3 | 4 | 5 | 6 | 7 | VII-1 | Fcgbp |
| 2686 | 3 | 4 | 5 | 6 | 7 | VII-1 | Fcgr3 |

Fig. 34 - 15

| | | | | | | | |
|---|---|---|---|---|---|---|---|
| 2687 | 3 | 4 | 5 | 6 | 7 | VII-1 | Fcgr4 |
| 2688 | 3 | 4 | 5 | 6 | 7 | VII-1 | Fcna |
| 2689 | 3 | 4 | 5 | 6 | 7 | VII-1 | Fcnb |
| 2690 | 3 | 4 | 5 | 6 | 7 | VII-1 | Fdft1 |
| 2691 | 3 | 4 | 5 | 6 | 7 | VII-1 | Fdps |
| 2692 | 3 | 4 | 5 | 6 | 7 | VII-1 | Fdx1l |
| 2693 | 3 | 4 | 5 | 6 | 7 | VII-1 | Fdxr |
| 2694 | 3 | 4 | 5 | 6 | 7 | VII-1 | Fech |
| 2695 | 3 | 4 | 5 | 6 | 7 | VII-1 | Fes |
| 2696 | 3 | 4 | 5 | 6 | 7 | VII-1 | Fez1 |
| 2697 | 3 | 4 | 5 | 6 | 7 | VII-1 | Fga |
| 2698 | 3 | 4 | 5 | 6 | 7 | VII-1 | Fgb |
| 2699 | 3 | 4 | 5 | 6 | 7 | VII-1 | Fgf21 |
| 2700 | 3 | 4 | 5 | 6 | 7 | VII-1 | Fgfr2 |
| 2701 | 3 | 4 | 5 | 6 | 7 | VII-1 | Fggy |
| 2702 | 3 | 4 | 5 | 6 | 7 | VII-1 | Fh1 |
| 2703 | 3 | 4 | 5 | 6 | 7 | VII-1 | Fhad1 |
| 2704 | 3 | 4 | 5 | 6 | 7 | VII-1 | Fhit |
| 2705 | 3 | 4 | 5 | 6 | 7 | VII-1 | Fhl3 |
| 2706 | 3 | 4 | 5 | 6 | 7 | VII-1 | Fhl4 |
| 2707 | 3 | 4 | 5 | 6 | 7 | VII-1 | Fis1 |
| 2708 | 3 | 4 | 5 | 6 | 7 | VII-1 | Fkbp11 |
| 2709 | 3 | 4 | 5 | 6 | 7 | VII-1 | Fkbp2 |
| 2710 | 3 | 4 | 5 | 6 | 7 | VII-1 | Fkbp5 |
| 2711 | 3 | 4 | 5 | 6 | 7 | VII-1 | Fkbpl |
| 2712 | 3 | 4 | 5 | 6 | 7 | VII-1 | Flt3l |
| 2713 | 3 | 4 | 5 | 6 | 7 | VII-1 | Flywch2 |
| 2714 | 3 | 4 | 5 | 6 | 7 | VII-1 | Fmn2 |
| 2715 | 3 | 4 | 5 | 6 | 7 | VII-1 | Fmo2 |
| 2716 | 3 | 4 | 5 | 6 | 7 | VII-1 | Fn3k |
| 2717 | 3 | 4 | 5 | 6 | 7 | VII-1 | Folr1 |
| 2718 | 3 | 4 | 5 | 6 | 7 | VII-1 | Fos |
| 2719 | 3 | 4 | 5 | 6 | 7 | VII-1 | Fosl2 |
| 2720 | 3 | 4 | 5 | 6 | 7 | VII-1 | Foxo3 |
| 2721 | 3 | 4 | 5 | 6 | 7 | VII-1 | Frg1 |
| 2722 | 3 | 4 | 5 | 6 | 7 | VII-1 | Frrs1 |
| 2723 | 3 | 4 | 5 | 6 | 7 | VII-1 | Frrs1l |
| 2724 | 3 | 4 | 5 | 6 | 7 | VII-1 | Fst |
| 2725 | 3 | 4 | 5 | 6 | 7 | VII-1 | Fth1 |
| 2726 | 3 | 4 | 5 | 6 | 7 | VII-1 | Ftsj1 |
| 2727 | 3 | 4 | 5 | 6 | 7 | VII-1 | Ftsj2 |
| 2728 | 3 | 4 | 5 | 6 | 7 | VII-1 | Fuca1 |
| 2729 | 3 | 4 | 5 | 6 | 7 | VII-1 | Fuom |
| 2730 | 3 | 4 | 5 | 6 | 7 | VII-1 | Fus |
| 2731 | 3 | 4 | 5 | 6 | 7 | VII-1 | Fxn |
| 2732 | 3 | 4 | 5 | 6 | 7 | VII-1 | Fxyd1 |
| 2733 | 3 | 4 | 5 | 6 | 7 | VII-1 | Fxyd2 |
| 2734 | 3 | 4 | 5 | 6 | 7 | VII-1 | Fxyd3 |
| 2735 | 3 | 4 | 5 | 6 | 7 | VII-1 | Fxyd5 |
| 2736 | 3 | 4 | 5 | 6 | 7 | VII-1 | Fxyd7 |
| 2737 | 3 | 4 | 5 | 6 | 7 | VII-1 | Gabarapl2 |
| 2738 | 3 | 4 | 5 | 6 | 7 | VII-1 | Gabra1 |
| 2739 | 3 | 4 | 5 | 6 | 7 | VII-1 | Gabra3 |
| 2740 | 3 | 4 | 5 | 6 | 7 | VII-1 | Gabrb3 |
| 2741 | 3 | 4 | 5 | 6 | 7 | VII-1 | Gabrq |
| 2742 | 3 | 4 | 5 | 6 | 7 | VII-1 | Gad1 |
| 2743 | 3 | 4 | 5 | 6 | 7 | VII-1 | Gad2 |
| 2744 | 3 | 4 | 5 | 6 | 7 | VII-1 | Gadd45b |
| 2745 | 3 | 4 | 5 | 6 | 7 | VII-1 | Gadd45g |
| 2746 | 3 | 4 | 5 | 6 | 7 | VII-1 | Gadd45gip1 |
| 2747 | 3 | 4 | 5 | 6 | 7 | VII-1 | Gains |
| 2748 | 3 | 4 | 5 | 6 | 7 | VII-1 | Galt |
| 2749 | 3 | 4 | 5 | 6 | 7 | VII-1 | Gap43 |
| 2750 | 3 | 4 | 5 | 6 | 7 | VII-1 | Gapdhs |
| 2751 | 3 | 4 | 5 | 6 | 7 | VII-1 | Gar1 |
| 2752 | 3 | 4 | 5 | 6 | 7 | VII-1 | Gas1 |
| 2753 | 3 | 4 | 5 | 6 | 7 | VII-1 | Gatad2b |
| 2754 | 3 | 4 | 5 | 6 | 7 | VII-1 | Gatsl3 |
| 2755 | 3 | 4 | 5 | 6 | 7 | VII-1 | Gba |
| 2756 | 3 | 4 | 5 | 6 | 7 | VII-1 | Gbp11 |
| 2757 | 3 | 4 | 5 | 6 | 7 | VII-1 | Gcat |
| 2758 | 3 | 4 | 5 | 6 | 7 | VII-1 | Gchfr |
| 2759 | 3 | 4 | 5 | 6 | 7 | VII-1 | Gcnl1 |
| 2760 | 3 | 4 | 5 | 6 | 7 | VII-1 | Gdf1 |
| 2761 | 3 | 4 | 5 | 6 | 7 | VII-1 | Gdf15 |
| 2762 | 3 | 4 | 5 | 6 | 7 | VII-1 | Gdpd3 |
| 2763 | 3 | 4 | 5 | 6 | 7 | VII-1 | Gdpd5 |
| 2764 | 3 | 4 | 5 | 6 | 7 | VII-1 | Gemin7 |
| 2765 | 3 | 4 | 5 | 6 | 7 | VII-1 | Gfer |
| 2766 | 3 | 4 | 5 | 6 | 7 | VII-1 | Gfod2 |
| 2767 | 3 | 4 | 5 | 6 | 7 | VII-1 | Ggct |
| 2768 | 3 | 4 | 5 | 6 | 7 | VII-1 | Ggnbp1 |
| 2769 | 3 | 4 | 5 | 6 | 7 | VII-1 | Ggt1 |
| 2770 | 3 | 4 | 5 | 6 | 7 | VII-1 | Ggt5 |
| 2771 | 3 | 4 | 5 | 6 | 7 | VII-1 | Gins4 |
| 2772 | 3 | 4 | 5 | 6 | 7 | VII-1 | Gjb4 |
| 2773 | 3 | 4 | 5 | 6 | 7 | VII-1 | Gk2 |
| 2774 | 3 | 4 | 5 | 6 | 7 | VII-1 | Glb1 |
| 2775 | 3 | 4 | 5 | 6 | 7 | VII-1 | Glmn |
| 2776 | 3 | 4 | 5 | 6 | 7 | VII-1 | Glo1 |
| 2777 | 3 | 4 | 5 | 6 | 7 | VII-1 | Glod5 |
| 2778 | 3 | 4 | 5 | 6 | 7 | VII-1 | Glrb |
| 2779 | 3 | 4 | 5 | 6 | 7 | VII-1 | Glrx3 |
| 2780 | 3 | 4 | 5 | 6 | 7 | VII-1 | Glul |
| 2781 | 3 | 4 | 5 | 6 | 7 | VII-1 | Gm10012 |
| 2782 | 3 | 4 | 5 | 6 | 7 | VII-1 | Gm10094 |
| 2783 | 3 | 4 | 5 | 6 | 7 | VII-1 | Gm10318 |
| 2784 | 3 | 4 | 5 | 6 | 7 | VII-1 | Gm10334 |
| 2785 | 3 | 4 | 5 | 6 | 7 | VII-1 | Gm10409 |
| 2786 | 3 | 4 | 5 | 6 | 7 | VII-1 | Gm10451 |
| 2787 | 3 | 4 | 5 | 6 | 7 | VII-1 | Gm10591 |
| 2788 | 3 | 4 | 5 | 6 | 7 | VII-1 | Gm10638 |
| 2789 | 3 | 4 | 5 | 6 | 7 | VII-1 | Gm10754 |
| 2790 | 3 | 4 | 5 | 6 | 7 | VII-1 | Gm11517 |
| 2791 | 3 | 4 | 5 | 6 | 7 | VII-1 | Gm11627 |
| 2792 | 3 | 4 | 5 | 6 | 7 | VII-1 | Gm11974 |
| 2793 | 3 | 4 | 5 | 6 | 7 | VII-1 | Gm12191 |
| 2794 | 3 | 4 | 5 | 6 | 7 | VII-1 | Gm13139 |
| 2795 | 3 | 4 | 5 | 6 | 7 | VII-1 | Gm13298 |
| 2796 | 3 | 4 | 5 | 6 | 7 | VII-1 | Gm13305 |
| 2797 | 3 | 4 | 5 | 6 | 7 | VII-1 | Gm13306 |
| 2798 | 3 | 4 | 5 | 6 | 7 | VII-1 | Gm13308 |
| 2799 | 3 | 4 | 5 | 6 | 7 | VII-1 | Gm13363 |
| 2800 | 3 | 4 | 5 | 6 | 7 | VII-1 | Gm13547 |
| 2801 | 3 | 4 | 5 | 6 | 7 | VII-1 | Gm13826 |
| 2802 | 3 | 4 | 5 | 6 | 7 | VII-1 | Gm13889 |
| 2803 | 3 | 4 | 5 | 6 | 7 | VII-1 | Gm14288 |
| 2804 | 3 | 4 | 5 | 6 | 7 | VII-1 | Gm14378 |
| 2805 | 3 | 4 | 5 | 6 | 7 | VII-1 | Gm14391 |
| 2806 | 3 | 4 | 5 | 6 | 7 | VII-1 | Gm14446 |
| 2807 | 3 | 4 | 5 | 6 | 7 | VII-1 | Gm14461 |
| 2808 | 3 | 4 | 5 | 6 | 7 | VII-1 | Gm15133 |
| 2809 | 3 | 4 | 5 | 6 | 7 | VII-1 | Gm15284 |
| 2810 | 3 | 4 | 5 | 6 | 7 | VII-1 | Gm15417 |
| 2811 | 3 | 4 | 5 | 6 | 7 | VII-1 | Gm15421 |
| 2812 | 3 | 4 | 5 | 6 | 7 | VII-1 | Gm15471 |
| 2813 | 3 | 4 | 5 | 6 | 7 | VII-1 | Gm15772 |
| 2814 | 3 | 4 | 5 | 6 | 7 | VII-1 | Gm15850 |
| 2815 | 3 | 4 | 5 | 6 | 7 | VII-1 | Gm16062 |
| 2816 | 3 | 4 | 5 | 6 | 7 | VII-1 | Gm16381 |
| 2817 | 3 | 4 | 5 | 6 | 7 | VII-1 | Gm166 |
| 2818 | 3 | 4 | 5 | 6 | 7 | VII-1 | Gm1673 |
| 2819 | 3 | 4 | 5 | 6 | 7 | VII-1 | Gm16740 |
| 2820 | 3 | 4 | 5 | 6 | 7 | VII-1 | Gm17757 |
| 2821 | 3 | 4 | 5 | 6 | 7 | VII-1 | Gm1943 |
| 2822 | 3 | 4 | 5 | 6 | 7 | VII-1 | Gm1966 |
| 2823 | 3 | 4 | 5 | 6 | 7 | VII-1 | Gm2002 |
| 2824 | 3 | 4 | 5 | 6 | 7 | VII-1 | Gm20604 |
| 2825 | 3 | 4 | 5 | 6 | 7 | VII-1 | Gm2083 |
| 2826 | 3 | 4 | 5 | 6 | 7 | VII-1 | Gm20878 |
| 2827 | 3 | 4 | 5 | 6 | 7 | VII-1 | Gm21586 |
| 2828 | 3 | 4 | 5 | 6 | 7 | VII-1 | Gm2663 |
| 2829 | 3 | 4 | 5 | 6 | 7 | VII-1 | Gm2696 |
| 2830 | 3 | 4 | 5 | 6 | 7 | VII-1 | Gm2897 |
| 2831 | 3 | 4 | 5 | 6 | 7 | VII-1 | Gm2913 |
| 2832 | 3 | 4 | 5 | 6 | 7 | VII-1 | Gm3219 |
| 2833 | 3 | 4 | 5 | 6 | 7 | VII-1 | Gm3417 |
| 2834 | 3 | 4 | 5 | 6 | 7 | VII-1 | Gm3500 |
| 2835 | 3 | 4 | 5 | 6 | 7 | VII-1 | Gm3696 |
| 2836 | 3 | 4 | 5 | 6 | 7 | VII-1 | Gm3893 |
| 2837 | 3 | 4 | 5 | 6 | 7 | VII-1 | Gm4013 |
| 2838 | 3 | 4 | 5 | 6 | 7 | VII-1 | Gm4070 |
| 2839 | 3 | 4 | 5 | 6 | 7 | VII-1 | Gm4951 |
| 2840 | 3 | 4 | 5 | 6 | 7 | VII-1 | Gm5 |
| 2841 | 3 | 4 | 5 | 6 | 7 | VII-1 | Gm525 |
| 2842 | 3 | 4 | 5 | 6 | 7 | VII-1 | Gm5441 |
| 2843 | 3 | 4 | 5 | 6 | 7 | VII-1 | Gm5483 |
| 2844 | 3 | 4 | 5 | 6 | 7 | VII-1 | Gm5512 |
| 2845 | 3 | 4 | 5 | 6 | 7 | VII-1 | Gm561 |
| 2846 | 3 | 4 | 5 | 6 | 7 | VII-1 | Gm5617 |
| 2847 | 3 | 4 | 5 | 6 | 7 | VII-1 | Gm5627 |
| 2848 | 3 | 4 | 5 | 6 | 7 | VII-1 | Gm5741 |
| 2849 | 3 | 4 | 5 | 6 | 7 | VII-1 | Gm5771 |
| 2850 | 3 | 4 | 5 | 6 | 7 | VII-1 | Gm6251 |
| 2851 | 3 | 4 | 5 | 6 | 7 | VII-1 | Gm6537 |
| 2852 | 3 | 4 | 5 | 6 | 7 | VII-1 | Gm6568 |
| 2853 | 3 | 4 | 5 | 6 | 7 | VII-1 | Gm6607 |
| 2854 | 3 | 4 | 5 | 6 | 7 | VII-1 | Gm6644 |
| 2855 | 3 | 4 | 5 | 6 | 7 | VII-1 | Gm6654 |
| 2856 | 3 | 4 | 5 | 6 | 7 | VII-1 | Gm694 |
| 2857 | 3 | 4 | 5 | 6 | 7 | VII-1 | Gm7325 |
| 2858 | 3 | 4 | 5 | 6 | 7 | VII-1 | Gm7334 |
| 2859 | 3 | 4 | 5 | 6 | 7 | VII-1 | Gm7367 |
| 2860 | 3 | 4 | 5 | 6 | 7 | VII-1 | Gm766 |
| 2861 | 3 | 4 | 5 | 6 | 7 | VII-1 | Gm8909 |
| 2862 | 3 | 4 | 5 | 6 | 7 | VII-1 | Gm8979 |
| 2863 | 3 | 4 | 5 | 6 | 7 | VII-1 | Gm8989 |
| 2864 | 3 | 4 | 5 | 6 | 7 | VII-1 | Gmds |
| 2865 | 3 | 4 | 5 | 6 | 7 | VII-1 | Gmfg |
| 2866 | 3 | 4 | 5 | 6 | 7 | VII-1 | Gmppa |
| 2867 | 3 | 4 | 5 | 6 | 7 | VII-1 | Gmppb |
| 2868 | 3 | 4 | 5 | 6 | 7 | VII-1 | Gmpr |
| 2869 | 3 | 4 | 5 | 6 | 7 | VII-1 | Gnao1 |
| 2870 | 3 | 4 | 5 | 6 | 7 | VII-1 | Gng3 |
| 2871 | 3 | 4 | 5 | 6 | 7 | VII-1 | Gng7 |
| 2872 | 3 | 4 | 5 | 6 | 7 | VII-1 | Gngt2 |
| 2873 | 3 | 4 | 5 | 6 | 7 | VII-1 | Gnl1 |
| 2874 | 3 | 4 | 5 | 6 | 7 | VII-1 | Gnmt |
| 2875 | 3 | 4 | 5 | 6 | 7 | VII-1 | Gnpnat1 |
| 2876 | 3 | 4 | 5 | 6 | 7 | VII-1 | Gnrh1 |
| 2877 | 3 | 4 | 5 | 6 | 7 | VII-1 | Gon4l |
| 2878 | 3 | 4 | 5 | 6 | 7 | VII-1 | Got1 |

Fig. 34 - 16

| | | | | | | | |
|---|---|---|---|---|---|---|---|
| 2879 | 3 | 4 | 5 | 6 | 7 | VII-1 | Gp1bb |
| 2880 | 3 | 4 | 5 | 6 | 7 | VII-1 | Gp2 |
| 2881 | 3 | 4 | 5 | 6 | 7 | VII-1 | Gpaa1 |
| 2882 | 3 | 4 | 5 | 6 | 7 | VII-1 | Gpank1 |
| 2883 | 3 | 4 | 5 | 6 | 7 | VII-1 | Gpatch3 |
| 2884 | 3 | 4 | 5 | 6 | 7 | VII-1 | Gpcpd1 |
| 2885 | 3 | 4 | 5 | 6 | 7 | VII-1 | Gpi1 |
| 2886 | 3 | 4 | 5 | 6 | 7 | VII-1 | Gpihbp1 |
| 2887 | 3 | 4 | 5 | 6 | 7 | VII-1 | Gpm6a |
| 2888 | 3 | 4 | 5 | 6 | 7 | VII-1 | Gpn1 |
| 2889 | 3 | 4 | 5 | 6 | 7 | VII-1 | Gpnmb |
| 2890 | 3 | 4 | 5 | 6 | 7 | VII-1 | Gpr137b-ps |
| 2891 | 3 | 4 | 5 | 6 | 7 | VII-1 | Gpr3711 |
| 2892 | 3 | 4 | 5 | 6 | 7 | VII-1 | Gpr4 |
| 2893 | 3 | 4 | 5 | 6 | 7 | VII-1 | Gpr64 |
| 2894 | 3 | 4 | 5 | 6 | 7 | VII-1 | Gpr89 |
| 2895 | 3 | 4 | 5 | 6 | 7 | VII-1 | Gpr97 |
| 2896 | 3 | 4 | 5 | 6 | 7 | VII-1 | Gprc5a |
| 2897 | 3 | 4 | 5 | 6 | 7 | VII-1 | Gpsm3 |
| 2898 | 3 | 4 | 5 | 6 | 7 | VII-1 | Gpx1 |
| 2899 | 3 | 4 | 5 | 6 | 7 | VII-1 | Gpx3 |
| 2900 | 3 | 4 | 5 | 6 | 7 | VII-1 | Gpx4 |
| 2901 | 3 | 4 | 5 | 6 | 7 | VII-1 | Gramd3 |
| 2902 | 3 | 4 | 5 | 6 | 7 | VII-1 | Grcc10 |
| 2903 | 3 | 4 | 5 | 6 | 7 | VII-1 | Grhpr |
| 2904 | 3 | 4 | 5 | 6 | 7 | VII-1 | Gria1 |
| 2905 | 3 | 4 | 5 | 6 | 7 | VII-1 | Gria2 |
| 2906 | 3 | 4 | 5 | 6 | 7 | VII-1 | Grin1 |
| 2907 | 3 | 4 | 5 | 6 | 7 | VII-1 | Grpel2 |
| 2908 | 3 | 4 | 5 | 6 | 7 | VII-1 | Grrp1 |
| 2909 | 3 | 4 | 5 | 6 | 7 | VII-1 | Gsg1 |
| 2910 | 3 | 4 | 5 | 6 | 7 | VII-1 | Gskip |
| 2911 | 3 | 4 | 5 | 6 | 7 | VII-1 | Gsn |
| 2912 | 3 | 4 | 5 | 6 | 7 | VII-1 | Gss |
| 2913 | 3 | 4 | 5 | 6 | 7 | VII-1 | Gsta3 |
| 2914 | 3 | 4 | 5 | 6 | 7 | VII-1 | Gstk1 |
| 2915 | 3 | 4 | 5 | 6 | 7 | VII-1 | Gstm2 |
| 2916 | 3 | 4 | 5 | 6 | 7 | VII-1 | Gstm5 |
| 2917 | 3 | 4 | 5 | 6 | 7 | VII-1 | Gstm6 |
| 2918 | 3 | 4 | 5 | 6 | 7 | VII-1 | Gstm7 |
| 2919 | 3 | 4 | 5 | 6 | 7 | VII-1 | Gstp1 |
| 2920 | 3 | 4 | 5 | 6 | 7 | VII-1 | Gstp2 |
| 2921 | 3 | 4 | 5 | 6 | 7 | VII-1 | Gstt2 |
| 2922 | 3 | 4 | 5 | 6 | 7 | VII-1 | Gtf2b |
| 2923 | 3 | 4 | 5 | 6 | 7 | VII-1 | Gtf2f2 |
| 2924 | 3 | 4 | 5 | 6 | 7 | VII-1 | Gtf2h4 |
| 2925 | 3 | 4 | 5 | 6 | 7 | VII-1 | Gtf2h5 |
| 2926 | 3 | 4 | 5 | 6 | 7 | VII-1 | Gtf3c6 |
| 2927 | 3 | 4 | 5 | 6 | 7 | VII-1 | Gti3 |
| 2928 | 3 | 4 | 5 | 6 | 7 | VII-1 | Gtpbp6 |
| 2929 | 3 | 4 | 5 | 6 | 7 | VII-1 | Guca1a |
| 2930 | 3 | 4 | 5 | 6 | 7 | VII-1 | Guca2a |
| 2931 | 3 | 4 | 5 | 6 | 7 | VII-1 | Guca2b |
| 2932 | 3 | 4 | 5 | 6 | 7 | VII-1 | Gusb |
| 2933 | 3 | 4 | 5 | 6 | 7 | VII-1 | Gxylt2 |
| 2934 | 3 | 4 | 5 | 6 | 7 | VII-1 | Gys2 |
| 2935 | 3 | 4 | 5 | 6 | 7 | VII-1 | Gzmm |
| 2936 | 3 | 4 | 5 | 6 | 7 | VII-1 | H13 |
| 2937 | 3 | 4 | 5 | 6 | 7 | VII-1 | H1fx |
| 2938 | 3 | 4 | 5 | 6 | 7 | VII-1 | H2-Bl |
| 2939 | 3 | 4 | 5 | 6 | 7 | VII-1 | H2-D1 |
| 2940 | 3 | 4 | 5 | 6 | 7 | VII-1 | H2-Ea-ps |
| 2941 | 3 | 4 | 5 | 6 | 7 | VII-1 | H2-K2 |
| 2942 | 3 | 4 | 5 | 6 | 7 | VII-1 | H2-Ke2 |
| 2943 | 3 | 4 | 5 | 6 | 7 | VII-1 | H2-Ke6 |
| 2944 | 3 | 4 | 5 | 6 | 7 | VII-1 | H2-Q1 |
| 2945 | 3 | 4 | 5 | 6 | 7 | VII-1 | H2-Q10 |
| 2946 | 3 | 4 | 5 | 6 | 7 | VII-1 | H2-T22 |
| 2947 | 3 | 4 | 5 | 6 | 7 | VII-1 | H2afb1 |
| 2948 | 3 | 4 | 5 | 6 | 7 | VII-1 | H2afj |
| 2949 | 3 | 4 | 5 | 6 | 7 | VII-1 | H2afv |
| 2950 | 3 | 4 | 5 | 6 | 7 | VII-1 | H60c |
| 2951 | 3 | 4 | 5 | 6 | 7 | VII-1 | Hadha |
| 2952 | 3 | 4 | 5 | 6 | 7 | VII-1 | Haghl |
| 2953 | 3 | 4 | 5 | 6 | 7 | VII-1 | Hal |
| 2954 | 3 | 4 | 5 | 6 | 7 | VII-1 | Hamp |
| 2955 | 3 | 4 | 5 | 6 | 7 | VII-1 | Hamp2 |
| 2956 | 3 | 4 | 5 | 6 | 7 | VII-1 | Hapln4 |
| 2957 | 3 | 4 | 5 | 6 | 7 | VII-1 | Haus7 |
| 2958 | 3 | 4 | 5 | 6 | 7 | VII-1 | Haus8 |
| 2959 | 3 | 4 | 5 | 6 | 7 | VII-1 | Hax1 |
| 2960 | 3 | 4 | 5 | 6 | 7 | VII-1 | Hba-a1 |
| 2961 | 3 | 4 | 5 | 6 | 7 | VII-1 | Hba-a2 |
| 2962 | 3 | 4 | 5 | 6 | 7 | VII-1 | Hbb-b1 |
| 2963 | 3 | 4 | 5 | 6 | 7 | VII-1 | Hbb-bs |
| 2964 | 3 | 4 | 5 | 6 | 7 | VII-1 | Hbb-bt |
| 2965 | 3 | 4 | 5 | 6 | 7 | VII-1 | Hbs1l |
| 2966 | 3 | 4 | 5 | 6 | 7 | VII-1 | Hcfc1r1 |
| 2967 | 3 | 4 | 5 | 6 | 7 | VII-1 | Hcls1 |
| 2968 | 3 | 4 | 5 | 6 | 7 | VII-1 | Hcn2 |
| 2969 | 3 | 4 | 5 | 6 | 7 | VII-1 | Hcrtr1 |
| 2970 | 3 | 4 | 5 | 6 | 7 | VII-1 | Hcst |
| 2971 | 3 | 4 | 5 | 6 | 7 | VII-1 | Hdac10 |
| 2972 | 3 | 4 | 5 | 6 | 7 | VII-1 | Hddc2 |
| 2973 | 3 | 4 | 5 | 6 | 7 | VII-1 | Hdgfrp2 |
| 2974 | 3 | 4 | 5 | 6 | 7 | VII-1 | Hebp2 |
| 2975 | 3 | 4 | 5 | 6 | 7 | VII-1 | Hexa |
| 2976 | 3 | 4 | 5 | 6 | 7 | VII-1 | Hgd |
| 2977 | 3 | 4 | 5 | 6 | 7 | VII-1 | Hgf |
| 2978 | 3 | 4 | 5 | 6 | 7 | VII-1 | Hgs |
| 2979 | 3 | 4 | 5 | 6 | 7 | VII-1 | Hhatl |
| 2980 | 3 | 4 | 5 | 6 | 7 | VII-1 | Higd1b |
| 2981 | 3 | 4 | 5 | 6 | 7 | VII-1 | Hilpda |
| 2982 | 3 | 4 | 5 | 6 | 7 | VII-1 | Hils1 |
| 2983 | 3 | 4 | 5 | 6 | 7 | VII-1 | Hint1 |
| 2984 | 3 | 4 | 5 | 6 | 7 | VII-1 | Hint2 |
| 2985 | 3 | 4 | 5 | 6 | 7 | VII-1 | Hip1r |
| 2986 | 3 | 4 | 5 | 6 | 7 | VII-1 | Hipk2 |
| 2987 | 3 | 4 | 5 | 6 | 7 | VII-1 | Hist1h1c |
| 2988 | 3 | 4 | 5 | 6 | 7 | VII-1 | Hist1h2ah |
| 2989 | 3 | 4 | 5 | 6 | 7 | VII-1 | Hist1h2ai |
| 2990 | 3 | 4 | 5 | 6 | 7 | VII-1 | Hist1h2ba |
| 2991 | 3 | 4 | 5 | 6 | 7 | VII-1 | Hist1h2bc |
| 2992 | 3 | 4 | 5 | 6 | 7 | VII-1 | Hist1h2be |
| 2993 | 3 | 4 | 5 | 6 | 7 | VII-1 | Hist1h2bg |
| 2994 | 3 | 4 | 5 | 6 | 7 | VII-1 | Hist1h2bj |
| 2995 | 3 | 4 | 5 | 6 | 7 | VII-1 | Hist1h4a |
| 2996 | 3 | 4 | 5 | 6 | 7 | VII-1 | Hist1h4b |
| 2997 | 3 | 4 | 5 | 6 | 7 | VII-1 | Hist1h4c |
| 2998 | 3 | 4 | 5 | 6 | 7 | VII-1 | Hist1h4f |
| 2999 | 3 | 4 | 5 | 6 | 7 | VII-1 | Hist1h4h |
| 3000 | 3 | 4 | 5 | 6 | 7 | VII-1 | Hist1h4i |
| 3001 | 3 | 4 | 5 | 6 | 7 | VII-1 | Hist1h4j |
| 3002 | 3 | 4 | 5 | 6 | 7 | VII-1 | Hist1h4k |
| 3003 | 3 | 4 | 5 | 6 | 7 | VII-1 | Hist1h4n |
| 3004 | 3 | 4 | 5 | 6 | 7 | VII-1 | Hist2h2aa1 |
| 3005 | 3 | 4 | 5 | 6 | 7 | VII-1 | Hist2h2aa2 |
| 3006 | 3 | 4 | 5 | 6 | 7 | VII-1 | Hist2h2ac |
| 3007 | 3 | 4 | 5 | 6 | 7 | VII-1 | Hist2h3c1 |
| 3008 | 3 | 4 | 5 | 6 | 7 | VII-1 | Hmg20b |
| 3009 | 3 | 4 | 5 | 6 | 7 | VII-1 | Hmga1-rs1 |
| 3010 | 3 | 4 | 5 | 6 | 7 | VII-1 | Hmgb4 |
| 3011 | 3 | 4 | 5 | 6 | 7 | VII-1 | Hmgcl |
| 3012 | 3 | 4 | 5 | 6 | 7 | VII-1 | Hmgcs2 |
| 3013 | 3 | 4 | 5 | 6 | 7 | VII-1 | Hmgn1 |
| 3014 | 3 | 4 | 5 | 6 | 7 | VII-1 | Hmox1 |
| 3015 | 3 | 4 | 5 | 6 | 7 | VII-1 | Hnrnpa1 |
| 3016 | 3 | 4 | 5 | 6 | 7 | VII-1 | Homer3 |
| 3017 | 3 | 4 | 5 | 6 | 7 | VII-1 | Hoxb7 |
| 3018 | 3 | 4 | 5 | 6 | 7 | VII-1 | Hp |
| 3019 | 3 | 4 | 5 | 6 | 7 | VII-1 | Hpca |
| 3020 | 3 | 4 | 5 | 6 | 7 | VII-1 | Hpcal4 |
| 3021 | 3 | 4 | 5 | 6 | 7 | VII-1 | Hpd |
| 3022 | 3 | 4 | 5 | 6 | 7 | VII-1 | Hpgd |
| 3023 | 3 | 4 | 5 | 6 | 7 | VII-1 | Hps1 |
| 3024 | 3 | 4 | 5 | 6 | 7 | VII-1 | Hr |
| 3025 | 3 | 4 | 5 | 6 | 7 | VII-1 | Hras |
| 3026 | 3 | 4 | 5 | 6 | 7 | VII-1 | Hrasls5 |
| 3027 | 3 | 4 | 5 | 6 | 7 | VII-1 | Hrct1 |
| 3028 | 3 | 4 | 5 | 6 | 7 | VII-1 | Hrsp12 |
| 3029 | 3 | 4 | 5 | 6 | 7 | VII-1 | Hsd17b10 |
| 3030 | 3 | 4 | 5 | 6 | 7 | VII-1 | Hsd17b11 |
| 3031 | 3 | 4 | 5 | 6 | 7 | VII-1 | Hsd17b7 |
| 3032 | 3 | 4 | 5 | 6 | 7 | VII-1 | Hspa1a |
| 3033 | 3 | 4 | 5 | 6 | 7 | VII-1 | Hspa1b |
| 3034 | 3 | 4 | 5 | 6 | 7 | VII-1 | Hspa2 |
| 3035 | 3 | 4 | 5 | 6 | 7 | VII-1 | Hspb1 |
| 3036 | 3 | 4 | 5 | 6 | 7 | VII-1 | Hspb11 |
| 3037 | 3 | 4 | 5 | 6 | 7 | VII-1 | Hspb2 |
| 3038 | 3 | 4 | 5 | 6 | 7 | VII-1 | Hspb3 |
| 3039 | 3 | 4 | 5 | 6 | 7 | VII-1 | Hspb9 |
| 3040 | 3 | 4 | 5 | 6 | 7 | VII-1 | Hspbp1 |
| 3041 | 3 | 4 | 5 | 6 | 7 | VII-1 | Htatip2 |
| 3042 | 3 | 4 | 5 | 6 | 7 | VII-1 | Htr5b |
| 3043 | 3 | 4 | 5 | 6 | 7 | VII-1 | Htra3 |
| 3044 | 3 | 4 | 5 | 6 | 7 | VII-1 | Hyi |
| 3045 | 3 | 4 | 5 | 6 | 7 | VII-1 | Hyls1 |
| 3046 | 3 | 4 | 5 | 6 | 7 | VII-1 | I830012O16Rik |
| 3047 | 3 | 4 | 5 | 6 | 7 | VII-1 | Icam2 |
| 3048 | 3 | 4 | 5 | 6 | 7 | VII-1 | Ict1 |
| 3049 | 3 | 4 | 5 | 6 | 7 | VII-1 | Idnk |
| 3050 | 3 | 4 | 5 | 6 | 7 | VII-1 | Ier2 |
| 3051 | 3 | 4 | 5 | 6 | 7 | VII-1 | Ier5 |
| 3052 | 3 | 4 | 5 | 6 | 7 | VII-1 | Ier5l |
| 3053 | 3 | 4 | 5 | 6 | 7 | VII-1 | Ifi203 |
| 3054 | 3 | 4 | 5 | 6 | 7 | VII-1 | Ifi204 |
| 3055 | 3 | 4 | 5 | 6 | 7 | VII-1 | Ifi205 |
| 3056 | 3 | 4 | 5 | 6 | 7 | VII-1 | Ifi27 |
| 3057 | 3 | 4 | 5 | 6 | 7 | VII-1 | Ifi27l2a |
| 3058 | 3 | 4 | 5 | 6 | 7 | VII-1 | Ifi35 |
| 3059 | 3 | 4 | 5 | 6 | 7 | VII-1 | Ifi44 |
| 3060 | 3 | 4 | 5 | 6 | 7 | VII-1 | Ifi47 |
| 3061 | 3 | 4 | 5 | 6 | 7 | VII-1 | Ifit1 |
| 3062 | 3 | 4 | 5 | 6 | 7 | VII-1 | Ifit3 |
| 3063 | 3 | 4 | 5 | 6 | 7 | VII-1 | Ifitm2 |
| 3064 | 3 | 4 | 5 | 6 | 7 | VII-1 | Ifrd1 |
| 3065 | 3 | 4 | 5 | 6 | 7 | VII-1 | Ift22 |
| 3066 | 3 | 4 | 5 | 6 | 7 | VII-1 | Ift27 |
| 3067 | 3 | 4 | 5 | 6 | 7 | VII-1 | Ift43 |
| 3068 | 3 | 4 | 5 | 6 | 7 | VII-1 | Ift46 |
| 3069 | 3 | 4 | 5 | 6 | 7 | VII-1 | Igfbp1 |
| 3070 | 3 | 4 | 5 | 6 | 7 | VII-1 | Igfbp2 |

Fig. 34 - 17

| | | | | | | | |
|---|---|---|---|---|---|---|---|
| 3071 | 3 | 4 | 5 | 6 | 7 | VII-1 | Igf1r1 |
| 3072 | 3 | 4 | 5 | 6 | 7 | VII-1 | Igj |
| 3073 | 3 | 4 | 5 | 6 | 7 | VII-1 | Igtp |
| 3074 | 3 | 4 | 5 | 6 | 7 | VII-1 | Ikbke |
| 3075 | 3 | 4 | 5 | 6 | 7 | VII-1 | Il11ra1 |
| 3076 | 3 | 4 | 5 | 6 | 7 | VII-1 | Il11ra2 |
| 3077 | 3 | 4 | 5 | 6 | 7 | VII-1 | Il17b |
| 3078 | 3 | 4 | 5 | 6 | 7 | VII-1 | Il17rc |
| 3079 | 3 | 4 | 5 | 6 | 7 | VII-1 | Il18 |
| 3080 | 3 | 4 | 5 | 6 | 7 | VII-1 | Il1r2 |
| 3081 | 3 | 4 | 5 | 6 | 7 | VII-1 | Il3ra |
| 3082 | 3 | 4 | 5 | 6 | 7 | VII-1 | Il5ra |
| 3083 | 3 | 4 | 5 | 6 | 7 | VII-1 | Il6ra |
| 3084 | 3 | 4 | 5 | 6 | 7 | VII-1 | Ilf2 |
| 3085 | 3 | 4 | 5 | 6 | 7 | VII-1 | Ikap |
| 3086 | 3 | 4 | 5 | 6 | 7 | VII-1 | Immp1l |
| 3087 | 3 | 4 | 5 | 6 | 7 | VII-1 | Immp2l |
| 3088 | 3 | 4 | 5 | 6 | 7 | VII-1 | Impdh1 |
| 3089 | 3 | 4 | 5 | 6 | 7 | VII-1 | Ina |
| 3090 | 3 | 4 | 5 | 6 | 7 | VII-1 | Inca1 |
| 3091 | 3 | 4 | 5 | 6 | 7 | VII-1 | Inmt |
| 3092 | 3 | 4 | 5 | 6 | 7 | VII-1 | Ino80b |
| 3093 | 3 | 4 | 5 | 6 | 7 | VII-1 | Inpp5a |
| 3094 | 3 | 4 | 5 | 6 | 7 | VII-1 | Ins2 |
| 3095 | 3 | 4 | 5 | 6 | 7 | VII-1 | Insig2 |
| 3096 | 3 | 4 | 5 | 6 | 7 | VII-1 | Insl3 |
| 3097 | 3 | 4 | 5 | 6 | 7 | VII-1 | Ints1 |
| 3098 | 3 | 4 | 5 | 6 | 7 | VII-1 | Ints3 |
| 3099 | 3 | 4 | 5 | 6 | 7 | VII-1 | Ipo5 |
| 3100 | 3 | 4 | 5 | 6 | 7 | VII-1 | Iqcj |
| 3101 | 3 | 4 | 5 | 6 | 7 | VII-1 | Iqck |
| 3102 | 3 | 4 | 5 | 6 | 7 | VII-1 | Irf4 |
| 3103 | 3 | 4 | 5 | 6 | 7 | VII-1 | Irf7 |
| 3104 | 3 | 4 | 5 | 6 | 7 | VII-1 | Irgc1 |
| 3105 | 3 | 4 | 5 | 6 | 7 | VII-1 | Irs2 |
| 3106 | 3 | 4 | 5 | 6 | 7 | VII-1 | Isg15 |
| 3107 | 3 | 4 | 5 | 6 | 7 | VII-1 | Isoc2a |
| 3108 | 3 | 4 | 5 | 6 | 7 | VII-1 | Isoc2b |
| 3109 | 3 | 4 | 5 | 6 | 7 | VII-1 | Isyna1 |
| 3110 | 3 | 4 | 5 | 6 | 7 | VII-1 | Itga11 |
| 3111 | 3 | 4 | 5 | 6 | 7 | VII-1 | Itga2b |
| 3112 | 3 | 4 | 5 | 6 | 7 | VII-1 | Itgb1bp2 |
| 3113 | 3 | 4 | 5 | 6 | 7 | VII-1 | Itgb5 |
| 3114 | 3 | 4 | 5 | 6 | 7 | VII-1 | Itih4 |
| 3115 | 3 | 4 | 5 | 6 | 7 | VII-1 | Itih5 |
| 3116 | 3 | 4 | 5 | 6 | 7 | VII-1 | Itln1 |
| 3117 | 3 | 4 | 5 | 6 | 7 | VII-1 | Itm2a |
| 3118 | 3 | 4 | 5 | 6 | 7 | VII-1 | Itpka |
| 3119 | 3 | 4 | 5 | 6 | 7 | VII-1 | Izumo4 |
| 3120 | 3 | 4 | 5 | 6 | 7 | VII-1 | Jmjd8 |
| 3121 | 3 | 4 | 5 | 6 | 7 | VII-1 | Josd2 |
| 3122 | 3 | 4 | 5 | 6 | 7 | VII-1 | Jph3 |
| 3123 | 3 | 4 | 5 | 6 | 7 | VII-1 | Jph4 |
| 3124 | 3 | 4 | 5 | 6 | 7 | VII-1 | Jsrp1 |
| 3125 | 3 | 4 | 5 | 6 | 7 | VII-1 | Junb |
| 3126 | 3 | 4 | 5 | 6 | 7 | VII-1 | Kap |
| 3127 | 3 | 4 | 5 | 6 | 7 | VII-1 | Kbtbd3 |
| 3128 | 3 | 4 | 5 | 6 | 7 | VII-1 | Kcnc1 |
| 3129 | 3 | 4 | 5 | 6 | 7 | VII-1 | Kcnj11 |
| 3130 | 3 | 4 | 5 | 6 | 7 | VII-1 | Kcnj4 |
| 3131 | 3 | 4 | 5 | 6 | 7 | VII-1 | Kcnk1 |
| 3132 | 3 | 4 | 5 | 6 | 7 | VII-1 | Kcnk3 |
| 3133 | 3 | 4 | 5 | 6 | 7 | VII-1 | Kcnk7 |
| 3134 | 3 | 4 | 5 | 6 | 7 | VII-1 | Kcnq2 |
| 3135 | 3 | 4 | 5 | 6 | 7 | VII-1 | Kdelr2 |
| 3136 | 3 | 4 | 5 | 6 | 7 | VII-1 | Kdm7a |
| 3137 | 3 | 4 | 5 | 6 | 7 | VII-1 | Khk |
| 3138 | 3 | 4 | 5 | 6 | 7 | VII-1 | Kif1a |
| 3139 | 3 | 4 | 5 | 6 | 7 | VII-1 | Kif5a |
| 3140 | 3 | 4 | 5 | 6 | 7 | VII-1 | Kif5c |
| 3141 | 3 | 4 | 5 | 6 | 7 | VII-1 | Kiss1 |
| 3142 | 3 | 4 | 5 | 6 | 7 | VII-1 | Klhdc3 |
| 3143 | 3 | 4 | 5 | 6 | 7 | VII-1 | Klhdc4 |
| 3144 | 3 | 4 | 5 | 6 | 7 | VII-1 | Klhl30 |
| 3145 | 3 | 4 | 5 | 6 | 7 | VII-1 | Klhl33 |
| 3146 | 3 | 4 | 5 | 6 | 7 | VII-1 | Klk13 |
| 3147 | 3 | 4 | 5 | 6 | 7 | VII-1 | Klk1b26 |
| 3148 | 3 | 4 | 5 | 6 | 7 | VII-1 | Klk6 |
| 3149 | 3 | 4 | 5 | 6 | 7 | VII-1 | Klk8 |
| 3150 | 3 | 4 | 5 | 6 | 7 | VII-1 | Klra17 |
| 3151 | 3 | 4 | 5 | 6 | 7 | VII-1 | Klra3 |
| 3152 | 3 | 4 | 5 | 6 | 7 | VII-1 | Klra5 |
| 3153 | 3 | 4 | 5 | 6 | 7 | VII-1 | Kncn |
| 3154 | 3 | 4 | 5 | 6 | 7 | VII-1 | Kng2 |
| 3155 | 3 | 4 | 5 | 6 | 7 | VII-1 | Kptn |
| 3156 | 3 | 4 | 5 | 6 | 7 | VII-1 | Kri1 |
| 3157 | 3 | 4 | 5 | 6 | 7 | VII-1 | Krt19 |
| 3158 | 3 | 4 | 5 | 6 | 7 | VII-1 | Krt32 |
| 3159 | 3 | 4 | 5 | 6 | 7 | VII-1 | Krt33b |
| 3160 | 3 | 4 | 5 | 6 | 7 | VII-1 | Krt79 |
| 3161 | 3 | 4 | 5 | 6 | 7 | VII-1 | Krtap10-10 |
| 3162 | 3 | 4 | 5 | 6 | 7 | VII-1 | Krtap22-2 |
| 3163 | 3 | 4 | 5 | 6 | 7 | VII-1 | Krtap3-2 |
| 3164 | 3 | 4 | 5 | 6 | 7 | VII-1 | Krtap5-1 |
| 3165 | 3 | 4 | 5 | 6 | 7 | VII-1 | Krtap5-2 |
| 3166 | 3 | 4 | 5 | 6 | 7 | VII-1 | Krtdap |
| 3167 | 3 | 4 | 5 | 6 | 7 | VII-1 | LOC100038947 |
| 3168 | 3 | 4 | 5 | 6 | 7 | VII-1 | LOC100504703 |
| 3169 | 3 | 4 | 5 | 6 | 7 | VII-1 | LOC100861615 |
| 3170 | 3 | 4 | 5 | 6 | 7 | VII-1 | LOC100861978 |
| 3171 | 3 | 4 | 5 | 6 | 7 | VII-1 | LOC101669761 |
| 3172 | 3 | 4 | 5 | 6 | 7 | VII-1 | LOC102632423 |
| 3173 | 3 | 4 | 5 | 6 | 7 | VII-1 | Lama3 |
| 3174 | 3 | 4 | 5 | 6 | 7 | VII-1 | Lama4 |
| 3175 | 3 | 4 | 5 | 6 | 7 | VII-1 | Lamc2 |
| 3176 | 3 | 4 | 5 | 6 | 7 | VII-1 | Lamp5 |
| 3177 | 3 | 4 | 5 | 6 | 7 | VII-1 | Lamtor2 |
| 3178 | 3 | 4 | 5 | 6 | 7 | VII-1 | Lamtor3 |
| 3179 | 3 | 4 | 5 | 6 | 7 | VII-1 | Lamtor4 |
| 3180 | 3 | 4 | 5 | 6 | 7 | VII-1 | Lars |
| 3181 | 3 | 4 | 5 | 6 | 7 | VII-1 | Lars2 |
| 3182 | 3 | 4 | 5 | 6 | 7 | VII-1 | Lat |
| 3183 | 3 | 4 | 5 | 6 | 7 | VII-1 | Lbp |
| 3184 | 3 | 4 | 5 | 6 | 7 | VII-1 | Lce1f |
| 3185 | 3 | 4 | 5 | 6 | 7 | VII-1 | Lce1g |
| 3186 | 3 | 4 | 5 | 6 | 7 | VII-1 | Lce1j |
| 3187 | 3 | 4 | 5 | 6 | 7 | VII-1 | Lce1m |
| 3188 | 3 | 4 | 5 | 6 | 7 | VII-1 | Lce3c |
| 3189 | 3 | 4 | 5 | 6 | 7 | VII-1 | Lce3d |
| 3190 | 3 | 4 | 5 | 6 | 7 | VII-1 | Lce3f |
| 3191 | 3 | 4 | 5 | 6 | 7 | VII-1 | Lcmt1 |
| 3192 | 3 | 4 | 5 | 6 | 7 | VII-1 | Lcn2 |
| 3193 | 3 | 4 | 5 | 6 | 7 | VII-1 | Ldhal6b |
| 3194 | 3 | 4 | 5 | 6 | 7 | VII-1 | Ldhb |
| 3195 | 3 | 4 | 5 | 6 | 7 | VII-1 | Ldhc |
| 3196 | 3 | 4 | 5 | 6 | 7 | VII-1 | Ldlr |
| 3197 | 3 | 4 | 5 | 6 | 7 | VII-1 | Leng1 |
| 3198 | 3 | 4 | 5 | 6 | 7 | VII-1 | Lepr |
| 3199 | 3 | 4 | 5 | 6 | 7 | VII-1 | Lgals1 |
| 3200 | 3 | 4 | 5 | 6 | 7 | VII-1 | Lgals4 |
| 3201 | 3 | 4 | 5 | 6 | 7 | VII-1 | Lgals7 |
| 3202 | 3 | 4 | 5 | 6 | 7 | VII-1 | Lgi3 |
| 3203 | 3 | 4 | 5 | 6 | 7 | VII-1 | Lgi4 |
| 3204 | 3 | 4 | 5 | 6 | 7 | VII-1 | Lhb |
| 3205 | 3 | 4 | 5 | 6 | 7 | VII-1 | Lhx1os |
| 3206 | 3 | 4 | 5 | 6 | 7 | VII-1 | Lifr |
| 3207 | 3 | 4 | 5 | 6 | 7 | VII-1 | Lig1 |
| 3208 | 3 | 4 | 5 | 6 | 7 | VII-1 | Lipe |
| 3209 | 3 | 4 | 5 | 6 | 7 | VII-1 | Liph |
| 3210 | 3 | 4 | 5 | 6 | 7 | VII-1 | Lmbr1l |
| 3211 | 3 | 4 | 5 | 6 | 7 | VII-1 | Lmcd1 |
| 3212 | 3 | 4 | 5 | 6 | 7 | VII-1 | Lmf1 |
| 3213 | 3 | 4 | 5 | 6 | 7 | VII-1 | Lmod2 |
| 3214 | 3 | 4 | 5 | 6 | 7 | VII-1 | Lmtk3 |
| 3215 | 3 | 4 | 5 | 6 | 7 | VII-1 | Lor |
| 3216 | 3 | 4 | 5 | 6 | 7 | VII-1 | Lox |
| 3217 | 3 | 4 | 5 | 6 | 7 | VII-1 | Lpcat3 |
| 3218 | 3 | 4 | 5 | 6 | 7 | VII-1 | Lpin2 |
| 3219 | 3 | 4 | 5 | 6 | 7 | VII-1 | Lrch4 |
| 3220 | 3 | 4 | 5 | 6 | 7 | VII-1 | Lrp11 |
| 3221 | 3 | 4 | 5 | 6 | 7 | VII-1 | Lrrc10 |
| 3222 | 3 | 4 | 5 | 6 | 7 | VII-1 | Lrrc20 |
| 3223 | 3 | 4 | 5 | 6 | 7 | VII-1 | Lrrc27 |
| 3224 | 3 | 4 | 5 | 6 | 7 | VII-1 | Lrrc30 |
| 3225 | 3 | 4 | 5 | 6 | 7 | VII-1 | Lrrc46 |
| 3226 | 3 | 4 | 5 | 6 | 7 | VII-1 | Lrrc4b |
| 3227 | 3 | 4 | 5 | 6 | 7 | VII-1 | Lrrc51 |
| 3228 | 3 | 4 | 5 | 6 | 7 | VII-1 | Lrrc73 |
| 3229 | 3 | 4 | 5 | 6 | 7 | VII-1 | Lrrc74 |
| 3230 | 3 | 4 | 5 | 6 | 7 | VII-1 | Lrrn2 |
| 3231 | 3 | 4 | 5 | 6 | 7 | VII-1 | Lrwd1 |
| 3232 | 3 | 4 | 5 | 6 | 7 | VII-1 | Lsm14a |
| 3233 | 3 | 4 | 5 | 6 | 7 | VII-1 | Lsm2 |
| 3234 | 3 | 4 | 5 | 6 | 7 | VII-1 | Lsm4 |
| 3235 | 3 | 4 | 5 | 6 | 7 | VII-1 | Lsm5 |
| 3236 | 3 | 4 | 5 | 6 | 7 | VII-1 | Lsm7 |
| 3237 | 3 | 4 | 5 | 6 | 7 | VII-1 | Lsm8 |
| 3238 | 3 | 4 | 5 | 6 | 7 | VII-1 | Lsp1 |
| 3239 | 3 | 4 | 5 | 6 | 7 | VII-1 | Lst1 |
| 3240 | 3 | 4 | 5 | 6 | 7 | VII-1 | Lta4h |
| 3241 | 3 | 4 | 5 | 6 | 7 | VII-1 | Ltc4s |
| 3242 | 3 | 4 | 5 | 6 | 7 | VII-1 | Ltf |
| 3243 | 3 | 4 | 5 | 6 | 7 | VII-1 | Lxn |
| 3244 | 3 | 4 | 5 | 6 | 7 | VII-1 | Ly6a |
| 3245 | 3 | 4 | 5 | 6 | 7 | VII-1 | Ly6d |
| 3246 | 3 | 4 | 5 | 6 | 7 | VII-1 | Ly6g6c |
| 3247 | 3 | 4 | 5 | 6 | 7 | VII-1 | Ly6g6d |
| 3248 | 3 | 4 | 5 | 6 | 7 | VII-1 | Ly6h |
| 3249 | 3 | 4 | 5 | 6 | 7 | VII-1 | Lypd2 |
| 3250 | 3 | 4 | 5 | 6 | 7 | VII-1 | Lypd8 |
| 3251 | 3 | 4 | 5 | 6 | 7 | VII-1 | Lyve1 |
| 3252 | 3 | 4 | 5 | 6 | 7 | VII-1 | Lyz1 |
| 3253 | 3 | 4 | 5 | 6 | 7 | VII-1 | Mad2l2 |
| 3254 | 3 | 4 | 5 | 6 | 7 | VII-1 | Mafb |
| 3255 | 3 | 4 | 5 | 6 | 7 | VII-1 | Maff |
| 3256 | 3 | 4 | 5 | 6 | 7 | VII-1 | Mag |
| 3257 | 3 | 4 | 5 | 6 | 7 | VII-1 | Magohb |
| 3258 | 3 | 4 | 5 | 6 | 7 | VII-1 | Mal2 |
| 3259 | 3 | 4 | 5 | 6 | 7 | VII-1 | Malat1 |
| 3260 | 3 | 4 | 5 | 6 | 7 | VII-1 | Malsu1 |
| 3261 | 3 | 4 | 5 | 6 | 7 | VII-1 | Man2c1 |
| 3262 | 3 | 4 | 5 | 6 | 7 | VII-1 | Map1a |

Fig. 34 - 18

| | | | | | | | |
|---|---|---|---|---|---|---|---|
| 3263 | 3 | 4 | 5 | 6 | 7 | VII-1 | Map1b |
| 3264 | 3 | 4 | 5 | 6 | 7 | VII-1 | Map1c3a |
| 3265 | 3 | 4 | 5 | 6 | 7 | VII-1 | Map2 |
| 3266 | 3 | 4 | 5 | 6 | 7 | VII-1 | Map2k2 |
| 3267 | 3 | 4 | 5 | 6 | 7 | VII-1 | Map3k6 |
| 3268 | 3 | 4 | 5 | 6 | 7 | VII-1 | Map6 |
| 3269 | 3 | 4 | 5 | 6 | 7 | VII-1 | Mapk12 |
| 3270 | 3 | 4 | 5 | 6 | 7 | VII-1 | Mapk13 |
| 3271 | 3 | 4 | 5 | 6 | 7 | VII-1 | Mapk8ip2 |
| 3272 | 3 | 4 | 5 | 6 | 7 | VII-1 | Mapt |
| 3273 | 3 | 4 | 5 | 6 | 7 | VII-1 | Marc1 |
| 3274 | 3 | 4 | 5 | 6 | 7 | VII-1 | Marc2 |
| 3275 | 3 | 4 | 5 | 6 | 7 | VII-1 | March7 |
| 3276 | 3 | 4 | 5 | 6 | 7 | VII-1 | Marco |
| 3277 | 3 | 4 | 5 | 6 | 7 | VII-1 | Mars |
| 3278 | 3 | 4 | 5 | 6 | 7 | VII-1 | Mat1a |
| 3279 | 3 | 4 | 5 | 6 | 7 | VII-1 | Matk |
| 3280 | 3 | 4 | 5 | 6 | 7 | VII-1 | Mb |
| 3281 | 3 | 4 | 5 | 6 | 7 | VII-1 | Mbd1 |
| 3282 | 3 | 4 | 5 | 6 | 7 | VII-1 | Mbp |
| 3283 | 3 | 4 | 5 | 6 | 7 | VII-1 | Mc2r |
| 3284 | 3 | 4 | 5 | 6 | 7 | VII-1 | Mc5r |
| 3285 | 3 | 4 | 5 | 6 | 7 | VII-1 | Mcee |
| 3286 | 3 | 4 | 5 | 6 | 7 | VII-1 | Mchr1 |
| 3287 | 3 | 4 | 5 | 6 | 7 | VII-1 | Mcpt4 |
| 3288 | 3 | 4 | 5 | 6 | 7 | VII-1 | Mcrs1 |
| 3289 | 3 | 4 | 5 | 6 | 7 | VII-1 | Mcts1 |
| 3290 | 3 | 4 | 5 | 6 | 7 | VII-1 | Mdp1 |
| 3291 | 3 | 4 | 5 | 6 | 7 | VII-1 | Mecr |
| 3292 | 3 | 4 | 5 | 6 | 7 | VII-1 | Med18 |
| 3293 | 3 | 4 | 5 | 6 | 7 | VII-1 | Med29 |
| 3294 | 3 | 4 | 5 | 6 | 7 | VII-1 | Med9os |
| 3295 | 3 | 4 | 5 | 6 | 7 | VII-1 | Mef2b |
| 3296 | 3 | 4 | 5 | 6 | 7 | VII-1 | Meg3 |
| 3297 | 3 | 4 | 5 | 6 | 7 | VII-1 | Meig1 |
| 3298 | 3 | 4 | 5 | 6 | 7 | VII-1 | Meis3 |
| 3299 | 3 | 4 | 5 | 6 | 7 | VII-1 | Mepce |
| 3300 | 3 | 4 | 5 | 6 | 7 | VII-1 | Mest |
| 3301 | 3 | 4 | 5 | 6 | 7 | VII-1 | Metap1d |
| 3302 | 3 | 4 | 5 | 6 | 7 | VII-1 | Metrn |
| 3303 | 3 | 4 | 5 | 6 | 7 | VII-1 | Metrnl |
| 3304 | 3 | 4 | 5 | 6 | 7 | VII-1 | Mettl10 |
| 3305 | 3 | 4 | 5 | 6 | 7 | VII-1 | Mettl7b |
| 3306 | 3 | 4 | 5 | 6 | 7 | VII-1 | Mfge8 |
| 3307 | 3 | 4 | 5 | 6 | 7 | VII-1 | Mfsd2a |
| 3308 | 3 | 4 | 5 | 6 | 7 | VII-1 | Mfsd6l |
| 3309 | 3 | 4 | 5 | 6 | 7 | VII-1 | Mgmt |
| 3310 | 3 | 4 | 5 | 6 | 7 | VII-1 | Mgp |
| 3311 | 3 | 4 | 5 | 6 | 7 | VII-1 | Mgst2 |
| 3312 | 3 | 4 | 5 | 6 | 7 | VII-1 | Mgst3 |
| 3313 | 3 | 4 | 5 | 6 | 7 | VII-1 | Mia |
| 3314 | 3 | 4 | 5 | 6 | 7 | VII-1 | Miat |
| 3315 | 3 | 4 | 5 | 6 | 7 | VII-1 | Mical1 |
| 3316 | 3 | 4 | 5 | 6 | 7 | VII-1 | Micall1 |
| 3317 | 3 | 4 | 5 | 6 | 7 | VII-1 | Mif |
| 3318 | 3 | 4 | 5 | 6 | 7 | VII-1 | Mif4gd |
| 3319 | 3 | 4 | 5 | 6 | 7 | VII-1 | Miip |
| 3320 | 3 | 4 | 5 | 6 | 7 | VII-1 | Minos1 |
| 3321 | 3 | 4 | 5 | 6 | 7 | VII-1 | Mir10a |
| 3322 | 3 | 4 | 5 | 6 | 7 | VII-1 | Mir1291 |
| 3323 | 3 | 4 | 5 | 6 | 7 | VII-1 | Mir142b |
| 3324 | 3 | 4 | 5 | 6 | 7 | VII-1 | Mir1957b |
| 3325 | 3 | 4 | 5 | 6 | 7 | VII-1 | Mir210 |
| 3326 | 3 | 4 | 5 | 6 | 7 | VII-1 | Mir214 |
| 3327 | 3 | 4 | 5 | 6 | 7 | VII-1 | Mir22hg |
| 3328 | 3 | 4 | 5 | 6 | 7 | VII-1 | Mir365-2 |
| 3329 | 3 | 4 | 5 | 6 | 7 | VII-1 | Mir466i |
| 3330 | 3 | 4 | 5 | 6 | 7 | VII-1 | Mir6236 |
| 3331 | 3 | 4 | 5 | 6 | 7 | VII-1 | Mir6340 |
| 3332 | 3 | 4 | 5 | 6 | 7 | VII-1 | Mir6357 |
| 3333 | 3 | 4 | 5 | 6 | 7 | VII-1 | Mir6418 |
| 3334 | 3 | 4 | 5 | 6 | 7 | VII-1 | Mir6538 |
| 3335 | 3 | 4 | 5 | 6 | 7 | VII-1 | Mir682 |
| 3336 | 3 | 4 | 5 | 6 | 7 | VII-1 | Mir6992 |
| 3337 | 3 | 4 | 5 | 6 | 7 | VII-1 | Mir7-1 |
| 3338 | 3 | 4 | 5 | 6 | 7 | VII-1 | Mir703 |
| 3339 | 3 | 4 | 5 | 6 | 7 | VII-1 | Mir719 |
| 3340 | 3 | 4 | 5 | 6 | 7 | VII-1 | Mir760 |
| 3341 | 3 | 4 | 5 | 6 | 7 | VII-1 | Mir8091 |
| 3342 | 3 | 4 | 5 | 6 | 7 | VII-1 | Mir8093 |
| 3343 | 3 | 4 | 5 | 6 | 7 | VII-1 | Mir8094 |
| 3344 | 3 | 4 | 5 | 6 | 7 | VII-1 | Mir8097 |
| 3345 | 3 | 4 | 5 | 6 | 7 | VII-1 | Mir8098 |
| 3346 | 3 | 4 | 5 | 6 | 7 | VII-1 | Mir8099-1 |
| 3347 | 3 | 4 | 5 | 6 | 7 | VII-1 | Mir8102 |
| 3348 | 3 | 4 | 5 | 6 | 7 | VII-1 | Mir8104 |
| 3349 | 3 | 4 | 5 | 6 | 7 | VII-1 | Mir8112 |
| 3350 | 3 | 4 | 5 | 6 | 7 | VII-1 | Mir8113 |
| 3351 | 3 | 4 | 5 | 6 | 7 | VII-1 | Mir8114 |
| 3352 | 3 | 4 | 5 | 6 | 7 | VII-1 | Mirlet7d |
| 3353 | 3 | 4 | 5 | 6 | 7 | VII-1 | Mkl1 |
| 3354 | 3 | 4 | 5 | 6 | 7 | VII-1 | Mlf1 |
| 3355 | 3 | 4 | 5 | 6 | 7 | VII-1 | Mlkl |
| 3356 | 3 | 4 | 5 | 6 | 7 | VII-1 | Mlx |
| 3357 | 3 | 4 | 5 | 6 | 7 | VII-1 | Mmd2 |
| 3358 | 3 | 4 | 5 | 6 | 7 | VII-1 | Mmp12 |
| 3359 | 3 | 4 | 5 | 6 | 7 | VII-1 | Mmp23 |
| 3360 | 3 | 4 | 5 | 6 | 7 | VII-1 | Mmp3 |
| 3361 | 3 | 4 | 5 | 6 | 7 | VII-1 | Mmp7 |
| 3362 | 3 | 4 | 5 | 6 | 7 | VII-1 | Mmp8 |
| 3363 | 3 | 4 | 5 | 6 | 7 | VII-1 | Mms19 |
| 3364 | 3 | 4 | 5 | 6 | 7 | VII-1 | Mnd1 |
| 3365 | 3 | 4 | 5 | 6 | 7 | VII-1 | Mnda |
| 3366 | 3 | 4 | 5 | 6 | 7 | VII-1 | Moap1 |
| 3367 | 3 | 4 | 5 | 6 | 7 | VII-1 | Mobp |
| 3368 | 3 | 4 | 5 | 6 | 7 | VII-1 | Mon1a |
| 3369 | 3 | 4 | 5 | 6 | 7 | VII-1 | Morn3 |
| 3370 | 3 | 4 | 5 | 6 | 7 | VII-1 | Mospd1 |
| 3371 | 3 | 4 | 5 | 6 | 7 | VII-1 | Mpc1 |
| 3372 | 3 | 4 | 5 | 6 | 7 | VII-1 | Mpc2 |
| 3373 | 3 | 4 | 5 | 6 | 7 | VII-1 | Mpnd |
| 3374 | 3 | 4 | 5 | 6 | 7 | VII-1 | Mpo |
| 3375 | 3 | 4 | 5 | 6 | 7 | VII-1 | Mpp3 |
| 3376 | 3 | 4 | 5 | 6 | 7 | VII-1 | Mpp7 |
| 3377 | 3 | 4 | 5 | 6 | 7 | VII-1 | Mpped1 |
| 3378 | 3 | 4 | 5 | 6 | 7 | VII-1 | Mpv17l2 |
| 3379 | 3 | 4 | 5 | 6 | 7 | VII-1 | Mpzl2 |
| 3380 | 3 | 4 | 5 | 6 | 7 | VII-1 | Mrap |
| 3381 | 3 | 4 | 5 | 6 | 7 | VII-1 | Mrap2 |
| 3382 | 3 | 4 | 5 | 6 | 7 | VII-1 | Mrgprg |
| 3383 | 3 | 4 | 5 | 6 | 7 | VII-1 | Mri1 |
| 3384 | 3 | 4 | 5 | 6 | 7 | VII-1 | Mroh1 |
| 3385 | 3 | 4 | 5 | 6 | 7 | VII-1 | Mrpl11 |
| 3386 | 3 | 4 | 5 | 6 | 7 | VII-1 | Mrpl12 |
| 3387 | 3 | 4 | 5 | 6 | 7 | VII-1 | Mrpl13 |
| 3388 | 3 | 4 | 5 | 6 | 7 | VII-1 | Mrpl14 |
| 3389 | 3 | 4 | 5 | 6 | 7 | VII-1 | Mrpl2 |
| 3390 | 3 | 4 | 5 | 6 | 7 | VII-1 | Mrpl22 |
| 3391 | 3 | 4 | 5 | 6 | 7 | VII-1 | Mrpl23 |
| 3392 | 3 | 4 | 5 | 6 | 7 | VII-1 | Mrpl24 |
| 3393 | 3 | 4 | 5 | 6 | 7 | VII-1 | Mrpl27 |
| 3394 | 3 | 4 | 5 | 6 | 7 | VII-1 | Mrpl28 |
| 3395 | 3 | 4 | 5 | 6 | 7 | VII-1 | Mrpl30 |
| 3396 | 3 | 4 | 5 | 6 | 7 | VII-1 | Mrpl32 |
| 3397 | 3 | 4 | 5 | 6 | 7 | VII-1 | Mrpl33 |
| 3398 | 3 | 4 | 5 | 6 | 7 | VII-1 | Mrpl38 |
| 3399 | 3 | 4 | 5 | 6 | 7 | VII-1 | Mrpl4 |
| 3400 | 3 | 4 | 5 | 6 | 7 | VII-1 | Mrpl41 |
| 3401 | 3 | 4 | 5 | 6 | 7 | VII-1 | Mrpl46 |
| 3402 | 3 | 4 | 5 | 6 | 7 | VII-1 | Mrpl47 |
| 3403 | 3 | 4 | 5 | 6 | 7 | VII-1 | Mrpl48 |
| 3404 | 3 | 4 | 5 | 6 | 7 | VII-1 | Mrpl52 |
| 3405 | 3 | 4 | 5 | 6 | 7 | VII-1 | Mrpl54 |
| 3406 | 3 | 4 | 5 | 6 | 7 | VII-1 | Mrps10 |
| 3407 | 3 | 4 | 5 | 6 | 7 | VII-1 | Mrps11 |
| 3408 | 3 | 4 | 5 | 6 | 7 | VII-1 | Mrps12 |
| 3409 | 3 | 4 | 5 | 6 | 7 | VII-1 | Mrps15 |
| 3410 | 3 | 4 | 5 | 6 | 7 | VII-1 | Mrps16 |
| 3411 | 3 | 4 | 5 | 6 | 7 | VII-1 | Mrps18a |
| 3412 | 3 | 4 | 5 | 6 | 7 | VII-1 | Mrps18c |
| 3413 | 3 | 4 | 5 | 6 | 7 | VII-1 | Mrps21 |
| 3414 | 3 | 4 | 5 | 6 | 7 | VII-1 | Mrps24 |
| 3415 | 3 | 4 | 5 | 6 | 7 | VII-1 | Mrps26 |
| 3416 | 3 | 4 | 5 | 6 | 7 | VII-1 | Mrps6 |
| 3417 | 3 | 4 | 5 | 6 | 7 | VII-1 | Mrto4 |
| 3418 | 3 | 4 | 5 | 6 | 7 | VII-1 | Ms4a7 |
| 3419 | 3 | 4 | 5 | 6 | 7 | VII-1 | Ms4a8a |
| 3420 | 3 | 4 | 5 | 6 | 7 | VII-1 | Msrb1 |
| 3421 | 3 | 4 | 5 | 6 | 7 | VII-1 | Msrb2 |
| 3422 | 3 | 4 | 5 | 6 | 7 | VII-1 | Mst1 |
| 3423 | 3 | 4 | 5 | 6 | 7 | VII-1 | Mstn |
| 3424 | 3 | 4 | 5 | 6 | 7 | VII-1 | Msto1 |
| 3425 | 3 | 4 | 5 | 6 | 7 | VII-1 | Mt1 |
| 3426 | 3 | 4 | 5 | 6 | 7 | VII-1 | Mt2 |
| 3427 | 3 | 4 | 5 | 6 | 7 | VII-1 | Mt3 |
| 3428 | 3 | 4 | 5 | 6 | 7 | VII-1 | Mthfd2 |
| 3429 | 3 | 4 | 5 | 6 | 7 | VII-1 | Mtmr14 |
| 3430 | 3 | 4 | 5 | 6 | 7 | VII-1 | Mtmr7 |
| 3431 | 3 | 4 | 5 | 6 | 7 | VII-1 | Mttp |
| 3432 | 3 | 4 | 5 | 6 | 7 | VII-1 | Mtx1 |
| 3433 | 3 | 4 | 5 | 6 | 7 | VII-1 | Muc13 |
| 3434 | 3 | 4 | 5 | 6 | 7 | VII-1 | Mup1 |
| 3435 | 3 | 4 | 5 | 6 | 7 | VII-1 | Mup10 |
| 3436 | 3 | 4 | 5 | 6 | 7 | VII-1 | Mup12 |
| 3437 | 3 | 4 | 5 | 6 | 7 | VII-1 | Mup13 |
| 3438 | 3 | 4 | 5 | 6 | 7 | VII-1 | Mup15 |
| 3439 | 3 | 4 | 5 | 6 | 7 | VII-1 | Mup16 |
| 3440 | 3 | 4 | 5 | 6 | 7 | VII-1 | Mup17 |
| 3441 | 3 | 4 | 5 | 6 | 7 | VII-1 | Mup2 |
| 3442 | 3 | 4 | 5 | 6 | 7 | VII-1 | Mup3 |
| 3443 | 3 | 4 | 5 | 6 | 7 | VII-1 | Mup8 |
| 3444 | 3 | 4 | 5 | 6 | 7 | VII-1 | Mup9 |
| 3445 | 3 | 4 | 5 | 6 | 7 | VII-1 | Musk |
| 3446 | 3 | 4 | 5 | 6 | 7 | VII-1 | Mustn1 |
| 3447 | 3 | 4 | 5 | 6 | 7 | VII-1 | Mvb12a |
| 3448 | 3 | 4 | 5 | 6 | 7 | VII-1 | Mx1 |
| 3449 | 3 | 4 | 5 | 6 | 7 | VII-1 | Mx2 |
| 3450 | 3 | 4 | 5 | 6 | 7 | VII-1 | Mybpc2 |
| 3451 | 3 | 4 | 5 | 6 | 7 | VII-1 | Mycl |
| 3452 | 3 | 4 | 5 | 6 | 7 | VII-1 | Myeov2 |
| 3453 | 3 | 4 | 5 | 6 | 7 | VII-1 | Myh1 |
| 3454 | 3 | 4 | 5 | 6 | 7 | VII-1 | Myl10 |

Fig. 34 - 19

| | | | | | | | |
|---|---|---|---|---|---|---|---|
| 3455 | 3 | 4 | 5 | 6 | 7 | VII-1 | Myl2 |
| 3456 | 3 | 4 | 5 | 6 | 7 | VII-1 | Myl3 |
| 3457 | 3 | 4 | 5 | 6 | 7 | VII-1 | Myl4 |
| 3458 | 3 | 4 | 5 | 6 | 7 | VII-1 | Myl6 |
| 3459 | 3 | 4 | 5 | 6 | 7 | VII-1 | Mylpf |
| 3460 | 3 | 4 | 5 | 6 | 7 | VII-1 | Myo1b |
| 3461 | 3 | 4 | 5 | 6 | 7 | VII-1 | Myo9b |
| 3462 | 3 | 4 | 5 | 6 | 7 | VII-1 | Myom1 |
| 3463 | 3 | 4 | 5 | 6 | 7 | VII-1 | Myzap |
| 3464 | 3 | 4 | 5 | 6 | 7 | VII-1 | N6amt2 |
| 3465 | 3 | 4 | 5 | 6 | 7 | VII-1 | Naa10 |
| 3466 | 3 | 4 | 5 | 6 | 7 | VII-1 | Naa38 |
| 3467 | 3 | 4 | 5 | 6 | 7 | VII-1 | Nanos3 |
| 3468 | 3 | 4 | 5 | 6 | 7 | VII-1 | Nap1l2 |
| 3469 | 3 | 4 | 5 | 6 | 7 | VII-1 | Nap1l5 |
| 3470 | 3 | 4 | 5 | 6 | 7 | VII-1 | Napb |
| 3471 | 3 | 4 | 5 | 6 | 7 | VII-1 | Napsa |
| 3472 | 3 | 4 | 5 | 6 | 7 | VII-1 | Nat9 |
| 3473 | 3 | 4 | 5 | 6 | 7 | VII-1 | Ncald |
| 3474 | 3 | 4 | 5 | 6 | 7 | VII-1 | Ncam1 |
| 3475 | 3 | 4 | 5 | 6 | 7 | VII-1 | Ncf1 |
| 3476 | 3 | 4 | 5 | 6 | 7 | VII-1 | Ncs1 |
| 3477 | 3 | 4 | 5 | 6 | 7 | VII-1 | Ndrg4 |
| 3478 | 3 | 4 | 5 | 6 | 7 | VII-1 | Ndufa10 |
| 3479 | 3 | 4 | 5 | 6 | 7 | VII-1 | Ndufa11 |
| 3480 | 3 | 4 | 5 | 6 | 7 | VII-1 | Ndufa13 |
| 3481 | 3 | 4 | 5 | 6 | 7 | VII-1 | Ndufa2 |
| 3482 | 3 | 4 | 5 | 6 | 7 | VII-1 | Ndufa3 |
| 3483 | 3 | 4 | 5 | 6 | 7 | VII-1 | Ndufa4 |
| 3484 | 3 | 4 | 5 | 6 | 7 | VII-1 | Ndufa4l2 |
| 3485 | 3 | 4 | 5 | 6 | 7 | VII-1 | Ndufa5 |
| 3486 | 3 | 4 | 5 | 6 | 7 | VII-1 | Ndufa7 |
| 3487 | 3 | 4 | 5 | 6 | 7 | VII-1 | Ndufa9 |
| 3488 | 3 | 4 | 5 | 6 | 7 | VII-1 | Ndufb10 |
| 3489 | 3 | 4 | 5 | 6 | 7 | VII-1 | Ndufb5 |
| 3490 | 3 | 4 | 5 | 6 | 7 | VII-1 | Ndufb6 |
| 3491 | 3 | 4 | 5 | 6 | 7 | VII-1 | Ndufb7 |
| 3492 | 3 | 4 | 5 | 6 | 7 | VII-1 | Ndufc1 |
| 3493 | 3 | 4 | 5 | 6 | 7 | VII-1 | Ndufs3 |
| 3494 | 3 | 4 | 5 | 6 | 7 | VII-1 | Ndufs6 |
| 3495 | 3 | 4 | 5 | 6 | 7 | VII-1 | Ndufs7 |
| 3496 | 3 | 4 | 5 | 6 | 7 | VII-1 | Ndufs8 |
| 3497 | 3 | 4 | 5 | 6 | 7 | VII-1 | Ndufv1 |
| 3498 | 3 | 4 | 5 | 6 | 7 | VII-1 | Ndufv2 |
| 3499 | 3 | 4 | 5 | 6 | 7 | VII-1 | Ndufv3 |
| 3500 | 3 | 4 | 5 | 6 | 7 | VII-1 | Nefh |
| 3501 | 3 | 4 | 5 | 6 | 7 | VII-1 | Nefl |
| 3502 | 3 | 4 | 5 | 6 | 7 | VII-1 | Nefm |
| 3503 | 3 | 4 | 5 | 6 | 7 | VII-1 | Negr1 |
| 3504 | 3 | 4 | 5 | 6 | 7 | VII-1 | Neil2 |
| 3505 | 3 | 4 | 5 | 6 | 7 | VII-1 | Nell2 |
| 3506 | 3 | 4 | 5 | 6 | 7 | VII-1 | Nenf |
| 3507 | 3 | 4 | 5 | 6 | 7 | VII-1 | Nfil3 |
| 3508 | 3 | 4 | 5 | 6 | 7 | VII-1 | Nfkbia |
| 3509 | 3 | 4 | 5 | 6 | 7 | VII-1 | Nfkbib |
| 3510 | 3 | 4 | 5 | 6 | 7 | VII-1 | Nfkbil1 |
| 3511 | 3 | 4 | 5 | 6 | 7 | VII-1 | Ngdn |
| 3512 | 3 | 4 | 5 | 6 | 7 | VII-1 | Ngef |
| 3513 | 3 | 4 | 5 | 6 | 7 | VII-1 | Ngp |
| 3514 | 3 | 4 | 5 | 6 | 7 | VII-1 | Nhp2 |
| 3515 | 3 | 4 | 5 | 6 | 7 | VII-1 | Nit1 |
| 3516 | 3 | 4 | 5 | 6 | 7 | VII-1 | Nkx6-2 |
| 3517 | 3 | 4 | 5 | 6 | 7 | VII-1 | Nmb |
| 3518 | 3 | 4 | 5 | 6 | 7 | VII-1 | Nme1 |
| 3519 | 3 | 4 | 5 | 6 | 7 | VII-1 | Nme2 |
| 3520 | 3 | 4 | 5 | 6 | 7 | VII-1 | Nme3 |
| 3521 | 3 | 4 | 5 | 6 | 7 | VII-1 | Nme5 |
| 3522 | 3 | 4 | 5 | 6 | 7 | VII-1 | Nme7 |
| 3523 | 3 | 4 | 5 | 6 | 7 | VII-1 | Nmi |
| 3524 | 3 | 4 | 5 | 6 | 7 | VII-1 | Nnat |
| 3525 | 3 | 4 | 5 | 6 | 7 | VII-1 | Nnmt |
| 3526 | 3 | 4 | 5 | 6 | 7 | VII-1 | Nob1 |
| 3527 | 3 | 4 | 5 | 6 | 7 | VII-1 | Noc2l |
| 3528 | 3 | 4 | 5 | 6 | 7 | VII-1 | Nol12 |
| 3529 | 3 | 4 | 5 | 6 | 7 | VII-1 | Nol7 |
| 3530 | 3 | 4 | 5 | 6 | 7 | VII-1 | Nop16 |
| 3531 | 3 | 4 | 5 | 6 | 7 | VII-1 | Npas2 |
| 3532 | 3 | 4 | 5 | 6 | 7 | VII-1 | Npc1 |
| 3533 | 3 | 4 | 5 | 6 | 7 | VII-1 | Npcd |
| 3534 | 3 | 4 | 5 | 6 | 7 | VII-1 | Npdc1 |
| 3535 | 3 | 4 | 5 | 6 | 7 | VII-1 | Npff |
| 3536 | 3 | 4 | 5 | 6 | 7 | VII-1 | Npl |
| 3537 | 3 | 4 | 5 | 6 | 7 | VII-1 | Npm3 |
| 3538 | 3 | 4 | 5 | 6 | 7 | VII-1 | Nppb |
| 3539 | 3 | 4 | 5 | 6 | 7 | VII-1 | Npr1 |
| 3540 | 3 | 4 | 5 | 6 | 7 | VII-1 | Nptx1 |
| 3541 | 3 | 4 | 5 | 6 | 7 | VII-1 | Nptxr |
| 3542 | 3 | 4 | 5 | 6 | 7 | VII-1 | Nr1h3 |
| 3543 | 3 | 4 | 5 | 6 | 7 | VII-1 | Nr1h4 |
| 3544 | 3 | 4 | 5 | 6 | 7 | VII-1 | Nr2c2ap |
| 3545 | 3 | 4 | 5 | 6 | 7 | VII-1 | Nr4a1 |
| 3546 | 3 | 4 | 5 | 6 | 7 | VII-1 | Nr4a2 |
| 3547 | 3 | 4 | 5 | 6 | 7 | VII-1 | Nr4a3 |
| 3548 | 3 | 4 | 5 | 6 | 7 | VII-1 | Nrbp1 |
| 3549 | 3 | 4 | 5 | 6 | 7 | VII-1 | Nrg4 |
| 3550 | 3 | 4 | 5 | 6 | 7 | VII-1 | Nrsn1 |
| 3551 | 3 | 4 | 5 | 6 | 7 | VII-1 | Nrsn2 |
| 3552 | 3 | 4 | 5 | 6 | 7 | VII-1 | Nrtn |
| 3553 | 3 | 4 | 5 | 6 | 7 | VII-1 | Nrxn1 |
| 3554 | 3 | 4 | 5 | 6 | 7 | VII-1 | Nsg1 |
| 3555 | 3 | 4 | 5 | 6 | 7 | VII-1 | Nsmce1 |
| 3556 | 3 | 4 | 5 | 6 | 7 | VII-1 | Nsun5 |
| 3557 | 3 | 4 | 5 | 6 | 7 | VII-1 | Nt5c |
| 3558 | 3 | 4 | 5 | 6 | 7 | VII-1 | Nt5dc2 |
| 3559 | 3 | 4 | 5 | 6 | 7 | VII-1 | Ntan1 |
| 3560 | 3 | 4 | 5 | 6 | 7 | VII-1 | Nthl1 |
| 3561 | 3 | 4 | 5 | 6 | 7 | VII-1 | Ntm |
| 3562 | 3 | 4 | 5 | 6 | 7 | VII-1 | Ntmt1 |
| 3563 | 3 | 4 | 5 | 6 | 7 | VII-1 | Ntn5 |
| 3564 | 3 | 4 | 5 | 6 | 7 | VII-1 | Ntrk2 |
| 3565 | 3 | 4 | 5 | 6 | 7 | VII-1 | Ntsr2 |
| 3566 | 3 | 4 | 5 | 6 | 7 | VII-1 | Nubp2 |
| 3567 | 3 | 4 | 5 | 6 | 7 | VII-1 | Nubpl |
| 3568 | 3 | 4 | 5 | 6 | 7 | VII-1 | Nudt1 |
| 3569 | 3 | 4 | 5 | 6 | 7 | VII-1 | Nudt14 |
| 3570 | 3 | 4 | 5 | 6 | 7 | VII-1 | Nudt18 |
| 3571 | 3 | 4 | 5 | 6 | 7 | VII-1 | Nudt8 |
| 3572 | 3 | 4 | 5 | 6 | 7 | VII-1 | Nufip1 |
| 3573 | 3 | 4 | 5 | 6 | 7 | VII-1 | Nupr1l |
| 3574 | 3 | 4 | 5 | 6 | 7 | VII-1 | Nxn |
| 3575 | 3 | 4 | 5 | 6 | 7 | VII-1 | Oas1a |
| 3576 | 3 | 4 | 5 | 6 | 7 | VII-1 | Oas1c |
| 3577 | 3 | 4 | 5 | 6 | 7 | VII-1 | Oas1g |
| 3578 | 3 | 4 | 5 | 6 | 7 | VII-1 | Oas2 |
| 3579 | 3 | 4 | 5 | 6 | 7 | VII-1 | Oas3 |
| 3580 | 3 | 4 | 5 | 6 | 7 | VII-1 | Oasl1 |
| 3581 | 3 | 4 | 5 | 6 | 7 | VII-1 | Oasl2 |
| 3582 | 3 | 4 | 5 | 6 | 7 | VII-1 | Oaz1-ps |
| 3583 | 3 | 4 | 5 | 6 | 7 | VII-1 | Oaz3 |
| 3584 | 3 | 4 | 5 | 6 | 7 | VII-1 | Obp2a |
| 3585 | 3 | 4 | 5 | 6 | 7 | VII-1 | Ocel1 |
| 3586 | 3 | 4 | 5 | 6 | 7 | VII-1 | Ocm |
| 3587 | 3 | 4 | 5 | 6 | 7 | VII-1 | Odf1 |
| 3588 | 3 | 4 | 5 | 6 | 7 | VII-1 | Odf3l2 |
| 3589 | 3 | 4 | 5 | 6 | 7 | VII-1 | Ogfod2 |
| 3590 | 3 | 4 | 5 | 6 | 7 | VII-1 | Ogfod3 |
| 3591 | 3 | 4 | 5 | 6 | 7 | VII-1 | Ogfr |
| 3592 | 3 | 4 | 5 | 6 | 7 | VII-1 | Ogfrl1 |
| 3593 | 3 | 4 | 5 | 6 | 7 | VII-1 | Olfm1 |
| 3594 | 3 | 4 | 5 | 6 | 7 | VII-1 | Olfm4 |
| 3595 | 3 | 4 | 5 | 6 | 7 | VII-1 | Olfml2b |
| 3596 | 3 | 4 | 5 | 6 | 7 | VII-1 | Olig1 |
| 3597 | 3 | 4 | 5 | 6 | 7 | VII-1 | Omg |
| 3598 | 3 | 4 | 5 | 6 | 7 | VII-1 | Orai2 |
| 3599 | 3 | 4 | 5 | 6 | 7 | VII-1 | Orm1 |
| 3600 | 3 | 4 | 5 | 6 | 7 | VII-1 | Orm2 |
| 3601 | 3 | 4 | 5 | 6 | 7 | VII-1 | Orm3 |
| 3602 | 3 | 4 | 5 | 6 | 7 | VII-1 | Osgep |
| 3603 | 3 | 4 | 5 | 6 | 7 | VII-1 | Osr2 |
| 3604 | 3 | 4 | 5 | 6 | 7 | VII-1 | Otos |
| 3605 | 3 | 4 | 5 | 6 | 7 | VII-1 | Otud1 |
| 3606 | 3 | 4 | 5 | 6 | 7 | VII-1 | Otulin |
| 3607 | 3 | 4 | 5 | 6 | 7 | VII-1 | P2rx5 |
| 3608 | 3 | 4 | 5 | 6 | 7 | VII-1 | P2rx6 |
| 3609 | 3 | 4 | 5 | 6 | 7 | VII-1 | Pacsin3 |
| 3610 | 3 | 4 | 5 | 6 | 7 | VII-1 | Padi1 |
| 3611 | 3 | 4 | 5 | 6 | 7 | VII-1 | Padi3 |
| 3612 | 3 | 4 | 5 | 6 | 7 | VII-1 | Paf1 |
| 3613 | 3 | 4 | 5 | 6 | 7 | VII-1 | Pah |
| 3614 | 3 | 4 | 5 | 6 | 7 | VII-1 | Palm |
| 3615 | 3 | 4 | 5 | 6 | 7 | VII-1 | Pam16 |
| 3616 | 3 | 4 | 5 | 6 | 7 | VII-1 | Panx2 |
| 3617 | 3 | 4 | 5 | 6 | 7 | VII-1 | Paox |
| 3618 | 3 | 4 | 5 | 6 | 7 | VII-1 | Papl |
| 3619 | 3 | 4 | 5 | 6 | 7 | VII-1 | Paqr6 |
| 3620 | 3 | 4 | 5 | 6 | 7 | VII-1 | Pard6a |
| 3621 | 3 | 4 | 5 | 6 | 7 | VII-1 | Park7 |
| 3622 | 3 | 4 | 5 | 6 | 7 | VII-1 | Parl |
| 3623 | 3 | 4 | 5 | 6 | 7 | VII-1 | Parp6 |
| 3624 | 3 | 4 | 5 | 6 | 7 | VII-1 | Pbld1 |
| 3625 | 3 | 4 | 5 | 6 | 7 | VII-1 | Pbx4 |
| 3626 | 3 | 4 | 5 | 6 | 7 | VII-1 | Pcbd2 |
| 3627 | 3 | 4 | 5 | 6 | 7 | VII-1 | Pcdhga10 |
| 3628 | 3 | 4 | 5 | 6 | 7 | VII-1 | Pcdhgc3 |
| 3629 | 3 | 4 | 5 | 6 | 7 | VII-1 | Pcdhgc5 |
| 3630 | 3 | 4 | 5 | 6 | 7 | VII-1 | Pck1 |
| 3631 | 3 | 4 | 5 | 6 | 7 | VII-1 | Pck2 |
| 3632 | 3 | 4 | 5 | 6 | 7 | VII-1 | Pcp4 |
| 3633 | 3 | 4 | 5 | 6 | 7 | VII-1 | Pcsk1n |
| 3634 | 3 | 4 | 5 | 6 | 7 | VII-1 | Pcsk2 |
| 3635 | 3 | 4 | 5 | 6 | 7 | VII-1 | Pcyt2 |
| 3636 | 3 | 4 | 5 | 6 | 7 | VII-1 | Pdcd5 |
| 3637 | 3 | 4 | 5 | 6 | 7 | VII-1 | Pddc1 |
| 3638 | 3 | 4 | 5 | 6 | 7 | VII-1 | Pde4b |
| 3639 | 3 | 4 | 5 | 6 | 7 | VII-1 | Pde4d |
| 3640 | 3 | 4 | 5 | 6 | 7 | VII-1 | Pde6h |
| 3641 | 3 | 4 | 5 | 6 | 7 | VII-1 | Pde9a |
| 3642 | 3 | 4 | 5 | 6 | 7 | VII-1 | Pdia2 |
| 3643 | 3 | 4 | 5 | 6 | 7 | VII-1 | Pdia6 |
| 3644 | 3 | 4 | 5 | 6 | 7 | VII-1 | Pdk4 |
| 3645 | 3 | 4 | 5 | 6 | 7 | VII-1 | Pdlim1 |
| 3646 | 3 | 4 | 5 | 6 | 7 | VII-1 | Pdlim2 |

Fig. 34 - 20

| | | | | | | | |
|---|---|---|---|---|---|---|---|
| 3647 | 3 | 4 | 5 | 6 | 7 | VII-1 | Pdlim7 |
| 3648 | 3 | 4 | 5 | 6 | 7 | VII-1 | Pdrg1 |
| 3649 | 3 | 4 | 5 | 6 | 7 | VII-1 | Pdzd9 |
| 3650 | 3 | 4 | 5 | 6 | 7 | VII-1 | Pdzk1ip1 |
| 3651 | 3 | 4 | 5 | 6 | 7 | VII-1 | Peg3 |
| 3652 | 3 | 4 | 5 | 6 | 7 | VII-1 | Peg3os |
| 3653 | 3 | 4 | 5 | 6 | 7 | VII-1 | Pemt |
| 3654 | 3 | 4 | 5 | 6 | 7 | VII-1 | Penk |
| 3655 | 3 | 4 | 5 | 6 | 7 | VII-1 | Perp |
| 3656 | 3 | 4 | 5 | 6 | 7 | VII-1 | Pet100 |
| 3657 | 3 | 4 | 5 | 6 | 7 | VII-1 | Pet112 |
| 3658 | 3 | 4 | 5 | 6 | 7 | VII-1 | Pex11g |
| 3659 | 3 | 4 | 5 | 6 | 7 | VII-1 | Pex16 |
| 3660 | 3 | 4 | 5 | 6 | 7 | VII-1 | Pex5l |
| 3661 | 3 | 4 | 5 | 6 | 7 | VII-1 | Pex6 |
| 3662 | 3 | 4 | 5 | 6 | 7 | VII-1 | Pfdn1 |
| 3663 | 3 | 4 | 5 | 6 | 7 | VII-1 | Pfdn2 |
| 3664 | 3 | 4 | 5 | 6 | 7 | VII-1 | Pfdn5 |
| 3665 | 3 | 4 | 5 | 6 | 7 | VII-1 | Pfkfb3 |
| 3666 | 3 | 4 | 5 | 6 | 7 | VII-1 | Pfn3 |
| 3667 | 3 | 4 | 5 | 6 | 7 | VII-1 | Pgam2 |
| 3668 | 3 | 4 | 5 | 6 | 7 | VII-1 | Pgbd5 |
| 3669 | 3 | 4 | 5 | 6 | 7 | VII-1 | Pgc |
| 3670 | 3 | 4 | 5 | 6 | 7 | VII-1 | Pgf |
| 3671 | 3 | 4 | 5 | 6 | 7 | VII-1 | Pgk2 |
| 3672 | 3 | 4 | 5 | 6 | 7 | VII-1 | Pgls |
| 3673 | 3 | 4 | 5 | 6 | 7 | VII-1 | Pglyrp1 |
| 3674 | 3 | 4 | 5 | 6 | 7 | VII-1 | Pgp |
| 3675 | 3 | 4 | 5 | 6 | 7 | VII-1 | Phactr1 |
| 3676 | 3 | 4 | 5 | 6 | 7 | VII-1 | Phax |
| 3677 | 3 | 4 | 5 | 6 | 7 | VII-1 | Phb |
| 3678 | 3 | 4 | 5 | 6 | 7 | VII-1 | Phf11c |
| 3679 | 3 | 4 | 5 | 6 | 7 | VII-1 | Phf7 |
| 3680 | 3 | 4 | 5 | 6 | 7 | VII-1 | Phkg2 |
| 3681 | 3 | 4 | 5 | 6 | 7 | VII-1 | Phpt1 |
| 3682 | 3 | 4 | 5 | 6 | 7 | VII-1 | Phyh |
| 3683 | 3 | 4 | 5 | 6 | 7 | VII-1 | Phyhd1 |
| 3684 | 3 | 4 | 5 | 6 | 7 | VII-1 | Phyhipl |
| 3685 | 3 | 4 | 5 | 6 | 7 | VII-1 | Pigb |
| 3686 | 3 | 4 | 5 | 6 | 7 | VII-1 | Pigr |
| 3687 | 3 | 4 | 5 | 6 | 7 | VII-1 | Pigu |
| 3688 | 3 | 4 | 5 | 6 | 7 | VII-1 | Pigx |
| 3689 | 3 | 4 | 5 | 6 | 7 | VII-1 | Pigyl |
| 3690 | 3 | 4 | 5 | 6 | 7 | VII-1 | Pih1d1 |
| 3691 | 3 | 4 | 5 | 6 | 7 | VII-1 | Pilra |
| 3692 | 3 | 4 | 5 | 6 | 7 | VII-1 | Pin4 |
| 3693 | 3 | 4 | 5 | 6 | 7 | VII-1 | Pinlyp |
| 3694 | 3 | 4 | 5 | 6 | 7 | VII-1 | Pir |
| 3695 | 3 | 4 | 5 | 6 | 7 | VII-1 | Pkdcc |
| 3696 | 3 | 4 | 5 | 6 | 7 | VII-1 | Pkig |
| 3697 | 3 | 4 | 5 | 6 | 7 | VII-1 | Pkn1 |
| 3698 | 3 | 4 | 5 | 6 | 7 | VII-1 | Pla2g12a |
| 3699 | 3 | 4 | 5 | 6 | 7 | VII-1 | Pla2g1b |
| 3700 | 3 | 4 | 5 | 6 | 7 | VII-1 | Pla2g2d |
| 3701 | 3 | 4 | 5 | 6 | 7 | VII-1 | Plac9a |
| 3702 | 3 | 4 | 5 | 6 | 7 | VII-1 | Plaur |
| 3703 | 3 | 4 | 5 | 6 | 7 | VII-1 | Plb1 |
| 3704 | 3 | 4 | 5 | 6 | 7 | VII-1 | Pld4 |
| 3705 | 3 | 4 | 5 | 6 | 7 | VII-1 | Plekhh1 |
| 3706 | 3 | 4 | 5 | 6 | 7 | VII-1 | Plekhf1 |
| 3707 | 3 | 4 | 5 | 6 | 7 | VII-1 | Plekhg1 |
| 3708 | 3 | 4 | 5 | 6 | 7 | VII-1 | Plekhm2 |
| 3709 | 3 | 4 | 5 | 6 | 7 | VII-1 | Plin5 |
| 3710 | 3 | 4 | 5 | 6 | 7 | VII-1 | Plk3 |
| 3711 | 3 | 4 | 5 | 6 | 7 | VII-1 | Plp1 |
| 3712 | 3 | 4 | 5 | 6 | 7 | VII-1 | Plrg1 |
| 3713 | 3 | 4 | 5 | 6 | 7 | VII-1 | Plvap |
| 3714 | 3 | 4 | 5 | 6 | 7 | VII-1 | Pmaip1 |
| 3715 | 3 | 4 | 5 | 6 | 7 | VII-1 | Pmf1 |
| 3716 | 3 | 4 | 5 | 6 | 7 | VII-1 | Pmm1 |
| 3717 | 3 | 4 | 5 | 6 | 7 | VII-1 | Pmvk |
| 3718 | 3 | 4 | 5 | 6 | 7 | VII-1 | Pnlip |
| 3719 | 3 | 4 | 5 | 6 | 7 | VII-1 | Pnliprp1 |
| 3720 | 3 | 4 | 5 | 6 | 7 | VII-1 | Pnliprp2 |
| 3721 | 3 | 4 | 5 | 6 | 7 | VII-1 | Pnpla7 |
| 3722 | 3 | 4 | 5 | 6 | 7 | VII-1 | Poc1a |
| 3723 | 3 | 4 | 5 | 6 | 7 | VII-1 | Pofut2 |
| 3724 | 3 | 4 | 5 | 6 | 7 | VII-1 | Pold2 |
| 3725 | 3 | 4 | 5 | 6 | 7 | VII-1 | Pole3 |
| 3726 | 3 | 4 | 5 | 6 | 7 | VII-1 | Pole4 |
| 3727 | 3 | 4 | 5 | 6 | 7 | VII-1 | Polr2c |
| 3728 | 3 | 4 | 5 | 6 | 7 | VII-1 | Polr2e |
| 3729 | 3 | 4 | 5 | 6 | 7 | VII-1 | Polr2f |
| 3730 | 3 | 4 | 5 | 6 | 7 | VII-1 | Polr2l |
| 3731 | 3 | 4 | 5 | 6 | 7 | VII-1 | Pomc |
| 3732 | 3 | 4 | 5 | 6 | 7 | VII-1 | Pomp |
| 3733 | 3 | 4 | 5 | 6 | 7 | VII-1 | Pop5 |
| 3734 | 3 | 4 | 5 | 6 | 7 | VII-1 | Por |
| 3735 | 3 | 4 | 5 | 6 | 7 | VII-1 | Ppa1 |
| 3736 | 3 | 4 | 5 | 6 | 7 | VII-1 | Ppa2 |
| 3737 | 3 | 4 | 5 | 6 | 7 | VII-1 | Ppan |
| 3738 | 3 | 4 | 5 | 6 | 7 | VII-1 | Ppargc1a |
| 3739 | 3 | 4 | 5 | 6 | 7 | VII-1 | Ppcdc |
| 3740 | 3 | 4 | 5 | 6 | 7 | VII-1 | Ppdpf |
| 3741 | 3 | 4 | 5 | 6 | 7 | VII-1 | Ppie |
| 3742 | 3 | 4 | 5 | 6 | 7 | VII-1 | Ppih |
| 3743 | 3 | 4 | 5 | 6 | 7 | VII-1 | Ppil2 |
| 3744 | 3 | 4 | 5 | 6 | 7 | VII-1 | Ppil6 |
| 3745 | 3 | 4 | 5 | 6 | 7 | VII-1 | Ppm1e |
| 3746 | 3 | 4 | 5 | 6 | 7 | VII-1 | Ppox |
| 3747 | 3 | 4 | 5 | 6 | 7 | VII-1 | Ppp1ca |
| 3748 | 3 | 4 | 5 | 6 | 7 | VII-1 | Ppp1r11 |
| 3749 | 3 | 4 | 5 | 6 | 7 | VII-1 | Ppp1r12c |
| 3750 | 3 | 4 | 5 | 6 | 7 | VII-1 | Ppp1r14d |
| 3751 | 3 | 4 | 5 | 6 | 7 | VII-1 | Ppp1r1b |
| 3752 | 3 | 4 | 5 | 6 | 7 | VII-1 | Ppp1r27 |
| 3753 | 3 | 4 | 5 | 6 | 7 | VII-1 | Ppp1r3g |
| 3754 | 3 | 4 | 5 | 6 | 7 | VII-1 | Ppp2r2c |
| 3755 | 3 | 4 | 5 | 6 | 7 | VII-1 | Ppp2r2d |
| 3756 | 3 | 4 | 5 | 6 | 7 | VII-1 | Ppp2r3d |
| 3757 | 3 | 4 | 5 | 6 | 7 | VII-1 | Ppp4c |
| 3758 | 3 | 4 | 5 | 6 | 7 | VII-1 | Pqbp1 |
| 3759 | 3 | 4 | 5 | 6 | 7 | VII-1 | Prap1 |
| 3760 | 3 | 4 | 5 | 6 | 7 | VII-1 | Prdx2 |
| 3761 | 3 | 4 | 5 | 6 | 7 | VII-1 | Prg2 |
| 3762 | 3 | 4 | 5 | 6 | 7 | VII-1 | Prg4 |
| 3763 | 3 | 4 | 5 | 6 | 7 | VII-1 | Prima1 |
| 3764 | 3 | 4 | 5 | 6 | 7 | VII-1 | Prkab2 |
| 3765 | 3 | 4 | 5 | 6 | 7 | VII-1 | Prkar2b |
| 3766 | 3 | 4 | 5 | 6 | 7 | VII-1 | Prkcg |
| 3767 | 3 | 4 | 5 | 6 | 7 | VII-1 | Prkcsh |
| 3768 | 3 | 4 | 5 | 6 | 7 | VII-1 | Prkcz |
| 3769 | 3 | 4 | 5 | 6 | 7 | VII-1 | Prkrip1 |
| 3770 | 3 | 4 | 5 | 6 | 7 | VII-1 | Prm1 |
| 3771 | 3 | 4 | 5 | 6 | 7 | VII-1 | Prm2 |
| 3772 | 3 | 4 | 5 | 6 | 7 | VII-1 | Prm3 |
| 3773 | 3 | 4 | 5 | 6 | 7 | VII-1 | Prmt5 |
| 3774 | 3 | 4 | 5 | 6 | 7 | VII-1 | Procr |
| 3775 | 3 | 4 | 5 | 6 | 7 | VII-1 | Proi1 |
| 3776 | 3 | 4 | 5 | 6 | 7 | VII-1 | Proser2 |
| 3777 | 3 | 4 | 5 | 6 | 7 | VII-1 | Prpf19 |
| 3778 | 3 | 4 | 5 | 6 | 7 | VII-1 | Prpf6 |
| 3779 | 3 | 4 | 5 | 6 | 7 | VII-1 | Prph |
| 3780 | 3 | 4 | 5 | 6 | 7 | VII-1 | Prpsap1 |
| 3781 | 3 | 4 | 5 | 6 | 7 | VII-1 | Prr15l |
| 3782 | 3 | 4 | 5 | 6 | 7 | VII-1 | Prr22 |
| 3783 | 3 | 4 | 5 | 6 | 7 | VII-1 | Prr30 |
| 3784 | 3 | 4 | 5 | 6 | 7 | VII-1 | Prss2 |
| 3785 | 3 | 4 | 5 | 6 | 7 | VII-1 | Prss22 |
| 3786 | 3 | 4 | 5 | 6 | 7 | VII-1 | Prss3 |
| 3787 | 3 | 4 | 5 | 6 | 7 | VII-1 | Prss53 |
| 3788 | 3 | 4 | 5 | 6 | 7 | VII-1 | Prtn3 |
| 3789 | 3 | 4 | 5 | 6 | 7 | VII-1 | Prune2 |
| 3790 | 3 | 4 | 5 | 6 | 7 | VII-1 | Psca |
| 3791 | 3 | 4 | 5 | 6 | 7 | VII-1 | Psen2 |
| 3792 | 3 | 4 | 5 | 6 | 7 | VII-1 | Psenen |
| 3793 | 3 | 4 | 5 | 6 | 7 | VII-1 | Psma5 |
| 3794 | 3 | 4 | 5 | 6 | 7 | VII-1 | Psma6 |
| 3795 | 3 | 4 | 5 | 6 | 7 | VII-1 | Psma7 |
| 3796 | 3 | 4 | 5 | 6 | 7 | VII-1 | Psmb1 |
| 3797 | 3 | 4 | 5 | 6 | 7 | VII-1 | Psmb10 |
| 3798 | 3 | 4 | 5 | 6 | 7 | VII-1 | Psmb3 |
| 3799 | 3 | 4 | 5 | 6 | 7 | VII-1 | Psmb6 |
| 3800 | 3 | 4 | 5 | 6 | 7 | VII-1 | Psmb7 |
| 3801 | 3 | 4 | 5 | 6 | 7 | VII-1 | Psmb8 |
| 3802 | 3 | 4 | 5 | 6 | 7 | VII-1 | Psmb9 |
| 3803 | 3 | 4 | 5 | 6 | 7 | VII-1 | Psmc1 |
| 3804 | 3 | 4 | 5 | 6 | 7 | VII-1 | Psmc2 |
| 3805 | 3 | 4 | 5 | 6 | 7 | VII-1 | Psmd12 |
| 3806 | 3 | 4 | 5 | 6 | 7 | VII-1 | Psmd13 |
| 3807 | 3 | 4 | 5 | 6 | 7 | VII-1 | Psmd2 |
| 3808 | 3 | 4 | 5 | 6 | 7 | VII-1 | Psmd4 |
| 3809 | 3 | 4 | 5 | 6 | 7 | VII-1 | Psme1 |
| 3810 | 3 | 4 | 5 | 6 | 7 | VII-1 | Psmg2 |
| 3811 | 3 | 4 | 5 | 6 | 7 | VII-1 | Psmg3 |
| 3812 | 3 | 4 | 5 | 6 | 7 | VII-1 | Psors1c2 |
| 3813 | 3 | 4 | 5 | 6 | 7 | VII-1 | Pstpip1 |
| 3814 | 3 | 4 | 5 | 6 | 7 | VII-1 | Ptgds |
| 3815 | 3 | 4 | 5 | 6 | 7 | VII-1 | Ptges3l |
| 3816 | 3 | 4 | 5 | 6 | 7 | VII-1 | Ptgis |
| 3817 | 3 | 4 | 5 | 6 | 7 | VII-1 | Ptgs1 |
| 3818 | 3 | 4 | 5 | 6 | 7 | VII-1 | Pth |
| 3819 | 3 | 4 | 5 | 6 | 7 | VII-1 | Pth1r |
| 3820 | 3 | 4 | 5 | 6 | 7 | VII-1 | Pth2 |
| 3821 | 3 | 4 | 5 | 6 | 7 | VII-1 | Ptpn18 |
| 3822 | 3 | 4 | 5 | 6 | 7 | VII-1 | Ptpn5 |
| 3823 | 3 | 4 | 5 | 6 | 7 | VII-1 | Ptprn |
| 3824 | 3 | 4 | 5 | 6 | 7 | VII-1 | Ptprn2 |
| 3825 | 3 | 4 | 5 | 6 | 7 | VII-1 | Pvalb |
| 3826 | 3 | 4 | 5 | 6 | 7 | VII-1 | Pvr |
| 3827 | 3 | 4 | 5 | 6 | 7 | VII-1 | Pxmp2 |
| 3828 | 3 | 4 | 5 | 6 | 7 | VII-1 | Pycr1 |
| 3829 | 3 | 4 | 5 | 6 | 7 | VII-1 | Pydc3 |
| 3830 | 3 | 4 | 5 | 6 | 7 | VII-1 | Pyroxd2 |
| 3831 | 3 | 4 | 5 | 6 | 7 | VII-1 | Pyy |
| 3832 | 3 | 4 | 5 | 6 | 7 | VII-1 | Qtrt1 |
| 3833 | 3 | 4 | 5 | 6 | 7 | VII-1 | Rab10os |
| 3834 | 3 | 4 | 5 | 6 | 7 | VII-1 | Rab13 |
| 3835 | 3 | 4 | 5 | 6 | 7 | VII-1 | Rab15 |
| 3836 | 3 | 4 | 5 | 6 | 7 | VII-1 | Rab17 |
| 3837 | 3 | 4 | 5 | 6 | 7 | VII-1 | Rab24 |
| 3838 | 3 | 4 | 5 | 6 | 7 | VII-1 | Rab26os |

Fig. 34 - 21

| | | | | | | | |
|---|---|---|---|---|---|---|---|
| 3839 | 3 | 4 | 5 | 6 | 7 | VII-1 | Rab30 |
| 3840 | 3 | 4 | 5 | 6 | 7 | VII-1 | Rab34 |
| 3841 | 3 | 4 | 5 | 6 | 7 | VII-1 | Rab3c |
| 3842 | 3 | 4 | 5 | 6 | 7 | VII-1 | Rab40b |
| 3843 | 3 | 4 | 5 | 6 | 7 | VII-1 | Rab4b |
| 3844 | 3 | 4 | 5 | 6 | 7 | VII-1 | Rab6b |
| 3845 | 3 | 4 | 5 | 6 | 7 | VII-1 | Rab7 |
| 3846 | 3 | 4 | 5 | 6 | 7 | VII-1 | Rab7l1 |
| 3847 | 3 | 4 | 5 | 6 | 7 | VII-1 | Rab9 |
| 3848 | 3 | 4 | 5 | 6 | 7 | VII-1 | Rabac1 |
| 3849 | 3 | 4 | 5 | 6 | 7 | VII-1 | Rabif |
| 3850 | 3 | 4 | 5 | 6 | 7 | VII-1 | Rad9a |
| 3851 | 3 | 4 | 5 | 6 | 7 | VII-1 | Rae1 |
| 3852 | 3 | 4 | 5 | 6 | 7 | VII-1 | Raet1d |
| 3853 | 3 | 4 | 5 | 6 | 7 | VII-1 | Rai2 |
| 3854 | 3 | 4 | 5 | 6 | 7 | VII-1 | Ranbp1 |
| 3855 | 3 | 4 | 5 | 6 | 7 | VII-1 | Rangrf |
| 3856 | 3 | 4 | 5 | 6 | 7 | VII-1 | Rap1gap2 |
| 3857 | 3 | 4 | 5 | 6 | 7 | VII-1 | Rarres2 |
| 3858 | 3 | 4 | 5 | 6 | 7 | VII-1 | Rasa3 |
| 3859 | 3 | 4 | 5 | 6 | 7 | VII-1 | Rasd1 |
| 3860 | 3 | 4 | 5 | 6 | 7 | VII-1 | Rasd2 |
| 3861 | 3 | 4 | 5 | 6 | 7 | VII-1 | Rasgrf1 |
| 3862 | 3 | 4 | 5 | 6 | 7 | VII-1 | Rasip1 |
| 3863 | 3 | 4 | 5 | 6 | 7 | VII-1 | Rasl10b |
| 3864 | 3 | 4 | 5 | 6 | 7 | VII-1 | Rassf4 |
| 3865 | 3 | 4 | 5 | 6 | 7 | VII-1 | Rbakdn |
| 3866 | 3 | 4 | 5 | 6 | 7 | VII-1 | Rbfa |
| 3867 | 3 | 4 | 5 | 6 | 7 | VII-1 | Rbfox1 |
| 3868 | 3 | 4 | 5 | 6 | 7 | VII-1 | Rbfox3 |
| 3869 | 3 | 4 | 5 | 6 | 7 | VII-1 | Rbks |
| 3870 | 3 | 4 | 5 | 6 | 7 | VII-1 | Rbp1 |
| 3871 | 3 | 4 | 5 | 6 | 7 | VII-1 | Rbp2 |
| 3872 | 3 | 4 | 5 | 6 | 7 | VII-1 | Rbp7 |
| 3873 | 3 | 4 | 5 | 6 | 7 | VII-1 | Rce1 |
| 3874 | 3 | 4 | 5 | 6 | 7 | VII-1 | Rdh14 |
| 3875 | 3 | 4 | 5 | 6 | 7 | VII-1 | Rdh5 |
| 3876 | 3 | 4 | 5 | 6 | 7 | VII-1 | Rdm1 |
| 3877 | 3 | 4 | 5 | 6 | 7 | VII-1 | Redrum |
| 3878 | 3 | 4 | 5 | 6 | 7 | VII-1 | Reep4 |
| 3879 | 3 | 4 | 5 | 6 | 7 | VII-1 | Reg1 |
| 3880 | 3 | 4 | 5 | 6 | 7 | VII-1 | Reg2 |
| 3881 | 3 | 4 | 5 | 6 | 7 | VII-1 | Reg3a |
| 3882 | 3 | 4 | 5 | 6 | 7 | VII-1 | Reg3b |
| 3883 | 3 | 4 | 5 | 6 | 7 | VII-1 | Reg3g |
| 3884 | 3 | 4 | 5 | 6 | 7 | VII-1 | Relb |
| 3885 | 3 | 4 | 5 | 6 | 7 | VII-1 | Rell2 |
| 3886 | 3 | 4 | 5 | 6 | 7 | VII-1 | Ren1 |
| 3887 | 3 | 4 | 5 | 6 | 7 | VII-1 | Renbp |
| 3888 | 3 | 4 | 5 | 6 | 7 | VII-1 | Rerg |
| 3889 | 3 | 4 | 5 | 6 | 7 | VII-1 | Rergl |
| 3890 | 3 | 4 | 5 | 6 | 7 | VII-1 | Retn |
| 3891 | 3 | 4 | 5 | 6 | 7 | VII-1 | Retnla |
| 3892 | 3 | 4 | 5 | 6 | 7 | VII-1 | Retnlg |
| 3893 | 3 | 4 | 5 | 6 | 7 | VII-1 | Retsat |
| 3894 | 3 | 4 | 5 | 6 | 7 | VII-1 | Rfc2 |
| 3895 | 3 | 4 | 5 | 6 | 7 | VII-1 | Rfc5 |
| 3896 | 3 | 4 | 5 | 6 | 7 | VII-1 | Rgl2 |
| 3897 | 3 | 4 | 5 | 6 | 7 | VII-1 | Rgs1 |
| 3898 | 3 | 4 | 5 | 6 | 7 | VII-1 | Rgs2 |
| 3899 | 3 | 4 | 5 | 6 | 7 | VII-1 | Rgs3 |
| 3900 | 3 | 4 | 5 | 6 | 7 | VII-1 | Rgs7bp |
| 3901 | 3 | 4 | 5 | 6 | 7 | VII-1 | Rgs8 |
| 3902 | 3 | 4 | 5 | 6 | 7 | VII-1 | Rhbdd3 |
| 3903 | 3 | 4 | 5 | 6 | 7 | VII-1 | Rhbg |
| 3904 | 3 | 4 | 5 | 6 | 7 | VII-1 | Rhobtb3 |
| 3905 | 3 | 4 | 5 | 6 | 7 | VII-1 | Rhou |
| 3906 | 3 | 4 | 5 | 6 | 7 | VII-1 | Riiad1 |
| 3907 | 3 | 4 | 5 | 6 | 7 | VII-1 | Rit2 |
| 3908 | 3 | 4 | 5 | 6 | 7 | VII-1 | Rmnd1 |
| 3909 | 3 | 4 | 5 | 6 | 7 | VII-1 | Rmrp |
| 3910 | 3 | 4 | 5 | 6 | 7 | VII-1 | Rn4.5s |
| 3911 | 3 | 4 | 5 | 6 | 7 | VII-1 | Rn45s |
| 3912 | 3 | 4 | 5 | 6 | 7 | VII-1 | Rnase1 |
| 3913 | 3 | 4 | 5 | 6 | 7 | VII-1 | Rnase10 |
| 3914 | 3 | 4 | 5 | 6 | 7 | VII-1 | Rnase12 |
| 3915 | 3 | 4 | 5 | 6 | 7 | VII-1 | Rnase2a |
| 3916 | 3 | 4 | 5 | 6 | 7 | VII-1 | Rnaseh1 |
| 3917 | 3 | 4 | 5 | 6 | 7 | VII-1 | Rnaseh2a |
| 3918 | 3 | 4 | 5 | 6 | 7 | VII-1 | Rnaseh2b |
| 3919 | 3 | 4 | 5 | 6 | 7 | VII-1 | Rnasek |
| 3920 | 3 | 4 | 5 | 6 | 7 | VII-1 | Rnaset2a |
| 3921 | 3 | 4 | 5 | 6 | 7 | VII-1 | Rnaset2b |
| 3922 | 3 | 4 | 5 | 6 | 7 | VII-1 | Rnf112 |
| 3923 | 3 | 4 | 5 | 6 | 7 | VII-1 | Rnf125 |
| 3924 | 3 | 4 | 5 | 6 | 7 | VII-1 | Rnf185 |
| 3925 | 3 | 4 | 5 | 6 | 7 | VII-1 | Rnf208 |
| 3926 | 3 | 4 | 5 | 6 | 7 | VII-1 | Rnf25 |
| 3927 | 3 | 4 | 5 | 6 | 7 | VII-1 | Rnu11 |
| 3928 | 3 | 4 | 5 | 6 | 7 | VII-1 | Rogdi |
| 3929 | 3 | 4 | 5 | 6 | 7 | VII-1 | Rom1 |
| 3930 | 3 | 4 | 5 | 6 | 7 | VII-1 | Romo1 |
| 3931 | 3 | 4 | 5 | 6 | 7 | VII-1 | Ropn1l |
| 3932 | 3 | 4 | 5 | 6 | 7 | VII-1 | Rpa2 |
| 3933 | 3 | 4 | 5 | 6 | 7 | VII-1 | Rpap3 |
| 3934 | 3 | 4 | 5 | 6 | 7 | VII-1 | Rpf2 |
| 3935 | 3 | 4 | 5 | 6 | 7 | VII-1 | Rpgrip1 |
| 3936 | 3 | 4 | 5 | 6 | 7 | VII-1 | Rph3a |
| 3937 | 3 | 4 | 5 | 6 | 7 | VII-1 | Rpl10 |
| 3938 | 3 | 4 | 5 | 6 | 7 | VII-1 | Rpl10a |
| 3939 | 3 | 4 | 5 | 6 | 7 | VII-1 | Rpl13 |
| 3940 | 3 | 4 | 5 | 6 | 7 | VII-1 | Rpl13a |
| 3941 | 3 | 4 | 5 | 6 | 7 | VII-1 | Rpl14 |
| 3942 | 3 | 4 | 5 | 6 | 7 | VII-1 | Rpl17 |
| 3943 | 3 | 4 | 5 | 6 | 7 | VII-1 | Rpl18 |
| 3944 | 3 | 4 | 5 | 6 | 7 | VII-1 | Rpl18a |
| 3945 | 3 | 4 | 5 | 6 | 7 | VII-1 | Rpl19 |
| 3946 | 3 | 4 | 5 | 6 | 7 | VII-1 | Rpl22 |
| 3947 | 3 | 4 | 5 | 6 | 7 | VII-1 | Rpl22l1 |
| 3948 | 3 | 4 | 5 | 6 | 7 | VII-1 | Rpl23 |
| 3949 | 3 | 4 | 5 | 6 | 7 | VII-1 | Rpl24 |
| 3950 | 3 | 4 | 5 | 6 | 7 | VII-1 | Rpl27a |
| 3951 | 3 | 4 | 5 | 6 | 7 | VII-1 | Rpl28 |
| 3952 | 3 | 4 | 5 | 6 | 7 | VII-1 | Rpl31 |
| 3953 | 3 | 4 | 5 | 6 | 7 | VII-1 | Rpl31-ps12 |
| 3954 | 3 | 4 | 5 | 6 | 7 | VII-1 | Rpl32 |
| 3955 | 3 | 4 | 5 | 6 | 7 | VII-1 | Rpl35 |
| 3956 | 3 | 4 | 5 | 6 | 7 | VII-1 | Rpl35a |
| 3957 | 3 | 4 | 5 | 6 | 7 | VII-1 | Rpl36 |
| 3958 | 3 | 4 | 5 | 6 | 7 | VII-1 | Rpl36a |
| 3959 | 3 | 4 | 5 | 6 | 7 | VII-1 | Rpl36al |
| 3960 | 3 | 4 | 5 | 6 | 7 | VII-1 | Rpl37a |
| 3961 | 3 | 4 | 5 | 6 | 7 | VII-1 | Rpl38 |
| 3962 | 3 | 4 | 5 | 6 | 7 | VII-1 | Rpl39 |
| 3963 | 3 | 4 | 5 | 6 | 7 | VII-1 | Rpl3l |
| 3964 | 3 | 4 | 5 | 6 | 7 | VII-1 | Rpl4 |
| 3965 | 3 | 4 | 5 | 6 | 7 | VII-1 | Rpl41 |
| 3966 | 3 | 4 | 5 | 6 | 7 | VII-1 | Rpl8 |
| 3967 | 3 | 4 | 5 | 6 | 7 | VII-1 | Rplp0 |
| 3968 | 3 | 4 | 5 | 6 | 7 | VII-1 | Rplp1 |
| 3969 | 3 | 4 | 5 | 6 | 7 | VII-1 | Rplp2 |
| 3970 | 3 | 4 | 5 | 6 | 7 | VII-1 | Rplp2-ps1 |
| 3971 | 3 | 4 | 5 | 6 | 7 | VII-1 | Rpp21 |
| 3972 | 3 | 4 | 5 | 6 | 7 | VII-1 | Rpp25l |
| 3973 | 3 | 4 | 5 | 6 | 7 | VII-1 | Rpp40 |
| 3974 | 3 | 4 | 5 | 6 | 7 | VII-1 | Rpph1 |
| 3975 | 3 | 4 | 5 | 6 | 7 | VII-1 | Rprl3 |
| 3976 | 3 | 4 | 5 | 6 | 7 | VII-1 | Rps12 |
| 3977 | 3 | 4 | 5 | 6 | 7 | VII-1 | Rps13 |
| 3978 | 3 | 4 | 5 | 6 | 7 | VII-1 | Rps14 |
| 3979 | 3 | 4 | 5 | 6 | 7 | VII-1 | Rps15 |
| 3980 | 3 | 4 | 5 | 6 | 7 | VII-1 | Rps15a-ps4 |
| 3981 | 3 | 4 | 5 | 6 | 7 | VII-1 | Rps15a-ps6 |
| 3982 | 3 | 4 | 5 | 6 | 7 | VII-1 | Rps16 |
| 3983 | 3 | 4 | 5 | 6 | 7 | VII-1 | Rps18 |
| 3984 | 3 | 4 | 5 | 6 | 7 | VII-1 | Rps19 |
| 3985 | 3 | 4 | 5 | 6 | 7 | VII-1 | Rps19-ps3 |
| 3986 | 3 | 4 | 5 | 6 | 7 | VII-1 | Rps20 |
| 3987 | 3 | 4 | 5 | 6 | 7 | VII-1 | Rps24 |
| 3988 | 3 | 4 | 5 | 6 | 7 | VII-1 | Rps25 |
| 3989 | 3 | 4 | 5 | 6 | 7 | VII-1 | Rps27a |
| 3990 | 3 | 4 | 5 | 6 | 7 | VII-1 | Rps27rt |
| 3991 | 3 | 4 | 5 | 6 | 7 | VII-1 | Rps29 |
| 3992 | 3 | 4 | 5 | 6 | 7 | VII-1 | Rps3 |
| 3993 | 3 | 4 | 5 | 6 | 7 | VII-1 | Rps4l |
| 3994 | 3 | 4 | 5 | 6 | 7 | VII-1 | Rps4x |
| 3995 | 3 | 4 | 5 | 6 | 7 | VII-1 | Rps6 |
| 3996 | 3 | 4 | 5 | 6 | 7 | VII-1 | Rps8 |
| 3997 | 3 | 4 | 5 | 6 | 7 | VII-1 | Rps9 |
| 3998 | 3 | 4 | 5 | 6 | 7 | VII-1 | Rpsa |
| 3999 | 3 | 4 | 5 | 6 | 7 | VII-1 | Rpusd3 |
| 4000 | 3 | 4 | 5 | 6 | 7 | VII-1 | Rrad |
| 4001 | 3 | 4 | 5 | 6 | 7 | VII-1 | Rrp12 |
| 4002 | 3 | 4 | 5 | 6 | 7 | VII-1 | Rrp7a |
| 4003 | 3 | 4 | 5 | 6 | 7 | VII-1 | Rsad2 |
| 4004 | 3 | 4 | 5 | 6 | 7 | VII-1 | Rsbn1 |
| 4005 | 3 | 4 | 5 | 6 | 7 | VII-1 | Rsl1d1 |
| 4006 | 3 | 4 | 5 | 6 | 7 | VII-1 | Rsph9 |
| 4007 | 3 | 4 | 5 | 6 | 7 | VII-1 | Rtcb |
| 4008 | 3 | 4 | 5 | 6 | 7 | VII-1 | Rtn1 |
| 4009 | 3 | 4 | 5 | 6 | 7 | VII-1 | Rtn2 |
| 4010 | 3 | 4 | 5 | 6 | 7 | VII-1 | Rtp4 |
| 4011 | 3 | 4 | 5 | 6 | 7 | VII-1 | Rxrg |
| 4012 | 3 | 4 | 5 | 6 | 7 | VII-1 | S100a10 |
| 4013 | 3 | 4 | 5 | 6 | 7 | VII-1 | S100a13 |
| 4014 | 3 | 4 | 5 | 6 | 7 | VII-1 | S100a16 |
| 4015 | 3 | 4 | 5 | 6 | 7 | VII-1 | S100a3 |
| 4016 | 3 | 4 | 5 | 6 | 7 | VII-1 | S100a4 |
| 4017 | 3 | 4 | 5 | 6 | 7 | VII-1 | S100a5 |
| 4018 | 3 | 4 | 5 | 6 | 7 | VII-1 | S100a6 |
| 4019 | 3 | 4 | 5 | 6 | 7 | VII-1 | S100a8 |
| 4020 | 3 | 4 | 5 | 6 | 7 | VII-1 | S100a9 |
| 4021 | 3 | 4 | 5 | 6 | 7 | VII-1 | S100b |
| 4022 | 3 | 4 | 5 | 6 | 7 | VII-1 | Saa1 |
| 4023 | 3 | 4 | 5 | 6 | 7 | VII-1 | Saa2 |
| 4024 | 3 | 4 | 5 | 6 | 7 | VII-1 | Saa3 |
| 4025 | 3 | 4 | 5 | 6 | 7 | VII-1 | Safb2 |
| 4026 | 3 | 4 | 5 | 6 | 7 | VII-1 | Samd11 |
| 4027 | 3 | 4 | 5 | 6 | 7 | VII-1 | Samm50 |
| 4028 | 3 | 4 | 5 | 6 | 7 | VII-1 | Sap25 |
| 4029 | 3 | 4 | 5 | 6 | 7 | VII-1 | Sap30l |
| 4030 | 3 | 4 | 5 | 6 | 7 | VII-1 | Sapcd1 |

Fig. 34 - 22

| | | | | | | | |
|---|---|---|---|---|---|---|---|
| 4031 | 3 | 4 | 5 | 6 | 7 | VII-1 | Sars |
| 4032 | 3 | 4 | 5 | 6 | 7 | VII-1 | Sars2 |
| 4033 | 3 | 4 | 5 | 6 | 7 | VII-1 | Sat1 |
| 4034 | 3 | 4 | 5 | 6 | 7 | VII-1 | Sat2 |
| 4035 | 3 | 4 | 5 | 6 | 7 | VII-1 | Saysd1 |
| 4036 | 3 | 4 | 5 | 6 | 7 | VII-1 | Sbsn |
| 4037 | 3 | 4 | 5 | 6 | 7 | VII-1 | Scand1 |
| 4038 | 3 | 4 | 5 | 6 | 7 | VII-1 | Scara5 |
| 4039 | 3 | 4 | 5 | 6 | 7 | VII-1 | Scarletltr |
| 4040 | 3 | 4 | 5 | 6 | 7 | VII-1 | Scarna6 |
| 4041 | 3 | 4 | 5 | 6 | 7 | VII-1 | Scarna8 |
| 4042 | 3 | 4 | 5 | 6 | 7 | VII-1 | Scd3 |
| 4043 | 3 | 4 | 5 | 6 | 7 | VII-1 | Scg2 |
| 4044 | 3 | 4 | 5 | 6 | 7 | VII-1 | Scg3 |
| 4045 | 3 | 4 | 5 | 6 | 7 | VII-1 | Scgb1a1 |
| 4046 | 3 | 4 | 5 | 6 | 7 | VII-1 | Scgb2b27 |
| 4047 | 3 | 4 | 5 | 6 | 7 | VII-1 | Scgb3a1 |
| 4048 | 3 | 4 | 5 | 6 | 7 | VII-1 | Scgn |
| 4049 | 3 | 4 | 5 | 6 | 7 | VII-1 | Scn3b |
| 4050 | 3 | 4 | 5 | 6 | 7 | VII-1 | Scn4b |
| 4051 | 3 | 4 | 5 | 6 | 7 | VII-1 | Scnm1 |
| 4052 | 3 | 4 | 5 | 6 | 7 | VII-1 | Scnn1b |
| 4053 | 3 | 4 | 5 | 6 | 7 | VII-1 | Sco2 |
| 4054 | 3 | 4 | 5 | 6 | 7 | VII-1 | Scrg1 |
| 4055 | 3 | 4 | 5 | 6 | 7 | VII-1 | Scrn1 |
| 4056 | 3 | 4 | 5 | 6 | 7 | VII-1 | Scrn2 |
| 4057 | 3 | 4 | 5 | 6 | 7 | VII-1 | Scrt1 |
| 4058 | 3 | 4 | 5 | 6 | 7 | VII-1 | Sct |
| 4059 | 3 | 4 | 5 | 6 | 7 | VII-1 | Sctr |
| 4060 | 3 | 4 | 5 | 6 | 7 | VII-1 | Sdc4 |
| 4061 | 3 | 4 | 5 | 6 | 7 | VII-1 | Sdcbp2 |
| 4062 | 3 | 4 | 5 | 6 | 7 | VII-1 | Sdf2l1 |
| 4063 | 3 | 4 | 5 | 6 | 7 | VII-1 | Sdsl |
| 4064 | 3 | 4 | 5 | 6 | 7 | VII-1 | Sec61b |
| 4065 | 3 | 4 | 5 | 6 | 7 | VII-1 | Sec61g |
| 4066 | 3 | 4 | 5 | 6 | 7 | VII-1 | Sectm1b |
| 4067 | 3 | 4 | 5 | 6 | 7 | VII-1 | Selenbp1 |
| 4068 | 3 | 4 | 5 | 6 | 7 | VII-1 | Selenbp2 |
| 4069 | 3 | 4 | 5 | 6 | 7 | VII-1 | Selk |
| 4070 | 3 | 4 | 5 | 6 | 7 | VII-1 | Selm |
| 4071 | 3 | 4 | 5 | 6 | 7 | VII-1 | Selo |
| 4072 | 3 | 4 | 5 | 6 | 7 | VII-1 | Sept1 |
| 4073 | 3 | 4 | 5 | 6 | 7 | VII-1 | Sept5 |
| 4074 | 3 | 4 | 5 | 6 | 7 | VII-1 | Sepw1 |
| 4075 | 3 | 4 | 5 | 6 | 7 | VII-1 | Serf1 |
| 4076 | 3 | 4 | 5 | 6 | 7 | VII-1 | Sergef |
| 4077 | 3 | 4 | 5 | 6 | 7 | VII-1 | Serhl |
| 4078 | 3 | 4 | 5 | 6 | 7 | VII-1 | Serp2 |
| 4079 | 3 | 4 | 5 | 6 | 7 | VII-1 | Serpina12 |
| 4080 | 3 | 4 | 5 | 6 | 7 | VII-1 | Serpina1a |
| 4081 | 3 | 4 | 5 | 6 | 7 | VII-1 | Serpina1b |
| 4082 | 3 | 4 | 5 | 6 | 7 | VII-1 | Serpina1c |
| 4083 | 3 | 4 | 5 | 6 | 7 | VII-1 | Serpina1d |
| 4084 | 3 | 4 | 5 | 6 | 7 | VII-1 | Serpina1e |
| 4085 | 3 | 4 | 5 | 6 | 7 | VII-1 | Serpina3a |
| 4086 | 3 | 4 | 5 | 6 | 7 | VII-1 | Serpina3g |
| 4087 | 3 | 4 | 5 | 6 | 7 | VII-1 | Serpina3k |
| 4088 | 3 | 4 | 5 | 6 | 7 | VII-1 | Serpina3m |
| 4089 | 3 | 4 | 5 | 6 | 7 | VII-1 | Serpina3n |
| 4090 | 3 | 4 | 5 | 6 | 7 | VII-1 | Serpina6 |
| 4091 | 3 | 4 | 5 | 6 | 7 | VII-1 | Serpinb1a |
| 4092 | 3 | 4 | 5 | 6 | 7 | VII-1 | Serpinb6a |
| 4093 | 3 | 4 | 5 | 6 | 7 | VII-1 | Serpinb6b |
| 4094 | 3 | 4 | 5 | 6 | 7 | VII-1 | Serpine2 |
| 4095 | 3 | 4 | 5 | 6 | 7 | VII-1 | Serping1 |
| 4096 | 3 | 4 | 5 | 6 | 7 | VII-1 | Sertad1 |
| 4097 | 3 | 4 | 5 | 6 | 7 | VII-1 | Sertad3 |
| 4098 | 3 | 4 | 5 | 6 | 7 | VII-1 | Sesn1 |
| 4099 | 3 | 4 | 5 | 6 | 7 | VII-1 | Setd4 |
| 4100 | 3 | 4 | 5 | 6 | 7 | VII-1 | Setd7 |
| 4101 | 3 | 4 | 5 | 6 | 7 | VII-1 | Setdb2 |
| 4102 | 3 | 4 | 5 | 6 | 7 | VII-1 | Sez6 |
| 4103 | 3 | 4 | 5 | 6 | 7 | VII-1 | Sez6l |
| 4104 | 3 | 4 | 5 | 6 | 7 | VII-1 | Sez6l2 |
| 4105 | 3 | 4 | 5 | 6 | 7 | VII-1 | Sf3a3 |
| 4106 | 3 | 4 | 5 | 6 | 7 | VII-1 | Sfn |
| 4107 | 3 | 4 | 5 | 6 | 7 | VII-1 | Sfta2 |
| 4108 | 3 | 4 | 5 | 6 | 7 | VII-1 | Sftpb |
| 4109 | 3 | 4 | 5 | 6 | 7 | VII-1 | Sftpc |
| 4110 | 3 | 4 | 5 | 6 | 7 | VII-1 | Sgca |
| 4111 | 3 | 4 | 5 | 6 | 7 | VII-1 | Sgk1 |
| 4112 | 3 | 4 | 5 | 6 | 7 | VII-1 | Sgk3 |
| 4113 | 3 | 4 | 5 | 6 | 7 | VII-1 | Sgsh |
| 4114 | 3 | 4 | 5 | 6 | 7 | VII-1 | Sh2d4a |
| 4115 | 3 | 4 | 5 | 6 | 7 | VII-1 | Sh2d7 |
| 4116 | 3 | 4 | 5 | 6 | 7 | VII-1 | Sh3bgr |
| 4117 | 3 | 4 | 5 | 6 | 7 | VII-1 | Sh3gl2 |
| 4118 | 3 | 4 | 5 | 6 | 7 | VII-1 | Sh3glb1 |
| 4119 | 3 | 4 | 5 | 6 | 7 | VII-1 | Shf |
| 4120 | 3 | 4 | 5 | 6 | 7 | VII-1 | Shmt1 |
| 4121 | 3 | 4 | 5 | 6 | 7 | VII-1 | Sigirr |
| 4122 | 3 | 4 | 5 | 6 | 7 | VII-1 | Sik1 |
| 4123 | 3 | 4 | 5 | 6 | 7 | VII-1 | Sil1 |
| 4124 | 3 | 4 | 5 | 6 | 7 | VII-1 | Sin3b |
| 4125 | 3 | 4 | 5 | 6 | 7 | VII-1 | Sirpb1b |
| 4126 | 3 | 4 | 5 | 6 | 7 | VII-1 | Siva1 |
| 4127 | 3 | 4 | 5 | 6 | 7 | VII-1 | Slamf9 |
| 4128 | 3 | 4 | 5 | 6 | 7 | VII-1 | Slc10a3-ubl4 |
| 4129 | 3 | 4 | 5 | 6 | 7 | VII-1 | Slc10a6 |
| 4130 | 3 | 4 | 5 | 6 | 7 | VII-1 | Slc11a1 |
| 4131 | 3 | 4 | 5 | 6 | 7 | VII-1 | Slc12a5 |
| 4132 | 3 | 4 | 5 | 6 | 7 | VII-1 | Slc15a3 |
| 4133 | 3 | 4 | 5 | 6 | 7 | VII-1 | Slc16a3 |
| 4134 | 3 | 4 | 5 | 6 | 7 | VII-1 | Slc17a7 |
| 4135 | 3 | 4 | 5 | 6 | 7 | VII-1 | Slc1a2 |
| 4136 | 3 | 4 | 5 | 6 | 7 | VII-1 | Slc22a13b-ps |
| 4137 | 3 | 4 | 5 | 6 | 7 | VII-1 | Slc22a18 |
| 4138 | 3 | 4 | 5 | 6 | 7 | VII-1 | Slc22a4 |
| 4139 | 3 | 4 | 5 | 6 | 7 | VII-1 | Slc24a2 |
| 4140 | 3 | 4 | 5 | 6 | 7 | VII-1 | Slc25a14 |
| 4141 | 3 | 4 | 5 | 6 | 7 | VII-1 | Slc25a25 |
| 4142 | 3 | 4 | 5 | 6 | 7 | VII-1 | Slc25a30 |
| 4143 | 3 | 4 | 5 | 6 | 7 | VII-1 | Slc25a32 |
| 4144 | 3 | 4 | 5 | 6 | 7 | VII-1 | Slc25a33 |
| 4145 | 3 | 4 | 5 | 6 | 7 | VII-1 | Slc25a34 |
| 4146 | 3 | 4 | 5 | 6 | 7 | VII-1 | Slc25a39 |
| 4147 | 3 | 4 | 5 | 6 | 7 | VII-1 | Slc25a42 |
| 4148 | 3 | 4 | 5 | 6 | 7 | VII-1 | Slc26a10 |
| 4149 | 3 | 4 | 5 | 6 | 7 | VII-1 | Slc27a4 |
| 4150 | 3 | 4 | 5 | 6 | 7 | VII-1 | Slc29a1 |
| 4151 | 3 | 4 | 5 | 6 | 7 | VII-1 | Slc32a1 |
| 4152 | 3 | 4 | 5 | 6 | 7 | VII-1 | Slc35e4 |
| 4153 | 3 | 4 | 5 | 6 | 7 | VII-1 | Slc38a2 |
| 4154 | 3 | 4 | 5 | 6 | 7 | VII-1 | Slc39a14 |
| 4155 | 3 | 4 | 5 | 6 | 7 | VII-1 | Slc43a1 |
| 4156 | 3 | 4 | 5 | 6 | 7 | VII-1 | Slc5a11 |
| 4157 | 3 | 4 | 5 | 6 | 7 | VII-1 | Slc6a1 |
| 4158 | 3 | 4 | 5 | 6 | 7 | VII-1 | Slc6a11 |
| 4159 | 3 | 4 | 5 | 6 | 7 | VII-1 | Slc6a17 |
| 4160 | 3 | 4 | 5 | 6 | 7 | VII-1 | Slc7a5 |
| 4161 | 3 | 4 | 5 | 6 | 7 | VII-1 | Slc7a8 |
| 4162 | 3 | 4 | 5 | 6 | 7 | VII-1 | Slc8a2 |
| 4163 | 3 | 4 | 5 | 6 | 7 | VII-1 | Slc8b1 |
| 4164 | 3 | 4 | 5 | 6 | 7 | VII-1 | Slco1a4 |
| 4165 | 3 | 4 | 5 | 6 | 7 | VII-1 | Slfn2 |
| 4166 | 3 | 4 | 5 | 6 | 7 | VII-1 | Slfn4 |
| 4167 | 3 | 4 | 5 | 6 | 7 | VII-1 | Slfn5 |
| 4168 | 3 | 4 | 5 | 6 | 7 | VII-1 | Slirp |
| 4169 | 3 | 4 | 5 | 6 | 7 | VII-1 | Sln |
| 4170 | 3 | 4 | 5 | 6 | 7 | VII-1 | Slpi |
| 4171 | 3 | 4 | 5 | 6 | 7 | VII-1 | Slurp1 |
| 4172 | 3 | 4 | 5 | 6 | 7 | VII-1 | Smagp |
| 4173 | 3 | 4 | 5 | 6 | 7 | VII-1 | Smap1 |
| 4174 | 3 | 4 | 5 | 6 | 7 | VII-1 | Smarcal1 |
| 4175 | 3 | 4 | 5 | 6 | 7 | VII-1 | Smarcd2 |
| 4176 | 3 | 4 | 5 | 6 | 7 | VII-1 | Smarcd3 |
| 4177 | 3 | 4 | 5 | 6 | 7 | VII-1 | Smcp |
| 4178 | 3 | 4 | 5 | 6 | 7 | VII-1 | Smg9 |
| 4179 | 3 | 4 | 5 | 6 | 7 | VII-1 | Smim1 |
| 4180 | 3 | 4 | 5 | 6 | 7 | VII-1 | Smim20 |
| 4181 | 3 | 4 | 5 | 6 | 7 | VII-1 | Smim22 |
| 4182 | 3 | 4 | 5 | 6 | 7 | VII-1 | Smim23 |
| 4183 | 3 | 4 | 5 | 6 | 7 | VII-1 | Smim24 |
| 4184 | 3 | 4 | 5 | 6 | 7 | VII-1 | Smpd2 |
| 4185 | 3 | 4 | 5 | 6 | 7 | VII-1 | Smpd5 |
| 4186 | 3 | 4 | 5 | 6 | 7 | VII-1 | Snap25 |
| 4187 | 3 | 4 | 5 | 6 | 7 | VII-1 | Snap91 |
| 4188 | 3 | 4 | 5 | 6 | 7 | VII-1 | Sncb |
| 4189 | 3 | 4 | 5 | 6 | 7 | VII-1 | Snf8 |
| 4190 | 3 | 4 | 5 | 6 | 7 | VII-1 | Snhg11 |
| 4191 | 3 | 4 | 5 | 6 | 7 | VII-1 | Snhg12 |
| 4192 | 3 | 4 | 5 | 6 | 7 | VII-1 | Snhg3 |
| 4193 | 3 | 4 | 5 | 6 | 7 | VII-1 | Snhg5 |
| 4194 | 3 | 4 | 5 | 6 | 7 | VII-1 | Snhg9 |
| 4195 | 3 | 4 | 5 | 6 | 7 | VII-1 | Snora15 |
| 4196 | 3 | 4 | 5 | 6 | 7 | VII-1 | Snora16a |
| 4197 | 3 | 4 | 5 | 6 | 7 | VII-1 | Snora17 |
| 4198 | 3 | 4 | 5 | 6 | 7 | VII-1 | Snora21 |
| 4199 | 3 | 4 | 5 | 6 | 7 | VII-1 | Snora23 |
| 4200 | 3 | 4 | 5 | 6 | 7 | VII-1 | Snora28 |
| 4201 | 3 | 4 | 5 | 6 | 7 | VII-1 | Snora3 |
| 4202 | 3 | 4 | 5 | 6 | 7 | VII-1 | Snora31 |
| 4203 | 3 | 4 | 5 | 6 | 7 | VII-1 | Snora33 |
| 4204 | 3 | 4 | 5 | 6 | 7 | VII-1 | Snora34 |
| 4205 | 3 | 4 | 5 | 6 | 7 | VII-1 | Snora41 |
| 4206 | 3 | 4 | 5 | 6 | 7 | VII-1 | Snora43 |
| 4207 | 3 | 4 | 5 | 6 | 7 | VII-1 | Snora44 |
| 4208 | 3 | 4 | 5 | 6 | 7 | VII-1 | Snora52 |
| 4209 | 3 | 4 | 5 | 6 | 7 | VII-1 | Snora62 |
| 4210 | 3 | 4 | 5 | 6 | 7 | VII-1 | Snora64 |
| 4211 | 3 | 4 | 5 | 6 | 7 | VII-1 | Snora65 |
| 4212 | 3 | 4 | 5 | 6 | 7 | VII-1 | Snora69 |
| 4213 | 3 | 4 | 5 | 6 | 7 | VII-1 | Snora70 |
| 4214 | 3 | 4 | 5 | 6 | 7 | VII-1 | Snora74a |
| 4215 | 3 | 4 | 5 | 6 | 7 | VII-1 | Snora75 |
| 4216 | 3 | 4 | 5 | 6 | 7 | VII-1 | Snora78 |
| 4217 | 3 | 4 | 5 | 6 | 7 | VII-1 | Snora7a |
| 4218 | 3 | 4 | 5 | 6 | 7 | VII-1 | Snora81 |
| 4219 | 3 | 4 | 5 | 6 | 7 | VII-1 | Snord15a |
| 4220 | 3 | 4 | 5 | 6 | 7 | VII-1 | Snord15b |
| 4221 | 3 | 4 | 5 | 6 | 7 | VII-1 | Snord17 |
| 4222 | 3 | 4 | 5 | 6 | 7 | VII-1 | Snord22 |

Fig. 34 - 23

| | | | | | | | |
|---|---|---|---|---|---|---|---|
| 4223 | 3 | 4 | 5 | 6 | 7 | VII-1 | Snord7 |
| 4224 | 3 | 4 | 5 | 6 | 7 | VII-1 | Snph |
| 4225 | 3 | 4 | 5 | 6 | 7 | VII-1 | Snrnp25 |
| 4226 | 3 | 4 | 5 | 6 | 7 | VII-1 | Snrnp27 |
| 4227 | 3 | 4 | 5 | 6 | 7 | VII-1 | Snrpa1 |
| 4228 | 3 | 4 | 5 | 6 | 7 | VII-1 | Snrpb |
| 4229 | 3 | 4 | 5 | 6 | 7 | VII-1 | Snrpc |
| 4230 | 3 | 4 | 5 | 6 | 7 | VII-1 | Snrpd2 |
| 4231 | 3 | 4 | 5 | 6 | 7 | VII-1 | Snrpe |
| 4232 | 3 | 4 | 5 | 6 | 7 | VII-1 | Snrpf |
| 4233 | 3 | 4 | 5 | 6 | 7 | VII-1 | Snrpg |
| 4234 | 3 | 4 | 5 | 6 | 7 | VII-1 | Snrpn |
| 4235 | 3 | 4 | 5 | 6 | 7 | VII-1 | Snurf |
| 4236 | 3 | 4 | 5 | 6 | 7 | VII-1 | Snx17 |
| 4237 | 3 | 4 | 5 | 6 | 7 | VII-1 | Snx20 |
| 4238 | 3 | 4 | 5 | 6 | 7 | VII-1 | Soat1 |
| 4239 | 3 | 4 | 5 | 6 | 7 | VII-1 | Soat2 |
| 4240 | 3 | 4 | 5 | 6 | 7 | VII-1 | Socs2 |
| 4241 | 3 | 4 | 5 | 6 | 7 | VII-1 | Sod1 |
| 4242 | 3 | 4 | 5 | 6 | 7 | VII-1 | Sod3 |
| 4243 | 3 | 4 | 5 | 6 | 7 | VII-1 | Sox11 |
| 4244 | 3 | 4 | 5 | 6 | 7 | VII-1 | Sox4 |
| 4245 | 3 | 4 | 5 | 6 | 7 | VII-1 | Sp110 |
| 4246 | 3 | 4 | 5 | 6 | 7 | VII-1 | Spa17 |
| 4247 | 3 | 4 | 5 | 6 | 7 | VII-1 | Spag11a |
| 4248 | 3 | 4 | 5 | 6 | 7 | VII-1 | Spata24 |
| 4249 | 3 | 4 | 5 | 6 | 7 | VII-1 | Spata3 |
| 4250 | 3 | 4 | 5 | 6 | 7 | VII-1 | Spc24 |
| 4251 | 3 | 4 | 5 | 6 | 7 | VII-1 | Spem1 |
| 4252 | 3 | 4 | 5 | 6 | 7 | VII-1 | Spg7 |
| 4253 | 3 | 4 | 5 | 6 | 7 | VII-1 | Spink1 |
| 4254 | 3 | 4 | 5 | 6 | 7 | VII-1 | Spink3 |
| 4255 | 3 | 4 | 5 | 6 | 7 | VII-1 | Spink6 |
| 4256 | 3 | 4 | 5 | 6 | 7 | VII-1 | Spink8 |
| 4257 | 3 | 4 | 5 | 6 | 7 | VII-1 | Spint3 |
| 4258 | 3 | 4 | 5 | 6 | 7 | VII-1 | Spock1 |
| 4259 | 3 | 4 | 5 | 6 | 7 | VII-1 | Spock2 |
| 4260 | 3 | 4 | 5 | 6 | 7 | VII-1 | Spp1 |
| 4261 | 3 | 4 | 5 | 6 | 7 | VII-1 | Sprn |
| 4262 | 3 | 4 | 5 | 6 | 7 | VII-1 | Sprr2i |
| 4263 | 3 | 4 | 5 | 6 | 7 | VII-1 | Spsb1 |
| 4264 | 3 | 4 | 5 | 6 | 7 | VII-1 | Spsb4 |
| 4265 | 3 | 4 | 5 | 6 | 7 | VII-1 | Spt1 |
| 4266 | 3 | 4 | 5 | 6 | 7 | VII-1 | Sptbn2 |
| 4267 | 3 | 4 | 5 | 6 | 7 | VII-1 | Spz1 |
| 4268 | 3 | 4 | 5 | 6 | 7 | VII-1 | Srcin1 |
| 4269 | 3 | 4 | 5 | 6 | 7 | VII-1 | Srm |
| 4270 | 3 | 4 | 5 | 6 | 7 | VII-1 | Srp19 |
| 4271 | 3 | 4 | 5 | 6 | 7 | VII-1 | Srp54c |
| 4272 | 3 | 4 | 5 | 6 | 7 | VII-1 | Srp9 |
| 4273 | 3 | 4 | 5 | 6 | 7 | VII-1 | Srpk3 |
| 4274 | 3 | 4 | 5 | 6 | 7 | VII-1 | Srrd |
| 4275 | 3 | 4 | 5 | 6 | 7 | VII-1 | Ssbp4 |
| 4276 | 3 | 4 | 5 | 6 | 7 | VII-1 | Ssna1 |
| 4277 | 3 | 4 | 5 | 6 | 7 | VII-1 | Ssr4 |
| 4278 | 3 | 4 | 5 | 6 | 7 | VII-1 | Sssca1 |
| 4279 | 3 | 4 | 5 | 6 | 7 | VII-1 | Sst |
| 4280 | 3 | 4 | 5 | 6 | 7 | VII-1 | St14 |
| 4281 | 3 | 4 | 5 | 6 | 7 | VII-1 | St3gal3 |
| 4282 | 3 | 4 | 5 | 6 | 7 | VII-1 | St6galnac2 |
| 4283 | 3 | 4 | 5 | 6 | 7 | VII-1 | Stard10 |
| 4284 | 3 | 4 | 5 | 6 | 7 | VII-1 | Stbd1 |
| 4285 | 3 | 4 | 5 | 6 | 7 | VII-1 | Stfa1 |
| 4286 | 3 | 4 | 5 | 6 | 7 | VII-1 | Stfa2l1 |
| 4287 | 3 | 4 | 5 | 6 | 7 | VII-1 | Stfa3 |
| 4288 | 3 | 4 | 5 | 6 | 7 | VII-1 | Stk19 |
| 4289 | 3 | 4 | 5 | 6 | 7 | VII-1 | Stk39 |
| 4290 | 3 | 4 | 5 | 6 | 7 | VII-1 | Stmn2 |
| 4291 | 3 | 4 | 5 | 6 | 7 | VII-1 | Stmn3 |
| 4292 | 3 | 4 | 5 | 6 | 7 | VII-1 | Stmn4 |
| 4293 | 3 | 4 | 5 | 6 | 7 | VII-1 | Ston1 |
| 4294 | 3 | 4 | 5 | 6 | 7 | VII-1 | Stx1b |
| 4295 | 3 | 4 | 5 | 6 | 7 | VII-1 | Stx4a |
| 4296 | 3 | 4 | 5 | 6 | 7 | VII-1 | Stx8 |
| 4297 | 3 | 4 | 5 | 6 | 7 | VII-1 | Suclg1 |
| 4298 | 3 | 4 | 5 | 6 | 7 | VII-1 | Sugt1 |
| 4299 | 3 | 4 | 5 | 6 | 7 | VII-1 | Sult1a1 |
| 4300 | 3 | 4 | 5 | 6 | 7 | VII-1 | Sult1e1 |
| 4301 | 3 | 4 | 5 | 6 | 7 | VII-1 | Sult2b1 |
| 4302 | 3 | 4 | 5 | 6 | 7 | VII-1 | Sult4a1 |
| 4303 | 3 | 4 | 5 | 6 | 7 | VII-1 | Sult5a1 |
| 4304 | 3 | 4 | 5 | 6 | 7 | VII-1 | Supt16 |
| 4305 | 3 | 4 | 5 | 6 | 7 | VII-1 | Supt3 |
| 4306 | 3 | 4 | 5 | 6 | 7 | VII-1 | Supt4a |
| 4307 | 3 | 4 | 5 | 6 | 7 | VII-1 | Supt5 |
| 4308 | 3 | 4 | 5 | 6 | 7 | VII-1 | Sv2b |
| 4309 | 3 | 4 | 5 | 6 | 7 | VII-1 | Syce3 |
| 4310 | 3 | 4 | 5 | 6 | 7 | VII-1 | Sycn |
| 4311 | 3 | 4 | 5 | 6 | 7 | VII-1 | Syde2 |
| 4312 | 3 | 4 | 5 | 6 | 7 | VII-1 | Syf2 |
| 4313 | 3 | 4 | 5 | 6 | 7 | VII-1 | Sympk |
| 4314 | 3 | 4 | 5 | 6 | 7 | VII-1 | Syn1 |
| 4315 | 3 | 4 | 5 | 6 | 7 | VII-1 | Syn2 |
| 4316 | 3 | 4 | 5 | 6 | 7 | VII-1 | Syngr1 |
| 4317 | 3 | 4 | 5 | 6 | 7 | VII-1 | Syngr3 |
| 4318 | 3 | 4 | 5 | 6 | 7 | VII-1 | Syp |
| 4319 | 3 | 4 | 5 | 6 | 7 | VII-1 | Syt1 |
| 4320 | 3 | 4 | 5 | 6 | 7 | VII-1 | Syt13 |
| 4321 | 3 | 4 | 5 | 6 | 7 | VII-1 | Syt4 |
| 4322 | 3 | 4 | 5 | 6 | 7 | VII-1 | Syt5 |
| 4323 | 3 | 4 | 5 | 6 | 7 | VII-1 | Syt7 |
| 4324 | 3 | 4 | 5 | 6 | 7 | VII-1 | Sytl1 |
| 4325 | 3 | 4 | 5 | 6 | 7 | VII-1 | Sytl3 |
| 4326 | 3 | 4 | 5 | 6 | 7 | VII-1 | Tac2 |
| 4327 | 3 | 4 | 5 | 6 | 7 | VII-1 | Tagln3 |
| 4328 | 3 | 4 | 5 | 6 | 7 | VII-1 | Taldo1 |
| 4329 | 3 | 4 | 5 | 6 | 7 | VII-1 | Tat |
| 4330 | 3 | 4 | 5 | 6 | 7 | VII-1 | Tbc1d10c |
| 4331 | 3 | 4 | 5 | 6 | 7 | VII-1 | Tbc1d17 |
| 4332 | 3 | 4 | 5 | 6 | 7 | VII-1 | Tbce |
| 4333 | 3 | 4 | 5 | 6 | 7 | VII-1 | Tcap |
| 4334 | 3 | 4 | 5 | 6 | 7 | VII-1 | Tceal5 |
| 4335 | 3 | 4 | 5 | 6 | 7 | VII-1 | Tceal6 |
| 4336 | 3 | 4 | 5 | 6 | 7 | VII-1 | Tceb1 |
| 4337 | 3 | 4 | 5 | 6 | 7 | VII-1 | Tceb2 |
| 4338 | 3 | 4 | 5 | 6 | 7 | VII-1 | Tcf25 |
| 4339 | 3 | 4 | 5 | 6 | 7 | VII-1 | Tcn2 |
| 4340 | 3 | 4 | 5 | 6 | 7 | VII-1 | Tcp11 |
| 4341 | 3 | 4 | 5 | 6 | 7 | VII-1 | Tcp11l2 |
| 4342 | 3 | 4 | 5 | 6 | 7 | VII-1 | Tcte3 |
| 4343 | 3 | 4 | 5 | 6 | 7 | VII-1 | Tead1 |
| 4344 | 3 | 4 | 5 | 6 | 7 | VII-1 | Tead4 |
| 4345 | 3 | 4 | 5 | 6 | 7 | VII-1 | Tecr |
| 4346 | 3 | 4 | 5 | 6 | 7 | VII-1 | Tekt1 |
| 4347 | 3 | 4 | 5 | 6 | 7 | VII-1 | Tekt2 |
| 4348 | 3 | 4 | 5 | 6 | 7 | VII-1 | Tesc |
| 4349 | 3 | 4 | 5 | 6 | 7 | VII-1 | Tex264 |
| 4350 | 3 | 4 | 5 | 6 | 7 | VII-1 | Tff1 |
| 4351 | 3 | 4 | 5 | 6 | 7 | VII-1 | Tff2 |
| 4352 | 3 | 4 | 5 | 6 | 7 | VII-1 | Tff3 |
| 4353 | 3 | 4 | 5 | 6 | 7 | VII-1 | Tgif1 |
| 4354 | 3 | 4 | 5 | 6 | 7 | VII-1 | Tgoln2 |
| 4355 | 3 | 4 | 5 | 6 | 7 | VII-1 | Tgtp1 |
| 4356 | 3 | 4 | 5 | 6 | 7 | VII-1 | Tgtp2 |
| 4357 | 3 | 4 | 5 | 6 | 7 | VII-1 | Thap3 |
| 4358 | 3 | 4 | 5 | 6 | 7 | VII-1 | Thap7 |
| 4359 | 3 | 4 | 5 | 6 | 7 | VII-1 | Thbs1 |
| 4360 | 3 | 4 | 5 | 6 | 7 | VII-1 | Thrsp |
| 4361 | 3 | 4 | 5 | 6 | 7 | VII-1 | Tigit |
| 4362 | 3 | 4 | 5 | 6 | 7 | VII-1 | Timm10b |
| 4363 | 3 | 4 | 5 | 6 | 7 | VII-1 | Timm13 |
| 4364 | 3 | 4 | 5 | 6 | 7 | VII-1 | Timm44 |
| 4365 | 3 | 4 | 5 | 6 | 7 | VII-1 | Timm50 |
| 4366 | 3 | 4 | 5 | 6 | 7 | VII-1 | Timp1 |
| 4367 | 3 | 4 | 5 | 6 | 7 | VII-1 | Tlcd2 |
| 4368 | 3 | 4 | 5 | 6 | 7 | VII-1 | Tma16 |
| 4369 | 3 | 4 | 5 | 6 | 7 | VII-1 | Tmc6 |
| 4370 | 3 | 4 | 5 | 6 | 7 | VII-1 | Tmco2 |
| 4371 | 3 | 4 | 5 | 6 | 7 | VII-1 | Tmed3 |
| 4372 | 3 | 4 | 5 | 6 | 7 | VII-1 | Tmem107 |
| 4373 | 3 | 4 | 5 | 6 | 7 | VII-1 | Tmem120a |
| 4374 | 3 | 4 | 5 | 6 | 7 | VII-1 | Tmem130 |
| 4375 | 3 | 4 | 5 | 6 | 7 | VII-1 | Tmem140 |
| 4376 | 3 | 4 | 5 | 6 | 7 | VII-1 | Tmem141 |
| 4377 | 3 | 4 | 5 | 6 | 7 | VII-1 | Tmem147 |
| 4378 | 3 | 4 | 5 | 6 | 7 | VII-1 | Tmem14c |
| 4379 | 3 | 4 | 5 | 6 | 7 | VII-1 | Tmem151a |
| 4380 | 3 | 4 | 5 | 6 | 7 | VII-1 | Tmem160 |
| 4381 | 3 | 4 | 5 | 6 | 7 | VII-1 | Tmem167b |
| 4382 | 3 | 4 | 5 | 6 | 7 | VII-1 | Tmem179 |
| 4383 | 3 | 4 | 5 | 6 | 7 | VII-1 | Tmem179b |
| 4384 | 3 | 4 | 5 | 6 | 7 | VII-1 | Tmem198b |
| 4385 | 3 | 4 | 5 | 6 | 7 | VII-1 | Tmem205 |
| 4386 | 3 | 4 | 5 | 6 | 7 | VII-1 | Tmem208 |
| 4387 | 3 | 4 | 5 | 6 | 7 | VII-1 | Tmem25 |
| 4388 | 3 | 4 | 5 | 6 | 7 | VII-1 | Tmem252 |
| 4389 | 3 | 4 | 5 | 6 | 7 | VII-1 | Tmem254c |
| 4390 | 3 | 4 | 5 | 6 | 7 | VII-1 | Tmem256 |
| 4391 | 3 | 4 | 5 | 6 | 7 | VII-1 | Tmem258 |
| 4392 | 3 | 4 | 5 | 6 | 7 | VII-1 | Tmem259 |
| 4393 | 3 | 4 | 5 | 6 | 7 | VII-1 | Tmem37 |
| 4394 | 3 | 4 | 5 | 6 | 7 | VII-1 | Tmem40 |
| 4395 | 3 | 4 | 5 | 6 | 7 | VII-1 | Tmem50a |
| 4396 | 3 | 4 | 5 | 6 | 7 | VII-1 | Tmem56 |
| 4397 | 3 | 4 | 5 | 6 | 7 | VII-1 | Tmem59l |
| 4398 | 3 | 4 | 5 | 6 | 7 | VII-1 | Tmem82 |
| 4399 | 3 | 4 | 5 | 6 | 7 | VII-1 | Tmem86b |
| 4400 | 3 | 4 | 5 | 6 | 7 | VII-1 | Tmem88 |
| 4401 | 3 | 4 | 5 | 6 | 7 | VII-1 | Tmod1 |
| 4402 | 3 | 4 | 5 | 6 | 7 | VII-1 | Tmod2 |
| 4403 | 3 | 4 | 5 | 6 | 7 | VII-1 | Tmod4 |
| 4404 | 3 | 4 | 5 | 6 | 7 | VII-1 | Tmprss2 |
| 4405 | 3 | 4 | 5 | 6 | 7 | VII-1 | Tmsb10 |
| 4406 | 3 | 4 | 5 | 6 | 7 | VII-1 | Tmsb15b1 |
| 4407 | 3 | 4 | 5 | 6 | 7 | VII-1 | Tmsb15b2 |
| 4408 | 3 | 4 | 5 | 6 | 7 | VII-1 | Tmsb4x |
| 4409 | 3 | 4 | 5 | 6 | 7 | VII-1 | Tmub1 |
| 4410 | 3 | 4 | 5 | 6 | 7 | VII-1 | Tnfrsf1b |
| 4411 | 3 | 4 | 5 | 6 | 7 | VII-1 | Tnfsf13 |
| 4412 | 3 | 4 | 5 | 6 | 7 | VII-1 | Tnmd |
| 4413 | 3 | 4 | 5 | 6 | 7 | VII-1 | Tnnc1 |
| 4414 | 3 | 4 | 5 | 6 | 7 | VII-1 | Tnnc2 |

Fig. 34 - 24

| | | | | | | | |
|---|---|---|---|---|---|---|---|
| 4415 | 3 | 4 | 5 | 6 | 7 | VII-1 | Tnni1 |
| 4416 | 3 | 4 | 5 | 6 | 7 | VII-1 | Tnni2 |
| 4417 | 3 | 4 | 5 | 6 | 7 | VII-1 | Tnni3 |
| 4418 | 3 | 4 | 5 | 6 | 7 | VII-1 | Tnnt1 |
| 4419 | 3 | 4 | 5 | 6 | 7 | VII-1 | Tnnt2 |
| 4420 | 3 | 4 | 5 | 6 | 7 | VII-1 | Tnnt3 |
| 4421 | 3 | 4 | 5 | 6 | 7 | VII-1 | Tnp1 |
| 4422 | 3 | 4 | 5 | 6 | 7 | VII-1 | Tnp2 |
| 4423 | 3 | 4 | 5 | 6 | 7 | VII-1 | Tnxb |
| 4424 | 3 | 4 | 5 | 6 | 7 | VII-1 | Tomm6 |
| 4425 | 3 | 4 | 5 | 6 | 7 | VII-1 | Top1mt |
| 4426 | 3 | 4 | 5 | 6 | 7 | VII-1 | Toporsos |
| 4427 | 3 | 4 | 5 | 6 | 7 | VII-1 | Tpd52l1 |
| 4428 | 3 | 4 | 5 | 6 | 7 | VII-1 | Tpgs1 |
| 4429 | 3 | 4 | 5 | 6 | 7 | VII-1 | Tppp |
| 4430 | 3 | 4 | 5 | 6 | 7 | VII-1 | Tppp3 |
| 4431 | 3 | 4 | 5 | 6 | 7 | VII-1 | Tpsab1 |
| 4432 | 3 | 4 | 5 | 6 | 7 | VII-1 | Tpsg1 |
| 4433 | 3 | 4 | 5 | 6 | 7 | VII-1 | Tpt1 |
| 4434 | 3 | 4 | 5 | 6 | 7 | VII-1 | Trafd1 |
| 4435 | 3 | 4 | 5 | 6 | 7 | VII-1 | Trank1 |
| 4436 | 3 | 4 | 5 | 6 | 7 | VII-1 | Trappc2l |
| 4437 | 3 | 4 | 5 | 6 | 7 | VII-1 | Trappc6a |
| 4438 | 3 | 4 | 5 | 6 | 7 | VII-1 | Trim12a |
| 4439 | 3 | 4 | 5 | 6 | 7 | VII-1 | Trim29 |
| 4440 | 3 | 4 | 5 | 6 | 7 | VII-1 | Trim30a |
| 4441 | 3 | 4 | 5 | 6 | 7 | VII-1 | Trim30b |
| 4442 | 3 | 4 | 5 | 6 | 7 | VII-1 | Trim30d |
| 4443 | 3 | 4 | 5 | 6 | 7 | VII-1 | Trim34a |
| 4444 | 3 | 4 | 5 | 6 | 7 | VII-1 | Trim54 |
| 4445 | 3 | 4 | 5 | 6 | 7 | VII-1 | Trim63 |
| 4446 | 3 | 4 | 5 | 6 | 7 | VII-1 | Trim9 |
| 4447 | 3 | 4 | 5 | 6 | 7 | VII-1 | Trmt1 |
| 4448 | 3 | 4 | 5 | 6 | 7 | VII-1 | Trmu |
| 4449 | 3 | 4 | 5 | 6 | 7 | VII-1 | Trnau1ap |
| 4450 | 3 | 4 | 5 | 6 | 7 | VII-1 | Trnp1 |
| 4451 | 3 | 4 | 5 | 6 | 7 | VII-1 | Tro |
| 4452 | 3 | 4 | 5 | 6 | 7 | VII-1 | Trp53inp1 |
| 4453 | 3 | 4 | 5 | 6 | 7 | VII-1 | Trub2 |
| 4454 | 3 | 4 | 5 | 6 | 7 | VII-1 | Try10 |
| 4455 | 3 | 4 | 5 | 6 | 7 | VII-1 | Try4 |
| 4456 | 3 | 4 | 5 | 6 | 7 | VII-1 | Try5 |
| 4457 | 3 | 4 | 5 | 6 | 7 | VII-1 | Tsacc |
| 4458 | 3 | 4 | 5 | 6 | 7 | VII-1 | Tsc2 |
| 4459 | 3 | 4 | 5 | 6 | 7 | VII-1 | Tsc22d3 |
| 4460 | 3 | 4 | 5 | 6 | 7 | VII-1 | Tspan11 |
| 4461 | 3 | 4 | 5 | 6 | 7 | VII-1 | Tspan17 |
| 4462 | 3 | 4 | 5 | 6 | 7 | VII-1 | Tspan2os |
| 4463 | 3 | 4 | 5 | 6 | 7 | VII-1 | Tspan8 |
| 4464 | 3 | 4 | 5 | 6 | 7 | VII-1 | Tspo |
| 4465 | 3 | 4 | 5 | 6 | 7 | VII-1 | Tssc1 |
| 4466 | 3 | 4 | 5 | 6 | 7 | VII-1 | Tssc4 |
| 4467 | 3 | 4 | 5 | 6 | 7 | VII-1 | Tsta3 |
| 4468 | 3 | 4 | 5 | 6 | 7 | VII-1 | Ttc27 |
| 4469 | 3 | 4 | 5 | 6 | 7 | VII-1 | Ttc36 |
| 4470 | 3 | 4 | 5 | 6 | 7 | VII-1 | Ttc39c |
| 4471 | 3 | 4 | 5 | 6 | 7 | VII-1 | Ttc9b |
| 4472 | 3 | 4 | 5 | 6 | 7 | VII-1 | Ttll7 |
| 4473 | 3 | 4 | 5 | 6 | 7 | VII-1 | Ttr |
| 4474 | 3 | 4 | 5 | 6 | 7 | VII-1 | Ttyh1 |
| 4475 | 3 | 4 | 5 | 6 | 7 | VII-1 | Tub |
| 4476 | 3 | 4 | 5 | 6 | 7 | VII-1 | Tuba3a |
| 4477 | 3 | 4 | 5 | 6 | 7 | VII-1 | Tuba3b |
| 4478 | 3 | 4 | 5 | 6 | 7 | VII-1 | Tuba8 |
| 4479 | 3 | 4 | 5 | 6 | 7 | VII-1 | Tubb2a |
| 4480 | 3 | 4 | 5 | 6 | 7 | VII-1 | Tubb2a-ps2 |
| 4481 | 3 | 4 | 5 | 6 | 7 | VII-1 | Tubb2b |
| 4482 | 3 | 4 | 5 | 6 | 7 | VII-1 | Tubb3 |
| 4483 | 3 | 4 | 5 | 6 | 7 | VII-1 | Tubb4a |
| 4484 | 3 | 4 | 5 | 6 | 7 | VII-1 | Tufm |
| 4485 | 3 | 4 | 5 | 6 | 7 | VII-1 | Txn1 |
| 4486 | 3 | 4 | 5 | 6 | 7 | VII-1 | Txndc17 |
| 4487 | 3 | 4 | 5 | 6 | 7 | VII-1 | Tyk2 |
| 4488 | 3 | 4 | 5 | 6 | 7 | VII-1 | U2af1 |
| 4489 | 3 | 4 | 5 | 6 | 7 | VII-1 | Uap1 |
| 4490 | 3 | 4 | 5 | 6 | 7 | VII-1 | Uba52 |
| 4491 | 3 | 4 | 5 | 6 | 7 | VII-1 | Ubald2 |
| 4492 | 3 | 4 | 5 | 6 | 7 | VII-1 | Ube2a |
| 4493 | 3 | 4 | 5 | 6 | 7 | VII-1 | Ube2c |
| 4494 | 3 | 4 | 5 | 6 | 7 | VII-1 | Ube2cbp |
| 4495 | 3 | 4 | 5 | 6 | 7 | VII-1 | Ube2h |
| 4496 | 3 | 4 | 5 | 6 | 7 | VII-1 | Ube2l6 |
| 4497 | 3 | 4 | 5 | 6 | 7 | VII-1 | Ube2m |
| 4498 | 3 | 4 | 5 | 6 | 7 | VII-1 | Ube2ql1 |
| 4499 | 3 | 4 | 5 | 6 | 7 | VII-1 | Ube2s |
| 4500 | 3 | 4 | 5 | 6 | 7 | VII-1 | Ubl5 |
| 4501 | 3 | 4 | 5 | 6 | 7 | VII-1 | Ubxn1 |
| 4502 | 3 | 4 | 5 | 6 | 7 | VII-1 | Ubxn11 |
| 4503 | 3 | 4 | 5 | 6 | 7 | VII-1 | Ubxn6 |
| 4504 | 3 | 4 | 5 | 6 | 7 | VII-1 | Uchl1 |
| 4505 | 3 | 4 | 5 | 6 | 7 | VII-1 | Uchl3 |
| 4506 | 3 | 4 | 5 | 6 | 7 | VII-1 | Ucma |
| 4507 | 3 | 4 | 5 | 6 | 7 | VII-1 | Ucp1 |
| 4508 | 3 | 4 | 5 | 6 | 7 | VII-1 | Ucp2 |
| 4509 | 3 | 4 | 5 | 6 | 7 | VII-1 | Ufc1 |
| 4510 | 3 | 4 | 5 | 6 | 7 | VII-1 | Ugdh |
| 4511 | 3 | 4 | 5 | 6 | 7 | VII-1 | Umps |
| 4512 | 3 | 4 | 5 | 6 | 7 | VII-1 | Upp1 |
| 4513 | 3 | 4 | 5 | 6 | 7 | VII-1 | Upp2 |
| 4514 | 3 | 4 | 5 | 6 | 7 | VII-1 | Uqcc2 |
| 4515 | 3 | 4 | 5 | 6 | 7 | VII-1 | Uqcr10 |
| 4516 | 3 | 4 | 5 | 6 | 7 | VII-1 | Uqcr11 |
| 4517 | 3 | 4 | 5 | 6 | 7 | VII-1 | Uqcrc1 |
| 4518 | 3 | 4 | 5 | 6 | 7 | VII-1 | Uqcrh |
| 4519 | 3 | 4 | 5 | 6 | 7 | VII-1 | Uqcrq |
| 4520 | 3 | 4 | 5 | 6 | 7 | VII-1 | Urah |
| 4521 | 3 | 4 | 5 | 6 | 7 | VII-1 | Urod |
| 4522 | 3 | 4 | 5 | 6 | 7 | VII-1 | Use1 |
| 4523 | 3 | 4 | 5 | 6 | 7 | VII-1 | Usp18 |
| 4524 | 3 | 4 | 5 | 6 | 7 | VII-1 | Usp3 |
| 4525 | 3 | 4 | 5 | 6 | 7 | VII-1 | Usp4 |
| 4526 | 3 | 4 | 5 | 6 | 7 | VII-1 | Usp54 |
| 4527 | 3 | 4 | 5 | 6 | 7 | VII-1 | Utf1 |
| 4528 | 3 | 4 | 5 | 6 | 7 | VII-1 | Utp11l |
| 4529 | 3 | 4 | 5 | 6 | 7 | VII-1 | Vamp3 |
| 4530 | 3 | 4 | 5 | 6 | 7 | VII-1 | Vamp5 |
| 4531 | 3 | 4 | 5 | 6 | 7 | VII-1 | Vamp8 |
| 4532 | 3 | 4 | 5 | 6 | 7 | VII-1 | Vars2 |
| 4533 | 3 | 4 | 5 | 6 | 7 | VII-1 | Vaultrc5 |
| 4534 | 3 | 4 | 5 | 6 | 7 | VII-1 | Vax1 |
| 4535 | 3 | 4 | 5 | 6 | 7 | VII-1 | Vcpkmt |
| 4536 | 3 | 4 | 5 | 6 | 7 | VII-1 | Vdr |
| 4537 | 3 | 4 | 5 | 6 | 7 | VII-1 | Vezt |
| 4538 | 3 | 4 | 5 | 6 | 7 | VII-1 | Vgf |
| 4539 | 3 | 4 | 5 | 6 | 7 | VII-1 | Vgll4 |
| 4540 | 3 | 4 | 5 | 6 | 7 | VII-1 | Vnn1 |
| 4541 | 3 | 4 | 5 | 6 | 7 | VII-1 | Vpreb3 |
| 4542 | 3 | 4 | 5 | 6 | 7 | VII-1 | Vps16 |
| 4543 | 3 | 4 | 5 | 6 | 7 | VII-1 | Vps28 |
| 4544 | 3 | 4 | 5 | 6 | 7 | VII-1 | Vps36 |
| 4545 | 3 | 4 | 5 | 6 | 7 | VII-1 | Vps45 |
| 4546 | 3 | 4 | 5 | 6 | 7 | VII-1 | Vps53 |
| 4547 | 3 | 4 | 5 | 6 | 7 | VII-1 | Vps8 |
| 4548 | 3 | 4 | 5 | 6 | 7 | VII-1 | Vsig8 |
| 4549 | 3 | 4 | 5 | 6 | 7 | VII-1 | Vsnl1 |
| 4550 | 3 | 4 | 5 | 6 | 7 | VII-1 | Wasf1 |
| 4551 | 3 | 4 | 5 | 6 | 7 | VII-1 | Wbscr22 |
| 4552 | 3 | 4 | 5 | 6 | 7 | VII-1 | Wdr34 |
| 4553 | 3 | 4 | 5 | 6 | 7 | VII-1 | Wdr65 |
| 4554 | 3 | 4 | 5 | 6 | 7 | VII-1 | Wdr74 |
| 4555 | 3 | 4 | 5 | 6 | 7 | VII-1 | Wdr83 |
| 4556 | 3 | 4 | 5 | 6 | 7 | VII-1 | Wdr83os |
| 4557 | 3 | 4 | 5 | 6 | 7 | VII-1 | Wdr92 |
| 4558 | 3 | 4 | 5 | 6 | 7 | VII-1 | Wdr95 |
| 4559 | 3 | 4 | 5 | 6 | 7 | VII-1 | Wfdc10 |
| 4560 | 3 | 4 | 5 | 6 | 7 | VII-1 | Wfdc12 |
| 4561 | 3 | 4 | 5 | 6 | 7 | VII-1 | Wfdc13 |
| 4562 | 3 | 4 | 5 | 6 | 7 | VII-1 | Wfdc15b |
| 4563 | 3 | 4 | 5 | 6 | 7 | VII-1 | Wfdc17 |
| 4564 | 3 | 4 | 5 | 6 | 7 | VII-1 | Wfdc18 |
| 4565 | 3 | 4 | 5 | 6 | 7 | VII-1 | Wfdc2 |
| 4566 | 3 | 4 | 5 | 6 | 7 | VII-1 | Wfdc3 |
| 4567 | 3 | 4 | 5 | 6 | 7 | VII-1 | Wfikkn1 |
| 4568 | 3 | 4 | 5 | 6 | 7 | VII-1 | Wibg |
| 4569 | 3 | 4 | 5 | 6 | 7 | VII-1 | Wif1 |
| 4570 | 3 | 4 | 5 | 6 | 7 | VII-1 | Wipf3 |
| 4571 | 3 | 4 | 5 | 6 | 7 | VII-1 | Wnt11 |
| 4572 | 3 | 4 | 5 | 6 | 7 | VII-1 | Wrap53 |
| 4573 | 3 | 4 | 5 | 6 | 7 | VII-1 | Xaf1 |
| 4574 | 3 | 4 | 5 | 6 | 7 | VII-1 | Xlr4c |
| 4575 | 3 | 4 | 5 | 6 | 7 | VII-1 | Xpnpep1 |
| 4576 | 3 | 4 | 5 | 6 | 7 | VII-1 | Xrcc1 |
| 4577 | 3 | 4 | 5 | 6 | 7 | VII-1 | Ybx2 |
| 4578 | 3 | 4 | 5 | 6 | 7 | VII-1 | Yif1b |
| 4579 | 3 | 4 | 5 | 6 | 7 | VII-1 | Yipf1 |
| 4580 | 3 | 4 | 5 | 6 | 7 | VII-1 | Yipf2 |
| 4581 | 3 | 4 | 5 | 6 | 7 | VII-1 | Ypel3 |
| 4582 | 3 | 4 | 5 | 6 | 7 | VII-1 | Zap70 |
| 4583 | 3 | 4 | 5 | 6 | 7 | VII-1 | Zbp1 |
| 4584 | 3 | 4 | 5 | 6 | 7 | VII-1 | Zbtb16 |
| 4585 | 3 | 4 | 5 | 6 | 7 | VII-1 | Zbtb22 |
| 4586 | 3 | 4 | 5 | 6 | 7 | VII-1 | Zbtb38 |
| 4587 | 3 | 4 | 5 | 6 | 7 | VII-1 | Zbtb8b |
| 4588 | 3 | 4 | 5 | 6 | 7 | VII-1 | Zbtb8os |
| 4589 | 3 | 4 | 5 | 6 | 7 | VII-1 | Zcchc12 |
| 4590 | 3 | 4 | 5 | 6 | 7 | VII-1 | Zcchc17 |
| 4591 | 3 | 4 | 5 | 6 | 7 | VII-1 | Zcwpw1 |
| 4592 | 3 | 4 | 5 | 6 | 7 | VII-1 | Zeb2os |
| 4593 | 3 | 4 | 5 | 6 | 7 | VII-1 | Zfand2b |
| 4594 | 3 | 4 | 5 | 6 | 7 | VII-1 | Zfp36 |
| 4595 | 3 | 4 | 5 | 6 | 7 | VII-1 | Zfp365 |
| 4596 | 3 | 4 | 5 | 6 | 7 | VII-1 | Zfp429 |
| 4597 | 3 | 4 | 5 | 6 | 7 | VII-1 | Zfp524 |
| 4598 | 3 | 4 | 5 | 6 | 7 | VII-1 | Zfp57 |
| 4599 | 3 | 4 | 5 | 6 | 7 | VII-1 | Zfp580 |
| 4600 | 3 | 4 | 5 | 6 | 7 | VII-1 | Zfp593 |
| 4601 | 3 | 4 | 5 | 6 | 7 | VII-1 | Zfp637 |
| 4602 | 3 | 4 | 5 | 6 | 7 | VII-1 | Zfp688 |
| 4603 | 3 | 4 | 5 | 6 | 7 | VII-1 | Zfp771 |
| 4604 | 3 | 4 | 5 | 6 | 7 | VII-1 | Zfp809 |
| 4605 | 3 | 4 | 5 | 6 | 7 | VII-1 | Zfp821 |
| 4606 | 3 | 4 | 5 | 6 | 7 | VII-1 | Zfp97 |

Fig. 34 - 25

| | | | | | | | |
|---|---|---|---|---|---|---|---|
| 4607 | 3 | 4 | 5 | 6 | 7 | VII-1 | Zfp11 |
| 4608 | 3 | 4 | 5 | 6 | 7 | VII-1 | Zg16 |
| 4609 | 3 | 4 | 5 | 6 | 7 | VII-1 | Zim1 |
| 4610 | 3 | 4 | 5 | 6 | 7 | VII-1 | Zkscan6 |
| 4611 | 3 | 4 | 5 | 6 | 7 | VII-1 | Znrd1 |
| 4612 | 3 | 4 | 5 | 6 | 7 | VII-1 | Znrd1as |
| 4613 | 3 | 4 | 5 | 6 | 7 | VII-1 | Znrf4 |
| 4614 | 3 | 4 | 5 | 6 | 7 | VII-1 | Zpr1 |
| 4615 | 3 | 4 | 5 | 6 | 7 | VII-1 | a |
| 4616 | 3 | 4 | 5 | 6 | | VI-2 | 0610007P14Rik |
| 4617 | 3 | 4 | 5 | 6 | | VI-2 | 0610009O20Rik |
| 4618 | 3 | 4 | 5 | 6 | | VI-2 | 0610030E20Rik |
| 4619 | 3 | 4 | 5 | 6 | | VI-2 | 0610038B21Rik |
| 4620 | 3 | 4 | 5 | 6 | | VI-2 | 0610040F04Rik |
| 4621 | 3 | 4 | 5 | 6 | | VI-2 | 1110008P14Rik |
| 4622 | 3 | 4 | 5 | 6 | | VI-2 | 1110032A03Rik |
| 4623 | 3 | 4 | 5 | 6 | | VI-2 | 1110037F02Rik |
| 4624 | 3 | 4 | 5 | 6 | | VI-2 | 1110057K04Rik |
| 4625 | 3 | 4 | 5 | 6 | | VI-2 | 1110059E24Rik |
| 4626 | 3 | 4 | 5 | 6 | | VI-2 | 1190002N15Rik |
| 4627 | 3 | 4 | 5 | 6 | | VI-2 | 1200014J11Rik |
| 4628 | 3 | 4 | 5 | 6 | | VI-2 | 1500004A13Rik |
| 4629 | 3 | 4 | 5 | 6 | | VI-2 | 1600002H07Rik |
| 4630 | 3 | 4 | 5 | 6 | | VI-2 | 1700001L05Rik |
| 4631 | 3 | 4 | 5 | 6 | | VI-2 | 1700003D09Rik |
| 4632 | 3 | 4 | 5 | 6 | | VI-2 | 1700003H04Rik |
| 4633 | 3 | 4 | 5 | 6 | | VI-2 | 1700003M07Rik |
| 4634 | 3 | 4 | 5 | 6 | | VI-2 | 1700007G11Rik |
| 4635 | 3 | 4 | 5 | 6 | | VI-2 | 1700008I05Rik |
| 4636 | 3 | 4 | 5 | 6 | | VI-2 | 1700008J07Rik |
| 4637 | 3 | 4 | 5 | 6 | | VI-2 | 1700009J07Rik |
| 4638 | 3 | 4 | 5 | 6 | | VI-2 | 1700011H03Rik |
| 4639 | 3 | 4 | 5 | 6 | | VI-2 | 1700015F17Rik |
| 4640 | 3 | 4 | 5 | 6 | | VI-2 | 1700017J07Rik |
| 4641 | 3 | 4 | 5 | 6 | | VI-2 | 1700018B24Rik |
| 4642 | 3 | 4 | 5 | 6 | | VI-2 | 1700018F24Rik |
| 4643 | 3 | 4 | 5 | 6 | | VI-2 | 1700019N19Rik |
| 4644 | 3 | 4 | 5 | 6 | | VI-2 | 1700021K19Rik |
| 4645 | 3 | 4 | 5 | 6 | | VI-2 | 1700022A22Rik |
| 4646 | 3 | 4 | 5 | 6 | | VI-2 | 1700022E09Rik |
| 4647 | 3 | 4 | 5 | 6 | | VI-2 | 1700029N11Rik |
| 4648 | 3 | 4 | 5 | 6 | | VI-2 | 1700030F04Rik |
| 4649 | 3 | 4 | 5 | 6 | | VI-2 | 1700030J22Rik |
| 4650 | 3 | 4 | 5 | 6 | | VI-2 | 1700031P21Rik |
| 4651 | 3 | 4 | 5 | 6 | | VI-2 | 1700034F02Rik |
| 4652 | 3 | 4 | 5 | 6 | | VI-2 | 1700034I23Rik |
| 4653 | 3 | 4 | 5 | 6 | | VI-2 | 1700034K08Rik |
| 4654 | 3 | 4 | 5 | 6 | | VI-2 | 1700037H04Rik |
| 4655 | 3 | 4 | 5 | 6 | | VI-2 | 1700041M19Rik |
| 4656 | 3 | 4 | 5 | 6 | | VI-2 | 1700046C09Rik |
| 4657 | 3 | 4 | 5 | 6 | | VI-2 | 1700055N04Rik |
| 4658 | 3 | 4 | 5 | 6 | | VI-2 | 1700067P10Rik |
| 4659 | 3 | 4 | 5 | 6 | | VI-2 | 1700069L16Rik |
| 4660 | 3 | 4 | 5 | 6 | | VI-2 | 1700092K14Rik |
| 4661 | 3 | 4 | 5 | 6 | | VI-2 | 1700096K18Rik |
| 4662 | 3 | 4 | 5 | 6 | | VI-2 | 1700100L14Rik |
| 4663 | 3 | 4 | 5 | 6 | | VI-2 | 1700102P08Rik |
| 4664 | 3 | 4 | 5 | 6 | | VI-2 | 1700110K17Rik |
| 4665 | 3 | 4 | 5 | 6 | | VI-2 | 1700113H08Rik |
| 4666 | 3 | 4 | 5 | 6 | | VI-2 | 1700119H24Rik |
| 4667 | 3 | 4 | 5 | 6 | | VI-2 | 1700120G07Rik |
| 4668 | 3 | 4 | 5 | 6 | | VI-2 | 1700122O11Rik |
| 4669 | 3 | 4 | 5 | 6 | | VI-2 | 1810026J23Rik |
| 4670 | 3 | 4 | 5 | 6 | | VI-2 | 1810037I17Rik |
| 4671 | 3 | 4 | 5 | 6 | | VI-2 | 1810065E05Rik |
| 4672 | 3 | 4 | 5 | 6 | | VI-2 | 2010315B03Rik |
| 4673 | 3 | 4 | 5 | 6 | | VI-2 | 2210016L21Rik |
| 4674 | 3 | 4 | 5 | 6 | | VI-2 | 2210404O09Rik |
| 4675 | 3 | 4 | 5 | 6 | | VI-2 | 2210409E12Rik |
| 4676 | 3 | 4 | 5 | 6 | | VI-2 | 2210416O15Rik |
| 4677 | 3 | 4 | 5 | 6 | | VI-2 | 2300005B03Rik |
| 4678 | 3 | 4 | 5 | 6 | | VI-2 | 2310002D06Rik |
| 4679 | 3 | 4 | 5 | 6 | | VI-2 | 2310005G13Rik |
| 4680 | 3 | 4 | 5 | 6 | | VI-2 | 2310020H05Rik |
| 4681 | 3 | 4 | 5 | 6 | | VI-2 | 2310033P09Rik |
| 4682 | 3 | 4 | 5 | 6 | | VI-2 | 2310065F04Rik |
| 4683 | 3 | 4 | 5 | 6 | | VI-2 | 2310067B10Rik |
| 4684 | 3 | 4 | 5 | 6 | | VI-2 | 2310069G16Rik |
| 4685 | 3 | 4 | 5 | 6 | | VI-2 | 2410016O06Rik |
| 4686 | 3 | 4 | 5 | 6 | | VI-2 | 2410076I21Rik |
| 4687 | 3 | 4 | 5 | 6 | | VI-2 | 2610018G03Rik |
| 4688 | 3 | 4 | 5 | 6 | | VI-2 | 2610020C07Rik |
| 4689 | 3 | 4 | 5 | 6 | | VI-2 | 2610100L16Rik |
| 4690 | 3 | 4 | 5 | 6 | | VI-2 | 2610301B20Rik |
| 4691 | 3 | 4 | 5 | 6 | | VI-2 | 2610305D13Rik |
| 4692 | 3 | 4 | 5 | 6 | | VI-2 | 2700046A06Rik |
| 4693 | 3 | 4 | 5 | 6 | | VI-2 | 2700049A03Rik |
| 4694 | 3 | 4 | 5 | 6 | | VI-2 | 2700099C18Rik |
| 4695 | 3 | 4 | 5 | 6 | | VI-2 | 2810006K23Rik |
| 4696 | 3 | 4 | 5 | 6 | | VI-2 | 2810007J24Rik |
| 4697 | 3 | 4 | 5 | 6 | | VI-2 | 2810055G20Rik |
| 4698 | 3 | 4 | 5 | 6 | | VI-2 | 2810408A11Rik |
| 4699 | 3 | 4 | 5 | 6 | | VI-2 | 2810410L24Rik |
| 4700 | 3 | 4 | 5 | 6 | | VI-2 | 2810417H13Rik |
| 4701 | 3 | 4 | 5 | 6 | | VI-2 | 2810442I21Rik |
| 4702 | 3 | 4 | 5 | 6 | | VI-2 | 2810442N19Rik |

| | | | | | | |
|---|---|---|---|---|---|---|
| 4703 | 3 | 4 | 5 | 6 | VI-2 | 2810454H06Rik |
| 4704 | 3 | 4 | 5 | 6 | VI-2 | 2900052N01Rik |
| 4705 | 3 | 4 | 5 | 6 | VI-2 | 2900097C17Rik |
| 4706 | 3 | 4 | 5 | 6 | VI-2 | 3110007F17Rik |
| 4707 | 3 | 4 | 5 | 6 | VI-2 | 3110082I17Rik |
| 4708 | 3 | 4 | 5 | 6 | VI-2 | 3110082J24Rik |
| 4709 | 3 | 4 | 5 | 6 | VI-2 | 4631405J19Rik |
| 4710 | 3 | 4 | 5 | 6 | VI-2 | 4632415L05Rik |
| 4711 | 3 | 4 | 5 | 6 | VI-2 | 4632427E13Rik |
| 4712 | 3 | 4 | 5 | 6 | VI-2 | 4632428C04Rik |
| 4713 | 3 | 4 | 5 | 6 | VI-2 | 4632434I11Rik |
| 4714 | 3 | 4 | 5 | 6 | VI-2 | 4833422C13Rik |
| 4715 | 3 | 4 | 5 | 6 | VI-2 | 4833423E24Rik |
| 4716 | 3 | 4 | 5 | 6 | VI-2 | 4921504A21Rik |
| 4717 | 3 | 4 | 5 | 6 | VI-2 | 4921506M07Rik |
| 4718 | 3 | 4 | 5 | 6 | VI-2 | 4921511M17Rik |
| 4719 | 3 | 4 | 5 | 6 | VI-2 | 4921531P14Rik |
| 4720 | 3 | 4 | 5 | 6 | VI-2 | 4921534H16Rik |
| 4721 | 3 | 4 | 5 | 6 | VI-2 | 4930404I05Rik |
| 4722 | 3 | 4 | 5 | 6 | VI-2 | 4930414L22Rik |
| 4723 | 3 | 4 | 5 | 6 | VI-2 | 4930414N06Rik |
| 4724 | 3 | 4 | 5 | 6 | VI-2 | 4930415O20Rik |
| 4725 | 3 | 4 | 5 | 6 | VI-2 | 4930423M02Rik |
| 4726 | 3 | 4 | 5 | 6 | VI-2 | 4930426L09Rik |
| 4727 | 3 | 4 | 5 | 6 | VI-2 | 4930427A07Rik |
| 4728 | 3 | 4 | 5 | 6 | VI-2 | 4930428D18Rik |
| 4729 | 3 | 4 | 5 | 6 | VI-2 | 4930430D24Rik |
| 4730 | 3 | 4 | 5 | 6 | VI-2 | 4930440C22Rik |
| 4731 | 3 | 4 | 5 | 6 | VI-2 | 4930447C04Rik |
| 4732 | 3 | 4 | 5 | 6 | VI-2 | 4930447N08Rik |
| 4733 | 3 | 4 | 5 | 6 | VI-2 | 4930449E01Rik |
| 4734 | 3 | 4 | 5 | 6 | VI-2 | 4930449I24Rik |
| 4735 | 3 | 4 | 5 | 6 | VI-2 | 4930451I11Rik |
| 4736 | 3 | 4 | 5 | 6 | VI-2 | 4930452B06Rik |
| 4737 | 3 | 4 | 5 | 6 | VI-2 | 4930453H23Rik |
| 4738 | 3 | 4 | 5 | 6 | VI-2 | 4930455B14Rik |
| 4739 | 3 | 4 | 5 | 6 | VI-2 | 4930467K11Rik |
| 4740 | 3 | 4 | 5 | 6 | VI-2 | 4930468A15Rik |
| 4741 | 3 | 4 | 5 | 6 | VI-2 | 4930474N09Rik |
| 4742 | 3 | 4 | 5 | 6 | VI-2 | 4930480E11Rik |
| 4743 | 3 | 4 | 5 | 6 | VI-2 | 4930480G23Rik |
| 4744 | 3 | 4 | 5 | 6 | VI-2 | 4930483J18Rik |
| 4745 | 3 | 4 | 5 | 6 | VI-2 | 4930486F22Rik |
| 4746 | 3 | 4 | 5 | 6 | VI-2 | 4930503E14Rik |
| 4747 | 3 | 4 | 5 | 6 | VI-2 | 4930503H13Rik |
| 4748 | 3 | 4 | 5 | 6 | VI-2 | 4930503L19Rik |
| 4749 | 3 | 4 | 5 | 6 | VI-2 | 4930506C21Rik |
| 4750 | 3 | 4 | 5 | 6 | VI-2 | 4930513D17Rik |
| 4751 | 3 | 4 | 5 | 6 | VI-2 | 4930515G01Rik |
| 4752 | 3 | 4 | 5 | 6 | VI-2 | 4930519F24Rik |
| 4753 | 3 | 4 | 5 | 6 | VI-2 | 4930519G04Rik |
| 4754 | 3 | 4 | 5 | 6 | VI-2 | 4930520O04Rik |
| 4755 | 3 | 4 | 5 | 6 | VI-2 | 4930528A17Rik |
| 4756 | 3 | 4 | 5 | 6 | VI-2 | 4930529L06Rik |
| 4757 | 3 | 4 | 5 | 6 | VI-2 | 4930532M18Rik |
| 4758 | 3 | 4 | 5 | 6 | VI-2 | 4930550C14Rik |
| 4759 | 3 | 4 | 5 | 6 | VI-2 | 4930550L24Rik |
| 4760 | 3 | 4 | 5 | 6 | VI-2 | 4930556M19Rik |
| 4761 | 3 | 4 | 5 | 6 | VI-2 | 4930558C23Rik |
| 4762 | 3 | 4 | 5 | 6 | VI-2 | 4930558K02Rik |
| 4763 | 3 | 4 | 5 | 6 | VI-2 | 4930562C15Rik |
| 4764 | 3 | 4 | 5 | 6 | VI-2 | 4930562F07Rik |
| 4765 | 3 | 4 | 5 | 6 | VI-2 | 4930563F08Rik |
| 4766 | 3 | 4 | 5 | 6 | VI-2 | 4930564B18Rik |
| 4767 | 3 | 4 | 5 | 6 | VI-2 | 4930565D16Rik |
| 4768 | 3 | 4 | 5 | 6 | VI-2 | 4930567K20Rik |
| 4769 | 3 | 4 | 5 | 6 | VI-2 | 4930570G19Rik |
| 4770 | 3 | 4 | 5 | 6 | VI-2 | 4930577N17Rik |
| 4771 | 3 | 4 | 5 | 6 | VI-2 | 4930578N18Rik |
| 4772 | 3 | 4 | 5 | 6 | VI-2 | 4930579G24Rik |
| 4773 | 3 | 4 | 5 | 6 | VI-2 | 4930579K19Rik |
| 4774 | 3 | 4 | 5 | 6 | VI-2 | 4930596I21Rik |
| 4775 | 3 | 4 | 5 | 6 | VI-2 | 4930599N23Rik |
| 4776 | 3 | 4 | 5 | 6 | VI-2 | 4931406C07Rik |
| 4777 | 3 | 4 | 5 | 6 | VI-2 | 4931414P19Rik |
| 4778 | 3 | 4 | 5 | 6 | VI-2 | 4931417E11Rik |
| 4779 | 3 | 4 | 5 | 6 | VI-2 | 4931428F04Rik |
| 4780 | 3 | 4 | 5 | 6 | VI-2 | 4931431B13Rik |
| 4781 | 3 | 4 | 5 | 6 | VI-2 | 4932414N04Rik |
| 4782 | 3 | 4 | 5 | 6 | VI-2 | 4932438A13Rik |
| 4783 | 3 | 4 | 5 | 6 | VI-2 | 4932443J19Rik |
| 4784 | 3 | 4 | 5 | 6 | VI-2 | 4933400A11Rik |
| 4785 | 3 | 4 | 5 | 6 | VI-2 | 4933400F21Rik |
| 4786 | 3 | 4 | 5 | 6 | VI-2 | 4933400L20Rik |
| 4787 | 3 | 4 | 5 | 6 | VI-2 | 4933402E13Rik |
| 4788 | 3 | 4 | 5 | 6 | VI-2 | 4933402N03Rik |
| 4789 | 3 | 4 | 5 | 6 | VI-2 | 4933403O08Rik |
| 4790 | 3 | 4 | 5 | 6 | VI-2 | 4933404G15Rik |
| 4791 | 3 | 4 | 5 | 6 | VI-2 | 4933404O12Rik |
| 4792 | 3 | 4 | 5 | 6 | VI-2 | 4933405L10Rik |
| 4793 | 3 | 4 | 5 | 6 | VI-2 | 4933405O20Rik |
| 4794 | 3 | 4 | 5 | 6 | VI-2 | 4933408B17Rik |
| 4795 | 3 | 4 | 5 | 6 | VI-2 | 4933411K20Rik |
| 4796 | 3 | 4 | 5 | 6 | VI-2 | 4933416M07Rik |
| 4797 | 3 | 4 | 5 | 6 | VI-2 | 4933422H20Rik |
| 4798 | 3 | 4 | 5 | 6 | VI-2 | 4933427D14Rik |

Fig. 34 - 26

| | | | | | | |
|---|---|---|---|---|---|---|
| 4799 | 3 | 4 | 5 | 6 | VI-2 | 4933433G08Rik |
| 4800 | 3 | 4 | 5 | 6 | VI-2 | 4933434I20Rik |
| 4801 | 3 | 4 | 5 | 6 | VI-2 | 4933436I01Rik |
| 4802 | 3 | 4 | 5 | 6 | VI-2 | 4933439K11Rik |
| 4803 | 3 | 4 | 5 | 6 | VI-2 | 5033403H07Rik |
| 4804 | 3 | 4 | 5 | 6 | VI-2 | 5033404E19Rik |
| 4805 | 3 | 4 | 5 | 6 | VI-2 | 5430417L22Rik |
| 4806 | 3 | 4 | 5 | 6 | VI-2 | 5430427M07Rik |
| 4807 | 3 | 4 | 5 | 6 | VI-2 | 5430427O19Rik |
| 4808 | 3 | 4 | 5 | 6 | VI-2 | 5430435G22Rik |
| 4809 | 3 | 4 | 5 | 6 | VI-2 | 5530601H04Rik |
| 4810 | 3 | 4 | 5 | 6 | VI-2 | 5730403I07Rik |
| 4811 | 3 | 4 | 5 | 6 | VI-2 | 5730422E09Rik |
| 4812 | 3 | 4 | 5 | 6 | VI-2 | 5730508B09Rik |
| 4813 | 3 | 4 | 5 | 6 | VI-2 | 5730559C18Rik |
| 4814 | 3 | 4 | 5 | 6 | VI-2 | 5830418K08Rik |
| 4815 | 3 | 4 | 5 | 6 | VI-2 | 5830428M24Rik |
| 4816 | 3 | 4 | 5 | 6 | VI-2 | 5830432E09Rik |
| 4817 | 3 | 4 | 5 | 6 | VI-2 | 5830444B04Rik |
| 4818 | 3 | 4 | 5 | 6 | VI-2 | 5830473C10Rik |
| 4819 | 3 | 4 | 5 | 6 | VI-2 | 5930403L14Rik |
| 4820 | 3 | 4 | 5 | 6 | VI-2 | 5930430L01Rik |
| 4821 | 3 | 4 | 5 | 6 | VI-2 | 6030468B19Rik |
| 4822 | 3 | 4 | 5 | 6 | VI-2 | 6330549D23Rik |
| 4823 | 3 | 4 | 5 | 6 | VI-2 | 6430503K07Rik |
| 4824 | 3 | 4 | 5 | 6 | VI-2 | 6430562O15Rik |
| 4825 | 3 | 4 | 5 | 6 | VI-2 | 6530402F18Rik |
| 4826 | 3 | 4 | 5 | 6 | VI-2 | 6720489N17Rik |
| 4827 | 3 | 4 | 5 | 6 | VI-2 | 8030462N17Rik |
| 4828 | 3 | 4 | 5 | 6 | VI-2 | 8430419L09Rik |
| 4829 | 3 | 4 | 5 | 6 | VI-2 | 8430427H17Rik |
| 4830 | 3 | 4 | 5 | 6 | VI-2 | 9030612E09Rik |
| 4831 | 3 | 4 | 5 | 6 | VI-2 | 9030619P08Rik |
| 4832 | 3 | 4 | 5 | 6 | VI-2 | 9130008F23Rik |
| 4833 | 3 | 4 | 5 | 6 | VI-2 | 9130011E15Rik |
| 4834 | 3 | 4 | 5 | 6 | VI-2 | 9130023H24Rik |
| 4835 | 3 | 4 | 5 | 6 | VI-2 | 9230116N13Rik |
| 4836 | 3 | 4 | 5 | 6 | VI-2 | 9330133O14Rik |
| 4837 | 3 | 4 | 5 | 6 | VI-2 | 9330159M07Rik |
| 4838 | 3 | 4 | 5 | 6 | VI-2 | 9330175E14Rik |
| 4839 | 3 | 4 | 5 | 6 | VI-2 | 9330182L06Rik |
| 4840 | 3 | 4 | 5 | 6 | VI-2 | 9330188P03Rik |
| 4841 | 3 | 4 | 5 | 6 | VI-2 | 9430014N10Rik |
| 4842 | 3 | 4 | 5 | 6 | VI-2 | 9430015G10Rik |
| 4843 | 3 | 4 | 5 | 6 | VI-2 | 9530052E02Rik |
| 4844 | 3 | 4 | 5 | 6 | VI-2 | 9530080O11Rik |
| 4845 | 3 | 4 | 5 | 6 | VI-2 | 9530082P21Rik |
| 4846 | 3 | 4 | 5 | 6 | VI-2 | 9930104L06Rik |
| 4847 | 3 | 4 | 5 | 6 | VI-2 | 9930111J21Rik1 |
| 4848 | 3 | 4 | 5 | 6 | VI-2 | 9930111J21Rik2 |
| 4849 | 3 | 4 | 5 | 6 | VI-2 | A130077B15Rik |
| 4850 | 3 | 4 | 5 | 6 | VI-2 | A1cf |
| 4851 | 3 | 4 | 5 | 6 | VI-2 | A230070E04Rik |
| 4852 | 3 | 4 | 5 | 6 | VI-2 | A230077H06Rik |
| 4853 | 3 | 4 | 5 | 6 | VI-2 | A230103H11Rik |
| 4854 | 3 | 4 | 5 | 6 | VI-2 | A330009N23Rik |
| 4855 | 3 | 4 | 5 | 6 | VI-2 | A330040F15Rik |
| 4856 | 3 | 4 | 5 | 6 | VI-2 | A330070K13Rik |
| 4857 | 3 | 4 | 5 | 6 | VI-2 | A330102I10Rik |
| 4858 | 3 | 4 | 5 | 6 | VI-2 | A430093F15Rik |
| 4859 | 3 | 4 | 5 | 6 | VI-2 | A430107P09Rik |
| 4860 | 3 | 4 | 5 | 6 | VI-2 | A4gnt |
| 4861 | 3 | 4 | 5 | 6 | VI-2 | A530053G22Rik |
| 4862 | 3 | 4 | 5 | 6 | VI-2 | A530054K11Rik |
| 4863 | 3 | 4 | 5 | 6 | VI-2 | A530058N18Rik |
| 4864 | 3 | 4 | 5 | 6 | VI-2 | A530099J19Rik |
| 4865 | 3 | 4 | 5 | 6 | VI-2 | A630001G21Rik |
| 4866 | 3 | 4 | 5 | 6 | VI-2 | A630020A06 |
| 4867 | 3 | 4 | 5 | 6 | VI-2 | A630066F11Rik |
| 4868 | 3 | 4 | 5 | 6 | VI-2 | A630077J23Rik |
| 4869 | 3 | 4 | 5 | 6 | VI-2 | A730036I17Rik |
| 4870 | 3 | 4 | 5 | 6 | VI-2 | A730090N16Rik |
| 4871 | 3 | 4 | 5 | 6 | VI-2 | A730098P11Rik |
| 4872 | 3 | 4 | 5 | 6 | VI-2 | A830018L16Rik |
| 4873 | 3 | 4 | 5 | 6 | VI-2 | A830052D11Rik |
| 4874 | 3 | 4 | 5 | 6 | VI-2 | A930004D18Rik |
| 4875 | 3 | 4 | 5 | 6 | VI-2 | A930013F10Rik |
| 4876 | 3 | 4 | 5 | 6 | VI-2 | AA413626 |
| 4877 | 3 | 4 | 5 | 6 | VI-2 | AA414768 |
| 4878 | 3 | 4 | 5 | 6 | VI-2 | AB041803 |
| 4879 | 3 | 4 | 5 | 6 | VI-2 | AI118078 |
| 4880 | 3 | 4 | 5 | 6 | VI-2 | AI450353 |
| 4881 | 3 | 4 | 5 | 6 | VI-2 | AI464131 |
| 4882 | 3 | 4 | 5 | 6 | VI-2 | AI606473 |
| 4883 | 3 | 4 | 5 | 6 | VI-2 | AI839979 |
| 4884 | 3 | 4 | 5 | 6 | VI-2 | AU022793 |
| 4885 | 3 | 4 | 5 | 6 | VI-2 | AW011738 |
| 4886 | 3 | 4 | 5 | 6 | VI-2 | AW146154 |
| 4887 | 3 | 4 | 5 | 6 | VI-2 | AW209491 |
| 4888 | 3 | 4 | 5 | 6 | VI-2 | AW549877 |
| 4889 | 3 | 4 | 5 | 6 | VI-2 | AW554918 |
| 4890 | 3 | 4 | 5 | 6 | VI-2 | AY358078 |
| 4891 | 3 | 4 | 5 | 6 | VI-2 | Aadacl2 |
| 4892 | 3 | 4 | 5 | 6 | VI-2 | Aagab |
| 4893 | 3 | 4 | 5 | 6 | VI-2 | Aak1 |
| 4894 | 3 | 4 | 5 | 6 | VI-2 | Aanat |
| 4895 | 3 | 4 | 5 | 6 | VI-2 | Aasdh |
| 4896 | 3 | 4 | 5 | 6 | VI-2 | Aasdhppt |
| 4897 | 3 | 4 | 5 | 6 | VI-2 | Abca1 |
| 4898 | 3 | 4 | 5 | 6 | VI-2 | Abca14 |
| 4899 | 3 | 4 | 5 | 6 | VI-2 | Abca15 |
| 4900 | 3 | 4 | 5 | 6 | VI-2 | Abca2 |
| 4901 | 3 | 4 | 5 | 6 | VI-2 | Abca3 |
| 4902 | 3 | 4 | 5 | 6 | VI-2 | Abca8a |
| 4903 | 3 | 4 | 5 | 6 | VI-2 | Abca8b |
| 4904 | 3 | 4 | 5 | 6 | VI-2 | Abcb10 |
| 4905 | 3 | 4 | 5 | 6 | VI-2 | Abcb7 |
| 4906 | 3 | 4 | 5 | 6 | VI-2 | Abcc1 |
| 4907 | 3 | 4 | 5 | 6 | VI-2 | Abcc10 |
| 4908 | 3 | 4 | 5 | 6 | VI-2 | Abcc4 |
| 4909 | 3 | 4 | 5 | 6 | VI-2 | Abcc6 |
| 4910 | 3 | 4 | 5 | 6 | VI-2 | Abcd3 |
| 4911 | 3 | 4 | 5 | 6 | VI-2 | Abce1 |
| 4912 | 3 | 4 | 5 | 6 | VI-2 | Abcf2 |
| 4913 | 3 | 4 | 5 | 6 | VI-2 | Abcg2 |
| 4914 | 3 | 4 | 5 | 6 | VI-2 | Abcg3 |
| 4915 | 3 | 4 | 5 | 6 | VI-2 | Abcg5 |
| 4916 | 3 | 4 | 5 | 6 | VI-2 | Abhd13 |
| 4917 | 3 | 4 | 5 | 6 | VI-2 | Abhd17c |
| 4918 | 3 | 4 | 5 | 6 | VI-2 | Abhd5 |
| 4919 | 3 | 4 | 5 | 6 | VI-2 | Abhd8 |
| 4920 | 3 | 4 | 5 | 6 | VI-2 | Abl2 |
| 4921 | 3 | 4 | 5 | 6 | VI-2 | Acaca |
| 4922 | 3 | 4 | 5 | 6 | VI-2 | Acad11 |
| 4923 | 3 | 4 | 5 | 6 | VI-2 | Acadsb |
| 4924 | 3 | 4 | 5 | 6 | VI-2 | Acan |
| 4925 | 3 | 4 | 5 | 6 | VI-2 | Acbd7 |
| 4926 | 3 | 4 | 5 | 6 | VI-2 | Ace3 |
| 4927 | 3 | 4 | 5 | 6 | VI-2 | Acer1 |
| 4928 | 3 | 4 | 5 | 6 | VI-2 | Acnat1 |
| 4929 | 3 | 4 | 5 | 6 | VI-2 | Aco1 |
| 4930 | 3 | 4 | 5 | 6 | VI-2 | Aco2 |
| 4931 | 3 | 4 | 5 | 6 | VI-2 | Acot11 |
| 4932 | 3 | 4 | 5 | 6 | VI-2 | Acox2 |
| 4933 | 3 | 4 | 5 | 6 | VI-2 | Acp1 |
| 4934 | 3 | 4 | 5 | 6 | VI-2 | Acp6 |
| 4935 | 3 | 4 | 5 | 6 | VI-2 | Acrv1 |
| 4936 | 3 | 4 | 5 | 6 | VI-2 | Acsf2 |
| 4937 | 3 | 4 | 5 | 6 | VI-2 | Acsl5 |
| 4938 | 3 | 4 | 5 | 6 | VI-2 | Actc1 |
| 4939 | 3 | 4 | 5 | 6 | VI-2 | Actl6a |
| 4940 | 3 | 4 | 5 | 6 | VI-2 | Actn1 |
| 4941 | 3 | 4 | 5 | 6 | VI-2 | Actr2 |
| 4942 | 3 | 4 | 5 | 6 | VI-2 | Actr3b |
| 4943 | 3 | 4 | 5 | 6 | VI-2 | Actr6 |
| 4944 | 3 | 4 | 5 | 6 | VI-2 | Actrt1 |
| 4945 | 3 | 4 | 5 | 6 | VI-2 | Acvr1 |
| 4946 | 3 | 4 | 5 | 6 | VI-2 | Acy3 |
| 4947 | 3 | 4 | 5 | 6 | VI-2 | Adad1 |
| 4948 | 3 | 4 | 5 | 6 | VI-2 | Adal |
| 4949 | 3 | 4 | 5 | 6 | VI-2 | Adam12 |
| 4950 | 3 | 4 | 5 | 6 | VI-2 | Adam17 |
| 4951 | 3 | 4 | 5 | 6 | VI-2 | Adam19 |
| 4952 | 3 | 4 | 5 | 6 | VI-2 | Adam1a |
| 4953 | 3 | 4 | 5 | 6 | VI-2 | Adam2 |
| 4954 | 3 | 4 | 5 | 6 | VI-2 | Adam20 |
| 4955 | 3 | 4 | 5 | 6 | VI-2 | Adam24 |
| 4956 | 3 | 4 | 5 | 6 | VI-2 | Adam25 |
| 4957 | 3 | 4 | 5 | 6 | VI-2 | Adam26a |
| 4958 | 3 | 4 | 5 | 6 | VI-2 | Adam6b |
| 4959 | 3 | 4 | 5 | 6 | VI-2 | Adamts10 |
| 4960 | 3 | 4 | 5 | 6 | VI-2 | Adamts12 |
| 4961 | 3 | 4 | 5 | 6 | VI-2 | Adamts5 |
| 4962 | 3 | 4 | 5 | 6 | VI-2 | Adamts6 |
| 4963 | 3 | 4 | 5 | 6 | VI-2 | Adamts7 |
| 4964 | 3 | 4 | 5 | 6 | VI-2 | Adamts8 |
| 4965 | 3 | 4 | 5 | 6 | VI-2 | Adamts9 |
| 4966 | 3 | 4 | 5 | 6 | VI-2 | Adamtsl3 |
| 4967 | 3 | 4 | 5 | 6 | VI-2 | Adamtsl5 |
| 4968 | 3 | 4 | 5 | 6 | VI-2 | Adcy9 |
| 4969 | 3 | 4 | 5 | 6 | VI-2 | Adh4 |
| 4970 | 3 | 4 | 5 | 6 | VI-2 | Adhfe1 |
| 4971 | 3 | 4 | 5 | 6 | VI-2 | Adi1 |
| 4972 | 3 | 4 | 5 | 6 | VI-2 | Adipor2 |
| 4973 | 3 | 4 | 5 | 6 | VI-2 | Adk |
| 4974 | 3 | 4 | 5 | 6 | VI-2 | Ado |
| 4975 | 3 | 4 | 5 | 6 | VI-2 | Adora2b |
| 4976 | 3 | 4 | 5 | 6 | VI-2 | Adpgk |
| 4977 | 3 | 4 | 5 | 6 | VI-2 | Adprh |
| 4978 | 3 | 4 | 5 | 6 | VI-2 | Adprm |
| 4979 | 3 | 4 | 5 | 6 | VI-2 | Adra1b |
| 4980 | 3 | 4 | 5 | 6 | VI-2 | Adss |
| 4981 | 3 | 4 | 5 | 6 | VI-2 | Afg3l2 |
| 4982 | 3 | 4 | 5 | 6 | VI-2 | Afm |
| 4983 | 3 | 4 | 5 | 6 | VI-2 | Afmid |
| 4984 | 3 | 4 | 5 | 6 | VI-2 | Agap2 |
| 4985 | 3 | 4 | 5 | 6 | VI-2 | Agbl4 |
| 4986 | 3 | 4 | 5 | 6 | VI-2 | Agk |
| 4987 | 3 | 4 | 5 | 6 | VI-2 | Ago1 |
| 4988 | 3 | 4 | 5 | 6 | VI-2 | Agpat1 |
| 4989 | 3 | 4 | 5 | 6 | VI-2 | Agpat9 |
| 4990 | 3 | 4 | 5 | 6 | VI-2 | Agrn |

Fig. 34 - 27

| | | | | | | |
|---|---|---|---|---|---|---|
| 4991 | 3 | 4 | 5 | 6 | VI-2 | Agtr1a |
| 4992 | 3 | 4 | 5 | 6 | VI-2 | Agxt2 |
| 4993 | 3 | 4 | 5 | 6 | VI-2 | Ahctf1 |
| 4994 | 3 | 4 | 5 | 6 | VI-2 | Ahdc1 |
| 4995 | 3 | 4 | 5 | 6 | VI-2 | Aifm1 |
| 4996 | 3 | 4 | 5 | 6 | VI-2 | Aim2 |
| 4997 | 3 | 4 | 5 | 6 | VI-2 | Ajap1 |
| 4998 | 3 | 4 | 5 | 6 | VI-2 | Ak3 |
| 4999 | 3 | 4 | 5 | 6 | VI-2 | Akap17b |
| 5000 | 3 | 4 | 5 | 6 | VI-2 | Akap8 |
| 5001 | 3 | 4 | 5 | 6 | VI-2 | Akap9 |
| 5002 | 3 | 4 | 5 | 6 | VI-2 | Akna |
| 5003 | 3 | 4 | 5 | 6 | VI-2 | Aknad1 |
| 5004 | 3 | 4 | 5 | 6 | VI-2 | Akr1a1 |
| 5005 | 3 | 4 | 5 | 6 | VI-2 | Akr1c20 |
| 5006 | 3 | 4 | 5 | 6 | VI-2 | Akr1c6 |
| 5007 | 3 | 4 | 5 | 6 | VI-2 | Akr1d1 |
| 5008 | 3 | 4 | 5 | 6 | VI-2 | Akt3 |
| 5009 | 3 | 4 | 5 | 6 | VI-2 | Aldh18a1 |
| 5010 | 3 | 4 | 5 | 6 | VI-2 | Aldh1a2 |
| 5011 | 3 | 4 | 5 | 6 | VI-2 | Aldh1a3 |
| 5012 | 3 | 4 | 5 | 6 | VI-2 | Aldh1b1 |
| 5013 | 3 | 4 | 5 | 6 | VI-2 | Aldh1l2 |
| 5014 | 3 | 4 | 5 | 6 | VI-2 | Aldh3a2 |
| 5015 | 3 | 4 | 5 | 6 | VI-2 | Aldh3b2 |
| 5016 | 3 | 4 | 5 | 6 | VI-2 | Aldh4a1 |
| 5017 | 3 | 4 | 5 | 6 | VI-2 | Aldh9a1 |
| 5018 | 3 | 4 | 5 | 6 | VI-2 | Alg11 |
| 5019 | 3 | 4 | 5 | 6 | VI-2 | Alg12 |
| 5020 | 3 | 4 | 5 | 6 | VI-2 | Alg13 |
| 5021 | 3 | 4 | 5 | 6 | VI-2 | Alg14 |
| 5022 | 3 | 4 | 5 | 6 | VI-2 | Alg6 |
| 5023 | 3 | 4 | 5 | 6 | VI-2 | Alkbh4 |
| 5024 | 3 | 4 | 5 | 6 | VI-2 | Alms1 |
| 5025 | 3 | 4 | 5 | 6 | VI-2 | Alms1-ps2 |
| 5026 | 3 | 4 | 5 | 6 | VI-2 | Alox12e |
| 5027 | 3 | 4 | 5 | 6 | VI-2 | Alpk1 |
| 5028 | 3 | 4 | 5 | 6 | VI-2 | Alppl2 |
| 5029 | 3 | 4 | 5 | 6 | VI-2 | Alx1 |
| 5030 | 3 | 4 | 5 | 6 | VI-2 | Alx3 |
| 5031 | 3 | 4 | 5 | 6 | VI-2 | Amacr |
| 5032 | 3 | 4 | 5 | 6 | VI-2 | Amer1 |
| 5033 | 3 | 4 | 5 | 6 | VI-2 | Amer2 |
| 5034 | 3 | 4 | 5 | 6 | VI-2 | Amigo1 |
| 5035 | 3 | 4 | 5 | 6 | VI-2 | Amigo2 |
| 5036 | 3 | 4 | 5 | 6 | VI-2 | Amigo3 |
| 5037 | 3 | 4 | 5 | 6 | VI-2 | Amotl1 |
| 5038 | 3 | 4 | 5 | 6 | VI-2 | Ampd2 |
| 5039 | 3 | 4 | 5 | 6 | VI-2 | Anapc10 |
| 5040 | 3 | 4 | 5 | 6 | VI-2 | Angel2 |
| 5041 | 3 | 4 | 5 | 6 | VI-2 | Angpt1 |
| 5042 | 3 | 4 | 5 | 6 | VI-2 | Angpt2 |
| 5043 | 3 | 4 | 5 | 6 | VI-2 | Angptl1 |
| 5044 | 3 | 4 | 5 | 6 | VI-2 | Angptl3 |
| 5045 | 3 | 4 | 5 | 6 | VI-2 | Ank |
| 5046 | 3 | 4 | 5 | 6 | VI-2 | Ankef1 |
| 5047 | 3 | 4 | 5 | 6 | VI-2 | Ankib1 |
| 5048 | 3 | 4 | 5 | 6 | VI-2 | Ankle1 |
| 5049 | 3 | 4 | 5 | 6 | VI-2 | Ankra2 |
| 5050 | 3 | 4 | 5 | 6 | VI-2 | Ankrd10 |
| 5051 | 3 | 4 | 5 | 6 | VI-2 | Ankrd12 |
| 5052 | 3 | 4 | 5 | 6 | VI-2 | Ankrd13c |
| 5053 | 3 | 4 | 5 | 6 | VI-2 | Ankrd17 |
| 5054 | 3 | 4 | 5 | 6 | VI-2 | Ankrd26 |
| 5055 | 3 | 4 | 5 | 6 | VI-2 | Ankrd27 |
| 5056 | 3 | 4 | 5 | 6 | VI-2 | Ankrd28 |
| 5057 | 3 | 4 | 5 | 6 | VI-2 | Ankrd32 |
| 5058 | 3 | 4 | 5 | 6 | VI-2 | Ankrd7 |
| 5059 | 3 | 4 | 5 | 6 | VI-2 | Ano8 |
| 5060 | 3 | 4 | 5 | 6 | VI-2 | Anp32e |
| 5061 | 3 | 4 | 5 | 6 | VI-2 | Antxr1 |
| 5062 | 3 | 4 | 5 | 6 | VI-2 | Anxa4 |
| 5063 | 3 | 4 | 5 | 6 | VI-2 | Anxa9 |
| 5064 | 3 | 4 | 5 | 6 | VI-2 | Aoc1 |
| 5065 | 3 | 4 | 5 | 6 | VI-2 | Aox1 |
| 5066 | 3 | 4 | 5 | 6 | VI-2 | Ap1m1 |
| 5067 | 3 | 4 | 5 | 6 | VI-2 | Ap1s3 |
| 5068 | 3 | 4 | 5 | 6 | VI-2 | Ap3b1 |
| 5069 | 3 | 4 | 5 | 6 | VI-2 | Ap3m1 |
| 5070 | 3 | 4 | 5 | 6 | VI-2 | Ap3m2 |
| 5071 | 3 | 4 | 5 | 6 | VI-2 | Apba3 |
| 5072 | 3 | 4 | 5 | 6 | VI-2 | Apbb1ip |
| 5073 | 3 | 4 | 5 | 6 | VI-2 | Api5 |
| 5074 | 3 | 4 | 5 | 6 | VI-2 | Apinr |
| 5075 | 3 | 4 | 5 | 6 | VI-2 | Apobec4 |
| 5076 | 3 | 4 | 5 | 6 | VI-2 | Apol10b |
| 5077 | 3 | 4 | 5 | 6 | VI-2 | Apol11a |
| 5078 | 3 | 4 | 5 | 6 | VI-2 | Apol11b |
| 5079 | 3 | 4 | 5 | 6 | VI-2 | Apol7c |
| 5080 | 3 | 4 | 5 | 6 | VI-2 | App |
| 5081 | 3 | 4 | 5 | 6 | VI-2 | Aqp7 |
| 5082 | 3 | 4 | 5 | 6 | VI-2 | Aqp8 |
| 5083 | 3 | 4 | 5 | 6 | VI-2 | Aqr |
| 5084 | 3 | 4 | 5 | 6 | VI-2 | Ar |
| 5085 | 3 | 4 | 5 | 6 | VI-2 | Arcn1 |
| 5086 | 3 | 4 | 5 | 6 | VI-2 | Arf1 |

| | | | | | | |
|---|---|---|---|---|---|---|
| 5087 | 3 | 4 | 5 | 6 | VI-2 | Arf3 |
| 5088 | 3 | 4 | 5 | 6 | VI-2 | Arf4 |
| 5089 | 3 | 4 | 5 | 6 | VI-2 | Arf6 |
| 5090 | 3 | 4 | 5 | 6 | VI-2 | Arfgef2 |
| 5091 | 3 | 4 | 5 | 6 | VI-2 | Arfrp1 |
| 5092 | 3 | 4 | 5 | 6 | VI-2 | Arhgap1 |
| 5093 | 3 | 4 | 5 | 6 | VI-2 | Arhgap11a |
| 5094 | 3 | 4 | 5 | 6 | VI-2 | Arhgap18 |
| 5095 | 3 | 4 | 5 | 6 | VI-2 | Arhgap19 |
| 5096 | 3 | 4 | 5 | 6 | VI-2 | Arhgap21 |
| 5097 | 3 | 4 | 5 | 6 | VI-2 | Arhgap23 |
| 5098 | 3 | 4 | 5 | 6 | VI-2 | Arhgap27 |
| 5099 | 3 | 4 | 5 | 6 | VI-2 | Arhgap33 |
| 5100 | 3 | 4 | 5 | 6 | VI-2 | Arhgap35 |
| 5101 | 3 | 4 | 5 | 6 | VI-2 | Arhgap39 |
| 5102 | 3 | 4 | 5 | 6 | VI-2 | Arhgdib |
| 5103 | 3 | 4 | 5 | 6 | VI-2 | Arhgef1 |
| 5104 | 3 | 4 | 5 | 6 | VI-2 | Arhgef10 |
| 5105 | 3 | 4 | 5 | 6 | VI-2 | Arhgef12 |
| 5106 | 3 | 4 | 5 | 6 | VI-2 | Arhgef17 |
| 5107 | 3 | 4 | 5 | 6 | VI-2 | Arhgef18 |
| 5108 | 3 | 4 | 5 | 6 | VI-2 | Arhgef39 |
| 5109 | 3 | 4 | 5 | 6 | VI-2 | Arhgef4 |
| 5110 | 3 | 4 | 5 | 6 | VI-2 | Arhgef40 |
| 5111 | 3 | 4 | 5 | 6 | VI-2 | Arid1a |
| 5112 | 3 | 4 | 5 | 6 | VI-2 | Arid1b |
| 5113 | 3 | 4 | 5 | 6 | VI-2 | Arid2 |
| 5114 | 3 | 4 | 5 | 6 | VI-2 | Arih1 |
| 5115 | 3 | 4 | 5 | 6 | VI-2 | Arl14 |
| 5116 | 3 | 4 | 5 | 6 | VI-2 | Arl14ep |
| 5117 | 3 | 4 | 5 | 6 | VI-2 | Arl5a |
| 5118 | 3 | 4 | 5 | 6 | VI-2 | Armcx2 |
| 5119 | 3 | 4 | 5 | 6 | VI-2 | Armcx4 |
| 5120 | 3 | 4 | 5 | 6 | VI-2 | Arsk |
| 5121 | 3 | 4 | 5 | 6 | VI-2 | Artn |
| 5122 | 3 | 4 | 5 | 6 | VI-2 | Asb10 |
| 5123 | 3 | 4 | 5 | 6 | VI-2 | Asb3 |
| 5124 | 3 | 4 | 5 | 6 | VI-2 | Asb7 |
| 5125 | 3 | 4 | 5 | 6 | VI-2 | Ascc3 |
| 5126 | 3 | 4 | 5 | 6 | VI-2 | Ascl1 |
| 5127 | 3 | 4 | 5 | 6 | VI-2 | Asf1a |
| 5128 | 3 | 4 | 5 | 6 | VI-2 | Ash1l |
| 5129 | 3 | 4 | 5 | 6 | VI-2 | Asic1 |
| 5130 | 3 | 4 | 5 | 6 | VI-2 | Asna1 |
| 5131 | 3 | 4 | 5 | 6 | VI-2 | Aspdh |
| 5132 | 3 | 4 | 5 | 6 | VI-2 | Aspm |
| 5133 | 3 | 4 | 5 | 6 | VI-2 | Astn2 |
| 5134 | 3 | 4 | 5 | 6 | VI-2 | Asxl2 |
| 5135 | 3 | 4 | 5 | 6 | VI-2 | Atad2 |
| 5136 | 3 | 4 | 5 | 6 | VI-2 | Atad5 |
| 5137 | 3 | 4 | 5 | 6 | VI-2 | Atat1 |
| 5138 | 3 | 4 | 5 | 6 | VI-2 | Atf2 |
| 5139 | 3 | 4 | 5 | 6 | VI-2 | Atf4 |
| 5140 | 3 | 4 | 5 | 6 | VI-2 | Atf5 |
| 5141 | 3 | 4 | 5 | 6 | VI-2 | Atg12 |
| 5142 | 3 | 4 | 5 | 6 | VI-2 | Atic |
| 5143 | 3 | 4 | 5 | 6 | VI-2 | Atl2 |
| 5144 | 3 | 4 | 5 | 6 | VI-2 | Atm |
| 5145 | 3 | 4 | 5 | 6 | VI-2 | Atmin |
| 5146 | 3 | 4 | 5 | 6 | VI-2 | Atp10b |
| 5147 | 3 | 4 | 5 | 6 | VI-2 | Atp11a |
| 5148 | 3 | 4 | 5 | 6 | VI-2 | Atp12a |
| 5149 | 3 | 4 | 5 | 6 | VI-2 | Atp1b4 |
| 5150 | 3 | 4 | 5 | 6 | VI-2 | Atp2a2 |
| 5151 | 3 | 4 | 5 | 6 | VI-2 | Atp2c1 |
| 5152 | 3 | 4 | 5 | 6 | VI-2 | Atp4a |
| 5153 | 3 | 4 | 5 | 6 | VI-2 | Atp5c1 |
| 5154 | 3 | 4 | 5 | 6 | VI-2 | Atp5f1 |
| 5155 | 3 | 4 | 5 | 6 | VI-2 | Atp6v1e2 |
| 5156 | 3 | 4 | 5 | 6 | VI-2 | Atp8b2 |
| 5157 | 3 | 4 | 5 | 6 | VI-2 | Atp8b5 |
| 5158 | 3 | 4 | 5 | 6 | VI-2 | Atpaf1 |
| 5159 | 3 | 4 | 5 | 6 | VI-2 | Atrn |
| 5160 | 3 | 4 | 5 | 6 | VI-2 | Atrnl1 |
| 5161 | 3 | 4 | 5 | 6 | VI-2 | Atxn10 |
| 5162 | 3 | 4 | 5 | 6 | VI-2 | Atxn2l |
| 5163 | 3 | 4 | 5 | 6 | VI-2 | Atxn7l2 |
| 5164 | 3 | 4 | 5 | 6 | VI-2 | Aurkb |
| 5165 | 3 | 4 | 5 | 6 | VI-2 | Avpr2 |
| 5166 | 3 | 4 | 5 | 6 | VI-2 | B130024G19Rik |
| 5167 | 3 | 4 | 5 | 6 | VI-2 | B130034C11Rik |
| 5168 | 3 | 4 | 5 | 6 | VI-2 | B230217C12Rik |
| 5169 | 3 | 4 | 5 | 6 | VI-2 | B3gat2 |
| 5170 | 3 | 4 | 5 | 6 | VI-2 | B3glct |
| 5171 | 3 | 4 | 5 | 6 | VI-2 | B3gnt4 |
| 5172 | 3 | 4 | 5 | 6 | VI-2 | B3gnt5 |
| 5173 | 3 | 4 | 5 | 6 | VI-2 | B3gnt8 |
| 5174 | 3 | 4 | 5 | 6 | VI-2 | B4galnt3 |
| 5175 | 3 | 4 | 5 | 6 | VI-2 | B4galnt4 |
| 5176 | 3 | 4 | 5 | 6 | VI-2 | B4galt5 |
| 5177 | 3 | 4 | 5 | 6 | VI-2 | B930003M22Rik |
| 5178 | 3 | 4 | 5 | 6 | VI-2 | BB031773 |
| 5179 | 3 | 4 | 5 | 6 | VI-2 | BC005624 |
| 5180 | 3 | 4 | 5 | 6 | VI-2 | BC005764 |
| 5181 | 3 | 4 | 5 | 6 | VI-2 | BC017158 |
| 5182 | 3 | 4 | 5 | 6 | VI-2 | BC024386 |

Fig. 34 - 28

| | | | | | | | |
|---|---|---|---|---|---|---|---|
| 5183 | 3 | 4 | 5 | 6 | VI-2 | BC025920 |
| 5184 | 3 | 4 | 5 | 6 | VI-2 | BC027231 |
| 5185 | 3 | 4 | 5 | 6 | VI-2 | BC030499 |
| 5186 | 3 | 4 | 5 | 6 | VI-2 | BC037034 |
| 5187 | 3 | 4 | 5 | 6 | VI-2 | BC037704 |
| 5188 | 3 | 4 | 5 | 6 | VI-2 | BC039966 |
| 5189 | 3 | 4 | 5 | 6 | VI-2 | BC048502 |
| 5190 | 3 | 4 | 5 | 6 | VI-2 | BC048507 |
| 5191 | 3 | 4 | 5 | 6 | VI-2 | BC048602 |
| 5192 | 3 | 4 | 5 | 6 | VI-2 | BC049352 |
| 5193 | 3 | 4 | 5 | 6 | VI-2 | BC051628 |
| 5194 | 3 | 4 | 5 | 6 | VI-2 | BC061194 |
| 5195 | 3 | 4 | 5 | 6 | VI-2 | Bace1 |
| 5196 | 3 | 4 | 5 | 6 | VI-2 | Bag5 |
| 5197 | 3 | 4 | 5 | 6 | VI-2 | Bahcc1 |
| 5198 | 3 | 4 | 5 | 6 | VI-2 | Baiap3 |
| 5199 | 3 | 4 | 5 | 6 | VI-2 | Bambi |
| 5200 | 3 | 4 | 5 | 6 | VI-2 | Bank1 |
| 5201 | 3 | 4 | 5 | 6 | VI-2 | Banp |
| 5202 | 3 | 4 | 5 | 6 | VI-2 | Bard1 |
| 5203 | 3 | 4 | 5 | 6 | VI-2 | Barx2 |
| 5204 | 3 | 4 | 5 | 6 | VI-2 | Baz1a |
| 5205 | 3 | 4 | 5 | 6 | VI-2 | Baz2a |
| 5206 | 3 | 4 | 5 | 6 | VI-2 | Baz2b |
| 5207 | 3 | 4 | 5 | 6 | VI-2 | Bbs10 |
| 5208 | 3 | 4 | 5 | 6 | VI-2 | Bbs12 |
| 5209 | 3 | 4 | 5 | 6 | VI-2 | Bbx |
| 5210 | 3 | 4 | 5 | 6 | VI-2 | Bcam |
| 5211 | 3 | 4 | 5 | 6 | VI-2 | Bccip |
| 5212 | 3 | 4 | 5 | 6 | VI-2 | Bche |
| 5213 | 3 | 4 | 5 | 6 | VI-2 | Bcl2l13 |
| 5214 | 3 | 4 | 5 | 6 | VI-2 | Bcl9 |
| 5215 | 3 | 4 | 5 | 6 | VI-2 | Bcor |
| 5216 | 3 | 4 | 5 | 6 | VI-2 | Bcorl1 |
| 5217 | 3 | 4 | 5 | 6 | VI-2 | Bdkrb1 |
| 5218 | 3 | 4 | 5 | 6 | VI-2 | Bdkrb2 |
| 5219 | 3 | 4 | 5 | 6 | VI-2 | Bdnf |
| 5220 | 3 | 4 | 5 | 6 | VI-2 | Bet1 |
| 5221 | 3 | 4 | 5 | 6 | VI-2 | Bhlhe40 |
| 5222 | 3 | 4 | 5 | 6 | VI-2 | Bhlhe41 |
| 5223 | 3 | 4 | 5 | 6 | VI-2 | Bicc1 |
| 5224 | 3 | 4 | 5 | 6 | VI-2 | Bin2 |
| 5225 | 3 | 4 | 5 | 6 | VI-2 | Birc2 |
| 5226 | 3 | 4 | 5 | 6 | VI-2 | Birc6 |
| 5227 | 3 | 4 | 5 | 6 | VI-2 | Birc7 |
| 5228 | 3 | 4 | 5 | 6 | VI-2 | Blzf1 |
| 5229 | 3 | 4 | 5 | 6 | VI-2 | Bmi1 |
| 5230 | 3 | 4 | 5 | 6 | VI-2 | Bmp5 |
| 5231 | 3 | 4 | 5 | 6 | VI-2 | Bmp8a |
| 5232 | 3 | 4 | 5 | 6 | VI-2 | Bmper |
| 5233 | 3 | 4 | 5 | 6 | VI-2 | Bnc1 |
| 5234 | 3 | 4 | 5 | 6 | VI-2 | Bnc2 |
| 5235 | 3 | 4 | 5 | 6 | VI-2 | Bod1l |
| 5236 | 3 | 4 | 5 | 6 | VI-2 | Bola3 |
| 5237 | 3 | 4 | 5 | 6 | VI-2 | Bora |
| 5238 | 3 | 4 | 5 | 6 | VI-2 | Bpgm |
| 5239 | 3 | 4 | 5 | 6 | VI-2 | Bphl |
| 5240 | 3 | 4 | 5 | 6 | VI-2 | Bpifa1 |
| 5241 | 3 | 4 | 5 | 6 | VI-2 | Bpifb2 |
| 5242 | 3 | 4 | 5 | 6 | VI-2 | Brat1 |
| 5243 | 3 | 4 | 5 | 6 | VI-2 | Brca1 |
| 5244 | 3 | 4 | 5 | 6 | VI-2 | Brca2 |
| 5245 | 3 | 4 | 5 | 6 | VI-2 | Brd1 |
| 5246 | 3 | 4 | 5 | 6 | VI-2 | Brd3 |
| 5247 | 3 | 4 | 5 | 6 | VI-2 | Brd8 |
| 5248 | 3 | 4 | 5 | 6 | VI-2 | Brdt |
| 5249 | 3 | 4 | 5 | 6 | VI-2 | Bre |
| 5250 | 3 | 4 | 5 | 6 | VI-2 | Bricd5 |
| 5251 | 3 | 4 | 5 | 6 | VI-2 | Brip1 |
| 5252 | 3 | 4 | 5 | 6 | VI-2 | Brpf3 |
| 5253 | 3 | 4 | 5 | 6 | VI-2 | Brwd1 |
| 5254 | 3 | 4 | 5 | 6 | VI-2 | Btbd6 |
| 5255 | 3 | 4 | 5 | 6 | VI-2 | Btd |
| 5256 | 3 | 4 | 5 | 6 | VI-2 | Btf3l4 |
| 5257 | 3 | 4 | 5 | 6 | VI-2 | Btla |
| 5258 | 3 | 4 | 5 | 6 | VI-2 | Btnl1 |
| 5259 | 3 | 4 | 5 | 6 | VI-2 | Btnl10 |
| 5260 | 3 | 4 | 5 | 6 | VI-2 | Btnl6 |
| 5261 | 3 | 4 | 5 | 6 | VI-2 | Bub1b |
| 5262 | 3 | 4 | 5 | 6 | VI-2 | Bzw1 |
| 5263 | 3 | 4 | 5 | 6 | VI-2 | C030013G03Rik |
| 5264 | 3 | 4 | 5 | 6 | VI-2 | C130030K03Rik |
| 5265 | 3 | 4 | 5 | 6 | VI-2 | C130071C03Rik |
| 5266 | 3 | 4 | 5 | 6 | VI-2 | C130079G13Rik |
| 5267 | 3 | 4 | 5 | 6 | VI-2 | C1qtnf1 |
| 5268 | 3 | 4 | 5 | 6 | VI-2 | C1qtnf7 |
| 5269 | 3 | 4 | 5 | 6 | VI-2 | C1ra |
| 5270 | 3 | 4 | 5 | 6 | VI-2 | C1rb |
| 5271 | 3 | 4 | 5 | 6 | VI-2 | C2 |
| 5272 | 3 | 4 | 5 | 6 | VI-2 | C230035I16Rik |
| 5273 | 3 | 4 | 5 | 6 | VI-2 | C2cd3 |
| 5274 | 3 | 4 | 5 | 6 | VI-2 | C2cd5 |
| 5275 | 3 | 4 | 5 | 6 | VI-2 | C330006A16Rik |
| 5276 | 3 | 4 | 5 | 6 | VI-2 | C330027C09Rik |
| 5277 | 3 | 4 | 5 | 6 | VI-2 | C4bp |
| 5278 | 3 | 4 | 5 | 6 | VI-2 | C530005A16Rik |
| 5279 | 3 | 4 | 5 | 6 | VI-2 | C77080 |
| 5280 | 3 | 4 | 5 | 6 | VI-2 | C87436 |
| 5281 | 3 | 4 | 5 | 6 | VI-2 | CK137956 |
| 5282 | 3 | 4 | 5 | 6 | VI-2 | Cables2 |
| 5283 | 3 | 4 | 5 | 6 | VI-2 | Cacna1d |
| 5284 | 3 | 4 | 5 | 6 | VI-2 | Cacnb3 |
| 5285 | 3 | 4 | 5 | 6 | VI-2 | Cactin |
| 5286 | 3 | 4 | 5 | 6 | VI-2 | Cad |
| 5287 | 3 | 4 | 5 | 6 | VI-2 | Cadm1 |
| 5288 | 3 | 4 | 5 | 6 | VI-2 | Cadm4 |
| 5289 | 3 | 4 | 5 | 6 | VI-2 | Calhm2 |
| 5290 | 3 | 4 | 5 | 6 | VI-2 | Calm1 |
| 5291 | 3 | 4 | 5 | 6 | VI-2 | Calm2 |
| 5292 | 3 | 4 | 5 | 6 | VI-2 | Calm5 |
| 5293 | 3 | 4 | 5 | 6 | VI-2 | Camk1d |
| 5294 | 3 | 4 | 5 | 6 | VI-2 | Camk2d |
| 5295 | 3 | 4 | 5 | 6 | VI-2 | Camkmt |
| 5296 | 3 | 4 | 5 | 6 | VI-2 | Camta2 |
| 5297 | 3 | 4 | 5 | 6 | VI-2 | Cand1 |
| 5298 | 3 | 4 | 5 | 6 | VI-2 | Capn1 |
| 5299 | 3 | 4 | 5 | 6 | VI-2 | Capn13 |
| 5300 | 3 | 4 | 5 | 6 | VI-2 | Capn7 |
| 5301 | 3 | 4 | 5 | 6 | VI-2 | Capns2 |
| 5302 | 3 | 4 | 5 | 6 | VI-2 | Caprin2 |
| 5303 | 3 | 4 | 5 | 6 | VI-2 | Capza1 |
| 5304 | 3 | 4 | 5 | 6 | VI-2 | Capza2 |
| 5305 | 3 | 4 | 5 | 6 | VI-2 | Car5a |
| 5306 | 3 | 4 | 5 | 6 | VI-2 | Card14 |
| 5307 | 3 | 4 | 5 | 6 | VI-2 | Card6 |
| 5308 | 3 | 4 | 5 | 6 | VI-2 | Card9 |
| 5309 | 3 | 4 | 5 | 6 | VI-2 | Carf |
| 5310 | 3 | 4 | 5 | 6 | VI-2 | Carns1 |
| 5311 | 3 | 4 | 5 | 6 | VI-2 | Casc5 |
| 5312 | 3 | 4 | 5 | 6 | VI-2 | Casd1 |
| 5313 | 3 | 4 | 5 | 6 | VI-2 | Casp7 |
| 5314 | 3 | 4 | 5 | 6 | VI-2 | Casp8ap2 |
| 5315 | 3 | 4 | 5 | 6 | VI-2 | Casq1 |
| 5316 | 3 | 4 | 5 | 6 | VI-2 | Cass4 |
| 5317 | 3 | 4 | 5 | 6 | VI-2 | Casz1 |
| 5318 | 3 | 4 | 5 | 6 | VI-2 | Catsperb |
| 5319 | 3 | 4 | 5 | 6 | VI-2 | Cav2 |
| 5320 | 3 | 4 | 5 | 6 | VI-2 | Cbfa2t2 |
| 5321 | 3 | 4 | 5 | 6 | VI-2 | Cbr4 |
| 5322 | 3 | 4 | 5 | 6 | VI-2 | Cbx4 |
| 5323 | 3 | 4 | 5 | 6 | VI-2 | Cbx5 |
| 5324 | 3 | 4 | 5 | 6 | VI-2 | Cbx6 |
| 5325 | 3 | 4 | 5 | 6 | VI-2 | Cbx8 |
| 5326 | 3 | 4 | 5 | 6 | VI-2 | Cby1 |
| 5327 | 3 | 4 | 5 | 6 | VI-2 | Cc2d2a |
| 5328 | 3 | 4 | 5 | 6 | VI-2 | Ccar1 |
| 5329 | 3 | 4 | 5 | 6 | VI-2 | Ccar2 |
| 5330 | 3 | 4 | 5 | 6 | VI-2 | Ccbe1 |
| 5331 | 3 | 4 | 5 | 6 | VI-2 | Ccdc105 |
| 5332 | 3 | 4 | 5 | 6 | VI-2 | Ccdc106 |
| 5333 | 3 | 4 | 5 | 6 | VI-2 | Ccdc110 |
| 5334 | 3 | 4 | 5 | 6 | VI-2 | Ccdc115 |
| 5335 | 3 | 4 | 5 | 6 | VI-2 | Ccdc117 |
| 5336 | 3 | 4 | 5 | 6 | VI-2 | Ccdc120 |
| 5337 | 3 | 4 | 5 | 6 | VI-2 | Ccdc122 |
| 5338 | 3 | 4 | 5 | 6 | VI-2 | Ccdc127 |
| 5339 | 3 | 4 | 5 | 6 | VI-2 | Ccdc132 |
| 5340 | 3 | 4 | 5 | 6 | VI-2 | Ccdc14 |
| 5341 | 3 | 4 | 5 | 6 | VI-2 | Ccdc142 |
| 5342 | 3 | 4 | 5 | 6 | VI-2 | Ccdc149 |
| 5343 | 3 | 4 | 5 | 6 | VI-2 | Ccdc160 |
| 5344 | 3 | 4 | 5 | 6 | VI-2 | Ccdc172 |
| 5345 | 3 | 4 | 5 | 6 | VI-2 | Ccdc173 |
| 5346 | 3 | 4 | 5 | 6 | VI-2 | Ccdc175 |
| 5347 | 3 | 4 | 5 | 6 | VI-2 | Ccdc176 |
| 5348 | 3 | 4 | 5 | 6 | VI-2 | Ccdc3 |
| 5349 | 3 | 4 | 5 | 6 | VI-2 | Ccdc30 |
| 5350 | 3 | 4 | 5 | 6 | VI-2 | Ccdc32 |
| 5351 | 3 | 4 | 5 | 6 | VI-2 | Ccdc34os |
| 5352 | 3 | 4 | 5 | 6 | VI-2 | Ccdc38 |
| 5353 | 3 | 4 | 5 | 6 | VI-2 | Ccdc51 |
| 5354 | 3 | 4 | 5 | 6 | VI-2 | Ccdc55 |
| 5355 | 3 | 4 | 5 | 6 | VI-2 | Ccdc62 |
| 5356 | 3 | 4 | 5 | 6 | VI-2 | Ccdc8 |
| 5357 | 3 | 4 | 5 | 6 | VI-2 | Ccdc88a |
| 5358 | 3 | 4 | 5 | 6 | VI-2 | Ccdc89 |
| 5359 | 3 | 4 | 5 | 6 | VI-2 | Ccdc90b |
| 5360 | 3 | 4 | 5 | 6 | VI-2 | Ccl11 |
| 5361 | 3 | 4 | 5 | 6 | VI-2 | Ccl12 |
| 5362 | 3 | 4 | 5 | 6 | VI-2 | Ccnb1 |
| 5363 | 3 | 4 | 5 | 6 | VI-2 | Ccnb1ip1 |
| 5364 | 3 | 4 | 5 | 6 | VI-2 | Ccne1 |
| 5365 | 3 | 4 | 5 | 6 | VI-2 | Ccnf |
| 5366 | 3 | 4 | 5 | 6 | VI-2 | Ccnj |
| 5367 | 3 | 4 | 5 | 6 | VI-2 | Ccny |
| 5368 | 3 | 4 | 5 | 6 | VI-2 | Ccr10 |
| 5369 | 3 | 4 | 5 | 6 | VI-2 | Ccr2 |
| 5370 | 3 | 4 | 5 | 6 | VI-2 | Ccr5 |
| 5371 | 3 | 4 | 5 | 6 | VI-2 | Ccr8 |
| 5372 | 3 | 4 | 5 | 6 | VI-2 | Ccr9 |
| 5373 | 3 | 4 | 5 | 6 | VI-2 | Ccser2 |
| 5374 | 3 | 4 | 5 | 6 | VI-2 | Cct2 |

Fig. 34 - 29

| | | | | | | | |
|---|---|---|---|---|---|---|---|
| 5375 | 3 | 4 | 5 | 6 | | VI-2 | Cd180 |
| 5376 | 3 | 4 | 5 | 6 | | VI-2 | Cd19 |
| 5377 | 3 | 4 | 5 | 6 | | VI-2 | Cd200 |
| 5378 | 3 | 4 | 5 | 6 | | VI-2 | Cd200r1 |
| 5379 | 3 | 4 | 5 | 6 | | VI-2 | Cd209a |
| 5380 | 3 | 4 | 5 | 6 | | VI-2 | Cd209e |
| 5381 | 3 | 4 | 5 | 6 | | VI-2 | Cd226 |
| 5382 | 3 | 4 | 5 | 6 | | VI-2 | Cd244 |
| 5383 | 3 | 4 | 5 | 6 | | VI-2 | Cd248 |
| 5384 | 3 | 4 | 5 | 6 | | VI-2 | Cd27 |
| 5385 | 3 | 4 | 5 | 6 | | VI-2 | Cd28 |
| 5386 | 3 | 4 | 5 | 6 | | VI-2 | Cd300c |
| 5387 | 3 | 4 | 5 | 6 | | VI-2 | Cd300e |
| 5388 | 3 | 4 | 5 | 6 | | VI-2 | Cd300lb |
| 5389 | 3 | 4 | 5 | 6 | | VI-2 | Cd36 |
| 5390 | 3 | 4 | 5 | 6 | | VI-2 | Cd4 |
| 5391 | 3 | 4 | 5 | 6 | | VI-2 | Cd40lg |
| 5392 | 3 | 4 | 5 | 6 | | VI-2 | Cd44 |
| 5393 | 3 | 4 | 5 | 6 | | VI-2 | Cd47 |
| 5394 | 3 | 4 | 5 | 6 | | VI-2 | Cd48 |
| 5395 | 3 | 4 | 5 | 6 | | VI-2 | Cd53 |
| 5396 | 3 | 4 | 5 | 6 | | VI-2 | Cd81 |
| 5397 | 3 | 4 | 5 | 6 | | VI-2 | Cd84 |
| 5398 | 3 | 4 | 5 | 6 | | VI-2 | Cd86 |
| 5399 | 3 | 4 | 5 | 6 | | VI-2 | Cd9 |
| 5400 | 3 | 4 | 5 | 6 | | VI-2 | Cdc20 |
| 5401 | 3 | 4 | 5 | 6 | | VI-2 | Cdc25b |
| 5402 | 3 | 4 | 5 | 6 | | VI-2 | Cdc42bpb |
| 5403 | 3 | 4 | 5 | 6 | | VI-2 | Cdc42ep1 |
| 5404 | 3 | 4 | 5 | 6 | | VI-2 | Cdc42ep4 |
| 5405 | 3 | 4 | 5 | 6 | | VI-2 | Cdc42se2 |
| 5406 | 3 | 4 | 5 | 6 | | VI-2 | Cdc45 |
| 5407 | 3 | 4 | 5 | 6 | | VI-2 | Cdc7 |
| 5408 | 3 | 4 | 5 | 6 | | VI-2 | Cdca2 |
| 5409 | 3 | 4 | 5 | 6 | | VI-2 | Cdca3 |
| 5410 | 3 | 4 | 5 | 6 | | VI-2 | Cdca4 |
| 5411 | 3 | 4 | 5 | 6 | | VI-2 | Cdca7 |
| 5412 | 3 | 4 | 5 | 6 | | VI-2 | Cdh1 |
| 5413 | 3 | 4 | 5 | 6 | | VI-2 | Cdh15 |
| 5414 | 3 | 4 | 5 | 6 | | VI-2 | Cdh19 |
| 5415 | 3 | 4 | 5 | 6 | | VI-2 | Cdh2 |
| 5416 | 3 | 4 | 5 | 6 | | VI-2 | Cdhr1 |
| 5417 | 3 | 4 | 5 | 6 | | VI-2 | Cdk1 |
| 5418 | 3 | 4 | 5 | 6 | | VI-2 | Cdk17 |
| 5419 | 3 | 4 | 5 | 6 | | VI-2 | Cdk2 |
| 5420 | 3 | 4 | 5 | 6 | | VI-2 | Cdk4 |
| 5421 | 3 | 4 | 5 | 6 | | VI-2 | Cdkl3 |
| 5422 | 3 | 4 | 5 | 6 | | VI-2 | Cdkl5 |
| 5423 | 3 | 4 | 5 | 6 | | VI-2 | Cdkn2a |
| 5424 | 3 | 4 | 5 | 6 | | VI-2 | Cdkn3 |
| 5425 | 3 | 4 | 5 | 6 | | VI-2 | Cdnf |
| 5426 | 3 | 4 | 5 | 6 | | VI-2 | Cdr1 |
| 5427 | 3 | 4 | 5 | 6 | | VI-2 | Cds2 |
| 5428 | 3 | 4 | 5 | 6 | | VI-2 | Ceacam16 |
| 5429 | 3 | 4 | 5 | 6 | | VI-2 | Cecr2 |
| 5430 | 3 | 4 | 5 | 6 | | VI-2 | Celf1 |
| 5431 | 3 | 4 | 5 | 6 | | VI-2 | Cemip |
| 5432 | 3 | 4 | 5 | 6 | | VI-2 | Cenpa |
| 5433 | 3 | 4 | 5 | 6 | | VI-2 | Cenpb |
| 5434 | 3 | 4 | 5 | 6 | | VI-2 | Cenpc1 |
| 5435 | 3 | 4 | 5 | 6 | | VI-2 | Cenpf |
| 5436 | 3 | 4 | 5 | 6 | | VI-2 | Cenph |
| 5437 | 3 | 4 | 5 | 6 | | VI-2 | Cenpj |
| 5438 | 3 | 4 | 5 | 6 | | VI-2 | Cenpl |
| 5439 | 3 | 4 | 5 | 6 | | VI-2 | Cenpn |
| 5440 | 3 | 4 | 5 | 6 | | VI-2 | Cenpp |
| 5441 | 3 | 4 | 5 | 6 | | VI-2 | Cenpq |
| 5442 | 3 | 4 | 5 | 6 | | VI-2 | Cep104 |
| 5443 | 3 | 4 | 5 | 6 | | VI-2 | Cep128 |
| 5444 | 3 | 4 | 5 | 6 | | VI-2 | Cep152 |
| 5445 | 3 | 4 | 5 | 6 | | VI-2 | Cep250 |
| 5446 | 3 | 4 | 5 | 6 | | VI-2 | Cep44 |
| 5447 | 3 | 4 | 5 | 6 | | VI-2 | Cep55 |
| 5448 | 3 | 4 | 5 | 6 | | VI-2 | Cep85 |
| 5449 | 3 | 4 | 5 | 6 | | VI-2 | Cep95 |
| 5450 | 3 | 4 | 5 | 6 | | VI-2 | Cept1 |
| 5451 | 3 | 4 | 5 | 6 | | VI-2 | Cercam |
| 5452 | 3 | 4 | 5 | 6 | | VI-2 | Cerk |
| 5453 | 3 | 4 | 5 | 6 | | VI-2 | Ces2f |
| 5454 | 3 | 4 | 5 | 6 | | VI-2 | Ces2g |
| 5455 | 3 | 4 | 5 | 6 | | VI-2 | Ces3b |
| 5456 | 3 | 4 | 5 | 6 | | VI-2 | Cetn2 |
| 5457 | 3 | 4 | 5 | 6 | | VI-2 | Cfhr1 |
| 5458 | 3 | 4 | 5 | 6 | | VI-2 | Cfi |
| 5459 | 3 | 4 | 5 | 6 | | VI-2 | Cfl1 |
| 5460 | 3 | 4 | 5 | 6 | | VI-2 | Ch25h |
| 5461 | 3 | 4 | 5 | 6 | | VI-2 | Chd2 |
| 5462 | 3 | 4 | 5 | 6 | | VI-2 | Chd3 |
| 5463 | 3 | 4 | 5 | 6 | | VI-2 | Chd4 |
| 5464 | 3 | 4 | 5 | 6 | | VI-2 | Chd6 |
| 5465 | 3 | 4 | 5 | 6 | | VI-2 | Chd7 |
| 5466 | 3 | 4 | 5 | 6 | | VI-2 | Chd9 |
| 5467 | 3 | 4 | 5 | 6 | | VI-2 | Chek1 |
| 5468 | 3 | 4 | 5 | 6 | | VI-2 | Cherp |
| 5469 | 3 | 4 | 5 | 6 | | VI-2 | Chml |
| 5470 | 3 | 4 | 5 | 6 | | VI-2 | Chmp1b |
| 5471 | 3 | 4 | 5 | 6 | | VI-2 | Chordc1 |
| 5472 | 3 | 4 | 5 | 6 | | VI-2 | Chrdl1 |
| 5473 | 3 | 4 | 5 | 6 | | VI-2 | Chrna3 |
| 5474 | 3 | 4 | 5 | 6 | | VI-2 | Chrna6 |
| 5475 | 3 | 4 | 5 | 6 | | VI-2 | Chst1 |
| 5476 | 3 | 4 | 5 | 6 | | VI-2 | Chst5 |
| 5477 | 3 | 4 | 5 | 6 | | VI-2 | Chsy3 |
| 5478 | 3 | 4 | 5 | 6 | | VI-2 | Ciapin1 |
| 5479 | 3 | 4 | 5 | 6 | | VI-2 | Ciita |
| 5480 | 3 | 4 | 5 | 6 | | VI-2 | Ckap2l |
| 5481 | 3 | 4 | 5 | 6 | | VI-2 | Ckap4 |
| 5482 | 3 | 4 | 5 | 6 | | VI-2 | Ckap5 |
| 5483 | 3 | 4 | 5 | 6 | | VI-2 | Cks1b |
| 5484 | 3 | 4 | 5 | 6 | | VI-2 | Cks1brt |
| 5485 | 3 | 4 | 5 | 6 | | VI-2 | Clca2 |
| 5486 | 3 | 4 | 5 | 6 | | VI-2 | Clcc1 |
| 5487 | 3 | 4 | 5 | 6 | | VI-2 | Clcn4-2 |
| 5488 | 3 | 4 | 5 | 6 | | VI-2 | Cldn19 |
| 5489 | 3 | 4 | 5 | 6 | | VI-2 | Cldn22 |
| 5490 | 3 | 4 | 5 | 6 | | VI-2 | Cldn24 |
| 5491 | 3 | 4 | 5 | 6 | | VI-2 | Clec12a |
| 5492 | 3 | 4 | 5 | 6 | | VI-2 | Clec14a |
| 5493 | 3 | 4 | 5 | 6 | | VI-2 | Clec18a |
| 5494 | 3 | 4 | 5 | 6 | | VI-2 | Clec2i |
| 5495 | 3 | 4 | 5 | 6 | | VI-2 | Clec3a |
| 5496 | 3 | 4 | 5 | 6 | | VI-2 | Clec4b1 |
| 5497 | 3 | 4 | 5 | 6 | | VI-2 | Clhc1 |
| 5498 | 3 | 4 | 5 | 6 | | VI-2 | Clmp |
| 5499 | 3 | 4 | 5 | 6 | | VI-2 | Clock |
| 5500 | 3 | 4 | 5 | 6 | | VI-2 | Clp1 |
| 5501 | 3 | 4 | 5 | 6 | | VI-2 | Clspn |
| 5502 | 3 | 4 | 5 | 6 | | VI-2 | Cmas |
| 5503 | 3 | 4 | 5 | 6 | | VI-2 | Cmip |
| 5504 | 3 | 4 | 5 | 6 | | VI-2 | Cntm8 |
| 5505 | 3 | 4 | 5 | 6 | | VI-2 | Cmtr2 |
| 5506 | 3 | 4 | 5 | 6 | | VI-2 | Cnepir1 |
| 5507 | 3 | 4 | 5 | 6 | | VI-2 | Cnn2 |
| 5508 | 3 | 4 | 5 | 6 | | VI-2 | Cnot6 |
| 5509 | 3 | 4 | 5 | 6 | | VI-2 | Cnot7 |
| 5510 | 3 | 4 | 5 | 6 | | VI-2 | Cnot8 |
| 5511 | 3 | 4 | 5 | 6 | | VI-2 | Cnpy4 |
| 5512 | 3 | 4 | 5 | 6 | | VI-2 | Cnr2 |
| 5513 | 3 | 4 | 5 | 6 | | VI-2 | Cnrip1 |
| 5514 | 3 | 4 | 5 | 6 | | VI-2 | Cnst |
| 5515 | 3 | 4 | 5 | 6 | | VI-2 | Cntln |
| 5516 | 3 | 4 | 5 | 6 | | VI-2 | Cntrob |
| 5517 | 3 | 4 | 5 | 6 | | VI-2 | Cog7 |
| 5518 | 3 | 4 | 5 | 6 | | VI-2 | Col11a1 |
| 5519 | 3 | 4 | 5 | 6 | | VI-2 | Col11a2 |
| 5520 | 3 | 4 | 5 | 6 | | VI-2 | Col12a1 |
| 5521 | 3 | 4 | 5 | 6 | | VI-2 | Col14a1 |
| 5522 | 3 | 4 | 5 | 6 | | VI-2 | Col15a1 |
| 5523 | 3 | 4 | 5 | 6 | | VI-2 | Col17a1 |
| 5524 | 3 | 4 | 5 | 6 | | VI-2 | Col1a1 |
| 5525 | 3 | 4 | 5 | 6 | | VI-2 | Col1a2 |
| 5526 | 3 | 4 | 5 | 6 | | VI-2 | Col2a1 |
| 5527 | 3 | 4 | 5 | 6 | | VI-2 | Col4a2 |
| 5528 | 3 | 4 | 5 | 6 | | VI-2 | Col4a5 |
| 5529 | 3 | 4 | 5 | 6 | | VI-2 | Col4a6 |
| 5530 | 3 | 4 | 5 | 6 | | VI-2 | Col5a1 |
| 5531 | 3 | 4 | 5 | 6 | | VI-2 | Col5a2 |
| 5532 | 3 | 4 | 5 | 6 | | VI-2 | Col6a3 |
| 5533 | 3 | 4 | 5 | 6 | | VI-2 | Col6a4 |
| 5534 | 3 | 4 | 5 | 6 | | VI-2 | Colec11 |
| 5535 | 3 | 4 | 5 | 6 | | VI-2 | Colq |
| 5536 | 3 | 4 | 5 | 6 | | VI-2 | Commd10 |
| 5537 | 3 | 4 | 5 | 6 | | VI-2 | Commd5 |
| 5538 | 3 | 4 | 5 | 6 | | VI-2 | Comt |
| 5539 | 3 | 4 | 5 | 6 | | VI-2 | Copb1 |
| 5540 | 3 | 4 | 5 | 6 | | VI-2 | Copg1 |
| 5541 | 3 | 4 | 5 | 6 | | VI-2 | Copg2 |
| 5542 | 3 | 4 | 5 | 6 | | VI-2 | Cops7a |
| 5543 | 3 | 4 | 5 | 6 | | VI-2 | Cops7b |
| 5544 | 3 | 4 | 5 | 6 | | VI-2 | Coro7 |
| 5545 | 3 | 4 | 5 | 6 | | VI-2 | Cox8a |
| 5546 | 3 | 4 | 5 | 6 | | VI-2 | Cpa4 |
| 5547 | 3 | 4 | 5 | 6 | | VI-2 | Cpa6 |
| 5548 | 3 | 4 | 5 | 6 | | VI-2 | Cpd |
| 5549 | 3 | 4 | 5 | 6 | | VI-2 | Cpox |
| 5550 | 3 | 4 | 5 | 6 | | VI-2 | Cpsf1 |
| 5551 | 3 | 4 | 5 | 6 | | VI-2 | Cpsf6 |
| 5552 | 3 | 4 | 5 | 6 | | VI-2 | Cpsf7 |
| 5553 | 3 | 4 | 5 | 6 | | VI-2 | Cpt1a |
| 5554 | 3 | 4 | 5 | 6 | | VI-2 | Cpvl |
| 5555 | 3 | 4 | 5 | 6 | | VI-2 | Cr1l |
| 5556 | 3 | 4 | 5 | 6 | | VI-2 | Cr2 |
| 5557 | 3 | 4 | 5 | 6 | | VI-2 | Crabp2 |
| 5558 | 3 | 4 | 5 | 6 | | VI-2 | Crb2 |
| 5559 | 3 | 4 | 5 | 6 | | VI-2 | Crbn |
| 5560 | 3 | 4 | 5 | 6 | | VI-2 | Crebzf |
| 5561 | 3 | 4 | 5 | 6 | | VI-2 | Crisp3 |
| 5562 | 3 | 4 | 5 | 6 | | VI-2 | Crispld1 |
| 5563 | 3 | 4 | 5 | 6 | | VI-2 | Crnn |
| 5564 | 3 | 4 | 5 | 6 | | VI-2 | Crtac1 |
| 5565 | 3 | 4 | 5 | 6 | | VI-2 | Crtap |
| 5566 | 3 | 4 | 5 | 6 | | VI-2 | Crtc1 |

Fig. 34 - 30

| | | | | | | |
|---|---|---|---|---|---|---|
| 5567 | 3 | 4 | 5 | 6 | VI-2 | Crtc3 |
| 5568 | 3 | 4 | 5 | 6 | VI-2 | Cryga |
| 5569 | 3 | 4 | 5 | 6 | VI-2 | Csf1r |
| 5570 | 3 | 4 | 5 | 6 | VI-2 | Csf2 |
| 5571 | 3 | 4 | 5 | 6 | VI-2 | Csnk2a1 |
| 5572 | 3 | 4 | 5 | 6 | VI-2 | Cspg4 |
| 5573 | 3 | 4 | 5 | 6 | VI-2 | Cspp1 |
| 5574 | 3 | 4 | 5 | 6 | VI-2 | Csrp1 |
| 5575 | 3 | 4 | 5 | 6 | VI-2 | Cst11 |
| 5576 | 3 | 4 | 5 | 6 | VI-2 | Cstad |
| 5577 | 3 | 4 | 5 | 6 | VI-2 | Cstf2 |
| 5578 | 3 | 4 | 5 | 6 | VI-2 | Cstf2t |
| 5579 | 3 | 4 | 5 | 6 | VI-2 | Ctage5 |
| 5580 | 3 | 4 | 5 | 6 | VI-2 | Ctbp1 |
| 5581 | 3 | 4 | 5 | 6 | VI-2 | Ctbp2 |
| 5582 | 3 | 4 | 5 | 6 | VI-2 | Cth |
| 5583 | 3 | 4 | 5 | 6 | VI-2 | Ctif |
| 5584 | 3 | 4 | 5 | 6 | VI-2 | Ctnnal1 |
| 5585 | 3 | 4 | 5 | 6 | VI-2 | Ctns |
| 5586 | 3 | 4 | 5 | 6 | VI-2 | Ctsc |
| 5587 | 3 | 4 | 5 | 6 | VI-2 | Ctsk |
| 5588 | 3 | 4 | 5 | 6 | VI-2 | Cttn |
| 5589 | 3 | 4 | 5 | 6 | VI-2 | Cul2 |
| 5590 | 3 | 4 | 5 | 6 | VI-2 | Cwc25 |
| 5591 | 3 | 4 | 5 | 6 | VI-2 | Cwh43 |
| 5592 | 3 | 4 | 5 | 6 | VI-2 | Cxadr |
| 5593 | 3 | 4 | 5 | 6 | VI-2 | Cxcl5 |
| 5594 | 3 | 4 | 5 | 6 | VI-2 | Cxcr1 |
| 5595 | 3 | 4 | 5 | 6 | VI-2 | Cxcr2 |
| 5596 | 3 | 4 | 5 | 6 | VI-2 | Cxcr5 |
| 5597 | 3 | 4 | 5 | 6 | VI-2 | Cxx1a |
| 5598 | 3 | 4 | 5 | 6 | VI-2 | Cyb5b |
| 5599 | 3 | 4 | 5 | 6 | VI-2 | Cybrd1 |
| 5600 | 3 | 4 | 5 | 6 | VI-2 | Cyc1 |
| 5601 | 3 | 4 | 5 | 6 | VI-2 | Cyct |
| 5602 | 3 | 4 | 5 | 6 | VI-2 | Cygb |
| 5603 | 3 | 4 | 5 | 6 | VI-2 | Cyhr1 |
| 5604 | 3 | 4 | 5 | 6 | VI-2 | Cylc1 |
| 5605 | 3 | 4 | 5 | 6 | VI-2 | Cyld |
| 5606 | 3 | 4 | 5 | 6 | VI-2 | Cym |
| 5607 | 3 | 4 | 5 | 6 | VI-2 | Cyp20a1 |
| 5608 | 3 | 4 | 5 | 6 | VI-2 | Cyp2a12 |
| 5609 | 3 | 4 | 5 | 6 | VI-2 | Cyp2b13 |
| 5610 | 3 | 4 | 5 | 6 | VI-2 | Cyp2c29 |
| 5611 | 3 | 4 | 5 | 6 | VI-2 | Cyp2c37 |
| 5612 | 3 | 4 | 5 | 6 | VI-2 | Cyp2c38 |
| 5613 | 3 | 4 | 5 | 6 | VI-2 | Cyp2c40 |
| 5614 | 3 | 4 | 5 | 6 | VI-2 | Cyp2c50 |
| 5615 | 3 | 4 | 5 | 6 | VI-2 | Cyp2c54 |
| 5616 | 3 | 4 | 5 | 6 | VI-2 | Cyp2c65 |
| 5617 | 3 | 4 | 5 | 6 | VI-2 | Cyp2c66 |
| 5618 | 3 | 4 | 5 | 6 | VI-2 | Cyp2d11 |
| 5619 | 3 | 4 | 5 | 6 | VI-2 | Cyp2d12 |
| 5620 | 3 | 4 | 5 | 6 | VI-2 | Cyp2d13 |
| 5621 | 3 | 4 | 5 | 6 | VI-2 | Cyp2d26 |
| 5622 | 3 | 4 | 5 | 6 | VI-2 | Cyp2d37-ps |
| 5623 | 3 | 4 | 5 | 6 | VI-2 | Cyp2j5 |
| 5624 | 3 | 4 | 5 | 6 | VI-2 | Cyp2j8 |
| 5625 | 3 | 4 | 5 | 6 | VI-2 | Cyp2u1 |
| 5626 | 3 | 4 | 5 | 6 | VI-2 | Cyp2w1 |
| 5627 | 3 | 4 | 5 | 6 | VI-2 | Cyp3a13 |
| 5628 | 3 | 4 | 5 | 6 | VI-2 | Cyp3a25 |
| 5629 | 3 | 4 | 5 | 6 | VI-2 | Cyp3a41a |
| 5630 | 3 | 4 | 5 | 6 | VI-2 | Cyp3a41b |
| 5631 | 3 | 4 | 5 | 6 | VI-2 | Cyp4a12a |
| 5632 | 3 | 4 | 5 | 6 | VI-2 | Cyp4a12b |
| 5633 | 3 | 4 | 5 | 6 | VI-2 | Cyp4a31 |
| 5634 | 3 | 4 | 5 | 6 | VI-2 | Cyp4a32 |
| 5635 | 3 | 4 | 5 | 6 | VI-2 | Cyp4v3 |
| 5636 | 3 | 4 | 5 | 6 | VI-2 | Cyp7a1 |
| 5637 | 3 | 4 | 5 | 6 | VI-2 | Cysltr1 |
| 5638 | 3 | 4 | 5 | 6 | VI-2 | Cysltr2 |
| 5639 | 3 | 4 | 5 | 6 | VI-2 | Cyth1 |
| 5640 | 3 | 4 | 5 | 6 | VI-2 | D030028A08Rik |
| 5641 | 3 | 4 | 5 | 6 | VI-2 | D11Wsu47e |
| 5642 | 3 | 4 | 5 | 6 | VI-2 | D130040H23Rik |
| 5643 | 3 | 4 | 5 | 6 | VI-2 | D2hgdh |
| 5644 | 3 | 4 | 5 | 6 | VI-2 | D430036I16Rik |
| 5645 | 3 | 4 | 5 | 6 | VI-2 | D430042O09Rik |
| 5646 | 3 | 4 | 5 | 6 | VI-2 | D5Ertd579e |
| 5647 | 3 | 4 | 5 | 6 | VI-2 | D630013N20Rik |
| 5648 | 3 | 4 | 5 | 6 | VI-2 | D630045J12Rik |
| 5649 | 3 | 4 | 5 | 6 | VI-2 | D7Ertd443e |
| 5650 | 3 | 4 | 5 | 6 | VI-2 | D7Ertd715e |
| 5651 | 3 | 4 | 5 | 6 | VI-2 | D830013O20Rik |
| 5652 | 3 | 4 | 5 | 6 | VI-2 | D830030K20Rik |
| 5653 | 3 | 4 | 5 | 6 | VI-2 | D8Ertd82e |
| 5654 | 3 | 4 | 5 | 6 | VI-2 | D930020B18Rik |
| 5655 | 3 | 4 | 5 | 6 | VI-2 | D930048N14Rik |
| 5656 | 3 | 4 | 5 | 6 | VI-2 | Daam2 |
| 5657 | 3 | 4 | 5 | 6 | VI-2 | Dab1 |
| 5658 | 3 | 4 | 5 | 6 | VI-2 | Dab2 |
| 5659 | 3 | 4 | 5 | 6 | VI-2 | Dab2ip |
| 5660 | 3 | 4 | 5 | 6 | VI-2 | Dact1 |
| 5661 | 3 | 4 | 5 | 6 | VI-2 | Dact3 |
| 5662 | 3 | 4 | 5 | 6 | VI-2 | Dad1 |
| 5663 | 3 | 4 | 5 | 6 | VI-2 | Daw1 |
| 5664 | 3 | 4 | 5 | 6 | VI-2 | Dbh |
| 5665 | 3 | 4 | 5 | 6 | VI-2 | Dbpht2 |
| 5666 | 3 | 4 | 5 | 6 | VI-2 | Dbr1 |
| 5667 | 3 | 4 | 5 | 6 | VI-2 | Dcaf13 |
| 5668 | 3 | 4 | 5 | 6 | VI-2 | Dcaf5 |
| 5669 | 3 | 4 | 5 | 6 | VI-2 | Dcaf7 |
| 5670 | 3 | 4 | 5 | 6 | VI-2 | Dclk2 |
| 5671 | 3 | 4 | 5 | 6 | VI-2 | Dclre1a |
| 5672 | 3 | 4 | 5 | 6 | VI-2 | Dcpp1 |
| 5673 | 3 | 4 | 5 | 6 | VI-2 | Dcstamp |
| 5674 | 3 | 4 | 5 | 6 | VI-2 | Dctd |
| 5675 | 3 | 4 | 5 | 6 | VI-2 | Dctn5 |
| 5676 | 3 | 4 | 5 | 6 | VI-2 | Dcun1d1 |
| 5677 | 3 | 4 | 5 | 6 | VI-2 | Dcun1d2 |
| 5678 | 3 | 4 | 5 | 6 | VI-2 | Ddhd1 |
| 5679 | 3 | 4 | 5 | 6 | VI-2 | Ddost |
| 5680 | 3 | 4 | 5 | 6 | VI-2 | Ddx19a |
| 5681 | 3 | 4 | 5 | 6 | VI-2 | Ddx46 |
| 5682 | 3 | 4 | 5 | 6 | VI-2 | Ddx51 |
| 5683 | 3 | 4 | 5 | 6 | VI-2 | Ddx59 |
| 5684 | 3 | 4 | 5 | 6 | VI-2 | Dear1 |
| 5685 | 3 | 4 | 5 | 6 | VI-2 | Def6 |
| 5686 | 3 | 4 | 5 | 6 | VI-2 | Defb15 |
| 5687 | 3 | 4 | 5 | 6 | VI-2 | Defb20 |
| 5688 | 3 | 4 | 5 | 6 | VI-2 | Defb21 |
| 5689 | 3 | 4 | 5 | 6 | VI-2 | Defb23 |
| 5690 | 3 | 4 | 5 | 6 | VI-2 | Defb26 |
| 5691 | 3 | 4 | 5 | 6 | VI-2 | Defb33 |
| 5692 | 3 | 4 | 5 | 6 | VI-2 | Defb41 |
| 5693 | 3 | 4 | 5 | 6 | VI-2 | Defb9 |
| 5694 | 3 | 4 | 5 | 6 | VI-2 | Dennd2c |
| 5695 | 3 | 4 | 5 | 6 | VI-2 | Dennd5a |
| 5696 | 3 | 4 | 5 | 6 | VI-2 | Depdc1a |
| 5697 | 3 | 4 | 5 | 6 | VI-2 | Depdc1b |
| 5698 | 3 | 4 | 5 | 6 | VI-2 | Depdc5 |
| 5699 | 3 | 4 | 5 | 6 | VI-2 | Depdc7 |
| 5700 | 3 | 4 | 5 | 6 | VI-2 | Det1 |
| 5701 | 3 | 4 | 5 | 6 | VI-2 | Dffb |
| 5702 | 3 | 4 | 5 | 6 | VI-2 | Dgcr2 |
| 5703 | 3 | 4 | 5 | 6 | VI-2 | Dgkd |
| 5704 | 3 | 4 | 5 | 6 | VI-2 | Dhcr7 |
| 5705 | 3 | 4 | 5 | 6 | VI-2 | Dhfr |
| 5706 | 3 | 4 | 5 | 6 | VI-2 | Dhh |
| 5707 | 3 | 4 | 5 | 6 | VI-2 | Dhtkd1 |
| 5708 | 3 | 4 | 5 | 6 | VI-2 | Dhx29 |
| 5709 | 3 | 4 | 5 | 6 | VI-2 | Dhx30 |
| 5710 | 3 | 4 | 5 | 6 | VI-2 | Dhx35 |
| 5711 | 3 | 4 | 5 | 6 | VI-2 | Dhx38 |
| 5712 | 3 | 4 | 5 | 6 | VI-2 | Dhx9 |
| 5713 | 3 | 4 | 5 | 6 | VI-2 | Diap3 |
| 5714 | 3 | 4 | 5 | 6 | VI-2 | Dicer1 |
| 5715 | 3 | 4 | 5 | 6 | VI-2 | Dido1 |
| 5716 | 3 | 4 | 5 | 6 | VI-2 | Dimt1 |
| 5717 | 3 | 4 | 5 | 6 | VI-2 | Dip2b |
| 5718 | 3 | 4 | 5 | 6 | VI-2 | Dis3 |
| 5719 | 3 | 4 | 5 | 6 | VI-2 | Dkc1 |
| 5720 | 3 | 4 | 5 | 6 | VI-2 | Dlc1 |
| 5721 | 3 | 4 | 5 | 6 | VI-2 | Dleu7 |
| 5722 | 3 | 4 | 5 | 6 | VI-2 | Dll4 |
| 5723 | 3 | 4 | 5 | 6 | VI-2 | Dlx2 |
| 5724 | 3 | 4 | 5 | 6 | VI-2 | Dlx5 |
| 5725 | 3 | 4 | 5 | 6 | VI-2 | Dlx6 |
| 5726 | 3 | 4 | 5 | 6 | VI-2 | Dlx6os1 |
| 5727 | 3 | 4 | 5 | 6 | VI-2 | Dmp1 |
| 5728 | 3 | 4 | 5 | 6 | VI-2 | Dmr |
| 5729 | 3 | 4 | 5 | 6 | VI-2 | Dmrt2 |
| 5730 | 3 | 4 | 5 | 6 | VI-2 | Dmrtc1b |
| 5731 | 3 | 4 | 5 | 6 | VI-2 | Dmrtc2 |
| 5732 | 3 | 4 | 5 | 6 | VI-2 | Dmtn |
| 5733 | 3 | 4 | 5 | 6 | VI-2 | Dmxl2 |
| 5734 | 3 | 4 | 5 | 6 | VI-2 | Dnaaf2 |
| 5735 | 3 | 4 | 5 | 6 | VI-2 | Dnaja1 |
| 5736 | 3 | 4 | 5 | 6 | VI-2 | Dnajb4 |
| 5737 | 3 | 4 | 5 | 6 | VI-2 | Dnajb5 |
| 5738 | 3 | 4 | 5 | 6 | VI-2 | Dnajc13 |
| 5739 | 3 | 4 | 5 | 6 | VI-2 | Dnajc14 |
| 5740 | 3 | 4 | 5 | 6 | VI-2 | Dnajc16 |
| 5741 | 3 | 4 | 5 | 6 | VI-2 | Dnajc5g |
| 5742 | 3 | 4 | 5 | 6 | VI-2 | Dnal4 |
| 5743 | 3 | 4 | 5 | 6 | VI-2 | Dnase1 |
| 5744 | 3 | 4 | 5 | 6 | VI-2 | Dnase1l1 |
| 5745 | 3 | 4 | 5 | 6 | VI-2 | Dnd1 |
| 5746 | 3 | 4 | 5 | 6 | VI-2 | Dnmt3a |
| 5747 | 3 | 4 | 5 | 6 | VI-2 | Dntt |
| 5748 | 3 | 4 | 5 | 6 | VI-2 | Doc2a |
| 5749 | 3 | 4 | 5 | 6 | VI-2 | Dock1 |
| 5750 | 3 | 4 | 5 | 6 | VI-2 | Dock10 |
| 5751 | 3 | 4 | 5 | 6 | VI-2 | Dock11 |
| 5752 | 3 | 4 | 5 | 6 | VI-2 | Dock4 |
| 5753 | 3 | 4 | 5 | 6 | VI-2 | Dock7 |
| 5754 | 3 | 4 | 5 | 6 | VI-2 | Dock8 |
| 5755 | 3 | 4 | 5 | 6 | VI-2 | Dok4 |
| 5756 | 3 | 4 | 5 | 6 | VI-2 | Dolpp1 |
| 5757 | 3 | 4 | 5 | 6 | VI-2 | Dpf2 |
| 5758 | 3 | 4 | 5 | 6 | VI-2 | Dpf3 |

Fig. 34 - 31

| | | | | | | | |
|---|---|---|---|---|---|---|---|
| 5759 | 3 | 4 | 5 | 6 | | VI-2 | Dph6 |
| 5760 | 3 | 4 | 5 | 6 | | VI-2 | Dph7 |
| 5761 | 3 | 4 | 5 | 6 | | VI-2 | Dpp4 |
| 5762 | 3 | 4 | 5 | 6 | | VI-2 | Dpp9 |
| 5763 | 3 | 4 | 5 | 6 | | VI-2 | Dpt |
| 5764 | 3 | 4 | 5 | 6 | | VI-2 | Dpy19l3 |
| 5765 | 3 | 4 | 5 | 6 | | VI-2 | Dpy19l4 |
| 5766 | 3 | 4 | 5 | 6 | | VI-2 | Drd1a |
| 5767 | 3 | 4 | 5 | 6 | | VI-2 | Drd2 |
| 5768 | 3 | 4 | 5 | 6 | | VI-2 | Dsc3 |
| 5769 | 3 | 4 | 5 | 6 | | VI-2 | Dscc1 |
| 5770 | 3 | 4 | 5 | 6 | | VI-2 | Dse |
| 5771 | 3 | 4 | 5 | 6 | | VI-2 | Dsg1a |
| 5772 | 3 | 4 | 5 | 6 | | VI-2 | Dsn1 |
| 5773 | 3 | 4 | 5 | 6 | | VI-2 | Dst |
| 5774 | 3 | 4 | 5 | 6 | | VI-2 | Dtd2 |
| 5775 | 3 | 4 | 5 | 6 | | VI-2 | Dtl |
| 5776 | 3 | 4 | 5 | 6 | | VI-2 | Dtx3 |
| 5777 | 3 | 4 | 5 | 6 | | VI-2 | Duox1 |
| 5778 | 3 | 4 | 5 | 6 | | VI-2 | Duoxa1 |
| 5779 | 3 | 4 | 5 | 6 | | VI-2 | Dusp16 |
| 5780 | 3 | 4 | 5 | 6 | | VI-2 | Dusp21 |
| 5781 | 3 | 4 | 5 | 6 | | VI-2 | Dusp28 |
| 5782 | 3 | 4 | 5 | 6 | | VI-2 | Dusp9 |
| 5783 | 3 | 4 | 5 | 6 | | VI-2 | Dut |
| 5784 | 3 | 4 | 5 | 6 | | VI-2 | Dynll1 |
| 5785 | 3 | 4 | 5 | 6 | | VI-2 | Dyrk1a |
| 5786 | 3 | 4 | 5 | 6 | | VI-2 | Dysf |
| 5787 | 3 | 4 | 5 | 6 | | VI-2 | Dzip1 |
| 5788 | 3 | 4 | 5 | 6 | | VI-2 | Dzip1l |
| 5789 | 3 | 4 | 5 | 6 | | VI-2 | E030003E18Rik |
| 5790 | 3 | 4 | 5 | 6 | | VI-2 | E130008D07Rik |
| 5791 | 3 | 4 | 5 | 6 | | VI-2 | E130112N10Rik |
| 5792 | 3 | 4 | 5 | 6 | | VI-2 | E130308A19Rik |
| 5793 | 3 | 4 | 5 | 6 | | VI-2 | E130309D02Rik |
| 5794 | 3 | 4 | 5 | 6 | | VI-2 | E130310I04Rik |
| 5795 | 3 | 4 | 5 | 6 | | VI-2 | E130311K13Rik |
| 5796 | 3 | 4 | 5 | 6 | | VI-2 | E2f2 |
| 5797 | 3 | 4 | 5 | 6 | | VI-2 | E2f5 |
| 5798 | 3 | 4 | 5 | 6 | | VI-2 | E2f8 |
| 5799 | 3 | 4 | 5 | 6 | | VI-2 | E330009J07Rik |
| 5800 | 3 | 4 | 5 | 6 | | VI-2 | E330011O21Rik |
| 5801 | 3 | 4 | 5 | 6 | | VI-2 | E330034G19Rik |
| 5802 | 3 | 4 | 5 | 6 | | VI-2 | E430025E21Rik |
| 5803 | 3 | 4 | 5 | 6 | | VI-2 | Ebf3 |
| 5804 | 3 | 4 | 5 | 6 | | VI-2 | Ece1 |
| 5805 | 3 | 4 | 5 | 6 | | VI-2 | Echs1 |
| 5806 | 3 | 4 | 5 | 6 | | VI-2 | Ect2 |
| 5807 | 3 | 4 | 5 | 6 | | VI-2 | Edaradd |
| 5808 | 3 | 4 | 5 | 6 | | VI-2 | Ednra |
| 5809 | 3 | 4 | 5 | 6 | | VI-2 | Eef1e1 |
| 5810 | 3 | 4 | 5 | 6 | | VI-2 | Eef2k |
| 5811 | 3 | 4 | 5 | 6 | | VI-2 | Eefsec |
| 5812 | 3 | 4 | 5 | 6 | | VI-2 | Efcab1 |
| 5813 | 3 | 4 | 5 | 6 | | VI-2 | Efcab3 |
| 5814 | 3 | 4 | 5 | 6 | | VI-2 | Efcc1 |
| 5815 | 3 | 4 | 5 | 6 | | VI-2 | Efhc1 |
| 5816 | 3 | 4 | 5 | 6 | | VI-2 | Efs |
| 5817 | 3 | 4 | 5 | 6 | | VI-2 | Eftud1 |
| 5818 | 3 | 4 | 5 | 6 | | VI-2 | Egfl6 |
| 5819 | 3 | 4 | 5 | 6 | | VI-2 | Egflam |
| 5820 | 3 | 4 | 5 | 6 | | VI-2 | Egln1 |
| 5821 | 3 | 4 | 5 | 6 | | VI-2 | Egr3 |
| 5822 | 3 | 4 | 5 | 6 | | VI-2 | Egr4 |
| 5823 | 3 | 4 | 5 | 6 | | VI-2 | Ehf |
| 5824 | 3 | 4 | 5 | 6 | | VI-2 | Eid1 |
| 5825 | 3 | 4 | 5 | 6 | | VI-2 | Eid2b |
| 5826 | 3 | 4 | 5 | 6 | | VI-2 | Eif4a2 |
| 5827 | 3 | 4 | 5 | 6 | | VI-2 | Eif4g2 |
| 5828 | 3 | 4 | 5 | 6 | | VI-2 | Eif5 |
| 5829 | 3 | 4 | 5 | 6 | | VI-2 | Eif5a2 |
| 5830 | 3 | 4 | 5 | 6 | | VI-2 | Eif4 |
| 5831 | 3 | 4 | 5 | 6 | | VI-2 | Elfn1 |
| 5832 | 3 | 4 | 5 | 6 | | VI-2 | Elfn2 |
| 5833 | 3 | 4 | 5 | 6 | | VI-2 | Elmo2 |
| 5834 | 3 | 4 | 5 | 6 | | VI-2 | Elovl4 |
| 5835 | 3 | 4 | 5 | 6 | | VI-2 | Elp4 |
| 5836 | 3 | 4 | 5 | 6 | | VI-2 | Emc4 |
| 5837 | 3 | 4 | 5 | 6 | | VI-2 | Emc7 |
| 5838 | 3 | 4 | 5 | 6 | | VI-2 | Emc8 |
| 5839 | 3 | 4 | 5 | 6 | | VI-2 | Eme2 |
| 5840 | 3 | 4 | 5 | 6 | | VI-2 | Emid1 |
| 5841 | 3 | 4 | 5 | 6 | | VI-2 | Emr1 |
| 5842 | 3 | 4 | 5 | 6 | | VI-2 | Emx2 |
| 5843 | 3 | 4 | 5 | 6 | | VI-2 | Endou |
| 5844 | 3 | 4 | 5 | 6 | | VI-2 | Eno1b |
| 5845 | 3 | 4 | 5 | 6 | | VI-2 | Enoph1 |
| 5846 | 3 | 4 | 5 | 6 | | VI-2 | Enpep |
| 5847 | 3 | 4 | 5 | 6 | | VI-2 | Enpp2 |
| 5848 | 3 | 4 | 5 | 6 | | VI-2 | Enpp3 |
| 5849 | 3 | 4 | 5 | 6 | | VI-2 | Enpp4 |
| 5850 | 3 | 4 | 5 | 6 | | VI-2 | Entpd3 |
| 5851 | 3 | 4 | 5 | 6 | | VI-2 | Entpd6 |
| 5852 | 3 | 4 | 5 | 6 | | VI-2 | Eny2 |
| 5853 | 3 | 4 | 5 | 6 | | VI-2 | Eomes |
| 5854 | 3 | 4 | 5 | 6 | | VI-2 | Ep300 |

| | | | | | | | |
|---|---|---|---|---|---|---|---|
| 5855 | 3 | 4 | 5 | 6 | | VI-2 | Ep400 |
| 5856 | 3 | 4 | 5 | 6 | | VI-2 | Epas1 |
| 5857 | 3 | 4 | 5 | 6 | | VI-2 | Epb4.1 |
| 5858 | 3 | 4 | 5 | 6 | | VI-2 | Epb4.1l3 |
| 5859 | 3 | 4 | 5 | 6 | | VI-2 | Epc1 |
| 5860 | 3 | 4 | 5 | 6 | | VI-2 | Epc2 |
| 5861 | 3 | 4 | 5 | 6 | | VI-2 | Epg5 |
| 5862 | 3 | 4 | 5 | 6 | | VI-2 | Ephb2 |
| 5863 | 3 | 4 | 5 | 6 | | VI-2 | Ephb3 |
| 5864 | 3 | 4 | 5 | 6 | | VI-2 | Ephx3 |
| 5865 | 3 | 4 | 5 | 6 | | VI-2 | Epm2a |
| 5866 | 3 | 4 | 5 | 6 | | VI-2 | Eps8l3 |
| 5867 | 3 | 4 | 5 | 6 | | VI-2 | Ept1 |
| 5868 | 3 | 4 | 5 | 6 | | VI-2 | Ercc6 |
| 5869 | 3 | 4 | 5 | 6 | | VI-2 | Ercc6l |
| 5870 | 3 | 4 | 5 | 6 | | VI-2 | Ercc8 |
| 5871 | 3 | 4 | 5 | 6 | | VI-2 | Ereg |
| 5872 | 3 | 4 | 5 | 6 | | VI-2 | Ergic1 |
| 5873 | 3 | 4 | 5 | 6 | | VI-2 | Ergic2 |
| 5874 | 3 | 4 | 5 | 6 | | VI-2 | Erlin2 |
| 5875 | 3 | 4 | 5 | 6 | | VI-2 | Ermap |
| 5876 | 3 | 4 | 5 | 6 | | VI-2 | Esco2 |
| 5877 | 3 | 4 | 5 | 6 | | VI-2 | Esf1 |
| 5878 | 3 | 4 | 5 | 6 | | VI-2 | Espl1 |
| 5879 | 3 | 4 | 5 | 6 | | VI-2 | Esr1 |
| 5880 | 3 | 4 | 5 | 6 | | VI-2 | Esrra |
| 5881 | 3 | 4 | 5 | 6 | | VI-2 | Esyt1 |
| 5882 | 3 | 4 | 5 | 6 | | VI-2 | Esyt3 |
| 5883 | 3 | 4 | 5 | 6 | | VI-2 | Ethe1 |
| 5884 | 3 | 4 | 5 | 6 | | VI-2 | Etl4 |
| 5885 | 3 | 4 | 5 | 6 | | VI-2 | Etnk1 |
| 5886 | 3 | 4 | 5 | 6 | | VI-2 | Ets1 |
| 5887 | 3 | 4 | 5 | 6 | | VI-2 | Ets2 |
| 5888 | 3 | 4 | 5 | 6 | | VI-2 | Evc |
| 5889 | 3 | 4 | 5 | 6 | | VI-2 | Evi2a |
| 5890 | 3 | 4 | 5 | 6 | | VI-2 | Ewsr1 |
| 5891 | 3 | 4 | 5 | 6 | | VI-2 | Exo1 |
| 5892 | 3 | 4 | 5 | 6 | | VI-2 | Exoc2 |
| 5893 | 3 | 4 | 5 | 6 | | VI-2 | Exoc4 |
| 5894 | 3 | 4 | 5 | 6 | | VI-2 | Exoc5 |
| 5895 | 3 | 4 | 5 | 6 | | VI-2 | Exoc6 |
| 5896 | 3 | 4 | 5 | 6 | | VI-2 | Exosc1 |
| 5897 | 3 | 4 | 5 | 6 | | VI-2 | Exosc10 |
| 5898 | 3 | 4 | 5 | 6 | | VI-2 | Exosc7 |
| 5899 | 3 | 4 | 5 | 6 | | VI-2 | Ext1 |
| 5900 | 3 | 4 | 5 | 6 | | VI-2 | Extl3 |
| 5901 | 3 | 4 | 5 | 6 | | VI-2 | Eya2 |
| 5902 | 3 | 4 | 5 | 6 | | VI-2 | Eya3 |
| 5903 | 3 | 4 | 5 | 6 | | VI-2 | Ezr |
| 5904 | 3 | 4 | 5 | 6 | | VI-2 | F2r |
| 5905 | 3 | 4 | 5 | 6 | | VI-2 | F2rl2 |
| 5906 | 3 | 4 | 5 | 6 | | VI-2 | F420014N23Rik |
| 5907 | 3 | 4 | 5 | 6 | | VI-2 | F630028O10Rik |
| 5908 | 3 | 4 | 5 | 6 | | VI-2 | F7 |
| 5909 | 3 | 4 | 5 | 6 | | VI-2 | F830002L21Rik |
| 5910 | 3 | 4 | 5 | 6 | | VI-2 | F830045P16Rik |
| 5911 | 3 | 4 | 5 | 6 | | VI-2 | Fa2h |
| 5912 | 3 | 4 | 5 | 6 | | VI-2 | Fadd |
| 5913 | 3 | 4 | 5 | 6 | | VI-2 | Fads1 |
| 5914 | 3 | 4 | 5 | 6 | | VI-2 | Fam101a |
| 5915 | 3 | 4 | 5 | 6 | | VI-2 | Fam105a |
| 5916 | 3 | 4 | 5 | 6 | | VI-2 | Fam109b |
| 5917 | 3 | 4 | 5 | 6 | | VI-2 | Fam110b |
| 5918 | 3 | 4 | 5 | 6 | | VI-2 | Fam114a1 |
| 5919 | 3 | 4 | 5 | 6 | | VI-2 | Fam115c |
| 5920 | 3 | 4 | 5 | 6 | | VI-2 | Fam115e |
| 5921 | 3 | 4 | 5 | 6 | | VI-2 | Fam126a |
| 5922 | 3 | 4 | 5 | 6 | | VI-2 | Fam126b |
| 5923 | 3 | 4 | 5 | 6 | | VI-2 | Fam136a |
| 5924 | 3 | 4 | 5 | 6 | | VI-2 | Fam149a |
| 5925 | 3 | 4 | 5 | 6 | | VI-2 | Fam149b |
| 5926 | 3 | 4 | 5 | 6 | | VI-2 | Fam150a |
| 5927 | 3 | 4 | 5 | 6 | | VI-2 | Fam154a |
| 5928 | 3 | 4 | 5 | 6 | | VI-2 | Fam161b |
| 5929 | 3 | 4 | 5 | 6 | | VI-2 | Fam168b |
| 5930 | 3 | 4 | 5 | 6 | | VI-2 | Fam174a |
| 5931 | 3 | 4 | 5 | 6 | | VI-2 | Fam175a |
| 5932 | 3 | 4 | 5 | 6 | | VI-2 | Fam178a |
| 5933 | 3 | 4 | 5 | 6 | | VI-2 | Fam184a |
| 5934 | 3 | 4 | 5 | 6 | | VI-2 | Fam185a |
| 5935 | 3 | 4 | 5 | 6 | | VI-2 | Fam189b |
| 5936 | 3 | 4 | 5 | 6 | | VI-2 | Fam193a |
| 5937 | 3 | 4 | 5 | 6 | | VI-2 | Fam198b |
| 5938 | 3 | 4 | 5 | 6 | | VI-2 | Fam199x |
| 5939 | 3 | 4 | 5 | 6 | | VI-2 | Fam210a |
| 5940 | 3 | 4 | 5 | 6 | | VI-2 | Fam210b |
| 5941 | 3 | 4 | 5 | 6 | | VI-2 | Fam213a |
| 5942 | 3 | 4 | 5 | 6 | | VI-2 | Fam217a |
| 5943 | 3 | 4 | 5 | 6 | | VI-2 | Fam221a |
| 5944 | 3 | 4 | 5 | 6 | | VI-2 | Fam227b |
| 5945 | 3 | 4 | 5 | 6 | | VI-2 | Fam46d |
| 5946 | 3 | 4 | 5 | 6 | | VI-2 | Fam47c |
| 5947 | 3 | 4 | 5 | 6 | | VI-2 | Fam47e |
| 5948 | 3 | 4 | 5 | 6 | | VI-2 | Fam58b |
| 5949 | 3 | 4 | 5 | 6 | | VI-2 | Fam63b |
| 5950 | 3 | 4 | 5 | 6 | | VI-2 | Fam64a |

Fig. 34 - 32

| | | | | | | | |
|---|---|---|---|---|---|---|---|
| 5951 | 3 | 4 | 5 | 6 | | VI-2 | Fam65a |
| 5952 | 3 | 4 | 5 | 6 | | VI-2 | Fam65b |
| 5953 | 3 | 4 | 5 | 6 | | VI-2 | Fam69c |
| 5954 | 3 | 4 | 5 | 6 | | VI-2 | Fam73a |
| 5955 | 3 | 4 | 5 | 6 | | VI-2 | Fam76a |
| 5956 | 3 | 4 | 5 | 6 | | VI-2 | Fam83b |
| 5957 | 3 | 4 | 5 | 6 | | VI-2 | Fam83f |
| 5958 | 3 | 4 | 5 | 6 | | VI-2 | Fam89a |
| 5959 | 3 | 4 | 5 | 6 | | VI-2 | Fam96a |
| 5960 | 3 | 4 | 5 | 6 | | VI-2 | Fan1 |
| 5961 | 3 | 4 | 5 | 6 | | VI-2 | Fancb |
| 5962 | 3 | 4 | 5 | 6 | | VI-2 | Fancd2os |
| 5963 | 3 | 4 | 5 | 6 | | VI-2 | Fance |
| 5964 | 3 | 4 | 5 | 6 | | VI-2 | Fancf |
| 5965 | 3 | 4 | 5 | 6 | | VI-2 | Fancm |
| 5966 | 3 | 4 | 5 | 6 | | VI-2 | Farp1 |
| 5967 | 3 | 4 | 5 | 6 | | VI-2 | Fastkd3 |
| 5968 | 3 | 4 | 5 | 6 | | VI-2 | Fat4 |
| 5969 | 3 | 4 | 5 | 6 | | VI-2 | Fblim1 |
| 5970 | 3 | 4 | 5 | 6 | | VI-2 | Fbln5 |
| 5971 | 3 | 4 | 5 | 6 | | VI-2 | Fbln7 |
| 5972 | 3 | 4 | 5 | 6 | | VI-2 | Fbn1 |
| 5973 | 3 | 4 | 5 | 6 | | VI-2 | Fbrsl1 |
| 5974 | 3 | 4 | 5 | 6 | | VI-2 | Fbxl17 |
| 5975 | 3 | 4 | 5 | 6 | | VI-2 | Fbxl20 |
| 5976 | 3 | 4 | 5 | 6 | | VI-2 | Fbxl21 |
| 5977 | 3 | 4 | 5 | 6 | | VI-2 | Fbxo18 |
| 5978 | 3 | 4 | 5 | 6 | | VI-2 | Fbxo28 |
| 5979 | 3 | 4 | 5 | 6 | | VI-2 | Fbxo33 |
| 5980 | 3 | 4 | 5 | 6 | | VI-2 | Fbxo43 |
| 5981 | 3 | 4 | 5 | 6 | | VI-2 | Fbxo45 |
| 5982 | 3 | 4 | 5 | 6 | | VI-2 | Fbxo46 |
| 5983 | 3 | 4 | 5 | 6 | | VI-2 | Fbxw11 |
| 5984 | 3 | 4 | 5 | 6 | | VI-2 | Fbxw2 |
| 5985 | 3 | 4 | 5 | 6 | | VI-2 | Fcamr |
| 5986 | 3 | 4 | 5 | 6 | | VI-2 | Fchsd1 |
| 5987 | 3 | 4 | 5 | 6 | | VI-2 | Fem1a |
| 5988 | 3 | 4 | 5 | 6 | | VI-2 | Fendrr |
| 5989 | 3 | 4 | 5 | 6 | | VI-2 | Fermt2 |
| 5990 | 3 | 4 | 5 | 6 | | VI-2 | Fert2 |
| 5991 | 3 | 4 | 5 | 6 | | VI-2 | Ffar2 |
| 5992 | 3 | 4 | 5 | 6 | | VI-2 | Fgd3 |
| 5993 | 3 | 4 | 5 | 6 | | VI-2 | Fgd4 |
| 5994 | 3 | 4 | 5 | 6 | | VI-2 | Fgd6 |
| 5995 | 3 | 4 | 5 | 6 | | VI-2 | Fgf1 |
| 5996 | 3 | 4 | 5 | 6 | | VI-2 | Fgf11 |
| 5997 | 3 | 4 | 5 | 6 | | VI-2 | Fgf16 |
| 5998 | 3 | 4 | 5 | 6 | | VI-2 | Fgf18 |
| 5999 | 3 | 4 | 5 | 6 | | VI-2 | Fgf2 |
| 6000 | 3 | 4 | 5 | 6 | | VI-2 | Fgf5 |
| 6001 | 3 | 4 | 5 | 6 | | VI-2 | Fgf7 |
| 6002 | 3 | 4 | 5 | 6 | | VI-2 | Fgfbp3 |
| 6003 | 3 | 4 | 5 | 6 | | VI-2 | Fgr |
| 6004 | 3 | 4 | 5 | 6 | | VI-2 | Fhl2 |
| 6005 | 3 | 4 | 5 | 6 | | VI-2 | Fibp |
| 6006 | 3 | 4 | 5 | 6 | | VI-2 | Ficd |
| 6007 | 3 | 4 | 5 | 6 | | VI-2 | Fignl2 |
| 6008 | 3 | 4 | 5 | 6 | | VI-2 | Fip1l1 |
| 6009 | 3 | 4 | 5 | 6 | | VI-2 | Firre |
| 6010 | 3 | 4 | 5 | 6 | | VI-2 | Fktn |
| 6011 | 3 | 4 | 5 | 6 | | VI-2 | Fli1 |
| 6012 | 3 | 4 | 5 | 6 | | VI-2 | Flii |
| 6013 | 3 | 4 | 5 | 6 | | VI-2 | Flrt1 |
| 6014 | 3 | 4 | 5 | 6 | | VI-2 | Fmr1nb |
| 6015 | 3 | 4 | 5 | 6 | | VI-2 | Fnbp1 |
| 6016 | 3 | 4 | 5 | 6 | | VI-2 | Fndc1 |
| 6017 | 3 | 4 | 5 | 6 | | VI-2 | Fndc7 |
| 6018 | 3 | 4 | 5 | 6 | | VI-2 | Folr2 |
| 6019 | 3 | 4 | 5 | 6 | | VI-2 | Foxa1 |
| 6020 | 3 | 4 | 5 | 6 | | VI-2 | Foxa2 |
| 6021 | 3 | 4 | 5 | 6 | | VI-2 | Foxb1 |
| 6022 | 3 | 4 | 5 | 6 | | VI-2 | Foxf1 |
| 6023 | 3 | 4 | 5 | 6 | | VI-2 | Foxl1 |
| 6024 | 3 | 4 | 5 | 6 | | VI-2 | Foxm1 |
| 6025 | 3 | 4 | 5 | 6 | | VI-2 | Foxn1 |
| 6026 | 3 | 4 | 5 | 6 | | VI-2 | Foxo4 |
| 6027 | 3 | 4 | 5 | 6 | | VI-2 | Foxo6 |
| 6028 | 3 | 4 | 5 | 6 | | VI-2 | Foxred2 |
| 6029 | 3 | 4 | 5 | 6 | | VI-2 | Frk |
| 6030 | 3 | 4 | 5 | 6 | | VI-2 | Frzb |
| 6031 | 3 | 4 | 5 | 6 | | VI-2 | Fsbp |
| 6032 | 3 | 4 | 5 | 6 | | VI-2 | Fscn1 |
| 6033 | 3 | 4 | 5 | 6 | | VI-2 | Fsd2 |
| 6034 | 3 | 4 | 5 | 6 | | VI-2 | Fsip1 |
| 6035 | 3 | 4 | 5 | 6 | | VI-2 | Ftx |
| 6036 | 3 | 4 | 5 | 6 | | VI-2 | Fubp3 |
| 6037 | 3 | 4 | 5 | 6 | | VI-2 | Fuk |
| 6038 | 3 | 4 | 5 | 6 | | VI-2 | Fut4 |
| 6039 | 3 | 4 | 5 | 6 | | VI-2 | Fut8 |
| 6040 | 3 | 4 | 5 | 6 | | VI-2 | Fyb |
| 6041 | 3 | 4 | 5 | 6 | | VI-2 | Fyco1 |
| 6042 | 3 | 4 | 5 | 6 | | VI-2 | Fyn |
| 6043 | 3 | 4 | 5 | 6 | | VI-2 | Fzd10 |
| 6044 | 3 | 4 | 5 | 6 | | VI-2 | Fzd5 |
| 6045 | 3 | 4 | 5 | 6 | | VI-2 | Fzd8 |
| 6046 | 3 | 4 | 5 | 6 | | VI-2 | G2e3 |
| 6047 | 3 | 4 | 5 | 6 | | VI-2 | G3bp2 |
| 6048 | 3 | 4 | 5 | 6 | | VI-2 | G630025P09Rik |
| 6049 | 3 | 4 | 5 | 6 | | VI-2 | G6b |
| 6050 | 3 | 4 | 5 | 6 | | VI-2 | G6pc2 |
| 6051 | 3 | 4 | 5 | 6 | | VI-2 | Gabpb2 |
| 6052 | 3 | 4 | 5 | 6 | | VI-2 | Gabrp |
| 6053 | 3 | 4 | 5 | 6 | | VI-2 | Gabrr2 |
| 6054 | 3 | 4 | 5 | 6 | | VI-2 | Galk2 |
| 6055 | 3 | 4 | 5 | 6 | | VI-2 | Galnt14 |
| 6056 | 3 | 4 | 5 | 6 | | VI-2 | Galnt5 |
| 6057 | 3 | 4 | 5 | 6 | | VI-2 | Galnt6 |
| 6058 | 3 | 4 | 5 | 6 | | VI-2 | Gan |
| 6059 | 3 | 4 | 5 | 6 | | VI-2 | Ganc |
| 6060 | 3 | 4 | 5 | 6 | | VI-2 | Garem |
| 6061 | 3 | 4 | 5 | 6 | | VI-2 | Gas2 |
| 6062 | 3 | 4 | 5 | 6 | | VI-2 | Gas2l3 |
| 6063 | 3 | 4 | 5 | 6 | | VI-2 | Gas6 |
| 6064 | 3 | 4 | 5 | 6 | | VI-2 | Gata4 |
| 6065 | 3 | 4 | 5 | 6 | | VI-2 | Gata5 |
| 6066 | 3 | 4 | 5 | 6 | | VI-2 | Gata6 |
| 6067 | 3 | 4 | 5 | 6 | | VI-2 | Gba2 |
| 6068 | 3 | 4 | 5 | 6 | | VI-2 | Gbas |
| 6069 | 3 | 4 | 5 | 6 | | VI-2 | Gbf1 |
| 6070 | 3 | 4 | 5 | 6 | | VI-2 | Gbgt1 |
| 6071 | 3 | 4 | 5 | 6 | | VI-2 | Gbp4 |
| 6072 | 3 | 4 | 5 | 6 | | VI-2 | Gbp8 |
| 6073 | 3 | 4 | 5 | 6 | | VI-2 | Gcc2 |
| 6074 | 3 | 4 | 5 | 6 | | VI-2 | Gcg |
| 6075 | 3 | 4 | 5 | 6 | | VI-2 | Gcnt4 |
| 6076 | 3 | 4 | 5 | 6 | | VI-2 | Gdf10 |
| 6077 | 3 | 4 | 5 | 6 | | VI-2 | Gdf6 |
| 6078 | 3 | 4 | 5 | 6 | | VI-2 | Gdpgp1 |
| 6079 | 3 | 4 | 5 | 6 | | VI-2 | Gemin4 |
| 6080 | 3 | 4 | 5 | 6 | | VI-2 | Gemin6 |
| 6081 | 3 | 4 | 5 | 6 | | VI-2 | Gemin8 |
| 6082 | 3 | 4 | 5 | 6 | | VI-2 | Gen1 |
| 6083 | 3 | 4 | 5 | 6 | | VI-2 | Gfi1b |
| 6084 | 3 | 4 | 5 | 6 | | VI-2 | Gfm1 |
| 6085 | 3 | 4 | 5 | 6 | | VI-2 | Gfpt1 |
| 6086 | 3 | 4 | 5 | 6 | | VI-2 | Gga3 |
| 6087 | 3 | 4 | 5 | 6 | | VI-2 | Ggcx |
| 6088 | 3 | 4 | 5 | 6 | | VI-2 | Ggt6 |
| 6089 | 3 | 4 | 5 | 6 | | VI-2 | Ggta1 |
| 6090 | 3 | 4 | 5 | 6 | | VI-2 | Ghr |
| 6091 | 3 | 4 | 5 | 6 | | VI-2 | Gid4 |
| 6092 | 3 | 4 | 5 | 6 | | VI-2 | Gid8 |
| 6093 | 3 | 4 | 5 | 6 | | VI-2 | Gigyf1 |
| 6094 | 3 | 4 | 5 | 6 | | VI-2 | Gigyf2 |
| 6095 | 3 | 4 | 5 | 6 | | VI-2 | Gimap5 |
| 6096 | 3 | 4 | 5 | 6 | | VI-2 | Gimap6 |
| 6097 | 3 | 4 | 5 | 6 | | VI-2 | Gimap7 |
| 6098 | 3 | 4 | 5 | 6 | | VI-2 | Gimap8 |
| 6099 | 3 | 4 | 5 | 6 | | VI-2 | Ginm1 |
| 6100 | 3 | 4 | 5 | 6 | | VI-2 | Gins2 |
| 6101 | 3 | 4 | 5 | 6 | | VI-2 | Gja3 |
| 6102 | 3 | 4 | 5 | 6 | | VI-2 | Gja6 |
| 6103 | 3 | 4 | 5 | 6 | | VI-2 | Gjb3 |
| 6104 | 3 | 4 | 5 | 6 | | VI-2 | Gjc1 |
| 6105 | 3 | 4 | 5 | 6 | | VI-2 | Glb1l3 |
| 6106 | 3 | 4 | 5 | 6 | | VI-2 | Glcci1 |
| 6107 | 3 | 4 | 5 | 6 | | VI-2 | Gli1 |
| 6108 | 3 | 4 | 5 | 6 | | VI-2 | Gli2 |
| 6109 | 3 | 4 | 5 | 6 | | VI-2 | Glis2 |
| 6110 | 3 | 4 | 5 | 6 | | VI-2 | Glt8d2 |
| 6111 | 3 | 4 | 5 | 6 | | VI-2 | Gltpd1 |
| 6112 | 3 | 4 | 5 | 6 | | VI-2 | Glyctk |
| 6113 | 3 | 4 | 5 | 6 | | VI-2 | Glyr1 |
| 6114 | 3 | 4 | 5 | 6 | | VI-2 | Gm10230 |
| 6115 | 3 | 4 | 5 | 6 | | VI-2 | Gm10488 |
| 6116 | 3 | 4 | 5 | 6 | | VI-2 | Gm10509 |
| 6117 | 3 | 4 | 5 | 6 | | VI-2 | Gm10516 |
| 6118 | 3 | 4 | 5 | 6 | | VI-2 | Gm10653 |
| 6119 | 3 | 4 | 5 | 6 | | VI-2 | Gm10681 |
| 6120 | 3 | 4 | 5 | 6 | | VI-2 | Gm10731 |
| 6121 | 3 | 4 | 5 | 6 | | VI-2 | Gm10767 |
| 6122 | 3 | 4 | 5 | 6 | | VI-2 | Gm10787 |
| 6123 | 3 | 4 | 5 | 6 | | VI-2 | Gm11346 |
| 6124 | 3 | 4 | 5 | 6 | | VI-2 | Gm1141 |
| 6125 | 3 | 4 | 5 | 6 | | VI-2 | Gm11545 |
| 6126 | 3 | 4 | 5 | 6 | | VI-2 | Gm11564 |
| 6127 | 3 | 4 | 5 | 6 | | VI-2 | Gm11565 |
| 6128 | 3 | 4 | 5 | 6 | | VI-2 | Gm11568 |
| 6129 | 3 | 4 | 5 | 6 | | VI-2 | Gm11595 |
| 6130 | 3 | 4 | 5 | 6 | | VI-2 | Gm11696 |
| 6131 | 3 | 4 | 5 | 6 | | VI-2 | Gm11944 |
| 6132 | 3 | 4 | 5 | 6 | | VI-2 | Gm12359 |
| 6133 | 3 | 4 | 5 | 6 | | VI-2 | Gm12504 |
| 6134 | 3 | 4 | 5 | 6 | | VI-2 | Gm12992 |
| 6135 | 3 | 4 | 5 | 6 | | VI-2 | Gm13154 |
| 6136 | 3 | 4 | 5 | 6 | | VI-2 | Gm13807 |
| 6137 | 3 | 4 | 5 | 6 | | VI-2 | Gm13944 |
| 6138 | 3 | 4 | 5 | 6 | | VI-2 | Gm14057 |
| 6139 | 3 | 4 | 5 | 6 | | VI-2 | Gm14169 |
| 6140 | 3 | 4 | 5 | 6 | | VI-2 | Gm14295 |
| 6141 | 3 | 4 | 5 | 6 | | VI-2 | Gm14305 |
| 6142 | 3 | 4 | 5 | 6 | | VI-2 | Gm14327 |

Fig. 34 - 33

| | | | | | | | |
|---|---|---|---|---|---|---|---|
| 6143 | 3 | 4 | 5 | 6 | | VI-2 | Gm14393 |
| 6144 | 3 | 4 | 5 | 6 | | VI-2 | Gm14405 |
| 6145 | 3 | 4 | 5 | 6 | | VI-2 | Gm14632 |
| 6146 | 3 | 4 | 5 | 6 | | VI-2 | Gm14718 |
| 6147 | 3 | 4 | 5 | 6 | | VI-2 | Gm14781 |
| 6148 | 3 | 4 | 5 | 6 | | VI-2 | Gm14819 |
| 6149 | 3 | 4 | 5 | 6 | | VI-2 | Gm14920 |
| 6150 | 3 | 4 | 5 | 6 | | VI-2 | Gm15140 |
| 6151 | 3 | 4 | 5 | 6 | | VI-2 | Gm15545 |
| 6152 | 3 | 4 | 5 | 6 | | VI-2 | Gm15800 |
| 6153 | 3 | 4 | 5 | 6 | | VI-2 | Gm15881 |
| 6154 | 3 | 4 | 5 | 6 | | VI-2 | Gm15915 |
| 6155 | 3 | 4 | 5 | 6 | | VI-2 | Gm16367 |
| 6156 | 3 | 4 | 5 | 6 | | VI-2 | Gm16390 |
| 6157 | 3 | 4 | 5 | 6 | | VI-2 | Gm16501 |
| 6158 | 3 | 4 | 5 | 6 | | VI-2 | Gm16576 |
| 6159 | 3 | 4 | 5 | 6 | | VI-2 | Gm16617 |
| 6160 | 3 | 4 | 5 | 6 | | VI-2 | Gm16712 |
| 6161 | 3 | 4 | 5 | 6 | | VI-2 | Gm16793 |
| 6162 | 3 | 4 | 5 | 6 | | VI-2 | Gm17296 |
| 6163 | 3 | 4 | 5 | 6 | | VI-2 | Gm17745 |
| 6164 | 3 | 4 | 5 | 6 | | VI-2 | Gm17746 |
| 6165 | 3 | 4 | 5 | 6 | | VI-2 | Gm19277 |
| 6166 | 3 | 4 | 5 | 6 | | VI-2 | Gm19345 |
| 6167 | 3 | 4 | 5 | 6 | | VI-2 | Gm1965 |
| 6168 | 3 | 4 | 5 | 6 | | VI-2 | Gm1976 |
| 6169 | 3 | 4 | 5 | 6 | | VI-2 | Gm19990 |
| 6170 | 3 | 4 | 5 | 6 | | VI-2 | Gm20172 |
| 6171 | 3 | 4 | 5 | 6 | | VI-2 | Gm20324 |
| 6172 | 3 | 4 | 5 | 6 | | VI-2 | Gm20337 |
| 6173 | 3 | 4 | 5 | 6 | | VI-2 | Gm20738 |
| 6174 | 3 | 4 | 5 | 6 | | VI-2 | Gm20743 |
| 6175 | 3 | 4 | 5 | 6 | | VI-2 | Gm20806 |
| 6176 | 3 | 4 | 5 | 6 | | VI-2 | Gm20826 |
| 6177 | 3 | 4 | 5 | 6 | | VI-2 | Gm20857 |
| 6178 | 3 | 4 | 5 | 6 | | VI-2 | Gm20865 |
| 6179 | 3 | 4 | 5 | 6 | | VI-2 | Gm20877 |
| 6180 | 3 | 4 | 5 | 6 | | VI-2 | Gm20917 |
| 6181 | 3 | 4 | 5 | 6 | | VI-2 | Gm2115 |
| 6182 | 3 | 4 | 5 | 6 | | VI-2 | Gm21284 |
| 6183 | 3 | 4 | 5 | 6 | | VI-2 | Gm21637 |
| 6184 | 3 | 4 | 5 | 6 | | VI-2 | Gm21671 |
| 6185 | 3 | 4 | 5 | 6 | | VI-2 | Gm21943 |
| 6186 | 3 | 4 | 5 | 6 | | VI-2 | Gm2382 |
| 6187 | 3 | 4 | 5 | 6 | | VI-2 | Gm2837 |
| 6188 | 3 | 4 | 5 | 6 | | VI-2 | Gm3230 |
| 6189 | 3 | 4 | 5 | 6 | | VI-2 | Gm3404 |
| 6190 | 3 | 4 | 5 | 6 | | VI-2 | Gm3409 |
| 6191 | 3 | 4 | 5 | 6 | | VI-2 | Gm3646 |
| 6192 | 3 | 4 | 5 | 6 | | VI-2 | Gm4532 |
| 6193 | 3 | 4 | 5 | 6 | | VI-2 | Gm4724 |
| 6194 | 3 | 4 | 5 | 6 | | VI-2 | Gm4841 |
| 6195 | 3 | 4 | 5 | 6 | | VI-2 | Gm4871 |
| 6196 | 3 | 4 | 5 | 6 | | VI-2 | Gm4922 |
| 6197 | 3 | 4 | 5 | 6 | | VI-2 | Gm4961 |
| 6198 | 3 | 4 | 5 | 6 | | VI-2 | Gm5065 |
| 6199 | 3 | 4 | 5 | 6 | | VI-2 | Gm5069 |
| 6200 | 3 | 4 | 5 | 6 | | VI-2 | Gm5083 |
| 6201 | 3 | 4 | 5 | 6 | | VI-2 | Gm5113 |
| 6202 | 3 | 4 | 5 | 6 | | VI-2 | Gm5124 |
| 6203 | 3 | 4 | 5 | 6 | | VI-2 | Gm5127 |
| 6204 | 3 | 4 | 5 | 6 | | VI-2 | Gm5129 |
| 6205 | 3 | 4 | 5 | 6 | | VI-2 | Gm5150 |
| 6206 | 3 | 4 | 5 | 6 | | VI-2 | Gm5176 |
| 6207 | 3 | 4 | 5 | 6 | | VI-2 | Gm527 |
| 6208 | 3 | 4 | 5 | 6 | | VI-2 | Gm5434 |
| 6209 | 3 | 4 | 5 | 6 | | VI-2 | Gm5549 |
| 6210 | 3 | 4 | 5 | 6 | | VI-2 | Gm5577 |
| 6211 | 3 | 4 | 5 | 6 | | VI-2 | Gm5615 |
| 6212 | 3 | 4 | 5 | 6 | | VI-2 | Gm5795 |
| 6213 | 3 | 4 | 5 | 6 | | VI-2 | Gm5803 |
| 6214 | 3 | 4 | 5 | 6 | | VI-2 | Gm6040 |
| 6215 | 3 | 4 | 5 | 6 | | VI-2 | Gm608 |
| 6216 | 3 | 4 | 5 | 6 | | VI-2 | Gm614 |
| 6217 | 3 | 4 | 5 | 6 | | VI-2 | Gm6225 |
| 6218 | 3 | 4 | 5 | 6 | | VI-2 | Gm6377 |
| 6219 | 3 | 4 | 5 | 6 | | VI-2 | Gm6408 |
| 6220 | 3 | 4 | 5 | 6 | | VI-2 | Gm6416 |
| 6221 | 3 | 4 | 5 | 6 | | VI-2 | Gm6455 |
| 6222 | 3 | 4 | 5 | 6 | | VI-2 | Gm6460 |
| 6223 | 3 | 4 | 5 | 6 | | VI-2 | Gm6588 |
| 6224 | 3 | 4 | 5 | 6 | | VI-2 | Gm6614 |
| 6225 | 3 | 4 | 5 | 6 | | VI-2 | Gm6880 |
| 6226 | 3 | 4 | 5 | 6 | | VI-2 | Gm7361 |
| 6227 | 3 | 4 | 5 | 6 | | VI-2 | Gm8221 |
| 6228 | 3 | 4 | 5 | 6 | | VI-2 | Gm8363 |
| 6229 | 3 | 4 | 5 | 6 | | VI-2 | Gm8615 |
| 6230 | 3 | 4 | 5 | 6 | | VI-2 | Gm884 |
| 6231 | 3 | 4 | 5 | 6 | | VI-2 | Gm8883 |
| 6232 | 3 | 4 | 5 | 6 | | VI-2 | Gm9054 |
| 6233 | 3 | 4 | 5 | 6 | | VI-2 | Gm9733 |
| 6234 | 3 | 4 | 5 | 6 | | VI-2 | Gm9926 |
| 6235 | 3 | 4 | 5 | 6 | | VI-2 | Gm9958 |
| 6236 | 3 | 4 | 5 | 6 | | VI-2 | Gm996 |
| 6237 | 3 | 4 | 5 | 6 | | VI-2 | Gmfb |
| 6238 | 3 | 4 | 5 | 6 | | VI-2 | Gna13 |

| | | | | | | | |
|---|---|---|---|---|---|---|---|
| 6239 | 3 | 4 | 5 | 6 | | VI-2 | Gnaq |
| 6240 | 3 | 4 | 5 | 6 | | VI-2 | Gnas |
| 6241 | 3 | 4 | 5 | 6 | | VI-2 | Gnaz |
| 6242 | 3 | 4 | 5 | 6 | | VI-2 | Gnb3 |
| 6243 | 3 | 4 | 5 | 6 | | VI-2 | Gnb4 |
| 6244 | 3 | 4 | 5 | 6 | | VI-2 | Gnpat |
| 6245 | 3 | 4 | 5 | 6 | | VI-2 | Gnptab |
| 6246 | 3 | 4 | 5 | 6 | | VI-2 | Golga1 |
| 6247 | 3 | 4 | 5 | 6 | | VI-2 | Golga5 |
| 6248 | 3 | 4 | 5 | 6 | | VI-2 | Golph3 |
| 6249 | 3 | 4 | 5 | 6 | | VI-2 | Gorab |
| 6250 | 3 | 4 | 5 | 6 | | VI-2 | Gosr1 |
| 6251 | 3 | 4 | 5 | 6 | | VI-2 | Gpalpp1 |
| 6252 | 3 | 4 | 5 | 6 | | VI-2 | Gpc2 |
| 6253 | 3 | 4 | 5 | 6 | | VI-2 | Gpd2 |
| 6254 | 3 | 4 | 5 | 6 | | VI-2 | Gpr110 |
| 6255 | 3 | 4 | 5 | 6 | | VI-2 | Gpr111 |
| 6256 | 3 | 4 | 5 | 6 | | VI-2 | Gpr115 |
| 6257 | 3 | 4 | 5 | 6 | | VI-2 | Gpr137b |
| 6258 | 3 | 4 | 5 | 6 | | VI-2 | Gpr141 |
| 6259 | 3 | 4 | 5 | 6 | | VI-2 | Gpr156 |
| 6260 | 3 | 4 | 5 | 6 | | VI-2 | Gpr160 |
| 6261 | 3 | 4 | 5 | 6 | | VI-2 | Gpr161 |
| 6262 | 3 | 4 | 5 | 6 | | VI-2 | Gpr18 |
| 6263 | 3 | 4 | 5 | 6 | | VI-2 | Gpr180 |
| 6264 | 3 | 4 | 5 | 6 | | VI-2 | Gpr182 |
| 6265 | 3 | 4 | 5 | 6 | | VI-2 | Gpr183 |
| 6266 | 3 | 4 | 5 | 6 | | VI-2 | Gpr19 |
| 6267 | 3 | 4 | 5 | 6 | | VI-2 | Gpr22 |
| 6268 | 3 | 4 | 5 | 6 | | VI-2 | Gpr25 |
| 6269 | 3 | 4 | 5 | 6 | | VI-2 | Gpr27 |
| 6270 | 3 | 4 | 5 | 6 | | VI-2 | Gpr56 |
| 6271 | 3 | 4 | 5 | 6 | | VI-2 | Gpr68 |
| 6272 | 3 | 4 | 5 | 6 | | VI-2 | Gpr75 |
| 6273 | 3 | 4 | 5 | 6 | | VI-2 | Gpr83 |
| 6274 | 3 | 4 | 5 | 6 | | VI-2 | Gpr87 |
| 6275 | 3 | 4 | 5 | 6 | | VI-2 | Gprasp2 |
| 6276 | 3 | 4 | 5 | 6 | | VI-2 | Gprc6a |
| 6277 | 3 | 4 | 5 | 6 | | VI-2 | Gprin2 |
| 6278 | 3 | 4 | 5 | 6 | | VI-2 | Gprin3 |
| 6279 | 3 | 4 | 5 | 6 | | VI-2 | Gps1 |
| 6280 | 3 | 4 | 5 | 6 | | VI-2 | Gpsm2 |
| 6281 | 3 | 4 | 5 | 6 | | VI-2 | Gpx2-ps1 |
| 6282 | 3 | 4 | 5 | 6 | | VI-2 | Grap2 |
| 6283 | 3 | 4 | 5 | 6 | | VI-2 | Grb2 |
| 6284 | 3 | 4 | 5 | 6 | | VI-2 | Greb1 |
| 6285 | 3 | 4 | 5 | 6 | | VI-2 | Grem1 |
| 6286 | 3 | 4 | 5 | 6 | | VI-2 | Grifin |
| 6287 | 3 | 4 | 5 | 6 | | VI-2 | Grin2a |
| 6288 | 3 | 4 | 5 | 6 | | VI-2 | Grin2b |
| 6289 | 3 | 4 | 5 | 6 | | VI-2 | Grin2d |
| 6290 | 3 | 4 | 5 | 6 | | VI-2 | Gsap |
| 6291 | 3 | 4 | 5 | 6 | | VI-2 | Gsdma2 |
| 6292 | 3 | 4 | 5 | 6 | | VI-2 | Gsdmc |
| 6293 | 3 | 4 | 5 | 6 | | VI-2 | Gsdmct-ps |
| 6294 | 3 | 4 | 5 | 6 | | VI-2 | Gspt1 |
| 6295 | 3 | 4 | 5 | 6 | | VI-2 | Gstcd |
| 6296 | 3 | 4 | 5 | 6 | | VI-2 | Gstm4 |
| 6297 | 3 | 4 | 5 | 6 | | VI-2 | Gstt1 |
| 6298 | 3 | 4 | 5 | 6 | | VI-2 | Gstz1 |
| 6299 | 3 | 4 | 5 | 6 | | VI-2 | Gtf2h1 |
| 6300 | 3 | 4 | 5 | 6 | | VI-2 | Gtf2h3 |
| 6301 | 3 | 4 | 5 | 6 | | VI-2 | Gtf2i |
| 6302 | 3 | 4 | 5 | 6 | | VI-2 | Gtf3c1 |
| 6303 | 3 | 4 | 5 | 6 | | VI-2 | Gtf3c2 |
| 6304 | 3 | 4 | 5 | 6 | | VI-2 | Gtf3c3 |
| 6305 | 3 | 4 | 5 | 6 | | VI-2 | Gtf3c4 |
| 6306 | 3 | 4 | 5 | 6 | | VI-2 | Gtpbp3 |
| 6307 | 3 | 4 | 5 | 6 | | VI-2 | Gtpbp8 |
| 6308 | 3 | 4 | 5 | 6 | | VI-2 | Gtse1 |
| 6309 | 3 | 4 | 5 | 6 | | VI-2 | Gtsf1 |
| 6310 | 3 | 4 | 5 | 6 | | VI-2 | Gucy1a2 |
| 6311 | 3 | 4 | 5 | 6 | | VI-2 | Gypa |
| 6312 | 3 | 4 | 5 | 6 | | VI-2 | Gypc |
| 6313 | 3 | 4 | 5 | 6 | | VI-2 | H2-DMa |
| 6314 | 3 | 4 | 5 | 6 | | VI-2 | H2-Eb2 |
| 6315 | 3 | 4 | 5 | 6 | | VI-2 | H2-M5 |
| 6316 | 3 | 4 | 5 | 6 | | VI-2 | H2-T10 |
| 6317 | 3 | 4 | 5 | 6 | | VI-2 | H2afy3 |
| 6318 | 3 | 4 | 5 | 6 | | VI-2 | H60b |
| 6319 | 3 | 4 | 5 | 6 | | VI-2 | Hadh |
| 6320 | 3 | 4 | 5 | 6 | | VI-2 | Hadhb |
| 6321 | 3 | 4 | 5 | 6 | | VI-2 | Hao2 |
| 6322 | 3 | 4 | 5 | 6 | | VI-2 | Hars |
| 6323 | 3 | 4 | 5 | 6 | | VI-2 | Haus6 |
| 6324 | 3 | 4 | 5 | 6 | | VI-2 | Havcr1 |
| 6325 | 3 | 4 | 5 | 6 | | VI-2 | Hcfc1 |
| 6326 | 3 | 4 | 5 | 6 | | VI-2 | Hcfc2 |
| 6327 | 3 | 4 | 5 | 6 | | VI-2 | Hcn3 |
| 6328 | 3 | 4 | 5 | 6 | | VI-2 | Hdac1 |
| 6329 | 3 | 4 | 5 | 6 | | VI-2 | Hdac7 |
| 6330 | 3 | 4 | 5 | 6 | | VI-2 | Hdac8 |
| 6331 | 3 | 4 | 5 | 6 | | VI-2 | Hdac9 |
| 6332 | 3 | 4 | 5 | 6 | | VI-2 | Hdhd2 |
| 6333 | 3 | 4 | 5 | 6 | | VI-2 | Heatr2 |
| 6334 | 3 | 4 | 5 | 6 | | VI-2 | Heatr6 |

Fig. 34 - 34

| | | | | | | | |
|---|---|---|---|---|---|---|---|
| 6335 | 3 | 4 | 5 | 6 | | VI-2 | Hectd2 |
| 6336 | 3 | 4 | 5 | 6 | | VI-2 | Hectd3 |
| 6337 | 3 | 4 | 5 | 6 | | VI-2 | Hells |
| 6338 | 3 | 4 | 5 | 6 | | VI-2 | Helq |
| 6339 | 3 | 4 | 5 | 6 | | VI-2 | Heph |
| 6340 | 3 | 4 | 5 | 6 | | VI-2 | Herc1 |
| 6341 | 3 | 4 | 5 | 6 | | VI-2 | Herc2 |
| 6342 | 3 | 4 | 5 | 6 | | VI-2 | Hexim1 |
| 6343 | 3 | 4 | 5 | 6 | | VI-2 | Hexim2 |
| 6344 | 3 | 4 | 5 | 6 | | VI-2 | Hey1 |
| 6345 | 3 | 4 | 5 | 6 | | VI-2 | Heyl |
| 6346 | 3 | 4 | 5 | 6 | | VI-2 | Hhex |
| 6347 | 3 | 4 | 5 | 6 | | VI-2 | Hhip |
| 6348 | 3 | 4 | 5 | 6 | | VI-2 | Hiat1 |
| 6349 | 3 | 4 | 5 | 6 | | VI-2 | Hiatl1 |
| 6350 | 3 | 4 | 5 | 6 | | VI-2 | Hic1 |
| 6351 | 3 | 4 | 5 | 6 | | VI-2 | Hif1a |
| 6352 | 3 | 4 | 5 | 6 | | VI-2 | Hira |
| 6353 | 3 | 4 | 5 | 6 | | VI-2 | Hirip3 |
| 6354 | 3 | 4 | 5 | 6 | | VI-2 | Hist1h1b |
| 6355 | 3 | 4 | 5 | 6 | | VI-2 | Hist1h2ak |
| 6356 | 3 | 4 | 5 | 6 | | VI-2 | Hist1h3b |
| 6357 | 3 | 4 | 5 | 6 | | VI-2 | Hist1h3g |
| 6358 | 3 | 4 | 5 | 6 | | VI-2 | Hist1h3h |
| 6359 | 3 | 4 | 5 | 6 | | VI-2 | Hist2h2ab |
| 6360 | 3 | 4 | 5 | 6 | | VI-2 | Hist3h2bb-ps |
| 6361 | 3 | 4 | 5 | 6 | | VI-2 | Hivep1 |
| 6362 | 3 | 4 | 5 | 6 | | VI-2 | Hivep3 |
| 6363 | 3 | 4 | 5 | 6 | | VI-2 | Hk1 |
| 6364 | 3 | 4 | 5 | 6 | | VI-2 | Hlcs |
| 6365 | 3 | 4 | 5 | 6 | | VI-2 | Hlf |
| 6366 | 3 | 4 | 5 | 6 | | VI-2 | Hlx |
| 6367 | 3 | 4 | 5 | 6 | | VI-2 | Hmcn1 |
| 6368 | 3 | 4 | 5 | 6 | | VI-2 | Hmgcr |
| 6369 | 3 | 4 | 5 | 6 | | VI-2 | Hmgn5 |
| 6370 | 3 | 4 | 5 | 6 | | VI-2 | Hmmr |
| 6371 | 3 | 4 | 5 | 6 | | VI-2 | Hmx2 |
| 6372 | 3 | 4 | 5 | 6 | | VI-2 | Hnmt |
| 6373 | 3 | 4 | 5 | 6 | | VI-2 | Hnrnpa0 |
| 6374 | 3 | 4 | 5 | 6 | | VI-2 | Hnrnpab |
| 6375 | 3 | 4 | 5 | 6 | | VI-2 | Hnrnpc |
| 6376 | 3 | 4 | 5 | 6 | | VI-2 | Hnrnpd |
| 6377 | 3 | 4 | 5 | 6 | | VI-2 | Hnrnpll |
| 6378 | 3 | 4 | 5 | 6 | | VI-2 | Hnrnpm |
| 6379 | 3 | 4 | 5 | 6 | | VI-2 | Hnrnpu |
| 6380 | 3 | 4 | 5 | 6 | | VI-2 | Homer1 |
| 6381 | 3 | 4 | 5 | 6 | | VI-2 | Homer2 |
| 6382 | 3 | 4 | 5 | 6 | | VI-2 | Hoxa11os |
| 6383 | 3 | 4 | 5 | 6 | | VI-2 | Hoxa13 |
| 6384 | 3 | 4 | 5 | 6 | | VI-2 | Hoxa7 |
| 6385 | 3 | 4 | 5 | 6 | | VI-2 | Hoxb2 |
| 6386 | 3 | 4 | 5 | 6 | | VI-2 | Hoxb6 |
| 6387 | 3 | 4 | 5 | 6 | | VI-2 | Hoxb9 |
| 6388 | 3 | 4 | 5 | 6 | | VI-2 | Hoxc4 |
| 6389 | 3 | 4 | 5 | 6 | | VI-2 | Hoxc5 |
| 6390 | 3 | 4 | 5 | 6 | | VI-2 | Hoxc8 |
| 6391 | 3 | 4 | 5 | 6 | | VI-2 | Hoxd3 |
| 6392 | 3 | 4 | 5 | 6 | | VI-2 | Hoxd3os1 |
| 6393 | 3 | 4 | 5 | 6 | | VI-2 | Hps6 |
| 6394 | 3 | 4 | 5 | 6 | | VI-2 | Hpse |
| 6395 | 3 | 4 | 5 | 6 | | VI-2 | Hrh2 |
| 6396 | 3 | 4 | 5 | 6 | | VI-2 | Hrnr |
| 6397 | 3 | 4 | 5 | 6 | | VI-2 | Hs2st1 |
| 6398 | 3 | 4 | 5 | 6 | | VI-2 | Hs3st2 |
| 6399 | 3 | 4 | 5 | 6 | | VI-2 | Hs3st5 |
| 6400 | 3 | 4 | 5 | 6 | | VI-2 | Hscb |
| 6401 | 3 | 4 | 5 | 6 | | VI-2 | Hsd17b3 |
| 6402 | 3 | 4 | 5 | 6 | | VI-2 | Hsd3b5 |
| 6403 | 3 | 4 | 5 | 6 | | VI-2 | Hsd3b6 |
| 6404 | 3 | 4 | 5 | 6 | | VI-2 | Hsd3b7 |
| 6405 | 3 | 4 | 5 | 6 | | VI-2 | Hsf2bp |
| 6406 | 3 | 4 | 5 | 6 | | VI-2 | Hspa14 |
| 6407 | 3 | 4 | 5 | 6 | | VI-2 | Hspa5 |
| 6408 | 3 | 4 | 5 | 6 | | VI-2 | Hspa8 |
| 6409 | 3 | 4 | 5 | 6 | | VI-2 | Hsph1 |
| 6410 | 3 | 4 | 5 | 6 | | VI-2 | Htatsf1 |
| 6411 | 3 | 4 | 5 | 6 | | VI-2 | Htr3a |
| 6412 | 3 | 4 | 5 | 6 | | VI-2 | Htr7 |
| 6413 | 3 | 4 | 5 | 6 | | VI-2 | Hus1 |
| 6414 | 3 | 4 | 5 | 6 | | VI-2 | Hyal2 |
| 6415 | 3 | 4 | 5 | 6 | | VI-2 | Hykk |
| 6416 | 3 | 4 | 5 | 6 | | VI-2 | I830077J02Rik |
| 6417 | 3 | 4 | 5 | 6 | | VI-2 | Icmt |
| 6418 | 3 | 4 | 5 | 6 | | VI-2 | Icosl |
| 6419 | 3 | 4 | 5 | 6 | | VI-2 | Idh1 |
| 6420 | 3 | 4 | 5 | 6 | | VI-2 | Idh2 |
| 6421 | 3 | 4 | 5 | 6 | | VI-2 | Idh3a |
| 6422 | 3 | 4 | 5 | 6 | | VI-2 | Idi1 |
| 6423 | 3 | 4 | 5 | 6 | | VI-2 | Idua |
| 6424 | 3 | 4 | 5 | 6 | | VI-2 | Ifi202b |
| 6425 | 3 | 4 | 5 | 6 | | VI-2 | Ifitm10 |
| 6426 | 3 | 4 | 5 | 6 | | VI-2 | Ifitm3 |
| 6427 | 3 | 4 | 5 | 6 | | VI-2 | Ifngr2 |
| 6428 | 3 | 4 | 5 | 6 | | VI-2 | Ifnlr1 |
| 6429 | 3 | 4 | 5 | 6 | | VI-2 | Ifrd2 |
| 6430 | 3 | 4 | 5 | 6 | | VI-2 | Ift57 |
| 6431 | 3 | 4 | 5 | 6 | | VI-2 | Ift80 |
| 6432 | 3 | 4 | 5 | 6 | | VI-2 | Igbp1 |
| 6433 | 3 | 4 | 5 | 6 | | VI-2 | Igdcc4 |
| 6434 | 3 | 4 | 5 | 6 | | VI-2 | Igf1 |
| 6435 | 3 | 4 | 5 | 6 | | VI-2 | Igf2 |
| 6436 | 3 | 4 | 5 | 6 | | VI-2 | Igf2r |
| 6437 | 3 | 4 | 5 | 6 | | VI-2 | Ighmbp2 |
| 6438 | 3 | 4 | 5 | 6 | | VI-2 | Igsf10 |
| 6439 | 3 | 4 | 5 | 6 | | VI-2 | Igsf21 |
| 6440 | 3 | 4 | 5 | 6 | | VI-2 | Igsf3 |
| 6441 | 3 | 4 | 5 | 6 | | VI-2 | Igsf8 |
| 6442 | 3 | 4 | 5 | 6 | | VI-2 | Igsf9 |
| 6443 | 3 | 4 | 5 | 6 | | VI-2 | Igsf9b |
| 6444 | 3 | 4 | 5 | 6 | | VI-2 | Ik |
| 6445 | 3 | 4 | 5 | 6 | | VI-2 | Ikzf1 |
| 6446 | 3 | 4 | 5 | 6 | | VI-2 | Ikzf2 |
| 6447 | 3 | 4 | 5 | 6 | | VI-2 | Ikzf3 |
| 6448 | 3 | 4 | 5 | 6 | | VI-2 | Ikzf4 |
| 6449 | 3 | 4 | 5 | 6 | | VI-2 | Il12a |
| 6450 | 3 | 4 | 5 | 6 | | VI-2 | Il12b |
| 6451 | 3 | 4 | 5 | 6 | | VI-2 | Il13ra1 |
| 6452 | 3 | 4 | 5 | 6 | | VI-2 | Il17c |
| 6453 | 3 | 4 | 5 | 6 | | VI-2 | Il17rd |
| 6454 | 3 | 4 | 5 | 6 | | VI-2 | Il1f5 |
| 6455 | 3 | 4 | 5 | 6 | | VI-2 | Il1rl1 |
| 6456 | 3 | 4 | 5 | 6 | | VI-2 | Il20rb |
| 6457 | 3 | 4 | 5 | 6 | | VI-2 | Il21 |
| 6458 | 3 | 4 | 5 | 6 | | VI-2 | Il21r |
| 6459 | 3 | 4 | 5 | 6 | | VI-2 | Il22ra2 |
| 6460 | 3 | 4 | 5 | 6 | | VI-2 | Il27ra |
| 6461 | 3 | 4 | 5 | 6 | | VI-2 | Il2ra |
| 6462 | 3 | 4 | 5 | 6 | | VI-2 | Il7 |
| 6463 | 3 | 4 | 5 | 6 | | VI-2 | Il9r |
| 6464 | 3 | 4 | 5 | 6 | | VI-2 | Ilf3 |
| 6465 | 3 | 4 | 5 | 6 | | VI-2 | Impa1 |
| 6466 | 3 | 4 | 5 | 6 | | VI-2 | Impa2 |
| 6467 | 3 | 4 | 5 | 6 | | VI-2 | Incenp |
| 6468 | 3 | 4 | 5 | 6 | | VI-2 | Ing5 |
| 6469 | 3 | 4 | 5 | 6 | | VI-2 | Inhbc |
| 6470 | 3 | 4 | 5 | 6 | | VI-2 | Ino80d |
| 6471 | 3 | 4 | 5 | 6 | | VI-2 | Inpp1 |
| 6472 | 3 | 4 | 5 | 6 | | VI-2 | Inpp5b |
| 6473 | 3 | 4 | 5 | 6 | | VI-2 | Inppl1 |
| 6474 | 3 | 4 | 5 | 6 | | VI-2 | Ints2 |
| 6475 | 3 | 4 | 5 | 6 | | VI-2 | Ints4 |
| 6476 | 3 | 4 | 5 | 6 | | VI-2 | Ipcef1 |
| 6477 | 3 | 4 | 5 | 6 | | VI-2 | Ipo8 |
| 6478 | 3 | 4 | 5 | 6 | | VI-2 | Ipp |
| 6479 | 3 | 4 | 5 | 6 | | VI-2 | Iqca |
| 6480 | 3 | 4 | 5 | 6 | | VI-2 | Iqce |
| 6481 | 3 | 4 | 5 | 6 | | VI-2 | Iqgap1 |
| 6482 | 3 | 4 | 5 | 6 | | VI-2 | Iqgap3 |
| 6483 | 3 | 4 | 5 | 6 | | VI-2 | Iqsec1 |
| 6484 | 3 | 4 | 5 | 6 | | VI-2 | Irak1 |
| 6485 | 3 | 4 | 5 | 6 | | VI-2 | Irf1 |
| 6486 | 3 | 4 | 5 | 6 | | VI-2 | Irf2bp1 |
| 6487 | 3 | 4 | 5 | 6 | | VI-2 | Irf8 |
| 6488 | 3 | 4 | 5 | 6 | | VI-2 | Irs3 |
| 6489 | 3 | 4 | 5 | 6 | | VI-2 | Irx1 |
| 6490 | 3 | 4 | 5 | 6 | | VI-2 | Irx4 |
| 6491 | 3 | 4 | 5 | 6 | | VI-2 | Irx5 |
| 6492 | 3 | 4 | 5 | 6 | | VI-2 | Islr |
| 6493 | 3 | 4 | 5 | 6 | | VI-2 | Itga1 |
| 6494 | 3 | 4 | 5 | 6 | | VI-2 | Itgb6 |
| 6495 | 3 | 4 | 5 | 6 | | VI-2 | Itih2 |
| 6496 | 3 | 4 | 5 | 6 | | VI-2 | Itpripl1 |
| 6497 | 3 | 4 | 5 | 6 | | VI-2 | Itsn1 |
| 6498 | 3 | 4 | 5 | 6 | | VI-2 | Iws1 |
| 6499 | 3 | 4 | 5 | 6 | | VI-2 | Jade3 |
| 6500 | 3 | 4 | 5 | 6 | | VI-2 | Jag1 |
| 6501 | 3 | 4 | 5 | 6 | | VI-2 | Jak3 |
| 6502 | 3 | 4 | 5 | 6 | | VI-2 | Jakmip1 |
| 6503 | 3 | 4 | 5 | 6 | | VI-2 | Jam2 |
| 6504 | 3 | 4 | 5 | 6 | | VI-2 | Jarid2 |
| 6505 | 3 | 4 | 5 | 6 | | VI-2 | Jmy |
| 6506 | 3 | 4 | 5 | 6 | | VI-2 | Kank4 |
| 6507 | 3 | 4 | 5 | 6 | | VI-2 | Kansl2 |
| 6508 | 3 | 4 | 5 | 6 | | VI-2 | Kansl3 |
| 6509 | 3 | 4 | 5 | 6 | | VI-2 | Kat6a |
| 6510 | 3 | 4 | 5 | 6 | | VI-2 | Kat7 |
| 6511 | 3 | 4 | 5 | 6 | | VI-2 | Kazn |
| 6512 | 3 | 4 | 5 | 6 | | VI-2 | Kbtbd13 |
| 6513 | 3 | 4 | 5 | 6 | | VI-2 | Kbtbd2 |
| 6514 | 3 | 4 | 5 | 6 | | VI-2 | Kbtbd4 |
| 6515 | 3 | 4 | 5 | 6 | | VI-2 | Kbtbd8 |
| 6516 | 3 | 4 | 5 | 6 | | VI-2 | Kcnab3 |
| 6517 | 3 | 4 | 5 | 6 | | VI-2 | Kcng4 |
| 6518 | 3 | 4 | 5 | 6 | | VI-2 | Kcnh1 |
| 6519 | 3 | 4 | 5 | 6 | | VI-2 | Kcnj5 |
| 6520 | 3 | 4 | 5 | 6 | | VI-2 | Kcnj6 |
| 6521 | 3 | 4 | 5 | 6 | | VI-2 | Kcnq4 |
| 6522 | 3 | 4 | 5 | 6 | | VI-2 | Kcp |
| 6523 | 3 | 4 | 5 | 6 | | VI-2 | Kctd1 |
| 6524 | 3 | 4 | 5 | 6 | | VI-2 | Kctd11 |
| 6525 | 3 | 4 | 5 | 6 | | VI-2 | Kctd12b |
| 6526 | 3 | 4 | 5 | 6 | | VI-2 | Kctd14 |

Fig. 34 - 35

| | | | | | | | |
|---|---|---|---|---|---|---|---|
| 6527 | 3 | 4 | 5 | 6 | | VI-2 | Kctd19 |
| 6528 | 3 | 4 | 5 | 6 | | VI-2 | Kctd21 |
| 6529 | 3 | 4 | 5 | 6 | | VI-2 | Kctd3 |
| 6530 | 3 | 4 | 5 | 6 | | VI-2 | Kdelc1 |
| 6531 | 3 | 4 | 5 | 6 | | VI-2 | Kdelr3 |
| 6532 | 3 | 4 | 5 | 6 | | VI-2 | Kdf1 |
| 6533 | 3 | 4 | 5 | 6 | | VI-2 | Kdm3a |
| 6534 | 3 | 4 | 5 | 6 | | VI-2 | Kdm5c |
| 6535 | 3 | 4 | 5 | 6 | | VI-2 | Kdm5d |
| 6536 | 3 | 4 | 5 | 6 | | VI-2 | Kera |
| 6537 | 3 | 4 | 5 | 6 | | VI-2 | Kidins220 |
| 6538 | 3 | 4 | 5 | 6 | | VI-2 | Kif11 |
| 6539 | 3 | 4 | 5 | 6 | | VI-2 | Kif12 |
| 6540 | 3 | 4 | 5 | 6 | | VI-2 | Kif14 |
| 6541 | 3 | 4 | 5 | 6 | | VI-2 | Kif15 |
| 6542 | 3 | 4 | 5 | 6 | | VI-2 | Kif16b |
| 6543 | 3 | 4 | 5 | 6 | | VI-2 | Kif18a |
| 6544 | 3 | 4 | 5 | 6 | | VI-2 | Kif18b |
| 6545 | 3 | 4 | 5 | 6 | | VI-2 | Kif1b |
| 6546 | 3 | 4 | 5 | 6 | | VI-2 | Kif1c |
| 6547 | 3 | 4 | 5 | 6 | | VI-2 | Kif20b |
| 6548 | 3 | 4 | 5 | 6 | | VI-2 | Kif22 |
| 6549 | 3 | 4 | 5 | 6 | | VI-2 | Kif23 |
| 6550 | 3 | 4 | 5 | 6 | | VI-2 | Kif24 |
| 6551 | 3 | 4 | 5 | 6 | | VI-2 | Kif26a |
| 6552 | 3 | 4 | 5 | 6 | | VI-2 | Kif3c |
| 6553 | 3 | 4 | 5 | 6 | | VI-2 | Kifc1 |
| 6554 | 3 | 4 | 5 | 6 | | VI-2 | Kiss1r |
| 6555 | 3 | 4 | 5 | 6 | | VI-2 | Kit |
| 6556 | 3 | 4 | 5 | 6 | | VI-2 | Klb |
| 6557 | 3 | 4 | 5 | 6 | | VI-2 | Klf11 |
| 6558 | 3 | 4 | 5 | 6 | | VI-2 | Klf12 |
| 6559 | 3 | 4 | 5 | 6 | | VI-2 | Klf13 |
| 6560 | 3 | 4 | 5 | 6 | | VI-2 | Klf14 |
| 6561 | 3 | 4 | 5 | 6 | | VI-2 | Klf8 |
| 6562 | 3 | 4 | 5 | 6 | | VI-2 | Klhdc7a |
| 6563 | 3 | 4 | 5 | 6 | | VI-2 | Klhl13 |
| 6564 | 3 | 4 | 5 | 6 | | VI-2 | Klhl17 |
| 6565 | 3 | 4 | 5 | 6 | | VI-2 | Klhl22 |
| 6566 | 3 | 4 | 5 | 6 | | VI-2 | Klhl28 |
| 6567 | 3 | 4 | 5 | 6 | | VI-2 | Klhl29 |
| 6568 | 3 | 4 | 5 | 6 | | VI-2 | Klhl36 |
| 6569 | 3 | 4 | 5 | 6 | | VI-2 | Klhl42 |
| 6570 | 3 | 4 | 5 | 6 | | VI-2 | Klhl8 |
| 6571 | 3 | 4 | 5 | 6 | | VI-2 | Klk10 |
| 6572 | 3 | 4 | 5 | 6 | | VI-2 | Klk1b21 |
| 6573 | 3 | 4 | 5 | 6 | | VI-2 | Klk1b22 |
| 6574 | 3 | 4 | 5 | 6 | | VI-2 | Klk1b24 |
| 6575 | 3 | 4 | 5 | 6 | | VI-2 | Klkb1 |
| 6576 | 3 | 4 | 5 | 6 | | VI-2 | Klra1 |
| 6577 | 3 | 4 | 5 | 6 | | VI-2 | Klra18 |
| 6578 | 3 | 4 | 5 | 6 | | VI-2 | Klrb1b |
| 6579 | 3 | 4 | 5 | 6 | | VI-2 | Klrb1c |
| 6580 | 3 | 4 | 5 | 6 | | VI-2 | Klrg1 |
| 6581 | 3 | 4 | 5 | 6 | | VI-2 | Kmt2b |
| 6582 | 3 | 4 | 5 | 6 | | VI-2 | Kpna1 |
| 6583 | 3 | 4 | 5 | 6 | | VI-2 | Kpna2 |
| 6584 | 3 | 4 | 5 | 6 | | VI-2 | Kpna4 |
| 6585 | 3 | 4 | 5 | 6 | | VI-2 | Kprp |
| 6586 | 3 | 4 | 5 | 6 | | VI-2 | Kras |
| 6587 | 3 | 4 | 5 | 6 | | VI-2 | Kremen2 |
| 6588 | 3 | 4 | 5 | 6 | | VI-2 | Krit1 |
| 6589 | 3 | 4 | 5 | 6 | | VI-2 | Krr1 |
| 6590 | 3 | 4 | 5 | 6 | | VI-2 | Krt1 |
| 6591 | 3 | 4 | 5 | 6 | | VI-2 | Krt13 |
| 6592 | 3 | 4 | 5 | 6 | | VI-2 | Krt14 |
| 6593 | 3 | 4 | 5 | 6 | | VI-2 | Krt16 |
| 6594 | 3 | 4 | 5 | 6 | | VI-2 | Krt2 |
| 6595 | 3 | 4 | 5 | 6 | | VI-2 | Krt24 |
| 6596 | 3 | 4 | 5 | 6 | | VI-2 | Krt4 |
| 6597 | 3 | 4 | 5 | 6 | | VI-2 | Krt5 |
| 6598 | 3 | 4 | 5 | 6 | | VI-2 | Krt73 |
| 6599 | 3 | 4 | 5 | 6 | | VI-2 | Krt78 |
| 6600 | 3 | 4 | 5 | 6 | | VI-2 | Krt84 |
| 6601 | 3 | 4 | 5 | 6 | | VI-2 | Krtap1-5 |
| 6602 | 3 | 4 | 5 | 6 | | VI-2 | Krtap16-1 |
| 6603 | 3 | 4 | 5 | 6 | | VI-2 | Krtap19-3 |
| 6604 | 3 | 4 | 5 | 6 | | VI-2 | Krtap19-5 |
| 6605 | 3 | 4 | 5 | 6 | | VI-2 | Krtap19-9b |
| 6606 | 3 | 4 | 5 | 6 | | VI-2 | Krtap4-7 |
| 6607 | 3 | 4 | 5 | 6 | | VI-2 | Krtap6-1 |
| 6608 | 3 | 4 | 5 | 6 | | VI-2 | Krtap6-5 |
| 6609 | 3 | 4 | 5 | 6 | | VI-2 | Ksr1 |
| 6610 | 3 | 4 | 5 | 6 | | VI-2 | Ksr2 |
| 6611 | 3 | 4 | 5 | 6 | | VI-2 | L1cam |
| 6612 | 3 | 4 | 5 | 6 | | VI-2 | L3hypdh |
| 6613 | 3 | 4 | 5 | 6 | | VI-2 | LOC100040786 |
| 6614 | 3 | 4 | 5 | 6 | | VI-2 | LOC101056043 |
| 6615 | 3 | 4 | 5 | 6 | | VI-2 | LOC102631757 |
| 6616 | 3 | 4 | 5 | 6 | | VI-2 | Lair1 |
| 6617 | 3 | 4 | 5 | 6 | | VI-2 | Lama2 |
| 6618 | 3 | 4 | 5 | 6 | | VI-2 | Lamc1 |
| 6619 | 3 | 4 | 5 | 6 | | VI-2 | Lamtor1 |
| 6620 | 3 | 4 | 5 | 6 | | VI-2 | Larp1 |
| 6621 | 3 | 4 | 5 | 6 | | VI-2 | Larp1b |
| 6622 | 3 | 4 | 5 | 6 | | VI-2 | Lasp1 |
| 6623 | 3 | 4 | 5 | 6 | | VI-2 | Lats1 |
| 6624 | 3 | 4 | 5 | 6 | | VI-2 | Lats2 |
| 6625 | 3 | 4 | 5 | 6 | | VI-2 | Layn |
| 6626 | 3 | 4 | 5 | 6 | | VI-2 | Lbh |
| 6627 | 3 | 4 | 5 | 6 | | VI-2 | Lce3a |
| 6628 | 3 | 4 | 5 | 6 | | VI-2 | Lclat1 |
| 6629 | 3 | 4 | 5 | 6 | | VI-2 | Lcmt2 |
| 6630 | 3 | 4 | 5 | 6 | | VI-2 | Lcn10 |
| 6631 | 3 | 4 | 5 | 6 | | VI-2 | Lcn8 |
| 6632 | 3 | 4 | 5 | 6 | | VI-2 | Lcn9 |
| 6633 | 3 | 4 | 5 | 6 | | VI-2 | Lcp1 |
| 6634 | 3 | 4 | 5 | 6 | | VI-2 | Lcp2 |
| 6635 | 3 | 4 | 5 | 6 | | VI-2 | Ldb3 |
| 6636 | 3 | 4 | 5 | 6 | | VI-2 | Ldoc1l |
| 6637 | 3 | 4 | 5 | 6 | | VI-2 | Lect2 |
| 6638 | 3 | 4 | 5 | 6 | | VI-2 | Lemd3 |
| 6639 | 3 | 4 | 5 | 6 | | VI-2 | Leo1 |
| 6640 | 3 | 4 | 5 | 6 | | VI-2 | Leprel2 |
| 6641 | 3 | 4 | 5 | 6 | | VI-2 | Letmd1 |
| 6642 | 3 | 4 | 5 | 6 | | VI-2 | Lgals6 |
| 6643 | 3 | 4 | 5 | 6 | | VI-2 | Lgr5 |
| 6644 | 3 | 4 | 5 | 6 | | VI-2 | Lgr6 |
| 6645 | 3 | 4 | 5 | 6 | | VI-2 | Lhfpl1 |
| 6646 | 3 | 4 | 5 | 6 | | VI-2 | Lhx5 |
| 6647 | 3 | 4 | 5 | 6 | | VI-2 | Lig4 |
| 6648 | 3 | 4 | 5 | 6 | | VI-2 | Lilra5 |
| 6649 | 3 | 4 | 5 | 6 | | VI-2 | Lilra6 |
| 6650 | 3 | 4 | 5 | 6 | | VI-2 | Limch1 |
| 6651 | 3 | 4 | 5 | 6 | | VI-2 | Lims1 |
| 6652 | 3 | 4 | 5 | 6 | | VI-2 | Lin37 |
| 6653 | 3 | 4 | 5 | 6 | | VI-2 | Lin9 |
| 6654 | 3 | 4 | 5 | 6 | | VI-2 | Lipa |
| 6655 | 3 | 4 | 5 | 6 | | VI-2 | Lipf |
| 6656 | 3 | 4 | 5 | 6 | | VI-2 | Lipm |
| 6657 | 3 | 4 | 5 | 6 | | VI-2 | Lipt1 |
| 6658 | 3 | 4 | 5 | 6 | | VI-2 | Lipt2 |
| 6659 | 3 | 4 | 5 | 6 | | VI-2 | Lman1 |
| 6660 | 3 | 4 | 5 | 6 | | VI-2 | Lman2 |
| 6661 | 3 | 4 | 5 | 6 | | VI-2 | Lmnb1 |
| 6662 | 3 | 4 | 5 | 6 | | VI-2 | Lmo2 |
| 6663 | 3 | 4 | 5 | 6 | | VI-2 | Lmtk2 |
| 6664 | 3 | 4 | 5 | 6 | | VI-2 | Lnx1 |
| 6665 | 3 | 4 | 5 | 6 | | VI-2 | Lnx2 |
| 6666 | 3 | 4 | 5 | 6 | | VI-2 | Lpar4 |
| 6667 | 3 | 4 | 5 | 6 | | VI-2 | Lpcat2b |
| 6668 | 3 | 4 | 5 | 6 | | VI-2 | Lpgat1 |
| 6669 | 3 | 4 | 5 | 6 | | VI-2 | Lphn2 |
| 6670 | 3 | 4 | 5 | 6 | | VI-2 | Lphn3 |
| 6671 | 3 | 4 | 5 | 6 | | VI-2 | Lpp |
| 6672 | 3 | 4 | 5 | 6 | | VI-2 | Lrig2 |
| 6673 | 3 | 4 | 5 | 6 | | VI-2 | Lrit1 |
| 6674 | 3 | 4 | 5 | 6 | | VI-2 | Lrit2 |
| 6675 | 3 | 4 | 5 | 6 | | VI-2 | Lrp10 |
| 6676 | 3 | 4 | 5 | 6 | | VI-2 | Lrp12 |
| 6677 | 3 | 4 | 5 | 6 | | VI-2 | Lrp2bp |
| 6678 | 3 | 4 | 5 | 6 | | VI-2 | Lrp5 |
| 6679 | 3 | 4 | 5 | 6 | | VI-2 | Lrp8 |
| 6680 | 3 | 4 | 5 | 6 | | VI-2 | Lrpprc |
| 6681 | 3 | 4 | 5 | 6 | | VI-2 | Lrrc15 |
| 6682 | 3 | 4 | 5 | 6 | | VI-2 | Lrrc26 |
| 6683 | 3 | 4 | 5 | 6 | | VI-2 | Lrrc32 |
| 6684 | 3 | 4 | 5 | 6 | | VI-2 | Lrrc34 |
| 6685 | 3 | 4 | 5 | 6 | | VI-2 | Lrrc39 |
| 6686 | 3 | 4 | 5 | 6 | | VI-2 | Lrrc55 |
| 6687 | 3 | 4 | 5 | 6 | | VI-2 | Lrrc75a |
| 6688 | 3 | 4 | 5 | 6 | | VI-2 | Lrrc75b |
| 6689 | 3 | 4 | 5 | 6 | | VI-2 | Lrrc8c |
| 6690 | 3 | 4 | 5 | 6 | | VI-2 | Lrrcc1 |
| 6691 | 3 | 4 | 5 | 6 | | VI-2 | Lrrfip1 |
| 6692 | 3 | 4 | 5 | 6 | | VI-2 | Lrriq3 |
| 6693 | 3 | 4 | 5 | 6 | | VI-2 | Lrm3 |
| 6694 | 3 | 4 | 5 | 6 | | VI-2 | Lsm12 |
| 6695 | 3 | 4 | 5 | 6 | | VI-2 | Lsmem1 |
| 6696 | 3 | 4 | 5 | 6 | | VI-2 | Lss |
| 6697 | 3 | 4 | 5 | 6 | | VI-2 | Ltb4r2 |
| 6698 | 3 | 4 | 5 | 6 | | VI-2 | Ltbp4 |
| 6699 | 3 | 4 | 5 | 6 | | VI-2 | Luc7l2 |
| 6700 | 3 | 4 | 5 | 6 | | VI-2 | Lum |
| 6701 | 3 | 4 | 5 | 6 | | VI-2 | Lurap1l |
| 6702 | 3 | 4 | 5 | 6 | | VI-2 | Luzp1 |
| 6703 | 3 | 4 | 5 | 6 | | VI-2 | Lyg2 |
| 6704 | 3 | 4 | 5 | 6 | | VI-2 | Lypd6 |
| 6705 | 3 | 4 | 5 | 6 | | VI-2 | Lypla1 |
| 6706 | 3 | 4 | 5 | 6 | | VI-2 | Lyrm7 |
| 6707 | 3 | 4 | 5 | 6 | | VI-2 | Lysmd2 |
| 6708 | 3 | 4 | 5 | 6 | | VI-2 | Lysmd4 |
| 6709 | 3 | 4 | 5 | 6 | | VI-2 | Lyst |
| 6710 | 3 | 4 | 5 | 6 | | VI-2 | Lyzl6 |
| 6711 | 3 | 4 | 5 | 6 | | VI-2 | Lztfl1 |
| 6712 | 3 | 4 | 5 | 6 | | VI-2 | Lzts1 |
| 6713 | 3 | 4 | 5 | 6 | | VI-2 | M6pr |
| 6714 | 3 | 4 | 5 | 6 | | VI-2 | Mab21l1 |
| 6715 | 3 | 4 | 5 | 6 | | VI-2 | Mab21l2 |
| 6716 | 3 | 4 | 5 | 6 | | VI-2 | Mab21l3 |
| 6717 | 3 | 4 | 5 | 6 | | VI-2 | Macc1 |
| 6718 | 3 | 4 | 5 | 6 | | VI-2 | Macf1 |

Fig. 34 - 36

| | | | | | | | |
|---|---|---|---|---|---|---|---|
| 6719 | 3 | 4 | 5 | 6 | | VI-2 | Macrod2 |
| 6720 | 3 | 4 | 5 | 6 | | VI-2 | Mad1l1 |
| 6721 | 3 | 4 | 5 | 6 | | VI-2 | Maea |
| 6722 | 3 | 4 | 5 | 6 | | VI-2 | Mafa |
| 6723 | 3 | 4 | 5 | 6 | | VI-2 | Mageb16 |
| 6724 | 3 | 4 | 5 | 6 | | VI-2 | Mageb3 |
| 6725 | 3 | 4 | 5 | 6 | | VI-2 | Mageb5 |
| 6726 | 3 | 4 | 5 | 6 | | VI-2 | Maged1 |
| 6727 | 3 | 4 | 5 | 6 | | VI-2 | Magi1 |
| 6728 | 3 | 4 | 5 | 6 | | VI-2 | Magi3 |
| 6729 | 3 | 4 | 5 | 6 | | VI-2 | Magix |
| 6730 | 3 | 4 | 5 | 6 | | VI-2 | Man2b1 |
| 6731 | 3 | 4 | 5 | 6 | | VI-2 | Man2c1os |
| 6732 | 3 | 4 | 5 | 6 | | VI-2 | Map2k4 |
| 6733 | 3 | 4 | 5 | 6 | | VI-2 | Map3k10 |
| 6734 | 3 | 4 | 5 | 6 | | VI-2 | Map3k12 |
| 6735 | 3 | 4 | 5 | 6 | | VI-2 | Map3k7 |
| 6736 | 3 | 4 | 5 | 6 | | VI-2 | Mapk1 |
| 6737 | 3 | 4 | 5 | 6 | | VI-2 | Mapk11 |
| 6738 | 3 | 4 | 5 | 6 | | VI-2 | Mapk1ip1l |
| 6739 | 3 | 4 | 5 | 6 | | VI-2 | Mapk8 |
| 6740 | 3 | 4 | 5 | 6 | | VI-2 | Mapk9 |
| 6741 | 3 | 4 | 5 | 6 | | VI-2 | Mapkap1 |
| 6742 | 3 | 4 | 5 | 6 | | VI-2 | Mapre2 |
| 6743 | 3 | 4 | 5 | 6 | | VI-2 | March1 |
| 6744 | 3 | 4 | 5 | 6 | | VI-2 | Marcks |
| 6745 | 3 | 4 | 5 | 6 | | VI-2 | Marcksl1 |
| 6746 | 3 | 4 | 5 | 6 | | VI-2 | Marf1 |
| 6747 | 3 | 4 | 5 | 6 | | VI-2 | Mark1 |
| 6748 | 3 | 4 | 5 | 6 | | VI-2 | Marveld1 |
| 6749 | 3 | 4 | 5 | 6 | | VI-2 | Marveld2 |
| 6750 | 3 | 4 | 5 | 6 | | VI-2 | Mas1 |
| 6751 | 3 | 4 | 5 | 6 | | VI-2 | Mast1 |
| 6752 | 3 | 4 | 5 | 6 | | VI-2 | Mastl |
| 6753 | 3 | 4 | 5 | 6 | | VI-2 | Maz |
| 6754 | 3 | 4 | 5 | 6 | | VI-2 | Mb21d1 |
| 6755 | 3 | 4 | 5 | 6 | | VI-2 | Mbd2 |
| 6756 | 3 | 4 | 5 | 6 | | VI-2 | Mbd5 |
| 6757 | 3 | 4 | 5 | 6 | | VI-2 | Mbd6 |
| 6758 | 3 | 4 | 5 | 6 | | VI-2 | Mbl2 |
| 6759 | 3 | 4 | 5 | 6 | | VI-2 | Mblac1 |
| 6760 | 3 | 4 | 5 | 6 | | VI-2 | Mbnl1 |
| 6761 | 3 | 4 | 5 | 6 | | VI-2 | Mbnl3 |
| 6762 | 3 | 4 | 5 | 6 | | VI-2 | Mboat1 |
| 6763 | 3 | 4 | 5 | 6 | | VI-2 | Mboat2 |
| 6764 | 3 | 4 | 5 | 6 | | VI-2 | Mboat7 |
| 6765 | 3 | 4 | 5 | 6 | | VI-2 | Mcc |
| 6766 | 3 | 4 | 5 | 6 | | VI-2 | Mccc2 |
| 6767 | 3 | 4 | 5 | 6 | | VI-2 | Mcm10 |
| 6768 | 3 | 4 | 5 | 6 | | VI-2 | Mcm2 |
| 6769 | 3 | 4 | 5 | 6 | | VI-2 | Mcm3 |
| 6770 | 3 | 4 | 5 | 6 | | VI-2 | Mcm4 |
| 6771 | 3 | 4 | 5 | 6 | | VI-2 | Mcm6 |
| 6772 | 3 | 4 | 5 | 6 | | VI-2 | Mcm8 |
| 6773 | 3 | 4 | 5 | 6 | | VI-2 | Mcm9 |
| 6774 | 3 | 4 | 5 | 6 | | VI-2 | Mcoln1 |
| 6775 | 3 | 4 | 5 | 6 | | VI-2 | Mcoln3 |
| 6776 | 3 | 4 | 5 | 6 | | VI-2 | Mcts2 |
| 6777 | 3 | 4 | 5 | 6 | | VI-2 | Mcur1 |
| 6778 | 3 | 4 | 5 | 6 | | VI-2 | Mdfi |
| 6779 | 3 | 4 | 5 | 6 | | VI-2 | Mdm1 |
| 6780 | 3 | 4 | 5 | 6 | | VI-2 | Mdm2 |
| 6781 | 3 | 4 | 5 | 6 | | VI-2 | Med12 |
| 6782 | 3 | 4 | 5 | 6 | | VI-2 | Med17 |
| 6783 | 3 | 4 | 5 | 6 | | VI-2 | Med20 |
| 6784 | 3 | 4 | 5 | 6 | | VI-2 | Med24 |
| 6785 | 3 | 4 | 5 | 6 | | VI-2 | Med26 |
| 6786 | 3 | 4 | 5 | 6 | | VI-2 | Med31 |
| 6787 | 3 | 4 | 5 | 6 | | VI-2 | Med7 |
| 6788 | 3 | 4 | 5 | 6 | | VI-2 | Megf6 |
| 6789 | 3 | 4 | 5 | 6 | | VI-2 | Melk |
| 6790 | 3 | 4 | 5 | 6 | | VI-2 | Memo1 |
| 6791 | 3 | 4 | 5 | 6 | | VI-2 | Meox1 |
| 6792 | 3 | 4 | 5 | 6 | | VI-2 | Meox2 |
| 6793 | 3 | 4 | 5 | 6 | | VI-2 | Mep1b |
| 6794 | 3 | 4 | 5 | 6 | | VI-2 | Met |
| 6795 | 3 | 4 | 5 | 6 | | VI-2 | Mettl11b |
| 6796 | 3 | 4 | 5 | 6 | | VI-2 | Mettl22 |
| 6797 | 3 | 4 | 5 | 6 | | VI-2 | Mettl24 |
| 6798 | 3 | 4 | 5 | 6 | | VI-2 | Mettl3 |
| 6799 | 3 | 4 | 5 | 6 | | VI-2 | Mettl4 |
| 6800 | 3 | 4 | 5 | 6 | | VI-2 | Mettl9 |
| 6801 | 3 | 4 | 5 | 6 | | VI-2 | Mex3a |
| 6802 | 3 | 4 | 5 | 6 | | VI-2 | Mex3b |
| 6803 | 3 | 4 | 5 | 6 | | VI-2 | Mex3d |
| 6804 | 3 | 4 | 5 | 6 | | VI-2 | Mfap2 |
| 6805 | 3 | 4 | 5 | 6 | | VI-2 | Mfap3 |
| 6806 | 3 | 4 | 5 | 6 | | VI-2 | Mfap3l |
| 6807 | 3 | 4 | 5 | 6 | | VI-2 | Mfsd1 |
| 6808 | 3 | 4 | 5 | 6 | | VI-2 | Mfsd12 |
| 6809 | 3 | 4 | 5 | 6 | | VI-2 | Mfsd7b |
| 6810 | 3 | 4 | 5 | 6 | | VI-2 | Mfsd7c |
| 6811 | 3 | 4 | 5 | 6 | | VI-2 | Mgarp |
| 6812 | 3 | 4 | 5 | 6 | | VI-2 | Mgat2 |
| 6813 | 3 | 4 | 5 | 6 | | VI-2 | Mgat3 |
| 6814 | 3 | 4 | 5 | 6 | | VI-2 | Mgll |
| 6815 | 3 | 4 | 5 | 6 | | VI-2 | Mgme1 |
| 6816 | 3 | 4 | 5 | 6 | | VI-2 | Mgrn1 |
| 6817 | 3 | 4 | 5 | 6 | | VI-2 | Mib1 |
| 6818 | 3 | 4 | 5 | 6 | | VI-2 | Mical3 |
| 6819 | 3 | 4 | 5 | 6 | | VI-2 | Micu3 |
| 6820 | 3 | 4 | 5 | 6 | | VI-2 | Mid1ip1 |
| 6821 | 3 | 4 | 5 | 6 | | VI-2 | Mill1 |
| 6822 | 3 | 4 | 5 | 6 | | VI-2 | Mill2 |
| 6823 | 3 | 4 | 5 | 6 | | VI-2 | Mink1 |
| 6824 | 3 | 4 | 5 | 6 | | VI-2 | Mir143hg |
| 6825 | 3 | 4 | 5 | 6 | | VI-2 | Mlrg |
| 6826 | 3 | 4 | 5 | 6 | | VI-2 | Mis12 |
| 6827 | 3 | 4 | 5 | 6 | | VI-2 | Mis18a |
| 6828 | 3 | 4 | 5 | 6 | | VI-2 | Mis18bp1 |
| 6829 | 3 | 4 | 5 | 6 | | VI-2 | Mitd1 |
| 6830 | 3 | 4 | 5 | 6 | | VI-2 | Mki67 |
| 6831 | 3 | 4 | 5 | 6 | | VI-2 | Mkln1os |
| 6832 | 3 | 4 | 5 | 6 | | VI-2 | Mks1 |
| 6833 | 3 | 4 | 5 | 6 | | VI-2 | Mlec |
| 6834 | 3 | 4 | 5 | 6 | | VI-2 | Mllt11 |
| 6835 | 3 | 4 | 5 | 6 | | VI-2 | Mllt6 |
| 6836 | 3 | 4 | 5 | 6 | | VI-2 | Mlxipl |
| 6837 | 3 | 4 | 5 | 6 | | VI-2 | Mmadhc |
| 6838 | 3 | 4 | 5 | 6 | | VI-2 | Mme |
| 6839 | 3 | 4 | 5 | 6 | | VI-2 | Mmp10 |
| 6840 | 3 | 4 | 5 | 6 | | VI-2 | Mmp14 |
| 6841 | 3 | 4 | 5 | 6 | | VI-2 | Mmp25 |
| 6842 | 3 | 4 | 5 | 6 | | VI-2 | Mmrn1 |
| 6843 | 3 | 4 | 5 | 6 | | VI-2 | Mmrn2 |
| 6844 | 3 | 4 | 5 | 6 | | VI-2 | Mms22l |
| 6845 | 3 | 4 | 5 | 6 | | VI-2 | Mnd1-ps |
| 6846 | 3 | 4 | 5 | 6 | | VI-2 | Mob1b |
| 6847 | 3 | 4 | 5 | 6 | | VI-2 | Mon2 |
| 6848 | 3 | 4 | 5 | 6 | | VI-2 | Morc2a |
| 6849 | 3 | 4 | 5 | 6 | | VI-2 | Morf4l2 |
| 6850 | 3 | 4 | 5 | 6 | | VI-2 | Mos |
| 6851 | 3 | 4 | 5 | 6 | | VI-2 | Mpdz |
| 6852 | 3 | 4 | 5 | 6 | | VI-2 | Mpkip |
| 6853 | 3 | 4 | 5 | 6 | | VI-2 | Mpp1 |
| 6854 | 3 | 4 | 5 | 6 | | VI-2 | Mpp2 |
| 6855 | 3 | 4 | 5 | 6 | | VI-2 | Mpped2 |
| 6856 | 3 | 4 | 5 | 6 | | VI-2 | Mptx1 |
| 6857 | 3 | 4 | 5 | 6 | | VI-2 | Mptx2 |
| 6858 | 3 | 4 | 5 | 6 | | VI-2 | Mras |
| 6859 | 3 | 4 | 5 | 6 | | VI-2 | Mrc2 |
| 6860 | 3 | 4 | 5 | 6 | | VI-2 | Mrgprb2 |
| 6861 | 3 | 4 | 5 | 6 | | VI-2 | Mrgprb3 |
| 6862 | 3 | 4 | 5 | 6 | | VI-2 | Mrgprh |
| 6863 | 3 | 4 | 5 | 6 | | VI-2 | Mrm1 |
| 6864 | 3 | 4 | 5 | 6 | | VI-2 | Mrpl19 |
| 6865 | 3 | 4 | 5 | 6 | | VI-2 | Mrpl21 |
| 6866 | 3 | 4 | 5 | 6 | | VI-2 | Mrpl39 |
| 6867 | 3 | 4 | 5 | 6 | | VI-2 | Mrpl44 |
| 6868 | 3 | 4 | 5 | 6 | | VI-2 | Mrpl53 |
| 6869 | 3 | 4 | 5 | 6 | | VI-2 | Mrs2 |
| 6870 | 3 | 4 | 5 | 6 | | VI-2 | Ms4a1 |
| 6871 | 3 | 4 | 5 | 6 | | VI-2 | Ms4a2 |
| 6872 | 3 | 4 | 5 | 6 | | VI-2 | Ms4a4b |
| 6873 | 3 | 4 | 5 | 6 | | VI-2 | Msantd4 |
| 6874 | 3 | 4 | 5 | 6 | | VI-2 | Msi2 |
| 6875 | 3 | 4 | 5 | 6 | | VI-2 | Msl1 |
| 6876 | 3 | 4 | 5 | 6 | | VI-2 | Msl3l2 |
| 6877 | 3 | 4 | 5 | 6 | | VI-2 | Msra |
| 6878 | 3 | 4 | 5 | 6 | | VI-2 | Mst1r |
| 6879 | 3 | 4 | 5 | 6 | | VI-2 | Msx1 |
| 6880 | 3 | 4 | 5 | 6 | | VI-2 | Msx1os |
| 6881 | 3 | 4 | 5 | 6 | | VI-2 | Mta2 |
| 6882 | 3 | 4 | 5 | 6 | | VI-2 | Mtag2 |
| 6883 | 3 | 4 | 5 | 6 | | VI-2 | Mtap |
| 6884 | 3 | 4 | 5 | 6 | | VI-2 | Mtap7d3 |
| 6885 | 3 | 4 | 5 | 6 | | VI-2 | Mtbp |
| 6886 | 3 | 4 | 5 | 6 | | VI-2 | Mtcl1 |
| 6887 | 3 | 4 | 5 | 6 | | VI-2 | Mtdh |
| 6888 | 3 | 4 | 5 | 6 | | VI-2 | Mtf1 |
| 6889 | 3 | 4 | 5 | 6 | | VI-2 | Mtfr1 |
| 6890 | 3 | 4 | 5 | 6 | | VI-2 | Mtfr2 |
| 6891 | 3 | 4 | 5 | 6 | | VI-2 | Mthfd1l |
| 6892 | 3 | 4 | 5 | 6 | | VI-2 | Mthfd2l |
| 6893 | 3 | 4 | 5 | 6 | | VI-2 | Mthfr |
| 6894 | 3 | 4 | 5 | 6 | | VI-2 | Mtmr12 |
| 6895 | 3 | 4 | 5 | 6 | | VI-2 | Mtmr3 |
| 6896 | 3 | 4 | 5 | 6 | | VI-2 | Mtmr6 |
| 6897 | 3 | 4 | 5 | 6 | | VI-2 | Mtnr1a |
| 6898 | 3 | 4 | 5 | 6 | | VI-2 | Mto1 |
| 6899 | 3 | 4 | 5 | 6 | | VI-2 | Mtor |
| 6900 | 3 | 4 | 5 | 6 | | VI-2 | Mtpn |
| 6901 | 3 | 4 | 5 | 6 | | VI-2 | Mtrr |
| 6902 | 3 | 4 | 5 | 6 | | VI-2 | Mtss1 |
| 6903 | 3 | 4 | 5 | 6 | | VI-2 | Mtus2 |
| 6904 | 3 | 4 | 5 | 6 | | VI-2 | Mtx2 |
| 6905 | 3 | 4 | 5 | 6 | | VI-2 | Mum1l1 |
| 6906 | 3 | 4 | 5 | 6 | | VI-2 | Mut |
| 6907 | 3 | 4 | 5 | 6 | | VI-2 | Mxd1 |
| 6908 | 3 | 4 | 5 | 6 | | VI-2 | Mxd3 |
| 6909 | 3 | 4 | 5 | 6 | | VI-2 | Mybl1 |
| 6910 | 3 | 4 | 5 | 6 | | VI-2 | Mybl2 |

Fig. 34 - 37

| | | | | | | | |
|---|---|---|---|---|---|---|---|
| 6911 | 3 | 4 | 5 | 6 | | VI-2 | Mybph |
| 6912 | 3 | 4 | 5 | 6 | | VI-2 | Mybphl |
| 6913 | 3 | 4 | 5 | 6 | | VI-2 | Mychp2 |
| 6914 | 3 | 4 | 5 | 6 | | VI-2 | Myef2 |
| 6915 | 3 | 4 | 5 | 6 | | VI-2 | Myh7b |
| 6916 | 3 | 4 | 5 | 6 | | VI-2 | Myh9 |
| 6917 | 3 | 4 | 5 | 6 | | VI-2 | Myl12a |
| 6918 | 3 | 4 | 5 | 6 | | VI-2 | Mylk3 |
| 6919 | 3 | 4 | 5 | 6 | | VI-2 | Mynn |
| 6920 | 3 | 4 | 5 | 6 | | VI-2 | Myo1d |
| 6921 | 3 | 4 | 5 | 6 | | VI-2 | Myo1f |
| 6922 | 3 | 4 | 5 | 6 | | VI-2 | Myo1g |
| 6923 | 3 | 4 | 5 | 6 | | VI-2 | Myo5a |
| 6924 | 3 | 4 | 5 | 6 | | VI-2 | Myo5c |
| 6925 | 3 | 4 | 5 | 6 | | VI-2 | Myo9a |
| 6926 | 3 | 4 | 5 | 6 | | VI-2 | Myoc |
| 6927 | 3 | 4 | 5 | 6 | | VI-2 | Myod1 |
| 6928 | 3 | 4 | 5 | 6 | | VI-2 | Myof |
| 6929 | 3 | 4 | 5 | 6 | | VI-2 | Myom3 |
| 6930 | 3 | 4 | 5 | 6 | | VI-2 | Mypop |
| 6931 | 3 | 4 | 5 | 6 | | VI-2 | N4bp1 |
| 6932 | 3 | 4 | 5 | 6 | | VI-2 | N4bp2 |
| 6933 | 3 | 4 | 5 | 6 | | VI-2 | N4bp2l2 |
| 6934 | 3 | 4 | 5 | 6 | | VI-2 | N6amt1 |
| 6935 | 3 | 4 | 5 | 6 | | VI-2 | Naa15 |
| 6936 | 3 | 4 | 5 | 6 | | VI-2 | Nacc1 |
| 6937 | 3 | 4 | 5 | 6 | | VI-2 | Nacc2 |
| 6938 | 3 | 4 | 5 | 6 | | VI-2 | Nadk2 |
| 6939 | 3 | 4 | 5 | 6 | | VI-2 | Nags |
| 6940 | 3 | 4 | 5 | 6 | | VI-2 | Naip6 |
| 6941 | 3 | 4 | 5 | 6 | | VI-2 | Nampt |
| 6942 | 3 | 4 | 5 | 6 | | VI-2 | Nanp |
| 6943 | 3 | 4 | 5 | 6 | | VI-2 | Napepld |
| 6944 | 3 | 4 | 5 | 6 | | VI-2 | Narf |
| 6945 | 3 | 4 | 5 | 6 | | VI-2 | Narfl |
| 6946 | 3 | 4 | 5 | 6 | | VI-2 | Nat6 |
| 6947 | 3 | 4 | 5 | 6 | | VI-2 | Nbas |
| 6948 | 3 | 4 | 5 | 6 | | VI-2 | Ncapd3 |
| 6949 | 3 | 4 | 5 | 6 | | VI-2 | Ncapg |
| 6950 | 3 | 4 | 5 | 6 | | VI-2 | Ncaph |
| 6951 | 3 | 4 | 5 | 6 | | VI-2 | Nceh1 |
| 6952 | 3 | 4 | 5 | 6 | | VI-2 | Nck2 |
| 6953 | 3 | 4 | 5 | 6 | | VI-2 | Nckap5 |
| 6954 | 3 | 4 | 5 | 6 | | VI-2 | Nckap5l |
| 6955 | 3 | 4 | 5 | 6 | | VI-2 | Nckipsd |
| 6956 | 3 | 4 | 5 | 6 | | VI-2 | Ncoa1 |
| 6957 | 3 | 4 | 5 | 6 | | VI-2 | Ncoa2 |
| 6958 | 3 | 4 | 5 | 6 | | VI-2 | Ncoa6 |
| 6959 | 3 | 4 | 5 | 6 | | VI-2 | Ncor2 |
| 6960 | 3 | 4 | 5 | 6 | | VI-2 | Ncr1 |
| 6961 | 3 | 4 | 5 | 6 | | VI-2 | Ndc1 |
| 6962 | 3 | 4 | 5 | 6 | | VI-2 | Ndn |
| 6963 | 3 | 4 | 5 | 6 | | VI-2 | Ndnf |
| 6964 | 3 | 4 | 5 | 6 | | VI-2 | Ndor1 |
| 6965 | 3 | 4 | 5 | 6 | | VI-2 | Ndp |
| 6966 | 3 | 4 | 5 | 6 | | VI-2 | Ndufaf4 |
| 6967 | 3 | 4 | 5 | 6 | | VI-2 | Ndufaf5 |
| 6968 | 3 | 4 | 5 | 6 | | VI-2 | Ndufaf6 |
| 6969 | 3 | 4 | 5 | 6 | | VI-2 | Ndufb4 |
| 6970 | 3 | 4 | 5 | 6 | | VI-2 | Ndufs1 |
| 6971 | 3 | 4 | 5 | 6 | | VI-2 | Necap1 |
| 6972 | 3 | 4 | 5 | 6 | | VI-2 | Necap2 |
| 6973 | 3 | 4 | 5 | 6 | | VI-2 | Neil1 |
| 6974 | 3 | 4 | 5 | 6 | | VI-2 | Neil3 |
| 6975 | 3 | 4 | 5 | 6 | | VI-2 | Nek11 |
| 6976 | 3 | 4 | 5 | 6 | | VI-2 | Nek2 |
| 6977 | 3 | 4 | 5 | 6 | | VI-2 | Nek4 |
| 6978 | 3 | 4 | 5 | 6 | | VI-2 | Nell1os |
| 6979 | 3 | 4 | 5 | 6 | | VI-2 | Neu2 |
| 6980 | 3 | 4 | 5 | 6 | | VI-2 | Nf1 |
| 6981 | 3 | 4 | 5 | 6 | | VI-2 | Nf2 |
| 6982 | 3 | 4 | 5 | 6 | | VI-2 | Nfasc |
| 6983 | 3 | 4 | 5 | 6 | | VI-2 | Nfatc1 |
| 6984 | 3 | 4 | 5 | 6 | | VI-2 | Nfe2l1 |
| 6985 | 3 | 4 | 5 | 6 | | VI-2 | Nfia |
| 6986 | 3 | 4 | 5 | 6 | | VI-2 | Nfic |
| 6987 | 3 | 4 | 5 | 6 | | VI-2 | Nfix |
| 6988 | 3 | 4 | 5 | 6 | | VI-2 | Nfrkb |
| 6989 | 3 | 4 | 5 | 6 | | VI-2 | Nfs1 |
| 6990 | 3 | 4 | 5 | 6 | | VI-2 | Nfxl1 |
| 6991 | 3 | 4 | 5 | 6 | | VI-2 | Ngly1 |
| 6992 | 3 | 4 | 5 | 6 | | VI-2 | Nhp2l1 |
| 6993 | 3 | 4 | 5 | 6 | | VI-2 | Nicn1 |
| 6994 | 3 | 4 | 5 | 6 | | VI-2 | Nid2 |
| 6995 | 3 | 4 | 5 | 6 | | VI-2 | Nim1k |
| 6996 | 3 | 4 | 5 | 6 | | VI-2 | Ninj2 |
| 6997 | 3 | 4 | 5 | 6 | | VI-2 | Ninl |
| 6998 | 3 | 4 | 5 | 6 | | VI-2 | Nipal4 |
| 6999 | 3 | 4 | 5 | 6 | | VI-2 | Nipbl |
| 7000 | 3 | 4 | 5 | 6 | | VI-2 | Nipsnap3b |
| 7001 | 3 | 4 | 5 | 6 | | VI-2 | Nkd1 |
| 7002 | 3 | 4 | 5 | 6 | | VI-2 | Nkd2 |
| 7003 | 3 | 4 | 5 | 6 | | VI-2 | Nkiras1 |
| 7004 | 3 | 4 | 5 | 6 | | VI-2 | Nktr |
| 7005 | 3 | 4 | 5 | 6 | | VI-2 | Nkx2-1 |
| 7006 | 3 | 4 | 5 | 6 | | VI-2 | Nlrc3 |
| 7007 | 3 | 4 | 5 | 6 | | VI-2 | Nlrp3 |
| 7008 | 3 | 4 | 5 | 6 | | VI-2 | Nlrx1 |
| 7009 | 3 | 4 | 5 | 6 | | VI-2 | Nmd3 |
| 7010 | 3 | 4 | 5 | 6 | | VI-2 | Nme9 |
| 7011 | 3 | 4 | 5 | 6 | | VI-2 | Nmnat1 |
| 7012 | 3 | 4 | 5 | 6 | | VI-2 | Nmrk2 |
| 7013 | 3 | 4 | 5 | 6 | | VI-2 | Noc3l |
| 7014 | 3 | 4 | 5 | 6 | | VI-2 | Nod1 |
| 7015 | 3 | 4 | 5 | 6 | | VI-2 | Nog |
| 7016 | 3 | 4 | 5 | 6 | | VI-2 | Nol10 |
| 7017 | 3 | 4 | 5 | 6 | | VI-2 | Nol6 |
| 7018 | 3 | 4 | 5 | 6 | | VI-2 | Nol8 |
| 7019 | 3 | 4 | 5 | 6 | | VI-2 | Nos1 |
| 7020 | 3 | 4 | 5 | 6 | | VI-2 | Nos2 |
| 7021 | 3 | 4 | 5 | 6 | | VI-2 | Nostrin |
| 7022 | 3 | 4 | 5 | 6 | | VI-2 | Notch2 |
| 7023 | 3 | 4 | 5 | 6 | | VI-2 | Nova1 |
| 7024 | 3 | 4 | 5 | 6 | | VI-2 | Npbwr1 |
| 7025 | 3 | 4 | 5 | 6 | | VI-2 | Nphp3 |
| 7026 | 3 | 4 | 5 | 6 | | VI-2 | Nphs2 |
| 7027 | 3 | 4 | 5 | 6 | | VI-2 | Npsr1 |
| 7028 | 3 | 4 | 5 | 6 | | VI-2 | Nptn |
| 7029 | 3 | 4 | 5 | 6 | | VI-2 | Npy6r |
| 7030 | 3 | 4 | 5 | 6 | | VI-2 | Nqo2 |
| 7031 | 3 | 4 | 5 | 6 | | VI-2 | Nr0b1 |
| 7032 | 3 | 4 | 5 | 6 | | VI-2 | Nr2c1 |
| 7033 | 3 | 4 | 5 | 6 | | VI-2 | Nr3c1 |
| 7034 | 3 | 4 | 5 | 6 | | VI-2 | Nr3c2 |
| 7035 | 3 | 4 | 5 | 6 | | VI-2 | Nr5a2 |
| 7036 | 3 | 4 | 5 | 6 | | VI-2 | Nr6a1 |
| 7037 | 3 | 4 | 5 | 6 | | VI-2 | Nrarp |
| 7038 | 3 | 4 | 5 | 6 | | VI-2 | Nrg1 |
| 7039 | 3 | 4 | 5 | 6 | | VI-2 | Nrp2 |
| 7040 | 3 | 4 | 5 | 6 | | VI-2 | Nrros |
| 7041 | 3 | 4 | 5 | 6 | | VI-2 | Nsf |
| 7042 | 3 | 4 | 5 | 6 | | VI-2 | Nsl1 |
| 7043 | 3 | 4 | 5 | 6 | | VI-2 | Nsmce2 |
| 7044 | 3 | 4 | 5 | 6 | | VI-2 | Nt5c1a |
| 7045 | 3 | 4 | 5 | 6 | | VI-2 | Nt5c3b |
| 7046 | 3 | 4 | 5 | 6 | | VI-2 | Nt5dc3 |
| 7047 | 3 | 4 | 5 | 6 | | VI-2 | Ntf5 |
| 7048 | 3 | 4 | 5 | 6 | | VI-2 | Ntn1 |
| 7049 | 3 | 4 | 5 | 6 | | VI-2 | Ntng2 |
| 7050 | 3 | 4 | 5 | 6 | | VI-2 | Ntrk1 |
| 7051 | 3 | 4 | 5 | 6 | | VI-2 | Ntrk3 |
| 7052 | 3 | 4 | 5 | 6 | | VI-2 | Nuak2 |
| 7053 | 3 | 4 | 5 | 6 | | VI-2 | Nudt13 |
| 7054 | 3 | 4 | 5 | 6 | | VI-2 | Nudt2 |
| 7055 | 3 | 4 | 5 | 6 | | VI-2 | Nudt6 |
| 7056 | 3 | 4 | 5 | 6 | | VI-2 | Nuf2 |
| 7057 | 3 | 4 | 5 | 6 | | VI-2 | Nufip2 |
| 7058 | 3 | 4 | 5 | 6 | | VI-2 | Numa1 |
| 7059 | 3 | 4 | 5 | 6 | | VI-2 | Nup107 |
| 7060 | 3 | 4 | 5 | 6 | | VI-2 | Nup155 |
| 7061 | 3 | 4 | 5 | 6 | | VI-2 | Nup160 |
| 7062 | 3 | 4 | 5 | 6 | | VI-2 | Nup205 |
| 7063 | 3 | 4 | 5 | 6 | | VI-2 | Nup210 |
| 7064 | 3 | 4 | 5 | 6 | | VI-2 | Nup54 |
| 7065 | 3 | 4 | 5 | 6 | | VI-2 | Nup62 |
| 7066 | 3 | 4 | 5 | 6 | | VI-2 | Nup62-il4i1 |
| 7067 | 3 | 4 | 5 | 6 | | VI-2 | Nup85 |
| 7068 | 3 | 4 | 5 | 6 | | VI-2 | Nup93 |
| 7069 | 3 | 4 | 5 | 6 | | VI-2 | Nup98 |
| 7070 | 3 | 4 | 5 | 6 | | VI-2 | Nwd1 |
| 7071 | 3 | 4 | 5 | 6 | | VI-2 | Nxpe2 |
| 7072 | 3 | 4 | 5 | 6 | | VI-2 | Nxph4 |
| 7073 | 3 | 4 | 5 | 6 | | VI-2 | Nxt1 |
| 7074 | 3 | 4 | 5 | 6 | | VI-2 | Nxt2 |
| 7075 | 3 | 4 | 5 | 6 | | VI-2 | Nynrin |
| 7076 | 3 | 4 | 5 | 6 | | VI-2 | Odf2l |
| 7077 | 3 | 4 | 5 | 6 | | VI-2 | Odf3 |
| 7078 | 3 | 4 | 5 | 6 | | VI-2 | Odf3l1 |
| 7079 | 3 | 4 | 5 | 6 | | VI-2 | Ogt |
| 7080 | 3 | 4 | 5 | 6 | | VI-2 | Oit3 |
| 7081 | 3 | 4 | 5 | 6 | | VI-2 | Olfm1 |
| 7082 | 3 | 4 | 5 | 6 | | VI-2 | Olfm2a |
| 7083 | 3 | 4 | 5 | 6 | | VI-2 | Olfm3 |
| 7084 | 3 | 4 | 5 | 6 | | VI-2 | Olfr1186 |
| 7085 | 3 | 4 | 5 | 6 | | VI-2 | Olfr165 |
| 7086 | 3 | 4 | 5 | 6 | | VI-2 | Olfr199 |
| 7087 | 3 | 4 | 5 | 6 | | VI-2 | Olfr23 |
| 7088 | 3 | 4 | 5 | 6 | | VI-2 | Olfr550 |
| 7089 | 3 | 4 | 5 | 6 | | VI-2 | Olfr697 |
| 7090 | 3 | 4 | 5 | 6 | | VI-2 | Olfr701 |
| 7091 | 3 | 4 | 5 | 6 | | VI-2 | Olfr733 |
| 7092 | 3 | 4 | 5 | 6 | | VI-2 | Olfr94 |
| 7093 | 3 | 4 | 5 | 6 | | VI-2 | Olig3 |
| 7094 | 3 | 4 | 5 | 6 | | VI-2 | Onecut1 |
| 7095 | 3 | 4 | 5 | 6 | | VI-2 | Onecut2 |
| 7096 | 3 | 4 | 5 | 6 | | VI-2 | Opalin |
| 7097 | 3 | 4 | 5 | 6 | | VI-2 | Oplah |
| 7098 | 3 | 4 | 5 | 6 | | VI-2 | Optc |
| 7099 | 3 | 4 | 5 | 6 | | VI-2 | Oraov1 |
| 7100 | 3 | 4 | 5 | 6 | | VI-2 | Orc1 |
| 7101 | 3 | 4 | 5 | 6 | | VI-2 | Orc3 |
| 7102 | 3 | 4 | 5 | 6 | | VI-2 | Orc4 |

Fig. 34 - 38

| | | | | | | | |
|---|---|---|---|---|---|---|---|
| 7103 | 3 | 4 | 5 | 6 | | VI-2 | Osbp |
| 7104 | 3 | 4 | 5 | 6 | | VI-2 | Osgepl1 |
| 7105 | 3 | 4 | 5 | 6 | | VI-2 | Osm |
| 7106 | 3 | 4 | 5 | 6 | | VI-2 | Otc |
| 7107 | 3 | 4 | 5 | 6 | | VI-2 | Otop1 |
| 7108 | 3 | 4 | 5 | 6 | | VI-2 | Otf |
| 7109 | 3 | 4 | 5 | 6 | | VI-2 | Otud6a |
| 7110 | 3 | 4 | 5 | 6 | | VI-2 | Otud6b |
| 7111 | 3 | 4 | 5 | 6 | | VI-2 | Otud7a |
| 7112 | 3 | 4 | 5 | 6 | | VI-2 | Ovol1 |
| 7113 | 3 | 4 | 5 | 6 | | VI-2 | Oxct1 |
| 7114 | 3 | 4 | 5 | 6 | | VI-2 | Oxsm |
| 7115 | 3 | 4 | 5 | 6 | | VI-2 | P2ry12 |
| 7116 | 3 | 4 | 5 | 6 | | VI-2 | P2ry13 |
| 7117 | 3 | 4 | 5 | 6 | | VI-2 | P2ry14 |
| 7118 | 3 | 4 | 5 | 6 | | VI-2 | P4ha3 |
| 7119 | 3 | 4 | 5 | 6 | | VI-2 | P4htm |
| 7120 | 3 | 4 | 5 | 6 | | VI-2 | Pabpn1 |
| 7121 | 3 | 4 | 5 | 6 | | VI-2 | Pacrgl |
| 7122 | 3 | 4 | 5 | 6 | | VI-2 | Pafah1b1 |
| 7123 | 3 | 4 | 5 | 6 | | VI-2 | Pafah2 |
| 7124 | 3 | 4 | 5 | 6 | | VI-2 | Pak2 |
| 7125 | 3 | 4 | 5 | 6 | | VI-2 | Pak3 |
| 7126 | 3 | 4 | 5 | 6 | | VI-2 | Pak6 |
| 7127 | 3 | 4 | 5 | 6 | | VI-2 | Palb2 |
| 7128 | 3 | 4 | 5 | 6 | | VI-2 | Palld |
| 7129 | 3 | 4 | 5 | 6 | | VI-2 | Palm3 |
| 7130 | 3 | 4 | 5 | 6 | | VI-2 | Pan3 |
| 7131 | 3 | 4 | 5 | 6 | | VI-2 | Pank4 |
| 7132 | 3 | 4 | 5 | 6 | | VI-2 | Panx3 |
| 7133 | 3 | 4 | 5 | 6 | | VI-2 | Papd4 |
| 7134 | 3 | 4 | 5 | 6 | | VI-2 | Papln |
| 7135 | 3 | 4 | 5 | 6 | | VI-2 | Papola |
| 7136 | 3 | 4 | 5 | 6 | | VI-2 | Papolb |
| 7137 | 3 | 4 | 5 | 6 | | VI-2 | Papolg |
| 7138 | 3 | 4 | 5 | 6 | | VI-2 | Paqr4 |
| 7139 | 3 | 4 | 5 | 6 | | VI-2 | Pard3b |
| 7140 | 3 | 4 | 5 | 6 | | VI-2 | Park2 |
| 7141 | 3 | 4 | 5 | 6 | | VI-2 | Parm1 |
| 7142 | 3 | 4 | 5 | 6 | | VI-2 | Parp11 |
| 7143 | 3 | 4 | 5 | 6 | | VI-2 | Parp16 |
| 7144 | 3 | 4 | 5 | 6 | | VI-2 | Parp2 |
| 7145 | 3 | 4 | 5 | 6 | | VI-2 | Parp3 |
| 7146 | 3 | 4 | 5 | 6 | | VI-2 | Pars2 |
| 7147 | 3 | 4 | 5 | 6 | | VI-2 | Pask |
| 7148 | 3 | 4 | 5 | 6 | | VI-2 | Pate4 |
| 7149 | 3 | 4 | 5 | 6 | | VI-2 | Patl1 |
| 7150 | 3 | 4 | 5 | 6 | | VI-2 | Pax2 |
| 7151 | 3 | 4 | 5 | 6 | | VI-2 | Pax5 |
| 7152 | 3 | 4 | 5 | 6 | | VI-2 | Paxip1 |
| 7153 | 3 | 4 | 5 | 6 | | VI-2 | Pbk |
| 7154 | 3 | 4 | 5 | 6 | | VI-2 | Pbp2 |
| 7155 | 3 | 4 | 5 | 6 | | VI-2 | Pbrm1 |
| 7156 | 3 | 4 | 5 | 6 | | VI-2 | Pbx1 |
| 7157 | 3 | 4 | 5 | 6 | | VI-2 | Pbx3 |
| 7158 | 3 | 4 | 5 | 6 | | VI-2 | Pcbp2 |
| 7159 | 3 | 4 | 5 | 6 | | VI-2 | Pcca |
| 7160 | 3 | 4 | 5 | 6 | | VI-2 | Pcdh18 |
| 7161 | 3 | 4 | 5 | 6 | | VI-2 | Pcdha5 |
| 7162 | 3 | 4 | 5 | 6 | | VI-2 | Pcdhb17 |
| 7163 | 3 | 4 | 5 | 6 | | VI-2 | Pcdhb2 |
| 7164 | 3 | 4 | 5 | 6 | | VI-2 | Pcdhga1 |
| 7165 | 3 | 4 | 5 | 6 | | VI-2 | Pcdhga2 |
| 7166 | 3 | 4 | 5 | 6 | | VI-2 | Pcdhga4 |
| 7167 | 3 | 4 | 5 | 6 | | VI-2 | Pcdhga5 |
| 7168 | 3 | 4 | 5 | 6 | | VI-2 | Pcdhga6 |
| 7169 | 3 | 4 | 5 | 6 | | VI-2 | Pcdhgb2 |
| 7170 | 3 | 4 | 5 | 6 | | VI-2 | Pcdhgb5 |
| 7171 | 3 | 4 | 5 | 6 | | VI-2 | Pcdhgb6 |
| 7172 | 3 | 4 | 5 | 6 | | VI-2 | Pcdhgc4 |
| 7173 | 3 | 4 | 5 | 6 | | VI-2 | Pced1b |
| 7174 | 3 | 4 | 5 | 6 | | VI-2 | Pcgf2 |
| 7175 | 3 | 4 | 5 | 6 | | VI-2 | Pcgf3 |
| 7176 | 3 | 4 | 5 | 6 | | VI-2 | Pcgf5 |
| 7177 | 3 | 4 | 5 | 6 | | VI-2 | Pcna |
| 7178 | 3 | 4 | 5 | 6 | | VI-2 | Pcolce2 |
| 7179 | 3 | 4 | 5 | 6 | | VI-2 | Pcsk6 |
| 7180 | 3 | 4 | 5 | 6 | | VI-2 | Pcsk7 |
| 7181 | 3 | 4 | 5 | 6 | | VI-2 | Pcx |
| 7182 | 3 | 4 | 5 | 6 | | VI-2 | Pcyox1 |
| 7183 | 3 | 4 | 5 | 6 | | VI-2 | Pcyt1a |
| 7184 | 3 | 4 | 5 | 6 | | VI-2 | Pcyt1b |
| 7185 | 3 | 4 | 5 | 6 | | VI-2 | Pdcd6 |
| 7186 | 3 | 4 | 5 | 6 | | VI-2 | Pdcl |
| 7187 | 3 | 4 | 5 | 6 | | VI-2 | Pde3a |
| 7188 | 3 | 4 | 5 | 6 | | VI-2 | Pde4a |
| 7189 | 3 | 4 | 5 | 6 | | VI-2 | Pde6d |
| 7190 | 3 | 4 | 5 | 6 | | VI-2 | Pdgfrb |
| 7191 | 3 | 4 | 5 | 6 | | VI-2 | Pdha2 |
| 7192 | 3 | 4 | 5 | 6 | | VI-2 | Pdia3 |
| 7193 | 3 | 4 | 5 | 6 | | VI-2 | Pdilt |
| 7194 | 3 | 4 | 5 | 6 | | VI-2 | Pdk1 |
| 7195 | 3 | 4 | 5 | 6 | | VI-2 | Pdk3 |
| 7196 | 3 | 4 | 5 | 6 | | VI-2 | Pdp2 |
| 7197 | 3 | 4 | 5 | 6 | | VI-2 | Pds5b |
| 7198 | 3 | 4 | 5 | 6 | | VI-2 | Pdxk |
| 7199 | 3 | 4 | 5 | 6 | | VI-2 | Pdzd11 |
| 7200 | 3 | 4 | 5 | 6 | | VI-2 | Pdzd8 |
| 7201 | 3 | 4 | 5 | 6 | | VI-2 | Pdzrn3 |
| 7202 | 3 | 4 | 5 | 6 | | VI-2 | Pdzrn4 |
| 7203 | 3 | 4 | 5 | 6 | | VI-2 | Pecam1 |
| 7204 | 3 | 4 | 5 | 6 | | VI-2 | Peg10 |
| 7205 | 3 | 4 | 5 | 6 | | VI-2 | Peg13 |
| 7206 | 3 | 4 | 5 | 6 | | VI-2 | Per2 |
| 7207 | 3 | 4 | 5 | 6 | | VI-2 | Pex1 |
| 7208 | 3 | 4 | 5 | 6 | | VI-2 | Pex11b |
| 7209 | 3 | 4 | 5 | 6 | | VI-2 | Pex14 |
| 7210 | 3 | 4 | 5 | 6 | | VI-2 | Pex19 |
| 7211 | 3 | 4 | 5 | 6 | | VI-2 | Pex26 |
| 7212 | 3 | 4 | 5 | 6 | | VI-2 | Pex3 |
| 7213 | 3 | 4 | 5 | 6 | | VI-2 | Pex5 |
| 7214 | 3 | 4 | 5 | 6 | | VI-2 | Pfas |
| 7215 | 3 | 4 | 5 | 6 | | VI-2 | Pfn1 |
| 7216 | 3 | 4 | 5 | 6 | | VI-2 | Pgap1 |
| 7217 | 3 | 4 | 5 | 6 | | VI-2 | Pgap3 |
| 7218 | 3 | 4 | 5 | 6 | | VI-2 | Pggt1b |
| 7219 | 3 | 4 | 5 | 6 | | VI-2 | Pgm2l1 |
| 7220 | 3 | 4 | 5 | 6 | | VI-2 | Pgs1 |
| 7221 | 3 | 4 | 5 | 6 | | VI-2 | Phactr2 |
| 7222 | 3 | 4 | 5 | 6 | | VI-2 | Phc3 |
| 7223 | 3 | 4 | 5 | 6 | | VI-2 | Phf13 |
| 7224 | 3 | 4 | 5 | 6 | | VI-2 | Phf19 |
| 7225 | 3 | 4 | 5 | 6 | | VI-2 | Phf6 |
| 7226 | 3 | 4 | 5 | 6 | | VI-2 | Phlda2 |
| 7227 | 3 | 4 | 5 | 6 | | VI-2 | Phldb2 |
| 7228 | 3 | 4 | 5 | 6 | | VI-2 | Phlpp1 |
| 7229 | 3 | 4 | 5 | 6 | | VI-2 | Phrf1 |
| 7230 | 3 | 4 | 5 | 6 | | VI-2 | Pianp |
| 7231 | 3 | 4 | 5 | 6 | | VI-2 | Pias2 |
| 7232 | 3 | 4 | 5 | 6 | | VI-2 | Pidd1 |
| 7233 | 3 | 4 | 5 | 6 | | VI-2 | Piezo2 |
| 7234 | 3 | 4 | 5 | 6 | | VI-2 | Pif1 |
| 7235 | 3 | 4 | 5 | 6 | | VI-2 | Pigf |
| 7236 | 3 | 4 | 5 | 6 | | VI-2 | Pigk |
| 7237 | 3 | 4 | 5 | 6 | | VI-2 | Pigl |
| 7238 | 3 | 4 | 5 | 6 | | VI-2 | Pign |
| 7239 | 3 | 4 | 5 | 6 | | VI-2 | Pigw |
| 7240 | 3 | 4 | 5 | 6 | | VI-2 | Pih1d2 |
| 7241 | 3 | 4 | 5 | 6 | | VI-2 | Pik3ap1 |
| 7242 | 3 | 4 | 5 | 6 | | VI-2 | Pik3c2b |
| 7243 | 3 | 4 | 5 | 6 | | VI-2 | Pik3ca |
| 7244 | 3 | 4 | 5 | 6 | | VI-2 | Pik3cd |
| 7245 | 3 | 4 | 5 | 6 | | VI-2 | Pik3r4 |
| 7246 | 3 | 4 | 5 | 6 | | VI-2 | Pik3r5 |
| 7247 | 3 | 4 | 5 | 6 | | VI-2 | Pikfyve |
| 7248 | 3 | 4 | 5 | 6 | | VI-2 | Pin1 |
| 7249 | 3 | 4 | 5 | 6 | | VI-2 | Pip4k2b |
| 7250 | 3 | 4 | 5 | 6 | | VI-2 | Pip4k2c |
| 7251 | 3 | 4 | 5 | 6 | | VI-2 | Pip5k1b |
| 7252 | 3 | 4 | 5 | 6 | | VI-2 | Pip5k1c |
| 7253 | 3 | 4 | 5 | 6 | | VI-2 | Pira1 |
| 7254 | 3 | 4 | 5 | 6 | | VI-2 | Pira6 |
| 7255 | 3 | 4 | 5 | 6 | | VI-2 | Pisd-ps3 |
| 7256 | 3 | 4 | 5 | 6 | | VI-2 | Pitpnm2 |
| 7257 | 3 | 4 | 5 | 6 | | VI-2 | Pitpnm2os1 |
| 7258 | 3 | 4 | 5 | 6 | | VI-2 | Pitpnm3 |
| 7259 | 3 | 4 | 5 | 6 | | VI-2 | Pja1 |
| 7260 | 3 | 4 | 5 | 6 | | VI-2 | Pja2 |
| 7261 | 3 | 4 | 5 | 6 | | VI-2 | Pklr |
| 7262 | 3 | 4 | 5 | 6 | | VI-2 | Pkmyt1 |
| 7263 | 3 | 4 | 5 | 6 | | VI-2 | Pknox1 |
| 7264 | 3 | 4 | 5 | 6 | | VI-2 | Pkp1 |
| 7265 | 3 | 4 | 5 | 6 | | VI-2 | Pla2g10 |
| 7266 | 3 | 4 | 5 | 6 | | VI-2 | Pla2g15 |
| 7267 | 3 | 4 | 5 | 6 | | VI-2 | Pla2g3 |
| 7268 | 3 | 4 | 5 | 6 | | VI-2 | Pla2g4c |
| 7269 | 3 | 4 | 5 | 6 | | VI-2 | Pla2g4e |
| 7270 | 3 | 4 | 5 | 6 | | VI-2 | Pla2r1 |
| 7271 | 3 | 4 | 5 | 6 | | VI-2 | Plagl2 |
| 7272 | 3 | 4 | 5 | 6 | | VI-2 | Plcb2 |
| 7273 | 3 | 4 | 5 | 6 | | VI-2 | Plcb3 |
| 7274 | 3 | 4 | 5 | 6 | | VI-2 | Plcd1 |
| 7275 | 3 | 4 | 5 | 6 | | VI-2 | Plcxd2 |
| 7276 | 3 | 4 | 5 | 6 | | VI-2 | Pld3 |
| 7277 | 3 | 4 | 5 | 6 | | VI-2 | Plek |
| 7278 | 3 | 4 | 5 | 6 | | VI-2 | Plekha2 |
| 7279 | 3 | 4 | 5 | 6 | | VI-2 | Plekha6 |
| 7280 | 3 | 4 | 5 | 6 | | VI-2 | Plekha7 |
| 7281 | 3 | 4 | 5 | 6 | | VI-2 | Plekhb2 |
| 7282 | 3 | 4 | 5 | 6 | | VI-2 | Plekhg2 |
| 7283 | 3 | 4 | 5 | 6 | | VI-2 | Plekhg3 |
| 7284 | 3 | 4 | 5 | 6 | | VI-2 | Plekhh2 |
| 7285 | 3 | 4 | 5 | 6 | | VI-2 | Plekho2 |
| 7286 | 3 | 4 | 5 | 6 | | VI-2 | Plk1 |
| 7287 | 3 | 4 | 5 | 6 | | VI-2 | Plk4 |
| 7288 | 3 | 4 | 5 | 6 | | VI-2 | Plod2 |
| 7289 | 3 | 4 | 5 | 6 | | VI-2 | Plxna3 |
| 7290 | 3 | 4 | 5 | 6 | | VI-2 | Plxna4 |
| 7291 | 3 | 4 | 5 | 6 | | VI-2 | Plxnc1 |
| 7292 | 3 | 4 | 5 | 6 | | VI-2 | Plxnd1 |
| 7293 | 3 | 4 | 5 | 6 | | VI-2 | Pm20d1 |
| 7294 | 3 | 4 | 5 | 6 | | VI-2 | Pml |

Fig. 34 - 39

| | | | | | | |
|---|---|---|---|---|---|---|
| 7295 | 3 | 4 | 5 | 6 | VI-2 | Pmm2 |
| 7296 | 3 | 4 | 5 | 6 | VI-2 | Pnldc1 |
| 7297 | 3 | 4 | 5 | 6 | VI-2 | Pnma1 |
| 7298 | 3 | 4 | 5 | 6 | VI-2 | Pnn |
| 7299 | 3 | 4 | 5 | 6 | VI-2 | Pnpla3 |
| 7300 | 3 | 4 | 5 | 6 | VI-2 | Pnpla6 |
| 7301 | 3 | 4 | 5 | 6 | VI-2 | Pnpt1 |
| 7302 | 3 | 4 | 5 | 6 | VI-2 | Pnrc2 |
| 7303 | 3 | 4 | 5 | 6 | VI-2 | Podn |
| 7304 | 3 | 4 | 5 | 6 | VI-2 | Podxl |
| 7305 | 3 | 4 | 5 | 6 | VI-2 | Pof1b |
| 7306 | 3 | 4 | 5 | 6 | VI-2 | Poglut1 |
| 7307 | 3 | 4 | 5 | 6 | VI-2 | Pogz |
| 7308 | 3 | 4 | 5 | 6 | VI-2 | Pola1 |
| 7309 | 3 | 4 | 5 | 6 | VI-2 | Pole |
| 7310 | 3 | 4 | 5 | 6 | VI-2 | Polk |
| 7311 | 3 | 4 | 5 | 6 | VI-2 | Polr2b |
| 7312 | 3 | 4 | 5 | 6 | VI-2 | Polr3c |
| 7313 | 3 | 4 | 5 | 6 | VI-2 | Polr3d |
| 7314 | 3 | 4 | 5 | 6 | VI-2 | Polr3e |
| 7315 | 3 | 4 | 5 | 6 | VI-2 | Pom121l12 |
| 7316 | 3 | 4 | 5 | 6 | VI-2 | Pop1 |
| 7317 | 3 | 4 | 5 | 6 | VI-2 | Pot1b |
| 7318 | 3 | 4 | 5 | 6 | VI-2 | Pou2f1 |
| 7319 | 3 | 4 | 5 | 6 | VI-2 | Pou3f4 |
| 7320 | 3 | 4 | 5 | 6 | VI-2 | Pou4f1 |
| 7321 | 3 | 4 | 5 | 6 | VI-2 | Pou5f2 |
| 7322 | 3 | 4 | 5 | 6 | VI-2 | Pou6f1 |
| 7323 | 3 | 4 | 5 | 6 | VI-2 | Pp2d1 |
| 7324 | 3 | 4 | 5 | 6 | VI-2 | Ppapdc1a |
| 7325 | 3 | 4 | 5 | 6 | VI-2 | Ppara |
| 7326 | 3 | 4 | 5 | 6 | VI-2 | Ppig |
| 7327 | 3 | 4 | 5 | 6 | VI-2 | Ppil1 |
| 7328 | 3 | 4 | 5 | 6 | VI-2 | Ppm1f |
| 7329 | 3 | 4 | 5 | 6 | VI-2 | Ppm1g |
| 7330 | 3 | 4 | 5 | 6 | VI-2 | Ppm1n |
| 7331 | 3 | 4 | 5 | 6 | VI-2 | Ppme1 |
| 7332 | 3 | 4 | 5 | 6 | VI-2 | Ppp1r13l |
| 7333 | 3 | 4 | 5 | 6 | VI-2 | Ppp1r16a |
| 7334 | 3 | 4 | 5 | 6 | VI-2 | Ppp1r2-ps9 |
| 7335 | 3 | 4 | 5 | 6 | VI-2 | Ppp1r3b |
| 7336 | 3 | 4 | 5 | 6 | VI-2 | Ppp1r3c |
| 7337 | 3 | 4 | 5 | 6 | VI-2 | Ppp1r3d |
| 7338 | 3 | 4 | 5 | 6 | VI-2 | Ppp1r3e |
| 7339 | 3 | 4 | 5 | 6 | VI-2 | Ppp1r3f |
| 7340 | 3 | 4 | 5 | 6 | VI-2 | Ppp1r8 |
| 7341 | 3 | 4 | 5 | 6 | VI-2 | Ppp1r9b |
| 7342 | 3 | 4 | 5 | 6 | VI-2 | Ppp2cb |
| 7343 | 3 | 4 | 5 | 6 | VI-2 | Ppp2r1a |
| 7344 | 3 | 4 | 5 | 6 | VI-2 | Ppp2r2cos |
| 7345 | 3 | 4 | 5 | 6 | VI-2 | Ppp2r5b |
| 7346 | 3 | 4 | 5 | 6 | VI-2 | Ppp2r5e |
| 7347 | 3 | 4 | 5 | 6 | VI-2 | Ppp3ca |
| 7348 | 3 | 4 | 5 | 6 | VI-2 | Ppp4r2 |
| 7349 | 3 | 4 | 5 | 6 | VI-2 | Ppp4r4 |
| 7350 | 3 | 4 | 5 | 6 | VI-2 | Ppt1 |
| 7351 | 3 | 4 | 5 | 6 | VI-2 | Ppt2 |
| 7352 | 3 | 4 | 5 | 6 | VI-2 | Pramef8 |
| 7353 | 3 | 4 | 5 | 6 | VI-2 | Prc1 |
| 7354 | 3 | 4 | 5 | 6 | VI-2 | Prdm16 |
| 7355 | 3 | 4 | 5 | 6 | VI-2 | Prdm8 |
| 7356 | 3 | 4 | 5 | 6 | VI-2 | Prdm9 |
| 7357 | 3 | 4 | 5 | 6 | VI-2 | Prdx5 |
| 7358 | 3 | 4 | 5 | 6 | VI-2 | Prelp |
| 7359 | 3 | 4 | 5 | 6 | VI-2 | Prepl |
| 7360 | 3 | 4 | 5 | 6 | VI-2 | Prickle4 |
| 7361 | 3 | 4 | 5 | 6 | VI-2 | Prim1 |
| 7362 | 3 | 4 | 5 | 6 | VI-2 | Prkaa1 |
| 7363 | 3 | 4 | 5 | 6 | VI-2 | Prkca |
| 7364 | 3 | 4 | 5 | 6 | VI-2 | Prkd2 |
| 7365 | 3 | 4 | 5 | 6 | VI-2 | Prkg1 |
| 7366 | 3 | 4 | 5 | 6 | VI-2 | Prl3c1 |
| 7367 | 3 | 4 | 5 | 6 | VI-2 | Prmt2 |
| 7368 | 3 | 4 | 5 | 6 | VI-2 | Prmt6 |
| 7369 | 3 | 4 | 5 | 6 | VI-2 | Prnp |
| 7370 | 3 | 4 | 5 | 6 | VI-2 | Prok2 |
| 7371 | 3 | 4 | 5 | 6 | VI-2 | Prokr2 |
| 7372 | 3 | 4 | 5 | 6 | VI-2 | Proser1 |
| 7373 | 3 | 4 | 5 | 6 | VI-2 | Prox2 |
| 7374 | 3 | 4 | 5 | 6 | VI-2 | Proz |
| 7375 | 3 | 4 | 5 | 6 | VI-2 | Prpf38a |
| 7376 | 3 | 4 | 5 | 6 | VI-2 | Prpf40b |
| 7377 | 3 | 4 | 5 | 6 | VI-2 | Prps2 |
| 7378 | 3 | 4 | 5 | 6 | VI-2 | Prr11 |
| 7379 | 3 | 4 | 5 | 6 | VI-2 | Prr12 |
| 7380 | 3 | 4 | 5 | 6 | VI-2 | Prr16 |
| 7381 | 3 | 4 | 5 | 6 | VI-2 | Prr27 |
| 7382 | 3 | 4 | 5 | 6 | VI-2 | Prr33 |
| 7383 | 3 | 4 | 5 | 6 | VI-2 | Prr5l |
| 7384 | 3 | 4 | 5 | 6 | VI-2 | Prrc2b |
| 7385 | 3 | 4 | 5 | 6 | VI-2 | Prrg1 |
| 7386 | 3 | 4 | 5 | 6 | VI-2 | Prrg2 |
| 7387 | 3 | 4 | 5 | 6 | VI-2 | Prrt4 |
| 7388 | 3 | 4 | 5 | 6 | VI-2 | Prrx1 |
| 7389 | 3 | 4 | 5 | 6 | VI-2 | Prrx2 |
| 7390 | 3 | 4 | 5 | 6 | VI-2 | Prss45 |
| 7391 | 3 | 4 | 5 | 6 | VI-2 | Prss48 |
| 7392 | 3 | 4 | 5 | 6 | VI-2 | Prune |
| 7393 | 3 | 4 | 5 | 6 | VI-2 | Psap1 |
| 7394 | 3 | 4 | 5 | 6 | VI-2 | Pskh1 |
| 7395 | 3 | 4 | 5 | 6 | VI-2 | Psma4 |
| 7396 | 3 | 4 | 5 | 6 | VI-2 | Psmc3ip |
| 7397 | 3 | 4 | 5 | 6 | VI-2 | Psmc5 |
| 7398 | 3 | 4 | 5 | 6 | VI-2 | Psmf1 |
| 7399 | 3 | 4 | 5 | 6 | VI-2 | Pspc1 |
| 7400 | 3 | 4 | 5 | 6 | VI-2 | Psph |
| 7401 | 3 | 4 | 5 | 6 | VI-2 | Psrc1 |
| 7402 | 3 | 4 | 5 | 6 | VI-2 | Ptafr |
| 7403 | 3 | 4 | 5 | 6 | VI-2 | Ptcd3 |
| 7404 | 3 | 4 | 5 | 6 | VI-2 | Ptcra |
| 7405 | 3 | 4 | 5 | 6 | VI-2 | Ptges3 |
| 7406 | 3 | 4 | 5 | 6 | VI-2 | Ptgfr |
| 7407 | 3 | 4 | 5 | 6 | VI-2 | Ptgfrn |
| 7408 | 3 | 4 | 5 | 6 | VI-2 | Ptgir |
| 7409 | 3 | 4 | 5 | 6 | VI-2 | Ptplad2 |
| 7410 | 3 | 4 | 5 | 6 | VI-2 | Ptpn1 |
| 7411 | 3 | 4 | 5 | 6 | VI-2 | Ptpn11 |
| 7412 | 3 | 4 | 5 | 6 | VI-2 | Ptpn12 |
| 7413 | 3 | 4 | 5 | 6 | VI-2 | Ptpn4 |
| 7414 | 3 | 4 | 5 | 6 | VI-2 | Ptpra |
| 7415 | 3 | 4 | 5 | 6 | VI-2 | Ptprc |
| 7416 | 3 | 4 | 5 | 6 | VI-2 | Ptpre |
| 7417 | 3 | 4 | 5 | 6 | VI-2 | Ptprf |
| 7418 | 3 | 4 | 5 | 6 | VI-2 | Ptprg |
| 7419 | 3 | 4 | 5 | 6 | VI-2 | Ptprj |
| 7420 | 3 | 4 | 5 | 6 | VI-2 | Ptrhd1 |
| 7421 | 3 | 4 | 5 | 6 | VI-2 | Ptx3 |
| 7422 | 3 | 4 | 5 | 6 | VI-2 | Pum1 |
| 7423 | 3 | 4 | 5 | 6 | VI-2 | Purb |
| 7424 | 3 | 4 | 5 | 6 | VI-2 | Purg |
| 7425 | 3 | 4 | 5 | 6 | VI-2 | Pwp1 |
| 7426 | 3 | 4 | 5 | 6 | VI-2 | Pxmp4 |
| 7427 | 3 | 4 | 5 | 6 | VI-2 | Pycard |
| 7428 | 3 | 4 | 5 | 6 | VI-2 | Pygb |
| 7429 | 3 | 4 | 5 | 6 | VI-2 | Qars |
| 7430 | 3 | 4 | 5 | 6 | VI-2 | Qpctl |
| 7431 | 3 | 4 | 5 | 6 | VI-2 | Qprt |
| 7432 | 3 | 4 | 5 | 6 | VI-2 | Qrich1 |
| 7433 | 3 | 4 | 5 | 6 | VI-2 | Qsox2 |
| 7434 | 3 | 4 | 5 | 6 | VI-2 | R3hdm2 |
| 7435 | 3 | 4 | 5 | 6 | VI-2 | Rab10 |
| 7436 | 3 | 4 | 5 | 6 | VI-2 | Rab11a |
| 7437 | 3 | 4 | 5 | 6 | VI-2 | Rab14 |
| 7438 | 3 | 4 | 5 | 6 | VI-2 | Rab1b |
| 7439 | 3 | 4 | 5 | 6 | VI-2 | Rab23 |
| 7440 | 3 | 4 | 5 | 6 | VI-2 | Rab26 |
| 7441 | 3 | 4 | 5 | 6 | VI-2 | Rab27b |
| 7442 | 3 | 4 | 5 | 6 | VI-2 | Rab2b |
| 7443 | 3 | 4 | 5 | 6 | VI-2 | Rab36 |
| 7444 | 3 | 4 | 5 | 6 | VI-2 | Rab38 |
| 7445 | 3 | 4 | 5 | 6 | VI-2 | Rab3gap2 |
| 7446 | 3 | 4 | 5 | 6 | VI-2 | Rab3il1 |
| 7447 | 3 | 4 | 5 | 6 | VI-2 | Rab42 |
| 7448 | 3 | 4 | 5 | 6 | VI-2 | Rab6a |
| 7449 | 3 | 4 | 5 | 6 | VI-2 | Rabgap1 |
| 7450 | 3 | 4 | 5 | 6 | VI-2 | Rac3 |
| 7451 | 3 | 4 | 5 | 6 | VI-2 | Racgap1 |
| 7452 | 3 | 4 | 5 | 6 | VI-2 | Rad1 |
| 7453 | 3 | 4 | 5 | 6 | VI-2 | Rad50 |
| 7454 | 3 | 4 | 5 | 6 | VI-2 | Rad51 |
| 7455 | 3 | 4 | 5 | 6 | VI-2 | Rad51b |
| 7456 | 3 | 4 | 5 | 6 | VI-2 | Rad51c |
| 7457 | 3 | 4 | 5 | 6 | VI-2 | Rad54b |
| 7458 | 3 | 4 | 5 | 6 | VI-2 | Rad54l |
| 7459 | 3 | 4 | 5 | 6 | VI-2 | Rai1 |
| 7460 | 3 | 4 | 5 | 6 | VI-2 | Rag1 |
| 7461 | 3 | 4 | 5 | 6 | VI-2 | Rag2 |
| 7462 | 3 | 4 | 5 | 6 | VI-2 | Ralgapa1 |
| 7463 | 3 | 4 | 5 | 6 | VI-2 | Rap1b |
| 7464 | 3 | 4 | 5 | 6 | VI-2 | Rap1gds1 |
| 7465 | 3 | 4 | 5 | 6 | VI-2 | Rap2a |
| 7466 | 3 | 4 | 5 | 6 | VI-2 | Rap2b |
| 7467 | 3 | 4 | 5 | 6 | VI-2 | Rap2c |
| 7468 | 3 | 4 | 5 | 6 | VI-2 | Rapgef2 |
| 7469 | 3 | 4 | 5 | 6 | VI-2 | Rarb |
| 7470 | 3 | 4 | 5 | 6 | VI-2 | Rarg |
| 7471 | 3 | 4 | 5 | 6 | VI-2 | Rasa1 |
| 7472 | 3 | 4 | 5 | 6 | VI-2 | Rasl10a |
| 7473 | 3 | 4 | 5 | 6 | VI-2 | Rassf5 |
| 7474 | 3 | 4 | 5 | 6 | VI-2 | Rassf7 |
| 7475 | 3 | 4 | 5 | 6 | VI-2 | Rassf9 |
| 7476 | 3 | 4 | 5 | 6 | VI-2 | Raver2 |
| 7477 | 3 | 4 | 5 | 6 | VI-2 | Rbak |
| 7478 | 3 | 4 | 5 | 6 | VI-2 | Rbl1 |
| 7479 | 3 | 4 | 5 | 6 | VI-2 | Rbm12b2 |
| 7480 | 3 | 4 | 5 | 6 | VI-2 | Rbm15 |
| 7481 | 3 | 4 | 5 | 6 | VI-2 | Rbm18 |
| 7482 | 3 | 4 | 5 | 6 | VI-2 | Rbm25 |
| 7483 | 3 | 4 | 5 | 6 | VI-2 | Rbm26 |
| 7484 | 3 | 4 | 5 | 6 | VI-2 | Rbm31y |
| 7485 | 3 | 4 | 5 | 6 | VI-2 | Rbm33 |
| 7486 | 3 | 4 | 5 | 6 | VI-2 | Rbm44 |

Fig. 34 - 40

| | | | | | | |
|---|---|---|---|---|---|---|
| 7487 | 3 | 4 | 5 | 6 | VI-2 | Rbm46 |
| 7488 | 3 | 4 | 5 | 6 | VI-2 | Rbm47 |
| 7489 | 3 | 4 | 5 | 6 | VI-2 | Rbms3 |
| 7490 | 3 | 4 | 5 | 6 | VI-2 | Rbmxl1 |
| 7491 | 3 | 4 | 5 | 6 | VI-2 | Rc3h1 |
| 7492 | 3 | 4 | 5 | 6 | VI-2 | Rccd1 |
| 7493 | 3 | 4 | 5 | 6 | VI-2 | Rcor2 |
| 7494 | 3 | 4 | 5 | 6 | VI-2 | Rdh1 |
| 7495 | 3 | 4 | 5 | 6 | VI-2 | Rdh9 |
| 7496 | 3 | 4 | 5 | 6 | VI-2 | Rdx |
| 7497 | 3 | 4 | 5 | 6 | VI-2 | Recql4 |
| 7498 | 3 | 4 | 5 | 6 | VI-2 | Reep1 |
| 7499 | 3 | 4 | 5 | 6 | VI-2 | Reep6 |
| 7500 | 3 | 4 | 5 | 6 | VI-2 | Rel |
| 7501 | 3 | 4 | 5 | 6 | VI-2 | Rell1 |
| 7502 | 3 | 4 | 5 | 6 | VI-2 | Reln |
| 7503 | 3 | 4 | 5 | 6 | VI-2 | Rem1 |
| 7504 | 3 | 4 | 5 | 6 | VI-2 | Repin1 |
| 7505 | 3 | 4 | 5 | 6 | VI-2 | Rev1 |
| 7506 | 3 | 4 | 5 | 6 | VI-2 | Rfpl3s |
| 7507 | 3 | 4 | 5 | 6 | VI-2 | Rfx4 |
| 7508 | 3 | 4 | 5 | 6 | VI-2 | Rfx7 |
| 7509 | 3 | 4 | 5 | 6 | VI-2 | Rfx8 |
| 7510 | 3 | 4 | 5 | 6 | VI-2 | Rfxank |
| 7511 | 3 | 4 | 5 | 6 | VI-2 | Rgag4 |
| 7512 | 3 | 4 | 5 | 6 | VI-2 | Rgl1 |
| 7513 | 3 | 4 | 5 | 6 | VI-2 | Rgs18 |
| 7514 | 3 | 4 | 5 | 6 | VI-2 | Rgs6 |
| 7515 | 3 | 4 | 5 | 6 | VI-2 | Rgsl1 |
| 7516 | 3 | 4 | 5 | 6 | VI-2 | Rhag |
| 7517 | 3 | 4 | 5 | 6 | VI-2 | Rhno1 |
| 7518 | 3 | 4 | 5 | 6 | VI-2 | Rhobtb2 |
| 7519 | 3 | 4 | 5 | 6 | VI-2 | Rhoh |
| 7520 | 3 | 4 | 5 | 6 | VI-2 | Rhoq |
| 7521 | 3 | 4 | 5 | 6 | VI-2 | Rhot1 |
| 7522 | 3 | 4 | 5 | 6 | VI-2 | Ric8b |
| 7523 | 3 | 4 | 5 | 6 | VI-2 | Rimkla |
| 7524 | 3 | 4 | 5 | 6 | VI-2 | Rims3 |
| 7525 | 3 | 4 | 5 | 6 | VI-2 | Ring1 |
| 7526 | 3 | 4 | 5 | 6 | VI-2 | Rmdn2 |
| 7527 | 3 | 4 | 5 | 6 | VI-2 | Rmi1 |
| 7528 | 3 | 4 | 5 | 6 | VI-2 | Rmi2 |
| 7529 | 3 | 4 | 5 | 6 | VI-2 | Rnasel |
| 7530 | 3 | 4 | 5 | 6 | VI-2 | Rnf111 |
| 7531 | 3 | 4 | 5 | 6 | VI-2 | Rnf113a1 |
| 7532 | 3 | 4 | 5 | 6 | VI-2 | Rnf123 |
| 7533 | 3 | 4 | 5 | 6 | VI-2 | Rnf13 |
| 7534 | 3 | 4 | 5 | 6 | VI-2 | Rnf135 |
| 7535 | 3 | 4 | 5 | 6 | VI-2 | Rnf138 |
| 7536 | 3 | 4 | 5 | 6 | VI-2 | Rnf150 |
| 7537 | 3 | 4 | 5 | 6 | VI-2 | Rnf152 |
| 7538 | 3 | 4 | 5 | 6 | VI-2 | Rnf157 |
| 7539 | 3 | 4 | 5 | 6 | VI-2 | Rnf168 |
| 7540 | 3 | 4 | 5 | 6 | VI-2 | Rnf216 |
| 7541 | 3 | 4 | 5 | 6 | VI-2 | Rnf217 |
| 7542 | 3 | 4 | 5 | 6 | VI-2 | Rnf219 |
| 7543 | 3 | 4 | 5 | 6 | VI-2 | Rnf26 |
| 7544 | 3 | 4 | 5 | 6 | VI-2 | Rnf41 |
| 7545 | 3 | 4 | 5 | 6 | VI-2 | Rnf43 |
| 7546 | 3 | 4 | 5 | 6 | VI-2 | Rnf5 |
| 7547 | 3 | 4 | 5 | 6 | VI-2 | Rnf6 |
| 7548 | 3 | 4 | 5 | 6 | VI-2 | Rnf7 |
| 7549 | 3 | 4 | 5 | 6 | VI-2 | Rngtt |
| 7550 | 3 | 4 | 5 | 6 | VI-2 | Rnls |
| 7551 | 3 | 4 | 5 | 6 | VI-2 | Robo1 |
| 7552 | 3 | 4 | 5 | 6 | VI-2 | Robo3 |
| 7553 | 3 | 4 | 5 | 6 | VI-2 | Rock2 |
| 7554 | 3 | 4 | 5 | 6 | VI-2 | Ror1 |
| 7555 | 3 | 4 | 5 | 6 | VI-2 | Rorc |
| 7556 | 3 | 4 | 5 | 6 | VI-2 | Rpe |
| 7557 | 3 | 4 | 5 | 6 | VI-2 | Rpl29 |
| 7558 | 3 | 4 | 5 | 6 | VI-2 | Rpl3 |
| 7559 | 3 | 4 | 5 | 6 | VI-2 | Rps2 |
| 7560 | 3 | 4 | 5 | 6 | VI-2 | Rptn |
| 7561 | 3 | 4 | 5 | 6 | VI-2 | Rptor |
| 7562 | 3 | 4 | 5 | 6 | VI-2 | Rpusd1 |
| 7563 | 3 | 4 | 5 | 6 | VI-2 | Rpusd4 |
| 7564 | 3 | 4 | 5 | 6 | VI-2 | Rragd |
| 7565 | 3 | 4 | 5 | 6 | VI-2 | Rreb1 |
| 7566 | 3 | 4 | 5 | 6 | VI-2 | Rrm1 |
| 7567 | 3 | 4 | 5 | 6 | VI-2 | Rrm2 |
| 7568 | 3 | 4 | 5 | 6 | VI-2 | Rrp36 |
| 7569 | 3 | 4 | 5 | 6 | VI-2 | Rsf1 |
| 7570 | 3 | 4 | 5 | 6 | VI-2 | Rsph3a |
| 7571 | 3 | 4 | 5 | 6 | VI-2 | Rsph3b |
| 7572 | 3 | 4 | 5 | 6 | VI-2 | Rspo3 |
| 7573 | 3 | 4 | 5 | 6 | VI-2 | Rsrc1 |
| 7574 | 3 | 4 | 5 | 6 | VI-2 | Rsrp1 |
| 7575 | 3 | 4 | 5 | 6 | VI-2 | Rtdr1 |
| 7576 | 3 | 4 | 5 | 6 | VI-2 | Rtn4 |
| 7577 | 3 | 4 | 5 | 6 | VI-2 | Rtn4r |
| 7578 | 3 | 4 | 5 | 6 | VI-2 | Rtn4rl1 |
| 7579 | 3 | 4 | 5 | 6 | VI-2 | Runx3 |
| 7580 | 3 | 4 | 5 | 6 | VI-2 | Rwdd3 |
| 7581 | 3 | 4 | 5 | 6 | VI-2 | Rwdd4a |
| 7582 | 3 | 4 | 5 | 6 | VI-2 | Rxfp4 |
| 7583 | 3 | 4 | 5 | 6 | VI-2 | S100a2 |
| 7584 | 3 | 4 | 5 | 6 | VI-2 | S1pr2 |
| 7585 | 3 | 4 | 5 | 6 | VI-2 | S1pr3 |
| 7586 | 3 | 4 | 5 | 6 | VI-2 | Saa4 |
| 7587 | 3 | 4 | 5 | 6 | VI-2 | Sae1 |
| 7588 | 3 | 4 | 5 | 6 | VI-2 | Safb |
| 7589 | 3 | 4 | 5 | 6 | VI-2 | Sall2 |
| 7590 | 3 | 4 | 5 | 6 | VI-2 | Samd1 |
| 7591 | 3 | 4 | 5 | 6 | VI-2 | Samd10 |
| 7592 | 3 | 4 | 5 | 6 | VI-2 | Samd12 |
| 7593 | 3 | 4 | 5 | 6 | VI-2 | Samsn1 |
| 7594 | 3 | 4 | 5 | 6 | VI-2 | Sap130 |
| 7595 | 3 | 4 | 5 | 6 | VI-2 | Sapcd2 |
| 7596 | 3 | 4 | 5 | 6 | VI-2 | Sar1b |
| 7597 | 3 | 4 | 5 | 6 | VI-2 | Sash3 |
| 7598 | 3 | 4 | 5 | 6 | VI-2 | Satb1 |
| 7599 | 3 | 4 | 5 | 6 | VI-2 | Sbk1 |
| 7600 | 3 | 4 | 5 | 6 | VI-2 | Sbk3 |
| 7601 | 3 | 4 | 5 | 6 | VI-2 | Sbno1 |
| 7602 | 3 | 4 | 5 | 6 | VI-2 | Sc5d |
| 7603 | 3 | 4 | 5 | 6 | VI-2 | Scaf1 |
| 7604 | 3 | 4 | 5 | 6 | VI-2 | Scai |
| 7605 | 3 | 4 | 5 | 6 | VI-2 | Scamp1 |
| 7606 | 3 | 4 | 5 | 6 | VI-2 | Scamp2 |
| 7607 | 3 | 4 | 5 | 6 | VI-2 | Scamp4 |
| 7608 | 3 | 4 | 5 | 6 | VI-2 | Scarb1 |
| 7609 | 3 | 4 | 5 | 6 | VI-2 | Scarf2 |
| 7610 | 3 | 4 | 5 | 6 | VI-2 | Scel |
| 7611 | 3 | 4 | 5 | 6 | VI-2 | Scrib |
| 7612 | 3 | 4 | 5 | 6 | VI-2 | Scrn3 |
| 7613 | 3 | 4 | 5 | 6 | VI-2 | Scube2 |
| 7614 | 3 | 4 | 5 | 6 | VI-2 | Sdad1 |
| 7615 | 3 | 4 | 5 | 6 | VI-2 | Sdc1 |
| 7616 | 3 | 4 | 5 | 6 | VI-2 | Sdhaf1 |
| 7617 | 3 | 4 | 5 | 6 | VI-2 | Sdhc |
| 7618 | 3 | 4 | 5 | 6 | VI-2 | Sdhd |
| 7619 | 3 | 4 | 5 | 6 | VI-2 | Sec22b |
| 7620 | 3 | 4 | 5 | 6 | VI-2 | Sec23a |
| 7621 | 3 | 4 | 5 | 6 | VI-2 | Sec23ip |
| 7622 | 3 | 4 | 5 | 6 | VI-2 | Sec31b |
| 7623 | 3 | 4 | 5 | 6 | VI-2 | Sectm1a |
| 7624 | 3 | 4 | 5 | 6 | VI-2 | Sell |
| 7625 | 3 | 4 | 5 | 6 | VI-2 | Sema3c |
| 7626 | 3 | 4 | 5 | 6 | VI-2 | Sema3e |
| 7627 | 3 | 4 | 5 | 6 | VI-2 | Sema4b |
| 7628 | 3 | 4 | 5 | 6 | VI-2 | Sema4g |
| 7629 | 3 | 4 | 5 | 6 | VI-2 | Sema5b |
| 7630 | 3 | 4 | 5 | 6 | VI-2 | Sema6a |
| 7631 | 3 | 4 | 5 | 6 | VI-2 | Senp7 |
| 7632 | 3 | 4 | 5 | 6 | VI-2 | Sept10 |
| 7633 | 3 | 4 | 5 | 6 | VI-2 | Sept2 |
| 7634 | 3 | 4 | 5 | 6 | VI-2 | Sept6 |
| 7635 | 3 | 4 | 5 | 6 | VI-2 | Serinc1 |
| 7636 | 3 | 4 | 5 | 6 | VI-2 | Serpina3b |
| 7637 | 3 | 4 | 5 | 6 | VI-2 | Serpina9 |
| 7638 | 3 | 4 | 5 | 6 | VI-2 | Serpinb11 |
| 7639 | 3 | 4 | 5 | 6 | VI-2 | Serpinb12 |
| 7640 | 3 | 4 | 5 | 6 | VI-2 | Serpinb13 |
| 7641 | 3 | 4 | 5 | 6 | VI-2 | Serpinb3c |
| 7642 | 3 | 4 | 5 | 6 | VI-2 | Serpinb5 |
| 7643 | 3 | 4 | 5 | 6 | VI-2 | Serpinb7 |
| 7644 | 3 | 4 | 5 | 6 | VI-2 | Serpinc1 |
| 7645 | 3 | 4 | 5 | 6 | VI-2 | Sesn3 |
| 7646 | 3 | 4 | 5 | 6 | VI-2 | Setd1b |
| 7647 | 3 | 4 | 5 | 6 | VI-2 | Setd2 |
| 7648 | 3 | 4 | 5 | 6 | VI-2 | Setd5 |
| 7649 | 3 | 4 | 5 | 6 | VI-2 | Setx |
| 7650 | 3 | 4 | 5 | 6 | VI-2 | Sf3b6 |
| 7651 | 3 | 4 | 5 | 6 | VI-2 | Sfmbt1 |
| 7652 | 3 | 4 | 5 | 6 | VI-2 | Sfpq |
| 7653 | 3 | 4 | 5 | 6 | VI-2 | Sfrp1 |
| 7654 | 3 | 4 | 5 | 6 | VI-2 | Sft2d2 |
| 7655 | 3 | 4 | 5 | 6 | VI-2 | Sft2d3 |
| 7656 | 3 | 4 | 5 | 6 | VI-2 | Sfxn3 |
| 7657 | 3 | 4 | 5 | 6 | VI-2 | Sfxn5 |
| 7658 | 3 | 4 | 5 | 6 | VI-2 | Sgol1 |
| 7659 | 3 | 4 | 5 | 6 | VI-2 | Sh2b2 |
| 7660 | 3 | 4 | 5 | 6 | VI-2 | Sh2d3c |
| 7661 | 3 | 4 | 5 | 6 | VI-2 | Sh3bp1 |
| 7662 | 3 | 4 | 5 | 6 | VI-2 | Sh3bp5l |
| 7663 | 3 | 4 | 5 | 6 | VI-2 | Sh3kbp1 |
| 7664 | 3 | 4 | 5 | 6 | VI-2 | Sh3pxd2a |
| 7665 | 3 | 4 | 5 | 6 | VI-2 | Sh3pxd2b |
| 7666 | 3 | 4 | 5 | 6 | VI-2 | Sh3rf2 |
| 7667 | 3 | 4 | 5 | 6 | VI-2 | Shank3 |
| 7668 | 3 | 4 | 5 | 6 | VI-2 | Shb |
| 7669 | 3 | 4 | 5 | 6 | VI-2 | Shcbp1 |
| 7670 | 3 | 4 | 5 | 6 | VI-2 | She |
| 7671 | 3 | 4 | 5 | 6 | VI-2 | Shisa2 |
| 7672 | 3 | 4 | 5 | 6 | VI-2 | Shisa6 |
| 7673 | 3 | 4 | 5 | 6 | VI-2 | Shoc2 |
| 7674 | 3 | 4 | 5 | 6 | VI-2 | Siae |
| 7675 | 3 | 4 | 5 | 6 | VI-2 | Siah1b |
| 7676 | 3 | 4 | 5 | 6 | VI-2 | Siah2 |
| 7677 | 3 | 4 | 5 | 6 | VI-2 | Siglec15 |
| 7678 | 3 | 4 | 5 | 6 | VI-2 | Siglec5 |

Fig. 34 - 41

| | | | | | | | |
|---|---|---|---|---|---|---|---|
| 7679 | 3 | 4 | 5 | 6 | | VI-2 | Siglecg |
| 7680 | 3 | 4 | 5 | 6 | | VI-2 | Sin3a |
| 7681 | 3 | 4 | 5 | 6 | | VI-2 | Sipa1l1 |
| 7682 | 3 | 4 | 5 | 6 | | VI-2 | Sipa1l2 |
| 7683 | 3 | 4 | 5 | 6 | | VI-2 | Sirpa |
| 7684 | 3 | 4 | 5 | 6 | | VI-2 | Sirt3 |
| 7685 | 3 | 4 | 5 | 6 | | VI-2 | Sirt4 |
| 7686 | 3 | 4 | 5 | 6 | | VI-2 | Sirt5 |
| 7687 | 3 | 4 | 5 | 6 | | VI-2 | Sirt6 |
| 7688 | 3 | 4 | 5 | 6 | | VI-2 | Six3os1 |
| 7689 | 3 | 4 | 5 | 6 | | VI-2 | Ska3 |
| 7690 | 3 | 4 | 5 | 6 | | VI-2 | Ski |
| 7691 | 3 | 4 | 5 | 6 | | VI-2 | Skint1 |
| 7692 | 3 | 4 | 5 | 6 | | VI-2 | Skint2 |
| 7693 | 3 | 4 | 5 | 6 | | VI-2 | Skint5 |
| 7694 | 3 | 4 | 5 | 6 | | VI-2 | Skiv2l |
| 7695 | 3 | 4 | 5 | 6 | | VI-2 | Skiv2l2 |
| 7696 | 3 | 4 | 5 | 6 | | VI-2 | Skp2 |
| 7697 | 3 | 4 | 5 | 6 | | VI-2 | Sla2 |
| 7698 | 3 | 4 | 5 | 6 | | VI-2 | Slain1 |
| 7699 | 3 | 4 | 5 | 6 | | VI-2 | Slain2 |
| 7700 | 3 | 4 | 5 | 6 | | VI-2 | Slamf7 |
| 7701 | 3 | 4 | 5 | 6 | | VI-2 | Slamf8 |
| 7702 | 3 | 4 | 5 | 6 | | VI-2 | Slbp |
| 7703 | 3 | 4 | 5 | 6 | | VI-2 | Slc10a1 |
| 7704 | 3 | 4 | 5 | 6 | | VI-2 | Slc10a5 |
| 7705 | 3 | 4 | 5 | 6 | | VI-2 | Slc11a2 |
| 7706 | 3 | 4 | 5 | 6 | | VI-2 | Slc13a2os |
| 7707 | 3 | 4 | 5 | 6 | | VI-2 | Slc13a4 |
| 7708 | 3 | 4 | 5 | 6 | | VI-2 | Slc14a1 |
| 7709 | 3 | 4 | 5 | 6 | | VI-2 | Slc16a12 |
| 7710 | 3 | 4 | 5 | 6 | | VI-2 | Slc16a13 |
| 7711 | 3 | 4 | 5 | 6 | | VI-2 | Slc16a8 |
| 7712 | 3 | 4 | 5 | 6 | | VI-2 | Slc17a1 |
| 7713 | 3 | 4 | 5 | 6 | | VI-2 | Slc17a2 |
| 7714 | 3 | 4 | 5 | 6 | | VI-2 | Slc17a9 |
| 7715 | 3 | 4 | 5 | 6 | | VI-2 | Slc18a3 |
| 7716 | 3 | 4 | 5 | 6 | | VI-2 | Slc18b1 |
| 7717 | 3 | 4 | 5 | 6 | | VI-2 | Slc1a5 |
| 7718 | 3 | 4 | 5 | 6 | | VI-2 | Slc22a15 |
| 7719 | 3 | 4 | 5 | 6 | | VI-2 | Slc22a2 |
| 7720 | 3 | 4 | 5 | 6 | | VI-2 | Slc22a21 |
| 7721 | 3 | 4 | 5 | 6 | | VI-2 | Slc22a28 |
| 7722 | 3 | 4 | 5 | 6 | | VI-2 | Slc22a30 |
| 7723 | 3 | 4 | 5 | 6 | | VI-2 | Slc22a8 |
| 7724 | 3 | 4 | 5 | 6 | | VI-2 | Slc23a1 |
| 7725 | 3 | 4 | 5 | 6 | | VI-2 | Slc24a5 |
| 7726 | 3 | 4 | 5 | 6 | | VI-2 | Slc25a10 |
| 7727 | 3 | 4 | 5 | 6 | | VI-2 | Slc25a2 |
| 7728 | 3 | 4 | 5 | 6 | | VI-2 | Slc25a21 |
| 7729 | 3 | 4 | 5 | 6 | | VI-2 | Slc25a23 |
| 7730 | 3 | 4 | 5 | 6 | | VI-2 | Slc25a31 |
| 7731 | 3 | 4 | 5 | 6 | | VI-2 | Slc25a4 |
| 7732 | 3 | 4 | 5 | 6 | | VI-2 | Slc25a40 |
| 7733 | 3 | 4 | 5 | 6 | | VI-2 | Slc25a48 |
| 7734 | 3 | 4 | 5 | 6 | | VI-2 | Slc25a54 |
| 7735 | 3 | 4 | 5 | 6 | | VI-2 | Slc26a1 |
| 7736 | 3 | 4 | 5 | 6 | | VI-2 | Slc26a6 |
| 7737 | 3 | 4 | 5 | 6 | | VI-2 | Slc27a3 |
| 7738 | 3 | 4 | 5 | 6 | | VI-2 | Slc27a5 |
| 7739 | 3 | 4 | 5 | 6 | | VI-2 | Slc29a2 |
| 7740 | 3 | 4 | 5 | 6 | | VI-2 | Slc29a3 |
| 7741 | 3 | 4 | 5 | 6 | | VI-2 | Slc2a2 |
| 7742 | 3 | 4 | 5 | 6 | | VI-2 | Slc2a4 |
| 7743 | 3 | 4 | 5 | 6 | | VI-2 | Slc2a9 |
| 7744 | 3 | 4 | 5 | 6 | | VI-2 | Slc30a6 |
| 7745 | 3 | 4 | 5 | 6 | | VI-2 | Slc34a2 |
| 7746 | 3 | 4 | 5 | 6 | | VI-2 | Slc35a2 |
| 7747 | 3 | 4 | 5 | 6 | | VI-2 | Slc35a3 |
| 7748 | 3 | 4 | 5 | 6 | | VI-2 | Slc35a4 |
| 7749 | 3 | 4 | 5 | 6 | | VI-2 | Slc35a5 |
| 7750 | 3 | 4 | 5 | 6 | | VI-2 | Slc35b1 |
| 7751 | 3 | 4 | 5 | 6 | | VI-2 | Slc35e2 |
| 7752 | 3 | 4 | 5 | 6 | | VI-2 | Slc35f4 |
| 7753 | 3 | 4 | 5 | 6 | | VI-2 | Slc35g2 |
| 7754 | 3 | 4 | 5 | 6 | | VI-2 | Slc35g3 |
| 7755 | 3 | 4 | 5 | 6 | | VI-2 | Slc36a1 |
| 7756 | 3 | 4 | 5 | 6 | | VI-2 | Slc36a3 |
| 7757 | 3 | 4 | 5 | 6 | | VI-2 | Slc36a4 |
| 7758 | 3 | 4 | 5 | 6 | | VI-2 | Slc38a1 |
| 7759 | 3 | 4 | 5 | 6 | | VI-2 | Slc38a7 |
| 7760 | 3 | 4 | 5 | 6 | | VI-2 | Slc39a12 |
| 7761 | 3 | 4 | 5 | 6 | | VI-2 | Slc39a2 |
| 7762 | 3 | 4 | 5 | 6 | | VI-2 | Slc39a3 |
| 7763 | 3 | 4 | 5 | 6 | | VI-2 | Slc39a9 |
| 7764 | 3 | 4 | 5 | 6 | | VI-2 | Slc3a1 |
| 7765 | 3 | 4 | 5 | 6 | | VI-2 | Slc41a1 |
| 7766 | 3 | 4 | 5 | 6 | | VI-2 | Slc44a2 |
| 7767 | 3 | 4 | 5 | 6 | | VI-2 | Slc44a3 |
| 7768 | 3 | 4 | 5 | 6 | | VI-2 | Slc46a1 |
| 7769 | 3 | 4 | 5 | 6 | | VI-2 | Slc46a3 |
| 7770 | 3 | 4 | 5 | 6 | | VI-2 | Slc4a1ap |
| 7771 | 3 | 4 | 5 | 6 | | VI-2 | Slc4a2 |
| 7772 | 3 | 4 | 5 | 6 | | VI-2 | Slc5a3 |
| 7773 | 3 | 4 | 5 | 6 | | VI-2 | Slc5a6 |
| 7774 | 3 | 4 | 5 | 6 | | VI-2 | Slc5a9 |
| 7775 | 3 | 4 | 5 | 6 | | VI-2 | Slc6a9 |
| 7776 | 3 | 4 | 5 | 6 | | VI-2 | Slc7a1 |
| 7777 | 3 | 4 | 5 | 6 | | VI-2 | Slc7a11 |
| 7778 | 3 | 4 | 5 | 6 | | VI-2 | Slc9a3r1 |
| 7779 | 3 | 4 | 5 | 6 | | VI-2 | Slc9a9 |
| 7780 | 3 | 4 | 5 | 6 | | VI-2 | Slco1a6 |
| 7781 | 3 | 4 | 5 | 6 | | VI-2 | Slco1b2 |
| 7782 | 3 | 4 | 5 | 6 | | VI-2 | Slco2b1 |
| 7783 | 3 | 4 | 5 | 6 | | VI-2 | Slco4c1 |
| 7784 | 3 | 4 | 5 | 6 | | VI-2 | Slco5a1 |
| 7785 | 3 | 4 | 5 | 6 | | VI-2 | Slco6c1 |
| 7786 | 3 | 4 | 5 | 6 | | VI-2 | Slfn14 |
| 7787 | 3 | 4 | 5 | 6 | | VI-2 | Slk |
| 7788 | 3 | 4 | 5 | 6 | | VI-2 | Slu7 |
| 7789 | 3 | 4 | 5 | 6 | | VI-2 | Slx1b |
| 7790 | 3 | 4 | 5 | 6 | | VI-2 | Slx4 |
| 7791 | 3 | 4 | 5 | 6 | | VI-2 | Slx4ip |
| 7792 | 3 | 4 | 5 | 6 | | VI-2 | Smad2 |
| 7793 | 3 | 4 | 5 | 6 | | VI-2 | Smad5 |
| 7794 | 3 | 4 | 5 | 6 | | VI-2 | Smad7 |
| 7795 | 3 | 4 | 5 | 6 | | VI-2 | Smad9 |
| 7796 | 3 | 4 | 5 | 6 | | VI-2 | Smarca5 |
| 7797 | 3 | 4 | 5 | 6 | | VI-2 | Smarcc1 |
| 7798 | 3 | 4 | 5 | 6 | | VI-2 | Smarcc2 |
| 7799 | 3 | 4 | 5 | 6 | | VI-2 | Smarcd1 |
| 7800 | 3 | 4 | 5 | 6 | | VI-2 | Smc2 |
| 7801 | 3 | 4 | 5 | 6 | | VI-2 | Smc2os |
| 7802 | 3 | 4 | 5 | 6 | | VI-2 | Smc6 |
| 7803 | 3 | 4 | 5 | 6 | | VI-2 | Smco1 |
| 7804 | 3 | 4 | 5 | 6 | | VI-2 | Smg6 |
| 7805 | 3 | 4 | 5 | 6 | | VI-2 | Smg7 |
| 7806 | 3 | 4 | 5 | 6 | | VI-2 | Smg8 |
| 7807 | 3 | 4 | 5 | 6 | | VI-2 | Smim15 |
| 7808 | 3 | 4 | 5 | 6 | | VI-2 | Smim5 |
| 7809 | 3 | 4 | 5 | 6 | | VI-2 | Smlr1 |
| 7810 | 3 | 4 | 5 | 6 | | VI-2 | Smndc1 |
| 7811 | 3 | 4 | 5 | 6 | | VI-2 | Smoc1 |
| 7812 | 3 | 4 | 5 | 6 | | VI-2 | Smoc2 |
| 7813 | 3 | 4 | 5 | 6 | | VI-2 | Smok2a |
| 7814 | 3 | 4 | 5 | 6 | | VI-2 | Smpdl3a |
| 7815 | 3 | 4 | 5 | 6 | | VI-2 | Smug1 |
| 7816 | 3 | 4 | 5 | 6 | | VI-2 | Smurf2 |
| 7817 | 3 | 4 | 5 | 6 | | VI-2 | Smyd3 |
| 7818 | 3 | 4 | 5 | 6 | | VI-2 | Snap23 |
| 7819 | 3 | 4 | 5 | 6 | | VI-2 | Snap29 |
| 7820 | 3 | 4 | 5 | 6 | | VI-2 | Snapc3 |
| 7821 | 3 | 4 | 5 | 6 | | VI-2 | Snrk |
| 7822 | 3 | 4 | 5 | 6 | | VI-2 | Sntg2 |
| 7823 | 3 | 4 | 5 | 6 | | VI-2 | Snx12 |
| 7824 | 3 | 4 | 5 | 6 | | VI-2 | Snx16 |
| 7825 | 3 | 4 | 5 | 6 | | VI-2 | Snx2 |
| 7826 | 3 | 4 | 5 | 6 | | VI-2 | Snx22 |
| 7827 | 3 | 4 | 5 | 6 | | VI-2 | Snx32 |
| 7828 | 3 | 4 | 5 | 6 | | VI-2 | Snx6 |
| 7829 | 3 | 4 | 5 | 6 | | VI-2 | Snx7 |
| 7830 | 3 | 4 | 5 | 6 | | VI-2 | Snx9 |
| 7831 | 3 | 4 | 5 | 6 | | VI-2 | Socs5 |
| 7832 | 3 | 4 | 5 | 6 | | VI-2 | Sod2 |
| 7833 | 3 | 4 | 5 | 6 | | VI-2 | Son |
| 7834 | 3 | 4 | 5 | 6 | | VI-2 | Sord |
| 7835 | 3 | 4 | 5 | 6 | | VI-2 | Sorl1 |
| 7836 | 3 | 4 | 5 | 6 | | VI-2 | Sos1 |
| 7837 | 3 | 4 | 5 | 6 | | VI-2 | Sost |
| 7838 | 3 | 4 | 5 | 6 | | VI-2 | Sowaha |
| 7839 | 3 | 4 | 5 | 6 | | VI-2 | Sox12 |
| 7840 | 3 | 4 | 5 | 6 | | VI-2 | Sox13 |
| 7841 | 3 | 4 | 5 | 6 | | VI-2 | Sox17 |
| 7842 | 3 | 4 | 5 | 6 | | VI-2 | Sox2 |
| 7843 | 3 | 4 | 5 | 6 | | VI-2 | Sp6 |
| 7844 | 3 | 4 | 5 | 6 | | VI-2 | Spaca6 |
| 7845 | 3 | 4 | 5 | 6 | | VI-2 | Spag5 |
| 7846 | 3 | 4 | 5 | 6 | | VI-2 | Spag7 |
| 7847 | 3 | 4 | 5 | 6 | | VI-2 | Sparc |
| 7848 | 3 | 4 | 5 | 6 | | VI-2 | Spata1 |
| 7849 | 3 | 4 | 5 | 6 | | VI-2 | Spata13 |
| 7850 | 3 | 4 | 5 | 6 | | VI-2 | Spata22 |
| 7851 | 3 | 4 | 5 | 6 | | VI-2 | Spata2L |
| 7852 | 3 | 4 | 5 | 6 | | VI-2 | Spata31 |
| 7853 | 3 | 4 | 5 | 6 | | VI-2 | Spata5l1 |
| 7854 | 3 | 4 | 5 | 6 | | VI-2 | Spats2 |
| 7855 | 3 | 4 | 5 | 6 | | VI-2 | Spats2l |
| 7856 | 3 | 4 | 5 | 6 | | VI-2 | Spc25 |
| 7857 | 3 | 4 | 5 | 6 | | VI-2 | Spdl1 |
| 7858 | 3 | 4 | 5 | 6 | | VI-2 | Spdya |
| 7859 | 3 | 4 | 5 | 6 | | VI-2 | Specc1 |
| 7860 | 3 | 4 | 5 | 6 | | VI-2 | Speer4b |
| 7861 | 3 | 4 | 5 | 6 | | VI-2 | Speer4c |
| 7862 | 3 | 4 | 5 | 6 | | VI-2 | Speer4e |
| 7863 | 3 | 4 | 5 | 6 | | VI-2 | Speer4f |
| 7864 | 3 | 4 | 5 | 6 | | VI-2 | Spesp1 |
| 7865 | 3 | 4 | 5 | 6 | | VI-2 | Spg20 |
| 7866 | 3 | 4 | 5 | 6 | | VI-2 | Sphk2 |
| 7867 | 3 | 4 | 5 | 6 | | VI-2 | Spib |
| 7868 | 3 | 4 | 5 | 6 | | VI-2 | Spin2-ps1 |
| 7869 | 3 | 4 | 5 | 6 | | VI-2 | Spin2c |
| 7870 | 3 | 4 | 5 | 6 | | VI-2 | Spink7 |

Fig. 34 - 42

| | | | | | | |
|---|---|---|---|---|---|---|
| 7871 | 3 | 4 | 5 | 6 | VI-2 | Spn |
| 7872 | 3 | 4 | 5 | 6 | VI-2 | Spn-ps |
| 7873 | 3 | 4 | 5 | 6 | VI-2 | Spop |
| 7874 | 3 | 4 | 5 | 6 | VI-2 | Spopl |
| 7875 | 3 | 4 | 5 | 6 | VI-2 | Sppl2b |
| 7876 | 3 | 4 | 5 | 6 | VI-2 | Sprr1a |
| 7877 | 3 | 4 | 5 | 6 | VI-2 | Sprr1b |
| 7878 | 3 | 4 | 5 | 6 | VI-2 | Sprr2f |
| 7879 | 3 | 4 | 5 | 6 | VI-2 | Sprr2g |
| 7880 | 3 | 4 | 5 | 6 | VI-2 | Sprr2h |
| 7881 | 3 | 4 | 5 | 6 | VI-2 | Spsb3 |
| 7882 | 3 | 4 | 5 | 6 | VI-2 | Srbd1 |
| 7883 | 3 | 4 | 5 | 6 | VI-2 | Srd5a3 |
| 7884 | 3 | 4 | 5 | 6 | VI-2 | Srek1 |
| 7885 | 3 | 4 | 5 | 6 | VI-2 | Srgap2 |
| 7886 | 3 | 4 | 5 | 6 | VI-2 | Srl |
| 7887 | 3 | 4 | 5 | 6 | VI-2 | Srms |
| 7888 | 3 | 4 | 5 | 6 | VI-2 | Srp14 |
| 7889 | 3 | 4 | 5 | 6 | VI-2 | Srsf1 |
| 7890 | 3 | 4 | 5 | 6 | VI-2 | Srsf10 |
| 7891 | 3 | 4 | 5 | 6 | VI-2 | Srsf2 |
| 7892 | 3 | 4 | 5 | 6 | VI-2 | Srsf6 |
| 7893 | 3 | 4 | 5 | 6 | VI-2 | Ssb |
| 7894 | 3 | 4 | 5 | 6 | VI-2 | Ssr5d |
| 7895 | 3 | 4 | 5 | 6 | VI-2 | Sspn |
| 7896 | 3 | 4 | 5 | 6 | VI-2 | Ssr1 |
| 7897 | 3 | 4 | 5 | 6 | VI-2 | Ssr3 |
| 7898 | 3 | 4 | 5 | 6 | VI-2 | Sstr2 |
| 7899 | 3 | 4 | 5 | 6 | VI-2 | Ssty2 |
| 7900 | 3 | 4 | 5 | 6 | VI-2 | St3gal2 |
| 7901 | 3 | 4 | 5 | 6 | VI-2 | St6gal1 |
| 7902 | 3 | 4 | 5 | 6 | VI-2 | St6galnac3 |
| 7903 | 3 | 4 | 5 | 6 | VI-2 | St8sia1 |
| 7904 | 3 | 4 | 5 | 6 | VI-2 | St8sia6 |
| 7905 | 3 | 4 | 5 | 6 | VI-2 | Stam2 |
| 7906 | 3 | 4 | 5 | 6 | VI-2 | Stambpl1 |
| 7907 | 3 | 4 | 5 | 6 | VI-2 | Stamos |
| 7908 | 3 | 4 | 5 | 6 | VI-2 | Stap1 |
| 7909 | 3 | 4 | 5 | 6 | VI-2 | Star |
| 7910 | 3 | 4 | 5 | 6 | VI-2 | Stard4 |
| 7911 | 3 | 4 | 5 | 6 | VI-2 | Stard5 |
| 7912 | 3 | 4 | 5 | 6 | VI-2 | Starf5a |
| 7913 | 3 | 4 | 5 | 6 | VI-2 | Stil |
| 7914 | 3 | 4 | 5 | 6 | VI-2 | Stip1 |
| 7915 | 3 | 4 | 5 | 6 | VI-2 | Stk25 |
| 7916 | 3 | 4 | 5 | 6 | VI-2 | Stk32b |
| 7917 | 3 | 4 | 5 | 6 | VI-2 | Stk35 |
| 7918 | 3 | 4 | 5 | 6 | VI-2 | Stk4 |
| 7919 | 3 | 4 | 5 | 6 | VI-2 | Stk40 |
| 7920 | 3 | 4 | 5 | 6 | VI-2 | Stmn1 |
| 7921 | 3 | 4 | 5 | 6 | VI-2 | Ston2 |
| 7922 | 3 | 4 | 5 | 6 | VI-2 | Strip1 |
| 7923 | 3 | 4 | 5 | 6 | VI-2 | Strn4 |
| 7924 | 3 | 4 | 5 | 6 | VI-2 | Stx12 |
| 7925 | 3 | 4 | 5 | 6 | VI-2 | Stx16 |
| 7926 | 3 | 4 | 5 | 6 | VI-2 | Stx18 |
| 7927 | 3 | 4 | 5 | 6 | VI-2 | Stx19 |
| 7928 | 3 | 4 | 5 | 6 | VI-2 | Stx1a |
| 7929 | 3 | 4 | 5 | 6 | VI-2 | Stx2 |
| 7930 | 3 | 4 | 5 | 6 | VI-2 | Stx7 |
| 7931 | 3 | 4 | 5 | 6 | VI-2 | Stxbp4 |
| 7932 | 3 | 4 | 5 | 6 | VI-2 | Suclg2 |
| 7933 | 3 | 4 | 5 | 6 | VI-2 | Sugp2 |
| 7934 | 3 | 4 | 5 | 6 | VI-2 | Sumo3 |
| 7935 | 3 | 4 | 5 | 6 | VI-2 | Suox |
| 7936 | 3 | 4 | 5 | 6 | VI-2 | Supt20 |
| 7937 | 3 | 4 | 5 | 6 | VI-2 | Supt7l |
| 7938 | 3 | 4 | 5 | 6 | VI-2 | Surf1 |
| 7939 | 3 | 4 | 5 | 6 | VI-2 | Surf2 |
| 7940 | 3 | 4 | 5 | 6 | VI-2 | Susd1 |
| 7941 | 3 | 4 | 5 | 6 | VI-2 | Suv420h1 |
| 7942 | 3 | 4 | 5 | 6 | VI-2 | Suv420h2 |
| 7943 | 3 | 4 | 5 | 6 | VI-2 | Svil |
| 7944 | 3 | 4 | 5 | 6 | VI-2 | Swap70 |
| 7945 | 3 | 4 | 5 | 6 | VI-2 | Swsap1 |
| 7946 | 3 | 4 | 5 | 6 | VI-2 | Syap1 |
| 7947 | 3 | 4 | 5 | 6 | VI-2 | Syk |
| 7948 | 3 | 4 | 5 | 6 | VI-2 | Syncrip |
| 7949 | 3 | 4 | 5 | 6 | VI-2 | Syne2 |
| 7950 | 3 | 4 | 5 | 6 | VI-2 | Synj1 |
| 7951 | 3 | 4 | 5 | 6 | VI-2 | Synj2 |
| 7952 | 3 | 4 | 5 | 6 | VI-2 | Syt10 |
| 7953 | 3 | 4 | 5 | 6 | VI-2 | Sytl5 |
| 7954 | 3 | 4 | 5 | 6 | VI-2 | Sytl2 |
| 7955 | 3 | 4 | 5 | 6 | VI-2 | Sytl4 |
| 7956 | 3 | 4 | 5 | 6 | VI-2 | Syvn1 |
| 7957 | 3 | 4 | 5 | 6 | VI-2 | Szrd1 |
| 7958 | 3 | 4 | 5 | 6 | VI-2 | Tab2 |
| 7959 | 3 | 4 | 5 | 6 | VI-2 | Taco1 |
| 7960 | 3 | 4 | 5 | 6 | VI-2 | Tacr2 |
| 7961 | 3 | 4 | 5 | 6 | VI-2 | Tagap |
| 7962 | 3 | 4 | 5 | 6 | VI-2 | Tagap1 |
| 7963 | 3 | 4 | 5 | 6 | VI-2 | Tal1 |
| 7964 | 3 | 4 | 5 | 6 | VI-2 | Taok3 |
| 7965 | 3 | 4 | 5 | 6 | VI-2 | Tatdn1 |
| 7966 | 3 | 4 | 5 | 6 | VI-2 | Tatdn3 |
| 7967 | 3 | 4 | 5 | 6 | VI-2 | Tax1bp1 |
| 7968 | 3 | 4 | 5 | 6 | VI-2 | Tax1bp3 |
| 7969 | 3 | 4 | 5 | 6 | VI-2 | Tbc1d1 |
| 7970 | 3 | 4 | 5 | 6 | VI-2 | Tbc1d16 |
| 7971 | 3 | 4 | 5 | 6 | VI-2 | Tbc1d24 |
| 7972 | 3 | 4 | 5 | 6 | VI-2 | Tbc1d2b |
| 7973 | 3 | 4 | 5 | 6 | VI-2 | Tbc1d31 |
| 7974 | 3 | 4 | 5 | 6 | VI-2 | Tbc1d32 |
| 7975 | 3 | 4 | 5 | 6 | VI-2 | Tbc1d4 |
| 7976 | 3 | 4 | 5 | 6 | VI-2 | Tbc1d9 |
| 7977 | 3 | 4 | 5 | 6 | VI-2 | Tbcd |
| 7978 | 3 | 4 | 5 | 6 | VI-2 | Tbk1 |
| 7979 | 3 | 4 | 5 | 6 | VI-2 | Tbp |
| 7980 | 3 | 4 | 5 | 6 | VI-2 | Tbx15 |
| 7981 | 3 | 4 | 5 | 6 | VI-2 | Tbx18 |
| 7982 | 3 | 4 | 5 | 6 | VI-2 | Tbx3 |
| 7983 | 3 | 4 | 5 | 6 | VI-2 | Tbx4 |
| 7984 | 3 | 4 | 5 | 6 | VI-2 | Tbx5 |
| 7985 | 3 | 4 | 5 | 6 | VI-2 | Tc2n |
| 7986 | 3 | 4 | 5 | 6 | VI-2 | Tcaim |
| 7987 | 3 | 4 | 5 | 6 | VI-2 | Tceal7 |
| 7988 | 3 | 4 | 5 | 6 | VI-2 | Tcerg1 |
| 7989 | 3 | 4 | 5 | 6 | VI-2 | Tcf20 |
| 7990 | 3 | 4 | 5 | 6 | VI-2 | Tcf7l1 |
| 7991 | 3 | 4 | 5 | 6 | VI-2 | Tcp1 |
| 7992 | 3 | 4 | 5 | 6 | VI-2 | Tcp11l1 |
| 7993 | 3 | 4 | 5 | 6 | VI-2 | Tcte2 |
| 7994 | 3 | 4 | 5 | 6 | VI-2 | Tctn1 |
| 7995 | 3 | 4 | 5 | 6 | VI-2 | Tdgf1 |
| 7996 | 3 | 4 | 5 | 6 | VI-2 | Tdp1 |
| 7997 | 3 | 4 | 5 | 6 | VI-2 | Tdrd7 |
| 7998 | 3 | 4 | 5 | 6 | VI-2 | Tdrkh |
| 7999 | 3 | 4 | 5 | 6 | VI-2 | Tec |
| 8000 | 3 | 4 | 5 | 6 | VI-2 | Tectb |
| 8001 | 3 | 4 | 5 | 6 | VI-2 | Tek |
| 8002 | 3 | 4 | 5 | 6 | VI-2 | Tenm2 |
| 8003 | 3 | 4 | 5 | 6 | VI-2 | Teskl |
| 8004 | 3 | 4 | 5 | 6 | VI-2 | Tex24 |
| 8005 | 3 | 4 | 5 | 6 | VI-2 | Tex30 |
| 8006 | 3 | 4 | 5 | 6 | VI-2 | Tfap2b |
| 8007 | 3 | 4 | 5 | 6 | VI-2 | Tfcp2 |
| 8008 | 3 | 4 | 5 | 6 | VI-2 | Tfdp1 |
| 8009 | 3 | 4 | 5 | 6 | VI-2 | Tfe3 |
| 8010 | 3 | 4 | 5 | 6 | VI-2 | Tgfb1 |
| 8011 | 3 | 4 | 5 | 6 | VI-2 | Tgfb1l1 |
| 8012 | 3 | 4 | 5 | 6 | VI-2 | Tgfb3 |
| 8013 | 3 | 4 | 5 | 6 | VI-2 | Tgif2 |
| 8014 | 3 | 4 | 5 | 6 | VI-2 | Tgif2lx1 |
| 8015 | 3 | 4 | 5 | 6 | VI-2 | Tgm5 |
| 8016 | 3 | 4 | 5 | 6 | VI-2 | Tgoln1 |
| 8017 | 3 | 4 | 5 | 6 | VI-2 | Thap1 |
| 8018 | 3 | 4 | 5 | 6 | VI-2 | Thap11 |
| 8019 | 3 | 4 | 5 | 6 | VI-2 | Thap2 |
| 8020 | 3 | 4 | 5 | 6 | VI-2 | Thbs4 |
| 8021 | 3 | 4 | 5 | 6 | VI-2 | Them4 |
| 8022 | 3 | 4 | 5 | 6 | VI-2 | Themis |
| 8023 | 3 | 4 | 5 | 6 | VI-2 | Thoc5 |
| 8024 | 3 | 4 | 5 | 6 | VI-2 | Thsd1 |
| 8025 | 3 | 4 | 5 | 6 | VI-2 | Thumpd1 |
| 8026 | 3 | 4 | 5 | 6 | VI-2 | Tiam1 |
| 8027 | 3 | 4 | 5 | 6 | VI-2 | Ticam2 |
| 8028 | 3 | 4 | 5 | 6 | VI-2 | Ticrr |
| 8029 | 3 | 4 | 5 | 6 | VI-2 | Tigd4 |
| 8030 | 3 | 4 | 5 | 6 | VI-2 | Tigd5 |
| 8031 | 3 | 4 | 5 | 6 | VI-2 | Timd2 |
| 8032 | 3 | 4 | 5 | 6 | VI-2 | Timeless |
| 8033 | 3 | 4 | 5 | 6 | VI-2 | Timm8a2 |
| 8034 | 3 | 4 | 5 | 6 | VI-2 | Timm9 |
| 8035 | 3 | 4 | 5 | 6 | VI-2 | Tiprl |
| 8036 | 3 | 4 | 5 | 6 | VI-2 | Tjap1 |
| 8037 | 3 | 4 | 5 | 6 | VI-2 | Tldc2 |
| 8038 | 3 | 4 | 5 | 6 | VI-2 | Tle2 |
| 8039 | 3 | 4 | 5 | 6 | VI-2 | Tln2 |
| 8040 | 3 | 4 | 5 | 6 | VI-2 | Tlr11 |
| 8041 | 3 | 4 | 5 | 6 | VI-2 | Tlr5 |
| 8042 | 3 | 4 | 5 | 6 | VI-2 | Tm2d1 |
| 8043 | 3 | 4 | 5 | 6 | VI-2 | Tm9sf4 |
| 8044 | 3 | 4 | 5 | 6 | VI-2 | Tmbim6 |
| 8045 | 3 | 4 | 5 | 6 | VI-2 | Tmcc2 |
| 8046 | 3 | 4 | 5 | 6 | VI-2 | Tmed7 |
| 8047 | 3 | 4 | 5 | 6 | VI-2 | Tmem104 |
| 8048 | 3 | 4 | 5 | 6 | VI-2 | Tmem106b |
| 8049 | 3 | 4 | 5 | 6 | VI-2 | Tmem115 |
| 8050 | 3 | 4 | 5 | 6 | VI-2 | Tmem117 |
| 8051 | 3 | 4 | 5 | 6 | VI-2 | Tmem129 |
| 8052 | 3 | 4 | 5 | 6 | VI-2 | Tmem132c |
| 8053 | 3 | 4 | 5 | 6 | VI-2 | Tmem135 |
| 8054 | 3 | 4 | 5 | 6 | VI-2 | Tmem138 |
| 8055 | 3 | 4 | 5 | 6 | VI-2 | Tmem150a |
| 8056 | 3 | 4 | 5 | 6 | VI-2 | Tmem150c |
| 8057 | 3 | 4 | 5 | 6 | VI-2 | Tmem154 |
| 8058 | 3 | 4 | 5 | 6 | VI-2 | Tmem158 |
| 8059 | 3 | 4 | 5 | 6 | VI-2 | Tmem163 |
| 8060 | 3 | 4 | 5 | 6 | VI-2 | Tmem165 |
| 8061 | 3 | 4 | 5 | 6 | VI-2 | Tmem17 |
| 8062 | 3 | 4 | 5 | 6 | VI-2 | Tmem175 |

Fig. 34 - 43

| | | | | | | | |
|---|---|---|---|---|---|---|---|
| 8063 | 3 | 4 | 5 | 6 | | VI-2 | Tmem180 |
| 8064 | 3 | 4 | 5 | 6 | | VI-2 | Tmem181a |
| 8065 | 3 | 4 | 5 | 6 | | VI-2 | Tmem181c-ps |
| 8066 | 3 | 4 | 5 | 6 | | VI-2 | Tmem184b |
| 8067 | 3 | 4 | 5 | 6 | | VI-2 | Tmem186 |
| 8068 | 3 | 4 | 5 | 6 | | VI-2 | Tmem194 |
| 8069 | 3 | 4 | 5 | 6 | | VI-2 | Tmem196 |
| 8070 | 3 | 4 | 5 | 6 | | VI-2 | Tmem215 |
| 8071 | 3 | 4 | 5 | 6 | | VI-2 | Tmem216 |
| 8072 | 3 | 4 | 5 | 6 | | VI-2 | Tmem218 |
| 8073 | 3 | 4 | 5 | 6 | | VI-2 | Tmem220 |
| 8074 | 3 | 4 | 5 | 6 | | VI-2 | Tmem222 |
| 8075 | 3 | 4 | 5 | 6 | | VI-2 | Tmem225 |
| 8076 | 3 | 4 | 5 | 6 | | VI-2 | Tmem229b |
| 8077 | 3 | 4 | 5 | 6 | | VI-2 | Tmem231 |
| 8078 | 3 | 4 | 5 | 6 | | VI-2 | Tmem237 |
| 8079 | 3 | 4 | 5 | 6 | | VI-2 | Tmem253 |
| 8080 | 3 | 4 | 5 | 6 | | VI-2 | Tmem29 |
| 8081 | 3 | 4 | 5 | 6 | | VI-2 | Tmem30a |
| 8082 | 3 | 4 | 5 | 6 | | VI-2 | Tmem30c |
| 8083 | 3 | 4 | 5 | 6 | | VI-2 | Tmem33 |
| 8084 | 3 | 4 | 5 | 6 | | VI-2 | Tmem39a |
| 8085 | 3 | 4 | 5 | 6 | | VI-2 | Tmem39b |
| 8086 | 3 | 4 | 5 | 6 | | VI-2 | Tmem50b |
| 8087 | 3 | 4 | 5 | 6 | | VI-2 | Tmem51 |
| 8088 | 3 | 4 | 5 | 6 | | VI-2 | Tmem64 |
| 8089 | 3 | 4 | 5 | 6 | | VI-2 | Tmem67 |
| 8090 | 3 | 4 | 5 | 6 | | VI-2 | Tmem70 |
| 8091 | 3 | 4 | 5 | 6 | | VI-2 | Tmem79 |
| 8092 | 3 | 4 | 5 | 6 | | VI-2 | Tmem80 |
| 8093 | 3 | 4 | 5 | 6 | | VI-2 | Tmem86a |
| 8094 | 3 | 4 | 5 | 6 | | VI-2 | Tmem87a |
| 8095 | 3 | 4 | 5 | 6 | | VI-2 | Tmem8b |
| 8096 | 3 | 4 | 5 | 6 | | VI-2 | Tmem98 |
| 8097 | 3 | 4 | 5 | 6 | | VI-2 | Tmie |
| 8098 | 3 | 4 | 5 | 6 | | VI-2 | Tmppe |
| 8099 | 3 | 4 | 5 | 6 | | VI-2 | Tmprss11e |
| 8100 | 3 | 4 | 5 | 6 | | VI-2 | Tmprss11f |
| 8101 | 3 | 4 | 5 | 6 | | VI-2 | Tmprss12 |
| 8102 | 3 | 4 | 5 | 6 | | VI-2 | Tmprss4 |
| 8103 | 3 | 4 | 5 | 6 | | VI-2 | Tmprss5 |
| 8104 | 3 | 4 | 5 | 6 | | VI-2 | Tmtc1 |
| 8105 | 3 | 4 | 5 | 6 | | VI-2 | Tmtc2 |
| 8106 | 3 | 4 | 5 | 6 | | VI-2 | Tmx4 |
| 8107 | 3 | 4 | 5 | 6 | | VI-2 | Tnc |
| 8108 | 3 | 4 | 5 | 6 | | VI-2 | Tnf |
| 8109 | 3 | 4 | 5 | 6 | | VI-2 | Tnfaip3 |
| 8110 | 3 | 4 | 5 | 6 | | VI-2 | Tnfrsf11a |
| 8111 | 3 | 4 | 5 | 6 | | VI-2 | Tnfrsf13b |
| 8112 | 3 | 4 | 5 | 6 | | VI-2 | Tnfrsf17 |
| 8113 | 3 | 4 | 5 | 6 | | VI-2 | Tnfrsf22 |
| 8114 | 3 | 4 | 5 | 6 | | VI-2 | Tnfrsf8 |
| 8115 | 3 | 4 | 5 | 6 | | VI-2 | Tnfrsf9 |
| 8116 | 3 | 4 | 5 | 6 | | VI-2 | Tnfsf11 |
| 8117 | 3 | 4 | 5 | 6 | | VI-2 | Tnfsf8 |
| 8118 | 3 | 4 | 5 | 6 | | VI-2 | Tnk2 |
| 8119 | 3 | 4 | 5 | 6 | | VI-2 | Tnk2os |
| 8120 | 3 | 4 | 5 | 6 | | VI-2 | Tnpo3 |
| 8121 | 3 | 4 | 5 | 6 | | VI-2 | Tob1 |
| 8122 | 3 | 4 | 5 | 6 | | VI-2 | Tob2 |
| 8123 | 3 | 4 | 5 | 6 | | VI-2 | Tom1l2 |
| 8124 | 3 | 4 | 5 | 6 | | VI-2 | Tomm22 |
| 8125 | 3 | 4 | 5 | 6 | | VI-2 | Tomm6os |
| 8126 | 3 | 4 | 5 | 6 | | VI-2 | Tomt |
| 8127 | 3 | 4 | 5 | 6 | | VI-2 | Tonsl |
| 8128 | 3 | 4 | 5 | 6 | | VI-2 | Top2a |
| 8129 | 3 | 4 | 5 | 6 | | VI-2 | Top2b |
| 8130 | 3 | 4 | 5 | 6 | | VI-2 | Top3b |
| 8131 | 3 | 4 | 5 | 6 | | VI-2 | Topors |
| 8132 | 3 | 4 | 5 | 6 | | VI-2 | Toporsl |
| 8133 | 3 | 4 | 5 | 6 | | VI-2 | Tor1aip2 |
| 8134 | 3 | 4 | 5 | 6 | | VI-2 | Tor4a |
| 8135 | 3 | 4 | 5 | 6 | | VI-2 | Tpcn1 |
| 8136 | 3 | 4 | 5 | 6 | | VI-2 | Tpd52 |
| 8137 | 3 | 4 | 5 | 6 | | VI-2 | Tpp1 |
| 8138 | 3 | 4 | 5 | 6 | | VI-2 | Tpp2 |
| 8139 | 3 | 4 | 5 | 6 | | VI-2 | Tpr |
| 8140 | 3 | 4 | 5 | 6 | | VI-2 | Tpst1 |
| 8141 | 3 | 4 | 5 | 6 | | VI-2 | Tpst2 |
| 8142 | 3 | 4 | 5 | 6 | | VI-2 | Tpx2 |
| 8143 | 3 | 4 | 5 | 6 | | VI-2 | Trabd2b |
| 8144 | 3 | 4 | 5 | 6 | | VI-2 | Traf3 |
| 8145 | 3 | 4 | 5 | 6 | | VI-2 | Traf3ip3 |
| 8146 | 3 | 4 | 5 | 6 | | VI-2 | Traf4 |
| 8147 | 3 | 4 | 5 | 6 | | VI-2 | Trak2 |
| 8148 | 3 | 4 | 5 | 6 | | VI-2 | Trap1a |
| 8149 | 3 | 4 | 5 | 6 | | VI-2 | Trappc13 |
| 8150 | 3 | 4 | 5 | 6 | | VI-2 | Trat1 |
| 8151 | 3 | 4 | 5 | 6 | | VI-2 | Trdmt1 |
| 8152 | 3 | 4 | 5 | 6 | | VI-2 | Trdn |
| 8153 | 3 | 4 | 5 | 6 | | VI-2 | Treml4 |
| 8154 | 3 | 4 | 5 | 6 | | VI-2 | Trex2 |
| 8155 | 3 | 4 | 5 | 6 | | VI-2 | Trh |
| 8156 | 3 | 4 | 5 | 6 | | VI-2 | Trib2 |
| 8157 | 3 | 4 | 5 | 6 | | VI-2 | Trim16 |
| 8158 | 3 | 4 | 5 | 6 | | VI-2 | Trim21 |
| 8159 | 3 | 4 | 5 | 6 | | VI-2 | Trim27 |
| 8160 | 3 | 4 | 5 | 6 | | VI-2 | Trim3 |
| 8161 | 3 | 4 | 5 | 6 | | VI-2 | Trim32 |
| 8162 | 3 | 4 | 5 | 6 | | VI-2 | Trim35 |
| 8163 | 3 | 4 | 5 | 6 | | VI-2 | Trim39 |
| 8164 | 3 | 4 | 5 | 6 | | VI-2 | Trim44 |
| 8165 | 3 | 4 | 5 | 6 | | VI-2 | Trim58 |
| 8166 | 3 | 4 | 5 | 6 | | VI-2 | Trim6 |
| 8167 | 3 | 4 | 5 | 6 | | VI-2 | Trim62 |
| 8168 | 3 | 4 | 5 | 6 | | VI-2 | Trim65 |
| 8169 | 3 | 4 | 5 | 6 | | VI-2 | Trim69 |
| 8170 | 3 | 4 | 5 | 6 | | VI-2 | Trip13 |
| 8171 | 3 | 4 | 5 | 6 | | VI-2 | Trip6 |
| 8172 | 3 | 4 | 5 | 6 | | VI-2 | Triqk |
| 8173 | 3 | 4 | 5 | 6 | | VI-2 | Trmt10a |
| 8174 | 3 | 4 | 5 | 6 | | VI-2 | Trmt2b |
| 8175 | 3 | 4 | 5 | 6 | | VI-2 | Trmt5 |
| 8176 | 3 | 4 | 5 | 6 | | VI-2 | Troap |
| 8177 | 3 | 4 | 5 | 6 | | VI-2 | Trp53bp1 |
| 8178 | 3 | 4 | 5 | 6 | | VI-2 | Trp53rk |
| 8179 | 3 | 4 | 5 | 6 | | VI-2 | Trp53tg5 |
| 8180 | 3 | 4 | 5 | 6 | | VI-2 | Trp73 |
| 8181 | 3 | 4 | 5 | 6 | | VI-2 | Trpc6 |
| 8182 | 3 | 4 | 5 | 6 | | VI-2 | Trps1 |
| 8183 | 3 | 4 | 5 | 6 | | VI-2 | Trrap |
| 8184 | 3 | 4 | 5 | 6 | | VI-2 | Trub1 |
| 8185 | 3 | 4 | 5 | 6 | | VI-2 | Tsfm |
| 8186 | 3 | 4 | 5 | 6 | | VI-2 | Tsga10 |
| 8187 | 3 | 4 | 5 | 6 | | VI-2 | Tslp |
| 8188 | 3 | 4 | 5 | 6 | | VI-2 | Tsnax |
| 8189 | 3 | 4 | 5 | 6 | | VI-2 | Tspan14 |
| 8190 | 3 | 4 | 5 | 6 | | VI-2 | Tspan2 |
| 8191 | 3 | 4 | 5 | 6 | | VI-2 | Tspan3 |
| 8192 | 3 | 4 | 5 | 6 | | VI-2 | Tspan6 |
| 8193 | 3 | 4 | 5 | 6 | | VI-2 | Tspyl1 |
| 8194 | 3 | 4 | 5 | 6 | | VI-2 | Tspyl3 |
| 8195 | 3 | 4 | 5 | 6 | | VI-2 | Tsr1 |
| 8196 | 3 | 4 | 5 | 6 | | VI-2 | Tst |
| 8197 | 3 | 4 | 5 | 6 | | VI-2 | Ttc12 |
| 8198 | 3 | 4 | 5 | 6 | | VI-2 | Ttc21b |
| 8199 | 3 | 4 | 5 | 6 | | VI-2 | Ttc23l |
| 8200 | 3 | 4 | 5 | 6 | | VI-2 | Ttc28 |
| 8201 | 3 | 4 | 5 | 6 | | VI-2 | Ttc30a2 |
| 8202 | 3 | 4 | 5 | 6 | | VI-2 | Ttc37 |
| 8203 | 3 | 4 | 5 | 6 | | VI-2 | Ttc39b |
| 8204 | 3 | 4 | 5 | 6 | | VI-2 | Ttc7 |
| 8205 | 3 | 4 | 5 | 6 | | VI-2 | Ttc7b |
| 8206 | 3 | 4 | 5 | 6 | | VI-2 | Ttf1 |
| 8207 | 3 | 4 | 5 | 6 | | VI-2 | Tti1 |
| 8208 | 3 | 4 | 5 | 6 | | VI-2 | Tti2 |
| 8209 | 3 | 4 | 5 | 6 | | VI-2 | Ttyh2 |
| 8210 | 3 | 4 | 5 | 6 | | VI-2 | Tuba1a |
| 8211 | 3 | 4 | 5 | 6 | | VI-2 | Tuba1b |
| 8212 | 3 | 4 | 5 | 6 | | VI-2 | Tubb1 |
| 8213 | 3 | 4 | 5 | 6 | | VI-2 | Tubb5 |
| 8214 | 3 | 4 | 5 | 6 | | VI-2 | Tubd1 |
| 8215 | 3 | 4 | 5 | 6 | | VI-2 | Tubgcp3 |
| 8216 | 3 | 4 | 5 | 6 | | VI-2 | Tubgcp5 |
| 8217 | 3 | 4 | 5 | 6 | | VI-2 | Tulp4 |
| 8218 | 3 | 4 | 5 | 6 | | VI-2 | Tvp23b |
| 8219 | 3 | 4 | 5 | 6 | | VI-2 | Twist2 |
| 8220 | 3 | 4 | 5 | 6 | | VI-2 | Txndc5 |
| 8221 | 3 | 4 | 5 | 6 | | VI-2 | Txnrd3 |
| 8222 | 3 | 4 | 5 | 6 | | VI-2 | Tyms-ps |
| 8223 | 3 | 4 | 5 | 6 | | VI-2 | Tyw3 |
| 8224 | 3 | 4 | 5 | 6 | | VI-2 | U2af2 |
| 8225 | 3 | 4 | 5 | 6 | | VI-2 | Uba2 |
| 8226 | 3 | 4 | 5 | 6 | | VI-2 | Uba6 |
| 8227 | 3 | 4 | 5 | 6 | | VI-2 | Ubac2 |
| 8228 | 3 | 4 | 5 | 6 | | VI-2 | Ubap1 |
| 8229 | 3 | 4 | 5 | 6 | | VI-2 | Ube2e1 |
| 8230 | 3 | 4 | 5 | 6 | | VI-2 | Ube2n |
| 8231 | 3 | 4 | 5 | 6 | | VI-2 | Ube2q1 |
| 8232 | 3 | 4 | 5 | 6 | | VI-2 | Ube2u |
| 8233 | 3 | 4 | 5 | 6 | | VI-2 | Ube2v2 |
| 8234 | 3 | 4 | 5 | 6 | | VI-2 | Ube4a |
| 8235 | 3 | 4 | 5 | 6 | | VI-2 | Ubn1 |
| 8236 | 3 | 4 | 5 | 6 | | VI-2 | Ubox5 |
| 8237 | 3 | 4 | 5 | 6 | | VI-2 | Ubr3 |
| 8238 | 3 | 4 | 5 | 6 | | VI-2 | Ubxn2b |
| 8239 | 3 | 4 | 5 | 6 | | VI-2 | Ucn |
| 8240 | 3 | 4 | 5 | 6 | | VI-2 | Ucn3 |
| 8241 | 3 | 4 | 5 | 6 | | VI-2 | Ufl1 |
| 8242 | 3 | 4 | 5 | 6 | | VI-2 | Ugp2 |
| 8243 | 3 | 4 | 5 | 6 | | VI-2 | Ugt1a2 |
| 8244 | 3 | 4 | 5 | 6 | | VI-2 | Ugt1a9 |
| 8245 | 3 | 4 | 5 | 6 | | VI-2 | Ugt2a3 |
| 8246 | 3 | 4 | 5 | 6 | | VI-2 | Uhrf2 |
| 8247 | 3 | 4 | 5 | 6 | | VI-2 | Uimc1 |
| 8248 | 3 | 4 | 5 | 6 | | VI-2 | Ulbp1 |
| 8249 | 3 | 4 | 5 | 6 | | VI-2 | Unc119b |
| 8250 | 3 | 4 | 5 | 6 | | VI-2 | Unc13c |
| 8251 | 3 | 4 | 5 | 6 | | VI-2 | Unc50 |
| 8252 | 3 | 4 | 5 | 6 | | VI-2 | Ung |
| 8253 | 3 | 4 | 5 | 6 | | VI-2 | Upk3a |
| 8254 | 3 | 4 | 5 | 6 | | VI-2 | Uqcrc2 |

Fig. 34 - 44

| | | | | | | | |
|---|---|---|---|---|---|---|---|
| 8255 | 3 | 4 | 5 | 6 | | VI-2 | Uqcrfs1 |
| 8256 | 3 | 4 | 5 | 6 | | VI-2 | Urb1 |
| 8257 | 3 | 4 | 5 | 6 | | VI-2 | Urb2 |
| 8258 | 3 | 4 | 5 | 6 | | VI-2 | Urgcp |
| 8259 | 3 | 4 | 5 | 6 | | VI-2 | Usb1 |
| 8260 | 3 | 4 | 5 | 6 | | VI-2 | Ushbp1 |
| 8261 | 3 | 4 | 5 | 6 | | VI-2 | Uso1 |
| 8262 | 3 | 4 | 5 | 6 | | VI-2 | Usp11 |
| 8263 | 3 | 4 | 5 | 6 | | VI-2 | Usp14 |
| 8264 | 3 | 4 | 5 | 6 | | VI-2 | Usp15 |
| 8265 | 3 | 4 | 5 | 6 | | VI-2 | Usp25 |
| 8266 | 3 | 4 | 5 | 6 | | VI-2 | Usp27x |
| 8267 | 3 | 4 | 5 | 6 | | VI-2 | Usp31 |
| 8268 | 3 | 4 | 5 | 6 | | VI-2 | Usp34 |
| 8269 | 3 | 4 | 5 | 6 | | VI-2 | Usp38 |
| 8270 | 3 | 4 | 5 | 6 | | VI-2 | Usp42 |
| 8271 | 3 | 4 | 5 | 6 | | VI-2 | Usp46 |
| 8272 | 3 | 4 | 5 | 6 | | VI-2 | Usp6nl |
| 8273 | 3 | 4 | 5 | 6 | | VI-2 | Usp9x |
| 8274 | 3 | 4 | 5 | 6 | | VI-2 | Utp14b |
| 8275 | 3 | 4 | 5 | 6 | | VI-2 | Utp15 |
| 8276 | 3 | 4 | 5 | 6 | | VI-2 | Utp18 |
| 8277 | 3 | 4 | 5 | 6 | | VI-2 | Vangl2 |
| 8278 | 3 | 4 | 5 | 6 | | VI-2 | Vapb |
| 8279 | 3 | 4 | 5 | 6 | | VI-2 | Vcpip1 |
| 8280 | 3 | 4 | 5 | 6 | | VI-2 | Vdac1 |
| 8281 | 3 | 4 | 5 | 6 | | VI-2 | Vegfb |
| 8282 | 3 | 4 | 5 | 6 | | VI-2 | Vegfc |
| 8283 | 3 | 4 | 5 | 6 | | VI-2 | Vkorc1l1 |
| 8284 | 3 | 4 | 5 | 6 | | VI-2 | Vma21 |
| 8285 | 3 | 4 | 5 | 6 | | VI-2 | Vmn2r-ps11 |
| 8286 | 3 | 4 | 5 | 6 | | VI-2 | Vmn2r84 |
| 8287 | 3 | 4 | 5 | 6 | | VI-2 | Vprbp |
| 8288 | 3 | 4 | 5 | 6 | | VI-2 | Vps11 |
| 8289 | 3 | 4 | 5 | 6 | | VI-2 | Vps13d |
| 8290 | 3 | 4 | 5 | 6 | | VI-2 | Vps26a |
| 8291 | 3 | 4 | 5 | 6 | | VI-2 | Vps33b |
| 8292 | 3 | 4 | 5 | 6 | | VI-2 | Vps37a |
| 8293 | 3 | 4 | 5 | 6 | | VI-2 | Vps39 |
| 8294 | 3 | 4 | 5 | 6 | | VI-2 | Vps54 |
| 8295 | 3 | 4 | 5 | 6 | | VI-2 | Vps72 |
| 8296 | 3 | 4 | 5 | 6 | | VI-2 | Vsig1 |
| 8297 | 3 | 4 | 5 | 6 | | VI-2 | Vsig10l |
| 8298 | 3 | 4 | 5 | 6 | | VI-2 | Vstm4 |
| 8299 | 3 | 4 | 5 | 6 | | VI-2 | Vsx1 |
| 8300 | 3 | 4 | 5 | 6 | | VI-2 | Vti1a |
| 8301 | 3 | 4 | 5 | 6 | | VI-2 | Vwa9 |
| 8302 | 3 | 4 | 5 | 6 | | VI-2 | Was |
| 8303 | 3 | 4 | 5 | 6 | | VI-2 | Wbp2 |
| 8304 | 3 | 4 | 5 | 6 | | VI-2 | Wdfy2 |
| 8305 | 3 | 4 | 5 | 6 | | VI-2 | Wdfy3 |
| 8306 | 3 | 4 | 5 | 6 | | VI-2 | Wdhd1 |
| 8307 | 3 | 4 | 5 | 6 | | VI-2 | Wdr11 |
| 8308 | 3 | 4 | 5 | 6 | | VI-2 | Wdr12 |
| 8309 | 3 | 4 | 5 | 6 | | VI-2 | Wdr13 |
| 8310 | 3 | 4 | 5 | 6 | | VI-2 | Wdr24 |
| 8311 | 3 | 4 | 5 | 6 | | VI-2 | Wdr37 |
| 8312 | 3 | 4 | 5 | 6 | | VI-2 | Wdr41 |
| 8313 | 3 | 4 | 5 | 6 | | VI-2 | Wdr5b |
| 8314 | 3 | 4 | 5 | 6 | | VI-2 | Wdr6 |
| 8315 | 3 | 4 | 5 | 6 | | VI-2 | Wdr61 |
| 8316 | 3 | 4 | 5 | 6 | | VI-2 | Wdr72 |
| 8317 | 3 | 4 | 5 | 6 | | VI-2 | Wdr76 |
| 8318 | 3 | 4 | 5 | 6 | | VI-2 | Wdr78 |
| 8319 | 3 | 4 | 5 | 6 | | VI-2 | Wdr82 |
| 8320 | 3 | 4 | 5 | 6 | | VI-2 | Wfdc8 |
| 8321 | 3 | 4 | 5 | 6 | | VI-2 | Wfdc9 |
| 8322 | 3 | 4 | 5 | 6 | | VI-2 | Whamm |
| 8323 | 3 | 4 | 5 | 6 | | VI-2 | Whrn |
| 8324 | 3 | 4 | 5 | 6 | | VI-2 | Whsc1 |
| 8325 | 3 | 4 | 5 | 6 | | VI-2 | Wipf2 |
| 8326 | 3 | 4 | 5 | 6 | | VI-2 | Wisp1 |
| 8327 | 3 | 4 | 5 | 6 | | VI-2 | Wnk1 |
| 8328 | 3 | 4 | 5 | 6 | | VI-2 | Wnt10b |
| 8329 | 3 | 4 | 5 | 6 | | VI-2 | Wnt2b |
| 8330 | 3 | 4 | 5 | 6 | | VI-2 | Wnt3a |
| 8331 | 3 | 4 | 5 | 6 | | VI-2 | Wnt6 |
| 8332 | 3 | 4 | 5 | 6 | | VI-2 | Wnt7a |
| 8333 | 3 | 4 | 5 | 6 | | VI-2 | Wrb |
| 8334 | 3 | 4 | 5 | 6 | | VI-2 | Wscd1 |
| 8335 | 3 | 4 | 5 | 6 | | VI-2 | Wscd2 |
| 8336 | 3 | 4 | 5 | 6 | | VI-2 | Wtap |
| 8337 | 3 | 4 | 5 | 6 | | VI-2 | Wwc2 |
| 8338 | 3 | 4 | 5 | 6 | | VI-2 | Wwox |
| 8339 | 3 | 4 | 5 | 6 | | VI-2 | Wwp1 |
| 8340 | 3 | 4 | 5 | 6 | | VI-2 | Wwtr1 |
| 8341 | 3 | 4 | 5 | 6 | | VI-2 | Xcr1 |
| 8342 | 3 | 4 | 5 | 6 | | VI-2 | Xkr8 |
| 8343 | 3 | 4 | 5 | 6 | | VI-2 | Xkrx |
| 8344 | 3 | 4 | 5 | 6 | | VI-2 | Xpo7 |
| 8345 | 3 | 4 | 5 | 6 | | VI-2 | Xrcc2 |
| 8346 | 3 | 4 | 5 | 6 | | VI-2 | Xrn1 |
| 8347 | 3 | 4 | 5 | 6 | | VI-2 | Xrra1 |
| 8348 | 3 | 4 | 5 | 6 | | VI-2 | Yae1d1 |
| 8349 | 3 | 4 | 5 | 6 | | VI-2 | Yap1 |
| 8350 | 3 | 4 | 5 | 6 | | VI-2 | Yars2 |
| 8351 | 3 | 4 | 5 | 6 | | VI-2 | Ydjc |
| 8352 | 3 | 4 | 5 | 6 | | VI-2 | Yipf5 |
| 8353 | 3 | 4 | 5 | 6 | | VI-2 | Ykt6 |
| 8354 | 3 | 4 | 5 | 6 | | VI-2 | Ylpm1 |
| 8355 | 3 | 4 | 5 | 6 | | VI-2 | Ythdc1 |
| 8356 | 3 | 4 | 5 | 6 | | VI-2 | Ythdc2 |
| 8357 | 3 | 4 | 5 | 6 | | VI-2 | Ywhag |
| 8358 | 3 | 4 | 5 | 6 | | VI-2 | Zak |
| 8359 | 3 | 4 | 5 | 6 | | VI-2 | Zbed4 |
| 8360 | 3 | 4 | 5 | 6 | | VI-2 | Zbtb14 |
| 8361 | 3 | 4 | 5 | 6 | | VI-2 | Zbtb34 |
| 8362 | 3 | 4 | 5 | 6 | | VI-2 | Zbtb37 |
| 8363 | 3 | 4 | 5 | 6 | | VI-2 | Zbtb43 |
| 8364 | 3 | 4 | 5 | 6 | | VI-2 | Zbtb49 |
| 8365 | 3 | 4 | 5 | 6 | | VI-2 | Zbtb5 |
| 8366 | 3 | 4 | 5 | 6 | | VI-2 | Zbtb7a |
| 8367 | 3 | 4 | 5 | 6 | | VI-2 | Zbtb7b |
| 8368 | 3 | 4 | 5 | 6 | | VI-2 | Zbtb7c |
| 8369 | 3 | 4 | 5 | 6 | | VI-2 | Zbtb8a |
| 8370 | 3 | 4 | 5 | 6 | | VI-2 | Zbtb8 |
| 8371 | 3 | 4 | 5 | 6 | | VI-2 | Zc3h18 |
| 8372 | 3 | 4 | 5 | 6 | | VI-2 | Zc3h7b |
| 8373 | 3 | 4 | 5 | 6 | | VI-2 | Zc3h8 |
| 8374 | 3 | 4 | 5 | 6 | | VI-2 | Zc3hav1l |
| 8375 | 3 | 4 | 5 | 6 | | VI-2 | Zc4h2 |
| 8376 | 3 | 4 | 5 | 6 | | VI-2 | Zcchc10 |
| 8377 | 3 | 4 | 5 | 6 | | VI-2 | Zcchc11 |
| 8378 | 3 | 4 | 5 | 6 | | VI-2 | Zcchc3 |
| 8379 | 3 | 4 | 5 | 6 | | VI-2 | Zcchc4 |
| 8380 | 3 | 4 | 5 | 6 | | VI-2 | Zdhhc11 |
| 8381 | 3 | 4 | 5 | 6 | | VI-2 | Zdhhc17 |
| 8382 | 3 | 4 | 5 | 6 | | VI-2 | Zdhhc24 |
| 8383 | 3 | 4 | 5 | 6 | | VI-2 | Zdhhc6 |
| 8384 | 3 | 4 | 5 | 6 | | VI-2 | Zdhhc8 |
| 8385 | 3 | 4 | 5 | 6 | | VI-2 | Zdhhc9 |
| 8386 | 3 | 4 | 5 | 6 | | VI-2 | Zeb1 |
| 8387 | 3 | 4 | 5 | 6 | | VI-2 | Zf12 |
| 8388 | 3 | 4 | 5 | 6 | | VI-2 | Zfhx3 |
| 8389 | 3 | 4 | 5 | 6 | | VI-2 | Zfp1 |
| 8390 | 3 | 4 | 5 | 6 | | VI-2 | Zfp101 |
| 8391 | 3 | 4 | 5 | 6 | | VI-2 | Zfp106 |
| 8392 | 3 | 4 | 5 | 6 | | VI-2 | Zfp109 |
| 8393 | 3 | 4 | 5 | 6 | | VI-2 | Zfp12 |
| 8394 | 3 | 4 | 5 | 6 | | VI-2 | Zfp131 |
| 8395 | 3 | 4 | 5 | 6 | | VI-2 | Zfp142 |
| 8396 | 3 | 4 | 5 | 6 | | VI-2 | Zfp148 |
| 8397 | 3 | 4 | 5 | 6 | | VI-2 | Zfp169 |
| 8398 | 3 | 4 | 5 | 6 | | VI-2 | Zfp180 |
| 8399 | 3 | 4 | 5 | 6 | | VI-2 | Zfp185 |
| 8400 | 3 | 4 | 5 | 6 | | VI-2 | Zfp191 |
| 8401 | 3 | 4 | 5 | 6 | | VI-2 | Zfp235 |
| 8402 | 3 | 4 | 5 | 6 | | VI-2 | Zfp236 |
| 8403 | 3 | 4 | 5 | 6 | | VI-2 | Zfp239 |
| 8404 | 3 | 4 | 5 | 6 | | VI-2 | Zfp251 |
| 8405 | 3 | 4 | 5 | 6 | | VI-2 | Zfp26 |
| 8406 | 3 | 4 | 5 | 6 | | VI-2 | Zfp263 |
| 8407 | 3 | 4 | 5 | 6 | | VI-2 | Zfp27 |
| 8408 | 3 | 4 | 5 | 6 | | VI-2 | Zfp276 |
| 8409 | 3 | 4 | 5 | 6 | | VI-2 | Zfp280b |
| 8410 | 3 | 4 | 5 | 6 | | VI-2 | Zfp30 |
| 8411 | 3 | 4 | 5 | 6 | | VI-2 | Zfp316 |
| 8412 | 3 | 4 | 5 | 6 | | VI-2 | Zfp319 |
| 8413 | 3 | 4 | 5 | 6 | | VI-2 | Zfp322a |
| 8414 | 3 | 4 | 5 | 6 | | VI-2 | Zfp324 |
| 8415 | 3 | 4 | 5 | 6 | | VI-2 | Zfp329 |
| 8416 | 3 | 4 | 5 | 6 | | VI-2 | Zfp346 |
| 8417 | 3 | 4 | 5 | 6 | | VI-2 | Zfp369 |
| 8418 | 3 | 4 | 5 | 6 | | VI-2 | Zfp382 |
| 8419 | 3 | 4 | 5 | 6 | | VI-2 | Zfp384 |
| 8420 | 3 | 4 | 5 | 6 | | VI-2 | Zfp386 |
| 8421 | 3 | 4 | 5 | 6 | | VI-2 | Zfp40 |
| 8422 | 3 | 4 | 5 | 6 | | VI-2 | Zfp41 |
| 8423 | 3 | 4 | 5 | 6 | | VI-2 | Zfp433 |
| 8424 | 3 | 4 | 5 | 6 | | VI-2 | Zfp438 |
| 8425 | 3 | 4 | 5 | 6 | | VI-2 | Zfp449 |
| 8426 | 3 | 4 | 5 | 6 | | VI-2 | Zfp451 |
| 8427 | 3 | 4 | 5 | 6 | | VI-2 | Zfp467 |
| 8428 | 3 | 4 | 5 | 6 | | VI-2 | Zfp507 |
| 8429 | 3 | 4 | 5 | 6 | | VI-2 | Zfp513 |
| 8430 | 3 | 4 | 5 | 6 | | VI-2 | Zfp518b |
| 8431 | 3 | 4 | 5 | 6 | | VI-2 | Zfp523 |
| 8432 | 3 | 4 | 5 | 6 | | VI-2 | Zfp53 |
| 8433 | 3 | 4 | 5 | 6 | | VI-2 | Zfp532 |
| 8434 | 3 | 4 | 5 | 6 | | VI-2 | Zfp534 |
| 8435 | 3 | 4 | 5 | 6 | | VI-2 | Zfp54 |
| 8436 | 3 | 4 | 5 | 6 | | VI-2 | Zfp541 |
| 8437 | 3 | 4 | 5 | 6 | | VI-2 | Zfp551 |
| 8438 | 3 | 4 | 5 | 6 | | VI-2 | Zfp563 |
| 8439 | 3 | 4 | 5 | 6 | | VI-2 | Zfp566 |
| 8440 | 3 | 4 | 5 | 6 | | VI-2 | Zfp568 |
| 8441 | 3 | 4 | 5 | 6 | | VI-2 | Zfp574 |
| 8442 | 3 | 4 | 5 | 6 | | VI-2 | Zfp579 |
| 8443 | 3 | 4 | 5 | 6 | | VI-2 | Zfp59 |
| 8444 | 3 | 4 | 5 | 6 | | VI-2 | Zfp597 |
| 8445 | 3 | 4 | 5 | 6 | | VI-2 | Zfp599 |
| 8446 | 3 | 4 | 5 | 6 | | VI-2 | Zfp60 |

Fig. 34 - 45

| | | | | | | |
|---|---|---|---|---|---|---|
| 8447 | 3 | 4 | 5 | 6 | VI-2 | Zfp606 |
| 8448 | 3 | 4 | 5 | 6 | VI-2 | Zfp607 |
| 8449 | 3 | 4 | 5 | 6 | VI-2 | Zfp609 |
| 8450 | 3 | 4 | 5 | 6 | VI-2 | Zfp618 |
| 8451 | 3 | 4 | 5 | 6 | VI-2 | Zfp64 |
| 8452 | 3 | 4 | 5 | 6 | VI-2 | Zfp641 |
| 8453 | 3 | 4 | 5 | 6 | VI-2 | Zfp647 |
| 8454 | 3 | 4 | 5 | 6 | VI-2 | Zfp653 |
| 8455 | 3 | 4 | 5 | 6 | VI-2 | Zfp654 |
| 8456 | 3 | 4 | 5 | 6 | VI-2 | Zfp661 |
| 8457 | 3 | 4 | 5 | 6 | VI-2 | Zfp663 |
| 8458 | 3 | 4 | 5 | 6 | VI-2 | Zfp664 |
| 8459 | 3 | 4 | 5 | 6 | VI-2 | Zfp667 |
| 8460 | 3 | 4 | 5 | 6 | VI-2 | Zfp668 |
| 8461 | 3 | 4 | 5 | 6 | VI-2 | Zfp687 |
| 8462 | 3 | 4 | 5 | 6 | VI-2 | Zfp691 |
| 8463 | 3 | 4 | 5 | 6 | VI-2 | Zfp7 |
| 8464 | 3 | 4 | 5 | 6 | VI-2 | Zfp706 |
| 8465 | 3 | 4 | 5 | 6 | VI-2 | Zfp711 |
| 8466 | 3 | 4 | 5 | 6 | VI-2 | Zfp712 |
| 8467 | 3 | 4 | 5 | 6 | VI-2 | Zfp72 |
| 8468 | 3 | 4 | 5 | 6 | VI-2 | Zfp738 |
| 8469 | 3 | 4 | 5 | 6 | VI-2 | Zfp74 |
| 8470 | 3 | 4 | 5 | 6 | VI-2 | Zfp750 |
| 8471 | 3 | 4 | 5 | 6 | VI-2 | Zfp760 |
| 8472 | 3 | 4 | 5 | 6 | VI-2 | Zfp790 |
| 8473 | 3 | 4 | 5 | 6 | VI-2 | Zfp808 |
| 8474 | 3 | 4 | 5 | 6 | VI-2 | Zfp81 |
| 8475 | 3 | 4 | 5 | 6 | VI-2 | Zfp810 |
| 8476 | 3 | 4 | 5 | 6 | VI-2 | Zfp82 |
| 8477 | 3 | 4 | 5 | 6 | VI-2 | Zfp827 |
| 8478 | 3 | 4 | 5 | 6 | VI-2 | Zfp830 |
| 8479 | 3 | 4 | 5 | 6 | VI-2 | Zfp84 |
| 8480 | 3 | 4 | 5 | 6 | VI-2 | Zfp846 |
| 8481 | 3 | 4 | 5 | 6 | VI-2 | Zfp867 |
| 8482 | 3 | 4 | 5 | 6 | VI-2 | Zfp868 |
| 8483 | 3 | 4 | 5 | 6 | VI-2 | Zfp870 |
| 8484 | 3 | 4 | 5 | 6 | VI-2 | Zfp9 |
| 8485 | 3 | 4 | 5 | 6 | VI-2 | Zfp931 |
| 8486 | 3 | 4 | 5 | 6 | VI-2 | Zfp933 |
| 8487 | 3 | 4 | 5 | 6 | VI-2 | Zfp938 |
| 8488 | 3 | 4 | 5 | 6 | VI-2 | Zfp939 |
| 8489 | 3 | 4 | 5 | 6 | VI-2 | Zfp94 |
| 8490 | 3 | 4 | 5 | 6 | VI-2 | Zfp949 |
| 8491 | 3 | 4 | 5 | 6 | VI-2 | Zfp952 |
| 8492 | 3 | 4 | 5 | 6 | VI-2 | Zfp958 |
| 8493 | 3 | 4 | 5 | 6 | VI-2 | Zfyve20 |
| 8494 | 3 | 4 | 5 | 6 | VI-2 | Zfyve21 |
| 8495 | 3 | 4 | 5 | 6 | VI-2 | Zfyve26 |
| 8496 | 3 | 4 | 5 | 6 | VI-2 | Zgpat |
| 8497 | 3 | 4 | 5 | 6 | VI-2 | Zgrf1 |
| 8498 | 3 | 4 | 5 | 6 | VI-2 | Zhx1 |
| 8499 | 3 | 4 | 5 | 6 | VI-2 | Zhx2 |
| 8500 | 3 | 4 | 5 | 6 | VI-2 | Zic4 |
| 8501 | 3 | 4 | 5 | 6 | VI-2 | Zim3 |
| 8502 | 3 | 4 | 5 | 6 | VI-2 | Zkscan3 |
| 8503 | 3 | 4 | 5 | 6 | VI-2 | Zkscan4 |
| 8504 | 3 | 4 | 5 | 6 | VI-2 | Zkscan8 |
| 8505 | 3 | 4 | 5 | 6 | VI-2 | Zmat3 |
| 8506 | 3 | 4 | 5 | 6 | VI-2 | Zmpste24 |
| 8507 | 3 | 4 | 5 | 6 | VI-2 | Zmym6 |
| 8508 | 3 | 4 | 5 | 6 | VI-2 | Zmynd11 |
| 8509 | 3 | 4 | 5 | 6 | VI-2 | Znhit3 |
| 8510 | 3 | 4 | 5 | 6 | VI-2 | Znrf2 |
| 8511 | 3 | 4 | 5 | 6 | VI-2 | Znrf3 |
| 8512 | 3 | 4 | 5 | 6 | VI-2 | Zpbp |
| 8513 | 3 | 4 | 5 | 6 | VI-2 | Zranb3 |
| 8514 | 3 | 4 | 5 | 6 | VI-2 | Zscan18 |
| 8515 | 3 | 4 | 5 | 6 | VI-2 | Zscan21 |
| 8516 | 3 | 4 | 5 | 6 | VI-2 | Zscan22 |
| 8517 | 3 | 4 | 5 | 6 | VI-2 | Zscan29 |
| 8518 | 3 | 4 | 5 | 6 | VI-2 | Zswim2 |
| 8519 | 3 | 4 | 5 | 6 | VI-2 | Zswim3 |
| 8520 | 3 | 4 | 5 | 6 | VI-2 | Zswim6 |
| 8521 | 3 | 4 | 5 | 6 | VI-2 | Zufsp |
| 8522 | 3 | 4 | 5 | 6 | VI-2 | Zwilch |
| 8523 | 3 | 4 | 5 | 6 | VI-2 | Zyg11b |
| 8524 | 3 | 4 | 5 | 6 | VI-2 | Zzef1 |
| 8525 | 3 | 4 | 5 | 6 | VI-1 | 0610005C13Rik |
| 8526 | 3 | 4 | 5 | 6 | VI-1 | 0610009B22Rik |
| 8527 | 3 | 4 | 5 | 6 | VI-1 | 0610011F06Rik |
| 8528 | 3 | 4 | 5 | 6 | VI-1 | 0610012G03Rik |
| 8529 | 3 | 4 | 5 | 6 | VI-1 | 0610031J06Rik |
| 8530 | 3 | 4 | 5 | 6 | VI-1 | 0610040J01Rik |
| 8531 | 3 | 4 | 5 | 6 | VI-1 | 1010001N08Rik |
| 8532 | 3 | 4 | 5 | 6 | VI-1 | 1110001J03Rik |
| 8533 | 3 | 4 | 5 | 6 | VI-1 | 1110004F10Rik |
| 8534 | 3 | 4 | 5 | 6 | VI-1 | 1110006O24Rik |
| 8535 | 3 | 4 | 5 | 6 | VI-1 | 1110008F13Rik |
| 8536 | 3 | 4 | 5 | 6 | VI-1 | 1110008L16Rik |
| 8537 | 3 | 4 | 5 | 6 | VI-1 | 1110012L19Rik |
| 8538 | 3 | 4 | 5 | 6 | VI-1 | 1110019D14Rik |
| 8539 | 3 | 4 | 5 | 6 | VI-1 | 1110025L11Rik |
| 8540 | 3 | 4 | 5 | 6 | VI-1 | 1110028F11Rik |
| 8541 | 3 | 4 | 5 | 6 | VI-1 | 1110038F14Rik |
| 8542 | 3 | 4 | 5 | 6 | VI-1 | 1110051M20Rik |
| 8543 | 3 | 4 | 5 | 6 | VI-1 | 1110058L19Rik |
| 8544 | 3 | 4 | 5 | 6 | VI-1 | 1110059G10Rik |
| 8545 | 3 | 4 | 5 | 6 | VI-1 | 1300002K09Rik |
| 8546 | 3 | 4 | 5 | 6 | VI-1 | 1300017J02Rik |
| 8547 | 3 | 4 | 5 | 6 | VI-1 | 1500009L16Rik |
| 8548 | 3 | 4 | 5 | 6 | VI-1 | 1500011B03Rik |
| 8549 | 3 | 4 | 5 | 6 | VI-1 | 1500011K16Rik |
| 8550 | 3 | 4 | 5 | 6 | VI-1 | 1500012K07Rik |
| 8551 | 3 | 4 | 5 | 6 | VI-1 | 1500015A07Rik |
| 8552 | 3 | 4 | 5 | 6 | VI-1 | 1600010M07Rik |
| 8553 | 3 | 4 | 5 | 6 | VI-1 | 1600012H06Rik |
| 8554 | 3 | 4 | 5 | 6 | VI-1 | 1600014C10Rik |
| 8555 | 3 | 4 | 5 | 6 | VI-1 | 1600025M17Rik |
| 8556 | 3 | 4 | 5 | 6 | VI-1 | 1700001C19Rik |
| 8557 | 3 | 4 | 5 | 6 | VI-1 | 1700001G11Rik |
| 8558 | 3 | 4 | 5 | 6 | VI-1 | 1700001J03Rik |
| 8559 | 3 | 4 | 5 | 6 | VI-1 | 1700001J11Rik |
| 8560 | 3 | 4 | 5 | 6 | VI-1 | 1700001K19Rik |
| 8561 | 3 | 4 | 5 | 6 | VI-1 | 1700001K23Rik |
| 8562 | 3 | 4 | 5 | 6 | VI-1 | 1700001L19Rik |
| 8563 | 3 | 4 | 5 | 6 | VI-1 | 1700003E24Rik |
| 8564 | 3 | 4 | 5 | 6 | VI-1 | 1700003M02Rik |
| 8565 | 3 | 4 | 5 | 6 | VI-1 | 1700007K09Rik |
| 8566 | 3 | 4 | 5 | 6 | VI-1 | 1700007K13Rik |
| 8567 | 3 | 4 | 5 | 6 | VI-1 | 1700007P06Rik |
| 8568 | 3 | 4 | 5 | 6 | VI-1 | 1700008O03Rik |
| 8569 | 3 | 4 | 5 | 6 | VI-1 | 1700009C05Rik |
| 8570 | 3 | 4 | 5 | 6 | VI-1 | 1700010B08Rik |
| 8571 | 3 | 4 | 5 | 6 | VI-1 | 1700010D01Rik |
| 8572 | 3 | 4 | 5 | 6 | VI-1 | 1700010I14Rik |
| 8573 | 3 | 4 | 5 | 6 | VI-1 | 1700011A15Rik |
| 8574 | 3 | 4 | 5 | 6 | VI-1 | 1700011L22Rik |
| 8575 | 3 | 4 | 5 | 6 | VI-1 | 1700011M02Rik |
| 8576 | 3 | 4 | 5 | 6 | VI-1 | 1700012B07Rik |
| 8577 | 3 | 4 | 5 | 6 | VI-1 | 1700012B09Rik |
| 8578 | 3 | 4 | 5 | 6 | VI-1 | 1700012D01Rik |
| 8579 | 3 | 4 | 5 | 6 | VI-1 | 1700012D14Rik |
| 8580 | 3 | 4 | 5 | 6 | VI-1 | 1700012L04Rik |
| 8581 | 3 | 4 | 5 | 6 | VI-1 | 1700012P22Rik |
| 8582 | 3 | 4 | 5 | 6 | VI-1 | 1700013D24Rik |
| 8583 | 3 | 4 | 5 | 6 | VI-1 | 1700013G24Rik |
| 8584 | 3 | 4 | 5 | 6 | VI-1 | 1700015G11Rik |
| 8585 | 3 | 4 | 5 | 6 | VI-1 | 1700016H13Rik |
| 8586 | 3 | 4 | 5 | 6 | VI-1 | 1700016K19Rik |
| 8587 | 3 | 4 | 5 | 6 | VI-1 | 1700016L04Rik |
| 8588 | 3 | 4 | 5 | 6 | VI-1 | 1700016P04Rik |
| 8589 | 3 | 4 | 5 | 6 | VI-1 | 1700018C11Rik |
| 8590 | 3 | 4 | 5 | 6 | VI-1 | 1700018G05Rik |
| 8591 | 3 | 4 | 5 | 6 | VI-1 | 1700018L02Rik |
| 8592 | 3 | 4 | 5 | 6 | VI-1 | 1700019B03Rik |
| 8593 | 3 | 4 | 5 | 6 | VI-1 | 1700019D03Rik |
| 8594 | 3 | 4 | 5 | 6 | VI-1 | 1700019L03Rik |
| 8595 | 3 | 4 | 5 | 6 | VI-1 | 1700019M22Rik |
| 8596 | 3 | 4 | 5 | 6 | VI-1 | 1700020D05Rik |
| 8597 | 3 | 4 | 5 | 6 | VI-1 | 1700020N01Rik |
| 8598 | 3 | 4 | 5 | 6 | VI-1 | 1700020N18Rik |
| 8599 | 3 | 4 | 5 | 6 | VI-1 | 1700021F05Rik |
| 8600 | 3 | 4 | 5 | 6 | VI-1 | 1700021F07Rik |
| 8601 | 3 | 4 | 5 | 6 | VI-1 | 1700021N21Rik |
| 8602 | 3 | 4 | 5 | 6 | VI-1 | 1700023F06Rik |
| 8603 | 3 | 4 | 5 | 6 | VI-1 | 1700024G13Rik |
| 8604 | 3 | 4 | 5 | 6 | VI-1 | 1700024P04Rik |
| 8605 | 3 | 4 | 5 | 6 | VI-1 | 1700024P16Rik |
| 8606 | 3 | 4 | 5 | 6 | VI-1 | 1700025N23Rik |
| 8607 | 3 | 4 | 5 | 6 | VI-1 | 1700026L06Rik |
| 8608 | 3 | 4 | 5 | 6 | VI-1 | 1700028J19Rik |
| 8609 | 3 | 4 | 5 | 6 | VI-1 | 1700028P14Rik |
| 8610 | 3 | 4 | 5 | 6 | VI-1 | 1700029B22Rik |
| 8611 | 3 | 4 | 5 | 6 | VI-1 | 1700029F12Rik |
| 8612 | 3 | 4 | 5 | 6 | VI-1 | 1700029J07Rik |
| 8613 | 3 | 4 | 5 | 6 | VI-1 | 1700030C10Rik |
| 8614 | 3 | 4 | 5 | 6 | VI-1 | 1700030K09Rik |
| 8615 | 3 | 4 | 5 | 6 | VI-1 | 1700030L20Rik |
| 8616 | 3 | 4 | 5 | 6 | VI-1 | 1700031F05Rik |
| 8617 | 3 | 4 | 5 | 6 | VI-1 | 1700034E13Rik |
| 8618 | 3 | 4 | 5 | 6 | VI-1 | 1700034G24Rik |
| 8619 | 3 | 4 | 5 | 6 | VI-1 | 1700034J05Rik |
| 8620 | 3 | 4 | 5 | 6 | VI-1 | 1700034O15Rik |
| 8621 | 3 | 4 | 5 | 6 | VI-1 | 1700034P13Rik |
| 8622 | 3 | 4 | 5 | 6 | VI-1 | 1700039E15Rik |
| 8623 | 3 | 4 | 5 | 6 | VI-1 | 1700040L02Rik |
| 8624 | 3 | 4 | 5 | 6 | VI-1 | 1700042G07Rik |
| 8625 | 3 | 4 | 5 | 6 | VI-1 | 1700047I17Rik2 |
| 8626 | 3 | 4 | 5 | 6 | VI-1 | 1700048M11Rik |
| 8627 | 3 | 4 | 5 | 6 | VI-1 | 1700054M17Rik |
| 8628 | 3 | 4 | 5 | 6 | VI-1 | 1700054O13Rik |
| 8629 | 3 | 4 | 5 | 6 | VI-1 | 1700055C04Rik |
| 8630 | 3 | 4 | 5 | 6 | VI-1 | 1700056E22Rik |
| 8631 | 3 | 4 | 5 | 6 | VI-1 | 1700057G04Rik |
| 8632 | 3 | 4 | 5 | 6 | VI-1 | 1700060C16Rik |
| 8633 | 3 | 4 | 5 | 6 | VI-1 | 1700060C20Rik |
| 8634 | 3 | 4 | 5 | 6 | VI-1 | 1700065J11Rik |
| 8635 | 3 | 4 | 5 | 6 | VI-1 | 1700065J18Rik |
| 8636 | 3 | 4 | 5 | 6 | VI-1 | 1700066B17Rik |
| 8637 | 3 | 4 | 5 | 6 | VI-1 | 1700066B19Rik |
| 8638 | 3 | 4 | 5 | 6 | VI-1 | 1700066M21Rik |

Fig. 34 - 46

| | | | | | | |
|---|---|---|---|---|---|---|
| 8639 | 3 | 4 | 5 | 6 | VI-1 | 1700066N21Rik |
| 8640 | 3 | 4 | 5 | 6 | VI-1 | 1700067K01Rik |
| 8641 | 3 | 4 | 5 | 6 | VI-1 | 1700071M16Rik |
| 8642 | 3 | 4 | 5 | 6 | VI-1 | 1700072B07Rik |
| 8643 | 3 | 4 | 5 | 6 | VI-1 | 1700080E11Rik |
| 8644 | 3 | 4 | 5 | 6 | VI-1 | 1700086L19Rik |
| 8645 | 3 | 4 | 5 | 6 | VI-1 | 1700086O06Rik |
| 8646 | 3 | 4 | 5 | 6 | VI-1 | 1700092C02Rik |
| 8647 | 3 | 4 | 5 | 6 | VI-1 | 1700092M07Rik |
| 8648 | 3 | 4 | 5 | 6 | VI-1 | 1700093K21Rik |
| 8649 | 3 | 4 | 5 | 6 | VI-1 | 1700094D03Rik |
| 8650 | 3 | 4 | 5 | 6 | VI-1 | 1700095A21Rik |
| 8651 | 3 | 4 | 5 | 6 | VI-1 | 1700097N02Rik |
| 8652 | 3 | 4 | 5 | 6 | VI-1 | 1700101E01Rik |
| 8653 | 3 | 4 | 5 | 6 | VI-1 | 1700108J01Rik |
| 8654 | 3 | 4 | 5 | 6 | VI-1 | 1700120O04Rik |
| 8655 | 3 | 4 | 5 | 6 | VI-1 | 1700123M08Rik |
| 8656 | 3 | 4 | 5 | 6 | VI-1 | 1700124L16Rik |
| 8657 | 3 | 4 | 5 | 6 | VI-1 | 1700128A07Rik |
| 8658 | 3 | 4 | 5 | 6 | VI-1 | 1700129C05Rik |
| 8659 | 3 | 4 | 5 | 6 | VI-1 | 1810008I18Rik |
| 8660 | 3 | 4 | 5 | 6 | VI-1 | 1810010D01Rik |
| 8661 | 3 | 4 | 5 | 6 | VI-1 | 1810011H11Rik |
| 8662 | 3 | 4 | 5 | 6 | VI-1 | 1810011O10Rik |
| 8663 | 3 | 4 | 5 | 6 | VI-1 | 1810013A23Rik |
| 8664 | 3 | 4 | 5 | 6 | VI-1 | 1810018F18Rik |
| 8665 | 3 | 4 | 5 | 6 | VI-1 | 1810019D21Rik |
| 8666 | 3 | 4 | 5 | 6 | VI-1 | 1810020O05Rik |
| 8667 | 3 | 4 | 5 | 6 | VI-1 | 1810034E14Rik |
| 8668 | 3 | 4 | 5 | 6 | VI-1 | 1810041L15Rik |
| 8669 | 3 | 4 | 5 | 6 | VI-1 | 1810043G02Rik |
| 8670 | 3 | 4 | 5 | 6 | VI-1 | 1810046K07Rik |
| 8671 | 3 | 4 | 5 | 6 | VI-1 | 1810055G02Rik |
| 8672 | 3 | 4 | 5 | 6 | VI-1 | 2010003K11Rik |
| 8673 | 3 | 4 | 5 | 6 | VI-1 | 2010012O05Rik |
| 8674 | 3 | 4 | 5 | 6 | VI-1 | 2010106E10Rik |
| 8675 | 3 | 4 | 5 | 6 | VI-1 | 2010107G23Rik |
| 8676 | 3 | 4 | 5 | 6 | VI-1 | 2010109A12Rik |
| 8677 | 3 | 4 | 5 | 6 | VI-1 | 2010111I01Rik |
| 8678 | 3 | 4 | 5 | 6 | VI-1 | 2010204K13Rik |
| 8679 | 3 | 4 | 5 | 6 | VI-1 | 2010308F09Rik |
| 8680 | 3 | 4 | 5 | 6 | VI-1 | 2210015D19Rik |
| 8681 | 3 | 4 | 5 | 6 | VI-1 | 2210016F16Rik |
| 8682 | 3 | 4 | 5 | 6 | VI-1 | 2210018M11Rik |
| 8683 | 3 | 4 | 5 | 6 | VI-1 | 2210414B05Rik |
| 8684 | 3 | 4 | 5 | 6 | VI-1 | 2210417A02Rik |
| 8685 | 3 | 4 | 5 | 6 | VI-1 | 2210420H20Rik |
| 8686 | 3 | 4 | 5 | 6 | VI-1 | 2300002M23Rik |
| 8687 | 3 | 4 | 5 | 6 | VI-1 | 2300009A05Rik |
| 8688 | 3 | 4 | 5 | 6 | VI-1 | 2310001K24Rik |
| 8689 | 3 | 4 | 5 | 6 | VI-1 | 2310002L09Rik |
| 8690 | 3 | 4 | 5 | 6 | VI-1 | 2310007B03Rik |
| 8691 | 3 | 4 | 5 | 6 | VI-1 | 2310007L24Rik |
| 8692 | 3 | 4 | 5 | 6 | VI-1 | 2310008N11Rik |
| 8693 | 3 | 4 | 5 | 6 | VI-1 | 2310009A05Rik |
| 8694 | 3 | 4 | 5 | 6 | VI-1 | 2310009B15Rik |
| 8695 | 3 | 4 | 5 | 6 | VI-1 | 2310011J03Rik |
| 8696 | 3 | 4 | 5 | 6 | VI-1 | 2310015D24Rik |
| 8697 | 3 | 4 | 5 | 6 | VI-1 | 2310030G06Rik |
| 8698 | 3 | 4 | 5 | 6 | VI-1 | 2310034G01Rik |
| 8699 | 3 | 4 | 5 | 6 | VI-1 | 2310039H08Rik |
| 8700 | 3 | 4 | 5 | 6 | VI-1 | 2310039L15Rik |
| 8701 | 3 | 4 | 5 | 6 | VI-1 | 2310040G24Rik |
| 8702 | 3 | 4 | 5 | 6 | VI-1 | 2310042E22Rik |
| 8703 | 3 | 4 | 5 | 6 | VI-1 | 2310043L19Rik |
| 8704 | 3 | 4 | 5 | 6 | VI-1 | 2310050C09Rik |
| 8705 | 3 | 4 | 5 | 6 | VI-1 | 2310061J03Rik |
| 8706 | 3 | 4 | 5 | 6 | VI-1 | 2310068J16Rik |
| 8707 | 3 | 4 | 5 | 6 | VI-1 | 2310081J21Rik |
| 8708 | 3 | 4 | 5 | 6 | VI-1 | 2410004B18Rik |
| 8709 | 3 | 4 | 5 | 6 | VI-1 | 2410004I01Rik |
| 8710 | 3 | 4 | 5 | 6 | VI-1 | 2410004P03Rik |
| 8711 | 3 | 4 | 5 | 6 | VI-1 | 2410088K16Rik |
| 8712 | 3 | 4 | 5 | 6 | VI-1 | 2410137M14Rik |
| 8713 | 3 | 4 | 5 | 6 | VI-1 | 2410141K09Rik |
| 8714 | 3 | 4 | 5 | 6 | VI-1 | 2500004C02Rik |
| 8715 | 3 | 4 | 5 | 6 | VI-1 | 2510002D24Rik |
| 8716 | 3 | 4 | 5 | 6 | VI-1 | 2510009E07Rik |
| 8717 | 3 | 4 | 5 | 6 | VI-1 | 2510039O18Rik |
| 8718 | 3 | 4 | 5 | 6 | VI-1 | 2610002M06Rik |
| 8719 | 3 | 4 | 5 | 6 | VI-1 | 2610005L07Rik |
| 8720 | 3 | 4 | 5 | 6 | VI-1 | 2610008E11Rik |
| 8721 | 3 | 4 | 5 | 6 | VI-1 | 2610020H08Rik |
| 8722 | 3 | 4 | 5 | 6 | VI-1 | 2610028H24Rik |
| 8723 | 3 | 4 | 5 | 6 | VI-1 | 2610034B18Rik |
| 8724 | 3 | 4 | 5 | 6 | VI-1 | 2610034M16Rik |
| 8725 | 3 | 4 | 5 | 6 | VI-1 | 2610044O15Rik8 |
| 8726 | 3 | 4 | 5 | 6 | VI-1 | 2610306M01Rik |
| 8727 | 3 | 4 | 5 | 6 | VI-1 | 2610316D01Rik |
| 8728 | 3 | 4 | 5 | 6 | VI-1 | 2610318N02Rik |
| 8729 | 3 | 4 | 5 | 6 | VI-1 | 2610507B11Rik |
| 8730 | 3 | 4 | 5 | 6 | VI-1 | 2610528A11Rik |
| 8731 | 3 | 4 | 5 | 6 | VI-1 | 2700029M09Rik |
| 8732 | 3 | 4 | 5 | 6 | VI-1 | 2700038G22Rik |
| 8733 | 3 | 4 | 5 | 6 | VI-1 | 2700062C07Rik |
| 8734 | 3 | 4 | 5 | 6 | VI-1 | 2700069I18Rik |

| | | | | | | |
|---|---|---|---|---|---|---|
| 8735 | 3 | 4 | 5 | 6 | VI-1 | 2700086A05Rik |
| 8736 | 3 | 4 | 5 | 6 | VI-1 | 2700089E24Rik |
| 8737 | 3 | 4 | 5 | 6 | VI-1 | 2700094K13Rik |
| 8738 | 3 | 4 | 5 | 6 | VI-1 | 2700097O09Rik |
| 8739 | 3 | 4 | 5 | 6 | VI-1 | 2810001G20Rik |
| 8740 | 3 | 4 | 5 | 6 | VI-1 | 2810008D09Rik |
| 8741 | 3 | 4 | 5 | 6 | VI-1 | 2810013P06Rik |
| 8742 | 3 | 4 | 5 | 6 | VI-1 | 2810021J22Rik |
| 8743 | 3 | 4 | 5 | 6 | VI-1 | 2810029C07Rik |
| 8744 | 3 | 4 | 5 | 6 | VI-1 | 2810032G03Rik |
| 8745 | 3 | 4 | 5 | 6 | VI-1 | 2810049E08Rik |
| 8746 | 3 | 4 | 5 | 6 | VI-1 | 2810403D21Rik |
| 8747 | 3 | 4 | 5 | 6 | VI-1 | 2810408I11Rik |
| 8748 | 3 | 4 | 5 | 6 | VI-1 | 2810433D01Rik |
| 8749 | 3 | 4 | 5 | 6 | VI-1 | 2810468N07Rik |
| 8750 | 3 | 4 | 5 | 6 | VI-1 | 2900026A02Rik |
| 8751 | 3 | 4 | 5 | 6 | VI-1 | 2900055J20Rik |
| 8752 | 3 | 4 | 5 | 6 | VI-1 | 2900056M20Rik |
| 8753 | 3 | 4 | 5 | 6 | VI-1 | 2900076A07Rik |
| 8754 | 3 | 4 | 5 | 6 | VI-1 | 3000002C10Rik |
| 8755 | 3 | 4 | 5 | 6 | VI-1 | 3110001I22Rik |
| 8756 | 3 | 4 | 5 | 6 | VI-1 | 3110002H16Rik |
| 8757 | 3 | 4 | 5 | 6 | VI-1 | 3110015C05Rik |
| 8758 | 3 | 4 | 5 | 6 | VI-1 | 3110039M20Rik |
| 8759 | 3 | 4 | 5 | 6 | VI-1 | 3110045C21Rik |
| 8760 | 3 | 4 | 5 | 6 | VI-1 | 3110056K07Rik |
| 8761 | 3 | 4 | 5 | 6 | VI-1 | 3110062M04Rik |
| 8762 | 3 | 4 | 5 | 6 | VI-1 | 3110070M22Rik |
| 8763 | 3 | 4 | 5 | 6 | VI-1 | 3300005D01Rik |
| 8764 | 3 | 4 | 5 | 6 | VI-1 | 3425401I19Rik |
| 8765 | 3 | 4 | 5 | 6 | VI-1 | 3632451O06Rik |
| 8766 | 3 | 4 | 5 | 6 | VI-1 | 3830403N18Rik |
| 8767 | 3 | 4 | 5 | 6 | VI-1 | 4430402I18Rik |
| 8768 | 3 | 4 | 5 | 6 | VI-1 | 4632428N05Rik |
| 8769 | 3 | 4 | 5 | 6 | VI-1 | 4732416N19Rik |
| 8770 | 3 | 4 | 5 | 6 | VI-1 | 4732491K20Rik |
| 8771 | 3 | 4 | 5 | 6 | VI-1 | 4833403I15Rik |
| 8772 | 3 | 4 | 5 | 6 | VI-1 | 4833412C05Rik |
| 8773 | 3 | 4 | 5 | 6 | VI-1 | 4833419F23Rik |
| 8774 | 3 | 4 | 5 | 6 | VI-1 | 4833420G17Rik |
| 8775 | 3 | 4 | 5 | 6 | VI-1 | 4833427G06Rik |
| 8776 | 3 | 4 | 5 | 6 | VI-1 | 4833428L15Rik |
| 8777 | 3 | 4 | 5 | 6 | VI-1 | 4921508O12Rik |
| 8778 | 3 | 4 | 5 | 6 | VI-1 | 4921509C19Rik |
| 8779 | 3 | 4 | 5 | 6 | VI-1 | 4921533I20Rik |
| 8780 | 3 | 4 | 5 | 6 | VI-1 | 4921536K21Rik |
| 8781 | 3 | 4 | 5 | 6 | VI-1 | 4922502H24Rik |
| 8782 | 3 | 4 | 5 | 6 | VI-1 | 4930401O10Rik |
| 8783 | 3 | 4 | 5 | 6 | VI-1 | 4930404N11Rik |
| 8784 | 3 | 4 | 5 | 6 | VI-1 | 4930405J17Rik |
| 8785 | 3 | 4 | 5 | 6 | VI-1 | 4930415F15Rik |
| 8786 | 3 | 4 | 5 | 6 | VI-1 | 4930426D05Rik |
| 8787 | 3 | 4 | 5 | 6 | VI-1 | 4930429F24Rik |
| 8788 | 3 | 4 | 5 | 6 | VI-1 | 4930430F08Rik |
| 8789 | 3 | 4 | 5 | 6 | VI-1 | 4930430J02Rik |
| 8790 | 3 | 4 | 5 | 6 | VI-1 | 4930432K21Rik |
| 8791 | 3 | 4 | 5 | 6 | VI-1 | 4930435E12Rik |
| 8792 | 3 | 4 | 5 | 6 | VI-1 | 4930441G19Rik |
| 8793 | 3 | 4 | 5 | 6 | VI-1 | 4930444G20Rik |
| 8794 | 3 | 4 | 5 | 6 | VI-1 | 4930444P10Rik |
| 8795 | 3 | 4 | 5 | 6 | VI-1 | 4930448C13Rik |
| 8796 | 3 | 4 | 5 | 6 | VI-1 | 4930448F12Rik |
| 8797 | 3 | 4 | 5 | 6 | VI-1 | 4930448I06Rik |
| 8798 | 3 | 4 | 5 | 6 | VI-1 | 4930451C15Rik |
| 8799 | 3 | 4 | 5 | 6 | VI-1 | 4930451G09Rik |
| 8800 | 3 | 4 | 5 | 6 | VI-1 | 4930453L07Rik |
| 8801 | 3 | 4 | 5 | 6 | VI-1 | 4930455C13Rik |
| 8802 | 3 | 4 | 5 | 6 | VI-1 | 4930455J16Rik |
| 8803 | 3 | 4 | 5 | 6 | VI-1 | 4930467E23Rik |
| 8804 | 3 | 4 | 5 | 6 | VI-1 | 4930486L24Rik |
| 8805 | 3 | 4 | 5 | 6 | VI-1 | 4930487D11Rik |
| 8806 | 3 | 4 | 5 | 6 | VI-1 | 4930500J02Rik |
| 8807 | 3 | 4 | 5 | 6 | VI-1 | 4930502E18Rik |
| 8808 | 3 | 4 | 5 | 6 | VI-1 | 4930503B20Rik |
| 8809 | 3 | 4 | 5 | 6 | VI-1 | 4930503E24Rik |
| 8810 | 3 | 4 | 5 | 6 | VI-1 | 4930506M07Rik |
| 8811 | 3 | 4 | 5 | 6 | VI-1 | 4930507D10Rik |
| 8812 | 3 | 4 | 5 | 6 | VI-1 | 4930515G16Rik |
| 8813 | 3 | 4 | 5 | 6 | VI-1 | 4930520P13Rik |
| 8814 | 3 | 4 | 5 | 6 | VI-1 | 4930523C07Rik |
| 8815 | 3 | 4 | 5 | 6 | VI-1 | 4930527F14Rik |
| 8816 | 3 | 4 | 5 | 6 | VI-1 | 4930538K18Rik |
| 8817 | 3 | 4 | 5 | 6 | VI-1 | 4930539E08Rik |
| 8818 | 3 | 4 | 5 | 6 | VI-1 | 4930544G11Rik |
| 8819 | 3 | 4 | 5 | 6 | VI-1 | 4930548G14Rik |
| 8820 | 3 | 4 | 5 | 6 | VI-1 | 4930548H24Rik |
| 8821 | 3 | 4 | 5 | 6 | VI-1 | 4930548K13Rik |
| 8822 | 3 | 4 | 5 | 6 | VI-1 | 4930555G01Rik |
| 8823 | 3 | 4 | 5 | 6 | VI-1 | 4930556J02Rik |
| 8824 | 3 | 4 | 5 | 6 | VI-1 | 4930557A04Rik |
| 8825 | 3 | 4 | 5 | 6 | VI-1 | 4930571K23Rik |
| 8826 | 3 | 4 | 5 | 6 | VI-1 | 4930578I06Rik |
| 8827 | 3 | 4 | 5 | 6 | VI-1 | 4930578M01Rik |
| 8828 | 3 | 4 | 5 | 6 | VI-1 | 4930581F22Rik |
| 8829 | 3 | 4 | 5 | 6 | VI-1 | 4930598F16Rik |
| 8830 | 3 | 4 | 5 | 6 | VI-1 | 4931403E22Rik |

Fig. 34 - 47

| | | | | | | |
|---|---|---|---|---|---|---|
| 8831 | 3 | 4 | 5 | 6 | VI-1 | 4931406H21Rik |
| 8832 | 3 | 4 | 5 | 6 | VI-1 | 4931406P16Rik |
| 8833 | 3 | 4 | 5 | 6 | VI-1 | 4931408D14Rik |
| 8834 | 3 | 4 | 5 | 6 | VI-1 | 4931430N09Rik |
| 8835 | 3 | 4 | 5 | 6 | VI-1 | 4931431C16Rik |
| 8836 | 3 | 4 | 5 | 6 | VI-1 | 4932413F04Rik |
| 8837 | 3 | 4 | 5 | 6 | VI-1 | 4933402P03Rik |
| 8838 | 3 | 4 | 5 | 6 | VI-1 | 4933406C10Rik |
| 8839 | 3 | 4 | 5 | 6 | VI-1 | 4933412E12Rik |
| 8840 | 3 | 4 | 5 | 6 | VI-1 | 4933415F23Rik |
| 8841 | 3 | 4 | 5 | 6 | VI-1 | 4933417A18Rik |
| 8842 | 3 | 4 | 5 | 6 | VI-1 | 4933417D19Rik |
| 8843 | 3 | 4 | 5 | 6 | VI-1 | 4933421O10Rik |
| 8844 | 3 | 4 | 5 | 6 | VI-1 | 4933424G06Rik |
| 8845 | 3 | 4 | 5 | 6 | VI-1 | 4933427G17Rik |
| 8846 | 3 | 4 | 5 | 6 | VI-1 | 4933430M04Rik |
| 8847 | 3 | 4 | 5 | 6 | VI-1 | 4933431E20Rik |
| 8848 | 3 | 4 | 5 | 6 | VI-1 | 4933433G15Rik |
| 8849 | 3 | 4 | 5 | 6 | VI-1 | 4933433G19Rik |
| 8850 | 3 | 4 | 5 | 6 | VI-1 | 4933434E20Rik |
| 8851 | 3 | 4 | 5 | 6 | VI-1 | 4933438817Rik |
| 8852 | 3 | 4 | 5 | 6 | VI-1 | 4933438K21Rik |
| 8853 | 3 | 4 | 5 | 6 | VI-1 | 5031410I06Rik |
| 8854 | 3 | 4 | 5 | 6 | VI-1 | 5031425E22Rik |
| 8855 | 3 | 4 | 5 | 6 | VI-1 | 5033406O09Rik |
| 8856 | 3 | 4 | 5 | 6 | VI-1 | 5133400J02Rik |
| 8857 | 3 | 4 | 5 | 6 | VI-1 | 5330426P16Rik |
| 8858 | 3 | 4 | 5 | 6 | VI-1 | 5430402O13Rik |
| 8859 | 3 | 4 | 5 | 6 | VI-1 | 5430416N02Rik |
| 8860 | 3 | 4 | 5 | 6 | VI-1 | 5430416O09Rik |
| 8861 | 3 | 4 | 5 | 6 | VI-1 | 5430440P10Rik |
| 8862 | 3 | 4 | 5 | 6 | VI-1 | 5730405O15Rik |
| 8863 | 3 | 4 | 5 | 6 | VI-1 | 5730408K05Rik |
| 8864 | 3 | 4 | 5 | 6 | VI-1 | 5730409E04Rik |
| 8865 | 3 | 4 | 5 | 6 | VI-1 | 5730420D15Rik |
| 8866 | 3 | 4 | 5 | 6 | VI-1 | 5730455P16Rik |
| 8867 | 3 | 4 | 5 | 6 | VI-1 | 5830411N06Rik |
| 8868 | 3 | 4 | 5 | 6 | VI-1 | 5830415F09Rik |
| 8869 | 3 | 4 | 5 | 6 | VI-1 | 6030498E09Rik |
| 8870 | 3 | 4 | 5 | 6 | VI-1 | 6230400D17Rik |
| 8871 | 3 | 4 | 5 | 6 | VI-1 | 6330403A02Rik |
| 8872 | 3 | 4 | 5 | 6 | VI-1 | 6330409D20Rik |
| 8873 | 3 | 4 | 5 | 6 | VI-1 | 6330416G13Rik |
| 8874 | 3 | 4 | 5 | 6 | VI-1 | 6330419J24Rik |
| 8875 | 3 | 4 | 5 | 6 | VI-1 | 6430548M08Rik |
| 8876 | 3 | 4 | 5 | 6 | VI-1 | 6430550D23Rik |
| 8877 | 3 | 4 | 5 | 6 | VI-1 | 6430573F11Rik |
| 8878 | 3 | 4 | 5 | 6 | VI-1 | 6720416L17Rik |
| 8879 | 3 | 4 | 5 | 6 | VI-1 | 6820408C15Rik |
| 8880 | 3 | 4 | 5 | 6 | VI-1 | 6820431F20Rik |
| 8881 | 3 | 4 | 5 | 6 | VI-1 | 7420461P10Rik |
| 8882 | 3 | 4 | 5 | 6 | VI-1 | 8030411F24Rik |
| 8883 | 3 | 4 | 5 | 6 | VI-1 | 8430426J06Rik |
| 8884 | 3 | 4 | 5 | 6 | VI-1 | 9030617O03Rik |
| 8885 | 3 | 4 | 5 | 6 | VI-1 | 9030624J02Rik |
| 8886 | 3 | 4 | 5 | 6 | VI-1 | 9130019O22Rik |
| 8887 | 3 | 4 | 5 | 6 | VI-1 | 9230110C19Rik |
| 8888 | 3 | 4 | 5 | 6 | VI-1 | 9230116L04Rik |
| 8889 | 3 | 4 | 5 | 6 | VI-1 | 9330102E08Rik |
| 8890 | 3 | 4 | 5 | 6 | VI-1 | 9330162O12Rik |
| 8891 | 3 | 4 | 5 | 6 | VI-1 | 9430008C03Rik |
| 8892 | 3 | 4 | 5 | 6 | VI-1 | 9430020K01Rik |
| 8893 | 3 | 4 | 5 | 6 | VI-1 | 9430038I01Rik |
| 8894 | 3 | 4 | 5 | 6 | VI-1 | 9530026P05Rik |
| 8895 | 3 | 4 | 5 | 6 | VI-1 | 9530077C05Rik |
| 8896 | 3 | 4 | 5 | 6 | VI-1 | 9930012K11Rik |
| 8897 | 3 | 4 | 5 | 6 | VI-1 | 9930021J03Rik |
| 8898 | 3 | 4 | 5 | 6 | VI-1 | A130010J15Rik |
| 8899 | 3 | 4 | 5 | 6 | VI-1 | A230046K03Rik |
| 8900 | 3 | 4 | 5 | 6 | VI-1 | A230050P20Rik |
| 8901 | 3 | 4 | 5 | 6 | VI-1 | A230072C01Rik |
| 8902 | 3 | 4 | 5 | 6 | VI-1 | A2m |
| 8903 | 3 | 4 | 5 | 6 | VI-1 | A330023F24Rik |
| 8904 | 3 | 4 | 5 | 6 | VI-1 | A330049N07Rik |
| 8905 | 3 | 4 | 5 | 6 | VI-1 | A430035B10Rik |
| 8906 | 3 | 4 | 5 | 6 | VI-1 | A430105I19Rik |
| 8907 | 3 | 4 | 5 | 6 | VI-1 | A530032D15Rik |
| 8908 | 3 | 4 | 5 | 6 | VI-1 | A530072M11Rik |
| 8909 | 3 | 4 | 5 | 6 | VI-1 | A530088E08Rik |
| 8910 | 3 | 4 | 5 | 6 | VI-1 | A630007B06Rik |
| 8911 | 3 | 4 | 5 | 6 | VI-1 | A630072M18Rik |
| 8912 | 3 | 4 | 5 | 6 | VI-1 | A630073D07Rik |
| 8913 | 3 | 4 | 5 | 6 | VI-1 | A730017C20Rik |
| 8914 | 3 | 4 | 5 | 6 | VI-1 | A730017L22Rik |
| 8915 | 3 | 4 | 5 | 6 | VI-1 | A730085K08Rik |
| 8916 | 3 | 4 | 5 | 6 | VI-1 | A830010M20Rik |
| 8917 | 3 | 4 | 5 | 6 | VI-1 | A830080D01Rik |
| 8918 | 3 | 4 | 5 | 6 | VI-1 | A930003A15Rik |
| 8919 | 3 | 4 | 5 | 6 | VI-1 | A930005H10Rik |
| 8920 | 3 | 4 | 5 | 6 | VI-1 | A930006K02Rik |
| 8921 | 3 | 4 | 5 | 6 | VI-1 | A930009A15Rik |
| 8922 | 3 | 4 | 5 | 6 | VI-1 | A930016O22Rik |
| 8923 | 3 | 4 | 5 | 6 | VI-1 | A930018P22Rik |
| 8924 | 3 | 4 | 5 | 6 | VI-1 | A930019D19Rik |
| 8925 | 3 | 4 | 5 | 6 | VI-1 | AA474331 |
| 8926 | 3 | 4 | 5 | 6 | VI-1 | AA986860 |

| | | | | | | |
|---|---|---|---|---|---|---|
| 8927 | 3 | 4 | 5 | 6 | VI-1 | AA987161 |
| 8928 | 3 | 4 | 5 | 6 | VI-1 | AF067061 |
| 8929 | 3 | 4 | 5 | 6 | VI-1 | AF251705 |
| 8930 | 3 | 4 | 5 | 6 | VI-1 | AI182371 |
| 8931 | 3 | 4 | 5 | 6 | VI-1 | AI314180 |
| 8932 | 3 | 4 | 5 | 6 | VI-1 | AI314278 |
| 8933 | 3 | 4 | 5 | 6 | VI-1 | AI317395 |
| 8934 | 3 | 4 | 5 | 6 | VI-1 | AI413582 |
| 8935 | 3 | 4 | 5 | 6 | VI-1 | AI429214 |
| 8936 | 3 | 4 | 5 | 6 | VI-1 | AI467606 |
| 8937 | 3 | 4 | 5 | 6 | VI-1 | AI646519 |
| 8938 | 3 | 4 | 5 | 6 | VI-1 | AI661453 |
| 8939 | 3 | 4 | 5 | 6 | VI-1 | AI662270 |
| 8940 | 3 | 4 | 5 | 6 | VI-1 | AI837181 |
| 8941 | 3 | 4 | 5 | 6 | VI-1 | AI846148 |
| 8942 | 3 | 4 | 5 | 6 | VI-1 | AI854703 |
| 8943 | 3 | 4 | 5 | 6 | VI-1 | AI987944 |
| 8944 | 3 | 4 | 5 | 6 | VI-1 | AK010878 |
| 8945 | 3 | 4 | 5 | 6 | VI-1 | AU015791 |
| 8946 | 3 | 4 | 5 | 6 | VI-1 | AU040320 |
| 8947 | 3 | 4 | 5 | 6 | VI-1 | AV051173 |
| 8948 | 3 | 4 | 5 | 6 | VI-1 | AW495222 |
| 8949 | 3 | 4 | 5 | 6 | VI-1 | AW549542 |
| 8950 | 3 | 4 | 5 | 6 | VI-1 | AW822252 |
| 8951 | 3 | 4 | 5 | 6 | VI-1 | Aaas |
| 8952 | 3 | 4 | 5 | 6 | VI-1 | Aadac |
| 8953 | 3 | 4 | 5 | 6 | VI-1 | Aadat |
| 8954 | 3 | 4 | 5 | 6 | VI-1 | Aaed1 |
| 8955 | 3 | 4 | 5 | 6 | VI-1 | Aamdc |
| 8956 | 3 | 4 | 5 | 6 | VI-1 | Aamp |
| 8957 | 3 | 4 | 5 | 6 | VI-1 | Aar2 |
| 8958 | 3 | 4 | 5 | 6 | VI-1 | Aard |
| 8959 | 3 | 4 | 5 | 6 | VI-1 | Aars |
| 8960 | 3 | 4 | 5 | 6 | VI-1 | Aars2 |
| 8961 | 3 | 4 | 5 | 6 | VI-1 | Aass |
| 8962 | 3 | 4 | 5 | 6 | VI-1 | Aatk |
| 8963 | 3 | 4 | 5 | 6 | VI-1 | Abca13 |
| 8964 | 3 | 4 | 5 | 6 | VI-1 | Abca4 |
| 8965 | 3 | 4 | 5 | 6 | VI-1 | Abca6 |
| 8966 | 3 | 4 | 5 | 6 | VI-1 | Abca9 |
| 8967 | 3 | 4 | 5 | 6 | VI-1 | Abcb4 |
| 8968 | 3 | 4 | 5 | 6 | VI-1 | Abcb8 |
| 8969 | 3 | 4 | 5 | 6 | VI-1 | Abcb9 |
| 8970 | 3 | 4 | 5 | 6 | VI-1 | Abcc2 |
| 8971 | 3 | 4 | 5 | 6 | VI-1 | Abcc3 |
| 8972 | 3 | 4 | 5 | 6 | VI-1 | Abcc5 |
| 8973 | 3 | 4 | 5 | 6 | VI-1 | Abcc9 |
| 8974 | 3 | 4 | 5 | 6 | VI-1 | Abcf3 |
| 8975 | 3 | 4 | 5 | 6 | VI-1 | Abcg1 |
| 8976 | 3 | 4 | 5 | 6 | VI-1 | Abcg8 |
| 8977 | 3 | 4 | 5 | 6 | VI-1 | Abhd10 |
| 8978 | 3 | 4 | 5 | 6 | VI-1 | Abhd11 |
| 8979 | 3 | 4 | 5 | 6 | VI-1 | Abhd12b |
| 8980 | 3 | 4 | 5 | 6 | VI-1 | Abhd14a |
| 8981 | 3 | 4 | 5 | 6 | VI-1 | Abhd14b |
| 8982 | 3 | 4 | 5 | 6 | VI-1 | Abhd16a |
| 8983 | 3 | 4 | 5 | 6 | VI-1 | Abhd17a |
| 8984 | 3 | 4 | 5 | 6 | VI-1 | Abhd17b |
| 8985 | 3 | 4 | 5 | 6 | VI-1 | Abhd3 |
| 8986 | 3 | 4 | 5 | 6 | VI-1 | Abhd4 |
| 8987 | 3 | 4 | 5 | 6 | VI-1 | Abhd6 |
| 8988 | 3 | 4 | 5 | 6 | VI-1 | Abi1 |
| 8989 | 3 | 4 | 5 | 6 | VI-1 | Abi2 |
| 8990 | 3 | 4 | 5 | 6 | VI-1 | Abi3 |
| 8991 | 3 | 4 | 5 | 6 | VI-1 | Abi3bp |
| 8992 | 3 | 4 | 5 | 6 | VI-1 | Ablim2 |
| 8993 | 3 | 4 | 5 | 6 | VI-1 | Ablim3 |
| 8994 | 3 | 4 | 5 | 6 | VI-1 | Abt1 |
| 8995 | 3 | 4 | 5 | 6 | VI-1 | Abtb2 |
| 8996 | 3 | 4 | 5 | 6 | VI-1 | Acaa1b |
| 8997 | 3 | 4 | 5 | 6 | VI-1 | Acaa2 |
| 8998 | 3 | 4 | 5 | 6 | VI-1 | Acacb |
| 8999 | 3 | 4 | 5 | 6 | VI-1 | Acad10 |
| 9000 | 3 | 4 | 5 | 6 | VI-1 | Acad12 |
| 9001 | 3 | 4 | 5 | 6 | VI-1 | Acads |
| 9002 | 3 | 4 | 5 | 6 | VI-1 | Acat2 |
| 9003 | 3 | 4 | 5 | 6 | VI-1 | Acbd5 |
| 9004 | 3 | 4 | 5 | 6 | VI-1 | Acbd6 |
| 9005 | 3 | 4 | 5 | 6 | VI-1 | Accsl |
| 9006 | 3 | 4 | 5 | 6 | VI-1 | Ace |
| 9007 | 3 | 4 | 5 | 6 | VI-1 | Acer2 |
| 9008 | 3 | 4 | 5 | 6 | VI-1 | Acer3 |
| 9009 | 3 | 4 | 5 | 6 | VI-1 | Ackr1 |
| 9010 | 3 | 4 | 5 | 6 | VI-1 | Ackr2 |
| 9011 | 3 | 4 | 5 | 6 | VI-1 | Ackr3 |
| 9012 | 3 | 4 | 5 | 6 | VI-1 | Acly |
| 9013 | 3 | 4 | 5 | 6 | VI-1 | Acn9 |
| 9014 | 3 | 4 | 5 | 6 | VI-1 | Acnat2 |
| 9015 | 3 | 4 | 5 | 6 | VI-1 | Acot10 |
| 9016 | 3 | 4 | 5 | 6 | VI-1 | Acot12 |
| 9017 | 3 | 4 | 5 | 6 | VI-1 | Acot13 |
| 9018 | 3 | 4 | 5 | 6 | VI-1 | Acot2 |
| 9019 | 3 | 4 | 5 | 6 | VI-1 | Acot4 |
| 9020 | 3 | 4 | 5 | 6 | VI-1 | Acot6 |
| 9021 | 3 | 4 | 5 | 6 | VI-1 | Acot8 |
| 9022 | 3 | 4 | 5 | 6 | VI-1 | Acot9 |

Fig. 34 - 48

| | | | | | | | |
|---|---|---|---|---|---|---|---|
| 9023 | 3 | 4 | 5 | 6 | VI-1 | Acp2 |
| 9024 | 3 | 4 | 5 | 6 | VI-1 | Acpp |
| 9025 | 3 | 4 | 5 | 6 | VI-1 | Acpt |
| 9026 | 3 | 4 | 5 | 6 | VI-1 | Acr |
| 9027 | 3 | 4 | 5 | 6 | VI-1 | Acrbp |
| 9028 | 3 | 4 | 5 | 6 | VI-1 | Acsl1 |
| 9029 | 3 | 4 | 5 | 6 | VI-1 | Acsl3 |
| 9030 | 3 | 4 | 5 | 6 | VI-1 | Acsl6 |
| 9031 | 3 | 4 | 5 | 6 | VI-1 | Acsm5 |
| 9032 | 3 | 4 | 5 | 6 | VI-1 | Acss1 |
| 9033 | 3 | 4 | 5 | 6 | VI-1 | Acss2 |
| 9034 | 3 | 4 | 5 | 6 | VI-1 | Acss2os |
| 9035 | 3 | 4 | 5 | 6 | VI-1 | Acss3 |
| 9036 | 3 | 4 | 5 | 6 | VI-1 | Acta2 |
| 9037 | 3 | 4 | 5 | 6 | VI-1 | Actg1 |
| 9038 | 3 | 4 | 5 | 6 | VI-1 | Actg2 |
| 9039 | 3 | 4 | 5 | 6 | VI-1 | Actl11 |
| 9040 | 3 | 4 | 5 | 6 | VI-1 | Actl7a |
| 9041 | 3 | 4 | 5 | 6 | VI-1 | Actl9 |
| 9042 | 3 | 4 | 5 | 6 | VI-1 | Actn4 |
| 9043 | 3 | 4 | 5 | 6 | VI-1 | Actr10 |
| 9044 | 3 | 4 | 5 | 6 | VI-1 | Actr1a |
| 9045 | 3 | 4 | 5 | 6 | VI-1 | Actr1b |
| 9046 | 3 | 4 | 5 | 6 | VI-1 | Actr3 |
| 9047 | 3 | 4 | 5 | 6 | VI-1 | Actr8 |
| 9048 | 3 | 4 | 5 | 6 | VI-1 | Actrt2 |
| 9049 | 3 | 4 | 5 | 6 | VI-1 | Acvr2a |
| 9050 | 3 | 4 | 5 | 6 | VI-1 | Acvr2b |
| 9051 | 3 | 4 | 5 | 6 | VI-1 | Acvrl1 |
| 9052 | 3 | 4 | 5 | 6 | VI-1 | Acy1 |
| 9053 | 3 | 4 | 5 | 6 | VI-1 | Acyp2 |
| 9054 | 3 | 4 | 5 | 6 | VI-1 | Adam10 |
| 9055 | 3 | 4 | 5 | 6 | VI-1 | Adam15 |
| 9056 | 3 | 4 | 5 | 6 | VI-1 | Adam22 |
| 9057 | 3 | 4 | 5 | 6 | VI-1 | Adam23 |
| 9058 | 3 | 4 | 5 | 6 | VI-1 | Adam28 |
| 9059 | 3 | 4 | 5 | 6 | VI-1 | Adam32 |
| 9060 | 3 | 4 | 5 | 6 | VI-1 | Adam33 |
| 9061 | 3 | 4 | 5 | 6 | VI-1 | Adam8 |
| 9062 | 3 | 4 | 5 | 6 | VI-1 | Adamdec1 |
| 9063 | 3 | 4 | 5 | 6 | VI-1 | Adamts1 |
| 9064 | 3 | 4 | 5 | 6 | VI-1 | Adamts13 |
| 9065 | 3 | 4 | 5 | 6 | VI-1 | Adamts14 |
| 9066 | 3 | 4 | 5 | 6 | VI-1 | Adamts15 |
| 9067 | 3 | 4 | 5 | 6 | VI-1 | Adamts2 |
| 9068 | 3 | 4 | 5 | 6 | VI-1 | Adamts4 |
| 9069 | 3 | 4 | 5 | 6 | VI-1 | Adamtsl1 |
| 9070 | 3 | 4 | 5 | 6 | VI-1 | Adamtsl2 |
| 9071 | 3 | 4 | 5 | 6 | VI-1 | Adap1 |
| 9072 | 3 | 4 | 5 | 6 | VI-1 | Adar |
| 9073 | 3 | 4 | 5 | 6 | VI-1 | Adarb1 |
| 9074 | 3 | 4 | 5 | 6 | VI-1 | Adat1 |
| 9075 | 3 | 4 | 5 | 6 | VI-1 | Adat3 |
| 9076 | 3 | 4 | 5 | 6 | VI-1 | Adck1 |
| 9077 | 3 | 4 | 5 | 6 | VI-1 | Adck2 |
| 9078 | 3 | 4 | 5 | 6 | VI-1 | Adck3 |
| 9079 | 3 | 4 | 5 | 6 | VI-1 | Adcy2 |
| 9080 | 3 | 4 | 5 | 6 | VI-1 | Adcy3 |
| 9081 | 3 | 4 | 5 | 6 | VI-1 | Adcy4 |
| 9082 | 3 | 4 | 5 | 6 | VI-1 | Adcy5 |
| 9083 | 3 | 4 | 5 | 6 | VI-1 | Adcyap1r1 |
| 9084 | 3 | 4 | 5 | 6 | VI-1 | Add3 |
| 9085 | 3 | 4 | 5 | 6 | VI-1 | Adh5 |
| 9086 | 3 | 4 | 5 | 6 | VI-1 | Adipoq |
| 9087 | 3 | 4 | 5 | 6 | VI-1 | Adm |
| 9088 | 3 | 4 | 5 | 6 | VI-1 | Adm2 |
| 9089 | 3 | 4 | 5 | 6 | VI-1 | Adprhl1 |
| 9090 | 3 | 4 | 5 | 6 | VI-1 | Adprhl2 |
| 9091 | 3 | 4 | 5 | 6 | VI-1 | Adra2a |
| 9092 | 3 | 4 | 5 | 6 | VI-1 | Adrbk1 |
| 9093 | 3 | 4 | 5 | 6 | VI-1 | Adrm1 |
| 9094 | 3 | 4 | 5 | 6 | VI-1 | Adsl |
| 9095 | 3 | 4 | 5 | 6 | VI-1 | Adssl1 |
| 9096 | 3 | 4 | 5 | 6 | VI-1 | Adtrp |
| 9097 | 3 | 4 | 5 | 6 | VI-1 | Aebp1 |
| 9098 | 3 | 4 | 5 | 6 | VI-1 | Afap1 |
| 9099 | 3 | 4 | 5 | 6 | VI-1 | Afap1l1 |
| 9100 | 3 | 4 | 5 | 6 | VI-1 | Aff1 |
| 9101 | 3 | 4 | 5 | 6 | VI-1 | Aff4 |
| 9102 | 3 | 4 | 5 | 6 | VI-1 | Afg3l1 |
| 9103 | 3 | 4 | 5 | 6 | VI-1 | Aftph |
| 9104 | 3 | 4 | 5 | 6 | VI-1 | Agap1 |
| 9105 | 3 | 4 | 5 | 6 | VI-1 | Agbl3 |
| 9106 | 3 | 4 | 5 | 6 | VI-1 | Agbl5 |
| 9107 | 3 | 4 | 5 | 6 | VI-1 | Agfg1 |
| 9108 | 3 | 4 | 5 | 6 | VI-1 | Agmat |
| 9109 | 3 | 4 | 5 | 6 | VI-1 | Ago2 |
| 9110 | 3 | 4 | 5 | 6 | VI-1 | Agpat3 |
| 9111 | 3 | 4 | 5 | 6 | VI-1 | Agpat4 |
| 9112 | 3 | 4 | 5 | 6 | VI-1 | Agpat5 |
| 9113 | 3 | 4 | 5 | 6 | VI-1 | Agpat6 |
| 9114 | 3 | 4 | 5 | 6 | VI-1 | Agps |
| 9115 | 3 | 4 | 5 | 6 | VI-1 | Agr3 |
| 9116 | 3 | 4 | 5 | 6 | VI-1 | Agtrap |
| 9117 | 3 | 4 | 5 | 6 | VI-1 | Agxt |
| 9118 | 3 | 4 | 5 | 6 | VI-1 | Ahi1 |
| 9119 | 3 | 4 | 5 | 6 | VI-1 | Ahnak |
| 9120 | 3 | 4 | 5 | 6 | VI-1 | Ahsa1 |
| 9121 | 3 | 4 | 5 | 6 | VI-1 | Ahsa2 |
| 9122 | 3 | 4 | 5 | 6 | VI-1 | Aida |
| 9123 | 3 | 4 | 5 | 6 | VI-1 | Aifl1 |
| 9124 | 3 | 4 | 5 | 6 | VI-1 | Alg1 |
| 9125 | 3 | 4 | 5 | 6 | VI-1 | Aim1 |
| 9126 | 3 | 4 | 5 | 6 | VI-1 | Aim1l |
| 9127 | 3 | 4 | 5 | 6 | VI-1 | Aip |
| 9128 | 3 | 4 | 5 | 6 | VI-1 | Ak2 |
| 9129 | 3 | 4 | 5 | 6 | VI-1 | Ak5 |
| 9130 | 3 | 4 | 5 | 6 | VI-1 | Ak7 |
| 9131 | 3 | 4 | 5 | 6 | VI-1 | Ak8 |
| 9132 | 3 | 4 | 5 | 6 | VI-1 | Akap1 |
| 9133 | 3 | 4 | 5 | 6 | VI-1 | Akap11 |
| 9134 | 3 | 4 | 5 | 6 | VI-1 | Akap12 |
| 9135 | 3 | 4 | 5 | 6 | VI-1 | Akap13 |
| 9136 | 3 | 4 | 5 | 6 | VI-1 | Akap3 |
| 9137 | 3 | 4 | 5 | 6 | VI-1 | Akap6 |
| 9138 | 3 | 4 | 5 | 6 | VI-1 | Akap7 |
| 9139 | 3 | 4 | 5 | 6 | VI-1 | Akirin1 |
| 9140 | 3 | 4 | 5 | 6 | VI-1 | Akr1b10 |
| 9141 | 3 | 4 | 5 | 6 | VI-1 | Akr1c12 |
| 9142 | 3 | 4 | 5 | 6 | VI-1 | Akr1c13 |
| 9143 | 3 | 4 | 5 | 6 | VI-1 | Akr1c14 |
| 9144 | 3 | 4 | 5 | 6 | VI-1 | Akr1c18 |
| 9145 | 3 | 4 | 5 | 6 | VI-1 | Akr1cl |
| 9146 | 3 | 4 | 5 | 6 | VI-1 | Akt1 |
| 9147 | 3 | 4 | 5 | 6 | VI-1 | Akt1s1 |
| 9148 | 3 | 4 | 5 | 6 | VI-1 | Akt2 |
| 9149 | 3 | 4 | 5 | 6 | VI-1 | Aktip |
| 9150 | 3 | 4 | 5 | 6 | VI-1 | Alad |
| 9151 | 3 | 4 | 5 | 6 | VI-1 | Alas2 |
| 9152 | 3 | 4 | 5 | 6 | VI-1 | Alcam |
| 9153 | 3 | 4 | 5 | 6 | VI-1 | Aldh16a1 |
| 9154 | 3 | 4 | 5 | 6 | VI-1 | Aldh1a7 |
| 9155 | 3 | 4 | 5 | 6 | VI-1 | Aldh3b1 |
| 9156 | 3 | 4 | 5 | 6 | VI-1 | Aldh5a1 |
| 9157 | 3 | 4 | 5 | 6 | VI-1 | Aldh6a1 |
| 9158 | 3 | 4 | 5 | 6 | VI-1 | Aldh8a1 |
| 9159 | 3 | 4 | 5 | 6 | VI-1 | Aldoa |
| 9160 | 3 | 4 | 5 | 6 | VI-1 | Alg10b |
| 9161 | 3 | 4 | 5 | 6 | VI-1 | Alg5 |
| 9162 | 3 | 4 | 5 | 6 | VI-1 | Alg8 |
| 9163 | 3 | 4 | 5 | 6 | VI-1 | Alg9 |
| 9164 | 3 | 4 | 5 | 6 | VI-1 | Alkbh6 |
| 9165 | 3 | 4 | 5 | 6 | VI-1 | Alox5 |
| 9166 | 3 | 4 | 5 | 6 | VI-1 | Alox5ap |
| 9167 | 3 | 4 | 5 | 6 | VI-1 | Aloxe3 |
| 9168 | 3 | 4 | 5 | 6 | VI-1 | Alpi |
| 9169 | 3 | 4 | 5 | 6 | VI-1 | Alpk2 |
| 9170 | 3 | 4 | 5 | 6 | VI-1 | Alpl |
| 9171 | 3 | 4 | 5 | 6 | VI-1 | Als2 |
| 9172 | 3 | 4 | 5 | 6 | VI-1 | Alyref2 |
| 9173 | 3 | 4 | 5 | 6 | VI-1 | Ambp |
| 9174 | 3 | 4 | 5 | 6 | VI-1 | Ambra1 |
| 9175 | 3 | 4 | 5 | 6 | VI-1 | Amdhd1 |
| 9176 | 3 | 4 | 5 | 6 | VI-1 | Amn |
| 9177 | 3 | 4 | 5 | 6 | VI-1 | Amn1 |
| 9178 | 3 | 4 | 5 | 6 | VI-1 | Amot |
| 9179 | 3 | 4 | 5 | 6 | VI-1 | Ampd1 |
| 9180 | 3 | 4 | 5 | 6 | VI-1 | Amy1 |
| 9181 | 3 | 4 | 5 | 6 | VI-1 | Amy2a2 |
| 9182 | 3 | 4 | 5 | 6 | VI-1 | Amz1 |
| 9183 | 3 | 4 | 5 | 6 | VI-1 | Amz2 |
| 9184 | 3 | 4 | 5 | 6 | VI-1 | Anapc4 |
| 9185 | 3 | 4 | 5 | 6 | VI-1 | Anapc5 |
| 9186 | 3 | 4 | 5 | 6 | VI-1 | Ang |
| 9187 | 3 | 4 | 5 | 6 | VI-1 | Angptl6 |
| 9188 | 3 | 4 | 5 | 6 | VI-1 | Ank1 |
| 9189 | 3 | 4 | 5 | 6 | VI-1 | Ank3 |
| 9190 | 3 | 4 | 5 | 6 | VI-1 | Ankdd1b |
| 9191 | 3 | 4 | 5 | 6 | VI-1 | Ankmy1 |
| 9192 | 3 | 4 | 5 | 6 | VI-1 | Ankmy2 |
| 9193 | 3 | 4 | 5 | 6 | VI-1 | Ankrd13a |
| 9194 | 3 | 4 | 5 | 6 | VI-1 | Ankrd13b |
| 9195 | 3 | 4 | 5 | 6 | VI-1 | Ankrd13d |
| 9196 | 3 | 4 | 5 | 6 | VI-1 | Ankrd16 |
| 9197 | 3 | 4 | 5 | 6 | VI-1 | Ankrd34a |
| 9198 | 3 | 4 | 5 | 6 | VI-1 | Ankrd35 |
| 9199 | 3 | 4 | 5 | 6 | VI-1 | Ankrd37 |
| 9200 | 3 | 4 | 5 | 6 | VI-1 | Ankrd39 |
| 9201 | 3 | 4 | 5 | 6 | VI-1 | Ankrd44 |
| 9202 | 3 | 4 | 5 | 6 | VI-1 | Ankrd45 |
| 9203 | 3 | 4 | 5 | 6 | VI-1 | Ankrd46 |
| 9204 | 3 | 4 | 5 | 6 | VI-1 | Ankrd54 |
| 9205 | 3 | 4 | 5 | 6 | VI-1 | Ankrd66 |
| 9206 | 3 | 4 | 5 | 6 | VI-1 | Ankrd9 |
| 9207 | 3 | 4 | 5 | 6 | VI-1 | Anks4b |
| 9208 | 3 | 4 | 5 | 6 | VI-1 | Ankzf1 |
| 9209 | 3 | 4 | 5 | 6 | VI-1 | Ano1 |
| 9210 | 3 | 4 | 5 | 6 | VI-1 | Ano10 |
| 9211 | 3 | 4 | 5 | 6 | VI-1 | Ano3 |
| 9212 | 3 | 4 | 5 | 6 | VI-1 | Ano9 |
| 9213 | 3 | 4 | 5 | 6 | VI-1 | Anp32b |
| 9214 | 3 | 4 | 5 | 6 | VI-1 | Anpep |

Fig. 34 - 49

| | | | | | | |
|---|---|---|---|---|---|---|
| 9215 | 3 | 4 | 5 | 6 | VI-1 | Antxr2 |
| 9216 | 3 | 4 | 5 | 6 | VI-1 | Anxa1 |
| 9217 | 3 | 4 | 5 | 6 | VI-1 | Anxa11 |
| 9218 | 3 | 4 | 5 | 6 | VI-1 | Anxa13 |
| 9219 | 3 | 4 | 5 | 6 | VI-1 | Anxa2 |
| 9220 | 3 | 4 | 5 | 6 | VI-1 | Anxa3 |
| 9221 | 3 | 4 | 5 | 6 | VI-1 | Anxa5 |
| 9222 | 3 | 4 | 5 | 6 | VI-1 | Anxa6 |
| 9223 | 3 | 4 | 5 | 6 | VI-1 | Anxa7 |
| 9224 | 3 | 4 | 5 | 6 | VI-1 | Anxa8 |
| 9225 | 3 | 4 | 5 | 6 | VI-1 | Aoc3 |
| 9226 | 3 | 4 | 5 | 6 | VI-1 | Ap1s1 |
| 9227 | 3 | 4 | 5 | 6 | VI-1 | Ap2a1 |
| 9228 | 3 | 4 | 5 | 6 | VI-1 | Ap2a2 |
| 9229 | 3 | 4 | 5 | 6 | VI-1 | Ap2b1 |
| 9230 | 3 | 4 | 5 | 6 | VI-1 | Ap2m1 |
| 9231 | 3 | 4 | 5 | 6 | VI-1 | Ap3b2 |
| 9232 | 3 | 4 | 5 | 6 | VI-1 | Ap3s1 |
| 9233 | 3 | 4 | 5 | 6 | VI-1 | Ap4b1 |
| 9234 | 3 | 4 | 5 | 6 | VI-1 | Ap4e1 |
| 9235 | 3 | 4 | 5 | 6 | VI-1 | Ap4m1 |
| 9236 | 3 | 4 | 5 | 6 | VI-1 | Ap4s1 |
| 9237 | 3 | 4 | 5 | 6 | VI-1 | Ap5b1 |
| 9238 | 3 | 4 | 5 | 6 | VI-1 | Ap5z1 |
| 9239 | 3 | 4 | 5 | 6 | VI-1 | Apba1 |
| 9240 | 3 | 4 | 5 | 6 | VI-1 | Apba2 |
| 9241 | 3 | 4 | 5 | 6 | VI-1 | Apbb3 |
| 9242 | 3 | 4 | 5 | 6 | VI-1 | Apc |
| 9243 | 3 | 4 | 5 | 6 | VI-1 | Apc2 |
| 9244 | 3 | 4 | 5 | 6 | VI-1 | Apela |
| 9245 | 3 | 4 | 5 | 6 | VI-1 | Apex2 |
| 9246 | 3 | 4 | 5 | 6 | VI-1 | Aph1a |
| 9247 | 3 | 4 | 5 | 6 | VI-1 | Aph1c |
| 9248 | 3 | 4 | 5 | 6 | VI-1 | Apln |
| 9249 | 3 | 4 | 5 | 6 | VI-1 | Apoa5 |
| 9250 | 3 | 4 | 5 | 6 | VI-1 | Apobec2 |
| 9251 | 3 | 4 | 5 | 6 | VI-1 | Apobec3 |
| 9252 | 3 | 4 | 5 | 6 | VI-1 | Apobr |
| 9253 | 3 | 4 | 5 | 6 | VI-1 | Apof |
| 9254 | 3 | 4 | 5 | 6 | VI-1 | Apol6 |
| 9255 | 3 | 4 | 5 | 6 | VI-1 | Apold1 |
| 9256 | 3 | 4 | 5 | 6 | VI-1 | Apoo |
| 9257 | 3 | 4 | 5 | 6 | VI-1 | Apool |
| 9258 | 3 | 4 | 5 | 6 | VI-1 | Appbp2 |
| 9259 | 3 | 4 | 5 | 6 | VI-1 | Appl1 |
| 9260 | 3 | 4 | 5 | 6 | VI-1 | Aptx |
| 9261 | 3 | 4 | 5 | 6 | VI-1 | Aqp1 |
| 9262 | 3 | 4 | 5 | 6 | VI-1 | Aqp12 |
| 9263 | 3 | 4 | 5 | 6 | VI-1 | Aqp2 |
| 9264 | 3 | 4 | 5 | 6 | VI-1 | Aqp3 |
| 9265 | 3 | 4 | 5 | 6 | VI-1 | Aqp4 |
| 9266 | 3 | 4 | 5 | 6 | VI-1 | Aqp9 |
| 9267 | 3 | 4 | 5 | 6 | VI-1 | Arap1 |
| 9268 | 3 | 4 | 5 | 6 | VI-1 | Arap3 |
| 9269 | 3 | 4 | 5 | 6 | VI-1 | Areg |
| 9270 | 3 | 4 | 5 | 6 | VI-1 | Arel1 |
| 9271 | 3 | 4 | 5 | 6 | VI-1 | Arf5 |
| 9272 | 3 | 4 | 5 | 6 | VI-1 | Arfgap1 |
| 9273 | 3 | 4 | 5 | 6 | VI-1 | Arfgap2 |
| 9274 | 3 | 4 | 5 | 6 | VI-1 | Arfgap3 |
| 9275 | 3 | 4 | 5 | 6 | VI-1 | Arfgef1 |
| 9276 | 3 | 4 | 5 | 6 | VI-1 | Arg2 |
| 9277 | 3 | 4 | 5 | 6 | VI-1 | Arglu1 |
| 9278 | 3 | 4 | 5 | 6 | VI-1 | Arhgap10 |
| 9279 | 3 | 4 | 5 | 6 | VI-1 | Arhgap15 |
| 9280 | 3 | 4 | 5 | 6 | VI-1 | Arhgap17 |
| 9281 | 3 | 4 | 5 | 6 | VI-1 | Arhgap20 |
| 9282 | 3 | 4 | 5 | 6 | VI-1 | Arhgap22 |
| 9283 | 3 | 4 | 5 | 6 | VI-1 | Arhgap25 |
| 9284 | 3 | 4 | 5 | 6 | VI-1 | Arhgap32 |
| 9285 | 3 | 4 | 5 | 6 | VI-1 | Arhgap33os |
| 9286 | 3 | 4 | 5 | 6 | VI-1 | Arhgap36 |
| 9287 | 3 | 4 | 5 | 6 | VI-1 | Arhgap44 |
| 9288 | 3 | 4 | 5 | 6 | VI-1 | Arhgap8 |
| 9289 | 3 | 4 | 5 | 6 | VI-1 | Arhgap9 |
| 9290 | 3 | 4 | 5 | 6 | VI-1 | Arhgdia |
| 9291 | 3 | 4 | 5 | 6 | VI-1 | Arhgef15 |
| 9292 | 3 | 4 | 5 | 6 | VI-1 | Arhgef16 |
| 9293 | 3 | 4 | 5 | 6 | VI-1 | Arhgef2 |
| 9294 | 3 | 4 | 5 | 6 | VI-1 | Arhgef25 |
| 9295 | 3 | 4 | 5 | 6 | VI-1 | Arhgef26 |
| 9296 | 3 | 4 | 5 | 6 | VI-1 | Arhgef28 |
| 9297 | 3 | 4 | 5 | 6 | VI-1 | Arhgef3 |
| 9298 | 3 | 4 | 5 | 6 | VI-1 | Arhgef5 |
| 9299 | 3 | 4 | 5 | 6 | VI-1 | Arhgef6 |
| 9300 | 3 | 4 | 5 | 6 | VI-1 | Arid3a |
| 9301 | 3 | 4 | 5 | 6 | VI-1 | Arid3c |
| 9302 | 3 | 4 | 5 | 6 | VI-1 | Arid4a |
| 9303 | 3 | 4 | 5 | 6 | VI-1 | Arid4b |
| 9304 | 3 | 4 | 5 | 6 | VI-1 | Arih2 |
| 9305 | 3 | 4 | 5 | 6 | VI-1 | Arl10 |
| 9306 | 3 | 4 | 5 | 6 | VI-1 | Arl11 |
| 9307 | 3 | 4 | 5 | 6 | VI-1 | Arl15 |
| 9308 | 3 | 4 | 5 | 6 | VI-1 | Arl2bp |
| 9309 | 3 | 4 | 5 | 6 | VI-1 | Arl4a |
| 9310 | 3 | 4 | 5 | 6 | VI-1 | Arl4c |
| 9311 | 3 | 4 | 5 | 6 | VI-1 | Arl5b |
| 9312 | 3 | 4 | 5 | 6 | VI-1 | Arl5c |
| 9313 | 3 | 4 | 5 | 6 | VI-1 | Arl6 |
| 9314 | 3 | 4 | 5 | 6 | VI-1 | Arl6ip4 |
| 9315 | 3 | 4 | 5 | 6 | VI-1 | Armc10 |
| 9316 | 3 | 4 | 5 | 6 | VI-1 | Armc5 |
| 9317 | 3 | 4 | 5 | 6 | VI-1 | Armc6 |
| 9318 | 3 | 4 | 5 | 6 | VI-1 | Armc7 |
| 9319 | 3 | 4 | 5 | 6 | VI-1 | Armcx3 |
| 9320 | 3 | 4 | 5 | 6 | VI-1 | Arnt |
| 9321 | 3 | 4 | 5 | 6 | VI-1 | Arnt2 |
| 9322 | 3 | 4 | 5 | 6 | VI-1 | Arntl2 |
| 9323 | 3 | 4 | 5 | 6 | VI-1 | Arpc1a |
| 9324 | 3 | 4 | 5 | 6 | VI-1 | Arpc1b |
| 9325 | 3 | 4 | 5 | 6 | VI-1 | Arpc2 |
| 9326 | 3 | 4 | 5 | 6 | VI-1 | Arpc5 |
| 9327 | 3 | 4 | 5 | 6 | VI-1 | Arpc5l |
| 9328 | 3 | 4 | 5 | 6 | VI-1 | Arpp19 |
| 9329 | 3 | 4 | 5 | 6 | VI-1 | Arrb1 |
| 9330 | 3 | 4 | 5 | 6 | VI-1 | Arrdc4 |
| 9331 | 3 | 4 | 5 | 6 | VI-1 | Arrdc5 |
| 9332 | 3 | 4 | 5 | 6 | VI-1 | Arsb |
| 9333 | 3 | 4 | 5 | 6 | VI-1 | Arsg |
| 9334 | 3 | 4 | 5 | 6 | VI-1 | Art1 |
| 9335 | 3 | 4 | 5 | 6 | VI-1 | Art2a-ps |
| 9336 | 3 | 4 | 5 | 6 | VI-1 | Art3 |
| 9337 | 3 | 4 | 5 | 6 | VI-1 | Arxes2 |
| 9338 | 3 | 4 | 5 | 6 | VI-1 | As3mt |
| 9339 | 3 | 4 | 5 | 6 | VI-1 | Asah1 |
| 9340 | 3 | 4 | 5 | 6 | VI-1 | Asah2 |
| 9341 | 3 | 4 | 5 | 6 | VI-1 | Asap3 |
| 9342 | 3 | 4 | 5 | 6 | VI-1 | Asb1 |
| 9343 | 3 | 4 | 5 | 6 | VI-1 | Asb14 |
| 9344 | 3 | 4 | 5 | 6 | VI-1 | Asb15 |
| 9345 | 3 | 4 | 5 | 6 | VI-1 | Asb16 |
| 9346 | 3 | 4 | 5 | 6 | VI-1 | Asb17 |
| 9347 | 3 | 4 | 5 | 6 | VI-1 | Asb18 |
| 9348 | 3 | 4 | 5 | 6 | VI-1 | Asb5 |
| 9349 | 3 | 4 | 5 | 6 | VI-1 | Ascl2 |
| 9350 | 3 | 4 | 5 | 6 | VI-1 | Ash2l |
| 9351 | 3 | 4 | 5 | 6 | VI-1 | Asic2 |
| 9352 | 3 | 4 | 5 | 6 | VI-1 | Asic4 |
| 9353 | 3 | 4 | 5 | 6 | VI-1 | Asic5 |
| 9354 | 3 | 4 | 5 | 6 | VI-1 | Asns |
| 9355 | 3 | 4 | 5 | 6 | VI-1 | Asnsd1 |
| 9356 | 3 | 4 | 5 | 6 | VI-1 | Aspa |
| 9357 | 3 | 4 | 5 | 6 | VI-1 | Aspn |
| 9358 | 3 | 4 | 5 | 6 | VI-1 | Asprv1 |
| 9359 | 3 | 4 | 5 | 6 | VI-1 | Aspscr1 |
| 9360 | 3 | 4 | 5 | 6 | VI-1 | Asrgl1 |
| 9361 | 3 | 4 | 5 | 6 | VI-1 | Ass1 |
| 9362 | 3 | 4 | 5 | 6 | VI-1 | Aste1 |
| 9363 | 3 | 4 | 5 | 6 | VI-1 | Astn1 |
| 9364 | 3 | 4 | 5 | 6 | VI-1 | Asxl1 |
| 9365 | 3 | 4 | 5 | 6 | VI-1 | Atad1 |
| 9366 | 3 | 4 | 5 | 6 | VI-1 | Atad3a |
| 9367 | 3 | 4 | 5 | 6 | VI-1 | Atad3aos |
| 9368 | 3 | 4 | 5 | 6 | VI-1 | Atcay |
| 9369 | 3 | 4 | 5 | 6 | VI-1 | Atcayos |
| 9370 | 3 | 4 | 5 | 6 | VI-1 | Ate1 |
| 9371 | 3 | 4 | 5 | 6 | VI-1 | Atf1 |
| 9372 | 3 | 4 | 5 | 6 | VI-1 | Atf6 |
| 9373 | 3 | 4 | 5 | 6 | VI-1 | Atf6b |
| 9374 | 3 | 4 | 5 | 6 | VI-1 | Atf7ip |
| 9375 | 3 | 4 | 5 | 6 | VI-1 | Atg10 |
| 9376 | 3 | 4 | 5 | 6 | VI-1 | Atg14 |
| 9377 | 3 | 4 | 5 | 6 | VI-1 | Atg16l1 |
| 9378 | 3 | 4 | 5 | 6 | VI-1 | Atg16l2 |
| 9379 | 3 | 4 | 5 | 6 | VI-1 | Atg2a |
| 9380 | 3 | 4 | 5 | 6 | VI-1 | Atg2b |
| 9381 | 3 | 4 | 5 | 6 | VI-1 | Atg3 |
| 9382 | 3 | 4 | 5 | 6 | VI-1 | Atg4b |
| 9383 | 3 | 4 | 5 | 6 | VI-1 | Atg4d |
| 9384 | 3 | 4 | 5 | 6 | VI-1 | Atg7 |
| 9385 | 3 | 4 | 5 | 6 | VI-1 | Atg9a |
| 9386 | 3 | 4 | 5 | 6 | VI-1 | Athl1 |
| 9387 | 3 | 4 | 5 | 6 | VI-1 | Atl1 |
| 9388 | 3 | 4 | 5 | 6 | VI-1 | Atl3 |
| 9389 | 3 | 4 | 5 | 6 | VI-1 | Atoh8 |
| 9390 | 3 | 4 | 5 | 6 | VI-1 | Atp10a |
| 9391 | 3 | 4 | 5 | 6 | VI-1 | Atp10d |
| 9392 | 3 | 4 | 5 | 6 | VI-1 | Atp11c |
| 9393 | 3 | 4 | 5 | 6 | VI-1 | Atp13a3 |
| 9394 | 3 | 4 | 5 | 6 | VI-1 | Atp1a4 |
| 9395 | 3 | 4 | 5 | 6 | VI-1 | Atp1b3 |
| 9396 | 3 | 4 | 5 | 6 | VI-1 | Atp2b1 |
| 9397 | 3 | 4 | 5 | 6 | VI-1 | Atp2b3 |
| 9398 | 3 | 4 | 5 | 6 | VI-1 | Atp2b4 |
| 9399 | 3 | 4 | 5 | 6 | VI-1 | Atp2c2 |
| 9400 | 3 | 4 | 5 | 6 | VI-1 | Atp5a1 |
| 9401 | 3 | 4 | 5 | 6 | VI-1 | Atp5b |
| 9402 | 3 | 4 | 5 | 6 | VI-1 | Atp5g1 |
| 9403 | 3 | 4 | 5 | 6 | VI-1 | Atp5g2 |
| 9404 | 3 | 4 | 5 | 6 | VI-1 | Atp6ap1l |
| 9405 | 3 | 4 | 5 | 6 | VI-1 | Atp6ap2 |
| 9406 | 3 | 4 | 5 | 6 | VI-1 | Atp6v0a1 |

Fig. 34 - 50

| | | | | | | |
|---|---|---|---|---|---|---|
| 9407 | 3 | 4 | 5 | 6 | VI-1 | Atp6v0a4 |
| 9408 | 3 | 4 | 5 | 6 | VI-1 | Atp6v0d1 |
| 9409 | 3 | 4 | 5 | 6 | VI-1 | Atp6v0e |
| 9410 | 3 | 4 | 5 | 6 | VI-1 | Atp6v0e2 |
| 9411 | 3 | 4 | 5 | 6 | VI-1 | Atp6v1b2 |
| 9412 | 3 | 4 | 5 | 6 | VI-1 | Atp6v1c1 |
| 9413 | 3 | 4 | 5 | 6 | VI-1 | Atp6v1c2 |
| 9414 | 3 | 4 | 5 | 6 | VI-1 | Atp6v1f |
| 9415 | 3 | 4 | 5 | 6 | VI-1 | Atp6v1g1 |
| 9416 | 3 | 4 | 5 | 6 | VI-1 | Atp7a |
| 9417 | 3 | 4 | 5 | 6 | VI-1 | Atp8a1 |
| 9418 | 3 | 4 | 5 | 6 | VI-1 | Atp8b1 |
| 9419 | 3 | 4 | 5 | 6 | VI-1 | Atpaf2 |
| 9420 | 3 | 4 | 5 | 6 | VI-1 | Atrip |
| 9421 | 3 | 4 | 5 | 6 | VI-1 | Atxn1 |
| 9422 | 3 | 4 | 5 | 6 | VI-1 | Atxn7 |
| 9423 | 3 | 4 | 5 | 6 | VI-1 | Aurka |
| 9424 | 3 | 4 | 5 | 6 | VI-1 | Auts2 |
| 9425 | 3 | 4 | 5 | 6 | VI-1 | Aven |
| 9426 | 3 | 4 | 5 | 6 | VI-1 | Avil |
| 9427 | 3 | 4 | 5 | 6 | VI-1 | Avl9 |
| 9428 | 3 | 4 | 5 | 6 | VI-1 | Avp |
| 9429 | 3 | 4 | 5 | 6 | VI-1 | Avpi1 |
| 9430 | 3 | 4 | 5 | 6 | VI-1 | Avpr1a |
| 9431 | 3 | 4 | 5 | 6 | VI-1 | Awat2 |
| 9432 | 3 | 4 | 5 | 6 | VI-1 | Axin1 |
| 9433 | 3 | 4 | 5 | 6 | VI-1 | Aym1 |
| 9434 | 3 | 4 | 5 | 6 | VI-1 | Azgp1 |
| 9435 | 3 | 4 | 5 | 6 | VI-1 | Azin1 |
| 9436 | 3 | 4 | 5 | 6 | VI-1 | B020031M17Rik |
| 9437 | 3 | 4 | 5 | 6 | VI-1 | B230118H07Rik |
| 9438 | 3 | 4 | 5 | 6 | VI-1 | B230208H11Rik |
| 9439 | 3 | 4 | 5 | 6 | VI-1 | B230216G23Rik |
| 9440 | 3 | 4 | 5 | 6 | VI-1 | B230216N24Rik |
| 9441 | 3 | 4 | 5 | 6 | VI-1 | B2m |
| 9442 | 3 | 4 | 5 | 6 | VI-1 | B3galnt1 |
| 9443 | 3 | 4 | 5 | 6 | VI-1 | B3galt4 |
| 9444 | 3 | 4 | 5 | 6 | VI-1 | B3galt5 |
| 9445 | 3 | 4 | 5 | 6 | VI-1 | B3galt6 |
| 9446 | 3 | 4 | 5 | 6 | VI-1 | B3gat3 |
| 9447 | 3 | 4 | 5 | 6 | VI-1 | B3gnt2 |
| 9448 | 3 | 4 | 5 | 6 | VI-1 | B3gnt3 |
| 9449 | 3 | 4 | 5 | 6 | VI-1 | B3gnt7 |
| 9450 | 3 | 4 | 5 | 6 | VI-1 | B3gntl1 |
| 9451 | 3 | 4 | 5 | 6 | VI-1 | B430212C06Rik |
| 9452 | 3 | 4 | 5 | 6 | VI-1 | B430306N03Rik |
| 9453 | 3 | 4 | 5 | 6 | VI-1 | B4galnt2 |
| 9454 | 3 | 4 | 5 | 6 | VI-1 | B4galt1 |
| 9455 | 3 | 4 | 5 | 6 | VI-1 | B4galt2 |
| 9456 | 3 | 4 | 5 | 6 | VI-1 | B4galt3 |
| 9457 | 3 | 4 | 5 | 6 | VI-1 | B4galt6 |
| 9458 | 3 | 4 | 5 | 6 | VI-1 | B4galt7 |
| 9459 | 3 | 4 | 5 | 6 | VI-1 | B630005N14Rik |
| 9460 | 3 | 4 | 5 | 6 | VI-1 | B630019K06Rik |
| 9461 | 3 | 4 | 5 | 6 | VI-1 | B830017H08Rik |
| 9462 | 3 | 4 | 5 | 6 | VI-1 | B930025P03Rik |
| 9463 | 3 | 4 | 5 | 6 | VI-1 | BB014433 |
| 9464 | 3 | 4 | 5 | 6 | VI-1 | BB123696 |
| 9465 | 3 | 4 | 5 | 6 | VI-1 | BB287469 |
| 9466 | 3 | 4 | 5 | 6 | VI-1 | BC002163 |
| 9467 | 3 | 4 | 5 | 6 | VI-1 | BC003331 |
| 9468 | 3 | 4 | 5 | 6 | VI-1 | BC003965 |
| 9469 | 3 | 4 | 5 | 6 | VI-1 | BC017643 |
| 9470 | 3 | 4 | 5 | 6 | VI-1 | BC018242 |
| 9471 | 3 | 4 | 5 | 6 | VI-1 | BC018507 |
| 9472 | 3 | 4 | 5 | 6 | VI-1 | BC020402 |
| 9473 | 3 | 4 | 5 | 6 | VI-1 | BC021767 |
| 9474 | 3 | 4 | 5 | 6 | VI-1 | BC024978 |
| 9475 | 3 | 4 | 5 | 6 | VI-1 | BC026585 |
| 9476 | 3 | 4 | 5 | 6 | VI-1 | BC029722 |
| 9477 | 3 | 4 | 5 | 6 | VI-1 | BC030867 |
| 9478 | 3 | 4 | 5 | 6 | VI-1 | BC031181 |
| 9479 | 3 | 4 | 5 | 6 | VI-1 | BC039771 |
| 9480 | 3 | 4 | 5 | 6 | VI-1 | BC048403 |
| 9481 | 3 | 4 | 5 | 6 | VI-1 | BC048562 |
| 9482 | 3 | 4 | 5 | 6 | VI-1 | BC048609 |
| 9483 | 3 | 4 | 5 | 6 | VI-1 | BC049635 |
| 9484 | 3 | 4 | 5 | 6 | VI-1 | BC049762 |
| 9485 | 3 | 4 | 5 | 6 | VI-1 | BC051019 |
| 9486 | 3 | 4 | 5 | 6 | VI-1 | BC053749 |
| 9487 | 3 | 4 | 5 | 6 | VI-1 | BC055111 |
| 9488 | 3 | 4 | 5 | 6 | VI-1 | BC068281 |
| 9489 | 3 | 4 | 5 | 6 | VI-1 | BC089491 |
| 9490 | 3 | 4 | 5 | 6 | VI-1 | BC089597 |
| 9491 | 3 | 4 | 5 | 6 | VI-1 | BC094916 |
| 9492 | 3 | 4 | 5 | 6 | VI-1 | BC100451 |
| 9493 | 3 | 4 | 5 | 6 | VI-1 | Babam1 |
| 9494 | 3 | 4 | 5 | 6 | VI-1 | Bace2 |
| 9495 | 3 | 4 | 5 | 6 | VI-1 | Bach1 |
| 9496 | 3 | 4 | 5 | 6 | VI-1 | Bach2 |
| 9497 | 3 | 4 | 5 | 6 | VI-1 | Bad |
| 9498 | 3 | 4 | 5 | 6 | VI-1 | Bag2 |
| 9499 | 3 | 4 | 5 | 6 | VI-1 | Bag3 |
| 9500 | 3 | 4 | 5 | 6 | VI-1 | Bag4 |
| 9501 | 3 | 4 | 5 | 6 | VI-1 | Bai2 |
| 9502 | 3 | 4 | 5 | 6 | VI-1 | Baiap2 |
| 9503 | 3 | 4 | 5 | 6 | VI-1 | Baiap2l2 |
| 9504 | 3 | 4 | 5 | 6 | VI-1 | Bak1 |
| 9505 | 3 | 4 | 5 | 6 | VI-1 | Bambi-ps1 |
| 9506 | 3 | 4 | 5 | 6 | VI-1 | Banf1 |
| 9507 | 3 | 4 | 5 | 6 | VI-1 | Banf2 |
| 9508 | 3 | 4 | 5 | 6 | VI-1 | Bap1 |
| 9509 | 3 | 4 | 5 | 6 | VI-1 | Batf |
| 9510 | 3 | 4 | 5 | 6 | VI-1 | Batf2 |
| 9511 | 3 | 4 | 5 | 6 | VI-1 | Bax |
| 9512 | 3 | 4 | 5 | 6 | VI-1 | Bbc3 |
| 9513 | 3 | 4 | 5 | 6 | VI-1 | Bbip1 |
| 9514 | 3 | 4 | 5 | 6 | VI-1 | Bbox1 |
| 9515 | 3 | 4 | 5 | 6 | VI-1 | Bbs1 |
| 9516 | 3 | 4 | 5 | 6 | VI-1 | Bbs2 |
| 9517 | 3 | 4 | 5 | 6 | VI-1 | Bbs4 |
| 9518 | 3 | 4 | 5 | 6 | VI-1 | Bbs5 |
| 9519 | 3 | 4 | 5 | 6 | VI-1 | Bbs7 |
| 9520 | 3 | 4 | 5 | 6 | VI-1 | Bcar1 |
| 9521 | 3 | 4 | 5 | 6 | VI-1 | Bcar3 |
| 9522 | 3 | 4 | 5 | 6 | VI-1 | Bcas3 |
| 9523 | 3 | 4 | 5 | 6 | VI-1 | Bcat1 |
| 9524 | 3 | 4 | 5 | 6 | VI-1 | Bcdin3d |
| 9525 | 3 | 4 | 5 | 6 | VI-1 | Bckdha |
| 9526 | 3 | 4 | 5 | 6 | VI-1 | Bcl11a |
| 9527 | 3 | 4 | 5 | 6 | VI-1 | Bcl11b |
| 9528 | 3 | 4 | 5 | 6 | VI-1 | Bcl2 |
| 9529 | 3 | 4 | 5 | 6 | VI-1 | Bcl2a1a |
| 9530 | 3 | 4 | 5 | 6 | VI-1 | Bcl2a1d |
| 9531 | 3 | 4 | 5 | 6 | VI-1 | Bcl2l1 |
| 9532 | 3 | 4 | 5 | 6 | VI-1 | Bcl2l10 |
| 9533 | 3 | 4 | 5 | 6 | VI-1 | Bcl2l11 |
| 9534 | 3 | 4 | 5 | 6 | VI-1 | Bcl2l12 |
| 9535 | 3 | 4 | 5 | 6 | VI-1 | Bcl2l14 |
| 9536 | 3 | 4 | 5 | 6 | VI-1 | Bcl6 |
| 9537 | 3 | 4 | 5 | 6 | VI-1 | Bcl6b |
| 9538 | 3 | 4 | 5 | 6 | VI-1 | Bcl7b |
| 9539 | 3 | 4 | 5 | 6 | VI-1 | Bclaf1 |
| 9540 | 3 | 4 | 5 | 6 | VI-1 | Bcmo1 |
| 9541 | 3 | 4 | 5 | 6 | VI-1 | Bco2 |
| 9542 | 3 | 4 | 5 | 6 | VI-1 | Bcr |
| 9543 | 3 | 4 | 5 | 6 | VI-1 | Bcs1l |
| 9544 | 3 | 4 | 5 | 6 | VI-1 | Bdh1 |
| 9545 | 3 | 4 | 5 | 6 | VI-1 | Bdp1 |
| 9546 | 3 | 4 | 5 | 6 | VI-1 | Bean1 |
| 9547 | 3 | 4 | 5 | 6 | VI-1 | Becn1 |
| 9548 | 3 | 4 | 5 | 6 | VI-1 | Begain |
| 9549 | 3 | 4 | 5 | 6 | VI-1 | Bend4 |
| 9550 | 3 | 4 | 5 | 6 | VI-1 | Bend5 |
| 9551 | 3 | 4 | 5 | 6 | VI-1 | Bend7 |
| 9552 | 3 | 4 | 5 | 6 | VI-1 | Best3 |
| 9553 | 3 | 4 | 5 | 6 | VI-1 | Bet1l |
| 9554 | 3 | 4 | 5 | 6 | VI-1 | Bfar |
| 9555 | 3 | 4 | 5 | 6 | VI-1 | Bfsp1 |
| 9556 | 3 | 4 | 5 | 6 | VI-1 | Bglap |
| 9557 | 3 | 4 | 5 | 6 | VI-1 | Bgn |
| 9558 | 3 | 4 | 5 | 6 | VI-1 | Bhlha15 |
| 9559 | 3 | 4 | 5 | 6 | VI-1 | Bhlhb9 |
| 9560 | 3 | 4 | 5 | 6 | VI-1 | Bhlhe22 |
| 9561 | 3 | 4 | 5 | 6 | VI-1 | Bhmt |
| 9562 | 3 | 4 | 5 | 6 | VI-1 | Bicd1 |
| 9563 | 3 | 4 | 5 | 6 | VI-1 | Bicd2 |
| 9564 | 3 | 4 | 5 | 6 | VI-1 | Birc3 |
| 9565 | 3 | 4 | 5 | 6 | VI-1 | Birc5 |
| 9566 | 3 | 4 | 5 | 6 | VI-1 | Bivm |
| 9567 | 3 | 4 | 5 | 6 | VI-1 | Blcap |
| 9568 | 3 | 4 | 5 | 6 | VI-1 | Blk |
| 9569 | 3 | 4 | 5 | 6 | VI-1 | Blm |
| 9570 | 3 | 4 | 5 | 6 | VI-1 | Blmh |
| 9571 | 3 | 4 | 5 | 6 | VI-1 | Bloc1s3 |
| 9572 | 3 | 4 | 5 | 6 | VI-1 | Bloc1s4 |
| 9573 | 3 | 4 | 5 | 6 | VI-1 | Bloc1s5 |
| 9574 | 3 | 4 | 5 | 6 | VI-1 | Bmf |
| 9575 | 3 | 4 | 5 | 6 | VI-1 | Bmp2k |
| 9576 | 3 | 4 | 5 | 6 | VI-1 | Bmp4 |
| 9577 | 3 | 4 | 5 | 6 | VI-1 | Bmp7 |
| 9578 | 3 | 4 | 5 | 6 | VI-1 | Bmpr1b |
| 9579 | 3 | 4 | 5 | 6 | VI-1 | Bmpr2 |
| 9580 | 3 | 4 | 5 | 6 | VI-1 | Bms1 |
| 9581 | 3 | 4 | 5 | 6 | VI-1 | Bmx |
| 9582 | 3 | 4 | 5 | 6 | VI-1 | Bnip2 |
| 9583 | 3 | 4 | 5 | 6 | VI-1 | Bnip3 |
| 9584 | 3 | 4 | 5 | 6 | VI-1 | Bnip3l |
| 9585 | 3 | 4 | 5 | 6 | VI-1 | Bnipl |
| 9586 | 3 | 4 | 5 | 6 | VI-1 | Boc |
| 9587 | 3 | 4 | 5 | 6 | VI-1 | Bod1 |
| 9588 | 3 | 4 | 5 | 6 | VI-1 | Bok |
| 9589 | 3 | 4 | 5 | 6 | VI-1 | Bop1 |
| 9590 | 3 | 4 | 5 | 6 | VI-1 | Bpifa2 |
| 9591 | 3 | 4 | 5 | 6 | VI-1 | Bpifa3 |
| 9592 | 3 | 4 | 5 | 6 | VI-1 | Bpifb1 |
| 9593 | 3 | 4 | 5 | 6 | VI-1 | Bpnt1 |
| 9594 | 3 | 4 | 5 | 6 | VI-1 | Braf |
| 9595 | 3 | 4 | 5 | 6 | VI-1 | Brap |
| 9596 | 3 | 4 | 5 | 6 | VI-1 | Brcc3 |
| 9597 | 3 | 4 | 5 | 6 | VI-1 | Brd2 |
| 9598 | 3 | 4 | 5 | 6 | VI-1 | Brd9 |

Fig. 34 - 51

| | | | | | | |
|---|---|---|---|---|---|---|
| 9599 | 3 | 4 | 5 | 6 | VI-1 | Brf1 |
| 9600 | 3 | 4 | 5 | 6 | VI-1 | Brf2 |
| 9601 | 3 | 4 | 5 | 6 | VI-1 | Bri3 |
| 9602 | 3 | 4 | 5 | 6 | VI-1 | Bri3bp |
| 9603 | 3 | 4 | 5 | 6 | VI-1 | Brinp2 |
| 9604 | 3 | 4 | 5 | 6 | VI-1 | Brix1 |
| 9605 | 3 | 4 | 5 | 6 | VI-1 | Brk1 |
| 9606 | 3 | 4 | 5 | 6 | VI-1 | Brsk2 |
| 9607 | 3 | 4 | 5 | 6 | VI-1 | Bsdc1 |
| 9608 | 3 | 4 | 5 | 6 | VI-1 | Bsg |
| 9609 | 3 | 4 | 5 | 6 | VI-1 | Bsn |
| 9610 | 3 | 4 | 5 | 6 | VI-1 | Bspry |
| 9611 | 3 | 4 | 5 | 6 | VI-1 | Bst1 |
| 9612 | 3 | 4 | 5 | 6 | VI-1 | Btbd1 |
| 9613 | 3 | 4 | 5 | 6 | VI-1 | Btbd11 |
| 9614 | 3 | 4 | 5 | 6 | VI-1 | Btbd16 |
| 9615 | 3 | 4 | 5 | 6 | VI-1 | Btbd19 |
| 9616 | 3 | 4 | 5 | 6 | VI-1 | Btbd7 |
| 9617 | 3 | 4 | 5 | 6 | VI-1 | Btc |
| 9618 | 3 | 4 | 5 | 6 | VI-1 | Btf3 |
| 9619 | 3 | 4 | 5 | 6 | VI-1 | Btg3 |
| 9620 | 3 | 4 | 5 | 6 | VI-1 | Btk |
| 9621 | 3 | 4 | 5 | 6 | VI-1 | Btn1a1 |
| 9622 | 3 | 4 | 5 | 6 | VI-1 | Btnl2 |
| 9623 | 3 | 4 | 5 | 6 | VI-1 | Btnl4 |
| 9624 | 3 | 4 | 5 | 6 | VI-1 | Bub3 |
| 9625 | 3 | 4 | 5 | 6 | VI-1 | Bud13 |
| 9626 | 3 | 4 | 5 | 6 | VI-1 | Bves |
| 9627 | 3 | 4 | 5 | 6 | VI-1 | Bysl |
| 9628 | 3 | 4 | 5 | 6 | VI-1 | Bzrap1 |
| 9629 | 3 | 4 | 5 | 6 | VI-1 | C030006K11Rik |
| 9630 | 3 | 4 | 5 | 6 | VI-1 | C030018K13Rik |
| 9631 | 3 | 4 | 5 | 6 | VI-1 | C030034I22Rik |
| 9632 | 3 | 4 | 5 | 6 | VI-1 | C030037D09Rik |
| 9633 | 3 | 4 | 5 | 6 | VI-1 | C130026I21Rik |
| 9634 | 3 | 4 | 5 | 6 | VI-1 | C1d |
| 9635 | 3 | 4 | 5 | 6 | VI-1 | C1galt1 |
| 9636 | 3 | 4 | 5 | 6 | VI-1 | C1qbp |
| 9637 | 3 | 4 | 5 | 6 | VI-1 | C1ql2 |
| 9638 | 3 | 4 | 5 | 6 | VI-1 | C1ql3 |
| 9639 | 3 | 4 | 5 | 6 | VI-1 | C1qtnf5 |
| 9640 | 3 | 4 | 5 | 6 | VI-1 | C1qtnf6 |
| 9641 | 3 | 4 | 5 | 6 | VI-1 | C1qtnf9 |
| 9642 | 3 | 4 | 5 | 6 | VI-1 | C1s2 |
| 9643 | 3 | 4 | 5 | 6 | VI-1 | C230037L18Rik |
| 9644 | 3 | 4 | 5 | 6 | VI-1 | C330007P06Rik |
| 9645 | 3 | 4 | 5 | 6 | VI-1 | C330013E15Rik |
| 9646 | 3 | 4 | 5 | 6 | VI-1 | C330021F23Rik |
| 9647 | 3 | 4 | 5 | 6 | VI-1 | C3ar1 |
| 9648 | 3 | 4 | 5 | 6 | VI-1 | C530008M17Rik |
| 9649 | 3 | 4 | 5 | 6 | VI-1 | C5ar1 |
| 9650 | 3 | 4 | 5 | 6 | VI-1 | C630043F03Rik |
| 9651 | 3 | 4 | 5 | 6 | VI-1 | C8g |
| 9652 | 3 | 4 | 5 | 6 | VI-1 | C9 |
| 9653 | 3 | 4 | 5 | 6 | VI-1 | C920006O11Rik |
| 9654 | 3 | 4 | 5 | 6 | VI-1 | C920021L13Rik |
| 9655 | 3 | 4 | 5 | 6 | VI-1 | C920025E04Rik |
| 9656 | 3 | 4 | 5 | 6 | VI-1 | Cabp1 |
| 9657 | 3 | 4 | 5 | 6 | VI-1 | Cabp2 |
| 9658 | 3 | 4 | 5 | 6 | VI-1 | Cabp4 |
| 9659 | 3 | 4 | 5 | 6 | VI-1 | Cabs1 |
| 9660 | 3 | 4 | 5 | 6 | VI-1 | Cabyr |
| 9661 | 3 | 4 | 5 | 6 | VI-1 | Cacfd1 |
| 9662 | 3 | 4 | 5 | 6 | VI-1 | Cacna1b |
| 9663 | 3 | 4 | 5 | 6 | VI-1 | Cacna1e |
| 9664 | 3 | 4 | 5 | 6 | VI-1 | Cacna1h |
| 9665 | 3 | 4 | 5 | 6 | VI-1 | Cacna1s |
| 9666 | 3 | 4 | 5 | 6 | VI-1 | Cacna2d1 |
| 9667 | 3 | 4 | 5 | 6 | VI-1 | Cacnb1 |
| 9668 | 3 | 4 | 5 | 6 | VI-1 | Cacnb2 |
| 9669 | 3 | 4 | 5 | 6 | VI-1 | Cacng4 |
| 9670 | 3 | 4 | 5 | 6 | VI-1 | Cacng7 |
| 9671 | 3 | 4 | 5 | 6 | VI-1 | Cacng8 |
| 9672 | 3 | 4 | 5 | 6 | VI-1 | Cacul1 |
| 9673 | 3 | 4 | 5 | 6 | VI-1 | Cadm2 |
| 9674 | 3 | 4 | 5 | 6 | VI-1 | Cadps |
| 9675 | 3 | 4 | 5 | 6 | VI-1 | Cadps2 |
| 9676 | 3 | 4 | 5 | 6 | VI-1 | Calcoco1 |
| 9677 | 3 | 4 | 5 | 6 | VI-1 | Calcrl |
| 9678 | 3 | 4 | 5 | 6 | VI-1 | Cald1 |
| 9679 | 3 | 4 | 5 | 6 | VI-1 | Calm3 |
| 9680 | 3 | 4 | 5 | 6 | VI-1 | Caln1 |
| 9681 | 3 | 4 | 5 | 6 | VI-1 | Calr3 |
| 9682 | 3 | 4 | 5 | 6 | VI-1 | Calr4 |
| 9683 | 3 | 4 | 5 | 6 | VI-1 | Calu |
| 9684 | 3 | 4 | 5 | 6 | VI-1 | Camk2g |
| 9685 | 3 | 4 | 5 | 6 | VI-1 | Camkk1 |
| 9686 | 3 | 4 | 5 | 6 | VI-1 | Camsap3 |
| 9687 | 3 | 4 | 5 | 6 | VI-1 | Camta1 |
| 9688 | 3 | 4 | 5 | 6 | VI-1 | Capns1 |
| 9689 | 3 | 4 | 5 | 6 | VI-1 | Capsl |
| 9690 | 3 | 4 | 5 | 6 | VI-1 | Capza3 |
| 9691 | 3 | 4 | 5 | 6 | VI-1 | Capzb |
| 9692 | 3 | 4 | 5 | 6 | VI-1 | Car10 |
| 9693 | 3 | 4 | 5 | 6 | VI-1 | Car11 |
| 9694 | 3 | 4 | 5 | 6 | VI-1 | Car13 |
| 9695 | 3 | 4 | 5 | 6 | VI-1 | Car4 |
| 9696 | 3 | 4 | 5 | 6 | VI-1 | Car5b |
| 9697 | 3 | 4 | 5 | 6 | VI-1 | Car8 |
| 9698 | 3 | 4 | 5 | 6 | VI-1 | Car9 |
| 9699 | 3 | 4 | 5 | 6 | VI-1 | Cartpt |
| 9700 | 3 | 4 | 5 | 6 | VI-1 | Casc1 |
| 9701 | 3 | 4 | 5 | 6 | VI-1 | Casc3 |
| 9702 | 3 | 4 | 5 | 6 | VI-1 | Casc4 |
| 9703 | 3 | 4 | 5 | 6 | VI-1 | Cask |
| 9704 | 3 | 4 | 5 | 6 | VI-1 | Caskin1 |
| 9705 | 3 | 4 | 5 | 6 | VI-1 | Casp1 |
| 9706 | 3 | 4 | 5 | 6 | VI-1 | Casp12 |
| 9707 | 3 | 4 | 5 | 6 | VI-1 | Casp14 |
| 9708 | 3 | 4 | 5 | 6 | VI-1 | Casp2 |
| 9709 | 3 | 4 | 5 | 6 | VI-1 | Casp3 |
| 9710 | 3 | 4 | 5 | 6 | VI-1 | Casp9 |
| 9711 | 3 | 4 | 5 | 6 | VI-1 | Cat |
| 9712 | 3 | 4 | 5 | 6 | VI-1 | Catip |
| 9713 | 3 | 4 | 5 | 6 | VI-1 | Catsper3 |
| 9714 | 3 | 4 | 5 | 6 | VI-1 | Catsperd |
| 9715 | 3 | 4 | 5 | 6 | VI-1 | Catsperg2 |
| 9716 | 3 | 4 | 5 | 6 | VI-1 | Cbfa2t3 |
| 9717 | 3 | 4 | 5 | 6 | VI-1 | Cbr1 |
| 9718 | 3 | 4 | 5 | 6 | VI-1 | Cbr2 |
| 9719 | 3 | 4 | 5 | 6 | VI-1 | Cbx2 |
| 9720 | 3 | 4 | 5 | 6 | VI-1 | Cbx3 |
| 9721 | 3 | 4 | 5 | 6 | VI-1 | Cbx7 |
| 9722 | 3 | 4 | 5 | 6 | VI-1 | Cc2d1b |
| 9723 | 3 | 4 | 5 | 6 | VI-1 | Ccbl1 |
| 9724 | 3 | 4 | 5 | 6 | VI-1 | Ccdc102a |
| 9725 | 3 | 4 | 5 | 6 | VI-1 | Ccdc103 |
| 9726 | 3 | 4 | 5 | 6 | VI-1 | Ccdc104 |
| 9727 | 3 | 4 | 5 | 6 | VI-1 | Ccdc108 |
| 9728 | 3 | 4 | 5 | 6 | VI-1 | Ccdc109b |
| 9729 | 3 | 4 | 5 | 6 | VI-1 | Ccdc112 |
| 9730 | 3 | 4 | 5 | 6 | VI-1 | Ccdc114 |
| 9731 | 3 | 4 | 5 | 6 | VI-1 | Ccdc121 |
| 9732 | 3 | 4 | 5 | 6 | VI-1 | Ccdc130 |
| 9733 | 3 | 4 | 5 | 6 | VI-1 | Ccdc134 |
| 9734 | 3 | 4 | 5 | 6 | VI-1 | Ccdc135 |
| 9735 | 3 | 4 | 5 | 6 | VI-1 | Ccdc136 |
| 9736 | 3 | 4 | 5 | 6 | VI-1 | Ccdc137 |
| 9737 | 3 | 4 | 5 | 6 | VI-1 | Ccdc141 |
| 9738 | 3 | 4 | 5 | 6 | VI-1 | Ccdc148 |
| 9739 | 3 | 4 | 5 | 6 | VI-1 | Ccdc151 |
| 9740 | 3 | 4 | 5 | 6 | VI-1 | Ccdc152 |
| 9741 | 3 | 4 | 5 | 6 | VI-1 | Ccdc154 |
| 9742 | 3 | 4 | 5 | 6 | VI-1 | Ccdc157 |
| 9743 | 3 | 4 | 5 | 6 | VI-1 | Ccdc162 |
| 9744 | 3 | 4 | 5 | 6 | VI-1 | Ccdc166 |
| 9745 | 3 | 4 | 5 | 6 | VI-1 | Ccdc167 |
| 9746 | 3 | 4 | 5 | 6 | VI-1 | Ccdc17 |
| 9747 | 3 | 4 | 5 | 6 | VI-1 | Ccdc174 |
| 9748 | 3 | 4 | 5 | 6 | VI-1 | Ccdc181 |
| 9749 | 3 | 4 | 5 | 6 | VI-1 | Ccdc184 |
| 9750 | 3 | 4 | 5 | 6 | VI-1 | Ccdc19 |
| 9751 | 3 | 4 | 5 | 6 | VI-1 | Ccdc24 |
| 9752 | 3 | 4 | 5 | 6 | VI-1 | Ccdc28a |
| 9753 | 3 | 4 | 5 | 6 | VI-1 | Ccdc33 |
| 9754 | 3 | 4 | 5 | 6 | VI-1 | Ccdc40 |
| 9755 | 3 | 4 | 5 | 6 | VI-1 | Ccdc54 |
| 9756 | 3 | 4 | 5 | 6 | VI-1 | Ccdc57 |
| 9757 | 3 | 4 | 5 | 6 | VI-1 | Ccdc58 |
| 9758 | 3 | 4 | 5 | 6 | VI-1 | Ccdc6 |
| 9759 | 3 | 4 | 5 | 6 | VI-1 | Ccdc60 |
| 9760 | 3 | 4 | 5 | 6 | VI-1 | Ccdc61 |
| 9761 | 3 | 4 | 5 | 6 | VI-1 | Ccdc63 |
| 9762 | 3 | 4 | 5 | 6 | VI-1 | Ccdc65 |
| 9763 | 3 | 4 | 5 | 6 | VI-1 | Ccdc68 |
| 9764 | 3 | 4 | 5 | 6 | VI-1 | Ccdc69 |
| 9765 | 3 | 4 | 5 | 6 | VI-1 | Ccdc70 |
| 9766 | 3 | 4 | 5 | 6 | VI-1 | Ccdc71l |
| 9767 | 3 | 4 | 5 | 6 | VI-1 | Ccdc77 |
| 9768 | 3 | 4 | 5 | 6 | VI-1 | Ccdc78 |
| 9769 | 3 | 4 | 5 | 6 | VI-1 | Ccdc84 |
| 9770 | 3 | 4 | 5 | 6 | VI-1 | Ccdc85a |
| 9771 | 3 | 4 | 5 | 6 | VI-1 | Ccdc85c |
| 9772 | 3 | 4 | 5 | 6 | VI-1 | Ccdc86 |
| 9773 | 3 | 4 | 5 | 6 | VI-1 | Ccdc88b |
| 9774 | 3 | 4 | 5 | 6 | VI-1 | Ccdc88c |
| 9775 | 3 | 4 | 5 | 6 | VI-1 | Ccdc91 |
| 9776 | 3 | 4 | 5 | 6 | VI-1 | Ccdc92 |
| 9777 | 3 | 4 | 5 | 6 | VI-1 | Ccdc93 |
| 9778 | 3 | 4 | 5 | 6 | VI-1 | Ccdc94 |
| 9779 | 3 | 4 | 5 | 6 | VI-1 | Ccdc96 |
| 9780 | 3 | 4 | 5 | 6 | VI-1 | Ccer1 |
| 9781 | 3 | 4 | 5 | 6 | VI-1 | Cchcr1 |
| 9782 | 3 | 4 | 5 | 6 | VI-1 | Ccl1 |
| 9783 | 3 | 4 | 5 | 6 | VI-1 | Ccl2 |
| 9784 | 3 | 4 | 5 | 6 | VI-1 | Ccl22 |
| 9785 | 3 | 4 | 5 | 6 | VI-1 | Ccl3 |
| 9786 | 3 | 4 | 5 | 6 | VI-1 | Ccl4 |
| 9787 | 3 | 4 | 5 | 6 | VI-1 | Ccl5 |
| 9788 | 3 | 4 | 5 | 6 | VI-1 | Ccl7 |
| 9789 | 3 | 4 | 5 | 6 | VI-1 | Ccm2l |
| 9790 | 3 | 4 | 5 | 6 | VI-1 | Ccna2 |

Fig. 34 - 52

| | | | | | | |
|---|---|---|---|---|---|---|
| 9791 | 3 | 4 | 5 | 6 | VI-1 | Ccnb2 |
| 9792 | 3 | 4 | 5 | 6 | VI-1 | Ccnd1 |
| 9793 | 3 | 4 | 5 | 6 | VI-1 | Ccnd3 |
| 9794 | 3 | 4 | 5 | 6 | VI-1 | Ccndbp1 |
| 9795 | 3 | 4 | 5 | 6 | VI-1 | Ccng1 |
| 9796 | 3 | 4 | 5 | 6 | VI-1 | Ccng2 |
| 9797 | 3 | 4 | 5 | 6 | VI-1 | Ccnj |
| 9798 | 3 | 4 | 5 | 6 | VI-1 | Ccnk |
| 9799 | 3 | 4 | 5 | 6 | VI-1 | Ccnl1 |
| 9800 | 3 | 4 | 5 | 6 | VI-1 | Ccnl2 |
| 9801 | 3 | 4 | 5 | 6 | VI-1 | Ccno |
| 9802 | 3 | 4 | 5 | 6 | VI-1 | Ccnt1 |
| 9803 | 3 | 4 | 5 | 6 | VI-1 | Ccnyl1 |
| 9804 | 3 | 4 | 5 | 6 | VI-1 | Ccp110 |
| 9805 | 3 | 4 | 5 | 6 | VI-1 | Ccpg1 |
| 9806 | 3 | 4 | 5 | 6 | VI-1 | Ccpg1os |
| 9807 | 3 | 4 | 5 | 6 | VI-1 | Ccr1 |
| 9808 | 3 | 4 | 5 | 6 | VI-1 | Ccr7 |
| 9809 | 3 | 4 | 5 | 6 | VI-1 | Ccrl2 |
| 9810 | 3 | 4 | 5 | 6 | VI-1 | Ccsap |
| 9811 | 3 | 4 | 5 | 6 | VI-1 | Cct3 |
| 9812 | 3 | 4 | 5 | 6 | VI-1 | Cct4 |
| 9813 | 3 | 4 | 5 | 6 | VI-1 | Cct5 |
| 9814 | 3 | 4 | 5 | 6 | VI-1 | Cct6a |
| 9815 | 3 | 4 | 5 | 6 | VI-1 | Cct8 |
| 9816 | 3 | 4 | 5 | 6 | VI-1 | Ccz1 |
| 9817 | 3 | 4 | 5 | 6 | VI-1 | Cd101 |
| 9818 | 3 | 4 | 5 | 6 | VI-1 | Cd151 |
| 9819 | 3 | 4 | 5 | 6 | VI-1 | Cd163 |
| 9820 | 3 | 4 | 5 | 6 | VI-1 | Cd163l1 |
| 9821 | 3 | 4 | 5 | 6 | VI-1 | Cd2 |
| 9822 | 3 | 4 | 5 | 6 | VI-1 | Cd200r2 |
| 9823 | 3 | 4 | 5 | 6 | VI-1 | Cd200r4 |
| 9824 | 3 | 4 | 5 | 6 | VI-1 | Cd209b |
| 9825 | 3 | 4 | 5 | 6 | VI-1 | Cd209g |
| 9826 | 3 | 4 | 5 | 6 | VI-1 | Cd22 |
| 9827 | 3 | 4 | 5 | 6 | VI-1 | Cd247 |
| 9828 | 3 | 4 | 5 | 6 | VI-1 | Cd24a |
| 9829 | 3 | 4 | 5 | 6 | VI-1 | Cd276 |
| 9830 | 3 | 4 | 5 | 6 | VI-1 | Cd300a |
| 9831 | 3 | 4 | 5 | 6 | VI-1 | Cd300lf |
| 9832 | 3 | 4 | 5 | 6 | VI-1 | Cd300lg |
| 9833 | 3 | 4 | 5 | 6 | VI-1 | Cd33 |
| 9834 | 3 | 4 | 5 | 6 | VI-1 | Cd37 |
| 9835 | 3 | 4 | 5 | 6 | VI-1 | Cd38 |
| 9836 | 3 | 4 | 5 | 6 | VI-1 | Cd3d |
| 9837 | 3 | 4 | 5 | 6 | VI-1 | Cd3e |
| 9838 | 3 | 4 | 5 | 6 | VI-1 | Cd3eap |
| 9839 | 3 | 4 | 5 | 6 | VI-1 | Cd3g |
| 9840 | 3 | 4 | 5 | 6 | VI-1 | Cd40 |
| 9841 | 3 | 4 | 5 | 6 | VI-1 | Cd5 |
| 9842 | 3 | 4 | 5 | 6 | VI-1 | Cd59a |
| 9843 | 3 | 4 | 5 | 6 | VI-1 | Cd59b |
| 9844 | 3 | 4 | 5 | 6 | VI-1 | Cd6 |
| 9845 | 3 | 4 | 5 | 6 | VI-1 | Cd68 |
| 9846 | 3 | 4 | 5 | 6 | VI-1 | Cd7 |
| 9847 | 3 | 4 | 5 | 6 | VI-1 | Cd74 |
| 9848 | 3 | 4 | 5 | 6 | VI-1 | Cd79a |
| 9849 | 3 | 4 | 5 | 6 | VI-1 | Cd79b |
| 9850 | 3 | 4 | 5 | 6 | VI-1 | Cd83 |
| 9851 | 3 | 4 | 5 | 6 | VI-1 | Cd8a |
| 9852 | 3 | 4 | 5 | 6 | VI-1 | Cd93 |
| 9853 | 3 | 4 | 5 | 6 | VI-1 | Cd96 |
| 9854 | 3 | 4 | 5 | 6 | VI-1 | Cdadc1 |
| 9855 | 3 | 4 | 5 | 6 | VI-1 | Cdc123 |
| 9856 | 3 | 4 | 5 | 6 | VI-1 | Cdc14a |
| 9857 | 3 | 4 | 5 | 6 | VI-1 | Cdc16 |
| 9858 | 3 | 4 | 5 | 6 | VI-1 | Cdc25a |
| 9859 | 3 | 4 | 5 | 6 | VI-1 | Cdc25c |
| 9860 | 3 | 4 | 5 | 6 | VI-1 | Cdc27 |
| 9861 | 3 | 4 | 5 | 6 | VI-1 | Cdc42bpa |
| 9862 | 3 | 4 | 5 | 6 | VI-1 | Cdc42ep2 |
| 9863 | 3 | 4 | 5 | 6 | VI-1 | Cdc42se1 |
| 9864 | 3 | 4 | 5 | 6 | VI-1 | Cdc5l |
| 9865 | 3 | 4 | 5 | 6 | VI-1 | Cdc73 |
| 9866 | 3 | 4 | 5 | 6 | VI-1 | Cdca5 |
| 9867 | 3 | 4 | 5 | 6 | VI-1 | Cdca7l |
| 9868 | 3 | 4 | 5 | 6 | VI-1 | Cdca8 |
| 9869 | 3 | 4 | 5 | 6 | VI-1 | Cdh17 |
| 9870 | 3 | 4 | 5 | 6 | VI-1 | Cdh18 |
| 9871 | 3 | 4 | 5 | 6 | VI-1 | Cdh20 |
| 9872 | 3 | 4 | 5 | 6 | VI-1 | Cdh26 |
| 9873 | 3 | 4 | 5 | 6 | VI-1 | Cdh4 |
| 9874 | 3 | 4 | 5 | 6 | VI-1 | Cdhr2 |
| 9875 | 3 | 4 | 5 | 6 | VI-1 | Cdhr3 |
| 9876 | 3 | 4 | 5 | 6 | VI-1 | Cdhr5 |
| 9877 | 3 | 4 | 5 | 6 | VI-1 | Cdipt |
| 9878 | 3 | 4 | 5 | 6 | VI-1 | Cdk12 |
| 9879 | 3 | 4 | 5 | 6 | VI-1 | Cdk13 |
| 9880 | 3 | 4 | 5 | 6 | VI-1 | Cdk18 |
| 9881 | 3 | 4 | 5 | 6 | VI-1 | Cdk19 |
| 9882 | 3 | 4 | 5 | 6 | VI-1 | Cdk2ap1 |
| 9883 | 3 | 4 | 5 | 6 | VI-1 | Cdk2ap2 |
| 9884 | 3 | 4 | 5 | 6 | VI-1 | Cdk3-ps |
| 9885 | 3 | 4 | 5 | 6 | VI-1 | Cdk5 |
| 9886 | 3 | 4 | 5 | 6 | VI-1 | Cdk6 |
| 9887 | 3 | 4 | 5 | 6 | VI-1 | Cdk8 |
| 9888 | 3 | 4 | 5 | 6 | VI-1 | Cdk9 |
| 9889 | 3 | 4 | 5 | 6 | VI-1 | Cdkal1 |
| 9890 | 3 | 4 | 5 | 6 | VI-1 | Cdkl1 |
| 9891 | 3 | 4 | 5 | 6 | VI-1 | Cdkl2 |
| 9892 | 3 | 4 | 5 | 6 | VI-1 | Cdkl4 |
| 9893 | 3 | 4 | 5 | 6 | VI-1 | Cdkn1b |
| 9894 | 3 | 4 | 5 | 6 | VI-1 | Cdkn1c |
| 9895 | 3 | 4 | 5 | 6 | VI-1 | Cdkn2aip |
| 9896 | 3 | 4 | 5 | 6 | VI-1 | Cdkn2aipnl |
| 9897 | 3 | 4 | 5 | 6 | VI-1 | Cdkn2b |
| 9898 | 3 | 4 | 5 | 6 | VI-1 | Cdkn2d |
| 9899 | 3 | 4 | 5 | 6 | VI-1 | Cdon |
| 9900 | 3 | 4 | 5 | 6 | VI-1 | Cdr2 |
| 9901 | 3 | 4 | 5 | 6 | VI-1 | Cdr2l |
| 9902 | 3 | 4 | 5 | 6 | VI-1 | Cdrt4 |
| 9903 | 3 | 4 | 5 | 6 | VI-1 | Cds1 |
| 9904 | 3 | 4 | 5 | 6 | VI-1 | Cdsn |
| 9905 | 3 | 4 | 5 | 6 | VI-1 | Cdv3 |
| 9906 | 3 | 4 | 5 | 6 | VI-1 | Cdyl |
| 9907 | 3 | 4 | 5 | 6 | VI-1 | Cdyl2 |
| 9908 | 3 | 4 | 5 | 6 | VI-1 | Ceacam18 |
| 9909 | 3 | 4 | 5 | 6 | VI-1 | Ceacam2 |
| 9910 | 3 | 4 | 5 | 6 | VI-1 | Cebpz |
| 9911 | 3 | 4 | 5 | 6 | VI-1 | Cebpzos |
| 9912 | 3 | 4 | 5 | 6 | VI-1 | Cecr5 |
| 9913 | 3 | 4 | 5 | 6 | VI-1 | Cecr6 |
| 9914 | 3 | 4 | 5 | 6 | VI-1 | Celf2 |
| 9915 | 3 | 4 | 5 | 6 | VI-1 | Celf3 |
| 9916 | 3 | 4 | 5 | 6 | VI-1 | Celsr1 |
| 9917 | 3 | 4 | 5 | 6 | VI-1 | Celsr2 |
| 9918 | 3 | 4 | 5 | 6 | VI-1 | Cenpk |
| 9919 | 3 | 4 | 5 | 6 | VI-1 | Cenpm |
| 9920 | 3 | 4 | 5 | 6 | VI-1 | Cenpt |
| 9921 | 3 | 4 | 5 | 6 | VI-1 | Cenpw |
| 9922 | 3 | 4 | 5 | 6 | VI-1 | Cep120 |
| 9923 | 3 | 4 | 5 | 6 | VI-1 | Cep131 |
| 9924 | 3 | 4 | 5 | 6 | VI-1 | Cep170 |
| 9925 | 3 | 4 | 5 | 6 | VI-1 | Cep19 |
| 9926 | 3 | 4 | 5 | 6 | VI-1 | Cep350 |
| 9927 | 3 | 4 | 5 | 6 | VI-1 | Cep41 |
| 9928 | 3 | 4 | 5 | 6 | VI-1 | Cep57l1 |
| 9929 | 3 | 4 | 5 | 6 | VI-1 | Cep70 |
| 9930 | 3 | 4 | 5 | 6 | VI-1 | Cep76 |
| 9931 | 3 | 4 | 5 | 6 | VI-1 | Cep78 |
| 9932 | 3 | 4 | 5 | 6 | VI-1 | Cep83 |
| 9933 | 3 | 4 | 5 | 6 | VI-1 | Cep83os |
| 9934 | 3 | 4 | 5 | 6 | VI-1 | Cep85l |
| 9935 | 3 | 4 | 5 | 6 | VI-1 | Cerk |
| 9936 | 3 | 4 | 5 | 6 | VI-1 | Cers1 |
| 9937 | 3 | 4 | 5 | 6 | VI-1 | Cers5 |
| 9938 | 3 | 4 | 5 | 6 | VI-1 | Cers6 |
| 9939 | 3 | 4 | 5 | 6 | VI-1 | Ces1b |
| 9940 | 3 | 4 | 5 | 6 | VI-1 | Ces1e |
| 9941 | 3 | 4 | 5 | 6 | VI-1 | Ces1g |
| 9942 | 3 | 4 | 5 | 6 | VI-1 | Ces2b |
| 9943 | 3 | 4 | 5 | 6 | VI-1 | Ces2c |
| 9944 | 3 | 4 | 5 | 6 | VI-1 | Ces2d-ps |
| 9945 | 3 | 4 | 5 | 6 | VI-1 | Ces2e |
| 9946 | 3 | 4 | 5 | 6 | VI-1 | Ces3a |
| 9947 | 3 | 4 | 5 | 6 | VI-1 | Ces4a |
| 9948 | 3 | 4 | 5 | 6 | VI-1 | Cetn4 |
| 9949 | 3 | 4 | 5 | 6 | VI-1 | Cfh |
| 9950 | 3 | 4 | 5 | 6 | VI-1 | Cfhr2 |
| 9951 | 3 | 4 | 5 | 6 | VI-1 | Cftr |
| 9952 | 3 | 4 | 5 | 6 | VI-1 | Cggbp1 |
| 9953 | 3 | 4 | 5 | 6 | VI-1 | Cgn |
| 9954 | 3 | 4 | 5 | 6 | VI-1 | Cgnl1 |
| 9955 | 3 | 4 | 5 | 6 | VI-1 | Cgrrf1 |
| 9956 | 3 | 4 | 5 | 6 | VI-1 | Chac2 |
| 9957 | 3 | 4 | 5 | 6 | VI-1 | Chad |
| 9958 | 3 | 4 | 5 | 6 | VI-1 | Chadl |
| 9959 | 3 | 4 | 5 | 6 | VI-1 | Chaf1a |
| 9960 | 3 | 4 | 5 | 6 | VI-1 | Champ1 |
| 9961 | 3 | 4 | 5 | 6 | VI-1 | Chchd3 |
| 9962 | 3 | 4 | 5 | 6 | VI-1 | Chchd4 |
| 9963 | 3 | 4 | 5 | 6 | VI-1 | Chchd5 |
| 9964 | 3 | 4 | 5 | 6 | VI-1 | Chd1 |
| 9965 | 3 | 4 | 5 | 6 | VI-1 | Chd1l |
| 9966 | 3 | 4 | 5 | 6 | VI-1 | Chd5 |
| 9967 | 3 | 4 | 5 | 6 | VI-1 | Chdh |
| 9968 | 3 | 4 | 5 | 6 | VI-1 | Chfr |
| 9969 | 3 | 4 | 5 | 6 | VI-1 | Chic1 |
| 9970 | 3 | 4 | 5 | 6 | VI-1 | Chid1 |
| 9971 | 3 | 4 | 5 | 6 | VI-1 | Chit1 |
| 9972 | 3 | 4 | 5 | 6 | VI-1 | Chka |
| 9973 | 3 | 4 | 5 | 6 | VI-1 | Chl1 |
| 9974 | 3 | 4 | 5 | 6 | VI-1 | Chm |
| 9975 | 3 | 4 | 5 | 6 | VI-1 | Chmp1a |
| 9976 | 3 | 4 | 5 | 6 | VI-1 | Chmp4b |
| 9977 | 3 | 4 | 5 | 6 | VI-1 | Chmp5 |
| 9978 | 3 | 4 | 5 | 6 | VI-1 | Chmp6 |
| 9979 | 3 | 4 | 5 | 6 | VI-1 | Chmp7 |
| 9980 | 3 | 4 | 5 | 6 | VI-1 | Chn2 |
| 9981 | 3 | 4 | 5 | 6 | VI-1 | Chodl |
| 9982 | 3 | 4 | 5 | 6 | VI-1 | Chp2 |

Fig. 34 - 53

| | | | | | | |
|---|---|---|---|---|---|---|
| 9983 | 3 | 4 | 5 | 6 | VI-1 | Chpf |
| 9984 | 3 | 4 | 5 | 6 | VI-1 | Chpt1 |
| 9985 | 3 | 4 | 5 | 6 | VI-1 | Chrac1 |
| 9986 | 3 | 4 | 5 | 6 | VI-1 | Chrm1 |
| 9987 | 3 | 4 | 5 | 6 | VI-1 | Chrm2 |
| 9988 | 3 | 4 | 5 | 6 | VI-1 | Chrm3 |
| 9989 | 3 | 4 | 5 | 6 | VI-1 | Chrna1 |
| 9990 | 3 | 4 | 5 | 6 | VI-1 | Chrna10 |
| 9991 | 3 | 4 | 5 | 6 | VI-1 | Chrna2 |
| 9992 | 3 | 4 | 5 | 6 | VI-1 | Chrnb1 |
| 9993 | 3 | 4 | 5 | 6 | VI-1 | Chst11 |
| 9994 | 3 | 4 | 5 | 6 | VI-1 | Chst12 |
| 9995 | 3 | 4 | 5 | 6 | VI-1 | Chst3 |
| 9996 | 3 | 4 | 5 | 6 | VI-1 | Chst8 |
| 9997 | 3 | 4 | 5 | 6 | VI-1 | Chsy1 |
| 9998 | 3 | 4 | 5 | 6 | VI-1 | Chtf18 |
| 9999 | 3 | 4 | 5 | 6 | VI-1 | Ciao1 |
| 10000 | 3 | 4 | 5 | 6 | VI-1 | Cib2 |
| 10001 | 3 | 4 | 5 | 6 | VI-1 | Cib4 |
| 10002 | 3 | 4 | 5 | 6 | VI-1 | Cilp |
| 10003 | 3 | 4 | 5 | 6 | VI-1 | Cinp |
| 10004 | 3 | 4 | 5 | 6 | VI-1 | Cipc |
| 10005 | 3 | 4 | 5 | 6 | VI-1 | Cir1 |
| 10006 | 3 | 4 | 5 | 6 | VI-1 | Cirbp |
| 10007 | 3 | 4 | 5 | 6 | VI-1 | Cirh1a |
| 10008 | 3 | 4 | 5 | 6 | VI-1 | Cisd1 |
| 10009 | 3 | 4 | 5 | 6 | VI-1 | Cited2 |
| 10010 | 3 | 4 | 5 | 6 | VI-1 | Cited4 |
| 10011 | 3 | 4 | 5 | 6 | VI-1 | Cklf |
| 10012 | 3 | 4 | 5 | 6 | VI-1 | Ckmt2 |
| 10013 | 3 | 4 | 5 | 6 | VI-1 | Clasp1 |
| 10014 | 3 | 4 | 5 | 6 | VI-1 | Clasrp |
| 10015 | 3 | 4 | 5 | 6 | VI-1 | Clca1 |
| 10016 | 3 | 4 | 5 | 6 | VI-1 | Clcn2 |
| 10017 | 3 | 4 | 5 | 6 | VI-1 | Clcn5 |
| 10018 | 3 | 4 | 5 | 6 | VI-1 | Clcn6 |
| 10019 | 3 | 4 | 5 | 6 | VI-1 | Cldn1 |
| 10020 | 3 | 4 | 5 | 6 | VI-1 | Cldn14 |
| 10021 | 3 | 4 | 5 | 6 | VI-1 | Cldn18 |
| 10022 | 3 | 4 | 5 | 6 | VI-1 | Cldn2 |
| 10023 | 3 | 4 | 5 | 6 | VI-1 | Cldn4 |
| 10024 | 3 | 4 | 5 | 6 | VI-1 | Cldn6 |
| 10025 | 3 | 4 | 5 | 6 | VI-1 | Cldn9 |
| 10026 | 3 | 4 | 5 | 6 | VI-1 | Clec11a |
| 10027 | 3 | 4 | 5 | 6 | VI-1 | Clec16a |
| 10028 | 3 | 4 | 5 | 6 | VI-1 | Clec2d |
| 10029 | 3 | 4 | 5 | 6 | VI-1 | Clec2e |
| 10030 | 3 | 4 | 5 | 6 | VI-1 | Clec2h |
| 10031 | 3 | 4 | 5 | 6 | VI-1 | Clec3b |
| 10032 | 3 | 4 | 5 | 6 | VI-1 | Clec4a1 |
| 10033 | 3 | 4 | 5 | 6 | VI-1 | Clec4a2 |
| 10034 | 3 | 4 | 5 | 6 | VI-1 | Clec4a3 |
| 10035 | 3 | 4 | 5 | 6 | VI-1 | Clec4b2 |
| 10036 | 3 | 4 | 5 | 6 | VI-1 | Clec4e |
| 10037 | 3 | 4 | 5 | 6 | VI-1 | Clec4g |
| 10038 | 3 | 4 | 5 | 6 | VI-1 | Clec4n |
| 10039 | 3 | 4 | 5 | 6 | VI-1 | Clec7a |
| 10040 | 3 | 4 | 5 | 6 | VI-1 | Clec9a |
| 10041 | 3 | 4 | 5 | 6 | VI-1 | Clic1 |
| 10042 | 3 | 4 | 5 | 6 | VI-1 | Clic3 |
| 10043 | 3 | 4 | 5 | 6 | VI-1 | Clic4 |
| 10044 | 3 | 4 | 5 | 6 | VI-1 | Clic5 |
| 10045 | 3 | 4 | 5 | 6 | VI-1 | Clic6 |
| 10046 | 3 | 4 | 5 | 6 | VI-1 | Clip1 |
| 10047 | 3 | 4 | 5 | 6 | VI-1 | Clip2 |
| 10048 | 3 | 4 | 5 | 6 | VI-1 | Clip3 |
| 10049 | 3 | 4 | 5 | 6 | VI-1 | Clip4 |
| 10050 | 3 | 4 | 5 | 6 | VI-1 | Clk1 |
| 10051 | 3 | 4 | 5 | 6 | VI-1 | Clk3 |
| 10052 | 3 | 4 | 5 | 6 | VI-1 | Clk4 |
| 10053 | 3 | 4 | 5 | 6 | VI-1 | Clmn |
| 10054 | 3 | 4 | 5 | 6 | VI-1 | Cln3 |
| 10055 | 3 | 4 | 5 | 6 | VI-1 | Cln6 |
| 10056 | 3 | 4 | 5 | 6 | VI-1 | Cln8 |
| 10057 | 3 | 4 | 5 | 6 | VI-1 | Clns1a |
| 10058 | 3 | 4 | 5 | 6 | VI-1 | Clpb |
| 10059 | 3 | 4 | 5 | 6 | VI-1 | Clptm1 |
| 10060 | 3 | 4 | 5 | 6 | VI-1 | Clptm1l |
| 10061 | 3 | 4 | 5 | 6 | VI-1 | Clpx |
| 10062 | 3 | 4 | 5 | 6 | VI-1 | Clrn3 |
| 10063 | 3 | 4 | 5 | 6 | VI-1 | Clstn1 |
| 10064 | 3 | 4 | 5 | 6 | VI-1 | Clstn2 |
| 10065 | 3 | 4 | 5 | 6 | VI-1 | Clta |
| 10066 | 3 | 4 | 5 | 6 | VI-1 | Cltb |
| 10067 | 3 | 4 | 5 | 6 | VI-1 | Clu |
| 10068 | 3 | 4 | 5 | 6 | VI-1 | Cluap1 |
| 10069 | 3 | 4 | 5 | 6 | VI-1 | Cluh |
| 10070 | 3 | 4 | 5 | 6 | VI-1 | Clvs1 |
| 10071 | 3 | 4 | 5 | 6 | VI-1 | Clybl |
| 10072 | 3 | 4 | 5 | 6 | VI-1 | Cmah |
| 10073 | 3 | 4 | 5 | 6 | VI-1 | Cmklr1 |
| 10074 | 3 | 4 | 5 | 6 | VI-1 | Cmtl1 |
| 10075 | 3 | 4 | 5 | 6 | VI-1 | Cml2 |
| 10076 | 3 | 4 | 5 | 6 | VI-1 | Cml3 |
| 10077 | 3 | 4 | 5 | 6 | VI-1 | Cml5 |
| 10078 | 3 | 4 | 5 | 6 | VI-1 | Cmpk2 |
| 10079 | 3 | 4 | 5 | 6 | VI-1 | Cmss1 |
| 10080 | 3 | 4 | 5 | 6 | VI-1 | Cmtm2a |
| 10081 | 3 | 4 | 5 | 6 | VI-1 | Cmtm3 |
| 10082 | 3 | 4 | 5 | 6 | VI-1 | Cmtm5 |
| 10083 | 3 | 4 | 5 | 6 | VI-1 | Cmtr1 |
| 10084 | 3 | 4 | 5 | 6 | VI-1 | Cmya5 |
| 10085 | 3 | 4 | 5 | 6 | VI-1 | Cnbd2 |
| 10086 | 3 | 4 | 5 | 6 | VI-1 | Cnbp |
| 10087 | 3 | 4 | 5 | 6 | VI-1 | Cndp2 |
| 10088 | 3 | 4 | 5 | 6 | VI-1 | Cnga3 |
| 10089 | 3 | 4 | 5 | 6 | VI-1 | Cngb1 |
| 10090 | 3 | 4 | 5 | 6 | VI-1 | Cnih3 |
| 10091 | 3 | 4 | 5 | 6 | VI-1 | Cnih4 |
| 10092 | 3 | 4 | 5 | 6 | VI-1 | Cnksr1 |
| 10093 | 3 | 4 | 5 | 6 | VI-1 | Cnksr2 |
| 10094 | 3 | 4 | 5 | 6 | VI-1 | Cnn1 |
| 10095 | 3 | 4 | 5 | 6 | VI-1 | Cnn3 |
| 10096 | 3 | 4 | 5 | 6 | VI-1 | Cnnm1 |
| 10097 | 3 | 4 | 5 | 6 | VI-1 | Cnnm2 |
| 10098 | 3 | 4 | 5 | 6 | VI-1 | Cnnm3 |
| 10099 | 3 | 4 | 5 | 6 | VI-1 | Cnot1 |
| 10100 | 3 | 4 | 5 | 6 | VI-1 | Cnot2 |
| 10101 | 3 | 4 | 5 | 6 | VI-1 | Cnot4 |
| 10102 | 3 | 4 | 5 | 6 | VI-1 | Cnot6l |
| 10103 | 3 | 4 | 5 | 6 | VI-1 | Cnp |
| 10104 | 3 | 4 | 5 | 6 | VI-1 | Cnppd1 |
| 10105 | 3 | 4 | 5 | 6 | VI-1 | Cnpy2 |
| 10106 | 3 | 4 | 5 | 6 | VI-1 | Cnr1 |
| 10107 | 3 | 4 | 5 | 6 | VI-1 | Cntf |
| 10108 | 3 | 4 | 5 | 6 | VI-1 | Cntn2 |
| 10109 | 3 | 4 | 5 | 6 | VI-1 | Cntnap2 |
| 10110 | 3 | 4 | 5 | 6 | VI-1 | Coa3 |
| 10111 | 3 | 4 | 5 | 6 | VI-1 | Coa4 |
| 10112 | 3 | 4 | 5 | 6 | VI-1 | Coa6 |
| 10113 | 3 | 4 | 5 | 6 | VI-1 | Coa7 |
| 10114 | 3 | 4 | 5 | 6 | VI-1 | Coasy |
| 10115 | 3 | 4 | 5 | 6 | VI-1 | Cobl |
| 10116 | 3 | 4 | 5 | 6 | VI-1 | Cobll1 |
| 10117 | 3 | 4 | 5 | 6 | VI-1 | Coch |
| 10118 | 3 | 4 | 5 | 6 | VI-1 | Cog2 |
| 10119 | 3 | 4 | 5 | 6 | VI-1 | Cog4 |
| 10120 | 3 | 4 | 5 | 6 | VI-1 | Cog5 |
| 10121 | 3 | 4 | 5 | 6 | VI-1 | Cog6 |
| 10122 | 3 | 4 | 5 | 6 | VI-1 | Cog8 |
| 10123 | 3 | 4 | 5 | 6 | VI-1 | Col16a1 |
| 10124 | 3 | 4 | 5 | 6 | VI-1 | Col19a1 |
| 10125 | 3 | 4 | 5 | 6 | VI-1 | Col20a1 |
| 10126 | 3 | 4 | 5 | 6 | VI-1 | Col23a1 |
| 10127 | 3 | 4 | 5 | 6 | VI-1 | Col26a1 |
| 10128 | 3 | 4 | 5 | 6 | VI-1 | Col27a1 |
| 10129 | 3 | 4 | 5 | 6 | VI-1 | Col4a1 |
| 10130 | 3 | 4 | 5 | 6 | VI-1 | Col5a3 |
| 10131 | 3 | 4 | 5 | 6 | VI-1 | Col6a1 |
| 10132 | 3 | 4 | 5 | 6 | VI-1 | Col6a2 |
| 10133 | 3 | 4 | 5 | 6 | VI-1 | Col8a1 |
| 10134 | 3 | 4 | 5 | 6 | VI-1 | Col8a2 |
| 10135 | 3 | 4 | 5 | 6 | VI-1 | Col9a2 |
| 10136 | 3 | 4 | 5 | 6 | VI-1 | Col9a3 |
| 10137 | 3 | 4 | 5 | 6 | VI-1 | Colec12 |
| 10138 | 3 | 4 | 5 | 6 | VI-1 | Commd1 |
| 10139 | 3 | 4 | 5 | 6 | VI-1 | Commd2 |
| 10140 | 3 | 4 | 5 | 6 | VI-1 | Commd3 |
| 10141 | 3 | 4 | 5 | 6 | VI-1 | Commd4 |
| 10142 | 3 | 4 | 5 | 6 | VI-1 | Commd7 |
| 10143 | 3 | 4 | 5 | 6 | VI-1 | Commd9 |
| 10144 | 3 | 4 | 5 | 6 | VI-1 | Comp |
| 10145 | 3 | 4 | 5 | 6 | VI-1 | Cope |
| 10146 | 3 | 4 | 5 | 6 | VI-1 | Coprs |
| 10147 | 3 | 4 | 5 | 6 | VI-1 | Cops2 |
| 10148 | 3 | 4 | 5 | 6 | VI-1 | Cops4 |
| 10149 | 3 | 4 | 5 | 6 | VI-1 | Cops5 |
| 10150 | 3 | 4 | 5 | 6 | VI-1 | Coq10a |
| 10151 | 3 | 4 | 5 | 6 | VI-1 | Coq10b |
| 10152 | 3 | 4 | 5 | 6 | VI-1 | Coq3 |
| 10153 | 3 | 4 | 5 | 6 | VI-1 | Coq4 |
| 10154 | 3 | 4 | 5 | 6 | VI-1 | Coq7 |
| 10155 | 3 | 4 | 5 | 6 | VI-1 | Coq9 |
| 10156 | 3 | 4 | 5 | 6 | VI-1 | Corin |
| 10157 | 3 | 4 | 5 | 6 | VI-1 | Coro1a |
| 10158 | 3 | 4 | 5 | 6 | VI-1 | Coro1b |
| 10159 | 3 | 4 | 5 | 6 | VI-1 | Coro2a |
| 10160 | 3 | 4 | 5 | 6 | VI-1 | Cotl1 |
| 10161 | 3 | 4 | 5 | 6 | VI-1 | Cox10 |
| 10162 | 3 | 4 | 5 | 6 | VI-1 | Cox14 |
| 10163 | 3 | 4 | 5 | 6 | VI-1 | Cox16 |
| 10164 | 3 | 4 | 5 | 6 | VI-1 | Cox18 |
| 10165 | 3 | 4 | 5 | 6 | VI-1 | Cox19 |
| 10166 | 3 | 4 | 5 | 6 | VI-1 | Cox5a |
| 10167 | 3 | 4 | 5 | 6 | VI-1 | Cox7a2l |
| 10168 | 3 | 4 | 5 | 6 | VI-1 | Cox7b2 |
| 10169 | 3 | 4 | 5 | 6 | VI-1 | Cp |
| 10170 | 3 | 4 | 5 | 6 | VI-1 | Cpa3 |
| 10171 | 3 | 4 | 5 | 6 | VI-1 | Cpeb1 |
| 10172 | 3 | 4 | 5 | 6 | VI-1 | Cpeb2 |
| 10173 | 3 | 4 | 5 | 6 | VI-1 | Cpeb3 |
| 10174 | 3 | 4 | 5 | 6 | VI-1 | Cplx4 |

Fig. 34 - 54

| | | | | | | |
|---|---|---|---|---|---|---|
| 10175 | 3 | 4 | 5 | 6 | VI-1 | Cpm |
| 10176 | 3 | 4 | 5 | 6 | VI-1 | Cpne2 |
| 10177 | 3 | 4 | 5 | 6 | VI-1 | Cpne5 |
| 10178 | 3 | 4 | 5 | 6 | VI-1 | Cpne6 |
| 10179 | 3 | 4 | 5 | 6 | VI-1 | Cpne7 |
| 10180 | 3 | 4 | 5 | 6 | VI-1 | Cpne8 |
| 10181 | 3 | 4 | 5 | 6 | VI-1 | Cps1 |
| 10182 | 3 | 4 | 5 | 6 | VI-1 | Cpsf2 |
| 10183 | 3 | 4 | 5 | 6 | VI-1 | Cpsf3 |
| 10184 | 3 | 4 | 5 | 6 | VI-1 | Cpt1b |
| 10185 | 3 | 4 | 5 | 6 | VI-1 | Cpt2 |
| 10186 | 3 | 4 | 5 | 6 | VI-1 | Cradd |
| 10187 | 3 | 4 | 5 | 6 | VI-1 | Crcp |
| 10188 | 3 | 4 | 5 | 6 | VI-1 | Crct1 |
| 10189 | 3 | 4 | 5 | 6 | VI-1 | Creb1 |
| 10190 | 3 | 4 | 5 | 6 | VI-1 | Creb3 |
| 10191 | 3 | 4 | 5 | 6 | VI-1 | Creb3l1 |
| 10192 | 3 | 4 | 5 | 6 | VI-1 | Creb3l2 |
| 10193 | 3 | 4 | 5 | 6 | VI-1 | Creb3l3 |
| 10194 | 3 | 4 | 5 | 6 | VI-1 | Creb3l4 |
| 10195 | 3 | 4 | 5 | 6 | VI-1 | Creg2 |
| 10196 | 3 | 4 | 5 | 6 | VI-1 | Creld1 |
| 10197 | 3 | 4 | 5 | 6 | VI-1 | Creld2 |
| 10198 | 3 | 4 | 5 | 6 | VI-1 | Crem |
| 10199 | 3 | 4 | 5 | 6 | VI-1 | Crh |
| 10200 | 3 | 4 | 5 | 6 | VI-1 | Crhr2 |
| 10201 | 3 | 4 | 5 | 6 | VI-1 | Crim1 |
| 10202 | 3 | 4 | 5 | 6 | VI-1 | Crip2 |
| 10203 | 3 | 4 | 5 | 6 | VI-1 | Crip3 |
| 10204 | 3 | 4 | 5 | 6 | VI-1 | Cript |
| 10205 | 3 | 4 | 5 | 6 | VI-1 | Crispld2 |
| 10206 | 3 | 4 | 5 | 6 | VI-1 | Crkl |
| 10207 | 3 | 4 | 5 | 6 | VI-1 | Crlf1 |
| 10208 | 3 | 4 | 5 | 6 | VI-1 | Crlf2 |
| 10209 | 3 | 4 | 5 | 6 | VI-1 | Crot |
| 10210 | 3 | 4 | 5 | 6 | VI-1 | Crtam |
| 10211 | 3 | 4 | 5 | 6 | VI-1 | Cryab |
| 10212 | 3 | 4 | 5 | 6 | VI-1 | Cryba2 |
| 10213 | 3 | 4 | 5 | 6 | VI-1 | Crybb1 |
| 10214 | 3 | 4 | 5 | 6 | VI-1 | Crybg3 |
| 10215 | 3 | 4 | 5 | 6 | VI-1 | Crygs |
| 10216 | 3 | 4 | 5 | 6 | VI-1 | Cryzl1 |
| 10217 | 3 | 4 | 5 | 6 | VI-1 | Csad |
| 10218 | 3 | 4 | 5 | 6 | VI-1 | Csde1 |
| 10219 | 3 | 4 | 5 | 6 | VI-1 | Csf2ra |
| 10220 | 3 | 4 | 5 | 6 | VI-1 | Csf2rb |
| 10221 | 3 | 4 | 5 | 6 | VI-1 | Csgalnact1 |
| 10222 | 3 | 4 | 5 | 6 | VI-1 | Csgalnact2 |
| 10223 | 3 | 4 | 5 | 6 | VI-1 | Csk |
| 10224 | 3 | 4 | 5 | 6 | VI-1 | Csnk1g1 |
| 10225 | 3 | 4 | 5 | 6 | VI-1 | Csnk1g2 |
| 10226 | 3 | 4 | 5 | 6 | VI-1 | Csnk2a2 |
| 10227 | 3 | 4 | 5 | 6 | VI-1 | Csnk2b |
| 10228 | 3 | 4 | 5 | 6 | VI-1 | Csnka2ip |
| 10229 | 3 | 4 | 5 | 6 | VI-1 | Csprs |
| 10230 | 3 | 4 | 5 | 6 | VI-1 | Csrp2 |
| 10231 | 3 | 4 | 5 | 6 | VI-1 | Csrp2bp |
| 10232 | 3 | 4 | 5 | 6 | VI-1 | Cst13 |
| 10233 | 3 | 4 | 5 | 6 | VI-1 | Cst7 |
| 10234 | 3 | 4 | 5 | 6 | VI-1 | Cst9 |
| 10235 | 3 | 4 | 5 | 6 | VI-1 | Csth |
| 10236 | 3 | 4 | 5 | 6 | VI-1 | Cstf3 |
| 10237 | 3 | 4 | 5 | 6 | VI-1 | Ctcf |
| 10238 | 3 | 4 | 5 | 6 | VI-1 | Ctcfl |
| 10239 | 3 | 4 | 5 | 6 | VI-1 | Ctdp1 |
| 10240 | 3 | 4 | 5 | 6 | VI-1 | Ctdsp1 |
| 10241 | 3 | 4 | 5 | 6 | VI-1 | Ctdspl |
| 10242 | 3 | 4 | 5 | 6 | VI-1 | Ctdspl2 |
| 10243 | 3 | 4 | 5 | 6 | VI-1 | Ctf1 |
| 10244 | 3 | 4 | 5 | 6 | VI-1 | Ctla4 |
| 10245 | 3 | 4 | 5 | 6 | VI-1 | Ctnna2 |
| 10246 | 3 | 4 | 5 | 6 | VI-1 | Ctnnbip1 |
| 10247 | 3 | 4 | 5 | 6 | VI-1 | Ctnnbl1 |
| 10248 | 3 | 4 | 5 | 6 | VI-1 | Ctnnd2 |
| 10249 | 3 | 4 | 5 | 6 | VI-1 | Ctps |
| 10250 | 3 | 4 | 5 | 6 | VI-1 | Ctps2 |
| 10251 | 3 | 4 | 5 | 6 | VI-1 | Ctr9 |
| 10252 | 3 | 4 | 5 | 6 | VI-1 | Ctrcos |
| 10253 | 3 | 4 | 5 | 6 | VI-1 | Ctsb |
| 10254 | 3 | 4 | 5 | 6 | VI-1 | Ctsf |
| 10255 | 3 | 4 | 5 | 6 | VI-1 | Ctso |
| 10256 | 3 | 4 | 5 | 6 | VI-1 | Ctss |
| 10257 | 3 | 4 | 5 | 6 | VI-1 | Ctsw |
| 10258 | 3 | 4 | 5 | 6 | VI-1 | Cttnbp2 |
| 10259 | 3 | 4 | 5 | 6 | VI-1 | Cttnbp2nl |
| 10260 | 3 | 4 | 5 | 6 | VI-1 | Cuedc1 |
| 10261 | 3 | 4 | 5 | 6 | VI-1 | Cul4b |
| 10262 | 3 | 4 | 5 | 6 | VI-1 | Cul7 |
| 10263 | 3 | 4 | 5 | 6 | VI-1 | Cul9 |
| 10264 | 3 | 4 | 5 | 6 | VI-1 | Cutal |
| 10265 | 3 | 4 | 5 | 6 | VI-1 | Cux1 |
| 10266 | 3 | 4 | 5 | 6 | VI-1 | Cwc15 |
| 10267 | 3 | 4 | 5 | 6 | VI-1 | Cwc27 |
| 10268 | 3 | 4 | 5 | 6 | VI-1 | Cwf19l1 |
| 10269 | 3 | 4 | 5 | 6 | VI-1 | Cx3cr1 |
| 10270 | 3 | 4 | 5 | 6 | VI-1 | Cxcl1 |
| 10271 | 3 | 4 | 5 | 6 | VI-1 | Cxcl10 |
| 10272 | 3 | 4 | 5 | 6 | VI-1 | Cxcl14 |
| 10273 | 3 | 4 | 5 | 6 | VI-1 | Cxcl16 |
| 10274 | 3 | 4 | 5 | 6 | VI-1 | Cxcl17 |
| 10275 | 3 | 4 | 5 | 6 | VI-1 | Cxcl2 |
| 10276 | 3 | 4 | 5 | 6 | VI-1 | Cxcr3 |
| 10277 | 3 | 4 | 5 | 6 | VI-1 | Cxcr4 |
| 10278 | 3 | 4 | 5 | 6 | VI-1 | Cxcr6 |
| 10279 | 3 | 4 | 5 | 6 | VI-1 | Cxx1b |
| 10280 | 3 | 4 | 5 | 6 | VI-1 | Cxx1c |
| 10281 | 3 | 4 | 5 | 6 | VI-1 | Cxxc1 |
| 10282 | 3 | 4 | 5 | 6 | VI-1 | Cyb561 |
| 10283 | 3 | 4 | 5 | 6 | VI-1 | Cyb561a3 |
| 10284 | 3 | 4 | 5 | 6 | VI-1 | Cyb561d2 |
| 10285 | 3 | 4 | 5 | 6 | VI-1 | Cyb5d1 |
| 10286 | 3 | 4 | 5 | 6 | VI-1 | Cyb5d2 |
| 10287 | 3 | 4 | 5 | 6 | VI-1 | Cyb5r2 |
| 10288 | 3 | 4 | 5 | 6 | VI-1 | Cyb5r3 |
| 10289 | 3 | 4 | 5 | 6 | VI-1 | Cyb5r4 |
| 10290 | 3 | 4 | 5 | 6 | VI-1 | Cybb |
| 10291 | 3 | 4 | 5 | 6 | VI-1 | Cycs |
| 10292 | 3 | 4 | 5 | 6 | VI-1 | Cyfip1 |
| 10293 | 3 | 4 | 5 | 6 | VI-1 | Cyp11a1 |
| 10294 | 3 | 4 | 5 | 6 | VI-1 | Cyp21a1 |
| 10295 | 3 | 4 | 5 | 6 | VI-1 | Cyp26a1 |
| 10296 | 3 | 4 | 5 | 6 | VI-1 | Cyp27a1 |
| 10297 | 3 | 4 | 5 | 6 | VI-1 | Cyp2b19 |
| 10298 | 3 | 4 | 5 | 6 | VI-1 | Cyp2c55 |
| 10299 | 3 | 4 | 5 | 6 | VI-1 | Cyp2c69 |
| 10300 | 3 | 4 | 5 | 6 | VI-1 | Cyp2c70 |
| 10301 | 3 | 4 | 5 | 6 | VI-1 | Cyp2d10 |
| 10302 | 3 | 4 | 5 | 6 | VI-1 | Cyp2d22 |
| 10303 | 3 | 4 | 5 | 6 | VI-1 | Cyp2d9 |
| 10304 | 3 | 4 | 5 | 6 | VI-1 | Cyp2f2 |
| 10305 | 3 | 4 | 5 | 6 | VI-1 | Cyp2g1 |
| 10306 | 3 | 4 | 5 | 6 | VI-1 | Cyp2j12 |
| 10307 | 3 | 4 | 5 | 6 | VI-1 | Cyp2j9 |
| 10308 | 3 | 4 | 5 | 6 | VI-1 | Cyp39a1 |
| 10309 | 3 | 4 | 5 | 6 | VI-1 | Cyp3a11 |
| 10310 | 3 | 4 | 5 | 6 | VI-1 | Cyp46a1 |
| 10311 | 3 | 4 | 5 | 6 | VI-1 | Cyp4b1 |
| 10312 | 3 | 4 | 5 | 6 | VI-1 | Cyp4b1-ps2 |
| 10313 | 3 | 4 | 5 | 6 | VI-1 | Cyp4f16 |
| 10314 | 3 | 4 | 5 | 6 | VI-1 | Cyp4f17 |
| 10315 | 3 | 4 | 5 | 6 | VI-1 | Cyp4f18 |
| 10316 | 3 | 4 | 5 | 6 | VI-1 | Cyp4f39 |
| 10317 | 3 | 4 | 5 | 6 | VI-1 | Cyp4f41-ps |
| 10318 | 3 | 4 | 5 | 6 | VI-1 | Cyp7b1 |
| 10319 | 3 | 4 | 5 | 6 | VI-1 | Cyp8b1 |
| 10320 | 3 | 4 | 5 | 6 | VI-1 | Cypt1 |
| 10321 | 3 | 4 | 5 | 6 | VI-1 | Cypt3 |
| 10322 | 3 | 4 | 5 | 6 | VI-1 | Cypt4 |
| 10323 | 3 | 4 | 5 | 6 | VI-1 | Cyr61 |
| 10324 | 3 | 4 | 5 | 6 | VI-1 | Cyth2 |
| 10325 | 3 | 4 | 5 | 6 | VI-1 | Cyth4 |
| 10326 | 3 | 4 | 5 | 6 | VI-1 | D10Jhu81e |
| 10327 | 3 | 4 | 5 | 6 | VI-1 | D130017N08Rik |
| 10328 | 3 | 4 | 5 | 6 | VI-1 | D130020L05Rik |
| 10329 | 3 | 4 | 5 | 6 | VI-1 | D16Ertd472e |
| 10330 | 3 | 4 | 5 | 6 | VI-1 | D17Wsu104e |
| 10331 | 3 | 4 | 5 | 6 | VI-1 | D17Wsu92e |
| 10332 | 3 | 4 | 5 | 6 | VI-1 | D1Ertd622e |
| 10333 | 3 | 4 | 5 | 6 | VI-1 | D1Pas1 |
| 10334 | 3 | 4 | 5 | 6 | VI-1 | D330023K18Rik |
| 10335 | 3 | 4 | 5 | 6 | VI-1 | D3Ertd751e |
| 10336 | 3 | 4 | 5 | 6 | VI-1 | D430020J02Rik |
| 10337 | 3 | 4 | 5 | 6 | VI-1 | D430041D05Rik |
| 10338 | 3 | 4 | 5 | 6 | VI-1 | D630003M21Rik |
| 10339 | 3 | 4 | 5 | 6 | VI-1 | D630023F18Rik |
| 10340 | 3 | 4 | 5 | 6 | VI-1 | D630024D03Rik |
| 10341 | 3 | 4 | 5 | 6 | VI-1 | D630032N06Rik |
| 10342 | 3 | 4 | 5 | 6 | VI-1 | D630033O11Rik |
| 10343 | 3 | 4 | 5 | 6 | VI-1 | D630039A03Rik |
| 10344 | 3 | 4 | 5 | 6 | VI-1 | D630045M09Rik |
| 10345 | 3 | 4 | 5 | 6 | VI-1 | D6Ertd527e |
| 10346 | 3 | 4 | 5 | 6 | VI-1 | D6Wsu163e |
| 10347 | 3 | 4 | 5 | 6 | VI-1 | D830005E20Rik |
| 10348 | 3 | 4 | 5 | 6 | VI-1 | D830015G02Rik |
| 10349 | 3 | 4 | 5 | 6 | VI-1 | D830031N03Rik |
| 10350 | 3 | 4 | 5 | 6 | VI-1 | D930015E06Rik |
| 10351 | 3 | 4 | 5 | 6 | VI-1 | D930015M05Rik |
| 10352 | 3 | 4 | 5 | 6 | VI-1 | Dach1 |
| 10353 | 3 | 4 | 5 | 6 | VI-1 | Dact2 |
| 10354 | 3 | 4 | 5 | 6 | VI-1 | Daf2 |
| 10355 | 3 | 4 | 5 | 6 | VI-1 | Dak |
| 10356 | 3 | 4 | 5 | 6 | VI-1 | Dalrd3 |
| 10357 | 3 | 4 | 5 | 6 | VI-1 | Dand5 |
| 10358 | 3 | 4 | 5 | 6 | VI-1 | Dapk2 |
| 10359 | 3 | 4 | 5 | 6 | VI-1 | Dapl1 |
| 10360 | 3 | 4 | 5 | 6 | VI-1 | Dars |
| 10361 | 3 | 4 | 5 | 6 | VI-1 | Dars2 |
| 10362 | 3 | 4 | 5 | 6 | VI-1 | Daxx |
| 10363 | 3 | 4 | 5 | 6 | VI-1 | Dazap1 |
| 10364 | 3 | 4 | 5 | 6 | VI-1 | Dbn1 |
| 10365 | 3 | 4 | 5 | 6 | VI-1 | Dbndd1 |
| 10366 | 3 | 4 | 5 | 6 | VI-1 | Dbndd2 |

Fig. 34 - 55

| | | | | | | |
|---|---|---|---|---|---|---|
| 10367 | 3 | 4 | 5 | 6 | VI-1 | Dbnl |
| 10368 | 3 | 4 | 5 | 6 | VI-1 | Dbx2 |
| 10369 | 3 | 4 | 5 | 6 | VI-1 | Dcaf10 |
| 10370 | 3 | 4 | 5 | 6 | VI-1 | Dcaf11 |
| 10371 | 3 | 4 | 5 | 6 | VI-1 | Dcaf12l1 |
| 10372 | 3 | 4 | 5 | 6 | VI-1 | Dcaf15 |
| 10373 | 3 | 4 | 5 | 6 | VI-1 | Dcaf4 |
| 10374 | 3 | 4 | 5 | 6 | VI-1 | Dcaf6 |
| 10375 | 3 | 4 | 5 | 6 | VI-1 | Dcakd |
| 10376 | 3 | 4 | 5 | 6 | VI-1 | Dcbld1 |
| 10377 | 3 | 4 | 5 | 6 | VI-1 | Dcdc2a |
| 10378 | 3 | 4 | 5 | 6 | VI-1 | Dcdc2b |
| 10379 | 3 | 4 | 5 | 6 | VI-1 | Dck |
| 10380 | 3 | 4 | 5 | 6 | VI-1 | Dclre1b |
| 10381 | 3 | 4 | 5 | 6 | VI-1 | Dclre1c |
| 10382 | 3 | 4 | 5 | 6 | VI-1 | Dcn |
| 10383 | 3 | 4 | 5 | 6 | VI-1 | Dcpp2 |
| 10384 | 3 | 4 | 5 | 6 | VI-1 | Dcst1 |
| 10385 | 3 | 4 | 5 | 6 | VI-1 | Dct |
| 10386 | 3 | 4 | 5 | 6 | VI-1 | Dctn6 |
| 10387 | 3 | 4 | 5 | 6 | VI-1 | Dcun1d4 |
| 10388 | 3 | 4 | 5 | 6 | VI-1 | Ddah1 |
| 10389 | 3 | 4 | 5 | 6 | VI-1 | Ddah2 |
| 10390 | 3 | 4 | 5 | 6 | VI-1 | Ddc |
| 10391 | 3 | 4 | 5 | 6 | VI-1 | Ddi1 |
| 10392 | 3 | 4 | 5 | 6 | VI-1 | Ddit4l |
| 10393 | 3 | 4 | 5 | 6 | VI-1 | Ddo |
| 10394 | 3 | 4 | 5 | 6 | VI-1 | Ddr2 |
| 10395 | 3 | 4 | 5 | 6 | VI-1 | Ddrgk1 |
| 10396 | 3 | 4 | 5 | 6 | VI-1 | Ddt |
| 10397 | 3 | 4 | 5 | 6 | VI-1 | Ddx1 |
| 10398 | 3 | 4 | 5 | 6 | VI-1 | Ddx18 |
| 10399 | 3 | 4 | 5 | 6 | VI-1 | Ddx21 |
| 10400 | 3 | 4 | 5 | 6 | VI-1 | Ddx24 |
| 10401 | 3 | 4 | 5 | 6 | VI-1 | Ddx27 |
| 10402 | 3 | 4 | 5 | 6 | VI-1 | Ddx28 |
| 10403 | 3 | 4 | 5 | 6 | VI-1 | Ddx31 |
| 10404 | 3 | 4 | 5 | 6 | VI-1 | Ddx39 |
| 10405 | 3 | 4 | 5 | 6 | VI-1 | Ddx3y |
| 10406 | 3 | 4 | 5 | 6 | VI-1 | Ddx41 |
| 10407 | 3 | 4 | 5 | 6 | VI-1 | Ddx52 |
| 10408 | 3 | 4 | 5 | 6 | VI-1 | Ddx54 |
| 10409 | 3 | 4 | 5 | 6 | VI-1 | Ddx55 |
| 10410 | 3 | 4 | 5 | 6 | VI-1 | Ddx60 |
| 10411 | 3 | 4 | 5 | 6 | VI-1 | Deaf1 |
| 10412 | 3 | 4 | 5 | 6 | VI-1 | Deb1 |
| 10413 | 3 | 4 | 5 | 6 | VI-1 | Decr2 |
| 10414 | 3 | 4 | 5 | 6 | VI-1 | Defb19 |
| 10415 | 3 | 4 | 5 | 6 | VI-1 | Defb29 |
| 10416 | 3 | 4 | 5 | 6 | VI-1 | Defb3 |
| 10417 | 3 | 4 | 5 | 6 | VI-1 | Defb4 |
| 10418 | 3 | 4 | 5 | 6 | VI-1 | Defb42 |
| 10419 | 3 | 4 | 5 | 6 | VI-1 | Dek |
| 10420 | 3 | 4 | 5 | 6 | VI-1 | Dennd1b |
| 10421 | 3 | 4 | 5 | 6 | VI-1 | Dennd1c |
| 10422 | 3 | 4 | 5 | 6 | VI-1 | Dennd2a |
| 10423 | 3 | 4 | 5 | 6 | VI-1 | Dennd2d |
| 10424 | 3 | 4 | 5 | 6 | VI-1 | Dennd4c |
| 10425 | 3 | 4 | 5 | 6 | VI-1 | Dennd5b |
| 10426 | 3 | 4 | 5 | 6 | VI-1 | Dennd6b |
| 10427 | 3 | 4 | 5 | 6 | VI-1 | Denr |
| 10428 | 3 | 4 | 5 | 6 | VI-1 | Dera |
| 10429 | 3 | 4 | 5 | 6 | VI-1 | Derl1 |
| 10430 | 3 | 4 | 5 | 6 | VI-1 | Desi1 |
| 10431 | 3 | 4 | 5 | 6 | VI-1 | Desi2 |
| 10432 | 3 | 4 | 5 | 6 | VI-1 | Dexi |
| 10433 | 3 | 4 | 5 | 6 | VI-1 | Dgat2l6 |
| 10434 | 3 | 4 | 5 | 6 | VI-1 | Dgcr14 |
| 10435 | 3 | 4 | 5 | 6 | VI-1 | Dgcr6 |
| 10436 | 3 | 4 | 5 | 6 | VI-1 | Dgcr8 |
| 10437 | 3 | 4 | 5 | 6 | VI-1 | Dgka |
| 10438 | 3 | 4 | 5 | 6 | VI-1 | Dgkb |
| 10439 | 3 | 4 | 5 | 6 | VI-1 | Dgke |
| 10440 | 3 | 4 | 5 | 6 | VI-1 | Dgkeos |
| 10441 | 3 | 4 | 5 | 6 | VI-1 | Dgkg |
| 10442 | 3 | 4 | 5 | 6 | VI-1 | Dgkh |
| 10443 | 3 | 4 | 5 | 6 | VI-1 | Dguok |
| 10444 | 3 | 4 | 5 | 6 | VI-1 | Dhcr24 |
| 10445 | 3 | 4 | 5 | 6 | VI-1 | Dhdds |
| 10446 | 3 | 4 | 5 | 6 | VI-1 | Dhodh |
| 10447 | 3 | 4 | 5 | 6 | VI-1 | Dhps |
| 10448 | 3 | 4 | 5 | 6 | VI-1 | Dhrs11 |
| 10449 | 3 | 4 | 5 | 6 | VI-1 | Dhrs2 |
| 10450 | 3 | 4 | 5 | 6 | VI-1 | Dhrs3 |
| 10451 | 3 | 4 | 5 | 6 | VI-1 | Dhrs4 |
| 10452 | 3 | 4 | 5 | 6 | VI-1 | Dhrs7 |
| 10453 | 3 | 4 | 5 | 6 | VI-1 | Dhrs7b |
| 10454 | 3 | 4 | 5 | 6 | VI-1 | Dhx15 |
| 10455 | 3 | 4 | 5 | 6 | VI-1 | Dhx16 |
| 10456 | 3 | 4 | 5 | 6 | VI-1 | Dhx32 |
| 10457 | 3 | 4 | 5 | 6 | VI-1 | Dhx33 |
| 10458 | 3 | 4 | 5 | 6 | VI-1 | Dhx34 |
| 10459 | 3 | 4 | 5 | 6 | VI-1 | Dhx36 |
| 10460 | 3 | 4 | 5 | 6 | VI-1 | Dhx37 |
| 10461 | 3 | 4 | 5 | 6 | VI-1 | Dhx40 |
| 10462 | 3 | 4 | 5 | 6 | VI-1 | Dhx57 |
| 10463 | 3 | 4 | 5 | 6 | VI-1 | Dhx8 |
| 10464 | 3 | 4 | 5 | 6 | VI-1 | Diablo |
| 10465 | 3 | 4 | 5 | 6 | VI-1 | Diap2 |
| 10466 | 3 | 4 | 5 | 6 | VI-1 | Diexf |
| 10467 | 3 | 4 | 5 | 6 | VI-1 | Dio1 |
| 10468 | 3 | 4 | 5 | 6 | VI-1 | Dio2 |
| 10469 | 3 | 4 | 5 | 6 | VI-1 | Dio3 |
| 10470 | 3 | 4 | 5 | 6 | VI-1 | Dirc2 |
| 10471 | 3 | 4 | 5 | 6 | VI-1 | Dis3l |
| 10472 | 3 | 4 | 5 | 6 | VI-1 | Dis3l2 |
| 10473 | 3 | 4 | 5 | 6 | VI-1 | Dixdc1 |
| 10474 | 3 | 4 | 5 | 6 | VI-1 | Dkk3 |
| 10475 | 3 | 4 | 5 | 6 | VI-1 | Dkkl1 |
| 10476 | 3 | 4 | 5 | 6 | VI-1 | Dleu2 |
| 10477 | 3 | 4 | 5 | 6 | VI-1 | Dlg5 |
| 10478 | 3 | 4 | 5 | 6 | VI-1 | Dlk2 |
| 10479 | 3 | 4 | 5 | 6 | VI-1 | Dlx1as |
| 10480 | 3 | 4 | 5 | 6 | VI-1 | Dmd |
| 10481 | 3 | 4 | 5 | 6 | VI-1 | Dmpk |
| 10482 | 3 | 4 | 5 | 6 | VI-1 | Dmrt3 |
| 10483 | 3 | 4 | 5 | 6 | VI-1 | Dmrta1 |
| 10484 | 3 | 4 | 5 | 6 | VI-1 | Dmrtb1 |
| 10485 | 3 | 4 | 5 | 6 | VI-1 | Dmxl1 |
| 10486 | 3 | 4 | 5 | 6 | VI-1 | Dna2 |
| 10487 | 3 | 4 | 5 | 6 | VI-1 | Dnaaf3 |
| 10488 | 3 | 4 | 5 | 6 | VI-1 | Dnah2 |
| 10489 | 3 | 4 | 5 | 6 | VI-1 | Dnah6 |
| 10490 | 3 | 4 | 5 | 6 | VI-1 | Dnaja4 |
| 10491 | 3 | 4 | 5 | 6 | VI-1 | Dnajb1 |
| 10492 | 3 | 4 | 5 | 6 | VI-1 | Dnajb11 |
| 10493 | 3 | 4 | 5 | 6 | VI-1 | Dnajb13 |
| 10494 | 3 | 4 | 5 | 6 | VI-1 | Dnajb6 |
| 10495 | 3 | 4 | 5 | 6 | VI-1 | Dnajb7 |
| 10496 | 3 | 4 | 5 | 6 | VI-1 | Dnajb8 |
| 10497 | 3 | 4 | 5 | 6 | VI-1 | Dnajc1 |
| 10498 | 3 | 4 | 5 | 6 | VI-1 | Dnajc12 |
| 10499 | 3 | 4 | 5 | 6 | VI-1 | Dnajc2 |
| 10500 | 3 | 4 | 5 | 6 | VI-1 | Dnajc21 |
| 10501 | 3 | 4 | 5 | 6 | VI-1 | Dnajc24 |
| 10502 | 3 | 4 | 5 | 6 | VI-1 | Dnajc25 |
| 10503 | 3 | 4 | 5 | 6 | VI-1 | Dnajc27 |
| 10504 | 3 | 4 | 5 | 6 | VI-1 | Dnajc30 |
| 10505 | 3 | 4 | 5 | 6 | VI-1 | Dnajc4 |
| 10506 | 3 | 4 | 5 | 6 | VI-1 | Dnajc5b |
| 10507 | 3 | 4 | 5 | 6 | VI-1 | Dnajc6 |
| 10508 | 3 | 4 | 5 | 6 | VI-1 | Dnajc7 |
| 10509 | 3 | 4 | 5 | 6 | VI-1 | Dnajc8 |
| 10510 | 3 | 4 | 5 | 6 | VI-1 | Dnal1 |
| 10511 | 3 | 4 | 5 | 6 | VI-1 | Dnali1 |
| 10512 | 3 | 4 | 5 | 6 | VI-1 | Dnase1l2 |
| 10513 | 3 | 4 | 5 | 6 | VI-1 | Dnase1l3 |
| 10514 | 3 | 4 | 5 | 6 | VI-1 | Dnlz |
| 10515 | 3 | 4 | 5 | 6 | VI-1 | Dnm1 |
| 10516 | 3 | 4 | 5 | 6 | VI-1 | Dnm2 |
| 10517 | 3 | 4 | 5 | 6 | VI-1 | Dnm3 |
| 10518 | 3 | 4 | 5 | 6 | VI-1 | Dnm3os |
| 10519 | 3 | 4 | 5 | 6 | VI-1 | Dnpep |
| 10520 | 3 | 4 | 5 | 6 | VI-1 | Dnttip2 |
| 10521 | 3 | 4 | 5 | 6 | VI-1 | Dock3 |
| 10522 | 3 | 4 | 5 | 6 | VI-1 | Dock9 |
| 10523 | 3 | 4 | 5 | 6 | VI-1 | Dohh |
| 10524 | 3 | 4 | 5 | 6 | VI-1 | Dok1 |
| 10525 | 3 | 4 | 5 | 6 | VI-1 | Dok2 |
| 10526 | 3 | 4 | 5 | 6 | VI-1 | Dok3 |
| 10527 | 3 | 4 | 5 | 6 | VI-1 | Dok7 |
| 10528 | 3 | 4 | 5 | 6 | VI-1 | Dolk |
| 10529 | 3 | 4 | 5 | 6 | VI-1 | Donson |
| 10530 | 3 | 4 | 5 | 6 | VI-1 | Dopey1 |
| 10531 | 3 | 4 | 5 | 6 | VI-1 | Dopey2 |
| 10532 | 3 | 4 | 5 | 6 | VI-1 | Dos |
| 10533 | 3 | 4 | 5 | 6 | VI-1 | Dpep2 |
| 10534 | 3 | 4 | 5 | 6 | VI-1 | Dpep3 |
| 10535 | 3 | 4 | 5 | 6 | VI-1 | Dph2 |
| 10536 | 3 | 4 | 5 | 6 | VI-1 | Dph3 |
| 10537 | 3 | 4 | 5 | 6 | VI-1 | Dpm1 |
| 10538 | 3 | 4 | 5 | 6 | VI-1 | Dpm2 |
| 10539 | 3 | 4 | 5 | 6 | VI-1 | Dpp10 |
| 10540 | 3 | 4 | 5 | 6 | VI-1 | Dpp3 |
| 10541 | 3 | 4 | 5 | 6 | VI-1 | Dppa5a |
| 10542 | 3 | 4 | 5 | 6 | VI-1 | Dpy19l1 |
| 10543 | 3 | 4 | 5 | 6 | VI-1 | Dpyd |
| 10544 | 3 | 4 | 5 | 6 | VI-1 | Dpysl4 |
| 10545 | 3 | 4 | 5 | 6 | VI-1 | Dpysl5 |
| 10546 | 3 | 4 | 5 | 6 | VI-1 | Dram2 |
| 10547 | 3 | 4 | 5 | 6 | VI-1 | Draxin |
| 10548 | 3 | 4 | 5 | 6 | VI-1 | Drc1 |
| 10549 | 3 | 4 | 5 | 6 | VI-1 | Drd4 |
| 10550 | 3 | 4 | 5 | 6 | VI-1 | Drd5 |
| 10551 | 3 | 4 | 5 | 6 | VI-1 | Drg1 |
| 10552 | 3 | 4 | 5 | 6 | VI-1 | Drg2 |
| 10553 | 3 | 4 | 5 | 6 | VI-1 | Dsc2 |
| 10554 | 3 | 4 | 5 | 6 | VI-1 | Dscr3 |
| 10555 | 3 | 4 | 5 | 6 | VI-1 | Dsel |
| 10556 | 3 | 4 | 5 | 6 | VI-1 | Dsg2 |
| 10557 | 3 | 4 | 5 | 6 | VI-1 | Dstn |
| 10558 | 3 | 4 | 5 | 6 | VI-1 | Dstyk |

Fig. 34 - 56

| | | | | | | |
|---|---|---|---|---|---|---|
| 10559 | 3 | 4 | 5 | 6 | VI-1 | Dtna |
| 10560 | 3 | 4 | 5 | 6 | VI-1 | Dtnbp1 |
| 10561 | 3 | 4 | 5 | 6 | VI-1 | Dtx1 |
| 10562 | 3 | 4 | 5 | 6 | VI-1 | Dtx2 |
| 10563 | 3 | 4 | 5 | 6 | VI-1 | Dtx3l |
| 10564 | 3 | 4 | 5 | 6 | VI-1 | Dtx4 |
| 10565 | 3 | 4 | 5 | 6 | VI-1 | Dtymk |
| 10566 | 3 | 4 | 5 | 6 | VI-1 | Duox2 |
| 10567 | 3 | 4 | 5 | 6 | VI-1 | Duoxa2 |
| 10568 | 3 | 4 | 5 | 6 | VI-1 | Dus3l |
| 10569 | 3 | 4 | 5 | 6 | VI-1 | Dus4l |
| 10570 | 3 | 4 | 5 | 6 | VI-1 | Dusp10 |
| 10571 | 3 | 4 | 5 | 6 | VI-1 | Dusp11 |
| 10572 | 3 | 4 | 5 | 6 | VI-1 | Dusp12 |
| 10573 | 3 | 4 | 5 | 6 | VI-1 | Dusp13 |
| 10574 | 3 | 4 | 5 | 6 | VI-1 | Dusp14 |
| 10575 | 3 | 4 | 5 | 6 | VI-1 | Dusp15 |
| 10576 | 3 | 4 | 5 | 6 | VI-1 | Dusp18 |
| 10577 | 3 | 4 | 5 | 6 | VI-1 | Dusp19 |
| 10578 | 3 | 4 | 5 | 6 | VI-1 | Dusp2 |
| 10579 | 3 | 4 | 5 | 6 | VI-1 | Dusp27 |
| 10580 | 3 | 4 | 5 | 6 | VI-1 | Dusp3 |
| 10581 | 3 | 4 | 5 | 6 | VI-1 | Dusp4 |
| 10582 | 3 | 4 | 5 | 6 | VI-1 | Dusp6 |
| 10583 | 3 | 4 | 5 | 6 | VI-1 | Dusp8 |
| 10584 | 3 | 4 | 5 | 6 | VI-1 | Dvl1 |
| 10585 | 3 | 4 | 5 | 6 | VI-1 | Dxo |
| 10586 | 3 | 4 | 5 | 6 | VI-1 | Dydc2 |
| 10587 | 3 | 4 | 5 | 6 | VI-1 | Dync1i1 |
| 10588 | 3 | 4 | 5 | 6 | VI-1 | Dync1li2 |
| 10589 | 3 | 4 | 5 | 6 | VI-1 | Dync2li1 |
| 10590 | 3 | 4 | 5 | 6 | VI-1 | Dynll2 |
| 10591 | 3 | 4 | 5 | 6 | VI-1 | Dynlrb2 |
| 10592 | 3 | 4 | 5 | 6 | VI-1 | Dynlt1a |
| 10593 | 3 | 4 | 5 | 6 | VI-1 | Dynlt1b |
| 10594 | 3 | 4 | 5 | 6 | VI-1 | Dynlt1f |
| 10595 | 3 | 4 | 5 | 6 | VI-1 | Dyrk2 |
| 10596 | 3 | 4 | 5 | 6 | VI-1 | Dyrk3 |
| 10597 | 3 | 4 | 5 | 6 | VI-1 | Dytn |
| 10598 | 3 | 4 | 5 | 6 | VI-1 | E030019B06Rik |
| 10599 | 3 | 4 | 5 | 6 | VI-1 | E030024N20Rik |
| 10600 | 3 | 4 | 5 | 6 | VI-1 | E130102H24Rik |
| 10601 | 3 | 4 | 5 | 6 | VI-1 | E130215H24Rik |
| 10602 | 3 | 4 | 5 | 6 | VI-1 | E130218I03Rik |
| 10603 | 3 | 4 | 5 | 6 | VI-1 | E130307A14Rik |
| 10604 | 3 | 4 | 5 | 6 | VI-1 | E130309D14Rik |
| 10605 | 3 | 4 | 5 | 6 | VI-1 | E230016M11Rik |
| 10606 | 3 | 4 | 5 | 6 | VI-1 | E230029C05Rik |
| 10607 | 3 | 4 | 5 | 6 | VI-1 | E2f1 |
| 10608 | 3 | 4 | 5 | 6 | VI-1 | E2f3 |
| 10609 | 3 | 4 | 5 | 6 | VI-1 | E2f4 |
| 10610 | 3 | 4 | 5 | 6 | VI-1 | E2f7 |
| 10611 | 3 | 4 | 5 | 6 | VI-1 | E4f1 |
| 10612 | 3 | 4 | 5 | 6 | VI-1 | Eaf2 |
| 10613 | 3 | 4 | 5 | 6 | VI-1 | Ear2 |
| 10614 | 3 | 4 | 5 | 6 | VI-1 | Ear7 |
| 10615 | 3 | 4 | 5 | 6 | VI-1 | Ears2 |
| 10616 | 3 | 4 | 5 | 6 | VI-1 | Ebf2 |
| 10617 | 3 | 4 | 5 | 6 | VI-1 | Ebna1bp2 |
| 10618 | 3 | 4 | 5 | 6 | VI-1 | Ece2 |
| 10619 | 3 | 4 | 5 | 6 | VI-1 | Ech1 |
| 10620 | 3 | 4 | 5 | 6 | VI-1 | Echdc3 |
| 10621 | 3 | 4 | 5 | 6 | VI-1 | Eci1 |
| 10622 | 3 | 4 | 5 | 6 | VI-1 | Ecm1 |
| 10623 | 3 | 4 | 5 | 6 | VI-1 | Ecm2 |
| 10624 | 3 | 4 | 5 | 6 | VI-1 | Eda |
| 10625 | 3 | 4 | 5 | 6 | VI-1 | Eda2r |
| 10626 | 3 | 4 | 5 | 6 | VI-1 | Edc4 |
| 10627 | 3 | 4 | 5 | 6 | VI-1 | Edem1 |
| 10628 | 3 | 4 | 5 | 6 | VI-1 | Edem2 |
| 10629 | 3 | 4 | 5 | 6 | VI-1 | Edem3 |
| 10630 | 3 | 4 | 5 | 6 | VI-1 | Edil3 |
| 10631 | 3 | 4 | 5 | 6 | VI-1 | Edn1 |
| 10632 | 3 | 4 | 5 | 6 | VI-1 | Edn3 |
| 10633 | 3 | 4 | 5 | 6 | VI-1 | Ednrb |
| 10634 | 3 | 4 | 5 | 6 | VI-1 | Edrf1 |
| 10635 | 3 | 4 | 5 | 6 | VI-1 | Eea1 |
| 10636 | 3 | 4 | 5 | 6 | VI-1 | Eef1a1 |
| 10637 | 3 | 4 | 5 | 6 | VI-1 | Eef1b2 |
| 10638 | 3 | 4 | 5 | 6 | VI-1 | Eef2 |
| 10639 | 3 | 4 | 5 | 6 | VI-1 | Eepd1 |
| 10640 | 3 | 4 | 5 | 6 | VI-1 | Efcab10 |
| 10641 | 3 | 4 | 5 | 6 | VI-1 | Efcab11 |
| 10642 | 3 | 4 | 5 | 6 | VI-1 | Efcab6 |
| 10643 | 3 | 4 | 5 | 6 | VI-1 | Efcab8 |
| 10644 | 3 | 4 | 5 | 6 | VI-1 | Efhd1 |
| 10645 | 3 | 4 | 5 | 6 | VI-1 | Efhd2 |
| 10646 | 3 | 4 | 5 | 6 | VI-1 | Efna1 |
| 10647 | 3 | 4 | 5 | 6 | VI-1 | Efna4 |
| 10648 | 3 | 4 | 5 | 6 | VI-1 | Efna5 |
| 10649 | 3 | 4 | 5 | 6 | VI-1 | Efnb3 |
| 10650 | 3 | 4 | 5 | 6 | VI-1 | Efr3b |
| 10651 | 3 | 4 | 5 | 6 | VI-1 | Eftud2 |
| 10652 | 3 | 4 | 5 | 6 | VI-1 | Egf |
| 10653 | 3 | 4 | 5 | 6 | VI-1 | Egfl8 |
| 10654 | 3 | 4 | 5 | 6 | VI-1 | Egfr |
| 10655 | 3 | 4 | 5 | 6 | VI-1 | Ehbp1l1 |
| 10656 | 3 | 4 | 5 | 6 | VI-1 | Ehd1 |
| 10657 | 3 | 4 | 5 | 6 | VI-1 | Ehd2 |
| 10658 | 3 | 4 | 5 | 6 | VI-1 | Ehd4 |
| 10659 | 3 | 4 | 5 | 6 | VI-1 | Ehmt2 |
| 10660 | 3 | 4 | 5 | 6 | VI-1 | Ei24 |
| 10661 | 3 | 4 | 5 | 6 | VI-1 | Eid2 |
| 10662 | 3 | 4 | 5 | 6 | VI-1 | Eid3 |
| 10663 | 3 | 4 | 5 | 6 | VI-1 | Eif1 |
| 10664 | 3 | 4 | 5 | 6 | VI-1 | Eif1ad |
| 10665 | 3 | 4 | 5 | 6 | VI-1 | Eif1ax |
| 10666 | 3 | 4 | 5 | 6 | VI-1 | Eif1b |
| 10667 | 3 | 4 | 5 | 6 | VI-1 | Eif2ak2 |
| 10668 | 3 | 4 | 5 | 6 | VI-1 | Eif2b1 |
| 10669 | 3 | 4 | 5 | 6 | VI-1 | Eif2b3 |
| 10670 | 3 | 4 | 5 | 6 | VI-1 | Eif2b5 |
| 10671 | 3 | 4 | 5 | 6 | VI-1 | Eif2d |
| 10672 | 3 | 4 | 5 | 6 | VI-1 | Eif2s1 |
| 10673 | 3 | 4 | 5 | 6 | VI-1 | Eif2s2 |
| 10674 | 3 | 4 | 5 | 6 | VI-1 | Eif3c |
| 10675 | 3 | 4 | 5 | 6 | VI-1 | Eif3g |
| 10676 | 3 | 4 | 5 | 6 | VI-1 | Eif3i |
| 10677 | 3 | 4 | 5 | 6 | VI-1 | Eif3j |
| 10678 | 3 | 4 | 5 | 6 | VI-1 | Eif4a1 |
| 10679 | 3 | 4 | 5 | 6 | VI-1 | Eif4e |
| 10680 | 3 | 4 | 5 | 6 | VI-1 | Eif4g1 |
| 10681 | 3 | 4 | 5 | 6 | VI-1 | Eif4g3 |
| 10682 | 3 | 4 | 5 | 6 | VI-1 | Eif4h |
| 10683 | 3 | 4 | 5 | 6 | VI-1 | Eif5a |
| 10684 | 3 | 4 | 5 | 6 | VI-1 | Eif5b |
| 10685 | 3 | 4 | 5 | 6 | VI-1 | Elac2 |
| 10686 | 3 | 4 | 5 | 6 | VI-1 | Elavl2 |
| 10687 | 3 | 4 | 5 | 6 | VI-1 | Elavl4 |
| 10688 | 3 | 4 | 5 | 6 | VI-1 | Elf2 |
| 10689 | 3 | 4 | 5 | 6 | VI-1 | Elf3 |
| 10690 | 3 | 4 | 5 | 6 | VI-1 | Elf5 |
| 10691 | 3 | 4 | 5 | 6 | VI-1 | Elk3 |
| 10692 | 3 | 4 | 5 | 6 | VI-1 | Ell |
| 10693 | 3 | 4 | 5 | 6 | VI-1 | Ell2 |
| 10694 | 3 | 4 | 5 | 6 | VI-1 | Ell3 |
| 10695 | 3 | 4 | 5 | 6 | VI-1 | Elmo3 |
| 10696 | 3 | 4 | 5 | 6 | VI-1 | Elmod2 |
| 10697 | 3 | 4 | 5 | 6 | VI-1 | Eln |
| 10698 | 3 | 4 | 5 | 6 | VI-1 | Elof1 |
| 10699 | 3 | 4 | 5 | 6 | VI-1 | Elovl1 |
| 10700 | 3 | 4 | 5 | 6 | VI-1 | Elovl7 |
| 10701 | 3 | 4 | 5 | 6 | VI-1 | Elp3 |
| 10702 | 3 | 4 | 5 | 6 | VI-1 | Elp5 |
| 10703 | 3 | 4 | 5 | 6 | VI-1 | Emb |
| 10704 | 3 | 4 | 5 | 6 | VI-1 | Emc1 |
| 10705 | 3 | 4 | 5 | 6 | VI-1 | Emc10 |
| 10706 | 3 | 4 | 5 | 6 | VI-1 | Emc2 |
| 10707 | 3 | 4 | 5 | 6 | VI-1 | Emc3 |
| 10708 | 3 | 4 | 5 | 6 | VI-1 | Emc6 |
| 10709 | 3 | 4 | 5 | 6 | VI-1 | Emcn |
| 10710 | 3 | 4 | 5 | 6 | VI-1 | Eme1 |
| 10711 | 3 | 4 | 5 | 6 | VI-1 | Emg1 |
| 10712 | 3 | 4 | 5 | 6 | VI-1 | Emilin1 |
| 10713 | 3 | 4 | 5 | 6 | VI-1 | Emilin2 |
| 10714 | 3 | 4 | 5 | 6 | VI-1 | Eml1 |
| 10715 | 3 | 4 | 5 | 6 | VI-1 | Eml2 |
| 10716 | 3 | 4 | 5 | 6 | VI-1 | Eml3 |
| 10717 | 3 | 4 | 5 | 6 | VI-1 | Eml5 |
| 10718 | 3 | 4 | 5 | 6 | VI-1 | En2 |
| 10719 | 3 | 4 | 5 | 6 | VI-1 | Enc1 |
| 10720 | 3 | 4 | 5 | 6 | VI-1 | Enkd1 |
| 10721 | 3 | 4 | 5 | 6 | VI-1 | Enkur |
| 10722 | 3 | 4 | 5 | 6 | VI-1 | Eno4 |
| 10723 | 3 | 4 | 5 | 6 | VI-1 | Enox2 |
| 10724 | 3 | 4 | 5 | 6 | VI-1 | Enpp5 |
| 10725 | 3 | 4 | 5 | 6 | VI-1 | Enthd2 |
| 10726 | 3 | 4 | 5 | 6 | VI-1 | Entpd1 |
| 10727 | 3 | 4 | 5 | 6 | VI-1 | Entpd2 |
| 10728 | 3 | 4 | 5 | 6 | VI-1 | Entpd4 |
| 10729 | 3 | 4 | 5 | 6 | VI-1 | Entpd5 |
| 10730 | 3 | 4 | 5 | 6 | VI-1 | Entpd8 |
| 10731 | 3 | 4 | 5 | 6 | VI-1 | Epb4.1l1 |
| 10732 | 3 | 4 | 5 | 6 | VI-1 | Epb4.1l5 |
| 10733 | 3 | 4 | 5 | 6 | VI-1 | Epha1 |
| 10734 | 3 | 4 | 5 | 6 | VI-1 | Epha2 |
| 10735 | 3 | 4 | 5 | 6 | VI-1 | Epha4 |
| 10736 | 3 | 4 | 5 | 6 | VI-1 | Ephb6 |
| 10737 | 3 | 4 | 5 | 6 | VI-1 | Epm2aip1 |
| 10738 | 3 | 4 | 5 | 6 | VI-1 | Epn2 |
| 10739 | 3 | 4 | 5 | 6 | VI-1 | Epn3 |
| 10740 | 3 | 4 | 5 | 6 | VI-1 | Epor |
| 10741 | 3 | 4 | 5 | 6 | VI-1 | Eppk1 |
| 10742 | 3 | 4 | 5 | 6 | VI-1 | Eps15 |
| 10743 | 3 | 4 | 5 | 6 | VI-1 | Eps8 |
| 10744 | 3 | 4 | 5 | 6 | VI-1 | Eps8l1 |
| 10745 | 3 | 4 | 5 | 6 | VI-1 | Eps8l2 |
| 10746 | 3 | 4 | 5 | 6 | VI-1 | Epsti1 |
| 10747 | 3 | 4 | 5 | 6 | VI-1 | Epx |
| 10748 | 3 | 4 | 5 | 6 | VI-1 | Erap1 |
| 10749 | 3 | 4 | 5 | 6 | VI-1 | Erc1 |
| 10750 | 3 | 4 | 5 | 6 | VI-1 | Erc2 |

Fig. 34 - 57

| | | | | | | |
|---|---|---|---|---|---|---|
| 10751 | 3 | 4 | 5 | 6 | VI-1 | Ercc1 |
| 10752 | 3 | 4 | 5 | 6 | VI-1 | Ercc2 |
| 10753 | 3 | 4 | 5 | 6 | VI-1 | Erf |
| 10754 | 3 | 4 | 5 | 6 | VI-1 | Ergic3 |
| 10755 | 3 | 4 | 5 | 6 | VI-1 | Erh |
| 10756 | 3 | 4 | 5 | 6 | VI-1 | Eri1 |
| 10757 | 3 | 4 | 5 | 6 | VI-1 | Eri2 |
| 10758 | 3 | 4 | 5 | 6 | VI-1 | Erich2 |
| 10759 | 3 | 4 | 5 | 6 | VI-1 | Erich4 |
| 10760 | 3 | 4 | 5 | 6 | VI-1 | Erich5 |
| 10761 | 3 | 4 | 5 | 6 | VI-1 | Erlec1 |
| 10762 | 3 | 4 | 5 | 6 | VI-1 | Erlin1 |
| 10763 | 3 | 4 | 5 | 6 | VI-1 | Ermard |
| 10764 | 3 | 4 | 5 | 6 | VI-1 | Ermn |
| 10765 | 3 | 4 | 5 | 6 | VI-1 | Erp29 |
| 10766 | 3 | 4 | 5 | 6 | VI-1 | Erp44 |
| 10767 | 3 | 4 | 5 | 6 | VI-1 | Erv3 |
| 10768 | 3 | 4 | 5 | 6 | VI-1 | Esam |
| 10769 | 3 | 4 | 5 | 6 | VI-1 | Esco1 |
| 10770 | 3 | 4 | 5 | 6 | VI-1 | Esrp1 |
| 10771 | 3 | 4 | 5 | 6 | VI-1 | Esrrb |
| 10772 | 3 | 4 | 5 | 6 | VI-1 | Esyt2 |
| 10773 | 3 | 4 | 5 | 6 | VI-1 | Etaa1 |
| 10774 | 3 | 4 | 5 | 6 | VI-1 | Etf1 |
| 10775 | 3 | 4 | 5 | 6 | VI-1 | Etfa |
| 10776 | 3 | 4 | 5 | 6 | VI-1 | Etfdh |
| 10777 | 3 | 4 | 5 | 6 | VI-1 | Etv1 |
| 10778 | 3 | 4 | 5 | 6 | VI-1 | Etv4 |
| 10779 | 3 | 4 | 5 | 6 | VI-1 | Etv5 |
| 10780 | 3 | 4 | 5 | 6 | VI-1 | Eva1b |
| 10781 | 3 | 4 | 5 | 6 | VI-1 | Evc2 |
| 10782 | 3 | 4 | 5 | 6 | VI-1 | Evi5l |
| 10783 | 3 | 4 | 5 | 6 | VI-1 | Evl |
| 10784 | 3 | 4 | 5 | 6 | VI-1 | Exo5 |
| 10785 | 3 | 4 | 5 | 6 | VI-1 | Exoc1 |
| 10786 | 3 | 4 | 5 | 6 | VI-1 | Exoc3 |
| 10787 | 3 | 4 | 5 | 6 | VI-1 | Exoc3l |
| 10788 | 3 | 4 | 5 | 6 | VI-1 | Exoc3l4 |
| 10789 | 3 | 4 | 5 | 6 | VI-1 | Exoc6b |
| 10790 | 3 | 4 | 5 | 6 | VI-1 | Exoc8 |
| 10791 | 3 | 4 | 5 | 6 | VI-1 | Exog |
| 10792 | 3 | 4 | 5 | 6 | VI-1 | Exosc2 |
| 10793 | 3 | 4 | 5 | 6 | VI-1 | Exosc4 |
| 10794 | 3 | 4 | 5 | 6 | VI-1 | Exosc5 |
| 10795 | 3 | 4 | 5 | 6 | VI-1 | Exosc6 |
| 10796 | 3 | 4 | 5 | 6 | VI-1 | Exosc8 |
| 10797 | 3 | 4 | 5 | 6 | VI-1 | Ext2 |
| 10798 | 3 | 4 | 5 | 6 | VI-1 | Eya1 |
| 10799 | 3 | 4 | 5 | 6 | VI-1 | Eya4 |
| 10800 | 3 | 4 | 5 | 6 | VI-1 | F10 |
| 10801 | 3 | 4 | 5 | 6 | VI-1 | F12 |
| 10802 | 3 | 4 | 5 | 6 | VI-1 | F2 |
| 10803 | 3 | 4 | 5 | 6 | VI-1 | F2rl3 |
| 10804 | 3 | 4 | 5 | 6 | VI-1 | F5 |
| 10805 | 3 | 4 | 5 | 6 | VI-1 | Faah |
| 10806 | 3 | 4 | 5 | 6 | VI-1 | Fabp4 |
| 10807 | 3 | 4 | 5 | 6 | VI-1 | Fads3 |
| 10808 | 3 | 4 | 5 | 6 | VI-1 | Faf2 |
| 10809 | 3 | 4 | 5 | 6 | VI-1 | Fahd1 |
| 10810 | 3 | 4 | 5 | 6 | VI-1 | Faim |
| 10811 | 3 | 4 | 5 | 6 | VI-1 | Fam102b |
| 10812 | 3 | 4 | 5 | 6 | VI-1 | Fam104a |
| 10813 | 3 | 4 | 5 | 6 | VI-1 | Fam109a |
| 10814 | 3 | 4 | 5 | 6 | VI-1 | Fam110a |
| 10815 | 3 | 4 | 5 | 6 | VI-1 | Fam110c |
| 10816 | 3 | 4 | 5 | 6 | VI-1 | Fam111a |
| 10817 | 3 | 4 | 5 | 6 | VI-1 | Fam114a2 |
| 10818 | 3 | 4 | 5 | 6 | VI-1 | Fam115a |
| 10819 | 3 | 4 | 5 | 6 | VI-1 | Fam117b |
| 10820 | 3 | 4 | 5 | 6 | VI-1 | Fam118b |
| 10821 | 3 | 4 | 5 | 6 | VI-1 | Fam120c |
| 10822 | 3 | 4 | 5 | 6 | VI-1 | Fam122b |
| 10823 | 3 | 4 | 5 | 6 | VI-1 | Fam124a |
| 10824 | 3 | 4 | 5 | 6 | VI-1 | Fam129b |
| 10825 | 3 | 4 | 5 | 6 | VI-1 | Fam131c |
| 10826 | 3 | 4 | 5 | 6 | VI-1 | Fam132b |
| 10827 | 3 | 4 | 5 | 6 | VI-1 | Fam133b |
| 10828 | 3 | 4 | 5 | 6 | VI-1 | Fam134b |
| 10829 | 3 | 4 | 5 | 6 | VI-1 | Fam134c |
| 10830 | 3 | 4 | 5 | 6 | VI-1 | Fam13a |
| 10831 | 3 | 4 | 5 | 6 | VI-1 | Fam13b |
| 10832 | 3 | 4 | 5 | 6 | VI-1 | Fam13c |
| 10833 | 3 | 4 | 5 | 6 | VI-1 | Fam150b |
| 10834 | 3 | 4 | 5 | 6 | VI-1 | Fam151b |
| 10835 | 3 | 4 | 5 | 6 | VI-1 | Fam155a |
| 10836 | 3 | 4 | 5 | 6 | VI-1 | Fam159a |
| 10837 | 3 | 4 | 5 | 6 | VI-1 | Fam160a1 |
| 10838 | 3 | 4 | 5 | 6 | VI-1 | Fam160a2 |
| 10839 | 3 | 4 | 5 | 6 | VI-1 | Fam160b1 |
| 10840 | 3 | 4 | 5 | 6 | VI-1 | Fam160b2 |
| 10841 | 3 | 4 | 5 | 6 | VI-1 | Fam161a |
| 10842 | 3 | 4 | 5 | 6 | VI-1 | Fam162a |
| 10843 | 3 | 4 | 5 | 6 | VI-1 | Fam166a |
| 10844 | 3 | 4 | 5 | 6 | VI-1 | Fam166b |
| 10845 | 3 | 4 | 5 | 6 | VI-1 | Fam168a |
| 10846 | 3 | 4 | 5 | 6 | VI-1 | Fam169b |
| 10847 | 3 | 4 | 5 | 6 | VI-1 | Fam171a1 |
| 10848 | 3 | 4 | 5 | 6 | VI-1 | Fam171a2 |
| 10849 | 3 | 4 | 5 | 6 | VI-1 | Fam172a |
| 10850 | 3 | 4 | 5 | 6 | VI-1 | Fam175b |
| 10851 | 3 | 4 | 5 | 6 | VI-1 | Fam178b |
| 10852 | 3 | 4 | 5 | 6 | VI-1 | Fam179a |
| 10853 | 3 | 4 | 5 | 6 | VI-1 | Fam179b |
| 10854 | 3 | 4 | 5 | 6 | VI-1 | Fam180a |
| 10855 | 3 | 4 | 5 | 6 | VI-1 | Fam181b |
| 10856 | 3 | 4 | 5 | 6 | VI-1 | Fam183b |
| 10857 | 3 | 4 | 5 | 6 | VI-1 | Fam187b |
| 10858 | 3 | 4 | 5 | 6 | VI-1 | Fam188a |
| 10859 | 3 | 4 | 5 | 6 | VI-1 | Fam188b |
| 10860 | 3 | 4 | 5 | 6 | VI-1 | Fam189a1 |
| 10861 | 3 | 4 | 5 | 6 | VI-1 | Fam189a2 |
| 10862 | 3 | 4 | 5 | 6 | VI-1 | Fam192a |
| 10863 | 3 | 4 | 5 | 6 | VI-1 | Fam193b |
| 10864 | 3 | 4 | 5 | 6 | VI-1 | Fam203a |
| 10865 | 3 | 4 | 5 | 6 | VI-1 | Fam206a |
| 10866 | 3 | 4 | 5 | 6 | VI-1 | Fam207a |
| 10867 | 3 | 4 | 5 | 6 | VI-1 | Fam208a |
| 10868 | 3 | 4 | 5 | 6 | VI-1 | Fam208b |
| 10869 | 3 | 4 | 5 | 6 | VI-1 | Fam209 |
| 10870 | 3 | 4 | 5 | 6 | VI-1 | Fam20a |
| 10871 | 3 | 4 | 5 | 6 | VI-1 | Fam20c |
| 10872 | 3 | 4 | 5 | 6 | VI-1 | Fam212b |
| 10873 | 3 | 4 | 5 | 6 | VI-1 | Fam214b |
| 10874 | 3 | 4 | 5 | 6 | VI-1 | Fam216a |
| 10875 | 3 | 4 | 5 | 6 | VI-1 | Fam216b |
| 10876 | 3 | 4 | 5 | 6 | VI-1 | Fam217b |
| 10877 | 3 | 4 | 5 | 6 | VI-1 | Fam220a |
| 10878 | 3 | 4 | 5 | 6 | VI-1 | Fam221b |
| 10879 | 3 | 4 | 5 | 6 | VI-1 | Fam227a |
| 10880 | 3 | 4 | 5 | 6 | VI-1 | Fam26f |
| 10881 | 3 | 4 | 5 | 6 | VI-1 | Fam32a |
| 10882 | 3 | 4 | 5 | 6 | VI-1 | Fam35a |
| 10883 | 3 | 4 | 5 | 6 | VI-1 | Fam3a |
| 10884 | 3 | 4 | 5 | 6 | VI-1 | Fam3b |
| 10885 | 3 | 4 | 5 | 6 | VI-1 | Fam46a |
| 10886 | 3 | 4 | 5 | 6 | VI-1 | Fam46b |
| 10887 | 3 | 4 | 5 | 6 | VI-1 | Fam46c |
| 10888 | 3 | 4 | 5 | 6 | VI-1 | Fam49b |
| 10889 | 3 | 4 | 5 | 6 | VI-1 | Fam50a |
| 10890 | 3 | 4 | 5 | 6 | VI-1 | Fam50b |
| 10891 | 3 | 4 | 5 | 6 | VI-1 | Fam53a |
| 10892 | 3 | 4 | 5 | 6 | VI-1 | Fam53c |
| 10893 | 3 | 4 | 5 | 6 | VI-1 | Fam69a |
| 10894 | 3 | 4 | 5 | 6 | VI-1 | Fam71e1 |
| 10895 | 3 | 4 | 5 | 6 | VI-1 | Fam71f1 |
| 10896 | 3 | 4 | 5 | 6 | VI-1 | Fam71f2 |
| 10897 | 3 | 4 | 5 | 6 | VI-1 | Fam73b |
| 10898 | 3 | 4 | 5 | 6 | VI-1 | Fam76b |
| 10899 | 3 | 4 | 5 | 6 | VI-1 | Fam81a |
| 10900 | 3 | 4 | 5 | 6 | VI-1 | Fam83d |
| 10901 | 3 | 4 | 5 | 6 | VI-1 | Fam83e |
| 10902 | 3 | 4 | 5 | 6 | VI-1 | Fam83g |
| 10903 | 3 | 4 | 5 | 6 | VI-1 | Fam83h |
| 10904 | 3 | 4 | 5 | 6 | VI-1 | Fam84a |
| 10905 | 3 | 4 | 5 | 6 | VI-1 | Fam86 |
| 10906 | 3 | 4 | 5 | 6 | VI-1 | Fam92a |
| 10907 | 3 | 4 | 5 | 6 | VI-1 | Fam98a |
| 10908 | 3 | 4 | 5 | 6 | VI-1 | Fam98b |
| 10909 | 3 | 4 | 5 | 6 | VI-1 | Fancc |
| 10910 | 3 | 4 | 5 | 6 | VI-1 | Fancg |
| 10911 | 3 | 4 | 5 | 6 | VI-1 | Fancl |
| 10912 | 3 | 4 | 5 | 6 | VI-1 | Fank1 |
| 10913 | 3 | 4 | 5 | 6 | VI-1 | Fap |
| 10914 | 3 | 4 | 5 | 6 | VI-1 | Far1 |
| 10915 | 3 | 4 | 5 | 6 | VI-1 | Fars2 |
| 10916 | 3 | 4 | 5 | 6 | VI-1 | Farsa |
| 10917 | 3 | 4 | 5 | 6 | VI-1 | Farsb |
| 10918 | 3 | 4 | 5 | 6 | VI-1 | Fas |
| 10919 | 3 | 4 | 5 | 6 | VI-1 | Fasl |
| 10920 | 3 | 4 | 5 | 6 | VI-1 | Fastk |
| 10921 | 3 | 4 | 5 | 6 | VI-1 | Fbf1 |
| 10922 | 3 | 4 | 5 | 6 | VI-1 | Fbl |
| 10923 | 3 | 4 | 5 | 6 | VI-1 | Fbln2 |
| 10924 | 3 | 4 | 5 | 6 | VI-1 | Fbp1 |
| 10925 | 3 | 4 | 5 | 6 | VI-1 | Fbp2 |
| 10926 | 3 | 4 | 5 | 6 | VI-1 | Fbrs |
| 10927 | 3 | 4 | 5 | 6 | VI-1 | Fbxl18 |
| 10928 | 3 | 4 | 5 | 6 | VI-1 | Fbxl19 |
| 10929 | 3 | 4 | 5 | 6 | VI-1 | Fbxl2 |
| 10930 | 3 | 4 | 5 | 6 | VI-1 | Fbxl3 |
| 10931 | 3 | 4 | 5 | 6 | VI-1 | Fbxl5 |
| 10932 | 3 | 4 | 5 | 6 | VI-1 | Fbxl6 |
| 10933 | 3 | 4 | 5 | 6 | VI-1 | Fbxl8 |
| 10934 | 3 | 4 | 5 | 6 | VI-1 | Fbxo10 |
| 10935 | 3 | 4 | 5 | 6 | VI-1 | Fbxo11 |
| 10936 | 3 | 4 | 5 | 6 | VI-1 | Fbxo15 |
| 10937 | 3 | 4 | 5 | 6 | VI-1 | Fbxo16 |
| 10938 | 3 | 4 | 5 | 6 | VI-1 | Fbxo17 |
| 10939 | 3 | 4 | 5 | 6 | VI-1 | Fbxo2 |
| 10940 | 3 | 4 | 5 | 6 | VI-1 | Fbxo22 |
| 10941 | 3 | 4 | 5 | 6 | VI-1 | Fbxo27 |
| 10942 | 3 | 4 | 5 | 6 | VI-1 | Fbxo30 |

Fig. 34 - 58

| | | | | | | | | | | | | | |
|---|---|---|---|---|---|---|---|---|---|---|---|---|---|
| 10943 | 3 | 4 | 5 | 6 | | VI-1 | Fbxo32 | 11039 | 3 | 4 | 5 | 6 | | VI-1 | Foxj2 |
| 10944 | 3 | 4 | 5 | 6 | | VI-1 | Fbxo34 | 11040 | 3 | 4 | 5 | 6 | | VI-1 | Foxn3 |
| 10945 | 3 | 4 | 5 | 6 | | VI-1 | Fbxo36 | 11041 | 3 | 4 | 5 | 6 | | VI-1 | Foxo1 |
| 10946 | 3 | 4 | 5 | 6 | | VI-1 | Fbxo38 | 11042 | 3 | 4 | 5 | 6 | | VI-1 | Foxp1 |
| 10947 | 3 | 4 | 5 | 6 | | VI-1 | Fbxo4 | 11043 | 3 | 4 | 5 | 6 | | VI-1 | Foxp3 |
| 10948 | 3 | 4 | 5 | 6 | | VI-1 | Fbxo40 | 11044 | 3 | 4 | 5 | 6 | | VI-1 | Foxp4 |
| 10949 | 3 | 4 | 5 | 6 | | VI-1 | Fbxo41 | 11045 | 3 | 4 | 5 | 6 | | VI-1 | Foxr1 |
| 10950 | 3 | 4 | 5 | 6 | | VI-1 | Fbxo42 | 11046 | 3 | 4 | 5 | 6 | | VI-1 | Foxred1 |
| 10951 | 3 | 4 | 5 | 6 | | VI-1 | Fbxo6 | 11047 | 3 | 4 | 5 | 6 | | VI-1 | Foxs1 |
| 10952 | 3 | 4 | 5 | 6 | | VI-1 | Fbxo9 | 11048 | 3 | 4 | 5 | 6 | | VI-1 | Fpgs |
| 10953 | 3 | 4 | 5 | 6 | | VI-1 | Fbxw17 | 11049 | 3 | 4 | 5 | 6 | | VI-1 | Fpr1 |
| 10954 | 3 | 4 | 5 | 6 | | VI-1 | Fbxw7 | 11050 | 3 | 4 | 5 | 6 | | VI-1 | Fpr2 |
| 10955 | 3 | 4 | 5 | 6 | | VI-1 | Fbxw8 | 11051 | 3 | 4 | 5 | 6 | | VI-1 | Fra10ac1 |
| 10956 | 3 | 4 | 5 | 6 | | VI-1 | Fbxw9 | 11052 | 3 | 4 | 5 | 6 | | VI-1 | Frat1 |
| 10957 | 3 | 4 | 5 | 6 | | VI-1 | Fcer1a | 11053 | 3 | 4 | 5 | 6 | | VI-1 | Frat2 |
| 10958 | 3 | 4 | 5 | 6 | | VI-1 | Fcgr1 | 11054 | 3 | 4 | 5 | 6 | | VI-1 | Frmd4b |
| 10959 | 3 | 4 | 5 | 6 | | VI-1 | Fcgr2b | 11055 | 3 | 4 | 5 | 6 | | VI-1 | Frmpd1 |
| 10960 | 3 | 4 | 5 | 6 | | VI-1 | Fcgrt | 11056 | 3 | 4 | 5 | 6 | | VI-1 | Frs3os |
| 10961 | 3 | 4 | 5 | 6 | | VI-1 | Fcrl1 | 11057 | 3 | 4 | 5 | 6 | | VI-1 | Fry |
| 10962 | 3 | 4 | 5 | 6 | | VI-1 | Fcrl5 | 11058 | 3 | 4 | 5 | 6 | | VI-1 | Fryl |
| 10963 | 3 | 4 | 5 | 6 | | VI-1 | Fcrla | 11059 | 3 | 4 | 5 | 6 | | VI-1 | Fscn2 |
| 10964 | 3 | 4 | 5 | 6 | | VI-1 | Fcrls | 11060 | 3 | 4 | 5 | 6 | | VI-1 | Fscn3 |
| 10965 | 3 | 4 | 5 | 6 | | VI-1 | Fdx1 | 11061 | 3 | 4 | 5 | 6 | | VI-1 | Fstl3 |
| 10966 | 3 | 4 | 5 | 6 | | VI-1 | Fem1b | 11062 | 3 | 4 | 5 | 6 | | VI-1 | Fstl4 |
| 10967 | 3 | 4 | 5 | 6 | | VI-1 | Fem1c | 11063 | 3 | 4 | 5 | 6 | | VI-1 | Ftl1 |
| 10968 | 3 | 4 | 5 | 6 | | VI-1 | Fen1 | 11064 | 3 | 4 | 5 | 6 | | VI-1 | Ftsj3 |
| 10969 | 3 | 4 | 5 | 6 | | VI-1 | Fermt3 | 11065 | 3 | 4 | 5 | 6 | | VI-1 | Fubp1 |
| 10970 | 3 | 4 | 5 | 6 | | VI-1 | Fev | 11066 | 3 | 4 | 5 | 6 | | VI-1 | Fuca2 |
| 10971 | 3 | 4 | 5 | 6 | | VI-1 | Fez2 | 11067 | 3 | 4 | 5 | 6 | | VI-1 | Fundc1 |
| 10972 | 3 | 4 | 5 | 6 | | VI-1 | Fezf2 | 11068 | 3 | 4 | 5 | 6 | | VI-1 | Fundc2 |
| 10973 | 3 | 4 | 5 | 6 | | VI-1 | Fgd2 | 11069 | 3 | 4 | 5 | 6 | | VI-1 | Fut1 |
| 10974 | 3 | 4 | 5 | 6 | | VI-1 | Fgf10 | 11070 | 3 | 4 | 5 | 6 | | VI-1 | Fut11 |
| 10975 | 3 | 4 | 5 | 6 | | VI-1 | Fgf12 | 11071 | 3 | 4 | 5 | 6 | | VI-1 | Fut2 |
| 10976 | 3 | 4 | 5 | 6 | | VI-1 | Fgf13 | 11072 | 3 | 4 | 5 | 6 | | VI-1 | Fut7 |
| 10977 | 3 | 4 | 5 | 6 | | VI-1 | Fgf14 | 11073 | 3 | 4 | 5 | 6 | | VI-1 | Fuz |
| 10978 | 3 | 4 | 5 | 6 | | VI-1 | Fgf6 | 11074 | 3 | 4 | 5 | 6 | | VI-1 | Fv1 |
| 10979 | 3 | 4 | 5 | 6 | | VI-1 | Fgfr1 | 11075 | 3 | 4 | 5 | 6 | | VI-1 | Fxr2 |
| 10980 | 3 | 4 | 5 | 6 | | VI-1 | Fgfr1op | 11076 | 3 | 4 | 5 | 6 | | VI-1 | Fxyd4 |
| 10981 | 3 | 4 | 5 | 6 | | VI-1 | Fgfr3 | 11077 | 3 | 4 | 5 | 6 | | VI-1 | Fxyd6 |
| 10982 | 3 | 4 | 5 | 6 | | VI-1 | Fgfr4 | 11078 | 3 | 4 | 5 | 6 | | VI-1 | Fyttd1 |
| 10983 | 3 | 4 | 5 | 6 | | VI-1 | Fgg | 11079 | 3 | 4 | 5 | 6 | | VI-1 | Fzd6 |
| 10984 | 3 | 4 | 5 | 6 | | VI-1 | Fgl1 | 11080 | 3 | 4 | 5 | 6 | | VI-1 | Fzd9 |
| 10985 | 3 | 4 | 5 | 6 | | VI-1 | Fgl2 | 11081 | 3 | 4 | 5 | 6 | | VI-1 | Fzr1 |
| 10986 | 3 | 4 | 5 | 6 | | VI-1 | Fhl1 | 11082 | 3 | 4 | 5 | 6 | | VI-1 | G3bp1 |
| 10987 | 3 | 4 | 5 | 6 | | VI-1 | Fhl5 | 11083 | 3 | 4 | 5 | 6 | | VI-1 | G630090E17Rik |
| 10988 | 3 | 4 | 5 | 6 | | VI-1 | Fhod3 | 11084 | 3 | 4 | 5 | 6 | | VI-1 | G6pc |
| 10989 | 3 | 4 | 5 | 6 | | VI-1 | Fibin | 11085 | 3 | 4 | 5 | 6 | | VI-1 | G6pc3 |
| 10990 | 3 | 4 | 5 | 6 | | VI-1 | Fig4 | 11086 | 3 | 4 | 5 | 6 | | VI-1 | G6pdx |
| 10991 | 3 | 4 | 5 | 6 | | VI-1 | Figf | 11087 | 3 | 4 | 5 | 6 | | VI-1 | Gaa |
| 10992 | 3 | 4 | 5 | 6 | | VI-1 | Filip1 | 11088 | 3 | 4 | 5 | 6 | | VI-1 | Gab1 |
| 10993 | 3 | 4 | 5 | 6 | | VI-1 | Fitm1 | 11089 | 3 | 4 | 5 | 6 | | VI-1 | Gab2 |
| 10994 | 3 | 4 | 5 | 6 | | VI-1 | Fitm2 | 11090 | 3 | 4 | 5 | 6 | | VI-1 | Gabarap |
| 10995 | 3 | 4 | 5 | 6 | | VI-1 | Fiz1 | 11091 | 3 | 4 | 5 | 6 | | VI-1 | Gabarapl1 |
| 10996 | 3 | 4 | 5 | 6 | | VI-1 | Fjx1 | 11092 | 3 | 4 | 5 | 6 | | VI-1 | Gabbr1 |
| 10997 | 3 | 4 | 5 | 6 | | VI-1 | Fkbp10 | 11093 | 3 | 4 | 5 | 6 | | VI-1 | Gabbr2 |
| 10998 | 3 | 4 | 5 | 6 | | VI-1 | Fkbp14 | 11094 | 3 | 4 | 5 | 6 | | VI-1 | Gabra4 |
| 10999 | 3 | 4 | 5 | 6 | | VI-1 | Fkbp1a | 11095 | 3 | 4 | 5 | 6 | | VI-1 | Gabra5 |
| 11000 | 3 | 4 | 5 | 6 | | VI-1 | Fkbp1b | 11096 | 3 | 4 | 5 | 6 | | VI-1 | Gabra6 |
| 11001 | 3 | 4 | 5 | 6 | | VI-1 | Fkbp3 | 11097 | 3 | 4 | 5 | 6 | | VI-1 | Gabrb1 |
| 11002 | 3 | 4 | 5 | 6 | | VI-1 | Fkbp4 | 11098 | 3 | 4 | 5 | 6 | | VI-1 | Gabrb2 |
| 11003 | 3 | 4 | 5 | 6 | | VI-1 | Fkbp7 | 11099 | 3 | 4 | 5 | 6 | | VI-1 | Gabrd |
| 11004 | 3 | 4 | 5 | 6 | | VI-1 | Fkbp8 | 11100 | 3 | 4 | 5 | 6 | | VI-1 | Gabrg1 |
| 11005 | 3 | 4 | 5 | 6 | | VI-1 | Flad1 | 11101 | 3 | 4 | 5 | 6 | | VI-1 | Gabrg2 |
| 11006 | 3 | 4 | 5 | 6 | | VI-1 | Flcn | 11102 | 3 | 4 | 5 | 6 | | VI-1 | Gadl1 |
| 11007 | 3 | 4 | 5 | 6 | | VI-1 | Flna | 11103 | 3 | 4 | 5 | 6 | | VI-1 | Gal |
| 11008 | 3 | 4 | 5 | 6 | | VI-1 | Flot1 | 11104 | 3 | 4 | 5 | 6 | | VI-1 | Gal3st1 |
| 11009 | 3 | 4 | 5 | 6 | | VI-1 | Flot2 | 11105 | 3 | 4 | 5 | 6 | | VI-1 | Gal3st3 |
| 11010 | 3 | 4 | 5 | 6 | | VI-1 | Flrt3 | 11106 | 3 | 4 | 5 | 6 | | VI-1 | Gal3st4 |
| 11011 | 3 | 4 | 5 | 6 | | VI-1 | Flt3 | 11107 | 3 | 4 | 5 | 6 | | VI-1 | Galc |
| 11012 | 3 | 4 | 5 | 6 | | VI-1 | Flt4 | 11108 | 3 | 4 | 5 | 6 | | VI-1 | Galk1 |
| 11013 | 3 | 4 | 5 | 6 | | VI-1 | Fmnl1 | 11109 | 3 | 4 | 5 | 6 | | VI-1 | Galnt1 |
| 11014 | 3 | 4 | 5 | 6 | | VI-1 | Fmnl2 | 11110 | 3 | 4 | 5 | 6 | | VI-1 | Galnt10 |
| 11015 | 3 | 4 | 5 | 6 | | VI-1 | Fmnl3 | 11111 | 3 | 4 | 5 | 6 | | VI-1 | Galnt16 |
| 11016 | 3 | 4 | 5 | 6 | | VI-1 | Fmo1 | 11112 | 3 | 4 | 5 | 6 | | VI-1 | Galnt18 |
| 11017 | 3 | 4 | 5 | 6 | | VI-1 | Fmo4 | 11113 | 3 | 4 | 5 | 6 | | VI-1 | Galnt4 |
| 11018 | 3 | 4 | 5 | 6 | | VI-1 | Fmo5 | 11114 | 3 | 4 | 5 | 6 | | VI-1 | Galnt9 |
| 11019 | 3 | 4 | 5 | 6 | | VI-1 | Fmod | 11115 | 3 | 4 | 5 | 6 | | VI-1 | Galr2 |
| 11020 | 3 | 4 | 5 | 6 | | VI-1 | Fn1 | 11116 | 3 | 4 | 5 | 6 | | VI-1 | Gapdh |
| 11021 | 3 | 4 | 5 | 6 | | VI-1 | Fnbp1l | 11117 | 3 | 4 | 5 | 6 | | VI-1 | Gars |
| 11022 | 3 | 4 | 5 | 6 | | VI-1 | Fnbp4 | 11118 | 3 | 4 | 5 | 6 | | VI-1 | Gart |
| 11023 | 3 | 4 | 5 | 6 | | VI-1 | Fndc3a | 11119 | 3 | 4 | 5 | 6 | | VI-1 | Gas2l1 |
| 11024 | 3 | 4 | 5 | 6 | | VI-1 | Fndc4 | 11120 | 3 | 4 | 5 | 6 | | VI-1 | Gas8 |
| 11025 | 3 | 4 | 5 | 6 | | VI-1 | Fndc5 | 11121 | 3 | 4 | 5 | 6 | | VI-1 | Gata1 |
| 11026 | 3 | 4 | 5 | 6 | | VI-1 | Fndc9 | 11122 | 3 | 4 | 5 | 6 | | VI-1 | Gata2 |
| 11027 | 3 | 4 | 5 | 6 | | VI-1 | Fnip1 | 11123 | 3 | 4 | 5 | 6 | | VI-1 | Gatad1 |
| 11028 | 3 | 4 | 5 | 6 | | VI-1 | Fnip2 | 11124 | 3 | 4 | 5 | 6 | | VI-1 | Gatm |
| 11029 | 3 | 4 | 5 | 6 | | VI-1 | Fnta | 11125 | 3 | 4 | 5 | 6 | | VI-1 | Gatsl2 |
| 11030 | 3 | 4 | 5 | 6 | | VI-1 | Fntb | 11126 | 3 | 4 | 5 | 6 | | VI-1 | Gbe1 |
| 11031 | 3 | 4 | 5 | 6 | | VI-1 | Folh1 | 11127 | 3 | 4 | 5 | 6 | | VI-1 | Gbp10 |
| 11032 | 3 | 4 | 5 | 6 | | VI-1 | Fopnl | 11128 | 3 | 4 | 5 | 6 | | VI-1 | Gbp2 |
| 11033 | 3 | 4 | 5 | 6 | | VI-1 | Foxa3 | 11129 | 3 | 4 | 5 | 6 | | VI-1 | Gbp2b |
| 11034 | 3 | 4 | 5 | 6 | | VI-1 | Foxc1 | 11130 | 3 | 4 | 5 | 6 | | VI-1 | Gbp3 |
| 11035 | 3 | 4 | 5 | 6 | | VI-1 | Foxd3 | 11131 | 3 | 4 | 5 | 6 | | VI-1 | Gbp5 |
| 11036 | 3 | 4 | 5 | 6 | | VI-1 | Foxg1 | 11132 | 3 | 4 | 5 | 6 | | VI-1 | Gbp6 |
| 11037 | 3 | 4 | 5 | 6 | | VI-1 | Foxi1 | 11133 | 3 | 4 | 5 | 6 | | VI-1 | Gbp7 |
| 11038 | 3 | 4 | 5 | 6 | | VI-1 | Foxj1 | 11134 | 3 | 4 | 5 | 6 | | VI-1 | Gbp9 |

Fig. 34 - 59

| | | | | | | | |
|---|---|---|---|---|---|---|---|
| 11135 | 3 | 4 | 5 | 6 | | VI-1 | Gc |
| 11136 | 3 | 4 | 5 | 6 | | VI-1 | Gcdh |
| 11137 | 3 | 4 | 5 | 6 | | VI-1 | Gcfc2 |
| 11138 | 3 | 4 | 5 | 6 | | VI-1 | Gcgr |
| 11139 | 3 | 4 | 5 | 6 | | VI-1 | Gch1 |
| 11140 | 3 | 4 | 5 | 6 | | VI-1 | Gckr |
| 11141 | 3 | 4 | 5 | 6 | | VI-1 | Gclc |
| 11142 | 3 | 4 | 5 | 6 | | VI-1 | Gclm |
| 11143 | 3 | 4 | 5 | 6 | | VI-1 | Gcnt1 |
| 11144 | 3 | 4 | 5 | 6 | | VI-1 | Gcnt2 |
| 11145 | 3 | 4 | 5 | 6 | | VI-1 | Gcsh |
| 11146 | 3 | 4 | 5 | 6 | | VI-1 | Gda |
| 11147 | 3 | 4 | 5 | 6 | | VI-1 | Gdap1 |
| 11148 | 3 | 4 | 5 | 6 | | VI-1 | Gdap1l1 |
| 11149 | 3 | 4 | 5 | 6 | | VI-1 | Gdap2 |
| 11150 | 3 | 4 | 5 | 6 | | VI-1 | Gde1 |
| 11151 | 3 | 4 | 5 | 6 | | VI-1 | Gdf2 |
| 11152 | 3 | 4 | 5 | 6 | | VI-1 | Gdf3 |
| 11153 | 3 | 4 | 5 | 6 | | VI-1 | Gdf5 |
| 11154 | 3 | 4 | 5 | 6 | | VI-1 | Gdi2 |
| 11155 | 3 | 4 | 5 | 6 | | VI-1 | Gdpd1 |
| 11156 | 3 | 4 | 5 | 6 | | VI-1 | Gdpd2 |
| 11157 | 3 | 4 | 5 | 6 | | VI-1 | Gem |
| 11158 | 3 | 4 | 5 | 6 | | VI-1 | Gemin2 |
| 11159 | 3 | 4 | 5 | 6 | | VI-1 | Get4 |
| 11160 | 3 | 4 | 5 | 6 | | VI-1 | Gfm2 |
| 11161 | 3 | 4 | 5 | 6 | | VI-1 | Gfpt2 |
| 11162 | 3 | 4 | 5 | 6 | | VI-1 | Gfra1 |
| 11163 | 3 | 4 | 5 | 6 | | VI-1 | Gfra2 |
| 11164 | 3 | 4 | 5 | 6 | | VI-1 | Gfra3 |
| 11165 | 3 | 4 | 5 | 6 | | VI-1 | Gfra4 |
| 11166 | 3 | 4 | 5 | 6 | | VI-1 | Gfy |
| 11167 | 3 | 4 | 5 | 6 | | VI-1 | Gga1 |
| 11168 | 3 | 4 | 5 | 6 | | VI-1 | Gga2 |
| 11169 | 3 | 4 | 5 | 6 | | VI-1 | Ggact |
| 11170 | 3 | 4 | 5 | 6 | | VI-1 | Ggh |
| 11171 | 3 | 4 | 5 | 6 | | VI-1 | Ggn |
| 11172 | 3 | 4 | 5 | 6 | | VI-1 | Ggps1 |
| 11173 | 3 | 4 | 5 | 6 | | VI-1 | Ggt7 |
| 11174 | 3 | 4 | 5 | 6 | | VI-1 | Ghdc |
| 11175 | 3 | 4 | 5 | 6 | | VI-1 | Ghrh |
| 11176 | 3 | 4 | 5 | 6 | | VI-1 | Ghrl |
| 11177 | 3 | 4 | 5 | 6 | | VI-1 | Gif |
| 11178 | 3 | 4 | 5 | 6 | | VI-1 | Gimap1 |
| 11179 | 3 | 4 | 5 | 6 | | VI-1 | Gimap3 |
| 11180 | 3 | 4 | 5 | 6 | | VI-1 | Gimap9 |
| 11181 | 3 | 4 | 5 | 6 | | VI-1 | Gin1 |
| 11182 | 3 | 4 | 5 | 6 | | VI-1 | Gins1 |
| 11183 | 3 | 4 | 5 | 6 | | VI-1 | Gins3 |
| 11184 | 3 | 4 | 5 | 6 | | VI-1 | Gipc2 |
| 11185 | 3 | 4 | 5 | 6 | | VI-1 | Git1 |
| 11186 | 3 | 4 | 5 | 6 | | VI-1 | Gja1 |
| 11187 | 3 | 4 | 5 | 6 | | VI-1 | Gja4 |
| 11188 | 3 | 4 | 5 | 6 | | VI-1 | Gjb1 |
| 11189 | 3 | 4 | 5 | 6 | | VI-1 | Gjb2 |
| 11190 | 3 | 4 | 5 | 6 | | VI-1 | Gjb5 |
| 11191 | 3 | 4 | 5 | 6 | | VI-1 | Gjb6 |
| 11192 | 3 | 4 | 5 | 6 | | VI-1 | Gjc2 |
| 11193 | 3 | 4 | 5 | 6 | | VI-1 | Gjc3 |
| 11194 | 3 | 4 | 5 | 6 | | VI-1 | Gkap1 |
| 11195 | 3 | 4 | 5 | 6 | | VI-1 | Gkn3 |
| 11196 | 3 | 4 | 5 | 6 | | VI-1 | Gla |
| 11197 | 3 | 4 | 5 | 6 | | VI-1 | Glb1l1 |
| 11198 | 3 | 4 | 5 | 6 | | VI-1 | Glb1l2 |
| 11199 | 3 | 4 | 5 | 6 | | VI-1 | Glce |
| 11200 | 3 | 4 | 5 | 6 | | VI-1 | Gldn |
| 11201 | 3 | 4 | 5 | 6 | | VI-1 | Glg1 |
| 11202 | 3 | 4 | 5 | 6 | | VI-1 | Gli3 |
| 11203 | 3 | 4 | 5 | 6 | | VI-1 | Glipr2 |
| 11204 | 3 | 4 | 5 | 6 | | VI-1 | Glrx |
| 11205 | 3 | 4 | 5 | 6 | | VI-1 | Glrx2 |
| 11206 | 3 | 4 | 5 | 6 | | VI-1 | Glrx5 |
| 11207 | 3 | 4 | 5 | 6 | | VI-1 | Gls |
| 11208 | 3 | 4 | 5 | 6 | | VI-1 | Gls2 |
| 11209 | 3 | 4 | 5 | 6 | | VI-1 | Glt1d1 |
| 11210 | 3 | 4 | 5 | 6 | | VI-1 | Glt28d2 |
| 11211 | 3 | 4 | 5 | 6 | | VI-1 | Glt8d1 |
| 11212 | 3 | 4 | 5 | 6 | | VI-1 | Gltscr2 |
| 11213 | 3 | 4 | 5 | 6 | | VI-1 | Glud1 |
| 11214 | 3 | 4 | 5 | 6 | | VI-1 | Gm10024 |
| 11215 | 3 | 4 | 5 | 6 | | VI-1 | Gm10069 |
| 11216 | 3 | 4 | 5 | 6 | | VI-1 | Gm10220 |
| 11217 | 3 | 4 | 5 | 6 | | VI-1 | Gm10319 |
| 11218 | 3 | 4 | 5 | 6 | | VI-1 | Gm10377 |
| 11219 | 3 | 4 | 5 | 6 | | VI-1 | Gm10406 |
| 11220 | 3 | 4 | 5 | 6 | | VI-1 | Gm10416 |
| 11221 | 3 | 4 | 5 | 6 | | VI-1 | Gm10487 |
| 11222 | 3 | 4 | 5 | 6 | | VI-1 | Gm10560 |
| 11223 | 3 | 4 | 5 | 6 | | VI-1 | Gm10584 |
| 11224 | 3 | 4 | 5 | 6 | | VI-1 | Gm10639 |
| 11225 | 3 | 4 | 5 | 6 | | VI-1 | Gm10658 |
| 11226 | 3 | 4 | 5 | 6 | | VI-1 | Gm10782 |
| 11227 | 3 | 4 | 5 | 6 | | VI-1 | Gm10785 |
| 11228 | 3 | 4 | 5 | 6 | | VI-1 | Gm10804 |
| 11229 | 3 | 4 | 5 | 6 | | VI-1 | Gm10872 |
| 11230 | 3 | 4 | 5 | 6 | | VI-1 | Gm10941 |
| 11231 | 3 | 4 | 5 | 6 | | VI-1 | Gm11128 |
| 11232 | 3 | 4 | 5 | 6 | | VI-1 | Gm11213 |
| 11233 | 3 | 4 | 5 | 6 | | VI-1 | Gm11562 |
| 11234 | 3 | 4 | 5 | 6 | | VI-1 | Gm11567 |
| 11235 | 3 | 4 | 5 | 6 | | VI-1 | Gm11570 |
| 11236 | 3 | 4 | 5 | 6 | | VI-1 | Gm11596 |
| 11237 | 3 | 4 | 5 | 6 | | VI-1 | Gm11651 |
| 11238 | 3 | 4 | 5 | 6 | | VI-1 | Gm11744 |
| 11239 | 3 | 4 | 5 | 6 | | VI-1 | Gm11780 |
| 11240 | 3 | 4 | 5 | 6 | | VI-1 | Gm11837 |
| 11241 | 3 | 4 | 5 | 6 | | VI-1 | Gm11938 |
| 11242 | 3 | 4 | 5 | 6 | | VI-1 | Gm12060 |
| 11243 | 3 | 4 | 5 | 6 | | VI-1 | Gm12216 |
| 11244 | 3 | 4 | 5 | 6 | | VI-1 | Gm12250 |
| 11245 | 3 | 4 | 5 | 6 | | VI-1 | Gm12295 |
| 11246 | 3 | 4 | 5 | 6 | | VI-1 | Gm12338 |
| 11247 | 3 | 4 | 5 | 6 | | VI-1 | Gm12409 |
| 11248 | 3 | 4 | 5 | 6 | | VI-1 | Gm12429 |
| 11249 | 3 | 4 | 5 | 6 | | VI-1 | Gm12709 |
| 11250 | 3 | 4 | 5 | 6 | | VI-1 | Gm128 |
| 11251 | 3 | 4 | 5 | 6 | | VI-1 | Gm12942 |
| 11252 | 3 | 4 | 5 | 6 | | VI-1 | Gm13011 |
| 11253 | 3 | 4 | 5 | 6 | | VI-1 | Gm13152 |
| 11254 | 3 | 4 | 5 | 6 | | VI-1 | Gm13157 |
| 11255 | 3 | 4 | 5 | 6 | | VI-1 | Gm13178 |
| 11256 | 3 | 4 | 5 | 6 | | VI-1 | Gm13212 |
| 11257 | 3 | 4 | 5 | 6 | | VI-1 | Gm13242 |
| 11258 | 3 | 4 | 5 | 6 | | VI-1 | Gm13539 |
| 11259 | 3 | 4 | 5 | 6 | | VI-1 | Gm13580 |
| 11260 | 3 | 4 | 5 | 6 | | VI-1 | Gm14005 |
| 11261 | 3 | 4 | 5 | 6 | | VI-1 | Gm14085 |
| 11262 | 3 | 4 | 5 | 6 | | VI-1 | Gm14137 |
| 11263 | 3 | 4 | 5 | 6 | | VI-1 | Gm14207 |
| 11264 | 3 | 4 | 5 | 6 | | VI-1 | Gm14325 |
| 11265 | 3 | 4 | 5 | 6 | | VI-1 | Gm14326 |
| 11266 | 3 | 4 | 5 | 6 | | VI-1 | Gm14374 |
| 11267 | 3 | 4 | 5 | 6 | | VI-1 | Gm14440 |
| 11268 | 3 | 4 | 5 | 6 | | VI-1 | Gm14482 |
| 11269 | 3 | 4 | 5 | 6 | | VI-1 | Gm14511 |
| 11270 | 3 | 4 | 5 | 6 | | VI-1 | Gm14625 |
| 11271 | 3 | 4 | 5 | 6 | | VI-1 | Gm14685 |
| 11272 | 3 | 4 | 5 | 6 | | VI-1 | Gm14851 |
| 11273 | 3 | 4 | 5 | 6 | | VI-1 | Gm15055 |
| 11274 | 3 | 4 | 5 | 6 | | VI-1 | Gm15056 |
| 11275 | 3 | 4 | 5 | 6 | | VI-1 | Gm15093 |
| 11276 | 3 | 4 | 5 | 6 | | VI-1 | Gm15179 |
| 11277 | 3 | 4 | 5 | 6 | | VI-1 | Gm15350 |
| 11278 | 3 | 4 | 5 | 6 | | VI-1 | Gm15401 |
| 11279 | 3 | 4 | 5 | 6 | | VI-1 | Gm15408 |
| 11280 | 3 | 4 | 5 | 6 | | VI-1 | Gm15441 |
| 11281 | 3 | 4 | 5 | 6 | | VI-1 | Gm15612 |
| 11282 | 3 | 4 | 5 | 6 | | VI-1 | Gm15645 |
| 11283 | 3 | 4 | 5 | 6 | | VI-1 | Gm15706 |
| 11284 | 3 | 4 | 5 | 6 | | VI-1 | Gm15787 |
| 11285 | 3 | 4 | 5 | 6 | | VI-1 | Gm15816 |
| 11286 | 3 | 4 | 5 | 6 | | VI-1 | Gm1604b |
| 11287 | 3 | 4 | 5 | 6 | | VI-1 | Gm16404 |
| 11288 | 3 | 4 | 5 | 6 | | VI-1 | Gm16405 |
| 11289 | 3 | 4 | 5 | 6 | | VI-1 | Gm16430 |
| 11290 | 3 | 4 | 5 | 6 | | VI-1 | Gm16515 |
| 11291 | 3 | 4 | 5 | 6 | | VI-1 | Gm16548 |
| 11292 | 3 | 4 | 5 | 6 | | VI-1 | Gm16551 |
| 11293 | 3 | 4 | 5 | 6 | | VI-1 | Gm16596 |
| 11294 | 3 | 4 | 5 | 6 | | VI-1 | Gm1661 |
| 11295 | 3 | 4 | 5 | 6 | | VI-1 | Gm16845 |
| 11296 | 3 | 4 | 5 | 6 | | VI-1 | Gm16853 |
| 11297 | 3 | 4 | 5 | 6 | | VI-1 | Gm16861 |
| 11298 | 3 | 4 | 5 | 6 | | VI-1 | Gm16907 |
| 11299 | 3 | 4 | 5 | 6 | | VI-1 | Gm16973 |
| 11300 | 3 | 4 | 5 | 6 | | VI-1 | Gm17455 |
| 11301 | 3 | 4 | 5 | 6 | | VI-1 | Gm17762 |
| 11302 | 3 | 4 | 5 | 6 | | VI-1 | Gm1821 |
| 11303 | 3 | 4 | 5 | 6 | | VI-1 | Gm18853 |
| 11304 | 3 | 4 | 5 | 6 | | VI-1 | Gm19395 |
| 11305 | 3 | 4 | 5 | 6 | | VI-1 | Gm19668 |
| 11306 | 3 | 4 | 5 | 6 | | VI-1 | Gm19705 |
| 11307 | 3 | 4 | 5 | 6 | | VI-1 | Gm19710 |
| 11308 | 3 | 4 | 5 | 6 | | VI-1 | Gm20257 |
| 11309 | 3 | 4 | 5 | 6 | | VI-1 | Gm2027 |
| 11310 | 3 | 4 | 5 | 6 | | VI-1 | Gm20752 |
| 11311 | 3 | 4 | 5 | 6 | | VI-1 | Gm21949 |
| 11312 | 3 | 4 | 5 | 6 | | VI-1 | Gm2518 |
| 11313 | 3 | 4 | 5 | 6 | | VI-1 | Gm266 |
| 11314 | 3 | 4 | 5 | 6 | | VI-1 | Gm2694 |
| 11315 | 3 | 4 | 5 | 6 | | VI-1 | Gm2799 |
| 11316 | 3 | 4 | 5 | 6 | | VI-1 | Gm2933 |
| 11317 | 3 | 4 | 5 | 6 | | VI-1 | Gm2a |
| 11318 | 3 | 4 | 5 | 6 | | VI-1 | Gm3258 |
| 11319 | 3 | 4 | 5 | 6 | | VI-1 | Gm3264 |
| 11320 | 3 | 4 | 5 | 6 | | VI-1 | Gm3285 |
| 11321 | 3 | 4 | 5 | 6 | | VI-1 | Gm3336 |
| 11322 | 3 | 4 | 5 | 6 | | VI-1 | Gm3383 |
| 11323 | 3 | 4 | 5 | 6 | | VI-1 | Gm3435 |
| 11324 | 3 | 4 | 5 | 6 | | VI-1 | Gm3558 |
| 11325 | 3 | 4 | 5 | 6 | | VI-1 | Gm3776 |
| 11326 | 3 | 4 | 5 | 6 | | VI-1 | Gm4262 |

Fig. 34 - 60

| | | | | | | |
|---|---|---|---|---|---|---|
| 11327 | 3 | 4 | 5 | 6 | VI-1 | Gm4349 |
| 11328 | 3 | 4 | 5 | 6 | VI-1 | Gm4477 |
| 11329 | 3 | 4 | 5 | 6 | VI-1 | Gm4566 |
| 11330 | 3 | 4 | 5 | 6 | VI-1 | Gm4952 |
| 11331 | 3 | 4 | 5 | 6 | VI-1 | Gm4956 |
| 11332 | 3 | 4 | 5 | 6 | VI-1 | Gm4980 |
| 11333 | 3 | 4 | 5 | 6 | VI-1 | Gm4984 |
| 11334 | 3 | 4 | 5 | 6 | VI-1 | Gm5108 |
| 11335 | 3 | 4 | 5 | 6 | VI-1 | Gm5132 |
| 11336 | 3 | 4 | 5 | 6 | VI-1 | Gm5134 |
| 11337 | 3 | 4 | 5 | 6 | VI-1 | Gm5142 |
| 11338 | 3 | 4 | 5 | 6 | VI-1 | Gm5148 |
| 11339 | 3 | 4 | 5 | 6 | VI-1 | Gm53 |
| 11340 | 3 | 4 | 5 | 6 | VI-1 | Gm5409 |
| 11341 | 3 | 4 | 5 | 6 | VI-1 | Gm5424 |
| 11342 | 3 | 4 | 5 | 6 | VI-1 | Gm5431 |
| 11343 | 3 | 4 | 5 | 6 | VI-1 | Gm5460 |
| 11344 | 3 | 4 | 5 | 6 | VI-1 | Gm5485 |
| 11345 | 3 | 4 | 5 | 6 | VI-1 | Gm5547 |
| 11346 | 3 | 4 | 5 | 6 | VI-1 | Gm5607 |
| 11347 | 3 | 4 | 5 | 6 | VI-1 | Gm5635 |
| 11348 | 3 | 4 | 5 | 6 | VI-1 | Gm5643 |
| 11349 | 3 | 4 | 5 | 6 | VI-1 | Gm5779 |
| 11350 | 3 | 4 | 5 | 6 | VI-1 | Gm5796 |
| 11351 | 3 | 4 | 5 | 6 | VI-1 | Gm5797 |
| 11352 | 3 | 4 | 5 | 6 | VI-1 | Gm5800 |
| 11353 | 3 | 4 | 5 | 6 | VI-1 | Gm5801 |
| 11354 | 3 | 4 | 5 | 6 | VI-1 | Gm5860 |
| 11355 | 3 | 4 | 5 | 6 | VI-1 | Gm5893 |
| 11356 | 3 | 4 | 5 | 6 | VI-1 | Gm590 |
| 11357 | 3 | 4 | 5 | 6 | VI-1 | Gm5941 |
| 11358 | 3 | 4 | 5 | 6 | VI-1 | Gm6034 |
| 11359 | 3 | 4 | 5 | 6 | VI-1 | Gm6083 |
| 11360 | 3 | 4 | 5 | 6 | VI-1 | Gm6086 |
| 11361 | 3 | 4 | 5 | 6 | VI-1 | Gm6297 |
| 11362 | 3 | 4 | 5 | 6 | VI-1 | Gm6300 |
| 11363 | 3 | 4 | 5 | 6 | VI-1 | Gm6329 |
| 11364 | 3 | 4 | 5 | 6 | VI-1 | Gm6432 |
| 11365 | 3 | 4 | 5 | 6 | VI-1 | Gm6484 |
| 11366 | 3 | 4 | 5 | 6 | VI-1 | Gm6525 |
| 11367 | 3 | 4 | 5 | 6 | VI-1 | Gm6642 |
| 11368 | 3 | 4 | 5 | 6 | VI-1 | Gm6787 |
| 11369 | 3 | 4 | 5 | 6 | VI-1 | Gm684 |
| 11370 | 3 | 4 | 5 | 6 | VI-1 | Gm6981 |
| 11371 | 3 | 4 | 5 | 6 | VI-1 | Gm7120 |
| 11372 | 3 | 4 | 5 | 6 | VI-1 | Gm7609 |
| 11373 | 3 | 4 | 5 | 6 | VI-1 | Gm7694 |
| 11374 | 3 | 4 | 5 | 6 | VI-1 | Gm826 |
| 11375 | 3 | 4 | 5 | 6 | VI-1 | Gm8369 |
| 11376 | 3 | 4 | 5 | 6 | VI-1 | Gm8801 |
| 11377 | 3 | 4 | 5 | 6 | VI-1 | Gm8994 |
| 11378 | 3 | 4 | 5 | 6 | VI-1 | Gm906 |
| 11379 | 3 | 4 | 5 | 6 | VI-1 | Gm9112 |
| 11380 | 3 | 4 | 5 | 6 | VI-1 | Gm9199 |
| 11381 | 3 | 4 | 5 | 6 | VI-1 | Gm9758 |
| 11382 | 3 | 4 | 5 | 6 | VI-1 | Gm9833 |
| 11383 | 3 | 4 | 5 | 6 | VI-1 | Gm9855 |
| 11384 | 3 | 4 | 5 | 6 | VI-1 | Gm9866 |
| 11385 | 3 | 4 | 5 | 6 | VI-1 | Gm9895 |
| 11386 | 3 | 4 | 5 | 6 | VI-1 | Gm9899 |
| 11387 | 3 | 4 | 5 | 6 | VI-1 | Gm9992 |
| 11388 | 3 | 4 | 5 | 6 | VI-1 | Gmcl1 |
| 11389 | 3 | 4 | 5 | 6 | VI-1 | Gmnn |
| 11390 | 3 | 4 | 5 | 6 | VI-1 | Gmpr2 |
| 11391 | 3 | 4 | 5 | 6 | VI-1 | Gmps |
| 11392 | 3 | 4 | 5 | 6 | VI-1 | Gna14 |
| 11393 | 3 | 4 | 5 | 6 | VI-1 | Gna15 |
| 11394 | 3 | 4 | 5 | 6 | VI-1 | Gnal |
| 11395 | 3 | 4 | 5 | 6 | VI-1 | Gnat1 |
| 11396 | 3 | 4 | 5 | 6 | VI-1 | Gnb1l |
| 11397 | 3 | 4 | 5 | 6 | VI-1 | Gnb2 |
| 11398 | 3 | 4 | 5 | 6 | VI-1 | Gnb2l1 |
| 11399 | 3 | 4 | 5 | 6 | VI-1 | Gnb5 |
| 11400 | 3 | 4 | 5 | 6 | VI-1 | Gne |
| 11401 | 3 | 4 | 5 | 6 | VI-1 | Gng11 |
| 11402 | 3 | 4 | 5 | 6 | VI-1 | Gng12 |
| 11403 | 3 | 4 | 5 | 6 | VI-1 | Gng13 |
| 11404 | 3 | 4 | 5 | 6 | VI-1 | Gng2 |
| 11405 | 3 | 4 | 5 | 6 | VI-1 | Gng4 |
| 11406 | 3 | 4 | 5 | 6 | VI-1 | Gng8 |
| 11407 | 3 | 4 | 5 | 6 | VI-1 | Gnl2 |
| 11408 | 3 | 4 | 5 | 6 | VI-1 | Gnl3 |
| 11409 | 3 | 4 | 5 | 6 | VI-1 | Gnl3l |
| 11410 | 3 | 4 | 5 | 6 | VI-1 | Gnpda2 |
| 11411 | 3 | 4 | 5 | 6 | VI-1 | Gnptg |
| 11412 | 3 | 4 | 5 | 6 | VI-1 | Golga3 |
| 11413 | 3 | 4 | 5 | 6 | VI-1 | Golga7b |
| 11414 | 3 | 4 | 5 | 6 | VI-1 | Golgb1 |
| 11415 | 3 | 4 | 5 | 6 | VI-1 | Golt1a |
| 11416 | 3 | 4 | 5 | 6 | VI-1 | Golt1b |
| 11417 | 3 | 4 | 5 | 6 | VI-1 | Gopc |
| 11418 | 3 | 4 | 5 | 6 | VI-1 | Gorasp2 |
| 11419 | 3 | 4 | 5 | 6 | VI-1 | Gosr2 |
| 11420 | 3 | 4 | 5 | 6 | VI-1 | Got1l1 |
| 11421 | 3 | 4 | 5 | 6 | VI-1 | Gp49a |
| 11422 | 3 | 4 | 5 | 6 | VI-1 | Gp5 |
| 11423 | 3 | 4 | 5 | 6 | VI-1 | Gp9 |
| 11424 | 3 | 4 | 5 | 6 | VI-1 | Gpa33 |
| 11425 | 3 | 4 | 5 | 6 | VI-1 | Gpatch11 |
| 11426 | 3 | 4 | 5 | 6 | VI-1 | Gpatch4 |
| 11427 | 3 | 4 | 5 | 6 | VI-1 | Gpbp1l1 |
| 11428 | 3 | 4 | 5 | 6 | VI-1 | Gpc1 |
| 11429 | 3 | 4 | 5 | 6 | VI-1 | Gpc3 |
| 11430 | 3 | 4 | 5 | 6 | VI-1 | Gpc5 |
| 11431 | 3 | 4 | 5 | 6 | VI-1 | Gper1 |
| 11432 | 3 | 4 | 5 | 6 | VI-1 | Gpha2 |
| 11433 | 3 | 4 | 5 | 6 | VI-1 | Gphn |
| 11434 | 3 | 4 | 5 | 6 | VI-1 | Gpld1 |
| 11435 | 3 | 4 | 5 | 6 | VI-1 | Gpn2 |
| 11436 | 3 | 4 | 5 | 6 | VI-1 | Gpr1 |
| 11437 | 3 | 4 | 5 | 6 | VI-1 | Gpr107 |
| 11438 | 3 | 4 | 5 | 6 | VI-1 | Gpr108 |
| 11439 | 3 | 4 | 5 | 6 | VI-1 | Gpr114 |
| 11440 | 3 | 4 | 5 | 6 | VI-1 | Gpr123 |
| 11441 | 3 | 4 | 5 | 6 | VI-1 | Gpr125 |
| 11442 | 3 | 4 | 5 | 6 | VI-1 | Gpr128 |
| 11443 | 3 | 4 | 5 | 6 | VI-1 | Gpr132 |
| 11444 | 3 | 4 | 5 | 6 | VI-1 | Gpr133 |
| 11445 | 3 | 4 | 5 | 6 | VI-1 | Gpr137 |
| 11446 | 3 | 4 | 5 | 6 | VI-1 | Gpr137c |
| 11447 | 3 | 4 | 5 | 6 | VI-1 | Gpr146 |
| 11448 | 3 | 4 | 5 | 6 | VI-1 | Gpr15 |
| 11449 | 3 | 4 | 5 | 6 | VI-1 | Gpr153 |
| 11450 | 3 | 4 | 5 | 6 | VI-1 | Gpr155 |
| 11451 | 3 | 4 | 5 | 6 | VI-1 | Gpr157 |
| 11452 | 3 | 4 | 5 | 6 | VI-1 | Gpr158 |
| 11453 | 3 | 4 | 5 | 6 | VI-1 | Gpr162 |
| 11454 | 3 | 4 | 5 | 6 | VI-1 | Gpr17 |
| 11455 | 3 | 4 | 5 | 6 | VI-1 | Gpr171 |
| 11456 | 3 | 4 | 5 | 6 | VI-1 | Gpr3 |
| 11457 | 3 | 4 | 5 | 6 | VI-1 | Gpr34 |
| 11458 | 3 | 4 | 5 | 6 | VI-1 | Gpr37 |
| 11459 | 3 | 4 | 5 | 6 | VI-1 | Gpr39 |
| 11460 | 3 | 4 | 5 | 6 | VI-1 | Gpr55 |
| 11461 | 3 | 4 | 5 | 6 | VI-1 | Gpr65 |
| 11462 | 3 | 4 | 5 | 6 | VI-1 | Gpr85 |
| 11463 | 3 | 4 | 5 | 6 | VI-1 | Gpr88 |
| 11464 | 3 | 4 | 5 | 6 | VI-1 | Gprc5b |
| 11465 | 3 | 4 | 5 | 6 | VI-1 | Gprc5c |
| 11466 | 3 | 4 | 5 | 6 | VI-1 | Gprc5d |
| 11467 | 3 | 4 | 5 | 6 | VI-1 | Gprin1 |
| 11468 | 3 | 4 | 5 | 6 | VI-1 | Gps2 |
| 11469 | 3 | 4 | 5 | 6 | VI-1 | Gpsm1 |
| 11470 | 3 | 4 | 5 | 6 | VI-1 | Gpt2 |
| 11471 | 3 | 4 | 5 | 6 | VI-1 | Gpx2 |
| 11472 | 3 | 4 | 5 | 6 | VI-1 | Gpx7 |
| 11473 | 3 | 4 | 5 | 6 | VI-1 | Gpx8 |
| 11474 | 3 | 4 | 5 | 6 | VI-1 | Gramd1a |
| 11475 | 3 | 4 | 5 | 6 | VI-1 | Gramd1b |
| 11476 | 3 | 4 | 5 | 6 | VI-1 | Gramd1c |
| 11477 | 3 | 4 | 5 | 6 | VI-1 | Gramd2 |
| 11478 | 3 | 4 | 5 | 6 | VI-1 | Grap |
| 11479 | 3 | 4 | 5 | 6 | VI-1 | Grasp |
| 11480 | 3 | 4 | 5 | 6 | VI-1 | Grb10 |
| 11481 | 3 | 4 | 5 | 6 | VI-1 | Grb14 |
| 11482 | 3 | 4 | 5 | 6 | VI-1 | Grb7 |
| 11483 | 3 | 4 | 5 | 6 | VI-1 | Grhl1 |
| 11484 | 3 | 4 | 5 | 6 | VI-1 | Gria3 |
| 11485 | 3 | 4 | 5 | 6 | VI-1 | Gria4 |
| 11486 | 3 | 4 | 5 | 6 | VI-1 | Grid1 |
| 11487 | 3 | 4 | 5 | 6 | VI-1 | Grik1 |
| 11488 | 3 | 4 | 5 | 6 | VI-1 | Grik5 |
| 11489 | 3 | 4 | 5 | 6 | VI-1 | Grin1os |
| 11490 | 3 | 4 | 5 | 6 | VI-1 | Grina |
| 11491 | 3 | 4 | 5 | 6 | VI-1 | Grip2 |
| 11492 | 3 | 4 | 5 | 6 | VI-1 | Grk6 |
| 11493 | 3 | 4 | 5 | 6 | VI-1 | Grm1 |
| 11494 | 3 | 4 | 5 | 6 | VI-1 | Grm4 |
| 11495 | 3 | 4 | 5 | 6 | VI-1 | Grm5 |
| 11496 | 3 | 4 | 5 | 6 | VI-1 | Grn |
| 11497 | 3 | 4 | 5 | 6 | VI-1 | Grp |
| 11498 | 3 | 4 | 5 | 6 | VI-1 | Grpel1 |
| 11499 | 3 | 4 | 5 | 6 | VI-1 | Grsf1 |
| 11500 | 3 | 4 | 5 | 6 | VI-1 | Grtp1 |
| 11501 | 3 | 4 | 5 | 6 | VI-1 | Grwd1 |
| 11502 | 3 | 4 | 5 | 6 | VI-1 | Gsdma |
| 11503 | 3 | 4 | 5 | 6 | VI-1 | Gsdmd |
| 11504 | 3 | 4 | 5 | 6 | VI-1 | Gse1 |
| 11505 | 3 | 4 | 5 | 6 | VI-1 | Gsg1l |
| 11506 | 3 | 4 | 5 | 6 | VI-1 | Gsg2 |
| 11507 | 3 | 4 | 5 | 6 | VI-1 | Gsk3b |
| 11508 | 3 | 4 | 5 | 6 | VI-1 | Gspt2 |
| 11509 | 3 | 4 | 5 | 6 | VI-1 | Gsta1 |
| 11510 | 3 | 4 | 5 | 6 | VI-1 | Gsta4 |
| 11511 | 3 | 4 | 5 | 6 | VI-1 | Gstm1 |
| 11512 | 3 | 4 | 5 | 6 | VI-1 | Gsto1 |
| 11513 | 3 | 4 | 5 | 6 | VI-1 | Gstt4 |
| 11514 | 3 | 4 | 5 | 6 | VI-1 | Gtdc1 |
| 11515 | 3 | 4 | 5 | 6 | VI-1 | Gtf2a1 |
| 11516 | 3 | 4 | 5 | 6 | VI-1 | Gtf2a2 |
| 11517 | 3 | 4 | 5 | 6 | VI-1 | Gtf2e1 |
| 11518 | 3 | 4 | 5 | 6 | VI-1 | Gtf2e2 |

Fig. 34 - 61

| | | | | | | |
|---|---|---|---|---|---|---|
| 11519 | 3 | 4 | 5 | 6 | VI-1 | Gtf2f1 |
| 11520 | 3 | 4 | 5 | 6 | VI-1 | Gtf2h2 |
| 11521 | 3 | 4 | 5 | 6 | VI-1 | Gtf3a |
| 11522 | 3 | 4 | 5 | 6 | VI-1 | Gtsf1l |
| 11523 | 3 | 4 | 5 | 6 | VI-1 | Gucd1 |
| 11524 | 3 | 4 | 5 | 6 | VI-1 | Gucy1a3 |
| 11525 | 3 | 4 | 5 | 6 | VI-1 | Gucy2d |
| 11526 | 3 | 4 | 5 | 6 | VI-1 | Guf1 |
| 11527 | 3 | 4 | 5 | 6 | VI-1 | Guk1 |
| 11528 | 3 | 4 | 5 | 6 | VI-1 | Gulp1 |
| 11529 | 3 | 4 | 5 | 6 | VI-1 | Gvin1 |
| 11530 | 3 | 4 | 5 | 6 | VI-1 | Gyg |
| 11531 | 3 | 4 | 5 | 6 | VI-1 | Gykl1 |
| 11532 | 3 | 4 | 5 | 6 | VI-1 | Gyltl1b |
| 11533 | 3 | 4 | 5 | 6 | VI-1 | Gys1 |
| 11534 | 3 | 4 | 5 | 6 | VI-1 | Gzma |
| 11535 | 3 | 4 | 5 | 6 | VI-1 | Gzmb |
| 11536 | 3 | 4 | 5 | 6 | VI-1 | Gzmc |
| 11537 | 3 | 4 | 5 | 6 | VI-1 | H19 |
| 11538 | 3 | 4 | 5 | 6 | VI-1 | H1fnt |
| 11539 | 3 | 4 | 5 | 6 | VI-1 | H2-DMb1 |
| 11540 | 3 | 4 | 5 | 6 | VI-1 | H2-M3 |
| 11541 | 3 | 4 | 5 | 6 | VI-1 | H2-M9 |
| 11542 | 3 | 4 | 5 | 6 | VI-1 | H2-T23 |
| 11543 | 3 | 4 | 5 | 6 | VI-1 | H2-T9 |
| 11544 | 3 | 4 | 5 | 6 | VI-1 | H2afx |
| 11545 | 3 | 4 | 5 | 6 | VI-1 | H2afy |
| 11546 | 3 | 4 | 5 | 6 | VI-1 | H2afy2 |
| 11547 | 3 | 4 | 5 | 6 | VI-1 | H2afz |
| 11548 | 3 | 4 | 5 | 6 | VI-1 | H3f3a |
| 11549 | 3 | 4 | 5 | 6 | VI-1 | H3f3b |
| 11550 | 3 | 4 | 5 | 6 | VI-1 | H6pd |
| 11551 | 3 | 4 | 5 | 6 | VI-1 | Haao |
| 11552 | 3 | 4 | 5 | 6 | VI-1 | Habp4 |
| 11553 | 3 | 4 | 5 | 6 | VI-1 | Hacl1 |
| 11554 | 3 | 4 | 5 | 6 | VI-1 | Hagh |
| 11555 | 3 | 4 | 5 | 6 | VI-1 | Hap1 |
| 11556 | 3 | 4 | 5 | 6 | VI-1 | Harbi1 |
| 11557 | 3 | 4 | 5 | 6 | VI-1 | Hars2 |
| 11558 | 3 | 4 | 5 | 6 | VI-1 | Hat1 |
| 11559 | 3 | 4 | 5 | 6 | VI-1 | Haus1 |
| 11560 | 3 | 4 | 5 | 6 | VI-1 | Haus3 |
| 11561 | 3 | 4 | 5 | 6 | VI-1 | Haus4 |
| 11562 | 3 | 4 | 5 | 6 | VI-1 | Hbegf |
| 11563 | 3 | 4 | 5 | 6 | VI-1 | Hbp1 |
| 11564 | 3 | 4 | 5 | 6 | VI-1 | Hbq1a |
| 11565 | 3 | 4 | 5 | 6 | VI-1 | Hbq1b |
| 11566 | 3 | 4 | 5 | 6 | VI-1 | Hc |
| 11567 | 3 | 4 | 5 | 6 | VI-1 | Hcrt |
| 11568 | 3 | 4 | 5 | 6 | VI-1 | Hdac11 |
| 11569 | 3 | 4 | 5 | 6 | VI-1 | Hdac3 |
| 11570 | 3 | 4 | 5 | 6 | VI-1 | Hdac4 |
| 11571 | 3 | 4 | 5 | 6 | VI-1 | Hdac5 |
| 11572 | 3 | 4 | 5 | 6 | VI-1 | Hdac6 |
| 11573 | 3 | 4 | 5 | 6 | VI-1 | Hdc |
| 11574 | 3 | 4 | 5 | 6 | VI-1 | Hddc3 |
| 11575 | 3 | 4 | 5 | 6 | VI-1 | Hdgf |
| 11576 | 3 | 4 | 5 | 6 | VI-1 | Hdgfl1 |
| 11577 | 3 | 4 | 5 | 6 | VI-1 | Hdgfrp3 |
| 11578 | 3 | 4 | 5 | 6 | VI-1 | Hdlbp |
| 11579 | 3 | 4 | 5 | 6 | VI-1 | Heatr5b |
| 11580 | 3 | 4 | 5 | 6 | VI-1 | Hebp1 |
| 11581 | 3 | 4 | 5 | 6 | VI-1 | Hectd1 |
| 11582 | 3 | 4 | 5 | 6 | VI-1 | Hecw2 |
| 11583 | 3 | 4 | 5 | 6 | VI-1 | Helz |
| 11584 | 3 | 4 | 5 | 6 | VI-1 | Helz2 |
| 11585 | 3 | 4 | 5 | 6 | VI-1 | Hemk1 |
| 11586 | 3 | 4 | 5 | 6 | VI-1 | Hepacam |
| 11587 | 3 | 4 | 5 | 6 | VI-1 | Hepacam2 |
| 11588 | 3 | 4 | 5 | 6 | VI-1 | Herc4 |
| 11589 | 3 | 4 | 5 | 6 | VI-1 | Herc6 |
| 11590 | 3 | 4 | 5 | 6 | VI-1 | Herpud1 |
| 11591 | 3 | 4 | 5 | 6 | VI-1 | Herpud2 |
| 11592 | 3 | 4 | 5 | 6 | VI-1 | Hes1 |
| 11593 | 3 | 4 | 5 | 6 | VI-1 | Hes6 |
| 11594 | 3 | 4 | 5 | 6 | VI-1 | Hes7 |
| 11595 | 3 | 4 | 5 | 6 | VI-1 | Hexb |
| 11596 | 3 | 4 | 5 | 6 | VI-1 | Hexdc |
| 11597 | 3 | 4 | 5 | 6 | VI-1 | Hey2 |
| 11598 | 3 | 4 | 5 | 6 | VI-1 | Hfe2 |
| 11599 | 3 | 4 | 5 | 6 | VI-1 | Hgsnat |
| 11600 | 3 | 4 | 5 | 6 | VI-1 | Hhat |
| 11601 | 3 | 4 | 5 | 6 | VI-1 | Hhipl1 |
| 11602 | 3 | 4 | 5 | 6 | VI-1 | Hhipl2 |
| 11603 | 3 | 4 | 5 | 6 | VI-1 | Hibch |
| 11604 | 3 | 4 | 5 | 6 | VI-1 | Hif3a |
| 11605 | 3 | 4 | 5 | 6 | VI-1 | Higd1a |
| 11606 | 3 | 4 | 5 | 6 | VI-1 | Hinfp |
| 11607 | 3 | 4 | 5 | 6 | VI-1 | Hint3 |
| 11608 | 3 | 4 | 5 | 6 | VI-1 | Hip1 |
| 11609 | 3 | 4 | 5 | 6 | VI-1 | Hipk3 |
| 11610 | 3 | 4 | 5 | 6 | VI-1 | Hipk4 |
| 11611 | 3 | 4 | 5 | 6 | VI-1 | Hist1h1a |
| 11612 | 3 | 4 | 5 | 6 | VI-1 | Hist1h1t |
| 11613 | 3 | 4 | 5 | 6 | VI-1 | Hist1h2ac |
| 11614 | 3 | 4 | 5 | 6 | VI-1 | Hist1h2ad |
| 11615 | 3 | 4 | 5 | 6 | VI-1 | Hist1h2ae |
| 11616 | 3 | 4 | 5 | 6 | VI-1 | Hist1h2an |
| 11617 | 3 | 4 | 5 | 6 | VI-1 | Hist1h2ao |
| 11618 | 3 | 4 | 5 | 6 | VI-1 | Hist1h2bb |
| 11619 | 3 | 4 | 5 | 6 | VI-1 | Hist1h2bf |
| 11620 | 3 | 4 | 5 | 6 | VI-1 | Hist1h2bh |
| 11621 | 3 | 4 | 5 | 6 | VI-1 | Hist1h2bl |
| 11622 | 3 | 4 | 5 | 6 | VI-1 | Hist1h2bm |
| 11623 | 3 | 4 | 5 | 6 | VI-1 | Hist1h2bn |
| 11624 | 3 | 4 | 5 | 6 | VI-1 | Hist1h2bp |
| 11625 | 3 | 4 | 5 | 6 | VI-1 | Hist1h2bq |
| 11626 | 3 | 4 | 5 | 6 | VI-1 | Hist1h3a |
| 11627 | 3 | 4 | 5 | 6 | VI-1 | Hist1h3d |
| 11628 | 3 | 4 | 5 | 6 | VI-1 | Hist1h3f |
| 11629 | 3 | 4 | 5 | 6 | VI-1 | Hist1h4m |
| 11630 | 3 | 4 | 5 | 6 | VI-1 | Hist2h3b |
| 11631 | 3 | 4 | 5 | 6 | VI-1 | Hist3h2ba |
| 11632 | 3 | 4 | 5 | 6 | VI-1 | Hist4h4 |
| 11633 | 3 | 4 | 5 | 6 | VI-1 | Hivep2 |
| 11634 | 3 | 4 | 5 | 6 | VI-1 | Hk1os |
| 11635 | 3 | 4 | 5 | 6 | VI-1 | Hk2 |
| 11636 | 3 | 4 | 5 | 6 | VI-1 | Hk3 |
| 11637 | 3 | 4 | 5 | 6 | VI-1 | Hltf |
| 11638 | 3 | 4 | 5 | 6 | VI-1 | Hmbox1 |
| 11639 | 3 | 4 | 5 | 6 | VI-1 | Hmbs |
| 11640 | 3 | 4 | 5 | 6 | VI-1 | Hmces |
| 11641 | 3 | 4 | 5 | 6 | VI-1 | Hmga1 |
| 11642 | 3 | 4 | 5 | 6 | VI-1 | Hmga2-ps1 |
| 11643 | 3 | 4 | 5 | 6 | VI-1 | Hmgb1 |
| 11644 | 3 | 4 | 5 | 6 | VI-1 | Hmgb2 |
| 11645 | 3 | 4 | 5 | 6 | VI-1 | Hmgb3 |
| 11646 | 3 | 4 | 5 | 6 | VI-1 | Hmgn2 |
| 11647 | 3 | 4 | 5 | 6 | VI-1 | Hmgn3 |
| 11648 | 3 | 4 | 5 | 6 | VI-1 | Hmgxb4 |
| 11649 | 3 | 4 | 5 | 6 | VI-1 | Hmha1 |
| 11650 | 3 | 4 | 5 | 6 | VI-1 | Hmox2 |
| 11651 | 3 | 4 | 5 | 6 | VI-1 | Hn1 |
| 11652 | 3 | 4 | 5 | 6 | VI-1 | Hnf1a |
| 11653 | 3 | 4 | 5 | 6 | VI-1 | Hnf4a |
| 11654 | 3 | 4 | 5 | 6 | VI-1 | Hnrnpa2b1 |
| 11655 | 3 | 4 | 5 | 6 | VI-1 | Hnrnpf |
| 11656 | 3 | 4 | 5 | 6 | VI-1 | Hnrnph3 |
| 11657 | 3 | 4 | 5 | 6 | VI-1 | Hoga1 |
| 11658 | 3 | 4 | 5 | 6 | VI-1 | Homez |
| 11659 | 3 | 4 | 5 | 6 | VI-1 | Hook2 |
| 11660 | 3 | 4 | 5 | 6 | VI-1 | Hook3 |
| 11661 | 3 | 4 | 5 | 6 | VI-1 | Hopx |
| 11662 | 3 | 4 | 5 | 6 | VI-1 | Hoxa2 |
| 11663 | 3 | 4 | 5 | 6 | VI-1 | Hoxa3 |
| 11664 | 3 | 4 | 5 | 6 | VI-1 | Hoxa5 |
| 11665 | 3 | 4 | 5 | 6 | VI-1 | Hoxb3 |
| 11666 | 3 | 4 | 5 | 6 | VI-1 | Hoxb5 |
| 11667 | 3 | 4 | 5 | 6 | VI-1 | Hoxc6 |
| 11668 | 3 | 4 | 5 | 6 | VI-1 | Hoxc9 |
| 11669 | 3 | 4 | 5 | 6 | VI-1 | Hoxd8 |
| 11670 | 3 | 4 | 5 | 6 | VI-1 | Hoxd9 |
| 11671 | 3 | 4 | 5 | 6 | VI-1 | Hpcal1 |
| 11672 | 3 | 4 | 5 | 6 | VI-1 | Hpdl |
| 11673 | 3 | 4 | 5 | 6 | VI-1 | Hpn |
| 11674 | 3 | 4 | 5 | 6 | VI-1 | Hps4 |
| 11675 | 3 | 4 | 5 | 6 | VI-1 | Hpx |
| 11676 | 3 | 4 | 5 | 6 | VI-1 | Hrg |
| 11677 | 3 | 4 | 5 | 6 | VI-1 | Hrh1 |
| 11678 | 3 | 4 | 5 | 6 | VI-1 | Hrh3 |
| 11679 | 3 | 4 | 5 | 6 | VI-1 | Hs3st3b1 |
| 11680 | 3 | 4 | 5 | 6 | VI-1 | Hs3st4 |
| 11681 | 3 | 4 | 5 | 6 | VI-1 | Hs3st6 |
| 11682 | 3 | 4 | 5 | 6 | VI-1 | Hs6st1 |
| 11683 | 3 | 4 | 5 | 6 | VI-1 | Hsbp1l1 |
| 11684 | 3 | 4 | 5 | 6 | VI-1 | Hsd11b1 |
| 11685 | 3 | 4 | 5 | 6 | VI-1 | Hsd11b2 |
| 11686 | 3 | 4 | 5 | 6 | VI-1 | Hsd17b1 |
| 11687 | 3 | 4 | 5 | 6 | VI-1 | Hsd17b12 |
| 11688 | 3 | 4 | 5 | 6 | VI-1 | Hsd17b13 |
| 11689 | 3 | 4 | 5 | 6 | VI-1 | Hsd17b14 |
| 11690 | 3 | 4 | 5 | 6 | VI-1 | Hsf1 |
| 11691 | 3 | 4 | 5 | 6 | VI-1 | Hsf2 |
| 11692 | 3 | 4 | 5 | 6 | VI-1 | Hsf4 |
| 11693 | 3 | 4 | 5 | 6 | VI-1 | Hsh2d |
| 11694 | 3 | 4 | 5 | 6 | VI-1 | Hsp90aa1 |
| 11695 | 3 | 4 | 5 | 6 | VI-1 | Hsp90ab1 |
| 11696 | 3 | 4 | 5 | 6 | VI-1 | Hsp90b1 |
| 11697 | 3 | 4 | 5 | 6 | VI-1 | Hspa12b |
| 11698 | 3 | 4 | 5 | 6 | VI-1 | Hspa13 |
| 11699 | 3 | 4 | 5 | 6 | VI-1 | Hspa1l |
| 11700 | 3 | 4 | 5 | 6 | VI-1 | Hspa4 |
| 11701 | 3 | 4 | 5 | 6 | VI-1 | Hspa4l |
| 11702 | 3 | 4 | 5 | 6 | VI-1 | Hspa9 |
| 11703 | 3 | 4 | 5 | 6 | VI-1 | Hspb7 |
| 11704 | 3 | 4 | 5 | 6 | VI-1 | Hspb8 |
| 11705 | 3 | 4 | 5 | 6 | VI-1 | Hspd1 |
| 11706 | 3 | 4 | 5 | 6 | VI-1 | Hspe1 |
| 11707 | 3 | 4 | 5 | 6 | VI-1 | Hspg2 |
| 11708 | 3 | 4 | 5 | 6 | VI-1 | Htr1b |
| 11709 | 3 | 4 | 5 | 6 | VI-1 | Htr2c |
| 11710 | 3 | 4 | 5 | 6 | VI-1 | Htra1 |

Fig. 34 - 62

| | | | | | | |
|---|---|---|---|---|---|---|
| 11711 | 3 | 4 | 5 | 6 | VI-1 | Htra2 |
| 11712 | 3 | 4 | 5 | 6 | VI-1 | Htra4 |
| 11713 | 3 | 4 | 5 | 6 | VI-1 | Hvcn1 |
| 11714 | 3 | 4 | 5 | 6 | VI-1 | Hypk |
| 11715 | 3 | 4 | 5 | 6 | VI-1 | Iah1 |
| 11716 | 3 | 4 | 5 | 6 | VI-1 | Iapp |
| 11717 | 3 | 4 | 5 | 6 | VI-1 | Iars |
| 11718 | 3 | 4 | 5 | 6 | VI-1 | Iars2 |
| 11719 | 3 | 4 | 5 | 6 | VI-1 | Iba57 |
| 11720 | 3 | 4 | 5 | 6 | VI-1 | Ibtk |
| 11721 | 3 | 4 | 5 | 6 | VI-1 | Ical1 |
| 11722 | 3 | 4 | 5 | 6 | VI-1 | Icam1 |
| 11723 | 3 | 4 | 5 | 6 | VI-1 | Icam5 |
| 11724 | 3 | 4 | 5 | 6 | VI-1 | Ick |
| 11725 | 3 | 4 | 5 | 6 | VI-1 | Id1 |
| 11726 | 3 | 4 | 5 | 6 | VI-1 | Id4 |
| 11727 | 3 | 4 | 5 | 6 | VI-1 | Idh3b |
| 11728 | 3 | 4 | 5 | 6 | VI-1 | Idh3g |
| 11729 | 3 | 4 | 5 | 6 | VI-1 | Ido1 |
| 11730 | 3 | 4 | 5 | 6 | VI-1 | Ido2 |
| 11731 | 3 | 4 | 5 | 6 | VI-1 | Ids |
| 11732 | 3 | 4 | 5 | 6 | VI-1 | Iffo1 |
| 11733 | 3 | 4 | 5 | 6 | VI-1 | Iffo2 |
| 11734 | 3 | 4 | 5 | 6 | VI-1 | If27l2b |
| 11735 | 3 | 4 | 5 | 6 | VI-1 | Ifi30 |
| 11736 | 3 | 4 | 5 | 6 | VI-1 | Ifih1 |
| 11737 | 3 | 4 | 5 | 6 | VI-1 | Ifit2 |
| 11738 | 3 | 4 | 5 | 6 | VI-1 | Ifitm1 |
| 11739 | 3 | 4 | 5 | 6 | VI-1 | Ifitm5 |
| 11740 | 3 | 4 | 5 | 6 | VI-1 | Ifitm7 |
| 11741 | 3 | 4 | 5 | 6 | VI-1 | Ifnab |
| 11742 | 3 | 4 | 5 | 6 | VI-1 | Ifnar2 |
| 11743 | 3 | 4 | 5 | 6 | VI-1 | Ift122 |
| 11744 | 3 | 4 | 5 | 6 | VI-1 | Ift172 |
| 11745 | 3 | 4 | 5 | 6 | VI-1 | Ift52 |
| 11746 | 3 | 4 | 5 | 6 | VI-1 | Ift74 |
| 11747 | 3 | 4 | 5 | 6 | VI-1 | Ift81 |
| 11748 | 3 | 4 | 5 | 6 | VI-1 | Ift88 |
| 11749 | 3 | 4 | 5 | 6 | VI-1 | Igf1r |
| 11750 | 3 | 4 | 5 | 6 | VI-1 | Igf2bp2 |
| 11751 | 3 | 4 | 5 | 6 | VI-1 | Igfbp3 |
| 11752 | 3 | 4 | 5 | 6 | VI-1 | Igfbp4 |
| 11753 | 3 | 4 | 5 | 6 | VI-1 | Igfbp6 |
| 11754 | 3 | 4 | 5 | 6 | VI-1 | Igip |
| 11755 | 3 | 4 | 5 | 6 | VI-1 | Igll1 |
| 11756 | 3 | 4 | 5 | 6 | VI-1 | Iglon5 |
| 11757 | 3 | 4 | 5 | 6 | VI-1 | Igsf11 |
| 11758 | 3 | 4 | 5 | 6 | VI-1 | Igsf5 |
| 11759 | 3 | 4 | 5 | 6 | VI-1 | Igsf6 |
| 11760 | 3 | 4 | 5 | 6 | VI-1 | Ihh |
| 11761 | 3 | 4 | 5 | 6 | VI-1 | Iigp1 |
| 11762 | 3 | 4 | 5 | 6 | VI-1 | Ikbip |
| 11763 | 3 | 4 | 5 | 6 | VI-1 | Ikbkap |
| 11764 | 3 | 4 | 5 | 6 | VI-1 | Ikbkb |
| 11765 | 3 | 4 | 5 | 6 | VI-1 | Ikbkg |
| 11766 | 3 | 4 | 5 | 6 | VI-1 | Il10 |
| 11767 | 3 | 4 | 5 | 6 | VI-1 | Il11 |
| 11768 | 3 | 4 | 5 | 6 | VI-1 | Il12rb2 |
| 11769 | 3 | 4 | 5 | 6 | VI-1 | Il13ra2 |
| 11770 | 3 | 4 | 5 | 6 | VI-1 | Il15 |
| 11771 | 3 | 4 | 5 | 6 | VI-1 | Il17d |
| 11772 | 3 | 4 | 5 | 6 | VI-1 | Il17ra |
| 11773 | 3 | 4 | 5 | 6 | VI-1 | Il17rb |
| 11774 | 3 | 4 | 5 | 6 | VI-1 | Il17re |
| 11775 | 3 | 4 | 5 | 6 | VI-1 | Il18bp |
| 11776 | 3 | 4 | 5 | 6 | VI-1 | Il18r1 |
| 11777 | 3 | 4 | 5 | 6 | VI-1 | Il18rap |
| 11778 | 3 | 4 | 5 | 6 | VI-1 | Il1f10 |
| 11779 | 3 | 4 | 5 | 6 | VI-1 | Il1f6 |
| 11780 | 3 | 4 | 5 | 6 | VI-1 | Il22ra1 |
| 11781 | 3 | 4 | 5 | 6 | VI-1 | Il34 |
| 11782 | 3 | 4 | 5 | 6 | VI-1 | Il4i1 |
| 11783 | 3 | 4 | 5 | 6 | VI-1 | Il4ra |
| 11784 | 3 | 4 | 5 | 6 | VI-1 | Il7r |
| 11785 | 3 | 4 | 5 | 6 | VI-1 | Ildr1 |
| 11786 | 3 | 4 | 5 | 6 | VI-1 | Ildr2 |
| 11787 | 3 | 4 | 5 | 6 | VI-1 | Ilk |
| 11788 | 3 | 4 | 5 | 6 | VI-1 | Ilvbl |
| 11789 | 3 | 4 | 5 | 6 | VI-1 | Imp3 |
| 11790 | 3 | 4 | 5 | 6 | VI-1 | Impdh2 |
| 11791 | 3 | 4 | 5 | 6 | VI-1 | Inf2 |
| 11792 | 3 | 4 | 5 | 6 | VI-1 | Ing1 |
| 11793 | 3 | 4 | 5 | 6 | VI-1 | Ing2 |
| 11794 | 3 | 4 | 5 | 6 | VI-1 | Ing3 |
| 11795 | 3 | 4 | 5 | 6 | VI-1 | Inha |
| 11796 | 3 | 4 | 5 | 6 | VI-1 | Inhbb |
| 11797 | 3 | 4 | 5 | 6 | VI-1 | Ino80 |
| 11798 | 3 | 4 | 5 | 6 | VI-1 | Ino80e |
| 11799 | 3 | 4 | 5 | 6 | VI-1 | Inpp4a |
| 11800 | 3 | 4 | 5 | 6 | VI-1 | Inpp5d |
| 11801 | 3 | 4 | 5 | 6 | VI-1 | Inpp5e |
| 11802 | 3 | 4 | 5 | 6 | VI-1 | Inpp5f |
| 11803 | 3 | 4 | 5 | 6 | VI-1 | Inpp5j |
| 11804 | 3 | 4 | 5 | 6 | VI-1 | Insc |
| 11805 | 3 | 4 | 5 | 6 | VI-1 | Insig1 |
| 11806 | 3 | 4 | 5 | 6 | VI-1 | Insl5 |
| 11807 | 3 | 4 | 5 | 6 | VI-1 | Insl6 |
| 11808 | 3 | 4 | 5 | 6 | VI-1 | Insr |
| 11809 | 3 | 4 | 5 | 6 | VI-1 | Ints10 |
| 11810 | 3 | 4 | 5 | 6 | VI-1 | Ints8 |
| 11811 | 3 | 4 | 5 | 6 | VI-1 | Ints9 |
| 11812 | 3 | 4 | 5 | 6 | VI-1 | Invs |
| 11813 | 3 | 4 | 5 | 6 | VI-1 | Ip6k1 |
| 11814 | 3 | 4 | 5 | 6 | VI-1 | Ip6k2 |
| 11815 | 3 | 4 | 5 | 6 | VI-1 | Ip6k3 |
| 11816 | 3 | 4 | 5 | 6 | VI-1 | Ipmk |
| 11817 | 3 | 4 | 5 | 6 | VI-1 | Ipo13 |
| 11818 | 3 | 4 | 5 | 6 | VI-1 | Ippk |
| 11819 | 3 | 4 | 5 | 6 | VI-1 | Iqcc |
| 11820 | 3 | 4 | 5 | 6 | VI-1 | Iqcd |
| 11821 | 3 | 4 | 5 | 6 | VI-1 | Iqcf1 |
| 11822 | 3 | 4 | 5 | 6 | VI-1 | Iqcf3 |
| 11823 | 3 | 4 | 5 | 6 | VI-1 | Iqcf4 |
| 11824 | 3 | 4 | 5 | 6 | VI-1 | Iqcf5 |
| 11825 | 3 | 4 | 5 | 6 | VI-1 | Iqcf6 |
| 11826 | 3 | 4 | 5 | 6 | VI-1 | Iqcg |
| 11827 | 3 | 4 | 5 | 6 | VI-1 | Iqgap2 |
| 11828 | 3 | 4 | 5 | 6 | VI-1 | Iqsec2 |
| 11829 | 3 | 4 | 5 | 6 | VI-1 | Iqsec3 |
| 11830 | 3 | 4 | 5 | 6 | VI-1 | Irak1bp1 |
| 11831 | 3 | 4 | 5 | 6 | VI-1 | Irak2 |
| 11832 | 3 | 4 | 5 | 6 | VI-1 | Irf2bp2 |
| 11833 | 3 | 4 | 5 | 6 | VI-1 | Irf3 |
| 11834 | 3 | 4 | 5 | 6 | VI-1 | Irf5 |
| 11835 | 3 | 4 | 5 | 6 | VI-1 | Irf6 |
| 11836 | 3 | 4 | 5 | 6 | VI-1 | Irf9 |
| 11837 | 3 | 4 | 5 | 6 | VI-1 | Irgm1 |
| 11838 | 3 | 4 | 5 | 6 | VI-1 | Irgm2 |
| 11839 | 3 | 4 | 5 | 6 | VI-1 | Irgq |
| 11840 | 3 | 4 | 5 | 6 | VI-1 | Irs1 |
| 11841 | 3 | 4 | 5 | 6 | VI-1 | Irs4 |
| 11842 | 3 | 4 | 5 | 6 | VI-1 | Irx3 |
| 11843 | 3 | 4 | 5 | 6 | VI-1 | Isca1 |
| 11844 | 3 | 4 | 5 | 6 | VI-1 | Isca2 |
| 11845 | 3 | 4 | 5 | 6 | VI-1 | Iscu |
| 11846 | 3 | 4 | 5 | 6 | VI-1 | Isg20 |
| 11847 | 3 | 4 | 5 | 6 | VI-1 | Isl1 |
| 11848 | 3 | 4 | 5 | 6 | VI-1 | Islr2 |
| 11849 | 3 | 4 | 5 | 6 | VI-1 | Isy1 |
| 11850 | 3 | 4 | 5 | 6 | VI-1 | Itch |
| 11851 | 3 | 4 | 5 | 6 | VI-1 | Itfg2 |
| 11852 | 3 | 4 | 5 | 6 | VI-1 | Itfg3 |
| 11853 | 3 | 4 | 5 | 6 | VI-1 | Itga2 |
| 11854 | 3 | 4 | 5 | 6 | VI-1 | Itga3 |
| 11855 | 3 | 4 | 5 | 6 | VI-1 | Itga4 |
| 11856 | 3 | 4 | 5 | 6 | VI-1 | Itga5 |
| 11857 | 3 | 4 | 5 | 6 | VI-1 | Itga6 |
| 11858 | 3 | 4 | 5 | 6 | VI-1 | Itga7 |
| 11859 | 3 | 4 | 5 | 6 | VI-1 | Itga8 |
| 11860 | 3 | 4 | 5 | 6 | VI-1 | Itgam |
| 11861 | 3 | 4 | 5 | 6 | VI-1 | Itgav |
| 11862 | 3 | 4 | 5 | 6 | VI-1 | Itgb1bp1 |
| 11863 | 3 | 4 | 5 | 6 | VI-1 | Itgb2 |
| 11864 | 3 | 4 | 5 | 6 | VI-1 | Itgb3 |
| 11865 | 3 | 4 | 5 | 6 | VI-1 | Itgb3bp |
| 11866 | 3 | 4 | 5 | 6 | VI-1 | Itgb7 |
| 11867 | 3 | 4 | 5 | 6 | VI-1 | Itgbl1 |
| 11868 | 3 | 4 | 5 | 6 | VI-1 | Itih1 |
| 11869 | 3 | 4 | 5 | 6 | VI-1 | Itpa |
| 11870 | 3 | 4 | 5 | 6 | VI-1 | Itpk1 |
| 11871 | 3 | 4 | 5 | 6 | VI-1 | Itpkc |
| 11872 | 3 | 4 | 5 | 6 | VI-1 | Itpr1 |
| 11873 | 3 | 4 | 5 | 6 | VI-1 | Itpr3 |
| 11874 | 3 | 4 | 5 | 6 | VI-1 | Itprip |
| 11875 | 3 | 4 | 5 | 6 | VI-1 | Itpripl2 |
| 11876 | 3 | 4 | 5 | 6 | VI-1 | Itsn2 |
| 11877 | 3 | 4 | 5 | 6 | VI-1 | Ivns1abp |
| 11878 | 3 | 4 | 5 | 6 | VI-1 | Izumo2 |
| 11879 | 3 | 4 | 5 | 6 | VI-1 | Jak1 |
| 11880 | 3 | 4 | 5 | 6 | VI-1 | Jak2 |
| 11881 | 3 | 4 | 5 | 6 | VI-1 | Jam3 |
| 11882 | 3 | 4 | 5 | 6 | VI-1 | Jazf1 |
| 11883 | 3 | 4 | 5 | 6 | VI-1 | Jdp2 |
| 11884 | 3 | 4 | 5 | 6 | VI-1 | Jkamp |
| 11885 | 3 | 4 | 5 | 6 | VI-1 | Jmjd1c |
| 11886 | 3 | 4 | 5 | 6 | VI-1 | Jmjd4 |
| 11887 | 3 | 4 | 5 | 6 | VI-1 | Jmjd6 |
| 11888 | 3 | 4 | 5 | 6 | VI-1 | Jmjd7 |
| 11889 | 3 | 4 | 5 | 6 | VI-1 | Jmjd7-pla2g4b |
| 11890 | 3 | 4 | 5 | 6 | VI-1 | Josd1 |
| 11891 | 3 | 4 | 5 | 6 | VI-1 | Jph1 |
| 11892 | 3 | 4 | 5 | 6 | VI-1 | Jph2 |
| 11893 | 3 | 4 | 5 | 6 | VI-1 | Jrkl |
| 11894 | 3 | 4 | 5 | 6 | VI-1 | Jtb |
| 11895 | 3 | 4 | 5 | 6 | VI-1 | Jun |
| 11896 | 3 | 4 | 5 | 6 | VI-1 | Jund |
| 11897 | 3 | 4 | 5 | 6 | VI-1 | Jup |
| 11898 | 3 | 4 | 5 | 6 | VI-1 | Kalrn |
| 11899 | 3 | 4 | 5 | 6 | VI-1 | Kank3 |
| 11900 | 3 | 4 | 5 | 6 | VI-1 | Kansl1l |
| 11901 | 3 | 4 | 5 | 6 | VI-1 | Kars |
| 11902 | 3 | 4 | 5 | 6 | VI-1 | Kat2b |

Fig. 34 - 63

| | | | | | | | |
|---|---|---|---|---|---|---|---|
| 11903 | 3 | 4 | 5 | 6 | | VI-1 | Kat5 |
| 11904 | 3 | 4 | 5 | 6 | | VI-1 | Kat8 |
| 11905 | 3 | 4 | 5 | 6 | | VI-1 | Katna1 |
| 11906 | 3 | 4 | 5 | 6 | | VI-1 | Katnal1 |
| 11907 | 3 | 4 | 5 | 6 | | VI-1 | Katnb1 |
| 11908 | 3 | 4 | 5 | 6 | | VI-1 | Katnbl1 |
| 11909 | 3 | 4 | 5 | 6 | | VI-1 | Kbtbd11 |
| 11910 | 3 | 4 | 5 | 6 | | VI-1 | Kbtbd12 |
| 11911 | 3 | 4 | 5 | 6 | | VI-1 | Kbtbd7 |
| 11912 | 3 | 4 | 5 | 6 | | VI-1 | Kcna1 |
| 11913 | 3 | 4 | 5 | 6 | | VI-1 | Kcna2 |
| 11914 | 3 | 4 | 5 | 6 | | VI-1 | Kcna5 |
| 11915 | 3 | 4 | 5 | 6 | | VI-1 | Kcna6 |
| 11916 | 3 | 4 | 5 | 6 | | VI-1 | Kcnab1 |
| 11917 | 3 | 4 | 5 | 6 | | VI-1 | Kcnb1 |
| 11918 | 3 | 4 | 5 | 6 | | VI-1 | Kcnc2 |
| 11919 | 3 | 4 | 5 | 6 | | VI-1 | Kcnc4 |
| 11920 | 3 | 4 | 5 | 6 | | VI-1 | Kcnd2 |
| 11921 | 3 | 4 | 5 | 6 | | VI-1 | Kcnd3 |
| 11922 | 3 | 4 | 5 | 6 | | VI-1 | Kcne3 |
| 11923 | 3 | 4 | 5 | 6 | | VI-1 | Kcne4 |
| 11924 | 3 | 4 | 5 | 6 | | VI-1 | Kcnf1 |
| 11925 | 3 | 4 | 5 | 6 | | VI-1 | Kcnh3 |
| 11926 | 3 | 4 | 5 | 6 | | VI-1 | Kcnip2 |
| 11927 | 3 | 4 | 5 | 6 | | VI-1 | Kcnip3 |
| 11928 | 3 | 4 | 5 | 6 | | VI-1 | Kcnip4 |
| 11929 | 3 | 4 | 5 | 6 | | VI-1 | Kcnj10 |
| 11930 | 3 | 4 | 5 | 6 | | VI-1 | Kcnj12 |
| 11931 | 3 | 4 | 5 | 6 | | VI-1 | Kcnj13 |
| 11932 | 3 | 4 | 5 | 6 | | VI-1 | Kcnj15 |
| 11933 | 3 | 4 | 5 | 6 | | VI-1 | Kcnj2 |
| 11934 | 3 | 4 | 5 | 6 | | VI-1 | Kcnj3 |
| 11935 | 3 | 4 | 5 | 6 | | VI-1 | Kcnj8 |
| 11936 | 3 | 4 | 5 | 6 | | VI-1 | Kcnj9 |
| 11937 | 3 | 4 | 5 | 6 | | VI-1 | Kcnk12 |
| 11938 | 3 | 4 | 5 | 6 | | VI-1 | Kcnk13 |
| 11939 | 3 | 4 | 5 | 6 | | VI-1 | Kcnk5 |
| 11940 | 3 | 4 | 5 | 6 | | VI-1 | Kcnk6 |
| 11941 | 3 | 4 | 5 | 6 | | VI-1 | Kcnmb1 |
| 11942 | 3 | 4 | 5 | 6 | | VI-1 | Kcnmb4 |
| 11943 | 3 | 4 | 5 | 6 | | VI-1 | Kcnmb4os1 |
| 11944 | 3 | 4 | 5 | 6 | | VI-1 | Kcnn2 |
| 11945 | 3 | 4 | 5 | 6 | | VI-1 | Kcnn4 |
| 11946 | 3 | 4 | 5 | 6 | | VI-1 | Kcnq1 |
| 11947 | 3 | 4 | 5 | 6 | | VI-1 | Kcnrg |
| 11948 | 3 | 4 | 5 | 6 | | VI-1 | Kcns2 |
| 11949 | 3 | 4 | 5 | 6 | | VI-1 | Kcns3 |
| 11950 | 3 | 4 | 5 | 6 | | VI-1 | Kcnt1 |
| 11951 | 3 | 4 | 5 | 6 | | VI-1 | Kctd12 |
| 11952 | 3 | 4 | 5 | 6 | | VI-1 | Kctd15 |
| 11953 | 3 | 4 | 5 | 6 | | VI-1 | Kctd17 |
| 11954 | 3 | 4 | 5 | 6 | | VI-1 | Kctd18 |
| 11955 | 3 | 4 | 5 | 6 | | VI-1 | Kctd2 |
| 11956 | 3 | 4 | 5 | 6 | | VI-1 | Kctd20 |
| 11957 | 3 | 4 | 5 | 6 | | VI-1 | Kctd6 |
| 11958 | 3 | 4 | 5 | 6 | | VI-1 | Kctd7 |
| 11959 | 3 | 4 | 5 | 6 | | VI-1 | Kctd9 |
| 11960 | 3 | 4 | 5 | 6 | | VI-1 | Kdm1a |
| 11961 | 3 | 4 | 5 | 6 | | VI-1 | Kdm1b |
| 11962 | 3 | 4 | 5 | 6 | | VI-1 | Kdm2b |
| 11963 | 3 | 4 | 5 | 6 | | VI-1 | Kdm3b |
| 11964 | 3 | 4 | 5 | 6 | | VI-1 | Kdm4c |
| 11965 | 3 | 4 | 5 | 6 | | VI-1 | Kdm5a |
| 11966 | 3 | 4 | 5 | 6 | | VI-1 | Kdm6a |
| 11967 | 3 | 4 | 5 | 6 | | VI-1 | Khdc1a |
| 11968 | 3 | 4 | 5 | 6 | | VI-1 | Khdc3 |
| 11969 | 3 | 4 | 5 | 6 | | VI-1 | Khdrbs1 |
| 11970 | 3 | 4 | 5 | 6 | | VI-1 | Khdrbs2 |
| 11971 | 3 | 4 | 5 | 6 | | VI-1 | Kif13b |
| 11972 | 3 | 4 | 5 | 6 | | VI-1 | Kif17 |
| 11973 | 3 | 4 | 5 | 6 | | VI-1 | Kif19a |
| 11974 | 3 | 4 | 5 | 6 | | VI-1 | Kif20a |
| 11975 | 3 | 4 | 5 | 6 | | VI-1 | Kif27 |
| 11976 | 3 | 4 | 5 | 6 | | VI-1 | Kif2a |
| 11977 | 3 | 4 | 5 | 6 | | VI-1 | Kif2b |
| 11978 | 3 | 4 | 5 | 6 | | VI-1 | Kif2c |
| 11979 | 3 | 4 | 5 | 6 | | VI-1 | Kif3a |
| 11980 | 3 | 4 | 5 | 6 | | VI-1 | Kif5b |
| 11981 | 3 | 4 | 5 | 6 | | VI-1 | Kifap3 |
| 11982 | 3 | 4 | 5 | 6 | | VI-1 | Kifc2 |
| 11983 | 3 | 4 | 5 | 6 | | VI-1 | Kifc3 |
| 11984 | 3 | 4 | 5 | 6 | | VI-1 | Kin |
| 11985 | 3 | 4 | 5 | 6 | | VI-1 | Kirrel2 |
| 11986 | 3 | 4 | 5 | 6 | | VI-1 | Kirrel3 |
| 11987 | 3 | 4 | 5 | 6 | | VI-1 | Kitl |
| 11988 | 3 | 4 | 5 | 6 | | VI-1 | Kl |
| 11989 | 3 | 4 | 5 | 6 | | VI-1 | Klc2 |
| 11990 | 3 | 4 | 5 | 6 | | VI-1 | Klc3 |
| 11991 | 3 | 4 | 5 | 6 | | VI-1 | Klc4 |
| 11992 | 3 | 4 | 5 | 6 | | VI-1 | Klf10 |
| 11993 | 3 | 4 | 5 | 6 | | VI-1 | Klf15 |
| 11994 | 3 | 4 | 5 | 6 | | VI-1 | Klf16 |
| 11995 | 3 | 4 | 5 | 6 | | VI-1 | Klf2 |
| 11996 | 3 | 4 | 5 | 6 | | VI-1 | Klf5 |
| 11997 | 3 | 4 | 5 | 6 | | VI-1 | Klf6 |
| 11998 | 3 | 4 | 5 | 6 | | VI-1 | Klhdc1 |
| 11999 | 3 | 4 | 5 | 6 | | VI-1 | Klhdc10 |
| 12000 | 3 | 4 | 5 | 6 | | VI-1 | Klhdc2 |
| 12001 | 3 | 4 | 5 | 6 | | VI-1 | Klhdc8a |
| 12002 | 3 | 4 | 5 | 6 | | VI-1 | Klhdc8b |
| 12003 | 3 | 4 | 5 | 6 | | VI-1 | Klhdc9 |
| 12004 | 3 | 4 | 5 | 6 | | VI-1 | Klhl10 |
| 12005 | 3 | 4 | 5 | 6 | | VI-1 | Klhl2 |
| 12006 | 3 | 4 | 5 | 6 | | VI-1 | Klhl21 |
| 12007 | 3 | 4 | 5 | 6 | | VI-1 | Klhl25 |
| 12008 | 3 | 4 | 5 | 6 | | VI-1 | Klhl26 |
| 12009 | 3 | 4 | 5 | 6 | | VI-1 | Klhl34 |
| 12010 | 3 | 4 | 5 | 6 | | VI-1 | Klhl35 |
| 12011 | 3 | 4 | 5 | 6 | | VI-1 | Klhl38 |
| 12012 | 3 | 4 | 5 | 6 | | VI-1 | Klhl40 |
| 12013 | 3 | 4 | 5 | 6 | | VI-1 | Klhl41 |
| 12014 | 3 | 4 | 5 | 6 | | VI-1 | Klhl5 |
| 12015 | 3 | 4 | 5 | 6 | | VI-1 | Klhl6 |
| 12016 | 3 | 4 | 5 | 6 | | VI-1 | Klhl7 |
| 12017 | 3 | 4 | 5 | 6 | | VI-1 | Klk1 |
| 12018 | 3 | 4 | 5 | 6 | | VI-1 | Klk11 |
| 12019 | 3 | 4 | 5 | 6 | | VI-1 | Klk14 |
| 12020 | 3 | 4 | 5 | 6 | | VI-1 | Klk1b1 |
| 12021 | 3 | 4 | 5 | 6 | | VI-1 | Klk1b11 |
| 12022 | 3 | 4 | 5 | 6 | | VI-1 | Klk1b27 |
| 12023 | 3 | 4 | 5 | 6 | | VI-1 | Klk1b4 |
| 12024 | 3 | 4 | 5 | 6 | | VI-1 | Klk1b5 |
| 12025 | 3 | 4 | 5 | 6 | | VI-1 | Klk1b8 |
| 12026 | 3 | 4 | 5 | 6 | | VI-1 | Klk1b9 |
| 12027 | 3 | 4 | 5 | 6 | | VI-1 | Klk5 |
| 12028 | 3 | 4 | 5 | 6 | | VI-1 | Klk9 |
| 12029 | 3 | 4 | 5 | 6 | | VI-1 | Klra2 |
| 12030 | 3 | 4 | 5 | 6 | | VI-1 | Klra7 |
| 12031 | 3 | 4 | 5 | 6 | | VI-1 | Klrb1f |
| 12032 | 3 | 4 | 5 | 6 | | VI-1 | Klrc1 |
| 12033 | 3 | 4 | 5 | 6 | | VI-1 | Klrg2 |
| 12034 | 3 | 4 | 5 | 6 | | VI-1 | Klrk1 |
| 12035 | 3 | 4 | 5 | 6 | | VI-1 | Kmo |
| 12036 | 3 | 4 | 5 | 6 | | VI-1 | Kmt2a |
| 12037 | 3 | 4 | 5 | 6 | | VI-1 | Kmt2c |
| 12038 | 3 | 4 | 5 | 6 | | VI-1 | Kndc1 |
| 12039 | 3 | 4 | 5 | 6 | | VI-1 | Kng1 |
| 12040 | 3 | 4 | 5 | 6 | | VI-1 | Knstrn |
| 12041 | 3 | 4 | 5 | 6 | | VI-1 | Kpna3 |
| 12042 | 3 | 4 | 5 | 6 | | VI-1 | Kpna6 |
| 12043 | 3 | 4 | 5 | 6 | | VI-1 | Krba1 |
| 12044 | 3 | 4 | 5 | 6 | | VI-1 | Krt12 |
| 12045 | 3 | 4 | 5 | 6 | | VI-1 | Krt15 |
| 12046 | 3 | 4 | 5 | 6 | | VI-1 | Krt17 |
| 12047 | 3 | 4 | 5 | 6 | | VI-1 | Krt18 |
| 12048 | 3 | 4 | 5 | 6 | | VI-1 | Krt20 |
| 12049 | 3 | 4 | 5 | 6 | | VI-1 | Krt222 |
| 12050 | 3 | 4 | 5 | 6 | | VI-1 | Krt23 |
| 12051 | 3 | 4 | 5 | 6 | | VI-1 | Krt27 |
| 12052 | 3 | 4 | 5 | 6 | | VI-1 | Krt28 |
| 12053 | 3 | 4 | 5 | 6 | | VI-1 | Krt31 |
| 12054 | 3 | 4 | 5 | 6 | | VI-1 | Krt33a |
| 12055 | 3 | 4 | 5 | 6 | | VI-1 | Krt34 |
| 12056 | 3 | 4 | 5 | 6 | | VI-1 | Krt35 |
| 12057 | 3 | 4 | 5 | 6 | | VI-1 | Krt42 |
| 12058 | 3 | 4 | 5 | 6 | | VI-1 | Krt6a |
| 12059 | 3 | 4 | 5 | 6 | | VI-1 | Krt7 |
| 12060 | 3 | 4 | 5 | 6 | | VI-1 | Krt77 |
| 12061 | 3 | 4 | 5 | 6 | | VI-1 | Krt8 |
| 12062 | 3 | 4 | 5 | 6 | | VI-1 | Krt81 |
| 12063 | 3 | 4 | 5 | 6 | | VI-1 | Krt82 |
| 12064 | 3 | 4 | 5 | 6 | | VI-1 | Krt85 |
| 12065 | 3 | 4 | 5 | 6 | | VI-1 | Krt86 |
| 12066 | 3 | 4 | 5 | 6 | | VI-1 | Krtap1-3 |
| 12067 | 3 | 4 | 5 | 6 | | VI-1 | Krtap1-4 |
| 12068 | 3 | 4 | 5 | 6 | | VI-1 | Krtap10-4 |
| 12069 | 3 | 4 | 5 | 6 | | VI-1 | Krtap11-1 |
| 12070 | 3 | 4 | 5 | 6 | | VI-1 | Krtap12-1 |
| 12071 | 3 | 4 | 5 | 6 | | VI-1 | Krtap13-1 |
| 12072 | 3 | 4 | 5 | 6 | | VI-1 | Krtap14 |
| 12073 | 3 | 4 | 5 | 6 | | VI-1 | Krtap15 |
| 12074 | 3 | 4 | 5 | 6 | | VI-1 | Krtap17-1 |
| 12075 | 3 | 4 | 5 | 6 | | VI-1 | Krtap19-1 |
| 12076 | 3 | 4 | 5 | 6 | | VI-1 | Krtap19-4 |
| 12077 | 3 | 4 | 5 | 6 | | VI-1 | Krtap2-4 |
| 12078 | 3 | 4 | 5 | 6 | | VI-1 | Krtap21-1 |
| 12079 | 3 | 4 | 5 | 6 | | VI-1 | Krtap24-1 |
| 12080 | 3 | 4 | 5 | 6 | | VI-1 | Krtap26-1 |
| 12081 | 3 | 4 | 5 | 6 | | VI-1 | Krtap3-1 |
| 12082 | 3 | 4 | 5 | 6 | | VI-1 | Krtap3-3 |
| 12083 | 3 | 4 | 5 | 6 | | VI-1 | Krtap5-3 |
| 12084 | 3 | 4 | 5 | 6 | | VI-1 | Krtap5-4 |
| 12085 | 3 | 4 | 5 | 6 | | VI-1 | Krtap5-5 |
| 12086 | 3 | 4 | 5 | 6 | | VI-1 | Krtap6-2 |
| 12087 | 3 | 4 | 5 | 6 | | VI-1 | Krtap7-1 |
| 12088 | 3 | 4 | 5 | 6 | | VI-1 | Krtap8-1 |
| 12089 | 3 | 4 | 5 | 6 | | VI-1 | Krtap9-3 |
| 12090 | 3 | 4 | 5 | 6 | | VI-1 | Krtcap2 |
| 12091 | 3 | 4 | 5 | 6 | | VI-1 | Ktl12 |
| 12092 | 3 | 4 | 5 | 6 | | VI-1 | Ktn1 |
| 12093 | 3 | 4 | 5 | 6 | | VI-1 | Kxd1 |
| 12094 | 3 | 4 | 5 | 6 | | VI-1 | L3mbtl2 |

Fig. 34 - 64

| | | | | | | |
|---|---|---|---|---|---|---|
| 12095 | 3 | 4 | 5 | 6 | VI-1 | L3mbtl3 |
| 12096 | 3 | 4 | 5 | 6 | VI-1 | LOC100503676 |
| 12097 | 3 | 4 | 5 | 6 | VI-1 | LOC102633315 |
| 12098 | 3 | 4 | 5 | 6 | VI-1 | LOC102636514 |
| 12099 | 3 | 4 | 5 | 6 | VI-1 | LOC666331 |
| 12100 | 3 | 4 | 5 | 6 | VI-1 | Lace1 |
| 12101 | 3 | 4 | 5 | 6 | VI-1 | Lad1 |
| 12102 | 3 | 4 | 5 | 6 | VI-1 | Lag3 |
| 12103 | 3 | 4 | 5 | 6 | VI-1 | Lalba |
| 12104 | 3 | 4 | 5 | 6 | VI-1 | Lamb1 |
| 12105 | 3 | 4 | 5 | 6 | VI-1 | Lamb2 |
| 12106 | 3 | 4 | 5 | 6 | VI-1 | Lamb3 |
| 12107 | 3 | 4 | 5 | 6 | VI-1 | Lamc3 |
| 12108 | 3 | 4 | 5 | 6 | VI-1 | Lamp3 |
| 12109 | 3 | 4 | 5 | 6 | VI-1 | Lamtor5 |
| 12110 | 3 | 4 | 5 | 6 | VI-1 | Lancl1 |
| 12111 | 3 | 4 | 5 | 6 | VI-1 | Lancl2 |
| 12112 | 3 | 4 | 5 | 6 | VI-1 | Lao1 |
| 12113 | 3 | 4 | 5 | 6 | VI-1 | Lap3 |
| 12114 | 3 | 4 | 5 | 6 | VI-1 | Laptm4b |
| 12115 | 3 | 4 | 5 | 6 | VI-1 | Laptm5 |
| 12116 | 3 | 4 | 5 | 6 | VI-1 | Large |
| 12117 | 3 | 4 | 5 | 6 | VI-1 | Larp4 |
| 12118 | 3 | 4 | 5 | 6 | VI-1 | Larp7 |
| 12119 | 3 | 4 | 5 | 6 | VI-1 | Las1l |
| 12120 | 3 | 4 | 5 | 6 | VI-1 | Lax1 |
| 12121 | 3 | 4 | 5 | 6 | VI-1 | Lbx1 |
| 12122 | 3 | 4 | 5 | 6 | VI-1 | Lbx2 |
| 12123 | 3 | 4 | 5 | 6 | VI-1 | Lca5l |
| 12124 | 3 | 4 | 5 | 6 | VI-1 | Lcat |
| 12125 | 3 | 4 | 5 | 6 | VI-1 | Lce1a1 |
| 12126 | 3 | 4 | 5 | 6 | VI-1 | Lce1a2 |
| 12127 | 3 | 4 | 5 | 6 | VI-1 | Lce1b |
| 12128 | 3 | 4 | 5 | 6 | VI-1 | Lce1c |
| 12129 | 3 | 4 | 5 | 6 | VI-1 | Lce1d |
| 12130 | 3 | 4 | 5 | 6 | VI-1 | Lce1e |
| 12131 | 3 | 4 | 5 | 6 | VI-1 | Lce1h |
| 12132 | 3 | 4 | 5 | 6 | VI-1 | Lce1k |
| 12133 | 3 | 4 | 5 | 6 | VI-1 | Lce1l |
| 12134 | 3 | 4 | 5 | 6 | VI-1 | Lce3e |
| 12135 | 3 | 4 | 5 | 6 | VI-1 | Lcorl |
| 12136 | 3 | 4 | 5 | 6 | VI-1 | Lctl |
| 12137 | 3 | 4 | 5 | 6 | VI-1 | Ldb1 |
| 12138 | 3 | 4 | 5 | 6 | VI-1 | Ldb2 |
| 12139 | 3 | 4 | 5 | 6 | VI-1 | Ldha |
| 12140 | 3 | 4 | 5 | 6 | VI-1 | Ldhd |
| 12141 | 3 | 4 | 5 | 6 | VI-1 | Ldlrad4 |
| 12142 | 3 | 4 | 5 | 6 | VI-1 | Ldlrap1 |
| 12143 | 3 | 4 | 5 | 6 | VI-1 | Lect1 |
| 12144 | 3 | 4 | 5 | 6 | VI-1 | Lef1 |
| 12145 | 3 | 4 | 5 | 6 | VI-1 | Lekr1 |
| 12146 | 3 | 4 | 5 | 6 | VI-1 | Lelp1 |
| 12147 | 3 | 4 | 5 | 6 | VI-1 | Lemd1 |
| 12148 | 3 | 4 | 5 | 6 | VI-1 | Lemd2 |
| 12149 | 3 | 4 | 5 | 6 | VI-1 | Lenep |
| 12150 | 3 | 4 | 5 | 6 | VI-1 | Leng9 |
| 12151 | 3 | 4 | 5 | 6 | VI-1 | Lepre1 |
| 12152 | 3 | 4 | 5 | 6 | VI-1 | Leprel1 |
| 12153 | 3 | 4 | 5 | 6 | VI-1 | Leprel4 |
| 12154 | 3 | 4 | 5 | 6 | VI-1 | Leprot |
| 12155 | 3 | 4 | 5 | 6 | VI-1 | Leprotl1 |
| 12156 | 3 | 4 | 5 | 6 | VI-1 | Letm1 |
| 12157 | 3 | 4 | 5 | 6 | VI-1 | Letm2 |
| 12158 | 3 | 4 | 5 | 6 | VI-1 | Lfng |
| 12159 | 3 | 4 | 5 | 6 | VI-1 | Lgals3 |
| 12160 | 3 | 4 | 5 | 6 | VI-1 | Lgals3bp |
| 12161 | 3 | 4 | 5 | 6 | VI-1 | Lgals8 |
| 12162 | 3 | 4 | 5 | 6 | VI-1 | Lgals9 |
| 12163 | 3 | 4 | 5 | 6 | VI-1 | Lgalsl |
| 12164 | 3 | 4 | 5 | 6 | VI-1 | Lgi1 |
| 12165 | 3 | 4 | 5 | 6 | VI-1 | Lgi2 |
| 12166 | 3 | 4 | 5 | 6 | VI-1 | Lgmn |
| 12167 | 3 | 4 | 5 | 6 | VI-1 | Lgr4 |
| 12168 | 3 | 4 | 5 | 6 | VI-1 | Lhfp |
| 12169 | 3 | 4 | 5 | 6 | VI-1 | Lhfpl2 |
| 12170 | 3 | 4 | 5 | 6 | VI-1 | Lhfpl3 |
| 12171 | 3 | 4 | 5 | 6 | VI-1 | Lhfpl4 |
| 12172 | 3 | 4 | 5 | 6 | VI-1 | Lhfpl5 |
| 12173 | 3 | 4 | 5 | 6 | VI-1 | Lhpp |
| 12174 | 3 | 4 | 5 | 6 | VI-1 | Lhx1 |
| 12175 | 3 | 4 | 5 | 6 | VI-1 | Lhx2 |
| 12176 | 3 | 4 | 5 | 6 | VI-1 | Lias |
| 12177 | 3 | 4 | 5 | 6 | VI-1 | Lilrb4 |
| 12178 | 3 | 4 | 5 | 6 | VI-1 | Limd2 |
| 12179 | 3 | 4 | 5 | 6 | VI-1 | Lime1 |
| 12180 | 3 | 4 | 5 | 6 | VI-1 | Limk1 |
| 12181 | 3 | 4 | 5 | 6 | VI-1 | Limk2 |
| 12182 | 3 | 4 | 5 | 6 | VI-1 | Lims2 |
| 12183 | 3 | 4 | 5 | 6 | VI-1 | Lin54 |
| 12184 | 3 | 4 | 5 | 6 | VI-1 | Lin7a |
| 12185 | 3 | 4 | 5 | 6 | VI-1 | Lin7b |
| 12186 | 3 | 4 | 5 | 6 | VI-1 | Lin7c |
| 12187 | 3 | 4 | 5 | 6 | VI-1 | Lingo3 |
| 12188 | 3 | 4 | 5 | 6 | VI-1 | Lipc |
| 12189 | 3 | 4 | 5 | 6 | VI-1 | Liph |
| 12190 | 3 | 4 | 5 | 6 | VI-1 | Lipn |
| 12191 | 3 | 4 | 5 | 6 | VI-1 | Litaf |
| 12192 | 3 | 4 | 5 | 6 | VI-1 | Lix1 |
| 12193 | 3 | 4 | 5 | 6 | VI-1 | Lkaaear1 |
| 12194 | 3 | 4 | 5 | 6 | VI-1 | Lman2l |
| 12195 | 3 | 4 | 5 | 6 | VI-1 | Lmf2 |
| 12196 | 3 | 4 | 5 | 6 | VI-1 | Lmna |
| 12197 | 3 | 4 | 5 | 6 | VI-1 | Lmnb2 |
| 12198 | 3 | 4 | 5 | 6 | VI-1 | Lmo1 |
| 12199 | 3 | 4 | 5 | 6 | VI-1 | Lmo3 |
| 12200 | 3 | 4 | 5 | 6 | VI-1 | Lmo4 |
| 12201 | 3 | 4 | 5 | 6 | VI-1 | Lmo7 |
| 12202 | 3 | 4 | 5 | 6 | VI-1 | Lmod1 |
| 12203 | 3 | 4 | 5 | 6 | VI-1 | Lmod3 |
| 12204 | 3 | 4 | 5 | 6 | VI-1 | Lnp |
| 12205 | 3 | 4 | 5 | 6 | VI-1 | Loh12cr1 |
| 12206 | 3 | 4 | 5 | 6 | VI-1 | Lonp1 |
| 12207 | 3 | 4 | 5 | 6 | VI-1 | Lonp2 |
| 12208 | 3 | 4 | 5 | 6 | VI-1 | Lonrf2 |
| 12209 | 3 | 4 | 5 | 6 | VI-1 | Lonrf3 |
| 12210 | 3 | 4 | 5 | 6 | VI-1 | Lox14 |
| 12211 | 3 | 4 | 5 | 6 | VI-1 | Lpar1 |
| 12212 | 3 | 4 | 5 | 6 | VI-1 | Lpar6 |
| 12213 | 3 | 4 | 5 | 6 | VI-1 | Lpcat4 |
| 12214 | 3 | 4 | 5 | 6 | VI-1 | Lpin1 |
| 12215 | 3 | 4 | 5 | 6 | VI-1 | Lpin3 |
| 12216 | 3 | 4 | 5 | 6 | VI-1 | Lpl |
| 12217 | 3 | 4 | 5 | 6 | VI-1 | Lpo |
| 12218 | 3 | 4 | 5 | 6 | VI-1 | Lpxn |
| 12219 | 3 | 4 | 5 | 6 | VI-1 | Lrba |
| 12220 | 3 | 4 | 5 | 6 | VI-1 | Lrfn1 |
| 12221 | 3 | 4 | 5 | 6 | VI-1 | Lrfn3 |
| 12222 | 3 | 4 | 5 | 6 | VI-1 | Lrfn4 |
| 12223 | 3 | 4 | 5 | 6 | VI-1 | Lrg1 |
| 12224 | 3 | 4 | 5 | 6 | VI-1 | Lrmp |
| 12225 | 3 | 4 | 5 | 6 | VI-1 | Lrp1 |
| 12226 | 3 | 4 | 5 | 6 | VI-1 | Lrp2 |
| 12227 | 3 | 4 | 5 | 6 | VI-1 | Lrp3 |
| 12228 | 3 | 4 | 5 | 6 | VI-1 | Lrrc10b |
| 12229 | 3 | 4 | 5 | 6 | VI-1 | Lrrc14 |
| 12230 | 3 | 4 | 5 | 6 | VI-1 | Lrrc18 |
| 12231 | 3 | 4 | 5 | 6 | VI-1 | Lrrc2 |
| 12232 | 3 | 4 | 5 | 6 | VI-1 | Lrrc23 |
| 12233 | 3 | 4 | 5 | 6 | VI-1 | Lrrc24 |
| 12234 | 3 | 4 | 5 | 6 | VI-1 | Lrrc25 |
| 12235 | 3 | 4 | 5 | 6 | VI-1 | Lrrc28 |
| 12236 | 3 | 4 | 5 | 6 | VI-1 | Lrrc29 |
| 12237 | 3 | 4 | 5 | 6 | VI-1 | Lrrc36 |
| 12238 | 3 | 4 | 5 | 6 | VI-1 | Lrrc4 |
| 12239 | 3 | 4 | 5 | 6 | VI-1 | Lrrc43 |
| 12240 | 3 | 4 | 5 | 6 | VI-1 | Lrrc45 |
| 12241 | 3 | 4 | 5 | 6 | VI-1 | Lrrc47 |
| 12242 | 3 | 4 | 5 | 6 | VI-1 | Lrrc49 |
| 12243 | 3 | 4 | 5 | 6 | VI-1 | Lrrc4c |
| 12244 | 3 | 4 | 5 | 6 | VI-1 | Lrrc56 |
| 12245 | 3 | 4 | 5 | 6 | VI-1 | Lrrc59 |
| 12246 | 3 | 4 | 5 | 6 | VI-1 | Lrrc61 |
| 12247 | 3 | 4 | 5 | 6 | VI-1 | Lrrc71 |
| 12248 | 3 | 4 | 5 | 6 | VI-1 | Lrrc8a |
| 12249 | 3 | 4 | 5 | 6 | VI-1 | Lrrfip2 |
| 12250 | 3 | 4 | 5 | 6 | VI-1 | Lrrn1 |
| 12251 | 3 | 4 | 5 | 6 | VI-1 | Lrrn4 |
| 12252 | 3 | 4 | 5 | 6 | VI-1 | Lrrn4cl |
| 12253 | 3 | 4 | 5 | 6 | VI-1 | Lrrtm1 |
| 12254 | 3 | 4 | 5 | 6 | VI-1 | Lrrtm3 |
| 12255 | 3 | 4 | 5 | 6 | VI-1 | Lrrtm4 |
| 12256 | 3 | 4 | 5 | 6 | VI-1 | Lrtm1 |
| 12257 | 3 | 4 | 5 | 6 | VI-1 | Lrtm2 |
| 12258 | 3 | 4 | 5 | 6 | VI-1 | Lsg1 |
| 12259 | 3 | 4 | 5 | 6 | VI-1 | Lsm1 |
| 12260 | 3 | 4 | 5 | 6 | VI-1 | Lsm10 |
| 12261 | 3 | 4 | 5 | 6 | VI-1 | Lsm11 |
| 12262 | 3 | 4 | 5 | 6 | VI-1 | Lsm14b |
| 12263 | 3 | 4 | 5 | 6 | VI-1 | Lsm3 |
| 12264 | 3 | 4 | 5 | 6 | VI-1 | Lsm6 |
| 12265 | 3 | 4 | 5 | 6 | VI-1 | Lsr |
| 12266 | 3 | 4 | 5 | 6 | VI-1 | Lta |
| 12267 | 3 | 4 | 5 | 6 | VI-1 | Ltb |
| 12268 | 3 | 4 | 5 | 6 | VI-1 | Ltb4r1 |
| 12269 | 3 | 4 | 5 | 6 | VI-1 | Ltbp1 |
| 12270 | 3 | 4 | 5 | 6 | VI-1 | Ltbp3 |
| 12271 | 3 | 4 | 5 | 6 | VI-1 | Ltbr |
| 12272 | 3 | 4 | 5 | 6 | VI-1 | Ltv1 |
| 12273 | 3 | 4 | 5 | 6 | VI-1 | Luc7l |
| 12274 | 3 | 4 | 5 | 6 | VI-1 | Lurap1 |
| 12275 | 3 | 4 | 5 | 6 | VI-1 | Luzp2 |
| 12276 | 3 | 4 | 5 | 6 | VI-1 | Ly6c1 |
| 12277 | 3 | 4 | 5 | 6 | VI-1 | Ly6c2 |
| 12278 | 3 | 4 | 5 | 6 | VI-1 | Ly6e |
| 12279 | 3 | 4 | 5 | 6 | VI-1 | Ly6i |
| 12280 | 3 | 4 | 5 | 6 | VI-1 | Ly6k |
| 12281 | 3 | 4 | 5 | 6 | VI-1 | Ly86 |
| 12282 | 3 | 4 | 5 | 6 | VI-1 | Ly96 |
| 12283 | 3 | 4 | 5 | 6 | VI-1 | Lyar |
| 12284 | 3 | 4 | 5 | 6 | VI-1 | Lyl1 |
| 12285 | 3 | 4 | 5 | 6 | VI-1 | Lyn |
| 12286 | 3 | 4 | 5 | 6 | VI-1 | Lynx1 |

Fig. 34 - 65

| | | | | | | |
|---|---|---|---|---|---|---|
| 12287 | 3 | 4 | 5 | 6 | VI-1 | Lypd4 |
| 12288 | 3 | 4 | 5 | 6 | VI-1 | Lypla2 |
| 12289 | 3 | 4 | 5 | 6 | VI-1 | Lyplal1 |
| 12290 | 3 | 4 | 5 | 6 | VI-1 | Lyrm1 |
| 12291 | 3 | 4 | 5 | 6 | VI-1 | Lyrm2 |
| 12292 | 3 | 4 | 5 | 6 | VI-1 | Lyrm4 |
| 12293 | 3 | 4 | 5 | 6 | VI-1 | Lyrm9 |
| 12294 | 3 | 4 | 5 | 6 | VI-1 | Lysmd3 |
| 12295 | 3 | 4 | 5 | 6 | VI-1 | Lyz2 |
| 12296 | 3 | 4 | 5 | 6 | VI-1 | Lyzl4 |
| 12297 | 3 | 4 | 5 | 6 | VI-1 | Lzic |
| 12298 | 3 | 4 | 5 | 6 | VI-1 | Lztr1 |
| 12299 | 3 | 4 | 5 | 6 | VI-1 | Lzts2 |
| 12300 | 3 | 4 | 5 | 6 | VI-1 | Lzts3 |
| 12301 | 3 | 4 | 5 | 6 | VI-1 | M1ap |
| 12302 | 3 | 4 | 5 | 6 | VI-1 | Maats1 |
| 12303 | 3 | 4 | 5 | 6 | VI-1 | Macrod1 |
| 12304 | 3 | 4 | 5 | 6 | VI-1 | Mad2l1bp |
| 12305 | 3 | 4 | 5 | 6 | VI-1 | Mael |
| 12306 | 3 | 4 | 5 | 6 | VI-1 | Maf1 |
| 12307 | 3 | 4 | 5 | 6 | VI-1 | Mafg |
| 12308 | 3 | 4 | 5 | 6 | VI-1 | Mafk |
| 12309 | 3 | 4 | 5 | 6 | VI-1 | Maged2 |
| 12310 | 3 | 4 | 5 | 6 | VI-1 | Mageh1 |
| 12311 | 3 | 4 | 5 | 6 | VI-1 | Magoh |
| 12312 | 3 | 4 | 5 | 6 | VI-1 | Mak16 |
| 12313 | 3 | 4 | 5 | 6 | VI-1 | Mall |
| 12314 | 3 | 4 | 5 | 6 | VI-1 | Malt1 |
| 12315 | 3 | 4 | 5 | 6 | VI-1 | Maml2 |
| 12316 | 3 | 4 | 5 | 6 | VI-1 | Mamld1 |
| 12317 | 3 | 4 | 5 | 6 | VI-1 | Mamstr |
| 12318 | 3 | 4 | 5 | 6 | VI-1 | Man1a |
| 12319 | 3 | 4 | 5 | 6 | VI-1 | Man2a1 |
| 12320 | 3 | 4 | 5 | 6 | VI-1 | Manba |
| 12321 | 3 | 4 | 5 | 6 | VI-1 | Manbal |
| 12322 | 3 | 4 | 5 | 6 | VI-1 | Manea |
| 12323 | 3 | 4 | 5 | 6 | VI-1 | Maneal |
| 12324 | 3 | 4 | 5 | 6 | VI-1 | Manf |
| 12325 | 3 | 4 | 5 | 6 | VI-1 | Mansc4 |
| 12326 | 3 | 4 | 5 | 6 | VI-1 | Maoa |
| 12327 | 3 | 4 | 5 | 6 | VI-1 | Maob |
| 12328 | 3 | 4 | 5 | 6 | VI-1 | Map10 |
| 12329 | 3 | 4 | 5 | 6 | VI-1 | Map1lc3b |
| 12330 | 3 | 4 | 5 | 6 | VI-1 | Map1s |
| 12331 | 3 | 4 | 5 | 6 | VI-1 | Map2k3 |
| 12332 | 3 | 4 | 5 | 6 | VI-1 | Map2k5 |
| 12333 | 3 | 4 | 5 | 6 | VI-1 | Map2k6 |
| 12334 | 3 | 4 | 5 | 6 | VI-1 | Map2k7 |
| 12335 | 3 | 4 | 5 | 6 | VI-1 | Map3k11 |
| 12336 | 3 | 4 | 5 | 6 | VI-1 | Map3k14 |
| 12337 | 3 | 4 | 5 | 6 | VI-1 | Map3k2 |
| 12338 | 3 | 4 | 5 | 6 | VI-1 | Map3k4 |
| 12339 | 3 | 4 | 5 | 6 | VI-1 | Map3k5 |
| 12340 | 3 | 4 | 5 | 6 | VI-1 | Map3k7cl |
| 12341 | 3 | 4 | 5 | 6 | VI-1 | Map3k8 |
| 12342 | 3 | 4 | 5 | 6 | VI-1 | Map3k9 |
| 12343 | 3 | 4 | 5 | 6 | VI-1 | Map4k1 |
| 12344 | 3 | 4 | 5 | 6 | VI-1 | Map4k2 |
| 12345 | 3 | 4 | 5 | 6 | VI-1 | Map4k4 |
| 12346 | 3 | 4 | 5 | 6 | VI-1 | Map4k5 |
| 12347 | 3 | 4 | 5 | 6 | VI-1 | Map6d1 |
| 12348 | 3 | 4 | 5 | 6 | VI-1 | Map7d1 |
| 12349 | 3 | 4 | 5 | 6 | VI-1 | Map7d2 |
| 12350 | 3 | 4 | 5 | 6 | VI-1 | Map9 |
| 12351 | 3 | 4 | 5 | 6 | VI-1 | Mapk10 |
| 12352 | 3 | 4 | 5 | 6 | VI-1 | Mapk14 |
| 12353 | 3 | 4 | 5 | 6 | VI-1 | Mapk15 |
| 12354 | 3 | 4 | 5 | 6 | VI-1 | Mapk1ip1 |
| 12355 | 3 | 4 | 5 | 6 | VI-1 | Mapk3 |
| 12356 | 3 | 4 | 5 | 6 | VI-1 | Mapk4 |
| 12357 | 3 | 4 | 5 | 6 | VI-1 | Mapk6 |
| 12358 | 3 | 4 | 5 | 6 | VI-1 | Mapk8ip1 |
| 12359 | 3 | 4 | 5 | 6 | VI-1 | Mapkapk2 |
| 12360 | 3 | 4 | 5 | 6 | VI-1 | Mapkapk5 |
| 12361 | 3 | 4 | 5 | 6 | VI-1 | Mapkbp1 |
| 12362 | 3 | 4 | 5 | 6 | VI-1 | Mapre3 |
| 12363 | 3 | 4 | 5 | 6 | VI-1 | March10 |
| 12364 | 3 | 4 | 5 | 6 | VI-1 | March11 |
| 12365 | 3 | 4 | 5 | 6 | VI-1 | March2 |
| 12366 | 3 | 4 | 5 | 6 | VI-1 | March9 |
| 12367 | 3 | 4 | 5 | 6 | VI-1 | Marveld3 |
| 12368 | 3 | 4 | 5 | 6 | VI-1 | Masp1 |
| 12369 | 3 | 4 | 5 | 6 | VI-1 | Masp2 |
| 12370 | 3 | 4 | 5 | 6 | VI-1 | Mat2a |
| 12371 | 3 | 4 | 5 | 6 | VI-1 | Matn2 |
| 12372 | 3 | 4 | 5 | 6 | VI-1 | Matn4 |
| 12373 | 3 | 4 | 5 | 6 | VI-1 | Matr3 |
| 12374 | 3 | 4 | 5 | 6 | VI-1 | Mb21d2 |
| 12375 | 3 | 4 | 5 | 6 | VI-1 | Mbd3 |
| 12376 | 3 | 4 | 5 | 6 | VI-1 | Mbd1 |
| 12377 | 3 | 4 | 5 | 6 | VI-1 | Mbnl2 |
| 12378 | 3 | 4 | 5 | 6 | VI-1 | Mbtd1 |
| 12379 | 3 | 4 | 5 | 6 | VI-1 | Mbtps2 |
| 12380 | 3 | 4 | 5 | 6 | VI-1 | Mc4r |
| 12381 | 3 | 4 | 5 | 6 | VI-1 | Mcat |
| 12382 | 3 | 4 | 5 | 6 | VI-1 | Mccc1 |
| 12383 | 3 | 4 | 5 | 6 | VI-1 | Mcf2l |
| 12384 | 3 | 4 | 5 | 6 | VI-1 | Mcfd2 |
| 12385 | 3 | 4 | 5 | 6 | VI-1 | Mcl1 |
| 12386 | 3 | 4 | 5 | 6 | VI-1 | Mcm7 |
| 12387 | 3 | 4 | 5 | 6 | VI-1 | Mcmbp |
| 12388 | 3 | 4 | 5 | 6 | VI-1 | Mcmdc2 |
| 12389 | 3 | 4 | 5 | 6 | VI-1 | Mcoln2 |
| 12390 | 3 | 4 | 5 | 6 | VI-1 | Mcph1 |
| 12391 | 3 | 4 | 5 | 6 | VI-1 | Mcpt-ps1 |
| 12392 | 3 | 4 | 5 | 6 | VI-1 | Mcpt1 |
| 12393 | 3 | 4 | 5 | 6 | VI-1 | Mcpt8 |
| 12394 | 3 | 4 | 5 | 6 | VI-1 | Mcu |
| 12395 | 3 | 4 | 5 | 6 | VI-1 | Mdc1 |
| 12396 | 3 | 4 | 5 | 6 | VI-1 | Mdfic |
| 12397 | 3 | 4 | 5 | 6 | VI-1 | Mdh1 |
| 12398 | 3 | 4 | 5 | 6 | VI-1 | Mdh2 |
| 12399 | 3 | 4 | 5 | 6 | VI-1 | Mdk |
| 12400 | 3 | 4 | 5 | 6 | VI-1 | Me1 |
| 12401 | 3 | 4 | 5 | 6 | VI-1 | Me2 |
| 12402 | 3 | 4 | 5 | 6 | VI-1 | Me3 |
| 12403 | 3 | 4 | 5 | 6 | VI-1 | Mea1 |
| 12404 | 3 | 4 | 5 | 6 | VI-1 | Meaf6 |
| 12405 | 3 | 4 | 5 | 6 | VI-1 | Mecp2 |
| 12406 | 3 | 4 | 5 | 6 | VI-1 | Med1 |
| 12407 | 3 | 4 | 5 | 6 | VI-1 | Med10 |
| 12408 | 3 | 4 | 5 | 6 | VI-1 | Med11 |
| 12409 | 3 | 4 | 5 | 6 | VI-1 | Med13 |
| 12410 | 3 | 4 | 5 | 6 | VI-1 | Med13l |
| 12411 | 3 | 4 | 5 | 6 | VI-1 | Med14 |
| 12412 | 3 | 4 | 5 | 6 | VI-1 | Med15 |
| 12413 | 3 | 4 | 5 | 6 | VI-1 | Med16 |
| 12414 | 3 | 4 | 5 | 6 | VI-1 | Med21 |
| 12415 | 3 | 4 | 5 | 6 | VI-1 | Med22 |
| 12416 | 3 | 4 | 5 | 6 | VI-1 | Med27 |
| 12417 | 3 | 4 | 5 | 6 | VI-1 | Med28 |
| 12418 | 3 | 4 | 5 | 6 | VI-1 | Med30 |
| 12419 | 3 | 4 | 5 | 6 | VI-1 | Med4 |
| 12420 | 3 | 4 | 5 | 6 | VI-1 | Med8 |
| 12421 | 3 | 4 | 5 | 6 | VI-1 | Med9 |
| 12422 | 3 | 4 | 5 | 6 | VI-1 | Medag |
| 12423 | 3 | 4 | 5 | 6 | VI-1 | Megf8 |
| 12424 | 3 | 4 | 5 | 6 | VI-1 | Meis1 |
| 12425 | 3 | 4 | 5 | 6 | VI-1 | Meis2 |
| 12426 | 3 | 4 | 5 | 6 | VI-1 | Men1 |
| 12427 | 3 | 4 | 5 | 6 | VI-1 | Mesdc1 |
| 12428 | 3 | 4 | 5 | 6 | VI-1 | Mesp2 |
| 12429 | 3 | 4 | 5 | 6 | VI-1 | Metap2 |
| 12430 | 3 | 4 | 5 | 6 | VI-1 | Mettl1 |
| 12431 | 3 | 4 | 5 | 6 | VI-1 | Mettl15 |
| 12432 | 3 | 4 | 5 | 6 | VI-1 | Mettl16 |
| 12433 | 3 | 4 | 5 | 6 | VI-1 | Mettl17 |
| 12434 | 3 | 4 | 5 | 6 | VI-1 | Mettl18 |
| 12435 | 3 | 4 | 5 | 6 | VI-1 | Mettl21a |
| 12436 | 3 | 4 | 5 | 6 | VI-1 | Mettl21c |
| 12437 | 3 | 4 | 5 | 6 | VI-1 | Mettl21e |
| 12438 | 3 | 4 | 5 | 6 | VI-1 | Mettl23 |
| 12439 | 3 | 4 | 5 | 6 | VI-1 | Mettl25 |
| 12440 | 3 | 4 | 5 | 6 | VI-1 | Mettl5 |
| 12441 | 3 | 4 | 5 | 6 | VI-1 | Mettl6 |
| 12442 | 3 | 4 | 5 | 6 | VI-1 | Mettl7a1 |
| 12443 | 3 | 4 | 5 | 6 | VI-1 | Mettl7a2 |
| 12444 | 3 | 4 | 5 | 6 | VI-1 | Mettl7a3 |
| 12445 | 3 | 4 | 5 | 6 | VI-1 | Mettl8 |
| 12446 | 3 | 4 | 5 | 6 | VI-1 | Mfap1a |
| 12447 | 3 | 4 | 5 | 6 | VI-1 | Mfap1b |
| 12448 | 3 | 4 | 5 | 6 | VI-1 | Mfap4 |
| 12449 | 3 | 4 | 5 | 6 | VI-1 | Mfap5 |
| 12450 | 3 | 4 | 5 | 6 | VI-1 | Mfhas1 |
| 12451 | 3 | 4 | 5 | 6 | VI-1 | Mfn1 |
| 12452 | 3 | 4 | 5 | 6 | VI-1 | Mfng |
| 12453 | 3 | 4 | 5 | 6 | VI-1 | Mfsd10 |
| 12454 | 3 | 4 | 5 | 6 | VI-1 | Mfsd11 |
| 12455 | 3 | 4 | 5 | 6 | VI-1 | Mfsd2b |
| 12456 | 3 | 4 | 5 | 6 | VI-1 | Mfsd3 |
| 12457 | 3 | 4 | 5 | 6 | VI-1 | Mfsd4 |
| 12458 | 3 | 4 | 5 | 6 | VI-1 | Mfsd5 |
| 12459 | 3 | 4 | 5 | 6 | VI-1 | Mfsd6 |
| 12460 | 3 | 4 | 5 | 6 | VI-1 | Mga |
| 12461 | 3 | 4 | 5 | 6 | VI-1 | Mgam |
| 12462 | 3 | 4 | 5 | 6 | VI-1 | Mgat1 |
| 12463 | 3 | 4 | 5 | 6 | VI-1 | Mgat5b |
| 12464 | 3 | 4 | 5 | 6 | VI-1 | Mgea5 |
| 12465 | 3 | 4 | 5 | 6 | VI-1 | Mgl2 |
| 12466 | 3 | 4 | 5 | 6 | VI-1 | Mgst1 |
| 12467 | 3 | 4 | 5 | 6 | VI-1 | Mib2 |
| 12468 | 3 | 4 | 5 | 6 | VI-1 | Micalcl |
| 12469 | 3 | 4 | 5 | 6 | VI-1 | Micall2 |
| 12470 | 3 | 4 | 5 | 6 | VI-1 | Micu2 |
| 12471 | 3 | 4 | 5 | 6 | VI-1 | Mid1 |
| 12472 | 3 | 4 | 5 | 6 | VI-1 | Midn |
| 12473 | 3 | 4 | 5 | 6 | VI-1 | Mief1 |
| 12474 | 3 | 4 | 5 | 6 | VI-1 | Mief2 |
| 12475 | 3 | 4 | 5 | 6 | VI-1 | Mien1 |
| 12476 | 3 | 4 | 5 | 6 | VI-1 | Mlr1 |
| 12477 | 3 | 4 | 5 | 6 | VI-1 | Mina |
| 12478 | 3 | 4 | 5 | 6 | VI-1 | Mios |

Fig. 34 - 66

| | | | | | | | |
|---|---|---|---|---|---|---|---|
| 12479 | 3 | 4 | 5 | 6 | | VI-1 | Mipep |
| 12480 | 3 | 4 | 5 | 6 | | VI-1 | Mir17hg |
| 12481 | 3 | 4 | 5 | 6 | | VI-1 | Mira |
| 12482 | 3 | 4 | 5 | 6 | | VI-1 | Mirlet7bhg |
| 12483 | 3 | 4 | 5 | 6 | | VI-1 | Misp |
| 12484 | 3 | 4 | 5 | 6 | | VI-1 | Mitf |
| 12485 | 3 | 4 | 5 | 6 | | VI-1 | Mkks |
| 12486 | 3 | 4 | 5 | 6 | | VI-1 | Mki2 |
| 12487 | 3 | 4 | 5 | 6 | | VI-1 | Mkln1 |
| 12488 | 3 | 4 | 5 | 6 | | VI-1 | Mknk1 |
| 12489 | 3 | 4 | 5 | 6 | | VI-1 | Mknk2 |
| 12490 | 3 | 4 | 5 | 6 | | VI-1 | Mkrn1 |
| 12491 | 3 | 4 | 5 | 6 | | VI-1 | Mlana |
| 12492 | 3 | 4 | 5 | 6 | | VI-1 | Mlc1 |
| 12493 | 3 | 4 | 5 | 6 | | VI-1 | Mlf2 |
| 12494 | 3 | 4 | 5 | 6 | | VI-1 | Mlh1 |
| 12495 | 3 | 4 | 5 | 6 | | VI-1 | Mlip |
| 12496 | 3 | 4 | 5 | 6 | | VI-1 | Mllt3 |
| 12497 | 3 | 4 | 5 | 6 | | VI-1 | Mlph |
| 12498 | 3 | 4 | 5 | 6 | | VI-1 | Mlxip |
| 12499 | 3 | 4 | 5 | 6 | | VI-1 | Mlycd |
| 12500 | 3 | 4 | 5 | 6 | | VI-1 | Mmaa |
| 12501 | 3 | 4 | 5 | 6 | | VI-1 | Mmel1 |
| 12502 | 3 | 4 | 5 | 6 | | VI-1 | Mmgt2 |
| 12503 | 3 | 4 | 5 | 6 | | VI-1 | Mmp11 |
| 12504 | 3 | 4 | 5 | 6 | | VI-1 | Mmp13 |
| 12505 | 3 | 4 | 5 | 6 | | VI-1 | Mmp15 |
| 12506 | 3 | 4 | 5 | 6 | | VI-1 | Mmp17 |
| 12507 | 3 | 4 | 5 | 6 | | VI-1 | Mmp9 |
| 12508 | 3 | 4 | 5 | 6 | | VI-1 | Mn1 |
| 12509 | 3 | 4 | 5 | 6 | | VI-1 | Mnat1 |
| 12510 | 3 | 4 | 5 | 6 | | VI-1 | Mnda |
| 12511 | 3 | 4 | 5 | 6 | | VI-1 | Mns1 |
| 12512 | 3 | 4 | 5 | 6 | | VI-1 | Mnt |
| 12513 | 3 | 4 | 5 | 6 | | VI-1 | Mob2 |
| 12514 | 3 | 4 | 5 | 6 | | VI-1 | Mob3b |
| 12515 | 3 | 4 | 5 | 6 | | VI-1 | Mob3c |
| 12516 | 3 | 4 | 5 | 6 | | VI-1 | Mob4 |
| 12517 | 3 | 4 | 5 | 6 | | VI-1 | Mocos |
| 12518 | 3 | 4 | 5 | 6 | | VI-1 | Mocs1 |
| 12519 | 3 | 4 | 5 | 6 | | VI-1 | Mocs2 |
| 12520 | 3 | 4 | 5 | 6 | | VI-1 | Mocs3 |
| 12521 | 3 | 4 | 5 | 6 | | VI-1 | Mog |
| 12522 | 3 | 4 | 5 | 6 | | VI-1 | Mogat1 |
| 12523 | 3 | 4 | 5 | 6 | | VI-1 | Mogat2 |
| 12524 | 3 | 4 | 5 | 6 | | VI-1 | Mok |
| 12525 | 3 | 4 | 5 | 6 | | VI-1 | Morc4 |
| 12526 | 3 | 4 | 5 | 6 | | VI-1 | Morf4l1 |
| 12527 | 3 | 4 | 5 | 6 | | VI-1 | Morn1 |
| 12528 | 3 | 4 | 5 | 6 | | VI-1 | Morn4 |
| 12529 | 3 | 4 | 5 | 6 | | VI-1 | Morn5 |
| 12530 | 3 | 4 | 5 | 6 | | VI-1 | Mospd3 |
| 12531 | 3 | 4 | 5 | 6 | | VI-1 | Mospd4 |
| 12532 | 3 | 4 | 5 | 6 | | VI-1 | Mov10 |
| 12533 | 3 | 4 | 5 | 6 | | VI-1 | Mpdu1 |
| 12534 | 3 | 4 | 5 | 6 | | VI-1 | Mpeg1 |
| 12535 | 3 | 4 | 5 | 6 | | VI-1 | Mpg |
| 12536 | 3 | 4 | 5 | 6 | | VI-1 | Mphosph10 |
| 12537 | 3 | 4 | 5 | 6 | | VI-1 | Mphosph6 |
| 12538 | 3 | 4 | 5 | 6 | | VI-1 | Mphosph8 |
| 12539 | 3 | 4 | 5 | 6 | | VI-1 | Mpi |
| 12540 | 3 | 4 | 5 | 6 | | VI-1 | Mpp4 |
| 12541 | 3 | 4 | 5 | 6 | | VI-1 | Mpp5 |
| 12542 | 3 | 4 | 5 | 6 | | VI-1 | Mpp6 |
| 12543 | 3 | 4 | 5 | 6 | | VI-1 | Mppe1 |
| 12544 | 3 | 4 | 5 | 6 | | VI-1 | Mprip |
| 12545 | 3 | 4 | 5 | 6 | | VI-1 | Mpst |
| 12546 | 3 | 4 | 5 | 6 | | VI-1 | Mpv17 |
| 12547 | 3 | 4 | 5 | 6 | | VI-1 | Mpv17l |
| 12548 | 3 | 4 | 5 | 6 | | VI-1 | Mpz |
| 12549 | 3 | 4 | 5 | 6 | | VI-1 | Mpzl1 |
| 12550 | 3 | 4 | 5 | 6 | | VI-1 | Mrc1 |
| 12551 | 3 | 4 | 5 | 6 | | VI-1 | Mre11a |
| 12552 | 3 | 4 | 5 | 6 | | VI-1 | Mreg |
| 12553 | 3 | 4 | 5 | 6 | | VI-1 | Mrgpre |
| 12554 | 3 | 4 | 5 | 6 | | VI-1 | Mrgprx2 |
| 12555 | 3 | 4 | 5 | 6 | | VI-1 | Mroh7 |
| 12556 | 3 | 4 | 5 | 6 | | VI-1 | Mrpl10 |
| 12557 | 3 | 4 | 5 | 6 | | VI-1 | Mrpl15 |
| 12558 | 3 | 4 | 5 | 6 | | VI-1 | Mrpl17 |
| 12559 | 3 | 4 | 5 | 6 | | VI-1 | Mrpl18 |
| 12560 | 3 | 4 | 5 | 6 | | VI-1 | Mrpl20 |
| 12561 | 3 | 4 | 5 | 6 | | VI-1 | Mrpl34 |
| 12562 | 3 | 4 | 5 | 6 | | VI-1 | Mrpl35 |
| 12563 | 3 | 4 | 5 | 6 | | VI-1 | Mrpl36 |
| 12564 | 3 | 4 | 5 | 6 | | VI-1 | Mrpl37 |
| 12565 | 3 | 4 | 5 | 6 | | VI-1 | Mrpl40 |
| 12566 | 3 | 4 | 5 | 6 | | VI-1 | Mrpl42 |
| 12567 | 3 | 4 | 5 | 6 | | VI-1 | Mrpl43 |
| 12568 | 3 | 4 | 5 | 6 | | VI-1 | Mrpl45 |
| 12569 | 3 | 4 | 5 | 6 | | VI-1 | Mrpl49 |
| 12570 | 3 | 4 | 5 | 6 | | VI-1 | Mrpl51 |
| 12571 | 3 | 4 | 5 | 6 | | VI-1 | Mrpl55 |
| 12572 | 3 | 4 | 5 | 6 | | VI-1 | Mrpl57 |
| 12573 | 3 | 4 | 5 | 6 | | VI-1 | Mrpl9 |
| 12574 | 3 | 4 | 5 | 6 | | VI-1 | Mrps14 |

| | | | | | | | |
|---|---|---|---|---|---|---|---|
| 12575 | 3 | 4 | 5 | 6 | | VI-1 | Mrps17 |
| 12576 | 3 | 4 | 5 | 6 | | VI-1 | Mrps18b |
| 12577 | 3 | 4 | 5 | 6 | | VI-1 | Mrps22 |
| 12578 | 3 | 4 | 5 | 6 | | VI-1 | Mrps23 |
| 12579 | 3 | 4 | 5 | 6 | | VI-1 | Mrps27 |
| 12580 | 3 | 4 | 5 | 6 | | VI-1 | Mrps28 |
| 12581 | 3 | 4 | 5 | 6 | | VI-1 | Mrps30 |
| 12582 | 3 | 4 | 5 | 6 | | VI-1 | Mrps33 |
| 12583 | 3 | 4 | 5 | 6 | | VI-1 | Mrps34 |
| 12584 | 3 | 4 | 5 | 6 | | VI-1 | Mrps35 |
| 12585 | 3 | 4 | 5 | 6 | | VI-1 | Mrps36 |
| 12586 | 3 | 4 | 5 | 6 | | VI-1 | Mrps5 |
| 12587 | 3 | 4 | 5 | 6 | | VI-1 | Mrps7 |
| 12588 | 3 | 4 | 5 | 6 | | VI-1 | Mrps9 |
| 12589 | 3 | 4 | 5 | 6 | | VI-1 | Mrvi1 |
| 12590 | 3 | 4 | 5 | 6 | | VI-1 | Ms4a3 |
| 12591 | 3 | 4 | 5 | 6 | | VI-1 | Ms4a4c |
| 12592 | 3 | 4 | 5 | 6 | | VI-1 | Ms4a4d |
| 12593 | 3 | 4 | 5 | 6 | | VI-1 | Ms4a6b |
| 12594 | 3 | 4 | 5 | 6 | | VI-1 | Ms4a6c |
| 12595 | 3 | 4 | 5 | 6 | | VI-1 | Ms4a6d |
| 12596 | 3 | 4 | 5 | 6 | | VI-1 | Msantd1 |
| 12597 | 3 | 4 | 5 | 6 | | VI-1 | Msantd2 |
| 12598 | 3 | 4 | 5 | 6 | | VI-1 | Msantd3 |
| 12599 | 3 | 4 | 5 | 6 | | VI-1 | Msc |
| 12600 | 3 | 4 | 5 | 6 | | VI-1 | Msh2 |
| 12601 | 3 | 4 | 5 | 6 | | VI-1 | Msh3 |
| 12602 | 3 | 4 | 5 | 6 | | VI-1 | Msh5 |
| 12603 | 3 | 4 | 5 | 6 | | VI-1 | Msh6 |
| 12604 | 3 | 4 | 5 | 6 | | VI-1 | Msi1 |
| 12605 | 3 | 4 | 5 | 6 | | VI-1 | Msmo1 |
| 12606 | 3 | 4 | 5 | 6 | | VI-1 | Msr1 |
| 12607 | 3 | 4 | 5 | 6 | | VI-1 | Msrb3 |
| 12608 | 3 | 4 | 5 | 6 | | VI-1 | Mss51 |
| 12609 | 3 | 4 | 5 | 6 | | VI-1 | Msx3 |
| 12610 | 3 | 4 | 5 | 6 | | VI-1 | Mt4 |
| 12611 | 3 | 4 | 5 | 6 | | VI-1 | Mta3 |
| 12612 | 3 | 4 | 5 | 6 | | VI-1 | Mtch1 |
| 12613 | 3 | 4 | 5 | 6 | | VI-1 | Mtch2 |
| 12614 | 3 | 4 | 5 | 6 | | VI-1 | Mtcp1 |
| 12615 | 3 | 4 | 5 | 6 | | VI-1 | Mterf1b |
| 12616 | 3 | 4 | 5 | 6 | | VI-1 | Mterfd1 |
| 12617 | 3 | 4 | 5 | 6 | | VI-1 | Mterfd2 |
| 12618 | 3 | 4 | 5 | 6 | | VI-1 | Mtf2 |
| 12619 | 3 | 4 | 5 | 6 | | VI-1 | Mtfmt |
| 12620 | 3 | 4 | 5 | 6 | | VI-1 | Mtfp1 |
| 12621 | 3 | 4 | 5 | 6 | | VI-1 | Mtfr1l |
| 12622 | 3 | 4 | 5 | 6 | | VI-1 | Mtg1 |
| 12623 | 3 | 4 | 5 | 6 | | VI-1 | Mtg2 |
| 12624 | 3 | 4 | 5 | 6 | | VI-1 | Mthfd1 |
| 12625 | 3 | 4 | 5 | 6 | | VI-1 | Mthfsd |
| 12626 | 3 | 4 | 5 | 6 | | VI-1 | Mtif2 |
| 12627 | 3 | 4 | 5 | 6 | | VI-1 | Mtif3 |
| 12628 | 3 | 4 | 5 | 6 | | VI-1 | Mtl5 |
| 12629 | 3 | 4 | 5 | 6 | | VI-1 | Mtmr1 |
| 12630 | 3 | 4 | 5 | 6 | | VI-1 | Mtmr10 |
| 12631 | 3 | 4 | 5 | 6 | | VI-1 | Mtmr11 |
| 12632 | 3 | 4 | 5 | 6 | | VI-1 | Mtpap |
| 12633 | 3 | 4 | 5 | 6 | | VI-1 | Mtr |
| 12634 | 3 | 4 | 5 | 6 | | VI-1 | Mtrf1 |
| 12635 | 3 | 4 | 5 | 6 | | VI-1 | Mtrf1l |
| 12636 | 3 | 4 | 5 | 6 | | VI-1 | Mtus1 |
| 12637 | 3 | 4 | 5 | 6 | | VI-1 | Muc1 |
| 12638 | 3 | 4 | 5 | 6 | | VI-1 | Muc2 |
| 12639 | 3 | 4 | 5 | 6 | | VI-1 | Muc20 |
| 12640 | 3 | 4 | 5 | 6 | | VI-1 | Muc4 |
| 12641 | 3 | 4 | 5 | 6 | | VI-1 | Muc5b |
| 12642 | 3 | 4 | 5 | 6 | | VI-1 | Mucl1 |
| 12643 | 3 | 4 | 5 | 6 | | VI-1 | Mug1 |
| 12644 | 3 | 4 | 5 | 6 | | VI-1 | Mul1 |
| 12645 | 3 | 4 | 5 | 6 | | VI-1 | Mup11 |
| 12646 | 3 | 4 | 5 | 6 | | VI-1 | Mup14 |
| 12647 | 3 | 4 | 5 | 6 | | VI-1 | Mup19 |
| 12648 | 3 | 4 | 5 | 6 | | VI-1 | Mup20 |
| 12649 | 3 | 4 | 5 | 6 | | VI-1 | Mup21 |
| 12650 | 3 | 4 | 5 | 6 | | VI-1 | Mup5 |
| 12651 | 3 | 4 | 5 | 6 | | VI-1 | Mup6 |
| 12652 | 3 | 4 | 5 | 6 | | VI-1 | Mup7 |
| 12653 | 3 | 4 | 5 | 6 | | VI-1 | Murc |
| 12654 | 3 | 4 | 5 | 6 | | VI-1 | Mus81 |
| 12655 | 3 | 4 | 5 | 6 | | VI-1 | Mutyh |
| 12656 | 3 | 4 | 5 | 6 | | VI-1 | Mvd |
| 12657 | 3 | 4 | 5 | 6 | | VI-1 | Mvk |
| 12658 | 3 | 4 | 5 | 6 | | VI-1 | Mvp |
| 12659 | 3 | 4 | 5 | 6 | | VI-1 | Mxra7 |
| 12660 | 3 | 4 | 5 | 6 | | VI-1 | Mxra8 |
| 12661 | 3 | 4 | 5 | 6 | | VI-1 | Myadm |
| 12662 | 3 | 4 | 5 | 6 | | VI-1 | Myadml2 |
| 12663 | 3 | 4 | 5 | 6 | | VI-1 | Mybbp1a |
| 12664 | 3 | 4 | 5 | 6 | | VI-1 | Mybpc1 |
| 12665 | 3 | 4 | 5 | 6 | | VI-1 | Mybpc3 |
| 12666 | 3 | 4 | 5 | 6 | | VI-1 | Mycbpap |
| 12667 | 3 | 4 | 5 | 6 | | VI-1 | Myct1 |
| 12668 | 3 | 4 | 5 | 6 | | VI-1 | Myd88 |
| 12669 | 3 | 4 | 5 | 6 | | VI-1 | Myf6 |
| 12670 | 3 | 4 | 5 | 6 | | VI-1 | Myg1 |

Fig. 34 - 67

| | | | | | | | |
|---|---|---|---|---|---|---|---|
| 12671 | 3 | 4 | 5 | 6 | | VI-1 | Myh10 |
| 12672 | 3 | 4 | 5 | 6 | | VI-1 | Myh11 |
| 12673 | 3 | 4 | 5 | 6 | | VI-1 | Myh14 |
| 12674 | 3 | 4 | 5 | 6 | | VI-1 | Myh2 |
| 12675 | 3 | 4 | 5 | 6 | | VI-1 | Myh4 |
| 12676 | 3 | 4 | 5 | 6 | | VI-1 | Myh6 |
| 12677 | 3 | 4 | 5 | 6 | | VI-1 | Myh7 |
| 12678 | 3 | 4 | 5 | 6 | | VI-1 | Myh8 |
| 12679 | 3 | 4 | 5 | 6 | | VI-1 | Myl1 |
| 12680 | 3 | 4 | 5 | 6 | | VI-1 | Myl12b |
| 12681 | 3 | 4 | 5 | 6 | | VI-1 | Myl6b |
| 12682 | 3 | 4 | 5 | 6 | | VI-1 | Myl7 |
| 12683 | 3 | 4 | 5 | 6 | | VI-1 | Myl9 |
| 12684 | 3 | 4 | 5 | 6 | | VI-1 | Mylk2 |
| 12685 | 3 | 4 | 5 | 6 | | VI-1 | Myo15 |
| 12686 | 3 | 4 | 5 | 6 | | VI-1 | Myo18b |
| 12687 | 3 | 4 | 5 | 6 | | VI-1 | Myo1e |
| 12688 | 3 | 4 | 5 | 6 | | VI-1 | Myo1h |
| 12689 | 3 | 4 | 5 | 6 | | VI-1 | Myo6 |
| 12690 | 3 | 4 | 5 | 6 | | VI-1 | Myo7a |
| 12691 | 3 | 4 | 5 | 6 | | VI-1 | Myog |
| 12692 | 3 | 4 | 5 | 6 | | VI-1 | Myot |
| 12693 | 3 | 4 | 5 | 6 | | VI-1 | Myoz1 |
| 12694 | 3 | 4 | 5 | 6 | | VI-1 | Myoz2 |
| 12695 | 3 | 4 | 5 | 6 | | VI-1 | Myoz3 |
| 12696 | 3 | 4 | 5 | 6 | | VI-1 | Mypn |
| 12697 | 3 | 4 | 5 | 6 | | VI-1 | Myrip |
| 12698 | 3 | 4 | 5 | 6 | | VI-1 | Myt1l |
| 12699 | 3 | 4 | 5 | 6 | | VI-1 | Mzb1 |
| 12700 | 3 | 4 | 5 | 6 | | VI-1 | Mzf1 |
| 12701 | 3 | 4 | 5 | 6 | | VI-1 | Mzt2 |
| 12702 | 3 | 4 | 5 | 6 | | VI-1 | N28178 |
| 12703 | 3 | 4 | 5 | 6 | | VI-1 | N4bp2l1 |
| 12704 | 3 | 4 | 5 | 6 | | VI-1 | N4bp3 |
| 12705 | 3 | 4 | 5 | 6 | | VI-1 | Naa20 |
| 12706 | 3 | 4 | 5 | 6 | | VI-1 | Naa25 |
| 12707 | 3 | 4 | 5 | 6 | | VI-1 | Naa35 |
| 12708 | 3 | 4 | 5 | 6 | | VI-1 | Naaa |
| 12709 | 3 | 4 | 5 | 6 | | VI-1 | Naalad2 |
| 12710 | 3 | 4 | 5 | 6 | | VI-1 | Nabp2 |
| 12711 | 3 | 4 | 5 | 6 | | VI-1 | Naca |
| 12712 | 3 | 4 | 5 | 6 | | VI-1 | Nacad |
| 12713 | 3 | 4 | 5 | 6 | | VI-1 | Nadsyn1 |
| 12714 | 3 | 4 | 5 | 6 | | VI-1 | Nae1 |
| 12715 | 3 | 4 | 5 | 6 | | VI-1 | Naga |
| 12716 | 3 | 4 | 5 | 6 | | VI-1 | Nagk |
| 12717 | 3 | 4 | 5 | 6 | | VI-1 | Naglu |
| 12718 | 3 | 4 | 5 | 6 | | VI-1 | Nagpa |
| 12719 | 3 | 4 | 5 | 6 | | VI-1 | Nans |
| 12720 | 3 | 4 | 5 | 6 | | VI-1 | Nap1l3 |
| 12721 | 3 | 4 | 5 | 6 | | VI-1 | Napa |
| 12722 | 3 | 4 | 5 | 6 | | VI-1 | Napg |
| 12723 | 3 | 4 | 5 | 6 | | VI-1 | Naprt1 |
| 12724 | 3 | 4 | 5 | 6 | | VI-1 | Nars |
| 12725 | 3 | 4 | 5 | 6 | | VI-1 | Nars2 |
| 12726 | 3 | 4 | 5 | 6 | | VI-1 | Nasp |
| 12727 | 3 | 4 | 5 | 6 | | VI-1 | Nat10 |
| 12728 | 3 | 4 | 5 | 6 | | VI-1 | Nat14 |
| 12729 | 3 | 4 | 5 | 6 | | VI-1 | Nat8 |
| 12730 | 3 | 4 | 5 | 6 | | VI-1 | Nat8l |
| 12731 | 3 | 4 | 5 | 6 | | VI-1 | Nav1 |
| 12732 | 3 | 4 | 5 | 6 | | VI-1 | Nav2 |
| 12733 | 3 | 4 | 5 | 6 | | VI-1 | Nbea |
| 12734 | 3 | 4 | 5 | 6 | | VI-1 | Nbeal2 |
| 12735 | 3 | 4 | 5 | 6 | | VI-1 | Nbl1 |
| 12736 | 3 | 4 | 5 | 6 | | VI-1 | Nbr1 |
| 12737 | 3 | 4 | 5 | 6 | | VI-1 | Ncan |
| 12738 | 3 | 4 | 5 | 6 | | VI-1 | Ncapd2 |
| 12739 | 3 | 4 | 5 | 6 | | VI-1 | Ncapg2 |
| 12740 | 3 | 4 | 5 | 6 | | VI-1 | Ncaph2 |
| 12741 | 3 | 4 | 5 | 6 | | VI-1 | Nccrp1 |
| 12742 | 3 | 4 | 5 | 6 | | VI-1 | Ncdn |
| 12743 | 3 | 4 | 5 | 6 | | VI-1 | Ncf2 |
| 12744 | 3 | 4 | 5 | 6 | | VI-1 | Ncf4 |
| 12745 | 3 | 4 | 5 | 6 | | VI-1 | Ncl |
| 12746 | 3 | 4 | 5 | 6 | | VI-1 | Ncln |
| 12747 | 3 | 4 | 5 | 6 | | VI-1 | Ncmap |
| 12748 | 3 | 4 | 5 | 6 | | VI-1 | Ncoa5 |
| 12749 | 3 | 4 | 5 | 6 | | VI-1 | Ncoa7 |
| 12750 | 3 | 4 | 5 | 6 | | VI-1 | Ncor1 |
| 12751 | 3 | 4 | 5 | 6 | | VI-1 | Nctc1 |
| 12752 | 3 | 4 | 5 | 6 | | VI-1 | Nde1 |
| 12753 | 3 | 4 | 5 | 6 | | VI-1 | Ndfip1 |
| 12754 | 3 | 4 | 5 | 6 | | VI-1 | Ndfip2 |
| 12755 | 3 | 4 | 5 | 6 | | VI-1 | Ndnl2 |
| 12756 | 3 | 4 | 5 | 6 | | VI-1 | Ndrg1 |
| 12757 | 3 | 4 | 5 | 6 | | VI-1 | Ndrg2 |
| 12758 | 3 | 4 | 5 | 6 | | VI-1 | Ndrg3 |
| 12759 | 3 | 4 | 5 | 6 | | VI-1 | Ndufa1 |
| 12760 | 3 | 4 | 5 | 6 | | VI-1 | Ndufa6 |
| 12761 | 3 | 4 | 5 | 6 | | VI-1 | Ndufa8 |
| 12762 | 3 | 4 | 5 | 6 | | VI-1 | Ndufab1 |
| 12763 | 3 | 4 | 5 | 6 | | VI-1 | Ndufaf1 |
| 12764 | 3 | 4 | 5 | 6 | | VI-1 | Ndufaf2 |
| 12765 | 3 | 4 | 5 | 6 | | VI-1 | Ndufaf7 |
| 12766 | 3 | 4 | 5 | 6 | | VI-1 | Ndufb11 |
| 12767 | 3 | 4 | 5 | 6 | | VI-1 | Ndufb2 |
| 12768 | 3 | 4 | 5 | 6 | | VI-1 | Ndufb3 |
| 12769 | 3 | 4 | 5 | 6 | | VI-1 | Ndufb8 |
| 12770 | 3 | 4 | 5 | 6 | | VI-1 | Ndufb9 |
| 12771 | 3 | 4 | 5 | 6 | | VI-1 | Ndufc2 |
| 12772 | 3 | 4 | 5 | 6 | | VI-1 | Ndufs2 |
| 12773 | 3 | 4 | 5 | 6 | | VI-1 | Ndufs4 |
| 12774 | 3 | 4 | 5 | 6 | | VI-1 | Neat1 |
| 12775 | 3 | 4 | 5 | 6 | | VI-1 | Necab1 |
| 12776 | 3 | 4 | 5 | 6 | | VI-1 | Necab2 |
| 12777 | 3 | 4 | 5 | 6 | | VI-1 | Necab3 |
| 12778 | 3 | 4 | 5 | 6 | | VI-1 | Nedd1 |
| 12779 | 3 | 4 | 5 | 6 | | VI-1 | Nedd4l |
| 12780 | 3 | 4 | 5 | 6 | | VI-1 | Nedd8 |
| 12781 | 3 | 4 | 5 | 6 | | VI-1 | Nek10 |
| 12782 | 3 | 4 | 5 | 6 | | VI-1 | Nek3 |
| 12783 | 3 | 4 | 5 | 6 | | VI-1 | Nek5 |
| 12784 | 3 | 4 | 5 | 6 | | VI-1 | Nek6 |
| 12785 | 3 | 4 | 5 | 6 | | VI-1 | Nek8 |
| 12786 | 3 | 4 | 5 | 6 | | VI-1 | Nelfa |
| 12787 | 3 | 4 | 5 | 6 | | VI-1 | Nelfcd |
| 12788 | 3 | 4 | 5 | 6 | | VI-1 | Nelfe |
| 12789 | 3 | 4 | 5 | 6 | | VI-1 | Nemf |
| 12790 | 3 | 4 | 5 | 6 | | VI-1 | Nes |
| 12791 | 3 | 4 | 5 | 6 | | VI-1 | Net1 |
| 12792 | 3 | 4 | 5 | 6 | | VI-1 | Neto2 |
| 12793 | 3 | 4 | 5 | 6 | | VI-1 | Neu1 |
| 12794 | 3 | 4 | 5 | 6 | | VI-1 | Neu3 |
| 12795 | 3 | 4 | 5 | 6 | | VI-1 | Neurl1a |
| 12796 | 3 | 4 | 5 | 6 | | VI-1 | Neurl1b |
| 12797 | 3 | 4 | 5 | 6 | | VI-1 | Neurl2 |
| 12798 | 3 | 4 | 5 | 6 | | VI-1 | Neurl3 |
| 12799 | 3 | 4 | 5 | 6 | | VI-1 | Neurl4 |
| 12800 | 3 | 4 | 5 | 6 | | VI-1 | Neurod1 |
| 12801 | 3 | 4 | 5 | 6 | | VI-1 | Neurod2 |
| 12802 | 3 | 4 | 5 | 6 | | VI-1 | Neurod6 |
| 12803 | 3 | 4 | 5 | 6 | | VI-1 | Nfatc2ip |
| 12804 | 3 | 4 | 5 | 6 | | VI-1 | Nfatc4 |
| 12805 | 3 | 4 | 5 | 6 | | VI-1 | Nfe2 |
| 12806 | 3 | 4 | 5 | 6 | | VI-1 | Nfe2l2 |
| 12807 | 3 | 4 | 5 | 6 | | VI-1 | Nfib |
| 12808 | 3 | 4 | 5 | 6 | | VI-1 | Nfkb2 |
| 12809 | 3 | 4 | 5 | 6 | | VI-1 | Nfkbid |
| 12810 | 3 | 4 | 5 | 6 | | VI-1 | Nfkbie |
| 12811 | 3 | 4 | 5 | 6 | | VI-1 | Nfkbiz |
| 12812 | 3 | 4 | 5 | 6 | | VI-1 | Nfu1 |
| 12813 | 3 | 4 | 5 | 6 | | VI-1 | Nfyb |
| 12814 | 3 | 4 | 5 | 6 | | VI-1 | Nfyc |
| 12815 | 3 | 4 | 5 | 6 | | VI-1 | Ngb |
| 12816 | 3 | 4 | 5 | 6 | | VI-1 | Ngf |
| 12817 | 3 | 4 | 5 | 6 | | VI-1 | Ngfrap1 |
| 12818 | 3 | 4 | 5 | 6 | | VI-1 | Nhej1 |
| 12819 | 3 | 4 | 5 | 6 | | VI-1 | Nhlrc1 |
| 12820 | 3 | 4 | 5 | 6 | | VI-1 | Nhlrc2 |
| 12821 | 3 | 4 | 5 | 6 | | VI-1 | Nhlrc3 |
| 12822 | 3 | 4 | 5 | 6 | | VI-1 | Nhlrc4 |
| 12823 | 3 | 4 | 5 | 6 | | VI-1 | Nhsl2 |
| 12824 | 3 | 4 | 5 | 6 | | VI-1 | Nif3l1 |
| 12825 | 3 | 4 | 5 | 6 | | VI-1 | Nifk |
| 12826 | 3 | 4 | 5 | 6 | | VI-1 | Nin |
| 12827 | 3 | 4 | 5 | 6 | | VI-1 | Ninj1 |
| 12828 | 3 | 4 | 5 | 6 | | VI-1 | Nip7 |
| 12829 | 3 | 4 | 5 | 6 | | VI-1 | Nipa1 |
| 12830 | 3 | 4 | 5 | 6 | | VI-1 | Nipa2 |
| 12831 | 3 | 4 | 5 | 6 | | VI-1 | Nipsnap1 |
| 12832 | 3 | 4 | 5 | 6 | | VI-1 | Nit2 |
| 12833 | 3 | 4 | 5 | 6 | | VI-1 | Nkain2 |
| 12834 | 3 | 4 | 5 | 6 | | VI-1 | Nkain4 |
| 12835 | 3 | 4 | 5 | 6 | | VI-1 | Nkap |
| 12836 | 3 | 4 | 5 | 6 | | VI-1 | Nkg7 |
| 12837 | 3 | 4 | 5 | 6 | | VI-1 | Nkpd1 |
| 12838 | 3 | 4 | 5 | 6 | | VI-1 | Nkrf |
| 12839 | 3 | 4 | 5 | 6 | | VI-1 | Nkx2-3 |
| 12840 | 3 | 4 | 5 | 6 | | VI-1 | Nle1 |
| 12841 | 3 | 4 | 5 | 6 | | VI-1 | Nlgn3 |
| 12842 | 3 | 4 | 5 | 6 | | VI-1 | Nlk |
| 12843 | 3 | 4 | 5 | 6 | | VI-1 | Nln |
| 12844 | 3 | 4 | 5 | 6 | | VI-1 | Nlrc4 |
| 12845 | 3 | 4 | 5 | 6 | | VI-1 | Nlrc5 |
| 12846 | 3 | 4 | 5 | 6 | | VI-1 | Nlrp6 |
| 12847 | 3 | 4 | 5 | 6 | | VI-1 | Nme4 |
| 12848 | 3 | 4 | 5 | 6 | | VI-1 | Nmnat2 |
| 12849 | 3 | 4 | 5 | 6 | | VI-1 | Nmnat3 |
| 12850 | 3 | 4 | 5 | 6 | | VI-1 | Nmral1 |
| 12851 | 3 | 4 | 5 | 6 | | VI-1 | Nmrk1 |
| 12852 | 3 | 4 | 5 | 6 | | VI-1 | Noc4l |
| 12853 | 3 | 4 | 5 | 6 | | VI-1 | Nol11 |
| 12854 | 3 | 4 | 5 | 6 | | VI-1 | Nol3 |
| 12855 | 3 | 4 | 5 | 6 | | VI-1 | Nol4 |
| 12856 | 3 | 4 | 5 | 6 | | VI-1 | Nol9 |
| 12857 | 3 | 4 | 5 | 6 | | VI-1 | Nolc1 |
| 12858 | 3 | 4 | 5 | 6 | | VI-1 | Nomo1 |
| 12859 | 3 | 4 | 5 | 6 | | VI-1 | Nop10 |
| 12860 | 3 | 4 | 5 | 6 | | VI-1 | Nop14 |
| 12861 | 3 | 4 | 5 | 6 | | VI-1 | Nop2 |
| 12862 | 3 | 4 | 5 | 6 | | VI-1 | Nop56 |

Fig. 34 - 68

| | | | | | | |
|---|---|---|---|---|---|---|
| 12863 | 3 | 4 | 5 | 6 | VI-1 | Nop9 |
| 12864 | 3 | 4 | 5 | 6 | VI-1 | Nos1ap |
| 12865 | 3 | 4 | 5 | 6 | VI-1 | Nos3 |
| 12866 | 3 | 4 | 5 | 6 | VI-1 | Nosip |
| 12867 | 3 | 4 | 5 | 6 | VI-1 | Notch4 |
| 12868 | 3 | 4 | 5 | 6 | VI-1 | Nov |
| 12869 | 3 | 4 | 5 | 6 | VI-1 | Nova2 |
| 12870 | 3 | 4 | 5 | 6 | VI-1 | Nox1 |
| 12871 | 3 | 4 | 5 | 6 | VI-1 | Nox4 |
| 12872 | 3 | 4 | 5 | 6 | VI-1 | Noxa1 |
| 12873 | 3 | 4 | 5 | 6 | VI-1 | Noxo1 |
| 12874 | 3 | 4 | 5 | 6 | VI-1 | Npas1 |
| 12875 | 3 | 4 | 5 | 6 | VI-1 | Npas3 |
| 12876 | 3 | 4 | 5 | 6 | VI-1 | Npas4 |
| 12877 | 3 | 4 | 5 | 6 | VI-1 | Npb |
| 12878 | 3 | 4 | 5 | 6 | VI-1 | Npc2 |
| 12879 | 3 | 4 | 5 | 6 | VI-1 | Npepl1 |
| 12880 | 3 | 4 | 5 | 6 | VI-1 | Nphp1 |
| 12881 | 3 | 4 | 5 | 6 | VI-1 | Nphp4 |
| 12882 | 3 | 4 | 5 | 6 | VI-1 | Nploc4 |
| 12883 | 3 | 4 | 5 | 6 | VI-1 | Npm1 |
| 12884 | 3 | 4 | 5 | 6 | VI-1 | Npm2 |
| 12885 | 3 | 4 | 5 | 6 | VI-1 | Npm3-ps1 |
| 12886 | 3 | 4 | 5 | 6 | VI-1 | Nppa |
| 12887 | 3 | 4 | 5 | 6 | VI-1 | Nppc |
| 12888 | 3 | 4 | 5 | 6 | VI-1 | Npr2 |
| 12889 | 3 | 4 | 5 | 6 | VI-1 | Nprl2 |
| 12890 | 3 | 4 | 5 | 6 | VI-1 | Nprl3 |
| 12891 | 3 | 4 | 5 | 6 | VI-1 | Nps |
| 12892 | 3 | 4 | 5 | 6 | VI-1 | Nptx2 |
| 12893 | 3 | 4 | 5 | 6 | VI-1 | Npy |
| 12894 | 3 | 4 | 5 | 6 | VI-1 | Npy4r |
| 12895 | 3 | 4 | 5 | 6 | VI-1 | Nqo1 |
| 12896 | 3 | 4 | 5 | 6 | VI-1 | Nr0b2 |
| 12897 | 3 | 4 | 5 | 6 | VI-1 | Nr1d1 |
| 12898 | 3 | 4 | 5 | 6 | VI-1 | Nr1h2 |
| 12899 | 3 | 4 | 5 | 6 | VI-1 | Nr1i3 |
| 12900 | 3 | 4 | 5 | 6 | VI-1 | Nr2f1 |
| 12901 | 3 | 4 | 5 | 6 | VI-1 | Nr2f2 |
| 12902 | 3 | 4 | 5 | 6 | VI-1 | Nr2f6 |
| 12903 | 3 | 4 | 5 | 6 | VI-1 | Nradd |
| 12904 | 3 | 4 | 5 | 6 | VI-1 | Nrap |
| 12905 | 3 | 4 | 5 | 6 | VI-1 | Nrbp2 |
| 12906 | 3 | 4 | 5 | 6 | VI-1 | Nrcam |
| 12907 | 3 | 4 | 5 | 6 | VI-1 | Nrde2 |
| 12908 | 3 | 4 | 5 | 6 | VI-1 | Nrg2 |
| 12909 | 3 | 4 | 5 | 6 | VI-1 | Nrip2 |
| 12910 | 3 | 4 | 5 | 6 | VI-1 | Nrip3 |
| 12911 | 3 | 4 | 5 | 6 | VI-1 | Nrm |
| 12912 | 3 | 4 | 5 | 6 | VI-1 | Nrn1l |
| 12913 | 3 | 4 | 5 | 6 | VI-1 | Nrp |
| 12914 | 3 | 4 | 5 | 6 | VI-1 | Nrp1 |
| 12915 | 3 | 4 | 5 | 6 | VI-1 | Nrxn2 |
| 12916 | 3 | 4 | 5 | 6 | VI-1 | Nrxn3 |
| 12917 | 3 | 4 | 5 | 6 | VI-1 | Nsa2 |
| 12918 | 3 | 4 | 5 | 6 | VI-1 | Nsfl1c |
| 12919 | 3 | 4 | 5 | 6 | VI-1 | Nsmaf |
| 12920 | 3 | 4 | 5 | 6 | VI-1 | Nsun2 |
| 12921 | 3 | 4 | 5 | 6 | VI-1 | Nsun4 |
| 12922 | 3 | 4 | 5 | 6 | VI-1 | Nsun6 |
| 12923 | 3 | 4 | 5 | 6 | VI-1 | Nt5c1b |
| 12924 | 3 | 4 | 5 | 6 | VI-1 | Nt5c2 |
| 12925 | 3 | 4 | 5 | 6 | VI-1 | Nt5c3 |
| 12926 | 3 | 4 | 5 | 6 | VI-1 | Nt5dc1 |
| 12927 | 3 | 4 | 5 | 6 | VI-1 | Nt5e |
| 12928 | 3 | 4 | 5 | 6 | VI-1 | Nt5m |
| 12929 | 3 | 4 | 5 | 6 | VI-1 | Ntf3 |
| 12930 | 3 | 4 | 5 | 6 | VI-1 | Ntpcr |
| 12931 | 3 | 4 | 5 | 6 | VI-1 | Nts |
| 12932 | 3 | 4 | 5 | 6 | VI-1 | Nub1 |
| 12933 | 3 | 4 | 5 | 6 | VI-1 | Nubp1 |
| 12934 | 3 | 4 | 5 | 6 | VI-1 | Nucb1 |
| 12935 | 3 | 4 | 5 | 6 | VI-1 | Nucb2 |
| 12936 | 3 | 4 | 5 | 6 | VI-1 | Nucks1 |
| 12937 | 3 | 4 | 5 | 6 | VI-1 | Nudcd1 |
| 12938 | 3 | 4 | 5 | 6 | VI-1 | Nudcd2 |
| 12939 | 3 | 4 | 5 | 6 | VI-1 | Nudcd3 |
| 12940 | 3 | 4 | 5 | 6 | VI-1 | Nudt10 |
| 12941 | 3 | 4 | 5 | 6 | VI-1 | Nudt11 |
| 12942 | 3 | 4 | 5 | 6 | VI-1 | Nudt16 |
| 12943 | 3 | 4 | 5 | 6 | VI-1 | Nudt16l1 |
| 12944 | 3 | 4 | 5 | 6 | VI-1 | Nudt17 |
| 12945 | 3 | 4 | 5 | 6 | VI-1 | Nudt21 |
| 12946 | 3 | 4 | 5 | 6 | VI-1 | Nudt5 |
| 12947 | 3 | 4 | 5 | 6 | VI-1 | Nudt7 |
| 12948 | 3 | 4 | 5 | 6 | VI-1 | Nudt9 |
| 12949 | 3 | 4 | 5 | 6 | VI-1 | Nuggc |
| 12950 | 3 | 4 | 5 | 6 | VI-1 | Numb |
| 12951 | 3 | 4 | 5 | 6 | VI-1 | Numbl |
| 12952 | 3 | 4 | 5 | 6 | VI-1 | Nup133 |
| 12953 | 3 | 4 | 5 | 6 | VI-1 | Nup37 |
| 12954 | 3 | 4 | 5 | 6 | VI-1 | Nup43 |
| 12955 | 3 | 4 | 5 | 6 | VI-1 | Nup50 |
| 12956 | 3 | 4 | 5 | 6 | VI-1 | Nupl1 |
| 12957 | 3 | 4 | 5 | 6 | VI-1 | Nupr1 |
| 12958 | 3 | 4 | 5 | 6 | VI-1 | Nusap1 |
| 12959 | 3 | 4 | 5 | 6 | VI-1 | Nutf2 |
| 12960 | 3 | 4 | 5 | 6 | VI-1 | Nvl |
| 12961 | 3 | 4 | 5 | 6 | VI-1 | Nxf1 |
| 12962 | 3 | 4 | 5 | 6 | VI-1 | Nxnl1 |
| 12963 | 3 | 4 | 5 | 6 | VI-1 | Nxnl2 |
| 12964 | 3 | 4 | 5 | 6 | VI-1 | Nxpe3 |
| 12965 | 3 | 4 | 5 | 6 | VI-1 | Nxpe4 |
| 12966 | 3 | 4 | 5 | 6 | VI-1 | Nxpe5 |
| 12967 | 3 | 4 | 5 | 6 | VI-1 | Nxph1 |
| 12968 | 3 | 4 | 5 | 6 | VI-1 | Nxph3 |
| 12969 | 3 | 4 | 5 | 6 | VI-1 | Nyap1 |
| 12970 | 3 | 4 | 5 | 6 | VI-1 | Oaf |
| 12971 | 3 | 4 | 5 | 6 | VI-1 | Oard1 |
| 12972 | 3 | 4 | 5 | 6 | VI-1 | Oas1b |
| 12973 | 3 | 4 | 5 | 6 | VI-1 | Oat |
| 12974 | 3 | 4 | 5 | 6 | VI-1 | Oaz1 |
| 12975 | 3 | 4 | 5 | 6 | VI-1 | Obfc1 |
| 12976 | 3 | 4 | 5 | 6 | VI-1 | Obscn |
| 12977 | 3 | 4 | 5 | 6 | VI-1 | Obsl1 |
| 12978 | 3 | 4 | 5 | 6 | VI-1 | Ociad2 |
| 12979 | 3 | 4 | 5 | 6 | VI-1 | Ocln |
| 12980 | 3 | 4 | 5 | 6 | VI-1 | Ocstamp |
| 12981 | 3 | 4 | 5 | 6 | VI-1 | Odc1 |
| 12982 | 3 | 4 | 5 | 6 | VI-1 | Odf2 |
| 12983 | 3 | 4 | 5 | 6 | VI-1 | Odf3b |
| 12984 | 3 | 4 | 5 | 6 | VI-1 | Odf4 |
| 12985 | 3 | 4 | 5 | 6 | VI-1 | Ofd1 |
| 12986 | 3 | 4 | 5 | 6 | VI-1 | Ogdh |
| 12987 | 3 | 4 | 5 | 6 | VI-1 | Ogdhl |
| 12988 | 3 | 4 | 5 | 6 | VI-1 | Ogn |
| 12989 | 3 | 4 | 5 | 6 | VI-1 | Oip5 |
| 12990 | 3 | 4 | 5 | 6 | VI-1 | Oit1 |
| 12991 | 3 | 4 | 5 | 6 | VI-1 | Olfm2 |
| 12992 | 3 | 4 | 5 | 6 | VI-1 | Olfr1372-ps1 |
| 12993 | 3 | 4 | 5 | 6 | VI-1 | Olfr1396 |
| 12994 | 3 | 4 | 5 | 6 | VI-1 | Olfr242 |
| 12995 | 3 | 4 | 5 | 6 | VI-1 | Olfr27 |
| 12996 | 3 | 4 | 5 | 6 | VI-1 | Olfr433 |
| 12997 | 3 | 4 | 5 | 6 | VI-1 | Olfr893 |
| 12998 | 3 | 4 | 5 | 6 | VI-1 | Oma1 |
| 12999 | 3 | 4 | 5 | 6 | VI-1 | Omd |
| 13000 | 3 | 4 | 5 | 6 | VI-1 | Onecut3 |
| 13001 | 3 | 4 | 5 | 6 | VI-1 | Opcml |
| 13002 | 3 | 4 | 5 | 6 | VI-1 | Ophn1 |
| 13003 | 3 | 4 | 5 | 6 | VI-1 | Opn1mw |
| 13004 | 3 | 4 | 5 | 6 | VI-1 | Opn3 |
| 13005 | 3 | 4 | 5 | 6 | VI-1 | Oprl1 |
| 13006 | 3 | 4 | 5 | 6 | VI-1 | Optn |
| 13007 | 3 | 4 | 5 | 6 | VI-1 | Orai1 |
| 13008 | 3 | 4 | 5 | 6 | VI-1 | Orai3 |
| 13009 | 3 | 4 | 5 | 6 | VI-1 | Orc5 |
| 13010 | 3 | 4 | 5 | 6 | VI-1 | Orc6 |
| 13011 | 3 | 4 | 5 | 6 | VI-1 | Ormdl1 |
| 13012 | 3 | 4 | 5 | 6 | VI-1 | Os9 |
| 13013 | 3 | 4 | 5 | 6 | VI-1 | Osbp2 |
| 13014 | 3 | 4 | 5 | 6 | VI-1 | Osbpl10 |
| 13015 | 3 | 4 | 5 | 6 | VI-1 | Osbpl11 |
| 13016 | 3 | 4 | 5 | 6 | VI-1 | Osbpl1a |
| 13017 | 3 | 4 | 5 | 6 | VI-1 | Osbpl3 |
| 13018 | 3 | 4 | 5 | 6 | VI-1 | Osbpl6 |
| 13019 | 3 | 4 | 5 | 6 | VI-1 | Osbpl7 |
| 13020 | 3 | 4 | 5 | 6 | VI-1 | Osbpl8 |
| 13021 | 3 | 4 | 5 | 6 | VI-1 | Osbpl9 |
| 13022 | 3 | 4 | 5 | 6 | VI-1 | Oscar |
| 13023 | 3 | 4 | 5 | 6 | VI-1 | Oscp1 |
| 13024 | 3 | 4 | 5 | 6 | VI-1 | Osgin1 |
| 13025 | 3 | 4 | 5 | 6 | VI-1 | Osmr |
| 13026 | 3 | 4 | 5 | 6 | VI-1 | Osr1 |
| 13027 | 3 | 4 | 5 | 6 | VI-1 | Ostf1 |
| 13028 | 3 | 4 | 5 | 6 | VI-1 | Otoa |
| 13029 | 3 | 4 | 5 | 6 | VI-1 | Otof |
| 13030 | 3 | 4 | 5 | 6 | VI-1 | Otop3 |
| 13031 | 3 | 4 | 5 | 6 | VI-1 | Otub1 |
| 13032 | 3 | 4 | 5 | 6 | VI-1 | Otub2 |
| 13033 | 3 | 4 | 5 | 6 | VI-1 | Otud3 |
| 13034 | 3 | 4 | 5 | 6 | VI-1 | Otud4 |
| 13035 | 3 | 4 | 5 | 6 | VI-1 | Otud5 |
| 13036 | 3 | 4 | 5 | 6 | VI-1 | Otud7b |
| 13037 | 3 | 4 | 5 | 6 | VI-1 | Otx1 |
| 13038 | 3 | 4 | 5 | 6 | VI-1 | Ovca2 |
| 13039 | 3 | 4 | 5 | 6 | VI-1 | Ovgp1 |
| 13040 | 3 | 4 | 5 | 6 | VI-1 | Ovol2 |
| 13041 | 3 | 4 | 5 | 6 | VI-1 | Oxa1l |
| 13042 | 3 | 4 | 5 | 6 | VI-1 | Oxct2b |
| 13043 | 3 | 4 | 5 | 6 | VI-1 | Oxld1 |
| 13044 | 3 | 4 | 5 | 6 | VI-1 | Oxnad1 |
| 13045 | 3 | 4 | 5 | 6 | VI-1 | Oxr1 |
| 13046 | 3 | 4 | 5 | 6 | VI-1 | P2rx1 |
| 13047 | 3 | 4 | 5 | 6 | VI-1 | P2rx4 |
| 13048 | 3 | 4 | 5 | 6 | VI-1 | P2rx7 |
| 13049 | 3 | 4 | 5 | 6 | VI-1 | P2ry10 |
| 13050 | 3 | 4 | 5 | 6 | VI-1 | P2ry4 |
| 13051 | 3 | 4 | 5 | 6 | VI-1 | P2ry6 |
| 13052 | 3 | 4 | 5 | 6 | VI-1 | P4ha1 |
| 13053 | 3 | 4 | 5 | 6 | VI-1 | P4ha2 |
| 13054 | 3 | 4 | 5 | 6 | VI-1 | P4hb |

Fig. 34 - 69

| | | | | | | |
|---|---|---|---|---|---|---|
| 13055 | 3 | 4 | 5 | 6 | VI-1 | Pa2g4 |
| 13056 | 3 | 4 | 5 | 6 | VI-1 | Pabpc1 |
| 13057 | 3 | 4 | 5 | 6 | VI-1 | Pabpc1l |
| 13058 | 3 | 4 | 5 | 6 | VI-1 | Pabpc2 |
| 13059 | 3 | 4 | 5 | 6 | VI-1 | Pabpc4 |
| 13060 | 3 | 4 | 5 | 6 | VI-1 | Pacrg |
| 13061 | 3 | 4 | 5 | 6 | VI-1 | Pacs1 |
| 13062 | 3 | 4 | 5 | 6 | VI-1 | Padi2 |
| 13063 | 3 | 4 | 5 | 6 | VI-1 | Pafah1b3 |
| 13064 | 3 | 4 | 5 | 6 | VI-1 | Pag1 |
| 13065 | 3 | 4 | 5 | 6 | VI-1 | Pagr1a |
| 13066 | 3 | 4 | 5 | 6 | VI-1 | Paip1 |
| 13067 | 3 | 4 | 5 | 6 | VI-1 | Paip2b |
| 13068 | 3 | 4 | 5 | 6 | VI-1 | Pak1ip1 |
| 13069 | 3 | 4 | 5 | 6 | VI-1 | Pak4 |
| 13070 | 3 | 4 | 5 | 6 | VI-1 | Pam |
| 13071 | 3 | 4 | 5 | 6 | VI-1 | Pamr1 |
| 13072 | 3 | 4 | 5 | 6 | VI-1 | Pan2 |
| 13073 | 3 | 4 | 5 | 6 | VI-1 | Pank1 |
| 13074 | 3 | 4 | 5 | 6 | VI-1 | Panx1 |
| 13075 | 3 | 4 | 5 | 6 | VI-1 | Papd5 |
| 13076 | 3 | 4 | 5 | 6 | VI-1 | Papd7 |
| 13077 | 3 | 4 | 5 | 6 | VI-1 | Papss1 |
| 13078 | 3 | 4 | 5 | 6 | VI-1 | Papss2 |
| 13079 | 3 | 4 | 5 | 6 | VI-1 | Paqr7 |
| 13080 | 3 | 4 | 5 | 6 | VI-1 | Paqr8 |
| 13081 | 3 | 4 | 5 | 6 | VI-1 | Pard3 |
| 13082 | 3 | 4 | 5 | 6 | VI-1 | Pard6b |
| 13083 | 3 | 4 | 5 | 6 | VI-1 | Parp10 |
| 13084 | 3 | 4 | 5 | 6 | VI-1 | Parp12 |
| 13085 | 3 | 4 | 5 | 6 | VI-1 | Parp14 |
| 13086 | 3 | 4 | 5 | 6 | VI-1 | Parp4 |
| 13087 | 3 | 4 | 5 | 6 | VI-1 | Parp8 |
| 13088 | 3 | 4 | 5 | 6 | VI-1 | Parp9 |
| 13089 | 3 | 4 | 5 | 6 | VI-1 | Parvb |
| 13090 | 3 | 4 | 5 | 6 | VI-1 | Parvg |
| 13091 | 3 | 4 | 5 | 6 | VI-1 | Pax1 |
| 13092 | 3 | 4 | 5 | 6 | VI-1 | Pbdc1 |
| 13093 | 3 | 4 | 5 | 6 | VI-1 | Pbld2 |
| 13094 | 3 | 4 | 5 | 6 | VI-1 | Pcbd1 |
| 13095 | 3 | 4 | 5 | 6 | VI-1 | Pcbp3 |
| 13096 | 3 | 4 | 5 | 6 | VI-1 | Pcbp4 |
| 13097 | 3 | 4 | 5 | 6 | VI-1 | Pccb |
| 13098 | 3 | 4 | 5 | 6 | VI-1 | Pcdh10 |
| 13099 | 3 | 4 | 5 | 6 | VI-1 | Pcdh17 |
| 13100 | 3 | 4 | 5 | 6 | VI-1 | Pcdh20 |
| 13101 | 3 | 4 | 5 | 6 | VI-1 | Pcdh9 |
| 13102 | 3 | 4 | 5 | 6 | VI-1 | Pcdha2 |
| 13103 | 3 | 4 | 5 | 6 | VI-1 | Pcdha6 |
| 13104 | 3 | 4 | 5 | 6 | VI-1 | Pcdhac2 |
| 13105 | 3 | 4 | 5 | 6 | VI-1 | Pcdhb20 |
| 13106 | 3 | 4 | 5 | 6 | VI-1 | Pcdhga7 |
| 13107 | 3 | 4 | 5 | 6 | VI-1 | Pcdhgb4 |
| 13108 | 3 | 4 | 5 | 6 | VI-1 | Pcdhgb7 |
| 13109 | 3 | 4 | 5 | 6 | VI-1 | Pcdhgb8 |
| 13110 | 3 | 4 | 5 | 6 | VI-1 | Pced1a |
| 13111 | 3 | 4 | 5 | 6 | VI-1 | Pcf11 |
| 13112 | 3 | 4 | 5 | 6 | VI-1 | Pcgf1 |
| 13113 | 3 | 4 | 5 | 6 | VI-1 | Pcgf6 |
| 13114 | 3 | 4 | 5 | 6 | VI-1 | Pcif1 |
| 13115 | 3 | 4 | 5 | 6 | VI-1 | Pclo |
| 13116 | 3 | 4 | 5 | 6 | VI-1 | Pcm1 |
| 13117 | 3 | 4 | 5 | 6 | VI-1 | Pcmtd1 |
| 13118 | 3 | 4 | 5 | 6 | VI-1 | Pcmtd2 |
| 13119 | 3 | 4 | 5 | 6 | VI-1 | Pcnt |
| 13120 | 3 | 4 | 5 | 6 | VI-1 | Pcolce |
| 13121 | 3 | 4 | 5 | 6 | VI-1 | Pcp2 |
| 13122 | 3 | 4 | 5 | 6 | VI-1 | Pcsk1 |
| 13123 | 3 | 4 | 5 | 6 | VI-1 | Pcsk4 |
| 13124 | 3 | 4 | 5 | 6 | VI-1 | Pcsk5 |
| 13125 | 3 | 4 | 5 | 6 | VI-1 | Pctp |
| 13126 | 3 | 4 | 5 | 6 | VI-1 | Pcyox1l |
| 13127 | 3 | 4 | 5 | 6 | VI-1 | Pdap1 |
| 13128 | 3 | 4 | 5 | 6 | VI-1 | Pdcd1 |
| 13129 | 3 | 4 | 5 | 6 | VI-1 | Pdcd10 |
| 13130 | 3 | 4 | 5 | 6 | VI-1 | Pdcd2 |
| 13131 | 3 | 4 | 5 | 6 | VI-1 | Pdcd2l |
| 13132 | 3 | 4 | 5 | 6 | VI-1 | Pdcd4 |
| 13133 | 3 | 4 | 5 | 6 | VI-1 | Pdcd7 |
| 13134 | 3 | 4 | 5 | 6 | VI-1 | Pdcl2 |
| 13135 | 3 | 4 | 5 | 6 | VI-1 | Pdcl3 |
| 13136 | 3 | 4 | 5 | 6 | VI-1 | Pde10a |
| 13137 | 3 | 4 | 5 | 6 | VI-1 | Pde1a |
| 13138 | 3 | 4 | 5 | 6 | VI-1 | Pde1b |
| 13139 | 3 | 4 | 5 | 6 | VI-1 | Pde2a |
| 13140 | 3 | 4 | 5 | 6 | VI-1 | Pde3b |
| 13141 | 3 | 4 | 5 | 6 | VI-1 | Pde4c |
| 13142 | 3 | 4 | 5 | 6 | VI-1 | Pde4dip |
| 13143 | 3 | 4 | 5 | 6 | VI-1 | Pde5a |
| 13144 | 3 | 4 | 5 | 6 | VI-1 | Pde7a |
| 13145 | 3 | 4 | 5 | 6 | VI-1 | Pde7b |
| 13146 | 3 | 4 | 5 | 6 | VI-1 | Pdgfb |
| 13147 | 3 | 4 | 5 | 6 | VI-1 | Pdgfc |
| 13148 | 3 | 4 | 5 | 6 | VI-1 | Pdgfd |
| 13149 | 3 | 4 | 5 | 6 | VI-1 | Pdgfra |
| 13150 | 3 | 4 | 5 | 6 | VI-1 | Pdhb |
| 13151 | 3 | 4 | 5 | 6 | VI-1 | Pdia5 |
| 13152 | 3 | 4 | 5 | 6 | VI-1 | Pdik1l |
| 13153 | 3 | 4 | 5 | 6 | VI-1 | Pdk2 |
| 13154 | 3 | 4 | 5 | 6 | VI-1 | Pdlim3 |
| 13155 | 3 | 4 | 5 | 6 | VI-1 | Pdlim4 |
| 13156 | 3 | 4 | 5 | 6 | VI-1 | Pdlim5 |
| 13157 | 3 | 4 | 5 | 6 | VI-1 | Pdp1 |
| 13158 | 3 | 4 | 5 | 6 | VI-1 | Pdpr |
| 13159 | 3 | 4 | 5 | 6 | VI-1 | Pds5a |
| 13160 | 3 | 4 | 5 | 6 | VI-1 | Pdss1 |
| 13161 | 3 | 4 | 5 | 6 | VI-1 | Pdxdc1 |
| 13162 | 3 | 4 | 5 | 6 | VI-1 | Pdzd3 |
| 13163 | 3 | 4 | 5 | 6 | VI-1 | Pdzd4 |
| 13164 | 3 | 4 | 5 | 6 | VI-1 | Pdzk1 |
| 13165 | 3 | 4 | 5 | 6 | VI-1 | Pear1 |
| 13166 | 3 | 4 | 5 | 6 | VI-1 | Pebp1 |
| 13167 | 3 | 4 | 5 | 6 | VI-1 | Pebp4 |
| 13168 | 3 | 4 | 5 | 6 | VI-1 | Pecr |
| 13169 | 3 | 4 | 5 | 6 | VI-1 | Peli1 |
| 13170 | 3 | 4 | 5 | 6 | VI-1 | Peli2 |
| 13171 | 3 | 4 | 5 | 6 | VI-1 | Peli3 |
| 13172 | 3 | 4 | 5 | 6 | VI-1 | Pelo |
| 13173 | 3 | 4 | 5 | 6 | VI-1 | Pelp1 |
| 13174 | 3 | 4 | 5 | 6 | VI-1 | Peo1 |
| 13175 | 3 | 4 | 5 | 6 | VI-1 | Pepd |
| 13176 | 3 | 4 | 5 | 6 | VI-1 | Per1 |
| 13177 | 3 | 4 | 5 | 6 | VI-1 | Pes1 |
| 13178 | 3 | 4 | 5 | 6 | VI-1 | Pex10 |
| 13179 | 3 | 4 | 5 | 6 | VI-1 | Pex13 |
| 13180 | 3 | 4 | 5 | 6 | VI-1 | Pex7 |
| 13181 | 3 | 4 | 5 | 6 | VI-1 | Pf4 |
| 13182 | 3 | 4 | 5 | 6 | VI-1 | Pfkfb1 |
| 13183 | 3 | 4 | 5 | 6 | VI-1 | Pfkm |
| 13184 | 3 | 4 | 5 | 6 | VI-1 | Pfkp |
| 13185 | 3 | 4 | 5 | 6 | VI-1 | Pga5 |
| 13186 | 3 | 4 | 5 | 6 | VI-1 | Pgam1 |
| 13187 | 3 | 4 | 5 | 6 | VI-1 | Pgam5 |
| 13188 | 3 | 4 | 5 | 6 | VI-1 | Pgap2 |
| 13189 | 3 | 4 | 5 | 6 | VI-1 | Pgd |
| 13190 | 3 | 4 | 5 | 6 | VI-1 | Pgk1 |
| 13191 | 3 | 4 | 5 | 6 | VI-1 | Pgm1 |
| 13192 | 3 | 4 | 5 | 6 | VI-1 | Pgm2 |
| 13193 | 3 | 4 | 5 | 6 | VI-1 | Pgm3 |
| 13194 | 3 | 4 | 5 | 6 | VI-1 | Pgr |
| 13195 | 3 | 4 | 5 | 6 | VI-1 | Pgrmc1 |
| 13196 | 3 | 4 | 5 | 6 | VI-1 | Pgrmc2 |
| 13197 | 3 | 4 | 5 | 6 | VI-1 | Phb2 |
| 13198 | 3 | 4 | 5 | 6 | VI-1 | Phc2 |
| 13199 | 3 | 4 | 5 | 6 | VI-1 | Phf1 |
| 13200 | 3 | 4 | 5 | 6 | VI-1 | Phf10 |
| 13201 | 3 | 4 | 5 | 6 | VI-1 | Phf11a |
| 13202 | 3 | 4 | 5 | 6 | VI-1 | Phf11b |
| 13203 | 3 | 4 | 5 | 6 | VI-1 | Phf11d |
| 13204 | 3 | 4 | 5 | 6 | VI-1 | Phf20 |
| 13205 | 3 | 4 | 5 | 6 | VI-1 | Phf20l1 |
| 13206 | 3 | 4 | 5 | 6 | VI-1 | Phf23 |
| 13207 | 3 | 4 | 5 | 6 | VI-1 | Phf3 |
| 13208 | 3 | 4 | 5 | 6 | VI-1 | Phf5a |
| 13209 | 3 | 4 | 5 | 6 | VI-1 | Phf8 |
| 13210 | 3 | 4 | 5 | 6 | VI-1 | Phgdh |
| 13211 | 3 | 4 | 5 | 6 | VI-1 | Phgr1 |
| 13212 | 3 | 4 | 5 | 6 | VI-1 | Phip |
| 13213 | 3 | 4 | 5 | 6 | VI-1 | Phka2 |
| 13214 | 3 | 4 | 5 | 6 | VI-1 | Phkb |
| 13215 | 3 | 4 | 5 | 6 | VI-1 | Phkg1 |
| 13216 | 3 | 4 | 5 | 6 | VI-1 | Phlda1 |
| 13217 | 3 | 4 | 5 | 6 | VI-1 | Phlda3 |
| 13218 | 3 | 4 | 5 | 6 | VI-1 | Phldb3 |
| 13219 | 3 | 4 | 5 | 6 | VI-1 | Phlpp2 |
| 13220 | 3 | 4 | 5 | 6 | VI-1 | Phospho1 |
| 13221 | 3 | 4 | 5 | 6 | VI-1 | Phox2a |
| 13222 | 3 | 4 | 5 | 6 | VI-1 | Phtf1 |
| 13223 | 3 | 4 | 5 | 6 | VI-1 | Phtf1os |
| 13224 | 3 | 4 | 5 | 6 | VI-1 | Phtf2 |
| 13225 | 3 | 4 | 5 | 6 | VI-1 | Pi4k2a |
| 13226 | 3 | 4 | 5 | 6 | VI-1 | Pi4k2b |
| 13227 | 3 | 4 | 5 | 6 | VI-1 | Pi4ka |
| 13228 | 3 | 4 | 5 | 6 | VI-1 | Pias1 |
| 13229 | 3 | 4 | 5 | 6 | VI-1 | Pias3 |
| 13230 | 3 | 4 | 5 | 6 | VI-1 | Pias4 |
| 13231 | 3 | 4 | 5 | 6 | VI-1 | Pibf1 |
| 13232 | 3 | 4 | 5 | 6 | VI-1 | Picalm |
| 13233 | 3 | 4 | 5 | 6 | VI-1 | Pick1 |
| 13234 | 3 | 4 | 5 | 6 | VI-1 | Pid1 |
| 13235 | 3 | 4 | 5 | 6 | VI-1 | Pifo |
| 13236 | 3 | 4 | 5 | 6 | VI-1 | Piga |
| 13237 | 3 | 4 | 5 | 6 | VI-1 | Pigm |
| 13238 | 3 | 4 | 5 | 6 | VI-1 | Pigo |
| 13239 | 3 | 4 | 5 | 6 | VI-1 | Pigq |
| 13240 | 3 | 4 | 5 | 6 | VI-1 | Pigs |
| 13241 | 3 | 4 | 5 | 6 | VI-1 | Pigt |
| 13242 | 3 | 4 | 5 | 6 | VI-1 | Pigv |
| 13243 | 3 | 4 | 5 | 6 | VI-1 | Pigz |
| 13244 | 3 | 4 | 5 | 6 | VI-1 | Pik3c2a |
| 13245 | 3 | 4 | 5 | 6 | VI-1 | Pik3c3 |
| 13246 | 3 | 4 | 5 | 6 | VI-1 | Pik3cb |

Fig. 34 - 70

| | | | | | | |
|---|---|---|---|---|---|---|
| 13247 | 3 | 4 | 5 | 6 | VI-1 | Pik3ip1 |
| 13248 | 3 | 4 | 5 | 6 | VI-1 | Pik3r2 |
| 13249 | 3 | 4 | 5 | 6 | VI-1 | Pilrb1 |
| 13250 | 3 | 4 | 5 | 6 | VI-1 | Pilrb2 |
| 13251 | 3 | 4 | 5 | 6 | VI-1 | Pim2 |
| 13252 | 3 | 4 | 5 | 6 | VI-1 | Pim3 |
| 13253 | 3 | 4 | 5 | 6 | VI-1 | Pink1 |
| 13254 | 3 | 4 | 5 | 6 | VI-1 | Pinx1 |
| 13255 | 3 | 4 | 5 | 6 | VI-1 | Pipox |
| 13256 | 3 | 4 | 5 | 6 | VI-1 | Pira2 |
| 13257 | 3 | 4 | 5 | 6 | VI-1 | Pirb |
| 13258 | 3 | 4 | 5 | 6 | VI-1 | Pisd-ps1 |
| 13259 | 3 | 4 | 5 | 6 | VI-1 | Pithd1 |
| 13260 | 3 | 4 | 5 | 6 | VI-1 | Pitpna |
| 13261 | 3 | 4 | 5 | 6 | VI-1 | Pitpnb |
| 13262 | 3 | 4 | 5 | 6 | VI-1 | Pitpnc1 |
| 13263 | 3 | 4 | 5 | 6 | VI-1 | Pitrm1 |
| 13264 | 3 | 4 | 5 | 6 | VI-1 | Pitx2 |
| 13265 | 3 | 4 | 5 | 6 | VI-1 | Pitx3 |
| 13266 | 3 | 4 | 5 | 6 | VI-1 | Piwil1 |
| 13267 | 3 | 4 | 5 | 6 | VI-1 | Pkd2l1 |
| 13268 | 3 | 4 | 5 | 6 | VI-1 | Pkd2l2 |
| 13269 | 3 | 4 | 5 | 6 | VI-1 | Pkib |
| 13270 | 3 | 4 | 5 | 6 | VI-1 | Pkm |
| 13271 | 3 | 4 | 5 | 6 | VI-1 | Pkn2 |
| 13272 | 3 | 4 | 5 | 6 | VI-1 | Pkn3 |
| 13273 | 3 | 4 | 5 | 6 | VI-1 | Pknox2 |
| 13274 | 3 | 4 | 5 | 6 | VI-1 | Pkp2 |
| 13275 | 3 | 4 | 5 | 6 | VI-1 | Pkp3 |
| 13276 | 3 | 4 | 5 | 6 | VI-1 | Pkp4 |
| 13277 | 3 | 4 | 5 | 6 | VI-1 | Pla1a |
| 13278 | 3 | 4 | 5 | 6 | VI-1 | Pla2g10os |
| 13279 | 3 | 4 | 5 | 6 | VI-1 | Pla2g16 |
| 13280 | 3 | 4 | 5 | 6 | VI-1 | Pla2g2a |
| 13281 | 3 | 4 | 5 | 6 | VI-1 | Pla2g2c |
| 13282 | 3 | 4 | 5 | 6 | VI-1 | Pla2g2e |
| 13283 | 3 | 4 | 5 | 6 | VI-1 | Pla2g4b |
| 13284 | 3 | 4 | 5 | 6 | VI-1 | Pla2g4f |
| 13285 | 3 | 4 | 5 | 6 | VI-1 | Pla2g5 |
| 13286 | 3 | 4 | 5 | 6 | VI-1 | Pla2g6 |
| 13287 | 3 | 4 | 5 | 6 | VI-1 | Pla2g7 |
| 13288 | 3 | 4 | 5 | 6 | VI-1 | Plaa |
| 13289 | 3 | 4 | 5 | 6 | VI-1 | Plac8 |
| 13290 | 3 | 4 | 5 | 6 | VI-1 | Plat |
| 13291 | 3 | 4 | 5 | 6 | VI-1 | Plbd1 |
| 13292 | 3 | 4 | 5 | 6 | VI-1 | Plbd2 |
| 13293 | 3 | 4 | 5 | 6 | VI-1 | Plcb1 |
| 13294 | 3 | 4 | 5 | 6 | VI-1 | Plcb4 |
| 13295 | 3 | 4 | 5 | 6 | VI-1 | Plcd3 |
| 13296 | 3 | 4 | 5 | 6 | VI-1 | Plcd4 |
| 13297 | 3 | 4 | 5 | 6 | VI-1 | Plce1 |
| 13298 | 3 | 4 | 5 | 6 | VI-1 | Plcg2 |
| 13299 | 3 | 4 | 5 | 6 | VI-1 | Plch2 |
| 13300 | 3 | 4 | 5 | 6 | VI-1 | Plcxd1 |
| 13301 | 3 | 4 | 5 | 6 | VI-1 | Pld6 |
| 13302 | 3 | 4 | 5 | 6 | VI-1 | Plek2 |
| 13303 | 3 | 4 | 5 | 6 | VI-1 | Plekha1 |
| 13304 | 3 | 4 | 5 | 6 | VI-1 | Plekha3 |
| 13305 | 3 | 4 | 5 | 6 | VI-1 | Plekha4 |
| 13306 | 3 | 4 | 5 | 6 | VI-1 | Plekha5 |
| 13307 | 3 | 4 | 5 | 6 | VI-1 | Plekhd1 |
| 13308 | 3 | 4 | 5 | 6 | VI-1 | Plekhg5 |
| 13309 | 3 | 4 | 5 | 6 | VI-1 | Plekhh3 |
| 13310 | 3 | 4 | 5 | 6 | VI-1 | Plekhj1 |
| 13311 | 3 | 4 | 5 | 6 | VI-1 | Plekhm1 |
| 13312 | 3 | 4 | 5 | 6 | VI-1 | Plekhm3 |
| 13313 | 3 | 4 | 5 | 6 | VI-1 | Plekho1 |
| 13314 | 3 | 4 | 5 | 6 | VI-1 | Plekhs1 |
| 13315 | 3 | 4 | 5 | 6 | VI-1 | Plet1 |
| 13316 | 3 | 4 | 5 | 6 | VI-1 | Plgrkt |
| 13317 | 3 | 4 | 5 | 6 | VI-1 | Plin1 |
| 13318 | 3 | 4 | 5 | 6 | VI-1 | Plin2 |
| 13319 | 3 | 4 | 5 | 6 | VI-1 | Plin3 |
| 13320 | 3 | 4 | 5 | 6 | VI-1 | Plin4 |
| 13321 | 3 | 4 | 5 | 6 | VI-1 | Plk2 |
| 13322 | 3 | 4 | 5 | 6 | VI-1 | Plk5 |
| 13323 | 3 | 4 | 5 | 6 | VI-1 | Pllp |
| 13324 | 3 | 4 | 5 | 6 | VI-1 | Pln |
| 13325 | 3 | 4 | 5 | 6 | VI-1 | Plod1 |
| 13326 | 3 | 4 | 5 | 6 | VI-1 | Plod3 |
| 13327 | 3 | 4 | 5 | 6 | VI-1 | Pls1 |
| 13328 | 3 | 4 | 5 | 6 | VI-1 | Pls3 |
| 13329 | 3 | 4 | 5 | 6 | VI-1 | Plxnb2 |
| 13330 | 3 | 4 | 5 | 6 | VI-1 | Pmch |
| 13331 | 3 | 4 | 5 | 6 | VI-1 | Pmel |
| 13332 | 3 | 4 | 5 | 6 | VI-1 | Pmepa1 |
| 13333 | 3 | 4 | 5 | 6 | VI-1 | Pmis2 |
| 13334 | 3 | 4 | 5 | 6 | VI-1 | Pmp22 |
| 13335 | 3 | 4 | 5 | 6 | VI-1 | Pms2 |
| 13336 | 3 | 4 | 5 | 6 | VI-1 | Pnck |
| 13337 | 3 | 4 | 5 | 6 | VI-1 | Pnkd |
| 13338 | 3 | 4 | 5 | 6 | VI-1 | Pnkp |
| 13339 | 3 | 4 | 5 | 6 | VI-1 | Pnmal1 |
| 13340 | 3 | 4 | 5 | 6 | VI-1 | Pnmt |
| 13341 | 3 | 4 | 5 | 6 | VI-1 | Pno1 |
| 13342 | 3 | 4 | 5 | 6 | VI-1 | Pnp |
| 13343 | 3 | 4 | 5 | 6 | VI-1 | Pnpla2 |
| 13344 | 3 | 4 | 5 | 6 | VI-1 | Pnpla8 |
| 13345 | 3 | 4 | 5 | 6 | VI-1 | Pnpo |
| 13346 | 3 | 4 | 5 | 6 | VI-1 | Pnrc1 |
| 13347 | 3 | 4 | 5 | 6 | VI-1 | Poc5 |
| 13348 | 3 | 4 | 5 | 6 | VI-1 | Podnl1 |
| 13349 | 3 | 4 | 5 | 6 | VI-1 | Podxl2 |
| 13350 | 3 | 4 | 5 | 6 | VI-1 | Pola2 |
| 13351 | 3 | 4 | 5 | 6 | VI-1 | Polb |
| 13352 | 3 | 4 | 5 | 6 | VI-1 | Pold1 |
| 13353 | 3 | 4 | 5 | 6 | VI-1 | Pold3 |
| 13354 | 3 | 4 | 5 | 6 | VI-1 | Pold4 |
| 13355 | 3 | 4 | 5 | 6 | VI-1 | Polg |
| 13356 | 3 | 4 | 5 | 6 | VI-1 | Polg2 |
| 13357 | 3 | 4 | 5 | 6 | VI-1 | Poli |
| 13358 | 3 | 4 | 5 | 6 | VI-1 | Poll |
| 13359 | 3 | 4 | 5 | 6 | VI-1 | Polr1a |
| 13360 | 3 | 4 | 5 | 6 | VI-1 | Polr1c |
| 13361 | 3 | 4 | 5 | 6 | VI-1 | Polr1d |
| 13362 | 3 | 4 | 5 | 6 | VI-1 | Polr1e |
| 13363 | 3 | 4 | 5 | 6 | VI-1 | Polr2d |
| 13364 | 3 | 4 | 5 | 6 | VI-1 | Polr2g |
| 13365 | 3 | 4 | 5 | 6 | VI-1 | Polr2h |
| 13366 | 3 | 4 | 5 | 6 | VI-1 | Polr2j |
| 13367 | 3 | 4 | 5 | 6 | VI-1 | Polr2k |
| 13368 | 3 | 4 | 5 | 6 | VI-1 | Polr3a |
| 13369 | 3 | 4 | 5 | 6 | VI-1 | Polr3b |
| 13370 | 3 | 4 | 5 | 6 | VI-1 | Polr3f |
| 13371 | 3 | 4 | 5 | 6 | VI-1 | Polr3gl |
| 13372 | 3 | 4 | 5 | 6 | VI-1 | Polr3h |
| 13373 | 3 | 4 | 5 | 6 | VI-1 | Pomgnt1 |
| 13374 | 3 | 4 | 5 | 6 | VI-1 | Pomgnt2 |
| 13375 | 3 | 4 | 5 | 6 | VI-1 | Pomt1 |
| 13376 | 3 | 4 | 5 | 6 | VI-1 | Pon1 |
| 13377 | 3 | 4 | 5 | 6 | VI-1 | Pon2 |
| 13378 | 3 | 4 | 5 | 6 | VI-1 | Pon3 |
| 13379 | 3 | 4 | 5 | 6 | VI-1 | Pop4 |
| 13380 | 3 | 4 | 5 | 6 | VI-1 | Pop7 |
| 13381 | 3 | 4 | 5 | 6 | VI-1 | Popdc2 |
| 13382 | 3 | 4 | 5 | 6 | VI-1 | Popdc3 |
| 13383 | 3 | 4 | 5 | 6 | VI-1 | Porcn |
| 13384 | 3 | 4 | 5 | 6 | VI-1 | Poteg |
| 13385 | 3 | 4 | 5 | 6 | VI-1 | Pou2af1 |
| 13386 | 3 | 4 | 5 | 6 | VI-1 | Pou2f2 |
| 13387 | 3 | 4 | 5 | 6 | VI-1 | Pou3f1 |
| 13388 | 3 | 4 | 5 | 6 | VI-1 | Pou3f3 |
| 13389 | 3 | 4 | 5 | 6 | VI-1 | Pou3f3os |
| 13390 | 3 | 4 | 5 | 6 | VI-1 | Pou5f1 |
| 13391 | 3 | 4 | 5 | 6 | VI-1 | Ppap2a |
| 13392 | 3 | 4 | 5 | 6 | VI-1 | Ppap2c |
| 13393 | 3 | 4 | 5 | 6 | VI-1 | Ppapdc2 |
| 13394 | 3 | 4 | 5 | 6 | VI-1 | Ppapdc3 |
| 13395 | 3 | 4 | 5 | 6 | VI-1 | Ppard |
| 13396 | 3 | 4 | 5 | 6 | VI-1 | Ppargc1b |
| 13397 | 3 | 4 | 5 | 6 | VI-1 | Ppat |
| 13398 | 3 | 4 | 5 | 6 | VI-1 | Ppbp |
| 13399 | 3 | 4 | 5 | 6 | VI-1 | Ppcs |
| 13400 | 3 | 4 | 5 | 6 | VI-1 | Ppfia3 |
| 13401 | 3 | 4 | 5 | 6 | VI-1 | Ppfia4 |
| 13402 | 3 | 4 | 5 | 6 | VI-1 | Ppfibp1 |
| 13403 | 3 | 4 | 5 | 6 | VI-1 | Ppfibp2 |
| 13404 | 3 | 4 | 5 | 6 | VI-1 | Ppia |
| 13405 | 3 | 4 | 5 | 6 | VI-1 | Ppib |
| 13406 | 3 | 4 | 5 | 6 | VI-1 | Ppic |
| 13407 | 3 | 4 | 5 | 6 | VI-1 | Ppid |
| 13408 | 3 | 4 | 5 | 6 | VI-1 | Ppif |
| 13409 | 3 | 4 | 5 | 6 | VI-1 | Ppil3 |
| 13410 | 3 | 4 | 5 | 6 | VI-1 | Ppil4 |
| 13411 | 3 | 4 | 5 | 6 | VI-1 | Ppip5k2 |
| 13412 | 3 | 4 | 5 | 6 | VI-1 | Ppl |
| 13413 | 3 | 4 | 5 | 6 | VI-1 | Ppm1d |
| 13414 | 3 | 4 | 5 | 6 | VI-1 | Ppm1h |
| 13415 | 3 | 4 | 5 | 6 | VI-1 | Ppm1j |
| 13416 | 3 | 4 | 5 | 6 | VI-1 | Ppm1k |
| 13417 | 3 | 4 | 5 | 6 | VI-1 | Ppm1l |
| 13418 | 3 | 4 | 5 | 6 | VI-1 | Ppm1m |
| 13419 | 3 | 4 | 5 | 6 | VI-1 | Ppp1cb |
| 13420 | 3 | 4 | 5 | 6 | VI-1 | Ppp1r10 |
| 13421 | 3 | 4 | 5 | 6 | VI-1 | Ppp1r12a |
| 13422 | 3 | 4 | 5 | 6 | VI-1 | Ppp1r12b |
| 13423 | 3 | 4 | 5 | 6 | VI-1 | Ppp1r13b |
| 13424 | 3 | 4 | 5 | 6 | VI-1 | Ppp1r14a |
| 13425 | 3 | 4 | 5 | 6 | VI-1 | Ppp1r14b |
| 13426 | 3 | 4 | 5 | 6 | VI-1 | Ppp1r15a |
| 13427 | 3 | 4 | 5 | 6 | VI-1 | Ppp1r15b |
| 13428 | 3 | 4 | 5 | 6 | VI-1 | Ppp1r16b |
| 13429 | 3 | 4 | 5 | 6 | VI-1 | Ppp1r18 |
| 13430 | 3 | 4 | 5 | 6 | VI-1 | Ppp1r21 |
| 13431 | 3 | 4 | 5 | 6 | VI-1 | Ppp1r32 |
| 13432 | 3 | 4 | 5 | 6 | VI-1 | Ppp1r35 |
| 13433 | 3 | 4 | 5 | 6 | VI-1 | Ppp1r36 |
| 13434 | 3 | 4 | 5 | 6 | VI-1 | Ppp1r37 |
| 13435 | 3 | 4 | 5 | 6 | VI-1 | Ppp1r3a |
| 13436 | 3 | 4 | 5 | 6 | VI-1 | Ppp1r42 |
| 13437 | 3 | 4 | 5 | 6 | VI-1 | Ppp1r7 |
| 13438 | 3 | 4 | 5 | 6 | VI-1 | Ppp1r9a |

Fig. 34 - 71

| | | | | | | | |
|---|---|---|---|---|---|---|---|
| 13439 | 3 | 4 | 5 | 6 | | VI-1 | Ppp2r1b |
| 13440 | 3 | 4 | 5 | 6 | | VI-1 | Ppp2r2b |
| 13441 | 3 | 4 | 5 | 6 | | VI-1 | Ppp2r3a |
| 13442 | 3 | 4 | 5 | 6 | | VI-1 | Ppp2r3c |
| 13443 | 3 | 4 | 5 | 6 | | VI-1 | Ppp2r4 |
| 13444 | 3 | 4 | 5 | 6 | | VI-1 | Ppp2r5a |
| 13445 | 3 | 4 | 5 | 6 | | VI-1 | Ppp2r5d |
| 13446 | 3 | 4 | 5 | 6 | | VI-1 | Ppp3cc |
| 13447 | 3 | 4 | 5 | 6 | | VI-1 | Ppp4r1 |
| 13448 | 3 | 4 | 5 | 6 | | VI-1 | Ppp6r1 |
| 13449 | 3 | 4 | 5 | 6 | | VI-1 | Pprc1 |
| 13450 | 3 | 4 | 5 | 6 | | VI-1 | Pptc7 |
| 13451 | 3 | 4 | 5 | 6 | | VI-1 | Ppy |
| 13452 | 3 | 4 | 5 | 6 | | VI-1 | Pqlc1 |
| 13453 | 3 | 4 | 5 | 6 | | VI-1 | Pqlc2 |
| 13454 | 3 | 4 | 5 | 6 | | VI-1 | Pqlc3 |
| 13455 | 3 | 4 | 5 | 6 | | VI-1 | Pradc1 |
| 13456 | 3 | 4 | 5 | 6 | | VI-1 | Praf2 |
| 13457 | 3 | 4 | 5 | 6 | | VI-1 | Pram1 |
| 13458 | 3 | 4 | 5 | 6 | | VI-1 | Prcc |
| 13459 | 3 | 4 | 5 | 6 | | VI-1 | Prdm11 |
| 13460 | 3 | 4 | 5 | 6 | | VI-1 | Prdm2 |
| 13461 | 3 | 4 | 5 | 6 | | VI-1 | Prdm4 |
| 13462 | 3 | 4 | 5 | 6 | | VI-1 | Prdm5 |
| 13463 | 3 | 4 | 5 | 6 | | VI-1 | Prdx1 |
| 13464 | 3 | 4 | 5 | 6 | | VI-1 | Prdx4 |
| 13465 | 3 | 4 | 5 | 6 | | VI-1 | Prdx6 |
| 13466 | 3 | 4 | 5 | 6 | | VI-1 | Preb |
| 13467 | 3 | 4 | 5 | 6 | | VI-1 | Prelid1 |
| 13468 | 3 | 4 | 5 | 6 | | VI-1 | Prelid2 |
| 13469 | 3 | 4 | 5 | 6 | | VI-1 | Prex1 |
| 13470 | 3 | 4 | 5 | 6 | | VI-1 | Prg3 |
| 13471 | 3 | 4 | 5 | 6 | | VI-1 | Prickle2 |
| 13472 | 3 | 4 | 5 | 6 | | VI-1 | Prickle3 |
| 13473 | 3 | 4 | 5 | 6 | | VI-1 | Prim2 |
| 13474 | 3 | 4 | 5 | 6 | | VI-1 | Prkaa2 |
| 13475 | 3 | 4 | 5 | 6 | | VI-1 | Prkag1 |
| 13476 | 3 | 4 | 5 | 6 | | VI-1 | Prkag2 |
| 13477 | 3 | 4 | 5 | 6 | | VI-1 | Prkag3 |
| 13478 | 3 | 4 | 5 | 6 | | VI-1 | Prkcd |
| 13479 | 3 | 4 | 5 | 6 | | VI-1 | Prkcdbp |
| 13480 | 3 | 4 | 5 | 6 | | VI-1 | Prkcq |
| 13481 | 3 | 4 | 5 | 6 | | VI-1 | Prkd1 |
| 13482 | 3 | 4 | 5 | 6 | | VI-1 | Prkd3 |
| 13483 | 3 | 4 | 5 | 6 | | VI-1 | Prkra |
| 13484 | 3 | 4 | 5 | 6 | | VI-1 | Prkrir |
| 13485 | 3 | 4 | 5 | 6 | | VI-1 | Prlh |
| 13486 | 3 | 4 | 5 | 6 | | VI-1 | Prlr |
| 13487 | 3 | 4 | 5 | 6 | | VI-1 | Prmt1 |
| 13488 | 3 | 4 | 5 | 6 | | VI-1 | Prmt10 |
| 13489 | 3 | 4 | 5 | 6 | | VI-1 | Prmt3 |
| 13490 | 3 | 4 | 5 | 6 | | VI-1 | Prmt7 |
| 13491 | 3 | 4 | 5 | 6 | | VI-1 | Prmt8 |
| 13492 | 3 | 4 | 5 | 6 | | VI-1 | Prnd |
| 13493 | 3 | 4 | 5 | 6 | | VI-1 | Prob1 |
| 13494 | 3 | 4 | 5 | 6 | | VI-1 | Proc |
| 13495 | 3 | 4 | 5 | 6 | | VI-1 | Proca1 |
| 13496 | 3 | 4 | 5 | 6 | | VI-1 | Prodh |
| 13497 | 3 | 4 | 5 | 6 | | VI-1 | Prom1 |
| 13498 | 3 | 4 | 5 | 6 | | VI-1 | Pros1 |
| 13499 | 3 | 4 | 5 | 6 | | VI-1 | Prosc |
| 13500 | 3 | 4 | 5 | 6 | | VI-1 | Prpf18 |
| 13501 | 3 | 4 | 5 | 6 | | VI-1 | Prpf3 |
| 13502 | 3 | 4 | 5 | 6 | | VI-1 | Prpf31 |
| 13503 | 3 | 4 | 5 | 6 | | VI-1 | Prpf38b |
| 13504 | 3 | 4 | 5 | 6 | | VI-1 | Prpf39 |
| 13505 | 3 | 4 | 5 | 6 | | VI-1 | Prpf4 |
| 13506 | 3 | 4 | 5 | 6 | | VI-1 | Prpf40a |
| 13507 | 3 | 4 | 5 | 6 | | VI-1 | Prpf4b |
| 13508 | 3 | 4 | 5 | 6 | | VI-1 | Prps1 |
| 13509 | 3 | 4 | 5 | 6 | | VI-1 | Prps1l3 |
| 13510 | 3 | 4 | 5 | 6 | | VI-1 | Prpsap2 |
| 13511 | 3 | 4 | 5 | 6 | | VI-1 | Prr14 |
| 13512 | 3 | 4 | 5 | 6 | | VI-1 | Prr14l |
| 13513 | 3 | 4 | 5 | 6 | | VI-1 | Prr15 |
| 13514 | 3 | 4 | 5 | 6 | | VI-1 | Prr18 |
| 13515 | 3 | 4 | 5 | 6 | | VI-1 | Prr24 |
| 13516 | 3 | 4 | 5 | 6 | | VI-1 | Prr5 |
| 13517 | 3 | 4 | 5 | 6 | | VI-1 | Prr7 |
| 13518 | 3 | 4 | 5 | 6 | | VI-1 | Prrc1 |
| 13519 | 3 | 4 | 5 | 6 | | VI-1 | Prrc2a |
| 13520 | 3 | 4 | 5 | 6 | | VI-1 | Prrg3 |
| 13521 | 3 | 4 | 5 | 6 | | VI-1 | Prrg4 |
| 13522 | 3 | 4 | 5 | 6 | | VI-1 | Prrt1 |
| 13523 | 3 | 4 | 5 | 6 | | VI-1 | Prrt3 |
| 13524 | 3 | 4 | 5 | 6 | | VI-1 | Prss1 |
| 13525 | 3 | 4 | 5 | 6 | | VI-1 | Prss12 |
| 13526 | 3 | 4 | 5 | 6 | | VI-1 | Prss16 |
| 13527 | 3 | 4 | 5 | 6 | | VI-1 | Prss23 |
| 13528 | 3 | 4 | 5 | 6 | | VI-1 | Prss29 |
| 13529 | 3 | 4 | 5 | 6 | | VI-1 | Prss32 |
| 13530 | 3 | 4 | 5 | 6 | | VI-1 | Prss34 |
| 13531 | 3 | 4 | 5 | 6 | | VI-1 | Prss36 |
| 13532 | 3 | 4 | 5 | 6 | | VI-1 | Prss38 |
| 13533 | 3 | 4 | 5 | 6 | | VI-1 | Prss39 |
| 13534 | 3 | 4 | 5 | 6 | | VI-1 | Prss41 |
| 13535 | 3 | 4 | 5 | 6 | | VI-1 | Prss50 |
| 13536 | 3 | 4 | 5 | 6 | | VI-1 | Prss56 |
| 13537 | 3 | 4 | 5 | 6 | | VI-1 | Prss57 |
| 13538 | 3 | 4 | 5 | 6 | | VI-1 | Prss8 |
| 13539 | 3 | 4 | 5 | 6 | | VI-1 | Prx |
| 13540 | 3 | 4 | 5 | 6 | | VI-1 | Psap |
| 13541 | 3 | 4 | 5 | 6 | | VI-1 | Psat1 |
| 13542 | 3 | 4 | 5 | 6 | | VI-1 | Psd |
| 13543 | 3 | 4 | 5 | 6 | | VI-1 | Psen1 |
| 13544 | 3 | 4 | 5 | 6 | | VI-1 | Psip1 |
| 13545 | 3 | 4 | 5 | 6 | | VI-1 | Psma1 |
| 13546 | 3 | 4 | 5 | 6 | | VI-1 | Psma2 |
| 13547 | 3 | 4 | 5 | 6 | | VI-1 | Psma3 |
| 13548 | 3 | 4 | 5 | 6 | | VI-1 | Psma8 |
| 13549 | 3 | 4 | 5 | 6 | | VI-1 | Psmb2 |
| 13550 | 3 | 4 | 5 | 6 | | VI-1 | Psmb4 |
| 13551 | 3 | 4 | 5 | 6 | | VI-1 | Psmb5 |
| 13552 | 3 | 4 | 5 | 6 | | VI-1 | Psmc3 |
| 13553 | 3 | 4 | 5 | 6 | | VI-1 | Psmc4 |
| 13554 | 3 | 4 | 5 | 6 | | VI-1 | Psmc6 |
| 13555 | 3 | 4 | 5 | 6 | | VI-1 | Psmd1 |
| 13556 | 3 | 4 | 5 | 6 | | VI-1 | Psmd10 |
| 13557 | 3 | 4 | 5 | 6 | | VI-1 | Psmd11 |
| 13558 | 3 | 4 | 5 | 6 | | VI-1 | Psmd14 |
| 13559 | 3 | 4 | 5 | 6 | | VI-1 | Psmd3 |
| 13560 | 3 | 4 | 5 | 6 | | VI-1 | Psmd6 |
| 13561 | 3 | 4 | 5 | 6 | | VI-1 | Psmd7 |
| 13562 | 3 | 4 | 5 | 6 | | VI-1 | Psmd8 |
| 13563 | 3 | 4 | 5 | 6 | | VI-1 | Psmd9 |
| 13564 | 3 | 4 | 5 | 6 | | VI-1 | Psme2 |
| 13565 | 3 | 4 | 5 | 6 | | VI-1 | Psme2b |
| 13566 | 3 | 4 | 5 | 6 | | VI-1 | Psme4 |
| 13567 | 3 | 4 | 5 | 6 | | VI-1 | Psmg1 |
| 13568 | 3 | 4 | 5 | 6 | | VI-1 | Psmg4 |
| 13569 | 3 | 4 | 5 | 6 | | VI-1 | Pstk |
| 13570 | 3 | 4 | 5 | 6 | | VI-1 | Ptar1 |
| 13571 | 3 | 4 | 5 | 6 | | VI-1 | Ptbp1 |
| 13572 | 3 | 4 | 5 | 6 | | VI-1 | Ptbp3 |
| 13573 | 3 | 4 | 5 | 6 | | VI-1 | Ptcd1 |
| 13574 | 3 | 4 | 5 | 6 | | VI-1 | Ptcd2 |
| 13575 | 3 | 4 | 5 | 6 | | VI-1 | Ptdss1 |
| 13576 | 3 | 4 | 5 | 6 | | VI-1 | Ptdss2 |
| 13577 | 3 | 4 | 5 | 6 | | VI-1 | Pten |
| 13578 | 3 | 4 | 5 | 6 | | VI-1 | Pter |
| 13579 | 3 | 4 | 5 | 6 | | VI-1 | Ptgdr |
| 13580 | 3 | 4 | 5 | 6 | | VI-1 | Ptgdr2 |
| 13581 | 3 | 4 | 5 | 6 | | VI-1 | Ptger2 |
| 13582 | 3 | 4 | 5 | 6 | | VI-1 | Ptger4 |
| 13583 | 3 | 4 | 5 | 6 | | VI-1 | Ptges |
| 13584 | 3 | 4 | 5 | 6 | | VI-1 | Ptges2 |
| 13585 | 3 | 4 | 5 | 6 | | VI-1 | Ptgr1 |
| 13586 | 3 | 4 | 5 | 6 | | VI-1 | Pthlh |
| 13587 | 3 | 4 | 5 | 6 | | VI-1 | Ptk2 |
| 13588 | 3 | 4 | 5 | 6 | | VI-1 | Ptk2b |
| 13589 | 3 | 4 | 5 | 6 | | VI-1 | Ptma |
| 13590 | 3 | 4 | 5 | 6 | | VI-1 | Ptms |
| 13591 | 3 | 4 | 5 | 6 | | VI-1 | Ptov1 |
| 13592 | 3 | 4 | 5 | 6 | | VI-1 | Ptp4a1 |
| 13593 | 3 | 4 | 5 | 6 | | VI-1 | Ptp4a2 |
| 13594 | 3 | 4 | 5 | 6 | | VI-1 | Ptp4a3 |
| 13595 | 3 | 4 | 5 | 6 | | VI-1 | Ptpla |
| 13596 | 3 | 4 | 5 | 6 | | VI-1 | Ptplad1 |
| 13597 | 3 | 4 | 5 | 6 | | VI-1 | Ptpib |
| 13598 | 3 | 4 | 5 | 6 | | VI-1 | Ptpmt1 |
| 13599 | 3 | 4 | 5 | 6 | | VI-1 | Ptpn13 |
| 13600 | 3 | 4 | 5 | 6 | | VI-1 | Ptpn14 |
| 13601 | 3 | 4 | 5 | 6 | | VI-1 | Ptpn2 |
| 13602 | 3 | 4 | 5 | 6 | | VI-1 | Ptpn21 |
| 13603 | 3 | 4 | 5 | 6 | | VI-1 | Ptpn22 |
| 13604 | 3 | 4 | 5 | 6 | | VI-1 | Ptprcap |
| 13605 | 3 | 4 | 5 | 6 | | VI-1 | Ptprd |
| 13606 | 3 | 4 | 5 | 6 | | VI-1 | Ptprk |
| 13607 | 3 | 4 | 5 | 6 | | VI-1 | Ptprm |
| 13608 | 3 | 4 | 5 | 6 | | VI-1 | Ptpro |
| 13609 | 3 | 4 | 5 | 6 | | VI-1 | Ptprr |
| 13610 | 3 | 4 | 5 | 6 | | VI-1 | Ptprs |
| 13611 | 3 | 4 | 5 | 6 | | VI-1 | Ptpru |
| 13612 | 3 | 4 | 5 | 6 | | VI-1 | Ptprv |
| 13613 | 3 | 4 | 5 | 6 | | VI-1 | Ptprz1 |
| 13614 | 3 | 4 | 5 | 6 | | VI-1 | Ptrf |
| 13615 | 3 | 4 | 5 | 6 | | VI-1 | Ptrh1 |
| 13616 | 3 | 4 | 5 | 6 | | VI-1 | Ptrh2 |
| 13617 | 3 | 4 | 5 | 6 | | VI-1 | Pts |
| 13618 | 3 | 4 | 5 | 6 | | VI-1 | Pttg1 |
| 13619 | 3 | 4 | 5 | 6 | | VI-1 | Puf60 |
| 13620 | 3 | 4 | 5 | 6 | | VI-1 | Pum2 |
| 13621 | 3 | 4 | 5 | 6 | | VI-1 | Pus1 |
| 13622 | 3 | 4 | 5 | 6 | | VI-1 | Pus3 |
| 13623 | 3 | 4 | 5 | 6 | | VI-1 | Pus7 |
| 13624 | 3 | 4 | 5 | 6 | | VI-1 | Pusl1 |
| 13625 | 3 | 4 | 5 | 6 | | VI-1 | Pvrl1 |
| 13626 | 3 | 4 | 5 | 6 | | VI-1 | Pvrl2 |
| 13627 | 3 | 4 | 5 | 6 | | VI-1 | Pvrl3 |
| 13628 | 3 | 4 | 5 | 6 | | VI-1 | Pvt1 |
| 13629 | 3 | 4 | 5 | 6 | | VI-1 | Pwp2 |
| 13630 | 3 | 4 | 5 | 6 | | VI-1 | Pwwp2a |

Fig. 34 - 72

| | | | | | | |
|---|---|---|---|---|---|---|
| 13631 | 3 | 4 | 5 | 6 | VI-1 | Pwwp2b |
| 13632 | 3 | 4 | 5 | 6 | VI-1 | Pxdc1 |
| 13633 | 3 | 4 | 5 | 6 | VI-1 | Pxdn |
| 13634 | 3 | 4 | 5 | 6 | VI-1 | Pxylp1 |
| 13635 | 3 | 4 | 5 | 6 | VI-1 | Pycr2 |
| 13636 | 3 | 4 | 5 | 6 | VI-1 | Pygl |
| 13637 | 3 | 4 | 5 | 6 | VI-1 | Pygm |
| 13638 | 3 | 4 | 5 | 6 | VI-1 | Pygo1 |
| 13639 | 3 | 4 | 5 | 6 | VI-1 | Pyhin1 |
| 13640 | 3 | 4 | 5 | 6 | VI-1 | Pyroxd1 |
| 13641 | 3 | 4 | 5 | 6 | VI-1 | Pyurf |
| 13642 | 3 | 4 | 5 | 6 | VI-1 | Qdpr |
| 13643 | 3 | 4 | 5 | 6 | VI-1 | Qk |
| 13644 | 3 | 4 | 5 | 6 | VI-1 | Qrfp |
| 13645 | 3 | 4 | 5 | 6 | VI-1 | Qrsl1 |
| 13646 | 3 | 4 | 5 | 6 | VI-1 | Qser1 |
| 13647 | 3 | 4 | 5 | 6 | VI-1 | Qsox1 |
| 13648 | 3 | 4 | 5 | 6 | VI-1 | R3hcc1 |
| 13649 | 3 | 4 | 5 | 6 | VI-1 | R3hdm1 |
| 13650 | 3 | 4 | 5 | 6 | VI-1 | R74862 |
| 13651 | 3 | 4 | 5 | 6 | VI-1 | Rab1 |
| 13652 | 3 | 4 | 5 | 6 | VI-1 | Rab11fip1 |
| 13653 | 3 | 4 | 5 | 6 | VI-1 | Rab11fip5 |
| 13654 | 3 | 4 | 5 | 6 | VI-1 | Rab22a |
| 13655 | 3 | 4 | 5 | 6 | VI-1 | Rab27a |
| 13656 | 3 | 4 | 5 | 6 | VI-1 | Rab31 |
| 13657 | 3 | 4 | 5 | 6 | VI-1 | Rab33a |
| 13658 | 3 | 4 | 5 | 6 | VI-1 | Rab33b |
| 13659 | 3 | 4 | 5 | 6 | VI-1 | Rab39b |
| 13660 | 3 | 4 | 5 | 6 | VI-1 | Rab3a |
| 13661 | 3 | 4 | 5 | 6 | VI-1 | Rab3d |
| 13662 | 3 | 4 | 5 | 6 | VI-1 | Rab3gap1 |
| 13663 | 3 | 4 | 5 | 6 | VI-1 | Rab3ip |
| 13664 | 3 | 4 | 5 | 6 | VI-1 | Rab43 |
| 13665 | 3 | 4 | 5 | 6 | VI-1 | Rab44 |
| 13666 | 3 | 4 | 5 | 6 | VI-1 | Rab4a |
| 13667 | 3 | 4 | 5 | 6 | VI-1 | Rab5a |
| 13668 | 3 | 4 | 5 | 6 | VI-1 | Rab5b |
| 13669 | 3 | 4 | 5 | 6 | VI-1 | Rab8a |
| 13670 | 3 | 4 | 5 | 6 | VI-1 | Rab8b |
| 13671 | 3 | 4 | 5 | 6 | VI-1 | Raben2 |
| 13672 | 3 | 4 | 5 | 6 | VI-1 | Rabepk |
| 13673 | 3 | 4 | 5 | 6 | VI-1 | Rabgef1 |
| 13674 | 3 | 4 | 5 | 6 | VI-1 | Rabggta |
| 13675 | 3 | 4 | 5 | 6 | VI-1 | Rabggtb |
| 13676 | 3 | 4 | 5 | 6 | VI-1 | Rabl2 |
| 13677 | 3 | 4 | 5 | 6 | VI-1 | Rabl6 |
| 13678 | 3 | 4 | 5 | 6 | VI-1 | Rac2 |
| 13679 | 3 | 4 | 5 | 6 | VI-1 | Rad17 |
| 13680 | 3 | 4 | 5 | 6 | VI-1 | Rad23a |
| 13681 | 3 | 4 | 5 | 6 | VI-1 | Rad51ap1 |
| 13682 | 3 | 4 | 5 | 6 | VI-1 | Rad51d |
| 13683 | 3 | 4 | 5 | 6 | VI-1 | Rad52 |
| 13684 | 3 | 4 | 5 | 6 | VI-1 | Rad54l2 |
| 13685 | 3 | 4 | 5 | 6 | VI-1 | Rad9b |
| 13686 | 3 | 4 | 5 | 6 | VI-1 | Ralb |
| 13687 | 3 | 4 | 5 | 6 | VI-1 | Ralgapa2 |
| 13688 | 3 | 4 | 5 | 6 | VI-1 | Ralgapb |
| 13689 | 3 | 4 | 5 | 6 | VI-1 | Ralgds |
| 13690 | 3 | 4 | 5 | 6 | VI-1 | Ralgps2 |
| 13691 | 3 | 4 | 5 | 6 | VI-1 | Raly |
| 13692 | 3 | 4 | 5 | 6 | VI-1 | Ralyl |
| 13693 | 3 | 4 | 5 | 6 | VI-1 | Ramp1 |
| 13694 | 3 | 4 | 5 | 6 | VI-1 | Ramp2 |
| 13695 | 3 | 4 | 5 | 6 | VI-1 | Ramp3 |
| 13696 | 3 | 4 | 5 | 6 | VI-1 | Ran |
| 13697 | 3 | 4 | 5 | 6 | VI-1 | Ranbp3 |
| 13698 | 3 | 4 | 5 | 6 | VI-1 | Ranbp6 |
| 13699 | 3 | 4 | 5 | 6 | VI-1 | Ranbp9 |
| 13700 | 3 | 4 | 5 | 6 | VI-1 | Rangap1 |
| 13701 | 3 | 4 | 5 | 6 | VI-1 | Rap1a |
| 13702 | 3 | 4 | 5 | 6 | VI-1 | Rap1gap |
| 13703 | 3 | 4 | 5 | 6 | VI-1 | Rapgef3 |
| 13704 | 3 | 4 | 5 | 6 | VI-1 | Rapgef4 |
| 13705 | 3 | 4 | 5 | 6 | VI-1 | Rapgef5 |
| 13706 | 3 | 4 | 5 | 6 | VI-1 | Rapgef6 |
| 13707 | 3 | 4 | 5 | 6 | VI-1 | Rapgefl1 |
| 13708 | 3 | 4 | 5 | 6 | VI-1 | Raph1 |
| 13709 | 3 | 4 | 5 | 6 | VI-1 | Rapsn |
| 13710 | 3 | 4 | 5 | 6 | VI-1 | Rara |
| 13711 | 3 | 4 | 5 | 6 | VI-1 | Rarres1 |
| 13712 | 3 | 4 | 5 | 6 | VI-1 | Rars2 |
| 13713 | 3 | 4 | 5 | 6 | VI-1 | Rasa2 |
| 13714 | 3 | 4 | 5 | 6 | VI-1 | Rasa4 |
| 13715 | 3 | 4 | 5 | 6 | VI-1 | Rasal1 |
| 13716 | 3 | 4 | 5 | 6 | VI-1 | Rasal2 |
| 13717 | 3 | 4 | 5 | 6 | VI-1 | Rasgef1a |
| 13718 | 3 | 4 | 5 | 6 | VI-1 | Rasgef1b |
| 13719 | 3 | 4 | 5 | 6 | VI-1 | Rasgef1c |
| 13720 | 3 | 4 | 5 | 6 | VI-1 | Rasgrf2 |
| 13721 | 3 | 4 | 5 | 6 | VI-1 | Rasgrp4 |
| 13722 | 3 | 4 | 5 | 6 | VI-1 | Rasl11a |
| 13723 | 3 | 4 | 5 | 6 | VI-1 | Rasl11b |
| 13724 | 3 | 4 | 5 | 6 | VI-1 | Rasl2 |
| 13725 | 3 | 4 | 5 | 6 | VI-1 | Rassf2 |
| 13726 | 3 | 4 | 5 | 6 | VI-1 | Rassf8 |
| 13727 | 3 | 4 | 5 | 6 | VI-1 | Rb1 |
| 13728 | 3 | 4 | 5 | 6 | VI-1 | Rb1cc1 |
| 13729 | 3 | 4 | 5 | 6 | VI-1 | Rbbp5 |
| 13730 | 3 | 4 | 5 | 6 | VI-1 | Rbbp6 |
| 13731 | 3 | 4 | 5 | 6 | VI-1 | Rbbp7 |
| 13732 | 3 | 4 | 5 | 6 | VI-1 | Rbbp8 |
| 13733 | 3 | 4 | 5 | 6 | VI-1 | Rbck1 |
| 13734 | 3 | 4 | 5 | 6 | VI-1 | Rbm10 |
| 13735 | 3 | 4 | 5 | 6 | VI-1 | Rbm12b1 |
| 13736 | 3 | 4 | 5 | 6 | VI-1 | Rbm14 |
| 13737 | 3 | 4 | 5 | 6 | VI-1 | Rbm14-rbm4 |
| 13738 | 3 | 4 | 5 | 6 | VI-1 | Rbm17 |
| 13739 | 3 | 4 | 5 | 6 | VI-1 | Rbm19 |
| 13740 | 3 | 4 | 5 | 6 | VI-1 | Rbm20 |
| 13741 | 3 | 4 | 5 | 6 | VI-1 | Rbm22 |
| 13742 | 3 | 4 | 5 | 6 | VI-1 | Rbm24 |
| 13743 | 3 | 4 | 5 | 6 | VI-1 | Rbm28 |
| 13744 | 3 | 4 | 5 | 6 | VI-1 | Rbm3 |
| 13745 | 3 | 4 | 5 | 6 | VI-1 | Rbm38 |
| 13746 | 3 | 4 | 5 | 6 | VI-1 | Rbm39 |
| 13747 | 3 | 4 | 5 | 6 | VI-1 | Rbm3os |
| 13748 | 3 | 4 | 5 | 6 | VI-1 | Rbm4 |
| 13749 | 3 | 4 | 5 | 6 | VI-1 | Rbm41 |
| 13750 | 3 | 4 | 5 | 6 | VI-1 | Rbm42 |
| 13751 | 3 | 4 | 5 | 6 | VI-1 | Rbm45 |
| 13752 | 3 | 4 | 5 | 6 | VI-1 | Rbm48 |
| 13753 | 3 | 4 | 5 | 6 | VI-1 | Rbm4b |
| 13754 | 3 | 4 | 5 | 6 | VI-1 | Rbm5 |
| 13755 | 3 | 4 | 5 | 6 | VI-1 | Rbm6 |
| 13756 | 3 | 4 | 5 | 6 | VI-1 | Rbm7 |
| 13757 | 3 | 4 | 5 | 6 | VI-1 | Rbm8a |
| 13758 | 3 | 4 | 5 | 6 | VI-1 | Rbp4 |
| 13759 | 3 | 4 | 5 | 6 | VI-1 | Rbpms |
| 13760 | 3 | 4 | 5 | 6 | VI-1 | Rbpms2 |
| 13761 | 3 | 4 | 5 | 6 | VI-1 | Rcan1 |
| 13762 | 3 | 4 | 5 | 6 | VI-1 | Rcan2 |
| 13763 | 3 | 4 | 5 | 6 | VI-1 | Rcbtb2 |
| 13764 | 3 | 4 | 5 | 6 | VI-1 | Rcc1 |
| 13765 | 3 | 4 | 5 | 6 | VI-1 | Rcc2 |
| 13766 | 3 | 4 | 5 | 6 | VI-1 | Rcl1 |
| 13767 | 3 | 4 | 5 | 6 | VI-1 | Rcn3 |
| 13768 | 3 | 4 | 5 | 6 | VI-1 | Rcor3 |
| 13769 | 3 | 4 | 5 | 6 | VI-1 | Rcsd1 |
| 13770 | 3 | 4 | 5 | 6 | VI-1 | Rdh11 |
| 13771 | 3 | 4 | 5 | 6 | VI-1 | Rdh12 |
| 13772 | 3 | 4 | 5 | 6 | VI-1 | Rdh13 |
| 13773 | 3 | 4 | 5 | 6 | VI-1 | Rdh18-ps |
| 13774 | 3 | 4 | 5 | 6 | VI-1 | Rdh7 |
| 13775 | 3 | 4 | 5 | 6 | VI-1 | Recql |
| 13776 | 3 | 4 | 5 | 6 | VI-1 | Recql5 |
| 13777 | 3 | 4 | 5 | 6 | VI-1 | Reep2 |
| 13778 | 3 | 4 | 5 | 6 | VI-1 | Reep5 |
| 13779 | 3 | 4 | 5 | 6 | VI-1 | Reg3d |
| 13780 | 3 | 4 | 5 | 6 | VI-1 | Reg4 |
| 13781 | 3 | 4 | 5 | 6 | VI-1 | Rela |
| 13782 | 3 | 4 | 5 | 6 | VI-1 | Rem2 |
| 13783 | 3 | 4 | 5 | 6 | VI-1 | Ren2 |
| 13784 | 3 | 4 | 5 | 6 | VI-1 | Reps1 |
| 13785 | 3 | 4 | 5 | 6 | VI-1 | Reps2 |
| 13786 | 3 | 4 | 5 | 6 | VI-1 | Rer1 |
| 13787 | 3 | 4 | 5 | 6 | VI-1 | Resp18 |
| 13788 | 3 | 4 | 5 | 6 | VI-1 | Retnlb |
| 13789 | 3 | 4 | 5 | 6 | VI-1 | Rex2 |
| 13790 | 3 | 4 | 5 | 6 | VI-1 | Rexo2 |
| 13791 | 3 | 4 | 5 | 6 | VI-1 | Rexo4 |
| 13792 | 3 | 4 | 5 | 6 | VI-1 | Rfc1 |
| 13793 | 3 | 4 | 5 | 6 | VI-1 | Rfc3 |
| 13794 | 3 | 4 | 5 | 6 | VI-1 | Rfc4 |
| 13795 | 3 | 4 | 5 | 6 | VI-1 | Rffl |
| 13796 | 3 | 4 | 5 | 6 | VI-1 | Rfk |
| 13797 | 3 | 4 | 5 | 6 | VI-1 | Rfng |
| 13798 | 3 | 4 | 5 | 6 | VI-1 | Rft1 |
| 13799 | 3 | 4 | 5 | 6 | VI-1 | Rftn2 |
| 13800 | 3 | 4 | 5 | 6 | VI-1 | Rfwd2 |
| 13801 | 3 | 4 | 5 | 6 | VI-1 | Rfx1 |
| 13802 | 3 | 4 | 5 | 6 | VI-1 | Rfx2 |
| 13803 | 3 | 4 | 5 | 6 | VI-1 | Rfx5 |
| 13804 | 3 | 4 | 5 | 6 | VI-1 | Rfxap |
| 13805 | 3 | 4 | 5 | 6 | VI-1 | Rgcc |
| 13806 | 3 | 4 | 5 | 6 | VI-1 | Rgl3 |
| 13807 | 3 | 4 | 5 | 6 | VI-1 | Rgma |
| 13808 | 3 | 4 | 5 | 6 | VI-1 | Rgs10 |
| 13809 | 3 | 4 | 5 | 6 | VI-1 | Rgs11 |
| 13810 | 3 | 4 | 5 | 6 | VI-1 | Rgs14 |
| 13811 | 3 | 4 | 5 | 6 | VI-1 | Rgs16 |
| 13812 | 3 | 4 | 5 | 6 | VI-1 | Rgs19 |
| 13813 | 3 | 4 | 5 | 6 | VI-1 | Rgs5 |
| 13814 | 3 | 4 | 5 | 6 | VI-1 | Rgs7 |
| 13815 | 3 | 4 | 5 | 6 | VI-1 | Rgs9 |
| 13816 | 3 | 4 | 5 | 6 | VI-1 | Rhbdd1 |
| 13817 | 3 | 4 | 5 | 6 | VI-1 | Rhbdf1 |
| 13818 | 3 | 4 | 5 | 6 | VI-1 | Rhebl1 |
| 13819 | 3 | 4 | 5 | 6 | VI-1 | Rhobtb1 |
| 13820 | 3 | 4 | 5 | 6 | VI-1 | Rhoc |
| 13821 | 3 | 4 | 5 | 6 | VI-1 | Rhod |
| 13822 | 3 | 4 | 5 | 6 | VI-1 | Rhof |

Fig. 34 - 73

| | | | | | | | |
|---|---|---|---|---|---|---|---|
| 13823 | 3 | 4 | 5 | 6 | | VI-1 | Rhog |
| 13824 | 3 | 4 | 5 | 6 | | VI-1 | Rhoj |
| 13825 | 3 | 4 | 5 | 6 | | VI-1 | Rhot2 |
| 13826 | 3 | 4 | 5 | 6 | | VI-1 | Rhov |
| 13827 | 3 | 4 | 5 | 6 | | VI-1 | Rhox10 |
| 13828 | 3 | 4 | 5 | 6 | | VI-1 | Rhox4a |
| 13829 | 3 | 4 | 5 | 6 | | VI-1 | Rhox5 |
| 13830 | 3 | 4 | 5 | 6 | | VI-1 | Rhox6 |
| 13831 | 3 | 4 | 5 | 6 | | VI-1 | Rhpn2 |
| 13832 | 3 | 4 | 5 | 6 | | VI-1 | Ric3 |
| 13833 | 3 | 4 | 5 | 6 | | VI-1 | Ric8 |
| 13834 | 3 | 4 | 5 | 6 | | VI-1 | Rif1 |
| 13835 | 3 | 4 | 5 | 6 | | VI-1 | Rilp |
| 13836 | 3 | 4 | 5 | 6 | | VI-1 | Rims1 |
| 13837 | 3 | 4 | 5 | 6 | | VI-1 | Rims2 |
| 13838 | 3 | 4 | 5 | 6 | | VI-1 | Rin2 |
| 13839 | 3 | 4 | 5 | 6 | | VI-1 | Rin3 |
| 13840 | 3 | 4 | 5 | 6 | | VI-1 | Rinl |
| 13841 | 3 | 4 | 5 | 6 | | VI-1 | Rint1 |
| 13842 | 3 | 4 | 5 | 6 | | VI-1 | Riok2 |
| 13843 | 3 | 4 | 5 | 6 | | VI-1 | Riok3 |
| 13844 | 3 | 4 | 5 | 6 | | VI-1 | Ripk3 |
| 13845 | 3 | 4 | 5 | 6 | | VI-1 | Ripk4 |
| 13846 | 3 | 4 | 5 | 6 | | VI-1 | Rit1 |
| 13847 | 3 | 4 | 5 | 6 | | VI-1 | Rita1 |
| 13848 | 3 | 4 | 5 | 6 | | VI-1 | Rlim |
| 13849 | 3 | 4 | 5 | 6 | | VI-1 | Rln3 |
| 13850 | 3 | 4 | 5 | 6 | | VI-1 | Rmdn1 |
| 13851 | 3 | 4 | 5 | 6 | | VI-1 | Rmnd5a |
| 13852 | 3 | 4 | 5 | 6 | | VI-1 | Rmnd5b |
| 13853 | 3 | 4 | 5 | 6 | | VI-1 | Rnase2b |
| 13854 | 3 | 4 | 5 | 6 | | VI-1 | Rnaseh2c |
| 13855 | 3 | 4 | 5 | 6 | | VI-1 | Rnd1 |
| 13856 | 3 | 4 | 5 | 6 | | VI-1 | Rnd2 |
| 13857 | 3 | 4 | 5 | 6 | | VI-1 | Rnf103 |
| 13858 | 3 | 4 | 5 | 6 | | VI-1 | Rnf113a2 |
| 13859 | 3 | 4 | 5 | 6 | | VI-1 | Rnf114 |
| 13860 | 3 | 4 | 5 | 6 | | VI-1 | Rnf121 |
| 13861 | 3 | 4 | 5 | 6 | | VI-1 | Rnf122 |
| 13862 | 3 | 4 | 5 | 6 | | VI-1 | Rnf126 |
| 13863 | 3 | 4 | 5 | 6 | | VI-1 | Rnf128 |
| 13864 | 3 | 4 | 5 | 6 | | VI-1 | Rnf133 |
| 13865 | 3 | 4 | 5 | 6 | | VI-1 | Rnf141 |
| 13866 | 3 | 4 | 5 | 6 | | VI-1 | Rnf144a |
| 13867 | 3 | 4 | 5 | 6 | | VI-1 | Rnf144b |
| 13868 | 3 | 4 | 5 | 6 | | VI-1 | Rnf149 |
| 13869 | 3 | 4 | 5 | 6 | | VI-1 | Rnf151 |
| 13870 | 3 | 4 | 5 | 6 | | VI-1 | Rnf166 |
| 13871 | 3 | 4 | 5 | 6 | | VI-1 | Rnf167 |
| 13872 | 3 | 4 | 5 | 6 | | VI-1 | Rnf169 |
| 13873 | 3 | 4 | 5 | 6 | | VI-1 | Rnf170 |
| 13874 | 3 | 4 | 5 | 6 | | VI-1 | Rnf182 |
| 13875 | 3 | 4 | 5 | 6 | | VI-1 | Rnf183 |
| 13876 | 3 | 4 | 5 | 6 | | VI-1 | Rnf2 |
| 13877 | 3 | 4 | 5 | 6 | | VI-1 | Rnf215 |
| 13878 | 3 | 4 | 5 | 6 | | VI-1 | Rnf220 |
| 13879 | 3 | 4 | 5 | 6 | | VI-1 | Rnf224 |
| 13880 | 3 | 4 | 5 | 6 | | VI-1 | Rnf31 |
| 13881 | 3 | 4 | 5 | 6 | | VI-1 | Rnf32 |
| 13882 | 3 | 4 | 5 | 6 | | VI-1 | Rnf4 |
| 13883 | 3 | 4 | 5 | 6 | | VI-1 | Rnf8 |
| 13884 | 3 | 4 | 5 | 6 | | VI-1 | Rnft2 |
| 13885 | 3 | 4 | 5 | 6 | | VI-1 | Rnh1 |
| 13886 | 3 | 4 | 5 | 6 | | VI-1 | Rnmt |
| 13887 | 3 | 4 | 5 | 6 | | VI-1 | Rnmtl1 |
| 13888 | 3 | 4 | 5 | 6 | | VI-1 | Rnpc3 |
| 13889 | 3 | 4 | 5 | 6 | | VI-1 | Rnpep |
| 13890 | 3 | 4 | 5 | 6 | | VI-1 | Rnpepl1 |
| 13891 | 3 | 4 | 5 | 6 | | VI-1 | Rnps1 |
| 13892 | 3 | 4 | 5 | 6 | | VI-1 | Robo4 |
| 13893 | 3 | 4 | 5 | 6 | | VI-1 | Rock1 |
| 13894 | 3 | 4 | 5 | 6 | | VI-1 | Ropn1 |
| 13895 | 3 | 4 | 5 | 6 | | VI-1 | Ror2 |
| 13896 | 3 | 4 | 5 | 6 | | VI-1 | Rora |
| 13897 | 3 | 4 | 5 | 6 | | VI-1 | Rp2h |
| 13898 | 3 | 4 | 5 | 6 | | VI-1 | Rp9 |
| 13899 | 3 | 4 | 5 | 6 | | VI-1 | Rpa1 |
| 13900 | 3 | 4 | 5 | 6 | | VI-1 | Rpain |
| 13901 | 3 | 4 | 5 | 6 | | VI-1 | Rpap1 |
| 13902 | 3 | 4 | 5 | 6 | | VI-1 | Rpap2 |
| 13903 | 3 | 4 | 5 | 6 | | VI-1 | Rpf1 |
| 13904 | 3 | 4 | 5 | 6 | | VI-1 | Rph3al |
| 13905 | 3 | 4 | 5 | 6 | | VI-1 | Rpia |
| 13906 | 3 | 4 | 5 | 6 | | VI-1 | Rpl10l |
| 13907 | 3 | 4 | 5 | 6 | | VI-1 | Rpl11 |
| 13908 | 3 | 4 | 5 | 6 | | VI-1 | Rpl14-ps1 |
| 13909 | 3 | 4 | 5 | 6 | | VI-1 | Rpl15 |
| 13910 | 3 | 4 | 5 | 6 | | VI-1 | Rpl23a |
| 13911 | 3 | 4 | 5 | 6 | | VI-1 | Rpl27 |
| 13912 | 3 | 4 | 5 | 6 | | VI-1 | Rpl34 |
| 13913 | 3 | 4 | 5 | 6 | | VI-1 | Rpl39l |
| 13914 | 3 | 4 | 5 | 6 | | VI-1 | Rpl5 |
| 13915 | 3 | 4 | 5 | 6 | | VI-1 | Rpl6 |
| 13916 | 3 | 4 | 5 | 6 | | VI-1 | Rpl7 |
| 13917 | 3 | 4 | 5 | 6 | | VI-1 | Rpl7a |
| 13918 | 3 | 4 | 5 | 6 | | VI-1 | Rpl7l1 |
| 13919 | 3 | 4 | 5 | 6 | | VI-1 | Rpt9 |
| 13920 | 3 | 4 | 5 | 6 | | VI-1 | Rpn1 |
| 13921 | 3 | 4 | 5 | 6 | | VI-1 | Rpn2 |
| 13922 | 3 | 4 | 5 | 6 | | VI-1 | Rpp14 |
| 13923 | 3 | 4 | 5 | 6 | | VI-1 | Rpp25 |
| 13924 | 3 | 4 | 5 | 6 | | VI-1 | Rpp30 |
| 13925 | 3 | 4 | 5 | 6 | | VI-1 | Rprd1a |
| 13926 | 3 | 4 | 5 | 6 | | VI-1 | Rpril |
| 13927 | 3 | 4 | 5 | 6 | | VI-1 | Rprm |
| 13928 | 3 | 4 | 5 | 6 | | VI-1 | Rps11 |
| 13929 | 3 | 4 | 5 | 6 | | VI-1 | Rps15a |
| 13930 | 3 | 4 | 5 | 6 | | VI-1 | Rps17 |
| 13931 | 3 | 4 | 5 | 6 | | VI-1 | Rps19bp1 |
| 13932 | 3 | 4 | 5 | 6 | | VI-1 | Rps23 |
| 13933 | 3 | 4 | 5 | 6 | | VI-1 | Rps26 |
| 13934 | 3 | 4 | 5 | 6 | | VI-1 | Rps27l |
| 13935 | 3 | 4 | 5 | 6 | | VI-1 | Rps28 |
| 13936 | 3 | 4 | 5 | 6 | | VI-1 | Rps3a1 |
| 13937 | 3 | 4 | 5 | 6 | | VI-1 | Rps5 |
| 13938 | 3 | 4 | 5 | 6 | | VI-1 | Rps6ka1 |
| 13939 | 3 | 4 | 5 | 6 | | VI-1 | Rps6ka2 |
| 13940 | 3 | 4 | 5 | 6 | | VI-1 | Rps6ka3 |
| 13941 | 3 | 4 | 5 | 6 | | VI-1 | Rps6ka4 |
| 13942 | 3 | 4 | 5 | 6 | | VI-1 | Rps6ka5 |
| 13943 | 3 | 4 | 5 | 6 | | VI-1 | Rps6kb1 |
| 13944 | 3 | 4 | 5 | 6 | | VI-1 | Rps6kb2 |
| 13945 | 3 | 4 | 5 | 6 | | VI-1 | Rps6kl1 |
| 13946 | 3 | 4 | 5 | 6 | | VI-1 | Rps7 |
| 13947 | 3 | 4 | 5 | 6 | | VI-1 | Rqcd1 |
| 13948 | 3 | 4 | 5 | 6 | | VI-1 | Rragb |
| 13949 | 3 | 4 | 5 | 6 | | VI-1 | Rras |
| 13950 | 3 | 4 | 5 | 6 | | VI-1 | Rras2 |
| 13951 | 3 | 4 | 5 | 6 | | VI-1 | Rrbp1 |
| 13952 | 3 | 4 | 5 | 6 | | VI-1 | Rrm2b |
| 13953 | 3 | 4 | 5 | 6 | | VI-1 | Rrnad1 |
| 13954 | 3 | 4 | 5 | 6 | | VI-1 | Rrp1 |
| 13955 | 3 | 4 | 5 | 6 | | VI-1 | Rrp15 |
| 13956 | 3 | 4 | 5 | 6 | | VI-1 | Rrp1b |
| 13957 | 3 | 4 | 5 | 6 | | VI-1 | Rrp9 |
| 13958 | 3 | 4 | 5 | 6 | | VI-1 | Rrs1 |
| 13959 | 3 | 4 | 5 | 6 | | VI-1 | Rsbn1l |
| 13960 | 3 | 4 | 5 | 6 | | VI-1 | Rsc1a1 |
| 13961 | 3 | 4 | 5 | 6 | | VI-1 | Rsl24d1 |
| 13962 | 3 | 4 | 5 | 6 | | VI-1 | Rsph1 |
| 13963 | 3 | 4 | 5 | 6 | | VI-1 | Rsph4a |
| 13964 | 3 | 4 | 5 | 6 | | VI-1 | Rspo1 |
| 13965 | 3 | 4 | 5 | 6 | | VI-1 | Rsrc2 |
| 13966 | 3 | 4 | 5 | 6 | | VI-1 | Rtbdn |
| 13967 | 3 | 4 | 5 | 6 | | VI-1 | Rtca |
| 13968 | 3 | 4 | 5 | 6 | | VI-1 | Rtfdc1 |
| 13969 | 3 | 4 | 5 | 6 | | VI-1 | Rtkn |
| 13970 | 3 | 4 | 5 | 6 | | VI-1 | Rtn4rl2 |
| 13971 | 3 | 4 | 5 | 6 | | VI-1 | Rufy1 |
| 13972 | 3 | 4 | 5 | 6 | | VI-1 | Rufy2 |
| 13973 | 3 | 4 | 5 | 6 | | VI-1 | Rufy3 |
| 13974 | 3 | 4 | 5 | 6 | | VI-1 | Rufy4 |
| 13975 | 3 | 4 | 5 | 6 | | VI-1 | Rundc1 |
| 13976 | 3 | 4 | 5 | 6 | | VI-1 | Rundc3a |
| 13977 | 3 | 4 | 5 | 6 | | VI-1 | Runx1 |
| 13978 | 3 | 4 | 5 | 6 | | VI-1 | Rusc1 |
| 13979 | 3 | 4 | 5 | 6 | | VI-1 | Ruvbl1 |
| 13980 | 3 | 4 | 5 | 6 | | VI-1 | Rwdd1 |
| 13981 | 3 | 4 | 5 | 6 | | VI-1 | Rwdd2a |
| 13982 | 3 | 4 | 5 | 6 | | VI-1 | Rwdd2b |
| 13983 | 3 | 4 | 5 | 6 | | VI-1 | Rxra |
| 13984 | 3 | 4 | 5 | 6 | | VI-1 | Rxrb |
| 13985 | 3 | 4 | 5 | 6 | | VI-1 | Ryk |
| 13986 | 3 | 4 | 5 | 6 | | VI-1 | Ryr1 |
| 13987 | 3 | 4 | 5 | 6 | | VI-1 | S100a1 |
| 13988 | 3 | 4 | 5 | 6 | | VI-1 | S100a11 |
| 13989 | 3 | 4 | 5 | 6 | | VI-1 | S100g |
| 13990 | 3 | 4 | 5 | 6 | | VI-1 | S100pbp |
| 13991 | 3 | 4 | 5 | 6 | | VI-1 | S100z |
| 13992 | 3 | 4 | 5 | 6 | | VI-1 | S1pr1 |
| 13993 | 3 | 4 | 5 | 6 | | VI-1 | S1pr4 |
| 13994 | 3 | 4 | 5 | 6 | | VI-1 | Saal1 |
| 13995 | 3 | 4 | 5 | 6 | | VI-1 | Sac3d1 |
| 13996 | 3 | 4 | 5 | 6 | | VI-1 | Sacm1l |
| 13997 | 3 | 4 | 5 | 6 | | VI-1 | Sag |
| 13998 | 3 | 4 | 5 | 6 | | VI-1 | Sall1 |
| 13999 | 3 | 4 | 5 | 6 | | VI-1 | Sall4 |
| 14000 | 3 | 4 | 5 | 6 | | VI-1 | Samd15 |
| 14001 | 3 | 4 | 5 | 6 | | VI-1 | Samd4 |
| 14002 | 3 | 4 | 5 | 6 | | VI-1 | Samd4b |
| 14003 | 3 | 4 | 5 | 6 | | VI-1 | Samd5 |
| 14004 | 3 | 4 | 5 | 6 | | VI-1 | Samd7 |
| 14005 | 3 | 4 | 5 | 6 | | VI-1 | Samd8 |
| 14006 | 3 | 4 | 5 | 6 | | VI-1 | Samd9l |
| 14007 | 3 | 4 | 5 | 6 | | VI-1 | Samhd1 |
| 14008 | 3 | 4 | 5 | 6 | | VI-1 | Sap30bp |
| 14009 | 3 | 4 | 5 | 6 | | VI-1 | Sardh |
| 14010 | 3 | 4 | 5 | 6 | | VI-1 | Sarnp |
| 14011 | 3 | 4 | 5 | 6 | | VI-1 | Sav1 |
| 14012 | 3 | 4 | 5 | 6 | | VI-1 | Sbds |
| 14013 | 3 | 4 | 5 | 6 | | VI-1 | Sbk2 |
| 14014 | 3 | 4 | 5 | 6 | | VI-1 | Scaf11 |

Fig. 34 - 74

| | | | | | | | |
|---|---|---|---|---|---|---|---|
| 14015 | 3 | 4 | 5 | 6 | | VI-1 | Scaf8 |
| 14016 | 3 | 4 | 5 | 6 | | VI-1 | Scamp5 |
| 14017 | 3 | 4 | 5 | 6 | | VI-1 | Scap |
| 14018 | 3 | 4 | 5 | 6 | | VI-1 | Scarb2 |
| 14019 | 3 | 4 | 5 | 6 | | VI-1 | Scarf1 |
| 14020 | 3 | 4 | 5 | 6 | | VI-1 | Sccpdh |
| 14021 | 3 | 4 | 5 | 6 | | VI-1 | Scgb1b7 |
| 14022 | 3 | 4 | 5 | 6 | | VI-1 | Scgb1c1 |
| 14023 | 3 | 4 | 5 | 6 | | VI-1 | Scgb2b15 |
| 14024 | 3 | 4 | 5 | 6 | | VI-1 | Scgb2b17 |
| 14025 | 3 | 4 | 5 | 6 | | VI-1 | Scgb2b7 |
| 14026 | 3 | 4 | 5 | 6 | | VI-1 | Scgb3a2 |
| 14027 | 3 | 4 | 5 | 6 | | VI-1 | Schip1 |
| 14028 | 3 | 4 | 5 | 6 | | VI-1 | Scimp |
| 14029 | 3 | 4 | 5 | 6 | | VI-1 | Scin |
| 14030 | 3 | 4 | 5 | 6 | | VI-1 | Scmh1 |
| 14031 | 3 | 4 | 5 | 6 | | VI-1 | Scn1a |
| 14032 | 3 | 4 | 5 | 6 | | VI-1 | Scn1b |
| 14033 | 3 | 4 | 5 | 6 | | VI-1 | Scn2a1 |
| 14034 | 3 | 4 | 5 | 6 | | VI-1 | Scn4a |
| 14035 | 3 | 4 | 5 | 6 | | VI-1 | Scn8a |
| 14036 | 3 | 4 | 5 | 6 | | VI-1 | Scnn1a |
| 14037 | 3 | 4 | 5 | 6 | | VI-1 | Scnn1g |
| 14038 | 3 | 4 | 5 | 6 | | VI-1 | Scoc |
| 14039 | 3 | 4 | 5 | 6 | | VI-1 | Scp2 |
| 14040 | 3 | 4 | 5 | 6 | | VI-1 | Scp2d1 |
| 14041 | 3 | 4 | 5 | 6 | | VI-1 | Scpep1 |
| 14042 | 3 | 4 | 5 | 6 | | VI-1 | Scx |
| 14043 | 3 | 4 | 5 | 6 | | VI-1 | Scyl1 |
| 14044 | 3 | 4 | 5 | 6 | | VI-1 | Scyl2 |
| 14045 | 3 | 4 | 5 | 6 | | VI-1 | Scyl3 |
| 14046 | 3 | 4 | 5 | 6 | | VI-1 | Sdc2 |
| 14047 | 3 | 4 | 5 | 6 | | VI-1 | Sdc3 |
| 14048 | 3 | 4 | 5 | 6 | | VI-1 | Sdcbp |
| 14049 | 3 | 4 | 5 | 6 | | VI-1 | Sdccag3 |
| 14050 | 3 | 4 | 5 | 6 | | VI-1 | Sdccag8 |
| 14051 | 3 | 4 | 5 | 6 | | VI-1 | Sdf2 |
| 14052 | 3 | 4 | 5 | 6 | | VI-1 | Sdf4 |
| 14053 | 3 | 4 | 5 | 6 | | VI-1 | Sdhb |
| 14054 | 3 | 4 | 5 | 6 | | VI-1 | Sdpr |
| 14055 | 3 | 4 | 5 | 6 | | VI-1 | Sdr16c5 |
| 14056 | 3 | 4 | 5 | 6 | | VI-1 | Sdr39u1 |
| 14057 | 3 | 4 | 5 | 6 | | VI-1 | Sdr42e1 |
| 14058 | 3 | 4 | 5 | 6 | | VI-1 | Sec1 |
| 14059 | 3 | 4 | 5 | 6 | | VI-1 | Sec11a |
| 14060 | 3 | 4 | 5 | 6 | | VI-1 | Sec11c |
| 14061 | 3 | 4 | 5 | 6 | | VI-1 | Sec13 |
| 14062 | 3 | 4 | 5 | 6 | | VI-1 | Sec14l2 |
| 14063 | 3 | 4 | 5 | 6 | | VI-1 | Sec14l3 |
| 14064 | 3 | 4 | 5 | 6 | | VI-1 | Sec14l4 |
| 14065 | 3 | 4 | 5 | 6 | | VI-1 | Sec16a |
| 14066 | 3 | 4 | 5 | 6 | | VI-1 | Sec24a |
| 14067 | 3 | 4 | 5 | 6 | | VI-1 | Sec61a1 |
| 14068 | 3 | 4 | 5 | 6 | | VI-1 | Sec63 |
| 14069 | 3 | 4 | 5 | 6 | | VI-1 | Seh1l |
| 14070 | 3 | 4 | 5 | 6 | | VI-1 | Sel1l |
| 14071 | 3 | 4 | 5 | 6 | | VI-1 | Sel1l3 |
| 14072 | 3 | 4 | 5 | 6 | | VI-1 | Selplg |
| 14073 | 3 | 4 | 5 | 6 | | VI-1 | Sema3a |
| 14074 | 3 | 4 | 5 | 6 | | VI-1 | Sema3b |
| 14075 | 3 | 4 | 5 | 6 | | VI-1 | Sema3f |
| 14076 | 3 | 4 | 5 | 6 | | VI-1 | Sema4a |
| 14077 | 3 | 4 | 5 | 6 | | VI-1 | Sema5a |
| 14078 | 3 | 4 | 5 | 6 | | VI-1 | Sema6b |
| 14079 | 3 | 4 | 5 | 6 | | VI-1 | Sema6c |
| 14080 | 3 | 4 | 5 | 6 | | VI-1 | Sema6d |
| 14081 | 3 | 4 | 5 | 6 | | VI-1 | Sema7a |
| 14082 | 3 | 4 | 5 | 6 | | VI-1 | Senp3 |
| 14083 | 3 | 4 | 5 | 6 | | VI-1 | Senp6 |
| 14084 | 3 | 4 | 5 | 6 | | VI-1 | Sephs2 |
| 14085 | 3 | 4 | 5 | 6 | | VI-1 | Sepn1 |
| 14086 | 3 | 4 | 5 | 6 | | VI-1 | Sepp1 |
| 14087 | 3 | 4 | 5 | 6 | | VI-1 | Sepsecs |
| 14088 | 3 | 4 | 5 | 6 | | VI-1 | Sept2 |
| 14089 | 3 | 4 | 5 | 6 | | VI-1 | Sept4 |
| 14090 | 3 | 4 | 5 | 6 | | VI-1 | Sept9 |
| 14091 | 3 | 4 | 5 | 6 | | VI-1 | Serf2 |
| 14092 | 3 | 4 | 5 | 6 | | VI-1 | Serinc2 |
| 14093 | 3 | 4 | 5 | 6 | | VI-1 | Serinc3 |
| 14094 | 3 | 4 | 5 | 6 | | VI-1 | Serinc5 |
| 14095 | 3 | 4 | 5 | 6 | | VI-1 | Serpina10 |
| 14096 | 3 | 4 | 5 | 6 | | VI-1 | Serpina3c |
| 14097 | 3 | 4 | 5 | 6 | | VI-1 | Serpina3h |
| 14098 | 3 | 4 | 5 | 6 | | VI-1 | Serpina4-ps1 |
| 14099 | 3 | 4 | 5 | 6 | | VI-1 | Serpinb1c |
| 14100 | 3 | 4 | 5 | 6 | | VI-1 | Serpinb6c |
| 14101 | 3 | 4 | 5 | 6 | | VI-1 | Serpinb6d |
| 14102 | 3 | 4 | 5 | 6 | | VI-1 | Serpinb8 |
| 14103 | 3 | 4 | 5 | 6 | | VI-1 | Serpinb9b |
| 14104 | 3 | 4 | 5 | 6 | | VI-1 | Serpind1 |
| 14105 | 3 | 4 | 5 | 6 | | VI-1 | Serpine1 |
| 14106 | 3 | 4 | 5 | 6 | | VI-1 | Serpinf1 |
| 14107 | 3 | 4 | 5 | 6 | | VI-1 | Serpinh1 |
| 14108 | 3 | 4 | 5 | 6 | | VI-1 | Serpini2 |
| 14109 | 3 | 4 | 5 | 6 | | VI-1 | Sertad2 |
| 14110 | 3 | 4 | 5 | 6 | | VI-1 | Sestd1 |
| 14111 | 3 | 4 | 5 | 6 | | VI-1 | Setbp1 |
| 14112 | 3 | 4 | 5 | 6 | | VI-1 | Setd1a |
| 14113 | 3 | 4 | 5 | 6 | | VI-1 | Setd3 |
| 14114 | 3 | 4 | 5 | 6 | | VI-1 | Setd6 |
| 14115 | 3 | 4 | 5 | 6 | | VI-1 | Setd8 |
| 14116 | 3 | 4 | 5 | 6 | | VI-1 | Setmar |
| 14117 | 3 | 4 | 5 | 6 | | VI-1 | Sf1 |
| 14118 | 3 | 4 | 5 | 6 | | VI-1 | Sf3a1 |
| 14119 | 3 | 4 | 5 | 6 | | VI-1 | Sf3a2 |
| 14120 | 3 | 4 | 5 | 6 | | VI-1 | Sf3b1 |
| 14121 | 3 | 4 | 5 | 6 | | VI-1 | Sf3b5 |
| 14122 | 3 | 4 | 5 | 6 | | VI-1 | Sfi1 |
| 14123 | 3 | 4 | 5 | 6 | | VI-1 | Sfr1 |
| 14124 | 3 | 4 | 5 | 6 | | VI-1 | Sfrp4 |
| 14125 | 3 | 4 | 5 | 6 | | VI-1 | Sfswap |
| 14126 | 3 | 4 | 5 | 6 | | VI-1 | Sftpa1 |
| 14127 | 3 | 4 | 5 | 6 | | VI-1 | Sfxn1 |
| 14128 | 3 | 4 | 5 | 6 | | VI-1 | Sfxn2 |
| 14129 | 3 | 4 | 5 | 6 | | VI-1 | Sfxn4 |
| 14130 | 3 | 4 | 5 | 6 | | VI-1 | Sgcb |
| 14131 | 3 | 4 | 5 | 6 | | VI-1 | Sgcd |
| 14132 | 3 | 4 | 5 | 6 | | VI-1 | Sgce |
| 14133 | 3 | 4 | 5 | 6 | | VI-1 | Sgcg |
| 14134 | 3 | 4 | 5 | 6 | | VI-1 | Sgip1 |
| 14135 | 3 | 4 | 5 | 6 | | VI-1 | Sgms1 |
| 14136 | 3 | 4 | 5 | 6 | | VI-1 | Sgol2 |
| 14137 | 3 | 4 | 5 | 6 | | VI-1 | Sgpp1 |
| 14138 | 3 | 4 | 5 | 6 | | VI-1 | Sgpp2 |
| 14139 | 3 | 4 | 5 | 6 | | VI-1 | Sgsm1 |
| 14140 | 3 | 4 | 5 | 6 | | VI-1 | Sgsm2 |
| 14141 | 3 | 4 | 5 | 6 | | VI-1 | Sgta |
| 14142 | 3 | 4 | 5 | 6 | | VI-1 | Sgtb |
| 14143 | 3 | 4 | 5 | 6 | | VI-1 | Sh2b3 |
| 14144 | 3 | 4 | 5 | 6 | | VI-1 | Sh2d1b1 |
| 14145 | 3 | 4 | 5 | 6 | | VI-1 | Sh2d2a |
| 14146 | 3 | 4 | 5 | 6 | | VI-1 | Sh2d4b |
| 14147 | 3 | 4 | 5 | 6 | | VI-1 | Sh2d5 |
| 14148 | 3 | 4 | 5 | 6 | | VI-1 | Sh3bgrl2 |
| 14149 | 3 | 4 | 5 | 6 | | VI-1 | Sh3bgrl3 |
| 14150 | 3 | 4 | 5 | 6 | | VI-1 | Sh3bp2 |
| 14151 | 3 | 4 | 5 | 6 | | VI-1 | Sh3bp4 |
| 14152 | 3 | 4 | 5 | 6 | | VI-1 | Sh3d19 |
| 14153 | 3 | 4 | 5 | 6 | | VI-1 | Sh3d21 |
| 14154 | 3 | 4 | 5 | 6 | | VI-1 | Sh3gl3 |
| 14155 | 3 | 4 | 5 | 6 | | VI-1 | Sh3glb2 |
| 14156 | 3 | 4 | 5 | 6 | | VI-1 | Sh3tc2 |
| 14157 | 3 | 4 | 5 | 6 | | VI-1 | Sh3yl1 |
| 14158 | 3 | 4 | 5 | 6 | | VI-1 | Shank1 |
| 14159 | 3 | 4 | 5 | 6 | | VI-1 | Shank2 |
| 14160 | 3 | 4 | 5 | 6 | | VI-1 | Shbg |
| 14161 | 3 | 4 | 5 | 6 | | VI-1 | Shc1 |
| 14162 | 3 | 4 | 5 | 6 | | VI-1 | Shc2 |
| 14163 | 3 | 4 | 5 | 6 | | VI-1 | Shd |
| 14164 | 3 | 4 | 5 | 6 | | VI-1 | Shfm1 |
| 14165 | 3 | 4 | 5 | 6 | | VI-1 | Shisa4 |
| 14166 | 3 | 4 | 5 | 6 | | VI-1 | Shisa5 |
| 14167 | 3 | 4 | 5 | 6 | | VI-1 | Shisa9 |
| 14168 | 3 | 4 | 5 | 6 | | VI-1 | Shkbp1 |
| 14169 | 3 | 4 | 5 | 6 | | VI-1 | Shmt2 |
| 14170 | 3 | 4 | 5 | 6 | | VI-1 | Shprh |
| 14171 | 3 | 4 | 5 | 6 | | VI-1 | Shq1 |
| 14172 | 3 | 4 | 5 | 6 | | VI-1 | Shroom2 |
| 14173 | 3 | 4 | 5 | 6 | | VI-1 | Shroom3 |
| 14174 | 3 | 4 | 5 | 6 | | VI-1 | Shroom4 |
| 14175 | 3 | 4 | 5 | 6 | | VI-1 | Siah1a |
| 14176 | 3 | 4 | 5 | 6 | | VI-1 | Siah3 |
| 14177 | 3 | 4 | 5 | 6 | | VI-1 | Sidt1 |
| 14178 | 3 | 4 | 5 | 6 | | VI-1 | Sidt2 |
| 14179 | 3 | 4 | 5 | 6 | | VI-1 | Siglec1 |
| 14180 | 3 | 4 | 5 | 6 | | VI-1 | Siglece |
| 14181 | 3 | 4 | 5 | 6 | | VI-1 | Siglech |
| 14182 | 3 | 4 | 5 | 6 | | VI-1 | Sigmar1 |
| 14183 | 3 | 4 | 5 | 6 | | VI-1 | Sim2 |
| 14184 | 3 | 4 | 5 | 6 | | VI-1 | Sirpb1a |
| 14185 | 3 | 4 | 5 | 6 | | VI-1 | Sirt1 |
| 14186 | 3 | 4 | 5 | 6 | | VI-1 | Sirt2 |
| 14187 | 3 | 4 | 5 | 6 | | VI-1 | Sirt7 |
| 14188 | 3 | 4 | 5 | 6 | | VI-1 | Six1 |
| 14189 | 3 | 4 | 5 | 6 | | VI-1 | Six2 |
| 14190 | 3 | 4 | 5 | 6 | | VI-1 | Ska1 |
| 14191 | 3 | 4 | 5 | 6 | | VI-1 | Ska2 |
| 14192 | 3 | 4 | 5 | 6 | | VI-1 | Skap1 |
| 14193 | 3 | 4 | 5 | 6 | | VI-1 | Skap2 |
| 14194 | 3 | 4 | 5 | 6 | | VI-1 | Skil |
| 14195 | 3 | 4 | 5 | 6 | | VI-1 | Skp1a |
| 14196 | 3 | 4 | 5 | 6 | | VI-1 | Sla |
| 14197 | 3 | 4 | 5 | 6 | | VI-1 | Slamf1 |
| 14198 | 3 | 4 | 5 | 6 | | VI-1 | Slc10a2 |
| 14199 | 3 | 4 | 5 | 6 | | VI-1 | Slc10a4 |
| 14200 | 3 | 4 | 5 | 6 | | VI-1 | Slc12a2 |
| 14201 | 3 | 4 | 5 | 6 | | VI-1 | Slc12a3 |
| 14202 | 3 | 4 | 5 | 6 | | VI-1 | Slc12a4 |
| 14203 | 3 | 4 | 5 | 6 | | VI-1 | Slc12a6 |
| 14204 | 3 | 4 | 5 | 6 | | VI-1 | Slc12a7 |
| 14205 | 3 | 4 | 5 | 6 | | VI-1 | Slc12a9 |
| 14206 | 3 | 4 | 5 | 6 | | VI-1 | Slc13a3 |

Fig. 34 - 75

| | | | | | | |
|---|---|---|---|---|---|---|
| 14207 | 3 | 4 | 5 | 6 | VI-1 | Slc15a2 |
| 14208 | 3 | 4 | 5 | 6 | VI-1 | Slc15a4 |
| 14209 | 3 | 4 | 5 | 6 | VI-1 | Slc15a5 |
| 14210 | 3 | 4 | 5 | 6 | VI-1 | Slc16a10 |
| 14211 | 3 | 4 | 5 | 6 | VI-1 | Slc16a11 |
| 14212 | 3 | 4 | 5 | 6 | VI-1 | Slc16a14 |
| 14213 | 3 | 4 | 5 | 6 | VI-1 | Slc16a4 |
| 14214 | 3 | 4 | 5 | 6 | VI-1 | Slc16a7 |
| 14215 | 3 | 4 | 5 | 6 | VI-1 | Slc16a9 |
| 14216 | 3 | 4 | 5 | 6 | VI-1 | Slc17a4 |
| 14217 | 3 | 4 | 5 | 6 | VI-1 | Slc17a6 |
| 14218 | 3 | 4 | 5 | 6 | VI-1 | Slc19a2 |
| 14219 | 3 | 4 | 5 | 6 | VI-1 | Slc19a3 |
| 14220 | 3 | 4 | 5 | 6 | VI-1 | Slc1a1 |
| 14221 | 3 | 4 | 5 | 6 | VI-1 | Slc1a3 |
| 14222 | 3 | 4 | 5 | 6 | VI-1 | Slc1a4 |
| 14223 | 3 | 4 | 5 | 6 | VI-1 | Slc20a1 |
| 14224 | 3 | 4 | 5 | 6 | VI-1 | Slc22a1 |
| 14225 | 3 | 4 | 5 | 6 | VI-1 | Slc22a12 |
| 14226 | 3 | 4 | 5 | 6 | VI-1 | Slc22a23 |
| 14227 | 3 | 4 | 5 | 6 | VI-1 | Slc22a26 |
| 14228 | 3 | 4 | 5 | 6 | VI-1 | Slc22a3 |
| 14229 | 3 | 4 | 5 | 6 | VI-1 | Slc22a7 |
| 14230 | 3 | 4 | 5 | 6 | VI-1 | Slc23a2 |
| 14231 | 3 | 4 | 5 | 6 | VI-1 | Slc23a3 |
| 14232 | 3 | 4 | 5 | 6 | VI-1 | Slc25a1 |
| 14233 | 3 | 4 | 5 | 6 | VI-1 | Slc25a11 |
| 14234 | 3 | 4 | 5 | 6 | VI-1 | Slc25a12 |
| 14235 | 3 | 4 | 5 | 6 | VI-1 | Slc25a13 |
| 14236 | 3 | 4 | 5 | 6 | VI-1 | Slc25a15 |
| 14237 | 3 | 4 | 5 | 6 | VI-1 | Slc25a17 |
| 14238 | 3 | 4 | 5 | 6 | VI-1 | Slc25a19 |
| 14239 | 3 | 4 | 5 | 6 | VI-1 | Slc25a22 |
| 14240 | 3 | 4 | 5 | 6 | VI-1 | Slc25a26 |
| 14241 | 3 | 4 | 5 | 6 | VI-1 | Slc25a27 |
| 14242 | 3 | 4 | 5 | 6 | VI-1 | Slc25a28 |
| 14243 | 3 | 4 | 5 | 6 | VI-1 | Slc25a29 |
| 14244 | 3 | 4 | 5 | 6 | VI-1 | Slc25a3 |
| 14245 | 3 | 4 | 5 | 6 | VI-1 | Slc25a37 |
| 14246 | 3 | 4 | 5 | 6 | VI-1 | Slc25a44 |
| 14247 | 3 | 4 | 5 | 6 | VI-1 | Slc25a45 |
| 14248 | 3 | 4 | 5 | 6 | VI-1 | Slc25a47 |
| 14249 | 3 | 4 | 5 | 6 | VI-1 | Slc25a5 |
| 14250 | 3 | 4 | 5 | 6 | VI-1 | Slc25a51 |
| 14251 | 3 | 4 | 5 | 6 | VI-1 | Slc25a53 |
| 14252 | 3 | 4 | 5 | 6 | VI-1 | Slc26a11 |
| 14253 | 3 | 4 | 5 | 6 | VI-1 | Slc26a4 |
| 14254 | 3 | 4 | 5 | 6 | VI-1 | Slc26a8 |
| 14255 | 3 | 4 | 5 | 6 | VI-1 | Slc26a9 |
| 14256 | 3 | 4 | 5 | 6 | VI-1 | Slc27a1 |
| 14257 | 3 | 4 | 5 | 6 | VI-1 | Slc27a2 |
| 14258 | 3 | 4 | 5 | 6 | VI-1 | Slc28a1 |
| 14259 | 3 | 4 | 5 | 6 | VI-1 | Slc28a2 |
| 14260 | 3 | 4 | 5 | 6 | VI-1 | Slc28a3 |
| 14261 | 3 | 4 | 5 | 6 | VI-1 | Slc2a1 |
| 14262 | 3 | 4 | 5 | 6 | VI-1 | Slc2a12 |
| 14263 | 3 | 4 | 5 | 6 | VI-1 | Slc2a13 |
| 14264 | 3 | 4 | 5 | 6 | VI-1 | Slc2a3 |
| 14265 | 3 | 4 | 5 | 6 | VI-1 | Slc2a4rg-ps |
| 14266 | 3 | 4 | 5 | 6 | VI-1 | Slc2a5 |
| 14267 | 3 | 4 | 5 | 6 | VI-1 | Slc2a6 |
| 14268 | 3 | 4 | 5 | 6 | VI-1 | Slc2a8 |
| 14269 | 3 | 4 | 5 | 6 | VI-1 | Slc30a1 |
| 14270 | 3 | 4 | 5 | 6 | VI-1 | Slc30a2 |
| 14271 | 3 | 4 | 5 | 6 | VI-1 | Slc30a3 |
| 14272 | 3 | 4 | 5 | 6 | VI-1 | Slc30a4 |
| 14273 | 3 | 4 | 5 | 6 | VI-1 | Slc30a5 |
| 14274 | 3 | 4 | 5 | 6 | VI-1 | Slc30a9 |
| 14275 | 3 | 4 | 5 | 6 | VI-1 | Slc31a2 |
| 14276 | 3 | 4 | 5 | 6 | VI-1 | Slc35a1 |
| 14277 | 3 | 4 | 5 | 6 | VI-1 | Slc35b2 |
| 14278 | 3 | 4 | 5 | 6 | VI-1 | Slc35b3 |
| 14279 | 3 | 4 | 5 | 6 | VI-1 | Slc35c2 |
| 14280 | 3 | 4 | 5 | 6 | VI-1 | Slc35d2 |
| 14281 | 3 | 4 | 5 | 6 | VI-1 | Slc35d3 |
| 14282 | 3 | 4 | 5 | 6 | VI-1 | Slc35e1 |
| 14283 | 3 | 4 | 5 | 6 | VI-1 | Slc35e3 |
| 14284 | 3 | 4 | 5 | 6 | VI-1 | Slc36a2 |
| 14285 | 3 | 4 | 5 | 6 | VI-1 | Slc37a1 |
| 14286 | 3 | 4 | 5 | 6 | VI-1 | Slc37a2 |
| 14287 | 3 | 4 | 5 | 6 | VI-1 | Slc37a3 |
| 14288 | 3 | 4 | 5 | 6 | VI-1 | Slc37a4 |
| 14289 | 3 | 4 | 5 | 6 | VI-1 | Slc38a3 |
| 14290 | 3 | 4 | 5 | 6 | VI-1 | Slc38a4 |
| 14291 | 3 | 4 | 5 | 6 | VI-1 | Slc38a5 |
| 14292 | 3 | 4 | 5 | 6 | VI-1 | Slc38a6 |
| 14293 | 3 | 4 | 5 | 6 | VI-1 | Slc38a9 |
| 14294 | 3 | 4 | 5 | 6 | VI-1 | Slc39a11 |
| 14295 | 3 | 4 | 5 | 6 | VI-1 | Slc39a4 |
| 14296 | 3 | 4 | 5 | 6 | VI-1 | Slc39a5 |
| 14297 | 3 | 4 | 5 | 6 | VI-1 | Slc39a6 |
| 14298 | 3 | 4 | 5 | 6 | VI-1 | Slc39a7 |
| 14299 | 3 | 4 | 5 | 6 | VI-1 | Slc39a8 |
| 14300 | 3 | 4 | 5 | 6 | VI-1 | Slc3a2 |
| 14301 | 3 | 4 | 5 | 6 | VI-1 | Slc41a3 |
| 14302 | 3 | 4 | 5 | 6 | VI-1 | Slc43a2 |
| 14303 | 3 | 4 | 5 | 6 | VI-1 | Slc43a3 |
| 14304 | 3 | 4 | 5 | 6 | VI-1 | Slc44a1 |
| 14305 | 3 | 4 | 5 | 6 | VI-1 | Slc44a4 |
| 14306 | 3 | 4 | 5 | 6 | VI-1 | Slc45a4 |
| 14307 | 3 | 4 | 5 | 6 | VI-1 | Slc47a1 |
| 14308 | 3 | 4 | 5 | 6 | VI-1 | Slc47a2 |
| 14309 | 3 | 4 | 5 | 6 | VI-1 | Slc4a1 |
| 14310 | 3 | 4 | 5 | 6 | VI-1 | Slc4a10 |
| 14311 | 3 | 4 | 5 | 6 | VI-1 | Slc4a11 |
| 14312 | 3 | 4 | 5 | 6 | VI-1 | Slc4a3 |
| 14313 | 3 | 4 | 5 | 6 | VI-1 | Slc4a4 |
| 14314 | 3 | 4 | 5 | 6 | VI-1 | Slc4a7 |
| 14315 | 3 | 4 | 5 | 6 | VI-1 | Slc4a8 |
| 14316 | 3 | 4 | 5 | 6 | VI-1 | Slc50a1 |
| 14317 | 3 | 4 | 5 | 6 | VI-1 | Slc51a |
| 14318 | 3 | 4 | 5 | 6 | VI-1 | Slc51b |
| 14319 | 3 | 4 | 5 | 6 | VI-1 | Slc5a1 |
| 14320 | 3 | 4 | 5 | 6 | VI-1 | Slc5a4b |
| 14321 | 3 | 4 | 5 | 6 | VI-1 | Slc6a12 |
| 14322 | 3 | 4 | 5 | 6 | VI-1 | Slc6a15 |
| 14323 | 3 | 4 | 5 | 6 | VI-1 | Slc6a19os |
| 14324 | 3 | 4 | 5 | 6 | VI-1 | Slc6a2 |
| 14325 | 3 | 4 | 5 | 6 | VI-1 | Slc6a20a |
| 14326 | 3 | 4 | 5 | 6 | VI-1 | Slc6a3 |
| 14327 | 3 | 4 | 5 | 6 | VI-1 | Slc6a4 |
| 14328 | 3 | 4 | 5 | 6 | VI-1 | Slc6a7 |
| 14329 | 3 | 4 | 5 | 6 | VI-1 | Slc6a8 |
| 14330 | 3 | 4 | 5 | 6 | VI-1 | Slc7a10 |
| 14331 | 3 | 4 | 5 | 6 | VI-1 | Slc7a14 |
| 14332 | 3 | 4 | 5 | 6 | VI-1 | Slc7a15 |
| 14333 | 3 | 4 | 5 | 6 | VI-1 | Slc7a2 |
| 14334 | 3 | 4 | 5 | 6 | VI-1 | Slc7a4 |
| 14335 | 3 | 4 | 5 | 6 | VI-1 | Slc7a6 |
| 14336 | 3 | 4 | 5 | 6 | VI-1 | Slc7a6os |
| 14337 | 3 | 4 | 5 | 6 | VI-1 | Slc7a9 |
| 14338 | 3 | 4 | 5 | 6 | VI-1 | Slc8a3 |
| 14339 | 3 | 4 | 5 | 6 | VI-1 | Slc9a1 |
| 14340 | 3 | 4 | 5 | 6 | VI-1 | Slc9a2 |
| 14341 | 3 | 4 | 5 | 6 | VI-1 | Slc9a3 |
| 14342 | 3 | 4 | 5 | 6 | VI-1 | Slc9a3r2 |
| 14343 | 3 | 4 | 5 | 6 | VI-1 | Slc9b1 |
| 14344 | 3 | 4 | 5 | 6 | VI-1 | Slco1a1 |
| 14345 | 3 | 4 | 5 | 6 | VI-1 | Slco1c1 |
| 14346 | 3 | 4 | 5 | 6 | VI-1 | Slco2a1 |
| 14347 | 3 | 4 | 5 | 6 | VI-1 | Slfn1 |
| 14348 | 3 | 4 | 5 | 6 | VI-1 | Slfn5os |
| 14349 | 3 | 4 | 5 | 6 | VI-1 | Slfn8 |
| 14350 | 3 | 4 | 5 | 6 | VI-1 | Slfnl1 |
| 14351 | 3 | 4 | 5 | 6 | VI-1 | Slit3 |
| 14352 | 3 | 4 | 5 | 6 | VI-1 | Slitrk1 |
| 14353 | 3 | 4 | 5 | 6 | VI-1 | Slitrk3 |
| 14354 | 3 | 4 | 5 | 6 | VI-1 | Slitrk5 |
| 14355 | 3 | 4 | 5 | 6 | VI-1 | Slmap |
| 14356 | 3 | 4 | 5 | 6 | VI-1 | Slmo1 |
| 14357 | 3 | 4 | 5 | 6 | VI-1 | Smad1 |
| 14358 | 3 | 4 | 5 | 6 | VI-1 | Smarca1 |
| 14359 | 3 | 4 | 5 | 6 | VI-1 | Smarca5-ps |
| 14360 | 3 | 4 | 5 | 6 | VI-1 | Smarcad1 |
| 14361 | 3 | 4 | 5 | 6 | VI-1 | Smarcb1 |
| 14362 | 3 | 4 | 5 | 6 | VI-1 | Smarce1 |
| 14363 | 3 | 4 | 5 | 6 | VI-1 | Smc3 |
| 14364 | 3 | 4 | 5 | 6 | VI-1 | Smc4 |
| 14365 | 3 | 4 | 5 | 6 | VI-1 | Smc5 |
| 14366 | 3 | 4 | 5 | 6 | VI-1 | Smchd1 |
| 14367 | 3 | 4 | 5 | 6 | VI-1 | Smco2 |
| 14368 | 3 | 4 | 5 | 6 | VI-1 | Smco3 |
| 14369 | 3 | 4 | 5 | 6 | VI-1 | Smco4 |
| 14370 | 3 | 4 | 5 | 6 | VI-1 | Smcr8 |
| 14371 | 3 | 4 | 5 | 6 | VI-1 | Smdt1 |
| 14372 | 3 | 4 | 5 | 6 | VI-1 | Smg5 |
| 14373 | 3 | 4 | 5 | 6 | VI-1 | Smim11 |
| 14374 | 3 | 4 | 5 | 6 | VI-1 | Smim12 |
| 14375 | 3 | 4 | 5 | 6 | VI-1 | Smim13 |
| 14376 | 3 | 4 | 5 | 6 | VI-1 | Smim14 |
| 14377 | 3 | 4 | 5 | 6 | VI-1 | Smim19 |
| 14378 | 3 | 4 | 5 | 6 | VI-1 | Smim4 |
| 14379 | 3 | 4 | 5 | 6 | VI-1 | Smim6 |
| 14380 | 3 | 4 | 5 | 6 | VI-1 | Smim7 |
| 14381 | 3 | 4 | 5 | 6 | VI-1 | Smim8 |
| 14382 | 3 | 4 | 5 | 6 | VI-1 | Smn1 |
| 14383 | 3 | 4 | 5 | 6 | VI-1 | Smok4a |
| 14384 | 3 | 4 | 5 | 6 | VI-1 | Smox |
| 14385 | 3 | 4 | 5 | 6 | VI-1 | Smpd1 |
| 14386 | 3 | 4 | 5 | 6 | VI-1 | Smpd3 |
| 14387 | 3 | 4 | 5 | 6 | VI-1 | Smpx |
| 14388 | 3 | 4 | 5 | 6 | VI-1 | Smtn |
| 14389 | 3 | 4 | 5 | 6 | VI-1 | Smtnl2 |
| 14390 | 3 | 4 | 5 | 6 | VI-1 | Smu1 |
| 14391 | 3 | 4 | 5 | 6 | VI-1 | Smurf1 |
| 14392 | 3 | 4 | 5 | 6 | VI-1 | Smyd1 |
| 14393 | 3 | 4 | 5 | 6 | VI-1 | Smyd2 |
| 14394 | 3 | 4 | 5 | 6 | VI-1 | Snai1 |
| 14395 | 3 | 4 | 5 | 6 | VI-1 | Snap47 |
| 14396 | 3 | 4 | 5 | 6 | VI-1 | Snapc2 |
| 14397 | 3 | 4 | 5 | 6 | VI-1 | Snapc4 |
| 14398 | 3 | 4 | 5 | 6 | VI-1 | Snapc5 |

Fig. 34 - 76

| | | | | | | | |
|---|---|---|---|---|---|---|---|
| 14399 | 3 | 4 | 5 | 6 | | VI-1 | Snapin |
| 14400 | 3 | 4 | 5 | 6 | | VI-1 | Sncaip |
| 14401 | 3 | 4 | 5 | 6 | | VI-1 | Sncg |
| 14402 | 3 | 4 | 5 | 6 | | VI-1 | Snd1 |
| 14403 | 3 | 4 | 5 | 6 | | VI-1 | Snhg10 |
| 14404 | 3 | 4 | 5 | 6 | | VI-1 | Snhg18 |
| 14405 | 3 | 4 | 5 | 6 | | VI-1 | Snhg4 |
| 14406 | 3 | 4 | 5 | 6 | | VI-1 | Snhg6 |
| 14407 | 3 | 4 | 5 | 6 | | VI-1 | Snhg7 |
| 14408 | 3 | 4 | 5 | 6 | | VI-1 | Snhg8 |
| 14409 | 3 | 4 | 5 | 6 | | VI-1 | Snip1 |
| 14410 | 3 | 4 | 5 | 6 | | VI-1 | Snrnp200 |
| 14411 | 3 | 4 | 5 | 6 | | VI-1 | Snrnp35 |
| 14412 | 3 | 4 | 5 | 6 | | VI-1 | Snrnp40 |
| 14413 | 3 | 4 | 5 | 6 | | VI-1 | Snrnp70 |
| 14414 | 3 | 4 | 5 | 6 | | VI-1 | Snrpa |
| 14415 | 3 | 4 | 5 | 6 | | VI-1 | Snrpb2 |
| 14416 | 3 | 4 | 5 | 6 | | VI-1 | Snrpd1 |
| 14417 | 3 | 4 | 5 | 6 | | VI-1 | Snrpd3 |
| 14418 | 3 | 4 | 5 | 6 | | VI-1 | Snta1 |
| 14419 | 3 | 4 | 5 | 6 | | VI-1 | Sntb2 |
| 14420 | 3 | 4 | 5 | 6 | | VI-1 | Sntn |
| 14421 | 3 | 4 | 5 | 6 | | VI-1 | Snupn |
| 14422 | 3 | 4 | 5 | 6 | | VI-1 | Snw1 |
| 14423 | 3 | 4 | 5 | 6 | | VI-1 | Snx1 |
| 14424 | 3 | 4 | 5 | 6 | | VI-1 | Snx10 |
| 14425 | 3 | 4 | 5 | 6 | | VI-1 | Snx15 |
| 14426 | 3 | 4 | 5 | 6 | | VI-1 | Snx21 |
| 14427 | 3 | 4 | 5 | 6 | | VI-1 | Snx25 |
| 14428 | 3 | 4 | 5 | 6 | | VI-1 | Snx27 |
| 14429 | 3 | 4 | 5 | 6 | | VI-1 | Snx29 |
| 14430 | 3 | 4 | 5 | 6 | | VI-1 | Snx31 |
| 14431 | 3 | 4 | 5 | 6 | | VI-1 | Snx33 |
| 14432 | 3 | 4 | 5 | 6 | | VI-1 | Snx4 |
| 14433 | 3 | 4 | 5 | 6 | | VI-1 | Snx5 |
| 14434 | 3 | 4 | 5 | 6 | | VI-1 | Snx8 |
| 14435 | 3 | 4 | 5 | 6 | | VI-1 | Sobp |
| 14436 | 3 | 4 | 5 | 6 | | VI-1 | Socs1 |
| 14437 | 3 | 4 | 5 | 6 | | VI-1 | Socs4 |
| 14438 | 3 | 4 | 5 | 6 | | VI-1 | Socs6 |
| 14439 | 3 | 4 | 5 | 6 | | VI-1 | Socs7 |
| 14440 | 3 | 4 | 5 | 6 | | VI-1 | Soga1 |
| 14441 | 3 | 4 | 5 | 6 | | VI-1 | Soga3 |
| 14442 | 3 | 4 | 5 | 6 | | VI-1 | Sorbs2 |
| 14443 | 3 | 4 | 5 | 6 | | VI-1 | Sorbs3 |
| 14444 | 3 | 4 | 5 | 6 | | VI-1 | Sorcs2 |
| 14445 | 3 | 4 | 5 | 6 | | VI-1 | Sort1 |
| 14446 | 3 | 4 | 5 | 6 | | VI-1 | Sos2 |
| 14447 | 3 | 4 | 5 | 6 | | VI-1 | Sowahc |
| 14448 | 3 | 4 | 5 | 6 | | VI-1 | Sox10 |
| 14449 | 3 | 4 | 5 | 6 | | VI-1 | Sox5 |
| 14450 | 3 | 4 | 5 | 6 | | VI-1 | Sox6 |
| 14451 | 3 | 4 | 5 | 6 | | VI-1 | Sox8 |
| 14452 | 3 | 4 | 5 | 6 | | VI-1 | Sox9 |
| 14453 | 3 | 4 | 5 | 6 | | VI-1 | Sp100 |
| 14454 | 3 | 4 | 5 | 6 | | VI-1 | Sp140 |
| 14455 | 3 | 4 | 5 | 6 | | VI-1 | Sp3os |
| 14456 | 3 | 4 | 5 | 6 | | VI-1 | Sp5 |
| 14457 | 3 | 4 | 5 | 6 | | VI-1 | Sp9 |
| 14458 | 3 | 4 | 5 | 6 | | VI-1 | Spaca3 |
| 14459 | 3 | 4 | 5 | 6 | | VI-1 | Spaca4 |
| 14460 | 3 | 4 | 5 | 6 | | VI-1 | Spaca7 |
| 14461 | 3 | 4 | 5 | 6 | | VI-1 | Spag16 |
| 14462 | 3 | 4 | 5 | 6 | | VI-1 | Spag6 |
| 14463 | 3 | 4 | 5 | 6 | | VI-1 | Spag8 |
| 14464 | 3 | 4 | 5 | 6 | | VI-1 | Sparcl1 |
| 14465 | 3 | 4 | 5 | 6 | | VI-1 | Spast |
| 14466 | 3 | 4 | 5 | 6 | | VI-1 | Spata16 |
| 14467 | 3 | 4 | 5 | 6 | | VI-1 | Spata18 |
| 14468 | 3 | 4 | 5 | 6 | | VI-1 | Spata19 |
| 14469 | 3 | 4 | 5 | 6 | | VI-1 | Spata20 |
| 14470 | 3 | 4 | 5 | 6 | | VI-1 | Spata21 |
| 14471 | 3 | 4 | 5 | 6 | | VI-1 | Spata25 |
| 14472 | 3 | 4 | 5 | 6 | | VI-1 | Spata31d1a |
| 14473 | 3 | 4 | 5 | 6 | | VI-1 | Spata33 |
| 14474 | 3 | 4 | 5 | 6 | | VI-1 | Spata4 |
| 14475 | 3 | 4 | 5 | 6 | | VI-1 | Spata45 |
| 14476 | 3 | 4 | 5 | 6 | | VI-1 | Spata5 |
| 14477 | 3 | 4 | 5 | 6 | | VI-1 | Spata6 |
| 14478 | 3 | 4 | 5 | 6 | | VI-1 | Spata7 |
| 14479 | 3 | 4 | 5 | 6 | | VI-1 | Spata9 |
| 14480 | 3 | 4 | 5 | 6 | | VI-1 | Spats1 |
| 14481 | 3 | 4 | 5 | 6 | | VI-1 | Spcs1 |
| 14482 | 3 | 4 | 5 | 6 | | VI-1 | Spcs2 |
| 14483 | 3 | 4 | 5 | 6 | | VI-1 | Speer9-ps1 |
| 14484 | 3 | 4 | 5 | 6 | | VI-1 | Spef1 |
| 14485 | 3 | 4 | 5 | 6 | | VI-1 | Speg |
| 14486 | 3 | 4 | 5 | 6 | | VI-1 | Spen |
| 14487 | 3 | 4 | 5 | 6 | | VI-1 | Spert |
| 14488 | 3 | 4 | 5 | 6 | | VI-1 | Spg21 |
| 14489 | 3 | 4 | 5 | 6 | | VI-1 | Sphkap |
| 14490 | 3 | 4 | 5 | 6 | | VI-1 | Spi1 |
| 14491 | 3 | 4 | 5 | 6 | | VI-1 | Spic |
| 14492 | 3 | 4 | 5 | 6 | | VI-1 | Spice1 |
| 14493 | 3 | 4 | 5 | 6 | | VI-1 | Spidr |
| 14494 | 3 | 4 | 5 | 6 | | VI-1 | Spink10 |
| 14495 | 3 | 4 | 5 | 6 | | VI-1 | Spink12 |
| 14496 | 3 | 4 | 5 | 6 | | VI-1 | Spink14 |
| 14497 | 3 | 4 | 5 | 6 | | VI-1 | Spink2 |
| 14498 | 3 | 4 | 5 | 6 | | VI-1 | Spink4 |
| 14499 | 3 | 4 | 5 | 6 | | VI-1 | Spink5 |
| 14500 | 3 | 4 | 5 | 6 | | VI-1 | Spint1 |
| 14501 | 3 | 4 | 5 | 6 | | VI-1 | Spint2 |
| 14502 | 3 | 4 | 5 | 6 | | VI-1 | Spire1 |
| 14503 | 3 | 4 | 5 | 6 | | VI-1 | Spire2 |
| 14504 | 3 | 4 | 5 | 6 | | VI-1 | Spns1 |
| 14505 | 3 | 4 | 5 | 6 | | VI-1 | Spns2 |
| 14506 | 3 | 4 | 5 | 6 | | VI-1 | Spock3 |
| 14507 | 3 | 4 | 5 | 6 | | VI-1 | Spon1 |
| 14508 | 3 | 4 | 5 | 6 | | VI-1 | Spon2 |
| 14509 | 3 | 4 | 5 | 6 | | VI-1 | Sppl2a |
| 14510 | 3 | 4 | 5 | 6 | | VI-1 | Sppl2c |
| 14511 | 3 | 4 | 5 | 6 | | VI-1 | Sppl3 |
| 14512 | 3 | 4 | 5 | 6 | | VI-1 | Spr |
| 14513 | 3 | 4 | 5 | 6 | | VI-1 | Spred1 |
| 14514 | 3 | 4 | 5 | 6 | | VI-1 | Spred3 |
| 14515 | 3 | 4 | 5 | 6 | | VI-1 | Sprr2d |
| 14516 | 3 | 4 | 5 | 6 | | VI-1 | Spryd3 |
| 14517 | 3 | 4 | 5 | 6 | | VI-1 | Spryd4 |
| 14518 | 3 | 4 | 5 | 6 | | VI-1 | Spsb2 |
| 14519 | 3 | 4 | 5 | 6 | | VI-1 | Sptbn4 |
| 14520 | 3 | 4 | 5 | 6 | | VI-1 | Sptlc1 |
| 14521 | 3 | 4 | 5 | 6 | | VI-1 | Sptlc2 |
| 14522 | 3 | 4 | 5 | 6 | | VI-1 | Sptssa |
| 14523 | 3 | 4 | 5 | 6 | | VI-1 | Spty2d1 |
| 14524 | 3 | 4 | 5 | 6 | | VI-1 | Sqle |
| 14525 | 3 | 4 | 5 | 6 | | VI-1 | Sqrdl |
| 14526 | 3 | 4 | 5 | 6 | | VI-1 | Sra1 |
| 14527 | 3 | 4 | 5 | 6 | | VI-1 | Src |
| 14528 | 3 | 4 | 5 | 6 | | VI-1 | Scrb4d |
| 14529 | 3 | 4 | 5 | 6 | | VI-1 | Srd5a2 |
| 14530 | 3 | 4 | 5 | 6 | | VI-1 | Srf |
| 14531 | 3 | 4 | 5 | 6 | | VI-1 | Srfbp1 |
| 14532 | 3 | 4 | 5 | 6 | | VI-1 | Srgap3 |
| 14533 | 3 | 4 | 5 | 6 | | VI-1 | Srgn |
| 14534 | 3 | 4 | 5 | 6 | | VI-1 | Sri |
| 14535 | 3 | 4 | 5 | 6 | | VI-1 | Srp54a |
| 14536 | 3 | 4 | 5 | 6 | | VI-1 | Srp54b |
| 14537 | 3 | 4 | 5 | 6 | | VI-1 | Srp68 |
| 14538 | 3 | 4 | 5 | 6 | | VI-1 | Srprb |
| 14539 | 3 | 4 | 5 | 6 | | VI-1 | Srpx |
| 14540 | 3 | 4 | 5 | 6 | | VI-1 | Srpx2 |
| 14541 | 3 | 4 | 5 | 6 | | VI-1 | Srr |
| 14542 | 3 | 4 | 5 | 6 | | VI-1 | Srrm1 |
| 14543 | 3 | 4 | 5 | 6 | | VI-1 | Srrm2 |
| 14544 | 3 | 4 | 5 | 6 | | VI-1 | Srrm4 |
| 14545 | 3 | 4 | 5 | 6 | | VI-1 | Srrt |
| 14546 | 3 | 4 | 5 | 6 | | VI-1 | Srsf3 |
| 14547 | 3 | 4 | 5 | 6 | | VI-1 | Srsf4 |
| 14548 | 3 | 4 | 5 | 6 | | VI-1 | Srsf7 |
| 14549 | 3 | 4 | 5 | 6 | | VI-1 | Srsf9 |
| 14550 | 3 | 4 | 5 | 6 | | VI-1 | Srxn1 |
| 14551 | 3 | 4 | 5 | 6 | | VI-1 | Ssfa2 |
| 14552 | 3 | 4 | 5 | 6 | | VI-1 | Ssh1 |
| 14553 | 3 | 4 | 5 | 6 | | VI-1 | Ssh2 |
| 14554 | 3 | 4 | 5 | 6 | | VI-1 | Ssmem1 |
| 14555 | 3 | 4 | 5 | 6 | | VI-1 | Ssr2 |
| 14556 | 3 | 4 | 5 | 6 | | VI-1 | Ssrp1 |
| 14557 | 3 | 4 | 5 | 6 | | VI-1 | Sstr3 |
| 14558 | 3 | 4 | 5 | 6 | | VI-1 | Ssu72 |
| 14559 | 3 | 4 | 5 | 6 | | VI-1 | Ssx2ip |
| 14560 | 3 | 4 | 5 | 6 | | VI-1 | St3gal1 |
| 14561 | 3 | 4 | 5 | 6 | | VI-1 | St3gal4 |
| 14562 | 3 | 4 | 5 | 6 | | VI-1 | St3gal6 |
| 14563 | 3 | 4 | 5 | 6 | | VI-1 | St5 |
| 14564 | 3 | 4 | 5 | 6 | | VI-1 | St6galnac1 |
| 14565 | 3 | 4 | 5 | 6 | | VI-1 | St6galnac4 |
| 14566 | 3 | 4 | 5 | 6 | | VI-1 | St7 |
| 14567 | 3 | 4 | 5 | 6 | | VI-1 | St7l |
| 14568 | 3 | 4 | 5 | 6 | | VI-1 | St8sia3 |
| 14569 | 3 | 4 | 5 | 6 | | VI-1 | St8sia5 |
| 14570 | 3 | 4 | 5 | 6 | | VI-1 | Stab1 |
| 14571 | 3 | 4 | 5 | 6 | | VI-1 | Stac3 |
| 14572 | 3 | 4 | 5 | 6 | | VI-1 | Stag2 |
| 14573 | 3 | 4 | 5 | 6 | | VI-1 | Stambp |
| 14574 | 3 | 4 | 5 | 6 | | VI-1 | Stap2 |
| 14575 | 3 | 4 | 5 | 6 | | VI-1 | Stard13 |
| 14576 | 3 | 4 | 5 | 6 | | VI-1 | Stard3 |
| 14577 | 3 | 4 | 5 | 6 | | VI-1 | Stard7 |
| 14578 | 3 | 4 | 5 | 6 | | VI-1 | Stat1 |
| 14579 | 3 | 4 | 5 | 6 | | VI-1 | Stat2 |
| 14580 | 3 | 4 | 5 | 6 | | VI-1 | Stat3 |
| 14581 | 3 | 4 | 5 | 6 | | VI-1 | Stat4 |
| 14582 | 3 | 4 | 5 | 6 | | VI-1 | Stau1 |
| 14583 | 3 | 4 | 5 | 6 | | VI-1 | Stau2 |
| 14584 | 3 | 4 | 5 | 6 | | VI-1 | Stc1 |
| 14585 | 3 | 4 | 5 | 6 | | VI-1 | Stc2 |
| 14586 | 3 | 4 | 5 | 6 | | VI-1 | Stfa2 |
| 14587 | 3 | 4 | 5 | 6 | | VI-1 | Stk11 |
| 14588 | 3 | 4 | 5 | 6 | | VI-1 | Stk11ip |
| 14589 | 3 | 4 | 5 | 6 | | VI-1 | Stk16 |
| 14590 | 3 | 4 | 5 | 6 | | VI-1 | Stk24 |

Fig. 34 - 77

| | | | | | | |
|---|---|---|---|---|---|---|
| 14591 | 3 | 4 | 5 | 6 | VI-1 | Stk3 |
| 14592 | 3 | 4 | 5 | 6 | VI-1 | Stk32a |
| 14593 | 3 | 4 | 5 | 6 | VI-1 | Stk32c |
| 14594 | 3 | 4 | 5 | 6 | VI-1 | Stk33 |
| 14595 | 3 | 4 | 5 | 6 | VI-1 | Stk38l |
| 14596 | 3 | 4 | 5 | 6 | VI-1 | Stmnd1 |
| 14597 | 3 | 4 | 5 | 6 | VI-1 | Stoml2 |
| 14598 | 3 | 4 | 5 | 6 | VI-1 | Stox1 |
| 14599 | 3 | 4 | 5 | 6 | VI-1 | Stox2 |
| 14600 | 3 | 4 | 5 | 6 | VI-1 | Stpg1 |
| 14601 | 3 | 4 | 5 | 6 | VI-1 | Stra13 |
| 14602 | 3 | 4 | 5 | 6 | VI-1 | Strip2 |
| 14603 | 3 | 4 | 5 | 6 | VI-1 | Strn3 |
| 14604 | 3 | 4 | 5 | 6 | VI-1 | Stx11 |
| 14605 | 3 | 4 | 5 | 6 | VI-1 | Stx17 |
| 14606 | 3 | 4 | 5 | 6 | VI-1 | Stx3 |
| 14607 | 3 | 4 | 5 | 6 | VI-1 | Stx5a |
| 14608 | 3 | 4 | 5 | 6 | VI-1 | Stx6 |
| 14609 | 3 | 4 | 5 | 6 | VI-1 | Stxbp2 |
| 14610 | 3 | 4 | 5 | 6 | VI-1 | Stxbp5 |
| 14611 | 3 | 4 | 5 | 6 | VI-1 | Stxbp6 |
| 14612 | 3 | 4 | 5 | 6 | VI-1 | Styxl1 |
| 14613 | 3 | 4 | 5 | 6 | VI-1 | Sub1 |
| 14614 | 3 | 4 | 5 | 6 | VI-1 | Sucla2 |
| 14615 | 3 | 4 | 5 | 6 | VI-1 | Suco |
| 14616 | 3 | 4 | 5 | 6 | VI-1 | Suds3 |
| 14617 | 3 | 4 | 5 | 6 | VI-1 | Sufu |
| 14618 | 3 | 4 | 5 | 6 | VI-1 | Sugp1 |
| 14619 | 3 | 4 | 5 | 6 | VI-1 | Sulf1 |
| 14620 | 3 | 4 | 5 | 6 | VI-1 | Sulf2 |
| 14621 | 3 | 4 | 5 | 6 | VI-1 | Sult1c2 |
| 14622 | 3 | 4 | 5 | 6 | VI-1 | Sult1d1 |
| 14623 | 3 | 4 | 5 | 6 | VI-1 | Sumf2 |
| 14624 | 3 | 4 | 5 | 6 | VI-1 | Sumo1 |
| 14625 | 3 | 4 | 5 | 6 | VI-1 | Sumo2 |
| 14626 | 3 | 4 | 5 | 6 | VI-1 | Sun1 |
| 14627 | 3 | 4 | 5 | 6 | VI-1 | Sun2 |
| 14628 | 3 | 4 | 5 | 6 | VI-1 | Sun3 |
| 14629 | 3 | 4 | 5 | 6 | VI-1 | Supt6 |
| 14630 | 3 | 4 | 5 | 6 | VI-1 | Supv3l1 |
| 14631 | 3 | 4 | 5 | 6 | VI-1 | Susd2 |
| 14632 | 3 | 4 | 5 | 6 | VI-1 | Susd4 |
| 14633 | 3 | 4 | 5 | 6 | VI-1 | Susd5 |
| 14634 | 3 | 4 | 5 | 6 | VI-1 | Suv39h1 |
| 14635 | 3 | 4 | 5 | 6 | VI-1 | Suv39h2 |
| 14636 | 3 | 4 | 5 | 6 | VI-1 | Svop |
| 14637 | 3 | 4 | 5 | 6 | VI-1 | Svopl |
| 14638 | 3 | 4 | 5 | 6 | VI-1 | Svs5 |
| 14639 | 3 | 4 | 5 | 6 | VI-1 | Svs6 |
| 14640 | 3 | 4 | 5 | 6 | VI-1 | Swi5 |
| 14641 | 3 | 4 | 5 | 6 | VI-1 | Swt1 |
| 14642 | 3 | 4 | 5 | 6 | VI-1 | Syce1l |
| 14643 | 3 | 4 | 5 | 6 | VI-1 | Syce2 |
| 14644 | 3 | 4 | 5 | 6 | VI-1 | Sycp1-ps1 |
| 14645 | 3 | 4 | 5 | 6 | VI-1 | Sycp3 |
| 14646 | 3 | 4 | 5 | 6 | VI-1 | Syde1 |
| 14647 | 3 | 4 | 5 | 6 | VI-1 | Syndig1 |
| 14648 | 3 | 4 | 5 | 6 | VI-1 | Syndig1l |
| 14649 | 3 | 4 | 5 | 6 | VI-1 | Syne1 |
| 14650 | 3 | 4 | 5 | 6 | VI-1 | Syne3 |
| 14651 | 3 | 4 | 5 | 6 | VI-1 | Syne4 |
| 14652 | 3 | 4 | 5 | 6 | VI-1 | Syngap1 |
| 14653 | 3 | 4 | 5 | 6 | VI-1 | Syngr2 |
| 14654 | 3 | 4 | 5 | 6 | VI-1 | Syngr4 |
| 14655 | 3 | 4 | 5 | 6 | VI-1 | Synj2bp |
| 14656 | 3 | 4 | 5 | 6 | VI-1 | Synm |
| 14657 | 3 | 4 | 5 | 6 | VI-1 | Synpo |
| 14658 | 3 | 4 | 5 | 6 | VI-1 | Synpo2l |
| 14659 | 3 | 4 | 5 | 6 | VI-1 | Synpr |
| 14660 | 3 | 4 | 5 | 6 | VI-1 | Synrg |
| 14661 | 3 | 4 | 5 | 6 | VI-1 | Sypl2 |
| 14662 | 3 | 4 | 5 | 6 | VI-1 | Sys1 |
| 14663 | 3 | 4 | 5 | 6 | VI-1 | Syt12 |
| 14664 | 3 | 4 | 5 | 6 | VI-1 | Syt14 |
| 14665 | 3 | 4 | 5 | 6 | VI-1 | Syt16 |
| 14666 | 3 | 4 | 5 | 6 | VI-1 | Syt2 |
| 14667 | 3 | 4 | 5 | 6 | VI-1 | Syt3 |
| 14668 | 3 | 4 | 5 | 6 | VI-1 | Syt8 |
| 14669 | 3 | 4 | 5 | 6 | VI-1 | T2 |
| 14670 | 3 | 4 | 5 | 6 | VI-1 | Tab1 |
| 14671 | 3 | 4 | 5 | 6 | VI-1 | Tab3 |
| 14672 | 3 | 4 | 5 | 6 | VI-1 | Tac1 |
| 14673 | 3 | 4 | 5 | 6 | VI-1 | Tac4 |
| 14674 | 3 | 4 | 5 | 6 | VI-1 | Tacc2 |
| 14675 | 3 | 4 | 5 | 6 | VI-1 | Tacc3 |
| 14676 | 3 | 4 | 5 | 6 | VI-1 | Tacstd2 |
| 14677 | 3 | 4 | 5 | 6 | VI-1 | Tada2a |
| 14678 | 3 | 4 | 5 | 6 | VI-1 | Tada3 |
| 14679 | 3 | 4 | 5 | 6 | VI-1 | Taf10 |
| 14680 | 3 | 4 | 5 | 6 | VI-1 | Taf11 |
| 14681 | 3 | 4 | 5 | 6 | VI-1 | Taf12 |
| 14682 | 3 | 4 | 5 | 6 | VI-1 | Taf13 |
| 14683 | 3 | 4 | 5 | 6 | VI-1 | Taf15 |
| 14684 | 3 | 4 | 5 | 6 | VI-1 | Taf1b |
| 14685 | 3 | 4 | 5 | 6 | VI-1 | Taf1c |
| 14686 | 3 | 4 | 5 | 6 | VI-1 | Taf4b |
| 14687 | 3 | 4 | 5 | 6 | VI-1 | Taf5 |
| 14688 | 3 | 4 | 5 | 6 | VI-1 | Taf6 |
| 14689 | 3 | 4 | 5 | 6 | VI-1 | Taf6l |
| 14690 | 3 | 4 | 5 | 6 | VI-1 | Taf8 |
| 14691 | 3 | 4 | 5 | 6 | VI-1 | Taf9 |
| 14692 | 3 | 4 | 5 | 6 | VI-1 | Taf9b |
| 14693 | 3 | 4 | 5 | 6 | VI-1 | Tagln |
| 14694 | 3 | 4 | 5 | 6 | VI-1 | Tagln2 |
| 14695 | 3 | 4 | 5 | 6 | VI-1 | Tanc1 |
| 14696 | 3 | 4 | 5 | 6 | VI-1 | Tango2 |
| 14697 | 3 | 4 | 5 | 6 | VI-1 | Tango6 |
| 14698 | 3 | 4 | 5 | 6 | VI-1 | Tap1 |
| 14699 | 3 | 4 | 5 | 6 | VI-1 | Tap2 |
| 14700 | 3 | 4 | 5 | 6 | VI-1 | Tapbp |
| 14701 | 3 | 4 | 5 | 6 | VI-1 | Tapbpl |
| 14702 | 3 | 4 | 5 | 6 | VI-1 | Tapt1 |
| 14703 | 3 | 4 | 5 | 6 | VI-1 | Tarm1 |
| 14704 | 3 | 4 | 5 | 6 | VI-1 | Tars |
| 14705 | 3 | 4 | 5 | 6 | VI-1 | Tars2 |
| 14706 | 3 | 4 | 5 | 6 | VI-1 | Tarsl2 |
| 14707 | 3 | 4 | 5 | 6 | VI-1 | Tas1r1 |
| 14708 | 3 | 4 | 5 | 6 | VI-1 | Tasp1 |
| 14709 | 3 | 4 | 5 | 6 | VI-1 | Taz |
| 14710 | 3 | 4 | 5 | 6 | VI-1 | Tbata |
| 14711 | 3 | 4 | 5 | 6 | VI-1 | Tbc1d10a |
| 14712 | 3 | 4 | 5 | 6 | VI-1 | Tbc1d12 |
| 14713 | 3 | 4 | 5 | 6 | VI-1 | Tbc1d14 |
| 14714 | 3 | 4 | 5 | 6 | VI-1 | Tbc1d15 |
| 14715 | 3 | 4 | 5 | 6 | VI-1 | Tbc1d19 |
| 14716 | 3 | 4 | 5 | 6 | VI-1 | Tbc1d22b |
| 14717 | 3 | 4 | 5 | 6 | VI-1 | Tbc1d30 |
| 14718 | 3 | 4 | 5 | 6 | VI-1 | Tbc1d8 |
| 14719 | 3 | 4 | 5 | 6 | VI-1 | Tbc1d8b |
| 14720 | 3 | 4 | 5 | 6 | VI-1 | Tbca |
| 14721 | 3 | 4 | 5 | 6 | VI-1 | Tbcb |
| 14722 | 3 | 4 | 5 | 6 | VI-1 | Tbcc |
| 14723 | 3 | 4 | 5 | 6 | VI-1 | Tbl1x |
| 14724 | 3 | 4 | 5 | 6 | VI-1 | Tbl1xr1 |
| 14725 | 3 | 4 | 5 | 6 | VI-1 | Tbl2 |
| 14726 | 3 | 4 | 5 | 6 | VI-1 | Tbl3 |
| 14727 | 3 | 4 | 5 | 6 | VI-1 | Tbr1 |
| 14728 | 3 | 4 | 5 | 6 | VI-1 | Tbrg1 |
| 14729 | 3 | 4 | 5 | 6 | VI-1 | Tbrg4 |
| 14730 | 3 | 4 | 5 | 6 | VI-1 | Tbx2 |
| 14731 | 3 | 4 | 5 | 6 | VI-1 | Tbx6 |
| 14732 | 3 | 4 | 5 | 6 | VI-1 | Tbxa2r |
| 14733 | 3 | 4 | 5 | 6 | VI-1 | Tbxas1 |
| 14734 | 3 | 4 | 5 | 6 | VI-1 | Tcea1 |
| 14735 | 3 | 4 | 5 | 6 | VI-1 | Tcea2 |
| 14736 | 3 | 4 | 5 | 6 | VI-1 | Tceal1 |
| 14737 | 3 | 4 | 5 | 6 | VI-1 | Tceanc |
| 14738 | 3 | 4 | 5 | 6 | VI-1 | Tceanc2 |
| 14739 | 3 | 4 | 5 | 6 | VI-1 | Tceb3 |
| 14740 | 3 | 4 | 5 | 6 | VI-1 | Tcf15 |
| 14741 | 3 | 4 | 5 | 6 | VI-1 | Tcf19 |
| 14742 | 3 | 4 | 5 | 6 | VI-1 | Tcf23 |
| 14743 | 3 | 4 | 5 | 6 | VI-1 | Tcf3 |
| 14744 | 3 | 4 | 5 | 6 | VI-1 | Tcfl5 |
| 14745 | 3 | 4 | 5 | 6 | VI-1 | Tchh |
| 14746 | 3 | 4 | 5 | 6 | VI-1 | Tchhl1 |
| 14747 | 3 | 4 | 5 | 6 | VI-1 | Tchp |
| 14748 | 3 | 4 | 5 | 6 | VI-1 | Tcirg1 |
| 14749 | 3 | 4 | 5 | 6 | VI-1 | Tcte1 |
| 14750 | 3 | 4 | 5 | 6 | VI-1 | Tctex1d1 |
| 14751 | 3 | 4 | 5 | 6 | VI-1 | Tctex1d2 |
| 14752 | 3 | 4 | 5 | 6 | VI-1 | Tctex1d4 |
| 14753 | 3 | 4 | 5 | 6 | VI-1 | Tctn2 |
| 14754 | 3 | 4 | 5 | 6 | VI-1 | Tdg |
| 14755 | 3 | 4 | 5 | 6 | VI-1 | Tdh |
| 14756 | 3 | 4 | 5 | 6 | VI-1 | Tdo2 |
| 14757 | 3 | 4 | 5 | 6 | VI-1 | Tdrd9 |
| 14758 | 3 | 4 | 5 | 6 | VI-1 | Tdrp |
| 14759 | 3 | 4 | 5 | 6 | VI-1 | Tead2 |
| 14760 | 3 | 4 | 5 | 6 | VI-1 | Tef |
| 14761 | 3 | 4 | 5 | 6 | VI-1 | Tekt4 |
| 14762 | 3 | 4 | 5 | 6 | VI-1 | Tekt5 |
| 14763 | 3 | 4 | 5 | 6 | VI-1 | Telo2 |
| 14764 | 3 | 4 | 5 | 6 | VI-1 | Ten1 |
| 14765 | 3 | 4 | 5 | 6 | VI-1 | Tenc1 |
| 14766 | 3 | 4 | 5 | 6 | VI-1 | Tenm3 |
| 14767 | 3 | 4 | 5 | 6 | VI-1 | Tep1 |
| 14768 | 3 | 4 | 5 | 6 | VI-1 | Terc |
| 14769 | 3 | 4 | 5 | 6 | VI-1 | Terf1 |
| 14770 | 3 | 4 | 5 | 6 | VI-1 | Terf2 |
| 14771 | 3 | 4 | 5 | 6 | VI-1 | Tes |
| 14772 | 3 | 4 | 5 | 6 | VI-1 | Tex101 |
| 14773 | 3 | 4 | 5 | 6 | VI-1 | Tex11 |
| 14774 | 3 | 4 | 5 | 6 | VI-1 | Tex12 |
| 14775 | 3 | 4 | 5 | 6 | VI-1 | Tex22 |
| 14776 | 3 | 4 | 5 | 6 | VI-1 | Tex261 |
| 14777 | 3 | 4 | 5 | 6 | VI-1 | Tex33 |
| 14778 | 3 | 4 | 5 | 6 | VI-1 | Tex38 |
| 14779 | 3 | 4 | 5 | 6 | VI-1 | Tex40 |
| 14780 | 3 | 4 | 5 | 6 | VI-1 | Tfam |
| 14781 | 3 | 4 | 5 | 6 | VI-1 | Tfb1m |
| 14782 | 3 | 4 | 5 | 6 | VI-1 | Tfcp2l1 |

Fig. 34 - 78

| | | | | | | |
|---|---|---|---|---|---|---|
| 14783 | 3 | 4 | 5 | 6 | VI-1 | Tfdp2 |
| 14784 | 3 | 4 | 5 | 6 | VI-1 | Tfeb |
| 14785 | 3 | 4 | 5 | 6 | VI-1 | Tfec |
| 14786 | 3 | 4 | 5 | 6 | VI-1 | Tfg |
| 14787 | 3 | 4 | 5 | 6 | VI-1 | Tfip11 |
| 14788 | 3 | 4 | 5 | 6 | VI-1 | Tfpi |
| 14789 | 3 | 4 | 5 | 6 | VI-1 | Tfpi2 |
| 14790 | 3 | 4 | 5 | 6 | VI-1 | Tfpt |
| 14791 | 3 | 4 | 5 | 6 | VI-1 | Tfr2 |
| 14792 | 3 | 4 | 5 | 6 | VI-1 | Tfrc |
| 14793 | 3 | 4 | 5 | 6 | VI-1 | Tg |
| 14794 | 3 | 4 | 5 | 6 | VI-1 | Tgds |
| 14795 | 3 | 4 | 5 | 6 | VI-1 | Tgfbi |
| 14796 | 3 | 4 | 5 | 6 | VI-1 | Tgfbr1 |
| 14797 | 3 | 4 | 5 | 6 | VI-1 | Tgfbr2 |
| 14798 | 3 | 4 | 5 | 6 | VI-1 | Tgfbr3 |
| 14799 | 3 | 4 | 5 | 6 | VI-1 | Tgm1 |
| 14800 | 3 | 4 | 5 | 6 | VI-1 | Tgm2 |
| 14801 | 3 | 4 | 5 | 6 | VI-1 | Th |
| 14802 | 3 | 4 | 5 | 6 | VI-1 | Tha1 |
| 14803 | 3 | 4 | 5 | 6 | VI-1 | Thbs2 |
| 14804 | 3 | 4 | 5 | 6 | VI-1 | Thbs3 |
| 14805 | 3 | 4 | 5 | 6 | VI-1 | Them5 |
| 14806 | 3 | 4 | 5 | 6 | VI-1 | Thg1l |
| 14807 | 3 | 4 | 5 | 6 | VI-1 | Thnsl1 |
| 14808 | 3 | 4 | 5 | 6 | VI-1 | Thoc1 |
| 14809 | 3 | 4 | 5 | 6 | VI-1 | Thoc6 |
| 14810 | 3 | 4 | 5 | 6 | VI-1 | Thoc7 |
| 14811 | 3 | 4 | 5 | 6 | VI-1 | Thop1 |
| 14812 | 3 | 4 | 5 | 6 | VI-1 | Thpo |
| 14813 | 3 | 4 | 5 | 6 | VI-1 | Thrap3 |
| 14814 | 3 | 4 | 5 | 6 | VI-1 | Thrb |
| 14815 | 3 | 4 | 5 | 6 | VI-1 | Thsd7a |
| 14816 | 3 | 4 | 5 | 6 | VI-1 | Thumpd2 |
| 14817 | 3 | 4 | 5 | 6 | VI-1 | Thyn1 |
| 14818 | 3 | 4 | 5 | 6 | VI-1 | Tia1 |
| 14819 | 3 | 4 | 5 | 6 | VI-1 | Tial1 |
| 14820 | 3 | 4 | 5 | 6 | VI-1 | Tiam2 |
| 14821 | 3 | 4 | 5 | 6 | VI-1 | Ticam1 |
| 14822 | 3 | 4 | 5 | 6 | VI-1 | Tie1 |
| 14823 | 3 | 4 | 5 | 6 | VI-1 | Tifab |
| 14824 | 3 | 4 | 5 | 6 | VI-1 | Tigd2 |
| 14825 | 3 | 4 | 5 | 6 | VI-1 | Timd4 |
| 14826 | 3 | 4 | 5 | 6 | VI-1 | Timm10 |
| 14827 | 3 | 4 | 5 | 6 | VI-1 | Timm17a |
| 14828 | 3 | 4 | 5 | 6 | VI-1 | Timm17b |
| 14829 | 3 | 4 | 5 | 6 | VI-1 | Timm22 |
| 14830 | 3 | 4 | 5 | 6 | VI-1 | Timm23 |
| 14831 | 3 | 4 | 5 | 6 | VI-1 | Timm8b |
| 14832 | 3 | 4 | 5 | 6 | VI-1 | Timmdc1 |
| 14833 | 3 | 4 | 5 | 6 | VI-1 | Timp4 |
| 14834 | 3 | 4 | 5 | 6 | VI-1 | Tinag |
| 14835 | 3 | 4 | 5 | 6 | VI-1 | Tinagl1 |
| 14836 | 3 | 4 | 5 | 6 | VI-1 | Tinf2 |
| 14837 | 3 | 4 | 5 | 6 | VI-1 | Tipin |
| 14838 | 3 | 4 | 5 | 6 | VI-1 | Tirap |
| 14839 | 3 | 4 | 5 | 6 | VI-1 | Tjp3 |
| 14840 | 3 | 4 | 5 | 6 | VI-1 | Tkt |
| 14841 | 3 | 4 | 5 | 6 | VI-1 | Tlcd1 |
| 14842 | 3 | 4 | 5 | 6 | VI-1 | Tle1 |
| 14843 | 3 | 4 | 5 | 6 | VI-1 | Tle3 |
| 14844 | 3 | 4 | 5 | 6 | VI-1 | Tle4 |
| 14845 | 3 | 4 | 5 | 6 | VI-1 | Tle6 |
| 14846 | 3 | 4 | 5 | 6 | VI-1 | Tlk2 |
| 14847 | 3 | 4 | 5 | 6 | VI-1 | Tlr1 |
| 14848 | 3 | 4 | 5 | 6 | VI-1 | Tlr12 |
| 14849 | 3 | 4 | 5 | 6 | VI-1 | Tlr13 |
| 14850 | 3 | 4 | 5 | 6 | VI-1 | Tlr2 |
| 14851 | 3 | 4 | 5 | 6 | VI-1 | Tlr4 |
| 14852 | 3 | 4 | 5 | 6 | VI-1 | Tlr6 |
| 14853 | 3 | 4 | 5 | 6 | VI-1 | Tlr7 |
| 14854 | 3 | 4 | 5 | 6 | VI-1 | Tlr8 |
| 14855 | 3 | 4 | 5 | 6 | VI-1 | Tlr9 |
| 14856 | 3 | 4 | 5 | 6 | VI-1 | Tm2d2 |
| 14857 | 3 | 4 | 5 | 6 | VI-1 | Tm2d3 |
| 14858 | 3 | 4 | 5 | 6 | VI-1 | Tm4sf1 |
| 14859 | 3 | 4 | 5 | 6 | VI-1 | Tm4sf20 |
| 14860 | 3 | 4 | 5 | 6 | VI-1 | Tm4sf4 |
| 14861 | 3 | 4 | 5 | 6 | VI-1 | Tm4sf5 |
| 14862 | 3 | 4 | 5 | 6 | VI-1 | Tm6sf2 |
| 14863 | 3 | 4 | 5 | 6 | VI-1 | Tm7sf2 |
| 14864 | 3 | 4 | 5 | 6 | VI-1 | Tma7 |
| 14865 | 3 | 4 | 5 | 6 | VI-1 | Tmbim1 |
| 14866 | 3 | 4 | 5 | 6 | VI-1 | Tmbim4 |
| 14867 | 3 | 4 | 5 | 6 | VI-1 | Tmc4 |
| 14868 | 3 | 4 | 5 | 6 | VI-1 | Tmc7 |
| 14869 | 3 | 4 | 5 | 6 | VI-1 | Tmc8 |
| 14870 | 3 | 4 | 5 | 6 | VI-1 | Tmcc1 |
| 14871 | 3 | 4 | 5 | 6 | VI-1 | Tmcc3 |
| 14872 | 3 | 4 | 5 | 6 | VI-1 | Tmco1 |
| 14873 | 3 | 4 | 5 | 6 | VI-1 | Tmco3 |
| 14874 | 3 | 4 | 5 | 6 | VI-1 | Tmco5 |
| 14875 | 3 | 4 | 5 | 6 | VI-1 | Tmco5b |
| 14876 | 3 | 4 | 5 | 6 | VI-1 | Tmco6 |
| 14877 | 3 | 4 | 5 | 6 | VI-1 | Tmed1 |
| 14878 | 3 | 4 | 5 | 6 | VI-1 | Tmed11 |
| 14879 | 3 | 4 | 5 | 6 | VI-1 | Tmed4 |
| 14880 | 3 | 4 | 5 | 6 | VI-1 | Tmed5 |
| 14881 | 3 | 4 | 5 | 6 | VI-1 | Tmed6 |
| 14882 | 3 | 4 | 5 | 6 | VI-1 | Tmed8 |
| 14883 | 3 | 4 | 5 | 6 | VI-1 | Tmem100 |
| 14884 | 3 | 4 | 5 | 6 | VI-1 | Tmem101 |
| 14885 | 3 | 4 | 5 | 6 | VI-1 | Tmem102 |
| 14886 | 3 | 4 | 5 | 6 | VI-1 | Tmem106a |
| 14887 | 3 | 4 | 5 | 6 | VI-1 | Tmem11 |
| 14888 | 3 | 4 | 5 | 6 | VI-1 | Tmem110 |
| 14889 | 3 | 4 | 5 | 6 | VI-1 | Tmem116 |
| 14890 | 3 | 4 | 5 | 6 | VI-1 | Tmem119 |
| 14891 | 3 | 4 | 5 | 6 | VI-1 | Tmem120b |
| 14892 | 3 | 4 | 5 | 6 | VI-1 | Tmem125 |
| 14893 | 3 | 4 | 5 | 6 | VI-1 | Tmem126a |
| 14894 | 3 | 4 | 5 | 6 | VI-1 | Tmem126b |
| 14895 | 3 | 4 | 5 | 6 | VI-1 | Tmem128 |
| 14896 | 3 | 4 | 5 | 6 | VI-1 | Tmem131 |
| 14897 | 3 | 4 | 5 | 6 | VI-1 | Tmem132b |
| 14898 | 3 | 4 | 5 | 6 | VI-1 | Tmem132e |
| 14899 | 3 | 4 | 5 | 6 | VI-1 | Tmem134 |
| 14900 | 3 | 4 | 5 | 6 | VI-1 | Tmem136 |
| 14901 | 3 | 4 | 5 | 6 | VI-1 | Tmem139 |
| 14902 | 3 | 4 | 5 | 6 | VI-1 | Tmem143 |
| 14903 | 3 | 4 | 5 | 6 | VI-1 | Tmem144 |
| 14904 | 3 | 4 | 5 | 6 | VI-1 | Tmem14a |
| 14905 | 3 | 4 | 5 | 6 | VI-1 | Tmem150b |
| 14906 | 3 | 4 | 5 | 6 | VI-1 | Tmem151b |
| 14907 | 3 | 4 | 5 | 6 | VI-1 | Tmem159 |
| 14908 | 3 | 4 | 5 | 6 | VI-1 | Tmem164 |
| 14909 | 3 | 4 | 5 | 6 | VI-1 | Tmem168 |
| 14910 | 3 | 4 | 5 | 6 | VI-1 | Tmem170 |
| 14911 | 3 | 4 | 5 | 6 | VI-1 | Tmem176a |
| 14912 | 3 | 4 | 5 | 6 | VI-1 | Tmem176b |
| 14913 | 3 | 4 | 5 | 6 | VI-1 | Tmem178 |
| 14914 | 3 | 4 | 5 | 6 | VI-1 | Tmem18 |
| 14915 | 3 | 4 | 5 | 6 | VI-1 | Tmem182 |
| 14916 | 3 | 4 | 5 | 6 | VI-1 | Tmem183a |
| 14917 | 3 | 4 | 5 | 6 | VI-1 | Tmem184a |
| 14918 | 3 | 4 | 5 | 6 | VI-1 | Tmem191c |
| 14919 | 3 | 4 | 5 | 6 | VI-1 | Tmem192 |
| 14920 | 3 | 4 | 5 | 6 | VI-1 | Tmem194b |
| 14921 | 3 | 4 | 5 | 6 | VI-1 | Tmem198 |
| 14922 | 3 | 4 | 5 | 6 | VI-1 | Tmem199 |
| 14923 | 3 | 4 | 5 | 6 | VI-1 | Tmem200a |
| 14924 | 3 | 4 | 5 | 6 | VI-1 | Tmem201 |
| 14925 | 3 | 4 | 5 | 6 | VI-1 | Tmem202 |
| 14926 | 3 | 4 | 5 | 6 | VI-1 | Tmem203 |
| 14927 | 3 | 4 | 5 | 6 | VI-1 | Tmem206 |
| 14928 | 3 | 4 | 5 | 6 | VI-1 | Tmem209 |
| 14929 | 3 | 4 | 5 | 6 | VI-1 | Tmem213 |
| 14930 | 3 | 4 | 5 | 6 | VI-1 | Tmem214 |
| 14931 | 3 | 4 | 5 | 6 | VI-1 | Tmem219 |
| 14932 | 3 | 4 | 5 | 6 | VI-1 | Tmem221 |
| 14933 | 3 | 4 | 5 | 6 | VI-1 | Tmem223 |
| 14934 | 3 | 4 | 5 | 6 | VI-1 | Tmem229a |
| 14935 | 3 | 4 | 5 | 6 | VI-1 | Tmem230 |
| 14936 | 3 | 4 | 5 | 6 | VI-1 | Tmem232 |
| 14937 | 3 | 4 | 5 | 6 | VI-1 | Tmem238 |
| 14938 | 3 | 4 | 5 | 6 | VI-1 | Tmem239 |
| 14939 | 3 | 4 | 5 | 6 | VI-1 | Tmem240 |
| 14940 | 3 | 4 | 5 | 6 | VI-1 | Tmem242 |
| 14941 | 3 | 4 | 5 | 6 | VI-1 | Tmem243 |
| 14942 | 3 | 4 | 5 | 6 | VI-1 | Tmem246 |
| 14943 | 3 | 4 | 5 | 6 | VI-1 | Tmem247 |
| 14944 | 3 | 4 | 5 | 6 | VI-1 | Tmem248 |
| 14945 | 3 | 4 | 5 | 6 | VI-1 | Tmem251 |
| 14946 | 3 | 4 | 5 | 6 | VI-1 | Tmem254a |
| 14947 | 3 | 4 | 5 | 6 | VI-1 | Tmem254b |
| 14948 | 3 | 4 | 5 | 6 | VI-1 | Tmem255a |
| 14949 | 3 | 4 | 5 | 6 | VI-1 | Tmem255b |
| 14950 | 3 | 4 | 5 | 6 | VI-1 | Tmem26 |
| 14951 | 3 | 4 | 5 | 6 | VI-1 | Tmem260 |
| 14952 | 3 | 4 | 5 | 6 | VI-1 | Tmem261 |
| 14953 | 3 | 4 | 5 | 6 | VI-1 | Tmem263 |
| 14954 | 3 | 4 | 5 | 6 | VI-1 | Tmem28 |
| 14955 | 3 | 4 | 5 | 6 | VI-1 | Tmem30b |
| 14956 | 3 | 4 | 5 | 6 | VI-1 | Tmem35 |
| 14957 | 3 | 4 | 5 | 6 | VI-1 | Tmem38a |
| 14958 | 3 | 4 | 5 | 6 | VI-1 | Tmem41a |
| 14959 | 3 | 4 | 5 | 6 | VI-1 | Tmem42 |
| 14960 | 3 | 4 | 5 | 6 | VI-1 | Tmem45b |
| 14961 | 3 | 4 | 5 | 6 | VI-1 | Tmem47 |
| 14962 | 3 | 4 | 5 | 6 | VI-1 | Tmem5 |
| 14963 | 3 | 4 | 5 | 6 | VI-1 | Tmem52 |
| 14964 | 3 | 4 | 5 | 6 | VI-1 | Tmem53 |
| 14965 | 3 | 4 | 5 | 6 | VI-1 | Tmem54 |
| 14966 | 3 | 4 | 5 | 6 | VI-1 | Tmem55a |
| 14967 | 3 | 4 | 5 | 6 | VI-1 | Tmem60 |
| 14968 | 3 | 4 | 5 | 6 | VI-1 | Tmem62 |
| 14969 | 3 | 4 | 5 | 6 | VI-1 | Tmem63a |
| 14970 | 3 | 4 | 5 | 6 | VI-1 | Tmem63b |
| 14971 | 3 | 4 | 5 | 6 | VI-1 | Tmem68 |
| 14972 | 3 | 4 | 5 | 6 | VI-1 | Tmem69 |
| 14973 | 3 | 4 | 5 | 6 | VI-1 | Tmem71 |
| 14974 | 3 | 4 | 5 | 6 | VI-1 | Tmem72 |

Fig. 34 - 79

| | | | | | | |
|---|---|---|---|---|---|---|
| 14975 | 3 | 4 | 5 | 6 | VI-1 | Tmem74b |
| 14976 | 3 | 4 | 5 | 6 | VI-1 | Tmem8 |
| 14977 | 3 | 4 | 5 | 6 | VI-1 | Tmem87b |
| 14978 | 3 | 4 | 5 | 6 | VI-1 | Tmem88b |
| 14979 | 3 | 4 | 5 | 6 | VI-1 | Tmem9 |
| 14980 | 3 | 4 | 5 | 6 | VI-1 | Tmem91 |
| 14981 | 3 | 4 | 5 | 6 | VI-1 | Tmem97 |
| 14982 | 3 | 4 | 5 | 6 | VI-1 | Tmem9b |
| 14983 | 3 | 4 | 5 | 6 | VI-1 | Tmevpg1 |
| 14984 | 3 | 4 | 5 | 6 | VI-1 | Tmf1 |
| 14985 | 3 | 4 | 5 | 6 | VI-1 | Tmie |
| 14986 | 3 | 4 | 5 | 6 | VI-1 | Tmigd1 |
| 14987 | 3 | 4 | 5 | 6 | VI-1 | Tmod3 |
| 14988 | 3 | 4 | 5 | 6 | VI-1 | Tmpo |
| 14989 | 3 | 4 | 5 | 6 | VI-1 | Tmprss13 |
| 14990 | 3 | 4 | 5 | 6 | VI-1 | Tmprss9 |
| 14991 | 3 | 4 | 5 | 6 | VI-1 | Tmsb15a |
| 14992 | 3 | 4 | 5 | 6 | VI-1 | Tmsb15l |
| 14993 | 3 | 4 | 5 | 6 | VI-1 | Tmtc4 |
| 14994 | 3 | 4 | 5 | 6 | VI-1 | Tmx1 |
| 14995 | 3 | 4 | 5 | 6 | VI-1 | Tmx2 |
| 14996 | 3 | 4 | 5 | 6 | VI-1 | Tmx3 |
| 14997 | 3 | 4 | 5 | 6 | VI-1 | Tnfaip1 |
| 14998 | 3 | 4 | 5 | 6 | VI-1 | Tnfaip2 |
| 14999 | 3 | 4 | 5 | 6 | VI-1 | Tnfaip6 |
| 15000 | 3 | 4 | 5 | 6 | VI-1 | Tnfaip8 |
| 15001 | 3 | 4 | 5 | 6 | VI-1 | Tnfaip8l1 |
| 15002 | 3 | 4 | 5 | 6 | VI-1 | Tnfaip8l2 |
| 15003 | 3 | 4 | 5 | 6 | VI-1 | Tnfrsf10b |
| 15004 | 3 | 4 | 5 | 6 | VI-1 | Tnfrsf12a |
| 15005 | 3 | 4 | 5 | 6 | VI-1 | Tnfrsf13c |
| 15006 | 3 | 4 | 5 | 6 | VI-1 | Tnfrsf18 |
| 15007 | 3 | 4 | 5 | 6 | VI-1 | Tnfrsf1a |
| 15008 | 3 | 4 | 5 | 6 | VI-1 | Tnfrsf21 |
| 15009 | 3 | 4 | 5 | 6 | VI-1 | Tnfrsf23 |
| 15010 | 3 | 4 | 5 | 6 | VI-1 | Tnfrsf25 |
| 15011 | 3 | 4 | 5 | 6 | VI-1 | Tnfrsf4 |
| 15012 | 3 | 4 | 5 | 6 | VI-1 | Tnfsf12 |
| 15013 | 3 | 4 | 5 | 6 | VI-1 | Tnfsf13b |
| 15014 | 3 | 4 | 5 | 6 | VI-1 | Tnfsf14 |
| 15015 | 3 | 4 | 5 | 6 | VI-1 | Tnfsf15 |
| 15016 | 3 | 4 | 5 | 6 | VI-1 | Tnfsf9 |
| 15017 | 3 | 4 | 5 | 6 | VI-1 | Tnik |
| 15018 | 3 | 4 | 5 | 6 | VI-1 | Tnip1 |
| 15019 | 3 | 4 | 5 | 6 | VI-1 | Tnip2 |
| 15020 | 3 | 4 | 5 | 6 | VI-1 | Tnks |
| 15021 | 3 | 4 | 5 | 6 | VI-1 | Tnks2 |
| 15022 | 3 | 4 | 5 | 6 | VI-1 | Topo1 |
| 15023 | 3 | 4 | 5 | 6 | VI-1 | Tnrc6b |
| 15024 | 3 | 4 | 5 | 6 | VI-1 | Tnrc6c |
| 15025 | 3 | 4 | 5 | 6 | VI-1 | Tns4 |
| 15026 | 3 | 4 | 5 | 6 | VI-1 | Toe1 |
| 15027 | 3 | 4 | 5 | 6 | VI-1 | Tollip |
| 15028 | 3 | 4 | 5 | 6 | VI-1 | Tom1 |
| 15029 | 3 | 4 | 5 | 6 | VI-1 | Tomm20 |
| 15030 | 3 | 4 | 5 | 6 | VI-1 | Tomm34 |
| 15031 | 3 | 4 | 5 | 6 | VI-1 | Tomm40 |
| 15032 | 3 | 4 | 5 | 6 | VI-1 | Tomm40l |
| 15033 | 3 | 4 | 5 | 6 | VI-1 | Tomm5 |
| 15034 | 3 | 4 | 5 | 6 | VI-1 | Tomm7 |
| 15035 | 3 | 4 | 5 | 6 | VI-1 | Top3a |
| 15036 | 3 | 4 | 5 | 6 | VI-1 | Tor1a |
| 15037 | 3 | 4 | 5 | 6 | VI-1 | Tor1aip1 |
| 15038 | 3 | 4 | 5 | 6 | VI-1 | Tor1b |
| 15039 | 3 | 4 | 5 | 6 | VI-1 | Tor2a |
| 15040 | 3 | 4 | 5 | 6 | VI-1 | Tor3a |
| 15041 | 3 | 4 | 5 | 6 | VI-1 | Tox |
| 15042 | 3 | 4 | 5 | 6 | VI-1 | Tox2 |
| 15043 | 3 | 4 | 5 | 6 | VI-1 | Tpbg |
| 15044 | 3 | 4 | 5 | 6 | VI-1 | Tpcn2 |
| 15045 | 3 | 4 | 5 | 6 | VI-1 | Tpd52l2 |
| 15046 | 3 | 4 | 5 | 6 | VI-1 | Tpgs2 |
| 15047 | 3 | 4 | 5 | 6 | VI-1 | Tph1 |
| 15048 | 3 | 4 | 5 | 6 | VI-1 | Tpi1 |
| 15049 | 3 | 4 | 5 | 6 | VI-1 | Tpk1 |
| 15050 | 3 | 4 | 5 | 6 | VI-1 | Tpm1 |
| 15051 | 3 | 4 | 5 | 6 | VI-1 | Tpm2 |
| 15052 | 3 | 4 | 5 | 6 | VI-1 | Tpm3 |
| 15053 | 3 | 4 | 5 | 6 | VI-1 | Tpmt |
| 15054 | 3 | 4 | 5 | 6 | VI-1 | Tppp2 |
| 15055 | 3 | 4 | 5 | 6 | VI-1 | Tpra1 |
| 15056 | 3 | 4 | 5 | 6 | VI-1 | Tprgl |
| 15057 | 3 | 4 | 5 | 6 | VI-1 | Tprkb |
| 15058 | 3 | 4 | 5 | 6 | VI-1 | Tprn |
| 15059 | 3 | 4 | 5 | 6 | VI-1 | Tpsb2 |
| 15060 | 3 | 4 | 5 | 6 | VI-1 | Tra2a |
| 15061 | 3 | 4 | 5 | 6 | VI-1 | Tra2b |
| 15062 | 3 | 4 | 5 | 6 | VI-1 | Trabd |
| 15063 | 3 | 4 | 5 | 6 | VI-1 | Tradd |
| 15064 | 3 | 4 | 5 | 6 | VI-1 | Traf1 |
| 15065 | 3 | 4 | 5 | 6 | VI-1 | Traf2 |
| 15066 | 3 | 4 | 5 | 6 | VI-1 | Traf3ip1 |
| 15067 | 3 | 4 | 5 | 6 | VI-1 | Traf3ip2 |
| 15068 | 3 | 4 | 5 | 6 | VI-1 | Traf6 |
| 15069 | 3 | 4 | 5 | 6 | VI-1 | Traf7 |
| 15070 | 3 | 4 | 5 | 6 | VI-1 | Traip |
| 15071 | 3 | 4 | 5 | 6 | VI-1 | Tram1l1 |
| 15072 | 3 | 4 | 5 | 6 | VI-1 | Tram2 |
| 15073 | 3 | 4 | 5 | 6 | VI-1 | Trap1 |
| 15074 | 3 | 4 | 5 | 6 | VI-1 | Trappc1 |
| 15075 | 3 | 4 | 5 | 6 | VI-1 | Trappc3 |
| 15076 | 3 | 4 | 5 | 6 | VI-1 | Trappc4 |
| 15077 | 3 | 4 | 5 | 6 | VI-1 | Trappc5 |
| 15078 | 3 | 4 | 5 | 6 | VI-1 | Trappc9 |
| 15079 | 3 | 4 | 5 | 6 | VI-1 | Treh |
| 15080 | 3 | 4 | 5 | 6 | VI-1 | Trem1 |
| 15081 | 3 | 4 | 5 | 6 | VI-1 | Trem2 |
| 15082 | 3 | 4 | 5 | 6 | VI-1 | Trem3 |
| 15083 | 3 | 4 | 5 | 6 | VI-1 | Treml1 |
| 15084 | 3 | 4 | 5 | 6 | VI-1 | Trerf1 |
| 15085 | 3 | 4 | 5 | 6 | VI-1 | Trex1 |
| 15086 | 3 | 4 | 5 | 6 | VI-1 | Trf |
| 15087 | 3 | 4 | 5 | 6 | VI-1 | Triap1 |
| 15088 | 3 | 4 | 5 | 6 | VI-1 | Trib1 |
| 15089 | 3 | 4 | 5 | 6 | VI-1 | Trib3 |
| 15090 | 3 | 4 | 5 | 6 | VI-1 | Tril |
| 15091 | 3 | 4 | 5 | 6 | VI-1 | Trim11 |
| 15092 | 3 | 4 | 5 | 6 | VI-1 | Trim12c |
| 15093 | 3 | 4 | 5 | 6 | VI-1 | Trim14 |
| 15094 | 3 | 4 | 5 | 6 | VI-1 | Trim15 |
| 15095 | 3 | 4 | 5 | 6 | VI-1 | Trim2 |
| 15096 | 3 | 4 | 5 | 6 | VI-1 | Trim23 |
| 15097 | 3 | 4 | 5 | 6 | VI-1 | Trim24 |
| 15098 | 3 | 4 | 5 | 6 | VI-1 | Trim25 |
| 15099 | 3 | 4 | 5 | 6 | VI-1 | Trim26 |
| 15100 | 3 | 4 | 5 | 6 | VI-1 | Trim28 |
| 15101 | 3 | 4 | 5 | 6 | VI-1 | Trim33 |
| 15102 | 3 | 4 | 5 | 6 | VI-1 | Trim34b |
| 15103 | 3 | 4 | 5 | 6 | VI-1 | Trim36 |
| 15104 | 3 | 4 | 5 | 6 | VI-1 | Trim37 |
| 15105 | 3 | 4 | 5 | 6 | VI-1 | Trim45 |
| 15106 | 3 | 4 | 5 | 6 | VI-1 | Trim46 |
| 15107 | 3 | 4 | 5 | 6 | VI-1 | Trim50 |
| 15108 | 3 | 4 | 5 | 6 | VI-1 | Trim67 |
| 15109 | 3 | 4 | 5 | 6 | VI-1 | Trim7 |
| 15110 | 3 | 4 | 5 | 6 | VI-1 | Trim72 |
| 15111 | 3 | 4 | 5 | 6 | VI-1 | Trio |
| 15112 | 3 | 4 | 5 | 6 | VI-1 | Triobp |
| 15113 | 3 | 4 | 5 | 6 | VI-1 | Trip11 |
| 15114 | 3 | 4 | 5 | 6 | VI-1 | Trip12 |
| 15115 | 3 | 4 | 5 | 6 | VI-1 | Trit1 |
| 15116 | 3 | 4 | 5 | 6 | VI-1 | Trmt10b |
| 15117 | 3 | 4 | 5 | 6 | VI-1 | Trmt112 |
| 15118 | 3 | 4 | 5 | 6 | VI-1 | Trmt1l |
| 15119 | 3 | 4 | 5 | 6 | VI-1 | Trmt2a |
| 15120 | 3 | 4 | 5 | 6 | VI-1 | Trmt44 |
| 15121 | 3 | 4 | 5 | 6 | VI-1 | Trmt61a |
| 15122 | 3 | 4 | 5 | 6 | VI-1 | Trnt1 |
| 15123 | 3 | 4 | 5 | 6 | VI-1 | Trove2 |
| 15124 | 3 | 4 | 5 | 6 | VI-1 | Trp53i11 |
| 15125 | 3 | 4 | 5 | 6 | VI-1 | Trp53i13 |
| 15126 | 3 | 4 | 5 | 6 | VI-1 | Trp53inp2 |
| 15127 | 3 | 4 | 5 | 6 | VI-1 | Trpc4ap |
| 15128 | 3 | 4 | 5 | 6 | VI-1 | Trpm2 |
| 15129 | 3 | 4 | 5 | 6 | VI-1 | Trpm4 |
| 15130 | 3 | 4 | 5 | 6 | VI-1 | Trpm5 |
| 15131 | 3 | 4 | 5 | 6 | VI-1 | Trpm6 |
| 15132 | 3 | 4 | 5 | 6 | VI-1 | Trpm8 |
| 15133 | 3 | 4 | 5 | 6 | VI-1 | Trpt1 |
| 15134 | 3 | 4 | 5 | 6 | VI-1 | Trpv2 |
| 15135 | 3 | 4 | 5 | 6 | VI-1 | Trpv4 |
| 15136 | 3 | 4 | 5 | 6 | VI-1 | Trpv6 |
| 15137 | 3 | 4 | 5 | 6 | VI-1 | Tsc1 |
| 15138 | 3 | 4 | 5 | 6 | VI-1 | Tsc22d1 |
| 15139 | 3 | 4 | 5 | 6 | VI-1 | Tsc22d2 |
| 15140 | 3 | 4 | 5 | 6 | VI-1 | Tsc22d4 |
| 15141 | 3 | 4 | 5 | 6 | VI-1 | Tsen15 |
| 15142 | 3 | 4 | 5 | 6 | VI-1 | Tsen54 |
| 15143 | 3 | 4 | 5 | 6 | VI-1 | Tsg101 |
| 15144 | 3 | 4 | 5 | 6 | VI-1 | Tsga13 |
| 15145 | 3 | 4 | 5 | 6 | VI-1 | Tsga8 |
| 15146 | 3 | 4 | 5 | 6 | VI-1 | Tsks |
| 15147 | 3 | 4 | 5 | 6 | VI-1 | Tsku |
| 15148 | 3 | 4 | 5 | 6 | VI-1 | Tsnaxip1 |
| 15149 | 3 | 4 | 5 | 6 | VI-1 | Tspan1 |
| 15150 | 3 | 4 | 5 | 6 | VI-1 | Tspan12 |
| 15151 | 3 | 4 | 5 | 6 | VI-1 | Tspan13 |
| 15152 | 3 | 4 | 5 | 6 | VI-1 | Tspan31 |
| 15153 | 3 | 4 | 5 | 6 | VI-1 | Tspan32 |
| 15154 | 3 | 4 | 5 | 6 | VI-1 | Tspan33 |
| 15155 | 3 | 4 | 5 | 6 | VI-1 | Tspan5 |
| 15156 | 3 | 4 | 5 | 6 | VI-1 | Tspan7 |
| 15157 | 3 | 4 | 5 | 6 | VI-1 | Tspan9 |
| 15158 | 3 | 4 | 5 | 6 | VI-1 | Tspyl2 |
| 15159 | 3 | 4 | 5 | 6 | VI-1 | Tspyl5 |
| 15160 | 3 | 4 | 5 | 6 | VI-1 | Tsr3 |
| 15161 | 3 | 4 | 5 | 6 | VI-1 | Tssk1 |
| 15162 | 3 | 4 | 5 | 6 | VI-1 | Tssk2 |
| 15163 | 3 | 4 | 5 | 6 | VI-1 | Tssk3 |
| 15164 | 3 | 4 | 5 | 6 | VI-1 | Tssk4 |
| 15165 | 3 | 4 | 5 | 6 | VI-1 | Tssk6 |
| 15166 | 3 | 4 | 5 | 6 | VI-1 | Tstd1 |

Fig. 34 - 80

| | | | | | | |
|---|---|---|---|---|---|---|
| 15167 | 3 | 4 | 5 | 6 | VI-1 | Tstd3 |
| 15168 | 3 | 4 | 5 | 6 | VI-1 | Tsx |
| 15169 | 3 | 4 | 5 | 6 | VI-1 | Ttbk2 |
| 15170 | 3 | 4 | 5 | 6 | VI-1 | Ttc1 |
| 15171 | 3 | 4 | 5 | 6 | VI-1 | Ttc13 |
| 15172 | 3 | 4 | 5 | 6 | VI-1 | Ttc14 |
| 15173 | 3 | 4 | 5 | 6 | VI-1 | Ttc16 |
| 15174 | 3 | 4 | 5 | 6 | VI-1 | Ttc17 |
| 15175 | 3 | 4 | 5 | 6 | VI-1 | Ttc21a |
| 15176 | 3 | 4 | 5 | 6 | VI-1 | Ttc23 |
| 15177 | 3 | 4 | 5 | 6 | VI-1 | Ttc24 |
| 15178 | 3 | 4 | 5 | 6 | VI-1 | Ttc25 |
| 15179 | 3 | 4 | 5 | 6 | VI-1 | Ttc29 |
| 15180 | 3 | 4 | 5 | 6 | VI-1 | Ttc32 |
| 15181 | 3 | 4 | 5 | 6 | VI-1 | Ttc33 |
| 15182 | 3 | 4 | 5 | 6 | VI-1 | Ttc34 |
| 15183 | 3 | 4 | 5 | 6 | VI-1 | Ttc39a |
| 15184 | 3 | 4 | 5 | 6 | VI-1 | Ttc39d |
| 15185 | 3 | 4 | 5 | 6 | VI-1 | Ttc5 |
| 15186 | 3 | 4 | 5 | 6 | VI-1 | Ttc8 |
| 15187 | 3 | 4 | 5 | 6 | VI-1 | Ttc9 |
| 15188 | 3 | 4 | 5 | 6 | VI-1 | Ttc9c |
| 15189 | 3 | 4 | 5 | 6 | VI-1 | Ttf2 |
| 15190 | 3 | 4 | 5 | 6 | VI-1 | Ttk |
| 15191 | 3 | 4 | 5 | 6 | VI-1 | Ttl |
| 15192 | 3 | 4 | 5 | 6 | VI-1 | Ttll1 |
| 15193 | 3 | 4 | 5 | 6 | VI-1 | Ttll10 |
| 15194 | 3 | 4 | 5 | 6 | VI-1 | Ttll11 |
| 15195 | 3 | 4 | 5 | 6 | VI-1 | Ttll3 |
| 15196 | 3 | 4 | 5 | 6 | VI-1 | Ttll4 |
| 15197 | 3 | 4 | 5 | 6 | VI-1 | Ttll6 |
| 15198 | 3 | 4 | 5 | 6 | VI-1 | Ttll8 |
| 15199 | 3 | 4 | 5 | 6 | VI-1 | Ttpa |
| 15200 | 3 | 4 | 5 | 6 | VI-1 | Ttyh3 |
| 15201 | 3 | 4 | 5 | 6 | VI-1 | Tuba1c |
| 15202 | 3 | 4 | 5 | 6 | VI-1 | Tuba4a |
| 15203 | 3 | 4 | 5 | 6 | VI-1 | Tubal3 |
| 15204 | 3 | 4 | 5 | 6 | VI-1 | Tubb4b |
| 15205 | 3 | 4 | 5 | 6 | VI-1 | Tubb6 |
| 15206 | 3 | 4 | 5 | 6 | VI-1 | Tubg1 |
| 15207 | 3 | 4 | 5 | 6 | VI-1 | Tubgcp2 |
| 15208 | 3 | 4 | 5 | 6 | VI-1 | Tubgcp6 |
| 15209 | 3 | 4 | 5 | 6 | VI-1 | Tug1 |
| 15210 | 3 | 4 | 5 | 6 | VI-1 | Tulp1 |
| 15211 | 3 | 4 | 5 | 6 | VI-1 | Tulp2 |
| 15212 | 3 | 4 | 5 | 6 | VI-1 | Tulp3 |
| 15213 | 3 | 4 | 5 | 6 | VI-1 | Tusc1 |
| 15214 | 3 | 4 | 5 | 6 | VI-1 | Tusc5 |
| 15215 | 3 | 4 | 5 | 6 | VI-1 | Twf2 |
| 15216 | 3 | 4 | 5 | 6 | VI-1 | Twsg1 |
| 15217 | 3 | 4 | 5 | 6 | VI-1 | Txlnb |
| 15218 | 3 | 4 | 5 | 6 | VI-1 | Txlng |
| 15219 | 3 | 4 | 5 | 6 | VI-1 | Txn2 |
| 15220 | 3 | 4 | 5 | 6 | VI-1 | Txndc11 |
| 15221 | 3 | 4 | 5 | 6 | VI-1 | Txndc12 |
| 15222 | 3 | 4 | 5 | 6 | VI-1 | Txndc15 |
| 15223 | 3 | 4 | 5 | 6 | VI-1 | Txndc16 |
| 15224 | 3 | 4 | 5 | 6 | VI-1 | Txndc2 |
| 15225 | 3 | 4 | 5 | 6 | VI-1 | Txndc8 |
| 15226 | 3 | 4 | 5 | 6 | VI-1 | Txndc9 |
| 15227 | 3 | 4 | 5 | 6 | VI-1 | Txnl1 |
| 15228 | 3 | 4 | 5 | 6 | VI-1 | Txnl4a |
| 15229 | 3 | 4 | 5 | 6 | VI-1 | Txnl4b |
| 15230 | 3 | 4 | 5 | 6 | VI-1 | Txnrd2 |
| 15231 | 3 | 4 | 5 | 6 | VI-1 | Tymp |
| 15232 | 3 | 4 | 5 | 6 | VI-1 | Tyms |
| 15233 | 3 | 4 | 5 | 6 | VI-1 | Tyro3 |
| 15234 | 3 | 4 | 5 | 6 | VI-1 | Tysnd1 |
| 15235 | 3 | 4 | 5 | 6 | VI-1 | Tyw1 |
| 15236 | 3 | 4 | 5 | 6 | VI-1 | Tyw5 |
| 15237 | 3 | 4 | 5 | 6 | VI-1 | U2af1l4 |
| 15238 | 3 | 4 | 5 | 6 | VI-1 | U90926 |
| 15239 | 3 | 4 | 5 | 6 | VI-1 | Uaca |
| 15240 | 3 | 4 | 5 | 6 | VI-1 | Uba1 |
| 15241 | 3 | 4 | 5 | 6 | VI-1 | Uba3 |
| 15242 | 3 | 4 | 5 | 6 | VI-1 | Uba5 |
| 15243 | 3 | 4 | 5 | 6 | VI-1 | Uba7 |
| 15244 | 3 | 4 | 5 | 6 | VI-1 | Ubac1 |
| 15245 | 3 | 4 | 5 | 6 | VI-1 | Ubald1 |
| 15246 | 3 | 4 | 5 | 6 | VI-1 | Ubash3b |
| 15247 | 3 | 4 | 5 | 6 | VI-1 | Ubc |
| 15248 | 3 | 4 | 5 | 6 | VI-1 | Ubd |
| 15249 | 3 | 4 | 5 | 6 | VI-1 | Ube2b |
| 15250 | 3 | 4 | 5 | 6 | VI-1 | Ube2d1 |
| 15251 | 3 | 4 | 5 | 6 | VI-1 | Ube2d2b |
| 15252 | 3 | 4 | 5 | 6 | VI-1 | Ube2e2 |
| 15253 | 3 | 4 | 5 | 6 | VI-1 | Ube2f |
| 15254 | 3 | 4 | 5 | 6 | VI-1 | Ube2g2 |
| 15255 | 3 | 4 | 5 | 6 | VI-1 | Ube2j1 |
| 15256 | 3 | 4 | 5 | 6 | VI-1 | Ube2j2 |
| 15257 | 3 | 4 | 5 | 6 | VI-1 | Ube2l3 |
| 15258 | 3 | 4 | 5 | 6 | VI-1 | Ube2o |
| 15259 | 3 | 4 | 5 | 6 | VI-1 | Ube2q2 |
| 15260 | 3 | 4 | 5 | 6 | VI-1 | Ube2r2 |
| 15261 | 3 | 4 | 5 | 6 | VI-1 | Ube2t |
| 15262 | 3 | 4 | 5 | 6 | VI-1 | Ube2v1 |
| 15263 | 3 | 4 | 5 | 6 | VI-1 | Ube3a |
| 15264 | 3 | 4 | 5 | 6 | VI-1 | Ube3c |
| 15265 | 3 | 4 | 5 | 6 | VI-1 | Ube4b |
| 15266 | 3 | 4 | 5 | 6 | VI-1 | Ubfd1 |
| 15267 | 3 | 4 | 5 | 6 | VI-1 | Ubl3 |
| 15268 | 3 | 4 | 5 | 6 | VI-1 | Ubl4 |
| 15269 | 3 | 4 | 5 | 6 | VI-1 | Ubl4b |
| 15270 | 3 | 4 | 5 | 6 | VI-1 | Ubl7 |
| 15271 | 3 | 4 | 5 | 6 | VI-1 | Ublcp1 |
| 15272 | 3 | 4 | 5 | 6 | VI-1 | Ubn2 |
| 15273 | 3 | 4 | 5 | 6 | VI-1 | Ubp1 |
| 15274 | 3 | 4 | 5 | 6 | VI-1 | Ubqln1 |
| 15275 | 3 | 4 | 5 | 6 | VI-1 | Ubqln2 |
| 15276 | 3 | 4 | 5 | 6 | VI-1 | Ubqln3 |
| 15277 | 3 | 4 | 5 | 6 | VI-1 | Ubqlnl |
| 15278 | 3 | 4 | 5 | 6 | VI-1 | Ubr1 |
| 15279 | 3 | 4 | 5 | 6 | VI-1 | Ubr4 |
| 15280 | 3 | 4 | 5 | 6 | VI-1 | Ubr5 |
| 15281 | 3 | 4 | 5 | 6 | VI-1 | Ubr7 |
| 15282 | 3 | 4 | 5 | 6 | VI-1 | Ubtd1 |
| 15283 | 3 | 4 | 5 | 6 | VI-1 | Ubtd2 |
| 15284 | 3 | 4 | 5 | 6 | VI-1 | Ubtf |
| 15285 | 3 | 4 | 5 | 6 | VI-1 | Ubxn10 |
| 15286 | 3 | 4 | 5 | 6 | VI-1 | Uchl4 |
| 15287 | 3 | 4 | 5 | 6 | VI-1 | Uchl5 |
| 15288 | 3 | 4 | 5 | 6 | VI-1 | Uck2 |
| 15289 | 3 | 4 | 5 | 6 | VI-1 | Uckl1 |
| 15290 | 3 | 4 | 5 | 6 | VI-1 | Ucn2 |
| 15291 | 3 | 4 | 5 | 6 | VI-1 | Ucp3 |
| 15292 | 3 | 4 | 5 | 6 | VI-1 | Ufd1l |
| 15293 | 3 | 4 | 5 | 6 | VI-1 | Ufsp2 |
| 15294 | 3 | 4 | 5 | 6 | VI-1 | Ugt1a6b |
| 15295 | 3 | 4 | 5 | 6 | VI-1 | Ugt1a7c |
| 15296 | 3 | 4 | 5 | 6 | VI-1 | Ugt2b34 |
| 15297 | 3 | 4 | 5 | 6 | VI-1 | Ugt2b38 |
| 15298 | 3 | 4 | 5 | 6 | VI-1 | Ugt2b5 |
| 15299 | 3 | 4 | 5 | 6 | VI-1 | Ugt3a1 |
| 15300 | 3 | 4 | 5 | 6 | VI-1 | Ugt3a2 |
| 15301 | 3 | 4 | 5 | 6 | VI-1 | Ugt8a |
| 15302 | 3 | 4 | 5 | 6 | VI-1 | Uhmk1 |
| 15303 | 3 | 4 | 5 | 6 | VI-1 | Uhrf1 |
| 15304 | 3 | 4 | 5 | 6 | VI-1 | Uhrf1bp1 |
| 15305 | 3 | 4 | 5 | 6 | VI-1 | Uhrf1bp1l |
| 15306 | 3 | 4 | 5 | 6 | VI-1 | Ulk1 |
| 15307 | 3 | 4 | 5 | 6 | VI-1 | Umod |
| 15308 | 3 | 4 | 5 | 6 | VI-1 | Unc119 |
| 15309 | 3 | 4 | 5 | 6 | VI-1 | Unc13a |
| 15310 | 3 | 4 | 5 | 6 | VI-1 | Unc13b |
| 15311 | 3 | 4 | 5 | 6 | VI-1 | Unc13d |
| 15312 | 3 | 4 | 5 | 6 | VI-1 | Unc45a |
| 15313 | 3 | 4 | 5 | 6 | VI-1 | Unc45b |
| 15314 | 3 | 4 | 5 | 6 | VI-1 | Unc5a |
| 15315 | 3 | 4 | 5 | 6 | VI-1 | Unc5cl |
| 15316 | 3 | 4 | 5 | 6 | VI-1 | Unc80 |
| 15317 | 3 | 4 | 5 | 6 | VI-1 | Unc93a |
| 15318 | 3 | 4 | 5 | 6 | VI-1 | Unc93b1 |
| 15319 | 3 | 4 | 5 | 6 | VI-1 | Unk |
| 15320 | 3 | 4 | 5 | 6 | VI-1 | Uox |
| 15321 | 3 | 4 | 5 | 6 | VI-1 | Upb1 |
| 15322 | 3 | 4 | 5 | 6 | VI-1 | Upf1 |
| 15323 | 3 | 4 | 5 | 6 | VI-1 | Upf3a |
| 15324 | 3 | 4 | 5 | 6 | VI-1 | Upk1a |
| 15325 | 3 | 4 | 5 | 6 | VI-1 | Upk1b |
| 15326 | 3 | 4 | 5 | 6 | VI-1 | Upk3bl |
| 15327 | 3 | 4 | 5 | 6 | VI-1 | Uqcc1 |
| 15328 | 3 | 4 | 5 | 6 | VI-1 | Uqcrb |
| 15329 | 3 | 4 | 5 | 6 | VI-1 | Urad |
| 15330 | 3 | 4 | 5 | 6 | VI-1 | Urm1 |
| 15331 | 3 | 4 | 5 | 6 | VI-1 | Uros |
| 15332 | 3 | 4 | 5 | 6 | VI-1 | Usf1 |
| 15333 | 3 | 4 | 5 | 6 | VI-1 | Usf2 |
| 15334 | 3 | 4 | 5 | 6 | VI-1 | Usp1 |
| 15335 | 3 | 4 | 5 | 6 | VI-1 | Usp13 |
| 15336 | 3 | 4 | 5 | 6 | VI-1 | Usp2 |
| 15337 | 3 | 4 | 5 | 6 | VI-1 | Usp20 |
| 15338 | 3 | 4 | 5 | 6 | VI-1 | Usp30 |
| 15339 | 3 | 4 | 5 | 6 | VI-1 | Usp35 |
| 15340 | 3 | 4 | 5 | 6 | VI-1 | Usp36 |
| 15341 | 3 | 4 | 5 | 6 | VI-1 | Usp37 |
| 15342 | 3 | 4 | 5 | 6 | VI-1 | Usp39 |
| 15343 | 3 | 4 | 5 | 6 | VI-1 | Usp40 |
| 15344 | 3 | 4 | 5 | 6 | VI-1 | Usp43 |
| 15345 | 3 | 4 | 5 | 6 | VI-1 | Usp44 |
| 15346 | 3 | 4 | 5 | 6 | VI-1 | Usp45 |
| 15347 | 3 | 4 | 5 | 6 | VI-1 | Usp48 |
| 15348 | 3 | 4 | 5 | 6 | VI-1 | Usp49 |
| 15349 | 3 | 4 | 5 | 6 | VI-1 | Usp5 |
| 15350 | 3 | 4 | 5 | 6 | VI-1 | Usp8 |
| 15351 | 3 | 4 | 5 | 6 | VI-1 | Uspl1 |
| 15352 | 3 | 4 | 5 | 6 | VI-1 | Ust |
| 15353 | 3 | 4 | 5 | 6 | VI-1 | Utp14a |
| 15354 | 3 | 4 | 5 | 6 | VI-1 | Utp23 |
| 15355 | 3 | 4 | 5 | 6 | VI-1 | Utp3 |
| 15356 | 3 | 4 | 5 | 6 | VI-1 | Utp6 |
| 15357 | 3 | 4 | 5 | 6 | VI-1 | Uts2b |
| 15358 | 3 | 4 | 5 | 6 | VI-1 | Uty |

Fig. 34 - 81

| | | | | | | | |
|---|---|---|---|---|---|---|---|
| 15359 | 3 | 4 | 5 | 6 | VI-1 | Uvssa |
| 15360 | 3 | 4 | 5 | 6 | VI-1 | Uxs1 |
| 15361 | 3 | 4 | 5 | 6 | VI-1 | Uxt |
| 15362 | 3 | 4 | 5 | 6 | VI-1 | Vac14 |
| 15363 | 3 | 4 | 5 | 6 | VI-1 | Vamp7 |
| 15364 | 3 | 4 | 5 | 6 | VI-1 | Vapa |
| 15365 | 3 | 4 | 5 | 6 | VI-1 | Vars |
| 15366 | 3 | 4 | 5 | 6 | VI-1 | Vash1 |
| 15367 | 3 | 4 | 5 | 6 | VI-1 | Vasn |
| 15368 | 3 | 4 | 5 | 6 | VI-1 | Vat1l |
| 15369 | 3 | 4 | 5 | 6 | VI-1 | Vav1 |
| 15370 | 3 | 4 | 5 | 6 | VI-1 | Vbp1 |
| 15371 | 3 | 4 | 5 | 6 | VI-1 | Vcam1 |
| 15372 | 3 | 4 | 5 | 6 | VI-1 | Vcan |
| 15373 | 3 | 4 | 5 | 6 | VI-1 | Vcl |
| 15374 | 3 | 4 | 5 | 6 | VI-1 | Vdac3 |
| 15375 | 3 | 4 | 5 | 6 | VI-1 | Vegfa |
| 15376 | 3 | 4 | 5 | 6 | VI-1 | Vezf1 |
| 15377 | 3 | 4 | 5 | 6 | VI-1 | Vgll2 |
| 15378 | 3 | 4 | 5 | 6 | VI-1 | Vgll3 |
| 15379 | 3 | 4 | 5 | 6 | VI-1 | Vil1 |
| 15380 | 3 | 4 | 5 | 6 | VI-1 | Vill |
| 15381 | 3 | 4 | 5 | 6 | VI-1 | Vim |
| 15382 | 3 | 4 | 5 | 6 | VI-1 | Vimp |
| 15383 | 3 | 4 | 5 | 6 | VI-1 | Vipas39 |
| 15384 | 3 | 4 | 5 | 6 | VI-1 | Vipr1 |
| 15385 | 3 | 4 | 5 | 6 | VI-1 | Vipr2 |
| 15386 | 3 | 4 | 5 | 6 | VI-1 | Vkorc1 |
| 15387 | 3 | 4 | 5 | 6 | VI-1 | Vldlr |
| 15388 | 3 | 4 | 5 | 6 | VI-1 | Vmac |
| 15389 | 3 | 4 | 5 | 6 | VI-1 | Vmn2r-ps54 |
| 15390 | 3 | 4 | 5 | 6 | VI-1 | Vmn2r29 |
| 15391 | 3 | 4 | 5 | 6 | VI-1 | Vmo1 |
| 15392 | 3 | 4 | 5 | 6 | VI-1 | Vmp1 |
| 15393 | 3 | 4 | 5 | 6 | VI-1 | Vnn3 |
| 15394 | 3 | 4 | 5 | 6 | VI-1 | Vopp1 |
| 15395 | 3 | 4 | 5 | 6 | VI-1 | Vpreb1 |
| 15396 | 3 | 4 | 5 | 6 | VI-1 | Vps13b |
| 15397 | 3 | 4 | 5 | 6 | VI-1 | Vps13c |
| 15398 | 3 | 4 | 5 | 6 | VI-1 | Vps25 |
| 15399 | 3 | 4 | 5 | 6 | VI-1 | Vps33a |
| 15400 | 3 | 4 | 5 | 6 | VI-1 | Vps35 |
| 15401 | 3 | 4 | 5 | 6 | VI-1 | Vps37d |
| 15402 | 3 | 4 | 5 | 6 | VI-1 | Vps41 |
| 15403 | 3 | 4 | 5 | 6 | VI-1 | Vps4a |
| 15404 | 3 | 4 | 5 | 6 | VI-1 | Vps51 |
| 15405 | 3 | 4 | 5 | 6 | VI-1 | Vps52 |
| 15406 | 3 | 4 | 5 | 6 | VI-1 | Vps9d1 |
| 15407 | 3 | 4 | 5 | 6 | VI-1 | Vrk1 |
| 15408 | 3 | 4 | 5 | 6 | VI-1 | Vrk2 |
| 15409 | 3 | 4 | 5 | 6 | VI-1 | Vrk3 |
| 15410 | 3 | 4 | 5 | 6 | VI-1 | Vsig10 |
| 15411 | 3 | 4 | 5 | 6 | VI-1 | Vsig2 |
| 15412 | 3 | 4 | 5 | 6 | VI-1 | Vsig4 |
| 15413 | 3 | 4 | 5 | 6 | VI-1 | Vstm2a |
| 15414 | 3 | 4 | 5 | 6 | VI-1 | Vstm2l |
| 15415 | 3 | 4 | 5 | 6 | VI-1 | Vstm5 |
| 15416 | 3 | 4 | 5 | 6 | VI-1 | Vta1 |
| 15417 | 3 | 4 | 5 | 6 | VI-1 | Vti1b |
| 15418 | 3 | 4 | 5 | 6 | VI-1 | Vtn |
| 15419 | 3 | 4 | 5 | 6 | VI-1 | Vwa2 |
| 15420 | 3 | 4 | 5 | 6 | VI-1 | Vwa3a |
| 15421 | 3 | 4 | 5 | 6 | VI-1 | Vwa5a |
| 15422 | 3 | 4 | 5 | 6 | VI-1 | Vwa5b1 |
| 15423 | 3 | 4 | 5 | 6 | VI-1 | Vwa7 |
| 15424 | 3 | 4 | 5 | 6 | VI-1 | Vwc2l |
| 15425 | 3 | 4 | 5 | 6 | VI-1 | Vwf |
| 15426 | 3 | 4 | 5 | 6 | VI-1 | Wapal |
| 15427 | 3 | 4 | 5 | 6 | VI-1 | Wars |
| 15428 | 3 | 4 | 5 | 6 | VI-1 | Wars2 |
| 15429 | 3 | 4 | 5 | 6 | VI-1 | Wasf3 |
| 15430 | 3 | 4 | 5 | 6 | VI-1 | Wash |
| 15431 | 3 | 4 | 5 | 6 | VI-1 | Wbp1 |
| 15432 | 3 | 4 | 5 | 6 | VI-1 | Wbp1l |
| 15433 | 3 | 4 | 5 | 6 | VI-1 | Wbp1l |
| 15434 | 3 | 4 | 5 | 6 | VI-1 | Wbp5 |
| 15435 | 3 | 4 | 5 | 6 | VI-1 | Wbscr16 |
| 15436 | 3 | 4 | 5 | 6 | VI-1 | Wbscr17 |
| 15437 | 3 | 4 | 5 | 6 | VI-1 | Wbscr25 |
| 15438 | 3 | 4 | 5 | 6 | VI-1 | Wbscr27 |
| 15439 | 3 | 4 | 5 | 6 | VI-1 | Wdpcp |
| 15440 | 3 | 4 | 5 | 6 | VI-1 | Wdr1 |
| 15441 | 3 | 4 | 5 | 6 | VI-1 | Wdr16 |
| 15442 | 3 | 4 | 5 | 6 | VI-1 | Wdr18 |
| 15443 | 3 | 4 | 5 | 6 | VI-1 | Wdr3 |
| 15444 | 3 | 4 | 5 | 6 | VI-1 | Wdr31 |
| 15445 | 3 | 4 | 5 | 6 | VI-1 | Wdr33 |
| 15446 | 3 | 4 | 5 | 6 | VI-1 | Wdr36 |
| 15447 | 3 | 4 | 5 | 6 | VI-1 | Wdr43 |
| 15448 | 3 | 4 | 5 | 6 | VI-1 | Wdr44 |
| 15449 | 3 | 4 | 5 | 6 | VI-1 | Wdr45 |
| 15450 | 3 | 4 | 5 | 6 | VI-1 | Wdr45b |
| 15451 | 3 | 4 | 5 | 6 | VI-1 | Wdr46 |
| 15452 | 3 | 4 | 5 | 6 | VI-1 | Wdr48 |
| 15453 | 3 | 4 | 5 | 6 | VI-1 | Wdr53 |
| 15454 | 3 | 4 | 5 | 6 | VI-1 | Wdr54 |
| 15455 | 3 | 4 | 5 | 6 | VI-1 | Wdr55 |
| 15456 | 3 | 4 | 5 | 6 | VI-1 | Wdr59 |
| 15457 | 3 | 4 | 5 | 6 | VI-1 | Wdr60 |
| 15458 | 3 | 4 | 5 | 6 | VI-1 | Wdr62 |
| 15459 | 3 | 4 | 5 | 6 | VI-1 | Wdr7 |
| 15460 | 3 | 4 | 5 | 6 | VI-1 | Wdr70 |
| 15461 | 3 | 4 | 5 | 6 | VI-1 | Wdr73 |
| 15462 | 3 | 4 | 5 | 6 | VI-1 | Wdr75 |
| 15463 | 3 | 4 | 5 | 6 | VI-1 | Wdr77 |
| 15464 | 3 | 4 | 5 | 6 | VI-1 | Wdr81 |
| 15465 | 3 | 4 | 5 | 6 | VI-1 | Wdr86 |
| 15466 | 3 | 4 | 5 | 6 | VI-1 | Wdr89 |
| 15467 | 3 | 4 | 5 | 6 | VI-1 | Wdr91 |
| 15468 | 3 | 4 | 5 | 6 | VI-1 | Wdr93 |
| 15469 | 3 | 4 | 5 | 6 | VI-1 | Wdsub1 |
| 15470 | 3 | 4 | 5 | 6 | VI-1 | Wdtc1 |
| 15471 | 3 | 4 | 5 | 6 | VI-1 | Wdyhv1 |
| 15472 | 3 | 4 | 5 | 6 | VI-1 | Wfdc1 |
| 15473 | 3 | 4 | 5 | 6 | VI-1 | Wfdc6b |
| 15474 | 3 | 4 | 5 | 6 | VI-1 | Wfikkn2 |
| 15475 | 3 | 4 | 5 | 6 | VI-1 | Whsc1l1 |
| 15476 | 3 | 4 | 5 | 6 | VI-1 | Wipf1 |
| 15477 | 3 | 4 | 5 | 6 | VI-1 | Wipi2 |
| 15478 | 3 | 4 | 5 | 6 | VI-1 | Wnk2 |
| 15479 | 3 | 4 | 5 | 6 | VI-1 | Wnk4 |
| 15480 | 3 | 4 | 5 | 6 | VI-1 | Wnt2 |
| 15481 | 3 | 4 | 5 | 6 | VI-1 | Wnt4 |
| 15482 | 3 | 4 | 5 | 6 | VI-1 | Wnt5b |
| 15483 | 3 | 4 | 5 | 6 | VI-1 | Wrn |
| 15484 | 3 | 4 | 5 | 6 | VI-1 | Wrnip1 |
| 15485 | 3 | 4 | 5 | 6 | VI-1 | Wsb1 |
| 15486 | 3 | 4 | 5 | 6 | VI-1 | Wsb2 |
| 15487 | 3 | 4 | 5 | 6 | VI-1 | Wtip |
| 15488 | 3 | 4 | 5 | 6 | VI-1 | Wwp2 |
| 15489 | 3 | 4 | 5 | 6 | VI-1 | Xab2 |
| 15490 | 3 | 4 | 5 | 6 | VI-1 | Xbp1 |
| 15491 | 3 | 4 | 5 | 6 | VI-1 | Xcl1 |
| 15492 | 3 | 4 | 5 | 6 | VI-1 | Xdh |
| 15493 | 3 | 4 | 5 | 6 | VI-1 | Xirp1 |
| 15494 | 3 | 4 | 5 | 6 | VI-1 | Xk |
| 15495 | 3 | 4 | 5 | 6 | VI-1 | Xkr9 |
| 15496 | 3 | 4 | 5 | 6 | VI-1 | Xlr3a |
| 15497 | 3 | 4 | 5 | 6 | VI-1 | Xlr3b |
| 15498 | 3 | 4 | 5 | 6 | VI-1 | Xlr3c |
| 15499 | 3 | 4 | 5 | 6 | VI-1 | Xlr4a |
| 15500 | 3 | 4 | 5 | 6 | VI-1 | Xlr4b |
| 15501 | 3 | 4 | 5 | 6 | VI-1 | Xpa |
| 15502 | 3 | 4 | 5 | 6 | VI-1 | Xpc |
| 15503 | 3 | 4 | 5 | 6 | VI-1 | Xpnpep2 |
| 15504 | 3 | 4 | 5 | 6 | VI-1 | Xpnpep3 |
| 15505 | 3 | 4 | 5 | 6 | VI-1 | Xpo1 |
| 15506 | 3 | 4 | 5 | 6 | VI-1 | Xpo4 |
| 15507 | 3 | 4 | 5 | 6 | VI-1 | Xpo5 |
| 15508 | 3 | 4 | 5 | 6 | VI-1 | Xpot |
| 15509 | 3 | 4 | 5 | 6 | VI-1 | Xrcc4 |
| 15510 | 3 | 4 | 5 | 6 | VI-1 | Xrcc5 |
| 15511 | 3 | 4 | 5 | 6 | VI-1 | Xrcc6 |
| 15512 | 3 | 4 | 5 | 6 | VI-1 | Xrn2 |
| 15513 | 3 | 4 | 5 | 6 | VI-1 | Xylt2 |
| 15514 | 3 | 4 | 5 | 6 | VI-1 | Yaf2 |
| 15515 | 3 | 4 | 5 | 6 | VI-1 | Yars |
| 15516 | 3 | 4 | 5 | 6 | VI-1 | Ybx1 |
| 15517 | 3 | 4 | 5 | 6 | VI-1 | Ybx3 |
| 15518 | 3 | 4 | 5 | 6 | VI-1 | Yeats4 |
| 15519 | 3 | 4 | 5 | 6 | VI-1 | Yes1 |
| 15520 | 3 | 4 | 5 | 6 | VI-1 | Yif1a |
| 15521 | 3 | 4 | 5 | 6 | VI-1 | Yipf3 |
| 15522 | 3 | 4 | 5 | 6 | VI-1 | Yipf7 |
| 15523 | 3 | 4 | 5 | 6 | VI-1 | Yod1 |
| 15524 | 3 | 4 | 5 | 6 | VI-1 | Ypel1 |
| 15525 | 3 | 4 | 5 | 6 | VI-1 | Ypel2 |
| 15526 | 3 | 4 | 5 | 6 | VI-1 | Ypel5 |
| 15527 | 3 | 4 | 5 | 6 | VI-1 | Yrdc |
| 15528 | 3 | 4 | 5 | 6 | VI-1 | Ythdf2 |
| 15529 | 3 | 4 | 5 | 6 | VI-1 | Ythdf3 |
| 15530 | 3 | 4 | 5 | 6 | VI-1 | Ywhah |
| 15531 | 3 | 4 | 5 | 6 | VI-1 | Ywhaq |
| 15532 | 3 | 4 | 5 | 6 | VI-1 | Yy2 |
| 15533 | 3 | 4 | 5 | 6 | VI-1 | Zadh2 |
| 15534 | 3 | 4 | 5 | 6 | VI-1 | Zbbx |
| 15535 | 3 | 4 | 5 | 6 | VI-1 | Zbtb10 |
| 15536 | 3 | 4 | 5 | 6 | VI-1 | Zbtb17 |
| 15537 | 3 | 4 | 5 | 6 | VI-1 | Zbtb21 |
| 15538 | 3 | 4 | 5 | 6 | VI-1 | Zbtb24 |
| 15539 | 3 | 4 | 5 | 6 | VI-1 | Zbtb32 |
| 15540 | 3 | 4 | 5 | 6 | VI-1 | Zbtb4 |
| 15541 | 3 | 4 | 5 | 6 | VI-1 | Zbtb40 |
| 15542 | 3 | 4 | 5 | 6 | VI-1 | Zbtb41 |
| 15543 | 3 | 4 | 5 | 6 | VI-1 | Zbtb42 |
| 15544 | 3 | 4 | 5 | 6 | VI-1 | Zbtb44 |
| 15545 | 3 | 4 | 5 | 6 | VI-1 | Zbtb46 |
| 15546 | 3 | 4 | 5 | 6 | VI-1 | Zbtb48 |
| 15547 | 3 | 4 | 5 | 6 | VI-1 | Zbtb6 |
| 15548 | 3 | 4 | 5 | 6 | VI-1 | Zc2hc1a |
| 15549 | 3 | 4 | 5 | 6 | VI-1 | Zc2hc1c |
| 15550 | 3 | 4 | 5 | 6 | VI-1 | Zc3h10 |

Fig. 34 - 82

| | | | | | | | |
|---|---|---|---|---|---|---|---|
| 15551 | 3 | 4 | 5 | 6 | | VI-1 | Zc3h12a |
| 15552 | 3 | 4 | 5 | 6 | | VI-1 | Zc3h12d |
| 15553 | 3 | 4 | 5 | 6 | | VI-1 | Zc3h14 |
| 15554 | 3 | 4 | 5 | 6 | | VI-1 | Zc3h15 |
| 15555 | 3 | 4 | 5 | 6 | | VI-1 | Zc3h7a |
| 15556 | 3 | 4 | 5 | 6 | | VI-1 | Zc3hav1 |
| 15557 | 3 | 4 | 5 | 6 | | VI-1 | Zc3hc1 |
| 15558 | 3 | 4 | 5 | 6 | | VI-1 | Zcchc8 |
| 15559 | 3 | 4 | 5 | 6 | | VI-1 | Zcrb1 |
| 15560 | 3 | 4 | 5 | 6 | | VI-1 | Zdhhc1 |
| 15561 | 3 | 4 | 5 | 6 | | VI-1 | Zdhhc12 |
| 15562 | 3 | 4 | 5 | 6 | | VI-1 | Zdhhc13 |
| 15563 | 3 | 4 | 5 | 6 | | VI-1 | Zdhhc14 |
| 15564 | 3 | 4 | 5 | 6 | | VI-1 | Zdhhc18 |
| 15565 | 3 | 4 | 5 | 6 | | VI-1 | Zdhhc19 |
| 15566 | 3 | 4 | 5 | 6 | | VI-1 | Zdhhc2 |
| 15567 | 3 | 4 | 5 | 6 | | VI-1 | Zdhhc20 |
| 15568 | 3 | 4 | 5 | 6 | | VI-1 | Zdhhc22 |
| 15569 | 3 | 4 | 5 | 6 | | VI-1 | Zdhhc23 |
| 15570 | 3 | 4 | 5 | 6 | | VI-1 | Zdhhc4 |
| 15571 | 3 | 4 | 5 | 6 | | VI-1 | Zdhhc7 |
| 15572 | 3 | 4 | 5 | 6 | | VI-1 | Zeb2 |
| 15573 | 3 | 4 | 5 | 6 | | VI-1 | Zer1 |
| 15574 | 3 | 4 | 5 | 6 | | VI-1 | Zfand1 |
| 15575 | 3 | 4 | 5 | 6 | | VI-1 | Zfand2a |
| 15576 | 3 | 4 | 5 | 6 | | VI-1 | Zfand4 |
| 15577 | 3 | 4 | 5 | 6 | | VI-1 | Zfand5 |
| 15578 | 3 | 4 | 5 | 6 | | VI-1 | Zfand6 |
| 15579 | 3 | 4 | 5 | 6 | | VI-1 | Zfhx2 |
| 15580 | 3 | 4 | 5 | 6 | | VI-1 | Zfhx2os |
| 15581 | 3 | 4 | 5 | 6 | | VI-1 | Zfhx4 |
| 15582 | 3 | 4 | 5 | 6 | | VI-1 | Zfml |
| 15583 | 3 | 4 | 5 | 6 | | VI-1 | Zfp110 |
| 15584 | 3 | 4 | 5 | 6 | | VI-1 | Zfp113 |
| 15585 | 3 | 4 | 5 | 6 | | VI-1 | Zfp119a |
| 15586 | 3 | 4 | 5 | 6 | | VI-1 | Zfp119b |
| 15587 | 3 | 4 | 5 | 6 | | VI-1 | Zfp120 |
| 15588 | 3 | 4 | 5 | 6 | | VI-1 | Zfp13 |
| 15589 | 3 | 4 | 5 | 6 | | VI-1 | Zfp143 |
| 15590 | 3 | 4 | 5 | 6 | | VI-1 | Zfp157 |
| 15591 | 3 | 4 | 5 | 6 | | VI-1 | Zfp182 |
| 15592 | 3 | 4 | 5 | 6 | | VI-1 | Zfp2 |
| 15593 | 3 | 4 | 5 | 6 | | VI-1 | Zfp212 |
| 15594 | 3 | 4 | 5 | 6 | | VI-1 | Zfp229 |
| 15595 | 3 | 4 | 5 | 6 | | VI-1 | Zfp260 |
| 15596 | 3 | 4 | 5 | 6 | | VI-1 | Zfp277 |
| 15597 | 3 | 4 | 5 | 6 | | VI-1 | Zfp28 |
| 15598 | 3 | 4 | 5 | 6 | | VI-1 | Zfp281 |
| 15599 | 3 | 4 | 5 | 6 | | VI-1 | Zfp282 |
| 15600 | 3 | 4 | 5 | 6 | | VI-1 | Zfp292 |
| 15601 | 3 | 4 | 5 | 6 | | VI-1 | Zfp296 |
| 15602 | 3 | 4 | 5 | 6 | | VI-1 | Zfp3 |
| 15603 | 3 | 4 | 5 | 6 | | VI-1 | Zfp317 |
| 15604 | 3 | 4 | 5 | 6 | | VI-1 | Zfp318 |
| 15605 | 3 | 4 | 5 | 6 | | VI-1 | Zfp330 |
| 15606 | 3 | 4 | 5 | 6 | | VI-1 | Zfp335 |
| 15607 | 3 | 4 | 5 | 6 | | VI-1 | Zfp35 |
| 15608 | 3 | 4 | 5 | 6 | | VI-1 | Zfp358 |
| 15609 | 3 | 4 | 5 | 6 | | VI-1 | Zfp362 |
| 15610 | 3 | 4 | 5 | 6 | | VI-1 | Zfp366 |
| 15611 | 3 | 4 | 5 | 6 | | VI-1 | Zfp36l1 |
| 15612 | 3 | 4 | 5 | 6 | | VI-1 | Zfp383 |
| 15613 | 3 | 4 | 5 | 6 | | VI-1 | Zfp385a |
| 15614 | 3 | 4 | 5 | 6 | | VI-1 | Zfp385b |
| 15615 | 3 | 4 | 5 | 6 | | VI-1 | Zfp385c |
| 15616 | 3 | 4 | 5 | 6 | | VI-1 | Zfp397 |
| 15617 | 3 | 4 | 5 | 6 | | VI-1 | Zfp398 |
| 15618 | 3 | 4 | 5 | 6 | | VI-1 | Zfp408 |
| 15619 | 3 | 4 | 5 | 6 | | VI-1 | Zfp410 |
| 15620 | 3 | 4 | 5 | 6 | | VI-1 | Zfp414 |
| 15621 | 3 | 4 | 5 | 6 | | VI-1 | Zfp422 |
| 15622 | 3 | 4 | 5 | 6 | | VI-1 | Zfp426 |
| 15623 | 3 | 4 | 5 | 6 | | VI-1 | Zfp428 |
| 15624 | 3 | 4 | 5 | 6 | | VI-1 | Zfp444 |
| 15625 | 3 | 4 | 5 | 6 | | VI-1 | Zfp445 |
| 15626 | 3 | 4 | 5 | 6 | | VI-1 | Zfp474 |
| 15627 | 3 | 4 | 5 | 6 | | VI-1 | Zfp493 |
| 15628 | 3 | 4 | 5 | 6 | | VI-1 | Zfp503 |
| 15629 | 3 | 4 | 5 | 6 | | VI-1 | Zfp511 |
| 15630 | 3 | 4 | 5 | 6 | | VI-1 | Zfp518a |
| 15631 | 3 | 4 | 5 | 6 | | VI-1 | Zfp52 |
| 15632 | 3 | 4 | 5 | 6 | | VI-1 | Zfp526 |
| 15633 | 3 | 4 | 5 | 6 | | VI-1 | Zfp558 |
| 15634 | 3 | 4 | 5 | 6 | | VI-1 | Zfp595 |
| 15635 | 3 | 4 | 5 | 6 | | VI-1 | Zfp598 |
| 15636 | 3 | 4 | 5 | 6 | | VI-1 | Zfp600 |
| 15637 | 3 | 4 | 5 | 6 | | VI-1 | Zfp605 |
| 15638 | 3 | 4 | 5 | 6 | | VI-1 | Zfp612 |
| 15639 | 3 | 4 | 5 | 6 | | VI-1 | Zfp617 |
| 15640 | 3 | 4 | 5 | 6 | | VI-1 | Zfp62 |
| 15641 | 3 | 4 | 5 | 6 | | VI-1 | Zfp622 |
| 15642 | 3 | 4 | 5 | 6 | | VI-1 | Zfp623 |
| 15643 | 3 | 4 | 5 | 6 | | VI-1 | Zfp628 |
| 15644 | 3 | 4 | 5 | 6 | | VI-1 | Zfp644 |
| 15645 | 3 | 4 | 5 | 6 | | VI-1 | Zfp65 |
| 15646 | 3 | 4 | 5 | 6 | | VI-1 | Zfp651 |
| 15647 | 3 | 4 | 5 | 6 | | VI-1 | Zfp652 |
| 15648 | 3 | 4 | 5 | 6 | | VI-1 | Zfp652os |
| 15649 | 3 | 4 | 5 | 6 | | VI-1 | Zfp655 |
| 15650 | 3 | 4 | 5 | 6 | | VI-1 | Zfp658 |
| 15651 | 3 | 4 | 5 | 6 | | VI-1 | Zfp672 |
| 15652 | 3 | 4 | 5 | 6 | | VI-1 | Zfp677 |
| 15653 | 3 | 4 | 5 | 6 | | VI-1 | Zfp68 |
| 15654 | 3 | 4 | 5 | 6 | | VI-1 | Zfp69 |
| 15655 | 3 | 4 | 5 | 6 | | VI-1 | Zfp692 |
| 15656 | 3 | 4 | 5 | 6 | | VI-1 | Zfp697 |
| 15657 | 3 | 4 | 5 | 6 | | VI-1 | Zfp703 |
| 15658 | 3 | 4 | 5 | 6 | | VI-1 | Zfp707 |
| 15659 | 3 | 4 | 5 | 6 | | VI-1 | Zfp747 |
| 15660 | 3 | 4 | 5 | 6 | | VI-1 | Zfp763 |
| 15661 | 3 | 4 | 5 | 6 | | VI-1 | Zfp768 |
| 15662 | 3 | 4 | 5 | 6 | | VI-1 | Zfp772 |
| 15663 | 3 | 4 | 5 | 6 | | VI-1 | Zfp775 |
| 15664 | 3 | 4 | 5 | 6 | | VI-1 | Zfp777 |
| 15665 | 3 | 4 | 5 | 6 | | VI-1 | Zfp78 |
| 15666 | 3 | 4 | 5 | 6 | | VI-1 | Zfp780b |
| 15667 | 3 | 4 | 5 | 6 | | VI-1 | Zfp783 |
| 15668 | 3 | 4 | 5 | 6 | | VI-1 | Zfp788 |
| 15669 | 3 | 4 | 5 | 6 | | VI-1 | Zfp791 |
| 15670 | 3 | 4 | 5 | 6 | | VI-1 | Zfp799 |
| 15671 | 3 | 4 | 5 | 6 | | VI-1 | Zfp800 |
| 15672 | 3 | 4 | 5 | 6 | | VI-1 | Zfp820 |
| 15673 | 3 | 4 | 5 | 6 | | VI-1 | Zfp825 |
| 15674 | 3 | 4 | 5 | 6 | | VI-1 | Zfp839 |
| 15675 | 3 | 4 | 5 | 6 | | VI-1 | Zfp85 |
| 15676 | 3 | 4 | 5 | 6 | | VI-1 | Zfp865 |
| 15677 | 3 | 4 | 5 | 6 | | VI-1 | Zfp869 |
| 15678 | 3 | 4 | 5 | 6 | | VI-1 | Zfp874a |
| 15679 | 3 | 4 | 5 | 6 | | VI-1 | Zfp874b |
| 15680 | 3 | 4 | 5 | 6 | | VI-1 | Zfp91 |
| 15681 | 3 | 4 | 5 | 6 | | VI-1 | Zfp935 |
| 15682 | 3 | 4 | 5 | 6 | | VI-1 | Zfp940 |
| 15683 | 3 | 4 | 5 | 6 | | VI-1 | Zfp941 |
| 15684 | 3 | 4 | 5 | 6 | | VI-1 | Zfp946 |
| 15685 | 3 | 4 | 5 | 6 | | VI-1 | Zfp951 |
| 15686 | 3 | 4 | 5 | 6 | | VI-1 | Zfp954 |
| 15687 | 3 | 4 | 5 | 6 | | VI-1 | Zfp959 |
| 15688 | 3 | 4 | 5 | 6 | | VI-1 | Zfp960 |
| 15689 | 3 | 4 | 5 | 6 | | VI-1 | Zfp963 |
| 15690 | 3 | 4 | 5 | 6 | | VI-1 | Zfr |
| 15691 | 3 | 4 | 5 | 6 | | VI-1 | Zfyve1 |
| 15692 | 3 | 4 | 5 | 6 | | VI-1 | Zfyve16 |
| 15693 | 3 | 4 | 5 | 6 | | VI-1 | Zfyve19 |
| 15694 | 3 | 4 | 5 | 6 | | VI-1 | Zfyve28 |
| 15695 | 3 | 4 | 5 | 6 | | VI-1 | Zglp1 |
| 15696 | 3 | 4 | 5 | 6 | | VI-1 | Zic1 |
| 15697 | 3 | 4 | 5 | 6 | | VI-1 | Zkscan14 |
| 15698 | 3 | 4 | 5 | 6 | | VI-1 | Zkscan17 |
| 15699 | 3 | 4 | 5 | 6 | | VI-1 | Zkscan7 |
| 15700 | 3 | 4 | 5 | 6 | | VI-1 | Zmat1 |
| 15701 | 3 | 4 | 5 | 6 | | VI-1 | Zmat2 |
| 15702 | 3 | 4 | 5 | 6 | | VI-1 | Zmym2 |
| 15703 | 3 | 4 | 5 | 6 | | VI-1 | Zmym5 |
| 15704 | 3 | 4 | 5 | 6 | | VI-1 | Zmynd10 |
| 15705 | 3 | 4 | 5 | 6 | | VI-1 | Zmynd15 |
| 15706 | 3 | 4 | 5 | 6 | | VI-1 | Zmynd19 |
| 15707 | 3 | 4 | 5 | 6 | | VI-1 | Znhit1 |
| 15708 | 3 | 4 | 5 | 6 | | VI-1 | Znhit2 |
| 15709 | 3 | 4 | 5 | 6 | | VI-1 | Znhit6 |
| 15710 | 3 | 4 | 5 | 6 | | VI-1 | Znrf1 |
| 15711 | 3 | 4 | 5 | 6 | | VI-1 | Zpbp2 |
| 15712 | 3 | 4 | 5 | 6 | | VI-1 | Zranb1 |
| 15713 | 3 | 4 | 5 | 6 | | VI-1 | Zranb2 |
| 15714 | 3 | 4 | 5 | 6 | | VI-1 | Zscan10 |
| 15715 | 3 | 4 | 5 | 6 | | VI-1 | Zscan12 |
| 15716 | 3 | 4 | 5 | 6 | | VI-1 | Zscan2 |
| 15717 | 3 | 4 | 5 | 6 | | VI-1 | Zswim1 |
| 15718 | 3 | 4 | 5 | 6 | | VI-1 | Zswim4 |
| 15719 | 3 | 4 | 5 | 6 | | VI-1 | Zswim7 |
| 15720 | 3 | 4 | 5 | 6 | | VI-1 | Zwint |
| 15721 | 3 | 4 | 5 | 6 | | VI-1 | Zxda |
| 15722 | 3 | 4 | 5 | 6 | | VI-1 | Zxdb |
| 15723 | 3 | 4 | 5 | 6 | | VI-1 | Zxdc |
| 15724 | 3 | 4 | 5 | 6 | | VI-1 | Zyx |
| 15725 | 3 | 4 | 5 | 6 | | VI-1 | Zzz3 |
| 15726 | 3 | 4 | 5 | | | V-2 | 1110032F04Rik |
| 15727 | 3 | 4 | 5 | | | V-2 | 1600027J07Rik |
| 15728 | 3 | 4 | 5 | | | V-2 | 1700001F09Rik |
| 15729 | 3 | 4 | 5 | | | V-2 | 1700007F19Rik |
| 15730 | 3 | 4 | 5 | | | V-2 | 1700008F21Rik |
| 15731 | 3 | 4 | 5 | | | V-2 | 1700010I02Rik |
| 15732 | 3 | 4 | 5 | | | V-2 | 1700011E24Rik |
| 15733 | 3 | 4 | 5 | | | V-2 | 1700016G22Rik |
| 15734 | 3 | 4 | 5 | | | V-2 | 1700020I14Rik |
| 15735 | 3 | 4 | 5 | | | V-2 | 1700026D11Rik |
| 15736 | 3 | 4 | 5 | | | V-2 | 1700026F02Rik |
| 15737 | 3 | 4 | 5 | | | V-2 | 1700027J24Rik |
| 15738 | 3 | 4 | 5 | | | V-2 | 1700027J07Rik |
| 15739 | 3 | 4 | 5 | | | V-2 | 1700028I16Rik |
| 15740 | 3 | 4 | 5 | | | V-2 | 1700030A11Rik |
| 15741 | 3 | 4 | 5 | | | V-2 | 1700030F18Rik |
| 15742 | 3 | 4 | 5 | | | V-2 | 1700031A10Rik |

Fig. 34 - 83

| | | | | | | | |
|---|---|---|---|---|---|---|---|
| 15743 | 3 | 4 | 5 | | | V-2 | 1700049G17Rik |
| 15744 | 3 | 4 | 5 | | | V-2 | 1700054A03Rik |
| 15745 | 3 | 4 | 5 | | | V-2 | 1700054K19Rik |
| 15746 | 3 | 4 | 5 | | | V-2 | 1700064M15Rik |
| 15747 | 3 | 4 | 5 | | | V-2 | 1700067G17Rik |
| 15748 | 3 | 4 | 5 | | | V-2 | 1700084J12Rik |
| 15749 | 3 | 4 | 5 | | | V-2 | 1700092E19Rik |
| 15750 | 3 | 4 | 5 | | | V-2 | 1700109K24Rik |
| 15751 | 3 | 4 | 5 | | | V-2 | 1700110I01Rik |
| 15752 | 3 | 4 | 5 | | | V-2 | 1700125H20Rik |
| 15753 | 3 | 4 | 5 | | | V-2 | 1810062O18Rik |
| 15754 | 3 | 4 | 5 | | | V-2 | 2310014L17Rik |
| 15755 | 3 | 4 | 5 | | | V-2 | 2310022A10Rik |
| 15756 | 3 | 4 | 5 | | | V-2 | 2310035C23Rik |
| 15757 | 3 | 4 | 5 | | | V-2 | 2610027K06Rik |
| 15758 | 3 | 4 | 5 | | | V-2 | 2610203C22Rik |
| 15759 | 3 | 4 | 5 | | | V-2 | 2610507H01Rik |
| 15760 | 3 | 4 | 5 | | | V-2 | 2700070M01Rik |
| 15761 | 3 | 4 | 5 | | | V-2 | 2810459M11Rik |
| 15762 | 3 | 4 | 5 | | | V-2 | 2810471M01Rik |
| 15763 | 3 | 4 | 5 | | | V-2 | 2900092D14Rik |
| 15764 | 3 | 4 | 5 | | | V-2 | 3110039J08Rik |
| 15765 | 3 | 4 | 5 | | | V-2 | 3110052M02Rik |
| 15766 | 3 | 4 | 5 | | | V-2 | 3110099E03Rik |
| 15767 | 3 | 4 | 5 | | | V-2 | 3632454L22Rik |
| 15768 | 3 | 4 | 5 | | | V-2 | 3830417A13Rik |
| 15769 | 3 | 4 | 5 | | | V-2 | 4833418N02Rik |
| 15770 | 3 | 4 | 5 | | | V-2 | 4921507L20Rik |
| 15771 | 3 | 4 | 5 | | | V-2 | 4921511H03Rik |
| 15772 | 3 | 4 | 5 | | | V-2 | 4930404H11Rik |
| 15773 | 3 | 4 | 5 | | | V-2 | 4930405A10Rik |
| 15774 | 3 | 4 | 5 | | | V-2 | 4930405L22Rik |
| 15775 | 3 | 4 | 5 | | | V-2 | 4930412D23Rik |
| 15776 | 3 | 4 | 5 | | | V-2 | 4930417O22Rik |
| 15777 | 3 | 4 | 5 | | | V-2 | 4930429B21Rik |
| 15778 | 3 | 4 | 5 | | | V-2 | 4930431F12Rik |
| 15779 | 3 | 4 | 5 | | | V-2 | 4930431P03Rik |
| 15780 | 3 | 4 | 5 | | | V-2 | 4930433I11Rik |
| 15781 | 3 | 4 | 5 | | | V-2 | 4930434J06Rik |
| 15782 | 3 | 4 | 5 | | | V-2 | 4930444M15Rik |
| 15783 | 3 | 4 | 5 | | | V-2 | 4930448H16Rik |
| 15784 | 3 | 4 | 5 | | | V-2 | 4930448K20Rik |
| 15785 | 3 | 4 | 5 | | | V-2 | 4930452A19Rik |
| 15786 | 3 | 4 | 5 | | | V-2 | 4930455F16Rik |
| 15787 | 3 | 4 | 5 | | | V-2 | 4930465K10Rik |
| 15788 | 3 | 4 | 5 | | | V-2 | 4930471G03Rik |
| 15789 | 3 | 4 | 5 | | | V-2 | 4930474N05Rik |
| 15790 | 3 | 4 | 5 | | | V-2 | 4930482G09Rik |
| 15791 | 3 | 4 | 5 | | | V-2 | 4930488L21Rik |
| 15792 | 3 | 4 | 5 | | | V-2 | 4930511A02Rik |
| 15793 | 3 | 4 | 5 | | | V-2 | 4930513N10Rik |
| 15794 | 3 | 4 | 5 | | | V-2 | 4930515L03Rik |
| 15795 | 3 | 4 | 5 | | | V-2 | 4930518P08Rik |
| 15796 | 3 | 4 | 5 | | | V-2 | 4930519D14Rik |
| 15797 | 3 | 4 | 5 | | | V-2 | 4930524C18Rik |
| 15798 | 3 | 4 | 5 | | | V-2 | 4930524N10Rik |
| 15799 | 3 | 4 | 5 | | | V-2 | 4930527G23Rik |
| 15800 | 3 | 4 | 5 | | | V-2 | 4930533B01Rik |
| 15801 | 3 | 4 | 5 | | | V-2 | 4930543E12Rik |
| 15802 | 3 | 4 | 5 | | | V-2 | 4930545L23Rik |
| 15803 | 3 | 4 | 5 | | | V-2 | 4930553E22Rik |
| 15804 | 3 | 4 | 5 | | | V-2 | 4930558J18Rik |
| 15805 | 3 | 4 | 5 | | | V-2 | 4930563E22Rik |
| 15806 | 3 | 4 | 5 | | | V-2 | 4930565N06Rik |
| 15807 | 3 | 4 | 5 | | | V-2 | 4930568E12Rik |
| 15808 | 3 | 4 | 5 | | | V-2 | 4930583K01Rik |
| 15809 | 3 | 4 | 5 | | | V-2 | 4930591A17Rik |
| 15810 | 3 | 4 | 5 | | | V-2 | 4930596D02Rik |
| 15811 | 3 | 4 | 5 | | | V-2 | 4931423N10Rik |
| 15812 | 3 | 4 | 5 | | | V-2 | 4931429I11Rik |
| 15813 | 3 | 4 | 5 | | | V-2 | 4932411E22Rik |
| 15814 | 3 | 4 | 5 | | | V-2 | 4932411N23Rik |
| 15815 | 3 | 4 | 5 | | | V-2 | 4933401B06Rik |
| 15816 | 3 | 4 | 5 | | | V-2 | 4933405D12Rik |
| 15817 | 3 | 4 | 5 | | | V-2 | 4933406G16Rik |
| 15818 | 3 | 4 | 5 | | | V-2 | 4933407L21Rik |
| 15819 | 3 | 4 | 5 | | | V-2 | 4933408J17Rik |
| 15820 | 3 | 4 | 5 | | | V-2 | 4933412E24Rik |
| 15821 | 3 | 4 | 5 | | | V-2 | 4933417E11Rik |
| 15822 | 3 | 4 | 5 | | | V-2 | 4933417O13Rik |
| 15823 | 3 | 4 | 5 | | | V-2 | 4933425B07Rik |
| 15824 | 3 | 4 | 5 | | | V-2 | 4933427E11Rik |
| 15825 | 3 | 4 | 5 | | | V-2 | 4933432K03Rik |
| 15826 | 3 | 4 | 5 | | | V-2 | 5430421F17Rik |
| 15827 | 3 | 4 | 5 | | | V-2 | 5730488B01Rik |
| 15828 | 3 | 4 | 5 | | | V-2 | 6330408A02Rik |
| 15829 | 3 | 4 | 5 | | | V-2 | 6430411K18Rik |
| 15830 | 3 | 4 | 5 | | | V-2 | 6430584L05Rik |
| 15831 | 3 | 4 | 5 | | | V-2 | 6430710C18Rik |
| 15832 | 3 | 4 | 5 | | | V-2 | 9030404E10Rik |
| 15833 | 3 | 4 | 5 | | | V-2 | 9130024F11Rik |
| 15834 | 3 | 4 | 5 | | | V-2 | 9130230L23Rik |
| 15835 | 3 | 4 | 5 | | | V-2 | 9230110F15Rik |
| 15836 | 3 | 4 | 5 | | | V-2 | 9230112J17Rik |
| 15837 | 3 | 4 | 5 | | | V-2 | 9230114K14Rik |
| 15838 | 3 | 4 | 5 | | | V-2 | 9330117O12Rik |
| 15839 | 3 | 4 | 5 | | | V-2 | 9530026F06Rik |
| 15840 | 3 | 4 | 5 | | | V-2 | 9530091C08Rik |
| 15841 | 3 | 4 | 5 | | | V-2 | 9630001P10Rik |
| 15842 | 3 | 4 | 5 | | | V-2 | 9830107B12Rik |
| 15843 | 3 | 4 | 5 | | | V-2 | 9830147E19Rik |
| 15844 | 3 | 4 | 5 | | | V-2 | 9930014A18Rik |
| 15845 | 3 | 4 | 5 | | | V-2 | A230056P14Rik |
| 15846 | 3 | 4 | 5 | | | V-2 | A330035P11Rik |
| 15847 | 3 | 4 | 5 | | | V-2 | A330093E20Rik |
| 15848 | 3 | 4 | 5 | | | V-2 | A430088P11Rik |
| 15849 | 3 | 4 | 5 | | | V-2 | A430090L17Rik |
| 15850 | 3 | 4 | 5 | | | V-2 | A630033H20Rik |
| 15851 | 3 | 4 | 5 | | | V-2 | A630076J17Rik |
| 15852 | 3 | 4 | 5 | | | V-2 | A630099N17Rik |
| 15853 | 3 | 4 | 5 | | | V-2 | A830082K12Rik |
| 15854 | 3 | 4 | 5 | | | V-2 | A830082N09Rik |
| 15855 | 3 | 4 | 5 | | | V-2 | A930017M01Rik |
| 15856 | 3 | 4 | 5 | | | V-2 | AI847159 |
| 15857 | 3 | 4 | 5 | | | V-2 | AU041133 |
| 15858 | 3 | 4 | 5 | | | V-2 | Aadacl3 |
| 15859 | 3 | 4 | 5 | | | V-2 | Abca17 |
| 15860 | 3 | 4 | 5 | | | V-2 | Abch11 |
| 15861 | 3 | 4 | 5 | | | V-2 | Abcb5 |
| 15862 | 3 | 4 | 5 | | | V-2 | Abcc12 |
| 15863 | 3 | 4 | 5 | | | V-2 | Acad9 |
| 15864 | 3 | 4 | 5 | | | V-2 | Acin1 |
| 15865 | 3 | 4 | 5 | | | V-2 | Adad2 |
| 15866 | 3 | 4 | 5 | | | V-2 | Adam21 |
| 15867 | 3 | 4 | 5 | | | V-2 | Adam26b |
| 15868 | 3 | 4 | 5 | | | V-2 | Adam29 |
| 15869 | 3 | 4 | 5 | | | V-2 | Adam34 |
| 15870 | 3 | 4 | 5 | | | V-2 | Adam4 |
| 15871 | 3 | 4 | 5 | | | V-2 | Adamts17 |
| 15872 | 3 | 4 | 5 | | | V-2 | Adcy10 |
| 15873 | 3 | 4 | 5 | | | V-2 | Aff3 |
| 15874 | 3 | 4 | 5 | | | V-2 | Agbl2 |
| 15875 | 3 | 4 | 5 | | | V-2 | Agl |
| 15876 | 3 | 4 | 5 | | | V-2 | Ago3 |
| 15877 | 3 | 4 | 5 | | | V-2 | Aipl1 |
| 15878 | 3 | 4 | 5 | | | V-2 | Akap14 |
| 15879 | 3 | 4 | 5 | | | V-2 | Akap5 |
| 15880 | 3 | 4 | 5 | | | V-2 | Alox12b |
| 15881 | 3 | 4 | 5 | | | V-2 | Alox15 |
| 15882 | 3 | 4 | 5 | | | V-2 | Amfr |
| 15883 | 3 | 4 | 5 | | | V-2 | Amt |
| 15884 | 3 | 4 | 5 | | | V-2 | Anapc2 |
| 15885 | 3 | 4 | 5 | | | V-2 | Ankfy1 |
| 15886 | 3 | 4 | 5 | | | V-2 | Ankrd22 |
| 15887 | 3 | 4 | 5 | | | V-2 | Ankrd24 |
| 15888 | 3 | 4 | 5 | | | V-2 | Ankrd36 |
| 15889 | 3 | 4 | 5 | | | V-2 | Ankrd40 |
| 15890 | 3 | 4 | 5 | | | V-2 | Ankrd6 |
| 15891 | 3 | 4 | 5 | | | V-2 | Anks6 |
| 15892 | 3 | 4 | 5 | | | V-2 | Ano5 |
| 15893 | 3 | 4 | 5 | | | V-2 | Anxa10 |
| 15894 | 3 | 4 | 5 | | | V-2 | Ap3s2 |
| 15895 | 3 | 4 | 5 | | | V-2 | Ap5m1 |
| 15896 | 3 | 4 | 5 | | | V-2 | Apaf1 |
| 15897 | 3 | 4 | 5 | | | V-2 | Apbb2 |
| 15898 | 3 | 4 | 5 | | | V-2 | Aplf |
| 15899 | 3 | 4 | 5 | | | V-2 | Arfip2 |
| 15900 | 3 | 4 | 5 | | | V-2 | Arhgap12 |
| 15901 | 3 | 4 | 5 | | | V-2 | Arhgap27os3 |
| 15902 | 3 | 4 | 5 | | | V-2 | Arhgap28 |
| 15903 | 3 | 4 | 5 | | | V-2 | Arhgap6 |
| 15904 | 3 | 4 | 5 | | | V-2 | Ari6ip1 |
| 15905 | 3 | 4 | 5 | | | V-2 | Armc1 |
| 15906 | 3 | 4 | 5 | | | V-2 | Armc2 |
| 15907 | 3 | 4 | 5 | | | V-2 | Armc8 |
| 15908 | 3 | 4 | 5 | | | V-2 | Arx |
| 15909 | 3 | 4 | 5 | | | V-2 | Asb4 |
| 15910 | 3 | 4 | 5 | | | V-2 | Asz1 |
| 15911 | 3 | 4 | 5 | | | V-2 | Atp13a4 |
| 15912 | 3 | 4 | 5 | | | V-2 | Atp6v0a2 |
| 15913 | 3 | 4 | 5 | | | V-2 | Atp8a2 |
| 15914 | 3 | 4 | 5 | | | V-2 | Atr |
| 15915 | 3 | 4 | 5 | | | V-2 | Azi2 |
| 15916 | 3 | 4 | 5 | | | V-2 | B230312C02Rik |
| 15917 | 3 | 4 | 5 | | | V-2 | B3gnt6 |
| 15918 | 3 | 4 | 5 | | | V-2 | BC030870 |
| 15919 | 3 | 4 | 5 | | | V-2 | BC049715 |
| 15920 | 3 | 4 | 5 | | | V-2 | BC055324 |
| 15921 | 3 | 4 | 5 | | | V-2 | BC061237 |
| 15922 | 3 | 4 | 5 | | | V-2 | Baat |
| 15923 | 3 | 4 | 5 | | | V-2 | Baz1b |
| 15924 | 3 | 4 | 5 | | | V-2 | Bcas1os2 |
| 15925 | 3 | 4 | 5 | | | V-2 | Bcas3os2 |
| 15926 | 3 | 4 | 5 | | | V-2 | Bex6 |
| 15927 | 3 | 4 | 5 | | | V-2 | Bhmt2 |
| 15928 | 3 | 4 | 5 | | | V-2 | Bloc1s6 |
| 15929 | 3 | 4 | 5 | | | V-2 | Brd7 |
| 15930 | 3 | 4 | 5 | | | V-2 | Brox |
| 15931 | 3 | 4 | 5 | | | V-2 | Bsnd |
| 15932 | 3 | 4 | 5 | | | V-2 | Btbd17 |
| 15933 | 3 | 4 | 5 | | | V-2 | Btbd2 |
| 15934 | 3 | 4 | 5 | | | V-2 | Btg4 |

Fig. 34 - 84

| | | | | | | | |
|---|---|---|---|---|---|---|---|
| 15935 | 3 | 4 | 5 | | V-2 | Btnl5-ps |
| 15936 | 3 | 4 | 5 | | V-2 | Bub1 |
| 15937 | 3 | 4 | 5 | | V-2 | C030016D13Rik |
| 15938 | 3 | 4 | 5 | | V-2 | C130026L21Rik |
| 15939 | 3 | 4 | 5 | | V-2 | C130050O18Rik |
| 15940 | 3 | 4 | 5 | | V-2 | C1rl |
| 15941 | 3 | 4 | 5 | | V-2 | C2cd4c |
| 15942 | 3 | 4 | 5 | | V-2 | C430049B03Rik |
| 15943 | 3 | 4 | 5 | | V-2 | C5ar2 |
| 15944 | 3 | 4 | 5 | | V-2 | C730027H18Rik |
| 15945 | 3 | 4 | 5 | | V-2 | C77370 |
| 15946 | 3 | 4 | 5 | | V-2 | C8a |
| 15947 | 3 | 4 | 5 | | V-2 | Cacna1g |
| 15948 | 3 | 4 | 5 | | V-2 | Cacna2d4 |
| 15949 | 3 | 4 | 5 | | V-2 | Cacng6 |
| 15950 | 3 | 4 | 5 | | V-2 | Capn3 |
| 15951 | 3 | 4 | 5 | | V-2 | Capn6 |
| 15952 | 3 | 4 | 5 | | V-2 | Caprin1 |
| 15953 | 3 | 4 | 5 | | V-2 | Card10 |
| 15954 | 3 | 4 | 5 | | V-2 | Ccdc116 |
| 15955 | 3 | 4 | 5 | | V-2 | Ccdc125 |
| 15956 | 3 | 4 | 5 | | V-2 | Ccdc129 |
| 15957 | 3 | 4 | 5 | | V-2 | Ccdc147 |
| 15958 | 3 | 4 | 5 | | V-2 | Ccdc177 |
| 15959 | 3 | 4 | 5 | | V-2 | Ccdc185 |
| 15960 | 3 | 4 | 5 | | V-2 | Ccdc25 |
| 15961 | 3 | 4 | 5 | | V-2 | Ccdc36 |
| 15962 | 3 | 4 | 5 | | V-2 | Ccdc39 |
| 15963 | 3 | 4 | 5 | | V-2 | Ccdc71 |
| 15964 | 3 | 4 | 5 | | V-2 | Ccdc97 |
| 15965 | 3 | 4 | 5 | | V-2 | Cckar |
| 15966 | 3 | 4 | 5 | | V-2 | Ccnh |
| 15967 | 3 | 4 | 5 | | V-2 | Ccrl1l1 |
| 15968 | 3 | 4 | 5 | | V-2 | Ccser1 |
| 15969 | 3 | 4 | 5 | | V-2 | Cd109 |
| 15970 | 3 | 4 | 5 | | V-2 | Cd209c |
| 15971 | 3 | 4 | 5 | | V-2 | Cd70 |
| 15972 | 3 | 4 | 5 | | V-2 | Cdc20b |
| 15973 | 3 | 4 | 5 | | V-2 | Cdc42 |
| 15974 | 3 | 4 | 5 | | V-2 | Cdh24 |
| 15975 | 3 | 4 | 5 | | V-2 | Cdk5rap2 |
| 15976 | 3 | 4 | 5 | | V-2 | Cdk7 |
| 15977 | 3 | 4 | 5 | | V-2 | Ceacam15 |
| 15978 | 3 | 4 | 5 | | V-2 | Ceacam19 |
| 15979 | 3 | 4 | 5 | | V-2 | Cenpi |
| 15980 | 3 | 4 | 5 | | V-2 | Cenpu |
| 15981 | 3 | 4 | 5 | | V-2 | Cep135 |
| 15982 | 3 | 4 | 5 | | V-2 | Cep164 |
| 15983 | 3 | 4 | 5 | | V-2 | Cep192 |
| 15984 | 3 | 4 | 5 | | V-2 | Cers2 |
| 15985 | 3 | 4 | 5 | | V-2 | Ces1c |
| 15986 | 3 | 4 | 5 | | V-2 | Ces2a |
| 15987 | 3 | 4 | 5 | | V-2 | Chd8 |
| 15988 | 3 | 4 | 5 | | V-2 | Chek2 |
| 15989 | 3 | 4 | 5 | | V-2 | Chrnb3 |
| 15990 | 3 | 4 | 5 | | V-2 | Chst10 |
| 15991 | 3 | 4 | 5 | | V-2 | Chst4 |
| 15992 | 3 | 4 | 5 | | V-2 | Cic |
| 15993 | 3 | 4 | 5 | | V-2 | Clcn1 |
| 15994 | 3 | 4 | 5 | | V-2 | Clcn7 |
| 15995 | 3 | 4 | 5 | | V-2 | Clcnkb |
| 15996 | 3 | 4 | 5 | | V-2 | Clec5a |
| 15997 | 3 | 4 | 5 | | V-2 | Cnga2 |
| 15998 | 3 | 4 | 5 | | V-2 | Cnga4 |
| 15999 | 3 | 4 | 5 | | V-2 | Cnpy1 |
| 16000 | 3 | 4 | 5 | | V-2 | Cntn4 |
| 16001 | 3 | 4 | 5 | | V-2 | Cntnap4 |
| 16002 | 3 | 4 | 5 | | V-2 | Col10a1 |
| 16003 | 3 | 4 | 5 | | V-2 | Col6a5 |
| 16004 | 3 | 4 | 5 | | V-2 | Col6a6 |
| 16005 | 3 | 4 | 5 | | V-2 | Col9a1 |
| 16006 | 3 | 4 | 5 | | V-2 | Colec10 |
| 16007 | 3 | 4 | 5 | | V-2 | Colgalt2 |
| 16008 | 3 | 4 | 5 | | V-2 | Copa |
| 16009 | 3 | 4 | 5 | | V-2 | Cox11 |
| 16010 | 3 | 4 | 5 | | V-2 | Cpne4 |
| 16011 | 3 | 4 | 5 | | V-2 | Cpped1 |
| 16012 | 3 | 4 | 5 | | V-2 | Crhr1 |
| 16013 | 3 | 4 | 5 | | V-2 | Crnkl1 |
| 16014 | 3 | 4 | 5 | | V-2 | Crygb |
| 16015 | 3 | 4 | 5 | | V-2 | Cryz |
| 16016 | 3 | 4 | 5 | | V-2 | Cs |
| 16017 | 3 | 4 | 5 | | V-2 | Cstl1 |
| 16018 | 3 | 4 | 5 | | V-2 | Ctnnb1 |
| 16019 | 3 | 4 | 5 | | V-2 | Cul5 |
| 16020 | 3 | 4 | 5 | | V-2 | Cxcl3 |
| 16021 | 3 | 4 | 5 | | V-2 | Cyp19a1 |
| 16022 | 3 | 4 | 5 | | V-2 | Cyp2c39 |
| 16023 | 3 | 4 | 5 | | V-2 | Cyp2c67 |
| 16024 | 3 | 4 | 5 | | V-2 | Cyp2c68 |
| 16025 | 3 | 4 | 5 | | V-2 | Cyp2d40 |
| 16026 | 3 | 4 | 5 | | V-2 | Cyp2r1 |
| 16027 | 3 | 4 | 5 | | V-2 | Cyp3a44 |
| 16028 | 3 | 4 | 5 | | V-2 | Cyp3a59 |
| 16029 | 3 | 4 | 5 | | V-2 | Cyp4f14 |
| 16030 | 3 | 4 | 5 | | V-2 | Cypt8 |
| 16031 | 3 | 4 | 5 | | V-2 | D108wg1379e |
| 16032 | 3 | 4 | 5 | | V-2 | D5Ertd605e |
| 16033 | 3 | 4 | 5 | | V-2 | D630041G03Rik |
| 16034 | 3 | 4 | 5 | | V-2 | D930028M14Rik |
| 16035 | 3 | 4 | 5 | | V-2 | Daam1 |
| 16036 | 3 | 4 | 5 | | V-2 | Daglb |
| 16037 | 3 | 4 | 5 | | V-2 | Dazl |
| 16038 | 3 | 4 | 5 | | V-2 | Dchs1 |
| 16039 | 3 | 4 | 5 | | V-2 | Dctn1 |
| 16040 | 3 | 4 | 5 | | V-2 | Dcx |
| 16041 | 3 | 4 | 5 | | V-2 | Ddhd2 |
| 16042 | 3 | 4 | 5 | | V-2 | Ddx11 |
| 16043 | 3 | 4 | 5 | | V-2 | Defb30 |
| 16044 | 3 | 4 | 5 | | V-2 | Defb5 |
| 16045 | 3 | 4 | 5 | | V-2 | Dfna5 |
| 16046 | 3 | 4 | 5 | | V-2 | Dgki |
| 16047 | 3 | 4 | 5 | | V-2 | Dgkz |
| 16048 | 3 | 4 | 5 | | V-2 | Dlg3 |
| 16049 | 3 | 4 | 5 | | V-2 | Dlst |
| 16050 | 3 | 4 | 5 | | V-2 | Dlx3 |
| 16051 | 3 | 4 | 5 | | V-2 | Dmrt1 |
| 16052 | 3 | 4 | 5 | | V-2 | Dmrtc1c2 |
| 16053 | 3 | 4 | 5 | | V-2 | Dnah17 |
| 16054 | 3 | 4 | 5 | | V-2 | Dnaic1 |
| 16055 | 3 | 4 | 5 | | V-2 | Dnajc5 |
| 16056 | 3 | 4 | 5 | | V-2 | Dnase2b |
| 16057 | 3 | 4 | 5 | | V-2 | Dnmt3b |
| 16058 | 3 | 4 | 5 | | V-2 | Dock2 |
| 16059 | 3 | 4 | 5 | | V-2 | Dok5 |
| 16060 | 3 | 4 | 5 | | V-2 | Dpy19l2 |
| 16061 | 3 | 4 | 5 | | V-2 | Dscaml1 |
| 16062 | 3 | 4 | 5 | | V-2 | Dydc1 |
| 16063 | 3 | 4 | 5 | | V-2 | Dync2h1 |
| 16064 | 3 | 4 | 5 | | V-2 | Dynlt3 |
| 16065 | 3 | 4 | 5 | | V-2 | Dzip3 |
| 16066 | 3 | 4 | 5 | | V-2 | E030013I19Rik |
| 16067 | 3 | 4 | 5 | | V-2 | E030019B13Rik |
| 16068 | 3 | 4 | 5 | | V-2 | E330033B04Rik |
| 16069 | 3 | 4 | 5 | | V-2 | E530001F21Rik |
| 16070 | 3 | 4 | 5 | | V-2 | Ebf4 |
| 16071 | 3 | 4 | 5 | | V-2 | Edc3 |
| 16072 | 3 | 4 | 5 | | V-2 | Edn2 |
| 16073 | 3 | 4 | 5 | | V-2 | Efcab4b |
| 16074 | 3 | 4 | 5 | | V-2 | Efcab7 |
| 16075 | 3 | 4 | 5 | | V-2 | Efhc2 |
| 16076 | 3 | 4 | 5 | | V-2 | Efna2 |
| 16077 | 3 | 4 | 5 | | V-2 | Elovl2 |
| 16078 | 3 | 4 | 5 | | V-2 | Emilin3 |
| 16079 | 3 | 4 | 5 | | V-2 | Emr4 |
| 16080 | 3 | 4 | 5 | | V-2 | Enthd1 |
| 16081 | 3 | 4 | 5 | | V-2 | Epha5 |
| 16082 | 3 | 4 | 5 | | V-2 | Epha8 |
| 16083 | 3 | 4 | 5 | | V-2 | Erich6 |
| 16084 | 3 | 4 | 5 | | V-2 | Ern2 |
| 16085 | 3 | 4 | 5 | | V-2 | Etd |
| 16086 | 3 | 4 | 5 | | V-2 | Exph5 |
| 16087 | 3 | 4 | 5 | | V-2 | F630042J09Rik |
| 16088 | 3 | 4 | 5 | | V-2 | Fam124b |
| 16089 | 3 | 4 | 5 | | V-2 | Fam135b |
| 16090 | 3 | 4 | 5 | | V-2 | Fam170a |
| 16091 | 3 | 4 | 5 | | V-2 | Fam174b |
| 16092 | 3 | 4 | 5 | | V-2 | Fam181a |
| 16093 | 3 | 4 | 5 | | V-2 | Fam198a |
| 16094 | 3 | 4 | 5 | | V-2 | Fam19a3 |
| 16095 | 3 | 4 | 5 | | V-2 | Fam219b |
| 16096 | 3 | 4 | 5 | | V-2 | Fam222b |
| 16097 | 3 | 4 | 5 | | V-2 | Fam228b |
| 16098 | 3 | 4 | 5 | | V-2 | Fam26d |
| 16099 | 3 | 4 | 5 | | V-2 | Fam45a |
| 16100 | 3 | 4 | 5 | | V-2 | Fam71a |
| 16101 | 3 | 4 | 5 | | V-2 | Fancd2 |
| 16102 | 3 | 4 | 5 | | V-2 | Fanci |
| 16103 | 3 | 4 | 5 | | V-2 | Fbn2 |
| 16104 | 3 | 4 | 5 | | V-2 | Fbxl2os |
| 16105 | 3 | 4 | 5 | | V-2 | Fbxl7 |
| 16106 | 3 | 4 | 5 | | V-2 | Fbxo24 |
| 16107 | 3 | 4 | 5 | | V-2 | Fbxo3 |
| 16108 | 3 | 4 | 5 | | V-2 | Fbxo48 |
| 16109 | 3 | 4 | 5 | | V-2 | Fcho1 |
| 16110 | 3 | 4 | 5 | | V-2 | Fcrl6 |
| 16111 | 3 | 4 | 5 | | V-2 | Fer1l4 |
| 16112 | 3 | 4 | 5 | | V-2 | Fgf9 |
| 16113 | 3 | 4 | 5 | | V-2 | Fibcd1 |
| 16114 | 3 | 4 | 5 | | V-2 | Focad |
| 16115 | 3 | 4 | 5 | | V-2 | Foxd2os |
| 16116 | 3 | 4 | 5 | | V-2 | Foxk2 |
| 16117 | 3 | 4 | 5 | | V-2 | Fras1 |
| 16118 | 3 | 4 | 5 | | V-2 | Fscb |
| 16119 | 3 | 4 | 5 | | V-2 | Fsd1l |
| 16120 | 3 | 4 | 5 | | V-2 | Ftcd |
| 16121 | 3 | 4 | 5 | | V-2 | Gad1os |
| 16122 | 3 | 4 | 5 | | V-2 | Gapt |
| 16123 | 3 | 4 | 5 | | V-2 | Gas2l2 |
| 16124 | 3 | 4 | 5 | | V-2 | Gbx2 |
| 16125 | 3 | 4 | 5 | | V-2 | Gdnf |
| 16126 | 3 | 4 | 5 | | V-2 | Gipc1 |

Fig. 34 - 85

| | | | | | | | |
|---|---|---|---|---|---|---|---|
| 16127 | 3 | 4 | 5 | | V-2 | Git2 |
| 16128 | 3 | 4 | 5 | | V-2 | Gldnos |
| 16129 | 3 | 4 | 5 | | V-2 | Glipr1l2 |
| 16130 | 3 | 4 | 5 | | V-2 | Glod4 |
| 16131 | 3 | 4 | 5 | | V-2 | Glra1 |
| 16132 | 3 | 4 | 5 | | V-2 | Glra2 |
| 16133 | 3 | 4 | 5 | | V-2 | Glycam1 |
| 16134 | 3 | 4 | 5 | | V-2 | Gm10033 |
| 16135 | 3 | 4 | 5 | | V-2 | Gm10125 |
| 16136 | 3 | 4 | 5 | | V-2 | Gm10229 |
| 16137 | 3 | 4 | 5 | | V-2 | Gm10364 |
| 16138 | 3 | 4 | 5 | | V-2 | Gm10375 |
| 16139 | 3 | 4 | 5 | | V-2 | Gm10433 |
| 16140 | 3 | 4 | 5 | | V-2 | Gm1045 |
| 16141 | 3 | 4 | 5 | | V-2 | Gm10532 |
| 16142 | 3 | 4 | 5 | | V-2 | Gm10778 |
| 16143 | 3 | 4 | 5 | | V-2 | Gm10791 |
| 16144 | 3 | 4 | 5 | | V-2 | Gm10814 |
| 16145 | 3 | 4 | 5 | | V-2 | Gm11149 |
| 16146 | 3 | 4 | 5 | | V-2 | Gm11166 |
| 16147 | 3 | 4 | 5 | | V-2 | Gm11201 |
| 16148 | 3 | 4 | 5 | | V-2 | Gm11554 |
| 16149 | 3 | 4 | 5 | | V-2 | Gm14479 |
| 16150 | 3 | 4 | 5 | | V-2 | Gm14484 |
| 16151 | 3 | 4 | 5 | | V-2 | Gm1527 |
| 16152 | 3 | 4 | 5 | | V-2 | Gm15446 |
| 16153 | 3 | 4 | 5 | | V-2 | Gm15663 |
| 16154 | 3 | 4 | 5 | | V-2 | Gm15708 |
| 16155 | 3 | 4 | 5 | | V-2 | Gm15760 |
| 16156 | 3 | 4 | 5 | | V-2 | Gm16157 |
| 16157 | 3 | 4 | 5 | | V-2 | Gm16445 |
| 16158 | 3 | 4 | 5 | | V-2 | Gm16982 |
| 16159 | 3 | 4 | 5 | | V-2 | Gm17252 |
| 16160 | 3 | 4 | 5 | | V-2 | Gm19461 |
| 16161 | 3 | 4 | 5 | | V-2 | Gm1979 |
| 16162 | 3 | 4 | 5 | | V-2 | Gm19897 |
| 16163 | 3 | 4 | 5 | | V-2 | Gm20268 |
| 16164 | 3 | 4 | 5 | | V-2 | Gm20300 |
| 16165 | 3 | 4 | 5 | | V-2 | Gm20736 |
| 16166 | 3 | 4 | 5 | | V-2 | Gm20740 |
| 16167 | 3 | 4 | 5 | | V-2 | Gm20747 |
| 16168 | 3 | 4 | 5 | | V-2 | Gm20854 |
| 16169 | 3 | 4 | 5 | | V-2 | Gm20858 |
| 16170 | 3 | 4 | 5 | | V-2 | Gm2762 |
| 16171 | 3 | 4 | 5 | | V-2 | Gm2848 |
| 16172 | 3 | 4 | 5 | | V-2 | Gm3317 |
| 16173 | 3 | 4 | 5 | | V-2 | Gm3414 |
| 16174 | 3 | 4 | 5 | | V-2 | Gm3604 |
| 16175 | 3 | 4 | 5 | | V-2 | Gm364 |
| 16176 | 3 | 4 | 5 | | V-2 | Gm41 |
| 16177 | 3 | 4 | 5 | | V-2 | Gm4251 |
| 16178 | 3 | 4 | 5 | | V-2 | Gm4489 |
| 16179 | 3 | 4 | 5 | | V-2 | Gm4598 |
| 16180 | 3 | 4 | 5 | | V-2 | Gm4846 |
| 16181 | 3 | 4 | 5 | | V-2 | Gm5141 |
| 16182 | 3 | 4 | 5 | | V-2 | Gm5416 |
| 16183 | 3 | 4 | 5 | | V-2 | Gm5478 |
| 16184 | 3 | 4 | 5 | | V-2 | Gm5592 |
| 16185 | 3 | 4 | 5 | | V-2 | Gm572 |
| 16186 | 3 | 4 | 5 | | V-2 | Gm5820 |
| 16187 | 3 | 4 | 5 | | V-2 | Gm5935 |
| 16188 | 3 | 4 | 5 | | V-2 | Gm597 |
| 16189 | 3 | 4 | 5 | | V-2 | Gm6026 |
| 16190 | 3 | 4 | 5 | | V-2 | Gm6268 |
| 16191 | 3 | 4 | 5 | | V-2 | Gm6567 |
| 16192 | 3 | 4 | 5 | | V-2 | Gm6760 |
| 16193 | 3 | 4 | 5 | | V-2 | Gm6792 |
| 16194 | 3 | 4 | 5 | | V-2 | Gm6793 |
| 16195 | 3 | 4 | 5 | | V-2 | Gm7008 |
| 16196 | 3 | 4 | 5 | | V-2 | Gm715 |
| 16197 | 3 | 4 | 5 | | V-2 | Gm7157 |
| 16198 | 3 | 4 | 5 | | V-2 | Gm8096 |
| 16199 | 3 | 4 | 5 | | V-2 | Gm8633 |
| 16200 | 3 | 4 | 5 | | V-2 | Gm9 |
| 16201 | 3 | 4 | 5 | | V-2 | Gm9079 |
| 16202 | 3 | 4 | 5 | | V-2 | Gm9731 |
| 16203 | 3 | 4 | 5 | | V-2 | Gmeb2 |
| 16204 | 3 | 4 | 5 | | V-2 | Gna11 |
| 16205 | 3 | 4 | 5 | | V-2 | Gnai2 |
| 16206 | 3 | 4 | 5 | | V-2 | Gnb1 |
| 16207 | 3 | 4 | 5 | | V-2 | Golga2 |
| 16208 | 3 | 4 | 5 | | V-2 | Gpbar1 |
| 16209 | 3 | 4 | 5 | | V-2 | Gpc6 |
| 16210 | 3 | 4 | 5 | | V-2 | Gpd1l |
| 16211 | 3 | 4 | 5 | | V-2 | Gpr12 |
| 16212 | 3 | 4 | 5 | | V-2 | Gpr126 |
| 16213 | 3 | 4 | 5 | | V-2 | Gpr174 |
| 16214 | 3 | 4 | 5 | | V-2 | Gpr63 |
| 16215 | 3 | 4 | 5 | | V-2 | Gpr84 |
| 16216 | 3 | 4 | 5 | | V-2 | Gpx6 |
| 16217 | 3 | 4 | 5 | | V-2 | Grk4 |
| 16218 | 3 | 4 | 5 | | V-2 | Grk5 |
| 16219 | 3 | 4 | 5 | | V-2 | Grm7 |
| 16220 | 3 | 4 | 5 | | V-2 | Gsdmc3 |
| 16221 | 3 | 4 | 5 | | V-2 | Gsdmc4 |
| 16222 | 3 | 4 | 5 | | V-2 | Gsdmcl1 |
| 16223 | 3 | 4 | 5 | | V-2 | Gtf2a1l |
| 16224 | 3 | 4 | 5 | | V-2 | Gucy2g |
| 16225 | 3 | 4 | 5 | | V-2 | Gulo |
| 16226 | 3 | 4 | 5 | | V-2 | H1f0 |
| 16227 | 3 | 4 | 5 | | V-2 | H2afb3 |
| 16228 | 3 | 4 | 5 | | V-2 | Hao1 |
| 16229 | 3 | 4 | 5 | | V-2 | Hapln3 |
| 16230 | 3 | 4 | 5 | | V-2 | Has3 |
| 16231 | 3 | 4 | 5 | | V-2 | Havcr2 |
| 16232 | 3 | 4 | 5 | | V-2 | Hcn4 |
| 16233 | 3 | 4 | 5 | | V-2 | Heatr5a |
| 16234 | 3 | 4 | 5 | | V-2 | Henmt1 |
| 16235 | 3 | 4 | 5 | | V-2 | Hes2 |
| 16236 | 3 | 4 | 5 | | V-2 | Hmg20a |
| 16237 | 3 | 4 | 5 | | V-2 | Hmga2 |
| 16238 | 3 | 4 | 5 | | V-2 | Hmgxb3 |
| 16239 | 3 | 4 | 5 | | V-2 | Hmx3 |
| 16240 | 3 | 4 | 5 | | V-2 | Hnrnpr |
| 16241 | 3 | 4 | 5 | | V-2 | Hormad1 |
| 16242 | 3 | 4 | 5 | | V-2 | Hottip |
| 16243 | 3 | 4 | 5 | | V-2 | Hoxa1 |
| 16244 | 3 | 4 | 5 | | V-2 | Hoxa10 |
| 16245 | 3 | 4 | 5 | | V-2 | Hoxa11 |
| 16246 | 3 | 4 | 5 | | V-2 | Hoxa6 |
| 16247 | 3 | 4 | 5 | | V-2 | Hoxa9 |
| 16248 | 3 | 4 | 5 | | V-2 | Hoxd11 |
| 16249 | 3 | 4 | 5 | | V-2 | Hoxd12 |
| 16250 | 3 | 4 | 5 | | V-2 | Hprt |
| 16251 | 3 | 4 | 5 | | V-2 | Hps5 |
| 16252 | 3 | 4 | 5 | | V-2 | Hpse2 |
| 16253 | 3 | 4 | 5 | | V-2 | Hrh4 |
| 16254 | 3 | 4 | 5 | | V-2 | Hs6st3 |
| 16255 | 3 | 4 | 5 | | V-2 | Hsf5 |
| 16256 | 3 | 4 | 5 | | V-2 | Htr1d |
| 16257 | 3 | 4 | 5 | | V-2 | Htr2b |
| 16258 | 3 | 4 | 5 | | V-2 | Htr4 |
| 16259 | 3 | 4 | 5 | | V-2 | Htr6 |
| 16260 | 3 | 4 | 5 | | V-2 | Huwe1 |
| 16261 | 3 | 4 | 5 | | V-2 | Hyal3 |
| 16262 | 3 | 4 | 5 | | V-2 | Hydin |
| 16263 | 3 | 4 | 5 | | V-2 | Icos |
| 16264 | 3 | 4 | 5 | | V-2 | Ifng |
| 16265 | 3 | 4 | 5 | | V-2 | Igsf1 |
| 16266 | 3 | 4 | 5 | | V-2 | Il22 |
| 16267 | 3 | 4 | 5 | | V-2 | Il31 |
| 16268 | 3 | 4 | 5 | | V-2 | Inhba |
| 16269 | 3 | 4 | 5 | | V-2 | Inhbe |
| 16270 | 3 | 4 | 5 | | V-2 | Inip |
| 16271 | 3 | 4 | 5 | | V-2 | Ino80c |
| 16272 | 3 | 4 | 5 | | V-2 | Inpp4b |
| 16273 | 3 | 4 | 5 | | V-2 | Inpp5k |
| 16274 | 3 | 4 | 5 | | V-2 | Ins1 |
| 16275 | 3 | 4 | 5 | | V-2 | Insm1 |
| 16276 | 3 | 4 | 5 | | V-2 | Ints5 |
| 16277 | 3 | 4 | 5 | | V-2 | Intu |
| 16278 | 3 | 4 | 5 | | V-2 | Iqch |
| 16279 | 3 | 4 | 5 | | V-2 | Irf2bp1 |
| 16280 | 3 | 4 | 5 | | V-2 | Itgad |
| 16281 | 3 | 4 | 5 | | V-2 | Itgal |
| 16282 | 3 | 4 | 5 | | V-2 | Itgb1 |
| 16283 | 3 | 4 | 5 | | V-2 | Jakmip2 |
| 16284 | 3 | 4 | 5 | | V-2 | Jakmip3 |
| 16285 | 3 | 4 | 5 | | V-2 | Jpx |
| 16286 | 3 | 4 | 5 | | V-2 | Jrk |
| 16287 | 3 | 4 | 5 | | V-2 | Kcne1 |
| 16288 | 3 | 4 | 5 | | V-2 | Kcne2 |
| 16289 | 3 | 4 | 5 | | V-2 | Kcnh7 |
| 16290 | 3 | 4 | 5 | | V-2 | Kcnk4 |
| 16291 | 3 | 4 | 5 | | V-2 | Kcnmb2 |
| 16292 | 3 | 4 | 5 | | V-2 | Kcnmb3 |
| 16293 | 3 | 4 | 5 | | V-2 | Kcnn3 |
| 16294 | 3 | 4 | 5 | | V-2 | Kcns1 |
| 16295 | 3 | 4 | 5 | | V-2 | Kcnv2 |
| 16296 | 3 | 4 | 5 | | V-2 | Kdm4d |
| 16297 | 3 | 4 | 5 | | V-2 | Kdm6b |
| 16298 | 3 | 4 | 5 | | V-2 | Kif4 |
| 16299 | 3 | 4 | 5 | | V-2 | Klhl23 |
| 16300 | 3 | 4 | 5 | | V-2 | Klhl32 |
| 16301 | 3 | 4 | 5 | | V-2 | Klhl4 |
| 16302 | 3 | 4 | 5 | | V-2 | Knop1 |
| 16303 | 3 | 4 | 5 | | V-2 | Kpna7 |
| 16304 | 3 | 4 | 5 | | V-2 | Kpnb1 |
| 16305 | 3 | 4 | 5 | | V-2 | Krt72 |
| 16306 | 3 | 4 | 5 | | V-2 | Krtap4-13 |
| 16307 | 3 | 4 | 5 | | V-2 | LOC102634401 |
| 16308 | 3 | 4 | 5 | | V-2 | LOC102635087 |
| 16309 | 3 | 4 | 5 | | V-2 | LOC381967 |
| 16310 | 3 | 4 | 5 | | V-2 | Lage3 |
| 16311 | 3 | 4 | 5 | | V-2 | Lama5 |
| 16312 | 3 | 4 | 5 | | V-2 | Lamp1 |
| 16313 | 3 | 4 | 5 | | V-2 | Lce6a |
| 16314 | 3 | 4 | 5 | | V-2 | Lefty2 |
| 16315 | 3 | 4 | 5 | | V-2 | Leng8 |
| 16316 | 3 | 4 | 5 | | V-2 | Lhcgr |
| 16317 | 3 | 4 | 5 | | V-2 | Lhx6 |
| 16318 | 3 | 4 | 5 | | V-2 | Lin28a |

Fig. 34 - 86

| | | | | | | | |
|---|---|---|---|---|---|---|---|
| 16319 | 3 | 4 | 5 | | V-2 | Lingo2 |
| 16320 | 3 | 4 | 5 | | V-2 | Lingo4 |
| 16321 | 3 | 4 | 5 | | V-2 | Lmbr1 |
| 16322 | 3 | 4 | 5 | | V-2 | Lrat |
| 16323 | 3 | 4 | 5 | | V-2 | Lrguk |
| 16324 | 3 | 4 | 5 | | V-2 | Lrrc6 |
| 16325 | 3 | 4 | 5 | | V-2 | Lrrc66 |
| 16326 | 3 | 4 | 5 | | V-2 | Lrrc69 |
| 16327 | 3 | 4 | 5 | | V-2 | Lrrd1 |
| 16328 | 3 | 4 | 5 | | V-2 | Lrriq4 |
| 16329 | 3 | 4 | 5 | | V-2 | Lrrk2 |
| 16330 | 3 | 4 | 5 | | V-2 | Luc7l3 |
| 16331 | 3 | 4 | 5 | | V-2 | Ly6g5c |
| 16332 | 3 | 4 | 5 | | V-2 | Ly6g6f |
| 16333 | 3 | 4 | 5 | | V-2 | Ly9 |
| 16334 | 3 | 4 | 5 | | V-2 | Lypd3 |
| 16335 | 3 | 4 | 5 | | V-2 | Lyrm5 |
| 16336 | 3 | 4 | 5 | | V-2 | Lyrm7os |
| 16337 | 3 | 4 | 5 | | V-2 | Madcam1 |
| 16338 | 3 | 4 | 5 | | V-2 | Magea3 |
| 16339 | 3 | 4 | 5 | | V-2 | Magea5 |
| 16340 | 3 | 4 | 5 | | V-2 | Mageb1 |
| 16341 | 3 | 4 | 5 | | V-2 | Map3k13 |
| 16342 | 3 | 4 | 5 | | V-2 | Mapk8ip3 |
| 16343 | 3 | 4 | 5 | | V-2 | Mapre1 |
| 16344 | 3 | 4 | 5 | | V-2 | Mark2 |
| 16345 | 3 | 4 | 5 | | V-2 | Mark3 |
| 16346 | 3 | 4 | 5 | | V-2 | Mars2 |
| 16347 | 3 | 4 | 5 | | V-2 | Mboat4 |
| 16348 | 3 | 4 | 5 | | V-2 | Mbtps1 |
| 16349 | 3 | 4 | 5 | | V-2 | Mdga1 |
| 16350 | 3 | 4 | 5 | | V-2 | Mdn1 |
| 16351 | 3 | 4 | 5 | | V-2 | Med19 |
| 16352 | 3 | 4 | 5 | | V-2 | Med23 |
| 16353 | 3 | 4 | 5 | | V-2 | Mefv |
| 16354 | 3 | 4 | 5 | | V-2 | Meiob |
| 16355 | 3 | 4 | 5 | | V-2 | Mesdc2 |
| 16356 | 3 | 4 | 5 | | V-2 | Mesp1 |
| 16357 | 3 | 4 | 5 | | V-2 | Mettl14 |
| 16358 | 3 | 4 | 5 | | V-2 | Mettl7a2Higd1c |
| 16359 | 3 | 4 | 5 | | V-2 | Mfn2 |
| 16360 | 3 | 4 | 5 | | V-2 | Mfsd9 |
| 16361 | 3 | 4 | 5 | | V-2 | Mgat4a |
| 16362 | 3 | 4 | 5 | | V-2 | Miox |
| 16363 | 3 | 4 | 5 | | V-2 | Mkrn3 |
| 16364 | 3 | 4 | 5 | | V-2 | Mmgt1 |
| 16365 | 3 | 4 | 5 | | V-2 | Mmp16 |
| 16366 | 3 | 4 | 5 | | V-2 | Mnx1 |
| 16367 | 3 | 4 | 5 | | V-2 | Mon1b |
| 16368 | 3 | 4 | 5 | | V-2 | Morc2b |
| 16369 | 3 | 4 | 5 | | V-2 | Mphosph9 |
| 16370 | 3 | 4 | 5 | | V-2 | Mpl |
| 16371 | 3 | 4 | 5 | | V-2 | Mrpl50 |
| 16372 | 3 | 4 | 5 | | V-2 | Mrps31 |
| 16373 | 3 | 4 | 5 | | V-2 | Ms4a10 |
| 16374 | 3 | 4 | 5 | | V-2 | Ms4a13 |
| 16375 | 3 | 4 | 5 | | V-2 | Msmb |
| 16376 | 3 | 4 | 5 | | V-2 | Mturn |
| 16377 | 3 | 4 | 5 | | V-2 | Mtx3 |
| 16378 | 3 | 4 | 5 | | V-2 | Muc5ac |
| 16379 | 3 | 4 | 5 | | V-2 | Muc6 |
| 16380 | 3 | 4 | 5 | | V-2 | Mum1 |
| 16381 | 3 | 4 | 5 | | V-2 | Myo10 |
| 16382 | 3 | 4 | 5 | | V-2 | Naa11 |
| 16383 | 3 | 4 | 5 | | V-2 | Naaladl1 |
| 16384 | 3 | 4 | 5 | | V-2 | Nadk |
| 16385 | 3 | 4 | 5 | | V-2 | Naif1 |
| 16386 | 3 | 4 | 5 | | V-2 | Naip1 |
| 16387 | 3 | 4 | 5 | | V-2 | Nanos1 |
| 16388 | 3 | 4 | 5 | | V-2 | Nbeal1 |
| 16389 | 3 | 4 | 5 | | V-2 | Ncbp1 |
| 16390 | 3 | 4 | 5 | | V-2 | Ncbp2 |
| 16391 | 3 | 4 | 5 | | V-2 | Ncoa3 |
| 16392 | 3 | 4 | 5 | | V-2 | Ndc80 |
| 16393 | 3 | 4 | 5 | | V-2 | Nek1 |
| 16394 | 3 | 4 | 5 | | V-2 | Neurog1 |
| 16395 | 3 | 4 | 5 | | V-2 | Nfam1 |
| 16396 | 3 | 4 | 5 | | V-2 | Nfatc3 |
| 16397 | 3 | 4 | 5 | | V-2 | Nhlh1 |
| 16398 | 3 | 4 | 5 | | V-2 | Nipsnap3a |
| 16399 | 3 | 4 | 5 | | V-2 | Nisch |
| 16400 | 3 | 4 | 5 | | V-2 | Nkx2-4 |
| 16401 | 3 | 4 | 5 | | V-2 | Nkx2-6 |
| 16402 | 3 | 4 | 5 | | V-2 | Nkx3-2 |
| 16403 | 3 | 4 | 5 | | V-2 | Nlgn1 |
| 16404 | 3 | 4 | 5 | | V-2 | Nlrp1b |
| 16405 | 3 | 4 | 5 | | V-2 | Nlrp9b |
| 16406 | 3 | 4 | 5 | | V-2 | Nono |
| 16407 | 3 | 4 | 5 | | V-2 | Nphs1 |
| 16408 | 3 | 4 | 5 | | V-2 | Nr5a1 |
| 16409 | 3 | 4 | 5 | | V-2 | Nrd1 |
| 16410 | 3 | 4 | 5 | | V-2 | Nudt19 |
| 16411 | 3 | 4 | 5 | | V-2 | Nudt3 |
| 16412 | 3 | 4 | 5 | | V-2 | Nup188 |
| 16413 | 3 | 4 | 5 | | V-2 | Nup62cl |
| 16414 | 3 | 4 | 5 | | V-2 | Nup88 |
| 16415 | 3 | 4 | 5 | | V-2 | Nus1 |
| 16416 | 3 | 4 | 5 | | V-2 | Nxf3 |
| 16417 | 3 | 4 | 5 | | V-2 | Oas1e |
| 16418 | 3 | 4 | 5 | | V-2 | Olfr126 |
| 16419 | 3 | 4 | 5 | | V-2 | Olfr127 |
| 16420 | 3 | 4 | 5 | | V-2 | Olfr128 |
| 16421 | 3 | 4 | 5 | | V-2 | Olfr212 |
| 16422 | 3 | 4 | 5 | | V-2 | Olfr303 |
| 16423 | 3 | 4 | 5 | | V-2 | Olfr31 |
| 16424 | 3 | 4 | 5 | | V-2 | Olfr419 |
| 16425 | 3 | 4 | 5 | | V-2 | Olfr521 |
| 16426 | 3 | 4 | 5 | | V-2 | Olfr99 |
| 16427 | 3 | 4 | 5 | | V-2 | Opa1 |
| 16428 | 3 | 4 | 5 | | V-2 | Opn4 |
| 16429 | 3 | 4 | 5 | | V-2 | Oprd1 |
| 16430 | 3 | 4 | 5 | | V-2 | Oprk1 |
| 16431 | 3 | 4 | 5 | | V-2 | Ostm1 |
| 16432 | 3 | 4 | 5 | | V-2 | Oxsr1 |
| 16433 | 3 | 4 | 5 | | V-2 | P2rx2 |
| 16434 | 3 | 4 | 5 | | V-2 | P2rx3 |
| 16435 | 3 | 4 | 5 | | V-2 | Pank2 |
| 16436 | 3 | 4 | 5 | | V-2 | Parpbp |
| 16437 | 3 | 4 | 5 | | V-2 | Pcdh19 |
| 16438 | 3 | 4 | 5 | | V-2 | Pcdhb21 |
| 16439 | 3 | 4 | 5 | | V-2 | Pcdhb22 |
| 16440 | 3 | 4 | 5 | | V-2 | Pcdhb3 |
| 16441 | 3 | 4 | 5 | | V-2 | Pcdhb7 |
| 16442 | 3 | 4 | 5 | | V-2 | Pcnxl4 |
| 16443 | 3 | 4 | 5 | | V-2 | Pcsk9 |
| 16444 | 3 | 4 | 5 | | V-2 | Pdcd1lg2 |
| 16445 | 3 | 4 | 5 | | V-2 | Pde1c |
| 16446 | 3 | 4 | 5 | | V-2 | Pdf |
| 16447 | 3 | 4 | 5 | | V-2 | Pdha1 |
| 16448 | 3 | 4 | 5 | | V-2 | Pdx1 |
| 16449 | 3 | 4 | 5 | | V-2 | Pea15a |
| 16450 | 3 | 4 | 5 | | V-2 | Pex2 |
| 16451 | 3 | 4 | 5 | | V-2 | Pgbd1 |
| 16452 | 3 | 4 | 5 | | V-2 | Pgm5 |
| 16453 | 3 | 4 | 5 | | V-2 | Phykpl |
| 16454 | 3 | 4 | 5 | | V-2 | Pih1d3 |
| 16455 | 3 | 4 | 5 | | V-2 | Pik3cg |
| 16456 | 3 | 4 | 5 | | V-2 | Pik3r3 |
| 16457 | 3 | 4 | 5 | | V-2 | Pik3r6 |
| 16458 | 3 | 4 | 5 | | V-2 | Pisd |
| 16459 | 3 | 4 | 5 | | V-2 | Pisd-ps2 |
| 16460 | 3 | 4 | 5 | | V-2 | Pla2g2f |
| 16461 | 3 | 4 | 5 | | V-2 | Plac1 |
| 16462 | 3 | 4 | 5 | | V-2 | Plcxd3 |
| 16463 | 3 | 4 | 5 | | V-2 | Pld5 |
| 16464 | 3 | 4 | 5 | | V-2 | Plxdc1 |
| 16465 | 3 | 4 | 5 | | V-2 | Pms1 |
| 16466 | 3 | 4 | 5 | | V-2 | Pnpla1 |
| 16467 | 3 | 4 | 5 | | V-2 | Pofut1 |
| 16468 | 3 | 4 | 5 | | V-2 | Pogk |
| 16469 | 3 | 4 | 5 | | V-2 | Pole2 |
| 16470 | 3 | 4 | 5 | | V-2 | Polq |
| 16471 | 3 | 4 | 5 | | V-2 | Pom121l2 |
| 16472 | 3 | 4 | 5 | | V-2 | Postn |
| 16473 | 3 | 4 | 5 | | V-2 | Ppip5k1 |
| 16474 | 3 | 4 | 5 | | V-2 | Ppm1a |
| 16475 | 3 | 4 | 5 | | V-2 | Ppp1r2-ps7 |
| 16476 | 3 | 4 | 5 | | V-2 | Ppp1r26 |
| 16477 | 3 | 4 | 5 | | V-2 | Ppp2r2a |
| 16478 | 3 | 4 | 5 | | V-2 | Prdm10 |
| 16479 | 3 | 4 | 5 | | V-2 | Prdm15 |
| 16480 | 3 | 4 | 5 | | V-2 | Prf1 |
| 16481 | 3 | 4 | 5 | | V-2 | Prickle1 |
| 16482 | 3 | 4 | 5 | | V-2 | Prkaca |
| 16483 | 3 | 4 | 5 | | V-2 | Prkar1a |
| 16484 | 3 | 4 | 5 | | V-2 | Prkg2 |
| 16485 | 3 | 4 | 5 | | V-2 | Prodh2 |
| 16486 | 3 | 4 | 5 | | V-2 | Prokr1 |
| 16487 | 3 | 4 | 5 | | V-2 | Prpf8 |
| 16488 | 3 | 4 | 5 | | V-2 | Prr9 |
| 16489 | 3 | 4 | 5 | | V-2 | Prss30 |
| 16490 | 3 | 4 | 5 | | V-2 | Prss35 |
| 16491 | 3 | 4 | 5 | | V-2 | Prss42 |
| 16492 | 3 | 4 | 5 | | V-2 | Prss51 |
| 16493 | 3 | 4 | 5 | | V-2 | Prss54 |
| 16494 | 3 | 4 | 5 | | V-2 | Pspn |
| 16495 | 3 | 4 | 5 | | V-2 | Ptchd3 |
| 16496 | 3 | 4 | 5 | | V-2 | Ptgr2 |
| 16497 | 3 | 4 | 5 | | V-2 | Ptpn7 |
| 16498 | 3 | 4 | 5 | | V-2 | Ptprh |
| 16499 | 3 | 4 | 5 | | V-2 | Pus7l |
| 16500 | 3 | 4 | 5 | | V-2 | Pygo2 |
| 16501 | 3 | 4 | 5 | | V-2 | Pzp |
| 16502 | 3 | 4 | 5 | | V-2 | R3hdm4 |
| 16503 | 3 | 4 | 5 | | V-2 | Rab25 |
| 16504 | 3 | 4 | 5 | | V-2 | Rab28 |
| 16505 | 3 | 4 | 5 | | V-2 | Rab3b |
| 16506 | 3 | 4 | 5 | | V-2 | Rabl3 |
| 16507 | 3 | 4 | 5 | | V-2 | Rala |
| 16508 | 3 | 4 | 5 | | V-2 | Ralgps1 |
| 16509 | 3 | 4 | 5 | | V-2 | Ranbp17 |
| 16510 | 3 | 4 | 5 | | V-2 | Ranbp3l |

Fig. 34 - 87

| | | | | | | | |
|---|---|---|---|---|---|---|---|
| 16511 | 3 | 4 | 5 | | V-2 | Rasgrp2 |
| 16512 | 3 | 4 | 5 | | V-2 | Raver1 |
| 16513 | 3 | 4 | 5 | | V-2 | Rbm43 |
| 16514 | 3 | 4 | 5 | | V-2 | Rbm46os |
| 16515 | 3 | 4 | 5 | | V-2 | Rbmx |
| 16516 | 3 | 4 | 5 | | V-2 | Rfx3 |
| 16517 | 3 | 4 | 5 | | V-2 | Rgp1 |
| 16518 | 3 | 4 | 5 | | V-2 | Rho |
| 16519 | 3 | 4 | 5 | | V-2 | Rhox13 |
| 16520 | 3 | 4 | 5 | | V-2 | Rhox3e |
| 16521 | 3 | 4 | 5 | | V-2 | Rhox3h |
| 16522 | 3 | 4 | 5 | | V-2 | Rimbp3 |
| 16523 | 3 | 4 | 5 | | V-2 | Rimklb |
| 16524 | 3 | 4 | 5 | | V-2 | Ripk1 |
| 16525 | 3 | 4 | 5 | | V-2 | Rlbp1 |
| 16526 | 3 | 4 | 5 | | V-2 | Rnase11 |
| 16527 | 3 | 4 | 5 | | V-2 | Rnf139 |
| 16528 | 3 | 4 | 5 | | V-2 | Rnf20 |
| 16529 | 3 | 4 | 5 | | V-2 | Rnf207 |
| 16530 | 3 | 4 | 5 | | V-2 | Robo2 |
| 16531 | 3 | 4 | 5 | | V-2 | Rorb |
| 16532 | 3 | 4 | 5 | | V-2 | Rpl34-ps1 |
| 16533 | 3 | 4 | 5 | | V-2 | Rrp8 |
| 16534 | 3 | 4 | 5 | | V-2 | Rtkn2 |
| 16535 | 3 | 4 | 5 | | V-2 | Rtl1 |
| 16536 | 3 | 4 | 5 | | V-2 | Rtn3 |
| 16537 | 3 | 4 | 5 | | V-2 | Runx2 |
| 16538 | 3 | 4 | 5 | | V-2 | Ryr3 |
| 16539 | 3 | 4 | 5 | | V-2 | S100a7a |
| 16540 | 3 | 4 | 5 | | V-2 | Samd3 |
| 16541 | 3 | 4 | 5 | | V-2 | Samt3 |
| 16542 | 3 | 4 | 5 | | V-2 | Sarm1 |
| 16543 | 3 | 4 | 5 | | V-2 | Sass6 |
| 16544 | 3 | 4 | 5 | | V-2 | Satb2 |
| 16545 | 3 | 4 | 5 | | V-2 | Scaper |
| 16546 | 3 | 4 | 5 | | V-2 | Sco1 |
| 16547 | 3 | 4 | 5 | | V-2 | Scpep1os |
| 16548 | 3 | 4 | 5 | | V-2 | Sec14l1 |
| 16549 | 3 | 4 | 5 | | V-2 | Sec22c |
| 16550 | 3 | 4 | 5 | | V-2 | Sec24c |
| 16551 | 3 | 4 | 5 | | V-2 | Sec62 |
| 16552 | 3 | 4 | 5 | | V-2 | Selt |
| 16553 | 3 | 4 | 5 | | V-2 | Sema4f |
| 16554 | 3 | 4 | 5 | | V-2 | Senp8 |
| 16555 | 3 | 4 | 5 | | V-2 | Sept7 |
| 16556 | 3 | 4 | 5 | | V-2 | Serac1 |
| 16557 | 3 | 4 | 5 | | V-2 | Serpina5 |
| 16558 | 3 | 4 | 5 | | V-2 | Serpinb6e |
| 16559 | 3 | 4 | 5 | | V-2 | Sf3b4 |
| 16560 | 3 | 4 | 5 | | V-2 | Sgms2 |
| 16561 | 3 | 4 | 5 | | V-2 | Sh3rf1 |
| 16562 | 3 | 4 | 5 | | V-2 | Sh3rf3 |
| 16563 | 3 | 4 | 5 | | V-2 | Shc3 |
| 16564 | 3 | 4 | 5 | | V-2 | Shcbp1l |
| 16565 | 3 | 4 | 5 | | V-2 | Shh |
| 16566 | 3 | 4 | 5 | | V-2 | Shisa3 |
| 16567 | 3 | 4 | 5 | | V-2 | Skida1 |
| 16568 | 3 | 4 | 5 | | V-2 | Skint11 |
| 16569 | 3 | 4 | 5 | | V-2 | Skint6 |
| 16570 | 3 | 4 | 5 | | V-2 | Skint7 |
| 16571 | 3 | 4 | 5 | | V-2 | Slc10a7 |
| 16572 | 3 | 4 | 5 | | V-2 | Slc16a5 |
| 16573 | 3 | 4 | 5 | | V-2 | Slc17a3 |
| 16574 | 3 | 4 | 5 | | V-2 | Slc17a8 |
| 16575 | 3 | 4 | 5 | | V-2 | Slc1a6 |
| 16576 | 3 | 4 | 5 | | V-2 | Slc22a16 |
| 16577 | 3 | 4 | 5 | | V-2 | Slc22a22 |
| 16578 | 3 | 4 | 5 | | V-2 | Slc22a6 |
| 16579 | 3 | 4 | 5 | | V-2 | Slc24a4 |
| 16580 | 3 | 4 | 5 | | V-2 | Slc25a38 |
| 16581 | 3 | 4 | 5 | | V-2 | Slc2a10 |
| 16582 | 3 | 4 | 5 | | V-2 | Slc30a10 |
| 16583 | 3 | 4 | 5 | | V-2 | Slc31a1 |
| 16584 | 3 | 4 | 5 | | V-2 | Slc33a1 |
| 16585 | 3 | 4 | 5 | | V-2 | Slc35c1 |
| 16586 | 3 | 4 | 5 | | V-2 | Slc39a1 |
| 16587 | 3 | 4 | 5 | | V-2 | Slc48a1 |
| 16588 | 3 | 4 | 5 | | V-2 | Slc4a5 |
| 16589 | 3 | 4 | 5 | | V-2 | Slc5a10 |
| 16590 | 3 | 4 | 5 | | V-2 | Slc9a4 |
| 16591 | 3 | 4 | 5 | | V-2 | Slc9a7 |
| 16592 | 3 | 4 | 5 | | V-2 | Slco3a1 |
| 16593 | 3 | 4 | 5 | | V-2 | Slco6b1 |
| 16594 | 3 | 4 | 5 | | V-2 | Slfn10-ps |
| 16595 | 3 | 4 | 5 | | V-2 | Smarca4 |
| 16596 | 3 | 4 | 5 | | V-2 | Smc1a |
| 16597 | 3 | 4 | 5 | | V-2 | Smim18 |
| 16598 | 3 | 4 | 5 | | V-2 | Sned1 |
| 16599 | 3 | 4 | 5 | | V-2 | Snx14 |
| 16600 | 3 | 4 | 5 | | V-2 | Sowahd |
| 16601 | 3 | 4 | 5 | | V-2 | Sox15 |
| 16602 | 3 | 4 | 5 | | V-2 | Spag4 |
| 16603 | 3 | 4 | 5 | | V-2 | Spata31d1d |
| 16604 | 3 | 4 | 5 | | V-2 | Spata32 |
| 16605 | 3 | 4 | 5 | | V-2 | Spdyb |
| 16606 | 3 | 4 | 5 | | V-2 | Speer4a |
| 16607 | 3 | 4 | 5 | | V-2 | Speer4d |
| 16608 | 3 | 4 | 5 | | V-2 | Spint5 |
| 16609 | 3 | 4 | 5 | | V-2 | Spp2 |
| 16610 | 3 | 4 | 5 | | V-2 | Srgap1 |
| 16611 | 3 | 4 | 5 | | V-2 | Srpk2 |
| 16612 | 3 | 4 | 5 | | V-2 | Srsf12 |
| 16613 | 3 | 4 | 5 | | V-2 | Sstr5 |
| 16614 | 3 | 4 | 5 | | V-2 | Ssxb6 |
| 16615 | 3 | 4 | 5 | | V-2 | St18 |
| 16616 | 3 | 4 | 5 | | V-2 | St6gal2 |
| 16617 | 3 | 4 | 5 | | V-2 | St6galnac6 |
| 16618 | 3 | 4 | 5 | | V-2 | St8sia3os |
| 16619 | 3 | 4 | 5 | | V-2 | Stac |
| 16620 | 3 | 4 | 5 | | V-2 | Stoml1 |
| 16621 | 3 | 4 | 5 | | V-2 | Stt3a |
| 16622 | 3 | 4 | 5 | | V-2 | Styk1 |
| 16623 | 3 | 4 | 5 | | V-2 | Surf4 |
| 16624 | 3 | 4 | 5 | | V-2 | Sv2c |
| 16625 | 3 | 4 | 5 | | V-2 | Syn3 |
| 16626 | 3 | 4 | 5 | | V-2 | Syt17 |
| 16627 | 3 | 4 | 5 | | V-2 | Sytl5 |
| 16628 | 3 | 4 | 5 | | V-2 | Tacr1 |
| 16629 | 3 | 4 | 5 | | V-2 | Taf3 |
| 16630 | 3 | 4 | 5 | | V-2 | Taf7l |
| 16631 | 3 | 4 | 5 | | V-2 | Tbc1d9b |
| 16632 | 3 | 4 | 5 | | V-2 | Tbpl1 |
| 16633 | 3 | 4 | 5 | | V-2 | Tcam1 |
| 16634 | 3 | 4 | 5 | | V-2 | Tcof1 |
| 16635 | 3 | 4 | 5 | | V-2 | Tctn3 |
| 16636 | 3 | 4 | 5 | | V-2 | Tdrd5 |
| 16637 | 3 | 4 | 5 | | V-2 | Tecpr2 |
| 16638 | 3 | 4 | 5 | | V-2 | Tenm1 |
| 16639 | 3 | 4 | 5 | | V-2 | Tet1 |
| 16640 | 3 | 4 | 5 | | V-2 | Tex26 |
| 16641 | 3 | 4 | 5 | | V-2 | Tgfbrap1 |
| 16642 | 3 | 4 | 5 | | V-2 | Tgm3 |
| 16643 | 3 | 4 | 5 | | V-2 | Thada |
| 16644 | 3 | 4 | 5 | | V-2 | Theg |
| 16645 | 3 | 4 | 5 | | V-2 | Themis3 |
| 16646 | 3 | 4 | 5 | | V-2 | Thtpa |
| 16647 | 3 | 4 | 5 | | V-2 | Thumpd3 |
| 16648 | 3 | 4 | 5 | | V-2 | Tigd3 |
| 16649 | 3 | 4 | 5 | | V-2 | Tktl1 |
| 16650 | 3 | 4 | 5 | | V-2 | Tll1 |
| 16651 | 3 | 4 | 5 | | V-2 | Tln1 |
| 16652 | 3 | 4 | 5 | | V-2 | Tlx1 |
| 16653 | 3 | 4 | 5 | | V-2 | Tm7sf3 |
| 16654 | 3 | 4 | 5 | | V-2 | Tmbim7 |
| 16655 | 3 | 4 | 5 | | V-2 | Tmc3 |
| 16656 | 3 | 4 | 5 | | V-2 | Tmed9 |
| 16657 | 3 | 4 | 5 | | V-2 | Tmem121 |
| 16658 | 3 | 4 | 5 | | V-2 | Tmem145 |
| 16659 | 3 | 4 | 5 | | V-2 | Tmem177 |
| 16660 | 3 | 4 | 5 | | V-2 | Tmem207 |
| 16661 | 3 | 4 | 5 | | V-2 | Tmem241 |
| 16662 | 3 | 4 | 5 | | V-2 | Tmem65 |
| 16663 | 3 | 4 | 5 | | V-2 | Tmprss3 |
| 16664 | 3 | 4 | 5 | | V-2 | Tmprss6 |
| 16665 | 3 | 4 | 5 | | V-2 | Tnfrsf26 |
| 16666 | 3 | 4 | 5 | | V-2 | Tnip3 |
| 16667 | 3 | 4 | 5 | | V-2 | Tomm20l |
| 16668 | 3 | 4 | 5 | | V-2 | Tph2 |
| 16669 | 3 | 4 | 5 | | V-2 | Tprg |
| 16670 | 3 | 4 | 5 | | V-2 | Trak1 |
| 16671 | 3 | 4 | 5 | | V-2 | Trappc11 |
| 16672 | 3 | 4 | 5 | | V-2 | Trim41 |
| 16673 | 3 | 4 | 5 | | V-2 | Trim52 |
| 16674 | 3 | 4 | 5 | | V-2 | Trim55 |
| 16675 | 3 | 4 | 5 | | V-2 | Trim61 |
| 16676 | 3 | 4 | 5 | | V-2 | Trim68 |
| 16677 | 3 | 4 | 5 | | V-2 | Trmt13 |
| 16678 | 3 | 4 | 5 | | V-2 | Trpc3 |
| 16679 | 3 | 4 | 5 | | V-2 | Trpc5os |
| 16680 | 3 | 4 | 5 | | V-2 | Trpd52l3 |
| 16681 | 3 | 4 | 5 | | V-2 | Trpm1 |
| 16682 | 3 | 4 | 5 | | V-2 | Tspan15 |
| 16683 | 3 | 4 | 5 | | V-2 | Tsr2 |
| 16684 | 3 | 4 | 5 | | V-2 | Ttc26 |
| 16685 | 3 | 4 | 5 | | V-2 | Ttc30a1 |
| 16686 | 3 | 4 | 5 | | V-2 | Tube1 |
| 16687 | 3 | 4 | 5 | | V-2 | Txina |
| 16688 | 3 | 4 | 5 | | V-2 | Ubash3a |
| 16689 | 3 | 4 | 5 | | V-2 | Ubqln4 |
| 16690 | 3 | 4 | 5 | | V-2 | Ubr2 |
| 16691 | 3 | 4 | 5 | | V-2 | Ugt1a10 |
| 16692 | 3 | 4 | 5 | | V-2 | Ugt2b36 |
| 16693 | 3 | 4 | 5 | | V-2 | Unc79 |
| 16694 | 3 | 4 | 5 | | V-2 | Uroc1 |
| 16695 | 3 | 4 | 5 | | V-2 | Ush1g |
| 16696 | 3 | 4 | 5 | | V-2 | Usp10 |
| 16697 | 3 | 4 | 5 | | V-2 | Usp19 |
| 16698 | 3 | 4 | 5 | | V-2 | Usp21 |
| 16699 | 3 | 4 | 5 | | V-2 | Usp24 |
| 16700 | 3 | 4 | 5 | | V-2 | Usp7 |
| 16701 | 3 | 4 | 5 | | V-2 | Utp20 |
| 16702 | 3 | 4 | 5 | | V-2 | Veph1 |

Fig. 34 - 88

| | | | | | | | |
|---|---|---|---|---|---|---|---|
| 16703 | 3 | 4 | 5 | | V-2 | Vmn1r181 |
| 16704 | 3 | 4 | 5 | | V-2 | Vps26b |
| 16705 | 3 | 4 | 5 | | V-2 | Vps29 |
| 16706 | 3 | 4 | 5 | | V-2 | Wdr19 |
| 16707 | 3 | 4 | 5 | | V-2 | Wdr20rt |
| 16708 | 3 | 4 | 5 | | V-2 | Wdr63 |
| 16709 | 3 | 4 | 5 | | V-2 | Wdr90 |
| 16710 | 3 | 4 | 5 | | V-2 | Wfdc15a |
| 16711 | 3 | 4 | 5 | | V-2 | Wls |
| 16712 | 3 | 4 | 5 | | V-2 | Wnt10a |
| 16713 | 3 | 4 | 5 | | V-2 | Wt1 |
| 16714 | 3 | 4 | 5 | | V-2 | Xkr4 |
| 16715 | 3 | 4 | 5 | | V-2 | Xkr5 |
| 16716 | 3 | 4 | 5 | | V-2 | Xkr6 |
| 16717 | 3 | 4 | 5 | | V-2 | Xndc1 |
| 16718 | 3 | 4 | 5 | | V-2 | Yipf6 |
| 16719 | 3 | 4 | 5 | | V-2 | Ywhab |
| 16720 | 3 | 4 | 5 | | V-2 | Ywhaz |
| 16721 | 3 | 4 | 5 | | V-2 | Zar1 |
| 16722 | 3 | 4 | 5 | | V-2 | Zbtb26 |
| 16723 | 3 | 4 | 5 | | V-2 | Zbtb3 |
| 16724 | 3 | 4 | 5 | | V-2 | Zbtb45 |
| 16725 | 3 | 4 | 5 | | V-2 | Zbtb9 |
| 16726 | 3 | 4 | 5 | | V-2 | Zc3h12b |
| 16727 | 3 | 4 | 5 | | V-2 | Zdhhc15 |
| 16728 | 3 | 4 | 5 | | V-2 | Zfand3 |
| 16729 | 3 | 4 | 5 | | V-2 | Zfat |
| 16730 | 3 | 4 | 5 | | V-2 | Zfp108 |
| 16731 | 3 | 4 | 5 | | V-2 | Zfp11 |
| 16732 | 3 | 4 | 5 | | V-2 | Zfp111 |
| 16733 | 3 | 4 | 5 | | V-2 | Zfp128 |
| 16734 | 3 | 4 | 5 | | V-2 | Zfp174 |
| 16735 | 3 | 4 | 5 | | V-2 | Zfp184 |
| 16736 | 3 | 4 | 5 | | V-2 | Zfp207 |
| 16737 | 3 | 4 | 5 | | V-2 | Zfp389 |
| 16738 | 3 | 4 | 5 | | V-2 | Zfp418 |
| 16739 | 3 | 4 | 5 | | V-2 | Zfp454 |
| 16740 | 3 | 4 | 5 | | V-2 | Zfp457 |
| 16741 | 3 | 4 | 5 | | V-2 | Zfp458 |
| 16742 | 3 | 4 | 5 | | V-2 | Zfp472 |
| 16743 | 3 | 4 | 5 | | V-2 | Zfp473 |
| 16744 | 3 | 4 | 5 | | V-2 | Zfp560 |
| 16745 | 3 | 4 | 5 | | V-2 | Zfp572 |
| 16746 | 3 | 4 | 5 | | V-2 | Zfp575 |
| 16747 | 3 | 4 | 5 | | V-2 | Zfp619 |
| 16748 | 3 | 4 | 5 | | V-2 | Zfp689 |
| 16749 | 3 | 4 | 5 | | V-2 | Zfp704 |
| 16750 | 3 | 4 | 5 | | V-2 | Zfp708 |
| 16751 | 3 | 4 | 5 | | V-2 | Zfp709 |
| 16752 | 3 | 4 | 5 | | V-2 | Zfp773 |
| 16753 | 3 | 4 | 5 | | V-2 | Zfp781 |
| 16754 | 3 | 4 | 5 | | V-2 | Zfp819 |
| 16755 | 3 | 4 | 5 | | V-2 | Zfp831 |
| 16756 | 3 | 4 | 5 | | V-2 | Zfp850 |
| 16757 | 3 | 4 | 5 | | V-2 | Zfp85os |
| 16758 | 3 | 4 | 5 | | V-2 | Zfp862-ps |
| 16759 | 3 | 4 | 5 | | V-2 | Zfp873 |
| 16760 | 3 | 4 | 5 | | V-2 | Zfp882 |
| 16761 | 3 | 4 | 5 | | V-2 | Zfp945 |
| 16762 | 3 | 4 | 5 | | V-2 | Zfp947 |
| 16763 | 3 | 4 | 5 | | V-2 | Zfp953 |
| 16764 | 3 | 4 | 5 | | V-2 | Zfp964 |
| 16765 | 3 | 4 | 5 | | V-2 | Zfy2 |
| 16766 | 3 | 4 | 5 | | V-2 | Zik1 |
| 16767 | 3 | 4 | 5 | | V-2 | Zkscan5 |
| 16768 | 3 | 4 | 5 | | V-2 | Zmat4 |
| 16769 | 3 | 4 | 5 | | V-2 | Zmym3 |
| 16770 | 3 | 4 | 5 | | V-2 | Zscan5b |
| 16771 | 3 | 4 | 5 | | V-1 | 0610010F05Rik |
| 16772 | 3 | 4 | 5 | | V-1 | 1600016N20Rik |
| 16773 | 3 | 4 | 5 | | V-1 | 1600023N17Rik |
| 16774 | 3 | 4 | 5 | | V-1 | 1700001G17Rik |
| 16775 | 3 | 4 | 5 | | V-1 | 1700003L19Rik |
| 16776 | 3 | 4 | 5 | | V-1 | 1700006E09Rik |
| 16777 | 3 | 4 | 5 | | V-1 | 1700006H21Rik |
| 16778 | 3 | 4 | 5 | | V-1 | 1700007J10Rik |
| 16779 | 3 | 4 | 5 | | V-1 | 1700010J16Rik |
| 16780 | 3 | 4 | 5 | | V-1 | 1700010X23Rik |
| 16781 | 3 | 4 | 5 | | V-1 | 1700011B04Rik |
| 16782 | 3 | 4 | 5 | | V-1 | 1700011H14Rik |
| 16783 | 3 | 4 | 5 | | V-1 | 1700012I11Rik |
| 16784 | 3 | 4 | 5 | | V-1 | 1700013F07Rik |
| 16785 | 3 | 4 | 5 | | V-1 | 1700015E13Rik |
| 16786 | 3 | 4 | 5 | | V-1 | 1700019B21Rik |
| 16787 | 3 | 4 | 5 | | V-1 | 1700019G17Rik |
| 16788 | 3 | 4 | 5 | | V-1 | 1700020A23Rik |
| 16789 | 3 | 4 | 5 | | V-1 | 1700022A21Rik |
| 16790 | 3 | 4 | 5 | | V-1 | 1700023E05Rik |
| 16791 | 3 | 4 | 5 | | V-1 | 1700024F13Rik |
| 16792 | 3 | 4 | 5 | | V-1 | 1700025G04Rik |
| 16793 | 3 | 4 | 5 | | V-1 | 1700026D08Rik |
| 16794 | 3 | 4 | 5 | | V-1 | 1700028K03Rik |
| 16795 | 3 | 4 | 5 | | V-1 | 1700028P15Rik |
| 16796 | 3 | 4 | 5 | | V-1 | 1700029H14Rik |
| 16797 | 3 | 4 | 5 | | V-1 | 1700030O20Rik |
| 16798 | 3 | 4 | 5 | | V-1 | 1700041C23Rik |
| 16799 | 3 | 4 | 5 | | V-1 | 1700044C05Rik |
| 16800 | 3 | 4 | 5 | | V-1 | 1700048O20Rik |
| 16801 | 3 | 4 | 5 | | V-1 | 1700049L16Rik |
| 16802 | 3 | 4 | 5 | | V-1 | 1700052K11Rik |
| 16803 | 3 | 4 | 5 | | V-1 | 1700052N19Rik |
| 16804 | 3 | 4 | 5 | | V-1 | 1700066O22Rik |
| 16805 | 3 | 4 | 5 | | V-1 | 1700074P13Rik |
| 16806 | 3 | 4 | 5 | | V-1 | 1700080N15Rik |
| 16807 | 3 | 4 | 5 | | V-1 | 1700092C10Rik |
| 16808 | 3 | 4 | 5 | | V-1 | 1700094J05Rik |
| 16809 | 3 | 4 | 5 | | V-1 | 1700095B10Rik |
| 16810 | 3 | 4 | 5 | | V-1 | 1700105P06Rik |
| 16811 | 3 | 4 | 5 | | V-1 | 1700109G15Rik |
| 16812 | 3 | 4 | 5 | | V-1 | 1700109H08Rik |
| 16813 | 3 | 4 | 5 | | V-1 | 1700120C14Rik |
| 16814 | 3 | 4 | 5 | | V-1 | 1700123O12Rik |
| 16815 | 3 | 4 | 5 | | V-1 | 1700123O20Rik |
| 16816 | 3 | 4 | 5 | | V-1 | 1700125H03Rik |
| 16817 | 3 | 4 | 5 | | V-1 | 1810013L24Rik |
| 16818 | 3 | 4 | 5 | | V-1 | 1810014B01Rik |
| 16819 | 3 | 4 | 5 | | V-1 | 1810062G17Rik |
| 16820 | 3 | 4 | 5 | | V-1 | 2010002M12Rik |
| 16821 | 3 | 4 | 5 | | V-1 | 2010009K17Rik |
| 16822 | 3 | 4 | 5 | | V-1 | 2010015L04Rik |
| 16823 | 3 | 4 | 5 | | V-1 | 2010107G12Rik |
| 16824 | 3 | 4 | 5 | | V-1 | 2200002J24Rik |
| 16825 | 3 | 4 | 5 | | V-1 | 2210039B01Rik |
| 16826 | 3 | 4 | 5 | | V-1 | 2210408I21Rik |
| 16827 | 3 | 4 | 5 | | V-1 | 2310022B05Rik |
| 16828 | 3 | 4 | 5 | | V-1 | 2310047M10Rik |
| 16829 | 3 | 4 | 5 | | V-1 | 2310061N02Rik |
| 16830 | 3 | 4 | 5 | | V-1 | 2310069B03Rik |
| 16831 | 3 | 4 | 5 | | V-1 | 2410002F23Rik |
| 16832 | 3 | 4 | 5 | | V-1 | 2410089E03Rik |
| 16833 | 3 | 4 | 5 | | V-1 | 2410124H12Rik |
| 16834 | 3 | 4 | 5 | | V-1 | 2410127L17Rik |
| 16835 | 3 | 4 | 5 | | V-1 | 2610015P09Rik |
| 16836 | 3 | 4 | 5 | | V-1 | 2700081O15Rik |
| 16837 | 3 | 4 | 5 | | V-1 | 2810002D19Rik |
| 16838 | 3 | 4 | 5 | | V-1 | 2900005J15Rik |
| 16839 | 3 | 4 | 5 | | V-1 | 2900041M22Rik |
| 16840 | 3 | 4 | 5 | | V-1 | 2900060B14Rik |
| 16841 | 3 | 4 | 5 | | V-1 | 3100003L05Rik |
| 16842 | 3 | 4 | 5 | | V-1 | 3110021N24Rik |
| 16843 | 3 | 4 | 5 | | V-1 | 3110057O12Rik |
| 16844 | 3 | 4 | 5 | | V-1 | 3830406C13Rik |
| 16845 | 3 | 4 | 5 | | V-1 | 3830408C21Rik |
| 16846 | 3 | 4 | 5 | | V-1 | 4732490B19Rik |
| 16847 | 3 | 4 | 5 | | V-1 | 4833427F10Rik |
| 16848 | 3 | 4 | 5 | | V-1 | 4921507P07Rik |
| 16849 | 3 | 4 | 5 | | V-1 | 4921524L21Rik |
| 16850 | 3 | 4 | 5 | | V-1 | 4921531C22Rik |
| 16851 | 3 | 4 | 5 | | V-1 | 4930405A21Rik |
| 16852 | 3 | 4 | 5 | | V-1 | 4930425K10Rik |
| 16853 | 3 | 4 | 5 | | V-1 | 4930429F11Rik |
| 16854 | 3 | 4 | 5 | | V-1 | 4930430A15Rik |
| 16855 | 3 | 4 | 5 | | V-1 | 4930438E09Rik |
| 16856 | 3 | 4 | 5 | | V-1 | 4930441J16Rik |
| 16857 | 3 | 4 | 5 | | V-1 | 4930453N24Rik |
| 16858 | 3 | 4 | 5 | | V-1 | 4930455D15Rik |
| 16859 | 3 | 4 | 5 | | V-1 | 4930456L19Rik |
| 16860 | 3 | 4 | 5 | | V-1 | 4930459C07Rik |
| 16861 | 3 | 4 | 5 | | V-1 | 4930461G14Rik |
| 16862 | 3 | 4 | 5 | | V-1 | 4930471C04Rik |
| 16863 | 3 | 4 | 5 | | V-1 | 4930474M22Rik |
| 16864 | 3 | 4 | 5 | | V-1 | 4930500F04Rik |
| 16865 | 3 | 4 | 5 | | V-1 | 4930502A04Rik |
| 16866 | 3 | 4 | 5 | | V-1 | 4930502E09Rik |
| 16867 | 3 | 4 | 5 | | V-1 | 4930504O13Rik |
| 16868 | 3 | 4 | 5 | | V-1 | 4930505A04Rik |
| 16869 | 3 | 4 | 5 | | V-1 | 4930513O06Rik |
| 16870 | 3 | 4 | 5 | | V-1 | 4930519F16Rik |
| 16871 | 3 | 4 | 5 | | V-1 | 4930519H02Rik |
| 16872 | 3 | 4 | 5 | | V-1 | 4930524O05Rik |
| 16873 | 3 | 4 | 5 | | V-1 | 4930525G20Rik |
| 16874 | 3 | 4 | 5 | | V-1 | 4930544D05Rik |
| 16875 | 3 | 4 | 5 | | V-1 | 4930545H06Rik |
| 16876 | 3 | 4 | 5 | | V-1 | 4930552P12Rik |
| 16877 | 3 | 4 | 5 | | V-1 | 4930556N09Rik |
| 16878 | 3 | 4 | 5 | | V-1 | 4930563D23Rik |
| 16879 | 3 | 4 | 5 | | V-1 | 4930567H12Rik |
| 16880 | 3 | 4 | 5 | | V-1 | 4930571O06Rik |
| 16881 | 3 | 4 | 5 | | V-1 | 4930573O16Rik |
| 16882 | 3 | 4 | 5 | | V-1 | 4930578C19Rik |
| 16883 | 3 | 4 | 5 | | V-1 | 4930578E11Rik |
| 16884 | 3 | 4 | 5 | | V-1 | 4930579F01Rik |
| 16885 | 3 | 4 | 5 | | V-1 | 4930579G18Rik |
| 16886 | 3 | 4 | 5 | | V-1 | 4931409K22Rik |
| 16887 | 3 | 4 | 5 | | V-1 | 4931419H13Rik |
| 16888 | 3 | 4 | 5 | | V-1 | 4931431F19Rik |
| 16889 | 3 | 4 | 5 | | V-1 | 4931440L10Rik |
| 16890 | 3 | 4 | 5 | | V-1 | 4931440P22Rik |
| 16891 | 3 | 4 | 5 | | V-1 | 4932412D23Rik |
| 16892 | 3 | 4 | 5 | | V-1 | 4932416H05Rik |
| 16893 | 3 | 4 | 5 | | V-1 | 4932429P05Rik |
| 16894 | 3 | 4 | 5 | | V-1 | 4932435O22Rik |

Fig. 34 - 89

| | | | | | | | |
|---|---|---|---|---|---|---|---|
| 16895 | 3 | 4 | 5 | | V-1 | 4932438H23Rik | |
| 16896 | 3 | 4 | 5 | | V-1 | 4933402D24Rik | |
| 16897 | 3 | 4 | 5 | | V-1 | 4933402J07Rik | |
| 16898 | 3 | 4 | 5 | | V-1 | 4933406F09Rik | |
| 16899 | 3 | 4 | 5 | | V-1 | 4933406I18Rik | |
| 16900 | 3 | 4 | 5 | | V-1 | 4933409G03Rik | |
| 16901 | 3 | 4 | 5 | | V-1 | 4933412O06Rik | |
| 16902 | 3 | 4 | 5 | | V-1 | 4933416I08Rik | |
| 16903 | 3 | 4 | 5 | | V-1 | 4933428C19Rik | |
| 16904 | 3 | 4 | 5 | | V-1 | 4933428G20Rik | |
| 16905 | 3 | 4 | 5 | | V-1 | 4933429O19Rik | |
| 16906 | 3 | 4 | 5 | | V-1 | 4933431G14Rik | |
| 16907 | 3 | 4 | 5 | | V-1 | 4933440J02Rik | |
| 16908 | 3 | 4 | 5 | | V-1 | 5031426D15Rik | |
| 16909 | 3 | 4 | 5 | | V-1 | 5031439G07Rik | |
| 16910 | 3 | 4 | 5 | | V-1 | 5330411J11Rik | |
| 16911 | 3 | 4 | 5 | | V-1 | 5830417I10Rik | |
| 16912 | 3 | 4 | 5 | | V-1 | 5830418P13Rik | |
| 16913 | 3 | 4 | 5 | | V-1 | 5930412G12Rik | |
| 16914 | 3 | 4 | 5 | | V-1 | 6030407O03Rik | |
| 16915 | 3 | 4 | 5 | | V-1 | 6030458C11Rik | |
| 16916 | 3 | 4 | 5 | | V-1 | 6030466F02Rik | |
| 16917 | 3 | 4 | 5 | | V-1 | 9130015A21Rik | |
| 16918 | 3 | 4 | 5 | | V-1 | 9330158H04Rik | |
| 16919 | 3 | 4 | 5 | | V-1 | 9330179D12Rik | |
| 16920 | 3 | 4 | 5 | | V-1 | 9430083A17Rik | |
| 16921 | 3 | 4 | 5 | | V-1 | 9430091E24Rik | |
| 16922 | 3 | 4 | 5 | | V-1 | 9530027J09Rik | |
| 16923 | 3 | 4 | 5 | | V-1 | 9530068E07Rik | |
| 16924 | 3 | 4 | 5 | | V-1 | 9830166K06Rik | |
| 16925 | 3 | 4 | 5 | | V-1 | A230001M10Rik | |
| 16926 | 3 | 4 | 5 | | V-1 | A330041J22Rik | |
| 16927 | 3 | 4 | 5 | | V-1 | A330048O09Rik | |
| 16928 | 3 | 4 | 5 | | V-1 | A430033K04Rik | |
| 16929 | 3 | 4 | 5 | | V-1 | A430078G23Rik | |
| 16930 | 3 | 4 | 5 | | V-1 | A4galt | |
| 16931 | 3 | 4 | 5 | | V-1 | A530064D06Rik | |
| 16932 | 3 | 4 | 5 | | V-1 | A630010A05Rik | |
| 16933 | 3 | 4 | 5 | | V-1 | A630023A22Rik | |
| 16934 | 3 | 4 | 5 | | V-1 | A630095E13Rik | |
| 16935 | 3 | 4 | 5 | | V-1 | A830009L08Rik | |
| 16936 | 3 | 4 | 5 | | V-1 | A930001A20Rik | |
| 16937 | 3 | 4 | 5 | | V-1 | A930024E05Rik | |
| 16938 | 3 | 4 | 5 | | V-1 | AA387883 | |
| 16939 | 3 | 4 | 5 | | V-1 | AA415398 | |
| 16940 | 3 | 4 | 5 | | V-1 | AA543186 | |
| 16941 | 3 | 4 | 5 | | V-1 | AB124611 | |
| 16942 | 3 | 4 | 5 | | V-1 | AI414108 | |
| 16943 | 3 | 4 | 5 | | V-1 | AI504432 | |
| 16944 | 3 | 4 | 5 | | V-1 | AI848285 | |
| 16945 | 3 | 4 | 5 | | V-1 | AI854517 | |
| 16946 | 3 | 4 | 5 | | V-1 | AK129341 | |
| 16947 | 3 | 4 | 5 | | V-1 | AU019823 | |
| 16948 | 3 | 4 | 5 | | V-1 | AU040972 | |
| 16949 | 3 | 4 | 5 | | V-1 | AV320801 | |
| 16950 | 3 | 4 | 5 | | V-1 | AW046200 | |
| 16951 | 3 | 4 | 5 | | V-1 | Abcc8 | |
| 16952 | 3 | 4 | 5 | | V-1 | Abhd12 | |
| 16953 | 3 | 4 | 5 | | V-1 | Abhd15 | |
| 16954 | 3 | 4 | 5 | | V-1 | Ablim1 | |
| 16955 | 3 | 4 | 5 | | V-1 | Abo | |
| 16956 | 3 | 4 | 5 | | V-1 | Acad8 | |
| 16957 | 3 | 4 | 5 | | V-1 | Acadl | |
| 16958 | 3 | 4 | 5 | | V-1 | Acap1 | |
| 16959 | 3 | 4 | 5 | | V-1 | Acap3 | |
| 16960 | 3 | 4 | 5 | | V-1 | Acat1 | |
| 16961 | 3 | 4 | 5 | | V-1 | Acd | |
| 16962 | 3 | 4 | 5 | | V-1 | Ace2 | |
| 16963 | 3 | 4 | 5 | | V-1 | Acox1 | |
| 16964 | 3 | 4 | 5 | | V-1 | Acox3 | |
| 16965 | 3 | 4 | 5 | | V-1 | Acsbg2 | |
| 16966 | 3 | 4 | 5 | | V-1 | Acsl4 | |
| 16967 | 3 | 4 | 5 | | V-1 | Actl10 | |
| 16968 | 3 | 4 | 5 | | V-1 | Actrt3 | |
| 16969 | 3 | 4 | 5 | | V-1 | Adam1b | |
| 16970 | 3 | 4 | 5 | | V-1 | Adam30 | |
| 16971 | 3 | 4 | 5 | | V-1 | Adam5 | |
| 16972 | 3 | 4 | 5 | | V-1 | Adcy8 | |
| 16973 | 3 | 4 | 5 | | V-1 | Adcyap1 | |
| 16974 | 3 | 4 | 5 | | V-1 | Add1 | |
| 16975 | 3 | 4 | 5 | | V-1 | Adgb | |
| 16976 | 3 | 4 | 5 | | V-1 | Adipor1 | |
| 16977 | 3 | 4 | 5 | | V-1 | Adora2a | |
| 16978 | 3 | 4 | 5 | | V-1 | Adora3 | |
| 16979 | 3 | 4 | 5 | | V-1 | Adra1a | |
| 16980 | 3 | 4 | 5 | | V-1 | Adra2c | |
| 16981 | 3 | 4 | 5 | | V-1 | Aen | |
| 16982 | 3 | 4 | 5 | | V-1 | Afp | |
| 16983 | 3 | 4 | 5 | | V-1 | Agap3 | |
| 16984 | 3 | 4 | 5 | | V-1 | Aggf1 | |
| 16985 | 3 | 4 | 5 | | V-1 | Agr2 | |
| 16986 | 3 | 4 | 5 | | V-1 | Agtpbp1 | |
| 16987 | 3 | 4 | 5 | | V-1 | Agtr1b | |
| 16988 | 3 | 4 | 5 | | V-1 | Ahcy | |
| 16989 | 3 | 4 | 5 | | V-1 | Ahcyl1 | |
| 16990 | 3 | 4 | 5 | | V-1 | Aicda | |
| 16991 | 3 | 4 | 5 | | V-1 | Aifm3 | |
| 16992 | 3 | 4 | 5 | | V-1 | Akr1e1 | |
| 16993 | 3 | 4 | 5 | | V-1 | Aldh2 | |
| 16994 | 3 | 4 | 5 | | V-1 | Alkbh1 | |
| 16995 | 3 | 4 | 5 | | V-1 | Alkbh5 | |
| 16996 | 3 | 4 | 5 | | V-1 | Alkbh8 | |
| 16997 | 3 | 4 | 5 | | V-1 | Alpk3 | |
| 16998 | 3 | 4 | 5 | | V-1 | Alx4 | |
| 16999 | 3 | 4 | 5 | | V-1 | Amh | |
| 17000 | 3 | 4 | 5 | | V-1 | Amhr2 | |
| 17001 | 3 | 4 | 5 | | V-1 | Anapc1 | |
| 17002 | 3 | 4 | 5 | | V-1 | Angel1 | |
| 17003 | 3 | 4 | 5 | | V-1 | Angpt4 | |
| 17004 | 3 | 4 | 5 | | V-1 | Ankle2 | |
| 17005 | 3 | 4 | 5 | | V-1 | Ankrd50 | |
| 17006 | 3 | 4 | 5 | | V-1 | Ankrd61 | |
| 17007 | 3 | 4 | 5 | | V-1 | Ankrd63 | |
| 17008 | 3 | 4 | 5 | | V-1 | Anks1 | |
| 17009 | 3 | 4 | 5 | | V-1 | Ano2 | |
| 17010 | 3 | 4 | 5 | | V-1 | Ano6 | |
| 17011 | 3 | 4 | 5 | | V-1 | Aoah | |
| 17012 | 3 | 4 | 5 | | V-1 | Ap1b1 | |
| 17013 | 3 | 4 | 5 | | V-1 | Ap1g1 | |
| 17014 | 3 | 4 | 5 | | V-1 | Ap1m2 | |
| 17015 | 3 | 4 | 5 | | V-1 | Ap1s2 | |
| 17016 | 3 | 4 | 5 | | V-1 | Ap3d1 | |
| 17017 | 3 | 4 | 5 | | V-1 | Apcs | |
| 17018 | 3 | 4 | 5 | | V-1 | Aplp2 | |
| 17019 | 3 | 4 | 5 | | V-1 | Apol7e | |
| 17020 | 3 | 4 | 5 | | V-1 | Apom | |
| 17021 | 3 | 4 | 5 | | V-1 | Apon | |
| 17022 | 3 | 4 | 5 | | V-1 | Apopt1 | |
| 17023 | 3 | 4 | 5 | | V-1 | Appl2 | |
| 17024 | 3 | 4 | 5 | | V-1 | Aqp5 | |
| 17025 | 3 | 4 | 5 | | V-1 | Aqp6 | |
| 17026 | 3 | 4 | 5 | | V-1 | Araf | |
| 17027 | 3 | 4 | 5 | | V-1 | Arf2 | |
| 17028 | 3 | 4 | 5 | | V-1 | Arhgap20os | |
| 17029 | 3 | 4 | 5 | | V-1 | Arhgap4 | |
| 17030 | 3 | 4 | 5 | | V-1 | Arhgef10l | |
| 17031 | 3 | 4 | 5 | | V-1 | Arhgef19 | |
| 17032 | 3 | 4 | 5 | | V-1 | Arhgef7 | |
| 17033 | 3 | 4 | 5 | | V-1 | Arl16 | |
| 17034 | 3 | 4 | 5 | | V-1 | Arl8b | |
| 17035 | 3 | 4 | 5 | | V-1 | Armc9 | |
| 17036 | 3 | 4 | 5 | | V-1 | Armcx6 | |
| 17037 | 3 | 4 | 5 | | V-1 | Arsa | |
| 17038 | 3 | 4 | 5 | | V-1 | Art2b | |
| 17039 | 3 | 4 | 5 | | V-1 | Arvcf | |
| 17040 | 3 | 4 | 5 | | V-1 | Asap1 | |
| 17041 | 3 | 4 | 5 | | V-1 | Asb6 | |
| 17042 | 3 | 4 | 5 | | V-1 | Asb8 | |
| 17043 | 3 | 4 | 5 | | V-1 | Asb9 | |
| 17044 | 3 | 4 | 5 | | V-1 | Asic3 | |
| 17045 | 3 | 4 | 5 | | V-1 | Asun | |
| 17046 | 3 | 4 | 5 | | V-1 | Atf7 | |
| 17047 | 3 | 4 | 5 | | V-1 | Atg13 | |
| 17048 | 3 | 4 | 5 | | V-1 | Atg5 | |
| 17049 | 3 | 4 | 5 | | V-1 | Atp1a1 | |
| 17050 | 3 | 4 | 5 | | V-1 | Atp5s | |
| 17051 | 3 | 4 | 5 | | V-1 | Atp5sl | |
| 17052 | 3 | 4 | 5 | | V-1 | Atp6ap1 | |
| 17053 | 3 | 4 | 5 | | V-1 | Atp6v1d | |
| 17054 | 3 | 4 | 5 | | V-1 | Atp7b | |
| 17055 | 3 | 4 | 5 | | V-1 | Atp8b4 | |
| 17056 | 3 | 4 | 5 | | V-1 | Atxn2 | |
| 17057 | 3 | 4 | 5 | | V-1 | Atxn3 | |
| 17058 | 3 | 4 | 5 | | V-1 | Axl | |
| 17059 | 3 | 4 | 5 | | V-1 | B230209E15Rik | |
| 17060 | 3 | 4 | 5 | | V-1 | B3galt1 | |
| 17061 | 3 | 4 | 5 | | V-1 | B3gnt1 | |
| 17062 | 3 | 4 | 5 | | V-1 | B430010I23Rik | |
| 17063 | 3 | 4 | 5 | | V-1 | B930059L03Rik | |
| 17064 | 3 | 4 | 5 | | V-1 | BC021891 | |
| 17065 | 3 | 4 | 5 | | V-1 | BC022687 | |
| 17066 | 3 | 4 | 5 | | V-1 | BC024139 | |
| 17067 | 3 | 4 | 5 | | V-1 | BC030500 | |
| 17068 | 3 | 4 | 5 | | V-1 | BC031361 | |
| 17069 | 3 | 4 | 5 | | V-1 | BC035044 | |
| 17070 | 3 | 4 | 5 | | V-1 | BC048671 | |
| 17071 | 3 | 4 | 5 | | V-1 | BC052040 | |
| 17072 | 3 | 4 | 5 | | V-1 | BC068157 | |
| 17073 | 3 | 4 | 5 | | V-1 | Bach2os | |
| 17074 | 3 | 4 | 5 | | V-1 | Baiap2l1 | |
| 17075 | 3 | 4 | 5 | | V-1 | Barx1 | |
| 17076 | 3 | 4 | 5 | | V-1 | Bbs9 | |
| 17077 | 3 | 4 | 5 | | V-1 | Bcap31 | |
| 17078 | 3 | 4 | 5 | | V-1 | Bcl3 | |
| 17079 | 3 | 4 | 5 | | V-1 | Bend3 | |
| 17080 | 3 | 4 | 5 | | V-1 | Bfsp2 | |
| 17081 | 3 | 4 | 5 | | V-1 | Bmp1 | |
| 17082 | 3 | 4 | 5 | | V-1 | Bmp2 | |
| 17083 | 3 | 4 | 5 | | V-1 | Bmp8b | |
| 17084 | 3 | 4 | 5 | | V-1 | Bpifb5 | |
| 17085 | 3 | 4 | 5 | | V-1 | Bptf | |
| 17086 | 3 | 4 | 5 | | V-1 | Brd4 | |

Fig. 34 - 90

| | | | | | | |
|---|---|---|---|---|---|---|
| 17087 | 3 | 4 | 5 | | V-1 | Brwd3 |
| 17088 | 3 | 4 | 5 | | V-1 | Btbd18 |
| 17089 | 3 | 4 | 5 | | V-1 | Btbd9 |
| 17090 | 3 | 4 | 5 | | V-1 | Btrc |
| 17091 | 3 | 4 | 5 | | V-1 | C030034L19Rik |
| 17092 | 3 | 4 | 5 | | V-1 | C130046K22Rik |
| 17093 | 3 | 4 | 5 | | V-1 | C130074G19Rik |
| 17094 | 3 | 4 | 5 | | V-1 | C1ql1 |
| 17095 | 3 | 4 | 5 | | V-1 | C1ql4 |
| 17096 | 3 | 4 | 5 | | V-1 | C1qtnf3 |
| 17097 | 3 | 4 | 5 | | V-1 | C230004F18Rik |
| 17098 | 3 | 4 | 5 | | V-1 | C230052I12Rik |
| 17099 | 3 | 4 | 5 | | V-1 | C2cd2 |
| 17100 | 3 | 4 | 5 | | V-1 | C2cd2l |
| 17101 | 3 | 4 | 5 | | V-1 | C330018D20Rik |
| 17102 | 3 | 4 | 5 | | V-1 | C330046G13Rik |
| 17103 | 3 | 4 | 5 | | V-1 | Cab39 |
| 17104 | 3 | 4 | 5 | | V-1 | Cabin1 |
| 17105 | 3 | 4 | 5 | | V-1 | Cachd1 |
| 17106 | 3 | 4 | 5 | | V-1 | Cacna1a |
| 17107 | 3 | 4 | 5 | | V-1 | Cacna2d2 |
| 17108 | 3 | 4 | 5 | | V-1 | Cacng2 |
| 17109 | 3 | 4 | 5 | | V-1 | Cacng5 |
| 17110 | 3 | 4 | 5 | | V-1 | Cacybp |
| 17111 | 3 | 4 | 5 | | V-1 | Cage1 |
| 17112 | 3 | 4 | 5 | | V-1 | Calcb |
| 17113 | 3 | 4 | 5 | | V-1 | Camk1g |
| 17114 | 3 | 4 | 5 | | V-1 | Camk4 |
| 17115 | 3 | 4 | 5 | | V-1 | Camkk2 |
| 17116 | 3 | 4 | 5 | | V-1 | Caml |
| 17117 | 3 | 4 | 5 | | V-1 | Camsap1 |
| 17118 | 3 | 4 | 5 | | V-1 | Camsap2 |
| 17119 | 3 | 4 | 5 | | V-1 | Canx |
| 17120 | 3 | 4 | 5 | | V-1 | Capn2 |
| 17121 | 3 | 4 | 5 | | V-1 | Capn5 |
| 17122 | 3 | 4 | 5 | | V-1 | Card11 |
| 17123 | 3 | 4 | 5 | | V-1 | Carhsp1 |
| 17124 | 3 | 4 | 5 | | V-1 | Casq2 |
| 17125 | 3 | 4 | 5 | | V-1 | Casr |
| 17126 | 3 | 4 | 5 | | V-1 | Catsper2 |
| 17127 | 3 | 4 | 5 | | V-1 | Catsperg1 |
| 17128 | 3 | 4 | 5 | | V-1 | Cblc |
| 17129 | 3 | 4 | 5 | | V-1 | Cbln1 |
| 17130 | 3 | 4 | 5 | | V-1 | Cbln2 |
| 17131 | 3 | 4 | 5 | | V-1 | Cbwd1 |
| 17132 | 3 | 4 | 5 | | V-1 | Ccdc11 |
| 17133 | 3 | 4 | 5 | | V-1 | Ccdc126 |
| 17134 | 3 | 4 | 5 | | V-1 | Ccdc138 |
| 17135 | 3 | 4 | 5 | | V-1 | Ccdc146 |
| 17136 | 3 | 4 | 5 | | V-1 | Ccdc159 |
| 17137 | 3 | 4 | 5 | | V-1 | Ccdc171 |
| 17138 | 3 | 4 | 5 | | V-1 | Ccdc27 |
| 17139 | 3 | 4 | 5 | | V-1 | Ccdc43 |
| 17140 | 3 | 4 | 5 | | V-1 | Ccdc64b |
| 17141 | 3 | 4 | 5 | | V-1 | Ccdc66 |
| 17142 | 3 | 4 | 5 | | V-1 | Ccdc67 |
| 17143 | 3 | 4 | 5 | | V-1 | Ccdc74a |
| 17144 | 3 | 4 | 5 | | V-1 | Ccin |
| 17145 | 3 | 4 | 5 | | V-1 | Ccnc |
| 17146 | 3 | 4 | 5 | | V-1 | Ccni |
| 17147 | 3 | 4 | 5 | | V-1 | Ccr3 |
| 17148 | 3 | 4 | 5 | | V-1 | Cct8l1 |
| 17149 | 3 | 4 | 5 | | V-1 | Cd160 |
| 17150 | 3 | 4 | 5 | | V-1 | Cd2ap |
| 17151 | 3 | 4 | 5 | | V-1 | Cd2bp2 |
| 17152 | 3 | 4 | 5 | | V-1 | Cd34 |
| 17153 | 3 | 4 | 5 | | V-1 | Cd69 |
| 17154 | 3 | 4 | 5 | | V-1 | Cd80 |
| 17155 | 3 | 4 | 5 | | V-1 | Cd8b1 |
| 17156 | 3 | 4 | 5 | | V-1 | Cd97 |
| 17157 | 3 | 4 | 5 | | V-1 | Cd99l2 |
| 17158 | 3 | 4 | 5 | | V-1 | Cdan1 |
| 17159 | 3 | 4 | 5 | | V-1 | Cdc37l1 |
| 17160 | 3 | 4 | 5 | | V-1 | Cdh22 |
| 17161 | 3 | 4 | 5 | | V-1 | Cdip1 |
| 17162 | 3 | 4 | 5 | | V-1 | Cdk16 |
| 17163 | 3 | 4 | 5 | | V-1 | Cdk5rap1 |
| 17164 | 3 | 4 | 5 | | V-1 | Cdt1 |
| 17165 | 3 | 4 | 5 | | V-1 | Cdx1 |
| 17166 | 3 | 4 | 5 | | V-1 | Ceacam13 |
| 17167 | 3 | 4 | 5 | | V-1 | Cebpg |
| 17168 | 3 | 4 | 5 | | V-1 | Celsr3 |
| 17169 | 3 | 4 | 5 | | V-1 | Cenpe |
| 17170 | 3 | 4 | 5 | | V-1 | Cep112 |
| 17171 | 3 | 4 | 5 | | V-1 | Cep57 |
| 17172 | 3 | 4 | 5 | | V-1 | Cep97 |
| 17173 | 3 | 4 | 5 | | V-1 | Cers3 |
| 17174 | 3 | 4 | 5 | | V-1 | Ces1a |
| 17175 | 3 | 4 | 5 | | V-1 | Cfc1 |
| 17176 | 3 | 4 | 5 | | V-1 | Cfl2 |
| 17177 | 3 | 4 | 5 | | V-1 | Chmp2b |
| 17178 | 3 | 4 | 5 | | V-1 | Chmp4c |
| 17179 | 3 | 4 | 5 | | V-1 | Chrd |
| 17180 | 3 | 4 | 5 | | V-1 | Chrna4 |
| 17181 | 3 | 4 | 5 | | V-1 | Chrna5 |
| 17182 | 3 | 4 | 5 | | V-1 | Chrnb2 |
| 17183 | 3 | 4 | 5 | | V-1 | Chrnd |
| 17184 | 3 | 4 | 5 | | V-1 | Chst7 |
| 17185 | 3 | 4 | 5 | | V-1 | Chtf8 |
| 17186 | 3 | 4 | 5 | | V-1 | Chtop |
| 17187 | 3 | 4 | 5 | | V-1 | Cit |
| 17188 | 3 | 4 | 5 | | V-1 | Ciz1 |
| 17189 | 3 | 4 | 5 | | V-1 | Clasp2 |
| 17190 | 3 | 4 | 5 | | V-1 | Clca6 |
| 17191 | 3 | 4 | 5 | | V-1 | Cldn12 |
| 17192 | 3 | 4 | 5 | | V-1 | Cldn26 |
| 17193 | 3 | 4 | 5 | | V-1 | Cldn8 |
| 17194 | 3 | 4 | 5 | | V-1 | Clec4a4 |
| 17195 | 3 | 4 | 5 | | V-1 | Clk2 |
| 17196 | 3 | 4 | 5 | | V-1 | Cln5 |
| 17197 | 3 | 4 | 5 | | V-1 | Cltc |
| 17198 | 3 | 4 | 5 | | V-1 | Clvs2 |
| 17199 | 3 | 4 | 5 | | V-1 | Cmtm4 |
| 17200 | 3 | 4 | 5 | | V-1 | Cndp1 |
| 17201 | 3 | 4 | 5 | | V-1 | Cnih1 |
| 17202 | 3 | 4 | 5 | | V-1 | Cnpy3 |
| 17203 | 3 | 4 | 5 | | V-1 | Cntnap5b |
| 17204 | 3 | 4 | 5 | | V-1 | Coa5 |
| 17205 | 3 | 4 | 5 | | V-1 | Coil |
| 17206 | 3 | 4 | 5 | | V-1 | Col18a1 |
| 17207 | 3 | 4 | 5 | | V-1 | Col28a1 |
| 17208 | 3 | 4 | 5 | | V-1 | Col4a4 |
| 17209 | 3 | 4 | 5 | | V-1 | Commd8 |
| 17210 | 3 | 4 | 5 | | V-1 | Copb2 |
| 17211 | 3 | 4 | 5 | | V-1 | Cops8 |
| 17212 | 3 | 4 | 5 | | V-1 | Coq5 |
| 17213 | 3 | 4 | 5 | | V-1 | Cpn1 |
| 17214 | 3 | 4 | 5 | | V-1 | Cpxm2 |
| 17215 | 3 | 4 | 5 | | V-1 | Crat |
| 17216 | 3 | 4 | 5 | | V-1 | Crb3 |
| 17217 | 3 | 4 | 5 | | V-1 | Creb5 |
| 17218 | 3 | 4 | 5 | | V-1 | Creg1 |
| 17219 | 3 | 4 | 5 | | V-1 | Crhbp |
| 17220 | 3 | 4 | 5 | | V-1 | Crocc |
| 17221 | 3 | 4 | 5 | | V-1 | Crp |
| 17222 | 3 | 4 | 5 | | V-1 | Crtc2 |
| 17223 | 3 | 4 | 5 | | V-1 | Cry1 |
| 17224 | 3 | 4 | 5 | | V-1 | Cry2 |
| 17225 | 3 | 4 | 5 | | V-1 | Cse1l |
| 17226 | 3 | 4 | 5 | | V-1 | Csf2rb2 |
| 17227 | 3 | 4 | 5 | | V-1 | Csf3r |
| 17228 | 3 | 4 | 5 | | V-1 | Csmd1 |
| 17229 | 3 | 4 | 5 | | V-1 | Csmd2 |
| 17230 | 3 | 4 | 5 | | V-1 | Csn2 |
| 17231 | 3 | 4 | 5 | | V-1 | Csnk1a1 |
| 17232 | 3 | 4 | 5 | | V-1 | Csnk1d |
| 17233 | 3 | 4 | 5 | | V-1 | Csnk1e |
| 17234 | 3 | 4 | 5 | | V-1 | Csnk1g3 |
| 17235 | 3 | 4 | 5 | | V-1 | Cstf1 |
| 17236 | 3 | 4 | 5 | | V-1 | Ctbs |
| 17237 | 3 | 4 | 5 | | V-1 | Ctdsp2 |
| 17238 | 3 | 4 | 5 | | V-1 | Ctnna1 |
| 17239 | 3 | 4 | 5 | | V-1 | Ctnna3 |
| 17240 | 3 | 4 | 5 | | V-1 | Ctu1 |
| 17241 | 3 | 4 | 5 | | V-1 | Ctxn2 |
| 17242 | 3 | 4 | 5 | | V-1 | Cul1 |
| 17243 | 3 | 4 | 5 | | V-1 | Cul3 |
| 17244 | 3 | 4 | 5 | | V-1 | Cux2 |
| 17245 | 3 | 4 | 5 | | V-1 | Cxcl15 |
| 17246 | 3 | 4 | 5 | | V-1 | Cxxc4 |
| 17247 | 3 | 4 | 5 | | V-1 | Cyb561d1 |
| 17248 | 3 | 4 | 5 | | V-1 | Cyp2b23 |
| 17249 | 3 | 4 | 5 | | V-1 | Cyp2j6 |
| 17250 | 3 | 4 | 5 | | V-1 | Cyp4f37 |
| 17251 | 3 | 4 | 5 | | V-1 | Cytip |
| 17252 | 3 | 4 | 5 | | V-1 | D030045P18Rik |
| 17253 | 3 | 4 | 5 | | V-1 | D10Wsu102e |
| 17254 | 3 | 4 | 5 | | V-1 | D15Ertd621e |
| 17255 | 3 | 4 | 5 | | V-1 | D16Ertd519e |
| 17256 | 3 | 4 | 5 | | V-1 | D3Ertd254e |
| 17257 | 3 | 4 | 5 | | V-1 | D4Ertd617e |
| 17258 | 3 | 4 | 5 | | V-1 | D630029K05Rik |
| 17259 | 3 | 4 | 5 | | V-1 | D6Ertd474e |
| 17260 | 3 | 4 | 5 | | V-1 | D730001G18Rik |
| 17261 | 3 | 4 | 5 | | V-1 | D7Ertd143e |
| 17262 | 3 | 4 | 5 | | V-1 | D830032E09Rik |
| 17263 | 3 | 4 | 5 | | V-1 | D830046C22Rik |
| 17264 | 3 | 4 | 5 | | V-1 | Dap |
| 17265 | 3 | 4 | 5 | | V-1 | Dazap2 |
| 17266 | 3 | 4 | 5 | | V-1 | Dcaf12 |
| 17267 | 3 | 4 | 5 | | V-1 | Dcaf17 |
| 17268 | 3 | 4 | 5 | | V-1 | Dcaf8 |
| 17269 | 3 | 4 | 5 | | V-1 | Dcbld2 |
| 17270 | 3 | 4 | 5 | | V-1 | Dcp1b |
| 17271 | 3 | 4 | 5 | | V-1 | Dcp2 |
| 17272 | 3 | 4 | 5 | | V-1 | Dcpp3 |
| 17273 | 3 | 4 | 5 | | V-1 | Dctn4 |
| 17274 | 3 | 4 | 5 | | V-1 | Dcun1d3 |
| 17275 | 3 | 4 | 5 | | V-1 | Dda1 |
| 17276 | 3 | 4 | 5 | | V-1 | Ddx10 |
| 17277 | 3 | 4 | 5 | | V-1 | Ddx17 |
| 17278 | 3 | 4 | 5 | | V-1 | Ddx25 |

Fig. 34 - 91

| | | | | | | | |
|---|---|---|---|---|---|---|---|
| 17279 | 3 | 4 | 5 | | V-1 | Ddx39b |
| 17280 | 3 | 4 | 5 | | V-1 | Ddx42 |
| 17281 | 3 | 4 | 5 | | V-1 | Ddx5 |
| 17282 | 3 | 4 | 5 | | V-1 | Ddx50 |
| 17283 | 3 | 4 | 5 | | V-1 | Ddx58 |
| 17284 | 3 | 4 | 5 | | V-1 | Ddx6 |
| 17285 | 3 | 4 | 5 | | V-1 | Dedd |
| 17286 | 3 | 4 | 5 | | V-1 | Degs1 |
| 17287 | 3 | 4 | 5 | | V-1 | Dennd1a |
| 17288 | 3 | 4 | 5 | | V-1 | Dennd3 |
| 17289 | 3 | 4 | 5 | | V-1 | Dennd4b |
| 17290 | 3 | 4 | 5 | | V-1 | Dennd6a |
| 17291 | 3 | 4 | 5 | | V-1 | Dip2c |
| 17292 | 3 | 4 | 5 | | V-1 | Dlat |
| 17293 | 3 | 4 | 5 | | V-1 | Dld |
| 17294 | 3 | 4 | 5 | | V-1 | Dlg1 |
| 17295 | 3 | 4 | 5 | | V-1 | Dlgap5 |
| 17296 | 3 | 4 | 5 | | V-1 | Dmrtc1a |
| 17297 | 3 | 4 | 5 | | V-1 | Dmwd |
| 17298 | 3 | 4 | 5 | | V-1 | Dnah8 |
| 17299 | 3 | 4 | 5 | | V-1 | Dnaic2 |
| 17300 | 3 | 4 | 5 | | V-1 | Dnaja2 |
| 17301 | 3 | 4 | 5 | | V-1 | Dnajc18 |
| 17302 | 3 | 4 | 5 | | V-1 | Dnajc28 |
| 17303 | 3 | 4 | 5 | | V-1 | Dnajc3 |
| 17304 | 3 | 4 | 5 | | V-1 | Dnmbp |
| 17305 | 3 | 4 | 5 | | V-1 | Dock5 |
| 17306 | 3 | 4 | 5 | | V-1 | Dock6 |
| 17307 | 3 | 4 | 5 | | V-1 | Dppa3 |
| 17308 | 3 | 4 | 5 | | V-1 | Dpysl2 |
| 17309 | 3 | 4 | 5 | | V-1 | Dpysl3 |
| 17310 | 3 | 4 | 5 | | V-1 | Dqx1 |
| 17311 | 3 | 4 | 5 | | V-1 | Drp2 |
| 17312 | 3 | 4 | 5 | | V-1 | Dsp |
| 17313 | 3 | 4 | 5 | | V-1 | Dtwd2 |
| 17314 | 3 | 4 | 5 | | V-1 | Dupd1 |
| 17315 | 3 | 4 | 5 | | V-1 | Dusp23 |
| 17316 | 3 | 4 | 5 | | V-1 | Dvl2 |
| 17317 | 3 | 4 | 5 | | V-1 | Dync1li2 |
| 17318 | 3 | 4 | 5 | | V-1 | Dyrk1b |
| 17319 | 3 | 4 | 5 | | V-1 | Dyx1c1 |
| 17320 | 3 | 4 | 5 | | V-1 | E130114P18Rik |
| 17321 | 3 | 4 | 5 | | V-1 | E130317F20Rik |
| 17322 | 3 | 4 | 5 | | V-1 | E230016K23Rik |
| 17323 | 3 | 4 | 5 | | V-1 | E330013P04Rik |
| 17324 | 3 | 4 | 5 | | V-1 | E430018J23Rik |
| 17325 | 3 | 4 | 5 | | V-1 | Ecd |
| 17326 | 3 | 4 | 5 | | V-1 | Ecsit |
| 17327 | 3 | 4 | 5 | | V-1 | Eed |
| 17328 | 3 | 4 | 5 | | V-1 | Efcab12 |
| 17329 | 3 | 4 | 5 | | V-1 | Efcab9 |
| 17330 | 3 | 4 | 5 | | V-1 | Efnb1 |
| 17331 | 3 | 4 | 5 | | V-1 | Ehbp1 |
| 17332 | 3 | 4 | 5 | | V-1 | Eif1a |
| 17333 | 3 | 4 | 5 | | V-1 | Eif2ak1 |
| 17334 | 3 | 4 | 5 | | V-1 | Eif2ak4 |
| 17335 | 3 | 4 | 5 | | V-1 | Eif2s3y |
| 17336 | 3 | 4 | 5 | | V-1 | Eif4b |
| 17337 | 3 | 4 | 5 | | V-1 | Eif4enif1 |
| 17338 | 3 | 4 | 5 | | V-1 | Elac1 |
| 17339 | 3 | 4 | 5 | | V-1 | Elavl1 |
| 17340 | 3 | 4 | 5 | | V-1 | Elk1 |
| 17341 | 3 | 4 | 5 | | V-1 | Elmod3 |
| 17342 | 3 | 4 | 5 | | V-1 | Elp2 |
| 17343 | 3 | 4 | 5 | | V-1 | Eltd1 |
| 17344 | 3 | 4 | 5 | | V-1 | Eml4 |
| 17345 | 3 | 4 | 5 | | V-1 | Emx2os |
| 17346 | 3 | 4 | 5 | | V-1 | En1 |
| 17347 | 3 | 4 | 5 | | V-1 | Enah |
| 17348 | 3 | 4 | 5 | | V-1 | Endod1 |
| 17349 | 3 | 4 | 5 | | V-1 | Endov |
| 17350 | 3 | 4 | 5 | | V-1 | Eng |
| 17351 | 3 | 4 | 5 | | V-1 | Enpp6 |
| 17352 | 3 | 4 | 5 | | V-1 | Ensa |
| 17353 | 3 | 4 | 5 | | V-1 | Entpd7 |
| 17354 | 3 | 4 | 5 | | V-1 | Epb4.1l4a |
| 17355 | 3 | 4 | 5 | | V-1 | Epb4.1l4b |
| 17356 | 3 | 4 | 5 | | V-1 | Epcam |
| 17357 | 3 | 4 | 5 | | V-1 | Epgn |
| 17358 | 3 | 4 | 5 | | V-1 | Ephb4 |
| 17359 | 3 | 4 | 5 | | V-1 | Ephx4 |
| 17360 | 3 | 4 | 5 | | V-1 | Eprs |
| 17361 | 3 | 4 | 5 | | V-1 | Eps15l1 |
| 17362 | 3 | 4 | 5 | | V-1 | Erbb2 |
| 17363 | 3 | 4 | 5 | | V-1 | Ercc3 |
| 17364 | 3 | 4 | 5 | | V-1 | Ercc4 |
| 17365 | 3 | 4 | 5 | | V-1 | Ercc5 |
| 17366 | 3 | 4 | 5 | | V-1 | Erich3 |
| 17367 | 3 | 4 | 5 | | V-1 | Ermp1 |
| 17368 | 3 | 4 | 5 | | V-1 | Ero1l |
| 17369 | 3 | 4 | 5 | | V-1 | Esr2 |
| 17370 | 3 | 4 | 5 | | V-1 | Etnk2 |
| 17371 | 3 | 4 | 5 | | V-1 | Evpl |
| 17372 | 3 | 4 | 5 | | V-1 | Exd1 |
| 17373 | 3 | 4 | 5 | | V-1 | Ezh1 |
| 17374 | 3 | 4 | 5 | | V-1 | F11r |
| 17375 | 3 | 4 | 5 | | V-1 | F8a |
| 17376 | 3 | 4 | 5 | | V-1 | Fabp12 |
| 17377 | 3 | 4 | 5 | | V-1 | Fabp2 |
| 17378 | 3 | 4 | 5 | | V-1 | Fam101b |
| 17379 | 3 | 4 | 5 | | V-1 | Fam118a |
| 17380 | 3 | 4 | 5 | | V-1 | Fam120a |
| 17381 | 3 | 4 | 5 | | V-1 | Fam120aos |
| 17382 | 3 | 4 | 5 | | V-1 | Fam120b |
| 17383 | 3 | 4 | 5 | | V-1 | Fam129c |
| 17384 | 3 | 4 | 5 | | V-1 | Fam154b |
| 17385 | 3 | 4 | 5 | | V-1 | Fam169a |
| 17386 | 3 | 4 | 5 | | V-1 | Fam170b |
| 17387 | 3 | 4 | 5 | | V-1 | Fam196b |
| 17388 | 3 | 4 | 5 | | V-1 | Fam19a2 |
| 17389 | 3 | 4 | 5 | | V-1 | Fam3c |
| 17390 | 3 | 4 | 5 | | V-1 | Fam63a |
| 17391 | 3 | 4 | 5 | | V-1 | Fam72a |
| 17392 | 3 | 4 | 5 | | V-1 | Fam78b |
| 17393 | 3 | 4 | 5 | | V-1 | Fam89b |
| 17394 | 3 | 4 | 5 | | V-1 | Farp2 |
| 17395 | 3 | 4 | 5 | | V-1 | Fastkd1 |
| 17396 | 3 | 4 | 5 | | V-1 | Fastkd2 |
| 17397 | 3 | 4 | 5 | | V-1 | Fat2 |
| 17398 | 3 | 4 | 5 | | V-1 | Fat3 |
| 17399 | 3 | 4 | 5 | | V-1 | Faxc |
| 17400 | 3 | 4 | 5 | | V-1 | Fbln1 |
| 17401 | 3 | 4 | 5 | | V-1 | Fbxl13 |
| 17402 | 3 | 4 | 5 | | V-1 | Fbxo25 |
| 17403 | 3 | 4 | 5 | | V-1 | Fbxo47 |
| 17404 | 3 | 4 | 5 | | V-1 | Fbxo8 |
| 17405 | 3 | 4 | 5 | | V-1 | Fbxw10 |
| 17406 | 3 | 4 | 5 | | V-1 | Fbxw13 |
| 17407 | 3 | 4 | 5 | | V-1 | Fdxacb1 |
| 17408 | 3 | 4 | 5 | | V-1 | Fgd1 |
| 17409 | 3 | 4 | 5 | | V-1 | Fgd5 |
| 17410 | 3 | 4 | 5 | | V-1 | Fhod1 |
| 17411 | 3 | 4 | 5 | | V-1 | Fkbp15 |
| 17412 | 3 | 4 | 5 | | V-1 | Fkbp6 |
| 17413 | 3 | 4 | 5 | | V-1 | Fkbp9 |
| 17414 | 3 | 4 | 5 | | V-1 | Flnb |
| 17415 | 3 | 4 | 5 | | V-1 | Flnc |
| 17416 | 3 | 4 | 5 | | V-1 | Flrt2 |
| 17417 | 3 | 4 | 5 | | V-1 | Fmn1 |
| 17418 | 3 | 4 | 5 | | V-1 | Fmo3 |
| 17419 | 3 | 4 | 5 | | V-1 | Folr4 |
| 17420 | 3 | 4 | 5 | | V-1 | Fosl1 |
| 17421 | 3 | 4 | 5 | | V-1 | Foxc2 |
| 17422 | 3 | 4 | 5 | | V-1 | Foxd2 |
| 17423 | 3 | 4 | 5 | | V-1 | Foxe3 |
| 17424 | 3 | 4 | 5 | | V-1 | Foxl2 |
| 17425 | 3 | 4 | 5 | | V-1 | Foxp2 |
| 17426 | 3 | 4 | 5 | | V-1 | Frem1 |
| 17427 | 3 | 4 | 5 | | V-1 | Frem2 |
| 17428 | 3 | 4 | 5 | | V-1 | Frmd3 |
| 17429 | 3 | 4 | 5 | | V-1 | Frmd7 |
| 17430 | 3 | 4 | 5 | | V-1 | Frmd8 |
| 17431 | 3 | 4 | 5 | | V-1 | Fsd1 |
| 17432 | 3 | 4 | 5 | | V-1 | Fstl5 |
| 17433 | 3 | 4 | 5 | | V-1 | Fto |
| 17434 | 3 | 4 | 5 | | V-1 | Furin |
| 17435 | 3 | 4 | 5 | | V-1 | Fut10 |
| 17436 | 3 | 4 | 5 | | V-1 | Fut9 |
| 17437 | 3 | 4 | 5 | | V-1 | Fxr1 |
| 17438 | 3 | 4 | 5 | | V-1 | Fzd2 |
| 17439 | 3 | 4 | 5 | | V-1 | Fzd3 |
| 17440 | 3 | 4 | 5 | | V-1 | G6bos |
| 17441 | 3 | 4 | 5 | | V-1 | Gab3 |
| 17442 | 3 | 4 | 5 | | V-1 | Gal3st2 |
| 17443 | 3 | 4 | 5 | | V-1 | Galnt12 |
| 17444 | 3 | 4 | 5 | | V-1 | Galnt2 |
| 17445 | 3 | 4 | 5 | | V-1 | Galnt3 |
| 17446 | 3 | 4 | 5 | | V-1 | Galntl5 |
| 17447 | 3 | 4 | 5 | | V-1 | Ganab |
| 17448 | 3 | 4 | 5 | | V-1 | Garnl3 |
| 17449 | 3 | 4 | 5 | | V-1 | Gast |
| 17450 | 3 | 4 | 5 | | V-1 | Gata3 |
| 17451 | 3 | 4 | 5 | | V-1 | Gata5os |
| 17452 | 3 | 4 | 5 | | V-1 | Gca |
| 17453 | 3 | 4 | 5 | | V-1 | Gcc1 |
| 17454 | 3 | 4 | 5 | | V-1 | Gdf9 |
| 17455 | 3 | 4 | 5 | | V-1 | Gdi1 |
| 17456 | 3 | 4 | 5 | | V-1 | Gemin5 |
| 17457 | 3 | 4 | 5 | | V-1 | Ggnbp2 |
| 17458 | 3 | 4 | 5 | | V-1 | Ghitm |
| 17459 | 3 | 4 | 5 | | V-1 | Gipc3 |
| 17460 | 3 | 4 | 5 | | V-1 | Gipr |
| 17461 | 3 | 4 | 5 | | V-1 | Gja5 |
| 17462 | 3 | 4 | 5 | | V-1 | Gjd3 |
| 17463 | 3 | 4 | 5 | | V-1 | Gle1 |
| 17464 | 3 | 4 | 5 | | V-1 | Glipr1 |
| 17465 | 3 | 4 | 5 | | V-1 | Glis1 |
| 17466 | 3 | 4 | 5 | | V-1 | Glis3 |
| 17467 | 3 | 4 | 5 | | V-1 | Glp1r |
| 17468 | 3 | 4 | 5 | | V-1 | Glyat |
| 17469 | 3 | 4 | 5 | | V-1 | Gm10228 |
| 17470 | 3 | 4 | 5 | | V-1 | Gm10354 |

Fig. 34 - 92

| | | | | | | | |
|---|---|---|---|---|---|---|---|
| 17471 | 3 | 4 | 5 | | V-1 | Gm10421 |
| 17472 | 3 | 4 | 5 | | V-1 | Gm10790 |
| 17473 | 3 | 4 | 5 | | V-1 | Gm10857 |
| 17474 | 3 | 4 | 5 | | V-1 | Gm10863 |
| 17475 | 3 | 4 | 5 | | V-1 | Gm10922 |
| 17476 | 3 | 4 | 5 | | V-1 | Gm11110 |
| 17477 | 3 | 4 | 5 | | V-1 | Gm11190 |
| 17478 | 3 | 4 | 5 | | V-1 | Gm11240 |
| 17479 | 3 | 4 | 5 | | V-1 | Gm11563 |
| 17480 | 3 | 4 | 5 | | V-1 | Gm11757 |
| 17481 | 3 | 4 | 5 | | V-1 | Gm13251 |
| 17482 | 3 | 4 | 5 | | V-1 | Gm13483 |
| 17483 | 3 | 4 | 5 | | V-1 | Gm13546 |
| 17484 | 3 | 4 | 5 | | V-1 | Gm136 |
| 17485 | 3 | 4 | 5 | | V-1 | Gm14151 |
| 17486 | 3 | 4 | 5 | | V-1 | Gm14347 |
| 17487 | 3 | 4 | 5 | | V-1 | Gm14477 |
| 17488 | 3 | 4 | 5 | | V-1 | Gm14499 |
| 17489 | 3 | 4 | 5 | | V-1 | Gm14501 |
| 17490 | 3 | 4 | 5 | | V-1 | Gm15127 |
| 17491 | 3 | 4 | 5 | | V-1 | Gm15328 |
| 17492 | 3 | 4 | 5 | | V-1 | Gm16023 |
| 17493 | 3 | 4 | 5 | | V-1 | Gm16325 |
| 17494 | 3 | 4 | 5 | | V-1 | Gm1647 |
| 17495 | 3 | 4 | 5 | | V-1 | Gm16677 |
| 17496 | 3 | 4 | 5 | | V-1 | Gm16863 |
| 17497 | 3 | 4 | 5 | | V-1 | Gm16894 |
| 17498 | 3 | 4 | 5 | | V-1 | Gm17019 |
| 17499 | 3 | 4 | 5 | | V-1 | Gm17066 |
| 17500 | 3 | 4 | 5 | | V-1 | Gm17769 |
| 17501 | 3 | 4 | 5 | | V-1 | Gm1993 |
| 17502 | 3 | 4 | 5 | | V-1 | Gm1995 |
| 17503 | 3 | 4 | 5 | | V-1 | Gm2011 |
| 17504 | 3 | 4 | 5 | | V-1 | Gm2042 |
| 17505 | 3 | 4 | 5 | | V-1 | Gm20554 |
| 17506 | 3 | 4 | 5 | | V-1 | Gm20611 |
| 17507 | 3 | 4 | 5 | | V-1 | Gm20753 |
| 17508 | 3 | 4 | 5 | | V-1 | Gm20822 |
| 17509 | 3 | 4 | 5 | | V-1 | Gm21002 |
| 17510 | 3 | 4 | 5 | | V-1 | Gm21119 |
| 17511 | 3 | 4 | 5 | | V-1 | Gm21221 |
| 17512 | 3 | 4 | 5 | | V-1 | Gm21269 |
| 17513 | 3 | 4 | 5 | | V-1 | Gm21693 |
| 17514 | 3 | 4 | 5 | | V-1 | Gm21708 |
| 17515 | 3 | 4 | 5 | | V-1 | Gm2825 |
| 17516 | 3 | 4 | 5 | | V-1 | Gm2927 |
| 17517 | 3 | 4 | 5 | | V-1 | Gm3716 |
| 17518 | 3 | 4 | 5 | | V-1 | Gm3763 |
| 17519 | 3 | 4 | 5 | | V-1 | Gm4285 |
| 17520 | 3 | 4 | 5 | | V-1 | Gm436 |
| 17521 | 3 | 4 | 5 | | V-1 | Gm4719 |
| 17522 | 3 | 4 | 5 | | V-1 | Gm4763 |
| 17523 | 3 | 4 | 5 | | V-1 | Gm4788 |
| 17524 | 3 | 4 | 5 | | V-1 | Gm4890 |
| 17525 | 3 | 4 | 5 | | V-1 | Gm4907 |
| 17526 | 3 | 4 | 5 | | V-1 | Gm4925 |
| 17527 | 3 | 4 | 5 | | V-1 | Gm4944 |
| 17528 | 3 | 4 | 5 | | V-1 | Gm5071 |
| 17529 | 3 | 4 | 5 | | V-1 | Gm5105 |
| 17530 | 3 | 4 | 5 | | V-1 | Gm5294 |
| 17531 | 3 | 4 | 5 | | V-1 | Gm5347 |
| 17532 | 3 | 4 | 5 | | V-1 | Gm5382 |
| 17533 | 3 | 4 | 5 | | V-1 | Gm5415 |
| 17534 | 3 | 4 | 5 | | V-1 | Gm5458 |
| 17535 | 3 | 4 | 5 | | V-1 | Gm5595 |
| 17536 | 3 | 4 | 5 | | V-1 | Gm5640 |
| 17537 | 3 | 4 | 5 | | V-1 | Gm5862 |
| 17538 | 3 | 4 | 5 | | V-1 | Gm595 |
| 17539 | 3 | 4 | 5 | | V-1 | Gm6277 |
| 17540 | 3 | 4 | 5 | | V-1 | Gm7102 |
| 17541 | 3 | 4 | 5 | | V-1 | Gm711 |
| 17542 | 3 | 4 | 5 | | V-1 | Gm7168 |
| 17543 | 3 | 4 | 5 | | V-1 | Gm732 |
| 17544 | 3 | 4 | 5 | | V-1 | Gm7788 |
| 17545 | 3 | 4 | 5 | | V-1 | Gm8580 |
| 17546 | 3 | 4 | 5 | | V-1 | Gm904 |
| 17547 | 3 | 4 | 5 | | V-1 | Gm9047 |
| 17548 | 3 | 4 | 5 | | V-1 | Gm973 |
| 17549 | 3 | 4 | 5 | | V-1 | Gm9776 |
| 17550 | 3 | 4 | 5 | | V-1 | Gm9839 |
| 17551 | 3 | 4 | 5 | | V-1 | Gm9994 |
| 17552 | 3 | 4 | 5 | | V-1 | Gm9999 |
| 17553 | 3 | 4 | 5 | | V-1 | Gmeb1 |
| 17554 | 3 | 4 | 5 | | V-1 | Gmip |
| 17555 | 3 | 4 | 5 | | V-1 | Gng10 |
| 17556 | 3 | 4 | 5 | | V-1 | Gns |
| 17557 | 3 | 4 | 5 | | V-1 | Golm1 |
| 17558 | 3 | 4 | 5 | | V-1 | Gorasp1 |
| 17559 | 3 | 4 | 5 | | V-1 | Got2 |
| 17560 | 3 | 4 | 5 | | V-1 | Gp1ba |
| 17561 | 3 | 4 | 5 | | V-1 | Gp6 |
| 17562 | 3 | 4 | 5 | | V-1 | Gpatch1 |
| 17563 | 3 | 4 | 5 | | V-1 | Gpbp1 |
| 17564 | 3 | 4 | 5 | | V-1 | Gpc4 |
| 17565 | 3 | 4 | 5 | | V-1 | Gpr113 |
| 17566 | 3 | 4 | 5 | | V-1 | Gpr179 |
| 17567 | 3 | 4 | 5 | | V-1 | Gpr20 |
| 17568 | 3 | 4 | 5 | | V-1 | Gpr26 |
| 17569 | 3 | 4 | 5 | | V-1 | Gpr35 |
| 17570 | 3 | 4 | 5 | | V-1 | Gpr61 |
| 17571 | 3 | 4 | 5 | | V-1 | Gpr62 |
| 17572 | 3 | 4 | 5 | | V-1 | Grik2 |
| 17573 | 3 | 4 | 5 | | V-1 | Grin2c |
| 17574 | 3 | 4 | 5 | | V-1 | Grin3b |
| 17575 | 3 | 4 | 5 | | V-1 | Grip1 |
| 17576 | 3 | 4 | 5 | | V-1 | Grip1os2 |
| 17577 | 3 | 4 | 5 | | V-1 | Gripap1 |
| 17578 | 3 | 4 | 5 | | V-1 | Grm2 |
| 17579 | 3 | 4 | 5 | | V-1 | Grm3 |
| 17580 | 3 | 4 | 5 | | V-1 | Gsk3a |
| 17581 | 3 | 4 | 5 | | V-1 | Gsr |
| 17582 | 3 | 4 | 5 | | V-1 | Gsto2 |
| 17583 | 3 | 4 | 5 | | V-1 | Gstt3 |
| 17584 | 3 | 4 | 5 | | V-1 | Gt(ROSA)26Sor |
| 17585 | 3 | 4 | 5 | | V-1 | Gtf2ird2 |
| 17586 | 3 | 4 | 5 | | V-1 | Gtf3c5 |
| 17587 | 3 | 4 | 5 | | V-1 | Gtpbp1 |
| 17588 | 3 | 4 | 5 | | V-1 | Gtpbp2 |
| 17589 | 3 | 4 | 5 | | V-1 | Gtpbp4 |
| 17590 | 3 | 4 | 5 | | V-1 | Gucy2c |
| 17591 | 3 | 4 | 5 | | V-1 | Gxylt1 |
| 17592 | 3 | 4 | 5 | | V-1 | Gzf1 |
| 17593 | 3 | 4 | 5 | | V-1 | Gzmk |
| 17594 | 3 | 4 | 5 | | V-1 | H2-Oa |
| 17595 | 3 | 4 | 5 | | V-1 | H2-Ob |
| 17596 | 3 | 4 | 5 | | V-1 | Habp2 |
| 17597 | 3 | 4 | 5 | | V-1 | Hand2 |
| 17598 | 3 | 4 | 5 | | V-1 | Hapln1 |
| 17599 | 3 | 4 | 5 | | V-1 | Hapln2 |
| 17600 | 3 | 4 | 5 | | V-1 | Haus5 |
| 17601 | 3 | 4 | 5 | | V-1 | Hck |
| 17602 | 3 | 4 | 5 | | V-1 | Heatr1 |
| 17603 | 3 | 4 | 5 | | V-1 | Heatr9 |
| 17604 | 3 | 4 | 5 | | V-1 | Helb |
| 17605 | 3 | 4 | 5 | | V-1 | Hgfac |
| 17606 | 3 | 4 | 5 | | V-1 | Hic2 |
| 17607 | 3 | 4 | 5 | | V-1 | Hid1 |
| 17608 | 3 | 4 | 5 | | V-1 | Hif1an |
| 17609 | 3 | 4 | 5 | | V-1 | Higd2a |
| 17610 | 3 | 4 | 5 | | V-1 | Hist1h2ab |
| 17611 | 3 | 4 | 5 | | V-1 | Hist2h2be |
| 17612 | 3 | 4 | 5 | | V-1 | Hjurp |
| 17613 | 3 | 4 | 5 | | V-1 | Hmgcll1 |
| 17614 | 3 | 4 | 5 | | V-1 | Hmx1 |
| 17615 | 3 | 4 | 5 | | V-1 | Hnf1b |
| 17616 | 3 | 4 | 5 | | V-1 | Hnf4g |
| 17617 | 3 | 4 | 5 | | V-1 | Hnrnpa3 |
| 17618 | 3 | 4 | 5 | | V-1 | Hnrnpdl |
| 17619 | 3 | 4 | 5 | | V-1 | Hnrnpk |
| 17620 | 3 | 4 | 5 | | V-1 | Hnrnpl |
| 17621 | 3 | 4 | 5 | | V-1 | Hoxb4 |
| 17622 | 3 | 4 | 5 | | V-1 | Hoxb8 |
| 17623 | 3 | 4 | 5 | | V-1 | Hoxc10 |
| 17624 | 3 | 4 | 5 | | V-1 | Hoxd10 |
| 17625 | 3 | 4 | 5 | | V-1 | Hoxd4 |
| 17626 | 3 | 4 | 5 | | V-1 | Hrasls |
| 17627 | 3 | 4 | 5 | | V-1 | Hs1bp3 |
| 17628 | 3 | 4 | 5 | | V-1 | Hs3st3a1 |
| 17629 | 3 | 4 | 5 | | V-1 | Hs6st2 |
| 17630 | 3 | 4 | 5 | | V-1 | Hsbp1 |
| 17631 | 3 | 4 | 5 | | V-1 | Hsd17b2 |
| 17632 | 3 | 4 | 5 | | V-1 | Hsd17b4 |
| 17633 | 3 | 4 | 5 | | V-1 | Hsdl1 |
| 17634 | 3 | 4 | 5 | | V-1 | Hspbap1 |
| 17635 | 3 | 4 | 5 | | V-1 | Hunk |
| 17636 | 3 | 4 | 5 | | V-1 | I730030J21Rik |
| 17637 | 3 | 4 | 5 | | V-1 | Ibsp |
| 17638 | 3 | 4 | 5 | | V-1 | Ica1 |
| 17639 | 3 | 4 | 5 | | V-1 | Idi2 |
| 17640 | 3 | 4 | 5 | | V-1 | Ier3ip1 |
| 17641 | 3 | 4 | 5 | | V-1 | Ifnar1 |
| 17642 | 3 | 4 | 5 | | V-1 | Ifngr1 |
| 17643 | 3 | 4 | 5 | | V-1 | Ifnz |
| 17644 | 3 | 4 | 5 | | V-1 | Ift140 |
| 17645 | 3 | 4 | 5 | | V-1 | Igfn1 |
| 17646 | 3 | 4 | 5 | | V-1 | Igsf23 |
| 17647 | 3 | 4 | 5 | | V-1 | Il10ra |
| 17648 | 3 | 4 | 5 | | V-1 | Il16 |
| 17649 | 3 | 4 | 5 | | V-1 | Il1b |
| 17650 | 3 | 4 | 5 | | V-1 | Il23a |
| 17651 | 3 | 4 | 5 | | V-1 | Il25 |
| 17652 | 3 | 4 | 5 | | V-1 | Il2rb |
| 17653 | 3 | 4 | 5 | | V-1 | Il2rg |
| 17654 | 3 | 4 | 5 | | V-1 | Il4 |
| 17655 | 3 | 4 | 5 | | V-1 | Il6st |
| 17656 | 3 | 4 | 5 | | V-1 | Immt |
| 17657 | 3 | 4 | 5 | | V-1 | Imp4 |
| 17658 | 3 | 4 | 5 | | V-1 | Inadl |
| 17659 | 3 | 4 | 5 | | V-1 | Ing4 |
| 17660 | 3 | 4 | 5 | | V-1 | Ints6 |
| 17661 | 3 | 4 | 5 | | V-1 | Ints7 |
| 17662 | 3 | 4 | 5 | | V-1 | Ipo4 |

Fig. 34 - 93

| | | | | | | | |
|---|---|---|---|---|---|---|---|
| 17663 | 3 | 4 | 5 | | V-1 | Ipo9 |
| 17664 | 3 | 4 | 5 | | V-1 | Iqcb1 |
| 17665 | 3 | 4 | 5 | | V-1 | Irak3 |
| 17666 | 3 | 4 | 5 | | V-1 | Irak4 |
| 17667 | 3 | 4 | 5 | | V-1 | Irx2 |
| 17668 | 3 | 4 | 5 | | V-1 | Ism1 |
| 17669 | 3 | 4 | 5 | | V-1 | Ispd |
| 17670 | 3 | 4 | 5 | | V-1 | Ist1 |
| 17671 | 3 | 4 | 5 | | V-1 | Itga9 |
| 17672 | 3 | 4 | 5 | | V-1 | Itgae |
| 17673 | 3 | 4 | 5 | | V-1 | Itgb4 |
| 17674 | 3 | 4 | 5 | | V-1 | Itgb8 |
| 17675 | 3 | 4 | 5 | | V-1 | Itih3 |
| 17676 | 3 | 4 | 5 | | V-1 | Itk |
| 17677 | 3 | 4 | 5 | | V-1 | Itm2b |
| 17678 | 3 | 4 | 5 | | V-1 | Itm2c |
| 17679 | 3 | 4 | 5 | | V-1 | Itpr2 |
| 17680 | 3 | 4 | 5 | | V-1 | Ivd |
| 17681 | 3 | 4 | 5 | | V-1 | Ivl |
| 17682 | 3 | 4 | 5 | | V-1 | Izumo1 |
| 17683 | 3 | 4 | 5 | | V-1 | Jade2 |
| 17684 | 3 | 4 | 5 | | V-1 | Jagn1 |
| 17685 | 3 | 4 | 5 | | V-1 | Kank2 |
| 17686 | 3 | 4 | 5 | | V-1 | Kat2a |
| 17687 | 3 | 4 | 5 | | V-1 | Katnal2 |
| 17688 | 3 | 4 | 5 | | V-1 | Kcmf1 |
| 17689 | 3 | 4 | 5 | | V-1 | Kcna7 |
| 17690 | 3 | 4 | 5 | | V-1 | Kcng1 |
| 17691 | 3 | 4 | 5 | | V-1 | Kcnh2 |
| 17692 | 3 | 4 | 5 | | V-1 | Kcnip1 |
| 17693 | 3 | 4 | 5 | | V-1 | Kcnj16 |
| 17694 | 3 | 4 | 5 | | V-1 | Kcnk10 |
| 17695 | 3 | 4 | 5 | | V-1 | Kcnk9 |
| 17696 | 3 | 4 | 5 | | V-1 | Kcnma1 |
| 17697 | 3 | 4 | 5 | | V-1 | Kcnn1 |
| 17698 | 3 | 4 | 5 | | V-1 | Kcnq5 |
| 17699 | 3 | 4 | 5 | | V-1 | Kcnu1 |
| 17700 | 3 | 4 | 5 | | V-1 | Kctd10 |
| 17701 | 3 | 4 | 5 | | V-1 | Kctd16 |
| 17702 | 3 | 4 | 5 | | V-1 | Kctd4 |
| 17703 | 3 | 4 | 5 | | V-1 | Kdm2a |
| 17704 | 3 | 4 | 5 | | V-1 | Kdm4b |
| 17705 | 3 | 4 | 5 | | V-1 | Kdm5b |
| 17706 | 3 | 4 | 5 | | V-1 | Kdm8 |
| 17707 | 3 | 4 | 5 | | V-1 | Kdsr |
| 17708 | 3 | 4 | 5 | | V-1 | Keap1 |
| 17709 | 3 | 4 | 5 | | V-1 | Khdrbs3 |
| 17710 | 3 | 4 | 5 | | V-1 | Khsrp |
| 17711 | 3 | 4 | 5 | | V-1 | Kif21b |
| 17712 | 3 | 4 | 5 | | V-1 | Kif9 |
| 17713 | 3 | 4 | 5 | | V-1 | Kiz |
| 17714 | 3 | 4 | 5 | | V-1 | Klc1 |
| 17715 | 3 | 4 | 5 | | V-1 | Klf17 |
| 17716 | 3 | 4 | 5 | | V-1 | Klhl1 |
| 17717 | 3 | 4 | 5 | | V-1 | Klhl11 |
| 17718 | 3 | 4 | 5 | | V-1 | Klhl12 |
| 17719 | 3 | 4 | 5 | | V-1 | Klhl15 |
| 17720 | 3 | 4 | 5 | | V-1 | Klhl18 |
| 17721 | 3 | 4 | 5 | | V-1 | Klhl3 |
| 17722 | 3 | 4 | 5 | | V-1 | Klhl31 |
| 17723 | 3 | 4 | 5 | | V-1 | Klk1b3 |
| 17724 | 3 | 4 | 5 | | V-1 | Klk7 |
| 17725 | 3 | 4 | 5 | | V-1 | Klrb1a |
| 17726 | 3 | 4 | 5 | | V-1 | Klre1 |
| 17727 | 3 | 4 | 5 | | V-1 | Klri1 |
| 17728 | 3 | 4 | 5 | | V-1 | Klri2 |
| 17729 | 3 | 4 | 5 | | V-1 | Krt25 |
| 17730 | 3 | 4 | 5 | | V-1 | Krt71 |
| 17731 | 3 | 4 | 5 | | V-1 | Krtap4-6 |
| 17732 | 3 | 4 | 5 | | V-1 | Krtap4-9 |
| 17733 | 3 | 4 | 5 | | V-1 | Kynu |
| 17734 | 3 | 4 | 5 | | V-1 | LOC100504808 |
| 17735 | 3 | 4 | 5 | | V-1 | LOC100505025 |
| 17736 | 3 | 4 | 5 | | V-1 | LOC101055769 |
| 17737 | 3 | 4 | 5 | | V-1 | LOC101056236 |
| 17738 | 3 | 4 | 5 | | V-1 | Lamp2 |
| 17739 | 3 | 4 | 5 | | V-1 | Laptm4a |
| 17740 | 3 | 4 | 5 | | V-1 | Larp6 |
| 17741 | 3 | 4 | 5 | | V-1 | Lbr |
| 17742 | 3 | 4 | 5 | | V-1 | Lce1i |
| 17743 | 3 | 4 | 5 | | V-1 | Lce3b |
| 17744 | 3 | 4 | 5 | | V-1 | Lck |
| 17745 | 3 | 4 | 5 | | V-1 | Lcn4 |
| 17746 | 3 | 4 | 5 | | V-1 | Ldlrad1 |
| 17747 | 3 | 4 | 5 | | V-1 | Ldoc1 |
| 17748 | 3 | 4 | 5 | | V-1 | Lhx8 |
| 17749 | 3 | 4 | 5 | | V-1 | Lif |
| 17750 | 3 | 4 | 5 | | V-1 | Lig3 |
| 17751 | 3 | 4 | 5 | | V-1 | Limd1 |
| 17752 | 3 | 4 | 5 | | V-1 | Lincrna-cox2 |
| 17753 | 3 | 4 | 5 | | V-1 | Lins |
| 17754 | 3 | 4 | 5 | | V-1 | Llgl1 |
| 17755 | 3 | 4 | 5 | | V-1 | Llgl2 |
| 17756 | 3 | 4 | 5 | | V-1 | Lman1l |
| 17757 | 3 | 4 | 5 | | V-1 | Lmbrd1 |
| 17758 | 3 | 4 | 5 | | V-1 | Lmbrd2 |
| 17759 | 3 | 4 | 5 | | V-1 | Lmx1a |
| 17760 | 3 | 4 | 5 | | V-1 | Loxl2 |
| 17761 | 3 | 4 | 5 | | V-1 | Loxl3 |
| 17762 | 3 | 4 | 5 | | V-1 | Lpar2 |
| 17763 | 3 | 4 | 5 | | V-1 | Lpcat2 |
| 17764 | 3 | 4 | 5 | | V-1 | Lrcol1 |
| 17765 | 3 | 4 | 5 | | V-1 | Lrfn5 |
| 17766 | 3 | 4 | 5 | | V-1 | Lrp6 |
| 17767 | 3 | 4 | 5 | | V-1 | Lrpap1 |
| 17768 | 3 | 4 | 5 | | V-1 | Lrrc1 |
| 17769 | 3 | 4 | 5 | | V-1 | Lrrc14b |
| 17770 | 3 | 4 | 5 | | V-1 | Lrrc3 |
| 17771 | 3 | 4 | 5 | | V-1 | Lrrc41 |
| 17772 | 3 | 4 | 5 | | V-1 | Lrrc42 |
| 17773 | 3 | 4 | 5 | | V-1 | Lrrc48 |
| 17774 | 3 | 4 | 5 | | V-1 | Lrrc8e |
| 17775 | 3 | 4 | 5 | | V-1 | Lrrc9 |
| 17776 | 3 | 4 | 5 | | V-1 | Lrrk1 |
| 17777 | 3 | 4 | 5 | | V-1 | Lrsam1 |
| 17778 | 3 | 4 | 5 | | V-1 | Ltk |
| 17779 | 3 | 4 | 5 | | V-1 | Ltn1 |
| 17780 | 3 | 4 | 5 | | V-1 | Lysmd1 |
| 17781 | 3 | 4 | 5 | | V-1 | Lyzl4os |
| 17782 | 3 | 4 | 5 | | V-1 | Madd |
| 17783 | 3 | 4 | 5 | | V-1 | Magi2 |
| 17784 | 3 | 4 | 5 | | V-1 | Man1a2 |
| 17785 | 3 | 4 | 5 | | V-1 | Man1c1 |
| 17786 | 3 | 4 | 5 | | V-1 | Man2a2 |
| 17787 | 3 | 4 | 5 | | V-1 | Manr |
| 17788 | 3 | 4 | 5 | | V-1 | Map3k15 |
| 17789 | 3 | 4 | 5 | | V-1 | Map4 |
| 17790 | 3 | 4 | 5 | | V-1 | March5 |
| 17791 | 3 | 4 | 5 | | V-1 | March6 |
| 17792 | 3 | 4 | 5 | | V-1 | Mast2 |
| 17793 | 3 | 4 | 5 | | V-1 | Mast3 |
| 17794 | 3 | 4 | 5 | | V-1 | Mau2 |
| 17795 | 3 | 4 | 5 | | V-1 | Max |
| 17796 | 3 | 4 | 5 | | V-1 | Mbd3l1 |
| 17797 | 3 | 4 | 5 | | V-1 | Mbd4 |
| 17798 | 3 | 4 | 5 | | V-1 | Mcemp1 |
| 17799 | 3 | 4 | 5 | | V-1 | Mcm3ap |
| 17800 | 3 | 4 | 5 | | V-1 | Mctp1 |
| 17801 | 3 | 4 | 5 | | V-1 | Mctp2 |
| 17802 | 3 | 4 | 5 | | V-1 | Mecom |
| 17803 | 3 | 4 | 5 | | V-1 | Med25 |
| 17804 | 3 | 4 | 5 | | V-1 | Mef2a |
| 17805 | 3 | 4 | 5 | | V-1 | Metap1 |
| 17806 | 3 | 4 | 5 | | V-1 | Mettl13 |
| 17807 | 3 | 4 | 5 | | V-1 | Mettl2 |
| 17808 | 3 | 4 | 5 | | V-1 | Mff |
| 17809 | 3 | 4 | 5 | | V-1 | Mfi2 |
| 17810 | 3 | 4 | 5 | | V-1 | Mfrp |
| 17811 | 3 | 4 | 5 | | V-1 | Mfsd7a |
| 17812 | 3 | 4 | 5 | | V-1 | Mgat4b |
| 17813 | 3 | 4 | 5 | | V-1 | Mia3 |
| 17814 | 3 | 4 | 5 | | V-1 | Micu1 |
| 17815 | 3 | 4 | 5 | | V-1 | Mier2 |
| 17816 | 3 | 4 | 5 | | V-1 | Mier3 |
| 17817 | 3 | 4 | 5 | | V-1 | Minpp1 |
| 17818 | 3 | 4 | 5 | | V-1 | Mipol1 |
| 17819 | 3 | 4 | 5 | | V-1 | Mkrn2 |
| 17820 | 3 | 4 | 5 | | V-1 | Mkx |
| 17821 | 3 | 4 | 5 | | V-1 | Mlh3 |
| 17822 | 3 | 4 | 5 | | V-1 | Mllt1 |
| 17823 | 3 | 4 | 5 | | V-1 | Mlst8 |
| 17824 | 3 | 4 | 5 | | V-1 | Mmachc |
| 17825 | 3 | 4 | 5 | | V-1 | Mmp2 |
| 17826 | 3 | 4 | 5 | | V-1 | Mmp24 |
| 17827 | 3 | 4 | 5 | | V-1 | Mob3a |
| 17828 | 3 | 4 | 5 | | V-1 | Morc1 |
| 17829 | 3 | 4 | 5 | | V-1 | Mrfap1 |
| 17830 | 3 | 4 | 5 | | V-1 | Mrgpra2a |
| 17831 | 3 | 4 | 5 | | V-1 | Mrgpra2b |
| 17832 | 3 | 4 | 5 | | V-1 | Mrgprb1 |
| 17833 | 3 | 4 | 5 | | V-1 | Mro |
| 17834 | 3 | 4 | 5 | | V-1 | Mroh8 |
| 17835 | 3 | 4 | 5 | | V-1 | Mrpl1 |
| 17836 | 3 | 4 | 5 | | V-1 | Mrpl16 |
| 17837 | 3 | 4 | 5 | | V-1 | Mrpl3 |
| 17838 | 3 | 4 | 5 | | V-1 | Mrps25 |
| 17839 | 3 | 4 | 5 | | V-1 | Ms4a15 |
| 17840 | 3 | 4 | 5 | | V-1 | Ms4a5 |
| 17841 | 3 | 4 | 5 | | V-1 | Msl3 |
| 17842 | 3 | 4 | 5 | | V-1 | Mta1 |
| 17843 | 3 | 4 | 5 | | V-1 | Mtmr2 |
| 17844 | 3 | 4 | 5 | | V-1 | Mtmr4 |
| 17845 | 3 | 4 | 5 | | V-1 | Mug-ps1 |
| 17846 | 3 | 4 | 5 | | V-1 | Mug2 |
| 17847 | 3 | 4 | 5 | | V-1 | Myb |
| 17848 | 3 | 4 | 5 | | V-1 | Mycbp |
| 17849 | 3 | 4 | 5 | | V-1 | Mycn |
| 17850 | 3 | 4 | 5 | | V-1 | Myh13 |
| 17851 | 3 | 4 | 5 | | V-1 | Myo18a |
| 17852 | 3 | 4 | 5 | | V-1 | Myo1a |
| 17853 | 3 | 4 | 5 | | V-1 | Myo1c |
| 17854 | 3 | 4 | 5 | | V-1 | Myo5b |

Fig. 34 - 94

| | | | | | | | |
|---|---|---|---|---|---|---|---|
| 17855 | 3 | 4 | 5 | | V-1 | Myocd |
| 17856 | 3 | 4 | 5 | | V-1 | Myom2 |
| 17857 | 3 | 4 | 5 | | V-1 | Myrf |
| 17858 | 3 | 4 | 5 | | V-1 | Myt1 |
| 17859 | 3 | 4 | 5 | | V-1 | Naa16 |
| 17860 | 3 | 4 | 5 | | V-1 | Naa30 |
| 17861 | 3 | 4 | 5 | | V-1 | Naa50 |
| 17862 | 3 | 4 | 5 | | V-1 | Nab1 |
| 17863 | 3 | 4 | 5 | | V-1 | Naip2 |
| 17864 | 3 | 4 | 5 | | V-1 | Naip5 |
| 17865 | 3 | 4 | 5 | | V-1 | Nap1l1 |
| 17866 | 3 | 4 | 5 | | V-1 | Nap1l4 |
| 17867 | 3 | 4 | 5 | | V-1 | Narg2 |
| 17868 | 3 | 4 | 5 | | V-1 | Nat1 |
| 17869 | 3 | 4 | 5 | | V-1 | Nckap1 |
| 17870 | 3 | 4 | 5 | | V-1 | Nckap1l |
| 17871 | 3 | 4 | 5 | | V-1 | Ndst2 |
| 17872 | 3 | 4 | 5 | | V-1 | Neb |
| 17873 | 3 | 4 | 5 | | V-1 | Nek9 |
| 17874 | 3 | 4 | 5 | | V-1 | Nelfb |
| 17875 | 3 | 4 | 5 | | V-1 | Neo1 |
| 17876 | 3 | 4 | 5 | | V-1 | Nefo1 |
| 17877 | 3 | 4 | 5 | | V-1 | Neu4 |
| 17878 | 3 | 4 | 5 | | V-1 | Neurog2 |
| 17879 | 3 | 4 | 5 | | V-1 | Nexn |
| 17880 | 3 | 4 | 5 | | V-1 | Nfatc2 |
| 17881 | 3 | 4 | 5 | | V-1 | Nfx1 |
| 17882 | 3 | 4 | 5 | | V-1 | Ngrn |
| 17883 | 3 | 4 | 5 | | V-1 | Nhs |
| 17884 | 3 | 4 | 5 | | V-1 | Nipal3 |
| 17885 | 3 | 4 | 5 | | V-1 | Nkap1 |
| 17886 | 3 | 4 | 5 | | V-1 | Nkiras2 |
| 17887 | 3 | 4 | 5 | | V-1 | Nlrp12 |
| 17888 | 3 | 4 | 5 | | V-1 | Nlrp5 |
| 17889 | 3 | 4 | 5 | | V-1 | Nmbr |
| 17890 | 3 | 4 | 5 | | V-1 | Nmt2 |
| 17891 | 3 | 4 | 5 | | V-1 | Nmu |
| 17892 | 3 | 4 | 5 | | V-1 | Nod2 |
| 17893 | 3 | 4 | 5 | | V-1 | Nom1 |
| 17894 | 3 | 4 | 5 | | V-1 | Nop58 |
| 17895 | 3 | 4 | 5 | | V-1 | Noxred1 |
| 17896 | 3 | 4 | 5 | | V-1 | Npat |
| 17897 | 3 | 4 | 5 | | V-1 | Nr1i2 |
| 17898 | 3 | 4 | 5 | | V-1 | Nras |
| 17899 | 3 | 4 | 5 | | V-1 | Nrf1 |
| 17900 | 3 | 4 | 5 | | V-1 | Nsmce4a |
| 17901 | 3 | 4 | 5 | | V-1 | Nsmf |
| 17902 | 3 | 4 | 5 | | V-1 | Ntn3 |
| 17903 | 3 | 4 | 5 | | V-1 | Nudc |
| 17904 | 3 | 4 | 5 | | V-1 | Nudt4 |
| 17905 | 3 | 4 | 5 | | V-1 | Nup214 |
| 17906 | 3 | 4 | 5 | | V-1 | Nup35 |
| 17907 | 3 | 4 | 5 | | V-1 | Nutm1 |
| 17908 | 3 | 4 | 5 | | V-1 | Nyx |
| 17909 | 3 | 4 | 5 | | V-1 | Oas1f |
| 17910 | 3 | 4 | 5 | | V-1 | Oaz2 |
| 17911 | 3 | 4 | 5 | | V-1 | Ociad1 |
| 17912 | 3 | 4 | 5 | | V-1 | Ogfod1 |
| 17913 | 3 | 4 | 5 | | V-1 | Ogg1 |
| 17914 | 3 | 4 | 5 | | V-1 | Ola1 |
| 17915 | 3 | 4 | 5 | | V-1 | Olfm3 |
| 17916 | 3 | 4 | 5 | | V-1 | Olfr112 |
| 17917 | 3 | 4 | 5 | | V-1 | Olfr1344 |
| 17918 | 3 | 4 | 5 | | V-1 | Olfr1392 |
| 17919 | 3 | 4 | 5 | | V-1 | Olfr1393 |
| 17920 | 3 | 4 | 5 | | V-1 | Olfr1413 |
| 17921 | 3 | 4 | 5 | | V-1 | Olfr1507 |
| 17922 | 3 | 4 | 5 | | V-1 | Olfr20 |
| 17923 | 3 | 4 | 5 | | V-1 | Olfr215 |
| 17924 | 3 | 4 | 5 | | V-1 | Olfr307 |
| 17925 | 3 | 4 | 5 | | V-1 | Olfr545 |
| 17926 | 3 | 4 | 5 | | V-1 | Olfr558 |
| 17927 | 3 | 4 | 5 | | V-1 | Olfr78 |
| 17928 | 3 | 4 | 5 | | V-1 | Olfr944 |
| 17929 | 3 | 4 | 5 | | V-1 | Olig2 |
| 17930 | 3 | 4 | 5 | | V-1 | Omp |
| 17931 | 3 | 4 | 5 | | V-1 | Orc2 |
| 17932 | 3 | 4 | 5 | | V-1 | Ormdl3 |
| 17933 | 3 | 4 | 5 | | V-1 | Osbpl2 |
| 17934 | 3 | 4 | 5 | | V-1 | Oser1 |
| 17935 | 3 | 4 | 5 | | V-1 | Osgin2 |
| 17936 | 3 | 4 | 5 | | V-1 | Ostc |
| 17937 | 3 | 4 | 5 | | V-1 | Otog |
| 17938 | 3 | 4 | 5 | | V-1 | Otop2 |
| 17939 | 3 | 4 | 5 | | V-1 | Oxct2a |
| 17940 | 3 | 4 | 5 | | V-1 | P2ry2 |
| 17941 | 3 | 4 | 5 | | V-1 | Pabpc6 |
| 17942 | 3 | 4 | 5 | | V-1 | Pacs2 |
| 17943 | 3 | 4 | 5 | | V-1 | Pacsin2 |
| 17944 | 3 | 4 | 5 | | V-1 | Padi4 |
| 17945 | 3 | 4 | 5 | | V-1 | Padi6 |
| 17946 | 3 | 4 | 5 | | V-1 | Pafah1b2 |
| 17947 | 3 | 4 | 5 | | V-1 | Paics |
| 17948 | 3 | 4 | 5 | | V-1 | Paip2 |
| 17949 | 3 | 4 | 5 | | V-1 | Paid1 |
| 17950 | 3 | 4 | 5 | | V-1 | Palm2 |
| 17951 | 3 | 4 | 5 | | V-1 | Pappa |
| 17952 | 3 | 4 | 5 | | V-1 | Pappa2 |
| 17953 | 3 | 4 | 5 | | V-1 | Paqr5 |
| 17954 | 3 | 4 | 5 | | V-1 | Parg |
| 17955 | 3 | 4 | 5 | | V-1 | Parn |
| 17956 | 3 | 4 | 5 | | V-1 | Parp1 |
| 17957 | 3 | 4 | 5 | | V-1 | Parva |
| 17958 | 3 | 4 | 5 | | V-1 | Patz1 |
| 17959 | 3 | 4 | 5 | | V-1 | Pax8 |
| 17960 | 3 | 4 | 5 | | V-1 | Pax9 |
| 17961 | 3 | 4 | 5 | | V-1 | Paxbp1 |
| 17962 | 3 | 4 | 5 | | V-1 | Pbx2 |
| 17963 | 3 | 4 | 5 | | V-1 | Pcdh12 |
| 17964 | 3 | 4 | 5 | | V-1 | Pcdhb12 |
| 17965 | 3 | 4 | 5 | | V-1 | Pcmt1 |
| 17966 | 3 | 4 | 5 | | V-1 | Pcnp |
| 17967 | 3 | 4 | 5 | | V-1 | Pcnx |
| 17968 | 3 | 4 | 5 | | V-1 | Pcnxl3 |
| 17969 | 3 | 4 | 5 | | V-1 | Pcsk2os1 |
| 17970 | 3 | 4 | 5 | | V-1 | Pdcd11 |
| 17971 | 3 | 4 | 5 | | V-1 | Pdcd6ip |
| 17972 | 3 | 4 | 5 | | V-1 | Pde6a |
| 17973 | 3 | 4 | 5 | | V-1 | Pde8b |
| 17974 | 3 | 4 | 5 | | V-1 | Pdhx |
| 17975 | 3 | 4 | 5 | | V-1 | Pdpn |
| 17976 | 3 | 4 | 5 | | V-1 | Pdyn |
| 17977 | 3 | 4 | 5 | | V-1 | Pdzd7 |
| 17978 | 3 | 4 | 5 | | V-1 | Pef1 |
| 17979 | 3 | 4 | 5 | | V-1 | Pex12 |
| 17980 | 3 | 4 | 5 | | V-1 | Pfkfb4 |
| 17981 | 3 | 4 | 5 | | V-1 | Pglyrp2 |
| 17982 | 3 | 4 | 5 | | V-1 | Pgpep1 |
| 17983 | 3 | 4 | 5 | | V-1 | Pgpep1l |
| 17984 | 3 | 4 | 5 | | V-1 | Phactr3 |
| 17985 | 3 | 4 | 5 | | V-1 | Phc1 |
| 17986 | 3 | 4 | 5 | | V-1 | Phf14 |
| 17987 | 3 | 4 | 5 | | V-1 | Phf21a |
| 17988 | 3 | 4 | 5 | | V-1 | Phf21b |
| 17989 | 3 | 4 | 5 | | V-1 | Phka1 |
| 17990 | 3 | 4 | 5 | | V-1 | Phldb1 |
| 17991 | 3 | 4 | 5 | | V-1 | Phospho2 |
| 17992 | 3 | 4 | 5 | | V-1 | Pi15 |
| 17993 | 3 | 4 | 5 | | V-1 | Pi4kb |
| 17994 | 3 | 4 | 5 | | V-1 | Pigc |
| 17995 | 3 | 4 | 5 | | V-1 | Pigo |
| 17996 | 3 | 4 | 5 | | V-1 | Pip4k2a |
| 17997 | 3 | 4 | 5 | | V-1 | Pitpnm1 |
| 17998 | 3 | 4 | 5 | | V-1 | Piwil2 |
| 17999 | 3 | 4 | 5 | | V-1 | Pkd1l3 |
| 18000 | 3 | 4 | 5 | | V-1 | Pla2g12b |
| 18001 | 3 | 4 | 5 | | V-1 | Pla2g4d |
| 18002 | 3 | 4 | 5 | | V-1 | Plac8l1 |
| 18003 | 3 | 4 | 5 | | V-1 | Plcl1 |
| 18004 | 3 | 4 | 5 | | V-1 | Pld1 |
| 18005 | 3 | 4 | 5 | | V-1 | Pld2 |
| 18006 | 3 | 4 | 5 | | V-1 | Plec |
| 18007 | 3 | 4 | 5 | | V-1 | Plekha8 |
| 18008 | 3 | 4 | 5 | | V-1 | Plekhd1os |
| 18009 | 3 | 4 | 5 | | V-1 | Plekhf2 |
| 18010 | 3 | 4 | 5 | | V-1 | Plekhg6 |
| 18011 | 3 | 4 | 5 | | V-1 | Plekhh1 |
| 18012 | 3 | 4 | 5 | | V-1 | Plekhn1 |
| 18013 | 3 | 4 | 5 | | V-1 | Plg |
| 18014 | 3 | 4 | 5 | | V-1 | Plscr3 |
| 18015 | 3 | 4 | 5 | | V-1 | Plxdc2 |
| 18016 | 3 | 4 | 5 | | V-1 | Plxnb1 |
| 18017 | 3 | 4 | 5 | | V-1 | Pmp2 |
| 18018 | 3 | 4 | 5 | | V-1 | Pmpca |
| 18019 | 3 | 4 | 5 | | V-1 | Pmpcb |
| 18020 | 3 | 4 | 5 | | V-1 | Pnma2 |
| 18021 | 3 | 4 | 5 | | V-1 | Pnma3 |
| 18022 | 3 | 4 | 5 | | V-1 | Pnoc |
| 18023 | 3 | 4 | 5 | | V-1 | Poc1b |
| 18024 | 3 | 4 | 5 | | V-1 | Poldip2 |
| 18025 | 3 | 4 | 5 | | V-1 | Polr1b |
| 18026 | 3 | 4 | 5 | | V-1 | Polr2a |
| 18027 | 3 | 4 | 5 | | V-1 | Polr3k |
| 18028 | 3 | 4 | 5 | | V-1 | Pomk |
| 18029 | 3 | 4 | 5 | | V-1 | Pomt2 |
| 18030 | 3 | 4 | 5 | | V-1 | Pot1a |
| 18031 | 3 | 4 | 5 | | V-1 | Ppfia1 |
| 18032 | 3 | 4 | 5 | | V-1 | Ppm1b |
| 18033 | 3 | 4 | 5 | | V-1 | Ppp1cc |
| 18034 | 3 | 4 | 5 | | V-1 | Ppp1r17 |
| 18035 | 3 | 4 | 5 | | V-1 | Ppp2ca |
| 18036 | 3 | 4 | 5 | | V-1 | Ppp2r5c |
| 18037 | 3 | 4 | 5 | | V-1 | Ppp3cb |
| 18038 | 3 | 4 | 5 | | V-1 | Ppp3r1 |
| 18039 | 3 | 4 | 5 | | V-1 | Ppp3r2 |
| 18040 | 3 | 4 | 5 | | V-1 | Ppp6c |
| 18041 | 3 | 4 | 5 | | V-1 | Ppp6r2 |
| 18042 | 3 | 4 | 5 | | V-1 | Pramef12 |
| 18043 | 3 | 4 | 5 | | V-1 | Prdm14 |
| 18044 | 3 | 4 | 5 | | V-1 | Prdm6 |
| 18045 | 3 | 4 | 5 | | V-1 | Primpol |
| 18046 | 3 | 4 | 5 | | V-1 | Prkab1 |

Fig. 34 - 95

| | | | | | | | |
|---|---|---|---|---|---|---|---|
| 18047 | 3 | 4 | 5 | | V-1 | Prkag2os1 | |
| 18048 | 3 | 4 | 5 | | V-1 | Prorsd1 | |
| 18049 | 3 | 4 | 5 | | V-1 | Prox1 | |
| 18050 | 3 | 4 | 5 | | V-1 | Prps1l1 | |
| 18051 | 3 | 4 | 5 | | V-1 | Prr13 | |
| 18052 | 3 | 4 | 5 | | V-1 | Prr19 | |
| 18053 | 3 | 4 | 5 | | V-1 | Prr3 | |
| 18054 | 3 | 4 | 5 | | V-1 | Prss27 | |
| 18055 | 3 | 4 | 5 | | V-1 | Prss28 | |
| 18056 | 3 | 4 | 5 | | V-1 | Prss40 | |
| 18057 | 3 | 4 | 5 | | V-1 | Prss44 | |
| 18058 | 3 | 4 | 5 | | V-1 | Prss46 | |
| 18059 | 3 | 4 | 5 | | V-1 | Prss55 | |
| 18060 | 3 | 4 | 5 | | V-1 | Prss58 | |
| 18061 | 3 | 4 | 5 | | V-1 | Psd2 | |
| 18062 | 3 | 4 | 5 | | V-1 | Psd4 | |
| 18063 | 3 | 4 | 5 | | V-1 | Psmd5 | |
| 18064 | 3 | 4 | 5 | | V-1 | Psme3 | |
| 18065 | 3 | 4 | 5 | | V-1 | Ptch2 | |
| 18066 | 3 | 4 | 5 | | V-1 | Ptf1a | |
| 18067 | 3 | 4 | 5 | | V-1 | Pth2r | |
| 18068 | 3 | 4 | 5 | | V-1 | Ptk6 | |
| 18069 | 3 | 4 | 5 | | V-1 | Ptpdc1 | |
| 18070 | 3 | 4 | 5 | | V-1 | Ptpn20 | |
| 18071 | 3 | 4 | 5 | | V-1 | Ptpn23 | |
| 18072 | 3 | 4 | 5 | | V-1 | Ptpn3 | |
| 18073 | 3 | 4 | 5 | | V-1 | Ptpn6 | |
| 18074 | 3 | 4 | 5 | | V-1 | Ptprt | |
| 18075 | 3 | 4 | 5 | | V-1 | Pttg1ip | |
| 18076 | 3 | 4 | 5 | | V-1 | Ptx4 | |
| 18077 | 3 | 4 | 5 | | V-1 | Pus10 | |
| 18078 | 3 | 4 | 5 | | V-1 | Pxn | |
| 18079 | 3 | 4 | 5 | | V-1 | Pycr1 | |
| 18080 | 3 | 4 | 5 | | V-1 | Qrfpr | |
| 18081 | 3 | 4 | 5 | | V-1 | Qrich2 | |
| 18082 | 3 | 4 | 5 | | V-1 | R3hcc1l | |
| 18083 | 3 | 4 | 5 | | V-1 | Rab11fip3 | |
| 18084 | 3 | 4 | 5 | | V-1 | Rab11fip4os2 | |
| 18085 | 3 | 4 | 5 | | V-1 | Rab18 | |
| 18086 | 3 | 4 | 5 | | V-1 | Rab19 | |
| 18087 | 3 | 4 | 5 | | V-1 | Rab21 | |
| 18088 | 3 | 4 | 5 | | V-1 | Rab2a | |
| 18089 | 3 | 4 | 5 | | V-1 | Rab35 | |
| 18090 | 3 | 4 | 5 | | V-1 | Rab37 | |
| 18091 | 3 | 4 | 5 | | V-1 | Rab39 | |
| 18092 | 3 | 4 | 5 | | V-1 | Rab9b | |
| 18093 | 3 | 4 | 5 | | V-1 | Rabep1 | |
| 18094 | 3 | 4 | 5 | | V-1 | Rabgap1l | |
| 18095 | 3 | 4 | 5 | | V-1 | Rac1 | |
| 18096 | 3 | 4 | 5 | | V-1 | Rad18 | |
| 18097 | 3 | 4 | 5 | | V-1 | Rad23b | |
| 18098 | 3 | 4 | 5 | | V-1 | Rad8 | |
| 18099 | 3 | 4 | 5 | | V-1 | Raet1c | |
| 18100 | 3 | 4 | 5 | | V-1 | Ralbp1 | |
| 18101 | 3 | 4 | 5 | | V-1 | Ranbp10 | |
| 18102 | 3 | 4 | 5 | | V-1 | Rars | |
| 18103 | 3 | 4 | 5 | | V-1 | Rasal3 | |
| 18104 | 3 | 4 | 5 | | V-1 | Rasef | |
| 18105 | 3 | 4 | 5 | | V-1 | Rassf1 | |
| 18106 | 3 | 4 | 5 | | V-1 | Rassf10 | |
| 18107 | 3 | 4 | 5 | | V-1 | Rbbp4 | |
| 18108 | 3 | 4 | 5 | | V-1 | Rbm27 | |
| 18109 | 3 | 4 | 5 | | V-1 | Rbm34 | |
| 18110 | 3 | 4 | 5 | | V-1 | Rbms2 | |
| 18111 | 3 | 4 | 5 | | V-1 | Rbpj | |
| 18112 | 3 | 4 | 5 | | V-1 | Rbpjl | |
| 18113 | 3 | 4 | 5 | | V-1 | Rbx1 | |
| 18114 | 3 | 4 | 5 | | V-1 | Rc3h2 | |
| 18115 | 3 | 4 | 5 | | V-1 | Rcan3 | |
| 18116 | 3 | 4 | 5 | | V-1 | Rcbtb1 | |
| 18117 | 3 | 4 | 5 | | V-1 | Rchy1 | |
| 18118 | 3 | 4 | 5 | | V-1 | Rcn1 | |
| 18119 | 3 | 4 | 5 | | V-1 | Rd3 | |
| 18120 | 3 | 4 | 5 | | V-1 | Rdh16 | |
| 18121 | 3 | 4 | 5 | | V-1 | Relt | |
| 18122 | 3 | 4 | 5 | | V-1 | Rep15 | |
| 18123 | 3 | 4 | 5 | | V-1 | Ret | |
| 18124 | 3 | 4 | 5 | | V-1 | Rev3l | |
| 18125 | 3 | 4 | 5 | | V-1 | Rexo1 | |
| 18126 | 3 | 4 | 5 | | V-1 | Rftn1 | |
| 18127 | 3 | 4 | 5 | | V-1 | Rfwd3 | |
| 18128 | 3 | 4 | 5 | | V-1 | Rgs12 | |
| 18129 | 3 | 4 | 5 | | V-1 | Rgs17 | |
| 18130 | 3 | 4 | 5 | | V-1 | Rhbdd2 | |
| 18131 | 3 | 4 | 5 | | V-1 | Rhcg | |
| 18132 | 3 | 4 | 5 | | V-1 | Rhob | |
| 18133 | 3 | 4 | 5 | | V-1 | Rhox8 | |
| 18134 | 3 | 4 | 5 | | V-1 | Ribc1 | |
| 18135 | 3 | 4 | 5 | | V-1 | Rilpl1 | |
| 18136 | 3 | 4 | 5 | | V-1 | Rims4 | |
| 18137 | 3 | 4 | 5 | | V-1 | Riok1 | |
| 18138 | 3 | 4 | 5 | | V-1 | Ripply2 | |
| 18139 | 3 | 4 | 5 | | V-1 | Rmdn3 | |
| 18140 | 3 | 4 | 5 | | V-1 | Rnf115 | |
| 18141 | 3 | 4 | 5 | | V-1 | Rnf130 | |
| 18142 | 3 | 4 | 5 | | V-1 | Rnf138rt1 | |
| 18143 | 3 | 4 | 5 | | V-1 | Rnf14 | |
| 18144 | 3 | 4 | 5 | | V-1 | Rnf180 | |
| 18145 | 3 | 4 | 5 | | V-1 | Rnf181 | |
| 18146 | 3 | 4 | 5 | | V-1 | Rnf187 | |
| 18147 | 3 | 4 | 5 | | V-1 | Rnf19a | |
| 18148 | 3 | 4 | 5 | | V-1 | Rnf214 | |
| 18149 | 3 | 4 | 5 | | V-1 | Rnf222 | |
| 18150 | 3 | 4 | 5 | | V-1 | Rnf223 | |
| 18151 | 3 | 4 | 5 | | V-1 | Rnf40 | |
| 18152 | 3 | 4 | 5 | | V-1 | Rpgr | |
| 18153 | 3 | 4 | 5 | | V-1 | Rpgrip1l | |
| 18154 | 3 | 4 | 5 | | V-1 | Rpl21 | |
| 18155 | 3 | 4 | 5 | | V-1 | Rps6ka6 | |
| 18156 | 3 | 4 | 5 | | V-1 | Rps6kc1 | |
| 18157 | 3 | 4 | 5 | | V-1 | Rptoros | |
| 18158 | 3 | 4 | 5 | | V-1 | Rpusd2 | |
| 18159 | 3 | 4 | 5 | | V-1 | Rragc | |
| 18160 | 3 | 4 | 5 | | V-1 | Rsad1 | |
| 18161 | 3 | 4 | 5 | | V-1 | Rsl1 | |
| 18162 | 3 | 4 | 5 | | V-1 | Rspo4 | |
| 18163 | 3 | 4 | 5 | | V-1 | Rspry1 | |
| 18164 | 3 | 4 | 5 | | V-1 | Rtel1 | |
| 18165 | 3 | 4 | 5 | | V-1 | Rtf1 | |
| 18166 | 3 | 4 | 5 | | V-1 | Rtn4ip1 | |
| 18167 | 3 | 4 | 5 | | V-1 | Rtp1 | |
| 18168 | 3 | 4 | 5 | | V-1 | Rundc3b | |
| 18169 | 3 | 4 | 5 | | V-1 | Runx1t1 | |
| 18170 | 3 | 4 | 5 | | V-1 | Ryr2 | |
| 18171 | 3 | 4 | 5 | | V-1 | S100a14 | |
| 18172 | 3 | 4 | 5 | | V-1 | Sap18 | |
| 18173 | 3 | 4 | 5 | | V-1 | Sar1a | |
| 18174 | 3 | 4 | 5 | | V-1 | Sart1 | |
| 18175 | 3 | 4 | 5 | | V-1 | Sart3 | |
| 18176 | 3 | 4 | 5 | | V-1 | Sbf1 | |
| 18177 | 3 | 4 | 5 | | V-1 | Scamp3 | |
| 18178 | 3 | 4 | 5 | | V-1 | Scfd1 | |
| 18179 | 3 | 4 | 5 | | V-1 | Scfd2 | |
| 18180 | 3 | 4 | 5 | | V-1 | Scgb1b29 | |
| 18181 | 3 | 4 | 5 | | V-1 | Scgb1b3 | |
| 18182 | 3 | 4 | 5 | | V-1 | Scgb2b20 | |
| 18183 | 3 | 4 | 5 | | V-1 | Sclt1 | |
| 18184 | 3 | 4 | 5 | | V-1 | Scly | |
| 18185 | 3 | 4 | 5 | | V-1 | Scml4 | |
| 18186 | 3 | 4 | 5 | | V-1 | Scn3a | |
| 18187 | 3 | 4 | 5 | | V-1 | Scube1 | |
| 18188 | 3 | 4 | 5 | | V-1 | Sdha | |
| 18189 | 3 | 4 | 5 | | V-1 | Sdhaf2 | |
| 18190 | 3 | 4 | 5 | | V-1 | Sdk2 | |
| 18191 | 3 | 4 | 5 | | V-1 | Sec16b | |
| 18192 | 3 | 4 | 5 | | V-1 | Sec22a | |
| 18193 | 3 | 4 | 5 | | V-1 | Sec23b | |
| 18194 | 3 | 4 | 5 | | V-1 | Sec24b | |
| 18195 | 3 | 4 | 5 | | V-1 | Sec61a2 | |
| 18196 | 3 | 4 | 5 | | V-1 | Sel1l2 | |
| 18197 | 3 | 4 | 5 | | V-1 | Selp | |
| 18198 | 3 | 4 | 5 | | V-1 | Senp1 | |
| 18199 | 3 | 4 | 5 | | V-1 | Senp2 | |
| 18200 | 3 | 4 | 5 | | V-1 | Sep15 | |
| 18201 | 3 | 4 | 5 | | V-1 | Sephs1 | |
| 18202 | 3 | 4 | 5 | | V-1 | Serbp1 | |
| 18203 | 3 | 4 | 5 | | V-1 | Serpina11 | |
| 18204 | 3 | 4 | 5 | | V-1 | Serpinb1b | |
| 18205 | 3 | 4 | 5 | | V-1 | Serpinb9 | |
| 18206 | 3 | 4 | 5 | | V-1 | Sertm1 | |
| 18207 | 3 | 4 | 5 | | V-1 | Set | |
| 18208 | 3 | 4 | 5 | | V-1 | Sf3b2 | |
| 18209 | 3 | 4 | 5 | | V-1 | Sfmbt2 | |
| 18210 | 3 | 4 | 5 | | V-1 | Sftpd | |
| 18211 | 3 | 4 | 5 | | V-1 | Sgsm3 | |
| 18212 | 3 | 4 | 5 | | V-1 | Sh3bgrl | |
| 18213 | 3 | 4 | 5 | | V-1 | Sh3tc1 | |
| 18214 | 3 | 4 | 5 | | V-1 | Sharpin | |
| 18215 | 3 | 4 | 5 | | V-1 | Shc4 | |
| 18216 | 3 | 4 | 5 | | V-1 | Shroom1 | |
| 18217 | 3 | 4 | 5 | | V-1 | Sike1 | |
| 18218 | 3 | 4 | 5 | | V-1 | Simc1 | |
| 18219 | 3 | 4 | 5 | | V-1 | Sipa1 | |
| 18220 | 3 | 4 | 5 | | V-1 | Sit1 | |
| 18221 | 3 | 4 | 5 | | V-1 | Six4 | |
| 18222 | 3 | 4 | 5 | | V-1 | Skint8 | |
| 18223 | 3 | 4 | 5 | | V-1 | Skor1 | |
| 18224 | 3 | 4 | 5 | | V-1 | Slc12a8 | |
| 18225 | 3 | 4 | 5 | | V-1 | Slc13a1 | |
| 18226 | 3 | 4 | 5 | | V-1 | Slc13a2 | |
| 18227 | 3 | 4 | 5 | | V-1 | Slc13a5 | |
| 18228 | 3 | 4 | 5 | | V-1 | Slc15a1 | |
| 18229 | 3 | 4 | 5 | | V-1 | Slc19a1 | |
| 18230 | 3 | 4 | 5 | | V-1 | Slc22a14 | |
| 18231 | 3 | 4 | 5 | | V-1 | Slc22a19 | |
| 18232 | 3 | 4 | 5 | | V-1 | Slc22a20 | |
| 18233 | 3 | 4 | 5 | | V-1 | Slc22a5 | |
| 18234 | 3 | 4 | 5 | | V-1 | Slc24a1 | |
| 18235 | 3 | 4 | 5 | | V-1 | Slc25a18 | |
| 18236 | 3 | 4 | 5 | | V-1 | Slc25a20 | |
| 18237 | 3 | 4 | 5 | | V-1 | Slc25a41 | |
| 18238 | 3 | 4 | 5 | | V-1 | Slc25a43 | |

Fig. 34 - 96

| | | | | | | | |
|---|---|---|---|---|---|---|---|
| 18239 | 3 | 4 | 5 | | V-1 | Slc25a46 |
| 18240 | 3 | 4 | 5 | | V-1 | Slc26a3 |
| 18241 | 3 | 4 | 5 | | V-1 | Slc26a7 |
| 18242 | 3 | 4 | 5 | | V-1 | Slc30a8 |
| 18243 | 3 | 4 | 5 | | V-1 | Slc34a1 |
| 18244 | 3 | 4 | 5 | | V-1 | Slc35f1 |
| 18245 | 3 | 4 | 5 | | V-1 | Slc35f3 |
| 18246 | 3 | 4 | 5 | | V-1 | Slc35f6 |
| 18247 | 3 | 4 | 5 | | V-1 | Slc36a1os |
| 18248 | 3 | 4 | 5 | | V-1 | Slc39a13 |
| 18249 | 3 | 4 | 5 | | V-1 | Slc41a2 |
| 18250 | 3 | 4 | 5 | | V-1 | Slc45a1 |
| 18251 | 3 | 4 | 5 | | V-1 | Slc46a2 |
| 18252 | 3 | 4 | 5 | | V-1 | Slc52a2 |
| 18253 | 3 | 4 | 5 | | V-1 | Slc52a3 |
| 18254 | 3 | 4 | 5 | | V-1 | Slc5a12 |
| 18255 | 3 | 4 | 5 | | V-1 | Slc5a2 |
| 18256 | 3 | 4 | 5 | | V-1 | Slc6a18 |
| 18257 | 3 | 4 | 5 | | V-1 | Slc7a7 |
| 18258 | 3 | 4 | 5 | | V-1 | Slc8a1 |
| 18259 | 3 | 4 | 5 | | V-1 | Slc9a5 |
| 18260 | 3 | 4 | 5 | | V-1 | Slc9a6 |
| 18261 | 3 | 4 | 5 | | V-1 | Slc9a8 |
| 18262 | 3 | 4 | 5 | | V-1 | Slc9b2 |
| 18263 | 3 | 4 | 5 | | V-1 | Slco1a5 |
| 18264 | 3 | 4 | 5 | | V-1 | Slit1 |
| 18265 | 3 | 4 | 5 | | V-1 | Slit2 |
| 18266 | 3 | 4 | 5 | | V-1 | Slmo2 |
| 18267 | 3 | 4 | 5 | | V-1 | Slxl1 |
| 18268 | 3 | 4 | 5 | | V-1 | Smad4 |
| 18269 | 3 | 4 | 5 | | V-1 | Smap2 |
| 18270 | 3 | 4 | 5 | | V-1 | Smarca2 |
| 18271 | 3 | 4 | 5 | | V-1 | Smek1 |
| 18272 | 3 | 4 | 5 | | V-1 | Smek2 |
| 18273 | 3 | 4 | 5 | | V-1 | Smim9 |
| 18274 | 3 | 4 | 5 | | V-1 | Smo |
| 18275 | 3 | 4 | 5 | | V-1 | Smok2b |
| 18276 | 3 | 4 | 5 | | V-1 | Smok3a |
| 18277 | 3 | 4 | 5 | | V-1 | Smok3b |
| 18278 | 3 | 4 | 5 | | V-1 | Smpd4 |
| 18279 | 3 | 4 | 5 | | V-1 | Smpdl3b |
| 18280 | 3 | 4 | 5 | | V-1 | Sms |
| 18281 | 3 | 4 | 5 | | V-1 | Smtnl1 |
| 18282 | 3 | 4 | 5 | | V-1 | Smyd4 |
| 18283 | 3 | 4 | 5 | | V-1 | Smyd5 |
| 18284 | 3 | 4 | 5 | | V-1 | Snapc1 |
| 18285 | 3 | 4 | 5 | | V-1 | Snhg1 |
| 18286 | 3 | 4 | 5 | | V-1 | Snx11 |
| 18287 | 3 | 4 | 5 | | V-1 | Snx19 |
| 18288 | 3 | 4 | 5 | | V-1 | Snx3 |
| 18289 | 3 | 4 | 5 | | V-1 | Snx30 |
| 18290 | 3 | 4 | 5 | | V-1 | Sowahb |
| 18291 | 3 | 4 | 5 | | V-1 | Sox2ot |
| 18292 | 3 | 4 | 5 | | V-1 | Sox30 |
| 18293 | 3 | 4 | 5 | | V-1 | Sp4 |
| 18294 | 3 | 4 | 5 | | V-1 | Spaca5 |
| 18295 | 3 | 4 | 5 | | V-1 | Spag17 |
| 18296 | 3 | 4 | 5 | | V-1 | Spata31d1b |
| 18297 | 3 | 4 | 5 | | V-1 | Spcs3 |
| 18298 | 3 | 4 | 5 | | V-1 | Spdef |
| 18299 | 3 | 4 | 5 | | V-1 | Specc1l |
| 18300 | 3 | 4 | 5 | | V-1 | Spg11 |
| 18301 | 3 | 4 | 5 | | V-1 | Spo11 |
| 18302 | 3 | 4 | 5 | | V-1 | Sprr2j-ps |
| 18303 | 3 | 4 | 5 | | V-1 | Sptan1 |
| 18304 | 3 | 4 | 5 | | V-1 | Sptlc3 |
| 18305 | 3 | 4 | 5 | | V-1 | Sqstm1 |
| 18306 | 3 | 4 | 5 | | V-1 | Srp72 |
| 18307 | 3 | 4 | 5 | | V-1 | Srpk1 |
| 18308 | 3 | 4 | 5 | | V-1 | Srpr |
| 18309 | 3 | 4 | 5 | | V-1 | Srrm3 |
| 18310 | 3 | 4 | 5 | | V-1 | Srrm4os |
| 18311 | 3 | 4 | 5 | | V-1 | Srsf11 |
| 18312 | 3 | 4 | 5 | | V-1 | Ss18 |
| 18313 | 3 | 4 | 5 | | V-1 | Ss18l1 |
| 18314 | 3 | 4 | 5 | | V-1 | Ssbp2 |
| 18315 | 3 | 4 | 5 | | V-1 | Ssbp3 |
| 18316 | 3 | 4 | 5 | | V-1 | Ssxb1 |
| 18317 | 3 | 4 | 5 | | V-1 | St13 |
| 18318 | 3 | 4 | 5 | | V-1 | Stab2 |
| 18319 | 3 | 4 | 5 | | V-1 | Stac2 |
| 18320 | 3 | 4 | 5 | | V-1 | Stag1 |
| 18321 | 3 | 4 | 5 | | V-1 | Stard8 |
| 18322 | 3 | 4 | 5 | | V-1 | Stat6 |
| 18323 | 3 | 4 | 5 | | V-1 | Steap1 |
| 18324 | 3 | 4 | 5 | | V-1 | Steap2 |
| 18325 | 3 | 4 | 5 | | V-1 | Stim2 |
| 18326 | 3 | 4 | 5 | | V-1 | Stk17b |
| 18327 | 3 | 4 | 5 | | V-1 | Stk31 |
| 18328 | 3 | 4 | 5 | | V-1 | Stk36 |
| 18329 | 3 | 4 | 5 | | V-1 | Stk38 |
| 18330 | 3 | 4 | 5 | | V-1 | Stom |
| 18331 | 3 | 4 | 5 | | V-1 | Stra6 |
| 18332 | 3 | 4 | 5 | | V-1 | Strap |
| 18333 | 3 | 4 | 5 | | V-1 | Strbp |
| 18334 | 3 | 4 | 5 | | V-1 | Stt3b |
| 18335 | 3 | 4 | 5 | | V-1 | Stxbp5l |
| 18336 | 3 | 4 | 5 | | V-1 | Sumf1 |
| 18337 | 3 | 4 | 5 | | V-1 | Surf6 |
| 18338 | 3 | 4 | 5 | | V-1 | Svip |
| 18339 | 3 | 4 | 5 | | V-1 | Syce1 |
| 18340 | 3 | 4 | 5 | | V-1 | Sycp2 |
| 18341 | 3 | 4 | 5 | | V-1 | Syna |
| 18342 | 3 | 4 | 5 | | V-1 | Sync |
| 18343 | 3 | 4 | 5 | | V-1 | Sypl |
| 18344 | 3 | 4 | 5 | | V-1 | Syt6 |
| 18345 | 3 | 4 | 5 | | V-1 | Szt2 |
| 18346 | 3 | 4 | 5 | | V-1 | Tada1 |
| 18347 | 3 | 4 | 5 | | V-1 | Taf1a |
| 18348 | 3 | 4 | 5 | | V-1 | Tanc2 |
| 18349 | 3 | 4 | 5 | | V-1 | Taok2 |
| 18350 | 3 | 4 | 5 | | V-1 | Tardbp |
| 18351 | 3 | 4 | 5 | | V-1 | Tatdn2 |
| 18352 | 3 | 4 | 5 | | V-1 | Tbc1d10b |
| 18353 | 3 | 4 | 5 | | V-1 | Tbc1d13 |
| 18354 | 3 | 4 | 5 | | V-1 | Tbc1d2 |
| 18355 | 3 | 4 | 5 | | V-1 | Tbc1d22a |
| 18356 | 3 | 4 | 5 | | V-1 | Tbkbp1 |
| 18357 | 3 | 4 | 5 | | V-1 | Tbx1 |
| 18358 | 3 | 4 | 5 | | V-1 | Tbx19 |
| 18359 | 3 | 4 | 5 | | V-1 | Tceal8 |
| 18360 | 3 | 4 | 5 | | V-1 | Tcf4 |
| 18361 | 3 | 4 | 5 | | V-1 | Tcf7l2 |
| 18362 | 3 | 4 | 5 | | V-1 | Tcp10b |
| 18363 | 3 | 4 | 5 | | V-1 | Tcp10c |
| 18364 | 3 | 4 | 5 | | V-1 | Tcta |
| 18365 | 3 | 4 | 5 | | V-1 | Tdp2 |
| 18366 | 3 | 4 | 5 | | V-1 | Tdpoz4 |
| 18367 | 3 | 4 | 5 | | V-1 | Tdrd12 |
| 18368 | 3 | 4 | 5 | | V-1 | Tdrd3 |
| 18369 | 3 | 4 | 5 | | V-1 | Tdrd6 |
| 18370 | 3 | 4 | 5 | | V-1 | Tecrl |
| 18371 | 3 | 4 | 5 | | V-1 | Tekt3 |
| 18372 | 3 | 4 | 5 | | V-1 | Tepp |
| 18373 | 3 | 4 | 5 | | V-1 | Terf2ip |
| 18374 | 3 | 4 | 5 | | V-1 | Tesc |
| 18375 | 3 | 4 | 5 | | V-1 | Tesk2 |
| 18376 | 3 | 4 | 5 | | V-1 | Tex15 |
| 18377 | 3 | 4 | 5 | | V-1 | Tex2 |
| 18378 | 3 | 4 | 5 | | V-1 | Tex37 |
| 18379 | 3 | 4 | 5 | | V-1 | Tex43 |
| 18380 | 3 | 4 | 5 | | V-1 | Tex9 |
| 18381 | 3 | 4 | 5 | | V-1 | Tfap2a |
| 18382 | 3 | 4 | 5 | | V-1 | Tfap2c |
| 18383 | 3 | 4 | 5 | | V-1 | Thap4 |
| 18384 | 3 | 4 | 5 | | V-1 | Thap6 |
| 18385 | 3 | 4 | 5 | | V-1 | Thoc3 |
| 18386 | 3 | 4 | 5 | | V-1 | Thsd4 |
| 18387 | 3 | 4 | 5 | | V-1 | Timm8a1 |
| 18388 | 3 | 4 | 5 | | V-1 | Timp2 |
| 18389 | 3 | 4 | 5 | | V-1 | Tjp2 |
| 18390 | 3 | 4 | 5 | | V-1 | Tk2 |
| 18391 | 3 | 4 | 5 | | V-1 | Tlk1 |
| 18392 | 3 | 4 | 5 | | V-1 | Tlr3 |
| 18393 | 3 | 4 | 5 | | V-1 | Tlx2 |
| 18394 | 3 | 4 | 5 | | V-1 | Tm9sf1 |
| 18395 | 3 | 4 | 5 | | V-1 | Tm9sf2 |
| 18396 | 3 | 4 | 5 | | V-1 | Tmc1 |
| 18397 | 3 | 4 | 5 | | V-1 | Tmc5 |
| 18398 | 3 | 4 | 5 | | V-1 | Tmco4 |
| 18399 | 3 | 4 | 5 | | V-1 | Tmed2 |
| 18400 | 3 | 4 | 5 | | V-1 | Tmeff2 |
| 18401 | 3 | 4 | 5 | | V-1 | Tmem106c |
| 18402 | 3 | 4 | 5 | | V-1 | Tmem108 |
| 18403 | 3 | 4 | 5 | | V-1 | Tmem109 |
| 18404 | 3 | 4 | 5 | | V-1 | Tmem132a |
| 18405 | 3 | 4 | 5 | | V-1 | Tmem132cos |
| 18406 | 3 | 4 | 5 | | V-1 | Tmem132d |
| 18407 | 3 | 4 | 5 | | V-1 | Tmem161a |
| 18408 | 3 | 4 | 5 | | V-1 | Tmem173 |
| 18409 | 3 | 4 | 5 | | V-1 | Tmem178b |
| 18410 | 3 | 4 | 5 | | V-1 | Tmem19 |
| 18411 | 3 | 4 | 5 | | V-1 | Tmem204 |
| 18412 | 3 | 4 | 5 | | V-1 | Tmem27 |
| 18413 | 3 | 4 | 5 | | V-1 | Tmem41b |
| 18414 | 3 | 4 | 5 | | V-1 | Tmem44 |
| 18415 | 3 | 4 | 5 | | V-1 | Tmem45a |
| 18416 | 3 | 4 | 5 | | V-1 | Tmem51os1 |
| 18417 | 3 | 4 | 5 | | V-1 | Tmem52b |
| 18418 | 3 | 4 | 5 | | V-1 | Tmem55b |
| 18419 | 3 | 4 | 5 | | V-1 | Tmem59 |
| 18420 | 3 | 4 | 5 | | V-1 | Tmem63c |
| 18421 | 3 | 4 | 5 | | V-1 | Tmem66 |
| 18422 | 3 | 4 | 5 | | V-1 | Tmem81 |
| 18423 | 3 | 4 | 5 | | V-1 | Tmem89 |
| 18424 | 3 | 4 | 5 | | V-1 | Tmprss11a |
| 18425 | 3 | 4 | 5 | | V-1 | Tmprss11bnl |
| 18426 | 3 | 4 | 5 | | V-1 | Tmprss7 |
| 18427 | 3 | 4 | 5 | | V-1 | Tmub2 |
| 18428 | 3 | 4 | 5 | | V-1 | Tnfaip8l3 |
| 18429 | 3 | 4 | 5 | | V-1 | Tnn |
| 18430 | 3 | 4 | 5 | | V-1 | Tnpo2 |

Fig. 34 - 97

| | | | | | | | |
|---|---|---|---|---|---|---|---|
| 18431 | 3 | 4 | 5 | | V-1 | Tnrc18 | |
| 18432 | 3 | 4 | 5 | | V-1 | Tnrc6a | |
| 18433 | 3 | 4 | 5 | | V-1 | Tox4 | |
| 18434 | 3 | 4 | 5 | | V-1 | Traf5 | |
| 18435 | 3 | 4 | 5 | | V-1 | Tram1 | |
| 18436 | 3 | 4 | 5 | | V-1 | Trappc12 | |
| 18437 | 3 | 4 | 5 | | V-1 | Treml2 | |
| 18438 | 3 | 4 | 5 | | V-1 | Trim31 | |
| 18439 | 3 | 4 | 5 | | V-1 | Trim40 | |
| 18440 | 3 | 4 | 5 | | V-1 | Trim47 | |
| 18441 | 3 | 4 | 5 | | V-1 | Trip10 | |
| 18442 | 3 | 4 | 5 | | V-1 | Trip4 | |
| 18443 | 3 | 4 | 5 | | V-1 | Trmt11 | |
| 18444 | 3 | 4 | 5 | | V-1 | Trmt12 | |
| 18445 | 3 | 4 | 5 | | V-1 | Trmt6 | |
| 18446 | 3 | 4 | 5 | | V-1 | Trpc1 | |
| 18447 | 3 | 4 | 5 | | V-1 | Trpc2 | |
| 18448 | 3 | 4 | 5 | | V-1 | Trpm3 | |
| 18449 | 3 | 4 | 5 | | V-1 | Tsen34 | |
| 18450 | 3 | 4 | 5 | | V-1 | Tshz3 | |
| 18451 | 3 | 4 | 5 | | V-1 | Tsn | |
| 18452 | 3 | 4 | 5 | | V-1 | Tspan10 | |
| 18453 | 3 | 4 | 5 | | V-1 | Tssk5 | |
| 18454 | 3 | 4 | 5 | | V-1 | Ttbk1 | |
| 18455 | 3 | 4 | 5 | | V-1 | Ttc18 | |
| 18456 | 3 | 4 | 5 | | V-1 | Ttc19 | |
| 18457 | 3 | 4 | 5 | | V-1 | Ttc22 | |
| 18458 | 3 | 4 | 5 | | V-1 | Ttc3 | |
| 18459 | 3 | 4 | 5 | | V-1 | Ttc38 | |
| 18460 | 3 | 4 | 5 | | V-1 | Ttc4 | |
| 18461 | 3 | 4 | 5 | | V-1 | Ttll12 | |
| 18462 | 3 | 4 | 5 | | V-1 | Ttll3 | |
| 18463 | 3 | 4 | 5 | | V-1 | Ttll5 | |
| 18464 | 3 | 4 | 5 | | V-1 | Ttll9 | |
| 18465 | 3 | 4 | 5 | | V-1 | Ttn | |
| 18466 | 3 | 4 | 5 | | V-1 | Ttpal | |
| 18467 | 3 | 4 | 5 | | V-1 | Tubg2 | |
| 18468 | 3 | 4 | 5 | | V-1 | Tubgcp4 | |
| 18469 | 3 | 4 | 5 | | V-1 | Tuft1 | |
| 18470 | 3 | 4 | 5 | | V-1 | Tusc2 | |
| 18471 | 3 | 4 | 5 | | V-1 | Tut1 | |
| 18472 | 3 | 4 | 5 | | V-1 | Tvp23a | |
| 18473 | 3 | 4 | 5 | | V-1 | Twistnb | |
| 18474 | 3 | 4 | 5 | | V-1 | Txk | |
| 18475 | 3 | 4 | 5 | | V-1 | Txnrd1 | |
| 18476 | 3 | 4 | 5 | | V-1 | Uba1y | |
| 18477 | 3 | 4 | 5 | | V-1 | Ubap2 | |
| 18478 | 3 | 4 | 5 | | V-1 | Ube2d2a | |
| 18479 | 3 | 4 | 5 | | V-1 | Ube2d3 | |
| 18480 | 3 | 4 | 5 | | V-1 | Ube2e3 | |
| 18481 | 3 | 4 | 5 | | V-1 | Ube2i | |
| 18482 | 3 | 4 | 5 | | V-1 | Ube2k | |
| 18483 | 3 | 4 | 5 | | V-1 | Ubxn4 | |
| 18484 | 3 | 4 | 5 | | V-1 | Ubxn8 | |
| 18485 | 3 | 4 | 5 | | V-1 | Uck1 | |
| 18486 | 3 | 4 | 5 | | V-1 | Ufsp1 | |
| 18487 | 3 | 4 | 5 | | V-1 | Uggt1 | |
| 18488 | 3 | 4 | 5 | | V-1 | Ugt1a5 | |
| 18489 | 3 | 4 | 5 | | V-1 | Ugt2b37 | |
| 18490 | 3 | 4 | 5 | | V-1 | Ulk2 | |
| 18491 | 3 | 4 | 5 | | V-1 | Upf2 | |
| 18492 | 3 | 4 | 5 | | V-1 | Upk2 | |
| 18493 | 3 | 4 | 5 | | V-1 | Uprt | |
| 18494 | 3 | 4 | 5 | | V-1 | Uri1 | |
| 18495 | 3 | 4 | 5 | | V-1 | Usp26 | |
| 18496 | 3 | 4 | 5 | | V-1 | Usp28 | |
| 18497 | 3 | 4 | 5 | | V-1 | Usp29 | |
| 18498 | 3 | 4 | 5 | | V-1 | Usp33 | |
| 18499 | 3 | 4 | 5 | | V-1 | Vangl1 | |
| 18500 | 3 | 4 | 5 | | V-1 | Vash2 | |
| 18501 | 3 | 4 | 5 | | V-1 | Vasp | |
| 18502 | 3 | 4 | 5 | | V-1 | Vat1 | |
| 18503 | 3 | 4 | 5 | | V-1 | Vav2 | |
| 18504 | 3 | 4 | 5 | | V-1 | Vax2 | |
| 18505 | 3 | 4 | 5 | | V-1 | Vdac2 | |
| 18506 | 3 | 4 | 5 | | V-1 | Vhl | |
| 18507 | 3 | 4 | 5 | | V-1 | Vip | |
| 18508 | 3 | 4 | 5 | | V-1 | Vit | |
| 18509 | 3 | 4 | 5 | | V-1 | Vmn2r-ps159 | |
| 18510 | 3 | 4 | 5 | | V-1 | Vmn2r4 | |
| 18511 | 3 | 4 | 5 | | V-1 | Vps13a | |
| 18512 | 3 | 4 | 5 | | V-1 | Vps18 | |
| 18513 | 3 | 4 | 5 | | V-1 | Vps37b | |
| 18514 | 3 | 4 | 5 | | V-1 | Vps4b | |
| 18515 | 3 | 4 | 5 | | V-1 | Vtcn1 | |
| 18516 | 3 | 4 | 5 | | V-1 | Vwa8 | |
| 18517 | 3 | 4 | 5 | | V-1 | Vwce | |
| 18518 | 3 | 4 | 5 | | V-1 | Wac | |
| 18519 | 3 | 4 | 5 | | V-1 | Wbp4 | |
| 18520 | 3 | 4 | 5 | | V-1 | Wbscr28 | |
| 18521 | 3 | 4 | 5 | | V-1 | Wdfy1 | |
| 18522 | 3 | 4 | 5 | | V-1 | Wdfy4 | |
| 18523 | 3 | 4 | 5 | | V-1 | Wdr25 | |
| 18524 | 3 | 4 | 5 | | V-1 | Wdr35 | |
| 18525 | 3 | 4 | 5 | | V-1 | Wdr4 | |
| 18526 | 3 | 4 | 5 | | V-1 | Wdr52 | |
| 18527 | 3 | 4 | 5 | | V-1 | Wdr96 | |
| 18528 | 3 | 4 | 5 | | V-1 | Wfdc11 | |
| 18529 | 3 | 4 | 5 | | V-1 | Wfdc5 | |
| 18530 | 3 | 4 | 5 | | V-1 | Wfs1 | |
| 18531 | 3 | 4 | 5 | | V-1 | Wnt1 | |
| 18532 | 3 | 4 | 5 | | V-1 | Wnt16 | |
| 18533 | 3 | 4 | 5 | | V-1 | Wnt7b | |
| 18534 | 3 | 4 | 5 | | V-1 | Wnt9a | |
| 18535 | 3 | 4 | 5 | | V-1 | Xirp2 | |
| 18536 | 3 | 4 | 5 | | V-1 | Xkr7 | |
| 18537 | 3 | 4 | 5 | | V-1 | Xlr | |
| 18538 | 3 | 4 | 5 | | V-1 | Xpo6 | |
| 18539 | 3 | 4 | 5 | | V-1 | Xylb | |
| 18540 | 3 | 4 | 5 | | V-1 | Xylt1 | |
| 18541 | 3 | 4 | 5 | | V-1 | Ybey | |
| 18542 | 3 | 4 | 5 | | V-1 | Yme1l1 | |
| 18543 | 3 | 4 | 5 | | V-1 | Ythdf1 | |
| 18544 | 3 | 4 | 5 | | V-1 | Ywhae | |
| 18545 | 3 | 4 | 5 | | V-1 | Yy1 | |
| 18546 | 3 | 4 | 5 | | V-1 | Zan | |
| 18547 | 3 | 4 | 5 | | V-1 | Zbtb2 | |
| 18548 | 3 | 4 | 5 | | V-1 | Zc3h12c | |
| 18549 | 3 | 4 | 5 | | V-1 | Zc3h8 | |
| 18550 | 3 | 4 | 5 | | V-1 | Zcchc24 | |
| 18551 | 3 | 4 | 5 | | V-1 | Zcchc7 | |
| 18552 | 3 | 4 | 5 | | V-1 | Zdbf2 | |
| 18553 | 3 | 4 | 5 | | V-1 | Zdhhc3 | |
| 18554 | 3 | 4 | 5 | | V-1 | Zdhhc5 | |
| 18555 | 3 | 4 | 5 | | V-1 | Zfc3h1 | |
| 18556 | 3 | 4 | 5 | | V-1 | Zfp105 | |
| 18557 | 3 | 4 | 5 | | V-1 | Zfp112 | |
| 18558 | 3 | 4 | 5 | | V-1 | Zfp189 | |
| 18559 | 3 | 4 | 5 | | V-1 | Zfp202 | |
| 18560 | 3 | 4 | 5 | | V-1 | Zfp213 | |
| 18561 | 3 | 4 | 5 | | V-1 | Zfp248 | |
| 18562 | 3 | 4 | 5 | | V-1 | Zfp273 | |
| 18563 | 3 | 4 | 5 | | V-1 | Zfp275 | |
| 18564 | 3 | 4 | 5 | | V-1 | Zfp286 | |
| 18565 | 3 | 4 | 5 | | V-1 | Zfp287 | |
| 18566 | 3 | 4 | 5 | | V-1 | Zfp326 | |
| 18567 | 3 | 4 | 5 | | V-1 | Zfp334 | |
| 18568 | 3 | 4 | 5 | | V-1 | Zfp341 | |
| 18569 | 3 | 4 | 5 | | V-1 | Zfp354a | |
| 18570 | 3 | 4 | 5 | | V-1 | Zfp354b | |
| 18571 | 3 | 4 | 5 | | V-1 | Zfp354c | |
| 18572 | 3 | 4 | 5 | | V-1 | Zfp37 | |
| 18573 | 3 | 4 | 5 | | V-1 | Zfp39 | |
| 18574 | 3 | 4 | 5 | | V-1 | Zfp407 | |
| 18575 | 3 | 4 | 5 | | V-1 | Zfp420 | |
| 18576 | 3 | 4 | 5 | | V-1 | Zfp442 | |
| 18577 | 3 | 4 | 5 | | V-1 | Zfp446 | |
| 18578 | 3 | 4 | 5 | | V-1 | Zfp455 | |
| 18579 | 3 | 4 | 5 | | V-1 | Zfp456 | |
| 18580 | 3 | 4 | 5 | | V-1 | Zfp459 | |
| 18581 | 3 | 4 | 5 | | V-1 | Zfp462 | |
| 18582 | 3 | 4 | 5 | | V-1 | Zfp521 | |
| 18583 | 3 | 4 | 5 | | V-1 | Zfp583 | |
| 18584 | 3 | 4 | 5 | | V-1 | Zfp592 | |
| 18585 | 3 | 4 | 5 | | V-1 | Zfp608 | |
| 18586 | 3 | 4 | 5 | | V-1 | Zfp61 | |
| 18587 | 3 | 4 | 5 | | V-1 | Zfp629 | |
| 18588 | 3 | 4 | 5 | | V-1 | Zfp639 | |
| 18589 | 3 | 4 | 5 | | V-1 | Zfp719 | |
| 18590 | 3 | 4 | 5 | | V-1 | Zfp748 | |
| 18591 | 3 | 4 | 5 | | V-1 | Zfp759 | |
| 18592 | 3 | 4 | 5 | | V-1 | Zfp764 | |
| 18593 | 3 | 4 | 5 | | V-1 | Zfp784 | |
| 18594 | 3 | 4 | 5 | | V-1 | Zfp787 | |
| 18595 | 3 | 4 | 5 | | V-1 | Zfp811 | |
| 18596 | 3 | 4 | 5 | | V-1 | Zfp87 | |
| 18597 | 3 | 4 | 5 | | V-1 | Zfp872 | |
| 18598 | 3 | 4 | 5 | | V-1 | Zfp879 | |
| 18599 | 3 | 4 | 5 | | V-1 | Zfp90 | |
| 18600 | 3 | 4 | 5 | | V-1 | Zfp93 | |
| 18601 | 3 | 4 | 5 | | V-1 | Zfp930 | |
| 18602 | 3 | 4 | 5 | | V-1 | Zfp932 | |
| 18603 | 3 | 4 | 5 | | V-1 | Zfp934 | |
| 18604 | 3 | 4 | 5 | | V-1 | Zfp944 | |
| 18605 | 3 | 4 | 5 | | V-1 | Zfp956 | |
| 18606 | 3 | 4 | 5 | | V-1 | Zfpm1 | |
| 18607 | 3 | 4 | 5 | | V-1 | Zfpm2 | |
| 18608 | 3 | 4 | 5 | | V-1 | Zfr2 | |
| 18609 | 3 | 4 | 5 | | V-1 | Zfyve27 | |
| 18610 | 3 | 4 | 5 | | V-1 | Zic2 | |
| 18611 | 3 | 4 | 5 | | V-1 | Zkscan1 | |
| 18612 | 3 | 4 | 5 | | V-1 | Zkscan16 | |
| 18613 | 3 | 4 | 5 | | V-1 | Zkscan2 | |
| 18614 | 3 | 4 | 5 | | V-1 | Zmiz2 | |
| 18615 | 3 | 4 | 5 | | V-1 | Zmym1 | |
| 18616 | 3 | 4 | 5 | | V-1 | Zmym4 | |
| 18617 | 3 | 4 | 5 | | V-1 | Zmynd12 | |
| 18618 | 3 | 4 | 5 | | V-1 | Zmynd8 | |
| 18619 | 3 | 4 | 5 | | V-1 | Zrsr2 | |
| 18620 | 3 | 4 | 5 | | V-1 | Zswim8 | |
| 18621 | 3 | 4 | 5 | | V-1 | Zw10 | |
| 18622 | 3 | 4 | | | IV-2 | 1700013H16Rik | |

Fig. 34 - 98

| | | | | | | |
|---|---|---|---|---|---|---|
| 18623 | 3 | 4 | | | IV-2 | 1700017N19Rik |
| 18624 | 3 | 4 | | | IV-2 | 1700020G17Rik |
| 18625 | 3 | 4 | | | IV-2 | 1700025M24Rik |
| 18626 | 3 | 4 | | | IV-2 | 1700029J03Rik |
| 18627 | 3 | 4 | | | IV-2 | 1700030M09Rik |
| 18628 | 3 | 4 | | | IV-2 | 1700036G14Rik |
| 18629 | 3 | 4 | | | IV-2 | 1700051A21Rik |
| 18630 | 3 | 4 | | | IV-2 | 1700052J22Rik |
| 18631 | 3 | 4 | | | IV-2 | 1700065D16Rik |
| 18632 | 3 | 4 | | | IV-2 | 1700065I16Rik |
| 18633 | 3 | 4 | | | IV-2 | 1700065O20Rik |
| 18634 | 3 | 4 | | | IV-2 | 1700072O05Rik |
| 18635 | 3 | 4 | | | IV-2 | 1700094M24Rik |
| 18636 | 3 | 4 | | | IV-2 | 1700101O22Rik |
| 18637 | 3 | 4 | | | IV-2 | 2310005A03Rik |
| 18638 | 3 | 4 | | | IV-2 | 2310030A07Rik |
| 18639 | 3 | 4 | | | IV-2 | 2310079G19Rik |
| 18640 | 3 | 4 | | | IV-2 | 2410007B07Rik |
| 18641 | 3 | 4 | | | IV-2 | 2610028E06Rik |
| 18642 | 3 | 4 | | | IV-2 | 2810047C21Rik1 |
| 18643 | 3 | 4 | | | IV-2 | 2900092C05Rik |
| 18644 | 3 | 4 | | | IV-2 | 3010001F23Rik |
| 18645 | 3 | 4 | | | IV-2 | 4930430F21Rik |
| 18646 | 3 | 4 | | | IV-2 | 4930432J09Rik |
| 18647 | 3 | 4 | | | IV-2 | 4930452G13Rik |
| 18648 | 3 | 4 | | | IV-2 | 4930470P17Rik |
| 18649 | 3 | 4 | | | IV-2 | 4930473O22Rik |
| 18650 | 3 | 4 | | | IV-2 | 4930507D05Rik |
| 18651 | 3 | 4 | | | IV-2 | 4930509E16Rik |
| 18652 | 3 | 4 | | | IV-2 | 4930522H14Rik |
| 18653 | 3 | 4 | | | IV-2 | 4930524B15Rik |
| 18654 | 3 | 4 | | | IV-2 | 4930525D18Rik |
| 18655 | 3 | 4 | | | IV-2 | 4930552N02Rik |
| 18656 | 3 | 4 | | | IV-2 | 4930572O03Rik |
| 18657 | 3 | 4 | | | IV-2 | 4930592I03Rik |
| 18658 | 3 | 4 | | | IV-2 | 4931440J10Rik |
| 18659 | 3 | 4 | | | IV-2 | 4933401H06Rik |
| 18660 | 3 | 4 | | | IV-2 | 4933411G11Rik |
| 18661 | 3 | 4 | | | IV-2 | 4933413L06Rik |
| 18662 | 3 | 4 | | | IV-2 | 4933425L06Rik |
| 18663 | 3 | 4 | | | IV-2 | 5031425F14Rik |
| 18664 | 3 | 4 | | | IV-2 | 5330434G04Rik |
| 18665 | 3 | 4 | | | IV-2 | 5430401F13Rik |
| 18666 | 3 | 4 | | | IV-2 | 5430437J10Rik |
| 18667 | 3 | 4 | | | IV-2 | 6330407A03Rik |
| 18668 | 3 | 4 | | | IV-2 | 7530416G11Rik |
| 18669 | 3 | 4 | | | IV-2 | 9130209A04Rik |
| 18670 | 3 | 4 | | | IV-2 | 9430041J12Rik |
| 18671 | 3 | 4 | | | IV-2 | 9430060I03Rik |
| 18672 | 3 | 4 | | | IV-2 | 9430069I07Rik |
| 18673 | 3 | 4 | | | IV-2 | 9630028B13Rik |
| 18674 | 3 | 4 | | | IV-2 | A230009B12Rik |
| 18675 | 3 | 4 | | | IV-2 | A230020G21Rik |
| 18676 | 3 | 4 | | | IV-2 | A230057D06Rik |
| 18677 | 3 | 4 | | | IV-2 | A230073K19Rik |
| 18678 | 3 | 4 | | | IV-2 | A230108P19Rik |
| 18679 | 3 | 4 | | | IV-2 | A330033J07Rik |
| 18680 | 3 | 4 | | | IV-2 | A330076C08Rik |
| 18681 | 3 | 4 | | | IV-2 | A330076H08Rik |
| 18682 | 3 | 4 | | | IV-2 | A630019J02Rik |
| 18683 | 3 | 4 | | | IV-2 | A730090H04Rik |
| 18684 | 3 | 4 | | | IV-2 | A930003O13Rik |
| 18685 | 3 | 4 | | | IV-2 | AU015836 |
| 18686 | 3 | 4 | | | IV-2 | Adarb2 |
| 18687 | 3 | 4 | | | IV-2 | Aff2 |
| 18688 | 3 | 4 | | | IV-2 | Ang2 |
| 18689 | 3 | 4 | | | IV-2 | Ankrd34c |
| 18690 | 3 | 4 | | | IV-2 | Ano4 |
| 18691 | 3 | 4 | | | IV-2 | Antxr1 |
| 18692 | 3 | 4 | | | IV-2 | Asxl3 |
| 18693 | 3 | 4 | | | IV-2 | Atf7ip2 |
| 18694 | 3 | 4 | | | IV-2 | Atp6v1b1 |
| 18695 | 3 | 4 | | | IV-2 | Bsph2 |
| 18696 | 3 | 4 | | | IV-2 | C030023E24Rik |
| 18697 | 3 | 4 | | | IV-2 | C130021I20Rik |
| 18698 | 3 | 4 | | | IV-2 | C130060K24Rik |
| 18699 | 3 | 4 | | | IV-2 | Capn11 |
| 18700 | 3 | 4 | | | IV-2 | Ccdc169 |
| 18701 | 3 | 4 | | | IV-2 | Cdh6 |
| 18702 | 3 | 4 | | | IV-2 | Clec4f |
| 18703 | 3 | 4 | | | IV-2 | Cntn5 |
| 18704 | 3 | 4 | | | IV-2 | Cntnap3 |
| 18705 | 3 | 4 | | | IV-2 | Cntnap5a |
| 18706 | 3 | 4 | | | IV-2 | Col24a1 |
| 18707 | 3 | 4 | | | IV-2 | Cpxcr1 |
| 18708 | 3 | 4 | | | IV-2 | Cyp2d34 |
| 18709 | 3 | 4 | | | IV-2 | D030047H15Rik |
| 18710 | 3 | 4 | | | IV-2 | D330045A20Rik |
| 18711 | 3 | 4 | | | IV-2 | D830026I12Rik |
| 18712 | 3 | 4 | | | IV-2 | D930007P13Rik |
| 18713 | 3 | 4 | | | IV-2 | Dach2 |
| 18714 | 3 | 4 | | | IV-2 | Dcc |
| 18715 | 3 | 4 | | | IV-2 | Defa6 |
| 18716 | 3 | 4 | | | IV-2 | Dlgap2 |
| 18717 | 3 | 4 | | | IV-2 | Dll3 |
| 18718 | 3 | 4 | | | IV-2 | Dmc1 |
| 18719 | 3 | 4 | | | IV-2 | Dnmt3aos |
| 18720 | 3 | 4 | | | IV-2 | E330012B07Rik |
| 18721 | 3 | 4 | | | IV-2 | E330017A01Rik |
| 18722 | 3 | 4 | | | IV-2 | E330021D16Rik |
| 18723 | 3 | 4 | | | IV-2 | E430016F16Rik |
| 18724 | 3 | 4 | | | IV-2 | Egfem1 |
| 18725 | 3 | 4 | | | IV-2 | Erbb4 |
| 18726 | 3 | 4 | | | IV-2 | Evx1 |
| 18727 | 3 | 4 | | | IV-2 | F11 |
| 18728 | 3 | 4 | | | IV-2 | Fam162b |
| 18729 | 3 | 4 | | | IV-2 | Fanca |
| 18730 | 3 | 4 | | | IV-2 | Fbxw15 |
| 18731 | 3 | 4 | | | IV-2 | Fbxw18 |
| 18732 | 3 | 4 | | | IV-2 | Fezf1 |
| 18733 | 3 | 4 | | | IV-2 | Fgf20 |
| 18734 | 3 | 4 | | | IV-2 | Fgf8 |
| 18735 | 3 | 4 | | | IV-2 | Fndc8 |
| 18736 | 3 | 4 | | | IV-2 | Foxi3 |
| 18737 | 3 | 4 | | | IV-2 | Gabrg3 |
| 18738 | 3 | 4 | | | IV-2 | Gabrr1 |
| 18739 | 3 | 4 | | | IV-2 | Galnt13 |
| 18740 | 3 | 4 | | | IV-2 | Gcm1 |
| 18741 | 3 | 4 | | | IV-2 | Gdf7 |
| 18742 | 3 | 4 | | | IV-2 | Gdpd4 |
| 18743 | 3 | 4 | | | IV-2 | Gm10324 |
| 18744 | 3 | 4 | | | IV-2 | Gm10619 |
| 18745 | 3 | 4 | | | IV-2 | Gm10865 |
| 18746 | 3 | 4 | | | IV-2 | Gm1110 |
| 18747 | 3 | 4 | | | IV-2 | Gm11437 |
| 18748 | 3 | 4 | | | IV-2 | Gm11978 |
| 18749 | 3 | 4 | | | IV-2 | Gm12522 |
| 18750 | 3 | 4 | | | IV-2 | Gm12530 |
| 18751 | 3 | 4 | | | IV-2 | Gm12633 |
| 18752 | 3 | 4 | | | IV-2 | Gm13003 |
| 18753 | 3 | 4 | | | IV-2 | Gm13031 |
| 18754 | 3 | 4 | | | IV-2 | Gm13032 |
| 18755 | 3 | 4 | | | IV-2 | Gm13238 |
| 18756 | 3 | 4 | | | IV-2 | Gm13285 |
| 18757 | 3 | 4 | | | IV-2 | Gm14204 |
| 18758 | 3 | 4 | | | IV-2 | Gm15091 |
| 18759 | 3 | 4 | | | IV-2 | Gm15348 |
| 18760 | 3 | 4 | | | IV-2 | Gm15386 |
| 18761 | 3 | 4 | | | IV-2 | Gm1553 |
| 18762 | 3 | 4 | | | IV-2 | Gm15910 |
| 18763 | 3 | 4 | | | IV-2 | Gm16130 |
| 18764 | 3 | 4 | | | IV-2 | Gm16386 |
| 18765 | 3 | 4 | | | IV-2 | Gm16702 |
| 18766 | 3 | 4 | | | IV-2 | Gm17365 |
| 18767 | 3 | 4 | | | IV-2 | Gm1968 |
| 18768 | 3 | 4 | | | IV-2 | Gm20199 |
| 18769 | 3 | 4 | | | IV-2 | Gm20735 |
| 18770 | 3 | 4 | | | IV-2 | Gm20754 |
| 18771 | 3 | 4 | | | IV-2 | Gm2087 |
| 18772 | 3 | 4 | | | IV-2 | Gm2176 |
| 18773 | 3 | 4 | | | IV-2 | Gm2721 |
| 18774 | 3 | 4 | | | IV-2 | Gm362 |
| 18775 | 3 | 4 | | | IV-2 | Gm3985 |
| 18776 | 3 | 4 | | | IV-2 | Gm4541 |
| 18777 | 3 | 4 | | | IV-2 | Gm4745 |
| 18778 | 3 | 4 | | | IV-2 | Gm5089 |
| 18779 | 3 | 4 | | | IV-2 | Gm5168 |
| 18780 | 3 | 4 | | | IV-2 | Gm5766 |
| 18781 | 3 | 4 | | | IV-2 | Gm6260 |
| 18782 | 3 | 4 | | | IV-2 | Gm6815 |
| 18783 | 3 | 4 | | | IV-2 | Gm6890 |
| 18784 | 3 | 4 | | | IV-2 | Gm765 |
| 18785 | 3 | 4 | | | IV-2 | Gm773 |
| 18786 | 3 | 4 | | | IV-2 | Gm7854 |
| 18787 | 3 | 4 | | | IV-2 | Gm806 |
| 18788 | 3 | 4 | | | IV-2 | Gm8773 |
| 18789 | 3 | 4 | | | IV-2 | Gm9573 |
| 18790 | 3 | 4 | | | IV-2 | Gm9961 |
| 18791 | 3 | 4 | | | IV-2 | Gm9962 |
| 18792 | 3 | 4 | | | IV-2 | Gmnc |
| 18793 | 3 | 4 | | | IV-2 | Gpr101 |
| 18794 | 3 | 4 | | | IV-2 | Gpr165 |
| 18795 | 3 | 4 | | | IV-2 | Gpr31b |
| 18796 | 3 | 4 | | | IV-2 | Gpr52 |
| 18797 | 3 | 4 | | | IV-2 | Grid2ip |
| 18798 | 3 | 4 | | | IV-2 | Grm6 |
| 18799 | 3 | 4 | | | IV-2 | Grpr |
| 18800 | 3 | 4 | | | IV-2 | Gucy2e |
| 18801 | 3 | 4 | | | IV-2 | Hand1 |
| 18802 | 3 | 4 | | | IV-2 | Hoxc11 |
| 18803 | 3 | 4 | | | IV-2 | Hoxd13 |
| 18804 | 3 | 4 | | | IV-2 | Htr1f |
| 18805 | 3 | 4 | | | IV-2 | Ifnk |
| 18806 | 3 | 4 | | | IV-2 | Il1rapl1 |
| 18807 | 3 | 4 | | | IV-2 | Il1fb |
| 18808 | 3 | 4 | | | IV-2 | Kcna4 |
| 18809 | 3 | 4 | | | IV-2 | Kcnb2 |
| 18810 | 3 | 4 | | | IV-2 | Kcnh4 |
| 18811 | 3 | 4 | | | IV-2 | Kcnh5 |
| 18812 | 3 | 4 | | | IV-2 | Kcnj1 |
| 18813 | 3 | 4 | | | IV-2 | Kcnk15 |
| 18814 | 3 | 4 | | | IV-2 | Kcnq1ot1 |

Fig. 34 - 99

| | | | | | | | |
|---|---|---|---|---|---|---|---|
| 18815 | 3 | 4 | | | IV-2 | Kcnq3 | |
| 18816 | 3 | 4 | | | IV-2 | Kcnt2 | |
| 18817 | 3 | 4 | | | IV-2 | Klk15 | |
| 18818 | 3 | 4 | | | IV-2 | Klk4 | |
| 18819 | 3 | 4 | | | IV-2 | Klra15 | |
| 18820 | 3 | 4 | | | IV-2 | Klra9 | |
| 18821 | 3 | 4 | | | IV-2 | Klrb1 | |
| 18822 | 3 | 4 | | | IV-2 | L3mbtl1 | |
| 18823 | 3 | 4 | | | IV-2 | LOC102634753 | |
| 18824 | 3 | 4 | | | IV-2 | Lct | |
| 18825 | 3 | 4 | | | IV-2 | Lrp1b | |
| 18826 | 3 | 4 | | | IV-2 | Lrrc7 | |
| 18827 | 3 | 4 | | | IV-2 | Mageb18 | |
| 18828 | 3 | 4 | | | IV-2 | Mc3r | |
| 18829 | 3 | 4 | | | IV-2 | Mei4 | |
| 18830 | 3 | 4 | | | IV-2 | Mip | |
| 18831 | 3 | 4 | | | IV-2 | Myf5 | |
| 18832 | 3 | 4 | | | IV-2 | Nav3 | |
| 18833 | 3 | 4 | | | IV-2 | Ncam2 | |
| 18834 | 3 | 4 | | | IV-2 | Nespas | |
| 18835 | 3 | 4 | | | IV-2 | Nkain3 | |
| 18836 | 3 | 4 | | | IV-2 | Nlrp1c-ps | |
| 18837 | 3 | 4 | | | IV-2 | Nlrp4c | |
| 18838 | 3 | 4 | | | IV-2 | Nmur1 | |
| 18839 | 3 | 4 | | | IV-2 | Nmur2 | |
| 18840 | 3 | 4 | | | IV-2 | Npffr1 | |
| 18841 | 3 | 4 | | | IV-2 | Nr2e1 | |
| 18842 | 3 | 4 | | | IV-2 | Nr2e3 | |
| 18843 | 3 | 4 | | | IV-2 | Nron | |
| 18844 | 3 | 4 | | | IV-2 | Ntsr1 | |
| 18845 | 3 | 4 | | | IV-2 | Nxph2 | |
| 18846 | 3 | 4 | | | IV-2 | Nyap2 | |
| 18847 | 3 | 4 | | | IV-2 | Olfr1279 | |
| 18848 | 3 | 4 | | | IV-2 | Olfr1420 | |
| 18849 | 3 | 4 | | | IV-2 | Olfr1494 | |
| 18850 | 3 | 4 | | | IV-2 | Olfr19 | |
| 18851 | 3 | 4 | | | IV-2 | Olfr360 | |
| 18852 | 3 | 4 | | | IV-2 | Olfr872 | |
| 18853 | 3 | 4 | | | IV-2 | Pak7 | |
| 18854 | 3 | 4 | | | IV-2 | Pcdh11x | |
| 18855 | 3 | 4 | | | IV-2 | Pcdha12 | |
| 18856 | 3 | 4 | | | IV-2 | Pcdhb15 | |
| 18857 | 3 | 4 | | | IV-2 | Pcdhb16 | |
| 18858 | 3 | 4 | | | IV-2 | Pcdhb19 | |
| 18859 | 3 | 4 | | | IV-2 | Peg12 | |
| 18860 | 3 | 4 | | | IV-2 | Pglyrp3 | |
| 18861 | 3 | 4 | | | IV-2 | Phxr4 | |
| 18862 | 3 | 4 | | | IV-2 | Pira11 | |
| 18863 | 3 | 4 | | | IV-2 | Pkhd1 | |
| 18864 | 3 | 4 | | | IV-2 | Pkhd1l1 | |
| 18865 | 3 | 4 | | | IV-2 | Plag1 | |
| 18866 | 3 | 4 | | | IV-2 | Plxnb3 | |
| 18867 | 3 | 4 | | | IV-2 | Ppef2 | |
| 18868 | 3 | 4 | | | IV-2 | Prok1 | |
| 18869 | 3 | 4 | | | IV-2 | Prss52 | |
| 18870 | 3 | 4 | | | IV-2 | Psg16 | |
| 18871 | 3 | 4 | | | IV-2 | Psg17 | |
| 18872 | 3 | 4 | | | IV-2 | R3hdml | |
| 18873 | 3 | 4 | | | IV-2 | Rbbp8nl | |
| 18874 | 3 | 4 | | | IV-2 | Rdh19 | |
| 18875 | 3 | 4 | | | IV-2 | Rgag1 | |
| 18876 | 3 | 4 | | | IV-2 | Rgs9bp | |
| 18877 | 3 | 4 | | | IV-2 | Rhox3g | |
| 18878 | 3 | 4 | | | IV-2 | Rspo2 | |
| 18879 | 3 | 4 | | | IV-2 | Rxfp1 | |
| 18880 | 3 | 4 | | | IV-2 | Sept14 | |
| 18881 | 3 | 4 | | | IV-2 | Serpine3 | |
| 18882 | 3 | 4 | | | IV-2 | Sh2d1b2 | |
| 18883 | 3 | 4 | | | IV-2 | Sis | |
| 18884 | 3 | 4 | | | IV-2 | Slc6a20b | |
| 18885 | 3 | 4 | | | IV-2 | Slc6a5 | |
| 18886 | 3 | 4 | | | IV-2 | Slitrk2 | |
| 18887 | 3 | 4 | | | IV-2 | Smr3a | |
| 18888 | 3 | 4 | | | IV-2 | Sntg1 | |
| 18889 | 3 | 4 | | | IV-2 | Sp7 | |
| 18890 | 3 | 4 | | | IV-2 | Sp8 | |
| 18891 | 3 | 4 | | | IV-2 | Spin4 | |
| 18892 | 3 | 4 | | | IV-2 | Spink1 | |
| 18893 | 3 | 4 | | | IV-2 | Spry3 | |
| 18894 | 3 | 4 | | | IV-2 | Sstr4 | |
| 18895 | 3 | 4 | | | IV-2 | Ssxb8 | |
| 18896 | 3 | 4 | | | IV-2 | Stpg2 | |
| 18897 | 3 | 4 | | | IV-2 | Sult2a4 | |
| 18898 | 3 | 4 | | | IV-2 | Sun5 | |
| 18899 | 3 | 4 | | | IV-2 | Tcl1 | |
| 18900 | 3 | 4 | | | IV-2 | Tex28 | |
| 18901 | 3 | 4 | | | IV-2 | Tex29 | |
| 18902 | 3 | 4 | | | IV-2 | Thsd7b | |
| 18903 | 3 | 4 | | | IV-2 | Tmem174 | |
| 18904 | 3 | 4 | | | IV-2 | Tmem210 | |
| 18905 | 3 | 4 | | | IV-2 | Tnfsf4 | |
| 18906 | 3 | 4 | | | IV-2 | Tnr | |
| 18907 | 3 | 4 | | | IV-2 | Trhr | |
| 18908 | 3 | 4 | | | IV-2 | Trim43c | |
| 18909 | 3 | 4 | | | IV-2 | Trpa1 | |
| 18910 | 3 | 4 | | | IV-2 | Trpc5 | |
| 18911 | 3 | 4 | | | IV-2 | Tspear | |
| 18912 | 3 | 4 | | | IV-2 | Unc5d | |
| 18913 | 3 | 4 | | | IV-2 | V1ra8 | |
| 18914 | 3 | 4 | | | IV-2 | Vmn1r2 | |
| 18915 | 3 | 4 | | | IV-2 | Vmn1r21 | |
| 18916 | 3 | 4 | | | IV-2 | Vmn1r233 | |
| 18917 | 3 | 4 | | | IV-2 | Vmn2r5 | |
| 18918 | 3 | 4 | | | IV-2 | Vmn2r87 | |
| 18919 | 3 | 4 | | | IV-2 | Wisp3 | |
| 18920 | 3 | 4 | | | IV-2 | Xlr5c | |
| 18921 | 3 | 4 | | | IV-2 | Zcchc16 | |
| 18922 | 3 | 4 | | | IV-2 | Zdhhc25 | |
| 18923 | 3 | 4 | | | IV-2 | Zfp114 | |
| 18924 | 3 | 4 | | | IV-2 | Zfp300 | |
| 18925 | 3 | 4 | | | IV-2 | Zfp536 | |
| 18926 | 3 | 4 | | | IV-2 | Zfp92 | |
| 18927 | 3 | 4 | | | IV-2 | Znf41-ps | |
| 18928 | 3 | 4 | | | IV-2 | Zpld1 | |
| 18929 | 3 | 4 | | | IV-1 | 0610039K10Rik | |
| 18930 | 3 | 4 | | | IV-1 | 1110015O18Rik | |
| 18931 | 3 | 4 | | | IV-1 | 1600002D24Rik | |
| 18932 | 3 | 4 | | | IV-1 | 1600014K23Rik | |
| 18933 | 3 | 4 | | | IV-1 | 1600029O15Rik | |
| 18934 | 3 | 4 | | | IV-1 | 1700001P01Rik | |
| 18935 | 3 | 4 | | | IV-1 | 1700003G18Rik | |
| 18936 | 3 | 4 | | | IV-1 | 1700003P14Rik | |
| 18937 | 3 | 4 | | | IV-1 | 1700006F04Rik | |
| 18938 | 3 | 4 | | | IV-1 | 1700007814Rik | |
| 18939 | 3 | 4 | | | IV-1 | 1700008P02Rik | |
| 18940 | 3 | 4 | | | IV-1 | 1700016C15Rik | |
| 18941 | 3 | 4 | | | IV-1 | 1700016D06Rik | |
| 18942 | 3 | 4 | | | IV-1 | 1700017D01Rik | |
| 18943 | 3 | 4 | | | IV-1 | 1700017G19Rik | |
| 18944 | 3 | 4 | | | IV-1 | 1700018A04Rik | |
| 18945 | 3 | 4 | | | IV-1 | 1700018B08Rik | |
| 18946 | 3 | 4 | | | IV-1 | 1700019A02Rik | |
| 18947 | 3 | 4 | | | IV-1 | 1700019G24Rik | |
| 18948 | 3 | 4 | | | IV-1 | 1700019O17Rik | |
| 18949 | 3 | 4 | | | IV-1 | 1700020N15Rik | |
| 18950 | 3 | 4 | | | IV-1 | 1700022I11Rik | |
| 18951 | 3 | 4 | | | IV-1 | 1700023C21Rik | |
| 18952 | 3 | 4 | | | IV-1 | 1700023F02Rik | |
| 18953 | 3 | 4 | | | IV-1 | 1700025B11Rik | |
| 18954 | 3 | 4 | | | IV-1 | 1700025C18Rik | |
| 18955 | 3 | 4 | | | IV-1 | 1700025F22Rik | |
| 18956 | 3 | 4 | | | IV-1 | 1700027F09Rik | |
| 18957 | 3 | 4 | | | IV-1 | 1700028D13Rik | |
| 18958 | 3 | 4 | | | IV-1 | 1700028E10Rik | |
| 18959 | 3 | 4 | | | IV-1 | 1700029M20Rik | |
| 18960 | 3 | 4 | | | IV-1 | 1700030N03Rik | |
| 18961 | 3 | 4 | | | IV-1 | 1700031M16Rik | |
| 18962 | 3 | 4 | | | IV-1 | 1700034H15Rik | |
| 18963 | 3 | 4 | | | IV-1 | 1700039E22Rik | |
| 18964 | 3 | 4 | | | IV-1 | 1700042814Rik | |
| 18965 | 3 | 4 | | | IV-1 | 1700042G15Rik | |
| 18966 | 3 | 4 | | | IV-1 | 1700042O10Rik | |
| 18967 | 3 | 4 | | | IV-1 | 1700047A11Rik | |
| 18968 | 3 | 4 | | | IV-1 | 1700047E10Rik | |
| 18969 | 3 | 4 | | | IV-1 | 1700047L14Rik | |
| 18970 | 3 | 4 | | | IV-1 | 1700049E22Rik | |
| 18971 | 3 | 4 | | | IV-1 | 1700061F12Rik | |
| 18972 | 3 | 4 | | | IV-1 | 1700061G19Rik | |
| 18973 | 3 | 4 | | | IV-1 | 1700061I17Rik | |
| 18974 | 3 | 4 | | | IV-1 | 1700065L07Rik | |
| 18975 | 3 | 4 | | | IV-1 | 1700071K01Rik | |
| 18976 | 3 | 4 | | | IV-1 | 1700073E17Rik | |
| 18977 | 3 | 4 | | | IV-1 | 1700074H08Rik | |
| 18978 | 3 | 4 | | | IV-1 | 1700080O16Rik | |
| 18979 | 3 | 4 | | | IV-1 | 1700081H04Rik | |
| 18980 | 3 | 4 | | | IV-1 | 1700085C21Rik | |
| 18981 | 3 | 4 | | | IV-1 | 1700091H14Rik | |
| 18982 | 3 | 4 | | | IV-1 | 1700096J18Rik | |
| 18983 | 3 | 4 | | | IV-1 | 1700106J16Rik | |
| 18984 | 3 | 4 | | | IV-1 | 1700108F19Rik | |
| 18985 | 3 | 4 | | | IV-1 | 1700109G14Rik | |
| 18986 | 3 | 4 | | | IV-1 | 1700109I08Rik | |
| 18987 | 3 | 4 | | | IV-1 | 1700110C19Rik | |
| 18988 | 3 | 4 | | | IV-1 | 1700112H15Rik | |
| 18989 | 3 | 4 | | | IV-1 | 1700112I05Rik | |
| 18990 | 3 | 4 | | | IV-1 | 1700120E14Rik | |
| 18991 | 3 | 4 | | | IV-1 | 1700123K08Rik | |
| 18992 | 3 | 4 | | | IV-1 | 1700125G22Rik | |
| 18993 | 3 | 4 | | | IV-1 | 1700126H18Rik | |
| 18994 | 3 | 4 | | | IV-1 | 1700128F08Rik | |
| 18995 | 3 | 4 | | | IV-1 | 1810006J02Rik | |
| 18996 | 3 | 4 | | | IV-1 | 1810024B03Rik | |
| 18997 | 3 | 4 | | | IV-1 | 2210019I11Rik | |
| 18998 | 3 | 4 | | | IV-1 | 2310043O21Rik | |
| 18999 | 3 | 4 | | | IV-1 | 2610035F20Rik | |
| 19000 | 3 | 4 | | | IV-1 | 2610206C17Rik | |
| 19001 | 3 | 4 | | | IV-1 | 2610207O16Rik | |
| 19002 | 3 | 4 | | | IV-1 | 2610307P16Rik | |
| 19003 | 3 | 4 | | | IV-1 | 2700046A07Rik | |
| 19004 | 3 | 4 | | | IV-1 | 2700054A10Rik | |
| 19005 | 3 | 4 | | | IV-1 | 2810408M09Rik | |
| 19006 | 3 | 4 | | | IV-1 | 3110021A11Rik | |

Fig. 34 - 100

| | | | | | | |
|---|---|---|---|---|---|---|
| 19007 | 3 | 4 | | | IV-1 | 4732456N10Rik |
| 19008 | 3 | 4 | | | IV-1 | 4831440E17Rik |
| 19009 | 3 | 4 | | | IV-1 | 4833424O15Rik |
| 19010 | 3 | 4 | | | IV-1 | 4833439L19Rik |
| 19011 | 3 | 4 | | | IV-1 | 4921501E09Rik |
| 19012 | 3 | 4 | | | IV-1 | 4921504E06Rik |
| 19013 | 3 | 4 | | | IV-1 | 4921511C20Rik |
| 19014 | 3 | 4 | | | IV-1 | 4921513I03Rik |
| 19015 | 3 | 4 | | | IV-1 | 4921515E04Rik |
| 19016 | 3 | 4 | | | IV-1 | 4921517D22Rik |
| 19017 | 3 | 4 | | | IV-1 | 4921530L21Rik |
| 19018 | 3 | 4 | | | IV-1 | 4921539E11Rik |
| 19019 | 3 | 4 | | | IV-1 | 4930402F06Rik |
| 19020 | 3 | 4 | | | IV-1 | 4930402K13Rik |
| 19021 | 3 | 4 | | | IV-1 | 4930404A10Rik |
| 19022 | 3 | 4 | | | IV-1 | 4930405D11Rik |
| 19023 | 3 | 4 | | | IV-1 | 4930406D18Rik |
| 19024 | 3 | 4 | | | IV-1 | 4930407I10Rik |
| 19025 | 3 | 4 | | | IV-1 | 4930413E15Rik |
| 19026 | 3 | 4 | | | IV-1 | 4930415L06Rik |
| 19027 | 3 | 4 | | | IV-1 | 4930417O13Rik |
| 19028 | 3 | 4 | | | IV-1 | 4930428E07Rik |
| 19029 | 3 | 4 | | | IV-1 | 4930428O21Rik |
| 19030 | 3 | 4 | | | IV-1 | 4930433B08Rik |
| 19031 | 3 | 4 | | | IV-1 | 4930433N12Rik |
| 19032 | 3 | 4 | | | IV-1 | 4930442J19Rik |
| 19033 | 3 | 4 | | | IV-1 | 4930442L01Rik |
| 19034 | 3 | 4 | | | IV-1 | 4930443O20Rik |
| 19035 | 3 | 4 | | | IV-1 | 4930444F02Rik |
| 19036 | 3 | 4 | | | IV-1 | 4930447J18Rik |
| 19037 | 3 | 4 | | | IV-1 | 4930459L07Rik |
| 19038 | 3 | 4 | | | IV-1 | 4930463O16Rik |
| 19039 | 3 | 4 | | | IV-1 | 4930467D21Rik |
| 19040 | 3 | 4 | | | IV-1 | 4930469G21Rik |
| 19041 | 3 | 4 | | | IV-1 | 4930471M09Rik |
| 19042 | 3 | 4 | | | IV-1 | 4930473A02Rik |
| 19043 | 3 | 4 | | | IV-1 | 4930478P22Rik |
| 19044 | 3 | 4 | | | IV-1 | 4930479D17Rik |
| 19045 | 3 | 4 | | | IV-1 | 4930483K19Rik |
| 19046 | 3 | 4 | | | IV-1 | 4930486I03Rik |
| 19047 | 3 | 4 | | | IV-1 | 4930487H11Rik |
| 19048 | 3 | 4 | | | IV-1 | 4930503O07Rik |
| 19049 | 3 | 4 | | | IV-1 | 4930515L19Rik |
| 19050 | 3 | 4 | | | IV-1 | 4930522O17Rik |
| 19051 | 3 | 4 | | | IV-1 | 4930524O08Rik |
| 19052 | 3 | 4 | | | IV-1 | 4930525M21Rik |
| 19053 | 3 | 4 | | | IV-1 | 4930526L06Rik |
| 19054 | 3 | 4 | | | IV-1 | 4930528D03Rik |
| 19055 | 3 | 4 | | | IV-1 | 4930529C04Rik |
| 19056 | 3 | 4 | | | IV-1 | 4930529M08Rik |
| 19057 | 3 | 4 | | | IV-1 | 4930539M17Rik |
| 19058 | 3 | 4 | | | IV-1 | 4930540M03Rik |
| 19059 | 3 | 4 | | | IV-1 | 4930542C21Rik |
| 19060 | 3 | 4 | | | IV-1 | 4930544M13Rik |
| 19061 | 3 | 4 | | | IV-1 | 4930545E07Rik |
| 19062 | 3 | 4 | | | IV-1 | 4930547E14Rik |
| 19063 | 3 | 4 | | | IV-1 | 4930548J01Rik |
| 19064 | 3 | 4 | | | IV-1 | 4930549C01Rik |
| 19065 | 3 | 4 | | | IV-1 | 4930549G23Rik |
| 19066 | 3 | 4 | | | IV-1 | 4930556C24Rik |
| 19067 | 3 | 4 | | | IV-1 | 4930557J02Rik |
| 19068 | 3 | 4 | | | IV-1 | 4930564C03Rik |
| 19069 | 3 | 4 | | | IV-1 | 4930564D02Rik |
| 19070 | 3 | 4 | | | IV-1 | 4930567H17Rik |
| 19071 | 3 | 4 | | | IV-1 | 4930567J20Rik |
| 19072 | 3 | 4 | | | IV-1 | 4930568D16Rik |
| 19073 | 3 | 4 | | | IV-1 | 4930568G15Rik |
| 19074 | 3 | 4 | | | IV-1 | 4930572K03Rik |
| 19075 | 3 | 4 | | | IV-1 | 4930572O13Rik |
| 19076 | 3 | 4 | | | IV-1 | 4930583P06Rik |
| 19077 | 3 | 4 | | | IV-1 | 4930584F24Rik |
| 19078 | 3 | 4 | | | IV-1 | 4930590J08Rik |
| 19079 | 3 | 4 | | | IV-1 | 4930592A05Rik |
| 19080 | 3 | 4 | | | IV-1 | 4930595M18Rik |
| 19081 | 3 | 4 | | | IV-1 | 4931403G20Rik |
| 19082 | 3 | 4 | | | IV-1 | 4931406B18Rik |
| 19083 | 3 | 4 | | | IV-1 | 4931408C20Rik |
| 19084 | 3 | 4 | | | IV-1 | 4931420L22Rik |
| 19085 | 3 | 4 | | | IV-1 | 4931429L15Rik |
| 19086 | 3 | 4 | | | IV-1 | 4931440F15Rik |
| 19087 | 3 | 4 | | | IV-1 | 4932415M13Rik |
| 19088 | 3 | 4 | | | IV-1 | 4932416K20Rik |
| 19089 | 3 | 4 | | | IV-1 | 4932418E24Rik |
| 19090 | 3 | 4 | | | IV-1 | 4933401D09Rik |
| 19091 | 3 | 4 | | | IV-1 | 4933402J10Rik |
| 19092 | 3 | 4 | | | IV-1 | 4933404K08Rik |
| 19093 | 3 | 4 | | | IV-1 | 4933406J08Rik |
| 19094 | 3 | 4 | | | IV-1 | 4933406M09Rik |
| 19095 | 3 | 4 | | | IV-1 | 4933407J05Rik |
| 19096 | 3 | 4 | | | IV-1 | 4933407K13Rik |
| 19097 | 3 | 4 | | | IV-1 | 4933408N05Rik |
| 19098 | 3 | 4 | | | IV-1 | 4933411E08Rik |
| 19099 | 3 | 4 | | | IV-1 | 4933411G06Rik |
| 19100 | 3 | 4 | | | IV-1 | 4933413G19Rik |
| 19101 | 3 | 4 | | | IV-1 | 4933413J09Rik |
| 19102 | 3 | 4 | | | IV-1 | 4933416C03Rik |
| 19103 | 3 | 4 | | | IV-1 | 4933416M06Rik |
| 19104 | 3 | 4 | | | IV-1 | 4933427D06Rik |
| 19105 | 3 | 4 | | | IV-1 | 4933429K18Rik |
| 19106 | 3 | 4 | | | IV-1 | 4933430H16Rik |
| 19107 | 3 | 4 | | | IV-1 | 4933430I17Rik |
| 19108 | 3 | 4 | | | IV-1 | 4933432I09Rik |
| 19109 | 3 | 4 | | | IV-1 | 4933433C11Rik |
| 19110 | 3 | 4 | | | IV-1 | 4933433H22Rik |
| 19111 | 3 | 4 | | | IV-1 | 4933436H12Rik |
| 19112 | 3 | 4 | | | IV-1 | 4933440M02Rik |
| 19113 | 3 | 4 | | | IV-1 | 5031414D18Rik |
| 19114 | 3 | 4 | | | IV-1 | 5330413P13Rik |
| 19115 | 3 | 4 | | | IV-1 | 5330417C22Rik |
| 19116 | 3 | 4 | | | IV-1 | 5330439B14Rik |
| 19117 | 3 | 4 | | | IV-1 | 5730480H06Rik |
| 19118 | 3 | 4 | | | IV-1 | 5730507C01Rik |
| 19119 | 3 | 4 | | | IV-1 | 5830416P10Rik |
| 19120 | 3 | 4 | | | IV-1 | 6030443J06Rik |
| 19121 | 3 | 4 | | | IV-1 | 6330410L21Rik |
| 19122 | 3 | 4 | | | IV-1 | 6720483E21Rik |
| 19123 | 3 | 4 | | | IV-1 | 9130019P16Rik |
| 19124 | 3 | 4 | | | IV-1 | 9230009I02Rik |
| 19125 | 3 | 4 | | | IV-1 | 9430021M05Rik |
| 19126 | 3 | 4 | | | IV-1 | 9630013A20Rik |
| 19127 | 3 | 4 | | | IV-1 | A330050F15Rik |
| 19128 | 3 | 4 | | | IV-1 | A330074K22Rik |
| 19129 | 3 | 4 | | | IV-1 | A530065N20Rik |
| 19130 | 3 | 4 | | | IV-1 | A630089N07Rik |
| 19131 | 3 | 4 | | | IV-1 | A730006G06Rik |
| 19132 | 3 | 4 | | | IV-1 | A730020E08Rik |
| 19133 | 3 | 4 | | | IV-1 | A730056A06Rik |
| 19134 | 3 | 4 | | | IV-1 | A930012L18Rik |
| 19135 | 3 | 4 | | | IV-1 | A930041C12Rik |
| 19136 | 3 | 4 | | | IV-1 | AF366264 |
| 19137 | 3 | 4 | | | IV-1 | AF529169 |
| 19138 | 3 | 4 | | | IV-1 | AI115009 |
| 19139 | 3 | 4 | | | IV-1 | AI506816 |
| 19140 | 3 | 4 | | | IV-1 | AU015228 |
| 19141 | 3 | 4 | | | IV-1 | AU018091 |
| 19142 | 3 | 4 | | | IV-1 | AU022751 |
| 19143 | 3 | 4 | | | IV-1 | AU022754 |
| 19144 | 3 | 4 | | | IV-1 | AW551984 |
| 19145 | 3 | 4 | | | IV-1 | AY512931 |
| 19146 | 3 | 4 | | | IV-1 | Abca16 |
| 19147 | 3 | 4 | | | IV-1 | Abhd16b |
| 19148 | 3 | 4 | | | IV-1 | Acsm2 |
| 19149 | 3 | 4 | | | IV-1 | Actbl2 |
| 19150 | 3 | 4 | | | IV-1 | Actl6b |
| 19151 | 3 | 4 | | | IV-1 | Adam18 |
| 19152 | 3 | 4 | | | IV-1 | Adam3 |
| 19153 | 3 | 4 | | | IV-1 | Adam39 |
| 19154 | 3 | 4 | | | IV-1 | Adam6a |
| 19155 | 3 | 4 | | | IV-1 | Adamts16 |
| 19156 | 3 | 4 | | | IV-1 | Adamts20 |
| 19157 | 3 | 4 | | | IV-1 | Adamts3 |
| 19158 | 3 | 4 | | | IV-1 | Adra2b |
| 19159 | 3 | 4 | | | IV-1 | Agtr2 |
| 19160 | 3 | 4 | | | IV-1 | Aire |
| 19161 | 3 | 4 | | | IV-1 | Alk |
| 19162 | 3 | 4 | | | IV-1 | Alc |
| 19163 | 3 | 4 | | | IV-1 | Als2cr11 |
| 19164 | 3 | 4 | | | IV-1 | Amer3 |
| 19165 | 3 | 4 | | | IV-1 | Ankar |
| 19166 | 3 | 4 | | | IV-1 | Ankrd34b |
| 19167 | 3 | 4 | | | IV-1 | Ankrd42 |
| 19168 | 3 | 4 | | | IV-1 | Ankrd53 |
| 19169 | 3 | 4 | | | IV-1 | Ankrd60 |
| 19170 | 3 | 4 | | | IV-1 | Aox2 |
| 19171 | 3 | 4 | | | IV-1 | Apol10a |
| 19172 | 3 | 4 | | | IV-1 | Apol7b |
| 19173 | 3 | 4 | | | IV-1 | Arhgef33 |
| 19174 | 3 | 4 | | | IV-1 | Arhgef38 |
| 19175 | 3 | 4 | | | IV-1 | Arl13a |
| 19176 | 3 | 4 | | | IV-1 | Arl14epl |
| 19177 | 3 | 4 | | | IV-1 | Armc4 |
| 19178 | 3 | 4 | | | IV-1 | Arsj |
| 19179 | 3 | 4 | | | IV-1 | Asb12 |
| 19180 | 3 | 4 | | | IV-1 | Ascl4 |
| 19181 | 3 | 4 | | | IV-1 | Asgr2 |
| 19182 | 3 | 4 | | | IV-1 | Atg9b |
| 19183 | 3 | 4 | | | IV-1 | Atoh1 |
| 19184 | 3 | 4 | | | IV-1 | Atoh7 |
| 19185 | 3 | 4 | | | IV-1 | Atp13a5 |
| 19186 | 3 | 4 | | | IV-1 | Atp6v1g3 |
| 19187 | 3 | 4 | | | IV-1 | Aurkc |
| 19188 | 3 | 4 | | | IV-1 | Avpr1b |
| 19189 | 3 | 4 | | | IV-1 | B430319G15Rik |
| 19190 | 3 | 4 | | | IV-1 | B930092H01Rik |
| 19191 | 3 | 4 | | | IV-1 | BB019430 |
| 19192 | 3 | 4 | | | IV-1 | BB283400 |
| 19193 | 3 | 4 | | | IV-1 | BC021785 |
| 19194 | 3 | 4 | | | IV-1 | BC027072 |
| 19195 | 3 | 4 | | | IV-1 | BC030307 |
| 19196 | 3 | 4 | | | IV-1 | BC048546 |
| 19197 | 3 | 4 | | | IV-1 | BC048644 |
| 19198 | 3 | 4 | | | IV-1 | BC065397 |

Fig. 34 - 101

| | | | | | | |
|---|---|---|---|---|---|---|
| 19199 | 3 | 4 | | | IV-1 | Bag6 |
| 19200 | 3 | 4 | | | IV-1 | Bai3 |
| 19201 | 3 | 4 | | | IV-1 | Barhl1 |
| 19202 | 3 | 4 | | | IV-1 | Barhl2 |
| 19203 | 3 | 4 | | | IV-1 | Best1 |
| 19204 | 3 | 4 | | | IV-1 | Boll |
| 19205 | 3 | 4 | | | IV-1 | Bpi |
| 19206 | 3 | 4 | | | IV-1 | Bpifb3 |
| 19207 | 3 | 4 | | | IV-1 | Brinp3 |
| 19208 | 3 | 4 | | | IV-1 | Btaf1 |
| 19209 | 3 | 4 | | | IV-1 | Btbd8 |
| 19210 | 3 | 4 | | | IV-1 | Btn2a2 |
| 19211 | 3 | 4 | | | IV-1 | C030039L03Rik |
| 19212 | 3 | 4 | | | IV-1 | C130060C02Rik |
| 19213 | 3 | 4 | | | IV-1 | C130080G10Rik |
| 19214 | 3 | 4 | | | IV-1 | C130083M11Rik |
| 19215 | 3 | 4 | | | IV-1 | C230024C17Rik |
| 19216 | 3 | 4 | | | IV-1 | C330013F16Rik |
| 19217 | 3 | 4 | | | IV-1 | C530044C16Rik |
| 19218 | 3 | 4 | | | IV-1 | C730002L08Rik |
| 19219 | 3 | 4 | | | IV-1 | C8b |
| 19220 | 3 | 4 | | | IV-1 | Cabp7 |
| 19221 | 3 | 4 | | | IV-1 | Cacna1i |
| 19222 | 3 | 4 | | | IV-1 | Cacna2d3 |
| 19223 | 3 | 4 | | | IV-1 | Caps2 |
| 19224 | 3 | 4 | | | IV-1 | Catsper1 |
| 19225 | 3 | 4 | | | IV-1 | Cbln4 |
| 19226 | 3 | 4 | | | IV-1 | Ccdc13 |
| 19227 | 3 | 4 | | | IV-1 | Ccdc144b |
| 19228 | 3 | 4 | | | IV-1 | Ccdc15 |
| 19229 | 3 | 4 | | | IV-1 | Ccdc150 |
| 19230 | 3 | 4 | | | IV-1 | Ccdc155 |
| 19231 | 3 | 4 | | | IV-1 | Ccdc158 |
| 19232 | 3 | 4 | | | IV-1 | Ccdc170 |
| 19233 | 3 | 4 | | | IV-1 | Ccdc178 |
| 19234 | 3 | 4 | | | IV-1 | Ccdc18 |
| 19235 | 3 | 4 | | | IV-1 | Ccdc183 |
| 19236 | 3 | 4 | | | IV-1 | Ccdc42 |
| 19237 | 3 | 4 | | | IV-1 | Ccdc42b |
| 19238 | 3 | 4 | | | IV-1 | Ccdc7 |
| 19239 | 3 | 4 | | | IV-1 | Ccdc73 |
| 19240 | 3 | 4 | | | IV-1 | Ccdc79 |
| 19241 | 3 | 4 | | | IV-1 | Ccdc81 |
| 19242 | 3 | 4 | | | IV-1 | Ccdc83 |
| 19243 | 3 | 4 | | | IV-1 | Ccdc87 |
| 19244 | 3 | 4 | | | IV-1 | Ccna1 |
| 19245 | 3 | 4 | | | IV-1 | Ccnb3 |
| 19246 | 3 | 4 | | | IV-1 | Cct6b |
| 19247 | 3 | 4 | | | IV-1 | Cd200r3 |
| 19248 | 3 | 4 | | | IV-1 | Cd46 |
| 19249 | 3 | 4 | | | IV-1 | Cdh10 |
| 19250 | 3 | 4 | | | IV-1 | Cdh12 |
| 19251 | 3 | 4 | | | IV-1 | Cdh23 |
| 19252 | 3 | 4 | | | IV-1 | Cdh7 |
| 19253 | 3 | 4 | | | IV-1 | Cdh8 |
| 19254 | 3 | 4 | | | IV-1 | Cdh9 |
| 19255 | 3 | 4 | | | IV-1 | Cdx2 |
| 19256 | 3 | 4 | | | IV-1 | Ceacam20 |
| 19257 | 3 | 4 | | | IV-1 | Ceacam3 |
| 19258 | 3 | 4 | | | IV-1 | Celf6 |
| 19259 | 3 | 4 | | | IV-1 | Celrr |
| 19260 | 3 | 4 | | | IV-1 | Cep162 |
| 19261 | 3 | 4 | | | IV-1 | Cep290 |
| 19262 | 3 | 4 | | | IV-1 | Cep72 |
| 19263 | 3 | 4 | | | IV-1 | Cga |
| 19264 | 3 | 4 | | | IV-1 | Chat |
| 19265 | 3 | 4 | | | IV-1 | Chn1os3 |
| 19266 | 3 | 4 | | | IV-1 | Chpf2 |
| 19267 | 3 | 4 | | | IV-1 | Chrdl2 |
| 19268 | 3 | 4 | | | IV-1 | Chrm4 |
| 19269 | 3 | 4 | | | IV-1 | Chrm5 |
| 19270 | 3 | 4 | | | IV-1 | Chrna7 |
| 19271 | 3 | 4 | | | IV-1 | Chrna9 |
| 19272 | 3 | 4 | | | IV-1 | Chrnb4 |
| 19273 | 3 | 4 | | | IV-1 | Chst13 |
| 19274 | 3 | 4 | | | IV-1 | Chst9 |
| 19275 | 3 | 4 | | | IV-1 | Cilp2 |
| 19276 | 3 | 4 | | | IV-1 | Clca4 |
| 19277 | 3 | 4 | | | IV-1 | Clcnka |
| 19278 | 3 | 4 | | | IV-1 | Cldn16 |
| 19279 | 3 | 4 | | | IV-1 | Cldn17 |
| 19280 | 3 | 4 | | | IV-1 | Cldn20 |
| 19281 | 3 | 4 | | | IV-1 | Cldnd2 |
| 19282 | 3 | 4 | | | IV-1 | Clrn1 |
| 19283 | 3 | 4 | | | IV-1 | Cma2 |
| 19284 | 3 | 4 | | | IV-1 | Cmtm1 |
| 19285 | 3 | 4 | | | IV-1 | Cnga1 |
| 19286 | 3 | 4 | | | IV-1 | Cngb3 |
| 19287 | 3 | 4 | | | IV-1 | Cntn3 |
| 19288 | 3 | 4 | | | IV-1 | Cntn6 |
| 19289 | 3 | 4 | | | IV-1 | Cntnap5c |
| 19290 | 3 | 4 | | | IV-1 | Col22a1 |
| 19291 | 3 | 4 | | | IV-1 | Col25a1 |
| 19292 | 3 | 4 | | | IV-1 | Coro1c |
| 19293 | 3 | 4 | | | IV-1 | Cpa5 |
| 19294 | 3 | 4 | | | IV-1 | Cpb2 |
| 19295 | 3 | 4 | | | IV-1 | Cplx3 |
| 19296 | 3 | 4 | | | IV-1 | Cpne9 |
| 19297 | 3 | 4 | | | IV-1 | Cpz |
| 19298 | 3 | 4 | | | IV-1 | Crb1 |
| 19299 | 3 | 4 | | | IV-1 | Cryge |
| 19300 | 3 | 4 | | | IV-1 | Csmd3 |
| 19301 | 3 | 4 | | | IV-1 | Csrnp3 |
| 19302 | 3 | 4 | | | IV-1 | Cst8 |
| 19303 | 3 | 4 | | | IV-1 | Ctag2 |
| 19304 | 3 | 4 | | | IV-1 | Cubn |
| 19305 | 3 | 4 | | | IV-1 | Cxcl11 |
| 19306 | 3 | 4 | | | IV-1 | Cylc2 |
| 19307 | 3 | 4 | | | IV-1 | Cyp2ab1 |
| 19308 | 3 | 4 | | | IV-1 | Cyp2j11 |
| 19309 | 3 | 4 | | | IV-1 | Cyp2j13 |
| 19310 | 3 | 4 | | | IV-1 | Cyp3a57 |
| 19311 | 3 | 4 | | | IV-1 | Cyp4f40 |
| 19312 | 3 | 4 | | | IV-1 | Cyp4x1 |
| 19313 | 3 | 4 | | | IV-1 | Cypt14 |
| 19314 | 3 | 4 | | | IV-1 | Cypt15 |
| 19315 | 3 | 4 | | | IV-1 | Cypt2 |
| 19316 | 3 | 4 | | | IV-1 | Cypt7 |
| 19317 | 3 | 4 | | | IV-1 | D030018L15Rik |
| 19318 | 3 | 4 | | | IV-1 | D030040B21Rik |
| 19319 | 3 | 4 | | | IV-1 | D130043K22Rik |
| 19320 | 3 | 4 | | | IV-1 | D230030E09Rik |
| 19321 | 3 | 4 | | | IV-1 | D330050G23Rik |
| 19322 | 3 | 4 | | | IV-1 | Dcaf12l2 |
| 19323 | 3 | 4 | | | IV-1 | Dcdc2c |
| 19324 | 3 | 4 | | | IV-1 | Ddx4 |
| 19325 | 3 | 4 | | | IV-1 | Ddx43 |
| 19326 | 3 | 4 | | | IV-1 | Defb47 |
| 19327 | 3 | 4 | | | IV-1 | Dgkk |
| 19328 | 3 | 4 | | | IV-1 | Diec1 |
| 19329 | 3 | 4 | | | IV-1 | Dlx1 |
| 19330 | 3 | 4 | | | IV-1 | Dlx4 |
| 19331 | 3 | 4 | | | IV-1 | Dmbx1 |
| 19332 | 3 | 4 | | | IV-1 | Dmgdh |
| 19333 | 3 | 4 | | | IV-1 | Dmrta2 |
| 19334 | 3 | 4 | | | IV-1 | Dnah1 |
| 19335 | 3 | 4 | | | IV-1 | Dnah10 |
| 19336 | 3 | 4 | | | IV-1 | Dnah5 |
| 19337 | 3 | 4 | | | IV-1 | Dnah7a |
| 19338 | 3 | 4 | | | IV-1 | Dnah7b |
| 19339 | 3 | 4 | | | IV-1 | Dnah9 |
| 19340 | 3 | 4 | | | IV-1 | Dnaja3 |
| 19341 | 3 | 4 | | | IV-1 | Dnajc10 |
| 19342 | 3 | 4 | | | IV-1 | Dnm1l |
| 19343 | 3 | 4 | | | IV-1 | Dnmt3l |
| 19344 | 3 | 4 | | | IV-1 | Dok6 |
| 19345 | 3 | 4 | | | IV-1 | Dpf1 |
| 19346 | 3 | 4 | | | IV-1 | Drd3 |
| 19347 | 3 | 4 | | | IV-1 | Dscam |
| 19348 | 3 | 4 | | | IV-1 | Dux |
| 19349 | 3 | 4 | | | IV-1 | Duxbl2 |
| 19350 | 3 | 4 | | | IV-1 | Dyrk4 |
| 19351 | 3 | 4 | | | IV-1 | E130018N17Rik |
| 19352 | 3 | 4 | | | IV-1 | E130309F12Rik |
| 19353 | 3 | 4 | | | IV-1 | E230025N22Rik |
| 19354 | 3 | 4 | | | IV-1 | E330020D12Rik |
| 19355 | 3 | 4 | | | IV-1 | Ecel1 |
| 19356 | 3 | 4 | | | IV-1 | Edar |
| 19357 | 3 | 4 | | | IV-1 | Efcab5 |
| 19358 | 3 | 4 | | | IV-1 | Efhb |
| 19359 | 3 | 4 | | | IV-1 | Eif2s3x |
| 19360 | 3 | 4 | | | IV-1 | Eif4e1b |
| 19361 | 3 | 4 | | | IV-1 | Eml6 |
| 19362 | 3 | 4 | | | IV-1 | Emx1 |
| 19363 | 3 | 4 | | | IV-1 | Enox1 |
| 19364 | 3 | 4 | | | IV-1 | Epha10 |
| 19365 | 3 | 4 | | | IV-1 | Epha3 |
| 19366 | 3 | 4 | | | IV-1 | Epha6 |
| 19367 | 3 | 4 | | | IV-1 | Epha7 |
| 19368 | 3 | 4 | | | IV-1 | Eqtn |
| 19369 | 3 | 4 | | | IV-1 | Esp8 |
| 19370 | 3 | 4 | | | IV-1 | Esx1 |
| 19371 | 3 | 4 | | | IV-1 | Etv2 |
| 19372 | 3 | 4 | | | IV-1 | Evx2 |
| 19373 | 3 | 4 | | | IV-1 | F730043M19Rik |
| 19374 | 3 | 4 | | | IV-1 | F8 |
| 19375 | 3 | 4 | | | IV-1 | F9 |
| 19376 | 3 | 4 | | | IV-1 | F930015N05Rik |
| 19377 | 3 | 4 | | | IV-1 | Fam163a |
| 19378 | 3 | 4 | | | IV-1 | Fam184b |
| 19379 | 3 | 4 | | | IV-1 | Fam186b |
| 19380 | 3 | 4 | | | IV-1 | Fam187a |
| 19381 | 3 | 4 | | | IV-1 | Fam196a |
| 19382 | 3 | 4 | | | IV-1 | Fam19a1 |
| 19383 | 3 | 4 | | | IV-1 | Fam19a4 |
| 19384 | 3 | 4 | | | IV-1 | Fam228a |
| 19385 | 3 | 4 | | | IV-1 | Fam43b |
| 19386 | 3 | 4 | | | IV-1 | Fam71b |
| 19387 | 3 | 4 | | | IV-1 | Fam71d |
| 19388 | 3 | 4 | | | IV-1 | Fam71e2 |
| 19389 | 3 | 4 | | | IV-1 | Fbxo39 |
| 19390 | 3 | 4 | | | IV-1 | Fbxw26 |

Fig. 34 - 102

| | | | | | | |
|---|---|---|---|---|---|---|
| 19391 | 3 | 4 | | | IV-1 | Fcrlb |
| 19392 | 3 | 4 | | | IV-1 | Fer1l5 |
| 19393 | 3 | 4 | | | IV-1 | Ffar3 |
| 19394 | 3 | 4 | | | IV-1 | Fgf17 |
| 19395 | 3 | 4 | | | IV-1 | Fgf3 |
| 19396 | 3 | 4 | | | IV-1 | Fgfr1op2 |
| 19397 | 3 | 4 | | | IV-1 | Figla |
| 19398 | 3 | 4 | | | IV-1 | Fign |
| 19399 | 3 | 4 | | | IV-1 | Foxd1 |
| 19400 | 3 | 4 | | | IV-1 | Foxh1 |
| 19401 | 3 | 4 | | | IV-1 | Foxr2 |
| 19402 | 3 | 4 | | | IV-1 | Frmd5 |
| 19403 | 3 | 4 | | | IV-1 | Frmpd4 |
| 19404 | 3 | 4 | | | IV-1 | Fshr |
| 19405 | 3 | 4 | | | IV-1 | Fthl17 |
| 19406 | 3 | 4 | | | IV-1 | Ftmt |
| 19407 | 3 | 4 | | | IV-1 | G630093K05Rik |
| 19408 | 3 | 4 | | | IV-1 | G730013B05Rik |
| 19409 | 3 | 4 | | | IV-1 | Gabra2 |
| 19410 | 3 | 4 | | | IV-1 | Gabre |
| 19411 | 3 | 4 | | | IV-1 | Galntl6 |
| 19412 | 3 | 4 | | | IV-1 | Galr1 |
| 19413 | 3 | 4 | | | IV-1 | Galr3 |
| 19414 | 3 | 4 | | | IV-1 | Garem1 |
| 19415 | 3 | 4 | | | IV-1 | Gatad2a |
| 19416 | 3 | 4 | | | IV-1 | Gatc |
| 19417 | 3 | 4 | | | IV-1 | Gcnt3 |
| 19418 | 3 | 4 | | | IV-1 | Gcsam |
| 19419 | 3 | 4 | | | IV-1 | Gdap10 |
| 19420 | 3 | 4 | | | IV-1 | Gfi1 |
| 19421 | 3 | 4 | | | IV-1 | Ghrhr |
| 19422 | 3 | 4 | | | IV-1 | Gip |
| 19423 | 3 | 4 | | | IV-1 | Gid2 |
| 19424 | 3 | 4 | | | IV-1 | Gje1 |
| 19425 | 3 | 4 | | | IV-1 | Glipr1l1 |
| 19426 | 3 | 4 | | | IV-1 | Glp2r |
| 19427 | 3 | 4 | | | IV-1 | Glra3 |
| 19428 | 3 | 4 | | | IV-1 | Glrp1 |
| 19429 | 3 | 4 | | | IV-1 | Glt25d1 |
| 19430 | 3 | 4 | | | IV-1 | Gltpd2 |
| 19431 | 3 | 4 | | | IV-1 | Gm10096 |
| 19432 | 3 | 4 | | | IV-1 | Gm101 |
| 19433 | 3 | 4 | | | IV-1 | Gm10147 |
| 19434 | 3 | 4 | | | IV-1 | Gm10432 |
| 19435 | 3 | 4 | | | IV-1 | Gm10439 |
| 19436 | 3 | 4 | | | IV-1 | Gm10471 |
| 19437 | 3 | 4 | | | IV-1 | Gm10640 |
| 19438 | 3 | 4 | | | IV-1 | Gm10677 |
| 19439 | 3 | 4 | | | IV-1 | Gm10684 |
| 19440 | 3 | 4 | | | IV-1 | Gm10845 |
| 19441 | 3 | 4 | | | IV-1 | Gm10921 |
| 19442 | 3 | 4 | | | IV-1 | Gm1123 |
| 19443 | 3 | 4 | | | IV-1 | Gm11538 |
| 19444 | 3 | 4 | | | IV-1 | Gm11549 |
| 19445 | 3 | 4 | | | IV-1 | Gm11762 |
| 19446 | 3 | 4 | | | IV-1 | Gm11981 |
| 19447 | 3 | 4 | | | IV-1 | Gm12159 |
| 19448 | 3 | 4 | | | IV-1 | Gm12185 |
| 19449 | 3 | 4 | | | IV-1 | Gm12298 |
| 19450 | 3 | 4 | | | IV-1 | Gm12695 |
| 19451 | 3 | 4 | | | IV-1 | Gm12718 |
| 19452 | 3 | 4 | | | IV-1 | Gm13290 |
| 19453 | 3 | 4 | | | IV-1 | Gm13293 |
| 19454 | 3 | 4 | | | IV-1 | Gm13315 |
| 19455 | 3 | 4 | | | IV-1 | Gm13446 |
| 19456 | 3 | 4 | | | IV-1 | Gm13490 |
| 19457 | 3 | 4 | | | IV-1 | Gm13629 |
| 19458 | 3 | 4 | | | IV-1 | Gm13871 |
| 19459 | 3 | 4 | | | IV-1 | Gm14023 |
| 19460 | 3 | 4 | | | IV-1 | Gm14164 |
| 19461 | 3 | 4 | | | IV-1 | Gm14351 |
| 19462 | 3 | 4 | | | IV-1 | Gm14379 |
| 19463 | 3 | 4 | | | IV-1 | Gm14458 |
| 19464 | 3 | 4 | | | IV-1 | Gm14474 |
| 19465 | 3 | 4 | | | IV-1 | Gm14483 |
| 19466 | 3 | 4 | | | IV-1 | Gm14525 |
| 19467 | 3 | 4 | | | IV-1 | Gm14634 |
| 19468 | 3 | 4 | | | IV-1 | Gm14725 |
| 19469 | 3 | 4 | | | IV-1 | Gm14827 |
| 19470 | 3 | 4 | | | IV-1 | Gm15097 |
| 19471 | 3 | 4 | | | IV-1 | Gm15107 |
| 19472 | 3 | 4 | | | IV-1 | Gm15114 |
| 19473 | 3 | 4 | | | IV-1 | Gm15217 |
| 19474 | 3 | 4 | | | IV-1 | Gm15319 |
| 19475 | 3 | 4 | | | IV-1 | Gm15412 |
| 19476 | 3 | 4 | | | IV-1 | Gm1564 |
| 19477 | 3 | 4 | | | IV-1 | Gm15698 |
| 19478 | 3 | 4 | | | IV-1 | Gm15880 |
| 19479 | 3 | 4 | | | IV-1 | Gm16063 |
| 19480 | 3 | 4 | | | IV-1 | Gm16523 |
| 19481 | 3 | 4 | | | IV-1 | Gm1653 |
| 19482 | 3 | 4 | | | IV-1 | Gm16532 |
| 19483 | 3 | 4 | | | IV-1 | Gm16701 |
| 19484 | 3 | 4 | | | IV-1 | Gm16880 |
| 19485 | 3 | 4 | | | IV-1 | Gm16897 |
| 19486 | 3 | 4 | | | IV-1 | Gm16938 |
| 19487 | 3 | 4 | | | IV-1 | Gm16998 |
| 19488 | 3 | 4 | | | IV-1 | Gm1720 |
| 19489 | 3 | 4 | | | IV-1 | Gm17359 |
| 19490 | 3 | 4 | | | IV-1 | Gm17801 |
| 19491 | 3 | 4 | | | IV-1 | Gm19522 |
| 19492 | 3 | 4 | | | IV-1 | Gm19557 |
| 19493 | 3 | 4 | | | IV-1 | Gm19583 |
| 19494 | 3 | 4 | | | IV-1 | Gm19619 |
| 19495 | 3 | 4 | | | IV-1 | Gm20063 |
| 19496 | 3 | 4 | | | IV-1 | Gm20098 |
| 19497 | 3 | 4 | | | IV-1 | Gm2012 |
| 19498 | 3 | 4 | | | IV-1 | Gm2016 |
| 19499 | 3 | 4 | | | IV-1 | Gm2030 |
| 19500 | 3 | 4 | | | IV-1 | Gm2061 |
| 19501 | 3 | 4 | | | IV-1 | Gm20751 |
| 19502 | 3 | 4 | | | IV-1 | Gm20823 |
| 19503 | 3 | 4 | | | IV-1 | Gm20831 |
| 19504 | 3 | 4 | | | IV-1 | Gm20867 |
| 19505 | 3 | 4 | | | IV-1 | Gm20871 |
| 19506 | 3 | 4 | | | IV-1 | Gm20939 |
| 19507 | 3 | 4 | | | IV-1 | Gm21057 |
| 19508 | 3 | 4 | | | IV-1 | Gm21283 |
| 19509 | 3 | 4 | | | IV-1 | Gm21950 |
| 19510 | 3 | 4 | | | IV-1 | Gm21951 |
| 19511 | 3 | 4 | | | IV-1 | Gm2863 |
| 19512 | 3 | 4 | | | IV-1 | Gm3002 |
| 19513 | 3 | 4 | | | IV-1 | Gm3143 |
| 19514 | 3 | 4 | | | IV-1 | Gm3458 |
| 19515 | 3 | 4 | | | IV-1 | Gm3488 |
| 19516 | 3 | 4 | | | IV-1 | Gm3706 |
| 19517 | 3 | 4 | | | IV-1 | Gm3750 |
| 19518 | 3 | 4 | | | IV-1 | Gm382 |
| 19519 | 3 | 4 | | | IV-1 | Gm4027 |
| 19520 | 3 | 4 | | | IV-1 | Gm4297 |
| 19521 | 3 | 4 | | | IV-1 | Gm438 |
| 19522 | 3 | 4 | | | IV-1 | Gm4776 |
| 19523 | 3 | 4 | | | IV-1 | Gm4787 |
| 19524 | 3 | 4 | | | IV-1 | Gm4814 |
| 19525 | 3 | 4 | | | IV-1 | Gm4827 |
| 19526 | 3 | 4 | | | IV-1 | Gm4884 |
| 19527 | 3 | 4 | | | IV-1 | Gm4926 |
| 19528 | 3 | 4 | | | IV-1 | Gm4937 |
| 19529 | 3 | 4 | | | IV-1 | Gm5072 |
| 19530 | 3 | 4 | | | IV-1 | Gm5084 |
| 19531 | 3 | 4 | | | IV-1 | Gm5086 |
| 19532 | 3 | 4 | | | IV-1 | Gm5091 |
| 19533 | 3 | 4 | | | IV-1 | Gm5111 |
| 19534 | 3 | 4 | | | IV-1 | Gm5114 |
| 19535 | 3 | 4 | | | IV-1 | Gm5122 |
| 19536 | 3 | 4 | | | IV-1 | Gm5126 |
| 19537 | 3 | 4 | | | IV-1 | Gm5136 |
| 19538 | 3 | 4 | | | IV-1 | Gm5169 |
| 19539 | 3 | 4 | | | IV-1 | Gm5334 |
| 19540 | 3 | 4 | | | IV-1 | Gm5346 |
| 19541 | 3 | 4 | | | IV-1 | Gm5464 |
| 19542 | 3 | 4 | | | IV-1 | Gm5468 |
| 19543 | 3 | 4 | | | IV-1 | Gm5475 |
| 19544 | 3 | 4 | | | IV-1 | Gm5523 |
| 19545 | 3 | 4 | | | IV-1 | Gm5591 |
| 19546 | 3 | 4 | | | IV-1 | Gm5622 |
| 19547 | 3 | 4 | | | IV-1 | Gm5634 |
| 19548 | 3 | 4 | | | IV-1 | Gm5662 |
| 19549 | 3 | 4 | | | IV-1 | Gm5878 |
| 19550 | 3 | 4 | | | IV-1 | Gm5925 |
| 19551 | 3 | 4 | | | IV-1 | Gm5934 |
| 19552 | 3 | 4 | | | IV-1 | Gm5936 |
| 19553 | 3 | 4 | | | IV-1 | Gm609 |
| 19554 | 3 | 4 | | | IV-1 | Gm6121 |
| 19555 | 3 | 4 | | | IV-1 | Gm6249 |
| 19556 | 3 | 4 | | | IV-1 | Gm6289 |
| 19557 | 3 | 4 | | | IV-1 | Gm6307 |
| 19558 | 3 | 4 | | | IV-1 | Gm648 |
| 19559 | 3 | 4 | | | IV-1 | Gm6583 |
| 19560 | 3 | 4 | | | IV-1 | Gm6639 |
| 19561 | 3 | 4 | | | IV-1 | Gm6756 |
| 19562 | 3 | 4 | | | IV-1 | Gm6812 |
| 19563 | 3 | 4 | | | IV-1 | Gm6902 |
| 19564 | 3 | 4 | | | IV-1 | Gm6904 |
| 19565 | 3 | 4 | | | IV-1 | Gm6927 |
| 19566 | 3 | 4 | | | IV-1 | Gm7104 |
| 19567 | 3 | 4 | | | IV-1 | Gm7444 |
| 19568 | 3 | 4 | | | IV-1 | Gm7904 |
| 19569 | 3 | 4 | | | IV-1 | Gm805 |
| 19570 | 3 | 4 | | | IV-1 | Gm8267 |
| 19571 | 3 | 4 | | | IV-1 | Gm8439 |
| 19572 | 3 | 4 | | | IV-1 | Gm853 |
| 19573 | 3 | 4 | | | IV-1 | Gm8765 |
| 19574 | 3 | 4 | | | IV-1 | Gm8787 |
| 19575 | 3 | 4 | | | IV-1 | Gm8817 |
| 19576 | 3 | 4 | | | IV-1 | Gm8884 |
| 19577 | 3 | 4 | | | IV-1 | Gm933 |
| 19578 | 3 | 4 | | | IV-1 | Gm960 |
| 19579 | 3 | 4 | | | IV-1 | Gml |
| 19580 | 3 | 4 | | | IV-1 | Gnat2 |
| 19581 | 3 | 4 | | | IV-1 | Gnat3 |
| 19582 | 3 | 4 | | | IV-1 | Gpat2 |

Fig. 34 - 103

| | | | | | | |
|---|---|---|---|---|---|---|
| 19583 | 3 | 4 | | | IV-1 | Gpr139 |
| 19584 | 3 | 4 | | | IV-1 | Gpr149 |
| 19585 | 3 | 4 | | | IV-1 | Gpr150 |
| 19586 | 3 | 4 | | | IV-1 | Gpr151 |
| 19587 | 3 | 4 | | | IV-1 | Gpr173 |
| 19588 | 3 | 4 | | | IV-1 | Gpr176 |
| 19589 | 3 | 4 | | | IV-1 | Gpr21 |
| 19590 | 3 | 4 | | | IV-1 | Gpr33 |
| 19591 | 3 | 4 | | | IV-1 | Gpr45 |
| 19592 | 3 | 4 | | | IV-1 | Gpr6 |
| 19593 | 3 | 4 | | | IV-1 | Gpr82 |
| 19594 | 3 | 4 | | | IV-1 | Greb1l |
| 19595 | 3 | 4 | | | IV-1 | Grid2 |
| 19596 | 3 | 4 | | | IV-1 | Grik3 |
| 19597 | 3 | 4 | | | IV-1 | Grik4 |
| 19598 | 3 | 4 | | | IV-1 | Grin3a |
| 19599 | 3 | 4 | | | IV-1 | Grm8 |
| 19600 | 3 | 4 | | | IV-1 | Gsc |
| 19601 | 3 | 4 | | | IV-1 | Gsc2 |
| 19602 | 3 | 4 | | | IV-1 | Gsdmcl2 |
| 19603 | 3 | 4 | | | IV-1 | Gzmn |
| 19604 | 3 | 4 | | | IV-1 | H2bfm |
| 19605 | 3 | 4 | | | IV-1 | Has1 |
| 19606 | 3 | 4 | | | IV-1 | Has2 |
| 19607 | 3 | 4 | | | IV-1 | Hba-x |
| 19608 | 3 | 4 | | | IV-1 | Hcn1 |
| 19609 | 3 | 4 | | | IV-1 | Hcrtr2 |
| 19610 | 3 | 4 | | | IV-1 | Hdhd1a |
| 19611 | 3 | 4 | | | IV-1 | Heatr3 |
| 19612 | 3 | 4 | | | IV-1 | Hecw1 |
| 19613 | 3 | 4 | | | IV-1 | Helt |
| 19614 | 3 | 4 | | | IV-1 | Hemt1 |
| 19615 | 3 | 4 | | | IV-1 | Hes3 |
| 19616 | 3 | 4 | | | IV-1 | Hes5 |
| 19617 | 3 | 4 | | | IV-1 | Hfm1 |
| 19618 | 3 | 4 | | | IV-1 | Hist1h2aa |
| 19619 | 3 | 4 | | | IV-1 | Hkdc1 |
| 19620 | 3 | 4 | | | IV-1 | Hmgb1-rs17 |
| 19621 | 3 | 4 | | | IV-1 | Hnrnpul2 |
| 19622 | 3 | 4 | | | IV-1 | Hormad2 |
| 19623 | 3 | 4 | | | IV-1 | Hoxb13 |
| 19624 | 3 | 4 | | | IV-1 | Hp1bp3 |
| 19625 | 3 | 4 | | | IV-1 | Hrk |
| 19626 | 3 | 4 | | | IV-1 | Hsd3b4 |
| 19627 | 3 | 4 | | | IV-1 | Hsfy2 |
| 19628 | 3 | 4 | | | IV-1 | Htr1a |
| 19629 | 3 | 4 | | | IV-1 | Htr2a |
| 19630 | 3 | 4 | | | IV-1 | Htr3b |
| 19631 | 3 | 4 | | | IV-1 | Htr5a |
| 19632 | 3 | 4 | | | IV-1 | Htt |
| 19633 | 3 | 4 | | | IV-1 | Hus1b |
| 19634 | 3 | 4 | | | IV-1 | Hyal5 |
| 19635 | 3 | 4 | | | IV-1 | Hyal6 |
| 19636 | 3 | 4 | | | IV-1 | Ide |
| 19637 | 3 | 4 | | | IV-1 | Ifitd1 |
| 19638 | 3 | 4 | | | IV-1 | Igbp1b |
| 19639 | 3 | 4 | | | IV-1 | Igf2bp1 |
| 19640 | 3 | 4 | | | IV-1 | Igf2bp3 |
| 19641 | 3 | 4 | | | IV-1 | Il12rb1 |
| 19642 | 3 | 4 | | | IV-1 | Il13 |
| 19643 | 3 | 4 | | | IV-1 | Il19 |
| 19644 | 3 | 4 | | | IV-1 | Il1bos |
| 19645 | 3 | 4 | | | IV-1 | Il27 |
| 19646 | 3 | 4 | | | IV-1 | Il31ra |
| 19647 | 3 | 4 | | | IV-1 | Il5 |
| 19648 | 3 | 4 | | | IV-1 | Impg1 |
| 19649 | 3 | 4 | | | IV-1 | Impg2 |
| 19650 | 3 | 4 | | | IV-1 | Insrr |
| 19651 | 3 | 4 | | | IV-1 | Ipo11 |
| 19652 | 3 | 4 | | | IV-1 | Iqub |
| 19653 | 3 | 4 | | | IV-1 | Irg1 |
| 19654 | 3 | 4 | | | IV-1 | Irx6 |
| 19655 | 3 | 4 | | | IV-1 | Isl2 |
| 19656 | 3 | 4 | | | IV-1 | Ism2 |
| 19657 | 3 | 4 | | | IV-1 | Isx |
| 19658 | 3 | 4 | | | IV-1 | Itfg1 |
| 19659 | 3 | 4 | | | IV-1 | Itga10 |
| 19660 | 3 | 4 | | | IV-1 | Itgb2l |
| 19661 | 3 | 4 | | | IV-1 | Izumo3 |
| 19662 | 3 | 4 | | | IV-1 | Kcnd1 |
| 19663 | 3 | 4 | | | IV-1 | Kcnd3os |
| 19664 | 3 | 4 | | | IV-1 | Kcnh6 |
| 19665 | 3 | 4 | | | IV-1 | Kcnh8 |
| 19666 | 3 | 4 | | | IV-1 | Kcnk16 |
| 19667 | 3 | 4 | | | IV-1 | Kctd8 |
| 19668 | 3 | 4 | | | IV-1 | Kdelr1 |
| 19669 | 3 | 4 | | | IV-1 | Kif26b |
| 19670 | 3 | 4 | | | IV-1 | Kif4-ps |
| 19671 | 3 | 4 | | | IV-1 | Kif6 |
| 19672 | 3 | 4 | | | IV-1 | Kif7 |
| 19673 | 3 | 4 | | | IV-1 | Klhl14 |
| 19674 | 3 | 4 | | | IV-1 | Klk12 |
| 19675 | 3 | 4 | | | IV-1 | Klk1b16 |
| 19676 | 3 | 4 | | | IV-1 | Klk1b7-ps |
| 19677 | 3 | 4 | | | IV-1 | Klra10 |
| 19678 | 3 | 4 | | | IV-1 | Klra13-ps |
| 19679 | 3 | 4 | | | IV-1 | Klrc3 |
| 19680 | 3 | 4 | | | IV-1 | Kntc1 |
| 19681 | 3 | 4 | | | IV-1 | Krt26 |
| 19682 | 3 | 4 | | | IV-1 | Krt36 |
| 19683 | 3 | 4 | | | IV-1 | Krt40 |
| 19684 | 3 | 4 | | | IV-1 | Krt75 |
| 19685 | 3 | 4 | | | IV-1 | Krt9 |
| 19686 | 3 | 4 | | | IV-1 | Krtap27-1 |
| 19687 | 3 | 4 | | | IV-1 | Krtap31-1 |
| 19688 | 3 | 4 | | | IV-1 | L1td1 |
| 19689 | 3 | 4 | | | IV-1 | L3mbtl4 |
| 19690 | 3 | 4 | | | IV-1 | LOC100048884 |
| 19691 | 3 | 4 | | | IV-1 | LOC100504039 |
| 19692 | 3 | 4 | | | IV-1 | LOC100862268 |
| 19693 | 3 | 4 | | | IV-1 | LOC101056136 |
| 19694 | 3 | 4 | | | IV-1 | LOC101056149 |
| 19695 | 3 | 4 | | | IV-1 | LOC102632430 |
| 19696 | 3 | 4 | | | IV-1 | Lama1 |
| 19697 | 3 | 4 | | | IV-1 | Lancl3 |
| 19698 | 3 | 4 | | | IV-1 | Lhx9 |
| 19699 | 3 | 4 | | | IV-1 | Lin28b |
| 19700 | 3 | 4 | | | IV-1 | Lipk |
| 19701 | 3 | 4 | | | IV-1 | Lmln |
| 19702 | 3 | 4 | | | IV-1 | Loxhd1 |
| 19703 | 3 | 4 | | | IV-1 | Lrch2 |
| 19704 | 3 | 4 | | | IV-1 | Lrfn2 |
| 19705 | 3 | 4 | | | IV-1 | Lrrc16b |
| 19706 | 3 | 4 | | | IV-1 | Lrrc19 |
| 19707 | 3 | 4 | | | IV-1 | Lrrc63 |
| 19708 | 3 | 4 | | | IV-1 | Lrrc72 |
| 19709 | 3 | 4 | | | IV-1 | Lrriq1 |
| 19710 | 3 | 4 | | | IV-1 | Lrrtm2 |
| 19711 | 3 | 4 | | | IV-1 | Lsamp |
| 19712 | 3 | 4 | | | IV-1 | Luzp4 |
| 19713 | 3 | 4 | | | IV-1 | Lypd6b |
| 19714 | 3 | 4 | | | IV-1 | Lyzl1 |
| 19715 | 3 | 4 | | | IV-1 | Magea10 |
| 19716 | 3 | 4 | | | IV-1 | Magea4 |
| 19717 | 3 | 4 | | | IV-1 | Magea6 |
| 19718 | 3 | 4 | | | IV-1 | Magea8 |
| 19719 | 3 | 4 | | | IV-1 | Mageb2 |
| 19720 | 3 | 4 | | | IV-1 | Mageb4 |
| 19721 | 3 | 4 | | | IV-1 | Magee2 |
| 19722 | 3 | 4 | | | IV-1 | Magel2 |
| 19723 | 3 | 4 | | | IV-1 | Mak |
| 19724 | 3 | 4 | | | IV-1 | Mamdc4 |
| 19725 | 3 | 4 | | | IV-1 | Man1b1 |
| 19726 | 3 | 4 | | | IV-1 | Map3k19 |
| 19727 | 3 | 4 | | | IV-1 | March4 |
| 19728 | 3 | 4 | | | IV-1 | Matn3 |
| 19729 | 3 | 4 | | | IV-1 | Mc1r |
| 19730 | 3 | 4 | | | IV-1 | Mccc1os |
| 19731 | 3 | 4 | | | IV-1 | Mcf2 |
| 19732 | 3 | 4 | | | IV-1 | Mcpt2 |
| 19733 | 3 | 4 | | | IV-1 | Mdga2 |
| 19734 | 3 | 4 | | | IV-1 | Mdh1b |
| 19735 | 3 | 4 | | | IV-1 | Med12l |
| 19736 | 3 | 4 | | | IV-1 | Megf10 |
| 19737 | 3 | 4 | | | IV-1 | Megf11 |
| 19738 | 3 | 4 | | | IV-1 | Mgat4c |
| 19739 | 3 | 4 | | | IV-1 | Mogs |
| 19740 | 3 | 4 | | | IV-1 | Mov10l1 |
| 19741 | 3 | 4 | | | IV-1 | Mrgprb8 |
| 19742 | 3 | 4 | | | IV-1 | Mroh2a |
| 19743 | 3 | 4 | | | IV-1 | Mroh2b |
| 19744 | 3 | 4 | | | IV-1 | Mroh4 |
| 19745 | 3 | 4 | | | IV-1 | Mroh5 |
| 19746 | 3 | 4 | | | IV-1 | Mroh9 |
| 19747 | 3 | 4 | | | IV-1 | Ms4a18 |
| 19748 | 3 | 4 | | | IV-1 | Msh4 |
| 19749 | 3 | 4 | | | IV-1 | Mup4 |
| 19750 | 3 | 4 | | | IV-1 | Myh15 |
| 19751 | 3 | 4 | | | IV-1 | Myh3 |
| 19752 | 3 | 4 | | | IV-1 | Myo16 |
| 19753 | 3 | 4 | | | IV-1 | Myo3b |
| 19754 | 3 | 4 | | | IV-1 | Myo7b |
| 19755 | 3 | 4 | | | IV-1 | Nalcn |
| 19756 | 3 | 4 | | | IV-1 | Nanos2 |
| 19757 | 3 | 4 | | | IV-1 | Ndst3 |
| 19758 | 3 | 4 | | | IV-1 | Ndst4 |
| 19759 | 3 | 4 | | | IV-1 | Nell1 |
| 19760 | 3 | 4 | | | IV-1 | Neurog3 |
| 19761 | 3 | 4 | | | IV-1 | Nhlh2 |
| 19762 | 3 | 4 | | | IV-1 | Nkx2-5 |
| 19763 | 3 | 4 | | | IV-1 | Nkx3-1 |
| 19764 | 3 | 4 | | | IV-1 | Nkx6-3 |
| 19765 | 3 | 4 | | | IV-1 | Nlrp14 |
| 19766 | 3 | 4 | | | IV-1 | Nlrp4e |
| 19767 | 3 | 4 | | | IV-1 | Nlrp5-ps |
| 19768 | 3 | 4 | | | IV-1 | Nme8 |
| 19769 | 3 | 4 | | | IV-1 | Noa1 |
| 19770 | 3 | 4 | | | IV-1 | Nodal |
| 19771 | 3 | 4 | | | IV-1 | Nox3 |
| 19772 | 3 | 4 | | | IV-1 | Npc1l1 |
| 19773 | 3 | 4 | | | IV-1 | Npy2r |
| 19774 | 3 | 4 | | | IV-1 | Npy5r |

Fig. 34 - 104

| | | | | | | |
|---|---|---|---|---|---|---|
| 19775 | 3 | 4 | | | IV-1 | Nrg3 |
| 19776 | 3 | 4 | | | IV-1 | Nrg3os |
| 19777 | 3 | 4 | | | IV-1 | Nrl |
| 19778 | 3 | 4 | | | IV-1 | Nsun7 |
| 19779 | 3 | 4 | | | IV-1 | Ntng1 |
| 19780 | 3 | 4 | | | IV-1 | Nup210l |
| 19781 | 3 | 4 | | | IV-1 | Nwd2 |
| 19782 | 3 | 4 | | | IV-1 | Nxf2 |
| 19783 | 3 | 4 | | | IV-1 | Oacyl |
| 19784 | 3 | 4 | | | IV-1 | Oca2 |
| 19785 | 3 | 4 | | | IV-1 | Olah |
| 19786 | 3 | 4 | | | IV-1 | Olfr13 |
| 19787 | 3 | 4 | | | IV-1 | Olfr1342 |
| 19788 | 3 | 4 | | | IV-1 | Olfr1383 |
| 19789 | 3 | 4 | | | IV-1 | Olfr1442 |
| 19790 | 3 | 4 | | | IV-1 | Olfr183 |
| 19791 | 3 | 4 | | | IV-1 | Olfr287 |
| 19792 | 3 | 4 | | | IV-1 | Olfr288 |
| 19793 | 3 | 4 | | | IV-1 | Olfr29-ps1 |
| 19794 | 3 | 4 | | | IV-1 | Olfr308 |
| 19795 | 3 | 4 | | | IV-1 | Olfr325 |
| 19796 | 3 | 4 | | | IV-1 | Olfr357 |
| 19797 | 3 | 4 | | | IV-1 | Olfr432 |
| 19798 | 3 | 4 | | | IV-1 | Olfr554 |
| 19799 | 3 | 4 | | | IV-1 | Olfr731 |
| 19800 | 3 | 4 | | | IV-1 | Olfr750 |
| 19801 | 3 | 4 | | | IV-1 | Olfr788 |
| 19802 | 3 | 4 | | | IV-1 | Olfr93 |
| 19803 | 3 | 4 | | | IV-1 | Oir1 |
| 19804 | 3 | 4 | | | IV-1 | Oosp1 |
| 19805 | 3 | 4 | | | IV-1 | Oosp2 |
| 19806 | 3 | 4 | | | IV-1 | Otp |
| 19807 | 3 | 4 | | | IV-1 | Otx2 |
| 19808 | 3 | 4 | | | IV-1 | Ovol3 |
| 19809 | 3 | 4 | | | IV-1 | Oxgr1 |
| 19810 | 3 | 4 | | | IV-1 | Oxt |
| 19811 | 3 | 4 | | | IV-1 | Pax6 |
| 19812 | 3 | 4 | | | IV-1 | Pbxip1 |
| 19813 | 3 | 4 | | | IV-1 | Pcdh15 |
| 19814 | 3 | 4 | | | IV-1 | Pcdh8 |
| 19815 | 3 | 4 | | | IV-1 | Pcdha1 |
| 19816 | 3 | 4 | | | IV-1 | Pcdha10 |
| 19817 | 3 | 4 | | | IV-1 | Pcdha11 |
| 19818 | 3 | 4 | | | IV-1 | Pcdha3 |
| 19819 | 3 | 4 | | | IV-1 | Pcdha4 |
| 19820 | 3 | 4 | | | IV-1 | Pcdha7 |
| 19821 | 3 | 4 | | | IV-1 | Pcdha9 |
| 19822 | 3 | 4 | | | IV-1 | Pcdhac1 |
| 19823 | 3 | 4 | | | IV-1 | Pcdhb1 |
| 19824 | 3 | 4 | | | IV-1 | Pcdhb10 |
| 19825 | 3 | 4 | | | IV-1 | Pcdhb11 |
| 19826 | 3 | 4 | | | IV-1 | Pcdhb13 |
| 19827 | 3 | 4 | | | IV-1 | Pcdhb14 |
| 19828 | 3 | 4 | | | IV-1 | Pcdhb18 |
| 19829 | 3 | 4 | | | IV-1 | Pcdhb4 |
| 19830 | 3 | 4 | | | IV-1 | Pcdhb5 |
| 19831 | 3 | 4 | | | IV-1 | Pcdhb6 |
| 19832 | 3 | 4 | | | IV-1 | Pcdhb8 |
| 19833 | 3 | 4 | | | IV-1 | Pcdhb9 |
| 19834 | 3 | 4 | | | IV-1 | Pcdhga12 |
| 19835 | 3 | 4 | | | IV-1 | Pcdhga3 |
| 19836 | 3 | 4 | | | IV-1 | Pcdhga8 |
| 19837 | 3 | 4 | | | IV-1 | Pcdhga9 |
| 19838 | 3 | 4 | | | IV-1 | Pcdhgb1 |
| 19839 | 3 | 4 | | | IV-1 | Pcnxl2 |
| 19840 | 3 | 4 | | | IV-1 | Pdxk-ps |
| 19841 | 3 | 4 | | | IV-1 | Pet2 |
| 19842 | 3 | 4 | | | IV-1 | Pglyrp4 |
| 19843 | 3 | 4 | | | IV-1 | Phox2b |
| 19844 | 3 | 4 | | | IV-1 | Pip |
| 19845 | 3 | 4 | | | IV-1 | Pitx1 |
| 19846 | 3 | 4 | | | IV-1 | Pkdrej |
| 19847 | 3 | 4 | | | IV-1 | Plch1 |
| 19848 | 3 | 4 | | | IV-1 | Plcz1 |
| 19849 | 3 | 4 | | | IV-1 | Pld1 |
| 19850 | 3 | 4 | | | IV-1 | Plekhg4 |
| 19851 | 3 | 4 | | | IV-1 | Plxna4os1 |
| 19852 | 3 | 4 | | | IV-1 | Pmfbp1 |
| 19853 | 3 | 4 | | | IV-1 | Pnma5 |
| 19854 | 3 | 4 | | | IV-1 | Poldip3 |
| 19855 | 3 | 4 | | | IV-1 | Polr2m |
| 19856 | 3 | 4 | | | IV-1 | Pou3f2 |
| 19857 | 3 | 4 | | | IV-1 | Pou6f2 |
| 19858 | 3 | 4 | | | IV-1 | Ppef1 |
| 19859 | 3 | 4 | | | IV-1 | Ppfia2 |
| 19860 | 3 | 4 | | | IV-1 | Pp1r1c |
| 19861 | 3 | 4 | | | IV-1 | Ppp1r2 |
| 19862 | 3 | 4 | | | IV-1 | Ppp4r1l-ps |
| 19863 | 3 | 4 | | | IV-1 | Ppp6r3 |
| 19864 | 3 | 4 | | | IV-1 | Prame |
| 19865 | 3 | 4 | | | IV-1 | Pramel1 |
| 19866 | 3 | 4 | | | IV-1 | Pramel3 |
| 19867 | 3 | 4 | | | IV-1 | Prkdc |
| 19868 | 3 | 4 | | | IV-1 | Prl2c4 |
| 19869 | 3 | 4 | | | IV-1 | Prl2c5 |
| 19870 | 3 | 4 | | | IV-1 | Prph2 |
| 19871 | 3 | 4 | | | IV-1 | Prr23a |
| 19872 | 3 | 4 | | | IV-1 | Prss21 |
| 19873 | 3 | 4 | | | IV-1 | Prss33 |
| 19874 | 3 | 4 | | | IV-1 | Prss37 |
| 19875 | 3 | 4 | | | IV-1 | Prss43 |
| 19876 | 3 | 4 | | | IV-1 | Psg19 |
| 19877 | 3 | 4 | | | IV-1 | Psg27 |
| 19878 | 3 | 4 | | | IV-1 | Ptchd1 |
| 19879 | 3 | 4 | | | IV-1 | Ptchd2 |
| 19880 | 3 | 4 | | | IV-1 | Rab11b |
| 19881 | 3 | 4 | | | IV-1 | Rab40c |
| 19882 | 3 | 4 | | | IV-1 | Rad51ap2 |
| 19883 | 3 | 4 | | | IV-1 | Raet1a |
| 19884 | 3 | 4 | | | IV-1 | Rapgef1 |
| 19885 | 3 | 4 | | | IV-1 | Raver1-fdx1l |
| 19886 | 3 | 4 | | | IV-1 | Rbm11 |
| 19887 | 3 | 4 | | | IV-1 | Rbmxl2 |
| 19888 | 3 | 4 | | | IV-1 | Rec8 |
| 19889 | 3 | 4 | | | IV-1 | Rfx6 |
| 19890 | 3 | 4 | | | IV-1 | Rgs13 |
| 19891 | 3 | 4 | | | IV-1 | Rgs22 |
| 19892 | 3 | 4 | | | IV-1 | Rhoa |
| 19893 | 3 | 4 | | | IV-1 | Rhox1 |
| 19894 | 3 | 4 | | | IV-1 | Rhox11 |
| 19895 | 3 | 4 | | | IV-1 | Rhox2a |
| 19896 | 3 | 4 | | | IV-1 | Rhox3c |
| 19897 | 3 | 4 | | | IV-1 | Rhox4b |
| 19898 | 3 | 4 | | | IV-1 | Rhox4c |
| 19899 | 3 | 4 | | | IV-1 | Rhpn1 |
| 19900 | 3 | 4 | | | IV-1 | Ribc2 |
| 19901 | 3 | 4 | | | IV-1 | Rimbp2 |
| 19902 | 3 | 4 | | | IV-1 | Rin1 |
| 19903 | 3 | 4 | | | IV-1 | Rltpr |
| 19904 | 3 | 4 | | | IV-1 | Rnase13 |
| 19905 | 3 | 4 | | | IV-1 | Rnf148 |
| 19906 | 3 | 4 | | | IV-1 | Rnf165 |
| 19907 | 3 | 4 | | | IV-1 | Rnf17 |
| 19908 | 3 | 4 | | | IV-1 | Rrn3 |
| 19909 | 3 | 4 | | | IV-1 | Rsican18 |
| 19910 | 3 | 4 | | | IV-1 | Rsph6a |
| 19911 | 3 | 4 | | | IV-1 | Rttn |
| 19912 | 3 | 4 | | | IV-1 | Rubie |
| 19913 | 3 | 4 | | | IV-1 | Rxfp2 |
| 19914 | 3 | 4 | | | IV-1 | Rxfp3 |
| 19915 | 3 | 4 | | | IV-1 | Sall3 |
| 19916 | 3 | 4 | | | IV-1 | Samt2 |
| 19917 | 3 | 4 | | | IV-1 | Samt4 |
| 19918 | 3 | 4 | | | IV-1 | Satl1 |
| 19919 | 3 | 4 | | | IV-1 | Sbp |
| 19920 | 3 | 4 | | | IV-1 | Sbspon |
| 19921 | 3 | 4 | | | IV-1 | Scgb2b23-ps |
| 19922 | 3 | 4 | | | IV-1 | Scml2 |
| 19923 | 3 | 4 | | | IV-1 | Scn5a |
| 19924 | 3 | 4 | | | IV-1 | Scrt2 |
| 19925 | 3 | 4 | | | IV-1 | Scube3 |
| 19926 | 3 | 4 | | | IV-1 | Sdk1 |
| 19927 | 3 | 4 | | | IV-1 | Sds |
| 19928 | 3 | 4 | | | IV-1 | Sebox |
| 19929 | 3 | 4 | | | IV-1 | Sec14l5 |
| 19930 | 3 | 4 | | | IV-1 | Sec31a |
| 19931 | 3 | 4 | | | IV-1 | Sele |
| 19932 | 3 | 4 | | | IV-1 | Serinc4 |
| 19933 | 3 | 4 | | | IV-1 | Serpinf2 |
| 19934 | 3 | 4 | | | IV-1 | Sf3b3 |
| 19935 | 3 | 4 | | | IV-1 | Sgcz |
| 19936 | 3 | 4 | | | IV-1 | Shox2 |
| 19937 | 3 | 4 | | | IV-1 | Sim1 |
| 19938 | 3 | 4 | | | IV-1 | Six3 |
| 19939 | 3 | 4 | | | IV-1 | Skor2 |
| 19940 | 3 | 4 | | | IV-1 | Slc12a1 |
| 19941 | 3 | 4 | | | IV-1 | Slc14a2 |
| 19942 | 3 | 4 | | | IV-1 | Slc18a1 |
| 19943 | 3 | 4 | | | IV-1 | Slc1a7 |
| 19944 | 3 | 4 | | | IV-1 | Slc20a2 |
| 19945 | 3 | 4 | | | IV-1 | Slc22a13 |
| 19946 | 3 | 4 | | | IV-1 | Slc22a29 |
| 19947 | 3 | 4 | | | IV-1 | Slc29a4 |
| 19948 | 3 | 4 | | | IV-1 | Slc34a3 |
| 19949 | 3 | 4 | | | IV-1 | Slc38a10 |
| 19950 | 3 | 4 | | | IV-1 | Slc38a11 |
| 19951 | 3 | 4 | | | IV-1 | Slc44a5 |
| 19952 | 3 | 4 | | | IV-1 | Slc4a9 |
| 19953 | 3 | 4 | | | IV-1 | Slc5a5 |
| 19954 | 3 | 4 | | | IV-1 | Slc5a7 |
| 19955 | 3 | 4 | | | IV-1 | Slc5a8 |
| 19956 | 3 | 4 | | | IV-1 | Slc7a13 |
| 19957 | 3 | 4 | | | IV-1 | Slc7a3 |
| 19958 | 3 | 4 | | | IV-1 | Slc9c1 |
| 19959 | 3 | 4 | | | IV-1 | Slco6d1 |
| 19960 | 3 | 4 | | | IV-1 | Slitrk4 |
| 19961 | 3 | 4 | | | IV-1 | Six |
| 19962 | 3 | 4 | | | IV-1 | Sly |
| 19963 | 3 | 4 | | | IV-1 | Smc1b |
| 19964 | 3 | 4 | | | IV-1 | Sohlh1 |
| 19965 | 3 | 4 | | | IV-1 | Sohlh2 |
| 19966 | 3 | 4 | | | IV-1 | Sorcs1 |

Fig. 34 - 105

| | | | | | | | | | | | | | |
|---|---|---|---|---|---|---|---|---|---|---|---|---|---|
| 19967 | 3 | 4 | | | IV-1 | Sorcs3 | 20063 | 3 | 4 | | | IV-1 | Ubap2l |
| 19968 | 3 | 4 | | | IV-1 | Sox1 | 20064 | 3 | 4 | | | IV-1 | Ube2dnl1 |
| 19969 | 3 | 4 | | | IV-1 | Sox14 | 20065 | 3 | 4 | | | IV-1 | Ube2dnl2 |
| 19970 | 3 | 4 | | | IV-1 | Sox3 | 20066 | 3 | 4 | | | IV-1 | Ube2z |
| 19971 | 3 | 4 | | | IV-1 | Sox5os3 | 20067 | 3 | 4 | | | IV-1 | Ube3b |
| 19972 | 3 | 4 | | | IV-1 | Spaca1 | 20068 | 3 | 4 | | | IV-1 | Ufm1 |
| 19973 | 3 | 4 | | | IV-1 | Spam1 | 20069 | 3 | 4 | | | IV-1 | Uggt2 |
| 19974 | 3 | 4 | | | IV-1 | Spata17 | 20070 | 3 | 4 | | | IV-1 | Ugt2b1 |
| 19975 | 3 | 4 | | | IV-1 | Spata31d1c | 20071 | 3 | 4 | | | IV-1 | Ugt2b35 |
| 19976 | 3 | 4 | | | IV-1 | Spatc1 | 20072 | 3 | 4 | | | IV-1 | Ulk4 |
| 19977 | 3 | 4 | | | IV-1 | Spatc1l | 20073 | 3 | 4 | | | IV-1 | Umodl1 |
| 19978 | 3 | 4 | | | IV-1 | Speer2 | 20074 | 3 | 4 | | | IV-1 | Unc5c |
| 19979 | 3 | 4 | | | IV-1 | Speer3 | 20075 | 3 | 4 | | | IV-1 | Uncx |
| 19980 | 3 | 4 | | | IV-1 | Speer5-ps1 | 20076 | 3 | 4 | | | IV-1 | Ush2a |
| 19981 | 3 | 4 | | | IV-1 | Speer6-ps1 | 20077 | 3 | 4 | | | IV-1 | Usp47 |
| 19982 | 3 | 4 | | | IV-1 | Speer7-ps1 | 20078 | 3 | 4 | | | IV-1 | Usp50 |
| 19983 | 3 | 4 | | | IV-1 | Speer8-ps1 | 20079 | 3 | 4 | | | IV-1 | Usp51 |
| 19984 | 3 | 4 | | | IV-1 | Spef2 | 20080 | 3 | 4 | | | IV-1 | Vamp2 |
| 19985 | 3 | 4 | | | IV-1 | Sprr2k | 20081 | 3 | 4 | | | IV-1 | Vax2os |
| 19986 | 3 | 4 | | | IV-1 | Sspo | 20082 | 3 | 4 | | | IV-1 | Vmn1r40 |
| 19987 | 3 | 4 | | | IV-1 | Sstr1 | 20083 | 3 | 4 | | | IV-1 | Vmn1r90 |
| 19988 | 3 | 4 | | | IV-1 | Ssty1 | 20084 | 3 | 4 | | | IV-1 | Vmn2r122 |
| 19989 | 3 | 4 | | | IV-1 | Ssxb2 | 20085 | 3 | 4 | | | IV-1 | Vmn2r6 |
| 19990 | 3 | 4 | | | IV-1 | St8sia2 | 20086 | 3 | 4 | | | IV-1 | Vmn2r68 |
| 19991 | 3 | 4 | | | IV-1 | Stag3 | 20087 | 3 | 4 | | | IV-1 | Vmn2r7 |
| 19992 | 3 | 4 | | | IV-1 | Stard6 | 20088 | 3 | 4 | | | IV-1 | Vmn2r96 |
| 19993 | 3 | 4 | | | IV-1 | Stoml3 | 20089 | 3 | 4 | | | IV-1 | Vwa5b2 |
| 19994 | 3 | 4 | | | IV-1 | Stra8 | 20090 | 3 | 4 | | | IV-1 | Vwc2 |
| 19995 | 3 | 4 | | | IV-1 | Suitlb1 | 20091 | 3 | 4 | | | IV-1 | Wbp2nl |
| 19996 | 3 | 4 | | | IV-1 | Sval1 | 20092 | 3 | 4 | | | IV-1 | Wdr17 |
| 19997 | 3 | 4 | | | IV-1 | Sycp1 | 20093 | 3 | 4 | | | IV-1 | Wdr27 |
| 19998 | 3 | 4 | | | IV-1 | Syt9 | 20094 | 3 | 4 | | | IV-1 | Wdr38 |
| 19999 | 3 | 4 | | | IV-1 | Tacr3 | 20095 | 3 | 4 | | | IV-1 | Wdr64 |
| 20000 | 3 | 4 | | | IV-1 | Tal2 | 20096 | 3 | 4 | | | IV-1 | Wnk3 |
| 20001 | 3 | 4 | | | IV-1 | Tas1r3 | 20097 | 3 | 4 | | | IV-1 | Wnt9b |
| 20002 | 3 | 4 | | | IV-1 | Tbc1d5 | 20098 | 3 | 4 | | | IV-1 | Wt1os |
| 20003 | 3 | 4 | | | IV-1 | Tbck | 20099 | 3 | 4 | | | IV-1 | Xlr5a |
| 20004 | 3 | 4 | | | IV-1 | Tbx10 | 20100 | 3 | 4 | | | IV-1 | Xlr5b |
| 20005 | 3 | 4 | | | IV-1 | Tbx20 | 20101 | 3 | 4 | | | IV-1 | Zc2hc1b |
| 20006 | 3 | 4 | | | IV-1 | Tbx22 | 20102 | 3 | 4 | | | IV-1 | Zcchc13 |
| 20007 | 3 | 4 | | | IV-1 | Tcerg1l | 20103 | 3 | 4 | | | IV-1 | Zcchc5 |
| 20008 | 3 | 4 | | | IV-1 | Tcp10a | 20104 | 3 | 4 | | | IV-1 | Zfa-ps |
| 20009 | 3 | 4 | | | IV-1 | Tcstv1 | 20105 | 3 | 4 | | | IV-1 | Zfp14 |
| 20010 | 3 | 4 | | | IV-1 | Tdrd1 | 20106 | 3 | 4 | | | IV-1 | Zfp42 |
| 20011 | 3 | 4 | | | IV-1 | Tert | 20107 | 3 | 4 | | | IV-1 | Zfp488 |
| 20012 | 3 | 4 | | | IV-1 | Tespa1 | 20108 | 3 | 4 | | | IV-1 | Zfp512 |
| 20013 | 3 | 4 | | | IV-1 | Tex13 | 20109 | 3 | 4 | | | IV-1 | Zfp648 |
| 20014 | 3 | 4 | | | IV-1 | Tex13a | 20110 | 3 | 4 | | | IV-1 | Zfp735 |
| 20015 | 3 | 4 | | | IV-1 | Tex14 | 20111 | 3 | 4 | | | IV-1 | Zfp786 |
| 20016 | 3 | 4 | | | IV-1 | Tex16 | 20112 | 3 | 4 | | | IV-1 | Zfp804a |
| 20017 | 3 | 4 | | | IV-1 | Tex19.1 | 20113 | 3 | 4 | | | IV-1 | Zfp936 |
| 20018 | 3 | 4 | | | IV-1 | Tex19.2 | 20114 | 3 | 4 | | | IV-1 | Zfp937 |
| 20019 | 3 | 4 | | | IV-1 | Tex21 | 20115 | 3 | 4 | | | IV-1 | Zfp957 |
| 20020 | 3 | 4 | | | IV-1 | Tex35 | 20116 | 3 | 4 | | | IV-1 | Zfy1 |
| 20021 | 3 | 4 | | | IV-1 | Tex36 | 20117 | 3 | 4 | | | IV-1 | Zic3 |
| 20022 | 3 | 4 | | | IV-1 | Tfap2e | 20118 | 3 | 4 | | | IV-1 | Zic5 |
| 20023 | 3 | 4 | | | IV-1 | Tgm6 | 20119 | 3 | 4 | | | IV-1 | Zp2 |
| 20024 | 3 | 4 | | | IV-1 | Them7 | 20120 | 3 | 4 | | | IV-1 | Zp3r |
| 20025 | 3 | 4 | | | IV-1 | Tktl2 | 20121 | 3 | 4 | | | IV-1 | Zscan20 |
| 20026 | 3 | 4 | | | IV-1 | Tlx3 | 20122 | 3 | 4 | | | IV-1 | Zswim5 |
| 20027 | 3 | 4 | | | IV-1 | Tm9sf3 | 20123 | 3 | 4 | | | IV-1 | Zyg11a |
| 20028 | 3 | 4 | | | IV-1 | Tmed10 | 20124 | 3 | | | | | 1110028F18Rik |
| 20029 | 3 | 4 | | | IV-1 | Tmem127 | 20125 | 3 | | | | | 1110036E04Rik |
| 20030 | 3 | 4 | | | IV-1 | Tmem167 | 20126 | 3 | | | | | 1190003K10Rik |
| 20031 | 3 | 4 | | | IV-1 | Tmem169 | 20127 | 3 | | | | | 1500015L24Rik |
| 20032 | 3 | 4 | | | IV-1 | Tmem190 | 20128 | 3 | | | | | 1600015I10Rik |
| 20033 | 3 | 4 | | | IV-1 | Tmem200c | 20129 | 3 | | | | | 1600019K03Rik |
| 20034 | 3 | 4 | | | IV-1 | Tmem217 | 20130 | 3 | | | | | 1700001D01Rik |
| 20035 | 3 | 4 | | | IV-1 | Tmem235 | 20131 | 3 | | | | | 1700016L21Rik |
| 20036 | 3 | 4 | | | IV-1 | Tmem236 | 20132 | 3 | | | | | 1700019E08Rik |
| 20037 | 3 | 4 | | | IV-1 | Tmem57 | 20133 | 3 | | | | | 1700020M21Rik |
| 20038 | 3 | 4 | | | IV-1 | Tmem74 | 20134 | 3 | | | | | 1700022H16Rik |
| 20039 | 3 | 4 | | | IV-1 | Tmem8c | 20135 | 3 | | | | | 1700024I18Rik |
| 20040 | 3 | 4 | | | IV-1 | Tmem95 | 20136 | 3 | | | | | 1700027H10Rik |
| 20041 | 3 | 4 | | | IV-1 | Tmprss11g | 20137 | 3 | | | | | 1700028M03Rik |
| 20042 | 3 | 4 | | | IV-1 | Tnfsf18 | 20138 | 3 | | | | | 1700049E15Rik |
| 20043 | 3 | 4 | | | IV-1 | Tomm70a | 20139 | 3 | | | | | 1700063A18Rik |
| 20044 | 3 | 4 | | | IV-1 | Topaz1 | 20140 | 3 | | | | | 1700063D05Rik |
| 20045 | 3 | 4 | | | IV-1 | Tox3 | 20141 | 3 | | | | | 1700063O14Rik |
| 20046 | 3 | 4 | | | IV-1 | Tpte | 20142 | 3 | | | | | 1700064J06Rik |
| 20047 | 3 | 4 | | | IV-1 | Trhde | 20143 | 3 | | | | | 1700069P05Rik |
| 20048 | 3 | 4 | | | IV-1 | Trhr2 | 20144 | 3 | | | | | 1700084F23Rik |
| 20049 | 3 | 4 | | | IV-1 | Trim17 | 20145 | 3 | | | | | 1700104L18Rik |
| 20050 | 3 | 4 | | | IV-1 | Trim38 | 20146 | 3 | | | | | 1700111N16Rik |
| 20051 | 3 | 4 | | | IV-1 | Trim42 | 20147 | 3 | | | | | 1700121L16Rik |
| 20052 | 3 | 4 | | | IV-1 | Trim66 | 20148 | 3 | | | | | 1700123O21Rik |
| 20053 | 3 | 4 | | | IV-1 | Triml1 | 20149 | 3 | | | | | 1700125G02Rik |
| 20054 | 3 | 4 | | | IV-1 | Trp53cor1 | 20150 | 3 | | | | | 1810007C17Rik |
| 20055 | 3 | 4 | | | IV-1 | Trpc4 | 20151 | 3 | | | | | 2010001E11Rik |
| 20056 | 3 | 4 | | | IV-1 | Trpc7 | 20152 | 3 | | | | | 2010106C02Rik |
| 20057 | 3 | 4 | | | IV-1 | Trpv3 | 20153 | 3 | | | | | 2010310C07Rik |
| 20058 | 3 | 4 | | | IV-1 | Trpv5 | 20154 | 3 | | | | | 2300003K06Rik |
| 20059 | 3 | 4 | | | IV-1 | Ttll2 | 20155 | 3 | | | | | 2310002F09Rik |
| 20060 | 3 | 4 | | | IV-1 | Tunar | 20156 | 3 | | | | | 2310005E17Rik |
| 20061 | 3 | 4 | | | IV-1 | Tyr | 20157 | 3 | | | | | 2310016D03Rik |
| 20062 | 3 | 4 | | | IV-1 | Ubap1l | 20158 | 3 | | | | | 2310034C09Rik |

Fig. 34 - 106

| | | | | | | |
|---|---|---|---|---|---|---|
| 20159 | 3 | | | | | 2310057N15Rik |
| 20160 | 3 | | | | | 2410003L11Rik |
| 20161 | 3 | | | | | 2410012E07Rik |
| 20162 | 3 | | | | | 2410012M07Rik |
| 20163 | 3 | | | | | 2410018L13Rik |
| 20164 | 3 | | | | | 2410021H03Rik |
| 20165 | 3 | | | | | 2410114N07Rik |
| 20166 | 3 | | | | | 2610037D02Rik |
| 20167 | 3 | | | | | 2700089I24Rik |
| 20168 | 3 | | | | | 2810404M03Rik |
| 20169 | 3 | | | | | 2810429I04Rik |
| 20170 | 3 | | | | | 2900057B20Rik |
| 20171 | 3 | | | | | 3110009F21Rik |
| 20172 | 3 | | | | | 3200001D21Rik |
| 20173 | 3 | | | | | 4833417C18Rik |
| 20174 | 3 | | | | | 4921509O07Rik |
| 20175 | 3 | | | | | 4921511C10Rik |
| 20176 | 3 | | | | | 4921511I17Rik |
| 20177 | 3 | | | | | 4921529L05Rik |
| 20178 | 3 | | | | | 4922502N22Rik |
| 20179 | 3 | | | | | 4930402F11Rik |
| 20180 | 3 | | | | | 4930412B13Rik |
| 20181 | 3 | | | | | 4930413M19Rik |
| 20182 | 3 | | | | | 4930419G24Rik |
| 20183 | 3 | | | | | 4930425O10Rik |
| 20184 | 3 | | | | | 4930428G15Rik |
| 20185 | 3 | | | | | 4930429D17Rik |
| 20186 | 3 | | | | | 4930432M17Rik |
| 20187 | 3 | | | | | 4930447A16Rik |
| 20188 | 3 | | | | | 4930448I18Rik |
| 20189 | 3 | | | | | 4930449E18Rik |
| 20190 | 3 | | | | | 4930452N14Rik |
| 20191 | 3 | | | | | 4930455H04Rik |
| 20192 | 3 | | | | | 4930465M20Rik |
| 20193 | 3 | | | | | 4930470H14Rik |
| 20194 | 3 | | | | | 4930474G06Rik |
| 20195 | 3 | | | | | 4930474H20Rik |
| 20196 | 3 | | | | | 4930478L05Rik |
| 20197 | 3 | | | | | 4930480K15Rik |
| 20198 | 3 | | | | | 4930480M12Rik |
| 20199 | 3 | | | | | 4930483O08Rik |
| 20200 | 3 | | | | | 4930488B22Rik |
| 20201 | 3 | | | | | 4930500L23Rik |
| 20202 | 3 | | | | | 4930505G20Rik |
| 20203 | 3 | | | | | 4930509J09Rik |
| 20204 | 3 | | | | | 4930509K18Rik |
| 20205 | 3 | | | | | 4930511E03Rik |
| 20206 | 3 | | | | | 4930512B01Rik |
| 20207 | 3 | | | | | 4930515B02Rik |
| 20208 | 3 | | | | | 4930517E11Rik |
| 20209 | 3 | | | | | 4930521E06Rik |
| 20210 | 3 | | | | | 4930528P14Rik |
| 20211 | 3 | | | | | 4930533P14Rik |
| 20212 | 3 | | | | | 4930539C22Rik |
| 20213 | 3 | | | | | 4930539N22Rik |
| 20214 | 3 | | | | | 4930542D17Rik |
| 20215 | 3 | | | | | 4930546C10Rik |
| 20216 | 3 | | | | | 4930546K05Rik |
| 20217 | 3 | | | | | 4930547E08Rik |
| 20218 | 3 | | | | | 4930554C24Rik |
| 20219 | 3 | | | | | 4930555B11Rik |
| 20220 | 3 | | | | | 4930556G01Rik |
| 20221 | 3 | | | | | 4930558G05Rik |
| 20222 | 3 | | | | | 4930563E18Rik |
| 20223 | 3 | | | | | 4930563M20Rik |
| 20224 | 3 | | | | | 4930590L20Rik |
| 20225 | 3 | | | | | 4930593A02Rik |
| 20226 | 3 | | | | | 4930597G03Rik |
| 20227 | 3 | | | | | 4931402G19Rik |
| 20228 | 3 | | | | | 4931412M21 |
| 20229 | 3 | | | | | 4931429P17Rik |
| 20230 | 3 | | | | | 4932441J04Rik |
| 20231 | 3 | | | | | 4933400B14Rik |
| 20232 | 3 | | | | | 4933400C23Rik |
| 20233 | 3 | | | | | 4933402J15Rik |
| 20234 | 3 | | | | | 4933405E24Rik |
| 20235 | 3 | | | | | 4933406D12Rik |
| 20236 | 3 | | | | | 4933406J10Rik |
| 20237 | 3 | | | | | 4933407G14Rik |
| 20238 | 3 | | | | | 4933416E03Rik |
| 20239 | 3 | | | | | 4933424G05Rik |
| 20240 | 3 | | | | | 4933427E13Rik |
| 20241 | 3 | | | | | 4933427I22Rik |
| 20242 | 3 | | | | | 4933432G23Rik |
| 20243 | 3 | | | | | 4933432I03Rik |
| 20244 | 3 | | | | | 4933433F19Rik |
| 20245 | 3 | | | | | 4933436E23Rik |
| 20246 | 3 | | | | | 5031434C07Rik |
| 20247 | 3 | | | | | 5430402E10Rik |
| 20248 | 3 | | | | | 5430403N17Rik |
| 20249 | 3 | | | | | 5430419D17Rik |
| 20250 | 3 | | | | | 5430428K19Rik |
| 20251 | 3 | | | | | 5430434I15Rik |
| 20252 | 3 | | | | | 5530400C23Rik |
| 20253 | 3 | | | | | 5530401A14Rik |
| 20254 | 3 | | | | | 5730412P04Rik |
| 20255 | 3 | | | | | 5730435O14Rik |
| 20256 | 3 | | | | | 5730457N03Rik |
| 20257 | 3 | | | | | 5730460C07Rik |
| 20258 | 3 | | | | | 5730522E02Rik |
| 20259 | 3 | | | | | 5830416I19Rik |
| 20260 | 3 | | | | | 5930438M14Rik |
| 20261 | 3 | | | | | 6030440G07Rik |
| 20262 | 3 | | | | | 6030469F06Rik |
| 20263 | 3 | | | | | 6330415B21Rik |
| 20264 | 3 | | | | | 6530411M01Rik |
| 20265 | 3 | | | | | 7420426K07Rik |
| 20266 | 3 | | | | | 7420700N18Rik |
| 20267 | 3 | | | | | 7420701I03Rik |
| 20268 | 3 | | | | | 7630403G23Rik |
| 20269 | 3 | | | | | 8030423F21Rik |
| 20270 | 3 | | | | | 8030423I24Rik |
| 20271 | 3 | | | | | 8030442B05Rik |
| 20272 | 3 | | | | | 8030443G20Rik |
| 20273 | 3 | | | | | 8430422H06Rik |
| 20274 | 3 | | | | | 8430423G03Rik |
| 20275 | 3 | | | | | 8430431K14Rik |
| 20276 | 3 | | | | | 8430436N08Rik |
| 20277 | 3 | | | | | 8430437L04Rik |
| 20278 | 3 | | | | | 9030204H09Rik |
| 20279 | 3 | | | | | 9030624G23Rik |
| 20280 | 3 | | | | | 9030625G05Rik |
| 20281 | 3 | | | | | 9130015L21Rik |
| 20282 | 3 | | | | | 9130221F21Rik |
| 20283 | 3 | | | | | 9130227L01Rik |
| 20284 | 3 | | | | | 9230102K24Rik |
| 20285 | 3 | | | | | 9230112D13Rik |
| 20286 | 3 | | | | | 9330111N05Rik |
| 20287 | 3 | | | | | 9330162B11Rik |
| 20288 | 3 | | | | | 9330175M20Rik |
| 20289 | 3 | | | | | 9330178D15Rik |
| 20290 | 3 | | | | | 9330182O14Rik |
| 20291 | 3 | | | | | 9430007A20Rik |
| 20292 | 3 | | | | | 9430018G01Rik |
| 20293 | 3 | | | | | 9430019J16Rik |
| 20294 | 3 | | | | | 9430076C15Rik |
| 20295 | 3 | | | | | 9530003J23Rik |
| 20296 | 3 | | | | | 9530036O11Rik |
| 20297 | 3 | | | | | 9530051G07Rik |
| 20298 | 3 | | | | | 9530059O14Rik |
| 20299 | 3 | | | | | 9630028H03Rik |
| 20300 | 3 | | | | | 9830132P13Rik |
| 20301 | 3 | | | | | 9930111H07Rik |
| 20302 | 3 | | | | | A1bg |
| 20303 | 3 | | | | | A230028O05Rik |
| 20304 | 3 | | | | | A230056J06Rik |
| 20305 | 3 | | | | | A230072E10Rik |
| 20306 | 3 | | | | | A330032B11Rik |
| 20307 | 3 | | | | | A3galt2 |
| 20308 | 3 | | | | | A430089I19Rik |
| 20309 | 3 | | | | | A530006G24Rik |
| 20310 | 3 | | | | | A530046M15Rik |
| 20311 | 3 | | | | | A630012P03Rik |
| 20312 | 3 | | | | | A630075F10Rik |
| 20313 | 3 | | | | | A730018C14Rik |
| 20314 | 3 | | | | | A730043L09Rik |
| 20315 | 3 | | | | | A730046J19Rik |
| 20316 | 3 | | | | | A730082K24Rik |
| 20317 | 3 | | | | | A830019L24Rik |
| 20318 | 3 | | | | | A930006I01Rik |
| 20319 | 3 | | | | | A930007I19Rik |
| 20320 | 3 | | | | | A930011G23Rik |
| 20321 | 3 | | | | | AA388235 |
| 20322 | 3 | | | | | AA536875 |
| 20323 | 3 | | | | | AA543401 |
| 20324 | 3 | | | | | AA545190 |
| 20325 | 3 | | | | | AA619741 |
| 20326 | 3 | | | | | AA792892 |
| 20327 | 3 | | | | | AF067063 |
| 20328 | 3 | | | | | AF357355 |
| 20329 | 3 | | | | | AF357359 |
| 20330 | 3 | | | | | AF357399 |
| 20331 | 3 | | | | | AF357425 |
| 20332 | 3 | | | | | AF357426 |
| 20333 | 3 | | | | | AI197445 |
| 20334 | 3 | | | | | AU016765 |
| 20335 | 3 | | | | | AU018829 |
| 20336 | 3 | | | | | AU019990 |
| 20337 | 3 | | | | | AU021063 |
| 20338 | 3 | | | | | AU023762 |
| 20339 | 3 | | | | | AY512915 |
| 20340 | 3 | | | | | AY761184 |
| 20341 | 3 | | | | | Acsm4 |
| 20342 | 3 | | | | | Adamts18 |
| 20343 | 3 | | | | | Adamts19 |
| 20344 | 3 | | | | | Agbl1 |
| 20345 | 3 | | | | | Ahrr |
| 20346 | 3 | | | | | Ambn |
| 20347 | 3 | | | | | Amelx |
| 20348 | 3 | | | | | Amtn |
| 20349 | 3 | | | | | Ang3 |
| 20350 | 3 | | | | | Ang5 |

Fig. 34 - 107

| | | | | | | | |
|---|---|---|---|---|---|---|---|
| 20351 | 3 | | | | | | Ang6 |
| 20352 | 3 | | | | | | Ankfn1 |
| 20353 | 3 | | | | | | Ankk1 |
| 20354 | 3 | | | | | | Ankrd33 |
| 20355 | 3 | | | | | | Ankub1 |
| 20356 | 3 | | | | | | Apol7d |
| 20357 | 3 | | | | | | Apoo-ps |
| 20358 | 3 | | | | | | Arhgap15os |
| 20359 | 3 | | | | | | Arr3 |
| 20360 | 3 | | | | | | Ascl5 |
| 20361 | 3 | | | | | | Asmt |
| 20362 | 3 | | | | | | Astl |
| 20363 | 3 | | | | | | B020004C17Rik |
| 20364 | 3 | | | | | | B020004J07Rik |
| 20365 | 3 | | | | | | B020014A21Rik |
| 20366 | 3 | | | | | | B020018J22Rik |
| 20367 | 3 | | | | | | B130006D01Rik |
| 20368 | 3 | | | | | | B230112J18Rik |
| 20369 | 3 | | | | | | B230119M05Rik |
| 20370 | 3 | | | | | | B230214G05Rik |
| 20371 | 3 | | | | | | B230319C09Rik |
| 20372 | 3 | | | | | | B230323A14Rik |
| 20373 | 3 | | | | | | B930018H19Rik |
| 20374 | 3 | | | | | | BB557941 |
| 20375 | 3 | | | | | | BC006965 |
| 20376 | 3 | | | | | | BC033916 |
| 20377 | 3 | | | | | | BC037032 |
| 20378 | 3 | | | | | | BC051665 |
| 20379 | 3 | | | | | | BC052688 |
| 20380 | 3 | | | | | | BC053393 |
| 20381 | 3 | | | | | | BC055402 |
| 20382 | 3 | | | | | | BC061212 |
| 20383 | 3 | | | | | | BC080695 |
| 20384 | 3 | | | | | | BC107364 |
| 20385 | 3 | | | | | | BC117090 |
| 20386 | 3 | | | | | | Bc1 |
| 20387 | 3 | | | | | | Bcas3os1 |
| 20388 | 3 | | | | | | Bcl2a1c |
| 20389 | 3 | | | | | | Becn2 |
| 20390 | 3 | | | | | | Bhlhe23 |
| 20391 | 3 | | | | | | Bmp15 |
| 20392 | 3 | | | | | | Bpifa5 |
| 20393 | 3 | | | | | | Bpifa6 |
| 20394 | 3 | | | | | | Bpifb4 |
| 20395 | 3 | | | | | | Bpifb6 |
| 20396 | 3 | | | | | | Bpifb9a |
| 20397 | 3 | | | | | | Bpifb9b |
| 20398 | 3 | | | | | | Brs3 |
| 20399 | 3 | | | | | | Bsph1 |
| 20400 | 3 | | | | | | Bsx |
| 20401 | 3 | | | | | | C030007H22Rik |
| 20402 | 3 | | | | | | C230029M16 |
| 20403 | 3 | | | | | | C230079O03Rik |
| 20404 | 3 | | | | | | C330011F03Rik |
| 20405 | 3 | | | | | | C330024C12Rik |
| 20406 | 3 | | | | | | C330024D21Rik |
| 20407 | 3 | | | | | | C430002E04Rik |
| 20408 | 3 | | | | | | C430002N11Rik |
| 20409 | 3 | | | | | | C630028M04Rik |
| 20410 | 3 | | | | | | C630031E19Rik |
| 20411 | 3 | | | | | | C86187 |
| 20412 | 3 | | | | | | C86695 |
| 20413 | 3 | | | | | | C87198 |
| 20414 | 3 | | | | | | C87414 |
| 20415 | 3 | | | | | | C87499 |
| 20416 | 3 | | | | | | C87977 |
| 20417 | 3 | | | | | | Cabp5 |
| 20418 | 3 | | | | | | Cacna1f |
| 20419 | 3 | | | | | | Calcoco2 |
| 20420 | 3 | | | | | | Calcr |
| 20421 | 3 | | | | | | Calhm1 |
| 20422 | 3 | | | | | | Ccl26 |
| 20423 | 3 | | | | | | Cdcp2 |
| 20424 | 3 | | | | | | Cdk15 |
| 20425 | 3 | | | | | | Cdx4 |
| 20426 | 3 | | | | | | Ceacam-ps1 |
| 20427 | 3 | | | | | | Ceacam11 |
| 20428 | 3 | | | | | | Ceacam14 |
| 20429 | 3 | | | | | | Ceacam5 |
| 20430 | 3 | | | | | | Ceacam9 |
| 20431 | 3 | | | | | | Cer1 |
| 20432 | 3 | | | | | | Chil6 |
| 20433 | 3 | | | | | | ChkbCpt1b |
| 20434 | 3 | | | | | | Chrng |
| 20435 | 3 | | | | | | Cistr-act |
| 20436 | 3 | | | | | | Clec2i |
| 20437 | 3 | | | | | | Clnk |
| 20438 | 3 | | | | | | Clpsl2 |
| 20439 | 3 | | | | | | Clrn2 |
| 20440 | 3 | | | | | | Cphx1 |
| 20441 | 3 | | | | | | Cphx2 |
| 20442 | 3 | | | | | | Crisp4 |
| 20443 | 3 | | | | | | Crx |
| 20444 | 3 | | | | | | Crxos |
| 20445 | 3 | | | | | | Cryba1 |
| 20446 | 3 | | | | | | Crybb2 |
| 20447 | 3 | | | | | | Crygd |
| 20448 | 3 | | | | | | Crygf |
| 20449 | 3 | | | | | | Csf3 |
| 20450 | 3 | | | | | | Csmd2os |
| 20451 | 3 | | | | | | Csn1s1 |
| 20452 | 3 | | | | | | Csn1s2a |
| 20453 | 3 | | | | | | Csn1s2b |
| 20454 | 3 | | | | | | Csn3 |
| 20455 | 3 | | | | | | Cst10 |
| 20456 | 3 | | | | | | Ctf2 |
| 20457 | 3 | | | | | | Cts3 |
| 20458 | 3 | | | | | | Cts6 |
| 20459 | 3 | | | | | | Cts7 |
| 20460 | 3 | | | | | | Cts8 |
| 20461 | 3 | | | | | | Cts8-ps |
| 20462 | 3 | | | | | | Ctsj |
| 20463 | 3 | | | | | | Ctsll3 |
| 20464 | 3 | | | | | | Ctsm |
| 20465 | 3 | | | | | | Ctsq |
| 20466 | 3 | | | | | | Ctsr |
| 20467 | 3 | | | | | | Cyp11b1 |
| 20468 | 3 | | | | | | Cyp11b2 |
| 20469 | 3 | | | | | | Cyp26c1 |
| 20470 | 3 | | | | | | Cyp2c53-ps |
| 20471 | 3 | | | | | | Cyp2t4 |
| 20472 | 3 | | | | | | Cyp3a16 |
| 20473 | 3 | | | | | | Cyp4a29 |
| 20474 | 3 | | | | | | Cyp4a30b |
| 20475 | 3 | | | | | | D030024E09Rik |
| 20476 | 3 | | | | | | D030025E07Rik |
| 20477 | 3 | | | | | | D030025P21Rik |
| 20478 | 3 | | | | | | D130009I18Rik |
| 20479 | 3 | | | | | | D130058E03 |
| 20480 | 3 | | | | | | D14Ertd670e |
| 20481 | 3 | | | | | | D17Ertd648e |
| 20482 | 3 | | | | | | D530049I02Rik |
| 20483 | 3 | | | | | | D5Ertd577e |
| 20484 | 3 | | | | | | D630010B17Rik |
| 20485 | 3 | | | | | | D730005E14Rik |
| 20486 | 3 | | | | | | D730045A05Rik |
| 20487 | 3 | | | | | | D730048I06Rik |
| 20488 | 3 | | | | | | D730050B12Rik |
| 20489 | 3 | | | | | | D930032P07Rik |
| 20490 | 3 | | | | | | DQ267100 |
| 20491 | 3 | | | | | | DQ267101 |
| 20492 | 3 | | | | | | DQ267102 |
| 20493 | 3 | | | | | | DXBay18 |
| 20494 | 3 | | | | | | Dbhos |
| 20495 | 3 | | | | | | Dbx1 |
| 20496 | 3 | | | | | | Defa-ps1 |
| 20497 | 3 | | | | | | Defa-ps12 |
| 20498 | 3 | | | | | | Defa-ps13 |
| 20499 | 3 | | | | | | Defa2 |
| 20500 | 3 | | | | | | Defa20 |
| 20501 | 3 | | | | | | Defa21 |
| 20502 | 3 | | | | | | Defa22 |
| 20503 | 3 | | | | | | Defa25 |
| 20504 | 3 | | | | | | Defa26 |
| 20505 | 3 | | | | | | Defa4 |
| 20506 | 3 | | | | | | Defa5 |
| 20507 | 3 | | | | | | Defb10 |
| 20508 | 3 | | | | | | Defb12 |
| 20509 | 3 | | | | | | Defb13 |
| 20510 | 3 | | | | | | Defb18 |
| 20511 | 3 | | | | | | Defb34 |
| 20512 | 3 | | | | | | Defb35 |
| 20513 | 3 | | | | | | Defb44-ps |
| 20514 | 3 | | | | | | Defb46 |
| 20515 | 3 | | | | | | Defb7 |
| 20516 | 3 | | | | | | Defb59 |
| 20517 | 3 | | | | | | Disc1 |
| 20518 | 3 | | | | | | Dkk1 |
| 20519 | 3 | | | | | | Dkk4 |
| 20520 | 3 | | | | | | Dlx6as2 |
| 20521 | 3 | | | | | | Dnah11 |
| 20522 | 3 | | | | | | Doxl2 |
| 20523 | 3 | | | | | | Dppa1 |
| 20524 | 3 | | | | | | Dppa2 |
| 20525 | 3 | | | | | | Dppa4 |
| 20526 | 3 | | | | | | Dsg4 |
| 20527 | 3 | | | | | | Dspp |
| 20528 | 3 | | | | | | Dthd1 |
| 20529 | 3 | | | | | | Duxbl1 |
| 20530 | 3 | | | | | | Duxbl3 |
| 20531 | 3 | | | | | | Dynap |
| 20532 | 3 | | | | | | E030002O03Rik |
| 20533 | 3 | | | | | | E030025P04Rik |
| 20534 | 3 | | | | | | E130304I02Rik |
| 20535 | 3 | | | | | | E230019M04Rik |
| 20536 | 3 | | | | | | E330014E10Rik |
| 20537 | 3 | | | | | | E330017L17Rik |
| 20538 | 3 | | | | | | E330023G01Rik |
| 20539 | 3 | | | | | | EU599041 |
| 20540 | 3 | | | | | | Ear14 |
| 20541 | 3 | | | | | | Ear4 |
| 20542 | 3 | | | | | | Ect2l |

Fig. 34 - 108

| | | | | | | |
|---|---|---|---|---|---|---|
| 20543 | 3 | | | | | Enam |
| 20544 | 3 | | | | | Enpp7 |
| 20545 | 3 | | | | | Epo |
| 20546 | 3 | | | | | Eras |
| 20547 | 3 | | | | | Esp1 |
| 20548 | 3 | | | | | Esp15 |
| 20549 | 3 | | | | | Esp16 |
| 20550 | 3 | | | | | Esp18 |
| 20551 | 3 | | | | | Esp23 |
| 20552 | 3 | | | | | Esp24 |
| 20553 | 3 | | | | | Esp3 |
| 20554 | 3 | | | | | Esp31 |
| 20555 | 3 | | | | | Esp34 |
| 20556 | 3 | | | | | Esp36 |
| 20557 | 3 | | | | | Esp38 |
| 20558 | 3 | | | | | Esp4 |
| 20559 | 3 | | | | | Esp5 |
| 20560 | 3 | | | | | Esp6 |
| 20561 | 3 | | | | | Esp6-esp5 |
| 20562 | 3 | | | | | Espnl |
| 20563 | 3 | | | | | Evi2a-evi2b |
| 20564 | 3 | | | | | F630111L10Rik |
| 20565 | 3 | | | | | F630206G17Rik |
| 20566 | 3 | | | | | F730035M05Rik |
| 20567 | 3 | | | | | F830016B08Rik |
| 20568 | 3 | | | | | Fam159b |
| 20569 | 3 | | | | | Fate1 |
| 20570 | 3 | | | | | Fbxw14 |
| 20571 | 3 | | | | | Fbxw16 |
| 20572 | 3 | | | | | Fbxw19 |
| 20573 | 3 | | | | | Fbxw20 |
| 20574 | 3 | | | | | Fbxw21 |
| 20575 | 3 | | | | | Fbxw22 |
| 20576 | 3 | | | | | Fbxw24 |
| 20577 | 3 | | | | | Fbxw28 |
| 20578 | 3 | | | | | Ferd3l |
| 20579 | 3 | | | | | Fgf15 |
| 20580 | 3 | | | | | Fgf23 |
| 20581 | 3 | | | | | Fgf4 |
| 20582 | 3 | | | | | Fhad1os1 |
| 20583 | 3 | | | | | Fmo6 |
| 20584 | 3 | | | | | Fmo9 |
| 20585 | 3 | | | | | Fnd3c2 |
| 20586 | 3 | | | | | Fndc3c1 |
| 20587 | 3 | | | | | Foxb2 |
| 20588 | 3 | | | | | Foxd4 |
| 20589 | 3 | | | | | Foxe1 |
| 20590 | 3 | | | | | Foxi2 |
| 20591 | 3 | | | | | Foxi2os |
| 20592 | 3 | | | | | Foxn4 |
| 20593 | 3 | | | | | Fpr-rs3 |
| 20594 | 3 | | | | | Fpr-rs4 |
| 20595 | 3 | | | | | Fpr-rs6 |
| 20596 | 3 | | | | | Fpr3 |
| 20597 | 3 | | | | | Frem3 |
| 20598 | 3 | | | | | Frmpd1os |
| 20599 | 3 | | | | | Frmpd3 |
| 20600 | 3 | | | | | Fshb |
| 20601 | 3 | | | | | Fut4-ps1 |
| 20602 | 3 | | | | | G530011O06Rik |
| 20603 | 3 | | | | | G630055G22Rik |
| 20604 | 3 | | | | | G630071F17Rik |
| 20605 | 3 | | | | | Gabrr3 |
| 20606 | 3 | | | | | Gaip |
| 20607 | 3 | | | | | Gbx1 |
| 20608 | 3 | | | | | Gcm2 |
| 20609 | 3 | | | | | Gcnt7 |
| 20610 | 3 | | | | | Gfral |
| 20611 | 3 | | | | | Ghsr |
| 20612 | 3 | | | | | Gja10 |
| 20613 | 3 | | | | | Gja8 |
| 20614 | 3 | | | | | Gjd4 |
| 20615 | 3 | | | | | Glra4 |
| 20616 | 3 | | | | | Glyatl3 |
| 20617 | 3 | | | | | Gm10007 |
| 20618 | 3 | | | | | Gm10052 |
| 20619 | 3 | | | | | Gm10057 |
| 20620 | 3 | | | | | Gm10081 |
| 20621 | 3 | | | | | Gm10104 |
| 20622 | 3 | | | | | Gm10248 |
| 20623 | 3 | | | | | Gm10267 |
| 20624 | 3 | | | | | Gm10280 |
| 20625 | 3 | | | | | Gm10373 |
| 20626 | 3 | | | | | Gm10389 |
| 20627 | 3 | | | | | Gm10390 |
| 20628 | 3 | | | | | Gm10400 |
| 20629 | 3 | | | | | Gm10408 |
| 20630 | 3 | | | | | Gm10415 |
| 20631 | 3 | | | | | Gm10436 |
| 20632 | 3 | | | | | Gm10440 |
| 20633 | 3 | | | | | Gm10445 |
| 20634 | 3 | | | | | Gm10466 |
| 20635 | 3 | | | | | Gm10474 |
| 20636 | 3 | | | | | Gm10494 |
| 20637 | 3 | | | | | Gm10510 |
| 20638 | 3 | | | | | Gm10512 |
| 20639 | 3 | | | | | Gm10536 |
| 20640 | 3 | | | | | Gm10538 |
| 20641 | 3 | | | | | Gm10548 |
| 20642 | 3 | | | | | Gm10549 |
| 20643 | 3 | | | | | Gm10556 |
| 20644 | 3 | | | | | Gm10578 |
| 20645 | 3 | | | | | Gm10635 |
| 20646 | 3 | | | | | Gm10636 |
| 20647 | 3 | | | | | Gm10637 |
| 20648 | 3 | | | | | Gm10649 |
| 20649 | 3 | | | | | Gm10662 |
| 20650 | 3 | | | | | Gm10665 |
| 20651 | 3 | | | | | Gm10666 |
| 20652 | 3 | | | | | Gm10670 |
| 20653 | 3 | | | | | Gm10696 |
| 20654 | 3 | | | | | Gm10714 |
| 20655 | 3 | | | | | Gm10745 |
| 20656 | 3 | | | | | Gm10789 |
| 20657 | 3 | | | | | Gm10823 |
| 20658 | 3 | | | | | Gm10825 |
| 20659 | 3 | | | | | Gm11186 |
| 20660 | 3 | | | | | Gm11237 |
| 20661 | 3 | | | | | Gm11351 |
| 20662 | 3 | | | | | Gm1140 |
| 20663 | 3 | | | | | Gm11413 |
| 20664 | 3 | | | | | Gm11426 |
| 20665 | 3 | | | | | Gm11468 |
| 20666 | 3 | | | | | Gm11487 |
| 20667 | 3 | | | | | Gm11529 |
| 20668 | 3 | | | | | Gm11541 |
| 20669 | 3 | | | | | Gm11544 |
| 20670 | 3 | | | | | Gm11548 |
| 20671 | 3 | | | | | Gm11569 |
| 20672 | 3 | | | | | Gm11747 |
| 20673 | 3 | | | | | Gm11758 |
| 20674 | 3 | | | | | Gm11961 |
| 20675 | 3 | | | | | Gm11985 |
| 20676 | 3 | | | | | Gm12 |
| 20677 | 3 | | | | | Gm12130 |
| 20678 | 3 | | | | | Gm12169 |
| 20679 | 3 | | | | | Gm12171 |
| 20680 | 3 | | | | | Gm12238 |
| 20681 | 3 | | | | | Gm12253 |
| 20682 | 3 | | | | | Gm12505 |
| 20683 | 3 | | | | | Gm12603 |
| 20684 | 3 | | | | | Gm12669 |
| 20685 | 3 | | | | | Gm12789 |
| 20686 | 3 | | | | | Gm12794 |
| 20687 | 3 | | | | | Gm12830 |
| 20688 | 3 | | | | | Gm12886 |
| 20689 | 3 | | | | | Gm12887 |
| 20690 | 3 | | | | | Gm13023 |
| 20691 | 3 | | | | | Gm13040 |
| 20692 | 3 | | | | | Gm13043 |
| 20693 | 3 | | | | | Gm13051 |
| 20694 | 3 | | | | | Gm13057 |
| 20695 | 3 | | | | | Gm13078 |
| 20696 | 3 | | | | | Gm13083 |
| 20697 | 3 | | | | | Gm13084 |
| 20698 | 3 | | | | | Gm13088 |
| 20699 | 3 | | | | | Gm13102 |
| 20700 | 3 | | | | | Gm13103 |
| 20701 | 3 | | | | | Gm13119 |
| 20702 | 3 | | | | | Gm13125 |
| 20703 | 3 | | | | | Gm13128 |
| 20704 | 3 | | | | | Gm1322 |
| 20705 | 3 | | | | | Gm13247 |
| 20706 | 3 | | | | | Gm13271 |
| 20707 | 3 | | | | | Gm13272 |
| 20708 | 3 | | | | | Gm13275 |
| 20709 | 3 | | | | | Gm13276 |
| 20710 | 3 | | | | | Gm13277 |
| 20711 | 3 | | | | | Gm13278 |
| 20712 | 3 | | | | | Gm13279 |
| 20713 | 3 | | | | | Gm13283 |
| 20714 | 3 | | | | | Gm13286 |
| 20715 | 3 | | | | | Gm13288 |
| 20716 | 3 | | | | | Gm13497 |
| 20717 | 3 | | | | | Gm13544 |
| 20718 | 3 | | | | | Gm13582 |
| 20719 | 3 | | | | | Gm13749 |
| 20720 | 3 | | | | | Gm13752 |
| 20721 | 3 | | | | | Gm13769 |
| 20722 | 3 | | | | | Gm13939 |
| 20723 | 3 | | | | | Gm14015 |
| 20724 | 3 | | | | | Gm14092 |
| 20725 | 3 | | | | | Gm14124 |
| 20726 | 3 | | | | | Gm14139 |
| 20727 | 3 | | | | | Gm14306 |
| 20728 | 3 | | | | | Gm14345 |
| 20729 | 3 | | | | | Gm14459 |
| 20730 | 3 | | | | | Gm14496 |
| 20731 | 3 | | | | | Gm14548 |
| 20732 | 3 | | | | | Gm14635 |
| 20733 | 3 | | | | | Gm14692 |
| 20734 | 3 | | | | | Gm14743 |

Fig. 34 - 109

| | | | | | | | | | | | | |
|---|---|---|---|---|---|---|---|---|---|---|---|---|
| 20735 | 3 | | | | | Gm14744 | 20831 | 3 | | | | Gm4224 |
| 20736 | 3 | | | | | Gm14812 | 20832 | 3 | | | | Gm4265 |
| 20737 | 3 | | | | | Gm14850 | 20833 | 3 | | | | Gm4278 |
| 20738 | 3 | | | | | Gm14858 | 20834 | 3 | | | | Gm428 |
| 20739 | 3 | | | | | Gm15008 | 20835 | 3 | | | | Gm4301 |
| 20740 | 3 | | | | | Gm15023 | 20836 | 3 | | | | Gm4302 |
| 20741 | 3 | | | | | Gm15292 | 20837 | 3 | | | | Gm4303 |
| 20742 | 3 | | | | | Gm15293 | 20838 | 3 | | | | Gm4307 |
| 20743 | 3 | | | | | Gm15299 | 20839 | 3 | | | | Gm4312 |
| 20744 | 3 | | | | | Gm15308 | 20840 | 3 | | | | Gm4340 |
| 20745 | 3 | | | | | Gm15315 | 20841 | 3 | | | | Gm4371 |
| 20746 | 3 | | | | | Gm15413 | 20842 | 3 | | | | Gm44 |
| 20747 | 3 | | | | | Gm156 | 20843 | 3 | | | | Gm4432 |
| 20748 | 3 | | | | | Gm15679 | 20844 | 3 | | | | Gm4461 |
| 20749 | 3 | | | | | Gm15713 | 20845 | 3 | | | | Gm4567 |
| 20750 | 3 | | | | | Gm1587 | 20846 | 3 | | | | Gm4710 |
| 20751 | 3 | | | | | Gm15941 | 20847 | 3 | | | | Gm4736 |
| 20752 | 3 | | | | | Gm15997 | 20848 | 3 | | | | Gm4791 |
| 20753 | 3 | | | | | Gm16287 | 20849 | 3 | | | | Gm4792 |
| 20754 | 3 | | | | | Gm16291 | 20850 | 3 | | | | Gm4794 |
| 20755 | 3 | | | | | Gm16294 | 20851 | 3 | | | | Gm4832 |
| 20756 | 3 | | | | | Gm1631 | 20852 | 3 | | | | Gm4847 |
| 20757 | 3 | | | | | Gm16336 | 20853 | 3 | | | | Gm4850 |
| 20758 | 3 | | | | | Gm16432 | 20854 | 3 | | | | Gm4858 |
| 20759 | 3 | | | | | Gm16451 | 20855 | 3 | | | | Gm4861 |
| 20760 | 3 | | | | | Gm16497 | 20856 | 3 | | | | Gm4872 |
| 20761 | 3 | | | | | Gm16796 | 20857 | 3 | | | | Gm4894 |
| 20762 | 3 | | | | | Gm16833 | 20858 | 3 | | | | Gm4906 |
| 20763 | 3 | | | | | Gm1715 | 20859 | 3 | | | | Gm4971 |
| 20764 | 3 | | | | | Gm17644 | 20860 | 3 | | | | Gm4975 |
| 20765 | 3 | | | | | Gm17660 | 20861 | 3 | | | | Gm4981 |
| 20766 | 3 | | | | | Gm17677 | 20862 | 3 | | | | Gm5039 |
| 20767 | 3 | | | | | Gm17689 | 20863 | 3 | | | | Gm5082 |
| 20768 | 3 | | | | | Gm17727 | 20864 | 3 | | | | Gm5087 |
| 20769 | 3 | | | | | Gm17751 | 20865 | 3 | | | | Gm5095 |
| 20770 | 3 | | | | | Gm17821 | 20866 | 3 | | | | Gm5166 |
| 20771 | 3 | | | | | Gm17830 | 20867 | 3 | | | | Gm5177 |
| 20772 | 3 | | | | | Gm18409 | 20868 | 3 | | | | Gm5414 |
| 20773 | 3 | | | | | Gm19276 | 20869 | 3 | | | | Gm5420 |
| 20774 | 3 | | | | | Gm19299 | 20870 | 3 | | | | Gm5476 |
| 20775 | 3 | | | | | Gm19303 | 20871 | 3 | | | | Gm5477 |
| 20776 | 3 | | | | | Gm19424 | 20872 | 3 | | | | Gm5531 |
| 20777 | 3 | | | | | Gm19434 | 20873 | 3 | | | | Gm5535 |
| 20778 | 3 | | | | | Gm19466 | 20874 | 3 | | | | Gm5544 |
| 20779 | 3 | | | | | Gm19510 | 20875 | 3 | | | | Gm5712 |
| 20780 | 3 | | | | | Gm19589 | 20876 | 3 | | | | Gm5725 |
| 20781 | 3 | | | | | Gm19689 | 20877 | 3 | | | | Gm5726 |
| 20782 | 3 | | | | | Gm19757 | 20878 | 3 | | | | Gm5728 |
| 20783 | 3 | | | | | Gm19782 | 20879 | 3 | | | | Gm5833 |
| 20784 | 3 | | | | | Gm19784 | 20880 | 3 | | | | Gm5868 |
| 20785 | 3 | | | | | Gm20110 | 20881 | 3 | | | | Gm5885 |
| 20786 | 3 | | | | | Gm20125 | 20882 | 3 | | | | Gm5886 |
| 20787 | 3 | | | | | Gm20139 | 20883 | 3 | | | | Gm5891 |
| 20788 | 3 | | | | | Gm20187 | 20884 | 3 | | | | Gm5916 |
| 20789 | 3 | | | | | Gm2022 | 20885 | 3 | | | | Gm5938 |
| 20790 | 3 | | | | | Gm20356 | 20886 | 3 | | | | Gm6042 |
| 20791 | 3 | | | | | Gm20362 | 20887 | 3 | | | | Gm6116 |
| 20792 | 3 | | | | | Gm20556 | 20888 | 3 | | | | Gm6150 |
| 20793 | 3 | | | | | Gm20597 | 20889 | 3 | | | | Gm6164 |
| 20794 | 3 | | | | | Gm20741 | 20890 | 3 | | | | Gm6213 |
| 20795 | 3 | | | | | Gm20744 | 20891 | 3 | | | | Gm6313 |
| 20796 | 3 | | | | | Gm20745 | 20892 | 3 | | | | Gm6367 |
| 20797 | 3 | | | | | Gm20750 | 20893 | 3 | | | | Gm6406 |
| 20798 | 3 | | | | | Gm20755 | 20894 | 3 | | | | Gm6498 |
| 20799 | 3 | | | | | Gm20756 | 20895 | 3 | | | | Gm6559 |
| 20800 | 3 | | | | | Gm20757 | 20896 | 3 | | | | Gm6592 |
| 20801 | 3 | | | | | Gm20758 | 20897 | 3 | | | | Gm6602 |
| 20802 | 3 | | | | | Gm20759 | 20898 | 3 | | | | Gm6634 |
| 20803 | 3 | | | | | Gm20765 | 20899 | 3 | | | | Gm6696 |
| 20804 | 3 | | | | | Gm20767 | 20900 | 3 | | | | Gm6763 |
| 20805 | 3 | | | | | Gm20816 | 20901 | 3 | | | | Gm6878 |
| 20806 | 3 | | | | | Gm2109 | 20902 | 3 | | | | Gm6936 |
| 20807 | 3 | | | | | Gm21276 | 20903 | 3 | | | | Gm6938 |
| 20808 | 3 | | | | | Gm21293 | 20904 | 3 | | | | Gm6994 |
| 20809 | 3 | | | | | Gm21304 | 20905 | 3 | | | | Gm7056 |
| 20810 | 3 | | | | | Gm21312 | 20906 | 3 | | | | Gm7134 |
| 20811 | 3 | | | | | Gm21319 | 20907 | 3 | | | | Gm7173 |
| 20812 | 3 | | | | | Gm21498 | 20908 | 3 | | | | Gm7257 |
| 20813 | 3 | | | | | Gm21944 | 20909 | 3 | | | | Gm7271 |
| 20814 | 3 | | | | | Gm2373 | 20910 | 3 | | | | Gm7337 |
| 20815 | 3 | | | | | Gm2381 | 20911 | 3 | | | | Gm7457 |
| 20816 | 3 | | | | | Gm2447 | 20912 | 3 | | | | Gm7534 |
| 20817 | 3 | | | | | Gm2516 | 20913 | 3 | | | | Gm7538 |
| 20818 | 3 | | | | | Gm3020 | 20914 | 3 | | | | Gm7550 |
| 20819 | 3 | | | | | Gm3139 | 20915 | 3 | | | | Gm7616 |
| 20820 | 3 | | | | | Gm3259 | 20916 | 3 | | | | Gm7714 |
| 20821 | 3 | | | | | Gm3279 | 20917 | 3 | | | | Gm7849 |
| 20822 | 3 | | | | | Gm3286 | 20918 | 3 | | | | Gm7861 |
| 20823 | 3 | | | | | Gm3428 | 20919 | 3 | | | | Gm7903 |
| 20824 | 3 | | | | | Gm3434 | 20920 | 3 | | | | Gm7977 |
| 20825 | 3 | | | | | Gm3701 | 20921 | 3 | | | | Gm7978 |
| 20826 | 3 | | | | | Gm4133 | 20922 | 3 | | | | Gm813 |
| 20827 | 3 | | | | | Gm4175 | 20923 | 3 | | | | Gm815 |
| 20828 | 3 | | | | | Gm4201 | 20924 | 3 | | | | Gm8179 |
| 20829 | 3 | | | | | Gm4214 | 20925 | 3 | | | | Gm8234 |
| 20830 | 3 | | | | | Gm4216 | 20926 | 3 | | | | Gm829 |

Fig. 34 - 110

| | | | | | | |
|---|---|---|---|---|---|---|
| 20927 | 3 | | | | | Gm8298 |
| 20928 | 3 | | | | | Gm8300 |
| 20929 | 3 | | | | | Gm833 |
| 20930 | 3 | | | | | Gm839 |
| 20931 | 3 | | | | | Gm8579 |
| 20932 | 3 | | | | | Gm8677 |
| 20933 | 3 | | | | | Gm8693 |
| 20934 | 3 | | | | | Gm8709 |
| 20935 | 3 | | | | | Gm8882 |
| 20936 | 3 | | | | | Gm9125 |
| 20937 | 3 | | | | | Gm9159 |
| 20938 | 3 | | | | | Gm9268 |
| 20939 | 3 | | | | | Gm9376 |
| 20940 | 3 | | | | | Gm9513 |
| 20941 | 3 | | | | | Gm9767 |
| 20942 | 3 | | | | | Gm9871 |
| 20943 | 3 | | | | | Gm9920 |
| 20944 | 3 | | | | | Gngt1 |
| 20945 | 3 | | | | | Gnrhr |
| 20946 | 3 | | | | | Gphb5 |
| 20947 | 3 | | | | | Gpr119 |
| 20948 | 3 | | | | | Gpr142 |
| 20949 | 3 | | | | | Gpr143 |
| 20950 | 3 | | | | | Gpr152 |
| 20951 | 3 | | | | | Gpr50 |
| 20952 | 3 | | | | | Gpr98 |
| 20953 | 3 | | | | | Grk1 |
| 20954 | 3 | | | | | Grxcr1 |
| 20955 | 3 | | | | | Grxcr2 |
| 20956 | 3 | | | | | Gsdma3 |
| 20957 | 3 | | | | | Gsx1 |
| 20958 | 3 | | | | | Gsx2 |
| 20959 | 3 | | | | | Guca1b |
| 20960 | 3 | | | | | Gucy1b2 |
| 20961 | 3 | | | | | Gucy2f |
| 20962 | 3 | | | | | Gzmd |
| 20963 | 3 | | | | | Gzme |
| 20964 | 3 | | | | | Gzmf |
| 20965 | 3 | | | | | Gzmg |
| 20966 | 3 | | | | | H1foo |
| 20967 | 3 | | | | | H2-L |
| 20968 | 3 | | | | | H2-M1 |
| 20969 | 3 | | | | | H2-M10.1 |
| 20970 | 3 | | | | | H2-M10.2 |
| 20971 | 3 | | | | | H2-M10.3 |
| 20972 | 3 | | | | | H2-M10.4 |
| 20973 | 3 | | | | | H2-M10.5 |
| 20974 | 3 | | | | | H2-M10.6 |
| 20975 | 3 | | | | | H2-M11 |
| 20976 | 3 | | | | | H2afb2 |
| 20977 | 3 | | | | | Has2os |
| 20978 | 3 | | | | | Hbb-bh1 |
| 20979 | 3 | | | | | Hbb-bh2 |
| 20980 | 3 | | | | | Hbb-y |
| 20981 | 3 | | | | | Hdx |
| 20982 | 3 | | | | | Hesx1 |
| 20983 | 3 | | | | | Hhla1 |
| 20984 | 3 | | | | | Higd1c |
| 20985 | 3 | | | | | Hotair |
| 20986 | 3 | | | | | Hoxb1 |
| 20987 | 3 | | | | | Hoxc12 |
| 20988 | 3 | | | | | Hoxd1 |
| 20989 | 3 | | | | | Hsf3 |
| 20990 | 3 | | | | | Hyal4 |
| 20991 | 3 | | | | | I730028E13Rik |
| 20992 | 3 | | | | | Ifi44l |
| 20993 | 3 | | | | | Ifna1 |
| 20994 | 3 | | | | | Ifna11 |
| 20995 | 3 | | | | | Ifna12 |
| 20996 | 3 | | | | | Ifna13 |
| 20997 | 3 | | | | | Ifna14 |
| 20998 | 3 | | | | | Ifna15 |
| 20999 | 3 | | | | | Ifna16 |
| 21000 | 3 | | | | | Ifna2 |
| 21001 | 3 | | | | | Ifna4 |
| 21002 | 3 | | | | | Ifna5 |
| 21003 | 3 | | | | | Ifna6 |
| 21004 | 3 | | | | | Ifna7 |
| 21005 | 3 | | | | | Ifna9 |
| 21006 | 3 | | | | | Ifnb1 |
| 21007 | 3 | | | | | Ifne |
| 21008 | 3 | | | | | Ifnl2 |
| 21009 | 3 | | | | | Ifnl3 |
| 21010 | 3 | | | | | Igdcc3 |
| 21011 | 3 | | | | | Igf2os |
| 21012 | 3 | | | | | Igfl3 |
| 21013 | 3 | | | | | Il17a |
| 21014 | 3 | | | | | Il17f |
| 21015 | 3 | | | | | Il1rapl2 |
| 21016 | 3 | | | | | Il2 |
| 21017 | 3 | | | | | Il20 |
| 21018 | 3 | | | | | Il23r |
| 21019 | 3 | | | | | Il24 |
| 21020 | 3 | | | | | Il3 |
| 21021 | 3 | | | | | Il6 |
| 21022 | 3 | | | | | Il9 |
| 21023 | 3 | | | | | Insm2 |
| 21024 | 3 | | | | | Kank4os |
| 21025 | 3 | | | | | Kcna10 |
| 21026 | 3 | | | | | Kcng3 |
| 21027 | 3 | | | | | Kcnk18 |
| 21028 | 3 | | | | | Khdc1b |
| 21029 | 3 | | | | | Khdc1c |
| 21030 | 3 | | | | | Kir3dl1 |
| 21031 | 3 | | | | | Kir3dl2 |
| 21032 | 3 | | | | | Kis2 |
| 21033 | 3 | | | | | Klhdc7b |
| 21034 | 3 | | | | | Klra12 |
| 21035 | 3 | | | | | Klra14-ps |
| 21036 | 3 | | | | | Klra19 |
| 21037 | 3 | | | | | Klra21 |
| 21038 | 3 | | | | | Klra23 |
| 21039 | 3 | | | | | Klra33 |
| 21040 | 3 | | | | | Klra4 |
| 21041 | 3 | | | | | Klra6 |
| 21042 | 3 | | | | | Klra8 |
| 21043 | 3 | | | | | Klrb1-ps1 |
| 21044 | 3 | | | | | Klrc2 |
| 21045 | 3 | | | | | Krt39 |
| 21046 | 3 | | | | | Krt74 |
| 21047 | 3 | | | | | Krt76 |
| 21048 | 3 | | | | | Krtap13 |
| 21049 | 3 | | | | | Krtap20-2 |
| 21050 | 3 | | | | | Krtap31-2 |
| 21051 | 3 | | | | | Krtap9-5 |
| 21052 | 3 | | | | | LOC100043315 |
| 21053 | 3 | | | | | LOC100502896 |
| 21054 | 3 | | | | | LOC100503280 |
| 21055 | 3 | | | | | LOC100862015 |
| 21056 | 3 | | | | | LOC101055863 |
| 21057 | 3 | | | | | LOC101243624 |
| 21058 | 3 | | | | | LOC102308570 |
| 21059 | 3 | | | | | LOC102633035 |
| 21060 | 3 | | | | | LOC102634101 |
| 21061 | 3 | | | | | LOC102634431 |
| 21062 | 3 | | | | | LOC171588 |
| 21063 | 3 | | | | | Lactbl1 |
| 21064 | 3 | | | | | Lcn11 |
| 21065 | 3 | | | | | Lcn12 |
| 21066 | 3 | | | | | Lcn3 |
| 21067 | 3 | | | | | Lcn5 |
| 21068 | 3 | | | | | Lcn6 |
| 21069 | 3 | | | | | Lcor |
| 21070 | 3 | | | | | Ldlrad2 |
| 21071 | 3 | | | | | Lgsn |
| 21072 | 3 | | | | | Lhx3 |
| 21073 | 3 | | | | | Lhx4 |
| 21074 | 3 | | | | | Lim2 |
| 21075 | 3 | | | | | Lipi |
| 21076 | 3 | | | | | Lnx1b |
| 21077 | 3 | | | | | Lrit3 |
| 21078 | 3 | | | | | Lyg1 |
| 21079 | 3 | | | | | Magea1 |
| 21080 | 3 | | | | | Magea2 |
| 21081 | 3 | | | | | Mageb16-ps1 |
| 21082 | 3 | | | | | Matn1 |
| 21083 | 3 | | | | | Mbd3l2 |
| 21084 | 3 | | | | | Mcidas |
| 21085 | 3 | | | | | Mcpt9 |
| 21086 | 3 | | | | | Mei1 |
| 21087 | 3 | | | | | Mepe |
| 21088 | 3 | | | | | Mir100 |
| 21089 | 3 | | | | | Mir101a |
| 21090 | 3 | | | | | Mir101b |
| 21091 | 3 | | | | | Mir101c |
| 21092 | 3 | | | | | Mir103-1 |
| 21093 | 3 | | | | | Mir103-2 |
| 21094 | 3 | | | | | Mir105 |
| 21095 | 3 | | | | | Mir106a |
| 21096 | 3 | | | | | Mir106b |
| 21097 | 3 | | | | | Mir107 |
| 21098 | 3 | | | | | Mir10b |
| 21099 | 3 | | | | | Mir1187 |
| 21100 | 3 | | | | | Mir1188 |
| 21101 | 3 | | | | | Mir1190 |
| 21102 | 3 | | | | | Mir1191 |
| 21103 | 3 | | | | | Mir1191b |
| 21104 | 3 | | | | | Mir1192 |
| 21105 | 3 | | | | | Mir1193 |
| 21106 | 3 | | | | | Mir1195 |
| 21107 | 3 | | | | | Mir1197 |
| 21108 | 3 | | | | | Mir1198 |
| 21109 | 3 | | | | | Mir1224 |
| 21110 | 3 | | | | | Mir122a |
| 21111 | 3 | | | | | Mir1231 |
| 21112 | 3 | | | | | Mir1247 |
| 21113 | 3 | | | | | Mir1249 |
| 21114 | 3 | | | | | Mir124a-1 |
| 21115 | 3 | | | | | Mir124a-2 |
| 21116 | 3 | | | | | Mir124a-3 |
| 21117 | 3 | | | | | Mir1251 |
| 21118 | 3 | | | | | Mir1258 |

Fig. 34 - 111

| | | | | | |
|---|---|---|---|---|---|
| 21119 | 3 | | | | Mir125a |
| 21120 | 3 | | | | Mir125b-1 |
| 21121 | 3 | | | | Mir125b-2 |
| 21122 | 3 | | | | Mir126 |
| 21123 | 3 | | | | Mir126a |
| 21124 | 3 | | | | Mir126b |
| 21125 | 3 | | | | Mir127 |
| 21126 | 3 | | | | Mir128-1 |
| 21127 | 3 | | | | Mir128-2 |
| 21128 | 3 | | | | Mir129-1 |
| 21129 | 3 | | | | Mir129-2 |
| 21130 | 3 | | | | Mir129a |
| 21131 | 3 | | | | Mir129b |
| 21132 | 3 | | | | Mir1306 |
| 21133 | 3 | | | | Mir130a |
| 21134 | 3 | | | | Mir130b |
| 21135 | 3 | | | | Mir130c |
| 21136 | 3 | | | | Mir132 |
| 21137 | 3 | | | | Mir133a-1 |
| 21138 | 3 | | | | Mir133a-2 |
| 21139 | 3 | | | | Mir133b |
| 21140 | 3 | | | | Mir133c |
| 21141 | 3 | | | | Mir134 |
| 21142 | 3 | | | | Mir135a-1 |
| 21143 | 3 | | | | Mir135a-2 |
| 21144 | 3 | | | | Mir135b |
| 21145 | 3 | | | | Mir136 |
| 21146 | 3 | | | | Mir137 |
| 21147 | 3 | | | | Mir138-1 |
| 21148 | 3 | | | | Mir138-2 |
| 21149 | 3 | | | | Mir139 |
| 21150 | 3 | | | | Mir140 |
| 21151 | 3 | | | | Mir141 |
| 21152 | 3 | | | | Mir142 |
| 21153 | 3 | | | | Mir143 |
| 21154 | 3 | | | | Mir144 |
| 21155 | 3 | | | | Mir145 |
| 21156 | 3 | | | | Mir145b |
| 21157 | 3 | | | | Mir146 |
| 21158 | 3 | | | | Mir146b |
| 21159 | 3 | | | | Mir147 |
| 21160 | 3 | | | | Mir148a |
| 21161 | 3 | | | | Mir148b |
| 21162 | 3 | | | | Mir149 |
| 21163 | 3 | | | | Mir150 |
| 21164 | 3 | | | | Mir152 |
| 21165 | 3 | | | | Mir153 |
| 21166 | 3 | | | | Mir154 |
| 21167 | 3 | | | | Mir155 |
| 21168 | 3 | | | | Mir15a |
| 21169 | 3 | | | | Mir15b |
| 21170 | 3 | | | | Mir16-1 |
| 21171 | 3 | | | | Mir16-2 |
| 21172 | 3 | | | | Mir1668 |
| 21173 | 3 | | | | Mir17 |
| 21174 | 3 | | | | Mir18 |
| 21175 | 3 | | | | Mir181a-1 |
| 21176 | 3 | | | | Mir181a-2 |
| 21177 | 3 | | | | Mir181b-1 |
| 21178 | 3 | | | | Mir181b-2 |
| 21179 | 3 | | | | Mir181c |
| 21180 | 3 | | | | Mir181d |
| 21181 | 3 | | | | Mir182 |
| 21182 | 3 | | | | Mir183 |
| 21183 | 3 | | | | Mir1839 |
| 21184 | 3 | | | | Mir184 |
| 21185 | 3 | | | | Mir1843 |
| 21186 | 3 | | | | Mir1843b |
| 21187 | 3 | | | | Mir185 |
| 21188 | 3 | | | | Mir186 |
| 21189 | 3 | | | | Mir187 |
| 21190 | 3 | | | | Mir188 |
| 21191 | 3 | | | | Mir1892 |
| 21192 | 3 | | | | Mir1893 |
| 21193 | 3 | | | | Mir1894 |
| 21194 | 3 | | | | Mir1895 |
| 21195 | 3 | | | | Mir1896 |
| 21196 | 3 | | | | Mir1897 |
| 21197 | 3 | | | | Mir1898 |
| 21198 | 3 | | | | Mir1899 |
| 21199 | 3 | | | | Mir18b |
| 21200 | 3 | | | | Mir190 |
| 21201 | 3 | | | | Mir1900 |
| 21202 | 3 | | | | Mir1901 |
| 21203 | 3 | | | | Mir1902 |
| 21204 | 3 | | | | Mir1903 |
| 21205 | 3 | | | | Mir1904 |
| 21206 | 3 | | | | Mir1905 |
| 21207 | 3 | | | | Mir1906-1 |
| 21208 | 3 | | | | Mir1907 |
| 21209 | 3 | | | | Mir190b |
| 21210 | 3 | | | | Mir191 |
| 21211 | 3 | | | | Mir1912 |
| 21212 | 3 | | | | Mir192 |
| 21213 | 3 | | | | Mir1928 |
| 21214 | 3 | | | | Mir1929 |
| 21215 | 3 | | | | Mir193 |
| 21216 | 3 | | | | Mir1930 |
| 21217 | 3 | | | | Mir1931 |
| 21218 | 3 | | | | Mir1932 |
| 21219 | 3 | | | | Mir1933 |
| 21220 | 3 | | | | Mir1934 |
| 21221 | 3 | | | | Mir1936 |
| 21222 | 3 | | | | Mir1938 |
| 21223 | 3 | | | | Mir193b |
| 21224 | 3 | | | | Mir194-1 |
| 21225 | 3 | | | | Mir194-2 |
| 21226 | 3 | | | | Mir1940 |
| 21227 | 3 | | | | Mir1941 |
| 21228 | 3 | | | | Mir1942 |
| 21229 | 3 | | | | Mir1943 |
| 21230 | 3 | | | | Mir1945 |
| 21231 | 3 | | | | Mir1946a |
| 21232 | 3 | | | | Mir1946b |
| 21233 | 3 | | | | Mir1947 |
| 21234 | 3 | | | | Mir1948 |
| 21235 | 3 | | | | Mir1949 |
| 21236 | 3 | | | | Mir195 |
| 21237 | 3 | | | | Mir1950 |
| 21238 | 3 | | | | Mir1951 |
| 21239 | 3 | | | | Mir1952 |
| 21240 | 3 | | | | Mir1953 |
| 21241 | 3 | | | | Mir1954 |
| 21242 | 3 | | | | Mir1955 |
| 21243 | 3 | | | | Mir1956 |
| 21244 | 3 | | | | Mir1957 |
| 21245 | 3 | | | | Mir1958 |
| 21246 | 3 | | | | Mir195b |
| 21247 | 3 | | | | Mir1960 |
| 21248 | 3 | | | | Mir1961 |
| 21249 | 3 | | | | Mir1962 |
| 21250 | 3 | | | | Mir1963 |
| 21251 | 3 | | | | Mir1964 |
| 21252 | 3 | | | | Mir1966 |
| 21253 | 3 | | | | Mir1967 |
| 21254 | 3 | | | | Mir1968 |
| 21255 | 3 | | | | Mir1969 |
| 21256 | 3 | | | | Mir196a-1 |
| 21257 | 3 | | | | Mir196a-2 |
| 21258 | 3 | | | | Mir196b |
| 21259 | 3 | | | | Mir1970 |
| 21260 | 3 | | | | Mir1971 |
| 21261 | 3 | | | | Mir1981 |
| 21262 | 3 | | | | Mir1982 |
| 21263 | 3 | | | | Mir1983 |
| 21264 | 3 | | | | Mir199a-1 |
| 21265 | 3 | | | | Mir199a-2 |
| 21266 | 3 | | | | Mir199b |
| 21267 | 3 | | | | Mir19a |
| 21268 | 3 | | | | Mir19b-1 |
| 21269 | 3 | | | | Mir19b-2 |
| 21270 | 3 | | | | Mir1a-1 |
| 21271 | 3 | | | | Mir1a-2 |
| 21272 | 3 | | | | Mir1b |
| 21273 | 3 | | | | Mir200a |
| 21274 | 3 | | | | Mir200b |
| 21275 | 3 | | | | Mir200c |
| 21276 | 3 | | | | Mir201 |
| 21277 | 3 | | | | Mir202 |
| 21278 | 3 | | | | Mir203 |
| 21279 | 3 | | | | Mir204 |
| 21280 | 3 | | | | Mir205 |
| 21281 | 3 | | | | Mir206 |
| 21282 | 3 | | | | Mir207 |
| 21283 | 3 | | | | Mir208a |
| 21284 | 3 | | | | Mir208b |
| 21285 | 3 | | | | Mir20a |
| 21286 | 3 | | | | Mir20b |
| 21287 | 3 | | | | Mir21 |
| 21288 | 3 | | | | Mir211 |
| 21289 | 3 | | | | Mir212 |
| 21290 | 3 | | | | Mir2136 |
| 21291 | 3 | | | | Mir2137 |
| 21292 | 3 | | | | Mir2139 |
| 21293 | 3 | | | | Mir216a |
| 21294 | 3 | | | | Mir216b |
| 21295 | 3 | | | | Mir216c |
| 21296 | 3 | | | | Mir217 |
| 21297 | 3 | | | | Mir218-1 |
| 21298 | 3 | | | | Mir218-2 |
| 21299 | 3 | | | | Mir219-1 |
| 21300 | 3 | | | | Mir219-2 |
| 21301 | 3 | | | | Mir219b |
| 21302 | 3 | | | | Mir219c |
| 21303 | 3 | | | | Mir21b |
| 21304 | 3 | | | | Mir21c |
| 21305 | 3 | | | | Mir22 |
| 21306 | 3 | | | | Mir221 |
| 21307 | 3 | | | | Mir222 |
| 21308 | 3 | | | | Mir223 |
| 21309 | 3 | | | | Mir23a |
| 21310 | 3 | | | | Mir23b |

Fig. 34 - 112

| | | | | | | |
|---|---|---|---|---|---|---|
| 21311 | 3 | | | | | Mir24-1 |
| 21312 | 3 | | | | | Mir24-2 |
| 21313 | 3 | | | | | Mir25 |
| 21314 | 3 | | | | | Mir26a-1 |
| 21315 | 3 | | | | | Mir26a-2 |
| 21316 | 3 | | | | | Mir26b |
| 21317 | 3 | | | | | Mir27a |
| 21318 | 3 | | | | | Mir27b |
| 21319 | 3 | | | | | Mir28 |
| 21320 | 3 | | | | | Mir2861 |
| 21321 | 3 | | | | | Mir28b |
| 21322 | 3 | | | | | Mir28c |
| 21323 | 3 | | | | | Mir290 |
| 21324 | 3 | | | | | Mir290b |
| 21325 | 3 | | | | | Mir291a |
| 21326 | 3 | | | | | Mir291b |
| 21327 | 3 | | | | | Mir292 |
| 21328 | 3 | | | | | Mir292b |
| 21329 | 3 | | | | | Mir293 |
| 21330 | 3 | | | | | Mir294 |
| 21331 | 3 | | | | | Mir295 |
| 21332 | 3 | | | | | Mir296 |
| 21333 | 3 | | | | | Mir297-1 |
| 21334 | 3 | | | | | Mir297-2 |
| 21335 | 3 | | | | | Mir297a-3 |
| 21336 | 3 | | | | | Mir297a-4 |
| 21337 | 3 | | | | | Mir297b |
| 21338 | 3 | | | | | Mir297c |
| 21339 | 3 | | | | | Mir298 |
| 21340 | 3 | | | | | Mir299 |
| 21341 | 3 | | | | | Mir299b |
| 21342 | 3 | | | | | Mir29a |
| 21343 | 3 | | | | | Mir29b-1 |
| 21344 | 3 | | | | | Mir29b-2 |
| 21345 | 3 | | | | | Mir29c |
| 21346 | 3 | | | | | Mir300 |
| 21347 | 3 | | | | | Mir301 |
| 21348 | 3 | | | | | Mir301b |
| 21349 | 3 | | | | | Mir302a |
| 21350 | 3 | | | | | Mir302b |
| 21351 | 3 | | | | | Mir302c |
| 21352 | 3 | | | | | Mir302d |
| 21353 | 3 | | | | | Mir3057 |
| 21354 | 3 | | | | | Mir3058 |
| 21355 | 3 | | | | | Mir3059 |
| 21356 | 3 | | | | | Mir3060 |
| 21357 | 3 | | | | | Mir3061 |
| 21358 | 3 | | | | | Mir3062 |
| 21359 | 3 | | | | | Mir3063 |
| 21360 | 3 | | | | | Mir3064 |
| 21361 | 3 | | | | | Mir3065 |
| 21362 | 3 | | | | | Mir3066 |
| 21363 | 3 | | | | | Mir3067 |
| 21364 | 3 | | | | | Mir3068 |
| 21365 | 3 | | | | | Mir3069 |
| 21366 | 3 | | | | | Mir3070a |
| 21367 | 3 | | | | | Mir3070b |
| 21368 | 3 | | | | | Mir3071 |
| 21369 | 3 | | | | | Mir3072 |
| 21370 | 3 | | | | | Mir3073 |
| 21371 | 3 | | | | | Mir3073b |
| 21372 | 3 | | | | | Mir3074-1 |
| 21373 | 3 | | | | | Mir3074-2 |
| 21374 | 3 | | | | | Mir3075 |
| 21375 | 3 | | | | | Mir3076 |
| 21376 | 3 | | | | | Mir3077 |
| 21377 | 3 | | | | | Mir3078 |
| 21378 | 3 | | | | | Mir3079 |
| 21379 | 3 | | | | | Mir3081 |
| 21380 | 3 | | | | | Mir3082 |
| 21381 | 3 | | | | | Mir3083 |
| 21382 | 3 | | | | | Mir3084 |
| 21383 | 3 | | | | | Mir3084-2 |
| 21384 | 3 | | | | | Mir3085 |
| 21385 | 3 | | | | | Mir3086 |
| 21386 | 3 | | | | | Mir3087 |
| 21387 | 3 | | | | | Mir3088 |
| 21388 | 3 | | | | | Mir3089 |
| 21389 | 3 | | | | | Mir3091 |
| 21390 | 3 | | | | | Mir3092 |
| 21391 | 3 | | | | | Mir3093 |
| 21392 | 3 | | | | | Mir3094 |
| 21393 | 3 | | | | | Mir3095 |
| 21394 | 3 | | | | | Mir3097 |
| 21395 | 3 | | | | | Mir3098 |
| 21396 | 3 | | | | | Mir3099 |
| 21397 | 3 | | | | | Mir30a |
| 21398 | 3 | | | | | Mir30b |
| 21399 | 3 | | | | | Mir30c-1 |
| 21400 | 3 | | | | | Mir30c-2 |
| 21401 | 3 | | | | | Mir30d |
| 21402 | 3 | | | | | Mir30f |
| 21403 | 3 | | | | | Mir31 |
| 21404 | 3 | | | | | Mir3100 |
| 21405 | 3 | | | | | Mir3101 |
| 21406 | 3 | | | | | Mir3102 |
| 21407 | 3 | | | | | Mir3103 |
| 21408 | 3 | | | | | Mir3104 |
| 21409 | 3 | | | | | Mir3106 |
| 21410 | 3 | | | | | Mir3107 |
| 21411 | 3 | | | | | Mir3108 |
| 21412 | 3 | | | | | Mir3109 |
| 21413 | 3 | | | | | Mir3110 |
| 21414 | 3 | | | | | Mir3112 |
| 21415 | 3 | | | | | Mir32 |
| 21416 | 3 | | | | | Mir320 |
| 21417 | 3 | | | | | Mir322 |
| 21418 | 3 | | | | | Mir323 |
| 21419 | 3 | | | | | Mir324 |
| 21420 | 3 | | | | | Mir325 |
| 21421 | 3 | | | | | Mir326 |
| 21422 | 3 | | | | | Mir328 |
| 21423 | 3 | | | | | Mir329 |
| 21424 | 3 | | | | | Mir33 |
| 21425 | 3 | | | | | Mir330 |
| 21426 | 3 | | | | | Mir331 |
| 21427 | 3 | | | | | Mir335 |
| 21428 | 3 | | | | | Mir337 |
| 21429 | 3 | | | | | Mir338 |
| 21430 | 3 | | | | | Mir339 |
| 21431 | 3 | | | | | Mir340 |
| 21432 | 3 | | | | | Mir341 |
| 21433 | 3 | | | | | Mir343 |
| 21434 | 3 | | | | | Mir344 |
| 21435 | 3 | | | | | Mir344-2 |
| 21436 | 3 | | | | | Mir344b |
| 21437 | 3 | | | | | Mir344c |
| 21438 | 3 | | | | | Mir344d-1 |
| 21439 | 3 | | | | | Mir344d-2 |
| 21440 | 3 | | | | | Mir344d-3 |
| 21441 | 3 | | | | | Mir344e |
| 21442 | 3 | | | | | Mir344f |
| 21443 | 3 | | | | | Mir344g |
| 21444 | 3 | | | | | Mir344h-1 |
| 21445 | 3 | | | | | Mir344i |
| 21446 | 3 | | | | | Mir345 |
| 21447 | 3 | | | | | Mir346 |
| 21448 | 3 | | | | | Mir3470a |
| 21449 | 3 | | | | | Mir3470b |
| 21450 | 3 | | | | | Mir3471-1 |
| 21451 | 3 | | | | | Mir3473 |
| 21452 | 3 | | | | | Mir3473c |
| 21453 | 3 | | | | | Mir3473d |
| 21454 | 3 | | | | | Mir3473e |
| 21455 | 3 | | | | | Mir3473f |
| 21456 | 3 | | | | | Mir3474 |
| 21457 | 3 | | | | | Mir3475 |
| 21458 | 3 | | | | | Mir34a |
| 21459 | 3 | | | | | Mir34b |
| 21460 | 3 | | | | | Mir34c |
| 21461 | 3 | | | | | Mir350 |
| 21462 | 3 | | | | | Mir351 |
| 21463 | 3 | | | | | Mir3535 |
| 21464 | 3 | | | | | Mir3544 |
| 21465 | 3 | | | | | Mir3547 |
| 21466 | 3 | | | | | Mir3569 |
| 21467 | 3 | | | | | Mir3572 |
| 21468 | 3 | | | | | Mir362 |
| 21469 | 3 | | | | | Mir3620 |
| 21470 | 3 | | | | | Mir363 |
| 21471 | 3 | | | | | Mir365-1 |
| 21472 | 3 | | | | | Mir367 |
| 21473 | 3 | | | | | Mir369 |
| 21474 | 3 | | | | | Mir370 |
| 21475 | 3 | | | | | Mir374 |
| 21476 | 3 | | | | | Mir374c |
| 21477 | 3 | | | | | Mir375 |
| 21478 | 3 | | | | | Mir376a |
| 21479 | 3 | | | | | Mir376b |
| 21480 | 3 | | | | | Mir376c |
| 21481 | 3 | | | | | Mir377 |
| 21482 | 3 | | | | | Mir378 |
| 21483 | 3 | | | | | Mir378b |
| 21484 | 3 | | | | | Mir378c |
| 21485 | 3 | | | | | Mir379 |
| 21486 | 3 | | | | | Mir380 |
| 21487 | 3 | | | | | Mir381 |
| 21488 | 3 | | | | | Mir382 |
| 21489 | 3 | | | | | Mir383 |
| 21490 | 3 | | | | | Mir384 |
| 21491 | 3 | | | | | Mir3960 |
| 21492 | 3 | | | | | Mir3962 |
| 21493 | 3 | | | | | Mir3963 |
| 21494 | 3 | | | | | Mir3964 |
| 21495 | 3 | | | | | Mir3965 |
| 21496 | 3 | | | | | Mir3966 |
| 21497 | 3 | | | | | Mir3967 |
| 21498 | 3 | | | | | Mir3968 |
| 21499 | 3 | | | | | Mir3969 |
| 21500 | 3 | | | | | Mir3970 |
| 21501 | 3 | | | | | Mir3971 |
| 21502 | 3 | | | | | Mir409 |

Fig. 34 - 113

| | | | | | | | | | | | | |
|---|---|---|---|---|---|---|---|---|---|---|---|---|
| 21503 | 3 | | | | | Mir410 | 21599 | 3 | | | | Mir5125 |
| 21504 | 3 | | | | | Mir411 | 21600 | 3 | | | | Mir5126 |
| 21505 | 3 | | | | | Mir412 | 21601 | 3 | | | | Mir5127 |
| 21506 | 3 | | | | | Mir421 | 21602 | 3 | | | | Mir5128 |
| 21507 | 3 | | | | | Mir423 | 21603 | 3 | | | | Mir5129 |
| 21508 | 3 | | | | | Mir425 | 21604 | 3 | | | | Mir5130 |
| 21509 | 3 | | | | | Mir429 | 21605 | 3 | | | | Mir5131 |
| 21510 | 3 | | | | | Mir431 | 21606 | 3 | | | | Mir5132 |
| 21511 | 3 | | | | | Mir432 | 21607 | 3 | | | | Mir5133 |
| 21512 | 3 | | | | | Mir433 | 21608 | 3 | | | | Mir5134 |
| 21513 | 3 | | | | | Mir434 | 21609 | 3 | | | | Mir5135 |
| 21514 | 3 | | | | | Mir448 | 21610 | 3 | | | | Mir5136 |
| 21515 | 3 | | | | | Mir449a | 21611 | 3 | | | | Mir532 |
| 21516 | 3 | | | | | Mir449b | 21612 | 3 | | | | Mir539 |
| 21517 | 3 | | | | | Mir449c | 21613 | 3 | | | | Mir540 |
| 21518 | 3 | | | | | Mir450-1 | 21614 | 3 | | | | Mir541 |
| 21519 | 3 | | | | | Mir450-2 | 21615 | 3 | | | | Mir542 |
| 21520 | 3 | | | | | Mir450b | 21616 | 3 | | | | Mir543 |
| 21521 | 3 | | | | | Mir451 | 21617 | 3 | | | | Mir544 |
| 21522 | 3 | | | | | Mir452 | 21618 | 3 | | | | Mir546 |
| 21523 | 3 | | | | | Mir453 | 21619 | 3 | | | | Mir547 |
| 21524 | 3 | | | | | Mir455 | 21620 | 3 | | | | Mir551b |
| 21525 | 3 | | | | | Mir463 | 21621 | 3 | | | | Mir5615-1 |
| 21526 | 3 | | | | | Mir465 | 21622 | 3 | | | | Mir5615-2 |
| 21527 | 3 | | | | | Mir465b-1 | 21623 | 3 | | | | Mir5616 |
| 21528 | 3 | | | | | Mir465c-1 | 21624 | 3 | | | | Mir5617 |
| 21529 | 3 | | | | | Mir465d | 21625 | 3 | | | | Mir5618 |
| 21530 | 3 | | | | | Mir466 | 21626 | 3 | | | | Mir5619 |
| 21531 | 3 | | | | | Mir466c | 21627 | 3 | | | | Mir5620 |
| 21532 | 3 | | | | | Mir466b-2 | 21628 | 3 | | | | Mir5621 |
| 21533 | 3 | | | | | Mir466b-3 | 21629 | 3 | | | | Mir5622 |
| 21534 | 3 | | | | | Mir466d | 21630 | 3 | | | | Mir5623 |
| 21535 | 3 | | | | | Mir466f-1 | 21631 | 3 | | | | Mir5624 |
| 21536 | 3 | | | | | Mir466f-2 | 21632 | 3 | | | | Mir5625 |
| 21537 | 3 | | | | | Mir466f-3 | 21633 | 3 | | | | Mir5626 |
| 21538 | 3 | | | | | Mir466g | 21634 | 3 | | | | Mir5627 |
| 21539 | 3 | | | | | Mir466h | 21635 | 3 | | | | Mir568 |
| 21540 | 3 | | | | | Mir466n | 21636 | 3 | | | | Mir5709 |
| 21541 | 3 | | | | | Mir466p | 21637 | 3 | | | | Mir5710 |
| 21542 | 3 | | | | | Mir467a-1 | 21638 | 3 | | | | Mir574 |
| 21543 | 3 | | | | | Mir467a-10 | 21639 | 3 | | | | Mir582 |
| 21544 | 3 | | | | | Mir467a-2 | 21640 | 3 | | | | Mir592 |
| 21545 | 3 | | | | | Mir467a-3 | 21641 | 3 | | | | Mir598 |
| 21546 | 3 | | | | | Mir467a-5 | 21642 | 3 | | | | Mir599 |
| 21547 | 3 | | | | | Mir467a-7 | 21643 | 3 | | | | Mir615 |
| 21548 | 3 | | | | | Mir467a-9 | 21644 | 3 | | | | Mir6237 |
| 21549 | 3 | | | | | Mir467b | 21645 | 3 | | | | Mir6238 |
| 21550 | 3 | | | | | Mir467c | 21646 | 3 | | | | Mir6239 |
| 21551 | 3 | | | | | Mir467d | 21647 | 3 | | | | Mir6241 |
| 21552 | 3 | | | | | Mir467e | 21648 | 3 | | | | Mir6244 |
| 21553 | 3 | | | | | Mir467f | 21649 | 3 | | | | Mir6335 |
| 21554 | 3 | | | | | Mir468 | 21650 | 3 | | | | Mir6336 |
| 21555 | 3 | | | | | Mir470 | 21651 | 3 | | | | Mir6337 |
| 21556 | 3 | | | | | Mir471 | 21652 | 3 | | | | Mir6338 |
| 21557 | 3 | | | | | Mir483 | 21653 | 3 | | | | Mir6339 |
| 21558 | 3 | | | | | Mir484 | 21654 | 3 | | | | Mir6341 |
| 21559 | 3 | | | | | Mir485 | 21655 | 3 | | | | Mir6342 |
| 21560 | 3 | | | | | Mir487b | 21656 | 3 | | | | Mir6343 |
| 21561 | 3 | | | | | Mir488 | 21657 | 3 | | | | Mir6344 |
| 21562 | 3 | | | | | Mir489 | 21658 | 3 | | | | Mir6348 |
| 21563 | 3 | | | | | Mir490 | 21659 | 3 | | | | Mir6349 |
| 21564 | 3 | | | | | Mir491 | 21660 | 3 | | | | Mir6350 |
| 21565 | 3 | | | | | Mir493 | 21661 | 3 | | | | Mir6352 |
| 21566 | 3 | | | | | Mir494 | 21662 | 3 | | | | Mir6353 |
| 21567 | 3 | | | | | Mir495 | 21663 | 3 | | | | Mir6354 |
| 21568 | 3 | | | | | Mir496 | 21664 | 3 | | | | Mir6355 |
| 21569 | 3 | | | | | Mir496b | 21665 | 3 | | | | Mir6356 |
| 21570 | 3 | | | | | Mir497 | 21666 | 3 | | | | Mir6358 |
| 21571 | 3 | | | | | Mir497b | 21667 | 3 | | | | Mir6359 |
| 21572 | 3 | | | | | Mir499 | 21668 | 3 | | | | Mir6360 |
| 21573 | 3 | | | | | Mir500 | 21669 | 3 | | | | Mir6361 |
| 21574 | 3 | | | | | Mir501 | 21670 | 3 | | | | Mir6362 |
| 21575 | 3 | | | | | Mir503 | 21671 | 3 | | | | Mir6364 |
| 21576 | 3 | | | | | Mir504 | 21672 | 3 | | | | Mir6365 |
| 21577 | 3 | | | | | Mir5046 | 21673 | 3 | | | | Mir6366 |
| 21578 | 3 | | | | | Mir505 | 21674 | 3 | | | | Mir6367 |
| 21579 | 3 | | | | | Mir509 | 21675 | 3 | | | | Mir6368 |
| 21580 | 3 | | | | | Mir5098 | 21676 | 3 | | | | Mir6369 |
| 21581 | 3 | | | | | Mir5100 | 21677 | 3 | | | | Mir6370 |
| 21582 | 3 | | | | | Mir5101 | 21678 | 3 | | | | Mir6372 |
| 21583 | 3 | | | | | Mir5103 | 21679 | 3 | | | | Mir6373 |
| 21584 | 3 | | | | | Mir5104 | 21680 | 3 | | | | Mir6374 |
| 21585 | 3 | | | | | Mir5106 | 21681 | 3 | | | | Mir6375 |
| 21586 | 3 | | | | | Mir5107 | 21682 | 3 | | | | Mir6376 |
| 21587 | 3 | | | | | Mir5108 | 21683 | 3 | | | | Mir6378 |
| 21588 | 3 | | | | | Mir511 | 21684 | 3 | | | | Mir6380 |
| 21589 | 3 | | | | | Mir5112 | 21685 | 3 | | | | Mir6381 |
| 21590 | 3 | | | | | Mir5113 | 21686 | 3 | | | | Mir6382 |
| 21591 | 3 | | | | | Mir5114 | 21687 | 3 | | | | Mir6383 |
| 21592 | 3 | | | | | Mir5116 | 21688 | 3 | | | | Mir6384 |
| 21593 | 3 | | | | | Mir5119 | 21689 | 3 | | | | Mir6385 |
| 21594 | 3 | | | | | Mir5120 | 21690 | 3 | | | | Mir6387 |
| 21595 | 3 | | | | | Mir5121 | 21691 | 3 | | | | Mir6388 |
| 21596 | 3 | | | | | Mir5122 | 21692 | 3 | | | | Mir6389 |
| 21597 | 3 | | | | | Mir5123 | 21693 | 3 | | | | Mir6390 |
| 21598 | 3 | | | | | Mir5124 | 21694 | 3 | | | | Mir6391 |

Fig. 34 - 114

| | | | | | | |
|---|---|---|---|---|---|---|
| 21695 | 3 | | | | | Mir6392 |
| 21696 | 3 | | | | | Mir6393 |
| 21697 | 3 | | | | | Mir6394 |
| 21698 | 3 | | | | | Mir6395 |
| 21699 | 3 | | | | | Mir6396 |
| 21700 | 3 | | | | | Mir6397 |
| 21701 | 3 | | | | | Mir6398 |
| 21702 | 3 | | | | | Mir6399 |
| 21703 | 3 | | | | | Mir6400 |
| 21704 | 3 | | | | | Mir6401 |
| 21705 | 3 | | | | | Mir6402 |
| 21706 | 3 | | | | | Mir6404 |
| 21707 | 3 | | | | | Mir6405 |
| 21708 | 3 | | | | | Mir6406 |
| 21709 | 3 | | | | | Mir6407 |
| 21710 | 3 | | | | | Mir6408 |
| 21711 | 3 | | | | | Mir6409 |
| 21712 | 3 | | | | | Mir6410 |
| 21713 | 3 | | | | | Mir6411 |
| 21714 | 3 | | | | | Mir6412 |
| 21715 | 3 | | | | | Mir6413 |
| 21716 | 3 | | | | | Mir6414 |
| 21717 | 3 | | | | | Mir6415 |
| 21718 | 3 | | | | | Mir6416 |
| 21719 | 3 | | | | | Mir6417 |
| 21720 | 3 | | | | | Mir6419 |
| 21721 | 3 | | | | | Mir6420 |
| 21722 | 3 | | | | | Mir6481 |
| 21723 | 3 | | | | | Mir653 |
| 21724 | 3 | | | | | Mir6537 |
| 21725 | 3 | | | | | Mir6539 |
| 21726 | 3 | | | | | Mir654 |
| 21727 | 3 | | | | | Mir6540 |
| 21728 | 3 | | | | | Mir6541 |
| 21729 | 3 | | | | | Mir6546 |
| 21730 | 3 | | | | | Mir664 |
| 21731 | 3 | | | | | Mir665 |
| 21732 | 3 | | | | | Mir666 |
| 21733 | 3 | | | | | Mir667 |
| 21734 | 3 | | | | | Mir668 |
| 21735 | 3 | | | | | Mir669a-1 |
| 21736 | 3 | | | | | Mir669a-2 |
| 21737 | 3 | | | | | Mir669a-3 |
| 21738 | 3 | | | | | Mir669a-4 |
| 21739 | 3 | | | | | Mir669b |
| 21740 | 3 | | | | | Mir669c |
| 21741 | 3 | | | | | Mir669e |
| 21742 | 3 | | | | | Mir669g |
| 21743 | 3 | | | | | Mir669h |
| 21744 | 3 | | | | | Mir669i |
| 21745 | 3 | | | | | Mir669j |
| 21746 | 3 | | | | | Mir669k |
| 21747 | 3 | | | | | Mir669m-1 |
| 21748 | 3 | | | | | Mir669m-2 |
| 21749 | 3 | | | | | Mir669p-1 |
| 21750 | 3 | | | | | Mir670 |
| 21751 | 3 | | | | | Mir671 |
| 21752 | 3 | | | | | Mir6715 |
| 21753 | 3 | | | | | Mir672 |
| 21754 | 3 | | | | | Mir673 |
| 21755 | 3 | | | | | Mir674 |
| 21756 | 3 | | | | | Mir675 |
| 21757 | 3 | | | | | Mir676 |
| 21758 | 3 | | | | | Mir6769b |
| 21759 | 3 | | | | | Mir677 |
| 21760 | 3 | | | | | Mir678 |
| 21761 | 3 | | | | | Mir679 |
| 21762 | 3 | | | | | Mir680-2 |
| 21763 | 3 | | | | | Mir680-3 |
| 21764 | 3 | | | | | Mir681 |
| 21765 | 3 | | | | | Mir683-1 |
| 21766 | 3 | | | | | Mir684-1 |
| 21767 | 3 | | | | | Mir684-2 |
| 21768 | 3 | | | | | Mir686 |
| 21769 | 3 | | | | | Mir687 |
| 21770 | 3 | | | | | Mir688 |
| 21771 | 3 | | | | | Mir6896 |
| 21772 | 3 | | | | | Mir6897 |
| 21773 | 3 | | | | | Mir6898 |
| 21774 | 3 | | | | | Mir6899 |
| 21775 | 3 | | | | | Mir690 |
| 21776 | 3 | | | | | Mir6900 |
| 21777 | 3 | | | | | Mir6901 |
| 21778 | 3 | | | | | Mir6902 |
| 21779 | 3 | | | | | Mir6903 |
| 21780 | 3 | | | | | Mir6904 |
| 21781 | 3 | | | | | Mir6905 |
| 21782 | 3 | | | | | Mir6906 |
| 21783 | 3 | | | | | Mir6907 |
| 21784 | 3 | | | | | Mir6908 |
| 21785 | 3 | | | | | Mir6909 |
| 21786 | 3 | | | | | Mir691 |
| 21787 | 3 | | | | | Mir6910 |
| 21788 | 3 | | | | | Mir6911 |
| 21789 | 3 | | | | | Mir6912 |
| 21790 | 3 | | | | | Mir6913 |
| 21791 | 3 | | | | | Mir6914 |
| 21792 | 3 | | | | | Mir6915 |
| 21793 | 3 | | | | | Mir6916 |
| 21794 | 3 | | | | | Mir6917 |
| 21795 | 3 | | | | | Mir6918 |
| 21796 | 3 | | | | | Mir6919 |
| 21797 | 3 | | | | | Mir692-1 |
| 21798 | 3 | | | | | Mir692-2b |
| 21799 | 3 | | | | | Mir6920 |
| 21800 | 3 | | | | | Mir6921 |
| 21801 | 3 | | | | | Mir6922 |
| 21802 | 3 | | | | | Mir6923 |
| 21803 | 3 | | | | | Mir6924 |
| 21804 | 3 | | | | | Mir6925 |
| 21805 | 3 | | | | | Mir6926 |
| 21806 | 3 | | | | | Mir6927 |
| 21807 | 3 | | | | | Mir6928 |
| 21808 | 3 | | | | | Mir6929 |
| 21809 | 3 | | | | | Mir693 |
| 21810 | 3 | | | | | Mir6930 |
| 21811 | 3 | | | | | Mir6931 |
| 21812 | 3 | | | | | Mir6932 |
| 21813 | 3 | | | | | Mir6933 |
| 21814 | 3 | | | | | Mir6934 |
| 21815 | 3 | | | | | Mir6935 |
| 21816 | 3 | | | | | Mir6936 |
| 21817 | 3 | | | | | Mir6937 |
| 21818 | 3 | | | | | Mir6938 |
| 21819 | 3 | | | | | Mir6939 |
| 21820 | 3 | | | | | Mir694 |
| 21821 | 3 | | | | | Mir6940 |
| 21822 | 3 | | | | | Mir6941 |
| 21823 | 3 | | | | | Mir6942 |
| 21824 | 3 | | | | | Mir6943 |
| 21825 | 3 | | | | | Mir6944 |
| 21826 | 3 | | | | | Mir6945 |
| 21827 | 3 | | | | | Mir6946 |
| 21828 | 3 | | | | | Mir6947 |
| 21829 | 3 | | | | | Mir6948 |
| 21830 | 3 | | | | | Mir6949 |
| 21831 | 3 | | | | | Mir695 |
| 21832 | 3 | | | | | Mir6950 |
| 21833 | 3 | | | | | Mir6951 |
| 21834 | 3 | | | | | Mir6952 |
| 21835 | 3 | | | | | Mir6953 |
| 21836 | 3 | | | | | Mir6954 |
| 21837 | 3 | | | | | Mir6955 |
| 21838 | 3 | | | | | Mir6956 |
| 21839 | 3 | | | | | Mir6957 |
| 21840 | 3 | | | | | Mir6958 |
| 21841 | 3 | | | | | Mir6959 |
| 21842 | 3 | | | | | Mir6960 |
| 21843 | 3 | | | | | Mir6961 |
| 21844 | 3 | | | | | Mir6962 |
| 21845 | 3 | | | | | Mir6963 |
| 21846 | 3 | | | | | Mir6964 |
| 21847 | 3 | | | | | Mir6965 |
| 21848 | 3 | | | | | Mir6966 |
| 21849 | 3 | | | | | Mir6968 |
| 21850 | 3 | | | | | Mir6969 |
| 21851 | 3 | | | | | Mir697 |
| 21852 | 3 | | | | | Mir6970 |
| 21853 | 3 | | | | | Mir6971 |
| 21854 | 3 | | | | | Mir6972 |
| 21855 | 3 | | | | | Mir6973a |
| 21856 | 3 | | | | | Mir6973b |
| 21857 | 3 | | | | | Mir6974 |
| 21858 | 3 | | | | | Mir6975 |
| 21859 | 3 | | | | | Mir6976 |
| 21860 | 3 | | | | | Mir6977 |
| 21861 | 3 | | | | | Mir6978 |
| 21862 | 3 | | | | | Mir6979 |
| 21863 | 3 | | | | | Mir698 |
| 21864 | 3 | | | | | Mir6980 |
| 21865 | 3 | | | | | Mir6982 |
| 21866 | 3 | | | | | Mir6983 |
| 21867 | 3 | | | | | Mir6984 |
| 21868 | 3 | | | | | Mir6985 |
| 21869 | 3 | | | | | Mir6986 |
| 21870 | 3 | | | | | Mir6987 |
| 21871 | 3 | | | | | Mir6988 |
| 21872 | 3 | | | | | Mir6989 |
| 21873 | 3 | | | | | Mir6990 |
| 21874 | 3 | | | | | Mir6991 |
| 21875 | 3 | | | | | Mir6993 |
| 21876 | 3 | | | | | Mir6994 |
| 21877 | 3 | | | | | Mir6995 |
| 21878 | 3 | | | | | Mir6996 |
| 21879 | 3 | | | | | Mir6997 |
| 21880 | 3 | | | | | Mir6998 |
| 21881 | 3 | | | | | Mir6999 |
| 21882 | 3 | | | | | Mir7-2 |
| 21883 | 3 | | | | | Mir700 |
| 21884 | 3 | | | | | Mir7000 |
| 21885 | 3 | | | | | Mir7001 |
| 21886 | 3 | | | | | Mir7002 |

Fig. 34 - 115

| | | | | | | |
|---|---|---|---|---|---|---|
| 21887 | 3 | | | | | Mir7003 |
| 21888 | 3 | | | | | Mir7004 |
| 21889 | 3 | | | | | Mir7005 |
| 21890 | 3 | | | | | Mir7006 |
| 21891 | 3 | | | | | Mir7007 |
| 21892 | 3 | | | | | Mir7008 |
| 21893 | 3 | | | | | Mir7009 |
| 21894 | 3 | | | | | Mir701 |
| 21895 | 3 | | | | | Mir7010 |
| 21896 | 3 | | | | | Mir7011 |
| 21897 | 3 | | | | | Mir7012 |
| 21898 | 3 | | | | | Mir7013 |
| 21899 | 3 | | | | | Mir7014 |
| 21900 | 3 | | | | | Mir7015 |
| 21901 | 3 | | | | | Mir7016 |
| 21902 | 3 | | | | | Mir7017 |
| 21903 | 3 | | | | | Mir7018 |
| 21904 | 3 | | | | | Mir7019 |
| 21905 | 3 | | | | | Mir702 |
| 21906 | 3 | | | | | Mir7020 |
| 21907 | 3 | | | | | Mir7021 |
| 21908 | 3 | | | | | Mir7022 |
| 21909 | 3 | | | | | Mir7023 |
| 21910 | 3 | | | | | Mir7024 |
| 21911 | 3 | | | | | Mir7025 |
| 21912 | 3 | | | | | Mir7026 |
| 21913 | 3 | | | | | Mir7027 |
| 21914 | 3 | | | | | Mir7028 |
| 21915 | 3 | | | | | Mir7029 |
| 21916 | 3 | | | | | Mir7030 |
| 21917 | 3 | | | | | Mir7031 |
| 21918 | 3 | | | | | Mir7032 |
| 21919 | 3 | | | | | Mir7033 |
| 21920 | 3 | | | | | Mir7034 |
| 21921 | 3 | | | | | Mir7035 |
| 21922 | 3 | | | | | Mir7036 |
| 21923 | 3 | | | | | Mir7036b |
| 21924 | 3 | | | | | Mir7037 |
| 21925 | 3 | | | | | Mir7038 |
| 21926 | 3 | | | | | Mir7039 |
| 21927 | 3 | | | | | Mir704 |
| 21928 | 3 | | | | | Mir7040 |
| 21929 | 3 | | | | | Mir7041 |
| 21930 | 3 | | | | | Mir7042 |
| 21931 | 3 | | | | | Mir7043 |
| 21932 | 3 | | | | | Mir7044 |
| 21933 | 3 | | | | | Mir7045 |
| 21934 | 3 | | | | | Mir7046 |
| 21935 | 3 | | | | | Mir7047 |
| 21936 | 3 | | | | | Mir7048 |
| 21937 | 3 | | | | | Mir7049 |
| 21938 | 3 | | | | | Mir705 |
| 21939 | 3 | | | | | Mir7050 |
| 21940 | 3 | | | | | Mir7051 |
| 21941 | 3 | | | | | Mir7052 |
| 21942 | 3 | | | | | Mir7053 |
| 21943 | 3 | | | | | Mir7054 |
| 21944 | 3 | | | | | Mir7055 |
| 21945 | 3 | | | | | Mir7056 |
| 21946 | 3 | | | | | Mir7057 |
| 21947 | 3 | | | | | Mir7058 |
| 21948 | 3 | | | | | Mir7059 |
| 21949 | 3 | | | | | Mir706 |
| 21950 | 3 | | | | | Mir7061 |
| 21951 | 3 | | | | | Mir7062 |
| 21952 | 3 | | | | | Mir7063 |
| 21953 | 3 | | | | | Mir7064 |
| 21954 | 3 | | | | | Mir7065 |
| 21955 | 3 | | | | | Mir7066 |
| 21956 | 3 | | | | | Mir7067 |
| 21957 | 3 | | | | | Mir7068 |
| 21958 | 3 | | | | | Mir7069 |
| 21959 | 3 | | | | | Mir707 |
| 21960 | 3 | | | | | Mir7070 |
| 21961 | 3 | | | | | Mir7071 |
| 21962 | 3 | | | | | Mir7072 |
| 21963 | 3 | | | | | Mir7073 |
| 21964 | 3 | | | | | Mir7074 |
| 21965 | 3 | | | | | Mir7075 |
| 21966 | 3 | | | | | Mir7076 |
| 21967 | 3 | | | | | Mir7077 |
| 21968 | 3 | | | | | Mir7078 |
| 21969 | 3 | | | | | Mir7079 |
| 21970 | 3 | | | | | Mir708 |
| 21971 | 3 | | | | | Mir7080 |
| 21972 | 3 | | | | | Mir7081 |
| 21973 | 3 | | | | | Mir7082 |
| 21974 | 3 | | | | | Mir7083 |
| 21975 | 3 | | | | | Mir7084 |
| 21976 | 3 | | | | | Mir7085 |
| 21977 | 3 | | | | | Mir7086 |
| 21978 | 3 | | | | | Mir7087 |
| 21979 | 3 | | | | | Mir7088 |
| 21980 | 3 | | | | | Mir7089 |
| 21981 | 3 | | | | | Mir709 |
| 21982 | 3 | | | | | Mir7090 |
| 21983 | 3 | | | | | Mir7091 |
| 21984 | 3 | | | | | Mir7092 |
| 21985 | 3 | | | | | Mir7093 |
| 21986 | 3 | | | | | Mir7094-1 |
| 21987 | 3 | | | | | Mir7094-2 |
| 21988 | 3 | | | | | Mir710 |
| 21989 | 3 | | | | | Mir711 |
| 21990 | 3 | | | | | Mir7115 |
| 21991 | 3 | | | | | Mir7117 |
| 21992 | 3 | | | | | Mir7118 |
| 21993 | 3 | | | | | Mir7119 |
| 21994 | 3 | | | | | Mir713 |
| 21995 | 3 | | | | | Mir717 |
| 21996 | 3 | | | | | Mir718 |
| 21997 | 3 | | | | | Mir721 |
| 21998 | 3 | | | | | Mir7210 |
| 21999 | 3 | | | | | Mir7211 |
| 22000 | 3 | | | | | Mir7212 |
| 22001 | 3 | | | | | Mir7213 |
| 22002 | 3 | | | | | Mir7214 |
| 22003 | 3 | | | | | Mir7215 |
| 22004 | 3 | | | | | Mir7216 |
| 22005 | 3 | | | | | Mir7217 |
| 22006 | 3 | | | | | Mir7218 |
| 22007 | 3 | | | | | Mir7219 |
| 22008 | 3 | | | | | Mir7220 |
| 22009 | 3 | | | | | Mir7221 |
| 22010 | 3 | | | | | Mir7222 |
| 22011 | 3 | | | | | Mir7223 |
| 22012 | 3 | | | | | Mir7224 |
| 22013 | 3 | | | | | Mir7225 |
| 22014 | 3 | | | | | Mir7226 |
| 22015 | 3 | | | | | Mir7227 |
| 22016 | 3 | | | | | Mir7228 |
| 22017 | 3 | | | | | Mir7229 |
| 22018 | 3 | | | | | Mir7230 |
| 22019 | 3 | | | | | Mir7231 |
| 22020 | 3 | | | | | Mir7232 |
| 22021 | 3 | | | | | Mir7233 |
| 22022 | 3 | | | | | Mir7234 |
| 22023 | 3 | | | | | Mir7235 |
| 22024 | 3 | | | | | Mir7236 |
| 22025 | 3 | | | | | Mir7237 |
| 22026 | 3 | | | | | Mir7238 |
| 22027 | 3 | | | | | Mir7239 |
| 22028 | 3 | | | | | Mir7240 |
| 22029 | 3 | | | | | Mir7241 |
| 22030 | 3 | | | | | Mir7242 |
| 22031 | 3 | | | | | Mir7243 |
| 22032 | 3 | | | | | Mir741 |
| 22033 | 3 | | | | | Mir742 |
| 22034 | 3 | | | | | Mir743 |
| 22035 | 3 | | | | | Mir743b |
| 22036 | 3 | | | | | Mir744 |
| 22037 | 3 | | | | | Mir7578 |
| 22038 | 3 | | | | | Mir758 |
| 22039 | 3 | | | | | Mir759 |
| 22040 | 3 | | | | | Mir761 |
| 22041 | 3 | | | | | Mir762 |
| 22042 | 3 | | | | | Mir764 |
| 22043 | 3 | | | | | Mir7646 |
| 22044 | 3 | | | | | Mir7647 |
| 22045 | 3 | | | | | Mir7648 |
| 22046 | 3 | | | | | Mir7649 |
| 22047 | 3 | | | | | Mir7650 |
| 22048 | 3 | | | | | Mir7652 |
| 22049 | 3 | | | | | Mir7653 |
| 22050 | 3 | | | | | Mir7654 |
| 22051 | 3 | | | | | Mir7655 |
| 22052 | 3 | | | | | Mir7656 |
| 22053 | 3 | | | | | Mir7657 |
| 22054 | 3 | | | | | Mir7658 |
| 22055 | 3 | | | | | Mir7661 |
| 22056 | 3 | | | | | Mir7662 |
| 22057 | 3 | | | | | Mir7663 |
| 22058 | 3 | | | | | Mir7665 |
| 22059 | 3 | | | | | Mir7666 |
| 22060 | 3 | | | | | Mir7667 |
| 22061 | 3 | | | | | Mir7668 |
| 22062 | 3 | | | | | Mir7669 |
| 22063 | 3 | | | | | Mir767 |
| 22064 | 3 | | | | | Mir7670 |
| 22065 | 3 | | | | | Mir7671 |
| 22066 | 3 | | | | | Mir7672 |
| 22067 | 3 | | | | | Mir7673 |
| 22068 | 3 | | | | | Mir7674 |
| 22069 | 3 | | | | | Mir7675 |
| 22070 | 3 | | | | | Mir7676-2 |
| 22071 | 3 | | | | | Mir7677 |
| 22072 | 3 | | | | | Mir7678 |
| 22073 | 3 | | | | | Mir7679 |
| 22074 | 3 | | | | | Mir7680 |
| 22075 | 3 | | | | | Mir7681 |
| 22076 | 3 | | | | | Mir7682 |
| 22077 | 3 | | | | | Mir7684 |
| 22078 | 3 | | | | | Mir7685 |

Fig. 34 - 116

| | | | | | | | | | | | | |
|---|---|---|---|---|---|---|---|---|---|---|---|---|
| 22079 | 3 | | | | | Mir7686 | 22175 | 3 | | | | Nlrp9a |
| 22080 | 3 | | | | | Mir7687 | 22176 | 3 | | | | Nlrp9c |
| 22081 | 3 | | | | | Mir770 | 22177 | 3 | | | | Nms |
| 22082 | 3 | | | | | Mir7b | 22178 | 3 | | | | Nobox |
| 22083 | 3 | | | | | Mir802 | 22179 | 3 | | | | Noto |
| 22084 | 3 | | | | | Mir804 | 22180 | 3 | | | | Npffr2 |
| 22085 | 3 | | | | | Mir8092 | 22181 | 3 | | | | Nphs1os |
| 22086 | 3 | | | | | Mir8095 | 22182 | 3 | | | | Npvf |
| 22087 | 3 | | | | | Mir8096 | 22183 | 3 | | | | Nrk |
| 22088 | 3 | | | | | Mir8100 | 22184 | 3 | | | | Nxf7 |
| 22089 | 3 | | | | | Mir8105 | 22185 | 3 | | | | Oas1d |
| 22090 | 3 | | | | | Mir8107 | 22186 | 3 | | | | Oas1h |
| 22091 | 3 | | | | | Mir8108 | 22187 | 3 | | | | Obox1 |
| 22092 | 3 | | | | | Mir8109 | 22188 | 3 | | | | Obox2 |
| 22093 | 3 | | | | | Mir8110 | 22189 | 3 | | | | Obox3 |
| 22094 | 3 | | | | | Mir8111 | 22190 | 3 | | | | Obox5 |
| 22095 | 3 | | | | | Mir8115 | 22191 | 3 | | | | Obox6 |
| 22096 | 3 | | | | | Mir8118 | 22192 | 3 | | | | Obp1a |
| 22097 | 3 | | | | | Mir8119 | 22193 | 3 | | | | Obp2b |
| 22098 | 3 | | | | | Mir8120 | 22194 | 3 | | | | Oc90 |
| 22099 | 3 | | | | | Mir871 | 22195 | 3 | | | | Odam |
| 22100 | 3 | | | | | Mir872 | 22196 | 3 | | | | Ofcc1 |
| 22101 | 3 | | | | | Mir873b | 22197 | 3 | | | | Olfr1 |
| 22102 | 3 | | | | | Mir874 | 22198 | 3 | | | | Olfr10 |
| 22103 | 3 | | | | | Mir875 | 22199 | 3 | | | | Olfr100 |
| 22104 | 3 | | | | | Mir876 | 22200 | 3 | | | | Olfr1000 |
| 22105 | 3 | | | | | Mir877 | 22201 | 3 | | | | Olfr1002 |
| 22106 | 3 | | | | | Mir878 | 22202 | 3 | | | | Olfr1006 |
| 22107 | 3 | | | | | Mir879 | 22203 | 3 | | | | Olfr1008 |
| 22108 | 3 | | | | | Mir880 | 22204 | 3 | | | | Olfr1009 |
| 22109 | 3 | | | | | Mir881 | 22205 | 3 | | | | Olfr101 |
| 22110 | 3 | | | | | Mir882 | 22206 | 3 | | | | Olfr1010 |
| 22111 | 3 | | | | | Mir883a | 22207 | 3 | | | | Olfr1012 |
| 22112 | 3 | | | | | Mir883b | 22208 | 3 | | | | Olfr1013 |
| 22113 | 3 | | | | | Mir9-1 | 22209 | 3 | | | | Olfr1014 |
| 22114 | 3 | | | | | Mir9-2 | 22210 | 3 | | | | Olfr1015 |
| 22115 | 3 | | | | | Mir9-3 | 22211 | 3 | | | | Olfr1016 |
| 22116 | 3 | | | | | Mir92-1 | 22212 | 3 | | | | Olfr1018 |
| 22117 | 3 | | | | | Mir92-2 | 22213 | 3 | | | | Olfr1019 |
| 22118 | 3 | | | | | Mir92b | 22214 | 3 | | | | Olfr102 |
| 22119 | 3 | | | | | Mir93 | 22215 | 3 | | | | Olfr1020 |
| 22120 | 3 | | | | | Mir96 | 22216 | 3 | | | | Olfr1022 |
| 22121 | 3 | | | | | Mir98 | 22217 | 3 | | | | Olfr1023 |
| 22122 | 3 | | | | | Mir99a | 22218 | 3 | | | | Olfr1024 |
| 22123 | 3 | | | | | Mir99b | 22219 | 3 | | | | Olfr1026 |
| 22124 | 3 | | | | | Mirlet7a-1 | 22220 | 3 | | | | Olfr1028 |
| 22125 | 3 | | | | | Mirlet7a-2 | 22221 | 3 | | | | Olfr1029 |
| 22126 | 3 | | | | | Mirlet7b | 22222 | 3 | | | | Olfr103 |
| 22127 | 3 | | | | | Mirlet7c-1 | 22223 | 3 | | | | Olfr1030 |
| 22128 | 3 | | | | | Mirlet7c-2 | 22224 | 3 | | | | Olfr1031 |
| 22129 | 3 | | | | | Mirlet7e | 22225 | 3 | | | | Olfr1032 |
| 22130 | 3 | | | | | Mirlet7f-1 | 22226 | 3 | | | | Olfr1033 |
| 22131 | 3 | | | | | Mirlet7f-2 | 22227 | 3 | | | | Olfr1034 |
| 22132 | 3 | | | | | Mirlet7g | 22228 | 3 | | | | Olfr1036 |
| 22133 | 3 | | | | | Mirlet7i | 22229 | 3 | | | | Olfr1037 |
| 22134 | 3 | | | | | Mirlet7j | 22230 | 3 | | | | Olfr1038-ps |
| 22135 | 3 | | | | | Mirlet7k | 22231 | 3 | | | | Olfr1039 |
| 22136 | 3 | | | | | Mixl1 | 22232 | 3 | | | | Olfr1040 |
| 22137 | 3 | | | | | Mmp1a | 22233 | 3 | | | | Olfr1042 |
| 22138 | 3 | | | | | Mmp1b | 22234 | 3 | | | | Olfr1043 |
| 22139 | 3 | | | | | Mmp20 | 22235 | 3 | | | | Olfr1044 |
| 22140 | 3 | | | | | Mmp21 | 22236 | 3 | | | | Olfr1045 |
| 22141 | 3 | | | | | Mmp27 | 22237 | 3 | | | | Olfr1046 |
| 22142 | 3 | | | | | Moxd2 | 22238 | 3 | | | | Olfr1047 |
| 22143 | 3 | | | | | Mrgpra1 | 22239 | 3 | | | | Olfr1048 |
| 22144 | 3 | | | | | Mrgpra3 | 22240 | 3 | | | | Olfr1049 |
| 22145 | 3 | | | | | Mrgpra4 | 22241 | 3 | | | | Olfr1051 |
| 22146 | 3 | | | | | Mrgpra6 | 22242 | 3 | | | | Olfr1052 |
| 22147 | 3 | | | | | Mrgpra9 | 22243 | 3 | | | | Olfr1053 |
| 22148 | 3 | | | | | Mrgprb4 | 22244 | 3 | | | | Olfr1054 |
| 22149 | 3 | | | | | Mrgprb5 | 22245 | 3 | | | | Olfr1055 |
| 22150 | 3 | | | | | Mrgprd | 22246 | 3 | | | | Olfr1056 |
| 22151 | 3 | | | | | Mrgprx1 | 22247 | 3 | | | | Olfr1057 |
| 22152 | 3 | | | | | Msgn1 | 22248 | 3 | | | | Olfr1058 |
| 22153 | 3 | | | | | Mslnl | 22249 | 3 | | | | Olfr1061 |
| 22154 | 3 | | | | | Mtnr1b | 22250 | 3 | | | | Olfr1062 |
| 22155 | 3 | | | | | Muc19 | 22251 | 3 | | | | Olfr1065 |
| 22156 | 3 | | | | | Mycs | 22252 | 3 | | | | Olfr1066 |
| 22157 | 3 | | | | | Myo3a | 22253 | 3 | | | | Olfr107 |
| 22158 | 3 | | | | | Myrfl | 22254 | 3 | | | | Olfr1076 |
| 22159 | 3 | | | | | Naip7 | 22255 | 3 | | | | Olfr1077-ps1 |
| 22160 | 3 | | | | | Nanog | 22256 | 3 | | | | Olfr1079 |
| 22161 | 3 | | | | | Nat3 | 22257 | 3 | | | | Olfr108 |
| 22162 | 3 | | | | | Ndufs5 | 22258 | 3 | | | | Olfr1080 |
| 22163 | 3 | | | | | Neurod4 | 22259 | 3 | | | | Olfr1082 |
| 22164 | 3 | | | | | Nkx1-1 | 22260 | 3 | | | | Olfr1084 |
| 22165 | 3 | | | | | Nkx1-2 | 22261 | 3 | | | | Olfr1085 |
| 22166 | 3 | | | | | Nkx2-2os | 22262 | 3 | | | | Olfr1086 |
| 22167 | 3 | | | | | Nkx2-9 | 22263 | 3 | | | | Olfr1087 |
| 22168 | 3 | | | | | Nkx6-1 | 22264 | 3 | | | | Olfr1089 |
| 22169 | 3 | | | | | Nlrp1a | 22265 | 3 | | | | Olfr109 |
| 22170 | 3 | | | | | Nlrp2 | 22266 | 3 | | | | Olfr1090 |
| 22171 | 3 | | | | | Nlrp4a | 22267 | 3 | | | | Olfr1093 |
| 22172 | 3 | | | | | Nlrp4b | 22268 | 3 | | | | Olfr1094 |
| 22173 | 3 | | | | | Nlrp4f | 22269 | 3 | | | | Olfr1095 |
| 22174 | 3 | | | | | Nlrp4g | 22270 | 3 | | | | Olfr1097 |

Fig. 34 - 117

| | | | | | |
|---|---|---|---|---|---|
| 22271 | 3 | | | | Olfr1098 |
| 22272 | 3 | | | | Olfr1099 |
| 22273 | 3 | | | | Olfr11 |
| 22274 | 3 | | | | Olfr110 |
| 22275 | 3 | | | | Olfr1100 |
| 22276 | 3 | | | | Olfr1101 |
| 22277 | 3 | | | | Olfr1102 |
| 22278 | 3 | | | | Olfr1104 |
| 22279 | 3 | | | | Olfr1105 |
| 22280 | 3 | | | | Olfr1106 |
| 22281 | 3 | | | | Olfr1107 |
| 22282 | 3 | | | | Olfr1109 |
| 22283 | 3 | | | | Olfr111 |
| 22284 | 3 | | | | Olfr1110 |
| 22285 | 3 | | | | Olfr1111 |
| 22286 | 3 | | | | Olfr1112 |
| 22287 | 3 | | | | Olfr1113 |
| 22288 | 3 | | | | Olfr1115 |
| 22289 | 3 | | | | Olfr1116-ps |
| 22290 | 3 | | | | Olfr1118 |
| 22291 | 3 | | | | Olfr1120 |
| 22292 | 3 | | | | Olfr1121 |
| 22293 | 3 | | | | Olfr1122 |
| 22294 | 3 | | | | Olfr1123 |
| 22295 | 3 | | | | Olfr1124 |
| 22296 | 3 | | | | Olfr1126 |
| 22297 | 3 | | | | Olfr1128 |
| 22298 | 3 | | | | Olfr1129 |
| 22299 | 3 | | | | Olfr113 |
| 22300 | 3 | | | | Olfr1130 |
| 22301 | 3 | | | | Olfr1131 |
| 22302 | 3 | | | | Olfr1132 |
| 22303 | 3 | | | | Olfr1133 |
| 22304 | 3 | | | | Olfr1134 |
| 22305 | 3 | | | | Olfr1135 |
| 22306 | 3 | | | | Olfr1136 |
| 22307 | 3 | | | | Olfr1137 |
| 22308 | 3 | | | | Olfr1138 |
| 22309 | 3 | | | | Olfr114 |
| 22310 | 3 | | | | Olfr1140 |
| 22311 | 3 | | | | Olfr1141 |
| 22312 | 3 | | | | Olfr1143 |
| 22313 | 3 | | | | Olfr1145 |
| 22314 | 3 | | | | Olfr1148 |
| 22315 | 3 | | | | Olfr115 |
| 22316 | 3 | | | | Olfr1151 |
| 22317 | 3 | | | | Olfr1152 |
| 22318 | 3 | | | | Olfr1153 |
| 22319 | 3 | | | | Olfr1154 |
| 22320 | 3 | | | | Olfr1155 |
| 22321 | 3 | | | | Olfr1156 |
| 22322 | 3 | | | | Olfr1157 |
| 22323 | 3 | | | | Olfr1158 |
| 22324 | 3 | | | | Olfr116 |
| 22325 | 3 | | | | Olfr1160 |
| 22326 | 3 | | | | Olfr1161 |
| 22327 | 3 | | | | Olfr1162 |
| 22328 | 3 | | | | Olfr1163 |
| 22329 | 3 | | | | Olfr1164 |
| 22330 | 3 | | | | Olfr1166 |
| 22331 | 3 | | | | Olfr1167 |
| 22332 | 3 | | | | Olfr1168 |
| 22333 | 3 | | | | Olfr117 |
| 22334 | 3 | | | | Olfr1170 |
| 22335 | 3 | | | | Olfr1173 |
| 22336 | 3 | | | | Olfr1176 |
| 22337 | 3 | | | | Olfr1178 |
| 22338 | 3 | | | | Olfr1179 |
| 22339 | 3 | | | | Olfr118 |
| 22340 | 3 | | | | Olfr1180 |
| 22341 | 3 | | | | Olfr1181 |
| 22342 | 3 | | | | Olfr1182 |
| 22343 | 3 | | | | Olfr1183 |
| 22344 | 3 | | | | Olfr1184 |
| 22345 | 3 | | | | Olfr1188 |
| 22346 | 3 | | | | Olfr1189 |
| 22347 | 3 | | | | Olfr119 |
| 22348 | 3 | | | | Olfr1193 |
| 22349 | 3 | | | | Olfr1195 |
| 22350 | 3 | | | | Olfr1196 |
| 22351 | 3 | | | | Olfr1197 |
| 22352 | 3 | | | | Olfr1198 |
| 22353 | 3 | | | | Olfr1199 |
| 22354 | 3 | | | | Olfr12 |
| 22355 | 3 | | | | Olfr120 |
| 22356 | 3 | | | | Olfr1200 |
| 22357 | 3 | | | | Olfr1201 |
| 22358 | 3 | | | | Olfr1202 |
| 22359 | 3 | | | | Olfr1204 |
| 22360 | 3 | | | | Olfr1205 |
| 22361 | 3 | | | | Olfr1206 |
| 22362 | 3 | | | | Olfr1208 |
| 22363 | 3 | | | | Olfr1209 |
| 22364 | 3 | | | | Olfr121 |
| 22365 | 3 | | | | Olfr1211 |
| 22366 | 3 | | | | Olfr1212 |
| 22367 | 3 | | | | Olfr1213 |
| 22368 | 3 | | | | Olfr1214 |
| 22369 | 3 | | | | Olfr1215 |
| 22370 | 3 | | | | Olfr1216 |
| 22371 | 3 | | | | Olfr1217 |
| 22372 | 3 | | | | Olfr1218 |
| 22373 | 3 | | | | Olfr1219 |
| 22374 | 3 | | | | Olfr122 |
| 22375 | 3 | | | | Olfr1220 |
| 22376 | 3 | | | | Olfr1221 |
| 22377 | 3 | | | | Olfr1222 |
| 22378 | 3 | | | | Olfr1223 |
| 22379 | 3 | | | | Olfr1225 |
| 22380 | 3 | | | | Olfr1226 |
| 22381 | 3 | | | | Olfr1228 |
| 22382 | 3 | | | | Olfr1229 |
| 22383 | 3 | | | | Olfr123 |
| 22384 | 3 | | | | Olfr1230 |
| 22385 | 3 | | | | Olfr1231 |
| 22386 | 3 | | | | Olfr1232 |
| 22387 | 3 | | | | Olfr1233 |
| 22388 | 3 | | | | Olfr1234 |
| 22389 | 3 | | | | Olfr1238 |
| 22390 | 3 | | | | Olfr1239 |
| 22391 | 3 | | | | Olfr124 |
| 22392 | 3 | | | | Olfr1240 |
| 22393 | 3 | | | | Olfr1241 |
| 22394 | 3 | | | | Olfr1242 |
| 22395 | 3 | | | | Olfr1243 |
| 22396 | 3 | | | | Olfr1245 |
| 22397 | 3 | | | | Olfr1246 |
| 22398 | 3 | | | | Olfr1247 |
| 22399 | 3 | | | | Olfr1248 |
| 22400 | 3 | | | | Olfr1249 |
| 22401 | 3 | | | | Olfr125 |
| 22402 | 3 | | | | Olfr1250 |
| 22403 | 3 | | | | Olfr1251 |
| 22404 | 3 | | | | Olfr1252 |
| 22405 | 3 | | | | Olfr1253 |
| 22406 | 3 | | | | Olfr1254 |
| 22407 | 3 | | | | Olfr1255 |
| 22408 | 3 | | | | Olfr1256 |
| 22409 | 3 | | | | Olfr1257 |
| 22410 | 3 | | | | Olfr1258 |
| 22411 | 3 | | | | Olfr1259 |
| 22412 | 3 | | | | Olfr1260 |
| 22413 | 3 | | | | Olfr1261 |
| 22414 | 3 | | | | Olfr1262 |
| 22415 | 3 | | | | Olfr1263 |
| 22416 | 3 | | | | Olfr1264 |
| 22417 | 3 | | | | Olfr1265 |
| 22418 | 3 | | | | Olfr1269 |
| 22419 | 3 | | | | Olfr1270 |
| 22420 | 3 | | | | Olfr1271 |
| 22421 | 3 | | | | Olfr1272 |
| 22422 | 3 | | | | Olfr1273-ps |
| 22423 | 3 | | | | Olfr1274-ps |
| 22424 | 3 | | | | Olfr1275 |
| 22425 | 3 | | | | Olfr1276 |
| 22426 | 3 | | | | Olfr1277 |
| 22427 | 3 | | | | Olfr1278 |
| 22428 | 3 | | | | Olfr1280 |
| 22429 | 3 | | | | Olfr1281 |
| 22430 | 3 | | | | Olfr1282 |
| 22431 | 3 | | | | Olfr1283 |
| 22432 | 3 | | | | Olfr1284 |
| 22433 | 3 | | | | Olfr1286 |
| 22434 | 3 | | | | Olfr1287 |
| 22435 | 3 | | | | Olfr1288 |
| 22436 | 3 | | | | Olfr1289 |
| 22437 | 3 | | | | Olfr129 |
| 22438 | 3 | | | | Olfr1290 |
| 22439 | 3 | | | | Olfr1294 |
| 22440 | 3 | | | | Olfr1295 |
| 22441 | 3 | | | | Olfr1297 |
| 22442 | 3 | | | | Olfr1298 |
| 22443 | 3 | | | | Olfr1299 |
| 22444 | 3 | | | | Olfr130 |
| 22445 | 3 | | | | Olfr1300-ps1 |
| 22446 | 3 | | | | Olfr1301 |
| 22447 | 3 | | | | Olfr1302 |
| 22448 | 3 | | | | Olfr1303 |
| 22449 | 3 | | | | Olfr1305 |
| 22450 | 3 | | | | Olfr1306 |
| 22451 | 3 | | | | Olfr1307 |
| 22452 | 3 | | | | Olfr1308 |
| 22453 | 3 | | | | Olfr1309 |
| 22454 | 3 | | | | Olfr131 |
| 22455 | 3 | | | | Olfr1310 |
| 22456 | 3 | | | | Olfr1311 |
| 22457 | 3 | | | | Olfr1312 |
| 22458 | 3 | | | | Olfr1313 |
| 22459 | 3 | | | | Olfr1314 |
| 22460 | 3 | | | | Olfr1316 |
| 22461 | 3 | | | | Olfr1317 |
| 22462 | 3 | | | | Olfr1318 |

Fig. 34 - 118

| | | | | | | |
|---|---|---|---|---|---|---|
| 22463 | 3 | | | | | Olfr132 |
| 22464 | 3 | | | | | Olfr1320 |
| 22465 | 3 | | | | | Olfr1321 |
| 22466 | 3 | | | | | Olfr1322 |
| 22467 | 3 | | | | | Olfr1323 |
| 22468 | 3 | | | | | Olfr1324 |
| 22469 | 3 | | | | | Olfr1325 |
| 22470 | 3 | | | | | Olfr1328 |
| 22471 | 3 | | | | | Olfr1329 |
| 22472 | 3 | | | | | Olfr133 |
| 22473 | 3 | | | | | Olfr1330 |
| 22474 | 3 | | | | | Olfr1331 |
| 22475 | 3 | | | | | Olfr1333 |
| 22476 | 3 | | | | | Olfr1335 |
| 22477 | 3 | | | | | Olfr1336 |
| 22478 | 3 | | | | | Olfr1337 |
| 22479 | 3 | | | | | Olfr1338 |
| 22480 | 3 | | | | | Olfr1339 |
| 22481 | 3 | | | | | Olfr134 |
| 22482 | 3 | | | | | Olfr1340 |
| 22483 | 3 | | | | | Olfr1341 |
| 22484 | 3 | | | | | Olfr1346 |
| 22485 | 3 | | | | | Olfr1347 |
| 22486 | 3 | | | | | Olfr1348 |
| 22487 | 3 | | | | | Olfr1349 |
| 22488 | 3 | | | | | Olfr135 |
| 22489 | 3 | | | | | Olfr1350 |
| 22490 | 3 | | | | | Olfr1351 |
| 22491 | 3 | | | | | Olfr1352 |
| 22492 | 3 | | | | | Olfr1353 |
| 22493 | 3 | | | | | Olfr1354 |
| 22494 | 3 | | | | | Olfr1355 |
| 22495 | 3 | | | | | Olfr1356 |
| 22496 | 3 | | | | | Olfr1357 |
| 22497 | 3 | | | | | Olfr1359 |
| 22498 | 3 | | | | | Olfr136 |
| 22499 | 3 | | | | | Olfr1360 |
| 22500 | 3 | | | | | Olfr1361 |
| 22501 | 3 | | | | | Olfr1362 |
| 22502 | 3 | | | | | Olfr1364 |
| 22503 | 3 | | | | | Olfr1366 |
| 22504 | 3 | | | | | Olfr1367 |
| 22505 | 3 | | | | | Olfr1368 |
| 22506 | 3 | | | | | Olfr137 |
| 22507 | 3 | | | | | Olfr1370 |
| 22508 | 3 | | | | | Olfr1371 |
| 22509 | 3 | | | | | Olfr1373 |
| 22510 | 3 | | | | | Olfr1377 |
| 22511 | 3 | | | | | Olfr1378 |
| 22512 | 3 | | | | | Olfr138 |
| 22513 | 3 | | | | | Olfr1380 |
| 22514 | 3 | | | | | Olfr1381 |
| 22515 | 3 | | | | | Olfr1382 |
| 22516 | 3 | | | | | Olfr1384 |
| 22517 | 3 | | | | | Olfr1385 |
| 22518 | 3 | | | | | Olfr1386 |
| 22519 | 3 | | | | | Olfr1387 |
| 22520 | 3 | | | | | Olfr1388 |
| 22521 | 3 | | | | | Olfr1389 |
| 22522 | 3 | | | | | Olfr139 |
| 22523 | 3 | | | | | Olfr1390 |
| 22524 | 3 | | | | | Olfr1391 |
| 22525 | 3 | | | | | Olfr1394 |
| 22526 | 3 | | | | | Olfr1395 |
| 22527 | 3 | | | | | Olfr140 |
| 22528 | 3 | | | | | Olfr1402 |
| 22529 | 3 | | | | | Olfr1404 |
| 22530 | 3 | | | | | Olfr1406 |
| 22531 | 3 | | | | | Olfr1408 |
| 22532 | 3 | | | | | Olfr141 |
| 22533 | 3 | | | | | Olfr1410 |
| 22534 | 3 | | | | | Olfr1411 |
| 22535 | 3 | | | | | Olfr1412 |
| 22536 | 3 | | | | | Olfr1414 |
| 22537 | 3 | | | | | Olfr1415 |
| 22538 | 3 | | | | | Olfr1416 |
| 22539 | 3 | | | | | Olfr1417 |
| 22540 | 3 | | | | | Olfr1418 |
| 22541 | 3 | | | | | Olfr1419 |
| 22542 | 3 | | | | | Olfr142 |
| 22543 | 3 | | | | | Olfr1423 |
| 22544 | 3 | | | | | Olfr1424 |
| 22545 | 3 | | | | | Olfr1425 |
| 22546 | 3 | | | | | Olfr1426 |
| 22547 | 3 | | | | | Olfr1427 |
| 22548 | 3 | | | | | Olfr1428 |
| 22549 | 3 | | | | | Olfr143 |
| 22550 | 3 | | | | | Olfr1431 |
| 22551 | 3 | | | | | Olfr1433 |
| 22552 | 3 | | | | | Olfr1434 |
| 22553 | 3 | | | | | Olfr1436 |
| 22554 | 3 | | | | | Olfr1437 |
| 22555 | 3 | | | | | Olfr1440 |
| 22556 | 3 | | | | | Olfr1441 |
| 22557 | 3 | | | | | Olfr1443 |
| 22558 | 3 | | | | | Olfr1444 |
| 22559 | 3 | | | | | Olfr1445 |
| 22560 | 3 | | | | | Olfr1446 |
| 22561 | 3 | | | | | Olfr1447 |
| 22562 | 3 | | | | | Olfr1448 |
| 22563 | 3 | | | | | Olfr1449 |
| 22564 | 3 | | | | | Olfr145 |
| 22565 | 3 | | | | | Olfr1450 |
| 22566 | 3 | | | | | Olfr1451 |
| 22567 | 3 | | | | | Olfr1453 |
| 22568 | 3 | | | | | Olfr1454 |
| 22569 | 3 | | | | | Olfr1457 |
| 22570 | 3 | | | | | Olfr1459 |
| 22571 | 3 | | | | | Olfr146 |
| 22572 | 3 | | | | | Olfr1461 |
| 22573 | 3 | | | | | Olfr1462 |
| 22574 | 3 | | | | | Olfr1463 |
| 22575 | 3 | | | | | Olfr1465 |
| 22576 | 3 | | | | | Olfr1466 |
| 22577 | 3 | | | | | Olfr1467 |
| 22578 | 3 | | | | | Olfr1469 |
| 22579 | 3 | | | | | Olfr147 |
| 22580 | 3 | | | | | Olfr1471 |
| 22581 | 3 | | | | | Olfr1472 |
| 22582 | 3 | | | | | Olfr1474 |
| 22583 | 3 | | | | | Olfr1475 |
| 22584 | 3 | | | | | Olfr1477 |
| 22585 | 3 | | | | | Olfr148 |
| 22586 | 3 | | | | | Olfr1480 |
| 22587 | 3 | | | | | Olfr1484 |
| 22588 | 3 | | | | | Olfr1487 |
| 22589 | 3 | | | | | Olfr1489 |
| 22590 | 3 | | | | | Olfr149 |
| 22591 | 3 | | | | | Olfr1490 |
| 22592 | 3 | | | | | Olfr1491 |
| 22593 | 3 | | | | | Olfr1495 |
| 22594 | 3 | | | | | Olfr1496 |
| 22595 | 3 | | | | | Olfr1497 |
| 22596 | 3 | | | | | Olfr1499 |
| 22597 | 3 | | | | | Olfr15 |
| 22598 | 3 | | | | | Olfr150 |
| 22599 | 3 | | | | | Olfr1500 |
| 22600 | 3 | | | | | Olfr1501 |
| 22601 | 3 | | | | | Olfr1502 |
| 22602 | 3 | | | | | Olfr1504 |
| 22603 | 3 | | | | | Olfr1505 |
| 22604 | 3 | | | | | Olfr1506 |
| 22605 | 3 | | | | | Olfr1508 |
| 22606 | 3 | | | | | Olfr1509 |
| 22607 | 3 | | | | | Olfr151 |
| 22608 | 3 | | | | | Olfr1510 |
| 22609 | 3 | | | | | Olfr1511 |
| 22610 | 3 | | | | | Olfr1512 |
| 22611 | 3 | | | | | Olfr1513 |
| 22612 | 3 | | | | | Olfr152 |
| 22613 | 3 | | | | | Olfr153 |
| 22614 | 3 | | | | | Olfr1532-ps1 |
| 22615 | 3 | | | | | Olfr1535 |
| 22616 | 3 | | | | | Olfr1537 |
| 22617 | 3 | | | | | Olfr154 |
| 22618 | 3 | | | | | Olfr155 |
| 22619 | 3 | | | | | Olfr156 |
| 22620 | 3 | | | | | Olfr157 |
| 22621 | 3 | | | | | Olfr159 |
| 22622 | 3 | | | | | Olfr16 |
| 22623 | 3 | | | | | Olfr160 |
| 22624 | 3 | | | | | Olfr161 |
| 22625 | 3 | | | | | Olfr164 |
| 22626 | 3 | | | | | Olfr166 |
| 22627 | 3 | | | | | Olfr167 |
| 22628 | 3 | | | | | Olfr168 |
| 22629 | 3 | | | | | Olfr169 |
| 22630 | 3 | | | | | Olfr17 |
| 22631 | 3 | | | | | Olfr170 |
| 22632 | 3 | | | | | Olfr171 |
| 22633 | 3 | | | | | Olfr172 |
| 22634 | 3 | | | | | Olfr173 |
| 22635 | 3 | | | | | Olfr175-ps1 |
| 22636 | 3 | | | | | Olfr176 |
| 22637 | 3 | | | | | Olfr177 |
| 22638 | 3 | | | | | Olfr178 |
| 22639 | 3 | | | | | Olfr18 |
| 22640 | 3 | | | | | Olfr180 |
| 22641 | 3 | | | | | Olfr181 |
| 22642 | 3 | | | | | Olfr186 |
| 22643 | 3 | | | | | Olfr187 |
| 22644 | 3 | | | | | Olfr190 |
| 22645 | 3 | | | | | Olfr191 |
| 22646 | 3 | | | | | Olfr192 |
| 22647 | 3 | | | | | Olfr193 |
| 22648 | 3 | | | | | Olfr194 |
| 22649 | 3 | | | | | Olfr195 |
| 22650 | 3 | | | | | Olfr196 |
| 22651 | 3 | | | | | Olfr197 |
| 22652 | 3 | | | | | Olfr198 |
| 22653 | 3 | | | | | Olfr2 |
| 22654 | 3 | | | | | Olfr201 |

Fig. 34 - 119

| | | | | | | |
|---|---|---|---|---|---|---|
| 22655 | 3 | | | | | Olfr202 |
| 22656 | 3 | | | | | Olfr203 |
| 22657 | 3 | | | | | Olfr204 |
| 22658 | 3 | | | | | Olfr205 |
| 22659 | 3 | | | | | Olfr206 |
| 22660 | 3 | | | | | Olfr209 |
| 22661 | 3 | | | | | Olfr211 |
| 22662 | 3 | | | | | Olfr213 |
| 22663 | 3 | | | | | Olfr214 |
| 22664 | 3 | | | | | Olfr218 |
| 22665 | 3 | | | | | Olfr220 |
| 22666 | 3 | | | | | Olfr221 |
| 22667 | 3 | | | | | Olfr222 |
| 22668 | 3 | | | | | Olfr223 |
| 22669 | 3 | | | | | Olfr224 |
| 22670 | 3 | | | | | Olfr225 |
| 22671 | 3 | | | | | Olfr228 |
| 22672 | 3 | | | | | Olfr229 |
| 22673 | 3 | | | | | Olfr231 |
| 22674 | 3 | | | | | Olfr235 |
| 22675 | 3 | | | | | Olfr237-ps1 |
| 22676 | 3 | | | | | Olfr239 |
| 22677 | 3 | | | | | Olfr24 |
| 22678 | 3 | | | | | Olfr243 |
| 22679 | 3 | | | | | Olfr247 |
| 22680 | 3 | | | | | Olfr248 |
| 22681 | 3 | | | | | Olfr25 |
| 22682 | 3 | | | | | Olfr259 |
| 22683 | 3 | | | | | Olfr26 |
| 22684 | 3 | | | | | Olfr262 |
| 22685 | 3 | | | | | Olfr263 |
| 22686 | 3 | | | | | Olfr266 |
| 22687 | 3 | | | | | Olfr267 |
| 22688 | 3 | | | | | Olfr270 |
| 22689 | 3 | | | | | Olfr272 |
| 22690 | 3 | | | | | Olfr273 |
| 22691 | 3 | | | | | Olfr275 |
| 22692 | 3 | | | | | Olfr279 |
| 22693 | 3 | | | | | Olfr281 |
| 22694 | 3 | | | | | Olfr282 |
| 22695 | 3 | | | | | Olfr283 |
| 22696 | 3 | | | | | Olfr284 |
| 22697 | 3 | | | | | Olfr285 |
| 22698 | 3 | | | | | Olfr286 |
| 22699 | 3 | | | | | Olfr290 |
| 22700 | 3 | | | | | Olfr291 |
| 22701 | 3 | | | | | Olfr292 |
| 22702 | 3 | | | | | Olfr293 |
| 22703 | 3 | | | | | Olfr294 |
| 22704 | 3 | | | | | Olfr295 |
| 22705 | 3 | | | | | Olfr297 |
| 22706 | 3 | | | | | Olfr298 |
| 22707 | 3 | | | | | Olfr299 |
| 22708 | 3 | | | | | Olfr3 |
| 22709 | 3 | | | | | Olfr30 |
| 22710 | 3 | | | | | Olfr301 |
| 22711 | 3 | | | | | Olfr304 |
| 22712 | 3 | | | | | Olfr305 |
| 22713 | 3 | | | | | Olfr309 |
| 22714 | 3 | | | | | Olfr310 |
| 22715 | 3 | | | | | Olfr311 |
| 22716 | 3 | | | | | Olfr312 |
| 22717 | 3 | | | | | Olfr313 |
| 22718 | 3 | | | | | Olfr314 |
| 22719 | 3 | | | | | Olfr315 |
| 22720 | 3 | | | | | Olfr316 |
| 22721 | 3 | | | | | Olfr317 |
| 22722 | 3 | | | | | Olfr318 |
| 22723 | 3 | | | | | Olfr319 |
| 22724 | 3 | | | | | Olfr32 |
| 22725 | 3 | | | | | Olfr320 |
| 22726 | 3 | | | | | Olfr322 |
| 22727 | 3 | | | | | Olfr323 |
| 22728 | 3 | | | | | Olfr324 |
| 22729 | 3 | | | | | Olfr328 |
| 22730 | 3 | | | | | Olfr329-ps |
| 22731 | 3 | | | | | Olfr33 |
| 22732 | 3 | | | | | Olfr330 |
| 22733 | 3 | | | | | Olfr331 |
| 22734 | 3 | | | | | Olfr332 |
| 22735 | 3 | | | | | Olfr338 |
| 22736 | 3 | | | | | Olfr339 |
| 22737 | 3 | | | | | Olfr340 |
| 22738 | 3 | | | | | Olfr341 |
| 22739 | 3 | | | | | Olfr342 |
| 22740 | 3 | | | | | Olfr344 |
| 22741 | 3 | | | | | Olfr345 |
| 22742 | 3 | | | | | Olfr346 |
| 22743 | 3 | | | | | Olfr347 |
| 22744 | 3 | | | | | Olfr348 |
| 22745 | 3 | | | | | Olfr350 |
| 22746 | 3 | | | | | Olfr351 |
| 22747 | 3 | | | | | Olfr352 |
| 22748 | 3 | | | | | Olfr353 |
| 22749 | 3 | | | | | Olfr354 |
| 22750 | 3 | | | | | Olfr355 |
| 22751 | 3 | | | | | Olfr356 |
| 22752 | 3 | | | | | Olfr358 |
| 22753 | 3 | | | | | Olfr361 |
| 22754 | 3 | | | | | Olfr362 |
| 22755 | 3 | | | | | Olfr365 |
| 22756 | 3 | | | | | Olfr366 |
| 22757 | 3 | | | | | Olfr367-ps |
| 22758 | 3 | | | | | Olfr368 |
| 22759 | 3 | | | | | Olfr370 |
| 22760 | 3 | | | | | Olfr371 |
| 22761 | 3 | | | | | Olfr372 |
| 22762 | 3 | | | | | Olfr373 |
| 22763 | 3 | | | | | Olfr374 |
| 22764 | 3 | | | | | Olfr376 |
| 22765 | 3 | | | | | Olfr378 |
| 22766 | 3 | | | | | Olfr38 |
| 22767 | 3 | | | | | Olfr380 |
| 22768 | 3 | | | | | Olfr381 |
| 22769 | 3 | | | | | Olfr382 |
| 22770 | 3 | | | | | Olfr384 |
| 22771 | 3 | | | | | Olfr385 |
| 22772 | 3 | | | | | Olfr389 |
| 22773 | 3 | | | | | Olfr39 |
| 22774 | 3 | | | | | Olfr390 |
| 22775 | 3 | | | | | Olfr391-ps |
| 22776 | 3 | | | | | Olfr392 |
| 22777 | 3 | | | | | Olfr393 |
| 22778 | 3 | | | | | Olfr394 |
| 22779 | 3 | | | | | Olfr395 |
| 22780 | 3 | | | | | Olfr397 |
| 22781 | 3 | | | | | Olfr398 |
| 22782 | 3 | | | | | Olfr399 |
| 22783 | 3 | | | | | Olfr401 |
| 22784 | 3 | | | | | Olfr402 |
| 22785 | 3 | | | | | Olfr403 |
| 22786 | 3 | | | | | Olfr406 |
| 22787 | 3 | | | | | Olfr410 |
| 22788 | 3 | | | | | Olfr411 |
| 22789 | 3 | | | | | Olfr412 |
| 22790 | 3 | | | | | Olfr414 |
| 22791 | 3 | | | | | Olfr417 |
| 22792 | 3 | | | | | Olfr418-ps1 |
| 22793 | 3 | | | | | Olfr420 |
| 22794 | 3 | | | | | Olfr421-ps1 |
| 22795 | 3 | | | | | Olfr424 |
| 22796 | 3 | | | | | Olfr426 |
| 22797 | 3 | | | | | Olfr427 |
| 22798 | 3 | | | | | Olfr429 |
| 22799 | 3 | | | | | Olfr43 |
| 22800 | 3 | | | | | Olfr430 |
| 22801 | 3 | | | | | Olfr434 |
| 22802 | 3 | | | | | Olfr435 |
| 22803 | 3 | | | | | Olfr437 |
| 22804 | 3 | | | | | Olfr44 |
| 22805 | 3 | | | | | Olfr441 |
| 22806 | 3 | | | | | Olfr444 |
| 22807 | 3 | | | | | Olfr446 |
| 22808 | 3 | | | | | Olfr447 |
| 22809 | 3 | | | | | Olfr448 |
| 22810 | 3 | | | | | Olfr449 |
| 22811 | 3 | | | | | Olfr45 |
| 22812 | 3 | | | | | Olfr450 |
| 22813 | 3 | | | | | Olfr452 |
| 22814 | 3 | | | | | Olfr453 |
| 22815 | 3 | | | | | Olfr455 |
| 22816 | 3 | | | | | Olfr456 |
| 22817 | 3 | | | | | Olfr457 |
| 22818 | 3 | | | | | Olfr458 |
| 22819 | 3 | | | | | Olfr459 |
| 22820 | 3 | | | | | Olfr46 |
| 22821 | 3 | | | | | Olfr460 |
| 22822 | 3 | | | | | Olfr461 |
| 22823 | 3 | | | | | Olfr462 |
| 22824 | 3 | | | | | Olfr463 |
| 22825 | 3 | | | | | Olfr464 |
| 22826 | 3 | | | | | Olfr466 |
| 22827 | 3 | | | | | Olfr467 |
| 22828 | 3 | | | | | Olfr469 |
| 22829 | 3 | | | | | Olfr47 |
| 22830 | 3 | | | | | Olfr470 |
| 22831 | 3 | | | | | Olfr472 |
| 22832 | 3 | | | | | Olfr473 |
| 22833 | 3 | | | | | Olfr474 |
| 22834 | 3 | | | | | Olfr476 |
| 22835 | 3 | | | | | Olfr477 |
| 22836 | 3 | | | | | Olfr478 |
| 22837 | 3 | | | | | Olfr479 |
| 22838 | 3 | | | | | Olfr48 |
| 22839 | 3 | | | | | Olfr480 |
| 22840 | 3 | | | | | Olfr481 |
| 22841 | 3 | | | | | Olfr482 |
| 22842 | 3 | | | | | Olfr483 |
| 22843 | 3 | | | | | Olfr484 |
| 22844 | 3 | | | | | Olfr485 |
| 22845 | 3 | | | | | Olfr486 |
| 22846 | 3 | | | | | Olfr487 |

Fig. 34 - 120

| | | | | | |
|---|---|---|---|---|---|
| 22847 | 3 | | | | Olfr488 |
| 22848 | 3 | | | | Olfr49 |
| 22849 | 3 | | | | Olfr490 |
| 22850 | 3 | | | | Olfr491 |
| 22851 | 3 | | | | Olfr492 |
| 22852 | 3 | | | | Olfr493 |
| 22853 | 3 | | | | Olfr494 |
| 22854 | 3 | | | | Olfr495 |
| 22855 | 3 | | | | Olfr497 |
| 22856 | 3 | | | | Olfr498 |
| 22857 | 3 | | | | Olfr5 |
| 22858 | 3 | | | | Olfr50 |
| 22859 | 3 | | | | Olfr502 |
| 22860 | 3 | | | | Olfr503 |
| 22861 | 3 | | | | Olfr504 |
| 22862 | 3 | | | | Olfr506 |
| 22863 | 3 | | | | Olfr507 |
| 22864 | 3 | | | | Olfr508 |
| 22865 | 3 | | | | Olfr509 |
| 22866 | 3 | | | | Olfr51 |
| 22867 | 3 | | | | Olfr510 |
| 22868 | 3 | | | | Olfr512 |
| 22869 | 3 | | | | Olfr513 |
| 22870 | 3 | | | | Olfr514 |
| 22871 | 3 | | | | Olfr516 |
| 22872 | 3 | | | | Olfr517 |
| 22873 | 3 | | | | Olfr518 |
| 22874 | 3 | | | | Olfr519 |
| 22875 | 3 | | | | Olfr52 |
| 22876 | 3 | | | | Olfr520 |
| 22877 | 3 | | | | Olfr522 |
| 22878 | 3 | | | | Olfr523 |
| 22879 | 3 | | | | Olfr524 |
| 22880 | 3 | | | | Olfr525 |
| 22881 | 3 | | | | Olfr527 |
| 22882 | 3 | | | | Olfr53 |
| 22883 | 3 | | | | Olfr530 |
| 22884 | 3 | | | | Olfr531 |
| 22885 | 3 | | | | Olfr532 |
| 22886 | 3 | | | | Olfr533 |
| 22887 | 3 | | | | Olfr535 |
| 22888 | 3 | | | | Olfr536 |
| 22889 | 3 | | | | Olfr538 |
| 22890 | 3 | | | | Olfr539 |
| 22891 | 3 | | | | Olfr54 |
| 22892 | 3 | | | | Olfr541 |
| 22893 | 3 | | | | Olfr543 |
| 22894 | 3 | | | | Olfr544 |
| 22895 | 3 | | | | Olfr547 |
| 22896 | 3 | | | | Olfr549 |
| 22897 | 3 | | | | Olfr55 |
| 22898 | 3 | | | | Olfr551 |
| 22899 | 3 | | | | Olfr552 |
| 22900 | 3 | | | | Olfr553 |
| 22901 | 3 | | | | Olfr555 |
| 22902 | 3 | | | | Olfr556 |
| 22903 | 3 | | | | Olfr557 |
| 22904 | 3 | | | | Olfr559 |
| 22905 | 3 | | | | Olfr56 |
| 22906 | 3 | | | | Olfr560 |
| 22907 | 3 | | | | Olfr561 |
| 22908 | 3 | | | | Olfr564 |
| 22909 | 3 | | | | Olfr566 |
| 22910 | 3 | | | | Olfr568 |
| 22911 | 3 | | | | Olfr569 |
| 22912 | 3 | | | | Olfr57 |
| 22913 | 3 | | | | Olfr570 |
| 22914 | 3 | | | | Olfr571 |
| 22915 | 3 | | | | Olfr572 |
| 22916 | 3 | | | | Olfr574 |
| 22917 | 3 | | | | Olfr575 |
| 22918 | 3 | | | | Olfr576 |
| 22919 | 3 | | | | Olfr577 |
| 22920 | 3 | | | | Olfr578 |
| 22921 | 3 | | | | Olfr58 |
| 22922 | 3 | | | | Olfr582 |
| 22923 | 3 | | | | Olfr583 |
| 22924 | 3 | | | | Olfr584 |
| 22925 | 3 | | | | Olfr585 |
| 22926 | 3 | | | | Olfr586 |
| 22927 | 3 | | | | Olfr589 |
| 22928 | 3 | | | | Olfr59 |
| 22929 | 3 | | | | Olfr591 |
| 22930 | 3 | | | | Olfr592 |
| 22931 | 3 | | | | Olfr593 |
| 22932 | 3 | | | | Olfr594 |
| 22933 | 3 | | | | Olfr596 |
| 22934 | 3 | | | | Olfr597 |
| 22935 | 3 | | | | Olfr598 |
| 22936 | 3 | | | | Olfr599 |
| 22937 | 3 | | | | Olfr6 |
| 22938 | 3 | | | | Olfr60 |
| 22939 | 3 | | | | Olfr600 |
| 22940 | 3 | | | | Olfr601 |
| 22941 | 3 | | | | Olfr603 |
| 22942 | 3 | | | | Olfr605 |
| 22943 | 3 | | | | Olfr606 |
| 22944 | 3 | | | | Olfr608 |
| 22945 | 3 | | | | Olfr609 |
| 22946 | 3 | | | | Olfr61 |
| 22947 | 3 | | | | Olfr610 |
| 22948 | 3 | | | | Olfr611 |
| 22949 | 3 | | | | Olfr612 |
| 22950 | 3 | | | | Olfr613 |
| 22951 | 3 | | | | Olfr615 |
| 22952 | 3 | | | | Olfr616 |
| 22953 | 3 | | | | Olfr617 |
| 22954 | 3 | | | | Olfr618 |
| 22955 | 3 | | | | Olfr619 |
| 22956 | 3 | | | | Olfr62 |
| 22957 | 3 | | | | Olfr620 |
| 22958 | 3 | | | | Olfr622 |
| 22959 | 3 | | | | Olfr623 |
| 22960 | 3 | | | | Olfr624 |
| 22961 | 3 | | | | Olfr628 |
| 22962 | 3 | | | | Olfr629 |
| 22963 | 3 | | | | Olfr63 |
| 22964 | 3 | | | | Olfr630 |
| 22965 | 3 | | | | Olfr631 |
| 22966 | 3 | | | | Olfr632 |
| 22967 | 3 | | | | Olfr633 |
| 22968 | 3 | | | | Olfr635 |
| 22969 | 3 | | | | Olfr638 |
| 22970 | 3 | | | | Olfr639 |
| 22971 | 3 | | | | Olfr64 |
| 22972 | 3 | | | | Olfr640 |
| 22973 | 3 | | | | Olfr641 |
| 22974 | 3 | | | | Olfr642 |
| 22975 | 3 | | | | Olfr643 |
| 22976 | 3 | | | | Olfr644 |
| 22977 | 3 | | | | Olfr645 |
| 22978 | 3 | | | | Olfr646 |
| 22979 | 3 | | | | Olfr648 |
| 22980 | 3 | | | | Olfr649 |
| 22981 | 3 | | | | Olfr65 |
| 22982 | 3 | | | | Olfr651 |
| 22983 | 3 | | | | Olfr652 |
| 22984 | 3 | | | | Olfr653 |
| 22985 | 3 | | | | Olfr654 |
| 22986 | 3 | | | | Olfr655 |
| 22987 | 3 | | | | Olfr656 |
| 22988 | 3 | | | | Olfr657 |
| 22989 | 3 | | | | Olfr658 |
| 22990 | 3 | | | | Olfr659 |
| 22991 | 3 | | | | Olfr66 |
| 22992 | 3 | | | | Olfr661 |
| 22993 | 3 | | | | Olfr663 |
| 22994 | 3 | | | | Olfr665 |
| 22995 | 3 | | | | Olfr666 |
| 22996 | 3 | | | | Olfr667 |
| 22997 | 3 | | | | Olfr668 |
| 22998 | 3 | | | | Olfr669 |
| 22999 | 3 | | | | Olfr67 |
| 23000 | 3 | | | | Olfr670 |
| 23001 | 3 | | | | Olfr671 |
| 23002 | 3 | | | | Olfr672 |
| 23003 | 3 | | | | Olfr675 |
| 23004 | 3 | | | | Olfr676 |
| 23005 | 3 | | | | Olfr677 |
| 23006 | 3 | | | | Olfr678 |
| 23007 | 3 | | | | Olfr679 |
| 23008 | 3 | | | | Olfr68 |
| 23009 | 3 | | | | Olfr681 |
| 23010 | 3 | | | | Olfr683 |
| 23011 | 3 | | | | Olfr684 |
| 23012 | 3 | | | | Olfr685 |
| 23013 | 3 | | | | Olfr686 |
| 23014 | 3 | | | | Olfr688 |
| 23015 | 3 | | | | Olfr689 |
| 23016 | 3 | | | | Olfr69 |
| 23017 | 3 | | | | Olfr690 |
| 23018 | 3 | | | | Olfr691 |
| 23019 | 3 | | | | Olfr692 |
| 23020 | 3 | | | | Olfr693 |
| 23021 | 3 | | | | Olfr694 |
| 23022 | 3 | | | | Olfr695 |
| 23023 | 3 | | | | Olfr698 |
| 23024 | 3 | | | | Olfr699 |
| 23025 | 3 | | | | Olfr70 |
| 23026 | 3 | | | | Olfr700 |
| 23027 | 3 | | | | Olfr702 |
| 23028 | 3 | | | | Olfr703 |
| 23029 | 3 | | | | Olfr704 |
| 23030 | 3 | | | | Olfr705 |
| 23031 | 3 | | | | Olfr706 |
| 23032 | 3 | | | | Olfr707 |
| 23033 | 3 | | | | Olfr71 |
| 23034 | 3 | | | | Olfr710 |
| 23035 | 3 | | | | Olfr711 |
| 23036 | 3 | | | | Olfr713 |
| 23037 | 3 | | | | Olfr714 |
| 23038 | 3 | | | | Olfr715 |

Fig. 34 - 121

| | | | | | |
|---|---|---|---|---|---|
| 23039 | 3 | | | | Olfr716 |
| 23040 | 3 | | | | Olfr720 |
| 23041 | 3 | | | | Olfr722 |
| 23042 | 3 | | | | Olfr723 |
| 23043 | 3 | | | | Olfr724 |
| 23044 | 3 | | | | Olfr725 |
| 23045 | 3 | | | | Olfr726 |
| 23046 | 3 | | | | Olfr727 |
| 23047 | 3 | | | | Olfr728 |
| 23048 | 3 | | | | Olfr729 |
| 23049 | 3 | | | | Olfr73 |
| 23050 | 3 | | | | Olfr730 |
| 23051 | 3 | | | | Olfr732 |
| 23052 | 3 | | | | Olfr734 |
| 23053 | 3 | | | | Olfr735 |
| 23054 | 3 | | | | Olfr736 |
| 23055 | 3 | | | | Olfr738 |
| 23056 | 3 | | | | Olfr739 |
| 23057 | 3 | | | | Olfr74 |
| 23058 | 3 | | | | Olfr740 |
| 23059 | 3 | | | | Olfr741 |
| 23060 | 3 | | | | Olfr742 |
| 23061 | 3 | | | | Olfr743 |
| 23062 | 3 | | | | Olfr744 |
| 23063 | 3 | | | | Olfr745 |
| 23064 | 3 | | | | Olfr746 |
| 23065 | 3 | | | | Olfr747 |
| 23066 | 3 | | | | Olfr748 |
| 23067 | 3 | | | | Olfr749 |
| 23068 | 3 | | | | Olfr75-ps1 |
| 23069 | 3 | | | | Olfr76 |
| 23070 | 3 | | | | Olfr763 |
| 23071 | 3 | | | | Olfr765 |
| 23072 | 3 | | | | Olfr767 |
| 23073 | 3 | | | | Olfr768 |
| 23074 | 3 | | | | Olfr769 |
| 23075 | 3 | | | | Olfr77 |
| 23076 | 3 | | | | Olfr770 |
| 23077 | 3 | | | | Olfr771 |
| 23078 | 3 | | | | Olfr772 |
| 23079 | 3 | | | | Olfr773 |
| 23080 | 3 | | | | Olfr774 |
| 23081 | 3 | | | | Olfr775 |
| 23082 | 3 | | | | Olfr776 |
| 23083 | 3 | | | | Olfr777 |
| 23084 | 3 | | | | Olfr780 |
| 23085 | 3 | | | | Olfr781 |
| 23086 | 3 | | | | Olfr782 |
| 23087 | 3 | | | | Olfr784 |
| 23088 | 3 | | | | Olfr786 |
| 23089 | 3 | | | | Olfr787 |
| 23090 | 3 | | | | Olfr790 |
| 23091 | 3 | | | | Olfr791 |
| 23092 | 3 | | | | Olfr792 |
| 23093 | 3 | | | | Olfr794 |
| 23094 | 3 | | | | Olfr796 |
| 23095 | 3 | | | | Olfr798 |
| 23096 | 3 | | | | Olfr799 |
| 23097 | 3 | | | | Olfr8 |
| 23098 | 3 | | | | Olfr800 |
| 23099 | 3 | | | | Olfr801 |
| 23100 | 3 | | | | Olfr802 |
| 23101 | 3 | | | | Olfr803 |
| 23102 | 3 | | | | Olfr804 |
| 23103 | 3 | | | | Olfr805 |
| 23104 | 3 | | | | Olfr806 |
| 23105 | 3 | | | | Olfr807 |
| 23106 | 3 | | | | Olfr808 |
| 23107 | 3 | | | | Olfr809 |
| 23108 | 3 | | | | Olfr810 |
| 23109 | 3 | | | | Olfr811 |
| 23110 | 3 | | | | Olfr812 |
| 23111 | 3 | | | | Olfr813 |
| 23112 | 3 | | | | Olfr814 |
| 23113 | 3 | | | | Olfr815 |
| 23114 | 3 | | | | Olfr816 |
| 23115 | 3 | | | | Olfr818 |
| 23116 | 3 | | | | Olfr819 |
| 23117 | 3 | | | | Olfr820 |
| 23118 | 3 | | | | Olfr821 |
| 23119 | 3 | | | | Olfr822 |
| 23120 | 3 | | | | Olfr823 |
| 23121 | 3 | | | | Olfr824 |
| 23122 | 3 | | | | Olfr825 |
| 23123 | 3 | | | | Olfr826 |
| 23124 | 3 | | | | Olfr827 |
| 23125 | 3 | | | | Olfr828 |
| 23126 | 3 | | | | Olfr829 |
| 23127 | 3 | | | | Olfr830 |
| 23128 | 3 | | | | Olfr832 |
| 23129 | 3 | | | | Olfr834 |
| 23130 | 3 | | | | Olfr835 |
| 23131 | 3 | | | | Olfr836 |
| 23132 | 3 | | | | Olfr837 |
| 23133 | 3 | | | | Olfr843 |
| 23134 | 3 | | | | Olfr845 |
| 23135 | 3 | | | | Olfr846 |
| 23136 | 3 | | | | Olfr847 |
| 23137 | 3 | | | | Olfr849 |
| 23138 | 3 | | | | Olfr850 |
| 23139 | 3 | | | | Olfr851 |
| 23140 | 3 | | | | Olfr853 |
| 23141 | 3 | | | | Olfr854 |
| 23142 | 3 | | | | Olfr855 |
| 23143 | 3 | | | | Olfr856-ps1 |
| 23144 | 3 | | | | Olfr857 |
| 23145 | 3 | | | | Olfr859 |
| 23146 | 3 | | | | Olfr860 |
| 23147 | 3 | | | | Olfr862 |
| 23148 | 3 | | | | Olfr866 |
| 23149 | 3 | | | | Olfr867 |
| 23150 | 3 | | | | Olfr868 |
| 23151 | 3 | | | | Olfr869 |
| 23152 | 3 | | | | Olfr870 |
| 23153 | 3 | | | | Olfr871 |
| 23154 | 3 | | | | Olfr873 |
| 23155 | 3 | | | | Olfr874 |
| 23156 | 3 | | | | Olfr875 |
| 23157 | 3 | | | | Olfr876 |
| 23158 | 3 | | | | Olfr877 |
| 23159 | 3 | | | | Olfr878 |
| 23160 | 3 | | | | Olfr881 |
| 23161 | 3 | | | | Olfr883 |
| 23162 | 3 | | | | Olfr884 |
| 23163 | 3 | | | | Olfr885 |
| 23164 | 3 | | | | Olfr887 |
| 23165 | 3 | | | | Olfr888 |
| 23166 | 3 | | | | Olfr889 |
| 23167 | 3 | | | | Olfr890 |
| 23168 | 3 | | | | Olfr891 |
| 23169 | 3 | | | | Olfr894 |
| 23170 | 3 | | | | Olfr895 |
| 23171 | 3 | | | | Olfr898 |
| 23172 | 3 | | | | Olfr899 |
| 23173 | 3 | | | | Olfr9 |
| 23174 | 3 | | | | Olfr90 |
| 23175 | 3 | | | | Olfr900 |
| 23176 | 3 | | | | Olfr901 |
| 23177 | 3 | | | | Olfr902 |
| 23178 | 3 | | | | Olfr904 |
| 23179 | 3 | | | | Olfr905 |
| 23180 | 3 | | | | Olfr906 |
| 23181 | 3 | | | | Olfr907 |
| 23182 | 3 | | | | Olfr908 |
| 23183 | 3 | | | | Olfr91 |
| 23184 | 3 | | | | Olfr910 |
| 23185 | 3 | | | | Olfr911-ps1 |
| 23186 | 3 | | | | Olfr912 |
| 23187 | 3 | | | | Olfr913 |
| 23188 | 3 | | | | Olfr914 |
| 23189 | 3 | | | | Olfr915 |
| 23190 | 3 | | | | Olfr916 |
| 23191 | 3 | | | | Olfr917 |
| 23192 | 3 | | | | Olfr918 |
| 23193 | 3 | | | | Olfr919 |
| 23194 | 3 | | | | Olfr92 |
| 23195 | 3 | | | | Olfr921 |
| 23196 | 3 | | | | Olfr922 |
| 23197 | 3 | | | | Olfr923 |
| 23198 | 3 | | | | Olfr924 |
| 23199 | 3 | | | | Olfr926 |
| 23200 | 3 | | | | Olfr930 |
| 23201 | 3 | | | | Olfr933 |
| 23202 | 3 | | | | Olfr934 |
| 23203 | 3 | | | | Olfr935 |
| 23204 | 3 | | | | Olfr936 |
| 23205 | 3 | | | | Olfr937 |
| 23206 | 3 | | | | Olfr938 |
| 23207 | 3 | | | | Olfr943 |
| 23208 | 3 | | | | Olfr945 |
| 23209 | 3 | | | | Olfr947-ps1 |
| 23210 | 3 | | | | Olfr948 |
| 23211 | 3 | | | | Olfr95 |
| 23212 | 3 | | | | Olfr951 |
| 23213 | 3 | | | | Olfr952 |
| 23214 | 3 | | | | Olfr954 |
| 23215 | 3 | | | | Olfr955 |
| 23216 | 3 | | | | Olfr957 |
| 23217 | 3 | | | | Olfr958 |
| 23218 | 3 | | | | Olfr959 |
| 23219 | 3 | | | | Olfr96 |
| 23220 | 3 | | | | Olfr960 |
| 23221 | 3 | | | | Olfr961 |
| 23222 | 3 | | | | Olfr963 |
| 23223 | 3 | | | | Olfr965 |
| 23224 | 3 | | | | Olfr967 |
| 23225 | 3 | | | | Olfr968 |
| 23226 | 3 | | | | Olfr969 |
| 23227 | 3 | | | | Olfr97 |
| 23228 | 3 | | | | Olfr970 |
| 23229 | 3 | | | | Olfr971 |
| 23230 | 3 | | | | Olfr972 |

Fig. 34 - 122

| | | | | | | |
|---|---|---|---|---|---|---|
| 23231 | 3 | | | | | Olfr974 |
| 23232 | 3 | | | | | Olfr975 |
| 23233 | 3 | | | | | Olfr976 |
| 23234 | 3 | | | | | Olfr978 |
| 23235 | 3 | | | | | Olfr979 |
| 23236 | 3 | | | | | Olfr98 |
| 23237 | 3 | | | | | Olfr980 |
| 23238 | 3 | | | | | Olfr981 |
| 23239 | 3 | | | | | Olfr982 |
| 23240 | 3 | | | | | Olfr983 |
| 23241 | 3 | | | | | Olfr984 |
| 23242 | 3 | | | | | Olfr985 |
| 23243 | 3 | | | | | Olfr986 |
| 23244 | 3 | | | | | Olfr987 |
| 23245 | 3 | | | | | Olfr988 |
| 23246 | 3 | | | | | Olfr992 |
| 23247 | 3 | | | | | Olfr993 |
| 23248 | 3 | | | | | Olfr994 |
| 23249 | 3 | | | | | Olfr995 |
| 23250 | 3 | | | | | Olfr996 |
| 23251 | 3 | | | | | Olfr998 |
| 23252 | 3 | | | | | Omt2a |
| 23253 | 3 | | | | | Omt2b |
| 23254 | 3 | | | | | Ooep |
| 23255 | 3 | | | | | Oog1 |
| 23256 | 3 | | | | | Oog2 |
| 23257 | 3 | | | | | Oog3 |
| 23258 | 3 | | | | | Oog4 |
| 23259 | 3 | | | | | Oosp3 |
| 23260 | 3 | | | | | Opn1sw |
| 23261 | 3 | | | | | Opn5 |
| 23262 | 3 | | | | | Oprm1 |
| 23263 | 3 | | | | | Otogl |
| 23264 | 3 | | | | | Otol1 |
| 23265 | 3 | | | | | Otor |
| 23266 | 3 | | | | | Otx2os1 |
| 23267 | 3 | | | | | Ovch2 |
| 23268 | 3 | | | | | Pabpc4l |
| 23269 | 3 | | | | | Pabpc5 |
| 23270 | 3 | | | | | Pabpn1l |
| 23271 | 3 | | | | | Patl2 |
| 23272 | 3 | | | | | Paupar |
| 23273 | 3 | | | | | Pax3 |
| 23274 | 3 | | | | | Pax4 |
| 23275 | 3 | | | | | Pax6os1 |
| 23276 | 3 | | | | | Pax7 |
| 23277 | 3 | | | | | Pcdha4-g |
| 23278 | 3 | | | | | Pcdha8 |
| 23279 | 3 | | | | | Pcsk2os2 |
| 23280 | 3 | | | | | Pdc |
| 23281 | 3 | | | | | Pde11a |
| 23282 | 3 | | | | | Pde6b |
| 23283 | 3 | | | | | Pde6c |
| 23284 | 3 | | | | | Pea15b |
| 23285 | 3 | | | | | Pefl |
| 23286 | 3 | | | | | Pet117 |
| 23287 | 3 | | | | | Pfpl |
| 23288 | 3 | | | | | Pgr15l |
| 23289 | 3 | | | | | Phex |
| 23290 | 3 | | | | | Pinc |
| 23291 | 3 | | | | | Pira7 |
| 23292 | 3 | | | | | Piwil4 |
| 23293 | 3 | | | | | Pkdl2 |
| 23294 | 3 | | | | | Piscr5 |
| 23295 | 3 | | | | | Pou1f1 |
| 23296 | 3 | | | | | Pou4f2 |
| 23297 | 3 | | | | | Pou4f3 |
| 23298 | 3 | | | | | Ppp1r3fos |
| 23299 | 3 | | | | | Pramef17 |
| 23300 | 3 | | | | | Pramef25 |
| 23301 | 3 | | | | | Pramef6 |
| 23302 | 3 | | | | | Pramel4 |
| 23303 | 3 | | | | | Pramel5 |
| 23304 | 3 | | | | | Pramel6 |
| 23305 | 3 | | | | | Pramel7 |
| 23306 | 3 | | | | | Prb1 |
| 23307 | 3 | | | | | Prdm12 |
| 23308 | 3 | | | | | Prdm13 |
| 23309 | 3 | | | | | Prh1 |
| 23310 | 3 | | | | | Prl |
| 23311 | 3 | | | | | Prl2a1 |
| 23312 | 3 | | | | | Prl2b1 |
| 23313 | 3 | | | | | Prl2c1 |
| 23314 | 3 | | | | | Prl2c2 |
| 23315 | 3 | | | | | Prl2c3 |
| 23316 | 3 | | | | | Prl3a1 |
| 23317 | 3 | | | | | Prl3b1 |
| 23318 | 3 | | | | | Prl3d1 |
| 23319 | 3 | | | | | Prl3d2 |
| 23320 | 3 | | | | | Prl3d3 |
| 23321 | 3 | | | | | Prl4a1 |
| 23322 | 3 | | | | | Prl5a1 |
| 23323 | 3 | | | | | Prl6a1 |
| 23324 | 3 | | | | | Prl7a1 |
| 23325 | 3 | | | | | Prl7a2 |
| 23326 | 3 | | | | | Prl7b1 |

| | | | | | | |
|---|---|---|---|---|---|---|
| 23327 | 3 | | | | | Prl7c1 |
| 23328 | 3 | | | | | Prl7d1 |
| 23329 | 3 | | | | | Prl8a1 |
| 23330 | 3 | | | | | Prl8a2 |
| 23331 | 3 | | | | | Prl8a6 |
| 23332 | 3 | | | | | Prl8a8 |
| 23333 | 3 | | | | | Prl8a9 |
| 23334 | 3 | | | | | Prlhr |
| 23335 | 3 | | | | | Prn |
| 23336 | 3 | | | | | Prop1 |
| 23337 | 3 | | | | | Prp2 |
| 23338 | 3 | | | | | Prpmp5 |
| 23339 | 3 | | | | | Prrxl1 |
| 23340 | 3 | | | | | Prtg |
| 23341 | 3 | | | | | Psg-ps1 |
| 23342 | 3 | | | | | Psg18 |
| 23343 | 3 | | | | | Psg20 |
| 23344 | 3 | | | | | Psg21 |
| 23345 | 3 | | | | | Psg22 |
| 23346 | 3 | | | | | Psg23 |
| 23347 | 3 | | | | | Psg25 |
| 23348 | 3 | | | | | Psg26 |
| 23349 | 3 | | | | | Psg28 |
| 23350 | 3 | | | | | Psg29 |
| 23351 | 3 | | | | | Ptchd4 |
| 23352 | 3 | | | | | Ptgs2os |
| 23353 | 3 | | | | | Ptprq |
| 23354 | 3 | | | | | Ptprtos |
| 23355 | 3 | | | | | Pydc4 |
| 23356 | 3 | | | | | Rab11fip4os1 |
| 23357 | 3 | | | | | Rad21l |
| 23358 | 3 | | | | | Raet1b |
| 23359 | 3 | | | | | Rax |
| 23360 | 3 | | | | | Rbmy |
| 23361 | 3 | | | | | Rbp3 |
| 23362 | 3 | | | | | Rcvrn |
| 23363 | 3 | | | | | Rd3l |
| 23364 | 3 | | | | | Rdh8 |
| 23365 | 3 | | | | | Rfpl4 |
| 23366 | 3 | | | | | Rfpl4b |
| 23367 | 3 | | | | | Rgr |
| 23368 | 3 | | | | | Rgs21 |
| 23369 | 3 | | | | | Rhox12 |
| 23370 | 3 | | | | | Rhox2b |
| 23371 | 3 | | | | | Rhox2c |
| 23372 | 3 | | | | | Rhox2d |
| 23373 | 3 | | | | | Rhox2e |
| 23374 | 3 | | | | | Rhox2f |
| 23375 | 3 | | | | | Rhox2g |
| 23376 | 3 | | | | | Rhox2h |
| 23377 | 3 | | | | | Rhox3a |
| 23378 | 3 | | | | | Rhox3f |
| 23379 | 3 | | | | | Rhox4d |
| 23380 | 3 | | | | | Rhox4e |
| 23381 | 3 | | | | | Rhox4f |
| 23382 | 3 | | | | | Rhox4g |
| 23383 | 3 | | | | | Rhox7 |
| 23384 | 3 | | | | | Rhox9 |
| 23385 | 3 | | | | | Ripply1 |
| 23386 | 3 | | | | | Rmst |
| 23387 | 3 | | | | | Rnu6 |
| 23388 | 3 | | | | | Rnu7 |
| 23389 | 3 | | | | | Rnu73b |
| 23390 | 3 | | | | | Ros1 |
| 23391 | 3 | | | | | Rp1 |
| 23392 | 3 | | | | | Rp1l1 |
| 23393 | 3 | | | | | Rpe65 |
| 23394 | 3 | | | | | Rpl26 |
| 23395 | 3 | | | | | Rps21 |
| 23396 | 3 | | | | | Rrh |
| 23397 | 3 | | | | | Rs1 |
| 23398 | 3 | | | | | Rsg1 |
| 23399 | 3 | | | | | Rtp2 |
| 23400 | 3 | | | | | Sacs |
| 23401 | 3 | | | | | Sbp1 |
| 23402 | 3 | | | | | Scarna10 |
| 23403 | 3 | | | | | Scarna17 |
| 23404 | 3 | | | | | Scarna2 |
| 23405 | 3 | | | | | Scarna9 |
| 23406 | 3 | | | | | Scgb1b19 |
| 23407 | 3 | | | | | Scgb1b2 |
| 23408 | 3 | | | | | Scgb1b20 |
| 23409 | 3 | | | | | Scgb1b24 |
| 23410 | 3 | | | | | Scgb1b30 |
| 23411 | 3 | | | | | Scgb2b12 |
| 23412 | 3 | | | | | Scgb2b19 |
| 23413 | 3 | | | | | Scgb2b2 |
| 23414 | 3 | | | | | Scgb2b24 |
| 23415 | 3 | | | | | Scgb2b26 |
| 23416 | 3 | | | | | Scgb2b3 |
| 23417 | 3 | | | | | Scn10a |
| 23418 | 3 | | | | | Scn11a |
| 23419 | 3 | | | | | Scn9a |
| 23420 | 3 | | | | | Serpinb3d |
| 23421 | 3 | | | | | Serpinb9c |
| 23422 | 3 | | | | | Serpinb9d |

Fig. 34 - 123

| | | | | | | |
|---|---|---|---|---|---|---|
| 23423 | 3 | | | | | Serpinb9e |
| 23424 | 3 | | | | | Serpinb9f |
| 23425 | 3 | | | | | Serpinb9g |
| 23426 | 3 | | | | | Six6 |
| 23427 | 3 | | | | | Skint3 |
| 23428 | 3 | | | | | Skint4 |
| 23429 | 3 | | | | | Skint9 |
| 23430 | 3 | | | | | Slain1os |
| 23431 | 3 | | | | | Slc22a27 |
| 23432 | 3 | | | | | Slc26a5 |
| 23433 | 3 | | | | | Slc2a7 |
| 23434 | 3 | | | | | Slc38a8 |
| 23435 | 3 | | | | | Slc45a2 |
| 23436 | 3 | | | | | Slc5a4a |
| 23437 | 3 | | | | | Slc7a12 |
| 23438 | 3 | | | | | Smgc |
| 23439 | 3 | | | | | Smr2 |
| 23440 | 3 | | | | | Snora19 |
| 23441 | 3 | | | | | Snora20 |
| 23442 | 3 | | | | | Snora2b |
| 23443 | 3 | | | | | Snora30 |
| 23444 | 3 | | | | | Snora35 |
| 23445 | 3 | | | | | Snora36b |
| 23446 | 3 | | | | | Snora47 |
| 23447 | 3 | | | | | Snora5c |
| 23448 | 3 | | | | | Snora61 |
| 23449 | 3 | | | | | Snord100 |
| 23450 | 3 | | | | | Snord104 |
| 23451 | 3 | | | | | Snord11 |
| 23452 | 3 | | | | | Snord110 |
| 23453 | 3 | | | | | Snord111 |
| 23454 | 3 | | | | | Snord116 |
| 23455 | 3 | | | | | Snord116l1 |
| 23456 | 3 | | | | | Snord116l2 |
| 23457 | 3 | | | | | Snord118 |
| 23458 | 3 | | | | | Snord12 |
| 23459 | 3 | | | | | Snord123 |
| 23460 | 3 | | | | | Snord14a |
| 23461 | 3 | | | | | Snord14c |
| 23462 | 3 | | | | | Snord14d |
| 23463 | 3 | | | | | Snord16a |
| 23464 | 3 | | | | | Snord19 |
| 23465 | 3 | | | | | Snord1a |
| 23466 | 3 | | | | | Snord1b |
| 23467 | 3 | | | | | Snord1c |
| 23468 | 3 | | | | | Snord2 |
| 23469 | 3 | | | | | Snord32a |
| 23470 | 3 | | | | | Snord33 |
| 23471 | 3 | | | | | Snord34 |
| 23472 | 3 | | | | | Snord35a |
| 23473 | 3 | | | | | Snord35b |
| 23474 | 3 | | | | | Snord37 |
| 23475 | 3 | | | | | Snord38a |
| 23476 | 3 | | | | | Snord42a |
| 23477 | 3 | | | | | Snord42b |
| 23478 | 3 | | | | | Snord43 |
| 23479 | 3 | | | | | Snord45b |
| 23480 | 3 | | | | | Snord45c |
| 23481 | 3 | | | | | Snord47 |
| 23482 | 3 | | | | | Snord49a |
| 23483 | 3 | | | | | Snord49b |
| 23484 | 3 | | | | | Snord4a |
| 23485 | 3 | | | | | Snord52 |
| 23486 | 3 | | | | | Snord53 |
| 23487 | 3 | | | | | Snord55 |
| 23488 | 3 | | | | | Snord57 |
| 23489 | 3 | | | | | Snord58b |
| 23490 | 3 | | | | | Snord61 |
| 23491 | 3 | | | | | Snord64 |
| 23492 | 3 | | | | | Snord65 |
| 23493 | 3 | | | | | Snord66 |
| 23494 | 3 | | | | | Snord67 |
| 23495 | 3 | | | | | Snord68 |
| 23496 | 3 | | | | | Snord69 |
| 23497 | 3 | | | | | Snord70 |
| 23498 | 3 | | | | | Snord71 |
| 23499 | 3 | | | | | Snord72 |
| 23500 | 3 | | | | | Snord73a |
| 23501 | 3 | | | | | Snord8 |
| 23502 | 3 | | | | | Snord82 |
| 23503 | 3 | | | | | Snord83b |
| 23504 | 3 | | | | | Snord85 |
| 23505 | 3 | | | | | Snord87 |
| 23506 | 3 | | | | | Snord88a |
| 23507 | 3 | | | | | Snord88c |
| 23508 | 3 | | | | | Snord89 |
| 23509 | 3 | | | | | Snord90 |
| 23510 | 3 | | | | | Snord91a |
| 23511 | 3 | | | | | Snord92 |
| 23512 | 3 | | | | | Snord93 |
| 23513 | 3 | | | | | Snord95 |
| 23514 | 3 | | | | | Snord96a |
| 23515 | 3 | | | | | Snord98 |
| 23516 | 3 | | | | | Snord99 |
| 23517 | 3 | | | | | Sorbs2os |
| 23518 | 3 | | | | | Spink11 |
| 23519 | 3 | | | | | Spink13 |
| 23520 | 3 | | | | | Spint4 |
| 23521 | 3 | | | | | Sry |
| 23522 | 3 | | | | | Ssu2 |
| 23523 | 3 | | | | | Ssx9 |
| 23524 | 3 | | | | | Ssxb10 |
| 23525 | 3 | | | | | Ssxb3 |
| 23526 | 3 | | | | | Ssxb5 |
| 23527 | 3 | | | | | Ssxb9 |
| 23528 | 3 | | | | | Stmn1-rs1 |
| 23529 | 3 | | | | | Strc |
| 23530 | 3 | | | | | Sult1c1 |
| 23531 | 3 | | | | | Sult2a1 |
| 23532 | 3 | | | | | Sult2a2 |
| 23533 | 3 | | | | | Sult2a3 |
| 23534 | 3 | | | | | Sult2a5 |
| 23535 | 3 | | | | | Sult2a6 |
| 23536 | 3 | | | | | Sult2a7 |
| 23537 | 3 | | | | | Sult3a1 |
| 23538 | 3 | | | | | Sult6b1 |
| 23539 | 3 | | | | | Sva |
| 23540 | 3 | | | | | Sval2 |
| 23541 | 3 | | | | | Sval3 |
| 23542 | 3 | | | | | Svs1 |
| 23543 | 3 | | | | | Svs2 |
| 23544 | 3 | | | | | Svs3a |
| 23545 | 3 | | | | | Svs3b |
| 23546 | 3 | | | | | Svs4 |
| 23547 | 3 | | | | | Synb |
| 23548 | 3 | | | | | T |
| 23549 | 3 | | | | | Taar1 |
| 23550 | 3 | | | | | Taar2 |
| 23551 | 3 | | | | | Taar3 |
| 23552 | 3 | | | | | Taar4 |
| 23553 | 3 | | | | | Taar5 |
| 23554 | 3 | | | | | Taar6 |
| 23555 | 3 | | | | | Taar7a |
| 23556 | 3 | | | | | Taar7b |
| 23557 | 3 | | | | | Taar7d |
| 23558 | 3 | | | | | Taar7e |
| 23559 | 3 | | | | | Taar7f |
| 23560 | 3 | | | | | Taar8a |
| 23561 | 3 | | | | | Taar8b |
| 23562 | 3 | | | | | Taar8c |
| 23563 | 3 | | | | | Taar9 |
| 23564 | 3 | | | | | Tas1r2 |
| 23565 | 3 | | | | | Tas2r102 |
| 23566 | 3 | | | | | Tas2r103 |
| 23567 | 3 | | | | | Tas2r104 |
| 23568 | 3 | | | | | Tas2r105 |
| 23569 | 3 | | | | | Tas2r106 |
| 23570 | 3 | | | | | Tas2r107 |
| 23571 | 3 | | | | | Tas2r108 |
| 23572 | 3 | | | | | Tas2r109 |
| 23573 | 3 | | | | | Tas2r110 |
| 23574 | 3 | | | | | Tas2r113 |
| 23575 | 3 | | | | | Tas2r114 |
| 23576 | 3 | | | | | Tas2r115 |
| 23577 | 3 | | | | | Tas2r116 |
| 23578 | 3 | | | | | Tas2r117 |
| 23579 | 3 | | | | | Tas2r118 |
| 23580 | 3 | | | | | Tas2r119 |
| 23581 | 3 | | | | | Tas2r120 |
| 23582 | 3 | | | | | Tas2r121 |
| 23583 | 3 | | | | | Tas2r122 |
| 23584 | 3 | | | | | Tas2r123 |
| 23585 | 3 | | | | | Tas2r124 |
| 23586 | 3 | | | | | Tas2r125 |
| 23587 | 3 | | | | | Tas2r126 |
| 23588 | 3 | | | | | Tas2r129 |
| 23589 | 3 | | | | | Tas2r130 |
| 23590 | 3 | | | | | Tas2r131 |
| 23591 | 3 | | | | | Tas2r134 |
| 23592 | 3 | | | | | Tas2r135 |
| 23593 | 3 | | | | | Tas2r136 |
| 23594 | 3 | | | | | Tas2r137 |
| 23595 | 3 | | | | | Tas2r138 |
| 23596 | 3 | | | | | Tas2r139 |
| 23597 | 3 | | | | | Tas2r140 |
| 23598 | 3 | | | | | Tas2r143 |
| 23599 | 3 | | | | | Tas2r144 |
| 23600 | 3 | | | | | Tbc1d22bos |
| 23601 | 3 | | | | | Tbpl2 |
| 23602 | 3 | | | | | Tbrg3 |
| 23603 | 3 | | | | | Tbx3os2 |
| 23604 | 3 | | | | | Tcl1b1 |
| 23605 | 3 | | | | | Tcl1b2 |
| 23606 | 3 | | | | | Tcl1b3 |
| 23607 | 3 | | | | | Tcl1b4 |
| 23608 | 3 | | | | | Tcl1b5 |
| 23609 | 3 | | | | | Tcstv3 |
| 23610 | 3 | | | | | Tdpoz1 |
| 23611 | 3 | | | | | Tdpoz2 |
| 23612 | 3 | | | | | Tdpoz3 |
| 23613 | 3 | | | | | Tdpoz5 |
| 23614 | 3 | | | | | Tecta |

Fig. 34 - 124

| | | | | | |
|---|---|---|---|---|---|
| 23615 | 3 | | | | Tfap2d |
| 23616 | 3 | | | | Tll2 |
| 23617 | 3 | | | | Tmc2 |
| 23618 | 3 | | | | Tmem150cos |
| 23619 | 3 | | | | Tmem211 |
| 23620 | 3 | | | | Tmem92 |
| 23621 | 3 | | | | Tmprss11c |
| 23622 | 3 | | | | Tmprss11d |
| 23623 | 3 | | | | Tmprss15 |
| 23624 | 3 | | | | Tnfsf12Tnfsf13 |
| 23625 | 3 | | | | Tpbpa |
| 23626 | 3 | | | | Tpbpb |
| 23627 | 3 | | | | Tpo |
| 23628 | 3 | | | | Trappc3l |
| 23629 | 3 | | | | Trcg1 |
| 23630 | 3 | | | | Trim30e-ps1 |
| 23631 | 3 | | | | Trim43a |
| 23632 | 3 | | | | Trim43b |
| 23633 | 3 | | | | Trim60 |
| 23634 | 3 | | | | Trim71 |
| 23635 | 3 | | | | Trim75 |
| 23636 | 3 | | | | Triml2 |
| 23637 | 3 | | | | Trpv1 |
| 23638 | 3 | | | | Tsix |
| 23639 | 3 | | | | Tspy-ps |
| 23640 | 3 | | | | Ubtfl1 |
| 23641 | 3 | | | | Uchl1os |
| 23642 | 3 | | | | Ugt2a1 |
| 23643 | 3 | | | | Ugt2a2 |
| 23644 | 3 | | | | Usp17la |
| 23645 | 3 | | | | Usp17lb |
| 23646 | 3 | | | | Usp17lc |
| 23647 | 3 | | | | Usp17ld |
| 23648 | 3 | | | | Usp17le |
| 23649 | 3 | | | | Usp9y |
| 23650 | 3 | | | | V1rd18 |
| 23651 | 3 | | | | V1rd19 |
| 23652 | 3 | | | | Vgll1 |
| 23653 | 3 | | | | Vmn1r-ps103 |
| 23654 | 3 | | | | Vmn1r-ps79 |
| 23655 | 3 | | | | Vmn1r1 |
| 23656 | 3 | | | | Vmn1r10 |
| 23657 | 3 | | | | Vmn1r100 |
| 23658 | 3 | | | | Vmn1r101 |
| 23659 | 3 | | | | Vmn1r103 |
| 23660 | 3 | | | | Vmn1r104 |
| 23661 | 3 | | | | Vmn1r107 |
| 23662 | 3 | | | | Vmn1r11 |
| 23663 | 3 | | | | Vmn1r112 |
| 23664 | 3 | | | | Vmn1r113 |
| 23665 | 3 | | | | Vmn1r114 |
| 23666 | 3 | | | | Vmn1r115 |
| 23667 | 3 | | | | Vmn1r116 |
| 23668 | 3 | | | | Vmn1r117 |
| 23669 | 3 | | | | Vmn1r118 |
| 23670 | 3 | | | | Vmn1r119 |
| 23671 | 3 | | | | Vmn1r12 |
| 23672 | 3 | | | | Vmn1r120 |
| 23673 | 3 | | | | Vmn1r121 |
| 23674 | 3 | | | | Vmn1r122 |
| 23675 | 3 | | | | Vmn1r123 |
| 23676 | 3 | | | | Vmn1r124 |
| 23677 | 3 | | | | Vmn1r125 |
| 23678 | 3 | | | | Vmn1r126 |
| 23679 | 3 | | | | Vmn1r127 |
| 23680 | 3 | | | | Vmn1r128 |
| 23681 | 3 | | | | Vmn1r129 |
| 23682 | 3 | | | | Vmn1r13 |
| 23683 | 3 | | | | Vmn1r130 |
| 23684 | 3 | | | | Vmn1r132 |
| 23685 | 3 | | | | Vmn1r135 |
| 23686 | 3 | | | | Vmn1r137 |
| 23687 | 3 | | | | Vmn1r138 |
| 23688 | 3 | | | | Vmn1r139 |
| 23689 | 3 | | | | Vmn1r14 |
| 23690 | 3 | | | | Vmn1r142 |
| 23691 | 3 | | | | Vmn1r148 |
| 23692 | 3 | | | | Vmn1r15 |
| 23693 | 3 | | | | Vmn1r151 |
| 23694 | 3 | | | | Vmn1r152 |
| 23695 | 3 | | | | Vmn1r157 |
| 23696 | 3 | | | | Vmn1r158 |
| 23697 | 3 | | | | Vmn1r159 |
| 23698 | 3 | | | | Vmn1r16 |
| 23699 | 3 | | | | Vmn1r160 |
| 23700 | 3 | | | | Vmn1r163 |
| 23701 | 3 | | | | Vmn1r165 |
| 23702 | 3 | | | | Vmn1r166 |
| 23703 | 3 | | | | Vmn1r167 |
| 23704 | 3 | | | | Vmn1r168 |
| 23705 | 3 | | | | Vmn1r169 |
| 23706 | 3 | | | | Vmn1r17 |
| 23707 | 3 | | | | Vmn1r170 |
| 23708 | 3 | | | | Vmn1r171 |
| 23709 | 3 | | | | Vmn1r172 |
| 23710 | 3 | | | | Vmn1r173 |
| 23711 | 3 | | | | Vmn1r174 |
| 23712 | 3 | | | | Vmn1r175 |
| 23713 | 3 | | | | Vmn1r176 |
| 23714 | 3 | | | | Vmn1r177 |
| 23715 | 3 | | | | Vmn1r178 |
| 23716 | 3 | | | | Vmn1r179 |
| 23717 | 3 | | | | Vmn1r18 |
| 23718 | 3 | | | | Vmn1r180 |
| 23719 | 3 | | | | Vmn1r183 |
| 23720 | 3 | | | | Vmn1r184 |
| 23721 | 3 | | | | Vmn1r185 |
| 23722 | 3 | | | | Vmn1r186 |
| 23723 | 3 | | | | Vmn1r187 |
| 23724 | 3 | | | | Vmn1r188 |
| 23725 | 3 | | | | Vmn1r189 |
| 23726 | 3 | | | | Vmn1r19 |
| 23727 | 3 | | | | Vmn1r191 |
| 23728 | 3 | | | | Vmn1r192 |
| 23729 | 3 | | | | Vmn1r193 |
| 23730 | 3 | | | | Vmn1r194 |
| 23731 | 3 | | | | Vmn1r195 |
| 23732 | 3 | | | | Vmn1r196 |
| 23733 | 3 | | | | Vmn1r197 |
| 23734 | 3 | | | | Vmn1r198 |
| 23735 | 3 | | | | Vmn1r199 |
| 23736 | 3 | | | | Vmn1r20 |
| 23737 | 3 | | | | Vmn1r200 |
| 23738 | 3 | | | | Vmn1r201 |
| 23739 | 3 | | | | Vmn1r202 |
| 23740 | 3 | | | | Vmn1r203 |
| 23741 | 3 | | | | Vmn1r204 |
| 23742 | 3 | | | | Vmn1r205 |
| 23743 | 3 | | | | Vmn1r206 |
| 23744 | 3 | | | | Vmn1r207-ps |
| 23745 | 3 | | | | Vmn1r208 |
| 23746 | 3 | | | | Vmn1r209 |
| 23747 | 3 | | | | Vmn1r210 |
| 23748 | 3 | | | | Vmn1r211 |
| 23749 | 3 | | | | Vmn1r212 |
| 23750 | 3 | | | | Vmn1r213 |
| 23751 | 3 | | | | Vmn1r214 |
| 23752 | 3 | | | | Vmn1r215 |
| 23753 | 3 | | | | Vmn1r216 |
| 23754 | 3 | | | | Vmn1r217 |
| 23755 | 3 | | | | Vmn1r218 |
| 23756 | 3 | | | | Vmn1r219 |
| 23757 | 3 | | | | Vmn1r22 |
| 23758 | 3 | | | | Vmn1r220 |
| 23759 | 3 | | | | Vmn1r221 |
| 23760 | 3 | | | | Vmn1r222 |
| 23761 | 3 | | | | Vmn1r223 |
| 23762 | 3 | | | | Vmn1r224 |
| 23763 | 3 | | | | Vmn1r225 |
| 23764 | 3 | | | | Vmn1r226 |
| 23765 | 3 | | | | Vmn1r227 |
| 23766 | 3 | | | | Vmn1r228 |
| 23767 | 3 | | | | Vmn1r229 |
| 23768 | 3 | | | | Vmn1r23 |
| 23769 | 3 | | | | Vmn1r230 |
| 23770 | 3 | | | | Vmn1r231 |
| 23771 | 3 | | | | Vmn1r232 |
| 23772 | 3 | | | | Vmn1r234 |
| 23773 | 3 | | | | Vmn1r235 |
| 23774 | 3 | | | | Vmn1r236 |
| 23775 | 3 | | | | Vmn1r237 |
| 23776 | 3 | | | | Vmn1r238 |
| 23777 | 3 | | | | Vmn1r24 |
| 23778 | 3 | | | | Vmn1r25 |
| 23779 | 3 | | | | Vmn1r26 |
| 23780 | 3 | | | | Vmn1r27 |
| 23781 | 3 | | | | Vmn1r28 |
| 23782 | 3 | | | | Vmn1r29 |
| 23783 | 3 | | | | Vmn1r3 |
| 23784 | 3 | | | | Vmn1r30 |
| 23785 | 3 | | | | Vmn1r31 |
| 23786 | 3 | | | | Vmn1r32 |
| 23787 | 3 | | | | Vmn1r33 |
| 23788 | 3 | | | | Vmn1r34 |
| 23789 | 3 | | | | Vmn1r35 |
| 23790 | 3 | | | | Vmn1r36 |
| 23791 | 3 | | | | Vmn1r37 |
| 23792 | 3 | | | | Vmn1r38 |
| 23793 | 3 | | | | Vmn1r39 |
| 23794 | 3 | | | | Vmn1r4 |
| 23795 | 3 | | | | Vmn1r41 |
| 23796 | 3 | | | | Vmn1r42 |
| 23797 | 3 | | | | Vmn1r43 |
| 23798 | 3 | | | | Vmn1r44 |
| 23799 | 3 | | | | Vmn1r45 |
| 23800 | 3 | | | | Vmn1r46 |
| 23801 | 3 | | | | Vmn1r47 |
| 23802 | 3 | | | | Vmn1r48 |
| 23803 | 3 | | | | Vmn1r49 |
| 23804 | 3 | | | | Vmn1r5 |
| 23805 | 3 | | | | Vmn1r50 |
| 23806 | 3 | | | | Vmn1r51 |

Fig. 34 - 125

| | | | | | | | | | | | |
|---|---|---|---|---|---|---|---|---|---|---|---|
| 23807 | 3 | | | | | Vmn1r52 | 23903 | 3 | | | | Vmn2r34 |
| 23808 | 3 | | | | | Vmn1r53 | 23904 | 3 | | | | Vmn2r35 |
| 23809 | 3 | | | | | Vmn1r54 | 23905 | 3 | | | | Vmn2r36 |
| 23810 | 3 | | | | | Vmn1r55 | 23906 | 3 | | | | Vmn2r37 |
| 23811 | 3 | | | | | Vmn1r56 | 23907 | 3 | | | | Vmn2r38 |
| 23812 | 3 | | | | | Vmn1r57 | 23908 | 3 | | | | Vmn2r39 |
| 23813 | 3 | | | | | Vmn1r58 | 23909 | 3 | | | | Vmn2r40 |
| 23814 | 3 | | | | | Vmn1r59 | 23910 | 3 | | | | Vmn2r41 |
| 23815 | 3 | | | | | Vmn1r6 | 23911 | 3 | | | | Vmn2r42 |
| 23816 | 3 | | | | | Vmn1r60 | 23912 | 3 | | | | Vmn2r43 |
| 23817 | 3 | | | | | Vmn1r61 | 23913 | 3 | | | | Vmn2r44 |
| 23818 | 3 | | | | | Vmn1r62 | 23914 | 3 | | | | Vmn2r45 |
| 23819 | 3 | | | | | Vmn1r63 | 23915 | 3 | | | | Vmn2r46 |
| 23820 | 3 | | | | | Vmn1r64 | 23916 | 3 | | | | Vmn2r47 |
| 23821 | 3 | | | | | Vmn1r65 | 23917 | 3 | | | | Vmn2r48 |
| 23822 | 3 | | | | | Vmn1r66 | 23918 | 3 | | | | Vmn2r49 |
| 23823 | 3 | | | | | Vmn1r67 | 23919 | 3 | | | | Vmn2r50 |
| 23824 | 3 | | | | | Vmn1r68 | 23920 | 3 | | | | Vmn2r51 |
| 23825 | 3 | | | | | Vmn1r69 | 23921 | 3 | | | | Vmn2r52 |
| 23826 | 3 | | | | | Vmn1r7 | 23922 | 3 | | | | Vmn2r53 |
| 23827 | 3 | | | | | Vmn1r70 | 23923 | 3 | | | | Vmn2r54 |
| 23828 | 3 | | | | | Vmn1r71 | 23924 | 3 | | | | Vmn2r55 |
| 23829 | 3 | | | | | Vmn1r72 | 23925 | 3 | | | | Vmn2r56 |
| 23830 | 3 | | | | | Vmn1r73 | 23926 | 3 | | | | Vmn2r57 |
| 23831 | 3 | | | | | Vmn1r74 | 23927 | 3 | | | | Vmn2r58 |
| 23832 | 3 | | | | | Vmn1r75 | 23928 | 3 | | | | Vmn2r59 |
| 23833 | 3 | | | | | Vmn1r76 | 23929 | 3 | | | | Vmn2r60 |
| 23834 | 3 | | | | | Vmn1r77 | 23930 | 3 | | | | Vmn2r61 |
| 23835 | 3 | | | | | Vmn1r78 | 23931 | 3 | | | | Vmn2r62 |
| 23836 | 3 | | | | | Vmn1r79 | 23932 | 3 | | | | Vmn2r63 |
| 23837 | 3 | | | | | Vmn1r8 | 23933 | 3 | | | | Vmn2r65 |
| 23838 | 3 | | | | | Vmn1r80 | 23934 | 3 | | | | Vmn2r66 |
| 23839 | 3 | | | | | Vmn1r81 | 23935 | 3 | | | | Vmn2r67 |
| 23840 | 3 | | | | | Vmn1r82 | 23936 | 3 | | | | Vmn2r69 |
| 23841 | 3 | | | | | Vmn1r83 | 23937 | 3 | | | | Vmn2r70 |
| 23842 | 3 | | | | | Vmn1r84 | 23938 | 3 | | | | Vmn2r71 |
| 23843 | 3 | | | | | Vmn1r85 | 23939 | 3 | | | | Vmn2r72 |
| 23844 | 3 | | | | | Vmn1r86 | 23940 | 3 | | | | Vmn2r73 |
| 23845 | 3 | | | | | Vmn1r87 | 23941 | 3 | | | | Vmn2r74 |
| 23846 | 3 | | | | | Vmn1r88 | 23942 | 3 | | | | Vmn2r75 |
| 23847 | 3 | | | | | Vmn1r89 | 23943 | 3 | | | | Vmn2r76 |
| 23848 | 3 | | | | | Vmn1r9 | 23944 | 3 | | | | Vmn2r77 |
| 23849 | 3 | | | | | Vmn1r91 | 23945 | 3 | | | | Vmn2r78 |
| 23850 | 3 | | | | | Vmn1r94 | 23946 | 3 | | | | Vmn2r79 |
| 23851 | 3 | | | | | Vmn1r95 | 23947 | 3 | | | | Vmn2r8 |
| 23852 | 3 | | | | | Vmn2r-ps129 | 23948 | 3 | | | | Vmn2r80 |
| 23853 | 3 | | | | | Vmn2r-ps60 | 23949 | 3 | | | | Vmn2r81 |
| 23854 | 3 | | | | | Vmn2r1 | 23950 | 3 | | | | Vmn2r82 |
| 23855 | 3 | | | | | Vmn2r10 | 23951 | 3 | | | | Vmn2r83 |
| 23856 | 3 | | | | | Vmn2r100 | 23952 | 3 | | | | Vmn2r85 |
| 23857 | 3 | | | | | Vmn2r101 | 23953 | 3 | | | | Vmn2r86 |
| 23858 | 3 | | | | | Vmn2r102 | 23954 | 3 | | | | Vmn2r88 |
| 23859 | 3 | | | | | Vmn2r103 | 23955 | 3 | | | | Vmn2r89 |
| 23860 | 3 | | | | | Vmn2r104 | 23956 | 3 | | | | Vmn2r9 |
| 23861 | 3 | | | | | Vmn2r105 | 23957 | 3 | | | | Vmn2r90 |
| 23862 | 3 | | | | | Vmn2r106 | 23958 | 3 | | | | Vmn2r91 |
| 23863 | 3 | | | | | Vmn2r107 | 23959 | 3 | | | | Vmn2r92 |
| 23864 | 3 | | | | | Vmn2r108 | 23960 | 3 | | | | Vmn2r93 |
| 23865 | 3 | | | | | Vmn2r109 | 23961 | 3 | | | | Vmn2r94 |
| 23866 | 3 | | | | | Vmn2r11 | 23962 | 3 | | | | Vmn2r95 |
| 23867 | 3 | | | | | Vmn2r110 | 23963 | 3 | | | | Vmn2r97 |
| 23868 | 3 | | | | | Vmn2r111 | 23964 | 3 | | | | Vmn2r98 |
| 23869 | 3 | | | | | Vmn2r112 | 23965 | 3 | | | | Vmn2r99 |
| 23870 | 3 | | | | | Vmn2r113 | 23966 | 3 | | | | Vrtn |
| 23871 | 3 | | | | | Vmn2r114 | 23967 | 3 | | | | Vsx2 |
| 23872 | 3 | | | | | Vmn2r115 | 23968 | 3 | | | | Vwde |
| 23873 | 3 | | | | | Vmn2r116 | 23969 | 3 | | | | Wap |
| 23874 | 3 | | | | | Vmn2r117 | 23970 | 3 | | | | Wee2 |
| 23875 | 3 | | | | | Vmn2r118 | 23971 | 3 | | | | Wnt8a |
| 23876 | 3 | | | | | Vmn2r12 | 23972 | 3 | | | | Wnt8b |
| 23877 | 3 | | | | | Vmn2r120 | 23973 | 3 | | | | Xist |
| 23878 | 3 | | | | | Vmn2r121 | 23974 | 3 | | | | Xntrpc |
| 23879 | 3 | | | | | Vmn2r123 | 23975 | 3 | | | | Zar1l |
| 23880 | 3 | | | | | Vmn2r124 | 23976 | 3 | | | | Zfp133-ps |
| 23881 | 3 | | | | | Vmn2r13 | 23977 | 3 | | | | Zfp345 |
| 23882 | 3 | | | | | Vmn2r14 | 23978 | 3 | | | | Zfp352 |
| 23883 | 3 | | | | | Vmn2r15 | 23979 | 3 | | | | Zfp363 |
| 23884 | 3 | | | | | Vmn2r16 | 23980 | 3 | | | | Zfp616 |
| 23885 | 3 | | | | | Vmn2r17 | 23981 | 3 | | | | Zfp804b |
| 23886 | 3 | | | | | Vmn2r18 | 23982 | 3 | | | | Zfp91Cntf |
| 23887 | 3 | | | | | Vmn2r19 | 23983 | 3 | | | | Zp1 |
| 23888 | 3 | | | | | Vmn2r2 | 23984 | 3 | | | | Zp3 |
| 23889 | 3 | | | | | Vmn2r20 | 23985 | 3 | | | | Zp4-ps |
| 23890 | 3 | | | | | Vmn2r21 | 23986 | 3 | | | | Zscan4a |
| 23891 | 3 | | | | | Vmn2r22 | 23987 | 3 | | | | Zscan4b |
| 23892 | 3 | | | | | Vmn2r23 | 23988 | 3 | | | | Zscan4c |
| 23893 | 3 | | | | | Vmn2r24 | 23989 | 3 | | | | Zscan4d |
| 23894 | 3 | | | | | Vmn2r25 | 23990 | 3 | | | | Zscan4e |
| 23895 | 3 | | | | | Vmn2r26 | 23991 | 3 | | | | Zscan4f |
| 23896 | 3 | | | | | Vmn2r27 | | | | | | |
| 23897 | 3 | | | | | Vmn2r28 | | | | | | |
| 23898 | 3 | | | | | Vmn2r3 | | | | | | |
| 23899 | 3 | | | | | Vmn2r30 | | | | | | |
| 23900 | 3 | | | | | Vmn2r31 | | | | | | |
| 23901 | 3 | | | | | Vmn2r32 | | | | | | |
| 23902 | 3 | | | | | Vmn2r33 | | | | | | |

Fig. 35-1

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| 0610010B08Rik | 0.35 | 0.40 | 0.49 | 0.54 | 0.70 | 0.51 | 0.18 | 0.28 | 0.22 | 0.59 | 0.47 | 0.29 |
| 0610031O16Rik | 1.00 | 1.00 | 1.00 | 1.00 | 1.00 | 1.00 | 1.00 | 1.00 | 1.00 | 1.00 | 1.00 | 1.00 |
| 1110007C09Rik | 1.77 | 1.48 | 1.18 | 0.33 | 1.04 | 1.01 | 1.16 | 0.90 | 0.82 | 0.43 | 0.79 | 0.83 |
| 1500017E21Rik | 1.04 | 1.36 | 0.91 | 1.00 | 1.00 | 1.00 | 0.74 | 0.99 | 0.88 | 1.00 | 1.00 | 0.97 |
| 1600029I14Rik | 1.00 | 1.00 | 1.00 | 1.00 | 1.00 | 1.00 | 1.00 | 1.00 | 1.00 | 0.06 | 0.13 | 0.09 |
| 1700001C02Rik | 1.00 | 1.00 | 1.00 | 1.00 | 1.00 | 1.00 | 1.00 | 1.00 | 1.00 | 2.99 | 2.65 | 1.13 |
| 1700003C15Rik | 1.00 | 1.00 | 1.00 | 1.00 | 1.00 | 1.00 | 1.00 | 1.00 | 1.00 | 1.00 | 1.00 | 1.00 |
| 1700006A11Rik | 1.00 | 1.00 | 1.00 | 1.00 | 1.00 | 1.00 | 1.00 | 1.00 | 1.00 | 1.00 | 1.00 | 1.00 |
| 1700020L24Rik | 0.73 | 1.08 | 1.54 | 0.98 | 1.82 | 1.42 | 1.60 | 1.06 | 1.11 | 0.17 | 0.32 | 0.90 |
| 1700023L04Rik | 1.00 | 1.00 | 1.00 | 1.00 | 1.00 | 1.00 | 1.00 | 1.00 | 1.00 | 0.27 | 1.48 | 0.93 |
| 1700025K24Rik | 1.00 | 1.00 | 1.00 | 1.00 | 1.00 | 1.00 | 1.00 | 1.00 | 1.00 | 1.00 | 1.00 | 1.00 |
| 1700028B04Rik | 0.71 | 0.28 | 0.47 | 0.15 | 0.29 | 0.90 | 0.63 | 0.49 | 0.68 | 1.00 | 1.00 | 1.00 |
| 1700029P11Rik | 1.00 | 1.00 | 1.00 | 1.00 | 1.00 | 1.00 | 1.00 | 1.00 | 1.00 | 1.00 | 1.00 | 1.00 |
| 1700044K03Rik | 1.00 | 1.00 | 1.00 | 1.00 | 1.00 | 1.00 | 1.00 | 1.00 | 1.00 | 1.00 | 1.00 | 1.00 |
| 1700045H11Rik | 1.00 | 1.00 | 1.00 | 1.00 | 1.00 | 1.00 | 1.00 | 1.00 | 1.00 | 1.00 | 1.00 | 1.00 |
| 1700047G03Rik | 1.00 | 1.00 | 1.00 | 1.00 | 1.00 | 1.00 | 1.00 | 1.00 | 1.00 | 1.00 | 1.00 | 1.00 |
| 1700088E04Rik | 1.00 | 1.00 | 1.00 | 1.00 | 1.00 | 1.00 | 1.00 | 1.00 | 1.00 | 1.98 | 4.92 | 1.60 |
| 1700123I01Rik | 1.00 | 1.00 | 1.00 | 1.00 | 1.00 | 1.00 | 1.00 | 1.00 | 1.00 | 1.00 | 1.00 | 1.00 |
| 1810007D17Rik | 1.00 | 1.00 | 1.00 | 1.00 | 1.00 | 1.00 | 1.00 | 1.00 | 1.00 | 1.00 | 1.00 | 1.00 |
| 1810021B22Rik | 0.93 | 0.60 | 0.95 | 0.34 | 3.33 | 0.73 | 1.14 | 0.54 | 0.77 | 1.60 | 1.34 | 1.22 |
| 1810030O07Rik | 0.72 | 1.08 | 0.99 | 1.35 | 0.70 | 0.95 | 0.84 | 0.83 | 0.82 | 0.52 | 0.48 | 0.88 |
| 1810043H04Rik | 0.90 | 0.66 | 0.69 | 0.16 | 3.71 | 0.96 | 1.35 | 0.55 | 0.92 | 1.00 | 1.47 | 0.85 |
| 1810064F22Rik | 1.00 | 1.00 | 1.00 | 1.00 | 1.00 | 1.00 | 1.00 | 1.00 | 1.00 | 1.35 | 0.76 | 1.20 |
| 2010016I18Rik | 1.00 | 1.00 | 1.00 | 1.00 | 1.00 | 1.00 | 1.00 | 1.00 | 1.00 | 0.31 | 0.82 | 0.74 |
| 2310015A10Rik | 0.62 | 0.98 | 0.94 | 1.57 | 0.75 | 1.07 | 0.91 | 1.07 | 0.92 | 0.70 | 0.64 | 1.11 |
| 2410017I17Rik | 1.00 | 1.00 | 1.00 | 1.00 | 1.00 | 1.00 | 1.00 | 1.00 | 1.00 | 1.00 | 1.00 | 1.00 |
| 2510003E04Rik | 1.06 | 1.44 | 0.96 | 0.92 | 0.35 | 1.13 | 1.13 | 1.00 | 0.96 | 0.36 | 0.47 | 0.94 |
| 2610001J05Rik | 1.01 | 1.21 | 0.80 | 0.86 | 0.60 | 0.85 | 0.92 | 1.08 | 0.98 | 0.55 | 0.57 | 1.18 |
| 2610035D17Rik | 0.19 | 0.38 | 0.13 | 0.71 | 0.71 | 0.52 | 0.17 | 0.27 | 0.14 | 0.28 | 0.28 | 0.16 |
| 2610203C20Rik | 0.80 | 1.16 | 1.17 | 3.06 | 0.36 | 0.79 | 0.70 | 0.84 | 1.05 | 0.90 | 0.23 | 1.00 |
| 2610528J11Rik | 1.00 | 1.00 | 1.00 | 1.00 | 1.00 | 1.00 | 1.00 | 1.00 | 1.00 | 0.44 | 0.78 | 0.93 |
| 2810004N23Rik | 0.85 | 0.87 | 0.89 | 0.92 | 4.74 | 1.25 | 0.98 | 1.07 | 1.12 | 0.84 | 1.09 | 0.90 |
| 2810403A07Rik | 1.30 | 1.60 | 1.17 | 1.23 | 0.39 | 0.95 | 0.87 | 0.86 | 0.92 | 0.38 | 0.40 | 0.94 |
| 3010033K07Rik | 1.01 | 1.79 | 1.00 | 0.20 | 0.89 | 0.70 | 1.00 | 1.00 | 1.00 | 1.00 | 1.00 | 1.00 |
| 4732471J01Rik | 1.00 | 1.00 | 1.00 | 0.11 | 0.24 | 0.97 | 1.00 | 1.00 | 1.00 | 1.00 | 1.00 | 1.98 |
| 4921524J17Rik | 1.04 | 2.69 | 0.89 | 1.66 | 0.39 | 1.02 | 0.88 | 0.95 | 0.73 | 0.21 | 0.20 | 1.02 |
| 4921525O09Rik | 1.00 | 1.00 | 1.00 | 1.00 | 1.00 | 1.00 | 1.00 | 1.00 | 1.00 | 1.00 | 1.00 | 1.00 |
| 4930401O12Rik | 1.00 | 1.00 | 1.00 | 1.00 | 1.00 | 1.00 | 1.00 | 1.00 | 1.00 | 1.00 | 1.00 | 1.00 |
| 4930402H24Rik | 1.00 | 1.00 | 1.04 | 2.27 | 0.13 | 0.98 | 1.09 | 1.46 | 1.28 | 1.00 | 1.00 | 1.06 |
| 4930412O13Rik | 1.00 | 1.00 | 1.00 | 1.00 | 1.00 | 1.00 | 1.00 | 1.00 | 1.00 | 1.00 | 1.00 | 1.00 |
| 4930413G21Rik | 1.21 | 1.84 | 0.93 | 1.67 | 0.93 | 0.81 | 1.54 | 1.23 | 1.18 | 0.15 | 0.67 | 1.11 |
| 4930519F09Rik | 0.79 | 1.60 | 1.04 | 1.22 | 0.20 | 0.92 | 0.99 | 1.50 | 1.05 | 0.94 | 0.66 | 1.01 |
| 4930594C11Rik | 0.93 | 1.34 | 0.81 | 2.14 | 0.11 | 0.88 | 0.83 | 1.08 | 1.23 | 1.00 | 0.35 | 1.22 |
| 4933402N22Rik | 1.00 | 1.00 | 1.00 | 1.00 | 1.00 | 1.00 | 1.00 | 1.00 | 1.00 | 1.00 | 1.00 | 1.00 |
| 4933417G07Rik | 1.45 | 4.64 | 0.91 | 0.52 | 0.11 | 0.81 | 1.01 | 0.95 | 1.06 | 0.46 | 0.14 | 1.07 |
| 4933421I07Rik | 1.00 | 1.00 | 1.00 | 1.00 | 1.00 | 1.00 | 1.00 | 1.00 | 1.00 | 1.00 | 1.00 | 1.00 |
| 4933426M11Rik | 1.05 | 2.44 | 1.09 | 1.63 | 0.09 | 1.06 | 2.30 | 2.39 | 1.36 | 0.21 | 0.16 | 1.30 |
| 4933430N04Rik | 1.00 | 1.00 | 1.00 | 1.00 | 1.00 | 1.00 | 1.00 | 1.00 | 1.00 | 1.00 | 1.00 | 1.00 |
| 5730416F02Rik | 0.16 | 0.17 | 0.22 | 0.45 | 0.42 | 0.38 | 0.12 | 0.12 | 0.27 | 0.05 | 0.17 | 0.26 |
| 5830403L16Rik | 1.00 | 1.00 | 1.00 | 1.00 | 1.00 | 1.00 | 1.00 | 1.00 | 1.00 | 1.00 | 1.00 | 1.00 |
| 5830454E08Rik | 0.53 | 0.41 | 1.10 | 0.60 | 2.41 | 1.38 | 1.20 | 0.84 | 0.75 | 0.32 | 0.88 | 0.70 |
| 6430571L13Rik | 0.15 | 0.20 | 0.28 | 0.41 | 0.54 | 0.43 | 0.29 | 0.27 | 0.38 | 1.00 | 1.00 | 1.00 |
| 6430706D22Rik | 0.83 | 1.00 | 0.82 | 1.15 | 0.31 | 0.93 | 0.96 | 1.31 | 1.28 | 0.52 | 0.43 | 1.09 |
| 8430429K09Rik | 0.93 | 1.34 | 0.75 | 0.84 | 0.47 | 0.97 | 0.95 | 0.91 | 0.87 | 0.78 | 0.20 | 1.02 |
| 9130221H12Rik | 1.10 | 1.40 | 0.93 | 0.49 | 0.46 | 0.95 | 0.92 | 0.78 | 0.80 | 0.68 | 0.69 | 0.90 |
| 9230104L09Rik | 0.94 | 1.00 | 1.00 | 1.00 | 1.29 | 1.00 | 2.00 | 2.52 | 1.00 | 0.54 | 1.16 | 1.22 |
| 9330151L19Rik | 0.82 | 1.54 | 0.84 | 1.05 | 0.26 | 1.21 | 0.85 | 0.67 | 0.79 | 0.93 | 0.29 | 0.93 |
| 9330159F19Rik | 0.32 | 0.62 | 0.40 | 0.51 | 0.18 | 0.15 | 1.00 | 1.17 | 1.00 | 0.85 | 0.59 | 0.47 |
| 9530002B09Rik | 1.00 | 1.00 | 1.00 | 1.00 | 1.00 | 1.00 | 1.00 | 1.00 | 1.00 | 1.00 | 1.00 | 1.00 |
| 9530053A07Rik | 1.00 | 1.00 | 1.00 | 1.00 | 1.00 | 1.00 | 1.00 | 1.00 | 1.00 | 1.81 | 1.44 | 1.00 |
| 9630033F20Rik | 0.52 | 0.37 | 0.53 | 0.50 | 0.28 | 0.55 | 0.95 | 1.05 | 1.03 | 0.31 | 0.69 | 1.03 |
| A530016L24Rik | 0.52 | 0.92 | 1.21 | 0.11 | 0.26 | 0.44 | 0.50 | 0.48 | 0.56 | 1.00 | 1.00 | 1.00 |
| A530050N04Rik | 0.53 | 1.00 | 0.88 | 1.33 | 2.93 | 2.02 | 0.46 | 0.65 | 0.54 | 1.00 | 0.66 | 0.41 |
| A730008H23Rik | 1.00 | 1.00 | 1.00 | 1.00 | 1.00 | 0.44 | 1.00 | 1.00 | 1.00 | 1.00 | 1.00 | 1.00 |

Fig. 35-2

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| 0610010B08Rik | 0.47 | 0.52 | 0.46 | 0.26 | 0.14 | 0.35 | 0.32 | 0.26 | 0.34 | 0.69 | 0.36 | 0.44 |
| 0610031O16Rik | 1.00 | 1.00 | 1.00 | 2.09 | 3.22 | 3.86 | 0.37 | 0.11 | 0.42 | 1.00 | 1.00 | 1.00 |
| 1110007C09Rik | 1.33 | 1.15 | 1.08 | 0.79 | 2.48 | 0.76 | 0.74 | 0.17 | 0.82 | 0.98 | 1.23 | 1.02 |
| 1500017E21Rik | 1.32 | 1.29 | 1.50 | 1.00 | 1.00 | 1.00 | 0.12 | 0.58 | 0.21 | 0.87 | 0.70 | 0.99 |
| 1600029I14Rik | 1.00 | 1.00 | 1.00 | 1.00 | 1.00 | 1.00 | 1.00 | 1.00 | 1.00 | 1.00 | 1.00 | 1.00 |
| 1700001C02Rik | 1.00 | 1.00 | 1.00 | 1.00 | 1.00 | 1.00 | 1.00 | 1.00 | 1.00 | 1.00 | 1.00 | 1.00 |
| 1700003C15Rik | 1.00 | 1.00 | 1.00 | 1.00 | 1.00 | 1.00 | 1.00 | 1.00 | 1.00 | 1.00 | 1.00 | 1.00 |
| 1700006A11Rik | 1.00 | 1.00 | 1.00 | 1.00 | 1.00 | 1.00 | 1.00 | 1.00 | 1.00 | 1.00 | 1.00 | 1.00 |
| 1700020L24Rik | 1.46 | 1.44 | 1.21 | 1.22 | 1.00 | 1.31 | 1.00 | 1.00 | 1.00 | 1.13 | 1.52 | 1.19 |
| 1700023L04Rik | 1.48 | 1.74 | 1.00 | 1.00 | 1.00 | 1.00 | 1.00 | 1.00 | 1.00 | 1.00 | 1.00 | 1.00 |
| 1700025K24Rik | 1.00 | 1.00 | 1.00 | 1.00 | 1.00 | 1.00 | 1.00 | 1.00 | 1.00 | 1.00 | 1.00 | 1.00 |
| 1700028B04Rik | 1.00 | 1.32 | 0.65 | 1.32 | 1.00 | 1.37 | 1.00 | 1.00 | 1.34 | 0.64 | 1.64 | 1.59 |
| 1700029P11Rik | 1.00 | 1.00 | 1.00 | 1.00 | 1.00 | 1.00 | 1.00 | 1.00 | 1.00 | 1.00 | 1.00 | 1.00 |
| 1700044K03Rik | 1.00 | 1.00 | 1.00 | 1.00 | 1.00 | 1.00 | 1.00 | 1.00 | 1.00 | 1.00 | 1.00 | 1.00 |
| 1700045H11Rik | 1.00 | 1.00 | 1.00 | 1.00 | 1.00 | 1.00 | 1.00 | 1.00 | 1.00 | 1.00 | 1.00 | 1.00 |
| 1700047G03Rik | 1.00 | 1.00 | 1.00 | 1.00 | 1.00 | 1.00 | 1.00 | 1.00 | 1.00 | 1.00 | 1.00 | 1.00 |
| 1700088E04Rik | 1.00 | 1.00 | 1.00 | 2.34 | 0.56 | 0.62 | 1.00 | 1.00 | 1.00 | 1.00 | 1.00 | 1.00 |
| 1700123I01Rik | 1.00 | 1.00 | 1.00 | 1.00 | 1.00 | 1.00 | 1.00 | 1.00 | 1.00 | 1.00 | 1.00 | 1.00 |
| 1810007D17Rik | 1.00 | 1.00 | 1.00 | 1.00 | 1.00 | 1.00 | 1.00 | 1.00 | 1.00 | 1.00 | 1.00 | 1.00 |
| 1810021B22Rik | 1.00 | 1.50 | 0.89 | 0.96 | 0.98 | 0.66 | 1.69 | 0.27 | 0.45 | 2.11 | 1.23 | 0.93 |
| 1810030O07Rik | 0.97 | 0.95 | 1.11 | 0.93 | 1.33 | 0.77 | 1.12 | 1.71 | 1.08 | 0.95 | 0.93 | 1.02 |
| 1810043H04Rik | 1.25 | 1.45 | 1.12 | 0.67 | 0.53 | 0.86 | 0.97 | 1.18 | 0.79 | 0.90 | 1.34 | 0.96 |
| 1810064F22Rik | 1.00 | 1.00 | 1.00 | 1.00 | 1.00 | 1.00 | 0.05 | 0.07 | 0.07 | 1.00 | 1.00 | 1.00 |
| 2010016I18Rik | 0.71 | 0.74 | 1.07 | 1.00 | 1.00 | 1.00 | 1.00 | 1.00 | 1.00 | 0.95 | 0.68 | 0.62 |
| 2310015A10Rik | 1.02 | 0.99 | 1.34 | 1.18 | 1.00 | 1.45 | 1.97 | 1.00 | 1.94 | 0.94 | 0.66 | 0.86 |
| 2410017I17Rik | 0.32 | 0.32 | 0.20 | 1.00 | 1.00 | 1.00 | 1.00 | 1.00 | 1.00 | 1.00 | 0.81 | 0.78 |
| 2510003E04Rik | 0.89 | 0.83 | 1.00 | 0.98 | 1.30 | 0.94 | 1.47 | 0.48 | 0.99 | 1.02 | 0.94 | 1.00 |
| 2610001J05Rik | 1.21 | 1.55 | 1.17 | 1.12 | 1.55 | 1.28 | 0.85 | 0.53 | 0.88 | 1.08 | 1.21 | 1.02 |
| 2610035D17Rik | 0.17 | 0.30 | 0.22 | 0.24 | 0.36 | 0.19 | 1.00 | 1.00 | 1.00 | 0.63 | 0.90 | 0.60 |
| 2610203C20Rik | 1.35 | 0.76 | 1.28 | 0.76 | 1.00 | 0.74 | 1.00 | 1.00 | 1.00 | 0.84 | 0.46 | 0.91 |
| 2610528J11Rik | 3.30 | 1.85 | 2.17 | 0.82 | 1.16 | 0.95 | 0.74 | 0.15 | 0.74 | 1.07 | 1.24 | 1.02 |
| 2810004N23Rik | 0.79 | 0.72 | 0.84 | 0.82 | 1.22 | 0.77 | 1.19 | 0.86 | 0.92 | 0.81 | 0.92 | 0.93 |
| 2810403A07Rik | 0.85 | 0.91 | 0.92 | 1.05 | 1.71 | 0.98 | 0.98 | 0.64 | 1.01 | 0.94 | 0.91 | 1.04 |
| 3010033K07Rik | 1.00 | 1.30 | 0.99 | 1.00 | 1.00 | 1.00 | 1.00 | 1.00 | 1.00 | 1.00 | 1.00 | 1.00 |
| 4732471J01Rik | 0.84 | 1.00 | 0.95 | 1.00 | 1.00 | 1.00 | 1.00 | 1.00 | 1.00 | 0.72 | 1.37 | 0.65 |
| 4921524J17Rik | 0.87 | 0.85 | 0.76 | 0.89 | 1.66 | 0.88 | 0.97 | 1.31 | 0.84 | 0.91 | 0.83 | 1.15 |
| 4921525O09Rik | 1.00 | 1.00 | 1.00 | 1.00 | 1.00 | 1.00 | 1.00 | 1.00 | 1.00 | 1.00 | 1.00 | 1.00 |
| 4930401O12Rik | 1.00 | 1.00 | 1.00 | 1.00 | 1.00 | 1.00 | 1.00 | 1.00 | 1.00 | 1.00 | 1.00 | 1.00 |
| 4930402H24Rik | 0.76 | 0.47 | 1.22 | 1.12 | 1.00 | 1.03 | 0.78 | 1.00 | 0.73 | 1.08 | 0.53 | 0.90 |
| 4930412O13Rik | 1.00 | 1.00 | 1.00 | 0.96 | 1.00 | 0.82 | 1.00 | 1.00 | 1.00 | 1.00 | 1.00 | 1.00 |
| 4930413G21Rik | 1.07 | 1.05 | 0.79 | 1.07 | 1.92 | 1.28 | 0.67 | 1.00 | 1.12 | 1.30 | 0.97 | 0.87 |
| 4930519F09Rik | 0.69 | 0.62 | 0.83 | 1.08 | 0.92 | 1.21 | 0.94 | 1.80 | 1.06 | 1.11 | 0.66 | 0.95 |
| 4930594C11Rik | 0.56 | 0.51 | 0.89 | 1.07 | 1.00 | 1.09 | 1.00 | 1.00 | 0.95 | 1.00 | 0.61 | 0.98 |
| 4933402N22Rik | 1.00 | 1.00 | 1.00 | 1.00 | 1.00 | 1.00 | 1.00 | 1.00 | 1.00 | 1.00 | 1.00 | 1.00 |
| 4933417G07Rik | 0.83 | 0.85 | 0.82 | 1.00 | 1.00 | 0.80 | 1.67 | 1.00 | 1.01 | 0.85 | 0.82 | 0.96 |
| 4933421I07Rik | 1.00 | 1.00 | 1.00 | 1.00 | 1.00 | 1.00 | 1.00 | 1.00 | 1.00 | 1.00 | 1.00 | 1.00 |
| 4933426M11Rik | 1.04 | 0.83 | 1.30 | 1.13 | 2.48 | 1.10 | 1.38 | 2.20 | 1.61 | 1.11 | 0.58 | 1.04 |
| 4933430N04Rik | 1.00 | 1.00 | 1.00 | 1.00 | 1.00 | 1.00 | 1.00 | 1.00 | 1.00 | 1.00 | 1.00 | 1.00 |
| 5730416F02Rik | 0.53 | 0.63 | 0.61 | 0.16 | 0.28 | 0.18 | 1.00 | 0.90 | 0.85 | 0.84 | 1.15 | 1.10 |
| 5830403L16Rik | 1.00 | 1.00 | 1.00 | 1.00 | 1.00 | 1.00 | 1.00 | 1.00 | 1.00 | 1.00 | 1.00 | 1.00 |
| 5830454E08Rik | 0.84 | 1.27 | 1.31 | 1.04 | 0.68 | 0.47 | 0.30 | 0.20 | 0.72 | 0.60 | 1.04 | 1.30 |
| 6430571L13Rik | 1.00 | 1.00 | 1.00 | 0.82 | 1.00 | 1.00 | 1.00 | 1.00 | 1.00 | 1.00 | 1.00 | 1.00 |
| 6430706D22Rik | 0.43 | 0.51 | 0.67 | 0.55 | 0.83 | 0.67 | 0.91 | 0.63 | 1.20 | 0.90 | 0.63 | 0.93 |
| 8430429K09Rik | 1.03 | 1.28 | 0.89 | 1.20 | 2.47 | 0.89 | 1.05 | 0.50 | 1.13 | 1.08 | 0.95 | 1.27 |
| 9130221H12Rik | 0.97 | 1.00 | 0.85 | 0.81 | 1.47 | 0.89 | 1.01 | 0.20 | 1.18 | 1.03 | 1.09 | 0.93 |
| 9230104L09Rik | 1.00 | 1.00 | 1.00 | 1.00 | 1.00 | 1.00 | 1.00 | 1.00 | 1.00 | 1.00 | 1.00 | 1.00 |
| 9330151L19Rik | 0.94 | 0.89 | 1.03 | 0.89 | 0.70 | 1.02 | 0.56 | 1.00 | 0.56 | 0.85 | 0.71 | 0.77 |
| 9330159F19Rik | 1.00 | 1.00 | 1.00 | 1.00 | 1.00 | 1.00 | 1.00 | 1.00 | 1.00 | 0.99 | 0.78 | 1.06 |
| 9530002B09Rik | 1.00 | 1.00 | 1.00 | 1.00 | 1.00 | 1.00 | 1.00 | 1.00 | 1.00 | 0.12 | 1.00 | 0.83 |
| 9530053A07Rik | 0.96 | 0.71 | 0.94 | 1.00 | 1.00 | 1.00 | 1.00 | 1.00 | 1.00 | 0.17 | 0.46 | 0.57 |
| 9630033F20Rik | 0.86 | 0.75 | 1.09 | 0.89 | 0.44 | 0.85 | 0.73 | 0.54 | 0.92 | 0.73 | 0.63 | 0.72 |
| A530016L24Rik | 0.67 | 0.61 | 0.35 | 1.00 | 1.00 | 1.00 | 1.00 | 1.00 | 1.00 | 1.00 | 1.00 | 1.00 |
| A530050N04Rik | 0.09 | 0.09 | 0.11 | 0.79 | 1.00 | 0.74 | 1.00 | 1.00 | 1.00 | 0.20 | 0.38 | 0.23 |
| A730008H23Rik | 1.00 | 0.17 | 1.00 | 0.81 | 1.00 | 1.07 | 0.78 | 1.00 | 1.94 | 0.86 | 1.00 | 0.60 |

Fig. 35- 3

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| 0610010B08Rik | 0.83 | 0.36 | 0.40 | 0.48 | 0.26 | 0.43 | 1.00 | 1.00 | 0.93 | 0.59 | 0.52 | 0.76 |
| 0610031O16Rik | 1.00 | 1.00 | 1.00 | 1.00 | 1.00 | 1.00 | 1.00 | 1.00 | 1.00 | 1.00 | 1.00 | 1.00 |
| 1110007C09Rik | 0.77 | 0.74 | 0.86 | 0.85 | 1.00 | 0.93 | 0.70 | 0.53 | 0.66 | 1.03 | 0.93 | 0.87 |
| 1500017E21Rik | 0.69 | 1.36 | 1.61 | 0.92 | 1.00 | 1.00 | 0.34 | 1.00 | 0.42 | 0.97 | 1.00 | 1.00 |
| 1600029I14Rik | 1.00 | 1.00 | 1.00 | 0.38 | 0.49 | 0.68 | 1.00 | 1.00 | 1.00 | 1.00 | 1.39 | 1.21 |
| 1700001C02Rik | 1.00 | 1.00 | 1.00 | 1.10 | 2.93 | 2.57 | 0.84 | 2.55 | 0.73 | 1.00 | 1.00 | 1.00 |
| 1700003C15Rik | 1.00 | 1.00 | 1.00 | 1.00 | 1.00 | 1.00 | 0.25 | 1.00 | 0.19 | 1.00 | 1.00 | 1.00 |
| 1700006A11Rik | 1.00 | 1.00 | 1.00 | 1.00 | 1.00 | 1.00 | 0.88 | 0.15 | 1.07 | 1.00 | 1.00 | 1.00 |
| 1700020L24Rik | 0.77 | 1.03 | 0.77 | 0.50 | 0.14 | 0.90 | 1.12 | 0.73 | 0.93 | 1.05 | 1.45 | 0.96 |
| 1700023L04Rik | 1.00 | 1.00 | 1.00 | 0.36 | 0.18 | 0.77 | 0.96 | 0.49 | 0.94 | 1.00 | 1.11 | 1.00 |
| 1700025K24Rik | 1.00 | 1.00 | 1.00 | 1.00 | 1.00 | 1.00 | 0.17 | 0.25 | 0.15 | 1.00 | 1.00 | 1.00 |
| 1700028B04Rik | 0.88 | 1.00 | 0.56 | 1.00 | 1.00 | 1.10 | 1.41 | 0.41 | 0.82 | 1.00 | 1.00 | 1.00 |
| 1700029P11Rik | 1.00 | 1.00 | 1.00 | 1.00 | 1.00 | 1.00 | 0.98 | 0.19 | 1.02 | 1.00 | 1.00 | 1.00 |
| 1700044K03Rik | 1.00 | 1.00 | 1.00 | 1.00 | 1.00 | 1.00 | 1.22 | 0.60 | 0.18 | 1.00 | 1.00 | 1.00 |
| 1700045H11Rik | 1.00 | 1.00 | 1.00 | 1.00 | 1.00 | 1.00 | 0.23 | 0.10 | 0.24 | 1.00 | 1.00 | 1.00 |
| 1700047G03Rik | 1.00 | 1.00 | 1.00 | 0.54 | 1.00 | 0.14 | 0.81 | 2.90 | 0.89 | 1.00 | 1.00 | 1.00 |
| 1700088E04Rik | 1.00 | 1.00 | 1.00 | 0.93 | 1.00 | 1.33 | 0.91 | 0.03 | 0.53 | 1.00 | 1.00 | 1.00 |
| 1700123I01Rik | 1.00 | 1.00 | 1.00 | 1.00 | 1.00 | 1.00 | 0.78 | 0.19 | 1.07 | 1.00 | 1.00 | 1.00 |
| 1810007D17Rik | 1.00 | 1.00 | 1.00 | 1.00 | 1.00 | 1.00 | 1.00 | 1.00 | 1.00 | 1.00 | 1.00 | 1.00 |
| 1810021B22Rik | 1.27 | 2.37 | 1.37 | 0.41 | 1.00 | 1.42 | 0.62 | 1.77 | 1.90 | 0.68 | 1.47 | 0.66 |
| 1810030O07Rik | 0.96 | 0.99 | 1.05 | 0.90 | 1.36 | 1.04 | 0.70 | 0.64 | 0.64 | 1.08 | 0.87 | 1.08 |
| 1810043H04Rik | 1.02 | 0.82 | 0.92 | 0.99 | 1.06 | 0.87 | 0.97 | 1.80 | 0.94 | 1.05 | 1.79 | 0.99 |
| 1810064F22Rik | 1.33 | 1.16 | 0.96 | 1.04 | 1.00 | 2.00 | 1.00 | 1.00 | 1.00 | 0.40 | 0.55 | 0.71 |
| 2010016I18Rik | 0.74 | 0.81 | 0.45 | 0.19 | 0.27 | 0.91 | 1.00 | 1.00 | 1.00 | 0.56 | 0.54 | 0.86 |
| 2310015A10Rik | 1.12 | 0.92 | 1.07 | 1.03 | 0.96 | 0.97 | 0.98 | 1.40 | 0.75 | 0.89 | 0.61 | 0.99 |
| 2410017I17Rik | 1.00 | 1.00 | 1.00 | 1.00 | 1.00 | 1.00 | 1.00 | 1.00 | 1.00 | 1.00 | 1.00 | 1.00 |
| 2510003E04Rik | 0.95 | 1.04 | 1.28 | 0.88 | 0.23 | 0.98 | 1.11 | 0.74 | 0.97 | 0.99 | 1.06 | 0.96 |
| 2610001J05Rik | 1.02 | 0.99 | 1.05 | 0.93 | 1.01 | 0.89 | 0.81 | 0.38 | 1.06 | 1.15 | 1.09 | 1.16 |
| 2610035D17Rik | 0.68 | 1.03 | 0.71 | 0.29 | 1.00 | 0.33 | 0.24 | 0.30 | 0.44 | 0.23 | 0.45 | 0.40 |
| 2610203C20Rik | 0.95 | 0.88 | 1.13 | 0.92 | 0.42 | 0.94 | 0.89 | 1.00 | 0.89 | 1.18 | 0.83 | 1.02 |
| 2610528J11Rik | 0.83 | 0.85 | 0.84 | 0.95 | 1.00 | 2.25 | 1.00 | 1.00 | 1.00 | 1.39 | 1.67 | 0.73 |
| 2810004N23Rik | 1.08 | 0.93 | 0.92 | 1.09 | 3.16 | 1.00 | 0.84 | 0.65 | 0.79 | 1.06 | 0.75 | 1.23 |
| 2810403A07Rik | 0.99 | 0.98 | 0.98 | 1.02 | 0.26 | 1.18 | 1.09 | 0.50 | 1.07 | 1.14 | 0.93 | 1.07 |
| 3010033K07Rik | 1.00 | 1.00 | 1.00 | 0.71 | 2.58 | 2.88 | 1.22 | 1.63 | 1.18 | 1.00 | 1.00 | 1.00 |
| 4732471J01Rik | 1.00 | 1.00 | 1.00 | 0.45 | 0.15 | 0.98 | 1.07 | 2.06 | 1.06 | 1.00 | 0.86 | 1.01 |
| 4921524J17Rik | 1.05 | 0.86 | 0.91 | 1.16 | 1.00 | 1.16 | 1.11 | 0.36 | 0.84 | 1.09 | 0.88 | 0.95 |
| 4921525O09Rik | 1.00 | 1.00 | 1.00 | 1.00 | 1.00 | 1.00 | 1.11 | 0.18 | 1.15 | 1.00 | 1.00 | 1.00 |
| 4930401O12Rik | 1.00 | 1.00 | 1.00 | 1.00 | 1.00 | 1.00 | 0.10 | 0.08 | 0.12 | 1.00 | 1.00 | 1.00 |
| 4930402H24Rik | 1.27 | 1.28 | 0.93 | 0.75 | 0.33 | 0.58 | 1.20 | 4.53 | 1.02 | 0.66 | 0.82 | 0.78 |
| 4930412O13Rik | 1.00 | 1.00 | 1.00 | 1.00 | 1.00 | 1.00 | 1.01 | 1.35 | 1.25 | 1.00 | 1.00 | 1.00 |
| 4930413G21Rik | 1.04 | 1.35 | 0.90 | 0.78 | 1.00 | 0.75 | 0.93 | 0.94 | 1.00 | 0.85 | 0.92 | 0.91 |
| 4930519F09Rik | 0.97 | 1.28 | 0.98 | 0.73 | 0.49 | 0.76 | 2.35 | 1.14 | 1.69 | 0.89 | 0.79 | 1.23 |
| 4930594C11Rik | 0.88 | 0.66 | 0.74 | 0.97 | 0.75 | 1.06 | 1.05 | 1.69 | 0.92 | 1.00 | 0.71 | 1.02 |
| 4933402N22Rik | 1.00 | 1.00 | 1.00 | 1.00 | 1.00 | 1.00 | 0.76 | 0.15 | 0.72 | 1.00 | 1.00 | 1.00 |
| 4933417G07Rik | 0.76 | 0.93 | 0.88 | 1.20 | 0.44 | 0.84 | 0.90 | 1.17 | 1.10 | 1.06 | 0.93 | 1.05 |
| 4933421I07Rik | 1.00 | 1.00 | 1.00 | 1.00 | 1.00 | 1.00 | 1.25 | 0.16 | 1.03 | 1.00 | 1.00 | 1.00 |
| 4933426M11Rik | 1.26 | 1.27 | 1.04 | 1.28 | 0.24 | 1.24 | 0.94 | 2.36 | 1.05 | 0.99 | 0.63 | 1.00 |
| 4933430N04Rik | 1.00 | 1.00 | 1.00 | 1.00 | 1.00 | 1.00 | 0.14 | 0.24 | 0.21 | 1.00 | 1.00 | 1.00 |
| 5730416F02Rik | 0.42 | 0.48 | 0.43 | 0.17 | 0.25 | 0.10 | 0.46 | 0.91 | 0.95 | 0.19 | 0.17 | 0.21 |
| 5830403L16Rik | 1.00 | 1.00 | 1.00 | 0.18 | 1.00 | 1.00 | 0.85 | 1.00 | 0.56 | 1.00 | 1.00 | 1.00 |
| 5830454E08Rik | 1.11 | 0.96 | 1.49 | 0.58 | 0.41 | 1.17 | 0.28 | 0.89 | 1.22 | 0.69 | 0.99 | 0.75 |
| 6430571L13Rik | 1.00 | 1.00 | 1.00 | 0.89 | 1.00 | 0.68 | 1.52 | 1.00 | 1.49 | 1.00 | 1.00 | 1.00 |
| 6430706D22Rik | 0.87 | 0.78 | 0.88 | 0.89 | 1.00 | 1.09 | 1.20 | 1.00 | 1.06 | 0.85 | 0.63 | 0.70 |
| 8430429K09Rik | 0.98 | 1.23 | 1.02 | 1.11 | 0.78 | 1.01 | 0.98 | 0.44 | 1.27 | 1.26 | 1.12 | 0.99 |
| 9130221H12Rik | 0.92 | 0.96 | 0.95 | 0.86 | 0.47 | 1.36 | 1.02 | 0.68 | 1.00 | 0.94 | 0.93 | 0.94 |
| 9230104L09Rik | 1.00 | 1.00 | 1.00 | 0.17 | 1.00 | 1.00 | 0.73 | 0.66 | 0.56 | 1.00 | 1.00 | 1.00 |
| 9330151L19Rik | 0.94 | 1.13 | 1.25 | 0.64 | 0.95 | 1.02 | 1.02 | 0.41 | 0.84 | 1.00 | 0.91 | 0.97 |
| 9330159F19Rik | 1.11 | 1.38 | 1.69 | 0.23 | 0.24 | 0.30 | 1.00 | 1.00 | 1.00 | 1.00 | 1.81 | 1.00 |
| 9530002B09Rik | 1.00 | 1.00 | 1.00 | 1.00 | 1.00 | 1.00 | 1.77 | 1.21 | 0.63 | 1.00 | 1.00 | 1.00 |
| 9530053A07Rik | 1.00 | 1.00 | 1.00 | 1.00 | 1.00 | 1.00 | 1.00 | 1.00 | 1.00 | 1.00 | 1.00 | 1.00 |
| 9630033F20Rik | 0.73 | 0.68 | 0.73 | 0.78 | 1.00 | 0.93 | 0.91 | 0.26 | 0.94 | 0.95 | 0.80 | 0.92 |
| A530016L24Rik | 1.00 | 1.00 | 1.00 | 0.07 | 0.07 | 0.27 | 1.00 | 1.00 | 1.00 | 1.00 | 1.00 | 1.00 |
| A530050N04Rik | 0.28 | 0.29 | 0.27 | 0.30 | 0.27 | 0.27 | 1.00 | 1.00 | 1.00 | 0.26 | 0.29 | 0.21 |
| A730008H23Rik | 0.45 | 0.36 | 0.27 | 1.00 | 1.00 | 0.60 | 1.36 | 1.00 | 1.33 | 0.45 | 0.98 | 0.99 |

Fig. 35- 4

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| 0610010B08Rik | 0.95 | 0.92 | 0.96 | 0.57 | 0.22 | 0.49 | 0.34 | 1.38 | 0.44 | 1.00 | 0.86 | 0.85 |
| 0610031O16Rik | 1.00 | 1.00 | 1.00 | 1.00 | 1.00 | 1.00 | 1.00 | 1.00 | 1.00 | 1.00 | 1.00 | 1.00 |
| 1110007C09Rik | 0.70 | 0.53 | 0.90 | 0.65 | 0.29 | 1.32 | 1.30 | 0.61 | 1.21 | 1.13 | 1.60 | 1.61 |
| 1500017E21Rik | 1.00 | 1.00 | 1.00 | 2.71 | 0.92 | 1.55 | 1.65 | 1.00 | 1.00 | 1.00 | 1.00 | 1.00 |
| 1600029I14Rik | 1.00 | 1.00 | 1.00 | 1.00 | 0.25 | 1.00 | 1.00 | 1.00 | 1.00 | 1.00 | 1.00 | 1.00 |
| 1700001C02Rik | 1.00 | 1.00 | 1.00 | 1.00 | 0.05 | 1.08 | 1.00 | 1.00 | 1.00 | 1.00 | 1.00 | 1.00 |
| 1700003C15Rik | 1.00 | 1.00 | 1.00 | 1.00 | 1.00 | 1.00 | 1.00 | 1.00 | 1.00 | 1.00 | 1.00 | 1.00 |
| 1700006A11Rik | 1.00 | 1.00 | 1.00 | 1.00 | 1.00 | 1.00 | 1.00 | 1.00 | 1.00 | 1.00 | 1.00 | 1.00 |
| 1700020L24Rik | 1.00 | 1.00 | 1.00 | 1.01 | 1.00 | 0.91 | 1.52 | 0.21 | 1.22 | 1.66 | 1.49 | 1.27 |
| 1700023L04Rik | 1.00 | 1.00 | 1.00 | 1.00 | 1.00 | 1.00 | 3.19 | 1.00 | 1.01 | 1.00 | 1.00 | 1.00 |
| 1700025K24Rik | 1.00 | 1.00 | 1.00 | 1.00 | 1.00 | 1.00 | 1.00 | 1.00 | 1.00 | 1.00 | 1.00 | 1.00 |
| 1700028B04Rik | 1.00 | 1.00 | 1.00 | 1.00 | 1.00 | 0.98 | 1.00 | 0.89 | 0.67 | 1.00 | 0.86 | 0.80 |
| 1700029P11Rik | 1.00 | 1.00 | 1.00 | 1.00 | 1.00 | 1.00 | 1.00 | 1.00 | 1.00 | 1.00 | 1.00 | 1.00 |
| 1700044K03Rik | 1.00 | 1.00 | 1.00 | 1.00 | 1.00 | 1.00 | 1.00 | 1.00 | 1.00 | 1.00 | 1.00 | 1.00 |
| 1700045H11Rik | 1.00 | 1.00 | 1.00 | 1.00 | 1.00 | 1.00 | 1.00 | 1.00 | 1.00 | 1.00 | 1.00 | 1.00 |
| 1700047G03Rik | 1.00 | 1.00 | 1.00 | 1.00 | 1.00 | 1.00 | 1.00 | 1.00 | 1.00 | 1.00 | 1.00 | 1.00 |
| 1700088E04Rik | 1.00 | 1.00 | 1.00 | 1.00 | 0.14 | 1.00 | 1.00 | 1.00 | 1.00 | 1.00 | 1.00 | 1.00 |
| 1700123I01Rik | 1.00 | 1.00 | 1.00 | 1.00 | 1.00 | 1.00 | 1.00 | 1.00 | 1.00 | 1.00 | 1.00 | 1.00 |
| 1810007D17Rik | 0.80 | 0.49 | 0.06 | 1.00 | 1.00 | 1.00 | 1.00 | 1.00 | 1.00 | 1.00 | 1.00 | 1.00 |
| 1810021B22Rik | 1.00 | 1.00 | 1.00 | 1.00 | 0.16 | 1.00 | 1.02 | 2.45 | 0.65 | 2.14 | 0.51 | 1.00 |
| 1810030O07Rik | 1.02 | 0.74 | 0.67 | 1.09 | 2.03 | 0.90 | 0.73 | 0.12 | 0.85 | 0.62 | 0.91 | 0.98 |
| 1810043H04Rik | 0.65 | 0.60 | 0.76 | 1.38 | 1.60 | 1.00 | 1.20 | 2.98 | 1.01 | 1.92 | 1.24 | 1.00 |
| 1810064F22Rik | 0.61 | 0.50 | 0.63 | 1.00 | 1.00 | 1.00 | 1.00 | 1.00 | 1.00 | 1.00 | 1.00 | 1.00 |
| 2010016I18Rik | 1.00 | 1.00 | 1.00 | 1.00 | 1.00 | 1.00 | 0.48 | 0.19 | 0.49 | 0.66 | 0.72 | 1.09 |
| 2310015A10Rik | 1.35 | 1.12 | 1.48 | 0.89 | 0.19 | 0.93 | 0.87 | 0.30 | 1.02 | 0.77 | 1.02 | 0.89 |
| 2410017I17Rik | 1.00 | 1.00 | 1.00 | 1.00 | 1.00 | 1.00 | 1.00 | 1.00 | 1.00 | 1.00 | 1.00 | 1.00 |
| 2510003E04Rik | 1.16 | 0.71 | 0.71 | 1.17 | 1.09 | 1.03 | 1.04 | 0.14 | 0.91 | 0.39 | 0.92 | 1.03 |
| 2610001J05Rik | 0.89 | 1.09 | 1.49 | 1.14 | 0.19 | 1.09 | 0.92 | 0.48 | 1.00 | 0.58 | 1.51 | 1.42 |
| 2610035D17Rik | 0.75 | 0.95 | 0.78 | 0.82 | 0.22 | 0.82 | 0.49 | 0.45 | 0.51 | 0.36 | 0.45 | 0.35 |
| 2610203C20Rik | 1.00 | 1.00 | 1.00 | 0.95 | 1.00 | 0.94 | 0.67 | 0.09 | 1.07 | 1.00 | 1.00 | 1.00 |
| 2610528J11Rik | 0.79 | 0.73 | 0.38 | 1.00 | 1.00 | 1.00 | 1.05 | 0.70 | 0.72 | 1.00 | 1.00 | 1.00 |
| 2810004N23Rik | 1.02 | 0.76 | 1.21 | 0.77 | 1.00 | 0.95 | 0.59 | 0.20 | 0.90 | 1.03 | 0.94 | 1.00 |
| 2810403A07Rik | 0.86 | 0.78 | 0.94 | 0.93 | 2.28 | 1.03 | 0.93 | 0.11 | 1.09 | 0.52 | 1.01 | 1.03 |
| 3010033K07Rik | 1.00 | 1.00 | 1.00 | 1.00 | 1.00 | 1.00 | 1.00 | 1.00 | 1.00 | 1.00 | 1.00 | 1.00 |
| 4732471J01Rik | 1.00 | 1.00 | 1.00 | 1.20 | 1.00 | 0.82 | 1.00 | 1.22 | 1.00 | 1.00 | 1.00 | 1.00 |
| 4921524J17Rik | 0.67 | 1.18 | 0.81 | 0.95 | 1.17 | 0.94 | 1.01 | 0.11 | 0.94 | 0.37 | 1.10 | 0.96 |
| 4921525O09Rik | 1.00 | 1.00 | 1.00 | 1.00 | 1.00 | 1.00 | 1.00 | 1.00 | 1.00 | 1.00 | 1.00 | 1.00 |
| 4930401O12Rik | 1.00 | 1.00 | 1.00 | 1.00 | 1.00 | 1.00 | 1.00 | 1.00 | 1.00 | 1.00 | 1.00 | 1.00 |
| 4930402H24Rik | 1.00 | 1.00 | 1.00 | 0.84 | 1.00 | 0.81 | 0.86 | 1.00 | 1.05 | 1.00 | 0.84 | 0.85 |
| 4930412O13Rik | 1.00 | 1.00 | 1.00 | 1.00 | 1.00 | 1.00 | 0.77 | 0.20 | 0.96 | 1.00 | 1.00 | 1.00 |
| 4930413G21Rik | 1.01 | 1.00 | 0.77 | 0.81 | 0.38 | 0.88 | 1.05 | 0.17 | 1.02 | 1.10 | 1.22 | 0.83 |
| 4930519F09Rik | 1.41 | 1.34 | 1.34 | 0.92 | 1.00 | 0.84 | 1.16 | 0.18 | 1.40 | 0.71 | 0.88 | 0.82 |
| 4930594C11Rik | 1.56 | 0.86 | 0.70 | 0.74 | 1.00 | 0.96 | 0.76 | 0.18 | 0.96 | 0.39 | 0.64 | 0.85 |
| 4933402N22Rik | 1.00 | 1.00 | 1.00 | 1.00 | 1.00 | 1.00 | 1.00 | 1.00 | 1.00 | 1.00 | 1.00 | 1.00 |
| 4933417G07Rik | 1.00 | 1.95 | 0.78 | 0.86 | 1.00 | 1.13 | 1.15 | 0.11 | 0.84 | 0.19 | 0.74 | 0.92 |
| 4933421I07Rik | 1.00 | 1.00 | 1.00 | 1.00 | 1.00 | 1.00 | 1.00 | 1.00 | 1.00 | 1.00 | 1.00 | 1.00 |
| 4933426M11Rik | 1.63 | 1.60 | 1.18 | 1.10 | 1.00 | 1.03 | 0.86 | 0.06 | 0.92 | 0.30 | 1.05 | 0.95 |
| 4933430N04Rik | 1.00 | 1.00 | 1.00 | 1.00 | 1.00 | 1.00 | 1.00 | 1.00 | 1.00 | 1.00 | 1.00 | 1.00 |
| 5730416F02Rik | 1.00 | 1.00 | 0.82 | 0.68 | 1.00 | 1.00 | 0.33 | 0.05 | 0.28 | 0.03 | 0.06 | 0.07 |
| 5830403L16Rik | 1.00 | 1.00 | 1.00 | 1.00 | 1.00 | 1.00 | 1.00 | 1.00 | 1.00 | 1.00 | 1.00 | 1.00 |
| 5830454E08Rik | 1.00 | 0.53 | 0.77 | 1.40 | 3.26 | 0.86 | 1.48 | 1.19 | 1.06 | 2.54 | 1.84 | 0.92 |
| 6430571L13Rik | 1.00 | 1.00 | 1.00 | 1.01 | 1.16 | 0.99 | 0.66 | 0.74 | 0.74 | 1.00 | 1.00 | 1.00 |
| 6430706D22Rik | 0.73 | 0.71 | 1.00 | 0.88 | 1.54 | 0.96 | 0.68 | 0.05 | 0.89 | 0.54 | 0.76 | 0.88 |
| 8430429K09Rik | 0.84 | 1.00 | 0.73 | 1.04 | 1.00 | 1.20 | 1.07 | 0.38 | 0.90 | 0.55 | 1.08 | 1.05 |
| 9130221H12Rik | 1.09 | 0.93 | 0.97 | 1.00 | 2.42 | 0.92 | 0.92 | 0.58 | 0.85 | 0.61 | 1.03 | 1.08 |
| 9230104L09Rik | 1.00 | 1.00 | 1.00 | 1.00 | 1.00 | 1.00 | 1.00 | 1.00 | 1.00 | 1.00 | 1.00 | 1.00 |
| 9330151L19Rik | 0.76 | 0.83 | 0.87 | 0.97 | 1.64 | 1.00 | 0.93 | 0.12 | 0.93 | 0.64 | 0.96 | 0.96 |
| 9330159F19Rik | 1.00 | 1.00 | 1.00 | 0.79 | 0.82 | 0.88 | 1.33 | 0.47 | 1.95 | 1.00 | 1.00 | 1.00 |
| 9530002B09Rik | 1.00 | 1.00 | 1.00 | 1.00 | 1.00 | 1.00 | 1.00 | 1.00 | 1.00 | 1.00 | 1.00 | 1.00 |
| 9530053A07Rik | 1.00 | 1.00 | 1.00 | 1.00 | 1.00 | 1.00 | 1.05 | 2.24 | 1.18 | 1.00 | 1.00 | 1.00 |
| 9630033F20Rik | 1.00 | 1.00 | 1.00 | 0.95 | 0.18 | 0.93 | 0.84 | 0.18 | 0.76 | 0.94 | 0.99 | 1.17 |
| A530016L24Rik | 1.00 | 1.00 | 1.00 | 1.00 | 0.34 | 1.00 | 0.48 | 1.40 | 0.54 | 1.00 | 1.00 | 1.00 |
| A530050N04Rik | 1.00 | 1.00 | 1.00 | 0.27 | 1.00 | 0.35 | 0.47 | 0.66 | 0.34 | 1.00 | 0.54 | 0.42 |
| A730008H23Rik | 1.00 | 1.00 | 1.00 | 0.46 | 1.00 | 0.69 | 0.17 | 0.77 | 1.06 | 1.00 | 1.00 | 1.00 |

Fig. 35- 5

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| A930015D03Rik | 0.71 | 1.92 | 1.08 | 0.59 | 0.15 | 0.96 | 0.83 | 0.87 | 0.74 | 0.14 | 0.28 | 0.95 |
| AA465934 | 1.00 | 0.66 | 1.00 | 0.17 | 1.68 | 0.89 | 1.00 | 0.86 | 1.40 | 1.23 | 0.56 | 0.95 |
| AI597479 | 0.70 | 1.76 | 0.79 | 1.43 | 0.29 | 1.02 | 1.17 | 1.29 | 0.91 | 0.31 | 0.29 | 1.04 |
| AI607873 | 0.99 | 1.39 | 1.51 | 1.55 | 0.47 | 0.82 | 0.43 | 0.59 | 0.63 | 1.08 | 1.07 | 0.92 |
| AI747448 | 1.00 | 1.00 | 1.00 | 1.00 | 1.00 | 1.00 | 1.00 | 1.00 | 1.00 | 1.00 | 1.00 | 1.00 |
| AY074887 | 1.00 | 1.00 | 1.00 | 1.00 | 1.00 | 1.00 | 1.00 | 1.00 | 1.51 | 1.00 | 1.00 | 1.00 |
| Abat | 1.29 | 1.00 | 1.00 | 1.00 | 0.15 | 1.00 | 1.56 | 1.87 | 1.27 | 1.00 | 1.00 | 1.28 |
| Abca12 | 1.00 | 1.00 | 1.00 | 1.00 | 1.00 | 1.00 | 1.00 | 1.00 | 1.00 | 1.00 | 1.00 | 1.00 |
| Abca5 | 1.07 | 1.80 | 0.98 | 2.16 | 0.48 | 1.02 | 0.96 | 1.00 | 1.17 | 0.44 | 0.40 | 1.18 |
| Abcd1 | 0.76 | 1.50 | 0.94 | 0.80 | 0.08 | 0.80 | 1.01 | 1.05 | 0.86 | 0.29 | 0.13 | 0.93 |
| Abcd2 | 0.36 | 0.78 | 0.55 | 2.59 | 0.40 | 0.67 | 1.21 | 1.29 | 0.94 | 0.67 | 0.58 | 0.79 |
| Abcg4 | 1.00 | 1.00 | 1.00 | 1.00 | 0.88 | 1.00 | 1.00 | 1.00 | 1.00 | 1.00 | 1.00 | 1.00 |
| Abhd1 | 1.17 | 0.95 | 0.84 | 0.11 | 1.12 | 0.43 | 1.12 | 0.76 | 0.62 | 1.16 | 0.77 | 0.90 |
| Abhd2 | 1.15 | 1.00 | 1.00 | 3.19 | 0.75 | 1.23 | 1.44 | 2.47 | 1.83 | 0.88 | 1.48 | 1.55 |
| Abl1 | 0.58 | 1.07 | 0.68 | 1.03 | 0.20 | 1.03 | 0.91 | 0.97 | 0.89 | 0.56 | 0.32 | 0.94 |
| Abr | 1.29 | 1.62 | 1.31 | 1.63 | 0.21 | 1.50 | 1.21 | 1.03 | 0.92 | 0.53 | 0.54 | 1.06 |
| Acadm | 0.69 | 0.83 | 0.65 | 0.85 | 0.67 | 0.93 | 0.65 | 0.71 | 0.61 | 0.29 | 0.48 | 0.85 |
| Acap2 | 0.89 | 1.62 | 0.90 | 2.50 | 0.21 | 1.12 | 1.10 | 1.41 | 1.15 | 0.28 | 0.32 | 0.96 |
| Acbd3 | 0.97 | 1.69 | 1.13 | 1.73 | 0.44 | 1.04 | 1.10 | 1.14 | 1.22 | 0.52 | 0.50 | 1.09 |
| Accs | 1.00 | 0.86 | 1.00 | 1.31 | 4.28 | 1.52 | 1.32 | 1.07 | 0.93 | 0.90 | 0.98 | 0.85 |
| Ache | 0.63 | 1.66 | 0.71 | 1.00 | 0.41 | 1.00 | 0.62 | 0.98 | 1.07 | 1.00 | 1.00 | 0.99 |
| Ackr4 | 1.02 | 1.00 | 1.00 | 1.00 | 1.00 | 0.86 | 0.86 | 0.71 | 0.55 | 0.33 | 0.13 | 0.25 |
| Acp5 | 0.84 | 1.24 | 1.41 | 0.36 | 1.75 | 0.64 | 0.86 | 0.43 | 1.76 | 0.97 | 1.56 | 0.77 |
| Acsbg1 | 1.00 | 1.00 | 1.00 | 1.00 | 0.38 | 1.00 | 1.00 | 1.00 | 1.00 | 1.00 | 1.00 | 1.00 |
| Acsm3 | 1.16 | 1.00 | 2.54 | 2.19 | 0.88 | 2.55 | 1.00 | 1.00 | 1.00 | 1.00 | 1.00 | 1.00 |
| Actn2 | 1.31 | 0.78 | 1.38 | 0.05 | 0.14 | 0.43 | 1.51 | 1.42 | 1.33 | 1.86 | 1.51 | 1.23 |
| Acvr1b | 1.10 | 2.27 | 1.55 | 1.65 | 0.23 | 1.35 | 1.31 | 1.40 | 1.51 | 1.00 | 0.21 | 1.07 |
| Acvr1c | 1.00 | 1.00 | 1.00 | 1.10 | 0.54 | 0.90 | 1.00 | 1.00 | 1.00 | 1.00 | 1.00 | 1.00 |
| Acyp1 | 1.52 | 1.28 | 1.12 | 0.65 | 4.16 | 0.82 | 0.94 | 1.03 | 0.72 | 0.50 | 1.01 | 0.91 |
| Adam11 | 1.00 | 1.00 | 1.00 | 1.21 | 0.31 | 1.14 | 1.11 | 0.88 | 0.84 | 1.00 | 1.00 | 0.87 |
| Adam7 | 1.00 | 1.00 | 1.00 | 1.00 | 1.00 | 1.00 | 1.00 | 1.00 | 1.00 | 1.00 | 1.00 | 1.00 |
| Adam9 | 0.99 | 1.86 | 0.93 | 1.32 | 0.44 | 0.98 | 1.07 | 1.26 | 1.23 | 0.37 | 0.42 | 1.18 |
| Adap2 | 0.99 | 1.00 | 2.71 | 4.55 | 0.89 | 1.71 | 1.17 | 1.35 | 1.60 | 1.00 | 0.55 | 1.54 |
| Adc | 1.00 | 1.00 | 1.00 | 0.77 | 0.60 | 0.66 | 1.00 | 1.00 | 0.77 | 0.68 | 0.69 | 0.89 |
| Adcy6 | 0.88 | 1.22 | 1.11 | 0.79 | 0.30 | 1.00 | 0.93 | 1.07 | 1.02 | 0.47 | 0.40 | 0.93 |
| Adcy7 | 0.83 | 1.00 | 1.00 | 1.00 | 1.00 | 1.05 | 0.79 | 0.76 | 1.00 | 0.55 | 0.34 | 0.85 |
| Add2 | 1.00 | 1.00 | 1.00 | 1.00 | 0.31 | 1.00 | 1.00 | 1.00 | 1.00 | 1.00 | 1.00 | 1.00 |
| Adnp | 0.73 | 1.58 | 0.95 | 1.34 | 0.20 | 0.98 | 1.02 | 1.08 | 1.03 | 0.20 | 0.21 | 0.95 |
| Adnp2 | 1.14 | 1.00 | 1.78 | 1.82 | 0.14 | 0.79 | 1.52 | 1.94 | 1.40 | 1.42 | 0.39 | 1.15 |
| Adra1d | 1.00 | 1.00 | 1.00 | 0.69 | 0.17 | 0.55 | 0.60 | 0.48 | 0.79 | 1.00 | 0.65 | 0.88 |
| Adrb1 | 1.00 | 1.00 | 1.00 | 0.52 | 0.08 | 0.74 | 0.69 | 0.90 | 0.93 | 0.26 | 0.08 | 0.55 |
| Adrb3 | 1.00 | 1.00 | 1.77 | 0.26 | 0.23 | 0.90 | 1.00 | 1.00 | 1.00 | 0.56 | 0.31 | 0.72 |
| Adrbk2 | 0.67 | 1.00 | 0.90 | 1.04 | 0.16 | 0.94 | 0.83 | 1.08 | 1.09 | 0.89 | 0.42 | 1.00 |
| Aebp2 | 1.23 | 1.58 | 1.30 | 1.30 | 0.78 | 1.10 | 1.12 | 1.26 | 1.07 | 0.96 | 0.64 | 1.07 |
| Afap1l2 | 1.00 | 1.00 | 1.06 | 1.00 | 0.96 | 0.85 | 0.93 | 0.76 | 0.88 | 0.94 | 0.59 | 1.29 |
| Aga | 0.80 | 0.73 | 0.77 | 0.68 | 2.06 | 0.86 | 0.81 | 0.77 | 0.75 | 0.57 | 1.33 | 0.73 |
| Agfg2 | 1.45 | 2.40 | 1.44 | 2.22 | 0.55 | 1.70 | 2.15 | 2.23 | 1.83 | 0.37 | 0.39 | 1.55 |
| Agmo | 1.52 | 1.00 | 1.01 | 2.69 | 0.19 | 1.28 | 1.12 | 1.90 | 1.09 | 0.75 | 0.28 | 0.82 |
| Ago4 | 0.67 | 1.00 | 0.79 | 2.13 | 0.71 | 0.94 | 1.26 | 1.25 | 0.95 | 0.68 | 0.33 | 0.88 |
| Agpat2 | 0.58 | 0.87 | 1.45 | 0.12 | 0.43 | 0.74 | 0.63 | 0.62 | 0.82 | 1.17 | 1.58 | 1.19 |
| Ahcyl2 | 0.76 | 2.23 | 0.91 | 2.52 | 0.23 | 1.02 | 1.09 | 1.02 | 1.07 | 0.57 | 0.50 | 1.33 |
| Ahr | 0.81 | 1.00 | 0.96 | 1.95 | 0.51 | 0.69 | 0.67 | 0.80 | 0.87 | 0.54 | 0.48 | 0.86 |
| Aim | 0.63 | 1.88 | 0.69 | 0.91 | 1.12 | 1.24 | 0.68 | 1.07 | 1.31 | 0.29 | 0.18 | 1.05 |
| Ajuba | 0.84 | 1.00 | 1.06 | 0.69 | 0.29 | 0.80 | 0.82 | 0.79 | 1.18 | 0.33 | 0.39 | 0.92 |
| Ak1 | 0.95 | 1.05 | 0.72 | 0.18 | 0.38 | 0.35 | 0.81 | 0.73 | 0.67 | 0.46 | 0.65 | 0.80 |
| Ak4 | 0.36 | 0.56 | 0.42 | 1.56 | 1.00 | 0.63 | 0.33 | 0.36 | 0.39 | 1.00 | 1.00 | 1.00 |
| Akap10 | 1.05 | 1.00 | 1.34 | 0.81 | 0.19 | 0.98 | 1.35 | 1.63 | 1.06 | 0.73 | 0.34 | 1.10 |
| Akap2 | 0.93 | 1.49 | 1.00 | 1.73 | 0.32 | 1.26 | 1.21 | 1.69 | 1.77 | 0.70 | 0.53 | 1.24 |
| Akirin2 | 1.64 | 2.05 | 1.48 | 0.94 | 0.59 | 1.13 | 1.04 | 1.11 | 0.95 | 0.32 | 0.42 | 0.89 |
| Akr1b3 | 0.13 | 0.18 | 0.46 | 0.16 | 0.31 | 0.43 | 3.36 | 0.57 | 1.16 | 2.16 | 2.20 | 0.78 |
| Akr1b7 | 1.00 | 1.00 | 1.00 | 1.00 | 1.00 | 1.00 | 1.00 | 1.00 | 1.00 | 0.64 | 0.69 | 0.85 |
| Akr1c19 | 1.00 | 1.00 | 1.00 | 1.00 | 1.00 | 1.00 | 1.00 | 1.00 | 1.00 | 0.45 | 1.11 | 0.48 |
| Akr1c21 | 1.00 | 1.00 | 1.00 | 1.00 | 1.00 | 1.00 | 1.00 | 1.00 | 1.00 | 1.00 | 1.00 | 1.00 |
| Alas1 | 1.07 | 1.32 | 1.25 | 0.15 | 0.76 | 0.73 | 0.87 | 0.94 | 1.01 | 0.99 | 1.39 | 0.97 |

Fig. 35- 6

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| A930015D03Rik | 0.91 | 0.86 | 0.93 | 1.05 | 1.51 | 1.00 | 0.65 | 1.00 | 1.07 | 1.01 | 0.99 | 0.87 |
| AA465934 | 1.09 | 0.77 | 0.64 | 1.00 | 0.39 | 1.48 | 1.00 | 1.00 | 1.00 | 1.28 | 1.88 | 0.60 |
| AI597479 | 0.81 | 0.70 | 0.99 | 1.03 | 1.00 | 1.01 | 1.13 | 1.00 | 1.04 | 1.05 | 0.63 | 0.93 |
| AI607873 | 1.12 | 0.97 | 1.44 | 1.00 | 1.00 | 1.00 | 1.51 | 1.00 | 2.35 | 0.84 | 0.73 | 1.17 |
| AI747448 | 1.00 | 1.00 | 1.00 | 1.00 | 1.00 | 1.00 | 1.00 | 1.00 | 1.00 | 0.92 | 0.19 | 1.14 |
| AY074887 | 1.00 | 1.00 | 1.00 | 0.75 | 0.20 | 0.70 | 0.66 | 1.00 | 1.37 | 1.00 | 1.00 | 1.00 |
| Abat | 1.37 | 1.10 | 1.54 | 1.00 | 0.91 | 0.97 | 0.90 | 0.90 | 1.09 | 0.93 | 0.67 | 0.90 |
| Abca12 | 1.00 | 1.00 | 1.00 | 1.00 | 1.00 | 1.00 | 1.00 | 1.00 | 1.00 | 1.86 | 1.00 | 1.30 |
| Abca5 | 1.44 | 1.15 | 1.71 | 1.13 | 1.00 | 0.96 | 0.91 | 1.00 | 0.97 | 1.12 | 0.73 | 1.05 |
| Abcd1 | 0.74 | 0.75 | 1.01 | 0.90 | 1.00 | 0.97 | 0.81 | 1.00 | 0.90 | 0.91 | 0.78 | 0.87 |
| Abcd2 | 0.83 | 0.60 | 0.70 | 1.00 | 1.00 | 1.00 | 0.24 | 1.00 | 0.30 | 0.92 | 1.00 | 1.00 |
| Abcg4 | 1.00 | 1.00 | 1.00 | 1.00 | 1.00 | 1.00 | 1.00 | 1.00 | 1.00 | 1.11 | 0.72 | 1.23 |
| Abhd1 | 1.00 | 0.75 | 0.88 | 1.05 | 0.60 | 0.99 | 1.57 | 2.04 | 1.32 | 1.17 | 0.91 | 1.32 |
| Abhd2 | 0.38 | 0.18 | 0.79 | 1.44 | 1.08 | 1.58 | 1.11 | 4.62 | 1.94 | 0.93 | 0.24 | 0.73 |
| Abl1 | 0.80 | 0.80 | 0.93 | 0.91 | 0.80 | 0.92 | 0.69 | 1.00 | 0.84 | 0.96 | 0.71 | 0.91 |
| Abr | 0.86 | 0.82 | 1.08 | 1.01 | 2.41 | 1.13 | 1.22 | 1.00 | 1.37 | 0.92 | 0.74 | 0.92 |
| Acadm | 0.60 | 0.81 | 0.49 | 0.82 | 1.48 | 0.80 | 0.90 | 0.16 | 0.81 | 0.97 | 1.16 | 1.04 |
| Acap2 | 0.84 | 0.77 | 0.93 | 1.09 | 1.00 | 1.13 | 0.91 | 1.00 | 1.00 | 0.93 | 0.52 | 0.85 |
| Acbd3 | 0.85 | 0.72 | 1.01 | 1.30 | 1.98 | 1.22 | 1.59 | 0.81 | 1.46 | 1.07 | 0.81 | 1.08 |
| Accs | 1.58 | 1.03 | 1.13 | 0.86 | 0.68 | 0.87 | 1.15 | 1.00 | 1.00 | 0.84 | 1.05 | 0.92 |
| Ache | 0.72 | 0.57 | 0.92 | 0.30 | 1.00 | 0.47 | 1.00 | 1.00 | 1.00 | 1.24 | 0.71 | 1.07 |
| Ackr4 | 3.77 | 3.40 | 2.29 | 1.00 | 1.00 | 1.00 | 1.00 | 1.00 | 0.99 | 0.92 | 0.71 | 1.04 |
| Acp5 | 1.88 | 2.24 | 1.42 | 0.82 | 0.75 | 0.82 | 0.65 | 0.69 | 0.72 | 1.07 | 1.40 | 0.98 |
| Acsbg1 | 1.14 | 1.28 | 1.60 | 1.00 | 1.00 | 1.00 | 1.00 | 1.00 | 1.00 | 1.00 | 1.00 | 1.00 |
| Acsm3 | 0.92 | 1.00 | 1.14 | 1.70 | 4.74 | 1.71 | 0.82 | 0.17 | 0.83 | 1.02 | 1.00 | 1.04 |
| Actn2 | 1.00 | 1.00 | 1.00 | 1.00 | 1.00 | 1.00 | 1.00 | 1.00 | 1.00 | 1.00 | 1.00 | 1.00 |
| Acvr1b | 0.66 | 0.52 | 1.06 | 1.21 | 1.00 | 1.14 | 1.05 | 1.00 | 1.56 | 0.92 | 0.37 | 0.87 |
| Acvr1c | 1.00 | 1.00 | 1.00 | 1.00 | 1.00 | 1.00 | 1.00 | 1.00 | 1.00 | 1.21 | 0.73 | 1.20 |
| Acyp1 | 1.11 | 1.32 | 0.96 | 0.80 | 1.30 | 0.96 | 0.84 | 0.78 | 0.89 | 1.27 | 1.48 | 1.31 |
| Adam11 | 0.43 | 0.47 | 0.56 | 0.98 | 1.24 | 1.27 | 0.12 | 0.12 | 0.25 | 0.94 | 0.93 | 0.95 |
| Adam7 | 1.00 | 1.00 | 1.00 | 1.00 | 1.00 | 1.00 | 1.00 | 1.00 | 1.00 | 1.00 | 1.00 | 1.00 |
| Adam9 | 1.79 | 1.47 | 1.56 | 1.14 | 2.01 | 1.00 | 0.83 | 0.46 | 0.82 | 1.03 | 0.90 | 1.03 |
| Adap2 | 1.08 | 0.92 | 2.09 | 1.17 | 1.00 | 1.21 | 0.76 | 1.00 | 1.02 | 1.06 | 0.34 | 0.76 |
| Adc | 1.26 | 0.88 | 0.86 | 0.53 | 0.87 | 0.84 | 1.00 | 1.00 | 0.92 | 0.95 | 0.94 | 1.39 |
| Adcy6 | 0.77 | 0.70 | 0.93 | 0.92 | 1.43 | 1.07 | 1.18 | 0.47 | 1.18 | 0.96 | 0.88 | 0.96 |
| Adcy7 | 1.03 | 0.95 | 1.45 | 0.92 | 1.00 | 1.19 | 1.00 | 1.00 | 1.00 | 0.91 | 0.49 | 0.97 |
| Add2 | 1.00 | 1.00 | 1.00 | 1.00 | 1.00 | 1.00 | 1.00 | 1.00 | 1.00 | 1.00 | 1.00 | 1.00 |
| Adnp | 0.63 | 0.56 | 0.87 | 0.95 | 1.45 | 0.94 | 1.14 | 1.13 | 1.11 | 0.98 | 0.63 | 0.99 |
| Adnp2 | 0.60 | 0.53 | 0.86 | 1.05 | 1.00 | 0.96 | 1.06 | 1.00 | 0.82 | 1.09 | 0.55 | 1.01 |
| Adra1d | 1.00 | 1.00 | 1.00 | 1.00 | 1.00 | 1.26 | 1.00 | 1.00 | 1.00 | 1.00 | 1.00 | 1.00 |
| Adrb1 | 1.04 | 0.79 | 1.25 | 0.57 | 1.00 | 0.51 | 1.00 | 1.00 | 1.00 | 0.61 | 0.57 | 0.81 |
| Adrb3 | 0.76 | 0.78 | 0.33 | 1.00 | 1.00 | 1.00 | 0.36 | 0.39 | 0.59 | 1.27 | 1.65 | 1.62 |
| Adrbk2 | 0.94 | 0.77 | 1.14 | 0.88 | 1.00 | 0.95 | 0.99 | 1.00 | 1.23 | 0.99 | 0.66 | 0.94 |
| Aebp2 | 0.77 | 0.76 | 0.89 | 1.16 | 1.17 | 1.14 | 1.23 | 1.64 | 1.26 | 1.13 | 1.14 | 1.15 |
| Afap1l2 | 1.17 | 0.84 | 1.23 | 0.74 | 1.09 | 0.76 | 1.00 | 1.00 | 1.00 | 1.34 | 0.78 | 1.12 |
| Aga | 1.42 | 1.26 | 0.90 | 0.85 | 1.12 | 0.88 | 0.89 | 0.47 | 0.72 | 1.15 | 1.36 | 1.01 |
| Agfg2 | 0.46 | 0.51 | 0.59 | 1.40 | 3.46 | 1.34 | 0.73 | 0.64 | 0.97 | 1.44 | 1.09 | 1.16 |
| Agmo | 1.54 | 0.83 | 1.68 | 1.65 | 1.00 | 1.47 | 0.69 | 0.69 | 0.70 | 0.62 | 0.63 | 0.69 |
| Ago4 | 1.43 | 1.18 | 1.26 | 1.05 | 1.00 | 1.02 | 1.06 | 1.00 | 1.09 | 1.03 | 0.68 | 0.94 |
| Agpat2 | 0.73 | 0.77 | 0.35 | 1.06 | 0.99 | 1.13 | 0.83 | 0.75 | 0.83 | 0.95 | 1.36 | 1.06 |
| Ahcyl2 | 0.93 | 0.77 | 1.20 | 0.92 | 1.11 | 0.90 | 1.09 | 1.00 | 0.92 | 1.02 | 0.75 | 1.00 |
| Ahr | 0.99 | 0.97 | 1.14 | 1.24 | 1.00 | 1.11 | 0.84 | 0.60 | 1.06 | 0.95 | 0.73 | 0.91 |
| Aim | 1.26 | 1.28 | 1.03 | 0.80 | 4.35 | 2.11 | 1.00 | 1.00 | 1.00 | 1.00 | 0.85 | 0.89 |
| Ajuba | 1.36 | 1.18 | 1.23 | 0.93 | 1.68 | 1.15 | 1.08 | 1.00 | 1.84 | 0.86 | 0.67 | 0.85 |
| Ak1 | 0.85 | 0.51 | 0.78 | 0.71 | 1.06 | 0.75 | 1.00 | 1.00 | 1.00 | 0.61 | 0.81 | 0.74 |
| Ak4 | 1.00 | 1.00 | 1.03 | 0.32 | 0.51 | 0.46 | 0.38 | 0.10 | 0.51 | 0.47 | 0.33 | 0.36 |
| Akap10 | 0.79 | 0.62 | 0.95 | 1.07 | 1.00 | 0.94 | 1.28 | 1.00 | 1.09 | 0.98 | 0.73 | 0.89 |
| Akap2 | 0.47 | 0.32 | 0.69 | 1.39 | 1.65 | 1.15 | 0.87 | 1.00 | 1.30 | 1.14 | 0.62 | 1.01 |
| Akirin2 | 0.94 | 0.99 | 0.97 | 0.85 | 2.20 | 1.02 | 0.97 | 1.01 | 0.80 | 1.00 | 1.03 | 0.97 |
| Akr1b3 | 0.29 | 0.41 | 0.54 | 0.85 | 1.00 | 2.82 | 1.00 | 3.01 | 1.00 | 0.24 | 0.49 | 0.77 |
| Akr1b7 | 1.00 | 1.00 | 1.00 | 0.54 | 0.56 | 0.63 | 1.00 | 1.00 | 1.00 | 1.12 | 2.54 | 1.00 |
| Akr1c19 | 1.00 | 1.00 | 1.00 | 0.52 | 0.50 | 0.65 | 0.19 | 0.33 | 0.20 | 0.82 | 0.93 | 0.84 |
| Akr1c21 | 1.00 | 1.00 | 1.00 | 0.15 | 0.14 | 0.16 | 1.00 | 1.00 | 1.00 | 1.00 | 1.00 | 1.00 |
| Alas1 | 1.46 | 1.56 | 1.39 | 1.53 | 2.38 | 1.33 | 0.47 | 0.67 | 0.71 | 1.08 | 1.22 | 0.98 |

Fig. 35-7

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| A930015D03Rik | 0.96 | 1.31 | 0.90 | 0.84 | 1.00 | 1.22 | 0.21 | 0.39 | 0.43 | 1.09 | 0.87 | 0.92 |
| AA465934 | 1.55 | 1.00 | 1.00 | 1.00 | 1.00 | 1.00 | 1.00 | 1.00 | 1.00 | 0.68 | 1.48 | 0.44 |
| AI597479 | 0.91 | 0.77 | 0.98 | 0.85 | 0.81 | 0.81 | 0.98 | 0.47 | 1.02 | 1.03 | 0.83 | 1.15 |
| AI607873 | 1.13 | 0.98 | 1.31 | 0.83 | 0.19 | 0.79 | 0.86 | 1.00 | 1.00 | 1.14 | 1.10 | 1.58 |
| AI747448 | 1.00 | 1.00 | 1.00 | 1.00 | 1.00 | 1.00 | 1.00 | 1.00 | 1.00 | 1.00 | 1.00 | 1.00 |
| AY074887 | 1.00 | 1.00 | 1.00 | 1.00 | 0.66 | 1.00 | 1.00 | 1.00 | 1.00 | 1.00 | 1.00 | 1.00 |
| Abat | 1.52 | 1.63 | 1.66 | 0.72 | 0.34 | 0.69 | 0.86 | 0.74 | 0.88 | 1.13 | 2.51 | 1.11 |
| Abca12 | 0.96 | 1.12 | 1.06 | 1.00 | 1.00 | 1.00 | 1.00 | 1.00 | 1.00 | 1.00 | 1.00 | 1.00 |
| Abca5 | 0.98 | 1.06 | 1.15 | 0.90 | 0.55 | 0.87 | 1.04 | 1.00 | 1.14 | 0.99 | 1.14 | 1.08 |
| Abcd1 | 1.17 | 1.15 | 0.94 | 0.75 | 0.36 | 0.76 | 1.18 | 0.72 | 1.05 | 0.89 | 0.78 | 1.02 |
| Abcd2 | 0.95 | 0.89 | 1.00 | 0.34 | 0.14 | 0.41 | 0.87 | 1.00 | 1.06 | 0.71 | 0.90 | 0.73 |
| Abcg4 | 1.00 | 1.00 | 1.00 | 0.94 | 1.00 | 1.00 | 1.00 | 1.00 | 1.00 | 0.23 | 1.00 | 0.23 |
| Abhd1 | 1.05 | 0.77 | 0.94 | 0.54 | 1.00 | 0.72 | 1.00 | 1.00 | 1.00 | 0.66 | 0.89 | 1.31 |
| Abhd2 | 0.91 | 0.96 | 0.50 | 3.09 | 0.91 | 0.55 | 0.93 | 1.50 | 0.98 | 0.91 | 0.39 | 1.30 |
| Abl1 | 0.97 | 1.05 | 1.01 | 0.96 | 0.28 | 0.87 | 0.99 | 2.30 | 1.17 | 0.84 | 0.73 | 1.00 |
| Abr | 0.90 | 0.93 | 0.92 | 1.32 | 0.34 | 1.34 | 0.83 | 0.73 | 0.87 | 1.04 | 1.13 | 1.08 |
| Acadm | 0.89 | 0.89 | 0.86 | 1.06 | 0.50 | 0.91 | 0.78 | 0.26 | 0.82 | 1.01 | 0.85 | 0.83 |
| Acap2 | 0.92 | 0.92 | 0.94 | 0.85 | 0.28 | 0.77 | 1.07 | 1.00 | 1.10 | 0.92 | 0.67 | 1.00 |
| Acbd3 | 1.01 | 0.91 | 1.00 | 1.16 | 0.44 | 0.98 | 1.21 | 1.00 | 1.08 | 1.42 | 0.97 | 1.33 |
| Accs | 1.08 | 1.20 | 1.31 | 0.77 | 0.64 | 1.17 | 1.00 | 1.00 | 1.00 | 0.96 | 1.14 | 1.22 |
| Ache | 1.54 | 1.52 | 1.40 | 0.99 | 1.00 | 1.00 | 1.00 | 1.00 | 1.00 | 0.84 | 0.66 | 0.52 |
| Ackr4 | 1.46 | 1.09 | 1.18 | 1.28 | 0.53 | 0.80 | 1.00 | 1.00 | 1.00 | 0.54 | 0.56 | 0.54 |
| Acp5 | 0.79 | 0.76 | 0.71 | 0.45 | 1.60 | 0.65 | 0.59 | 0.65 | 0.78 | 1.34 | 1.85 | 1.18 |
| Acsbg1 | 0.81 | 0.98 | 1.18 | 1.77 | 1.00 | 3.09 | 0.81 | 0.13 | 0.82 | 1.20 | 2.11 | 0.77 |
| Acsm3 | 1.88 | 1.73 | 1.70 | 0.51 | 0.42 | 3.31 | 1.00 | 1.00 | 1.00 | 1.00 | 1.00 | 1.00 |
| Actn2 | 2.84 | 1.70 | 2.10 | 0.09 | 0.36 | 0.08 | 0.18 | 0.33 | 0.19 | 0.52 | 0.83 | 0.68 |
| Acvr1b | 0.99 | 0.95 | 0.86 | 1.27 | 0.29 | 1.20 | 1.00 | 1.00 | 1.12 | 0.81 | 0.63 | 1.08 |
| Acvr1c | 0.94 | 0.92 | 1.01 | 0.21 | 0.09 | 0.60 | 1.00 | 1.00 | 1.00 | 1.00 | 1.00 | 1.00 |
| Acyp1 | 0.98 | 1.23 | 1.21 | 0.89 | 0.92 | 0.63 | 1.07 | 0.73 | 1.07 | 0.94 | 1.20 | 0.89 |
| Adam11 | 1.57 | 1.69 | 1.93 | 1.28 | 1.00 | 2.00 | 0.94 | 0.77 | 1.12 | 0.54 | 0.66 | 0.61 |
| Adam7 | 1.00 | 1.00 | 1.00 | 0.37 | 2.01 | 0.09 | 1.00 | 1.00 | 1.00 | 1.00 | 1.00 | 1.00 |
| Adam9 | 1.06 | 1.08 | 0.94 | 1.02 | 0.20 | 0.90 | 0.96 | 0.74 | 1.09 | 1.42 | 1.16 | 1.20 |
| Adap2 | 0.97 | 1.22 | 1.04 | 2.07 | 0.14 | 1.45 | 1.00 | 1.00 | 1.00 | 0.98 | 0.62 | 1.15 |
| Adc | 1.03 | 1.00 | 0.73 | 0.60 | 0.72 | 0.60 | 0.87 | 1.22 | 1.09 | 0.87 | 0.84 | 0.83 |
| Adcy6 | 1.05 | 1.13 | 1.03 | 0.77 | 0.14 | 0.91 | 0.62 | 0.74 | 0.69 | 0.69 | 0.65 | 0.76 |
| Adcy7 | 0.99 | 0.88 | 1.31 | 0.79 | 1.00 | 0.53 | 0.69 | 1.00 | 0.69 | 1.16 | 0.68 | 1.23 |
| Add2 | 1.00 | 1.00 | 1.00 | 1.00 | 1.00 | 1.00 | 0.75 | 1.71 | 1.01 | 0.30 | 0.84 | 0.15 |
| Adnp | 0.88 | 0.84 | 0.90 | 0.89 | 0.13 | 0.88 | 1.21 | 0.62 | 1.07 | 0.92 | 0.63 | 1.07 |
| Adnp2 | 0.83 | 0.84 | 0.93 | 1.17 | 0.90 | 0.86 | 1.17 | 0.54 | 0.83 | 0.86 | 0.55 | 1.05 |
| Adra1d | 1.00 | 1.00 | 1.00 | 0.54 | 0.61 | 0.49 | 0.90 | 1.18 | 0.96 | 1.06 | 1.47 | 1.79 |
| Adrb1 | 1.00 | 1.00 | 1.00 | 0.48 | 1.00 | 0.56 | 1.00 | 1.00 | 0.95 | 0.81 | 1.13 | 0.88 |
| Adrb3 | 1.00 | 1.00 | 1.10 | 0.10 | 0.04 | 0.47 | 1.00 | 1.00 | 1.00 | 1.00 | 1.00 | 1.00 |
| Adrbk2 | 1.02 | 0.90 | 1.15 | 0.96 | 0.75 | 1.08 | 1.24 | 1.63 | 1.07 | 0.63 | 0.54 | 1.20 |
| Aebp2 | 1.01 | 1.00 | 0.80 | 0.86 | 0.19 | 1.05 | 1.20 | 1.59 | 1.24 | 0.91 | 0.67 | 0.92 |
| Afap1l2 | 0.87 | 0.87 | 1.39 | 1.02 | 1.00 | 1.15 | 0.72 | 1.93 | 0.76 | 0.89 | 0.67 | 0.87 |
| Aga | 1.06 | 1.22 | 1.27 | 0.79 | 1.00 | 0.67 | 1.11 | 1.06 | 1.17 | 1.09 | 0.95 | 1.16 |
| Agfg2 | 1.38 | 1.50 | 1.35 | 1.46 | 0.81 | 1.47 | 1.15 | 0.51 | 0.93 | 0.94 | 1.08 | 0.78 |
| Agmo | 0.88 | 0.84 | 0.71 | 0.76 | 0.20 | 0.77 | 1.00 | 1.00 | 1.00 | 0.78 | 1.01 | 0.86 |
| Ago4 | 0.94 | 0.95 | 0.92 | 0.82 | 1.00 | 0.82 | 1.11 | 0.88 | 1.25 | 0.87 | 0.70 | 1.00 |
| Agpat2 | 0.61 | 0.67 | 0.60 | 0.56 | 1.38 | 1.19 | 0.80 | 1.09 | 1.03 | 1.40 | 1.13 | 1.12 |
| Ahcyl2 | 2.00 | 2.04 | 1.57 | 0.69 | 0.17 | 0.62 | 1.06 | 1.05 | 1.03 | 1.30 | 1.30 | 1.50 |
| Ahr | 0.83 | 0.91 | 0.83 | 0.84 | 0.75 | 0.90 | 1.00 | 1.00 | 1.00 | 0.74 | 0.47 | 1.03 |
| Aim | 0.65 | 0.62 | 0.71 | 0.80 | 0.17 | 1.14 | 0.98 | 1.00 | 0.98 | 0.74 | 1.32 | 0.80 |
| Ajuba | 0.76 | 0.67 | 1.02 | 0.76 | 0.35 | 0.76 | 1.12 | 0.61 | 0.92 | 0.72 | 0.69 | 1.16 |
| Ak1 | 0.87 | 0.92 | 1.00 | 0.79 | 0.46 | 0.83 | 1.03 | 1.42 | 0.92 | 0.59 | 0.97 | 0.72 |
| Ak4 | 1.36 | 1.30 | 1.49 | 1.43 | 1.00 | 0.91 | 0.95 | 0.98 | 0.81 | 1.00 | 1.47 | 1.00 |
| Akap10 | 0.91 | 0.80 | 0.82 | 1.02 | 0.79 | 0.96 | 1.11 | 2.03 | 0.99 | 0.89 | 0.65 | 1.02 |
| Akap2 | 1.46 | 1.70 | 1.02 | 1.35 | 0.19 | 0.87 | 1.24 | 1.15 | 1.01 | 0.78 | 0.59 | 0.86 |
| Akirin2 | 1.07 | 0.96 | 1.00 | 0.96 | 0.39 | 1.04 | 0.93 | 0.46 | 0.95 | 0.97 | 0.96 | 0.88 |
| Akr1b3 | 3.40 | 0.34 | 2.23 | 0.46 | 1.00 | 0.82 | 0.79 | 4.99 | 4.30 | 0.88 | 2.10 | 1.22 |
| Akr1b7 | 1.00 | 1.00 | 1.00 | 4.88 | 0.02 | 0.01 | 1.00 | 1.00 | 1.00 | 0.25 | 0.25 | 0.38 |
| Akr1c19 | 0.46 | 0.49 | 0.46 | 0.94 | 3.85 | 0.21 | 1.00 | 0.73 | 1.00 | 1.00 | 0.90 | 1.00 |
| Akr1c21 | 1.00 | 1.00 | 1.00 | 1.00 | 1.00 | 1.00 | 1.00 | 1.00 | 1.00 | 1.00 | 1.00 | 1.00 |
| Alas1 | 0.81 | 0.93 | 0.76 | 0.61 | 1.60 | 0.68 | 0.91 | 0.62 | 0.83 | 1.13 | 1.37 | 1.08 |

Fig. 35-8

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| A930015D03Rik | 1.00 | 1.04 | 0.67 | 0.74 | 1.00 | 1.15 | 0.91 | 0.09 | 1.02 | 0.33 | 1.03 | 0.95 |
| AA465934 | 1.00 | 1.00 | 1.00 | 1.28 | 3.12 | 1.14 | 0.84 | 4.55 | 0.87 | 1.82 | 0.72 | 0.45 |
| AI597479 | 1.51 | 1.21 | 0.82 | 0.97 | 1.00 | 0.88 | 0.88 | 0.10 | 0.95 | 0.31 | 0.80 | 0.96 |
| AI607873 | 0.57 | 1.00 | 1.00 | 1.00 | 1.00 | 1.00 | 0.69 | 0.35 | 1.55 | 1.36 | 1.90 | 3.20 |
| AI747448 | 1.00 | 1.00 | 1.00 | 1.00 | 1.00 | 1.00 | 1.00 | 1.00 | 1.00 | 1.00 | 1.00 | 1.00 |
| AY074887 | 1.00 | 1.00 | 1.00 | 1.00 | 1.00 | 1.00 | 1.00 | 1.00 | 1.00 | 1.00 | 1.00 | 1.00 |
| Abat | 1.00 | 1.00 | 1.00 | 0.95 | 1.02 | 0.98 | 1.00 | 1.00 | 1.32 | 1.00 | 0.76 | 0.90 |
| Abca12 | 1.00 | 1.00 | 1.00 | 1.00 | 1.00 | 1.00 | 0.60 | 0.17 | 0.53 | 1.00 | 1.00 | 1.00 |
| Abca5 | 0.95 | 1.00 | 1.00 | 0.93 | 1.00 | 1.08 | 0.67 | 0.16 | 0.80 | 1.00 | 1.00 | 1.00 |
| Abcd1 | 0.84 | 0.93 | 0.88 | 0.68 | 1.00 | 0.80 | 1.07 | 0.37 | 1.07 | 0.35 | 0.98 | 0.98 |
| Abcd2 | 1.00 | 1.00 | 1.00 | 1.02 | 0.88 | 1.01 | 0.58 | 0.74 | 1.64 | 1.23 | 1.64 | 1.26 |
| Abcg4 | 1.00 | 1.00 | 1.00 | 1.05 | 1.00 | 1.02 | 0.89 | 0.14 | 0.93 | 0.12 | 0.73 | 0.90 |
| Abhd1 | 0.76 | 1.00 | 1.00 | 1.00 | 0.57 | 0.98 | 1.44 | 1.00 | 1.00 | 1.00 | 0.97 | 0.95 |
| Abhd2 | 0.77 | 1.33 | 1.00 | 0.93 | 0.50 | 0.84 | 0.80 | 0.77 | 1.23 | 1.00 | 0.61 | 0.55 |
| Abl1 | 0.93 | 0.88 | 0.84 | 0.92 | 1.04 | 0.91 | 1.08 | 0.16 | 1.14 | 0.41 | 0.86 | 0.77 |
| Abr | 1.45 | 1.18 | 1.10 | 1.10 | 1.09 | 1.03 | 0.76 | 0.13 | 0.84 | 0.66 | 1.06 | 1.13 |
| Acadm | 1.08 | 1.20 | 0.95 | 1.00 | 1.00 | 0.91 | 0.72 | 0.21 | 0.70 | 0.44 | 1.12 | 1.02 |
| Acap2 | 0.91 | 1.08 | 0.97 | 0.89 | 0.72 | 0.94 | 0.65 | 0.08 | 0.77 | 0.55 | 1.05 | 1.08 |
| Acbd3 | 1.74 | 1.40 | 1.37 | 1.01 | 1.00 | 1.03 | 0.78 | 0.12 | 0.83 | 0.52 | 1.00 | 1.01 |
| Accs | 1.00 | 1.00 | 1.00 | 1.02 | 0.20 | 0.96 | 0.89 | 1.76 | 0.90 | 1.86 | 1.32 | 1.24 |
| Ache | 1.00 | 1.00 | 1.00 | 1.11 | 0.62 | 1.14 | 0.87 | 0.16 | 0.97 | 0.51 | 0.56 | 0.63 |
| Ackr4 | 1.00 | 1.00 | 1.00 | 1.10 | 1.00 | 1.00 | 1.14 | 0.43 | 1.28 | 1.00 | 1.00 | 1.30 |
| Acp5 | 0.55 | 0.55 | 0.95 | 1.00 | 0.16 | 1.00 | 0.98 | 2.28 | 0.80 | 2.20 | 1.77 | 1.83 |
| Acsbg1 | 1.00 | 1.00 | 1.00 | 1.05 | 2.40 | 1.01 | 1.41 | 0.19 | 1.52 | 1.00 | 1.00 | 1.00 |
| Acsm3 | 1.00 | 1.00 | 1.00 | 1.00 | 1.00 | 1.00 | 2.43 | 0.55 | 1.84 | 1.00 | 1.00 | 1.00 |
| Actn2 | 1.00 | 1.00 | 1.00 | 1.17 | 4.72 | 1.10 | 1.63 | 2.54 | 2.06 | 1.00 | 1.00 | 1.00 |
| Acvr1b | 0.84 | 0.60 | 0.98 | 0.96 | 0.50 | 0.90 | 0.71 | 0.03 | 0.98 | 0.98 | 0.86 | 0.72 |
| Acvr1c | 1.00 | 1.00 | 1.00 | 0.86 | 1.11 | 0.82 | 1.00 | 1.00 | 1.00 | 1.00 | 1.00 | 1.00 |
| Acyp1 | 2.00 | 0.87 | 0.74 | 1.09 | 0.20 | 1.01 | 1.16 | 0.50 | 1.03 | 1.26 | 0.98 | 1.08 |
| Adam11 | 1.00 | 1.00 | 1.00 | 1.06 | 1.40 | 1.05 | 1.79 | 1.00 | 1.64 | 0.67 | 1.03 | 1.05 |
| Adam7 | 1.00 | 1.00 | 1.00 | 1.00 | 1.00 | 1.00 | 1.00 | 1.00 | 1.00 | 1.00 | 1.00 | 1.00 |
| Adam9 | 0.90 | 1.68 | 1.55 | 0.96 | 1.00 | 0.95 | 0.89 | 0.07 | 1.12 | 0.92 | 1.20 | 1.42 |
| Adap2 | 1.54 | 1.00 | 1.73 | 0.83 | 1.00 | 1.30 | 1.94 | 1.00 | 2.52 | 1.00 | 0.78 | 1.10 |
| Adc | 1.00 | 1.00 | 1.00 | 1.19 | 0.47 | 1.05 | 1.21 | 0.18 | 0.95 | 1.00 | 1.00 | 1.37 |
| Adcy6 | 1.23 | 1.08 | 1.31 | 1.03 | 2.00 | 1.08 | 1.05 | 0.12 | 1.17 | 0.33 | 0.64 | 0.75 |
| Adcy7 | 1.00 | 1.00 | 1.00 | 1.10 | 0.74 | 1.18 | 0.84 | 0.18 | 1.19 | 0.59 | 0.99 | 1.08 |
| Add2 | 1.00 | 1.00 | 1.00 | 0.96 | 1.08 | 0.94 | 0.74 | 2.38 | 0.84 | 0.73 | 0.60 | 0.58 |
| Adnp | 1.00 | 0.91 | 1.07 | 0.97 | 0.98 | 1.02 | 0.83 | 0.07 | 1.04 | 0.29 | 0.83 | 0.92 |
| Adnp2 | 0.80 | 0.89 | 1.00 | 0.94 | 1.00 | 1.00 | 0.60 | 0.19 | 0.86 | 0.65 | 0.64 | 0.72 |
| Adra1d | 1.00 | 1.00 | 1.00 | 1.35 | 1.00 | 1.01 | 1.00 | 1.00 | 1.00 | 1.00 | 1.00 | 1.00 |
| Adrb1 | 1.00 | 1.00 | 0.65 | 0.88 | 1.00 | 1.00 | 1.00 | 1.00 | 1.00 | 1.00 | 1.00 | 1.00 |
| Adrb3 | 1.00 | 1.00 | 1.00 | 1.00 | 0.90 | 1.00 | 2.36 | 1.04 | 1.72 | 1.00 | 1.00 | 1.00 |
| Adrbk2 | 1.00 | 1.00 | 1.00 | 0.96 | 1.09 | 0.98 | 0.70 | 0.35 | 0.73 | 0.53 | 0.84 | 0.86 |
| Aebp2 | 1.06 | 0.92 | 1.27 | 1.07 | 0.85 | 1.10 | 0.92 | 0.30 | 1.07 | 0.65 | 0.89 | 0.94 |
| Afap1l2 | 1.00 | 1.00 | 1.00 | 0.80 | 1.00 | 0.71 | 0.91 | 0.15 | 1.07 | 1.00 | 1.00 | 1.00 |
| Aga | 0.75 | 0.80 | 0.54 | 0.92 | 0.14 | 0.79 | 0.85 | 1.11 | 0.92 | 1.16 | 1.42 | 1.21 |
| Agfg2 | 1.93 | 1.89 | 2.33 | 1.18 | 1.00 | 1.08 | 1.06 | 0.13 | 0.75 | 0.25 | 0.82 | 0.88 |
| Agmo | 0.93 | 0.75 | 1.00 | 1.10 | 1.00 | 0.91 | 1.23 | 0.65 | 1.38 | 1.00 | 1.00 | 1.00 |
| Ago4 | 1.32 | 1.25 | 1.05 | 0.85 | 1.00 | 1.07 | 0.78 | 0.14 | 1.17 | 0.62 | 1.05 | 0.84 |
| Agpat2 | 1.02 | 1.13 | 0.97 | 1.00 | 0.97 | 1.12 | 1.12 | 2.56 | 1.10 | 1.62 | 1.40 | 1.32 |
| Ahcyl2 | 0.75 | 0.93 | 0.91 | 1.02 | 1.53 | 1.03 | 0.65 | 0.14 | 0.90 | 0.37 | 0.94 | 0.97 |
| Ahr | 1.00 | 1.00 | 1.00 | 0.84 | 1.00 | 0.93 | 0.88 | 0.19 | 1.06 | 1.00 | 1.29 | 1.11 |
| Aim | 1.00 | 0.89 | 1.08 | 1.41 | 1.00 | 0.74 | 0.60 | 0.58 | 1.63 | 1.00 | 1.26 | 0.95 |
| Ajuba | 1.00 | 1.00 | 1.00 | 1.25 | 1.00 | 1.00 | 0.62 | 0.11 | 0.80 | 1.00 | 1.00 | 1.00 |
| Ak1 | 0.31 | 0.31 | 0.40 | 1.00 | 1.19 | 1.01 | 1.25 | 0.91 | 1.34 | 1.00 | 1.00 | 1.00 |
| Ak4 | 1.17 | 1.00 | 1.38 | 1.36 | 1.46 | 1.25 | 0.57 | 0.19 | 0.71 | 1.00 | 1.01 | 1.00 |
| Akap10 | 1.11 | 0.97 | 1.00 | 0.72 | 1.00 | 0.85 | 0.85 | 0.27 | 0.98 | 0.45 | 0.89 | 1.14 |
| Akap2 | 1.34 | 1.69 | 1.74 | 0.99 | 1.70 | 0.98 | 1.37 | 0.35 | 1.52 | 1.00 | 1.00 | 1.00 |
| Akirin2 | 1.18 | 0.61 | 0.93 | 0.99 | 1.21 | 0.94 | 1.07 | 0.20 | 1.11 | 0.52 | 0.91 | 1.05 |
| Akr1b3 | 0.71 | 1.00 | 1.00 | 0.39 | 1.00 | 0.58 | 2.47 | 0.39 | 3.53 | 1.53 | 4.53 | 0.61 |
| Akr1b7 | 1.00 | 1.00 | 1.00 | 1.00 | 1.00 | 1.00 | 1.00 | 1.00 | 1.00 | 1.00 | 1.00 | 1.00 |
| Akr1c19 | 1.00 | 1.00 | 1.00 | 1.00 | 1.00 | 1.00 | 1.00 | 1.00 | 1.00 | 1.00 | 1.00 | 1.00 |
| Akr1c21 | 1.00 | 1.00 | 1.00 | 1.00 | 1.00 | 1.00 | 1.00 | 1.00 | 1.00 | 1.00 | 1.00 | 1.00 |
| Alas1 | 0.87 | 0.74 | 0.79 | 1.04 | 0.95 | 0.96 | 1.19 | 1.26 | 1.00 | 1.55 | 1.30 | 1.24 |

Fig. 35- 9

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Aldoart1 | 1.12 | 2.54 | 0.90 | 0.90 | 0.34 | 1.17 | 0.98 | 0.92 | 0.87 | 0.14 | 0.31 | 1.09 |
| Aldoart2 | 1.07 | 4.76 | 0.91 | 0.82 | 0.05 | 1.16 | 0.89 | 1.00 | 0.93 | 0.25 | 0.08 | 1.21 |
| Alg2 | 0.34 | 0.74 | 0.52 | 1.06 | 0.18 | 1.18 | 0.62 | 0.68 | 0.94 | 0.33 | 0.24 | 0.90 |
| Alox12 | 1.00 | 1.00 | 1.00 | 1.00 | 1.00 | 1.04 | 0.83 | 0.62 | 1.14 | 0.69 | 1.22 | 1.51 |
| Alox8 | 1.00 | 1.00 | 1.00 | 1.00 | 1.00 | 1.00 | 1.00 | 1.00 | 1.00 | 1.00 | 1.00 | 1.00 |
| Als2cl | 0.90 | 1.11 | 1.09 | 1.09 | 0.26 | 1.06 | 1.01 | 1.10 | 1.05 | 0.47 | 0.32 | 1.04 |
| Ammecr1 | 0.87 | 1.00 | 1.00 | 1.00 | 1.00 | 1.00 | 0.87 | 1.25 | 1.51 | 1.00 | 1.00 | 0.89 |
| Ammecr1l | 1.00 | 2.30 | 0.96 | 0.98 | 0.22 | 0.79 | 0.92 | 1.09 | 1.05 | 0.54 | 0.54 | 1.02 |
| Amotl2 | 0.83 | 1.15 | 1.09 | 1.26 | 0.17 | 1.13 | 1.20 | 1.27 | 1.26 | 0.37 | 0.19 | 1.09 |
| Angptl2 | 0.50 | 0.67 | 0.52 | 0.61 | 0.32 | 0.64 | 0.58 | 0.59 | 0.75 | 0.25 | 0.25 | 0.60 |
| Ankhd1 | 1.11 | 1.51 | 1.53 | 1.80 | 0.19 | 0.86 | 1.38 | 1.46 | 1.21 | 1.00 | 0.51 | 0.97 |
| Ankrd11 | 0.90 | 1.78 | 1.55 | 1.51 | 0.09 | 0.93 | 1.25 | 1.91 | 1.32 | 1.00 | 0.21 | 1.14 |
| Ankrd23 | 0.63 | 2.15 | 0.77 | 1.13 | 0.14 | 0.83 | 1.27 | 1.30 | 1.16 | 1.18 | 0.25 | 1.07 |
| Ankrd29 | 0.92 | 1.00 | 1.00 | 1.00 | 1.00 | 1.00 | 0.72 | 0.88 | 0.62 | 0.49 | 0.45 | 0.76 |
| Ankrd49 | 0.69 | 1.55 | 1.59 | 2.19 | 0.20 | 1.00 | 1.22 | 1.02 | 1.07 | 1.00 | 0.29 | 0.80 |
| Ankrd52 | 0.44 | 0.97 | 0.83 | 1.22 | 0.16 | 0.87 | 0.82 | 1.53 | 1.40 | 1.00 | 1.00 | 1.06 |
| Anln | 1.00 | 1.00 | 1.00 | 1.00 | 1.00 | 1.00 | 1.00 | 1.00 | 1.00 | 1.00 | 1.00 | 1.62 |
| Ano7 | 1.00 | 1.00 | 1.00 | 1.00 | 1.00 | 1.00 | 1.00 | 1.00 | 1.00 | 1.00 | 1.00 | 1.00 |
| Aox3 | 1.00 | 1.00 | 1.00 | 1.00 | 1.00 | 1.00 | 1.00 | 1.00 | 1.00 | 0.58 | 1.08 | 1.41 |
| Ap1ar | 0.75 | 1.83 | 0.87 | 0.86 | 0.16 | 0.86 | 0.94 | 1.01 | 0.85 | 0.36 | 0.16 | 1.14 |
| Apcdd1 | 0.69 | 1.00 | 1.16 | 0.55 | 0.61 | 0.48 | 0.88 | 1.00 | 0.98 | 1.00 | 0.40 | 0.75 |
| Aph1b | 0.72 | 1.00 | 0.97 | 3.05 | 0.99 | 0.88 | 1.11 | 1.01 | 0.95 | 1.20 | 0.68 | 0.90 |
| Apitd1 | 1.00 | 1.02 | 1.00 | 1.00 | 1.44 | 1.00 | 0.66 | 0.80 | 1.00 | 1.11 | 3.21 | 0.84 |
| Apmap | 1.24 | 2.01 | 1.48 | 0.73 | 0.65 | 1.28 | 0.90 | 0.86 | 0.88 | 0.41 | 0.61 | 0.94 |
| Apobec1 | 1.73 | 1.09 | 1.97 | 0.42 | 0.18 | 0.41 | 1.48 | 1.40 | 1.53 | 0.70 | 0.29 | 1.02 |
| Apol7a | 1.00 | 1.00 | 1.00 | 1.00 | 1.00 | 1.00 | 1.00 | 1.00 | 1.00 | 1.00 | 1.00 | 1.00 |
| Apol8 | 1.00 | 1.00 | 1.00 | 1.00 | 1.00 | 1.00 | 1.00 | 1.00 | 1.00 | 1.00 | 1.00 | 1.00 |
| Arap2 | 1.00 | 1.00 | 1.00 | 1.80 | 0.86 | 0.98 | 1.24 | 1.19 | 1.38 | 0.43 | 0.29 | 0.84 |
| Arfip1 | 0.86 | 2.83 | 1.10 | 1.47 | 0.27 | 0.96 | 0.91 | 0.99 | 0.84 | 0.36 | 0.40 | 0.88 |
| Arg1 | 1.00 | 1.00 | 1.00 | 1.00 | 1.00 | 1.00 | 1.47 | 1.00 | 1.00 | 0.56 | 0.84 | 0.60 |
| Arhgap24 | 1.35 | 1.67 | 1.74 | 0.87 | 0.22 | 0.41 | 1.60 | 1.98 | 1.30 | 0.38 | 0.23 | 0.67 |
| Arhgap29 | 0.63 | 0.95 | 0.93 | 1.50 | 0.44 | 0.91 | 0.78 | 0.84 | 0.90 | 0.36 | 0.31 | 0.87 |
| Arhgap30 | 1.00 | 1.00 | 1.00 | 1.00 | 1.00 | 1.00 | 0.93 | 0.94 | 1.59 | 0.47 | 0.28 | 0.90 |
| Arhgap31 | 0.71 | 1.34 | 1.37 | 1.46 | 0.36 | 0.95 | 1.08 | 1.26 | 1.36 | 0.56 | 0.57 | 1.17 |
| Arhgap40 | 1.00 | 1.00 | 1.00 | 1.00 | 1.00 | 1.00 | 1.00 | 1.00 | 1.00 | 1.00 | 0.74 | 2.21 |
| Arhgdig | 1.00 | 0.91 | 2.07 | 0.20 | 2.04 | 0.73 | 1.00 | 0.79 | 1.92 | 2.28 | 4.71 | 1.09 |
| Arhgef11 | 0.81 | 1.00 | 0.93 | 0.82 | 0.13 | 0.79 | 1.28 | 1.31 | 0.94 | 1.00 | 0.52 | 0.95 |
| Arhgef37 | 0.32 | 1.00 | 0.40 | 0.33 | 0.07 | 0.10 | 1.44 | 1.66 | 0.86 | 1.00 | 1.00 | 0.51 |
| Arid3b | 1.04 | 1.00 | 1.22 | 0.97 | 0.93 | 1.30 | 0.94 | 0.60 | 1.02 | 0.48 | 0.20 | 1.00 |
| Arl1 | 1.17 | 1.16 | 0.71 | 0.33 | 0.09 | 0.96 | 1.24 | 1.19 | 0.94 | 1.06 | 0.25 | 0.86 |
| Arl6ip5 | 1.09 | 1.87 | 0.98 | 1.61 | 0.55 | 1.25 | 0.89 | 0.76 | 0.86 | 0.26 | 0.33 | 0.99 |
| Arl6ip6 | 1.06 | 1.70 | 0.82 | 1.80 | 0.17 | 1.07 | 1.13 | 1.08 | 0.80 | 0.74 | 0.27 | 0.93 |
| Arl8a | 1.61 | 1.95 | 1.38 | 1.63 | 0.65 | 1.15 | 1.10 | 1.00 | 1.24 | 0.31 | 0.47 | 1.06 |
| Arl9 | 1.00 | 1.00 | 1.00 | 1.00 | 1.00 | 1.00 | 1.00 | 1.00 | 1.00 | 1.00 | 1.00 | 1.00 |
| Armcx1 | 0.85 | 1.18 | 0.91 | 2.06 | 0.37 | 0.74 | 0.75 | 0.66 | 0.96 | 0.61 | 0.30 | 0.85 |
| Armcx5 | 0.80 | 2.28 | 1.18 | 3.44 | 0.30 | 1.56 | 1.09 | 1.41 | 0.96 | 1.00 | 0.30 | 1.04 |
| Art4 | 1.00 | 1.00 | 1.00 | 1.00 | 1.00 | 1.00 | 0.16 | 0.14 | 0.12 | 0.30 | 0.38 | 0.80 |
| Arxes1 | 0.83 | 1.00 | 1.54 | 0.42 | 0.42 | 0.85 | 1.00 | 1.00 | 1.09 | 1.00 | 0.92 | 0.70 |
| Asap2 | 1.19 | 1.00 | 1.22 | 2.16 | 0.27 | 1.34 | 1.47 | 1.49 | 1.39 | 0.60 | 0.32 | 0.92 |
| Asb13 | 0.77 | 1.08 | 0.84 | 1.52 | 0.77 | 0.95 | 0.92 | 1.13 | 0.99 | 0.60 | 0.73 | 1.18 |
| Asb17os | 1.00 | 1.00 | 1.00 | 1.00 | 1.00 | 1.00 | 1.00 | 1.00 | 1.00 | 1.00 | 1.00 | 1.00 |
| Asf1b | 1.00 | 1.00 | 1.40 | 0.31 | 0.32 | 0.81 | 0.79 | 0.42 | 0.96 | 0.89 | 0.49 | 0.85 |
| Atad2b | 0.88 | 1.00 | 1.03 | 2.90 | 0.43 | 1.07 | 0.80 | 1.13 | 1.04 | 0.95 | 0.49 | 0.97 |
| Atg4a | 0.91 | 2.54 | 0.93 | 1.76 | 0.19 | 0.94 | 0.97 | 1.09 | 1.04 | 1.00 | 0.24 | 0.86 |
| Atg4c | 0.42 | 1.00 | 0.49 | 1.11 | 0.16 | 0.72 | 0.90 | 0.68 | 0.82 | 0.68 | 0.33 | 0.99 |
| Atn1 | 0.90 | 1.38 | 0.92 | 1.15 | 0.17 | 0.83 | 1.07 | 0.94 | 0.98 | 0.50 | 0.54 | 0.98 |
| Atp11b | 0.71 | 1.38 | 0.99 | 2.93 | 0.82 | 1.28 | 0.98 | 1.15 | 0.83 | 0.45 | 0.47 | 1.05 |
| Atp1b1 | 0.40 | 0.46 | 0.60 | 0.60 | 0.15 | 0.68 | 0.82 | 0.92 | 1.04 | 1.26 | 1.49 | 1.38 |
| Atp1b2 | 0.66 | 0.92 | 0.70 | 1.77 | 0.16 | 1.32 | 0.97 | 0.88 | 0.88 | 0.63 | 0.40 | 1.10 |
| Atp4b | 1.00 | 1.00 | 1.00 | 1.00 | 1.00 | 1.00 | 1.00 | 1.00 | 1.00 | 0.18 | 1.00 | 1.00 |
| Atp5j | 1.00 | 1.11 | 0.75 | 0.57 | 0.95 | 0.95 | 0.81 | 0.82 | 0.75 | 0.39 | 0.60 | 0.90 |
| Atp6v0d2 | 1.00 | 1.00 | 1.00 | 1.00 | 1.00 | 1.00 | 1.00 | 1.00 | 1.00 | 1.41 | 1.66 | 1.08 |
| Atp6v1a | 1.42 | 2.28 | 1.16 | 0.97 | 0.16 | 1.02 | 0.92 | 0.95 | 0.96 | 0.25 | 0.34 | 1.01 |
| Atp6v1h | 2.40 | 2.15 | 1.89 | 0.98 | 0.53 | 1.06 | 1.11 | 1.14 | 1.24 | 0.54 | 0.61 | 0.97 |

Fig. 35- 10

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Aldoart1 | 1.00 | 1.20 | 1.03 | 1.02 | 3.00 | 1.03 | 1.73 | 0.39 | 1.40 | 1.01 | 1.02 | 0.99 |
| Aldoart2 | 0.86 | 1.10 | 0.98 | 1.11 | 1.71 | 1.06 | 1.78 | 1.00 | 1.88 | 0.96 | 0.71 | 1.00 |
| Alg2 | 0.70 | 0.64 | 1.14 | 1.10 | 1.29 | 1.01 | 1.12 | 1.07 | 1.18 | 0.84 | 0.65 | 0.84 |
| Alox12 | 1.00 | 1.00 | 1.00 | 0.68 | 1.00 | 0.71 | 1.00 | 1.00 | 1.00 | 1.00 | 1.00 | 1.00 |
| Alox8 | 1.00 | 1.00 | 1.00 | 1.00 | 1.00 | 1.00 | 1.00 | 1.00 | 1.00 | 1.00 | 1.00 | 1.00 |
| Als2cl | 0.99 | 1.10 | 1.20 | 0.99 | 1.27 | 1.05 | 0.77 | 0.73 | 1.05 | 0.83 | 0.57 | 0.80 |
| Ammecr1 | 0.23 | 0.16 | 0.63 | 0.90 | 1.00 | 0.88 | 1.00 | 1.00 | 1.00 | 0.98 | 0.90 | 0.89 |
| Ammecr1l | 0.81 | 0.69 | 1.03 | 1.08 | 1.10 | 1.02 | 1.23 | 0.49 | 0.98 | 1.02 | 0.67 | 1.01 |
| Amotl2 | 1.30 | 1.03 | 1.31 | 0.92 | 0.71 | 1.24 | 0.58 | 0.61 | 0.83 | 1.04 | 0.70 | 1.25 |
| Angptl2 | 0.63 | 0.58 | 0.85 | 0.65 | 1.12 | 0.76 | 0.74 | 0.92 | 1.08 | 0.64 | 0.55 | 0.74 |
| Ankhd1 | 0.57 | 0.44 | 0.84 | 1.20 | 1.00 | 1.00 | 0.83 | 1.00 | 0.93 | 0.95 | 0.43 | 0.88 |
| Ankrd11 | 0.58 | 0.45 | 0.92 | 1.16 | 1.00 | 1.16 | 0.90 | 1.00 | 1.28 | 1.01 | 0.46 | 0.88 |
| Ankrd23 | 1.01 | 1.22 | 1.10 | 0.85 | 1.00 | 0.92 | 0.86 | 1.00 | 0.64 | 0.81 | 0.79 | 0.95 |
| Ankrd29 | 0.80 | 0.77 | 0.79 | 1.03 | 1.03 | 1.10 | 1.00 | 1.00 | 1.00 | 1.00 | 1.00 | 1.00 |
| Ankrd49 | 0.78 | 0.69 | 1.04 | 1.10 | 1.00 | 0.82 | 1.58 | 1.00 | 1.48 | 0.81 | 0.51 | 0.86 |
| Ankrd52 | 0.52 | 0.36 | 0.98 | 1.22 | 1.00 | 1.18 | 1.02 | 1.00 | 1.21 | 1.03 | 0.29 | 0.83 |
| Anln | 0.41 | 0.45 | 0.61 | 1.00 | 1.00 | 1.00 | 1.00 | 1.00 | 1.00 | 1.31 | 0.75 | 0.90 |
| Ano7 | 1.00 | 1.00 | 1.00 | 1.00 | 1.00 | 1.00 | 1.00 | 1.00 | 1.00 | 1.30 | 1.00 | 1.27 |
| Aox3 | 1.00 | 1.00 | 1.00 | 1.00 | 1.00 | 1.00 | 0.26 | 0.17 | 0.38 | 1.00 | 1.00 | 1.00 |
| Ap1ar | 0.92 | 0.92 | 1.10 | 0.87 | 2.35 | 1.08 | 0.86 | 1.00 | 0.77 | 0.80 | 0.57 | 0.98 |
| Apcdd1 | 1.09 | 0.57 | 1.32 | 0.65 | 1.00 | 0.56 | 1.00 | 1.00 | 1.00 | 1.31 | 0.50 | 0.80 |
| Aph1b | 1.26 | 1.00 | 1.00 | 1.28 | 0.93 | 0.98 | 0.77 | 1.00 | 1.09 | 1.17 | 0.85 | 0.86 |
| Apitd1 | 0.41 | 0.41 | 0.62 | 1.00 | 0.18 | 1.00 | 1.00 | 1.00 | 1.00 | 1.00 | 1.19 | 0.81 |
| Apmap | 1.08 | 1.07 | 0.95 | 0.85 | 1.20 | 0.93 | 0.86 | 0.19 | 0.82 | 1.01 | 1.08 | 1.10 |
| Apobec1 | 1.17 | 0.95 | 1.21 | 1.00 | 1.00 | 0.93 | 0.73 | 0.72 | 0.55 | 0.96 | 0.83 | 0.79 |
| Apol7a | 1.00 | 1.00 | 1.00 | 1.00 | 1.00 | 1.00 | 0.26 | 0.17 | 0.59 | 1.69 | 1.71 | 1.64 |
| Apol8 | 1.00 | 1.00 | 1.00 | 1.00 | 1.00 | 1.00 | 1.00 | 1.00 | 1.00 | 1.00 | 1.00 | 1.00 |
| Arap2 | 1.22 | 1.12 | 1.17 | 1.30 | 1.82 | 1.14 | 1.24 | 1.00 | 0.91 | 1.10 | 0.78 | 0.99 |
| Arfip1 | 0.85 | 0.88 | 0.92 | 1.09 | 1.29 | 0.89 | 1.27 | 0.89 | 1.16 | 1.06 | 0.90 | 0.99 |
| Arg1 | 4.93 | 1.48 | 2.14 | 1.00 | 1.00 | 1.00 | 1.66 | 0.62 | 1.31 | 1.00 | 1.00 | 0.58 |
| Arhgap24 | 1.47 | 1.07 | 0.89 | 0.86 | 1.38 | 0.73 | 0.71 | 1.00 | 0.59 | 1.11 | 1.06 | 1.08 |
| Arhgap29 | 0.78 | 0.69 | 0.80 | 0.91 | 1.09 | 0.92 | 0.51 | 0.44 | 0.57 | 0.82 | 0.63 | 0.87 |
| Arhgap30 | 0.65 | 0.57 | 0.93 | 0.72 | 1.00 | 0.87 | 0.90 | 1.00 | 1.00 | 0.82 | 0.57 | 0.93 |
| Arhgap31 | 0.74 | 0.59 | 1.07 | 1.14 | 1.00 | 1.13 | 0.86 | 1.00 | 1.22 | 0.95 | 0.67 | 1.00 |
| Arhgap40 | 1.00 | 1.00 | 1.00 | 1.00 | 1.00 | 1.00 | 1.00 | 1.00 | 1.00 | 1.00 | 1.00 | 1.00 |
| Arhgdig | 1.00 | 1.00 | 1.00 | 1.05 | 0.86 | 0.83 | 1.00 | 1.00 | 1.00 | 1.25 | 2.74 | 1.99 |
| Arhgef11 | 0.74 | 0.72 | 0.99 | 1.08 | 1.00 | 0.97 | 0.90 | 1.00 | 0.87 | 0.95 | 0.47 | 1.00 |
| Arhgef37 | 0.14 | 0.08 | 0.16 | 1.03 | 1.00 | 0.50 | 0.44 | 1.00 | 0.40 | 0.49 | 0.25 | 0.43 |
| Arid3b | 0.61 | 0.65 | 0.78 | 0.84 | 1.00 | 1.29 | 0.60 | 1.00 | 0.87 | 0.87 | 0.79 | 1.06 |
| Arl1 | 0.78 | 0.93 | 0.95 | 0.88 | 0.97 | 0.97 | 1.26 | 1.00 | 1.21 | 0.99 | 0.57 | 1.02 |
| Arl6ip5 | 1.35 | 1.47 | 1.35 | 0.82 | 1.87 | 0.97 | 1.02 | 0.29 | 1.00 | 1.01 | 1.10 | 1.08 |
| Arl6ip6 | 0.72 | 0.59 | 0.83 | 0.74 | 1.14 | 0.87 | 0.96 | 1.00 | 1.16 | 0.92 | 0.67 | 1.00 |
| Arl8a | 1.13 | 1.07 | 1.20 | 1.13 | 3.42 | 1.06 | 1.30 | 0.33 | 1.15 | 1.01 | 1.11 | 1.11 |
| Arl9 | 1.00 | 1.00 | 1.00 | 1.00 | 1.00 | 1.00 | 1.00 | 1.00 | 1.00 | 1.00 | 1.00 | 1.00 |
| Armcx1 | 1.21 | 0.95 | 1.01 | 0.86 | 0.90 | 0.78 | 0.70 | 1.00 | 0.88 | 0.93 | 0.93 | 1.11 |
| Armcx5 | 1.03 | 1.00 | 1.04 | 1.31 | 1.00 | 0.96 | 2.65 | 1.00 | 1.33 | 1.07 | 0.74 | 1.21 |
| Art4 | 0.58 | 0.47 | 0.48 | 0.38 | 0.83 | 0.46 | 0.95 | 1.39 | 0.98 | 1.00 | 1.00 | 1.00 |
| Arxes1 | 0.64 | 0.57 | 0.52 | 1.00 | 1.00 | 1.00 | 1.00 | 1.00 | 1.00 | 0.80 | 1.00 | 1.00 |
| Asap2 | 1.02 | 0.66 | 1.11 | 0.92 | 1.00 | 0.93 | 1.53 | 1.00 | 1.43 | 1.00 | 0.64 | 1.00 |
| Asb13 | 1.13 | 1.09 | 1.29 | 1.48 | 1.56 | 1.19 | 0.79 | 0.58 | 0.79 | 0.96 | 0.81 | 1.02 |
| Asb17os | 0.29 | 0.35 | 0.28 | 1.00 | 0.98 | 1.00 | 1.00 | 1.00 | 1.00 | 1.00 | 1.00 | 1.00 |
| Asf1b | 0.34 | 0.48 | 0.47 | 1.00 | 1.00 | 1.00 | 1.00 | 1.00 | 1.00 | 0.83 | 0.80 | 0.87 |
| Atad2b | 0.57 | 0.53 | 0.84 | 0.97 | 1.00 | 0.83 | 1.14 | 1.00 | 1.09 | 1.00 | 0.58 | 0.94 |
| Atg4a | 0.75 | 0.54 | 1.08 | 1.14 | 1.00 | 1.08 | 0.81 | 1.00 | 0.74 | 1.15 | 0.52 | 0.86 |
| Atg4c | 1.22 | 0.90 | 1.50 | 1.14 | 1.00 | 0.87 | 0.77 | 1.00 | 0.89 | 0.71 | 0.66 | 0.84 |
| Atn1 | 1.00 | 0.78 | 1.32 | 1.05 | 1.45 | 0.98 | 1.10 | 0.86 | 1.10 | 1.04 | 0.63 | 0.95 |
| Atp11b | 0.78 | 0.76 | 0.99 | 1.09 | 1.02 | 0.97 | 1.10 | 1.24 | 0.85 | 1.04 | 0.84 | 1.03 |
| Atp1b1 | 1.13 | 1.17 | 1.20 | 0.76 | 1.00 | 0.87 | 1.56 | 2.32 | 0.84 | 1.19 | 1.17 | 1.11 |
| Atp1b2 | 1.11 | 0.84 | 1.25 | 0.68 | 1.53 | 0.74 | 1.00 | 1.00 | 1.00 | 0.89 | 0.78 | 0.94 |
| Atp4b | 1.00 | 1.00 | 1.00 | 1.00 | 1.00 | 1.00 | 1.00 | 1.00 | 1.00 | 1.00 | 1.00 | 1.00 |
| Atp5j | 0.90 | 1.06 | 0.88 | 0.83 | 1.46 | 0.78 | 0.89 | 0.37 | 0.81 | 0.98 | 1.33 | 1.00 |
| Atp6v0d2 | 2.50 | 2.27 | 2.15 | 0.97 | 1.19 | 1.06 | 1.00 | 1.00 | 1.00 | 1.00 | 1.00 | 1.00 |
| Atp6v1a | 1.06 | 0.96 | 1.13 | 1.11 | 2.17 | 1.08 | 0.75 | 0.58 | 0.79 | 1.01 | 0.79 | 0.95 |
| Atp6v1h | 0.96 | 1.06 | 1.02 | 0.93 | 2.34 | 0.95 | 1.07 | 0.51 | 1.01 | 1.07 | 1.19 | 1.15 |

Fig. 35-11

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Aldoart1 | 1.03 | 1.01 | 0.90 | 1.21 | 0.21 | 1.20 | 0.98 | 0.34 | 0.91 | 0.98 | 1.20 | 0.92 |
| Aldoart2 | 1.07 | 1.20 | 0.90 | 1.22 | 0.15 | 1.09 | 1.01 | 0.83 | 1.02 | 0.94 | 1.20 | 0.82 |
| Alg2 | 1.04 | 1.00 | 1.19 | 1.03 | 0.44 | 1.02 | 0.79 | 0.63 | 0.75 | 1.01 | 0.94 | 1.14 |
| Alox12 | 1.23 | 0.94 | 1.39 | 1.03 | 0.99 | 2.05 | 0.95 | 1.06 | 1.03 | 1.30 | 0.85 | 0.72 |
| Alox8 | 1.00 | 1.00 | 1.00 | 1.00 | 1.00 | 1.00 | 1.00 | 1.00 | 1.00 | 1.00 | 1.00 | 1.00 |
| Als2cl | 0.90 | 0.85 | 0.85 | 1.05 | 0.25 | 1.10 | 1.00 | 1.00 | 1.14 | 0.78 | 0.70 | 1.03 |
| Ammecr1 | 0.83 | 0.84 | 0.66 | 1.00 | 1.00 | 0.78 | 1.85 | 1.00 | 0.95 | 0.69 | 0.32 | 0.82 |
| Ammecr1l | 0.84 | 0.87 | 0.86 | 0.99 | 0.52 | 0.96 | 1.07 | 0.49 | 0.97 | 1.03 | 0.68 | 1.08 |
| Amotl2 | 1.25 | 1.25 | 1.11 | 0.67 | 0.11 | 0.63 | 0.50 | 1.00 | 0.70 | 1.01 | 0.95 | 1.39 |
| Angptl2 | 0.52 | 0.63 | 0.72 | 0.60 | 0.51 | 0.57 | 0.96 | 1.38 | 1.15 | 0.54 | 0.47 | 0.75 |
| Ankhd1 | 0.93 | 0.92 | 0.83 | 1.13 | 0.31 | 0.80 | 1.36 | 1.00 | 1.19 | 0.94 | 0.53 | 1.13 |
| Ankrd11 | 0.95 | 1.03 | 0.74 | 1.14 | 0.15 | 0.86 | 1.28 | 1.14 | 1.17 | 0.91 | 0.61 | 1.19 |
| Ankrd23 | 1.12 | 1.50 | 1.49 | 0.87 | 1.00 | 0.54 | 0.83 | 1.00 | 1.04 | 1.31 | 1.02 | 1.16 |
| Ankrd29 | 1.00 | 1.00 | 1.00 | 0.95 | 1.00 | 0.61 | 1.00 | 1.00 | 1.00 | 0.69 | 1.00 | 0.96 |
| Ankrd49 | 0.90 | 1.09 | 0.79 | 1.10 | 0.61 | 0.87 | 1.00 | 0.59 | 0.86 | 1.09 | 0.63 | 1.04 |
| Ankrd52 | 0.96 | 0.84 | 0.71 | 1.21 | 0.35 | 0.97 | 1.23 | 1.00 | 1.12 | 0.80 | 0.44 | 1.07 |
| Anln | 0.84 | 0.56 | 0.79 | 0.48 | 1.00 | 0.55 | 1.05 | 0.81 | 0.89 | 0.58 | 0.97 | 0.55 |
| Ano7 | 0.83 | 0.76 | 0.68 | 1.00 | 1.00 | 1.00 | 1.00 | 1.00 | 1.00 | 1.00 | 1.00 | 1.00 |
| Aox3 | 1.00 | 1.00 | 1.18 | 0.59 | 1.00 | 0.83 | 1.18 | 0.58 | 1.08 | 1.00 | 1.00 | 1.00 |
| Ap1ar | 0.82 | 0.78 | 0.93 | 1.00 | 1.00 | 1.05 | 1.07 | 1.00 | 1.08 | 0.98 | 0.83 | 0.97 |
| Apcdd1 | 0.76 | 0.92 | 0.84 | 0.14 | 0.09 | 0.43 | 1.15 | 1.00 | 1.04 | 0.50 | 0.59 | 0.46 |
| Aph1b | 0.88 | 1.08 | 0.90 | 0.95 | 0.65 | 0.65 | 1.22 | 2.20 | 0.97 | 1.16 | 1.16 | 1.05 |
| Apitd1 | 0.71 | 0.49 | 0.47 | 0.97 | 1.00 | 1.00 | 0.90 | 1.77 | 1.10 | 1.14 | 1.23 | 1.21 |
| Apmap | 0.92 | 0.90 | 0.96 | 1.08 | 0.80 | 1.68 | 1.06 | 0.33 | 0.69 | 1.18 | 1.15 | 0.99 |
| Apobec1 | 0.57 | 0.62 | 0.43 | 0.61 | 0.28 | 0.37 | 1.00 | 1.00 | 1.19 | 1.46 | 1.36 | 1.28 |
| Apol7a | 1.32 | 1.76 | 0.77 | 1.00 | 1.00 | 1.00 | 1.00 | 1.00 | 1.00 | 1.00 | 1.00 | 1.00 |
| Apol8 | 1.00 | 1.00 | 1.00 | 1.00 | 1.00 | 1.00 | 1.00 | 1.00 | 1.00 | 0.36 | 0.36 | 0.22 |
| Arap2 | 0.93 | 0.81 | 0.66 | 1.20 | 1.00 | 1.03 | 0.97 | 0.89 | 0.98 | 1.39 | 0.98 | 1.30 |
| Arfip1 | 0.85 | 0.75 | 0.77 | 0.94 | 0.70 | 0.98 | 0.97 | 1.00 | 0.97 | 1.12 | 0.75 | 1.05 |
| Arg1 | 1.79 | 1.54 | 1.37 | 1.00 | 1.00 | 1.00 | 1.00 | 1.00 | 1.00 | 1.00 | 1.00 | 1.00 |
| Arhgap24 | 0.95 | 1.05 | 1.09 | 0.75 | 0.67 | 0.65 | 0.65 | 1.00 | 0.88 | 0.98 | 0.82 | 0.99 |
| Arhgap29 | 1.07 | 0.98 | 1.00 | 0.75 | 0.17 | 0.66 | 1.12 | 1.34 | 1.09 | 0.72 | 0.52 | 0.87 |
| Arhgap30 | 1.41 | 1.03 | 1.41 | 0.74 | 0.62 | 0.64 | 0.93 | 1.00 | 1.02 | 0.81 | 0.57 | 0.93 |
| Arhgap31 | 1.09 | 1.27 | 1.18 | 1.06 | 0.13 | 0.94 | 1.36 | 1.00 | 1.15 | 0.85 | 0.66 | 1.01 |
| Arhgap40 | 0.51 | 0.46 | 0.73 | 1.00 | 1.00 | 1.00 | 1.00 | 1.00 | 1.00 | 1.00 | 1.00 | 1.00 |
| Arhgdig | 1.06 | 1.33 | 1.03 | 0.98 | 0.96 | 2.08 | 1.26 | 1.56 | 0.51 | 1.00 | 1.96 | 1.00 |
| Arhgef11 | 1.10 | 1.10 | 1.05 | 1.05 | 1.00 | 0.89 | 1.12 | 1.00 | 0.97 | 0.95 | 0.77 | 0.99 |
| Arhgef37 | 0.76 | 0.88 | 0.48 | 0.46 | 0.12 | 0.20 | 0.32 | 1.62 | 0.41 | 0.13 | 0.16 | 0.10 |
| Arid3b | 0.96 | 0.94 | 0.79 | 0.73 | 1.00 | 0.98 | 1.15 | 0.61 | 1.10 | 0.92 | 0.60 | 1.01 |
| Arl1 | 0.85 | 0.94 | 0.91 | 0.88 | 0.42 | 0.83 | 0.82 | 1.60 | 0.93 | 0.80 | 0.79 | 1.15 |
| Arl6ip5 | 1.04 | 1.08 | 1.09 | 1.09 | 0.30 | 1.04 | 1.18 | 0.47 | 0.70 | 1.03 | 0.99 | 1.05 |
| Arl6ip6 | 0.86 | 0.84 | 0.85 | 1.07 | 1.00 | 1.06 | 0.99 | 0.58 | 1.05 | 1.04 | 0.71 | 0.94 |
| Arl8a | 1.11 | 1.21 | 1.19 | 0.97 | 0.43 | 1.21 | 0.92 | 0.17 | 0.92 | 0.98 | 1.04 | 0.93 |
| Arl9 | 1.00 | 1.00 | 1.00 | 1.14 | 1.00 | 1.00 | 0.99 | 0.20 | 0.96 | 1.00 | 1.00 | 1.00 |
| Armcx1 | 1.01 | 0.72 | 1.14 | 0.87 | 1.39 | 0.97 | 1.06 | 1.00 | 0.63 | 0.86 | 1.32 | 0.83 |
| Armcx5 | 1.05 | 1.11 | 1.21 | 0.97 | 0.52 | 0.99 | 0.86 | 1.00 | 1.01 | 1.20 | 0.95 | 1.14 |
| Art4 | 0.53 | 0.70 | 1.00 | 1.97 | 1.00 | 1.13 | 0.58 | 0.94 | 0.52 | 0.61 | 0.45 | 0.60 |
| Arxes1 | 0.80 | 1.00 | 0.96 | 0.28 | 0.16 | 0.49 | 1.00 | 1.00 | 1.42 | 1.06 | 3.85 | 1.00 |
| Asap2 | 0.86 | 0.83 | 0.68 | 1.21 | 0.59 | 0.96 | 1.14 | 1.00 | 1.02 | 1.07 | 0.90 | 1.02 |
| Asb13 | 1.51 | 1.55 | 1.15 | 0.85 | 0.55 | 1.15 | 0.91 | 1.00 | 1.02 | 1.40 | 1.05 | 1.28 |
| Asb17os | 1.00 | 1.00 | 1.00 | 1.00 | 1.00 | 1.00 | 0.87 | 0.88 | 0.93 | 0.11 | 0.40 | 0.17 |
| Asf1b | 0.53 | 0.34 | 0.65 | 0.74 | 1.00 | 0.63 | 1.00 | 0.69 | 1.06 | 0.67 | 0.66 | 0.56 |
| Atad2b | 0.88 | 0.76 | 0.76 | 1.04 | 0.87 | 0.80 | 1.07 | 1.00 | 0.92 | 0.95 | 0.56 | 0.97 |
| Atg4a | 0.99 | 0.74 | 1.06 | 0.96 | 1.00 | 0.72 | 1.14 | 1.00 | 0.88 | 0.69 | 0.52 | 0.87 |
| Atg4c | 0.96 | 0.63 | 1.12 | 0.81 | 0.64 | 0.76 | 0.95 | 1.26 | 1.07 | 0.79 | 0.73 | 0.92 |
| Atn1 | 1.07 | 1.23 | 1.06 | 0.99 | 0.21 | 1.03 | 0.83 | 0.73 | 0.96 | 0.78 | 0.75 | 0.89 |
| Atp11b | 0.84 | 0.80 | 0.82 | 1.72 | 0.60 | 1.10 | 1.05 | 0.48 | 0.97 | 1.16 | 0.79 | 1.04 |
| Atp1b1 | 1.41 | 1.60 | 1.26 | 0.78 | 1.01 | 1.64 | 0.99 | 0.62 | 0.87 | 1.45 | 3.76 | 1.36 |
| Atp1b2 | 0.97 | 0.79 | 1.51 | 0.81 | 0.76 | 0.98 | 0.95 | 0.47 | 0.92 | 1.16 | 2.87 | 0.80 |
| Atp4b | 1.29 | 1.47 | 1.29 | 1.00 | 1.00 | 1.00 | 1.00 | 1.00 | 1.00 | 1.00 | 1.00 | 1.00 |
| Atp5j | 0.98 | 0.99 | 0.94 | 0.80 | 0.84 | 0.95 | 0.98 | 0.20 | 0.94 | 0.97 | 1.33 | 1.03 |
| Atp6v0d2 | 0.28 | 0.19 | 0.19 | 0.21 | 1.00 | 0.09 | 1.00 | 1.00 | 1.00 | 1.00 | 1.00 | 0.63 |
| Atp6v1a | 0.95 | 0.94 | 0.94 | 0.74 | 0.21 | 0.61 | 1.06 | 0.45 | 0.97 | 0.91 | 1.18 | 0.89 |
| Atp6v1h | 0.91 | 0.88 | 0.85 | 1.18 | 0.96 | 1.03 | 0.91 | 0.16 | 1.11 | 1.24 | 1.04 | 1.01 |

Fig. 35-12

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Aldoart1 | 0.86 | 0.82 | 0.85 | 1.15 | 1.37 | 1.03 | 1.31 | 0.07 | 1.33 | 0.36 | 1.04 | 1.01 |
| Aldoart2 | 1.00 | 0.91 | 0.77 | 1.13 | 0.24 | 0.98 | 1.41 | 0.06 | 1.46 | 0.15 | 0.89 | 0.91 |
| Alg2 | 0.93 | 1.16 | 1.12 | 1.07 | 2.11 | 1.04 | 0.60 | 0.17 | 1.02 | 0.37 | 0.74 | 1.27 |
| Alox12 | 1.00 | 1.00 | 1.00 | 1.00 | 1.00 | 1.00 | 0.46 | 0.18 | 0.31 | 0.93 | 0.61 | 1.98 |
| Alox8 | 1.00 | 1.00 | 1.00 | 1.00 | 0.93 | 1.00 | 0.19 | 0.43 | 0.26 | 1.00 | 1.00 | 1.00 |
| Als2cl | 0.85 | 0.78 | 1.04 | 0.86 | 1.00 | 1.03 | 0.83 | 0.14 | 0.97 | 1.00 | 1.11 | 1.00 |
| Ammecr1 | 1.00 | 1.00 | 1.00 | 1.07 | 1.00 | 1.07 | 0.60 | 0.53 | 0.85 | 1.00 | 0.49 | 0.44 |
| Ammecr1l | 1.08 | 1.32 | 1.07 | 0.94 | 0.82 | 0.92 | 1.05 | 0.14 | 1.17 | 0.47 | 0.92 | 0.96 |
| Amotl2 | 1.12 | 0.97 | 1.23 | 0.98 | 1.00 | 0.99 | 0.73 | 0.19 | 0.83 | 1.00 | 0.62 | 0.92 |
| Angptl2 | 0.38 | 0.50 | 0.46 | 0.69 | 1.00 | 0.68 | 0.83 | 0.11 | 0.90 | 1.00 | 0.71 | 0.47 |
| Ankhd1 | 0.80 | 0.82 | 0.97 | 0.76 | 1.00 | 0.88 | 0.80 | 0.17 | 0.94 | 0.70 | 0.79 | 0.87 |
| Ankrd11 | 1.16 | 1.66 | 1.18 | 0.82 | 0.99 | 0.89 | 0.77 | 0.04 | 1.08 | 0.32 | 0.83 | 0.66 |
| Ankrd23 | 1.30 | 1.05 | 1.55 | 1.13 | 1.00 | 0.98 | 1.42 | 0.04 | 1.52 | 0.61 | 1.17 | 1.38 |
| Ankrd29 | 1.00 | 1.00 | 1.00 | 0.98 | 0.19 | 0.93 | 0.53 | 0.16 | 0.64 | 1.00 | 1.00 | 1.00 |
| Ankrd49 | 1.12 | 0.72 | 0.86 | 1.18 | 1.00 | 0.96 | 0.81 | 0.11 | 0.77 | 0.19 | 0.74 | 0.81 |
| Ankrd52 | 0.77 | 0.78 | 1.09 | 0.87 | 1.00 | 0.90 | 0.78 | 0.09 | 1.14 | 0.77 | 0.53 | 0.52 |
| Anln | 1.00 | 1.00 | 1.00 | 0.90 | 1.00 | 0.92 | 0.63 | 0.18 | 0.91 | 0.31 | 0.89 | 0.95 |
| Ano7 | 1.00 | 1.00 | 1.00 | 1.00 | 1.00 | 1.00 | 0.33 | 0.14 | 0.28 | 1.00 | 1.00 | 1.00 |
| Aox3 | 1.00 | 1.00 | 1.00 | 1.00 | 1.00 | 1.00 | 1.00 | 1.00 | 1.00 | 1.00 | 1.00 | 1.00 |
| Ap1ar | 0.94 | 1.03 | 0.84 | 1.00 | 0.56 | 1.02 | 0.83 | 0.03 | 0.84 | 0.15 | 0.65 | 0.78 |
| Apcdd1 | 1.00 | 1.00 | 1.00 | 0.98 | 1.00 | 0.74 | 1.32 | 0.03 | 1.34 | 1.00 | 1.00 | 1.30 |
| Aph1b | 1.00 | 1.00 | 1.00 | 1.05 | 1.48 | 0.94 | 0.74 | 0.18 | 1.00 | 0.89 | 1.28 | 1.15 |
| Apitd1 | 1.00 | 1.00 | 1.00 | 2.13 | 0.88 | 1.47 | 0.78 | 2.69 | 0.55 | 2.39 | 0.77 | 1.15 |
| Apmap | 0.55 | 0.81 | 0.82 | 1.18 | 1.80 | 1.08 | 1.27 | 0.26 | 1.24 | 0.70 | 1.15 | 1.17 |
| Apobec1 | 1.00 | 1.15 | 1.00 | 1.00 | 1.00 | 0.71 | 0.96 | 0.26 | 1.12 | 0.56 | 1.34 | 1.34 |
| Apol7a | 1.16 | 1.12 | 0.74 | 1.00 | 1.00 | 1.00 | 1.94 | 2.15 | 2.04 | 1.00 | 1.00 | 1.00 |
| Apol8 | 1.00 | 1.00 | 1.00 | 0.87 | 1.00 | 0.92 | 1.22 | 0.62 | 1.09 | 0.14 | 0.73 | 0.66 |
| Arap2 | 1.00 | 1.00 | 1.00 | 0.85 | 0.59 | 0.86 | 0.88 | 0.16 | 0.92 | 0.92 | 1.21 | 0.97 |
| Arfip1 | 1.05 | 1.25 | 1.00 | 0.97 | 1.00 | 0.93 | 0.75 | 0.17 | 0.88 | 0.39 | 0.92 | 1.22 |
| Arg1 | 1.00 | 1.00 | 1.00 | 1.00 | 1.00 | 1.00 | 1.38 | 0.18 | 1.61 | 1.00 | 1.00 | 1.00 |
| Arhgap24 | 1.92 | 1.06 | 0.84 | 1.23 | 0.56 | 0.99 | 0.90 | 0.15 | 1.00 | 0.91 | 1.22 | 0.85 |
| Arhgap29 | 0.79 | 1.04 | 0.87 | 0.80 | 1.00 | 0.78 | 0.65 | 0.28 | 0.71 | 1.00 | 1.00 | 1.00 |
| Arhgap30 | 1.00 | 1.00 | 1.00 | 0.75 | 1.00 | 0.87 | 0.93 | 0.17 | 1.25 | 0.49 | 0.96 | 0.97 |
| Arhgap31 | 0.96 | 1.38 | 1.01 | 1.06 | 1.00 | 0.98 | 1.13 | 0.31 | 1.50 | 1.00 | 1.21 | 1.18 |
| Arhgap40 | 1.00 | 1.00 | 1.00 | 1.00 | 1.00 | 1.00 | 0.90 | 0.11 | 0.77 | 1.00 | 1.00 | 1.00 |
| Arhgdig | 1.33 | 1.76 | 1.67 | 1.13 | 1.00 | 1.15 | 1.00 | 2.72 | 1.13 | 1.00 | 1.00 | 1.00 |
| Arhgef11 | 0.94 | 1.07 | 1.01 | 1.08 | 1.00 | 0.99 | 0.94 | 0.13 | 1.10 | 1.00 | 0.99 | 0.95 |
| Arhgef37 | 1.69 | 2.14 | 1.09 | 0.41 | 1.15 | 0.31 | 0.37 | 0.05 | 0.50 | 0.87 | 0.15 | 0.13 |
| Arid3b | 1.00 | 1.00 | 1.00 | 0.66 | 1.00 | 0.86 | 1.00 | 1.00 | 1.00 | 0.48 | 1.01 | 1.08 |
| Arl1 | 0.92 | 1.32 | 0.70 | 1.14 | 1.00 | 0.95 | 0.84 | 0.10 | 0.89 | 1.00 | 0.76 | 0.92 |
| Arl6ip5 | 1.23 | 0.84 | 1.06 | 0.74 | 0.78 | 0.76 | 1.16 | 0.19 | 1.16 | 0.57 | 1.18 | 1.12 |
| Arl6ip6 | 0.77 | 1.10 | 1.00 | 1.07 | 0.82 | 0.99 | 0.88 | 0.20 | 1.03 | 0.18 | 0.81 | 1.00 |
| Arl8a | 1.36 | 1.37 | 1.08 | 1.02 | 1.08 | 1.01 | 1.28 | 0.29 | 1.16 | 0.47 | 1.18 | 1.29 |
| Arl9 | 1.00 | 1.00 | 1.00 | 1.00 | 1.00 | 1.00 | 1.60 | 1.00 | 1.00 | 1.00 | 1.00 | 1.00 |
| Armcx1 | 1.00 | 1.00 | 1.00 | 1.04 | 1.23 | 0.93 | 0.71 | 0.18 | 0.87 | 1.00 | 0.88 | 0.87 |
| Armcx5 | 1.18 | 0.63 | 1.00 | 1.15 | 1.00 | 0.98 | 0.85 | 0.08 | 1.17 | 0.57 | 1.13 | 0.91 |
| Art4 | 1.00 | 1.00 | 1.00 | 1.00 | 1.00 | 1.00 | 1.13 | 0.93 | 1.37 | 0.66 | 0.90 | 0.89 |
| Arxes1 | 1.00 | 1.00 | 1.00 | 1.02 | 1.29 | 1.04 | 1.08 | 0.90 | 1.01 | 1.00 | 1.00 | 1.00 |
| Asap2 | 0.60 | 0.63 | 1.00 | 1.07 | 1.00 | 0.99 | 0.78 | 0.11 | 1.09 | 1.00 | 0.76 | 1.10 |
| Asb13 | 1.07 | 1.17 | 1.37 | 1.24 | 1.63 | 1.27 | 0.69 | 0.18 | 0.83 | 1.04 | 1.30 | 1.23 |
| Asb17os | 1.00 | 1.00 | 1.00 | 1.00 | 1.00 | 1.00 | 1.00 | 1.00 | 1.00 | 0.68 | 0.45 | 0.38 |
| Asf1b | 1.00 | 1.00 | 1.00 | 0.86 | 1.00 | 1.00 | 0.61 | 0.17 | 0.72 | 0.51 | 0.93 | 0.98 |
| Atad2b | 1.00 | 1.00 | 1.00 | 0.80 | 1.00 | 0.91 | 0.77 | 0.19 | 1.08 | 0.42 | 0.76 | 0.80 |
| Atg4a | 0.69 | 0.69 | 0.95 | 0.67 | 1.00 | 0.75 | 0.86 | 0.20 | 1.17 | 0.10 | 0.72 | 0.76 |
| Atg4c | 0.82 | 0.76 | 1.15 | 0.95 | 1.00 | 0.95 | 0.72 | 0.40 | 1.08 | 0.64 | 0.90 | 0.79 |
| Atn1 | 1.21 | 1.44 | 1.36 | 0.97 | 1.49 | 1.02 | 0.93 | 0.20 | 1.01 | 0.65 | 1.00 | 0.83 |
| Atp11b | 1.35 | 1.04 | 1.10 | 0.74 | 0.89 | 0.84 | 0.94 | 0.18 | 1.12 | 0.53 | 1.18 | 1.05 |
| Atp1b1 | 1.27 | 1.41 | 1.27 | 1.10 | 1.13 | 1.06 | 1.11 | 1.13 | 1.51 | 0.75 | 0.94 | 1.08 |
| Atp1b2 | 0.88 | 1.00 | 1.14 | 1.02 | 1.27 | 1.03 | 0.88 | 0.45 | 1.29 | 0.29 | 0.73 | 0.79 |
| Atp4b | 1.00 | 1.00 | 0.67 | 1.00 | 1.49 | 1.00 | 1.00 | 1.00 | 1.00 | 1.00 | 1.00 | 1.00 |
| Atp5j | 0.78 | 0.96 | 0.92 | 1.05 | 1.62 | 1.03 | 0.95 | 0.24 | 1.01 | 0.66 | 1.04 | 1.11 |
| Atp6v0d2 | 1.00 | 1.00 | 1.00 | 1.00 | 1.00 | 1.00 | 0.78 | 0.91 | 0.49 | 1.00 | 1.00 | 1.00 |
| Atp6v1a | 0.82 | 0.88 | 0.84 | 1.09 | 0.77 | 1.01 | 0.95 | 0.14 | 1.04 | 0.51 | 1.03 | 1.14 |
| Atp6v1h | 1.25 | 0.93 | 1.03 | 1.12 | 3.01 | 1.02 | 0.98 | 0.32 | 0.96 | 0.80 | 1.05 | 1.17 |

Fig. 35- 13

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Atrx | 0.76 | 1.52 | 1.01 | 4.49 | 0.36 | 1.21 | 0.89 | 1.07 | 1.11 | 0.52 | 0.40 | 0.97 |
| Atxn1l | 0.94 | 1.07 | 1.27 | 2.19 | 0.14 | 1.15 | 1.47 | 1.68 | 1.56 | 0.54 | 0.25 | 1.18 |
| Atxn7l1 | 1.25 | 1.45 | 0.89 | 1.78 | 0.65 | 1.11 | 1.28 | 1.15 | 1.20 | 0.67 | 0.44 | 0.96 |
| Atxn7l3 | 1.14 | 1.63 | 0.99 | 0.82 | 0.18 | 0.84 | 0.93 | 0.86 | 1.01 | 0.34 | 0.30 | 1.01 |
| Atxn7l3b | 1.14 | 1.28 | 1.04 | 1.38 | 0.16 | 0.87 | 0.97 | 1.07 | 1.01 | 0.44 | 0.46 | 0.94 |
| Auh | 0.26 | 0.23 | 0.18 | 0.20 | 0.18 | 0.25 | 0.36 | 0.25 | 0.32 | 0.13 | 0.25 | 0.54 |
| Axin2 | 1.74 | 1.31 | 1.38 | 1.06 | 0.27 | 1.09 | 1.20 | 0.82 | 1.05 | 0.48 | 0.31 | 0.87 |
| B230206H07Rik | 1.00 | 1.00 | 1.00 | 1.00 | 1.00 | 1.00 | 1.00 | 1.00 | 1.00 | 1.00 | 1.00 | 1.79 |
| B230217O12Rik | 1.00 | 1.00 | 1.00 | 1.00 | 1.00 | 1.00 | 1.00 | 1.00 | 1.00 | 1.00 | 1.00 | 1.00 |
| B230219D22Rik | 0.83 | 1.80 | 0.88 | 1.74 | 0.27 | 1.01 | 0.96 | 1.19 | 1.02 | 0.39 | 0.42 | 0.92 |
| B3galnt2 | 1.36 | 1.59 | 1.10 | 1.02 | 0.61 | 0.68 | 0.73 | 0.75 | 0.74 | 0.55 | 0.70 | 1.05 |
| B3galt2 | 0.64 | 1.00 | 2.34 | 2.17 | 0.22 | 2.01 | 0.60 | 0.54 | 0.58 | 1.00 | 1.00 | 1.00 |
| B930041F14Rik | 0.83 | 0.96 | 1.08 | 0.49 | 0.85 | 0.93 | 0.80 | 0.64 | 0.80 | 0.99 | 0.95 | 0.74 |
| B9d1 | 1.00 | 0.66 | 0.90 | 0.53 | 2.28 | 0.90 | 1.09 | 1.38 | 0.98 | 0.51 | 1.97 | 0.68 |
| BC016579 | 1.00 | 1.00 | 1.00 | 1.00 | 1.00 | 1.00 | 1.00 | 1.00 | 1.00 | 1.00 | 1.00 | 1.00 |
| BC023829 | 0.81 | 2.58 | 0.84 | 0.98 | 0.13 | 0.95 | 1.13 | 0.96 | 1.11 | 0.36 | 0.14 | 1.00 |
| BC028528 | 1.00 | 1.00 | 1.00 | 0.35 | 0.11 | 0.41 | 1.51 | 1.70 | 1.93 | 0.37 | 0.22 | 0.88 |
| BC030336 | 0.99 | 1.84 | 1.04 | 1.82 | 0.13 | 0.86 | 0.91 | 1.15 | 1.00 | 0.61 | 0.36 | 0.99 |
| BC051537 | 1.00 | 1.00 | 1.00 | 1.00 | 1.00 | 1.00 | 1.00 | 1.00 | 1.00 | 1.00 | 1.00 | 1.00 |
| BC061195 | 1.00 | 1.00 | 1.00 | 1.00 | 1.00 | 1.00 | 1.00 | 1.00 | 1.00 | 1.00 | 1.00 | 1.00 |
| BC100530 | 1.00 | 1.00 | 1.00 | 1.00 | 1.00 | 1.00 | 1.00 | 1.00 | 1.00 | 1.00 | 1.00 | 1.00 |
| Bahd1 | 0.99 | 1.48 | 1.34 | 1.42 | 0.33 | 1.03 | 1.12 | 1.17 | 0.96 | 0.51 | 0.42 | 1.03 |
| Basp1 | 0.60 | 1.00 | 1.65 | 1.00 | 0.08 | 1.00 | 1.00 | 1.00 | 1.00 | 0.93 | 0.98 | 0.91 |
| Bcap29 | 0.83 | 1.26 | 0.66 | 1.43 | 0.54 | 0.90 | 0.77 | 0.95 | 0.84 | 0.20 | 0.42 | 0.98 |
| Bcl10 | 1.20 | 1.77 | 1.12 | 1.37 | 0.68 | 1.29 | 1.23 | 1.11 | 1.02 | 0.43 | 0.42 | 1.06 |
| Bcl2l2 | 0.75 | 1.83 | 0.95 | 1.30 | 0.17 | 1.01 | 0.98 | 1.12 | 1.10 | 0.73 | 0.30 | 1.18 |
| Bcl7a | 0.66 | 1.60 | 0.70 | 2.99 | 0.57 | 1.45 | 1.00 | 1.02 | 0.89 | 0.33 | 0.41 | 0.98 |
| Bcl9l | 0.43 | 0.99 | 0.79 | 0.94 | 0.32 | 1.01 | 1.01 | 1.20 | 1.29 | 1.05 | 0.88 | 1.12 |
| Bend6 | 1.00 | 1.00 | 1.00 | 1.00 | 0.18 | 1.00 | 1.00 | 1.00 | 1.30 | 1.00 | 1.00 | 1.00 |
| Bex4 | 1.00 | 1.00 | 1.00 | 1.00 | 0.73 | 1.00 | 0.68 | 1.30 | 1.31 | 0.48 | 1.06 | 1.09 |
| Bglap2 | 1.00 | 1.00 | 1.00 | 1.00 | 1.00 | 1.00 | 1.00 | 1.00 | 1.00 | 1.00 | 1.00 | 1.00 |
| Bmp10 | 1.00 | 1.00 | 1.00 | 1.00 | 1.00 | 1.00 | 0.43 | 0.19 | 2.11 | 1.00 | 1.00 | 1.00 |
| Bmp3 | 1.00 | 1.00 | 1.00 | 1.20 | 1.00 | 1.16 | 1.00 | 1.00 | 1.00 | 0.47 | 0.61 | 0.84 |
| Bmp6 | 0.96 | 1.40 | 1.12 | 1.25 | 0.06 | 1.48 | 1.66 | 1.84 | 1.54 | 0.32 | 0.04 | 0.88 |
| Bmpr1a | 0.56 | 1.15 | 0.66 | 1.78 | 0.37 | 1.03 | 0.79 | 0.98 | 0.83 | 0.40 | 0.39 | 1.04 |
| Bpifc | 1.00 | 1.00 | 1.00 | 1.00 | 1.00 | 1.00 | 1.00 | 1.00 | 1.00 | 1.00 | 1.00 | 1.00 |
| Brms1l | 0.85 | 1.09 | 1.02 | 0.92 | 0.22 | 0.82 | 0.87 | 0.78 | 0.82 | 0.37 | 0.40 | 0.95 |
| Brpf1 | 1.03 | 1.64 | 1.11 | 1.08 | 0.39 | 0.95 | 1.14 | 1.27 | 1.20 | 0.61 | 0.48 | 1.19 |
| Btbd10 | 0.72 | 1.36 | 1.07 | 0.83 | 0.22 | 0.95 | 1.02 | 0.84 | 0.99 | 0.37 | 0.38 | 0.84 |
| Btbd3 | 0.65 | 1.20 | 0.81 | 1.34 | 0.20 | 0.99 | 1.04 | 1.23 | 1.07 | 0.80 | 0.51 | 1.22 |
| Btnl9 | 1.00 | 1.00 | 1.18 | 3.22 | 0.13 | 1.07 | 1.12 | 1.65 | 1.74 | 1.00 | 1.00 | 1.00 |
| C030029H02Rik | 1.00 | 1.00 | 1.00 | 1.00 | 1.00 | 1.00 | 1.00 | 1.00 | 1.00 | 1.00 | 1.00 | 1.00 |
| C030046E11Rik | 1.45 | 2.58 | 1.59 | 1.13 | 0.28 | 0.75 | 1.21 | 1.59 | 1.20 | 1.00 | 0.72 | 1.21 |
| C1galt1c1 | 1.37 | 2.78 | 1.20 | 0.76 | 0.17 | 0.87 | 0.85 | 1.10 | 1.12 | 0.17 | 0.17 | 1.14 |
| C1s1 | 1.09 | 1.73 | 1.56 | 1.65 | 0.52 | 1.16 | 0.84 | 0.77 | 1.19 | 0.36 | 0.33 | 0.94 |
| C230091D08Rik | 0.71 | 1.00 | 0.84 | 2.70 | 0.17 | 0.89 | 0.75 | 1.10 | 1.04 | 1.00 | 0.89 | 0.82 |
| C2cd4d | 1.00 | 1.00 | 1.00 | 1.00 | 1.29 | 1.00 | 1.00 | 1.00 | 1.00 | 1.00 | 1.00 | 1.00 |
| C330022C24Rik | 1.00 | 1.00 | 1.00 | 1.00 | 1.00 | 1.00 | 1.00 | 1.00 | 1.00 | 1.00 | 1.00 | 1.00 |
| C4a | 1.00 | 1.00 | 1.00 | 0.45 | 3.16 | 0.73 | 1.00 | 1.00 | 1.00 | 1.43 | 1.13 | 0.40 |
| C6 | 1.00 | 1.00 | 1.00 | 0.89 | 0.34 | 0.79 | 1.00 | 1.00 | 1.00 | 0.19 | 0.40 | 0.86 |
| C730036E19Rik | 1.00 | 1.00 | 1.00 | 1.00 | 1.00 | 1.00 | 0.96 | 0.89 | 1.00 | 1.00 | 1.00 | 1.00 |
| C78339 | 0.89 | 2.01 | 1.25 | 2.13 | 0.80 | 1.05 | 1.43 | 1.86 | 1.65 | 1.55 | 1.24 | 0.99 |
| C920009B18Rik | 1.00 | 1.00 | 1.00 | 1.00 | 1.00 | 1.00 | 1.00 | 1.00 | 1.00 | 1.00 | 1.00 | 1.00 |
| Calm4 | 1.00 | 0.81 | 1.00 | 1.00 | 1.00 | 1.00 | 0.60 | 1.20 | 1.00 | 1.00 | 1.00 | 1.00 |
| Calml3 | 1.00 | 1.00 | 1.00 | 1.00 | 1.10 | 2.60 | 1.00 | 1.00 | 1.00 | 0.20 | 0.11 | 0.33 |
| Camk2n1 | 1.56 | 1.79 | 1.26 | 2.04 | 0.20 | 1.78 | 1.35 | 1.50 | 1.12 | 0.65 | 0.73 | 1.04 |
| Cap1 | 1.15 | 1.83 | 1.13 | 1.38 | 0.38 | 1.30 | 0.82 | 0.77 | 0.86 | 0.29 | 0.38 | 0.96 |
| Capg | 0.22 | 0.15 | 0.21 | 0.22 | 0.57 | 0.32 | 0.14 | 0.12 | 0.24 | 0.68 | 0.68 | 0.26 |
| Capn15 | 0.94 | 1.00 | 1.24 | 1.12 | 0.21 | 1.03 | 1.12 | 1.18 | 1.62 | 1.00 | 1.00 | 1.11 |
| Car1 | 1.00 | 1.00 | 0.09 | 1.00 | 1.00 | 0.51 | 1.00 | 1.00 | 1.00 | 1.00 | 1.00 | 0.60 |
| Car12 | 1.00 | 1.00 | 1.00 | 1.00 | 1.00 | 1.00 | 1.00 | 1.00 | 1.00 | 1.00 | 1.00 | 1.00 |
| Car2 | 0.68 | 1.04 | 0.67 | 0.48 | 0.23 | 0.53 | 0.70 | 0.85 | 0.52 | 0.26 | 0.22 | 0.69 |
| Car3 | 2.21 | 3.03 | 1.10 | 0.51 | 0.17 | 0.22 | 0.38 | 0.35 | 1.66 | 0.36 | 0.24 | 0.39 |
| Car7 | 0.69 | 0.76 | 0.39 | 0.30 | 0.30 | 0.37 | 0.21 | 0.14 | 0.16 | 1.00 | 1.00 | 1.00 |

Fig. 35- 14

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Atrx | 0.66 | 0.63 | 0.79 | 1.03 | 1.00 | 1.09 | 0.77 | 1.00 | 0.84 | 0.96 | 0.61 | 1.01 |
| Atxn1l | 0.69 | 0.58 | 1.00 | 1.30 | 1.07 | 1.26 | 0.99 | 1.00 | 1.11 | 1.08 | 0.51 | 0.95 |
| Atxn7l1 | 0.82 | 0.77 | 0.98 | 1.24 | 2.87 | 1.05 | 0.74 | 1.00 | 0.88 | 1.21 | 0.76 | 1.13 |
| Atxn7l3 | 0.73 | 0.73 | 0.92 | 1.04 | 1.30 | 1.01 | 1.08 | 0.94 | 1.20 | 0.99 | 0.75 | 0.98 |
| Atxn7l3b | 0.82 | 0.72 | 0.96 | 0.96 | 1.15 | 0.97 | 0.95 | 0.43 | 1.07 | 1.06 | 0.69 | 0.99 |
| Auh | 0.59 | 0.57 | 0.49 | 0.41 | 0.68 | 0.49 | 0.33 | 0.17 | 0.22 | 0.52 | 0.51 | 0.46 |
| Axin2 | 0.74 | 0.70 | 1.02 | 1.00 | 1.00 | 1.00 | 0.88 | 1.00 | 2.18 | 1.14 | 0.78 | 1.05 |
| B230206H07Rik | 1.52 | 1.00 | 1.16 | 1.16 | 1.00 | 1.52 | 1.16 | 1.00 | 1.04 | 0.97 | 0.47 | 0.91 |
| B230217O12Rik | 0.52 | 0.37 | 0.65 | 1.00 | 1.00 | 1.00 | 1.07 | 1.00 | 1.26 | 1.00 | 1.00 | 1.00 |
| B230219D22Rik | 0.61 | 0.54 | 0.74 | 0.95 | 1.90 | 0.93 | 0.81 | 0.44 | 0.78 | 0.91 | 0.65 | 0.93 |
| B3galnt2 | 0.79 | 0.86 | 0.89 | 1.07 | 1.41 | 1.11 | 0.70 | 0.44 | 0.77 | 0.98 | 0.91 | 1.17 |
| B3galt2 | 1.16 | 0.96 | 1.51 | 1.00 | 1.00 | 1.00 | 1.00 | 1.00 | 1.00 | 1.25 | 0.83 | 1.41 |
| B930041F14Rik | 0.91 | 0.87 | 0.81 | 0.80 | 0.64 | 0.83 | 1.00 | 1.00 | 1.00 | 0.92 | 0.96 | 0.84 |
| B9d1 | 1.25 | 2.16 | 1.96 | 1.06 | 1.38 | 0.79 | 1.00 | 1.00 | 1.00 | 0.92 | 1.17 | 1.19 |
| BC016579 | 1.00 | 1.00 | 1.00 | 1.00 | 1.00 | 1.00 | 1.00 | 1.00 | 1.00 | 1.24 | 0.88 | 1.08 |
| BC023829 | 0.84 | 0.87 | 0.98 | 0.95 | 1.42 | 1.07 | 1.05 | 1.00 | 0.88 | 1.01 | 0.74 | 1.23 |
| BC028528 | 1.00 | 3.86 | 2.21 | 1.00 | 1.00 | 1.00 | 1.00 | 1.00 | 1.00 | 1.00 | 1.00 | 1.00 |
| BC030336 | 0.75 | 0.70 | 0.88 | 1.22 | 1.00 | 1.01 | 0.98 | 1.00 | 0.84 | 0.94 | 0.52 | 1.00 |
| BC051537 | 0.11 | 0.14 | 0.13 | 1.00 | 1.00 | 1.00 | 1.00 | 1.00 | 1.00 | 1.00 | 1.00 | 1.00 |
| BC061195 | 1.00 | 1.00 | 1.00 | 1.00 | 1.00 | 1.00 | 1.00 | 1.00 | 1.00 | 1.00 | 1.00 | 1.00 |
| BC100530 | 1.00 | 1.00 | 1.00 | 1.00 | 1.00 | 1.00 | 1.00 | 1.00 | 1.00 | 1.00 | 1.00 | 1.00 |
| Bahd1 | 0.79 | 0.77 | 1.04 | 1.13 | 1.23 | 1.05 | 1.23 | 1.00 | 1.29 | 1.04 | 0.75 | 1.03 |
| Basp1 | 1.00 | 0.96 | 1.28 | 1.00 | 1.00 | 1.00 | 1.00 | 1.00 | 1.00 | 0.90 | 1.02 | 0.82 |
| Bcap29 | 1.20 | 0.98 | 1.13 | 0.85 | 1.18 | 0.70 | 1.30 | 0.57 | 1.32 | 0.97 | 1.01 | 0.94 |
| Bcl10 | 0.97 | 0.91 | 1.08 | 1.03 | 1.62 | 0.99 | 1.47 | 0.54 | 1.44 | 1.23 | 1.14 | 1.15 |
| Bcl2l2 | 1.06 | 0.84 | 1.11 | 1.02 | 1.24 | 1.00 | 1.11 | 0.68 | 0.95 | 0.93 | 0.61 | 0.99 |
| Bcl7a | 0.56 | 0.54 | 0.64 | 0.95 | 1.28 | 0.90 | 1.21 | 1.00 | 1.15 | 0.90 | 0.69 | 0.98 |
| Bcl9l | 0.74 | 0.57 | 1.40 | 1.13 | 0.99 | 1.17 | 0.77 | 2.02 | 1.12 | 0.92 | 0.39 | 1.01 |
| Bend6 | 1.55 | 0.97 | 1.30 | 1.00 | 1.00 | 1.00 | 1.00 | 1.00 | 1.00 | 1.00 | 1.00 | 1.00 |
| Bex4 | 1.90 | 2.71 | 1.53 | 1.00 | 1.55 | 0.84 | 1.00 | 1.00 | 1.00 | 1.13 | 1.48 | 1.03 |
| Bglap2 | 1.00 | 1.00 | 1.00 | 1.00 | 1.00 | 1.00 | 1.00 | 1.00 | 1.00 | 1.00 | 1.23 | 1.39 |
| Bmp10 | 1.00 | 1.00 | 1.00 | 1.00 | 1.00 | 1.00 | 0.73 | 1.00 | 1.65 | 1.00 | 1.00 | 1.00 |
| Bmp3 | 0.79 | 0.76 | 1.00 | 1.00 | 1.00 | 1.00 | 1.00 | 1.00 | 1.00 | 1.03 | 1.00 | 0.99 |
| Bmp6 | 1.29 | 1.20 | 1.48 | 1.30 | 1.00 | 1.28 | 1.63 | 1.00 | 1.52 | 0.85 | 0.60 | 0.99 |
| Bmpr1a | 1.51 | 1.03 | 1.33 | 1.13 | 1.52 | 1.02 | 1.03 | 0.95 | 1.02 | 1.10 | 0.76 | 0.98 |
| Bpifc | 1.47 | 0.83 | 1.06 | 1.00 | 1.00 | 1.00 | 1.00 | 1.00 | 1.00 | 1.00 | 1.00 | 1.00 |
| Brms1l | 0.84 | 0.87 | 0.88 | 0.88 | 1.09 | 0.86 | 0.82 | 1.00 | 0.63 | 0.83 | 0.92 | 1.04 |
| Brpf1 | 0.65 | 0.61 | 0.82 | 1.13 | 0.99 | 1.08 | 1.42 | 1.00 | 1.29 | 1.10 | 0.72 | 0.96 |
| Btbd10 | 0.74 | 0.62 | 0.80 | 1.18 | 1.00 | 0.92 | 1.42 | 1.00 | 1.00 | 0.96 | 0.80 | 0.94 |
| Btbd3 | 1.07 | 0.82 | 1.36 | 1.16 | 1.20 | 1.16 | 0.76 | 1.00 | 1.19 | 1.16 | 0.86 | 1.06 |
| Btnl9 | 1.00 | 1.00 | 0.97 | 0.63 | 1.00 | 0.88 | 1.00 | 1.00 | 1.11 | 0.96 | 1.00 | 0.92 |
| C030029H02Rik | 1.00 | 1.00 | 1.00 | 1.00 | 1.00 | 1.00 | 1.00 | 1.00 | 1.00 | 1.00 | 1.00 | 1.00 |
| C030046E11Rik | 0.58 | 0.44 | 0.84 | 1.35 | 1.00 | 1.09 | 1.17 | 1.00 | 1.28 | 0.96 | 0.48 | 0.87 |
| C1galt1c1 | 1.01 | 0.86 | 1.04 | 1.03 | 2.67 | 0.96 | 1.06 | 0.32 | 0.99 | 1.20 | 1.12 | 1.15 |
| C1s1 | 1.72 | 1.21 | 1.66 | 0.96 | 1.42 | 1.03 | 0.57 | 0.32 | 0.82 | 0.85 | 0.80 | 0.91 |
| C230091D08Rik | 0.49 | 0.35 | 0.90 | 1.08 | 1.00 | 1.02 | 1.18 | 1.00 | 1.15 | 1.06 | 0.31 | 1.00 |
| C2cd4d | 0.25 | 0.16 | 0.89 | 1.00 | 1.04 | 1.24 | 1.00 | 1.52 | 0.75 | 1.00 | 1.00 | 1.00 |
| C330022C24Rik | 1.00 | 1.00 | 1.00 | 1.00 | 1.00 | 1.00 | 0.80 | 0.59 | 0.81 | 1.00 | 1.00 | 1.00 |
| C4a | 1.00 | 1.00 | 0.83 | 0.39 | 0.17 | 0.37 | 0.26 | 0.54 | 0.61 | 0.78 | 0.67 | 0.54 |
| C6 | 1.01 | 1.07 | 1.19 | 1.00 | 1.00 | 1.00 | 1.14 | 0.84 | 0.96 | 1.00 | 1.00 | 1.00 |
| C730036E19Rik | 1.00 | 1.00 | 1.00 | 1.00 | 1.00 | 1.00 | 0.03 | 0.06 | 0.01 | 1.00 | 1.00 | 1.00 |
| C78339 | 0.60 | 0.35 | 1.37 | 1.04 | 4.23 | 1.25 | 0.81 | 2.62 | 1.04 | 1.00 | 0.46 | 0.92 |
| C920009B18Rik | 0.16 | 0.14 | 0.20 | 1.00 | 1.00 | 1.00 | 1.00 | 1.00 | 1.00 | 1.00 | 1.00 | 1.00 |
| Calm4 | 0.61 | 0.58 | 0.33 | 1.00 | 1.00 | 1.09 | 1.00 | 1.00 | 1.27 | 1.00 | 1.00 | 0.16 |
| Calml3 | 1.24 | 1.17 | 1.45 | 1.04 | 1.00 | 1.46 | 1.00 | 1.00 | 1.00 | 1.00 | 1.00 | 0.63 |
| Camk2n1 | 1.97 | 1.97 | 1.92 | 1.07 | 1.40 | 1.00 | 0.67 | 0.45 | 0.71 | 0.91 | 1.01 | 1.03 |
| Cap1 | 0.82 | 0.85 | 0.99 | 0.98 | 2.18 | 0.91 | 0.91 | 0.59 | 0.93 | 0.99 | 0.90 | 0.97 |
| Capg | 0.61 | 0.57 | 0.89 | 0.13 | 0.16 | 0.17 | 1.00 | 1.44 | 0.99 | 0.76 | 1.19 | 0.83 |
| Capn15 | 0.50 | 0.41 | 0.95 | 1.07 | 1.00 | 0.94 | 1.12 | 1.00 | 0.90 | 0.76 | 0.27 | 0.87 |
| Car1 | 1.00 | 1.00 | 0.72 | 1.00 | 1.00 | 1.00 | 0.21 | 0.41 | 0.36 | 1.86 | 2.65 | 1.76 |
| Car12 | 0.47 | 0.39 | 0.87 | 0.75 | 0.87 | 0.89 | 1.00 | 1.00 | 1.00 | 1.35 | 0.98 | 1.32 |
| Car2 | 0.22 | 0.22 | 0.27 | 0.64 | 1.25 | 0.70 | 0.71 | 1.00 | 0.85 | 0.71 | 0.76 | 0.81 |
| Car3 | 0.17 | 0.26 | 0.19 | 0.72 | 0.86 | 0.72 | 0.02 | 0.01 | 0.06 | 0.47 | 1.33 | 0.50 |
| Car7 | 1.13 | 0.91 | 0.85 | 0.36 | 1.00 | 0.34 | 1.00 | 1.00 | 1.00 | 1.00 | 1.00 | 0.99 |

Fig. 35- 15

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Atrx | 1.06 | 0.87 | 0.88 | 1.18 | 0.27 | 0.96 | 0.77 | 1.00 | 0.84 | 1.11 | 0.76 | 1.17 |
| Atxn1l | 1.23 | 1.13 | 0.95 | 1.19 | 0.31 | 0.78 | 1.36 | 0.90 | 1.18 | 0.99 | 0.61 | 1.24 |
| Atxn7l1 | 0.92 | 1.21 | 1.04 | 1.28 | 0.61 | 1.00 | 1.09 | 0.35 | 0.99 | 0.98 | 0.83 | 1.17 |
| Atxn7l3 | 0.87 | 1.04 | 0.94 | 1.00 | 0.59 | 1.02 | 1.08 | 0.94 | 1.00 | 0.86 | 0.79 | 0.99 |
| Atxn7l3b | 0.92 | 0.99 | 0.88 | 1.03 | 0.22 | 0.99 | 1.00 | 0.48 | 1.06 | 0.98 | 0.83 | 1.07 |
| Auh | 0.73 | 0.87 | 0.75 | 0.27 | 0.32 | 0.21 | 0.82 | 0.78 | 0.70 | 0.48 | 0.63 | 0.46 |
| Axin2 | 0.97 | 0.92 | 1.59 | 1.69 | 1.00 | 1.43 | 0.80 | 1.00 | 0.89 | 0.65 | 0.59 | 0.88 |
| B230206H07Rik | 1.20 | 1.30 | 0.81 | 1.59 | 1.00 | 1.18 | 1.00 | 1.00 | 1.00 | 1.00 | 1.00 | 1.00 |
| B230217O12Rik | 1.00 | 1.00 | 1.00 | 1.00 | 1.00 | 1.00 | 0.63 | 1.00 | 1.01 | 0.47 | 0.37 | 0.62 |
| B230219D22Rik | 0.95 | 0.88 | 0.89 | 1.02 | 0.20 | 0.83 | 1.12 | 0.82 | 0.99 | 0.91 | 0.65 | 0.97 |
| B3galnt2 | 1.00 | 0.83 | 1.04 | 0.85 | 0.64 | 1.01 | 0.43 | 0.19 | 0.41 | 0.92 | 0.75 | 0.93 |
| B3galt2 | 1.00 | 1.00 | 1.00 | 0.24 | 0.03 | 1.03 | 1.00 | 1.00 | 1.00 | 1.00 | 1.27 | 1.00 |
| B930041F14Rik | 1.23 | 1.25 | 1.05 | 0.97 | 1.34 | 1.28 | 0.60 | 0.76 | 0.47 | 0.93 | 1.37 | 0.85 |
| B9d1 | 0.92 | 0.66 | 0.77 | 1.01 | 2.11 | 0.85 | 1.06 | 0.69 | 0.93 | 1.34 | 1.16 | 1.33 |
| BC016579 | 0.77 | 0.76 | 0.72 | 1.00 | 1.00 | 1.00 | 1.00 | 1.00 | 1.00 | 1.42 | 1.00 | 1.00 |
| BC023829 | 0.86 | 1.04 | 0.80 | 0.88 | 1.00 | 1.05 | 0.92 | 0.85 | 0.93 | 1.05 | 1.02 | 1.05 |
| BC028528 | 1.00 | 1.00 | 1.00 | 1.27 | 1.00 | 1.76 | 1.00 | 1.00 | 1.00 | 1.41 | 0.71 | 0.31 |
| BC030336 | 1.19 | 1.18 | 1.10 | 1.12 | 0.26 | 0.95 | 1.06 | 0.60 | 1.14 | 1.11 | 0.79 | 1.06 |
| BC051537 | 1.00 | 1.00 | 1.00 | 1.00 | 1.00 | 1.00 | 1.00 | 1.00 | 1.00 | 0.43 | 0.36 | 0.37 |
| BC061195 | 1.00 | 1.00 | 1.00 | 1.00 | 1.00 | 1.00 | 0.81 | 0.06 | 0.63 | 1.00 | 1.00 | 1.00 |
| BC100530 | 1.00 | 0.72 | 1.73 | 1.00 | 1.00 | 1.00 | 1.00 | 1.12 | 1.00 | 1.00 | 1.00 | 1.00 |
| Bahd1 | 1.03 | 0.99 | 0.88 | 0.91 | 0.95 | 0.94 | 0.99 | 0.54 | 0.99 | 1.06 | 0.75 | 1.09 |
| Basp1 | 1.17 | 0.51 | 0.70 | 0.43 | 0.69 | 0.38 | 0.92 | 0.45 | 1.01 | 0.63 | 1.54 | 0.63 |
| Bcap29 | 0.83 | 0.94 | 1.33 | 0.94 | 0.29 | 1.16 | 0.92 | 0.24 | 0.94 | 1.23 | 1.19 | 1.17 |
| Bcl10 | 1.00 | 0.83 | 0.89 | 1.19 | 0.37 | 1.09 | 0.94 | 0.73 | 1.06 | 1.03 | 0.71 | 0.96 |
| Bcl2l2 | 1.06 | 0.96 | 0.90 | 0.85 | 0.32 | 0.85 | 1.06 | 1.33 | 1.00 | 0.90 | 1.00 | 0.96 |
| Bcl7a | 1.04 | 1.06 | 1.12 | 1.10 | 0.72 | 1.76 | 1.08 | 1.00 | 0.85 | 1.27 | 1.12 | 1.03 |
| Bcl9l | 1.14 | 1.34 | 0.96 | 1.05 | 0.21 | 1.11 | 1.16 | 1.00 | 1.22 | 0.70 | 0.44 | 1.00 |
| Bend6 | 1.00 | 1.00 | 1.00 | 1.00 | 1.00 | 1.00 | 0.90 | 1.00 | 1.00 | 0.76 | 4.02 | 1.29 |
| Bex4 | 1.12 | 1.01 | 1.51 | 1.11 | 1.31 | 3.73 | 0.78 | 0.27 | 0.74 | 0.50 | 1.28 | 0.19 |
| Bglap2 | 1.00 | 1.00 | 1.00 | 1.00 | 1.00 | 1.00 | 1.00 | 1.00 | 1.00 | 1.00 | 1.00 | 1.00 |
| Bmp10 | 1.00 | 1.00 | 1.00 | 1.00 | 1.00 | 1.00 | 1.00 | 1.00 | 1.00 | 1.00 | 1.00 | 1.00 |
| Bmp3 | 0.85 | 1.02 | 1.13 | 0.29 | 1.00 | 0.13 | 1.04 | 1.00 | 0.98 | 1.00 | 1.00 | 1.00 |
| Bmp6 | 1.03 | 1.46 | 1.01 | 1.13 | 0.23 | 1.24 | 0.90 | 1.00 | 0.46 | 0.80 | 0.59 | 0.84 |
| Bmpr1a | 1.00 | 0.96 | 0.89 | 0.97 | 0.22 | 0.92 | 1.19 | 0.92 | 0.98 | 1.05 | 0.94 | 1.26 |
| Bpifc | 0.79 | 1.03 | 1.08 | 1.00 | 1.00 | 1.00 | 1.00 | 1.00 | 1.00 | 1.00 | 1.00 | 1.00 |
| Brms1l | 1.10 | 1.13 | 1.01 | 0.97 | 1.00 | 1.09 | 1.09 | 0.77 | 0.87 | 0.97 | 0.99 | 1.03 |
| Brpf1 | 1.06 | 1.02 | 0.96 | 1.64 | 0.65 | 1.18 | 1.14 | 0.83 | 0.99 | 0.97 | 0.79 | 1.01 |
| Btbd10 | 0.89 | 0.85 | 0.83 | 0.93 | 1.00 | 0.88 | 0.94 | 0.51 | 0.94 | 0.88 | 0.89 | 0.79 |
| Btbd3 | 1.28 | 1.36 | 1.14 | 1.06 | 0.25 | 0.90 | 1.35 | 1.00 | 1.34 | 0.96 | 1.49 | 1.26 |
| Btnl9 | 0.43 | 0.41 | 0.71 | 0.88 | 0.12 | 0.62 | 1.00 | 1.00 | 1.00 | 0.40 | 0.39 | 0.52 |
| C030029H02Rik | 1.00 | 1.00 | 1.00 | 1.00 | 1.00 | 1.00 | 1.00 | 1.00 | 1.00 | 1.00 | 1.00 | 1.00 |
| C030046E11Rik | 1.09 | 0.94 | 0.96 | 1.19 | 0.53 | 0.79 | 1.22 | 1.00 | 1.15 | 0.98 | 0.58 | 1.06 |
| C1galt1c1 | 1.05 | 0.90 | 0.87 | 1.33 | 0.60 | 1.13 | 1.35 | 1.92 | 0.68 | 0.99 | 0.91 | 1.01 |
| C1s1 | 1.02 | 0.89 | 1.51 | 0.71 | 0.47 | 0.97 | 0.71 | 0.47 | 0.82 | 0.90 | 0.78 | 1.13 |
| C230091D08Rik | 0.98 | 0.80 | 0.88 | 1.05 | 0.50 | 0.87 | 0.86 | 1.00 | 0.80 | 1.06 | 0.58 | 1.12 |
| C2cd4d | 1.00 | 1.00 | 1.00 | 1.00 | 1.00 | 1.00 | 1.00 | 1.00 | 1.00 | 1.00 | 1.00 | 1.00 |
| C330022C24Rik | 1.00 | 1.00 | 1.00 | 1.00 | 1.00 | 1.00 | 1.12 | 1.08 | 1.00 | 1.00 | 1.00 | 1.00 |
| C4a | 0.84 | 0.95 | 0.89 | 0.26 | 0.48 | 0.30 | 1.54 | 4.96 | 1.86 | 0.44 | 0.36 | 0.54 |
| C6 | 1.00 | 1.00 | 1.00 | 1.39 | 0.73 | 1.09 | 1.00 | 1.00 | 1.00 | 0.85 | 1.13 | 1.05 |
| C730036E19Rik | 1.00 | 1.00 | 1.00 | 1.00 | 1.00 | 1.00 | 1.00 | 1.00 | 1.00 | 1.00 | 1.00 | 1.00 |
| C78339 | 0.84 | 0.93 | 0.97 | 1.08 | 0.74 | 0.75 | 0.78 | 1.09 | 1.07 | 0.85 | 0.56 | 1.48 |
| C920009B18Rik | 1.00 | 1.00 | 1.00 | 1.00 | 1.00 | 1.00 | 1.00 | 1.00 | 1.00 | 0.31 | 0.27 | 0.22 |
| Calm4 | 1.18 | 1.32 | 1.22 | 1.00 | 1.00 | 4.18 | 1.01 | 1.34 | 1.55 | 1.00 | 1.00 | 0.62 |
| Calml3 | 0.88 | 1.13 | 1.10 | 1.70 | 2.13 | 3.20 | 1.41 | 0.84 | 1.99 | 1.00 | 1.00 | 1.00 |
| Camk2n1 | 1.21 | 1.24 | 1.13 | 1.16 | 1.71 | 1.48 | 0.93 | 0.52 | 0.99 | 1.48 | 4.54 | 2.01 |
| Cap1 | 0.82 | 0.85 | 0.82 | 1.23 | 0.25 | 1.07 | 0.96 | 0.26 | 0.93 | 0.82 | 0.68 | 0.83 |
| Capg | 0.53 | 0.53 | 0.44 | 0.12 | 0.30 | 0.12 | 1.00 | 0.71 | 0.69 | 0.15 | 0.18 | 0.23 |
| Capn15 | 0.91 | 0.98 | 0.76 | 1.31 | 0.57 | 1.07 | 1.22 | 1.00 | 1.32 | 0.77 | 0.51 | 1.10 |
| Car1 | 1.00 | 1.00 | 1.00 | 0.54 | 1.00 | 0.90 | 1.00 | 1.00 | 1.00 | 0.49 | 0.37 | 0.15 |
| Car12 | 0.95 | 0.86 | 1.03 | 1.00 | 1.00 | 1.00 | 1.00 | 1.00 | 1.00 | 1.33 | 1.17 | 1.11 |
| Car2 | 0.49 | 0.47 | 0.47 | 0.95 | 0.67 | 0.87 | 0.89 | 2.01 | 0.97 | 0.41 | 0.38 | 0.19 |
| Car3 | 0.47 | 0.39 | 0.68 | 0.11 | 0.07 | 0.23 | 0.44 | 1.00 | 1.55 | 0.48 | 0.88 | 0.92 |
| Car7 | 1.27 | 1.73 | 1.52 | 0.11 | 1.00 | 0.12 | 2.06 | 1.00 | 2.48 | 0.43 | 0.53 | 0.47 |

Fig. 35- 16

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Atrx | 1.09 | 1.19 | 1.11 | 0.92 | 0.98 | 0.93 | 0.76 | 0.17 | 1.09 | 0.59 | 1.04 | 1.00 |
| Atxn1l | 1.31 | 1.12 | 1.27 | 0.86 | 1.00 | 0.88 | 0.78 | 0.10 | 1.20 | 0.64 | 0.90 | 0.95 |
| Atxn7l1 | 0.90 | 0.82 | 0.83 | 1.21 | 0.32 | 1.03 | 0.88 | 0.11 | 0.95 | 0.55 | 0.96 | 0.90 |
| Atxn7l3 | 1.15 | 1.27 | 1.08 | 1.06 | 1.51 | 1.00 | 1.06 | 0.14 | 1.02 | 0.45 | 1.10 | 1.07 |
| Atxn7l3b | 0.95 | 0.94 | 0.86 | 1.02 | 1.35 | 0.99 | 0.88 | 0.16 | 1.01 | 0.43 | 0.99 | 0.93 |
| Auh | 0.50 | 0.45 | 0.41 | 0.51 | 0.42 | 0.61 | 0.73 | 0.15 | 0.68 | 0.25 | 0.34 | 0.30 |
| Axin2 | 1.00 | 1.00 | 1.00 | 0.88 | 1.00 | 0.88 | 0.83 | 0.07 | 0.91 | 1.00 | 0.87 | 1.06 |
| B230206H07Rik | 1.00 | 1.00 | 1.00 | 0.87 | 1.00 | 1.06 | 1.00 | 0.13 | 1.15 | 1.00 | 1.00 | 1.00 |
| B230217O12Rik | 1.00 | 1.00 | 1.00 | 0.18 | 1.00 | 0.15 | 0.42 | 0.74 | 0.55 | 1.00 | 0.60 | 0.75 |
| B230219D22Rik | 1.06 | 0.87 | 1.30 | 0.92 | 0.69 | 0.97 | 0.95 | 0.16 | 1.18 | 0.55 | 0.82 | 0.86 |
| B3galnt2 | 0.81 | 0.80 | 0.94 | 0.87 | 1.00 | 1.08 | 0.78 | 0.75 | 0.88 | 0.78 | 0.68 | 0.74 |
| B3galt2 | 1.00 | 1.00 | 1.00 | 1.12 | 0.50 | 0.90 | 0.82 | 0.99 | 1.75 | 1.00 | 1.00 | 1.00 |
| B930041F14Rik | 0.29 | 0.19 | 0.28 | 1.07 | 0.98 | 0.97 | 0.71 | 1.34 | 0.65 | 1.29 | 0.90 | 0.81 |
| B9d1 | 1.00 | 1.00 | 1.00 | 0.89 | 0.04 | 1.00 | 1.48 | 2.32 | 0.49 | 1.00 | 1.00 | 1.00 |
| BC016579 | 1.00 | 1.00 | 1.00 | 1.00 | 1.00 | 1.00 | 0.76 | 0.11 | 0.77 | 1.00 | 1.00 | 1.00 |
| BC023829 | 0.86 | 0.88 | 1.43 | 1.17 | 1.00 | 1.03 | 1.38 | 0.13 | 1.43 | 0.41 | 0.86 | 0.87 |
| BC028528 | 1.00 | 1.00 | 1.00 | 1.00 | 1.00 | 1.00 | 1.43 | 1.00 | 1.00 | 0.49 | 1.41 | 1.94 |
| BC030336 | 1.39 | 1.16 | 1.04 | 0.95 | 1.70 | 0.99 | 0.88 | 0.18 | 1.31 | 0.59 | 0.83 | 0.83 |
| BC051537 | 1.00 | 1.00 | 1.00 | 1.00 | 1.00 | 1.00 | 1.00 | 1.00 | 1.00 | 1.18 | 2.58 | 3.00 |
| BC061195 | 1.00 | 1.00 | 1.00 | 1.00 | 1.00 | 1.00 | 1.00 | 1.00 | 1.00 | 1.00 | 1.00 | 1.00 |
| BC100530 | 1.00 | 1.00 | 1.00 | 1.00 | 1.00 | 1.00 | 0.15 | 0.96 | 0.38 | 4.87 | 4.08 | 1.89 |
| Bahd1 | 1.57 | 1.52 | 1.30 | 0.91 | 0.63 | 0.94 | 1.02 | 0.13 | 0.81 | 0.36 | 0.87 | 0.82 |
| Basp1 | 1.00 | 1.00 | 1.00 | 1.05 | 0.95 | 1.05 | 2.66 | 0.26 | 1.46 | 0.50 | 1.05 | 0.81 |
| Bcap29 | 0.96 | 0.57 | 1.00 | 0.95 | 0.72 | 1.06 | 0.81 | 0.08 | 0.89 | 0.37 | 0.89 | 0.93 |
| Bcl10 | 1.87 | 1.04 | 0.96 | 1.08 | 1.00 | 1.14 | 0.90 | 0.16 | 0.96 | 0.67 | 1.39 | 1.31 |
| Bcl2l2 | 1.05 | 0.94 | 1.14 | 1.05 | 1.82 | 0.95 | 0.99 | 0.12 | 1.07 | 0.55 | 0.71 | 0.96 |
| Bcl7a | 0.86 | 0.62 | 0.64 | 1.00 | 0.37 | 1.00 | 0.86 | 0.18 | 1.05 | 0.21 | 0.57 | 0.79 |
| Bcl9l | 1.64 | 1.17 | 1.48 | 0.83 | 0.92 | 0.92 | 0.80 | 0.09 | 0.94 | 1.00 | 0.76 | 0.73 |
| Bend6 | 1.00 | 1.00 | 1.00 | 1.06 | 1.35 | 1.02 | 1.00 | 1.00 | 1.00 | 1.00 | 1.00 | 1.00 |
| Bex4 | 0.23 | 0.28 | 1.00 | 0.89 | 0.24 | 0.88 | 1.83 | 1.00 | 1.00 | 0.66 | 0.83 | 0.97 |
| Bglap2 | 1.00 | 1.00 | 1.00 | 1.00 | 0.06 | 1.00 | 1.00 | 0.88 | 0.28 | 0.60 | 1.00 | 1.00 |
| Bmp10 | 1.00 | 1.00 | 1.00 | 1.00 | 1.00 | 1.00 | 1.00 | 1.00 | 1.00 | 1.00 | 1.00 | 1.00 |
| Bmp3 | 1.03 | 0.87 | 0.81 | 0.63 | 0.78 | 0.67 | 0.81 | 0.36 | 1.47 | 1.00 | 1.00 | 1.00 |
| Bmp6 | 1.00 | 1.00 | 1.00 | 1.04 | 1.00 | 1.15 | 1.25 | 0.63 | 1.53 | 1.00 | 1.00 | 1.00 |
| Bmpr1a | 1.19 | 1.15 | 1.02 | 0.91 | 1.07 | 0.92 | 0.76 | 0.14 | 0.99 | 1.00 | 1.48 | 1.21 |
| Bpifc | 1.00 | 1.00 | 1.00 | 1.00 | 1.00 | 1.00 | 0.79 | 0.09 | 0.66 | 1.00 | 1.00 | 1.00 |
| Brms1l | 1.00 | 1.00 | 1.00 | 0.92 | 0.41 | 0.97 | 0.82 | 0.12 | 0.98 | 0.42 | 0.69 | 0.79 |
| Brpf1 | 1.55 | 1.48 | 1.65 | 0.86 | 1.00 | 1.05 | 1.07 | 0.12 | 1.10 | 0.48 | 0.95 | 0.87 |
| Btbd10 | 1.00 | 1.00 | 1.00 | 1.16 | 3.59 | 1.12 | 0.98 | 0.14 | 0.80 | 0.50 | 0.96 | 1.03 |
| Btbd3 | 3.51 | 4.10 | 2.17 | 0.97 | 0.55 | 0.96 | 0.82 | 0.24 | 1.00 | 1.00 | 1.00 | 1.00 |
| Btnl9 | 1.00 | 1.00 | 1.00 | 1.00 | 1.00 | 1.00 | 1.00 | 1.00 | 1.00 | 1.00 | 1.02 | 0.93 |
| C030029H02Rik | 1.00 | 1.00 | 1.00 | 1.00 | 0.13 | 0.83 | 1.00 | 1.00 | 1.00 | 1.00 | 1.00 | 1.00 |
| C030046E11Rik | 1.52 | 1.77 | 1.77 | 0.79 | 1.00 | 0.93 | 0.88 | 0.14 | 1.05 | 1.00 | 0.81 | 0.95 |
| C1galt1c1 | 1.17 | 1.05 | 1.13 | 1.05 | 1.00 | 1.01 | 0.91 | 0.07 | 0.85 | 0.29 | 0.92 | 1.19 |
| C1s1 | 0.57 | 1.25 | 1.39 | 1.00 | 1.00 | 1.00 | 0.86 | 0.16 | 1.13 | 1.00 | 1.00 | 1.00 |
| C230091D08Rik | 1.18 | 0.81 | 1.09 | 1.00 | 1.19 | 0.93 | 0.87 | 0.28 | 1.21 | 1.00 | 0.78 | 0.87 |
| C2cd4d | 1.00 | 1.00 | 1.00 | 1.00 | 1.01 | 1.00 | 1.00 | 1.00 | 0.99 | 1.00 | 1.00 | 1.00 |
| C330022C24Rik | 1.00 | 1.00 | 1.00 | 1.00 | 1.00 | 1.00 | 1.15 | 0.18 | 1.02 | 1.00 | 1.00 | 1.00 |
| C4a | 1.00 | 1.00 | 1.00 | 1.00 | 1.47 | 0.84 | 0.96 | 3.85 | 1.08 | 1.06 | 1.00 | 1.00 |
| C6 | 1.00 | 1.00 | 1.00 | 1.00 | 1.00 | 1.00 | 1.00 | 1.00 | 1.00 | 1.00 | 1.00 | 1.00 |
| C730036E19Rik | 1.00 | 1.00 | 1.00 | 1.00 | 1.00 | 1.00 | 1.00 | 1.00 | 1.00 | 1.00 | 1.00 | 0.76 |
| C78339 | 1.74 | 0.76 | 1.30 | 0.90 | 0.60 | 0.88 | 1.06 | 0.15 | 1.23 | 1.56 | 1.22 | 0.74 |
| C920009B18Rik | 1.00 | 1.00 | 1.00 | 1.00 | 1.00 | 1.00 | 1.00 | 1.00 | 1.00 | 1.00 | 0.78 | 1.00 |
| Calm4 | 1.00 | 1.00 | 1.21 | 1.00 | 0.92 | 1.00 | 0.75 | 1.98 | 0.58 | 1.00 | 1.00 | 1.00 |
| Calml3 | 1.00 | 1.00 | 1.00 | 1.00 | 1.00 | 1.00 | 1.15 | 0.43 | 0.79 | 1.00 | 1.00 | 1.00 |
| Camk2n1 | 0.95 | 0.85 | 1.16 | 1.12 | 0.95 | 1.04 | 1.44 | 0.33 | 1.32 | 1.00 | 1.00 | 1.00 |
| Cap1 | 1.20 | 1.36 | 0.88 | 1.09 | 0.88 | 1.06 | 0.83 | 0.16 | 0.76 | 0.55 | 1.14 | 1.20 |
| Capg | 1.00 | 1.00 | 1.00 | 1.00 | 0.09 | 0.86 | 0.35 | 2.84 | 0.37 | 0.14 | 0.05 | 0.07 |
| Capn15 | 1.61 | 1.14 | 1.49 | 0.87 | 1.00 | 0.99 | 0.95 | 0.09 | 0.99 | 1.00 | 0.57 | 0.53 |
| Car1 | 1.00 | 1.00 | 1.00 | 1.00 | 1.00 | 1.00 | 1.00 | 1.00 | 1.00 | 0.32 | 0.54 | 0.80 |
| Car12 | 1.00 | 1.00 | 1.00 | 1.01 | 1.00 | 0.84 | 0.54 | 0.05 | 0.64 | 1.00 | 1.00 | 1.00 |
| Car2 | 1.00 | 1.00 | 1.00 | 0.55 | 0.54 | 0.58 | 1.18 | 0.65 | 0.85 | 0.31 | 0.78 | 0.81 |
| Car3 | 0.19 | 0.33 | 0.16 | 0.67 | 1.00 | 2.59 | 1.04 | 0.14 | 0.92 | 0.59 | 0.20 | 0.34 |
| Car7 | 1.00 | 1.00 | 1.00 | 1.23 | 0.49 | 1.22 | 1.00 | 1.00 | 1.00 | 1.00 | 1.00 | 1.00 |

Fig. 35- 17

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Caskin2 | 0.89 | 2.23 | 1.07 | 0.74 | 0.22 | 0.96 | 1.02 | 1.02 | 1.10 | 0.39 | 0.38 | 1.03 |
| Casp6 | 1.90 | 0.60 | 0.63 | 1.04 | 0.87 | 1.35 | 1.32 | 0.80 | 0.83 | 0.39 | 0.33 | 0.98 |
| Casp8 | 0.83 | 1.00 | 1.05 | 0.93 | 0.30 | 0.96 | 0.99 | 0.71 | 0.99 | 0.21 | 0.33 | 1.00 |
| Cav1 | 0.79 | 1.17 | 0.82 | 0.82 | 0.25 | 0.75 | 0.88 | 0.88 | 0.97 | 0.47 | 0.37 | 1.00 |
| Cbfb | 0.91 | 1.78 | 0.88 | 2.36 | 0.41 | 1.31 | 1.02 | 1.13 | 1.14 | 0.39 | 0.39 | 0.93 |
| Cbl | 1.00 | 1.00 | 1.00 | 1.00 | 1.00 | 1.00 | 1.03 | 1.00 | 1.86 | 1.00 | 1.00 | 1.03 |
| Cbx1 | 0.79 | 1.24 | 0.83 | 0.85 | 0.18 | 0.79 | 0.88 | 0.88 | 1.07 | 0.92 | 0.26 | 0.86 |
| Ccdc34 | 1.00 | 1.00 | 0.77 | 1.03 | 1.00 | 0.79 | 0.90 | 0.81 | 1.02 | 0.68 | 0.56 | 0.90 |
| Ccdc47 | 1.09 | 2.02 | 0.98 | 1.09 | 0.36 | 1.04 | 0.88 | 0.91 | 0.84 | 0.55 | 0.34 | 0.98 |
| Ccdc50 | 1.08 | 1.95 | 0.79 | 1.56 | 0.67 | 0.87 | 0.95 | 1.23 | 1.15 | 0.39 | 0.56 | 0.88 |
| Ccdc64 | 1.00 | 1.00 | 1.00 | 1.00 | 0.90 | 1.00 | 1.00 | 1.00 | 1.00 | 1.00 | 0.91 | 1.25 |
| Ccdc80 | 1.22 | 0.96 | 0.98 | 1.59 | 0.53 | 0.69 | 0.85 | 1.02 | 1.27 | 0.66 | 0.59 | 0.72 |
| Ccdc82 | 0.80 | 1.58 | 1.04 | 1.70 | 0.51 | 1.08 | 0.93 | 1.09 | 0.93 | 0.73 | 0.40 | 0.95 |
| Cckbr | 1.00 | 1.00 | 1.00 | 1.00 | 1.00 | 1.00 | 1.00 | 1.00 | 1.00 | 1.00 | 1.00 | 1.00 |
| Ccl20 | 1.00 | 1.00 | 1.00 | 1.00 | 1.00 | 1.00 | 1.00 | 1.00 | 1.00 | 1.00 | 1.00 | 1.00 |
| Ccl21a | 0.52 | 0.17 | 0.37 | 0.06 | 0.63 | 0.27 | 0.39 | 0.30 | 0.44 | 0.26 | 0.57 | 0.33 |
| Ccl21c | 1.00 | 1.56 | 0.68 | 0.86 | 1.00 | 1.00 | 2.11 | 1.00 | 0.55 | 0.21 | 0.08 | 0.44 |
| Ccnd2 | 0.57 | 1.00 | 0.95 | 1.90 | 0.30 | 1.07 | 0.42 | 0.51 | 0.55 | 0.64 | 0.19 | 1.25 |
| Ccne2 | 1.00 | 1.02 | 0.91 | 1.58 | 2.38 | 1.00 | 1.00 | 1.00 | 1.00 | 0.49 | 2.09 | 1.00 |
| Ccnt2 | 0.87 | 2.21 | 0.99 | 1.39 | 0.38 | 0.95 | 1.13 | 1.34 | 1.08 | 0.83 | 0.64 | 0.93 |
| Ccr4 | 1.00 | 1.00 | 1.00 | 1.00 | 1.00 | 1.00 | 1.00 | 1.00 | 1.00 | 1.00 | 1.00 | 1.00 |
| Ccr6 | 1.00 | 1.00 | 1.00 | 1.00 | 1.00 | 1.00 | 1.00 | 1.00 | 1.00 | 1.00 | 1.00 | 0.59 |
| Cd164 | 1.18 | 2.30 | 1.20 | 2.24 | 0.38 | 1.03 | 0.97 | 1.07 | 0.91 | 0.40 | 0.45 | 1.02 |
| Cd1d1 | 0.54 | 0.57 | 0.59 | 0.42 | 0.37 | 0.51 | 0.73 | 0.67 | 0.82 | 0.58 | 0.44 | 0.60 |
| Cd1d2 | 1.00 | 1.00 | 1.00 | 0.22 | 0.31 | 0.54 | 1.00 | 1.00 | 1.00 | 1.00 | 1.00 | 0.89 |
| Cd207 | 1.00 | 1.00 | 1.00 | 1.00 | 1.00 | 1.00 | 0.97 | 1.00 | 1.41 | 1.00 | 1.00 | 1.00 |
| Cd209f | 0.71 | 0.41 | 1.53 | 1.01 | 1.56 | 1.23 | 1.00 | 0.57 | 0.57 | 0.43 | 0.62 | 0.76 |
| Cd274 | 0.95 | 1.00 | 1.47 | 0.40 | 0.08 | 0.72 | 1.25 | 1.02 | 1.25 | 0.40 | 0.28 | 0.85 |
| Cd300ld | 1.00 | 1.00 | 1.00 | 1.00 | 1.00 | 1.00 | 1.00 | 1.00 | 1.49 | 1.00 | 0.80 | 0.51 |
| Cd300lh | 0.81 | 1.00 | 2.77 | 2.49 | 0.64 | 0.70 | 0.69 | 0.80 | 1.03 | 1.00 | 1.00 | 0.50 |
| Cd302 | 1.38 | 1.19 | 1.17 | 0.78 | 1.63 | 0.91 | 0.89 | 1.03 | 1.07 | 0.50 | 0.92 | 0.96 |
| Cd52 | 1.26 | 0.76 | 4.19 | 0.58 | 2.71 | 0.70 | 0.48 | 1.30 | 1.82 | 0.83 | 1.30 | 0.78 |
| Cdc14b | 0.97 | 1.22 | 0.87 | 3.96 | 0.65 | 1.02 | 0.62 | 0.66 | 0.55 | 0.65 | 0.26 | 0.69 |
| Cdc23 | 0.79 | 2.04 | 0.91 | 1.62 | 0.27 | 1.07 | 1.00 | 1.06 | 0.92 | 0.32 | 0.13 | 1.00 |
| Cdc40 | 0.89 | 1.74 | 0.94 | 2.48 | 0.74 | 1.16 | 1.10 | 1.11 | 0.94 | 0.33 | 0.41 | 0.95 |
| Cdc42bpg | 0.66 | 1.00 | 0.69 | 0.82 | 0.56 | 1.19 | 1.15 | 1.10 | 1.03 | 0.56 | 0.32 | 1.41 |
| Cdc42ep3 | 0.66 | 1.61 | 0.50 | 3.20 | 0.37 | 1.29 | 0.74 | 0.70 | 0.98 | 0.17 | 0.14 | 0.95 |
| Cdc6 | 1.00 | 1.00 | 1.00 | 1.00 | 1.00 | 1.00 | 1.00 | 1.00 | 1.00 | 1.00 | 1.00 | 1.00 |
| Cdcp1 | 1.00 | 1.00 | 1.00 | 1.00 | 1.00 | 1.00 | 1.00 | 1.00 | 1.00 | 1.00 | 1.00 | 1.36 |
| Cdh11 | 1.00 | 1.00 | 1.00 | 1.00 | 0.95 | 1.00 | 0.65 | 0.47 | 0.85 | 0.32 | 0.19 | 0.74 |
| Cdh13 | 0.65 | 1.14 | 0.84 | 1.14 | 0.18 | 0.98 | 0.90 | 1.11 | 0.98 | 1.00 | 0.62 | 1.04 |
| Cdh3 | 1.00 | 1.00 | 1.00 | 1.00 | 1.00 | 1.00 | 1.00 | 1.00 | 1.00 | 1.00 | 1.00 | 1.00 |
| Cdh5 | 0.73 | 1.46 | 0.89 | 1.41 | 0.15 | 1.12 | 1.28 | 1.20 | 1.10 | 0.35 | 0.18 | 0.95 |
| Cdk14 | 0.45 | 1.00 | 0.67 | 0.84 | 0.13 | 0.49 | 0.49 | 0.60 | 0.53 | 0.32 | 0.17 | 0.69 |
| Cdk5r1 | 1.00 | 1.00 | 1.00 | 1.00 | 0.16 | 1.00 | 1.00 | 1.00 | 1.00 | 1.00 | 1.00 | 1.00 |
| Cdkn2c | 1.22 | 2.28 | 1.42 | 0.49 | 0.31 | 0.88 | 1.07 | 0.89 | 0.93 | 0.19 | 0.25 | 0.79 |
| Ceacam1 | 0.97 | 1.47 | 0.72 | 1.95 | 0.19 | 1.03 | 1.06 | 1.25 | 0.94 | 0.17 | 0.21 | 0.92 |
| Ceacam10 | 1.00 | 1.00 | 1.00 | 1.00 | 1.00 | 1.00 | 1.00 | 1.00 | 1.00 | 1.00 | 1.00 | 1.00 |
| Cebpa | 0.88 | 1.26 | 1.83 | 0.49 | 0.38 | 0.82 | 1.00 | 0.82 | 1.54 | 1.05 | 0.71 | 0.97 |
| Cebpb | 3.10 | 2.53 | 1.74 | 0.19 | 0.86 | 0.73 | 1.24 | 1.57 | 1.13 | 0.77 | 1.44 | 1.03 |
| Cep170b | 1.60 | 1.94 | 1.26 | 2.16 | 0.23 | 1.61 | 1.27 | 1.37 | 1.41 | 0.71 | 0.66 | 1.25 |
| Cep68 | 0.60 | 1.46 | 0.98 | 2.15 | 0.25 | 0.91 | 1.10 | 1.24 | 1.09 | 0.82 | 0.26 | 0.92 |
| Ces1f | 1.00 | 1.00 | 1.00 | 0.40 | 1.53 | 0.54 | 1.00 | 1.00 | 1.00 | 0.88 | 1.25 | 1.09 |
| Ces5a | 1.00 | 1.00 | 1.00 | 1.00 | 1.00 | 1.00 | 1.00 | 1.00 | 1.00 | 1.00 | 1.00 | 1.00 |
| Cetn3 | 0.92 | 1.80 | 1.00 | 0.98 | 0.88 | 0.98 | 0.64 | 0.87 | 0.77 | 0.40 | 0.38 | 0.85 |
| Cflar | 0.63 | 0.86 | 0.80 | 1.26 | 0.53 | 0.83 | 0.93 | 1.13 | 1.19 | 0.47 | 0.43 | 1.14 |
| Chd3os | 1.00 | 1.00 | 1.00 | 1.14 | 0.15 | 0.60 | 1.00 | 1.00 | 0.99 | 1.00 | 0.50 | 0.36 |
| Chp1 | 1.11 | 2.14 | 1.13 | 1.19 | 0.21 | 0.96 | 1.17 | 1.23 | 1.07 | 0.64 | 0.47 | 1.21 |
| Chst14 | 0.47 | 1.42 | 0.87 | 1.25 | 0.35 | 1.15 | 0.84 | 0.57 | 0.88 | 0.27 | 0.23 | 0.87 |
| Chst15 | 0.87 | 1.00 | 1.43 | 3.25 | 0.58 | 2.99 | 1.13 | 1.40 | 0.85 | 0.94 | 0.19 | 1.34 |
| Chuk | 1.06 | 1.20 | 0.86 | 1.53 | 0.73 | 1.15 | 0.83 | 0.95 | 0.84 | 0.52 | 0.82 | 0.99 |
| Ciart | 0.47 | 0.51 | 0.29 | 0.13 | 0.42 | 0.48 | 0.72 | 0.86 | 0.54 | 0.25 | 0.56 | 0.80 |
| Cideb | 1.00 | 1.00 | 1.00 | 0.09 | 0.37 | 0.56 | 0.77 | 0.40 | 0.65 | 1.00 | 0.72 | 1.09 |
| Cish | 2.02 | 0.50 | 0.22 | 0.21 | 0.14 | 0.39 | 0.27 | 0.28 | 0.41 | 1.11 | 1.71 | 1.19 |

Fig. 35- 18

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Caskin2 | 1.69 | 1.29 | 1.51 | 0.91 | 1.17 | 0.94 | 0.96 | 1.00 | 1.07 | 0.82 | 0.62 | 1.00 |
| Casp6 | 1.02 | 1.20 | 1.10 | 0.90 | 1.66 | 0.99 | 0.72 | 0.16 | 1.02 | 1.23 | 1.28 | 0.95 |
| Casp8 | 1.00 | 1.00 | 1.05 | 0.87 | 2.42 | 0.90 | 1.04 | 0.73 | 0.84 | 1.06 | 1.10 | 1.09 |
| Cav1 | 1.17 | 0.96 | 0.71 | 0.93 | 1.76 | 0.84 | 2.98 | 1.00 | 1.72 | 0.97 | 0.78 | 0.96 |
| Cbfb | 0.64 | 0.62 | 0.81 | 1.09 | 2.16 | 0.90 | 0.75 | 0.65 | 0.80 | 0.94 | 0.84 | 1.04 |
| Cbl | 0.15 | 0.14 | 0.45 | 1.74 | 1.00 | 1.90 | 1.00 | 1.00 | 1.00 | 1.06 | 1.00 | 0.80 |
| Cbx1 | 0.56 | 0.54 | 0.76 | 1.01 | 0.95 | 0.94 | 0.97 | 1.00 | 0.98 | 0.95 | 0.54 | 0.92 |
| Ccdc34 | 0.76 | 0.89 | 0.66 | 0.81 | 0.83 | 0.83 | 1.00 | 1.00 | 1.00 | 1.01 | 0.92 | 0.88 |
| Ccdc47 | 0.92 | 0.89 | 1.07 | 1.11 | 1.26 | 0.96 | 0.97 | 1.29 | 0.93 | 1.02 | 0.86 | 0.96 |
| Ccdc50 | 0.96 | 0.80 | 1.20 | 1.13 | 1.58 | 0.99 | 0.78 | 0.50 | 0.77 | 0.95 | 0.79 | 0.97 |
| Ccdc64 | 0.58 | 0.55 | 0.68 | 1.34 | 1.00 | 1.33 | 1.00 | 1.00 | 1.00 | 0.79 | 0.67 | 1.18 |
| Ccdc80 | 1.40 | 0.89 | 0.90 | 1.00 | 1.00 | 1.03 | 0.96 | 1.00 | 1.30 | 1.12 | 0.80 | 0.96 |
| Ccdc82 | 0.74 | 0.65 | 0.88 | 1.04 | 1.10 | 0.93 | 0.87 | 1.00 | 0.91 | 0.94 | 0.66 | 0.96 |
| Cckbr | 1.00 | 1.00 | 1.00 | 1.00 | 1.00 | 1.00 | 1.00 | 1.00 | 1.00 | 1.00 | 1.00 | 1.00 |
| Ccl20 | 2.01 | 3.10 | 1.00 | 1.00 | 1.00 | 1.00 | 1.00 | 1.00 | 1.00 | 1.64 | 1.52 | 1.33 |
| Ccl21a | 1.64 | 1.59 | 1.11 | 0.76 | 0.28 | 1.29 | 0.85 | 0.21 | 0.35 | 0.50 | 0.78 | 0.62 |
| Ccl21c | 2.74 | 1.89 | 1.80 | 1.00 | 1.00 | 1.23 | 1.00 | 1.00 | 1.00 | 0.37 | 0.60 | 0.58 |
| Ccnd2 | 0.51 | 0.41 | 1.14 | 1.15 | 1.00 | 1.00 | 0.53 | 1.00 | 0.59 | 1.14 | 0.55 | 1.19 |
| Ccne2 | 0.23 | 0.11 | 0.23 | 1.00 | 1.00 | 1.00 | 1.00 | 1.00 | 1.00 | 1.00 | 1.00 | 1.00 |
| Ccnt2 | 0.56 | 0.50 | 0.86 | 1.08 | 1.24 | 1.03 | 1.11 | 1.00 | 0.90 | 1.05 | 0.63 | 0.90 |
| Ccr4 | 0.79 | 0.61 | 1.30 | 1.00 | 1.00 | 1.00 | 1.00 | 1.00 | 1.00 | 1.00 | 1.00 | 1.00 |
| Ccr6 | 0.70 | 0.44 | 1.31 | 1.00 | 1.00 | 1.00 | 1.00 | 1.00 | 1.00 | 1.24 | 0.84 | 1.13 |
| Cd164 | 0.80 | 0.77 | 0.90 | 1.02 | 1.41 | 0.98 | 0.85 | 0.47 | 0.97 | 1.09 | 0.91 | 1.16 |
| Cd1d1 | 1.07 | 1.10 | 0.94 | 0.96 | 1.00 | 0.89 | 0.59 | 0.41 | 0.78 | 0.96 | 0.99 | 0.88 |
| Cd1d2 | 0.91 | 0.93 | 0.64 | 1.00 | 1.00 | 1.00 | 0.78 | 1.00 | 0.66 | 1.00 | 1.00 | 1.00 |
| Cd207 | 0.21 | 0.19 | 0.16 | 1.00 | 1.00 | 1.00 | 0.61 | 0.27 | 0.62 | 0.77 | 0.62 | 0.98 |
| Cd209f | 1.59 | 1.75 | 1.17 | 1.00 | 1.00 | 1.00 | 1.00 | 1.00 | 1.00 | 1.06 | 1.46 | 0.70 |
| Cd274 | 0.57 | 0.44 | 0.87 | 1.34 | 1.00 | 1.03 | 1.00 | 1.00 | 1.00 | 1.26 | 0.57 | 0.88 |
| Cd300ld | 1.00 | 1.00 | 1.14 | 1.00 | 1.00 | 0.89 | 0.77 | 1.00 | 0.92 | 1.00 | 1.00 | 1.00 |
| Cd300lh | 2.60 | 0.91 | 2.83 | 0.89 | 1.00 | 2.60 | 0.91 | 1.00 | 0.46 | 1.37 | 0.66 | 1.34 |
| Cd302 | 1.64 | 1.52 | 1.70 | 0.86 | 0.90 | 0.83 | 1.08 | 0.70 | 1.16 | 0.83 | 1.10 | 0.89 |
| Cd52 | 0.80 | 1.02 | 0.90 | 0.50 | 0.48 | 1.19 | 0.83 | 0.75 | 0.59 | 0.70 | 1.04 | 0.83 |
| Cdc14b | 2.00 | 1.31 | 1.85 | 1.07 | 1.34 | 0.98 | 0.52 | 1.00 | 0.67 | 0.83 | 0.61 | 0.79 |
| Cdc23 | 0.77 | 0.77 | 0.84 | 0.87 | 1.00 | 0.93 | 1.19 | 1.00 | 0.92 | 0.92 | 0.77 | 0.92 |
| Cdc40 | 0.86 | 0.91 | 0.95 | 1.06 | 1.45 | 0.90 | 1.33 | 1.04 | 1.02 | 1.10 | 0.91 | 1.02 |
| Cdc42bpg | 1.36 | 1.14 | 1.48 | 1.18 | 1.38 | 1.10 | 0.79 | 1.00 | 0.82 | 0.96 | 0.70 | 1.06 |
| Cdc42ep3 | 1.07 | 0.98 | 1.14 | 0.97 | 1.00 | 0.99 | 1.09 | 1.00 | 1.00 | 1.03 | 0.82 | 1.14 |
| Cdc6 | 0.18 | 0.25 | 0.34 | 1.00 | 1.00 | 1.00 | 1.00 | 1.00 | 1.00 | 1.00 | 1.00 | 1.00 |
| Cdcp1 | 1.13 | 0.73 | 2.02 | 1.94 | 1.00 | 1.56 | 1.36 | 1.00 | 1.09 | 1.18 | 0.35 | 1.10 |
| Cdh11 | 0.72 | 0.73 | 1.03 | 0.75 | 1.00 | 0.56 | 1.00 | 1.00 | 1.00 | 0.73 | 0.53 | 0.79 |
| Cdh13 | 1.27 | 0.91 | 1.07 | 1.04 | 1.00 | 1.46 | 1.00 | 1.00 | 1.00 | 0.85 | 0.41 | 0.68 |
| Cdh3 | 1.97 | 1.74 | 1.97 | 0.73 | 1.00 | 0.57 | 1.00 | 1.00 | 1.00 | 1.00 | 1.00 | 1.00 |
| Cdh5 | 1.55 | 1.11 | 1.31 | 1.02 | 1.00 | 0.99 | 1.08 | 1.00 | 1.00 | 0.97 | 0.80 | 1.02 |
| Cdk14 | 0.48 | 0.39 | 0.59 | 0.55 | 1.00 | 0.61 | 1.00 | 1.00 | 1.00 | 0.49 | 0.29 | 0.44 |
| Cdk5r1 | 0.54 | 0.39 | 0.76 | 1.00 | 1.00 | 1.00 | 1.00 | 1.00 | 1.00 | 1.00 | 1.00 | 1.00 |
| Cdkn2c | 0.79 | 0.92 | 0.70 | 0.87 | 3.46 | 1.09 | 0.66 | 1.00 | 0.62 | 0.99 | 1.29 | 1.09 |
| Ceacam1 | 0.86 | 0.83 | 1.69 | 1.20 | 1.63 | 1.09 | 0.80 | 0.34 | 0.83 | 1.25 | 0.83 | 1.03 |
| Ceacam10 | 1.51 | 0.83 | 1.14 | 1.00 | 1.00 | 1.00 | 1.00 | 1.00 | 1.00 | 2.07 | 2.36 | 1.40 |
| Cebpa | 1.19 | 1.05 | 1.14 | 0.78 | 0.71 | 1.10 | 0.43 | 0.67 | 0.58 | 0.97 | 0.89 | 0.93 |
| Cebpb | 1.73 | 2.18 | 1.18 | 2.03 | 3.42 | 1.99 | 1.16 | 0.86 | 1.34 | 0.94 | 1.60 | 0.89 |
| Cep170b | 1.49 | 1.23 | 1.53 | 1.32 | 1.24 | 1.25 | 1.32 | 0.88 | 1.34 | 0.96 | 0.81 | 1.02 |
| Cep68 | 0.61 | 0.52 | 0.86 | 0.92 | 1.00 | 0.97 | 0.82 | 1.00 | 0.90 | 0.98 | 0.62 | 1.00 |
| Ces1f | 0.95 | 1.05 | 0.74 | 1.02 | 1.20 | 1.09 | 0.13 | 0.16 | 0.29 | 3.01 | 4.16 | 2.13 |
| Ces5a | 1.00 | 1.00 | 1.00 | 1.00 | 1.00 | 1.00 | 1.00 | 1.00 | 1.00 | 1.00 | 1.00 | 1.00 |
| Cetn3 | 0.97 | 1.00 | 0.88 | 0.84 | 2.96 | 0.82 | 0.89 | 0.94 | 0.89 | 0.93 | 1.19 | 1.09 |
| Cflar | 0.63 | 0.60 | 0.92 | 0.93 | 1.10 | 0.97 | 0.76 | 0.33 | 0.84 | 1.03 | 0.82 | 1.00 |
| Chd3os | 0.31 | 0.32 | 0.49 | 0.71 | 1.00 | 0.79 | 1.00 | 1.00 | 0.90 | 0.79 | 0.71 | 0.76 |
| Chp1 | 0.82 | 0.80 | 0.97 | 0.98 | 1.68 | 0.99 | 1.09 | 0.48 | 0.94 | 1.04 | 0.75 | 1.02 |
| Chst14 | 1.04 | 1.00 | 1.09 | 0.91 | 1.00 | 0.98 | 1.05 | 1.00 | 1.01 | 0.93 | 0.91 | 0.84 |
| Chst15 | 1.08 | 0.84 | 1.26 | 1.37 | 1.00 | 1.69 | 1.11 | 1.00 | 1.40 | 0.90 | 0.56 | 0.93 |
| Chuk | 0.91 | 0.94 | 0.84 | 1.08 | 1.69 | 0.90 | 0.97 | 0.42 | 0.93 | 0.99 | 1.07 | 1.06 |
| Ciart | 1.26 | 2.05 | 1.08 | 0.31 | 1.85 | 0.76 | 0.67 | 0.25 | 0.49 | 0.84 | 1.28 | 0.89 |
| Cideb | 1.00 | 1.00 | 1.00 | 0.86 | 1.14 | 0.86 | 1.09 | 0.41 | 1.02 | 1.27 | 1.54 | 1.30 |
| Cish | 1.19 | 1.07 | 1.05 | 1.08 | 3.12 | 1.42 | 0.30 | 1.07 | 0.45 | 0.66 | 0.78 | 0.85 |

Fig. 35- 19

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Caskin2 | 1.00 | 1.06 | 0.86 | 1.04 | 0.14 | 1.11 | 0.90 | 1.00 | 1.05 | 0.98 | 0.98 | 1.03 |
| Casp6 | 0.96 | 1.04 | 0.94 | 0.89 | 0.58 | 1.03 | 0.91 | 0.32 | 0.98 | 1.38 | 1.02 | 1.26 |
| Casp8 | 0.90 | 0.87 | 0.73 | 0.92 | 0.25 | 1.01 | 0.82 | 1.00 | 0.81 | 1.01 | 0.82 | 0.96 |
| Cav1 | 1.09 | 1.03 | 1.43 | 0.68 | 0.19 | 0.49 | 1.06 | 0.49 | 1.26 | 0.95 | 0.71 | 0.98 |
| Cbfb | 0.97 | 0.86 | 1.04 | 1.02 | 0.34 | 1.07 | 1.04 | 0.36 | 0.91 | 0.97 | 0.69 | 0.96 |
| Cbl | 0.83 | 0.58 | 0.31 | 1.00 | 0.45 | 0.51 | 1.18 | 1.77 | 1.04 | 0.79 | 0.36 | 1.39 |
| Cbx1 | 0.95 | 0.80 | 0.85 | 1.03 | 1.00 | 0.88 | 1.25 | 1.19 | 1.18 | 1.07 | 0.67 | 1.19 |
| Ccdc34 | 0.70 | 0.51 | 0.67 | 0.61 | 1.00 | 0.73 | 0.95 | 0.41 | 0.94 | 0.81 | 1.02 | 0.75 |
| Ccdc47 | 0.96 | 0.88 | 0.90 | 1.13 | 0.95 | 1.21 | 0.97 | 0.59 | 1.00 | 1.04 | 0.82 | 1.05 |
| Ccdc50 | 0.99 | 0.82 | 0.84 | 0.93 | 0.18 | 0.80 | 1.08 | 0.88 | 1.00 | 0.86 | 0.53 | 1.02 |
| Ccdc64 | 0.87 | 0.92 | 0.66 | 0.65 | 1.00 | 0.47 | 0.99 | 1.00 | 0.81 | 0.55 | 0.69 | 1.12 |
| Ccdc80 | 0.85 | 0.90 | 0.97 | 0.43 | 0.16 | 0.35 | 0.80 | 1.00 | 1.09 | 0.70 | 0.42 | 0.72 |
| Ccdc82 | 0.92 | 1.01 | 1.06 | 0.95 | 0.58 | 0.89 | 0.94 | 1.00 | 1.05 | 0.88 | 0.68 | 0.89 |
| Cckbr | 1.84 | 1.80 | 1.51 | 1.00 | 1.00 | 1.00 | 1.00 | 1.00 | 1.00 | 1.00 | 1.62 | 1.00 |
| Ccl20 | 1.19 | 2.23 | 1.00 | 1.00 | 1.00 | 1.00 | 1.00 | 1.00 | 1.00 | 1.00 | 1.00 | 1.00 |
| Ccl21a | 0.66 | 0.63 | 0.69 | 1.03 | 0.57 | 0.79 | 0.98 | 0.82 | 1.44 | 0.93 | 0.99 | 0.84 |
| Ccl21c | 1.00 | 0.73 | 0.80 | 0.61 | 1.00 | 1.25 | 1.00 | 1.00 | 1.00 | 1.54 | 1.51 | 1.41 |
| Ccnd2 | 0.61 | 0.53 | 0.66 | 0.59 | 0.06 | 0.61 | 1.41 | 1.00 | 1.19 | 0.79 | 0.42 | 1.03 |
| Ccne2 | 1.00 | 0.88 | 1.00 | 1.00 | 1.00 | 1.00 | 0.93 | 0.70 | 0.77 | 0.54 | 1.17 | 0.68 |
| Ccnt2 | 0.93 | 0.91 | 0.76 | 1.13 | 0.29 | 0.82 | 1.01 | 0.72 | 0.97 | 0.97 | 0.58 | 0.99 |
| Ccr4 | 1.00 | 1.00 | 1.00 | 1.00 | 1.00 | 1.00 | 0.87 | 1.32 | 1.05 | 0.52 | 0.38 | 0.76 |
| Ccr6 | 1.00 | 1.00 | 1.00 | 1.00 | 1.00 | 1.00 | 0.93 | 1.33 | 0.72 | 0.54 | 0.15 | 0.51 |
| Cd164 | 1.04 | 0.95 | 0.99 | 0.95 | 0.33 | 0.90 | 0.98 | 0.69 | 0.92 | 1.20 | 0.89 | 1.07 |
| Cd1d1 | 0.69 | 0.61 | 0.88 | 0.14 | 0.13 | 0.27 | 1.00 | 1.00 | 1.00 | 1.07 | 0.98 | 1.17 |
| Cd1d2 | 1.00 | 1.00 | 1.00 | 0.18 | 0.95 | 0.28 | 1.00 | 1.00 | 1.00 | 0.89 | 0.81 | 1.29 |
| Cd207 | 1.00 | 1.00 | 1.00 | 1.00 | 1.00 | 1.00 | 1.00 | 1.00 | 1.00 | 0.07 | 0.06 | 0.08 |
| Cd209f | 1.00 | 0.67 | 0.96 | 0.68 | 1.66 | 0.92 | 1.00 | 0.64 | 0.57 | 1.00 | 1.00 | 1.00 |
| Cd274 | 1.17 | 0.72 | 1.51 | 0.83 | 1.00 | 0.78 | 1.44 | 1.00 | 1.20 | 0.91 | 0.72 | 1.01 |
| Cd300ld | 1.00 | 1.00 | 1.00 | 0.41 | 1.00 | 0.16 | 1.00 | 1.00 | 1.00 | 0.36 | 0.34 | 0.58 |
| Cd300lh | 1.32 | 1.24 | 0.70 | 0.64 | 0.19 | 0.58 | 0.56 | 1.00 | 0.40 | 0.98 | 0.87 | 1.51 |
| Cd302 | 1.07 | 0.84 | 1.09 | 0.71 | 0.89 | 1.04 | 0.70 | 0.64 | 0.76 | 0.93 | 1.25 | 0.92 |
| Cd52 | 1.65 | 0.53 | 1.95 | 0.49 | 1.33 | 0.11 | 1.00 | 1.01 | 0.45 | 0.72 | 0.75 | 0.77 |
| Cdc14b | 0.80 | 0.84 | 0.90 | 1.01 | 1.00 | 0.79 | 0.90 | 0.98 | 1.13 | 0.87 | 0.59 | 1.15 |
| Cdc23 | 0.90 | 0.76 | 0.87 | 0.88 | 0.72 | 0.94 | 0.91 | 0.89 | 0.90 | 1.00 | 0.79 | 1.00 |
| Cdc40 | 1.15 | 1.09 | 0.92 | 1.06 | 0.33 | 1.26 | 0.96 | 0.98 | 0.99 | 1.16 | 0.94 | 1.06 |
| Cdc42bpg | 1.17 | 1.27 | 0.99 | 0.97 | 1.00 | 1.20 | 0.90 | 1.00 | 1.07 | 0.88 | 0.71 | 1.06 |
| Cdc42ep3 | 0.82 | 0.84 | 1.41 | 1.11 | 0.44 | 1.28 | 0.98 | 0.18 | 1.03 | 0.88 | 0.63 | 0.89 |
| Cdc6 | 0.58 | 0.50 | 0.47 | 1.00 | 1.00 | 1.00 | 1.41 | 0.86 | 1.41 | 0.40 | 0.39 | 0.41 |
| Cdcp1 | 0.97 | 0.98 | 0.71 | 1.00 | 1.00 | 1.00 | 1.00 | 1.00 | 1.00 | 1.00 | 1.00 | 0.99 |
| Cdh11 | 0.73 | 0.64 | 0.97 | 0.93 | 1.00 | 0.88 | 1.21 | 1.00 | 0.85 | 0.80 | 0.67 | 0.86 |
| Cdh13 | 1.04 | 0.90 | 1.18 | 1.02 | 0.12 | 1.12 | 1.27 | 1.00 | 1.14 | 1.00 | 1.42 | 1.00 |
| Cdh3 | 0.70 | 0.78 | 0.61 | 1.01 | 1.00 | 2.15 | 0.92 | 1.00 | 1.04 | 1.01 | 1.00 | 1.06 |
| Cdh5 | 1.14 | 1.24 | 1.15 | 1.14 | 0.13 | 1.13 | 1.21 | 1.00 | 1.06 | 1.03 | 0.79 | 1.13 |
| Cdk14 | 0.42 | 0.40 | 0.38 | 0.39 | 0.35 | 0.30 | 1.02 | 1.27 | 1.10 | 0.58 | 0.74 | 0.74 |
| Cdk5r1 | 1.00 | 1.00 | 1.00 | 1.42 | 1.00 | 1.12 | 0.95 | 1.00 | 1.25 | 0.97 | 2.25 | 1.03 |
| Cdkn2c | 1.03 | 0.78 | 1.38 | 0.61 | 0.54 | 0.89 | 0.90 | 0.55 | 0.96 | 0.81 | 0.92 | 0.84 |
| Ceacam1 | 1.36 | 1.34 | 1.38 | 1.37 | 0.44 | 1.30 | 0.99 | 0.76 | 1.05 | 0.94 | 0.51 | 0.85 |
| Ceacam10 | 1.42 | 1.80 | 1.79 | 1.00 | 3.83 | 0.08 | 0.93 | 1.00 | 1.25 | 1.00 | 1.44 | 1.01 |
| Cebpa | 0.80 | 0.88 | 1.08 | 0.29 | 0.16 | 0.70 | 0.84 | 2.50 | 0.93 | 0.78 | 0.78 | 0.78 |
| Cebpb | 0.96 | 1.34 | 1.21 | 1.79 | 3.91 | 1.21 | 1.08 | 1.01 | 1.29 | 1.43 | 2.23 | 0.98 |
| Cep170b | 0.88 | 1.04 | 0.79 | 1.59 | 0.58 | 1.63 | 1.20 | 1.69 | 1.20 | 1.15 | 2.03 | 1.17 |
| Cep68 | 0.99 | 0.86 | 0.94 | 0.85 | 0.40 | 0.76 | 1.33 | 1.00 | 1.11 | 1.13 | 0.63 | 1.24 |
| Ces1f | 0.96 | 1.36 | 1.69 | 0.35 | 1.37 | 0.62 | 1.00 | 1.00 | 1.00 | 1.00 | 1.00 | 1.00 |
| Ces5a | 1.00 | 1.00 | 1.00 | 1.00 | 1.91 | 0.03 | 1.11 | 0.99 | 0.79 | 1.00 | 1.00 | 1.00 |
| Cetn3 | 0.83 | 0.80 | 1.02 | 0.88 | 0.70 | 0.93 | 1.07 | 0.15 | 0.86 | 1.11 | 1.03 | 0.87 |
| Cflar | 1.03 | 0.96 | 0.88 | 1.04 | 0.14 | 0.88 | 1.07 | 1.00 | 1.07 | 0.88 | 0.59 | 0.96 |
| Chd3os | 1.00 | 1.04 | 1.23 | 0.74 | 1.00 | 1.00 | 0.92 | 0.42 | 0.94 | 0.61 | 2.34 | 0.81 |
| Chp1 | 0.97 | 0.98 | 0.91 | 0.87 | 0.22 | 1.00 | 0.98 | 0.45 | 0.90 | 0.94 | 0.91 | 0.96 |
| Chst14 | 1.00 | 0.81 | 1.25 | 0.75 | 0.53 | 0.75 | 0.97 | 1.00 | 1.29 | 0.99 | 0.77 | 0.97 |
| Chst15 | 1.17 | 1.18 | 1.11 | 1.46 | 0.44 | 1.25 | 1.09 | 1.09 | 0.86 | 1.20 | 0.95 | 1.39 |
| Chuk | 0.77 | 0.59 | 0.68 | 1.05 | 0.53 | 1.22 | 0.67 | 0.42 | 0.75 | 1.09 | 0.89 | 1.01 |
| Ciart | 0.49 | 0.84 | 0.65 | 0.24 | 1.00 | 0.75 | 0.93 | 0.58 | 1.06 | 0.68 | 0.97 | 0.67 |
| Cideb | 1.03 | 1.02 | 0.77 | 2.06 | 1.00 | 2.96 | 1.00 | 1.00 | 1.00 | 1.00 | 1.00 | 1.00 |
| Cish | 1.15 | 1.38 | 0.99 | 0.61 | 3.98 | 0.81 | 0.87 | 0.94 | 0.47 | 0.60 | 0.63 | 0.71 |

Fig. 35- 20

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Caskin2 | 0.92 | 0.95 | 1.51 | 0.89 | 1.00 | 1.02 | 0.89 | 0.15 | 0.99 | 1.00 | 0.57 | 0.90 |
| Casp6 | 1.10 | 0.65 | 1.07 | 0.78 | 1.00 | 0.76 | 0.72 | 0.21 | 0.91 | 0.81 | 1.20 | 1.40 |
| Casp8 | 1.04 | 0.57 | 0.96 | 0.86 | 1.00 | 1.00 | 0.89 | 0.13 | 0.92 | 0.33 | 1.03 | 1.08 |
| Cav1 | 0.73 | 1.04 | 1.13 | 0.67 | 1.00 | 1.10 | 1.08 | 0.25 | 1.29 | 1.00 | 1.00 | 1.00 |
| Cbfb | 1.77 | 1.55 | 0.91 | 0.87 | 1.00 | 1.02 | 0.79 | 0.08 | 0.96 | 0.53 | 1.02 | 1.05 |
| Cbl | 1.00 | 1.00 | 1.00 | 0.62 | 1.00 | 0.68 | 1.00 | 1.00 | 1.00 | 1.00 | 1.00 | 1.00 |
| Cbx1 | 1.35 | 1.27 | 1.90 | 0.86 | 2.43 | 0.77 | 0.86 | 0.14 | 1.00 | 0.22 | 0.73 | 0.77 |
| Ccdc34 | 1.00 | 1.00 | 1.00 | 1.08 | 1.32 | 0.95 | 1.05 | 0.13 | 0.96 | 0.51 | 0.94 | 0.95 |
| Ccdc47 | 1.07 | 0.91 | 1.28 | 1.06 | 1.13 | 0.98 | 0.98 | 0.12 | 1.17 | 0.40 | 0.95 | 0.94 |
| Ccdc50 | 0.85 | 0.95 | 1.31 | 0.86 | 0.92 | 1.01 | 0.90 | 0.16 | 1.11 | 0.62 | 0.86 | 0.83 |
| Ccdc64 | 1.00 | 1.00 | 1.00 | 0.86 | 1.00 | 0.91 | 0.88 | 0.05 | 0.73 | 1.00 | 1.00 | 1.00 |
| Ccdc80 | 0.70 | 0.84 | 1.04 | 0.78 | 0.59 | 0.99 | 1.27 | 0.79 | 1.46 | 1.00 | 1.00 | 1.00 |
| Ccdc82 | 0.97 | 1.00 | 1.00 | 0.94 | 1.00 | 1.04 | 1.02 | 0.17 | 1.17 | 0.48 | 0.85 | 0.92 |
| Cckbr | 1.00 | 1.00 | 1.00 | 0.80 | 0.10 | 0.78 | 1.00 | 1.00 | 1.00 | 1.00 | 1.00 | 1.00 |
| Ccl20 | 1.00 | 1.00 | 1.00 | 1.00 | 1.00 | 1.00 | 0.36 | 0.19 | 0.34 | 1.00 | 1.00 | 1.00 |
| Ccl21a | 0.35 | 0.48 | 0.48 | 1.00 | 0.70 | 1.00 | 0.79 | 1.97 | 0.63 | 1.00 | 1.00 | 1.00 |
| Ccl21c | 1.00 | 1.00 | 1.00 | 1.00 | 1.00 | 1.00 | 1.43 | 0.28 | 0.93 | 1.00 | 1.00 | 1.00 |
| Ccnd2 | 0.55 | 0.83 | 0.64 | 0.80 | 1.00 | 0.86 | 0.57 | 0.04 | 0.74 | 0.35 | 0.65 | 0.81 |
| Ccne2 | 1.00 | 1.00 | 1.00 | 0.88 | 1.12 | 0.80 | 1.25 | 2.04 | 0.71 | 0.38 | 0.69 | 0.67 |
| Ccnt2 | 1.13 | 1.74 | 1.42 | 0.79 | 0.51 | 0.78 | 0.86 | 0.20 | 1.21 | 0.58 | 0.86 | 0.82 |
| Ccr4 | 1.00 | 1.00 | 1.00 | 1.00 | 1.00 | 1.00 | 0.51 | 0.19 | 0.85 | 1.00 | 1.00 | 1.00 |
| Ccr6 | 1.00 | 1.00 | 1.00 | 0.56 | 1.00 | 0.81 | 1.00 | 1.00 | 1.48 | 1.00 | 0.44 | 0.40 |
| Cd164 | 1.00 | 0.83 | 0.72 | 0.95 | 0.65 | 0.95 | 0.92 | 0.17 | 1.11 | 0.59 | 1.36 | 1.35 |
| Cd1d1 | 1.00 | 1.00 | 1.00 | 0.84 | 1.39 | 1.21 | 0.80 | 0.51 | 0.87 | 0.86 | 0.79 | 1.01 |
| Cd1d2 | 1.00 | 1.00 | 1.00 | 1.00 | 1.00 | 1.00 | 1.00 | 1.00 | 1.00 | 1.00 | 0.94 | 0.72 |
| Cd207 | 1.00 | 1.00 | 1.00 | 1.00 | 1.00 | 1.00 | 0.74 | 0.80 | 1.04 | 1.00 | 1.00 | 1.00 |
| Cd209f | 1.00 | 1.00 | 1.11 | 1.00 | 1.00 | 1.00 | 0.48 | 0.85 | 0.53 | 0.19 | 0.15 | 0.12 |
| Cd274 | 1.00 | 1.00 | 1.00 | 1.00 | 1.00 | 0.99 | 0.91 | 0.29 | 1.22 | 0.80 | 0.99 | 0.96 |
| Cd300ld | 1.00 | 1.00 | 1.00 | 1.00 | 1.00 | 1.00 | 1.00 | 1.00 | 1.00 | 0.69 | 0.70 | 0.74 |
| Cd300lh | 0.93 | 1.00 | 1.17 | 1.00 | 1.00 | 0.50 | 0.97 | 0.07 | 1.96 | 1.00 | 1.32 | 0.62 |
| Cd302 | 1.00 | 0.59 | 0.86 | 1.12 | 0.08 | 1.02 | 1.10 | 1.50 | 1.28 | 0.85 | 0.89 | 0.95 |
| Cd52 | 1.00 | 1.96 | 0.50 | 0.90 | 2.54 | 1.90 | 0.58 | 3.98 | 0.75 | 2.67 | 1.45 | 1.41 |
| Cdc14b | 1.00 | 1.00 | 1.00 | 0.85 | 1.00 | 1.00 | 0.64 | 0.11 | 0.88 | 1.00 | 1.12 | 0.91 |
| Cdc23 | 1.01 | 0.69 | 0.64 | 0.94 | 1.00 | 0.98 | 0.77 | 0.11 | 1.05 | 0.18 | 0.80 | 0.95 |
| Cdc40 | 1.53 | 1.00 | 1.40 | 0.95 | 0.90 | 1.03 | 1.19 | 0.13 | 1.23 | 0.53 | 1.17 | 1.11 |
| Cdc42bpg | 1.15 | 0.69 | 0.95 | 0.80 | 1.00 | 0.82 | 1.05 | 0.06 | 1.02 | 1.00 | 1.02 | 1.00 |
| Cdc42ep3 | 1.93 | 0.62 | 1.41 | 1.03 | 0.62 | 1.10 | 1.09 | 0.08 | 1.16 | 0.34 | 0.98 | 1.13 |
| Cdc6 | 1.00 | 1.00 | 1.00 | 1.00 | 1.00 | 1.00 | 1.09 | 1.18 | 0.83 | 0.55 | 0.65 | 0.81 |
| Cdcp1 | 1.11 | 0.72 | 1.20 | 1.00 | 1.00 | 1.00 | 0.68 | 0.16 | 0.95 | 1.00 | 1.00 | 1.00 |
| Cdh11 | 1.00 | 1.00 | 1.00 | 0.87 | 1.00 | 0.92 | 0.96 | 0.21 | 1.18 | 1.00 | 1.00 | 1.00 |
| Cdh13 | 1.00 | 1.00 | 1.00 | 0.93 | 1.00 | 1.03 | 0.92 | 0.08 | 1.15 | 1.00 | 1.00 | 1.00 |
| Cdh3 | 1.00 | 1.00 | 1.00 | 1.00 | 1.00 | 1.00 | 0.87 | 0.16 | 1.05 | 1.00 | 1.00 | 1.00 |
| Cdh5 | 1.14 | 1.21 | 1.13 | 0.94 | 1.00 | 1.05 | 1.46 | 0.21 | 1.85 | 1.00 | 1.26 | 1.54 |
| Cdk14 | 1.00 | 1.00 | 1.00 | 1.02 | 0.54 | 0.96 | 0.64 | 0.28 | 0.68 | 1.00 | 0.32 | 0.36 |
| Cdk5r1 | 1.00 | 1.00 | 1.00 | 1.02 | 2.77 | 0.94 | 0.93 | 0.23 | 0.82 | 0.74 | 0.91 | 0.92 |
| Cdkn2c | 1.02 | 1.36 | 1.40 | 1.03 | 1.00 | 1.58 | 0.72 | 0.12 | 0.89 | 0.35 | 0.96 | 1.05 |
| Ceacam1 | 0.78 | 0.78 | 0.95 | 0.81 | 1.00 | 1.02 | 1.24 | 0.46 | 1.46 | 0.28 | 0.87 | 0.94 |
| Ceacam10 | 1.00 | 1.00 | 1.00 | 1.00 | 1.95 | 1.00 | 1.00 | 1.00 | 1.00 | 0.96 | 0.84 | 1.23 |
| Cebpa | 0.90 | 0.87 | 0.96 | 0.97 | 0.72 | 1.16 | 0.93 | 0.51 | 0.81 | 1.21 | 1.66 | 1.50 |
| Cebpb | 1.89 | 1.84 | 1.07 | 1.21 | 1.97 | 1.27 | 1.96 | 0.96 | 1.09 | 2.97 | 3.81 | 1.62 |
| Cep170b | 1.35 | 1.06 | 1.23 | 1.14 | 1.55 | 1.03 | 0.82 | 0.13 | 0.83 | 1.00 | 1.00 | 1.00 |
| Cep68 | 0.69 | 0.84 | 1.01 | 0.89 | 1.00 | 0.94 | 0.60 | 0.14 | 0.87 | 0.50 | 0.73 | 0.76 |
| Ces1f | 1.00 | 1.00 | 1.00 | 1.00 | 1.22 | 1.00 | 1.00 | 1.47 | 1.00 | 1.00 | 1.00 | 1.00 |
| Ces5a | 1.00 | 1.00 | 1.00 | 1.00 | 1.00 | 1.00 | 1.00 | 1.00 | 1.00 | 1.00 | 1.00 | 1.00 |
| Cetn3 | 0.83 | 0.99 | 0.83 | 1.05 | 2.35 | 0.96 | 0.81 | 0.27 | 0.99 | 0.56 | 1.04 | 1.19 |
| Cflar | 0.86 | 1.08 | 1.10 | 0.93 | 1.00 | 0.93 | 0.81 | 0.33 | 1.02 | 0.72 | 0.93 | 1.08 |
| Chd3os | 1.00 | 1.00 | 1.00 | 1.12 | 2.56 | 1.02 | 0.76 | 0.19 | 0.73 | 0.76 | 0.48 | 0.87 |
| Chp1 | 1.23 | 1.34 | 1.12 | 1.15 | 1.00 | 1.03 | 1.08 | 0.11 | 1.08 | 0.45 | 1.12 | 1.01 |
| Chst14 | 1.00 | 1.00 | 0.93 | 0.90 | 1.00 | 0.94 | 0.81 | 0.08 | 1.09 | 0.50 | 0.95 | 0.98 |
| Chst15 | 1.00 | 1.00 | 1.00 | 1.00 | 1.00 | 0.99 | 0.84 | 0.16 | 0.90 | 0.39 | 0.91 | 0.88 |
| Chuk | 1.34 | 1.20 | 1.19 | 0.94 | 0.18 | 0.97 | 1.02 | 0.34 | 1.06 | 0.72 | 1.07 | 1.12 |
| Ciart | 0.80 | 0.58 | 0.69 | 0.68 | 0.43 | 0.74 | 0.93 | 0.38 | 0.86 | 1.00 | 1.00 | 1.00 |
| Cideb | 1.00 | 1.00 | 1.00 | 1.33 | 0.51 | 0.66 | 1.00 | 1.00 | 1.00 | 1.00 | 1.00 | 1.00 |
| Cish | 0.89 | 1.32 | 0.95 | 1.00 | 1.54 | 1.03 | 1.12 | 0.67 | 0.71 | 0.63 | 1.04 | 0.94 |

Fig. 35-21

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ckap2 | 1.00 | 1.00 | 1.00 | 1.00 | 1.00 | 1.00 | 1.00 | 1.00 | 1.00 | 1.00 | 1.00 | 1.00 |
| Cks2 | 1.00 | 1.00 | 1.00 | 1.68 | 1.00 | 1.00 | 0.64 | 1.00 | 1.00 | 0.60 | 1.08 | 0.76 |
| Clca5 | 1.00 | 1.00 | 1.00 | 1.00 | 1.00 | 1.00 | 1.00 | 1.00 | 1.00 | 1.00 | 1.00 | 1.00 |
| Clcf1 | 1.00 | 1.00 | 1.00 | 1.02 | 1.00 | 1.00 | 1.26 | 0.79 | 0.75 | 1.00 | 0.19 | 0.89 |
| Clcn3 | 0.67 | 1.60 | 0.87 | 1.31 | 0.19 | 0.86 | 0.77 | 0.83 | 0.95 | 0.30 | 0.48 | 0.99 |
| Cldn13 | 1.00 | 1.00 | 1.00 | 1.00 | 1.00 | 1.00 | 1.00 | 1.00 | 1.00 | 2.18 | 1.25 | 1.00 |
| Cldn23 | 1.00 | 1.00 | 1.00 | 1.00 | 1.00 | 1.00 | 1.00 | 1.00 | 1.35 | 1.00 | 0.64 | 1.21 |
| Cldn25 | 1.47 | 2.04 | 0.92 | 1.56 | 0.24 | 1.01 | 0.89 | 0.96 | 0.97 | 0.26 | 0.26 | 1.08 |
| Clec1a | 0.78 | 1.00 | 1.44 | 2.65 | 0.51 | 1.47 | 1.28 | 1.25 | 1.29 | 0.30 | 0.17 | 0.72 |
| Clec2g | 1.00 | 1.00 | 1.00 | 1.00 | 1.00 | 1.00 | 1.00 | 1.00 | 1.00 | 1.00 | 1.00 | 1.00 |
| Clgn | 1.00 | 1.00 | 1.00 | 1.00 | 1.00 | 1.00 | 1.00 | 1.00 | 1.00 | 1.00 | 1.00 | 1.00 |
| Cmbl | 1.04 | 1.08 | 0.57 | 0.39 | 0.77 | 0.91 | 1.11 | 0.91 | 0.61 | 0.37 | 0.71 | 0.97 |
| Cmpk1 | 0.99 | 1.97 | 1.14 | 1.07 | 0.28 | 0.96 | 0.75 | 1.00 | 1.06 | 0.17 | 0.19 | 1.04 |
| Cmtm6 | 0.99 | 1.76 | 1.26 | 1.38 | 0.36 | 0.98 | 0.93 | 1.01 | 1.10 | 0.48 | 0.43 | 1.06 |
| Cnnm4 | 0.76 | 1.00 | 1.13 | 1.13 | 0.47 | 1.36 | 1.14 | 1.44 | 1.07 | 1.00 | 0.56 | 1.20 |
| Cnot3 | 0.83 | 1.00 | 0.86 | 0.63 | 0.18 | 0.98 | 1.04 | 0.81 | 1.08 | 0.51 | 0.23 | 0.93 |
| Cntfr | 1.59 | 3.15 | 1.21 | 0.33 | 0.19 | 0.54 | 1.19 | 1.61 | 0.95 | 0.62 | 0.81 | 1.26 |
| Cog1 | 1.05 | 1.77 | 1.24 | 1.21 | 0.15 | 1.01 | 1.70 | 1.24 | 1.11 | 0.85 | 0.22 | 1.15 |
| Cog3 | 0.86 | 2.23 | 0.90 | 1.09 | 0.42 | 1.06 | 1.08 | 0.98 | 0.84 | 0.56 | 0.58 | 0.98 |
| Col13a1 | 1.00 | 1.00 | 1.00 | 1.00 | 1.00 | 1.00 | 1.00 | 1.00 | 1.00 | 0.87 | 0.17 | 0.84 |
| Col3a1 | 0.73 | 0.66 | 0.85 | 0.66 | 0.37 | 0.39 | 0.52 | 0.37 | 0.85 | 0.19 | 0.25 | 0.73 |
| Col4a3 | 1.46 | 1.00 | 1.00 | 1.00 | 1.00 | 1.00 | 1.54 | 1.03 | 1.00 | 0.30 | 0.14 | 1.40 |
| Col4a3bp | 0.85 | 1.56 | 0.99 | 1.52 | 0.43 | 0.99 | 0.98 | 1.03 | 1.10 | 0.50 | 0.61 | 0.99 |
| Coq2 | 0.87 | 0.94 | 0.82 | 0.78 | 1.29 | 0.93 | 0.88 | 0.91 | 0.81 | 0.50 | 0.90 | 0.88 |
| Cox15 | 0.82 | 1.52 | 1.01 | 0.73 | 0.11 | 0.83 | 0.87 | 0.98 | 0.80 | 0.69 | 0.23 | 0.93 |
| Cox6c | 1.07 | 0.51 | 0.66 | 0.14 | 2.64 | 0.71 | 0.83 | 0.70 | 0.72 | 0.97 | 1.81 | 0.75 |
| Cpeb4 | 0.87 | 1.86 | 0.89 | 3.62 | 0.21 | 0.93 | 1.08 | 1.72 | 1.21 | 0.50 | 0.43 | 1.04 |
| Cped1 | 1.10 | 1.00 | 1.47 | 1.31 | 0.11 | 0.74 | 1.44 | 1.62 | 1.36 | 1.00 | 0.21 | 1.01 |
| Cpn2 | 1.00 | 1.00 | 1.00 | 0.11 | 0.09 | 0.25 | 0.89 | 1.00 | 1.03 | 1.00 | 1.00 | 1.00 |
| Cpne1 | 0.82 | 2.38 | 1.07 | 1.58 | 0.08 | 0.91 | 0.90 | 0.99 | 0.85 | 0.25 | 0.15 | 0.93 |
| Cpne3 | 0.93 | 0.86 | 1.26 | 2.24 | 0.48 | 1.02 | 1.02 | 1.03 | 1.13 | 0.45 | 0.37 | 0.91 |
| Cpq | 0.73 | 1.72 | 0.68 | 0.77 | 0.31 | 0.77 | 0.83 | 0.91 | 0.91 | 0.16 | 0.40 | 0.93 |
| Cramp1l | 1.11 | 1.20 | 1.10 | 1.83 | 0.48 | 1.01 | 1.29 | 1.44 | 1.30 | 0.57 | 0.60 | 1.10 |
| Crebbp | 0.96 | 1.00 | 1.28 | 1.63 | 0.28 | 1.21 | 1.53 | 2.03 | 1.20 | 1.00 | 1.00 | 1.04 |
| Crebl2 | 0.91 | 1.00 | 0.94 | 1.72 | 0.09 | 0.90 | 1.22 | 1.32 | 1.19 | 1.00 | 0.14 | 1.44 |
| Crebrf | 1.53 | 1.80 | 1.39 | 2.32 | 0.81 | 1.04 | 1.40 | 1.82 | 1.22 | 0.86 | 0.64 | 0.99 |
| Crisp1 | 1.00 | 1.00 | 1.00 | 1.00 | 1.00 | 1.00 | 1.00 | 1.00 | 1.00 | 1.00 | 1.00 | 1.00 |
| Crk | 0.92 | 2.03 | 0.88 | 1.22 | 0.17 | 1.03 | 1.00 | 1.12 | 1.16 | 0.42 | 0.27 | 1.05 |
| Crlf3 | 0.79 | 1.11 | 1.04 | 1.00 | 0.19 | 1.19 | 0.90 | 0.86 | 0.89 | 0.40 | 0.24 | 1.00 |
| Crygc | 1.00 | 1.00 | 1.00 | 1.00 | 1.00 | 1.00 | 1.00 | 1.00 | 1.00 | 1.00 | 1.00 | 1.00 |
| Cryl1 | 0.73 | 1.23 | 0.64 | 0.68 | 1.14 | 0.94 | 0.68 | 0.77 | 0.80 | 0.34 | 0.56 | 0.84 |
| Csdc2 | 1.11 | 1.24 | 0.75 | 0.95 | 0.13 | 1.00 | 1.60 | 1.37 | 1.20 | 1.51 | 1.28 | 1.21 |
| Csf1 | 0.92 | 0.67 | 0.91 | 0.77 | 0.54 | 0.70 | 0.51 | 0.54 | 0.94 | 0.48 | 0.48 | 0.79 |
| Csl | 0.72 | 1.53 | 0.91 | 0.90 | 0.20 | 0.69 | 1.12 | 1.33 | 0.97 | 0.53 | 0.32 | 0.99 |
| Cst12 | 1.00 | 1.00 | 1.00 | 1.00 | 1.00 | 1.00 | 1.00 | 1.00 | 1.00 | 1.00 | 1.00 | 1.00 |
| Cthrc1 | 1.00 | 1.00 | 1.00 | 1.00 | 1.00 | 1.00 | 1.00 | 1.00 | 1.00 | 0.88 | 0.33 | 0.68 |
| Ctnnd1 | 0.89 | 1.73 | 1.01 | 2.07 | 0.34 | 1.04 | 1.10 | 1.24 | 1.20 | 0.26 | 0.36 | 1.00 |
| Ctse | 0.51 | 1.00 | 1.00 | 1.00 | 1.00 | 1.00 | 1.00 | 1.00 | 1.00 | 0.33 | 0.54 | 0.83 |
| Cul4a | 0.87 | 1.73 | 0.85 | 1.19 | 0.38 | 0.97 | 0.98 | 1.07 | 0.90 | 0.57 | 0.20 | 1.06 |
| Cwc22 | 1.68 | 1.74 | 1.68 | 1.40 | 1.31 | 1.57 | 1.12 | 1.13 | 0.88 | 0.57 | 0.49 | 1.18 |
| Cwf19l2 | 0.96 | 2.16 | 1.24 | 4.21 | 0.38 | 1.30 | 1.05 | 1.39 | 1.21 | 0.69 | 0.29 | 1.10 |
| Cxcl12 | 0.87 | 1.27 | 1.05 | 1.16 | 0.33 | 0.97 | 0.82 | 0.81 | 0.83 | 0.22 | 0.19 | 0.60 |
| Cxcl9 | 1.00 | 1.00 | 1.00 | 1.00 | 1.00 | 1.00 | 1.00 | 1.00 | 1.00 | 1.00 | 1.00 | 2.13 |
| Cxxc5 | 0.41 | 0.18 | 0.39 | 0.48 | 1.11 | 0.51 | 0.65 | 0.47 | 0.75 | 1.74 | 2.16 | 0.86 |
| Cyb5 | 1.61 | 2.06 | 1.48 | 2.22 | 3.14 | 2.09 | 0.89 | 0.73 | 0.84 | 0.39 | 0.73 | 1.02 |
| Cyb5r1 | 1.07 | 0.99 | 0.80 | 0.59 | 1.61 | 1.01 | 0.95 | 0.82 | 0.91 | 0.94 | 0.83 | 0.84 |
| Cyfip2 | 1.00 | 1.00 | 1.00 | 1.00 | 0.13 | 1.00 | 0.58 | 0.46 | 0.35 | 0.73 | 0.55 | 0.81 |
| Cyp1a1 | 1.00 | 1.00 | 1.00 | 1.00 | 1.00 | 1.00 | 1.00 | 1.00 | 1.00 | 1.00 | 1.00 | 1.00 |
| Cyp1a2 | 1.00 | 1.00 | 1.00 | 1.00 | 1.00 | 1.00 | 1.00 | 1.00 | 1.00 | 1.00 | 1.00 | 1.00 |
| Cyp2a22 | 1.00 | 1.00 | 1.00 | 1.00 | 1.00 | 1.00 | 1.00 | 1.00 | 1.00 | 1.00 | 1.00 | 1.00 |
| Cyp2a4 | 1.00 | 1.00 | 1.00 | 1.00 | 1.00 | 1.00 | 1.00 | 1.00 | 1.00 | 1.00 | 0.74 | 1.54 |
| Cyp2a5 | 1.00 | 1.00 | 1.00 | 1.00 | 1.00 | 1.00 | 1.00 | 1.00 | 1.00 | 0.54 | 2.12 | 1.29 |
| Cyp2b9 | 1.00 | 1.00 | 1.00 | 1.00 | 1.00 | 1.00 | 1.00 | 1.00 | 1.00 | 1.00 | 1.00 | 1.00 |
| Cyp2c44 | 0.85 | 1.00 | 0.99 | 1.00 | 1.00 | 1.00 | 1.00 | 1.00 | 1.00 | 1.00 | 1.00 | 1.00 |

Fig. 35- 22

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ckap2 | 0.68 | 0.68 | 0.53 | 1.00 | 1.00 | 1.00 | 1.00 | 1.00 | 1.00 | 1.33 | 1.15 | 0.81 |
| Cks2 | 0.61 | 0.87 | 0.61 | 0.65 | 1.38 | 0.78 | 0.99 | 0.11 | 1.07 | 1.28 | 2.06 | 1.67 |
| Clca5 | 3.98 | 2.86 | 3.49 | 1.00 | 1.00 | 1.00 | 1.00 | 1.00 | 1.00 | 1.00 | 1.00 | 1.00 |
| Clcf1 | 1.02 | 0.90 | 1.69 | 0.66 | 1.00 | 0.81 | 1.02 | 1.00 | 1.00 | 0.85 | 0.53 | 0.67 |
| Clcn3 | 0.84 | 0.69 | 0.91 | 0.92 | 1.37 | 0.84 | 0.75 | 0.94 | 0.87 | 1.04 | 0.73 | 0.92 |
| Cldn13 | 1.42 | 0.90 | 1.53 | 1.00 | 1.00 | 1.00 | 1.00 | 1.00 | 1.00 | 1.00 | 1.00 | 1.00 |
| Cldn23 | 1.00 | 1.05 | 1.24 | 1.00 | 1.00 | 1.00 | 1.00 | 1.00 | 1.00 | 1.16 | 0.99 | 1.08 |
| Cldn25 | 1.01 | 1.00 | 1.21 | 1.00 | 0.88 | 0.93 | 1.31 | 0.87 | 1.02 | 1.06 | 0.95 | 1.29 |
| Clec1a | 1.00 | 1.00 | 1.00 | 1.32 | 1.00 | 1.48 | 1.00 | 1.00 | 1.00 | 1.46 | 1.00 | 0.97 |
| Clec2g | 1.00 | 1.00 | 1.00 | 1.00 | 1.00 | 1.00 | 1.00 | 1.00 | 1.00 | 1.00 | 1.00 | 1.00 |
| Clgn | 1.00 | 1.00 | 1.00 | 1.00 | 1.00 | 1.00 | 1.00 | 1.00 | 1.00 | 1.00 | 1.00 | 1.00 |
| Cmbl | 1.46 | 1.51 | 0.76 | 1.04 | 1.48 | 1.08 | 1.17 | 0.56 | 1.18 | 0.95 | 1.15 | 1.08 |
| Cmpk1 | 0.78 | 0.84 | 0.84 | 0.93 | 2.06 | 1.02 | 1.11 | 0.36 | 0.92 | 0.96 | 0.95 | 1.01 |
| Cmtm6 | 0.78 | 0.69 | 0.96 | 1.20 | 1.54 | 1.05 | 0.77 | 0.44 | 0.69 | 0.99 | 0.71 | 0.98 |
| Cnnm4 | 0.67 | 0.73 | 1.02 | 1.04 | 1.00 | 1.13 | 1.96 | 1.00 | 1.63 | 0.89 | 0.70 | 0.96 |
| Cnot3 | 0.76 | 0.73 | 0.93 | 0.73 | 1.00 | 1.01 | 0.86 | 1.00 | 0.82 | 0.90 | 0.63 | 0.90 |
| Cntfr | 3.37 | 2.97 | 1.63 | 0.91 | 1.21 | 1.05 | 1.29 | 1.00 | 1.03 | 1.26 | 1.38 | 1.04 |
| Cog1 | 0.76 | 0.67 | 0.85 | 1.19 | 1.00 | 1.11 | 1.57 | 1.00 | 1.09 | 1.10 | 0.71 | 1.01 |
| Cog3 | 0.91 | 0.95 | 1.01 | 1.03 | 2.33 | 0.85 | 0.89 | 0.91 | 1.09 | 1.08 | 0.94 | 1.04 |
| Col13a1 | 1.00 | 1.00 | 1.00 | 1.84 | 1.00 | 1.00 | 1.33 | 1.00 | 1.92 | 1.00 | 1.00 | 1.00 |
| Col3a1 | 0.99 | 0.57 | 0.94 | 0.46 | 1.00 | 0.35 | 0.98 | 1.00 | 1.00 | 0.68 | 0.56 | 0.76 |
| Col4a3 | 1.00 | 1.00 | 1.00 | 1.25 | 1.56 | 1.04 | 1.00 | 1.00 | 1.00 | 1.00 | 1.00 | 1.00 |
| Col4a3bp | 0.89 | 0.79 | 0.92 | 1.07 | 1.51 | 0.91 | 0.77 | 0.44 | 0.92 | 1.02 | 1.00 | 1.14 |
| Coq2 | 1.06 | 1.30 | 1.05 | 1.05 | 1.26 | 0.97 | 0.98 | 0.15 | 0.84 | 0.97 | 1.42 | 1.04 |
| Cox15 | 0.82 | 0.80 | 0.94 | 0.91 | 1.62 | 0.97 | 0.67 | 1.00 | 0.72 | 1.02 | 0.79 | 1.04 |
| Cox6c | 0.79 | 1.28 | 0.58 | 0.70 | 0.82 | 0.62 | 0.57 | 0.57 | 0.77 | 0.91 | 1.56 | 0.79 |
| Cpeb4 | 0.75 | 0.58 | 0.91 | 1.30 | 1.62 | 1.21 | 1.02 | 1.00 | 1.20 | 1.11 | 0.73 | 1.04 |
| Cped1 | 1.16 | 0.81 | 0.90 | 1.07 | 1.00 | 1.02 | 1.02 | 1.00 | 0.97 | 1.02 | 0.40 | 0.96 |
| Cpn2 | 1.00 | 1.00 | 1.00 | 1.00 | 1.00 | 1.00 | 0.90 | 1.05 | 1.18 | 1.00 | 1.00 | 1.00 |
| Cpne1 | 0.69 | 0.63 | 0.90 | 0.92 | 1.00 | 1.10 | 0.79 | 1.00 | 0.88 | 1.02 | 0.65 | 1.09 |
| Cpne3 | 0.84 | 0.77 | 1.13 | 0.94 | 0.75 | 1.00 | 0.84 | 0.44 | 0.93 | 0.97 | 0.68 | 0.98 |
| Cpq | 1.41 | 1.41 | 1.12 | 1.21 | 3.32 | 1.07 | 0.71 | 0.35 | 0.67 | 1.05 | 1.03 | 0.97 |
| Cramp1l | 0.65 | 0.59 | 0.83 | 1.18 | 1.07 | 1.26 | 0.97 | 1.00 | 1.16 | 1.00 | 0.61 | 0.95 |
| Crebbp | 0.56 | 0.48 | 1.05 | 1.18 | 1.00 | 1.28 | 0.82 | 1.00 | 1.10 | 1.01 | 0.29 | 1.03 |
| Crebl2 | 0.83 | 0.59 | 1.24 | 1.34 | 1.00 | 1.16 | 0.79 | 1.00 | 0.76 | 0.95 | 0.42 | 1.02 |
| Crebrf | 0.95 | 0.92 | 1.09 | 1.37 | 1.20 | 1.19 | 1.11 | 1.02 | 0.94 | 1.23 | 0.86 | 1.08 |
| Crisp1 | 1.00 | 1.00 | 1.00 | 1.00 | 1.00 | 1.00 | 1.00 | 1.00 | 1.00 | 1.00 | 1.00 | 1.00 |
| Crk | 0.82 | 0.69 | 1.03 | 1.04 | 1.73 | 1.06 | 0.98 | 0.52 | 1.04 | 1.04 | 0.70 | 1.02 |
| Crlf3 | 0.83 | 0.87 | 0.97 | 0.94 | 1.19 | 1.12 | 1.58 | 1.00 | 0.88 | 1.00 | 0.81 | 0.97 |
| Crygc | 1.00 | 1.00 | 1.00 | 1.00 | 1.00 | 1.00 | 1.00 | 1.00 | 1.00 | 1.00 | 1.00 | 1.00 |
| Cryl1 | 1.48 | 1.37 | 1.22 | 1.03 | 1.77 | 0.97 | 0.55 | 0.11 | 0.55 | 0.93 | 1.06 | 0.98 |
| Csdc2 | 1.00 | 0.93 | 1.00 | 0.84 | 0.48 | 0.70 | 1.00 | 1.00 | 1.00 | 1.02 | 1.05 | 1.24 |
| Csf1 | 1.42 | 0.98 | 1.36 | 1.01 | 0.72 | 0.96 | 0.76 | 1.00 | 0.88 | 0.77 | 0.66 | 0.75 |
| Csl | 0.60 | 0.50 | 0.69 | 0.93 | 1.61 | 0.97 | 0.91 | 0.41 | 0.90 | 1.01 | 0.47 | 0.89 |
| Cst12 | 1.00 | 1.00 | 1.00 | 1.00 | 1.00 | 1.00 | 1.00 | 1.00 | 1.00 | 1.00 | 1.00 | 1.00 |
| Cthrc1 | 1.00 | 1.00 | 1.00 | 1.00 | 1.00 | 1.00 | 1.00 | 1.00 | 1.00 | 1.00 | 1.00 | 1.00 |
| Ctnnd1 | 1.54 | 1.26 | 1.82 | 1.03 | 1.61 | 1.07 | 1.11 | 0.29 | 1.26 | 1.00 | 0.78 | 0.94 |
| Ctse | 1.22 | 1.35 | 1.02 | 1.00 | 1.00 | 1.02 | 0.38 | 0.08 | 0.36 | 1.32 | 1.35 | 1.11 |
| Cul4a | 0.99 | 0.89 | 0.93 | 1.07 | 1.27 | 1.03 | 0.86 | 0.75 | 0.83 | 0.97 | 0.86 | 1.08 |
| Cwc22 | 1.14 | 1.12 | 1.04 | 1.45 | 1.87 | 1.14 | 1.34 | 1.00 | 0.94 | 1.06 | 1.25 | 1.14 |
| Cwf19l2 | 0.89 | 0.85 | 1.15 | 1.41 | 1.00 | 1.19 | 1.07 | 1.00 | 1.28 | 1.10 | 0.93 | 1.03 |
| Cxcl12 | 0.87 | 0.93 | 1.27 | 0.68 | 1.07 | 0.82 | 0.55 | 0.22 | 0.76 | 0.73 | 0.69 | 0.85 |
| Cxcl9 | 1.17 | 1.04 | 1.88 | 1.00 | 1.00 | 1.00 | 1.00 | 1.00 | 1.02 | 0.76 | 0.23 | 0.52 |
| Cxxc5 | 0.74 | 0.84 | 0.81 | 0.97 | 0.61 | 1.06 | 0.71 | 1.50 | 0.90 | 0.87 | 1.12 | 0.91 |
| Cyb5 | 1.25 | 1.41 | 0.96 | 0.86 | 1.56 | 0.82 | 0.82 | 0.24 | 0.83 | 0.83 | 1.24 | 0.87 |
| Cyb5r1 | 1.17 | 1.09 | 0.94 | 0.81 | 0.88 | 0.93 | 0.72 | 0.17 | 0.70 | 0.90 | 1.19 | 1.15 |
| Cyfip2 | 0.68 | 0.66 | 0.84 | 0.81 | 0.79 | 0.95 | 1.00 | 1.00 | 1.00 | 0.76 | 0.55 | 1.01 |
| Cyp1a1 | 1.00 | 1.00 | 1.00 | 1.00 | 1.00 | 1.00 | 1.00 | 1.00 | 1.00 | 1.06 | 1.09 | 1.00 |
| Cyp1a2 | 1.00 | 1.00 | 1.00 | 1.00 | 1.00 | 1.00 | 0.41 | 0.18 | 0.41 | 1.00 | 1.00 | 1.00 |
| Cyp2a22 | 1.00 | 1.00 | 1.00 | 1.00 | 1.00 | 1.00 | 0.44 | 0.07 | 0.43 | 1.00 | 1.00 | 1.00 |
| Cyp2a4 | 1.41 | 1.00 | 1.00 | 0.84 | 1.06 | 0.71 | 0.15 | 0.12 | 0.23 | 1.00 | 1.00 | 1.00 |
| Cyp2a5 | 4.78 | 3.53 | 1.82 | 1.44 | 1.82 | 0.75 | 0.15 | 0.14 | 0.27 | 1.00 | 1.00 | 1.00 |
| Cyp2b9 | 1.00 | 1.00 | 1.00 | 1.00 | 1.00 | 1.00 | 1.00 | 0.83 | 0.09 | 1.00 | 1.00 | 1.00 |
| Cyp2c44 | 1.00 | 1.00 | 1.00 | 0.84 | 1.00 | 0.70 | 0.01 | 0.02 | 0.01 | 1.00 | 1.00 | 1.00 |

Fig. 35- 23

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ckap2 | 0.46 | 0.48 | 0.55 | 1.00 | 1.00 | 1.00 | 1.04 | 0.42 | 1.01 | 0.76 | 0.61 | 0.44 |
| Cks2 | 0.82 | 0.33 | 0.77 | 0.68 | 1.00 | 0.55 | 0.88 | 0.43 | 0.94 | 0.81 | 0.93 | 0.86 |
| Clca5 | 0.86 | 1.75 | 1.35 | 1.11 | 1.00 | 1.00 | 1.00 | 1.00 | 1.00 | 1.00 | 1.00 | 1.00 |
| Clcf1 | 0.88 | 0.98 | 0.94 | 1.34 | 0.32 | 1.67 | 1.37 | 1.00 | 0.47 | 0.80 | 0.56 | 0.91 |
| Clcn3 | 1.23 | 1.09 | 1.01 | 0.90 | 0.44 | 0.92 | 1.05 | 0.79 | 0.96 | 0.91 | 0.84 | 0.83 |
| Cldn13 | 1.00 | 1.00 | 1.00 | 1.00 | 1.00 | 1.00 | 1.08 | 2.60 | 1.17 | 0.39 | 0.32 | 0.17 |
| Cldn23 | 1.05 | 1.39 | 1.23 | 1.00 | 1.00 | 0.32 | 1.11 | 1.00 | 1.50 | 1.00 | 1.00 | 1.00 |
| Cldn25 | 0.95 | 1.01 | 0.91 | 0.97 | 0.31 | 1.13 | 1.02 | 0.64 | 0.83 | 1.17 | 0.98 | 1.20 |
| Clec1a | 0.80 | 0.71 | 0.94 | 1.30 | 0.61 | 1.13 | 1.00 | 1.00 | 1.00 | 1.06 | 0.55 | 0.95 |
| Clec2g | 1.00 | 1.00 | 1.00 | 1.00 | 1.00 | 1.00 | 1.00 | 1.00 | 1.00 | 0.82 | 1.00 | 0.65 |
| Clgn | 1.00 | 1.00 | 1.00 | 1.30 | 1.00 | 1.00 | 1.07 | 2.35 | 1.03 | 1.00 | 1.00 | 1.00 |
| Cmbl | 1.03 | 1.09 | 1.26 | 0.54 | 1.54 | 0.70 | 0.75 | 0.45 | 0.76 | 0.92 | 1.24 | 1.00 |
| Cmpk1 | 0.85 | 0.84 | 0.79 | 1.26 | 0.38 | 1.31 | 1.04 | 0.54 | 0.95 | 1.09 | 0.87 | 1.01 |
| Cmtm6 | 1.02 | 1.00 | 0.96 | 1.04 | 0.23 | 1.11 | 1.06 | 0.90 | 0.98 | 1.00 | 0.74 | 1.11 |
| Cnnm4 | 0.81 | 0.82 | 0.73 | 1.11 | 1.00 | 1.12 | 1.00 | 0.77 | 1.07 | 0.92 | 0.64 | 1.11 |
| Cnot3 | 0.90 | 0.89 | 0.98 | 0.95 | 0.57 | 1.06 | 1.17 | 1.00 | 1.14 | 0.87 | 0.63 | 0.95 |
| Cntfr | 1.15 | 2.12 | 1.40 | 0.88 | 1.00 | 0.75 | 0.77 | 0.38 | 0.96 | 1.46 | 2.28 | 1.63 |
| Cog1 | 1.05 | 1.14 | 0.89 | 1.07 | 0.57 | 0.98 | 1.09 | 0.47 | 1.14 | 1.01 | 0.80 | 1.02 |
| Cog3 | 1.12 | 0.98 | 0.93 | 0.99 | 0.50 | 1.02 | 1.05 | 0.55 | 1.12 | 1.07 | 0.85 | 1.02 |
| Col13a1 | 1.50 | 2.05 | 1.19 | 1.00 | 1.00 | 1.00 | 1.00 | 1.00 | 1.00 | 1.00 | 1.39 | 0.94 |
| Col3a1 | 0.57 | 0.48 | 0.65 | 0.61 | 0.26 | 0.60 | 0.68 | 0.49 | 0.96 | 0.73 | 0.50 | 0.62 |
| Col4a3 | 1.30 | 1.37 | 1.14 | 0.90 | 1.00 | 1.19 | 0.87 | 1.00 | 0.82 | 1.00 | 1.00 | 1.00 |
| Col4a3bp | 0.83 | 0.86 | 0.78 | 1.02 | 0.36 | 0.79 | 1.05 | 0.80 | 1.05 | 1.06 | 0.96 | 1.10 |
| Coq2 | 1.08 | 1.03 | 1.14 | 0.80 | 3.22 | 1.01 | 0.82 | 0.46 | 0.88 | 1.12 | 1.24 | 0.93 |
| Cox15 | 0.94 | 1.07 | 1.07 | 0.85 | 1.00 | 0.89 | 0.98 | 1.00 | 0.84 | 1.08 | 0.82 | 0.97 |
| Cox6c | 0.80 | 1.11 | 0.82 | 0.60 | 1.35 | 0.62 | 0.83 | 0.88 | 0.85 | 1.12 | 1.10 | 0.83 |
| Cpeb4 | 1.13 | 0.92 | 0.80 | 1.36 | 0.29 | 0.96 | 1.27 | 0.88 | 1.07 | 0.74 | 0.60 | 0.76 |
| Cped1 | 1.02 | 1.08 | 1.19 | 0.95 | 0.18 | 0.62 | 1.22 | 1.00 | 0.96 | 1.08 | 0.63 | 1.12 |
| Cpn2 | 1.00 | 1.00 | 1.00 | 1.00 | 1.00 | 1.00 | 1.00 | 1.00 | 1.00 | 1.00 | 1.00 | 1.00 |
| Cpne1 | 1.01 | 0.96 | 1.23 | 0.83 | 0.32 | 0.96 | 1.14 | 1.00 | 0.89 | 1.06 | 0.66 | 1.12 |
| Cpne3 | 1.08 | 0.97 | 0.85 | 0.76 | 0.27 | 0.75 | 1.12 | 1.00 | 0.88 | 1.10 | 0.75 | 1.05 |
| Cpq | 1.07 | 1.06 | 1.10 | 0.68 | 0.19 | 0.65 | 0.97 | 0.20 | 0.83 | 1.04 | 0.91 | 0.97 |
| Cramp1l | 1.03 | 0.94 | 1.00 | 1.07 | 0.46 | 0.86 | 1.11 | 0.73 | 0.96 | 0.93 | 0.70 | 1.08 |
| Crebbp | 1.09 | 1.13 | 0.89 | 1.24 | 0.21 | 0.95 | 1.45 | 1.00 | 1.24 | 0.94 | 0.55 | 1.20 |
| Crebl2 | 1.07 | 1.09 | 1.11 | 1.15 | 0.27 | 0.82 | 1.02 | 1.00 | 0.96 | 1.53 | 0.87 | 1.34 |
| Crebrf | 1.40 | 1.50 | 1.19 | 0.91 | 0.20 | 0.79 | 0.98 | 0.62 | 0.96 | 1.26 | 0.92 | 1.31 |
| Crisp1 | 1.80 | 1.26 | 1.01 | 0.75 | 1.15 | 0.01 | 1.00 | 1.00 | 1.00 | 1.00 | 1.00 | 1.00 |
| Crk | 0.95 | 0.88 | 0.74 | 0.97 | 0.22 | 0.97 | 0.87 | 0.48 | 0.96 | 1.09 | 0.73 | 1.11 |
| Crlf3 | 1.09 | 1.07 | 1.19 | 0.81 | 0.91 | 0.91 | 0.84 | 1.00 | 1.09 | 1.42 | 1.08 | 1.32 |
| Crygc | 1.00 | 1.00 | 1.00 | 1.00 | 0.14 | 0.11 | 1.00 | 1.00 | 1.00 | 1.00 | 1.00 | 1.00 |
| Cryl1 | 0.78 | 0.90 | 1.10 | 0.65 | 1.62 | 0.72 | 0.66 | 0.52 | 0.79 | 1.22 | 1.11 | 0.84 |
| Csdc2 | 0.87 | 1.55 | 1.76 | 1.33 | 2.27 | 1.77 | 0.77 | 0.88 | 0.73 | 1.53 | 4.02 | 1.59 |
| Csf1 | 0.75 | 0.65 | 0.97 | 0.71 | 0.93 | 0.74 | 0.56 | 1.04 | 0.67 | 0.73 | 0.73 | 0.92 |
| Csl | 0.88 | 0.82 | 0.62 | 0.68 | 0.15 | 0.76 | 1.12 | 1.70 | 1.08 | 0.90 | 0.61 | 0.95 |
| Cst12 | 1.00 | 1.00 | 1.00 | 0.11 | 1.00 | 1.00 | 0.86 | 1.19 | 0.84 | 1.00 | 1.00 | 1.00 |
| Cthrc1 | 1.91 | 0.47 | 0.89 | 0.76 | 0.99 | 1.50 | 1.00 | 1.00 | 1.00 | 1.00 | 1.00 | 1.00 |
| Ctnnd1 | 0.94 | 0.93 | 0.79 | 1.14 | 0.15 | 1.08 | 1.11 | 0.44 | 0.95 | 0.90 | 0.90 | 1.09 |
| Ctse | 0.83 | 0.95 | 0.79 | 0.81 | 1.00 | 1.74 | 1.00 | 1.00 | 1.00 | 0.90 | 1.01 | 0.83 |
| Cul4a | 1.00 | 0.92 | 0.94 | 0.93 | 0.22 | 1.02 | 1.01 | 0.62 | 1.05 | 0.91 | 0.73 | 0.79 |
| Cwc22 | 1.12 | 1.35 | 1.12 | 1.27 | 0.61 | 1.19 | 1.21 | 1.00 | 0.94 | 1.34 | 1.16 | 1.08 |
| Cwf19l2 | 1.13 | 1.10 | 1.06 | 1.03 | 1.00 | 0.97 | 1.15 | 1.00 | 1.08 | 1.22 | 0.85 | 1.30 |
| Cxcl12 | 0.97 | 0.91 | 1.15 | 0.82 | 0.20 | 1.09 | 0.55 | 0.27 | 0.59 | 1.30 | 1.18 | 1.40 |
| Cxcl9 | 1.54 | 1.00 | 1.29 | 0.18 | 1.18 | 0.48 | 1.00 | 1.00 | 1.00 | 0.51 | 0.37 | 0.48 |
| Cxxc5 | 1.03 | 0.97 | 1.10 | 0.71 | 0.91 | 0.91 | 0.99 | 1.95 | 0.96 | 1.07 | 1.08 | 1.09 |
| Cyb5 | 0.97 | 1.06 | 0.92 | 1.06 | 1.03 | 1.19 | 0.68 | 0.12 | 0.76 | 0.89 | 0.96 | 0.83 |
| Cyb5r1 | 0.77 | 0.74 | 1.00 | 0.78 | 1.51 | 0.83 | 0.86 | 0.70 | 0.91 | 0.91 | 0.94 | 0.93 |
| Cyfip2 | 0.91 | 0.93 | 1.42 | 0.75 | 1.00 | 1.07 | 0.93 | 1.00 | 1.28 | 1.04 | 0.92 | 0.98 |
| Cyp1a1 | 1.00 | 1.00 | 1.00 | 1.00 | 1.00 | 1.00 | 1.00 | 1.00 | 1.00 | 1.00 | 1.00 | 1.00 |
| Cyp1a2 | 1.00 | 1.00 | 1.00 | 1.00 | 1.00 | 1.00 | 1.00 | 1.00 | 1.00 | 1.00 | 1.00 | 1.00 |
| Cyp2a22 | 1.00 | 1.00 | 1.00 | 1.00 | 1.00 | 1.00 | 1.00 | 1.00 | 1.00 | 1.00 | 1.00 | 1.00 |
| Cyp2a4 | 1.00 | 1.00 | 1.00 | 1.00 | 1.00 | 1.00 | 1.00 | 1.00 | 1.00 | 1.00 | 1.00 | 1.00 |
| Cyp2a5 | 1.00 | 1.00 | 1.00 | 1.00 | 1.00 | 1.00 | 1.00 | 1.00 | 1.00 | 1.00 | 1.00 | 1.00 |
| Cyp2b9 | 1.00 | 1.00 | 1.00 | 1.00 | 1.00 | 1.00 | 1.00 | 1.00 | 1.00 | 1.00 | 1.00 | 1.00 |
| Cyp2c44 | 0.56 | 0.53 | 0.74 | 1.00 | 1.00 | 1.00 | 1.00 | 1.00 | 1.00 | 1.00 | 1.00 | 1.00 |

Fig. 35- 24

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ckap2 | 1.00 | 1.00 | 1.00 | 1.00 | 1.00 | 1.00 | 0.51 | 0.14 | 0.88 | 0.53 | 0.76 | 0.90 |
| Cks2 | 0.73 | 0.89 | 1.00 | 0.65 | 1.00 | 1.00 | 0.71 | 0.68 | 0.69 | 0.77 | 0.94 | 1.18 |
| Clca5 | 1.00 | 1.00 | 1.00 | 1.00 | 1.00 | 1.00 | 0.56 | 0.13 | 0.65 | 1.00 | 1.00 | 1.00 |
| Clcf1 | 1.00 | 1.00 | 1.00 | 1.00 | 1.00 | 1.00 | 0.95 | 0.12 | 0.93 | 0.32 | 0.74 | 0.72 |
| Clcn3 | 1.34 | 1.41 | 1.34 | 0.95 | 1.12 | 0.93 | 0.76 | 0.11 | 0.99 | 0.31 | 0.85 | 0.76 |
| Cldn13 | 1.00 | 1.00 | 1.00 | 1.00 | 1.00 | 1.00 | 1.00 | 1.00 | 1.00 | 0.98 | 0.76 | 0.79 |
| Cldn23 | 1.00 | 1.00 | 1.00 | 1.00 | 0.58 | 1.00 | 0.79 | 0.19 | 0.47 | 1.00 | 1.00 | 1.00 |
| Cldn25 | 1.58 | 1.24 | 1.19 | 0.98 | 0.49 | 1.15 | 0.81 | 0.03 | 0.93 | 0.39 | 0.88 | 1.08 |
| Clec1a | 1.00 | 1.00 | 1.00 | 1.00 | 1.00 | 1.00 | 1.00 | 1.00 | 1.00 | 1.00 | 1.00 | 1.00 |
| Clec2g | 1.00 | 1.00 | 1.00 | 1.00 | 1.00 | 1.00 | 0.10 | 0.17 | 0.12 | 1.00 | 1.00 | 1.00 |
| Clgn | 1.00 | 1.00 | 1.00 | 1.29 | 0.16 | 0.90 | 1.44 | 1.00 | 1.00 | 1.00 | 1.00 | 1.00 |
| Cmbl | 0.17 | 0.21 | 0.47 | 0.97 | 2.84 | 0.94 | 1.75 | 2.17 | 1.71 | 1.25 | 0.92 | 1.07 |
| Cmpk1 | 1.16 | 1.21 | 1.22 | 1.07 | 1.36 | 1.08 | 0.90 | 0.04 | 0.99 | 0.33 | 0.98 | 1.04 |
| Cmtm6 | 1.24 | 0.92 | 1.12 | 0.93 | 0.70 | 0.89 | 0.72 | 0.16 | 0.84 | 0.64 | 1.07 | 1.05 |
| Cnnm4 | 1.00 | 1.00 | 1.00 | 0.99 | 1.00 | 0.91 | 0.62 | 0.15 | 0.67 | 0.53 | 1.02 | 1.02 |
| Cnot3 | 0.61 | 0.83 | 0.87 | 0.85 | 1.00 | 0.97 | 0.99 | 0.13 | 1.06 | 0.45 | 1.02 | 0.92 |
| Cntfr | 0.89 | 1.00 | 1.00 | 1.05 | 0.87 | 1.02 | 2.14 | 0.53 | 1.82 | 1.00 | 1.00 | 1.00 |
| Cog1 | 1.08 | 0.80 | 1.34 | 1.03 | 1.00 | 0.98 | 0.91 | 0.14 | 1.14 | 0.30 | 0.86 | 0.78 |
| Cog3 | 1.06 | 0.98 | 0.80 | 1.11 | 0.61 | 0.97 | 0.99 | 0.19 | 1.09 | 0.67 | 1.01 | 0.93 |
| Col13a1 | 1.00 | 1.00 | 1.00 | 1.00 | 1.00 | 1.00 | 1.00 | 1.00 | 1.00 | 1.00 | 1.00 | 1.00 |
| Col3a1 | 0.54 | 0.96 | 0.78 | 0.99 | 1.00 | 1.00 | 0.85 | 0.29 | 1.18 | 1.00 | 1.00 | 1.00 |
| Col4a3 | 1.00 | 1.00 | 1.00 | 1.00 | 1.00 | 1.00 | 1.00 | 1.00 | 1.00 | 1.00 | 1.00 | 1.00 |
| Col4a3bp | 1.25 | 0.97 | 1.24 | 0.94 | 0.68 | 0.93 | 0.94 | 0.18 | 1.11 | 0.85 | 1.21 | 1.12 |
| Coq2 | 0.84 | 0.76 | 0.80 | 1.06 | 3.30 | 1.02 | 0.89 | 0.39 | 0.84 | 0.83 | 0.99 | 1.09 |
| Cox15 | 0.78 | 0.91 | 0.77 | 1.09 | 0.82 | 1.00 | 0.85 | 0.15 | 1.07 | 0.28 | 0.83 | 0.97 |
| Cox6c | 0.48 | 1.17 | 1.08 | 0.84 | 1.20 | 0.97 | 1.19 | 1.84 | 0.88 | 1.32 | 1.08 | 0.96 |
| Cpeb4 | 2.34 | 3.93 | 1.00 | 0.88 | 1.00 | 0.91 | 0.89 | 0.12 | 1.02 | 0.34 | 0.75 | 0.70 |
| Cped1 | 1.00 | 1.00 | 1.00 | 1.00 | 1.00 | 1.26 | 1.04 | 0.47 | 1.38 | 1.00 | 1.00 | 1.00 |
| Cpn2 | 1.00 | 1.00 | 1.00 | 1.00 | 1.00 | 1.00 | 1.00 | 1.00 | 1.00 | 1.00 | 1.00 | 1.00 |
| Cpne1 | 1.15 | 1.09 | 1.46 | 0.87 | 1.00 | 1.05 | 0.92 | 0.09 | 1.09 | 0.17 | 0.97 | 1.21 |
| Cpne3 | 1.34 | 1.35 | 1.26 | 0.86 | 0.90 | 0.86 | 0.77 | 0.19 | 1.01 | 0.62 | 1.17 | 1.15 |
| Cpq | 0.53 | 0.87 | 0.72 | 0.95 | 1.00 | 0.84 | 0.93 | 0.11 | 1.10 | 0.46 | 0.89 | 0.90 |
| Cramp1l | 0.97 | 0.91 | 1.00 | 0.95 | 1.00 | 0.87 | 1.02 | 0.15 | 1.12 | 0.48 | 0.84 | 0.82 |
| Crebbp | 1.15 | 1.15 | 1.00 | 0.82 | 1.00 | 0.96 | 0.94 | 0.14 | 1.28 | 1.00 | 0.72 | 0.72 |
| Crebl2 | 1.09 | 0.75 | 1.07 | 0.94 | 1.00 | 1.01 | 1.04 | 0.16 | 1.28 | 1.00 | 0.85 | 0.95 |
| Crebrf | 1.27 | 1.13 | 1.51 | 0.94 | 1.86 | 1.07 | 1.19 | 0.61 | 1.51 | 0.80 | 1.24 | 1.14 |
| Crisp1 | 1.00 | 1.00 | 1.00 | 1.00 | 1.00 | 1.00 | 1.00 | 1.00 | 1.00 | 1.00 | 1.00 | 1.00 |
| Crk | 1.23 | 1.03 | 1.17 | 1.03 | 0.72 | 0.96 | 0.85 | 0.13 | 1.07 | 0.41 | 0.81 | 1.04 |
| Crlf3 | 1.00 | 1.00 | 1.15 | 0.81 | 1.00 | 1.07 | 0.81 | 0.07 | 1.01 | 0.39 | 1.13 | 1.16 |
| Crygc | 1.00 | 1.00 | 1.00 | 1.00 | 1.00 | 1.00 | 1.00 | 1.00 | 1.00 | 1.00 | 1.00 | 1.00 |
| Cryl1 | 0.63 | 0.74 | 0.95 | 1.20 | 1.86 | 0.98 | 1.16 | 0.10 | 1.02 | 0.63 | 1.01 | 1.06 |
| Csdc2 | 1.00 | 1.00 | 1.00 | 1.14 | 1.22 | 1.06 | 1.50 | 2.41 | 1.27 | 1.00 | 1.00 | 1.00 |
| Csf1 | 0.85 | 1.00 | 1.00 | 0.93 | 0.18 | 0.92 | 0.81 | 0.55 | 0.81 | 1.07 | 1.40 | 1.36 |
| Csl | 1.01 | 0.95 | 1.08 | 1.00 | 1.96 | 1.01 | 0.91 | 0.08 | 1.03 | 0.56 | 0.77 | 0.79 |
| Cst12 | 1.00 | 1.00 | 1.00 | 1.00 | 1.00 | 1.00 | 1.66 | 1.00 | 1.00 | 1.00 | 1.00 | 1.00 |
| Cthrc1 | 1.00 | 1.00 | 1.00 | 1.25 | 1.00 | 1.03 | 0.98 | 0.16 | 1.00 | 1.00 | 1.00 | 1.00 |
| Ctnnd1 | 1.38 | 1.41 | 1.36 | 0.94 | 0.31 | 0.98 | 0.79 | 0.10 | 0.90 | 0.47 | 1.02 | 1.03 |
| Ctse | 1.00 | 1.00 | 0.82 | 1.00 | 1.00 | 1.00 | 1.30 | 1.84 | 1.29 | 0.61 | 0.89 | 0.91 |
| Cul4a | 1.02 | 0.73 | 1.00 | 1.08 | 1.13 | 0.91 | 0.92 | 0.08 | 1.01 | 0.34 | 0.89 | 0.96 |
| Cwc22 | 1.26 | 1.40 | 1.29 | 1.17 | 1.34 | 1.06 | 1.18 | 0.16 | 1.23 | 0.39 | 0.99 | 1.05 |
| Cwf19l2 | 1.00 | 1.00 | 1.00 | 0.88 | 1.00 | 0.99 | 0.83 | 0.17 | 1.26 | 0.46 | 1.16 | 1.00 |
| Cxcl12 | 0.61 | 0.51 | 0.67 | 0.85 | 0.32 | 0.86 | 0.89 | 0.24 | 1.21 | 0.26 | 0.43 | 1.15 |
| Cxcl9 | 1.00 | 1.00 | 1.00 | 1.00 | 1.00 | 1.00 | 1.00 | 1.00 | 1.00 | 1.00 | 0.92 | 1.00 |
| Cxxc5 | 0.84 | 0.87 | 0.81 | 0.87 | 0.78 | 0.88 | 0.59 | 2.17 | 0.79 | 1.48 | 0.81 | 1.00 |
| Cyb5 | 0.60 | 0.49 | 0.57 | 0.96 | 0.15 | 0.95 | 1.37 | 0.39 | 1.04 | 0.58 | 0.94 | 0.93 |
| Cyb5r1 | 0.95 | 1.41 | 1.16 | 1.16 | 0.77 | 1.15 | 1.04 | 1.42 | 0.84 | 1.05 | 1.18 | 1.20 |
| Cyfip2 | 1.04 | 0.95 | 1.04 | 1.04 | 1.11 | 1.03 | 0.72 | 0.50 | 0.69 | 0.68 | 0.91 | 0.98 |
| Cyp1a1 | 1.00 | 1.00 | 1.00 | 1.00 | 1.00 | 1.00 | 1.90 | 0.15 | 1.91 | 1.00 | 1.00 | 1.00 |
| Cyp1a2 | 1.00 | 1.00 | 1.00 | 1.00 | 1.00 | 1.00 | 1.00 | 1.00 | 1.00 | 1.00 | 1.00 | 1.00 |
| Cyp2a22 | 1.00 | 1.00 | 1.00 | 1.00 | 1.00 | 1.00 | 1.00 | 1.00 | 1.00 | 1.00 | 1.00 | 1.00 |
| Cyp2a4 | 1.00 | 1.00 | 1.00 | 1.00 | 1.00 | 1.00 | 1.00 | 1.00 | 1.00 | 1.00 | 1.00 | 1.00 |
| Cyp2a5 | 1.00 | 1.00 | 1.00 | 0.46 | 1.00 | 1.00 | 1.57 | 1.21 | 1.64 | 1.00 | 1.00 | 1.00 |
| Cyp2b9 | 1.00 | 1.00 | 1.00 | 1.00 | 1.00 | 1.00 | 1.00 | 1.00 | 1.00 | 1.00 | 1.00 | 1.00 |
| Cyp2c44 | 1.00 | 1.00 | 1.00 | 1.00 | 1.00 | 1.00 | 1.00 | 1.00 | 1.00 | 1.00 | 1.00 | 1.00 |

Fig. 35- 25

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Cypt9 | 1.00 | 1.00 | 1.00 | 1.00 | 1.00 | 1.00 | 1.00 | 1.00 | 1.00 | 1.00 | 1.00 | 1.00 |
| Cystm1 | 1.38 | 1.15 | 0.98 | 1.11 | 0.46 | 1.50 | 1.19 | 1.08 | 1.17 | 0.50 | 0.18 | 1.31 |
| Cyth3 | 1.07 | 2.72 | 1.28 | 1.38 | 0.50 | 1.33 | 1.30 | 1.24 | 1.27 | 0.50 | 0.35 | 0.92 |
| Cyyr1 | 0.84 | 1.00 | 1.91 | 2.46 | 0.13 | 0.68 | 1.37 | 2.66 | 2.10 | 1.00 | 0.56 | 0.96 |
| D030056L22Rik | 0.77 | 1.11 | 0.88 | 2.46 | 0.41 | 0.99 | 0.88 | 0.71 | 0.95 | 0.48 | 0.27 | 0.86 |
| D430019H16Rik | 1.00 | 1.00 | 1.00 | 1.00 | 0.52 | 1.00 | 1.00 | 1.00 | 1.00 | 0.21 | 0.17 | 0.31 |
| D930016D06Rik | 1.49 | 2.53 | 1.01 | 1.11 | 0.39 | 0.99 | 0.84 | 1.08 | 1.04 | 0.45 | 0.71 | 1.01 |
| Dag1 | 1.06 | 1.76 | 1.18 | 0.79 | 0.14 | 0.61 | 1.09 | 1.27 | 1.08 | 0.44 | 0.55 | 1.24 |
| Dagla | 0.44 | 1.00 | 0.49 | 0.69 | 0.15 | 0.79 | 0.93 | 1.10 | 1.14 | 0.91 | 0.44 | 0.99 |
| Dapk1 | 2.17 | 3.08 | 2.15 | 3.94 | 0.93 | 1.79 | 1.22 | 1.25 | 1.05 | 0.63 | 0.82 | 1.61 |
| Dbf4 | 1.00 | 1.00 | 1.00 | 1.00 | 1.00 | 1.00 | 1.00 | 1.23 | 1.00 | 0.82 | 0.53 | 1.29 |
| Dbp | 0.13 | 0.15 | 0.16 | 0.13 | 0.12 | 0.38 | 0.24 | 0.21 | 0.39 | 0.22 | 0.36 | 0.53 |
| Dbt | 0.89 | 1.77 | 1.08 | 1.50 | 0.20 | 1.02 | 0.89 | 1.09 | 0.90 | 1.00 | 0.56 | 1.46 |
| Dclk3 | 1.00 | 1.00 | 1.00 | 1.00 | 0.68 | 1.00 | 1.00 | 1.00 | 1.00 | 1.00 | 1.00 | 1.85 |
| Dcp1a | 0.98 | 1.16 | 1.13 | 1.06 | 0.23 | 1.06 | 1.05 | 1.30 | 1.19 | 0.44 | 0.38 | 1.05 |
| Ddb2 | 0.74 | 1.00 | 0.52 | 2.29 | 0.59 | 1.27 | 0.78 | 0.49 | 1.14 | 0.59 | 0.19 | 1.10 |
| Ddr1 | 1.06 | 1.25 | 0.95 | 0.63 | 0.20 | 0.51 | 0.94 | 0.72 | 0.86 | 0.65 | 0.56 | 1.35 |
| Ddx19b | 0.84 | 1.51 | 0.95 | 0.95 | 0.31 | 0.97 | 0.96 | 1.12 | 1.12 | 0.99 | 0.41 | 1.07 |
| Ddx20 | 0.90 | 2.27 | 1.15 | 1.53 | 0.29 | 0.93 | 1.10 | 1.05 | 0.89 | 0.54 | 0.22 | 1.01 |
| Ddx23 | 1.07 | 1.32 | 0.96 | 0.95 | 0.75 | 1.10 | 1.08 | 1.10 | 1.09 | 0.43 | 0.64 | 1.11 |
| Ddx26b | 0.48 | 0.83 | 0.82 | 1.83 | 0.78 | 0.98 | 0.80 | 0.61 | 0.97 | 0.30 | 0.40 | 0.83 |
| Ddx3x | 1.03 | 1.87 | 1.03 | 2.13 | 0.34 | 1.10 | 0.90 | 1.09 | 1.22 | 0.44 | 0.51 | 1.14 |
| Def8 | 0.60 | 1.08 | 0.69 | 0.49 | 0.32 | 0.96 | 0.78 | 0.76 | 0.80 | 0.35 | 0.37 | 1.01 |
| Defb38 | 1.00 | 1.00 | 1.00 | 1.00 | 1.00 | 1.00 | 1.00 | 1.00 | 1.00 | 1.00 | 1.00 | 1.00 |
| Defb43 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Defb50 | 1.00 | 1.00 | 1.00 | 1.00 | 1.00 | 1.00 | 1.00 | 1.00 | 1.00 | 1.00 | 1.00 | 1.00 |
| Defb8 | 1.00 | 1.00 | 1.00 | 1.00 | 1.00 | 1.00 | 1.00 | 1.00 | 1.00 | 1.00 | 1.00 | 1.00 |
| Dffa | 0.79 | 1.63 | 0.81 | 0.57 | 0.27 | 0.99 | 1.05 | 1.02 | 1.07 | 0.46 | 0.59 | 1.06 |
| Dgat2 | 0.42 | 0.75 | 0.85 | 0.13 | 0.40 | 0.61 | 0.75 | 0.74 | 0.53 | 0.51 | 1.04 | 0.86 |
| Dgkq | 0.86 | 1.00 | 1.20 | 0.85 | 0.17 | 0.93 | 0.96 | 0.96 | 1.08 | 1.00 | 0.40 | 1.06 |
| Dhdh | 0.65 | 4.52 | 0.81 | 1.38 | 0.09 | 1.04 | 0.99 | 1.25 | 0.96 | 1.00 | 0.35 | 0.97 |
| Dhrs1 | 0.98 | 0.96 | 0.78 | 0.40 | 1.08 | 0.73 | 0.88 | 0.98 | 0.84 | 0.66 | 0.74 | 1.09 |
| Dhrs9 | 1.00 | 1.00 | 1.00 | 0.79 | 0.17 | 0.79 | 1.00 | 1.00 | 1.00 | 1.00 | 1.00 | 1.00 |
| Diap1 | 1.60 | 2.02 | 1.40 | 1.15 | 0.15 | 1.15 | 1.27 | 1.34 | 1.43 | 1.00 | 0.15 | 1.18 |
| Dip2a | 1.34 | 1.13 | 1.11 | 0.56 | 0.21 | 0.70 | 0.88 | 1.15 | 1.04 | 0.47 | 0.31 | 0.87 |
| Diras2 | 1.00 | 1.00 | 1.00 | 1.00 | 0.15 | 1.00 | 1.00 | 1.00 | 1.00 | 1.59 | 1.85 | 1.09 |
| Disp1 | 0.76 | 1.00 | 1.27 | 0.86 | 0.33 | 0.70 | 1.15 | 1.05 | 1.02 | 0.82 | 0.43 | 0.62 |
| Dkk2 | 1.24 | 1.61 | 1.37 | 1.00 | 1.00 | 1.00 | 1.00 | 1.00 | 1.00 | 1.00 | 1.00 | 1.00 |
| Dlg2 | 1.00 | 1.00 | 1.00 | 1.00 | 0.24 | 1.00 | 1.00 | 1.00 | 1.00 | 1.00 | 1.00 | 1.00 |
| Dlg4 | 0.90 | 1.02 | 0.92 | 1.00 | 0.12 | 1.00 | 1.15 | 0.61 | 1.02 | 0.36 | 0.57 | 1.26 |
| Dlk1 | 1.00 | 1.00 | 1.00 | 0.19 | 0.24 | 0.34 | 1.00 | 1.00 | 1.00 | 1.00 | 1.00 | 1.00 |
| Dll1 | 0.63 | 1.00 | 1.07 | 0.71 | 0.50 | 0.64 | 0.65 | 0.78 | 0.85 | 0.66 | 0.27 | 1.41 |
| Dmtf1 | 0.94 | 0.85 | 0.89 | 1.19 | 0.41 | 1.01 | 0.78 | 0.97 | 0.85 | 1.01 | 1.12 | 0.81 |
| Dnajb3 | 1.00 | 1.00 | 1.00 | 0.91 | 0.43 | 1.36 | 1.16 | 1.00 | 0.93 | 1.46 | 0.79 | 0.88 |
| Dnajb9 | 1.72 | 4.24 | 1.45 | 2.50 | 0.31 | 1.25 | 1.25 | 1.46 | 1.15 | 0.24 | 0.33 | 1.12 |
| Dnmt1 | 0.83 | 1.00 | 0.89 | 0.86 | 0.75 | 1.00 | 1.04 | 1.09 | 1.04 | 0.66 | 0.30 | 0.96 |
| Dot1l | 0.75 | 1.00 | 1.15 | 0.76 | 0.08 | 0.66 | 0.76 | 0.98 | 1.10 | 1.00 | 0.59 | 1.16 |
| Dpcr1 | 0.16 | 1.00 | 1.00 | 1.00 | 1.00 | 1.00 | 1.00 | 1.00 | 1.00 | 0.19 | 1.68 | 1.75 |
| Dpp8 | 1.24 | 2.94 | 1.63 | 1.40 | 0.52 | 0.87 | 1.02 | 1.33 | 1.06 | 0.76 | 0.64 | 1.00 |
| Dpys | 1.00 | 1.00 | 1.00 | 1.00 | 1.00 | 1.00 | 1.00 | 1.00 | 1.00 | 1.00 | 1.00 | 1.00 |
| Dr1 | 0.70 | 2.25 | 0.85 | 2.40 | 0.09 | 1.01 | 1.05 | 1.16 | 1.10 | 0.40 | 0.13 | 1.06 |
| Dram1 | 0.62 | 1.29 | 1.47 | 1.40 | 0.78 | 1.56 | 1.08 | 0.91 | 1.23 | 0.52 | 0.57 | 1.12 |
| Dsc1 | 1.00 | 1.00 | 1.00 | 1.00 | 1.00 | 1.00 | 1.00 | 1.00 | 1.00 | 1.00 | 1.00 | 1.00 |
| Dsg1b | 1.00 | 1.00 | 1.00 | 1.00 | 1.00 | 1.00 | 1.00 | 1.00 | 1.00 | 1.00 | 1.00 | 1.00 |
| Dsg1c | 1.00 | 1.00 | 1.00 | 1.00 | 1.00 | 1.00 | 1.00 | 1.00 | 1.00 | 1.00 | 1.00 | 1.00 |
| Dsg3 | 1.00 | 1.00 | 1.00 | 1.00 | 1.00 | 1.00 | 1.00 | 1.00 | 1.00 | 1.00 | 1.00 | 1.00 |
| Dtd1 | 0.59 | 1.15 | 0.96 | 0.82 | 1.74 | 1.38 | 0.90 | 1.01 | 0.83 | 0.22 | 0.82 | 0.94 |
| Dtwd1 | 0.91 | 1.14 | 0.85 | 1.23 | 0.27 | 0.84 | 0.77 | 0.50 | 0.59 | 0.92 | 0.25 | 0.97 |
| Dusp5 | 1.00 | 1.00 | 1.00 | 1.00 | 1.00 | 1.00 | 0.93 | 0.89 | 1.32 | 1.00 | 0.51 | 0.96 |
| Dusp7 | 0.54 | 0.95 | 0.57 | 0.62 | 0.13 | 0.74 | 0.73 | 0.62 | 0.95 | 0.37 | 0.27 | 1.15 |
| Dvl3 | 0.79 | 1.01 | 1.05 | 1.13 | 0.11 | 0.83 | 1.27 | 1.48 | 1.07 | 1.00 | 1.00 | 1.14 |
| E030011O05Rik | 1.00 | 1.00 | 1.00 | 2.82 | 1.07 | 0.95 | 1.79 | 2.98 | 1.42 | 1.00 | 1.00 | 0.65 |
| E130006D01Rik | 1.00 | 1.00 | 1.00 | 1.00 | 1.00 | 1.00 | 1.00 | 1.00 | 1.00 | 1.00 | 1.00 | 1.00 |

Fig. 35- 26

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Cypt9 | 1.00 | 1.00 | 1.00 | 1.00 | 1.00 | 1.00 | 1.00 | 1.00 | 1.00 | 1.00 | 1.00 | 1.00 |
| Cystm1 | 2.11 | 1.40 | 1.32 | 1.04 | 0.68 | 0.93 | 0.83 | 0.49 | 0.63 | 1.20 | 1.39 | 1.37 |
| Cyth3 | 1.10 | 1.09 | 1.24 | 1.06 | 1.23 | 1.05 | 1.00 | 1.00 | 1.14 | 1.12 | 0.95 | 1.12 |
| Cyyr1 | 0.87 | 0.62 | 0.83 | 1.28 | 1.00 | 1.16 | 0.76 | 1.00 | 0.91 | 1.28 | 1.00 | 0.90 |
| D030056L22Rik | 0.76 | 0.68 | 0.78 | 0.83 | 1.77 | 0.82 | 1.04 | 1.00 | 0.93 | 0.97 | 0.80 | 1.35 |
| D430019H16Rik | 1.24 | 0.84 | 1.28 | 1.00 | 1.00 | 0.91 | 1.00 | 1.00 | 1.00 | 1.08 | 1.19 | 1.02 |
| D930016D06Rik | 0.73 | 0.68 | 0.81 | 1.11 | 2.79 | 0.98 | 1.11 | 1.00 | 1.08 | 1.08 | 0.83 | 1.06 |
| Dag1 | 0.89 | 0.69 | 1.16 | 0.93 | 1.24 | 0.98 | 0.71 | 0.24 | 0.87 | 1.04 | 0.62 | 0.97 |
| Dagla | 0.87 | 0.91 | 0.68 | 0.76 | 1.00 | 0.78 | 1.00 | 1.00 | 1.00 | 0.75 | 0.66 | 0.83 |
| Dapk1 | 0.94 | 0.82 | 1.11 | 1.57 | 2.88 | 1.20 | 1.03 | 0.69 | 0.87 | 1.07 | 0.87 | 1.03 |
| Dbf4 | 0.56 | 0.60 | 0.64 | 1.24 | 1.00 | 0.94 | 1.00 | 1.00 | 1.00 | 1.06 | 1.02 | 1.04 |
| Dbp | 0.78 | 0.83 | 0.85 | 0.27 | 0.22 | 0.54 | 0.25 | 0.06 | 0.46 | 0.51 | 0.66 | 0.61 |
| Dbt | 0.81 | 0.77 | 0.95 | 0.88 | 1.70 | 0.88 | 0.76 | 2.19 | 0.77 | 1.05 | 0.75 | 1.04 |
| Dclk3 | 1.00 | 1.00 | 1.00 | 1.16 | 1.25 | 1.16 | 0.15 | 0.49 | 0.32 | 2.51 | 2.07 | 3.28 |
| Dcp1a | 0.69 | 0.66 | 0.89 | 1.06 | 1.00 | 1.06 | 0.86 | 1.00 | 0.92 | 1.00 | 0.66 | 1.04 |
| Ddb2 | 0.86 | 1.03 | 0.94 | 0.70 | 1.00 | 0.94 | 0.59 | 1.00 | 1.16 | 1.06 | 0.79 | 1.04 |
| Ddr1 | 1.18 | 1.11 | 1.26 | 0.72 | 1.19 | 0.80 | 1.00 | 1.00 | 1.00 | 0.82 | 0.76 | 0.89 |
| Ddx19b | 0.75 | 0.69 | 0.85 | 1.07 | 1.12 | 1.03 | 0.73 | 1.00 | 0.78 | 1.09 | 0.72 | 1.03 |
| Ddx20 | 0.80 | 0.73 | 0.74 | 1.24 | 1.00 | 1.10 | 1.36 | 1.00 | 1.13 | 0.93 | 0.98 | 0.87 |
| Ddx23 | 1.00 | 0.99 | 0.96 | 1.19 | 1.84 | 1.01 | 0.99 | 0.30 | 1.06 | 1.02 | 1.01 | 1.00 |
| Ddx26b | 1.10 | 1.26 | 1.14 | 1.21 | 1.65 | 0.93 | 1.00 | 1.00 | 1.09 | 0.91 | 0.99 | 0.86 |
| Ddx3x | 0.64 | 0.63 | 0.84 | 1.08 | 1.68 | 0.99 | 1.06 | 0.56 | 1.04 | 1.20 | 0.91 | 1.13 |
| Def8 | 1.06 | 1.13 | 1.04 | 0.96 | 1.27 | 0.91 | 1.37 | 0.65 | 1.12 | 0.77 | 0.72 | 0.80 |
| Defb38 | 1.00 | 1.00 | 1.00 | 1.00 | 1.00 | 1.00 | 1.00 | 1.00 | 1.00 | 1.00 | 1.00 | 1.00 |
| Defb43 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Defb50 | 1.00 | 1.00 | 1.00 | 1.00 | 1.00 | 1.00 | 1.00 | 1.00 | 1.00 | 0.13 | 1.00 | 1.00 |
| Defb8 | 1.00 | 1.00 | 1.00 | 1.00 | 1.00 | 1.00 | 1.00 | 1.00 | 1.00 | 1.00 | 1.00 | 1.00 |
| Dffa | 0.78 | 0.86 | 0.99 | 0.88 | 0.81 | 0.93 | 0.68 | 0.32 | 0.76 | 0.82 | 0.93 | 0.88 |
| Dgat2 | 0.50 | 0.57 | 0.34 | 0.77 | 0.93 | 0.87 | 0.59 | 0.39 | 0.74 | 0.69 | 0.81 | 0.80 |
| Dgkq | 0.82 | 0.73 | 0.97 | 1.24 | 1.00 | 1.24 | 1.00 | 1.00 | 0.93 | 0.96 | 0.58 | 0.89 |
| Dhdh | 0.98 | 0.64 | 1.16 | 0.92 | 1.00 | 0.84 | 0.71 | 0.75 | 0.77 | 1.00 | 0.66 | 0.79 |
| Dhrs1 | 1.08 | 1.33 | 1.11 | 0.75 | 1.33 | 0.83 | 0.71 | 0.17 | 0.69 | 0.98 | 1.19 | 0.80 |
| Dhrs9 | 1.00 | 1.00 | 1.00 | 1.00 | 1.00 | 1.00 | 1.00 | 1.00 | 1.00 | 1.09 | 0.48 | 0.92 |
| Diap1 | 0.73 | 0.57 | 0.98 | 1.23 | 1.00 | 1.16 | 1.08 | 1.00 | 1.18 | 0.97 | 0.49 | 0.92 |
| Dip2a | 0.92 | 0.74 | 0.92 | 0.98 | 1.00 | 1.07 | 1.00 | 1.00 | 1.00 | 0.86 | 0.65 | 0.93 |
| Diras2 | 1.34 | 1.09 | 2.01 | 1.00 | 1.00 | 1.00 | 1.00 | 1.00 | 1.00 | 0.76 | 0.58 | 0.94 |
| Disp1 | 0.69 | 0.67 | 0.89 | 1.36 | 1.00 | 1.58 | 1.00 | 1.00 | 1.00 | 0.99 | 0.67 | 0.86 |
| Dkk2 | 1.46 | 1.66 | 1.47 | 0.79 | 0.92 | 0.77 | 1.00 | 1.00 | 1.00 | 1.00 | 1.00 | 1.00 |
| Dlg2 | 1.02 | 0.82 | 1.21 | 1.00 | 1.00 | 1.00 | 1.00 | 1.00 | 1.00 | 1.20 | 0.72 | 0.91 |
| Dlg4 | 0.60 | 0.62 | 0.87 | 0.65 | 1.00 | 1.05 | 1.00 | 1.00 | 1.00 | 0.89 | 0.81 | 0.88 |
| Dlk1 | 1.00 | 1.00 | 1.00 | 1.00 | 1.00 | 1.00 | 1.00 | 1.00 | 1.00 | 1.00 | 1.00 | 1.00 |
| Dll1 | 2.81 | 1.59 | 2.32 | 0.87 | 1.00 | 0.87 | 0.51 | 1.00 | 0.52 | 0.75 | 0.52 | 0.86 |
| Dmtf1 | 0.62 | 0.67 | 0.79 | 0.85 | 0.58 | 0.70 | 1.03 | 1.54 | 1.11 | 0.90 | 0.87 | 0.88 |
| Dnajb3 | 1.22 | 1.11 | 0.53 | 1.00 | 1.00 | 1.00 | 1.00 | 1.00 | 1.00 | 0.96 | 1.00 | 1.00 |
| Dnajb9 | 1.11 | 0.98 | 1.45 | 1.16 | 1.76 | 1.08 | 1.10 | 0.74 | 0.95 | 1.14 | 0.90 | 1.13 |
| Dnmt1 | 0.39 | 0.44 | 0.61 | 0.81 | 1.00 | 0.80 | 0.77 | 1.00 | 0.91 | 0.85 | 0.74 | 0.78 |
| Dot1l | 0.51 | 0.40 | 0.78 | 1.11 | 1.00 | 1.01 | 1.17 | 1.00 | 1.35 | 0.90 | 0.41 | 0.83 |
| Dpcr1 | 1.00 | 0.11 | 1.00 | 1.00 | 1.00 | 1.00 | 1.00 | 1.51 | 1.00 | 0.73 | 1.00 | 1.00 |
| Dpp8 | 0.76 | 0.71 | 0.94 | 1.24 | 1.12 | 1.27 | 0.87 | 1.08 | 0.99 | 1.01 | 0.63 | 0.90 |
| Dpys | 1.00 | 1.00 | 1.00 | 0.12 | 0.10 | 0.08 | 1.07 | 0.85 | 1.30 | 1.00 | 1.00 | 1.00 |
| Dr1 | 0.69 | 0.58 | 0.93 | 1.04 | 1.47 | 1.09 | 1.10 | 1.00 | 0.99 | 1.01 | 0.59 | 1.02 |
| Dram1 | 1.05 | 0.93 | 1.05 | 0.52 | 0.80 | 0.74 | 1.00 | 1.00 | 1.00 | 0.80 | 0.71 | 0.87 |
| Dsc1 | 1.00 | 1.00 | 1.00 | 1.00 | 1.00 | 1.00 | 1.00 | 1.00 | 1.00 | 1.00 | 1.00 | 1.00 |
| Dsg1b | 1.00 | 1.00 | 1.00 | 1.00 | 1.00 | 1.00 | 1.00 | 1.00 | 1.00 | 1.00 | 1.00 | 1.00 |
| Dsg1c | 1.00 | 1.00 | 1.00 | 1.00 | 1.00 | 1.00 | 0.15 | 1.00 | 0.14 | 1.00 | 1.00 | 1.00 |
| Dsg3 | 1.00 | 1.00 | 1.00 | 1.00 | 1.00 | 1.00 | 1.00 | 1.00 | 1.00 | 1.00 | 1.00 | 1.00 |
| Dtd1 | 1.25 | 1.11 | 1.18 | 0.87 | 1.43 | 0.95 | 0.98 | 0.37 | 0.83 | 0.96 | 1.19 | 1.04 |
| Dtwd1 | 1.12 | 1.14 | 0.82 | 1.27 | 0.69 | 0.95 | 1.11 | 0.53 | 1.08 | 0.97 | 1.18 | 1.08 |
| Dusp5 | 1.15 | 1.15 | 1.22 | 1.25 | 1.00 | 2.13 | 1.00 | 1.00 | 1.00 | 1.16 | 0.93 | 1.26 |
| Dusp7 | 0.94 | 0.85 | 1.17 | 1.03 | 2.00 | 1.16 | 0.83 | 1.00 | 1.02 | 0.92 | 0.67 | 1.27 |
| Dvl3 | 0.61 | 0.44 | 1.11 | 1.10 | 1.32 | 1.06 | 0.94 | 1.00 | 1.04 | 0.86 | 0.37 | 0.91 |
| E030011O05Rik | 1.00 | 1.00 | 1.00 | 1.54 | 1.00 | 1.02 | 1.00 | 1.00 | 1.00 | 1.00 | 0.98 | 0.50 |
| E130006D01Rik | 1.00 | 1.00 | 1.00 | 1.00 | 1.00 | 1.00 | 1.00 | 1.00 | 1.00 | 1.00 | 1.00 | 1.00 |

Fig. 35- 27

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Cypt9 | 1.00 | 1.00 | 1.00 | 4.79 | 1.00 | 1.00 | 0.67 | 0.00 | 0.66 | 1.00 | 1.00 | 1.00 |
| Cystm1 | 0.94 | 1.13 | 0.82 | 1.27 | 0.56 | 0.82 | 0.92 | 2.55 | 1.11 | 0.79 | 2.37 | 0.81 |
| Cyth3 | 1.29 | 1.65 | 1.15 | 1.23 | 0.22 | 1.15 | 0.97 | 0.68 | 0.95 | 1.00 | 0.99 | 0.92 |
| Cyyr1 | 1.06 | 1.09 | 0.92 | 1.29 | 0.09 | 0.85 | 1.08 | 1.00 | 2.17 | 0.99 | 0.48 | 0.99 |
| D030056L22Rik | 0.78 | 0.63 | 1.14 | 1.11 | 0.80 | 1.27 | 0.83 | 0.48 | 0.92 | 0.88 | 0.73 | 0.87 |
| D430019H16Rik | 1.00 | 1.00 | 1.00 | 0.48 | 1.00 | 0.29 | 1.00 | 1.00 | 1.00 | 0.72 | 1.31 | 0.73 |
| D930016D06Rik | 1.20 | 1.03 | 1.11 | 1.21 | 1.00 | 1.16 | 1.10 | 1.71 | 1.10 | 1.08 | 0.85 | 1.06 |
| Dag1 | 0.90 | 0.88 | 0.73 | 0.93 | 0.14 | 0.91 | 1.13 | 0.48 | 1.02 | 0.87 | 0.73 | 1.03 |
| Dagla | 0.82 | 0.90 | 0.78 | 0.78 | 1.00 | 0.68 | 1.00 | 1.00 | 1.00 | 0.90 | 2.16 | 1.51 |
| Dapk1 | 1.19 | 1.20 | 0.97 | 3.76 | 0.53 | 1.72 | 1.03 | 1.00 | 1.00 | 1.34 | 1.18 | 1.12 |
| Dbf4 | 0.76 | 0.55 | 0.69 | 0.69 | 1.00 | 0.80 | 0.72 | 0.22 | 0.70 | 0.81 | 0.73 | 0.71 |
| Dbp | 0.20 | 0.33 | 0.69 | 0.13 | 0.15 | 0.35 | 0.76 | 0.34 | 0.93 | 0.32 | 0.63 | 0.61 |
| Dbt | 1.22 | 1.25 | 1.09 | 0.88 | 0.25 | 1.18 | 0.89 | 1.00 | 0.83 | 1.19 | 0.86 | 1.16 |
| Dclk3 | 1.00 | 1.00 | 1.00 | 0.68 | 1.00 | 0.74 | 1.00 | 1.00 | 1.00 | 1.00 | 1.38 | 1.00 |
| Dcp1a | 1.05 | 0.93 | 0.87 | 1.07 | 0.62 | 0.94 | 0.96 | 1.45 | 1.07 | 0.97 | 0.68 | 1.08 |
| Ddb2 | 1.13 | 0.83 | 1.01 | 0.71 | 1.00 | 1.18 | 0.97 | 1.00 | 0.92 | 1.22 | 1.01 | 1.07 |
| Ddr1 | 1.10 | 1.24 | 0.87 | 0.84 | 0.37 | 0.98 | 1.22 | 1.33 | 1.91 | 0.46 | 0.53 | 0.67 |
| Ddx19b | 0.88 | 0.85 | 0.65 | 0.82 | 0.98 | 0.88 | 1.12 | 1.22 | 1.03 | 1.09 | 0.73 | 1.16 |
| Ddx20 | 0.99 | 0.99 | 1.01 | 1.13 | 0.57 | 1.32 | 1.13 | 0.18 | 0.95 | 1.06 | 0.86 | 1.03 |
| Ddx23 | 1.00 | 1.12 | 0.94 | 1.19 | 0.33 | 1.06 | 1.09 | 0.59 | 0.93 | 1.11 | 1.03 | 1.09 |
| Ddx26b | 1.07 | 1.20 | 1.19 | 0.94 | 1.00 | 0.98 | 0.71 | 0.76 | 0.86 | 1.06 | 0.98 | 0.92 |
| Ddx3x | 1.10 | 0.99 | 0.90 | 1.20 | 0.36 | 0.97 | 0.90 | 0.52 | 0.91 | 1.13 | 0.76 | 1.07 |
| Def8 | 0.97 | 0.95 | 0.98 | 0.93 | 0.38 | 1.18 | 0.86 | 1.00 | 0.78 | 0.97 | 1.07 | 0.96 |
| Defb38 | 1.00 | 1.00 | 1.00 | 1.00 | 3.40 | 0.12 | 1.00 | 1.00 | 1.00 | 1.00 | 1.00 | 1.00 |
| Defb43 | 1.00 | 1.00 | 1.00 | 1.00 | 3.42 | 0.06 | 0.78 | 0.72 | 1.21 | 1.00 | 1.00 | 1.00 |
| Defb48 | 1.00 | 1.00 | 1.00 | 0.10 | 1.00 | 0.71 | 1.00 | 1.39 | 1.00 | 1.00 | 1.00 | 1.00 |
| Defb50 | 1.00 | 1.00 | 1.00 | 1.00 | 1.00 | 1.00 | 1.00 | 1.00 | 1.00 | 1.00 | 1.00 | 1.00 |
| Defb8 | 1.00 | 1.00 | 1.00 | 1.00 | 1.00 | 1.00 | 1.00 | 2.31 | 1.00 | 1.00 | 1.00 | 1.00 |
| Dffa | 0.84 | 0.66 | 0.78 | 0.84 | 1.00 | 0.97 | 1.19 | 0.53 | 0.88 | 1.14 | 0.94 | 0.97 |
| Dgat2 | 0.81 | 0.97 | 0.81 | 0.17 | 0.15 | 0.27 | 0.90 | 1.26 | 0.93 | 0.68 | 1.30 | 0.78 |
| Dgkq | 1.16 | 1.01 | 1.19 | 1.05 | 1.00 | 1.05 | 0.90 | 1.00 | 0.83 | 1.05 | 0.64 | 1.10 |
| Dhdh | 1.26 | 0.77 | 1.43 | 0.48 | 0.10 | 0.68 | 0.90 | 1.01 | 0.80 | 0.87 | 0.63 | 1.29 |
| Dhrs1 | 1.02 | 0.95 | 0.99 | 0.72 | 0.55 | 0.80 | 0.96 | 0.42 | 1.08 | 0.70 | 0.82 | 0.80 |
| Dhrs9 | 1.21 | 1.57 | 0.77 | 1.00 | 1.00 | 0.51 | 1.00 | 1.00 | 1.00 | 1.00 | 1.00 | 1.00 |
| Diap1 | 1.02 | 1.22 | 0.78 | 1.17 | 0.41 | 0.88 | 1.02 | 0.73 | 1.01 | 0.97 | 0.58 | 0.95 |
| Dip2a | 0.98 | 0.93 | 0.90 | 0.98 | 1.00 | 0.89 | 1.28 | 1.08 | 1.14 | 0.91 | 0.86 | 0.91 |
| Diras2 | 0.80 | 0.99 | 0.86 | 1.00 | 1.00 | 1.06 | 0.46 | 0.89 | 0.35 | 1.35 | 3.33 | 2.08 |
| Disp1 | 1.09 | 1.29 | 1.00 | 0.67 | 0.99 | 0.83 | 0.85 | 1.00 | 0.83 | 0.91 | 0.67 | 1.06 |
| Dkk2 | 0.92 | 1.00 | 1.00 | 1.00 | 1.00 | 1.00 | 1.00 | 1.00 | 1.00 | 1.00 | 1.00 | 1.00 |
| Dlg2 | 0.95 | 0.99 | 1.09 | 1.00 | 1.00 | 1.00 | 0.85 | 1.00 | 1.00 | 0.81 | 1.98 | 0.55 |
| Dlg4 | 1.00 | 0.86 | 1.09 | 0.85 | 1.00 | 0.95 | 1.00 | 1.00 | 1.21 | 0.70 | 2.36 | 1.08 |
| Dlk1 | 1.00 | 1.00 | 1.00 | 1.00 | 1.00 | 1.00 | 1.00 | 1.00 | 1.00 | 1.00 | 1.72 | 1.00 |
| Dll1 | 0.69 | 0.78 | 0.75 | 0.73 | 1.00 | 1.02 | 1.00 | 1.00 | 1.00 | 0.93 | 0.66 | 1.00 |
| Dmtf1 | 0.97 | 0.78 | 0.97 | 0.93 | 0.39 | 0.89 | 0.97 | 0.58 | 0.78 | 0.99 | 0.79 | 0.99 |
| Dnajb3 | 1.26 | 1.00 | 0.79 | 2.84 | 0.24 | 1.85 | 0.88 | 0.43 | 0.99 | 0.53 | 0.38 | 0.36 |
| Dnajb9 | 1.10 | 0.91 | 0.94 | 1.15 | 0.45 | 1.56 | 0.98 | 0.38 | 0.95 | 1.09 | 0.86 | 1.22 |
| Dnmt1 | 0.63 | 0.66 | 0.69 | 0.81 | 1.00 | 0.82 | 1.15 | 0.95 | 1.18 | 0.77 | 0.67 | 0.85 |
| Dot1l | 0.83 | 0.90 | 0.67 | 0.92 | 0.82 | 0.80 | 1.29 | 1.36 | 1.16 | 0.71 | 0.56 | 1.02 |
| Dpcr1 | 0.77 | 0.92 | 0.56 | 1.00 | 1.00 | 0.57 | 1.00 | 1.00 | 0.85 | 1.00 | 1.00 | 1.00 |
| Dpp8 | 0.97 | 0.87 | 0.79 | 1.05 | 0.18 | 0.80 | 1.19 | 1.08 | 1.09 | 0.99 | 0.74 | 1.12 |
| Dpys | 1.00 | 1.00 | 1.00 | 1.00 | 1.00 | 1.00 | 1.00 | 0.93 | 1.00 | 1.00 | 1.00 | 1.00 |
| Dr1 | 0.98 | 0.84 | 0.81 | 0.89 | 0.30 | 0.86 | 1.06 | 0.62 | 1.04 | 1.05 | 0.64 | 1.02 |
| Dram1 | 0.84 | 0.79 | 0.97 | 0.35 | 0.11 | 0.63 | 1.00 | 0.41 | 1.02 | 0.76 | 0.57 | 0.65 |
| Dsc1 | 0.87 | 0.88 | 0.93 | 1.00 | 1.00 | 1.00 | 1.00 | 1.00 | 1.00 | 1.00 | 1.00 | 1.00 |
| Dsg1b | 0.98 | 1.10 | 0.79 | 1.00 | 1.00 | 1.00 | 1.05 | 1.58 | 0.90 | 1.00 | 1.00 | 1.00 |
| Dsg1c | 1.00 | 1.00 | 1.00 | 1.00 | 1.00 | 1.00 | 1.30 | 1.00 | 1.21 | 1.00 | 1.00 | 1.00 |
| Dsg3 | 0.99 | 1.14 | 1.07 | 1.00 | 1.00 | 1.00 | 1.00 | 1.00 | 1.00 | 1.00 | 1.00 | 1.00 |
| Dtd1 | 0.86 | 0.85 | 1.15 | 0.78 | 0.55 | 0.85 | 1.20 | 0.52 | 1.01 | 1.11 | 1.41 | 0.93 |
| Dtwd1 | 0.70 | 0.72 | 0.89 | 0.84 | 0.32 | 1.27 | 0.87 | 0.40 | 1.23 | 1.27 | 1.08 | 0.96 |
| Dusp5 | 0.81 | 0.85 | 0.81 | 1.26 | 1.00 | 0.67 | 0.88 | 1.00 | 1.19 | 0.50 | 1.33 | 0.90 |
| Dusp7 | 0.81 | 1.02 | 1.13 | 0.85 | 0.58 | 1.05 | 1.00 | 1.00 | 0.94 | 1.03 | 0.80 | 1.04 |
| Dvl3 | 0.84 | 0.89 | 0.86 | 1.09 | 0.62 | 0.99 | 1.11 | 1.00 | 1.52 | 0.86 | 0.45 | 1.01 |
| E030011O05Rik | 1.00 | 1.00 | 1.00 | 1.01 | 0.20 | 0.89 | 1.00 | 1.00 | 1.00 | 1.00 | 1.00 | 1.00 |
| E130006D01Rik | 1.00 | 1.00 | 1.00 | 1.00 | 0.83 | 1.00 | 1.00 | 1.94 | 1.00 | 1.00 | 1.00 | 1.00 |

Fig. 35- 28

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Cypt9 | 1.00 | 1.00 | 1.00 | 1.00 | 2.98 | 1.00 | 1.00 | 1.00 | 1.00 | 1.00 | 1.00 | 1.00 |
| Cystm1 | 1.93 | 1.68 | 1.37 | 0.99 | 1.56 | 0.92 | 2.06 | 1.60 | 1.55 | 1.00 | 1.00 | 1.00 |
| Cyth3 | 1.68 | 2.06 | 3.03 | 1.08 | 1.00 | 1.05 | 1.02 | 0.12 | 1.13 | 0.43 | 0.91 | 0.88 |
| Cyyr1 | 1.00 | 1.00 | 1.00 | 0.44 | 1.00 | 1.04 | 1.00 | 1.00 | 1.05 | 1.00 | 1.00 | 1.00 |
| D030056L22Rik | 1.15 | 1.32 | 1.07 | 1.04 | 1.00 | 0.94 | 1.03 | 0.17 | 0.97 | 0.25 | 0.76 | 0.84 |
| D430019H16Rik | 1.00 | 1.00 | 1.00 | 0.93 | 1.13 | 0.91 | 1.00 | 1.00 | 1.00 | 1.00 | 1.00 | 1.00 |
| D930016D06Rik | 1.35 | 1.29 | 1.00 | 0.92 | 1.18 | 0.98 | 1.06 | 0.18 | 1.10 | 0.63 | 0.90 | 0.84 |
| Dag1 | 1.29 | 0.98 | 1.28 | 0.91 | 1.04 | 0.92 | 0.78 | 0.17 | 0.93 | 0.60 | 0.82 | 0.68 |
| Dagla | 0.87 | 0.83 | 0.98 | 1.07 | 1.02 | 0.98 | 0.81 | 1.00 | 0.67 | 1.00 | 1.00 | 1.00 |
| Dapk1 | 1.21 | 1.64 | 1.41 | 1.14 | 0.82 | 1.11 | 1.47 | 0.17 | 1.67 | 0.84 | 0.99 | 1.19 |
| Dbf4 | 1.00 | 1.00 | 1.00 | 1.00 | 1.00 | 1.00 | 0.60 | 0.16 | 0.92 | 0.32 | 0.93 | 1.01 |
| Dbp | 0.08 | 0.09 | 0.22 | 0.63 | 0.60 | 0.69 | 0.31 | 0.15 | 0.38 | 0.90 | 1.02 | 0.97 |
| Dbt | 0.76 | 0.79 | 0.70 | 1.07 | 0.67 | 0.95 | 1.09 | 0.28 | 0.94 | 0.93 | 0.82 | 0.84 |
| Dclk3 | 1.00 | 1.00 | 1.00 | 1.10 | 3.24 | 1.04 | 1.21 | 1.00 | 1.39 | 1.00 | 1.00 | 1.00 |
| Dcp1a | 1.07 | 0.96 | 0.86 | 0.84 | 1.00 | 1.00 | 0.77 | 0.13 | 0.96 | 0.38 | 0.86 | 0.84 |
| Ddb2 | 0.67 | 1.42 | 0.98 | 1.21 | 1.00 | 0.94 | 0.92 | 0.13 | 1.25 | 0.27 | 1.29 | 1.27 |
| Ddr1 | 1.18 | 1.12 | 0.98 | 0.94 | 0.96 | 0.97 | 0.99 | 0.13 | 0.93 | 0.61 | 0.81 | 0.64 |
| Ddx19b | 1.21 | 1.20 | 1.00 | 0.94 | 1.00 | 0.99 | 0.75 | 0.17 | 0.93 | 0.60 | 0.82 | 0.88 |
| Ddx20 | 0.97 | 1.02 | 0.84 | 1.05 | 1.00 | 0.79 | 0.93 | 0.12 | 0.97 | 0.37 | 0.83 | 0.93 |
| Ddx23 | 1.22 | 1.34 | 1.05 | 1.18 | 1.26 | 1.06 | 1.16 | 0.12 | 1.01 | 0.70 | 0.96 | 0.85 |
| Ddx26b | 0.95 | 0.95 | 1.37 | 0.86 | 0.79 | 0.94 | 0.85 | 0.19 | 1.07 | 0.67 | 1.18 | 1.08 |
| Ddx3x | 1.35 | 1.68 | 1.44 | 1.06 | 0.56 | 1.06 | 0.83 | 0.16 | 1.01 | 0.46 | 0.88 | 0.95 |
| Def8 | 0.87 | 1.00 | 0.89 | 0.90 | 1.00 | 0.98 | 0.96 | 0.19 | 0.81 | 0.56 | 0.94 | 0.89 |
| Defb38 | 1.00 | 1.00 | 1.00 | 1.00 | 1.00 | 1.00 | 1.00 | 1.00 | 1.00 | 1.00 | 1.00 | 1.00 |
| Defb43 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Defb50 | 1.00 | 1.00 | 1.00 | 1.00 | 1.00 | 1.00 | 1.00 | 1.00 | 1.00 | 1.00 | 1.00 | 1.00 |
| Defb8 | 1.00 | 1.00 | 1.00 | 1.00 | 1.00 | 1.00 | 0.12 | 0.19 | 0.06 | 1.00 | 1.00 | 1.00 |
| Dffa | 0.61 | 1.18 | 0.95 | 1.12 | 1.95 | 1.05 | 0.75 | 0.20 | 0.72 | 0.52 | 1.05 | 0.95 |
| Dgat2 | 0.68 | 1.00 | 0.69 | 1.13 | 1.85 | 1.02 | 0.83 | 0.98 | 0.61 | 1.69 | 1.63 | 1.07 |
| Dgkq | 1.42 | 1.00 | 1.00 | 0.89 | 1.08 | 0.95 | 0.89 | 0.09 | 0.96 | 0.65 | 0.89 | 0.93 |
| Dhdh | 1.00 | 1.00 | 1.00 | 0.96 | 1.00 | 0.78 | 1.03 | 0.69 | 1.02 | 1.00 | 0.65 | 0.72 |
| Dhrs1 | 1.40 | 1.15 | 0.77 | 1.00 | 0.66 | 1.07 | 1.23 | 0.78 | 0.77 | 1.27 | 1.21 | 1.20 |
| Dhrs9 | 1.00 | 1.00 | 1.00 | 1.00 | 1.00 | 1.00 | 1.00 | 1.00 | 1.00 | 1.00 | 1.38 | 1.11 |
| Diap1 | 1.21 | 1.10 | 1.21 | 0.89 | 0.96 | 0.99 | 1.04 | 0.10 | 1.01 | 0.24 | 1.07 | 0.88 |
| Dip2a | 1.00 | 1.00 | 1.00 | 0.93 | 1.00 | 0.91 | 0.71 | 0.19 | 0.86 | 1.00 | 1.08 | 1.13 |
| Diras2 | 1.00 | 1.00 | 1.00 | 1.03 | 0.97 | 0.97 | 1.00 | 1.00 | 1.28 | 0.72 | 0.50 | 0.76 |
| Disp1 | 1.00 | 1.00 | 1.00 | 0.81 | 1.00 | 1.16 | 0.59 | 0.13 | 0.67 | 0.84 | 0.74 | 1.01 |
| Dkk2 | 1.00 | 1.00 | 1.00 | 1.00 | 1.00 | 1.00 | 1.56 | 0.16 | 1.39 | 1.00 | 1.00 | 1.00 |
| Dlg2 | 1.00 | 1.00 | 1.00 | 0.97 | 1.11 | 0.97 | 0.65 | 0.20 | 0.66 | 1.06 | 1.08 | 1.05 |
| Dlg4 | 1.00 | 1.00 | 1.00 | 1.07 | 0.73 | 1.00 | 0.74 | 0.89 | 1.11 | 1.00 | 1.29 | 1.15 |
| Dlk1 | 1.00 | 1.00 | 1.00 | 1.09 | 1.73 | 1.14 | 0.74 | 0.52 | 0.90 | 1.00 | 1.00 | 1.00 |
| Dll1 | 1.00 | 1.00 | 1.00 | 0.84 | 0.60 | 0.94 | 0.80 | 0.09 | 1.07 | 1.00 | 1.00 | 1.00 |
| Dmtf1 | 0.63 | 0.95 | 0.97 | 0.76 | 0.20 | 0.85 | 0.67 | 0.35 | 0.82 | 0.70 | 0.94 | 1.07 |
| Dnajb3 | 1.00 | 1.00 | 1.00 | 0.55 | 1.57 | 0.83 | 2.75 | 0.16 | 0.53 | 0.37 | 0.66 | 0.70 |
| Dnajb9 | 0.91 | 0.84 | 0.87 | 1.09 | 0.79 | 1.03 | 1.31 | 0.14 | 1.49 | 0.25 | 0.97 | 0.92 |
| Dnmt1 | 1.00 | 1.00 | 1.00 | 0.86 | 1.00 | 0.97 | 0.82 | 0.13 | 0.74 | 0.37 | 0.75 | 0.73 |
| Dot1l | 1.34 | 1.22 | 1.50 | 0.84 | 1.00 | 0.90 | 1.01 | 0.13 | 1.09 | 0.43 | 0.60 | 0.56 |
| Dpcr1 | 1.00 | 1.00 | 0.30 | 1.00 | 1.00 | 0.57 | 1.00 | 1.00 | 1.00 | 1.00 | 1.00 | 1.00 |
| Dpp8 | 0.88 | 1.12 | 1.22 | 0.85 | 2.17 | 0.96 | 0.77 | 0.40 | 1.05 | 0.63 | 0.92 | 0.91 |
| Dpys | 1.00 | 1.00 | 1.00 | 1.00 | 1.00 | 1.00 | 1.00 | 1.00 | 1.00 | 1.00 | 1.00 | 1.00 |
| Dr1 | 1.12 | 1.00 | 1.20 | 0.95 | 1.00 | 0.90 | 0.68 | 0.05 | 0.95 | 0.23 | 0.96 | 0.95 |
| Dram1 | 0.99 | 1.04 | 1.18 | 1.00 | 1.00 | 1.00 | 0.85 | 0.38 | 1.03 | 0.68 | 1.23 | 1.10 |
| Dsc1 | 1.00 | 1.00 | 1.00 | 1.00 | 1.00 | 1.00 | 0.45 | 0.07 | 0.44 | 1.00 | 1.00 | 1.00 |
| Dsg1b | 1.00 | 1.00 | 1.00 | 1.00 | 1.00 | 1.00 | 0.37 | 0.12 | 0.48 | 1.00 | 1.00 | 1.00 |
| Dsg1c | 1.00 | 1.00 | 1.00 | 1.00 | 1.00 | 1.00 | 0.84 | 0.61 | 1.13 | 1.00 | 1.00 | 1.00 |
| Dsg3 | 1.00 | 1.00 | 1.00 | 1.00 | 1.00 | 1.00 | 0.56 | 0.12 | 1.18 | 1.00 | 1.00 | 1.00 |
| Dtd1 | 0.79 | 0.85 | 0.67 | 1.10 | 0.20 | 0.94 | 0.97 | 0.71 | 0.89 | 0.74 | 1.40 | 0.92 |
| Dtwd1 | 1.74 | 0.53 | 0.95 | 1.09 | 1.00 | 1.36 | 0.96 | 0.15 | 1.04 | 0.35 | 0.85 | 1.06 |
| Dusp5 | 1.00 | 1.00 | 1.00 | 1.57 | 1.00 | 1.28 | 0.92 | 0.20 | 0.93 | 0.72 | 0.68 | 0.75 |
| Dusp7 | 1.31 | 0.99 | 1.10 | 1.06 | 0.85 | 1.04 | 0.64 | 0.08 | 0.72 | 0.27 | 0.93 | 0.98 |
| Dvl3 | 0.70 | 0.59 | 0.70 | 0.85 | 2.60 | 1.00 | 0.86 | 0.12 | 1.05 | 1.00 | 0.67 | 0.90 |
| E030011O05Rik | 1.00 | 1.00 | 1.00 | 1.00 | 1.00 | 1.00 | 0.81 | 1.00 | 1.06 | 1.00 | 1.00 | 1.00 |
| E130006D01Rik | 1.00 | 1.00 | 1.00 | 1.00 | 0.17 | 1.00 | 1.13 | 3.07 | 1.00 | 1.00 | 1.00 | 1.00 |

Fig. 35-29

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| E2f6 | 1.03 | 1.11 | 0.85 | 0.73 | 0.50 | 0.79 | 0.88 | 0.87 | 0.89 | 0.75 | 0.56 | 1.05 |
| Eaf1 | 0.86 | 1.16 | 1.01 | 1.85 | 0.25 | 1.01 | 1.07 | 1.13 | 1.05 | 0.38 | 0.50 | 1.05 |
| Ear10 | 1.00 | 1.00 | 1.00 | 1.00 | 1.00 | 1.00 | 1.00 | 1.00 | 1.00 | 0.26 | 0.23 | 0.95 |
| Ebag9 | 0.99 | 2.06 | 0.84 | 0.62 | 0.60 | 1.15 | 0.73 | 0.91 | 0.79 | 0.58 | 0.44 | 0.95 |
| Ebf1 | 0.70 | 1.15 | 1.30 | 1.03 | 0.18 | 0.65 | 1.00 | 1.22 | 0.99 | 0.90 | 0.46 | 0.93 |
| Echdc1 | 0.72 | 0.21 | 0.64 | 0.78 | 0.38 | 0.41 | 1.18 | 1.85 | 1.32 | 2.61 | 3.25 | 1.14 |
| Eci3 | 0.57 | 1.00 | 0.40 | 0.24 | 2.42 | 0.17 | 0.25 | 0.19 | 0.19 | 1.00 | 1.00 | 0.40 |
| Efcab14 | 0.83 | 1.44 | 0.70 | 1.03 | 0.28 | 0.98 | 0.93 | 1.06 | 0.90 | 0.36 | 0.45 | 1.07 |
| Efna3 | 1.00 | 1.00 | 1.00 | 1.00 | 1.00 | 1.00 | 1.00 | 1.00 | 1.00 | 1.00 | 0.63 | 1.70 |
| Efnb2 | 0.66 | 1.00 | 0.86 | 1.75 | 0.18 | 0.96 | 0.89 | 0.98 | 0.87 | 0.50 | 0.28 | 1.06 |
| Efr3a | 1.06 | 1.49 | 0.88 | 1.42 | 0.39 | 1.13 | 1.07 | 1.24 | 0.88 | 0.44 | 0.59 | 1.01 |
| Egr2 | 1.02 | 1.00 | 1.00 | 1.00 | 1.00 | 1.00 | 1.00 | 1.00 | 1.60 | 0.77 | 0.55 | 1.11 |
| Ehd3 | 0.68 | 1.48 | 0.87 | 1.87 | 0.21 | 1.37 | 0.95 | 1.22 | 0.80 | 0.18 | 0.22 | 0.50 |
| Ehmt1 | 0.90 | 1.17 | 0.99 | 1.26 | 0.50 | 1.01 | 0.97 | 1.11 | 1.00 | 0.80 | 0.31 | 0.92 |
| Eif2a | 1.05 | 1.45 | 1.02 | 1.19 | 0.64 | 1.10 | 0.95 | 1.07 | 0.94 | 0.59 | 0.64 | 1.11 |
| Eif2ak3 | 0.98 | 1.00 | 0.87 | 0.90 | 0.18 | 0.80 | 0.76 | 1.09 | 1.10 | 0.34 | 0.18 | 0.86 |
| Eif3a | 1.44 | 2.48 | 1.45 | 2.02 | 0.59 | 1.37 | 1.33 | 1.57 | 1.37 | 0.60 | 0.49 | 1.05 |
| Eif3e | 1.07 | 0.70 | 0.85 | 0.59 | 3.19 | 1.15 | 0.85 | 0.90 | 0.85 | 1.36 | 1.83 | 1.07 |
| Eif4a3 | 1.47 | 0.90 | 1.17 | 0.19 | 3.18 | 1.19 | 1.16 | 1.03 | 1.05 | 1.80 | 2.28 | 1.05 |
| Eif4e3 | 1.30 | 3.35 | 1.18 | 2.26 | 0.31 | 0.92 | 1.17 | 1.27 | 1.08 | 0.33 | 0.22 | 1.01 |
| Eif4ebp2 | 0.90 | 3.83 | 1.37 | 1.74 | 0.04 | 0.93 | 1.46 | 1.98 | 1.81 | 1.00 | 0.14 | 1.17 |
| Elf1 | 1.04 | 1.29 | 1.08 | 3.44 | 0.31 | 1.05 | 1.24 | 1.32 | 1.17 | 0.23 | 0.23 | 1.02 |
| Elmo1 | 1.31 | 1.68 | 0.75 | 1.27 | 0.18 | 0.82 | 1.01 | 0.78 | 0.74 | 0.51 | 0.29 | 0.75 |
| Elmsan1 | 1.84 | 1.53 | 1.44 | 3.00 | 0.25 | 1.20 | 1.08 | 1.15 | 1.25 | 0.61 | 0.46 | 1.16 |
| Elovl5 | 0.91 | 1.34 | 0.96 | 1.64 | 0.46 | 1.22 | 0.80 | 0.79 | 0.76 | 0.59 | 0.52 | 1.12 |
| Elovl6 | 1.11 | 1.00 | 1.81 | 0.78 | 0.27 | 0.77 | 1.00 | 1.00 | 1.00 | 1.00 | 1.00 | 1.13 |
| Emp1 | 1.03 | 1.07 | 0.74 | 1.09 | 0.17 | 0.61 | 0.79 | 0.84 | 1.00 | 0.43 | 0.33 | 0.77 |
| Emp2 | 1.44 | 2.50 | 1.82 | 1.42 | 0.47 | 1.01 | 0.88 | 0.88 | 0.99 | 0.44 | 0.48 | 1.12 |
| Eno1 | 1.00 | 1.00 | 1.00 | 0.07 | 1.00 | 1.84 | 1.00 | 1.00 | 1.00 | 1.00 | 1.00 | 0.46 |
| Eogt | 0.94 | 1.00 | 0.88 | 1.25 | 0.24 | 0.94 | 1.06 | 1.13 | 1.19 | 1.84 | 0.44 | 0.82 |
| Epb4.1l2 | 0.92 | 1.68 | 0.94 | 1.15 | 0.44 | 0.60 | 0.87 | 0.91 | 0.89 | 0.26 | 0.35 | 0.77 |
| Epb4.2 | 1.00 | 1.00 | 1.00 | 1.00 | 1.00 | 1.00 | 1.00 | 1.00 | 1.00 | 1.00 | 1.00 | 1.00 |
| Ephb1 | 1.00 | 1.00 | 1.00 | 1.00 | 1.00 | 1.00 | 0.32 | 0.25 | 0.19 | 1.00 | 1.08 | 1.32 |
| Ephx1 | 0.71 | 0.79 | 0.71 | 0.62 | 0.76 | 0.97 | 0.76 | 0.81 | 0.87 | 0.30 | 0.50 | 0.82 |
| Eppin | 1.00 | 1.00 | 1.00 | 1.00 | 1.00 | 1.00 | 1.00 | 1.00 | 1.00 | 2.43 | 1.00 | 1.00 |
| Epyc | 1.00 | 1.00 | 1.00 | 1.00 | 1.00 | 1.00 | 0.94 | 1.00 | 1.00 | 1.00 | 1.00 | 1.00 |
| Eral1 | 0.94 | 1.77 | 0.81 | 0.57 | 0.30 | 0.83 | 1.12 | 0.84 | 0.71 | 0.25 | 0.27 | 0.94 |
| Erbb2ip | 1.70 | 3.60 | 1.58 | 4.01 | 0.19 | 1.19 | 1.26 | 1.57 | 1.24 | 0.38 | 0.21 | 0.96 |
| Erbb3 | 0.99 | 1.00 | 1.00 | 1.00 | 1.00 | 1.00 | 1.27 | 2.27 | 1.13 | 1.00 | 1.00 | 1.26 |
| Ercc6l2 | 0.64 | 1.26 | 0.82 | 1.96 | 0.31 | 1.06 | 0.93 | 1.01 | 0.82 | 0.82 | 0.38 | 0.85 |
| Erdr1 | 0.52 | 0.32 | 0.49 | 0.08 | 0.93 | 0.58 | 0.42 | 0.26 | 0.41 | 0.28 | 0.52 | 0.30 |
| Erg | 0.52 | 1.00 | 0.87 | 0.99 | 0.19 | 1.07 | 1.10 | 1.13 | 0.98 | 0.90 | 0.08 | 1.05 |
| Erich1 | 0.69 | 1.00 | 0.77 | 1.22 | 0.64 | 1.43 | 1.59 | 1.45 | 0.89 | 0.92 | 0.24 | 1.09 |
| Esrp2 | 1.00 | 1.00 | 1.00 | 1.10 | 1.00 | 1.00 | 1.00 | 1.00 | 1.00 | 2.53 | 0.90 | 1.30 |
| Esrrg | 0.52 | 1.00 | 0.74 | 1.62 | 0.20 | 0.84 | 0.87 | 1.28 | 0.91 | 1.00 | 1.00 | 1.02 |
| Etv3 | 1.21 | 2.24 | 1.28 | 2.42 | 0.20 | 1.36 | 1.15 | 1.49 | 1.28 | 0.42 | 0.31 | 1.11 |
| Etv6 | 1.07 | 1.51 | 0.87 | 1.07 | 0.49 | 1.05 | 1.03 | 1.15 | 1.16 | 0.37 | 0.53 | 0.83 |
| Evi2b | 1.00 | 1.00 | 1.00 | 1.00 | 1.00 | 1.00 | 1.00 | 1.00 | 1.08 | 0.41 | 0.18 | 0.73 |
| Evi5 | 1.09 | 2.34 | 1.23 | 1.70 | 0.41 | 0.95 | 0.84 | 1.05 | 0.92 | 0.53 | 0.38 | 0.96 |
| Exd2 | 0.65 | 0.82 | 0.63 | 1.58 | 0.44 | 0.96 | 1.04 | 1.02 | 0.83 | 0.94 | 0.51 | 0.92 |
| Exosc3 | 1.07 | 0.84 | 1.08 | 0.63 | 1.82 | 0.90 | 1.19 | 0.78 | 0.87 | 0.85 | 1.20 | 0.99 |
| Exosc9 | 0.83 | 1.24 | 0.78 | 0.81 | 1.53 | 0.82 | 0.92 | 1.05 | 0.98 | 0.30 | 0.77 | 0.77 |
| Extl2 | 0.56 | 0.95 | 0.57 | 1.09 | 0.37 | 0.69 | 0.61 | 0.76 | 0.81 | 0.56 | 0.42 | 0.87 |
| F13b | 1.00 | 1.00 | 1.00 | 1.00 | 1.00 | 1.00 | 1.00 | 1.00 | 1.00 | 1.00 | 1.00 | 1.00 |
| F2rl1 | 1.00 | 1.00 | 1.00 | 1.00 | 1.00 | 1.00 | 1.00 | 1.00 | 1.00 | 1.00 | 0.42 | 1.76 |
| Fabp1 | 1.14 | 0.47 | 1.00 | 1.00 | 0.28 | 0.64 | 1.84 | 0.47 | 1.00 | 0.03 | 0.14 | 0.39 |
| Fabp5 | 0.70 | 0.63 | 0.66 | 0.12 | 1.17 | 0.36 | 0.43 | 0.49 | 0.54 | 1.27 | 2.01 | 0.57 |
| Fabp7 | 1.00 | 1.00 | 1.00 | 1.00 | 1.00 | 1.00 | 1.00 | 1.00 | 1.00 | 1.00 | 1.00 | 1.00 |
| Fam102a | 0.61 | 1.00 | 1.00 | 0.96 | 0.20 | 0.67 | 0.55 | 0.47 | 0.85 | 0.92 | 0.66 | 0.94 |
| Fam103a1 | 1.05 | 1.74 | 0.77 | 1.24 | 0.58 | 0.94 | 0.95 | 1.02 | 0.88 | 0.39 | 0.36 | 0.97 |
| Fam107b | 1.37 | 1.97 | 1.30 | 1.20 | 0.26 | 0.69 | 1.61 | 2.24 | 1.57 | 0.24 | 0.31 | 0.90 |
| Fam117a | 0.83 | 1.34 | 1.03 | 1.43 | 0.34 | 1.47 | 0.47 | 0.39 | 0.75 | 0.39 | 0.33 | 1.04 |
| Fam122a | 0.93 | 1.49 | 0.88 | 0.83 | 0.48 | 1.10 | 0.82 | 0.99 | 1.03 | 0.54 | 0.68 | 1.02 |
| Fam122c | 1.00 | 1.00 | 1.00 | 1.00 | 1.00 | 1.00 | 1.00 | 1.00 | 1.00 | 1.00 | 1.00 | 1.00 |

Fig. 35- 30

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| E2f6 | 0.67 | 0.77 | 0.84 | 1.23 | 0.99 | 1.02 | 1.11 | 0.60 | 1.25 | 0.93 | 1.04 | 1.17 |
| Eaf1 | 0.69 | 0.55 | 0.80 | 1.03 | 1.34 | 0.99 | 0.94 | 0.73 | 1.03 | 1.06 | 0.83 | 1.11 |
| Ear10 | 0.98 | 1.35 | 1.01 | 1.00 | 1.00 | 1.00 | 1.00 | 1.00 | 0.94 | 0.80 | 1.00 | 1.00 |
| Ebag9 | 0.99 | 1.19 | 1.04 | 1.07 | 1.56 | 0.98 | 0.79 | 0.44 | 0.73 | 0.95 | 1.27 | 1.07 |
| Ebf1 | 1.43 | 0.79 | 1.34 | 0.89 | 1.00 | 1.01 | 1.00 | 1.00 | 1.00 | 1.25 | 0.73 | 1.11 |
| Echdc1 | 0.49 | 0.35 | 0.72 | 0.60 | 0.39 | 0.69 | 0.67 | 1.06 | 0.55 | 0.82 | 0.48 | 0.89 |
| Eci3 | 0.41 | 0.60 | 0.43 | 1.63 | 1.30 | 1.60 | 0.15 | 1.00 | 0.12 | 1.45 | 2.36 | 1.02 |
| Efcab14 | 0.91 | 0.92 | 1.07 | 1.09 | 2.50 | 1.01 | 0.99 | 1.00 | 1.03 | 0.99 | 0.92 | 0.96 |
| Efna3 | 0.82 | 1.00 | 1.00 | 0.91 | 1.00 | 1.00 | 1.00 | 1.00 | 1.00 | 1.16 | 1.08 | 0.90 |
| Efnb2 | 0.95 | 0.66 | 1.43 | 0.79 | 1.00 | 0.98 | 0.67 | 1.00 | 1.05 | 1.09 | 0.63 | 0.99 |
| Efr3a | 0.86 | 0.88 | 0.99 | 1.04 | 1.89 | 0.98 | 1.03 | 0.53 | 0.93 | 1.03 | 0.93 | 1.02 |
| Egr2 | 0.77 | 0.69 | 1.25 | 1.00 | 1.00 | 1.00 | 1.00 | 1.00 | 1.00 | 1.00 | 1.00 | 1.00 |
| Ehd3 | 0.25 | 0.24 | 0.34 | 0.79 | 1.51 | 1.00 | 1.18 | 1.09 | 1.35 | 0.83 | 0.66 | 0.89 |
| Ehmt1 | 0.79 | 0.76 | 0.86 | 0.98 | 1.25 | 1.02 | 0.67 | 0.82 | 0.82 | 1.01 | 0.81 | 1.00 |
| Eif2a | 1.29 | 1.24 | 0.92 | 0.99 | 1.25 | 0.91 | 0.92 | 0.78 | 0.99 | 1.10 | 1.10 | 0.93 |
| Eif2ak3 | 0.49 | 0.51 | 0.57 | 1.62 | 1.55 | 1.25 | 0.87 | 1.00 | 1.27 | 0.88 | 0.68 | 0.81 |
| Eif3a | 0.71 | 0.60 | 0.90 | 1.43 | 1.99 | 1.07 | 1.09 | 0.80 | 1.13 | 1.07 | 0.83 | 1.02 |
| Eif3e | 1.21 | 1.36 | 1.13 | 0.84 | 1.07 | 1.01 | 1.19 | 0.74 | 1.19 | 1.17 | 1.55 | 0.94 |
| Eif4a3 | 0.88 | 1.14 | 0.77 | 0.85 | 0.61 | 1.03 | 1.00 | 0.78 | 0.94 | 0.95 | 1.29 | 1.11 |
| Eif4e3 | 0.73 | 0.67 | 0.78 | 1.18 | 1.00 | 1.19 | 2.04 | 1.00 | 1.58 | 1.10 | 0.93 | 0.98 |
| Eif4ebp2 | 0.65 | 0.50 | 0.99 | 1.44 | 1.00 | 1.72 | 0.69 | 1.00 | 0.97 | 1.16 | 0.48 | 1.03 |
| Elf1 | 0.66 | 0.58 | 0.88 | 1.09 | 1.22 | 1.21 | 1.02 | 1.00 | 1.21 | 1.05 | 0.61 | 1.03 |
| Elmo1 | 0.74 | 0.81 | 0.90 | 0.96 | 1.00 | 1.04 | 1.00 | 1.00 | 1.00 | 1.05 | 0.90 | 0.94 |
| Elmsan1 | 0.71 | 0.59 | 1.04 | 1.17 | 1.00 | 1.20 | 1.06 | 1.00 | 1.51 | 0.99 | 0.55 | 0.91 |
| Elovl5 | 1.07 | 1.02 | 1.16 | 0.76 | 1.40 | 0.84 | 1.17 | 0.53 | 1.38 | 0.97 | 0.79 | 0.88 |
| Elovl6 | 0.71 | 0.64 | 0.80 | 0.78 | 1.00 | 0.90 | 1.09 | 1.00 | 0.79 | 0.95 | 0.62 | 0.88 |
| Emp1 | 0.67 | 0.62 | 0.69 | 0.70 | 0.79 | 0.68 | 1.00 | 1.00 | 1.00 | 1.44 | 1.13 | 1.39 |
| Emp2 | 1.14 | 0.80 | 1.10 | 0.86 | 1.31 | 0.86 | 1.09 | 0.96 | 1.18 | 0.97 | 0.72 | 0.98 |
| Eno1 | 1.38 | 1.00 | 1.67 | 1.30 | 1.00 | 1.84 | 0.53 | 1.00 | 2.10 | 1.37 | 1.00 | 0.30 |
| Eogt | 0.56 | 0.47 | 0.83 | 0.70 | 1.00 | 0.87 | 0.88 | 1.00 | 0.82 | 0.85 | 0.45 | 0.92 |
| Epb4.1l2 | 0.77 | 0.73 | 0.83 | 0.69 | 0.90 | 0.67 | 0.70 | 0.61 | 0.74 | 0.89 | 0.85 | 0.79 |
| Epb4.2 | 1.00 | 1.00 | 1.00 | 1.00 | 1.00 | 1.00 | 1.00 | 1.00 | 1.00 | 1.00 | 1.00 | 1.00 |
| Ephb1 | 1.00 | 1.00 | 1.00 | 1.00 | 1.00 | 1.00 | 1.00 | 1.00 | 1.00 | 1.00 | 1.00 | 1.00 |
| Ephx1 | 1.40 | 1.28 | 1.20 | 0.82 | 2.04 | 0.80 | 0.58 | 0.24 | 0.61 | 0.88 | 1.10 | 1.01 |
| Eppin | 1.00 | 1.00 | 1.00 | 1.00 | 1.00 | 1.00 | 1.00 | 1.00 | 1.00 | 1.00 | 1.00 | 1.00 |
| Epyc | 1.00 | 1.00 | 1.00 | 1.00 | 1.00 | 1.00 | 1.00 | 1.00 | 1.00 | 1.00 | 1.00 | 1.00 |
| Eral1 | 0.99 | 1.18 | 0.85 | 0.86 | 0.77 | 1.00 | 0.79 | 1.00 | 0.76 | 0.84 | 1.14 | 1.13 |
| Erbb2ip | 0.71 | 0.69 | 0.89 | 1.31 | 1.84 | 1.05 | 1.04 | 0.90 | 1.04 | 1.09 | 0.72 | 0.98 |
| Erbb3 | 0.88 | 0.91 | 1.42 | 1.95 | 1.00 | 2.15 | 1.22 | 1.00 | 1.51 | 1.08 | 0.24 | 0.97 |
| Ercc6l2 | 0.79 | 0.80 | 0.99 | 1.02 | 1.00 | 1.00 | 0.68 | 1.00 | 0.89 | 1.01 | 0.65 | 0.89 |
| Erdr1 | 0.25 | 0.36 | 0.28 | 0.31 | 0.22 | 0.53 | 0.49 | 0.41 | 0.45 | 0.34 | 0.37 | 0.45 |
| Erg | 1.10 | 0.98 | 0.83 | 0.75 | 1.00 | 0.83 | 0.77 | 1.00 | 0.74 | 0.81 | 0.49 | 0.91 |
| Erich1 | 0.88 | 0.93 | 1.00 | 1.06 | 0.64 | 1.04 | 1.44 | 1.00 | 1.76 | 1.13 | 1.04 | 1.12 |
| Esrp2 | 0.71 | 0.67 | 0.94 | 1.37 | 0.97 | 1.11 | 0.76 | 0.73 | 0.96 | 1.04 | 0.58 | 0.95 |
| Esrrg | 1.00 | 1.00 | 1.00 | 0.84 | 0.93 | 0.89 | 0.91 | 1.00 | 1.04 | 1.05 | 1.00 | 1.15 |
| Etv3 | 0.79 | 0.65 | 1.06 | 1.20 | 1.00 | 1.20 | 0.89 | 1.00 | 1.06 | 1.05 | 0.61 | 0.92 |
| Etv6 | 0.91 | 0.74 | 1.17 | 0.91 | 1.40 | 0.98 | 1.25 | 1.00 | 1.16 | 1.04 | 0.83 | 0.94 |
| Evi2b | 0.81 | 0.77 | 1.02 | 1.00 | 1.00 | 1.00 | 1.00 | 1.00 | 0.95 | 0.73 | 0.63 | 0.84 |
| Evi5 | 1.17 | 0.99 | 1.04 | 1.09 | 1.33 | 0.94 | 0.94 | 0.59 | 1.00 | 0.94 | 0.76 | 1.02 |
| Exd2 | 0.84 | 0.83 | 1.02 | 1.04 | 1.28 | 1.01 | 0.70 | 0.87 | 0.81 | 1.06 | 0.98 | 1.02 |
| Exosc3 | 0.82 | 0.98 | 0.86 | 0.74 | 1.11 | 0.99 | 0.89 | 0.57 | 1.04 | 0.89 | 1.01 | 1.14 |
| Exosc9 | 0.86 | 1.06 | 0.85 | 0.84 | 1.30 | 0.91 | 0.94 | 0.56 | 1.16 | 1.03 | 1.20 | 1.13 |
| Extl2 | 1.05 | 1.08 | 1.07 | 0.86 | 1.04 | 0.90 | 0.64 | 1.00 | 0.77 | 1.02 | 0.87 | 0.90 |
| F13b | 1.00 | 1.00 | 1.00 | 1.16 | 4.70 | 1.18 | 0.69 | 0.15 | 0.89 | 1.00 | 1.00 | 1.00 |
| F2rl1 | 1.08 | 0.82 | 1.36 | 1.65 | 1.47 | 1.60 | 1.00 | 1.00 | 1.00 | 1.06 | 0.63 | 1.03 |
| Fabp1 | 4.89 | 2.79 | 0.66 | 0.00 | 0.01 | 0.00 | 0.73 | 0.16 | 0.59 | 1.28 | 1.00 | 4.18 |
| Fabp5 | 0.47 | 0.48 | 0.49 | 0.70 | 1.28 | 0.49 | 1.38 | 1.52 | 0.37 | 0.62 | 0.69 | 0.51 |
| Fabp7 | 1.00 | 1.00 | 1.00 | 0.72 | 0.18 | 0.62 | 0.80 | 0.26 | 0.79 | 1.00 | 1.00 | 1.00 |
| Fam102a | 0.69 | 0.73 | 1.22 | 0.91 | 0.96 | 0.86 | 0.65 | 0.66 | 0.96 | 1.01 | 0.89 | 1.03 |
| Fam103a1 | 1.10 | 1.16 | 1.08 | 1.00 | 2.91 | 0.93 | 1.01 | 0.77 | 1.08 | 1.08 | 1.07 | 1.09 |
| Fam107b | 0.72 | 0.69 | 0.88 | 0.78 | 1.53 | 0.77 | 0.94 | 0.39 | 0.96 | 0.85 | 0.71 | 0.91 |
| Fam117a | 0.87 | 0.91 | 0.90 | 0.74 | 1.00 | 0.99 | 0.85 | 1.00 | 1.00 | 0.89 | 1.01 | 1.19 |
| Fam122a | 1.01 | 1.04 | 1.06 | 0.90 | 1.43 | 0.90 | 1.21 | 0.70 | 0.94 | 0.88 | 0.95 | 0.74 |
| Fam122c | 1.00 | 1.00 | 1.00 | 1.00 | 1.00 | 1.00 | 1.00 | 1.00 | 1.00 | 1.00 | 1.00 | 1.00 |

Fig. 35- 31

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| E2f6 | 1.05 | 0.99 | 1.16 | 0.96 | 0.27 | 1.06 | 0.89 | 0.40 | 0.76 | 0.88 | 0.89 | 0.94 |
| Eaf1 | 0.87 | 0.87 | 0.72 | 1.29 | 0.40 | 1.03 | 1.06 | 0.51 | 1.15 | 0.92 | 0.68 | 1.00 |
| Ear10 | 1.00 | 1.00 | 1.00 | 1.65 | 1.00 | 0.16 | 1.00 | 1.00 | 1.00 | 0.72 | 0.65 | 0.70 |
| Ebag9 | 0.94 | 1.00 | 0.96 | 0.79 | 0.53 | 0.97 | 0.96 | 1.93 | 1.16 | 1.26 | 0.97 | 1.07 |
| Ebf1 | 1.39 | 1.10 | 0.83 | 0.56 | 0.18 | 0.69 | 1.00 | 1.00 | 1.00 | 1.37 | 0.92 | 1.33 |
| Echdc1 | 1.25 | 0.72 | 0.70 | 0.19 | 0.39 | 0.43 | 1.42 | 1.00 | 0.72 | 1.60 | 1.00 | 0.55 |
| Eci3 | 1.00 | 1.00 | 0.64 | 0.27 | 1.08 | 0.50 | 1.00 | 1.00 | 1.00 | 0.68 | 1.00 | 1.00 |
| Efcab14 | 1.19 | 1.21 | 1.14 | 0.97 | 0.35 | 0.97 | 1.09 | 0.40 | 1.01 | 0.96 | 0.90 | 1.05 |
| Efna3 | 0.70 | 0.95 | 0.91 | 1.78 | 1.00 | 1.21 | 1.00 | 1.00 | 0.85 | 1.00 | 2.69 | 1.00 |
| Efnb2 | 0.72 | 0.63 | 0.64 | 0.88 | 0.38 | 0.87 | 1.61 | 1.56 | 1.61 | 0.55 | 0.45 | 0.66 |
| Efr3a | 1.12 | 1.00 | 1.00 | 0.85 | 0.53 | 0.85 | 1.15 | 0.34 | 1.02 | 1.02 | 0.93 | 1.03 |
| Egr2 | 1.00 | 1.44 | 1.00 | 0.59 | 1.00 | 0.19 | 1.00 | 1.00 | 1.00 | 0.59 | 0.41 | 0.81 |
| Ehd3 | 0.88 | 1.14 | 1.04 | 0.91 | 0.69 | 0.74 | 0.82 | 1.00 | 0.89 | 0.87 | 0.71 | 0.80 |
| Ehmt1 | 1.03 | 1.07 | 1.01 | 1.04 | 0.42 | 0.98 | 1.20 | 1.00 | 1.09 | 0.91 | 0.79 | 1.08 |
| Eif2a | 1.02 | 1.00 | 1.01 | 0.94 | 0.70 | 1.00 | 0.92 | 0.72 | 1.04 | 1.11 | 1.09 | 1.09 |
| Eif2ak3 | 1.09 | 1.29 | 0.91 | 0.99 | 0.79 | 0.85 | 1.10 | 1.00 | 0.68 | 0.94 | 0.77 | 0.93 |
| Eif3a | 1.01 | 1.01 | 0.78 | 1.34 | 0.28 | 1.00 | 1.19 | 1.55 | 1.02 | 0.97 | 0.73 | 1.03 |
| Eif3e | 1.02 | 0.98 | 1.16 | 0.97 | 1.52 | 1.11 | 0.98 | 0.58 | 1.04 | 1.21 | 1.30 | 1.20 |
| Eif4a3 | 1.04 | 1.16 | 0.91 | 1.28 | 3.79 | 0.96 | 0.75 | 1.21 | 1.01 | 1.05 | 1.01 | 0.92 |
| Eif4e3 | 1.22 | 1.03 | 1.03 | 1.22 | 0.41 | 1.13 | 0.68 | 3.55 | 0.90 | 0.82 | 0.67 | 0.95 |
| Eif4ebp2 | 0.89 | 0.96 | 0.72 | 1.60 | 0.17 | 1.13 | 1.21 | 1.44 | 1.05 | 1.03 | 0.63 | 1.23 |
| Elf1 | 1.15 | 1.11 | 0.97 | 1.28 | 0.45 | 0.98 | 1.00 | 1.00 | 0.98 | 1.05 | 0.66 | 1.00 |
| Elmo1 | 1.02 | 1.07 | 0.89 | 1.09 | 0.69 | 1.08 | 1.06 | 0.78 | 1.15 | 1.29 | 1.38 | 1.36 |
| Elmsan1 | 0.97 | 1.01 | 0.85 | 1.39 | 0.57 | 1.16 | 1.00 | 1.00 | 1.00 | 0.84 | 0.51 | 0.94 |
| Elovl5 | 1.23 | 1.18 | 1.16 | 0.85 | 0.32 | 1.00 | 0.81 | 0.31 | 0.71 | 1.31 | 1.06 | 1.20 |
| Elovl6 | 0.84 | 0.79 | 0.77 | 1.12 | 1.00 | 0.74 | 1.08 | 0.92 | 0.80 | 1.20 | 1.26 | 1.18 |
| Emp1 | 1.21 | 1.26 | 1.08 | 1.27 | 0.30 | 0.57 | 0.97 | 1.00 | 1.18 | 0.89 | 0.57 | 0.88 |
| Emp2 | 0.98 | 1.09 | 1.09 | 1.19 | 0.32 | 1.34 | 0.73 | 1.00 | 0.87 | 0.87 | 0.71 | 0.79 |
| Eno1 | 0.59 | 1.00 | 1.10 | 1.00 | 1.00 | 1.40 | 0.25 | 1.00 | 0.65 | 1.00 | 1.00 | 1.00 |
| Eogt | 0.92 | 1.21 | 1.05 | 0.80 | 1.00 | 0.70 | 0.86 | 1.00 | 1.02 | 0.52 | 0.32 | 0.72 |
| Epb4.1l2 | 1.02 | 0.96 | 0.95 | 0.70 | 0.10 | 0.57 | 1.07 | 0.94 | 0.97 | 0.89 | 0.78 | 0.90 |
| Epb4.2 | 1.00 | 1.00 | 1.00 | 1.00 | 1.00 | 1.00 | 1.00 | 1.00 | 1.00 | 0.43 | 0.32 | 0.19 |
| Ephb1 | 0.81 | 1.00 | 0.71 | 1.00 | 1.00 | 1.00 | 0.95 | 1.42 | 1.58 | 1.00 | 1.05 | 1.00 |
| Ephx1 | 1.02 | 1.02 | 1.24 | 0.62 | 0.19 | 0.67 | 0.63 | 0.25 | 0.52 | 1.09 | 1.25 | 1.31 |
| Eppin | 1.00 | 1.00 | 1.00 | 1.00 | 1.83 | 0.15 | 1.10 | 1.50 | 1.07 | 1.00 | 1.00 | 1.00 |
| Epyc | 1.00 | 1.00 | 1.00 | 0.82 | 1.00 | 1.60 | 0.97 | 0.15 | 1.20 | 1.00 | 1.00 | 1.00 |
| Eral1 | 0.99 | 1.14 | 1.01 | 0.81 | 0.40 | 1.02 | 1.03 | 0.45 | 1.22 | 1.04 | 1.08 | 0.91 |
| Erbb2ip | 1.00 | 0.95 | 0.78 | 1.17 | 0.24 | 0.94 | 1.08 | 0.91 | 0.90 | 1.04 | 0.73 | 1.02 |
| Erbb3 | 1.24 | 1.22 | 0.88 | 1.55 | 1.00 | 1.54 | 1.00 | 1.00 | 1.00 | 1.00 | 1.00 | 1.00 |
| Ercc6l2 | 1.02 | 0.91 | 0.90 | 0.95 | 1.00 | 0.94 | 1.22 | 0.95 | 1.03 | 1.01 | 0.70 | 1.04 |
| Erdr1 | 0.40 | 0.47 | 0.43 | 0.45 | 0.53 | 0.45 | 0.24 | 0.39 | 0.27 | 0.40 | 0.57 | 0.42 |
| Erg | 1.25 | 1.69 | 1.09 | 0.79 | 0.50 | 0.71 | 1.00 | 1.00 | 1.19 | 0.81 | 0.57 | 0.97 |
| Erich1 | 0.97 | 0.72 | 1.06 | 0.98 | 1.00 | 1.10 | 0.98 | 0.44 | 0.66 | 1.12 | 1.04 | 1.04 |
| Esrp2 | 0.82 | 0.81 | 0.73 | 1.00 | 1.00 | 1.00 | 1.00 | 1.00 | 1.00 | 1.00 | 1.00 | 1.00 |
| Esrrg | 1.11 | 1.06 | 0.85 | 1.11 | 1.00 | 1.00 | 1.00 | 1.00 | 1.00 | 1.00 | 1.48 | 1.00 |
| Etv3 | 0.83 | 0.74 | 0.68 | 0.74 | 0.15 | 1.08 | 1.06 | 1.00 | 1.07 | 1.01 | 0.67 | 1.06 |
| Etv6 | 1.14 | 0.97 | 0.94 | 1.06 | 0.45 | 0.89 | 1.31 | 1.00 | 0.99 | 0.91 | 0.76 | 0.88 |
| Evi2b | 1.42 | 0.98 | 1.30 | 0.49 | 0.52 | 0.78 | 1.00 | 1.00 | 1.00 | 0.99 | 0.56 | 0.91 |
| Evi5 | 1.09 | 1.03 | 0.99 | 0.95 | 0.34 | 0.85 | 0.93 | 0.88 | 1.01 | 0.81 | 0.75 | 0.86 |
| Exd2 | 1.00 | 0.90 | 0.94 | 0.73 | 0.86 | 0.88 | 1.21 | 0.69 | 1.05 | 1.02 | 1.02 | 1.19 |
| Exosc3 | 0.85 | 0.62 | 0.93 | 1.18 | 1.64 | 1.05 | 0.94 | 0.75 | 0.94 | 0.95 | 0.99 | 1.17 |
| Exosc9 | 0.70 | 0.90 | 1.07 | 0.93 | 1.00 | 1.02 | 0.90 | 0.94 | 0.86 | 1.14 | 1.08 | 1.09 |
| Extl2 | 1.06 | 0.83 | 1.00 | 0.79 | 1.00 | 0.73 | 0.90 | 0.29 | 1.02 | 1.21 | 1.51 | 1.27 |
| F13b | 1.00 | 1.00 | 1.00 | 1.00 | 1.00 | 1.00 | 1.00 | 1.00 | 1.00 | 1.00 | 1.00 | 1.00 |
| F2rl1 | 0.94 | 0.91 | 0.82 | 1.07 | 1.00 | 1.06 | 1.00 | 1.00 | 1.00 | 1.02 | 0.63 | 1.09 |
| Fabp1 | 2.06 | 0.64 | 4.75 | 0.68 | 1.00 | 1.00 | 1.00 | 1.00 | 0.69 | 1.74 | 1.51 | 1.33 |
| Fabp5 | 0.48 | 0.57 | 0.50 | 0.25 | 1.16 | 0.35 | 0.66 | 0.33 | 0.33 | 0.71 | 1.01 | 0.41 |
| Fabp7 | 1.00 | 1.00 | 1.00 | 1.00 | 1.00 | 0.55 | 1.00 | 1.00 | 1.00 | 1.75 | 1.30 | 1.00 |
| Fam102a | 0.84 | 0.95 | 0.80 | 1.23 | 0.50 | 1.53 | 0.83 | 0.49 | 0.98 | 0.91 | 0.72 | 1.00 |
| Fam103a1 | 0.90 | 0.94 | 0.97 | 0.98 | 1.10 | 1.03 | 1.07 | 0.49 | 1.04 | 1.15 | 1.11 | 0.96 |
| Fam107b | 0.80 | 0.67 | 0.72 | 1.10 | 0.45 | 0.88 | 0.98 | 1.08 | 1.04 | 2.15 | 1.70 | 1.61 |
| Fam117a | 0.73 | 0.76 | 0.93 | 0.81 | 0.56 | 0.90 | 1.06 | 0.64 | 0.90 | 0.93 | 0.98 | 0.92 |
| Fam122a | 0.94 | 1.11 | 0.89 | 1.13 | 0.36 | 1.02 | 0.76 | 0.64 | 1.00 | 1.04 | 1.07 | 1.03 |
| Fam122c | 1.00 | 1.00 | 1.00 | 1.00 | 1.00 | 1.00 | 1.12 | 0.16 | 1.24 | 1.00 | 1.00 | 1.00 |

Fig. 35- 32

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| E2f6 | 1.20 | 0.54 | 0.95 | 0.99 | 0.83 | 1.15 | 0.81 | 0.15 | 0.93 | 0.52 | 0.70 | 0.71 |
| Eaf1 | 1.02 | 1.07 | 1.05 | 0.92 | 1.00 | 1.11 | 0.96 | 0.15 | 1.04 | 0.53 | 0.79 | 0.85 |
| Ear10 | 1.00 | 1.00 | 1.00 | 1.00 | 1.00 | 1.00 | 1.00 | 1.00 | 1.00 | 0.21 | 0.50 | 0.98 |
| Ebag9 | 1.08 | 0.61 | 0.60 | 1.01 | 1.00 | 1.05 | 0.96 | 0.18 | 1.05 | 0.75 | 1.18 | 1.09 |
| Ebf1 | 1.00 | 1.00 | 1.00 | 0.94 | 1.00 | 1.32 | 0.89 | 0.34 | 1.18 | 0.46 | 0.71 | 0.93 |
| Echdc1 | 1.00 | 1.00 | 1.00 | 0.88 | 0.85 | 0.89 | 1.19 | 0.95 | 1.28 | 1.00 | 1.00 | 1.00 |
| Eci3 | 0.99 | 0.95 | 1.40 | 1.00 | 1.00 | 1.00 | 0.49 | 4.45 | 0.44 | 1.00 | 1.00 | 0.89 |
| Efcab14 | 1.03 | 0.90 | 0.92 | 0.93 | 0.73 | 0.95 | 0.85 | 0.10 | 0.93 | 0.57 | 1.21 | 1.19 |
| Efna3 | 1.00 | 1.00 | 1.00 | 0.94 | 1.00 | 0.95 | 0.79 | 0.02 | 0.56 | 1.00 | 1.00 | 1.00 |
| Efnb2 | 1.00 | 1.00 | 1.00 | 0.93 | 1.00 | 0.92 | 1.06 | 0.09 | 1.10 | 1.00 | 1.00 | 1.00 |
| Efr3a | 1.09 | 0.98 | 0.78 | 1.02 | 1.48 | 1.06 | 0.99 | 0.18 | 1.11 | 0.60 | 0.96 | 0.95 |
| Egr2 | 1.00 | 1.00 | 1.00 | 1.45 | 1.00 | 1.08 | 1.10 | 0.53 | 1.05 | 1.00 | 1.00 | 1.00 |
| Ehd3 | 1.00 | 1.00 | 1.00 | 0.99 | 1.68 | 0.98 | 1.42 | 0.19 | 1.43 | 0.27 | 0.54 | 0.57 |
| Ehmt1 | 0.81 | 1.49 | 0.99 | 0.97 | 1.00 | 0.99 | 0.93 | 0.14 | 1.00 | 0.58 | 1.00 | 0.89 |
| Eif2a | 1.05 | 0.99 | 0.92 | 1.09 | 0.60 | 1.02 | 0.84 | 0.16 | 0.95 | 0.57 | 0.96 | 1.05 |
| Eif2ak3 | 0.81 | 0.75 | 0.75 | 0.84 | 1.00 | 0.86 | 0.85 | 0.12 | 0.99 | 0.27 | 0.80 | 0.89 |
| Eif3a | 1.04 | 0.97 | 1.06 | 1.04 | 1.23 | 0.94 | 0.84 | 0.14 | 0.94 | 0.40 | 0.70 | 0.74 |
| Eif3e | 1.07 | 0.86 | 1.20 | 1.36 | 0.12 | 1.12 | 0.93 | 2.07 | 0.91 | 1.69 | 1.16 | 1.17 |
| Eif4a3 | 1.01 | 1.81 | 0.85 | 0.87 | 1.28 | 1.09 | 1.40 | 2.72 | 0.98 | 1.53 | 0.90 | 0.94 |
| Eif4e3 | 1.00 | 1.00 | 1.00 | 0.86 | 1.00 | 0.87 | 0.97 | 0.10 | 1.34 | 0.23 | 0.83 | 1.00 |
| Eif4ebp2 | 1.01 | 0.73 | 1.26 | 0.75 | 1.00 | 0.89 | 0.80 | 0.03 | 1.23 | 0.08 | 0.88 | 0.79 |
| Elf1 | 1.49 | 1.60 | 1.51 | 0.98 | 1.00 | 0.98 | 0.79 | 0.05 | 1.03 | 0.30 | 0.83 | 0.89 |
| Elmo1 | 1.00 | 1.00 | 1.00 | 1.15 | 0.86 | 1.04 | 1.59 | 0.74 | 1.30 | 0.43 | 1.31 | 1.13 |
| Elmsan1 | 1.07 | 0.91 | 1.00 | 0.97 | 1.00 | 0.96 | 0.90 | 0.20 | 1.26 | 0.58 | 0.83 | 0.79 |
| Elovl5 | 0.80 | 0.79 | 1.16 | 0.91 | 0.24 | 0.98 | 1.09 | 0.14 | 1.61 | 0.75 | 1.50 | 1.31 |
| Elovl6 | 1.00 | 1.00 | 1.00 | 0.88 | 1.16 | 0.91 | 0.78 | 0.17 | 1.06 | 0.84 | 0.68 | 0.89 |
| Emp1 | 0.94 | 0.92 | 0.83 | 1.35 | 1.00 | 1.07 | 0.68 | 0.16 | 0.81 | 0.26 | 0.61 | 0.74 |
| Emp2 | 1.15 | 0.94 | 1.15 | 0.95 | 1.38 | 0.79 | 0.81 | 0.15 | 0.68 | 1.00 | 1.00 | 1.00 |
| Eno1 | 1.00 | 1.00 | 1.00 | 0.34 | 1.00 | 0.77 | 0.85 | 0.96 | 0.39 | 1.00 | 0.66 | 1.52 |
| Eogt | 1.10 | 1.23 | 1.00 | 0.76 | 1.00 | 0.86 | 0.50 | 0.13 | 0.71 | 1.00 | 0.31 | 0.35 |
| Epb4.1l2 | 1.19 | 1.24 | 1.28 | 0.86 | 1.00 | 0.90 | 1.05 | 0.21 | 1.30 | 0.52 | 0.91 | 0.99 |
| Epb4.2 | 1.00 | 1.00 | 1.00 | 1.00 | 1.00 | 1.00 | 1.00 | 1.00 | 1.00 | 0.35 | 0.68 | 0.73 |
| Ephb1 | 1.00 | 1.00 | 1.00 | 0.93 | 1.36 | 0.88 | 1.00 | 1.00 | 1.00 | 1.00 | 1.00 | 1.00 |
| Ephx1 | 1.12 | 1.20 | 1.01 | 0.68 | 0.45 | 0.90 | 0.86 | 0.51 | 0.78 | 0.74 | 0.86 | 1.14 |
| Eppin | 1.00 | 1.00 | 1.00 | 1.00 | 1.00 | 1.00 | 1.00 | 1.00 | 1.00 | 1.00 | 1.00 | 1.00 |
| Epyc | 1.00 | 1.00 | 1.00 | 1.00 | 1.00 | 1.00 | 1.08 | 1.00 | 1.00 | 1.00 | 1.00 | 1.00 |
| Eral1 | 0.96 | 0.85 | 0.71 | 0.95 | 0.99 | 0.91 | 1.12 | 0.08 | 1.01 | 0.41 | 0.89 | 1.05 |
| Erbb2ip | 1.53 | 1.19 | 1.17 | 0.86 | 1.00 | 0.90 | 0.80 | 0.12 | 1.18 | 0.22 | 0.84 | 0.84 |
| Erbb3 | 2.10 | 0.88 | 1.58 | 0.82 | 1.00 | 0.96 | 0.93 | 0.12 | 1.27 | 1.00 | 1.00 | 1.00 |
| Ercc6l2 | 0.83 | 1.25 | 1.00 | 0.91 | 1.00 | 0.81 | 0.97 | 0.19 | 1.13 | 0.49 | 0.78 | 0.71 |
| Erdr1 | 0.48 | 0.30 | 0.41 | 0.37 | 0.13 | 0.38 | 0.35 | 0.84 | 0.39 | 0.46 | 0.36 | 0.37 |
| Erg | 1.00 | 1.00 | 1.00 | 0.78 | 1.00 | 0.85 | 0.92 | 0.29 | 1.26 | 0.45 | 0.92 | 0.68 |
| Erich1 | 1.14 | 1.00 | 1.00 | 1.01 | 0.40 | 1.46 | 0.74 | 0.18 | 0.88 | 0.47 | 1.24 | 0.77 |
| Esrp2 | 1.23 | 1.46 | 1.42 | 1.00 | 1.00 | 1.00 | 0.66 | 0.09 | 0.73 | 1.00 | 1.00 | 1.00 |
| Esrrg | 0.95 | 0.90 | 1.00 | 0.99 | 1.00 | 0.97 | 0.90 | 1.00 | 1.02 | 1.00 | 1.00 | 1.00 |
| Etv3 | 1.08 | 1.12 | 1.26 | 1.00 | 1.00 | 1.03 | 0.82 | 0.06 | 0.96 | 0.43 | 1.05 | 0.96 |
| Etv6 | 0.71 | 0.69 | 0.79 | 1.05 | 1.00 | 0.98 | 0.74 | 0.09 | 0.94 | 0.67 | 0.99 | 1.05 |
| Evi2b | 1.00 | 1.00 | 1.00 | 1.00 | 1.00 | 1.00 | 0.71 | 0.36 | 0.93 | 0.39 | 1.09 | 1.18 |
| Evi5 | 1.43 | 1.16 | 1.07 | 0.89 | 0.60 | 0.93 | 0.80 | 0.16 | 1.05 | 0.54 | 0.86 | 0.73 |
| Exd2 | 0.88 | 0.64 | 0.79 | 0.95 | 0.30 | 1.00 | 0.79 | 0.19 | 0.99 | 0.49 | 1.01 | 0.98 |
| Exosc3 | 2.00 | 1.11 | 1.08 | 1.02 | 0.16 | 1.00 | 0.85 | 0.93 | 0.80 | 0.98 | 0.94 | 0.97 |
| Exosc9 | 1.38 | 1.06 | 1.00 | 1.19 | 0.32 | 0.99 | 1.03 | 0.18 | 0.97 | 0.46 | 0.71 | 0.95 |
| Extl2 | 0.82 | 0.86 | 1.00 | 1.08 | 1.40 | 1.03 | 0.78 | 0.19 | 0.94 | 0.66 | 1.05 | 1.24 |
| F13b | 1.00 | 1.00 | 1.00 | 1.00 | 1.00 | 1.00 | 1.00 | 1.00 | 1.00 | 1.00 | 1.00 | 1.00 |
| F2rl1 | 1.00 | 1.00 | 1.00 | 1.00 | 1.00 | 1.00 | 1.23 | 0.16 | 1.34 | 1.00 | 1.00 | 1.00 |
| Fabp1 | 1.00 | 1.00 | 1.00 | 0.27 | 1.00 | 1.01 | 1.00 | 1.00 | 1.92 | 1.00 | 1.00 | 1.00 |
| Fabp5 | 1.71 | 1.46 | 0.32 | 0.70 | 0.97 | 0.48 | 0.97 | 1.42 | 0.69 | 1.87 | 0.86 | 0.92 |
| Fabp7 | 1.00 | 1.00 | 1.00 | 0.68 | 1.01 | 0.53 | 1.00 | 1.00 | 1.00 | 1.13 | 1.54 | 1.00 |
| Fam102a | 0.78 | 0.72 | 0.88 | 1.05 | 1.11 | 0.94 | 1.04 | 0.54 | 0.96 | 0.82 | 1.07 | 1.05 |
| Fam103a1 | 1.09 | 1.03 | 0.96 | 1.05 | 0.42 | 1.04 | 1.05 | 0.14 | 1.10 | 0.58 | 1.24 | 1.02 |
| Fam107b | 0.75 | 1.13 | 1.48 | 1.18 | 1.12 | 1.06 | 1.05 | 0.19 | 1.05 | 0.54 | 1.10 | 1.02 |
| Fam117a | 0.65 | 0.66 | 0.71 | 1.08 | 1.00 | 1.09 | 0.83 | 0.10 | 0.92 | 0.33 | 0.99 | 0.95 |
| Fam122a | 1.40 | 1.37 | 1.20 | 1.02 | 3.80 | 1.12 | 1.19 | 0.08 | 0.92 | 0.58 | 0.99 | 1.09 |
| Fam122c | 1.00 | 1.00 | 1.00 | 1.00 | 1.00 | 1.00 | 1.00 | 1.00 | 1.00 | 1.00 | 1.00 | 1.00 |

Fig. 35- 33

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Fam129a | 0.67 | 1.00 | 0.84 | 1.34 | 0.24 | 0.86 | 0.87 | 1.03 | 1.28 | 0.26 | 0.40 | 0.75 |
| Fam131a | 0.81 | 1.39 | 0.73 | 0.74 | 0.17 | 0.84 | 0.76 | 0.71 | 0.47 | 0.94 | 1.01 | 1.24 |
| Fam135a | 0.58 | 0.94 | 0.69 | 2.70 | 0.46 | 0.93 | 0.81 | 1.15 | 1.01 | 0.48 | 0.45 | 0.95 |
| Fam167a | 1.00 | 1.00 | 1.00 | 1.00 | 1.00 | 1.00 | 1.00 | 1.00 | 1.00 | 0.81 | 0.81 | 1.42 |
| Fam173b | 0.94 | 0.97 | 0.94 | 0.42 | 1.64 | 0.81 | 1.13 | 0.81 | 0.99 | 0.63 | 1.23 | 0.91 |
| Fam204a | 0.78 | 1.90 | 0.88 | 1.47 | 0.42 | 1.02 | 0.85 | 0.90 | 0.97 | 0.47 | 0.44 | 1.29 |
| Fam20b | 0.69 | 1.39 | 0.87 | 0.92 | 0.42 | 0.80 | 0.91 | 1.05 | 1.01 | 0.58 | 0.61 | 1.11 |
| Fam219a | 1.15 | 1.83 | 1.23 | 0.97 | 0.26 | 1.23 | 1.93 | 2.18 | 1.37 | 2.97 | 0.66 | 1.15 |
| Fam26e | 1.03 | 1.69 | 0.68 | 1.00 | 1.00 | 1.00 | 1.95 | 1.66 | 1.79 | 0.46 | 0.19 | 1.09 |
| Fam43a | 0.93 | 1.32 | 0.89 | 0.88 | 0.23 | 0.96 | 1.01 | 0.99 | 1.09 | 0.67 | 0.27 | 1.18 |
| Fam57a | 1.00 | 1.00 | 1.00 | 0.71 | 0.63 | 0.77 | 0.79 | 1.06 | 0.57 | 1.00 | 0.65 | 0.89 |
| Fam60a | 1.00 | 1.00 | 1.00 | 1.21 | 1.00 | 1.00 | 1.00 | 1.00 | 1.00 | 1.00 | 0.33 | 1.15 |
| Fam65c | 1.00 | 1.00 | 1.00 | 1.00 | 1.00 | 1.00 | 1.00 | 1.00 | 1.00 | 1.00 | 1.00 | 1.00 |
| Fam78a | 0.22 | 0.41 | 0.14 | 1.00 | 1.00 | 1.00 | 0.30 | 0.26 | 0.51 | 0.55 | 0.58 | 0.79 |
| Fam83c | 1.00 | 1.00 | 1.00 | 1.00 | 1.00 | 1.00 | 1.00 | 1.00 | 1.00 | 1.00 | 1.00 | 1.00 |
| Fam84b | 0.60 | 1.00 | 0.78 | 1.91 | 0.33 | 0.61 | 1.01 | 0.85 | 1.25 | 0.26 | 0.36 | 1.06 |
| Far2 | 0.99 | 1.04 | 0.86 | 1.11 | 0.73 | 1.20 | 0.96 | 1.66 | 0.76 | 1.00 | 0.68 | 1.02 |
| Fastkd5 | 1.13 | 1.75 | 1.10 | 0.86 | 0.18 | 0.69 | 1.09 | 1.06 | 0.94 | 0.80 | 0.55 | 1.07 |
| Fat1 | 1.00 | 1.00 | 1.00 | 1.16 | 0.54 | 0.87 | 0.91 | 0.77 | 1.18 | 0.91 | 0.34 | 0.96 |
| Fbxl12 | 0.85 | 1.14 | 0.97 | 0.95 | 0.62 | 1.12 | 0.66 | 0.64 | 0.75 | 0.41 | 0.52 | 0.91 |
| Fbxl14 | 0.71 | 1.56 | 0.87 | 0.72 | 0.19 | 0.78 | 1.12 | 0.94 | 1.15 | 0.63 | 0.37 | 1.01 |
| Fbxl15 | 1.10 | 0.88 | 1.06 | 0.27 | 1.24 | 0.63 | 0.80 | 0.76 | 0.75 | 0.51 | 2.50 | 0.77 |
| Fbxl4 | 0.95 | 1.67 | 1.04 | 1.66 | 0.44 | 1.33 | 1.33 | 1.08 | 1.02 | 0.32 | 0.23 | 0.99 |
| Fbxo21 | 0.52 | 1.30 | 0.80 | 1.22 | 0.78 | 1.55 | 0.75 | 0.66 | 0.71 | 0.52 | 0.52 | 0.93 |
| Fbxo44 | 0.59 | 0.33 | 0.41 | 0.10 | 0.41 | 0.10 | 0.15 | 0.12 | 0.19 | 1.49 | 1.70 | 0.66 |
| Fbxo5 | 1.00 | 1.00 | 1.00 | 1.01 | 1.39 | 0.99 | 0.77 | 0.91 | 0.97 | 0.42 | 0.59 | 0.65 |
| Fcer2a | 1.00 | 1.00 | 1.00 | 1.00 | 1.00 | 1.00 | 1.00 | 1.00 | 1.00 | 0.28 | 0.13 | 0.20 |
| Fcho2 | 1.00 | 1.61 | 1.18 | 4.41 | 0.68 | 1.11 | 1.02 | 1.35 | 1.08 | 0.39 | 0.48 | 1.03 |
| Fchsd2 | 0.84 | 1.00 | 0.70 | 1.37 | 0.43 | 1.08 | 1.18 | 1.29 | 0.94 | 0.35 | 0.29 | 0.77 |
| Fermt1 | 1.00 | 1.00 | 1.00 | 1.00 | 1.00 | 1.00 | 1.00 | 1.00 | 1.00 | 1.00 | 1.00 | 0.86 |
| Fetub | 1.00 | 1.00 | 1.00 | 1.00 | 4.89 | 1.00 | 2.03 | 1.04 | 3.14 | 1.62 | 3.33 | 1.11 |
| Ffar1 | 1.00 | 1.00 | 1.00 | 1.00 | 1.00 | 1.00 | 1.00 | 1.00 | 1.00 | 1.00 | 1.00 | 1.00 |
| Ffar4 | 1.85 | 1.00 | 1.00 | 0.43 | 0.18 | 0.74 | 1.73 | 2.38 | 1.00 | 0.51 | 0.91 | 1.20 |
| Fgf22 | 1.00 | 1.00 | 1.00 | 1.00 | 1.00 | 1.00 | 1.00 | 1.00 | 1.00 | 1.00 | 1.00 | 1.00 |
| Fgfbp1 | 1.00 | 1.00 | 1.00 | 1.00 | 1.00 | 1.00 | 1.00 | 1.00 | 3.22 | 0.55 | 0.87 | 1.67 |
| Fgfrl1 | 0.81 | 1.37 | 0.83 | 0.61 | 0.45 | 1.00 | 1.09 | 0.85 | 0.79 | 0.48 | 0.57 | 1.04 |
| Fhdc1 | 1.00 | 1.00 | 1.00 | 1.41 | 0.36 | 1.67 | 1.00 | 1.00 | 1.00 | 0.60 | 0.29 | 1.03 |
| Fignl1 | 1.00 | 1.00 | 1.00 | 1.00 | 1.00 | 1.00 | 1.00 | 1.00 | 1.00 | 1.00 | 1.00 | 1.00 |
| Filip1l | 0.68 | 2.01 | 0.71 | 2.31 | 0.22 | 1.17 | 1.27 | 1.40 | 1.23 | 0.45 | 0.24 | 1.02 |
| Fkrp | 0.87 | 1.68 | 0.96 | 0.88 | 0.27 | 1.15 | 0.88 | 0.81 | 0.91 | 0.36 | 0.31 | 1.00 |
| Flg2 | 1.00 | 1.00 | 1.00 | 1.00 | 1.00 | 1.00 | 1.00 | 1.00 | 1.00 | 1.00 | 1.00 | 1.00 |
| Flt1 | 1.02 | 2.03 | 1.51 | 2.07 | 0.08 | 1.05 | 1.55 | 2.02 | 1.33 | 0.60 | 0.32 | 1.43 |
| Flywch1 | 1.03 | 3.82 | 1.38 | 0.54 | 0.04 | 0.85 | 1.06 | 1.43 | 1.30 | 1.04 | 0.19 | 1.14 |
| Fmr1 | 0.95 | 2.06 | 0.90 | 2.99 | 0.42 | 0.88 | 0.84 | 1.14 | 0.83 | 0.61 | 0.65 | 0.98 |
| Fn3krp | 0.84 | 1.00 | 0.83 | 1.43 | 0.12 | 0.99 | 0.96 | 0.99 | 1.02 | 1.00 | 0.26 | 0.98 |
| Fndc3b | 1.49 | 1.78 | 1.14 | 2.96 | 0.47 | 0.94 | 0.95 | 1.12 | 1.07 | 0.46 | 0.63 | 1.16 |
| Fosb | 1.00 | 1.00 | 1.00 | 1.00 | 1.00 | 1.03 | 1.00 | 1.00 | 1.00 | 1.79 | 2.73 | 2.28 |
| Foxf2 | 1.00 | 1.00 | 1.00 | 1.00 | 1.00 | 1.00 | 1.00 | 1.00 | 1.00 | 0.32 | 0.19 | 0.71 |
| Foxj3 | 1.09 | 1.71 | 1.08 | 2.29 | 0.38 | 1.15 | 1.43 | 1.62 | 1.09 | 0.39 | 0.52 | 0.99 |
| Foxk1 | 1.18 | 2.45 | 1.66 | 1.97 | 0.30 | 1.00 | 1.63 | 1.95 | 1.44 | 0.69 | 0.33 | 0.93 |
| Foxn2 | 1.14 | 1.43 | 1.42 | 3.23 | 0.86 | 1.07 | 1.34 | 1.48 | 1.01 | 0.94 | 0.57 | 1.03 |
| Foxq1 | 1.00 | 1.00 | 1.00 | 1.40 | 1.00 | 1.00 | 1.00 | 1.02 | 1.00 | 0.72 | 0.31 | 0.90 |
| Fpgt | 0.79 | 1.34 | 1.12 | 1.84 | 0.30 | 1.26 | 0.78 | 1.20 | 0.92 | 0.66 | 0.64 | 1.01 |
| Frmd4a | 1.10 | 1.00 | 1.30 | 2.45 | 0.38 | 1.22 | 1.19 | 1.23 | 1.32 | 0.60 | 0.41 | 0.92 |
| Frmd6 | 0.67 | 1.30 | 0.94 | 1.70 | 0.47 | 1.08 | 0.88 | 0.81 | 0.95 | 0.29 | 0.25 | 0.98 |
| Frs2 | 0.86 | 1.03 | 0.86 | 1.93 | 0.17 | 0.91 | 1.01 | 1.41 | 1.11 | 0.61 | 0.50 | 1.04 |
| Frs3 | 0.89 | 1.06 | 0.90 | 0.91 | 0.30 | 0.99 | 1.01 | 0.90 | 0.73 | 0.45 | 0.31 | 0.88 |
| Fstl1 | 0.73 | 0.87 | 0.86 | 1.05 | 0.42 | 0.92 | 0.68 | 0.62 | 1.05 | 0.34 | 0.43 | 0.75 |
| Fzd1 | 0.63 | 1.00 | 0.94 | 1.01 | 0.16 | 0.95 | 0.92 | 0.65 | 1.30 | 0.35 | 0.11 | 0.87 |
| Fzd4 | 1.00 | 2.46 | 1.70 | 1.01 | 0.24 | 0.58 | 1.54 | 3.29 | 1.78 | 1.09 | 0.69 | 1.18 |
| Fzd7 | 0.40 | 0.63 | 0.56 | 1.01 | 0.13 | 0.94 | 0.90 | 1.29 | 1.26 | 0.45 | 0.28 | 0.86 |
| G0s2 | 0.41 | 0.40 | 0.56 | 0.06 | 0.59 | 0.64 | 0.30 | 0.21 | 0.57 | 0.38 | 0.74 | 0.94 |
| G6pd2 | 1.39 | 1.00 | 1.64 | 1.21 | 0.01 | 0.82 | 1.07 | 1.26 | 1.37 | 1.00 | 0.13 | 1.27 |
| Gabpa | 0.93 | 1.59 | 1.01 | 1.03 | 0.34 | 0.87 | 0.84 | 1.22 | 1.04 | 0.22 | 0.37 | 0.95 |

Fig. 35- 34

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Fam129a | 0.75 | 0.49 | 1.07 | 0.82 | 1.00 | 0.81 | 0.88 | 1.00 | 1.00 | 0.94 | 0.41 | 0.90 |
| Fam131a | 0.99 | 1.00 | 1.25 | 1.36 | 1.38 | 1.08 | 1.00 | 1.00 | 1.00 | 0.91 | 1.12 | 0.96 |
| Fam135a | 1.45 | 1.00 | 1.21 | 1.22 | 1.24 | 1.07 | 1.06 | 1.00 | 0.88 | 0.99 | 0.74 | 0.98 |
| Fam167a | 1.04 | 0.93 | 1.22 | 1.00 | 1.00 | 1.00 | 1.00 | 1.00 | 1.00 | 1.00 | 1.00 | 1.00 |
| Fam173b | 0.87 | 1.23 | 0.74 | 1.20 | 1.24 | 1.05 | 1.66 | 0.60 | 1.36 | 0.80 | 1.09 | 0.90 |
| Fam204a | 0.78 | 0.88 | 0.93 | 1.06 | 1.15 | 1.19 | 0.95 | 1.00 | 1.02 | 1.25 | 1.15 | 1.05 |
| Fam20b | 0.77 | 0.70 | 0.99 | 0.95 | 1.53 | 0.99 | 1.01 | 0.49 | 1.04 | 1.05 | 0.83 | 0.95 |
| Fam219a | 1.44 | 1.12 | 1.47 | 1.20 | 0.92 | 1.31 | 1.24 | 1.69 | 1.80 | 1.39 | 0.88 | 1.28 |
| Fam26e | 1.03 | 1.81 | 1.19 | 0.93 | 1.00 | 1.00 | 1.00 | 1.00 | 1.00 | 0.87 | 0.88 | 0.80 |
| Fam43a | 1.01 | 0.91 | 1.24 | 0.93 | 0.82 | 1.23 | 0.57 | 1.00 | 0.80 | 1.93 | 1.80 | 1.27 |
| Fam57a | 0.68 | 0.35 | 1.28 | 1.06 | 1.00 | 0.90 | 1.53 | 1.00 | 0.82 | 1.02 | 0.46 | 0.97 |
| Fam60a | 0.58 | 0.54 | 0.89 | 0.81 | 1.00 | 0.94 | 1.00 | 1.00 | 1.00 | 1.10 | 0.62 | 1.06 |
| Fam65c | 1.00 | 1.00 | 1.00 | 0.77 | 1.00 | 0.99 | 1.00 | 1.00 | 1.00 | 1.00 | 1.00 | 1.00 |
| Fam78a | 0.71 | 0.72 | 0.82 | 1.35 | 1.40 | 1.35 | 1.00 | 1.00 | 1.00 | 1.19 | 0.98 | 0.94 |
| Fam83c | 1.00 | 1.00 | 1.00 | 1.00 | 1.00 | 1.00 | 1.00 | 1.00 | 1.00 | 0.65 | 0.39 | 0.81 |
| Fam84b | 0.84 | 0.73 | 1.15 | 0.99 | 1.15 | 1.09 | 1.45 | 1.00 | 1.09 | 1.05 | 0.66 | 1.09 |
| Far2 | 1.03 | 0.94 | 0.84 | 1.66 | 1.61 | 1.33 | 0.85 | 0.67 | 0.93 | 1.06 | 1.02 | 1.06 |
| Fastkd5 | 0.67 | 0.71 | 0.88 | 0.93 | 0.95 | 0.91 | 0.96 | 1.00 | 0.92 | 0.91 | 1.01 | 1.17 |
| Fat1 | 1.39 | 1.13 | 1.40 | 1.20 | 1.00 | 1.02 | 1.03 | 1.00 | 1.06 | 1.03 | 0.72 | 0.89 |
| Fbxl12 | 0.65 | 0.80 | 0.67 | 0.82 | 0.90 | 0.93 | 1.05 | 0.58 | 0.98 | 0.90 | 0.86 | 0.94 |
| Fbxl14 | 0.61 | 0.61 | 0.75 | 0.95 | 1.25 | 1.04 | 1.04 | 1.03 | 0.98 | 1.02 | 0.84 | 1.04 |
| Fbxl15 | 1.34 | 1.12 | 0.98 | 1.03 | 1.12 | 1.09 | 0.57 | 0.09 | 0.80 | 0.83 | 1.37 | 0.85 |
| Fbxl4 | 0.87 | 0.89 | 0.89 | 1.11 | 1.80 | 1.06 | 1.18 | 1.00 | 0.93 | 1.25 | 0.87 | 0.96 |
| Fbxo21 | 0.83 | 0.90 | 0.96 | 1.12 | 1.77 | 1.50 | 0.89 | 0.29 | 1.20 | 0.97 | 0.68 | 1.02 |
| Fbxo44 | 0.43 | 0.86 | 0.66 | 0.59 | 0.48 | 0.66 | 1.00 | 1.00 | 1.00 | 0.60 | 0.87 | 0.70 |
| Fbxo5 | 0.40 | 0.42 | 0.46 | 0.69 | 1.00 | 0.92 | 1.00 | 1.00 | 0.91 | 0.72 | 0.89 | 1.18 |
| Fcer2a | 0.78 | 0.59 | 0.43 | 1.00 | 1.00 | 1.00 | 1.00 | 1.00 | 1.00 | 0.47 | 0.26 | 0.53 |
| Fcho2 | 1.07 | 0.87 | 1.21 | 1.27 | 1.71 | 1.03 | 1.07 | 0.74 | 1.19 | 1.02 | 0.78 | 1.03 |
| Fchsd2 | 0.72 | 0.67 | 0.89 | 1.16 | 1.00 | 1.10 | 1.03 | 1.04 | 1.10 | 0.88 | 0.80 | 0.99 |
| Fermt1 | 1.28 | 1.07 | 1.56 | 0.98 | 1.35 | 1.03 | 1.00 | 1.00 | 1.00 | 1.05 | 0.69 | 1.07 |
| Fetub | 1.80 | 1.42 | 1.20 | 1.00 | 0.85 | 1.00 | 1.05 | 1.38 | 1.19 | 1.00 | 1.00 | 1.00 |
| Ffar1 | 1.00 | 1.00 | 1.00 | 1.00 | 1.00 | 1.00 | 1.00 | 1.00 | 1.00 | 0.77 | 1.00 | 1.00 |
| Ffar4 | 0.47 | 0.53 | 0.53 | 1.00 | 1.00 | 1.00 | 1.00 | 1.00 | 1.34 | 0.88 | 1.22 | 1.27 |
| Fgf22 | 1.00 | 1.00 | 1.00 | 1.00 | 1.00 | 1.00 | 1.00 | 1.00 | 1.00 | 1.00 | 1.00 | 1.00 |
| Fgfbp1 | 3.29 | 2.77 | 1.24 | 1.55 | 3.71 | 1.92 | 1.00 | 1.00 | 1.00 | 1.14 | 1.34 | 1.18 |
| Fgfrl1 | 1.07 | 0.98 | 0.90 | 0.98 | 0.82 | 1.00 | 0.82 | 1.24 | 0.83 | 0.95 | 0.82 | 1.14 |
| Fhdc1 | 1.00 | 1.00 | 1.09 | 1.00 | 1.00 | 1.00 | 1.00 | 1.00 | 1.00 | 1.41 | 1.38 | 1.12 |
| Fignl1 | 0.22 | 0.20 | 0.36 | 0.87 | 1.00 | 0.65 | 1.00 | 1.00 | 1.00 | 0.75 | 0.86 | 0.96 |
| Filip1l | 1.04 | 0.80 | 1.66 | 1.14 | 1.00 | 1.05 | 1.29 | 1.00 | 1.13 | 1.12 | 0.66 | 1.11 |
| Fkrp | 0.92 | 0.78 | 1.06 | 1.09 | 1.27 | 1.11 | 1.67 | 1.00 | 1.22 | 1.05 | 0.93 | 1.02 |
| Flg2 | 1.00 | 1.00 | 1.00 | 1.00 | 1.00 | 1.00 | 1.00 | 1.00 | 1.00 | 1.00 | 1.00 | 1.00 |
| Flt1 | 1.33 | 1.02 | 0.90 | 1.48 | 1.00 | 1.40 | 1.38 | 1.00 | 1.27 | 1.14 | 0.74 | 0.81 |
| Flywch1 | 0.89 | 0.74 | 1.11 | 1.14 | 1.00 | 1.06 | 1.15 | 1.00 | 1.08 | 1.06 | 0.58 | 0.88 |
| Fmr1 | 0.72 | 0.71 | 0.81 | 1.09 | 1.65 | 0.97 | 1.29 | 0.94 | 1.14 | 1.01 | 0.76 | 1.06 |
| Fn3krp | 0.77 | 0.75 | 1.01 | 1.01 | 1.00 | 1.05 | 0.82 | 1.00 | 0.77 | 1.03 | 0.63 | 1.02 |
| Fndc3b | 1.68 | 1.31 | 1.43 | 1.30 | 1.00 | 1.16 | 2.34 | 1.00 | 2.08 | 0.97 | 0.78 | 1.01 |
| Fosb | 1.32 | 1.54 | 1.19 | 1.00 | 1.00 | 1.00 | 1.00 | 1.00 | 1.00 | 1.26 | 1.53 | 1.50 |
| Foxf2 | 1.00 | 1.00 | 1.00 | 1.00 | 1.00 | 1.00 | 1.00 | 1.00 | 1.00 | 0.80 | 0.72 | 0.81 |
| Foxj3 | 0.73 | 0.68 | 0.84 | 1.02 | 1.38 | 1.12 | 1.07 | 1.00 | 1.02 | 1.10 | 0.73 | 0.99 |
| Foxk1 | 0.53 | 0.43 | 1.07 | 1.24 | 1.25 | 1.34 | 0.86 | 1.00 | 0.94 | 1.00 | 0.50 | 0.94 |
| Foxn2 | 0.66 | 0.54 | 0.87 | 1.10 | 1.00 | 0.94 | 1.25 | 1.00 | 1.15 | 1.02 | 0.75 | 1.08 |
| Foxq1 | 1.68 | 1.82 | 2.81 | 1.39 | 1.98 | 1.55 | 0.49 | 0.67 | 0.84 | 0.89 | 0.62 | 0.78 |
| Fpgt | 0.80 | 0.74 | 1.05 | 1.10 | 1.48 | 1.15 | 0.92 | 1.00 | 1.10 | 1.15 | 0.83 | 1.24 |
| Frmd4a | 1.23 | 0.95 | 1.41 | 0.90 | 1.00 | 1.31 | 0.74 | 1.00 | 0.96 | 0.96 | 0.63 | 0.87 |
| Frmd6 | 1.52 | 1.41 | 1.32 | 0.81 | 1.00 | 1.04 | 1.30 | 1.00 | 1.39 | 1.03 | 0.69 | 0.98 |
| Frs2 | 0.57 | 0.48 | 0.86 | 1.15 | 1.05 | 1.08 | 1.06 | 1.00 | 1.11 | 1.02 | 0.47 | 0.90 |
| Frs3 | 1.21 | 1.26 | 1.01 | 0.98 | 1.14 | 1.12 | 0.91 | 0.82 | 1.30 | 0.94 | 0.79 | 0.79 |
| Fstl1 | 0.90 | 0.67 | 0.94 | 0.66 | 1.33 | 0.85 | 1.00 | 1.00 | 1.00 | 0.78 | 0.70 | 0.97 |
| Fzd1 | 1.34 | 1.09 | 1.41 | 0.70 | 1.83 | 1.02 | 1.05 | 1.00 | 0.99 | 1.05 | 0.77 | 0.93 |
| Fzd4 | 0.51 | 0.51 | 0.47 | 1.23 | 1.24 | 1.28 | 0.56 | 1.00 | 0.97 | 1.05 | 0.59 | 0.85 |
| Fzd7 | 1.46 | 0.94 | 1.57 | 0.92 | 0.83 | 1.08 | 1.07 | 1.00 | 1.68 | 0.96 | 0.60 | 0.88 |
| G0s2 | 0.96 | 1.02 | 0.67 | 0.63 | 0.74 | 0.74 | 0.55 | 0.10 | 0.67 | 0.89 | 0.96 | 0.68 |
| G6pd2 | 1.01 | 0.80 | 1.12 | 1.17 | 1.00 | 0.93 | 0.63 | 1.00 | 1.32 | 1.05 | 0.52 | 0.97 |
| Gabpa | 0.70 | 0.65 | 0.84 | 1.04 | 1.39 | 1.03 | 0.89 | 0.66 | 0.90 | 0.99 | 0.81 | 0.96 |

Fig. 35- 35

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Fam129a | 0.79 | 0.80 | 0.69 | 0.76 | 0.20 | 0.46 | 0.55 | 0.52 | 0.50 | 0.51 | 0.32 | 0.63 |
| Fam131a | 1.04 | 1.44 | 1.41 | 0.76 | 1.00 | 1.45 | 1.05 | 2.29 | 1.08 | 1.02 | 2.54 | 1.02 |
| Fam135a | 0.95 | 0.93 | 0.81 | 1.01 | 0.86 | 0.76 | 1.20 | 0.34 | 1.12 | 0.78 | 0.91 | 1.05 |
| Fam167a | 1.00 | 1.00 | 1.00 | 0.95 | 1.00 | 1.78 | 1.09 | 1.40 | 0.93 | 0.86 | 0.68 | 0.81 |
| Fam173b | 0.87 | 1.10 | 0.93 | 1.17 | 1.21 | 0.99 | 1.10 | 0.66 | 1.18 | 0.70 | 0.89 | 0.80 |
| Fam204a | 1.20 | 1.00 | 1.05 | 1.25 | 0.86 | 0.89 | 1.12 | 0.73 | 0.85 | 0.95 | 0.94 | 1.00 |
| Fam20b | 0.93 | 0.91 | 0.78 | 0.72 | 0.22 | 0.71 | 1.13 | 0.76 | 1.06 | 1.04 | 0.89 | 1.16 |
| Fam219a | 1.22 | 1.26 | 1.38 | 1.43 | 0.59 | 1.30 | 1.19 | 3.43 | 1.14 | 1.43 | 1.79 | 1.50 |
| Fam26e | 1.24 | 1.22 | 1.41 | 1.00 | 1.00 | 0.93 | 1.00 | 1.00 | 1.00 | 0.99 | 1.08 | 1.07 |
| Fam43a | 0.86 | 0.86 | 0.91 | 1.26 | 0.10 | 1.13 | 1.00 | 1.00 | 1.00 | 0.78 | 0.68 | 0.89 |
| Fam57a | 1.03 | 0.97 | 0.92 | 1.25 | 1.00 | 1.28 | 1.00 | 1.00 | 1.00 | 0.87 | 0.68 | 0.66 |
| Fam60a | 0.99 | 0.99 | 1.15 | 1.26 | 1.00 | 2.11 | 0.85 | 1.00 | 0.98 | 1.11 | 0.65 | 1.22 |
| Fam65c | 0.81 | 1.27 | 0.99 | 1.00 | 1.00 | 1.00 | 1.00 | 1.00 | 1.00 | 1.06 | 0.79 | 0.78 |
| Fam78a | 1.00 | 1.00 | 1.00 | 1.04 | 1.00 | 1.00 | 0.86 | 1.02 | 1.02 | 1.05 | 0.85 | 1.13 |
| Fam83c | 0.80 | 0.72 | 0.59 | 1.00 | 1.00 | 1.00 | 1.00 | 1.00 | 1.00 | 1.00 | 1.00 | 1.00 |
| Fam84b | 1.14 | 1.03 | 0.89 | 0.78 | 0.45 | 0.81 | 0.82 | 1.00 | 0.91 | 1.10 | 0.77 | 1.28 |
| Far2 | 1.34 | 1.09 | 1.06 | 0.90 | 1.65 | 0.93 | 1.04 | 1.56 | 1.03 | 1.17 | 1.06 | 1.22 |
| Fastkd5 | 0.88 | 0.75 | 0.76 | 1.40 | 1.00 | 0.98 | 1.36 | 1.00 | 0.97 | 1.27 | 0.90 | 1.05 |
| Fat1 | 0.99 | 0.95 | 0.82 | 0.97 | 0.23 | 0.90 | 1.10 | 1.00 | 1.05 | 0.78 | 0.95 | 0.83 |
| Fbxl12 | 0.89 | 1.14 | 1.15 | 1.03 | 1.67 | 1.04 | 0.90 | 0.16 | 0.85 | 1.34 | 1.20 | 1.08 |
| Fbxl14 | 1.07 | 1.01 | 0.93 | 0.92 | 0.42 | 1.00 | 1.03 | 0.65 | 1.13 | 0.98 | 0.75 | 1.01 |
| Fbxl15 | 0.95 | 2.13 | 0.91 | 0.95 | 0.56 | 0.80 | 0.81 | 1.13 | 0.93 | 1.04 | 1.23 | 1.21 |
| Fbxl4 | 0.98 | 1.14 | 1.01 | 0.79 | 0.61 | 0.97 | 0.80 | 1.00 | 1.12 | 1.02 | 0.94 | 1.03 |
| Fbxo21 | 0.99 | 0.96 | 1.09 | 0.50 | 0.17 | 0.77 | 1.06 | 0.42 | 0.90 | 1.10 | 1.25 | 1.14 |
| Fbxo44 | 0.84 | 0.87 | 0.63 | 0.82 | 2.27 | 1.31 | 0.74 | 1.30 | 0.82 | 0.88 | 3.40 | 0.67 |
| Fbxo5 | 0.74 | 0.53 | 0.76 | 0.55 | 1.00 | 0.93 | 0.70 | 0.93 | 1.08 | 0.68 | 0.65 | 0.61 |
| Fcer2a | 1.00 | 1.00 | 1.00 | 1.00 | 1.00 | 1.00 | 1.00 | 1.00 | 1.00 | 0.39 | 0.25 | 0.46 |
| Fcho2 | 1.10 | 1.00 | 0.91 | 1.28 | 0.46 | 1.03 | 1.09 | 0.80 | 0.99 | 1.00 | 0.73 | 0.93 |
| Fchsd2 | 1.28 | 1.31 | 1.19 | 0.72 | 0.98 | 0.88 | 0.98 | 0.60 | 0.83 | 0.90 | 0.49 | 0.86 |
| Fermt1 | 0.91 | 0.81 | 0.79 | 1.39 | 1.00 | 2.79 | 1.00 | 1.00 | 1.00 | 1.00 | 1.00 | 1.00 |
| Fetub | 1.05 | 1.20 | 1.04 | 1.00 | 1.00 | 1.00 | 1.03 | 2.44 | 1.18 | 1.00 | 1.00 | 1.00 |
| Ffar1 | 1.00 | 1.00 | 1.00 | 1.00 | 1.00 | 1.00 | 1.00 | 1.00 | 1.00 | 0.69 | 0.17 | 1.17 |
| Ffar4 | 0.35 | 0.25 | 0.26 | 0.17 | 0.50 | 0.51 | 1.00 | 1.00 | 1.00 | 0.97 | 0.50 | 0.62 |
| Fgf22 | 1.59 | 1.11 | 0.61 | 1.00 | 1.00 | 1.00 | 1.00 | 1.00 | 1.00 | 1.00 | 1.00 | 1.00 |
| Fgfbp1 | 0.62 | 0.67 | 0.63 | 3.38 | 1.00 | 3.17 | 1.00 | 1.00 | 1.00 | 1.54 | 2.05 | 1.26 |
| Fgfrl1 | 0.81 | 0.84 | 1.11 | 0.33 | 0.19 | 0.47 | 0.85 | 0.86 | 0.78 | 1.07 | 1.18 | 1.05 |
| Fhdc1 | 0.89 | 0.93 | 0.80 | 1.00 | 1.00 | 1.00 | 0.93 | 0.38 | 1.15 | 0.51 | 0.41 | 0.34 |
| Fignl1 | 0.36 | 0.42 | 0.42 | 1.00 | 1.00 | 1.00 | 1.16 | 0.67 | 1.08 | 0.47 | 0.33 | 0.45 |
| Filip1l | 1.10 | 1.02 | 1.09 | 1.05 | 0.16 | 1.02 | 0.95 | 1.00 | 0.89 | 1.31 | 0.74 | 1.24 |
| Fkrp | 1.19 | 1.28 | 1.07 | 1.24 | 0.34 | 1.07 | 0.87 | 1.00 | 0.91 | 0.97 | 0.92 | 0.99 |
| Flg2 | 1.77 | 1.86 | 1.24 | 1.00 | 1.00 | 1.00 | 1.00 | 1.00 | 1.00 | 1.00 | 1.00 | 1.00 |
| Flt1 | 1.34 | 1.56 | 1.14 | 1.19 | 0.28 | 1.15 | 1.00 | 1.36 | 1.00 | 0.78 | 0.63 | 0.80 |
| Flywch1 | 1.09 | 1.26 | 0.96 | 1.12 | 0.24 | 1.03 | 1.05 | 2.18 | 1.14 | 0.87 | 1.41 | 1.11 |
| Fmr1 | 0.93 | 0.90 | 0.93 | 0.78 | 0.31 | 0.67 | 0.97 | 0.60 | 0.98 | 1.08 | 0.85 | 1.08 |
| Fn3krp | 1.06 | 0.95 | 1.07 | 1.10 | 0.37 | 0.98 | 1.00 | 1.76 | 1.07 | 0.66 | 0.61 | 0.64 |
| Fndc3b | 1.22 | 0.95 | 0.94 | 1.60 | 0.31 | 0.74 | 1.01 | 0.71 | 0.97 | 1.10 | 0.81 | 1.06 |
| Fosb | 1.73 | 1.69 | 0.79 | 3.55 | 1.00 | 1.72 | 0.90 | 1.00 | 0.89 | 0.88 | 1.23 | 1.43 |
| Foxf2 | 0.91 | 1.00 | 1.10 | 1.00 | 1.00 | 0.68 | 1.00 | 1.00 | 1.00 | 1.00 | 1.00 | 1.00 |
| Foxj3 | 1.03 | 1.08 | 0.93 | 1.16 | 0.36 | 1.09 | 1.01 | 0.70 | 0.94 | 1.05 | 0.78 | 1.08 |
| Foxk1 | 0.99 | 1.10 | 0.90 | 1.33 | 0.30 | 1.24 | 1.10 | 1.19 | 1.10 | 0.87 | 0.49 | 1.09 |
| Foxn2 | 1.09 | 0.94 | 0.85 | 1.21 | 0.73 | 0.89 | 1.25 | 1.00 | 0.89 | 1.13 | 0.66 | 1.14 |
| Foxq1 | 1.01 | 1.10 | 1.00 | 1.00 | 1.00 | 1.00 | 0.93 | 0.99 | 0.89 | 1.00 | 1.00 | 1.00 |
| Fpgt | 1.05 | 0.91 | 0.76 | 0.89 | 1.00 | 0.94 | 0.99 | 0.53 | 0.94 | 1.04 | 0.70 | 1.07 |
| Frmd4a | 1.04 | 1.05 | 1.27 | 1.42 | 0.67 | 1.08 | 1.45 | 1.15 | 0.99 | 0.85 | 0.75 | 0.89 |
| Frmd6 | 1.06 | 1.06 | 1.26 | 0.90 | 0.44 | 0.83 | 0.96 | 1.10 | 1.15 | 1.03 | 0.70 | 1.06 |
| Frs2 | 0.99 | 1.02 | 0.87 | 1.09 | 0.42 | 0.76 | 1.26 | 1.00 | 1.03 | 1.00 | 0.55 | 1.00 |
| Frs3 | 1.15 | 1.07 | 1.56 | 0.56 | 1.00 | 0.94 | 0.93 | 0.11 | 1.13 | 1.00 | 1.44 | 0.96 |
| Fstl1 | 0.78 | 0.72 | 0.86 | 0.76 | 0.31 | 0.70 | 0.94 | 0.81 | 0.83 | 0.85 | 0.69 | 0.85 |
| Fzd1 | 1.06 | 1.14 | 1.07 | 0.95 | 0.25 | 0.80 | 0.81 | 1.00 | 0.99 | 0.84 | 0.70 | 1.05 |
| Fzd4 | 1.10 | 1.11 | 0.69 | 0.59 | 0.05 | 0.19 | 1.25 | 1.00 | 0.80 | 0.96 | 0.62 | 1.34 |
| Fzd7 | 1.02 | 0.95 | 1.06 | 0.77 | 0.46 | 0.95 | 0.95 | 1.00 | 1.16 | 0.69 | 0.56 | 0.95 |
| G0s2 | 0.71 | 0.59 | 1.25 | 0.39 | 0.07 | 0.55 | 0.30 | 0.22 | 0.71 | 0.93 | 1.24 | 1.14 |
| G6pd2 | 0.77 | 0.73 | 0.61 | 1.04 | 0.08 | 0.71 | 1.37 | 1.00 | 1.02 | 1.10 | 0.70 | 1.01 |
| Gabpa | 0.98 | 0.87 | 0.85 | 0.90 | 0.55 | 0.82 | 0.99 | 0.46 | 1.07 | 1.02 | 0.67 | 1.02 |

Fig. 35- 36

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Fam129a | 1.12 | 1.97 | 1.33 | 1.00 | 1.00 | 1.00 | 0.94 | 0.31 | 1.34 | 0.50 | 0.53 | 0.47 |
| Fam131a | 1.00 | 1.00 | 1.00 | 1.16 | 0.85 | 1.06 | 1.27 | 0.87 | 1.01 | 1.00 | 1.16 | 1.50 |
| Fam135a | 1.33 | 1.54 | 1.21 | 0.82 | 1.00 | 0.88 | 0.66 | 0.14 | 0.79 | 1.00 | 1.00 | 1.00 |
| Fam167a | 1.00 | 1.00 | 1.00 | 0.96 | 1.00 | 1.05 | 0.78 | 0.17 | 0.97 | 1.00 | 1.00 | 0.93 |
| Fam173b | 0.95 | 0.98 | 0.85 | 0.92 | 0.20 | 0.87 | 1.00 | 1.03 | 0.72 | 0.78 | 0.76 | 0.88 |
| Fam204a | 0.87 | 0.70 | 0.94 | 0.99 | 1.98 | 0.97 | 0.92 | 0.16 | 0.85 | 0.57 | 1.25 | 0.87 |
| Fam20b | 0.89 | 0.84 | 0.81 | 1.03 | 0.64 | 0.99 | 0.76 | 0.19 | 0.77 | 0.64 | 0.83 | 0.92 |
| Fam219a | 1.00 | 1.00 | 1.19 | 1.11 | 1.40 | 1.06 | 1.37 | 0.14 | 1.48 | 2.23 | 1.87 | 1.67 |
| Fam26e | 1.00 | 1.00 | 1.00 | 1.21 | 1.00 | 0.96 | 0.88 | 0.16 | 0.74 | 1.00 | 1.00 | 1.00 |
| Fam43a | 1.00 | 1.00 | 0.94 | 1.02 | 1.28 | 1.03 | 1.03 | 0.13 | 1.06 | 0.33 | 0.93 | 0.86 |
| Fam57a | 1.00 | 1.00 | 1.00 | 1.07 | 1.00 | 0.92 | 0.53 | 0.04 | 0.52 | 1.00 | 1.00 | 1.00 |
| Fam60a | 0.86 | 1.14 | 1.00 | 1.00 | 1.00 | 1.00 | 0.90 | 0.11 | 0.95 | 0.45 | 0.74 | 1.16 |
| Fam65c | 1.00 | 1.00 | 1.00 | 1.00 | 1.00 | 1.00 | 0.94 | 0.14 | 0.80 | 1.00 | 1.00 | 1.00 |
| Fam78a | 1.00 | 1.00 | 1.00 | 1.13 | 1.00 | 0.99 | 1.29 | 1.00 | 1.00 | 0.61 | 0.76 | 0.82 |
| Fam83c | 1.00 | 1.00 | 1.00 | 1.00 | 1.00 | 1.00 | 0.69 | 0.10 | 0.72 | 1.00 | 1.00 | 1.00 |
| Fam84b | 1.49 | 1.37 | 1.38 | 0.75 | 1.00 | 0.86 | 0.77 | 0.18 | 1.06 | 1.00 | 1.16 | 1.08 |
| Far2 | 1.69 | 1.57 | 1.01 | 1.08 | 0.14 | 0.85 | 1.03 | 0.17 | 1.27 | 1.12 | 1.36 | 1.37 |
| Fastkd5 | 1.01 | 1.04 | 1.00 | 1.11 | 1.59 | 0.96 | 0.75 | 0.19 | 0.85 | 0.40 | 0.75 | 1.02 |
| Fat1 | 1.00 | 1.00 | 1.00 | 0.74 | 1.00 | 0.83 | 0.90 | 0.09 | 0.98 | 1.00 | 1.00 | 1.00 |
| Fbxl12 | 0.85 | 0.70 | 1.05 | 0.82 | 0.42 | 1.08 | 0.97 | 0.37 | 0.94 | 0.54 | 1.15 | 1.05 |
| Fbxl14 | 1.09 | 0.67 | 0.89 | 0.97 | 0.78 | 1.07 | 0.91 | 0.17 | 1.05 | 0.60 | 1.20 | 1.04 |
| Fbxl15 | 1.00 | 1.00 | 1.27 | 1.03 | 1.18 | 0.98 | 0.93 | 1.64 | 0.55 | 1.09 | 1.08 | 0.73 |
| Fbxl4 | 0.82 | 0.84 | 1.00 | 1.00 | 1.00 | 0.99 | 0.98 | 0.15 | 1.11 | 0.58 | 0.87 | 0.87 |
| Fbxo21 | 1.08 | 0.73 | 1.13 | 1.09 | 0.36 | 1.02 | 1.00 | 0.27 | 1.17 | 0.58 | 0.99 | 0.87 |
| Fbxo44 | 1.00 | 1.00 | 1.00 | 0.94 | 1.13 | 0.96 | 0.60 | 1.46 | 0.62 | 1.00 | 1.00 | 1.00 |
| Fbxo5 | 1.00 | 1.00 | 1.00 | 1.00 | 1.00 | 0.95 | 0.64 | 0.17 | 1.07 | 0.58 | 0.85 | 0.95 |
| Fcer2a | 1.00 | 1.00 | 0.91 | 1.00 | 1.00 | 1.00 | 1.00 | 1.00 | 1.00 | 0.34 | 0.36 | 0.42 |
| Fcho2 | 0.97 | 0.99 | 1.26 | 0.87 | 1.00 | 0.87 | 0.86 | 0.13 | 1.29 | 0.58 | 1.03 | 0.89 |
| Fchsd2 | 0.81 | 0.78 | 0.90 | 0.94 | 1.00 | 0.97 | 0.74 | 0.11 | 0.77 | 0.53 | 0.71 | 0.80 |
| Fermt1 | 1.00 | 1.00 | 1.00 | 1.00 | 1.00 | 1.00 | 0.68 | 0.17 | 0.92 | 1.00 | 1.00 | 1.00 |
| Fetub | 0.05 | 0.05 | 0.07 | 1.00 | 1.48 | 1.00 | 0.53 | 2.85 | 0.88 | 1.00 | 1.00 | 1.00 |
| Ffar1 | 1.00 | 1.00 | 1.00 | 1.00 | 1.00 | 1.00 | 1.00 | 1.00 | 1.00 | 1.00 | 0.77 | 0.70 |
| Ffar4 | 1.00 | 1.00 | 1.00 | 1.00 | 1.00 | 1.00 | 4.05 | 1.05 | 2.30 | 1.00 | 1.00 | 1.00 |
| Fgf22 | 1.00 | 1.00 | 1.00 | 0.77 | 1.00 | 1.47 | 0.76 | 0.09 | 0.40 | 1.00 | 1.00 | 1.00 |
| Fgfbp1 | 1.00 | 1.09 | 1.00 | 2.17 | 1.00 | 1.06 | 0.69 | 0.16 | 0.52 | 1.00 | 1.00 | 1.00 |
| Fgfrl1 | 1.04 | 0.79 | 0.75 | 0.68 | 0.97 | 0.99 | 1.11 | 0.40 | 1.19 | 0.54 | 0.71 | 1.16 |
| Fhdc1 | 1.00 | 1.00 | 1.00 | 1.10 | 1.00 | 1.04 | 1.02 | 0.11 | 1.00 | 0.28 | 0.83 | 0.73 |
| Fignl1 | 1.00 | 1.00 | 1.00 | 1.00 | 1.00 | 1.00 | 0.45 | 0.52 | 0.49 | 0.35 | 0.58 | 0.76 |
| Filip1l | 0.93 | 1.94 | 1.48 | 0.89 | 1.00 | 0.79 | 1.03 | 0.06 | 1.32 | 0.24 | 0.87 | 0.91 |
| Fkrp | 1.35 | 1.32 | 0.95 | 1.12 | 1.16 | 1.08 | 0.90 | 0.16 | 1.07 | 0.31 | 0.92 | 1.08 |
| Flg2 | 1.00 | 1.00 | 1.00 | 1.00 | 1.00 | 1.00 | 0.59 | 0.14 | 0.59 | 1.00 | 1.00 | 1.00 |
| Flt1 | 1.43 | 1.84 | 1.49 | 0.80 | 1.00 | 0.96 | 1.60 | 1.00 | 1.53 | 1.00 | 1.00 | 1.00 |
| Flywch1 | 0.74 | 0.85 | 1.40 | 1.01 | 1.18 | 1.01 | 1.22 | 0.08 | 1.19 | 0.80 | 0.62 | 0.75 |
| Fmr1 | 1.58 | 1.28 | 1.07 | 0.98 | 1.93 | 0.92 | 0.89 | 0.14 | 1.12 | 0.53 | 1.02 | 1.04 |
| Fn3krp | 0.67 | 0.84 | 0.81 | 0.87 | 1.00 | 0.96 | 0.89 | 0.25 | 0.96 | 0.15 | 0.76 | 0.86 |
| Fndc3b | 1.10 | 1.36 | 1.06 | 0.95 | 1.00 | 1.09 | 0.97 | 0.16 | 1.28 | 0.67 | 1.16 | 1.13 |
| Fosb | 1.00 | 1.00 | 1.00 | 1.59 | 1.47 | 1.04 | 0.31 | 0.11 | 0.35 | 1.00 | 1.00 | 1.00 |
| Foxf2 | 1.00 | 1.00 | 1.00 | 0.96 | 1.00 | 0.87 | 1.00 | 1.00 | 1.00 | 1.00 | 1.00 | 1.00 |
| Foxj3 | 1.30 | 1.02 | 1.36 | 0.99 | 0.56 | 1.01 | 0.97 | 0.16 | 1.04 | 0.50 | 0.86 | 0.82 |
| Foxk1 | 0.93 | 0.77 | 0.94 | 0.92 | 1.00 | 0.88 | 0.78 | 0.12 | 1.02 | 0.58 | 0.81 | 0.85 |
| Foxn2 | 1.31 | 1.30 | 1.14 | 0.92 | 1.00 | 0.99 | 0.85 | 0.20 | 0.95 | 0.51 | 0.95 | 0.90 |
| Foxq1 | 1.00 | 1.00 | 1.00 | 0.88 | 1.00 | 0.79 | 0.87 | 0.08 | 0.84 | 1.00 | 1.00 | 1.00 |
| Fpgt | 0.88 | 1.27 | 1.00 | 0.98 | 1.00 | 0.99 | 0.73 | 0.18 | 0.98 | 1.00 | 0.79 | 1.13 |
| Frmd4a | 1.00 | 1.00 | 1.00 | 1.00 | 1.00 | 1.03 | 0.85 | 0.19 | 1.14 | 0.51 | 0.89 | 0.85 |
| Frmd6 | 1.36 | 1.87 | 1.06 | 1.01 | 0.79 | 0.88 | 0.65 | 0.08 | 0.82 | 1.00 | 0.87 | 0.88 |
| Frs2 | 0.98 | 1.14 | 0.96 | 0.86 | 1.00 | 0.96 | 0.76 | 0.12 | 1.03 | 0.74 | 0.66 | 0.86 |
| Frs3 | 1.00 | 1.00 | 1.00 | 1.16 | 1.00 | 1.07 | 1.17 | 0.32 | 1.20 | 1.00 | 1.00 | 1.00 |
| Fstl1 | 0.57 | 1.62 | 1.14 | 0.97 | 3.53 | 1.03 | 0.89 | 0.20 | 1.01 | 1.00 | 0.57 | 1.06 |
| Fzd1 | 1.00 | 1.00 | 1.00 | 1.07 | 1.00 | 1.12 | 0.99 | 0.08 | 1.33 | 1.00 | 1.00 | 1.00 |
| Fzd4 | 1.20 | 0.98 | 1.08 | 0.82 | 1.00 | 0.96 | 1.01 | 0.50 | 1.80 | 1.00 | 1.00 | 1.00 |
| Fzd7 | 1.00 | 1.00 | 1.00 | 0.82 | 1.00 | 0.79 | 0.61 | 0.07 | 0.76 | 1.00 | 0.61 | 0.65 |
| G0s2 | 0.58 | 0.56 | 0.14 | 0.95 | 2.80 | 1.05 | 0.54 | 0.51 | 0.57 | 1.43 | 1.65 | 1.36 |
| G6pd2 | 0.81 | 1.18 | 0.99 | 1.10 | 1.00 | 0.95 | 0.85 | 0.03 | 0.90 | 0.04 | 0.85 | 0.99 |
| Gabpa | 0.88 | 0.90 | 0.94 | 0.87 | 1.00 | 0.93 | 0.82 | 0.13 | 1.02 | 0.48 | 0.87 | 0.94 |

Fig. 35- 37

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Gabpb1 | 1.21 | 2.70 | 1.07 | 2.00 | 0.55 | 0.93 | 0.83 | 0.77 | 0.99 | 0.21 | 0.26 | 0.89 |
| Gadd45a | 1.49 | 2.35 | 2.19 | 2.23 | 3.67 | 1.95 | 1.31 | 1.36 | 0.52 | 0.70 | 0.81 | 0.81 |
| Gak | 1.28 | 1.49 | 1.12 | 0.83 | 0.34 | 0.99 | 1.17 | 1.13 | 1.13 | 0.70 | 0.42 | 1.12 |
| Gale | 1.00 | 1.00 | 1.00 | 0.15 | 1.55 | 0.40 | 1.00 | 1.00 | 1.00 | 1.33 | 3.43 | 1.09 |
| Galm | 1.00 | 1.44 | 1.41 | 0.62 | 0.49 | 0.50 | 0.61 | 0.62 | 0.43 | 0.38 | 0.74 | 0.99 |
| Galnt11 | 1.51 | 2.58 | 0.95 | 1.12 | 0.20 | 0.97 | 0.93 | 1.02 | 0.82 | 0.27 | 0.34 | 1.00 |
| Galnt15 | 1.10 | 1.00 | 2.58 | 4.91 | 0.26 | 2.13 | 1.62 | 4.46 | 3.21 | 1.00 | 0.56 | 1.81 |
| Galnt7 | 1.34 | 1.49 | 1.64 | 2.90 | 0.62 | 1.28 | 1.04 | 1.18 | 1.11 | 0.92 | 0.53 | 0.90 |
| Gamt | 1.18 | 0.64 | 0.77 | 0.68 | 1.85 | 1.06 | 1.29 | 0.59 | 0.59 | 0.72 | 0.83 | 0.65 |
| Gapvd1 | 0.76 | 1.00 | 1.00 | 1.25 | 0.21 | 0.94 | 1.09 | 1.43 | 1.13 | 0.99 | 0.44 | 1.02 |
| Gas5 | 1.10 | 2.08 | 1.86 | 2.23 | 0.20 | 0.95 | 1.03 | 1.06 | 1.16 | 0.76 | 0.23 | 1.00 |
| Gas7 | 1.04 | 1.00 | 1.57 | 2.50 | 0.16 | 1.24 | 1.09 | 0.97 | 1.18 | 0.48 | 0.44 | 1.16 |
| Gck | 3.22 | 1.82 | 1.56 | 1.00 | 1.35 | 1.23 | 0.79 | 0.84 | 0.96 | 3.27 | 1.76 | 1.44 |
| Gdf11 | 0.97 | 1.00 | 0.83 | 1.00 | 1.00 | 1.00 | 1.00 | 1.02 | 1.29 | 1.00 | 1.00 | 1.00 |
| Gfap | 1.00 | 1.00 | 1.00 | 1.00 | 0.19 | 1.00 | 1.00 | 1.00 | 1.00 | 1.00 | 1.00 | 1.00 |
| Gfod1 | 0.75 | 1.00 | 1.14 | 1.89 | 0.26 | 0.90 | 1.42 | 2.10 | 1.82 | 1.00 | 0.62 | 1.15 |
| Gh | 1.00 | 1.00 | 1.00 | 1.00 | 1.00 | 1.00 | 1.00 | 1.00 | 1.00 | 1.82 | 1.00 | 4.51 |
| Gimap4 | 0.78 | 1.50 | 0.81 | 1.02 | 0.94 | 0.77 | 0.96 | 0.84 | 1.02 | 0.83 | 0.80 | 1.00 |
| Gk5 | 1.00 | 1.00 | 1.00 | 2.53 | 1.00 | 1.53 | 1.00 | 1.00 | 1.00 | 1.00 | 1.00 | 1.00 |
| Gkn1 | 0.03 | 1.05 | 1.00 | 1.00 | 1.00 | 0.64 | 0.39 | 1.00 | 1.00 | 0.04 | 1.00 | 1.00 |
| Gkn2 | 0.04 | 1.00 | 1.00 | 1.71 | 1.00 | 0.51 | 0.74 | 1.00 | 1.00 | 0.07 | 1.00 | 1.00 |
| Gldc | 1.00 | 1.00 | 1.00 | 1.00 | 1.00 | 1.00 | 1.00 | 1.00 | 1.00 | 1.00 | 1.00 | 1.00 |
| Glt6d1 | 1.00 | 1.00 | 1.00 | 1.00 | 1.00 | 1.00 | 1.00 | 1.00 | 1.00 | 1.00 | 1.00 | 1.00 |
| Gltp | 1.11 | 3.08 | 0.85 | 1.37 | 0.10 | 1.05 | 1.16 | 1.02 | 0.94 | 0.16 | 0.11 | 0.98 |
| Gltscr1 | 0.70 | 1.00 | 0.88 | 0.95 | 0.21 | 0.73 | 1.20 | 1.17 | 1.11 | 1.00 | 0.39 | 0.98 |
| Gltscr1l | 0.82 | 1.00 | 1.01 | 2.31 | 0.25 | 0.80 | 1.37 | 1.49 | 1.21 | 0.65 | 0.44 | 1.04 |
| Gm10046 | 1.00 | 1.00 | 1.00 | 1.00 | 1.00 | 1.00 | 1.00 | 1.00 | 1.00 | 1.09 | 1.75 | 1.00 |
| Gm10058 | 1.00 | 1.00 | 1.00 | 1.00 | 1.00 | 1.00 | 1.00 | 1.00 | 1.00 | 1.00 | 1.00 | 1.00 |
| Gm10100 | 1.00 | 1.00 | 1.00 | 1.00 | 1.00 | 1.00 | 1.00 | 1.00 | 1.00 | 1.00 | 1.00 | 1.00 |
| Gm10142 | 1.00 | 1.00 | 1.00 | 1.00 | 1.00 | 1.00 | 1.00 | 1.00 | 1.00 | 1.00 | 1.00 | 1.00 |
| Gm10190 | 1.00 | 1.00 | 1.00 | 1.00 | 1.00 | 1.00 | 1.00 | 1.00 | 1.00 | 1.00 | 1.00 | 1.00 |
| Gm10272 | 1.00 | 1.00 | 1.00 | 1.00 | 1.00 | 1.00 | 1.00 | 1.00 | 1.00 | 1.00 | 1.00 | 1.00 |
| Gm10336 | 2.73 | 4.31 | 2.18 | 2.88 | 0.25 | 0.93 | 0.54 | 0.68 | 0.62 | 0.33 | 0.24 | 0.85 |
| Gm10413 | 1.00 | 1.00 | 1.00 | 1.00 | 1.00 | 1.00 | 1.00 | 1.00 | 1.00 | 1.00 | 1.00 | 1.00 |
| Gm10486 | 1.00 | 1.00 | 1.00 | 1.00 | 1.00 | 1.00 | 1.00 | 1.00 | 1.00 | 1.00 | 1.00 | 1.00 |
| Gm10768 | 1.00 | 1.00 | 1.00 | 1.00 | 1.00 | 1.00 | 1.00 | 1.00 | 1.00 | 1.00 | 1.00 | 1.00 |
| Gm11127 | 0.38 | 1.00 | 0.36 | 0.15 | 0.14 | 0.17 | 0.32 | 0.33 | 0.31 | 0.10 | 0.04 | 0.20 |
| Gm11559 | 1.00 | 1.00 | 1.00 | 1.00 | 1.00 | 1.00 | 1.00 | 1.00 | 1.00 | 1.00 | 1.00 | 1.00 |
| Gm11710 | 0.84 | 1.00 | 2.47 | 1.00 | 1.00 | 0.96 | 1.60 | 1.64 | 1.98 | 1.00 | 1.00 | 1.09 |
| Gm11937 | 1.00 | 1.00 | 1.00 | 1.00 | 1.00 | 1.00 | 1.00 | 1.00 | 1.00 | 1.00 | 1.00 | 1.00 |
| Gm11992 | 1.00 | 1.00 | 1.00 | 1.38 | 1.00 | 1.00 | 1.00 | 1.00 | 1.00 | 1.00 | 1.00 | 0.91 |
| Gm12070 | 1.18 | 1.82 | 0.85 | 0.59 | 0.60 | 1.08 | 1.00 | 0.95 | 0.87 | 0.26 | 0.40 | 1.06 |
| Gm12657 | 0.83 | 3.78 | 0.83 | 1.13 | 0.13 | 1.07 | 0.60 | 0.77 | 0.74 | 0.38 | 0.09 | 1.05 |
| Gm12888 | 1.00 | 1.00 | 1.00 | 1.00 | 1.00 | 1.00 | 1.00 | 1.00 | 1.00 | 1.00 | 1.00 | 1.00 |
| Gm13034 | 0.84 | 1.00 | 1.21 | 2.93 | 0.47 | 1.07 | 1.25 | 1.22 | 1.11 | 1.00 | 1.00 | 1.31 |
| Gm13124 | 1.00 | 1.00 | 1.00 | 1.00 | 1.00 | 1.00 | 1.00 | 1.00 | 1.00 | 1.00 | 1.00 | 1.00 |
| Gm13177 | 1.00 | 1.00 | 1.00 | 1.00 | 1.00 | 1.00 | 1.00 | 1.00 | 1.00 | 1.00 | 1.00 | 1.00 |
| Gm13304 | 0.41 | 1.59 | 0.95 | 0.60 | 0.53 | 0.37 | 0.68 | 0.13 | 0.44 | 0.09 | 0.02 | 0.34 |
| Gm13375 | 2.27 | 3.04 | 1.85 | 2.05 | 1.21 | 1.09 | 1.68 | 1.52 | 1.46 | 0.40 | 0.33 | 1.24 |
| Gm13498 | 1.38 | 4.41 | 1.40 | 1.26 | 0.21 | 1.80 | 1.48 | 1.43 | 1.44 | 0.18 | 0.22 | 1.54 |
| Gm13710 | 1.00 | 1.00 | 1.00 | 1.00 | 1.00 | 1.00 | 1.00 | 0.70 | 1.09 | 1.00 | 1.00 | 1.00 |
| Gm14308 | 0.45 | 0.31 | 0.32 | 0.67 | 0.71 | 0.48 | 0.23 | 0.19 | 0.19 | 0.82 | 0.49 | 0.44 |
| Gm14322 | 0.76 | 0.32 | 0.73 | 0.73 | 1.31 | 0.82 | 0.42 | 0.46 | 0.39 | 0.76 | 0.75 | 0.68 |
| Gm14346 | 1.00 | 1.00 | 1.00 | 1.00 | 1.00 | 1.00 | 1.00 | 1.00 | 1.00 | 1.00 | 1.00 | 1.00 |
| Gm14403 | 0.14 | 0.13 | 0.15 | 0.47 | 1.01 | 0.37 | 0.23 | 0.29 | 0.21 | 0.90 | 0.63 | 0.35 |
| Gm14420 | 0.43 | 0.35 | 0.44 | 1.00 | 1.30 | 0.75 | 0.17 | 0.24 | 0.24 | 1.14 | 0.83 | 0.55 |
| Gm14431 | 0.29 | 1.00 | 0.50 | 1.51 | 0.61 | 0.69 | 0.21 | 0.29 | 0.30 | 1.00 | 1.00 | 0.42 |
| Gm14436 | 0.67 | 1.00 | 0.84 | 1.49 | 0.97 | 0.64 | 0.25 | 0.34 | 0.33 | 1.00 | 0.74 | 0.65 |
| Gm14475 | 1.00 | 1.00 | 1.00 | 1.00 | 1.00 | 1.00 | 1.00 | 1.00 | 1.00 | 1.00 | 1.00 | 1.00 |
| Gm14476 | 1.00 | 1.00 | 1.00 | 1.00 | 1.00 | 1.00 | 1.00 | 1.48 | 1.00 | 1.00 | 1.00 | 1.00 |
| Gm14478 | 1.00 | 1.00 | 1.00 | 1.00 | 1.00 | 1.00 | 1.00 | 1.00 | 1.00 | 1.00 | 1.00 | 1.00 |
| Gm15104 | 1.00 | 1.00 | 1.00 | 1.00 | 1.00 | 1.00 | 1.00 | 1.00 | 1.00 | 1.00 | 1.00 | 1.00 |
| Gm15455 | 0.84 | 1.35 | 0.85 | 0.91 | 0.30 | 1.17 | 0.98 | 1.00 | 1.02 | 0.42 | 0.32 | 1.02 |
| Gm15987 | 1.00 | 1.00 | 1.00 | 1.00 | 1.00 | 1.00 | 1.00 | 1.00 | 1.00 | 1.00 | 1.00 | 1.06 |

Fig. 35- 38

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Gabpb1 | 0.81 | 0.83 | 0.79 | 0.84 | 1.68 | 0.84 | 0.95 | 2.18 | 1.01 | 1.04 | 0.89 | 1.11 |
| Gadd45a | 1.51 | 1.31 | 1.30 | 0.85 | 1.14 | 0.61 | 0.33 | 0.38 | 0.47 | 1.88 | 2.83 | 1.47 |
| Gak | 0.97 | 0.99 | 1.03 | 1.13 | 1.78 | 1.10 | 0.96 | 0.82 | 0.98 | 1.07 | 0.93 | 1.04 |
| Gale | 0.70 | 0.92 | 0.74 | 0.80 | 0.76 | 0.53 | 2.18 | 0.35 | 1.69 | 0.99 | 1.57 | 1.02 |
| Galm | 0.95 | 0.92 | 1.05 | 0.71 | 0.56 | 0.70 | 0.42 | 0.17 | 0.50 | 0.44 | 0.47 | 0.41 |
| Galnt11 | 0.93 | 0.93 | 0.90 | 0.95 | 2.51 | 0.94 | 1.48 | 1.00 | 1.35 | 0.98 | 0.90 | 0.96 |
| Galnt15 | 1.54 | 0.48 | 1.66 | 1.62 | 1.00 | 1.34 | 1.00 | 1.00 | 1.00 | 1.60 | 0.50 | 1.15 |
| Galnt7 | 0.52 | 0.49 | 0.76 | 1.80 | 1.00 | 1.26 | 1.23 | 1.00 | 1.16 | 1.20 | 0.87 | 1.14 |
| Gamt | 0.63 | 0.77 | 0.98 | 0.35 | 0.40 | 0.84 | 0.19 | 0.40 | 0.41 | 0.44 | 1.28 | 1.66 |
| Gapvd1 | 0.56 | 0.49 | 0.80 | 1.13 | 1.00 | 0.93 | 0.94 | 1.00 | 0.99 | 1.00 | 0.55 | 0.92 |
| Gas5 | 0.64 | 0.48 | 0.90 | 0.93 | 1.00 | 1.05 | 0.91 | 1.00 | 1.31 | 0.77 | 0.59 | 1.12 |
| Gas7 | 1.19 | 0.73 | 1.14 | 1.54 | 1.00 | 1.38 | 1.00 | 1.00 | 1.00 | 1.00 | 0.73 | 1.03 |
| Gck | 1.17 | 1.00 | 1.00 | 1.00 | 1.00 | 1.00 | 0.12 | 0.26 | 0.27 | 1.00 | 1.00 | 1.14 |
| Gdf11 | 0.59 | 0.37 | 1.33 | 0.71 | 1.00 | 1.66 | 1.00 | 1.00 | 1.00 | 1.03 | 1.00 | 0.99 |
| Gfap | 0.99 | 1.00 | 1.00 | 1.00 | 1.00 | 1.00 | 1.00 | 1.00 | 1.00 | 1.39 | 1.04 | 1.15 |
| Gfod1 | 0.87 | 0.58 | 1.02 | 1.00 | 1.00 | 1.00 | 1.00 | 1.00 | 1.00 | 0.95 | 0.58 | 0.76 |
| Gh | 1.00 | 1.00 | 4.75 | 1.00 | 1.00 | 1.00 | 1.00 | 4.47 | 1.00 | 1.00 | 1.00 | 1.00 |
| Gimap4 | 1.00 | 1.10 | 1.41 | 0.76 | 0.84 | 0.81 | 0.45 | 0.59 | 0.90 | 0.92 | 0.96 | 0.96 |
| Gk5 | 0.77 | 0.61 | 1.29 | 0.76 | 1.00 | 0.80 | 1.00 | 1.00 | 1.00 | 0.78 | 0.54 | 0.81 |
| Gkn1 | 1.00 | 0.03 | 1.00 | 1.20 | 1.00 | 1.05 | 1.26 | 0.83 | 0.95 | 0.23 | 0.44 | 0.95 |
| Gkn2 | 1.00 | 0.02 | 1.00 | 0.73 | 0.50 | 1.19 | 1.70 | 1.36 | 1.43 | 0.15 | 0.39 | 0.54 |
| Gldc | 1.00 | 1.00 | 1.00 | 2.30 | 2.56 | 1.53 | 1.36 | 1.03 | 1.82 | 1.00 | 1.00 | 1.00 |
| Glt6d1 | 1.00 | 1.00 | 1.00 | 1.00 | 1.00 | 1.00 | 1.00 | 1.00 | 1.00 | 1.00 | 1.00 | 1.00 |
| Gltp | 0.77 | 0.79 | 0.91 | 0.89 | 2.20 | 0.94 | 0.94 | 1.00 | 1.12 | 0.97 | 0.81 | 1.01 |
| Gltscr1 | 0.61 | 0.55 | 1.05 | 0.73 | 1.00 | 1.04 | 0.75 | 1.00 | 1.10 | 0.84 | 0.50 | 0.90 |
| Gltscr1l | 0.63 | 0.56 | 0.96 | 1.07 | 1.00 | 1.21 | 0.77 | 1.00 | 0.95 | 0.99 | 0.56 | 0.92 |
| Gm10046 | 1.00 | 1.00 | 1.00 | 1.00 | 1.00 | 1.00 | 1.00 | 1.00 | 1.00 | 1.00 | 1.00 | 1.00 |
| Gm10058 | 1.00 | 1.00 | 1.00 | 1.00 | 1.00 | 1.00 | 1.00 | 1.00 | 1.00 | 1.00 | 1.00 | 1.00 |
| Gm10100 | 1.00 | 1.00 | 1.00 | 1.00 | 1.00 | 1.00 | 1.00 | 1.00 | 1.00 | 1.00 | 1.00 | 1.00 |
| Gm10142 | 1.00 | 1.00 | 1.00 | 1.00 | 1.00 | 1.00 | 1.00 | 1.00 | 1.00 | 1.00 | 1.00 | 1.00 |
| Gm10190 | 1.12 | 1.16 | 1.10 | 1.00 | 1.00 | 1.00 | 1.00 | 1.00 | 1.00 | 1.00 | 1.00 | 1.00 |
| Gm10272 | 1.00 | 1.00 | 1.00 | 1.00 | 1.00 | 1.00 | 1.00 | 1.00 | 1.00 | 1.00 | 1.00 | 1.00 |
| Gm10336 | 0.61 | 0.50 | 0.84 | 1.10 | 0.66 | 1.20 | 0.93 | 1.00 | 0.73 | 0.85 | 0.61 | 0.91 |
| Gm10413 | 1.00 | 1.00 | 1.00 | 1.00 | 1.00 | 1.00 | 1.00 | 1.00 | 1.00 | 1.00 | 1.00 | 1.00 |
| Gm10486 | 1.00 | 1.00 | 1.00 | 1.00 | 1.00 | 1.00 | 1.00 | 1.00 | 1.00 | 1.00 | 1.00 | 1.00 |
| Gm10768 | 1.00 | 1.00 | 1.00 | 0.75 | 2.07 | 0.72 | 0.61 | 0.07 | 0.64 | 0.85 | 1.00 | 1.00 |
| Gm11127 | 0.09 | 0.10 | 0.12 | 0.50 | 1.00 | 0.47 | 0.23 | 0.57 | 0.28 | 0.24 | 0.18 | 0.18 |
| Gm11559 | 1.00 | 1.00 | 1.00 | 1.00 | 1.00 | 1.00 | 1.00 | 1.00 | 1.00 | 1.00 | 1.00 | 1.00 |
| Gm11710 | 0.76 | 1.12 | 2.47 | 1.00 | 1.00 | 0.84 | 0.73 | 1.00 | 1.00 | 0.77 | 0.49 | 0.44 |
| Gm11937 | 1.00 | 1.00 | 1.00 | 1.00 | 1.00 | 1.00 | 1.00 | 1.00 | 1.00 | 1.00 | 1.00 | 1.00 |
| Gm11992 | 1.00 | 1.00 | 1.00 | 1.08 | 2.58 | 1.28 | 1.00 | 1.00 | 1.00 | 1.07 | 1.00 | 1.00 |
| Gm12070 | 0.77 | 0.99 | 0.76 | 0.94 | 2.04 | 0.89 | 1.13 | 0.24 | 1.15 | 0.96 | 1.03 | 0.96 |
| Gm12657 | 0.86 | 0.90 | 0.88 | 0.87 | 0.85 | 0.88 | 0.72 | 1.61 | 0.85 | 0.96 | 0.89 | 1.09 |
| Gm12888 | 1.00 | 2.40 | 2.37 | 1.00 | 1.00 | 1.00 | 1.00 | 1.00 | 1.00 | 1.00 | 1.00 | 1.00 |
| Gm13034 | 0.25 | 0.18 | 0.64 | 1.50 | 1.00 | 1.36 | 1.08 | 1.00 | 1.80 | 1.08 | 0.73 | 0.68 |
| Gm13124 | 1.00 | 1.00 | 1.00 | 1.00 | 1.00 | 1.00 | 1.00 | 1.00 | 1.00 | 1.00 | 1.00 | 1.00 |
| Gm13177 | 1.00 | 1.00 | 1.00 | 1.00 | 1.00 | 1.00 | 1.00 | 1.00 | 1.00 | 1.00 | 1.00 | 1.00 |
| Gm13304 | 2.50 | 2.53 | 1.79 | 0.77 | 1.00 | 1.00 | 1.00 | 1.00 | 1.00 | 0.76 | 1.07 | 1.00 |
| Gm13375 | 2.23 | 2.10 | 2.09 | 1.11 | 1.90 | 1.47 | 1.25 | 1.00 | 1.42 | 1.55 | 1.60 | 1.58 |
| Gm13498 | 1.21 | 1.17 | 1.18 | 1.39 | 3.59 | 1.45 | 1.36 | 0.42 | 1.51 | 1.58 | 1.81 | 1.66 |
| Gm13710 | 1.63 | 2.27 | 1.89 | 1.00 | 1.00 | 1.00 | 1.00 | 1.00 | 1.00 | 1.84 | 1.11 | 0.99 |
| Gm14308 | 0.49 | 0.46 | 0.57 | 0.34 | 0.21 | 0.39 | 0.17 | 0.23 | 0.16 | 0.41 | 0.45 | 0.57 |
| Gm14322 | 0.51 | 0.49 | 0.60 | 0.78 | 0.11 | 0.78 | 0.73 | 0.44 | 0.76 | 0.54 | 0.41 | 0.48 |
| Gm14346 | 1.00 | 1.00 | 1.00 | 1.00 | 1.00 | 1.00 | 1.00 | 1.00 | 1.00 | 1.00 | 1.00 | 1.00 |
| Gm14403 | 0.12 | 0.09 | 0.12 | 0.20 | 0.14 | 0.18 | 0.38 | 0.77 | 0.29 | 0.10 | 0.12 | 0.10 |
| Gm14420 | 0.51 | 0.48 | 0.49 | 0.44 | 0.30 | 0.46 | 0.18 | 0.29 | 0.16 | 0.41 | 0.37 | 0.43 |
| Gm14431 | 0.16 | 0.08 | 0.26 | 0.35 | 0.72 | 0.47 | 0.20 | 1.00 | 0.26 | 0.35 | 0.26 | 0.29 |
| Gm14436 | 0.37 | 0.19 | 0.67 | 0.72 | 1.00 | 0.87 | 0.30 | 1.00 | 0.29 | 0.86 | 0.60 | 0.63 |
| Gm14475 | 1.00 | 1.00 | 1.00 | 1.00 | 1.00 | 1.00 | 1.00 | 1.00 | 1.00 | 1.00 | 1.00 | 1.00 |
| Gm14476 | 1.00 | 1.00 | 1.00 | 1.00 | 1.00 | 1.00 | 1.00 | 1.00 | 1.00 | 1.00 | 1.00 | 1.00 |
| Gm14478 | 1.00 | 1.00 | 1.00 | 1.00 | 1.00 | 1.00 | 1.00 | 1.00 | 1.00 | 1.00 | 1.00 | 1.00 |
| Gm15104 | 1.00 | 1.00 | 1.00 | 1.00 | 1.00 | 1.00 | 1.00 | 1.00 | 1.00 | 1.00 | 1.00 | 1.00 |
| Gm15455 | 0.75 | 0.74 | 1.00 | 0.83 | 1.26 | 0.93 | 0.85 | 1.00 | 0.99 | 0.76 | 0.65 | 0.76 |
| Gm15987 | 2.17 | 1.59 | 3.14 | 1.00 | 1.00 | 1.00 | 1.00 | 1.00 | 1.00 | 1.32 | 1.00 | 1.00 |

Fig. 35- 39

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Gabpb1 | 0.90 | 0.82 | 0.79 | 1.25 | 1.00 | 1.12 | 0.97 | 0.54 | 1.00 | 0.92 | 0.82 | 0.92 |
| Gadd45a | 1.48 | 1.26 | 1.18 | 1.08 | 1.36 | 0.75 | 0.99 | 0.69 | 1.14 | 1.01 | 1.26 | 0.84 |
| Gak | 1.03 | 1.03 | 0.85 | 1.10 | 0.34 | 0.97 | 1.01 | 0.72 | 1.02 | 1.06 | 0.96 | 1.03 |
| Gale | 0.69 | 0.63 | 0.63 | 1.03 | 1.03 | 1.31 | 1.26 | 1.20 | 1.42 | 0.79 | 1.01 | 0.81 |
| Galm | 0.80 | 0.89 | 0.80 | 0.67 | 0.68 | 0.53 | 2.62 | 3.10 | 2.64 | 0.67 | 0.65 | 0.82 |
| Galnt11 | 0.98 | 0.97 | 0.92 | 1.23 | 0.51 | 1.01 | 1.14 | 1.00 | 1.12 | 1.10 | 0.87 | 1.06 |
| Galnt15 | 2.19 | 2.52 | 1.83 | 2.13 | 0.19 | 1.13 | 1.09 | 1.00 | 1.15 | 1.00 | 0.73 | 1.95 |
| Galnt7 | 0.90 | 0.75 | 0.71 | 1.04 | 1.00 | 0.82 | 1.11 | 0.79 | 1.01 | 0.97 | 0.75 | 1.17 |
| Gamt | 0.65 | 0.65 | 0.86 | 0.60 | 1.64 | 0.37 | 0.81 | 1.79 | 0.86 | 1.16 | 1.15 | 0.67 |
| Gapvd1 | 0.88 | 0.86 | 0.75 | 0.99 | 0.44 | 0.80 | 1.32 | 1.24 | 0.94 | 0.88 | 0.55 | 0.96 |
| Gas5 | 0.73 | 0.48 | 0.89 | 1.57 | 0.51 | 1.38 | 0.92 | 1.00 | 0.99 | 0.98 | 0.67 | 1.07 |
| Gas7 | 1.23 | 1.16 | 1.31 | 0.92 | 0.30 | 0.73 | 1.27 | 0.79 | 1.02 | 0.91 | 1.58 | 0.97 |
| Gck | 1.00 | 1.00 | 1.00 | 1.00 | 1.00 | 1.00 | 0.99 | 1.17 | 1.21 | 1.00 | 1.00 | 1.00 |
| Gdf11 | 1.00 | 1.00 | 1.00 | 0.99 | 1.00 | 0.91 | 0.97 | 1.00 | 1.00 | 0.59 | 0.14 | 0.81 |
| Gfap | 3.16 | 2.29 | 1.97 | 1.00 | 1.00 | 0.92 | 1.64 | 1.00 | 1.47 | 0.24 | 2.93 | 0.40 |
| Gfod1 | 0.90 | 0.83 | 0.67 | 0.97 | 0.40 | 0.99 | 1.00 | 1.00 | 1.00 | 1.24 | 1.51 | 1.28 |
| Gh | 1.00 | 1.00 | 1.00 | 1.00 | 0.14 | 1.00 | 1.00 | 1.00 | 1.00 | 0.77 | 0.53 | 0.72 |
| Gimap4 | 1.45 | 0.77 | 1.78 | 1.21 | 2.60 | 1.66 | 1.38 | 1.00 | 1.23 | 0.99 | 0.83 | 1.05 |
| Gk5 | 0.74 | 0.74 | 0.57 | 1.04 | 1.00 | 0.86 | 1.10 | 1.00 | 1.18 | 1.12 | 0.80 | 1.70 |
| Gkn1 | 0.85 | 1.07 | 0.75 | 0.60 | 0.57 | 0.51 | 1.22 | 1.00 | 0.71 | 1.00 | 1.00 | 0.91 |
| Gkn2 | 0.80 | 1.01 | 0.70 | 1.02 | 0.34 | 0.41 | 2.66 | 1.00 | 0.89 | 1.00 | 1.00 | 0.69 |
| Gldc | 0.12 | 0.11 | 0.12 | 1.00 | 1.00 | 0.32 | 0.71 | 0.90 | 1.21 | 1.00 | 1.00 | 1.00 |
| Glt6d1 | 1.00 | 1.00 | 1.00 | 1.00 | 1.00 | 1.00 | 0.81 | 0.16 | 0.84 | 1.00 | 1.00 | 1.00 |
| Gltp | 0.77 | 0.87 | 1.02 | 1.02 | 0.42 | 0.72 | 0.97 | 1.00 | 0.77 | 0.75 | 0.78 | 0.85 |
| Gltscr1 | 1.00 | 1.04 | 0.84 | 1.14 | 0.50 | 0.91 | 0.85 | 1.00 | 1.28 | 0.91 | 0.64 | 1.06 |
| Gltscr1l | 1.08 | 1.00 | 0.99 | 1.08 | 0.43 | 0.84 | 1.22 | 0.70 | 0.99 | 1.01 | 0.61 | 1.20 |
| Gm10046 | 1.00 | 1.00 | 1.00 | 1.00 | 1.00 | 1.00 | 1.32 | 4.39 | 0.78 | 1.00 | 1.00 | 1.00 |
| Gm10058 | 1.00 | 1.00 | 1.00 | 1.00 | 1.00 | 1.00 | 1.99 | 0.09 | 1.48 | 1.00 | 1.00 | 1.00 |
| Gm10100 | 1.00 | 1.00 | 1.00 | 1.00 | 1.00 | 1.00 | 1.00 | 1.00 | 1.00 | 1.00 | 1.00 | 1.00 |
| Gm10142 | 1.00 | 1.00 | 1.00 | 1.00 | 1.00 | 1.00 | 1.00 | 1.00 | 1.00 | 1.00 | 1.00 | 1.00 |
| Gm10190 | 1.00 | 1.00 | 1.00 | 1.49 | 1.00 | 1.28 | 0.19 | 0.25 | 0.14 | 1.00 | 1.20 | 1.00 |
| Gm10272 | 1.00 | 1.00 | 1.00 | 1.00 | 1.00 | 1.00 | 1.00 | 1.00 | 1.00 | 1.00 | 1.00 | 1.00 |
| Gm10336 | 1.01 | 0.82 | 1.02 | 0.83 | 0.49 | 0.67 | 0.84 | 0.51 | 0.89 | 0.83 | 0.55 | 0.89 |
| Gm10413 | 1.00 | 1.00 | 1.00 | 1.00 | 1.00 | 1.00 | 0.43 | 0.10 | 0.29 | 1.00 | 1.00 | 1.00 |
| Gm10486 | 1.00 | 1.00 | 1.00 | 1.00 | 1.00 | 1.00 | 1.00 | 0.09 | 0.94 | 1.00 | 1.00 | 1.00 |
| Gm10768 | 1.19 | 1.00 | 1.13 | 1.00 | 1.00 | 1.00 | 1.00 | 1.00 | 1.00 | 1.00 | 1.00 | 1.00 |
| Gm11127 | 0.16 | 0.12 | 0.12 | 0.15 | 0.19 | 0.15 | 0.59 | 1.00 | 0.47 | 0.17 | 0.14 | 0.15 |
| Gm11559 | 1.00 | 1.00 | 1.00 | 1.00 | 1.00 | 1.00 | 1.00 | 1.00 | 1.00 | 1.00 | 1.00 | 1.00 |
| Gm11710 | 0.51 | 0.64 | 2.03 | 0.70 | 0.53 | 0.60 | 1.34 | 1.00 | 2.03 | 0.92 | 1.00 | 1.68 |
| Gm11937 | 1.00 | 1.00 | 1.00 | 1.00 | 1.00 | 1.00 | 1.00 | 1.00 | 1.00 | 1.00 | 1.00 | 1.00 |
| Gm11992 | 0.71 | 0.98 | 0.99 | 1.34 | 1.00 | 1.83 | 1.18 | 0.46 | 1.08 | 1.00 | 1.00 | 1.00 |
| Gm12070 | 0.83 | 0.92 | 0.77 | 1.03 | 0.27 | 0.86 | 0.82 | 0.38 | 0.74 | 1.09 | 1.33 | 0.98 |
| Gm12657 | 1.07 | 0.87 | 0.98 | 0.90 | 0.23 | 1.00 | 0.99 | 0.66 | 1.10 | 0.96 | 0.88 | 1.05 |
| Gm12888 | 0.17 | 0.25 | 0.25 | 1.00 | 1.00 | 1.00 | 1.00 | 2.28 | 1.16 | 1.00 | 1.00 | 1.00 |
| Gm13034 | 1.17 | 0.89 | 0.48 | 1.43 | 1.00 | 0.73 | 1.34 | 1.28 | 1.13 | 0.72 | 0.36 | 1.07 |
| Gm13124 | 1.00 | 1.00 | 1.00 | 1.00 | 1.00 | 1.00 | 1.00 | 1.00 | 1.00 | 1.00 | 1.00 | 1.00 |
| Gm13177 | 1.00 | 1.00 | 1.00 | 1.00 | 1.00 | 1.00 | 1.00 | 1.00 | 1.00 | 1.00 | 1.00 | 1.00 |
| Gm13304 | 0.69 | 0.49 | 0.80 | 0.74 | 1.00 | 1.00 | 1.08 | 1.00 | 1.48 | 1.34 | 1.38 | 1.19 |
| Gm13375 | 1.56 | 1.38 | 1.90 | 0.89 | 1.00 | 0.94 | 0.98 | 1.00 | 0.95 | 1.44 | 1.71 | 1.51 |
| Gm13498 | 1.31 | 1.29 | 1.18 | 1.84 | 0.70 | 2.20 | 1.06 | 0.60 | 1.04 | 1.67 | 1.39 | 1.42 |
| Gm13710 | 1.00 | 0.81 | 1.00 | 1.00 | 1.00 | 1.00 | 1.00 | 1.00 | 1.00 | 0.81 | 1.02 | 0.77 |
| Gm14308 | 0.51 | 0.45 | 0.61 | 0.54 | 0.22 | 0.47 | 0.55 | 2.91 | 0.72 | 0.59 | 0.48 | 0.77 |
| Gm14322 | 0.87 | 0.54 | 0.72 | 1.04 | 0.97 | 1.00 | 1.00 | 1.00 | 1.00 | 0.61 | 0.38 | 0.48 |
| Gm14346 | 1.00 | 1.00 | 1.00 | 1.00 | 1.00 | 1.00 | 1.00 | 1.00 | 0.07 | 1.00 | 1.00 | 1.00 |
| Gm14403 | 0.19 | 0.13 | 0.15 | 0.24 | 0.44 | 0.19 | 0.25 | 0.42 | 0.36 | 0.16 | 0.15 | 0.17 |
| Gm14420 | 0.59 | 0.65 | 0.50 | 0.57 | 0.67 | 0.32 | 0.45 | 1.19 | 0.42 | 0.73 | 0.74 | 0.81 |
| Gm14431 | 0.38 | 0.30 | 0.19 | 0.39 | 0.17 | 0.20 | 0.94 | 1.00 | 1.00 | 0.30 | 0.15 | 0.65 |
| Gm14436 | 0.87 | 0.76 | 0.56 | 0.63 | 0.68 | 0.41 | 1.00 | 1.00 | 1.00 | 0.72 | 0.41 | 1.15 |
| Gm14475 | 1.00 | 1.00 | 1.00 | 1.00 | 1.00 | 1.00 | 0.83 | 0.04 | 0.10 | 1.00 | 1.00 | 1.00 |
| Gm14476 | 1.00 | 1.00 | 1.00 | 1.00 | 1.00 | 1.00 | 0.70 | 0.03 | 0.67 | 1.00 | 1.00 | 1.00 |
| Gm14478 | 1.00 | 1.00 | 1.00 | 1.00 | 1.00 | 1.00 | 0.77 | 0.01 | 0.78 | 1.00 | 1.00 | 1.00 |
| Gm15104 | 1.00 | 1.00 | 1.00 | 1.00 | 1.00 | 1.00 | 0.91 | 0.14 | 1.02 | 1.00 | 1.00 | 1.00 |
| Gm15455 | 0.83 | 0.89 | 0.77 | 1.16 | 0.93 | 1.09 | 0.85 | 0.88 | 0.89 | 0.81 | 0.81 | 1.06 |
| Gm15987 | 1.00 | 1.00 | 1.00 | 1.00 | 1.00 | 1.00 | 1.00 | 1.00 | 1.00 | 1.27 | 0.84 | 1.67 |

Fig. 35- 40

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Gabpb1 | 0.74 | 0.61 | 0.83 | 1.11 | 0.34 | 1.03 | 0.81 | 0.12 | 0.92 | 0.48 | 0.98 | 1.09 |
| Gadd45a | 1.00 | 1.00 | 1.00 | 0.98 | 0.18 | 1.08 | 0.75 | 0.29 | 0.91 | 0.61 | 0.91 | 0.80 |
| Gak | 1.16 | 1.14 | 1.21 | 1.13 | 1.94 | 1.03 | 1.11 | 0.14 | 0.98 | 0.68 | 1.13 | 1.08 |
| Gale | 0.54 | 0.57 | 0.44 | 1.10 | 0.76 | 1.09 | 0.99 | 3.34 | 0.68 | 2.20 | 0.82 | 1.17 |
| Galm | 0.97 | 0.84 | 0.90 | 1.48 | 1.69 | 1.38 | 0.84 | 0.35 | 0.85 | 0.29 | 0.55 | 0.56 |
| Galnt11 | 1.03 | 0.95 | 1.00 | 1.01 | 1.00 | 1.09 | 1.04 | 0.12 | 0.99 | 0.31 | 0.96 | 0.95 |
| Galnt15 | 1.57 | 1.70 | 2.51 | 0.97 | 1.00 | 0.95 | 1.36 | 0.27 | 2.40 | 1.00 | 1.00 | 1.00 |
| Galnt7 | 1.23 | 1.22 | 1.09 | 0.85 | 1.00 | 1.02 | 0.64 | 0.19 | 0.78 | 0.62 | 0.86 | 1.01 |
| Gamt | 0.20 | 0.29 | 0.46 | 1.08 | 0.43 | 1.00 | 1.20 | 2.58 | 1.30 | 2.33 | 1.12 | 1.34 |
| Gapvd1 | 1.25 | 1.07 | 1.28 | 0.88 | 1.12 | 0.89 | 0.69 | 0.14 | 0.77 | 0.45 | 0.82 | 0.87 |
| Gas5 | 1.07 | 1.58 | 1.54 | 0.88 | 1.00 | 0.98 | 0.76 | 0.06 | 0.83 | 0.12 | 0.49 | 0.67 |
| Gas7 | 1.00 | 1.00 | 1.00 | 0.95 | 0.69 | 0.93 | 0.72 | 0.22 | 0.74 | 0.68 | 1.06 | 1.00 |
| Gck | 1.54 | 1.61 | 1.02 | 1.00 | 1.00 | 1.46 | 1.04 | 0.79 | 1.13 | 1.00 | 1.00 | 1.00 |
| Gdf11 | 1.00 | 1.00 | 1.00 | 0.96 | 1.00 | 0.91 | 1.00 | 1.00 | 1.00 | 1.00 | 0.96 | 0.87 |
| Gfap | 1.00 | 1.00 | 1.00 | 1.48 | 1.21 | 1.76 | 1.00 | 1.00 | 1.00 | 0.48 | 0.40 | 0.58 |
| Gfod1 | 1.00 | 1.00 | 1.00 | 1.12 | 1.00 | 1.08 | 0.84 | 0.18 | 0.82 | 0.47 | 0.65 | 0.62 |
| Gh | 1.00 | 1.00 | 1.00 | 1.00 | 1.00 | 1.00 | 1.00 | 2.50 | 1.00 | 0.59 | 1.00 | 1.17 |
| Gimap4 | 0.59 | 1.31 | 1.29 | 1.00 | 0.18 | 1.00 | 0.80 | 2.40 | 1.01 | 1.16 | 1.34 | 1.25 |
| Gk5 | 1.00 | 1.00 | 1.00 | 1.00 | 1.00 | 1.00 | 0.78 | 0.09 | 1.13 | 1.00 | 0.99 | 1.02 |
| Gkn1 | 1.00 | 1.00 | 0.17 | 1.00 | 1.52 | 0.34 | 1.00 | 1.12 | 1.12 | 1.00 | 1.00 | 1.00 |
| Gkn2 | 1.75 | 1.00 | 0.15 | 1.00 | 1.37 | 0.32 | 1.00 | 4.08 | 1.00 | 3.07 | 0.96 | 1.00 |
| Gldc | 1.00 | 1.00 | 1.00 | 1.03 | 1.10 | 1.09 | 0.55 | 0.90 | 0.64 | 1.00 | 1.00 | 1.00 |
| Glt6d1 | 1.00 | 1.00 | 1.00 | 1.00 | 1.00 | 1.00 | 1.00 | 1.00 | 1.00 | 1.00 | 1.00 | 1.00 |
| Gltp | 0.90 | 0.85 | 0.83 | 0.97 | 1.00 | 0.92 | 0.76 | 0.03 | 0.56 | 0.26 | 1.08 | 1.13 |
| Gltscr1 | 1.00 | 1.00 | 1.00 | 0.95 | 1.00 | 1.12 | 0.90 | 0.17 | 1.00 | 0.43 | 0.94 | 0.97 |
| Gltscr1l | 0.76 | 1.08 | 0.86 | 1.04 | 1.00 | 1.11 | 0.73 | 0.14 | 1.12 | 0.38 | 0.84 | 0.83 |
| Gm10046 | 1.00 | 1.00 | 1.00 | 0.90 | 0.14 | 1.00 | 1.00 | 1.00 | 1.00 | 1.00 | 1.00 | 1.00 |
| Gm10058 | 1.00 | 1.00 | 1.00 | 1.00 | 1.00 | 1.00 | 1.00 | 1.00 | 1.00 | 1.00 | 1.00 | 1.00 |
| Gm10100 | 1.00 | 1.00 | 1.00 | 1.00 | 1.00 | 1.00 | 2.02 | 0.06 | 0.99 | 1.00 | 1.00 | 1.00 |
| Gm10142 | 1.00 | 1.00 | 1.00 | 1.00 | 1.00 | 1.00 | 3.37 | 0.09 | 1.17 | 1.00 | 1.00 | 1.00 |
| Gm10190 | 1.00 | 1.00 | 1.00 | 1.14 | 1.00 | 1.52 | 1.86 | 1.00 | 3.63 | 1.00 | 1.00 | 1.00 |
| Gm10272 | 1.00 | 1.00 | 1.00 | 1.00 | 1.00 | 1.00 | 3.38 | 0.07 | 1.01 | 1.00 | 1.00 | 1.00 |
| Gm10336 | 1.00 | 0.87 | 1.00 | 0.79 | 1.00 | 0.74 | 0.81 | 0.13 | 0.96 | 0.20 | 0.58 | 0.61 |
| Gm10413 | 1.00 | 1.00 | 1.00 | 1.00 | 1.00 | 1.00 | 1.00 | 1.00 | 1.00 | 1.00 | 1.00 | 1.00 |
| Gm10486 | 1.00 | 1.00 | 1.00 | 1.00 | 1.00 | 1.00 | 1.00 | 1.00 | 1.00 | 1.00 | 1.00 | 1.00 |
| Gm10768 | 1.00 | 1.00 | 1.00 | 1.00 | 1.00 | 1.00 | 1.00 | 1.00 | 1.00 | 1.00 | 1.23 | 1.71 |
| Gm11127 | 0.44 | 0.70 | 0.30 | 1.00 | 1.00 | 0.61 | 0.26 | 0.06 | 0.19 | 0.06 | 0.16 | 0.16 |
| Gm11559 | 1.00 | 1.00 | 1.00 | 1.00 | 1.00 | 1.00 | 2.27 | 0.07 | 0.49 | 1.00 | 1.00 | 1.00 |
| Gm11710 | 1.00 | 0.94 | 1.00 | 1.00 | 1.00 | 1.00 | 1.05 | 0.14 | 1.49 | 1.00 | 0.26 | 0.38 |
| Gm11937 | 1.00 | 1.00 | 1.00 | 1.00 | 1.00 | 1.00 | 2.53 | 0.07 | 0.81 | 1.00 | 1.00 | 1.00 |
| Gm11992 | 1.00 | 1.00 | 1.00 | 1.00 | 1.00 | 0.98 | 0.62 | 0.11 | 0.65 | 1.00 | 1.00 | 1.00 |
| Gm12070 | 1.02 | 0.93 | 0.72 | 1.15 | 0.66 | 0.98 | 1.25 | 0.17 | 1.14 | 0.57 | 1.03 | 1.00 |
| Gm12657 | 1.08 | 1.04 | 0.70 | 1.02 | 0.10 | 0.82 | 0.96 | 0.11 | 0.82 | 0.18 | 0.96 | 0.97 |
| Gm12888 | 1.00 | 1.00 | 1.00 | 1.00 | 1.00 | 1.00 | 1.00 | 1.00 | 1.00 | 1.00 | 1.00 | 1.00 |
| Gm13034 | 1.11 | 1.00 | 1.00 | 0.81 | 1.00 | 0.75 | 0.56 | 1.00 | 0.89 | 1.00 | 0.55 | 0.66 |
| Gm13124 | 1.00 | 1.00 | 1.00 | 1.00 | 1.00 | 1.00 | 1.09 | 0.05 | 0.83 | 1.00 | 1.00 | 1.00 |
| Gm13177 | 1.00 | 1.00 | 1.00 | 1.00 | 1.00 | 1.00 | 1.44 | 0.13 | 1.07 | 1.00 | 1.00 | 1.00 |
| Gm13304 | 1.00 | 1.00 | 1.00 | 1.00 | 1.00 | 1.00 | 1.31 | 0.08 | 0.84 | 1.00 | 1.00 | 1.00 |
| Gm13375 | 1.10 | 1.00 | 1.92 | 1.59 | 1.27 | 1.77 | 1.27 | 0.14 | 1.17 | 0.72 | 1.71 | 1.49 |
| Gm13498 | 1.52 | 1.37 | 1.34 | 1.48 | 1.17 | 1.35 | 1.39 | 0.05 | 1.31 | 0.28 | 1.22 | 1.38 |
| Gm13710 | 1.00 | 1.00 | 1.00 | 1.00 | 0.15 | 1.00 | 0.85 | 1.00 | 1.30 | 0.51 | 0.95 | 1.23 |
| Gm14308 | 0.48 | 0.39 | 0.62 | 0.51 | 0.32 | 0.49 | 0.47 | 1.49 | 0.54 | 0.96 | 0.56 | 0.57 |
| Gm14322 | 1.00 | 1.00 | 1.00 | 2.03 | 0.38 | 1.52 | 0.51 | 1.56 | 0.34 | 1.00 | 0.86 | 0.85 |
| Gm14346 | 1.00 | 1.00 | 1.00 | 1.00 | 1.00 | 1.00 | 1.00 | 1.00 | 1.00 | 1.00 | 1.00 | 1.00 |
| Gm14403 | 0.10 | 0.15 | 0.19 | 0.16 | 0.16 | 0.17 | 0.06 | 0.27 | 0.05 | 0.27 | 0.14 | 0.17 |
| Gm14420 | 0.50 | 0.59 | 0.33 | 0.49 | 0.29 | 0.53 | 0.39 | 0.81 | 0.41 | 0.74 | 0.49 | 0.43 |
| Gm14431 | 0.48 | 0.89 | 1.00 | 0.30 | 0.14 | 0.31 | 0.34 | 0.52 | 0.35 | 1.00 | 1.00 | 0.80 |
| Gm14436 | 1.00 | 1.00 | 1.00 | 0.77 | 0.38 | 0.73 | 0.68 | 1.00 | 0.61 | 1.00 | 1.00 | 1.00 |
| Gm14475 | 1.00 | 1.00 | 1.00 | 1.00 | 1.00 | 1.00 | 1.00 | 1.00 | 1.00 | 1.00 | 1.00 | 1.00 |
| Gm14476 | 1.00 | 1.00 | 1.00 | 1.00 | 1.00 | 1.00 | 1.00 | 1.00 | 1.00 | 1.00 | 1.00 | 1.00 |
| Gm14478 | 1.00 | 1.00 | 1.00 | 1.00 | 1.00 | 1.00 | 1.00 | 1.00 | 1.00 | 1.00 | 1.00 | 1.00 |
| Gm15104 | 1.00 | 1.00 | 1.00 | 1.00 | 1.00 | 1.00 | 1.00 | 1.00 | 1.00 | 1.00 | 1.00 | 1.00 |
| Gm15455 | 1.01 | 1.13 | 1.02 | 1.10 | 0.97 | 0.83 | 0.98 | 0.20 | 0.90 | 0.34 | 0.83 | 0.70 |
| Gm15987 | 1.00 | 1.00 | 1.00 | 1.00 | 1.00 | 1.00 | 0.64 | 0.08 | 0.90 | 0.72 | 1.40 | 1.58 |

Fig. 35- 41

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Gm16039 | 0.96 | 1.75 | 0.74 | 0.93 | 0.19 | 1.18 | 0.94 | 1.01 | 0.90 | 0.60 | 0.21 | 1.00 |
| Gm16675 | 1.00 | 1.00 | 1.00 | 1.00 | 1.00 | 1.00 | 1.00 | 1.00 | 1.00 | 1.00 | 1.00 | 0.87 |
| Gm19402 | 1.00 | 1.00 | 1.00 | 1.00 | 1.00 | 1.00 | 1.00 | 1.00 | 1.00 | 1.00 | 1.00 | 1.00 |
| Gm1987 | 1.00 | 1.00 | 1.00 | 1.00 | 1.00 | 1.00 | 1.00 | 1.00 | 1.00 | 1.00 | 1.00 | 1.00 |
| Gm20319 | 1.00 | 1.00 | 1.00 | 1.00 | 1.00 | 1.00 | 1.00 | 1.00 | 1.39 | 1.00 | 1.00 | 1.00 |
| Gm20594 | 1.00 | 1.00 | 1.00 | 1.00 | 1.00 | 1.00 | 1.44 | 2.01 | 1.00 | 1.00 | 1.00 | 1.30 |
| Gm20605 | 0.82 | 0.52 | 0.77 | 0.60 | 0.18 | 0.97 | 0.83 | 0.94 | 1.07 | 0.24 | 0.10 | 0.95 |
| Gm20748 | 1.33 | 0.54 | 0.89 | 0.42 | 3.87 | 1.44 | 1.00 | 0.83 | 0.86 | 0.88 | 1.66 | 0.75 |
| Gm20809 | 1.00 | 1.00 | 1.00 | 1.00 | 1.00 | 1.00 | 1.00 | 1.00 | 1.00 | 1.00 | 1.00 | 1.00 |
| Gm20815 | 1.00 | 1.00 | 1.00 | 1.00 | 1.00 | 1.00 | 1.00 | 1.00 | 1.00 | 1.00 | 1.00 | 1.00 |
| Gm21541 | 1.98 | 0.82 | 0.48 | 0.46 | 0.46 | 1.00 | 0.69 | 0.46 | 0.68 | 0.09 | 0.04 | 0.48 |
| Gm3086 | 1.00 | 1.00 | 1.00 | 3.09 | 0.88 | 1.95 | 1.00 | 1.00 | 1.00 | 1.00 | 1.00 | 1.00 |
| Gm3238 | 1.00 | 1.00 | 1.00 | 1.00 | 1.00 | 1.00 | 1.00 | 1.00 | 1.00 | 1.00 | 1.00 | 1.00 |
| Gm3402 | 1.00 | 1.00 | 1.00 | 1.00 | 1.00 | 1.00 | 1.00 | 1.00 | 1.00 | 1.00 | 1.00 | 1.00 |
| Gm3415 | 1.00 | 1.00 | 1.00 | 1.00 | 1.00 | 1.00 | 1.00 | 1.00 | 1.00 | 1.00 | 1.00 | 1.00 |
| Gm4559 | 1.00 | 1.00 | 1.00 | 1.00 | 1.00 | 1.00 | 1.00 | 1.00 | 1.00 | 1.00 | 1.00 | 1.00 |
| Gm4759 | 1.00 | 1.00 | 1.00 | 1.00 | 1.00 | 1.00 | 1.00 | 1.00 | 1.00 | 1.00 | 1.00 | 1.00 |
| Gm4836 | 1.00 | 1.00 | 1.00 | 1.00 | 1.00 | 1.00 | 1.00 | 1.00 | 1.00 | 1.00 | 1.00 | 1.00 |
| Gm5088 | 1.37 | 2.36 | 1.13 | 1.30 | 0.53 | 1.40 | 1.14 | 1.22 | 1.05 | 0.32 | 0.44 | 0.95 |
| Gm5538 | 1.00 | 1.00 | 1.00 | 1.00 | 1.00 | 1.00 | 1.00 | 1.00 | 1.00 | 1.00 | 1.00 | 1.00 |
| Gm5901 | 1.00 | 1.00 | 1.00 | 1.00 | 1.00 | 1.00 | 1.00 | 1.00 | 1.00 | 1.00 | 1.00 | 1.00 |
| Gm6194 | 1.75 | 1.31 | 2.02 | 0.96 | 0.07 | 1.01 | 1.24 | 1.30 | 1.32 | 1.00 | 0.19 | 1.31 |
| Gm6370 | 1.00 | 1.00 | 1.00 | 1.00 | 1.00 | 1.00 | 1.00 | 1.00 | 1.00 | 1.00 | 1.00 | 1.00 |
| Gm6402 | 1.24 | 1.27 | 0.88 | 0.19 | 1.57 | 0.99 | 1.25 | 0.87 | 0.85 | 0.38 | 0.86 | 0.94 |
| Gm6524 | 0.99 | 1.46 | 0.97 | 1.75 | 0.39 | 1.00 | 1.14 | 1.60 | 1.09 | 0.25 | 0.32 | 0.98 |
| Gm6548 | 1.10 | 1.64 | 1.15 | 0.72 | 0.09 | 1.03 | 0.84 | 0.91 | 1.16 | 0.06 | 0.07 | 0.97 |
| Gm6578 | 1.11 | 3.23 | 0.96 | 1.29 | 0.21 | 0.71 | 1.13 | 1.13 | 0.73 | 0.28 | 0.17 | 1.10 |
| Gm6623 | 1.24 | 1.00 | 1.13 | 0.88 | 0.18 | 1.02 | 1.02 | 1.23 | 1.16 | 1.00 | 0.66 | 1.28 |
| Gm6682 | 1.50 | 3.71 | 1.56 | 0.58 | 0.06 | 0.66 | 0.68 | 0.95 | 1.10 | 0.15 | 0.11 | 0.93 |
| Gm6710 | 0.36 | 1.00 | 0.27 | 1.14 | 0.30 | 0.35 | 0.08 | 0.15 | 0.12 | 1.00 | 0.35 | 0.37 |
| Gm7030 | 0.99 | 1.00 | 1.16 | 0.38 | 0.33 | 0.64 | 1.95 | 0.57 | 1.41 | 0.43 | 0.23 | 0.67 |
| Gm7073 | 1.00 | 1.00 | 1.00 | 1.00 | 1.00 | 1.00 | 1.00 | 1.00 | 1.00 | 1.00 | 1.00 | 1.00 |
| Gm7244 | 1.84 | 1.74 | 0.81 | 0.84 | 0.66 | 1.67 | 2.05 | 0.59 | 1.15 | 0.92 | 0.34 | 1.33 |
| Gm867 | 1.00 | 1.11 | 1.00 | 1.64 | 1.31 | 1.37 | 1.00 | 1.00 | 1.00 | 0.73 | 0.83 | 1.12 |
| Gm8898 | 0.34 | 1.00 | 0.35 | 0.98 | 0.40 | 0.29 | 0.22 | 0.33 | 0.46 | 1.00 | 0.53 | 0.41 |
| Gm94 | 1.00 | 1.00 | 1.00 | 1.00 | 1.00 | 1.00 | 1.00 | 1.00 | 1.00 | 1.00 | 1.00 | 1.00 |
| Gm9696 | 1.00 | 1.00 | 1.00 | 1.00 | 1.00 | 1.00 | 1.00 | 1.00 | 1.00 | 1.00 | 1.00 | 1.00 |
| Gmcl1 | 1.00 | 1.00 | 1.00 | 1.00 | 1.00 | 1.00 | 1.00 | 1.00 | 1.00 | 1.00 | 1.00 | 1.00 |
| Gna12 | 1.45 | 1.00 | 1.11 | 1.53 | 0.03 | 1.04 | 1.15 | 1.22 | 0.95 | 1.00 | 0.14 | 1.01 |
| Gnai1 | 0.55 | 0.88 | 0.97 | 1.58 | 0.39 | 0.91 | 1.33 | 1.22 | 1.27 | 0.68 | 0.45 | 0.80 |
| Gnai3 | 1.14 | 2.38 | 1.22 | 1.79 | 0.41 | 0.98 | 0.94 | 1.06 | 1.06 | 0.44 | 0.40 | 0.98 |
| Gng5 | 1.05 | 0.84 | 0.73 | 0.81 | 1.24 | 0.93 | 0.85 | 0.80 | 0.84 | 0.37 | 0.79 | 0.89 |
| Gnpda1 | 1.15 | 1.25 | 1.03 | 1.38 | 0.53 | 0.87 | 0.91 | 0.85 | 0.83 | 0.26 | 0.44 | 0.84 |
| Golga4 | 0.92 | 1.25 | 1.12 | 2.06 | 0.54 | 0.98 | 1.41 | 2.07 | 1.58 | 0.82 | 0.81 | 1.33 |
| Golga7 | 0.84 | 1.39 | 0.83 | 1.18 | 0.44 | 0.92 | 0.86 | 1.02 | 0.92 | 0.36 | 0.37 | 1.01 |
| Golim4 | 0.76 | 1.00 | 1.10 | 2.42 | 0.15 | 1.04 | 1.07 | 1.09 | 1.15 | 0.33 | 0.18 | 0.93 |
| Golph3l | 0.85 | 1.37 | 0.84 | 1.67 | 0.37 | 0.91 | 1.01 | 1.22 | 0.90 | 0.63 | 0.49 | 1.06 |
| Gpam | 0.25 | 1.00 | 0.53 | 0.64 | 0.17 | 1.02 | 0.90 | 1.38 | 1.30 | 1.00 | 0.72 | 1.25 |
| Gpatch2 | 1.01 | 1.37 | 0.99 | 1.12 | 0.20 | 1.11 | 0.99 | 1.27 | 1.01 | 0.98 | 0.31 | 1.03 |
| Gpatch2l | 0.65 | 2.18 | 0.99 | 1.51 | 0.20 | 1.07 | 1.07 | 1.14 | 1.07 | 0.73 | 0.45 | 1.10 |
| Gpatch8 | 0.78 | 2.14 | 1.03 | 2.63 | 0.16 | 1.02 | 1.30 | 1.42 | 1.20 | 0.49 | 0.38 | 1.13 |
| Gpd1 | 0.77 | 0.94 | 0.67 | 0.36 | 0.36 | 0.66 | 1.32 | 1.23 | 1.56 | 1.40 | 1.38 | 1.22 |
| Gpkow | 0.68 | 0.94 | 0.84 | 1.79 | 0.26 | 1.01 | 1.02 | 1.03 | 1.06 | 0.48 | 0.47 | 1.23 |
| Gpm6b | 0.95 | 1.18 | 0.92 | 2.67 | 0.07 | 1.46 | 0.85 | 0.85 | 0.98 | 0.38 | 0.40 | 0.90 |
| Gpn3 | 0.90 | 1.34 | 0.90 | 0.78 | 0.95 | 1.14 | 1.09 | 1.00 | 0.87 | 0.15 | 0.31 | 1.07 |
| Gpr116 | 0.70 | 1.26 | 0.89 | 1.27 | 0.46 | 0.90 | 1.05 | 1.17 | 1.01 | 0.67 | 0.56 | 0.99 |
| Gpr124 | 0.58 | 1.00 | 0.97 | 1.30 | 0.75 | 1.18 | 1.22 | 1.12 | 1.25 | 0.46 | 0.34 | 0.87 |
| Gpr135 | 1.00 | 1.00 | 1.00 | 0.47 | 0.10 | 0.49 | 1.00 | 1.00 | 1.00 | 1.00 | 1.00 | 1.27 |
| Gprasp1 | 0.97 | 1.09 | 0.85 | 1.71 | 0.12 | 0.89 | 0.68 | 0.76 | 0.93 | 0.91 | 0.84 | 0.80 |
| Gpt | 0.60 | 0.63 | 1.12 | 0.16 | 1.39 | 0.94 | 0.79 | 0.78 | 0.51 | 1.11 | 1.19 | 0.98 |
| Gpx5 | 1.00 | 1.00 | 1.00 | 1.00 | 1.00 | 1.00 | 1.00 | 1.00 | 1.00 | 1.00 | 1.00 | 1.00 |
| Gramd4 | 1.78 | 2.79 | 1.32 | 1.30 | 0.27 | 1.27 | 1.02 | 1.08 | 1.02 | 0.29 | 0.33 | 1.11 |
| Grem2 | 0.35 | 0.76 | 0.35 | 1.00 | 1.00 | 1.00 | 1.00 | 1.00 | 1.00 | 0.40 | 0.58 | 0.96 |
| Grhl2 | 1.00 | 1.00 | 1.00 | 1.00 | 1.00 | 1.00 | 1.00 | 1.00 | 1.00 | 0.64 | 0.32 | 1.18 |

Fig. 35- 42

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Gm16039 | 1.06 | 0.89 | 1.06 | 0.95 | 1.74 | 0.97 | 0.66 | 1.00 | 0.67 | 1.28 | 1.04 | 1.26 |
| Gm16675 | 0.32 | 0.49 | 0.72 | 1.00 | 1.00 | 1.00 | 0.85 | 1.00 | 1.33 | 1.02 | 0.51 | 0.96 |
| Gm19402 | 1.00 | 1.00 | 1.00 | 1.00 | 1.00 | 1.00 | 1.00 | 1.00 | 1.00 | 1.00 | 1.00 | 1.00 |
| Gm1987 | 1.00 | 1.00 | 1.00 | 1.00 | 1.00 | 0.32 | 0.64 | 1.00 | 1.00 | 1.00 | 1.00 | 1.00 |
| Gm20319 | 1.00 | 1.00 | 1.00 | 1.00 | 1.00 | 1.00 | 0.75 | 0.98 | 0.79 | 1.00 | 1.00 | 1.00 |
| Gm20594 | 1.00 | 1.00 | 1.00 | 1.00 | 1.00 | 1.00 | 1.00 | 1.00 | 1.00 | 1.00 | 1.00 | 1.00 |
| Gm20605 | 0.71 | 0.73 | 0.86 | 0.93 | 0.65 | 0.95 | 0.50 | 1.00 | 0.88 | 0.98 | 0.88 | 0.92 |
| Gm20748 | 0.69 | 0.55 | 0.70 | 0.55 | 0.51 | 1.03 | 0.56 | 0.99 | 0.93 | 0.90 | 0.92 | 1.05 |
| Gm20809 | 1.00 | 1.00 | 1.00 | 1.00 | 1.00 | 1.00 | 1.00 | 1.00 | 1.00 | 1.00 | 1.00 | 1.00 |
| Gm20815 | 1.00 | 1.00 | 1.00 | 1.00 | 1.00 | 1.00 | 1.00 | 1.00 | 1.00 | 1.00 | 1.00 | 1.00 |
| Gm21541 | 2.79 | 2.62 | 2.05 | 1.00 | 1.00 | 0.91 | 1.00 | 1.00 | 1.00 | 0.79 | 1.09 | 0.77 |
| Gm3086 | 2.05 | 1.75 | 0.87 | 1.00 | 1.00 | 1.00 | 1.00 | 1.00 | 1.00 | 1.00 | 1.00 | 1.01 |
| Gm3238 | 1.00 | 1.00 | 1.00 | 1.00 | 1.00 | 1.00 | 1.00 | 1.00 | 1.00 | 1.00 | 1.00 | 1.00 |
| Gm3402 | 1.00 | 1.00 | 1.00 | 1.00 | 1.00 | 1.00 | 1.00 | 1.00 | 1.00 | 1.00 | 1.00 | 1.00 |
| Gm3415 | 1.00 | 1.00 | 1.00 | 1.00 | 1.00 | 1.00 | 1.00 | 1.00 | 1.00 | 1.00 | 1.00 | 1.00 |
| Gm4559 | 1.00 | 1.00 | 1.00 | 1.00 | 1.00 | 1.00 | 1.00 | 1.00 | 1.00 | 1.00 | 1.00 | 1.00 |
| Gm4759 | 1.00 | 1.00 | 1.00 | 1.00 | 1.00 | 1.00 | 1.00 | 1.00 | 1.00 | 1.00 | 1.00 | 1.00 |
| Gm4836 | 1.00 | 1.00 | 1.00 | 1.00 | 1.00 | 1.00 | 1.00 | 1.00 | 1.00 | 1.00 | 1.00 | 1.00 |
| Gm5088 | 0.88 | 0.93 | 0.94 | 1.46 | 3.29 | 1.30 | 1.69 | 0.66 | 1.78 | 1.18 | 1.02 | 1.14 |
| Gm5538 | 1.00 | 1.00 | 1.00 | 1.00 | 1.00 | 1.00 | 1.00 | 1.00 | 1.00 | 1.00 | 1.00 | 1.00 |
| Gm5901 | 1.00 | 1.00 | 1.00 | 1.00 | 1.00 | 1.00 | 1.00 | 1.00 | 1.00 | 1.00 | 1.00 | 1.00 |
| Gm6194 | 0.84 | 0.91 | 0.98 | 1.45 | 1.00 | 1.34 | 2.18 | 1.00 | 1.64 | 1.15 | 0.70 | 1.27 |
| Gm6370 | 1.00 | 1.00 | 1.00 | 1.00 | 1.00 | 1.00 | 1.00 | 1.00 | 1.00 | 1.00 | 1.00 | 1.00 |
| Gm6402 | 1.31 | 1.63 | 0.89 | 1.01 | 2.25 | 0.87 | 1.04 | 0.21 | 1.13 | 1.07 | 1.70 | 1.12 |
| Gm6524 | 0.92 | 0.96 | 0.96 | 0.89 | 2.85 | 0.90 | 0.92 | 0.68 | 1.02 | 1.07 | 1.18 | 1.02 |
| Gm6548 | 0.93 | 0.96 | 1.04 | 0.81 | 0.59 | 0.91 | 0.89 | 0.22 | 1.12 | 0.96 | 0.87 | 1.02 |
| Gm6578 | 1.18 | 1.10 | 0.94 | 0.93 | 1.77 | 1.03 | 0.87 | 1.00 | 1.10 | 1.27 | 0.98 | 1.06 |
| Gm6623 | 0.78 | 0.68 | 0.79 | 1.15 | 1.00 | 0.69 | 1.29 | 1.00 | 0.77 | 1.02 | 0.82 | 1.12 |
| Gm6682 | 0.50 | 0.58 | 0.58 | 0.87 | 2.40 | 0.81 | 0.93 | 1.00 | 1.08 | 0.99 | 0.88 | 1.00 |
| Gm6710 | 0.64 | 0.49 | 0.76 | 0.45 | 0.71 | 0.44 | 0.10 | 0.77 | 0.10 | 0.48 | 0.50 | 0.65 |
| Gm7030 | 0.63 | 0.63 | 0.55 | 0.93 | 2.89 | 0.69 | 0.77 | 0.32 | 0.93 | 0.80 | 0.81 | 0.62 |
| Gm7073 | 1.00 | 1.00 | 1.00 | 1.00 | 1.00 | 1.00 | 1.00 | 1.00 | 1.00 | 1.00 | 1.00 | 1.00 |
| Gm7244 | 0.84 | 1.47 | 1.06 | 0.69 | 1.46 | 0.44 | 2.16 | 1.00 | 1.16 | 1.26 | 2.00 | 0.64 |
| Gm867 | 1.00 | 1.00 | 1.00 | 1.00 | 1.00 | 1.00 | 1.00 | 1.00 | 1.00 | 1.00 | 1.00 | 1.00 |
| Gm8898 | 0.23 | 0.13 | 0.25 | 0.36 | 1.00 | 0.40 | 0.20 | 1.00 | 0.22 | 0.29 | 0.16 | 0.25 |
| Gm94 | 1.21 | 0.35 | 1.00 | 1.00 | 1.00 | 1.00 | 1.00 | 1.00 | 1.00 | 1.00 | 1.00 | 1.00 |
| Gm9696 | 1.00 | 1.00 | 1.00 | 1.00 | 1.00 | 1.00 | 1.00 | 1.00 | 1.00 | 1.00 | 1.00 | 1.00 |
| Gmcl1 | 1.00 | 1.00 | 1.00 | 1.00 | 1.00 | 1.00 | 1.00 | 1.00 | 1.00 | 1.00 | 1.00 | 1.00 |
| Gna12 | 0.96 | 0.70 | 1.48 | 1.11 | 1.00 | 1.34 | 0.88 | 1.20 | 0.98 | 1.05 | 0.43 | 1.01 |
| Gnai1 | 0.89 | 0.81 | 0.67 | 1.51 | 2.01 | 1.34 | 1.20 | 1.00 | 1.47 | 1.47 | 1.36 | 1.46 |
| Gnai3 | 0.75 | 0.76 | 0.95 | 1.00 | 1.51 | 0.92 | 0.91 | 0.59 | 0.91 | 1.02 | 0.79 | 0.93 |
| Gng5 | 0.98 | 1.23 | 1.01 | 0.74 | 0.97 | 0.94 | 0.81 | 0.10 | 0.81 | 0.94 | 1.50 | 1.08 |
| Gnpda1 | 1.20 | 1.31 | 1.22 | 1.04 | 2.14 | 1.14 | 0.87 | 0.85 | 0.80 | 0.78 | 0.98 | 0.96 |
| Golga4 | 0.65 | 0.50 | 0.90 | 1.39 | 1.36 | 1.31 | 1.37 | 0.78 | 1.34 | 1.02 | 0.72 | 0.86 |
| Golga7 | 0.91 | 0.97 | 0.90 | 0.93 | 2.30 | 0.82 | 0.92 | 0.44 | 0.92 | 0.98 | 0.89 | 1.04 |
| Golim4 | 1.08 | 0.86 | 1.20 | 1.03 | 1.00 | 1.20 | 1.15 | 0.89 | 1.20 | 0.98 | 0.66 | 0.86 |
| Golph3l | 0.81 | 0.98 | 0.98 | 1.08 | 1.47 | 0.90 | 0.67 | 1.00 | 1.27 | 0.99 | 0.80 | 1.03 |
| Gpam | 0.49 | 0.38 | 0.78 | 1.49 | 1.28 | 1.67 | 1.62 | 1.53 | 1.63 | 1.35 | 0.41 | 1.17 |
| Gpatch2 | 0.73 | 0.62 | 0.84 | 1.15 | 1.00 | 1.21 | 1.29 | 1.00 | 1.28 | 0.90 | 0.60 | 0.89 |
| Gpatch2l | 0.66 | 0.59 | 0.91 | 1.12 | 1.00 | 1.13 | 1.22 | 1.00 | 1.70 | 0.92 | 0.60 | 0.91 |
| Gpatch8 | 0.63 | 0.55 | 0.86 | 1.18 | 1.19 | 1.04 | 0.87 | 1.00 | 1.06 | 0.96 | 0.55 | 0.89 |
| Gpd1 | 0.18 | 0.37 | 0.18 | 0.64 | 0.60 | 0.81 | 0.85 | 0.79 | 1.09 | 1.04 | 0.95 | 1.17 |
| Gpkow | 0.84 | 0.95 | 1.12 | 0.99 | 0.90 | 0.99 | 0.96 | 1.00 | 0.87 | 1.07 | 0.82 | 1.14 |
| Gpm6b | 1.16 | 1.37 | 1.37 | 0.78 | 1.00 | 0.76 | 1.00 | 1.00 | 1.00 | 0.88 | 0.93 | 1.05 |
| Gpn3 | 0.93 | 1.07 | 0.83 | 0.94 | 0.83 | 0.94 | 0.62 | 0.69 | 0.80 | 0.81 | 1.09 | 0.88 |
| Gpr116 | 1.39 | 1.02 | 1.16 | 1.03 | 1.52 | 1.09 | 0.87 | 1.09 | 1.01 | 0.98 | 0.77 | 0.98 |
| Gpr124 | 0.17 | 0.16 | 0.34 | 2.17 | 1.51 | 2.12 | 0.93 | 1.00 | 1.78 | 0.95 | 0.69 | 0.99 |
| Gpr135 | 1.00 | 1.00 | 1.00 | 0.92 | 1.00 | 1.87 | 0.64 | 1.00 | 0.98 | 1.00 | 1.00 | 1.00 |
| Gprasp1 | 0.76 | 0.57 | 0.95 | 0.86 | 1.05 | 0.96 | 0.85 | 1.00 | 0.85 | 0.98 | 0.67 | 0.86 |
| Gpt | 0.76 | 0.99 | 0.66 | 1.25 | 0.96 | 0.98 | 0.79 | 0.68 | 0.87 | 1.03 | 1.31 | 1.18 |
| Gpx5 | 1.00 | 1.00 | 1.00 | 1.00 | 1.00 | 1.00 | 1.00 | 1.00 | 1.00 | 1.00 | 1.00 | 1.00 |
| Gramd4 | 0.94 | 0.83 | 1.18 | 0.94 | 2.29 | 0.96 | 1.10 | 1.00 | 1.45 | 0.99 | 0.80 | 1.04 |
| Grem2 | 1.00 | 1.00 | 1.00 | 2.06 | 1.00 | 0.97 | 1.08 | 0.88 | 0.51 | 1.20 | 0.92 | 1.19 |
| Grhl2 | 2.18 | 1.41 | 1.76 | 1.01 | 1.00 | 1.06 | 1.00 | 1.00 | 1.00 | 1.02 | 0.88 | 1.18 |

Fig. 35- 43

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Gm16039 | 1.02 | 0.81 | 0.86 | 0.80 | 0.90 | 0.91 | 1.04 | 0.51 | 1.02 | 0.92 | 0.83 | 1.01 |
| Gm16675 | 0.88 | 1.12 | 1.30 | 0.96 | 1.00 | 0.92 | 1.00 | 1.00 | 1.00 | 0.80 | 0.19 | 1.31 |
| Gm19402 | 1.00 | 1.00 | 1.00 | 1.00 | 1.00 | 1.00 | 1.00 | 1.00 | 1.00 | 1.00 | 1.00 | 1.00 |
| Gm1987 | 1.00 | 1.00 | 1.00 | 0.03 | 1.00 | 1.00 | 1.00 | 1.00 | 1.00 | 1.00 | 1.00 | 0.04 |
| Gm20319 | 1.00 | 1.00 | 1.00 | 1.00 | 1.00 | 1.00 | 1.13 | 1.00 | 0.97 | 1.00 | 1.00 | 1.00 |
| Gm20594 | 1.00 | 1.00 | 1.00 | 1.00 | 0.12 | 1.00 | 1.00 | 1.00 | 1.00 | 1.00 | 1.00 | 1.00 |
| Gm20605 | 0.90 | 0.90 | 1.11 | 0.92 | 0.33 | 0.89 | 0.91 | 3.74 | 1.07 | 0.91 | 0.74 | 0.92 |
| Gm20748 | 1.30 | 1.10 | 1.31 | 0.75 | 3.71 | 0.99 | 1.17 | 1.17 | 1.69 | 0.84 | 0.34 | 0.76 |
| Gm20809 | 1.00 | 1.00 | 1.00 | 1.00 | 1.00 | 1.00 | 1.23 | 0.14 | 1.03 | 1.00 | 1.00 | 1.00 |
| Gm20815 | 1.00 | 1.00 | 1.00 | 1.00 | 1.00 | 1.00 | 1.19 | 0.17 | 0.84 | 1.00 | 1.00 | 1.00 |
| Gm21541 | 0.37 | 0.55 | 1.26 | 0.91 | 1.00 | 0.97 | 1.00 | 1.00 | 2.17 | 1.55 | 1.50 | 1.30 |
| Gm3086 | 1.00 | 1.00 | 1.00 | 3.21 | 1.00 | 1.01 | 1.53 | 1.21 | 1.16 | 1.30 | 1.32 | 1.08 |
| Gm3238 | 1.00 | 1.00 | 1.00 | 1.00 | 1.00 | 1.00 | 1.00 | 1.00 | 1.00 | 1.00 | 1.00 | 1.00 |
| Gm3402 | 1.00 | 1.00 | 1.00 | 1.00 | 1.00 | 1.00 | 1.53 | 0.14 | 1.44 | 1.00 | 1.00 | 1.00 |
| Gm3415 | 1.00 | 1.00 | 1.00 | 1.00 | 1.00 | 1.00 | 1.16 | 1.00 | 0.10 | 1.00 | 1.00 | 1.00 |
| Gm4559 | 1.00 | 1.00 | 1.00 | 1.00 | 1.00 | 1.00 | 1.00 | 1.00 | 1.00 | 1.00 | 1.00 | 1.00 |
| Gm4759 | 1.00 | 1.00 | 1.00 | 1.00 | 1.00 | 1.00 | 1.00 | 1.00 | 1.00 | 0.42 | 0.55 | 0.18 |
| Gm4836 | 1.00 | 1.00 | 1.00 | 1.00 | 1.00 | 1.00 | 0.60 | 1.00 | 0.10 | 1.00 | 1.00 | 1.00 |
| Gm5088 | 1.18 | 1.20 | 1.21 | 1.30 | 0.52 | 1.38 | 1.07 | 1.00 | 0.84 | 0.92 | 0.96 | 0.88 |
| Gm5538 | 1.00 | 1.00 | 1.00 | 1.00 | 1.00 | 1.00 | 0.78 | 1.00 | 1.05 | 1.00 | 1.00 | 1.00 |
| Gm5901 | 1.00 | 1.00 | 1.00 | 1.00 | 1.00 | 1.00 | 0.92 | 0.09 | 1.16 | 1.00 | 1.00 | 1.00 |
| Gm6194 | 0.68 | 0.77 | 0.57 | 2.08 | 0.38 | 1.18 | 0.87 | 0.79 | 1.03 | 1.12 | 1.00 | 1.11 |
| Gm6370 | 1.00 | 1.00 | 1.00 | 1.00 | 1.00 | 1.00 | 1.08 | 0.12 | 0.95 | 1.00 | 1.00 | 1.00 |
| Gm6402 | 0.97 | 1.08 | 1.03 | 1.07 | 0.76 | 1.14 | 0.83 | 0.17 | 1.03 | 1.40 | 1.59 | 1.15 |
| Gm6524 | 0.83 | 0.79 | 0.71 | 0.94 | 1.00 | 1.36 | 1.12 | 0.27 | 1.16 | 1.04 | 0.87 | 1.12 |
| Gm6548 | 0.97 | 1.05 | 0.96 | 1.00 | 0.12 | 1.07 | 0.93 | 0.26 | 0.96 | 1.04 | 0.95 | 1.05 |
| Gm6578 | 0.93 | 1.05 | 1.06 | 1.04 | 1.00 | 1.21 | 0.90 | 0.36 | 1.24 | 1.05 | 1.25 | 1.02 |
| Gm6623 | 0.95 | 0.94 | 0.77 | 1.00 | 1.00 | 0.89 | 0.85 | 0.58 | 0.94 | 1.12 | 0.68 | 1.03 |
| Gm6682 | 0.75 | 0.67 | 0.68 | 1.08 | 0.18 | 0.74 | 0.82 | 1.05 | 1.22 | 0.77 | 0.87 | 0.72 |
| Gm6710 | 0.65 | 0.41 | 0.60 | 0.60 | 0.52 | 0.41 | 0.88 | 1.00 | 1.00 | 0.69 | 0.44 | 1.14 |
| Gm7030 | 0.62 | 0.58 | 0.48 | 0.63 | 0.17 | 0.52 | 0.58 | 1.00 | 0.53 | 0.64 | 0.54 | 0.52 |
| Gm7073 | 1.00 | 1.00 | 1.00 | 1.00 | 1.00 | 1.00 | 0.98 | 0.17 | 0.95 | 1.00 | 1.00 | 1.00 |
| Gm7244 | 0.54 | 0.67 | 1.91 | 1.00 | 1.00 | 1.16 | 1.56 | 0.88 | 0.69 | 1.30 | 2.07 | 1.52 |
| Gm867 | 1.00 | 1.00 | 1.00 | 1.41 | 1.00 | 2.26 | 0.82 | 1.00 | 1.17 | 0.37 | 0.40 | 0.20 |
| Gm8898 | 0.45 | 0.35 | 0.16 | 0.41 | 0.54 | 0.13 | 0.64 | 1.00 | 0.58 | 0.33 | 0.19 | 0.44 |
| Gm94 | 1.13 | 1.09 | 1.49 | 1.00 | 1.00 | 1.00 | 1.00 | 1.00 | 1.00 | 1.00 | 1.00 | 1.00 |
| Gm9696 | 0.85 | 0.92 | 1.31 | 1.00 | 1.00 | 1.00 | 1.00 | 1.00 | 1.00 | 1.00 | 1.00 | 1.00 |
| Gmcl1 | 1.00 | 1.00 | 1.00 | 1.00 | 1.00 | 1.00 | 0.07 | 1.61 | 0.07 | 1.00 | 1.00 | 1.00 |
| Gna12 | 0.99 | 0.99 | 1.00 | 1.15 | 0.10 | 0.94 | 1.12 | 1.00 | 1.01 | 0.79 | 0.74 | 0.92 |
| Gnai1 | 0.90 | 0.80 | 0.95 | 0.48 | 0.23 | 0.60 | 1.23 | 1.14 | 0.97 | 0.80 | 4.38 | 0.88 |
| Gnai3 | 0.86 | 0.82 | 0.79 | 1.06 | 0.26 | 0.94 | 0.98 | 0.49 | 1.00 | 1.01 | 0.64 | 0.93 |
| Gng5 | 0.88 | 1.07 | 1.03 | 0.96 | 0.56 | 0.96 | 0.80 | 0.16 | 1.10 | 1.20 | 1.08 | 0.88 |
| Gnpda1 | 1.09 | 1.20 | 1.16 | 0.74 | 0.46 | 0.82 | 0.88 | 0.24 | 0.90 | 1.14 | 1.05 | 0.95 |
| Golga4 | 1.08 | 1.09 | 0.74 | 1.21 | 0.17 | 0.75 | 1.40 | 1.37 | 1.26 | 0.93 | 0.70 | 1.09 |
| Golga7 | 1.13 | 1.19 | 1.09 | 1.01 | 0.23 | 1.08 | 1.05 | 0.69 | 1.01 | 1.06 | 0.92 | 0.98 |
| Golim4 | 1.05 | 0.98 | 1.04 | 0.87 | 0.45 | 0.78 | 1.01 | 1.00 | 1.26 | 1.00 | 0.61 | 0.89 |
| Golph3l | 0.84 | 0.74 | 0.83 | 1.14 | 0.76 | 0.83 | 0.93 | 0.53 | 1.02 | 1.01 | 0.73 | 0.92 |
| Gpam | 1.17 | 1.36 | 0.96 | 0.63 | 0.14 | 0.98 | 1.19 | 1.00 | 0.90 | 1.01 | 0.69 | 1.12 |
| Gpatch2 | 1.01 | 1.02 | 0.94 | 1.02 | 0.62 | 0.95 | 1.04 | 1.51 | 1.02 | 1.10 | 0.73 | 0.94 |
| Gpatch2l | 0.93 | 0.75 | 0.79 | 0.91 | 0.84 | 0.75 | 1.00 | 1.17 | 1.00 | 0.97 | 0.59 | 1.10 |
| Gpatch8 | 1.01 | 1.01 | 0.86 | 1.23 | 0.60 | 1.03 | 1.12 | 0.81 | 1.06 | 1.01 | 0.68 | 1.04 |
| Gpd1 | 1.07 | 0.94 | 0.81 | 0.27 | 0.22 | 0.41 | 1.09 | 0.92 | 0.94 | 0.72 | 1.32 | 0.68 |
| Gpkow | 1.10 | 0.99 | 0.97 | 1.07 | 0.67 | 1.07 | 1.01 | 0.69 | 1.01 | 1.24 | 0.94 | 1.25 |
| Gpm6b | 0.90 | 0.88 | 1.20 | 0.71 | 0.79 | 0.78 | 1.05 | 0.46 | 0.97 | 0.67 | 1.58 | 0.64 |
| Gpn3 | 0.98 | 1.05 | 1.06 | 0.79 | 1.00 | 0.98 | 0.94 | 0.43 | 1.14 | 1.20 | 1.20 | 0.91 |
| Gpr116 | 1.18 | 1.21 | 1.14 | 0.64 | 0.19 | 0.59 | 1.00 | 1.00 | 1.00 | 0.96 | 0.74 | 1.12 |
| Gpr124 | 1.10 | 1.06 | 1.28 | 1.21 | 0.54 | 1.11 | 1.00 | 1.00 | 1.00 | 0.37 | 0.29 | 0.40 |
| Gpr135 | 1.00 | 1.00 | 1.00 | 0.61 | 1.00 | 0.64 | 0.54 | 1.00 | 0.63 | 1.00 | 1.00 | 1.00 |
| Gprasp1 | 0.95 | 0.84 | 0.98 | 0.91 | 0.50 | 1.10 | 0.94 | 0.77 | 0.84 | 0.93 | 1.48 | 1.10 |
| Gpt | 0.90 | 1.02 | 0.68 | 0.37 | 0.65 | 0.25 | 1.00 | 1.00 | 1.00 | 1.00 | 1.01 | 0.77 |
| Gpx5 | 1.00 | 1.00 | 1.00 | 0.06 | 1.00 | 1.00 | 1.00 | 1.00 | 1.00 | 1.00 | 1.00 | 1.00 |
| Gramd4 | 0.89 | 0.86 | 0.79 | 1.19 | 0.78 | 0.91 | 0.99 | 1.00 | 0.74 | 1.16 | 0.99 | 1.26 |
| Grem2 | 0.97 | 0.95 | 1.19 | 0.52 | 0.19 | 1.92 | 1.00 | 1.00 | 1.00 | 0.90 | 0.69 | 0.95 |
| Grhl2 | 1.13 | 1.08 | 0.99 | 1.00 | 1.00 | 1.00 | 0.63 | 1.00 | 0.73 | 1.00 | 1.00 | 1.00 |

Fig. 35- 44

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Gm16039 | 0.94 | 0.86 | 1.17 | 1.09 | 1.00 | 0.90 | 0.73 | 0.31 | 1.03 | 0.37 | 1.01 | 1.00 |
| Gm16675 | 1.00 | 1.00 | 1.00 | 1.00 | 1.00 | 1.00 | 0.87 | 1.00 | 0.91 | 1.00 | 0.86 | 0.66 |
| Gm19402 | 1.00 | 1.00 | 1.00 | 1.00 | 1.00 | 1.00 | 2.94 | 0.10 | 1.09 | 1.00 | 1.00 | 1.00 |
| Gm1987 | 1.00 | 1.00 | 1.00 | 1.00 | 0.92 | 1.00 | 1.00 | 1.00 | 1.00 | 1.00 | 1.00 | 1.00 |
| Gm20319 | 1.00 | 1.00 | 1.00 | 1.71 | 0.07 | 1.00 | 1.00 | 1.00 | 1.00 | 1.00 | 1.00 | 1.00 |
| Gm20594 | 1.00 | 1.00 | 1.00 | 1.00 | 1.00 | 1.00 | 1.00 | 1.00 | 1.00 | 1.00 | 1.00 | 1.00 |
| Gm20605 | 0.75 | 0.92 | 1.13 | 0.91 | 1.00 | 1.11 | 1.21 | 0.04 | 1.18 | 0.27 | 1.14 | 0.87 |
| Gm20748 | 1.01 | 1.00 | 1.00 | 0.78 | 0.18 | 0.38 | 1.08 | 3.60 | 0.87 | 1.00 | 1.00 | 1.00 |
| Gm20809 | 1.00 | 1.00 | 1.00 | 1.00 | 1.00 | 1.00 | 1.00 | 1.00 | 1.00 | 1.00 | 1.00 | 1.00 |
| Gm20815 | 1.00 | 1.00 | 1.00 | 1.00 | 1.00 | 1.00 | 1.00 | 1.00 | 1.00 | 1.00 | 1.00 | 1.00 |
| Gm21541 | 1.00 | 1.00 | 0.47 | 1.00 | 1.00 | 1.00 | 1.79 | 0.09 | 1.17 | 1.00 | 1.00 | 1.00 |
| Gm3086 | 1.00 | 1.00 | 1.00 | 0.67 | 0.16 | 1.04 | 2.18 | 1.00 | 2.30 | 1.00 | 1.00 | 0.95 |
| Gm3238 | 1.00 | 1.00 | 1.00 | 1.00 | 1.00 | 1.00 | 3.05 | 0.09 | 0.98 | 1.00 | 1.00 | 1.00 |
| Gm3402 | 1.00 | 1.00 | 1.00 | 1.00 | 1.00 | 1.00 | 1.00 | 1.00 | 1.00 | 1.00 | 1.00 | 1.00 |
| Gm3415 | 1.00 | 1.00 | 1.00 | 1.00 | 1.00 | 1.00 | 1.00 | 1.00 | 1.00 | 1.00 | 1.00 | 1.00 |
| Gm4559 | 1.00 | 1.00 | 1.00 | 1.00 | 1.00 | 1.00 | 2.43 | 0.17 | 0.87 | 1.00 | 1.00 | 1.00 |
| Gm4759 | 1.00 | 1.00 | 1.00 | 1.00 | 1.00 | 1.00 | 1.00 | 1.00 | 1.00 | 1.00 | 1.00 | 1.00 |
| Gm4836 | 1.00 | 1.00 | 1.00 | 1.00 | 1.00 | 1.00 | 1.00 | 1.00 | 1.00 | 1.00 | 1.00 | 1.00 |
| Gm5088 | 0.86 | 0.73 | 0.82 | 1.02 | 1.00 | 0.95 | 1.09 | 0.09 | 1.27 | 0.35 | 0.74 | 0.72 |
| Gm5538 | 1.00 | 1.00 | 1.00 | 1.00 | 1.00 | 1.00 | 1.64 | 0.02 | 1.54 | 1.00 | 1.00 | 1.00 |
| Gm5901 | 1.00 | 1.00 | 1.00 | 1.00 | 1.00 | 1.00 | 1.00 | 1.00 | 1.00 | 1.00 | 1.00 | 1.00 |
| Gm6194 | 1.94 | 2.12 | 1.77 | 1.00 | 1.00 | 1.03 | 1.45 | 0.05 | 1.41 | 0.43 | 1.10 | 1.08 |
| Gm6370 | 1.00 | 1.00 | 1.00 | 1.00 | 1.00 | 1.00 | 1.00 | 1.00 | 1.00 | 1.00 | 1.00 | 1.00 |
| Gm6402 | 0.79 | 0.80 | 0.97 | 0.98 | 0.99 | 1.07 | 0.96 | 0.50 | 1.12 | 1.07 | 0.83 | 0.97 |
| Gm6524 | 1.33 | 1.20 | 1.07 | 0.83 | 1.00 | 1.16 | 0.71 | 0.06 | 1.04 | 0.25 | 0.88 | 1.03 |
| Gm6548 | 0.97 | 0.93 | 1.04 | 1.04 | 0.38 | 0.96 | 0.89 | 0.03 | 0.82 | 0.14 | 0.88 | 0.93 |
| Gm6578 | 0.83 | 0.51 | 0.61 | 1.29 | 1.00 | 0.78 | 1.23 | 0.14 | 0.81 | 0.37 | 1.25 | 1.12 |
| Gm6623 | 1.00 | 1.00 | 1.00 | 1.08 | 1.00 | 0.99 | 0.88 | 0.37 | 0.84 | 0.60 | 1.08 | 0.90 |
| Gm6682 | 1.10 | 2.06 | 0.59 | 1.00 | 0.31 | 0.95 | 0.96 | 0.05 | 0.74 | 0.17 | 0.77 | 0.79 |
| Gm6710 | 0.85 | 0.71 | 1.09 | 0.45 | 1.00 | 0.36 | 0.56 | 0.36 | 0.67 | 1.00 | 0.68 | 0.88 |
| Gm7030 | 0.65 | 0.62 | 0.55 | 1.00 | 1.00 | 1.00 | 1.31 | 0.09 | 0.62 | 0.17 | 0.90 | 0.59 |
| Gm7073 | 1.00 | 1.00 | 1.00 | 1.00 | 1.00 | 1.00 | 1.00 | 1.00 | 1.00 | 1.00 | 1.00 | 1.00 |
| Gm7244 | 1.00 | 1.00 | 0.78 | 0.80 | 0.18 | 1.32 | 0.88 | 0.30 | 0.90 | 0.57 | 1.84 | 1.12 |
| Gm867 | 1.00 | 1.00 | 1.00 | 1.00 | 2.04 | 1.00 | 1.00 | 1.00 | 1.00 | 0.42 | 0.63 | 0.81 |
| Gm8898 | 0.38 | 0.31 | 0.88 | 0.36 | 0.09 | 0.40 | 0.24 | 0.23 | 0.31 | 1.00 | 0.68 | 0.76 |
| Gm94 | 1.00 | 1.00 | 1.00 | 1.00 | 1.00 | 1.00 | 0.74 | 0.08 | 0.62 | 1.00 | 1.00 | 1.00 |
| Gm9696 | 1.00 | 1.00 | 1.00 | 1.00 | 1.00 | 1.00 | 0.49 | 0.19 | 0.64 | 1.00 | 1.00 | 1.00 |
| Gmcl1 | 1.00 | 1.00 | 1.00 | 1.00 | 1.00 | 1.00 | 1.00 | 1.00 | 1.00 | 1.00 | 1.00 | 1.00 |
| Gna12 | 0.99 | 0.78 | 0.98 | 0.83 | 1.00 | 0.82 | 0.93 | 0.07 | 1.16 | 0.37 | 0.78 | 0.83 |
| Gnai1 | 0.57 | 0.44 | 0.72 | 1.00 | 0.92 | 1.01 | 0.54 | 0.17 | 0.60 | 1.00 | 1.00 | 1.00 |
| Gnai3 | 1.04 | 1.00 | 1.02 | 0.91 | 1.62 | 0.87 | 0.62 | 0.14 | 0.70 | 0.58 | 1.10 | 1.19 |
| Gng5 | 0.75 | 0.82 | 0.72 | 0.87 | 1.49 | 1.36 | 1.02 | 0.66 | 0.84 | 1.12 | 1.36 | 1.43 |
| Gnpda1 | 0.99 | 1.02 | 0.96 | 1.05 | 1.00 | 1.10 | 1.04 | 0.13 | 1.08 | 0.61 | 1.22 | 1.22 |
| Golga4 | 1.08 | 1.07 | 1.12 | 0.91 | 0.55 | 0.94 | 0.91 | 0.44 | 1.13 | 0.83 | 0.86 | 0.74 |
| Golga7 | 1.82 | 1.22 | 1.17 | 0.99 | 0.47 | 0.95 | 0.93 | 0.18 | 0.96 | 0.45 | 1.10 | 1.10 |
| Golim4 | 1.05 | 0.89 | 0.88 | 0.91 | 1.00 | 0.98 | 0.92 | 0.06 | 1.19 | 0.38 | 0.92 | 0.99 |
| Golph3l | 0.97 | 0.86 | 0.91 | 1.00 | 0.53 | 1.12 | 0.91 | 0.12 | 0.97 | 0.50 | 0.79 | 0.85 |
| Gpam | 1.31 | 1.23 | 1.64 | 0.83 | 1.00 | 0.84 | 0.71 | 0.19 | 1.01 | 1.00 | 0.54 | 0.59 |
| Gpatch2 | 1.00 | 1.25 | 0.91 | 0.81 | 1.00 | 0.91 | 0.98 | 0.18 | 1.03 | 0.52 | 0.86 | 1.04 |
| Gpatch2l | 0.77 | 0.63 | 0.86 | 0.91 | 1.15 | 0.84 | 0.87 | 0.16 | 1.13 | 0.60 | 0.86 | 0.99 |
| Gpatch8 | 1.12 | 1.09 | 1.33 | 0.89 | 0.72 | 0.94 | 0.86 | 0.14 | 1.21 | 0.35 | 0.76 | 0.79 |
| Gpd1 | 1.24 | 1.19 | 0.76 | 1.31 | 1.32 | 1.19 | 1.92 | 2.73 | 1.79 | 0.65 | 0.65 | 1.00 |
| Gpkow | 0.96 | 0.92 | 1.00 | 0.99 | 0.71 | 0.96 | 0.87 | 0.16 | 1.05 | 0.56 | 1.07 | 1.15 |
| Gpm6b | 1.00 | 1.00 | 1.00 | 0.97 | 0.87 | 0.97 | 0.85 | 0.25 | 1.14 | 1.00 | 1.00 | 1.00 |
| Gpn3 | 0.65 | 0.43 | 0.57 | 1.13 | 0.50 | 1.10 | 1.14 | 0.36 | 0.96 | 0.57 | 0.87 | 0.92 |
| Gpr116 | 1.10 | 1.00 | 1.29 | 0.72 | 1.32 | 0.90 | 1.17 | 0.38 | 1.63 | 1.00 | 1.00 | 1.00 |
| Gpr124 | 1.00 | 1.00 | 1.00 | 0.91 | 1.00 | 0.92 | 0.84 | 0.24 | 1.36 | 1.00 | 1.00 | 1.00 |
| Gpr135 | 1.00 | 1.00 | 1.00 | 1.04 | 1.00 | 0.94 | 1.00 | 1.00 | 1.05 | 1.00 | 1.00 | 1.00 |
| Gprasp1 | 0.89 | 1.00 | 1.00 | 0.93 | 1.10 | 0.97 | 0.84 | 0.50 | 0.73 | 0.91 | 0.96 | 1.03 |
| Gpt | 0.67 | 0.68 | 0.82 | 1.33 | 0.68 | 0.90 | 0.65 | 0.83 | 0.63 | 1.25 | 1.35 | 0.67 |
| Gpx5 | 1.00 | 1.00 | 1.00 | 1.00 | 1.00 | 1.00 | 1.00 | 1.00 | 1.00 | 1.00 | 1.00 | 1.00 |
| Gramd4 | 1.14 | 0.71 | 1.09 | 0.96 | 1.00 | 0.91 | 0.90 | 0.08 | 1.00 | 0.41 | 0.91 | 0.81 |
| Grem2 | 1.00 | 1.00 | 1.00 | 0.99 | 1.64 | 1.06 | 1.00 | 1.00 | 1.00 | 1.00 | 1.00 | 1.00 |
| Grhl2 | 0.84 | 1.04 | 1.10 | 1.00 | 1.00 | 1.00 | 0.85 | 0.13 | 0.87 | 1.00 | 1.00 | 1.00 |

Fig. 35- 45

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Grhl3 | 1.00 | 1.00 | 1.00 | 1.00 | 1.00 | 1.00 | 1.00 | 1.00 | 1.00 | 1.00 | 1.00 | 1.00 |
| Gsdmc2 | 1.00 | 1.00 | 1.00 | 1.00 | 1.00 | 1.00 | 1.00 | 1.00 | 1.00 | 1.00 | 1.00 | 1.00 |
| Gsta2 | 1.00 | 1.00 | 1.00 | 1.00 | 1.00 | 1.00 | 1.00 | 1.00 | 1.00 | 0.65 | 1.80 | 1.16 |
| Gstm3 | 1.00 | 1.00 | 1.00 | 1.00 | 1.00 | 1.00 | 1.00 | 1.00 | 1.00 | 1.00 | 1.00 | 1.00 |
| Gtf2ird1 | 0.96 | 1.00 | 1.14 | 0.48 | 0.26 | 0.78 | 0.97 | 1.08 | 1.00 | 0.73 | 0.82 | 1.09 |
| Gtpbp10 | 0.49 | 1.30 | 0.68 | 1.33 | 0.18 | 1.06 | 1.08 | 1.04 | 0.77 | 0.55 | 0.30 | 0.79 |
| Gucy1b3 | 0.72 | 1.21 | 1.00 | 1.57 | 0.17 | 1.08 | 0.96 | 0.95 | 0.98 | 0.17 | 0.20 | 0.89 |
| Gyk | 1.00 | 1.00 | 1.00 | 0.74 | 0.16 | 0.64 | 0.78 | 1.13 | 0.95 | 0.89 | 0.57 | 1.11 |
| H2-Aa | 1.26 | 0.60 | 2.16 | 0.32 | 1.63 | 0.83 | 0.46 | 0.52 | 1.65 | 0.48 | 0.63 | 0.55 |
| H2-Ab1 | 1.22 | 0.70 | 1.86 | 0.33 | 1.11 | 0.72 | 0.47 | 0.39 | 1.30 | 0.51 | 0.67 | 0.62 |
| H2-DMb2 | 1.00 | 1.00 | 1.32 | 1.00 | 1.00 | 1.00 | 1.00 | 1.00 | 1.15 | 0.25 | 0.07 | 0.63 |
| H2-Eb1 | 1.02 | 0.39 | 1.29 | 0.16 | 0.83 | 0.59 | 0.32 | 0.18 | 0.90 | 0.21 | 0.32 | 0.30 |
| H2-K1 | 1.69 | 1.12 | 2.03 | 0.91 | 3.53 | 1.41 | 1.79 | 1.64 | 2.19 | 1.47 | 1.57 | 1.38 |
| H2-M2 | 1.00 | 1.00 | 1.00 | 1.00 | 1.00 | 1.00 | 1.00 | 1.00 | 1.00 | 1.00 | 1.00 | 1.00 |
| H2-Q2 | 1.00 | 1.00 | 0.76 | 0.95 | 1.00 | 0.41 | 1.00 | 1.00 | 0.66 | 1.00 | 0.11 | 0.06 |
| H2-Q4 | 1.19 | 2.67 | 1.37 | 0.81 | 0.39 | 1.29 | 1.71 | 1.55 | 1.78 | 0.45 | 0.32 | 1.06 |
| H2-Q5 | 1.00 | 1.00 | 1.00 | 0.36 | 0.65 | 0.31 | 1.00 | 0.78 | 0.70 | 0.90 | 0.17 | 0.21 |
| H2-Q6 | 2.07 | 1.52 | 3.29 | 1.17 | 0.54 | 1.23 | 3.67 | 2.03 | 2.15 | 0.40 | 0.13 | 0.48 |
| H2-Q7 | 1.46 | 1.00 | 1.56 | 1.61 | 0.49 | 1.30 | 1.90 | 2.60 | 1.71 | 0.05 | 0.06 | 0.35 |
| H2-Q8 | 1.00 | 1.00 | 1.00 | 1.00 | 1.00 | 1.00 | 1.00 | 1.00 | 1.00 | 1.00 | 1.00 | 1.00 |
| H2-Q9 | 1.00 | 1.00 | 1.00 | 1.00 | 1.00 | 1.00 | 1.00 | 1.00 | 1.00 | 1.00 | 0.20 | 0.28 |
| H2-T24 | 1.08 | 1.00 | 2.87 | 2.79 | 0.28 | 1.70 | 1.48 | 2.34 | 1.81 | 1.28 | 0.07 | 1.77 |
| H2-T3 | 1.00 | 1.00 | 1.00 | 1.00 | 1.00 | 1.00 | 1.00 | 1.00 | 1.00 | 1.00 | 1.00 | 1.00 |
| Hace1 | 1.00 | 1.00 | 1.00 | 1.82 | 0.90 | 1.00 | 1.24 | 1.02 | 0.89 | 0.68 | 0.45 | 0.75 |
| Haus2 | 0.95 | 2.06 | 0.97 | 1.87 | 0.22 | 1.06 | 0.97 | 1.16 | 1.19 | 0.77 | 0.19 | 1.00 |
| Hcar1 | 1.00 | 1.00 | 1.00 | 0.36 | 0.41 | 0.24 | 1.00 | 1.00 | 1.00 | 1.00 | 1.00 | 1.00 |
| Hcar2 | 1.00 | 1.00 | 1.00 | 1.21 | 0.89 | 0.65 | 1.00 | 1.00 | 1.00 | 0.32 | 0.64 | 0.78 |
| Hccs | 0.79 | 1.12 | 0.87 | 0.88 | 0.20 | 0.80 | 0.60 | 0.80 | 0.79 | 0.30 | 0.29 | 0.81 |
| Hdac2 | 0.99 | 1.44 | 0.76 | 1.34 | 0.75 | 1.02 | 0.83 | 0.77 | 0.81 | 0.24 | 0.38 | 1.01 |
| Hdhd3 | 0.27 | 0.70 | 0.42 | 0.14 | 0.39 | 0.50 | 0.37 | 0.30 | 0.54 | 0.44 | 0.91 | 1.04 |
| Heca | 1.19 | 1.18 | 1.26 | 3.68 | 0.15 | 1.26 | 2.38 | 3.01 | 1.92 | 0.63 | 0.28 | 1.14 |
| Heg1 | 0.71 | 1.00 | 1.00 | 2.07 | 0.79 | 0.88 | 1.44 | 3.07 | 1.85 | 1.03 | 0.60 | 1.12 |
| Hemgn | 1.00 | 1.00 | 1.00 | 1.00 | 1.00 | 1.00 | 1.00 | 1.00 | 1.00 | 1.00 | 1.00 | 0.73 |
| Hephl1 | 1.00 | 1.00 | 1.00 | 1.00 | 1.00 | 1.00 | 1.00 | 1.00 | 1.00 | 1.00 | 1.00 | 1.00 |
| Herc3 | 0.80 | 1.23 | 0.87 | 0.67 | 0.13 | 0.62 | 0.96 | 1.11 | 1.11 | 1.00 | 0.58 | 0.98 |
| Hfe | 1.10 | 1.15 | 0.74 | 0.64 | 0.41 | 0.74 | 1.09 | 0.94 | 0.96 | 0.27 | 0.40 | 0.86 |
| Hibadh | 0.91 | 1.41 | 0.84 | 1.03 | 0.52 | 1.01 | 0.94 | 0.98 | 0.83 | 0.40 | 0.54 | 1.11 |
| Hipk1 | 1.93 | 3.54 | 1.82 | 2.75 | 0.75 | 1.53 | 1.70 | 2.20 | 1.62 | 0.55 | 0.48 | 1.15 |
| Hist1h1d | 0.94 | 1.81 | 0.98 | 1.21 | 1.00 | 1.55 | 3.59 | 4.59 | 3.45 | 1.00 | 1.00 | 1.58 |
| Hist1h1e | 1.33 | 2.96 | 1.39 | 2.96 | 0.59 | 1.22 | 3.70 | 4.14 | 2.56 | 1.16 | 0.87 | 2.03 |
| Hist1h2af | 1.48 | 1.00 | 2.21 | 1.00 | 1.00 | 1.00 | 1.20 | 1.87 | 1.05 | 1.00 | 1.00 | 1.00 |
| Hist1h2ag | 1.00 | 1.00 | 1.00 | 0.59 | 1.00 | 1.00 | 1.00 | 1.00 | 1.00 | 1.00 | 1.00 | 1.00 |
| Hist1h2ap | 1.00 | 0.70 | 1.00 | 0.30 | 0.90 | 0.68 | 1.12 | 1.95 | 1.00 | 1.00 | 2.29 | 0.61 |
| Hist1h2bk | 1.35 | 3.57 | 1.17 | 0.86 | 0.33 | 1.21 | 2.21 | 1.50 | 1.27 | 0.28 | 0.46 | 2.25 |
| Hist1h3c | 1.00 | 1.00 | 1.00 | 1.00 | 1.00 | 1.00 | 1.00 | 1.00 | 1.00 | 1.00 | 1.00 | 1.00 |
| Hist1h3e | 1.00 | 1.00 | 1.00 | 1.00 | 1.00 | 2.32 | 1.00 | 1.11 | 1.30 | 1.00 | 1.00 | 1.00 |
| Hist1h3i | 0.98 | 1.84 | 2.08 | 1.00 | 1.00 | 1.00 | 1.00 | 1.00 | 1.00 | 1.00 | 1.00 | 1.00 |
| Hist1h4d | 1.00 | 0.97 | 1.00 | 1.00 | 3.44 | 1.00 | 1.60 | 1.12 | 1.00 | 1.81 | 1.41 | 1.00 |
| Hist2h2bb | 1.00 | 1.00 | 1.00 | 1.00 | 1.00 | 1.00 | 1.10 | 3.80 | 1.94 | 1.00 | 1.00 | 1.02 |
| Hist2h3c2 | 2.50 | 1.49 | 0.95 | 0.24 | 0.17 | 0.95 | 2.59 | 2.04 | 1.28 | 0.71 | 0.34 | 1.35 |
| Hist2h4 | 1.00 | 1.00 | 0.98 | 1.00 | 2.41 | 1.00 | 1.00 | 1.00 | 1.00 | 1.00 | 1.00 | 1.00 |
| Hist3h2a | 1.26 | 1.92 | 0.81 | 0.83 | 0.10 | 1.06 | 1.87 | 1.70 | 0.76 | 0.11 | 0.12 | 0.98 |
| Hmgcs1 | 0.85 | 1.22 | 0.81 | 0.73 | 0.19 | 0.69 | 0.83 | 1.00 | 0.90 | 0.84 | 0.85 | 1.33 |
| Hn1l | 0.68 | 0.94 | 0.89 | 1.97 | 0.67 | 1.03 | 1.06 | 0.95 | 1.35 | 1.29 | 0.55 | 1.06 |
| Hnf4aos | 1.00 | 1.00 | 1.00 | 1.00 | 1.00 | 1.00 | 1.00 | 1.00 | 1.00 | 1.00 | 1.00 | 1.00 |
| Hnrnph1 | 0.95 | 1.43 | 1.01 | 1.14 | 0.48 | 0.88 | 0.83 | 0.85 | 0.89 | 0.45 | 0.37 | 0.92 |
| Hnrnph2 | 0.98 | 2.14 | 1.04 | 1.71 | 0.24 | 1.09 | 0.95 | 1.06 | 1.10 | 0.24 | 0.23 | 1.06 |
| Hnrnpul1 | 0.83 | 1.69 | 1.03 | 1.81 | 0.04 | 1.10 | 1.25 | 1.31 | 1.20 | 0.72 | 0.10 | 0.97 |
| Hook1 | 0.57 | 1.00 | 1.02 | 1.33 | 0.46 | 0.79 | 0.97 | 1.43 | 1.23 | 1.00 | 1.00 | 0.93 |
| Hoxa4 | 0.61 | 1.66 | 0.92 | 0.39 | 0.22 | 0.51 | 1.00 | 1.00 | 1.00 | 0.30 | 0.18 | 0.82 |
| Hoxc13 | 1.00 | 1.00 | 1.00 | 1.00 | 1.00 | 1.00 | 1.00 | 1.00 | 1.00 | 1.00 | 1.00 | 1.00 |
| Hpgds | 1.00 | 1.00 | 1.00 | 1.00 | 1.00 | 1.00 | 0.88 | 0.68 | 0.94 | 1.00 | 1.00 | 1.23 |
| Hps3 | 0.95 | 1.21 | 1.11 | 1.92 | 0.60 | 1.20 | 1.03 | 1.26 | 0.90 | 0.58 | 0.58 | 0.89 |
| Hrc | 0.62 | 1.43 | 0.71 | 0.80 | 0.32 | 0.67 | 1.00 | 1.16 | 0.87 | 0.69 | 0.35 | 0.78 |

Fig. 35- 46

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Grhl3 | 1.00 | 1.00 | 1.00 | 1.00 | 1.00 | 1.00 | 1.00 | 1.00 | 1.00 | 1.00 | 1.00 | 1.00 |
| Gsdmc2 | 1.00 | 1.00 | 1.00 | 0.62 | 1.00 | 0.82 | 1.00 | 1.00 | 1.00 | 0.87 | 0.51 | 0.61 |
| Gsta2 | 1.01 | 1.00 | 1.00 | 0.56 | 0.42 | 0.47 | 0.38 | 0.26 | 0.18 | 1.28 | 1.44 | 0.57 |
| Gstm3 | 1.00 | 1.00 | 1.00 | 1.00 | 1.00 | 1.00 | 0.46 | 0.23 | 0.70 | 0.28 | 0.39 | 0.29 |
| Gtf2ird1 | 0.65 | 0.63 | 0.81 | 0.98 | 1.00 | 0.98 | 1.56 | 1.00 | 1.56 | 1.04 | 0.75 | 0.98 |
| Gtpbp10 | 1.00 | 1.02 | 0.86 | 0.89 | 0.93 | 0.81 | 1.05 | 0.92 | 1.08 | 0.97 | 0.76 | 1.11 |
| Gucy1b3 | 2.49 | 1.67 | 1.47 | 0.86 | 1.00 | 0.75 | 1.17 | 1.00 | 1.30 | 0.94 | 0.58 | 0.91 |
| Gyk | 0.93 | 0.74 | 0.65 | 0.91 | 1.46 | 0.84 | 1.06 | 0.51 | 1.08 | 0.70 | 0.58 | 0.82 |
| H2-Aa | 1.14 | 1.15 | 1.13 | 0.59 | 0.48 | 0.67 | 0.31 | 0.18 | 0.52 | 0.75 | 0.86 | 0.70 |
| H2-Ab1 | 1.14 | 1.16 | 1.13 | 0.51 | 0.52 | 0.74 | 0.23 | 0.08 | 0.54 | 0.75 | 0.88 | 0.71 |
| H2-DMb2 | 0.82 | 0.85 | 1.00 | 0.73 | 1.00 | 0.73 | 1.00 | 1.00 | 1.00 | 0.75 | 0.60 | 0.60 |
| H2-Eb1 | 0.79 | 0.83 | 0.78 | 0.33 | 0.28 | 0.44 | 0.33 | 0.18 | 0.41 | 0.51 | 0.55 | 0.50 |
| H2-K1 | 1.12 | 1.21 | 1.15 | 0.55 | 0.41 | 0.61 | 1.73 | 1.73 | 1.97 | 1.47 | 1.61 | 1.30 |
| H2-M2 | 0.74 | 0.50 | 1.00 | 1.00 | 1.00 | 1.00 | 1.00 | 1.00 | 1.00 | 0.93 | 1.00 | 0.68 |
| H2-Q2 | 0.02 | 0.02 | 0.01 | 0.96 | 1.00 | 0.63 | 0.13 | 1.00 | 0.13 | 0.05 | 0.07 | 0.04 |
| H2-Q4 | 1.69 | 1.71 | 1.57 | 0.99 | 1.45 | 0.86 | 1.01 | 0.77 | 1.08 | 1.04 | 0.86 | 0.88 |
| H2-Q5 | 0.14 | 0.12 | 0.19 | 0.63 | 1.00 | 0.36 | 0.49 | 1.00 | 0.76 | 0.60 | 0.22 | 0.32 |
| H2-Q6 | 0.28 | 0.28 | 0.26 | 1.00 | 1.00 | 0.58 | 2.32 | 1.00 | 2.54 | 1.33 | 0.85 | 0.81 |
| H2-Q7 | 0.27 | 0.26 | 0.20 | 0.77 | 0.19 | 0.60 | 1.49 | 0.15 | 1.63 | 1.06 | 0.72 | 0.73 |
| H2-Q8 | 1.00 | 0.13 | 0.43 | 1.00 | 1.00 | 1.00 | 1.00 | 1.00 | 1.00 | 1.00 | 1.00 | 1.00 |
| H2-Q9 | 0.11 | 0.11 | 0.07 | 0.79 | 1.00 | 1.00 | 1.00 | 1.00 | 0.93 | 1.00 | 0.29 | 0.52 |
| H2-T24 | 1.28 | 0.91 | 1.97 | 1.84 | 1.00 | 2.91 | 1.11 | 1.00 | 2.36 | 3.68 | 1.30 | 2.66 |
| H2-T3 | 0.00 | 0.00 | 0.00 | 1.00 | 1.00 | 1.00 | 1.00 | 1.00 | 1.00 | 0.79 | 0.73 | 0.92 |
| Hace1 | 0.82 | 0.84 | 0.89 | 0.85 | 1.00 | 0.94 | 1.00 | 1.00 | 1.00 | 1.03 | 0.94 | 0.90 |
| Haus2 | 0.55 | 0.55 | 0.74 | 0.93 | 1.00 | 0.75 | 0.94 | 1.00 | 1.04 | 1.10 | 0.71 | 0.99 |
| Hcar1 | 1.00 | 1.00 | 0.61 | 0.56 | 1.00 | 0.83 | 1.00 | 1.00 | 1.00 | 0.62 | 0.54 | 0.89 |
| Hcar2 | 0.83 | 0.72 | 0.63 | 1.00 | 1.00 | 1.00 | 1.00 | 1.00 | 1.00 | 0.87 | 0.88 | 0.80 |
| Hccs | 0.67 | 0.74 | 0.81 | 0.81 | 3.04 | 0.91 | 0.87 | 0.66 | 0.90 | 1.04 | 0.87 | 1.07 |
| Hdac2 | 0.80 | 0.78 | 0.80 | 0.98 | 1.75 | 0.93 | 0.97 | 0.56 | 1.01 | 0.84 | 1.02 | 1.01 |
| Hdhd3 | 1.07 | 0.77 | 0.70 | 0.60 | 0.47 | 0.68 | 0.31 | 0.18 | 0.43 | 0.84 | 0.98 | 0.87 |
| Heca | 0.80 | 0.58 | 1.25 | 2.29 | 1.00 | 1.64 | 2.06 | 1.00 | 1.93 | 1.33 | 0.65 | 1.16 |
| Heg1 | 0.30 | 0.26 | 0.72 | 1.59 | 1.00 | 1.55 | 0.90 | 1.00 | 1.39 | 1.08 | 0.63 | 0.77 |
| Hemgn | 0.33 | 0.69 | 0.43 | 1.00 | 1.00 | 1.00 | 1.00 | 1.00 | 1.00 | 1.00 | 1.00 | 1.00 |
| Hephl1 | 1.00 | 1.00 | 1.00 | 1.00 | 1.00 | 1.00 | 1.00 | 1.00 | 1.00 | 1.00 | 1.00 | 1.00 |
| Herc3 | 1.18 | 1.08 | 1.30 | 0.77 | 0.71 | 0.83 | 0.59 | 1.00 | 0.73 | 1.04 | 0.74 | 0.80 |
| Hfe | 1.64 | 1.82 | 1.74 | 1.09 | 2.42 | 0.83 | 1.06 | 0.31 | 1.13 | 0.85 | 0.88 | 0.84 |
| Hibadh | 0.85 | 0.90 | 0.79 | 0.95 | 2.01 | 0.94 | 0.78 | 0.21 | 0.77 | 1.02 | 1.05 | 1.00 |
| Hipk1 | 0.75 | 0.68 | 0.90 | 1.63 | 2.39 | 1.36 | 1.06 | 0.57 | 1.05 | 1.33 | 0.95 | 1.16 |
| Hist1h1d | 1.90 | 3.36 | 1.54 | 1.64 | 0.88 | 2.02 | 1.51 | 1.00 | 1.00 | 1.54 | 0.81 | 0.86 |
| Hist1h1e | 2.74 | 2.73 | 1.80 | 2.15 | 0.79 | 1.79 | 3.80 | 3.00 | 1.79 | 1.41 | 0.84 | 1.35 |
| Hist1h2af | 0.42 | 0.77 | 0.44 | 1.00 | 1.00 | 1.00 | 1.00 | 1.00 | 1.00 | 1.00 | 1.00 | 0.77 |
| Hist1h2ag | 0.20 | 0.27 | 0.12 | 1.00 | 1.00 | 1.00 | 1.00 | 1.00 | 1.00 | 1.00 | 1.25 | 1.00 |
| Hist1h2ap | 0.36 | 0.38 | 0.52 | 1.00 | 1.00 | 1.00 | 1.00 | 1.00 | 1.00 | 0.94 | 1.07 | 0.73 |
| Hist1h2bk | 1.72 | 1.48 | 0.87 | 1.37 | 3.56 | 1.19 | 1.76 | 0.34 | 1.32 | 1.70 | 1.61 | 1.33 |
| Hist1h3c | 0.56 | 0.36 | 0.14 | 1.10 | 1.00 | 1.00 | 1.00 | 1.00 | 1.00 | 1.00 | 1.00 | 1.00 |
| Hist1h3e | 0.87 | 1.00 | 1.24 | 1.00 | 1.00 | 1.00 | 1.00 | 3.59 | 1.00 | 1.00 | 1.00 | 1.00 |
| Hist1h3i | 0.63 | 0.27 | 0.19 | 1.00 | 1.00 | 1.00 | 1.00 | 1.00 | 1.00 | 1.00 | 1.00 | 1.00 |
| Hist1h4d | 1.05 | 1.17 | 0.66 | 1.00 | 1.48 | 1.00 | 1.00 | 1.42 | 1.00 | 1.00 | 1.27 | 1.14 |
| Hist2h2bb | 0.45 | 0.43 | 0.28 | 1.00 | 1.00 | 1.00 | 1.00 | 1.00 | 1.00 | 1.00 | 1.00 | 0.69 |
| Hist2h3c2 | 1.18 | 1.39 | 1.44 | 3.06 | 1.00 | 1.77 | 3.03 | 1.00 | 2.87 | 1.73 | 0.43 | 1.81 |
| Hist2h4 | 0.51 | 0.90 | 0.68 | 1.00 | 1.00 | 1.00 | 1.00 | 1.00 | 1.00 | 1.00 | 1.00 | 0.72 |
| Hist3h2a | 0.94 | 0.86 | 0.84 | 1.11 | 1.05 | 1.09 | 1.04 | 1.00 | 0.71 | 0.94 | 0.79 | 0.79 |
| Hmgcs1 | 0.83 | 0.73 | 0.81 | 0.90 | 1.07 | 0.85 | 0.64 | 0.57 | 1.08 | 1.46 | 1.05 | 1.15 |
| Hn1l | 0.52 | 0.51 | 0.78 | 1.18 | 1.31 | 1.07 | 0.57 | 0.97 | 1.08 | 1.07 | 0.72 | 1.01 |
| Hnf4aos | 1.00 | 1.00 | 1.00 | 0.67 | 0.41 | 0.64 | 0.29 | 0.14 | 0.45 | 1.00 | 1.00 | 1.00 |
| Hnrnph1 | 0.81 | 0.88 | 0.79 | 0.92 | 1.38 | 0.89 | 1.19 | 0.71 | 1.11 | 0.96 | 0.98 | 1.02 |
| Hnrnph2 | 0.82 | 0.79 | 0.89 | 1.02 | 1.80 | 1.04 | 1.03 | 0.53 | 1.05 | 1.00 | 0.75 | 1.06 |
| Hnrnpul1 | 0.62 | 0.60 | 0.93 | 1.01 | 1.00 | 1.11 | 0.96 | 1.00 | 1.03 | 1.09 | 0.54 | 0.99 |
| Hook1 | 0.53 | 0.41 | 0.92 | 1.14 | 0.74 | 1.01 | 0.89 | 1.00 | 0.86 | 1.07 | 0.34 | 0.91 |
| Hoxa4 | 1.66 | 1.09 | 0.83 | 0.71 | 1.00 | 0.99 | 1.00 | 1.00 | 1.00 | 1.77 | 1.38 | 1.27 |
| Hoxc13 | 1.00 | 1.00 | 1.00 | 1.00 | 1.00 | 1.00 | 1.00 | 1.00 | 1.00 | 1.00 | 1.00 | 1.00 |
| Hpgds | 1.44 | 0.98 | 1.10 | 1.00 | 1.00 | 1.00 | 1.00 | 1.00 | 1.00 | 0.23 | 0.16 | 0.21 |
| Hps3 | 0.86 | 0.92 | 1.04 | 1.13 | 1.00 | 1.05 | 0.79 | 1.00 | 1.07 | 1.28 | 0.91 | 0.99 |
| Hrc | 1.00 | 1.00 | 1.00 | 1.00 | 1.00 | 1.00 | 1.00 | 1.00 | 1.00 | 0.88 | 0.64 | 0.69 |

Fig. 35- 47

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Grhl3 | 0.86 | 0.87 | 0.98 | 1.00 | 1.00 | 1.00 | 1.00 | 1.00 | 1.00 | 1.00 | 1.00 | 1.00 |
| Gsdmc2 | 0.33 | 0.22 | 0.20 | 1.00 | 1.00 | 1.00 | 1.00 | 1.09 | 1.00 | 1.00 | 1.00 | 1.00 |
| Gsta2 | 0.53 | 0.67 | 0.56 | 1.00 | 1.00 | 1.00 | 1.34 | 1.28 | 1.73 | 1.00 | 1.00 | 1.00 |
| Gstm3 | 0.15 | 0.11 | 0.20 | 1.00 | 1.00 | 1.00 | 1.00 | 1.00 | 1.00 | 1.00 | 1.00 | 1.00 |
| Gtf2ird1 | 1.08 | 1.14 | 0.93 | 1.41 | 1.00 | 1.80 | 1.00 | 1.00 | 0.75 | 0.62 | 0.78 | 1.23 |
| Gtpbp10 | 0.97 | 0.86 | 0.98 | 0.84 | 1.00 | 0.92 | 1.00 | 0.86 | 0.90 | 1.04 | 0.81 | 0.81 |
| Gucy1b3 | 0.91 | 0.98 | 1.06 | 0.97 | 1.00 | 1.08 | 1.00 | 1.00 | 1.00 | 1.21 | 1.27 | 0.96 |
| Gyk | 0.52 | 0.44 | 0.48 | 1.01 | 1.00 | 1.48 | 1.00 | 1.00 | 1.00 | 1.37 | 1.24 | 0.81 |
| H2-Aa | 1.80 | 0.80 | 1.81 | 0.64 | 1.11 | 0.66 | 0.53 | 0.70 | 1.41 | 0.89 | 0.86 | 0.73 |
| H2-Ab1 | 1.69 | 0.79 | 2.13 | 0.63 | 0.87 | 0.71 | 0.07 | 0.05 | 0.13 | 0.75 | 0.74 | 0.73 |
| H2-DMb2 | 1.54 | 0.88 | 1.10 | 0.65 | 1.00 | 0.98 | 0.98 | 1.00 | 0.61 | 0.74 | 0.57 | 0.63 |
| H2-Eb1 | 0.93 | 0.52 | 1.05 | 0.36 | 0.85 | 0.38 | 0.81 | 0.72 | 1.38 | 0.55 | 0.61 | 0.57 |
| H2-K1 | 1.25 | 1.36 | 1.13 | 1.07 | 2.31 | 1.18 | 0.43 | 0.42 | 0.52 | 1.17 | 1.16 | 0.98 |
| H2-M2 | 1.00 | 1.00 | 1.00 | 1.00 | 1.00 | 1.00 | 1.00 | 1.00 | 1.00 | 0.55 | 0.22 | 0.72 |
| H2-Q2 | 0.31 | 0.28 | 0.22 | 0.16 | 1.00 | 0.05 | 0.22 | 1.00 | 0.17 | 0.06 | 0.09 | 0.05 |
| H2-Q4 | 1.11 | 1.19 | 0.87 | 0.76 | 0.15 | 0.72 | 1.02 | 1.22 | 1.17 | 1.13 | 0.95 | 0.87 |
| H2-Q5 | 0.31 | 0.36 | 0.27 | 0.22 | 1.00 | 0.15 | 1.00 | 1.00 | 1.00 | 0.21 | 0.20 | 0.21 |
| H2-Q6 | 2.39 | 1.39 | 1.75 | 1.07 | 0.37 | 0.88 | 1.01 | 1.00 | 0.75 | 0.21 | 0.16 | 0.14 |
| H2-Q7 | 2.50 | 1.55 | 1.34 | 0.77 | 0.69 | 0.67 | 1.00 | 0.59 | 1.07 | 0.17 | 0.15 | 0.12 |
| H2-Q8 | 1.00 | 1.00 | 1.00 | 0.55 | 1.00 | 0.49 | 1.00 | 1.00 | 1.00 | 0.18 | 0.15 | 0.11 |
| H2-Q9 | 1.00 | 1.00 | 1.00 | 0.49 | 1.00 | 1.00 | 1.00 | 1.00 | 1.00 | 0.07 | 0.03 | 0.02 |
| H2-T24 | 1.93 | 2.69 | 2.27 | 1.72 | 0.76 | 2.04 | 1.00 | 1.00 | 1.00 | 1.44 | 0.77 | 1.30 |
| H2-T3 | 1.00 | 1.00 | 1.00 | 1.00 | 1.00 | 1.00 | 1.00 | 1.00 | 1.00 | 1.00 | 1.00 | 0.83 |
| Hace1 | 0.83 | 0.82 | 1.17 | 0.75 | 1.00 | 0.77 | 0.92 | 0.88 | 1.03 | 0.69 | 0.87 | 0.73 |
| Haus2 | 0.82 | 0.81 | 1.04 | 1.03 | 1.00 | 1.01 | 0.98 | 0.84 | 1.01 | 1.02 | 0.82 | 0.95 |
| Hcar1 | 0.56 | 0.62 | 0.86 | 0.17 | 0.13 | 0.25 | 1.00 | 1.00 | 1.00 | 0.64 | 0.92 | 0.78 |
| Hcar2 | 0.81 | 1.12 | 1.26 | 0.16 | 0.27 | 0.46 | 1.00 | 1.00 | 1.00 | 0.45 | 0.38 | 0.64 |
| Hccs | 0.99 | 0.83 | 0.84 | 0.80 | 1.00 | 0.99 | 1.05 | 1.00 | 0.82 | 1.15 | 0.90 | 1.00 |
| Hdac2 | 1.00 | 0.84 | 0.90 | 0.92 | 0.41 | 1.02 | 1.09 | 0.23 | 0.90 | 0.95 | 0.91 | 0.94 |
| Hdhd3 | 0.63 | 0.77 | 0.71 | 0.36 | 0.13 | 0.84 | 0.61 | 0.57 | 0.81 | 0.97 | 0.76 | 0.76 |
| Heca | 1.48 | 1.60 | 1.11 | 1.52 | 0.18 | 0.76 | 1.19 | 1.41 | 1.24 | 1.17 | 0.52 | 1.24 |
| Heg1 | 1.28 | 1.55 | 0.77 | 0.83 | 0.11 | 0.26 | 1.60 | 1.00 | 1.11 | 0.79 | 0.34 | 1.23 |
| Hemgn | 1.00 | 1.00 | 1.00 | 1.00 | 1.00 | 1.00 | 0.84 | 0.61 | 1.00 | 0.38 | 0.32 | 0.19 |
| Hephl1 | 1.00 | 1.00 | 1.00 | 1.00 | 1.00 | 1.00 | 1.00 | 1.00 | 1.00 | 1.00 | 1.00 | 1.00 |
| Herc3 | 1.03 | 1.16 | 1.26 | 0.58 | 1.00 | 0.64 | 1.00 | 1.00 | 1.00 | 1.32 | 1.09 | 1.33 |
| Hfe | 1.23 | 1.56 | 1.24 | 0.87 | 0.38 | 0.67 | 0.84 | 0.55 | 1.01 | 0.95 | 1.14 | 1.08 |
| Hibadh | 1.18 | 1.21 | 1.07 | 0.70 | 0.34 | 0.99 | 0.89 | 0.17 | 0.87 | 1.02 | 1.04 | 1.01 |
| Hipk1 | 1.28 | 1.26 | 0.98 | 1.71 | 0.25 | 1.16 | 1.07 | 0.74 | 1.05 | 1.22 | 0.85 | 1.35 |
| Hist1h1d | 1.28 | 1.72 | 0.96 | 2.93 | 0.17 | 1.28 | 1.00 | 1.33 | 1.00 | 1.25 | 0.83 | 1.11 |
| Hist1h1e | 1.25 | 3.14 | 0.84 | 1.30 | 0.09 | 0.66 | 1.00 | 1.00 | 1.00 | 0.87 | 1.27 | 0.64 |
| Hist1h2af | 1.00 | 1.00 | 1.13 | 1.00 | 0.19 | 1.00 | 1.00 | 1.02 | 1.13 | 0.53 | 1.00 | 1.00 |
| Hist1h2ag | 1.00 | 1.00 | 1.00 | 1.00 | 0.51 | 1.00 | 0.50 | 1.50 | 2.02 | 0.95 | 1.00 | 0.69 |
| Hist1h2ap | 1.00 | 1.00 | 0.66 | 1.00 | 0.72 | 0.46 | 0.55 | 1.15 | 0.74 | 1.23 | 1.00 | 0.50 |
| Hist1h2bk | 1.47 | 1.53 | 1.17 | 0.96 | 0.17 | 0.71 | 1.22 | 0.20 | 1.30 | 1.25 | 1.54 | 1.08 |
| Hist1h3c | 1.00 | 1.00 | 1.00 | 1.00 | 1.00 | 1.00 | 1.00 | 1.00 | 1.18 | 0.97 | 1.00 | 1.00 |
| Hist1h3e | 1.00 | 1.00 | 1.00 | 1.00 | 0.08 | 0.61 | 1.00 | 1.00 | 1.00 | 1.00 | 1.00 | 1.00 |
| Hist1h3i | 1.00 | 1.00 | 1.00 | 1.00 | 0.27 | 1.00 | 0.66 | 0.27 | 0.95 | 0.56 | 1.08 | 1.24 |
| Hist1h4d | 1.00 | 1.00 | 1.00 | 1.00 | 0.04 | 0.91 | 1.00 | 1.00 | 1.00 | 0.62 | 1.00 | 1.00 |
| Hist2h2bb | 1.16 | 0.63 | 1.37 | 1.61 | 0.11 | 1.00 | 2.02 | 1.00 | 0.87 | 1.30 | 0.97 | 1.53 |
| Hist2h3c2 | 0.62 | 1.88 | 1.26 | 1.79 | 0.27 | 1.40 | 0.54 | 0.91 | 0.97 | 0.92 | 0.69 | 1.04 |
| Hist2h4 | 0.73 | 1.00 | 1.54 | 1.00 | 0.19 | 1.00 | 1.00 | 1.00 | 1.00 | 1.00 | 0.80 | 1.00 |
| Hist3h2a | 0.90 | 0.95 | 1.03 | 0.81 | 0.24 | 0.80 | 1.05 | 2.19 | 1.22 | 0.83 | 1.01 | 0.98 |
| Hmgcs1 | 0.91 | 0.97 | 0.83 | 0.83 | 0.28 | 0.89 | 0.95 | 1.16 | 1.00 | 0.99 | 1.21 | 1.03 |
| Hn1l | 0.85 | 0.64 | 0.75 | 0.76 | 0.57 | 0.65 | 1.05 | 0.69 | 1.02 | 1.02 | 0.68 | 1.07 |
| Hnf4aos | 1.00 | 1.00 | 1.00 | 1.00 | 1.00 | 1.00 | 1.00 | 1.00 | 1.00 | 1.00 | 1.00 | 1.00 |
| Hnrnph1 | 0.91 | 0.79 | 0.99 | 1.04 | 0.62 | 1.10 | 0.96 | 0.63 | 0.95 | 1.07 | 0.89 | 1.01 |
| Hnrnph2 | 1.13 | 1.00 | 0.96 | 1.23 | 0.15 | 1.05 | 1.15 | 0.86 | 1.02 | 1.06 | 0.82 | 0.92 |
| Hnrnpul1 | 0.90 | 0.97 | 0.85 | 1.26 | 0.13 | 1.19 | 1.12 | 2.81 | 1.07 | 0.91 | 0.65 | 0.96 |
| Hook1 | 0.94 | 0.80 | 0.88 | 1.43 | 1.00 | 0.95 | 0.95 | 2.55 | 1.00 | 1.02 | 0.88 | 1.08 |
| Hoxa4 | 0.69 | 1.07 | 1.11 | 0.83 | 1.00 | 0.84 | 1.06 | 0.32 | 1.06 | 1.03 | 0.91 | 1.12 |
| Hoxc13 | 1.00 | 1.00 | 1.00 | 1.00 | 1.00 | 1.00 | 1.00 | 1.00 | 1.00 | 1.00 | 1.00 | 1.00 |
| Hpgds | 0.76 | 0.54 | 1.18 | 0.72 | 0.44 | 0.47 | 1.00 | 1.00 | 1.00 | 0.78 | 0.64 | 0.71 |
| Hps3 | 1.07 | 1.15 | 1.11 | 0.77 | 0.80 | 0.92 | 0.95 | 1.00 | 0.96 | 1.00 | 0.82 | 0.99 |
| Hrc | 1.87 | 1.13 | 2.12 | 1.00 | 1.00 | 1.00 | 1.00 | 1.00 | 1.00 | 1.00 | 1.00 | 1.00 |

Fig. 35- 48

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Grhl3 | 1.00 | 1.00 | 1.00 | 1.00 | 1.00 | 1.00 | 0.68 | 0.06 | 0.60 | 1.00 | 1.00 | 1.00 |
| Gsdmc2 | 1.00 | 1.00 | 1.00 | 1.00 | 1.00 | 1.00 | 1.00 | 1.00 | 1.00 | 1.00 | 1.00 | 1.00 |
| Gsta2 | 1.00 | 1.00 | 1.00 | 1.00 | 1.00 | 1.00 | 0.88 | 2.80 | 0.43 | 1.00 | 1.00 | 1.00 |
| Gstm3 | 1.00 | 1.00 | 1.00 | 1.00 | 1.00 | 1.00 | 1.00 | 1.00 | 1.00 | 1.00 | 1.00 | 1.00 |
| Gtf2ird1 | 1.00 | 1.00 | 1.00 | 1.00 | 1.00 | 1.05 | 0.79 | 0.12 | 0.93 | 1.00 | 1.00 | 1.06 |
| Gtpbp10 | 0.77 | 1.00 | 1.00 | 0.92 | 1.00 | 1.21 | 1.02 | 0.14 | 1.16 | 0.44 | 0.81 | 0.76 |
| Gucy1b3 | 1.00 | 1.00 | 1.00 | 0.96 | 1.53 | 0.97 | 1.81 | 0.63 | 2.55 | 1.00 | 1.00 | 1.15 |
| Gyk | 1.00 | 1.00 | 1.00 | 0.98 | 1.08 | 1.08 | 0.76 | 0.28 | 1.09 | 0.71 | 0.86 | 0.97 |
| H2-Aa | 0.39 | 1.94 | 0.74 | 0.69 | 0.18 | 0.60 | 0.62 | 1.13 | 0.61 | 1.06 | 1.19 | 0.97 |
| H2-Ab1 | 0.53 | 1.27 | 0.85 | 1.00 | 1.12 | 0.78 | 0.57 | 1.03 | 0.67 | 1.05 | 0.84 | 0.85 |
| H2-DMb2 | 0.86 | 1.00 | 0.61 | 1.00 | 1.00 | 1.00 | 0.52 | 0.07 | 0.66 | 0.14 | 0.71 | 0.69 |
| H2-Eb1 | 0.32 | 0.84 | 0.57 | 0.99 | 0.52 | 0.45 | 0.53 | 0.59 | 0.51 | 0.58 | 0.61 | 0.51 |
| H2-K1 | 0.89 | 1.00 | 0.87 | 1.09 | 0.19 | 1.25 | 1.56 | 2.44 | 1.12 | 1.29 | 1.43 | 1.24 |
| H2-M2 | 1.00 | 1.00 | 1.00 | 1.00 | 1.00 | 1.00 | 0.64 | 0.14 | 0.63 | 1.00 | 1.00 | 1.00 |
| H2-Q2 | 0.83 | 1.00 | 0.49 | 1.00 | 1.00 | 1.00 | 0.19 | 0.22 | 0.08 | 0.23 | 0.08 | 0.08 |
| H2-Q4 | 0.84 | 0.91 | 0.77 | 0.87 | 0.39 | 0.90 | 1.31 | 0.21 | 0.89 | 0.35 | 1.07 | 0.80 |
| H2-Q5 | 1.00 | 1.00 | 1.00 | 1.00 | 1.00 | 1.00 | 0.33 | 0.23 | 0.29 | 0.48 | 0.20 | 0.18 |
| H2-Q6 | 1.09 | 1.00 | 0.52 | 1.00 | 1.00 | 1.00 | 1.53 | 0.14 | 1.03 | 0.20 | 0.49 | 0.36 |
| H2-Q7 | 1.00 | 1.00 | 0.25 | 1.00 | 1.00 | 1.00 | 1.58 | 0.17 | 0.96 | 0.09 | 0.52 | 0.27 |
| H2-Q8 | 1.00 | 1.00 | 1.00 | 1.00 | 1.00 | 1.00 | 1.00 | 1.00 | 1.00 | 1.00 | 1.00 | 0.41 |
| H2-Q9 | 1.00 | 1.00 | 1.00 | 1.00 | 1.00 | 1.00 | 1.00 | 1.00 | 1.00 | 1.00 | 0.16 | 0.15 |
| H2-T24 | 1.00 | 1.00 | 1.00 | 1.33 | 1.00 | 1.60 | 1.08 | 1.00 | 1.64 | 0.19 | 1.20 | 1.04 |
| H2-T3 | 1.00 | 1.00 | 1.00 | 1.00 | 1.00 | 1.00 | 1.00 | 1.00 | 1.00 | 1.00 | 1.00 | 1.00 |
| Hace1 | 1.00 | 1.00 | 1.00 | 0.99 | 1.63 | 0.89 | 0.74 | 0.15 | 0.70 | 0.45 | 0.98 | 0.84 |
| Haus2 | 0.89 | 1.11 | 0.94 | 1.10 | 0.73 | 1.06 | 0.77 | 0.11 | 0.97 | 0.25 | 0.74 | 0.86 |
| Hcar1 | 1.00 | 1.00 | 1.00 | 1.12 | 1.00 | 1.00 | 1.00 | 1.00 | 1.00 | 1.00 | 1.00 | 1.00 |
| Hcar2 | 1.00 | 1.00 | 1.00 | 1.00 | 1.00 | 1.00 | 0.63 | 0.33 | 0.48 | 0.44 | 0.88 | 0.77 |
| Hccs | 0.90 | 1.14 | 1.09 | 1.01 | 1.00 | 1.07 | 0.85 | 0.17 | 1.17 | 0.49 | 0.89 | 0.96 |
| Hdac2 | 0.91 | 0.80 | 0.94 | 1.06 | 1.00 | 0.93 | 0.71 | 0.11 | 0.84 | 0.50 | 0.82 | 0.88 |
| Hdhd3 | 0.64 | 0.50 | 0.44 | 0.89 | 0.80 | 0.91 | 0.46 | 0.53 | 0.45 | 0.42 | 0.55 | 0.86 |
| Heca | 1.73 | 1.43 | 1.16 | 0.89 | 1.00 | 0.94 | 0.76 | 0.06 | 1.28 | 0.53 | 1.06 | 1.02 |
| Heg1 | 1.00 | 1.00 | 1.00 | 0.69 | 1.00 | 0.85 | 1.03 | 1.00 | 1.31 | 1.00 | 0.71 | 0.73 |
| Hemgn | 1.00 | 1.00 | 1.00 | 1.00 | 1.00 | 1.00 | 1.00 | 1.00 | 1.00 | 0.39 | 0.87 | 0.77 |
| Hephl1 | 1.00 | 1.00 | 1.00 | 1.00 | 1.00 | 1.00 | 0.51 | 0.10 | 0.72 | 1.00 | 1.00 | 1.00 |
| Herc3 | 1.00 | 1.00 | 1.00 | 1.01 | 2.28 | 0.98 | 1.12 | 0.45 | 1.47 | 0.78 | 1.19 | 1.28 |
| Hfe | 0.63 | 1.21 | 1.12 | 0.91 | 1.00 | 0.95 | 1.27 | 0.15 | 1.26 | 0.45 | 0.90 | 1.03 |
| Hibadh | 0.71 | 0.73 | 0.83 | 1.05 | 0.22 | 1.00 | 1.06 | 0.17 | 1.00 | 0.51 | 0.86 | 1.02 |
| Hipk1 | 1.37 | 1.38 | 1.23 | 1.03 | 1.49 | 1.03 | 1.14 | 0.18 | 1.24 | 0.54 | 1.12 | 1.00 |
| Hist1h1d | 1.00 | 1.00 | 1.00 | 1.00 | 1.00 | 1.00 | 1.08 | 1.09 | 0.83 | 2.38 | 1.96 | 1.38 |
| Hist1h1e | 1.00 | 1.00 | 1.00 | 1.41 | 1.00 | 1.41 | 0.98 | 0.83 | 1.24 | 1.73 | 1.77 | 1.49 |
| Hist1h2af | 1.00 | 1.00 | 1.00 | 1.00 | 0.94 | 1.00 | 1.00 | 1.00 | 1.00 | 1.26 | 0.97 | 1.13 |
| Hist1h2ag | 1.00 | 1.00 | 1.00 | 1.00 | 1.00 | 1.00 | 0.99 | 2.09 | 1.27 | 1.76 | 0.47 | 0.83 |
| Hist1h2ap | 1.00 | 1.00 | 1.00 | 1.00 | 1.00 | 1.00 | 1.00 | 3.33 | 0.64 | 0.15 | 0.45 | 4.35 |
| Hist1h2bk | 0.48 | 1.15 | 1.10 | 0.97 | 1.00 | 1.36 | 1.92 | 0.43 | 1.01 | 1.51 | 1.66 | 1.11 |
| Hist1h3c | 1.00 | 1.00 | 1.00 | 1.00 | 1.00 | 1.00 | 1.00 | 1.00 | 1.00 | 1.61 | 2.23 | 1.02 |
| Hist1h3e | 1.00 | 1.00 | 1.00 | 1.00 | 1.00 | 1.00 | 1.00 | 1.58 | 1.27 | 2.53 | 1.33 | 2.38 |
| Hist1h3i | 1.00 | 1.00 | 1.00 | 1.00 | 1.00 | 1.00 | 1.00 | 1.00 | 1.00 | 1.41 | 1.24 | 1.51 |
| Hist1h4d | 1.00 | 1.00 | 1.00 | 1.00 | 0.18 | 1.00 | 0.67 | 1.52 | 1.53 | 2.45 | 0.85 | 0.81 |
| Hist2h2bb | 1.00 | 1.00 | 1.00 | 0.55 | 1.00 | 0.73 | 1.00 | 1.00 | 1.04 | 1.23 | 0.85 | 1.45 |
| Hist2h3c2 | 0.63 | 1.47 | 0.63 | 1.56 | 1.00 | 1.84 | 1.61 | 0.44 | 2.72 | 1.20 | 1.34 | 1.77 |
| Hist2h4 | 1.00 | 1.00 | 1.00 | 1.00 | 0.09 | 1.00 | 1.00 | 1.00 | 1.00 | 0.87 | 1.80 | 1.20 |
| Hist3h2a | 0.37 | 0.82 | 0.44 | 1.29 | 1.00 | 0.99 | 1.25 | 0.07 | 1.04 | 0.23 | 1.05 | 1.02 |
| Hmgcs1 | 1.19 | 0.60 | 0.83 | 0.86 | 1.14 | 0.95 | 0.87 | 0.50 | 1.00 | 1.00 | 1.50 | 1.49 |
| Hn1l | 1.34 | 0.74 | 1.11 | 0.80 | 1.00 | 1.17 | 0.66 | 0.12 | 0.72 | 0.53 | 0.69 | 0.85 |
| Hnf4aos | 1.00 | 1.00 | 1.00 | 1.00 | 1.00 | 1.00 | 1.00 | 1.00 | 1.00 | 1.00 | 1.00 | 1.00 |
| Hnrnph1 | 0.82 | 1.31 | 1.19 | 0.93 | 0.99 | 0.95 | 0.94 | 0.16 | 1.02 | 0.46 | 0.94 | 0.93 |
| Hnrnph2 | 1.51 | 1.52 | 1.36 | 1.17 | 0.21 | 1.05 | 0.86 | 0.06 | 0.92 | 0.39 | 1.03 | 0.90 |
| Hnrnpul1 | 1.11 | 0.62 | 0.95 | 0.92 | 1.00 | 0.95 | 0.87 | 0.05 | 0.98 | 0.16 | 0.79 | 0.79 |
| Hook1 | 1.10 | 1.24 | 1.37 | 0.89 | 1.00 | 0.85 | 0.76 | 0.13 | 1.00 | 1.00 | 0.85 | 0.97 |
| Hoxa4 | 1.00 | 1.00 | 1.00 | 1.00 | 1.00 | 1.77 | 1.40 | 0.54 | 0.94 | 1.00 | 1.00 | 1.00 |
| Hoxc13 | 1.00 | 1.00 | 1.00 | 1.00 | 1.00 | 1.00 | 0.93 | 0.16 | 0.92 | 1.00 | 1.00 | 1.00 |
| Hpgds | 1.00 | 1.00 | 1.00 | 0.53 | 0.68 | 0.73 | 0.69 | 0.57 | 0.90 | 0.90 | 0.41 | 0.63 |
| Hps3 | 2.03 | 2.56 | 2.79 | 0.83 | 0.30 | 0.90 | 0.81 | 0.16 | 1.22 | 0.60 | 1.21 | 1.18 |
| Hrc | 1.00 | 1.00 | 1.00 | 1.00 | 1.00 | 1.00 | 1.50 | 0.12 | 1.71 | 1.00 | 1.00 | 1.00 |

Fig. 35- 49

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Hs3st1 | 0.96 | 1.00 | 1.34 | 1.01 | 0.63 | 1.63 | 0.86 | 0.86 | 1.28 | 0.27 | 0.13 | 0.80 |
| Hsd17b6 | 1.00 | 1.00 | 1.00 | 1.00 | 1.00 | 1.00 | 1.00 | 1.00 | 1.00 | 1.00 | 1.00 | 1.00 |
| Hsd3b1 | 1.00 | 1.00 | 1.00 | 1.00 | 1.00 | 1.00 | 1.00 | 0.81 | 1.00 | 1.00 | 1.00 | 1.00 |
| Hsd3b2 | 1.00 | 1.00 | 1.00 | 1.00 | 1.00 | 1.00 | 1.00 | 1.00 | 1.00 | 1.00 | 1.00 | 1.00 |
| Hsd3b3 | 1.00 | 1.00 | 1.00 | 1.00 | 1.00 | 1.00 | 1.00 | 1.00 | 1.00 | 1.00 | 1.00 | 1.00 |
| Hsdl2 | 0.66 | 1.15 | 0.79 | 0.98 | 0.32 | 0.75 | 0.65 | 0.64 | 0.62 | 0.41 | 0.29 | 1.02 |
| Hspa12a | 0.46 | 1.00 | 0.61 | 0.66 | 0.23 | 0.49 | 0.52 | 0.66 | 0.58 | 0.46 | 0.39 | 0.47 |
| Hspb6 | 1.19 | 1.27 | 0.98 | 1.14 | 0.77 | 0.88 | 0.90 | 0.81 | 0.84 | 0.81 | 0.64 | 1.01 |
| Hyal1 | 0.43 | 1.00 | 0.86 | 0.32 | 0.04 | 0.41 | 1.26 | 1.81 | 1.35 | 0.61 | 0.12 | 1.21 |
| Hyou1 | 0.93 | 1.63 | 0.97 | 0.77 | 0.26 | 1.11 | 0.84 | 0.80 | 1.01 | 0.28 | 0.32 | 1.22 |
| Icam4 | 1.00 | 1.32 | 1.00 | 1.00 | 1.00 | 1.00 | 1.00 | 0.71 | 1.00 | 1.00 | 0.74 | 1.47 |
| Id2 | 0.91 | 1.37 | 1.17 | 1.64 | 0.66 | 1.08 | 0.94 | 0.87 | 1.00 | 0.26 | 0.31 | 0.94 |
| Id3 | 1.22 | 1.23 | 0.88 | 0.54 | 1.55 | 0.98 | 1.07 | 0.73 | 0.96 | 0.49 | 0.87 | 1.02 |
| Ier3 | 1.77 | 1.89 | 1.23 | 1.16 | 0.18 | 0.52 | 0.49 | 0.34 | 0.68 | 0.90 | 0.63 | 1.29 |
| Ifitm6 | 1.19 | 1.00 | 1.44 | 1.00 | 1.00 | 1.00 | 1.00 | 1.00 | 1.00 | 0.67 | 0.38 | 0.94 |
| Ift20 | 1.02 | 1.53 | 1.04 | 0.51 | 0.41 | 0.81 | 1.02 | 0.73 | 0.78 | 0.52 | 0.60 | 0.99 |
| Igfals | 1.00 | 1.00 | 0.93 | 0.38 | 0.70 | 0.70 | 0.17 | 0.19 | 0.19 | 1.00 | 1.00 | 1.00 |
| Igfbp5 | 0.41 | 0.83 | 0.44 | 1.88 | 0.13 | 0.66 | 0.64 | 0.70 | 1.01 | 0.46 | 0.32 | 1.18 |
| Igfbp7 | 1.17 | 1.35 | 1.02 | 0.59 | 0.93 | 1.11 | 0.95 | 0.76 | 1.02 | 0.48 | 0.78 | 1.00 |
| Igfbpl1 | 1.00 | 1.00 | 1.00 | 1.00 | 1.00 | 1.00 | 1.00 | 1.00 | 1.00 | 1.00 | 1.00 | 1.00 |
| Ikzf5 | 1.13 | 1.73 | 1.03 | 2.07 | 0.33 | 0.95 | 0.87 | 1.31 | 0.99 | 0.32 | 0.42 | 1.15 |
| Il10rb | 0.74 | 1.57 | 1.09 | 1.31 | 0.42 | 1.09 | 0.78 | 0.81 | 0.73 | 0.39 | 0.38 | 0.94 |
| Il15ra | 1.29 | 2.31 | 0.99 | 0.47 | 0.24 | 0.99 | 0.72 | 0.63 | 0.79 | 0.29 | 0.20 | 1.11 |
| Il1a | 1.00 | 1.00 | 1.00 | 1.00 | 1.00 | 1.00 | 1.00 | 1.00 | 1.00 | 0.97 | 0.53 | 0.72 |
| Il1f8 | 1.00 | 1.00 | 1.00 | 1.00 | 1.00 | 1.00 | 1.00 | 1.00 | 1.00 | 1.00 | 1.00 | 1.00 |
| Il1f9 | 1.00 | 1.00 | 1.00 | 1.00 | 1.00 | 1.00 | 1.00 | 1.00 | 1.00 | 1.00 | 0.70 | 1.00 |
| Il1r1 | 3.49 | 4.80 | 4.23 | 2.18 | 0.39 | 0.78 | 1.03 | 1.25 | 1.48 | 0.59 | 0.16 | 0.99 |
| Il1rap | 0.73 | 1.00 | 1.30 | 2.04 | 0.84 | 1.02 | 0.95 | 1.15 | 1.26 | 0.57 | 0.41 | 1.07 |
| Il1rl2 | 1.00 | 1.00 | 1.00 | 1.00 | 1.00 | 1.00 | 1.00 | 1.00 | 1.00 | 1.00 | 1.00 | 0.87 |
| Il1rn | 1.00 | 1.00 | 1.00 | 2.28 | 1.78 | 1.43 | 1.00 | 1.00 | 1.00 | 1.02 | 1.25 | 1.06 |
| Il20ra | 1.00 | 1.00 | 1.00 | 1.00 | 1.00 | 1.00 | 1.00 | 1.00 | 1.00 | 1.00 | 1.00 | 1.00 |
| Il33 | 0.78 | 0.94 | 1.09 | 1.00 | 0.45 | 0.92 | 0.50 | 0.60 | 1.61 | 0.78 | 0.71 | 0.78 |
| Impact | 3.15 | 3.17 | 1.97 | 1.62 | 0.32 | 1.27 | 1.06 | 1.00 | 1.06 | 0.24 | 0.39 | 1.00 |
| Impad1 | 0.82 | 1.00 | 0.83 | 1.98 | 0.11 | 0.85 | 1.02 | 1.49 | 1.19 | 1.00 | 0.54 | 1.02 |
| Ino80dos | 0.53 | 1.00 | 0.67 | 1.58 | 0.19 | 0.72 | 0.61 | 0.87 | 0.92 | 1.18 | 0.84 | 0.86 |
| Ints12 | 1.02 | 1.95 | 1.01 | 1.54 | 0.51 | 1.70 | 0.92 | 1.25 | 0.94 | 0.48 | 0.60 | 0.92 |
| Ipo7 | 1.06 | 1.00 | 1.28 | 1.65 | 0.14 | 1.07 | 1.17 | 1.55 | 1.29 | 1.00 | 0.95 | 1.08 |
| Ipw | 1.00 | 1.00 | 1.00 | 1.00 | 1.00 | 1.00 | 1.00 | 1.00 | 1.00 | 1.00 | 1.00 | 1.00 |
| Ireb2 | 0.89 | 1.31 | 0.94 | 2.13 | 0.55 | 0.94 | 0.85 | 1.08 | 1.04 | 0.55 | 0.56 | 1.05 |
| Irf2 | 1.46 | 3.97 | 1.29 | 1.84 | 0.20 | 1.09 | 1.23 | 1.36 | 1.07 | 0.49 | 0.23 | 0.91 |
| Isg20l2 | 1.02 | 2.33 | 1.13 | 1.66 | 0.34 | 1.16 | 0.94 | 0.81 | 1.06 | 0.33 | 0.35 | 0.90 |
| Isoc1 | 0.56 | 1.01 | 0.69 | 0.56 | 0.07 | 0.35 | 0.81 | 1.15 | 0.83 | 0.26 | 0.10 | 0.72 |
| Itgax | 1.00 | 1.00 | 1.00 | 1.00 | 1.00 | 1.00 | 1.00 | 1.00 | 1.00 | 1.22 | 1.49 | 0.71 |
| Itpkb | 0.53 | 1.00 | 0.82 | 0.68 | 0.04 | 0.66 | 0.75 | 1.21 | 1.04 | 1.00 | 0.16 | 0.94 |
| Iyd | 1.00 | 1.00 | 1.00 | 1.00 | 1.00 | 1.00 | 1.00 | 1.00 | 1.00 | 0.44 | 0.30 | 0.42 |
| Jade1 | 0.82 | 1.37 | 0.88 | 2.68 | 0.41 | 1.32 | 0.75 | 1.06 | 0.96 | 0.53 | 0.54 | 1.08 |
| Jag2 | 0.92 | 1.43 | 0.93 | 0.69 | 0.32 | 0.89 | 1.14 | 1.00 | 0.96 | 0.60 | 0.43 | 0.91 |
| Kank1 | 2.95 | 3.93 | 3.13 | 1.80 | 0.57 | 1.30 | 1.76 | 2.28 | 1.66 | 0.84 | 0.73 | 1.18 |
| Kansl1 | 1.06 | 1.95 | 0.95 | 1.39 | 0.22 | 0.97 | 1.03 | 1.42 | 1.09 | 0.38 | 0.31 | 0.98 |
| Kat6b | 0.82 | 1.30 | 1.10 | 1.71 | 0.28 | 0.95 | 1.44 | 1.42 | 1.24 | 0.81 | 0.48 | 1.05 |
| Kazald1 | 0.29 | 0.40 | 0.18 | 1.00 | 2.03 | 1.86 | 1.33 | 1.04 | 1.24 | 0.41 | 0.91 | 0.71 |
| Kcna3 | 1.00 | 1.00 | 1.00 | 1.00 | 1.00 | 1.00 | 1.00 | 1.00 | 1.00 | 1.00 | 1.00 | 1.00 |
| Kcnab2 | 1.00 | 1.00 | 1.00 | 1.00 | 0.13 | 1.00 | 1.00 | 1.00 | 1.39 | 0.81 | 0.78 | 0.84 |
| Kcnc3 | 0.69 | 1.00 | 0.69 | 1.03 | 0.19 | 1.29 | 1.88 | 2.15 | 1.20 | 1.31 | 0.70 | 1.14 |
| Kcne1l | 0.56 | 1.00 | 1.00 | 1.00 | 0.98 | 1.00 | 1.00 | 1.00 | 1.00 | 1.00 | 1.00 | 1.00 |
| Kcng2 | 1.00 | 1.00 | 1.00 | 0.05 | 0.08 | 0.05 | 0.93 | 0.89 | 1.06 | 1.00 | 1.00 | 0.97 |
| Kcnj14 | 1.00 | 1.00 | 1.00 | 1.00 | 1.00 | 1.00 | 0.60 | 0.39 | 0.33 | 0.36 | 0.34 | 0.35 |
| Kcnk2 | 0.90 | 1.00 | 0.78 | 0.21 | 0.12 | 0.43 | 0.70 | 0.93 | 0.81 | 1.01 | 0.78 | 1.07 |
| Kcnv1 | 1.00 | 1.00 | 1.00 | 1.00 | 0.75 | 1.00 | 1.00 | 1.00 | 1.00 | 1.00 | 1.00 | 1.00 |
| Kctd13 | 0.88 | 1.67 | 1.44 | 0.78 | 0.48 | 1.15 | 1.25 | 0.99 | 0.85 | 0.28 | 0.41 | 1.05 |
| Kctd5 | 0.96 | 1.28 | 1.14 | 1.19 | 0.65 | 1.34 | 1.16 | 1.03 | 1.00 | 0.48 | 0.40 | 0.99 |
| Kdelc2 | 0.92 | 1.51 | 0.85 | 1.65 | 0.59 | 0.79 | 0.64 | 0.74 | 0.81 | 0.39 | 0.40 | 0.82 |
| Kdm4a | 1.53 | 3.11 | 1.05 | 0.81 | 0.12 | 0.92 | 1.09 | 1.31 | 0.97 | 0.36 | 0.22 | 1.00 |
| Kdr | 0.53 | 1.00 | 0.74 | 1.50 | 0.04 | 0.80 | 0.93 | 0.93 | 1.05 | 0.55 | 0.05 | 0.72 |

Fig. 35- 50

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Hs3st1 | 1.74 | 1.56 | 0.93 | 0.62 | 1.00 | 0.61 | 1.00 | 1.00 | 1.00 | 1.24 | 0.99 | 1.12 |
| Hsd17b6 | 1.00 | 1.00 | 1.00 | 1.00 | 1.00 | 1.00 | 0.15 | 0.02 | 0.27 | 1.00 | 1.00 | 1.00 |
| Hsd3b1 | 1.00 | 1.00 | 1.00 | 1.00 | 1.00 | 1.00 | 1.00 | 1.00 | 1.00 | 1.00 | 1.00 | 1.00 |
| Hsd3b2 | 1.00 | 1.00 | 1.00 | 1.06 | 1.59 | 0.90 | 0.09 | 0.20 | 0.25 | 0.96 | 0.70 | 1.05 |
| Hsd3b3 | 1.00 | 1.00 | 1.00 | 0.58 | 0.73 | 0.72 | 0.21 | 0.13 | 0.44 | 1.05 | 1.07 | 1.05 |
| Hsdl2 | 0.98 | 1.01 | 1.00 | 0.97 | 1.62 | 1.04 | 1.44 | 0.47 | 1.28 | 1.01 | 0.75 | 1.12 |
| Hspa12a | 0.98 | 0.76 | 0.73 | 0.47 | 0.58 | 0.67 | 1.00 | 1.00 | 1.00 | 0.28 | 0.18 | 0.19 |
| Hspb6 | 1.11 | 1.49 | 0.75 | 0.90 | 1.06 | 0.93 | 0.59 | 0.19 | 0.47 | 1.03 | 0.99 | 1.26 |
| Hyal1 | 1.26 | 0.67 | 1.19 | 1.61 | 1.00 | 1.53 | 0.82 | 1.00 | 0.92 | 0.76 | 0.60 | 0.90 |
| Hyou1 | 0.93 | 0.92 | 1.12 | 1.04 | 1.81 | 0.91 | 1.11 | 0.31 | 1.05 | 1.05 | 0.80 | 0.97 |
| Icam4 | 1.00 | 1.00 | 1.00 | 1.00 | 1.00 | 1.00 | 0.93 | 1.16 | 0.80 | 1.00 | 1.00 | 1.00 |
| Id2 | 1.10 | 1.14 | 1.36 | 0.69 | 1.12 | 0.86 | 0.93 | 0.42 | 1.12 | 0.91 | 0.85 | 0.84 |
| Id3 | 0.76 | 0.89 | 0.89 | 0.74 | 1.34 | 1.08 | 1.11 | 0.46 | 1.33 | 0.87 | 1.40 | 1.02 |
| Ier3 | 1.66 | 1.42 | 1.41 | 0.99 | 1.46 | 1.05 | 2.70 | 2.34 | 2.08 | 1.00 | 1.60 | 1.20 |
| Ifitm6 | 0.18 | 0.92 | 1.02 | 1.00 | 1.00 | 1.00 | 1.12 | 1.00 | 2.06 | 1.00 | 1.60 | 0.96 |
| Ift20 | 1.00 | 1.16 | 0.95 | 0.79 | 2.24 | 0.83 | 1.20 | 0.50 | 1.10 | 1.17 | 1.25 | 1.19 |
| Igfals | 0.96 | 0.87 | 0.88 | 1.39 | 1.42 | 1.35 | 0.20 | 0.12 | 0.32 | 1.00 | 1.00 | 1.00 |
| Igfbp5 | 4.02 | 2.27 | 2.77 | 0.63 | 0.73 | 0.78 | 0.53 | 1.00 | 0.87 | 0.87 | 0.52 | 0.83 |
| Igfbp7 | 1.45 | 1.49 | 1.37 | 0.87 | 1.19 | 1.08 | 1.03 | 0.62 | 1.10 | 0.98 | 1.09 | 0.90 |
| Igfbpl1 | 1.00 | 1.00 | 1.00 | 1.00 | 1.00 | 1.00 | 1.00 | 1.00 | 1.00 | 1.00 | 1.00 | 1.00 |
| Ikzf5 | 0.63 | 0.58 | 0.75 | 1.03 | 1.00 | 0.91 | 1.05 | 1.00 | 1.20 | 0.98 | 0.76 | 1.15 |
| Il10rb | 1.39 | 1.30 | 1.54 | 0.78 | 1.35 | 0.84 | 0.81 | 0.62 | 0.90 | 0.94 | 0.83 | 1.00 |
| Il15ra | 1.13 | 0.97 | 1.24 | 0.73 | 2.20 | 0.73 | 0.71 | 0.15 | 0.91 | 0.85 | 0.80 | 0.89 |
| Il1a | 2.72 | 2.68 | 2.26 | 1.00 | 1.00 | 1.00 | 0.77 | 1.00 | 0.91 | 1.00 | 1.00 | 1.00 |
| Il1f8 | 1.00 | 1.00 | 1.00 | 1.00 | 1.00 | 1.00 | 1.00 | 1.00 | 1.00 | 1.00 | 1.00 | 1.00 |
| Il1f9 | 1.00 | 1.00 | 1.00 | 1.00 | 1.00 | 1.00 | 1.00 | 1.00 | 1.00 | 1.00 | 1.00 | 1.00 |
| Il1r1 | 1.44 | 1.11 | 1.36 | 1.23 | 1.00 | 1.00 | 2.04 | 1.00 | 2.52 | 0.95 | 0.64 | 1.03 |
| Il1rap | 0.87 | 0.69 | 1.32 | 0.87 | 1.00 | 0.96 | 0.60 | 0.24 | 0.67 | 1.20 | 0.72 | 1.10 |
| Il1rl2 | 0.64 | 0.32 | 1.24 | 1.00 | 1.00 | 1.00 | 1.00 | 1.00 | 1.00 | 0.97 | 1.00 | 1.00 |
| Il1rn | 1.07 | 0.89 | 1.41 | 1.00 | 1.00 | 1.00 | 3.72 | 2.41 | 3.99 | 0.92 | 0.88 | 0.95 |
| Il20ra | 1.00 | 1.00 | 1.00 | 1.00 | 1.00 | 1.00 | 1.00 | 1.00 | 1.00 | 1.00 | 1.00 | 1.00 |
| Il33 | 1.25 | 1.06 | 1.07 | 1.06 | 0.94 | 1.15 | 0.94 | 1.00 | 1.00 | 0.71 | 0.77 | 0.65 |
| Impact | 1.07 | 1.00 | 1.21 | 1.34 | 1.67 | 1.02 | 2.13 | 0.81 | 1.56 | 1.07 | 0.78 | 1.10 |
| Impad1 | 0.50 | 0.41 | 0.84 | 1.25 | 1.00 | 1.10 | 1.27 | 1.00 | 1.22 | 1.18 | 0.38 | 0.97 |
| Ino80dos | 0.86 | 0.94 | 0.96 | 0.74 | 1.00 | 1.11 | 0.67 | 1.00 | 1.00 | 0.85 | 0.53 | 1.32 |
| Ints12 | 0.89 | 0.96 | 0.83 | 1.07 | 1.99 | 1.03 | 1.03 | 1.00 | 1.15 | 1.04 | 1.03 | 0.93 |
| Ipo7 | 0.53 | 0.38 | 0.86 | 1.45 | 1.00 | 1.19 | 1.08 | 1.00 | 1.13 | 1.07 | 0.32 | 0.94 |
| Ipw | 1.00 | 1.00 | 1.00 | 1.00 | 1.00 | 1.00 | 1.00 | 1.00 | 1.00 | 1.00 | 1.00 | 1.00 |
| Ireb2 | 0.76 | 0.70 | 0.86 | 1.27 | 1.69 | 0.91 | 1.12 | 0.50 | 1.12 | 1.11 | 0.81 | 0.96 |
| Irf2 | 1.01 | 0.89 | 1.16 | 0.97 | 1.52 | 0.98 | 1.01 | 0.57 | 1.11 | 1.06 | 0.88 | 1.08 |
| Isg20l2 | 0.83 | 0.81 | 0.92 | 0.90 | 2.15 | 0.95 | 0.94 | 0.81 | 1.00 | 0.91 | 0.76 | 0.97 |
| Isoc1 | 0.42 | 0.35 | 0.61 | 0.78 | 0.49 | 0.80 | 0.43 | 0.22 | 0.47 | 0.83 | 0.36 | 0.76 |
| Itgax | 1.23 | 1.07 | 1.42 | 1.00 | 1.00 | 1.00 | 1.00 | 1.00 | 1.00 | 0.72 | 0.76 | 0.64 |
| Itpkb | 0.56 | 0.38 | 0.99 | 1.08 | 1.00 | 1.30 | 0.61 | 1.00 | 1.10 | 0.85 | 0.21 | 0.76 |
| Iyd | 1.00 | 1.00 | 1.00 | 0.62 | 0.40 | 0.65 | 0.39 | 0.09 | 0.45 | 0.19 | 0.28 | 0.27 |
| Jade1 | 0.54 | 0.45 | 0.77 | 0.99 | 1.43 | 1.29 | 0.80 | 0.91 | 1.03 | 1.01 | 0.64 | 0.93 |
| Jag2 | 1.25 | 0.91 | 1.38 | 1.06 | 1.00 | 1.26 | 1.00 | 1.00 | 1.00 | 0.82 | 0.60 | 0.82 |
| Kank1 | 1.42 | 1.16 | 1.27 | 1.09 | 1.42 | 1.13 | 0.66 | 1.02 | 0.91 | 0.93 | 0.65 | 0.83 |
| Kansl1 | 0.70 | 0.65 | 0.92 | 1.02 | 1.32 | 1.01 | 0.95 | 1.00 | 1.02 | 0.93 | 0.64 | 0.95 |
| Kat6b | 0.71 | 0.55 | 0.93 | 1.11 | 1.00 | 1.17 | 0.94 | 1.00 | 0.92 | 1.02 | 0.55 | 0.91 |
| Kazald1 | 1.95 | 1.34 | 1.41 | 1.13 | 1.50 | 0.83 | 1.00 | 1.00 | 1.00 | 1.39 | 1.70 | 1.15 |
| Kcna3 | 0.22 | 0.17 | 0.61 | 1.00 | 1.00 | 1.00 | 1.00 | 1.00 | 1.00 | 1.00 | 1.00 | 1.00 |
| Kcnab2 | 0.70 | 0.81 | 0.86 | 1.00 | 1.00 | 1.00 | 1.00 | 1.00 | 1.00 | 0.75 | 0.88 | 1.08 |
| Kcnc3 | 2.26 | 1.96 | 1.95 | 0.94 | 0.80 | 0.94 | 0.75 | 1.74 | 0.92 | 2.05 | 0.89 | 0.86 |
| Kcne1l | 1.00 | 1.00 | 1.00 | 0.62 | 1.00 | 0.63 | 1.00 | 1.00 | 1.00 | 1.00 | 1.00 | 1.00 |
| Kcng2 | 1.00 | 1.00 | 1.00 | 1.00 | 1.00 | 1.00 | 1.00 | 1.00 | 1.00 | 1.00 | 1.00 | 1.00 |
| Kcnj14 | 1.00 | 1.00 | 1.00 | 1.00 | 1.00 | 1.00 | 1.00 | 1.00 | 1.00 | 1.00 | 1.00 | 1.00 |
| Kcnk2 | 3.10 | 2.85 | 2.29 | 1.00 | 1.00 | 1.00 | 1.00 | 1.00 | 1.00 | 1.19 | 1.06 | 1.28 |
| Kcnv1 | 1.00 | 1.00 | 1.00 | 1.00 | 1.00 | 1.00 | 1.00 | 1.00 | 1.00 | 1.00 | 1.00 | 1.00 |
| Kctd13 | 1.03 | 0.97 | 0.92 | 1.11 | 3.43 | 1.15 | 1.86 | 0.90 | 1.49 | 1.15 | 0.95 | 0.97 |
| Kctd5 | 0.90 | 0.95 | 0.99 | 1.20 | 1.28 | 1.07 | 0.89 | 1.00 | 1.03 | 1.17 | 1.06 | 1.09 |
| Kdelc2 | 1.58 | 1.02 | 1.08 | 1.13 | 1.00 | 0.91 | 0.72 | 1.00 | 0.77 | 0.80 | 0.75 | 0.90 |
| Kdm4a | 0.86 | 0.82 | 0.97 | 1.07 | 1.69 | 1.12 | 1.40 | 1.00 | 1.35 | 0.94 | 0.77 | 0.93 |
| Kdr | 0.93 | 0.94 | 0.78 | 1.05 | 1.00 | 1.07 | 0.56 | 1.00 | 0.78 | 0.88 | 0.52 | 0.86 |

Fig. 35- 51

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Hs3st1 | 0.73 | 0.68 | 0.65 | 1.50 | 1.00 | 1.39 | 1.00 | 1.00 | 0.74 | 1.32 | 1.26 | 1.27 |
| Hsd17b6 | 0.85 | 0.89 | 0.59 | 1.00 | 1.00 | 1.00 | 1.00 | 1.00 | 1.00 | 1.00 | 1.00 | 1.00 |
| Hsd3b1 | 1.00 | 1.00 | 1.00 | 0.34 | 1.00 | 1.00 | 0.48 | 0.14 | 0.55 | 1.00 | 1.00 | 1.00 |
| Hsd3b2 | 1.00 | 1.00 | 1.00 | 1.00 | 1.00 | 1.00 | 0.55 | 1.00 | 0.50 | 1.00 | 1.00 | 1.00 |
| Hsd3b3 | 1.00 | 1.00 | 1.00 | 1.00 | 1.00 | 1.00 | 0.65 | 1.00 | 0.47 | 1.00 | 1.00 | 1.00 |
| Hsdl2 | 0.83 | 0.90 | 1.02 | 0.92 | 0.21 | 0.79 | 1.01 | 0.42 | 1.14 | 1.01 | 0.91 | 0.94 |
| Hspa12a | 0.57 | 0.57 | 0.64 | 0.26 | 0.31 | 0.16 | 0.55 | 1.00 | 0.62 | 0.85 | 3.15 | 1.41 |
| Hspb6 | 1.06 | 1.22 | 1.50 | 0.64 | 1.40 | 0.74 | 0.87 | 0.48 | 0.90 | 0.84 | 1.19 | 1.03 |
| Hyal1 | 0.73 | 0.79 | 0.60 | 1.26 | 0.45 | 1.29 | 1.30 | 1.00 | 1.11 | 0.67 | 0.71 | 0.91 |
| Hyou1 | 0.96 | 0.79 | 0.89 | 1.57 | 0.46 | 1.35 | 1.05 | 0.24 | 1.05 | 1.05 | 0.96 | 1.09 |
| Icam4 | 1.00 | 1.00 | 1.00 | 1.00 | 1.00 | 1.00 | 1.00 | 1.00 | 1.00 | 0.28 | 0.25 | 0.19 |
| Id2 | 0.89 | 0.98 | 0.92 | 1.10 | 0.23 | 1.28 | 1.09 | 0.30 | 0.82 | 0.81 | 0.82 | 0.75 |
| Id3 | 0.82 | 0.95 | 0.85 | 0.68 | 1.11 | 0.65 | 0.49 | 0.15 | 0.75 | 0.79 | 0.92 | 1.01 |
| Ier3 | 0.90 | 0.92 | 0.96 | 1.30 | 0.82 | 1.69 | 0.60 | 1.28 | 0.95 | 0.96 | 0.86 | 0.69 |
| Ifitm6 | 1.00 | 1.00 | 1.00 | 0.86 | 0.37 | 0.79 | 1.00 | 1.00 | 1.00 | 1.91 | 1.42 | 1.43 |
| Ift20 | 1.11 | 1.01 | 0.92 | 0.96 | 0.29 | 0.80 | 0.91 | 0.23 | 0.95 | 1.00 | 1.26 | 0.97 |
| Igfals | 1.00 | 1.00 | 1.00 | 0.14 | 1.00 | 0.30 | 1.21 | 1.00 | 1.24 | 1.00 | 1.00 | 0.95 |
| Igfbp5 | 0.70 | 0.61 | 0.83 | 0.73 | 0.15 | 0.83 | 1.00 | 1.00 | 1.01 | 0.52 | 0.59 | 0.85 |
| Igfbp7 | 0.85 | 1.10 | 1.23 | 0.93 | 0.93 | 1.13 | 0.56 | 0.14 | 0.61 | 0.82 | 0.94 | 0.82 |
| Igfbpl1 | 1.00 | 1.00 | 1.00 | 1.00 | 1.00 | 1.00 | 1.00 | 1.00 | 1.00 | 1.00 | 1.00 | 1.00 |
| Ikzf5 | 0.96 | 1.02 | 0.94 | 1.06 | 0.69 | 0.84 | 1.07 | 0.81 | 1.20 | 0.89 | 0.62 | 1.04 |
| Il10rb | 0.88 | 0.92 | 1.03 | 0.76 | 0.35 | 0.77 | 0.82 | 0.44 | 0.83 | 0.90 | 0.74 | 0.87 |
| Il15ra | 1.13 | 1.02 | 1.26 | 0.57 | 0.21 | 1.18 | 1.08 | 1.00 | 0.68 | 1.19 | 1.13 | 1.00 |
| Il1a | 1.00 | 1.00 | 1.00 | 1.00 | 1.00 | 1.00 | 1.00 | 1.00 | 1.00 | 1.06 | 1.28 | 0.78 |
| Il1f8 | 0.89 | 0.59 | 0.99 | 1.00 | 1.00 | 1.00 | 1.00 | 1.00 | 1.00 | 1.00 | 1.00 | 1.00 |
| Il1f9 | 1.51 | 1.52 | 2.21 | 1.00 | 1.00 | 1.00 | 1.00 | 1.00 | 1.00 | 1.00 | 1.00 | 1.00 |
| Il1r1 | 0.82 | 0.66 | 0.79 | 1.28 | 0.68 | 1.23 | 1.02 | 1.00 | 0.75 | 1.02 | 0.65 | 0.88 |
| Il1rap | 1.08 | 1.08 | 1.42 | 0.84 | 1.00 | 0.82 | 1.49 | 1.00 | 1.00 | 1.43 | 0.95 | 1.30 |
| Il1rl2 | 1.01 | 1.00 | 0.87 | 1.09 | 1.00 | 0.54 | 1.00 | 1.00 | 1.00 | 0.68 | 0.63 | 0.92 |
| Il1rn | 0.97 | 1.00 | 1.01 | 0.34 | 1.00 | 0.15 | 1.00 | 1.00 | 1.00 | 0.99 | 0.65 | 0.81 |
| Il20ra | 1.00 | 1.00 | 1.00 | 1.00 | 1.00 | 1.00 | 1.06 | 1.00 | 1.01 | 1.00 | 1.00 | 1.00 |
| Il33 | 0.41 | 0.37 | 0.19 | 1.00 | 1.03 | 0.88 | 1.02 | 1.00 | 1.15 | 0.76 | 0.64 | 0.48 |
| Impact | 1.27 | 1.12 | 1.18 | 1.22 | 0.33 | 1.06 | 0.87 | 0.91 | 0.89 | 1.22 | 1.19 | 0.98 |
| Impad1 | 0.90 | 0.73 | 0.60 | 1.10 | 0.19 | 0.74 | 0.91 | 1.33 | 1.02 | 0.89 | 0.71 | 1.07 |
| Ino80dos | 0.82 | 0.55 | 1.18 | 0.65 | 1.00 | 0.65 | 1.12 | 1.00 | 1.06 | 1.18 | 1.00 | 1.08 |
| Ints12 | 1.15 | 1.16 | 1.18 | 0.94 | 1.00 | 1.09 | 1.04 | 0.40 | 0.93 | 1.04 | 0.91 | 1.01 |
| Ipo7 | 1.05 | 0.82 | 0.94 | 1.31 | 0.45 | 1.06 | 1.25 | 1.00 | 1.10 | 1.04 | 0.56 | 0.96 |
| Ipw | 1.00 | 1.00 | 1.00 | 1.00 | 1.00 | 1.00 | 1.00 | 1.00 | 1.00 | 1.00 | 1.00 | 1.00 |
| Ireb2 | 1.06 | 0.93 | 0.82 | 1.00 | 0.65 | 1.03 | 1.06 | 0.52 | 1.00 | 1.04 | 0.73 | 1.02 |
| Irf2 | 1.07 | 1.17 | 1.17 | 0.77 | 0.23 | 0.98 | 0.98 | 0.85 | 1.02 | 1.11 | 0.80 | 1.11 |
| Isg20l2 | 0.99 | 0.88 | 0.98 | 1.10 | 0.75 | 1.24 | 0.94 | 1.92 | 0.92 | 1.12 | 0.82 | 1.08 |
| Isoc1 | 0.72 | 0.71 | 0.72 | 0.36 | 0.13 | 0.39 | 0.87 | 1.00 | 0.73 | 0.58 | 0.34 | 0.56 |
| Itgax | 1.00 | 0.86 | 1.00 | 0.37 | 1.39 | 0.10 | 1.00 | 1.00 | 1.00 | 0.72 | 0.66 | 0.73 |
| Itpkb | 0.98 | 1.04 | 0.81 | 0.86 | 0.08 | 0.84 | 0.94 | 1.30 | 0.95 | 0.77 | 0.40 | 1.02 |
| Iyd | 0.14 | 0.12 | 0.13 | 0.66 | 1.00 | 1.26 | 1.00 | 1.00 | 1.00 | 1.00 | 1.00 | 1.00 |
| Jade1 | 1.12 | 0.98 | 0.98 | 0.91 | 0.28 | 0.84 | 1.03 | 0.76 | 1.14 | 0.95 | 0.80 | 1.11 |
| Jag2 | 0.74 | 0.88 | 0.85 | 1.33 | 0.62 | 1.49 | 1.00 | 1.00 | 1.15 | 0.54 | 0.97 | 0.71 |
| Kank1 | 1.11 | 1.07 | 0.94 | 0.76 | 0.19 | 0.65 | 1.21 | 0.82 | 1.14 | 0.59 | 0.72 | 0.98 |
| Kansl1 | 1.07 | 1.18 | 0.94 | 1.15 | 0.29 | 0.97 | 1.12 | 1.33 | 1.10 | 1.01 | 0.81 | 1.07 |
| Kat6b | 1.10 | 1.02 | 0.94 | 1.12 | 0.49 | 0.85 | 1.12 | 1.00 | 1.04 | 0.96 | 0.76 | 1.10 |
| Kazald1 | 0.91 | 1.06 | 0.99 | 0.69 | 1.42 | 1.03 | 1.79 | 1.45 | 1.53 | 1.41 | 1.80 | 1.56 |
| Kcna3 | 1.00 | 1.00 | 1.00 | 1.00 | 1.00 | 1.00 | 1.00 | 1.00 | 1.00 | 0.67 | 0.50 | 1.38 |
| Kcnab2 | 1.11 | 1.33 | 1.37 | 1.06 | 1.00 | 0.70 | 1.18 | 0.83 | 1.04 | 0.91 | 1.04 | 0.95 |
| Kcnc3 | 1.27 | 2.25 | 1.28 | 2.03 | 1.10 | 1.78 | 1.00 | 1.00 | 1.00 | 1.15 | 3.34 | 1.23 |
| Kcne1l | 1.00 | 1.00 | 1.00 | 0.33 | 1.00 | 0.18 | 1.00 | 1.00 | 1.00 | 1.00 | 1.00 | 1.00 |
| Kcng2 | 1.00 | 1.00 | 1.00 | 1.00 | 1.00 | 1.00 | 0.35 | 0.56 | 0.66 | 0.55 | 0.97 | 0.65 |
| Kcnj14 | 1.00 | 1.00 | 1.00 | 0.28 | 1.00 | 0.13 | 1.00 | 1.00 | 1.00 | 0.89 | 0.85 | 0.77 |
| Kcnk2 | 0.98 | 1.00 | 1.00 | 0.18 | 0.35 | 0.39 | 1.26 | 1.25 | 1.15 | 1.00 | 2.47 | 1.00 |
| Kcnv1 | 1.00 | 1.00 | 1.00 | 1.00 | 1.00 | 1.00 | 1.00 | 1.00 | 1.00 | 1.00 | 1.94 | 1.00 |
| Kctd13 | 0.97 | 1.13 | 1.00 | 0.99 | 0.67 | 1.48 | 0.93 | 0.36 | 0.98 | 1.07 | 1.32 | 1.02 |
| Kctd5 | 0.88 | 0.76 | 0.78 | 1.22 | 1.48 | 1.10 | 1.11 | 1.12 | 0.96 | 1.06 | 0.85 | 0.96 |
| Kdelc2 | 0.81 | 0.67 | 1.13 | 0.83 | 0.66 | 0.83 | 0.82 | 1.00 | 0.92 | 0.84 | 0.80 | 1.02 |
| Kdm4a | 1.06 | 1.21 | 0.97 | 1.01 | 0.33 | 0.96 | 1.13 | 1.77 | 1.10 | 0.90 | 0.70 | 0.97 |
| Kdr | 1.01 | 0.97 | 0.97 | 1.03 | 0.13 | 1.22 | 0.96 | 1.00 | 1.03 | 0.59 | 0.42 | 0.86 |

Fig. 35- 52

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Hs3st1 | 1.00 | 1.00 | 1.00 | 0.93 | 1.00 | 1.00 | 1.16 | 0.34 | 1.03 | 0.59 | 0.77 | 0.75 |
| Hsd17b6 | 1.00 | 1.00 | 1.00 | 1.00 | 1.00 | 1.00 | 0.98 | 0.36 | 0.96 | 1.00 | 1.00 | 1.00 |
| Hsd3b1 | 1.00 | 1.00 | 1.00 | 1.00 | 1.00 | 1.00 | 1.00 | 1.00 | 1.00 | 1.00 | 1.00 | 1.00 |
| Hsd3b2 | 1.00 | 1.00 | 1.00 | 1.00 | 1.00 | 1.00 | 1.00 | 1.00 | 1.00 | 1.00 | 1.00 | 1.00 |
| Hsd3b3 | 1.00 | 1.00 | 1.00 | 1.00 | 1.00 | 1.00 | 1.00 | 1.00 | 1.00 | 1.00 | 1.00 | 1.00 |
| Hsdl2 | 0.81 | 0.70 | 0.77 | 1.02 | 1.00 | 0.93 | 1.04 | 0.17 | 1.19 | 0.51 | 0.85 | 0.98 |
| Hspa12a | 1.00 | 1.00 | 1.00 | 0.99 | 1.17 | 0.96 | 0.17 | 0.09 | 0.16 | 1.00 | 1.00 | 0.92 |
| Hspb6 | 1.16 | 0.95 | 0.69 | 1.01 | 1.05 | 1.06 | 1.15 | 0.84 | 1.55 | 0.59 | 0.87 | 0.80 |
| Hyal1 | 1.00 | 1.00 | 1.00 | 0.67 | 1.00 | 0.91 | 0.97 | 0.08 | 0.91 | 1.00 | 0.74 | 1.00 |
| Hyou1 | 1.20 | 1.15 | 1.04 | 1.12 | 1.80 | 1.01 | 1.28 | 0.16 | 0.96 | 0.39 | 0.85 | 1.00 |
| Icam4 | 1.00 | 1.00 | 1.00 | 1.00 | 1.00 | 1.00 | 0.91 | 1.00 | 0.70 | 0.55 | 0.62 | 0.65 |
| Id2 | 0.53 | 0.50 | 0.70 | 1.17 | 0.79 | 0.99 | 0.84 | 0.10 | 0.97 | 0.69 | 1.44 | 1.36 |
| Id3 | 0.82 | 1.28 | 1.26 | 0.88 | 0.86 | 0.90 | 1.25 | 0.53 | 1.04 | 0.55 | 0.59 | 0.93 |
| Ier3 | 1.31 | 1.55 | 1.14 | 0.92 | 0.87 | 1.09 | 0.96 | 0.54 | 1.02 | 1.03 | 1.66 | 1.37 |
| Ifitm6 | 1.00 | 1.00 | 1.00 | 1.00 | 0.96 | 1.00 | 1.18 | 1.00 | 1.00 | 0.70 | 1.26 | 1.45 |
| Ift20 | 0.58 | 0.65 | 0.82 | 0.99 | 0.23 | 1.24 | 0.97 | 0.12 | 0.72 | 0.46 | 1.06 | 0.81 |
| Igfals | 1.00 | 1.00 | 1.00 | 1.00 | 0.94 | 1.00 | 1.00 | 1.00 | 0.87 | 1.00 | 1.00 | 1.00 |
| Igfbp5 | 0.38 | 0.48 | 0.93 | 0.89 | 0.39 | 0.86 | 0.69 | 0.13 | 0.92 | 0.90 | 0.29 | 0.56 |
| Igfbp7 | 1.06 | 1.46 | 1.23 | 1.15 | 1.52 | 1.03 | 1.57 | 0.58 | 1.35 | 0.36 | 1.04 | 1.10 |
| Igfbpl1 | 1.00 | 1.00 | 1.00 | 1.00 | 0.20 | 1.00 | 1.00 | 1.00 | 1.00 | 1.00 | 1.00 | 1.00 |
| Ikzf5 | 1.15 | 1.18 | 1.24 | 0.94 | 0.42 | 1.02 | 0.84 | 0.11 | 0.96 | 0.48 | 0.82 | 0.79 |
| Il10rb | 0.81 | 0.69 | 0.66 | 0.91 | 0.45 | 1.06 | 0.87 | 0.19 | 0.84 | 0.48 | 1.21 | 1.17 |
| Il15ra | 1.26 | 1.05 | 1.83 | 1.22 | 1.00 | 1.00 | 1.08 | 0.10 | 0.91 | 1.01 | 2.49 | 1.65 |
| Il1a | 1.00 | 1.00 | 1.00 | 1.00 | 1.00 | 1.00 | 0.81 | 0.18 | 0.89 | 1.00 | 1.00 | 1.00 |
| Il1f8 | 1.00 | 1.00 | 1.00 | 1.00 | 1.00 | 1.00 | 0.75 | 0.04 | 0.57 | 1.00 | 1.00 | 1.00 |
| Il1f9 | 1.00 | 1.00 | 1.00 | 1.00 | 1.00 | 1.00 | 0.55 | 0.08 | 0.49 | 0.24 | 0.55 | 0.83 |
| Il1r1 | 0.83 | 1.00 | 0.76 | 1.21 | 1.00 | 1.45 | 1.03 | 0.09 | 1.25 | 0.73 | 0.66 | 0.74 |
| Il1rap | 0.88 | 1.01 | 1.00 | 0.94 | 1.05 | 1.04 | 0.72 | 0.11 | 0.98 | 0.79 | 1.77 | 1.80 |
| Il1rl2 | 1.00 | 1.00 | 1.00 | 1.00 | 1.00 | 1.00 | 0.55 | 0.14 | 0.96 | 1.00 | 0.97 | 0.59 |
| Il1rn | 1.00 | 1.00 | 1.00 | 1.00 | 1.00 | 1.00 | 0.57 | 0.46 | 0.52 | 1.16 | 1.36 | 1.28 |
| Il20ra | 1.00 | 1.00 | 1.00 | 1.00 | 1.00 | 1.00 | 0.86 | 0.15 | 1.29 | 1.00 | 1.00 | 1.00 |
| Il33 | 1.00 | 1.00 | 1.00 | 0.81 | 0.83 | 0.73 | 0.76 | 0.57 | 1.04 | 1.00 | 1.00 | 1.00 |
| Impact | 0.82 | 0.86 | 1.30 | 1.14 | 1.07 | 1.07 | 0.98 | 0.17 | 1.12 | 0.42 | 1.06 | 1.15 |
| Impad1 | 1.31 | 1.52 | 1.67 | 0.90 | 0.71 | 0.93 | 0.72 | 0.11 | 1.04 | 0.68 | 0.94 | 0.88 |
| Ino80dos | 1.00 | 1.00 | 1.00 | 0.92 | 2.05 | 0.88 | 1.23 | 0.72 | 1.27 | 0.79 | 0.52 | 1.29 |
| Ints12 | 1.02 | 0.87 | 1.01 | 1.03 | 1.00 | 0.94 | 0.93 | 0.14 | 0.98 | 0.68 | 0.97 | 1.07 |
| Ipo7 | 1.20 | 0.89 | 1.21 | 0.84 | 1.00 | 0.95 | 0.90 | 0.28 | 1.18 | 1.00 | 0.70 | 0.71 |
| Ipw | 1.00 | 1.00 | 1.00 | 0.18 | 1.00 | 0.27 | 1.00 | 1.00 | 1.00 | 1.00 | 1.00 | 1.00 |
| Ireb2 | 1.08 | 1.03 | 1.09 | 0.91 | 0.56 | 1.00 | 0.97 | 0.16 | 1.15 | 0.55 | 1.03 | 0.90 |
| Irf2 | 1.02 | 1.08 | 1.26 | 0.99 | 1.85 | 0.98 | 1.11 | 0.14 | 1.13 | 0.36 | 1.26 | 1.12 |
| Isg20l2 | 1.27 | 0.80 | 1.00 | 0.93 | 1.00 | 1.02 | 0.92 | 0.10 | 0.98 | 0.28 | 0.81 | 0.90 |
| Isoc1 | 0.45 | 0.34 | 0.57 | 0.78 | 0.55 | 0.75 | 0.62 | 0.05 | 0.83 | 0.15 | 0.50 | 0.57 |
| Itgax | 1.00 | 1.00 | 1.00 | 1.00 | 1.00 | 1.00 | 0.92 | 2.44 | 0.99 | 0.97 | 0.62 | 0.68 |
| Itpkb | 1.06 | 1.17 | 1.30 | 0.91 | 1.00 | 0.98 | 0.83 | 0.08 | 0.75 | 1.00 | 0.77 | 0.67 |
| Iyd | 1.00 | 1.00 | 1.00 | 1.00 | 1.00 | 1.00 | 1.00 | 1.00 | 1.00 | 1.00 | 1.00 | 1.00 |
| Jade1 | 0.78 | 0.96 | 1.02 | 0.90 | 1.00 | 0.94 | 0.80 | 0.19 | 1.16 | 0.52 | 0.93 | 0.83 |
| Jag2 | 1.00 | 1.00 | 1.00 | 0.97 | 0.71 | 0.90 | 0.67 | 0.19 | 0.85 | 1.00 | 1.00 | 1.00 |
| Kank1 | 1.11 | 1.00 | 1.00 | 0.83 | 0.62 | 1.02 | 1.07 | 0.61 | 1.20 | 1.00 | 1.00 | 1.00 |
| Kansl1 | 1.04 | 1.22 | 1.11 | 0.96 | 1.00 | 0.98 | 1.02 | 0.13 | 1.09 | 0.40 | 1.06 | 0.90 |
| Kat6b | 0.72 | 0.77 | 1.01 | 0.88 | 1.00 | 0.91 | 0.87 | 0.16 | 1.31 | 0.87 | 0.98 | 0.78 |
| Kazald1 | 0.99 | 0.60 | 0.59 | 1.41 | 0.95 | 0.98 | 0.58 | 1.08 | 0.54 | 1.00 | 1.00 | 1.00 |
| Kcna3 | 1.00 | 1.00 | 1.00 | 1.03 | 1.00 | 0.84 | 1.00 | 1.00 | 1.00 | 1.00 | 1.00 | 1.00 |
| Kcnab2 | 1.00 | 1.00 | 1.00 | 1.09 | 1.09 | 1.00 | 0.94 | 1.68 | 1.06 | 1.17 | 1.11 | 1.00 |
| Kcnc3 | 1.79 | 1.48 | 1.25 | 0.96 | 0.79 | 0.95 | 0.88 | 0.52 | 0.89 | 1.00 | 1.00 | 1.00 |
| Kcne1l | 1.00 | 1.00 | 1.00 | 1.20 | 1.06 | 1.19 | 2.02 | 1.69 | 1.74 | 1.00 | 1.00 | 1.00 |
| Kcng2 | 1.00 | 1.00 | 1.00 | 1.10 | 0.71 | 1.10 | 1.00 | 1.00 | 1.00 | 1.00 | 1.46 | 2.13 |
| Kcnj14 | 1.00 | 1.00 | 1.00 | 1.34 | 1.03 | 1.19 | 1.00 | 1.00 | 1.00 | 1.00 | 1.00 | 1.00 |
| Kcnk2 | 1.00 | 1.00 | 1.00 | 1.28 | 1.40 | 1.11 | 0.82 | 0.79 | 0.82 | 1.00 | 1.00 | 1.00 |
| Kcnv1 | 1.00 | 1.00 | 1.00 | 0.92 | 0.12 | 0.81 | 1.00 | 1.00 | 1.00 | 1.00 | 1.00 | 1.00 |
| Kctd13 | 1.33 | 0.72 | 0.59 | 1.03 | 1.15 | 1.06 | 1.35 | 0.11 | 1.06 | 0.58 | 1.16 | 1.29 |
| Kctd5 | 1.41 | 1.01 | 1.10 | 0.99 | 4.18 | 0.96 | 0.88 | 0.13 | 0.79 | 0.66 | 0.81 | 1.09 |
| Kdelc2 | 1.00 | 1.00 | 1.00 | 0.86 | 1.00 | 1.10 | 0.74 | 0.20 | 0.98 | 1.00 | 1.29 | 1.00 |
| Kdm4a | 0.79 | 1.04 | 0.96 | 1.07 | 1.00 | 1.06 | 0.97 | 0.05 | 1.05 | 0.29 | 1.08 | 0.91 |
| Kdr | 1.09 | 1.00 | 0.99 | 0.95 | 1.00 | 0.91 | 0.91 | 0.54 | 1.38 | 1.00 | 1.00 | 1.00 |

Fig. 35- 53

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Keg1 | 1.00 | 1.00 | 1.00 | 1.00 | 1.00 | 1.00 | 1.00 | 1.00 | 1.00 | 1.00 | 1.00 | 1.00 |
| Kel | 1.00 | 1.00 | 1.00 | 1.00 | 1.00 | 1.00 | 1.00 | 1.00 | 1.00 | 1.00 | 1.00 | 1.00 |
| Khnyn | 0.72 | 1.00 | 1.04 | 2.13 | 0.58 | 1.03 | 1.47 | 1.89 | 1.44 | 1.10 | 0.64 | 1.23 |
| Kif13a | 0.97 | 2.00 | 1.03 | 1.53 | 0.35 | 1.35 | 0.84 | 0.94 | 0.78 | 0.36 | 0.37 | 0.98 |
| Kif21a | 1.25 | 1.16 | 0.84 | 1.69 | 0.34 | 0.71 | 1.43 | 1.41 | 1.03 | 1.00 | 0.45 | 1.04 |
| Kif3b | 0.78 | 1.00 | 1.00 | 0.68 | 0.27 | 0.73 | 1.03 | 1.12 | 1.14 | 0.81 | 0.51 | 1.09 |
| Kifc5b | 1.00 | 1.00 | 1.00 | 1.00 | 1.00 | 1.00 | 1.00 | 1.00 | 1.00 | 1.00 | 1.00 | 1.00 |
| Kirrel | 0.83 | 1.45 | 1.24 | 2.77 | 0.43 | 1.07 | 1.04 | 1.37 | 1.16 | 0.43 | 0.35 | 1.00 |
| Klf1 | 1.00 | 1.00 | 1.00 | 1.00 | 1.00 | 1.00 | 1.00 | 1.00 | 1.00 | 1.00 | 0.94 | 1.00 |
| Klf3 | 0.95 | 1.00 | 1.44 | 1.72 | 0.32 | 0.82 | 1.30 | 2.18 | 1.66 | 1.03 | 0.87 | 1.09 |
| Klf4 | 1.77 | 2.62 | 1.50 | 1.46 | 0.21 | 1.03 | 1.07 | 1.08 | 1.13 | 0.15 | 0.26 | 0.89 |
| Klf7 | 1.00 | 1.00 | 1.30 | 1.56 | 1.00 | 0.55 | 1.92 | 2.85 | 1.93 | 1.00 | 1.00 | 1.17 |
| Klf9 | 0.99 | 3.09 | 1.25 | 1.63 | 0.08 | 1.04 | 1.53 | 2.43 | 1.26 | 1.00 | 0.10 | 1.14 |
| Klhl20 | 0.90 | 1.11 | 0.75 | 1.48 | 0.29 | 0.83 | 1.13 | 1.24 | 1.17 | 0.66 | 0.23 | 0.98 |
| Klhl24 | 1.02 | 2.79 | 1.54 | 2.37 | 0.23 | 1.08 | 1.66 | 2.46 | 1.33 | 0.46 | 0.28 | 1.02 |
| Klhl9 | 1.07 | 1.61 | 1.20 | 2.01 | 0.54 | 1.21 | 0.88 | 1.07 | 1.01 | 0.58 | 0.48 | 1.04 |
| Klra22 | 1.00 | 1.00 | 1.00 | 1.00 | 1.00 | 1.00 | 1.00 | 1.00 | 1.00 | 1.00 | 1.00 | 1.00 |
| Klrd1 | 1.00 | 1.00 | 1.00 | 1.00 | 1.00 | 1.00 | 1.00 | 1.00 | 1.00 | 0.32 | 0.39 | 0.56 |
| Kmt2d | 0.87 | 0.88 | 1.26 | 1.17 | 0.57 | 0.86 | 1.04 | 1.21 | 1.38 | 1.24 | 1.06 | 1.11 |
| Kmt2e | 0.81 | 1.30 | 0.87 | 1.76 | 0.09 | 1.00 | 1.05 | 1.05 | 1.08 | 0.49 | 0.13 | 0.95 |
| Krcc1 | 0.76 | 1.66 | 0.91 | 2.26 | 0.18 | 0.82 | 1.06 | 1.19 | 1.04 | 0.08 | 0.25 | 1.00 |
| Kremen1 | 1.04 | 1.73 | 1.14 | 1.41 | 0.32 | 1.10 | 1.01 | 1.22 | 1.25 | 0.36 | 0.40 | 1.15 |
| Krt10 | 1.00 | 0.50 | 1.06 | 0.59 | 1.58 | 0.65 | 0.53 | 0.99 | 0.94 | 0.17 | 1.27 | 0.90 |
| Krt6b | 1.00 | 1.00 | 1.00 | 1.00 | 1.00 | 1.00 | 1.00 | 1.00 | 1.00 | 1.00 | 1.00 | 1.00 |
| Krt80 | 2.55 | 1.00 | 2.29 | 1.00 | 1.00 | 1.00 | 3.44 | 3.07 | 3.30 | 1.00 | 0.07 | 1.51 |
| Krt83 | 1.00 | 1.00 | 1.00 | 1.00 | 1.00 | 1.00 | 1.00 | 1.00 | 1.00 | 1.00 | 1.00 | 1.00 |
| Krtap16-3 | 1.00 | 1.00 | 1.00 | 1.00 | 1.00 | 1.00 | 1.00 | 1.00 | 1.00 | 1.00 | 1.00 | 1.00 |
| Krtap4-1 | 1.00 | 1.00 | 1.00 | 1.00 | 1.00 | 1.00 | 1.00 | 1.00 | 1.00 | 1.00 | 1.00 | 1.00 |
| Krtap4-16 | 1.00 | 1.00 | 1.00 | 1.00 | 1.00 | 1.00 | 1.00 | 1.00 | 1.00 | 1.00 | 1.00 | 1.00 |
| Krtap4-2 | 1.00 | 1.00 | 1.00 | 1.00 | 1.00 | 1.00 | 1.00 | 1.00 | 1.00 | 1.00 | 1.00 | 1.00 |
| Krtap4-8 | 1.00 | 1.00 | 1.00 | 1.00 | 1.00 | 1.00 | 1.00 | 1.00 | 1.00 | 1.00 | 1.00 | 1.00 |
| Krtap9-1 | 1.00 | 1.00 | 1.00 | 1.00 | 1.00 | 1.00 | 1.00 | 1.00 | 1.00 | 1.00 | 1.00 | 1.00 |
| Krtcap3 | 1.00 | 1.00 | 1.00 | 0.80 | 1.00 | 0.61 | 1.00 | 1.00 | 1.09 | 0.20 | 0.52 | 0.89 |
| Ky | 0.20 | 0.30 | 0.13 | 1.00 | 1.00 | 1.00 | 0.37 | 0.25 | 0.37 | 1.00 | 1.69 | 4.77 |
| L2hgdh | 0.73 | 1.00 | 0.84 | 1.02 | 0.47 | 0.89 | 0.93 | 0.96 | 0.92 | 0.80 | 0.40 | 0.96 |
| LOC100503496 | 1.00 | 1.00 | 1.00 | 1.00 | 1.00 | 1.00 | 0.54 | 1.97 | 0.96 | 1.00 | 1.00 | 1.74 |
| LOC106740 | 0.55 | 0.86 | 0.55 | 1.42 | 0.25 | 1.13 | 0.48 | 0.64 | 0.57 | 0.41 | 0.32 | 1.18 |
| Lacc1 | 1.00 | 1.00 | 1.00 | 1.00 | 1.00 | 0.94 | 0.97 | 1.26 | 1.34 | 1.00 | 0.38 | 0.91 |
| Lactb | 0.85 | 1.06 | 0.70 | 0.50 | 0.54 | 0.77 | 0.73 | 0.90 | 0.80 | 0.61 | 0.82 | 1.11 |
| Lactb2 | 1.22 | 1.68 | 1.28 | 1.38 | 0.15 | 0.76 | 1.08 | 1.26 | 0.96 | 0.58 | 0.23 | 1.02 |
| Larp4b | 0.68 | 1.34 | 0.86 | 2.27 | 0.14 | 0.89 | 0.83 | 1.19 | 1.03 | 1.25 | 0.42 | 1.20 |
| Lat2 | 1.00 | 0.97 | 1.00 | 1.00 | 1.83 | 0.92 | 0.68 | 0.77 | 1.02 | 2.03 | 1.40 | 0.61 |
| Lca5 | 1.00 | 1.00 | 1.00 | 1.00 | 1.00 | 1.00 | 0.79 | 0.75 | 0.97 | 1.00 | 0.72 | 0.83 |
| Ldlrad3 | 2.28 | 2.95 | 2.22 | 2.35 | 0.38 | 1.35 | 1.24 | 1.52 | 1.63 | 0.32 | 0.35 | 1.14 |
| Leap2 | 1.00 | 1.00 | 1.00 | 1.00 | 1.00 | 1.00 | 1.00 | 1.00 | 1.00 | 1.00 | 1.00 | 1.00 |
| Lefty1 | 1.00 | 0.91 | 0.81 | 1.00 | 1.00 | 1.00 | 0.69 | 0.55 | 0.54 | 0.37 | 0.26 | 0.37 |
| Lep | 0.44 | 0.75 | 0.13 | 1.00 | 1.00 | 0.13 | 1.00 | 1.00 | 1.00 | 1.00 | 1.00 | 1.00 |
| Lgals12 | 0.77 | 1.00 | 0.55 | 0.58 | 0.18 | 0.65 | 1.00 | 1.00 | 1.00 | 1.00 | 1.00 | 1.05 |
| Lgals2 | 1.00 | 1.00 | 1.00 | 1.00 | 1.00 | 1.00 | 1.03 | 1.00 | 1.00 | 0.17 | 1.87 | 1.04 |
| Lima1 | 0.82 | 1.00 | 0.93 | 0.94 | 0.12 | 0.91 | 0.74 | 0.79 | 0.89 | 0.37 | 0.37 | 0.87 |
| Lin52 | 0.92 | 2.24 | 1.06 | 1.17 | 0.09 | 1.05 | 1.04 | 1.13 | 0.84 | 0.37 | 0.14 | 1.05 |
| Lingo1 | 1.00 | 1.00 | 1.00 | 1.00 | 0.15 | 1.00 | 1.00 | 0.84 | 0.75 | 1.00 | 0.99 | 0.74 |
| Lipg | 1.00 | 1.00 | 1.00 | 1.00 | 1.00 | 0.61 | 1.00 | 1.00 | 1.00 | 0.40 | 0.16 | 1.00 |
| Lipo1 | 0.90 | 1.76 | 0.76 | 2.05 | 0.29 | 0.85 | 0.87 | 1.04 | 1.05 | 0.45 | 0.15 | 0.92 |
| Lix1l | 0.60 | 1.00 | 0.74 | 1.49 | 0.40 | 1.06 | 0.90 | 0.93 | 1.03 | 0.87 | 0.31 | 0.96 |
| Lnpep | 1.31 | 1.00 | 1.00 | 2.02 | 0.44 | 1.01 | 1.57 | 1.65 | 1.33 | 1.00 | 1.00 | 1.08 |
| Lonrf1 | 1.02 | 1.27 | 1.18 | 1.45 | 0.67 | 0.77 | 0.81 | 0.97 | 0.65 | 1.00 | 0.29 | 0.64 |
| Loxl1 | 1.20 | 0.89 | 1.02 | 0.20 | 0.36 | 0.46 | 1.03 | 0.72 | 1.19 | 0.69 | 0.66 | 0.82 |
| Lpar3 | 1.00 | 1.00 | 1.00 | 1.00 | 1.00 | 1.00 | 1.00 | 1.00 | 1.00 | 0.93 | 1.02 | 1.11 |
| Lpar5 | 1.00 | 1.00 | 1.00 | 1.00 | 1.00 | 1.00 | 1.00 | 1.00 | 1.00 | 1.00 | 1.00 | 0.93 |
| Lpcat1 | 1.00 | 1.00 | 1.00 | 0.97 | 1.00 | 1.60 | 1.40 | 1.75 | 1.13 | 1.00 | 0.13 | 1.24 |
| Lphn1 | 0.94 | 0.90 | 0.74 | 0.62 | 0.18 | 0.79 | 0.83 | 0.95 | 0.89 | 1.07 | 0.72 | 0.87 |
| Lrch1 | 1.12 | 1.00 | 1.08 | 2.23 | 0.45 | 1.34 | 2.32 | 2.88 | 1.15 | 0.69 | 0.53 | 1.00 |
| Lrch3 | 0.91 | 1.00 | 1.03 | 3.10 | 0.17 | 1.10 | 1.18 | 1.20 | 1.01 | 1.00 | 0.41 | 0.99 |

Fig. 35- 54

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Keg1 | 1.00 | 1.00 | 1.00 | 1.01 | 1.49 | 1.11 | 0.23 | 0.04 | 0.20 | 1.00 | 1.00 | 1.00 |
| Kel | 1.00 | 1.00 | 1.00 | 1.00 | 1.00 | 1.00 | 1.00 | 1.00 | 1.00 | 1.00 | 1.00 | 1.00 |
| Khnyn | 0.62 | 0.45 | 1.17 | 1.48 | 2.02 | 1.58 | 1.01 | 2.09 | 1.46 | 0.97 | 0.34 | 0.95 |
| Kif13a | 1.42 | 1.15 | 1.28 | 1.01 | 1.00 | 0.92 | 0.97 | 1.00 | 0.91 | 1.10 | 0.75 | 0.96 |
| Kif21a | 2.00 | 1.61 | 1.32 | 1.41 | 2.02 | 1.10 | 1.40 | 1.00 | 1.01 | 1.14 | 0.80 | 0.83 |
| Kif3b | 0.74 | 0.65 | 0.95 | 1.16 | 1.26 | 1.04 | 1.00 | 1.00 | 0.98 | 0.97 | 0.82 | 0.93 |
| Kifc5b | 0.63 | 0.84 | 0.67 | 0.88 | 1.00 | 0.76 | 1.00 | 1.00 | 1.00 | 1.00 | 1.09 | 0.93 |
| Kirrel | 1.65 | 1.16 | 1.54 | 1.13 | 1.00 | 1.29 | 1.00 | 1.00 | 1.00 | 0.92 | 0.69 | 0.92 |
| Klf1 | 1.00 | 1.00 | 1.00 | 0.96 | 0.71 | 1.12 | 0.62 | 1.12 | 1.00 | 1.00 | 1.00 | 1.00 |
| Klf3 | 0.41 | 0.27 | 0.78 | 1.12 | 1.10 | 1.33 | 1.69 | 1.56 | 1.33 | 1.06 | 0.50 | 0.85 |
| Klf4 | 1.48 | 1.18 | 1.12 | 1.42 | 1.00 | 1.27 | 1.26 | 1.00 | 1.00 | 1.14 | 0.88 | 1.05 |
| Klf7 | 0.38 | 0.15 | 0.51 | 2.05 | 1.00 | 2.08 | 1.00 | 1.00 | 1.00 | 1.18 | 1.00 | 0.82 |
| Klf9 | 1.98 | 1.26 | 1.61 | 1.66 | 1.10 | 1.57 | 0.99 | 1.19 | 1.16 | 1.31 | 0.40 | 0.93 |
| Klhl20 | 0.69 | 0.67 | 0.91 | 0.86 | 1.00 | 1.13 | 1.06 | 1.00 | 0.97 | 0.87 | 0.65 | 1.00 |
| Klhl24 | 0.83 | 0.66 | 1.01 | 1.41 | 1.45 | 1.18 | 1.25 | 1.00 | 1.09 | 1.15 | 0.57 | 0.98 |
| Klhl9 | 0.91 | 0.78 | 1.06 | 1.00 | 0.97 | 1.11 | 1.05 | 0.28 | 1.14 | 1.14 | 0.89 | 1.11 |
| Klra22 | 1.00 | 0.80 | 1.00 | 1.00 | 1.00 | 1.00 | 1.00 | 1.00 | 1.00 | 1.00 | 1.00 | 1.00 |
| Klrd1 | 3.30 | 1.70 | 1.09 | 1.00 | 1.00 | 1.00 | 1.00 | 1.00 | 1.00 | 1.00 | 0.77 | 1.00 |
| Kmt2d | 0.55 | 0.44 | 1.05 | 1.08 | 0.78 | 1.18 | 0.82 | 1.26 | 1.20 | 0.92 | 0.59 | 0.90 |
| Kmt2e | 0.59 | 0.50 | 1.00 | 1.05 | 1.00 | 0.96 | 0.88 | 1.00 | 1.15 | 0.92 | 0.51 | 0.94 |
| Krcc1 | 0.75 | 0.64 | 0.88 | 0.78 | 1.36 | 0.76 | 1.10 | 0.19 | 1.18 | 1.03 | 0.82 | 1.01 |
| Kremen1 | 0.56 | 0.57 | 0.64 | 1.16 | 2.22 | 1.09 | 0.98 | 1.00 | 1.03 | 1.03 | 0.75 | 0.99 |
| Krt10 | 0.71 | 0.59 | 0.55 | 0.86 | 0.65 | 0.84 | 0.87 | 0.55 | 1.09 | 0.91 | 2.00 | 0.33 |
| Krt6b | 1.00 | 1.00 | 1.00 | 1.00 | 1.00 | 1.00 | 1.00 | 1.00 | 1.00 | 1.00 | 1.00 | 1.00 |
| Krt80 | 0.49 | 0.85 | 1.00 | 1.35 | 1.00 | 1.21 | 1.00 | 1.00 | 1.00 | 1.00 | 1.00 | 0.73 |
| Krt83 | 1.00 | 1.00 | 1.00 | 1.00 | 1.00 | 1.00 | 1.00 | 1.00 | 1.00 | 1.00 | 1.00 | 1.35 |
| Krtap16-3 | 1.00 | 1.00 | 1.00 | 1.00 | 1.00 | 1.00 | 1.00 | 1.00 | 1.00 | 1.00 | 1.00 | 1.00 |
| Krtap4-1 | 1.00 | 1.00 | 1.00 | 1.00 | 1.00 | 1.00 | 1.00 | 1.00 | 1.00 | 1.00 | 1.00 | 1.00 |
| Krtap4-16 | 1.00 | 1.00 | 1.00 | 1.00 | 1.00 | 1.00 | 1.00 | 1.00 | 1.00 | 1.00 | 1.00 | 1.00 |
| Krtap4-2 | 1.00 | 1.00 | 1.00 | 1.00 | 1.00 | 1.00 | 1.00 | 1.00 | 1.00 | 1.00 | 1.00 | 1.00 |
| Krtap4-8 | 1.00 | 1.00 | 1.00 | 1.00 | 1.00 | 1.00 | 1.00 | 1.00 | 1.00 | 1.00 | 1.00 | 1.00 |
| Krtap9-1 | 1.00 | 1.00 | 1.00 | 1.00 | 1.00 | 1.00 | 1.00 | 1.00 | 1.00 | 1.00 | 1.00 | 1.00 |
| Krtcap3 | 1.22 | 0.86 | 1.03 | 0.80 | 1.65 | 0.70 | 1.00 | 1.00 | 1.00 | 0.94 | 1.00 | 0.93 |
| Ky | 1.00 | 1.00 | 1.00 | 1.00 | 1.00 | 1.00 | 1.00 | 1.00 | 1.00 | 1.00 | 1.00 | 1.00 |
| L2hgdh | 0.88 | 0.66 | 0.87 | 0.75 | 1.53 | 0.85 | 0.68 | 0.22 | 0.74 | 1.10 | 0.81 | 1.00 |
| LOC100503496 | 0.62 | 0.40 | 0.47 | 1.51 | 1.00 | 0.79 | 1.00 | 1.00 | 1.00 | 1.08 | 0.56 | 0.80 |
| LOC106740 | 0.74 | 0.75 | 0.80 | 0.96 | 1.00 | 0.84 | 0.74 | 1.00 | 1.25 | 0.98 | 0.72 | 1.41 |
| Lacc1 | 1.62 | 1.08 | 1.48 | 1.03 | 1.00 | 0.93 | 2.28 | 1.00 | 2.07 | 0.95 | 0.93 | 0.85 |
| Lactb | 0.93 | 0.92 | 1.16 | 1.09 | 1.61 | 0.98 | 0.46 | 0.19 | 0.53 | 0.69 | 0.85 | 0.77 |
| Lactb2 | 0.75 | 0.68 | 0.98 | 1.17 | 1.44 | 1.05 | 0.86 | 0.44 | 0.92 | 1.13 | 0.65 | 1.07 |
| Larp4b | 0.49 | 0.40 | 0.80 | 1.38 | 1.29 | 1.21 | 0.84 | 1.00 | 0.73 | 1.09 | 0.56 | 1.06 |
| Lat2 | 1.08 | 1.17 | 1.24 | 0.95 | 0.82 | 1.00 | 1.00 | 1.00 | 1.00 | 0.78 | 0.69 | 0.89 |
| Lca5 | 0.13 | 0.13 | 0.15 | 1.00 | 1.00 | 1.00 | 1.00 | 1.00 | 1.00 | 0.78 | 1.00 | 0.64 |
| Ldlrad3 | 0.57 | 0.38 | 0.74 | 0.93 | 0.96 | 0.89 | 0.49 | 1.00 | 1.05 | 0.82 | 0.62 | 0.92 |
| Leap2 | 1.00 | 1.00 | 1.00 | 1.00 | 1.00 | 1.00 | 0.16 | 0.38 | 0.35 | 1.00 | 1.00 | 1.00 |
| Lefty1 | 0.78 | 0.65 | 0.56 | 1.00 | 0.96 | 1.00 | 1.00 | 1.00 | 1.00 | 0.14 | 0.11 | 0.15 |
| Lep | 1.00 | 1.00 | 0.29 | 1.00 | 1.00 | 1.00 | 1.00 | 1.00 | 1.00 | 1.00 | 1.00 | 1.00 |
| Lgals12 | 0.46 | 0.23 | 0.23 | 1.00 | 1.00 | 1.00 | 1.00 | 1.00 | 1.00 | 1.18 | 1.12 | 1.03 |
| Lgals2 | 2.61 | 0.63 | 1.00 | 1.00 | 1.00 | 1.00 | 1.00 | 1.00 | 1.00 | 0.95 | 1.04 | 4.58 |
| Lima1 | 1.06 | 0.82 | 1.32 | 0.87 | 1.46 | 1.02 | 0.46 | 0.24 | 0.66 | 0.90 | 0.69 | 0.94 |
| Lin52 | 0.78 | 0.80 | 0.78 | 0.90 | 0.96 | 0.90 | 0.78 | 1.00 | 0.96 | 0.99 | 0.86 | 1.02 |
| Lingo1 | 0.86 | 0.85 | 1.00 | 1.00 | 1.00 | 1.00 | 1.00 | 1.00 | 1.00 | 1.00 | 1.00 | 1.00 |
| Lipg | 1.39 | 1.12 | 1.11 | 0.88 | 1.00 | 1.00 | 0.45 | 1.00 | 0.96 | 1.24 | 0.60 | 1.06 |
| Lipo1 | 0.96 | 0.91 | 1.08 | 1.06 | 2.32 | 0.96 | 1.00 | 1.00 | 1.00 | 1.00 | 0.91 | 1.21 |
| Lix1l | 0.90 | 0.80 | 1.32 | 0.91 | 1.00 | 1.14 | 0.99 | 1.00 | 1.35 | 0.90 | 0.41 | 1.01 |
| Lnpep | 0.78 | 0.46 | 1.08 | 1.19 | 1.00 | 1.00 | 1.00 | 1.00 | 1.00 | 1.25 | 1.00 | 0.79 |
| Lonrf1 | 0.86 | 0.64 | 0.83 | 0.81 | 1.00 | 0.93 | 1.45 | 1.00 | 0.85 | 0.86 | 0.67 | 0.75 |
| Loxl1 | 0.61 | 0.69 | 0.89 | 1.01 | 0.63 | 0.88 | 1.00 | 1.00 | 1.00 | 0.86 | 0.77 | 0.93 |
| Lpar3 | 1.10 | 0.86 | 1.08 | 0.87 | 0.96 | 0.97 | 1.00 | 1.00 | 1.00 | 0.99 | 1.17 | 1.76 |
| Lpar5 | 0.36 | 0.28 | 0.81 | 1.00 | 1.00 | 1.00 | 1.00 | 1.00 | 1.00 | 0.83 | 0.36 | 1.21 |
| Lpcat1 | 0.58 | 0.50 | 1.13 | 0.94 | 1.00 | 1.76 | 1.00 | 1.00 | 1.00 | 1.20 | 0.53 | 1.18 |
| Lphn1 | 0.43 | 0.48 | 0.58 | 0.78 | 0.85 | 0.89 | 0.50 | 1.00 | 0.82 | 0.87 | 0.82 | 0.87 |
| Lrch1 | 0.86 | 0.85 | 0.96 | 0.96 | 1.09 | 1.06 | 0.96 | 1.00 | 1.04 | 1.08 | 0.86 | 0.95 |
| Lrch3 | 0.71 | 0.57 | 0.91 | 1.21 | 1.00 | 1.03 | 1.13 | 1.00 | 1.29 | 1.06 | 0.35 | 0.93 |

Fig. 35-55

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Keg1 | 1.00 | 1.00 | 1.00 | 1.18 | 1.00 | 2.21 | 1.00 | 1.00 | 1.00 | 1.00 | 1.00 | 1.00 |
| Kel | 1.00 | 1.00 | 1.00 | 1.00 | 1.00 | 1.00 | 1.00 | 1.00 | 1.00 | 0.39 | 0.34 | 0.17 |
| Khnyn | 1.05 | 1.04 | 0.70 | 1.37 | 0.70 | 1.04 | 1.06 | 1.00 | 1.30 | 0.96 | 0.42 | 1.29 |
| Kif13a | 1.03 | 1.11 | 0.78 | 1.11 | 0.35 | 1.28 | 0.78 | 1.00 | 0.85 | 0.88 | 0.69 | 0.85 |
| Kif21a | 1.50 | 1.62 | 1.07 | 0.83 | 1.00 | 0.62 | 0.87 | 0.85 | 0.96 | 1.00 | 2.72 | 1.00 |
| Kif3b | 0.99 | 1.05 | 0.74 | 0.93 | 0.61 | 0.67 | 1.24 | 1.27 | 1.06 | 0.84 | 0.84 | 0.98 |
| Kifc5b | 0.50 | 0.63 | 0.72 | 1.00 | 1.00 | 0.95 | 0.91 | 1.00 | 1.10 | 0.79 | 0.70 | 0.74 |
| Kirrel | 1.10 | 1.10 | 0.98 | 1.07 | 0.26 | 0.75 | 1.06 | 1.00 | 0.93 | 1.10 | 0.80 | 1.37 |
| Klf1 | 1.00 | 1.00 | 1.00 | 1.00 | 1.00 | 1.00 | 0.74 | 0.86 | 0.86 | 0.31 | 0.32 | 0.16 |
| Klf3 | 0.88 | 0.97 | 0.59 | 1.29 | 0.16 | 0.73 | 1.06 | 1.00 | 1.27 | 0.75 | 0.47 | 1.01 |
| Klf4 | 0.82 | 0.99 | 0.79 | 1.26 | 0.13 | 1.18 | 1.13 | 0.57 | 0.99 | 1.11 | 1.01 | 0.77 |
| Klf7 | 0.99 | 0.99 | 0.38 | 1.42 | 0.48 | 0.26 | 1.05 | 1.00 | 1.00 | 0.73 | 0.40 | 0.98 |
| Klf9 | 1.53 | 1.89 | 1.20 | 1.41 | 0.41 | 0.92 | 1.18 | 1.05 | 1.07 | 1.51 | 1.18 | 1.63 |
| Klhl20 | 0.93 | 1.02 | 1.08 | 0.87 | 1.00 | 0.84 | 1.16 | 1.00 | 0.90 | 0.94 | 0.70 | 1.05 |
| Klhl24 | 1.41 | 1.51 | 1.09 | 1.18 | 0.20 | 0.78 | 1.13 | 0.72 | 1.04 | 1.22 | 0.68 | 1.42 |
| Klhl9 | 0.97 | 0.97 | 0.94 | 0.84 | 0.12 | 0.91 | 1.17 | 0.44 | 0.93 | 1.06 | 0.96 | 1.28 |
| Klra22 | 1.00 | 1.00 | 1.00 | 1.00 | 1.00 | 0.83 | 1.00 | 1.00 | 1.00 | 1.00 | 0.60 | 1.00 |
| Klrd1 | 1.00 | 1.00 | 1.00 | 0.61 | 1.00 | 1.00 | 1.00 | 1.00 | 1.00 | 0.81 | 0.71 | 0.58 |
| Kmt2d | 0.95 | 0.92 | 0.83 | 1.09 | 0.18 | 1.07 | 1.48 | 1.26 | 1.35 | 0.89 | 0.51 | 1.29 |
| Kmt2e | 0.99 | 1.06 | 1.03 | 0.96 | 0.24 | 1.01 | 1.07 | 1.09 | 0.99 | 0.93 | 0.55 | 1.07 |
| Krcc1 | 0.92 | 0.93 | 0.96 | 0.79 | 0.20 | 0.82 | 0.95 | 0.12 | 0.90 | 0.91 | 0.63 | 0.92 |
| Kremen1 | 0.98 | 1.01 | 0.92 | 1.24 | 0.61 | 1.15 | 1.22 | 1.16 | 1.26 | 0.93 | 0.87 | 1.07 |
| Krt10 | 0.82 | 1.11 | 1.05 | 1.03 | 1.00 | 3.97 | 1.15 | 0.60 | 1.14 | 0.95 | 2.07 | 1.13 |
| Krt6b | 0.69 | 0.97 | 0.84 | 1.00 | 1.00 | 1.00 | 1.00 | 1.00 | 1.00 | 1.00 | 1.00 | 1.00 |
| Krt80 | 0.99 | 0.93 | 0.92 | 0.89 | 1.00 | 1.28 | 1.00 | 1.00 | 1.00 | 0.57 | 0.37 | 0.49 |
| Krt83 | 1.00 | 1.00 | 1.00 | 1.00 | 1.00 | 1.00 | 1.00 | 1.00 | 1.00 | 1.00 | 1.00 | 1.00 |
| Krtap16-3 | 1.00 | 1.00 | 1.00 | 1.00 | 1.00 | 1.00 | 1.00 | 1.00 | 1.00 | 1.00 | 1.00 | 1.00 |
| Krtap4-1 | 1.00 | 1.00 | 1.00 | 1.00 | 1.00 | 1.00 | 1.00 | 1.00 | 1.00 | 1.00 | 1.00 | 1.00 |
| Krtap4-16 | 1.00 | 1.00 | 1.00 | 1.00 | 1.00 | 1.00 | 1.00 | 1.00 | 1.00 | 1.00 | 1.00 | 1.00 |
| Krtap4-2 | 1.00 | 1.00 | 1.00 | 1.00 | 1.00 | 1.00 | 1.00 | 1.00 | 1.00 | 1.00 | 1.00 | 1.00 |
| Krtap4-8 | 1.00 | 1.00 | 1.00 | 1.00 | 1.00 | 1.00 | 1.00 | 1.00 | 1.00 | 1.00 | 1.00 | 1.00 |
| Krtap9-1 | 1.00 | 1.00 | 1.00 | 1.00 | 1.00 | 1.00 | 1.00 | 1.00 | 1.00 | 1.00 | 1.00 | 1.00 |
| Krtcap3 | 1.10 | 1.31 | 0.92 | 1.08 | 1.00 | 1.40 | 1.01 | 0.61 | 0.80 | 0.71 | 1.01 | 1.12 |
| Ky | 1.00 | 1.00 | 1.00 | 1.00 | 1.00 | 1.00 | 1.00 | 1.00 | 1.00 | 1.00 | 1.00 | 1.00 |
| L2hgdh | 0.94 | 1.01 | 0.96 | 0.79 | 1.00 | 0.98 | 0.98 | 0.50 | 0.88 | 1.42 | 1.13 | 0.91 |
| LOC100503496 | 2.20 | 0.52 | 1.00 | 2.03 | 0.50 | 0.86 | 1.00 | 1.00 | 1.00 | 1.08 | 0.16 | 0.72 |
| LOC106740 | 1.02 | 0.81 | 1.39 | 1.10 | 0.91 | 1.28 | 0.91 | 0.55 | 0.78 | 0.79 | 0.80 | 1.06 |
| Lacc1 | 0.74 | 0.74 | 0.80 | 0.76 | 1.00 | 0.69 | 1.28 | 1.00 | 0.74 | 1.39 | 0.94 | 1.33 |
| Lactb | 0.87 | 0.83 | 0.82 | 0.69 | 0.66 | 0.92 | 0.78 | 0.29 | 0.85 | 1.10 | 1.04 | 0.88 |
| Lactb2 | 0.99 | 0.76 | 0.87 | 0.88 | 0.94 | 1.00 | 1.00 | 1.00 | 1.21 | 1.05 | 0.72 | 0.97 |
| Larp4b | 1.06 | 1.01 | 0.75 | 1.20 | 0.30 | 0.58 | 1.21 | 0.96 | 1.08 | 0.93 | 0.60 | 0.99 |
| Lat2 | 0.59 | 0.69 | 0.98 | 0.41 | 0.38 | 0.28 | 0.75 | 3.00 | 0.90 | 0.66 | 0.60 | 0.82 |
| Lca5 | 0.50 | 0.48 | 0.51 | 0.57 | 1.00 | 0.61 | 0.91 | 0.38 | 0.92 | 0.24 | 0.20 | 0.22 |
| Ldlrad3 | 0.98 | 1.04 | 1.11 | 1.08 | 0.43 | 1.07 | 0.90 | 1.00 | 0.89 | 1.20 | 0.71 | 0.98 |
| Leap2 | 1.00 | 1.00 | 1.00 | 1.00 | 1.00 | 1.00 | 1.00 | 1.00 | 1.00 | 1.00 | 1.00 | 1.00 |
| Lefty1 | 0.37 | 0.38 | 0.28 | 0.52 | 1.00 | 0.62 | 1.00 | 1.00 | 1.00 | 0.19 | 0.20 | 0.24 |
| Lep | 1.00 | 1.00 | 1.00 | 0.05 | 0.06 | 0.06 | 1.00 | 1.00 | 1.00 | 1.00 | 1.00 | 1.00 |
| Lgals12 | 0.80 | 0.78 | 0.66 | 0.11 | 0.09 | 0.30 | 1.00 | 1.00 | 1.00 | 1.00 | 1.00 | 1.00 |
| Lgals2 | 0.55 | 0.56 | 0.49 | 1.43 | 1.31 | 2.29 | 1.00 | 1.00 | 1.00 | 1.00 | 1.00 | 1.00 |
| Lima1 | 0.70 | 0.71 | 0.61 | 0.82 | 0.15 | 0.73 | 0.77 | 0.92 | 0.98 | 0.72 | 0.56 | 0.89 |
| Lin52 | 1.23 | 1.16 | 1.19 | 0.74 | 0.97 | 0.97 | 1.01 | 0.64 | 1.14 | 1.14 | 0.81 | 1.00 |
| Lingo1 | 1.00 | 1.00 | 1.00 | 1.00 | 1.00 | 1.00 | 1.02 | 0.97 | 1.16 | 0.73 | 3.22 | 0.79 |
| Lipg | 0.81 | 0.82 | 0.68 | 2.09 | 1.00 | 0.79 | 0.63 | 1.00 | 0.61 | 1.08 | 1.00 | 1.00 |
| Lipo1 | 0.94 | 1.04 | 0.72 | 0.88 | 1.00 | 0.86 | 1.15 | 1.00 | 1.01 | 1.17 | 0.80 | 1.14 |
| Lix1l | 1.02 | 0.95 | 1.01 | 0.72 | 0.26 | 0.73 | 1.01 | 0.96 | 0.93 | 1.08 | 0.72 | 1.21 |
| Lnpep | 1.06 | 1.12 | 0.62 | 0.89 | 0.10 | 0.69 | 1.00 | 1.00 | 1.00 | 0.81 | 0.76 | 1.21 |
| Lonrf1 | 0.77 | 0.87 | 0.82 | 0.62 | 1.00 | 0.69 | 0.76 | 1.00 | 1.05 | 1.10 | 0.98 | 0.73 |
| Loxl1 | 0.99 | 1.20 | 0.92 | 1.07 | 0.96 | 0.76 | 1.16 | 1.37 | 1.19 | 0.89 | 0.73 | 1.19 |
| Lpar3 | 0.67 | 0.73 | 0.50 | 0.61 | 1.00 | 0.62 | 0.88 | 0.62 | 0.96 | 0.84 | 0.69 | 0.81 |
| Lpar5 | 0.89 | 0.86 | 0.63 | 0.84 | 1.00 | 0.44 | 1.72 | 1.00 | 1.24 | 0.77 | 0.50 | 1.14 |
| Lpcat1 | 0.63 | 0.67 | 0.87 | 1.15 | 1.00 | 1.35 | 1.00 | 1.00 | 1.00 | 0.70 | 0.42 | 0.82 |
| Lphn1 | 0.84 | 0.91 | 0.94 | 0.78 | 0.87 | 0.91 | 1.07 | 1.09 | 1.03 | 0.61 | 1.16 | 0.82 |
| Lrch1 | 1.16 | 1.19 | 1.25 | 1.15 | 0.59 | 0.90 | 1.00 | 1.00 | 1.00 | 0.97 | 0.70 | 0.92 |
| Lrch3 | 1.01 | 1.01 | 0.95 | 0.98 | 0.28 | 0.80 | 1.09 | 1.00 | 1.03 | 1.00 | 0.53 | 0.95 |

Fig. 35- 56

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Keg1 | 1.00 | 1.00 | 1.00 | 1.00 | 1.00 | 1.00 | 1.00 | 1.00 | 1.00 | 1.00 | 1.00 | 1.00 |
| Kel | 1.00 | 1.00 | 1.00 | 1.00 | 1.00 | 1.00 | 1.00 | 1.00 | 1.00 | 1.38 | 0.72 | 0.73 |
| Khnyn | 1.27 | 0.99 | 1.47 | 0.85 | 1.03 | 0.93 | 0.99 | 0.16 | 1.40 | 0.60 | 0.76 | 0.57 |
| Kif13a | 1.00 | 0.98 | 1.00 | 0.91 | 1.00 | 0.95 | 0.73 | 0.07 | 1.14 | 0.55 | 0.67 | 0.62 |
| Kif21a | 1.16 | 1.58 | 1.04 | 0.99 | 1.00 | 0.95 | 1.22 | 0.09 | 1.47 | 1.00 | 1.00 | 1.00 |
| Kif3b | 1.09 | 1.14 | 1.31 | 0.95 | 0.28 | 0.98 | 0.97 | 0.14 | 1.01 | 0.65 | 0.93 | 0.97 |
| Kifc5b | 1.00 | 1.00 | 1.00 | 1.06 | 1.00 | 1.19 | 0.72 | 0.31 | 1.21 | 0.20 | 1.06 | 0.94 |
| Kirrel | 1.00 | 1.00 | 1.00 | 0.94 | 0.79 | 1.10 | 1.00 | 0.12 | 1.33 | 1.00 | 1.00 | 1.00 |
| Klf1 | 1.00 | 1.00 | 1.00 | 1.00 | 1.00 | 1.00 | 1.00 | 1.00 | 1.00 | 0.55 | 0.65 | 0.81 |
| Klf3 | 1.25 | 1.80 | 1.30 | 0.81 | 1.00 | 0.83 | 0.61 | 0.08 | 0.71 | 0.63 | 0.94 | 0.58 |
| Klf4 | 1.00 | 1.76 | 1.21 | 1.12 | 1.00 | 0.86 | 0.82 | 0.05 | 0.77 | 0.30 | 0.76 | 0.80 |
| Klf7 | 1.00 | 1.00 | 1.00 | 0.77 | 1.00 | 0.74 | 1.00 | 1.00 | 1.00 | 1.00 | 0.74 | 0.60 |
| Klf9 | 1.06 | 1.21 | 1.23 | 1.02 | 1.00 | 1.03 | 1.54 | 0.08 | 2.14 | 1.00 | 1.73 | 1.04 |
| Klhl20 | 1.00 | 0.73 | 1.00 | 1.09 | 1.00 | 1.10 | 0.80 | 0.10 | 1.10 | 0.38 | 0.87 | 0.95 |
| Klhl24 | 1.10 | 1.31 | 1.52 | 0.88 | 1.00 | 0.91 | 1.17 | 0.17 | 1.75 | 0.53 | 1.31 | 0.99 |
| Klhl9 | 0.90 | 0.92 | 1.05 | 1.15 | 1.31 | 1.10 | 0.97 | 0.25 | 1.15 | 0.73 | 1.03 | 1.14 |
| Klra22 | 1.00 | 1.00 | 1.00 | 1.00 | 1.00 | 1.00 | 0.11 | 0.15 | 0.20 | 1.00 | 0.60 | 1.00 |
| Klrd1 | 1.00 | 1.00 | 1.00 | 1.00 | 1.00 | 1.00 | 0.18 | 0.69 | 0.37 | 0.53 | 0.91 | 0.56 |
| Kmt2d | 1.00 | 0.86 | 1.38 | 0.86 | 0.76 | 0.95 | 0.95 | 0.72 | 1.32 | 1.00 | 0.81 | 0.85 |
| Kmt2e | 1.02 | 1.06 | 1.19 | 0.87 | 0.35 | 0.91 | 0.83 | 0.08 | 1.09 | 0.27 | 0.77 | 1.00 |
| Krcc1 | 0.94 | 0.77 | 0.97 | 0.97 | 1.00 | 0.96 | 0.74 | 0.04 | 0.77 | 0.29 | 0.95 | 1.26 |
| Kremen1 | 1.65 | 1.32 | 1.05 | 1.11 | 1.00 | 1.07 | 0.96 | 0.10 | 0.99 | 0.80 | 1.03 | 0.76 |
| Krt10 | 1.00 | 1.00 | 1.45 | 0.91 | 1.93 | 0.78 | 0.58 | 0.40 | 0.37 | 1.15 | 1.00 | 1.00 |
| Krt6b | 1.00 | 1.00 | 1.00 | 1.00 | 1.00 | 1.00 | 0.47 | 0.16 | 0.93 | 1.00 | 1.00 | 1.00 |
| Krt80 | 1.00 | 1.00 | 1.00 | 0.97 | 1.00 | 1.11 | 0.84 | 0.01 | 0.65 | 1.00 | 0.71 | 1.12 |
| Krt83 | 1.00 | 1.00 | 1.00 | 1.00 | 1.00 | 1.00 | 2.02 | 0.09 | 0.93 | 1.00 | 1.00 | 1.00 |
| Krtap16-3 | 1.00 | 1.00 | 1.00 | 1.00 | 1.00 | 1.00 | 1.57 | 0.10 | 0.56 | 1.00 | 1.00 | 1.00 |
| Krtap4-1 | 1.00 | 1.00 | 1.00 | 1.00 | 1.00 | 1.00 | 1.54 | 0.11 | 0.47 | 1.00 | 1.00 | 1.00 |
| Krtap4-16 | 1.00 | 1.00 | 1.00 | 1.00 | 1.00 | 1.00 | 2.13 | 0.14 | 0.57 | 1.00 | 1.00 | 1.00 |
| Krtap4-2 | 1.00 | 1.00 | 1.00 | 1.00 | 1.00 | 1.00 | 1.46 | 0.12 | 0.74 | 1.00 | 1.00 | 1.00 |
| Krtap4-8 | 1.00 | 1.00 | 1.00 | 1.00 | 1.00 | 1.00 | 2.75 | 0.11 | 0.70 | 1.00 | 1.00 | 1.00 |
| Krtap9-1 | 1.00 | 1.00 | 1.00 | 1.00 | 1.00 | 1.00 | 2.82 | 0.05 | 0.44 | 1.00 | 1.00 | 1.00 |
| Krtcap3 | 1.45 | 0.94 | 1.62 | 1.00 | 1.00 | 1.00 | 0.83 | 0.14 | 0.80 | 1.32 | 1.28 | 1.06 |
| Ky | 1.00 | 1.00 | 1.00 | 1.16 | 1.00 | 1.24 | 0.74 | 1.00 | 1.21 | 1.00 | 1.00 | 1.00 |
| L2hgdh | 0.76 | 0.86 | 0.67 | 0.96 | 1.00 | 0.94 | 0.87 | 0.14 | 0.82 | 0.46 | 0.83 | 0.74 |
| LOC100503496 | 0.92 | 0.92 | 1.00 | 0.42 | 1.81 | 1.40 | 0.69 | 0.37 | 0.67 | 1.00 | 1.12 | 2.65 |
| LOC106740 | 1.00 | 1.94 | 0.90 | 0.92 | 0.38 | 0.93 | 0.97 | 0.20 | 1.16 | 0.52 | 0.92 | 1.04 |
| Lacc1 | 1.00 | 1.00 | 1.00 | 1.28 | 1.00 | 1.08 | 0.65 | 0.16 | 0.80 | 0.88 | 1.26 | 1.05 |
| Lactb | 1.37 | 0.95 | 0.78 | 0.99 | 2.08 | 1.15 | 0.86 | 0.64 | 1.03 | 0.86 | 1.27 | 1.02 |
| Lactb2 | 1.08 | 0.77 | 0.63 | 1.16 | 1.00 | 0.94 | 0.65 | 0.41 | 0.73 | 0.45 | 0.83 | 1.06 |
| Larp4b | 0.93 | 1.04 | 1.32 | 0.88 | 2.69 | 0.91 | 0.96 | 0.22 | 1.05 | 0.39 | 0.81 | 0.73 |
| Lat2 | 1.00 | 1.00 | 1.00 | 0.78 | 0.19 | 0.92 | 1.46 | 4.99 | 1.08 | 1.11 | 1.05 | 0.83 |
| Lca5 | 1.00 | 1.00 | 1.00 | 0.30 | 1.00 | 0.39 | 0.40 | 0.69 | 0.50 | 1.00 | 1.00 | 0.95 |
| Ldlrad3 | 1.09 | 1.02 | 1.12 | 1.02 | 1.00 | 0.99 | 0.88 | 0.17 | 0.99 | 0.53 | 0.88 | 1.02 |
| Leap2 | 1.00 | 1.00 | 1.00 | 1.00 | 1.00 | 1.00 | 1.00 | 1.00 | 1.00 | 1.00 | 1.00 | 1.00 |
| Lefty1 | 0.64 | 1.00 | 0.91 | 1.00 | 1.00 | 0.84 | 0.12 | 0.19 | 0.09 | 0.28 | 0.31 | 0.30 |
| Lep | 1.00 | 1.00 | 1.00 | 1.00 | 1.00 | 1.00 | 0.19 | 0.22 | 0.39 | 1.00 | 1.00 | 1.00 |
| Lgals12 | 0.48 | 0.47 | 0.40 | 1.00 | 1.00 | 1.00 | 0.51 | 0.26 | 0.92 | 1.00 | 1.00 | 1.00 |
| Lgals2 | 1.00 | 0.86 | 0.78 | 1.00 | 1.00 | 0.94 | 1.00 | 1.00 | 1.00 | 1.00 | 1.00 | 1.00 |
| Lima1 | 0.68 | 0.72 | 0.84 | 0.99 | 1.00 | 1.00 | 0.64 | 0.07 | 0.85 | 0.48 | 0.73 | 0.98 |
| Lin52 | 1.13 | 1.07 | 0.93 | 1.12 | 0.40 | 0.97 | 1.12 | 0.14 | 1.33 | 0.28 | 0.88 | 0.84 |
| Lingo1 | 1.00 | 1.00 | 1.00 | 1.07 | 0.89 | 1.03 | 0.92 | 0.62 | 0.83 | 1.00 | 1.00 | 1.00 |
| Lipg | 1.00 | 1.00 | 1.00 | 1.03 | 1.00 | 1.19 | 1.00 | 1.00 | 1.00 | 1.00 | 2.31 | 1.39 |
| Lipo1 | 1.00 | 1.00 | 1.00 | 0.80 | 1.00 | 1.03 | 0.71 | 0.26 | 1.21 | 0.83 | 1.04 | 1.29 |
| Lix1l | 1.00 | 1.00 | 1.00 | 0.97 | 1.92 | 0.88 | 0.67 | 0.16 | 1.17 | 1.00 | 1.00 | 1.00 |
| Lnpep | 1.00 | 1.00 | 1.00 | 0.62 | 1.00 | 0.46 | 1.00 | 1.00 | 1.00 | 1.00 | 1.04 | 1.44 |
| Lonrf1 | 1.00 | 1.00 | 0.86 | 1.02 | 1.00 | 0.83 | 0.96 | 0.11 | 0.72 | 0.49 | 0.90 | 1.09 |
| Loxl1 | 1.00 | 1.00 | 1.00 | 1.16 | 1.00 | 1.00 | 0.91 | 1.48 | 0.91 | 1.00 | 1.00 | 1.00 |
| Lpar3 | 1.00 | 1.00 | 1.00 | 1.00 | 1.00 | 1.00 | 0.63 | 0.16 | 0.93 | 1.00 | 1.00 | 1.00 |
| Lpar5 | 1.00 | 1.00 | 1.00 | 1.00 | 1.00 | 1.00 | 0.43 | 0.16 | 0.65 | 1.00 | 0.51 | 0.81 |
| Lpcat1 | 1.00 | 1.00 | 1.00 | 0.84 | 1.00 | 1.03 | 1.00 | 1.00 | 0.76 | 0.35 | 0.79 | 0.65 |
| Lphn1 | 1.00 | 1.00 | 1.00 | 1.01 | 0.84 | 0.99 | 0.97 | 0.67 | 1.04 | 1.00 | 0.68 | 0.55 |
| Lrch1 | 1.00 | 1.00 | 1.00 | 0.92 | 1.00 | 0.96 | 0.89 | 0.12 | 0.96 | 0.57 | 1.08 | 0.99 |
| Lrch3 | 1.08 | 1.21 | 0.93 | 0.88 | 1.00 | 0.93 | 0.81 | 0.09 | 1.17 | 1.00 | 1.02 | 1.14 |

Fig. 35-57

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Lrif1 | 1.18 | 1.66 | 1.24 | 2.91 | 0.58 | 0.93 | 1.03 | 1.23 | 1.22 | 0.37 | 0.32 | 0.98 |
| Lrig1 | 1.42 | 2.01 | 0.74 | 1.08 | 0.51 | 0.93 | 1.45 | 1.42 | 0.94 | 0.33 | 0.49 | 1.04 |
| Lrig3 | 0.86 | 1.00 | 1.08 | 1.30 | 0.81 | 0.86 | 1.00 | 1.00 | 1.01 | 1.00 | 0.53 | 1.12 |
| Lrp4 | 0.84 | 1.00 | 0.68 | 1.00 | 1.00 | 1.00 | 0.77 | 0.90 | 0.86 | 0.59 | 0.53 | 0.95 |
| Lrr1 | 1.00 | 1.00 | 1.00 | 1.00 | 1.00 | 1.00 | 1.00 | 1.00 | 1.00 | 1.00 | 1.00 | 1.00 |
| Lrrc16a | 1.00 | 1.00 | 1.00 | 2.12 | 1.00 | 1.23 | 1.86 | 2.27 | 1.54 | 0.55 | 0.59 | 1.05 |
| Lrrc17 | 0.47 | 0.60 | 0.75 | 1.00 | 1.00 | 1.00 | 0.39 | 0.26 | 0.49 | 0.51 | 0.39 | 0.39 |
| Lrrc38 | 0.19 | 0.26 | 0.17 | 1.00 | 1.00 | 1.00 | 1.00 | 1.00 | 1.00 | 1.00 | 1.00 | 1.00 |
| Lrrc3b | 0.78 | 0.99 | 0.55 | 0.49 | 0.45 | 0.98 | 0.47 | 0.36 | 0.57 | 1.00 | 0.79 | 0.47 |
| Lrrc40 | 0.78 | 1.51 | 0.79 | 1.27 | 0.59 | 0.84 | 0.60 | 0.60 | 0.70 | 0.38 | 0.46 | 0.78 |
| Lrrc52 | 2.90 | 2.03 | 1.51 | 0.04 | 0.09 | 0.98 | 0.80 | 1.34 | 0.74 | 1.00 | 1.00 | 1.00 |
| Lrrc57 | 0.77 | 1.78 | 1.03 | 1.32 | 0.60 | 1.02 | 1.15 | 1.20 | 0.97 | 0.31 | 0.36 | 0.93 |
| Lrrc58 | 2.29 | 1.42 | 1.73 | 2.13 | 0.38 | 1.69 | 1.44 | 1.60 | 1.22 | 0.46 | 0.23 | 1.03 |
| Lrrc8b | 1.00 | 1.00 | 1.00 | 1.00 | 0.83 | 0.93 | 1.33 | 1.26 | 1.89 | 1.00 | 1.00 | 0.87 |
| Lrrc8d | 1.10 | 1.03 | 1.25 | 0.72 | 0.25 | 0.80 | 1.11 | 1.26 | 1.12 | 0.72 | 0.63 | 0.94 |
| Ltbp2 | 1.00 | 1.00 | 1.00 | 0.18 | 0.39 | 0.53 | 1.16 | 0.99 | 1.11 | 1.20 | 0.85 | 0.77 |
| Ly6f | 1.00 | 1.00 | 1.00 | 1.00 | 1.00 | 1.00 | 1.00 | 1.00 | 1.00 | 1.00 | 1.00 | 1.00 |
| Ly6g5b | 1.00 | 1.00 | 1.00 | 1.00 | 1.00 | 1.00 | 1.00 | 1.00 | 1.00 | 1.00 | 0.90 | 0.47 |
| Ly6g6e | 1.00 | 1.00 | 1.00 | 1.00 | 1.00 | 1.00 | 1.00 | 1.00 | 1.00 | 1.00 | 0.63 | 0.84 |
| Ly75 | 1.00 | 1.00 | 1.00 | 1.00 | 1.00 | 1.00 | 1.00 | 1.00 | 1.00 | 1.00 | 1.00 | 1.17 |
| Lypd1 | 1.00 | 1.00 | 1.00 | 1.00 | 0.30 | 1.00 | 1.00 | 1.00 | 0.87 | 1.00 | 1.00 | 1.00 |
| Lypd5 | 1.00 | 1.00 | 1.00 | 1.00 | 1.00 | 1.00 | 1.00 | 1.00 | 1.00 | 1.00 | 1.00 | 1.00 |
| Mad2l1 | 1.00 | 1.00 | 0.80 | 2.33 | 1.00 | 1.00 | 0.85 | 1.36 | 0.97 | 1.00 | 0.40 | 0.90 |
| Maf | 0.47 | 1.11 | 0.72 | 3.47 | 0.84 | 1.29 | 1.15 | 1.15 | 1.24 | 0.78 | 0.68 | 0.91 |
| Magee1 | 1.08 | 1.00 | 1.00 | 2.17 | 0.14 | 1.18 | 0.73 | 0.97 | 0.80 | 0.96 | 0.36 | 0.87 |
| Magt1 | 0.61 | 1.67 | 0.82 | 0.91 | 0.25 | 0.75 | 0.74 | 0.73 | 0.87 | 0.44 | 0.35 | 0.94 |
| Mal | 0.65 | 1.36 | 1.15 | 1.57 | 0.19 | 1.27 | 1.28 | 1.08 | 1.01 | 0.85 | 1.04 | 0.97 |
| Mamdc2 | 0.70 | 1.00 | 1.27 | 1.92 | 0.73 | 1.82 | 0.69 | 0.72 | 0.74 | 0.16 | 0.18 | 0.63 |
| Maml1 | 1.16 | 1.10 | 1.56 | 2.09 | 0.26 | 1.29 | 1.32 | 1.30 | 1.20 | 0.60 | 0.35 | 1.12 |
| Maml3 | 0.71 | 1.00 | 1.00 | 2.37 | 0.90 | 1.57 | 1.77 | 2.15 | 1.37 | 1.00 | 0.46 | 1.03 |
| Man2b2 | 0.85 | 1.00 | 1.16 | 0.69 | 0.31 | 1.14 | 1.31 | 1.05 | 1.19 | 0.37 | 0.37 | 0.94 |
| Mansc1 | 0.94 | 1.00 | 1.00 | 1.11 | 0.74 | 0.98 | 0.99 | 0.71 | 0.70 | 0.44 | 0.27 | 0.94 |
| Map2k1 | 1.12 | 2.12 | 0.82 | 0.80 | 0.20 | 0.97 | 0.93 | 0.79 | 0.94 | 0.32 | 0.37 | 1.09 |
| Map2k3os | 2.31 | 4.38 | 1.47 | 0.21 | 0.18 | 0.63 | 1.31 | 1.00 | 0.82 | 0.68 | 0.56 | 1.03 |
| Map3k1 | 0.70 | 1.00 | 0.93 | 1.38 | 0.29 | 0.68 | 0.74 | 0.99 | 0.98 | 0.49 | 0.25 | 0.90 |
| Map3k3 | 0.93 | 1.00 | 1.17 | 2.23 | 0.11 | 1.01 | 1.41 | 1.61 | 1.39 | 1.00 | 0.15 | 1.09 |
| Map4k3 | 0.65 | 0.88 | 0.67 | 1.44 | 0.58 | 0.93 | 0.70 | 0.69 | 0.75 | 0.44 | 0.44 | 0.80 |
| Map7 | 0.50 | 0.95 | 0.77 | 2.89 | 0.29 | 0.96 | 1.58 | 1.58 | 1.18 | 0.76 | 0.46 | 1.12 |
| Mapk7 | 0.74 | 1.02 | 0.97 | 0.78 | 0.26 | 0.94 | 1.08 | 0.89 | 1.15 | 0.38 | 0.37 | 0.97 |
| Mapkapk3 | 0.95 | 1.29 | 0.77 | 0.68 | 0.34 | 0.75 | 0.83 | 0.68 | 0.60 | 0.44 | 0.50 | 1.02 |
| March3 | 1.00 | 1.00 | 1.00 | 0.57 | 0.30 | 1.76 | 1.27 | 1.09 | 1.08 | 1.00 | 1.00 | 0.88 |
| March8 | 1.35 | 2.28 | 1.41 | 2.24 | 0.32 | 1.22 | 1.34 | 1.35 | 1.31 | 0.54 | 0.50 | 1.44 |
| Marcksl1-ps4 | 1.00 | 1.00 | 1.00 | 1.00 | 1.00 | 1.00 | 1.00 | 1.00 | 1.00 | 1.00 | 0.72 | 0.63 |
| Mark4 | 1.08 | 1.00 | 1.19 | 1.13 | 0.21 | 0.98 | 1.54 | 1.31 | 1.31 | 1.00 | 0.24 | 1.19 |
| Mast4 | 0.90 | 1.48 | 1.03 | 2.18 | 0.38 | 1.09 | 1.01 | 1.22 | 1.15 | 0.80 | 0.44 | 0.98 |
| Mat2b | 0.87 | 1.45 | 0.77 | 1.11 | 0.50 | 0.80 | 0.85 | 0.86 | 0.75 | 0.36 | 0.36 | 0.91 |
| Mavs | 0.88 | 1.08 | 1.10 | 0.47 | 0.24 | 0.87 | 1.04 | 1.12 | 0.87 | 0.51 | 0.50 | 1.01 |
| Mbip | 0.67 | 1.42 | 0.77 | 1.11 | 0.56 | 0.77 | 0.88 | 0.83 | 0.89 | 0.19 | 0.57 | 0.90 |
| Mblac2 | 1.00 | 1.00 | 0.92 | 1.73 | 0.32 | 0.52 | 0.99 | 1.15 | 0.94 | 1.00 | 0.59 | 0.94 |
| Mcam | 1.19 | 2.09 | 1.15 | 0.88 | 0.45 | 1.63 | 1.18 | 1.07 | 1.19 | 0.21 | 0.32 | 0.99 |
| Mcm5 | 1.00 | 1.00 | 1.00 | 1.00 | 1.00 | 1.00 | 1.00 | 1.00 | 1.00 | 1.10 | 1.36 | 0.78 |
| Mdm4 | 0.71 | 1.10 | 0.90 | 4.01 | 0.75 | 0.72 | 1.27 | 2.11 | 1.67 | 0.71 | 0.80 | 0.98 |
| Med6 | 1.18 | 0.99 | 1.36 | 0.83 | 1.14 | 1.21 | 0.69 | 0.80 | 1.00 | 0.49 | 0.79 | 1.02 |
| Mef2c | 0.52 | 0.86 | 0.62 | 1.74 | 0.19 | 0.98 | 0.81 | 0.91 | 0.99 | 0.44 | 0.43 | 0.72 |
| Mef2d | 0.81 | 3.78 | 1.08 | 0.70 | 0.07 | 0.88 | 1.33 | 1.66 | 1.24 | 1.00 | 0.37 | 1.02 |
| Megf9 | 1.00 | 1.00 | 1.00 | 0.94 | 0.23 | 0.27 | 2.31 | 2.15 | 1.57 | 1.00 | 1.00 | 1.25 |
| Mep1a | 1.00 | 1.00 | 1.00 | 1.00 | 1.00 | 1.00 | 1.00 | 1.00 | 1.00 | 1.00 | 1.00 | 1.00 |
| Mertk | 1.11 | 1.00 | 1.69 | 1.63 | 0.39 | 1.66 | 1.93 | 1.47 | 1.65 | 1.00 | 0.20 | 1.27 |
| Mettl20 | 1.50 | 2.88 | 1.64 | 2.24 | 1.05 | 2.11 | 4.66 | 4.12 | 2.92 | 0.33 | 0.48 | 1.39 |
| Mex3c | 1.12 | 2.32 | 1.18 | 2.18 | 0.20 | 1.06 | 1.07 | 1.30 | 1.07 | 0.42 | 0.31 | 1.12 |
| Mfsd8 | 0.70 | 1.61 | 0.74 | 1.22 | 0.35 | 0.93 | 0.82 | 0.81 | 0.83 | 0.40 | 0.37 | 0.90 |
| Mgat5 | 1.00 | 1.00 | 1.00 | 1.00 | 1.00 | 1.00 | 1.00 | 1.00 | 1.22 | 1.00 | 1.00 | 1.47 |
| Mia2 | 1.00 | 1.00 | 1.00 | 1.00 | 1.00 | 1.00 | 1.00 | 1.00 | 1.00 | 1.00 | 1.00 | 1.00 |
| Mical2 | 2.03 | 3.28 | 2.32 | 3.31 | 0.91 | 2.35 | 1.34 | 1.56 | 1.35 | 0.82 | 0.57 | 1.38 |

Fig. 35- 58

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Lrif1 | 1.08 | 1.27 | 0.99 | 0.93 | 2.78 | 1.05 | 0.87 | 0.57 | 1.06 | 0.94 | 1.17 | 1.18 |
| Lrig1 | 0.80 | 0.73 | 0.85 | 1.62 | 3.03 | 1.37 | 0.74 | 1.00 | 0.70 | 1.04 | 0.92 | 1.05 |
| Lrig3 | 2.03 | 1.69 | 2.22 | 1.06 | 1.00 | 0.98 | 0.76 | 1.00 | 0.97 | 1.31 | 1.16 | 1.22 |
| Lrp4 | 1.41 | 0.89 | 1.61 | 1.00 | 1.34 | 1.18 | 0.40 | 0.66 | 0.62 | 0.79 | 0.62 | 0.88 |
| Lrr1 | 0.18 | 0.41 | 0.35 | 1.00 | 1.00 | 1.00 | 1.00 | 1.00 | 1.00 | 1.00 | 1.00 | 1.00 |
| Lrrc16a | 1.87 | 1.11 | 1.27 | 0.80 | 1.33 | 0.93 | 1.56 | 1.00 | 0.61 | 1.03 | 0.83 | 1.05 |
| Lrrc17 | 0.95 | 0.52 | 1.00 | 1.00 | 1.00 | 1.00 | 1.00 | 1.00 | 1.00 | 0.63 | 0.70 | 0.70 |
| Lrrc38 | 1.00 | 1.00 | 1.00 | 1.00 | 1.00 | 1.00 | 1.00 | 1.00 | 1.00 | 1.00 | 1.00 | 1.00 |
| Lrrc3b | 0.17 | 0.33 | 0.39 | 0.72 | 1.00 | 0.67 | 1.00 | 1.00 | 1.00 | 1.00 | 1.00 | 1.00 |
| Lrrc40 | 0.79 | 0.86 | 0.92 | 0.61 | 0.72 | 0.85 | 0.61 | 0.69 | 0.92 | 0.86 | 0.77 | 0.97 |
| Lrrc52 | 1.00 | 1.00 | 1.00 | 0.83 | 0.44 | 1.17 | 1.00 | 1.00 | 1.00 | 1.00 | 1.00 | 1.00 |
| Lrrc57 | 0.73 | 0.76 | 0.84 | 0.89 | 0.68 | 1.12 | 1.03 | 1.00 | 1.02 | 1.09 | 0.93 | 0.91 |
| Lrrc58 | 0.74 | 0.71 | 0.89 | 1.12 | 1.11 | 0.87 | 1.17 | 1.10 | 1.03 | 1.08 | 0.95 | 1.10 |
| Lrrc8b | 0.21 | 0.14 | 0.55 | 1.56 | 1.00 | 1.21 | 1.00 | 1.00 | 1.00 | 1.42 | 0.70 | 1.00 |
| Lrrc8d | 1.07 | 1.04 | 1.20 | 1.27 | 1.97 | 1.09 | 0.79 | 0.54 | 0.86 | 1.22 | 0.93 | 1.05 |
| Ltbp2 | 1.16 | 0.86 | 1.07 | 1.00 | 1.00 | 1.00 | 1.00 | 1.00 | 1.00 | 1.00 | 1.00 | 1.00 |
| Ly6f | 1.00 | 1.00 | 1.00 | 1.00 | 1.00 | 1.00 | 1.00 | 1.00 | 1.00 | 1.00 | 1.00 | 1.00 |
| Ly6g5b | 0.86 | 1.02 | 0.80 | 1.00 | 1.00 | 1.00 | 1.00 | 1.00 | 1.00 | 1.00 | 0.81 | 1.00 |
| Ly6g6e | 1.09 | 1.31 | 1.04 | 1.00 | 1.00 | 1.00 | 1.00 | 1.00 | 1.00 | 0.93 | 1.48 | 1.32 |
| Ly75 | 0.27 | 0.19 | 0.63 | 1.00 | 1.00 | 1.00 | 1.00 | 1.00 | 1.00 | 1.50 | 1.00 | 0.83 |
| Lypd1 | 0.61 | 1.14 | 2.15 | 1.00 | 1.00 | 1.00 | 1.00 | 1.00 | 1.00 | 1.00 | 1.00 | 1.00 |
| Lypd5 | 1.00 | 1.00 | 1.00 | 1.00 | 1.00 | 1.00 | 1.00 | 1.00 | 1.00 | 1.00 | 1.00 | 1.00 |
| Mad2l1 | 0.58 | 0.58 | 0.58 | 0.89 | 1.00 | 0.45 | 1.00 | 1.00 | 1.00 | 0.94 | 1.51 | 0.96 |
| Maf | 1.53 | 1.18 | 1.66 | 1.09 | 1.55 | 1.27 | 0.80 | 0.44 | 0.95 | 1.27 | 1.04 | 1.20 |
| Magee1 | 0.84 | 0.69 | 1.00 | 1.20 | 1.00 | 0.99 | 0.83 | 1.00 | 0.76 | 0.92 | 0.61 | 1.02 |
| Magt1 | 0.76 | 0.64 | 0.98 | 1.02 | 2.34 | 1.11 | 0.71 | 0.39 | 0.70 | 0.99 | 0.81 | 1.00 |
| Mal | 1.15 | 0.78 | 1.86 | 0.88 | 0.74 | 0.90 | 1.00 | 1.00 | 1.00 | 1.71 | 2.70 | 1.94 |
| Mamdc2 | 1.00 | 1.00 | 1.00 | 1.00 | 1.00 | 1.00 | 0.73 | 1.00 | 0.87 | 0.96 | 0.69 | 1.00 |
| Maml1 | 0.74 | 0.70 | 1.01 | 1.02 | 1.00 | 1.10 | 1.04 | 1.00 | 1.15 | 1.05 | 0.66 | 0.98 |
| Maml3 | 0.99 | 0.61 | 1.26 | 0.98 | 1.00 | 1.17 | 0.92 | 1.00 | 1.00 | 0.95 | 0.51 | 0.90 |
| Man2b2 | 1.35 | 1.12 | 1.45 | 1.25 | 1.61 | 1.21 | 0.92 | 1.09 | 1.22 | 1.00 | 0.71 | 0.99 |
| Mansc1 | 1.14 | 1.00 | 0.96 | 0.62 | 1.00 | 0.61 | 1.12 | 1.00 | 1.00 | 1.28 | 0.82 | 1.14 |
| Map2k1 | 0.85 | 0.92 | 0.92 | 0.91 | 1.43 | 0.98 | 0.94 | 0.38 | 0.90 | 1.00 | 0.98 | 1.10 |
| Map2k3os | 0.67 | 1.23 | 1.03 | 0.86 | 1.02 | 1.18 | 0.66 | 1.00 | 1.55 | 1.17 | 1.59 | 1.25 |
| Map3k1 | 0.62 | 0.59 | 0.84 | 0.94 | 1.00 | 0.85 | 1.27 | 1.00 | 1.31 | 0.98 | 0.63 | 0.97 |
| Map3k3 | 0.70 | 0.59 | 1.11 | 1.40 | 1.00 | 1.11 | 1.15 | 1.00 | 1.05 | 0.96 | 0.41 | 1.02 |
| Map4k3 | 1.08 | 0.90 | 0.93 | 1.01 | 1.25 | 0.99 | 1.06 | 0.70 | 1.02 | 0.94 | 0.97 | 1.01 |
| Map7 | 1.21 | 1.52 | 1.43 | 0.90 | 1.24 | 0.84 | 2.38 | 1.69 | 1.37 | 1.14 | 0.89 | 1.16 |
| Mapk7 | 0.72 | 0.70 | 0.85 | 0.95 | 1.27 | 0.95 | 0.98 | 1.00 | 1.14 | 0.98 | 0.82 | 1.10 |
| Mapkapk3 | 1.30 | 1.21 | 1.36 | 0.93 | 1.00 | 0.90 | 1.00 | 1.00 | 1.00 | 1.02 | 1.07 | 1.08 |
| March3 | 1.02 | 1.00 | 1.20 | 0.71 | 1.00 | 1.15 | 1.00 | 1.00 | 1.00 | 1.22 | 0.67 | 1.10 |
| March8 | 1.55 | 1.05 | 1.70 | 1.45 | 1.78 | 1.35 | 1.00 | 0.51 | 1.11 | 1.12 | 0.75 | 1.09 |
| Marcksl1-ps4 | 1.00 | 1.14 | 1.00 | 0.32 | 1.00 | 0.28 | 0.10 | 0.34 | 0.09 | 0.20 | 0.01 | 0.18 |
| Mark4 | 0.76 | 0.85 | 1.09 | 1.11 | 1.00 | 1.07 | 1.41 | 1.00 | 1.06 | 0.99 | 0.55 | 1.02 |
| Mast4 | 0.88 | 0.65 | 1.17 | 0.88 | 1.00 | 1.04 | 1.00 | 1.00 | 1.00 | 1.09 | 0.63 | 0.98 |
| Mat2b | 1.01 | 0.99 | 0.85 | 0.99 | 1.53 | 1.01 | 1.05 | 0.15 | 0.92 | 0.94 | 0.97 | 1.05 |
| Mavs | 1.05 | 0.98 | 1.03 | 0.88 | 0.97 | 0.96 | 0.77 | 0.75 | 0.87 | 1.02 | 0.74 | 0.94 |
| Mbip | 1.12 | 1.33 | 1.16 | 1.24 | 0.83 | 0.75 | 1.04 | 1.00 | 1.61 | 1.29 | 1.17 | 0.78 |
| Mblac2 | 0.65 | 0.57 | 0.92 | 1.17 | 1.00 | 0.99 | 0.76 | 1.00 | 0.86 | 0.86 | 0.72 | 0.72 |
| Mcam | 0.85 | 0.90 | 0.79 | 0.93 | 1.71 | 1.23 | 0.92 | 1.00 | 1.17 | 1.07 | 1.09 | 1.02 |
| Mcm5 | 0.37 | 0.56 | 0.47 | 0.32 | 0.19 | 0.37 | 1.00 | 1.00 | 1.00 | 0.69 | 0.95 | 0.86 |
| Mdm4 | 0.30 | 0.20 | 0.64 | 1.30 | 1.00 | 0.99 | 0.95 | 1.00 | 0.94 | 0.97 | 0.47 | 0.75 |
| Med6 | 1.12 | 1.44 | 0.94 | 1.01 | 1.82 | 1.04 | 1.82 | 0.34 | 0.86 | 1.04 | 1.72 | 0.97 |
| Mef2c | 0.84 | 0.94 | 1.31 | 0.85 | 1.00 | 0.86 | 1.00 | 1.00 | 1.00 | 0.88 | 0.69 | 0.81 |
| Mef2d | 0.46 | 0.37 | 0.80 | 1.13 | 1.00 | 1.36 | 1.40 | 1.00 | 1.41 | 0.94 | 0.42 | 0.88 |
| Megf9 | 0.26 | 0.23 | 0.60 | 1.61 | 1.00 | 1.60 | 1.32 | 1.00 | 1.20 | 1.46 | 1.00 | 1.16 |
| Mep1a | 1.00 | 1.00 | 1.00 | 0.02 | 0.02 | 0.04 | 1.00 | 1.00 | 1.00 | 0.20 | 0.20 | 0.22 |
| Mertk | 1.49 | 1.14 | 2.33 | 1.19 | 1.00 | 1.21 | 0.76 | 1.00 | 0.81 | 0.94 | 0.40 | 0.86 |
| Mettl20 | 2.20 | 2.53 | 1.66 | 1.66 | 4.19 | 1.26 | 0.90 | 1.04 | 0.65 | 1.19 | 1.05 | 1.02 |
| Mex3c | 0.61 | 0.45 | 0.81 | 1.26 | 1.08 | 1.07 | 1.24 | 1.00 | 1.16 | 1.15 | 0.74 | 1.11 |
| Mfsd8 | 1.10 | 1.11 | 0.91 | 0.98 | 1.00 | 0.80 | 0.81 | 1.00 | 0.76 | 1.04 | 1.00 | 1.03 |
| Mgat5 | 0.28 | 0.16 | 0.62 | 1.12 | 1.00 | 1.18 | 1.00 | 1.00 | 1.00 | 1.24 | 0.45 | 1.06 |
| Mia2 | 1.00 | 1.00 | 1.00 | 1.63 | 1.00 | 1.27 | 1.13 | 1.00 | 1.42 | 0.90 | 0.16 | 0.76 |
| Mical2 | 0.83 | 0.81 | 1.26 | 1.30 | 1.00 | 1.29 | 0.98 | 1.00 | 1.09 | 1.00 | 0.67 | 0.94 |

Fig. 35- 59

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Lrif1 | 1.21 | 1.14 | 1.14 | 1.10 | 0.58 | 1.14 | 1.23 | 0.28 | 0.94 | 1.31 | 1.07 | 1.00 |
| Lrig1 | 1.05 | 1.10 | 1.10 | 0.51 | 0.34 | 0.82 | 1.01 | 1.00 | 0.86 | 0.86 | 0.77 | 0.82 |
| Lrig3 | 1.26 | 1.43 | 1.19 | 1.26 | 1.00 | 1.21 | 1.00 | 1.00 | 1.00 | 0.89 | 1.00 | 1.00 |
| Lrp4 | 0.76 | 0.75 | 0.92 | 1.10 | 1.00 | 1.05 | 1.00 | 1.00 | 1.00 | 0.99 | 1.04 | 1.21 |
| Lrr1 | 0.82 | 0.79 | 1.00 | 1.00 | 1.00 | 1.00 | 1.30 | 0.70 | 0.75 | 0.54 | 0.48 | 0.77 |
| Lrrc16a | 1.24 | 1.17 | 0.96 | 2.16 | 1.00 | 1.58 | 1.30 | 0.54 | 0.98 | 1.89 | 1.39 | 1.35 |
| Lrrc17 | 0.57 | 0.67 | 1.16 | 0.42 | 1.00 | 0.54 | 0.88 | 0.81 | 0.95 | 1.00 | 1.00 | 1.00 |
| Lrrc38 | 1.00 | 1.00 | 1.00 | 1.00 | 1.00 | 1.00 | 1.00 | 1.00 | 1.00 | 1.00 | 1.00 | 1.00 |
| Lrrc3b | 1.48 | 0.87 | 1.29 | 0.67 | 0.92 | 1.10 | 1.00 | 1.00 | 1.00 | 0.97 | 1.15 | 1.02 |
| Lrrc40 | 0.72 | 0.64 | 0.71 | 0.75 | 1.00 | 0.73 | 0.77 | 0.97 | 0.66 | 1.08 | 0.92 | 0.99 |
| Lrrc52 | 1.00 | 1.00 | 1.00 | 1.00 | 1.00 | 1.00 | 1.22 | 0.86 | 1.30 | 1.00 | 1.00 | 1.00 |
| Lrrc57 | 0.87 | 1.07 | 1.04 | 0.81 | 0.92 | 1.01 | 0.85 | 1.12 | 1.01 | 0.96 | 0.79 | 1.06 |
| Lrrc58 | 0.86 | 0.82 | 0.77 | 1.15 | 0.13 | 0.96 | 0.84 | 0.87 | 0.90 | 0.83 | 0.69 | 0.89 |
| Lrrc8b | 0.75 | 0.69 | 0.39 | 2.24 | 0.82 | 0.39 | 1.02 | 0.77 | 1.06 | 0.72 | 0.96 | 0.90 |
| Lrrc8d | 1.20 | 1.03 | 0.87 | 0.93 | 0.20 | 1.26 | 1.09 | 0.72 | 0.95 | 1.11 | 1.07 | 1.08 |
| Ltbp2 | 1.00 | 1.00 | 1.00 | 1.09 | 1.00 | 1.00 | 0.81 | 1.00 | 1.00 | 0.82 | 0.54 | 0.66 |
| Ly6f | 1.00 | 1.00 | 1.00 | 1.00 | 1.00 | 0.14 | 1.00 | 1.00 | 1.00 | 1.00 | 1.00 | 1.00 |
| Ly6g5b | 1.00 | 1.00 | 1.00 | 0.24 | 1.00 | 1.00 | 0.56 | 1.00 | 0.93 | 0.75 | 0.88 | 0.73 |
| Ly6g6e | 0.58 | 0.68 | 0.60 | 1.00 | 1.00 | 1.00 | 1.00 | 1.00 | 1.00 | 1.00 | 1.00 | 1.00 |
| Ly75 | 1.00 | 1.00 | 1.00 | 1.00 | 1.00 | 1.00 | 1.00 | 1.00 | 1.00 | 0.87 | 0.46 | 1.00 |
| Lypd1 | 1.00 | 1.00 | 1.00 | 0.18 | 1.00 | 0.31 | 1.53 | 1.00 | 2.27 | 1.00 | 4.57 | 1.00 |
| Lypd5 | 0.87 | 1.21 | 1.26 | 1.00 | 1.00 | 1.00 | 0.89 | 1.24 | 1.22 | 1.00 | 1.00 | 1.00 |
| Mad2l1 | 0.61 | 0.28 | 0.55 | 0.77 | 1.00 | 0.86 | 1.19 | 0.88 | 1.19 | 1.07 | 1.03 | 0.99 |
| Maf | 1.10 | 0.87 | 1.39 | 1.00 | 0.40 | 0.88 | 0.78 | 1.00 | 0.93 | 1.04 | 0.83 | 1.04 |
| Magee1 | 1.07 | 0.90 | 1.22 | 0.74 | 0.55 | 0.77 | 1.05 | 1.96 | 1.09 | 0.80 | 1.94 | 1.06 |
| Magt1 | 1.01 | 0.84 | 0.85 | 1.13 | 0.35 | 0.83 | 0.96 | 1.00 | 0.78 | 1.02 | 0.64 | 0.95 |
| Mal | 0.64 | 0.63 | 0.57 | 1.45 | 1.43 | 1.42 | 0.77 | 1.11 | 1.11 | 0.54 | 3.57 | 0.73 |
| Mamdc2 | 1.45 | 1.32 | 1.34 | 0.83 | 1.00 | 0.98 | 1.00 | 1.00 | 1.08 | 1.00 | 1.00 | 1.00 |
| Maml1 | 1.04 | 1.24 | 1.06 | 1.34 | 0.37 | 1.18 | 1.09 | 1.00 | 1.04 | 1.04 | 0.70 | 1.14 |
| Maml3 | 1.04 | 1.47 | 0.90 | 1.33 | 1.00 | 0.94 | 0.91 | 1.00 | 0.91 | 0.90 | 0.67 | 1.38 |
| Man2b2 | 1.08 | 1.11 | 0.94 | 0.92 | 0.50 | 0.74 | 1.02 | 0.46 | 1.11 | 0.95 | 1.02 | 1.21 |
| Mansc1 | 1.63 | 1.59 | 1.30 | 0.85 | 0.57 | 0.75 | 1.00 | 1.00 | 1.00 | 1.36 | 1.05 | 1.28 |
| Map2k1 | 0.90 | 0.92 | 0.84 | 0.95 | 0.42 | 0.90 | 0.96 | 0.78 | 0.71 | 1.05 | 0.96 | 0.89 |
| Map2k3os | 1.12 | 0.64 | 1.27 | 0.56 | 1.00 | 0.74 | 1.14 | 0.93 | 1.10 | 1.45 | 1.09 | 1.09 |
| Map3k1 | 1.03 | 0.89 | 0.94 | 0.85 | 0.36 | 0.91 | 1.33 | 0.99 | 1.04 | 1.04 | 0.66 | 1.17 |
| Map3k3 | 1.27 | 1.25 | 1.12 | 1.12 | 0.27 | 0.93 | 1.22 | 1.00 | 0.95 | 1.05 | 0.68 | 1.13 |
| Map4k3 | 1.16 | 1.01 | 1.13 | 0.76 | 0.28 | 0.91 | 1.00 | 0.92 | 1.00 | 0.87 | 0.75 | 0.86 |
| Map7 | 1.14 | 1.18 | 1.06 | 0.94 | 1.00 | 1.00 | 0.90 | 0.93 | 0.97 | 1.21 | 1.61 | 1.52 |
| Mapk7 | 0.93 | 1.07 | 1.03 | 0.87 | 0.45 | 0.80 | 0.90 | 0.69 | 0.94 | 0.97 | 0.83 | 1.02 |
| Mapkapk3 | 1.01 | 1.03 | 1.06 | 0.89 | 1.00 | 0.94 | 1.01 | 0.78 | 1.08 | 1.20 | 0.99 | 1.15 |
| March3 | 0.87 | 0.82 | 0.83 | 0.68 | 0.87 | 0.74 | 1.24 | 1.00 | 1.27 | 0.88 | 0.56 | 0.78 |
| March8 | 1.26 | 1.23 | 1.08 | 1.49 | 0.30 | 1.27 | 1.01 | 1.58 | 1.11 | 0.57 | 0.54 | 0.47 |
| Marcksl1-ps4 | 0.25 | 0.19 | 0.21 | 0.99 | 1.00 | 0.64 | 1.00 | 1.00 | 1.00 | 0.79 | 1.00 | 1.03 |
| Mark4 | 0.96 | 1.45 | 1.10 | 0.82 | 1.00 | 0.96 | 1.02 | 1.00 | 1.10 | 1.00 | 0.84 | 1.03 |
| Mast4 | 1.18 | 1.15 | 0.86 | 1.40 | 0.47 | 0.92 | 1.15 | 0.82 | 1.19 | 0.88 | 0.63 | 1.00 |
| Mat2b | 1.03 | 1.06 | 1.09 | 0.89 | 0.40 | 0.94 | 1.09 | 0.31 | 0.97 | 1.00 | 0.91 | 0.99 |
| Mavs | 0.91 | 0.87 | 0.92 | 0.75 | 0.30 | 0.96 | 0.84 | 0.55 | 0.79 | 0.96 | 0.76 | 1.06 |
| Mbip | 0.72 | 0.66 | 0.81 | 1.22 | 1.00 | 0.81 | 1.01 | 0.36 | 0.72 | 1.12 | 1.04 | 1.01 |
| Mblac2 | 0.91 | 1.19 | 1.25 | 0.38 | 1.00 | 0.52 | 0.75 | 1.00 | 0.58 | 0.94 | 0.79 | 1.06 |
| Mcam | 1.13 | 1.30 | 1.37 | 0.65 | 0.11 | 0.86 | 0.87 | 0.62 | 1.03 | 1.05 | 1.06 | 1.08 |
| Mcm5 | 0.56 | 0.48 | 0.53 | 0.95 | 1.00 | 0.88 | 1.18 | 0.97 | 1.09 | 0.82 | 0.83 | 0.65 |
| Mdm4 | 0.93 | 0.71 | 0.57 | 1.19 | 0.34 | 0.34 | 1.23 | 0.72 | 1.28 | 0.91 | 0.35 | 1.24 |
| Med6 | 0.81 | 0.77 | 1.24 | 1.12 | 0.46 | 0.87 | 0.88 | 0.16 | 0.84 | 0.90 | 1.16 | 1.20 |
| Mef2c | 1.01 | 0.66 | 1.09 | 0.88 | 0.59 | 0.74 | 1.17 | 1.00 | 1.15 | 0.98 | 0.75 | 0.90 |
| Mef2d | 0.95 | 1.13 | 0.78 | 1.42 | 0.29 | 1.11 | 1.14 | 1.00 | 1.08 | 0.83 | 0.46 | 1.07 |
| Megf9 | 1.62 | 1.45 | 0.82 | 1.00 | 0.49 | 0.19 | 1.52 | 1.00 | 1.25 | 0.97 | 3.34 | 1.00 |
| Mep1a | 1.00 | 1.00 | 1.00 | 1.00 | 1.00 | 1.00 | 1.00 | 1.00 | 1.00 | 1.00 | 1.00 | 1.00 |
| Mertk | 1.42 | 1.53 | 1.73 | 1.50 | 0.35 | 1.56 | 0.92 | 1.00 | 1.17 | 0.99 | 0.80 | 1.11 |
| Mettl20 | 2.16 | 2.23 | 2.14 | 4.48 | 2.69 | 3.07 | 1.22 | 0.64 | 0.94 | 1.32 | 1.09 | 1.02 |
| Mex3c | 0.98 | 0.85 | 0.87 | 1.14 | 0.27 | 0.93 | 1.06 | 0.35 | 1.08 | 0.96 | 0.66 | 1.17 |
| Mfsd8 | 0.82 | 0.98 | 0.75 | 0.60 | 0.42 | 0.80 | 0.94 | 1.00 | 1.41 | 1.19 | 1.06 | 1.29 |
| Mgat5 | 0.97 | 1.40 | 0.53 | 1.00 | 0.48 | 0.46 | 0.92 | 1.38 | 1.10 | 0.85 | 0.60 | 1.08 |
| Mia2 | 1.25 | 1.00 | 0.80 | 1.71 | 1.00 | 1.55 | 1.00 | 1.00 | 1.00 | 1.00 | 1.00 | 1.00 |
| Mical2 | 1.18 | 1.15 | 0.98 | 3.40 | 0.92 | 1.95 | 1.42 | 1.00 | 1.08 | 0.99 | 1.77 | 1.22 |

Fig. 35- 60

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Lrif1 | 1.17 | 2.27 | 0.64 | 0.85 | 1.00 | 1.00 | 0.88 | 0.05 | 0.96 | 0.52 | 1.31 | 1.23 |
| Lrig1 | 0.78 | 0.70 | 0.83 | 0.92 | 0.44 | 0.97 | 1.01 | 0.10 | 1.09 | 1.00 | 1.01 | 0.73 |
| Lrig3 | 1.00 | 1.00 | 1.00 | 1.00 | 1.00 | 1.06 | 1.19 | 0.10 | 1.51 | 1.00 | 1.00 | 1.00 |
| Lrp4 | 0.65 | 0.53 | 0.75 | 0.98 | 0.91 | 0.85 | 0.43 | 0.19 | 0.63 | 1.00 | 1.12 | 1.13 |
| Lrr1 | 1.00 | 1.00 | 1.00 | 1.00 | 1.00 | 1.00 | 0.45 | 0.65 | 0.46 | 0.45 | 1.06 | 0.83 |
| Lrrc16a | 2.14 | 2.16 | 1.30 | 0.93 | 1.00 | 0.99 | 0.76 | 0.16 | 0.89 | 1.00 | 1.17 | 1.00 |
| Lrrc17 | 1.00 | 1.00 | 1.00 | 1.00 | 0.65 | 1.00 | 0.39 | 0.20 | 0.50 | 1.00 | 1.00 | 1.00 |
| Lrrc38 | 1.00 | 1.00 | 1.00 | 1.08 | 2.48 | 1.26 | 1.00 | 1.00 | 1.00 | 1.00 | 1.00 | 1.00 |
| Lrrc3b | 1.00 | 1.00 | 1.00 | 0.98 | 1.00 | 0.99 | 1.00 | 1.00 | 1.00 | 1.00 | 1.00 | 1.00 |
| Lrrc40 | 0.75 | 0.83 | 1.00 | 0.88 | 4.15 | 0.98 | 0.71 | 0.13 | 0.89 | 0.50 | 0.88 | 0.74 |
| Lrrc52 | 1.00 | 1.00 | 1.00 | 1.00 | 1.00 | 1.00 | 1.33 | 0.80 | 0.91 | 1.00 | 1.00 | 1.00 |
| Lrrc57 | 0.53 | 0.51 | 0.74 | 0.98 | 1.00 | 1.01 | 0.96 | 0.12 | 1.11 | 0.42 | 1.08 | 0.97 |
| Lrrc58 | 1.26 | 1.27 | 1.08 | 1.11 | 0.78 | 1.04 | 0.97 | 0.17 | 1.03 | 0.28 | 0.97 | 1.11 |
| Lrrc8b | 1.00 | 1.00 | 1.00 | 0.72 | 1.00 | 0.78 | 2.76 | 1.00 | 1.33 | 1.00 | 1.00 | 0.93 |
| Lrrc8d | 1.15 | 1.21 | 0.89 | 0.98 | 0.95 | 1.02 | 0.66 | 0.15 | 0.90 | 0.44 | 0.93 | 0.87 |
| Ltbp2 | 1.00 | 1.00 | 1.00 | 1.55 | 0.62 | 1.82 | 1.41 | 1.53 | 1.37 | 1.00 | 1.00 | 1.00 |
| Ly6f | 1.00 | 1.00 | 1.00 | 1.00 | 1.00 | 1.00 | 1.00 | 1.00 | 1.00 | 1.00 | 1.00 | 1.00 |
| Ly6g5b | 1.00 | 1.00 | 1.00 | 1.00 | 0.87 | 0.97 | 1.08 | 0.12 | 0.78 | 0.66 | 0.98 | 0.91 |
| Ly6g6e | 1.00 | 1.00 | 1.00 | 0.85 | 1.98 | 0.68 | 1.39 | 0.18 | 0.82 | 1.00 | 1.00 | 1.00 |
| Ly75 | 1.00 | 1.00 | 1.00 | 1.00 | 1.00 | 1.00 | 1.00 | 1.00 | 1.00 | 1.00 | 0.96 | 0.68 |
| Lypd1 | 1.00 | 1.00 | 1.00 | 1.19 | 2.10 | 1.12 | 1.00 | 1.00 | 1.00 | 1.00 | 1.00 | 1.00 |
| Lypd5 | 1.00 | 1.00 | 1.00 | 1.00 | 1.00 | 1.00 | 0.68 | 0.03 | 0.59 | 1.00 | 1.00 | 1.00 |
| Mad2l1 | 1.00 | 1.00 | 1.00 | 1.22 | 1.00 | 1.13 | 0.71 | 0.16 | 0.75 | 0.35 | 0.99 | 1.00 |
| Maf | 1.16 | 1.00 | 0.79 | 0.81 | 1.00 | 0.94 | 0.52 | 0.12 | 0.62 | 1.16 | 1.19 | 1.23 |
| Magee1 | 1.00 | 1.00 | 1.00 | 1.09 | 1.30 | 1.01 | 0.93 | 0.31 | 1.04 | 1.00 | 0.68 | 0.70 |
| Magt1 | 0.81 | 0.76 | 0.75 | 0.84 | 1.00 | 0.74 | 0.92 | 0.11 | 0.97 | 0.54 | 0.92 | 0.91 |
| Mal | 1.00 | 1.00 | 1.00 | 0.98 | 0.94 | 1.01 | 1.41 | 1.31 | 1.51 | 1.00 | 1.00 | 1.00 |
| Mamdc2 | 1.00 | 1.00 | 1.00 | 0.90 | 1.00 | 1.02 | 0.83 | 0.27 | 1.04 | 1.00 | 1.00 | 1.00 |
| Maml1 | 1.19 | 0.91 | 1.22 | 0.98 | 0.83 | 0.95 | 0.94 | 0.13 | 1.12 | 0.40 | 0.95 | 1.00 |
| Maml3 | 1.12 | 1.08 | 1.00 | 1.10 | 1.00 | 1.24 | 0.66 | 0.15 | 0.96 | 1.00 | 0.81 | 0.71 |
| Man2b2 | 0.74 | 1.07 | 1.32 | 1.15 | 1.00 | 1.08 | 1.08 | 0.19 | 1.08 | 0.46 | 1.05 | 1.03 |
| Mansc1 | 0.74 | 0.76 | 1.25 | 0.89 | 1.00 | 0.71 | 0.57 | 0.17 | 0.57 | 1.00 | 1.03 | 1.00 |
| Map2k1 | 0.87 | 0.95 | 1.18 | 0.94 | 0.95 | 0.97 | 0.91 | 0.10 | 0.93 | 0.53 | 1.22 | 1.08 |
| Map2k3os | 1.00 | 1.00 | 1.00 | 0.96 | 1.00 | 0.78 | 0.96 | 0.25 | 0.75 | 1.00 | 0.70 | 1.07 |
| Map3k1 | 1.09 | 1.42 | 1.25 | 0.88 | 1.00 | 0.86 | 0.85 | 0.08 | 1.17 | 0.44 | 0.91 | 0.92 |
| Map3k3 | 1.42 | 1.38 | 1.54 | 0.98 | 0.75 | 0.90 | 1.00 | 0.07 | 1.17 | 0.18 | 1.13 | 1.00 |
| Map4k3 | 1.04 | 1.22 | 0.81 | 1.14 | 0.83 | 1.11 | 0.63 | 0.14 | 0.76 | 1.00 | 0.88 | 1.28 |
| Map7 | 1.22 | 1.23 | 1.05 | 1.03 | 1.08 | 0.97 | 0.74 | 0.18 | 0.78 | 0.42 | 0.80 | 0.96 |
| Mapk7 | 1.10 | 1.00 | 1.16 | 0.84 | 1.00 | 0.89 | 1.03 | 0.19 | 1.02 | 0.60 | 1.24 | 1.00 |
| Mapkapk3 | 1.68 | 1.24 | 1.43 | 0.75 | 0.91 | 0.81 | 0.82 | 0.13 | 0.68 | 0.60 | 1.12 | 1.22 |
| March3 | 1.00 | 1.00 | 1.00 | 1.31 | 1.00 | 0.92 | 1.12 | 0.14 | 0.67 | 0.39 | 0.93 | 0.94 |
| March8 | 0.75 | 0.73 | 0.76 | 1.22 | 1.00 | 1.14 | 1.02 | 0.12 | 1.12 | 0.28 | 0.63 | 0.65 |
| Marcksl1-ps4 | 1.00 | 1.00 | 1.00 | 1.00 | 1.00 | 1.00 | 1.00 | 1.00 | 1.00 | 1.00 | 1.00 | 1.00 |
| Mark4 | 1.86 | 1.38 | 1.61 | 1.01 | 1.00 | 1.02 | 0.94 | 0.08 | 0.83 | 0.66 | 1.13 | 1.03 |
| Mast4 | 1.00 | 1.00 | 1.00 | 1.03 | 1.00 | 1.08 | 0.90 | 0.16 | 1.17 | 1.00 | 0.66 | 0.74 |
| Mat2b | 0.86 | 0.79 | 0.95 | 1.02 | 1.41 | 0.96 | 0.90 | 0.18 | 1.07 | 0.52 | 1.03 | 0.99 |
| Mavs | 0.73 | 0.84 | 0.86 | 0.96 | 1.00 | 1.03 | 0.78 | 0.20 | 0.77 | 0.40 | 0.74 | 0.98 |
| Mbip | 0.94 | 1.19 | 1.00 | 0.96 | 1.15 | 0.97 | 0.84 | 0.09 | 1.24 | 0.41 | 1.36 | 0.90 |
| Mblac2 | 1.00 | 1.00 | 1.00 | 1.00 | 1.21 | 0.98 | 0.58 | 0.13 | 0.80 | 1.00 | 0.94 | 0.95 |
| Mcam | 1.15 | 1.00 | 1.56 | 0.96 | 1.00 | 0.78 | 1.24 | 0.11 | 1.27 | 0.93 | 0.39 | 0.50 |
| Mcm5 | 1.00 | 1.00 | 1.00 | 0.90 | 1.20 | 1.06 | 0.62 | 0.62 | 0.45 | 0.94 | 0.80 | 0.85 |
| Mdm4 | 1.10 | 1.63 | 1.12 | 0.69 | 1.00 | 0.79 | 0.57 | 0.64 | 0.91 | 1.16 | 0.87 | 0.78 |
| Med6 | 0.93 | 0.68 | 1.12 | 1.05 | 1.82 | 1.11 | 0.85 | 0.37 | 0.89 | 0.67 | 1.20 | 1.30 |
| Mef2c | 1.00 | 1.00 | 1.00 | 0.89 | 0.87 | 0.88 | 1.01 | 0.47 | 1.66 | 0.73 | 0.86 | 0.80 |
| Mef2d | 1.18 | 1.09 | 1.41 | 0.98 | 1.00 | 0.96 | 1.22 | 0.13 | 1.64 | 0.32 | 0.56 | 0.64 |
| Megf9 | 1.26 | 1.84 | 1.00 | 0.88 | 1.00 | 0.95 | 0.65 | 0.25 | 1.04 | 1.00 | 0.56 | 0.51 |
| Mep1a | 1.00 | 1.00 | 1.00 | 1.00 | 1.00 | 1.00 | 1.00 | 1.00 | 1.00 | 1.00 | 1.00 | 1.00 |
| Mertk | 1.00 | 1.00 | 1.00 | 1.12 | 1.00 | 1.22 | 1.05 | 0.21 | 1.60 | 1.00 | 1.22 | 1.15 |
| Mettl20 | 2.01 | 2.20 | 1.60 | 0.87 | 1.00 | 1.10 | 1.51 | 0.19 | 1.34 | 0.37 | 1.19 | 0.72 |
| Mex3c | 1.09 | 1.29 | 1.05 | 0.87 | 1.00 | 0.92 | 0.82 | 0.09 | 1.04 | 0.43 | 0.77 | 0.96 |
| Mfsd8 | 0.88 | 1.00 | 1.00 | 0.93 | 0.81 | 0.88 | 0.83 | 0.13 | 1.09 | 0.53 | 0.98 | 1.15 |
| Mgat5 | 1.00 | 1.00 | 1.00 | 0.66 | 1.00 | 0.88 | 1.00 | 1.00 | 1.00 | 1.00 | 1.00 | 1.00 |
| Mia2 | 1.39 | 1.08 | 1.36 | 1.00 | 1.00 | 1.00 | 1.00 | 1.00 | 1.00 | 1.00 | 1.00 | 1.00 |
| Mical2 | 1.26 | 1.32 | 1.12 | 1.21 | 1.04 | 1.08 | 1.20 | 0.18 | 1.22 | 1.00 | 1.00 | 0.91 |

Fig. 35- 61

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Mid2 | 0.70 | 1.00 | 1.10 | 2.27 | 0.30 | 0.94 | 1.14 | 1.39 | 1.42 | 0.47 | 0.29 | 0.92 |
| Mier1 | 1.77 | 3.67 | 1.71 | 2.44 | 0.41 | 1.05 | 1.11 | 1.37 | 1.09 | 0.40 | 0.37 | 1.04 |
| Mir1199 | 1.00 | 1.00 | 1.00 | 1.00 | 1.00 | 1.00 | 1.00 | 1.00 | 1.00 | 1.00 | 1.00 | 1.00 |
| Mir215 | 1.00 | 1.00 | 1.00 | 1.00 | 1.00 | 1.00 | 1.00 | 1.00 | 1.00 | 1.00 | 1.00 | 1.00 |
| Mir3473g | 1.00 | 1.00 | 1.00 | 1.00 | 1.00 | 1.00 | 1.00 | 1.00 | 1.00 | 1.00 | 1.00 | 1.00 |
| Mir486 | 1.00 | 0.05 | 1.00 | 1.00 | 1.00 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 1.00 | 1.00 | 1.00 | 1.00 |
| Mir6363 | 1.00 | 1.00 | 1.00 | 1.00 | 1.00 | 1.00 | 1.00 | 1.00 | 1.00 | 1.00 | 1.00 | 1.00 |
| Mir6386 | 1.00 | 1.00 | 1.00 | 1.00 | 1.00 | 1.00 | 1.00 | 1.00 | 1.00 | 1.00 | 1.00 | 1.00 |
| Mir6403 | 1.00 | 1.00 | 1.00 | 1.00 | 1.00 | 1.00 | 1.00 | 1.00 | 1.00 | 1.00 | 1.00 | 1.00 |
| Mir6516 | 1.00 | 1.00 | 1.00 | 0.08 | 1.00 | 1.00 | 1.00 | 1.00 | 1.00 | 1.00 | 1.00 | 1.00 |
| Mir683-2 | 1.00 | 1.00 | 1.00 | 1.00 | 1.00 | 1.00 | 1.00 | 1.00 | 1.00 | 1.00 | 1.00 | 1.00 |
| Mir6981 | 1.00 | 1.00 | 1.00 | 0.13 | 1.00 | 1.00 | 1.00 | 1.00 | 1.00 | 1.00 | 1.00 | 1.00 |
| Mir7060 | 1.00 | 1.00 | 1.00 | 1.00 | 1.00 | 1.00 | 1.00 | 1.00 | 1.00 | 1.00 | 1.00 | 1.00 |
| Mir8101 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 1.00 | 1.00 |
| Mir8106 | 1.00 | 1.00 | 1.00 | 1.00 | 1.00 | 1.00 | 1.00 | 1.00 | 1.00 | 1.00 | 1.00 | 1.00 |
| Mir8116 | 1.00 | 1.00 | 1.00 | 1.00 | 1.00 | 1.00 | 1.00 | 1.00 | 1.00 | 1.00 | 1.00 | 1.00 |
| Mllt10 | 1.10 | 2.95 | 1.14 | 1.60 | 0.18 | 0.94 | 0.91 | 1.02 | 1.05 | 0.44 | 0.16 | 0.97 |
| Mllt4 | 0.58 | 0.74 | 0.78 | 1.55 | 0.32 | 0.84 | 1.20 | 1.11 | 1.12 | 0.39 | 0.40 | 1.13 |
| Mmab | 0.78 | 0.96 | 0.76 | 0.59 | 0.83 | 0.63 | 1.00 | 1.05 | 0.95 | 1.12 | 0.59 | 1.07 |
| Mmd | 0.69 | 0.91 | 1.11 | 0.93 | 0.37 | 0.75 | 0.68 | 0.53 | 0.83 | 0.65 | 0.63 | 0.96 |
| Mmp19 | 1.64 | 1.02 | 2.16 | 0.80 | 0.13 | 0.80 | 0.85 | 0.81 | 1.91 | 0.61 | 0.33 | 1.34 |
| Mmp28 | 0.71 | 1.00 | 1.62 | 3.00 | 0.27 | 1.30 | 1.69 | 1.14 | 1.30 | 1.00 | 0.32 | 0.82 |
| Mob1a | 0.80 | 1.00 | 1.36 | 2.61 | 0.13 | 0.82 | 0.91 | 1.86 | 1.43 | 1.00 | 0.59 | 1.15 |
| Morc3 | 0.67 | 1.23 | 0.90 | 1.36 | 0.28 | 0.93 | 0.84 | 1.01 | 1.11 | 0.50 | 0.38 | 0.99 |
| Morn2 | 0.16 | 0.12 | 0.19 | 0.16 | 2.20 | 0.39 | 0.29 | 0.25 | 0.22 | 1.25 | 1.85 | 0.58 |
| Mospd2 | 1.31 | 2.25 | 1.66 | 2.50 | 0.19 | 0.96 | 1.12 | 1.37 | 1.03 | 0.27 | 0.18 | 1.21 |
| Moxd1 | 1.00 | 1.00 | 1.00 | 1.00 | 1.00 | 1.00 | 0.98 | 1.04 | 1.17 | 1.00 | 1.00 | 1.00 |
| Mpzl3 | 1.00 | 1.00 | 1.00 | 1.09 | 1.00 | 1.07 | 1.00 | 1.00 | 1.00 | 1.00 | 1.00 | 1.12 |
| Mr1 | 0.78 | 1.41 | 0.82 | 1.12 | 0.60 | 0.57 | 0.92 | 1.19 | 1.00 | 0.32 | 0.32 | 0.94 |
| Mrgbp | 1.11 | 1.00 | 1.12 | 0.66 | 0.18 | 1.01 | 1.06 | 0.71 | 1.19 | 1.00 | 0.28 | 0.95 |
| Mrgprf | 0.75 | 0.94 | 0.86 | 0.73 | 0.78 | 1.78 | 0.72 | 0.52 | 0.88 | 0.70 | 0.34 | 1.13 |
| Mroh6 | 1.00 | 1.00 | 1.00 | 1.00 | 1.00 | 1.00 | 1.00 | 1.00 | 1.00 | 1.00 | 1.00 | 1.00 |
| Mrps2 | 1.11 | 1.69 | 1.27 | 0.88 | 0.34 | 0.99 | 1.00 | 1.05 | 0.99 | 0.47 | 0.49 | 1.04 |
| Mrrf | 1.28 | 1.01 | 1.11 | 0.60 | 2.67 | 0.91 | 1.11 | 1.11 | 0.91 | 1.14 | 1.81 | 0.85 |
| Msi2 | 0.98 | 1.57 | 1.09 | 1.66 | 0.43 | 1.02 | 0.86 | 0.99 | 1.04 | 0.52 | 0.59 | 1.01 |
| Msln | 1.00 | 1.00 | 1.00 | 1.00 | 1.00 | 1.00 | 1.00 | 1.00 | 1.85 | 1.01 | 1.98 | 1.13 |
| Msmp | 1.00 | 1.00 | 1.00 | 1.00 | 1.00 | 1.00 | 1.00 | 1.00 | 1.00 | 1.00 | 1.00 | 1.00 |
| Msn | 1.16 | 1.71 | 1.24 | 2.36 | 0.20 | 1.05 | 1.29 | 1.25 | 1.48 | 0.29 | 0.28 | 0.98 |
| Msx2 | 1.00 | 1.00 | 1.00 | 1.00 | 1.00 | 1.00 | 1.00 | 1.00 | 1.00 | 1.00 | 1.00 | 1.00 |
| Mterf1a | 0.86 | 0.72 | 1.68 | 1.43 | 2.10 | 0.89 | 1.05 | 0.71 | 0.57 | 0.99 | 1.05 | 0.74 |
| Mterfd3 | 0.50 | 0.81 | 0.85 | 0.70 | 0.19 | 0.64 | 0.82 | 1.00 | 0.79 | 0.51 | 0.55 | 0.80 |
| Mthfs | 1.43 | 0.99 | 0.98 | 0.45 | 0.88 | 0.62 | 0.94 | 0.91 | 1.17 | 0.20 | 0.69 | 0.93 |
| Mtm1 | 0.79 | 1.65 | 0.89 | 1.14 | 0.25 | 0.74 | 0.94 | 0.93 | 0.87 | 0.58 | 0.43 | 1.01 |
| Mtmr9 | 0.84 | 1.00 | 1.34 | 1.11 | 0.11 | 0.64 | 1.39 | 2.03 | 1.55 | 0.71 | 0.55 | 1.07 |
| Mtss1l | 0.71 | 0.99 | 0.76 | 0.98 | 0.14 | 0.94 | 1.12 | 0.98 | 0.99 | 0.73 | 0.32 | 0.92 |
| Muc15 | 1.00 | 1.00 | 1.00 | 1.00 | 1.00 | 1.00 | 1.00 | 1.00 | 1.00 | 1.00 | 1.00 | 1.00 |
| Mvb12b | 0.73 | 0.93 | 0.68 | 0.91 | 0.40 | 0.97 | 1.06 | 1.06 | 0.87 | 0.51 | 0.63 | 0.94 |
| Mxd4 | 0.71 | 0.98 | 1.28 | 0.76 | 1.22 | 1.13 | 1.44 | 1.96 | 1.62 | 0.94 | 1.15 | 1.39 |
| Mxi1 | 0.81 | 1.43 | 0.90 | 2.19 | 0.58 | 1.24 | 1.08 | 1.07 | 0.96 | 0.43 | 0.32 | 0.89 |
| Myc | 1.48 | 3.64 | 2.38 | 1.23 | 0.61 | 0.95 | 1.70 | 1.38 | 1.85 | 0.39 | 0.21 | 1.01 |
| Mylip | 0.64 | 0.89 | 0.74 | 1.55 | 0.28 | 1.47 | 0.82 | 0.92 | 0.83 | 0.31 | 0.22 | 0.89 |
| Mylk | 1.16 | 2.10 | 1.65 | 1.16 | 0.24 | 1.11 | 1.37 | 1.64 | 1.70 | 0.36 | 0.24 | 0.90 |
| Mylk4 | 0.17 | 0.67 | 0.25 | 1.00 | 0.61 | 0.18 | 0.40 | 0.65 | 0.40 | 1.00 | 1.00 | 0.44 |
| Myo19 | 1.00 | 1.00 | 0.98 | 0.41 | 0.23 | 0.78 | 0.56 | 0.61 | 0.99 | 1.00 | 0.61 | 1.32 |
| Mysm1 | 0.82 | 1.00 | 1.05 | 3.20 | 0.41 | 1.14 | 1.00 | 1.24 | 1.09 | 0.86 | 0.37 | 0.85 |
| Mzt1 | 0.64 | 2.63 | 0.74 | 2.50 | 0.19 | 1.13 | 0.76 | 1.10 | 0.87 | 0.34 | 0.23 | 1.03 |
| Naa40 | 0.95 | 1.05 | 0.87 | 0.93 | 0.27 | 0.97 | 0.74 | 0.65 | 0.77 | 0.51 | 0.36 | 0.98 |
| Naa60 | 0.77 | 1.04 | 0.64 | 0.70 | 0.29 | 0.92 | 0.87 | 0.77 | 0.70 | 0.24 | 0.34 | 0.79 |
| Nab2 | 1.08 | 1.35 | 1.34 | 1.74 | 0.60 | 1.81 | 0.96 | 1.20 | 1.50 | 0.37 | 0.41 | 1.09 |
| Nabp1 | 0.92 | 2.10 | 1.18 | 0.67 | 0.13 | 0.60 | 0.71 | 1.05 | 1.12 | 0.53 | 0.48 | 1.27 |
| Naf1 | 0.71 | 0.79 | 0.89 | 2.43 | 1.21 | 1.32 | 1.19 | 0.97 | 1.14 | 0.99 | 0.85 | 0.94 |
| Nat2 | 1.14 | 1.03 | 1.38 | 3.03 | 1.43 | 1.39 | 1.41 | 0.97 | 1.09 | 0.66 | 0.77 | 0.94 |

Fig. 35- 62

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Mid2 | 1.45 | 1.26 | 1.95 | 1.18 | 1.00 | 1.19 | 0.87 | 1.00 | 0.84 | 1.04 | 0.64 | 0.98 |
| Mier1 | 0.56 | 0.50 | 0.66 | 1.24 | 1.63 | 0.99 | 1.16 | 1.00 | 1.05 | 0.91 | 0.67 | 1.03 |
| Mir1199 | 1.00 | 1.00 | 1.00 | 1.00 | 1.00 | 1.00 | 1.00 | 1.00 | 1.00 | 0.07 | 1.00 | 1.00 |
| Mir215 | 1.00 | 1.00 | 1.00 | 1.00 | 1.00 | 1.00 | 1.00 | 1.00 | 1.00 | 1.00 | 1.00 | 0.03 |
| Mir3473g | 1.00 | 1.00 | 1.00 | 1.00 | 1.00 | 1.00 | 1.00 | 1.00 | 1.00 | 1.00 | 1.00 | 1.00 |
| Mir486 | 1.00 | 1.00 | 1.00 | 1.00 | 1.00 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 1.00 | 1.00 | 1.00 | 1.00 |
| Mir6363 | 1.00 | 1.00 | 3.19 | 1.00 | 1.00 | 1.00 | 1.00 | 1.00 | 1.00 | 1.00 | 1.00 | 1.00 |
| Mir6386 | 1.00 | 1.00 | 1.00 | 1.00 | 1.00 | 0.01 | 1.00 | 1.00 | 1.00 | 1.00 | 1.00 | 1.00 |
| Mir6403 | 1.00 | 1.00 | 1.00 | 1.00 | 1.00 | 1.00 | 1.00 | 1.00 | 1.00 | 1.00 | 1.00 | 0.11 |
| Mir6516 | 1.00 | 1.00 | 1.00 | 1.00 | 1.00 | 1.00 | 1.00 | 1.00 | 1.00 | 1.00 | 1.00 | 1.00 |
| Mir683-2 | 1.00 | 1.00 | 1.00 | 1.00 | 1.00 | 1.00 | 1.00 | 1.00 | 1.00 | 1.00 | 1.00 | 1.00 |
| Mir6981 | 1.00 | 1.00 | 1.00 | 1.00 | 1.00 | 1.00 | 1.00 | 1.00 | 1.00 | 1.00 | 1.00 | 1.00 |
| Mir7060 | 1.00 | 1.00 | 1.00 | 1.00 | 1.00 | 1.00 | 1.00 | 1.00 | 1.00 | 1.00 | 1.00 | 1.00 |
| Mir8101 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 1.00 | 0.02 |
| Mir8106 | 1.00 | 1.00 | 1.00 | 1.00 | 1.00 | 1.00 | 1.00 | 1.00 | 1.00 | 0.08 | 1.00 | 1.00 |
| Mir8116 | 0.00 | 1.00 | 1.00 | 1.00 | 1.00 | 1.00 | 1.00 | 1.00 | 1.00 | 1.00 | 1.00 | 1.00 |
| Mllt10 | 0.64 | 0.57 | 0.83 | 1.23 | 1.00 | 0.95 | 0.84 | 1.00 | 0.98 | 0.95 | 0.76 | 1.03 |
| Mllt4 | 1.00 | 0.87 | 1.11 | 1.38 | 1.82 | 1.13 | 1.29 | 1.00 | 1.40 | 1.05 | 0.73 | 0.98 |
| Mmab | 1.13 | 1.00 | 1.17 | 0.70 | 0.91 | 0.84 | 0.44 | 2.08 | 0.60 | 0.94 | 0.86 | 0.91 |
| Mmd | 0.92 | 1.03 | 0.92 | 0.72 | 0.59 | 0.95 | 0.94 | 0.56 | 0.90 | 0.92 | 0.72 | 1.08 |
| Mmp19 | 1.88 | 1.26 | 1.19 | 1.00 | 1.00 | 1.00 | 0.45 | 0.32 | 0.67 | 1.05 | 1.39 | 1.20 |
| Mmp28 | 1.01 | 0.59 | 1.20 | 1.12 | 1.00 | 1.17 | 1.00 | 1.00 | 1.00 | 1.16 | 0.52 | 1.23 |
| Mob1a | 0.45 | 0.22 | 0.93 | 1.25 | 1.00 | 1.24 | 1.15 | 1.00 | 1.10 | 1.04 | 0.15 | 0.98 |
| Morc3 | 0.71 | 0.72 | 0.93 | 0.94 | 0.80 | 0.95 | 0.93 | 1.14 | 0.87 | 1.01 | 0.74 | 0.94 |
| Morn2 | 0.53 | 0.80 | 0.25 | 0.51 | 0.29 | 0.41 | 0.55 | 0.69 | 0.67 | 0.78 | 0.59 | 0.45 |
| Mospd2 | 1.15 | 0.90 | 1.29 | 1.00 | 1.00 | 0.84 | 0.71 | 1.00 | 0.82 | 0.96 | 0.68 | 1.13 |
| Moxd1 | 0.78 | 0.51 | 0.51 | 1.00 | 1.00 | 1.00 | 1.02 | 1.00 | 1.00 | 0.77 | 1.00 | 0.74 |
| Mpzl3 | 0.91 | 0.44 | 1.07 | 1.24 | 1.00 | 1.00 | 2.03 | 1.00 | 1.32 | 1.88 | 0.52 | 0.93 |
| Mr1 | 0.58 | 0.53 | 0.67 | 0.85 | 1.00 | 0.99 | 0.76 | 1.00 | 0.89 | 0.89 | 0.63 | 0.92 |
| Mrgbp | 0.83 | 0.92 | 0.81 | 0.86 | 1.00 | 0.96 | 0.93 | 1.00 | 1.28 | 1.14 | 0.91 | 0.90 |
| Mrgprf | 2.17 | 1.98 | 2.15 | 1.00 | 1.00 | 1.00 | 1.00 | 1.00 | 1.00 | 0.89 | 0.72 | 1.02 |
| Mroh6 | 1.00 | 1.00 | 1.00 | 1.00 | 1.00 | 1.00 | 1.00 | 1.00 | 1.13 | 1.00 | 1.00 | 1.00 |
| Mrps2 | 0.84 | 0.85 | 0.87 | 1.05 | 1.36 | 0.99 | 1.08 | 0.49 | 0.88 | 0.91 | 0.76 | 0.99 |
| Mrrf | 1.18 | 1.37 | 1.09 | 1.07 | 0.99 | 1.10 | 1.41 | 0.76 | 1.05 | 1.03 | 1.34 | 0.92 |
| Msi2 | 0.68 | 0.62 | 0.84 | 1.05 | 1.49 | 1.03 | 0.85 | 1.03 | 1.04 | 0.95 | 0.72 | 0.95 |
| Msln | 2.34 | 2.52 | 1.16 | 1.00 | 1.00 | 1.00 | 1.00 | 1.00 | 1.00 | 1.00 | 1.00 | 1.00 |
| Msmp | 1.00 | 1.00 | 1.00 | 1.00 | 1.00 | 1.00 | 1.00 | 1.00 | 1.00 | 1.00 | 1.00 | 1.00 |
| Msn | 0.64 | 0.62 | 0.96 | 0.99 | 1.50 | 0.97 | 0.90 | 1.00 | 0.82 | 0.98 | 0.54 | 1.06 |
| Msx2 | 1.00 | 1.00 | 1.00 | 1.00 | 1.00 | 1.00 | 1.00 | 1.00 | 1.00 | 1.00 | 1.00 | 1.00 |
| Mterf1a | 1.16 | 0.98 | 0.87 | 0.80 | 1.18 | 0.52 | 1.14 | 0.56 | 0.97 | 1.07 | 1.19 | 0.90 |
| Mterfd3 | 0.99 | 1.08 | 0.77 | 0.80 | 0.54 | 0.75 | 1.10 | 1.09 | 0.86 | 0.96 | 0.97 | 1.05 |
| Mthfs | 1.26 | 1.56 | 1.16 | 0.79 | 1.29 | 0.95 | 1.01 | 0.45 | 1.00 | 0.77 | 1.29 | 0.85 |
| Mtm1 | 1.32 | 1.29 | 1.65 | 1.16 | 1.13 | 1.22 | 0.99 | 1.00 | 0.91 | 0.93 | 0.76 | 1.02 |
| Mtmr9 | 0.59 | 0.44 | 0.77 | 1.16 | 1.00 | 1.21 | 0.89 | 1.00 | 1.19 | 1.01 | 0.60 | 0.85 |
| Mtss1l | 0.59 | 0.44 | 0.91 | 0.47 | 1.00 | 0.65 | 0.69 | 1.00 | 0.79 | 0.87 | 0.57 | 0.90 |
| Muc15 | 1.00 | 1.00 | 1.00 | 1.00 | 1.00 | 1.00 | 1.00 | 1.00 | 1.00 | 1.00 | 1.00 | 1.00 |
| Mvb12b | 0.94 | 0.95 | 0.84 | 1.01 | 1.05 | 0.99 | 1.00 | 1.00 | 1.00 | 1.07 | 0.92 | 1.09 |
| Mxd4 | 0.73 | 0.62 | 1.12 | 1.34 | 1.30 | 1.46 | 1.34 | 0.76 | 1.54 | 1.06 | 0.83 | 1.01 |
| Mxi1 | 0.80 | 0.85 | 0.96 | 0.94 | 1.53 | 1.03 | 0.95 | 0.51 | 0.86 | 0.92 | 0.80 | 0.94 |
| Myc | 0.66 | 0.54 | 0.75 | 1.00 | 1.55 | 1.05 | 1.11 | 1.00 | 2.09 | 1.00 | 0.81 | 1.18 |
| Mylip | 1.07 | 1.00 | 1.28 | 1.36 | 4.66 | 1.35 | 0.72 | 1.00 | 0.81 | 0.88 | 0.73 | 0.97 |
| Mylk | 1.28 | 0.80 | 0.97 | 1.09 | 1.53 | 1.08 | 0.95 | 0.98 | 1.02 | 1.01 | 0.72 | 0.97 |
| Mylk4 | 1.00 | 1.00 | 1.00 | 1.00 | 1.00 | 1.00 | 1.00 | 1.00 | 1.00 | 1.00 | 1.00 | 1.00 |
| Myo19 | 0.53 | 0.65 | 1.08 | 0.94 | 1.90 | 0.98 | 1.03 | 1.00 | 1.08 | 1.23 | 1.10 | 1.05 |
| Mysm1 | 0.75 | 0.68 | 0.99 | 1.17 | 0.95 | 1.07 | 1.18 | 1.00 | 1.08 | 1.04 | 0.68 | 0.98 |
| Mzt1 | 0.66 | 0.63 | 0.79 | 1.03 | 2.77 | 0.95 | 1.18 | 1.00 | 1.05 | 1.13 | 0.91 | 1.02 |
| Naa40 | 0.70 | 0.70 | 0.71 | 0.92 | 1.24 | 0.91 | 1.16 | 0.96 | 0.97 | 0.96 | 0.71 | 0.93 |
| Naa60 | 0.91 | 1.01 | 1.08 | 0.78 | 1.39 | 0.83 | 0.72 | 0.24 | 0.72 | 0.95 | 0.91 | 0.91 |
| Nab2 | 1.12 | 0.96 | 1.59 | 0.77 | 1.47 | 0.98 | 1.23 | 0.32 | 1.23 | 0.87 | 0.77 | 0.87 |
| Nabp1 | 0.36 | 0.30 | 0.61 | 0.94 | 1.47 | 1.17 | 1.46 | 1.00 | 1.30 | 0.98 | 0.60 | 1.01 |
| Naf1 | 0.98 | 0.85 | 1.13 | 0.91 | 0.94 | 1.03 | 1.26 | 0.96 | 1.13 | 1.05 | 1.00 | 1.02 |
| Nat2 | 0.96 | 1.16 | 1.02 | 1.13 | 3.05 | 1.06 | 0.75 | 0.52 | 0.99 | 1.16 | 1.02 | 1.12 |

Fig. 35- 63

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Mid2 | 1.09 | 1.02 | 0.95 | 1.25 | 1.00 | 0.85 | 1.00 | 1.00 | 1.00 | 0.79 | 0.62 | 1.00 |
| Mier1 | 1.13 | 0.97 | 0.98 | 1.26 | 0.38 | 1.12 | 1.08 | 2.92 | 1.03 | 1.03 | 0.65 | 1.08 |
| Mir1199 | 1.00 | 1.00 | 1.00 | 1.00 | 1.00 | 1.00 | 1.00 | 1.00 | 1.00 | 1.00 | 1.00 | 1.00 |
| Mir215 | 1.00 | 1.00 | 1.00 | 1.00 | 1.00 | 1.00 | 1.00 | 1.00 | 1.00 | 1.00 | 1.00 | 1.00 |
| Mir3473g | 1.00 | 1.00 | 1.00 | 1.00 | 1.00 | 1.00 | 1.00 | 1.00 | 1.00 | 1.00 | 1.00 | 1.00 |
| Mir486 | 1.00 | 1.00 | 1.00 | 1.00 | 1.00 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 1.00 | 1.00 | 1.00 | 1.00 |
| Mir6363 | 1.00 | 1.00 | 1.00 | 1.00 | 1.00 | 1.00 | 1.00 | 1.00 | 1.00 | 1.00 | 1.00 | 1.00 |
| Mir6386 | 1.00 | 1.00 | 1.00 | 1.00 | 1.00 | 1.00 | 1.00 | 1.00 | 1.00 | 1.00 | 1.00 | 0.01 |
| Mir6403 | 1.00 | 1.00 | 1.00 | 1.00 | 1.00 | 1.00 | 1.00 | 1.00 | 1.00 | 1.00 | 1.00 | 1.00 |
| Mir6516 | 1.00 | 1.00 | 1.00 | 1.00 | 1.00 | 1.00 | 1.00 | 1.00 | 1.00 | 1.00 | 1.00 | 1.00 |
| Mir683-2 | 1.00 | 1.00 | 1.00 | 1.00 | 1.00 | 1.00 | 1.00 | 1.00 | 0.02 | 1.00 | 1.00 | 1.00 |
| Mir6981 | 1.00 | 1.00 | 1.00 | 0.02 | 1.00 | 1.00 | 1.00 | 1.00 | 1.00 | 1.00 | 1.00 | 1.00 |
| Mir7060 | 1.00 | 1.00 | 1.00 | 1.00 | 1.00 | 0.20 | 0.09 | 1.00 | 1.00 | 1.00 | 1.00 | 1.00 |
| Mir8101 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 0.01 | 0.02 |
| Mir8106 | 1.00 | 1.00 | 1.00 | 1.00 | 1.00 | 1.00 | 1.00 | 1.00 | 1.00 | 1.00 | 1.00 | 1.00 |
| Mir8116 | 1.00 | 1.00 | 1.00 | 1.00 | 1.00 | 1.00 | 1.00 | 1.00 | 1.00 | 1.00 | 1.00 | 1.00 |
| Mllt10 | 0.99 | 0.94 | 0.94 | 0.93 | 0.41 | 1.07 | 1.01 | 0.45 | 1.08 | 1.00 | 0.69 | 0.96 |
| Mllt4 | 0.98 | 0.94 | 0.79 | 1.08 | 0.22 | 0.87 | 1.34 | 1.00 | 1.02 | 0.84 | 0.87 | 1.05 |
| Mmab | 0.84 | 0.94 | 1.02 | 0.58 | 0.86 | 0.76 | 0.82 | 1.00 | 0.93 | 1.16 | 0.93 | 1.05 |
| Mmd | 0.81 | 0.90 | 1.31 | 0.24 | 0.10 | 0.35 | 1.58 | 1.00 | 1.06 | 1.19 | 1.18 | 0.98 |
| Mmp19 | 1.10 | 1.34 | 0.87 | 1.97 | 0.63 | 1.03 | 1.00 | 1.00 | 0.99 | 1.20 | 0.89 | 0.90 |
| Mmp28 | 0.69 | 0.77 | 0.71 | 0.68 | 0.36 | 0.73 | 1.00 | 1.00 | 1.00 | 0.87 | 0.73 | 1.12 |
| Mob1a | 0.91 | 0.87 | 0.71 | 1.13 | 0.11 | 0.52 | 1.42 | 1.00 | 0.99 | 0.78 | 0.24 | 1.08 |
| Morc3 | 1.06 | 0.88 | 0.90 | 0.89 | 0.44 | 0.72 | 1.07 | 0.70 | 1.08 | 1.03 | 0.73 | 1.06 |
| Morn2 | 0.37 | 0.34 | 0.51 | 0.50 | 1.23 | 0.47 | 1.12 | 2.22 | 1.24 | 0.60 | 0.91 | 0.63 |
| Mospd2 | 0.97 | 0.88 | 0.87 | 0.91 | 0.84 | 0.78 | 1.08 | 1.00 | 1.04 | 1.05 | 0.74 | 0.96 |
| Moxd1 | 1.25 | 1.11 | 1.22 | 1.00 | 1.00 | 1.00 | 0.75 | 0.68 | 1.00 | 1.00 | 1.00 | 1.00 |
| Mpzl3 | 0.84 | 0.63 | 0.57 | 1.00 | 1.00 | 1.00 | 1.00 | 1.00 | 1.00 | 1.00 | 0.72 | 0.79 |
| Mr1 | 0.98 | 0.91 | 1.10 | 0.71 | 0.55 | 0.76 | 0.73 | 1.00 | 1.02 | 0.96 | 0.80 | 1.12 |
| Mrgbp | 0.75 | 1.07 | 0.71 | 1.02 | 1.00 | 1.20 | 0.89 | 0.50 | 1.06 | 1.13 | 0.85 | 1.26 |
| Mrgprf | 0.90 | 0.79 | 1.23 | 1.14 | 1.00 | 1.70 | 1.00 | 1.00 | 1.00 | 1.00 | 1.00 | 1.00 |
| Mroh6 | 0.73 | 0.90 | 0.72 | 1.00 | 1.00 | 1.00 | 1.00 | 1.00 | 1.00 | 1.00 | 1.00 | 1.00 |
| Mrps2 | 0.94 | 1.02 | 1.09 | 1.01 | 0.40 | 1.13 | 1.05 | 0.61 | 0.92 | 0.93 | 0.89 | 0.89 |
| Mrrf | 1.10 | 0.97 | 1.17 | 0.83 | 4.63 | 0.95 | 0.86 | 0.82 | 0.97 | 0.97 | 1.32 | 0.96 |
| Msi2 | 1.00 | 0.93 | 0.90 | 1.09 | 0.19 | 1.05 | 1.00 | 0.73 | 0.98 | 0.97 | 0.63 | 1.07 |
| Msin | 1.00 | 0.92 | 1.00 | 1.41 | 2.35 | 1.52 | 1.00 | 1.00 | 1.00 | 1.00 | 1.05 | 1.25 |
| Msmp | 1.00 | 1.00 | 1.00 | 0.62 | 0.20 | 0.68 | 1.00 | 1.00 | 1.00 | 1.00 | 1.00 | 1.00 |
| Msn | 1.12 | 1.01 | 1.21 | 1.32 | 0.20 | 1.11 | 1.10 | 1.00 | 0.98 | 0.91 | 0.53 | 0.91 |
| Msx2 | 1.00 | 1.00 | 1.00 | 1.00 | 1.00 | 1.00 | 0.76 | 1.00 | 0.68 | 1.00 | 1.00 | 1.00 |
| Mterf1a | 0.77 | 0.85 | 0.91 | 1.03 | 2.22 | 1.00 | 0.78 | 0.58 | 0.96 | 1.07 | 0.99 | 0.95 |
| Mterfd3 | 0.98 | 0.99 | 1.21 | 0.77 | 1.03 | 0.59 | 1.20 | 0.66 | 0.84 | 1.32 | 1.07 | 0.97 |
| Mthfs | 0.89 | 1.10 | 0.88 | 0.94 | 1.00 | 0.72 | 0.86 | 0.50 | 0.63 | 1.00 | 1.07 | 0.71 |
| Mtm1 | 1.04 | 0.90 | 0.97 | 0.79 | 0.96 | 1.11 | 0.75 | 0.70 | 0.77 | 1.33 | 1.08 | 1.35 |
| Mtmr9 | 0.76 | 1.00 | 0.59 | 1.14 | 0.25 | 0.63 | 1.03 | 0.52 | 1.08 | 0.97 | 0.82 | 1.19 |
| Mtss1l | 0.94 | 0.94 | 1.14 | 0.87 | 0.31 | 0.99 | 0.77 | 1.00 | 0.61 | 0.97 | 0.90 | 0.93 |
| Muc15 | 1.00 | 0.70 | 1.68 | 1.00 | 1.00 | 1.00 | 1.00 | 1.00 | 1.00 | 1.00 | 1.00 | 1.00 |
| Mvb12b | 0.93 | 1.01 | 1.10 | 0.79 | 0.61 | 0.84 | 0.99 | 1.00 | 1.02 | 0.90 | 1.17 | 0.85 |
| Mxd4 | 1.15 | 1.13 | 1.08 | 1.18 | 0.76 | 0.93 | 1.01 | 0.98 | 1.08 | 0.89 | 0.68 | 1.31 |
| Mxi1 | 1.01 | 1.06 | 1.18 | 1.25 | 0.85 | 1.20 | 0.96 | 0.37 | 0.92 | 1.03 | 1.04 | 0.91 |
| Myc | 0.97 | 0.95 | 1.14 | 1.26 | 0.58 | 1.32 | 1.00 | 1.00 | 1.00 | 1.66 | 1.65 | 1.45 |
| Mylip | 1.06 | 1.10 | 1.44 | 1.14 | 0.19 | 0.97 | 0.99 | 1.00 | 0.94 | 1.03 | 0.76 | 1.03 |
| Mylk | 1.06 | 1.10 | 1.20 | 1.42 | 0.15 | 1.14 | 1.03 | 0.78 | 0.91 | 0.93 | 0.60 | 1.06 |
| Mylk4 | 1.00 | 1.00 | 1.00 | 1.00 | 1.00 | 1.00 | 1.00 | 1.00 | 1.00 | 1.00 | 1.00 | 1.00 |
| Myo19 | 1.07 | 1.27 | 0.82 | 0.78 | 1.00 | 0.94 | 1.05 | 0.57 | 1.09 | 1.21 | 0.93 | 0.93 |
| Mysm1 | 1.21 | 0.93 | 1.07 | 1.07 | 0.66 | 0.91 | 1.02 | 1.00 | 0.98 | 1.09 | 0.67 | 1.08 |
| Mzt1 | 1.00 | 1.00 | 1.10 | 0.86 | 1.00 | 1.09 | 1.20 | 0.92 | 1.04 | 1.05 | 0.86 | 0.88 |
| Naa40 | 0.85 | 0.87 | 0.91 | 0.88 | 0.31 | 1.07 | 0.94 | 0.67 | 1.01 | 0.93 | 0.89 | 0.92 |
| Naa60 | 0.93 | 0.93 | 0.89 | 0.74 | 0.40 | 0.89 | 0.89 | 2.19 | 0.96 | 1.01 | 0.87 | 0.95 |
| Nab2 | 0.75 | 0.87 | 1.01 | 0.78 | 0.45 | 0.85 | 1.12 | 0.54 | 1.01 | 0.63 | 0.55 | 1.05 |
| Nabp1 | 0.90 | 0.73 | 0.85 | 0.44 | 0.29 | 0.62 | 1.07 | 0.93 | 1.05 | 0.68 | 0.37 | 0.88 |
| Naf1 | 1.06 | 1.09 | 0.96 | 1.14 | 1.00 | 1.15 | 1.14 | 0.83 | 1.03 | 1.19 | 0.88 | 0.99 |
| Nat2 | 1.13 | 0.90 | 0.79 | 1.06 | 1.00 | 1.31 | 0.93 | 1.00 | 0.97 | 0.97 | 0.86 | 1.05 |

Fig. 35- 64

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Mid2 | 0.91 | 1.12 | 1.23 | 1.00 | 1.00 | 0.94 | 0.71 | 0.12 | 0.84 | 1.00 | 1.00 | 1.00 |
| Mier1 | 1.14 | 1.33 | 1.13 | 0.95 | 1.00 | 0.94 | 0.94 | 0.06 | 1.25 | 0.51 | 0.99 | 0.88 |
| Mir1199 | 1.00 | 1.00 | 1.00 | 1.00 | 1.00 | 1.00 | 1.00 | 1.00 | 1.00 | 1.00 | 1.00 | 1.00 |
| Mir215 | 1.00 | 1.00 | 1.00 | 1.00 | 1.00 | 1.00 | 1.00 | 1.00 | 1.00 | 1.00 | 1.00 | 1.00 |
| Mir3473g | 1.00 | 1.00 | 1.00 | 1.00 | 1.00 | 0.18 | 1.00 | 1.00 | 1.00 | 1.00 | 1.00 | 1.00 |
| Mir486 | 1.00 | 1.00 | 1.00 | 1.00 | 1.00 | 0.06 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 0.13 | 1.00 | 1.00 | 1.00 |
| Mir6363 | 1.00 | 1.00 | 1.00 | 1.00 | 1.00 | 1.00 | 1.00 | 0.09 | 1.00 | 1.00 | 1.00 | 1.00 |
| Mir6386 | 1.00 | 1.00 | 1.00 | 1.00 | 1.00 | 1.00 | 1.00 | 1.00 | 1.00 | 1.00 | 1.00 | 1.00 |
| Mir6403 | 1.00 | 1.00 | 1.00 | 1.00 | 1.00 | 1.00 | 1.00 | 1.00 | 1.00 | 1.00 | 1.00 | 1.00 |
| Mir6516 | 1.00 | 1.00 | 1.00 | 1.00 | 1.00 | 0.03 | 1.00 | 1.00 | 1.00 | 0.02 | 1.00 | 1.00 |
| Mir683-2 | 1.00 | 1.00 | 1.00 | 1.00 | 1.00 | 1.00 | 1.00 | 1.00 | 1.00 | 1.00 | 1.00 | 1.00 |
| Mir6981 | 1.00 | 1.00 | 1.00 | 1.00 | 1.00 | 1.00 | 1.00 | 1.00 | 1.00 | 1.00 | 1.00 | 0.04 |
| Mir7060 | 1.00 | 1.00 | 1.00 | 1.00 | 1.00 | 1.00 | 1.00 | 1.00 | 1.00 | 1.00 | 1.00 | 1.00 |
| Mir8101 | 1.00 | 1.00 | 1.00 | 1.00 | 1.00 | 0.11 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 1.00 | 1.00 |
| Mir8106 | 1.00 | 1.00 | 1.00 | 1.00 | 1.00 | 1.00 | 1.00 | 1.00 | 1.00 | 1.00 | 1.00 | 1.00 |
| Mir8116 | 1.00 | 1.00 | 1.00 | 1.00 | 1.00 | 1.00 | 1.00 | 1.00 | 1.00 | 1.00 | 1.00 | 1.00 |
| Mllt10 | 1.00 | 0.87 | 1.09 | 0.88 | 0.87 | 1.00 | 0.79 | 0.08 | 1.04 | 0.15 | 0.98 | 0.92 |
| Mllt4 | 1.15 | 0.92 | 1.30 | 0.98 | 1.00 | 0.96 | 0.96 | 0.14 | 1.15 | 1.00 | 0.90 | 0.84 |
| Mmab | 1.00 | 1.00 | 1.00 | 1.12 | 0.50 | 1.14 | 0.62 | 0.13 | 0.61 | 0.69 | 0.69 | 1.14 |
| Mmd | 1.00 | 1.00 | 1.00 | 1.14 | 1.52 | 1.08 | 0.79 | 0.21 | 0.78 | 0.61 | 1.06 | 1.45 |
| Mmp19 | 1.00 | 1.00 | 1.00 | 1.00 | 1.00 | 1.00 | 1.00 | 0.40 | 1.16 | 1.00 | 1.13 | 1.32 |
| Mmp28 | 1.00 | 1.00 | 1.00 | 0.76 | 1.00 | 0.90 | 0.99 | 0.10 | 1.16 | 1.00 | 1.00 | 1.00 |
| Mob1a | 1.02 | 0.95 | 1.19 | 0.77 | 1.00 | 0.91 | 0.56 | 0.12 | 1.00 | 0.86 | 0.57 | 0.63 |
| Morc3 | 0.86 | 0.80 | 0.99 | 0.98 | 1.00 | 0.87 | 0.81 | 0.12 | 0.94 | 0.56 | 0.93 | 1.02 |
| Morn2 | 0.47 | 1.37 | 0.68 | 0.30 | 0.22 | 0.26 | 3.33 | 3.44 | 0.33 | 0.39 | 0.47 | 0.35 |
| Mospd2 | 0.81 | 1.13 | 1.03 | 0.85 | 1.00 | 0.99 | 0.74 | 0.09 | 0.98 | 0.42 | 1.25 | 1.22 |
| Moxd1 | 1.00 | 1.00 | 1.00 | 1.04 | 1.00 | 0.86 | 0.71 | 0.13 | 0.92 | 1.00 | 1.00 | 1.00 |
| Mpzl3 | 1.00 | 1.00 | 1.00 | 1.00 | 1.00 | 1.09 | 0.61 | 0.13 | 0.89 | 1.00 | 1.14 | 1.34 |
| Mr1 | 0.57 | 1.00 | 0.68 | 0.87 | 1.00 | 1.04 | 0.69 | 0.18 | 0.94 | 0.68 | 0.90 | 0.92 |
| Mrgbp | 1.30 | 0.69 | 1.39 | 0.70 | 1.00 | 0.86 | 1.05 | 0.09 | 1.05 | 0.27 | 0.86 | 1.02 |
| Mrgprf | 1.00 | 1.00 | 1.00 | 0.95 | 1.00 | 1.04 | 0.57 | 0.19 | 0.56 | 1.00 | 1.00 | 1.00 |
| Mroh6 | 1.00 | 1.00 | 1.00 | 1.00 | 1.00 | 1.00 | 0.87 | 0.08 | 1.03 | 1.00 | 1.00 | 1.00 |
| Mrps2 | 1.00 | 0.87 | 0.85 | 1.05 | 0.36 | 0.92 | 0.76 | 0.19 | 0.76 | 0.47 | 0.67 | 0.90 |
| Mrrf | 1.32 | 0.97 | 0.82 | 1.00 | 0.20 | 1.07 | 1.08 | 3.16 | 1.02 | 1.33 | 0.95 | 0.99 |
| Msi2 | 0.86 | 1.06 | 0.90 | 0.91 | 3.29 | 1.02 | 0.80 | 0.26 | 0.93 | 0.61 | 0.90 | 0.92 |
| Msin | 1.00 | 1.00 | 1.00 | 1.00 | 0.20 | 1.00 | 1.00 | 1.23 | 1.00 | 1.00 | 1.00 | 1.00 |
| Msmp | 1.00 | 1.00 | 1.00 | 0.58 | 1.00 | 1.00 | 0.63 | 0.77 | 0.20 | 1.00 | 1.00 | 1.00 |
| Msn | 0.85 | 1.10 | 1.29 | 1.01 | 1.00 | 1.02 | 0.75 | 0.11 | 1.06 | 0.41 | 0.96 | 1.02 |
| Msx2 | 1.00 | 1.00 | 1.00 | 0.97 | 1.00 | 1.36 | 0.72 | 0.06 | 0.55 | 1.00 | 1.00 | 1.00 |
| Mterf1a | 1.00 | 1.00 | 1.00 | 0.92 | 0.18 | 1.33 | 0.90 | 1.33 | 0.81 | 1.12 | 1.20 | 0.90 |
| Mterfd3 | 0.86 | 1.00 | 1.00 | 0.96 | 1.38 | 1.09 | 0.74 | 0.80 | 0.87 | 0.86 | 1.12 | 1.13 |
| Mthfs | 0.77 | 0.41 | 0.65 | 1.17 | 0.82 | 0.83 | 0.96 | 0.20 | 0.99 | 1.08 | 1.56 | 1.43 |
| Mtm1 | 0.85 | 0.83 | 1.00 | 1.45 | 1.00 | 1.33 | 1.09 | 0.16 | 1.51 | 0.51 | 1.02 | 1.07 |
| Mtmr9 | 1.36 | 0.80 | 1.29 | 0.91 | 1.00 | 0.80 | 0.70 | 0.21 | 0.90 | 0.58 | 0.70 | 0.87 |
| Mtss1l | 1.00 | 1.00 | 1.00 | 0.99 | 1.15 | 0.97 | 0.66 | 0.16 | 0.96 | 1.00 | 1.00 | 1.00 |
| Muc15 | 1.00 | 1.00 | 1.00 | 1.00 | 1.00 | 1.00 | 0.66 | 0.14 | 0.75 | 1.00 | 1.00 | 1.00 |
| Mvb12b | 0.96 | 1.02 | 1.05 | 1.04 | 2.24 | 0.99 | 0.96 | 0.14 | 1.01 | 0.83 | 1.10 | 0.93 |
| Mxd4 | 1.25 | 0.97 | 1.07 | 1.11 | 0.95 | 1.14 | 1.15 | 0.14 | 1.13 | 1.07 | 0.90 | 0.85 |
| Mxi1 | 0.73 | 0.92 | 0.77 | 1.03 | 1.64 | 1.02 | 0.88 | 0.18 | 0.97 | 0.47 | 1.03 | 1.01 |
| Myc | 1.17 | 1.17 | 1.08 | 1.20 | 1.00 | 1.02 | 1.05 | 0.03 | 0.92 | 0.27 | 0.72 | 0.97 |
| Mylip | 1.02 | 0.90 | 1.72 | 0.76 | 1.00 | 0.85 | 0.77 | 0.04 | 1.01 | 0.29 | 0.74 | 0.74 |
| Mylk | 1.00 | 1.00 | 1.78 | 0.88 | 1.00 | 0.96 | 1.07 | 0.23 | 1.33 | 1.00 | 0.92 | 1.52 |
| Mylk4 | 1.00 | 1.00 | 1.00 | 1.00 | 1.00 | 1.00 | 1.45 | 0.63 | 1.26 | 1.00 | 1.00 | 1.00 |
| Myo19 | 1.00 | 1.00 | 1.00 | 0.81 | 1.00 | 0.75 | 0.86 | 0.15 | 0.78 | 0.80 | 0.74 | 0.65 |
| Mysm1 | 0.99 | 1.42 | 1.00 | 0.89 | 1.17 | 0.88 | 0.87 | 0.16 | 1.12 | 0.54 | 1.04 | 0.93 |
| Mzt1 | 0.95 | 0.77 | 0.68 | 1.00 | 1.00 | 1.03 | 0.86 | 0.10 | 1.08 | 0.33 | 1.04 | 0.90 |
| Naa40 | 0.88 | 0.88 | 0.69 | 0.92 | 1.81 | 0.94 | 0.98 | 0.16 | 1.01 | 0.31 | 0.89 | 0.89 |
| Naa60 | 0.73 | 0.52 | 0.70 | 1.00 | 1.91 | 0.97 | 1.02 | 0.15 | 0.98 | 0.48 | 1.13 | 1.17 |
| Nab2 | 1.00 | 1.00 | 1.00 | 0.99 | 1.66 | 1.08 | 0.74 | 0.07 | 0.74 | 0.77 | 0.62 | 0.88 |
| Nabp1 | 1.00 | 1.00 | 1.00 | 1.01 | 1.00 | 0.92 | 0.87 | 0.46 | 0.56 | 0.39 | 0.67 | 1.10 |
| Naf1 | 1.02 | 1.23 | 1.00 | 0.71 | 0.18 | 1.01 | 0.63 | 0.72 | 0.92 | 0.70 | 0.93 | 0.84 |
| Nat2 | 1.16 | 0.61 | 0.76 | 0.84 | 1.00 | 1.00 | 0.79 | 0.12 | 1.04 | 0.40 | 0.90 | 1.08 |

Fig. 35- 65

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Nbn | 0.93 | 2.45 | 0.93 | 1.31 | 0.12 | 0.86 | 1.04 | 1.05 | 0.87 | 0.70 | 0.25 | 0.90 |
| Nck1 | 1.03 | 1.06 | 1.12 | 1.35 | 0.51 | 1.17 | 0.76 | 0.76 | 0.86 | 0.36 | 0.38 | 0.92 |
| Ncoa4 | 0.92 | 2.02 | 0.96 | 0.83 | 0.12 | 0.84 | 0.88 | 0.96 | 0.96 | 0.26 | 0.25 | 1.03 |
| Ncstn | 0.92 | 1.65 | 1.04 | 0.74 | 0.46 | 1.01 | 0.89 | 0.83 | 0.84 | 0.28 | 0.39 | 0.95 |
| Ndel1 | 1.02 | 1.71 | 0.87 | 0.93 | 0.21 | 1.01 | 1.29 | 1.21 | 0.95 | 0.34 | 0.41 | 1.04 |
| Ndst1 | 0.68 | 1.00 | 1.29 | 1.90 | 0.09 | 0.83 | 1.29 | 1.80 | 1.73 | 1.16 | 0.26 | 1.65 |
| Ndufa12 | 0.58 | 0.28 | 0.30 | 0.15 | 2.43 | 0.34 | 0.38 | 0.36 | 0.30 | 0.62 | 0.99 | 0.29 |
| Ndufaf3 | 0.83 | 0.51 | 0.76 | 0.19 | 2.78 | 0.81 | 1.13 | 0.93 | 0.78 | 1.38 | 1.58 | 0.93 |
| Nebl | 1.00 | 1.00 | 1.00 | 1.00 | 0.86 | 1.00 | 1.11 | 1.96 | 1.16 | 1.00 | 1.00 | 1.02 |
| Nedd4 | 0.78 | 1.84 | 0.96 | 1.37 | 0.21 | 1.07 | 0.97 | 0.99 | 0.93 | 0.22 | 0.19 | 0.89 |
| Nedd9 | 1.23 | 1.00 | 1.37 | 0.95 | 0.15 | 0.73 | 1.42 | 1.46 | 1.51 | 0.63 | 0.51 | 1.09 |
| Nek7 | 0.85 | 4.59 | 0.87 | 3.59 | 0.12 | 1.20 | 1.26 | 1.64 | 1.25 | 0.61 | 0.20 | 1.39 |
| Nepn | 1.00 | 1.00 | 1.00 | 0.19 | 0.14 | 0.13 | 0.77 | 0.91 | 0.84 | 1.00 | 1.00 | 1.00 |
| Nfat5 | 1.15 | 1.85 | 1.27 | 1.63 | 0.51 | 0.91 | 1.04 | 1.16 | 1.10 | 0.61 | 0.69 | 0.98 |
| Nfe2l3 | 1.00 | 1.00 | 1.00 | 3.01 | 1.61 | 1.00 | 1.00 | 1.00 | 1.00 | 1.02 | 0.45 | 1.46 |
| Nfkb1 | 1.00 | 1.44 | 1.03 | 0.77 | 0.72 | 0.97 | 0.93 | 1.01 | 1.12 | 0.31 | 0.38 | 0.93 |
| Nfya | 0.81 | 1.32 | 1.16 | 1.50 | 0.33 | 1.20 | 1.02 | 1.00 | 0.96 | 0.37 | 0.36 | 0.91 |
| Ngfr | 0.99 | 2.23 | 1.88 | 0.55 | 0.67 | 0.97 | 1.00 | 1.00 | 1.00 | 1.00 | 1.00 | 1.00 |
| Nhsl1 | 0.87 | 1.15 | 0.76 | 1.00 | 1.00 | 1.00 | 0.90 | 1.02 | 0.92 | 1.00 | 0.73 | 0.63 |
| Nid1 | 1.31 | 2.12 | 1.66 | 3.97 | 0.15 | 1.48 | 1.38 | 1.51 | 1.42 | 0.25 | 0.26 | 1.61 |
| Nipal1 | 1.00 | 1.00 | 1.00 | 1.00 | 1.00 | 1.00 | 1.00 | 1.00 | 1.00 | 1.00 | 1.00 | 1.09 |
| Nipal2 | 1.00 | 1.00 | 1.00 | 1.00 | 1.00 | 1.00 | 1.00 | 1.00 | 1.00 | 0.54 | 0.51 | 0.40 |
| Nkain1 | 0.77 | 0.78 | 0.50 | 0.21 | 0.17 | 0.18 | 0.57 | 0.49 | 0.54 | 0.27 | 0.26 | 0.46 |
| Nkx2-2 | 1.00 | 1.00 | 1.00 | 1.00 | 1.00 | 1.00 | 1.00 | 1.00 | 1.00 | 1.00 | 1.00 | 1.00 |
| Nlgn2 | 0.89 | 0.80 | 1.14 | 0.94 | 0.14 | 1.10 | 1.05 | 0.95 | 1.13 | 0.53 | 0.50 | 0.90 |
| Nlrp10 | 1.00 | 1.00 | 1.00 | 1.00 | 1.00 | 1.00 | 1.50 | 1.78 | 1.30 | 1.00 | 1.00 | 1.00 |
| Nme6 | 1.90 | 0.72 | 1.13 | 0.80 | 4.30 | 1.34 | 1.51 | 1.30 | 1.37 | 1.60 | 2.17 | 1.24 |
| Nmt1 | 1.26 | 1.67 | 1.43 | 0.70 | 1.07 | 1.23 | 1.35 | 1.10 | 1.04 | 0.67 | 0.80 | 1.14 |
| Nnt | 0.68 | 0.84 | 0.78 | 1.88 | 0.42 | 0.86 | 0.79 | 0.88 | 0.76 | 0.46 | 0.36 | 0.85 |
| Notch1 | 0.88 | 1.17 | 1.00 | 1.60 | 0.60 | 1.50 | 1.20 | 1.33 | 1.20 | 0.68 | 0.58 | 1.22 |
| Notch3 | 0.88 | 1.00 | 1.15 | 1.03 | 0.10 | 0.90 | 1.18 | 1.00 | 1.22 | 0.53 | 0.12 | 1.00 |
| Notum | 1.00 | 1.00 | 1.00 | 1.00 | 1.00 | 1.00 | 1.00 | 1.00 | 1.00 | 0.18 | 0.63 | 0.60 |
| Npepps | 1.01 | 1.50 | 0.87 | 1.29 | 0.43 | 1.14 | 0.83 | 0.85 | 0.83 | 0.41 | 0.45 | 1.02 |
| Npnt | 2.18 | 3.13 | 2.01 | 0.99 | 0.60 | 1.14 | 2.04 | 1.08 | 1.17 | 0.33 | 0.33 | 0.73 |
| Npr3 | 0.83 | 1.00 | 0.70 | 2.78 | 0.72 | 0.86 | 0.79 | 0.99 | 1.09 | 2.93 | 2.09 | 2.52 |
| Npw | 1.00 | 1.00 | 1.00 | 1.00 | 1.00 | 1.00 | 1.00 | 1.00 | 1.00 | 1.16 | 2.39 | 0.79 |
| Npy1r | 0.98 | 1.65 | 0.96 | 1.92 | 0.81 | 1.42 | 1.09 | 0.98 | 0.78 | 0.74 | 0.50 | 0.73 |
| Nr1d2 | 0.72 | 1.12 | 0.92 | 2.04 | 0.33 | 0.89 | 0.84 | 1.23 | 0.84 | 0.31 | 0.32 | 0.75 |
| Nr1h5 | 1.00 | 1.00 | 1.00 | 1.00 | 1.00 | 1.00 | 1.00 | 1.00 | 1.00 | 1.00 | 1.00 | 1.00 |
| Nr2c2 | 0.53 | 1.00 | 1.25 | 2.13 | 0.62 | 0.61 | 1.17 | 2.85 | 2.31 | 1.00 | 1.00 | 1.11 |
| Nrbf2 | 1.24 | 2.65 | 1.47 | 1.58 | 0.38 | 2.31 | 1.41 | 1.17 | 1.06 | 0.43 | 0.28 | 1.05 |
| Nrep | 0.68 | 0.94 | 0.42 | 1.29 | 0.34 | 1.10 | 0.52 | 0.29 | 0.38 | 0.30 | 0.18 | 0.38 |
| Nrgn | 0.73 | 1.00 | 1.00 | 2.56 | 0.11 | 1.89 | 1.90 | 1.73 | 1.83 | 2.20 | 2.67 | 1.26 |
| Nrip1 | 0.78 | 1.00 | 1.06 | 2.07 | 1.00 | 0.83 | 1.59 | 2.75 | 1.55 | 1.00 | 1.00 | 0.82 |
| Nrn1 | 1.00 | 1.00 | 1.00 | 1.67 | 0.18 | 1.62 | 1.48 | 1.21 | 1.52 | 0.38 | 0.31 | 0.87 |
| Nsd1 | 0.82 | 1.14 | 1.00 | 1.42 | 0.50 | 0.89 | 1.01 | 1.11 | 1.17 | 0.82 | 0.78 | 1.17 |
| Nsdhl | 0.75 | 0.93 | 0.94 | 0.59 | 0.20 | 0.62 | 1.11 | 1.07 | 0.98 | 0.44 | 0.51 | 1.28 |
| Nsg2 | 1.00 | 1.00 | 1.00 | 1.00 | 0.05 | 1.00 | 1.00 | 1.00 | 1.00 | 1.06 | 0.72 | 1.30 |
| Nsun3 | 0.47 | 1.00 | 1.09 | 1.11 | 0.18 | 0.71 | 1.03 | 1.51 | 1.01 | 1.00 | 1.00 | 0.82 |
| Ntn4 | 1.48 | 1.00 | 1.83 | 1.83 | 0.49 | 1.16 | 0.70 | 1.14 | 0.87 | 1.13 | 0.17 | 0.89 |
| Nuak1 | 1.68 | 4.17 | 1.89 | 1.36 | 0.22 | 1.16 | 0.91 | 1.53 | 1.56 | 0.83 | 0.26 | 0.61 |
| Nudt12 | 1.07 | 1.00 | 1.56 | 2.69 | 0.14 | 1.11 | 1.29 | 1.23 | 1.09 | 1.00 | 1.00 | 1.23 |
| Nudt15 | 0.93 | 1.00 | 0.85 | 0.43 | 0.17 | 0.48 | 1.04 | 1.15 | 0.87 | 1.00 | 1.00 | 1.15 |
| Nudt22 | 0.64 | 1.14 | 0.84 | 0.17 | 0.54 | 0.55 | 0.84 | 0.79 | 0.86 | 0.58 | 1.04 | 1.33 |
| Nup153 | 0.77 | 1.72 | 0.97 | 2.20 | 0.30 | 0.92 | 1.16 | 1.20 | 1.14 | 0.77 | 0.43 | 0.97 |
| Nupl2 | 1.06 | 1.46 | 0.91 | 1.03 | 0.64 | 1.18 | 1.25 | 0.98 | 1.06 | 0.64 | 0.65 | 0.90 |
| Nutf2-ps1 | 0.39 | 0.39 | 0.14 | 0.43 | 1.95 | 0.73 | 0.38 | 0.68 | 0.65 | 0.11 | 0.33 | 0.45 |
| OTTMUSG00000016609 | 1.00 | 1.00 | 1.00 | 1.00 | 1.00 | 0.80 | 1.00 | 1.00 | 1.00 | 1.00 | 1.00 | 1.00 |
| Ocrl | 1.18 | 1.64 | 1.16 | 1.98 | 0.26 | 1.15 | 1.29 | 1.21 | 1.01 | 0.64 | 0.30 | 0.94 |
| Olfr761 | 1.00 | 1.00 | 1.00 | 1.00 | 1.00 | 1.00 | 1.00 | 1.00 | 1.00 | 1.00 | 1.00 | 1.00 |
| Olfr920 | 1.00 | 1.00 | 1.00 | 1.00 | 1.00 | 1.00 | 1.00 | 1.00 | 1.00 | 0.70 | 0.53 | 0.70 |
| Opa3 | 0.70 | 1.68 | 0.96 | 1.02 | 0.06 | 0.69 | 1.02 | 1.20 | 1.03 | 1.00 | 0.39 | 1.26 |
| Ormdl2 | 1.00 | 1.12 | 1.00 | 0.54 | 3.29 | 0.79 | 1.53 | 0.53 | 1.25 | 0.37 | 0.99 | 0.78 |
| Osbpl5 | 1.20 | 2.22 | 1.20 | 2.70 | 2.29 | 1.44 | 1.02 | 0.88 | 1.00 | 0.49 | 0.45 | 0.97 |

Fig. 35-66

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Nbn | 0.87 | 0.55 | 0.59 | 1.12 | 1.00 | 0.86 | 0.97 | 1.00 | 0.99 | 0.95 | 0.95 | 0.88 |
| Nck1 | 0.83 | 0.80 | 1.05 | 0.76 | 2.53 | 0.83 | 1.21 | 0.37 | 1.14 | 0.94 | 0.94 | 1.24 |
| Ncoa4 | 0.98 | 0.81 | 1.09 | 1.96 | 3.03 | 1.71 | 1.56 | 1.35 | 1.38 | 0.87 | 0.62 | 0.88 |
| Ncstn | 1.09 | 1.18 | 1.02 | 0.94 | 1.87 | 0.94 | 1.06 | 0.48 | 0.97 | 1.02 | 1.14 | 1.07 |
| Ndel1 | 0.95 | 1.03 | 1.05 | 0.80 | 1.18 | 0.90 | 0.96 | 0.64 | 0.90 | 1.12 | 1.05 | 1.12 |
| Ndst1 | 0.81 | 0.58 | 1.30 | 1.36 | 1.00 | 1.61 | 0.69 | 1.00 | 1.04 | 1.03 | 0.29 | 0.98 |
| Ndufa12 | 0.56 | 0.59 | 0.35 | 0.43 | 0.35 | 0.32 | 0.39 | 0.53 | 0.35 | 0.47 | 0.91 | 0.41 |
| Ndufaf3 | 0.88 | 0.99 | 0.86 | 0.90 | 0.54 | 0.83 | 1.55 | 0.71 | 0.69 | 0.80 | 1.73 | 1.06 |
| Nebl | 0.20 | 0.12 | 0.53 | 1.00 | 1.00 | 1.00 | 1.00 | 1.00 | 1.00 | 1.00 | 1.00 | 1.00 |
| Nedd4 | 1.05 | 0.87 | 1.13 | 0.94 | 2.23 | 0.92 | 0.95 | 0.33 | 1.01 | 0.90 | 0.66 | 0.94 |
| Nedd9 | 0.64 | 0.64 | 0.93 | 0.95 | 0.80 | 0.98 | 1.20 | 1.00 | 1.12 | 0.98 | 0.75 | 0.90 |
| Nek7 | 0.88 | 0.68 | 1.08 | 1.41 | 1.40 | 1.14 | 1.16 | 1.00 | 0.99 | 1.13 | 0.59 | 1.09 |
| Nepn | 1.00 | 1.00 | 1.00 | 1.05 | 0.99 | 1.62 | 1.00 | 1.00 | 1.00 | 1.00 | 1.00 | 1.00 |
| Nfat5 | 0.79 | 0.66 | 0.93 | 1.19 | 1.17 | 1.04 | 0.87 | 0.79 | 0.89 | 0.99 | 1.15 | 0.93 |
| Nfe2l3 | 1.63 | 1.35 | 1.73 | 0.92 | 1.00 | 1.00 | 1.00 | 1.00 | 1.00 | 0.82 | 0.71 | 0.64 |
| Nfkb1 | 1.30 | 1.24 | 1.34 | 0.86 | 1.82 | 0.93 | 1.25 | 0.69 | 1.13 | 0.92 | 0.90 | 0.94 |
| Nfya | 0.57 | 0.51 | 0.79 | 0.55 | 0.40 | 0.58 | 0.93 | 1.00 | 0.94 | 0.70 | 0.53 | 1.01 |
| Ngfr | 0.57 | 0.44 | 0.49 | 1.00 | 1.00 | 1.00 | 1.00 | 1.00 | 1.00 | 1.15 | 1.00 | 0.96 |
| Nhsl1 | 0.81 | 0.76 | 0.79 | 1.07 | 1.28 | 1.10 | 0.90 | 1.00 | 0.83 | 1.02 | 0.63 | 0.94 |
| Nid1 | 2.20 | 1.38 | 1.78 | 1.27 | 1.00 | 1.16 | 2.09 | 1.00 | 2.05 | 1.36 | 0.77 | 1.22 |
| Nipal1 | 0.64 | 0.51 | 0.69 | 1.28 | 1.00 | 1.00 | 2.82 | 1.00 | 3.62 | 1.31 | 1.14 | 1.35 |
| Nipal2 | 0.88 | 0.78 | 0.85 | 0.14 | 0.16 | 0.09 | 1.00 | 1.00 | 1.00 | 0.85 | 1.11 | 0.76 |
| Nkain1 | 1.00 | 1.00 | 1.00 | 0.70 | 0.71 | 1.12 | 1.00 | 1.00 | 1.00 | 0.79 | 0.81 | 0.98 |
| Nkx2-2 | 1.00 | 1.00 | 1.00 | 1.00 | 1.00 | 1.00 | 1.00 | 1.00 | 1.00 | 1.63 | 0.93 | 1.21 |
| Nlgn2 | 1.25 | 0.91 | 1.20 | 0.75 | 1.00 | 1.19 | 1.00 | 1.00 | 0.81 | 0.89 | 0.67 | 0.94 |
| Nlrp10 | 1.00 | 1.00 | 1.00 | 1.00 | 1.00 | 1.00 | 1.00 | 1.00 | 1.00 | 0.74 | 0.81 | 0.85 |
| Nme6 | 2.18 | 1.38 | 1.05 | 1.06 | 0.91 | 1.23 | 1.40 | 1.27 | 1.42 | 1.32 | 2.08 | 1.78 |
| Nmt1 | 0.98 | 0.98 | 1.05 | 1.07 | 1.76 | 1.05 | 1.26 | 0.23 | 1.17 | 1.15 | 1.25 | 1.02 |
| Nnt | 0.73 | 0.77 | 0.82 | 0.86 | 1.29 | 0.96 | 0.63 | 0.50 | 0.77 | 0.84 | 0.86 | 0.95 |
| Notch1 | 0.65 | 0.62 | 1.03 | 0.95 | 1.00 | 1.27 | 1.14 | 0.99 | 1.20 | 0.85 | 0.73 | 1.09 |
| Notch3 | 0.55 | 0.63 | 0.86 | 1.13 | 1.00 | 1.30 | 1.00 | 1.00 | 1.00 | 1.02 | 0.53 | 1.00 |
| Notum | 1.00 | 1.00 | 1.00 | 1.06 | 1.30 | 1.06 | 0.46 | 0.17 | 0.80 | 1.00 | 1.00 | 1.00 |
| Npepps | 0.78 | 0.78 | 0.93 | 0.98 | 1.37 | 1.05 | 0.79 | 0.69 | 0.96 | 0.99 | 0.78 | 0.96 |
| Npnt | 0.85 | 1.06 | 1.13 | 1.44 | 1.60 | 1.27 | 1.68 | 1.00 | 1.00 | 1.03 | 0.64 | 0.95 |
| Npr3 | 1.00 | 1.00 | 1.00 | 0.61 | 1.00 | 0.57 | 1.00 | 1.00 | 1.00 | 1.00 | 1.00 | 1.00 |
| Npw | 1.00 | 1.00 | 1.00 | 1.00 | 0.86 | 1.00 | 1.00 | 1.00 | 1.00 | 1.00 | 1.00 | 1.00 |
| Npy1r | 2.26 | 2.22 | 1.74 | 1.05 | 1.49 | 1.15 | 1.00 | 1.00 | 1.00 | 1.05 | 0.88 | 1.01 |
| Nr1d2 | 0.82 | 0.73 | 0.85 | 0.92 | 1.55 | 0.92 | 1.06 | 0.50 | 0.91 | 0.89 | 0.78 | 0.91 |
| Nr1h5 | 1.00 | 1.00 | 1.00 | 1.00 | 1.00 | 1.00 | 0.93 | 1.00 | 1.00 | 0.11 | 0.10 | 0.11 |
| Nr2c2 | 0.24 | 0.15 | 0.52 | 1.41 | 1.00 | 1.34 | 0.97 | 1.00 | 0.98 | 1.04 | 0.32 | 0.89 |
| Nrbf2 | 1.19 | 1.17 | 0.95 | 1.18 | 3.10 | 1.16 | 1.26 | 0.55 | 1.18 | 1.10 | 0.87 | 1.23 |
| Nrep | 1.08 | 0.68 | 0.60 | 0.79 | 0.78 | 0.72 | 0.15 | 0.21 | 0.11 | 0.69 | 0.66 | 0.78 |
| Nrgn | 1.15 | 1.17 | 0.99 | 0.86 | 0.43 | 1.19 | 1.00 | 2.58 | 1.04 | 1.52 | 1.24 | 1.16 |
| Nrip1 | 0.40 | 0.31 | 0.79 | 1.57 | 1.00 | 1.24 | 0.95 | 1.00 | 1.13 | 1.13 | 0.42 | 0.71 |
| Nrn1 | 1.12 | 1.07 | 1.27 | 1.00 | 1.00 | 1.00 | 0.30 | 0.13 | 0.54 | 0.82 | 1.15 | 1.26 |
| Nsd1 | 0.73 | 0.68 | 0.94 | 1.18 | 1.41 | 1.11 | 1.01 | 0.98 | 1.19 | 1.05 | 0.83 | 1.00 |
| Nsdhl | 0.95 | 0.98 | 1.00 | 0.99 | 2.19 | 0.88 | 0.75 | 1.00 | 0.89 | 1.10 | 0.84 | 0.98 |
| Nsg2 | 0.73 | 0.95 | 0.68 | 0.70 | 1.00 | 1.00 | 1.00 | 1.00 | 1.00 | 1.05 | 1.08 | 1.17 |
| Nsun3 | 0.45 | 0.59 | 0.75 | 0.84 | 1.00 | 0.93 | 0.89 | 1.00 | 1.69 | 1.11 | 0.42 | 0.73 |
| Ntn4 | 0.93 | 0.67 | 1.17 | 1.07 | 1.00 | 1.07 | 0.93 | 1.00 | 0.85 | 1.43 | 0.47 | 1.14 |
| Nuak1 | 0.98 | 0.68 | 1.16 | 0.90 | 1.00 | 0.99 | 0.98 | 1.00 | 1.00 | 0.80 | 0.71 | 0.90 |
| Nudt12 | 0.94 | 0.57 | 1.04 | 1.19 | 1.00 | 1.24 | 0.99 | 1.00 | 1.11 | 1.51 | 0.41 | 1.21 |
| Nudt15 | 0.76 | 0.77 | 0.80 | 1.11 | 1.00 | 1.04 | 1.00 | 1.00 | 1.00 | 1.13 | 0.81 | 0.98 |
| Nudt22 | 1.05 | 1.47 | 1.00 | 0.75 | 0.85 | 0.84 | 0.93 | 0.84 | 1.11 | 1.23 | 1.53 | 1.16 |
| Nup153 | 0.56 | 0.49 | 0.83 | 1.02 | 0.94 | 0.93 | 1.05 | 1.00 | 1.03 | 1.05 | 0.55 | 0.90 |
| Nupl2 | 0.75 | 1.03 | 0.90 | 1.03 | 1.58 | 0.88 | 1.16 | 1.34 | 0.87 | 1.23 | 1.02 | 0.90 |
| Nutf2-ps1 | 0.60 | 0.74 | 0.68 | 0.64 | 1.71 | 1.11 | 1.99 | 0.12 | 0.96 | 0.80 | 1.31 | 1.08 |
| OTTMUSG00000016609 | 1.00 | 1.00 | 1.00 | 1.64 | 1.00 | 1.28 | 0.75 | 1.00 | 1.00 | 0.36 | 1.00 | 0.47 |
| Ocrl | 1.14 | 0.98 | 1.24 | 0.99 | 1.00 | 1.14 | 1.30 | 1.00 | 1.08 | 1.14 | 0.68 | 0.98 |
| Olfr761 | 1.00 | 1.00 | 1.00 | 1.00 | 1.00 | 1.00 | 1.00 | 1.00 | 1.00 | 1.00 | 1.00 | 1.00 |
| Olfr920 | 0.38 | 0.30 | 0.35 | 1.00 | 1.00 | 1.00 | 1.00 | 1.00 | 1.00 | 0.74 | 1.00 | 1.00 |
| Opa3 | 0.73 | 0.50 | 0.90 | 1.18 | 1.00 | 1.01 | 0.66 | 1.00 | 0.84 | 1.05 | 0.48 | 0.92 |
| Ormdl2 | 1.01 | 1.45 | 1.01 | 0.69 | 1.43 | 0.75 | 0.81 | 0.54 | 0.95 | 0.82 | 1.68 | 0.98 |
| Osbpl5 | 1.29 | 1.32 | 1.26 | 0.96 | 1.48 | 1.09 | 0.29 | 1.00 | 0.42 | 0.98 | 0.94 | 1.14 |

Fig. 35-67

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Nbn | 0.95 | 0.83 | 0.80 | 1.10 | 1.00 | 0.82 | 1.03 | 1.00 | 0.82 | 0.87 | 0.68 | 0.62 |
| Nck1 | 0.93 | 0.92 | 1.05 | 1.01 | 0.25 | 1.21 | 1.09 | 0.44 | 1.02 | 0.95 | 0.73 | 0.90 |
| Ncoa4 | 1.04 | 0.93 | 0.75 | 0.54 | 0.11 | 0.97 | 1.08 | 0.34 | 1.05 | 0.81 | 0.64 | 0.71 |
| Ncstn | 0.94 | 1.14 | 0.99 | 0.96 | 0.61 | 1.05 | 0.96 | 0.24 | 0.89 | 1.06 | 1.04 | 0.99 |
| Ndel1 | 1.01 | 1.08 | 1.05 | 1.16 | 0.44 | 1.15 | 0.93 | 1.06 | 1.03 | 0.98 | 1.01 | 1.00 |
| Ndst1 | 1.10 | 1.05 | 0.73 | 1.43 | 0.47 | 1.02 | 1.53 | 1.00 | 1.19 | 1.29 | 0.81 | 1.72 |
| Ndufa12 | 0.50 | 0.54 | 0.36 | 0.27 | 0.81 | 0.27 | 0.34 | 0.39 | 0.33 | 0.63 | 0.68 | 0.37 |
| Ndufaf3 | 0.99 | 0.88 | 1.09 | 0.69 | 1.95 | 0.67 | 0.88 | 1.27 | 0.99 | 0.92 | 1.23 | 0.83 |
| Nebl | 1.15 | 0.90 | 0.72 | 1.00 | 0.81 | 1.00 | 1.00 | 1.00 | 1.00 | 1.29 | 1.18 | 1.05 |
| Nedd4 | 0.91 | 0.86 | 1.01 | 0.75 | 0.10 | 0.90 | 0.94 | 0.33 | 0.85 | 0.94 | 0.75 | 0.92 |
| Nedd9 | 0.96 | 1.03 | 0.72 | 1.35 | 0.47 | 1.03 | 1.23 | 1.00 | 0.86 | 0.86 | 0.52 | 0.91 |
| Nek7 | 1.12 | 1.00 | 0.95 | 1.20 | 0.16 | 0.89 | 0.92 | 1.00 | 0.89 | 1.00 | 0.56 | 1.14 |
| Nepn | 1.00 | 1.00 | 1.00 | 0.18 | 1.00 | 0.33 | 1.00 | 1.00 | 1.00 | 1.00 | 1.00 | 1.00 |
| Nfat5 | 1.19 | 1.08 | 0.87 | 1.07 | 0.19 | 1.03 | 1.07 | 0.67 | 0.98 | 1.00 | 0.79 | 1.08 |
| Nfe2l3 | 0.78 | 0.78 | 0.82 | 2.30 | 1.00 | 1.40 | 1.04 | 1.00 | 1.27 | 0.89 | 0.65 | 1.06 |
| Nfkb1 | 0.98 | 0.92 | 0.95 | 1.03 | 0.46 | 1.08 | 0.92 | 1.11 | 0.82 | 0.95 | 0.83 | 0.96 |
| Nfya | 0.75 | 0.59 | 0.79 | 1.19 | 1.00 | 0.94 | 1.01 | 1.16 | 1.15 | 0.83 | 0.55 | 0.87 |
| Ngfr | 1.26 | 1.58 | 1.42 | 0.74 | 1.00 | 0.86 | 0.83 | 0.59 | 0.71 | 0.33 | 0.20 | 0.37 |
| Nhsl1 | 1.00 | 1.10 | 0.84 | 0.86 | 1.00 | 0.76 | 1.25 | 0.93 | 1.13 | 0.74 | 0.99 | 0.96 |
| Nid1 | 1.13 | 1.11 | 1.12 | 1.17 | 0.08 | 1.07 | 1.49 | 1.00 | 1.45 | 0.98 | 0.59 | 1.16 |
| Nipal1 | 1.13 | 1.22 | 0.87 | 1.00 | 1.00 | 1.00 | 1.00 | 1.00 | 1.00 | 1.00 | 0.80 | 1.00 |
| Nipal2 | 0.73 | 0.74 | 0.60 | 0.88 | 1.00 | 1.00 | 1.00 | 1.00 | 1.00 | 1.00 | 1.00 | 1.00 |
| Nkain1 | 0.56 | 0.40 | 0.81 | 0.41 | 1.00 | 0.41 | 1.34 | 1.50 | 1.08 | 1.00 | 3.82 | 1.00 |
| Nkx2-2 | 1.00 | 1.00 | 0.80 | 1.00 | 1.00 | 1.00 | 1.00 | 1.00 | 1.00 | 1.00 | 1.00 | 1.00 |
| Nlgn2 | 0.99 | 1.06 | 1.14 | 0.82 | 1.00 | 1.05 | 1.06 | 1.00 | 1.06 | 0.86 | 1.45 | 1.07 |
| Nlrp10 | 1.13 | 1.04 | 1.19 | 1.00 | 1.00 | 1.00 | 1.00 | 1.00 | 1.00 | 0.90 | 0.65 | 0.89 |
| Nme6 | 2.01 | 1.02 | 1.48 | 1.58 | 0.69 | 1.48 | 1.27 | 1.28 | 1.29 | 1.26 | 1.41 | 1.22 |
| Nmt1 | 1.11 | 0.93 | 1.04 | 1.15 | 0.30 | 1.12 | 1.07 | 0.20 | 0.96 | 0.91 | 0.93 | 0.80 |
| Nnt | 1.12 | 1.28 | 1.27 | 0.68 | 0.20 | 0.77 | 1.03 | 0.51 | 1.04 | 1.02 | 0.82 | 0.96 |
| Notch1 | 1.04 | 1.18 | 1.10 | 0.74 | 0.17 | 1.13 | 1.07 | 1.00 | 1.44 | 0.89 | 0.67 | 1.05 |
| Notch3 | 0.82 | 0.92 | 0.97 | 0.99 | 0.25 | 1.02 | 1.00 | 1.00 | 1.12 | 0.60 | 0.42 | 0.75 |
| Notum | 1.00 | 1.00 | 1.00 | 0.53 | 1.00 | 2.40 | 1.00 | 1.00 | 1.00 | 1.00 | 1.00 | 1.00 |
| Npepps | 1.03 | 0.98 | 0.93 | 0.98 | 0.48 | 1.22 | 1.05 | 0.43 | 0.98 | 1.00 | 0.97 | 0.97 |
| Npnt | 0.97 | 0.92 | 0.98 | 1.68 | 1.00 | 2.11 | 0.91 | 1.03 | 1.00 | 0.70 | 0.65 | 0.80 |
| Npr3 | 1.00 | 1.00 | 1.00 | 0.31 | 0.06 | 0.17 | 1.00 | 1.00 | 1.00 | 1.00 | 1.00 | 1.00 |
| Npw | 0.80 | 1.02 | 0.68 | 1.00 | 1.00 | 1.00 | 1.00 | 2.00 | 1.00 | 1.00 | 1.00 | 1.00 |
| Npy1r | 0.70 | 1.13 | 0.91 | 2.23 | 1.00 | 2.72 | 1.00 | 1.00 | 1.00 | 1.00 | 1.07 | 1.15 |
| Nr1d2 | 0.81 | 0.86 | 0.91 | 0.53 | 0.18 | 0.68 | 0.96 | 0.65 | 0.90 | 0.85 | 0.82 | 0.97 |
| Nr1h5 | 1.00 | 1.00 | 1.00 | 1.00 | 1.00 | 1.00 | 1.00 | 1.00 | 1.00 | 1.00 | 1.00 | 1.00 |
| Nr2c2 | 1.11 | 1.01 | 0.60 | 1.31 | 0.47 | 0.22 | 1.92 | 1.00 | 1.67 | 0.79 | 0.40 | 1.19 |
| Nrbf2 | 1.00 | 0.87 | 1.10 | 1.68 | 0.80 | 1.54 | 0.97 | 0.74 | 1.19 | 1.07 | 0.92 | 1.00 |
| Nrep | 0.51 | 0.47 | 0.48 | 0.77 | 0.86 | 0.71 | 0.96 | 0.92 | 0.86 | 0.47 | 2.00 | 0.45 |
| Nrgn | 1.39 | 1.01 | 0.91 | 1.30 | 3.73 | 0.83 | 1.54 | 2.70 | 1.27 | 1.92 | 3.09 | 1.08 |
| Nrip1 | 1.30 | 1.01 | 0.51 | 0.65 | 0.07 | 0.12 | 1.35 | 1.00 | 1.71 | 0.78 | 0.46 | 0.96 |
| Nrn1 | 0.80 | 0.82 | 1.16 | 1.65 | 1.00 | 1.79 | 1.44 | 0.38 | 0.82 | 0.41 | 1.56 | 0.52 |
| Nsd1 | 1.01 | 0.96 | 0.79 | 0.94 | 0.14 | 0.85 | 1.28 | 0.78 | 1.23 | 1.01 | 0.74 | 1.16 |
| Nsdhl | 0.76 | 0.81 | 0.89 | 0.92 | 0.67 | 1.05 | 0.95 | 1.11 | 0.91 | 0.87 | 0.88 | 0.96 |
| Nsg2 | 1.52 | 1.01 | 1.10 | 1.00 | 1.00 | 1.00 | 1.00 | 1.00 | 1.00 | 1.00 | 2.72 | 1.36 |
| Nsun3 | 0.96 | 1.08 | 0.71 | 1.17 | 1.00 | 0.66 | 1.01 | 1.00 | 0.83 | 0.87 | 0.40 | 1.07 |
| Ntn4 | 1.24 | 1.33 | 0.95 | 1.36 | 1.00 | 0.97 | 1.06 | 1.00 | 1.14 | 0.55 | 0.52 | 0.79 |
| Nuak1 | 0.69 | 0.87 | 0.91 | 0.72 | 0.49 | 0.66 | 1.00 | 1.00 | 1.00 | 0.64 | 0.81 | 1.01 |
| Nudt12 | 1.04 | 1.20 | 1.05 | 0.98 | 0.39 | 0.88 | 1.47 | 1.00 | 1.27 | 1.00 | 1.00 | 1.00 |
| Nudt15 | 0.90 | 0.68 | 1.03 | 1.00 | 1.00 | 0.84 | 0.93 | 1.00 | 0.80 | 1.02 | 0.55 | 1.10 |
| Nudt22 | 0.91 | 1.34 | 1.00 | 0.65 | 1.00 | 0.94 | 0.57 | 0.31 | 0.45 | 1.25 | 0.98 | 0.87 |
| Nup153 | 0.87 | 0.77 | 0.75 | 1.04 | 0.47 | 0.74 | 1.18 | 0.85 | 1.11 | 0.88 | 0.53 | 0.95 |
| Nupl2 | 0.90 | 1.23 | 0.98 | 0.92 | 0.90 | 1.16 | 0.99 | 0.43 | 0.85 | 1.07 | 0.83 | 0.94 |
| Nutf2-ps1 | 0.73 | 0.74 | 1.03 | 0.92 | 1.00 | 1.27 | 1.65 | 0.21 | 0.86 | 0.87 | 1.65 | 0.90 |
| OTTMUSG00000016609 | 1.00 | 0.69 | 1.00 | 1.00 | 1.00 | 1.00 | 1.00 | 1.00 | 1.00 | 1.00 | 1.00 | 1.00 |
| Ocrl | 1.07 | 1.19 | 1.19 | 0.80 | 0.59 | 0.57 | 0.79 | 1.00 | 0.67 | 0.99 | 1.02 | 0.89 |
| Olfr761 | 1.00 | 1.00 | 1.00 | 1.00 | 1.00 | 1.00 | 0.21 | 0.08 | 0.35 | 1.00 | 1.00 | 1.00 |
| Olfr920 | 1.00 | 1.00 | 1.00 | 1.00 | 1.00 | 1.00 | 1.00 | 1.00 | 1.00 | 0.60 | 0.80 | 1.00 |
| Opa3 | 0.98 | 0.93 | 0.70 | 1.12 | 0.30 | 0.98 | 0.92 | 1.00 | 1.10 | 0.87 | 0.68 | 1.00 |
| Ormdl2 | 0.83 | 0.86 | 1.06 | 1.06 | 1.59 | 1.33 | 0.85 | 0.07 | 0.87 | 0.95 | 1.50 | 0.85 |
| Osbpl5 | 0.90 | 1.02 | 0.94 | 1.40 | 0.66 | 1.19 | 0.75 | 1.00 | 1.03 | 1.06 | 0.86 | 1.11 |

Fig. 35- 68

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Nbn | 0.78 | 0.98 | 1.17 | 0.92 | 0.62 | 0.97 | 0.87 | 0.17 | 1.00 | 0.35 | 0.81 | 0.85 |
| Nck1 | 0.90 | 1.17 | 0.91 | 0.96 | 0.22 | 0.96 | 0.81 | 0.16 | 0.94 | 0.57 | 0.95 | 1.07 |
| Ncoa4 | 1.14 | 1.29 | 1.27 | 0.95 | 1.00 | 0.91 | 1.06 | 0.11 | 1.07 | 0.36 | 0.95 | 0.99 |
| Ncstn | 1.06 | 0.88 | 0.81 | 1.03 | 1.00 | 1.02 | 1.02 | 0.10 | 0.98 | 0.62 | 1.21 | 1.16 |
| Ndel1 | 0.95 | 1.19 | 1.04 | 1.06 | 0.82 | 1.01 | 0.98 | 0.12 | 0.81 | 0.34 | 1.16 | 1.06 |
| Ndst1 | 1.51 | 1.34 | 1.82 | 0.97 | 1.00 | 1.00 | 0.88 | 0.07 | 1.18 | 0.99 | 1.05 | 0.84 |
| Ndufa12 | 0.20 | 0.28 | 0.26 | 0.53 | 0.57 | 0.44 | 0.62 | 2.70 | 0.35 | 1.17 | 0.52 | 0.50 |
| Ndufaf3 | 1.39 | 1.19 | 0.91 | 0.96 | 0.80 | 0.99 | 1.38 | 2.15 | 0.63 | 2.31 | 0.93 | 1.04 |
| Nebl | 1.00 | 1.00 | 1.00 | 0.74 | 1.00 | 0.78 | 1.00 | 1.00 | 1.00 | 1.00 | 1.00 | 1.00 |
| Nedd4 | 0.92 | 0.88 | 0.96 | 1.01 | 0.77 | 1.02 | 0.79 | 0.05 | 1.06 | 0.29 | 0.74 | 0.90 |
| Nedd9 | 1.07 | 3.42 | 1.03 | 1.28 | 1.00 | 1.14 | 0.85 | 0.26 | 1.32 | 0.65 | 1.20 | 0.98 |
| Nek7 | 2.11 | 2.64 | 1.36 | 1.17 | 1.00 | 1.14 | 0.89 | 0.05 | 1.30 | 0.28 | 0.94 | 0.87 |
| Nepn | 1.00 | 1.00 | 1.00 | 1.00 | 1.00 | 1.00 | 1.00 | 1.00 | 1.00 | 1.00 | 1.00 | 1.00 |
| Nfat5 | 1.14 | 1.19 | 1.41 | 0.85 | 1.50 | 0.87 | 0.73 | 0.47 | 0.93 | 0.96 | 1.16 | 1.01 |
| Nfe2l3 | 1.00 | 1.00 | 1.00 | 0.83 | 0.51 | 1.00 | 0.91 | 0.19 | 0.85 | 1.00 | 1.00 | 1.00 |
| Nfkb1 | 1.12 | 1.26 | 1.03 | 0.72 | 1.00 | 1.00 | 0.94 | 0.17 | 1.00 | 0.67 | 1.12 | 1.07 |
| Nfya | 0.87 | 0.69 | 0.64 | 0.84 | 1.00 | 0.98 | 0.84 | 0.19 | 0.88 | 0.36 | 0.78 | 0.90 |
| Ngfr | 1.00 | 1.00 | 1.00 | 0.97 | 1.00 | 0.91 | 0.25 | 0.19 | 0.39 | 1.00 | 1.00 | 1.00 |
| Nhsl1 | 1.01 | 1.55 | 1.01 | 0.99 | 1.00 | 1.00 | 0.56 | 0.14 | 0.65 | 1.00 | 1.00 | 1.00 |
| Nid1 | 1.16 | 1.53 | 2.27 | 1.31 | 1.00 | 1.23 | 1.51 | 0.10 | 2.37 | 1.00 | 1.00 | 1.22 |
| Nipal1 | 1.00 | 1.00 | 1.00 | 1.00 | 1.00 | 1.00 | 0.55 | 0.12 | 0.57 | 1.00 | 1.00 | 1.00 |
| Nipal2 | 0.77 | 0.95 | 0.72 | 0.49 | 2.25 | 0.55 | 0.63 | 1.02 | 0.59 | 1.00 | 1.00 | 1.00 |
| Nkain1 | 1.00 | 1.00 | 1.00 | 0.94 | 0.88 | 0.97 | 0.93 | 0.71 | 0.76 | 1.00 | 1.00 | 1.00 |
| Nkx2-2 | 1.00 | 1.00 | 1.00 | 0.78 | 0.20 | 0.74 | 1.00 | 1.00 | 1.00 | 1.00 | 1.00 | 1.00 |
| Nlgn2 | 1.00 | 1.00 | 1.00 | 1.02 | 1.30 | 1.03 | 0.72 | 0.15 | 0.90 | 0.63 | 0.80 | 0.80 |
| Nlrp10 | 1.00 | 1.00 | 1.00 | 1.00 | 1.00 | 1.00 | 0.50 | 0.20 | 0.60 | 1.00 | 1.00 | 1.00 |
| Nme6 | 1.16 | 0.81 | 1.37 | 1.89 | 0.16 | 1.53 | 1.29 | 3.27 | 0.84 | 1.65 | 1.35 | 1.54 |
| Nmt1 | 0.97 | 1.03 | 0.95 | 1.13 | 2.19 | 0.98 | 1.11 | 0.47 | 0.94 | 0.77 | 0.92 | 1.03 |
| Nnt | 0.79 | 0.72 | 0.79 | 1.04 | 1.52 | 0.99 | 0.90 | 0.34 | 1.23 | 0.56 | 0.96 | 1.07 |
| Notch1 | 2.60 | 2.31 | 2.17 | 0.87 | 1.00 | 1.01 | 0.66 | 0.17 | 0.79 | 0.76 | 1.19 | 1.13 |
| Notch3 | 1.00 | 1.00 | 1.00 | 0.92 | 1.00 | 1.00 | 0.79 | 0.08 | 0.78 | 1.00 | 1.00 | 1.00 |
| Notum | 1.00 | 1.00 | 1.00 | 0.80 | 0.45 | 1.26 | 1.41 | 0.63 | 1.38 | 1.00 | 1.00 | 1.00 |
| Npepps | 1.32 | 1.23 | 1.47 | 1.06 | 0.99 | 1.02 | 0.97 | 0.16 | 0.94 | 0.69 | 1.29 | 1.29 |
| Npnt | 1.00 | 1.00 | 1.00 | 1.02 | 1.00 | 0.78 | 0.79 | 0.17 | 0.93 | 1.00 | 1.00 | 1.00 |
| Npr3 | 1.00 | 1.00 | 1.00 | 1.07 | 1.00 | 1.02 | 0.94 | 0.30 | 1.62 | 1.00 | 1.00 | 1.00 |
| Npw | 2.11 | 1.13 | 1.48 | 1.00 | 0.08 | 1.00 | 1.00 | 1.00 | 1.00 | 1.00 | 1.00 | 1.00 |
| Npy1r | 1.00 | 1.00 | 1.00 | 0.98 | 1.00 | 0.90 | 0.61 | 0.20 | 0.96 | 1.00 | 1.00 | 1.00 |
| Nr1d2 | 0.64 | 0.87 | 1.00 | 0.88 | 1.44 | 0.87 | 0.82 | 0.18 | 1.08 | 0.65 | 0.80 | 0.88 |
| Nr1h5 | 1.00 | 1.00 | 1.00 | 1.00 | 1.00 | 1.00 | 0.16 | 0.21 | 0.19 | 1.00 | 1.00 | 1.00 |
| Nr2c2 | 1.00 | 1.05 | 1.00 | 0.77 | 1.00 | 0.93 | 0.71 | 0.79 | 1.13 | 1.00 | 0.79 | 0.41 |
| Nrbf2 | 1.72 | 1.64 | 0.94 | 0.97 | 1.00 | 1.05 | 1.09 | 0.08 | 1.18 | 0.40 | 1.17 | 1.03 |
| Nrep | 0.86 | 0.75 | 1.00 | 1.01 | 0.64 | 0.85 | 0.67 | 0.24 | 0.86 | 1.00 | 1.00 | 0.98 |
| Nrgn | 1.00 | 1.00 | 1.00 | 1.26 | 1.12 | 1.24 | 1.94 | 1.95 | 1.43 | 2.12 | 1.23 | 2.60 |
| Nrip1 | 1.00 | 1.00 | 1.00 | 0.77 | 1.00 | 0.81 | 0.94 | 1.00 | 1.00 | 1.00 | 1.00 | 1.00 |
| Nrn1 | 1.00 | 1.00 | 1.00 | 1.25 | 0.90 | 1.06 | 1.24 | 0.46 | 1.43 | 1.00 | 1.00 | 1.00 |
| Nsd1 | 1.10 | 1.22 | 1.27 | 0.86 | 0.49 | 0.93 | 0.88 | 0.36 | 1.08 | 0.73 | 0.98 | 1.02 |
| Nsdhl | 1.00 | 1.00 | 1.00 | 1.00 | 1.00 | 0.95 | 1.16 | 0.17 | 0.85 | 0.55 | 1.16 | 1.27 |
| Nsg2 | 1.00 | 1.00 | 1.00 | 1.09 | 1.19 | 1.06 | 1.00 | 1.00 | 1.00 | 1.09 | 1.25 | 1.48 |
| Nsun3 | 1.44 | 1.00 | 1.00 | 1.22 | 1.00 | 0.99 | 0.64 | 0.43 | 1.08 | 1.00 | 0.93 | 0.75 |
| Ntn4 | 1.51 | 1.04 | 1.00 | 0.86 | 1.00 | 0.87 | 1.32 | 0.26 | 1.63 | 1.00 | 1.22 | 1.00 |
| Nuak1 | 0.90 | 0.75 | 1.59 | 1.01 | 1.00 | 0.97 | 0.86 | 0.08 | 1.15 | 1.00 | 0.41 | 0.74 |
| Nudt12 | 1.14 | 1.00 | 1.00 | 0.92 | 1.00 | 1.12 | 0.66 | 0.62 | 1.45 | 1.00 | 0.91 | 1.00 |
| Nudt15 | 1.00 | 1.00 | 1.00 | 1.07 | 1.00 | 1.13 | 1.00 | 1.00 | 1.00 | 1.00 | 0.74 | 0.92 |
| Nudt22 | 1.24 | 0.85 | 0.86 | 1.19 | 1.99 | 0.98 | 0.86 | 0.92 | 0.74 | 1.49 | 0.99 | 1.16 |
| Nup153 | 1.35 | 1.21 | 1.24 | 0.81 | 0.87 | 0.89 | 0.85 | 0.20 | 1.01 | 0.44 | 0.78 | 0.79 |
| Nupl2 | 1.00 | 1.06 | 1.00 | 0.99 | 0.38 | 0.82 | 1.04 | 0.18 | 1.04 | 0.70 | 0.91 | 0.75 |
| Nutf2-ps1 | 1.20 | 0.93 | 0.63 | 1.00 | 1.00 | 1.00 | 0.98 | 0.13 | 0.39 | 0.84 | 0.81 | 0.95 |
| OTTMUSG00000016609 | 1.00 | 1.00 | 1.00 | 0.09 | 1.00 | 0.36 | 1.00 | 1.00 | 1.00 | 1.00 | 1.00 | 1.00 |
| Ocrl | 1.34 | 1.79 | 2.08 | 1.05 | 0.96 | 1.04 | 0.85 | 0.08 | 0.96 | 0.46 | 1.14 | 1.16 |
| Olfr761 | 1.00 | 1.00 | 1.00 | 1.00 | 1.00 | 1.00 | 1.00 | 1.00 | 1.00 | 1.00 | 1.00 | 1.00 |
| Olfr920 | 1.00 | 1.00 | 1.00 | 1.00 | 1.00 | 1.00 | 0.10 | 0.13 | 0.16 | 1.00 | 1.00 | 1.00 |
| Opa3 | 1.98 | 1.02 | 1.09 | 1.00 | 1.00 | 0.94 | 0.97 | 0.11 | 0.88 | 0.47 | 0.80 | 0.68 |
| Ormdl2 | 0.51 | 1.08 | 1.36 | 1.22 | 1.00 | 0.93 | 1.19 | 0.66 | 0.57 | 0.86 | 0.93 | 1.15 |
| Osbpl5 | 1.28 | 0.90 | 1.04 | 0.96 | 1.08 | 1.21 | 0.94 | 0.16 | 0.81 | 0.81 | 1.09 | 1.21 |

Fig. 35- 69

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ost4 | 1.02 | 0.83 | 0.94 | 0.56 | 1.87 | 1.03 | 0.89 | 0.83 | 0.88 | 0.39 | 0.81 | 0.87 |
| Ostn | 0.84 | 0.41 | 0.12 | 1.00 | 1.00 | 1.00 | 1.00 | 1.00 | 1.00 | 1.00 | 1.00 | 1.00 |
| Oxtr | 1.00 | 1.00 | 1.00 | 1.00 | 1.00 | 1.00 | 1.00 | 1.00 | 1.00 | 1.00 | 1.00 | 1.00 |
| P2ry1 | 0.74 | 1.56 | 0.93 | 0.75 | 0.18 | 0.44 | 0.64 | 0.78 | 0.61 | 1.00 | 0.62 | 1.14 |
| Pacsin1 | 1.00 | 1.00 | 1.00 | 1.00 | 0.14 | 1.00 | 1.00 | 1.00 | 0.64 | 1.00 | 1.00 | 1.00 |
| Pak1 | 0.73 | 0.73 | 0.64 | 1.00 | 0.11 | 1.00 | 1.00 | 1.00 | 1.00 | 1.55 | 1.11 | 0.99 |
| Palmd | 1.76 | 4.10 | 2.04 | 0.83 | 0.19 | 0.93 | 1.08 | 0.96 | 1.11 | 0.44 | 0.25 | 0.80 |
| Pank3 | 0.83 | 1.44 | 0.99 | 1.07 | 0.14 | 0.84 | 0.71 | 0.80 | 0.81 | 0.35 | 0.22 | 0.93 |
| Paqr3 | 1.00 | 1.00 | 1.00 | 1.00 | 1.00 | 1.00 | 1.00 | 1.00 | 1.00 | 1.00 | 1.00 | 1.09 |
| Paqr9 | 0.79 | 1.00 | 0.71 | 0.19 | 0.07 | 0.35 | 0.60 | 0.65 | 0.61 | 1.00 | 1.00 | 1.42 |
| Pard6g | 0.54 | 1.00 | 1.14 | 2.35 | 0.70 | 1.69 | 0.69 | 0.50 | 0.75 | 0.32 | 0.28 | 0.80 |
| Pate2 | 1.00 | 1.00 | 1.00 | 1.00 | 1.00 | 1.00 | 1.00 | 1.00 | 1.00 | 1.00 | 1.00 | 1.00 |
| Pawr | 1.23 | 1.00 | 1.04 | 2.23 | 0.47 | 1.04 | 1.30 | 1.08 | 0.88 | 1.00 | 0.16 | 1.11 |
| Pbsn | 1.00 | 1.00 | 1.00 | 1.00 | 1.00 | 1.00 | 1.00 | 1.00 | 1.00 | 1.00 | 1.00 | 1.00 |
| Pcbp1 | 1.20 | 1.77 | 1.02 | 0.94 | 0.47 | 1.12 | 0.98 | 0.89 | 0.94 | 0.60 | 0.56 | 1.03 |
| Pcdh1 | 0.69 | 1.21 | 0.94 | 0.90 | 0.13 | 1.01 | 0.99 | 0.97 | 1.12 | 0.29 | 0.25 | 0.85 |
| Pcdh7 | 0.87 | 1.00 | 1.00 | 1.00 | 0.73 | 1.00 | 1.05 | 1.50 | 1.22 | 1.00 | 1.00 | 1.02 |
| Pcdhga11 | 1.00 | 0.92 | 1.00 | 1.00 | 0.68 | 1.00 | 0.59 | 0.64 | 0.94 | 1.00 | 1.00 | 0.97 |
| Pcid2 | 1.27 | 0.98 | 1.39 | 1.12 | 0.27 | 1.01 | 1.08 | 1.07 | 0.90 | 0.36 | 0.29 | 0.98 |
| Pcp4l1 | 1.78 | 1.24 | 1.08 | 0.98 | 0.51 | 1.13 | 2.68 | 2.90 | 2.17 | 0.89 | 0.83 | 0.71 |
| Pde12 | 0.90 | 1.59 | 0.73 | 0.71 | 0.20 | 0.77 | 1.25 | 1.40 | 1.52 | 0.54 | 0.70 | 1.08 |
| Pde6g | 1.71 | 0.74 | 1.00 | 0.55 | 2.25 | 1.10 | 1.00 | 1.00 | 1.00 | 1.00 | 1.00 | 1.00 |
| Pde8a | 0.80 | 1.00 | 1.11 | 0.59 | 0.14 | 0.70 | 1.69 | 1.32 | 1.01 | 1.00 | 0.93 | 1.17 |
| Pdgfa | 1.51 | 1.31 | 1.13 | 0.65 | 0.40 | 0.81 | 0.84 | 0.70 | 1.36 | 0.29 | 0.35 | 0.85 |
| Pdgfrl | 0.57 | 0.67 | 0.56 | 0.73 | 0.97 | 0.92 | 0.83 | 0.67 | 1.15 | 0.25 | 0.23 | 0.56 |
| Pdia4 | 0.71 | 2.10 | 1.14 | 1.50 | 0.40 | 1.45 | 0.89 | 0.84 | 1.16 | 0.26 | 0.30 | 1.11 |
| Pdpk1 | 0.89 | 2.81 | 1.19 | 2.01 | 0.11 | 0.90 | 1.36 | 1.89 | 1.47 | 0.73 | 0.27 | 0.94 |
| Pdss2 | 0.70 | 2.45 | 0.74 | 0.67 | 0.11 | 0.66 | 1.00 | 1.23 | 0.92 | 1.00 | 0.89 | 0.91 |
| Pdxp | 1.00 | 0.75 | 0.39 | 1.00 | 0.15 | 0.43 | 0.74 | 0.91 | 0.66 | 0.99 | 0.66 | 0.64 |
| Pdzd2 | 0.63 | 1.00 | 0.89 | 3.51 | 0.47 | 1.44 | 0.87 | 1.09 | 0.96 | 0.87 | 0.47 | 1.20 |
| Peak1 | 0.64 | 1.00 | 0.81 | 1.55 | 0.34 | 0.75 | 1.18 | 1.45 | 1.17 | 0.45 | 0.46 | 0.97 |
| Per3 | 0.20 | 0.57 | 0.49 | 0.73 | 0.18 | 0.44 | 0.62 | 0.63 | 0.62 | 0.18 | 0.18 | 0.65 |
| Perm1 | 0.51 | 0.54 | 0.86 | 0.18 | 0.16 | 0.75 | 0.54 | 0.79 | 0.88 | 1.13 | 1.14 | 0.82 |
| Pex11a | 0.49 | 1.00 | 0.84 | 1.04 | 0.02 | 1.40 | 0.92 | 1.03 | 0.94 | 1.00 | 0.31 | 1.64 |
| Pfdn4 | 0.80 | 1.68 | 0.95 | 0.60 | 0.63 | 1.20 | 0.82 | 0.79 | 0.80 | 0.18 | 0.56 | 0.95 |
| Pfkfb2 | 0.98 | 1.65 | 0.94 | 0.97 | 0.26 | 0.76 | 0.87 | 0.96 | 0.63 | 0.57 | 0.44 | 1.11 |
| Pfkl | 1.35 | 0.55 | 1.39 | 0.15 | 2.00 | 0.50 | 0.93 | 0.82 | 0.67 | 1.83 | 2.57 | 1.04 |
| Pfn2 | 0.59 | 0.89 | 0.64 | 1.26 | 0.10 | 0.76 | 0.80 | 0.65 | 0.75 | 0.75 | 0.64 | 1.01 |
| Pfn4 | 1.00 | 1.00 | 1.00 | 0.95 | 0.66 | 0.87 | 0.85 | 1.22 | 0.51 | 1.00 | 1.00 | 1.00 |
| Phactr4 | 1.12 | 2.09 | 1.03 | 1.68 | 0.36 | 1.12 | 1.31 | 1.40 | 1.04 | 0.29 | 0.41 | 0.97 |
| Phf12 | 0.83 | 1.21 | 1.13 | 1.49 | 0.36 | 0.98 | 0.89 | 0.75 | 1.04 | 0.61 | 0.60 | 0.97 |
| Phf2 | 0.87 | 1.90 | 1.05 | 2.57 | 0.24 | 1.30 | 1.24 | 1.09 | 0.94 | 0.24 | 0.29 | 1.02 |
| Phyhip | 1.00 | 1.00 | 1.00 | 1.00 | 0.07 | 1.00 | 0.28 | 0.21 | 0.58 | 1.00 | 1.00 | 1.00 |
| Pi16 | 0.75 | 0.40 | 0.79 | 0.58 | 1.87 | 0.71 | 0.74 | 0.66 | 0.88 | 1.26 | 1.01 | 0.95 |
| Piezo1 | 1.42 | 1.00 | 1.37 | 0.82 | 0.10 | 1.27 | 1.68 | 2.21 | 1.71 | 1.00 | 0.31 | 1.56 |
| Pigg | 0.61 | 1.00 | 1.06 | 1.42 | 0.22 | 0.92 | 1.26 | 1.08 | 1.08 | 1.00 | 0.51 | 1.19 |
| Pigh | 0.99 | 1.00 | 1.07 | 1.13 | 0.62 | 0.96 | 0.79 | 0.78 | 0.71 | 1.09 | 1.24 | 0.82 |
| Pik3c2g | 1.00 | 1.00 | 1.00 | 1.00 | 1.00 | 1.00 | 1.00 | 1.00 | 1.00 | 1.00 | 1.00 | 1.00 |
| Pik3r1 | 0.90 | 2.17 | 1.06 | 0.72 | 0.17 | 0.59 | 0.90 | 1.13 | 0.87 | 0.22 | 0.19 | 0.89 |
| Pim1 | 3.79 | 2.25 | 1.90 | 1.51 | 0.25 | 0.98 | 2.18 | 2.61 | 1.57 | 0.96 | 0.13 | 1.14 |
| Pin1rt1 | 0.91 | 1.59 | 0.95 | 0.82 | 0.44 | 0.70 | 0.84 | 0.87 | 0.93 | 0.29 | 0.37 | 1.07 |
| Pip5k1a | 1.04 | 1.38 | 1.29 | 1.30 | 0.15 | 1.09 | 1.14 | 1.55 | 1.39 | 1.00 | 0.62 | 1.18 |
| Pip5kl1 | 1.00 | 1.00 | 1.00 | 1.00 | 1.00 | 1.00 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 1.00 |
| Pirt | 1.00 | 1.00 | 1.00 | 1.00 | 1.00 | 1.00 | 0.16 | 0.17 | 0.30 | 1.00 | 1.00 | 1.00 |
| Pkd1 | 0.93 | 1.00 | 1.22 | 1.74 | 0.26 | 1.08 | 1.05 | 1.20 | 1.45 | 1.00 | 0.15 | 1.00 |
| Pkd2 | 0.99 | 2.84 | 1.07 | 2.39 | 0.18 | 1.16 | 1.16 | 1.15 | 1.19 | 0.55 | 0.32 | 1.30 |
| Pkia | 0.58 | 0.69 | 0.55 | 1.43 | 0.20 | 0.46 | 0.55 | 0.70 | 0.63 | 0.68 | 0.69 | 0.87 |
| Pla2g4a | 1.00 | 1.00 | 1.00 | 1.00 | 1.00 | 1.00 | 0.72 | 0.72 | 1.05 | 0.55 | 0.61 | 1.04 |
| Plac9b | 1.09 | 0.66 | 0.76 | 0.98 | 3.91 | 0.85 | 1.02 | 0.59 | 0.88 | 0.74 | 1.13 | 0.75 |
| Plagl1 | 0.84 | 1.00 | 1.00 | 1.13 | 1.00 | 1.00 | 0.63 | 0.72 | 0.88 | 0.47 | 0.20 | 0.85 |
| Plau | 0.80 | 1.49 | 0.80 | 0.74 | 0.19 | 0.91 | 0.77 | 0.45 | 0.89 | 1.00 | 0.38 | 0.73 |
| Plcg1 | 0.74 | 1.00 | 1.04 | 1.46 | 0.13 | 0.95 | 1.21 | 1.51 | 1.29 | 1.00 | 0.26 | 1.25 |
| Plcl2 | 1.15 | 1.28 | 1.42 | 1.82 | 0.76 | 1.37 | 0.69 | 0.89 | 0.63 | 1.43 | 1.68 | 0.76 |

Fig. 35- 70

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ost4 | 1.01 | 1.12 | 0.84 | 0.72 | 0.91 | 0.76 | 1.01 | 0.19 | 0.87 | 1.02 | 1.42 | 0.99 |
| Ostn | 1.00 | 1.00 | 1.00 | 1.00 | 1.00 | 1.00 | 1.00 | 1.00 | 1.00 | 1.00 | 1.00 | 1.00 |
| Oxtr | 1.00 | 1.00 | 1.00 | 1.00 | 1.00 | 1.00 | 1.00 | 1.00 | 1.00 | 1.00 | 1.00 | 1.00 |
| P2ry1 | 1.00 | 0.70 | 0.90 | 0.89 | 1.00 | 1.10 | 0.87 | 1.23 | 1.06 | 1.05 | 0.82 | 1.08 |
| Pacsin1 | 0.61 | 0.64 | 0.96 | 1.00 | 1.00 | 1.00 | 1.00 | 1.00 | 1.00 | 0.95 | 1.85 | 1.06 |
| Pak1 | 1.49 | 1.27 | 1.32 | 1.04 | 0.98 | 1.02 | 1.00 | 1.00 | 1.00 | 1.03 | 1.16 | 1.02 |
| Palmd | 1.64 | 1.64 | 1.17 | 1.53 | 1.00 | 1.44 | 0.78 | 0.64 | 0.80 | 1.16 | 0.91 | 1.23 |
| Pank3 | 0.53 | 0.45 | 0.74 | 1.02 | 1.97 | 0.88 | 0.81 | 0.48 | 0.82 | 0.95 | 0.57 | 0.89 |
| Paqr3 | 1.00 | 1.00 | 1.00 | 1.00 | 1.00 | 0.99 | 2.25 | 1.00 | 2.02 | 1.00 | 1.00 | 1.00 |
| Paqr9 | 1.49 | 1.09 | 1.50 | 1.12 | 1.41 | 1.49 | 0.84 | 0.36 | 1.04 | 1.00 | 1.00 | 1.00 |
| Pard6g | 1.06 | 0.94 | 1.21 | 1.26 | 1.00 | 1.80 | 1.00 | 1.00 | 1.00 | 0.64 | 0.46 | 0.50 |
| Pate2 | 1.00 | 1.00 | 1.00 | 1.00 | 1.00 | 1.00 | 1.00 | 1.00 | 1.00 | 1.00 | 1.00 | 1.00 |
| Pawr | 1.31 | 0.94 | 1.31 | 1.18 | 1.48 | 1.26 | 1.32 | 1.00 | 1.00 | 1.02 | 0.82 | 0.94 |
| Pbsn | 1.00 | 1.00 | 1.00 | 1.00 | 1.00 | 1.00 | 1.00 | 1.00 | 1.00 | 0.08 | 1.00 | 0.52 |
| Pcbp1 | 0.78 | 0.77 | 0.80 | 0.91 | 1.30 | 0.96 | 0.92 | 0.45 | 0.92 | 0.99 | 0.93 | 1.03 |
| Pcdh1 | 1.11 | 0.84 | 1.42 | 1.17 | 1.53 | 1.30 | 0.90 | 0.50 | 1.02 | 1.07 | 0.74 | 1.00 |
| Pcdh7 | 1.48 | 0.67 | 0.94 | 0.50 | 1.00 | 0.34 | 1.00 | 1.00 | 1.00 | 0.98 | 0.51 | 0.99 |
| Pcdhga11 | 1.00 | 1.00 | 1.13 | 1.00 | 1.00 | 1.00 | 1.00 | 1.00 | 1.00 | 0.99 | 1.00 | 0.92 |
| Pcid2 | 0.83 | 0.93 | 0.85 | 0.87 | 1.00 | 0.98 | 0.75 | 1.00 | 0.85 | 0.87 | 0.97 | 0.97 |
| Pcp4l1 | 1.89 | 1.44 | 0.97 | 1.28 | 1.84 | 1.76 | 0.13 | 0.11 | 0.14 | 1.04 | 1.19 | 1.20 |
| Pde12 | 0.64 | 0.68 | 0.81 | 1.21 | 2.10 | 1.12 | 0.98 | 0.99 | 0.88 | 1.04 | 0.93 | 1.01 |
| Pde6g | 1.00 | 1.00 | 1.00 | 1.00 | 1.00 | 1.02 | 1.00 | 1.00 | 1.00 | 1.00 | 1.00 | 1.00 |
| Pde8a | 1.03 | 1.00 | 1.17 | 1.12 | 1.00 | 0.88 | 0.70 | 1.00 | 0.69 | 0.81 | 0.75 | 0.81 |
| Pdgfa | 1.38 | 1.24 | 1.05 | 1.13 | 1.91 | 0.95 | 1.71 | 1.00 | 1.75 | 1.01 | 1.24 | 1.06 |
| Pdgfrl | 2.60 | 1.90 | 2.17 | 1.00 | 1.00 | 1.00 | 1.00 | 1.00 | 1.00 | 0.52 | 0.72 | 0.94 |
| Pdia4 | 1.03 | 1.00 | 1.34 | 1.11 | 1.94 | 1.09 | 1.06 | 0.18 | 1.14 | 1.07 | 0.97 | 1.02 |
| Pdpk1 | 0.52 | 0.46 | 0.71 | 1.23 | 1.00 | 1.14 | 1.39 | 1.00 | 1.32 | 1.07 | 0.56 | 0.94 |
| Pdss2 | 0.81 | 0.79 | 0.86 | 1.06 | 1.00 | 0.93 | 0.91 | 1.27 | 0.81 | 1.00 | 1.10 | 0.90 |
| Pdxp | 0.46 | 0.55 | 0.58 | 1.00 | 1.00 | 1.00 | 1.00 | 1.00 | 1.00 | 1.13 | 1.00 | 1.06 |
| Pdzd2 | 1.37 | 1.06 | 1.29 | 1.35 | 1.51 | 1.44 | 1.00 | 1.00 | 1.00 | 0.95 | 0.66 | 0.80 |
| Peak1 | 0.79 | 0.72 | 1.12 | 1.10 | 1.00 | 0.97 | 1.33 | 1.00 | 1.00 | 0.98 | 0.72 | 0.85 |
| Per3 | 0.93 | 0.84 | 0.90 | 0.53 | 1.00 | 0.67 | 0.41 | 0.89 | 0.63 | 0.67 | 0.59 | 0.74 |
| Perm1 | 0.73 | 0.66 | 0.83 | 0.49 | 0.62 | 0.65 | 1.00 | 1.00 | 1.00 | 1.47 | 1.00 | 1.02 |
| Pex11a | 1.31 | 1.04 | 1.51 | 0.90 | 1.22 | 0.86 | 1.58 | 1.81 | 1.52 | 1.01 | 0.46 | 1.11 |
| Pfdn4 | 1.05 | 0.77 | 0.80 | 1.20 | 3.65 | 1.09 | 1.04 | 0.44 | 0.80 | 1.25 | 1.52 | 0.99 |
| Pfkfb2 | 0.89 | 0.77 | 0.98 | 1.00 | 1.12 | 0.94 | 2.35 | 1.08 | 2.13 | 1.10 | 0.76 | 0.93 |
| Pfkl | 1.07 | 1.25 | 0.95 | 0.89 | 0.71 | 0.90 | 0.60 | 0.75 | 0.66 | 0.80 | 1.12 | 0.91 |
| Pfn2 | 0.95 | 0.85 | 1.05 | 0.86 | 0.84 | 0.88 | 1.08 | 1.00 | 0.99 | 1.09 | 1.05 | 1.23 |
| Pfn4 | 1.00 | 1.00 | 1.00 | 0.45 | 1.00 | 0.46 | 1.00 | 1.00 | 1.00 | 1.00 | 1.00 | 1.00 |
| Phactr4 | 0.73 | 0.71 | 0.85 | 1.11 | 2.13 | 1.13 | 0.94 | 0.76 | 0.95 | 0.94 | 0.62 | 0.91 |
| Phf12 | 0.76 | 0.77 | 0.92 | 0.93 | 1.61 | 0.94 | 0.92 | 0.74 | 1.07 | 0.96 | 0.73 | 0.91 |
| Phf2 | 0.56 | 0.51 | 0.71 | 0.92 | 1.00 | 1.05 | 0.98 | 1.00 | 0.94 | 0.96 | 0.64 | 0.97 |
| Phyhip | 1.00 | 1.00 | 1.00 | 0.46 | 0.48 | 0.63 | 1.00 | 1.00 | 1.00 | 1.00 | 1.00 | 1.00 |
| Pi16 | 0.62 | 0.55 | 0.62 | 1.17 | 1.02 | 1.66 | 1.00 | 1.00 | 1.00 | 0.88 | 1.18 | 0.92 |
| Piezo1 | 0.63 | 0.42 | 1.01 | 1.37 | 1.00 | 1.25 | 1.00 | 1.00 | 1.00 | 1.13 | 0.46 | 1.01 |
| Pigg | 0.61 | 0.60 | 0.97 | 1.24 | 1.00 | 1.11 | 1.04 | 1.00 | 0.81 | 1.06 | 0.45 | 0.90 |
| Pigh | 0.99 | 1.00 | 1.00 | 0.79 | 1.01 | 0.80 | 0.89 | 1.00 | 0.87 | 1.09 | 1.68 | 1.06 |
| Pik3c2g | 1.00 | 1.00 | 1.00 | 0.18 | 0.62 | 0.17 | 2.34 | 1.35 | 1.15 | 2.87 | 3.07 | 2.61 |
| Pik3r1 | 1.02 | 0.97 | 1.11 | 1.05 | 1.16 | 0.93 | 0.67 | 0.53 | 0.65 | 0.90 | 0.71 | 0.83 |
| Pim1 | 0.87 | 0.80 | 1.03 | 1.76 | 1.00 | 1.25 | 1.05 | 2.67 | 1.22 | 1.13 | 0.70 | 1.05 |
| Pin1rt1 | 0.91 | 0.97 | 0.72 | 0.78 | 1.74 | 0.90 | 1.32 | 1.57 | 1.07 | 1.02 | 1.06 | 1.15 |
| Pip5k1a | 0.66 | 0.57 | 0.86 | 1.27 | 1.00 | 0.84 | 0.91 | 1.00 | 1.03 | 1.03 | 0.46 | 1.01 |
| Pip5kl1 | 1.00 | 1.00 | 1.00 | 1.00 | 1.00 | 1.00 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 1.00 |
| Pirt | 1.00 | 1.00 | 1.00 | 1.00 | 1.00 | 1.00 | 1.00 | 1.00 | 1.00 | 1.12 | 0.38 | 0.82 |
| Pkd1 | 0.77 | 0.69 | 1.12 | 1.24 | 1.00 | 1.22 | 0.81 | 1.00 | 1.16 | 1.03 | 0.65 | 1.04 |
| Pkd2 | 1.68 | 1.18 | 1.47 | 0.98 | 2.09 | 1.11 | 0.83 | 1.00 | 0.94 | 0.99 | 0.67 | 1.03 |
| Pkia | 0.99 | 0.75 | 1.42 | 0.87 | 0.78 | 0.84 | 1.00 | 1.00 | 1.00 | 1.04 | 0.85 | 0.98 |
| Pla2g4a | 1.04 | 0.92 | 1.09 | 0.75 | 1.00 | 0.88 | 1.00 | 1.00 | 1.00 | 1.08 | 0.98 | 1.05 |
| Plac9b | 2.06 | 1.06 | 1.16 | 1.64 | 1.15 | 0.96 | 1.27 | 2.95 | 1.33 | 1.01 | 1.41 | 1.15 |
| Plagl1 | 0.87 | 0.72 | 0.94 | 0.90 | 1.00 | 1.06 | 1.00 | 1.00 | 1.00 | 0.82 | 0.53 | 0.96 |
| Plau | 0.91 | 0.72 | 1.17 | 1.32 | 2.13 | 1.44 | 1.00 | 1.00 | 1.00 | 0.83 | 0.78 | 0.81 |
| Plcg1 | 0.67 | 0.54 | 0.98 | 1.39 | 1.00 | 1.24 | 0.62 | 1.00 | 0.88 | 1.01 | 0.48 | 1.03 |
| Plcl2 | 1.11 | 1.14 | 1.47 | 0.19 | 0.15 | 0.19 | 0.21 | 0.62 | 0.20 | 1.09 | 0.83 | 0.93 |

Fig. 35-71

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ost4 | 0.94 | 1.00 | 1.00 | 0.94 | 0.88 | 0.99 | 0.87 | 0.65 | 0.90 | 0.97 | 0.90 | 0.86 |
| Ostn | 1.00 | 1.00 | 1.00 | 1.00 | 1.00 | 1.00 | 1.00 | 1.00 | 1.00 | 1.00 | 1.00 | 1.00 |
| Oxtr | 1.00 | 1.00 | 1.00 | 0.26 | 1.00 | 0.12 | 0.74 | 0.87 | 0.64 | 1.00 | 1.00 | 1.00 |
| P2ry1 | 0.95 | 0.83 | 0.74 | 0.54 | 1.00 | 0.51 | 1.00 | 1.00 | 1.00 | 1.33 | 0.76 | 0.63 |
| Pacsin1 | 1.62 | 1.33 | 2.34 | 1.29 | 1.00 | 1.63 | 1.24 | 1.00 | 2.24 | 0.73 | 1.28 | 0.79 |
| Pak1 | 0.90 | 0.90 | 0.89 | 1.26 | 2.89 | 1.16 | 0.95 | 1.83 | 1.00 | 0.77 | 1.72 | 0.91 |
| Palmd | 1.10 | 1.08 | 1.50 | 0.40 | 0.09 | 0.42 | 1.00 | 1.00 | 1.15 | 1.33 | 1.53 | 1.57 |
| Pank3 | 0.88 | 0.77 | 0.76 | 0.39 | 0.05 | 0.56 | 1.09 | 1.00 | 1.06 | 0.91 | 0.61 | 1.07 |
| Paqr3 | 1.00 | 1.00 | 1.00 | 0.68 | 0.43 | 0.64 | 1.45 | 1.00 | 1.10 | 1.00 | 1.00 | 1.27 |
| Paqr9 | 1.00 | 1.00 | 1.00 | 0.40 | 0.70 | 0.31 | 0.95 | 1.08 | 1.07 | 0.53 | 0.49 | 0.57 |
| Pard6g | 0.69 | 0.70 | 0.83 | 0.54 | 1.00 | 0.86 | 0.72 | 0.73 | 0.84 | 1.07 | 1.16 | 1.70 |
| Pate2 | 1.00 | 1.00 | 1.00 | 1.00 | 1.00 | 0.14 | 1.00 | 1.00 | 1.00 | 1.00 | 1.00 | 1.00 |
| Pawr | 0.99 | 0.92 | 0.95 | 0.86 | 0.28 | 1.24 | 0.80 | 1.00 | 1.55 | 0.73 | 0.78 | 1.05 |
| Pbsn | 1.00 | 1.00 | 1.00 | 1.00 | 1.00 | 1.00 | 1.00 | 1.00 | 1.00 | 1.00 | 1.00 | 1.00 |
| Pcbp1 | 0.88 | 0.88 | 0.83 | 1.14 | 0.59 | 1.13 | 0.96 | 0.42 | 1.00 | 0.96 | 0.89 | 0.92 |
| Pcdh1 | 1.00 | 1.14 | 0.84 | 1.34 | 0.22 | 1.38 | 1.00 | 1.00 | 1.00 | 0.82 | 1.24 | 1.04 |
| Pcdh7 | 0.96 | 0.74 | 0.77 | 0.71 | 0.35 | 0.62 | 1.00 | 1.00 | 1.00 | 1.99 | 2.96 | 2.19 |
| Pcdhga11 | 1.09 | 1.06 | 1.00 | 1.21 | 1.00 | 1.03 | 1.00 | 1.00 | 1.00 | 1.00 | 1.84 | 1.00 |
| Pcid2 | 1.14 | 0.90 | 1.13 | 1.09 | 1.00 | 0.98 | 0.91 | 0.27 | 0.93 | 1.05 | 0.96 | 1.08 |
| Pcp4l1 | 1.08 | 1.12 | 1.13 | 2.13 | 1.87 | 3.76 | 0.58 | 0.33 | 0.63 | 0.57 | 1.00 | 0.38 |
| Pde12 | 0.95 | 0.94 | 0.78 | 0.99 | 1.00 | 0.90 | 1.07 | 1.00 | 1.27 | 0.98 | 0.89 | 1.11 |
| Pde6g | 1.00 | 1.00 | 1.00 | 1.00 | 1.00 | 1.00 | 1.59 | 0.70 | 1.32 | 1.00 | 1.00 | 1.00 |
| Pde8a | 1.05 | 1.15 | 0.88 | 0.90 | 1.00 | 0.74 | 1.06 | 1.00 | 1.07 | 0.99 | 0.82 | 1.17 |
| Pdgfa | 1.14 | 1.24 | 0.88 | 1.10 | 1.00 | 1.29 | 1.21 | 0.97 | 1.21 | 0.79 | 1.02 | 0.89 |
| Pdgfrl | 0.78 | 1.29 | 1.24 | 1.07 | 1.00 | 1.16 | 0.77 | 1.00 | 0.91 | 1.09 | 1.28 | 1.00 |
| Pdia4 | 1.03 | 0.77 | 0.90 | 1.04 | 0.13 | 1.17 | 0.92 | 0.53 | 0.92 | 1.49 | 1.25 | 1.56 |
| Pdpk1 | 1.00 | 0.85 | 0.81 | 1.05 | 0.25 | 0.82 | 0.91 | 1.70 | 1.08 | 0.90 | 0.63 | 1.07 |
| Pdss2 | 0.91 | 0.90 | 0.71 | 0.95 | 0.77 | 0.93 | 0.94 | 1.00 | 0.72 | 1.09 | 0.85 | 1.17 |
| Pdxp | 0.61 | 0.70 | 0.88 | 0.28 | 0.90 | 0.54 | 1.06 | 0.82 | 1.43 | 0.82 | 1.32 | 0.87 |
| Pdzd2 | 1.14 | 1.09 | 0.93 | 0.67 | 0.13 | 0.68 | 1.19 | 1.00 | 1.10 | 1.06 | 1.05 | 1.50 |
| Peak1 | 1.04 | 0.91 | 0.83 | 1.00 | 0.19 | 0.54 | 1.30 | 1.00 | 1.25 | 1.02 | 0.69 | 1.15 |
| Per3 | 0.38 | 0.61 | 0.68 | 0.20 | 0.24 | 0.37 | 0.78 | 1.00 | 0.75 | 0.56 | 0.53 | 0.74 |
| Perm1 | 1.06 | 1.08 | 1.01 | 1.00 | 1.00 | 0.94 | 1.16 | 1.00 | 1.06 | 0.86 | 0.80 | 0.93 |
| Pex11a | 1.29 | 1.40 | 1.44 | 1.05 | 0.59 | 1.55 | 1.17 | 1.41 | 0.85 | 1.57 | 1.25 | 1.44 |
| Pfdn4 | 1.42 | 0.85 | 0.98 | 1.07 | 0.81 | 1.04 | 1.22 | 0.43 | 0.94 | 0.95 | 1.06 | 1.02 |
| Pfkfb2 | 1.17 | 1.15 | 0.88 | 0.85 | 0.42 | 0.69 | 0.94 | 1.14 | 0.96 | 0.82 | 0.67 | 0.89 |
| Pfkl | 0.93 | 1.17 | 0.91 | 0.68 | 2.67 | 0.85 | 0.98 | 1.45 | 0.82 | 1.12 | 1.20 | 1.01 |
| Pfn2 | 1.22 | 0.76 | 1.10 | 0.90 | 0.91 | 1.04 | 0.98 | 0.50 | 0.93 | 0.84 | 3.74 | 0.95 |
| Pfn4 | 1.00 | 1.00 | 1.00 | 1.00 | 1.00 | 1.00 | 1.03 | 0.19 | 0.87 | 1.00 | 1.00 | 1.00 |
| Phactr4 | 0.99 | 0.92 | 0.92 | 1.45 | 0.55 | 1.39 | 1.16 | 0.70 | 1.00 | 0.95 | 0.75 | 0.97 |
| Phf12 | 0.86 | 1.10 | 1.14 | 1.05 | 0.46 | 1.21 | 1.01 | 0.74 | 1.13 | 0.97 | 0.81 | 0.96 |
| Phf2 | 0.96 | 1.02 | 0.94 | 0.98 | 0.33 | 1.11 | 0.94 | 0.25 | 1.12 | 0.92 | 0.73 | 0.96 |
| Phyhip | 0.79 | 0.82 | 0.92 | 1.00 | 1.00 | 1.47 | 1.00 | 1.00 | 1.00 | 0.35 | 4.33 | 0.18 |
| Pi16 | 1.30 | 1.23 | 1.22 | 0.68 | 0.75 | 0.77 | 1.15 | 2.19 | 0.97 | 1.58 | 0.85 | 1.05 |
| Piezo1 | 0.99 | 1.28 | 0.88 | 1.30 | 0.20 | 1.18 | 0.85 | 1.00 | 1.12 | 0.64 | 0.39 | 0.96 |
| Pigg | 1.09 | 0.91 | 0.85 | 0.94 | 1.00 | 0.84 | 1.22 | 1.49 | 1.26 | 1.12 | 0.67 | 0.94 |
| Pigh | 1.02 | 1.07 | 1.12 | 0.72 | 0.62 | 1.04 | 0.81 | 1.10 | 0.99 | 0.86 | 0.76 | 0.98 |
| Pik3c2g | 1.32 | 1.21 | 1.26 | 1.00 | 1.00 | 1.00 | 1.00 | 1.00 | 1.00 | 1.00 | 1.00 | 1.00 |
| Pik3r1 | 0.97 | 0.95 | 1.01 | 0.60 | 0.17 | 0.55 | 0.90 | 1.00 | 0.74 | 0.98 | 0.76 | 1.02 |
| Pim1 | 1.03 | 1.18 | 0.96 | 2.97 | 0.87 | 1.45 | 0.98 | 1.85 | 1.12 | 1.00 | 0.72 | 1.04 |
| Pin1rt1 | 0.94 | 1.02 | 1.08 | 0.89 | 1.00 | 0.89 | 1.05 | 0.13 | 0.91 | 1.22 | 1.18 | 1.07 |
| Pip5k1a | 1.07 | 1.05 | 0.85 | 1.26 | 1.00 | 0.98 | 1.29 | 1.86 | 0.87 | 0.93 | 0.61 | 0.93 |
| Pip5kl1 | 1.00 | 1.00 | 1.00 | 1.00 | 1.00 | 1.00 | 0.69 | 0.19 | 1.01 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 1.00 |
| Pirt | 1.54 | 1.17 | 1.25 | 1.00 | 1.00 | 1.00 | 1.00 | 1.00 | 1.00 | 1.00 | 1.00 | 1.00 |
| Pkd1 | 1.25 | 1.55 | 1.14 | 1.21 | 0.16 | 1.08 | 1.13 | 1.00 | 1.15 | 0.95 | 0.78 | 1.21 |
| Pkd2 | 1.33 | 1.35 | 1.31 | 1.00 | 0.32 | 0.88 | 1.05 | 0.98 | 1.02 | 1.07 | 0.80 | 1.01 |
| Pkia | 1.33 | 0.98 | 1.46 | 1.08 | 0.83 | 0.73 | 1.55 | 1.00 | 1.09 | 0.88 | 1.56 | 1.15 |
| Pla2g4a | 0.97 | 0.79 | 0.91 | 0.88 | 1.00 | 0.78 | 1.00 | 1.00 | 1.00 | 0.79 | 0.59 | 0.61 |
| Plac9b | 0.82 | 0.91 | 1.01 | 1.14 | 2.79 | 1.18 | 1.89 | 1.18 | 1.29 | 0.83 | 1.18 | 1.14 |
| Plagl1 | 1.00 | 0.98 | 1.07 | 0.83 | 0.30 | 0.59 | 0.91 | 1.00 | 1.12 | 1.40 | 2.05 | 1.00 |
| Plau | 0.54 | 0.43 | 0.53 | 0.73 | 0.28 | 0.81 | 1.00 | 1.00 | 1.00 | 0.76 | 0.56 | 0.58 |
| Plcg1 | 1.18 | 1.18 | 0.95 | 0.92 | 0.41 | 0.87 | 1.20 | 1.00 | 0.99 | 1.25 | 0.82 | 1.41 |
| Plcl2 | 1.20 | 0.97 | 1.39 | 1.20 | 2.33 | 0.96 | 1.28 | 2.75 | 0.79 | 0.91 | 0.87 | 0.97 |

Fig. 35- 72

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ost4 | 1.13 | 1.00 | 0.84 | 1.19 | 0.26 | 1.03 | 1.22 | 0.37 | 0.90 | 1.08 | 1.10 | 1.13 |
| Ostn | 1.00 | 1.00 | 1.00 | 1.00 | 1.00 | 1.00 | 1.12 | 2.77 | 0.99 | 1.00 | 1.00 | 1.00 |
| Oxtr | 1.00 | 1.00 | 1.00 | 1.09 | 0.64 | 1.15 | 0.87 | 0.83 | 1.01 | 1.00 | 1.00 | 1.00 |
| P2ry1 | 1.00 | 1.00 | 1.00 | 1.03 | 1.00 | 1.20 | 0.42 | 0.16 | 0.56 | 0.62 | 0.63 | 0.91 |
| Pacsin1 | 1.00 | 1.00 | 1.00 | 1.02 | 0.92 | 1.03 | 1.00 | 1.00 | 1.00 | 1.04 | 0.79 | 0.74 |
| Pak1 | 1.00 | 1.00 | 1.00 | 1.16 | 1.17 | 1.06 | 0.81 | 1.49 | 0.82 | 1.73 | 1.21 | 1.14 |
| Palmd | 1.00 | 1.00 | 1.00 | 0.81 | 1.00 | 0.78 | 0.89 | 0.10 | 0.98 | 1.00 | 1.00 | 1.00 |
| Pank3 | 1.09 | 1.25 | 0.86 | 0.79 | 1.00 | 0.93 | 0.84 | 0.15 | 1.09 | 0.50 | 0.94 | 0.94 |
| Paqr3 | 1.00 | 1.00 | 1.00 | 0.67 | 1.00 | 0.99 | 0.75 | 0.19 | 0.81 | 1.00 | 1.00 | 1.00 |
| Paqr9 | 1.00 | 1.00 | 1.00 | 0.87 | 0.39 | 1.04 | 1.16 | 1.00 | 1.00 | 0.46 | 0.68 | 0.91 |
| Pard6g | 1.00 | 1.00 | 1.00 | 0.63 | 0.46 | 0.61 | 0.67 | 0.10 | 0.74 | 1.00 | 1.17 | 1.03 |
| Pate2 | 1.00 | 1.00 | 1.00 | 1.00 | 1.00 | 1.00 | 1.00 | 1.00 | 1.00 | 1.00 | 1.00 | 1.00 |
| Pawr | 1.19 | 1.18 | 0.84 | 1.00 | 1.00 | 1.00 | 1.42 | 0.17 | 1.27 | 0.63 | 1.55 | 0.97 |
| Pbsn | 1.00 | 1.00 | 1.00 | 1.00 | 1.00 | 1.00 | 1.00 | 1.00 | 1.00 | 1.00 | 1.00 | 1.00 |
| Pcbp1 | 1.24 | 1.23 | 0.98 | 1.11 | 1.27 | 1.01 | 0.94 | 0.20 | 0.85 | 0.49 | 0.86 | 1.00 |
| Pcdh1 | 0.95 | 0.70 | 1.11 | 0.76 | 1.00 | 0.88 | 0.91 | 0.17 | 0.73 | 1.00 | 1.00 | 1.00 |
| Pcdh7 | 1.00 | 1.00 | 1.00 | 0.93 | 0.90 | 0.94 | 0.32 | 0.16 | 0.43 | 1.00 | 1.00 | 1.00 |
| Pcdhga11 | 1.00 | 1.00 | 1.00 | 0.98 | 0.20 | 0.87 | 0.89 | 0.92 | 0.95 | 1.00 | 1.00 | 1.00 |
| Pcid2 | 0.74 | 0.75 | 0.60 | 1.10 | 2.26 | 1.06 | 1.10 | 0.11 | 0.97 | 0.48 | 0.98 | 1.07 |
| Pcp4l1 | 0.90 | 1.36 | 1.25 | 1.14 | 1.72 | 1.11 | 0.80 | 0.89 | 0.87 | 0.30 | 0.31 | 0.48 |
| Pde12 | 1.14 | 1.14 | 1.00 | 1.04 | 1.00 | 1.07 | 0.74 | 0.28 | 0.70 | 0.43 | 0.82 | 0.92 |
| Pde6g | 1.00 | 1.00 | 1.00 | 1.00 | 0.16 | 1.00 | 1.00 | 1.00 | 1.00 | 1.00 | 1.00 | 1.00 |
| Pde8a | 1.00 | 1.00 | 1.00 | 0.68 | 1.00 | 0.87 | 1.16 | 0.43 | 1.54 | 1.00 | 1.27 | 0.87 |
| Pdgfa | 1.23 | 1.06 | 0.56 | 0.86 | 1.06 | 1.11 | 1.16 | 0.16 | 0.83 | 1.00 | 1.00 | 1.00 |
| Pdgfrl | 1.00 | 1.00 | 1.00 | 0.98 | 1.00 | 0.84 | 1.09 | 0.19 | 1.15 | 1.00 | 1.00 | 1.00 |
| Pdia4 | 1.12 | 0.85 | 0.74 | 0.92 | 1.35 | 0.95 | 0.74 | 0.08 | 0.93 | 0.37 | 1.13 | 1.27 |
| Pdpk1 | 1.22 | 1.20 | 1.32 | 0.92 | 1.00 | 0.95 | 0.83 | 0.10 | 1.05 | 0.31 | 0.82 | 0.91 |
| Pdss2 | 1.00 | 1.00 | 1.00 | 0.92 | 1.00 | 1.11 | 1.29 | 0.61 | 1.00 | 1.00 | 1.08 | 1.10 |
| Pdxp | 0.72 | 0.98 | 0.52 | 1.04 | 1.02 | 1.03 | 0.82 | 0.40 | 0.72 | 0.56 | 0.78 | 0.80 |
| Pdzd2 | 1.00 | 1.00 | 1.00 | 0.92 | 1.00 | 0.97 | 0.64 | 0.19 | 0.82 | 1.00 | 1.00 | 1.00 |
| Peak1 | 1.00 | 1.00 | 1.00 | 0.92 | 0.74 | 0.98 | 0.75 | 0.26 | 1.04 | 1.00 | 0.85 | 0.89 |
| Per3 | 0.17 | 0.28 | 0.55 | 0.81 | 1.59 | 0.76 | 0.48 | 0.04 | 0.60 | 1.00 | 1.27 | 1.21 |
| Perm1 | 1.00 | 1.00 | 1.00 | 0.95 | 1.12 | 1.06 | 0.92 | 0.12 | 1.07 | 1.00 | 1.00 | 1.00 |
| Pex11a | 0.80 | 1.15 | 1.12 | 1.49 | 1.00 | 0.64 | 1.41 | 0.08 | 1.31 | 1.00 | 1.61 | 1.11 |
| Pfdn4 | 1.84 | 0.87 | 0.82 | 0.92 | 2.32 | 0.80 | 0.79 | 0.11 | 0.88 | 0.88 | 1.06 | 1.00 |
| Pfkfb2 | 1.35 | 1.10 | 1.37 | 0.93 | 1.14 | 0.89 | 0.88 | 0.17 | 1.07 | 0.40 | 0.84 | 0.82 |
| Pfkl | 1.16 | 1.00 | 1.20 | 1.08 | 1.21 | 0.97 | 1.00 | 3.68 | 0.79 | 2.09 | 1.17 | 1.06 |
| Pfn2 | 1.00 | 1.00 | 1.00 | 1.14 | 1.13 | 1.03 | 0.96 | 0.31 | 1.16 | 1.00 | 1.00 | 0.94 |
| Pfn4 | 1.00 | 1.00 | 1.00 | 1.31 | 1.00 | 1.40 | 1.37 | 1.00 | 1.00 | 1.00 | 1.00 | 1.00 |
| Phactr4 | 1.66 | 1.14 | 1.10 | 1.08 | 1.00 | 1.09 | 0.88 | 0.18 | 1.08 | 0.38 | 0.88 | 0.84 |
| Phf12 | 1.23 | 1.18 | 0.97 | 0.96 | 0.31 | 1.04 | 0.99 | 0.18 | 1.09 | 0.74 | 1.02 | 0.97 |
| Phf2 | 0.88 | 1.01 | 0.80 | 0.94 | 1.00 | 1.07 | 0.99 | 0.08 | 1.18 | 0.29 | 0.89 | 0.86 |
| Phyhip | 1.00 | 1.00 | 1.00 | 1.00 | 0.76 | 0.97 | 0.66 | 0.99 | 0.54 | 0.51 | 0.62 | 0.59 |
| Pi16 | 0.78 | 0.62 | 0.75 | 1.15 | 0.14 | 0.91 | 1.49 | 3.19 | 1.16 | 1.64 | 1.30 | 0.92 |
| Piezo1 | 1.00 | 1.00 | 1.00 | 1.00 | 1.00 | 1.15 | 0.99 | 0.15 | 1.06 | 0.91 | 0.60 | 0.59 |
| Pigg | 1.02 | 0.67 | 0.89 | 0.94 | 1.00 | 0.99 | 0.75 | 0.18 | 0.80 | 1.00 | 0.73 | 0.75 |
| Pigh | 0.93 | 0.99 | 1.33 | 0.90 | 0.20 | 0.82 | 0.84 | 0.78 | 0.85 | 0.66 | 0.87 | 1.07 |
| Pik3c2g | 2.15 | 3.22 | 1.65 | 1.00 | 1.00 | 1.00 | 0.89 | 0.98 | 1.15 | 1.00 | 1.00 | 1.00 |
| Pik3r1 | 1.85 | 1.90 | 1.33 | 0.97 | 2.50 | 0.97 | 1.29 | 0.20 | 1.70 | 0.32 | 0.90 | 0.84 |
| Pim1 | 1.44 | 0.74 | 1.05 | 1.29 | 0.77 | 1.21 | 0.97 | 0.03 | 0.93 | 0.23 | 1.10 | 0.81 |
| Pin1rt1 | 0.55 | 1.05 | 0.59 | 1.09 | 1.00 | 1.01 | 0.86 | 0.06 | 0.91 | 0.25 | 1.05 | 0.95 |
| Pip5k1a | 1.36 | 1.17 | 1.04 | 1.06 | 2.14 | 0.97 | 0.84 | 0.10 | 1.00 | 1.00 | 0.70 | 0.69 |
| Pip5kl1 | 1.00 | 1.00 | 1.00 | 1.14 | 1.00 | 0.80 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 0.18 |
| Pirt | 1.00 | 1.00 | 1.00 | 1.00 | 1.00 | 1.00 | 1.00 | 1.00 | 1.00 | 1.00 | 1.00 | 1.00 |
| Pkd1 | 1.13 | 1.18 | 1.36 | 0.75 | 1.00 | 0.90 | 1.12 | 0.11 | 1.38 | 1.00 | 0.80 | 0.83 |
| Pkd2 | 1.01 | 0.91 | 1.20 | 0.87 | 1.00 | 0.93 | 0.87 | 0.11 | 1.23 | 1.00 | 0.94 | 0.97 |
| Pkia | 1.00 | 1.00 | 1.00 | 0.91 | 0.85 | 0.88 | 0.84 | 1.45 | 1.24 | 1.00 | 1.00 | 1.00 |
| Pla2g4a | 1.00 | 1.00 | 1.00 | 1.00 | 1.00 | 1.00 | 0.50 | 0.17 | 0.71 | 0.42 | 0.79 | 1.26 |
| Plac9b | 1.51 | 0.84 | 0.52 | 1.76 | 0.18 | 0.67 | 1.28 | 4.42 | 1.32 | 1.00 | 1.00 | 1.00 |
| Plagl1 | 0.50 | 0.55 | 0.73 | 1.17 | 1.00 | 1.34 | 0.87 | 0.34 | 0.82 | 1.00 | 1.00 | 1.00 |
| Plau | 0.56 | 0.84 | 0.62 | 1.00 | 1.00 | 1.45 | 0.36 | 0.05 | 0.47 | 0.52 | 0.56 | 1.21 |
| Plcg1 | 0.87 | 1.00 | 1.00 | 0.90 | 1.00 | 0.90 | 0.79 | 0.12 | 0.94 | 1.00 | 0.94 | 0.66 |
| Plcl2 | 1.02 | 1.11 | 1.19 | 1.41 | 3.26 | 1.15 | 1.68 | 3.21 | 1.71 | 1.67 | 1.12 | 1.01 |

Fig. 35- 73

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Plet1os | 0.24 | 0.20 | 0.44 | 0.62 | 3.62 | 0.59 | 0.94 | 0.89 | 1.02 | 1.00 | 1.00 | 1.00 |
| Plp2 | 2.17 | 2.11 | 1.13 | 0.79 | 0.51 | 1.16 | 0.67 | 0.75 | 0.78 | 0.21 | 0.55 | 1.10 |
| Plscr1 | 1.00 | 1.00 | 1.00 | 1.00 | 1.00 | 0.86 | 0.90 | 0.99 | 1.90 | 0.16 | 0.23 | 0.85 |
| Plscr2 | 1.00 | 1.00 | 0.51 | 0.39 | 0.26 | 0.38 | 0.86 | 1.23 | 1.10 | 0.13 | 0.18 | 0.90 |
| Plscr4 | 0.88 | 1.04 | 1.03 | 1.52 | 0.39 | 1.23 | 1.03 | 1.19 | 1.08 | 0.28 | 0.35 | 0.80 |
| Pltp | 0.49 | 0.48 | 0.74 | 0.30 | 1.02 | 0.96 | 0.38 | 0.33 | 0.49 | 0.90 | 0.93 | 0.62 |
| Plxna1 | 0.79 | 1.00 | 0.87 | 0.74 | 0.17 | 0.71 | 1.07 | 1.08 | 1.15 | 0.62 | 0.35 | 0.98 |
| Plxna2 | 1.05 | 1.05 | 1.34 | 1.27 | 0.33 | 0.89 | 1.29 | 1.76 | 1.29 | 0.92 | 1.25 | 1.88 |
| Pm20d2 | 0.58 | 1.33 | 0.93 | 0.87 | 0.35 | 0.70 | 0.79 | 0.97 | 0.76 | 1.00 | 1.00 | 1.00 |
| Pnisr | 0.82 | 1.27 | 0.85 | 1.94 | 0.21 | 1.00 | 0.79 | 0.88 | 0.85 | 0.48 | 0.34 | 0.91 |
| Pnmal2 | 1.00 | 1.00 | 1.00 | 1.00 | 0.10 | 1.00 | 0.70 | 0.68 | 0.66 | 1.81 | 1.49 | 1.07 |
| Pnp2 | 1.11 | 1.00 | 1.32 | 0.25 | 0.10 | 0.67 | 1.47 | 1.59 | 0.89 | 1.00 | 0.56 | 1.10 |
| Pnpla5 | 1.00 | 1.00 | 1.00 | 1.00 | 1.00 | 1.00 | 1.00 | 1.00 | 1.00 | 1.00 | 1.00 | 1.03 |
| Polh | 0.55 | 1.00 | 0.63 | 1.38 | 0.54 | 1.13 | 0.96 | 1.30 | 0.98 | 1.00 | 0.86 | 1.04 |
| Polm | 0.65 | 0.64 | 0.53 | 1.37 | 0.86 | 1.28 | 1.11 | 0.95 | 1.14 | 0.40 | 0.35 | 1.00 |
| Poln | 1.00 | 1.00 | 1.00 | 0.14 | 2.86 | 0.51 | 1.06 | 1.00 | 1.00 | 1.73 | 1.11 | 1.00 |
| Polr2i | 1.00 | 0.62 | 0.71 | 0.17 | 0.91 | 1.00 | 1.21 | 1.00 | 1.00 | 1.17 | 0.83 | 1.00 |
| Polr3g | 0.86 | 1.00 | 0.77 | 1.09 | 0.48 | 0.72 | 1.09 | 1.22 | 0.94 | 1.00 | 0.71 | 1.26 |
| Polrmt | 0.73 | 1.27 | 0.90 | 0.37 | 0.14 | 0.80 | 1.17 | 1.17 | 1.09 | 1.00 | 0.57 | 1.07 |
| Pom121 | 1.35 | 1.75 | 1.27 | 1.78 | 0.10 | 1.25 | 1.24 | 1.46 | 1.23 | 1.00 | 0.26 | 1.10 |
| Pou2f3 | 1.00 | 1.00 | 1.00 | 3.54 | 1.00 | 1.00 | 1.00 | 1.00 | 1.00 | 1.00 | 1.00 | 1.00 |
| Ppap2b | 1.21 | 1.95 | 1.28 | 1.30 | 0.19 | 0.74 | 0.80 | 0.81 | 0.87 | 0.31 | 0.23 | 0.91 |
| Ppapdc1b | 0.92 | 1.59 | 1.38 | 0.87 | 0.59 | 0.98 | 1.15 | 1.02 | 0.86 | 0.59 | 0.67 | 0.85 |
| Pparg | 1.00 | 1.97 | 1.50 | 1.14 | 0.67 | 1.28 | 0.86 | 0.85 | 1.09 | 0.21 | 0.45 | 0.76 |
| Pphln1 | 0.80 | 1.28 | 0.96 | 1.99 | 0.55 | 1.02 | 1.01 | 1.05 | 0.84 | 0.66 | 0.54 | 0.74 |
| Ppifos | 1.00 | 1.00 | 1.00 | 0.46 | 0.26 | 1.07 | 0.59 | 0.65 | 0.93 | 1.00 | 1.00 | 0.98 |
| Ppp1r14c | 0.51 | 0.93 | 0.43 | 1.00 | 1.00 | 1.00 | 0.30 | 0.36 | 0.45 | 0.25 | 0.26 | 0.54 |
| Ppp1r1a | 0.24 | 0.04 | 0.20 | 0.18 | 0.71 | 0.89 | 0.91 | 1.00 | 0.89 | 0.33 | 0.50 | 0.81 |
| Ppp1r2-ps3 | 0.84 | 1.63 | 0.76 | 1.83 | 0.18 | 1.20 | 1.16 | 0.96 | 1.31 | 0.61 | 0.20 | 1.18 |
| Ppp5c | 0.98 | 1.09 | 0.97 | 0.39 | 0.49 | 0.89 | 1.34 | 1.11 | 0.96 | 0.40 | 0.70 | 1.11 |
| Ppwd1 | 0.88 | 1.04 | 0.59 | 1.28 | 0.37 | 1.05 | 0.91 | 1.00 | 0.67 | 0.88 | 0.47 | 1.00 |
| Prcp | 0.78 | 1.00 | 1.34 | 1.31 | 0.61 | 1.03 | 0.77 | 0.86 | 1.01 | 0.19 | 0.31 | 0.76 |
| Prdm1 | 1.00 | 1.00 | 1.00 | 1.00 | 1.00 | 1.00 | 1.00 | 1.00 | 1.00 | 0.67 | 0.27 | 0.90 |
| Prdx3 | 0.91 | 1.25 | 0.82 | 0.90 | 0.81 | 0.99 | 0.85 | 0.93 | 0.81 | 0.44 | 0.62 | 0.97 |
| Prdx6b | 1.00 | 4.14 | 1.00 | 1.65 | 0.50 | 1.06 | 0.93 | 1.08 | 0.89 | 0.31 | 0.33 | 1.33 |
| Prep | 1.13 | 1.62 | 0.90 | 0.89 | 0.22 | 0.93 | 1.55 | 1.24 | 1.15 | 0.18 | 0.25 | 0.79 |
| Prex2 | 0.92 | 1.00 | 0.99 | 3.48 | 0.18 | 1.17 | 0.97 | 1.25 | 1.12 | 0.27 | 0.18 | 0.83 |
| Prkacb | 0.92 | 1.72 | 1.01 | 1.14 | 0.20 | 0.89 | 1.00 | 1.03 | 1.04 | 0.43 | 0.43 | 0.90 |
| Prkar1b | 1.00 | 1.30 | 0.99 | 0.86 | 0.11 | 0.85 | 0.91 | 0.80 | 1.13 | 1.34 | 1.11 | 1.10 |
| Prkar2a | 0.83 | 3.62 | 0.87 | 2.23 | 0.13 | 0.98 | 1.05 | 1.45 | 1.20 | 1.00 | 0.17 | 1.36 |
| Prkcb | 1.00 | 1.00 | 1.00 | 1.00 | 0.13 | 1.00 | 1.00 | 1.00 | 1.00 | 0.87 | 0.73 | 0.78 |
| Prkce | 0.60 | 1.14 | 0.95 | 0.91 | 0.13 | 0.93 | 0.68 | 0.93 | 0.82 | 0.79 | 0.54 | 1.04 |
| Prkch | 1.04 | 1.12 | 0.99 | 1.59 | 0.91 | 1.20 | 1.07 | 1.09 | 0.99 | 0.68 | 0.87 | 1.50 |
| Prkci | 0.84 | 1.00 | 1.11 | 1.79 | 0.43 | 0.89 | 0.91 | 1.14 | 1.11 | 0.42 | 0.40 | 1.08 |
| Prkx | 0.96 | 1.00 | 0.88 | 4.21 | 0.28 | 1.09 | 1.23 | 1.51 | 1.32 | 1.00 | 0.60 | 1.10 |
| Prom2 | 1.00 | 1.00 | 1.00 | 1.00 | 1.00 | 1.00 | 1.00 | 1.00 | 1.00 | 1.00 | 1.00 | 1.10 |
| Prr32 | 1.00 | 1.00 | 1.00 | 1.00 | 1.00 | 1.00 | 1.00 | 1.00 | 1.00 | 1.00 | 1.00 | 1.00 |
| Prrc2c | 0.97 | 2.00 | 1.27 | 1.71 | 0.38 | 0.95 | 1.17 | 1.54 | 1.36 | 0.84 | 0.52 | 0.98 |
| Prrt2 | 0.45 | 1.00 | 0.88 | 1.00 | 0.08 | 0.96 | 0.49 | 0.73 | 1.13 | 1.00 | 0.35 | 0.89 |
| Psd3 | 1.02 | 1.39 | 1.18 | 2.05 | 0.18 | 0.94 | 0.83 | 1.03 | 1.07 | 0.66 | 0.47 | 0.93 |
| Psmb11 | 1.00 | 1.00 | 1.00 | 1.00 | 1.00 | 1.00 | 1.00 | 1.00 | 1.00 | 1.00 | 1.00 | 1.00 |
| Pstpip2 | 1.28 | 3.96 | 1.26 | 1.00 | 1.00 | 1.05 | 1.00 | 1.14 | 0.88 | 1.00 | 1.00 | 1.23 |
| Ptbp2 | 0.82 | 1.47 | 0.99 | 3.49 | 0.71 | 1.17 | 0.91 | 1.22 | 1.02 | 0.53 | 0.43 | 0.86 |
| Ptch1 | 0.66 | 1.00 | 1.00 | 1.22 | 1.00 | 0.63 | 2.00 | 2.27 | 1.58 | 1.00 | 1.00 | 1.16 |
| Ptger1 | 0.91 | 0.76 | 1.07 | 0.19 | 0.31 | 0.51 | 1.46 | 1.21 | 1.02 | 1.31 | 1.66 | 0.89 |
| Ptger3 | 1.00 | 1.00 | 1.00 | 0.38 | 0.18 | 0.30 | 1.00 | 1.00 | 1.00 | 1.00 | 1.00 | 1.00 |
| Ptgs2 | 1.00 | 1.00 | 1.00 | 1.00 | 1.00 | 1.00 | 1.00 | 1.00 | 1.25 | 1.00 | 0.69 | 1.31 |
| Ptk7 | 1.00 | 1.00 | 1.00 | 1.00 | 1.00 | 1.00 | 0.83 | 0.79 | 0.94 | 0.20 | 0.18 | 0.96 |
| Ptn | 1.00 | 1.00 | 1.00 | 1.00 | 0.41 | 1.00 | 1.00 | 1.00 | 1.00 | 1.00 | 1.00 | 1.00 |
| Ptpn9 | 1.33 | 1.48 | 1.35 | 3.42 | 0.64 | 1.35 | 1.21 | 1.16 | 1.27 | 0.26 | 0.30 | 1.10 |
| Ptprb | 0.87 | 0.98 | 0.98 | 1.46 | 0.40 | 0.91 | 1.19 | 1.31 | 1.18 | 0.88 | 0.65 | 1.14 |
| Pura | 0.84 | 1.00 | 1.39 | 0.60 | 0.12 | 1.03 | 1.20 | 1.78 | 1.68 | 1.00 | 0.36 | 1.22 |
| Pvrl4 | 1.00 | 1.00 | 1.00 | 1.00 | 1.00 | 1.00 | 1.00 | 1.00 | 1.00 | 0.52 | 0.66 | 1.61 |
| Pxk | 1.19 | 2.25 | 1.08 | 1.56 | 0.91 | 1.55 | 1.11 | 0.99 | 0.90 | 0.38 | 0.43 | 0.91 |

Fig. 35- 74

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Plet1os | 1.00 | 1.00 | 1.00 | 1.00 | 1.00 | 1.00 | 0.92 | 1.69 | 1.00 | 1.00 | 1.00 | 1.00 |
| Plp2 | 1.02 | 1.49 | 1.02 | 0.53 | 1.54 | 0.77 | 0.59 | 1.00 | 1.00 | 0.81 | 1.09 | 0.96 |
| Plscr1 | 2.04 | 1.54 | 1.75 | 0.80 | 1.61 | 0.83 | 2.77 | 1.00 | 3.07 | 1.23 | 1.12 | 1.22 |
| Plscr2 | 1.56 | 0.77 | 1.04 | 0.88 | 2.49 | 0.83 | 1.85 | 1.00 | 1.26 | 0.16 | 0.14 | 0.19 |
| Plscr4 | 1.33 | 1.22 | 1.13 | 0.69 | 0.71 | 0.71 | 1.20 | 1.00 | 0.92 | 0.58 | 0.50 | 0.61 |
| Pltp | 1.77 | 1.65 | 1.64 | 0.48 | 1.00 | 0.42 | 1.22 | 1.00 | 1.20 | 0.72 | 0.81 | 0.87 |
| Plxna1 | 0.81 | 0.57 | 1.14 | 1.11 | 1.00 | 0.99 | 0.62 | 1.00 | 0.89 | 1.03 | 0.62 | 0.94 |
| Plxna2 | 0.78 | 0.57 | 0.99 | 1.41 | 1.00 | 1.21 | 0.59 | 1.00 | 0.64 | 0.87 | 0.73 | 0.84 |
| Pm20d2 | 1.00 | 1.00 | 1.00 | 1.05 | 1.00 | 0.99 | 0.71 | 1.00 | 1.08 | 1.19 | 0.60 | 1.06 |
| Pnisr | 0.84 | 0.72 | 0.95 | 1.03 | 1.04 | 0.89 | 0.92 | 0.71 | 0.92 | 1.00 | 0.68 | 0.98 |
| Pnmal2 | 0.89 | 0.70 | 0.78 | 0.79 | 0.65 | 0.74 | 1.00 | 1.00 | 1.00 | 0.84 | 0.97 | 0.97 |
| Pnp2 | 0.85 | 1.57 | 1.35 | 1.12 | 1.00 | 0.94 | 1.22 | 1.00 | 0.66 | 1.14 | 0.94 | 0.88 |
| Pnpla5 | 1.00 | 1.00 | 1.00 | 1.00 | 1.00 | 1.00 | 1.00 | 1.00 | 1.00 | 1.00 | 1.00 | 1.00 |
| Polh | 0.49 | 0.47 | 0.74 | 1.15 | 1.00 | 1.04 | 0.89 | 1.00 | 0.51 | 0.89 | 0.55 | 1.21 |
| Polm | 1.18 | 1.15 | 1.14 | 0.98 | 0.61 | 0.78 | 1.23 | 1.00 | 1.16 | 0.97 | 0.90 | 0.88 |
| Poln | 1.00 | 1.00 | 1.00 | 1.00 | 1.00 | 1.00 | 1.00 | 1.00 | 1.00 | 1.00 | 1.00 | 1.00 |
| Polr2i | 1.29 | 1.60 | 1.11 | 1.00 | 0.36 | 1.00 | 1.00 | 1.00 | 1.00 | 1.04 | 1.56 | 1.00 |
| Polr3g | 0.83 | 0.83 | 1.20 | 1.30 | 1.00 | 0.94 | 0.78 | 1.00 | 0.80 | 0.79 | 0.64 | 0.75 |
| Polrmt | 0.72 | 0.69 | 0.94 | 1.24 | 0.60 | 1.16 | 1.34 | 1.00 | 1.25 | 0.87 | 0.56 | 0.96 |
| Pom121 | 0.71 | 0.61 | 0.87 | 0.91 | 1.00 | 1.12 | 1.20 | 1.00 | 1.04 | 1.06 | 0.57 | 1.08 |
| Pou2f3 | 1.07 | 0.67 | 0.87 | 1.00 | 1.00 | 1.00 | 1.00 | 1.00 | 1.00 | 1.33 | 1.00 | 1.00 |
| Ppap2b | 1.80 | 1.35 | 1.45 | 0.91 | 1.48 | 0.97 | 0.59 | 0.30 | 1.00 | 0.98 | 0.80 | 1.06 |
| Ppapdc1b | 1.23 | 1.32 | 1.14 | 1.38 | 1.66 | 1.01 | 1.64 | 0.38 | 1.51 | 0.96 | 0.88 | 0.94 |
| Pparg | 1.13 | 1.15 | 1.03 | 0.26 | 1.00 | 0.34 | 1.09 | 1.00 | 1.00 | 1.24 | 1.39 | 1.02 |
| Pphln1 | 0.71 | 0.65 | 0.78 | 0.95 | 1.84 | 1.03 | 1.12 | 0.57 | 0.90 | 0.92 | 0.74 | 0.96 |
| Ppifos | 0.57 | 0.45 | 0.91 | 0.72 | 1.00 | 0.83 | 0.91 | 1.00 | 0.83 | 1.39 | 0.36 | 1.18 |
| Ppp1r14c | 0.97 | 0.80 | 1.00 | 1.00 | 1.00 | 1.00 | 1.00 | 1.00 | 1.00 | 1.00 | 1.00 | 1.03 |
| Ppp1r1a | 0.74 | 1.23 | 1.00 | 0.14 | 0.04 | 0.19 | 1.00 | 1.00 | 1.00 | 1.00 | 1.00 | 1.00 |
| Ppp1r2-ps3 | 1.49 | 1.18 | 1.27 | 1.00 | 1.00 | 1.30 | 1.35 | 1.00 | 1.10 | 1.12 | 0.79 | 0.82 |
| Ppp5c | 0.84 | 0.92 | 0.88 | 0.97 | 1.24 | 1.11 | 0.84 | 0.43 | 0.75 | 1.03 | 0.97 | 0.98 |
| Ppwd1 | 0.83 | 0.98 | 0.87 | 1.06 | 1.00 | 0.88 | 0.96 | 1.00 | 0.98 | 0.91 | 0.68 | 0.89 |
| Prcp | 1.24 | 1.18 | 1.42 | 0.86 | 0.99 | 0.99 | 0.58 | 1.00 | 0.77 | 0.98 | 1.05 | 1.07 |
| Prdm1 | 1.01 | 1.30 | 1.53 | 1.00 | 1.00 | 0.98 | 1.00 | 1.00 | 1.00 | 1.00 | 0.79 | 0.76 |
| Prdx3 | 1.02 | 1.12 | 0.99 | 0.90 | 1.44 | 0.88 | 1.12 | 0.48 | 0.93 | 1.10 | 1.13 | 1.06 |
| Prdx6b | 1.73 | 1.55 | 1.08 | 1.04 | 2.24 | 0.99 | 0.82 | 0.48 | 0.85 | 1.22 | 1.19 | 1.11 |
| Prep | 0.55 | 0.59 | 0.70 | 1.03 | 1.83 | 1.08 | 0.86 | 0.42 | 0.81 | 0.79 | 0.73 | 0.99 |
| Prex2 | 1.13 | 0.88 | 1.00 | 1.02 | 1.00 | 1.01 | 1.86 | 1.00 | 1.65 | 0.96 | 0.50 | 0.87 |
| Prkacb | 0.72 | 0.68 | 0.88 | 0.83 | 1.78 | 0.92 | 0.90 | 0.51 | 0.79 | 1.18 | 0.93 | 1.22 |
| Prkar1b | 1.65 | 1.46 | 1.58 | 0.66 | 0.81 | 0.86 | 1.00 | 1.00 | 1.00 | 1.12 | 1.05 | 1.25 |
| Prkar2a | 0.92 | 0.66 | 1.28 | 1.22 | 1.00 | 1.19 | 0.89 | 1.00 | 1.03 | 0.96 | 0.37 | 0.88 |
| Prkcb | 0.60 | 0.54 | 0.68 | 1.00 | 1.00 | 1.00 | 1.00 | 1.00 | 1.00 | 0.96 | 0.80 | 0.67 |
| Prkce | 1.07 | 0.87 | 1.19 | 1.11 | 1.05 | 1.23 | 0.95 | 1.00 | 1.01 | 1.02 | 0.75 | 1.01 |
| Prkch | 1.29 | 1.29 | 1.17 | 1.32 | 1.63 | 1.02 | 1.09 | 1.00 | 1.42 | 1.16 | 1.10 | 0.92 |
| Prkci | 1.02 | 0.88 | 1.26 | 0.97 | 1.92 | 1.02 | 0.85 | 1.00 | 0.94 | 0.84 | 0.55 | 0.90 |
| Prkx | 0.51 | 0.47 | 1.13 | 1.25 | 1.00 | 1.01 | 1.41 | 1.00 | 1.19 | 1.26 | 0.46 | 1.19 |
| Prom2 | 1.11 | 0.89 | 1.28 | 0.96 | 1.01 | 0.92 | 1.00 | 1.00 | 1.00 | 1.00 | 1.00 | 1.00 |
| Prr32 | 0.89 | 0.58 | 0.75 | 1.00 | 1.00 | 1.00 | 1.00 | 1.00 | 1.00 | 1.00 | 1.00 | 1.00 |
| Prrc2c | 0.77 | 0.77 | 0.91 | 1.20 | 1.15 | 1.13 | 1.05 | 1.00 | 1.07 | 1.09 | 0.67 | 0.81 |
| Prrt2 | 0.39 | 0.27 | 0.59 | 0.55 | 1.00 | 0.86 | 1.00 | 1.00 | 1.00 | 0.69 | 0.42 | 0.75 |
| Psd3 | 0.66 | 0.51 | 0.76 | 0.93 | 1.00 | 0.84 | 0.69 | 1.00 | 0.70 | 1.05 | 0.79 | 1.04 |
| Psmb11 | 0.13 | 0.15 | 0.35 | 1.00 | 1.00 | 1.00 | 1.00 | 1.00 | 1.00 | 1.00 | 1.00 | 1.00 |
| Pstpip2 | 0.62 | 0.46 | 1.05 | 1.08 | 1.00 | 1.32 | 0.96 | 1.00 | 0.90 | 0.91 | 0.53 | 0.85 |
| Ptbp2 | 0.97 | 1.09 | 0.85 | 1.12 | 1.33 | 1.11 | 1.04 | 0.65 | 0.91 | 0.94 | 0.86 | 1.08 |
| Ptch1 | 0.24 | 0.17 | 0.56 | 1.53 | 1.00 | 1.71 | 0.88 | 1.00 | 1.08 | 0.79 | 0.38 | 0.76 |
| Ptger1 | 0.72 | 0.72 | 0.84 | 0.83 | 1.05 | 0.98 | 1.37 | 2.15 | 1.01 | 1.02 | 0.66 | 0.94 |
| Ptger3 | 0.86 | 0.56 | 0.71 | 0.91 | 0.99 | 1.23 | 1.00 | 1.00 | 1.00 | 0.99 | 1.26 | 1.16 |
| Ptgs2 | 0.29 | 0.24 | 0.95 | 1.00 | 1.00 | 1.00 | 1.00 | 1.00 | 1.00 | 0.74 | 0.70 | 1.02 |
| Ptk7 | 1.19 | 1.12 | 1.18 | 0.85 | 1.00 | 0.99 | 1.00 | 1.00 | 1.00 | 0.81 | 0.73 | 0.96 |
| Ptn | 0.90 | 0.61 | 1.28 | 1.00 | 1.00 | 1.00 | 1.00 | 1.00 | 1.00 | 0.80 | 0.37 | 1.09 |
| Ptpn9 | 1.14 | 0.93 | 1.24 | 1.01 | 1.96 | 1.15 | 1.17 | 1.00 | 1.16 | 1.04 | 0.82 | 1.01 |
| Ptprb | 1.28 | 0.80 | 0.94 | 1.39 | 1.66 | 1.36 | 0.94 | 0.55 | 1.13 | 1.16 | 0.80 | 0.95 |
| Pura | 0.55 | 0.58 | 0.97 | 1.28 | 1.00 | 1.20 | 0.88 | 1.00 | 0.85 | 1.06 | 0.61 | 1.06 |
| Pvrl4 | 0.92 | 0.73 | 1.25 | 0.85 | 1.00 | 0.85 | 1.00 | 1.00 | 1.00 | 1.06 | 0.76 | 0.99 |
| Pxk | 0.85 | 0.93 | 0.94 | 0.91 | 1.77 | 0.88 | 2.51 | 2.03 | 1.94 | 0.70 | 0.64 | 0.70 |

Fig. 35- 75

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Plet1os | 1.00 | 1.00 | 1.00 | 1.00 | 1.00 | 1.00 | 1.00 | 1.00 | 1.00 | 1.00 | 1.00 | 1.00 |
| Plp2 | 0.84 | 0.82 | 0.98 | 0.73 | 0.35 | 0.71 | 0.69 | 1.00 | 0.61 | 1.15 | 1.00 | 1.04 |
| Plscr1 | 0.95 | 1.06 | 0.76 | 0.78 | 1.00 | 1.33 | 1.00 | 1.00 | 1.00 | 1.51 | 0.85 | 1.40 |
| Plscr2 | 0.89 | 0.80 | 1.08 | 0.58 | 1.00 | 0.68 | 1.00 | 1.00 | 1.00 | 1.74 | 1.90 | 1.72 |
| Plscr4 | 1.38 | 1.08 | 1.65 | 0.89 | 0.43 | 0.84 | 0.85 | 1.00 | 0.80 | 1.28 | 1.19 | 1.22 |
| Pltp | 0.64 | 0.75 | 1.60 | 0.55 | 0.66 | 0.63 | 0.60 | 1.00 | 0.86 | 0.91 | 1.01 | 1.12 |
| Plxna1 | 0.80 | 0.84 | 0.71 | 0.85 | 0.35 | 0.65 | 1.02 | 1.08 | 0.92 | 0.64 | 0.76 | 0.90 |
| Plxna2 | 0.86 | 0.79 | 0.67 | 1.10 | 0.18 | 0.97 | 1.17 | 1.17 | 1.17 | 0.91 | 1.83 | 1.02 |
| Pm20d2 | 0.89 | 0.85 | 0.92 | 0.32 | 1.00 | 0.64 | 1.22 | 1.00 | 0.82 | 1.00 | 1.00 | 1.00 |
| Pnisr | 1.05 | 1.02 | 1.09 | 0.91 | 0.23 | 1.00 | 1.00 | 0.65 | 0.98 | 1.05 | 0.74 | 1.06 |
| Pnmal2 | 1.00 | 1.12 | 1.17 | 1.21 | 1.24 | 1.72 | 1.27 | 1.98 | 1.20 | 0.91 | 4.31 | 1.17 |
| Pnp2 | 1.75 | 1.19 | 0.72 | 1.16 | 1.00 | 1.25 | 1.00 | 1.00 | 1.00 | 0.66 | 1.15 | 0.74 |
| Pnpla5 | 1.00 | 1.00 | 1.00 | 1.00 | 1.00 | 1.00 | 1.00 | 1.00 | 1.00 | 1.00 | 1.00 | 1.00 |
| Polh | 0.76 | 0.55 | 0.88 | 0.66 | 0.91 | 0.82 | 1.14 | 1.00 | 1.13 | 0.87 | 0.50 | 0.88 |
| Polm | 0.91 | 0.89 | 0.93 | 0.88 | 1.00 | 1.01 | 0.94 | 1.00 | 0.81 | 0.99 | 0.78 | 1.00 |
| Poln | 1.00 | 1.00 | 1.00 | 1.00 | 1.00 | 1.00 | 0.97 | 1.18 | 1.25 | 1.00 | 1.00 | 1.00 |
| Polr2i | 1.00 | 1.00 | 1.00 | 1.00 | 1.00 | 1.00 | 1.00 | 1.63 | 1.14 | 1.00 | 1.00 | 1.02 |
| Polr3g | 0.82 | 0.76 | 0.84 | 0.48 | 1.00 | 0.70 | 1.01 | 0.67 | 0.81 | 0.91 | 0.89 | 0.95 |
| Polrmt | 0.92 | 1.11 | 0.81 | 0.90 | 1.00 | 0.99 | 1.11 | 1.00 | 1.02 | 0.83 | 0.79 | 1.06 |
| Pom121 | 0.95 | 0.98 | 0.85 | 1.27 | 0.37 | 1.28 | 1.02 | 1.07 | 1.08 | 1.06 | 0.74 | 1.02 |
| Pou2f3 | 1.40 | 0.78 | 0.99 | 1.35 | 1.00 | 1.00 | 1.00 | 0.86 | 1.00 | 1.00 | 1.00 | 1.00 |
| Ppap2b | 0.89 | 0.99 | 1.24 | 0.82 | 0.14 | 0.88 | 1.06 | 0.56 | 0.99 | 0.77 | 0.96 | 0.90 |
| Ppapdc1b | 0.94 | 0.86 | 0.88 | 1.09 | 0.27 | 1.03 | 0.91 | 1.00 | 0.92 | 1.25 | 0.92 | 0.88 |
| Pparg | 0.65 | 0.64 | 0.64 | 0.71 | 0.28 | 1.16 | 0.53 | 1.00 | 0.67 | 0.93 | 0.91 | 0.80 |
| Pphln1 | 0.88 | 0.81 | 0.94 | 1.06 | 0.63 | 1.11 | 1.15 | 0.87 | 0.94 | 1.05 | 0.72 | 1.10 |
| Ppifos | 0.80 | 0.82 | 0.81 | 1.02 | 1.00 | 0.95 | 1.07 | 1.29 | 0.76 | 1.01 | 0.50 | 1.16 |
| Ppp1r14c | 1.26 | 0.98 | 1.65 | 1.00 | 1.00 | 1.00 | 1.00 | 1.00 | 1.00 | 1.00 | 1.00 | 1.00 |
| Ppp1r1a | 1.00 | 1.00 | 1.00 | 0.21 | 0.15 | 0.75 | 1.00 | 1.00 | 1.00 | 1.16 | 2.47 | 1.10 |
| Ppp1r2-ps3 | 1.21 | 1.21 | 0.86 | 1.33 | 0.53 | 1.51 | 1.38 | 1.03 | 1.73 | 1.20 | 0.84 | 0.93 |
| Ppp5c | 1.03 | 1.03 | 0.92 | 1.10 | 1.71 | 1.03 | 0.99 | 0.38 | 1.13 | 1.12 | 1.18 | 0.93 |
| Ppwd1 | 0.78 | 0.88 | 0.78 | 0.74 | 1.00 | 1.01 | 0.94 | 0.65 | 1.02 | 1.30 | 0.78 | 0.92 |
| Prcp | 1.05 | 0.97 | 1.02 | 0.72 | 1.00 | 0.74 | 0.75 | 1.08 | 1.10 | 0.89 | 0.92 | 0.96 |
| Prdm1 | 0.96 | 1.00 | 0.92 | 1.00 | 1.00 | 0.69 | 1.00 | 1.00 | 1.00 | 1.41 | 1.27 | 1.46 |
| Prdx3 | 1.00 | 0.87 | 1.04 | 0.93 | 0.56 | 1.10 | 0.68 | 0.20 | 0.77 | 0.97 | 0.96 | 0.93 |
| Prdx6b | 1.05 | 1.08 | 0.92 | 1.08 | 0.17 | 0.91 | 0.96 | 0.72 | 0.99 | 1.24 | 1.33 | 0.97 |
| Prep | 0.90 | 0.76 | 0.76 | 1.09 | 0.79 | 1.00 | 0.90 | 1.00 | 0.88 | 0.91 | 0.71 | 0.92 |
| Prex2 | 0.98 | 1.03 | 0.86 | 0.86 | 0.50 | 0.60 | 1.00 | 1.00 | 1.00 | 1.25 | 0.96 | 1.11 |
| Prkacb | 1.02 | 0.87 | 0.97 | 0.91 | 0.44 | 0.93 | 1.05 | 1.00 | 0.90 | 1.00 | 0.89 | 0.99 |
| Prkar1b | 1.07 | 1.31 | 1.16 | 1.28 | 0.64 | 1.15 | 1.06 | 1.48 | 0.83 | 0.82 | 4.52 | 0.79 |
| Prkar2a | 0.90 | 0.82 | 0.71 | 1.36 | 0.31 | 0.92 | 0.94 | 1.47 | 1.04 | 0.80 | 0.68 | 0.99 |
| Prkcb | 0.94 | 0.81 | 0.83 | 0.88 | 1.00 | 0.56 | 0.97 | 1.00 | 0.73 | 0.83 | 0.78 | 1.08 |
| Prkce | 1.42 | 1.15 | 1.36 | 0.69 | 0.38 | 0.73 | 1.04 | 1.00 | 1.26 | 1.15 | 1.73 | 1.33 |
| Prkch | 1.15 | 1.32 | 1.14 | 1.18 | 0.96 | 1.15 | 1.34 | 1.00 | 0.85 | 0.94 | 1.00 | 0.92 |
| Prkci | 0.93 | 0.77 | 0.87 | 0.71 | 0.53 | 0.69 | 0.92 | 0.88 | 0.91 | 0.94 | 0.87 | 1.13 |
| Prkx | 1.07 | 0.96 | 0.75 | 1.08 | 0.28 | 0.74 | 1.26 | 1.00 | 1.43 | 0.97 | 0.43 | 0.95 |
| Prom2 | 0.77 | 0.90 | 0.94 | 1.01 | 1.00 | 0.23 | 1.00 | 1.00 | 1.00 | 1.00 | 1.00 | 1.00 |
| Prr32 | 1.00 | 1.00 | 1.00 | 0.16 | 1.00 | 0.10 | 1.11 | 0.26 | 0.91 | 1.00 | 1.00 | 1.00 |
| Prrc2c | 0.94 | 0.98 | 0.74 | 1.18 | 0.14 | 0.83 | 1.12 | 1.64 | 1.13 | 1.08 | 0.74 | 1.16 |
| Prrt2 | 0.53 | 0.71 | 0.89 | 0.66 | 0.76 | 0.76 | 0.78 | 1.00 | 0.64 | 0.50 | 1.83 | 0.85 |
| Psd3 | 1.29 | 1.21 | 0.90 | 0.93 | 0.58 | 0.75 | 0.94 | 0.79 | 0.96 | 1.07 | 2.84 | 1.08 |
| Psmb11 | 1.00 | 1.00 | 1.00 | 1.00 | 1.00 | 1.00 | 1.00 | 1.00 | 1.00 | 1.00 | 1.00 | 1.00 |
| Pstpip2 | 1.28 | 1.05 | 1.34 | 1.06 | 1.00 | 0.80 | 1.19 | 1.00 | 1.17 | 0.90 | 0.78 | 1.19 |
| Ptbp2 | 1.10 | 1.13 | 1.19 | 1.25 | 0.63 | 1.18 | 0.98 | 0.30 | 0.99 | 1.26 | 1.20 | 1.05 |
| Ptch1 | 0.86 | 0.89 | 0.67 | 1.21 | 0.51 | 0.26 | 0.93 | 1.00 | 0.81 | 0.80 | 0.54 | 1.20 |
| Ptger1 | 0.95 | 1.22 | 0.76 | 1.27 | 1.20 | 0.99 | 1.15 | 1.11 | 0.92 | 0.97 | 0.79 | 0.86 |
| Ptger3 | 0.87 | 0.67 | 0.69 | 0.20 | 1.00 | 0.16 | 1.00 | 1.00 | 1.00 | 1.39 | 0.66 | 0.68 |
| Ptgs2 | 0.81 | 0.64 | 0.88 | 1.00 | 0.27 | 0.19 | 1.00 | 1.00 | 1.00 | 1.00 | 1.00 | 1.00 |
| Ptk7 | 0.87 | 1.00 | 1.10 | 0.85 | 1.00 | 1.36 | 0.90 | 1.00 | 1.18 | 0.88 | 0.92 | 0.97 |
| Ptn | 0.64 | 0.87 | 1.19 | 0.80 | 1.00 | 1.04 | 1.00 | 1.00 | 1.00 | 1.00 | 4.33 | 1.00 |
| Ptpn9 | 1.12 | 1.02 | 0.84 | 1.54 | 0.32 | 1.29 | 1.07 | 0.62 | 0.96 | 1.06 | 0.73 | 0.93 |
| Ptprb | 1.28 | 1.50 | 1.12 | 0.86 | 0.14 | 0.68 | 1.00 | 1.00 | 1.00 | 1.08 | 0.79 | 1.16 |
| Pura | 0.94 | 0.95 | 0.71 | 1.27 | 0.35 | 1.11 | 1.01 | 1.42 | 0.99 | 0.85 | 0.59 | 1.15 |
| Pvrl4 | 1.12 | 1.25 | 1.07 | 1.66 | 1.00 | 1.83 | 0.63 | 0.75 | 0.69 | 1.70 | 1.05 | 1.29 |
| Pxk | 0.81 | 0.97 | 0.80 | 1.39 | 1.81 | 1.54 | 1.04 | 2.36 | 0.91 | 0.79 | 0.59 | 0.67 |

Fig. 35- 76

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Plet1os | 1.00 | 1.00 | 1.00 | 1.00 | 0.21 | 1.00 | 1.00 | 1.00 | 1.00 | 1.00 | 1.00 | 1.00 |
| Plp2 | 0.93 | 0.89 | 0.75 | 0.85 | 1.00 | 1.23 | 0.99 | 0.09 | 0.80 | 0.59 | 1.38 | 1.33 |
| Plscr1 | 1.00 | 1.00 | 1.00 | 1.00 | 1.00 | 1.00 | 1.00 | 1.00 | 1.00 | 0.66 | 1.44 | 1.46 |
| Plscr2 | 1.00 | 0.97 | 1.00 | 0.63 | 1.00 | 0.94 | 1.00 | 1.00 | 1.00 | 1.00 | 1.00 | 1.00 |
| Plscr4 | 1.00 | 1.00 | 1.00 | 1.06 | 1.00 | 1.00 | 0.81 | 0.14 | 1.06 | 0.88 | 0.87 | 0.99 |
| Pltp | 0.57 | 1.00 | 0.99 | 0.62 | 0.31 | 0.75 | 1.21 | 0.10 | 1.09 | 0.72 | 0.74 | 0.85 |
| Plxna1 | 0.78 | 0.91 | 0.84 | 0.97 | 1.58 | 0.99 | 0.79 | 0.24 | 1.01 | 1.00 | 0.57 | 0.72 |
| Plxna2 | 0.79 | 0.85 | 0.92 | 1.00 | 1.72 | 0.98 | 0.93 | 0.33 | 1.02 | 1.00 | 1.00 | 1.00 |
| Pm20d2 | 0.63 | 0.95 | 0.82 | 0.97 | 1.00 | 1.08 | 0.64 | 0.14 | 0.92 | 1.00 | 1.00 | 1.00 |
| Pnisr | 0.93 | 0.73 | 1.10 | 0.93 | 1.17 | 0.95 | 0.98 | 0.07 | 1.07 | 0.41 | 0.98 | 0.84 |
| Pnmal2 | 0.89 | 0.72 | 1.00 | 1.08 | 0.99 | 0.98 | 0.90 | 1.00 | 1.00 | 1.00 | 1.00 | 1.00 |
| Pnp2 | 1.00 | 1.00 | 1.00 | 1.00 | 1.00 | 0.98 | 1.65 | 1.00 | 1.52 | 0.46 | 1.16 | 1.22 |
| Pnpla5 | 1.00 | 1.00 | 1.00 | 1.00 | 1.00 | 1.00 | 1.46 | 0.12 | 1.20 | 1.00 | 1.00 | 1.00 |
| Polh | 1.00 | 1.00 | 1.00 | 1.33 | 1.00 | 0.93 | 0.60 | 0.18 | 0.80 | 0.26 | 0.76 | 0.81 |
| Polm | 0.93 | 0.82 | 1.08 | 1.05 | 1.00 | 1.17 | 0.88 | 0.16 | 0.93 | 0.51 | 0.96 | 1.21 |
| Poln | 1.00 | 1.00 | 1.00 | 1.00 | 1.00 | 1.00 | 1.00 | 2.82 | 1.00 | 1.00 | 1.00 | 1.00 |
| Polr2i | 1.00 | 1.00 | 1.00 | 1.00 | 1.00 | 1.12 | 2.40 | 3.15 | 1.78 | 1.00 | 0.69 | 1.00 |
| Polr3g | 1.00 | 0.77 | 0.91 | 0.92 | 1.00 | 0.94 | 0.71 | 0.20 | 0.84 | 0.63 | 0.97 | 0.76 |
| Polrmt | 1.10 | 0.99 | 1.27 | 1.05 | 1.00 | 0.89 | 1.07 | 0.27 | 0.97 | 1.00 | 0.83 | 0.81 |
| Pom121 | 1.06 | 1.00 | 1.10 | 1.06 | 1.00 | 1.03 | 1.00 | 0.08 | 1.12 | 0.19 | 0.79 | 0.81 |
| Pou2f3 | 1.00 | 1.00 | 1.00 | 1.00 | 1.00 | 1.00 | 0.58 | 0.15 | 0.65 | 1.00 | 1.00 | 1.00 |
| Ppap2b | 1.02 | 0.84 | 1.03 | 0.81 | 0.44 | 0.86 | 0.99 | 0.16 | 1.38 | 0.78 | 0.64 | 0.90 |
| Ppapdc1b | 0.82 | 0.84 | 0.88 | 1.13 | 1.18 | 1.11 | 1.05 | 0.19 | 1.02 | 0.42 | 1.04 | 0.99 |
| Pparg | 1.00 | 1.00 | 1.00 | 1.23 | 1.00 | 1.43 | 0.95 | 0.10 | 1.01 | 0.56 | 0.56 | 0.64 |
| Pphln1 | 1.05 | 0.87 | 1.08 | 1.03 | 2.56 | 1.02 | 0.78 | 0.17 | 1.03 | 0.66 | 0.83 | 0.97 |
| Ppifos | 1.00 | 1.00 | 1.00 | 1.00 | 1.00 | 0.68 | 0.59 | 0.10 | 0.67 | 1.00 | 0.43 | 0.70 |
| Ppp1r14c | 1.00 | 1.00 | 1.00 | 0.93 | 1.24 | 0.98 | 0.65 | 0.15 | 0.76 | 1.00 | 1.00 | 1.00 |
| Ppp1r1a | 1.00 | 1.00 | 1.00 | 0.64 | 0.11 | 0.58 | 2.74 | 0.62 | 2.03 | 1.00 | 1.42 | 1.00 |
| Ppp1r2-ps3 | 0.87 | 1.33 | 1.00 | 1.40 | 1.00 | 0.86 | 0.86 | 0.14 | 0.96 | 0.63 | 1.17 | 1.20 |
| Ppp5c | 0.78 | 0.69 | 0.81 | 1.05 | 0.67 | 1.03 | 0.85 | 0.15 | 0.81 | 0.70 | 0.82 | 0.90 |
| Ppwd1 | 1.00 | 1.00 | 1.00 | 1.28 | 1.00 | 0.97 | 0.70 | 0.20 | 0.88 | 0.46 | 0.74 | 0.88 |
| Prcp | 1.00 | 1.00 | 1.00 | 1.00 | 1.00 | 0.79 | 0.97 | 0.29 | 1.05 | 0.48 | 0.88 | 1.02 |
| Prdm1 | 1.00 | 1.00 | 1.00 | 1.00 | 1.00 | 1.00 | 0.82 | 0.16 | 0.78 | 1.00 | 1.92 | 1.22 |
| Prdx3 | 1.05 | 0.89 | 0.89 | 1.02 | 3.49 | 0.97 | 1.28 | 0.42 | 1.23 | 0.43 | 0.89 | 0.96 |
| Prdx6b | 0.92 | 0.56 | 0.68 | 1.01 | 0.30 | 0.98 | 0.92 | 0.13 | 0.85 | 0.64 | 1.35 | 1.05 |
| Prep | 1.32 | 1.35 | 1.34 | 0.98 | 1.00 | 0.86 | 0.82 | 0.23 | 0.77 | 0.48 | 0.84 | 1.03 |
| Prex2 | 1.00 | 1.00 | 1.00 | 0.78 | 1.00 | 0.90 | 0.98 | 0.90 | 1.37 | 1.00 | 1.00 | 1.00 |
| Prkacb | 0.83 | 1.04 | 0.87 | 1.04 | 0.96 | 0.99 | 0.69 | 0.13 | 0.96 | 0.45 | 0.84 | 0.90 |
| Prkar1b | 1.00 | 1.00 | 1.00 | 1.09 | 0.96 | 1.05 | 0.91 | 2.02 | 0.74 | 1.00 | 1.00 | 1.00 |
| Prkar2a | 1.17 | 1.00 | 1.15 | 0.96 | 1.00 | 0.99 | 0.79 | 0.07 | 0.93 | 1.00 | 0.76 | 0.66 |
| Prkcb | 1.00 | 1.00 | 1.00 | 0.91 | 1.32 | 0.98 | 1.12 | 0.77 | 0.97 | 1.22 | 0.97 | 1.05 |
| Prkce | 1.11 | 1.05 | 1.16 | 1.03 | 1.89 | 0.99 | 1.03 | 0.68 | 1.27 | 0.62 | 0.95 | 1.00 |
| Prkch | 1.00 | 1.00 | 1.00 | 0.93 | 1.00 | 0.87 | 0.81 | 0.19 | 0.89 | 0.65 | 1.39 | 1.11 |
| Prkci | 0.68 | 0.85 | 0.76 | 0.96 | 1.01 | 0.92 | 0.74 | 0.13 | 0.96 | 0.71 | 1.07 | 1.11 |
| Prkx | 1.35 | 1.00 | 1.00 | 0.95 | 1.00 | 0.79 | 0.82 | 0.12 | 1.02 | 1.00 | 0.85 | 0.82 |
| Prom2 | 1.93 | 2.60 | 1.81 | 1.00 | 1.00 | 1.00 | 0.76 | 0.16 | 0.71 | 1.00 | 1.00 | 1.00 |
| Prr32 | 1.00 | 1.00 | 1.00 | 1.22 | 0.21 | 0.78 | 1.00 | 1.00 | 1.00 | 1.00 | 1.00 | 1.00 |
| Prrc2c | 1.01 | 1.16 | 1.27 | 0.85 | 0.42 | 0.90 | 0.86 | 0.23 | 1.05 | 0.68 | 0.97 | 0.89 |
| Prrt2 | 1.00 | 1.00 | 1.00 | 0.95 | 0.90 | 0.92 | 0.64 | 0.16 | 1.06 | 1.00 | 0.80 | 0.89 |
| Psd3 | 1.00 | 1.00 | 1.00 | 0.87 | 0.95 | 0.86 | 0.75 | 0.25 | 0.88 | 1.00 | 0.69 | 0.78 |
| Psmb11 | 1.00 | 1.00 | 1.00 | 1.00 | 0.88 | 1.00 | 1.00 | 1.00 | 1.00 | 1.00 | 1.00 | 1.00 |
| Pstpip2 | 1.00 | 1.00 | 1.00 | 1.18 | 1.00 | 1.18 | 1.29 | 0.17 | 1.20 | 0.23 | 0.96 | 1.00 |
| Ptbp2 | 1.42 | 0.90 | 1.00 | 1.01 | 2.29 | 0.99 | 1.00 | 0.12 | 1.35 | 0.51 | 1.40 | 0.99 |
| Ptch1 | 1.00 | 1.00 | 1.00 | 0.78 | 1.00 | 0.80 | 0.67 | 1.00 | 1.16 | 1.00 | 1.00 | 1.00 |
| Ptger1 | 1.19 | 1.42 | 1.09 | 0.93 | 0.61 | 0.85 | 1.44 | 0.71 | 1.60 | 1.89 | 1.37 | 0.95 |
| Ptger3 | 0.73 | 0.67 | 0.81 | 1.00 | 1.00 | 1.20 | 1.02 | 0.52 | 1.18 | 0.52 | 1.71 | 0.96 |
| Ptgs2 | 1.00 | 1.00 | 1.00 | 1.25 | 1.00 | 1.17 | 1.00 | 1.00 | 1.00 | 1.00 | 1.00 | 1.00 |
| Ptk7 | 0.77 | 1.38 | 1.58 | 0.97 | 1.00 | 1.02 | 0.79 | 0.05 | 0.82 | 1.00 | 1.00 | 1.00 |
| Ptn | 1.00 | 1.00 | 1.00 | 0.90 | 1.00 | 0.88 | 0.82 | 0.16 | 0.85 | 1.00 | 1.00 | 1.00 |
| Ptpn9 | 1.21 | 1.73 | 1.06 | 1.04 | 1.00 | 1.04 | 0.84 | 0.11 | 1.05 | 0.39 | 1.03 | 1.08 |
| Ptprb | 1.10 | 1.25 | 1.28 | 0.73 | 0.71 | 0.77 | 1.49 | 1.00 | 1.50 | 1.00 | 1.00 | 1.00 |
| Pura | 1.37 | 1.11 | 1.43 | 0.85 | 1.52 | 0.83 | 1.06 | 0.09 | 1.20 | 0.71 | 0.71 | 0.70 |
| Pvrl4 | 1.00 | 1.00 | 1.00 | 1.38 | 1.00 | 1.34 | 0.96 | 0.09 | 0.67 | 1.00 | 1.66 | 2.33 |
| Pxk | 1.16 | 1.11 | 0.93 | 1.18 | 1.00 | 1.01 | 1.28 | 0.09 | 1.28 | 0.36 | 0.81 | 0.78 |

Fig. 35- 77

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Pxt1 | 1.00 | 1.00 | 1.00 | 1.03 | 1.00 | 1.00 | 1.00 | 1.00 | 1.00 | 1.00 | 1.00 | 1.00 |
| Qpct | 0.68 | 0.78 | 0.95 | 0.72 | 0.65 | 0.89 | 0.44 | 0.50 | 0.59 | 0.55 | 0.47 | 1.10 |
| Qtrtd1 | 0.98 | 1.27 | 0.99 | 1.55 | 0.44 | 1.10 | 0.80 | 1.02 | 0.78 | 0.52 | 0.90 | 0.88 |
| Rab11fip2 | 0.89 | 2.24 | 1.17 | 4.39 | 0.58 | 1.06 | 1.23 | 1.37 | 1.22 | 0.46 | 0.35 | 0.98 |
| Rab11fip4 | 1.00 | 1.00 | 1.00 | 1.00 | 0.55 | 1.00 | 1.00 | 1.00 | 1.00 | 1.00 | 1.00 | 1.07 |
| Rab12 | 1.08 | 2.01 | 1.03 | 1.17 | 0.25 | 0.95 | 1.07 | 1.10 | 0.98 | 0.32 | 0.29 | 1.07 |
| Rab20 | 2.13 | 2.81 | 2.06 | 1.44 | 0.34 | 1.69 | 1.13 | 1.18 | 1.09 | 0.21 | 0.08 | 1.34 |
| Rab32 | 0.95 | 1.00 | 0.76 | 1.34 | 0.86 | 1.62 | 0.85 | 1.04 | 1.01 | 0.41 | 0.58 | 1.04 |
| Rab5c | 1.12 | 1.67 | 0.89 | 0.59 | 0.30 | 0.84 | 0.97 | 0.83 | 0.98 | 0.22 | 0.43 | 0.93 |
| Rad21 | 0.92 | 1.39 | 0.98 | 2.74 | 0.69 | 1.24 | 0.93 | 1.14 | 1.03 | 0.44 | 0.46 | 0.98 |
| Raet1e | 1.00 | 1.00 | 1.00 | 1.00 | 1.00 | 1.00 | 1.00 | 1.00 | 1.00 | 1.00 | 0.42 | 0.42 |
| Rai1 | 0.75 | 1.11 | 0.87 | 1.23 | 0.20 | 0.91 | 0.87 | 0.96 | 1.39 | 0.46 | 0.28 | 1.10 |
| Rai14 | 0.87 | 2.21 | 0.81 | 2.27 | 1.01 | 1.22 | 1.27 | 1.72 | 1.22 | 0.45 | 0.61 | 1.13 |
| Ranbp2 | 1.21 | 2.81 | 1.23 | 2.92 | 0.26 | 1.03 | 1.10 | 1.54 | 1.42 | 0.54 | 0.38 | 1.06 |
| Rasgrp1 | 1.00 | 1.00 | 1.00 | 1.00 | 0.17 | 1.00 | 1.00 | 1.00 | 1.00 | 1.00 | 0.53 | 0.61 |
| Rasgrp3 | 0.49 | 0.72 | 0.40 | 0.85 | 0.23 | 0.51 | 0.71 | 0.80 | 0.93 | 0.21 | 0.18 | 0.63 |
| Rasl2-9 | 1.08 | 1.51 | 1.13 | 0.64 | 0.21 | 1.11 | 1.11 | 0.97 | 0.90 | 0.95 | 0.21 | 1.15 |
| Rassf3 | 1.28 | 2.02 | 1.32 | 1.55 | 0.43 | 1.39 | 0.84 | 0.94 | 0.88 | 0.52 | 0.44 | 1.14 |
| Rassf6 | 1.00 | 1.00 | 1.00 | 0.98 | 1.20 | 0.91 | 1.00 | 1.00 | 1.00 | 0.54 | 1.20 | 1.03 |
| Rbbp9 | 0.68 | 1.50 | 0.88 | 1.65 | 0.28 | 0.95 | 0.90 | 0.93 | 0.77 | 0.48 | 0.26 | 0.96 |
| Rbfox2 | 0.53 | 0.84 | 0.60 | 1.01 | 0.16 | 0.88 | 0.82 | 0.78 | 0.89 | 0.73 | 0.28 | 0.93 |
| Rbl2 | 0.89 | 2.77 | 1.18 | 2.17 | 0.26 | 1.29 | 1.36 | 1.40 | 1.01 | 0.34 | 0.19 | 1.07 |
| Rbm12 | 1.12 | 1.37 | 1.30 | 1.95 | 0.65 | 1.07 | 0.98 | 1.18 | 1.07 | 0.68 | 0.49 | 0.92 |
| Rbm15b | 1.33 | 1.00 | 1.24 | 1.48 | 0.25 | 1.01 | 1.34 | 1.56 | 1.59 | 0.63 | 0.37 | 1.21 |
| Rbms1 | 0.92 | 0.90 | 0.86 | 2.79 | 0.65 | 1.15 | 0.97 | 1.35 | 1.28 | 0.78 | 0.50 | 1.01 |
| Rbmx2 | 0.69 | 0.84 | 0.55 | 0.43 | 1.20 | 1.03 | 0.87 | 0.95 | 0.65 | 0.34 | 0.90 | 0.72 |
| Rcn2 | 0.91 | 1.65 | 0.93 | 1.19 | 0.31 | 1.10 | 0.95 | 0.79 | 0.82 | 0.22 | 0.23 | 0.86 |
| Rcor1 | 0.62 | 1.00 | 1.11 | 1.83 | 0.40 | 0.85 | 0.93 | 1.58 | 1.49 | 1.00 | 1.00 | 1.08 |
| Rdh10 | 0.83 | 1.00 | 1.05 | 1.14 | 0.38 | 1.17 | 1.04 | 0.92 | 1.03 | 0.74 | 0.35 | 0.81 |
| Reck | 0.70 | 1.00 | 0.98 | 1.14 | 0.90 | 0.94 | 0.67 | 0.62 | 0.77 | 0.24 | 0.15 | 0.74 |
| Reep3 | 1.36 | 2.54 | 1.16 | 1.84 | 0.45 | 1.15 | 1.01 | 1.09 | 1.00 | 0.39 | 0.34 | 0.97 |
| Rere | 1.13 | 1.69 | 0.94 | 1.68 | 0.34 | 0.92 | 1.28 | 1.45 | 1.09 | 0.36 | 0.32 | 0.85 |
| Rest | 0.61 | 1.00 | 2.18 | 1.48 | 1.00 | 0.80 | 1.50 | 2.68 | 2.63 | 1.00 | 1.00 | 1.14 |
| Rfesd | 0.93 | 1.12 | 0.80 | 0.76 | 1.76 | 0.85 | 1.14 | 0.76 | 0.87 | 0.79 | 1.61 | 1.01 |
| Rgmb | 0.74 | 1.49 | 0.98 | 1.12 | 0.15 | 0.98 | 0.89 | 1.47 | 1.09 | 0.40 | 0.23 | 1.09 |
| Rgn | 1.00 | 1.00 | 1.00 | 1.00 | 1.00 | 1.00 | 1.00 | 1.00 | 1.00 | 1.00 | 1.00 | 1.00 |
| Rgs20 | 1.00 | 1.00 | 1.00 | 1.00 | 1.00 | 1.00 | 1.00 | 1.00 | 1.00 | 1.00 | 1.00 | 1.00 |
| Rgs4 | 0.50 | 0.73 | 0.70 | 1.11 | 0.14 | 0.92 | 0.60 | 0.65 | 0.75 | 0.44 | 0.32 | 0.69 |
| Rhbdf2 | 2.02 | 2.21 | 1.36 | 1.00 | 0.83 | 1.10 | 1.29 | 1.34 | 0.81 | 0.41 | 0.64 | 1.08 |
| Rhbdl1 | 0.81 | 0.53 | 0.54 | 0.19 | 1.01 | 0.75 | 0.87 | 0.24 | 0.83 | 1.39 | 2.04 | 0.90 |
| Rhbdl2 | 1.00 | 1.00 | 1.00 | 1.00 | 1.00 | 1.00 | 1.00 | 1.00 | 1.00 | 1.00 | 1.00 | 1.00 |
| Rhbdl3 | 0.82 | 1.31 | 0.62 | 1.00 | 1.00 | 0.98 | 0.57 | 0.55 | 0.94 | 1.00 | 0.79 | 0.80 |
| Rhd | 1.00 | 1.00 | 1.00 | 1.00 | 1.00 | 1.00 | 1.06 | 0.72 | 1.10 | 1.00 | 1.40 | 1.00 |
| Rheb | 1.37 | 2.55 | 1.01 | 1.03 | 0.45 | 1.13 | 0.95 | 0.97 | 0.95 | 0.19 | 0.33 | 0.89 |
| Rian | 1.11 | 1.00 | 0.83 | 0.87 | 0.14 | 1.15 | 0.71 | 0.72 | 0.91 | 1.00 | 1.00 | 1.00 |
| Rictor | 1.02 | 2.51 | 1.08 | 3.42 | 0.38 | 1.02 | 1.06 | 1.14 | 1.21 | 0.46 | 0.45 | 1.01 |
| Rilpl2 | 1.26 | 0.85 | 0.93 | 0.14 | 0.88 | 0.89 | 1.38 | 1.09 | 0.95 | 1.03 | 1.35 | 1.01 |
| Rin1 | 1.00 | 1.00 | 1.00 | 1.12 | 0.51 | 0.85 | 1.49 | 1.50 | 1.97 | 1.00 | 0.91 | 1.66 |
| Ripk2 | 0.79 | 1.28 | 1.52 | 1.41 | 1.00 | 0.94 | 1.08 | 0.62 | 1.25 | 0.30 | 0.55 | 0.95 |
| Ripply3 | 1.94 | 1.24 | 1.26 | 0.85 | 0.24 | 0.82 | 0.98 | 0.91 | 0.78 | 0.31 | 0.18 | 0.72 |
| Rlf | 1.07 | 1.49 | 1.08 | 2.40 | 0.37 | 1.26 | 1.66 | 2.00 | 1.40 | 0.67 | 0.42 | 0.93 |
| Rnase4 | 1.39 | 2.32 | 1.31 | 2.14 | 0.57 | 1.27 | 1.24 | 1.07 | 1.31 | 0.34 | 0.31 | 1.05 |
| Rnase6 | 1.00 | 1.00 | 1.37 | 1.00 | 1.00 | 1.00 | 1.00 | 1.00 | 1.00 | 0.18 | 0.17 | 0.47 |
| Rnase9 | 1.00 | 1.00 | 1.00 | 1.00 | 1.00 | 1.00 | 1.00 | 1.00 | 1.00 | 1.00 | 1.00 | 1.00 |
| Rnd3 | 1.04 | 1.96 | 1.04 | 1.80 | 0.41 | 1.00 | 0.73 | 0.76 | 1.03 | 0.51 | 0.19 | 0.79 |
| Rnf10 | 0.98 | 1.53 | 0.97 | 0.81 | 0.20 | 0.82 | 1.19 | 1.23 | 1.08 | 0.52 | 0.35 | 1.07 |
| Rnf11 | 0.92 | 2.19 | 0.77 | 1.04 | 0.11 | 0.76 | 0.78 | 0.92 | 0.86 | 0.37 | 0.22 | 0.92 |
| Rnf145 | 0.65 | 1.60 | 1.15 | 1.04 | 0.32 | 1.07 | 0.92 | 0.95 | 1.00 | 0.46 | 0.42 | 0.91 |
| Rnf146 | 1.08 | 1.84 | 1.01 | 1.06 | 0.27 | 0.79 | 1.00 | 1.20 | 0.93 | 0.54 | 0.56 | 0.98 |
| Rnf186 | 1.00 | 1.00 | 1.00 | 1.00 | 1.00 | 1.00 | 1.00 | 1.00 | 1.00 | 1.68 | 2.02 | 1.12 |
| Rnf19b | 1.45 | 1.61 | 1.02 | 1.03 | 0.87 | 1.12 | 1.70 | 1.40 | 1.41 | 0.36 | 0.59 | 1.12 |
| Rnf24 | 1.00 | 1.00 | 1.00 | 0.39 | 0.10 | 0.56 | 0.88 | 1.05 | 1.09 | 1.00 | 1.00 | 1.15 |
| Rnf34 | 0.93 | 1.37 | 0.95 | 1.51 | 0.79 | 1.06 | 0.82 | 1.00 | 0.82 | 0.69 | 0.52 | 1.04 |
| Rnf38 | 1.08 | 1.72 | 1.13 | 2.42 | 0.33 | 1.01 | 1.39 | 1.46 | 1.11 | 0.32 | 0.37 | 0.98 |

Fig. 35- 78

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Pxt1 | 1.00 | 1.00 | 1.00 | 1.00 | 1.00 | 1.00 | 1.00 | 1.00 | 1.00 | 1.00 | 1.00 | 1.00 |
| Qpct | 2.09 | 1.52 | 1.33 | 1.00 | 1.00 | 1.00 | 0.98 | 0.51 | 0.76 | 1.11 | 1.13 | 1.43 |
| Qtrtd1 | 0.92 | 0.80 | 0.98 | 0.73 | 0.62 | 0.88 | 1.09 | 0.97 | 1.17 | 0.98 | 0.82 | 1.11 |
| Rab11fip2 | 1.07 | 0.83 | 0.99 | 1.16 | 1.25 | 1.05 | 0.93 | 1.00 | 1.00 | 1.05 | 0.71 | 0.88 |
| Rab11fip4 | 0.39 | 0.13 | 0.86 | 1.14 | 1.00 | 1.22 | 0.65 | 1.00 | 1.06 | 0.95 | 0.36 | 0.79 |
| Rab12 | 1.05 | 1.11 | 1.00 | 0.98 | 2.60 | 1.10 | 0.94 | 0.68 | 0.99 | 1.13 | 1.15 | 0.96 |
| Rab20 | 2.30 | 2.21 | 1.86 | 1.29 | 2.23 | 1.30 | 0.73 | 1.00 | 0.61 | 1.26 | 1.07 | 1.29 |
| Rab32 | 1.03 | 0.89 | 1.31 | 1.13 | 0.77 | 0.88 | 0.54 | 0.17 | 0.66 | 1.14 | 1.16 | 0.90 |
| Rab5c | 0.94 | 1.04 | 1.01 | 0.90 | 1.88 | 0.98 | 1.00 | 0.34 | 0.91 | 1.06 | 0.98 | 1.03 |
| Rad21 | 0.64 | 0.65 | 0.71 | 1.11 | 1.91 | 0.92 | 1.03 | 0.53 | 0.99 | 1.00 | 0.87 | 1.05 |
| Raet1e | 1.00 | 1.00 | 1.00 | 1.00 | 1.00 | 1.00 | 0.24 | 0.51 | 0.15 | 0.12 | 0.11 | 0.21 |
| Rai1 | 0.53 | 0.48 | 0.79 | 1.17 | 1.00 | 0.99 | 0.94 | 1.00 | 1.49 | 0.91 | 0.61 | 0.89 |
| Rai14 | 1.34 | 0.88 | 1.34 | 1.12 | 2.11 | 1.08 | 0.87 | 0.76 | 0.95 | 0.93 | 0.76 | 0.90 |
| Ranbp2 | 0.62 | 0.49 | 0.84 | 1.24 | 1.00 | 1.05 | 1.27 | 1.00 | 1.21 | 1.08 | 0.70 | 0.95 |
| Rasgrp1 | 0.64 | 0.63 | 0.81 | 0.88 | 1.00 | 0.99 | 1.00 | 1.00 | 1.00 | 0.96 | 0.90 | 0.86 |
| Rasgrp3 | 1.10 | 0.67 | 1.37 | 0.70 | 1.00 | 0.82 | 0.45 | 1.00 | 0.69 | 0.78 | 0.55 | 1.33 |
| Rasl2-9 | 0.56 | 0.61 | 0.70 | 1.14 | 2.22 | 1.17 | 1.11 | 0.76 | 1.10 | 0.84 | 0.59 | 0.85 |
| Rassf3 | 0.92 | 0.81 | 1.37 | 0.43 | 0.82 | 0.49 | 0.81 | 0.26 | 0.93 | 0.63 | 0.42 | 0.64 |
| Rassf6 | 2.14 | 1.65 | 1.57 | 1.11 | 1.40 | 1.07 | 0.77 | 0.23 | 0.93 | 1.10 | 1.32 | 1.15 |
| Rbbp9 | 1.08 | 0.97 | 1.19 | 0.76 | 1.16 | 0.81 | 0.94 | 0.50 | 0.79 | 0.88 | 0.79 | 0.95 |
| Rbfox2 | 1.16 | 0.91 | 1.33 | 0.97 | 1.00 | 0.85 | 0.76 | 1.00 | 0.83 | 0.89 | 0.58 | 0.91 |
| Rbl2 | 0.88 | 0.81 | 1.00 | 1.21 | 1.78 | 1.14 | 1.10 | 1.10 | 1.08 | 1.01 | 0.90 | 1.01 |
| Rbm12 | 0.68 | 0.57 | 0.75 | 0.83 | 1.36 | 0.71 | 1.30 | 1.00 | 1.69 | 0.95 | 0.87 | 0.91 |
| Rbm15b | 0.60 | 0.49 | 0.83 | 1.23 | 1.00 | 1.09 | 1.08 | 1.00 | 1.22 | 1.03 | 0.65 | 0.92 |
| Rbms1 | 0.64 | 0.42 | 0.91 | 1.19 | 1.32 | 1.17 | 1.47 | 1.00 | 1.47 | 1.08 | 0.48 | 1.08 |
| Rbmx2 | 0.78 | 0.85 | 0.76 | 0.61 | 1.35 | 0.71 | 1.00 | 1.00 | 1.00 | 1.25 | 1.12 | 1.28 |
| Rcn2 | 0.93 | 0.83 | 0.92 | 0.77 | 1.12 | 0.81 | 1.02 | 1.00 | 0.66 | 0.88 | 0.77 | 0.91 |
| Rcor1 | 0.33 | 0.16 | 0.67 | 1.18 | 1.00 | 0.99 | 1.09 | 1.00 | 1.14 | 1.04 | 0.20 | 0.96 |
| Rdh10 | 0.42 | 0.39 | 0.56 | 1.09 | 1.03 | 1.07 | 0.60 | 0.68 | 0.72 | 1.02 | 1.05 | 0.94 |
| Reck | 1.03 | 1.19 | 1.11 | 0.90 | 1.00 | 1.04 | 1.05 | 1.00 | 1.00 | 0.76 | 0.53 | 0.79 |
| Reep3 | 0.95 | 0.83 | 1.13 | 1.16 | 2.22 | 1.13 | 0.82 | 0.44 | 0.82 | 1.03 | 0.74 | 0.97 |
| Rere | 0.94 | 0.87 | 1.17 | 0.87 | 1.36 | 0.97 | 0.81 | 1.00 | 0.86 | 0.92 | 0.71 | 0.90 |
| Rest | 0.20 | 0.13 | 0.55 | 1.60 | 1.00 | 1.50 | 0.96 | 1.00 | 1.37 | 0.96 | 0.69 | 0.74 |
| Rfesd | 1.22 | 1.26 | 1.10 | 1.11 | 0.88 | 0.96 | 0.90 | 0.46 | 0.94 | 1.13 | 1.23 | 0.85 |
| Rgmb | 1.14 | 0.83 | 1.31 | 1.00 | 1.00 | 1.10 | 1.11 | 1.00 | 1.18 | 1.06 | 0.68 | 1.17 |
| Rgn | 1.00 | 1.00 | 1.00 | 0.71 | 1.00 | 0.87 | 0.41 | 0.25 | 0.37 | 0.96 | 0.99 | 0.76 |
| Rgs20 | 1.37 | 0.80 | 0.76 | 1.00 | 1.00 | 1.00 | 1.00 | 1.00 | 1.00 | 1.00 | 1.00 | 1.00 |
| Rgs4 | 1.92 | 1.53 | 2.60 | 0.68 | 0.87 | 0.50 | 1.30 | 1.00 | 0.80 | 0.69 | 0.51 | 0.75 |
| Rhbdf2 | 1.11 | 1.10 | 1.05 | 1.60 | 1.86 | 1.30 | 2.00 | 1.00 | 1.46 | 1.18 | 1.13 | 1.15 |
| Rhbdl1 | 0.89 | 1.16 | 0.91 | 0.93 | 0.48 | 1.10 | 0.33 | 0.98 | 0.83 | 0.81 | 1.14 | 1.06 |
| Rhbdl2 | 0.91 | 1.03 | 0.95 | 1.00 | 1.00 | 1.00 | 1.00 | 1.00 | 1.00 | 1.07 | 0.86 | 0.94 |
| Rhbdl3 | 0.76 | 0.53 | 1.03 | 1.04 | 1.00 | 0.71 | 1.00 | 1.00 | 1.00 | 0.94 | 0.89 | 0.95 |
| Rhd | 1.00 | 1.00 | 1.00 | 1.00 | 1.00 | 1.00 | 1.00 | 1.00 | 1.00 | 1.00 | 1.00 | 1.00 |
| Rheb | 1.05 | 1.21 | 1.08 | 0.97 | 2.77 | 0.99 | 1.21 | 0.45 | 1.11 | 0.98 | 1.23 | 0.96 |
| Rian | 1.00 | 1.00 | 1.00 | 1.00 | 1.00 | 1.00 | 1.00 | 1.00 | 0.60 | 1.11 | 0.71 | 1.12 |
| Rictor | 0.68 | 0.63 | 0.87 | 1.26 | 1.00 | 1.03 | 1.13 | 1.00 | 1.22 | 1.14 | 0.69 | 1.01 |
| Rilpl2 | 1.80 | 1.96 | 1.47 | 1.02 | 1.13 | 1.16 | 0.89 | 0.50 | 0.81 | 0.89 | 1.16 | 1.02 |
| Rin1 | 0.81 | 0.71 | 1.15 | 1.09 | 1.00 | 1.00 | 1.00 | 1.00 | 1.00 | 0.96 | 0.62 | 0.94 |
| Ripk2 | 0.85 | 0.57 | 0.89 | 1.35 | 1.00 | 0.77 | 0.93 | 1.00 | 1.09 | 0.72 | 1.07 | 1.36 |
| Ripply3 | 1.46 | 1.11 | 1.62 | 0.97 | 1.00 | 0.92 | 0.81 | 1.00 | 0.91 | 0.73 | 0.75 | 1.36 |
| Rlf | 0.70 | 0.72 | 0.85 | 1.17 | 1.18 | 1.07 | 1.45 | 1.00 | 0.92 | 1.05 | 0.80 | 0.94 |
| Rnase4 | 2.77 | 1.89 | 1.61 | 0.95 | 0.99 | 1.02 | 0.19 | 0.11 | 0.26 | 0.97 | 0.95 | 1.12 |
| Rnase6 | 0.74 | 0.72 | 0.92 | 1.19 | 1.00 | 2.25 | 1.00 | 1.00 | 1.00 | 1.07 | 0.86 | 0.78 |
| Rnase9 | 1.00 | 1.00 | 1.00 | 1.00 | 1.00 | 1.00 | 1.00 | 1.00 | 1.00 | 1.00 | 1.00 | 1.00 |
| Rnd3 | 0.74 | 0.81 | 0.94 | 1.02 | 1.00 | 0.90 | 0.76 | 0.90 | 0.84 | 1.00 | 0.77 | 0.92 |
| Rnf10 | 0.81 | 0.77 | 0.99 | 1.09 | 1.66 | 1.13 | 1.01 | 0.63 | 1.08 | 1.06 | 0.79 | 0.99 |
| Rnf11 | 1.05 | 0.90 | 1.15 | 1.11 | 2.24 | 0.95 | 0.96 | 0.91 | 0.88 | 1.01 | 0.77 | 1.14 |
| Rnf145 | 0.84 | 0.88 | 0.85 | 0.80 | 0.96 | 0.89 | 0.53 | 0.38 | 0.58 | 0.91 | 0.75 | 0.91 |
| Rnf146 | 0.91 | 0.86 | 0.91 | 1.02 | 2.72 | 0.93 | 1.09 | 1.05 | 1.02 | 1.09 | 0.95 | 1.05 |
| Rnf186 | 1.00 | 0.72 | 1.04 | 1.08 | 1.03 | 1.14 | 0.17 | 0.48 | 0.53 | 1.12 | 1.57 | 1.20 |
| Rnf19b | 1.16 | 1.24 | 1.27 | 1.32 | 1.68 | 1.17 | 1.10 | 0.56 | 1.03 | 1.21 | 1.28 | 1.04 |
| Rnf24 | 0.64 | 0.47 | 0.93 | 0.58 | 1.00 | 0.64 | 0.67 | 1.00 | 0.82 | 1.27 | 0.51 | 0.97 |
| Rnf34 | 0.92 | 0.88 | 0.95 | 0.98 | 1.08 | 1.04 | 0.71 | 0.89 | 1.18 | 0.94 | 0.97 | 0.94 |
| Rnf38 | 0.70 | 0.64 | 0.88 | 1.24 | 1.45 | 0.99 | 1.07 | 1.00 | 1.00 | 1.00 | 0.77 | 1.03 |

Fig. 35- 79

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Pxt1 | 1.00 | 1.00 | 1.00 | 1.27 | 1.00 | 1.00 | 0.93 | 0.11 | 0.98 | 1.00 | 1.00 | 1.00 |
| Qpct | 0.52 | 0.62 | 0.86 | 0.86 | 0.54 | 0.92 | 0.97 | 0.55 | 0.93 | 1.00 | 1.65 | 1.10 |
| Qtrtd1 | 0.83 | 0.92 | 0.88 | 1.04 | 1.00 | 1.07 | 0.81 | 0.89 | 0.80 | 1.02 | 0.81 | 1.07 |
| Rab11fip2 | 1.20 | 1.08 | 0.89 | 1.56 | 0.48 | 1.07 | 1.16 | 0.70 | 1.05 | 1.20 | 0.86 | 1.19 |
| Rab11fip4 | 0.96 | 1.04 | 0.69 | 1.50 | 1.00 | 1.00 | 0.97 | 1.98 | 1.09 | 0.69 | 1.18 | 1.45 |
| Rab12 | 1.12 | 1.13 | 1.45 | 0.90 | 0.49 | 0.99 | 0.83 | 0.38 | 0.99 | 0.95 | 0.93 | 0.95 |
| Rab20 | 1.54 | 1.74 | 1.05 | 3.11 | 1.00 | 2.22 | 0.75 | 0.95 | 0.63 | 1.06 | 1.60 | 0.99 |
| Rab32 | 0.98 | 0.89 | 0.90 | 0.42 | 0.16 | 0.41 | 1.00 | 1.00 | 1.00 | 0.86 | 0.78 | 0.89 |
| Rab5c | 0.93 | 0.94 | 0.85 | 1.00 | 0.14 | 1.03 | 0.90 | 0.35 | 0.93 | 1.02 | 1.03 | 0.90 |
| Rad21 | 0.92 | 0.88 | 0.88 | 0.95 | 0.30 | 1.32 | 1.02 | 0.83 | 1.02 | 0.93 | 0.74 | 0.92 |
| Raet1e | 0.33 | 0.40 | 0.39 | 1.00 | 1.00 | 1.00 | 1.00 | 1.00 | 1.00 | 1.00 | 1.00 | 1.00 |
| Rai1 | 0.93 | 1.04 | 0.81 | 1.03 | 0.35 | 0.96 | 0.83 | 1.00 | 0.95 | 0.77 | 0.81 | 1.06 |
| Rai14 | 0.98 | 0.99 | 0.92 | 1.46 | 0.59 | 1.10 | 1.01 | 0.48 | 0.98 | 0.85 | 0.63 | 0.82 |
| Ranbp2 | 1.03 | 0.88 | 0.70 | 1.22 | 0.20 | 0.76 | 1.27 | 0.71 | 1.07 | 0.99 | 0.61 | 1.07 |
| Rasgrp1 | 0.92 | 0.66 | 0.91 | 1.00 | 1.00 | 1.00 | 1.00 | 1.00 | 1.00 | 0.70 | 0.72 | 1.05 |
| Rasgrp3 | 1.22 | 1.38 | 1.29 | 0.58 | 0.39 | 0.92 | 1.00 | 1.00 | 1.00 | 0.84 | 0.41 | 0.81 |
| Rasl2-9 | 0.89 | 0.78 | 0.78 | 1.25 | 1.00 | 1.17 | 0.93 | 0.27 | 0.98 | 0.86 | 0.83 | 1.00 |
| Rassf3 | 0.69 | 0.72 | 0.64 | 0.84 | 0.17 | 0.86 | 0.98 | 1.00 | 1.13 | 0.85 | 0.65 | 0.89 |
| Rassf6 | 1.16 | 0.80 | 0.86 | 0.20 | 0.88 | 1.26 | 1.10 | 1.00 | 1.00 | 0.51 | 0.46 | 0.46 |
| Rbbp9 | 1.07 | 1.24 | 1.23 | 0.78 | 0.59 | 0.74 | 0.68 | 1.00 | 0.89 | 1.10 | 0.87 | 0.98 |
| Rbfox2 | 0.93 | 0.93 | 1.08 | 0.80 | 0.24 | 1.06 | 1.23 | 1.10 | 0.90 | 0.68 | 1.41 | 0.79 |
| Rbl2 | 1.50 | 1.68 | 1.55 | 1.14 | 0.29 | 1.24 | 1.11 | 2.54 | 1.07 | 1.07 | 0.84 | 1.02 |
| Rbm12 | 0.92 | 0.83 | 0.67 | 1.67 | 0.45 | 0.99 | 1.21 | 0.72 | 1.18 | 0.84 | 0.58 | 1.00 |
| Rbm15b | 0.88 | 0.90 | 0.80 | 1.45 | 0.36 | 0.98 | 1.11 | 0.61 | 1.05 | 0.79 | 0.64 | 1.14 |
| Rbms1 | 1.07 | 1.05 | 0.69 | 1.05 | 0.18 | 0.67 | 1.16 | 1.01 | 0.93 | 0.91 | 0.43 | 1.09 |
| Rbmx2 | 0.73 | 0.79 | 0.90 | 0.79 | 1.00 | 1.01 | 1.08 | 0.77 | 1.00 | 0.95 | 0.90 | 0.91 |
| Rcn2 | 0.94 | 0.82 | 0.96 | 0.91 | 0.28 | 0.97 | 0.79 | 0.21 | 0.80 | 1.05 | 0.85 | 0.91 |
| Rcor1 | 0.65 | 0.75 | 0.55 | 1.06 | 0.84 | 0.44 | 1.43 | 0.67 | 1.06 | 0.71 | 0.35 | 1.08 |
| Rdh10 | 0.75 | 0.64 | 0.65 | 0.87 | 0.75 | 1.02 | 0.76 | 0.60 | 0.90 | 0.76 | 0.55 | 0.73 |
| Reck | 0.94 | 0.87 | 1.05 | 0.76 | 1.00 | 0.83 | 0.79 | 1.00 | 0.88 | 1.22 | 1.14 | 1.25 |
| Reep3 | 1.11 | 1.01 | 0.99 | 1.38 | 0.63 | 1.27 | 0.79 | 1.00 | 0.73 | 0.90 | 0.67 | 0.92 |
| Rere | 0.95 | 1.05 | 0.98 | 0.78 | 0.15 | 0.76 | 1.16 | 0.35 | 1.07 | 1.05 | 0.80 | 1.23 |
| Rest | 0.97 | 0.78 | 0.61 | 1.00 | 0.42 | 0.30 | 1.55 | 1.00 | 1.38 | 0.75 | 0.25 | 1.29 |
| Rfesd | 0.90 | 0.94 | 0.92 | 0.73 | 0.45 | 0.85 | 1.06 | 0.53 | 0.90 | 1.14 | 1.20 | 0.85 |
| Rgmb | 0.93 | 0.90 | 0.97 | 0.82 | 0.28 | 0.89 | 0.98 | 1.00 | 0.81 | 0.77 | 0.82 | 1.03 |
| Rgn | 0.86 | 1.00 | 1.00 | 1.00 | 1.00 | 0.98 | 1.00 | 1.00 | 1.00 | 1.00 | 1.00 | 1.00 |
| Rgs20 | 1.00 | 1.00 | 1.00 | 1.00 | 1.00 | 1.00 | 1.00 | 1.00 | 1.00 | 1.00 | 1.57 | 1.00 |
| Rgs4 | 0.89 | 0.86 | 1.21 | 0.62 | 0.39 | 0.79 | 0.49 | 1.00 | 0.68 | 0.28 | 2.54 | 0.62 |
| Rhbdf2 | 0.96 | 1.33 | 1.07 | 1.10 | 1.00 | 1.36 | 0.76 | 1.00 | 0.86 | 0.87 | 0.70 | 0.81 |
| Rhbdl1 | 0.81 | 0.91 | 1.12 | 0.18 | 0.38 | 0.45 | 0.53 | 1.13 | 0.93 | 1.20 | 1.45 | 0.88 |
| Rhbdl2 | 0.49 | 0.63 | 0.58 | 1.00 | 1.00 | 1.00 | 1.00 | 1.18 | 1.00 | 1.00 | 1.00 | 0.97 |
| Rhbdl3 | 0.91 | 1.38 | 0.78 | 0.62 | 1.00 | 0.97 | 0.98 | 1.47 | 1.00 | 0.84 | 0.73 | 0.87 |
| Rhd | 1.00 | 1.00 | 1.00 | 1.00 | 1.00 | 1.00 | 1.00 | 1.54 | 1.00 | 0.34 | 0.39 | 0.16 |
| Rheb | 1.00 | 1.00 | 1.14 | 0.90 | 0.22 | 1.00 | 1.01 | 0.36 | 1.01 | 1.05 | 1.09 | 0.94 |
| Rian | 0.99 | 1.08 | 1.29 | 0.60 | 1.00 | 1.23 | 1.00 | 1.00 | 0.88 | 0.22 | 3.02 | 0.35 |
| Rictor | 1.16 | 0.99 | 0.90 | 1.14 | 0.69 | 0.94 | 1.11 | 1.00 | 1.04 | 0.92 | 0.64 | 1.05 |
| Rilpl2 | 0.90 | 1.74 | 1.31 | 0.75 | 0.50 | 1.00 | 0.93 | 0.63 | 0.97 | 1.24 | 1.37 | 1.29 |
| Rin1 | 0.72 | 0.72 | 0.69 | 1.25 | 1.00 | 1.60 | 1.23 | 1.19 | 1.03 | 1.00 | 2.27 | 1.00 |
| Ripk2 | 1.34 | 1.27 | 2.04 | 0.83 | 1.00 | 0.91 | 1.02 | 1.00 | 1.11 | 1.19 | 0.93 | 1.01 |
| Ripply3 | 0.62 | 0.65 | 0.64 | 0.86 | 0.75 | 0.97 | 1.00 | 1.00 | 1.00 | 0.87 | 0.70 | 1.07 |
| Rlf | 0.97 | 0.98 | 0.84 | 1.27 | 1.00 | 0.93 | 1.11 | 0.93 | 0.96 | 1.11 | 0.79 | 1.05 |
| Rnase4 | 1.27 | 1.22 | 1.04 | 1.10 | 0.48 | 1.11 | 0.85 | 0.87 | 0.94 | 1.20 | 0.96 | 1.21 |
| Rnase6 | 1.00 | 0.72 | 1.00 | 0.80 | 0.56 | 1.21 | 1.00 | 1.00 | 1.00 | 0.88 | 0.73 | 0.98 |
| Rnase9 | 1.00 | 1.00 | 1.00 | 1.00 | 1.46 | 0.04 | 1.00 | 1.00 | 1.00 | 1.00 | 1.00 | 1.00 |
| Rnd3 | 0.79 | 0.91 | 0.79 | 0.87 | 0.31 | 0.75 | 0.79 | 1.00 | 1.29 | 0.88 | 0.74 | 0.88 |
| Rnf10 | 0.95 | 1.05 | 0.89 | 1.09 | 0.26 | 0.97 | 1.13 | 0.53 | 1.15 | 0.75 | 0.71 | 0.75 |
| Rnf11 | 1.00 | 0.94 | 0.98 | 0.85 | 0.15 | 0.84 | 0.97 | 1.03 | 1.04 | 0.82 | 0.80 | 0.73 |
| Rnf145 | 0.92 | 0.84 | 0.93 | 0.83 | 0.33 | 0.74 | 0.93 | 0.40 | 0.99 | 1.18 | 0.97 | 0.99 |
| Rnf146 | 1.10 | 1.16 | 1.07 | 0.92 | 0.33 | 0.97 | 1.04 | 0.81 | 0.97 | 1.04 | 0.91 | 1.13 |
| Rnf186 | 1.28 | 1.54 | 1.20 | 1.12 | 1.00 | 1.90 | 1.00 | 1.00 | 1.00 | 0.65 | 0.68 | 0.66 |
| Rnf19b | 1.20 | 1.32 | 0.97 | 1.75 | 0.40 | 1.14 | 0.98 | 0.61 | 1.04 | 1.04 | 0.95 | 0.81 |
| Rnf24 | 0.82 | 0.97 | 0.70 | 0.62 | 0.61 | 0.50 | 0.84 | 0.63 | 1.04 | 1.05 | 1.16 | 1.04 |
| Rnf34 | 1.06 | 1.23 | 1.18 | 1.10 | 0.44 | 1.11 | 1.03 | 0.48 | 1.00 | 1.20 | 1.11 | 1.19 |
| Rnf38 | 1.17 | 1.12 | 1.01 | 1.04 | 0.44 | 0.95 | 1.00 | 1.16 | 0.99 | 0.88 | 0.64 | 1.01 |

Fig. 35- 80

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Pxt1 | 1.00 | 1.00 | 1.00 | 1.00 | 1.00 | 1.00 | 1.18 | 1.00 | 1.00 | 1.00 | 1.71 | 2.00 |
| Qpct | 1.00 | 1.00 | 1.00 | 1.19 | 0.15 | 0.98 | 0.89 | 0.79 | 1.12 | 1.00 | 0.59 | 0.71 |
| Qtrtd1 | 0.89 | 0.68 | 0.93 | 1.10 | 0.25 | 1.09 | 0.88 | 0.19 | 0.99 | 0.55 | 0.96 | 0.86 |
| Rab11fip2 | 0.75 | 1.18 | 1.00 | 0.92 | 1.00 | 1.00 | 0.87 | 0.20 | 1.23 | 0.76 | 0.81 | 0.80 |
| Rab11fip4 | 0.81 | 1.00 | 1.20 | 0.79 | 1.00 | 0.79 | 0.49 | 0.20 | 0.86 | 1.00 | 0.69 | 0.51 |
| Rab12 | 0.87 | 1.83 | 0.95 | 1.05 | 0.58 | 1.03 | 1.00 | 0.08 | 1.14 | 0.27 | 1.23 | 1.00 |
| Rab20 | 1.39 | 2.33 | 1.08 | 1.00 | 1.00 | 1.00 | 1.67 | 0.29 | 0.97 | 0.35 | 1.87 | 1.44 |
| Rab32 | 1.00 | 1.00 | 1.00 | 1.46 | 1.00 | 1.11 | 0.47 | 0.12 | 0.44 | 0.58 | 0.91 | 1.00 |
| Rab5c | 1.03 | 1.11 | 0.97 | 1.03 | 1.45 | 1.04 | 1.09 | 0.13 | 0.91 | 0.51 | 1.10 | 1.16 |
| Rad21 | 1.20 | 0.94 | 1.14 | 1.04 | 1.09 | 1.06 | 0.78 | 0.19 | 1.10 | 0.48 | 0.91 | 0.96 |
| Raet1e | 0.93 | 0.45 | 1.00 | 1.00 | 1.00 | 1.00 | 1.00 | 1.00 | 1.00 | 1.00 | 1.00 | 1.00 |
| Rai1 | 0.85 | 0.85 | 1.18 | 0.81 | 0.53 | 0.95 | 0.72 | 0.16 | 1.07 | 0.31 | 0.82 | 0.75 |
| Rai14 | 1.46 | 1.13 | 0.99 | 0.98 | 1.00 | 0.85 | 0.66 | 0.15 | 0.75 | 1.00 | 1.00 | 1.00 |
| Ranbp2 | 1.09 | 1.34 | 1.20 | 0.84 | 1.00 | 0.86 | 0.83 | 0.26 | 1.18 | 0.47 | 0.80 | 0.76 |
| Rasgrp1 | 1.00 | 1.00 | 1.00 | 0.99 | 2.37 | 0.98 | 0.78 | 0.29 | 0.77 | 0.46 | 0.80 | 0.91 |
| Rasgrp3 | 1.00 | 1.00 | 1.00 | 0.72 | 1.00 | 0.70 | 0.70 | 1.00 | 0.89 | 0.81 | 0.78 | 0.87 |
| Rasl2-9 | 1.59 | 1.11 | 0.89 | 1.06 | 1.00 | 1.09 | 1.29 | 0.12 | 0.68 | 0.09 | 0.84 | 0.82 |
| Rassf3 | 0.70 | 0.73 | 0.75 | 0.44 | 1.00 | 0.47 | 0.79 | 0.11 | 0.90 | 0.50 | 0.90 | 0.80 |
| Rassf6 | 1.00 | 0.73 | 0.90 | 0.86 | 1.00 | 1.00 | 0.67 | 0.43 | 0.97 | 1.00 | 1.00 | 1.00 |
| Rbbp9 | 0.87 | 0.85 | 0.93 | 0.98 | 1.00 | 0.82 | 0.78 | 0.08 | 0.96 | 0.53 | 1.33 | 1.32 |
| Rbfox2 | 0.98 | 1.44 | 1.30 | 0.98 | 0.74 | 1.01 | 1.02 | 0.14 | 1.32 | 1.00 | 1.00 | 1.00 |
| Rbl2 | 1.02 | 0.94 | 0.90 | 1.11 | 1.00 | 1.08 | 1.01 | 0.08 | 1.28 | 0.30 | 1.05 | 1.10 |
| Rbm12 | 1.03 | 1.41 | 1.00 | 0.89 | 1.00 | 0.78 | 0.59 | 0.20 | 0.94 | 0.67 | 0.64 | 0.73 |
| Rbm15b | 1.01 | 1.45 | 1.09 | 0.84 | 1.30 | 0.94 | 0.77 | 0.15 | 0.89 | 0.40 | 0.79 | 0.70 |
| Rbms1 | 1.00 | 1.00 | 1.00 | 0.92 | 0.56 | 0.88 | 0.89 | 0.27 | 1.06 | 1.42 | 1.06 | 0.88 |
| Rbmx2 | 1.00 | 1.00 | 1.00 | 0.84 | 1.00 | 1.11 | 0.93 | 0.15 | 0.94 | 0.55 | 1.12 | 0.79 |
| Rcn2 | 0.91 | 0.98 | 0.69 | 1.04 | 0.94 | 0.99 | 0.85 | 0.19 | 1.02 | 0.34 | 0.96 | 0.90 |
| Rcor1 | 1.53 | 1.43 | 1.07 | 0.77 | 1.00 | 0.83 | 0.57 | 0.38 | 1.15 | 1.00 | 0.59 | 0.46 |
| Rdh10 | 0.99 | 0.90 | 1.00 | 0.93 | 0.32 | 0.98 | 0.81 | 0.11 | 1.05 | 0.43 | 0.60 | 1.01 |
| Reck | 1.00 | 1.00 | 1.00 | 0.66 | 1.00 | 0.66 | 0.85 | 0.08 | 1.16 | 0.59 | 1.00 | 1.43 |
| Reep3 | 1.33 | 1.45 | 0.80 | 0.81 | 1.00 | 0.93 | 0.75 | 0.16 | 1.05 | 0.70 | 1.20 | 1.19 |
| Rere | 0.62 | 0.72 | 0.82 | 0.97 | 0.46 | 0.99 | 0.95 | 0.19 | 1.30 | 0.55 | 1.01 | 0.99 |
| Rest | 1.00 | 1.00 | 1.00 | 0.64 | 1.00 | 1.02 | 0.52 | 1.00 | 1.60 | 1.00 | 0.64 | 0.65 |
| Rfesd | 1.00 | 1.00 | 1.00 | 0.99 | 0.15 | 1.04 | 0.98 | 1.70 | 0.91 | 0.96 | 1.25 | 0.73 |
| Rgmb | 1.22 | 0.99 | 1.18 | 0.91 | 1.00 | 1.05 | 0.87 | 0.04 | 0.82 | 1.00 | 0.93 | 0.99 |
| Rgn | 1.00 | 1.00 | 1.00 | 1.00 | 1.00 | 1.00 | 0.66 | 0.18 | 0.62 | 1.00 | 1.00 | 1.00 |
| Rgs20 | 1.00 | 1.00 | 1.00 | 1.10 | 0.57 | 0.95 | 0.64 | 0.20 | 0.58 | 1.00 | 1.00 | 1.00 |
| Rgs4 | 1.00 | 1.00 | 1.00 | 0.95 | 0.86 | 0.85 | 0.64 | 0.61 | 0.62 | 1.00 | 1.00 | 1.00 |
| Rhbdf2 | 2.17 | 1.62 | 1.58 | 1.00 | 1.00 | 1.00 | 1.06 | 0.14 | 0.86 | 0.55 | 1.14 | 1.02 |
| Rhbdl1 | 1.00 | 1.00 | 0.83 | 0.98 | 0.87 | 0.94 | 0.96 | 1.57 | 1.10 | 1.58 | 1.32 | 0.90 |
| Rhbdl2 | 1.00 | 1.00 | 1.00 | 1.00 | 1.00 | 1.00 | 0.59 | 0.12 | 0.55 | 1.00 | 1.00 | 1.00 |
| Rhbdl3 | 1.00 | 1.00 | 1.00 | 1.19 | 1.58 | 1.10 | 0.62 | 0.20 | 0.70 | 1.00 | 1.00 | 1.00 |
| Rhd | 1.00 | 1.00 | 1.00 | 1.00 | 1.15 | 1.00 | 1.00 | 1.00 | 1.00 | 1.19 | 0.71 | 0.73 |
| Rheb | 1.00 | 1.01 | 1.01 | 1.28 | 0.66 | 1.03 | 1.04 | 0.09 | 1.08 | 0.48 | 1.02 | 1.18 |
| Rian | 1.00 | 1.00 | 1.00 | 0.96 | 1.61 | 0.92 | 0.82 | 1.00 | 1.00 | 1.00 | 1.00 | 1.00 |
| Rictor | 1.45 | 1.32 | 1.00 | 0.90 | 1.00 | 0.93 | 0.97 | 0.14 | 1.23 | 0.64 | 0.97 | 0.83 |
| Rilpl2 | 1.00 | 0.86 | 1.37 | 1.21 | 2.64 | 1.24 | 1.41 | 0.82 | 1.10 | 1.28 | 1.52 | 1.29 |
| Rin1 | 1.00 | 1.00 | 1.00 | 1.18 | 1.22 | 1.03 | 0.43 | 0.11 | 0.55 | 1.00 | 1.00 | 1.00 |
| Ripk2 | 1.00 | 1.00 | 1.00 | 1.23 | 1.00 | 1.00 | 0.75 | 0.17 | 0.75 | 0.74 | 1.04 | 1.19 |
| Ripply3 | 1.00 | 1.00 | 1.00 | 1.00 | 1.00 | 1.00 | 0.80 | 0.48 | 0.94 | 1.00 | 1.23 | 1.00 |
| Rif | 1.00 | 1.23 | 1.00 | 0.94 | 1.00 | 1.00 | 0.89 | 0.17 | 1.00 | 0.46 | 1.08 | 0.86 |
| Rnase4 | 0.48 | 0.41 | 0.49 | 0.69 | 1.00 | 0.71 | 1.24 | 0.16 | 1.33 | 0.53 | 1.38 | 1.74 |
| Rnase6 | 1.00 | 1.00 | 1.00 | 1.00 | 1.00 | 1.00 | 0.33 | 0.25 | 0.86 | 0.59 | 0.79 | 0.79 |
| Rnase9 | 1.00 | 1.00 | 1.00 | 1.00 | 1.00 | 1.00 | 1.00 | 1.00 | 1.00 | 1.00 | 1.00 | 1.00 |
| Rnd3 | 0.72 | 1.00 | 1.00 | 0.89 | 1.47 | 0.88 | 0.66 | 0.04 | 0.90 | 0.44 | 1.05 | 1.12 |
| Rnf10 | 1.07 | 1.03 | 1.03 | 0.96 | 0.75 | 0.97 | 1.06 | 0.13 | 1.03 | 0.42 | 0.89 | 0.86 |
| Rnf11 | 1.13 | 1.19 | 0.89 | 1.03 | 2.87 | 1.02 | 0.81 | 0.14 | 0.90 | 0.34 | 0.86 | 0.91 |
| Rnf145 | 1.19 | 1.11 | 1.38 | 0.92 | 0.40 | 0.94 | 0.67 | 0.17 | 0.87 | 0.51 | 0.97 | 0.81 |
| Rnf146 | 0.96 | 0.95 | 1.13 | 1.03 | 0.17 | 1.04 | 1.01 | 0.52 | 1.29 | 0.76 | 1.08 | 1.06 |
| Rnf186 | 1.11 | 0.59 | 0.95 | 1.00 | 1.00 | 1.00 | 1.00 | 1.00 | 1.00 | 1.00 | 1.00 | 1.00 |
| Rnf19b | 0.99 | 1.39 | 0.97 | 1.10 | 0.76 | 1.08 | 1.10 | 0.18 | 0.90 | 0.83 | 1.28 | 1.14 |
| Rnf24 | 1.00 | 1.00 | 1.00 | 0.91 | 0.60 | 0.95 | 0.54 | 0.45 | 0.80 | 1.00 | 0.98 | 1.25 |
| Rnf34 | 1.01 | 1.22 | 0.91 | 0.91 | 0.73 | 1.04 | 0.91 | 0.10 | 1.09 | 0.70 | 1.37 | 1.21 |
| Rnf38 | 1.19 | 1.37 | 1.36 | 1.09 | 0.71 | 1.12 | 0.88 | 0.10 | 1.10 | 0.39 | 0.98 | 0.92 |

Fig. 35-81

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Rnf39 | 1.37 | 1.00 | 1.30 | 1.00 | 1.00 | 1.00 | 2.80 | 1.73 | 1.46 | 0.41 | 0.06 | 1.26 |
| Rnf44 | 1.10 | 1.58 | 1.12 | 1.39 | 0.25 | 0.91 | 1.22 | 1.20 | 1.05 | 0.48 | 0.48 | 1.02 |
| Rnft1 | 1.07 | 2.33 | 1.08 | 3.26 | 0.31 | 1.29 | 1.00 | 1.32 | 1.14 | 0.54 | 0.29 | 1.11 |
| Rnu12 | 1.00 | 1.00 | 1.00 | 1.00 | 1.00 | 1.00 | 1.00 | 1.00 | 1.00 | 1.00 | 1.00 | 1.00 |
| Rpa3 | 0.77 | 1.42 | 0.78 | 0.57 | 1.06 | 1.13 | 1.34 | 0.59 | 0.28 | 0.12 | 1.22 | 0.83 |
| Rpl12 | 1.72 | 0.27 | 1.11 | 0.16 | 3.28 | 1.52 | 1.44 | 0.60 | 1.15 | 1.11 | 2.74 | 0.54 |
| Rpl30 | 1.19 | 0.67 | 1.13 | 0.52 | 2.21 | 1.19 | 1.07 | 0.83 | 0.90 | 0.17 | 2.02 | 0.68 |
| Rpl37 | 1.53 | 0.96 | 1.17 | 0.14 | 2.99 | 1.19 | 1.10 | 0.78 | 1.12 | 0.59 | 1.09 | 0.84 |
| Rpp38 | 1.01 | 1.36 | 0.79 | 1.59 | 1.24 | 1.27 | 1.14 | 0.85 | 1.01 | 0.34 | 0.41 | 0.97 |
| Rprd1b | 0.98 | 1.44 | 1.04 | 1.19 | 0.36 | 0.95 | 0.95 | 0.93 | 0.96 | 0.56 | 0.47 | 1.14 |
| Rprd2 | 0.96 | 1.38 | 1.05 | 1.96 | 0.40 | 1.04 | 1.04 | 1.31 | 1.21 | 0.39 | 0.50 | 1.01 |
| Rprl2 | 1.00 | 1.00 | 1.00 | 1.00 | 1.00 | 1.00 | 1.00 | 1.00 | 1.00 | 1.00 | 1.00 | 1.00 |
| Rprml | 1.00 | 1.00 | 0.84 | 1.00 | 0.28 | 1.00 | 1.00 | 1.00 | 1.00 | 0.73 | 0.60 | 0.64 |
| Rps10 | 1.70 | 0.73 | 0.92 | 0.18 | 3.46 | 1.07 | 0.83 | 0.61 | 0.90 | 0.84 | 1.31 | 0.89 |
| Rps27 | 1.15 | 2.29 | 1.25 | 0.69 | 3.22 | 1.41 | 1.29 | 0.97 | 0.70 | 0.11 | 1.34 | 0.67 |
| Rraga | 1.00 | 1.86 | 0.90 | 0.73 | 0.19 | 1.04 | 1.04 | 1.03 | 0.88 | 0.48 | 0.23 | 1.06 |
| Rsu1 | 1.35 | 2.86 | 0.75 | 2.01 | 0.19 | 0.95 | 0.96 | 1.01 | 0.75 | 0.11 | 0.20 | 0.86 |
| Rtp3 | 0.80 | 1.00 | 0.81 | 1.09 | 0.49 | 1.06 | 0.80 | 0.71 | 1.04 | 0.46 | 0.25 | 0.69 |
| Rusc2 | 1.64 | 3.02 | 1.60 | 3.14 | 0.60 | 1.76 | 3.14 | 3.18 | 1.90 | 0.32 | 0.22 | 1.12 |
| Ruvbl2 | 0.88 | 0.97 | 0.80 | 0.13 | 0.46 | 0.60 | 1.03 | 1.18 | 1.14 | 0.68 | 0.76 | 1.26 |
| Rybp | 0.88 | 1.00 | 1.10 | 2.87 | 0.41 | 1.28 | 1.10 | 1.34 | 1.14 | 0.38 | 0.49 | 1.08 |
| S1pr5 | 1.00 | 1.00 | 1.00 | 0.07 | 0.12 | 0.16 | 0.56 | 0.67 | 0.60 | 0.99 | 0.40 | 0.46 |
| Samd14 | 1.79 | 1.00 | 1.15 | 1.82 | 0.12 | 1.60 | 1.24 | 1.20 | 0.98 | 1.27 | 0.96 | 1.13 |
| Sap30 | 4.29 | 4.03 | 2.22 | 0.45 | 0.38 | 0.85 | 2.25 | 1.97 | 1.16 | 0.52 | 0.92 | 1.18 |
| Sash1 | 1.03 | 1.47 | 1.06 | 2.13 | 0.22 | 0.84 | 1.20 | 1.76 | 1.21 | 0.86 | 0.40 | 1.16 |
| Sbf2 | 0.88 | 1.00 | 1.27 | 1.15 | 0.51 | 1.11 | 1.14 | 1.29 | 0.98 | 0.57 | 0.42 | 1.01 |
| Sbno2 | 2.52 | 2.14 | 1.25 | 0.33 | 0.44 | 0.76 | 1.45 | 1.09 | 1.73 | 0.41 | 0.63 | 1.17 |
| Scaf4 | 1.15 | 1.51 | 1.25 | 0.69 | 0.17 | 1.16 | 0.90 | 0.92 | 1.27 | 0.58 | 0.32 | 1.03 |
| Scara3 | 0.60 | 0.72 | 0.92 | 0.76 | 0.61 | 0.81 | 0.62 | 0.66 | 0.72 | 0.74 | 0.36 | 0.69 |
| Scarna13 | 1.00 | 1.00 | 1.00 | 0.94 | 1.00 | 1.00 | 1.00 | 0.65 | 1.15 | 1.59 | 0.28 | 1.15 |
| Scarna3a | 1.00 | 1.00 | 1.00 | 1.00 | 1.00 | 1.00 | 1.00 | 1.00 | 1.00 | 1.00 | 1.00 | 1.00 |
| Scarna3b | 1.00 | 1.00 | 1.00 | 1.00 | 1.00 | 1.00 | 1.00 | 1.00 | 1.00 | 1.00 | 1.00 | 1.00 |
| Scd1 | 0.83 | 1.51 | 1.67 | 1.00 | 0.26 | 0.75 | 0.95 | 1.13 | 1.55 | 0.69 | 0.70 | 1.33 |
| Scd2 | 0.48 | 0.46 | 0.77 | 1.18 | 0.09 | 0.64 | 0.43 | 0.49 | 0.55 | 1.10 | 0.74 | 1.06 |
| Scd4 | 1.00 | 1.00 | 1.00 | 1.68 | 0.59 | 0.64 | 0.04 | 0.05 | 0.05 | 1.00 | 1.75 | 1.61 |
| Scg5 | 1.00 | 1.00 | 1.00 | 1.00 | 0.18 | 1.00 | 1.00 | 1.00 | 1.00 | 1.18 | 1.00 | 1.00 |
| Scgb1b27 | 1.00 | 1.00 | 1.00 | 1.00 | 1.00 | 1.00 | 1.00 | 1.00 | 1.00 | 1.00 | 1.00 | 1.00 |
| Scn2b | 1.14 | 1.00 | 1.46 | 1.00 | 0.16 | 1.00 | 1.38 | 1.00 | 2.06 | 1.00 | 1.00 | 1.06 |
| Scn7a | 1.25 | 1.49 | 1.33 | 2.67 | 0.82 | 1.37 | 0.88 | 1.04 | 1.19 | 0.16 | 0.18 | 0.42 |
| Sde2 | 1.09 | 1.78 | 1.23 | 1.73 | 0.76 | 1.35 | 1.13 | 1.09 | 1.23 | 0.51 | 0.57 | 1.23 |
| Sdr16c6 | 1.00 | 1.00 | 1.00 | 1.00 | 1.00 | 1.00 | 1.00 | 1.00 | 1.00 | 1.00 | 1.00 | 1.00 |
| Sdr9c7 | 1.00 | 1.00 | 1.00 | 1.00 | 1.00 | 1.00 | 1.00 | 1.00 | 1.00 | 1.00 | 1.00 | 1.00 |
| Sec24d | 1.37 | 1.00 | 1.19 | 2.33 | 0.43 | 1.23 | 0.72 | 0.68 | 0.86 | 0.48 | 0.27 | 0.94 |
| Secisbp2 | 1.56 | 2.64 | 1.43 | 1.02 | 0.25 | 1.22 | 1.35 | 1.46 | 1.22 | 0.76 | 0.38 | 1.08 |
| Secisbp2l | 0.89 | 1.23 | 1.25 | 3.18 | 0.36 | 0.99 | 1.08 | 1.47 | 1.30 | 0.51 | 0.55 | 1.11 |
| Sema3d | 1.00 | 1.00 | 1.00 | 1.00 | 1.00 | 1.00 | 0.91 | 1.01 | 1.08 | 1.00 | 0.85 | 0.79 |
| Sema3g | 1.06 | 1.02 | 1.29 | 1.42 | 0.08 | 1.28 | 1.36 | 1.44 | 1.28 | 0.77 | 0.10 | 1.16 |
| Sema4c | 0.93 | 1.56 | 1.03 | 0.87 | 0.32 | 1.03 | 0.89 | 0.90 | 1.02 | 0.62 | 0.36 | 1.04 |
| Sema4d | 0.98 | 1.00 | 1.23 | 1.00 | 1.00 | 1.00 | 0.99 | 1.12 | 1.10 | 0.76 | 0.56 | 0.79 |
| Senp5 | 1.33 | 1.14 | 1.15 | 1.36 | 0.29 | 0.82 | 1.06 | 1.29 | 1.30 | 0.59 | 0.54 | 0.96 |
| Sept11 | 0.51 | 1.10 | 0.67 | 1.47 | 0.20 | 0.91 | 1.11 | 1.04 | 1.27 | 0.70 | 0.30 | 0.80 |
| Sept3 | 1.00 | 1.00 | 1.00 | 1.00 | 0.15 | 1.00 | 1.00 | 1.00 | 1.00 | 1.00 | 1.00 | 0.79 |
| Sept8 | 0.93 | 1.16 | 1.21 | 1.23 | 0.50 | 1.19 | 0.91 | 0.94 | 1.07 | 0.61 | 0.59 | 0.85 |
| Serp1 | 0.92 | 1.33 | 1.21 | 1.45 | 0.43 | 0.99 | 0.85 | 1.01 | 1.19 | 0.47 | 0.38 | 0.96 |
| Serpina1f | 1.00 | 1.00 | 1.00 | 1.00 | 1.00 | 1.00 | 1.00 | 1.00 | 1.00 | 1.00 | 1.00 | 1.00 |
| Serpina3f | 1.00 | 1.00 | 1.00 | 1.00 | 1.00 | 1.00 | 1.00 | 1.00 | 0.83 | 0.80 | 0.28 | 0.87 |
| Serpina3i | 1.00 | 1.00 | 1.00 | 1.13 | 1.00 | 1.00 | 2.46 | 1.63 | 3.08 | 1.00 | 0.59 | 2.26 |
| Serpina3j | 1.00 | 1.00 | 1.00 | 1.00 | 1.00 | 1.00 | 1.00 | 1.00 | 1.00 | 1.00 | 1.00 | 1.00 |
| Serpina7 | 1.00 | 1.00 | 1.00 | 1.00 | 1.00 | 1.00 | 1.00 | 1.00 | 1.00 | 1.00 | 1.00 | 1.00 |
| Serpinb10 | 1.00 | 1.00 | 1.00 | 1.00 | 1.00 | 1.00 | 1.00 | 1.00 | 1.00 | 1.00 | 1.00 | 1.00 |
| Serpinb2 | 1.00 | 1.00 | 1.00 | 1.00 | 1.00 | 1.00 | 1.00 | 1.00 | 1.00 | 1.00 | 1.00 | 1.00 |
| Serpinb3a | 1.00 | 1.00 | 1.00 | 1.00 | 1.00 | 1.00 | 1.00 | 1.00 | 1.00 | 1.00 | 1.00 | 1.00 |
| Serpinb3b | 1.00 | 1.00 | 1.00 | 1.00 | 1.00 | 1.00 | 1.00 | 1.00 | 1.00 | 1.00 | 1.00 | 1.00 |
| Serpini1 | 1.00 | 1.00 | 1.00 | 1.41 | 0.19 | 1.01 | 1.12 | 1.01 | 1.02 | 1.00 | 1.00 | 0.99 |

Fig. 35- 82

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Rnf39 | 1.72 | 2.09 | 2.01 | 0.76 | 1.00 | 1.00 | 1.50 | 1.00 | 1.22 | 0.53 | 0.37 | 0.46 |
| Rnf44 | 0.74 | 0.69 | 0.95 | 1.02 | 1.36 | 0.99 | 1.11 | 0.75 | 1.06 | 0.99 | 0.73 | 1.07 |
| Rnft1 | 1.03 | 0.91 | 1.16 | 1.24 | 1.85 | 0.92 | 1.02 | 1.00 | 1.06 | 1.01 | 0.78 | 0.94 |
| Rnu12 | 1.00 | 1.00 | 1.00 | 1.00 | 1.00 | 1.00 | 1.00 | 1.00 | 1.00 | 1.00 | 1.00 | 1.00 |
| Rpa3 | 0.82 | 1.52 | 0.67 | 0.64 | 1.52 | 0.69 | 0.65 | 0.66 | 0.50 | 0.85 | 1.62 | 0.85 |
| Rpl12 | 1.45 | 2.84 | 1.01 | 1.00 | 0.39 | 0.72 | 1.07 | 2.68 | 1.79 | 1.19 | 1.98 | 0.82 |
| Rpl30 | 1.22 | 2.65 | 1.34 | 1.37 | 4.22 | 0.90 | 1.04 | 0.53 | 1.35 | 2.00 | 1.72 | 1.41 |
| Rpl37 | 1.18 | 2.17 | 1.01 | 1.21 | 1.71 | 0.97 | 1.17 | 0.30 | 1.02 | 1.37 | 1.54 | 1.11 |
| Rpp38 | 1.32 | 1.32 | 0.86 | 1.04 | 0.75 | 1.05 | 1.84 | 0.78 | 1.20 | 1.02 | 1.24 | 0.89 |
| Rprd1b | 0.71 | 0.77 | 0.80 | 0.97 | 1.10 | 0.94 | 0.91 | 0.83 | 0.90 | 0.91 | 0.78 | 0.99 |
| Rprd2 | 0.67 | 0.59 | 0.92 | 0.96 | 1.06 | 1.06 | 0.85 | 1.00 | 1.10 | 0.98 | 0.61 | 0.98 |
| Rprl2 | 1.00 | 1.00 | 1.00 | 1.00 | 1.00 | 1.00 | 1.00 | 1.00 | 1.00 | 1.00 | 1.00 | 1.00 |
| Rprml | 1.00 | 1.00 | 1.00 | 1.00 | 1.00 | 1.00 | 1.00 | 1.00 | 1.00 | 1.56 | 1.11 | 0.85 |
| Rps10 | 1.26 | 1.79 | 1.00 | 0.90 | 0.94 | 0.88 | 1.01 | 0.67 | 1.06 | 0.83 | 1.59 | 1.14 |
| Rps27 | 1.07 | 1.63 | 1.36 | 0.87 | 3.69 | 1.49 | 1.21 | 0.16 | 0.63 | 0.71 | 1.61 | 1.01 |
| Rraga | 0.93 | 0.92 | 0.98 | 0.87 | 2.41 | 0.97 | 0.96 | 0.35 | 1.02 | 1.09 | 0.88 | 0.96 |
| Rsu1 | 1.05 | 1.23 | 1.17 | 0.88 | 2.73 | 0.85 | 0.74 | 1.00 | 0.76 | 0.93 | 0.87 | 0.92 |
| Rtp3 | 1.00 | 1.00 | 1.00 | 0.21 | 0.14 | 0.34 | 0.30 | 0.15 | 0.37 | 1.00 | 1.00 | 1.00 |
| Rusc2 | 2.36 | 1.37 | 0.99 | 1.26 | 1.10 | 1.24 | 1.14 | 0.78 | 1.35 | 0.80 | 0.67 | 0.73 |
| Ruvbl2 | 0.74 | 0.92 | 0.83 | 1.01 | 1.37 | 0.81 | 1.15 | 1.00 | 0.84 | 0.98 | 1.26 | 0.91 |
| Rybp | 0.69 | 0.53 | 0.93 | 0.97 | 1.45 | 0.91 | 1.05 | 1.00 | 1.28 | 1.04 | 0.75 | 1.03 |
| S1pr5 | 1.00 | 1.00 | 0.65 | 1.00 | 1.00 | 1.00 | 0.11 | 0.11 | 0.34 | 1.00 | 1.00 | 1.00 |
| Samd14 | 0.98 | 1.06 | 0.89 | 1.20 | 0.63 | 1.19 | 1.61 | 1.00 | 1.06 | 0.87 | 0.97 | 1.09 |
| Sap30 | 0.80 | 0.92 | 1.02 | 0.82 | 0.81 | 1.03 | 1.20 | 0.71 | 1.36 | 1.04 | 0.97 | 1.00 |
| Sash1 | 1.94 | 1.31 | 1.93 | 1.62 | 1.64 | 1.21 | 1.10 | 1.00 | 0.94 | 0.94 | 0.65 | 0.80 |
| Sbf2 | 1.07 | 0.89 | 1.20 | 0.98 | 1.38 | 1.11 | 1.10 | 1.00 | 0.98 | 1.01 | 0.67 | 1.05 |
| Sbno2 | 0.96 | 1.01 | 0.95 | 0.99 | 1.78 | 1.02 | 1.20 | 0.56 | 1.40 | 1.03 | 0.98 | 1.09 |
| Scaf4 | 0.68 | 0.58 | 0.88 | 1.15 | 1.46 | 1.19 | 0.98 | 1.00 | 1.19 | 0.91 | 0.65 | 1.03 |
| Scara3 | 1.65 | 1.00 | 1.26 | 1.00 | 1.00 | 1.00 | 1.00 | 1.00 | 1.00 | 0.63 | 0.66 | 0.76 |
| Scarna13 | 1.67 | 3.27 | 1.06 | 0.79 | 1.00 | 1.00 | 1.00 | 1.09 | 2.75 | 1.34 | 1.00 | 1.35 |
| Scarna3a | 1.00 | 1.00 | 1.00 | 1.00 | 1.00 | 1.00 | 1.00 | 1.00 | 1.00 | 1.00 | 1.00 | 1.00 |
| Scarna3b | 1.00 | 1.00 | 1.00 | 1.00 | 1.00 | 0.11 | 1.00 | 1.00 | 1.00 | 1.00 | 1.00 | 1.00 |
| Scd1 | 0.46 | 0.60 | 0.37 | 0.61 | 1.06 | 0.76 | 0.21 | 0.23 | 0.24 | 1.11 | 0.98 | 1.00 |
| Scd2 | 0.55 | 0.52 | 0.82 | 1.23 | 1.09 | 1.10 | 0.42 | 1.00 | 0.59 | 1.30 | 0.97 | 0.91 |
| Scd4 | 1.11 | 1.80 | 0.92 | 1.00 | 1.00 | 1.00 | 1.00 | 1.00 | 1.00 | 1.00 | 1.00 | 1.00 |
| Scg5 | 1.08 | 1.08 | 0.99 | 1.42 | 1.89 | 1.03 | 1.00 | 1.00 | 1.00 | 1.49 | 1.67 | 1.21 |
| Scgb1b27 | 1.00 | 1.00 | 0.20 | 1.00 | 1.00 | 1.00 | 1.00 | 1.00 | 1.00 | 1.00 | 1.00 | 1.00 |
| Scn2b | 0.58 | 0.53 | 0.75 | 1.34 | 1.00 | 1.57 | 1.00 | 1.00 | 1.00 | 1.10 | 0.95 | 1.30 |
| Scn7a | 2.24 | 1.45 | 1.44 | 1.00 | 1.00 | 1.00 | 1.00 | 1.00 | 1.00 | 1.18 | 1.05 | 1.08 |
| Sde2 | 0.81 | 0.85 | 0.94 | 1.03 | 1.23 | 1.21 | 1.24 | 0.65 | 1.25 | 1.31 | 0.87 | 1.19 |
| Sdr16c6 | 1.00 | 1.00 | 1.00 | 1.00 | 1.00 | 1.00 | 1.00 | 1.00 | 1.00 | 1.00 | 1.00 | 1.00 |
| Sdr9c7 | 0.99 | 1.00 | 1.00 | 1.00 | 1.00 | 1.00 | 0.32 | 0.11 | 0.75 | 1.00 | 1.00 | 1.00 |
| Sec24d | 1.10 | 1.12 | 1.20 | 1.37 | 1.00 | 1.34 | 1.66 | 0.88 | 1.73 | 0.96 | 0.89 | 0.97 |
| Secisbp2 | 0.79 | 0.69 | 0.83 | 0.90 | 0.75 | 1.10 | 1.30 | 1.00 | 1.44 | 1.01 | 0.96 | 0.95 |
| Secisbp2l | 0.72 | 0.58 | 0.93 | 1.05 | 1.58 | 1.08 | 1.07 | 0.77 | 1.20 | 1.08 | 0.64 | 0.99 |
| Sema3d | 1.00 | 1.00 | 1.00 | 1.03 | 1.00 | 1.00 | 1.00 | 1.00 | 1.00 | 1.12 | 1.00 | 1.00 |
| Sema3g | 1.86 | 1.61 | 1.61 | 0.98 | 1.00 | 1.17 | 1.00 | 1.00 | 1.00 | 1.21 | 0.89 | 1.35 |
| Sema4c | 1.23 | 1.05 | 1.11 | 1.45 | 1.00 | 1.21 | 1.49 | 1.00 | 0.95 | 0.90 | 0.85 | 1.15 |
| Sema4d | 0.86 | 0.82 | 1.02 | 0.73 | 0.93 | 0.82 | 1.00 | 1.00 | 1.00 | 0.96 | 0.64 | 1.01 |
| Senp5 | 0.69 | 0.57 | 0.84 | 1.20 | 1.36 | 1.10 | 0.93 | 1.00 | 1.14 | 0.94 | 0.69 | 0.97 |
| Sept11 | 0.50 | 0.44 | 0.85 | 0.94 | 1.08 | 1.03 | 1.15 | 1.00 | 1.38 | 0.89 | 0.56 | 0.91 |
| Sept3 | 0.41 | 0.45 | 0.83 | 1.00 | 1.00 | 1.00 | 1.00 | 1.00 | 1.00 | 0.84 | 0.97 | 0.98 |
| Sept8 | 0.88 | 0.80 | 0.86 | 0.95 | 1.37 | 1.08 | 0.91 | 1.00 | 1.03 | 0.93 | 0.68 | 0.95 |
| Serp1 | 0.91 | 0.88 | 1.19 | 1.05 | 1.14 | 1.00 | 1.21 | 0.83 | 1.00 | 1.10 | 0.91 | 1.03 |
| Serpina1f | 1.00 | 1.00 | 1.00 | 0.81 | 0.79 | 0.70 | 1.00 | 1.00 | 1.00 | 1.00 | 1.00 | 1.00 |
| Serpina3f | 0.93 | 0.64 | 0.95 | 1.00 | 1.00 | 1.00 | 0.24 | 1.00 | 0.17 | 0.91 | 0.59 | 0.94 |
| Serpina3i | 1.73 | 1.30 | 1.51 | 1.00 | 1.00 | 1.00 | 1.38 | 1.00 | 0.97 | 1.00 | 1.00 | 1.00 |
| Serpina3j | 2.21 | 1.12 | 1.00 | 1.00 | 1.00 | 1.00 | 1.00 | 1.00 | 1.00 | 1.00 | 1.00 | 0.73 |
| Serpina7 | 1.04 | 1.00 | 1.00 | 1.00 | 1.00 | 1.00 | 0.27 | 1.00 | 0.15 | 1.00 | 1.00 | 1.00 |
| Serpinb10 | 1.02 | 1.32 | 1.00 | 1.00 | 1.00 | 1.00 | 1.00 | 1.00 | 1.00 | 1.00 | 1.00 | 1.00 |
| Serpinb2 | 0.74 | 0.63 | 0.66 | 1.00 | 1.00 | 1.00 | 1.00 | 1.00 | 1.00 | 1.00 | 1.00 | 1.00 |
| Serpinb3a | 1.18 | 0.57 | 1.69 | 1.00 | 1.00 | 1.00 | 1.00 | 1.00 | 1.00 | 1.00 | 1.00 | 1.00 |
| Serpinb3b | 1.00 | 1.00 | 1.00 | 1.00 | 1.00 | 1.00 | 1.00 | 1.00 | 1.00 | 1.00 | 1.00 | 1.00 |
| Serpini1 | 0.71 | 0.90 | 1.14 | 0.84 | 1.00 | 0.71 | 1.00 | 1.00 | 1.00 | 1.32 | 1.11 | 1.12 |

Fig. 35- 83

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Rnf39 | 1.23 | 1.55 | 1.51 | 1.42 | 1.00 | 1.41 | 1.00 | 1.00 | 1.00 | 1.00 | 1.00 | 1.00 |
| Rnf44 | 1.02 | 1.02 | 0.95 | 1.08 | 0.46 | 1.09 | 1.01 | 3.22 | 1.04 | 1.08 | 0.75 | 1.12 |
| Rnft1 | 0.99 | 0.93 | 0.89 | 1.20 | 1.00 | 1.17 | 1.01 | 0.38 | 0.96 | 1.22 | 0.77 | 1.12 |
| Rnu12 | 1.00 | 1.00 | 1.00 | 1.00 | 0.02 | 1.00 | 1.00 | 1.00 | 1.00 | 1.00 | 1.00 | 1.00 |
| Rpa3 | 1.04 | 0.61 | 1.21 | 0.58 | 0.39 | 1.08 | 0.54 | 0.54 | 1.46 | 0.69 | 0.98 | 0.85 |
| Rpl12 | 1.29 | 0.85 | 0.90 | 0.98 | 2.38 | 1.11 | 0.92 | 0.56 | 1.62 | 1.16 | 1.33 | 1.23 |
| Rpl30 | 1.01 | 1.35 | 1.47 | 1.86 | 1.00 | 1.30 | 1.01 | 0.83 | 0.77 | 0.97 | 1.67 | 1.45 |
| Rpl37 | 1.20 | 1.17 | 0.95 | 0.73 | 1.69 | 1.29 | 1.05 | 0.54 | 1.37 | 1.23 | 1.37 | 1.19 |
| Rpp38 | 0.65 | 0.56 | 1.04 | 1.44 | 1.00 | 1.08 | 1.15 | 0.40 | 1.06 | 1.04 | 0.98 | 1.15 |
| Rprd1b | 1.02 | 0.92 | 0.93 | 1.18 | 0.47 | 1.19 | 0.97 | 0.57 | 0.97 | 0.95 | 0.73 | 0.93 |
| Rprd2 | 1.00 | 0.85 | 0.88 | 1.17 | 0.51 | 1.00 | 1.04 | 0.45 | 1.01 | 1.03 | 0.64 | 1.17 |
| Rprl2 | 1.00 | 1.00 | 1.00 | 1.00 | 0.10 | 1.00 | 1.00 | 1.70 | 1.00 | 1.00 | 1.00 | 1.00 |
| Rprml | 1.00 | 1.00 | 1.00 | 0.15 | 0.50 | 0.13 | 0.76 | 1.01 | 0.48 | 1.00 | 3.55 | 1.00 |
| Rps10 | 1.08 | 1.31 | 1.00 | 0.99 | 4.63 | 1.06 | 0.68 | 0.75 | 1.13 | 1.12 | 1.58 | 1.07 |
| Rps27 | 0.67 | 1.06 | 0.67 | 1.02 | 1.50 | 1.25 | 1.90 | 0.80 | 0.75 | 1.00 | 1.60 | 0.83 |
| Rraga | 0.90 | 1.00 | 0.96 | 1.12 | 0.21 | 1.01 | 0.68 | 0.50 | 0.82 | 0.88 | 0.72 | 0.84 |
| Rsu1 | 1.06 | 1.06 | 1.20 | 0.78 | 0.70 | 0.72 | 0.99 | 1.00 | 1.00 | 1.17 | 1.04 | 0.98 |
| Rtp3 | 1.00 | 1.00 | 1.02 | 0.83 | 0.54 | 1.02 | 0.73 | 1.00 | 1.29 | 1.86 | 1.01 | 2.02 |
| Rusc2 | 1.10 | 1.39 | 1.18 | 2.13 | 0.48 | 1.36 | 0.77 | 0.48 | 0.80 | 0.92 | 1.41 | 1.21 |
| Ruvbl2 | 0.81 | 1.55 | 0.77 | 0.69 | 1.46 | 0.86 | 1.15 | 0.72 | 1.02 | 1.40 | 0.97 | 0.96 |
| Rybp | 0.94 | 0.82 | 0.88 | 1.10 | 1.00 | 0.76 | 1.05 | 0.41 | 0.98 | 1.02 | 0.73 | 1.07 |
| S1pr5 | 0.59 | 0.75 | 0.69 | 1.00 | 1.00 | 1.00 | 1.00 | 1.00 | 1.00 | 0.48 | 0.48 | 0.34 |
| Samd14 | 1.33 | 1.10 | 1.20 | 1.81 | 1.85 | 1.45 | 0.84 | 1.00 | 1.17 | 0.79 | 0.88 | 0.48 |
| Sap30 | 1.24 | 1.68 | 1.62 | 1.19 | 1.00 | 1.19 | 0.84 | 0.63 | 1.09 | 1.52 | 0.87 | 0.80 |
| Sash1 | 1.86 | 2.17 | 1.54 | 1.19 | 0.19 | 0.64 | 1.03 | 1.00 | 0.98 | 0.71 | 0.64 | 0.88 |
| Sbf2 | 0.98 | 1.12 | 0.92 | 0.91 | 0.48 | 0.81 | 1.17 | 0.68 | 1.17 | 0.88 | 0.95 | 1.13 |
| Sbno2 | 1.16 | 1.40 | 0.91 | 1.21 | 1.00 | 1.34 | 1.16 | 0.65 | 1.16 | 0.84 | 0.79 | 0.89 |
| Scaf4 | 0.93 | 0.90 | 0.98 | 0.96 | 0.66 | 1.06 | 0.94 | 0.78 | 1.03 | 0.91 | 0.70 | 1.00 |
| Scara3 | 1.02 | 1.15 | 1.34 | 0.43 | 0.80 | 0.54 | 0.82 | 1.00 | 0.84 | 0.53 | 0.66 | 0.74 |
| Scarna13 | 0.72 | 1.65 | 1.00 | 0.66 | 0.02 | 1.00 | 2.70 | 1.00 | 0.57 | 1.31 | 0.60 | 1.07 |
| Scarna3a | 1.00 | 1.00 | 1.00 | 1.00 | 0.01 | 1.00 | 1.00 | 1.00 | 1.00 | 1.00 | 1.00 | 1.00 |
| Scarna3b | 1.00 | 1.00 | 1.00 | 1.00 | 1.00 | 1.00 | 1.00 | 1.00 | 1.00 | 1.00 | 1.00 | 1.00 |
| Scd1 | 0.99 | 1.09 | 1.72 | 0.58 | 0.13 | 0.54 | 1.02 | 0.61 | 0.79 | 1.21 | 1.07 | 1.07 |
| Scd2 | 1.13 | 1.15 | 1.07 | 0.76 | 0.46 | 0.65 | 1.02 | 0.84 | 0.84 | 0.87 | 1.52 | 0.98 |
| Scd4 | 1.00 | 1.00 | 1.00 | 0.74 | 0.31 | 0.29 | 1.00 | 1.00 | 1.00 | 1.16 | 1.00 | 1.00 |
| Scg5 | 1.17 | 1.33 | 1.33 | 1.07 | 1.19 | 1.37 | 1.00 | 1.32 | 1.00 | 0.58 | 3.42 | 0.74 |
| Scgb1b27 | 1.00 | 1.00 | 1.00 | 1.00 | 1.00 | 1.00 | 1.00 | 1.00 | 1.00 | 1.00 | 1.00 | 1.00 |
| Scn2b | 1.17 | 1.02 | 1.24 | 1.80 | 1.00 | 1.99 | 1.00 | 1.00 | 1.00 | 0.83 | 1.22 | 1.14 |
| Scn7a | 1.42 | 1.18 | 1.50 | 0.50 | 0.22 | 0.55 | 1.00 | 1.00 | 1.00 | 1.81 | 1.26 | 2.01 |
| Sde2 | 0.97 | 1.11 | 1.10 | 1.59 | 0.63 | 1.39 | 0.97 | 1.31 | 0.86 | 1.04 | 0.66 | 1.05 |
| Sdr16c6 | 1.60 | 1.40 | 1.59 | 1.00 | 1.00 | 1.00 | 1.00 | 1.00 | 1.00 | 1.00 | 1.00 | 1.00 |
| Sdr9c7 | 1.27 | 1.42 | 1.32 | 1.00 | 1.00 | 1.00 | 1.00 | 1.00 | 1.00 | 1.00 | 1.00 | 1.00 |
| Sec24d | 0.96 | 0.81 | 0.76 | 1.07 | 0.65 | 0.90 | 1.00 | 1.00 | 0.89 | 1.00 | 0.74 | 0.94 |
| Secisbp2 | 0.89 | 0.81 | 0.79 | 1.20 | 1.00 | 1.37 | 0.99 | 1.81 | 1.20 | 0.93 | 0.82 | 1.15 |
| Secisbp2l | 1.07 | 0.96 | 0.84 | 1.20 | 0.16 | 0.73 | 0.97 | 1.00 | 1.14 | 0.99 | 0.72 | 1.09 |
| Sema3d | 1.00 | 1.00 | 1.00 | 0.86 | 1.00 | 0.63 | 1.00 | 1.00 | 1.00 | 0.65 | 0.47 | 0.67 |
| Sema3g | 1.68 | 1.78 | 1.49 | 1.15 | 0.22 | 1.00 | 1.00 | 1.00 | 1.00 | 0.95 | 0.89 | 1.13 |
| Sema4c | 0.90 | 0.95 | 0.99 | 1.10 | 0.53 | 1.45 | 0.77 | 1.00 | 0.84 | 0.91 | 0.99 | 0.85 |
| Sema4d | 1.06 | 0.98 | 0.88 | 0.65 | 1.00 | 0.50 | 1.16 | 1.00 | 0.99 | 0.90 | 0.60 | 0.81 |
| Senp5 | 0.95 | 0.83 | 0.85 | 1.07 | 0.64 | 0.89 | 1.15 | 0.88 | 0.98 | 0.90 | 0.71 | 1.04 |
| Sept11 | 0.78 | 0.63 | 0.74 | 1.23 | 0.23 | 0.99 | 0.84 | 1.00 | 0.81 | 0.85 | 0.57 | 1.12 |
| Sept3 | 1.00 | 1.00 | 1.00 | 1.45 | 1.00 | 2.04 | 1.13 | 0.60 | 0.91 | 0.64 | 4.94 | 0.95 |
| Sept8 | 0.80 | 0.87 | 0.84 | 1.11 | 0.20 | 0.99 | 0.92 | 1.00 | 0.81 | 0.70 | 0.69 | 0.63 |
| Serp1 | 0.96 | 0.87 | 0.80 | 1.48 | 0.97 | 1.05 | 0.89 | 0.94 | 1.03 | 1.24 | 0.89 | 1.24 |
| Serpina1f | 1.00 | 1.00 | 1.00 | 1.00 | 0.42 | 0.09 | 1.00 | 1.00 | 1.00 | 1.00 | 1.00 | 1.00 |
| Serpina3f | 1.00 | 1.00 | 1.00 | 0.46 | 1.00 | 0.32 | 1.00 | 1.00 | 1.00 | 0.83 | 0.45 | 0.47 |
| Serpina3i | 1.00 | 1.00 | 1.00 | 1.77 | 0.91 | 1.38 | 1.00 | 1.00 | 1.00 | 1.47 | 0.85 | 1.14 |
| Serpina3j | 0.57 | 0.46 | 0.46 | 1.00 | 1.00 | 1.00 | 1.00 | 1.00 | 1.00 | 1.00 | 1.00 | 1.00 |
| Serpina7 | 1.00 | 1.00 | 1.16 | 1.00 | 1.00 | 1.00 | 1.00 | 1.00 | 1.21 | 1.00 | 1.00 | 1.00 |
| Serpinb10 | 0.98 | 1.00 | 1.39 | 1.00 | 1.00 | 1.00 | 1.00 | 1.00 | 1.00 | 1.54 | 0.85 | 0.68 |
| Serpinb2 | 0.62 | 0.65 | 1.07 | 1.00 | 1.00 | 1.00 | 1.00 | 1.00 | 1.00 | 1.13 | 0.67 | 0.80 |
| Serpinb3a | 0.94 | 1.08 | 1.42 | 1.00 | 1.00 | 1.00 | 1.00 | 1.00 | 1.00 | 1.00 | 1.00 | 1.00 |
| Serpinb3b | 0.40 | 0.44 | 0.93 | 1.00 | 1.00 | 1.00 | 1.00 | 1.00 | 1.00 | 1.00 | 1.00 | 1.00 |
| Serpini1 | 0.88 | 1.16 | 1.50 | 1.44 | 1.00 | 1.00 | 1.47 | 1.00 | 0.91 | 1.32 | 2.25 | 1.19 |

Fig. 35- 84

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Rnf39 | 1.25 | 2.09 | 1.41 | 1.03 | 1.36 | 1.04 | 1.22 | 0.02 | 1.04 | 1.00 | 1.00 | 1.00 |
| Rnf44 | 1.08 | 0.82 | 1.07 | 1.00 | 0.86 | 0.97 | 1.04 | 0.19 | 1.15 | 0.56 | 1.12 | 1.02 |
| Rnft1 | 0.91 | 0.82 | 0.75 | 0.84 | 1.00 | 0.86 | 0.81 | 0.08 | 1.00 | 0.55 | 1.00 | 1.04 |
| Rnu12 | 1.00 | 1.00 | 1.00 | 1.00 | 0.02 | 1.00 | 1.00 | 1.00 | 0.33 | 1.00 | 1.00 | 1.00 |
| Rpa3 | 1.00 | 1.00 | 1.00 | 1.09 | 1.00 | 0.71 | 1.14 | 0.25 | 0.65 | 0.54 | 0.83 | 0.97 |
| Rpl12 | 0.76 | 0.60 | 0.85 | 1.00 | 0.58 | 0.99 | 1.02 | 4.89 | 1.15 | 2.69 | 1.34 | 1.13 |
| Rpl30 | 1.16 | 1.44 | 2.07 | 1.44 | 1.35 | 1.94 | 0.68 | 2.67 | 0.99 | 1.64 | 1.25 | 0.92 |
| Rpl37 | 1.06 | 0.77 | 1.05 | 1.24 | 0.83 | 1.06 | 1.59 | 1.08 | 0.88 | 1.27 | 0.96 | 1.24 |
| Rpp38 | 0.69 | 1.13 | 0.76 | 0.94 | 1.00 | 0.99 | 0.84 | 0.40 | 0.70 | 0.20 | 0.79 | 0.68 |
| Rprd1b | 0.90 | 0.96 | 0.78 | 0.87 | 1.00 | 1.07 | 0.94 | 0.17 | 1.06 | 0.44 | 0.77 | 0.86 |
| Rprd2 | 1.12 | 0.89 | 1.03 | 0.85 | 0.64 | 0.94 | 0.80 | 0.20 | 1.08 | 0.49 | 0.82 | 0.89 |
| Rprl2 | 1.00 | 1.00 | 1.00 | 1.00 | 1.00 | 1.00 | 1.00 | 1.00 | 1.00 | 1.00 | 1.00 | 1.00 |
| Rprml | 1.00 | 1.00 | 1.00 | 1.39 | 1.42 | 1.09 | 1.00 | 1.00 | 1.00 | 1.00 | 1.00 | 1.00 |
| Rps10 | 0.85 | 0.90 | 0.83 | 0.73 | 1.10 | 1.12 | 1.47 | 1.67 | 0.81 | 1.63 | 1.17 | 1.14 |
| Rps27 | 1.52 | 0.82 | 0.62 | 1.20 | 1.00 | 0.93 | 1.07 | 1.36 | 0.98 | 1.18 | 1.26 | 0.94 |
| Rraga | 1.44 | 1.45 | 1.07 | 1.15 | 0.48 | 1.10 | 0.96 | 0.11 | 0.86 | 0.25 | 0.82 | 0.93 |
| Rsu1 | 1.17 | 1.11 | 1.26 | 1.11 | 1.00 | 0.83 | 1.06 | 0.14 | 1.14 | 0.46 | 1.22 | 1.31 |
| Rtp3 | 1.00 | 1.00 | 1.00 | 1.00 | 1.00 | 1.00 | 1.00 | 1.00 | 1.00 | 1.00 | 1.00 | 1.00 |
| Rusc2 | 1.00 | 1.00 | 1.00 | 1.06 | 1.00 | 1.04 | 1.33 | 0.14 | 1.31 | 1.00 | 1.00 | 1.00 |
| Ruvbl2 | 1.00 | 1.00 | 1.00 | 0.86 | 0.49 | 1.10 | 1.23 | 0.52 | 0.76 | 0.50 | 0.84 | 1.00 |
| Rybp | 1.27 | 1.00 | 1.31 | 0.94 | 1.00 | 0.90 | 0.90 | 0.16 | 0.98 | 0.67 | 0.91 | 1.00 |
| S1pr5 | 0.91 | 0.41 | 0.40 | 0.81 | 0.68 | 0.81 | 0.44 | 0.65 | 0.32 | 0.41 | 0.35 | 0.37 |
| Samd14 | 0.77 | 1.00 | 1.00 | 1.13 | 0.79 | 1.15 | 1.16 | 0.76 | 0.89 | 0.73 | 0.76 | 0.79 |
| Sap30 | 3.28 | 1.17 | 1.52 | 1.35 | 1.00 | 1.13 | 0.94 | 0.18 | 0.93 | 1.08 | 1.81 | 1.32 |
| Sash1 | 1.63 | 1.98 | 2.17 | 0.85 | 1.00 | 0.85 | 1.17 | 0.25 | 1.40 | 1.00 | 1.00 | 1.07 |
| Sbf2 | 1.16 | 1.45 | 0.97 | 0.99 | 1.00 | 0.97 | 1.20 | 0.18 | 1.29 | 1.00 | 1.00 | 1.00 |
| Sbno2 | 1.00 | 1.05 | 1.00 | 1.20 | 1.00 | 0.99 | 1.06 | 0.18 | 0.95 | 0.86 | 1.23 | 1.18 |
| Scaf4 | 1.28 | 1.54 | 1.32 | 0.87 | 1.00 | 1.01 | 1.24 | 0.15 | 1.06 | 0.31 | 0.83 | 0.90 |
| Scara3 | 1.03 | 1.28 | 1.19 | 0.96 | 1.00 | 0.92 | 1.00 | 0.20 | 1.11 | 1.00 | 1.00 | 1.00 |
| Scarna13 | 1.00 | 1.00 | 1.00 | 1.39 | 1.00 | 0.52 | 1.26 | 2.56 | 1.00 | 0.30 | 2.39 | 2.62 |
| Scarna3a | 1.00 | 1.00 | 1.00 | 1.00 | 1.00 | 1.00 | 1.00 | 1.00 | 1.00 | 1.00 | 1.00 | 1.00 |
| Scarna3b | 1.00 | 1.00 | 1.00 | 1.00 | 1.00 | 1.00 | 1.00 | 1.00 | 1.00 | 1.00 | 1.00 | 1.00 |
| Scd1 | 0.73 | 0.86 | 0.67 | 0.94 | 0.41 | 0.99 | 1.23 | 0.29 | 1.57 | 0.49 | 0.83 | 0.57 |
| Scd2 | 0.59 | 0.64 | 0.75 | 0.93 | 1.06 | 0.95 | 0.48 | 0.34 | 0.55 | 0.46 | 0.61 | 0.54 |
| Scd4 | 1.00 | 1.00 | 1.00 | 1.00 | 1.00 | 1.00 | 1.14 | 0.55 | 1.53 | 1.00 | 1.00 | 1.00 |
| Scg5 | 0.66 | 0.69 | 0.78 | 1.14 | 1.20 | 1.03 | 1.00 | 1.00 | 1.00 | 1.00 | 1.00 | 1.00 |
| Scgb1b27 | 1.00 | 1.00 | 1.00 | 1.00 | 1.00 | 1.00 | 0.93 | 3.81 | 1.35 | 1.00 | 1.00 | 1.00 |
| Scn2b | 1.00 | 1.00 | 1.00 | 1.06 | 1.00 | 1.01 | 1.34 | 1.00 | 2.29 | 0.90 | 0.96 | 1.00 |
| Scn7a | 1.01 | 1.00 | 1.00 | 1.00 | 1.00 | 1.00 | 1.04 | 0.42 | 1.79 | 1.00 | 1.00 | 1.00 |
| Sde2 | 1.13 | 1.46 | 1.09 | 1.03 | 0.38 | 1.02 | 0.88 | 0.18 | 0.98 | 0.61 | 0.86 | 1.06 |
| Sdr16c6 | 1.00 | 1.00 | 1.00 | 1.00 | 1.00 | 1.00 | 0.99 | 0.01 | 1.13 | 1.00 | 1.00 | 1.00 |
| Sdr9c7 | 1.07 | 1.02 | 1.91 | 1.00 | 1.00 | 1.00 | 0.56 | 0.08 | 0.59 | 1.00 | 1.00 | 1.00 |
| Sec24d | 0.86 | 0.62 | 0.91 | 0.90 | 1.00 | 0.99 | 0.66 | 0.16 | 0.98 | 0.57 | 0.95 | 0.99 |
| Secisbp2 | 1.33 | 1.00 | 0.93 | 0.96 | 1.00 | 1.02 | 0.75 | 0.19 | 0.79 | 0.40 | 0.79 | 0.82 |
| Secisbp2l | 1.09 | 1.01 | 0.92 | 0.92 | 1.00 | 0.98 | 0.97 | 0.10 | 1.39 | 0.67 | 0.87 | 0.77 |
| Sema3d | 1.00 | 1.00 | 1.00 | 0.79 | 1.00 | 1.05 | 0.57 | 0.11 | 0.77 | 1.00 | 1.00 | 1.00 |
| Sema3g | 1.42 | 1.00 | 1.58 | 1.50 | 1.00 | 1.47 | 1.60 | 0.50 | 1.99 | 1.00 | 1.00 | 1.00 |
| Sema4c | 1.00 | 1.00 | 1.00 | 1.04 | 0.56 | 1.13 | 0.72 | 0.08 | 0.64 | 0.61 | 0.79 | 0.86 |
| Sema4d | 1.07 | 1.17 | 1.01 | 0.88 | 0.41 | 0.83 | 0.60 | 0.19 | 0.74 | 0.83 | 0.97 | 0.96 |
| Senp5 | 0.88 | 1.46 | 1.00 | 1.02 | 1.12 | 0.96 | 0.95 | 0.13 | 1.13 | 0.60 | 0.86 | 0.95 |
| Sept11 | 1.12 | 1.00 | 1.04 | 0.85 | 0.56 | 0.87 | 0.85 | 0.15 | 0.94 | 0.40 | 0.64 | 0.85 |
| Sept3 | 1.00 | 1.00 | 1.00 | 1.02 | 0.83 | 1.02 | 0.39 | 0.32 | 0.73 | 1.00 | 1.00 | 1.00 |
| Sept8 | 0.89 | 0.96 | 1.04 | 0.88 | 1.52 | 0.91 | 0.70 | 0.20 | 0.69 | 0.45 | 0.52 | 0.67 |
| Serp1 | 0.87 | 0.83 | 0.91 | 1.01 | 0.44 | 0.95 | 0.84 | 0.16 | 0.98 | 0.54 | 1.00 | 1.18 |
| Serpina1f | 1.00 | 1.00 | 1.00 | 1.00 | 1.00 | 1.00 | 1.00 | 1.00 | 1.00 | 1.00 | 1.00 | 1.00 |
| Serpina3f | 1.00 | 1.00 | 1.00 | 1.00 | 1.00 | 1.00 | 0.71 | 0.40 | 0.92 | 0.58 | 0.66 | 0.52 |
| Serpina3i | 1.00 | 1.00 | 1.00 | 1.00 | 1.00 | 1.00 | 0.74 | 0.05 | 0.93 | 1.00 | 1.00 | 1.00 |
| Serpina3j | 1.00 | 1.00 | 1.00 | 1.00 | 1.00 | 1.00 | 0.04 | 0.10 | 0.06 | 1.00 | 1.00 | 1.00 |
| Serpina7 | 1.00 | 1.00 | 1.00 | 1.00 | 1.00 | 1.00 | 1.00 | 1.00 | 1.00 | 1.00 | 1.00 | 1.00 |
| Serpinb10 | 1.00 | 1.00 | 1.00 | 1.00 | 1.00 | 1.00 | 0.42 | 0.12 | 0.55 | 0.76 | 1.16 | 1.32 |
| Serpinb2 | 1.00 | 1.00 | 1.00 | 1.00 | 1.00 | 1.00 | 0.54 | 0.06 | 0.77 | 0.59 | 0.45 | 0.94 |
| Serpinb3a | 1.00 | 1.00 | 1.00 | 1.00 | 1.00 | 1.00 | 0.15 | 0.31 | 0.36 | 1.00 | 1.00 | 1.00 |
| Serpinb3b | 1.00 | 1.00 | 1.00 | 1.00 | 1.00 | 1.00 | 0.38 | 0.06 | 0.50 | 1.00 | 1.00 | 1.00 |
| Serpini1 | 1.13 | 1.55 | 0.75 | 1.11 | 1.01 | 1.01 | 1.00 | 1.00 | 1.00 | 1.00 | 0.80 | 0.97 |

Fig. 35- 85

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Sertad4 | 0.81 | 1.00 | 0.70 | 1.00 | 1.00 | 1.00 | 0.54 | 0.39 | 0.64 | 1.00 | 1.00 | 0.65 |
| Sesn2 | 1.83 | 1.00 | 2.00 | 3.68 | 0.15 | 2.61 | 1.28 | 2.04 | 1.20 | 1.00 | 0.40 | 1.18 |
| Setdb1 | 0.97 | 1.18 | 1.33 | 0.97 | 0.34 | 0.86 | 1.08 | 1.06 | 0.87 | 0.33 | 0.34 | 1.03 |
| Sfrp2 | 0.36 | 0.69 | 0.61 | 0.91 | 0.80 | 0.43 | 0.50 | 0.35 | 0.50 | 1.00 | 1.00 | 1.00 |
| Sfrp5 | 1.18 | 0.86 | 1.21 | 0.91 | 2.89 | 1.35 | 0.62 | 0.62 | 0.90 | 1.00 | 1.18 | 1.00 |
| Sft2d1 | 1.06 | 0.63 | 1.33 | 0.18 | 0.62 | 0.90 | 0.98 | 0.64 | 0.83 | 0.18 | 0.34 | 0.91 |
| Sgk2 | 1.00 | 1.00 | 1.00 | 0.14 | 0.23 | 0.71 | 1.00 | 1.00 | 1.00 | 1.00 | 1.00 | 1.00 |
| Sgpl1 | 1.46 | 2.43 | 2.44 | 2.07 | 0.64 | 2.28 | 1.13 | 1.21 | 1.10 | 0.44 | 0.48 | 0.97 |
| Sh2b1 | 0.77 | 1.16 | 1.02 | 0.57 | 0.28 | 0.87 | 0.92 | 0.96 | 0.92 | 0.31 | 0.70 | 1.03 |
| Sh2d1a | 1.00 | 1.00 | 1.00 | 1.00 | 1.00 | 1.00 | 1.00 | 1.00 | 1.00 | 0.68 | 1.06 | 0.68 |
| Sh3bp5 | 0.73 | 3.20 | 0.86 | 1.50 | 0.12 | 0.98 | 0.92 | 0.90 | 0.95 | 0.23 | 0.11 | 0.88 |
| Sh3gl1 | 1.55 | 1.53 | 1.12 | 0.68 | 0.87 | 0.98 | 0.97 | 0.91 | 1.02 | 0.35 | 0.68 | 0.91 |
| Shisa7 | 1.00 | 1.00 | 1.00 | 1.00 | 0.41 | 1.00 | 1.00 | 1.00 | 1.00 | 0.78 | 0.85 | 0.65 |
| Shpk | 0.73 | 1.00 | 0.99 | 0.72 | 0.37 | 0.84 | 1.03 | 0.47 | 0.90 | 0.61 | 0.53 | 0.95 |
| Sik2 | 1.04 | 1.51 | 2.35 | 2.25 | 0.24 | 1.37 | 1.89 | 3.72 | 1.63 | 1.00 | 1.00 | 1.32 |
| Sik3 | 1.54 | 2.26 | 1.26 | 1.61 | 0.56 | 1.28 | 1.49 | 1.55 | 1.08 | 0.51 | 0.52 | 0.95 |
| Sipa1l3 | 1.00 | 1.00 | 1.00 | 1.23 | 0.36 | 0.72 | 1.18 | 1.01 | 1.43 | 0.63 | 0.57 | 1.21 |
| Six5 | 0.56 | 1.00 | 0.84 | 1.09 | 0.60 | 0.97 | 0.62 | 0.55 | 0.65 | 0.39 | 0.39 | 0.68 |
| Skint10 | 1.00 | 1.00 | 1.00 | 1.00 | 1.00 | 1.00 | 1.00 | 1.00 | 1.00 | 1.00 | 1.00 | 1.00 |
| Slamf6 | 1.00 | 1.00 | 1.00 | 1.00 | 1.00 | 1.00 | 1.00 | 1.00 | 1.00 | 1.00 | 0.32 | 0.46 |
| Slc10a3 | 1.21 | 2.07 | 1.96 | 1.01 | 0.57 | 1.06 | 1.45 | 1.15 | 1.55 | 0.65 | 0.54 | 1.03 |
| Slc16a1 | 1.72 | 2.49 | 1.40 | 0.48 | 0.19 | 0.54 | 0.69 | 0.90 | 1.01 | 0.49 | 0.70 | 1.21 |
| Slc16a2 | 0.76 | 1.00 | 1.00 | 1.31 | 0.31 | 0.93 | 0.89 | 0.91 | 0.88 | 0.95 | 0.70 | 0.88 |
| Slc16a6 | 1.13 | 1.00 | 0.78 | 1.13 | 0.89 | 0.90 | 1.16 | 1.10 | 1.13 | 1.00 | 0.68 | 0.91 |
| Slc17a5 | 1.56 | 2.03 | 1.22 | 2.09 | 1.01 | 1.66 | 1.53 | 1.61 | 1.21 | 0.58 | 0.44 | 1.09 |
| Slc18a2 | 0.86 | 1.00 | 0.88 | 1.00 | 1.00 | 1.00 | 1.14 | 1.58 | 1.00 | 1.00 | 1.00 | 0.75 |
| Slc22a17 | 0.59 | 0.68 | 1.06 | 0.61 | 0.19 | 0.73 | 0.64 | 0.49 | 0.80 | 0.33 | 0.80 | 0.72 |
| Slc24a3 | 0.74 | 1.00 | 1.48 | 0.77 | 0.13 | 0.79 | 1.00 | 1.11 | 1.23 | 0.54 | 0.20 | 1.00 |
| Slc25a16 | 0.77 | 1.91 | 0.86 | 1.35 | 0.24 | 1.00 | 0.90 | 1.04 | 0.94 | 0.43 | 0.29 | 1.04 |
| Slc25a24 | 1.54 | 1.52 | 1.46 | 2.73 | 0.73 | 0.70 | 1.09 | 0.88 | 1.00 | 0.19 | 0.39 | 0.84 |
| Slc25a35 | 0.84 | 0.79 | 0.91 | 0.52 | 0.15 | 0.50 | 1.19 | 1.22 | 0.82 | 0.64 | 0.49 | 1.22 |
| Slc25a36 | 0.75 | 1.00 | 0.94 | 2.42 | 0.21 | 0.76 | 1.29 | 1.73 | 1.53 | 0.82 | 0.63 | 0.98 |
| Slc26a2 | 0.53 | 1.00 | 0.79 | 0.53 | 1.08 | 0.32 | 0.62 | 1.09 | 1.36 | 2.32 | 1.98 | 0.82 |
| Slc27a6 | 1.00 | 1.00 | 1.00 | 1.00 | 1.00 | 1.00 | 1.00 | 0.97 | 1.00 | 1.00 | 0.86 | 0.32 |
| Slc30a7 | 0.85 | 1.00 | 1.01 | 1.61 | 0.37 | 1.14 | 1.03 | 1.01 | 1.10 | 0.79 | 0.55 | 0.92 |
| Slc35b4 | 1.15 | 0.95 | 0.90 | 1.56 | 0.65 | 1.28 | 0.84 | 0.73 | 1.33 | 0.57 | 0.54 | 0.93 |
| Slc35d1 | 0.52 | 1.00 | 0.67 | 2.47 | 0.44 | 0.89 | 1.00 | 0.88 | 0.89 | 1.00 | 1.00 | 0.94 |
| Slc35f2 | 1.00 | 1.00 | 1.00 | 1.00 | 1.00 | 1.00 | 1.00 | 1.00 | 1.00 | 1.00 | 1.00 | 1.00 |
| Slc35f5 | 1.74 | 3.36 | 1.57 | 1.22 | 0.32 | 0.96 | 1.10 | 1.14 | 1.07 | 0.18 | 0.30 | 1.14 |
| Slc35g1 | 0.79 | 1.00 | 1.18 | 0.98 | 0.21 | 0.70 | 1.03 | 1.25 | 0.76 | 0.67 | 0.84 | 1.78 |
| Slc39a10 | 0.57 | 1.00 | 0.80 | 1.40 | 0.17 | 0.81 | 0.80 | 0.79 | 1.21 | 0.54 | 0.43 | 0.79 |
| Slc40a1 | 0.68 | 0.90 | 0.72 | 1.54 | 0.82 | 0.89 | 0.33 | 0.24 | 0.32 | 0.44 | 0.36 | 0.72 |
| Slc45a3 | 0.78 | 1.00 | 1.22 | 1.00 | 1.00 | 1.00 | 0.93 | 0.93 | 1.59 | 0.87 | 0.37 | 1.27 |
| Slc6a13 | 1.00 | 1.00 | 1.00 | 1.00 | 1.00 | 1.00 | 1.00 | 1.00 | 1.00 | 1.00 | 1.00 | 1.00 |
| Slc6a14 | 1.00 | 1.00 | 1.00 | 1.00 | 1.00 | 1.00 | 1.00 | 1.00 | 1.00 | 0.44 | 0.59 | 1.28 |
| Slc6a19 | 1.00 | 1.00 | 1.00 | 1.66 | 2.54 | 1.97 | 1.00 | 1.00 | 1.00 | 1.00 | 1.00 | 1.00 |
| Slc6a6 | 0.73 | 1.01 | 0.90 | 1.13 | 0.16 | 0.89 | 0.76 | 0.82 | 0.93 | 0.58 | 0.36 | 0.93 |
| Slco4a1 | 1.00 | 1.00 | 1.00 | 0.14 | 0.21 | 0.25 | 1.00 | 1.00 | 1.00 | 1.00 | 1.00 | 1.61 |
| Slfn3 | 1.00 | 1.00 | 1.00 | 1.00 | 1.00 | 1.00 | 1.40 | 1.70 | 1.31 | 1.00 | 1.00 | 1.39 |
| Slfn9 | 1.00 | 1.00 | 1.00 | 1.00 | 1.00 | 1.00 | 1.00 | 1.00 | 1.00 | 1.00 | 1.00 | 1.00 |
| Slitrk6 | 1.00 | 1.00 | 1.00 | 1.00 | 1.00 | 1.00 | 1.00 | 1.00 | 1.00 | 1.00 | 1.00 | 1.00 |
| Sltm | 1.17 | 1.66 | 1.39 | 1.20 | 0.78 | 0.95 | 0.99 | 1.38 | 1.12 | 0.60 | 0.50 | 1.11 |
| Smad3 | 1.21 | 2.10 | 0.90 | 1.14 | 0.12 | 0.71 | 1.03 | 1.14 | 1.04 | 0.39 | 0.56 | 1.10 |
| Smad6 | 0.65 | 1.00 | 0.46 | 0.61 | 0.33 | 1.09 | 1.31 | 1.29 | 1.06 | 0.50 | 0.49 | 1.18 |
| Smg1 | 1.35 | 2.39 | 1.30 | 2.76 | 0.58 | 1.12 | 1.77 | 2.57 | 1.31 | 0.67 | 0.43 | 1.01 |
| Smim3 | 1.25 | 1.36 | 0.67 | 1.00 | 0.73 | 0.55 | 0.06 | 0.08 | 0.10 | 0.61 | 0.55 | 1.04 |
| Snai2 | 0.68 | 1.00 | 1.09 | 1.00 | 0.50 | 0.70 | 0.71 | 0.48 | 1.16 | 0.22 | 0.17 | 0.35 |
| Snai3 | 1.78 | 0.88 | 0.71 | 1.00 | 1.00 | 0.63 | 0.20 | 0.50 | 0.28 | 1.00 | 1.00 | 1.00 |
| Snca | 1.00 | 1.00 | 1.00 | 0.98 | 0.21 | 1.03 | 0.68 | 1.45 | 0.36 | 1.16 | 0.93 | 1.21 |
| Snn | 0.61 | 0.81 | 0.91 | 1.43 | 0.32 | 1.36 | 0.84 | 0.86 | 0.92 | 0.75 | 0.46 | 0.94 |
| Snora24 | 1.00 | 1.00 | 1.00 | 1.00 | 1.00 | 1.00 | 1.00 | 1.00 | 1.00 | 1.00 | 1.00 | 1.00 |
| Snora26 | 1.00 | 1.00 | 1.00 | 1.00 | 1.00 | 1.00 | 1.00 | 1.00 | 1.00 | 1.00 | 1.00 | 1.00 |
| Snora68 | 1.00 | 1.00 | 1.00 | 1.00 | 1.00 | 1.00 | 1.00 | 1.00 | 1.00 | 1.00 | 1.00 | 1.00 |
| Snord23 | 1.00 | 1.00 | 1.00 | 0.01 | 1.00 | 1.00 | 1.00 | 1.00 | 1.00 | 1.00 | 1.00 | 1.00 |

Fig. 35- 86

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Sertad4 | 1.51 | 1.13 | 1.32 | 0.88 | 1.00 | 0.58 | 1.00 | 1.00 | 0.96 | 1.14 | 0.58 | 1.17 |
| Sesn2 | 1.10 | 1.22 | 1.70 | 3.37 | 1.01 | 2.17 | 2.48 | 1.00 | 2.05 | 0.95 | 0.54 | 0.80 |
| Setdb1 | 0.73 | 0.67 | 0.85 | 0.97 | 1.69 | 0.98 | 0.93 | 1.00 | 1.12 | 0.98 | 0.82 | 1.01 |
| Sfrp2 | 0.79 | 0.85 | 0.91 | 0.57 | 1.13 | 0.79 | 1.00 | 1.00 | 1.00 | 0.36 | 0.42 | 0.68 |
| Sfrp5 | 1.49 | 1.18 | 1.00 | 1.00 | 1.00 | 0.98 | 1.00 | 1.00 | 1.00 | 1.55 | 1.11 | 1.37 |
| Sft2d1 | 1.08 | 1.19 | 1.07 | 0.73 | 3.69 | 0.75 | 0.74 | 0.23 | 0.70 | 0.98 | 1.52 | 1.25 |
| Sgk2 | 1.00 | 1.00 | 1.00 | 0.72 | 0.97 | 1.00 | 0.85 | 0.63 | 1.39 | 1.02 | 1.44 | 0.91 |
| Sgpl1 | 0.63 | 0.53 | 0.90 | 1.04 | 1.59 | 1.05 | 0.83 | 0.47 | 0.86 | 0.97 | 0.71 | 0.96 |
| Sh2b1 | 0.85 | 0.84 | 1.00 | 1.07 | 1.94 | 1.02 | 1.22 | 0.41 | 1.10 | 0.98 | 0.90 | 0.95 |
| Sh2d1a | 0.91 | 1.17 | 0.83 | 1.00 | 1.00 | 1.00 | 1.00 | 1.00 | 1.00 | 1.00 | 1.00 | 1.00 |
| Sh3bp5 | 1.60 | 1.49 | 1.49 | 1.09 | 3.30 | 1.05 | 0.73 | 0.90 | 0.87 | 0.94 | 0.76 | 1.00 |
| Sh3gl1 | 0.87 | 1.06 | 0.95 | 0.97 | 1.13 | 0.95 | 1.06 | 0.14 | 1.12 | 0.90 | 1.02 | 0.91 |
| Shisa7 | 1.00 | 1.00 | 1.00 | 0.14 | 0.14 | 0.10 | 1.00 | 1.00 | 1.00 | 1.18 | 1.00 | 1.35 |
| Shpk | 1.09 | 1.15 | 1.21 | 1.02 | 0.96 | 0.98 | 0.70 | 0.59 | 0.67 | 0.99 | 0.85 | 1.00 |
| Sik2 | 0.44 | 0.35 | 0.85 | 1.51 | 1.00 | 1.34 | 1.33 | 1.00 | 1.72 | 1.09 | 0.65 | 0.88 |
| Sik3 | 0.89 | 0.85 | 0.92 | 1.23 | 1.61 | 1.10 | 1.54 | 2.09 | 1.24 | 1.11 | 0.84 | 0.96 |
| Sipa1l3 | 0.76 | 0.78 | 1.10 | 1.02 | 1.01 | 1.12 | 0.62 | 1.00 | 0.84 | 0.94 | 0.67 | 0.93 |
| Six5 | 1.28 | 1.39 | 1.43 | 0.87 | 1.38 | 1.00 | 1.21 | 1.00 | 0.98 | 0.73 | 0.60 | 0.83 |
| Skint10 | 1.41 | 0.80 | 0.98 | 1.00 | 1.00 | 1.00 | 1.00 | 1.00 | 1.00 | 1.00 | 1.00 | 1.00 |
| Slamf6 | 0.87 | 0.86 | 0.80 | 1.00 | 1.00 | 1.00 | 1.00 | 1.00 | 1.00 | 0.61 | 0.41 | 0.66 |
| Slc10a3 | 0.98 | 0.96 | 1.10 | 1.24 | 1.78 | 1.03 | 1.45 | 0.92 | 1.93 | 1.08 | 0.87 | 1.16 |
| Slc16a1 | 0.39 | 0.35 | 0.43 | 2.74 | 2.79 | 1.79 | 1.16 | 0.51 | 1.26 | 0.85 | 0.75 | 1.08 |
| Slc16a2 | 1.60 | 1.06 | 1.33 | 0.92 | 1.07 | 1.02 | 0.32 | 0.19 | 0.47 | 0.83 | 0.56 | 0.72 |
| Slc16a6 | 0.67 | 0.72 | 0.91 | 1.17 | 1.00 | 0.76 | 1.66 | 1.00 | 1.40 | 1.12 | 0.75 | 1.21 |
| Slc17a5 | 1.05 | 0.95 | 0.94 | 1.16 | 1.92 | 1.25 | 0.86 | 0.60 | 1.09 | 1.00 | 0.82 | 1.02 |
| Slc18a2 | 0.17 | 0.15 | 0.24 | 1.36 | 1.00 | 1.00 | 1.00 | 1.00 | 1.00 | 1.25 | 1.04 | 1.37 |
| Slc22a17 | 1.39 | 1.30 | 1.15 | 0.88 | 1.12 | 1.01 | 1.00 | 1.00 | 0.98 | 0.83 | 0.88 | 0.83 |
| Slc24a3 | 0.54 | 0.62 | 0.68 | 1.10 | 1.00 | 1.00 | 1.00 | 1.00 | 1.00 | 0.85 | 0.62 | 0.88 |
| Slc25a16 | 0.86 | 0.81 | 0.92 | 1.01 | 1.62 | 0.97 | 0.76 | 0.53 | 0.77 | 0.96 | 0.86 | 0.90 |
| Slc25a24 | 1.05 | 0.79 | 1.20 | 1.02 | 1.00 | 0.77 | 1.00 | 1.00 | 1.00 | 0.95 | 0.72 | 1.06 |
| Slc25a35 | 0.73 | 0.54 | 0.68 | 0.88 | 1.04 | 0.99 | 1.00 | 1.00 | 1.00 | 1.20 | 0.84 | 0.90 |
| Slc25a36 | 0.75 | 0.52 | 1.15 | 1.12 | 1.26 | 1.06 | 1.00 | 1.00 | 1.00 | 0.96 | 0.36 | 0.91 |
| Slc26a2 | 0.23 | 0.21 | 0.45 | 0.93 | 1.00 | 1.12 | 0.92 | 1.00 | 0.84 | 1.31 | 0.82 | 1.06 |
| Slc27a6 | 1.52 | 1.36 | 2.79 | 1.00 | 1.00 | 1.00 | 1.00 | 1.00 | 1.00 | 1.00 | 1.00 | 1.00 |
| Slc30a7 | 0.71 | 0.67 | 0.94 | 1.02 | 1.11 | 1.02 | 0.76 | 1.00 | 1.01 | 1.03 | 0.80 | 0.94 |
| Slc35b4 | 0.52 | 0.43 | 0.63 | 1.21 | 1.53 | 1.17 | 0.73 | 0.86 | 0.84 | 0.98 | 0.84 | 0.94 |
| Slc35d1 | 0.80 | 0.61 | 1.17 | 0.99 | 1.00 | 0.94 | 0.73 | 1.00 | 0.78 | 1.06 | 0.44 | 0.94 |
| Slc35f2 | 0.86 | 0.78 | 1.04 | 0.72 | 0.62 | 0.84 | 1.00 | 1.00 | 1.00 | 0.94 | 0.83 | 0.94 |
| Slc35f5 | 1.26 | 1.05 | 1.71 | 1.09 | 1.46 | 1.01 | 1.27 | 0.54 | 1.45 | 1.02 | 0.98 | 1.04 |
| Slc35g1 | 0.73 | 0.67 | 0.90 | 1.25 | 1.99 | 1.23 | 1.43 | 1.17 | 1.58 | 0.81 | 0.65 | 0.84 |
| Slc39a10 | 0.66 | 0.55 | 0.80 | 0.92 | 1.00 | 1.12 | 1.00 | 1.00 | 1.00 | 0.72 | 0.51 | 1.05 |
| Slc40a1 | 2.01 | 1.49 | 2.47 | 1.13 | 1.66 | 0.97 | 0.57 | 0.33 | 0.79 | 1.56 | 1.07 | 1.24 |
| Slc45a3 | 1.94 | 1.78 | 1.61 | 1.35 | 2.99 | 1.19 | 1.38 | 0.49 | 1.47 | 0.76 | 0.61 | 0.78 |
| Slc6a13 | 2.81 | 3.47 | 2.81 | 1.97 | 1.86 | 1.47 | 0.65 | 0.57 | 0.70 | 1.00 | 1.00 | 1.00 |
| Slc6a14 | 1.00 | 1.00 | 1.00 | 1.00 | 1.00 | 1.00 | 1.00 | 1.00 | 1.00 | 0.75 | 0.63 | 0.74 |
| Slc6a19 | 0.70 | 0.60 | 0.65 | 1.37 | 1.73 | 1.60 | 1.00 | 1.00 | 1.00 | 1.40 | 2.00 | 2.88 |
| Slc6a6 | 0.83 | 0.69 | 1.09 | 1.33 | 1.76 | 1.31 | 0.44 | 0.36 | 0.69 | 1.24 | 0.95 | 1.18 |
| Slco4a1 | 0.87 | 0.92 | 0.89 | 0.93 | 1.44 | 1.37 | 1.00 | 1.00 | 1.00 | 0.70 | 0.45 | 0.76 |
| Slfn3 | 0.25 | 0.20 | 0.38 | 1.05 | 1.00 | 1.00 | 1.00 | 1.00 | 1.00 | 1.00 | 1.00 | 1.00 |
| Slfn9 | 0.32 | 0.19 | 0.56 | 1.00 | 1.00 | 1.00 | 1.00 | 1.00 | 1.00 | 1.05 | 1.00 | 0.98 |
| Slitrk6 | 1.00 | 1.00 | 1.00 | 0.41 | 1.00 | 0.70 | 1.00 | 1.00 | 1.00 | 0.59 | 0.51 | 0.77 |
| Sltm | 0.85 | 0.90 | 0.96 | 1.01 | 2.13 | 1.04 | 1.28 | 0.64 | 1.05 | 1.04 | 1.03 | 1.08 |
| Smad3 | 0.68 | 0.58 | 0.91 | 0.74 | 1.20 | 0.93 | 0.81 | 1.00 | 0.94 | 0.96 | 0.62 | 0.94 |
| Smad6 | 2.12 | 1.71 | 1.72 | 0.96 | 1.46 | 1.29 | 0.62 | 1.00 | 1.26 | 0.81 | 0.70 | 0.82 |
| Smg1 | 0.59 | 0.54 | 0.81 | 1.16 | 1.00 | 0.95 | 1.40 | 1.00 | 1.15 | 1.12 | 0.72 | 0.98 |
| Smim3 | 2.46 | 2.60 | 2.07 | 0.51 | 0.78 | 0.49 | 1.00 | 1.00 | 1.00 | 1.05 | 0.94 | 0.97 |
| Snai2 | 1.97 | 1.67 | 1.94 | 0.83 | 1.00 | 0.87 | 1.36 | 0.72 | 0.94 | 0.42 | 0.56 | 0.70 |
| Snai3 | 0.75 | 0.83 | 0.90 | 1.00 | 1.00 | 1.00 | 1.00 | 1.00 | 1.00 | 1.00 | 1.00 | 1.00 |
| Snca | 0.82 | 1.00 | 1.00 | 0.95 | 0.71 | 1.04 | 1.00 | 1.00 | 1.00 | 0.99 | 1.51 | 1.30 |
| Snn | 0.70 | 0.66 | 0.96 | 0.66 | 0.91 | 0.71 | 0.77 | 1.00 | 0.84 | 0.89 | 0.71 | 0.95 |
| Snora24 | 1.00 | 1.00 | 1.00 | 1.00 | 1.00 | 1.00 | 1.00 | 1.00 | 1.00 | 1.00 | 1.00 | 1.00 |
| Snora26 | 1.00 | 1.00 | 1.00 | 1.00 | 1.00 | 1.00 | 1.00 | 1.00 | 1.00 | 1.00 | 1.00 | 1.00 |
| Snora68 | 1.00 | 1.00 | 0.00 | 1.00 | 1.00 | 1.00 | 1.00 | 1.00 | 1.00 | 1.00 | 1.00 | 1.00 |
| Snord23 | 1.00 | 1.00 | 1.00 | 1.00 | 1.00 | 1.00 | 1.00 | 1.00 | 1.00 | 1.00 | 1.00 | 1.00 |

Fig. 35- 87

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Sertad4 | 0.58 | 0.52 | 0.70 | 0.66 | 1.00 | 1.08 | 1.14 | 1.00 | 1.30 | 0.87 | 1.09 | 1.00 |
| Sesn2 | 1.08 | 0.91 | 0.99 | 3.54 | 0.64 | 3.07 | 1.05 | 1.00 | 1.10 | 0.91 | 0.78 | 1.13 |
| Setdb1 | 1.12 | 0.86 | 0.80 | 0.95 | 0.68 | 0.96 | 1.14 | 0.33 | 1.07 | 0.99 | 0.83 | 1.12 |
| Sfrp2 | 0.57 | 0.71 | 1.13 | 0.38 | 0.31 | 0.65 | 1.00 | 1.00 | 1.00 | 1.00 | 1.00 | 1.00 |
| Sfrp5 | 1.37 | 0.88 | 0.95 | 0.13 | 0.19 | 0.13 | 1.00 | 1.00 | 1.00 | 1.00 | 1.00 | 1.00 |
| Sft2d1 | 0.99 | 1.19 | 1.20 | 0.89 | 0.55 | 0.99 | 0.78 | 0.27 | 1.09 | 0.87 | 1.15 | 0.83 |
| Sgk2 | 0.61 | 0.62 | 0.54 | 1.00 | 1.00 | 1.00 | 0.98 | 1.18 | 0.69 | 1.00 | 1.00 | 1.00 |
| Sgpl1 | 0.95 | 0.94 | 0.98 | 1.72 | 0.50 | 1.65 | 1.06 | 0.56 | 1.04 | 1.00 | 0.78 | 1.01 |
| Sh2b1 | 0.97 | 1.09 | 0.99 | 0.93 | 0.53 | 1.10 | 0.94 | 0.34 | 1.14 | 0.91 | 0.82 | 1.03 |
| Sh2d1a | 1.00 | 1.00 | 1.00 | 1.00 | 0.65 | 1.00 | 1.00 | 2.00 | 1.00 | 0.85 | 1.16 | 0.96 |
| Sh3bp5 | 1.13 | 0.99 | 0.90 | 1.01 | 0.15 | 0.98 | 0.83 | 0.96 | 0.97 | 1.01 | 0.73 | 1.11 |
| Sh3gl1 | 0.92 | 0.91 | 1.03 | 1.11 | 1.38 | 1.05 | 1.01 | 0.39 | 1.02 | 0.96 | 0.99 | 0.85 |
| Shisa7 | 0.88 | 0.92 | 0.86 | 1.00 | 1.00 | 1.00 | 1.03 | 1.46 | 0.77 | 1.00 | 4.57 | 1.63 |
| Shpk | 1.18 | 0.96 | 1.05 | 0.59 | 1.00 | 0.87 | 1.10 | 1.00 | 1.13 | 1.29 | 1.07 | 1.07 |
| Sik2 | 1.21 | 1.03 | 0.70 | 0.99 | 0.07 | 0.81 | 1.30 | 0.72 | 0.97 | 0.80 | 0.61 | 1.04 |
| Sik3 | 1.16 | 1.38 | 1.11 | 2.36 | 1.19 | 2.29 | 1.08 | 1.10 | 1.11 | 1.15 | 1.11 | 0.96 |
| Sipa1l3 | 0.92 | 0.98 | 0.71 | 0.95 | 1.00 | 0.94 | 1.19 | 1.44 | 1.32 | 0.86 | 0.81 | 0.78 |
| Six5 | 0.92 | 0.73 | 1.09 | 0.59 | 0.43 | 0.95 | 0.63 | 1.00 | 0.90 | 0.80 | 0.65 | 0.68 |
| Skint10 | 1.00 | 1.00 | 1.00 | 1.00 | 1.00 | 1.00 | 0.59 | 0.81 | 0.52 | 1.00 | 1.00 | 1.00 |
| Slamf6 | 1.00 | 1.00 | 1.00 | 0.64 | 1.00 | 0.89 | 1.00 | 1.00 | 1.00 | 0.78 | 0.47 | 0.66 |
| Slc10a3 | 1.00 | 0.91 | 0.92 | 1.35 | 0.35 | 0.90 | 1.11 | 0.86 | 0.86 | 0.97 | 0.79 | 1.03 |
| Slc16a1 | 0.65 | 0.62 | 0.62 | 1.69 | 0.91 | 1.21 | 1.03 | 0.64 | 1.02 | 0.67 | 0.57 | 0.67 |
| Slc16a2 | 0.81 | 0.83 | 0.91 | 0.92 | 0.54 | 1.02 | 1.15 | 1.00 | 1.08 | 0.84 | 1.05 | 1.11 |
| Slc16a6 | 0.63 | 0.62 | 0.63 | 1.72 | 1.00 | 1.15 | 0.74 | 1.00 | 0.83 | 0.94 | 0.83 | 1.00 |
| Slc17a5 | 1.21 | 1.24 | 1.27 | 2.01 | 0.61 | 1.59 | 0.95 | 1.00 | 1.18 | 1.21 | 1.07 | 1.10 |
| Slc18a2 | 1.05 | 1.00 | 1.01 | 1.00 | 1.00 | 1.03 | 1.06 | 1.00 | 1.00 | 1.28 | 1.23 | 1.00 |
| Slc22a17 | 0.85 | 0.90 | 1.08 | 0.84 | 0.62 | 1.39 | 0.80 | 0.60 | 0.78 | 0.70 | 3.66 | 0.98 |
| Slc24a3 | 0.62 | 0.77 | 1.20 | 0.59 | 0.23 | 0.63 | 0.79 | 0.86 | 1.00 | 1.13 | 2.06 | 0.80 |
| Slc25a16 | 1.01 | 1.04 | 1.21 | 0.99 | 0.25 | 1.04 | 0.66 | 1.00 | 1.00 | 1.11 | 0.94 | 0.96 |
| Slc25a24 | 0.73 | 0.63 | 0.59 | 1.32 | 1.00 | 0.90 | 0.84 | 0.41 | 0.90 | 0.79 | 0.53 | 0.78 |
| Slc25a35 | 0.98 | 0.92 | 1.00 | 0.33 | 0.58 | 0.59 | 1.01 | 0.39 | 0.98 | 0.71 | 0.52 | 0.75 |
| Slc25a36 | 0.96 | 0.83 | 0.81 | 1.14 | 0.44 | 0.68 | 1.04 | 1.00 | 0.88 | 1.11 | 0.53 | 1.10 |
| Slc26a2 | 0.65 | 0.60 | 0.25 | 0.37 | 0.24 | 0.14 | 1.80 | 3.29 | 1.67 | 0.51 | 0.32 | 0.87 |
| Slc27a6 | 2.97 | 2.56 | 2.93 | 0.20 | 1.00 | 0.10 | 0.85 | 1.00 | 0.99 | 1.00 | 1.00 | 1.00 |
| Slc30a7 | 0.98 | 0.76 | 0.78 | 0.92 | 0.44 | 0.84 | 1.00 | 1.00 | 1.05 | 1.09 | 0.71 | 1.19 |
| Slc35b4 | 1.03 | 0.97 | 0.98 | 0.79 | 0.43 | 0.81 | 1.11 | 0.83 | 0.96 | 0.77 | 0.67 | 0.91 |
| Slc35d1 | 0.77 | 0.66 | 0.66 | 1.35 | 1.00 | 1.27 | 1.17 | 1.38 | 0.94 | 0.90 | 0.54 | 1.16 |
| Slc35f2 | 0.92 | 0.89 | 1.06 | 1.18 | 1.00 | 0.20 | 0.83 | 0.53 | 0.89 | 1.18 | 0.92 | 0.86 |
| Slc35f5 | 0.97 | 0.98 | 0.87 | 0.96 | 0.41 | 1.09 | 0.85 | 0.66 | 0.90 | 1.07 | 0.99 | 1.14 |
| Slc35g1 | 0.79 | 0.75 | 0.63 | 1.04 | 1.00 | 1.08 | 1.05 | 1.00 | 0.91 | 0.57 | 0.41 | 0.82 |
| Slc39a10 | 0.73 | 0.53 | 0.59 | 0.88 | 0.76 | 0.82 | 1.40 | 1.21 | 1.18 | 0.90 | 1.04 | 0.91 |
| Slc40a1 | 0.78 | 0.69 | 1.01 | 0.91 | 0.64 | 0.87 | 1.31 | 1.00 | 0.77 | 0.69 | 0.67 | 0.72 |
| Slc45a3 | 1.09 | 1.16 | 0.90 | 3.76 | 1.00 | 1.98 | 0.57 | 0.86 | 0.58 | 0.91 | 1.11 | 0.97 |
| Slc6a13 | 1.00 | 1.00 | 1.00 | 0.30 | 0.98 | 0.17 | 1.00 | 1.00 | 1.00 | 1.00 | 1.71 | 1.06 |
| Slc6a14 | 1.00 | 1.00 | 1.00 | 1.00 | 1.00 | 1.00 | 1.08 | 1.00 | 0.72 | 1.00 | 1.00 | 1.00 |
| Slc6a19 | 1.28 | 1.51 | 1.15 | 1.23 | 1.00 | 1.00 | 1.00 | 1.00 | 1.00 | 1.00 | 1.00 | 1.00 |
| Slc6a6 | 1.06 | 1.23 | 0.99 | 1.11 | 0.16 | 1.25 | 1.36 | 0.62 | 0.91 | 0.81 | 0.67 | 0.91 |
| Slco4a1 | 0.78 | 0.88 | 0.51 | 1.00 | 1.00 | 1.00 | 1.00 | 1.00 | 1.00 | 0.94 | 0.77 | 0.77 |
| Slfn3 | 1.02 | 1.00 | 1.00 | 1.00 | 1.00 | 0.68 | 1.00 | 1.00 | 0.78 | 1.36 | 0.77 | 1.25 |
| Slfn9 | 0.52 | 0.21 | 0.37 | 1.00 | 1.00 | 1.00 | 1.00 | 1.00 | 1.00 | 1.00 | 0.62 | 1.15 |
| Slitrk6 | 0.37 | 0.30 | 0.62 | 1.00 | 1.00 | 1.00 | 1.00 | 1.00 | 1.00 | 1.00 | 1.00 | 1.00 |
| Sltm | 1.01 | 0.97 | 0.79 | 1.23 | 0.74 | 1.04 | 1.06 | 0.86 | 1.00 | 1.14 | 0.96 | 1.19 |
| Smad3 | 0.98 | 0.95 | 0.90 | 1.49 | 0.48 | 1.47 | 1.21 | 1.00 | 1.11 | 1.27 | 1.05 | 1.38 |
| Smad6 | 0.66 | 0.88 | 0.74 | 1.28 | 0.57 | 1.25 | 0.98 | 0.61 | 1.10 | 0.77 | 1.04 | 1.13 |
| Smg1 | 1.00 | 0.87 | 0.79 | 1.11 | 0.26 | 0.96 | 1.11 | 0.74 | 1.04 | 1.09 | 0.71 | 1.18 |
| Smim3 | 1.52 | 1.45 | 1.20 | 1.48 | 1.00 | 1.83 | 0.83 | 1.00 | 1.22 | 1.21 | 1.00 | 0.82 |
| Snai2 | 0.79 | 0.56 | 0.76 | 0.56 | 1.00 | 0.87 | 1.24 | 0.46 | 1.17 | 0.59 | 0.59 | 1.01 |
| Snai3 | 1.25 | 0.89 | 1.17 | 1.00 | 1.00 | 1.00 | 1.09 | 0.93 | 0.86 | 0.78 | 0.74 | 1.00 |
| Snca | 1.54 | 0.73 | 0.77 | 1.27 | 0.33 | 0.78 | 1.00 | 1.00 | 1.00 | 0.42 | 0.43 | 0.19 |
| Snn | 0.87 | 0.75 | 1.11 | 1.11 | 0.72 | 1.15 | 1.06 | 2.10 | 1.18 | 0.97 | 0.73 | 1.10 |
| Snora24 | 1.00 | 1.00 | 1.00 | 1.00 | 0.07 | 1.00 | 1.00 | 1.00 | 1.00 | 1.00 | 1.00 | 1.00 |
| Snora26 | 1.00 | 1.00 | 1.00 | 1.00 | 0.00 | 1.00 | 1.00 | 1.00 | 1.00 | 1.00 | 1.00 | 1.00 |
| Snora68 | 1.00 | 1.00 | 1.00 | 1.00 | 1.00 | 1.00 | 1.00 | 1.00 | 1.00 | 1.00 | 1.00 | 1.00 |
| Snord23 | 1.00 | 1.00 | 1.00 | 1.00 | 1.00 | 1.00 | 1.00 | 1.00 | 1.00 | 1.00 | 1.00 | 1.00 |

Fig. 35- 88

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Sertad4 | 1.00 | 1.00 | 1.00 | 1.12 | 1.00 | 0.87 | 0.43 | 0.08 | 0.83 | 1.00 | 1.00 | 1.00 |
| Sesn2 | 1.04 | 1.00 | 1.00 | 1.14 | 1.00 | 0.96 | 1.63 | 0.18 | 1.07 | 0.49 | 1.25 | 0.88 |
| Setdb1 | 1.03 | 1.02 | 1.23 | 0.88 | 0.92 | 0.89 | 0.86 | 0.10 | 0.99 | 0.48 | 0.84 | 0.97 |
| Sfrp2 | 1.00 | 1.00 | 1.00 | 0.94 | 1.00 | 1.16 | 0.55 | 0.10 | 0.72 | 1.00 | 1.00 | 1.00 |
| Sfrp5 | 1.00 | 1.00 | 0.64 | 0.60 | 0.45 | 0.79 | 1.37 | 3.51 | 1.51 | 1.00 | 1.00 | 1.00 |
| Sft2d1 | 1.31 | 1.60 | 1.01 | 0.82 | 0.31 | 1.02 | 1.24 | 0.22 | 1.32 | 0.71 | 1.42 | 0.99 |
| Sgk2 | 0.50 | 0.51 | 0.63 | 1.00 | 1.00 | 1.00 | 1.00 | 1.00 | 1.00 | 1.00 | 1.00 | 1.00 |
| Sgpl1 | 0.95 | 1.06 | 1.00 | 0.88 | 1.00 | 0.91 | 1.05 | 0.16 | 1.02 | 0.50 | 0.97 | 0.97 |
| Sh2b1 | 0.86 | 1.06 | 1.06 | 1.05 | 1.27 | 0.99 | 1.05 | 0.17 | 1.06 | 0.79 | 1.09 | 0.99 |
| Sh2d1a | 1.00 | 1.00 | 1.00 | 1.00 | 0.17 | 1.00 | 1.00 | 1.00 | 1.00 | 3.29 | 1.36 | 1.52 |
| Sh3bp5 | 0.48 | 0.86 | 0.97 | 1.10 | 0.69 | 0.96 | 1.19 | 0.09 | 1.25 | 0.15 | 0.90 | 0.85 |
| Sh3gl1 | 0.97 | 0.75 | 0.75 | 1.06 | 1.07 | 1.20 | 1.21 | 0.40 | 0.96 | 0.79 | 1.09 | 1.12 |
| Shisa7 | 1.00 | 1.00 | 1.00 | 1.12 | 0.97 | 1.03 | 1.00 | 1.10 | 1.15 | 1.00 | 1.00 | 1.00 |
| Shpk | 1.16 | 0.90 | 0.79 | 1.10 | 1.20 | 0.92 | 1.17 | 0.18 | 1.15 | 0.75 | 1.04 | 1.13 |
| Sik2 | 1.00 | 1.00 | 1.00 | 0.82 | 0.67 | 0.84 | 0.95 | 0.38 | 1.43 | 1.00 | 0.78 | 0.73 |
| Sik3 | 1.34 | 1.21 | 1.02 | 1.20 | 1.17 | 1.06 | 1.21 | 0.19 | 1.40 | 0.74 | 1.43 | 1.08 |
| Sipa1l3 | 1.06 | 0.92 | 1.26 | 1.00 | 0.40 | 1.11 | 0.61 | 0.14 | 0.80 | 0.47 | 0.90 | 0.81 |
| Six5 | 0.92 | 0.72 | 0.82 | 0.66 | 1.00 | 0.72 | 0.79 | 0.19 | 0.91 | 1.00 | 0.91 | 0.84 |
| Skint10 | 1.00 | 1.00 | 1.00 | 1.00 | 1.00 | 1.00 | 0.66 | 0.18 | 0.60 | 1.00 | 1.00 | 1.00 |
| Slamf6 | 1.00 | 1.00 | 1.00 | 1.00 | 1.00 | 1.00 | 1.00 | 1.00 | 1.00 | 0.17 | 0.59 | 0.55 |
| Slc10a3 | 1.88 | 1.24 | 1.36 | 0.89 | 1.00 | 0.98 | 0.85 | 0.09 | 0.73 | 0.65 | 1.06 | 1.00 |
| Slc16a1 | 0.89 | 1.00 | 1.00 | 0.70 | 0.34 | 0.81 | 0.73 | 0.25 | 0.91 | 0.34 | 0.67 | 0.65 |
| Slc16a2 | 1.00 | 1.00 | 1.00 | 0.84 | 0.48 | 0.78 | 0.87 | 0.54 | 1.16 | 1.00 | 1.00 | 1.00 |
| Slc16a6 | 1.37 | 1.12 | 1.17 | 1.05 | 1.00 | 0.92 | 0.68 | 0.08 | 0.65 | 0.39 | 0.76 | 0.71 |
| Slc17a5 | 1.16 | 0.91 | 1.23 | 1.07 | 0.75 | 1.06 | 1.22 | 0.16 | 1.31 | 0.75 | 1.32 | 1.19 |
| Slc18a2 | 1.00 | 1.00 | 1.00 | 1.26 | 1.00 | 0.96 | 1.53 | 0.42 | 1.94 | 0.73 | 1.10 | 0.96 |
| Slc22a17 | 0.83 | 0.54 | 0.65 | 1.12 | 1.15 | 1.06 | 1.07 | 0.74 | 0.82 | 1.00 | 1.00 | 0.72 |
| Slc24a3 | 1.00 | 1.00 | 1.00 | 1.03 | 1.08 | 1.06 | 1.18 | 0.09 | 1.12 | 1.00 | 1.42 | 1.15 |
| Slc25a16 | 0.86 | 0.91 | 0.90 | 1.06 | 1.00 | 1.03 | 0.80 | 0.09 | 1.19 | 0.51 | 0.96 | 0.90 |
| Slc25a24 | 1.00 | 1.00 | 1.00 | 0.87 | 1.00 | 1.08 | 0.73 | 0.16 | 0.97 | 0.60 | 0.94 | 1.03 |
| Slc25a35 | 1.06 | 0.91 | 0.79 | 0.67 | 1.00 | 0.88 | 0.71 | 0.21 | 0.83 | 1.00 | 0.82 | 0.85 |
| Slc25a36 | 1.12 | 1.17 | 1.13 | 0.93 | 1.00 | 0.88 | 0.49 | 0.16 | 0.95 | 0.96 | 0.83 | 0.86 |
| Slc26a2 | 1.00 | 1.00 | 1.00 | 0.62 | 1.00 | 0.72 | 0.49 | 1.54 | 0.77 | 1.00 | 1.00 | 1.00 |
| Slc27a6 | 1.00 | 1.00 | 1.00 | 1.00 | 1.00 | 1.00 | 0.59 | 0.45 | 0.78 | 1.00 | 1.00 | 1.00 |
| Slc30a7 | 1.19 | 1.20 | 1.10 | 0.90 | 1.00 | 0.91 | 0.86 | 0.19 | 1.05 | 0.85 | 1.11 | 1.01 |
| Slc35b4 | 0.81 | 1.00 | 0.82 | 0.92 | 2.50 | 0.92 | 0.82 | 0.16 | 0.97 | 0.63 | 0.65 | 0.71 |
| Slc35d1 | 0.92 | 1.00 | 1.00 | 1.01 | 1.00 | 0.87 | 0.70 | 0.18 | 1.44 | 1.00 | 0.59 | 0.61 |
| Slc35f2 | 1.00 | 1.00 | 1.00 | 1.03 | 1.00 | 1.08 | 0.37 | 0.22 | 0.53 | 1.00 | 1.00 | 1.00 |
| Slc35f5 | 1.20 | 0.85 | 0.92 | 1.01 | 1.00 | 1.01 | 1.01 | 0.04 | 0.95 | 0.56 | 1.26 | 1.11 |
| Slc35g1 | 1.24 | 1.36 | 1.00 | 1.04 | 0.83 | 1.00 | 0.65 | 0.15 | 0.90 | 0.60 | 0.48 | 0.76 |
| Slc39a10 | 1.00 | 1.00 | 1.00 | 0.93 | 0.87 | 0.88 | 0.70 | 0.20 | 0.86 | 0.71 | 0.71 | 0.92 |
| Slc40a1 | 1.28 | 0.92 | 1.03 | 0.65 | 1.00 | 0.73 | 0.63 | 0.19 | 0.68 | 0.43 | 0.66 | 0.78 |
| Slc45a3 | 1.00 | 1.00 | 1.00 | 1.00 | 1.00 | 1.00 | 1.18 | 0.17 | 0.98 | 0.56 | 0.80 | 0.78 |
| Slc6a13 | 1.00 | 1.00 | 1.00 | 1.39 | 2.72 | 0.98 | 1.00 | 1.00 | 1.00 | 2.24 | 1.90 | 1.55 |
| Slc6a14 | 1.00 | 1.00 | 1.00 | 1.00 | 1.00 | 1.00 | 0.60 | 0.14 | 0.60 | 1.00 | 1.00 | 1.00 |
| Slc6a19 | 1.00 | 1.00 | 1.00 | 1.00 | 1.00 | 1.00 | 1.35 | 0.11 | 1.14 | 1.00 | 1.00 | 1.00 |
| Slc6a6 | 1.03 | 1.27 | 1.55 | 0.83 | 1.00 | 0.96 | 1.10 | 0.22 | 1.58 | 0.50 | 0.99 | 0.88 |
| Slco4a1 | 1.00 | 1.00 | 1.00 | 1.14 | 1.00 | 1.13 | 0.94 | 0.58 | 1.23 | 0.52 | 0.82 | 1.51 |
| Slfn3 | 1.00 | 1.00 | 1.00 | 1.00 | 1.00 | 1.00 | 1.00 | 1.00 | 1.00 | 0.96 | 0.86 | 0.56 |
| Slfn9 | 1.00 | 1.00 | 1.00 | 1.00 | 1.00 | 1.00 | 1.00 | 1.00 | 1.00 | 1.00 | 0.93 | 0.82 |
| Slitrk6 | 1.00 | 1.00 | 1.00 | 0.91 | 1.00 | 1.05 | 0.49 | 0.16 | 0.78 | 1.00 | 1.00 | 1.00 |
| Sltm | 1.33 | 1.90 | 1.56 | 1.00 | 1.00 | 1.06 | 0.87 | 0.08 | 0.86 | 0.60 | 1.05 | 0.95 |
| Smad3 | 0.87 | 0.62 | 0.65 | 0.85 | 2.63 | 0.87 | 1.09 | 0.25 | 1.40 | 0.78 | 1.33 | 1.19 |
| Smad6 | 0.90 | 0.87 | 0.99 | 1.05 | 1.00 | 0.91 | 1.33 | 0.18 | 1.03 | 1.00 | 1.00 | 1.00 |
| Smg1 | 1.21 | 1.12 | 1.10 | 0.82 | 1.00 | 0.89 | 0.92 | 0.18 | 1.10 | 0.53 | 0.98 | 0.94 |
| Smim3 | 2.16 | 2.83 | 1.41 | 2.67 | 3.37 | 2.12 | 0.89 | 0.51 | 1.11 | 1.13 | 1.73 | 1.66 |
| Snai2 | 1.00 | 1.00 | 1.00 | 1.00 | 1.00 | 1.00 | 0.51 | 0.38 | 0.93 | 1.00 | 1.00 | 1.00 |
| Snai3 | 1.00 | 0.90 | 0.94 | 1.00 | 0.94 | 1.00 | 1.00 | 2.51 | 1.00 | 1.00 | 1.00 | 1.00 |
| Snca | 1.00 | 1.00 | 1.00 | 1.08 | 1.02 | 0.96 | 2.12 | 1.00 | 1.69 | 0.54 | 0.77 | 0.77 |
| Snn | 0.62 | 0.40 | 0.66 | 0.98 | 0.96 | 0.96 | 0.82 | 0.18 | 0.80 | 0.46 | 0.70 | 0.88 |
| Snora24 | 1.00 | 1.00 | 1.00 | 1.00 | 1.00 | 1.00 | 1.00 | 1.00 | 1.00 | 1.00 | 1.00 | 1.00 |
| Snora26 | 1.00 | 1.00 | 1.00 | 1.00 | 1.00 | 1.00 | 1.00 | 1.00 | 1.00 | 1.00 | 1.00 | 1.00 |
| Snora68 | 1.00 | 1.00 | 1.00 | 1.00 | 1.00 | 1.00 | 1.00 | 1.00 | 1.00 | 1.00 | 1.00 | 1.00 |
| Snord23 | 1.00 | 1.00 | 1.00 | 1.00 | 1.00 | 1.00 | 1.00 | 1.00 | 1.00 | 1.00 | 1.00 | 1.00 |

Fig. 35- 89

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Snrnp48 | 1.39 | 1.45 | 1.05 | 2.91 | 1.40 | 1.63 | 1.74 | 1.70 | 1.34 | 0.93 | 0.83 | 0.85 |
| Sntb1 | 1.00 | 1.00 | 1.00 | 1.39 | 0.58 | 0.88 | 1.52 | 1.00 | 1.00 | 1.00 | 1.00 | 1.23 |
| Snx13 | 0.94 | 1.99 | 0.95 | 1.76 | 0.25 | 0.92 | 1.10 | 1.12 | 0.93 | 0.54 | 0.52 | 1.12 |
| Snx18 | 0.90 | 1.46 | 1.23 | 1.24 | 0.35 | 0.92 | 0.97 | 1.17 | 1.06 | 0.48 | 0.59 | 1.18 |
| Snx24 | 0.89 | 1.83 | 1.00 | 2.83 | 0.62 | 1.57 | 1.62 | 1.62 | 1.29 | 0.20 | 0.25 | 1.14 |
| Socs3 | 4.06 | 4.16 | 1.14 | 1.72 | 0.88 | 2.23 | 1.30 | 1.44 | 2.65 | 0.87 | 0.80 | 1.16 |
| Sorbs1 | 1.62 | 2.30 | 1.87 | 1.31 | 0.22 | 0.85 | 1.31 | 1.71 | 1.33 | 0.55 | 0.56 | 1.14 |
| Sostdc1 | 1.00 | 1.00 | 1.00 | 1.00 | 1.00 | 1.00 | 1.00 | 1.00 | 1.00 | 1.00 | 1.00 | 1.00 |
| Sox18 | 1.03 | 1.89 | 1.17 | 0.71 | 0.19 | 1.05 | 1.40 | 0.92 | 0.99 | 0.26 | 0.23 | 1.11 |
| Sox21 | 1.00 | 1.00 | 1.00 | 1.00 | 1.00 | 1.00 | 1.00 | 1.00 | 1.00 | 1.00 | 1.00 | 1.00 |
| Sox7 | 0.64 | 1.14 | 0.66 | 1.34 | 0.20 | 0.75 | 0.81 | 0.76 | 0.78 | 0.21 | 0.13 | 0.66 |
| Sp1 | 1.37 | 2.64 | 1.42 | 2.67 | 0.34 | 1.00 | 1.17 | 1.21 | 1.14 | 0.46 | 0.33 | 0.93 |
| Sp2 | 0.93 | 1.06 | 1.16 | 1.16 | 0.33 | 1.06 | 1.16 | 1.02 | 0.81 | 0.66 | 0.56 | 1.08 |
| Sp3 | 0.96 | 1.17 | 0.85 | 3.81 | 0.43 | 1.05 | 0.78 | 0.98 | 1.06 | 0.76 | 0.35 | 1.01 |
| Spag1 | 1.00 | 1.00 | 1.00 | 1.00 | 1.00 | 1.00 | 1.00 | 1.00 | 1.00 | 1.00 | 1.00 | 0.85 |
| Spag11b | 1.00 | 1.00 | 1.00 | 1.00 | 1.00 | 1.00 | 1.00 | 1.00 | 1.00 | 1.00 | 1.00 | 1.00 |
| Spag9 | 0.93 | 1.86 | 0.97 | 1.90 | 0.22 | 0.95 | 1.01 | 1.28 | 1.11 | 0.42 | 0.30 | 0.99 |
| Spata2 | 0.89 | 1.27 | 0.92 | 0.85 | 0.15 | 0.84 | 1.21 | 1.27 | 1.09 | 0.57 | 0.49 | 1.05 |
| Speer1-ps1 | 1.00 | 1.00 | 1.00 | 1.00 | 1.00 | 1.00 | 1.00 | 1.00 | 1.00 | 1.00 | 1.00 | 1.00 |
| Spin1 | 1.01 | 2.42 | 1.07 | 2.37 | 0.50 | 1.26 | 1.14 | 1.28 | 1.02 | 0.50 | 0.53 | 1.01 |
| Spin2d | 1.00 | 1.00 | 1.00 | 1.00 | 1.00 | 1.00 | 1.00 | 1.00 | 1.00 | 1.00 | 1.00 | 1.00 |
| Spns3 | 1.00 | 1.00 | 1.00 | 1.00 | 1.00 | 1.00 | 1.00 | 1.00 | 1.00 | 1.00 | 1.00 | 1.00 |
| Spred2 | 0.73 | 1.00 | 0.94 | 2.45 | 0.10 | 1.14 | 1.34 | 1.80 | 1.46 | 1.00 | 1.00 | 1.03 |
| Sprr2a1 | 1.00 | 1.00 | 1.00 | 1.00 | 1.00 | 1.00 | 1.00 | 1.00 | 1.00 | 0.10 | 1.00 | 1.00 |
| Sprr2a2 | 1.00 | 1.00 | 1.00 | 1.00 | 1.00 | 1.00 | 1.00 | 1.00 | 1.00 | 0.09 | 1.00 | 1.00 |
| Sprr2b | 1.00 | 1.00 | 1.00 | 1.00 | 1.00 | 1.00 | 1.00 | 1.00 | 1.00 | 1.00 | 1.00 | 1.00 |
| Sprr2e | 1.00 | 1.00 | 1.00 | 1.00 | 1.00 | 1.00 | 1.00 | 1.00 | 1.00 | 1.00 | 1.00 | 1.00 |
| Sprr3 | 1.00 | 1.00 | 1.00 | 1.00 | 1.00 | 1.00 | 1.00 | 1.00 | 1.00 | 0.22 | 1.00 | 1.00 |
| Sprr4 | 1.00 | 1.00 | 1.00 | 1.00 | 1.00 | 1.00 | 1.00 | 1.00 | 1.00 | 1.00 | 1.00 | 1.00 |
| Sprtn | 0.51 | 1.00 | 1.24 | 1.48 | 0.09 | 0.82 | 1.14 | 1.68 | 1.14 | 1.00 | 1.00 | 1.00 |
| Spry1 | 0.92 | 1.56 | 1.00 | 1.99 | 0.65 | 1.62 | 1.26 | 1.37 | 1.26 | 0.73 | 0.43 | 1.19 |
| Spry2 | 1.03 | 1.48 | 0.99 | 0.86 | 0.47 | 0.87 | 0.98 | 0.94 | 1.19 | 0.60 | 0.54 | 1.24 |
| Spry4 | 1.18 | 1.00 | 1.13 | 0.99 | 0.12 | 1.15 | 1.13 | 1.31 | 1.55 | 1.63 | 1.74 | 2.32 |
| Spryd7 | 1.11 | 2.21 | 1.02 | 1.17 | 0.35 | 0.91 | 0.74 | 0.88 | 0.73 | 0.32 | 0.52 | 1.17 |
| Spta1 | 1.00 | 1.00 | 1.00 | 1.00 | 1.00 | 1.00 | 1.00 | 1.00 | 1.00 | 1.00 | 1.00 | 1.00 |
| Sptb | 0.83 | 0.88 | 1.08 | 1.00 | 0.47 | 1.15 | 1.18 | 1.40 | 1.07 | 1.00 | 1.00 | 1.00 |
| Sptbn1 | 1.03 | 1.62 | 1.18 | 1.06 | 0.44 | 0.97 | 1.08 | 1.29 | 1.22 | 0.40 | 0.43 | 1.00 |
| Sptssb | 0.98 | 1.00 | 1.00 | 1.00 | 1.00 | 1.00 | 1.00 | 1.00 | 1.00 | 0.58 | 1.00 | 0.94 |
| Srd5a1 | 1.00 | 1.00 | 1.00 | 1.00 | 1.00 | 1.00 | 1.00 | 1.00 | 1.00 | 1.00 | 0.95 | 1.06 |
| Srebf1 | 0.61 | 0.66 | 0.66 | 0.20 | 0.23 | 0.74 | 0.66 | 0.57 | 0.69 | 0.63 | 1.09 | 1.06 |
| Srebf2 | 1.21 | 1.00 | 1.30 | 0.73 | 0.19 | 1.19 | 1.78 | 1.42 | 1.34 | 0.87 | 0.48 | 1.23 |
| Srek1ip1 | 0.69 | 1.27 | 0.75 | 0.75 | 0.33 | 0.90 | 0.57 | 0.82 | 0.78 | 0.70 | 0.65 | 1.01 |
| Srsf5 | 1.15 | 1.85 | 1.03 | 2.01 | 0.96 | 1.27 | 0.72 | 0.80 | 0.96 | 0.32 | 0.44 | 0.96 |
| Ssbp1 | 0.88 | 0.93 | 0.97 | 0.88 | 0.32 | 1.12 | 1.10 | 0.84 | 0.91 | 0.69 | 0.28 | 0.91 |
| Ssh3 | 1.27 | 1.00 | 0.93 | 1.22 | 0.40 | 1.24 | 1.15 | 1.15 | 1.01 | 0.58 | 0.32 | 1.04 |
| St3gal5 | 0.94 | 1.32 | 0.76 | 0.31 | 0.32 | 0.79 | 0.61 | 0.64 | 0.59 | 0.65 | 0.73 | 0.85 |
| St6galnac5 | 0.83 | 0.69 | 1.00 | 0.90 | 0.87 | 0.86 | 1.00 | 1.00 | 1.00 | 0.66 | 0.79 | 0.27 |
| St8sia4 | 0.80 | 1.00 | 1.00 | 2.12 | 0.45 | 0.74 | 0.66 | 0.52 | 0.92 | 0.27 | 0.17 | 0.35 |
| Stam | 0.95 | 1.55 | 1.21 | 1.33 | 0.40 | 0.97 | 1.12 | 1.17 | 0.97 | 0.79 | 0.50 | 1.09 |
| Stard3nl | 1.76 | 3.32 | 1.61 | 2.33 | 1.30 | 0.79 | 1.33 | 0.65 | 0.85 | 0.19 | 0.38 | 0.74 |
| Stat5b | 0.90 | 1.51 | 1.24 | 1.01 | 0.44 | 0.97 | 1.29 | 1.31 | 0.86 | 0.40 | 0.37 | 0.92 |
| Steap3 | 0.61 | 1.10 | 0.76 | 0.43 | 0.11 | 0.40 | 0.73 | 0.84 | 0.82 | 0.25 | 0.18 | 0.67 |
| Steap4 | 1.38 | 4.21 | 1.30 | 2.05 | 0.25 | 1.02 | 1.52 | 1.55 | 1.35 | 1.03 | 0.64 | 2.39 |
| Stim1 | 0.89 | 3.30 | 0.90 | 1.49 | 0.06 | 1.22 | 1.52 | 1.49 | 1.32 | 0.42 | 0.11 | 1.55 |
| Stk10 | 1.00 | 1.00 | 1.09 | 1.27 | 0.37 | 1.09 | 1.21 | 1.21 | 1.23 | 0.54 | 0.41 | 0.87 |
| Strada | 0.95 | 1.02 | 0.70 | 0.64 | 0.78 | 1.15 | 0.92 | 0.91 | 0.82 | 0.75 | 0.50 | 0.84 |
| Stradb | 1.02 | 1.88 | 0.82 | 0.99 | 0.41 | 0.80 | 1.28 | 1.12 | 1.09 | 0.26 | 0.37 | 1.01 |
| Strn | 1.00 | 1.00 | 1.00 | 1.79 | 0.51 | 0.79 | 0.71 | 0.94 | 0.81 | 1.00 | 1.00 | 0.74 |
| Stub1 | 0.98 | 0.92 | 0.95 | 0.30 | 1.02 | 0.93 | 1.17 | 0.85 | 0.91 | 0.87 | 0.64 | 0.99 |
| Stxbp1 | 1.22 | 1.22 | 1.05 | 1.06 | 0.11 | 0.84 | 0.94 | 0.92 | 0.78 | 1.05 | 0.95 | 1.00 |
| Stxbp3a | 0.90 | 1.37 | 0.70 | 2.21 | 1.04 | 1.29 | 1.10 | 1.05 | 0.83 | 0.33 | 0.40 | 0.89 |
| Stxbp3b | 0.60 | 1.00 | 0.73 | 4.00 | 0.18 | 1.16 | 1.24 | 1.10 | 1.33 | 1.00 | 0.36 | 1.35 |
| Styx | 0.66 | 2.44 | 0.56 | 2.50 | 0.49 | 1.01 | 0.86 | 1.14 | 0.85 | 0.98 | 0.35 | 0.88 |
| Sucnr1 | 1.00 | 1.00 | 1.00 | 1.00 | 1.00 | 0.90 | 1.00 | 1.00 | 1.00 | 1.00 | 1.00 | 1.00 |

Fig. 35- 90

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Snrnp48 | 1.01 | 1.03 | 0.94 | 1.36 | 1.81 | 1.44 | 1.06 | 0.62 | 1.12 | 0.92 | 1.05 | 1.07 |
| Sntb1 | 1.00 | 1.00 | 1.18 | 0.63 | 1.00 | 1.00 | 1.44 | 1.77 | 1.76 | 0.97 | 1.00 | 1.11 |
| Snx13 | 0.85 | 0.83 | 0.89 | 1.14 | 1.80 | 1.00 | 0.92 | 1.00 | 0.79 | 0.98 | 0.80 | 0.97 |
| Snx18 | 1.20 | 1.01 | 1.27 | 1.07 | 1.55 | 1.19 | 0.91 | 0.66 | 1.04 | 1.02 | 0.75 | 0.91 |
| Snx24 | 2.54 | 2.30 | 1.29 | 1.15 | 1.25 | 0.85 | 1.58 | 1.00 | 1.07 | 1.06 | 1.07 | 1.01 |
| Socs3 | 0.98 | 0.88 | 1.15 | 1.33 | 1.00 | 0.99 | 1.44 | 2.30 | 1.76 | 0.86 | 1.01 | 1.29 |
| Sorbs1 | 0.65 | 0.54 | 0.60 | 0.80 | 1.10 | 0.91 | 0.80 | 0.72 | 1.16 | 1.16 | 0.73 | 1.12 |
| Sostdc1 | 0.46 | 0.40 | 0.55 | 0.81 | 1.77 | 1.06 | 1.00 | 1.00 | 1.00 | 1.08 | 0.52 | 0.85 |
| Sox18 | 1.43 | 1.11 | 1.03 | 0.78 | 1.87 | 1.07 | 0.80 | 1.00 | 0.87 | 0.73 | 0.70 | 0.88 |
| Sox21 | 0.86 | 0.86 | 0.99 | 1.00 | 1.00 | 1.00 | 1.00 | 1.00 | 1.00 | 0.93 | 0.65 | 0.75 |
| Sox7 | 1.44 | 1.05 | 0.78 | 0.88 | 1.00 | 0.96 | 0.83 | 1.00 | 1.00 | 1.21 | 0.98 | 1.23 |
| Sp1 | 0.61 | 0.55 | 0.80 | 1.13 | 1.40 | 0.99 | 1.06 | 1.00 | 1.21 | 1.07 | 0.76 | 0.94 |
| Sp2 | 0.72 | 0.75 | 0.87 | 1.03 | 1.10 | 0.96 | 1.23 | 1.00 | 1.27 | 1.16 | 0.87 | 1.04 |
| Sp3 | 0.52 | 0.46 | 0.77 | 1.41 | 1.63 | 1.12 | 1.11 | 0.87 | 1.16 | 0.97 | 0.61 | 0.93 |
| Spag1 | 0.79 | 0.73 | 1.20 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 | 1.00 | 1.00 |
| Spag9 | 0.82 | 0.78 | 1.06 | 1.20 | 2.48 | 1.07 | 0.95 | 1.15 | 1.02 | 0.96 | 0.62 | 1.02 |
| Spata2 | 0.82 | 0.72 | 1.00 | 1.05 | 0.97 | 1.05 | 1.10 | 1.00 | 1.05 | 1.12 | 0.66 | 1.09 |
| Speer1-ps1 | 1.00 | 1.00 | 1.00 | 1.00 | 1.00 | 1.00 | 1.00 | 1.00 | 1.00 | 1.00 | 1.00 | 1.00 |
| Spin1 | 0.91 | 0.84 | 1.10 | 1.10 | 1.83 | 0.99 | 2.41 | 1.85 | 1.77 | 1.15 | 0.87 | 1.09 |
| Spin2d | 1.00 | 1.00 | 1.00 | 1.00 | 1.00 | 1.00 | 1.00 | 1.00 | 1.00 | 1.00 | 1.00 | 1.00 |
| Spns3 | 1.26 | 0.79 | 0.65 | 1.00 | 0.09 | 0.52 | 1.00 | 1.00 | 1.00 | 1.00 | 1.00 | 1.00 |
| Spred2 | 0.47 | 0.32 | 0.86 | 1.10 | 1.00 | 1.14 | 1.01 | 1.00 | 0.97 | 1.09 | 0.23 | 1.07 |
| Sprr2a1 | 0.82 | 0.50 | 1.00 | 1.00 | 1.00 | 1.00 | 1.00 | 1.00 | 1.00 | 1.00 | 0.99 | 0.95 |
| Sprr2a2 | 0.82 | 0.42 | 1.00 | 1.00 | 1.00 | 1.00 | 1.00 | 1.00 | 1.00 | 1.03 | 0.96 | 0.94 |
| Sprr2b | 0.55 | 1.00 | 1.00 | 1.00 | 1.00 | 1.00 | 1.00 | 1.00 | 1.00 | 0.66 | 1.05 | 1.74 |
| Sprr2e | 0.69 | 1.00 | 1.00 | 1.00 | 1.00 | 1.00 | 1.00 | 1.00 | 1.00 | 1.00 | 1.00 | 1.00 |
| Sprr3 | 1.00 | 1.00 | 1.00 | 1.00 | 1.00 | 1.00 | 1.00 | 1.00 | 1.00 | 1.00 | 1.00 | 1.00 |
| Sprr4 | 0.48 | 1.00 | 1.00 | 1.00 | 1.00 | 1.00 | 1.00 | 1.00 | 1.00 | 1.00 | 1.00 | 1.00 |
| Sprtn | 0.37 | 0.22 | 0.74 | 0.98 | 1.00 | 1.17 | 1.04 | 1.00 | 0.92 | 0.87 | 0.24 | 0.86 |
| Spry1 | 2.86 | 2.40 | 1.80 | 0.97 | 0.81 | 1.09 | 1.73 | 1.00 | 1.19 | 1.24 | 0.96 | 1.11 |
| Spry2 | 2.00 | 1.50 | 1.79 | 1.16 | 0.90 | 1.18 | 1.16 | 1.00 | 1.14 | 0.86 | 0.79 | 0.92 |
| Spry4 | 1.00 | 1.00 | 1.09 | 1.22 | 1.04 | 1.12 | 0.92 | 1.00 | 0.65 | 1.22 | 1.05 | 1.07 |
| Spryd7 | 1.20 | 1.07 | 1.30 | 1.13 | 1.46 | 1.19 | 1.61 | 0.52 | 1.24 | 1.01 | 1.07 | 1.17 |
| Spta1 | 1.00 | 1.00 | 1.00 | 1.00 | 1.00 | 1.00 | 1.00 | 1.00 | 1.00 | 1.00 | 1.00 | 1.00 |
| Sptb | 1.17 | 1.26 | 1.68 | 1.00 | 1.00 | 1.00 | 1.00 | 1.00 | 1.00 | 1.12 | 1.00 | 0.94 |
| Sptbn1 | 0.85 | 0.76 | 0.94 | 1.22 | 1.67 | 1.19 | 1.27 | 0.58 | 1.31 | 1.04 | 0.79 | 0.89 |
| Sptssb | 0.36 | 0.19 | 0.34 | 0.55 | 1.00 | 0.73 | 1.00 | 1.00 | 1.00 | 1.39 | 1.31 | 1.05 |
| Srd5a1 | 1.08 | 0.82 | 0.85 | 1.28 | 2.23 | 1.27 | 1.11 | 0.48 | 1.30 | 0.79 | 0.67 | 0.75 |
| Srebf1 | 0.80 | 0.95 | 0.82 | 1.07 | 2.00 | 1.01 | 0.24 | 0.18 | 0.31 | 1.12 | 1.06 | 0.95 |
| Srebf2 | 0.75 | 0.68 | 0.89 | 1.18 | 1.27 | 1.29 | 0.84 | 0.88 | 1.03 | 1.14 | 0.73 | 0.96 |
| Srek1ip1 | 0.88 | 0.76 | 0.89 | 0.91 | 1.67 | 0.97 | 1.11 | 0.65 | 0.95 | 1.04 | 0.84 | 1.09 |
| Srsf5 | 1.06 | 1.18 | 0.88 | 0.98 | 1.47 | 0.86 | 0.97 | 0.54 | 0.94 | 0.97 | 1.18 | 1.00 |
| Ssbp1 | 0.91 | 1.01 | 1.06 | 0.93 | 1.16 | 0.93 | 0.78 | 1.00 | 1.03 | 0.93 | 0.67 | 1.13 |
| Ssh3 | 1.06 | 1.07 | 1.20 | 1.03 | 0.98 | 0.96 | 1.39 | 1.00 | 1.03 | 0.92 | 0.75 | 1.01 |
| St3gal5 | 0.91 | 0.71 | 0.91 | 0.54 | 1.13 | 0.62 | 1.85 | 2.86 | 2.02 | 1.75 | 1.12 | 1.52 |
| St6galnac5 | 1.00 | 1.00 | 1.00 | 0.60 | 1.00 | 1.00 | 1.00 | 1.00 | 1.00 | 0.51 | 0.78 | 0.64 |
| St8sia4 | 0.49 | 0.48 | 0.65 | 1.00 | 1.00 | 1.00 | 1.00 | 1.00 | 1.00 | 0.77 | 0.73 | 0.94 |
| Stam | 0.81 | 0.82 | 0.82 | 1.32 | 1.71 | 1.08 | 0.86 | 1.00 | 1.18 | 1.02 | 0.81 | 1.15 |
| Stard3nl | 0.76 | 0.93 | 0.82 | 0.68 | 2.30 | 0.82 | 1.20 | 1.00 | 0.84 | 0.71 | 0.86 | 0.79 |
| Stat5b | 0.83 | 0.87 | 0.91 | 1.29 | 1.71 | 1.08 | 0.95 | 0.71 | 0.89 | 1.03 | 0.80 | 0.93 |
| Steap3 | 0.91 | 0.64 | 0.90 | 0.85 | 1.43 | 0.98 | 0.61 | 0.49 | 0.72 | 0.83 | 0.72 | 0.80 |
| Steap4 | 2.58 | 1.72 | 1.52 | 3.85 | 1.00 | 2.46 | 1.67 | 2.54 | 1.22 | 1.90 | 1.19 | 1.64 |
| Stim1 | 0.88 | 0.77 | 0.96 | 1.45 | 1.00 | 1.37 | 1.07 | 1.00 | 1.05 | 1.18 | 0.74 | 1.11 |
| Stk10 | 0.78 | 0.78 | 1.15 | 0.75 | 1.00 | 0.91 | 1.45 | 1.00 | 1.14 | 1.08 | 0.81 | 1.13 |
| Strada | 1.06 | 1.18 | 1.13 | 0.94 | 1.24 | 0.95 | 0.97 | 1.00 | 1.38 | 1.07 | 0.97 | 0.84 |
| Stradb | 0.87 | 1.01 | 1.01 | 0.91 | 1.85 | 1.01 | 1.06 | 0.87 | 0.90 | 0.93 | 0.91 | 1.00 |
| Strn | 0.28 | 0.18 | 0.63 | 1.25 | 1.00 | 0.85 | 0.81 | 1.00 | 0.72 | 0.76 | 0.57 | 0.74 |
| Stub1 | 0.96 | 1.22 | 1.01 | 0.83 | 1.70 | 1.02 | 0.73 | 0.25 | 0.85 | 1.03 | 1.17 | 0.96 |
| Stxbp1 | 1.03 | 0.83 | 1.06 | 0.76 | 0.98 | 0.80 | 1.00 | 1.00 | 1.00 | 0.78 | 0.66 | 0.77 |
| Stxbp3a | 1.03 | 1.02 | 0.99 | 1.02 | 2.51 | 0.95 | 1.44 | 0.79 | 1.10 | 1.00 | 1.04 | 0.93 |
| Stxbp3b | 0.55 | 0.43 | 1.16 | 1.18 | 1.00 | 1.06 | 1.15 | 1.00 | 1.06 | 0.96 | 0.38 | 1.04 |
| Styx | 0.83 | 0.61 | 0.83 | 0.91 | 0.97 | 0.76 | 1.07 | 1.17 | 0.76 | 1.02 | 0.64 | 0.96 |
| Sucnr1 | 1.00 | 1.00 | 1.00 | 0.39 | 0.40 | 0.54 | 0.22 | 1.00 | 0.45 | 1.00 | 1.00 | 1.00 |

Fig. 35- 91

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Snrnp48 | 1.08 | 1.20 | 0.77 | 1.27 | 1.51 | 1.66 | 0.80 | 0.61 | 0.82 | 1.08 | 1.06 | 1.00 |
| Sntb1 | 1.27 | 1.21 | 0.83 | 0.46 | 0.12 | 0.29 | 1.00 | 1.00 | 1.00 | 0.78 | 0.45 | 0.89 |
| Snx13 | 1.05 | 0.83 | 0.72 | 0.91 | 0.88 | 0.85 | 1.15 | 0.61 | 0.96 | 0.91 | 0.82 | 1.10 |
| Snx18 | 1.01 | 1.09 | 0.84 | 1.06 | 0.24 | 0.83 | 1.02 | 1.00 | 1.03 | 0.92 | 0.83 | 1.04 |
| Snx24 | 1.17 | 1.00 | 1.17 | 1.93 | 0.94 | 1.32 | 1.00 | 1.00 | 1.00 | 0.71 | 0.95 | 0.72 |
| Socs3 | 1.00 | 1.05 | 0.76 | 1.28 | 1.00 | 1.23 | 1.08 | 1.00 | 1.00 | 1.20 | 0.82 | 0.88 |
| Sorbs1 | 1.16 | 1.17 | 1.22 | 0.50 | 0.16 | 0.47 | 1.02 | 1.00 | 0.93 | 0.73 | 0.92 | 0.94 |
| Sostdc1 | 1.53 | 2.00 | 1.70 | 1.00 | 0.65 | 1.00 | 0.79 | 1.38 | 0.96 | 1.02 | 0.71 | 0.67 |
| Sox18 | 1.08 | 1.15 | 1.47 | 0.94 | 0.10 | 1.05 | 0.56 | 1.00 | 0.82 | 0.91 | 0.67 | 0.94 |
| Sox21 | 1.04 | 1.23 | 0.96 | 1.00 | 1.00 | 1.00 | 1.00 | 1.00 | 1.00 | 1.00 | 1.00 | 1.00 |
| Sox7 | 0.59 | 0.76 | 0.99 | 0.62 | 0.21 | 1.42 | 0.86 | 1.00 | 1.08 | 0.69 | 0.71 | 0.85 |
| Sp1 | 1.01 | 0.94 | 0.81 | 1.07 | 0.21 | 0.90 | 1.15 | 0.57 | 1.22 | 0.99 | 0.62 | 1.10 |
| Sp2 | 1.15 | 1.34 | 1.15 | 0.94 | 0.61 | 0.86 | 0.91 | 0.84 | 1.11 | 0.85 | 0.73 | 0.87 |
| Sp3 | 0.96 | 0.89 | 0.88 | 0.97 | 0.15 | 0.92 | 1.19 | 1.15 | 0.91 | 0.93 | 0.59 | 1.04 |
| Spag1 | 1.10 | 1.38 | 1.07 | 1.18 | 1.00 | 1.00 | 1.06 | 0.41 | 1.02 | 1.01 | 1.27 | 1.31 |
| Spag11b | 1.00 | 1.00 | 1.00 | 0.15 | 1.00 | 1.00 | 1.00 | 1.00 | 1.00 | 1.00 | 1.00 | 1.00 |
| Spag9 | 1.05 | 0.97 | 0.98 | 0.87 | 0.26 | 0.76 | 1.01 | 1.35 | 1.02 | 0.94 | 0.78 | 0.91 |
| Spata2 | 0.86 | 0.96 | 0.88 | 1.08 | 0.86 | 1.00 | 1.07 | 0.84 | 1.02 | 0.95 | 0.87 | 1.08 |
| Speer1-ps1 | 1.00 | 1.00 | 1.00 | 1.00 | 1.00 | 1.00 | 0.29 | 0.06 | 0.32 | 1.00 | 1.00 | 1.00 |
| Spin1 | 1.08 | 1.10 | 0.98 | 2.21 | 0.62 | 1.60 | 1.16 | 0.54 | 0.85 | 1.12 | 0.99 | 1.25 |
| Spin2d | 1.00 | 1.00 | 1.00 | 1.00 | 1.00 | 1.00 | 0.79 | 0.18 | 1.23 | 1.00 | 1.00 | 1.00 |
| Spns3 | 1.00 | 1.00 | 1.00 | 1.00 | 1.00 | 1.00 | 1.00 | 1.66 | 1.00 | 0.86 | 0.81 | 0.59 |
| Spred2 | 1.23 | 1.26 | 0.94 | 0.95 | 0.58 | 0.94 | 0.89 | 1.00 | 1.27 | 1.00 | 0.72 | 1.07 |
| Sprr2a1 | 0.57 | 0.60 | 0.63 | 1.00 | 1.00 | 1.00 | 1.00 | 1.00 | 1.00 | 1.00 | 1.00 | 1.00 |
| Sprr2a2 | 0.56 | 0.61 | 0.63 | 1.00 | 1.00 | 1.00 | 1.00 | 1.00 | 1.00 | 1.00 | 1.00 | 1.00 |
| Sprr2b | 0.72 | 1.32 | 2.12 | 1.00 | 1.00 | 1.00 | 1.00 | 1.00 | 1.00 | 1.00 | 1.00 | 1.00 |
| Sprr2e | 0.95 | 1.26 | 1.20 | 1.00 | 1.00 | 1.00 | 1.00 | 1.00 | 1.00 | 1.00 | 1.00 | 1.00 |
| Sprr3 | 0.86 | 1.06 | 1.11 | 1.00 | 1.00 | 1.00 | 1.00 | 1.00 | 1.00 | 1.00 | 1.00 | 1.00 |
| Sprr4 | 0.88 | 1.00 | 1.00 | 1.00 | 1.00 | 1.00 | 1.00 | 1.00 | 1.00 | 1.00 | 1.00 | 1.00 |
| Sprtn | 0.97 | 0.81 | 0.62 | 0.85 | 0.44 | 0.52 | 1.48 | 2.39 | 1.43 | 0.76 | 0.26 | 1.09 |
| Spry1 | 1.18 | 1.26 | 1.30 | 1.47 | 0.60 | 1.27 | 1.06 | 0.86 | 1.17 | 1.75 | 1.14 | 1.15 |
| Spry2 | 0.93 | 0.88 | 0.95 | 1.09 | 0.34 | 1.12 | 0.77 | 1.00 | 0.98 | 0.98 | 1.15 | 0.77 |
| Spry4 | 1.32 | 1.40 | 1.07 | 1.58 | 0.38 | 1.70 | 0.78 | 1.00 | 0.94 | 1.16 | 1.33 | 1.10 |
| Spryd7 | 0.99 | 0.86 | 0.81 | 1.07 | 1.00 | 1.00 | 0.94 | 0.27 | 0.90 | 1.04 | 1.13 | 1.18 |
| Spta1 | 1.00 | 1.00 | 1.00 | 1.00 | 1.00 | 1.00 | 0.92 | 1.00 | 0.93 | 0.40 | 0.27 | 0.19 |
| Sptb | 1.24 | 1.20 | 1.07 | 1.00 | 1.00 | 1.00 | 1.00 | 1.00 | 1.00 | 0.32 | 0.69 | 0.24 |
| Sptbn1 | 1.03 | 1.00 | 0.80 | 0.91 | 0.16 | 0.54 | 1.19 | 1.12 | 1.14 | 0.92 | 0.86 | 1.12 |
| Sptssb | 0.66 | 0.64 | 0.62 | 1.00 | 1.00 | 1.00 | 1.00 | 1.00 | 1.00 | 1.00 | 1.00 | 1.00 |
| Srd5a1 | 0.66 | 0.71 | 0.67 | 0.66 | 1.00 | 0.71 | 0.70 | 1.10 | 0.89 | 1.00 | 1.00 | 1.00 |
| Srebf1 | 1.11 | 1.21 | 0.89 | 0.50 | 0.28 | 0.65 | 0.89 | 0.52 | 0.96 | 0.99 | 1.07 | 1.00 |
| Srebf2 | 0.84 | 0.92 | 0.74 | 1.27 | 0.40 | 1.47 | 1.10 | 0.79 | 1.04 | 0.95 | 0.78 | 1.08 |
| Srek1ip1 | 0.88 | 0.82 | 0.97 | 0.81 | 0.94 | 0.85 | 0.88 | 0.91 | 0.95 | 0.91 | 0.74 | 1.04 |
| Srsf5 | 1.02 | 1.17 | 1.01 | 0.99 | 0.58 | 1.13 | 0.88 | 0.87 | 0.94 | 1.11 | 0.94 | 0.89 |
| Ssbp1 | 0.95 | 1.04 | 1.12 | 0.97 | 0.83 | 1.17 | 0.68 | 1.00 | 1.11 | 1.15 | 0.98 | 1.14 |
| Ssh3 | 0.91 | 0.91 | 0.89 | 1.05 | 0.84 | 0.96 | 0.76 | 1.00 | 1.09 | 0.99 | 0.93 | 1.06 |
| St3gal5 | 0.87 | 0.85 | 0.89 | 0.97 | 0.38 | 0.91 | 0.58 | 1.61 | 0.64 | 0.32 | 0.35 | 0.19 |
| St6galnac5 | 1.00 | 0.96 | 0.65 | 0.18 | 0.23 | 0.30 | 1.00 | 1.00 | 1.00 | 0.34 | 0.99 | 0.32 |
| St8sia4 | 0.63 | 0.62 | 1.00 | 0.68 | 0.67 | 0.57 | 1.00 | 1.00 | 1.00 | 0.89 | 0.58 | 0.95 |
| Stam | 1.06 | 0.86 | 1.00 | 1.10 | 1.00 | 0.86 | 1.17 | 0.78 | 0.92 | 0.86 | 0.91 | 0.84 |
| Stard3nl | 0.81 | 0.90 | 0.80 | 0.93 | 1.00 | 0.76 | 0.46 | 0.18 | 0.51 | 0.57 | 0.77 | 0.65 |
| Stat5b | 1.13 | 1.04 | 1.05 | 1.02 | 0.40 | 0.97 | 0.92 | 1.00 | 0.89 | 0.97 | 0.77 | 0.98 |
| Steap3 | 0.74 | 0.75 | 0.86 | 0.66 | 0.30 | 0.68 | 0.90 | 1.00 | 0.90 | 0.51 | 0.49 | 0.46 |
| Steap4 | 1.95 | 1.30 | 0.99 | 0.50 | 0.31 | 0.48 | 2.92 | 1.00 | 1.40 | 1.52 | 1.27 | 2.72 |
| Stim1 | 1.46 | 1.62 | 1.30 | 1.92 | 0.23 | 1.36 | 1.09 | 0.41 | 1.00 | 1.14 | 1.08 | 1.31 |
| Stk10 | 1.01 | 1.15 | 1.12 | 1.23 | 0.73 | 1.02 | 1.06 | 0.75 | 0.95 | 0.78 | 0.60 | 0.95 |
| Strada | 1.04 | 0.97 | 1.38 | 0.78 | 0.73 | 0.89 | 0.99 | 0.48 | 1.05 | 1.10 | 1.12 | 1.03 |
| Stradb | 1.07 | 1.10 | 0.99 | 0.64 | 1.00 | 0.86 | 0.83 | 0.40 | 0.88 | 0.81 | 0.80 | 0.85 |
| Strn | 0.85 | 0.82 | 0.50 | 0.78 | 0.50 | 0.31 | 0.86 | 0.85 | 0.70 | 0.78 | 0.61 | 1.31 |
| Stub1 | 0.85 | 1.16 | 1.01 | 0.95 | 0.08 | 1.18 | 0.92 | 1.20 | 0.94 | 0.95 | 1.09 | 0.89 |
| Stxbp1 | 1.24 | 1.45 | 1.31 | 0.85 | 1.43 | 1.01 | 0.93 | 0.65 | 0.98 | 0.86 | 4.30 | 0.77 |
| Stxbp3a | 1.04 | 0.95 | 0.87 | 1.16 | 0.79 | 1.02 | 0.74 | 0.90 | 0.74 | 1.02 | 0.75 | 0.85 |
| Stxbp3b | 1.02 | 0.90 | 0.78 | 1.22 | 0.59 | 0.75 | 0.97 | 1.00 | 0.77 | 0.74 | 0.40 | 0.84 |
| Styx | 0.98 | 0.91 | 0.76 | 0.64 | 1.00 | 0.68 | 1.06 | 0.64 | 1.14 | 0.95 | 0.71 | 0.99 |
| Sucnr1 | 1.00 | 1.00 | 1.00 | 0.23 | 0.20 | 0.38 | 1.00 | 1.00 | 1.00 | 0.83 | 0.59 | 0.85 |

Fig. 35- 92

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Snrnp48 | 0.97 | 0.78 | 1.00 | 0.94 | 1.98 | 0.90 | 1.02 | 0.17 | 1.17 | 0.73 | 1.02 | 0.96 |
| Sntb1 | 1.62 | 1.70 | 1.60 | 0.81 | 1.00 | 0.94 | 0.85 | 1.00 | 1.36 | 1.00 | 0.72 | 0.87 |
| Snx13 | 1.13 | 1.33 | 1.42 | 1.00 | 1.00 | 0.93 | 0.89 | 0.13 | 1.12 | 0.57 | 1.05 | 0.96 |
| Snx18 | 1.13 | 0.95 | 1.04 | 0.86 | 1.00 | 0.97 | 0.93 | 0.19 | 1.03 | 0.88 | 1.55 | 1.14 |
| Snx24 | 1.00 | 1.00 | 1.00 | 1.06 | 1.00 | 0.94 | 1.25 | 0.17 | 1.29 | 0.74 | 1.68 | 1.19 |
| Socs3 | 1.53 | 1.50 | 1.75 | 1.23 | 1.00 | 0.99 | 0.93 | 0.19 | 0.93 | 1.62 | 2.16 | 1.74 |
| Sorbs1 | 0.76 | 0.74 | 0.99 | 1.11 | 2.71 | 1.08 | 1.25 | 0.40 | 1.62 | 0.35 | 0.63 | 0.68 |
| Sostdc1 | 0.84 | 0.58 | 0.94 | 0.81 | 1.00 | 0.95 | 0.59 | 0.15 | 0.70 | 1.00 | 1.00 | 1.00 |
| Sox18 | 1.06 | 1.03 | 1.27 | 1.11 | 1.00 | 1.13 | 0.99 | 0.18 | 1.11 | 1.00 | 1.00 | 1.03 |
| Sox21 | 1.00 | 1.00 | 1.00 | 0.76 | 1.00 | 0.90 | 0.56 | 0.06 | 0.56 | 1.00 | 1.00 | 1.00 |
| Sox7 | 1.01 | 0.83 | 0.97 | 0.98 | 1.00 | 1.00 | 0.79 | 0.38 | 0.69 | 1.00 | 1.00 | 1.00 |
| Sp1 | 1.27 | 1.46 | 1.00 | 0.82 | 1.00 | 0.88 | 0.68 | 0.13 | 0.94 | 0.39 | 0.91 | 0.99 |
| Sp2 | 1.37 | 1.16 | 1.04 | 1.15 | 1.00 | 1.05 | 0.81 | 0.17 | 1.02 | 0.64 | 0.93 | 0.94 |
| Sp3 | 0.90 | 0.87 | 1.37 | 0.87 | 0.46 | 0.98 | 0.75 | 0.25 | 1.07 | 0.50 | 0.85 | 0.82 |
| Spag1 | 1.00 | 1.00 | 1.00 | 0.98 | 1.00 | 0.88 | 1.09 | 0.12 | 0.88 | 1.00 | 1.00 | 1.00 |
| Spag11b | 1.00 | 1.00 | 1.00 | 1.00 | 1.00 | 1.00 | 1.00 | 1.00 | 1.00 | 1.00 | 1.00 | 1.00 |
| Spag9 | 1.40 | 1.29 | 1.37 | 0.96 | 0.55 | 0.95 | 0.85 | 0.10 | 1.11 | 0.43 | 0.97 | 0.88 |
| Spata2 | 1.08 | 0.98 | 0.79 | 1.07 | 2.24 | 0.98 | 1.13 | 0.23 | 1.07 | 0.50 | 0.95 | 0.81 |
| Speer1-ps1 | 1.00 | 1.00 | 1.00 | 1.00 | 1.00 | 1.00 | 1.00 | 1.00 | 1.00 | 1.00 | 1.00 | 1.00 |
| Spin1 | 1.11 | 1.18 | 1.11 | 1.10 | 0.82 | 1.08 | 0.91 | 0.15 | 1.13 | 0.67 | 1.03 | 1.11 |
| Spin2d | 1.00 | 1.00 | 1.00 | 1.00 | 1.00 | 1.00 | 1.00 | 1.00 | 1.00 | 1.00 | 1.00 | 1.00 |
| Spns3 | 1.00 | 1.00 | 1.00 | 1.00 | 1.00 | 1.00 | 1.00 | 2.27 | 1.00 | 1.66 | 0.73 | 0.90 |
| Spred2 | 2.07 | 0.95 | 1.33 | 1.05 | 1.00 | 0.94 | 0.56 | 0.12 | 1.17 | 1.00 | 0.61 | 0.74 |
| Sprr2a1 | 1.00 | 1.00 | 1.00 | 1.00 | 0.73 | 1.00 | 0.09 | 0.51 | 0.16 | 1.00 | 1.00 | 1.00 |
| Sprr2a2 | 1.00 | 1.00 | 1.00 | 1.00 | 1.00 | 1.00 | 0.08 | 0.41 | 0.16 | 1.00 | 1.00 | 1.00 |
| Sprr2b | 1.00 | 1.00 | 1.00 | 1.00 | 1.00 | 1.00 | 0.17 | 0.41 | 0.26 | 1.00 | 1.00 | 1.00 |
| Sprr2e | 1.00 | 1.00 | 1.00 | 1.00 | 1.00 | 1.00 | 0.19 | 0.18 | 0.48 | 1.00 | 1.00 | 1.00 |
| Sprr3 | 1.00 | 1.00 | 1.00 | 1.00 | 0.19 | 1.00 | 1.00 | 1.00 | 1.00 | 1.00 | 1.00 | 1.00 |
| Sprr4 | 1.00 | 1.00 | 1.00 | 1.00 | 1.00 | 1.00 | 0.77 | 0.03 | 0.26 | 1.00 | 1.00 | 1.00 |
| Sprtn | 1.04 | 1.63 | 0.83 | 0.92 | 0.94 | 0.85 | 0.63 | 0.15 | 0.87 | 1.00 | 0.60 | 0.54 |
| Spry1 | 1.05 | 1.23 | 0.84 | 1.15 | 1.00 | 0.92 | 0.90 | 0.20 | 0.89 | 1.00 | 1.09 | 1.59 |
| Spry2 | 0.87 | 1.34 | 0.91 | 1.15 | 0.15 | 1.04 | 1.71 | 0.58 | 1.65 | 0.60 | 0.94 | 1.09 |
| Spry4 | 1.00 | 1.00 | 1.00 | 1.39 | 0.73 | 1.17 | 1.65 | 1.00 | 1.52 | 1.00 | 1.00 | 1.00 |
| Spryd7 | 1.70 | 1.73 | 0.83 | 0.96 | 0.12 | 0.95 | 0.93 | 0.23 | 0.88 | 0.84 | 0.95 | 1.10 |
| Spta1 | 1.00 | 1.00 | 1.00 | 1.00 | 1.00 | 1.00 | 1.00 | 1.00 | 1.00 | 0.40 | 0.69 | 0.70 |
| Sptb | 1.00 | 1.00 | 1.00 | 0.93 | 0.99 | 0.99 | 1.21 | 2.08 | 1.90 | 0.16 | 0.58 | 0.42 |
| Sptbn1 | 0.95 | 1.40 | 1.23 | 0.90 | 0.96 | 0.94 | 0.96 | 0.30 | 1.13 | 0.64 | 1.09 | 1.16 |
| Sptssb | 1.00 | 1.00 | 1.00 | 0.97 | 0.68 | 1.11 | 1.00 | 1.00 | 1.00 | 1.00 | 1.00 | 1.00 |
| Srd5a1 | 1.00 | 1.00 | 1.00 | 0.99 | 1.00 | 0.75 | 0.90 | 0.15 | 0.69 | 1.00 | 1.00 | 1.00 |
| Srebf1 | 0.95 | 0.78 | 1.10 | 0.93 | 1.15 | 1.06 | 0.73 | 0.35 | 0.73 | 0.96 | 0.94 | 0.95 |
| Srebf2 | 1.30 | 0.89 | 1.12 | 0.92 | 0.79 | 0.91 | 0.76 | 0.25 | 0.67 | 1.09 | 1.63 | 1.60 |
| Srek1ip1 | 0.57 | 1.31 | 0.79 | 1.03 | 1.15 | 1.03 | 1.12 | 0.10 | 0.93 | 0.49 | 0.98 | 1.03 |
| Srsf5 | 0.91 | 0.91 | 1.01 | 1.16 | 0.58 | 0.99 | 0.88 | 0.10 | 1.07 | 0.55 | 1.18 | 1.01 |
| Ssbp1 | 0.75 | 1.48 | 0.68 | 1.00 | 1.50 | 0.93 | 1.04 | 0.18 | 1.09 | 0.39 | 1.34 | 1.10 |
| Ssh3 | 1.54 | 1.08 | 0.97 | 0.95 | 1.00 | 1.00 | 1.00 | 0.15 | 0.99 | 0.33 | 1.09 | 1.18 |
| St3gal5 | 0.56 | 0.55 | 0.65 | 1.30 | 2.05 | 1.08 | 0.99 | 0.77 | 0.78 | 0.38 | 0.57 | 0.49 |
| St6galnac5 | 1.00 | 1.00 | 1.00 | 0.84 | 0.98 | 0.80 | 0.88 | 3.45 | 2.11 | 1.00 | 1.00 | 1.00 |
| St8sia4 | 1.00 | 1.00 | 1.00 | 0.68 | 1.46 | 0.69 | 0.57 | 1.00 | 0.98 | 0.69 | 0.85 | 0.88 |
| Stam | 1.70 | 0.99 | 1.10 | 1.08 | 1.00 | 0.96 | 0.92 | 0.19 | 1.18 | 0.55 | 0.85 | 1.22 |
| Stard3nl | 1.16 | 0.65 | 0.56 | 0.83 | 1.38 | 0.85 | 0.73 | 0.16 | 0.84 | 0.58 | 0.73 | 0.79 |
| Stat5b | 1.20 | 1.60 | 1.58 | 0.96 | 1.00 | 1.00 | 0.99 | 0.15 | 1.09 | 0.59 | 1.05 | 0.99 |
| Steap3 | 0.75 | 0.62 | 0.90 | 0.73 | 0.52 | 0.83 | 0.63 | 0.41 | 0.95 | 0.28 | 0.53 | 0.63 |
| Steap4 | 0.99 | 1.13 | 1.33 | 1.00 | 1.00 | 1.00 | 1.00 | 0.20 | 0.91 | 0.68 | 0.94 | 1.48 |
| Stim1 | 1.18 | 1.10 | 1.03 | 1.00 | 1.00 | 1.07 | 1.11 | 0.02 | 1.19 | 0.16 | 0.97 | 0.96 |
| Stk10 | 1.00 | 1.00 | 1.00 | 0.98 | 1.00 | 0.99 | 0.98 | 0.14 | 0.82 | 0.46 | 0.93 | 0.88 |
| Strada | 0.87 | 1.00 | 0.97 | 0.88 | 0.77 | 1.00 | 1.06 | 0.17 | 0.98 | 0.65 | 1.15 | 1.17 |
| Stradb | 1.23 | 0.92 | 0.71 | 1.07 | 0.27 | 1.00 | 0.97 | 0.16 | 1.26 | 0.43 | 1.03 | 1.05 |
| Strn | 1.00 | 1.00 | 1.00 | 0.74 | 1.00 | 0.74 | 0.54 | 0.51 | 0.68 | 1.00 | 0.50 | 0.66 |
| Stub1 | 0.76 | 0.85 | 0.89 | 1.08 | 2.49 | 1.08 | 1.14 | 0.66 | 0.84 | 1.13 | 1.01 | 1.15 |
| Stxbp1 | 0.96 | 0.85 | 0.88 | 1.10 | 1.07 | 1.01 | 1.06 | 0.57 | 1.01 | 0.85 | 0.81 | 0.68 |
| Stxbp3a | 1.67 | 1.15 | 1.43 | 1.39 | 0.67 | 1.12 | 0.96 | 0.17 | 0.94 | 0.58 | 1.05 | 1.00 |
| Stxbp3b | 1.39 | 1.41 | 1.17 | 0.92 | 1.00 | 1.00 | 0.97 | 0.06 | 0.93 | 1.00 | 0.71 | 0.76 |
| Styx | 0.79 | 1.00 | 1.00 | 0.76 | 1.00 | 0.93 | 0.65 | 0.14 | 0.98 | 0.72 | 1.03 | 0.79 |
| Sucnr1 | 1.00 | 1.00 | 1.00 | 1.00 | 1.00 | 1.00 | 0.57 | 0.48 | 0.67 | 1.00 | 1.00 | 1.00 |

Fig. 35- 93

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Sugct | 1.00 | 1.00 | 1.00 | 0.74 | 0.82 | 1.41 | 1.00 | 1.00 | 1.00 | 1.00 | 1.00 | 1.00 |
| Susd3 | 1.00 | 1.00 | 1.00 | 1.00 | 1.00 | 1.00 | 1.00 | 1.00 | 0.87 | 0.85 | 0.57 | 0.93 |
| Suz12 | 0.83 | 1.48 | 1.06 | 2.24 | 0.44 | 1.04 | 1.01 | 1.24 | 1.07 | 0.51 | 0.44 | 0.93 |
| Sv2a | 1.00 | 1.00 | 1.00 | 1.00 | 0.11 | 1.00 | 0.66 | 0.54 | 0.63 | 1.00 | 1.00 | 1.00 |
| Svep1 | 0.78 | 1.00 | 1.41 | 0.97 | 0.35 | 0.66 | 0.88 | 0.97 | 0.91 | 0.79 | 0.34 | 1.03 |
| Sybu | 0.90 | 1.00 | 1.00 | 0.60 | 0.25 | 0.57 | 0.54 | 0.28 | 0.44 | 0.61 | 0.29 | 0.72 |
| Synpo2 | 0.38 | 1.20 | 0.84 | 1.80 | 0.62 | 0.67 | 0.96 | 1.40 | 1.23 | 1.00 | 0.63 | 1.03 |
| Syt11 | 0.79 | 1.06 | 1.06 | 1.49 | 0.09 | 0.98 | 0.93 | 1.16 | 1.24 | 1.02 | 0.70 | 0.99 |
| Tacc1 | 0.93 | 1.63 | 1.18 | 1.18 | 0.28 | 0.89 | 1.49 | 1.48 | 1.33 | 0.31 | 0.44 | 1.26 |
| Tada2b | 1.10 | 1.73 | 0.94 | 0.99 | 0.18 | 0.84 | 1.08 | 1.09 | 1.04 | 0.82 | 0.46 | 1.08 |
| Taf1 | 1.06 | 1.20 | 0.97 | 1.20 | 0.28 | 0.84 | 0.92 | 1.10 | 0.93 | 0.50 | 0.36 | 0.96 |
| Taf1d | 2.51 | 2.54 | 1.44 | 2.63 | 1.16 | 1.51 | 1.49 | 2.11 | 1.41 | 2.12 | 1.11 | 0.98 |
| Taf2 | 1.00 | 1.30 | 1.30 | 0.77 | 0.15 | 0.75 | 1.12 | 1.27 | 0.83 | 0.56 | 0.36 | 0.91 |
| Taf4a | 1.16 | 1.76 | 1.07 | 1.66 | 0.25 | 1.41 | 0.90 | 0.92 | 0.90 | 0.34 | 0.27 | 0.98 |
| Taf5l | 1.55 | 2.14 | 1.27 | 0.94 | 0.54 | 0.98 | 0.99 | 1.14 | 1.12 | 0.56 | 0.55 | 1.14 |
| Taf7 | 1.69 | 3.29 | 1.45 | 1.62 | 0.52 | 1.04 | 1.08 | 1.11 | 1.01 | 0.59 | 0.47 | 1.00 |
| Tamm41 | 0.92 | 0.71 | 0.72 | 0.64 | 2.00 | 1.08 | 0.86 | 0.76 | 0.98 | 1.34 | 1.12 | 1.19 |
| Tank | 1.04 | 2.24 | 0.87 | 1.13 | 0.16 | 0.84 | 1.08 | 1.03 | 0.93 | 0.41 | 0.37 | 0.91 |
| Taok1 | 0.78 | 1.60 | 0.98 | 1.25 | 0.31 | 0.93 | 0.89 | 1.09 | 1.03 | 0.46 | 0.41 | 1.03 |
| Tarbp2 | 1.70 | 0.76 | 0.93 | 0.17 | 3.87 | 0.96 | 1.22 | 0.79 | 0.96 | 1.49 | 2.18 | 0.89 |
| Tbc1d20 | 1.24 | 1.25 | 1.71 | 1.35 | 0.10 | 1.04 | 1.37 | 1.68 | 1.52 | 1.66 | 0.17 | 1.30 |
| Tbc1d21 | 1.00 | 1.00 | 1.00 | 1.00 | 1.00 | 1.00 | 1.00 | 1.00 | 1.00 | 1.00 | 1.00 | 1.00 |
| Tbc1d23 | 1.02 | 2.07 | 0.91 | 1.64 | 0.36 | 1.13 | 1.05 | 0.96 | 0.95 | 0.58 | 0.46 | 0.93 |
| Tbc1d25 | 1.46 | 1.73 | 1.29 | 1.04 | 0.48 | 1.09 | 1.01 | 1.30 | 1.03 | 0.39 | 0.43 | 1.01 |
| Tbc1d7 | 0.86 | 0.84 | 0.57 | 0.12 | 0.80 | 0.53 | 0.77 | 0.86 | 0.95 | 0.72 | 0.63 | 1.09 |
| Tbccd1 | 0.62 | 1.03 | 0.91 | 0.90 | 0.46 | 0.81 | 0.89 | 0.97 | 0.81 | 0.62 | 0.42 | 0.97 |
| Tbce | 0.94 | 1.78 | 1.13 | 1.33 | 0.18 | 0.88 | 1.46 | 1.80 | 1.39 | 0.30 | 0.33 | 1.20 |
| Tbx21 | 1.00 | 1.00 | 1.00 | 1.00 | 1.00 | 1.00 | 1.00 | 1.00 | 1.00 | 1.00 | 0.71 | 0.93 |
| Tcea3 | 0.74 | 0.67 | 0.64 | 1.00 | 1.00 | 0.57 | 0.70 | 0.75 | 0.60 | 0.91 | 1.49 | 1.05 |
| Tceal3 | 0.76 | 1.88 | 1.13 | 1.00 | 0.16 | 1.00 | 1.00 | 0.91 | 0.84 | 1.01 | 1.51 | 1.03 |
| Tcf12 | 0.92 | 1.69 | 1.00 | 1.35 | 0.32 | 0.97 | 1.09 | 1.13 | 1.00 | 0.29 | 0.30 | 0.83 |
| Tcf21 | 1.00 | 1.00 | 1.00 | 1.00 | 1.00 | 1.00 | 0.57 | 0.54 | 0.97 | 0.20 | 0.13 | 0.58 |
| Tcf24 | 1.00 | 1.00 | 1.00 | 1.00 | 1.00 | 1.00 | 1.00 | 1.00 | 1.00 | 1.00 | 1.00 | 1.00 |
| Tcf7 | 0.88 | 1.00 | 1.00 | 1.00 | 1.00 | 1.00 | 1.00 | 1.00 | 1.00 | 0.37 | 0.08 | 0.73 |
| Tead3 | 0.83 | 0.72 | 0.77 | 0.84 | 0.60 | 1.05 | 1.20 | 0.82 | 1.08 | 0.42 | 0.41 | 0.99 |
| Tecpr1 | 0.84 | 1.00 | 1.17 | 1.04 | 0.04 | 0.93 | 1.72 | 2.52 | 1.46 | 1.00 | 0.27 | 1.16 |
| Teddm1 | 1.00 | 1.00 | 1.00 | 1.00 | 1.00 | 1.00 | 1.00 | 1.00 | 1.00 | 1.00 | 1.00 | 1.00 |
| Tefm | 0.95 | 1.52 | 0.84 | 0.57 | 0.55 | 1.03 | 0.78 | 0.96 | 1.04 | 0.30 | 0.36 | 1.04 |
| Tenm4 | 1.00 | 1.00 | 1.00 | 0.65 | 0.64 | 0.78 | 1.00 | 1.00 | 1.00 | 1.00 | 1.00 | 1.00 |
| Tet2 | 0.72 | 1.00 | 0.99 | 1.78 | 0.49 | 1.16 | 0.87 | 0.89 | 1.12 | 1.00 | 0.40 | 0.88 |
| Tet3 | 0.61 | 1.00 | 0.80 | 1.81 | 0.31 | 0.66 | 0.92 | 1.08 | 1.00 | 0.57 | 0.27 | 0.83 |
| Tex10 | 0.90 | 0.84 | 1.12 | 1.25 | 0.54 | 1.08 | 1.36 | 1.71 | 1.29 | 0.78 | 0.68 | 1.09 |
| Tfap4 | 0.92 | 2.03 | 0.89 | 1.58 | 1.67 | 1.12 | 1.13 | 0.84 | 0.90 | 0.62 | 0.41 | 0.90 |
| Tfb2m | 0.89 | 1.34 | 0.87 | 1.45 | 0.57 | 0.99 | 0.95 | 1.08 | 0.85 | 0.25 | 0.46 | 1.00 |
| Tgfa | 1.00 | 1.00 | 1.00 | 1.00 | 0.85 | 1.00 | 1.08 | 1.00 | 1.00 | 1.00 | 0.29 | 1.42 |
| Tgfb2 | 0.41 | 0.99 | 0.52 | 1.00 | 1.00 | 1.00 | 0.87 | 0.94 | 1.57 | 0.80 | 0.31 | 1.10 |
| Tgif2lx2 | 1.00 | 1.00 | 1.00 | 1.00 | 1.00 | 1.00 | 1.00 | 1.00 | 1.00 | 1.00 | 1.00 | 1.00 |
| Tgm4 | 1.15 | 0.65 | 0.79 | 0.66 | 4.42 | 0.95 | 1.05 | 1.01 | 0.80 | 1.81 | 2.27 | 1.07 |
| Tgm7 | 1.00 | 1.00 | 1.00 | 1.00 | 1.00 | 1.00 | 1.00 | 1.00 | 1.00 | 1.00 | 1.00 | 1.00 |
| Tgs1 | 1.15 | 1.24 | 1.26 | 2.22 | 0.30 | 1.28 | 0.94 | 1.38 | 1.15 | 1.04 | 0.38 | 0.99 |
| Thbd | 2.56 | 3.67 | 1.30 | 1.06 | 0.15 | 0.74 | 0.85 | 1.02 | 1.10 | 0.32 | 0.24 | 0.72 |
| Them6 | 1.01 | 0.90 | 0.65 | 0.60 | 0.52 | 0.80 | 0.90 | 0.72 | 0.95 | 0.55 | 0.59 | 0.94 |
| Themis2 | 1.00 | 1.00 | 1.20 | 2.04 | 0.89 | 1.58 | 1.12 | 1.03 | 1.67 | 1.00 | 0.25 | 1.15 |
| Thnsl2 | 0.33 | 0.21 | 0.41 | 0.36 | 1.21 | 0.49 | 0.41 | 0.45 | 0.31 | 0.18 | 0.28 | 0.67 |
| Thoc2 | 0.92 | 1.33 | 0.98 | 2.69 | 0.31 | 0.89 | 0.87 | 1.21 | 1.14 | 0.78 | 0.42 | 0.95 |
| Thra | 0.88 | 2.51 | 1.14 | 0.70 | 0.05 | 0.93 | 1.08 | 1.28 | 1.19 | 0.64 | 0.12 | 1.14 |
| Thy1 | 0.75 | 0.93 | 0.85 | 0.34 | 0.15 | 0.72 | 0.98 | 0.78 | 1.01 | 0.66 | 0.79 | 0.65 |
| Tifa | 1.19 | 1.00 | 1.29 | 2.20 | 0.94 | 0.86 | 1.51 | 1.06 | 1.68 | 0.84 | 0.45 | 1.12 |
| Timm21 | 0.82 | 1.42 | 0.84 | 0.96 | 0.45 | 0.72 | 0.85 | 0.96 | 0.76 | 0.19 | 0.53 | 0.86 |
| Timp3 | 0.71 | 1.49 | 0.88 | 2.73 | 0.25 | 1.10 | 0.89 | 1.18 | 1.00 | 0.36 | 0.43 | 1.31 |
| Tiparp | 2.03 | 3.92 | 1.91 | 4.36 | 1.13 | 1.07 | 1.33 | 2.41 | 1.56 | 0.54 | 0.57 | 1.07 |
| Tjp1 | 0.58 | 0.84 | 0.83 | 2.99 | 0.35 | 0.87 | 0.96 | 1.03 | 1.02 | 0.66 | 0.47 | 1.16 |
| Tk1 | 0.34 | 0.34 | 0.31 | 1.00 | 1.00 | 1.00 | 1.44 | 1.63 | 0.79 | 0.47 | 1.25 | 0.67 |
| Tldc1 | 0.66 | 1.00 | 0.99 | 1.59 | 0.73 | 1.38 | 0.77 | 0.95 | 0.74 | 0.77 | 0.30 | 1.00 |

Fig. 35- 94

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Sugct | 1.00 | 1.00 | 1.00 | 0.76 | 1.08 | 0.67 | 0.46 | 0.08 | 0.28 | 1.00 | 1.00 | 1.00 |
| Susd3 | 1.22 | 2.56 | 2.03 | 0.83 | 1.26 | 0.85 | 1.00 | 1.00 | 1.00 | 0.96 | 1.31 | 0.73 |
| Suz12 | 0.56 | 0.58 | 0.71 | 1.15 | 2.06 | 0.94 | 1.17 | 0.82 | 0.95 | 1.05 | 0.74 | 1.07 |
| Sv2a | 0.56 | 0.49 | 0.77 | 0.96 | 1.00 | 1.23 | 1.00 | 1.00 | 1.00 | 1.08 | 0.91 | 1.12 |
| Svep1 | 1.00 | 1.00 | 0.98 | 1.54 | 1.00 | 1.39 | 1.00 | 1.00 | 1.00 | 0.79 | 0.43 | 0.74 |
| Sybu | 1.00 | 1.00 | 1.13 | 1.00 | 1.00 | 1.00 | 1.00 | 1.00 | 1.00 | 1.53 | 1.34 | 1.41 |
| Synpo2 | 1.05 | 0.77 | 1.14 | 1.00 | 1.00 | 1.00 | 1.00 | 1.00 | 1.00 | 1.04 | 0.72 | 0.96 |
| Syt11 | 0.96 | 0.96 | 1.87 | 0.85 | 1.28 | 1.22 | 1.00 | 1.00 | 1.00 | 1.13 | 0.92 | 1.04 |
| Tacc1 | 0.82 | 0.78 | 1.07 | 1.31 | 1.96 | 1.28 | 0.95 | 0.92 | 0.76 | 1.00 | 0.68 | 1.04 |
| Tada2b | 0.87 | 0.69 | 0.94 | 1.03 | 1.95 | 0.98 | 0.91 | 0.58 | 1.02 | 1.10 | 0.65 | 1.10 |
| Taf1 | 0.69 | 0.67 | 0.83 | 1.01 | 1.00 | 0.88 | 1.05 | 1.00 | 1.07 | 0.94 | 0.81 | 0.86 |
| Taf1d | 0.77 | 0.68 | 0.96 | 1.08 | 1.21 | 0.83 | 1.43 | 1.45 | 1.08 | 1.28 | 1.17 | 1.13 |
| Taf2 | 0.72 | 0.72 | 0.76 | 0.86 | 1.00 | 0.91 | 1.25 | 1.00 | 0.80 | 0.89 | 0.82 | 0.77 |
| Taf4a | 0.63 | 0.72 | 0.84 | 1.27 | 1.23 | 0.96 | 1.02 | 1.00 | 1.05 | 0.97 | 0.81 | 0.96 |
| Taf5l | 0.79 | 0.82 | 0.79 | 1.08 | 2.00 | 0.97 | 0.98 | 1.09 | 1.09 | 1.00 | 0.93 | 1.02 |
| Taf7 | 0.94 | 0.94 | 0.87 | 0.97 | 1.00 | 1.11 | 0.69 | 1.00 | 1.06 | 1.12 | 1.15 | 1.03 |
| Tamm41 | 0.78 | 0.73 | 0.85 | 0.87 | 0.62 | 0.69 | 0.78 | 1.16 | 0.80 | 1.22 | 0.99 | 0.84 |
| Tank | 0.83 | 0.76 | 1.05 | 1.06 | 1.19 | 1.00 | 1.57 | 1.00 | 1.25 | 0.94 | 0.86 | 0.91 |
| Taok1 | 0.71 | 0.64 | 0.93 | 1.05 | 1.14 | 0.93 | 1.07 | 1.00 | 1.05 | 1.04 | 0.76 | 0.97 |
| Tarbp2 | 1.26 | 1.46 | 1.01 | 1.25 | 0.88 | 0.87 | 1.20 | 1.71 | 0.88 | 1.02 | 1.53 | 1.10 |
| Tbc1d20 | 0.74 | 0.55 | 1.00 | 1.19 | 0.91 | 1.18 | 1.05 | 1.41 | 1.17 | 1.04 | 0.38 | 1.03 |
| Tbc1d21 | 1.00 | 1.00 | 1.00 | 1.00 | 1.00 | 1.00 | 1.00 | 1.00 | 1.00 | 1.00 | 1.00 | 1.00 |
| Tbc1d23 | 0.99 | 1.02 | 1.00 | 1.01 | 1.58 | 1.00 | 1.30 | 1.00 | 1.17 | 1.01 | 0.90 | 1.02 |
| Tbc1d25 | 0.80 | 0.87 | 1.03 | 1.24 | 1.86 | 1.14 | 1.16 | 1.00 | 0.76 | 1.17 | 0.83 | 1.05 |
| Tbc1d7 | 1.19 | 1.20 | 0.89 | 0.97 | 1.93 | 0.89 | 0.81 | 0.30 | 1.05 | 0.90 | 0.89 | 0.54 |
| Tbccd1 | 0.97 | 0.99 | 1.03 | 0.96 | 1.23 | 0.81 | 0.64 | 0.39 | 0.72 | 1.18 | 1.14 | 1.09 |
| Tbcel | 0.73 | 0.67 | 0.93 | 1.15 | 1.92 | 1.05 | 0.85 | 0.83 | 1.18 | 1.04 | 0.71 | 1.00 |
| Tbx21 | 1.34 | 0.86 | 1.66 | 1.00 | 1.00 | 1.00 | 1.00 | 1.00 | 1.00 | 1.00 | 1.00 | 1.00 |
| Tcea3 | 0.99 | 0.97 | 0.64 | 0.65 | 0.81 | 0.94 | 0.33 | 0.19 | 0.43 | 0.81 | 1.11 | 0.94 |
| Tceal3 | 2.27 | 2.57 | 0.81 | 1.00 | 1.00 | 0.78 | 1.00 | 1.00 | 1.00 | 0.81 | 0.98 | 0.97 |
| Tcf12 | 0.61 | 0.59 | 0.76 | 0.97 | 1.28 | 0.90 | 1.26 | 1.00 | 1.12 | 1.07 | 0.74 | 1.09 |
| Tcf21 | 1.00 | 1.00 | 1.00 | 0.57 | 0.85 | 0.64 | 1.51 | 1.00 | 1.08 | 0.47 | 0.51 | 0.69 |
| Tcf24 | 1.00 | 1.00 | 1.00 | 0.94 | 0.97 | 1.02 | 0.08 | 0.61 | 0.17 | 1.00 | 1.00 | 1.00 |
| Tcf7 | 0.56 | 0.60 | 0.80 | 1.00 | 1.00 | 1.00 | 0.86 | 1.00 | 0.78 | 0.94 | 0.76 | 0.92 |
| Tead3 | 1.51 | 1.37 | 1.55 | 1.08 | 1.46 | 0.97 | 0.91 | 1.67 | 1.30 | 0.86 | 0.89 | 1.04 |
| Tecpr1 | 0.75 | 0.72 | 1.09 | 1.42 | 1.00 | 1.25 | 0.80 | 1.00 | 1.32 | 1.05 | 0.57 | 0.97 |
| Teddm1 | 1.00 | 1.00 | 1.00 | 1.00 | 1.00 | 1.00 | 1.00 | 1.00 | 1.00 | 1.00 | 1.00 | 1.00 |
| Tefm | 0.97 | 1.22 | 1.01 | 0.91 | 1.13 | 0.86 | 0.86 | 0.81 | 0.99 | 0.91 | 0.92 | 0.95 |
| Tenm4 | 1.00 | 0.86 | 1.31 | 1.00 | 1.00 | 1.00 | 1.00 | 1.00 | 1.00 | 1.00 | 1.00 | 1.00 |
| Tet2 | 0.76 | 0.65 | 1.04 | 1.00 | 1.00 | 1.12 | 0.86 | 1.00 | 0.92 | 1.02 | 0.73 | 0.85 |
| Tet3 | 0.52 | 0.45 | 0.82 | 0.95 | 1.00 | 1.08 | 0.75 | 1.00 | 1.04 | 0.88 | 0.56 | 0.90 |
| Tex10 | 0.66 | 0.64 | 0.89 | 1.16 | 1.00 | 0.91 | 1.14 | 1.00 | 1.50 | 1.33 | 0.92 | 1.11 |
| Tfap4 | 0.90 | 1.00 | 0.95 | 1.32 | 0.52 | 1.20 | 0.56 | 1.13 | 0.70 | 1.05 | 0.92 | 0.86 |
| Tfb2m | 0.94 | 0.98 | 0.89 | 0.97 | 1.73 | 0.97 | 1.03 | 0.27 | 0.99 | 0.96 | 1.02 | 1.09 |
| Tgfa | 1.06 | 1.19 | 1.76 | 1.39 | 1.00 | 1.04 | 1.23 | 1.00 | 1.15 | 1.27 | 0.69 | 1.17 |
| Tgfb2 | 1.28 | 0.71 | 1.25 | 1.00 | 1.00 | 1.00 | 1.00 | 1.00 | 1.00 | 0.78 | 0.46 | 0.92 |
| Tgif2lx2 | 1.00 | 1.00 | 1.00 | 1.00 | 1.00 | 1.00 | 1.00 | 1.00 | 1.00 | 1.00 | 1.00 | 1.00 |
| Tgm4 | 1.11 | 1.27 | 1.02 | 0.85 | 0.86 | 1.23 | 0.76 | 1.40 | 1.14 | 0.13 | 1.37 | 0.60 |
| Tgm7 | 1.00 | 1.00 | 1.00 | 1.00 | 1.00 | 1.00 | 1.00 | 1.00 | 1.00 | 0.74 | 0.61 | 0.82 |
| Tgs1 | 0.79 | 0.68 | 0.91 | 1.25 | 1.00 | 1.35 | 1.33 | 1.00 | 1.66 | 1.02 | 0.84 | 1.00 |
| Thbd | 0.98 | 0.70 | 0.94 | 1.41 | 2.31 | 1.19 | 3.39 | 1.00 | 3.20 | 0.94 | 0.63 | 0.95 |
| Them6 | 0.54 | 0.71 | 0.57 | 0.94 | 1.34 | 0.97 | 0.62 | 0.28 | 0.71 | 1.00 | 1.10 | 0.86 |
| Themis2 | 1.12 | 0.80 | 2.06 | 1.00 | 1.00 | 1.00 | 0.83 | 1.00 | 1.39 | 0.75 | 0.44 | 0.86 |
| Thnsl2 | 1.32 | 1.03 | 0.59 | 0.44 | 0.37 | 0.45 | 0.86 | 0.33 | 0.74 | 0.30 | 0.31 | 0.31 |
| Thoc2 | 0.74 | 0.72 | 0.91 | 0.99 | 1.09 | 0.87 | 0.98 | 1.00 | 1.09 | 0.92 | 0.65 | 0.99 |
| Thra | 0.74 | 0.54 | 1.06 | 1.06 | 1.00 | 1.24 | 0.72 | 1.00 | 0.86 | 0.81 | 0.61 | 0.98 |
| Thy1 | 0.68 | 0.87 | 0.69 | 1.00 | 0.92 | 0.71 | 1.00 | 1.49 | 1.21 | 0.92 | 1.22 | 1.09 |
| Tifa | 1.34 | 1.53 | 1.66 | 1.18 | 1.00 | 0.86 | 0.90 | 0.84 | 0.84 | 0.97 | 0.96 | 1.17 |
| Timm21 | 0.95 | 0.85 | 0.76 | 0.80 | 1.19 | 0.86 | 0.74 | 0.63 | 0.78 | 0.87 | 0.84 | 0.94 |
| Timp3 | 1.05 | 0.77 | 0.97 | 1.41 | 1.85 | 1.18 | 1.05 | 0.64 | 1.19 | 0.80 | 0.53 | 0.74 |
| Tiparp | 1.59 | 1.25 | 1.15 | 1.22 | 2.05 | 1.12 | 2.18 | 1.00 | 1.23 | 1.27 | 1.11 | 1.05 |
| Tjp1 | 1.29 | 0.88 | 1.08 | 1.04 | 1.63 | 1.07 | 0.98 | 1.46 | 1.28 | 1.01 | 0.71 | 0.94 |
| Tk1 | 0.35 | 0.59 | 0.46 | 0.41 | 0.33 | 0.41 | 0.17 | 0.06 | 0.29 | 0.61 | 1.07 | 1.06 |
| Tldc1 | 0.95 | 1.04 | 1.12 | 1.03 | 1.00 | 1.00 | 1.08 | 1.00 | 1.20 | 1.10 | 0.84 | 1.07 |

Fig. 35- 95

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Sugct | 1.00 | 1.00 | 1.00 | 0.64 | 1.00 | 1.31 | 0.99 | 1.00 | 1.00 | 1.00 | 1.00 | 1.00 |
| Susd3 | 1.02 | 1.00 | 1.00 | 0.85 | 1.47 | 1.18 | 0.85 | 0.44 | 0.93 | 1.34 | 1.18 | 1.25 |
| Suz12 | 1.01 | 0.93 | 0.86 | 1.01 | 0.38 | 1.15 | 1.14 | 0.40 | 1.02 | 1.00 | 0.78 | 0.97 |
| Sv2a | 0.64 | 0.94 | 1.05 | 1.00 | 1.00 | 1.00 | 1.00 | 1.00 | 1.00 | 0.79 | 4.80 | 0.88 |
| Svep1 | 0.87 | 0.89 | 0.88 | 0.82 | 0.14 | 0.65 | 1.00 | 1.00 | 1.00 | 1.16 | 0.70 | 1.46 |
| Sybu | 1.13 | 1.32 | 1.13 | 0.50 | 1.00 | 0.55 | 0.76 | 1.00 | 0.59 | 1.00 | 4.39 | 1.00 |
| Synpo2 | 1.57 | 1.47 | 1.41 | 1.07 | 0.15 | 0.26 | 1.00 | 1.00 | 1.00 | 1.28 | 0.81 | 1.11 |
| Syt11 | 1.22 | 1.04 | 1.23 | 0.97 | 1.00 | 0.82 | 1.08 | 0.75 | 0.99 | 0.71 | 3.69 | 0.77 |
| Tacc1 | 1.18 | 1.32 | 1.36 | 0.87 | 0.09 | 0.85 | 1.21 | 0.34 | 0.99 | 1.14 | 0.86 | 1.07 |
| Tada2b | 1.00 | 1.14 | 0.91 | 1.13 | 0.31 | 1.20 | 1.07 | 0.79 | 0.96 | 0.99 | 0.68 | 1.02 |
| Taf1 | 1.06 | 0.93 | 0.92 | 0.97 | 1.00 | 0.76 | 1.15 | 1.00 | 0.91 | 1.06 | 0.82 | 1.06 |
| Taf1d | 0.96 | 0.75 | 0.81 | 1.59 | 1.34 | 1.39 | 1.14 | 0.98 | 0.86 | 1.21 | 1.19 | 1.29 |
| Taf2 | 0.88 | 0.74 | 0.83 | 0.91 | 1.00 | 0.87 | 1.07 | 0.47 | 0.95 | 0.89 | 0.69 | 0.87 |
| Taf4a | 1.06 | 0.95 | 0.96 | 0.95 | 0.95 | 1.11 | 0.92 | 1.00 | 1.13 | 0.93 | 0.83 | 1.03 |
| Taf5l | 1.06 | 0.95 | 0.83 | 1.30 | 1.00 | 1.33 | 1.22 | 0.83 | 0.98 | 1.12 | 0.97 | 1.04 |
| Taf7 | 0.92 | 0.97 | 0.92 | 1.10 | 1.00 | 1.31 | 0.95 | 0.26 | 0.99 | 0.99 | 0.99 | 1.11 |
| Tamm41 | 1.13 | 0.71 | 0.68 | 0.75 | 1.00 | 0.87 | 1.10 | 1.31 | 0.71 | 1.58 | 0.73 | 1.12 |
| Tank | 1.10 | 0.90 | 1.15 | 1.02 | 0.57 | 0.99 | 0.91 | 1.40 | 0.70 | 0.87 | 0.77 | 0.85 |
| Taok1 | 0.97 | 0.88 | 0.83 | 0.90 | 0.15 | 0.75 | 1.13 | 0.73 | 1.06 | 1.03 | 0.70 | 1.10 |
| Tarbp2 | 0.79 | 1.32 | 1.12 | 1.04 | 1.22 | 1.31 | 0.94 | 1.72 | 1.02 | 1.03 | 1.13 | 0.88 |
| Tbc1d20 | 0.99 | 1.01 | 0.80 | 1.26 | 0.60 | 1.17 | 0.99 | 2.37 | 1.07 | 0.99 | 0.55 | 1.12 |
| Tbc1d21 | 1.00 | 1.00 | 1.00 | 1.00 | 1.00 | 1.00 | 1.07 | 0.18 | 0.92 | 1.00 | 1.00 | 1.00 |
| Tbc1d23 | 1.00 | 0.88 | 0.96 | 0.91 | 0.59 | 0.86 | 0.97 | 1.02 | 0.89 | 1.14 | 0.98 | 1.08 |
| Tbc1d25 | 0.86 | 0.92 | 1.06 | 1.28 | 1.00 | 1.05 | 1.05 | 0.64 | 1.10 | 0.84 | 0.70 | 1.12 |
| Tbc1d7 | 0.81 | 0.82 | 0.75 | 0.51 | 1.00 | 0.52 | 0.60 | 0.25 | 0.68 | 0.83 | 0.98 | 0.55 |
| Tbccd1 | 1.03 | 1.04 | 0.96 | 0.85 | 0.59 | 0.82 | 0.99 | 0.25 | 0.97 | 0.99 | 0.92 | 0.89 |
| Tbcel | 1.21 | 1.36 | 1.16 | 1.21 | 1.00 | 0.95 | 1.06 | 1.65 | 1.00 | 0.80 | 0.63 | 0.88 |
| Tbx21 | 1.00 | 1.00 | 1.00 | 1.00 | 1.00 | 1.00 | 1.00 | 1.19 | 1.00 | 0.86 | 0.63 | 0.92 |
| Tcea3 | 1.10 | 1.44 | 1.22 | 1.34 | 1.00 | 1.90 | 1.00 | 1.00 | 1.00 | 1.00 | 0.65 | 1.00 |
| Tceal3 | 1.06 | 1.15 | 1.69 | 1.52 | 4.83 | 2.62 | 0.84 | 1.22 | 0.94 | 0.74 | 3.59 | 0.65 |
| Tcf12 | 0.99 | 0.79 | 1.07 | 1.10 | 0.33 | 1.03 | 1.17 | 0.87 | 1.20 | 1.00 | 0.78 | 1.10 |
| Tcf21 | 0.67 | 0.75 | 0.98 | 1.02 | 0.75 | 1.22 | 0.60 | 0.65 | 0.87 | 0.83 | 1.03 | 1.20 |
| Tcf24 | 0.89 | 1.00 | 0.96 | 1.00 | 1.00 | 1.00 | 1.09 | 1.00 | 1.00 | 1.00 | 1.00 | 1.00 |
| Tcf7 | 1.09 | 0.72 | 1.41 | 0.84 | 0.78 | 2.07 | 1.01 | 1.00 | 1.03 | 0.78 | 0.57 | 0.88 |
| Tead3 | 0.93 | 0.97 | 1.16 | 1.08 | 1.00 | 1.42 | 0.87 | 1.00 | 1.00 | 1.05 | 1.08 | 1.51 |
| Tecpr1 | 0.86 | 0.99 | 0.85 | 2.80 | 0.50 | 1.44 | 0.95 | 1.00 | 1.00 | 0.92 | 0.74 | 0.93 |
| Teddm1 | 1.00 | 1.00 | 1.00 | 0.18 | 1.00 | 1.00 | 1.00 | 1.00 | 1.00 | 1.00 | 1.00 | 1.00 |
| Tefm | 1.01 | 1.09 | 0.85 | 0.82 | 0.92 | 0.98 | 1.31 | 0.49 | 0.88 | 1.50 | 1.17 | 1.28 |
| Tenm4 | 1.05 | 1.01 | 0.84 | 0.32 | 0.18 | 0.21 | 0.90 | 1.30 | 1.00 | 0.79 | 1.18 | 1.46 |
| Tet2 | 1.10 | 1.11 | 0.86 | 0.96 | 0.53 | 0.74 | 1.00 | 1.00 | 1.00 | 0.95 | 0.57 | 1.10 |
| Tet3 | 0.79 | 0.82 | 0.67 | 0.86 | 0.37 | 0.63 | 1.26 | 1.00 | 1.28 | 0.88 | 0.52 | 1.12 |
| Tex10 | 1.05 | 0.81 | 0.94 | 1.08 | 1.00 | 0.83 | 1.15 | 0.16 | 1.03 | 1.07 | 0.86 | 1.00 |
| Tfap4 | 0.90 | 0.88 | 1.15 | 0.89 | 1.00 | 1.01 | 1.25 | 1.00 | 1.02 | 1.30 | 1.20 | 1.36 |
| Tfb2m | 1.08 | 0.92 | 1.15 | 1.34 | 0.36 | 1.50 | 0.87 | 0.54 | 1.00 | 1.03 | 0.89 | 0.96 |
| Tgfa | 0.80 | 0.84 | 0.69 | 1.35 | 0.77 | 1.93 | 0.95 | 1.00 | 0.86 | 1.00 | 2.48 | 0.94 |
| Tgfb2 | 0.94 | 1.52 | 1.34 | 0.99 | 1.00 | 0.90 | 1.00 | 1.00 | 1.00 | 0.70 | 1.01 | 1.00 |
| Tgif2lx2 | 1.00 | 1.00 | 1.00 | 1.00 | 1.00 | 1.00 | 1.44 | 0.11 | 0.18 | 1.00 | 1.00 | 1.00 |
| Tgm4 | 0.81 | 1.03 | 0.98 | 0.86 | 3.88 | 0.91 | 1.00 | 2.17 | 1.00 | 1.01 | 1.00 | 0.76 |
| Tgm7 | 1.00 | 1.00 | 1.00 | 1.00 | 1.00 | 1.00 | 1.00 | 1.00 | 1.00 | 1.00 | 1.00 | 1.00 |
| Tgs1 | 1.07 | 0.87 | 1.06 | 1.23 | 1.00 | 1.27 | 1.19 | 1.00 | 1.13 | 1.23 | 0.82 | 1.18 |
| Thbd | 1.01 | 1.02 | 0.96 | 1.17 | 0.28 | 1.16 | 0.79 | 1.00 | 0.86 | 0.99 | 0.72 | 0.97 |
| Them6 | 0.98 | 0.93 | 1.08 | 0.86 | 1.00 | 0.87 | 0.76 | 0.52 | 0.90 | 1.20 | 1.31 | 0.91 |
| Themis2 | 1.36 | 0.95 | 1.37 | 0.79 | 1.00 | 0.80 | 1.00 | 1.00 | 1.00 | 0.73 | 0.47 | 0.88 |
| Thnsl2 | 1.56 | 1.53 | 1.24 | 0.34 | 0.83 | 0.40 | 0.39 | 0.43 | 0.47 | 0.87 | 0.87 | 0.82 |
| Thoc2 | 0.95 | 0.90 | 1.02 | 0.95 | 0.48 | 0.88 | 0.90 | 1.00 | 0.89 | 1.08 | 0.73 | 1.12 |
| Thra | 0.97 | 1.04 | 1.00 | 0.80 | 0.30 | 1.14 | 1.12 | 1.00 | 1.04 | 0.79 | 1.80 | 1.13 |
| Thy1 | 1.20 | 1.08 | 1.40 | 0.91 | 1.54 | 1.14 | 1.00 | 1.00 | 1.00 | 0.80 | 1.38 | 0.99 |
| Tifa | 1.35 | 1.66 | 1.51 | 1.35 | 1.00 | 0.94 | 1.26 | 1.00 | 0.69 | 1.04 | 0.76 | 0.86 |
| Timm21 | 1.10 | 0.84 | 1.03 | 0.65 | 0.38 | 0.95 | 1.04 | 1.00 | 0.91 | 1.18 | 1.02 | 1.13 |
| Timp3 | 0.87 | 0.96 | 0.92 | 0.80 | 0.15 | 0.87 | 0.85 | 0.49 | 0.77 | 1.37 | 1.10 | 1.45 |
| Tiparp | 1.27 | 1.24 | 1.09 | 1.90 | 1.29 | 0.86 | 1.12 | 0.58 | 0.96 | 1.44 | 1.00 | 1.41 |
| Tjp1 | 0.95 | 0.89 | 0.77 | 0.92 | 0.15 | 0.74 | 1.25 | 1.83 | 1.07 | 0.81 | 0.72 | 1.01 |
| Tk1 | 0.46 | 0.52 | 0.54 | 0.51 | 1.00 | 0.58 | 0.81 | 0.64 | 1.05 | 0.49 | 0.53 | 0.39 |
| Tldc1 | 0.92 | 1.00 | 0.90 | 1.00 | 1.00 | 1.00 | 0.92 | 1.29 | 1.06 | 1.00 | 0.97 | 0.98 |

Fig. 35- 96

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Sugct | 1.00 | 1.00 | 1.00 | 0.67 | 1.00 | 1.01 | 1.00 | 1.00 | 1.00 | 1.00 | 1.00 | 1.00 |
| Susd3 | 1.39 | 3.64 | 2.47 | 0.90 | 0.12 | 1.00 | 0.73 | 0.68 | 1.57 | 1.25 | 1.16 | 1.30 |
| Suz12 | 1.18 | 1.07 | 1.33 | 0.95 | 0.48 | 0.88 | 0.73 | 0.14 | 1.05 | 0.47 | 0.83 | 0.84 |
| Sv2a | 1.00 | 1.00 | 1.00 | 1.09 | 0.86 | 1.00 | 0.93 | 1.00 | 1.00 | 1.00 | 1.00 | 1.00 |
| Svep1 | 1.00 | 1.00 | 1.00 | 1.00 | 1.00 | 0.89 | 1.00 | 0.45 | 1.36 | 1.00 | 1.00 | 1.00 |
| Sybu | 0.95 | 1.07 | 1.21 | 0.92 | 0.20 | 0.82 | 0.88 | 0.19 | 0.76 | 1.00 | 1.00 | 1.00 |
| Synpo2 | 1.00 | 1.00 | 1.00 | 0.95 | 1.00 | 0.94 | 1.04 | 0.52 | 1.78 | 1.00 | 1.00 | 1.00 |
| Syt11 | 1.00 | 1.00 | 1.00 | 0.99 | 1.06 | 0.97 | 1.20 | 0.74 | 1.21 | 1.00 | 1.27 | 0.99 |
| Tacc1 | 1.24 | 1.54 | 1.44 | 0.96 | 1.38 | 1.00 | 1.17 | 0.09 | 1.41 | 0.45 | 0.99 | 1.01 |
| Tada2b | 0.96 | 0.80 | 0.76 | 1.04 | 0.50 | 0.95 | 0.98 | 0.11 | 1.32 | 0.31 | 0.82 | 0.84 |
| Taf1 | 1.00 | 1.00 | 1.00 | 0.90 | 1.00 | 0.95 | 0.95 | 0.13 | 1.21 | 0.25 | 0.85 | 1.01 |
| Taf1d | 1.04 | 0.81 | 1.05 | 0.90 | 0.16 | 0.91 | 1.08 | 0.96 | 0.86 | 0.97 | 1.11 | 0.89 |
| Taf2 | 1.00 | 1.00 | 1.00 | 0.99 | 1.00 | 0.93 | 0.75 | 0.16 | 0.80 | 0.24 | 0.76 | 0.79 |
| Taf4a | 1.20 | 0.96 | 0.72 | 0.95 | 1.00 | 0.93 | 0.89 | 0.12 | 0.99 | 0.33 | 1.18 | 1.07 |
| Taf5l | 1.05 | 1.35 | 1.62 | 1.05 | 1.00 | 1.00 | 0.92 | 0.16 | 0.96 | 0.52 | 0.96 | 0.90 |
| Taf7 | 1.00 | 1.00 | 1.00 | 1.13 | 1.00 | 1.08 | 0.86 | 0.15 | 1.01 | 0.52 | 0.97 | 0.95 |
| Tamm41 | 1.00 | 1.00 | 1.00 | 1.38 | 0.06 | 0.60 | 1.19 | 1.64 | 0.78 | 1.07 | 1.09 | 0.68 |
| Tank | 1.31 | 1.24 | 1.23 | 0.88 | 1.37 | 1.01 | 0.85 | 0.17 | 1.09 | 0.45 | 1.02 | 1.01 |
| Taok1 | 1.03 | 1.06 | 1.00 | 0.88 | 1.00 | 0.99 | 0.74 | 0.35 | 0.91 | 0.53 | 1.09 | 1.11 |
| Tarbp2 | 1.16 | 0.80 | 0.86 | 1.05 | 1.00 | 0.78 | 1.59 | 4.14 | 0.75 | 1.90 | 1.09 | 1.04 |
| Tbc1d20 | 1.09 | 1.02 | 0.93 | 1.02 | 1.65 | 0.95 | 1.01 | 0.08 | 1.28 | 0.42 | 1.21 | 0.87 |
| Tbc1d21 | 1.00 | 1.00 | 1.00 | 1.00 | 1.00 | 1.00 | 1.00 | 1.00 | 1.00 | 1.00 | 1.00 | 1.00 |
| Tbc1d23 | 1.44 | 0.96 | 1.18 | 0.85 | 1.01 | 0.89 | 0.76 | 0.13 | 1.00 | 0.66 | 1.73 | 1.50 |
| Tbc1d25 | 1.15 | 0.92 | 1.59 | 0.94 | 0.44 | 0.97 | 1.08 | 0.16 | 1.04 | 0.49 | 1.00 | 1.03 |
| Tbc1d7 | 1.00 | 1.00 | 1.00 | 0.86 | 1.25 | 0.99 | 0.87 | 0.34 | 0.94 | 0.94 | 0.57 | 0.56 |
| Tbccd1 | 0.70 | 0.78 | 0.80 | 0.95 | 0.71 | 1.02 | 0.91 | 0.19 | 1.05 | 0.62 | 0.77 | 0.69 |
| Tbcel | 1.18 | 1.14 | 1.23 | 0.97 | 1.00 | 0.92 | 1.06 | 0.17 | 1.32 | 0.37 | 0.78 | 0.67 |
| Tbx21 | 1.00 | 1.00 | 1.00 | 1.00 | 0.19 | 1.00 | 1.00 | 1.00 | 1.00 | 1.02 | 1.29 | 1.80 |
| Tcea3 | 0.39 | 0.52 | 0.52 | 1.00 | 1.00 | 1.00 | 1.27 | 1.67 | 1.12 | 1.00 | 1.00 | 1.00 |
| Tceal3 | 1.00 | 1.00 | 1.00 | 1.23 | 0.84 | 1.00 | 0.92 | 1.24 | 0.93 | 0.56 | 0.41 | 0.73 |
| Tcf12 | 0.81 | 1.03 | 0.62 | 1.00 | 1.00 | 0.99 | 0.77 | 0.15 | 1.03 | 0.37 | 0.79 | 0.91 |
| Tcf21 | 1.00 | 1.00 | 1.00 | 1.00 | 1.00 | 1.00 | 1.00 | 1.00 | 1.00 | 1.00 | 1.00 | 1.00 |
| Tcf24 | 1.00 | 1.00 | 1.00 | 1.00 | 1.00 | 1.00 | 1.01 | 1.00 | 1.35 | 1.00 | 1.00 | 1.00 |
| Tcf7 | 1.51 | 1.85 | 1.16 | 1.04 | 1.00 | 1.06 | 0.70 | 0.11 | 0.83 | 0.26 | 1.28 | 1.19 |
| Tead3 | 1.29 | 1.03 | 1.26 | 1.26 | 1.00 | 0.76 | 0.89 | 0.17 | 0.85 | 1.00 | 1.00 | 1.00 |
| Tecpr1 | 0.73 | 0.85 | 0.97 | 1.03 | 0.64 | 0.93 | 1.31 | 0.27 | 1.21 | 1.00 | 0.99 | 0.85 |
| Teddm1 | 1.00 | 1.00 | 1.00 | 1.00 | 1.00 | 1.00 | 1.00 | 1.00 | 1.00 | 1.00 | 1.00 | 1.00 |
| Tefm | 1.19 | 1.31 | 0.61 | 0.95 | 1.00 | 0.98 | 0.90 | 0.18 | 0.85 | 0.30 | 1.19 | 0.87 |
| Tenm4 | 1.00 | 1.00 | 1.00 | 0.85 | 1.00 | 0.90 | 0.68 | 0.88 | 0.98 | 1.00 | 1.00 | 1.00 |
| Tet2 | 1.00 | 1.00 | 1.00 | 0.93 | 1.00 | 0.99 | 1.09 | 0.17 | 1.43 | 0.61 | 1.17 | 1.02 |
| Tet3 | 0.91 | 1.00 | 1.09 | 0.76 | 1.00 | 0.87 | 0.60 | 0.09 | 0.87 | 0.32 | 0.69 | 0.75 |
| Tex10 | 1.00 | 1.08 | 1.00 | 0.78 | 1.00 | 0.91 | 0.80 | 0.23 | 1.10 | 0.62 | 0.88 | 0.87 |
| Tfap4 | 0.77 | 0.58 | 0.82 | 0.88 | 1.00 | 1.12 | 0.95 | 0.13 | 0.96 | 0.29 | 0.94 | 0.83 |
| Tfb2m | 1.07 | 0.98 | 0.89 | 1.05 | 1.00 | 0.99 | 0.99 | 0.09 | 1.08 | 0.65 | 0.90 | 1.11 |
| Tgfa | 0.90 | 0.57 | 0.78 | 0.95 | 1.00 | 0.90 | 0.93 | 0.11 | 0.87 | 1.00 | 1.00 | 1.00 |
| Tgfb2 | 1.00 | 1.00 | 1.00 | 0.79 | 1.00 | 0.83 | 0.77 | 0.14 | 1.08 | 1.00 | 1.00 | 1.00 |
| Tgif2lx2 | 1.00 | 1.00 | 1.00 | 1.00 | 1.00 | 1.00 | 1.00 | 1.00 | 1.00 | 1.00 | 1.00 | 1.00 |
| Tgm4 | 1.00 | 1.00 | 1.00 | 1.00 | 1.46 | 1.00 | 1.17 | 3.85 | 1.09 | 1.46 | 1.08 | 1.22 |
| Tgm7 | 1.00 | 1.00 | 1.00 | 1.00 | 1.00 | 1.00 | 0.70 | 0.16 | 1.25 | 1.00 | 1.00 | 1.00 |
| Tgs1 | 1.00 | 1.00 | 1.00 | 0.96 | 1.09 | 1.13 | 0.82 | 0.16 | 1.00 | 0.49 | 0.95 | 1.19 |
| Thbd | 0.75 | 0.92 | 1.26 | 0.87 | 1.00 | 1.06 | 1.04 | 0.19 | 1.22 | 0.44 | 0.65 | 0.75 |
| Them6 | 0.72 | 0.68 | 0.69 | 1.20 | 1.03 | 1.12 | 0.77 | 0.12 | 0.73 | 0.49 | 0.72 | 0.88 |
| Themis2 | 1.00 | 1.00 | 1.00 | 1.00 | 1.00 | 1.00 | 0.86 | 0.67 | 0.82 | 0.13 | 1.17 | 0.98 |
| Thnsl2 | 0.77 | 0.95 | 0.49 | 0.57 | 1.00 | 0.56 | 0.65 | 0.54 | 0.61 | 1.00 | 1.00 | 1.00 |
| Thoc2 | 1.07 | 0.99 | 1.00 | 0.93 | 0.77 | 0.96 | 0.85 | 0.17 | 1.15 | 0.37 | 0.93 | 0.96 |
| Thra | 1.11 | 0.85 | 1.12 | 1.06 | 0.31 | 0.99 | 0.85 | 0.05 | 1.14 | 0.74 | 0.69 | 0.68 |
| Thy1 | 1.00 | 1.14 | 1.23 | 1.12 | 1.08 | 1.08 | 0.88 | 1.46 | 1.00 | 1.46 | 1.29 | 1.20 |
| Tifa | 1.04 | 1.86 | 1.06 | 1.27 | 1.00 | 0.82 | 0.99 | 0.14 | 1.19 | 0.33 | 0.79 | 0.94 |
| Timm21 | 0.81 | 0.68 | 0.85 | 0.94 | 0.35 | 0.90 | 0.81 | 0.10 | 1.03 | 0.62 | 1.06 | 0.84 |
| Timp3 | 0.74 | 0.78 | 1.03 | 0.81 | 0.70 | 0.85 | 0.64 | 0.06 | 0.70 | 1.00 | 0.74 | 1.80 |
| Tiparp | 1.00 | 1.00 | 1.00 | 1.27 | 1.00 | 1.24 | 0.95 | 0.20 | 1.26 | 1.01 | 1.53 | 1.34 |
| Tjp1 | 1.22 | 1.04 | 1.04 | 0.83 | 0.46 | 0.87 | 0.71 | 0.25 | 1.03 | 1.00 | 1.00 | 1.00 |
| Tk1 | 1.00 | 1.00 | 1.00 | 1.00 | 1.00 | 1.00 | 0.48 | 1.10 | 0.48 | 0.82 | 0.85 | 0.86 |
| Tldc1 | 0.89 | 0.65 | 0.93 | 0.80 | 1.00 | 0.85 | 0.76 | 0.19 | 0.79 | 0.75 | 1.21 | 0.98 |

Fig. 35- 97

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Tm4sf19 | 1.00 | 1.00 | 1.00 | 1.00 | 1.00 | 1.00 | 1.00 | 1.00 | 1.00 | 1.00 | 1.00 | 1.00 |
| Tm6sf1 | 1.16 | 1.66 | 1.11 | 1.40 | 0.75 | 1.01 | 0.81 | 1.03 | 1.36 | 0.19 | 0.20 | 0.75 |
| Tmeff1 | 1.00 | 1.00 | 1.00 | 1.00 | 0.14 | 0.72 | 0.67 | 0.76 | 0.72 | 0.18 | 0.18 | 0.80 |
| Tmem123 | 1.03 | 1.49 | 1.05 | 3.17 | 0.80 | 1.25 | 1.03 | 1.16 | 0.97 | 0.46 | 0.49 | 0.92 |
| Tmem161b | 0.79 | 2.08 | 0.98 | 1.26 | 0.28 | 0.97 | 0.63 | 0.73 | 0.87 | 0.44 | 0.21 | 1.09 |
| Tmem170b | 1.06 | 1.82 | 1.11 | 2.00 | 0.38 | 1.25 | 1.11 | 1.19 | 0.94 | 0.54 | 0.57 | 1.14 |
| Tmem171 | 1.00 | 1.00 | 1.00 | 0.24 | 0.10 | 0.42 | 0.67 | 0.43 | 0.88 | 1.00 | 1.00 | 1.70 |
| Tmem181b-ps | 0.50 | 0.55 | 0.72 | 1.11 | 0.24 | 0.60 | 0.77 | 0.79 | 0.69 | 0.94 | 0.48 | 0.67 |
| Tmem184c | 0.85 | 1.32 | 0.61 | 1.70 | 0.16 | 0.78 | 1.08 | 1.11 | 1.14 | 0.47 | 0.23 | 0.93 |
| Tmem185b | 1.53 | 1.54 | 1.43 | 0.92 | 0.24 | 0.84 | 1.02 | 1.06 | 1.09 | 0.50 | 0.23 | 0.90 |
| Tmem189 | 1.87 | 2.98 | 1.85 | 0.76 | 0.50 | 0.99 | 1.29 | 1.08 | 1.02 | 0.65 | 0.60 | 1.23 |
| Tmem2 | 0.75 | 1.00 | 0.78 | 2.02 | 0.55 | 1.14 | 1.29 | 1.11 | 1.29 | 0.31 | 0.17 | 0.74 |
| Tmem200b | 0.99 | 1.19 | 1.46 | 1.11 | 0.16 | 0.87 | 1.37 | 1.19 | 1.46 | 1.00 | 0.08 | 0.89 |
| Tmem212 | 1.00 | 1.00 | 1.00 | 1.00 | 1.00 | 1.00 | 1.00 | 1.00 | 1.00 | 0.87 | 1.98 | 1.15 |
| Tmem233 | 0.18 | 0.99 | 0.18 | 1.00 | 1.00 | 1.00 | 1.00 | 1.00 | 1.00 | 1.00 | 1.00 | 1.00 |
| Tmem234 | 1.00 | 3.77 | 1.22 | 0.55 | 0.25 | 0.97 | 1.21 | 0.98 | 1.02 | 0.11 | 0.15 | 1.09 |
| Tmem245 | 1.00 | 1.00 | 1.00 | 1.89 | 0.74 | 1.27 | 0.96 | 1.05 | 1.05 | 1.00 | 1.00 | 1.00 |
| Tmem38b | 1.45 | 2.73 | 1.37 | 1.18 | 0.27 | 0.88 | 1.52 | 1.53 | 1.45 | 0.30 | 0.30 | 1.13 |
| Tmem43 | 2.02 | 2.59 | 1.66 | 1.09 | 0.63 | 1.03 | 1.06 | 1.15 | 1.20 | 0.74 | 0.81 | 1.25 |
| Tmtc3 | 0.78 | 1.00 | 1.13 | 2.46 | 0.45 | 0.84 | 0.89 | 1.34 | 1.20 | 1.00 | 0.47 | 1.10 |
| Tnfrsf11b | 1.00 | 1.00 | 1.00 | 1.00 | 1.00 | 1.00 | 1.00 | 1.00 | 1.00 | 1.00 | 1.00 | 1.00 |
| Tnfrsf14 | 1.00 | 1.00 | 1.00 | 1.00 | 1.00 | 1.00 | 1.00 | 1.00 | 1.77 | 1.00 | 1.00 | 1.01 |
| Tnfrsf19 | 2.47 | 2.59 | 2.42 | 1.00 | 1.00 | 1.00 | 1.36 | 1.39 | 0.83 | 0.35 | 0.36 | 0.82 |
| Tnfsf10 | 0.37 | 0.45 | 0.37 | 4.13 | 0.37 | 0.87 | 0.79 | 0.93 | 0.95 | 0.51 | 0.20 | 0.53 |
| Tnk1 | 1.00 | 1.00 | 1.00 | 1.00 | 1.00 | 1.00 | 1.00 | 1.00 | 1.00 | 1.00 | 0.42 | 0.95 |
| Tnks1bp1 | 1.58 | 1.99 | 2.06 | 1.19 | 0.58 | 0.99 | 0.92 | 1.38 | 1.26 | 0.84 | 0.55 | 1.07 |
| Tnni3k | 1.00 | 1.00 | 1.00 | 1.00 | 1.00 | 1.00 | 0.13 | 0.11 | 0.10 | 1.00 | 1.00 | 1.00 |
| Tns1 | 0.93 | 1.67 | 1.21 | 1.10 | 0.27 | 1.00 | 1.48 | 1.74 | 1.44 | 1.09 | 0.76 | 1.26 |
| Tns3 | 1.83 | 3.62 | 1.62 | 1.42 | 0.43 | 1.03 | 0.90 | 0.95 | 1.25 | 0.22 | 0.14 | 0.84 |
| Tom1l1 | 1.10 | 1.36 | 0.79 | 1.37 | 0.45 | 1.50 | 1.06 | 0.89 | 0.74 | 0.24 | 0.44 | 1.08 |
| Top1 | 1.14 | 2.52 | 1.10 | 2.35 | 0.35 | 0.94 | 1.14 | 1.41 | 0.89 | 0.46 | 0.29 | 1.02 |
| Topbp1 | 0.93 | 1.00 | 0.94 | 1.93 | 0.60 | 0.97 | 1.24 | 1.47 | 1.15 | 0.50 | 0.28 | 0.99 |
| Tpm4 | 1.35 | 2.03 | 1.10 | 1.44 | 0.24 | 1.07 | 0.86 | 0.95 | 0.95 | 0.22 | 0.29 | 1.05 |
| Trappc10 | 0.90 | 1.58 | 1.03 | 0.80 | 0.30 | 0.86 | 1.11 | 1.29 | 1.09 | 0.52 | 0.63 | 1.02 |
| Trappc2 | 0.68 | 2.47 | 0.73 | 0.91 | 0.16 | 0.84 | 0.71 | 1.30 | 0.85 | 0.56 | 0.12 | 0.96 |
| Trappc6b | 1.04 | 1.32 | 0.81 | 0.83 | 0.78 | 1.15 | 1.04 | 0.94 | 1.01 | 0.26 | 0.46 | 1.10 |
| Trappc8 | 1.00 | 2.72 | 1.03 | 1.94 | 0.15 | 1.01 | 1.23 | 1.32 | 1.05 | 0.54 | 0.22 | 1.04 |
| Trim10 | 1.00 | 1.00 | 1.00 | 1.00 | 1.00 | 1.00 | 1.00 | 1.00 | 1.00 | 1.00 | 1.00 | 1.00 |
| Trim13 | 0.55 | 0.95 | 0.82 | 2.66 | 0.24 | 1.37 | 0.70 | 0.82 | 0.92 | 0.40 | 0.47 | 1.23 |
| Trim56 | 0.80 | 1.00 | 1.00 | 1.04 | 1.00 | 0.62 | 1.36 | 2.16 | 3.38 | 1.00 | 1.00 | 1.39 |
| Trim59 | 1.00 | 1.00 | 1.00 | 1.00 | 1.00 | 1.00 | 1.00 | 1.00 | 1.00 | 1.00 | 0.57 | 0.84 |
| Trim8 | 0.92 | 1.14 | 1.16 | 0.93 | 0.29 | 0.98 | 1.35 | 1.24 | 1.13 | 0.51 | 0.40 | 1.07 |
| Trmt10c | 1.00 | 1.93 | 1.13 | 0.88 | 0.21 | 0.69 | 0.82 | 1.16 | 0.95 | 0.24 | 0.44 | 1.08 |
| Trmt61b | 0.65 | 1.00 | 0.89 | 0.50 | 0.86 | 0.50 | 0.48 | 0.35 | 0.72 | 0.18 | 0.45 | 0.72 |
| Trp53 | 1.13 | 1.12 | 0.86 | 0.99 | 0.76 | 0.87 | 0.80 | 0.73 | 0.86 | 0.40 | 0.46 | 0.81 |
| Trp53bp2 | 1.50 | 2.37 | 1.81 | 0.95 | 0.30 | 1.15 | 1.06 | 1.07 | 1.24 | 0.14 | 0.22 | 1.08 |
| Trp63 | 1.15 | 1.33 | 1.80 | 1.00 | 1.14 | 1.00 | 1.52 | 1.10 | 1.25 | 1.00 | 1.00 | 1.00 |
| Trpm7 | 1.06 | 2.11 | 0.82 | 2.19 | 0.29 | 1.00 | 0.83 | 1.09 | 0.97 | 0.25 | 0.26 | 0.98 |
| Tsen2 | 0.28 | 0.22 | 0.31 | 0.16 | 1.00 | 0.19 | 0.59 | 0.43 | 0.62 | 1.47 | 1.67 | 0.45 |
| Tshb | 1.00 | 1.00 | 1.00 | 1.00 | 1.00 | 1.00 | 1.00 | 1.00 | 1.00 | 0.12 | 0.51 | 0.27 |
| Tshr | 1.00 | 1.00 | 1.00 | 0.75 | 0.23 | 1.26 | 1.00 | 1.00 | 1.00 | 1.00 | 1.00 | 1.00 |
| Tshz1 | 1.00 | 1.28 | 1.51 | 1.49 | 0.21 | 0.90 | 1.07 | 1.24 | 1.35 | 0.92 | 0.67 | 1.12 |
| Tshz2 | 0.76 | 1.00 | 1.10 | 1.48 | 0.09 | 0.79 | 1.34 | 1.70 | 1.42 | 1.00 | 0.57 | 1.11 |
| Tspan18 | 0.75 | 1.00 | 1.33 | 0.70 | 0.17 | 0.85 | 1.06 | 1.00 | 0.72 | 0.68 | 0.62 | 1.26 |
| Tspan4 | 0.95 | 0.40 | 0.65 | 0.74 | 3.56 | 0.86 | 0.77 | 0.63 | 1.01 | 0.82 | 1.10 | 0.70 |
| Tspo2 | 1.00 | 1.00 | 1.00 | 1.00 | 1.00 | 1.00 | 1.00 | 1.00 | 1.00 | 1.48 | 1.00 | 1.00 |
| Tspyl4 | 0.86 | 1.00 | 1.10 | 1.86 | 0.06 | 0.95 | 1.24 | 1.16 | 1.06 | 0.51 | 0.53 | 1.00 |
| Tstd2 | 0.54 | 0.71 | 0.72 | 0.99 | 0.14 | 0.89 | 0.91 | 1.01 | 1.22 | 1.00 | 0.51 | 0.95 |
| Ttc30b | 0.49 | 1.09 | 0.94 | 0.72 | 0.15 | 0.74 | 0.52 | 0.41 | 0.85 | 0.26 | 0.38 | 0.98 |
| Tusc3 | 0.76 | 1.00 | 0.89 | 0.85 | 0.11 | 1.03 | 1.12 | 1.34 | 1.33 | 0.89 | 0.09 | 0.95 |
| Twf1 | 1.33 | 1.45 | 1.22 | 0.73 | 0.45 | 0.91 | 1.18 | 1.06 | 1.04 | 0.36 | 0.67 | 1.04 |
| Twist1 | 0.99 | 2.41 | 0.93 | 0.86 | 0.54 | 0.81 | 1.00 | 1.20 | 1.28 | 1.00 | 1.00 | 1.00 |
| Txnip | 1.56 | 2.05 | 1.17 | 2.35 | 1.06 | 1.68 | 0.67 | 0.55 | 0.89 | 0.31 | 0.50 | 0.96 |
| Tyrobp | 1.81 | 0.82 | 1.90 | 0.63 | 3.93 | 1.25 | 0.94 | 0.72 | 1.19 | 1.12 | 1.72 | 0.82 |

Fig. 35- 98

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Tm4sf19 | 1.00 | 1.00 | 1.00 | 1.00 | 1.00 | 1.00 | 1.00 | 1.00 | 1.00 | 1.00 | 1.00 | 1.00 |
| Tm6sf1 | 0.84 | 0.95 | 1.12 | 1.21 | 1.00 | 1.11 | 1.41 | 1.00 | 1.03 | 1.16 | 0.96 | 1.66 |
| Tmeff1 | 0.97 | 1.21 | 0.82 | 1.00 | 1.00 | 1.00 | 1.00 | 1.00 | 1.00 | 1.30 | 0.95 | 1.22 |
| Tmem123 | 0.82 | 0.75 | 1.09 | 1.21 | 1.49 | 1.02 | 0.83 | 0.51 | 0.68 | 0.98 | 0.74 | 0.94 |
| Tmem161b | 1.06 | 1.11 | 0.92 | 1.01 | 2.17 | 0.93 | 1.05 | 0.97 | 1.04 | 1.08 | 0.91 | 0.98 |
| Tmem170b | 0.71 | 0.57 | 1.02 | 1.27 | 1.00 | 1.12 | 0.98 | 1.00 | 0.83 | 1.15 | 0.72 | 1.05 |
| Tmem171 | 1.00 | 1.00 | 1.00 | 1.32 | 1.19 | 1.19 | 1.00 | 1.00 | 1.00 | 0.98 | 1.06 | 0.94 |
| Tmem181b-ps | 0.53 | 0.50 | 0.71 | 0.74 | 1.00 | 0.99 | 0.99 | 1.00 | 1.00 | 0.71 | 0.48 | 0.79 |
| Tmem184c | 0.78 | 0.72 | 0.96 | 1.04 | 1.08 | 1.09 | 2.44 | 1.00 | 1.90 | 1.14 | 0.87 | 0.98 |
| Tmem185b | 0.77 | 0.68 | 0.82 | 0.84 | 1.26 | 0.91 | 1.24 | 1.00 | 0.95 | 0.87 | 0.69 | 1.08 |
| Tmem189 | 0.94 | 1.05 | 0.99 | 1.27 | 1.91 | 1.22 | 1.44 | 0.73 | 1.61 | 1.15 | 1.08 | 1.19 |
| Tmem2 | 2.16 | 1.34 | 1.81 | 0.97 | 1.00 | 1.00 | 0.93 | 1.00 | 1.08 | 1.08 | 0.74 | 0.92 |
| Tmem200b | 1.12 | 1.24 | 1.25 | 1.05 | 1.00 | 1.17 | 0.71 | 1.00 | 1.37 | 0.83 | 0.45 | 0.83 |
| Tmem212 | 1.00 | 1.22 | 1.00 | 1.00 | 1.00 | 1.00 | 1.00 | 1.00 | 1.00 | 1.00 | 1.00 | 1.00 |
| Tmem233 | 1.00 | 1.00 | 1.00 | 1.00 | 1.00 | 1.00 | 1.00 | 1.00 | 1.00 | 1.00 | 1.00 | 1.00 |
| Tmem234 | 0.86 | 1.03 | 0.89 | 0.89 | 3.36 | 1.19 | 0.98 | 1.01 | 0.86 | 1.07 | 0.89 | 1.12 |
| Tmem245 | 0.82 | 0.58 | 0.93 | 1.93 | 1.00 | 1.18 | 1.00 | 1.00 | 1.00 | 1.00 | 1.00 | 1.00 |
| Tmem38b | 1.38 | 1.22 | 1.08 | 0.99 | 3.39 | 1.06 | 0.79 | 0.38 | 0.91 | 1.00 | 0.97 | 1.16 |
| Tmem43 | 0.89 | 0.95 | 0.92 | 1.16 | 1.32 | 1.02 | 1.43 | 0.62 | 1.30 | 1.02 | 1.07 | 1.02 |
| Tmtc3 | 0.74 | 0.54 | 0.87 | 1.00 | 1.00 | 1.08 | 0.74 | 1.00 | 0.81 | 1.04 | 0.67 | 0.84 |
| Tnfrsf11b | 0.54 | 0.54 | 0.91 | 1.00 | 1.00 | 1.00 | 0.84 | 1.00 | 1.11 | 0.56 | 0.68 | 1.03 |
| Tnfrsf14 | 0.58 | 0.39 | 1.13 | 1.00 | 1.00 | 1.00 | 1.00 | 1.00 | 1.34 | 0.97 | 0.68 | 0.93 |
| Tnfrsf19 | 1.63 | 1.63 | 1.97 | 1.00 | 1.00 | 1.00 | 0.65 | 1.00 | 0.55 | 0.81 | 0.87 | 0.99 |
| Tnfsf10 | 0.85 | 0.60 | 1.00 | 0.81 | 0.85 | 0.94 | 0.36 | 0.54 | 0.60 | 0.90 | 0.38 | 0.75 |
| Tnk1 | 2.41 | 1.22 | 1.99 | 0.97 | 1.00 | 1.53 | 1.00 | 1.00 | 1.00 | 0.89 | 0.84 | 1.15 |
| Tnks1bp1 | 1.19 | 0.94 | 1.33 | 1.23 | 1.18 | 1.08 | 0.72 | 0.64 | 1.04 | 0.94 | 0.72 | 0.95 |
| Tnni3k | 1.00 | 1.00 | 1.00 | 1.00 | 1.00 | 1.00 | 1.00 | 1.00 | 1.00 | 1.00 | 1.00 | 1.00 |
| Tns1 | 0.97 | 0.79 | 1.06 | 1.13 | 1.42 | 1.07 | 1.25 | 1.69 | 1.46 | 1.05 | 0.70 | 1.04 |
| Tns3 | 1.20 | 0.89 | 1.43 | 1.09 | 1.69 | 1.02 | 0.53 | 1.00 | 0.76 | 0.84 | 0.51 | 0.83 |
| Tom1l1 | 1.34 | 1.59 | 1.81 | 1.24 | 1.23 | 1.00 | 1.28 | 1.00 | 0.86 | 0.90 | 1.16 | 1.03 |
| Top1 | 0.69 | 0.65 | 0.81 | 0.91 | 1.22 | 0.76 | 0.87 | 0.64 | 0.90 | 0.90 | 0.74 | 1.00 |
| Topbp1 | 0.58 | 0.58 | 0.66 | 0.81 | 1.00 | 0.68 | 0.93 | 1.00 | 0.67 | 0.99 | 0.80 | 0.98 |
| Tpm4 | 0.92 | 0.84 | 1.10 | 1.05 | 1.57 | 0.98 | 2.06 | 1.53 | 1.39 | 0.98 | 0.83 | 0.98 |
| Trappc10 | 0.87 | 0.78 | 0.99 | 1.13 | 1.60 | 1.07 | 0.88 | 0.85 | 0.89 | 1.03 | 0.94 | 1.12 |
| Trappc2 | 0.73 | 0.62 | 0.82 | 0.74 | 1.00 | 0.64 | 2.37 | 0.84 | 1.29 | 0.79 | 0.55 | 0.97 |
| Trappc6b | 0.96 | 0.99 | 0.89 | 1.01 | 1.69 | 1.17 | 1.05 | 0.20 | 1.04 | 1.09 | 1.13 | 1.06 |
| Trappc8 | 0.77 | 0.74 | 1.01 | 1.24 | 1.04 | 1.01 | 1.28 | 1.00 | 1.18 | 0.99 | 0.78 | 0.98 |
| Trim10 | 1.00 | 1.00 | 1.00 | 1.00 | 1.00 | 1.00 | 1.00 | 1.00 | 1.00 | 1.00 | 1.00 | 1.00 |
| Trim13 | 0.87 | 0.80 | 1.06 | 0.86 | 0.67 | 0.90 | 1.31 | 1.00 | 0.96 | 0.94 | 0.89 | 0.77 |
| Trim56 | 0.18 | 0.12 | 0.53 | 1.28 | 1.00 | 1.75 | 0.87 | 1.00 | 1.53 | 1.26 | 1.00 | 0.90 |
| Trim59 | 0.60 | 0.55 | 0.68 | 1.00 | 1.00 | 1.00 | 1.00 | 1.00 | 1.00 | 1.17 | 0.69 | 0.93 |
| Trim8 | 0.79 | 0.86 | 1.14 | 1.02 | 1.33 | 1.11 | 1.09 | 0.80 | 1.14 | 0.95 | 0.78 | 1.05 |
| Trmt10c | 0.80 | 0.80 | 0.90 | 0.95 | 2.73 | 0.84 | 0.90 | 0.44 | 0.84 | 0.99 | 0.83 | 1.06 |
| Trmt61b | 0.77 | 0.83 | 0.62 | 0.54 | 0.63 | 0.44 | 0.41 | 0.30 | 0.68 | 0.42 | 0.64 | 0.38 |
| Trp53 | 0.87 | 1.02 | 0.97 | 0.82 | 2.31 | 0.90 | 0.86 | 0.33 | 0.98 | 1.04 | 1.07 | 1.06 |
| Trp53bp2 | 0.91 | 0.84 | 1.04 | 0.99 | 4.60 | 1.05 | 1.13 | 1.00 | 1.39 | 1.07 | 0.82 | 0.95 |
| Trp63 | 2.21 | 1.61 | 1.75 | 1.00 | 1.00 | 1.00 | 1.00 | 1.00 | 1.00 | 1.00 | 1.00 | 1.00 |
| Trpm7 | 0.88 | 0.83 | 0.93 | 1.18 | 1.90 | 0.98 | 0.77 | 1.00 | 0.81 | 1.07 | 0.72 | 1.00 |
| Tsen2 | 0.64 | 0.55 | 0.51 | 0.73 | 0.59 | 0.57 | 0.64 | 1.38 | 0.63 | 0.43 | 0.63 | 0.37 |
| Tshb | 1.00 | 1.00 | 1.00 | 1.00 | 1.00 | 1.00 | 1.00 | 1.00 | 1.00 | 1.00 | 1.00 | 1.00 |
| Tshr | 1.00 | 1.00 | 1.00 | 1.60 | 1.00 | 1.06 | 1.00 | 1.00 | 1.00 | 1.00 | 1.00 | 1.00 |
| Tshz1 | 0.62 | 0.51 | 1.00 | 1.10 | 1.31 | 1.02 | 0.96 | 1.00 | 1.03 | 1.01 | 0.52 | 0.95 |
| Tshz2 | 1.02 | 0.63 | 0.91 | 1.19 | 1.00 | 1.14 | 0.73 | 1.00 | 0.92 | 0.87 | 0.50 | 0.90 |
| Tspan18 | 0.47 | 0.39 | 0.53 | 0.44 | 0.88 | 0.56 | 0.95 | 1.00 | 0.90 | 0.98 | 0.73 | 0.83 |
| Tspan4 | 1.86 | 1.92 | 1.27 | 0.68 | 0.64 | 0.76 | 0.59 | 0.48 | 0.68 | 0.51 | 0.93 | 0.73 |
| Tspo2 | 1.00 | 1.00 | 1.00 | 1.00 | 1.00 | 1.00 | 1.00 | 1.00 | 1.00 | 1.00 | 1.00 | 1.00 |
| Tspyl4 | 0.74 | 0.71 | 0.79 | 0.85 | 1.02 | 0.81 | 1.00 | 1.00 | 1.00 | 1.09 | 0.74 | 0.98 |
| Tstd2 | 0.79 | 0.64 | 0.93 | 1.00 | 1.00 | 0.60 | 1.07 | 1.00 | 1.03 | 0.93 | 0.52 | 0.86 |
| Ttc30b | 1.26 | 1.00 | 1.18 | 0.96 | 1.37 | 0.90 | 1.14 | 1.00 | 0.86 | 1.06 | 0.89 | 1.10 |
| Tusc3 | 0.93 | 0.63 | 1.00 | 1.10 | 1.00 | 1.29 | 1.25 | 1.00 | 1.07 | 1.02 | 0.83 | 1.08 |
| Twf1 | 1.17 | 1.01 | 1.08 | 1.00 | 1.69 | 1.06 | 1.03 | 0.62 | 1.18 | 1.16 | 0.99 | 1.18 |
| Twist1 | 1.23 | 1.58 | 0.65 | 1.12 | 1.00 | 1.21 | 1.00 | 1.00 | 1.00 | 0.62 | 1.13 | 0.81 |
| Txnip | 1.88 | 1.99 | 1.46 | 1.07 | 2.25 | 1.15 | 1.79 | 1.06 | 1.29 | 0.88 | 0.79 | 0.91 |
| Tyrobp | 1.85 | 2.23 | 1.64 | 0.73 | 0.68 | 0.84 | 0.85 | 0.32 | 0.86 | 1.14 | 1.26 | 0.82 |

Fig. 35- 99

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Tm4sf19 | 1.00 | 1.00 | 1.00 | 1.00 | 1.00 | 0.17 | 1.00 | 1.00 | 1.00 | 1.00 | 1.00 | 1.00 |
| Tm6sf1 | 0.56 | 1.41 | 1.43 | 0.79 | 0.59 | 0.52 | 1.17 | 1.00 | 1.00 | 1.17 | 0.86 | 0.87 |
| Tmeff1 | 1.17 | 0.99 | 0.95 | 0.41 | 1.00 | 0.58 | 0.97 | 0.45 | 0.96 | 1.00 | 3.22 | 1.42 |
| Tmem123 | 1.00 | 0.92 | 1.06 | 1.08 | 0.39 | 1.03 | 0.90 | 0.28 | 0.80 | 1.04 | 0.76 | 1.01 |
| Tmem161b | 1.10 | 1.16 | 1.11 | 1.00 | 1.00 | 1.23 | 1.09 | 2.27 | 1.03 | 1.31 | 0.89 | 1.01 |
| Tmem170b | 1.16 | 0.99 | 1.13 | 0.92 | 0.42 | 1.11 | 1.14 | 1.00 | 1.06 | 1.26 | 0.97 | 1.29 |
| Tmem171 | 0.77 | 0.95 | 0.63 | 1.00 | 1.00 | 1.00 | 1.00 | 1.00 | 1.00 | 1.00 | 1.00 | 1.00 |
| Tmem181b-ps | 0.69 | 0.58 | 0.63 | 0.72 | 0.34 | 0.67 | 1.06 | 1.16 | 0.98 | 0.61 | 0.45 | 0.63 |
| Tmem184c | 0.98 | 0.77 | 1.06 | 0.79 | 0.83 | 0.85 | 1.10 | 0.29 | 0.92 | 1.16 | 0.86 | 1.08 |
| Tmem185b | 0.85 | 0.75 | 1.18 | 1.07 | 0.87 | 1.09 | 0.85 | 0.74 | 1.12 | 1.20 | 0.77 | 1.13 |
| Tmem189 | 0.71 | 0.77 | 0.66 | 2.16 | 1.13 | 1.29 | 0.89 | 3.77 | 1.01 | 1.12 | 1.04 | 1.07 |
| Tmem2 | 1.02 | 0.96 | 0.69 | 1.23 | 1.00 | 0.92 | 1.00 | 1.00 | 1.00 | 1.09 | 0.69 | 0.97 |
| Tmem200b | 1.00 | 1.04 | 0.97 | 1.34 | 0.46 | 1.35 | 0.96 | 1.00 | 1.21 | 0.79 | 0.71 | 0.81 |
| Tmem212 | 1.00 | 1.00 | 1.00 | 1.12 | 2.43 | 2.89 | 1.00 | 1.00 | 1.00 | 1.00 | 1.00 | 1.00 |
| Tmem233 | 1.00 | 1.00 | 1.00 | 1.00 | 1.00 | 1.00 | 1.00 | 1.00 | 1.00 | 1.00 | 1.00 | 1.00 |
| Tmem234 | 0.94 | 1.15 | 1.09 | 1.02 | 0.30 | 1.05 | 0.83 | 0.49 | 1.10 | 1.05 | 1.02 | 1.01 |
| Tmem245 | 1.00 | 0.88 | 0.74 | 0.97 | 0.14 | 0.95 | 1.00 | 1.00 | 1.00 | 1.00 | 0.95 | 1.18 |
| Tmem38b | 1.33 | 1.21 | 1.27 | 1.10 | 0.46 | 1.25 | 0.90 | 0.47 | 0.82 | 1.54 | 1.27 | 1.15 |
| Tmem43 | 0.97 | 0.98 | 0.90 | 0.23 | 0.08 | 0.38 | 0.89 | 0.50 | 0.98 | 1.18 | 0.98 | 1.03 |
| Tmtc3 | 0.86 | 0.81 | 0.75 | 0.78 | 0.95 | 0.78 | 0.94 | 1.00 | 0.84 | 0.76 | 0.54 | 1.17 |
| Tnfrsf11b | 0.64 | 0.80 | 0.78 | 0.18 | 1.00 | 0.16 | 1.00 | 1.00 | 1.00 | 1.00 | 1.00 | 1.00 |
| Tnfrsf14 | 1.73 | 0.89 | 1.00 | 2.00 | 1.00 | 1.01 | 1.00 | 1.00 | 1.00 | 0.51 | 0.15 | 0.93 |
| Tnfrsf19 | 0.90 | 0.69 | 0.72 | 1.00 | 1.00 | 1.00 | 1.00 | 1.00 | 1.00 | 0.64 | 1.62 | 1.38 |
| Tnfsf10 | 0.96 | 0.56 | 0.94 | 0.62 | 0.73 | 0.58 | 1.00 | 1.00 | 1.00 | 0.91 | 0.51 | 0.93 |
| Tnk1 | 1.12 | 1.10 | 0.80 | 1.09 | 1.00 | 1.17 | 1.13 | 1.00 | 1.67 | 1.00 | 1.00 | 1.00 |
| Tnks1bp1 | 0.96 | 1.08 | 0.71 | 0.91 | 0.17 | 0.90 | 1.03 | 1.00 | 1.00 | 0.87 | 0.86 | 1.03 |
| Tnni3k | 1.00 | 1.00 | 1.00 | 1.00 | 1.00 | 1.00 | 1.00 | 1.00 | 1.00 | 1.00 | 1.00 | 1.00 |
| Tns1 | 1.21 | 1.37 | 1.27 | 0.89 | 0.17 | 0.72 | 1.12 | 0.99 | 1.10 | 1.15 | 1.00 | 1.37 |
| Tns3 | 1.04 | 1.07 | 0.83 | 1.07 | 0.34 | 1.01 | 1.29 | 1.00 | 1.17 | 0.89 | 0.61 | 1.01 |
| Tom1l1 | 0.87 | 0.77 | 0.80 | 0.94 | 1.00 | 1.51 | 1.54 | 1.00 | 0.77 | 0.79 | 0.68 | 0.57 |
| Top1 | 0.85 | 0.81 | 0.78 | 1.04 | 0.55 | 0.91 | 0.89 | 0.51 | 0.99 | 0.95 | 0.74 | 0.95 |
| Topbp1 | 0.77 | 0.64 | 0.72 | 0.85 | 1.00 | 0.68 | 1.13 | 0.45 | 1.10 | 1.14 | 0.92 | 1.06 |
| Tpm4 | 0.75 | 0.71 | 0.70 | 1.28 | 0.25 | 0.90 | 0.76 | 0.93 | 0.78 | 1.06 | 0.74 | 0.85 |
| Trappc10 | 1.07 | 0.97 | 0.94 | 1.05 | 0.73 | 0.94 | 1.13 | 0.82 | 0.98 | 0.81 | 0.81 | 0.95 |
| Trappc2 | 0.69 | 1.00 | 0.82 | 0.67 | 0.30 | 0.69 | 0.77 | 1.00 | 1.57 | 1.18 | 1.05 | 1.12 |
| Trappc6b | 1.00 | 1.24 | 1.06 | 0.67 | 0.13 | 0.70 | 0.96 | 0.21 | 1.00 | 1.02 | 1.07 | 0.93 |
| Trappc8 | 0.93 | 0.86 | 0.79 | 1.10 | 0.55 | 0.85 | 1.17 | 1.00 | 1.11 | 1.03 | 0.84 | 1.00 |
| Trim10 | 1.00 | 1.00 | 1.00 | 1.00 | 1.00 | 1.00 | 1.00 | 1.00 | 1.00 | 0.41 | 0.39 | 0.15 |
| Trim13 | 1.12 | 1.20 | 1.00 | 1.18 | 0.99 | 1.06 | 1.05 | 0.21 | 0.94 | 1.09 | 0.81 | 0.96 |
| Trim56 | 1.10 | 1.16 | 0.55 | 1.00 | 0.32 | 0.23 | 1.00 | 1.00 | 1.00 | 0.71 | 0.23 | 1.32 |
| Trim59 | 0.68 | 0.41 | 0.63 | 0.75 | 0.90 | 0.79 | 1.02 | 0.63 | 0.79 | 0.77 | 0.46 | 0.72 |
| Trim8 | 0.83 | 1.16 | 0.91 | 1.00 | 0.16 | 1.27 | 0.72 | 0.89 | 0.86 | 0.84 | 0.69 | 0.97 |
| Trmt10c | 0.91 | 0.91 | 1.15 | 0.98 | 0.44 | 0.95 | 0.98 | 0.49 | 1.05 | 1.00 | 0.86 | 1.16 |
| Trmt61b | 0.44 | 0.74 | 0.67 | 0.37 | 1.00 | 0.73 | 0.62 | 0.63 | 0.60 | 0.85 | 0.92 | 0.56 |
| Trp53 | 1.04 | 0.86 | 1.13 | 1.11 | 1.00 | 1.14 | 0.87 | 0.22 | 0.98 | 1.13 | 1.05 | 0.96 |
| Trp53bp2 | 0.96 | 1.17 | 0.89 | 1.03 | 0.65 | 0.96 | 0.91 | 1.00 | 0.98 | 1.16 | 0.83 | 1.19 |
| Trp63 | 0.84 | 1.06 | 1.06 | 1.60 | 1.00 | 1.00 | 1.00 | 1.00 | 1.00 | 1.00 | 1.00 | 1.00 |
| Trpm7 | 1.12 | 1.02 | 0.92 | 1.00 | 0.38 | 0.93 | 1.06 | 1.00 | 1.07 | 1.05 | 0.82 | 1.05 |
| Tsen2 | 0.36 | 0.37 | 0.36 | 0.28 | 1.00 | 0.53 | 0.37 | 0.65 | 0.32 | 0.53 | 0.77 | 0.49 |
| Tshb | 1.00 | 1.00 | 1.00 | 1.00 | 1.00 | 1.00 | 1.00 | 1.00 | 1.00 | 1.00 | 1.00 | 1.00 |
| Tshr | 1.00 | 1.00 | 1.00 | 0.37 | 0.15 | 0.80 | 0.71 | 1.00 | 0.71 | 1.00 | 1.00 | 1.00 |
| Tshz1 | 1.00 | 0.98 | 0.91 | 1.21 | 0.34 | 1.07 | 0.96 | 1.00 | 0.88 | 0.84 | 0.61 | 0.93 |
| Tshz2 | 1.23 | 1.22 | 1.32 | 1.04 | 0.10 | 1.03 | 0.96 | 1.00 | 0.74 | 1.08 | 0.83 | 1.36 |
| Tspan18 | 0.65 | 0.81 | 1.11 | 0.77 | 0.38 | 0.85 | 0.94 | 1.00 | 0.78 | 0.59 | 0.50 | 0.67 |
| Tspan4 | 0.57 | 0.70 | 0.70 | 0.53 | 0.91 | 0.69 | 0.66 | 0.19 | 0.74 | 0.80 | 1.08 | 0.74 |
| Tspo2 | 1.00 | 1.00 | 1.00 | 1.00 | 0.76 | 1.00 | 1.00 | 1.00 | 1.00 | 0.15 | 0.14 | 0.08 |
| Tspyl4 | 1.16 | 1.18 | 1.24 | 1.23 | 0.66 | 0.92 | 1.15 | 0.34 | 1.07 | 1.02 | 2.63 | 0.91 |
| Tstd2 | 0.92 | 0.82 | 0.84 | 0.89 | 0.33 | 0.86 | 0.97 | 1.00 | 0.85 | 0.93 | 0.68 | 0.99 |
| Ttc30b | 1.15 | 1.13 | 0.87 | 0.87 | 0.46 | 0.91 | 1.24 | 0.46 | 1.09 | 1.03 | 1.11 | 0.93 |
| Tusc3 | 1.04 | 1.09 | 0.89 | 1.00 | 0.48 | 0.77 | 0.95 | 0.96 | 1.01 | 0.72 | 1.11 | 0.83 |
| Twf1 | 0.92 | 0.82 | 0.84 | 0.96 | 0.38 | 1.06 | 0.92 | 0.37 | 0.96 | 1.20 | 1.05 | 1.06 |
| Twist1 | 1.20 | 0.69 | 1.34 | 0.57 | 0.40 | 0.68 | 0.80 | 1.00 | 1.08 | 1.01 | 0.60 | 0.79 |
| Txnip | 1.07 | 1.11 | 1.18 | 1.02 | 0.31 | 1.11 | 0.92 | 0.17 | 0.79 | 1.32 | 1.26 | 1.24 |
| Tyrobp | 0.89 | 0.88 | 0.90 | 0.82 | 1.63 | 0.56 | 0.52 | 0.83 | 0.78 | 0.92 | 1.19 | 0.85 |

Fig. 35- 100

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Tm4sf19 | 1.00 | 1.00 | 1.00 | 1.00 | 1.00 | 1.00 | 1.00 | 1.00 | 1.00 | 1.00 | 1.00 | 1.00 |
| Tm6sf1 | 1.00 | 1.00 | 1.00 | 1.22 | 0.25 | 1.11 | 1.49 | 1.00 | 1.26 | 0.83 | 1.18 | 1.44 |
| Tmeff1 | 1.45 | 1.44 | 0.98 | 0.91 | 1.00 | 0.95 | 1.13 | 0.65 | 1.29 | 1.00 | 1.00 | 1.00 |
| Tmem123 | 0.96 | 1.12 | 1.04 | 0.94 | 0.71 | 1.05 | 0.67 | 0.19 | 0.82 | 0.43 | 0.92 | 1.02 |
| Tmem161b | 1.43 | 0.88 | 1.02 | 1.11 | 1.00 | 0.90 | 0.86 | 0.15 | 1.22 | 0.33 | 1.21 | 1.09 |
| Tmem170b | 1.00 | 1.00 | 1.00 | 0.83 | 1.00 | 0.95 | 0.91 | 0.16 | 1.21 | 0.85 | 1.39 | 1.25 |
| Tmem171 | 1.00 | 1.00 | 1.00 | 1.00 | 1.00 | 1.00 | 1.25 | 0.91 | 1.35 | 1.00 | 1.00 | 1.00 |
| Tmem181b-ps | 0.68 | 0.78 | 0.80 | 0.62 | 0.36 | 0.62 | 0.66 | 0.11 | 0.79 | 0.68 | 0.76 | 0.83 |
| Tmem184c | 1.48 | 1.23 | 1.00 | 1.11 | 1.00 | 1.11 | 0.81 | 0.14 | 0.94 | 0.34 | 0.96 | 0.94 |
| Tmem185b | 1.04 | 0.81 | 0.73 | 1.00 | 1.00 | 1.02 | 0.74 | 0.19 | 0.87 | 0.26 | 0.98 | 1.15 |
| Tmem189 | 1.74 | 2.43 | 1.68 | 1.03 | 1.00 | 0.98 | 1.43 | 0.19 | 1.14 | 0.77 | 1.29 | 1.16 |
| Tmem2 | 1.00 | 1.00 | 1.00 | 1.10 | 1.00 | 1.18 | 1.40 | 0.38 | 1.37 | 0.37 | 1.09 | 1.02 |
| Tmem200b | 1.56 | 1.00 | 1.06 | 1.38 | 1.00 | 1.19 | 0.98 | 0.14 | 1.16 | 1.00 | 1.00 | 1.00 |
| Tmem212 | 1.00 | 1.00 | 1.00 | 0.50 | 0.06 | 1.07 | 1.00 | 1.00 | 1.00 | 1.00 | 1.00 | 1.00 |
| Tmem233 | 1.00 | 1.00 | 1.00 | 1.00 | 1.00 | 1.00 | 1.00 | 1.00 | 1.00 | 1.00 | 1.00 | 1.00 |
| Tmem234 | 0.94 | 1.11 | 0.91 | 1.19 | 2.85 | 0.93 | 1.09 | 0.02 | 1.01 | 0.19 | 1.14 | 0.93 |
| Tmem245 | 1.00 | 1.00 | 1.00 | 0.42 | 1.00 | 0.65 | 1.00 | 1.00 | 1.00 | 1.00 | 1.00 | 1.00 |
| Tmem38b | 1.30 | 1.96 | 1.32 | 0.96 | 1.00 | 1.06 | 1.13 | 0.15 | 1.30 | 0.58 | 1.29 | 1.22 |
| Tmem43 | 0.70 | 1.07 | 1.17 | 1.26 | 1.18 | 0.94 | 0.96 | 0.41 | 0.83 | 0.87 | 1.21 | 1.16 |
| Tmtc3 | 1.41 | 1.12 | 1.00 | 0.98 | 1.00 | 0.79 | 0.59 | 0.16 | 1.02 | 1.00 | 0.75 | 0.78 |
| Tnfrsf11b | 1.00 | 1.00 | 1.00 | 0.92 | 1.00 | 1.00 | 0.55 | 0.35 | 0.85 | 1.00 | 1.00 | 1.00 |
| Tnfrsf14 | 1.00 | 1.00 | 1.00 | 1.00 | 1.00 | 1.00 | 1.00 | 1.00 | 1.00 | 1.48 | 0.45 | 0.48 |
| Tnfrsf19 | 1.00 | 1.00 | 1.00 | 0.83 | 0.51 | 0.85 | 0.62 | 0.18 | 0.78 | 0.35 | 0.62 | 0.88 |
| Tnfsf10 | 0.48 | 0.56 | 0.72 | 1.00 | 1.00 | 1.00 | 0.74 | 1.00 | 1.00 | 1.00 | 0.95 | 0.85 |
| Tnk1 | 1.01 | 1.54 | 1.07 | 1.00 | 1.00 | 1.00 | 1.45 | 0.14 | 1.29 | 0.61 | 0.63 | 0.55 |
| Tnks1bp1 | 0.96 | 1.15 | 1.17 | 1.00 | 1.23 | 0.92 | 0.96 | 0.32 | 0.91 | 0.74 | 0.94 | 0.88 |
| Tnni3k | 1.00 | 1.00 | 1.00 | 1.00 | 1.00 | 1.00 | 1.00 | 1.00 | 1.00 | 1.00 | 1.00 | 1.00 |
| Tns1 | 0.86 | 0.81 | 1.19 | 1.07 | 0.57 | 1.15 | 1.29 | 0.37 | 1.50 | 0.66 | 0.67 | 0.63 |
| Tns3 | 0.96 | 0.89 | 1.15 | 1.17 | 1.00 | 1.08 | 0.81 | 0.06 | 1.08 | 0.38 | 0.72 | 0.86 |
| Tom1l1 | 0.93 | 0.74 | 1.04 | 0.81 | 1.00 | 0.73 | 0.76 | 0.13 | 0.82 | 0.28 | 0.82 | 1.04 |
| Top1 | 1.20 | 1.29 | 0.98 | 1.08 | 1.00 | 0.92 | 0.87 | 0.17 | 0.99 | 0.37 | 0.88 | 0.95 |
| Topbp1 | 1.00 | 1.00 | 1.00 | 0.85 | 1.00 | 1.03 | 0.85 | 0.16 | 1.06 | 0.42 | 0.86 | 0.87 |
| Tpm4 | 1.45 | 1.82 | 0.95 | 1.11 | 0.41 | 1.21 | 0.72 | 0.15 | 0.75 | 0.32 | 0.89 | 1.20 |
| Trappc10 | 0.96 | 0.84 | 0.87 | 0.92 | 1.00 | 0.96 | 0.98 | 0.13 | 1.05 | 0.38 | 0.65 | 0.67 |
| Trappc2 | 0.83 | 0.64 | 1.00 | 1.46 | 1.00 | 1.17 | 0.66 | 0.43 | 0.83 | 0.31 | 0.96 | 1.27 |
| Trappc6b | 1.17 | 0.93 | 0.62 | 1.01 | 0.94 | 0.96 | 1.02 | 0.21 | 0.99 | 0.52 | 1.10 | 1.24 |
| Trappc8 | 1.66 | 0.85 | 1.12 | 1.01 | 1.00 | 1.06 | 0.83 | 0.14 | 0.93 | 0.32 | 1.11 | 1.14 |
| Trim10 | 1.00 | 1.00 | 1.00 | 1.00 | 1.00 | 1.00 | 1.00 | 1.00 | 1.00 | 0.43 | 0.72 | 0.61 |
| Trim13 | 2.15 | 2.26 | 1.06 | 0.88 | 1.00 | 1.32 | 0.82 | 0.20 | 0.89 | 0.45 | 0.96 | 1.20 |
| Trim56 | 1.00 | 1.00 | 1.00 | 0.68 | 1.00 | 0.92 | 1.00 | 1.00 | 1.00 | 1.00 | 0.73 | 0.57 |
| Trim59 | 1.00 | 1.00 | 1.00 | 0.69 | 1.00 | 0.78 | 0.53 | 0.19 | 0.78 | 0.45 | 0.67 | 0.82 |
| Trim8 | 1.10 | 1.26 | 1.02 | 0.97 | 1.31 | 0.97 | 0.97 | 0.17 | 0.92 | 0.42 | 0.97 | 0.98 |
| Trmt10c | 1.04 | 1.18 | 0.96 | 1.16 | 0.43 | 0.88 | 1.02 | 0.07 | 0.93 | 0.37 | 0.93 | 0.98 |
| Trmt61b | 0.78 | 1.00 | 0.68 | 0.80 | 3.55 | 0.79 | 0.34 | 0.13 | 0.54 | 0.35 | 0.54 | 0.47 |
| Trp53 | 1.26 | 1.34 | 0.85 | 0.89 | 1.00 | 0.95 | 1.07 | 0.14 | 0.76 | 0.58 | 0.86 | 1.06 |
| Trp53bp2 | 1.43 | 1.26 | 1.19 | 0.98 | 1.00 | 1.01 | 1.11 | 0.08 | 1.33 | 0.50 | 1.12 | 1.10 |
| Trp63 | 1.00 | 1.00 | 1.00 | 1.00 | 1.00 | 1.00 | 0.75 | 0.14 | 1.04 | 1.00 | 1.00 | 1.00 |
| Trpm7 | 1.06 | 1.27 | 1.10 | 0.87 | 1.00 | 0.84 | 0.92 | 0.20 | 1.08 | 0.29 | 1.01 | 0.93 |
| Tsen2 | 0.27 | 0.31 | 0.24 | 0.71 | 0.79 | 0.65 | 0.52 | 3.93 | 0.52 | 0.99 | 0.43 | 0.55 |
| Tshb | 1.00 | 1.00 | 1.00 | 1.00 | 1.00 | 0.99 | 1.00 | 1.00 | 1.00 | 1.00 | 1.00 | 1.00 |
| Tshr | 1.00 | 1.00 | 1.00 | 1.00 | 1.00 | 1.00 | 1.00 | 1.00 | 1.00 | 1.00 | 1.10 | 1.87 |
| Tshz1 | 0.61 | 0.62 | 0.78 | 0.88 | 1.22 | 0.87 | 1.11 | 0.09 | 1.17 | 0.75 | 0.68 | 0.71 |
| Tshz2 | 0.81 | 0.89 | 1.09 | 0.92 | 1.00 | 1.06 | 0.99 | 0.18 | 1.40 | 1.00 | 1.00 | 1.00 |
| Tspan18 | 1.00 | 1.00 | 1.00 | 0.92 | 0.86 | 1.13 | 0.56 | 0.14 | 0.88 | 1.00 | 1.00 | 1.00 |
| Tspan4 | 0.78 | 0.51 | 0.79 | 1.47 | 0.47 | 1.12 | 1.32 | 3.10 | 0.99 | 1.02 | 0.68 | 0.94 |
| Tspo2 | 1.00 | 1.00 | 1.00 | 1.00 | 1.00 | 1.00 | 1.00 | 1.00 | 1.00 | 0.66 | 0.34 | 0.36 |
| Tspyl4 | 0.83 | 0.71 | 0.93 | 1.07 | 1.16 | 1.02 | 0.66 | 0.29 | 0.96 | 1.00 | 1.64 | 1.02 |
| Tstd2 | 0.90 | 0.70 | 1.09 | 0.94 | 1.24 | 0.96 | 0.78 | 0.12 | 0.98 | 0.43 | 0.85 | 1.00 |
| Ttc30b | 0.78 | 1.08 | 0.93 | 0.93 | 0.36 | 0.90 | 0.66 | 0.16 | 0.80 | 1.00 | 1.27 | 1.00 |
| Tusc3 | 1.21 | 0.72 | 0.84 | 0.99 | 1.00 | 0.98 | 1.19 | 0.11 | 1.09 | 0.41 | 0.82 | 0.89 |
| Twf1 | 1.89 | 1.66 | 1.20 | 1.01 | 1.74 | 0.99 | 0.71 | 0.16 | 0.88 | 0.63 | 1.14 | 1.03 |
| Twist1 | 1.00 | 1.00 | 1.00 | 1.00 | 1.00 | 1.00 | 1.43 | 0.15 | 1.51 | 1.00 | 1.00 | 1.00 |
| Txnip | 1.47 | 1.44 | 1.20 | 0.95 | 2.53 | 1.11 | 2.20 | 0.43 | 2.69 | 0.76 | 1.56 | 1.11 |
| Tyrobp | 1.34 | 0.81 | 0.72 | 1.40 | 0.10 | 1.66 | 1.41 | 2.65 | 1.26 | 2.19 | 1.54 | 1.29 |

Fig. 35- 101

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Tyrp1 | 1.00 | 1.00 | 1.00 | 1.00 | 1.00 | 1.00 | 1.00 | 1.00 | 1.00 | 1.00 | 1.00 | 1.00 |
| U2surp | 1.02 | 1.53 | 0.98 | 1.94 | 0.52 | 0.86 | 0.93 | 1.12 | 1.02 | 0.61 | 0.63 | 0.92 |
| Uap1l1 | 0.54 | 0.20 | 0.42 | 0.11 | 1.00 | 0.79 | 0.34 | 0.28 | 0.41 | 1.36 | 1.25 | 0.68 |
| Ubb | 1.89 | 2.64 | 1.32 | 0.70 | 0.63 | 1.25 | 1.22 | 1.06 | 0.93 | 0.17 | 0.37 | 0.99 |
| Ube2g1 | 1.00 | 1.95 | 1.22 | 1.81 | 0.38 | 0.94 | 1.03 | 1.11 | 0.97 | 0.45 | 0.40 | 0.99 |
| Ube2w | 1.00 | 1.55 | 0.85 | 1.13 | 0.23 | 0.67 | 0.82 | 1.01 | 0.92 | 0.27 | 0.28 | 0.90 |
| Ubiad1 | 0.98 | 1.72 | 1.02 | 0.55 | 0.18 | 0.94 | 0.75 | 0.75 | 0.94 | 0.34 | 0.55 | 1.22 |
| Ubxn2a | 0.68 | 2.46 | 0.90 | 3.65 | 0.28 | 1.16 | 1.20 | 1.94 | 1.46 | 0.54 | 0.76 | 1.62 |
| Ubxn7 | 0.91 | 1.67 | 1.16 | 3.10 | 0.61 | 1.27 | 1.16 | 1.23 | 1.19 | 0.51 | 0.46 | 1.13 |
| Uckl1os | 1.21 | 0.72 | 1.06 | 1.00 | 1.00 | 1.12 | 2.63 | 2.13 | 1.40 | 0.89 | 1.08 | 1.89 |
| Uevld | 0.83 | 1.04 | 0.81 | 1.37 | 0.30 | 0.75 | 0.89 | 0.91 | 1.16 | 1.00 | 0.46 | 0.87 |
| Ugcg | 0.79 | 1.44 | 1.27 | 1.84 | 0.55 | 1.09 | 0.94 | 1.04 | 0.98 | 0.44 | 0.50 | 0.92 |
| Ugt1a1 | 1.00 | 1.00 | 1.00 | 1.00 | 1.00 | 1.00 | 1.00 | 1.00 | 1.00 | 1.00 | 1.00 | 1.00 |
| Ugt1a6a | 1.29 | 1.00 | 1.42 | 2.71 | 0.14 | 2.09 | 0.69 | 0.75 | 1.27 | 1.00 | 0.49 | 0.93 |
| Ulk3 | 0.84 | 1.16 | 0.92 | 1.39 | 0.37 | 0.80 | 0.93 | 0.81 | 1.15 | 0.45 | 0.53 | 0.93 |
| Unc5b | 1.00 | 1.00 | 1.00 | 0.73 | 0.43 | 0.49 | 0.81 | 0.68 | 0.91 | 0.57 | 0.44 | 0.71 |
| Unki | 1.28 | 1.17 | 1.26 | 2.44 | 0.47 | 1.65 | 1.25 | 0.99 | 1.06 | 0.64 | 0.29 | 0.90 |
| Upf3b | 0.95 | 1.92 | 0.88 | 1.34 | 0.25 | 0.99 | 0.96 | 0.98 | 0.70 | 0.22 | 0.23 | 0.93 |
| Upk3b | 1.00 | 1.00 | 1.00 | 1.00 | 1.00 | 1.00 | 0.73 | 0.90 | 1.93 | 0.55 | 0.12 | 0.82 |
| Ush1c | 1.00 | 0.18 | 0.47 | 1.00 | 1.00 | 1.00 | 0.16 | 0.15 | 0.21 | 1.00 | 1.00 | 1.00 |
| Usmg5 | 1.08 | 0.51 | 1.09 | 0.32 | 3.45 | 0.78 | 1.15 | 0.82 | 0.55 | 1.26 | 3.05 | 0.51 |
| Usp12 | 0.82 | 1.26 | 0.92 | 0.95 | 0.31 | 0.85 | 1.10 | 1.27 | 1.12 | 0.81 | 0.57 | 1.08 |
| Usp16 | 1.21 | 1.76 | 1.03 | 1.09 | 0.83 | 1.19 | 1.10 | 1.28 | 0.95 | 0.83 | 0.74 | 1.13 |
| Usp22 | 0.86 | 1.33 | 1.02 | 2.31 | 0.65 | 1.19 | 1.18 | 1.03 | 0.97 | 0.47 | 0.53 | 0.91 |
| Usp32 | 1.03 | 1.16 | 1.15 | 1.31 | 0.19 | 1.01 | 1.24 | 1.43 | 1.09 | 0.74 | 0.42 | 1.00 |
| Usp53 | 0.85 | 1.00 | 1.18 | 1.86 | 0.68 | 0.98 | 1.72 | 2.18 | 2.26 | 1.00 | 1.00 | 0.85 |
| Utrn | 0.89 | 0.95 | 1.17 | 1.67 | 0.52 | 0.78 | 1.17 | 1.32 | 1.22 | 0.63 | 0.70 | 1.03 |
| Uts2 | 1.00 | 1.00 | 1.00 | 1.00 | 1.00 | 1.00 | 1.00 | 1.00 | 1.00 | 1.00 | 1.00 | 1.00 |
| Uts2r | 0.67 | 0.76 | 0.24 | 1.00 | 1.00 | 1.00 | 1.00 | 1.00 | 1.00 | 1.00 | 1.00 | 1.00 |
| Uvrag | 1.34 | 1.91 | 1.33 | 1.42 | 0.55 | 0.95 | 2.27 | 2.11 | 1.44 | 0.69 | 0.57 | 1.09 |
| Vamp1 | 0.67 | 0.72 | 0.50 | 1.01 | 0.18 | 0.77 | 0.86 | 0.68 | 0.75 | 0.39 | 0.31 | 0.74 |
| Vamp4 | 0.69 | 1.05 | 0.82 | 2.13 | 0.33 | 1.60 | 0.91 | 0.97 | 0.80 | 0.63 | 0.51 | 0.96 |
| Vav3 | 0.73 | 1.00 | 1.10 | 1.38 | 0.72 | 1.01 | 0.78 | 1.00 | 1.00 | 0.53 | 0.49 | 1.24 |
| Vcp | 0.44 | 0.34 | 0.44 | 0.14 | 0.33 | 0.33 | 0.36 | 0.31 | 0.32 | 0.23 | 0.34 | 0.39 |
| Vpreb2 | 1.00 | 1.00 | 1.00 | 1.00 | 1.00 | 1.00 | 1.00 | 1.00 | 1.00 | 1.00 | 1.00 | 1.00 |
| Vps37c | 0.97 | 1.91 | 1.00 | 1.71 | 0.35 | 1.26 | 1.15 | 1.17 | 1.18 | 0.24 | 0.31 | 1.07 |
| Vstm2b | 1.00 | 1.00 | 1.00 | 1.00 | 1.00 | 1.00 | 1.00 | 1.00 | 1.00 | 1.00 | 1.00 | 1.00 |
| Vwa1 | 1.07 | 1.03 | 0.80 | 0.66 | 0.59 | 1.10 | 0.97 | 0.72 | 0.89 | 0.41 | 0.38 | 0.81 |
| Wasf2 | 0.99 | 1.07 | 1.56 | 2.53 | 0.08 | 1.12 | 1.51 | 1.89 | 1.65 | 0.98 | 0.15 | 1.28 |
| Wasl | 1.18 | 2.44 | 1.27 | 1.89 | 0.19 | 1.06 | 1.02 | 1.18 | 1.14 | 0.31 | 0.26 | 1.01 |
| Wdr20 | 0.80 | 1.04 | 1.13 | 1.18 | 0.21 | 0.95 | 1.05 | 1.10 | 0.97 | 0.66 | 0.23 | 1.11 |
| Wdr26 | 1.11 | 2.08 | 1.21 | 1.52 | 0.41 | 0.97 | 1.30 | 1.45 | 1.17 | 0.48 | 0.48 | 1.15 |
| Wdr47 | 0.86 | 1.00 | 0.97 | 1.65 | 0.24 | 1.09 | 1.19 | 1.26 | 1.20 | 0.65 | 0.24 | 0.99 |
| Wdr5 | 0.86 | 1.34 | 0.92 | 1.16 | 0.67 | 1.07 | 1.28 | 1.21 | 0.91 | 0.73 | 0.57 | 0.99 |
| Wdr8 | 1.13 | 0.77 | 1.19 | 0.20 | 0.78 | 0.53 | 0.99 | 0.72 | 0.71 | 0.92 | 1.12 | 1.14 |
| Wee1 | 1.06 | 0.94 | 0.61 | 1.81 | 0.82 | 0.84 | 1.33 | 1.70 | 1.01 | 0.73 | 0.64 | 0.88 |
| Wfdc16 | 1.00 | 1.00 | 1.00 | 1.00 | 1.00 | 1.00 | 1.00 | 1.00 | 1.00 | 0.85 | 1.00 | 0.83 |
| Wfdc6a | 1.00 | 1.00 | 1.00 | 1.00 | 1.00 | 1.00 | 1.00 | 1.00 | 1.00 | 2.43 | 3.06 | 0.91 |
| Wipi1 | 1.23 | 2.26 | 0.90 | 1.31 | 0.62 | 1.01 | 1.58 | 1.41 | 1.00 | 0.39 | 0.36 | 0.96 |
| Wisp2 | 1.11 | 0.60 | 0.54 | 0.91 | 1.15 | 0.66 | 0.60 | 0.24 | 0.64 | 0.45 | 0.19 | 0.55 |
| Wiz | 0.96 | 1.58 | 1.05 | 1.57 | 0.20 | 0.98 | 1.10 | 1.03 | 0.89 | 0.33 | 0.27 | 1.01 |
| Wnt3 | 1.00 | 1.00 | 1.00 | 1.00 | 1.00 | 1.00 | 1.00 | 1.00 | 1.00 | 1.00 | 1.00 | 1.00 |
| Wnt5a | 0.56 | 1.00 | 0.44 | 0.82 | 0.20 | 0.54 | 0.49 | 0.38 | 0.61 | 1.00 | 0.70 | 0.85 |
| Wwc1 | 1.00 | 1.00 | 1.00 | 1.00 | 1.00 | 1.00 | 1.00 | 1.00 | 1.00 | 1.00 | 0.11 | 1.30 |
| Xiap | 0.68 | 1.90 | 0.90 | 2.26 | 0.18 | 1.03 | 0.95 | 1.04 | 1.06 | 0.28 | 0.28 | 0.89 |
| Xpr1 | 0.71 | 1.24 | 0.78 | 1.79 | 0.33 | 1.18 | 1.31 | 1.43 | 1.23 | 0.53 | 0.52 | 0.94 |
| Xrcc3 | 0.99 | 1.00 | 1.63 | 0.58 | 0.56 | 0.87 | 1.12 | 1.43 | 1.22 | 1.12 | 0.32 | 0.97 |
| Xrcc6bp1 | 0.83 | 0.54 | 0.58 | 0.55 | 1.07 | 0.60 | 0.80 | 0.61 | 0.90 | 1.20 | 1.26 | 1.34 |
| Xxylt1 | 0.61 | 1.00 | 0.83 | 1.14 | 0.16 | 0.93 | 0.82 | 1.07 | 1.06 | 0.74 | 0.28 | 0.86 |
| Yeats2 | 0.93 | 1.00 | 1.03 | 1.10 | 0.51 | 0.91 | 0.70 | 0.74 | 0.89 | 0.50 | 0.21 | 0.86 |
| Yipf4 | 1.12 | 1.55 | 1.14 | 2.39 | 0.81 | 0.92 | 1.22 | 1.16 | 1.11 | 0.60 | 0.72 | 1.06 |
| Ypel4 | 1.00 | 1.00 | 1.00 | 1.00 | 0.74 | 1.00 | 1.55 | 0.75 | 0.70 | 1.00 | 1.00 | 1.00 |
| Zbed3 | 1.41 | 1.63 | 1.14 | 1.51 | 0.46 | 1.34 | 1.16 | 0.98 | 0.91 | 0.48 | 0.45 | 1.04 |
| Zbed5 | 1.35 | 1.41 | 0.84 | 0.35 | 1.15 | 1.15 | 1.10 | 0.84 | 0.88 | 0.31 | 0.61 | 1.03 |

Fig. 35- 102

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Tyrp1 | 1.00 | 1.00 | 1.00 | 1.00 | 1.00 | 1.00 | 1.00 | 1.00 | 1.00 | 1.00 | 1.00 | 1.00 |
| U2surp | 0.80 | 0.77 | 0.91 | 0.90 | 1.08 | 0.89 | 0.86 | 0.79 | 1.01 | 1.06 | 1.03 | 1.17 |
| Uap1l1 | 1.06 | 0.96 | 0.97 | 0.48 | 0.26 | 0.64 | 0.60 | 2.44 | 1.06 | 0.72 | 0.71 | 0.76 |
| Ubb | 1.05 | 1.30 | 1.00 | 1.51 | 3.24 | 1.21 | 1.24 | 0.21 | 1.26 | 1.08 | 1.25 | 1.10 |
| Ube2g1 | 0.77 | 0.73 | 0.87 | 1.01 | 1.11 | 0.92 | 1.15 | 0.46 | 1.06 | 0.96 | 0.87 | 0.99 |
| Ube2w | 0.88 | 0.88 | 0.95 | 0.95 | 1.75 | 1.00 | 1.03 | 0.92 | 1.13 | 0.89 | 0.80 | 1.09 |
| Ubiad1 | 1.02 | 0.95 | 1.08 | 1.02 | 1.68 | 0.90 | 1.04 | 0.69 | 1.20 | 1.03 | 0.82 | 0.97 |
| Ubxn2a | 0.82 | 0.65 | 1.21 | 1.15 | 1.11 | 1.12 | 1.17 | 2.19 | 1.26 | 1.36 | 0.72 | 1.18 |
| Ubxn7 | 0.77 | 0.75 | 0.94 | 1.38 | 1.76 | 1.18 | 1.16 | 1.02 | 1.02 | 1.09 | 0.90 | 1.14 |
| Uckl1os | 1.01 | 1.00 | 0.91 | 1.00 | 0.32 | 1.18 | 1.00 | 1.00 | 1.00 | 1.24 | 1.00 | 0.87 |
| Uevld | 0.66 | 0.67 | 0.85 | 0.97 | 1.00 | 0.94 | 0.74 | 1.00 | 0.76 | 0.81 | 0.68 | 0.87 |
| Ugcg | 0.79 | 0.82 | 0.90 | 0.91 | 1.17 | 0.89 | 0.59 | 0.48 | 1.04 | 1.11 | 1.02 | 1.09 |
| Ugt1a1 | 1.49 | 1.00 | 1.00 | 0.62 | 1.00 | 0.38 | 1.24 | 2.39 | 1.02 | 1.23 | 0.60 | 1.23 |
| Ugt1a6a | 1.44 | 1.14 | 1.53 | 1.55 | 1.00 | 1.81 | 1.09 | 1.00 | 0.92 | 1.24 | 0.45 | 1.13 |
| Ulk3 | 0.95 | 1.02 | 0.98 | 1.12 | 1.56 | 1.07 | 1.09 | 1.00 | 0.90 | 0.79 | 0.94 | 0.99 |
| Unc5b | 1.09 | 0.82 | 1.10 | 0.85 | 1.00 | 0.82 | 1.89 | 1.00 | 1.36 | 1.06 | 0.78 | 0.98 |
| Unkl | 0.80 | 0.77 | 0.97 | 0.96 | 1.00 | 1.07 | 1.76 | 1.00 | 1.48 | 0.90 | 0.79 | 1.16 |
| Upf3b | 0.98 | 1.02 | 0.99 | 0.90 | 1.71 | 0.90 | 0.86 | 1.00 | 0.83 | 0.95 | 0.94 | 1.04 |
| Upk3b | 1.69 | 1.37 | 0.75 | 1.00 | 1.00 | 1.00 | 1.00 | 1.00 | 1.00 | 1.00 | 1.00 | 1.00 |
| Ush1c | 1.00 | 1.00 | 1.00 | 0.91 | 0.79 | 0.97 | 1.00 | 1.00 | 1.00 | 0.99 | 1.43 | 0.97 |
| Usmg5 | 1.23 | 1.27 | 0.65 | 1.05 | 1.06 | 0.58 | 0.51 | 0.69 | 0.70 | 0.19 | 1.37 | 0.73 |
| Usp12 | 0.79 | 0.68 | 1.14 | 0.89 | 1.11 | 0.94 | 0.88 | 1.37 | 0.97 | 1.04 | 0.73 | 0.94 |
| Usp16 | 0.93 | 0.99 | 0.95 | 1.25 | 1.89 | 0.99 | 1.52 | 0.68 | 1.20 | 1.00 | 1.05 | 0.97 |
| Usp22 | 0.79 | 0.73 | 0.96 | 1.02 | 1.19 | 0.97 | 1.26 | 0.45 | 1.25 | 0.93 | 0.76 | 0.93 |
| Usp32 | 0.76 | 0.77 | 0.92 | 1.10 | 2.05 | 1.01 | 1.10 | 1.00 | 1.04 | 1.12 | 0.79 | 0.97 |
| Usp53 | 0.74 | 0.54 | 1.33 | 1.73 | 1.00 | 1.25 | 1.28 | 1.00 | 0.99 | 0.94 | 0.46 | 0.86 |
| Utrn | 1.05 | 1.03 | 1.16 | 0.99 | 1.05 | 1.18 | 0.96 | 1.00 | 0.93 | 0.85 | 0.68 | 0.80 |
| Uts2 | 1.00 | 1.00 | 1.00 | 1.00 | 1.00 | 1.00 | 1.00 | 1.00 | 1.00 | 1.00 | 1.00 | 1.00 |
| Uts2r | 1.00 | 1.00 | 1.00 | 1.00 | 1.00 | 1.00 | 1.00 | 1.00 | 1.00 | 1.00 | 1.00 | 1.00 |
| Uvrag | 1.09 | 1.21 | 1.04 | 1.06 | 0.97 | 1.05 | 1.52 | 0.80 | 1.05 | 1.09 | 0.88 | 1.01 |
| Vamp1 | 0.70 | 0.72 | 0.73 | 0.58 | 0.84 | 0.71 | 0.48 | 1.76 | 0.68 | 1.03 | 0.82 | 1.01 |
| Vamp4 | 0.84 | 1.02 | 1.09 | 0.81 | 1.68 | 0.89 | 0.70 | 1.00 | 0.70 | 1.01 | 0.90 | 1.00 |
| Vav3 | 1.16 | 0.87 | 1.24 | 0.88 | 0.78 | 0.88 | 1.00 | 1.00 | 1.00 | 1.59 | 1.24 | 1.50 |
| Vcp | 0.36 | 0.37 | 0.44 | 0.26 | 0.10 | 0.34 | 0.33 | 0.17 | 0.34 | 0.29 | 0.33 | 0.35 |
| Vpreb2 | 1.00 | 1.00 | 1.00 | 1.00 | 1.00 | 1.00 | 1.00 | 1.00 | 1.00 | 1.00 | 1.00 | 1.00 |
| Vps37c | 0.93 | 0.91 | 1.12 | 1.08 | 3.36 | 1.12 | 1.40 | 1.00 | 1.37 | 0.92 | 0.76 | 0.94 |
| Vstm2b | 1.00 | 1.00 | 1.00 | 1.00 | 1.00 | 1.00 | 1.00 | 1.00 | 1.00 | 1.00 | 1.00 | 1.00 |
| Vwa1 | 1.50 | 1.03 | 1.08 | 1.03 | 1.28 | 1.05 | 1.00 | 1.00 | 1.00 | 1.03 | 0.97 | 1.03 |
| Wasf2 | 0.68 | 0.52 | 0.95 | 1.20 | 0.54 | 1.19 | 1.18 | 1.00 | 1.52 | 0.97 | 0.31 | 0.92 |
| Wasl | 0.85 | 0.83 | 0.98 | 1.05 | 1.67 | 0.96 | 1.24 | 0.71 | 1.12 | 1.10 | 0.76 | 1.02 |
| Wdr20 | 0.80 | 0.76 | 0.87 | 0.92 | 1.24 | 0.87 | 0.84 | 1.00 | 1.03 | 0.91 | 0.90 | 0.97 |
| Wdr26 | 0.81 | 0.72 | 0.99 | 1.34 | 1.63 | 1.17 | 1.08 | 0.94 | 1.13 | 1.03 | 0.76 | 1.03 |
| Wdr47 | 0.72 | 0.66 | 0.89 | 1.01 | 1.00 | 0.98 | 1.00 | 1.00 | 1.00 | 0.86 | 0.72 | 1.07 |
| Wdr5 | 0.82 | 0.82 | 0.83 | 0.94 | 1.40 | 0.97 | 1.01 | 0.71 | 0.91 | 0.95 | 0.89 | 0.99 |
| Wdr8 | 0.82 | 0.98 | 0.77 | 0.99 | 1.32 | 1.42 | 0.72 | 0.90 | 0.96 | 0.67 | 1.33 | 0.66 |
| Wee1 | 0.70 | 0.78 | 0.73 | 0.58 | 0.78 | 0.73 | 0.45 | 0.24 | 0.58 | 0.73 | 0.62 | 0.73 |
| Wfdc16 | 1.00 | 1.00 | 1.00 | 2.53 | 0.71 | 0.63 | 1.00 | 1.00 | 1.00 | 1.00 | 1.00 | 1.00 |
| Wfdc6a | 1.00 | 1.00 | 1.00 | 1.00 | 1.00 | 1.00 | 1.00 | 1.00 | 1.00 | 1.00 | 1.00 | 1.00 |
| Wipi1 | 1.57 | 1.26 | 1.61 | 1.52 | 2.93 | 1.45 | 3.60 | 1.00 | 2.42 | 0.86 | 1.09 | 1.15 |
| Wisp2 | 0.88 | 1.00 | 0.77 | 1.00 | 1.00 | 1.00 | 1.00 | 1.00 | 1.00 | 1.00 | 1.00 | 1.00 |
| Wiz | 0.76 | 0.76 | 0.94 | 1.12 | 1.04 | 0.97 | 1.16 | 1.18 | 1.05 | 0.97 | 0.77 | 1.10 |
| Wnt3 | 1.00 | 1.00 | 1.00 | 1.00 | 1.00 | 1.00 | 1.00 | 1.00 | 1.00 | 1.00 | 1.00 | 1.00 |
| Wnt5a | 1.00 | 1.00 | 0.92 | 0.99 | 1.00 | 1.03 | 0.54 | 1.00 | 1.02 | 0.80 | 0.44 | 0.83 |
| Wwc1 | 1.61 | 0.93 | 2.09 | 1.16 | 0.93 | 1.00 | 0.47 | 1.00 | 0.75 | 0.94 | 0.48 | 1.01 |
| Xiap | 0.56 | 0.46 | 0.86 | 1.12 | 1.34 | 0.94 | 1.02 | 0.70 | 0.99 | 1.08 | 0.62 | 0.99 |
| Xpr1 | 0.86 | 0.75 | 0.94 | 1.07 | 1.84 | 1.10 | 0.87 | 1.00 | 0.89 | 0.90 | 0.75 | 0.93 |
| Xrcc3 | 0.65 | 0.60 | 0.84 | 0.85 | 0.67 | 1.04 | 0.83 | 0.81 | 0.93 | 0.94 | 0.49 | 1.02 |
| Xrcc6bp1 | 0.86 | 1.08 | 1.25 | 0.79 | 0.93 | 0.55 | 0.59 | 0.17 | 0.75 | 0.58 | 1.40 | 0.87 |
| Xxylt1 | 1.07 | 0.86 | 0.96 | 0.88 | 1.00 | 0.93 | 0.98 | 1.00 | 0.84 | 0.88 | 0.57 | 1.04 |
| Yeats2 | 0.72 | 0.65 | 0.83 | 1.09 | 1.00 | 1.01 | 0.56 | 1.00 | 0.83 | 0.82 | 0.61 | 0.90 |
| Yipf4 | 1.10 | 1.01 | 1.16 | 1.09 | 2.08 | 1.27 | 1.31 | 0.85 | 1.14 | 1.21 | 1.29 | 1.17 |
| Ypel4 | 1.00 | 1.00 | 1.00 | 1.00 | 1.00 | 1.00 | 1.00 | 1.00 | 1.00 | 0.62 | 0.34 | 1.25 |
| Zbed3 | 1.21 | 1.19 | 1.23 | 0.90 | 1.54 | 0.99 | 1.49 | 0.91 | 1.45 | 1.15 | 0.85 | 1.08 |
| Zbed5 | 1.00 | 1.55 | 0.94 | 1.02 | 2.14 | 1.24 | 1.42 | 0.21 | 1.19 | 1.00 | 1.14 | 0.99 |

Fig. 35- 103

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Tyrp1 | 1.00 | 1.00 | 1.00 | 1.00 | 1.00 | 1.00 | 1.00 | 1.00 | 1.00 | 1.00 | 1.00 | 1.00 |
| U2surp | 1.01 | 1.03 | 1.14 | 0.83 | 0.55 | 0.96 | 0.95 | 0.59 | 1.10 | 1.09 | 0.84 | 1.01 |
| Uap1l1 | 0.55 | 0.66 | 0.70 | 0.40 | 0.85 | 0.38 | 0.67 | 2.42 | 0.52 | 0.33 | 0.50 | 0.47 |
| Ubb | 1.19 | 1.32 | 1.09 | 1.48 | 0.29 | 1.18 | 0.96 | 0.16 | 1.03 | 1.02 | 1.20 | 0.91 |
| Ube2g1 | 0.97 | 0.98 | 1.03 | 0.82 | 0.30 | 0.97 | 0.91 | 0.40 | 0.99 | 1.12 | 0.90 | 1.13 |
| Ube2w | 0.91 | 0.96 | 1.05 | 0.89 | 0.38 | 0.79 | 0.83 | 0.92 | 0.85 | 0.92 | 0.84 | 0.92 |
| Ubiad1 | 0.99 | 0.92 | 1.05 | 1.02 | 0.99 | 1.05 | 1.19 | 0.56 | 1.11 | 1.25 | 0.86 | 1.18 |
| Ubxn2a | 1.23 | 1.21 | 0.94 | 1.59 | 0.21 | 1.18 | 1.53 | 1.00 | 1.55 | 1.18 | 0.92 | 1.14 |
| Ubxn7 | 1.13 | 1.24 | 1.15 | 1.39 | 0.38 | 1.14 | 1.05 | 0.62 | 0.96 | 1.24 | 0.90 | 1.28 |
| Uckl1os | 1.21 | 0.90 | 1.00 | 1.81 | 0.86 | 2.14 | 1.70 | 1.37 | 2.57 | 0.83 | 0.87 | 2.50 |
| Uevld | 0.86 | 0.85 | 0.95 | 0.60 | 1.00 | 0.72 | 1.14 | 1.00 | 0.98 | 1.00 | 0.72 | 0.87 |
| Ugcg | 0.98 | 1.00 | 0.94 | 0.87 | 0.38 | 0.91 | 0.90 | 0.36 | 0.94 | 0.95 | 0.74 | 1.01 |
| Ugt1a1 | 1.45 | 1.38 | 1.81 | 1.00 | 1.00 | 1.00 | 1.00 | 1.00 | 1.00 | 1.00 | 1.00 | 1.00 |
| Ugt1a6a | 0.83 | 0.67 | 0.70 | 0.64 | 0.16 | 0.73 | 0.90 | 1.00 | 0.85 | 1.44 | 1.33 | 1.83 |
| Ulk3 | 0.95 | 0.94 | 0.95 | 0.76 | 1.00 | 1.00 | 1.20 | 0.82 | 0.66 | 1.05 | 0.87 | 0.96 |
| Unc5b | 0.76 | 0.96 | 0.69 | 1.13 | 0.97 | 1.05 | 1.00 | 1.00 | 1.00 | 0.55 | 0.65 | 0.72 |
| Unki | 1.11 | 1.09 | 1.26 | 1.64 | 1.00 | 1.29 | 1.18 | 1.00 | 0.88 | 1.07 | 0.93 | 1.10 |
| Upf3b | 1.05 | 0.98 | 1.01 | 0.93 | 0.50 | 1.15 | 0.86 | 0.47 | 0.76 | 1.42 | 1.19 | 1.17 |
| Upk3b | 1.00 | 1.00 | 1.00 | 0.84 | 0.44 | 1.11 | 1.00 | 1.00 | 1.00 | 0.62 | 0.69 | 1.91 |
| Ush1c | 1.00 | 1.00 | 1.00 | 1.00 | 2.44 | 1.77 | 1.00 | 1.89 | 1.00 | 1.00 | 1.00 | 1.00 |
| Usmg5 | 0.92 | 0.95 | 1.26 | 0.50 | 1.28 | 0.71 | 1.00 | 1.22 | 1.75 | 0.58 | 1.94 | 0.47 |
| Usp12 | 0.90 | 0.91 | 0.69 | 1.04 | 0.46 | 0.90 | 0.98 | 2.68 | 0.98 | 0.75 | 0.62 | 0.92 |
| Usp16 | 1.20 | 0.94 | 1.01 | 1.42 | 0.71 | 1.16 | 1.04 | 0.47 | 1.02 | 1.14 | 0.93 | 0.98 |
| Usp22 | 0.94 | 0.92 | 0.93 | 1.14 | 0.37 | 1.10 | 1.04 | 0.41 | 0.92 | 1.14 | 1.16 | 1.15 |
| Usp32 | 1.10 | 1.18 | 0.90 | 1.07 | 0.87 | 0.92 | 1.13 | 1.04 | 1.02 | 0.86 | 0.75 | 0.85 |
| Usp53 | 1.25 | 1.26 | 1.03 | 1.32 | 1.00 | 0.59 | 1.04 | 0.76 | 1.04 | 0.96 | 0.63 | 1.16 |
| Utrn | 1.27 | 1.18 | 0.94 | 0.62 | 0.12 | 0.62 | 1.03 | 1.00 | 0.86 | 1.03 | 0.75 | 1.09 |
| Uts2 | 0.43 | 0.20 | 0.18 | 1.00 | 1.00 | 1.00 | 1.13 | 1.91 | 1.00 | 1.00 | 1.00 | 1.00 |
| Uts2r | 1.00 | 1.00 | 1.00 | 1.00 | 1.00 | 1.00 | 1.00 | 1.00 | 1.00 | 1.00 | 1.00 | 1.00 |
| Uvrag | 1.25 | 1.35 | 0.96 | 1.22 | 0.49 | 1.05 | 0.99 | 1.20 | 1.03 | 1.24 | 1.00 | 0.98 |
| Vamp1 | 1.11 | 1.08 | 1.24 | 0.80 | 0.63 | 1.00 | 0.98 | 1.00 | 0.98 | 0.89 | 0.97 | 1.03 |
| Vamp4 | 0.92 | 1.33 | 1.24 | 0.81 | 1.00 | 1.13 | 0.94 | 0.47 | 1.00 | 1.13 | 0.97 | 1.12 |
| Vav3 | 0.87 | 1.01 | 1.04 | 0.84 | 0.64 | 0.93 | 0.40 | 0.30 | 0.30 | 1.19 | 0.83 | 1.14 |
| Vcp | 0.27 | 0.27 | 0.28 | 0.37 | 0.27 | 0.43 | 0.27 | 0.19 | 0.31 | 0.34 | 0.46 | 0.42 |
| Vpreb2 | 1.00 | 1.00 | 1.00 | 1.00 | 1.00 | 1.00 | 1.00 | 1.00 | 1.00 | 1.00 | 1.00 | 1.00 |
| Vps37c | 1.08 | 1.06 | 1.08 | 1.41 | 0.31 | 1.17 | 0.92 | 0.28 | 1.02 | 0.98 | 0.79 | 0.95 |
| Vstm2b | 2.23 | 2.63 | 1.88 | 0.36 | 0.91 | 0.19 | 1.00 | 1.00 | 1.00 | 1.00 | 1.31 | 1.00 |
| Vwa1 | 0.88 | 1.03 | 1.32 | 1.22 | 0.57 | 1.41 | 0.87 | 0.43 | 1.05 | 0.98 | 1.21 | 1.02 |
| Wasf2 | 0.94 | 0.98 | 0.71 | 1.47 | 0.29 | 1.04 | 0.93 | 2.56 | 1.01 | 1.00 | 0.50 | 1.30 |
| Wasl | 1.06 | 0.94 | 0.87 | 1.01 | 0.20 | 0.97 | 1.20 | 0.58 | 1.03 | 1.04 | 0.89 | 1.04 |
| Wdr20 | 0.92 | 0.98 | 0.77 | 0.99 | 0.34 | 1.08 | 1.17 | 0.78 | 1.05 | 1.08 | 0.82 | 1.13 |
| Wdr26 | 1.04 | 1.02 | 0.95 | 1.03 | 0.20 | 0.93 | 1.01 | 0.34 | 0.94 | 1.02 | 0.70 | 1.00 |
| Wdr47 | 1.03 | 0.99 | 1.04 | 0.88 | 0.87 | 0.75 | 1.10 | 0.92 | 0.95 | 0.84 | 1.07 | 1.01 |
| Wdr5 | 0.85 | 0.84 | 0.96 | 1.09 | 0.48 | 1.23 | 1.05 | 0.92 | 0.93 | 1.04 | 0.94 | 0.96 |
| Wdr8 | 1.11 | 0.88 | 0.83 | 0.83 | 1.00 | 0.80 | 0.74 | 1.04 | 0.90 | 1.15 | 0.88 | 1.27 |
| Wee1 | 0.79 | 0.95 | 0.81 | 0.95 | 1.00 | 0.73 | 1.09 | 0.82 | 1.11 | 0.96 | 0.80 | 0.91 |
| Wfdc16 | 1.00 | 1.00 | 1.00 | 1.00 | 4.32 | 0.03 | 1.00 | 1.00 | 1.00 | 1.00 | 1.00 | 1.00 |
| Wfdc6a | 1.00 | 1.00 | 1.00 | 1.00 | 1.53 | 0.18 | 1.15 | 1.56 | 1.02 | 1.00 | 1.00 | 1.00 |
| Wipi1 | 1.28 | 1.60 | 1.31 | 1.16 | 1.00 | 1.02 | 0.83 | 0.99 | 1.00 | 0.85 | 1.13 | 0.91 |
| Wisp2 | 1.00 | 1.00 | 1.00 | 1.07 | 1.16 | 0.30 | 0.58 | 0.93 | 1.00 | 0.84 | 0.82 | 0.85 |
| Wiz | 0.97 | 1.03 | 0.99 | 1.02 | 0.42 | 1.15 | 1.08 | 0.43 | 1.09 | 0.96 | 0.83 | 1.07 |
| Wnt3 | 1.00 | 1.00 | 1.00 | 1.00 | 1.00 | 1.00 | 0.92 | 1.14 | 1.19 | 1.00 | 1.00 | 1.00 |
| Wnt5a | 0.56 | 0.44 | 0.45 | 0.73 | 0.83 | 0.69 | 0.95 | 1.00 | 0.72 | 0.58 | 0.48 | 0.74 |
| Wwc1 | 1.10 | 0.77 | 0.83 | 1.56 | 1.00 | 2.32 | 1.00 | 1.00 | 1.35 | 1.00 | 1.25 | 1.00 |
| Xiap | 1.00 | 0.82 | 0.83 | 1.10 | 0.11 | 0.87 | 0.84 | 1.00 | 0.89 | 0.90 | 0.59 | 1.07 |
| Xpr1 | 1.19 | 1.11 | 1.12 | 0.84 | 0.68 | 0.84 | 1.10 | 0.52 | 0.96 | 0.92 | 0.85 | 1.00 |
| Xrcc3 | 0.90 | 0.91 | 0.85 | 1.03 | 0.53 | 1.18 | 1.24 | 1.88 | 0.90 | 1.01 | 0.65 | 1.08 |
| Xrcc6bp1 | 0.89 | 0.82 | 0.70 | 0.72 | 0.45 | 1.08 | 0.96 | 0.72 | 0.64 | 1.44 | 1.47 | 0.98 |
| Xxylt1 | 0.80 | 0.74 | 0.89 | 0.80 | 0.60 | 0.92 | 1.00 | 1.00 | 1.15 | 1.04 | 0.89 | 1.01 |
| Yeats2 | 0.72 | 0.84 | 0.88 | 0.76 | 0.92 | 0.76 | 0.93 | 1.00 | 0.96 | 0.83 | 0.75 | 1.00 |
| Yipf4 | 1.27 | 1.10 | 1.40 | 1.05 | 0.32 | 1.11 | 1.21 | 0.95 | 1.10 | 1.20 | 0.99 | 1.05 |
| Ypel4 | 1.72 | 1.19 | 1.10 | 1.22 | 1.00 | 0.66 | 0.92 | 1.00 | 0.63 | 0.53 | 0.57 | 0.19 |
| Zbed3 | 1.01 | 1.03 | 1.06 | 1.21 | 0.53 | 1.32 | 1.15 | 0.44 | 1.06 | 1.13 | 1.03 | 1.21 |
| Zbed5 | 1.05 | 1.36 | 0.90 | 1.11 | 0.77 | 1.01 | 0.77 | 0.17 | 1.05 | 0.94 | 1.19 | 0.89 |

Fig. 35- 104

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Tyrp1 | 1.00 | 1.00 | 1.00 | 1.00 | 1.00 | 1.00 | 1.36 | 0.20 | 1.43 | 1.00 | 1.00 | 1.00 |
| U2surp | 0.81 | 0.99 | 1.00 | 0.94 | 1.96 | 0.96 | 0.81 | 0.18 | 0.98 | 0.57 | 0.89 | 0.94 |
| Uap1l1 | 1.05 | 1.06 | 0.75 | 0.80 | 0.46 | 1.01 | 0.57 | 4.46 | 0.59 | 0.72 | 0.38 | 0.40 |
| Ubb | 0.98 | 0.96 | 0.89 | 1.19 | 1.02 | 1.05 | 1.51 | 0.12 | 1.19 | 0.47 | 1.16 | 1.11 |
| Ube2g1 | 1.03 | 0.90 | 0.94 | 1.01 | 2.03 | 0.92 | 0.80 | 0.18 | 1.01 | 0.47 | 0.96 | 0.98 |
| Ube2w | 0.98 | 1.47 | 0.86 | 0.95 | 0.53 | 1.03 | 0.90 | 0.13 | 0.90 | 0.36 | 1.02 | 1.19 |
| Ubiad1 | 1.24 | 0.82 | 1.09 | 1.47 | 1.00 | 1.23 | 1.11 | 0.11 | 1.19 | 0.69 | 0.83 | 0.96 |
| Ubxn2a | 1.22 | 1.63 | 1.28 | 1.16 | 0.42 | 1.13 | 0.85 | 0.18 | 1.12 | 0.89 | 1.01 | 1.00 |
| Ubxn7 | 1.59 | 1.28 | 1.48 | 0.98 | 1.03 | 0.96 | 0.92 | 0.16 | 1.25 | 0.56 | 1.07 | 1.02 |
| Uckl1os | 1.00 | 1.00 | 1.00 | 1.17 | 0.19 | 1.16 | 1.43 | 4.52 | 1.66 | 1.00 | 1.00 | 1.00 |
| Uevld | 1.00 | 1.01 | 1.00 | 0.93 | 1.00 | 0.92 | 0.66 | 0.19 | 1.04 | 0.51 | 0.70 | 0.82 |
| Ugcg | 1.22 | 1.44 | 0.89 | 0.98 | 3.75 | 0.98 | 0.70 | 0.19 | 0.79 | 0.58 | 0.98 | 0.93 |
| Ugt1a1 | 1.00 | 1.00 | 1.00 | 1.00 | 1.00 | 1.00 | 0.91 | 0.10 | 0.95 | 1.00 | 1.00 | 1.00 |
| Ugt1a6a | 1.00 | 1.00 | 1.00 | 1.00 | 1.00 | 1.00 | 1.12 | 0.19 | 1.13 | 1.00 | 1.00 | 1.00 |
| Ulk3 | 1.35 | 1.86 | 1.11 | 0.98 | 1.00 | 1.06 | 0.94 | 0.17 | 0.92 | 0.43 | 1.14 | 0.94 |
| Unc5b | 1.00 | 1.00 | 0.88 | 0.90 | 1.00 | 0.79 | 1.45 | 0.18 | 1.40 | 1.00 | 1.00 | 1.00 |
| Unkl | 1.13 | 0.92 | 1.45 | 0.93 | 0.49 | 0.93 | 0.97 | 0.14 | 1.06 | 0.64 | 1.10 | 0.92 |
| Upf3b | 1.09 | 0.92 | 0.91 | 1.02 | 1.06 | 0.94 | 1.07 | 0.18 | 0.96 | 0.25 | 0.98 | 0.95 |
| Upk3b | 0.47 | 0.56 | 1.00 | 1.00 | 1.00 | 1.00 | 1.00 | 1.00 | 1.00 | 1.00 | 1.00 | 1.00 |
| Ush1c | 1.00 | 1.00 | 1.00 | 1.00 | 1.66 | 1.00 | 1.00 | 1.00 | 1.00 | 1.00 | 1.00 | 1.00 |
| Usmg5 | 1.00 | 1.00 | 1.00 | 1.26 | 0.86 | 1.48 | 2.36 | 2.49 | 2.55 | 2.00 | 0.51 | 1.28 |
| Usp12 | 1.17 | 1.34 | 1.22 | 1.09 | 1.22 | 0.94 | 0.85 | 0.18 | 0.97 | 0.64 | 0.86 | 0.90 |
| Usp16 | 1.08 | 1.03 | 0.85 | 1.01 | 0.17 | 1.09 | 0.93 | 0.30 | 0.93 | 0.72 | 1.09 | 0.97 |
| Usp22 | 0.93 | 0.91 | 0.86 | 0.97 | 0.65 | 0.98 | 0.87 | 0.15 | 1.00 | 0.59 | 0.97 | 1.04 |
| Usp32 | 1.02 | 1.54 | 1.00 | 0.97 | 0.71 | 1.03 | 0.79 | 0.20 | 0.94 | 0.40 | 0.93 | 0.82 |
| Usp53 | 1.00 | 1.34 | 1.00 | 0.74 | 1.00 | 0.86 | 0.98 | 0.18 | 1.30 | 1.00 | 1.24 | 0.96 |
| Utrn | 0.88 | 0.79 | 1.08 | 0.94 | 0.62 | 0.92 | 0.84 | 0.46 | 1.03 | 1.07 | 1.40 | 1.22 |
| Uts2 | 1.00 | 1.00 | 1.00 | 1.00 | 1.47 | 1.00 | 1.00 | 1.00 | 1.00 | 1.00 | 1.00 | 1.00 |
| Uts2r | 1.00 | 1.00 | 1.00 | 1.00 | 1.00 | 1.00 | 0.29 | 0.18 | 0.47 | 1.00 | 1.00 | 1.00 |
| Uvrag | 1.42 | 0.95 | 0.78 | 1.16 | 2.16 | 1.08 | 1.12 | 0.13 | 1.20 | 0.71 | 1.25 | 1.12 |
| Vamp1 | 0.54 | 0.60 | 0.68 | 1.02 | 0.63 | 1.00 | 0.93 | 0.24 | 0.89 | 0.52 | 0.87 | 0.91 |
| Vamp4 | 0.85 | 0.62 | 0.80 | 0.98 | 0.41 | 1.09 | 0.73 | 0.15 | 0.98 | 0.58 | 1.61 | 1.32 |
| Vav3 | 1.00 | 1.00 | 1.00 | 1.03 | 1.00 | 1.03 | 0.67 | 0.13 | 0.75 | 0.80 | 1.37 | 1.36 |
| Vcp | 0.32 | 0.34 | 0.38 | 0.30 | 0.07 | 0.35 | 0.29 | 0.27 | 0.30 | 0.33 | 0.34 | 0.34 |
| Vpreb2 | 1.00 | 1.00 | 1.00 | 1.00 | 1.00 | 1.00 | 1.00 | 1.00 | 1.00 | 0.18 | 0.28 | 0.42 |
| Vps37c | 1.36 | 1.41 | 0.85 | 1.09 | 1.00 | 1.04 | 1.01 | 0.09 | 1.02 | 0.41 | 1.42 | 1.16 |
| Vstm2b | 1.00 | 1.00 | 1.00 | 0.98 | 0.80 | 0.95 | 1.00 | 1.00 | 1.00 | 1.00 | 1.00 | 1.00 |
| Vwa1 | 1.08 | 1.05 | 1.12 | 0.96 | 0.74 | 0.93 | 1.36 | 0.20 | 0.99 | 1.00 | 1.00 | 1.00 |
| Wasf2 | 1.21 | 0.99 | 1.58 | 0.93 | 0.98 | 0.97 | 0.85 | 0.04 | 1.22 | 0.27 | 0.78 | 0.69 |
| Wasl | 1.09 | 1.23 | 0.93 | 0.99 | 0.76 | 1.00 | 0.92 | 0.15 | 1.04 | 0.41 | 0.99 | 0.83 |
| Wdr20 | 1.03 | 1.34 | 1.20 | 0.88 | 0.94 | 0.94 | 0.88 | 0.07 | 1.01 | 0.54 | 0.90 | 0.95 |
| Wdr26 | 1.31 | 1.46 | 1.27 | 0.96 | 0.63 | 1.00 | 0.86 | 0.18 | 1.02 | 0.58 | 1.24 | 1.21 |
| Wdr47 | 1.00 | 1.00 | 1.00 | 1.03 | 1.66 | 1.03 | 0.60 | 0.09 | 0.59 | 0.97 | 0.94 | 1.05 |
| Wdr5 | 0.99 | 0.79 | 1.03 | 0.90 | 0.30 | 0.98 | 1.05 | 0.17 | 0.91 | 0.52 | 1.01 | 1.06 |
| Wdr8 | 1.00 | 1.00 | 1.00 | 1.52 | 1.97 | 1.21 | 0.85 | 0.62 | 0.72 | 1.13 | 0.97 | 0.90 |
| Wee1 | 0.79 | 0.65 | 0.83 | 1.00 | 0.63 | 0.94 | 0.95 | 0.16 | 1.39 | 0.64 | 0.75 | 0.92 |
| Wfdc16 | 1.00 | 1.00 | 1.00 | 1.00 | 1.00 | 1.00 | 1.00 | 1.00 | 1.00 | 1.00 | 1.00 | 1.00 |
| Wfdc6a | 1.00 | 1.00 | 1.00 | 1.00 | 1.00 | 1.00 | 1.00 | 1.00 | 1.00 | 1.00 | 1.00 | 1.00 |
| Wipi1 | 1.44 | 1.16 | 0.79 | 0.89 | 1.00 | 0.93 | 1.62 | 0.17 | 1.37 | 0.47 | 1.41 | 1.12 |
| Wisp2 | 1.00 | 1.00 | 1.00 | 1.00 | 1.00 | 1.00 | 0.75 | 1.64 | 0.70 | 1.00 | 1.00 | 1.00 |
| Wiz | 1.09 | 0.94 | 1.07 | 1.08 | 2.07 | 1.02 | 0.89 | 0.14 | 0.97 | 0.35 | 0.90 | 0.85 |
| Wnt3 | 1.00 | 1.00 | 1.00 | 1.37 | 1.06 | 1.32 | 0.37 | 0.16 | 0.37 | 1.00 | 1.00 | 1.00 |
| Wnt5a | 1.00 | 1.00 | 1.00 | 0.95 | 1.00 | 0.88 | 0.57 | 0.33 | 0.85 | 1.00 | 1.00 | 1.00 |
| Wwc1 | 1.46 | 1.08 | 1.63 | 1.20 | 1.00 | 1.04 | 0.83 | 0.20 | 0.85 | 1.00 | 1.00 | 1.00 |
| Xiap | 1.13 | 0.98 | 1.59 | 0.89 | 1.00 | 0.88 | 0.86 | 0.17 | 1.06 | 0.42 | 0.91 | 0.92 |
| Xpr1 | 1.00 | 1.00 | 1.00 | 0.91 | 2.37 | 1.00 | 0.80 | 0.19 | 0.94 | 0.54 | 1.09 | 0.97 |
| Xrcc3 | 1.19 | 0.95 | 0.90 | 0.98 | 0.72 | 0.97 | 0.92 | 0.14 | 0.95 | 0.73 | 0.75 | 0.70 |
| Xrcc6bp1 | 1.12 | 0.42 | 0.39 | 1.04 | 0.62 | 1.08 | 0.74 | 1.50 | 0.80 | 2.69 | 0.95 | 1.29 |
| Xxylt1 | 0.91 | 1.08 | 0.90 | 0.92 | 2.33 | 0.99 | 0.67 | 0.34 | 0.84 | 0.71 | 0.80 | 0.92 |
| Yeats2 | 1.00 | 1.00 | 1.00 | 0.78 | 1.00 | 0.88 | 0.74 | 0.15 | 0.87 | 0.47 | 0.83 | 0.86 |
| Yipf4 | 1.35 | 1.28 | 1.20 | 0.99 | 0.18 | 1.06 | 0.88 | 0.57 | 1.12 | 1.63 | 1.92 | 2.11 |
| Ypel4 | 1.00 | 1.00 | 1.00 | 1.21 | 1.00 | 0.95 | 1.27 | 0.61 | 1.23 | 0.08 | 0.78 | 0.75 |
| Zbed3 | 1.15 | 0.85 | 0.69 | 1.03 | 1.00 | 0.93 | 1.11 | 0.18 | 1.03 | 0.52 | 0.84 | 0.89 |
| Zbed5 | 1.15 | 1.44 | 0.84 | 0.94 | 0.94 | 0.99 | 1.22 | 0.38 | 1.03 | 0.71 | 1.24 | 1.21 |

Fig. 35- 105

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Zbed6 | 1.00 | 1.00 | 1.00 | 1.00 | 1.00 | 1.00 | 1.00 | 1.00 | 1.92 | 1.00 | 1.00 | 1.00 |
| Zbtb1 | 0.77 | 1.15 | 0.99 | 2.12 | 0.33 | 0.66 | 0.92 | 1.16 | 0.97 | 0.66 | 0.30 | 1.14 |
| Zbtb11 | 2.36 | 2.96 | 1.54 | 2.26 | 0.20 | 1.08 | 1.18 | 1.58 | 1.24 | 0.75 | 0.35 | 1.06 |
| Zbtb12 | 0.77 | 1.00 | 1.25 | 0.80 | 0.60 | 0.68 | 1.14 | 0.92 | 1.11 | 1.00 | 0.31 | 1.08 |
| Zbtb18 | 0.83 | 1.55 | 0.92 | 1.21 | 0.22 | 0.71 | 0.78 | 0.94 | 0.96 | 1.20 | 0.73 | 1.12 |
| Zbtb20 | 1.74 | 1.68 | 1.85 | 0.57 | 1.60 | 1.21 | 1.53 | 1.86 | 0.85 | 1.11 | 1.00 | 1.00 |
| Zbtb25 | 0.60 | 0.99 | 0.83 | 1.57 | 0.44 | 0.91 | 0.96 | 0.95 | 0.93 | 0.38 | 0.52 | 1.09 |
| Zbtb33 | 0.91 | 1.00 | 0.84 | 3.54 | 0.22 | 0.72 | 0.90 | 1.40 | 1.13 | 1.00 | 0.45 | 0.97 |
| Zbtb39 | 1.25 | 1.27 | 1.25 | 1.49 | 0.52 | 1.23 | 1.20 | 1.53 | 1.37 | 0.91 | 0.78 | 1.16 |
| Zc3h11a | 1.05 | 2.10 | 1.14 | 1.95 | 0.35 | 0.90 | 0.84 | 0.95 | 0.97 | 0.35 | 0.36 | 0.97 |
| Zc3h13 | 0.93 | 1.23 | 1.15 | 1.45 | 0.24 | 0.92 | 1.25 | 1.63 | 1.34 | 0.53 | 0.44 | 1.03 |
| Zc3h4 | 0.96 | 1.74 | 1.15 | 1.87 | 0.26 | 0.91 | 1.37 | 1.40 | 1.17 | 0.54 | 0.48 | 1.12 |
| Zc3h6 | 0.39 | 0.50 | 0.65 | 3.68 | 0.56 | 1.23 | 0.95 | 1.53 | 1.11 | 1.04 | 0.62 | 1.05 |
| Zcchc14 | 0.81 | 1.59 | 1.05 | 1.78 | 0.18 | 1.19 | 1.21 | 1.39 | 1.20 | 0.34 | 0.24 | 1.08 |
| Zcchc18 | 1.00 | 1.00 | 1.00 | 1.00 | 0.13 | 1.00 | 1.00 | 1.00 | 1.00 | 1.00 | 1.00 | 1.00 |
| Zcchc2 | 1.22 | 1.34 | 1.30 | 1.07 | 0.16 | 0.63 | 1.03 | 1.04 | 1.02 | 0.58 | 0.39 | 1.21 |
| Zcchc6 | 0.89 | 1.00 | 0.99 | 2.36 | 0.20 | 0.91 | 1.10 | 1.63 | 1.36 | 1.00 | 0.34 | 1.14 |
| Zcchc9 | 1.04 | 1.87 | 0.97 | 0.89 | 0.27 | 1.11 | 0.80 | 0.90 | 0.76 | 0.40 | 0.27 | 1.03 |
| Zdhhc16 | 1.17 | 1.46 | 0.90 | 0.76 | 1.62 | 1.11 | 1.01 | 0.70 | 0.90 | 0.19 | 0.69 | 0.97 |
| Zdhhc21 | 0.70 | 1.00 | 0.79 | 1.26 | 0.57 | 0.60 | 0.96 | 0.98 | 0.97 | 0.67 | 0.53 | 1.03 |
| Zfp146 | 1.10 | 1.02 | 1.09 | 1.14 | 0.06 | 0.95 | 0.74 | 0.87 | 0.95 | 1.00 | 0.12 | 1.01 |
| Zfp160 | 0.71 | 1.01 | 1.04 | 1.88 | 0.32 | 0.97 | 0.85 | 0.91 | 1.06 | 0.34 | 0.30 | 0.91 |
| Zfp217 | 0.96 | 1.00 | 1.29 | 1.23 | 0.29 | 0.72 | 1.10 | 1.46 | 1.40 | 0.71 | 0.19 | 1.10 |
| Zfp219 | 1.17 | 1.67 | 1.05 | 0.47 | 0.19 | 0.78 | 1.00 | 0.82 | 1.00 | 0.42 | 0.38 | 1.00 |
| Zfp266 | 0.70 | 1.34 | 0.86 | 2.38 | 0.24 | 0.93 | 1.08 | 1.19 | 1.01 | 0.42 | 0.20 | 0.97 |
| Zfp280c | 0.79 | 1.00 | 0.92 | 2.91 | 0.38 | 1.08 | 0.78 | 1.34 | 0.92 | 0.84 | 0.41 | 0.85 |
| Zfp280d | 1.19 | 2.34 | 1.25 | 2.42 | 0.37 | 0.98 | 1.06 | 1.30 | 0.91 | 0.72 | 0.25 | 0.96 |
| Zfp367 | 0.58 | 1.07 | 0.62 | 2.83 | 0.60 | 0.85 | 0.83 | 0.88 | 0.86 | 0.71 | 0.56 | 0.84 |
| Zfp36l2 | 0.84 | 1.16 | 1.36 | 0.89 | 0.08 | 0.66 | 1.07 | 0.96 | 1.28 | 0.29 | 0.31 | 1.00 |
| Zfp395 | 0.58 | 1.19 | 0.73 | 1.19 | 0.42 | 0.68 | 0.85 | 0.71 | 0.95 | 0.22 | 0.30 | 0.90 |
| Zfp423 | 0.75 | 0.96 | 0.78 | 0.33 | 0.20 | 0.64 | 1.26 | 0.96 | 0.98 | 1.03 | 1.00 | 0.96 |
| Zfp46 | 0.44 | 0.85 | 0.67 | 0.77 | 0.20 | 0.86 | 0.84 | 0.77 | 0.91 | 0.48 | 0.33 | 0.90 |
| Zfp51 | 0.62 | 1.43 | 0.71 | 2.12 | 0.33 | 0.85 | 0.84 | 0.98 | 1.01 | 0.89 | 0.26 | 1.11 |
| Zfp516 | 0.80 | 1.07 | 0.97 | 1.81 | 0.51 | 1.18 | 1.11 | 1.26 | 1.26 | 0.67 | 0.58 | 1.23 |
| Zfp553 | 0.81 | 1.69 | 1.01 | 1.33 | 0.22 | 0.89 | 1.14 | 1.13 | 1.09 | 0.51 | 0.36 | 1.19 |
| Zfp58 | 0.48 | 0.76 | 0.41 | 1.38 | 0.51 | 0.62 | 0.65 | 0.58 | 0.66 | 0.82 | 0.31 | 0.61 |
| Zfp646 | 1.17 | 1.18 | 1.10 | 1.00 | 0.16 | 0.89 | 1.05 | 1.43 | 1.37 | 0.56 | 0.16 | 1.05 |
| Zfp710 | 0.66 | 0.58 | 0.76 | 0.70 | 0.27 | 0.95 | 1.05 | 0.94 | 1.01 | 0.34 | 0.38 | 0.86 |
| Zfp715 | 0.83 | 1.76 | 1.12 | 2.38 | 0.18 | 1.00 | 1.07 | 1.27 | 1.13 | 0.47 | 0.30 | 0.74 |
| Zfp740 | 0.92 | 2.24 | 1.08 | 1.11 | 0.19 | 0.96 | 1.00 | 1.05 | 1.07 | 0.26 | 0.27 | 1.02 |
| Zfp746 | 1.42 | 2.45 | 1.38 | 1.33 | 0.26 | 1.10 | 1.14 | 1.08 | 1.04 | 0.50 | 0.40 | 1.08 |
| Zfp758 | 1.12 | 1.61 | 0.88 | 3.80 | 0.30 | 1.33 | 1.05 | 1.29 | 1.09 | 0.67 | 0.26 | 1.03 |
| Zfp770 | 0.80 | 1.42 | 1.03 | 1.68 | 0.19 | 0.87 | 0.63 | 1.06 | 1.43 | 0.82 | 0.45 | 1.07 |
| Zfp866 | 0.62 | 0.86 | 1.02 | 0.99 | 0.26 | 0.82 | 0.69 | 0.71 | 0.97 | 0.57 | 0.44 | 1.07 |
| Zfp871 | 1.27 | 1.61 | 1.10 | 2.62 | 0.33 | 1.12 | 1.08 | 1.37 | 1.19 | 0.79 | 0.52 | 0.99 |
| Zfp942 | 0.62 | 0.96 | 0.65 | 2.22 | 0.45 | 0.95 | 0.80 | 0.94 | 0.84 | 0.58 | 0.75 | 0.96 |
| Zfp943 | 0.83 | 1.37 | 0.81 | 2.77 | 0.44 | 1.06 | 0.97 | 0.94 | 0.83 | 0.46 | 0.42 | 0.97 |
| Zfp948 | 1.40 | 1.69 | 1.43 | 2.60 | 0.34 | 1.29 | 1.56 | 1.55 | 1.35 | 0.46 | 0.29 | 0.90 |
| Zfp955a | 0.76 | 1.00 | 0.73 | 1.70 | 0.35 | 0.91 | 0.90 | 0.95 | 0.95 | 1.00 | 0.55 | 0.99 |
| Zfp955b | 0.80 | 1.00 | 0.97 | 1.71 | 0.35 | 0.89 | 0.99 | 0.93 | 1.14 | 0.87 | 0.52 | 1.05 |
| Zfp961 | 1.10 | 1.00 | 0.99 | 1.03 | 0.17 | 0.71 | 0.55 | 0.59 | 0.88 | 0.39 | 0.22 | 0.90 |
| Zfx | 1.17 | 2.12 | 1.00 | 1.84 | 0.43 | 1.03 | 0.97 | 1.12 | 1.06 | 0.53 | 0.36 | 0.85 |
| Zfyve9 | 0.77 | 2.12 | 0.98 | 0.80 | 0.27 | 0.80 | 1.36 | 1.60 | 0.92 | 1.00 | 0.80 | 0.80 |
| Zhx3 | 0.86 | 1.00 | 1.80 | 1.45 | 0.60 | 0.79 | 2.18 | 2.69 | 1.68 | 1.17 | 1.53 | 1.75 |
| Zmat5 | 1.10 | 0.66 | 0.80 | 0.19 | 4.44 | 0.80 | 1.15 | 0.75 | 0.83 | 1.73 | 2.51 | 0.96 |
| Zmiz1 | 1.18 | 1.87 | 1.35 | 2.87 | 0.37 | 1.85 | 1.45 | 1.46 | 1.24 | 0.81 | 0.63 | 1.09 |
| Znf512b | 0.75 | 0.90 | 1.02 | 1.07 | 0.27 | 1.06 | 0.98 | 0.93 | 1.10 | 0.58 | 0.50 | 1.04 |
| Znfx1 | 0.95 | 1.44 | 1.21 | 0.76 | 0.28 | 1.01 | 1.42 | 1.39 | 1.29 | 0.57 | 0.58 | 1.09 |
| Zrsr1 | 1.68 | 3.27 | 1.59 | 1.81 | 0.16 | 1.37 | 1.04 | 1.05 | 1.11 | 0.28 | 0.26 | 1.04 |
| Zscan25 | 1.64 | 1.28 | 1.69 | 1.15 | 0.14 | 1.06 | 1.68 | 1.33 | 1.16 | 1.00 | 0.27 | 1.07 |
| Zscan26 | 1.41 | 4.67 | 1.51 | 1.75 | 0.15 | 1.13 | 1.03 | 1.17 | 0.95 | 0.17 | 0.19 | 0.95 |
| l7Rn6 | 1.20 | 1.04 | 1.04 | 1.20 | 1.83 | 1.04 | 0.99 | 0.92 | 0.96 | 0.59 | 1.15 | 0.91 |
| 0610009L18Rik | 1.47 | 0.68 | 0.97 | 0.93 | 7.62 | 1.13 | 1.37 | 1.37 | 1.29 | 1.54 | 2.08 | 1.06 |
| 0610010K14Rik | 0.98 | 0.55 | 0.88 | 0.45 | 8.15 | 1.02 | 0.87 | 0.76 | 0.88 | 2.20 | 3.30 | 0.92 |

Fig. 35- 106

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Zbed6 | 1.00 | 1.00 | 1.00 | 1.57 | 1.00 | 0.83 | 1.00 | 1.00 | 1.00 | 1.59 | 1.00 | 0.70 |
| Zbtb1 | 0.53 | 0.43 | 0.82 | 1.13 | 1.00 | 1.06 | 0.84 | 1.00 | 1.10 | 1.02 | 0.66 | 0.93 |
| Zbtb11 | 0.57 | 0.49 | 0.81 | 1.20 | 1.00 | 1.16 | 1.04 | 1.00 | 1.02 | 0.89 | 0.73 | 1.01 |
| Zbtb12 | 0.75 | 0.71 | 1.10 | 0.90 | 1.00 | 1.19 | 0.86 | 1.00 | 1.00 | 0.72 | 0.72 | 0.88 |
| Zbtb18 | 0.43 | 0.39 | 0.60 | 1.33 | 1.68 | 1.13 | 0.66 | 0.43 | 0.76 | 1.04 | 0.68 | 0.89 |
| Zbtb20 | 1.00 | 1.00 | 1.00 | 0.81 | 1.40 | 1.39 | 0.90 | 1.00 | 1.30 | 1.00 | 1.00 | 1.00 |
| Zbtb25 | 0.76 | 0.72 | 0.78 | 1.04 | 1.00 | 1.07 | 1.21 | 1.00 | 1.10 | 1.05 | 0.87 | 0.82 |
| Zbtb33 | 0.62 | 0.52 | 0.88 | 1.00 | 1.00 | 1.08 | 0.76 | 1.00 | 0.94 | 1.02 | 0.62 | 1.03 |
| Zbtb39 | 0.86 | 0.66 | 0.99 | 1.30 | 1.19 | 1.29 | 1.01 | 1.00 | 1.16 | 0.99 | 0.71 | 0.98 |
| Zc3h11a | 0.86 | 0.78 | 0.95 | 0.91 | 1.03 | 0.87 | 0.73 | 0.57 | 0.79 | 1.01 | 0.87 | 1.02 |
| Zc3h13 | 0.69 | 0.64 | 0.90 | 0.88 | 1.13 | 1.02 | 1.07 | 1.00 | 1.22 | 0.97 | 0.71 | 0.91 |
| Zc3h4 | 0.73 | 0.70 | 0.92 | 1.14 | 2.15 | 1.15 | 1.02 | 1.00 | 1.19 | 1.06 | 0.69 | 0.93 |
| Zc3h6 | 0.66 | 0.69 | 1.05 | 1.16 | 1.00 | 1.14 | 0.96 | 1.00 | 0.97 | 1.24 | 0.75 | 0.88 |
| Zcchc14 | 1.49 | 0.93 | 1.48 | 1.23 | 2.29 | 1.24 | 0.83 | 1.00 | 1.01 | 1.04 | 0.62 | 0.93 |
| Zcchc18 | 2.74 | 2.25 | 2.76 | 1.00 | 1.00 | 1.00 | 1.00 | 1.00 | 1.00 | 1.03 | 1.12 | 1.03 |
| Zcchc2 | 0.88 | 0.77 | 1.10 | 1.19 | 1.00 | 1.14 | 0.92 | 1.00 | 1.11 | 1.24 | 0.80 | 1.12 |
| Zcchc6 | 0.61 | 0.43 | 0.92 | 1.21 | 1.00 | 1.26 | 0.92 | 1.00 | 0.93 | 1.05 | 0.37 | 0.88 |
| Zcchc9 | 0.91 | 0.97 | 0.96 | 0.85 | 2.62 | 0.81 | 0.81 | 0.65 | 0.77 | 0.98 | 0.96 | 1.15 |
| Zdhhc16 | 0.98 | 1.16 | 0.93 | 1.04 | 0.84 | 0.93 | 1.00 | 0.59 | 0.78 | 0.89 | 1.06 | 0.99 |
| Zdhhc21 | 0.69 | 0.56 | 0.74 | 1.08 | 1.00 | 1.01 | 1.22 | 1.00 | 1.30 | 1.15 | 0.92 | 1.13 |
| Zfp146 | 0.76 | 0.59 | 1.09 | 0.97 | 1.00 | 0.98 | 1.01 | 1.00 | 0.86 | 0.88 | 0.39 | 0.91 |
| Zfp160 | 0.82 | 0.67 | 0.95 | 0.88 | 1.13 | 1.01 | 1.05 | 1.00 | 1.16 | 1.02 | 0.63 | 0.97 |
| Zfp217 | 0.58 | 0.44 | 0.87 | 1.12 | 1.00 | 1.06 | 0.98 | 1.00 | 1.16 | 0.97 | 0.64 | 1.02 |
| Zfp219 | 1.09 | 1.14 | 1.10 | 0.80 | 1.90 | 1.05 | 0.85 | 0.53 | 0.98 | 0.91 | 0.66 | 1.00 |
| Zfp266 | 0.68 | 0.59 | 0.86 | 1.09 | 1.00 | 1.00 | 1.26 | 1.00 | 1.39 | 0.86 | 0.56 | 1.11 |
| Zfp280c | 0.86 | 0.90 | 0.86 | 0.80 | 1.00 | 0.79 | 1.37 | 1.00 | 1.35 | 1.01 | 0.86 | 0.83 |
| Zfp280d | 0.50 | 0.56 | 0.54 | 1.02 | 1.00 | 0.76 | 0.99 | 1.00 | 1.06 | 0.96 | 0.74 | 0.99 |
| Zfp367 | 0.36 | 0.34 | 0.39 | 0.69 | 0.77 | 0.68 | 0.66 | 0.93 | 0.66 | 1.10 | 0.73 | 0.99 |
| Zfp36l2 | 1.79 | 2.71 | 2.35 | 1.28 | 1.60 | 1.36 | 1.86 | 0.65 | 1.66 | 0.92 | 0.64 | 0.89 |
| Zfp395 | 0.81 | 0.91 | 0.96 | 0.98 | 1.57 | 1.06 | 0.74 | 0.37 | 0.81 | 0.96 | 0.88 | 0.96 |
| Zfp423 | 1.00 | 1.00 | 1.00 | 1.00 | 1.00 | 1.00 | 1.00 | 1.00 | 1.00 | 1.00 | 1.00 | 1.00 |
| Zfp46 | 0.73 | 0.76 | 1.14 | 1.09 | 1.00 | 0.97 | 0.80 | 1.00 | 0.93 | 0.95 | 0.56 | 1.04 |
| Zfp51 | 0.89 | 0.94 | 1.07 | 1.06 | 1.00 | 0.83 | 1.16 | 1.00 | 1.09 | 1.09 | 0.74 | 0.97 |
| Zfp516 | 1.15 | 0.74 | 1.42 | 1.44 | 1.00 | 1.33 | 1.10 | 1.00 | 1.78 | 1.11 | 0.74 | 0.99 |
| Zfp553 | 1.37 | 1.25 | 1.13 | 1.27 | 0.90 | 1.04 | 1.61 | 1.00 | 1.33 | 1.08 | 0.78 | 0.95 |
| Zfp58 | 0.64 | 0.59 | 0.82 | 0.91 | 0.69 | 0.75 | 0.54 | 1.00 | 0.67 | 0.67 | 0.57 | 0.56 |
| Zfp646 | 0.74 | 0.64 | 0.90 | 1.06 | 1.00 | 1.11 | 0.93 | 1.00 | 1.08 | 0.96 | 0.76 | 0.92 |
| Zfp710 | 0.72 | 0.63 | 0.98 | 1.12 | 1.34 | 1.06 | 0.89 | 1.00 | 1.03 | 0.96 | 0.72 | 0.96 |
| Zfp715 | 0.76 | 0.60 | 1.02 | 1.03 | 1.00 | 0.87 | 1.04 | 1.00 | 1.07 | 1.06 | 0.61 | 1.11 |
| Zfp740 | 0.83 | 0.84 | 0.95 | 1.08 | 1.50 | 1.06 | 0.84 | 0.58 | 0.96 | 0.99 | 0.84 | 1.02 |
| Zfp746 | 0.85 | 0.82 | 0.94 | 1.09 | 1.43 | 1.25 | 2.31 | 2.64 | 2.09 | 0.98 | 0.79 | 1.03 |
| Zfp758 | 0.75 | 0.69 | 1.04 | 0.91 | 1.00 | 1.19 | 0.86 | 1.00 | 1.26 | 0.97 | 0.71 | 1.00 |
| Zfp770 | 0.87 | 0.76 | 0.90 | 0.97 | 1.00 | 1.15 | 0.83 | 1.00 | 1.02 | 0.83 | 0.66 | 0.91 |
| Zfp866 | 0.66 | 0.59 | 0.83 | 0.90 | 1.00 | 0.91 | 0.68 | 1.00 | 0.87 | 0.94 | 0.58 | 0.96 |
| Zfp871 | 0.65 | 0.59 | 0.80 | 0.91 | 0.99 | 0.93 | 0.85 | 1.17 | 0.82 | 1.01 | 0.61 | 1.01 |
| Zfp942 | 0.77 | 0.73 | 0.88 | 0.82 | 1.15 | 0.96 | 0.89 | 0.73 | 0.82 | 0.99 | 0.83 | 0.93 |
| Zfp943 | 0.87 | 0.77 | 0.83 | 0.94 | 2.06 | 0.83 | 0.82 | 0.82 | 0.93 | 1.08 | 0.79 | 1.10 |
| Zfp948 | 1.50 | 1.23 | 1.56 | 0.93 | 1.00 | 0.78 | 1.35 | 1.00 | 1.09 | 1.16 | 0.91 | 0.93 |
| Zfp955a | 0.68 | 0.66 | 0.84 | 1.04 | 1.00 | 0.98 | 1.05 | 1.00 | 1.17 | 1.04 | 0.71 | 0.99 |
| Zfp955b | 0.78 | 0.70 | 0.88 | 1.16 | 1.00 | 1.04 | 0.98 | 1.00 | 1.05 | 1.14 | 0.88 | 0.92 |
| Zfp961 | 0.82 | 0.67 | 0.86 | 0.73 | 1.09 | 0.85 | 0.88 | 1.00 | 0.84 | 0.86 | 0.69 | 0.89 |
| Zfx | 0.63 | 0.56 | 0.78 | 1.07 | 1.00 | 0.95 | 0.94 | 1.00 | 0.98 | 1.07 | 0.65 | 0.98 |
| Zfyve9 | 1.09 | 0.93 | 1.14 | 1.18 | 1.00 | 1.51 | 0.76 | 1.00 | 1.14 | 0.88 | 0.57 | 0.86 |
| Zhx3 | 0.62 | 0.51 | 0.87 | 1.71 | 2.47 | 1.79 | 0.98 | 1.00 | 1.28 | 1.30 | 0.75 | 0.98 |
| Zmat5 | 1.02 | 1.72 | 0.99 | 0.78 | 0.59 | 0.92 | 1.41 | 1.78 | 0.74 | 1.16 | 1.70 | 1.01 |
| Zmiz1 | 0.57 | 0.49 | 0.93 | 1.34 | 2.05 | 1.14 | 1.04 | 1.00 | 1.24 | 1.07 | 0.62 | 0.90 |
| Znf512b | 0.66 | 0.64 | 0.86 | 0.84 | 0.91 | 0.95 | 0.84 | 0.53 | 0.92 | 0.81 | 0.62 | 0.93 |
| Znfx1 | 0.91 | 0.86 | 1.18 | 1.03 | 1.35 | 1.09 | 0.88 | 0.60 | 1.35 | 1.27 | 0.82 | 1.09 |
| Zrsr1 | 1.45 | 1.24 | 1.57 | 1.26 | 1.00 | 1.15 | 1.22 | 1.00 | 1.44 | 1.17 | 0.91 | 1.11 |
| Zscan25 | 0.81 | 0.84 | 1.06 | 1.20 | 1.00 | 1.17 | 1.13 | 1.00 | 0.90 | 1.12 | 0.65 | 0.97 |
| Zscan26 | 0.83 | 0.79 | 1.22 | 1.02 | 1.75 | 0.96 | 0.91 | 1.00 | 0.97 | 0.97 | 0.63 | 1.02 |
| l7Rn6 | 0.97 | 0.91 | 0.97 | 1.00 | 1.83 | 0.87 | 0.91 | 1.32 | 0.99 | 0.88 | 1.34 | 1.15 |
| 0610009L18Rik | 1.79 | 1.48 | 0.98 | 1.07 | 0.62 | 1.61 | 1.00 | 0.91 | 1.00 | 0.77 | 1.38 | 1.76 |
| 0610010K14Rik | 0.93 | 1.35 | 0.82 | 0.85 | 0.51 | 0.81 | 1.26 | 1.38 | 1.33 | 1.02 | 2.10 | 1.02 |

Fig. 35- 107

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Zbed6 | 0.78 | 0.49 | 0.25 | 1.00 | 0.15 | 0.92 | 1.00 | 1.00 | 1.00 | 1.01 | 1.58 | 1.97 |
| Zbtb1 | 0.84 | 0.77 | 0.82 | 1.01 | 0.75 | 0.88 | 1.07 | 1.00 | 0.98 | 0.95 | 0.56 | 1.05 |
| Zbtb11 | 1.01 | 0.98 | 0.94 | 1.07 | 0.66 | 1.12 | 1.05 | 0.91 | 1.18 | 1.00 | 0.61 | 1.08 |
| Zbtb12 | 1.16 | 0.90 | 0.93 | 0.75 | 0.75 | 1.46 | 1.11 | 1.00 | 0.74 | 1.29 | 0.85 | 1.30 |
| Zbtb18 | 1.00 | 1.05 | 0.83 | 0.84 | 0.25 | 0.96 | 1.15 | 1.08 | 1.17 | 0.95 | 0.82 | 0.96 |
| Zbtb20 | 1.00 | 1.00 | 1.00 | 0.98 | 0.11 | 0.79 | 1.19 | 1.47 | 1.23 | 1.00 | 1.08 | 1.49 |
| Zbtb25 | 1.19 | 1.05 | 1.11 | 1.07 | 0.83 | 1.02 | 1.10 | 0.27 | 0.93 | 1.10 | 0.84 | 1.37 |
| Zbtb33 | 1.04 | 0.88 | 0.76 | 1.06 | 0.39 | 0.89 | 1.00 | 1.00 | 1.07 | 1.09 | 0.64 | 1.19 |
| Zbtb39 | 1.05 | 0.99 | 0.76 | 1.30 | 0.81 | 1.13 | 1.31 | 1.00 | 1.08 | 1.19 | 0.75 | 1.26 |
| Zc3h11a | 1.04 | 1.01 | 0.91 | 0.99 | 0.19 | 0.99 | 1.02 | 0.77 | 0.91 | 1.05 | 0.83 | 1.10 |
| Zc3h13 | 0.93 | 0.95 | 0.75 | 0.95 | 0.47 | 0.78 | 1.11 | 1.94 | 1.24 | 0.92 | 0.80 | 1.00 |
| Zc3h4 | 0.97 | 1.11 | 0.81 | 1.12 | 0.27 | 1.03 | 1.11 | 0.52 | 1.12 | 0.90 | 0.67 | 0.99 |
| Zc3h6 | 0.99 | 1.41 | 1.01 | 1.16 | 1.00 | 0.87 | 0.94 | 0.99 | 1.15 | 1.24 | 0.70 | 1.05 |
| Zcchc14 | 1.02 | 1.05 | 1.00 | 1.21 | 0.35 | 1.28 | 1.20 | 0.92 | 1.24 | 0.99 | 1.07 | 1.47 |
| Zcchc18 | 1.33 | 1.54 | 1.38 | 1.20 | 1.00 | 1.75 | 1.31 | 1.14 | 1.05 | 1.92 | 2.78 | 1.94 |
| Zcchc2 | 0.97 | 1.20 | 1.07 | 0.98 | 0.50 | 0.84 | 1.16 | 0.45 | 1.06 | 1.39 | 0.86 | 1.19 |
| Zcchc6 | 1.14 | 1.13 | 0.83 | 1.29 | 0.44 | 0.69 | 1.44 | 1.00 | 1.15 | 0.82 | 0.54 | 1.00 |
| Zcchc9 | 1.13 | 0.93 | 0.95 | 0.89 | 0.29 | 1.06 | 0.99 | 0.88 | 1.09 | 0.99 | 0.72 | 1.02 |
| Zdhhc16 | 0.99 | 0.93 | 0.93 | 1.03 | 2.82 | 1.13 | 0.74 | 0.32 | 0.88 | 1.13 | 0.96 | 1.08 |
| Zdhhc21 | 0.76 | 0.71 | 0.73 | 1.08 | 1.00 | 0.76 | 1.06 | 1.00 | 0.94 | 0.95 | 0.80 | 0.92 |
| Zfp146 | 1.04 | 0.94 | 1.01 | 1.38 | 0.46 | 0.95 | 1.17 | 1.00 | 0.89 | 1.00 | 0.73 | 1.26 |
| Zfp160 | 1.05 | 0.87 | 0.97 | 0.86 | 0.44 | 0.84 | 1.10 | 1.00 | 0.85 | 0.96 | 0.69 | 1.15 |
| Zfp217 | 0.96 | 1.05 | 0.88 | 1.06 | 0.48 | 0.97 | 1.16 | 1.40 | 1.03 | 0.79 | 0.51 | 1.01 |
| Zfp219 | 0.92 | 1.07 | 0.99 | 0.79 | 0.35 | 0.98 | 0.88 | 0.40 | 1.08 | 0.92 | 1.05 | 1.22 |
| Zfp266 | 1.05 | 0.95 | 0.93 | 0.88 | 0.32 | 0.77 | 0.94 | 1.00 | 0.79 | 1.10 | 0.71 | 1.10 |
| Zfp280c | 1.16 | 0.88 | 1.11 | 0.87 | 1.00 | 0.86 | 1.01 | 1.00 | 0.78 | 1.14 | 1.01 | 1.23 |
| Zfp280d | 0.94 | 0.98 | 0.97 | 1.15 | 1.00 | 1.22 | 0.88 | 0.57 | 0.84 | 0.97 | 0.69 | 1.11 |
| Zfp367 | 0.88 | 0.67 | 0.84 | 0.49 | 1.00 | 0.46 | 1.03 | 0.82 | 1.05 | 0.58 | 0.55 | 0.60 |
| Zfp36l2 | 0.99 | 1.00 | 1.09 | 0.99 | 0.15 | 0.89 | 0.91 | 1.00 | 1.00 | 1.64 | 1.59 | 1.92 |
| Zfp395 | 0.97 | 0.98 | 1.04 | 0.60 | 0.34 | 0.82 | 0.87 | 0.60 | 0.88 | 1.13 | 0.99 | 1.18 |
| Zfp423 | 0.97 | 0.83 | 1.09 | 0.63 | 0.24 | 0.65 | 0.86 | 1.30 | 1.00 | 1.21 | 0.89 | 0.85 |
| Zfp46 | 1.10 | 1.22 | 1.34 | 0.87 | 1.00 | 0.90 | 1.12 | 1.00 | 0.86 | 0.90 | 0.69 | 0.95 |
| Zfp51 | 1.00 | 0.72 | 0.82 | 1.08 | 1.00 | 1.11 | 1.30 | 0.75 | 1.25 | 1.01 | 0.81 | 1.23 |
| Zfp516 | 0.97 | 1.09 | 0.80 | 1.11 | 0.51 | 1.00 | 1.01 | 2.44 | 1.05 | 0.89 | 0.65 | 1.39 |
| Zfp553 | 1.17 | 1.20 | 1.04 | 1.14 | 1.00 | 1.28 | 0.89 | 1.12 | 1.10 | 0.99 | 0.92 | 1.12 |
| Zfp58 | 0.73 | 0.51 | 0.69 | 0.55 | 0.43 | 0.84 | 1.56 | 1.80 | 1.20 | 0.80 | 0.55 | 0.86 |
| Zfp646 | 1.01 | 0.98 | 0.88 | 1.31 | 0.44 | 0.87 | 1.39 | 0.52 | 1.12 | 0.98 | 0.85 | 1.25 |
| Zfp710 | 0.88 | 0.97 | 0.82 | 1.02 | 0.73 | 0.80 | 0.91 | 1.00 | 0.93 | 0.73 | 0.60 | 0.82 |
| Zfp715 | 1.01 | 0.92 | 0.92 | 1.18 | 0.64 | 0.89 | 1.22 | 1.00 | 1.09 | 1.13 | 0.62 | 1.18 |
| Zfp740 | 1.28 | 1.16 | 1.12 | 1.10 | 0.29 | 1.23 | 1.09 | 0.75 | 0.94 | 1.05 | 0.82 | 1.13 |
| Zfp746 | 1.12 | 1.14 | 1.21 | 1.18 | 0.86 | 1.21 | 1.05 | 0.41 | 0.92 | 1.16 | 0.94 | 1.04 |
| Zfp758 | 1.19 | 0.83 | 0.92 | 1.13 | 0.86 | 1.11 | 1.24 | 1.00 | 0.89 | 0.98 | 0.68 | 0.97 |
| Zfp770 | 1.06 | 0.78 | 0.85 | 0.84 | 1.00 | 0.64 | 1.51 | 1.00 | 1.02 | 1.00 | 0.71 | 1.13 |
| Zfp866 | 0.92 | 0.87 | 0.94 | 0.95 | 0.59 | 1.00 | 0.95 | 1.00 | 1.13 | 1.02 | 0.57 | 1.17 |
| Zfp871 | 1.16 | 1.05 | 0.95 | 1.75 | 0.24 | 1.19 | 1.10 | 1.00 | 0.85 | 1.02 | 0.66 | 1.15 |
| Zfp942 | 1.01 | 0.91 | 1.12 | 0.84 | 0.85 | 0.95 | 1.06 | 0.63 | 0.97 | 1.04 | 0.77 | 1.08 |
| Zfp943 | 0.96 | 1.11 | 1.05 | 1.03 | 0.79 | 0.90 | 1.01 | 0.44 | 0.98 | 1.06 | 0.74 | 1.06 |
| Zfp948 | 1.10 | 0.98 | 0.94 | 1.03 | 0.44 | 0.88 | 0.72 | 1.00 | 1.14 | 1.00 | 0.83 | 1.25 |
| Zfp955a | 1.00 | 1.02 | 0.91 | 1.10 | 0.77 | 1.03 | 1.04 | 1.10 | 1.14 | 1.20 | 0.69 | 1.33 |
| Zfp955b | 1.00 | 1.01 | 0.94 | 0.90 | 1.00 | 0.84 | 1.19 | 0.70 | 1.16 | 1.24 | 1.14 | 1.29 |
| Zfp961 | 0.95 | 0.97 | 1.02 | 0.81 | 0.74 | 1.01 | 0.76 | 1.00 | 1.03 | 1.18 | 0.69 | 1.15 |
| Zfx | 1.05 | 0.86 | 0.89 | 1.01 | 0.58 | 0.89 | 0.99 | 1.00 | 0.93 | 1.00 | 0.58 | 1.04 |
| Zfyve9 | 1.05 | 1.17 | 0.90 | 1.00 | 1.00 | 0.91 | 0.81 | 1.00 | 0.73 | 0.89 | 1.59 | 0.82 |
| Zhx3 | 1.40 | 1.31 | 0.86 | 1.45 | 0.18 | 0.71 | 1.32 | 0.66 | 1.15 | 1.18 | 1.08 | 1.62 |
| Zmat5 | 1.39 | 0.94 | 1.35 | 0.86 | 1.75 | 0.71 | 1.25 | 1.81 | 0.88 | 0.97 | 1.50 | 0.96 |
| Zmiz1 | 1.00 | 1.04 | 0.79 | 1.51 | 0.23 | 1.30 | 0.99 | 1.61 | 1.05 | 0.89 | 0.66 | 0.95 |
| Znf512b | 0.98 | 0.98 | 0.92 | 0.85 | 0.48 | 1.03 | 1.04 | 0.42 | 1.02 | 0.92 | 0.82 | 1.05 |
| Znfx1 | 1.34 | 1.35 | 1.16 | 0.67 | 0.18 | 0.96 | 1.09 | 0.68 | 1.06 | 1.04 | 0.77 | 0.97 |
| Zrsr1 | 1.16 | 1.50 | 1.50 | 0.99 | 0.43 | 1.04 | 0.94 | 1.00 | 0.96 | 1.29 | 1.06 | 1.29 |
| Zscan25 | 1.03 | 1.06 | 1.01 | 1.34 | 1.00 | 1.26 | 0.99 | 1.00 | 1.07 | 1.08 | 0.85 | 1.16 |
| Zscan26 | 1.04 | 0.93 | 0.97 | 1.03 | 0.23 | 0.98 | 1.15 | 0.71 | 0.90 | 1.07 | 0.72 | 1.08 |
| l7Rn6 | 0.82 | 0.90 | 1.20 | 0.89 | 0.72 | 0.97 | 0.91 | 0.25 | 1.02 | 1.09 | 1.22 | 0.89 |
| 0610009L18Rik | 1.93 | 1.87 | 1.12 | 0.92 | 1.66 | 0.64 | 0.87 | 1.96 | 1.03 | 0.97 | 0.94 | 1.02 |
| 0610010K14Rik | 1.22 | 0.71 | 0.89 | 0.89 | 2.49 | 1.04 | 0.97 | 1.69 | 1.11 | 1.08 | 1.17 | 0.80 |

Fig. 35- 108

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Zbed6 | 1.00 | 1.00 | 1.00 | 0.42 | 1.00 | 0.62 | 1.00 | 1.00 | 1.00 | 1.00 | 1.00 | 1.00 |
| Zbtb1 | 1.43 | 0.77 | 1.29 | 0.83 | 1.00 | 0.97 | 0.66 | 0.19 | 0.89 | 0.28 | 0.62 | 0.73 |
| Zbtb11 | 0.96 | 1.21 | 1.11 | 1.04 | 1.00 | 0.99 | 0.91 | 0.18 | 0.96 | 0.43 | 0.88 | 0.87 |
| Zbtb12 | 1.07 | 0.87 | 0.95 | 0.96 | 0.50 | 1.09 | 0.96 | 0.20 | 1.00 | 0.41 | 0.76 | 0.88 |
| Zbtb18 | 1.02 | 1.05 | 1.07 | 1.10 | 1.60 | 1.04 | 0.86 | 0.18 | 1.07 | 0.65 | 0.84 | 0.84 |
| Zbtb20 | 1.00 | 1.00 | 1.00 | 1.00 | 1.00 | 1.00 | 1.00 | 1.00 | 1.00 | 1.00 | 1.00 | 1.00 |
| Zbtb25 | 0.98 | 1.06 | 1.00 | 0.87 | 1.00 | 0.80 | 0.85 | 0.19 | 1.03 | 0.42 | 1.01 | 0.93 |
| Zbtb33 | 1.15 | 1.42 | 1.61 | 0.98 | 1.00 | 0.94 | 0.74 | 0.12 | 1.06 | 0.56 | 0.81 | 1.11 |
| Zbtb39 | 1.39 | 1.00 | 1.00 | 0.73 | 1.00 | 0.89 | 0.93 | 0.18 | 1.08 | 0.66 | 1.06 | 0.94 |
| Zc3h11a | 0.95 | 1.15 | 1.21 | 0.95 | 0.87 | 0.99 | 0.83 | 0.17 | 1.06 | 0.61 | 0.98 | 1.06 |
| Zc3h13 | 1.27 | 1.08 | 0.99 | 0.98 | 0.52 | 0.94 | 0.78 | 0.16 | 1.02 | 0.58 | 0.71 | 0.78 |
| Zc3h4 | 1.09 | 1.15 | 1.03 | 1.02 | 1.35 | 0.97 | 1.01 | 0.14 | 1.15 | 0.49 | 0.79 | 0.80 |
| Zc3h6 | 1.00 | 1.00 | 1.00 | 0.91 | 1.00 | 0.98 | 0.86 | 0.19 | 1.30 | 1.00 | 0.76 | 0.88 |
| Zcchc14 | 0.82 | 0.78 | 0.96 | 0.92 | 0.81 | 0.98 | 0.89 | 0.09 | 1.16 | 1.00 | 1.00 | 1.00 |
| Zcchc18 | 1.00 | 1.00 | 1.00 | 1.16 | 1.04 | 1.07 | 1.00 | 1.00 | 1.00 | 1.07 | 1.83 | 1.45 |
| Zcchc2 | 0.85 | 0.80 | 1.19 | 0.93 | 1.00 | 0.98 | 0.90 | 0.11 | 1.02 | 0.49 | 1.11 | 1.07 |
| Zcchc6 | 1.19 | 1.62 | 1.11 | 0.93 | 1.00 | 0.99 | 0.83 | 0.16 | 1.04 | 0.22 | 0.84 | 0.72 |
| Zcchc9 | 1.20 | 1.08 | 0.95 | 1.06 | 1.84 | 1.04 | 0.94 | 0.15 | 0.96 | 0.33 | 0.94 | 1.06 |
| Zdhhc16 | 0.90 | 1.03 | 1.04 | 0.93 | 1.00 | 0.99 | 1.02 | 0.98 | 1.10 | 0.89 | 1.12 | 1.11 |
| Zdhhc21 | 1.15 | 1.00 | 1.00 | 0.83 | 1.00 | 0.87 | 0.81 | 0.19 | 0.99 | 0.53 | 0.96 | 0.86 |
| Zfp146 | 1.13 | 0.91 | 0.88 | 1.03 | 1.00 | 1.00 | 0.90 | 0.05 | 1.03 | 0.18 | 0.76 | 0.87 |
| Zfp160 | 1.04 | 1.08 | 1.00 | 0.74 | 0.44 | 0.90 | 0.63 | 0.14 | 0.83 | 0.52 | 1.00 | 1.01 |
| Zfp217 | 1.72 | 0.96 | 0.95 | 0.70 | 1.00 | 1.00 | 0.98 | 0.10 | 1.07 | 0.36 | 0.75 | 0.79 |
| Zfp219 | 1.32 | 0.93 | 1.03 | 1.02 | 1.61 | 0.98 | 1.05 | 0.25 | 0.89 | 0.50 | 0.93 | 0.87 |
| Zfp266 | 0.80 | 0.91 | 1.00 | 0.92 | 1.00 | 0.89 | 0.63 | 0.08 | 0.83 | 0.45 | 0.84 | 0.91 |
| Zfp280c | 1.00 | 0.99 | 1.00 | 0.86 | 1.00 | 1.01 | 0.83 | 0.13 | 1.22 | 0.51 | 1.03 | 1.20 |
| Zfp280d | 0.94 | 1.16 | 1.22 | 0.91 | 1.00 | 0.95 | 0.80 | 0.07 | 1.07 | 0.29 | 0.74 | 0.86 |
| Zfp367 | 1.00 | 1.00 | 1.00 | 0.73 | 0.87 | 0.86 | 0.79 | 0.16 | 0.78 | 0.52 | 0.74 | 0.72 |
| Zfp36l2 | 0.85 | 1.34 | 1.33 | 1.03 | 1.00 | 1.10 | 1.10 | 0.11 | 1.33 | 0.53 | 1.38 | 1.02 |
| Zfp395 | 0.60 | 0.57 | 0.79 | 0.98 | 1.00 | 1.01 | 0.84 | 0.08 | 1.05 | 0.59 | 1.14 | 1.11 |
| Zfp423 | 1.00 | 1.00 | 1.00 | 1.02 | 0.86 | 1.08 | 0.89 | 1.09 | 0.92 | 1.00 | 1.00 | 1.00 |
| Zfp46 | 1.00 | 1.00 | 1.00 | 0.90 | 1.00 | 1.01 | 0.90 | 0.16 | 1.16 | 0.65 | 0.83 | 1.22 |
| Zfp51 | 1.14 | 1.13 | 1.03 | 1.13 | 1.00 | 0.99 | 0.78 | 0.16 | 1.13 | 0.37 | 1.16 | 1.24 |
| Zfp516 | 1.00 | 1.00 | 1.00 | 0.89 | 1.00 | 0.89 | 0.79 | 0.18 | 1.03 | 0.84 | 1.11 | 1.01 |
| Zfp553 | 1.43 | 1.21 | 1.00 | 0.99 | 0.70 | 0.93 | 1.35 | 0.12 | 1.28 | 0.27 | 0.74 | 0.88 |
| Zfp58 | 0.89 | 1.00 | 1.00 | 0.53 | 0.18 | 0.60 | 0.66 | 1.27 | 0.75 | 0.71 | 0.79 | 0.96 |
| Zfp646 | 1.16 | 0.94 | 1.47 | 0.85 | 1.00 | 0.98 | 1.04 | 0.11 | 1.00 | 0.22 | 0.88 | 0.80 |
| Zfp710 | 1.39 | 2.08 | 1.34 | 0.95 | 1.00 | 1.03 | 0.67 | 0.16 | 0.74 | 0.52 | 0.78 | 0.91 |
| Zfp715 | 1.19 | 1.12 | 1.36 | 1.02 | 0.83 | 0.87 | 0.81 | 0.32 | 0.96 | 0.42 | 0.82 | 1.04 |
| Zfp740 | 1.01 | 0.97 | 1.20 | 0.96 | 1.04 | 1.02 | 1.13 | 0.07 | 1.19 | 0.34 | 1.15 | 0.94 |
| Zfp746 | 1.44 | 0.85 | 0.91 | 0.98 | 1.00 | 1.07 | 1.05 | 0.13 | 1.08 | 0.58 | 1.10 | 1.03 |
| Zfp758 | 1.14 | 1.19 | 1.08 | 0.71 | 1.00 | 0.88 | 0.67 | 0.18 | 1.10 | 0.49 | 0.96 | 1.00 |
| Zfp770 | 1.00 | 1.00 | 1.00 | 0.86 | 1.00 | 0.95 | 0.87 | 0.43 | 1.08 | 0.75 | 0.63 | 0.86 |
| Zfp866 | 0.90 | 0.93 | 0.91 | 0.81 | 1.00 | 0.89 | 0.78 | 0.17 | 0.96 | 0.54 | 0.78 | 0.92 |
| Zfp871 | 0.69 | 0.62 | 0.94 | 0.82 | 1.08 | 0.90 | 0.85 | 0.17 | 1.12 | 0.50 | 0.98 | 1.04 |
| Zfp942 | 1.00 | 1.00 | 1.00 | 0.93 | 0.67 | 0.92 | 0.67 | 0.16 | 1.10 | 0.63 | 1.03 | 1.04 |
| Zfp943 | 0.87 | 0.82 | 0.70 | 0.94 | 1.00 | 1.06 | 0.72 | 0.14 | 1.07 | 0.54 | 1.03 | 1.11 |
| Zfp948 | 1.43 | 1.46 | 1.00 | 1.12 | 1.00 | 1.08 | 0.94 | 0.19 | 1.27 | 0.50 | 0.84 | 1.36 |
| Zfp955a | 1.32 | 0.87 | 1.00 | 0.86 | 1.00 | 0.94 | 0.72 | 0.19 | 1.06 | 0.90 | 1.23 | 0.85 |
| Zfp955b | 1.02 | 0.82 | 1.00 | 0.87 | 0.43 | 0.83 | 0.90 | 0.18 | 1.15 | 0.85 | 1.09 | 1.04 |
| Zfp961 | 0.79 | 0.54 | 0.67 | 0.91 | 0.94 | 0.84 | 0.59 | 0.16 | 0.92 | 0.36 | 0.80 | 0.85 |
| Zfx | 1.25 | 1.26 | 1.00 | 0.90 | 0.85 | 0.95 | 0.87 | 0.17 | 1.07 | 0.32 | 0.98 | 0.96 |
| Zfyve9 | 1.20 | 1.00 | 1.13 | 0.99 | 1.00 | 1.01 | 0.76 | 0.13 | 0.82 | 1.00 | 1.00 | 1.00 |
| Zhx3 | 1.59 | 1.87 | 1.00 | 0.74 | 1.25 | 0.87 | 0.87 | 0.40 | 1.13 | 1.00 | 1.00 | 1.00 |
| Zmat5 | 1.23 | 0.39 | 0.71 | 1.37 | 0.60 | 1.05 | 1.09 | 4.34 | 1.21 | 2.56 | 1.43 | 1.05 |
| Zmiz1 | 1.26 | 1.15 | 1.18 | 0.99 | 0.74 | 0.97 | 1.03 | 0.17 | 1.19 | 0.49 | 0.84 | 0.80 |
| Znf512b | 1.22 | 1.38 | 1.02 | 0.95 | 0.57 | 1.03 | 0.86 | 0.12 | 0.97 | 0.62 | 0.79 | 0.83 |
| Znfx1 | 1.13 | 0.93 | 1.59 | 1.15 | 0.91 | 1.06 | 1.10 | 0.32 | 1.18 | 0.85 | 1.04 | 1.13 |
| Zrsr1 | 0.84 | 0.63 | 0.86 | 1.01 | 1.00 | 1.01 | 1.05 | 0.17 | 1.37 | 0.26 | 0.96 | 1.03 |
| Zscan25 | 1.20 | 1.09 | 1.49 | 1.15 | 1.00 | 1.25 | 0.97 | 0.06 | 1.15 | 0.46 | 0.91 | 1.00 |
| Zscan26 | 0.76 | 0.76 | 0.92 | 0.89 | 0.68 | 0.95 | 0.91 | 0.05 | 1.11 | 0.22 | 0.96 | 0.92 |
| l7Rn6 | 1.03 | 1.62 | 1.96 | 0.95 | 0.14 | 1.12 | 0.86 | 1.13 | 0.85 | 1.18 | 1.22 | 1.13 |
| 0610009L18Rik | 1.18 | 1.00 | 1.00 | 0.82 | 0.63 | 1.32 | 1.28 | 11.74 | 0.76 | 3.67 | 1.13 | 1.49 |
| 0610010K14Rik | 0.70 | 0.73 | 0.63 | 1.02 | 0.90 | 0.86 | 1.15 | 7.40 | 0.86 | 2.93 | 1.48 | 1.32 |

Fig. 35- 109

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| 0610037L13Rik | 0.98 | 0.64 | 0.83 | 0.57 | 4.17 | 0.88 | 0.85 | 0.84 | 0.96 | 1.86 | 1.67 | 1.09 |
| 0610040B10Rik | 1.27 | 1.01 | 1.07 | 1.95 | 14.73 | 1.32 | 0.90 | 1.60 | 0.86 | 0.91 | 2.37 | 0.92 |
| 0610043K17Rik | 1.00 | 1.00 | 1.35 | 2.37 | 2.01 | 3.16 | 1.00 | 1.00 | 1.00 | 1.00 | 1.00 | 1.00 |
| 1100001G20Rik | 2.74 | 2.86 | 1.00 | 2.01 | 7.82 | 1.00 | 1.00 | 1.00 | 1.00 | 2.18 | 6.78 | 1.53 |
| 1110002L01Rik | 1.00 | 1.00 | 1.00 | 1.03 | 1.00 | 0.47 | 5.33 | 4.68 | 1.62 | 1.80 | 1.00 | 0.99 |
| 1110004E09Rik | 1.15 | 0.75 | 0.75 | 0.70 | 1.75 | 1.02 | 1.16 | 1.25 | 0.83 | 1.50 | 1.81 | 0.94 |
| 1110017D15Rik | 1.00 | 1.00 | 1.00 | 1.00 | 1.00 | 1.00 | 1.00 | 1.00 | 1.00 | 3.92 | 3.35 | 1.06 |
| 1110020A21Rik | 1.66 | 1.33 | 0.76 | 2.33 | 6.79 | 1.19 | 1.81 | 1.37 | 0.74 | 2.21 | 1.53 | 1.45 |
| 1110034G24Rik | 1.80 | 1.29 | 1.05 | 0.86 | 2.79 | 0.87 | 1.00 | 1.17 | 0.70 | 1.35 | 1.47 | 0.82 |
| 1110038B12Rik | 0.81 | 0.58 | 0.56 | 0.35 | 3.41 | 0.67 | 0.68 | 1.11 | 0.48 | 0.77 | 1.43 | 0.64 |
| 1110046J04Rik | 4.02 | 1.53 | 2.02 | 1.00 | 1.80 | 1.00 | 0.92 | 0.91 | 1.61 | 5.44 | 4.97 | 1.70 |
| 1110054M08Rik | 1.05 | 0.51 | 0.84 | 1.24 | 11.83 | 1.04 | 0.89 | 0.86 | 0.87 | 1.63 | 1.97 | 0.88 |
| 1110065P20Rik | 1.24 | 0.69 | 0.91 | 0.44 | 6.42 | 0.83 | 1.05 | 0.74 | 0.76 | 1.66 | 2.85 | 0.80 |
| 1190002F15Rik | 1.00 | 1.00 | 1.00 | 1.00 | 1.00 | 1.00 | 1.00 | 1.00 | 1.00 | 2.85 | 2.41 | 0.92 |
| 1190005I06Rik | 0.69 | 0.78 | 1.93 | 0.36 | 10.67 | 1.04 | 0.97 | 0.52 | 0.76 | 2.21 | 3.66 | 0.73 |
| 1190007I07Rik | 1.69 | 1.19 | 0.85 | 1.39 | 5.47 | 1.33 | 0.87 | 0.79 | 1.33 | 0.72 | 1.32 | 0.65 |
| 1300002E11Rik | 0.87 | 0.74 | 0.84 | 2.29 | 5.56 | 1.54 | 0.77 | 0.99 | 0.69 | 0.89 | 1.07 | 0.91 |
| 1500009C09Rik | 1.00 | 1.00 | 1.00 | 1.00 | 0.19 | 1.00 | 1.00 | 1.00 | 1.00 | 1.00 | 1.00 | 1.00 |
| 1500012F01Rik | 2.05 | 0.98 | 0.86 | 0.41 | 9.35 | 1.91 | 1.78 | 1.08 | 1.08 | 2.09 | 3.82 | 1.30 |
| 1500015O10Rik | 0.69 | 1.09 | 1.95 | 1.00 | 1.00 | 1.00 | 2.19 | 0.41 | 0.72 | 2.14 | 1.00 | 1.00 |
| 1600002K03Rik | 1.69 | 0.64 | 1.31 | 0.55 | 16.20 | 1.03 | 1.14 | 0.64 | 0.87 | 2.55 | 3.99 | 1.09 |
| 1600014C23Rik | 1.00 | 1.00 | 1.00 | 1.00 | 1.02 | 1.01 | 1.25 | 1.00 | 1.58 | 1.00 | 1.00 | 1.00 |
| 1600020E01Rik | 2.04 | 0.64 | 1.03 | 0.65 | 12.73 | 1.07 | 1.25 | 1.06 | 1.29 | 3.01 | 5.06 | 0.90 |
| 1700001O22Rik | 4.52 | 1.61 | 2.18 | 1.00 | 6.28 | 1.18 | 1.00 | 0.98 | 1.00 | 1.48 | 1.04 | 1.00 |
| 1700003E16Rik | 1.00 | 1.00 | 1.00 | 1.00 | 0.84 | 1.00 | 0.67 | 0.75 | 0.83 | 2.16 | 2.10 | 1.10 |
| 1700003F12Rik | 1.00 | 1.00 | 1.00 | 1.00 | 7.73 | 1.00 | 1.00 | 1.00 | 1.00 | 2.96 | 5.88 | 1.00 |
| 1700003G13Rik | 1.00 | 1.00 | 1.00 | 1.00 | 1.00 | 1.00 | 1.00 | 1.00 | 1.00 | 1.00 | 1.00 | 1.00 |
| 1700007L15Rik | 1.35 | 1.49 | 0.83 | 0.68 | 2.88 | 1.08 | 1.07 | 0.83 | 1.18 | 0.80 | 1.22 | 1.50 |
| 1700008K24Rik | 1.00 | 1.00 | 1.00 | 1.00 | 1.00 | 1.00 | 1.00 | 1.00 | 1.00 | 1.37 | 1.00 | 1.00 |
| 1700009N14Rik | 1.00 | 1.00 | 1.00 | 1.00 | 1.00 | 1.00 | 1.00 | 1.00 | 1.00 | 1.00 | 1.00 | 1.00 |
| 1700009P17Rik | 1.10 | 2.25 | 1.51 | 4.31 | 16.46 | 4.67 | 2.64 | 1.94 | 1.03 | 2.33 | 3.55 | 0.93 |
| 1700012A03Rik | 1.00 | 1.00 | 1.00 | 1.00 | 1.00 | 1.00 | 1.00 | 1.00 | 1.00 | 1.65 | 1.00 | 1.00 |
| 1700017B05Rik | 2.24 | 2.54 | 2.28 | 1.64 | 3.15 | 1.66 | 1.54 | 1.66 | 1.48 | 2.17 | 1.81 | 1.28 |
| 1700025F24Rik | 1.00 | 1.00 | 1.00 | 1.00 | 1.00 | 1.00 | 1.00 | 1.00 | 1.00 | 1.00 | 1.00 | 1.00 |
| 1700027A15Rik | 1.00 | 1.00 | 1.00 | 1.00 | 1.00 | 1.00 | 1.00 | 1.00 | 1.00 | 1.06 | 1.00 | 1.00 |
| 1700029I15Rik | 1.00 | 1.00 | 1.00 | 0.74 | 6.58 | 1.00 | 1.00 | 1.00 | 1.00 | 2.87 | 3.24 | 1.00 |
| 1700037C18Rik | 1.04 | 0.66 | 0.75 | 0.45 | 5.89 | 1.45 | 0.91 | 1.02 | 0.78 | 2.65 | 3.57 | 1.26 |
| 1700047M11Rik | 1.00 | 1.00 | 1.00 | 1.00 | 0.93 | 1.00 | 1.00 | 1.00 | 1.00 | 2.74 | 1.00 | 1.00 |
| 1700057H15Rik | 1.00 | 1.00 | 1.00 | 1.00 | 1.00 | 1.00 | 1.00 | 1.00 | 1.00 | 1.00 | 1.00 | 1.00 |
| 1700084C01Rik | 1.00 | 1.00 | 1.00 | 1.00 | 1.00 | 1.00 | 1.00 | 1.00 | 1.00 | 0.26 | 0.23 | 0.12 |
| 1700084E18Rik | 1.11 | 0.95 | 1.60 | 0.39 | 6.54 | 1.25 | 1.06 | 0.81 | 0.35 | 0.94 | 2.66 | 1.61 |
| 1700101I11Rik | 6.72 | 10.37 | 8.78 | 2.63 | 4.36 | 1.46 | 2.02 | 2.69 | 2.04 | 1.44 | 1.28 | 1.00 |
| 1700102H20Rik | 1.00 | 0.87 | 1.00 | 1.00 | 1.00 | 1.00 | 1.00 | 0.91 | 0.50 | 3.67 | 1.83 | 1.00 |
| 1700112E06Rik | 1.00 | 0.87 | 1.00 | 0.63 | 14.88 | 1.42 | 1.00 | 0.61 | 0.62 | 1.69 | 2.88 | 0.91 |
| 1700113A16Rik | 1.31 | 0.64 | 0.82 | 1.29 | 4.88 | 0.93 | 0.78 | 0.67 | 0.66 | 1.48 | 3.17 | 0.91 |
| 1700121N20Rik | 1.00 | 1.00 | 1.00 | 1.00 | 1.00 | 1.00 | 1.00 | 1.00 | 1.00 | 1.00 | 1.00 | 1.00 |
| 1700123L14Rik | 1.00 | 1.00 | 1.00 | 1.00 | 1.00 | 1.00 | 1.00 | 1.00 | 1.00 | 1.00 | 1.00 | 1.00 |
| 1810009A15Rik | 1.05 | 0.87 | 0.90 | 1.16 | 5.08 | 1.39 | 1.01 | 0.78 | 0.75 | 1.23 | 2.07 | 0.92 |
| 1810009J06Rik | 1.00 | 1.00 | 1.00 | 1.00 | 1.00 | 1.00 | 1.00 | 1.00 | 1.00 | 1.00 | 1.00 | 1.00 |
| 1810010H24Rik | 0.79 | 0.39 | 0.45 | 1.47 | 5.54 | 1.99 | 0.77 | 0.81 | 0.82 | 1.05 | 1.18 | 0.78 |
| 1810012K16Rik | 1.00 | 1.00 | 1.00 | 1.00 | 1.00 | 1.00 | 1.00 | 1.00 | 1.00 | 1.00 | 1.00 | 1.00 |
| 1810022K09Rik | 1.33 | 0.34 | 0.68 | 0.34 | 3.64 | 0.65 | 1.30 | 0.50 | 0.88 | 1.63 | 2.92 | 0.64 |
| 1810026B05Rik | 1.46 | 1.34 | 1.44 | 1.43 | 5.62 | 1.05 | 0.75 | 0.82 | 0.83 | 1.84 | 2.38 | 0.76 |
| 1810032O08Rik | 2.91 | 1.31 | 2.10 | 0.84 | 6.90 | 0.95 | 1.40 | 1.60 | 0.99 | 2.69 | 3.85 | 1.38 |
| 1810044D09Rik | 1.00 | 0.74 | 0.96 | 0.38 | 10.77 | 2.37 | 1.42 | 1.03 | 1.31 | 4.20 | 3.54 | 0.67 |
| 1810053B23Rik | 1.00 | 1.00 | 1.00 | 1.00 | 1.00 | 1.00 | 1.00 | 1.00 | 1.00 | 1.00 | 1.00 | 1.00 |
| 1810058I24Rik | 1.86 | 1.00 | 1.23 | 1.25 | 8.64 | 1.60 | 1.11 | 1.12 | 1.06 | 1.40 | 2.09 | 1.07 |
| 2010005H15Rik | 1.00 | 1.00 | 1.00 | 1.00 | 1.00 | 1.00 | 1.00 | 1.00 | 1.00 | 6.51 | 2.23 | 1.00 |
| 2010010A06Rik | 1.00 | 1.00 | 1.00 | 1.00 | 1.00 | 1.00 | 1.00 | 1.18 | 1.00 | 0.33 | 0.36 | 0.53 |
| 2010107E04Rik | 1.06 | 0.49 | 0.80 | 0.41 | 9.63 | 0.89 | 0.88 | 0.77 | 0.80 | 2.70 | 3.98 | 0.87 |
| 2010109I03Rik | 1.00 | 1.00 | 1.00 | 1.00 | 1.00 | 1.00 | 1.00 | 1.00 | 1.00 | 2.80 | 3.54 | 1.26 |
| 2010300C02Rik | 1.00 | 1.00 | 1.00 | 1.00 | 0.23 | 1.00 | 1.00 | 1.00 | 1.00 | 1.73 | 1.84 | 1.12 |
| 2010320M18Rik | 1.18 | 0.74 | 0.93 | 0.49 | 2.31 | 0.71 | 0.97 | 0.69 | 0.74 | 1.10 | 1.93 | 1.19 |
| 2200002D01Rik | 1.00 | 0.71 | 0.89 | 0.51 | 4.47 | 1.67 | 1.06 | 1.00 | 2.07 | 3.56 | 5.88 | 1.15 |

Fig. 35-110

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| 0610037L13Rik | 1.24 | 1.55 | 0.80 | 0.89 | 0.72 | 0.74 | 1.13 | 1.18 | 1.17 | 1.22 | 1.31 | 1.12 |
| 0610040B10Rik | 2.64 | 2.90 | 1.87 | 0.86 | 0.59 | 1.46 | 0.89 | 0.91 | 1.48 | 1.79 | 1.71 | 0.60 |
| 0610043K17Rik | 1.55 | 1.49 | 1.21 | 0.49 | 0.39 | 0.15 | 0.82 | 1.40 | 1.10 | 1.00 | 1.00 | 1.00 |
| 1100001G20Rik | 0.84 | 0.97 | 1.00 | 1.00 | 1.00 | 1.00 | 1.29 | 1.86 | 1.29 | 1.00 | 1.00 | 1.00 |
| 1110002L01Rik | 0.54 | 0.50 | 0.74 | 0.84 | 1.25 | 0.96 | 0.64 | 1.02 | 0.70 | 0.97 | 0.92 | 1.01 |
| 1110004E09Rik | 0.86 | 1.19 | 0.76 | 1.10 | 0.92 | 0.95 | 1.05 | 0.97 | 1.01 | 1.14 | 1.42 | 0.85 |
| 1110017D15Rik | 1.00 | 1.00 | 1.00 | 1.00 | 0.95 | 1.00 | 1.00 | 1.28 | 1.00 | 1.00 | 1.00 | 1.00 |
| 1110020A21Rik | 1.15 | 1.81 | 0.80 | 1.08 | 0.69 | 0.60 | 1.17 | 2.08 | 0.76 | 1.22 | 1.88 | 1.15 |
| 1110034G24Rik | 1.35 | 1.70 | 1.09 | 1.10 | 0.89 | 0.50 | 2.77 | 8.03 | 2.17 | 0.90 | 1.35 | 0.99 |
| 1110038B12Rik | 1.03 | 1.22 | 0.79 | 0.80 | 0.84 | 0.76 | 1.21 | 1.01 | 0.98 | 0.75 | 1.36 | 0.78 |
| 1110046J04Rik | 1.14 | 1.28 | 1.09 | 1.00 | 0.83 | 1.00 | 1.00 | 1.39 | 1.00 | 1.00 | 1.13 | 1.15 |
| 1110054M08Rik | 1.68 | 1.69 | 1.28 | 0.87 | 0.83 | 0.91 | 1.15 | 1.52 | 1.04 | 0.99 | 1.79 | 0.76 |
| 1110065P20Rik | 1.13 | 1.41 | 0.81 | 0.79 | 0.73 | 0.93 | 0.84 | 1.49 | 0.80 | 0.94 | 1.60 | 0.99 |
| 1190002F15Rik | 0.82 | 1.19 | 0.60 | 1.02 | 0.93 | 1.00 | 1.00 | 1.00 | 1.00 | 0.74 | 2.15 | 2.12 |
| 1190005I06Rik | 0.70 | 1.65 | 0.49 | 0.56 | 0.59 | 1.89 | 0.41 | 1.38 | 0.77 | 1.37 | 2.38 | 0.99 |
| 1190007I07Rik | 0.71 | 1.20 | 0.95 | 0.67 | 0.81 | 1.07 | 0.79 | 0.72 | 0.71 | 0.78 | 1.84 | 1.63 |
| 1300002E11Rik | 0.87 | 0.95 | 0.79 | 0.88 | 1.17 | 0.89 | 1.34 | 0.76 | 1.11 | 0.94 | 1.03 | 0.99 |
| 1500009C09Rik | 1.00 | 1.00 | 1.00 | 1.00 | 1.00 | 1.00 | 1.00 | 1.00 | 1.00 | 1.00 | 1.00 | 1.00 |
| 1500012F01Rik | 1.33 | 1.97 | 0.99 | 0.61 | 0.91 | 0.98 | 1.45 | 1.41 | 0.91 | 0.64 | 2.47 | 1.24 |
| 1500015O10Rik | 1.00 | 1.00 | 1.00 | 1.00 | 1.00 | 1.00 | 1.00 | 1.00 | 1.00 | 1.00 | 1.00 | 1.00 |
| 1600002K03Rik | 1.32 | 1.47 | 0.83 | 0.78 | 0.66 | 1.00 | 1.09 | 2.54 | 0.68 | 1.60 | 1.85 | 1.12 |
| 1600014C23Rik | 1.00 | 1.00 | 1.00 | 1.00 | 1.00 | 1.00 | 1.00 | 1.00 | 1.00 | 1.00 | 1.00 | 1.00 |
| 1600020E01Rik | 1.08 | 1.20 | 0.85 | 1.36 | 0.52 | 0.68 | 0.52 | 1.17 | 0.83 | 0.80 | 2.81 | 0.68 |
| 1700001O22Rik | 1.00 | 1.00 | 1.01 | 1.00 | 0.75 | 0.81 | 1.00 | 1.00 | 1.00 | 0.72 | 0.59 | 0.75 |
| 1700003E16Rik | 1.00 | 1.00 | 1.00 | 0.75 | 0.60 | 0.76 | 0.48 | 1.00 | 0.61 | 0.81 | 0.71 | 0.79 |
| 1700003F12Rik | 1.75 | 1.48 | 1.36 | 1.00 | 1.31 | 1.00 | 1.00 | 1.48 | 1.00 | 1.00 | 1.00 | 1.00 |
| 1700003G13Rik | 1.00 | 1.00 | 1.00 | 1.00 | 1.00 | 1.00 | 1.00 | 1.00 | 1.00 | 1.00 | 1.00 | 1.00 |
| 1700007L15Rik | 1.00 | 1.33 | 0.92 | 0.72 | 0.44 | 0.54 | 1.10 | 0.76 | 0.79 | 0.70 | 0.68 | 0.89 |
| 1700008K24Rik | 1.00 | 1.00 | 1.00 | 1.00 | 1.00 | 1.00 | 1.00 | 1.00 | 1.00 | 1.00 | 1.00 | 1.00 |
| 1700009N14Rik | 1.00 | 1.00 | 1.00 | 1.00 | 1.00 | 1.00 | 1.00 | 1.00 | 1.00 | 1.00 | 1.00 | 1.00 |
| 1700009P17Rik | 4.67 | 5.12 | 1.46 | 5.16 | 8.19 | 5.78 | 1.44 | 3.32 | 1.13 | 1.79 | 3.67 | 1.90 |
| 1700012A03Rik | 1.00 | 1.00 | 1.00 | 1.00 | 1.00 | 1.00 | 1.00 | 1.00 | 1.00 | 1.00 | 1.00 | 1.00 |
| 1700017B05Rik | 0.91 | 0.94 | 0.94 | 1.02 | 0.68 | 0.94 | 3.00 | 6.65 | 1.94 | 1.08 | 0.99 | 1.04 |
| 1700025F24Rik | 1.00 | 1.00 | 1.00 | 1.00 | 1.00 | 1.00 | 1.00 | 1.00 | 1.00 | 1.00 | 1.00 | 1.00 |
| 1700027A15Rik | 1.00 | 1.00 | 1.00 | 1.00 | 1.24 | 1.00 | 1.00 | 1.00 | 1.00 | 1.00 | 1.00 | 1.00 |
| 1700029I15Rik | 0.92 | 1.00 | 1.00 | 1.00 | 0.51 | 1.00 | 1.00 | 4.13 | 1.00 | 1.00 | 1.00 | 0.52 |
| 1700037C18Rik | 1.32 | 1.23 | 1.03 | 0.91 | 0.51 | 0.68 | 1.00 | 8.84 | 1.00 | 1.14 | 1.63 | 0.70 |
| 1700047M11Rik | 1.00 | 1.00 | 1.00 | 1.00 | 1.00 | 1.00 | 0.92 | 1.06 | 1.00 | 1.00 | 0.85 | 1.00 |
| 1700057H15Rik | 1.00 | 1.00 | 1.00 | 1.00 | 1.00 | 1.00 | 1.00 | 1.00 | 1.00 | 1.00 | 1.00 | 1.00 |
| 1700084C01Rik | 8.51 | 5.86 | 6.78 | 1.00 | 1.00 | 1.00 | 1.00 | 1.00 | 1.00 | 1.00 | 1.00 | 1.00 |
| 1700084E18Rik | 1.62 | 1.42 | 0.77 | 0.74 | 0.84 | 0.96 | 1.90 | 1.62 | 0.59 | 1.00 | 1.43 | 1.67 |
| 1700101I11Rik | 1.00 | 1.00 | 1.00 | 1.59 | 1.19 | 1.29 | 1.00 | 1.00 | 1.00 | 1.00 | 1.00 | 1.00 |
| 1700102H20Rik | 1.00 | 1.00 | 1.00 | 0.50 | 2.56 | 0.88 | 1.00 | 0.55 | 1.00 | 1.00 | 1.00 | 1.00 |
| 1700112E06Rik | 1.40 | 1.27 | 1.42 | 0.97 | 0.76 | 1.64 | 1.00 | 2.31 | 1.00 | 1.64 | 1.07 | 0.56 |
| 1700113A16Rik | 1.22 | 1.57 | 0.95 | 0.83 | 0.96 | 0.87 | 0.94 | 1.24 | 0.96 | 1.07 | 1.95 | 1.11 |
| 1700121N20Rik | 1.00 | 1.00 | 1.00 | 1.00 | 1.00 | 1.00 | 1.00 | 1.00 | 1.00 | 1.00 | 1.00 | 1.00 |
| 1700123L14Rik | 1.00 | 1.00 | 1.00 | 1.00 | 1.00 | 1.00 | 1.00 | 1.00 | 1.00 | 1.00 | 1.00 | 1.00 |
| 1810009A15Rik | 1.13 | 1.19 | 1.10 | 1.00 | 0.86 | 0.88 | 0.93 | 0.83 | 1.15 | 0.72 | 1.31 | 0.93 |
| 1810009J06Rik | 1.00 | 1.00 | 1.00 | 1.00 | 1.00 | 1.00 | 1.00 | 1.00 | 1.00 | 1.18 | 4.81 | 1.00 |
| 1810010H24Rik | 2.39 | 1.80 | 0.89 | 1.01 | 1.47 | 1.01 | 1.51 | 1.94 | 1.44 | 0.82 | 1.23 | 0.91 |
| 1810012K16Rik | 1.00 | 1.00 | 0.96 | 1.00 | 1.00 | 1.00 | 1.00 | 1.00 | 1.00 | 1.10 | 1.00 | 1.39 |
| 1810022K09Rik | 0.79 | 0.96 | 1.42 | 0.90 | 0.36 | 0.83 | 0.47 | 1.84 | 0.84 | 2.03 | 1.87 | 0.60 |
| 1810026B05Rik | 0.89 | 0.92 | 0.89 | 0.92 | 0.62 | 0.75 | 1.14 | 0.99 | 1.09 | 0.94 | 1.57 | 0.88 |
| 1810032O08Rik | 1.05 | 1.36 | 1.10 | 0.80 | 0.73 | 1.01 | 1.03 | 3.31 | 0.95 | 1.25 | 1.57 | 1.21 |
| 1810044D09Rik | 1.16 | 2.22 | 0.95 | 0.89 | 0.49 | 0.97 | 1.54 | 1.58 | 1.19 | 0.72 | 1.98 | 1.25 |
| 1810053B23Rik | 0.88 | 0.88 | 0.58 | 1.00 | 1.00 | 1.00 | 3.04 | 4.29 | 6.57 | 1.00 | 1.00 | 1.00 |
| 1810058I24Rik | 1.61 | 2.23 | 1.29 | 0.93 | 0.87 | 1.05 | 0.49 | 0.48 | 0.68 | 1.23 | 1.83 | 1.12 |
| 2010005H15Rik | 1.00 | 1.00 | 1.00 | 1.00 | 0.31 | 1.00 | 1.00 | 1.00 | 1.00 | 1.00 | 1.05 | 1.00 |
| 2010010A06Rik | 5.60 | 3.04 | 1.86 | 0.76 | 1.32 | 1.09 | 0.68 | 0.29 | 0.79 | 0.66 | 1.07 | 1.13 |
| 2010107E04Rik | 1.21 | 1.14 | 0.89 | 0.76 | 0.58 | 0.76 | 0.76 | 1.87 | 0.90 | 1.05 | 1.83 | 0.95 |
| 2010109I03Rik | 1.16 | 1.09 | 1.00 | 1.00 | 1.00 | 1.00 | 1.00 | 1.00 | 1.00 | 1.70 | 2.44 | 1.65 |
| 2010300C02Rik | 0.87 | 0.87 | 0.88 | 1.00 | 1.00 | 1.00 | 1.00 | 1.00 | 1.00 | 0.93 | 0.93 | 0.97 |
| 2010320M18Rik | 1.44 | 1.96 | 0.97 | 0.77 | 0.91 | 0.80 | 1.16 | 0.88 | 1.03 | 1.11 | 1.95 | 1.28 |
| 2200002D01Rik | 1.40 | 1.66 | 1.20 | 0.56 | 0.51 | 1.27 | 1.04 | 3.52 | 1.19 | 0.89 | 1.87 | 0.95 |

Fig. 35-111

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| 0610037L13Rik | 1.19 | 0.95 | 1.14 | 0.92 | 3.45 | 0.95 | 1.05 | 1.98 | 0.93 | 0.92 | 0.97 | 0.87 |
| 0610040B10Rik | 1.93 | 0.94 | 1.69 | 1.72 | 2.53 | 1.77 | 0.96 | 0.79 | 0.97 | 1.10 | 2.21 | 0.93 |
| 0610043K17Rik | 1.00 | 1.00 | 1.00 | 5.15 | 4.47 | 2.16 | 1.00 | 1.00 | 1.00 | 1.00 | 1.00 | 1.00 |
| 1100001G20Rik | 0.61 | 1.07 | 1.00 | 0.77 | 1.11 | 0.67 | 1.00 | 1.00 | 1.00 | 4.97 | 5.67 | 5.14 |
| 1110002L01Rik | 0.96 | 1.02 | 1.00 | 1.07 | 1.00 | 1.00 | 0.85 | 0.56 | 0.96 | 0.95 | 0.44 | 1.06 |
| 1110004E09Rik | 0.90 | 0.88 | 0.76 | 1.30 | 4.34 | 1.19 | 0.98 | 1.10 | 0.99 | 0.98 | 1.34 | 1.03 |
| 1110017D15Rik | 1.00 | 1.00 | 1.00 | 1.51 | 9.76 | 4.13 | 0.85 | 3.95 | 0.86 | 1.00 | 1.00 | 1.00 |
| 1110020A21Rik | 1.34 | 0.93 | 1.01 | 1.18 | 0.68 | 0.75 | 0.81 | 0.89 | 0.91 | 0.71 | 1.22 | 0.89 |
| 1110034G24Rik | 0.87 | 1.58 | 1.04 | 1.45 | 2.37 | 1.31 | 0.80 | 1.15 | 1.11 | 0.98 | 1.07 | 0.86 |
| 1110038B12Rik | 0.38 | 0.58 | 0.58 | 1.01 | 8.99 | 1.22 | 0.69 | 0.49 | 0.68 | 0.87 | 1.11 | 0.82 |
| 1110046J04Rik | 1.10 | 1.00 | 1.02 | 0.97 | 1.01 | 0.69 | 1.69 | 4.57 | 2.03 | 1.00 | 1.49 | 1.02 |
| 1110054M08Rik | 1.24 | 1.28 | 1.29 | 0.72 | 1.23 | 0.84 | 0.54 | 1.79 | 0.71 | 0.75 | 0.92 | 1.03 |
| 1110065P20Rik | 0.99 | 1.00 | 1.05 | 0.83 | 2.23 | 0.99 | 0.90 | 1.90 | 1.01 | 0.91 | 1.94 | 1.13 |
| 1190002F15Rik | 0.95 | 0.65 | 0.46 | 1.00 | 1.00 | 1.00 | 1.00 | 1.00 | 1.00 | 0.54 | 0.82 | 0.56 |
| 1190005I06Rik | 0.67 | 1.40 | 1.37 | 0.31 | 0.97 | 0.86 | 0.76 | 2.48 | 1.01 | 1.00 | 2.68 | 0.69 |
| 1190007I07Rik | 1.05 | 0.59 | 1.04 | 0.67 | 0.49 | 1.09 | 0.76 | 1.32 | 1.03 | 1.23 | 1.57 | 0.93 |
| 1300002E11Rik | 0.71 | 0.78 | 1.16 | 2.29 | 2.44 | 1.35 | 0.95 | 0.81 | 0.91 | 1.07 | 0.96 | 1.11 |
| 1500009C09Rik | 0.29 | 0.26 | 0.21 | 1.00 | 1.00 | 1.00 | 1.38 | 1.84 | 0.83 | 1.00 | 8.95 | 1.00 |
| 1500012F01Rik | 1.39 | 2.91 | 1.72 | 1.46 | 2.45 | 2.18 | 1.00 | 1.11 | 1.01 | 1.20 | 1.35 | 1.02 |
| 1500015O10Rik | 1.00 | 1.00 | 1.00 | 1.27 | 4.73 | 2.79 | 0.67 | 1.27 | 0.80 | 0.76 | 1.30 | 0.45 |
| 1600002K03Rik | 0.95 | 0.88 | 0.98 | 1.44 | 3.37 | 1.00 | 0.62 | 2.85 | 1.27 | 1.02 | 1.60 | 1.07 |
| 1600014C23Rik | 1.00 | 1.00 | 1.00 | 1.00 | 1.00 | 1.00 | 3.19 | 11.85 | 1.94 | 1.00 | 1.00 | 1.00 |
| 1600020E01Rik | 2.18 | 1.26 | 1.55 | 0.72 | 4.60 | 0.86 | 0.72 | 2.64 | 1.40 | 1.07 | 1.24 | 1.09 |
| 1700001O22Rik | 1.26 | 1.34 | 0.82 | 1.32 | 1.06 | 1.52 | 0.77 | 1.63 | 1.05 | 1.00 | 1.00 | 1.00 |
| 1700003E16Rik | 0.93 | 0.73 | 0.84 | 2.00 | 2.98 | 1.78 | 0.97 | 1.25 | 1.06 | 1.00 | 1.54 | 1.00 |
| 1700003F12Rik | 1.00 | 1.00 | 1.00 | 2.72 | 8.77 | 0.99 | 0.85 | 3.62 | 0.98 | 0.94 | 0.91 | 0.38 |
| 1700003G13Rik | 1.00 | 1.00 | 1.00 | 1.00 | 1.00 | 1.00 | 0.46 | 2.94 | 2.79 | 1.00 | 1.00 | 1.00 |
| 1700007L15Rik | 0.78 | 0.92 | 1.68 | 0.57 | 1.00 | 0.82 | 0.76 | 0.76 | 0.90 | 1.17 | 0.87 | 0.75 |
| 1700008K24Rik | 1.00 | 1.00 | 1.00 | 2.93 | 1.00 | 1.00 | 0.86 | 1.01 | 0.95 | 1.00 | 1.00 | 1.00 |
| 1700009N14Rik | 1.00 | 1.00 | 1.00 | 3.45 | 1.00 | 1.00 | 0.89 | 0.74 | 0.87 | 1.00 | 1.00 | 1.00 |
| 1700009P17Rik | 2.70 | 2.30 | 1.23 | 1.75 | 6.40 | 2.39 | 0.83 | 1.08 | 0.80 | 1.67 | 1.60 | 1.09 |
| 1700012A03Rik | 1.00 | 1.00 | 1.00 | 3.07 | 5.71 | 1.00 | 0.98 | 2.94 | 1.00 | 1.00 | 1.00 | 1.00 |
| 1700017B05Rik | 1.11 | 0.88 | 1.17 | 2.57 | 3.42 | 2.58 | 1.04 | 1.38 | 1.14 | 1.43 | 1.48 | 1.34 |
| 1700025F24Rik | 1.00 | 1.00 | 1.00 | 1.00 | 1.00 | 1.00 | 7.20 | 6.37 | 5.36 | 1.00 | 1.00 | 1.00 |
| 1700027A15Rik | 1.00 | 1.00 | 1.00 | 4.18 | 10.45 | 1.42 | 0.89 | 2.37 | 0.96 | 1.00 | 0.61 | 1.00 |
| 1700029I15Rik | 1.00 | 1.00 | 1.00 | 1.03 | 1.22 | 1.77 | 0.86 | 4.03 | 0.76 | 1.00 | 1.56 | 1.00 |
| 1700037C18Rik | 0.99 | 0.88 | 0.94 | 1.39 | 0.71 | 0.54 | 0.84 | 2.90 | 1.08 | 1.28 | 0.91 | 0.82 |
| 1700047M11Rik | 1.00 | 1.00 | 1.00 | 1.00 | 2.17 | 1.00 | 1.41 | 3.41 | 0.88 | 1.07 | 2.69 | 1.00 |
| 1700057H15Rik | 1.00 | 1.00 | 1.00 | 1.00 | 1.00 | 1.00 | 1.00 | 16.32 | 1.00 | 1.00 | 1.00 | 1.00 |
| 1700084C01Rik | 1.00 | 1.00 | 1.00 | 1.00 | 1.00 | 1.00 | 1.38 | 1.24 | 2.08 | 1.00 | 2.09 | 1.42 |
| 1700084E18Rik | 0.60 | 2.65 | 0.86 | 1.36 | 6.04 | 1.07 | 0.62 | 1.89 | 1.01 | 0.74 | 1.30 | 1.64 |
| 1700101I11Rik | 2.33 | 2.38 | 1.98 | 1.29 | 1.00 | 1.00 | 0.72 | 1.43 | 1.07 | 1.00 | 1.00 | 1.00 |
| 1700102H20Rik | 1.00 | 1.00 | 1.00 | 1.00 | 1.00 | 1.00 | 1.70 | 0.71 | 0.89 | 1.00 | 0.87 | 1.00 |
| 1700112E06Rik | 0.69 | 1.49 | 2.06 | 0.68 | 0.51 | 0.68 | 0.78 | 2.41 | 0.79 | 0.63 | 1.52 | 1.09 |
| 1700113A16Rik | 1.28 | 1.30 | 1.26 | 0.89 | 3.41 | 0.91 | 0.82 | 0.84 | 0.68 | 1.21 | 1.45 | 0.84 |
| 1700121N20Rik | 1.00 | 1.00 | 1.00 | 1.00 | 1.00 | 1.00 | 6.42 | 16.20 | 7.06 | 1.00 | 1.00 | 1.00 |
| 1700123L14Rik | 1.00 | 1.00 | 1.00 | 2.39 | 1.00 | 1.00 | 0.99 | 0.70 | 1.00 | 1.00 | 1.00 | 1.00 |
| 1810009A15Rik | 1.03 | 0.66 | 0.69 | 1.09 | 5.42 | 1.01 | 0.89 | 1.10 | 1.09 | 1.02 | 1.09 | 0.93 |
| 1810009J06Rik | 1.00 | 2.17 | 2.80 | 1.00 | 1.00 | 1.00 | 1.00 | 1.00 | 1.00 | 1.00 | 5.28 | 1.00 |
| 1810010H24Rik | 1.07 | 0.65 | 1.10 | 0.44 | 1.17 | 1.30 | 1.00 | 2.25 | 0.68 | 1.34 | 1.72 | 1.29 |
| 1810012K16Rik | 1.00 | 1.00 | 1.00 | 1.00 | 1.00 | 1.00 | 2.42 | 34.92 | 2.37 | 1.00 | 1.00 | 1.18 |
| 1810022K09Rik | 0.37 | 0.75 | 1.93 | 1.31 | 4.82 | 0.80 | 1.00 | 0.34 | 0.87 | 1.09 | 1.02 | 1.13 |
| 1810026B05Rik | 1.17 | 0.98 | 1.27 | 0.83 | 1.19 | 1.15 | 0.85 | 1.43 | 1.05 | 1.01 | 0.91 | 1.00 |
| 1810032O08Rik | 0.85 | 0.65 | 1.04 | 1.11 | 17.67 | 1.51 | 0.53 | 2.77 | 0.86 | 1.24 | 1.20 | 0.93 |
| 1810044D09Rik | 0.93 | 0.94 | 1.24 | 1.20 | 1.44 | 1.17 | 0.83 | 2.63 | 0.92 | 1.04 | 1.34 | 1.30 |
| 1810053B23Rik | 1.00 | 1.00 | 1.00 | 1.00 | 1.00 | 1.00 | 0.84 | 0.37 | 1.00 | 0.62 | 1.00 | 1.00 |
| 1810058I24Rik | 1.32 | 1.39 | 1.26 | 0.77 | 2.24 | 0.83 | 0.87 | 0.98 | 1.05 | 1.01 | 1.29 | 0.82 |
| 2010005H15Rik | 1.00 | 1.00 | 1.00 | 1.00 | 1.99 | 1.00 | 1.00 | 1.00 | 1.00 | 1.00 | 1.00 | 1.00 |
| 2010010A06Rik | 1.04 | 0.88 | 1.17 | 0.82 | 1.00 | 1.00 | 1.00 | 1.00 | 1.00 | 1.00 | 1.00 | 1.00 |
| 2010107E04Rik | 0.85 | 0.84 | 0.84 | 0.69 | 3.71 | 0.92 | 0.82 | 2.31 | 0.88 | 1.02 | 1.51 | 1.14 |
| 2010109I03Rik | 0.78 | 1.02 | 0.76 | 1.00 | 1.00 | 1.00 | 1.22 | 2.64 | 0.92 | 1.00 | 1.00 | 1.00 |
| 2010300C02Rik | 1.09 | 1.24 | 0.85 | 1.76 | 1.00 | 2.06 | 1.30 | 0.87 | 0.91 | 1.00 | 6.98 | 1.00 |
| 2010320M18Rik | 1.27 | 1.07 | 1.32 | 0.92 | 5.60 | 0.80 | 1.04 | 0.97 | 1.06 | 0.91 | 1.17 | 0.90 |
| 2200002D01Rik | 0.50 | 0.53 | 0.67 | 1.18 | 1.87 | 1.58 | 1.00 | 5.99 | 1.00 | 1.03 | 0.58 | 1.27 |

Fig. 35-112

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| 0610037L13Rik | 1.40 | 0.92 | 0.87 | 1.00 | 0.87 | 0.94 | 1.23 | 5.07 | 0.95 | 1.97 | 1.13 | 1.01 |
| 0610040B10Rik | 0.65 | 1.24 | 2.37 | 1.23 | 0.29 | 1.33 | 0.95 | 5.76 | 0.59 | 1.29 | 0.87 | 1.38 |
| 0610043K17Rik | 1.00 | 1.00 | 1.00 | 1.00 | 1.00 | 1.00 | 1.39 | 1.00 | 1.77 | 1.00 | 1.00 | 1.00 |
| 1100001G20Rik | 1.00 | 1.00 | 1.00 | 1.00 | 1.00 | 1.00 | 0.85 | 11.45 | 0.59 | 3.67 | 1.75 | 1.36 |
| 1110002L01Rik | 1.00 | 1.00 | 1.00 | 1.31 | 1.16 | 0.87 | 0.81 | 0.80 | 1.00 | 0.73 | 0.37 | 0.79 |
| 1110004E09Rik | 1.28 | 1.25 | 0.85 | 1.11 | 8.27 | 0.81 | 0.99 | 1.67 | 0.89 | 1.05 | 1.23 | 0.78 |
| 1110017D15Rik | 1.00 | 1.00 | 1.00 | 0.69 | 0.93 | 0.92 | 1.45 | 1.00 | 1.00 | 1.00 | 1.00 | 1.00 |
| 1110020A21Rik | 1.00 | 1.00 | 1.00 | 1.15 | 0.12 | 1.27 | 1.33 | 2.94 | 1.15 | 1.77 | 1.20 | 1.04 |
| 1110034G24Rik | 1.10 | 0.57 | 1.00 | 1.09 | 0.73 | 0.94 | 1.26 | 2.27 | 0.86 | 1.16 | 1.20 | 1.13 |
| 1110038B12Rik | 0.96 | 1.20 | 0.93 | 0.62 | 1.23 | 0.46 | 0.39 | 0.53 | 0.32 | 0.89 | 0.69 | 0.73 |
| 1110046J04Rik | 1.00 | 1.00 | 1.00 | 1.20 | 0.91 | 1.52 | 1.77 | 21.23 | 2.25 | 1.00 | 1.00 | 1.00 |
| 1110054M08Rik | 0.80 | 0.85 | 0.62 | 1.09 | 0.81 | 1.21 | 1.00 | 9.98 | 0.83 | 2.74 | 1.43 | 1.52 |
| 1110065P20Rik | 1.00 | 0.74 | 0.65 | 0.99 | 0.96 | 1.02 | 1.14 | 9.47 | 0.93 | 2.37 | 0.99 | 1.09 |
| 1190002F15Rik | 1.00 | 1.00 | 1.00 | 1.00 | 1.00 | 1.00 | 0.55 | 13.95 | 0.80 | 2.52 | 1.02 | 0.77 |
| 1190005I06Rik | 1.00 | 1.00 | 0.56 | 1.42 | 1.43 | 1.21 | 1.00 | 15.31 | 0.71 | 3.95 | 1.00 | 1.00 |
| 1190007I07Rik | 1.19 | 0.45 | 0.39 | 1.63 | 0.75 | 0.84 | 0.63 | 1.00 | 1.30 | 1.64 | 0.70 | 1.02 |
| 1300002E11Rik | 0.70 | 0.66 | 0.56 | 0.84 | 0.56 | 1.05 | 0.61 | 1.61 | 0.84 | 1.45 | 0.77 | 1.15 |
| 1500009C09Rik | 1.00 | 1.00 | 1.00 | 1.00 | 0.94 | 0.95 | 1.00 | 1.00 | 1.00 | 1.00 | 1.00 | 1.00 |
| 1500012F01Rik | 1.00 | 0.45 | 0.71 | 1.31 | 2.56 | 0.90 | 1.62 | 8.41 | 1.21 | 2.15 | 0.99 | 0.98 |
| 1500015O10Rik | 1.00 | 1.00 | 1.00 | 0.72 | 6.31 | 0.75 | 1.14 | 2.09 | 1.07 | 1.00 | 1.00 | 1.00 |
| 1600002K03Rik | 1.25 | 2.32 | 1.20 | 1.14 | 1.53 | 0.65 | 1.47 | 18.36 | 0.85 | 2.78 | 1.44 | 0.72 |
| 1600014C23Rik | 1.00 | 1.00 | 1.00 | 1.00 | 1.55 | 1.00 | 1.00 | 5.96 | 1.00 | 1.00 | 1.00 | 1.00 |
| 1600020E01Rik | 1.01 | 1.49 | 1.06 | 0.50 | 1.03 | 1.16 | 1.29 | 21.28 | 1.29 | 3.54 | 1.05 | 1.13 |
| 1700001O22Rik | 1.00 | 1.00 | 1.00 | 1.05 | 1.01 | 0.98 | 1.70 | 4.43 | 0.33 | 1.00 | 1.00 | 1.00 |
| 1700003E16Rik | 0.73 | 0.39 | 0.57 | 1.07 | 0.83 | 1.11 | 5.93 | 2.18 | 0.59 | 1.00 | 1.00 | 1.00 |
| 1700003F12Rik | 1.00 | 1.27 | 1.00 | 0.77 | 1.07 | 0.65 | 5.42 | 30.54 | 2.33 | 1.06 | 1.00 | 1.00 |
| 1700003G13Rik | 1.00 | 1.00 | 1.00 | 1.00 | 1.00 | 1.00 | 0.81 | 14.42 | 1.06 | 1.00 | 1.00 | 1.00 |
| 1700007L15Rik | 0.57 | 0.74 | 0.67 | 0.61 | 0.21 | 1.00 | 1.29 | 5.04 | 0.74 | 0.65 | 1.10 | 1.63 |
| 1700008K24Rik | 1.00 | 1.00 | 1.00 | 1.00 | 1.00 | 1.00 | 6.90 | 1.00 | 1.00 | 1.00 | 1.00 | 1.00 |
| 1700009N14Rik | 1.00 | 1.00 | 1.00 | 1.00 | 1.00 | 1.00 | 6.43 | 1.00 | 1.00 | 1.00 | 1.00 | 1.00 |
| 1700009P17Rik | 1.00 | 1.00 | 1.00 | 1.33 | 1.07 | 1.30 | 1.87 | 1.00 | 1.00 | 2.26 | 1.00 | 1.53 |
| 1700012A03Rik | 1.00 | 1.00 | 1.00 | 1.00 | 1.27 | 1.00 | 1.09 | 1.00 | 1.00 | 1.00 | 1.00 | 1.00 |
| 1700017B05Rik | 1.39 | 0.79 | 0.87 | 1.07 | 0.98 | 1.19 | 1.62 | 2.46 | 1.19 | 1.02 | 0.99 | 0.98 |
| 1700025F24Rik | 1.00 | 1.00 | 1.00 | 1.00 | 1.00 | 1.00 | 1.00 | 1.00 | 1.00 | 1.00 | 1.00 | 1.00 |
| 1700027A15Rik | 1.00 | 1.00 | 1.00 | 1.00 | 1.00 | 1.00 | 7.91 | 1.00 | 1.00 | 1.00 | 1.00 | 1.00 |
| 1700029I15Rik | 1.00 | 1.00 | 1.00 | 1.00 | 0.21 | 1.00 | 1.00 | 10.05 | 0.85 | 1.09 | 1.00 | 1.00 |
| 1700037C18Rik | 1.00 | 1.00 | 1.00 | 0.93 | 1.13 | 0.98 | 1.96 | 14.39 | 1.08 | 2.92 | 1.33 | 1.25 |
| 1700047M11Rik | 1.00 | 1.00 | 1.00 | 0.49 | 0.44 | 0.68 | 1.35 | 7.30 | 1.00 | 2.83 | 0.83 | 0.88 |
| 1700057H15Rik | 1.00 | 1.00 | 1.00 | 1.00 | 1.00 | 1.00 | 1.00 | 1.00 | 1.00 | 1.00 | 1.00 | 1.00 |
| 1700084C01Rik | 1.00 | 1.00 | 1.00 | 0.78 | 1.08 | 0.91 | 1.00 | 1.00 | 1.00 | 1.00 | 1.00 | 1.00 |
| 1700084E18Rik | 1.00 | 1.00 | 1.00 | 0.80 | 0.27 | 1.26 | 2.37 | 3.33 | 1.09 | 3.63 | 1.00 | 1.54 |
| 1700101I11Rik | 1.00 | 1.00 | 1.00 | 0.74 | 0.64 | 0.79 | 4.74 | 5.99 | 3.86 | 1.00 | 1.07 | 1.00 |
| 1700102H20Rik | 1.00 | 1.00 | 1.00 | 1.00 | 1.00 | 1.00 | 0.78 | 7.93 | 1.00 | 1.00 | 1.00 | 1.00 |
| 1700112E06Rik | 1.00 | 1.00 | 0.73 | 1.07 | 0.51 | 1.00 | 1.43 | 2.70 | 1.31 | 1.65 | 1.35 | 1.74 |
| 1700113A16Rik | 0.77 | 0.88 | 0.87 | 1.16 | 0.91 | 1.07 | 1.52 | 6.09 | 1.17 | 1.84 | 1.22 | 0.93 |
| 1700121N20Rik | 1.00 | 1.00 | 1.00 | 1.00 | 1.00 | 1.00 | 1.00 | 1.00 | 1.00 | 1.00 | 1.00 | 1.00 |
| 1700123L14Rik | 1.00 | 1.00 | 1.00 | 1.00 | 1.00 | 1.00 | 7.20 | 1.00 | 1.00 | 1.00 | 1.00 | 1.00 |
| 1810009A15Rik | 1.33 | 0.96 | 0.49 | 1.17 | 1.48 | 1.21 | 0.86 | 2.94 | 0.83 | 1.58 | 0.89 | 1.06 |
| 1810009J06Rik | 2.08 | 12.97 | 0.27 | 1.00 | 1.00 | 1.00 | 1.00 | 1.00 | 1.00 | 1.00 | 1.00 | 1.00 |
| 1810010H24Rik | 1.52 | 0.41 | 0.85 | 1.09 | 1.96 | 1.31 | 1.24 | 3.15 | 0.90 | 1.00 | 1.00 | 1.25 |
| 1810012K16Rik | 1.00 | 1.00 | 1.00 | 1.00 | 0.11 | 1.00 | 1.00 | 1.00 | 1.00 | 1.00 | 1.00 | 1.00 |
| 1810022K09Rik | 0.57 | 0.80 | 1.82 | 1.22 | 0.57 | 1.38 | 0.89 | 8.32 | 0.87 | 1.51 | 1.20 | 1.33 |
| 1810026B05Rik | 1.05 | 1.40 | 1.01 | 0.81 | 0.71 | 1.00 | 1.07 | 5.03 | 0.92 | 2.33 | 1.37 | 1.16 |
| 1810032O08Rik | 1.00 | 1.38 | 1.00 | 0.92 | 1.05 | 0.75 | 1.50 | 7.57 | 1.24 | 2.49 | 1.23 | 0.86 |
| 1810044D09Rik | 0.41 | 0.69 | 0.56 | 0.59 | 1.26 | 1.18 | 1.05 | 15.98 | 1.38 | 2.32 | 1.83 | 0.97 |
| 1810053B23Rik | 0.99 | 1.32 | 1.24 | 1.00 | 1.00 | 1.00 | 1.00 | 1.00 | 1.00 | 0.88 | 0.94 | 0.97 |
| 1810058I24Rik | 1.08 | 0.84 | 0.83 | 1.17 | 1.04 | 1.09 | 1.24 | 4.28 | 1.04 | 1.57 | 1.23 | 1.04 |
| 2010005H15Rik | 1.00 | 1.00 | 1.00 | 1.00 | 1.00 | 1.00 | 1.00 | 1.00 | 1.00 | 5.26 | 3.60 | 1.32 |
| 2010010A06Rik | 1.00 | 1.00 | 1.00 | 1.00 | 1.00 | 1.00 | 0.87 | 0.36 | 0.87 | 1.00 | 1.00 | 1.00 |
| 2010107E04Rik | 1.04 | 0.81 | 0.82 | 1.07 | 1.03 | 0.93 | 1.34 | 16.02 | 0.69 | 3.07 | 1.13 | 1.21 |
| 2010109I03Rik | 1.00 | 1.00 | 1.00 | 1.00 | 1.00 | 1.00 | 0.99 | 7.17 | 0.74 | 1.00 | 1.00 | 1.00 |
| 2010300C02Rik | 0.74 | 0.62 | 0.94 | 1.08 | 1.22 | 1.09 | 0.69 | 0.74 | 0.76 | 1.00 | 1.00 | 1.00 |
| 2010320M18Rik | 1.74 | 2.20 | 1.29 | 1.43 | 1.65 | 1.13 | 1.18 | 2.52 | 1.08 | 1.59 | 1.29 | 0.90 |
| 2200002D01Rik | 1.00 | 1.00 | 1.00 | 1.00 | 0.43 | 1.00 | 1.53 | 25.72 | 0.66 | 1.73 | 1.00 | 1.00 |

Fig. 35- 113

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| 2210010C04Rik | 1.00 | 1.00 | 1.00 | 1.00 | 1.00 | 1.00 | 1.00 | 1.00 | 1.00 | 1.00 | 1.00 | 1.37 |
| 2210011C24Rik | 0.68 | 0.82 | 1.17 | 1.00 | 1.00 | 1.00 | 1.00 | 1.00 | 1.00 | 0.85 | 1.34 | 0.79 |
| 2210013O21Rik | 0.87 | 0.72 | 0.75 | 0.54 | 2.75 | 0.56 | 0.97 | 0.98 | 0.81 | 1.35 | 1.46 | 0.90 |
| 2210407C18Rik | 0.87 | 1.00 | 1.00 | 1.00 | 1.00 | 1.00 | 2.01 | 1.51 | 1.44 | 0.29 | 1.00 | 1.00 |
| 2210408F21Rik | 1.82 | 0.43 | 1.09 | 0.53 | 12.69 | 0.84 | 0.95 | 1.37 | 0.95 | 5.98 | 3.16 | 2.15 |
| 2210409D07Rik | 1.00 | 1.00 | 1.00 | 2.53 | 5.79 | 1.00 | 1.00 | 1.00 | 1.00 | 1.01 | 1.00 | 1.00 |
| 2310001H17Rik | 1.08 | 0.66 | 0.85 | 1.32 | 9.28 | 1.38 | 1.18 | 0.94 | 2.15 | 1.22 | 1.83 | 0.86 |
| 2310002J15Rik | 1.00 | 1.00 | 1.00 | 1.00 | 1.00 | 1.00 | 1.00 | 1.00 | 1.00 | 2.17 | 1.00 | 1.00 |
| 2310003H01Rik | 1.11 | 0.85 | 0.79 | 0.42 | 3.55 | 1.02 | 0.74 | 0.80 | 0.58 | 2.93 | 3.61 | 0.97 |
| 2310010J17Rik | 1.93 | 0.66 | 1.05 | 0.37 | 10.58 | 1.64 | 0.79 | 0.65 | 0.72 | 2.39 | 4.68 | 0.92 |
| 2310015B20Rik | 1.32 | 0.75 | 1.01 | 1.00 | 4.81 | 0.82 | 0.49 | 0.46 | 0.66 | 3.22 | 5.32 | 0.94 |
| 2310034O05Rik | 1.00 | 1.00 | 1.00 | 1.00 | 1.00 | 1.00 | 1.00 | 1.00 | 1.00 | 0.97 | 2.48 | 1.38 |
| 2310036O22Rik | 1.44 | 0.83 | 1.03 | 0.57 | 3.85 | 0.77 | 1.07 | 0.90 | 0.94 | 2.03 | 2.43 | 1.00 |
| 2310045N01Rik | 0.98 | 0.80 | 1.23 | 0.20 | 3.16 | 1.15 | 1.92 | 1.09 | 1.51 | 0.61 | 2.16 | 1.06 |
| 2310057J18Rik | 1.00 | 1.00 | 1.00 | 1.00 | 1.00 | 1.00 | 1.00 | 1.00 | 1.00 | 1.00 | 1.00 | 1.00 |
| 2310057M21Rik | 1.21 | 1.39 | 1.27 | 0.79 | 0.72 | 1.01 | 1.30 | 1.28 | 1.50 | 1.13 | 0.83 | 1.15 |
| 2310061I04Rik | 0.93 | 0.67 | 0.78 | 0.54 | 1.61 | 0.97 | 1.03 | 0.92 | 0.72 | 1.19 | 1.69 | 0.83 |
| 2410004N09Rik | 1.92 | 1.09 | 1.41 | 2.09 | 27.07 | 2.11 | 2.70 | 0.85 | 0.72 | 1.99 | 3.60 | 0.77 |
| 2410006H16Rik | 4.72 | 1.68 | 2.38 | 0.86 | 14.14 | 2.05 | 1.65 | 1.77 | 0.55 | 1.90 | 1.75 | 0.81 |
| 2410015M20Rik | 1.18 | 0.54 | 0.98 | 0.21 | 5.72 | 0.88 | 0.94 | 0.79 | 0.85 | 2.14 | 3.00 | 0.84 |
| 2410131K14Rik | 1.25 | 1.38 | 1.07 | 1.08 | 2.98 | 0.88 | 0.89 | 1.38 | 1.21 | 1.20 | 1.27 | 1.10 |
| 2510049J12Rik | 1.00 | 1.00 | 1.00 | 1.00 | 1.00 | 1.00 | 1.00 | 1.04 | 1.00 | 1.00 | 1.00 | 1.00 |
| 2610002J02Rik | 0.86 | 0.89 | 1.68 | 0.52 | 4.21 | 0.98 | 1.01 | 0.92 | 0.93 | 1.70 | 2.13 | 0.87 |
| 2610016A17Rik | 2.17 | 2.26 | 1.04 | 0.57 | 6.95 | 1.47 | 1.00 | 1.00 | 1.00 | 1.00 | 1.23 | 1.00 |
| 2610524H06Rik | 1.00 | 0.52 | 1.00 | 1.00 | 1.31 | 1.00 | 0.66 | 0.47 | 1.31 | 0.72 | 0.55 | 0.53 |
| 2700060E02Rik | 1.14 | 0.55 | 0.88 | 0.65 | 13.93 | 1.27 | 0.93 | 0.79 | 0.85 | 2.76 | 4.18 | 0.95 |
| 2810025M15Rik | 1.17 | 0.64 | 0.92 | 1.00 | 6.54 | 1.54 | 1.16 | 0.95 | 0.97 | 1.87 | 1.97 | 1.07 |
| 2810405F15Rik | 1.00 | 1.00 | 1.00 | 1.00 | 1.00 | 1.00 | 1.00 | 1.00 | 1.00 | 1.00 | 1.00 | 1.00 |
| 2810428I15Rik | 1.39 | 0.46 | 0.82 | 0.15 | 15.09 | 0.65 | 1.13 | 0.72 | 0.88 | 3.83 | 6.11 | 0.98 |
| 2810474O19Rik | 1.27 | 1.23 | 1.15 | 1.16 | 1.00 | 0.61 | 5.13 | 7.67 | 3.46 | 0.81 | 0.97 | 1.19 |
| 2900008C10Rik | 1.15 | 0.53 | 0.60 | 0.39 | 9.23 | 1.03 | 0.85 | 0.58 | 0.70 | 2.19 | 3.64 | 0.98 |
| 2900009J06Rik | 1.33 | 1.11 | 2.23 | 0.63 | 5.98 | 1.07 | 1.55 | 2.65 | 1.15 | 1.98 | 1.26 | 1.00 |
| 2900011O08Rik | 1.00 | 1.00 | 1.00 | 1.00 | 0.15 | 1.00 | 1.00 | 1.00 | 1.00 | 1.00 | 1.00 | 1.00 |
| 2900079G21Rik | 2.94 | 1.54 | 2.06 | 1.00 | 1.73 | 1.00 | 1.00 | 1.00 | 1.00 | 1.00 | 1.00 | 1.00 |
| 3010026O09Rik | 0.99 | 1.47 | 1.25 | 1.24 | 3.64 | 0.70 | 1.62 | 1.42 | 1.30 | 0.83 | 2.04 | 1.03 |
| 3110009E18Rik | 1.00 | 1.00 | 1.00 | 0.44 | 2.98 | 1.00 | 1.00 | 1.00 | 0.72 | 3.07 | 3.85 | 1.52 |
| 3110035E14Rik | 1.00 | 1.00 | 1.00 | 1.00 | 0.16 | 1.00 | 1.00 | 1.00 | 1.00 | 1.00 | 1.00 | 1.00 |
| 3110040N11Rik | 0.70 | 0.83 | 0.74 | 1.53 | 2.41 | 1.11 | 0.59 | 0.76 | 0.83 | 0.75 | 0.77 | 0.79 |
| 3110043O21Rik | 0.79 | 0.95 | 0.88 | 1.02 | 0.45 | 0.93 | 0.83 | 0.92 | 0.85 | 0.80 | 0.73 | 0.98 |
| 3110079O15Rik | 1.00 | 1.00 | 1.00 | 1.00 | 1.81 | 1.00 | 1.00 | 1.00 | 1.00 | 1.00 | 1.00 | 1.00 |
| 3300002I08Rik | 1.00 | 0.49 | 1.00 | 1.00 | 1.00 | 1.00 | 1.00 | 1.00 | 1.00 | 0.93 | 1.23 | 1.00 |
| 3930402G23Rik | 1.00 | 1.00 | 1.00 | 2.01 | 18.44 | 2.91 | 1.00 | 1.00 | 1.00 | 2.17 | 1.73 | 1.00 |
| 4833411C07Rik | 1.00 | 1.00 | 1.00 | 2.33 | 8.04 | 2.60 | 1.00 | 1.19 | 1.00 | 1.00 | 1.44 | 1.10 |
| 4922502D21Rik | 1.00 | 1.00 | 1.00 | 1.00 | 1.00 | 1.00 | 1.00 | 1.00 | 1.00 | 1.20 | 1.00 | 1.00 |
| 4930401C15Rik | 1.00 | 1.00 | 1.00 | 1.00 | 1.00 | 1.00 | 1.00 | 1.00 | 1.00 | 1.00 | 1.00 | 1.00 |
| 4930404A05Rik | 1.00 | 1.00 | 1.00 | 1.00 | 1.00 | 1.00 | 1.00 | 1.00 | 1.00 | 1.00 | 1.00 | 1.00 |
| 4930412C18Rik | 1.00 | 1.00 | 1.00 | 7.13 | 5.75 | 9.70 | 1.00 | 1.00 | 1.00 | 1.00 | 1.00 | 1.45 |
| 4930413F20Rik | 1.00 | 1.00 | 1.00 | 1.00 | 1.00 | 1.00 | 1.00 | 1.00 | 1.00 | 1.00 | 1.00 | 0.85 |
| 4930447K03Rik | 1.00 | 1.00 | 1.00 | 1.00 | 1.00 | 1.00 | 1.00 | 1.00 | 1.00 | 1.00 | 1.00 | 1.00 |
| 4930481A15Rik | 2.78 | 1.89 | 2.23 | 0.46 | 6.08 | 0.87 | 1.62 | 1.42 | 0.90 | 1.82 | 2.57 | 1.50 |
| 4930511M06Rik | 1.00 | 1.02 | 1.00 | 1.00 | 1.00 | 1.00 | 1.25 | 1.33 | 1.00 | 1.00 | 1.00 | 1.00 |
| 4930523O13Rik | 1.00 | 1.00 | 1.00 | 1.00 | 1.00 | 1.00 | 1.00 | 1.00 | 1.00 | 1.00 | 1.00 | 1.00 |
| 4930526I15Rik | 1.53 | 0.77 | 1.33 | 0.53 | 10.29 | 0.97 | 1.09 | 1.05 | 0.89 | 2.38 | 3.64 | 0.98 |
| 4930529K09Rik | 1.00 | 1.00 | 1.00 | 1.00 | 1.00 | 1.00 | 1.00 | 1.00 | 1.00 | 1.00 | 1.00 | 1.00 |
| 4930539J05Rik | 1.00 | 1.00 | 1.67 | 0.62 | 0.90 | 1.81 | 0.45 | 1.69 | 1.05 | 1.79 | 1.98 | 1.00 |
| 4930593C16Rik | 1.00 | 1.00 | 1.00 | 1.00 | 1.00 | 1.00 | 1.00 | 1.00 | 1.00 | 1.00 | 1.00 | 1.00 |
| 4931428L18Rik | 1.00 | 1.00 | 1.00 | 1.00 | 1.00 | 1.00 | 1.00 | 1.00 | 1.00 | 1.34 | 1.13 | 1.00 |
| 4932414J04Rik | 1.00 | 1.00 | 1.00 | 1.00 | 1.00 | 1.00 | 1.00 | 1.00 | 1.00 | 1.00 | 1.00 | 1.00 |
| 4932702P03Rik | 1.00 | 1.09 | 1.00 | 0.34 | 10.97 | 1.00 | 1.00 | 1.00 | 1.19 | 5.79 | 1.00 | 1.00 |
| 4933402C06Rik | 1.00 | 1.00 | 1.00 | 1.00 | 1.00 | 1.00 | 1.00 | 1.00 | 1.00 | 1.00 | 1.00 | 1.00 |
| 4933406K04Rik | 1.00 | 1.00 | 1.00 | 1.00 | 1.00 | 1.00 | 1.00 | 1.00 | 1.00 | 1.00 | 1.00 | 1.00 |
| 4933407E24Rik | 1.00 | 1.00 | 1.00 | 1.00 | 1.00 | 1.00 | 1.00 | 1.00 | 1.00 | 1.00 | 1.00 | 1.00 |
| 4933409K07Rik | 1.98 | 1.16 | 1.83 | 2.38 | 1.56 | 2.56 | 1.95 | 2.25 | 1.96 | 4.50 | 5.16 | 7.34 |
| 4933411K16Rik | 1.00 | 1.00 | 1.00 | 1.00 | 1.00 | 1.00 | 1.00 | 1.00 | 1.00 | 2.03 | 1.00 | 1.00 |

Fig. 35- 114

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| 2210010C04Rik | 1.00 | 1.00 | 1.31 | 1.00 | 1.00 | 0.83 | 1.00 | 1.00 | 0.63 | 0.44 | 2.42 | 28.02 |
| 2210011C24Rik | 1.00 | 1.00 | 1.00 | 1.41 | 1.19 | 1.43 | 1.00 | 1.00 | 1.00 | 0.81 | 1.60 | 1.27 |
| 2210013O21Rik | 1.11 | 1.33 | 0.95 | 1.05 | 0.73 | 0.67 | 1.04 | 2.69 | 1.00 | 1.02 | 1.21 | 0.82 |
| 2210407C18Rik | 5.44 | 1.48 | 1.53 | 1.00 | 1.00 | 1.00 | 1.00 | 1.00 | 1.00 | 2.57 | 4.11 | 2.20 |
| 2210408F21Rik | 1.00 | 1.08 | 0.88 | 1.51 | 0.76 | 1.11 | 1.37 | 2.51 | 1.93 | 1.00 | 1.00 | 1.00 |
| 2210409D07Rik | 1.00 | 1.00 | 1.00 | 1.00 | 1.00 | 1.00 | 1.00 | 1.00 | 1.00 | 1.00 | 1.31 | 1.00 |
| 2310001H17Rik | 1.69 | 1.38 | 1.46 | 0.31 | 0.52 | 0.71 | 0.44 | 1.09 | 0.43 | 0.75 | 2.29 | 1.29 |
| 2310002J15Rik | 1.18 | 1.00 | 1.00 | 1.00 | 1.01 | 0.77 | 1.00 | 1.00 | 1.00 | 1.00 | 1.00 | 1.00 |
| 2310003H01Rik | 0.74 | 0.73 | 0.82 | 1.12 | 0.54 | 0.94 | 1.58 | 4.38 | 1.03 | 0.86 | 0.94 | 0.89 |
| 2310010J17Rik | 0.95 | 1.62 | 1.47 | 0.72 | 0.50 | 0.67 | 0.92 | 1.63 | 0.85 | 1.11 | 1.64 | 0.80 |
| 2310015B20Rik | 1.26 | 1.61 | 1.00 | 1.00 | 0.81 | 1.00 | 1.00 | 1.00 | 1.00 | 1.00 | 1.38 | 1.40 |
| 2310034O05Rik | 1.00 | 1.00 | 1.00 | 1.00 | 1.00 | 1.00 | 1.33 | 8.90 | 1.39 | 1.00 | 1.00 | 1.00 |
| 2310036O22Rik | 0.99 | 1.32 | 0.84 | 0.93 | 0.76 | 1.06 | 1.10 | 1.40 | 1.00 | 0.99 | 1.58 | 1.07 |
| 2310045N01Rik | 1.26 | 1.47 | 1.16 | 0.61 | 1.00 | 0.91 | 0.90 | 0.46 | 0.76 | 0.92 | 0.99 | 1.04 |
| 2310057J18Rik | 1.00 | 1.00 | 1.00 | 1.00 | 1.00 | 1.00 | 1.00 | 1.00 | 1.00 | 1.00 | 1.00 | 1.00 |
| 2310057M21Rik | 0.72 | 0.80 | 0.95 | 1.00 | 1.12 | 0.97 | 1.00 | 1.00 | 1.38 | 1.06 | 0.90 | 0.80 |
| 2310061I04Rik | 0.60 | 0.68 | 0.68 | 1.10 | 1.17 | 0.90 | 1.03 | 1.66 | 0.97 | 1.03 | 1.18 | 0.97 |
| 2410004N09Rik | 1.42 | 2.43 | 0.95 | 1.17 | 1.02 | 1.02 | 0.37 | 1.12 | 1.40 | 1.15 | 1.80 | 1.01 |
| 2410006H16Rik | 1.52 | 1.66 | 1.08 | 1.01 | 1.08 | 1.75 | 1.23 | 2.11 | 0.89 | 0.81 | 1.65 | 1.07 |
| 2410015M20Rik | 1.10 | 1.50 | 0.96 | 0.81 | 0.57 | 0.75 | 0.92 | 1.61 | 0.90 | 0.83 | 1.53 | 1.02 |
| 2410131K14Rik | 0.89 | 0.80 | 1.21 | 1.41 | 2.42 | 1.36 | 3.34 | 3.85 | 1.86 | 1.09 | 0.74 | 0.81 |
| 2510049J12Rik | 1.60 | 1.00 | 1.09 | 1.67 | 3.79 | 1.58 | 6.14 | 10.12 | 5.63 | 2.24 | 2.50 | 2.05 |
| 2610002J02Rik | 1.18 | 1.49 | 0.99 | 0.89 | 0.75 | 0.96 | 1.63 | 2.11 | 1.49 | 0.90 | 1.54 | 1.10 |
| 2610016A17Rik | 1.66 | 1.45 | 1.35 | 1.00 | 0.85 | 1.01 | 1.00 | 1.00 | 1.00 | 1.00 | 1.00 | 1.00 |
| 2610524H06Rik | 0.78 | 0.92 | 0.73 | 0.63 | 0.39 | 0.55 | 1.00 | 1.66 | 1.00 | 0.56 | 0.79 | 0.85 |
| 2700060E02Rik | 1.25 | 1.71 | 1.03 | 0.94 | 0.76 | 0.98 | 1.19 | 2.07 | 0.87 | 1.11 | 1.67 | 1.02 |
| 2810025M15Rik | 1.83 | 1.56 | 1.73 | 0.85 | 0.64 | 0.79 | 0.63 | 1.05 | 0.87 | 1.05 | 1.58 | 0.90 |
| 2810405F15Rik | 1.04 | 1.04 | 0.94 | 1.00 | 1.00 | 1.00 | 1.00 | 1.00 | 1.00 | 1.00 | 1.00 | 1.00 |
| 2810428I15Rik | 0.93 | 1.45 | 0.88 | 0.87 | 0.47 | 1.12 | 0.95 | 2.67 | 0.80 | 0.91 | 1.76 | 1.08 |
| 2810474O19Rik | 1.07 | 1.03 | 1.20 | 1.31 | 2.29 | 0.84 | 0.83 | 0.71 | 0.72 | 0.97 | 0.65 | 0.91 |
| 2900008C10Rik | 0.78 | 1.61 | 1.06 | 1.00 | 0.57 | 1.00 | 1.00 | 2.35 | 1.00 | 1.00 | 1.40 | 1.25 |
| 2900009J06Rik | 1.59 | 2.29 | 1.45 | 1.00 | 0.67 | 0.50 | 1.42 | 6.64 | 1.00 | 1.00 | 0.82 | 0.92 |
| 2900011O08Rik | 1.00 | 1.00 | 1.00 | 1.00 | 1.00 | 1.00 | 1.00 | 1.00 | 1.00 | 1.13 | 1.00 | 1.00 |
| 2900079G21Rik | 0.74 | 1.41 | 0.62 | 1.00 | 1.00 | 1.00 | 1.00 | 1.00 | 1.00 | 1.00 | 1.00 | 1.00 |
| 3010026O09Rik | 1.17 | 1.07 | 0.72 | 1.49 | 1.28 | 1.76 | 0.59 | 0.38 | 0.76 | 1.13 | 1.97 | 1.05 |
| 3110009E18Rik | 1.19 | 0.84 | 0.78 | 1.00 | 0.46 | 1.00 | 1.00 | 1.00 | 1.00 | 0.87 | 1.52 | 0.46 |
| 3110035E14Rik | 1.00 | 1.00 | 1.00 | 1.00 | 1.00 | 1.00 | 1.00 | 1.00 | 1.00 | 1.00 | 1.00 | 1.00 |
| 3110040N11Rik | 1.25 | 1.34 | 1.17 | 0.99 | 0.92 | 0.79 | 1.10 | 0.30 | 1.20 | 0.90 | 1.40 | 0.74 |
| 3110043O21Rik | 0.96 | 0.90 | 0.95 | 1.12 | 1.37 | 0.90 | 5.51 | 0.88 | 2.08 | 1.08 | 0.88 | 1.09 |
| 3110079O15Rik | 1.00 | 1.00 | 1.00 | 1.00 | 1.00 | 1.00 | 1.00 | 1.00 | 1.00 | 1.00 | 1.00 | 1.00 |
| 3300002I08Rik | 1.00 | 1.00 | 1.00 | 1.00 | 0.38 | 1.00 | 1.00 | 1.00 | 1.00 | 1.00 | 1.00 | 1.00 |
| 3930402G23Rik | 1.00 | 1.00 | 1.00 | 1.00 | 1.00 | 1.00 | 1.97 | 12.13 | 1.00 | 1.02 | 1.00 | 1.00 |
| 4833411C07Rik | 1.17 | 2.09 | 1.67 | 2.06 | 3.08 | 2.03 | 0.99 | 0.90 | 0.70 | 1.00 | 1.00 | 1.00 |
| 4922502D21Rik | 1.00 | 1.00 | 1.00 | 1.00 | 1.00 | 1.00 | 1.00 | 1.00 | 1.00 | 1.00 | 1.00 | 1.00 |
| 4930401C15Rik | 1.00 | 1.00 | 1.00 | 1.00 | 1.00 | 1.00 | 1.00 | 1.00 | 1.00 | 1.00 | 1.00 | 1.00 |
| 4930404A05Rik | 1.00 | 1.00 | 1.00 | 1.00 | 1.00 | 1.00 | 1.00 | 1.00 | 1.00 | 1.00 | 1.00 | 1.00 |
| 4930412C18Rik | 1.00 | 1.00 | 1.00 | 2.98 | 1.00 | 2.34 | 2.28 | 1.00 | 2.02 | 1.00 | 1.00 | 1.00 |
| 4930413F20Rik | 1.00 | 1.00 | 1.00 | 0.82 | 1.00 | 0.39 | 1.00 | 1.00 | 1.00 | 0.82 | 0.83 | 0.73 |
| 4930447K03Rik | 1.00 | 1.15 | 1.00 | 1.00 | 1.00 | 1.00 | 1.00 | 1.00 | 1.00 | 1.00 | 1.00 | 1.00 |
| 4930481A15Rik | 1.35 | 1.00 | 1.00 | 1.92 | 1.31 | 1.19 | 1.00 | 2.14 | 1.00 | 2.21 | 1.53 | 1.35 |
| 4930511M06Rik | 1.00 | 1.00 | 1.00 | 1.00 | 1.00 | 1.00 | 1.00 | 1.00 | 1.00 | 1.00 | 1.00 | 1.00 |
| 4930523O13Rik | 1.00 | 1.00 | 1.00 | 1.00 | 1.00 | 1.00 | 1.00 | 1.00 | 1.00 | 1.00 | 1.00 | 1.00 |
| 4930526I15Rik | 0.84 | 0.92 | 0.89 | 0.80 | 0.49 | 1.22 | 1.03 | 3.39 | 1.04 | 0.89 | 1.34 | 1.04 |
| 4930529K09Rik | 1.00 | 1.00 | 1.00 | 1.00 | 1.00 | 1.00 | 1.00 | 1.00 | 1.00 | 1.00 | 1.00 | 1.00 |
| 4930539J05Rik | 1.35 | 0.52 | 1.27 | 0.83 | 1.00 | 0.77 | 1.00 | 1.00 | 2.51 | 1.00 | 1.00 | 0.66 |
| 4930593C16Rik | 1.00 | 1.00 | 1.00 | 1.00 | 1.00 | 1.00 | 1.00 | 1.00 | 1.00 | 1.00 | 1.00 | 1.00 |
| 4931428L18Rik | 1.00 | 1.00 | 1.00 | 1.00 | 1.00 | 1.00 | 1.00 | 1.00 | 1.00 | 1.00 | 1.00 | 1.00 |
| 4932414J04Rik | 1.00 | 1.00 | 1.00 | 1.00 | 1.00 | 1.00 | 1.00 | 1.00 | 1.00 | 1.00 | 1.00 | 1.00 |
| 4932702P03Rik | 1.00 | 1.00 | 1.00 | 0.82 | 0.87 | 1.03 | 0.50 | 2.80 | 1.00 | 1.00 | 1.00 | 1.00 |
| 4933402C06Rik | 1.00 | 1.00 | 1.00 | 1.00 | 1.00 | 1.00 | 1.00 | 1.00 | 1.00 | 1.00 | 1.00 | 1.00 |
| 4933406K04Rik | 1.00 | 1.00 | 1.00 | 1.00 | 1.00 | 1.00 | 1.00 | 1.00 | 1.00 | 1.00 | 1.00 | 1.00 |
| 4933407E24Rik | 1.00 | 1.00 | 1.00 | 1.00 | 1.00 | 1.00 | 1.00 | 1.00 | 1.00 | 1.00 | 1.00 | 1.00 |
| 4933409K07Rik | 4.96 | 3.83 | 5.24 | 2.95 | 1.22 | 2.81 | 2.99 | 2.63 | 2.05 | 1.85 | 1.00 | 1.69 |
| 4933411K16Rik | 1.00 | 1.00 | 1.00 | 1.27 | 0.50 | 1.37 | 0.58 | 2.36 | 1.14 | 1.00 | 1.00 | 0.89 |

Fig. 35-115

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| 2210010C04Rik | 32.77 | 1.84 | 2.50 | 1.00 | 1.00 | 0.57 | 1.00 | 1.35 | 1.19 | 2.15 | 12.16 | 0.88 |
| 2210011C24Rik | 0.77 | 1.22 | 0.93 | 0.74 | 1.00 | 1.08 | 0.94 | 1.23 | 0.87 | 1.00 | 1.00 | 1.00 |
| 2210013O21Rik | 1.06 | 0.80 | 1.11 | 0.72 | 1.97 | 0.72 | 0.93 | 1.38 | 0.79 | 0.78 | 1.08 | 1.00 |
| 2210407C18Rik | 1.22 | 1.60 | 0.95 | 1.00 | 1.00 | 1.00 | 1.00 | 1.00 | 1.00 | 1.00 | 1.00 | 1.00 |
| 2210408F21Rik | 1.26 | 0.85 | 0.51 | 1.90 | 3.31 | 2.22 | 1.00 | 2.22 | 1.00 | 1.04 | 1.00 | 0.68 |
| 2210409D07Rik | 1.00 | 1.00 | 1.00 | 1.00 | 1.00 | 1.00 | 1.00 | 1.00 | 1.00 | 1.00 | 1.00 | 1.00 |
| 2310001H17Rik | 2.16 | 1.66 | 1.93 | 0.46 | 3.69 | 1.63 | 1.00 | 1.00 | 1.00 | 0.91 | 0.74 | 0.95 |
| 2310002J15Rik | 0.77 | 0.98 | 0.88 | 1.00 | 1.00 | 1.00 | 1.29 | 1.00 | 1.15 | 1.00 | 1.00 | 1.00 |
| 2310003H01Rik | 0.88 | 0.97 | 0.72 | 1.07 | 1.32 | 0.91 | 1.13 | 4.38 | 1.15 | 0.99 | 1.05 | 1.12 |
| 2310010J17Rik | 1.73 | 1.04 | 2.67 | 0.60 | 1.97 | 0.84 | 1.33 | 2.79 | 0.65 | 1.08 | 1.45 | 1.20 |
| 2310015B20Rik | 1.00 | 1.30 | 1.23 | 1.00 | 1.00 | 1.00 | 1.00 | 3.33 | 1.00 | 1.02 | 1.33 | 1.00 |
| 2310034O05Rik | 1.00 | 1.00 | 1.00 | 1.00 | 1.00 | 1.00 | 1.00 | 1.00 | 1.00 | 1.25 | 2.19 | 1.00 |
| 2310036O22Rik | 0.99 | 1.10 | 0.96 | 1.01 | 3.13 | 1.13 | 1.08 | 1.78 | 0.93 | 1.00 | 1.05 | 0.87 |
| 2310045N01Rik | 1.64 | 0.71 | 1.20 | 1.49 | 5.12 | 1.21 | 0.57 | 0.78 | 0.93 | 0.55 | 1.14 | 1.03 |
| 2310057J18Rik | 11.28 | 1.19 | 26.71 | 1.00 | 1.00 | 1.00 | 1.00 | 1.00 | 1.00 | 1.00 | 1.00 | 1.00 |
| 2310057M21Rik | 1.04 | 0.98 | 1.09 | 1.01 | 1.00 | 0.87 | 0.98 | 0.73 | 0.98 | 1.00 | 1.01 | 0.92 |
| 2310061I04Rik | 0.84 | 1.02 | 0.89 | 0.63 | 7.44 | 0.91 | 0.96 | 1.13 | 1.01 | 0.84 | 0.64 | 0.71 |
| 2410004N09Rik | 1.16 | 1.64 | 1.25 | 1.40 | 5.69 | 2.59 | 0.70 | 1.13 | 0.95 | 0.85 | 1.44 | 1.43 |
| 2410006H16Rik | 1.85 | 1.23 | 1.76 | 1.59 | 2.33 | 1.51 | 0.61 | 3.58 | 0.90 | 1.09 | 1.34 | 1.26 |
| 2410015M20Rik | 1.08 | 1.29 | 1.09 | 0.74 | 1.84 | 0.86 | 0.80 | 1.86 | 0.79 | 1.04 | 1.01 | 0.95 |
| 2410131K14Rik | 1.18 | 1.01 | 0.69 | 2.08 | 8.72 | 1.27 | 1.17 | 0.90 | 1.30 | 0.99 | 0.83 | 1.17 |
| 2510049J12Rik | 1.19 | 1.50 | 1.07 | 1.00 | 1.00 | 1.00 | 1.00 | 1.00 | 1.00 | 1.00 | 1.00 | 1.00 |
| 2610002J02Rik | 1.11 | 1.10 | 1.19 | 0.64 | 1.42 | 0.76 | 1.09 | 2.07 | 1.49 | 1.02 | 1.06 | 0.92 |
| 2610016A17Rik | 1.00 | 1.00 | 1.00 | 0.52 | 1.69 | 1.27 | 1.00 | 1.00 | 1.00 | 1.00 | 1.00 | 1.00 |
| 2610524H06Rik | 0.75 | 0.72 | 0.84 | 0.75 | 6.74 | 0.60 | 0.75 | 1.40 | 0.90 | 1.01 | 0.88 | 0.84 |
| 2700060E02Rik | 0.89 | 0.95 | 1.03 | 0.99 | 2.89 | 1.23 | 0.82 | 2.42 | 0.95 | 1.20 | 1.56 | 1.10 |
| 2810025M15Rik | 0.94 | 0.97 | 0.93 | 1.17 | 2.58 | 1.22 | 0.97 | 1.73 | 0.97 | 0.83 | 0.96 | 0.87 |
| 2810405F15Rik | 1.00 | 1.00 | 1.00 | 1.00 | 1.00 | 1.00 | 1.00 | 1.00 | 1.00 | 1.00 | 1.00 | 1.00 |
| 2810428I15Rik | 1.02 | 1.42 | 0.81 | 0.77 | 1.27 | 0.73 | 0.88 | 5.62 | 0.92 | 0.88 | 1.35 | 0.72 |
| 2810474O19Rik | 1.15 | 1.31 | 0.71 | 1.00 | 0.29 | 0.64 | 1.11 | 0.80 | 0.97 | 1.13 | 0.77 | 1.19 |
| 2900008C10Rik | 1.00 | 1.00 | 1.23 | 1.00 | 1.18 | 1.00 | 1.00 | 1.00 | 1.00 | 1.12 | 1.46 | 1.42 |
| 2900009J06Rik | 1.00 | 1.00 | 0.96 | 1.33 | 1.00 | 1.00 | 0.92 | 1.50 | 0.50 | 1.00 | 1.00 | 1.00 |
| 2900011O08Rik | 1.00 | 1.00 | 1.00 | 1.00 | 1.00 | 1.00 | 0.81 | 0.60 | 0.89 | 1.00 | 10.03 | 1.00 |
| 2900079G21Rik | 1.00 | 1.00 | 1.00 | 1.00 | 1.00 | 1.00 | 1.00 | 1.00 | 1.00 | 1.00 | 1.92 | 1.00 |
| 3010026O09Rik | 0.76 | 0.47 | 0.91 | 0.70 | 2.06 | 0.59 | 0.82 | 1.46 | 0.92 | 1.27 | 1.75 | 1.03 |
| 3110009E18Rik | 1.00 | 1.00 | 0.44 | 1.00 | 1.00 | 1.43 | 0.78 | 1.28 | 1.48 | 1.91 | 0.87 | 1.28 |
| 3110035E14Rik | 1.00 | 1.00 | 1.00 | 1.00 | 1.00 | 1.00 | 0.92 | 1.00 | 0.98 | 1.00 | 9.75 | 1.00 |
| 3110040N11Rik | 1.34 | 0.64 | 1.29 | 0.51 | 1.00 | 0.62 | 0.87 | 1.15 | 0.73 | 1.06 | 0.90 | 0.85 |
| 3110043O21Rik | 0.89 | 0.82 | 0.83 | 0.71 | 0.38 | 0.79 | 0.87 | 0.49 | 0.96 | 0.93 | 0.84 | 1.00 |
| 3110079O15Rik | 1.00 | 1.00 | 1.00 | 1.00 | 0.74 | 1.00 | 1.00 | 1.00 | 1.00 | 1.00 | 1.00 | 1.00 |
| 3300002I08Rik | 1.00 | 1.00 | 1.00 | 1.00 | 2.45 | 0.85 | 1.00 | 0.73 | 1.00 | 1.00 | 1.00 | 1.00 |
| 3930402G23Rik | 1.11 | 1.57 | 1.00 | 4.93 | 12.29 | 1.98 | 1.00 | 2.03 | 1.00 | 1.00 | 1.00 | 1.00 |
| 4833411C07Rik | 1.00 | 1.00 | 1.00 | 2.51 | 1.16 | 3.14 | 1.00 | 1.00 | 1.00 | 0.65 | 1.86 | 1.17 |
| 4922502D21Rik | 1.00 | 1.00 | 1.00 | 2.98 | 1.00 | 1.12 | 1.02 | 1.22 | 1.03 | 1.00 | 1.00 | 1.00 |
| 4930401C15Rik | 1.00 | 1.00 | 1.00 | 1.00 | 1.00 | 1.00 | 1.00 | 5.14 | 1.00 | 1.00 | 1.00 | 1.00 |
| 4930404A05Rik | 1.00 | 1.00 | 1.00 | 1.00 | 1.00 | 1.00 | 4.17 | 9.17 | 1.89 | 1.00 | 1.00 | 1.00 |
| 4930412C18Rik | 1.00 | 1.08 | 1.00 | 2.15 | 1.00 | 2.74 | 1.19 | 1.00 | 1.08 | 1.00 | 1.00 | 1.00 |
| 4930413F20Rik | 0.83 | 1.17 | 0.63 | 1.00 | 1.00 | 1.00 | 1.87 | 7.84 | 2.34 | 1.00 | 1.00 | 1.00 |
| 4930447K03Rik | 1.00 | 1.00 | 1.00 | 1.00 | 1.00 | 1.00 | 4.06 | 8.72 | 2.33 | 1.00 | 1.00 | 1.00 |
| 4930481A15Rik | 1.00 | 1.00 | 1.00 | 5.32 | 7.62 | 4.88 | 1.00 | 2.17 | 1.00 | 1.69 | 5.39 | 3.57 |
| 4930511M06Rik | 1.00 | 1.00 | 1.00 | 1.00 | 1.00 | 1.00 | 3.97 | 9.80 | 5.62 | 1.00 | 1.00 | 1.00 |
| 4930523O13Rik | 1.00 | 1.00 | 1.00 | 1.00 | 1.00 | 1.00 | 12.68 | 20.32 | 13.84 | 1.00 | 1.00 | 1.00 |
| 4930526I15Rik | 0.99 | 1.31 | 1.15 | 1.04 | 2.44 | 0.88 | 0.93 | 4.71 | 0.91 | 1.06 | 0.92 | 1.06 |
| 4930529K09Rik | 1.00 | 1.00 | 1.00 | 1.00 | 1.00 | 1.00 | 3.80 | 2.25 | 8.10 | 1.00 | 1.00 | 1.00 |
| 4930539J05Rik | 1.00 | 1.18 | 0.67 | 0.89 | 0.28 | 1.56 | 0.86 | 2.01 | 0.98 | 1.00 | 1.00 | 1.78 |
| 4930593C16Rik | 1.00 | 1.00 | 1.00 | 1.00 | 1.00 | 1.00 | 5.32 | 0.99 | 1.56 | 1.00 | 1.00 | 1.00 |
| 4931428L18Rik | 1.00 | 1.00 | 1.00 | 1.00 | 1.00 | 1.00 | 1.04 | 1.15 | 1.19 | 1.00 | 1.00 | 1.00 |
| 4932414J04Rik | 1.00 | 1.00 | 1.00 | 1.00 | 1.00 | 1.00 | 10.09 | 1.00 | 5.77 | 1.00 | 1.00 | 1.00 |
| 4932702P03Rik | 1.00 | 1.00 | 1.00 | 1.00 | 1.25 | 1.00 | 1.71 | 1.00 | 1.88 | 1.00 | 1.00 | 1.00 |
| 4933402C06Rik | 1.00 | 1.00 | 1.00 | 1.00 | 1.00 | 1.00 | 9.67 | 33.75 | 9.87 | 1.00 | 1.00 | 1.00 |
| 4933406K04Rik | 1.00 | 1.00 | 1.00 | 1.00 | 1.00 | 1.00 | 3.95 | 1.00 | 6.08 | 1.00 | 1.00 | 1.00 |
| 4933407E24Rik | 1.00 | 1.00 | 1.00 | 1.00 | 1.00 | 1.00 | 1.55 | 5.10 | 1.83 | 1.00 | 1.00 | 1.00 |
| 4933409K07Rik | 1.08 | 1.00 | 1.00 | 2.61 | 1.00 | 2.30 | 5.81 | 4.26 | 5.55 | 9.60 | 6.77 | 10.80 |
| 4933411K16Rik | 1.00 | 1.00 | 1.00 | 3.66 | 4.63 | 1.24 | 1.01 | 2.51 | 1.05 | 1.00 | 1.00 | 1.00 |

Fig. 35-116

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| 2210010C04Rik | 0.98 | 0.87 | 0.87 | 1.00 | 1.00 | 0.59 | 1.00 | 1.00 | 0.87 | 1.00 | 0.53 | 1.22 |
| 2210011C24Rik | 1.00 | 1.00 | 1.00 | 1.00 | 0.14 | 1.13 | 0.97 | 5.32 | 0.72 | 1.00 | 1.00 | 1.00 |
| 2210013O21Rik | 0.71 | 1.06 | 1.30 | 1.11 | 0.88 | 1.02 | 1.80 | 5.56 | 1.05 | 1.82 | 1.42 | 1.46 |
| 2210407C18Rik | 1.00 | 1.00 | 1.00 | 1.00 | 1.00 | 1.00 | 1.00 | 1.00 | 1.00 | 1.00 | 1.00 | 1.00 |
| 2210408F21Rik | 1.00 | 1.00 | 1.00 | 1.40 | 0.49 | 1.10 | 1.07 | 10.62 | 1.00 | 1.00 | 1.00 | 1.00 |
| 2210409D07Rik | 1.00 | 1.00 | 1.00 | 1.00 | 1.00 | 1.00 | 1.09 | 11.99 | 1.75 | 1.00 | 1.00 | 1.00 |
| 2310001H17Rik | 1.20 | 1.79 | 0.87 | 1.00 | 1.83 | 1.00 | 1.19 | 5.80 | 1.30 | 3.31 | 1.23 | 1.05 |
| 2310002J15Rik | 1.00 | 1.00 | 1.00 | 1.00 | 2.76 | 1.00 | 1.07 | 6.19 | 0.67 | 1.00 | 1.00 | 1.00 |
| 2310003H01Rik | 0.97 | 0.68 | 1.05 | 0.92 | 0.62 | 1.00 | 0.79 | 5.09 | 0.62 | 2.62 | 0.99 | 0.76 |
| 2310010J17Rik | 1.00 | 0.58 | 0.23 | 0.70 | 0.37 | 1.83 | 1.59 | 23.59 | 1.14 | 4.63 | 1.06 | 1.20 |
| 2310015B20Rik | 1.00 | 1.00 | 1.00 | 0.62 | 0.13 | 1.00 | 1.52 | 24.01 | 3.27 | 1.00 | 1.00 | 1.00 |
| 2310034O05Rik | 1.00 | 1.00 | 1.00 | 1.00 | 1.00 | 1.00 | 1.00 | 1.00 | 1.00 | 1.28 | 1.00 | 1.30 |
| 2310036O22Rik | 1.20 | 1.23 | 1.14 | 1.14 | 0.91 | 0.98 | 1.01 | 5.62 | 0.96 | 2.09 | 1.10 | 1.10 |
| 2310045N01Rik | 1.00 | 1.09 | 1.00 | 1.00 | 0.78 | 1.23 | 1.17 | 1.14 | 0.79 | 1.29 | 1.36 | 1.01 |
| 2310057J18Rik | 1.00 | 1.00 | 1.00 | 1.00 | 1.00 | 1.00 | 1.00 | 1.00 | 1.00 | 1.00 | 1.00 | 1.00 |
| 2310057M21Rik | 1.00 | 1.00 | 1.00 | 1.00 | 5.14 | 0.96 | 1.02 | 0.65 | 1.06 | 0.67 | 0.94 | 0.99 |
| 2310061I04Rik | 0.94 | 0.94 | 0.90 | 0.97 | 1.13 | 0.90 | 1.13 | 1.82 | 0.89 | 0.87 | 0.72 | 0.76 |
| 2410004N09Rik | 1.08 | 0.61 | 0.93 | 0.57 | 1.24 | 1.11 | 1.35 | 8.85 | 1.34 | 1.87 | 1.31 | 1.73 |
| 2410006H16Rik | 0.76 | 0.41 | 0.57 | 1.62 | 0.60 | 0.89 | 1.39 | 4.05 | 1.08 | 1.89 | 1.54 | 0.85 |
| 2410015M20Rik | 1.12 | 1.46 | 0.68 | 1.04 | 0.91 | 0.96 | 1.11 | 9.05 | 0.88 | 2.65 | 0.91 | 1.11 |
| 2410131K14Rik | 1.00 | 1.01 | 1.15 | 1.16 | 0.85 | 0.93 | 1.11 | 0.57 | 1.27 | 1.26 | 0.97 | 0.87 |
| 2510049J12Rik | 1.00 | 1.11 | 1.00 | 0.65 | 1.00 | 0.60 | 1.00 | 1.23 | 1.00 | 1.00 | 1.00 | 1.00 |
| 2610002J02Rik | 1.14 | 1.11 | 0.91 | 1.13 | 0.98 | 1.09 | 1.14 | 5.68 | 0.92 | 2.14 | 1.11 | 1.14 |
| 2610016A17Rik | 1.00 | 1.00 | 1.00 | 1.00 | 1.00 | 1.00 | 1.00 | 1.00 | 1.00 | 1.00 | 1.00 | 1.00 |
| 2610524H06Rik | 1.00 | 1.00 | 1.00 | 0.95 | 1.79 | 1.06 | 0.70 | 1.53 | 0.67 | 0.86 | 0.64 | 0.98 |
| 2700060E02Rik | 0.69 | 0.85 | 1.06 | 0.91 | 0.98 | 0.91 | 1.25 | 13.72 | 1.02 | 2.74 | 1.14 | 1.10 |
| 2810025M15Rik | 1.19 | 1.13 | 2.05 | 1.23 | 1.47 | 1.09 | 1.05 | 4.27 | 0.79 | 2.03 | 0.99 | 1.04 |
| 2810405F15Rik | 1.00 | 1.00 | 1.00 | 1.00 | 1.49 | 1.00 | 0.98 | 6.15 | 0.99 | 1.00 | 1.00 | 1.00 |
| 2810428I15Rik | 1.22 | 1.15 | 0.80 | 1.14 | 0.68 | 1.16 | 0.94 | 34.51 | 0.85 | 4.53 | 0.97 | 1.09 |
| 2810474O19Rik | 1.21 | 1.83 | 1.00 | 0.90 | 1.00 | 0.77 | 1.33 | 1.00 | 1.46 | 0.91 | 0.99 | 0.85 |
| 2900008C10Rik | 1.00 | 1.00 | 1.00 | 1.46 | 0.36 | 1.32 | 1.20 | 5.31 | 0.83 | 2.70 | 1.37 | 1.88 |
| 2900009J06Rik | 1.00 | 1.00 | 1.00 | 1.30 | 1.81 | 0.69 | 1.00 | 1.60 | 1.09 | 1.00 | 1.00 | 1.00 |
| 2900011O08Rik | 1.00 | 1.00 | 1.00 | 1.16 | 0.95 | 1.09 | 1.00 | 1.00 | 1.00 | 1.00 | 1.00 | 1.00 |
| 2900079G21Rik | 1.00 | 1.00 | 1.00 | 1.14 | 1.00 | 1.19 | 3.98 | 28.27 | 4.45 | 1.00 | 1.00 | 1.00 |
| 3010026O09Rik | 1.00 | 1.00 | 1.00 | 0.94 | 0.86 | 1.01 | 1.12 | 5.69 | 1.01 | 1.79 | 1.14 | 0.99 |
| 3110009E18Rik | 1.00 | 1.00 | 1.00 | 1.00 | 1.00 | 1.00 | 1.00 | 5.35 | 0.72 | 1.64 | 1.00 | 0.68 |
| 3110035E14Rik | 1.00 | 1.00 | 1.00 | 1.23 | 1.51 | 1.07 | 1.00 | 1.00 | 1.00 | 1.00 | 1.00 | 1.00 |
| 3110040N11Rik | 0.67 | 1.27 | 0.73 | 1.01 | 7.13 | 1.00 | 1.03 | 0.68 | 0.90 | 0.80 | 1.24 | 1.21 |
| 3110043O21Rik | 1.01 | 1.24 | 1.15 | 0.97 | 1.02 | 1.09 | 1.07 | 0.43 | 1.16 | 0.75 | 1.39 | 1.08 |
| 3110079O15Rik | 1.00 | 1.00 | 1.00 | 1.00 | 3.64 | 1.00 | 1.84 | 18.44 | 1.56 | 1.00 | 1.00 | 1.00 |
| 3300002I08Rik | 1.00 | 1.00 | 1.00 | 0.93 | 5.02 | 1.32 | 1.00 | 4.09 | 1.00 | 1.00 | 1.00 | 1.00 |
| 3930402G23Rik | 1.00 | 1.00 | 1.00 | 1.00 | 1.00 | 1.00 | 1.44 | 3.78 | 1.00 | 1.00 | 1.00 | 1.00 |
| 4833411C07Rik | 1.00 | 1.00 | 1.00 | 1.00 | 1.00 | 1.00 | 1.08 | 2.12 | 1.00 | 1.00 | 1.00 | 1.00 |
| 4922502D21Rik | 1.00 | 1.00 | 1.00 | 1.00 | 1.00 | 1.00 | 7.16 | 1.00 | 1.00 | 1.00 | 1.00 | 1.00 |
| 4930401C15Rik | 1.00 | 1.00 | 1.00 | 1.00 | 1.00 | 1.00 | 1.00 | 1.00 | 1.00 | 1.00 | 1.00 | 1.00 |
| 4930404A05Rik | 1.00 | 1.00 | 1.00 | 1.00 | 1.00 | 1.00 | 1.00 | 1.00 | 1.00 | 1.00 | 1.00 | 1.00 |
| 4930412C18Rik | 1.00 | 1.00 | 1.00 | 1.69 | 1.00 | 1.13 | 1.00 | 1.00 | 1.00 | 1.00 | 1.00 | 1.00 |
| 4930413F20Rik | 1.06 | 0.86 | 0.89 | 0.98 | 1.00 | 1.00 | 0.55 | 0.23 | 0.45 | 1.00 | 1.00 | 1.00 |
| 4930447K03Rik | 1.00 | 1.00 | 1.00 | 1.00 | 1.00 | 1.00 | 1.00 | 1.00 | 1.00 | 1.00 | 1.00 | 1.00 |
| 4930481A15Rik | 1.00 | 1.00 | 1.00 | 1.00 | 2.27 | 1.00 | 2.31 | 3.96 | 1.40 | 1.00 | 1.00 | 1.00 |
| 4930511M06Rik | 1.00 | 1.00 | 1.00 | 1.00 | 1.00 | 1.00 | 1.00 | 1.00 | 1.00 | 1.00 | 1.00 | 1.00 |
| 4930523O13Rik | 1.00 | 1.00 | 1.00 | 1.00 | 1.00 | 1.00 | 1.00 | 1.00 | 1.00 | 1.00 | 1.00 | 1.00 |
| 4930526I15Rik | 0.68 | 2.10 | 1.25 | 0.70 | 0.58 | 1.06 | 1.19 | 12.28 | 1.09 | 4.19 | 1.18 | 1.04 |
| 4930529K09Rik | 1.00 | 1.00 | 1.00 | 1.00 | 1.00 | 1.00 | 1.00 | 1.00 | 1.00 | 1.00 | 1.00 | 1.00 |
| 4930539J05Rik | 1.00 | 1.00 | 1.00 | 1.04 | 4.35 | 1.04 | 1.16 | 10.17 | 0.77 | 1.00 | 1.00 | 1.00 |
| 4930593C16Rik | 1.00 | 1.00 | 1.00 | 1.00 | 1.00 | 1.00 | 1.00 | 1.00 | 1.00 | 1.00 | 1.00 | 1.00 |
| 4931428L18Rik | 1.00 | 1.00 | 1.00 | 1.00 | 1.00 | 1.00 | 1.00 | 1.00 | 1.00 | 5.05 | 1.86 | 1.58 |
| 4932414J04Rik | 1.00 | 1.00 | 1.00 | 1.00 | 1.00 | 1.00 | 1.00 | 1.00 | 1.00 | 1.00 | 1.00 | 1.00 |
| 4932702P03Rik | 1.00 | 1.00 | 1.00 | 1.00 | 1.00 | 1.00 | 1.00 | 3.13 | 1.00 | 1.00 | 1.00 | 1.00 |
| 4933402C06Rik | 1.00 | 1.00 | 1.00 | 1.00 | 1.00 | 1.00 | 1.00 | 1.00 | 1.00 | 1.00 | 1.00 | 1.00 |
| 4933406K04Rik | 1.00 | 1.00 | 1.00 | 1.00 | 1.00 | 1.00 | 1.00 | 1.00 | 1.00 | 1.00 | 1.00 | 1.00 |
| 4933407E24Rik | 1.00 | 1.00 | 1.00 | 1.00 | 1.00 | 1.00 | 1.00 | 1.00 | 1.00 | 1.00 | 1.00 | 1.00 |
| 4933409K07Rik | 1.00 | 1.00 | 1.00 | 7.10 | 0.23 | 10.09 | 11.08 | 9.47 | 16.75 | 1.00 | 1.00 | 1.00 |
| 4933411K16Rik | 1.00 | 1.06 | 1.00 | 1.00 | 1.00 | 1.00 | 13.16 | 1.00 | 1.00 | 1.00 | 1.00 | 1.00 |

Fig. 35- 117

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| 4933422A05Rik | 1.00 | 1.00 | 1.00 | 1.00 | 1.00 | 1.00 | 1.00 | 1.00 | 1.00 | 1.00 | 1.00 | 1.00 |
| 4933439C10Rik | 1.00 | 0.67 | 0.87 | 1.28 | 4.12 | 1.53 | 1.00 | 0.90 | 1.32 | 3.32 | 2.64 | 0.90 |
| 5031434O11Rik | 1.31 | 0.87 | 2.10 | 1.82 | 15.74 | 0.84 | 1.08 | 1.22 | 1.02 | 1.07 | 3.07 | 1.00 |
| 5430405H02Rik | 1.15 | 0.61 | 0.64 | 0.59 | 4.83 | 1.16 | 1.11 | 0.90 | 0.78 | 3.38 | 2.22 | 1.36 |
| 5430421N21Rik | 1.00 | 1.00 | 1.00 | 1.00 | 1.00 | 1.00 | 1.00 | 1.00 | 1.00 | 1.00 | 1.00 | 1.00 |
| 5430425K12Rik | 1.49 | 1.62 | 1.00 | 1.90 | 2.21 | 1.00 | 1.00 | 1.00 | 1.00 | 0.62 | 0.91 | 0.84 |
| 6030408B16Rik | 1.00 | 1.67 | 1.00 | 11.29 | 94.98 | 10.53 | 1.11 | 1.23 | 1.39 | 2.21 | 3.87 | 1.20 |
| 6030419C18Rik | 0.92 | 1.07 | 0.77 | 0.59 | 0.24 | 0.64 | 0.92 | 0.86 | 0.90 | 0.69 | 0.59 | 1.12 |
| 6330403K07Rik | 0.88 | 0.53 | 0.81 | 0.67 | 0.12 | 1.17 | 0.78 | 0.62 | 0.76 | 0.90 | 0.88 | 0.63 |
| 6330418K02Rik | 1.00 | 0.37 | 1.00 | 0.91 | 3.54 | 0.71 | 0.48 | 0.72 | 1.55 | 1.53 | 1.45 | 0.77 |
| 6430531B16Rik | 1.00 | 1.00 | 1.00 | 1.00 | 1.00 | 1.00 | 1.00 | 1.00 | 1.00 | 1.70 | 3.28 | 0.90 |
| 6720468P15Rik | 1.00 | 1.00 | 1.00 | 1.00 | 1.00 | 1.00 | 2.68 | 2.10 | 3.45 | 1.00 | 1.00 | 1.00 |
| 8430408G22Rik | 4.90 | 10.20 | 14.34 | 9.93 | 22.30 | 7.65 | 1.91 | 1.78 | 1.14 | 2.74 | 2.93 | 1.10 |
| 9030025P20Rik | 1.21 | 1.27 | 1.04 | 0.60 | 2.39 | 1.06 | 0.81 | 0.79 | 1.34 | 1.90 | 2.11 | 1.03 |
| 9130204L05Rik | 1.00 | 1.00 | 1.00 | 1.00 | 1.00 | 1.00 | 1.00 | 1.00 | 1.00 | 1.00 | 1.00 | 1.00 |
| 9130401M01Rik | 0.62 | 0.52 | 0.52 | 0.50 | 3.06 | 0.65 | 1.04 | 0.73 | 0.78 | 1.99 | 2.32 | 0.90 |
| 9130409I23Rik | 1.00 | 1.00 | 1.00 | 1.00 | 1.00 | 1.00 | 1.00 | 1.00 | 1.00 | 1.00 | 1.00 | 1.00 |
| 9230102O04Rik | 1.00 | 1.00 | 1.00 | 1.00 | 1.00 | 1.00 | 1.00 | 1.00 | 1.00 | 1.00 | 1.00 | 1.00 |
| 9230105E05Rik | 1.00 | 1.00 | 1.00 | 1.00 | 1.00 | 1.00 | 1.00 | 1.00 | 1.00 | 1.00 | 1.00 | 1.00 |
| 9330020H09Rik | 1.00 | 0.46 | 1.00 | 0.58 | 4.94 | 0.73 | 1.00 | 1.00 | 1.00 | 2.70 | 3.56 | 1.00 |
| 9430016H08Rik | 1.01 | 0.88 | 1.02 | 0.79 | 1.40 | 1.00 | 0.89 | 0.96 | 0.83 | 1.88 | 1.53 | 1.06 |
| 9430037G07Rik | 0.75 | 1.00 | 1.00 | 1.00 | 0.93 | 0.59 | 1.00 | 1.00 | 1.00 | 1.00 | 1.00 | 1.00 |
| A230065H16Rik | 1.00 | 1.00 | 1.00 | 1.00 | 1.00 | 1.00 | 1.00 | 1.00 | 1.00 | 1.00 | 1.00 | 1.00 |
| A330021E22Rik | 1.00 | 1.00 | 1.00 | 1.00 | 1.00 | 1.00 | 1.00 | 1.00 | 1.00 | 5.25 | 5.75 | 2.05 |
| A330069E16Rik | 1.04 | 0.43 | 0.44 | 1.00 | 6.32 | 1.32 | 0.85 | 0.75 | 1.00 | 4.24 | 2.99 | 1.00 |
| A430005L14Rik | 1.04 | 0.64 | 0.86 | 0.65 | 6.15 | 0.89 | 0.96 | 1.04 | 0.83 | 1.78 | 3.09 | 0.97 |
| A530013C23Rik | 1.00 | 0.68 | 0.77 | 1.86 | 10.24 | 1.07 | 1.12 | 1.32 | 1.00 | 2.12 | 2.93 | 0.85 |
| A630023P12Rik | 1.00 | 1.00 | 1.00 | 1.00 | 1.00 | 1.00 | 1.00 | 1.00 | 1.00 | 0.65 | 0.93 | 0.43 |
| A730020M07Rik | 1.00 | 1.00 | 1.00 | 1.20 | 2.20 | 0.70 | 1.69 | 1.81 | 1.10 | 5.33 | 2.20 | 2.32 |
| A930001C03Rik | 1.00 | 1.00 | 1.00 | 0.10 | 0.48 | 0.81 | 1.00 | 1.00 | 1.04 | 0.52 | 1.96 | 1.00 |
| A930011O12Rik | 1.00 | 1.00 | 1.00 | 1.00 | 0.19 | 1.00 | 1.00 | 1.00 | 1.00 | 1.00 | 1.00 | 1.00 |
| AA467197 | 1.00 | 1.00 | 1.00 | 1.00 | 1.00 | 1.00 | 1.00 | 1.00 | 1.00 | 2.15 | 1.25 | 1.00 |
| AI427809 | 1.00 | 1.00 | 1.00 | 1.00 | 1.00 | 1.00 | 0.84 | 1.00 | 0.69 | 1.00 | 1.00 | 1.00 |
| AI462493 | 1.39 | 0.63 | 0.91 | 0.27 | 7.85 | 1.09 | 1.06 | 0.77 | 0.79 | 1.94 | 3.19 | 1.03 |
| AI463170 | 1.00 | 1.00 | 1.00 | 1.00 | 1.00 | 1.00 | 1.00 | 1.00 | 1.00 | 3.64 | 4.33 | 1.00 |
| AI507597 | 1.00 | 1.00 | 1.00 | 0.28 | 0.19 | 0.54 | 0.41 | 0.37 | 0.43 | 0.53 | 0.29 | 1.36 |
| AI593442 | 1.00 | 1.00 | 1.00 | 1.00 | 0.36 | 1.00 | 1.00 | 1.00 | 1.00 | 1.00 | 1.00 | 1.00 |
| AU021092 | 1.28 | 0.59 | 2.24 | 0.43 | 2.68 | 1.05 | 1.17 | 1.08 | 1.12 | 1.58 | 2.28 | 0.95 |
| AU022252 | 0.46 | 0.73 | 0.68 | 1.03 | 5.93 | 1.04 | 1.15 | 1.23 | 1.92 | 1.79 | 2.87 | 1.12 |
| AV039307 | 0.57 | 1.00 | 1.52 | 1.00 | 1.00 | 1.19 | 1.00 | 1.01 | 1.19 | 1.25 | 1.00 | 1.15 |
| AW112010 | 0.97 | 0.89 | 0.99 | 4.46 | 13.73 | 3.82 | 0.70 | 0.70 | 0.81 | 0.90 | 1.34 | 1.38 |
| AY761185 | 1.00 | 1.00 | 1.00 | 1.00 | 1.00 | 1.00 | 1.00 | 1.00 | 1.00 | 1.00 | 1.00 | 1.00 |
| Aacs | 5.86 | 3.24 | 2.83 | 1.03 | 1.26 | 1.26 | 1.56 | 1.83 | 1.37 | 0.95 | 0.94 | 1.41 |
| Aarsd1 | 1.12 | 0.51 | 0.77 | 0.91 | 11.59 | 1.51 | 0.96 | 0.99 | 0.84 | 3.75 | 3.50 | 1.11 |
| Aatf | 1.35 | 0.74 | 0.97 | 0.68 | 6.23 | 1.10 | 1.48 | 1.16 | 1.07 | 1.64 | 0.97 | 1.18 |
| Abca7 | 0.80 | 0.58 | 1.09 | 0.42 | 3.01 | 0.69 | 0.99 | 0.99 | 1.01 | 2.94 | 3.31 | 1.08 |
| Abcb1a | 2.61 | 2.42 | 3.46 | 4.54 | 1.44 | 6.06 | 3.90 | 3.81 | 3.21 | 1.48 | 1.54 | 2.57 |
| Abcb1b | 1.19 | 1.64 | 1.06 | 2.27 | 1.70 | 3.10 | 1.69 | 2.72 | 1.20 | 1.00 | 1.00 | 0.68 |
| Abcb6 | 0.88 | 0.56 | 0.67 | 0.52 | 3.43 | 0.96 | 1.13 | 1.35 | 1.12 | 2.23 | 3.21 | 1.07 |
| Abcd4 | 0.73 | 0.58 | 0.86 | 0.57 | 3.99 | 0.86 | 1.09 | 1.26 | 1.37 | 1.64 | 2.28 | 0.96 |
| Abcf1 | 1.29 | 0.73 | 1.14 | 0.72 | 6.38 | 1.21 | 1.07 | 1.21 | 1.13 | 2.28 | 3.25 | 1.04 |
| Abhd11os | 1.00 | 0.97 | 0.89 | 0.99 | 3.22 | 0.49 | 1.00 | 1.00 | 0.54 | 1.37 | 2.47 | 0.94 |
| Abra | 1.44 | 2.21 | 1.26 | 1.19 | 1.08 | 1.09 | 4.66 | 6.16 | 1.92 | 1.25 | 1.42 | 0.78 |
| Abracl | 0.99 | 1.01 | 0.86 | 1.44 | 6.88 | 2.25 | 0.58 | 0.50 | 0.64 | 1.45 | 1.53 | 0.81 |
| Abtb1 | 1.05 | 0.64 | 0.91 | 0.48 | 6.43 | 1.10 | 1.71 | 1.19 | 1.17 | 2.13 | 2.54 | 1.01 |
| Acaa1a | 1.04 | 0.52 | 1.09 | 0.30 | 3.48 | 0.88 | 1.07 | 0.87 | 0.91 | 1.86 | 2.66 | 1.11 |
| Acadvl | 0.98 | 0.53 | 0.92 | 0.43 | 3.40 | 0.89 | 0.83 | 0.85 | 0.77 | 1.96 | 2.62 | 1.15 |
| Acat3 | 1.16 | 0.41 | 0.75 | 0.63 | 3.12 | 0.74 | 0.89 | 1.34 | 0.89 | 2.58 | 2.38 | 1.26 |
| Acbd4 | 0.77 | 0.50 | 0.74 | 0.93 | 5.50 | 0.93 | 0.90 | 0.85 | 1.15 | 2.12 | 2.84 | 1.01 |
| Acmsd | 1.00 | 1.00 | 1.00 | 1.00 | 1.00 | 1.00 | 1.00 | 1.00 | 1.00 | 1.00 | 1.00 | 1.00 |
| Acot1 | 0.18 | 0.16 | 0.55 | 0.48 | 1.10 | 0.79 | 0.38 | 0.25 | 0.35 | 2.07 | 1.35 | 1.12 |
| Acot3 | 1.00 | 1.00 | 1.00 | 1.79 | 0.62 | 0.70 | 0.21 | 0.18 | 0.16 | 1.00 | 1.00 | 1.00 |
| Acot5 | 1.00 | 1.00 | 1.00 | 5.36 | 8.54 | 4.88 | 0.56 | 1.00 | 0.74 | 1.00 | 1.00 | 1.06 |
| Acot7 | 0.62 | 0.56 | 0.77 | 0.37 | 2.14 | 0.80 | 0.76 | 0.69 | 0.68 | 1.71 | 2.50 | 1.29 |

Fig. 35- 118

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| 4933422A05Rik | 1.00 | 1.00 | 1.00 | 1.00 | 1.00 | 1.00 | 1.00 | 1.00 | 1.00 | 1.00 | 1.00 | 1.00 |
| 4933439C10Rik | 1.09 | 1.20 | 0.87 | 0.70 | 0.55 | 0.97 | 0.70 | 3.08 | 0.75 | 0.99 | 1.31 | 1.07 |
| 5031434O11Rik | 0.88 | 1.73 | 0.89 | 1.00 | 2.14 | 1.00 | 1.00 | 1.00 | 1.00 | 1.22 | 1.97 | 1.30 |
| 5430405H02Rik | 1.84 | 1.62 | 0.95 | 1.11 | 0.69 | 0.92 | 0.96 | 1.42 | 1.81 | 1.03 | 1.05 | 0.99 |
| 5430421N21Rik | 1.28 | 1.14 | 1.00 | 1.00 | 1.00 | 1.00 | 1.00 | 1.00 | 1.00 | 1.00 | 1.00 | 1.00 |
| 5430425K12Rik | 1.00 | 1.00 | 1.00 | 1.00 | 1.00 | 1.00 | 1.00 | 1.00 | 1.00 | 1.00 | 1.00 | 1.00 |
| 6030408B16Rik | 1.00 | 1.04 | 1.00 | 1.00 | 1.00 | 1.00 | 1.00 | 1.00 | 1.00 | 1.00 | 1.00 | 1.00 |
| 6030419C18Rik | 0.80 | 0.77 | 0.71 | 1.00 | 0.68 | 1.00 | 1.00 | 1.00 | 1.00 | 1.49 | 1.13 | 1.30 |
| 6330403K07Rik | 0.99 | 1.09 | 1.01 | 1.00 | 1.00 | 1.00 | 1.00 | 1.00 | 1.00 | 0.80 | 1.02 | 1.14 |
| 6330418K02Rik | 1.60 | 2.03 | 1.08 | 1.32 | 0.63 | 0.75 | 1.00 | 0.56 | 0.73 | 1.53 | 1.71 | 0.85 |
| 6430531B16Rik | 1.10 | 1.00 | 0.99 | 1.00 | 1.00 | 1.00 | 1.00 | 1.00 | 1.00 | 1.00 | 1.00 | 1.00 |
| 6720468P15Rik | 1.00 | 1.00 | 1.00 | 1.00 | 1.00 | 1.00 | 1.00 | 1.00 | 1.00 | 7.26 | 10.88 | 6.48 |
| 8430408G22Rik | 29.52 | 36.48 | 14.46 | 26.72 | 50.11 | 14.60 | 2.71 | 4.43 | 1.44 | 1.96 | 2.11 | 1.97 |
| 9030025P20Rik | 1.70 | 1.96 | 1.43 | 0.94 | 1.52 | 1.19 | 0.64 | 1.05 | 0.70 | 0.83 | 1.41 | 1.16 |
| 9130204L05Rik | 1.00 | 1.00 | 1.00 | 1.00 | 1.00 | 1.00 | 1.00 | 1.00 | 1.00 | 1.00 | 1.00 | 1.00 |
| 9130401M01Rik | 0.86 | 1.32 | 0.95 | 0.86 | 0.75 | 0.79 | 0.63 | 1.22 | 0.46 | 1.01 | 1.25 | 0.81 |
| 9130409I23Rik | 1.00 | 1.00 | 1.00 | 1.00 | 1.00 | 1.00 | 6.03 | 1.61 | 8.10 | 1.00 | 1.00 | 1.00 |
| 9230102O04Rik | 1.00 | 1.00 | 1.00 | 1.05 | 1.01 | 0.95 | 1.00 | 1.00 | 1.00 | 1.00 | 1.00 | 1.00 |
| 9230105E05Rik | 1.00 | 1.00 | 1.00 | 1.00 | 1.00 | 1.00 | 1.00 | 1.00 | 1.00 | 2.29 | 3.86 | 2.94 |
| 9330020H09Rik | 0.99 | 1.29 | 1.18 | 0.83 | 0.40 | 0.92 | 1.00 | 2.95 | 1.00 | 0.83 | 1.31 | 1.25 |
| 9430016H08Rik | 1.07 | 1.41 | 0.96 | 0.93 | 0.91 | 1.11 | 1.00 | 1.13 | 1.08 | 1.09 | 1.37 | 0.90 |
| 9430037G07Rik | 1.00 | 1.00 | 1.00 | 1.00 | 1.00 | 1.00 | 8.05 | 3.91 | 8.67 | 0.86 | 1.00 | 0.94 |
| A230065H16Rik | 1.00 | 1.14 | 1.00 | 1.00 | 1.00 | 1.00 | 1.00 | 1.00 | 1.00 | 1.00 | 1.00 | 1.00 |
| A330021E22Rik | 1.00 | 1.00 | 1.00 | 1.32 | 0.61 | 1.15 | 1.00 | 1.00 | 1.00 | 1.00 | 1.00 | 1.00 |
| A330069E16Rik | 1.24 | 1.95 | 0.70 | 0.91 | 0.59 | 1.40 | 0.91 | 0.55 | 0.89 | 1.00 | 1.29 | 1.00 |
| A430005L14Rik | 1.19 | 1.28 | 0.96 | 1.11 | 0.89 | 0.81 | 1.12 | 2.15 | 0.98 | 0.91 | 1.54 | 1.06 |
| A530013C23Rik | 1.00 | 1.00 | 1.00 | 1.00 | 0.84 | 1.00 | 1.00 | 1.82 | 1.00 | 1.00 | 1.00 | 1.00 |
| A630023P12Rik | 1.01 | 0.99 | 0.96 | 1.00 | 1.00 | 1.00 | 1.00 | 1.00 | 1.00 | 0.76 | 1.60 | 0.67 |
| A730020M07Rik | 1.00 | 1.40 | 0.83 | 0.65 | 0.57 | 0.79 | 1.00 | 1.00 | 1.00 | 1.00 | 1.00 | 1.00 |
| A930001C03Rik | 1.21 | 1.53 | 0.98 | 1.32 | 1.23 | 1.02 | 0.67 | 0.56 | 0.84 | 1.00 | 0.94 | 0.84 |
| A930011O12Rik | 1.00 | 1.00 | 1.00 | 1.00 | 1.00 | 1.00 | 1.00 | 1.00 | 1.00 | 1.00 | 1.00 | 1.00 |
| AA467197 | 4.57 | 8.90 | 2.18 | 1.00 | 1.96 | 1.00 | 1.00 | 1.00 | 1.00 | 0.88 | 1.34 | 0.82 |
| AI427809 | 2.14 | 2.28 | 2.12 | 1.00 | 1.00 | 1.00 | 1.00 | 1.00 | 1.00 | 1.37 | 1.19 | 1.68 |
| AI462493 | 1.28 | 1.56 | 1.01 | 0.87 | 0.62 | 0.97 | 1.01 | 1.50 | 0.98 | 1.17 | 1.77 | 1.20 |
| AI463170 | 1.00 | 1.00 | 1.00 | 1.00 | 1.00 | 1.00 | 1.00 | 1.45 | 1.04 | 1.00 | 0.92 | 1.00 |
| AI507597 | 1.00 | 1.00 | 1.00 | 0.84 | 5.52 | 0.87 | 1.08 | 1.71 | 1.26 | 0.89 | 0.90 | 1.02 |
| AI593442 | 1.00 | 1.00 | 1.00 | 1.00 | 1.00 | 1.00 | 1.00 | 1.00 | 1.00 | 1.00 | 1.00 | 1.00 |
| AU021092 | 1.00 | 0.83 | 0.90 | 1.04 | 0.92 | 1.02 | 1.00 | 2.13 | 1.01 | 0.96 | 1.37 | 0.88 |
| AU022252 | 0.47 | 0.41 | 0.61 | 1.36 | 0.64 | 1.26 | 1.24 | 1.79 | 1.39 | 0.90 | 0.65 | 0.75 |
| AV039307 | 0.86 | 0.55 | 0.73 | 0.73 | 0.54 | 0.93 | 1.00 | 1.00 | 1.00 | 1.35 | 1.00 | 1.26 |
| AW112010 | 1.76 | 1.92 | 1.58 | 1.58 | 2.53 | 0.86 | 0.57 | 0.37 | 0.70 | 1.16 | 1.28 | 1.04 |
| AY761185 | 1.29 | 2.31 | 1.00 | 1.00 | 1.00 | 1.00 | 1.00 | 1.00 | 1.00 | 1.00 | 1.00 | 1.00 |
| Aacs | 0.71 | 0.95 | 0.97 | 0.79 | 0.94 | 0.87 | 0.57 | 0.46 | 0.49 | 1.26 | 0.95 | 1.08 |
| Aarsd1 | 0.87 | 1.17 | 0.76 | 0.80 | 0.53 | 1.01 | 1.45 | 2.22 | 0.74 | 1.08 | 1.16 | 0.88 |
| Aatf | 0.97 | 1.12 | 0.88 | 1.29 | 0.46 | 1.23 | 1.93 | 2.33 | 1.26 | 1.00 | 1.34 | 1.42 |
| Abca7 | 0.78 | 0.71 | 0.86 | 1.01 | 0.57 | 1.00 | 0.97 | 1.49 | 0.93 | 0.95 | 1.08 | 1.00 |
| Abcb1a | 2.10 | 2.16 | 2.88 | 1.28 | 1.00 | 2.10 | 1.80 | 1.00 | 1.46 | 2.67 | 2.86 | 2.26 |
| Abcb1b | 1.00 | 1.00 | 1.00 | 1.28 | 1.00 | 2.13 | 1.03 | 1.00 | 1.21 | 1.84 | 0.43 | 1.52 |
| Abcb6 | 1.18 | 1.09 | 1.17 | 1.06 | 0.72 | 1.12 | 0.78 | 1.25 | 0.98 | 0.94 | 1.05 | 0.87 |
| Abcd4 | 1.45 | 1.51 | 1.15 | 1.54 | 1.75 | 1.50 | 2.34 | 2.34 | 1.73 | 0.98 | 1.43 | 0.71 |
| Abcf1 | 1.18 | 1.31 | 1.02 | 1.25 | 0.84 | 1.04 | 1.25 | 2.01 | 1.16 | 1.05 | 1.50 | 1.07 |
| Abhd11os | 0.49 | 0.95 | 1.13 | 1.50 | 1.33 | 0.71 | 1.00 | 0.56 | 1.00 | 0.87 | 1.67 | 0.93 |
| Abra | 1.00 | 1.00 | 1.00 | 1.00 | 1.00 | 1.00 | 1.00 | 1.00 | 1.00 | 1.00 | 1.00 | 1.00 |
| Abracl | 1.09 | 1.09 | 1.09 | 1.04 | 1.34 | 1.10 | 1.60 | 1.85 | 1.47 | 1.02 | 1.46 | 0.91 |
| Abtb1 | 1.40 | 1.80 | 1.03 | 1.67 | 0.85 | 1.30 | 0.98 | 1.43 | 0.93 | 1.06 | 1.52 | 1.11 |
| Acaa1a | 1.28 | 1.50 | 1.04 | 0.75 | 0.80 | 0.95 | 0.95 | 0.87 | 0.84 | 1.01 | 1.39 | 1.09 |
| Acadvl | 1.04 | 1.27 | 0.78 | 0.81 | 0.57 | 0.82 | 0.98 | 1.50 | 0.90 | 0.91 | 1.11 | 0.95 |
| Acat3 | 1.08 | 1.11 | 0.86 | 1.45 | 1.06 | 0.79 | 0.27 | 0.68 | 0.54 | 0.76 | 1.19 | 1.07 |
| Acbd4 | 1.32 | 1.42 | 1.00 | 0.85 | 0.57 | 0.91 | 0.48 | 0.72 | 0.73 | 1.00 | 1.46 | 1.15 |
| Acmsd | 1.00 | 1.00 | 1.00 | 1.54 | 1.17 | 1.20 | 7.82 | 1.17 | 4.51 | 1.00 | 1.00 | 1.00 |
| Acot1 | 3.79 | 2.39 | 2.81 | 0.91 | 0.61 | 1.13 | 0.66 | 1.55 | 0.88 | 1.06 | 1.11 | 1.70 |
| Acot3 | 1.00 | 1.00 | 1.00 | 0.50 | 3.32 | 0.92 | 0.14 | 1.52 | 0.41 | 1.00 | 1.00 | 1.00 |
| Acot5 | 1.62 | 1.59 | 1.12 | 0.93 | 1.00 | 1.10 | 0.45 | 1.00 | 0.65 | 1.00 | 1.00 | 1.00 |
| Acot7 | 0.84 | 0.93 | 0.65 | 0.93 | 0.90 | 0.69 | 0.67 | 1.56 | 0.69 | 1.22 | 1.80 | 1.15 |

Fig. 35- 119

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| 4933422A05Rik | 1.00 | 1.00 | 1.00 | 1.00 | 1.00 | 1.00 | 5.66 | 4.66 | 3.91 | 1.00 | 1.00 | 1.00 |
| 4933439C10Rik | 0.90 | 0.88 | 1.28 | 0.88 | 0.95 | 1.34 | 1.01 | 3.97 | 0.98 | 1.04 | 1.30 | 1.24 |
| 5031434O11Rik | 1.83 | 1.66 | 2.29 | 2.75 | 4.12 | 2.33 | 1.00 | 1.00 | 1.00 | 1.48 | 1.21 | 1.34 |
| 5430405H02Rik | 0.95 | 2.63 | 1.68 | 1.04 | 1.36 | 1.82 | 1.51 | 6.62 | 1.07 | 1.20 | 1.03 | 1.45 |
| 5430421N21Rik | 1.00 | 1.00 | 1.00 | 1.00 | 1.00 | 1.00 | 1.00 | 1.00 | 1.00 | 1.00 | 1.00 | 1.00 |
| 5430425K12Rik | 1.00 | 1.00 | 1.00 | 6.59 | 1.00 | 1.00 | 1.00 | 1.00 | 1.00 | 1.00 | 1.00 | 1.00 |
| 6030408B16Rik | 1.00 | 1.00 | 1.00 | 6.76 | 20.22 | 5.69 | 1.21 | 2.17 | 1.06 | 1.00 | 1.00 | 1.00 |
| 6030419C18Rik | 1.04 | 2.13 | 1.77 | 0.71 | 1.00 | 0.82 | 1.00 | 1.00 | 0.96 | 1.00 | 9.22 | 1.00 |
| 6330403K07Rik | 0.97 | 0.81 | 0.85 | 0.84 | 2.06 | 0.86 | 1.00 | 1.00 | 0.91 | 1.01 | 5.95 | 0.94 |
| 6330418K02Rik | 0.59 | 1.33 | 0.71 | 0.54 | 0.53 | 1.13 | 1.04 | 1.33 | 0.72 | 0.77 | 0.75 | 1.63 |
| 6430531B16Rik | 1.00 | 1.00 | 1.00 | 0.76 | 1.15 | 1.00 | 1.15 | 2.64 | 1.19 | 1.00 | 1.00 | 1.00 |
| 6720468P15Rik | 9.94 | 12.51 | 7.47 | 1.00 | 1.00 | 1.00 | 1.23 | 2.76 | 1.11 | 1.00 | 1.00 | 1.00 |
| 8430408G22Rik | 3.84 | 4.79 | 2.80 | 2.40 | 7.05 | 2.16 | 1.00 | 1.66 | 1.00 | 1.40 | 2.91 | 1.23 |
| 9030025P20Rik | 1.25 | 0.98 | 1.28 | 0.80 | 1.82 | 1.06 | 0.97 | 1.17 | 0.96 | 1.08 | 1.29 | 1.18 |
| 9130204L05Rik | 0.61 | 0.50 | 0.46 | 1.00 | 1.00 | 1.00 | 0.63 | 0.84 | 0.62 | 1.00 | 1.00 | 1.00 |
| 9130401M01Rik | 0.63 | 0.78 | 0.79 | 0.53 | 1.79 | 0.57 | 0.92 | 1.63 | 0.88 | 1.13 | 1.22 | 0.97 |
| 9130409I23Rik | 0.98 | 1.08 | 1.04 | 1.00 | 1.00 | 1.00 | 1.00 | 1.00 | 1.00 | 1.00 | 1.00 | 1.00 |
| 9230102O04Rik | 1.00 | 1.00 | 1.00 | 1.00 | 1.00 | 1.00 | 0.77 | 2.13 | 1.15 | 1.00 | 1.00 | 1.00 |
| 9230105E05Rik | 1.00 | 1.00 | 1.00 | 1.00 | 1.00 | 1.00 | 2.07 | 5.23 | 2.98 | 1.00 | 1.00 | 1.00 |
| 9330020H09Rik | 1.32 | 1.21 | 0.83 | 0.83 | 0.80 | 0.92 | 0.97 | 2.83 | 1.11 | 1.07 | 1.39 | 0.98 |
| 9430016H08Rik | 0.93 | 0.89 | 0.81 | 0.91 | 6.01 | 1.02 | 1.00 | 1.22 | 0.99 | 1.12 | 1.52 | 0.99 |
| 9430037G07Rik | 1.00 | 1.00 | 1.00 | 1.00 | 1.00 | 1.00 | 1.00 | 1.00 | 1.00 | 1.00 | 1.00 | 1.00 |
| A230065H16Rik | 1.00 | 1.00 | 1.00 | 1.00 | 1.00 | 1.00 | 1.00 | 3.60 | 1.00 | 1.00 | 0.81 | 0.48 |
| A330021E22Rik | 1.21 | 0.85 | 0.70 | 0.94 | 1.00 | 1.22 | 1.07 | 3.24 | 1.12 | 1.00 | 1.00 | 1.00 |
| A330069E16Rik | 1.00 | 1.00 | 1.00 | 0.99 | 0.28 | 0.98 | 0.89 | 5.33 | 1.00 | 2.13 | 0.98 | 1.20 |
| A430005L14Rik | 0.99 | 0.85 | 0.93 | 0.94 | 1.91 | 1.11 | 0.89 | 2.25 | 0.95 | 0.83 | 1.03 | 0.88 |
| A530013C23Rik | 1.00 | 1.00 | 1.00 | 0.69 | 0.65 | 0.49 | 1.00 | 1.00 | 1.00 | 1.00 | 1.00 | 1.00 |
| A630023P12Rik | 1.00 | 1.00 | 1.00 | 1.00 | 1.00 | 1.77 | 0.83 | 1.93 | 1.72 | 1.15 | 1.13 | 0.94 |
| A730020M07Rik | 1.00 | 1.00 | 1.00 | 0.83 | 1.00 | 0.77 | 1.00 | 1.00 | 1.00 | 0.62 | 0.60 | 0.56 |
| A930001C03Rik | 0.62 | 0.69 | 0.83 | 0.85 | 1.00 | 1.15 | 1.00 | 0.50 | 1.40 | 1.00 | 1.00 | 1.00 |
| A930011O12Rik | 1.00 | 1.00 | 1.00 | 1.00 | 1.00 | 1.00 | 1.00 | 1.00 | 1.00 | 1.00 | 9.13 | 1.00 |
| AA467197 | 0.64 | 1.00 | 0.79 | 1.67 | 2.17 | 2.16 | 0.91 | 0.67 | 0.96 | 2.93 | 1.68 | 1.22 |
| AI427809 | 1.00 | 1.00 | 1.00 | 0.78 | 1.00 | 0.92 | 1.00 | 1.00 | 1.00 | 1.28 | 1.47 | 5.54 |
| AI462493 | 1.32 | 1.21 | 1.10 | 0.99 | 3.76 | 1.12 | 0.92 | 1.86 | 0.88 | 1.01 | 1.38 | 1.02 |
| AI463170 | 1.00 | 1.00 | 0.99 | 1.00 | 1.00 | 1.00 | 1.00 | 1.00 | 1.00 | 1.00 | 1.00 | 1.00 |
| AI507597 | 0.71 | 1.69 | 1.39 | 4.50 | 1.82 | 2.72 | 0.87 | 0.81 | 0.98 | 1.73 | 1.15 | 1.68 |
| AI593442 | 1.00 | 1.00 | 1.00 | 1.00 | 1.00 | 1.00 | 1.00 | 1.00 | 1.00 | 1.00 | 5.14 | 1.00 |
| AU021092 | 1.15 | 1.32 | 1.24 | 1.30 | 3.25 | 1.82 | 1.11 | 1.18 | 0.75 | 1.02 | 1.17 | 0.99 |
| AU022252 | 1.04 | 0.89 | 0.88 | 2.08 | 12.49 | 0.91 | 0.82 | 1.58 | 0.89 | 0.70 | 0.69 | 1.24 |
| AV039307 | 1.05 | 2.05 | 1.00 | 1.00 | 0.19 | 0.78 | 0.81 | 1.41 | 0.95 | 0.89 | 0.74 | 0.97 |
| AW112010 | 1.20 | 1.55 | 1.43 | 1.35 | 6.00 | 0.67 | 1.00 | 0.97 | 1.00 | 1.01 | 0.89 | 0.78 |
| AY761185 | 1.00 | 1.00 | 1.00 | 1.00 | 6.03 | 0.06 | 1.00 | 1.00 | 1.00 | 1.00 | 1.00 | 1.00 |
| Aacs | 0.85 | 0.94 | 0.85 | 1.05 | 0.87 | 1.46 | 1.10 | 0.69 | 0.91 | 1.16 | 0.92 | 1.05 |
| Aarsd1 | 1.02 | 0.84 | 0.94 | 1.45 | 2.43 | 1.49 | 0.81 | 3.80 | 0.76 | 0.96 | 1.13 | 0.90 |
| Aatf | 1.15 | 0.96 | 0.96 | 1.41 | 1.54 | 1.35 | 0.91 | 2.38 | 0.84 | 1.22 | 1.26 | 0.95 |
| Abca7 | 1.24 | 1.29 | 0.92 | 0.95 | 2.57 | 0.96 | 1.00 | 2.62 | 1.00 | 0.72 | 0.71 | 0.86 |
| Abcb1a | 1.57 | 1.76 | 1.97 | 8.33 | 1.00 | 5.34 | 1.50 | 1.00 | 1.14 | 1.97 | 1.76 | 1.22 |
| Abcb1b | 1.00 | 1.00 | 1.00 | 5.07 | 1.00 | 2.82 | 1.00 | 1.00 | 1.00 | 0.31 | 0.32 | 0.22 |
| Abcb6 | 0.69 | 0.69 | 0.63 | 1.22 | 4.20 | 1.21 | 1.20 | 1.75 | 1.14 | 0.71 | 0.95 | 0.65 |
| Abcd4 | 1.16 | 1.13 | 1.02 | 1.61 | 2.33 | 1.13 | 1.00 | 1.31 | 1.00 | 1.04 | 1.38 | 1.11 |
| Abcf1 | 1.13 | 1.19 | 1.07 | 1.18 | 2.29 | 1.23 | 0.98 | 2.08 | 1.09 | 1.06 | 1.25 | 1.07 |
| Abhd11os | 1.49 | 0.68 | 1.64 | 1.06 | 6.95 | 0.25 | 1.00 | 1.00 | 1.00 | 1.00 | 0.70 | 0.52 |
| Abra | 2.55 | 1.70 | 2.38 | 1.00 | 1.00 | 1.00 | 0.88 | 0.81 | 0.86 | 1.00 | 1.00 | 1.00 |
| Abracl | 1.11 | 1.04 | 0.99 | 0.82 | 1.90 | 0.85 | 1.43 | 1.47 | 1.23 | 1.06 | 1.06 | 1.00 |
| Abtb1 | 1.32 | 1.54 | 1.32 | 0.98 | 3.11 | 0.90 | 0.98 | 1.86 | 0.94 | 1.08 | 1.26 | 0.95 |
| Acaa1a | 0.85 | 0.87 | 0.84 | 0.82 | 2.07 | 1.18 | 0.90 | 2.30 | 0.75 | 0.95 | 1.40 | 1.04 |
| Acadvl | 1.02 | 1.03 | 1.07 | 0.77 | 3.30 | 0.86 | 0.98 | 1.82 | 0.71 | 0.97 | 0.97 | 1.09 |
| Acat3 | 1.38 | 0.77 | 1.09 | 0.88 | 6.93 | 0.97 | 0.85 | 3.34 | 1.25 | 1.08 | 1.43 | 1.17 |
| Acbd4 | 0.99 | 0.97 | 1.21 | 0.69 | 1.83 | 0.73 | 1.08 | 2.00 | 1.03 | 1.10 | 1.13 | 1.25 |
| Acmsd | 1.00 | 1.00 | 1.00 | 1.00 | 1.00 | 1.00 | 1.00 | 1.00 | 1.00 | 0.49 | 0.95 | 1.00 |
| Acot1 | 0.85 | 0.95 | 1.30 | 1.53 | 5.24 | 2.23 | 0.74 | 1.91 | 0.54 | 0.54 | 0.71 | 0.63 |
| Acot3 | 0.70 | 0.95 | 1.00 | 4.67 | 1.44 | 11.89 | 1.00 | 1.00 | 1.00 | 1.00 | 1.00 | 1.00 |
| Acot5 | 1.00 | 1.00 | 1.00 | 18.92 | 17.80 | 19.30 | 1.00 | 1.00 | 1.00 | 1.00 | 1.00 | 1.00 |
| Acot7 | 1.05 | 0.85 | 1.12 | 0.98 | 2.99 | 0.81 | 0.94 | 1.45 | 1.03 | 0.91 | 1.82 | 0.65 |

Fig. 35- 120

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| 4933422A05Rik | 1.00 | 1.00 | 1.00 | 1.00 | 1.00 | 1.00 | 1.00 | 1.00 | 1.00 | 1.00 | 1.00 | 1.00 |
| 4933439C10Rik | 0.74 | 1.00 | 0.96 | 1.15 | 0.92 | 0.92 | 1.29 | 5.12 | 1.07 | 1.83 | 0.87 | 0.84 |
| 5031434O11Rik | 1.00 | 1.02 | 1.00 | 1.08 | 1.08 | 1.61 | 1.27 | 5.63 | 1.30 | 2.52 | 1.20 | 1.59 |
| 5430405H02Rik | 1.00 | 0.90 | 1.00 | 1.15 | 0.31 | 1.11 | 1.13 | 5.80 | 0.99 | 2.84 | 1.21 | 1.25 |
| 5430421N21Rik | 1.00 | 1.00 | 1.00 | 1.00 | 1.00 | 1.00 | 2.82 | 5.71 | 1.00 | 6.05 | 3.81 | 1.23 |
| 5430425K12Rik | 1.00 | 1.00 | 1.00 | 1.00 | 1.00 | 1.00 | 1.00 | 1.87 | 1.00 | 2.63 | 3.08 | 1.72 |
| 6030408B16Rik | 1.00 | 1.00 | 1.00 | 1.00 | 0.41 | 1.00 | 1.00 | 4.27 | 1.00 | 1.00 | 1.00 | 1.00 |
| 6030419C18Rik | 1.00 | 1.00 | 1.00 | 1.11 | 0.98 | 1.06 | 0.81 | 0.66 | 1.14 | 1.00 | 1.00 | 1.00 |
| 6330403K07Rik | 1.00 | 1.00 | 1.00 | 1.16 | 1.16 | 1.08 | 0.93 | 1.33 | 1.13 | 1.00 | 1.00 | 1.00 |
| 6330418K02Rik | 1.00 | 0.61 | 1.00 | 0.78 | 0.66 | 1.23 | 0.88 | 6.28 | 0.81 | 3.00 | 1.32 | 1.23 |
| 6430531B16Rik | 1.00 | 1.00 | 1.00 | 1.00 | 2.74 | 1.00 | 1.53 | 4.92 | 1.66 | 5.17 | 1.46 | 1.60 |
| 6720468P15Rik | 1.00 | 1.00 | 1.00 | 1.00 | 1.00 | 1.00 | 1.00 | 1.00 | 1.00 | 1.00 | 1.00 | 1.00 |
| 8430408G22Rik | 2.97 | 2.13 | 2.91 | 0.99 | 1.51 | 0.88 | 4.23 | 8.89 | 3.82 | 1.00 | 0.82 | 1.00 |
| 9030025P20Rik | 1.23 | 1.00 | 1.05 | 0.97 | 2.14 | 0.97 | 1.32 | 5.00 | 1.64 | 1.71 | 1.36 | 1.11 |
| 9130204L05Rik | 1.00 | 1.00 | 1.00 | 1.00 | 1.00 | 1.00 | 1.17 | 2.47 | 5.07 | 1.00 | 1.00 | 1.00 |
| 9130401M01Rik | 1.00 | 1.43 | 0.67 | 0.95 | 1.71 | 0.92 | 1.14 | 6.39 | 1.02 | 1.25 | 0.77 | 0.67 |
| 9130409I23Rik | 1.00 | 1.00 | 1.00 | 1.00 | 1.00 | 1.00 | 1.00 | 1.00 | 1.00 | 1.00 | 1.00 | 1.00 |
| 9230102O04Rik | 1.00 | 1.00 | 1.00 | 1.00 | 1.32 | 1.00 | 0.56 | 7.06 | 0.87 | 1.00 | 1.00 | 1.00 |
| 9230105E05Rik | 1.00 | 1.00 | 1.00 | 1.00 | 1.00 | 1.00 | 1.00 | 1.00 | 1.00 | 1.00 | 1.00 | 1.00 |
| 9330020H09Rik | 1.00 | 1.00 | 1.00 | 1.00 | 0.84 | 1.00 | 1.21 | 9.82 | 0.93 | 3.39 | 1.32 | 0.95 |
| 9430016H08Rik | 0.71 | 1.22 | 1.05 | 1.24 | 0.90 | 1.10 | 1.38 | 1.46 | 0.98 | 1.41 | 1.05 | 0.75 |
| 9430037G07Rik | 1.00 | 1.00 | 1.00 | 0.98 | 1.00 | 1.00 | 1.00 | 1.00 | 1.00 | 1.00 | 1.00 | 1.00 |
| A230065H16Rik | 1.00 | 1.00 | 1.00 | 0.76 | 0.73 | 1.01 | 1.00 | 6.37 | 1.00 | 1.00 | 1.00 | 1.00 |
| A330021E22Rik | 1.00 | 1.00 | 1.00 | 0.90 | 1.29 | 0.93 | 1.00 | 1.00 | 1.00 | 1.00 | 1.00 | 1.00 |
| A330069E16Rik | 1.00 | 1.00 | 1.00 | 1.30 | 2.08 | 1.03 | 2.67 | 12.68 | 0.63 | 3.46 | 1.11 | 0.81 |
| A430005L14Rik | 0.74 | 1.24 | 0.84 | 1.01 | 0.92 | 1.08 | 1.00 | 5.79 | 0.82 | 2.01 | 1.15 | 0.99 |
| A530013C23Rik | 1.00 | 1.00 | 1.00 | 1.00 | 1.00 | 1.00 | 2.09 | 10.02 | 1.67 | 1.00 | 1.08 | 1.00 |
| A630023P12Rik | 1.00 | 1.00 | 1.00 | 1.00 | 5.05 | 0.77 | 1.00 | 1.00 | 1.00 | 1.70 | 1.35 | 0.97 |
| A730020M07Rik | 1.00 | 1.00 | 1.00 | 1.93 | 1.00 | 1.72 | 1.00 | 1.09 | 1.00 | 1.00 | 1.00 | 1.00 |
| A930001C03Rik | 1.00 | 1.00 | 1.00 | 1.52 | 1.00 | 1.17 | 1.03 | 6.97 | 0.81 | 1.00 | 1.00 | 1.00 |
| A930011O12Rik | 1.00 | 1.00 | 1.00 | 0.94 | 1.12 | 1.00 | 1.00 | 1.00 | 1.00 | 1.00 | 1.00 | 1.00 |
| AA467197 | 1.00 | 1.00 | 1.00 | 1.00 | 1.00 | 1.00 | 3.32 | 2.21 | 0.69 | 2.72 | 1.69 | 1.73 |
| AI427809 | 0.63 | 0.76 | 1.38 | 1.00 | 1.00 | 1.00 | 1.00 | 1.00 | 0.82 | 0.79 | 0.46 | 0.85 |
| AI462493 | 1.25 | 0.89 | 1.05 | 1.22 | 0.71 | 1.05 | 1.24 | 6.99 | 0.94 | 2.94 | 1.19 | 1.16 |
| AI463170 | 1.91 | 1.00 | 1.00 | 1.00 | 1.00 | 1.00 | 1.86 | 8.66 | 1.07 | 6.39 | 1.44 | 1.32 |
| AI507597 | 1.00 | 1.08 | 1.00 | 1.00 | 1.00 | 1.00 | 4.00 | 1.00 | 1.76 | 1.00 | 1.00 | 1.00 |
| AI593442 | 1.00 | 1.00 | 1.00 | 1.02 | 1.61 | 0.96 | 1.00 | 1.00 | 1.00 | 1.00 | 1.00 | 1.00 |
| AU021092 | 1.00 | 1.00 | 1.00 | 0.86 | 0.67 | 0.92 | 2.49 | 7.60 | 1.06 | 1.00 | 1.00 | 1.00 |
| AU022252 | 1.10 | 1.16 | 0.93 | 0.73 | 1.51 | 0.72 | 0.44 | 1.13 | 0.54 | 2.42 | 0.58 | 0.52 |
| AV039307 | 1.00 | 1.00 | 1.00 | 0.46 | 5.04 | 0.96 | 1.00 | 1.00 | 1.39 | 1.00 | 1.00 | 0.90 |
| AW112010 | 1.37 | 0.80 | 1.40 | 0.92 | 0.17 | 1.00 | 2.62 | 1.64 | 1.21 | 1.57 | 1.73 | 1.26 |
| AY761185 | 1.00 | 1.00 | 1.00 | 1.00 | 1.00 | 1.00 | 1.00 | 1.00 | 1.00 | 1.00 | 1.00 | 1.00 |
| Aacs | 1.00 | 1.00 | 1.03 | 1.15 | 0.56 | 0.96 | 0.87 | 0.35 | 0.73 | 0.72 | 1.43 | 1.27 |
| Aarsd1 | 1.43 | 0.73 | 1.13 | 1.07 | 1.12 | 0.97 | 1.14 | 12.48 | 0.90 | 2.07 | 0.68 | 0.78 |
| Aatf | 1.05 | 0.68 | 1.43 | 0.98 | 1.49 | 1.03 | 0.92 | 1.42 | 0.92 | 0.84 | 0.93 | 0.85 |
| Abca7 | 1.00 | 1.00 | 1.00 | 0.94 | 1.24 | 0.95 | 0.79 | 5.97 | 0.95 | 3.43 | 1.05 | 0.87 |
| Abcb1a | 1.00 | 1.00 | 1.00 | 2.98 | 1.00 | 3.02 | 1.84 | 1.00 | 1.71 | 1.00 | 1.00 | 1.00 |
| Abcb1b | 1.00 | 1.00 | 1.00 | 1.00 | 1.00 | 1.00 | 0.62 | 0.45 | 0.73 | 1.00 | 1.00 | 0.88 |
| Abcb6 | 1.13 | 0.84 | 0.89 | 1.05 | 0.77 | 0.93 | 1.13 | 5.73 | 1.11 | 1.45 | 0.69 | 0.79 |
| Abcd4 | 1.00 | 1.00 | 1.00 | 1.12 | 1.39 | 1.05 | 0.99 | 5.12 | 0.90 | 2.61 | 2.11 | 1.92 |
| Abcf1 | 1.22 | 1.09 | 1.15 | 1.20 | 0.98 | 1.10 | 1.18 | 8.41 | 0.98 | 2.13 | 1.13 | 0.91 |
| Abhd11os | 1.00 | 1.00 | 1.74 | 0.92 | 1.51 | 1.20 | 0.89 | 6.01 | 0.71 | 1.00 | 1.00 | 1.00 |
| Abra | 1.00 | 1.00 | 1.00 | 1.00 | 1.00 | 1.00 | 1.33 | 0.48 | 1.72 | 1.00 | 1.00 | 1.00 |
| Abracl | 1.43 | 0.94 | 0.91 | 1.68 | 0.82 | 1.04 | 1.01 | 4.26 | 1.05 | 1.83 | 1.30 | 1.26 |
| Abtb1 | 1.19 | 1.15 | 0.91 | 1.00 | 1.01 | 1.04 | 1.37 | 6.00 | 1.23 | 2.87 | 1.56 | 1.26 |
| Acaa1a | 0.85 | 0.73 | 0.71 | 0.94 | 1.67 | 0.95 | 1.30 | 6.15 | 0.99 | 2.48 | 1.40 | 1.38 |
| Acadvl | 0.88 | 0.79 | 0.84 | 1.10 | 0.68 | 1.04 | 1.12 | 5.52 | 0.94 | 2.46 | 1.12 | 1.04 |
| Acat3 | 1.00 | 1.00 | 1.00 | 1.08 | 1.08 | 1.11 | 0.93 | 7.26 | 1.08 | 1.97 | 1.58 | 0.85 |
| Acbd4 | 1.18 | 1.29 | 1.01 | 1.08 | 1.18 | 1.09 | 0.94 | 3.90 | 0.89 | 2.34 | 1.27 | 1.28 |
| Acmsd | 1.00 | 1.00 | 1.00 | 1.00 | 1.00 | 1.00 | 1.00 | 1.00 | 1.00 | 0.32 | 0.59 | 0.52 |
| Acot1 | 0.57 | 0.62 | 0.70 | 0.97 | 0.83 | 0.70 | 1.10 | 2.96 | 0.96 | 0.91 | 0.79 | 1.09 |
| Acot3 | 1.00 | 1.00 | 1.00 | 0.57 | 1.00 | 0.70 | 1.00 | 1.00 | 1.00 | 1.00 | 1.00 | 1.00 |
| Acot5 | 1.00 | 1.00 | 1.00 | 1.06 | 1.00 | 1.06 | 7.93 | 5.66 | 4.83 | 1.00 | 1.00 | 1.00 |
| Acot7 | 1.43 | 1.25 | 0.62 | 1.08 | 0.98 | 1.03 | 1.54 | 6.30 | 1.21 | 2.35 | 1.36 | 1.03 |

Fig. 35- 121

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Acoxl | 1.00 | 1.00 | 1.00 | 1.00 | 1.00 | 1.00 | 1.00 | 1.00 | 1.00 | 5.77 | 6.01 | 5.70 |
| Acsf3 | 0.76 | 0.60 | 0.95 | 0.47 | 2.72 | 0.72 | 1.08 | 1.11 | 0.95 | 2.13 | 2.53 | 0.88 |
| Acsm1 | 1.00 | 1.00 | 1.00 | 1.00 | 1.00 | 1.00 | 1.00 | 1.00 | 1.00 | 3.31 | 3.74 | 1.26 |
| Acta1 | 1.38 | 0.87 | 1.09 | 0.90 | 4.57 | 1.15 | 2.06 | 1.20 | 1.60 | 2.34 | 2.10 | 2.33 |
| Actb | 0.94 | 0.64 | 1.01 | 0.65 | 5.28 | 1.75 | 0.84 | 0.63 | 0.99 | 2.32 | 2.60 | 0.94 |
| Actl7b | 1.00 | 1.00 | 1.00 | 1.00 | 1.00 | 1.00 | 1.00 | 1.00 | 1.00 | 1.00 | 1.00 | 1.00 |
| Actn3 | 1.00 | 0.70 | 0.97 | 2.05 | 7.55 | 1.82 | 1.00 | 1.00 | 1.00 | 1.00 | 1.00 | 1.00 |
| Actr5 | 1.40 | 0.58 | 1.14 | 0.80 | 9.06 | 1.05 | 1.32 | 0.95 | 0.98 | 3.64 | 5.08 | 1.08 |
| Ada | 1.00 | 1.00 | 1.00 | 1.00 | 1.00 | 1.00 | 1.00 | 1.00 | 1.00 | 8.46 | 5.86 | 1.09 |
| Adamtsl4 | 0.44 | 0.55 | 0.59 | 1.15 | 0.94 | 0.57 | 1.00 | 0.92 | 0.89 | 0.86 | 1.03 | 1.32 |
| Adat2 | 0.89 | 1.72 | 1.66 | 0.51 | 2.56 | 1.12 | 1.80 | 1.74 | 1.95 | 6.99 | 6.22 | 2.34 |
| Adck4 | 2.03 | 1.03 | 1.28 | 0.66 | 6.84 | 0.84 | 1.10 | 0.95 | 1.03 | 2.57 | 3.48 | 1.12 |
| Adck5 | 0.79 | 0.44 | 1.46 | 0.41 | 5.09 | 1.87 | 1.03 | 0.94 | 1.20 | 2.05 | 3.43 | 0.86 |
| Adcy1 | 1.00 | 1.00 | 1.00 | 1.00 | 0.19 | 1.00 | 1.00 | 1.00 | 2.04 | 1.00 | 1.00 | 1.00 |
| Adh1 | 0.51 | 0.45 | 0.70 | 1.94 | 5.68 | 5.00 | 0.51 | 0.59 | 0.68 | 0.51 | 0.36 | 0.78 |
| Adh6-ps1 | 1.00 | 1.00 | 1.00 | 1.00 | 1.00 | 1.00 | 1.00 | 1.00 | 1.00 | 1.00 | 1.00 | 1.00 |
| Adh6a | 1.00 | 1.00 | 1.00 | 1.00 | 1.00 | 1.00 | 1.00 | 1.00 | 1.00 | 1.00 | 1.00 | 1.00 |
| Adh7 | 1.00 | 1.00 | 1.00 | 1.00 | 1.00 | 1.00 | 1.00 | 1.00 | 1.00 | 1.74 | 2.19 | 1.27 |
| Adig | 1.55 | 0.94 | 2.48 | 0.54 | 8.76 | 1.34 | 0.64 | 0.38 | 1.09 | 1.93 | 3.34 | 1.00 |
| Adora1 | 0.67 | 0.35 | 0.49 | 0.95 | 0.64 | 0.81 | 1.94 | 2.45 | 1.69 | 1.72 | 1.82 | 1.38 |
| Adrb2 | 2.36 | 2.62 | 1.24 | 4.17 | 20.79 | 3.04 | 0.74 | 0.92 | 1.01 | 2.94 | 2.18 | 1.57 |
| Aes | 1.15 | 0.64 | 0.73 | 0.42 | 3.48 | 0.79 | 0.82 | 0.78 | 0.78 | 1.73 | 2.06 | 0.97 |
| Ager | 1.00 | 1.00 | 1.00 | 0.79 | 7.38 | 1.00 | 1.00 | 1.00 | 1.00 | 3.17 | 3.88 | 1.32 |
| Agrp | 1.00 | 1.00 | 1.00 | 1.00 | 1.00 | 1.00 | 1.00 | 1.00 | 1.00 | 4.14 | 6.97 | 1.08 |
| Agt | 13.52 | 8.28 | 2.84 | 8.98 | 9.31 | 5.14 | 1.01 | 1.02 | 1.17 | 13.08 | 29.64 | 8.12 |
| Ahsg | 1.79 | 1.01 | 1.00 | 1.09 | 0.74 | 0.50 | 2.13 | 0.93 | 2.17 | 0.05 | 1.07 | 1.08 |
| Aif1 | 1.00 | 1.00 | 1.00 | 1.00 | 1.17 | 1.00 | 1.00 | 1.00 | 0.74 | 2.78 | 2.11 | 1.78 |
| Aifm2 | 1.17 | 0.87 | 1.58 | 1.36 | 4.39 | 1.45 | 0.91 | 1.01 | 0.91 | 2.91 | 2.53 | 1.01 |
| Aimp1 | 1.09 | 0.88 | 0.87 | 0.65 | 3.50 | 1.30 | 1.05 | 0.96 | 0.98 | 1.24 | 1.89 | 1.10 |
| Aimp2 | 0.94 | 0.60 | 0.63 | 0.64 | 4.29 | 0.91 | 0.97 | 0.91 | 0.83 | 1.40 | 2.09 | 0.94 |
| Ak6 | 1.24 | 0.87 | 0.85 | 0.75 | 3.99 | 1.00 | 1.02 | 1.06 | 0.86 | 1.38 | 1.57 | 1.20 |
| Akap4 | 1.00 | 1.00 | 1.00 | 1.00 | 1.00 | 1.00 | 1.00 | 1.00 | 1.00 | 1.00 | 1.00 | 1.00 |
| Akap8l | 0.99 | 0.60 | 1.12 | 0.96 | 6.32 | 1.10 | 1.20 | 1.01 | 0.92 | 2.62 | 3.42 | 1.01 |
| Akip1 | 2.14 | 1.24 | 1.65 | 2.16 | 11.59 | 1.17 | 1.18 | 0.82 | 0.86 | 1.40 | 1.58 | 1.07 |
| Akp3 | 1.00 | 1.00 | 1.00 | 1.00 | 1.00 | 1.00 | 1.50 | 1.00 | 1.00 | 1.00 | 1.00 | 1.00 |
| Akr1b8 | 1.05 | 0.70 | 1.56 | 0.25 | 3.97 | 0.52 | 1.04 | 0.80 | 1.45 | 1.47 | 3.27 | 1.11 |
| Akr7a5 | 1.29 | 0.50 | 0.89 | 0.56 | 8.01 | 1.21 | 1.04 | 0.82 | 0.96 | 3.22 | 3.60 | 0.95 |
| Alb | 2.97 | 0.79 | 1.00 | 1.22 | 0.40 | 0.61 | 14.77 | 0.11 | 1.99 | 0.06 | 0.66 | 1.36 |
| Aldh1a1 | 1.34 | 1.27 | 1.17 | 1.48 | 3.60 | 1.94 | 1.01 | 1.04 | 0.89 | 1.73 | 1.76 | 1.01 |
| Aldh1l1 | 1.06 | 0.86 | 1.10 | 0.76 | 16.78 | 1.40 | 1.69 | 1.15 | 1.57 | 6.77 | 7.60 | 2.22 |
| Aldh3a1 | 1.03 | 1.37 | 1.00 | 1.00 | 1.00 | 1.00 | 0.91 | 1.33 | 1.00 | 4.53 | 4.17 | 1.49 |
| Aldh7a1 | 0.61 | 0.43 | 1.09 | 0.60 | 2.32 | 0.88 | 1.05 | 0.89 | 0.93 | 2.39 | 3.02 | 1.12 |
| Aldob | 1.00 | 1.24 | 1.00 | 1.00 | 1.05 | 1.00 | 2.67 | 0.59 | 0.66 | 0.34 | 1.00 | 1.00 |
| Aldoc | 1.00 | 1.00 | 1.00 | 1.00 | 0.04 | 1.00 | 1.00 | 1.00 | 1.00 | 0.90 | 1.42 | 0.85 |
| Alg1 | 1.20 | 1.11 | 1.34 | 0.44 | 0.33 | 1.26 | 1.19 | 0.96 | 1.22 | 0.31 | 0.61 | 0.99 |
| Alg3 | 1.26 | 0.57 | 0.76 | 0.26 | 2.20 | 1.05 | 0.86 | 0.51 | 0.86 | 2.82 | 3.79 | 0.90 |
| Alkbh2 | 0.87 | 0.66 | 0.64 | 0.79 | 10.21 | 1.03 | 0.71 | 0.95 | 0.93 | 2.19 | 3.26 | 1.12 |
| Alkbh3 | 1.42 | 1.26 | 1.01 | 0.41 | 2.83 | 0.95 | 0.98 | 0.80 | 0.90 | 0.96 | 1.54 | 0.97 |
| Alkbh7 | 1.36 | 0.64 | 0.77 | 0.25 | 3.28 | 0.72 | 1.05 | 0.80 | 0.74 | 3.29 | 3.25 | 1.06 |
| Als2cr12 | 1.00 | 1.00 | 1.00 | 0.57 | 5.25 | 1.55 | 1.00 | 1.00 | 1.00 | 1.00 | 1.00 | 1.00 |
| Alyref | 0.97 | 0.93 | 1.22 | 0.47 | 2.16 | 0.52 | 0.67 | 0.81 | 0.83 | 1.15 | 1.34 | 0.86 |
| Amd1 | 0.83 | 0.91 | 1.77 | 1.00 | 0.17 | 1.00 | 0.10 | 1.00 | 0.12 | 0.70 | 0.21 | 1.00 |
| Amd2 | 1.97 | 95.54 | 0.49 | 0.85 | 0.84 | 0.65 | 0.53 | 0.53 | 0.77 | 1.00 | 0.49 | 0.85 |
| Amdhd2 | 1.07 | 0.34 | 1.01 | 0.36 | 8.88 | 1.19 | 1.05 | 1.05 | 1.28 | 4.17 | 4.85 | 0.96 |
| Amica1 | 1.85 | 1.88 | 1.12 | 2.63 | 3.33 | 1.37 | 3.25 | 2.89 | 1.56 | 1.02 | 1.38 | 1.38 |
| Ampd3 | 4.81 | 7.56 | 3.83 | 2.14 | 0.54 | 1.16 | 2.98 | 3.03 | 1.76 | 0.84 | 1.06 | 1.73 |
| Amph | 1.00 | 1.00 | 1.00 | 1.00 | 0.35 | 1.00 | 1.41 | 1.58 | 1.10 | 0.96 | 0.91 | 1.37 |
| Amy2a5 | 1.00 | 1.00 | 1.00 | 3.94 | 1.00 | 1.00 | 1.00 | 1.00 | 1.00 | 2.67 | 1.00 | 3.12 |
| Amy2b | 1.00 | 1.00 | 1.00 | 1.00 | 1.00 | 1.00 | 1.00 | 1.00 | 1.00 | 1.00 | 1.00 | 1.02 |
| Anapc11 | 1.05 | 0.51 | 0.91 | 0.34 | 5.53 | 1.03 | 0.89 | 0.84 | 0.78 | 2.06 | 2.67 | 0.85 |
| Anapc13 | 1.09 | 0.49 | 0.71 | 0.27 | 7.62 | 0.88 | 0.90 | 0.77 | 0.73 | 1.40 | 2.69 | 0.73 |
| Anapc15 | 1.32 | 0.57 | 0.72 | 0.34 | 12.18 | 1.16 | 0.93 | 0.76 | 0.89 | 3.80 | 4.42 | 1.60 |
| Anapc16 | 2.09 | 1.79 | 1.65 | 1.40 | 6.29 | 1.56 | 1.47 | 1.36 | 1.01 | 1.48 | 1.76 | 1.25 |
| Anapc7 | 0.97 | 0.58 | 0.95 | 0.61 | 4.62 | 1.06 | 1.30 | 1.15 | 1.02 | 1.86 | 2.62 | 0.97 |

Fig. 35- 122

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Acoxl | 1.00 | 1.00 | 1.00 | 1.00 | 1.00 | 1.00 | 1.00 | 1.00 | 1.00 | 1.00 | 1.00 | 1.00 |
| Acsf3 | 0.89 | 1.06 | 0.77 | 1.04 | 0.74 | 0.92 | 1.15 | 1.74 | 0.83 | 0.95 | 0.97 | 0.93 |
| Acsm1 | 1.00 | 1.00 | 1.00 | 1.17 | 0.74 | 1.25 | 0.73 | 1.95 | 0.76 | 1.00 | 1.00 | 1.00 |
| Acta1 | 0.49 | 0.31 | 1.00 | 1.00 | 1.00 | 1.00 | 1.00 | 1.00 | 1.00 | 0.68 | 0.72 | 0.84 |
| Actb | 0.81 | 0.86 | 0.92 | 0.86 | 0.56 | 0.95 | 0.90 | 1.73 | 0.77 | 1.05 | 1.31 | 1.06 |
| Actl7b | 1.00 | 1.00 | 1.00 | 1.00 | 1.00 | 1.00 | 1.00 | 1.00 | 1.00 | 1.00 | 1.00 | 1.00 |
| Actn3 | 0.95 | 0.57 | 0.62 | 1.00 | 1.00 | 1.00 | 1.00 | 1.00 | 1.00 | 1.00 | 1.00 | 1.00 |
| Actr5 | 0.89 | 1.14 | 0.79 | 1.29 | 0.60 | 1.01 | 0.95 | 2.94 | 0.86 | 0.85 | 1.29 | 0.93 |
| Ada | 1.04 | 1.28 | 0.87 | 1.65 | 0.83 | 1.00 | 1.19 | 4.11 | 1.33 | 1.01 | 1.03 | 0.89 |
| Adamtsl4 | 1.83 | 1.93 | 1.52 | 1.26 | 1.00 | 1.06 | 1.00 | 1.00 | 1.49 | 1.06 | 0.91 | 0.96 |
| Adat2 | 1.26 | 1.34 | 1.18 | 1.73 | 2.28 | 2.37 | 1.40 | 6.22 | 2.27 | 1.85 | 2.79 | 1.55 |
| Adck4 | 1.25 | 1.68 | 0.93 | 0.88 | 0.63 | 0.92 | 0.89 | 1.47 | 0.75 | 0.94 | 1.48 | 0.89 |
| Adck5 | 1.34 | 1.29 | 1.07 | 1.07 | 0.78 | 1.12 | 1.48 | 2.85 | 0.79 | 0.97 | 1.58 | 1.10 |
| Adcy1 | 0.51 | 0.51 | 0.54 | 1.51 | 1.00 | 1.28 | 3.15 | 1.00 | 1.00 | 1.00 | 1.00 | 1.00 |
| Adh1 | 2.48 | 2.00 | 1.78 | 2.31 | 2.46 | 1.28 | 0.45 | 0.41 | 0.61 | 0.73 | 1.07 | 0.76 |
| Adh6-ps1 | 1.00 | 1.00 | 1.00 | 1.00 | 1.00 | 1.00 | 4.82 | 1.23 | 9.25 | 1.00 | 1.00 | 1.00 |
| Adh6a | 1.00 | 1.00 | 1.00 | 1.00 | 1.00 | 1.00 | 1.00 | 1.00 | 1.00 | 1.00 | 1.00 | 1.00 |
| Adh7 | 1.00 | 1.00 | 1.00 | 1.00 | 1.00 | 1.00 | 1.45 | 10.78 | 1.01 | 1.00 | 1.00 | 1.00 |
| Adig | 0.87 | 2.59 | 0.69 | 1.00 | 0.61 | 1.00 | 1.00 | 1.00 | 1.00 | 1.00 | 1.76 | 2.18 |
| Adora1 | 0.60 | 0.57 | 0.53 | 0.89 | 1.28 | 1.04 | 0.68 | 1.15 | 0.63 | 1.20 | 0.97 | 1.21 |
| Adrb2 | 1.15 | 1.15 | 1.02 | 0.66 | 0.46 | 0.41 | 1.03 | 5.51 | 1.04 | 0.68 | 0.86 | 0.69 |
| Aes | 0.96 | 1.35 | 0.83 | 0.89 | 0.74 | 0.90 | 0.72 | 1.24 | 0.74 | 0.95 | 1.42 | 0.97 |
| Ager | 0.55 | 0.87 | 0.59 | 1.00 | 0.52 | 1.00 | 1.00 | 1.00 | 1.00 | 1.00 | 0.60 | 0.64 |
| Agrp | 1.28 | 1.32 | 0.54 | 1.00 | 0.36 | 1.00 | 1.00 | 1.00 | 1.00 | 1.00 | 1.00 | 1.00 |
| Agt | 4.27 | 1.72 | 1.88 | 0.65 | 0.44 | 0.64 | 1.00 | 1.91 | 1.01 | 1.02 | 1.06 | 1.28 |
| Ahsg | 13.44 | 1.31 | 0.45 | 1.21 | 0.57 | 0.53 | 0.93 | 0.94 | 0.94 | 1.78 | 1.72 | 1.00 |
| Aif1 | 2.14 | 2.40 | 1.45 | 1.00 | 0.26 | 1.00 | 0.89 | 0.63 | 0.82 | 0.78 | 1.15 | 0.89 |
| Aifm2 | 1.56 | 1.45 | 1.18 | 0.84 | 0.65 | 0.86 | 1.29 | 3.04 | 1.33 | 0.95 | 1.10 | 0.89 |
| Aimp1 | 1.24 | 1.35 | 1.02 | 1.04 | 0.99 | 1.14 | 1.39 | 1.05 | 1.14 | 0.97 | 1.56 | 1.11 |
| Aimp2 | 0.86 | 1.06 | 1.06 | 0.88 | 0.85 | 0.81 | 1.06 | 1.63 | 0.92 | 1.02 | 1.32 | 1.06 |
| Ak6 | 0.69 | 0.81 | 0.85 | 0.86 | 0.91 | 1.09 | 1.22 | 1.13 | 1.05 | 1.02 | 1.67 | 1.11 |
| Akap4 | 1.00 | 1.00 | 1.00 | 1.00 | 1.00 | 1.00 | 1.00 | 1.00 | 1.00 | 1.00 | 1.00 | 1.00 |
| Akap8l | 1.19 | 1.35 | 1.19 | 1.16 | 0.69 | 1.37 | 0.82 | 1.49 | 0.97 | 1.05 | 1.45 | 1.08 |
| Akip1 | 1.21 | 1.62 | 1.36 | 1.10 | 0.93 | 0.98 | 1.42 | 1.62 | 1.20 | 0.98 | 1.47 | 1.17 |
| Akp3 | 1.00 | 1.00 | 1.00 | 1.00 | 1.00 | 1.00 | 1.00 | 1.00 | 1.00 | 1.00 | 1.00 | 1.00 |
| Akr1b8 | 3.43 | 3.41 | 1.80 | 0.45 | 0.36 | 0.49 | 2.44 | 5.54 | 3.00 | 1.71 | 2.93 | 1.65 |
| Akr7a5 | 1.24 | 1.48 | 1.25 | 1.02 | 0.66 | 1.13 | 1.00 | 2.29 | 1.17 | 0.98 | 1.35 | 1.06 |
| Alb | 9.10 | 1.23 | 0.23 | 1.15 | 0.57 | 0.83 | 0.80 | 0.73 | 0.80 | 3.77 | 1.36 | 1.43 |
| Aldh1a1 | 3.77 | 3.40 | 1.86 | 0.22 | 0.21 | 0.22 | 0.62 | 0.95 | 0.70 | 1.03 | 1.27 | 1.01 |
| Aldh1l1 | 1.79 | 1.70 | 1.42 | 1.14 | 0.68 | 1.01 | 1.03 | 2.81 | 1.10 | 1.16 | 1.38 | 0.89 |
| Aldh3a1 | 1.73 | 0.84 | 1.01 | 1.00 | 1.00 | 1.00 | 1.00 | 1.00 | 1.00 | 1.00 | 1.00 | 1.00 |
| Aldh7a1 | 0.97 | 0.90 | 0.92 | 0.91 | 0.58 | 0.92 | 0.72 | 1.73 | 0.94 | 0.82 | 1.14 | 0.90 |
| Aldob | 8.25 | 2.67 | 1.51 | 0.89 | 1.11 | 0.81 | 1.23 | 0.87 | 1.19 | 0.94 | 1.12 | 1.05 |
| Aldoc | 1.27 | 1.45 | 0.89 | 0.93 | 1.02 | 0.96 | 0.63 | 0.31 | 1.01 | 0.85 | 1.09 | 0.83 |
| Alg1 | 1.25 | 1.14 | 1.07 | 0.93 | 1.07 | 0.97 | 0.98 | 0.50 | 1.44 | 1.35 | 1.37 | 0.74 |
| Alg3 | 0.94 | 1.01 | 1.06 | 0.85 | 0.64 | 0.95 | 1.24 | 3.03 | 1.28 | 0.88 | 1.53 | 1.26 |
| Alkbh2 | 1.09 | 1.53 | 1.08 | 0.98 | 0.69 | 1.03 | 0.94 | 1.38 | 1.08 | 1.18 | 1.62 | 1.17 |
| Alkbh3 | 1.34 | 1.60 | 0.99 | 0.81 | 0.89 | 0.77 | 1.39 | 0.60 | 0.94 | 0.99 | 1.75 | 0.97 |
| Alkbh7 | 1.19 | 1.63 | 1.22 | 0.98 | 0.70 | 1.03 | 0.87 | 1.93 | 0.82 | 1.10 | 1.98 | 1.15 |
| Als2cr12 | 1.00 | 1.00 | 1.00 | 0.76 | 1.14 | 1.16 | 1.00 | 1.00 | 1.00 | 1.00 | 1.00 | 1.06 |
| Alyref | 0.59 | 0.76 | 0.70 | 0.82 | 0.77 | 0.92 | 0.89 | 0.26 | 0.95 | 0.73 | 1.40 | 0.90 |
| Amd1 | 1.00 | 0.15 | 1.00 | 1.00 | 0.16 | 1.00 | 1.00 | 1.00 | 1.00 | 1.00 | 1.00 | 0.12 |
| Amd2 | 0.78 | 0.94 | 0.86 | 0.70 | 5.05 | 0.66 | 0.55 | 0.58 | 0.62 | 0.99 | 0.94 | 1.54 |
| Amdhd2 | 1.30 | 1.42 | 1.17 | 0.93 | 0.47 | 1.11 | 0.89 | 2.90 | 0.90 | 0.92 | 1.43 | 0.85 |
| Amica1 | 1.21 | 1.55 | 1.40 | 1.21 | 1.00 | 1.05 | 3.63 | 15.77 | 1.00 | 1.21 | 2.09 | 1.39 |
| Ampd3 | 1.32 | 1.20 | 1.34 | 1.29 | 1.36 | 1.15 | 1.00 | 1.00 | 1.00 | 0.97 | 0.75 | 1.07 |
| Amph | 1.22 | 1.03 | 1.00 | 1.00 | 1.00 | 1.00 | 1.00 | 1.00 | 1.00 | 0.68 | 0.52 | 0.64 |
| Amy2a5 | 1.00 | 0.87 | 2.50 | 1.00 | 0.33 | 0.98 | 1.00 | 1.83 | 0.87 | 0.47 | 2.84 | 30.67 |
| Amy2b | 1.00 | 1.00 | 1.00 | 1.00 | 1.00 | 1.33 | 1.00 | 1.00 | 1.29 | 0.45 | 2.43 | 30.59 |
| Anapc11 | 1.02 | 1.16 | 1.10 | 0.71 | 0.44 | 0.78 | 0.81 | 1.73 | 0.87 | 1.14 | 1.54 | 1.02 |
| Anapc13 | 1.05 | 1.84 | 0.86 | 0.64 | 0.59 | 0.67 | 0.66 | 0.68 | 0.53 | 1.00 | 1.46 | 0.72 |
| Anapc15 | 0.86 | 1.04 | 0.73 | 1.07 | 0.55 | 1.25 | 0.49 | 1.59 | 0.77 | 0.85 | 2.12 | 0.98 |
| Anapc16 | 1.38 | 1.69 | 1.28 | 1.25 | 1.05 | 1.08 | 2.03 | 2.10 | 1.42 | 1.19 | 1.60 | 1.20 |
| Anapc7 | 0.91 | 1.11 | 0.90 | 1.23 | 0.82 | 1.01 | 1.13 | 2.03 | 0.87 | 1.02 | 1.37 | 1.10 |

Fig. 35- 123

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Acoxl | 1.00 | 1.00 | 1.00 | 1.00 | 1.00 | 1.00 | 1.08 | 1.00 | 1.16 | 1.00 | 1.00 | 1.00 |
| Acsf3 | 1.00 | 1.09 | 0.85 | 0.56 | 1.60 | 0.74 | 1.01 | 2.36 | 1.04 | 1.04 | 1.07 | 1.11 |
| Acsm1 | 1.00 | 1.00 | 1.00 | 1.00 | 1.00 | 1.00 | 1.00 | 1.00 | 1.00 | 1.00 | 1.00 | 1.00 |
| Acta1 | 3.17 | 1.46 | 2.72 | 0.50 | 0.50 | 0.28 | 0.76 | 0.95 | 0.86 | 1.00 | 0.99 | 1.00 |
| Actb | 0.76 | 0.77 | 0.77 | 0.87 | 1.31 | 0.84 | 0.80 | 1.74 | 0.93 | 0.75 | 0.72 | 0.82 |
| Actl7b | 1.00 | 1.00 | 1.00 | 4.01 | 1.52 | 1.35 | 1.04 | 1.48 | 1.05 | 1.00 | 1.00 | 1.00 |
| Actn3 | 1.74 | 1.64 | 1.92 | 1.00 | 1.00 | 1.00 | 1.02 | 3.14 | 1.04 | 1.00 | 1.00 | 1.00 |
| Actr5 | 1.20 | 1.10 | 0.96 | 1.33 | 4.07 | 0.94 | 1.01 | 3.94 | 0.90 | 1.00 | 1.46 | 1.21 |
| Ada | 0.73 | 1.04 | 1.10 | 1.20 | 4.89 | 1.82 | 1.00 | 1.85 | 0.79 | 1.45 | 1.82 | 1.18 |
| Adamtsl4 | 1.30 | 1.48 | 1.12 | 0.91 | 0.47 | 0.74 | 1.00 | 1.00 | 1.00 | 1.44 | 1.26 | 2.66 |
| Adat2 | 1.28 | 1.02 | 1.24 | 1.42 | 1.21 | 1.60 | 1.35 | 2.35 | 1.41 | 1.44 | 1.61 | 1.37 |
| Adck4 | 0.88 | 0.85 | 0.88 | 1.47 | 4.49 | 1.43 | 1.04 | 2.05 | 1.09 | 1.22 | 1.57 | 1.20 |
| Adck5 | 1.49 | 1.47 | 1.02 | 0.90 | 2.98 | 1.28 | 0.93 | 1.89 | 1.33 | 0.97 | 1.31 | 0.95 |
| Adcy1 | 1.00 | 0.98 | 1.00 | 1.00 | 1.00 | 1.00 | 1.00 | 1.00 | 1.00 | 0.90 | 5.02 | 1.18 |
| Adh1 | 1.18 | 1.22 | 1.39 | 0.74 | 1.22 | 1.27 | 0.29 | 0.22 | 0.32 | 0.46 | 0.59 | 0.34 |
| Adh6-ps1 | 1.00 | 1.00 | 1.00 | 1.00 | 1.00 | 1.00 | 1.00 | 1.00 | 1.00 | 1.00 | 1.00 | 1.00 |
| Adh6a | 2.20 | 1.27 | 2.27 | 1.00 | 1.00 | 1.00 | 1.00 | 1.00 | 1.00 | 1.00 | 1.00 | 1.00 |
| Adh7 | 1.11 | 1.20 | 1.17 | 1.00 | 1.00 | 1.00 | 1.00 | 1.77 | 0.83 | 1.00 | 1.00 | 1.00 |
| Adig | 0.70 | 1.90 | 1.34 | 0.76 | 3.30 | 1.24 | 0.85 | 1.90 | 1.06 | 1.00 | 1.00 | 1.00 |
| Adora1 | 0.93 | 0.93 | 0.82 | 0.74 | 0.60 | 1.19 | 1.05 | 0.74 | 1.06 | 1.00 | 7.38 | 1.00 |
| Adrb2 | 0.52 | 0.57 | 0.50 | 2.35 | 12.76 | 3.43 | 1.00 | 1.00 | 1.00 | 1.28 | 1.12 | 1.13 |
| Aes | 0.92 | 1.08 | 0.96 | 0.71 | 1.53 | 0.77 | 0.75 | 1.54 | 0.79 | 0.96 | 1.29 | 0.90 |
| Ager | 1.00 | 1.00 | 1.00 | 0.46 | 2.68 | 0.95 | 1.00 | 1.00 | 1.00 | 0.37 | 1.01 | 0.52 |
| Agrp | 1.00 | 1.00 | 1.00 | 1.00 | 1.00 | 1.00 | 0.79 | 1.00 | 1.02 | 1.00 | 1.00 | 1.00 |
| Agt | 1.72 | 2.53 | 1.87 | 2.09 | 10.60 | 4.19 | 1.91 | 3.25 | 1.33 | 1.23 | 5.67 | 1.09 |
| Ahsg | 2.00 | 4.08 | 3.53 | 0.59 | 1.27 | 1.15 | 1.18 | 1.92 | 0.48 | 1.00 | 3.27 | 1.17 |
| Aif1 | 1.17 | 0.87 | 0.86 | 1.09 | 2.22 | 0.92 | 0.85 | 2.95 | 0.99 | 0.68 | 0.97 | 0.82 |
| Aifm2 | 1.31 | 1.21 | 1.12 | 1.46 | 3.53 | 1.51 | 0.78 | 2.72 | 1.00 | 1.12 | 1.35 | 0.97 |
| Aimp1 | 1.02 | 0.89 | 1.00 | 1.21 | 7.33 | 1.25 | 0.98 | 0.76 | 0.95 | 1.09 | 1.20 | 1.13 |
| Aimp2 | 0.91 | 0.95 | 0.79 | 0.91 | 2.14 | 1.07 | 0.95 | 1.78 | 0.97 | 1.02 | 1.35 | 0.99 |
| Ak6 | 0.86 | 1.00 | 1.14 | 0.91 | 5.52 | 0.91 | 1.14 | 1.50 | 1.10 | 1.02 | 0.82 | 0.90 |
| Akap4 | 1.00 | 1.00 | 1.00 | 3.88 | 1.00 | 1.00 | 0.97 | 0.87 | 0.99 | 1.00 | 1.00 | 1.00 |
| Akap8l | 1.08 | 1.08 | 1.29 | 0.98 | 2.31 | 1.20 | 1.18 | 2.71 | 1.13 | 1.10 | 1.31 | 1.10 |
| Akip1 | 0.78 | 1.00 | 0.95 | 2.03 | 13.86 | 1.79 | 0.87 | 1.35 | 0.82 | 1.28 | 1.00 | 1.09 |
| Akp3 | 41.14 | 3.37 | 51.24 | 1.00 | 1.00 | 1.00 | 1.00 | 1.00 | 1.00 | 1.00 | 1.00 | 1.00 |
| Akr1b8 | 0.56 | 0.61 | 0.63 | 0.83 | 0.91 | 0.78 | 0.73 | 1.05 | 0.76 | 1.24 | 1.67 | 1.28 |
| Akr7a5 | 1.27 | 1.27 | 1.29 | 1.01 | 2.39 | 1.08 | 0.80 | 2.77 | 1.03 | 1.10 | 1.71 | 1.02 |
| Alb | 1.22 | 3.57 | 2.27 | 0.37 | 2.05 | 1.39 | 1.02 | 1.02 | 0.84 | 1.00 | 5.89 | 0.87 |
| Aldh1a1 | 0.88 | 0.91 | 0.77 | 1.69 | 5.60 | 1.20 | 1.28 | 1.86 | 0.91 | 1.14 | 2.03 | 1.11 |
| Aldh1l1 | 1.55 | 1.95 | 1.10 | 1.53 | 6.75 | 2.16 | 1.08 | 2.26 | 0.75 | 0.86 | 2.49 | 1.13 |
| Aldh3a1 | 1.11 | 1.38 | 0.89 | 1.00 | 1.00 | 1.00 | 1.00 | 2.85 | 1.00 | 1.00 | 0.98 | 0.74 |
| Aldh7a1 | 0.99 | 1.16 | 1.44 | 0.71 | 3.23 | 0.77 | 0.94 | 2.45 | 1.04 | 1.03 | 1.07 | 0.96 |
| Aldob | 3.09 | 3.17 | 5.75 | 1.30 | 1.30 | 2.80 | 1.00 | 1.40 | 0.75 | 1.00 | 1.00 | 1.00 |
| Aldoc | 1.17 | 1.36 | 1.40 | 1.07 | 1.20 | 1.86 | 1.01 | 0.82 | 0.65 | 0.93 | 16.97 | 0.89 |
| Alg1 | 0.99 | 1.35 | 1.13 | 1.53 | 1.00 | 1.12 | 0.92 | 1.00 | 0.65 | 0.98 | 1.15 | 0.95 |
| Alg3 | 0.93 | 0.93 | 1.12 | 1.02 | 1.56 | 1.11 | 0.99 | 2.97 | 0.74 | 1.22 | 1.03 | 1.00 |
| Alkbh2 | 1.05 | 1.60 | 0.95 | 0.90 | 4.19 | 0.79 | 0.80 | 1.58 | 0.94 | 1.45 | 1.53 | 1.39 |
| Alkbh3 | 1.02 | 1.03 | 0.73 | 0.86 | 5.07 | 1.17 | 0.85 | 0.79 | 0.98 | 1.36 | 1.41 | 1.04 |
| Alkbh7 | 0.95 | 1.21 | 0.88 | 0.89 | 2.44 | 0.89 | 0.90 | 2.28 | 1.06 | 0.87 | 1.53 | 1.07 |
| Als2cr12 | 1.00 | 1.00 | 1.00 | 1.00 | 1.00 | 0.84 | 0.97 | 0.74 | 0.96 | 0.59 | 0.85 | 0.61 |
| Alyref | 0.66 | 0.77 | 0.86 | 1.17 | 7.07 | 1.05 | 1.23 | 0.91 | 1.31 | 1.03 | 0.93 | 0.91 |
| Amd1 | 1.00 | 1.00 | 1.00 | 1.00 | 1.00 | 1.00 | 1.00 | 0.19 | 1.00 | 1.00 | 14.10 | 1.00 |
| Amd2 | 0.79 | 0.69 | 0.89 | 0.88 | 0.94 | 1.25 | 0.98 | 1.15 | 0.87 | 1.00 | 0.43 | 0.86 |
| Amdhd2 | 1.09 | 1.76 | 1.30 | 0.68 | 1.20 | 0.80 | 0.97 | 5.22 | 0.94 | 1.00 | 1.22 | 0.62 |
| Amica1 | 2.65 | 2.19 | 2.06 | 3.22 | 1.95 | 2.56 | 1.00 | 1.00 | 1.00 | 1.14 | 0.98 | 1.20 |
| Ampd3 | 1.14 | 1.02 | 1.13 | 1.20 | 0.43 | 1.03 | 0.99 | 1.00 | 0.89 | 0.88 | 0.65 | 0.81 |
| Amph | 1.00 | 1.00 | 1.00 | 1.00 | 1.00 | 1.53 | 1.64 | 2.25 | 1.31 | 1.00 | 6.58 | 1.00 |
| Amy2a5 | 183.09 | 3.47 | 2.97 | 1.00 | 0.63 | 0.81 | 0.94 | 2.14 | 1.15 | 3.59 | 10.07 | 0.79 |
| Amy2b | 36.12 | 3.90 | 2.81 | 1.00 | 1.00 | 0.76 | 1.00 | 1.96 | 0.97 | 2.16 | 8.70 | 0.89 |
| Anapc11 | 0.90 | 1.06 | 1.09 | 0.88 | 1.91 | 0.82 | 0.86 | 2.55 | 1.01 | 0.99 | 1.18 | 0.96 |
| Anapc13 | 0.82 | 0.88 | 0.94 | 0.59 | 1.71 | 0.73 | 0.71 | 1.34 | 0.70 | 0.81 | 1.51 | 1.04 |
| Anapc15 | 0.52 | 0.91 | 0.95 | 0.77 | 1.76 | 0.85 | 0.82 | 2.47 | 0.85 | 0.99 | 1.19 | 0.74 |
| Anapc16 | 1.25 | 1.46 | 1.11 | 1.80 | 4.35 | 1.55 | 1.01 | 1.40 | 0.85 | 1.28 | 1.47 | 1.24 |
| Anapc7 | 0.94 | 1.04 | 1.00 | 1.24 | 3.42 | 1.11 | 0.98 | 2.03 | 0.94 | 1.06 | 1.24 | 0.99 |

Fig. 35- 124

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Acox1 | 1.00 | 1.00 | 1.00 | 1.00 | 1.00 | 1.00 | 13.63 | 13.70 | 13.12 | 1.00 | 1.00 | 1.00 |
| Acsf3 | 1.06 | 1.08 | 0.76 | 0.89 | 0.84 | 1.07 | 0.90 | 5.06 | 0.88 | 2.58 | 0.91 | 1.02 |
| Acsm1 | 1.00 | 1.00 | 1.00 | 1.00 | 1.00 | 1.00 | 1.00 | 5.30 | 1.00 | 1.00 | 1.00 | 1.00 |
| Acta1 | 0.73 | 1.00 | 1.00 | 1.01 | 0.96 | 1.38 | 1.77 | 7.47 | 2.09 | 2.13 | 1.03 | 1.00 |
| Actb | 1.16 | 1.08 | 0.92 | 1.18 | 0.89 | 1.10 | 0.81 | 4.43 | 0.75 | 2.38 | 1.13 | 1.17 |
| Actl7b | 1.00 | 1.00 | 1.00 | 1.00 | 1.00 | 1.00 | 5.26 | 1.00 | 1.00 | 2.23 | 1.15 | 1.00 |
| Actn3 | 1.00 | 1.00 | 1.00 | 1.00 | 0.41 | 1.00 | 2.68 | 15.16 | 3.98 | 1.00 | 1.00 | 1.00 |
| Actr5 | 1.03 | 1.44 | 0.87 | 1.03 | 1.04 | 0.78 | 1.13 | 10.50 | 1.00 | 3.36 | 1.17 | 0.96 |
| Ada | 1.00 | 1.00 | 1.00 | 1.00 | 3.28 | 1.00 | 0.72 | 6.54 | 0.94 | 2.43 | 1.36 | 0.85 |
| Adamtsl4 | 1.02 | 1.00 | 1.00 | 0.84 | 1.00 | 0.72 | 1.27 | 0.26 | 1.11 | 2.07 | 6.86 | 3.33 |
| Adat2 | 1.48 | 1.24 | 1.76 | 1.67 | 5.26 | 1.31 | 1.84 | 8.51 | 1.79 | 6.17 | 2.44 | 2.37 |
| Adck4 | 1.05 | 1.25 | 1.00 | 1.09 | 0.85 | 1.03 | 1.58 | 7.20 | 1.19 | 2.60 | 1.56 | 1.27 |
| Adck5 | 1.00 | 0.92 | 1.07 | 1.04 | 1.06 | 0.91 | 1.37 | 6.10 | 0.96 | 2.37 | 1.17 | 0.88 |
| Adcy1 | 1.00 | 1.00 | 1.00 | 0.86 | 1.17 | 0.89 | 1.50 | 0.88 | 1.66 | 1.00 | 1.00 | 1.00 |
| Adh1 | 1.13 | 1.15 | 1.33 | 1.00 | 1.00 | 1.00 | 1.67 | 1.71 | 1.46 | 1.00 | 1.00 | 1.00 |
| Adh6-ps1 | 1.00 | 1.00 | 1.00 | 1.00 | 1.00 | 1.00 | 1.00 | 1.00 | 1.00 | 1.00 | 1.00 | 1.00 |
| Adh6a | 1.00 | 1.00 | 1.00 | 1.00 | 1.00 | 1.00 | 1.67 | 7.53 | 1.46 | 1.00 | 1.00 | 1.00 |
| Adh7 | 1.00 | 1.00 | 1.00 | 1.00 | 1.00 | 1.00 | 3.90 | 10.42 | 5.65 | 1.00 | 1.00 | 1.00 |
| Adig | 1.00 | 1.00 | 1.00 | 1.00 | 1.00 | 1.00 | 1.56 | 12.40 | 1.39 | 1.00 | 1.00 | 1.00 |
| Adora1 | 0.57 | 0.52 | 0.50 | 1.05 | 1.17 | 0.94 | 3.27 | 1.82 | 2.08 | 1.00 | 1.00 | 1.00 |
| Adrb2 | 2.08 | 1.74 | 2.20 | 1.18 | 1.09 | 1.40 | 1.30 | 3.30 | 1.64 | 1.39 | 1.03 | 0.84 |
| Aes | 0.70 | 0.93 | 0.86 | 1.08 | 0.91 | 1.07 | 1.26 | 5.89 | 0.96 | 2.54 | 1.28 | 1.18 |
| Ager | 1.00 | 1.00 | 1.00 | 1.00 | 1.17 | 1.00 | 0.99 | 4.04 | 0.73 | 1.46 | 0.77 | 0.61 |
| Agrp | 1.00 | 1.00 | 1.00 | 1.00 | 2.47 | 1.00 | 0.99 | 41.28 | 0.91 | 1.00 | 1.00 | 1.00 |
| Agt | 3.84 | 5.38 | 1.67 | 1.92 | 1.67 | 1.78 | 5.25 | 20.61 | 3.51 | 1.00 | 0.87 | 1.47 |
| Ahsg | 0.68 | 1.42 | 0.17 | 0.31 | 1.00 | 1.77 | 0.92 | 1.00 | 1.65 | 1.00 | 1.00 | 1.00 |
| Aif1 | 1.00 | 1.00 | 1.00 | 1.19 | 1.12 | 1.31 | 2.38 | 19.49 | 1.64 | 4.24 | 1.04 | 1.21 |
| Aifm2 | 1.04 | 0.92 | 1.32 | 1.03 | 0.81 | 1.01 | 1.70 | 8.40 | 1.51 | 2.05 | 1.35 | 0.83 |
| Aimp1 | 0.98 | 0.88 | 1.29 | 1.16 | 0.78 | 0.95 | 1.21 | 2.33 | 1.01 | 1.23 | 1.05 | 1.04 |
| Aimp2 | 1.22 | 0.81 | 0.71 | 1.34 | 1.04 | 1.14 | 1.10 | 5.54 | 0.92 | 1.42 | 1.04 | 0.88 |
| Ak6 | 1.82 | 1.14 | 1.33 | 1.19 | 1.61 | 0.98 | 1.22 | 4.79 | 1.03 | 1.58 | 0.98 | 1.21 |
| Akap4 | 1.00 | 1.00 | 1.00 | 1.00 | 1.00 | 1.00 | 8.35 | 1.00 | 1.00 | 1.00 | 1.00 | 1.00 |
| Akap8l | 1.12 | 1.07 | 1.37 | 0.89 | 0.97 | 1.04 | 1.19 | 9.17 | 1.18 | 3.47 | 1.37 | 1.15 |
| Akip1 | 1.27 | 1.28 | 1.15 | 0.67 | 0.10 | 0.75 | 1.66 | 3.69 | 1.30 | 1.24 | 0.77 | 0.82 |
| Akp3 | 1.00 | 1.00 | 1.00 | 1.00 | 1.00 | 1.00 | 1.00 | 1.00 | 1.00 | 1.00 | 1.00 | 1.00 |
| Akr1b8 | 1.00 | 1.00 | 1.00 | 1.00 | 1.00 | 1.00 | 2.08 | 7.53 | 1.29 | 1.00 | 1.00 | 1.00 |
| Akr7a5 | 1.00 | 0.87 | 0.87 | 1.05 | 0.85 | 0.89 | 1.38 | 13.05 | 1.01 | 3.21 | 1.23 | 1.21 |
| Alb | 1.39 | 1.00 | 0.73 | 0.10 | 1.00 | 1.24 | 0.78 | 1.00 | 1.43 | 1.00 | 1.00 | 1.00 |
| Aldh1a1 | 0.99 | 1.56 | 1.54 | 0.97 | 0.86 | 0.98 | 1.93 | 7.74 | 2.38 | 1.38 | 1.00 | 0.97 |
| Aldh1l1 | 1.01 | 1.50 | 0.86 | 1.10 | 0.84 | 1.10 | 1.44 | 25.86 | 1.24 | 1.00 | 1.00 | 1.00 |
| Aldh3a1 | 1.00 | 1.00 | 1.00 | 1.00 | 0.53 | 1.00 | 1.66 | 10.77 | 1.48 | 1.00 | 1.00 | 1.00 |
| Aldh7a1 | 0.71 | 0.89 | 0.89 | 0.94 | 1.23 | 1.04 | 0.81 | 6.64 | 0.84 | 1.50 | 1.00 | 1.00 |
| Aldob | 0.81 | 1.67 | 0.53 | 0.71 | 2.18 | 1.44 | 1.00 | 1.00 | 1.00 | 1.00 | 1.00 | 1.00 |
| Aldoc | 1.00 | 1.00 | 1.00 | 1.16 | 0.99 | 1.12 | 0.91 | 1.02 | 0.59 | 1.00 | 1.09 | 1.43 |
| Alg1 | 1.43 | 1.22 | 0.88 | 1.20 | 8.42 | 0.93 | 1.62 | 0.28 | 0.93 | 0.63 | 1.26 | 1.23 |
| Alg3 | 1.87 | 0.89 | 1.18 | 0.75 | 1.59 | 0.91 | 0.90 | 5.69 | 0.71 | 1.95 | 0.87 | 1.33 |
| Alkbh2 | 1.84 | 0.50 | 0.81 | 0.88 | 1.79 | 1.05 | 0.82 | 9.66 | 0.76 | 3.65 | 1.23 | 1.25 |
| Alkbh3 | 0.98 | 0.84 | 0.82 | 1.12 | 4.69 | 1.30 | 1.05 | 2.18 | 1.16 | 1.64 | 1.10 | 1.34 |
| Alkbh7 | 1.28 | 0.91 | 0.46 | 1.32 | 1.06 | 0.93 | 1.60 | 6.87 | 0.96 | 2.72 | 1.57 | 1.58 |
| Als2cr12 | 1.00 | 1.00 | 1.00 | 1.00 | 1.00 | 1.00 | 1.00 | 1.00 | 1.00 | 1.00 | 1.00 | 1.00 |
| Alyref | 0.67 | 0.87 | 0.88 | 1.05 | 0.96 | 0.98 | 0.92 | 1.27 | 0.77 | 1.06 | 0.97 | 0.93 |
| Amd1 | 1.00 | 1.00 | 1.00 | 1.00 | 16.43 | 1.71 | 7.41 | 0.19 | 1.00 | 1.29 | 1.00 | 6.42 |
| Amd2 | 0.74 | 0.74 | 0.79 | 1.11 | 0.06 | 0.85 | 0.46 | 0.67 | 0.76 | 0.26 | 0.62 | 0.62 |
| Amdhd2 | 1.00 | 1.09 | 0.91 | 1.08 | 0.83 | 0.93 | 0.68 | 21.15 | 1.16 | 4.68 | 1.08 | 1.17 |
| Amica1 | 1.00 | 1.00 | 1.00 | 1.00 | 1.00 | 1.02 | 1.81 | 1.41 | 2.29 | 1.76 | 2.30 | 1.55 |
| Ampd3 | 1.00 | 1.00 | 1.00 | 0.94 | 1.00 | 1.02 | 1.11 | 0.19 | 1.22 | 0.65 | 1.07 | 1.08 |
| Amph | 1.00 | 1.00 | 1.00 | 1.20 | 1.32 | 1.11 | 1.00 | 1.00 | 1.00 | 1.00 | 1.00 | 1.00 |
| Amy2a5 | 1.03 | 1.11 | 1.06 | 0.91 | 0.60 | 0.67 | 0.26 | 5.79 | 0.96 | 1.00 | 0.35 | 1.25 |
| Amy2b | 1.02 | 1.04 | 1.05 | 1.00 | 1.00 | 0.56 | 1.00 | 1.00 | 0.65 | 1.00 | 1.00 | 0.96 |
| Anapc11 | 0.61 | 0.54 | 0.55 | 1.11 | 0.96 | 1.08 | 1.31 | 6.93 | 1.04 | 2.75 | 1.16 | 1.10 |
| Anapc13 | 0.68 | 0.62 | 0.73 | 1.27 | 1.12 | 0.91 | 1.40 | 7.98 | 0.81 | 3.19 | 1.16 | 0.96 |
| Anapc15 | 1.00 | 1.00 | 1.06 | 0.99 | 0.84 | 1.14 | 1.20 | 20.98 | 0.88 | 3.22 | 0.96 | 1.22 |
| Anapc16 | 1.48 | 1.62 | 1.14 | 1.16 | 1.43 | 1.08 | 1.48 | 2.45 | 1.44 | 1.54 | 1.29 | 1.24 |
| Anapc7 | 1.02 | 0.90 | 0.88 | 1.06 | 0.92 | 1.05 | 1.08 | 6.08 | 1.03 | 2.09 | 1.17 | 1.00 |

Fig. 35- 125

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ang4 | 1.00 | 1.00 | 1.00 | 1.00 | 1.00 | 1.00 | 1.00 | 1.00 | 1.00 | 1.00 | 1.00 | 1.00 |
| Angptl4 | 1.06 | 0.78 | 1.30 | 1.35 | 3.35 | 1.51 | 0.39 | 0.22 | 0.74 | 0.98 | 1.39 | 1.33 |
| Angptl7 | 1.71 | 2.92 | 1.52 | 10.11 | 5.06 | 1.69 | 1.94 | 2.53 | 1.18 | 8.62 | 12.61 | 14.15 |
| Ank2 | 0.79 | 0.82 | 0.72 | 0.52 | 0.11 | 0.45 | 0.87 | 1.05 | 0.86 | 1.00 | 1.00 | 1.00 |
| Ankrd1 | 8.37 | 5.20 | 5.90 | 1.00 | 1.00 | 1.00 | 0.71 | 0.91 | 1.77 | 1.24 | 1.65 | 1.37 |
| Ankrd2 | 2.50 | 0.56 | 1.50 | 1.00 | 1.38 | 0.70 | 1.00 | 1.00 | 1.39 | 1.00 | 1.00 | 1.00 |
| Ankrd33b | 6.17 | 6.80 | 3.79 | 10.88 | 3.77 | 2.98 | 1.81 | 1.80 | 1.22 | 0.61 | 0.36 | 0.89 |
| Ankrd55 | 1.00 | 1.56 | 1.00 | 1.00 | 1.00 | 1.00 | 1.53 | 1.51 | 0.92 | 1.00 | 1.00 | 1.00 |
| Anks1b | 1.00 | 1.00 | 1.00 | 1.00 | 0.34 | 1.00 | 1.00 | 1.00 | 1.00 | 1.00 | 1.00 | 1.00 |
| Anks3 | 1.38 | 0.54 | 1.04 | 0.32 | 3.33 | 0.83 | 1.22 | 0.72 | 0.92 | 1.66 | 2.63 | 0.88 |
| Anp32a | 1.40 | 0.97 | 0.92 | 0.89 | 6.23 | 0.98 | 0.94 | 0.85 | 0.86 | 1.03 | 1.21 | 0.88 |
| Aoc2 | 1.11 | 1.00 | 1.00 | 1.32 | 3.11 | 1.21 | 0.92 | 1.60 | 1.70 | 2.59 | 2.74 | 1.03 |
| Aox4 | 1.00 | 1.00 | 1.00 | 1.00 | 1.00 | 1.00 | 1.00 | 1.00 | 1.00 | 1.00 | 1.00 | 1.00 |
| Ap1g2 | 1.00 | 0.34 | 1.75 | 0.74 | 4.92 | 1.05 | 0.94 | 0.86 | 0.88 | 1.78 | 2.40 | 0.79 |
| Ap2s1 | 1.41 | 0.52 | 0.96 | 0.23 | 9.19 | 0.87 | 0.95 | 0.61 | 0.84 | 2.76 | 4.56 | 0.95 |
| Ap5s1 | 1.05 | 0.55 | 0.87 | 0.43 | 2.75 | 0.85 | 0.97 | 0.77 | 0.88 | 2.78 | 2.63 | 1.02 |
| Apbb1 | 1.15 | 0.77 | 0.83 | 0.46 | 0.77 | 0.49 | 0.35 | 0.33 | 0.41 | 2.11 | 2.84 | 1.09 |
| Apeh | 0.79 | 0.40 | 1.08 | 0.37 | 6.84 | 0.80 | 1.04 | 0.88 | 0.94 | 4.06 | 5.19 | 1.06 |
| Apex1 | 0.88 | 0.88 | 0.68 | 1.61 | 3.03 | 0.77 | 0.85 | 0.95 | 1.00 | 4.09 | 1.67 | 1.27 |
| Apip | 1.08 | 0.56 | 0.91 | 0.53 | 6.33 | 1.39 | 1.06 | 1.00 | 0.89 | 1.62 | 2.71 | 0.76 |
| Aplp1 | 1.00 | 1.00 | 1.00 | 1.00 | 0.07 | 1.00 | 1.32 | 0.97 | 1.08 | 0.66 | 0.82 | 1.42 |
| Apoa1 | 3.28 | 1.15 | 1.23 | 3.49 | 5.10 | 2.06 | 18.97 | 0.26 | 1.51 | 0.02 | 2.58 | 2.42 |
| Apoa1bp | 0.93 | 0.52 | 0.71 | 0.37 | 4.88 | 0.77 | 0.87 | 0.86 | 0.66 | 2.18 | 3.02 | 0.79 |
| Apoa2 | 2.09 | 0.33 | 1.00 | 2.53 | 6.34 | 1.16 | 8.33 | 0.20 | 2.01 | 0.04 | 1.68 | 1.41 |
| Apoa4 | 0.75 | 4.78 | 1.16 | 1.00 | 5.88 | 9.03 | 10.63 | 1.65 | 0.66 | 0.43 | 2.17 | 1.00 |
| Apob | 1.00 | 1.00 | 1.00 | 1.00 | 1.00 | 1.00 | 1.00 | 1.00 | 1.00 | 1.30 | 1.63 | 1.18 |
| Apoc1 | 5.93 | 2.22 | 7.28 | 0.58 | 14.72 | 1.71 | 2.54 | 0.31 | 3.51 | 2.29 | 3.90 | 1.36 |
| Apoc2 | 1.00 | 2.09 | 1.70 | 2.87 | 20.01 | 6.02 | 1.00 | 1.20 | 1.00 | 4.48 | 4.66 | 1.00 |
| Apoc3 | 6.60 | 1.53 | 9.12 | 14.66 | 78.27 | 13.95 | 1.92 | 0.81 | 1.00 | 0.09 | 3.98 | 1.00 |
| Apoc4 | 1.05 | 1.09 | 1.00 | 2.08 | 27.81 | 1.21 | 2.50 | 0.51 | 1.00 | 0.16 | 1.46 | 1.00 |
| Apod | 2.49 | 1.20 | 1.57 | 1.06 | 4.59 | 2.19 | 1.21 | 0.90 | 1.24 | 1.91 | 2.25 | 1.18 |
| Apoe | 1.95 | 1.23 | 2.22 | 1.25 | 8.67 | 3.64 | 1.03 | 0.64 | 0.91 | 0.65 | 1.20 | 0.92 |
| Apoh | 1.00 | 1.00 | 1.00 | 1.00 | 0.97 | 1.00 | 2.66 | 0.74 | 1.03 | 0.45 | 1.00 | 1.00 |
| Apol9a | 1.00 | 1.00 | 1.00 | 1.00 | 1.00 | 1.00 | 1.00 | 1.00 | 1.00 | 1.00 | 3.06 | 1.88 |
| Apol9b | 1.00 | 1.00 | 1.00 | 1.00 | 1.00 | 1.00 | 1.00 | 1.00 | 1.28 | 1.81 | 2.95 | 3.52 |
| Aprt | 1.34 | 0.72 | 1.18 | 0.91 | 12.44 | 1.47 | 0.99 | 1.07 | 0.86 | 2.65 | 4.33 | 1.32 |
| Aqp11 | 1.00 | 1.18 | 1.26 | 1.40 | 2.90 | 1.89 | 1.37 | 0.90 | 0.79 | 2.59 | 1.37 | 1.17 |
| Arc | 1.00 | 1.00 | 1.00 | 1.03 | 0.35 | 0.60 | 1.44 | 0.97 | 0.92 | 1.00 | 1.00 | 1.00 |
| Arhgap26 | 2.25 | 6.23 | 2.46 | 1.91 | 0.73 | 0.85 | 1.12 | 1.47 | 0.94 | 0.86 | 1.03 | 1.08 |
| Arhgap42 | 1.11 | 1.00 | 1.72 | 6.29 | 1.20 | 1.55 | 1.02 | 2.05 | 1.46 | 0.77 | 0.25 | 0.88 |
| Arhgap5 | 0.64 | 1.00 | 0.99 | 5.23 | 0.18 | 0.75 | 1.25 | 1.57 | 1.32 | 1.00 | 1.00 | 1.10 |
| Arhgef9 | 0.60 | 0.89 | 0.86 | 2.33 | 0.14 | 0.60 | 0.73 | 0.95 | 0.70 | 1.00 | 1.00 | 0.80 |
| Arid5a | 2.71 | 1.73 | 2.41 | 2.34 | 5.81 | 1.04 | 3.22 | 3.89 | 2.18 | 4.35 | 3.83 | 1.47 |
| Arid5b | 1.10 | 1.00 | 1.79 | 14.25 | 1.14 | 1.06 | 2.23 | 3.65 | 2.33 | 1.00 | 1.00 | 1.24 |
| Arl13b | 1.86 | 1.34 | 1.49 | 3.49 | 0.56 | 0.97 | 1.13 | 1.58 | 1.16 | 0.55 | 0.25 | 0.93 |
| Arl2 | 1.17 | 0.54 | 0.89 | 0.31 | 8.26 | 1.02 | 0.79 | 0.81 | 0.78 | 2.56 | 3.93 | 0.95 |
| Arl3 | 0.63 | 0.61 | 0.66 | 0.46 | 5.29 | 1.20 | 1.02 | 0.81 | 0.76 | 1.35 | 2.44 | 1.04 |
| Arl4d | 9.30 | 18.77 | 4.59 | 5.26 | 5.34 | 2.11 | 1.79 | 1.71 | 1.03 | 1.15 | 1.68 | 1.70 |
| Armc12 | 1.00 | 1.00 | 1.00 | 1.00 | 1.00 | 1.00 | 1.00 | 1.00 | 1.00 | 1.00 | 1.00 | 1.00 |
| Armc3 | 1.00 | 1.00 | 1.00 | 1.00 | 1.00 | 1.00 | 1.00 | 1.00 | 1.00 | 4.26 | 5.72 | 1.96 |
| Arntl | 3.20 | 4.53 | 3.21 | 1.59 | 1.19 | 0.90 | 3.28 | 2.71 | 2.66 | 1.34 | 1.30 | 2.58 |
| Arpc3 | 1.39 | 1.19 | 1.23 | 0.39 | 3.36 | 1.09 | 1.08 | 0.90 | 0.89 | 0.89 | 1.72 | 1.10 |
| Arpc4 | 1.20 | 0.73 | 1.00 | 0.51 | 5.26 | 1.04 | 0.91 | 0.81 | 0.89 | 1.80 | 2.65 | 0.89 |
| Arpp21 | 2.20 | 3.81 | 1.94 | 1.00 | 0.13 | 1.00 | 1.00 | 1.00 | 1.00 | 1.00 | 1.00 | 1.00 |
| Arrb2 | 1.41 | 0.48 | 1.14 | 0.35 | 7.19 | 0.91 | 1.05 | 0.70 | 0.99 | 1.91 | 2.80 | 0.89 |
| Arrdc1 | 1.91 | 1.03 | 1.36 | 1.14 | 6.08 | 1.29 | 0.97 | 0.62 | 0.88 | 3.10 | 3.09 | 0.98 |
| Arrdc2 | 1.34 | 1.30 | 1.76 | 2.08 | 3.72 | 1.48 | 2.18 | 2.53 | 1.32 | 1.85 | 2.64 | 2.07 |
| Arrdc3 | 3.14 | 5.58 | 3.59 | 11.57 | 5.27 | 2.12 | 2.59 | 3.32 | 1.36 | 1.15 | 0.98 | 1.08 |
| Arsi | 1.00 | 1.00 | 1.00 | 1.00 | 1.00 | 1.00 | 1.00 | 1.00 | 0.88 | 1.00 | 1.00 | 1.00 |
| Art5 | 1.24 | 0.60 | 1.27 | 1.00 | 1.61 | 1.12 | 2.03 | 1.65 | 1.09 | 4.23 | 4.32 | 0.98 |
| Arv1 | 1.00 | 0.83 | 1.52 | 0.79 | 2.14 | 0.98 | 1.19 | 0.74 | 1.15 | 1.30 | 1.73 | 1.69 |
| Asb11 | 1.84 | 1.42 | 1.33 | 1.45 | 2.92 | 1.44 | 1.05 | 1.09 | 0.93 | 1.65 | 2.15 | 0.51 |
| Asb2 | 1.11 | 0.72 | 0.94 | 0.83 | 2.49 | 1.07 | 0.64 | 0.55 | 0.60 | 1.56 | 2.38 | 0.72 |
| Ascc1 | 1.56 | 0.85 | 1.23 | 0.77 | 12.10 | 1.54 | 1.24 | 0.77 | 1.01 | 3.08 | 4.52 | 0.97 |

Fig. 35- 126

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ang4 | 1.77 | 1.78 | 5.63 | 1.00 | 1.00 | 1.00 | 1.00 | 1.00 | 1.00 | 0.94 | 0.18 | 0.23 |
| Angptl4 | 2.34 | 2.05 | 2.05 | 1.35 | 1.39 | 1.50 | 1.38 | 0.66 | 1.22 | 1.55 | 1.44 | 2.20 |
| Angptl7 | 2.29 | 2.36 | 1.65 | 4.69 | 7.92 | 2.94 | 1.00 | 1.00 | 1.00 | 1.41 | 1.64 | 1.25 |
| Ank2 | 1.32 | 0.83 | 1.20 | 1.27 | 1.00 | 1.27 | 1.00 | 1.00 | 1.00 | 0.95 | 0.95 | 1.17 |
| Ankrd1 | 1.00 | 1.00 | 1.00 | 1.00 | 1.00 | 1.00 | 1.00 | 1.00 | 1.00 | 1.00 | 1.00 | 1.00 |
| Ankrd2 | 1.00 | 1.00 | 1.00 | 1.00 | 1.00 | 1.00 | 1.00 | 1.00 | 1.00 | 1.00 | 1.00 | 1.00 |
| Ankrd33b | 0.85 | 0.82 | 1.27 | 1.36 | 1.48 | 1.18 | 1.22 | 2.24 | 1.37 | 1.00 | 1.00 | 1.00 |
| Ankrd55 | 1.58 | 1.23 | 0.87 | 1.00 | 1.95 | 1.00 | 0.34 | 1.03 | 0.68 | 1.00 | 1.00 | 1.00 |
| Anks1b | 1.00 | 1.00 | 1.00 | 1.00 | 1.00 | 1.00 | 1.00 | 1.00 | 1.00 | 1.00 | 1.00 | 1.00 |
| Anks3 | 1.34 | 1.33 | 0.99 | 0.91 | 0.76 | 0.89 | 0.69 | 1.13 | 0.90 | 0.98 | 1.29 | 0.98 |
| Anp32a | 0.93 | 0.95 | 0.90 | 1.05 | 0.87 | 0.91 | 0.86 | 0.74 | 0.95 | 1.01 | 1.35 | 0.99 |
| Aoc2 | 0.85 | 0.87 | 1.01 | 1.05 | 0.72 | 1.05 | 1.81 | 3.18 | 2.03 | 1.21 | 0.89 | 1.39 |
| Aox4 | 1.00 | 1.00 | 1.00 | 1.00 | 1.00 | 1.00 | 1.00 | 1.00 | 1.00 | 1.00 | 1.00 | 1.00 |
| Ap1g2 | 0.97 | 1.22 | 1.09 | 1.03 | 0.74 | 0.90 | 1.08 | 2.00 | 1.02 | 1.11 | 1.21 | 0.94 |
| Ap2s1 | 1.23 | 1.78 | 0.98 | 0.92 | 0.55 | 0.98 | 1.07 | 1.97 | 0.92 | 1.00 | 1.75 | 1.00 |
| Ap5s1 | 1.33 | 1.47 | 1.13 | 1.01 | 0.54 | 0.77 | 0.96 | 2.93 | 1.02 | 0.95 | 1.23 | 0.98 |
| Apbb1 | 1.59 | 1.23 | 1.10 | 0.59 | 0.68 | 0.70 | 1.00 | 0.95 | 1.00 | 0.82 | 1.33 | 0.98 |
| Apeh | 1.11 | 1.50 | 1.13 | 1.15 | 0.68 | 1.03 | 0.79 | 2.53 | 0.90 | 1.01 | 1.28 | 1.00 |
| Apex1 | 0.81 | 0.50 | 0.56 | 0.84 | 0.88 | 0.81 | 0.94 | 0.76 | 0.67 | 0.97 | 1.47 | 0.86 |
| Apip | 1.69 | 1.24 | 1.03 | 0.82 | 0.75 | 0.97 | 1.64 | 1.14 | 0.64 | 0.89 | 1.57 | 0.95 |
| Aplp1 | 2.54 | 1.93 | 1.57 | 0.92 | 1.14 | 1.29 | 1.00 | 1.00 | 1.00 | 1.30 | 1.21 | 1.02 |
| Apoa1 | 10.86 | 2.03 | 0.79 | 1.54 | 2.00 | 1.05 | 1.25 | 1.72 | 1.21 | 2.56 | 3.16 | 5.96 |
| Apoa1bp | 1.27 | 1.39 | 0.92 | 0.72 | 0.54 | 0.79 | 0.78 | 2.04 | 0.62 | 0.99 | 1.40 | 1.06 |
| Apoa2 | 6.98 | 1.09 | 0.52 | 1.49 | 1.53 | 1.54 | 0.78 | 1.23 | 0.79 | 3.71 | 9.29 | 1.72 |
| Apoa4 | 7.12 | 3.86 | 1.63 | 2.42 | 2.31 | 2.17 | 7.90 | 5.01 | 6.54 | 1.43 | 1.25 | 2.62 |
| Apob | 1.00 | 1.00 | 1.00 | 85.19 | 31.66 | 57.10 | 0.68 | 0.63 | 0.88 | 3.99 | 2.74 | 2.79 |
| Apoc1 | 2.60 | 2.19 | 0.86 | 0.79 | 1.39 | 0.89 | 0.66 | 1.18 | 0.72 | 1.62 | 8.15 | 2.31 |
| Apoc2 | 5.03 | 5.06 | 1.80 | 1.00 | 1.44 | 1.00 | 1.00 | 0.93 | 1.01 | 1.69 | 3.14 | 1.66 |
| Apoc3 | 18.18 | 2.37 | 6.07 | 2.95 | 2.58 | 1.91 | 1.18 | 1.52 | 1.08 | 2.39 | 5.43 | 3.18 |
| Apoc4 | 7.36 | 3.28 | 0.83 | 1.00 | 0.52 | 1.00 | 0.97 | 1.35 | 1.03 | 1.00 | 1.08 | 1.00 |
| Apod | 5.36 | 4.19 | 2.66 | 1.00 | 1.26 | 1.00 | 1.00 | 1.00 | 1.00 | 2.23 | 3.46 | 2.30 |
| Apoe | 2.73 | 2.87 | 1.91 | 1.10 | 1.33 | 1.08 | 0.73 | 0.53 | 0.85 | 1.02 | 1.46 | 1.03 |
| Apoh | 3.17 | 1.00 | 1.00 | 7.13 | 4.13 | 3.23 | 0.81 | 1.10 | 0.81 | 1.00 | 1.00 | 1.00 |
| Apol9a | 1.09 | 1.52 | 1.19 | 1.00 | 2.06 | 1.77 | 2.43 | 4.11 | 14.79 | 11.41 | 9.93 | 5.46 |
| Apol9b | 1.08 | 1.36 | 1.05 | 1.00 | 2.22 | 1.84 | 1.23 | 0.93 | 5.07 | 13.41 | 11.21 | 6.83 |
| Aprt | 1.16 | 1.68 | 1.28 | 1.07 | 0.69 | 1.04 | 1.42 | 2.47 | 1.78 | 0.90 | 1.62 | 1.03 |
| Aqp11 | 0.84 | 0.90 | 0.87 | 0.94 | 0.94 | 1.04 | 0.85 | 0.62 | 0.98 | 0.91 | 1.00 | 0.99 |
| Arc | 0.49 | 0.43 | 0.62 | 0.66 | 1.00 | 0.69 | 1.00 | 1.00 | 1.00 | 1.00 | 1.00 | 1.00 |
| Arhgap26 | 1.25 | 0.96 | 1.47 | 1.25 | 1.03 | 1.03 | 0.76 | 0.66 | 0.71 | 1.05 | 0.72 | 1.11 |
| Arhgap42 | 2.22 | 1.66 | 1.66 | 1.07 | 1.69 | 0.85 | 1.12 | 1.00 | 0.87 | 0.83 | 0.64 | 0.89 |
| Arhgap5 | 0.48 | 0.35 | 0.89 | 1.32 | 1.00 | 1.09 | 1.07 | 1.00 | 1.03 | 1.22 | 0.24 | 1.07 |
| Arhgef9 | 0.81 | 0.63 | 1.12 | 0.77 | 1.00 | 0.89 | 1.00 | 1.00 | 1.00 | 0.99 | 0.62 | 0.83 |
| Arid5a | 1.96 | 1.94 | 1.36 | 1.00 | 1.00 | 1.00 | 1.00 | 3.09 | 1.00 | 1.07 | 1.39 | 1.36 |
| Arid5b | 0.43 | 0.29 | 1.06 | 1.46 | 1.00 | 1.57 | 0.86 | 1.60 | 0.87 | 0.99 | 0.52 | 0.80 |
| Arl13b | 1.08 | 0.96 | 1.46 | 0.84 | 1.00 | 1.13 | 6.51 | 1.00 | 2.41 | 1.17 | 0.73 | 1.12 |
| Arl2 | 1.16 | 1.71 | 1.01 | 0.71 | 0.57 | 0.83 | 1.09 | 2.51 | 1.61 | 1.03 | 1.66 | 0.99 |
| Arl3 | 1.14 | 1.89 | 1.21 | 0.78 | 0.79 | 0.83 | 0.93 | 0.72 | 1.02 | 1.16 | 1.60 | 1.25 |
| Arl4d | 5.92 | 3.55 | 1.41 | 3.16 | 2.98 | 1.40 | 3.47 | 2.15 | 2.87 | 1.94 | 2.84 | 1.34 |
| Armc12 | 1.00 | 1.00 | 1.00 | 1.95 | 1.68 | 1.09 | 1.00 | 1.00 | 1.00 | 1.00 | 1.00 | 1.00 |
| Armc3 | 1.00 | 1.00 | 1.00 | 1.00 | 1.00 | 1.00 | 1.00 | 1.00 | 1.00 | 1.00 | 1.00 | 1.00 |
| Arntl | 0.84 | 1.02 | 0.73 | 3.32 | 1.00 | 1.87 | 1.00 | 1.00 | 1.52 | 2.43 | 2.11 | 2.03 |
| Arpc3 | 1.08 | 1.39 | 0.98 | 0.94 | 1.23 | 1.00 | 1.18 | 0.47 | 0.95 | 1.07 | 1.46 | 1.04 |
| Arpc4 | 1.17 | 1.53 | 0.93 | 0.80 | 0.62 | 0.94 | 0.92 | 1.71 | 0.93 | 0.97 | 1.57 | 1.01 |
| Arpp21 | 0.63 | 0.75 | 0.61 | 1.00 | 1.00 | 1.00 | 1.00 | 1.00 | 1.00 | 1.00 | 1.00 | 1.00 |
| Arrb2 | 1.07 | 1.52 | 1.12 | 0.97 | 0.67 | 0.86 | 0.55 | 1.44 | 0.92 | 0.77 | 1.49 | 0.96 |
| Arrdc1 | 1.20 | 1.38 | 1.02 | 0.91 | 0.77 | 1.03 | 0.64 | 2.97 | 1.03 | 1.10 | 1.50 | 1.26 |
| Arrdc2 | 1.32 | 1.57 | 1.03 | 2.48 | 5.32 | 1.57 | 0.72 | 0.47 | 0.71 | 1.22 | 1.34 | 1.11 |
| Arrdc3 | 3.60 | 2.99 | 1.72 | 1.43 | 1.22 | 1.11 | 0.57 | 0.39 | 0.65 | 1.13 | 0.89 | 0.97 |
| Arsi | 8.22 | 13.53 | 14.54 | 1.00 | 1.00 | 1.00 | 1.00 | 1.00 | 1.00 | 1.00 | 1.00 | 1.00 |
| Art5 | 1.16 | 1.15 | 0.81 | 1.00 | 0.48 | 1.00 | 1.00 | 1.00 | 1.00 | 1.32 | 0.90 | 0.99 |
| Arv1 | 0.71 | 0.74 | 0.78 | 0.87 | 0.82 | 1.57 | 1.66 | 0.69 | 1.44 | 0.80 | 1.38 | 1.27 |
| Asb11 | 1.00 | 1.00 | 1.00 | 3.22 | 2.73 | 1.74 | 1.00 | 1.00 | 1.00 | 0.68 | 1.42 | 1.00 |
| Asb2 | 1.23 | 1.37 | 1.35 | 1.00 | 1.27 | 1.00 | 1.00 | 1.00 | 1.00 | 1.14 | 1.13 | 0.93 |
| Ascc1 | 1.20 | 2.03 | 1.26 | 0.77 | 0.47 | 0.75 | 1.17 | 2.28 | 0.99 | 1.18 | 1.61 | 1.26 |

Fig. 35- 127

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ang4 | 1.00 | 1.00 | 1.05 | 1.00 | 1.00 | 1.00 | 1.00 | 1.00 | 1.00 | 1.00 | 1.00 | 1.00 |
| Angptl4 | 1.41 | 1.31 | 2.05 | 0.96 | 1.20 | 0.88 | 1.09 | 0.51 | 0.72 | 1.66 | 1.69 | 1.56 |
| Angptl7 | 3.30 | 4.71 | 3.12 | 11.81 | 1.00 | 1.07 | 1.58 | 1.00 | 2.55 | 0.82 | 1.14 | 0.93 |
| Ank2 | 1.46 | 1.28 | 1.37 | 0.55 | 0.95 | 0.52 | 1.12 | 0.53 | 0.92 | 0.68 | 5.27 | 0.70 |
| Ankrd1 | 1.00 | 1.00 | 1.00 | 1.00 | 1.00 | 1.00 | 1.00 | 1.00 | 1.00 | 1.00 | 1.00 | 1.00 |
| Ankrd2 | 1.00 | 1.00 | 1.00 | 1.00 | 1.00 | 1.00 | 1.00 | 3.09 | 1.00 | 1.04 | 0.70 | 0.48 |
| Ankrd33b | 1.00 | 1.00 | 1.00 | 1.68 | 1.00 | 1.00 | 1.41 | 1.00 | 1.12 | 1.06 | 0.94 | 1.06 |
| Ankrd55 | 1.00 | 1.00 | 1.00 | 1.00 | 1.00 | 1.00 | 0.84 | 0.62 | 0.99 | 1.91 | 1.35 | 1.44 |
| Anks1b | 1.00 | 1.00 | 1.00 | 1.00 | 1.00 | 1.00 | 1.00 | 1.00 | 1.00 | 1.00 | 5.30 | 1.00 |
| Anks3 | 0.89 | 0.97 | 1.05 | 0.96 | 1.88 | 1.06 | 0.92 | 2.22 | 0.88 | 1.07 | 1.11 | 0.98 |
| Anp32a | 0.76 | 0.76 | 0.69 | 1.02 | 5.05 | 1.09 | 0.69 | 0.87 | 0.69 | 1.03 | 1.10 | 1.00 |
| Aoc2 | 1.30 | 1.09 | 1.08 | 1.33 | 1.94 | 1.33 | 1.26 | 2.82 | 1.00 | 1.14 | 1.21 | 1.16 |
| Aox4 | 0.94 | 1.13 | 1.16 | 1.00 | 1.00 | 1.00 | 1.00 | 1.00 | 1.00 | 1.00 | 1.00 | 1.00 |
| Ap1g2 | 0.90 | 0.96 | 0.97 | 0.89 | 6.70 | 0.85 | 1.00 | 1.28 | 1.00 | 0.88 | 0.97 | 1.03 |
| Ap2s1 | 0.96 | 1.08 | 0.90 | 0.90 | 1.77 | 0.87 | 0.91 | 3.21 | 1.04 | 1.12 | 1.29 | 0.87 |
| Ap5s1 | 1.06 | 1.01 | 1.04 | 0.77 | 1.38 | 0.98 | 0.80 | 2.95 | 0.79 | 0.96 | 1.25 | 0.99 |
| Apbb1 | 0.88 | 0.86 | 0.95 | 0.72 | 1.85 | 0.64 | 0.96 | 2.39 | 0.97 | 1.01 | 3.46 | 1.09 |
| Apeh | 0.95 | 0.94 | 0.80 | 0.87 | 2.12 | 0.97 | 0.94 | 4.00 | 0.68 | 0.70 | 0.81 | 0.90 |
| Apex1 | 1.10 | 0.89 | 0.93 | 0.78 | 5.80 | 0.72 | 1.12 | 0.78 | 0.94 | 1.39 | 1.60 | 1.42 |
| Apip | 0.92 | 0.76 | 1.05 | 0.94 | 3.41 | 1.27 | 1.01 | 1.41 | 1.04 | 1.08 | 1.14 | 0.69 |
| Aplp1 | 1.24 | 1.48 | 1.07 | 0.66 | 1.00 | 1.06 | 1.15 | 0.40 | 1.03 | 1.19 | 15.21 | 0.92 |
| Apoa1 | 1.87 | 1.96 | 1.54 | 0.80 | 6.23 | 2.28 | 1.95 | 14.07 | 0.85 | 1.00 | 8.85 | 1.20 |
| Apoa1bp | 0.86 | 0.81 | 0.89 | 0.63 | 0.99 | 0.84 | 1.00 | 2.48 | 0.84 | 1.10 | 1.60 | 1.09 |
| Apoa2 | 1.48 | 2.04 | 2.31 | 0.18 | 2.89 | 1.01 | 0.32 | 0.90 | 0.27 | 1.00 | 2.93 | 0.80 |
| Apoa4 | 2.05 | 1.72 | 2.06 | 1.74 | 1.00 | 1.42 | 1.00 | 1.55 | 1.00 | 1.00 | 3.79 | 1.33 |
| Apob | 1.82 | 1.38 | 0.95 | 1.00 | 1.00 | 1.00 | 1.00 | 1.00 | 1.00 | 1.00 | 1.00 | 1.00 |
| Apoc1 | 1.12 | 1.31 | 2.99 | 2.45 | 6.86 | 3.15 | 0.94 | 2.40 | 0.96 | 0.63 | 0.93 | 0.37 |
| Apoc2 | 6.32 | 1.94 | 7.80 | 8.68 | 21.28 | 8.34 | 1.13 | 2.32 | 1.74 | 2.46 | 1.82 | 1.44 |
| Apoc3 | 1.44 | 3.07 | 10.93 | 8.10 | 18.65 | 32.01 | 1.00 | 1.59 | 1.00 | 1.00 | 1.47 | 1.00 |
| Apoc4 | 1.97 | 3.55 | 1.00 | 7.90 | 38.72 | 11.52 | 1.00 | 1.12 | 1.00 | 1.00 | 1.00 | 1.00 |
| Apod | 3.10 | 3.38 | 3.44 | 0.98 | 3.19 | 1.84 | 1.00 | 1.00 | 1.00 | 2.81 | 8.07 | 1.77 |
| Apoe | 1.22 | 1.33 | 1.46 | 1.22 | 2.85 | 1.45 | 0.64 | 0.54 | 0.70 | 1.06 | 1.66 | 1.10 |
| Apoh | 1.87 | 1.45 | 1.72 | 1.00 | 1.69 | 1.00 | 1.07 | 1.53 | 0.92 | 1.00 | 1.00 | 1.00 |
| Apol9a | 19.59 | 31.12 | 16.42 | 1.39 | 1.50 | 1.51 | 1.00 | 1.00 | 1.00 | 1.00 | 0.60 | 1.26 |
| Apol9b | 12.82 | 24.80 | 10.87 | 1.60 | 1.39 | 2.14 | 1.00 | 1.00 | 1.00 | 0.57 | 0.68 | 0.64 |
| Aprt | 0.84 | 0.91 | 0.87 | 1.45 | 3.23 | 1.60 | 0.96 | 2.39 | 1.02 | 1.08 | 1.56 | 1.03 |
| Aqp11 | 1.09 | 1.08 | 0.93 | 1.50 | 1.00 | 1.02 | 0.97 | 0.84 | 1.00 | 1.00 | 1.20 | 1.00 |
| Arc | 0.63 | 0.83 | 0.63 | 5.24 | 1.00 | 5.44 | 1.09 | 0.40 | 1.08 | 0.56 | 2.78 | 0.82 |
| Arhgap26 | 1.28 | 1.32 | 1.00 | 1.19 | 0.65 | 1.07 | 1.06 | 1.27 | 1.04 | 1.44 | 1.22 | 1.47 |
| Arhgap42 | 0.85 | 0.80 | 0.70 | 1.12 | 0.44 | 1.17 | 1.00 | 1.00 | 1.00 | 0.89 | 1.18 | 1.17 |
| Arhgap5 | 0.99 | 0.76 | 0.62 | 1.07 | 0.14 | 0.59 | 1.27 | 1.96 | 1.26 | 0.76 | 0.99 | 1.09 |
| Arhgef9 | 0.87 | 0.72 | 0.95 | 0.61 | 1.00 | 0.74 | 1.00 | 1.00 | 1.00 | 0.76 | 5.11 | 0.92 |
| Arid5a | 2.16 | 2.71 | 1.28 | 2.49 | 5.01 | 2.11 | 1.08 | 1.90 | 1.01 | 1.33 | 1.36 | 1.19 |
| Arid5b | 1.33 | 1.23 | 0.83 | 2.70 | 0.28 | 0.56 | 1.55 | 1.00 | 1.43 | 0.77 | 0.36 | 1.31 |
| Arl13b | 1.44 | 1.19 | 1.18 | 2.09 | 1.00 | 1.30 | 1.36 | 0.47 | 1.12 | 1.07 | 0.77 | 1.07 |
| Arl2 | 1.04 | 1.22 | 1.27 | 0.70 | 2.30 | 1.04 | 1.07 | 2.51 | 1.05 | 0.84 | 1.50 | 1.06 |
| Arl3 | 1.27 | 1.68 | 1.24 | 0.94 | 1.26 | 0.97 | 0.94 | 1.19 | 0.98 | 1.20 | 1.86 | 1.09 |
| Arl4d | 2.08 | 2.32 | 1.70 | 3.54 | 8.57 | 1.80 | 0.70 | 0.56 | 1.11 | 1.30 | 1.43 | 0.84 |
| Armc12 | 1.00 | 1.00 | 1.00 | 1.14 | 1.04 | 1.00 | 0.89 | 2.61 | 1.03 | 1.00 | 1.00 | 1.00 |
| Armc3 | 1.00 | 1.00 | 1.00 | 1.00 | 1.43 | 1.66 | 1.11 | 1.69 | 1.08 | 1.00 | 1.49 | 1.35 |
| Arntl | 3.01 | 3.14 | 2.11 | 7.49 | 1.00 | 3.15 | 1.33 | 1.00 | 1.18 | 1.23 | 1.33 | 1.16 |
| Arpc3 | 0.89 | 0.95 | 0.84 | 1.00 | 7.08 | 1.02 | 0.84 | 0.47 | 0.85 | 1.03 | 1.12 | 0.88 |
| Arpc4 | 0.81 | 0.93 | 0.85 | 0.96 | 2.35 | 0.91 | 0.83 | 2.23 | 0.93 | 0.95 | 1.06 | 0.83 |
| Arpp21 | 1.00 | 1.00 | 1.00 | 1.00 | 1.00 | 1.00 | 1.00 | 1.00 | 1.00 | 1.00 | 13.02 | 1.00 |
| Arrb2 | 1.28 | 1.19 | 1.32 | 0.74 | 2.00 | 0.86 | 0.49 | 2.11 | 1.38 | 1.04 | 1.27 | 0.93 |
| Arrdc1 | 1.12 | 1.18 | 1.06 | 0.79 | 3.84 | 1.01 | 1.03 | 3.72 | 1.02 | 0.94 | 0.99 | 0.94 |
| Arrdc2 | 1.25 | 1.42 | 1.13 | 2.23 | 4.54 | 1.70 | 1.08 | 0.84 | 1.09 | 1.13 | 1.09 | 0.91 |
| Arrdc3 | 1.21 | 1.37 | 1.00 | 2.85 | 1.97 | 1.16 | 1.02 | 0.63 | 1.01 | 1.57 | 1.46 | 0.94 |
| Arsi | 1.00 | 1.00 | 1.00 | 0.49 | 1.00 | 0.38 | 1.00 | 1.00 | 1.00 | 0.61 | 0.43 | 0.39 |
| Art5 | 1.00 | 1.00 | 1.00 | 1.00 | 1.00 | 1.00 | 0.92 | 3.04 | 0.95 | 1.00 | 1.00 | 1.00 |
| Arv1 | 0.83 | 1.07 | 0.72 | 0.82 | 0.99 | 0.86 | 1.22 | 1.37 | 0.94 | 0.71 | 0.61 | 1.28 |
| Asb11 | 4.31 | 2.65 | 2.37 | 0.66 | 1.00 | 0.70 | 1.00 | 1.00 | 1.01 | 1.00 | 1.00 | 1.00 |
| Asb2 | 1.26 | 1.35 | 1.55 | 1.33 | 1.20 | 2.07 | 0.70 | 0.79 | 0.80 | 0.64 | 0.83 | 0.70 |
| Ascc1 | 1.15 | 1.57 | 1.14 | 1.21 | 2.59 | 1.73 | 0.98 | 2.86 | 0.94 | 1.31 | 1.57 | 1.18 |

Fig. 35- 128

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ang4 | 1.00 | 1.00 | 1.00 | 1.00 | 1.00 | 1.00 | 1.00 | 1.00 | 1.00 | 1.00 | 1.00 | 1.00 |
| Angptl4 | 0.50 | 0.49 | 0.84 | 1.16 | 0.79 | 1.48 | 4.64 | 11.36 | 5.18 | 1.08 | 0.86 | 1.10 |
| Angptl7 | 1.37 | 1.44 | 1.84 | 1.57 | 1.00 | 1.69 | 1.74 | 0.70 | 1.86 | 0.72 | 1.24 | 1.18 |
| Ank2 | 1.00 | 1.00 | 1.00 | 0.93 | 1.07 | 1.04 | 0.99 | 0.76 | 1.15 | 1.00 | 1.00 | 1.00 |
| Ankrd1 | 1.00 | 1.00 | 1.00 | 1.00 | 1.00 | 1.00 | 2.62 | 2.68 | 3.73 | 1.00 | 1.00 | 1.00 |
| Ankrd2 | 1.00 | 1.00 | 1.00 | 1.00 | 0.33 | 1.00 | 1.94 | 7.88 | 1.47 | 1.00 | 1.00 | 1.00 |
| Ankrd33b | 1.00 | 1.00 | 1.00 | 1.08 | 0.45 | 0.97 | 2.17 | 0.76 | 3.09 | 0.53 | 1.23 | 0.97 |
| Ankrd55 | 1.00 | 1.00 | 1.00 | 1.06 | 1.00 | 1.09 | 2.75 | 18.39 | 1.67 | 1.00 | 1.00 | 1.00 |
| Anks1b | 1.00 | 1.00 | 1.00 | 1.02 | 0.89 | 0.99 | 1.00 | 1.00 | 1.00 | 1.00 | 1.00 | 1.00 |
| Anks3 | 1.00 | 1.00 | 1.00 | 1.01 | 1.13 | 1.02 | 1.07 | 6.28 | 0.98 | 2.96 | 1.21 | 1.00 |
| Anp32a | 1.11 | 1.12 | 1.24 | 0.95 | 0.82 | 0.87 | 0.85 | 1.96 | 0.77 | 1.87 | 1.23 | 1.21 |
| Aoc2 | 1.42 | 1.86 | 1.25 | 0.97 | 0.84 | 1.25 | 1.52 | 5.89 | 1.39 | 1.30 | 0.87 | 0.62 |
| Aox4 | 1.00 | 1.00 | 1.00 | 1.00 | 1.00 | 1.00 | 1.02 | 5.07 | 1.01 | 1.00 | 1.00 | 1.00 |
| Ap1g2 | 1.79 | 0.62 | 1.02 | 0.74 | 0.64 | 0.94 | 0.89 | 6.17 | 0.88 | 2.67 | 0.89 | 0.95 |
| Ap2s1 | 0.92 | 1.54 | 0.89 | 1.19 | 0.87 | 1.04 | 1.33 | 17.46 | 0.93 | 4.29 | 1.39 | 1.28 |
| Ap5s1 | 0.51 | 0.60 | 0.88 | 1.28 | 0.82 | 0.97 | 1.27 | 6.35 | 1.07 | 2.45 | 1.61 | 1.22 |
| Apbb1 | 1.00 | 1.00 | 1.00 | 1.09 | 0.87 | 1.01 | 1.24 | 5.20 | 1.09 | 1.00 | 1.00 | 1.00 |
| Apeh | 0.98 | 1.11 | 0.92 | 1.03 | 0.90 | 1.05 | 1.14 | 15.27 | 1.02 | 2.91 | 0.79 | 0.95 |
| Apex1 | 1.29 | 2.39 | 1.12 | 1.19 | 2.15 | 1.45 | 1.08 | 2.89 | 0.87 | 1.02 | 0.71 | 0.94 |
| Apip | 1.74 | 0.59 | 0.44 | 0.81 | 1.39 | 1.03 | 1.28 | 6.00 | 0.99 | 1.82 | 1.15 | 0.88 |
| Aplp1 | 1.12 | 1.28 | 1.20 | 1.07 | 1.16 | 1.01 | 1.84 | 1.00 | 1.11 | 1.27 | 2.16 | 2.24 |
| Apoa1 | 3.37 | 1.00 | 0.45 | 0.16 | 1.62 | 1.87 | 4.26 | 10.22 | 1.22 | 1.00 | 1.00 | 1.00 |
| Apoa1bp | 0.62 | 0.74 | 0.85 | 1.05 | 0.69 | 0.98 | 0.96 | 7.79 | 0.89 | 2.42 | 1.09 | 1.22 |
| Apoa2 | 3.77 | 1.00 | 1.03 | 0.40 | 27.20 | 2.46 | 1.00 | 1.36 | 1.94 | 1.87 | 1.00 | 1.00 |
| Apoa4 | 1.00 | 1.00 | 0.61 | 1.00 | 1.00 | 1.65 | 5.68 | 1.00 | 1.00 | 1.00 | 1.00 | 1.00 |
| Apob | 1.00 | 1.00 | 1.00 | 1.00 | 1.00 | 1.00 | 1.00 | 1.00 | 1.00 | 1.00 | 1.00 | 1.00 |
| Apoc1 | 0.52 | 1.07 | 2.04 | 1.56 | 0.59 | 2.29 | 1.34 | 14.32 | 1.06 | 5.51 | 2.61 | 0.49 |
| Apoc2 | 1.00 | 1.00 | 1.00 | 1.00 | 1.67 | 1.00 | 2.46 | 18.90 | 1.02 | 8.79 | 4.49 | 2.79 |
| Apoc3 | 1.00 | 1.00 | 1.00 | 1.00 | 11.01 | 1.98 | 1.73 | 5.97 | 1.35 | 1.00 | 1.00 | 1.00 |
| Apoc4 | 1.00 | 1.00 | 1.00 | 1.00 | 1.00 | 1.00 | 2.16 | 9.17 | 1.45 | 1.00 | 1.00 | 1.00 |
| Apod | 0.53 | 1.25 | 1.47 | 1.48 | 1.47 | 1.42 | 1.35 | 4.03 | 1.27 | 1.03 | 1.00 | 1.00 |
| Apoe | 0.78 | 1.41 | 1.10 | 1.06 | 0.96 | 1.01 | 1.41 | 2.14 | 1.04 | 2.90 | 2.48 | 1.79 |
| Apoh | 1.00 | 1.00 | 1.00 | 1.00 | 1.00 | 1.00 | 1.00 | 1.00 | 1.00 | 1.00 | 1.00 | 1.00 |
| Apol9a | 1.00 | 1.00 | 1.00 | 1.00 | 1.00 | 1.00 | 6.47 | 12.62 | 5.93 | 1.00 | 1.00 | 1.00 |
| Apol9b | 1.00 | 1.00 | 1.00 | 1.00 | 1.00 | 1.00 | 2.15 | 1.79 | 3.17 | 1.00 | 1.00 | 1.00 |
| Aprt | 1.23 | 0.78 | 0.85 | 0.96 | 0.84 | 1.00 | 1.18 | 9.55 | 0.80 | 3.68 | 1.37 | 1.39 |
| Aqp11 | 1.00 | 1.00 | 1.00 | 1.06 | 3.00 | 0.94 | 6.52 | 1.00 | 1.00 | 1.50 | 1.20 | 1.00 |
| Arc | 1.00 | 1.00 | 1.00 | 1.30 | 2.57 | 1.40 | 1.64 | 0.48 | 0.62 | 1.00 | 1.00 | 1.00 |
| Arhgap26 | 0.75 | 1.02 | 1.10 | 1.10 | 1.01 | 1.03 | 1.58 | 1.00 | 1.87 | 1.13 | 1.20 | 1.20 |
| Arhgap42 | 1.00 | 1.00 | 1.00 | 0.76 | 1.00 | 0.98 | 1.02 | 0.20 | 1.10 | 1.00 | 1.00 | 1.00 |
| Arhgap5 | 1.43 | 1.32 | 1.45 | 0.74 | 0.61 | 0.73 | 0.66 | 0.43 | 1.11 | 1.00 | 1.00 | 1.00 |
| Arhgef9 | 1.00 | 1.00 | 1.00 | 1.00 | 1.04 | 0.95 | 0.89 | 1.00 | 1.18 | 1.00 | 1.00 | 1.00 |
| Arid5a | 1.00 | 1.00 | 1.00 | 1.16 | 0.85 | 0.94 | 1.65 | 6.16 | 1.78 | 2.49 | 1.46 | 1.24 |
| Arid5b | 1.40 | 1.41 | 1.00 | 0.80 | 1.00 | 0.79 | 0.89 | 0.23 | 0.99 | 1.00 | 1.00 | 1.00 |
| Arl13b | 1.00 | 1.00 | 1.00 | 1.12 | 1.00 | 0.96 | 1.25 | 0.13 | 1.15 | 1.00 | 1.03 | 1.20 |
| Arl2 | 0.67 | 0.38 | 0.78 | 1.03 | 0.87 | 1.08 | 1.20 | 10.67 | 0.96 | 2.53 | 1.25 | 1.10 |
| Arl3 | 1.09 | 0.69 | 0.62 | 1.14 | 1.07 | 1.06 | 1.52 | 4.59 | 1.05 | 1.55 | 1.51 | 1.30 |
| Arl4d | 1.07 | 2.16 | 1.73 | 1.56 | 0.52 | 1.30 | 1.29 | 0.79 | 0.81 | 0.53 | 0.44 | 0.62 |
| Armc12 | 1.00 | 1.00 | 1.00 | 1.00 | 1.00 | 1.00 | 1.74 | 5.76 | 1.54 | 1.29 | 1.71 | 1.00 |
| Armc3 | 1.00 | 1.00 | 1.00 | 1.00 | 2.37 | 1.00 | 1.00 | 1.17 | 1.00 | 4.04 | 1.36 | 1.17 |
| Arntl | 2.08 | 1.19 | 1.00 | 1.15 | 1.00 | 1.09 | 1.18 | 0.16 | 1.20 | 0.24 | 0.60 | 1.04 |
| Arpc3 | 1.48 | 0.76 | 0.65 | 1.08 | 1.80 | 1.05 | 0.99 | 1.91 | 1.01 | 1.76 | 1.24 | 1.23 |
| Arpc4 | 1.17 | 1.37 | 0.94 | 1.09 | 0.88 | 1.04 | 1.12 | 7.28 | 0.92 | 2.69 | 1.30 | 1.22 |
| Arpp21 | 1.00 | 1.00 | 1.00 | 1.01 | 2.03 | 0.95 | 1.59 | 1.00 | 1.65 | 1.00 | 1.00 | 1.00 |
| Arrb2 | 0.81 | 1.13 | 1.69 | 0.95 | 1.10 | 0.98 | 1.38 | 5.94 | 1.19 | 3.78 | 1.84 | 1.49 |
| Arrdc1 | 1.11 | 0.92 | 1.08 | 0.99 | 1.36 | 1.29 | 1.04 | 6.58 | 0.79 | 3.06 | 1.32 | 1.14 |
| Arrdc2 | 0.77 | 1.06 | 1.34 | 1.63 | 2.48 | 1.45 | 1.76 | 2.90 | 1.61 | 1.11 | 0.99 | 1.08 |
| Arrdc3 | 1.41 | 1.27 | 1.30 | 0.89 | 0.78 | 0.94 | 1.28 | 0.96 | 1.42 | 0.97 | 1.28 | 0.86 |
| Arsi | 1.00 | 1.00 | 1.00 | 1.00 | 1.00 | 1.00 | 0.96 | 1.00 | 1.00 | 1.00 | 1.00 | 1.00 |
| Art5 | 1.00 | 1.00 | 1.00 | 1.00 | 1.00 | 1.00 | 2.65 | 20.91 | 1.69 | 1.00 | 1.00 | 1.00 |
| Arv1 | 1.00 | 1.13 | 1.00 | 0.61 | 8.84 | 1.51 | 0.52 | 0.54 | 0.39 | 0.55 | 0.52 | 0.97 |
| Asb11 | 1.81 | 2.83 | 1.41 | 1.30 | 6.32 | 0.75 | 2.12 | 2.78 | 2.00 | 1.00 | 1.00 | 1.00 |
| Asb2 | 1.00 | 1.00 | 1.00 | 1.32 | 1.92 | 1.11 | 1.43 | 5.84 | 0.97 | 1.15 | 0.85 | 0.76 |
| Ascc1 | 0.74 | 2.16 | 1.39 | 0.82 | 0.63 | 1.08 | 1.61 | 13.38 | 1.03 | 2.78 | 1.31 | 1.43 |

Fig. 35- 129

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ascc2 | 0.89 | 0.81 | 1.04 | 0.63 | 6.33 | 1.38 | 1.45 | 2.05 | 1.54 | 4.40 | 4.58 | 1.14 |
| Ascl3 | 1.00 | 1.00 | 1.00 | 1.00 | 1.00 | 1.00 | 1.00 | 1.00 | 1.00 | 1.00 | 1.00 | 1.00 |
| Asgr1 | 1.00 | 1.00 | 1.00 | 1.00 | 1.00 | 1.00 | 1.00 | 1.00 | 1.00 | 2.03 | 2.51 | 2.04 |
| Asl | 1.00 | 1.88 | 1.17 | 2.62 | 88.39 | 3.63 | 1.95 | 1.00 | 1.25 | 2.96 | 4.74 | 0.81 |
| Aspg | 4.51 | 4.89 | 2.82 | 2.33 | 11.68 | 2.50 | 1.00 | 1.00 | 1.00 | 3.86 | 3.14 | 1.34 |
| Asph | 0.79 | 0.78 | 0.83 | 8.87 | 4.51 | 3.92 | 0.57 | 0.68 | 0.56 | 0.53 | 0.54 | 0.83 |
| Asphd1 | 1.00 | 1.00 | 1.00 | 1.00 | 1.02 | 1.00 | 1.00 | 1.00 | 1.00 | 1.00 | 1.00 | 1.00 |
| Asphd2 | 1.00 | 1.00 | 1.00 | 1.00 | 0.35 | 1.00 | 1.00 | 1.08 | 1.31 | 1.00 | 1.00 | 1.00 |
| Atf3 | 18.76 | 20.30 | 8.07 | 7.48 | 0.88 | 1.91 | 7.16 | 10.20 | 2.65 | 0.46 | 0.87 | 1.92 |
| Atg101 | 0.94 | 0.64 | 0.89 | 1.59 | 21.51 | 2.36 | 1.36 | 1.30 | 1.29 | 2.76 | 2.69 | 1.02 |
| Atox1 | 1.40 | 0.50 | 0.95 | 0.30 | 8.05 | 0.87 | 0.99 | 0.86 | 0.85 | 2.41 | 3.74 | 0.87 |
| Atp13a1 | 1.24 | 0.68 | 1.30 | 0.47 | 3.41 | 1.10 | 1.27 | 1.04 | 1.01 | 2.36 | 3.21 | 1.07 |
| Atp13a2 | 1.24 | 0.53 | 0.91 | 0.64 | 3.23 | 1.00 | 1.45 | 1.17 | 1.01 | 2.55 | 2.83 | 0.96 |
| Atp1a2 | 0.78 | 1.00 | 0.90 | 0.58 | 0.78 | 1.00 | 1.00 | 1.04 | 0.98 | 2.06 | 0.86 | 0.80 |
| Atp1a3 | 1.00 | 1.00 | 1.00 | 1.00 | 0.03 | 0.75 | 1.00 | 1.00 | 1.00 | 1.00 | 0.91 | 0.72 |
| Atp2a1 | 0.87 | 0.94 | 0.90 | 1.21 | 1.18 | 1.10 | 0.69 | 1.13 | 1.50 | 1.68 | 1.00 | 1.00 |
| Atp2a3 | 1.29 | 1.00 | 1.62 | 1.31 | 2.76 | 1.50 | 1.34 | 1.33 | 1.16 | 2.61 | 1.90 | 0.91 |
| Atp2b2 | 1.00 | 1.00 | 1.00 | 1.00 | 0.14 | 1.00 | 1.00 | 1.00 | 1.00 | 1.00 | 0.97 | 0.89 |
| Atp5d | 1.13 | 0.62 | 0.88 | 0.26 | 5.72 | 0.88 | 1.06 | 0.76 | 0.82 | 2.22 | 3.37 | 1.00 |
| Atp5e | 1.01 | 0.38 | 0.73 | 0.45 | 21.99 | 0.87 | 0.85 | 0.70 | 0.76 | 3.73 | 6.71 | 0.86 |
| Atp5g3 | 0.87 | 0.58 | 0.73 | 0.80 | 5.69 | 1.24 | 0.74 | 0.77 | 0.72 | 1.15 | 2.08 | 0.86 |
| Atp5h | 1.23 | 0.39 | 0.77 | 0.31 | 10.37 | 0.84 | 0.86 | 0.72 | 0.77 | 2.95 | 4.16 | 0.94 |
| Atp5j2 | 1.17 | 0.39 | 0.81 | 0.20 | 10.33 | 0.82 | 1.03 | 0.85 | 0.77 | 3.57 | 4.02 | 0.85 |
| Atp5k | 3.07 | 0.28 | 0.75 | 0.23 | 13.24 | 0.78 | 1.00 | 0.62 | 0.70 | 5.75 | 5.39 | 0.91 |
| Atp5l | 1.39 | 0.57 | 0.81 | 0.32 | 6.43 | 0.94 | 0.70 | 0.79 | 0.71 | 2.06 | 3.33 | 0.96 |
| Atp5o | 0.96 | 0.40 | 0.82 | 0.15 | 9.95 | 0.87 | 1.01 | 0.78 | 0.77 | 3.37 | 4.36 | 0.86 |
| Atp6v0b | 1.36 | 0.62 | 1.04 | 0.27 | 5.88 | 1.07 | 1.08 | 0.94 | 0.93 | 2.91 | 3.99 | 0.93 |
| Atp6v0c | 1.28 | 9.15 | 0.93 | 0.36 | 0.09 | 0.99 | 0.96 | 0.82 | 0.84 | 0.12 | 0.01 | 1.06 |
| Atp6v0c-ps2 | 0.55 | 0.89 | 3.48 | 2.73 | 103.08 | 1.97 | 1.51 | 2.37 | 2.50 | 1.50 | 6.35 | 0.70 |
| Atp6v1e1 | 1.11 | 0.99 | 0.74 | 0.67 | 3.74 | 1.53 | 0.82 | 0.71 | 0.67 | 1.01 | 1.56 | 1.12 |
| Atp6v1g2 | 0.99 | 0.76 | 0.68 | 0.49 | 0.06 | 0.61 | 1.08 | 0.81 | 1.43 | 0.93 | 0.92 | 1.48 |
| Atp8b3 | 1.00 | 1.00 | 1.00 | 1.00 | 1.00 | 1.00 | 1.00 | 1.00 | 1.00 | 1.00 | 1.00 | 1.00 |
| Atp9a | 1.55 | 0.72 | 1.17 | 0.27 | 5.10 | 0.90 | 0.99 | 0.87 | 0.93 | 2.78 | 3.48 | 0.93 |
| Atp9b | 1.85 | 0.84 | 1.23 | 0.56 | 5.89 | 1.28 | 1.36 | 1.25 | 1.22 | 3.76 | 3.88 | 1.17 |
| Atpif1 | 1.12 | 0.52 | 0.59 | 0.61 | 2.23 | 1.35 | 1.03 | 0.79 | 0.84 | 1.28 | 1.67 | 0.89 |
| Atraid | 1.52 | 0.74 | 0.97 | 0.56 | 4.50 | 1.00 | 0.94 | 0.93 | 0.91 | 1.11 | 2.16 | 1.05 |
| Aup1 | 1.39 | 0.84 | 1.13 | 0.43 | 4.05 | 1.11 | 1.53 | 1.22 | 1.16 | 2.31 | 2.76 | 0.98 |
| Aurkaip1 | 1.15 | 0.71 | 0.92 | 0.46 | 4.18 | 0.89 | 0.88 | 0.81 | 0.90 | 1.78 | 2.27 | 0.95 |
| Awat1 | 1.00 | 1.00 | 1.00 | 1.00 | 1.00 | 1.00 | 1.00 | 1.00 | 1.00 | 1.00 | 1.00 | 1.00 |
| B330016D10Rik | 1.47 | 1.25 | 0.97 | 0.90 | 1.97 | 0.89 | 0.99 | 0.84 | 1.11 | 1.23 | 1.39 | 1.18 |
| B3gat1 | 1.00 | 1.00 | 1.00 | 1.00 | 0.22 | 1.00 | 1.00 | 1.00 | 1.00 | 1.00 | 1.00 | 1.00 |
| B3gnt9 | 0.60 | 0.31 | 0.78 | 0.89 | 29.23 | 0.86 | 0.68 | 0.59 | 1.00 | 5.31 | 5.35 | 0.72 |
| B4galnt1 | 1.39 | 1.41 | 2.15 | 0.58 | 0.46 | 0.76 | 0.82 | 0.63 | 1.10 | 2.13 | 2.50 | 0.93 |
| B4galt4 | 0.91 | 2.02 | 1.39 | 0.77 | 0.46 | 1.03 | 1.08 | 1.17 | 1.20 | 0.27 | 0.34 | 0.86 |
| B9d2 | 1.22 | 0.57 | 1.17 | 0.21 | 2.76 | 0.75 | 1.06 | 0.49 | 0.83 | 1.64 | 3.08 | 1.05 |
| BC004004 | 0.81 | 0.59 | 0.85 | 0.49 | 3.76 | 0.93 | 0.89 | 0.81 | 0.75 | 3.56 | 3.15 | 1.00 |
| BC005537 | 1.39 | 7.38 | 1.59 | 1.93 | 0.10 | 0.85 | 1.32 | 1.78 | 1.28 | 1.00 | 0.21 | 1.07 |
| BC005561 | 1.00 | 0.92 | 1.00 | 1.00 | 3.75 | 1.00 | 1.00 | 1.03 | 1.00 | 3.40 | 1.81 | 1.00 |
| BC018473 | 1.61 | 1.48 | 2.77 | 1.54 | 4.66 | 1.11 | 2.18 | 2.20 | 2.39 | 1.76 | 1.45 | 1.43 |
| BC021614 | 1.00 | 1.00 | 1.00 | 1.01 | 25.01 | 2.31 | 1.00 | 1.00 | 1.00 | 2.31 | 3.08 | 1.02 |
| BC029214 | 1.38 | 0.66 | 1.48 | 0.32 | 4.28 | 0.43 | 1.61 | 1.06 | 0.95 | 2.78 | 3.33 | 1.07 |
| BC048679 | 0.32 | 0.46 | 0.35 | 1.00 | 1.00 | 1.00 | 1.00 | 1.00 | 1.00 | 1.00 | 1.00 | 1.00 |
| BC049730 | 1.00 | 1.00 | 1.00 | 1.00 | 1.00 | 1.00 | 1.00 | 1.00 | 1.00 | 1.00 | 1.00 | 1.00 |
| BC051142 | 1.00 | 1.00 | 1.00 | 1.00 | 1.00 | 1.49 | 1.00 | 1.00 | 1.00 | 1.00 | 1.00 | 1.89 |
| BC051226 | 0.65 | 0.34 | 1.21 | 3.23 | 13.53 | 2.62 | 0.77 | 0.60 | 0.67 | 1.80 | 1.58 | 2.33 |
| BC064078 | 1.00 | 1.00 | 1.00 | 1.00 | 1.00 | 1.00 | 1.00 | 1.00 | 1.67 | 0.98 | 1.00 | 3.13 |
| BC147527 | 1.00 | 1.00 | 1.00 | 1.00 | 1.00 | 1.00 | 1.00 | 1.00 | 1.00 | 1.69 | 1.24 | 1.25 |
| Baalc | 1.00 | 1.00 | 1.00 | 1.00 | 0.22 | 1.00 | 1.00 | 1.00 | 1.00 | 1.00 | 1.00 | 1.00 |
| Bag1 | 1.06 | 0.46 | 0.85 | 0.52 | 5.98 | 1.10 | 1.01 | 0.98 | 0.91 | 5.36 | 4.79 | 1.20 |
| Bai1 | 1.00 | 1.00 | 1.00 | 1.00 | 0.31 | 1.00 | 1.00 | 1.00 | 1.00 | 1.00 | 1.00 | 1.00 |
| Batf3 | 1.00 | 1.79 | 1.00 | 1.00 | 5.51 | 1.00 | 1.00 | 1.00 | 1.00 | 0.96 | 1.97 | 0.70 |
| Bcan | 1.00 | 1.00 | 1.00 | 1.00 | 0.18 | 1.00 | 1.00 | 1.00 | 1.00 | 1.00 | 1.00 | 1.00 |
| Bcas1 | 1.00 | 1.00 | 1.00 | 1.00 | 0.27 | 1.00 | 1.00 | 1.00 | 1.00 | 1.16 | 1.94 | 1.57 |
| Bcas2 | 0.91 | 1.10 | 0.80 | 0.91 | 3.69 | 1.40 | 0.80 | 0.81 | 0.98 | 1.21 | 1.38 | 1.06 |

Fig. 35- 130

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ascc2 | 0.87 | 0.80 | 1.06 | 1.07 | 0.59 | 1.08 | 1.05 | 2.84 | 0.97 | 0.99 | 1.06 | 1.01 |
| Ascl3 | 4.00 | 7.78 | 3.91 | 1.09 | 2.07 | 1.00 | 1.00 | 1.00 | 1.00 | 1.00 | 1.00 | 1.00 |
| Asgr1 | 1.22 | 1.00 | 1.00 | 1.00 | 0.80 | 1.00 | 0.76 | 0.54 | 0.82 | 1.00 | 1.00 | 1.00 |
| Asl | 1.47 | 1.60 | 1.32 | 1.50 | 1.05 | 1.21 | 2.28 | 4.25 | 1.65 | 0.84 | 1.44 | 0.86 |
| Aspg | 2.22 | 4.24 | 1.12 | 1.29 | 1.05 | 1.39 | 1.07 | 2.02 | 0.97 | 1.27 | 1.87 | 1.43 |
| Asph | 2.38 | 1.77 | 1.75 | 0.77 | 0.87 | 1.01 | 0.79 | 0.62 | 0.80 | 0.81 | 0.65 | 0.81 |
| Asphd1 | 1.00 | 1.00 | 1.00 | 1.00 | 1.00 | 1.00 | 1.00 | 1.00 | 1.00 | 1.00 | 1.00 | 1.00 |
| Asphd2 | 1.00 | 1.00 | 1.00 | 1.00 | 1.00 | 1.00 | 1.00 | 1.00 | 1.00 | 1.00 | 1.36 | 1.00 |
| Atf3 | 1.85 | 2.73 | 1.59 | 1.00 | 1.00 | 1.02 | 2.61 | 1.00 | 6.08 | 1.34 | 1.57 | 1.13 |
| Atg101 | 1.19 | 1.38 | 0.98 | 1.00 | 0.77 | 1.13 | 0.93 | 1.59 | 0.73 | 0.97 | 1.46 | 1.01 |
| Atox1 | 1.22 | 1.51 | 1.18 | 0.73 | 0.56 | 0.85 | 0.83 | 1.82 | 0.88 | 1.10 | 1.77 | 0.95 |
| Atp13a1 | 0.87 | 1.00 | 0.96 | 1.09 | 0.78 | 1.05 | 1.08 | 1.83 | 1.22 | 1.08 | 1.03 | 1.01 |
| Atp13a2 | 1.22 | 1.54 | 1.41 | 0.93 | 0.77 | 1.10 | 0.86 | 1.70 | 0.96 | 0.99 | 1.26 | 1.03 |
| Atp1a2 | 1.07 | 0.78 | 0.46 | 1.00 | 1.00 | 0.88 | 1.00 | 1.00 | 1.00 | 0.81 | 1.01 | 0.82 |
| Atp1a3 | 1.10 | 0.90 | 1.03 | 1.00 | 1.00 | 1.00 | 1.00 | 1.00 | 1.00 | 1.00 | 1.00 | 0.91 |
| Atp2a1 | 0.33 | 0.39 | 1.00 | 1.00 | 1.00 | 1.00 | 1.00 | 1.00 | 1.00 | 1.00 | 1.00 | 0.81 |
| Atp2a3 | 0.81 | 0.91 | 0.90 | 0.93 | 0.53 | 0.96 | 1.00 | 1.00 | 1.00 | 1.04 | 0.97 | 1.04 |
| Atp2b2 | 1.00 | 1.00 | 1.00 | 1.00 | 1.00 | 1.00 | 1.00 | 1.00 | 1.00 | 1.00 | 1.00 | 1.00 |
| Atp5d | 0.99 | 1.38 | 0.90 | 0.87 | 0.65 | 0.95 | 0.90 | 1.57 | 0.82 | 1.03 | 1.57 | 0.99 |
| Atp5e | 1.07 | 1.43 | 0.82 | 0.80 | 0.50 | 0.78 | 0.97 | 2.91 | 0.78 | 0.98 | 2.01 | 0.96 |
| Atp5g3 | 1.08 | 1.17 | 0.79 | 0.72 | 0.83 | 0.71 | 0.84 | 0.80 | 0.73 | 0.94 | 1.58 | 0.94 |
| Atp5h | 1.08 | 1.52 | 0.90 | 0.67 | 0.59 | 0.78 | 1.09 | 1.73 | 0.88 | 0.94 | 1.90 | 0.83 |
| Atp5j2 | 0.99 | 1.24 | 0.78 | 0.74 | 0.48 | 0.80 | 1.06 | 2.51 | 1.01 | 1.09 | 1.87 | 1.00 |
| Atp5k | 0.42 | 1.02 | 0.83 | 0.85 | 0.46 | 0.79 | 0.15 | 3.18 | 1.00 | 0.70 | 1.21 | 0.64 |
| Atp5l | 1.61 | 1.49 | 0.81 | 0.71 | 0.67 | 0.68 | 1.23 | 1.57 | 0.80 | 0.87 | 1.88 | 0.91 |
| Atp5o | 1.04 | 1.39 | 0.73 | 0.88 | 0.48 | 0.81 | 0.99 | 2.21 | 0.81 | 1.09 | 1.86 | 0.99 |
| Atp6v0b | 1.45 | 1.97 | 1.21 | 0.96 | 0.63 | 0.99 | 0.92 | 2.46 | 0.83 | 1.08 | 1.79 | 1.06 |
| Atp6v0c | 1.18 | 1.48 | 1.16 | 0.95 | 1.30 | 1.09 | 1.10 | 1.00 | 0.99 | 0.99 | 1.17 | 1.14 |
| Atp6v0c-ps2 | 1.24 | 1.88 | 0.39 | 1.00 | 0.84 | 0.67 | 1.00 | 1.36 | 0.36 | 1.00 | 5.66 | 0.84 |
| Atp6v1e1 | 1.43 | 1.75 | 1.10 | 1.05 | 1.19 | 1.12 | 1.11 | 1.02 | 1.18 | 1.18 | 1.60 | 1.03 |
| Atp6v1g2 | 1.24 | 1.20 | 1.38 | 0.66 | 0.50 | 0.64 | 1.00 | 1.00 | 0.88 | 0.91 | 0.79 | 1.09 |
| Atp8b3 | 1.00 | 1.00 | 1.00 | 1.00 | 1.00 | 1.00 | 1.00 | 1.00 | 1.00 | 1.00 | 1.00 | 1.00 |
| Atp9a | 1.25 | 1.27 | 1.15 | 1.02 | 0.51 | 0.97 | 1.09 | 2.09 | 1.19 | 0.97 | 1.31 | 1.10 |
| Atp9b | 1.37 | 1.54 | 1.14 | 1.51 | 0.72 | 1.46 | 1.29 | 3.88 | 1.29 | 1.33 | 1.71 | 1.30 |
| Atpif1 | 1.14 | 1.18 | 0.88 | 0.70 | 0.95 | 0.75 | 0.90 | 0.58 | 0.43 | 1.00 | 1.43 | 0.95 |
| Atraid | 1.64 | 2.08 | 1.30 | 0.87 | 1.03 | 0.92 | 0.95 | 0.64 | 0.93 | 1.00 | 1.86 | 1.08 |
| Aup1 | 1.28 | 1.37 | 1.15 | 1.01 | 0.74 | 1.08 | 0.96 | 1.55 | 0.94 | 1.09 | 1.46 | 1.12 |
| Aurkaip1 | 1.12 | 1.52 | 0.95 | 0.88 | 0.72 | 0.90 | 1.06 | 1.57 | 0.97 | 1.09 | 1.64 | 1.02 |
| Awat1 | 1.00 | 1.00 | 1.00 | 1.00 | 1.00 | 1.00 | 1.00 | 1.00 | 1.00 | 1.00 | 1.00 | 1.00 |
| B330016D10Rik | 1.10 | 1.46 | 1.11 | 0.87 | 0.79 | 0.91 | 0.64 | 0.52 | 0.77 | 1.08 | 1.29 | 1.36 |
| B3gat1 | 1.00 | 1.00 | 1.00 | 1.00 | 1.00 | 1.00 | 1.00 | 1.00 | 1.00 | 1.00 | 1.00 | 1.00 |
| B3gnt9 | 0.97 | 1.15 | 0.93 | 0.85 | 1.26 | 0.78 | 1.00 | 2.88 | 1.00 | 1.21 | 1.18 | 0.89 |
| B4galnt1 | 1.41 | 1.65 | 1.41 | 0.61 | 0.78 | 0.86 | 1.27 | 2.29 | 1.12 | 1.16 | 1.43 | 1.20 |
| B4galt4 | 2.11 | 1.35 | 1.19 | 1.50 | 1.00 | 1.30 | 1.00 | 1.00 | 1.00 | 1.06 | 1.08 | 1.17 |
| B9d2 | 1.15 | 1.66 | 0.90 | 0.98 | 0.84 | 0.95 | 0.62 | 1.28 | 0.91 | 0.61 | 1.45 | 1.19 |
| BC004004 | 1.33 | 1.35 | 1.01 | 0.93 | 0.50 | 1.04 | 1.05 | 2.80 | 1.18 | 1.22 | 1.49 | 1.02 |
| BC005537 | 0.67 | 0.52 | 0.96 | 1.16 | 1.15 | 1.04 | 0.92 | 1.80 | 1.09 | 1.07 | 0.52 | 1.01 |
| BC005561 | 0.68 | 0.81 | 0.99 | 1.39 | 0.57 | 0.67 | 1.00 | 2.54 | 1.00 | 1.28 | 1.00 | 0.69 |
| BC018473 | 0.70 | 0.95 | 0.74 | 1.10 | 0.78 | 0.91 | 1.55 | 1.79 | 1.48 | 1.28 | 1.44 | 1.15 |
| BC021614 | 1.71 | 2.31 | 1.97 | 1.00 | 2.56 | 0.74 | 0.47 | 0.82 | 0.54 | 1.34 | 2.20 | 0.98 |
| BC029214 | 0.90 | 1.29 | 0.87 | 0.79 | 0.43 | 0.89 | 1.60 | 4.89 | 1.35 | 0.80 | 1.34 | 0.96 |
| BC048679 | 1.00 | 1.00 | 1.00 | 1.00 | 1.00 | 1.00 | 1.00 | 1.00 | 1.00 | 1.00 | 1.00 | 1.00 |
| BC049730 | 1.00 | 1.00 | 1.00 | 1.00 | 1.00 | 1.00 | 1.00 | 1.00 | 1.00 | 1.00 | 1.00 | 1.00 |
| BC051142 | 1.88 | 2.71 | 1.65 | 1.00 | 1.00 | 1.00 | 1.00 | 1.00 | 1.00 | 1.70 | 1.15 | 0.98 |
| BC051226 | 1.97 | 2.29 | 1.36 | 1.53 | 0.77 | 0.94 | 0.60 | 0.32 | 0.80 | 1.48 | 2.27 | 1.92 |
| BC064078 | 2.88 | 2.59 | 2.74 | 1.03 | 2.96 | 0.84 | 1.00 | 1.00 | 1.00 | 10.44 | 15.00 | 10.80 |
| BC147527 | 1.19 | 1.35 | 1.11 | 1.00 | 1.00 | 1.00 | 1.00 | 1.00 | 1.00 | 1.00 | 1.00 | 1.00 |
| Baalc | 1.00 | 1.00 | 1.00 | 1.00 | 1.00 | 1.00 | 1.00 | 1.00 | 1.00 | 1.00 | 1.00 | 1.00 |
| Bag1 | 1.10 | 1.19 | 1.04 | 0.99 | 0.49 | 1.01 | 0.91 | 3.21 | 0.92 | 1.10 | 1.34 | 1.11 |
| Bai1 | 1.00 | 1.00 | 1.00 | 1.00 | 1.00 | 1.00 | 1.00 | 1.00 | 1.00 | 1.00 | 1.00 | 1.00 |
| Batf3 | 1.07 | 1.32 | 1.28 | 1.00 | 0.67 | 0.77 | 1.00 | 0.28 | 1.00 | 1.22 | 0.94 | 1.06 |
| Bcan | 1.00 | 1.00 | 1.00 | 1.00 | 1.00 | 1.00 | 1.00 | 1.00 | 1.00 | 1.00 | 1.00 | 1.00 |
| Bcas1 | 0.65 | 0.59 | 0.67 | 1.00 | 1.00 | 1.00 | 1.00 | 1.00 | 1.00 | 1.18 | 1.21 | 1.30 |
| Bcas2 | 1.28 | 1.42 | 1.02 | 1.02 | 0.95 | 1.02 | 1.07 | 1.52 | 0.97 | 1.11 | 1.74 | 1.19 |

Fig. 35- 131

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ascc2 | 1.00 | 0.95 | 0.84 | 1.24 | 1.77 | 0.96 | 1.04 | 4.37 | 1.04 | 0.97 | 0.90 | 1.07 |
| Ascl3 | 1.00 | 1.00 | 1.00 | 1.00 | 1.00 | 1.00 | 0.87 | 3.59 | 1.00 | 1.00 | 1.00 | 1.00 |
| Asgr1 | 1.00 | 1.00 | 1.00 | 1.00 | 1.00 | 1.00 | 1.00 | 0.87 | 1.00 | 1.00 | 1.00 | 1.00 |
| Asl | 1.20 | 1.90 | 1.05 | 3.64 | 22.72 | 1.38 | 0.92 | 2.40 | 0.77 | 0.85 | 1.33 | 1.27 |
| Aspg | 1.03 | 1.45 | 1.51 | 8.05 | 4.51 | 0.70 | 1.00 | 1.37 | 1.00 | 1.00 | 1.00 | 1.00 |
| Asph | 0.82 | 0.74 | 0.89 | 0.58 | 0.45 | 0.89 | 0.69 | 0.70 | 1.01 | 0.83 | 0.95 | 0.87 |
| Asphd1 | 1.00 | 1.00 | 1.00 | 4.82 | 46.04 | 3.73 | 1.00 | 3.81 | 1.00 | 1.00 | 1.00 | 1.00 |
| Asphd2 | 1.00 | 1.00 | 1.09 | 0.85 | 1.00 | 0.56 | 1.00 | 1.00 | 1.00 | 1.00 | 6.56 | 1.00 |
| Atf3 | 1.01 | 1.10 | 0.67 | 0.82 | 0.81 | 0.19 | 1.00 | 1.00 | 1.00 | 1.04 | 0.76 | 1.25 |
| Atg101 | 1.08 | 1.03 | 1.17 | 2.88 | 7.44 | 2.03 | 1.19 | 2.98 | 0.90 | 1.02 | 1.16 | 1.11 |
| Atox1 | 0.87 | 0.81 | 0.87 | 0.75 | 1.46 | 0.91 | 0.86 | 3.09 | 0.88 | 0.87 | 1.22 | 0.79 |
| Atp13a1 | 0.99 | 0.89 | 0.85 | 1.35 | 2.24 | 1.24 | 1.09 | 2.32 | 1.06 | 0.97 | 1.08 | 1.11 |
| Atp13a2 | 1.43 | 1.18 | 1.14 | 0.80 | 1.88 | 0.67 | 1.01 | 2.46 | 1.01 | 0.92 | 1.30 | 1.03 |
| Atp1a2 | 1.28 | 1.03 | 1.68 | 0.61 | 1.47 | 0.76 | 1.00 | 0.91 | 0.76 | 1.23 | 10.28 | 1.55 |
| Atp1a3 | 1.00 | 1.00 | 1.00 | 0.40 | 1.00 | 0.21 | 1.00 | 1.00 | 1.00 | 0.83 | 10.21 | 0.59 |
| Atp2a1 | 5.35 | 1.77 | 3.22 | 1.00 | 1.00 | 1.00 | 1.00 | 1.00 | 1.00 | 0.90 | 0.88 | 0.94 |
| Atp2a3 | 0.96 | 0.95 | 0.87 | 1.09 | 1.68 | 1.33 | 1.05 | 3.82 | 1.01 | 1.03 | 0.76 | 0.99 |
| Atp2b2 | 1.00 | 1.00 | 1.00 | 1.00 | 1.00 | 1.00 | 1.00 | 1.00 | 1.00 | 1.00 | 10.08 | 1.00 |
| Atp5d | 0.94 | 1.12 | 0.87 | 0.86 | 2.61 | 0.90 | 0.99 | 2.26 | 0.89 | 1.01 | 1.30 | 0.89 |
| Atp5e | 0.87 | 1.06 | 0.97 | 0.76 | 1.41 | 0.82 | 1.01 | 5.13 | 0.98 | 1.19 | 1.44 | 1.05 |
| Atp5g3 | 0.86 | 0.93 | 0.77 | 0.79 | 2.76 | 1.02 | 0.83 | 0.78 | 0.75 | 1.04 | 1.18 | 0.80 |
| Atp5h | 1.00 | 1.12 | 0.95 | 0.66 | 2.31 | 0.97 | 0.83 | 2.80 | 1.01 | 0.92 | 1.38 | 0.86 |
| Atp5j2 | 0.78 | 0.95 | 0.92 | 0.68 | 2.10 | 0.83 | 0.73 | 4.10 | 0.95 | 0.95 | 1.20 | 1.00 |
| Atp5k | 0.89 | 1.38 | 0.71 | 0.70 | 1.20 | 0.57 | 1.66 | 6.14 | 3.66 | 1.16 | 0.79 | 0.35 |
| Atp5l | 0.81 | 1.13 | 0.84 | 0.72 | 3.06 | 0.91 | 0.81 | 1.95 | 0.78 | 1.00 | 1.33 | 0.75 |
| Atp5o | 0.74 | 0.91 | 0.94 | 0.69 | 1.60 | 0.72 | 0.81 | 3.69 | 0.87 | 1.12 | 1.32 | 0.82 |
| Atp6v0b | 1.00 | 1.14 | 0.98 | 0.98 | 2.62 | 0.90 | 1.05 | 3.03 | 1.09 | 1.01 | 1.29 | 0.86 |
| Atp6v0c | 0.96 | 1.30 | 0.95 | 1.05 | 1.71 | 0.86 | 0.98 | 0.21 | 0.89 | 1.01 | 1.39 | 0.90 |
| Atp6v0c-ps2 | 1.00 | 0.62 | 0.96 | 1.00 | 1.59 | 5.34 | 1.00 | 1.24 | 1.00 | 1.00 | 1.67 | 0.20 |
| Atp6v1e1 | 1.26 | 1.35 | 1.29 | 3.04 | 5.82 | 1.65 | 0.77 | 0.56 | 1.09 | 1.34 | 1.63 | 1.04 |
| Atp6v1g2 | 0.89 | 1.00 | 1.29 | 1.23 | 1.00 | 1.43 | 1.11 | 0.41 | 0.75 | 1.13 | 5.79 | 1.48 |
| Atp8b3 | 1.00 | 1.00 | 1.00 | 3.49 | 1.00 | 1.00 | 1.04 | 0.64 | 1.09 | 1.00 | 1.00 | 1.00 |
| Atp9a | 0.88 | 0.90 | 0.77 | 0.80 | 1.26 | 0.79 | 1.05 | 3.77 | 1.14 | 0.77 | 1.65 | 1.05 |
| Atp9b | 1.47 | 1.51 | 1.34 | 1.52 | 2.42 | 1.44 | 1.03 | 3.53 | 0.93 | 1.45 | 1.49 | 1.37 |
| Atpif1 | 0.86 | 1.01 | 1.07 | 0.92 | 7.27 | 0.86 | 1.05 | 0.85 | 0.97 | 0.66 | 1.08 | 0.66 |
| Atraid | 1.04 | 1.29 | 1.27 | 0.73 | 5.37 | 0.86 | 0.86 | 0.87 | 1.00 | 1.15 | 1.66 | 1.01 |
| Aup1 | 1.06 | 1.23 | 1.11 | 1.31 | 3.75 | 1.19 | 0.95 | 2.03 | 1.12 | 1.05 | 1.14 | 0.94 |
| Aurkaip1 | 0.95 | 1.06 | 1.03 | 0.89 | 2.50 | 0.94 | 0.93 | 1.77 | 1.01 | 1.07 | 1.26 | 0.97 |
| Awat1 | 1.00 | 1.00 | 1.00 | 1.00 | 1.00 | 1.00 | 1.00 | 1.00 | 1.00 | 1.00 | 1.00 | 1.00 |
| B330016D10Rik | 1.11 | 1.08 | 1.26 | 0.87 | 3.01 | 1.07 | 1.04 | 2.62 | 1.07 | 1.34 | 1.02 | 0.93 |
| B3gat1 | 1.00 | 1.00 | 1.00 | 1.00 | 1.00 | 1.00 | 1.00 | 1.00 | 1.00 | 1.00 | 6.22 | 1.00 |
| B3gnt9 | 0.77 | 0.49 | 0.83 | 1.00 | 5.71 | 0.96 | 0.63 | 0.58 | 0.70 | 0.85 | 0.86 | 1.09 |
| B4galnt1 | 1.21 | 1.50 | 1.10 | 0.78 | 1.30 | 0.77 | 0.97 | 2.10 | 1.05 | 0.92 | 0.95 | 0.88 |
| B4galt4 | 1.52 | 1.28 | 1.72 | 1.16 | 0.56 | 1.40 | 0.94 | 1.00 | 0.97 | 1.08 | 0.88 | 1.02 |
| B9d2 | 1.03 | 2.03 | 1.38 | 0.88 | 1.95 | 0.99 | 1.00 | 1.83 | 1.13 | 0.83 | 1.15 | 0.78 |
| BC004004 | 1.08 | 1.03 | 0.99 | 0.94 | 2.58 | 1.00 | 1.10 | 4.24 | 1.02 | 1.19 | 1.18 | 1.01 |
| BC005537 | 1.07 | 1.02 | 0.88 | 1.15 | 0.09 | 0.82 | 1.12 | 1.68 | 1.09 | 0.98 | 0.62 | 1.06 |
| BC005561 | 1.00 | 0.87 | 0.89 | 1.00 | 1.17 | 1.00 | 1.24 | 1.61 | 1.20 | 1.00 | 1.00 | 1.44 |
| BC018473 | 2.45 | 1.76 | 2.94 | 1.89 | 1.07 | 1.06 | 1.00 | 1.00 | 1.00 | 1.69 | 1.59 | 2.15 |
| BC021614 | 0.78 | 0.71 | 1.34 | 1.00 | 5.79 | 1.81 | 1.00 | 1.00 | 1.00 | 1.19 | 0.85 | 0.87 |
| BC029214 | 1.05 | 1.48 | 1.04 | 0.50 | 1.15 | 0.75 | 0.23 | 1.28 | 0.34 | 1.17 | 1.16 | 0.94 |
| BC048679 | 1.00 | 1.00 | 1.00 | 1.00 | 5.36 | 0.03 | 1.00 | 1.08 | 0.96 | 1.00 | 1.00 | 1.00 |
| BC049730 | 1.00 | 1.00 | 1.00 | 1.00 | 1.00 | 1.00 | 1.05 | 1.56 | 1.13 | 1.00 | 1.00 | 1.00 |
| BC051142 | 1.00 | 1.00 | 1.00 | 2.47 | 1.00 | 2.93 | 1.00 | 0.36 | 0.95 | 2.06 | 1.81 | 1.86 |
| BC051226 | 1.72 | 2.47 | 1.86 | 1.64 | 2.02 | 1.41 | 1.33 | 0.93 | 0.97 | 1.72 | 1.99 | 1.73 |
| BC064078 | 3.21 | 2.44 | 4.46 | 0.76 | 1.00 | 1.56 | 1.00 | 1.00 | 1.00 | 1.45 | 1.68 | 1.49 |
| BC147527 | 1.00 | 1.00 | 1.00 | 1.00 | 1.98 | 1.00 | 1.00 | 1.00 | 1.00 | 1.81 | 1.75 | 1.68 |
| Baalc | 1.00 | 1.00 | 1.00 | 0.75 | 1.00 | 0.92 | 1.00 | 1.00 | 1.00 | 1.00 | 6.80 | 1.00 |
| Bag1 | 0.97 | 1.15 | 0.96 | 0.94 | 1.70 | 1.00 | 0.93 | 5.04 | 0.98 | 0.99 | 1.20 | 0.86 |
| Bai1 | 0.55 | 0.97 | 0.60 | 1.00 | 1.00 | 1.00 | 0.70 | 1.52 | 0.94 | 1.00 | 5.03 | 1.00 |
| Batf3 | 0.99 | 1.00 | 0.99 | 1.02 | 2.15 | 1.26 | 1.00 | 1.48 | 1.00 | 0.71 | 0.85 | 0.71 |
| Bcan | 1.00 | 1.00 | 1.00 | 1.00 | 1.00 | 1.00 | 1.00 | 1.00 | 1.00 | 1.00 | 7.16 | 1.00 |
| Bcas1 | 0.66 | 0.66 | 0.55 | 1.00 | 1.00 | 1.00 | 1.36 | 1.13 | 1.08 | 1.00 | 6.72 | 1.00 |
| Bcas2 | 1.04 | 1.01 | 1.19 | 0.97 | 5.18 | 1.37 | 1.35 | 1.99 | 1.26 | 1.21 | 1.26 | 0.91 |

Fig. 35- 132

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ascc2 | 0.73 | 1.15 | 1.12 | 0.60 | 1.10 | 1.00 | 0.97 | 13.77 | 0.83 | 3.63 | 0.79 | 0.89 |
| Ascl3 | 1.00 | 1.00 | 1.00 | 1.00 | 1.00 | 1.00 | 1.00 | 1.22 | 1.00 | 1.00 | 1.00 | 1.00 |
| Asgr1 | 1.00 | 1.00 | 1.00 | 0.98 | 6.00 | 0.97 | 1.00 | 1.00 | 1.00 | 1.00 | 1.00 | 1.00 |
| Asl | 1.57 | 1.09 | 1.17 | 1.08 | 1.13 | 1.48 | 1.36 | 14.11 | 0.74 | 4.48 | 1.20 | 1.73 |
| Aspg | 1.00 | 1.00 | 1.00 | 1.51 | 0.94 | 1.64 | 1.07 | 3.62 | 0.74 | 1.00 | 1.00 | 1.00 |
| Asph | 0.72 | 0.62 | 0.64 | 0.87 | 0.76 | 0.89 | 0.87 | 0.78 | 1.20 | 0.60 | 0.74 | 0.76 |
| Asphd1 | 1.00 | 1.00 | 1.00 | 1.34 | 0.85 | 1.18 | 1.00 | 1.00 | 1.00 | 1.00 | 1.00 | 1.00 |
| Asphd2 | 1.00 | 1.00 | 1.00 | 1.11 | 0.89 | 1.08 | 1.53 | 1.08 | 0.79 | 1.00 | 1.00 | 1.00 |
| Atf3 | 1.38 | 2.75 | 1.00 | 1.00 | 1.00 | 1.00 | 0.73 | 0.14 | 0.55 | 1.00 | 0.82 | 0.68 |
| Atg101 | 0.81 | 1.22 | 1.21 | 1.37 | 0.77 | 1.08 | 1.38 | 9.90 | 0.97 | 2.62 | 1.45 | 1.25 |
| Atox1 | 1.23 | 1.17 | 0.98 | 1.25 | 0.88 | 1.19 | 1.03 | 14.41 | 0.82 | 3.53 | 1.54 | 1.40 |
| Atp13a1 | 1.04 | 1.20 | 1.26 | 1.10 | 0.91 | 0.99 | 1.07 | 5.25 | 1.10 | 2.47 | 1.06 | 0.94 |
| Atp13a2 | 0.98 | 0.81 | 0.88 | 1.10 | 1.11 | 1.04 | 1.12 | 5.06 | 1.10 | 2.35 | 1.02 | 0.91 |
| Atp1a2 | 1.00 | 1.00 | 1.00 | 1.01 | 2.01 | 0.95 | 2.21 | 3.11 | 2.20 | 1.00 | 1.00 | 1.00 |
| Atp1a3 | 1.00 | 1.00 | 1.00 | 1.14 | 1.09 | 1.05 | 1.00 | 1.00 | 1.20 | 1.26 | 1.40 | 1.26 |
| Atp2a1 | 1.00 | 1.00 | 1.00 | 1.00 | 0.22 | 1.00 | 1.92 | 2.68 | 3.15 | 1.17 | 1.00 | 1.00 |
| Atp2a3 | 0.82 | 0.81 | 1.10 | 0.95 | 0.80 | 0.95 | 1.27 | 5.13 | 1.44 | 1.92 | 0.95 | 0.97 |
| Atp2b2 | 1.00 | 1.00 | 1.00 | 1.00 | 0.81 | 1.02 | 1.00 | 1.00 | 1.00 | 1.00 | 1.00 | 1.00 |
| Atp5d | 1.06 | 1.15 | 0.90 | 1.16 | 0.98 | 1.03 | 1.37 | 8.76 | 0.88 | 2.50 | 1.11 | 1.13 |
| Atp5e | 1.07 | 1.17 | 0.91 | 1.31 | 0.82 | 1.11 | 1.11 | 47.52 | 0.97 | 5.43 | 1.17 | 1.13 |
| Atp5g3 | 0.84 | 0.91 | 0.91 | 1.11 | 1.30 | 0.94 | 1.07 | 3.22 | 1.00 | 1.61 | 0.96 | 1.07 |
| Atp5h | 0.79 | 0.55 | 0.98 | 0.91 | 1.04 | 1.09 | 1.13 | 14.49 | 1.00 | 4.01 | 1.01 | 1.22 |
| Atp5j2 | 0.68 | 0.73 | 1.03 | 1.13 | 0.84 | 1.17 | 1.07 | 19.43 | 0.87 | 3.60 | 1.29 | 1.14 |
| Atp5k | 0.61 | 0.44 | 1.84 | 0.48 | 1.00 | 0.83 | 2.31 | 74.29 | 0.89 | 8.91 | 0.40 | 0.68 |
| Atp5l | 1.03 | 0.72 | 1.09 | 1.04 | 0.98 | 0.99 | 1.08 | 7.31 | 1.05 | 2.86 | 1.06 | 1.26 |
| Atp5o | 0.84 | 0.75 | 1.01 | 1.07 | 1.08 | 1.14 | 1.12 | 18.25 | 0.86 | 3.72 | 1.00 | 1.30 |
| Atp6v0b | 1.23 | 1.18 | 1.07 | 1.17 | 0.95 | 1.12 | 1.35 | 12.29 | 0.93 | 3.39 | 1.49 | 1.10 |
| Atp6v0c | 1.27 | 1.28 | 0.88 | 1.14 | 1.00 | 1.08 | 1.14 | 0.01 | 0.96 | 0.10 | 1.53 | 1.25 |
| Atp6v0c-ps2 | 1.00 | 1.00 | 1.00 | 1.00 | 0.91 | 1.39 | 2.00 | 33.79 | 0.26 | 2.70 | 0.92 | 4.87 |
| Atp6v1e1 | 0.93 | 1.34 | 1.00 | 1.07 | 1.15 | 0.98 | 1.24 | 1.85 | 1.08 | 1.85 | 1.68 | 1.55 |
| Atp6v1g2 | 1.07 | 1.00 | 0.84 | 0.87 | 0.85 | 0.79 | 1.98 | 1.59 | 1.79 | 0.97 | 1.14 | 1.33 |
| Atp8b3 | 1.00 | 1.00 | 1.00 | 1.00 | 1.00 | 1.00 | 5.14 | 1.00 | 1.00 | 1.00 | 1.00 | 1.00 |
| Atp9a | 0.80 | 0.68 | 0.86 | 1.08 | 0.88 | 1.06 | 1.21 | 12.47 | 0.93 | 1.18 | 1.00 | 1.00 |
| Atp9b | 1.36 | 1.18 | 1.22 | 1.34 | 1.03 | 1.24 | 1.39 | 8.98 | 1.30 | 3.57 | 1.93 | 1.62 |
| Atpif1 | 0.75 | 1.35 | 0.86 | 1.19 | 0.89 | 1.08 | 0.85 | 2.16 | 0.86 | 1.42 | 0.99 | 1.02 |
| Atraid | 0.79 | 0.87 | 0.86 | 1.10 | 1.21 | 0.96 | 1.28 | 3.33 | 1.08 | 2.39 | 1.46 | 1.30 |
| Aup1 | 1.18 | 1.11 | 0.99 | 1.18 | 0.68 | 1.10 | 1.11 | 6.24 | 1.08 | 2.15 | 0.99 | 1.09 |
| Aurkaip1 | 1.09 | 1.00 | 0.94 | 1.08 | 0.90 | 0.98 | 1.31 | 5.91 | 0.80 | 2.06 | 1.30 | 1.21 |
| Awat1 | 1.00 | 1.00 | 1.00 | 1.00 | 1.00 | 1.00 | 1.64 | 9.23 | 0.97 | 1.00 | 1.00 | 1.00 |
| B330016D10Rik | 1.00 | 1.00 | 1.00 | 1.04 | 2.95 | 0.93 | 1.58 | 5.30 | 1.35 | 1.17 | 1.04 | 0.88 |
| B3gat1 | 1.00 | 1.00 | 1.00 | 0.96 | 0.85 | 0.97 | 1.00 | 1.00 | 1.00 | 1.00 | 1.00 | 1.00 |
| B3gnt9 | 1.00 | 1.00 | 1.00 | 0.79 | 0.68 | 0.79 | 0.72 | 4.51 | 0.95 | 7.45 | 1.35 | 1.26 |
| B4galnt1 | 1.23 | 1.13 | 1.04 | 1.04 | 0.80 | 1.08 | 1.62 | 5.96 | 1.39 | 2.22 | 1.25 | 1.07 |
| B4galt4 | 3.14 | 5.33 | 1.69 | 0.89 | 1.00 | 0.98 | 1.17 | 0.71 | 1.02 | 1.01 | 0.86 | 1.10 |
| B9d2 | 1.00 | 1.00 | 1.00 | 1.41 | 1.06 | 1.12 | 1.21 | 5.91 | 1.07 | 2.01 | 1.24 | 1.03 |
| BC004004 | 0.84 | 1.06 | 0.83 | 1.18 | 0.77 | 0.93 | 1.09 | 10.44 | 1.02 | 2.59 | 1.01 | 1.11 |
| BC005537 | 1.09 | 1.40 | 1.14 | 0.95 | 0.24 | 0.94 | 0.98 | 0.08 | 1.14 | 0.39 | 0.85 | 0.84 |
| BC005561 | 1.00 | 1.00 | 1.00 | 0.69 | 0.64 | 0.67 | 1.36 | 5.85 | 0.84 | 1.00 | 1.00 | 1.00 |
| BC018473 | 1.00 | 1.00 | 1.05 | 1.00 | 1.00 | 1.00 | 3.44 | 7.57 | 3.01 | 1.52 | 1.92 | 1.40 |
| BC021614 | 1.00 | 1.00 | 1.00 | 1.00 | 1.00 | 1.00 | 2.49 | 20.96 | 1.25 | 2.89 | 0.88 | 1.40 |
| BC029214 | 0.87 | 0.67 | 0.56 | 0.95 | 0.66 | 1.27 | 0.89 | 15.76 | 0.76 | 3.53 | 1.35 | 1.02 |
| BC048679 | 1.00 | 1.00 | 1.00 | 1.00 | 1.00 | 1.00 | 1.00 | 1.00 | 1.00 | 1.00 | 1.00 | 1.00 |
| BC049730 | 1.00 | 1.00 | 1.00 | 1.00 | 1.00 | 1.00 | 1.00 | 1.00 | 1.00 | 6.15 | 1.28 | 2.07 |
| BC051142 | 1.00 | 1.00 | 1.00 | 1.39 | 1.00 | 1.39 | 7.26 | 1.00 | 3.84 | 1.00 | 1.00 | 1.00 |
| BC051226 | 1.31 | 0.45 | 0.63 | 1.88 | 4.77 | 1.55 | 1.51 | 4.06 | 0.92 | 2.10 | 2.31 | 1.75 |
| BC064078 | 1.06 | 1.00 | 1.88 | 0.27 | 1.00 | 0.46 | 0.95 | 0.33 | 0.97 | 0.78 | 1.57 | 1.38 |
| BC147527 | 1.00 | 1.00 | 1.00 | 1.00 | 1.00 | 1.00 | 1.00 | 1.00 | 1.00 | 5.95 | 2.65 | 3.18 |
| Baalc | 1.00 | 1.00 | 1.00 | 0.90 | 0.84 | 0.81 | 0.62 | 1.00 | 0.91 | 1.00 | 1.00 | 1.00 |
| Bag1 | 0.90 | 0.75 | 1.06 | 1.12 | 0.78 | 1.06 | 1.00 | 13.33 | 0.81 | 2.91 | 1.02 | 0.93 |
| Bai1 | 1.00 | 1.00 | 1.00 | 0.97 | 0.88 | 1.00 | 1.00 | 1.23 | 1.00 | 1.00 | 1.00 | 1.00 |
| Batf3 | 1.00 | 1.00 | 1.00 | 0.93 | 0.70 | 1.18 | 2.33 | 6.25 | 1.29 | 4.72 | 1.97 | 2.88 |
| Bcan | 1.00 | 1.00 | 1.00 | 0.90 | 1.24 | 0.98 | 1.00 | 1.00 | 1.00 | 1.00 | 1.00 | 1.00 |
| Bcas1 | 1.00 | 1.00 | 1.00 | 1.07 | 1.37 | 1.00 | 1.51 | 1.43 | 1.41 | 1.00 | 1.00 | 1.00 |
| Bcas2 | 1.05 | 0.94 | 0.95 | 1.05 | 0.88 | 1.04 | 1.00 | 2.56 | 1.08 | 1.40 | 1.36 | 1.31 |

Fig. 35- 133

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Bcat2 | 1.34 | 1.03 | 1.12 | 0.46 | 6.36 | 1.77 | 0.90 | 0.87 | 0.96 | 2.53 | 2.97 | 1.13 |
| Bckdhb | 0.91 | 1.08 | 0.78 | 0.70 | 2.11 | 0.76 | 0.93 | 0.88 | 0.69 | 1.67 | 1.72 | 0.92 |
| Bckdk | 0.84 | 0.52 | 0.79 | 0.42 | 3.62 | 0.88 | 0.94 | 0.91 | 0.92 | 2.13 | 2.64 | 0.93 |
| Bcl2a1b | 1.00 | 1.00 | 1.00 | 1.00 | 1.00 | 1.00 | 1.06 | 1.88 | 2.28 | 1.01 | 2.34 | 1.45 |
| Bcl2l15 | 1.00 | 1.00 | 1.00 | 1.09 | 5.63 | 1.00 | 1.00 | 1.00 | 1.00 | 3.26 | 3.06 | 1.00 |
| Bcl7c | 0.75 | 0.64 | 0.82 | 0.87 | 6.51 | 1.04 | 1.02 | 0.86 | 1.19 | 1.99 | 1.60 | 0.92 |
| Bdh2 | 1.00 | 1.00 | 1.00 | 1.00 | 1.00 | 1.00 | 1.00 | 1.00 | 1.00 | 1.00 | 1.29 | 1.00 |
| Best2 | 1.00 | 1.00 | 1.00 | 1.00 | 1.00 | 1.00 | 1.00 | 1.00 | 1.00 | 1.00 | 1.00 | 1.00 |
| Bex1 | 0.66 | 0.47 | 0.63 | 1.00 | 0.62 | 1.00 | 0.59 | 0.50 | 0.69 | 0.35 | 0.86 | 1.04 |
| Bex2 | 1.00 | 1.00 | 1.00 | 1.00 | 0.09 | 1.00 | 1.00 | 1.00 | 1.00 | 0.58 | 0.84 | 0.71 |
| Bglap3 | 1.00 | 1.00 | 1.00 | 1.00 | 1.00 | 1.00 | 1.00 | 1.00 | 1.00 | 4.99 | 1.16 | 1.00 |
| Bhlha9 | 1.00 | 1.00 | 1.00 | 1.00 | 1.00 | 1.00 | 1.00 | 1.00 | 1.00 | 1.00 | 1.00 | 1.00 |
| Bid | 1.27 | 2.04 | 1.89 | 5.22 | 2.59 | 1.86 | 1.59 | 4.23 | 2.31 | 0.61 | 1.06 | 1.44 |
| Bik | 1.00 | 0.39 | 0.92 | 1.74 | 7.57 | 1.30 | 1.36 | 0.77 | 0.77 | 2.61 | 3.88 | 1.19 |
| Bin1 | 1.27 | 0.60 | 0.92 | 1.08 | 5.57 | 1.11 | 0.60 | 0.63 | 1.32 | 2.68 | 3.62 | 1.00 |
| Bin3 | 1.01 | 0.67 | 1.05 | 1.53 | 5.61 | 1.72 | 0.95 | 0.69 | 0.74 | 1.34 | 1.83 | 0.93 |
| Blnk | 1.00 | 1.00 | 1.00 | 1.00 | 1.49 | 1.00 | 1.00 | 1.00 | 0.97 | 1.19 | 1.69 | 0.86 |
| Bloc1s1 | 1.30 | 0.44 | 0.92 | 0.17 | 7.22 | 1.02 | 1.05 | 0.86 | 0.83 | 1.89 | 3.03 | 0.83 |
| Bloc1s2 | 1.09 | 0.52 | 1.01 | 1.04 | 6.71 | 1.23 | 0.99 | 0.90 | 0.87 | 1.03 | 2.29 | 0.87 |
| Blvra | 0.86 | 0.58 | 0.75 | 0.69 | 6.94 | 1.17 | 0.95 | 1.07 | 0.90 | 1.78 | 2.61 | 0.77 |
| Blvrb | 1.30 | 0.42 | 0.84 | 0.21 | 4.39 | 0.73 | 0.79 | 0.65 | 0.86 | 1.48 | 2.57 | 1.15 |
| Bmyc | 1.06 | 1.17 | 0.90 | 1.24 | 2.21 | 2.87 | 2.24 | 1.23 | 1.54 | 0.26 | 0.47 | 0.83 |
| Bnip1 | 1.16 | 0.81 | 0.96 | 0.64 | 4.43 | 0.92 | 0.98 | 0.78 | 0.69 | 1.59 | 2.70 | 0.97 |
| Bola1 | 1.06 | 0.65 | 0.83 | 0.32 | 7.06 | 1.11 | 1.24 | 0.85 | 0.89 | 1.70 | 2.88 | 1.03 |
| Bola2 | 1.54 | 0.60 | 0.70 | 0.44 | 17.25 | 1.00 | 0.93 | 0.86 | 0.85 | 3.73 | 7.40 | 1.06 |
| Brinp1 | 1.00 | 1.00 | 1.00 | 1.00 | 0.29 | 1.00 | 1.00 | 1.00 | 1.00 | 1.00 | 1.00 | 1.00 |
| Brms1 | 1.45 | 0.63 | 1.14 | 0.58 | 12.64 | 1.06 | 1.45 | 1.05 | 0.91 | 3.27 | 4.48 | 1.07 |
| Brsk1 | 1.00 | 1.00 | 1.00 | 1.00 | 0.35 | 1.00 | 1.00 | 1.00 | 1.00 | 2.82 | 3.02 | 1.17 |
| Bscl2 | 1.26 | 0.39 | 1.60 | 0.33 | 4.26 | 1.15 | 1.00 | 1.07 | 1.18 | 3.04 | 3.34 | 0.87 |
| Bst2 | 2.02 | 1.15 | 1.62 | 0.44 | 3.34 | 2.38 | 2.01 | 1.11 | 2.53 | 0.70 | 1.13 | 1.66 |
| Btg1 | 2.93 | 6.18 | 3.17 | 2.85 | 1.06 | 1.50 | 1.05 | 1.20 | 0.96 | 0.36 | 0.47 | 0.97 |
| Btg2 | 4.63 | 10.39 | 4.13 | 4.30 | 2.07 | 2.07 | 2.74 | 2.72 | 1.94 | 0.85 | 0.82 | 1.28 |
| Bud31 | 1.20 | 0.76 | 1.10 | 0.53 | 5.47 | 0.98 | 1.18 | 0.85 | 0.83 | 1.37 | 2.62 | 1.14 |
| Bzw2 | 0.69 | 0.60 | 0.65 | 2.13 | 6.18 | 1.52 | 0.68 | 0.78 | 0.82 | 0.83 | 1.49 | 0.80 |
| C130036L24Rik | 1.23 | 0.41 | 1.41 | 1.00 | 7.15 | 1.00 | 0.85 | 0.71 | 0.95 | 2.34 | 5.59 | 1.00 |
| C1qa | 2.32 | 0.95 | 1.96 | 2.19 | 8.97 | 1.44 | 1.19 | 1.17 | 1.37 | 2.55 | 3.73 | 1.33 |
| C1qb | 3.50 | 1.45 | 2.56 | 1.20 | 5.86 | 1.64 | 1.57 | 1.12 | 1.53 | 1.10 | 2.29 | 1.47 |
| C1qc | 2.38 | 1.25 | 2.23 | 1.39 | 5.09 | 1.52 | 1.42 | 1.08 | 1.38 | 1.64 | 2.40 | 1.39 |
| C1qtnf2 | 0.79 | 0.61 | 0.36 | 0.80 | 1.23 | 0.84 | 0.67 | 0.60 | 0.57 | 0.64 | 0.65 | 0.62 |
| C1qtnf4 | 0.44 | 0.45 | 0.51 | 0.40 | 1.31 | 2.24 | 1.07 | 0.59 | 0.74 | 1.90 | 4.02 | 0.83 |
| C2cd4a | 1.00 | 1.00 | 1.00 | 1.00 | 1.00 | 1.00 | 1.00 | 1.00 | 1.00 | 1.00 | 1.00 | 1.00 |
| C2cd4b | 1.00 | 1.00 | 1.00 | 1.00 | 1.00 | 1.00 | 0.70 | 0.57 | 0.79 | 1.40 | 3.53 | 1.14 |
| C3 | 1.56 | 0.86 | 2.06 | 0.79 | 2.71 | 1.57 | 1.65 | 1.65 | 2.03 | 3.01 | 3.79 | 1.48 |
| C4b | 0.75 | 0.38 | 1.11 | 0.21 | 0.87 | 0.45 | 0.59 | 0.63 | 0.94 | 0.45 | 0.68 | 0.26 |
| C4bp-ps1 | 1.00 | 1.00 | 1.00 | 1.00 | 1.00 | 1.00 | 0.89 | 1.34 | 1.00 | 1.98 | 3.99 | 1.00 |
| C7 | 2.74 | 1.75 | 3.67 | 3.21 | 0.66 | 2.69 | 2.36 | 2.88 | 2.13 | 0.95 | 0.10 | 1.24 |
| Caap1 | 1.40 | 1.04 | 0.87 | 1.95 | 1.01 | 0.76 | 1.06 | 1.06 | 1.24 | 1.02 | 0.84 | 1.04 |
| Cab39l | 1.15 | 0.91 | 1.00 | 5.21 | 5.60 | 1.07 | 1.88 | 1.58 | 0.92 | 1.23 | 1.24 | 0.97 |
| Cables1 | 2.01 | 2.13 | 1.86 | 0.60 | 1.60 | 1.17 | 1.57 | 1.77 | 1.38 | 2.12 | 1.85 | 1.31 |
| Cacna1c | 1.00 | 1.00 | 1.00 | 1.00 | 0.95 | 1.00 | 1.00 | 1.18 | 1.00 | 0.69 | 0.41 | 0.97 |
| Cacnb4 | 1.00 | 1.00 | 1.00 | 1.00 | 0.33 | 1.04 | 1.00 | 1.00 | 1.00 | 1.00 | 1.00 | 1.00 |
| Cacng1 | 1.35 | 1.13 | 1.27 | 1.00 | 3.83 | 2.06 | 1.00 | 1.00 | 1.00 | 1.00 | 1.00 | 1.00 |
| Cacng3 | 1.00 | 1.00 | 1.00 | 1.00 | 0.43 | 1.00 | 1.00 | 1.00 | 1.00 | 1.00 | 1.00 | 1.00 |
| Cadm3 | 1.01 | 0.74 | 1.12 | 0.88 | 0.28 | 1.28 | 0.62 | 0.65 | 0.66 | 1.00 | 1.00 | 1.00 |
| Calb1 | 1.00 | 1.00 | 1.00 | 1.00 | 0.25 | 1.00 | 1.00 | 1.00 | 1.00 | 1.00 | 1.00 | 1.00 |
| Calb2 | 1.00 | 1.00 | 1.00 | 1.00 | 0.27 | 1.00 | 1.00 | 1.00 | 1.00 | 1.00 | 1.00 | 1.00 |
| Calca | 1.00 | 1.00 | 1.00 | 1.00 | 6.93 | 2.01 | 1.00 | 1.00 | 1.00 | 9.88 | 13.32 | 2.23 |
| Calml4 | 1.25 | 0.44 | 0.36 | 0.85 | 1.00 | 1.07 | 1.00 | 0.80 | 0.53 | 0.73 | 0.96 | 0.71 |
| Calr | 1.09 | 0.61 | 0.95 | 0.57 | 3.56 | 1.01 | 0.96 | 0.84 | 0.99 | 2.23 | 2.83 | 1.02 |
| Caly | 3.35 | 3.84 | 1.27 | 1.00 | 0.27 | 1.00 | 1.00 | 1.00 | 1.00 | 1.00 | 1.00 | 1.00 |
| Camk1 | 0.98 | 0.69 | 0.90 | 0.38 | 4.03 | 1.33 | 1.33 | 0.98 | 1.11 | 1.59 | 2.26 | 1.33 |
| Camk2a | 0.62 | 1.38 | 0.55 | 1.00 | 0.03 | 0.76 | 0.72 | 0.78 | 0.76 | 1.00 | 1.00 | 0.87 |
| Camk2b | 0.72 | 0.57 | 0.62 | 1.06 | 0.09 | 0.74 | 1.26 | 1.05 | 0.87 | 1.00 | 1.00 | 1.00 |
| Camk2n2 | 1.12 | 1.00 | 0.76 | 1.12 | 1.00 | 1.30 | 1.25 | 1.61 | 1.19 | 1.51 | 3.20 | 1.93 |

Fig. 35- 134

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Bcat2 | 0.91 | 1.25 | 0.87 | 1.00 | 1.26 | 1.12 | 0.73 | 1.82 | 0.97 | 0.97 | 1.66 | 1.24 |
| Bckdhb | 1.19 | 1.21 | 0.85 | 1.49 | 1.47 | 1.08 | 1.35 | 1.88 | 1.02 | 0.73 | 1.19 | 0.94 |
| Bckdk | 0.90 | 1.14 | 0.98 | 0.79 | 0.55 | 0.91 | 0.94 | 1.83 | 1.04 | 0.88 | 1.23 | 0.98 |
| Bcl2a1b | 2.22 | 2.50 | 2.21 | 1.00 | 1.97 | 1.00 | 1.26 | 2.16 | 1.41 | 1.00 | 2.09 | 1.01 |
| Bcl2l15 | 1.43 | 1.56 | 1.46 | 1.03 | 1.00 | 1.00 | 1.00 | 1.00 | 1.00 | 1.00 | 1.00 | 2.17 |
| Bcl7c | 0.68 | 1.11 | 0.86 | 1.18 | 0.84 | 1.42 | 1.49 | 1.73 | 1.07 | 1.06 | 1.25 | 0.56 |
| Bdh2 | 1.00 | 1.00 | 1.00 | 0.75 | 0.78 | 0.93 | 0.45 | 0.25 | 0.34 | 0.56 | 0.74 | 0.94 |
| Best2 | 1.00 | 1.00 | 1.00 | 1.00 | 1.00 | 1.00 | 1.00 | 1.00 | 1.00 | 1.51 | 2.13 | 1.63 |
| Bex1 | 0.91 | 0.99 | 1.05 | 0.85 | 1.21 | 0.94 | 1.00 | 1.00 | 1.00 | 1.23 | 2.23 | 1.39 |
| Bex2 | 0.89 | 1.10 | 0.62 | 1.00 | 0.47 | 0.90 | 1.00 | 1.36 | 1.00 | 1.44 | 1.41 | 1.02 |
| Bglap3 | 1.58 | 1.00 | 1.00 | 1.00 | 1.67 | 0.63 | 1.00 | 3.46 | 1.00 | 1.23 | 2.48 | 1.26 |
| Bhlha9 | 1.00 | 1.00 | 1.00 | 1.00 | 1.00 | 1.00 | 1.00 | 1.00 | 1.00 | 1.00 | 1.00 | 1.00 |
| Bid | 0.61 | 0.64 | 0.63 | 1.59 | 3.56 | 1.53 | 1.44 | 1.09 | 2.33 | 1.93 | 1.63 | 1.90 |
| Bik | 1.08 | 1.05 | 0.83 | 1.13 | 0.68 | 1.22 | 0.86 | 1.71 | 1.01 | 1.02 | 1.09 | 0.75 |
| Bin1 | 1.04 | 1.34 | 1.00 | 1.08 | 0.73 | 1.14 | 0.83 | 1.89 | 0.70 | 0.78 | 1.42 | 1.04 |
| Bin3 | 1.15 | 1.40 | 1.00 | 1.07 | 0.88 | 0.87 | 1.03 | 1.48 | 0.79 | 1.03 | 1.41 | 0.99 |
| Blnk | 1.54 | 1.69 | 1.66 | 0.75 | 0.59 | 0.80 | 1.00 | 1.00 | 1.00 | 0.98 | 1.47 | 0.95 |
| Bloc1s1 | 1.54 | 1.69 | 1.07 | 0.83 | 0.63 | 0.87 | 0.82 | 1.17 | 0.74 | 1.14 | 1.48 | 0.99 |
| Bloc1s2 | 0.76 | 1.05 | 0.74 | 1.21 | 0.87 | 1.18 | 0.93 | 1.21 | 0.93 | 0.94 | 1.58 | 0.89 |
| Blvra | 1.09 | 1.26 | 1.14 | 0.86 | 0.72 | 1.01 | 0.83 | 0.74 | 0.87 | 0.91 | 1.82 | 1.10 |
| Blvrb | 1.35 | 1.71 | 1.33 | 0.95 | 0.86 | 1.07 | 0.77 | 0.69 | 0.68 | 1.09 | 1.55 | 1.15 |
| Bmyc | 1.43 | 2.26 | 1.25 | 1.49 | 5.65 | 0.98 | 2.61 | 0.37 | 1.49 | 1.05 | 1.25 | 1.06 |
| Bnip1 | 1.14 | 1.39 | 0.80 | 1.04 | 0.73 | 0.99 | 1.29 | 1.28 | 0.99 | 1.08 | 1.66 | 1.06 |
| Bola1 | 1.19 | 1.82 | 1.20 | 0.85 | 0.73 | 0.90 | 1.06 | 0.79 | 0.89 | 0.95 | 1.67 | 1.06 |
| Bola2 | 0.90 | 1.28 | 1.28 | 1.06 | 0.42 | 0.98 | 1.47 | 2.78 | 1.25 | 0.77 | 2.03 | 1.38 |
| Brinp1 | 1.00 | 1.00 | 1.00 | 1.00 | 1.00 | 1.00 | 1.00 | 1.00 | 1.00 | 1.00 | 1.00 | 1.00 |
| Brms1 | 1.33 | 1.73 | 1.09 | 1.00 | 0.77 | 0.85 | 1.47 | 2.38 | 0.99 | 1.13 | 1.83 | 1.07 |
| Brsk1 | 1.00 | 1.00 | 1.00 | 1.00 | 1.00 | 1.00 | 1.00 | 1.00 | 1.00 | 0.76 | 0.64 | 1.14 |
| Bscl2 | 1.19 | 1.36 | 1.04 | 0.99 | 0.54 | 1.07 | 1.03 | 2.68 | 0.83 | 1.05 | 1.24 | 0.99 |
| Bst2 | 1.38 | 1.63 | 1.24 | 1.61 | 2.62 | 2.97 | 0.96 | 0.38 | 0.86 | 1.94 | 3.40 | 1.76 |
| Btg1 | 0.96 | 1.05 | 1.02 | 1.21 | 2.14 | 1.02 | 1.55 | 0.75 | 1.26 | 0.96 | 0.91 | 0.98 |
| Btg2 | 0.76 | 0.74 | 0.95 | 1.60 | 3.83 | 1.14 | 7.02 | 14.54 | 3.63 | 0.92 | 1.08 | 1.02 |
| Bud31 | 0.97 | 1.25 | 0.98 | 1.00 | 0.96 | 0.98 | 1.20 | 1.06 | 1.07 | 0.82 | 1.64 | 1.08 |
| Bzw2 | 0.78 | 0.89 | 0.82 | 0.94 | 0.90 | 0.87 | 1.30 | 0.61 | 0.91 | 0.90 | 1.17 | 1.03 |
| C130036L24Rik | 0.95 | 1.09 | 0.81 | 1.00 | 0.44 | 1.00 | 1.00 | 4.28 | 1.00 | 1.00 | 1.00 | 1.00 |
| C1qa | 2.55 | 2.80 | 2.08 | 1.14 | 1.02 | 0.88 | 1.34 | 2.26 | 1.05 | 1.28 | 1.68 | 1.03 |
| C1qb | 3.03 | 3.27 | 2.44 | 1.41 | 1.66 | 1.11 | 1.43 | 0.97 | 1.10 | 1.37 | 1.79 | 1.07 |
| C1qc | 2.79 | 3.09 | 2.36 | 1.20 | 0.95 | 1.18 | 1.33 | 1.48 | 1.10 | 1.35 | 1.53 | 1.25 |
| C1qtnf2 | 1.53 | 1.13 | 1.01 | 0.56 | 0.69 | 1.33 | 1.00 | 1.94 | 1.00 | 0.65 | 1.12 | 0.72 |
| C1qtnf4 | 2.16 | 2.26 | 1.51 | 0.74 | 0.46 | 1.04 | 1.00 | 2.91 | 1.00 | 1.06 | 1.52 | 0.91 |
| C2cd4a | 1.00 | 1.00 | 1.00 | 1.00 | 1.00 | 1.00 | 1.00 | 1.00 | 1.00 | 1.00 | 1.63 | 0.75 |
| C2cd4b | 1.00 | 1.00 | 1.00 | 1.00 | 1.00 | 1.00 | 1.00 | 1.00 | 1.00 | 1.47 | 3.49 | 1.93 |
| C3 | 1.28 | 0.88 | 1.35 | 1.03 | 0.66 | 0.89 | 1.07 | 1.91 | 1.24 | 1.13 | 0.93 | 0.87 |
| C4b | 0.88 | 0.59 | 0.67 | 0.64 | 0.56 | 0.60 | 0.25 | 0.37 | 0.50 | 0.42 | 0.31 | 0.38 |
| C4bp-ps1 | 1.00 | 1.00 | 1.00 | 1.00 | 0.34 | 1.00 | 2.56 | 4.85 | 1.00 | 1.00 | 1.00 | 1.00 |
| C7 | 5.86 | 1.94 | 1.96 | 4.09 | 1.00 | 4.15 | 1.00 | 1.00 | 1.00 | 1.28 | 1.00 | 1.30 |
| Caap1 | 0.92 | 1.05 | 0.89 | 0.81 | 1.19 | 0.81 | 1.36 | 0.92 | 0.90 | 1.05 | 1.04 | 0.98 |
| Cab39l | 4.04 | 3.89 | 2.31 | 0.90 | 0.86 | 0.88 | 2.44 | 2.94 | 1.12 | 1.01 | 1.10 | 1.02 |
| Cables1 | 3.06 | 2.74 | 1.62 | 1.49 | 1.52 | 1.33 | 3.60 | 11.79 | 3.03 | 1.39 | 1.43 | 1.33 |
| Cacna1c | 1.31 | 2.80 | 5.50 | 1.00 | 1.00 | 1.00 | 1.00 | 1.00 | 1.00 | 0.99 | 0.65 | 1.04 |
| Cacnb4 | 1.02 | 1.25 | 1.48 | 1.06 | 1.00 | 0.82 | 1.00 | 1.00 | 1.00 | 1.00 | 1.00 | 1.00 |
| Cacng1 | 1.00 | 1.00 | 1.00 | 1.00 | 1.00 | 1.00 | 1.00 | 1.00 | 1.00 | 1.00 | 1.00 | 1.00 |
| Cacng3 | 1.00 | 1.00 | 1.00 | 1.00 | 1.00 | 1.00 | 1.00 | 1.00 | 1.00 | 1.00 | 1.00 | 1.00 |
| Cadm3 | 1.00 | 1.00 | 0.79 | 1.00 | 1.00 | 1.00 | 1.00 | 1.15 | 1.33 | 1.01 | 1.08 | 0.99 |
| Calb1 | 1.00 | 1.00 | 1.00 | 1.16 | 1.97 | 1.31 | 1.00 | 1.00 | 1.00 | 1.00 | 1.00 | 1.00 |
| Calb2 | 0.96 | 1.00 | 1.00 | 1.00 | 1.00 | 1.00 | 1.00 | 1.00 | 1.00 | 1.03 | 1.92 | 1.15 |
| Calca | 1.16 | 1.19 | 0.45 | 1.00 | 1.00 | 1.00 | 1.00 | 1.00 | 1.00 | 1.00 | 1.00 | 1.00 |
| Calml4 | 1.12 | 1.02 | 1.28 | 0.44 | 0.53 | 0.52 | 0.53 | 0.72 | 0.64 | 0.63 | 0.95 | 0.75 |
| Calr | 1.05 | 1.05 | 1.10 | 0.88 | 0.59 | 0.93 | 0.84 | 1.20 | 0.81 | 1.04 | 1.31 | 1.04 |
| Caly | 1.00 | 1.00 | 1.00 | 1.00 | 1.00 | 1.00 | 1.00 | 1.41 | 1.00 | 1.00 | 1.41 | 1.54 |
| Camk1 | 3.24 | 3.19 | 1.78 | 0.92 | 0.82 | 1.16 | 1.23 | 1.00 | 0.92 | 0.99 | 1.62 | 1.17 |
| Camk2a | 1.44 | 1.78 | 1.85 | 1.00 | 1.00 | 1.00 | 1.00 | 1.00 | 1.00 | 0.93 | 0.59 | 0.74 |
| Camk2b | 1.03 | 1.00 | 1.00 | 1.00 | 1.00 | 1.00 | 1.00 | 1.00 | 1.19 | 1.03 | 1.23 | 1.18 |
| Camk2n2 | 1.23 | 1.17 | 0.83 | 1.48 | 1.15 | 1.35 | 3.27 | 2.73 | 1.44 | 1.21 | 1.38 | 1.02 |

Fig. 35- 135

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Bcat2 | 1.24 | 1.40 | 1.21 | 0.80 | 4.84 | 1.97 | 1.00 | 2.14 | 0.97 | 0.89 | 0.92 | 0.94 |
| Bckdhb | 1.26 | 1.22 | 1.12 | 1.21 | 6.45 | 1.31 | 0.59 | 1.03 | 1.46 | 0.73 | 1.25 | 0.64 |
| Bckdk | 0.97 | 1.05 | 1.04 | 0.66 | 1.91 | 0.99 | 0.63 | 2.19 | 0.85 | 0.85 | 1.06 | 0.93 |
| Bcl2a1b | 1.47 | 1.26 | 2.20 | 0.83 | 1.00 | 0.74 | 1.00 | 1.00 | 1.00 | 0.90 | 1.14 | 0.84 |
| Bcl2l15 | 1.00 | 1.00 | 1.00 | 1.00 | 1.00 | 1.00 | 1.24 | 1.23 | 0.87 | 1.42 | 1.16 | 0.67 |
| Bcl7c | 1.12 | 1.10 | 0.96 | 0.87 | 1.86 | 0.86 | 0.99 | 1.93 | 1.04 | 1.12 | 1.58 | 1.09 |
| Bdh2 | 1.00 | 1.00 | 1.00 | 1.21 | 1.97 | 1.57 | 1.00 | 1.67 | 1.00 | 1.00 | 1.00 | 1.00 |
| Best2 | 1.00 | 1.00 | 1.00 | 1.00 | 1.00 | 1.00 | 1.00 | 1.00 | 1.00 | 1.00 | 1.00 | 1.00 |
| Bex1 | 1.07 | 0.97 | 1.91 | 1.87 | 2.52 | 4.03 | 0.74 | 0.73 | 0.97 | 1.00 | 8.41 | 1.00 |
| Bex2 | 1.24 | 1.52 | 1.25 | 1.14 | 1.41 | 2.49 | 0.97 | 0.71 | 0.83 | 1.00 | 20.70 | 0.77 |
| Bglap3 | 0.91 | 0.98 | 0.59 | 1.00 | 1.00 | 1.00 | 1.00 | 1.00 | 1.00 | 1.00 | 1.00 | 1.00 |
| Bhlha9 | 1.00 | 1.00 | 1.00 | 1.00 | 1.00 | 1.00 | 0.79 | 2.50 | 1.00 | 1.00 | 1.00 | 1.00 |
| Bid | 1.45 | 1.14 | 1.39 | 1.53 | 1.31 | 1.51 | 1.14 | 0.87 | 1.32 | 1.19 | 1.14 | 1.12 |
| Bik | 1.49 | 1.47 | 1.04 | 0.95 | 2.90 | 2.99 | 0.69 | 1.41 | 0.56 | 1.22 | 1.18 | 0.92 |
| Bin1 | 0.98 | 1.02 | 1.18 | 0.82 | 1.35 | 0.91 | 1.00 | 1.93 | 0.92 | 0.89 | 1.03 | 0.79 |
| Bin3 | 1.00 | 0.85 | 0.90 | 1.19 | 2.60 | 1.21 | 0.87 | 1.25 | 1.09 | 1.12 | 1.05 | 0.97 |
| Blnk | 1.17 | 1.19 | 1.00 | 0.56 | 1.80 | 0.47 | 1.00 | 1.09 | 1.00 | 1.51 | 1.42 | 1.13 |
| Bloc1s1 | 1.20 | 1.32 | 1.29 | 0.63 | 1.37 | 0.73 | 0.67 | 2.41 | 1.09 | 1.13 | 1.43 | 0.93 |
| Bloc1s2 | 1.04 | 0.83 | 0.90 | 1.01 | 5.41 | 1.16 | 0.88 | 1.14 | 0.69 | 0.79 | 0.97 | 0.84 |
| Blvra | 0.82 | 0.81 | 0.98 | 0.91 | 6.67 | 0.64 | 0.83 | 1.85 | 1.12 | 0.89 | 1.21 | 0.91 |
| Blvrb | 0.76 | 0.99 | 0.81 | 0.68 | 4.43 | 0.83 | 0.62 | 1.33 | 0.60 | 0.58 | 0.84 | 0.47 |
| Bmyc | 2.04 | 3.26 | 1.89 | 1.08 | 0.30 | 1.03 | 0.84 | 0.27 | 0.66 | 1.20 | 1.30 | 0.92 |
| Bnip1 | 0.97 | 0.93 | 0.94 | 0.91 | 0.85 | 0.91 | 0.89 | 1.58 | 0.99 | 1.20 | 1.37 | 1.06 |
| Bola1 | 0.85 | 1.28 | 1.01 | 1.14 | 3.08 | 1.01 | 1.15 | 1.43 | 1.12 | 1.20 | 1.56 | 1.05 |
| Bola2 | 1.21 | 0.95 | 1.14 | 1.13 | 2.48 | 1.06 | 0.95 | 4.20 | 0.79 | 0.81 | 1.40 | 0.78 |
| Brinp1 | 1.00 | 1.00 | 1.00 | 1.00 | 1.00 | 1.00 | 1.00 | 1.00 | 1.00 | 1.00 | 7.16 | 1.00 |
| Brms1 | 0.91 | 1.11 | 0.83 | 1.16 | 3.94 | 1.21 | 1.04 | 2.90 | 0.95 | 1.13 | 1.50 | 0.93 |
| Brsk1 | 1.44 | 1.19 | 1.06 | 1.00 | 1.00 | 0.88 | 0.86 | 2.64 | 0.98 | 0.75 | 5.53 | 1.00 |
| Bscl2 | 1.00 | 0.96 | 1.13 | 0.87 | 2.22 | 1.39 | 1.03 | 3.68 | 1.07 | 0.99 | 1.09 | 1.01 |
| Bst2 | 5.10 | 7.29 | 4.35 | 1.44 | 5.06 | 1.60 | 0.80 | 0.94 | 1.10 | 1.07 | 1.19 | 0.99 |
| Btg1 | 1.11 | 1.20 | 1.18 | 1.52 | 0.34 | 1.42 | 0.90 | 1.07 | 1.03 | 1.33 | 1.15 | 1.08 |
| Btg2 | 1.33 | 1.67 | 1.15 | 1.90 | 1.66 | 1.06 | 0.84 | 0.87 | 1.43 | 1.11 | 0.95 | 1.30 |
| Bud31 | 0.78 | 0.94 | 0.75 | 1.45 | 7.79 | 1.02 | 0.84 | 1.16 | 1.08 | 0.94 | 1.28 | 0.87 |
| Bzw2 | 0.92 | 0.95 | 0.95 | 1.63 | 3.72 | 1.47 | 0.91 | 1.42 | 1.00 | 1.15 | 1.20 | 0.90 |
| C130036L24Rik | 1.00 | 1.00 | 1.00 | 1.00 | 5.91 | 1.00 | 1.00 | 3.64 | 1.00 | 1.09 | 0.73 | 0.89 |
| C1qa | 1.41 | 1.30 | 1.36 | 1.13 | 2.24 | 1.01 | 0.94 | 2.04 | 0.77 | 1.20 | 1.88 | 1.07 |
| C1qb | 1.31 | 1.43 | 1.56 | 1.33 | 3.06 | 1.20 | 0.93 | 0.83 | 0.78 | 1.32 | 2.21 | 1.25 |
| C1qc | 1.26 | 1.23 | 1.65 | 1.31 | 2.24 | 1.16 | 0.82 | 1.20 | 0.89 | 1.23 | 1.78 | 1.13 |
| C1qtnf2 | 0.82 | 1.00 | 1.12 | 0.89 | 5.17 | 0.92 | 0.96 | 0.96 | 0.83 | 0.48 | 0.82 | 0.74 |
| C1qtnf4 | 0.74 | 1.02 | 0.81 | 1.33 | 4.50 | 1.79 | 0.79 | 2.59 | 0.92 | 0.76 | 6.25 | 0.80 |
| C2cd4a | 0.40 | 0.35 | 0.55 | 1.00 | 1.00 | 1.00 | 1.00 | 1.00 | 1.00 | 1.00 | 1.00 | 1.00 |
| C2cd4b | 3.01 | 2.07 | 1.58 | 1.00 | 1.00 | 1.00 | 0.72 | 0.71 | 1.11 | 1.00 | 1.00 | 1.00 |
| C3 | 1.57 | 1.35 | 1.71 | 0.90 | 1.98 | 1.00 | 0.90 | 2.03 | 1.05 | 0.95 | 0.79 | 1.18 |
| C4b | 0.53 | 0.46 | 0.51 | 0.22 | 0.39 | 0.28 | 3.66 | 7.21 | 3.74 | 0.40 | 0.31 | 0.46 |
| C4bp-ps1 | 1.00 | 1.00 | 1.00 | 1.00 | 1.00 | 1.00 | 0.83 | 1.65 | 0.74 | 1.00 | 1.00 | 1.00 |
| C7 | 1.97 | 2.30 | 2.40 | 1.86 | 0.30 | 1.50 | 1.07 | 1.00 | 1.29 | 6.12 | 2.47 | 3.82 |
| Caap1 | 0.73 | 1.01 | 0.96 | 1.07 | 1.00 | 1.10 | 1.24 | 0.76 | 0.96 | 0.91 | 0.84 | 0.93 |
| Cab39l | 0.99 | 0.93 | 1.04 | 2.86 | 5.31 | 1.35 | 1.07 | 1.51 | 0.97 | 1.51 | 1.12 | 1.33 |
| Cables1 | 1.35 | 1.56 | 1.58 | 1.30 | 1.41 | 1.07 | 0.96 | 1.00 | 1.39 | 2.72 | 3.15 | 1.72 |
| Cacna1c | 1.04 | 1.04 | 1.19 | 1.87 | 1.00 | 1.58 | 1.00 | 1.00 | 1.00 | 1.00 | 1.18 | 1.00 |
| Cacnb4 | 1.00 | 1.00 | 1.00 | 0.98 | 1.00 | 0.97 | 1.00 | 1.00 | 1.00 | 1.01 | 5.44 | 1.11 |
| Cacng1 | 1.93 | 1.61 | 3.04 | 1.00 | 1.00 | 1.00 | 1.00 | 1.00 | 1.00 | 1.00 | 1.00 | 1.00 |
| Cacng3 | 1.00 | 1.00 | 1.00 | 1.00 | 1.00 | 1.00 | 1.00 | 1.00 | 1.00 | 1.00 | 6.81 | 1.00 |
| Cadm3 | 1.38 | 1.57 | 1.25 | 0.76 | 1.12 | 0.88 | 1.00 | 1.00 | 1.00 | 0.41 | 5.83 | 0.57 |
| Calb1 | 1.00 | 1.00 | 1.00 | 1.00 | 1.00 | 1.00 | 1.00 | 1.00 | 1.00 | 1.00 | 5.48 | 1.00 |
| Calb2 | 1.00 | 1.00 | 1.00 | 1.00 | 1.00 | 1.00 | 1.00 | 1.31 | 1.00 | 1.00 | 5.55 | 1.00 |
| Calca | 2.63 | 3.36 | 1.00 | 3.84 | 15.14 | 4.75 | 0.70 | 0.49 | 0.70 | 1.00 | 1.00 | 1.00 |
| Calml4 | 0.47 | 0.55 | 0.71 | 0.75 | 4.77 | 1.34 | 0.32 | 0.15 | 0.19 | 1.02 | 1.02 | 0.78 |
| Calr | 0.85 | 0.72 | 0.82 | 1.32 | 2.65 | 1.18 | 0.97 | 2.00 | 0.89 | 1.03 | 1.01 | 0.89 |
| Caly | 1.00 | 1.00 | 1.00 | 1.62 | 1.00 | 3.18 | 0.81 | 0.69 | 0.92 | 1.00 | 6.58 | 1.00 |
| Camk1 | 1.17 | 0.95 | 1.36 | 0.71 | 5.81 | 0.95 | 1.00 | 1.00 | 1.00 | 1.01 | 1.36 | 1.29 |
| Camk2a | 1.00 | 1.00 | 1.00 | 1.00 | 1.00 | 0.46 | 1.00 | 1.00 | 1.00 | 0.56 | 12.75 | 0.62 |
| Camk2b | 1.09 | 1.19 | 1.35 | 1.00 | 0.85 | 1.05 | 1.00 | 1.00 | 1.00 | 1.00 | 22.93 | 1.00 |
| Camk2n2 | 1.20 | 1.62 | 0.94 | 1.13 | 0.55 | 0.72 | 1.08 | 1.08 | 1.16 | 1.00 | 8.77 | 0.76 |

Fig. 35- 136

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Bcat2 | 0.81 | 0.69 | 0.76 | 0.97 | 1.20 | 1.11 | 1.81 | 5.55 | 1.20 | 2.61 | 1.18 | 1.21 |
| Bckdhb | 0.72 | 0.63 | 0.76 | 0.83 | 2.05 | 0.76 | 0.62 | 1.40 | 0.62 | 1.16 | 0.59 | 0.76 |
| Bckdk | 0.83 | 0.81 | 0.86 | 1.06 | 0.91 | 1.07 | 1.05 | 7.44 | 0.77 | 2.31 | 0.91 | 1.09 |
| Bcl2a1b | 1.00 | 1.00 | 1.00 | 1.00 | 1.00 | 1.15 | 0.81 | 5.36 | 1.71 | 1.22 | 2.13 | 1.14 |
| Bcl2l15 | 1.00 | 1.00 | 1.00 | 0.87 | 1.00 | 1.00 | 1.54 | 3.10 | 2.36 | 13.13 | 6.63 | 4.32 |
| Bcl7c | 0.67 | 1.10 | 1.12 | 0.74 | 0.63 | 1.04 | 0.97 | 3.61 | 0.81 | 1.74 | 1.37 | 1.15 |
| Bdh2 | 0.18 | 0.18 | 0.12 | 1.00 | 1.23 | 1.00 | 1.30 | 17.01 | 1.09 | 1.00 | 1.00 | 1.00 |
| Best2 | 1.00 | 1.00 | 1.00 | 1.00 | 1.00 | 1.00 | 2.19 | 8.08 | 3.53 | 1.00 | 1.00 | 1.00 |
| Bex1 | 0.68 | 1.00 | 1.00 | 1.26 | 2.09 | 0.97 | 1.99 | 1.81 | 2.69 | 0.73 | 0.70 | 1.10 |
| Bex2 | 0.75 | 0.42 | 0.56 | 1.16 | 1.38 | 1.06 | 0.61 | 1.00 | 0.54 | 1.00 | 1.00 | 1.00 |
| Bglap3 | 0.87 | 0.35 | 0.18 | 1.00 | 1.96 | 1.00 | 0.88 | 5.74 | 0.65 | 2.17 | 1.00 | 1.00 |
| Bhlha9 | 1.00 | 1.00 | 1.00 | 1.11 | 0.84 | 1.02 | 1.92 | 8.23 | 1.09 | 1.00 | 1.00 | 1.00 |
| Bid | 1.00 | 1.00 | 1.00 | 1.21 | 2.14 | 1.33 | 0.98 | 0.36 | 0.98 | 0.58 | 1.16 | 1.08 |
| Bik | 1.00 | 1.00 | 0.99 | 1.00 | 1.00 | 1.00 | 0.88 | 2.81 | 0.92 | 1.16 | 1.00 | 1.00 |
| Bin1 | 0.86 | 0.93 | 0.91 | 1.04 | 0.79 | 0.94 | 1.21 | 13.60 | 1.38 | 2.39 | 0.80 | 0.97 |
| Bin3 | 0.62 | 0.67 | 0.57 | 0.93 | 1.07 | 0.90 | 0.97 | 2.59 | 0.78 | 1.75 | 1.33 | 1.25 |
| Blnk | 1.00 | 1.00 | 1.00 | 0.90 | 2.29 | 1.27 | 1.33 | 8.99 | 0.65 | 1.82 | 0.99 | 1.17 |
| Bloc1s1 | 0.95 | 1.44 | 1.06 | 0.78 | 0.62 | 0.91 | 1.36 | 9.99 | 0.92 | 3.64 | 1.37 | 1.23 |
| Bloc1s2 | 0.81 | 0.87 | 0.95 | 0.92 | 0.85 | 1.02 | 0.84 | 3.18 | 0.66 | 1.29 | 0.66 | 0.68 |
| Blvra | 1.22 | 1.03 | 1.65 | 1.25 | 1.36 | 1.09 | 1.00 | 6.17 | 0.86 | 1.95 | 0.79 | 1.05 |
| Blvrb | 0.64 | 0.55 | 0.83 | 1.08 | 1.23 | 0.78 | 1.26 | 7.16 | 1.04 | 1.54 | 0.90 | 0.89 |
| Bmyc | 0.44 | 0.76 | 0.39 | 1.26 | 1.31 | 1.04 | 1.43 | 0.16 | 0.83 | 0.85 | 1.17 | 1.14 |
| Bnip1 | 0.72 | 0.78 | 0.86 | 1.03 | 1.09 | 1.17 | 1.32 | 5.60 | 1.07 | 1.89 | 1.17 | 0.98 |
| Bola1 | 1.19 | 0.83 | 0.82 | 1.08 | 1.02 | 1.19 | 1.05 | 3.31 | 0.80 | 1.83 | 0.92 | 0.85 |
| Bola2 | 0.74 | 1.27 | 1.22 | 0.81 | 0.98 | 1.06 | 1.24 | 33.19 | 1.06 | 4.03 | 1.24 | 1.04 |
| Brinp1 | 1.00 | 1.00 | 1.00 | 1.10 | 0.81 | 1.01 | 1.00 | 1.00 | 1.00 | 1.00 | 1.00 | 1.00 |
| Brms1 | 1.06 | 2.13 | 0.80 | 1.06 | 0.71 | 1.25 | 1.22 | 11.72 | 1.05 | 3.67 | 1.33 | 1.13 |
| Brsk1 | 1.00 | 1.00 | 1.00 | 1.03 | 0.73 | 1.09 | 1.00 | 1.90 | 1.00 | 1.00 | 1.00 | 1.00 |
| Bscl2 | 0.73 | 0.63 | 0.82 | 1.13 | 0.85 | 1.18 | 1.65 | 9.61 | 1.04 | 3.13 | 1.30 | 1.13 |
| Bst2 | 0.81 | 2.31 | 1.05 | 1.06 | 1.00 | 3.61 | 2.78 | 1.70 | 2.85 | 1.83 | 1.95 | 1.55 |
| Btg1 | 1.38 | 1.64 | 1.41 | 0.93 | 0.59 | 0.96 | 1.23 | 0.21 | 1.36 | 0.58 | 1.62 | 1.16 |
| Btg2 | 2.55 | 3.88 | 1.55 | 1.13 | 1.88 | 1.14 | 1.17 | 0.63 | 1.03 | 0.42 | 0.83 | 0.97 |
| Bud31 | 0.91 | 1.65 | 0.82 | 1.12 | 1.76 | 1.15 | 1.17 | 5.88 | 0.98 | 2.12 | 1.03 | 1.19 |
| Bzw2 | 1.29 | 1.52 | 1.12 | 1.05 | 1.46 | 1.02 | 0.90 | 1.50 | 0.89 | 1.16 | 0.73 | 0.81 |
| C130036L24Rik | 1.00 | 1.00 | 1.00 | 1.00 | 0.87 | 0.97 | 0.60 | 30.33 | 1.19 | 3.03 | 1.00 | 0.92 |
| C1qa | 1.32 | 1.74 | 1.43 | 1.00 | 1.08 | 1.04 | 1.90 | 12.59 | 1.76 | 1.81 | 0.99 | 0.89 |
| C1qb | 1.06 | 2.07 | 1.40 | 1.44 | 1.78 | 1.39 | 2.53 | 3.70 | 2.05 | 1.31 | 1.03 | 1.15 |
| C1qc | 1.08 | 1.85 | 1.82 | 1.28 | 0.96 | 1.27 | 1.97 | 3.70 | 1.80 | 1.41 | 0.98 | 1.11 |
| C1qtnf2 | 1.00 | 1.00 | 1.00 | 1.00 | 3.50 | 0.89 | 0.77 | 2.42 | 1.22 | 1.00 | 1.00 | 1.00 |
| C1qtnf4 | 1.00 | 1.00 | 1.00 | 1.01 | 0.81 | 1.02 | 1.09 | 11.19 | 0.83 | 2.15 | 1.21 | 1.00 |
| C2cd4a | 1.00 | 1.00 | 1.00 | 1.00 | 1.00 | 1.00 | 1.68 | 11.59 | 2.58 | 1.00 | 1.00 | 1.00 |
| C2cd4b | 5.13 | 12.52 | 3.44 | 1.22 | 1.16 | 1.08 | 1.00 | 1.00 | 1.00 | 1.00 | 1.00 | 1.00 |
| C3 | 0.66 | 1.29 | 1.35 | 1.00 | 1.00 | 1.00 | 1.10 | 5.22 | 1.49 | 3.93 | 1.23 | 0.98 |
| C4b | 1.00 | 1.00 | 0.87 | 0.97 | 0.39 | 0.69 | 1.24 | 5.24 | 1.09 | 1.00 | 1.00 | 1.00 |
| C4bp-ps1 | 1.00 | 1.00 | 1.00 | 1.00 | 0.27 | 1.00 | 1.28 | 6.78 | 1.00 | 1.00 | 1.00 | 1.00 |
| C7 | 1.51 | 1.44 | 3.43 | 1.00 | 1.00 | 1.00 | 2.27 | 0.44 | 2.93 | 1.00 | 1.00 | 1.00 |
| Caap1 | 0.79 | 0.69 | 1.00 | 1.09 | 5.19 | 1.14 | 0.80 | 1.31 | 0.89 | 0.57 | 1.09 | 0.93 |
| Cab39l | 1.05 | 0.95 | 0.97 | 1.09 | 0.88 | 1.11 | 0.80 | 1.13 | 0.89 | 1.32 | 1.02 | 1.00 |
| Cables1 | 1.27 | 1.05 | 1.19 | 1.02 | 0.88 | 0.91 | 1.08 | 1.46 | 1.25 | 2.02 | 3.53 | 1.66 |
| Cacna1c | 1.00 | 1.00 | 1.00 | 0.95 | 1.26 | 0.91 | 1.00 | 1.00 | 1.00 | 1.00 | 1.00 | 1.00 |
| Cacnb4 | 1.00 | 1.00 | 1.00 | 0.91 | 0.34 | 0.87 | 0.78 | 1.05 | 0.95 | 1.00 | 1.00 | 1.00 |
| Cacng1 | 1.00 | 1.00 | 1.00 | 1.00 | 1.11 | 1.00 | 2.14 | 5.47 | 2.44 | 1.00 | 1.00 | 1.00 |
| Cacng3 | 1.00 | 1.00 | 1.00 | 1.05 | 1.16 | 1.01 | 1.00 | 1.00 | 1.00 | 1.00 | 1.00 | 1.00 |
| Cadm3 | 1.00 | 1.00 | 1.00 | 0.97 | 0.95 | 0.92 | 1.45 | 2.41 | 1.66 | 1.00 | 0.92 | 0.73 |
| Calb1 | 1.00 | 1.00 | 1.00 | 1.02 | 1.35 | 1.04 | 1.00 | 1.00 | 1.00 | 1.00 | 1.00 | 1.00 |
| Calb2 | 1.00 | 1.00 | 1.00 | 1.06 | 0.73 | 1.03 | 1.00 | 1.00 | 1.00 | 1.00 | 1.00 | 1.00 |
| Calca | 1.00 | 1.00 | 1.00 | 0.90 | 2.07 | 1.04 | 1.00 | 2.82 | 1.00 | 4.88 | 2.24 | 1.00 |
| Calml4 | 1.00 | 1.19 | 1.00 | 0.66 | 5.42 | 0.70 | 4.26 | 18.55 | 3.18 | 1.49 | 1.00 | 1.00 |
| Calr | 0.80 | 0.71 | 0.71 | 1.19 | 1.06 | 1.02 | 1.10 | 5.29 | 0.82 | 2.23 | 0.91 | 1.00 |
| Caly | 1.00 | 1.00 | 1.00 | 0.90 | 0.42 | 0.79 | 1.00 | 1.00 | 1.00 | 1.00 | 1.00 | 1.00 |
| Camk1 | 0.90 | 2.73 | 1.27 | 1.43 | 1.30 | 1.12 | 1.47 | 4.07 | 1.17 | 4.46 | 2.31 | 2.29 |
| Camk2a | 1.00 | 1.00 | 1.00 | 1.01 | 1.54 | 0.99 | 0.97 | 1.05 | 1.74 | 1.00 | 1.00 | 1.14 |
| Camk2b | 1.00 | 1.00 | 1.00 | 1.04 | 0.93 | 0.96 | 1.23 | 1.26 | 1.42 | 1.00 | 1.00 | 1.00 |
| Camk2n2 | 3.04 | 1.22 | 0.42 | 1.08 | 1.43 | 1.05 | 2.50 | 3.14 | 0.69 | 1.00 | 1.00 | 1.05 |

Fig. 35- 137

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Camkv | 1.00 | 1.00 | 1.00 | 1.00 | 0.12 | 1.00 | 1.00 | 1.00 | 1.00 | 1.00 | 1.00 | 1.00 |
| Camp | 1.00 | 1.35 | 1.72 | 1.31 | 1.00 | 1.00 | 1.00 | 1.00 | 1.00 | 1.85 | 1.84 | 0.92 |
| Cand2 | 0.77 | 5.57 | 1.26 | 1.00 | 1.00 | 1.00 | 1.09 | 1.37 | 1.14 | 1.00 | 1.00 | 0.73 |
| Cant1 | 1.18 | 0.66 | 1.07 | 0.98 | 4.21 | 1.21 | 0.92 | 0.89 | 1.09 | 3.22 | 2.83 | 1.05 |
| Cap2 | 0.84 | 1.08 | 0.83 | 1.04 | 0.23 | 0.96 | 0.93 | 1.06 | 0.95 | 0.87 | 0.63 | 0.84 |
| Capn10 | 0.95 | 1.30 | 0.98 | 0.45 | 0.42 | 0.70 | 2.44 | 2.30 | 1.43 | 1.14 | 1.25 | 1.00 |
| Capn12 | 1.00 | 1.00 | 1.00 | 1.00 | 3.72 | 1.28 | 1.00 | 1.00 | 1.00 | 7.32 | 6.68 | 1.00 |
| Capn8 | 1.00 | 1.00 | 1.00 | 1.00 | 1.00 | 1.00 | 1.00 | 1.00 | 1.00 | 1.00 | 1.00 | 1.00 |
| Capn9 | 1.00 | 1.00 | 1.00 | 1.00 | 1.00 | 1.08 | 1.00 | 1.00 | 1.00 | 1.00 | 1.00 | 1.00 |
| Car14 | 0.78 | 1.04 | 0.75 | 0.14 | 0.08 | 0.15 | 0.92 | 1.04 | 0.71 | 1.00 | 0.43 | 0.78 |
| Car15 | 1.00 | 1.00 | 1.00 | 0.68 | 1.82 | 0.98 | 1.00 | 0.90 | 1.00 | 1.33 | 1.86 | 0.73 |
| Car6 | 1.00 | 1.00 | 1.00 | 1.00 | 1.00 | 1.00 | 1.00 | 1.00 | 1.00 | 1.00 | 1.00 | 1.00 |
| Carkd | 1.53 | 0.75 | 0.99 | 0.46 | 5.00 | 1.09 | 1.05 | 0.90 | 0.90 | 1.95 | 2.89 | 1.11 |
| Carm1 | 1.41 | 5.18 | 1.10 | 1.24 | 0.17 | 1.48 | 1.23 | 1.06 | 0.93 | 1.39 | 0.13 | 1.06 |
| Cars | 0.96 | 0.61 | 1.00 | 0.35 | 3.96 | 1.04 | 1.91 | 1.24 | 1.19 | 2.17 | 3.72 | 0.89 |
| Cars2 | 1.35 | 0.71 | 0.91 | 0.72 | 11.12 | 3.09 | 1.31 | 1.06 | 0.94 | 2.24 | 2.33 | 1.11 |
| Casp4 | 1.00 | 1.86 | 2.02 | 1.00 | 1.76 | 1.00 | 1.08 | 1.81 | 1.35 | 2.11 | 2.15 | 1.16 |
| Cast | 1.41 | 2.13 | 1.30 | 4.43 | 1.60 | 1.54 | 0.95 | 1.24 | 1.17 | 0.64 | 0.90 | 1.08 |
| Catsper4 | 2.15 | 0.68 | 1.49 | 1.00 | 1.00 | 1.00 | 1.00 | 1.00 | 1.00 | 4.06 | 1.91 | 1.00 |
| Cav3 | 1.51 | 0.92 | 1.03 | 1.00 | 1.40 | 0.70 | 0.89 | 0.76 | 1.07 | 1.07 | 1.27 | 0.94 |
| Cblb | 1.34 | 3.90 | 2.06 | 6.51 | 2.65 | 1.87 | 1.70 | 2.06 | 1.72 | 0.88 | 0.86 | 0.99 |
| Cbln1 | 1.00 | 1.00 | 1.00 | 1.00 | 0.31 | 1.00 | 1.00 | 1.00 | 1.00 | 1.00 | 1.00 | 1.00 |
| Cbln3 | 1.00 | 1.00 | 1.00 | 1.00 | 0.32 | 1.00 | 1.00 | 1.00 | 1.00 | 1.00 | 1.00 | 1.00 |
| Cbr3 | 1.20 | 0.82 | 0.88 | 1.08 | 7.15 | 1.10 | 1.37 | 0.70 | 1.30 | 1.58 | 2.28 | 1.00 |
| Cbs | 1.00 | 1.00 | 1.00 | 16.17 | 58.31 | 15.41 | 1.00 | 1.00 | 1.00 | 4.13 | 5.31 | 2.66 |
| Cc2d1a | 0.88 | 0.62 | 0.85 | 0.63 | 4.39 | 1.05 | 0.97 | 0.81 | 1.19 | 1.95 | 2.83 | 0.79 |
| Ccbl2 | 1.44 | 0.93 | 1.16 | 0.75 | 3.58 | 1.53 | 1.22 | 1.15 | 0.93 | 1.30 | 2.11 | 1.00 |
| Ccdc101 | 1.09 | 0.49 | 1.17 | 0.41 | 5.29 | 1.12 | 0.90 | 0.97 | 0.97 | 2.24 | 2.51 | 1.09 |
| Ccdc107 | 1.16 | 0.56 | 1.15 | 0.49 | 8.95 | 1.15 | 1.33 | 0.82 | 1.03 | 3.46 | 4.38 | 1.15 |
| Ccdc113 | 1.00 | 1.00 | 1.00 | 1.00 | 1.00 | 1.00 | 1.00 | 1.00 | 1.00 | 2.08 | 1.72 | 1.46 |
| Ccdc12 | 2.32 | 1.38 | 1.41 | 0.40 | 18.55 | 1.52 | 1.91 | 1.39 | 1.49 | 7.03 | 9.21 | 1.83 |
| Ccdc124 | 1.23 | 0.58 | 0.89 | 0.40 | 9.37 | 1.06 | 1.05 | 0.87 | 0.89 | 2.66 | 4.00 | 1.04 |
| Ccdc153 | 1.00 | 1.00 | 1.00 | 1.00 | 1.00 | 1.00 | 1.00 | 1.00 | 1.00 | 4.00 | 4.78 | 1.38 |
| Ccdc163 | 1.00 | 1.12 | 1.00 | 0.69 | 4.23 | 2.01 | 1.13 | 1.00 | 0.93 | 1.70 | 2.22 | 0.89 |
| Ccdc22 | 0.96 | 0.48 | 0.91 | 0.68 | 7.98 | 0.94 | 1.05 | 1.01 | 0.98 | 4.14 | 5.34 | 1.21 |
| Ccdc23 | 1.05 | 0.64 | 0.76 | 0.77 | 6.63 | 0.82 | 0.76 | 0.70 | 0.83 | 1.67 | 2.42 | 1.21 |
| Ccdc28b | 0.63 | 0.47 | 0.57 | 0.27 | 6.94 | 0.89 | 1.43 | 0.60 | 0.57 | 2.55 | 2.44 | 0.84 |
| Ccdc37 | 1.00 | 1.22 | 1.00 | 1.00 | 4.10 | 1.00 | 1.00 | 1.00 | 1.00 | 3.81 | 3.95 | 1.15 |
| Ccdc53 | 1.73 | 0.75 | 1.06 | 0.85 | 5.27 | 1.18 | 0.95 | 1.14 | 1.00 | 1.45 | 2.26 | 0.97 |
| Ccdc59 | 1.21 | 1.55 | 1.11 | 1.54 | 2.32 | 1.24 | 0.85 | 0.97 | 0.82 | 1.32 | 1.35 | 0.99 |
| Ccdc85b | 0.91 | 0.50 | 0.73 | 0.65 | 8.97 | 1.07 | 0.85 | 0.62 | 0.94 | 2.33 | 3.46 | 0.89 |
| Ccdc9 | 1.03 | 0.82 | 1.09 | 0.59 | 6.34 | 1.38 | 1.26 | 1.11 | 1.36 | 2.48 | 3.22 | 1.01 |
| Cck | 1.00 | 1.00 | 1.00 | 1.00 | 0.07 | 1.00 | 1.00 | 1.00 | 1.00 | 1.00 | 1.00 | 1.00 |
| Ccl17 | 1.00 | 1.00 | 1.00 | 1.00 | 1.00 | 1.00 | 1.00 | 1.00 | 1.00 | 1.94 | 7.29 | 2.86 |
| Ccl19 | 18.10 | 23.19 | 13.56 | 2.90 | 29.81 | 1.95 | 2.15 | 2.03 | 1.87 | 16.23 | 18.22 | 3.14 |
| Ccl21b | 0.91 | 0.20 | 0.29 | 1.08 | 8.27 | 0.47 | 0.43 | 0.82 | 1.95 | 1.39 | 9.10 | 4.32 |
| Ccl24 | 1.70 | 0.34 | 0.62 | 0.90 | 4.70 | 1.41 | 0.45 | 0.84 | 0.68 | 1.68 | 2.42 | 1.00 |
| Ccl25 | 1.38 | 1.03 | 0.58 | 0.72 | 1.97 | 1.47 | 0.79 | 1.00 | 1.00 | 0.63 | 0.72 | 0.99 |
| Ccl27a | 0.99 | 0.43 | 1.12 | 0.34 | 4.04 | 0.59 | 0.64 | 0.64 | 0.23 | 3.27 | 3.52 | 0.93 |
| Ccl27b | 1.00 | 0.57 | 1.00 | 0.77 | 1.00 | 1.00 | 1.00 | 1.00 | 1.00 | 2.63 | 1.00 | 1.00 |
| Ccl28 | 1.00 | 1.00 | 1.00 | 1.23 | 1.00 | 1.00 | 1.00 | 1.00 | 1.00 | 1.00 | 1.00 | 1.25 |
| Ccl6 | 4.84 | 3.02 | 3.50 | 2.89 | 6.54 | 2.65 | 2.57 | 2.79 | 3.07 | 1.34 | 1.80 | 1.16 |
| Ccl8 | 1.93 | 4.29 | 6.04 | 1.00 | 1.04 | 1.00 | 1.00 | 1.30 | 2.30 | 1.39 | 1.79 | 3.20 |
| Ccl9 | 3.43 | 2.76 | 3.16 | 4.96 | 6.10 | 1.86 | 2.51 | 3.31 | 2.38 | 3.61 | 4.85 | 1.52 |
| Ccm2 | 0.92 | 0.73 | 0.93 | 0.64 | 5.08 | 1.64 | 0.97 | 0.64 | 0.84 | 0.99 | 1.76 | 0.88 |
| Ccrn4l | 0.93 | 1.75 | 1.06 | 0.96 | 0.84 | 1.22 | 0.77 | 1.24 | 1.09 | 1.66 | 2.50 | 1.28 |
| Ccs | 0.93 | 0.60 | 0.80 | 0.45 | 8.81 | 1.11 | 1.06 | 0.68 | 0.71 | 1.45 | 2.54 | 0.98 |
| Cct7 | 1.10 | 0.70 | 0.91 | 0.43 | 5.12 | 1.24 | 1.07 | 0.88 | 1.06 | 2.15 | 2.50 | 0.95 |
| Cd14 | 2.65 | 2.39 | 1.84 | 1.45 | 4.97 | 1.27 | 1.75 | 2.39 | 1.34 | 1.72 | 2.85 | 1.01 |
| Cd164l2 | 1.00 | 1.00 | 1.00 | 1.00 | 6.29 | 1.00 | 1.00 | 1.00 | 1.00 | 3.73 | 9.97 | 1.47 |
| Cd177 | 1.00 | 1.00 | 1.00 | 1.00 | 1.00 | 1.00 | 1.00 | 1.00 | 1.00 | 3.31 | 7.90 | 1.56 |
| Cd209d | 1.00 | 0.47 | 0.86 | 0.72 | 1.05 | 0.91 | 1.00 | 1.00 | 1.16 | 0.46 | 1.33 | 0.82 |
| Cd320 | 1.38 | 0.77 | 0.97 | 0.61 | 4.69 | 1.00 | 0.94 | 1.26 | 0.96 | 3.13 | 3.81 | 1.70 |
| Cd55 | 1.10 | 2.10 | 1.08 | 5.86 | 2.08 | 1.65 | 0.58 | 0.86 | 0.75 | 0.61 | 0.38 | 1.02 |

Fig. 35- 138

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Camkv | 0.48 | 0.50 | 0.53 | 1.00 | 1.00 | 1.00 | 1.00 | 1.00 | 1.00 | 1.00 | 1.00 | 1.00 |
| Camp | 0.08 | 0.33 | 0.98 | 1.00 | 1.00 | 1.00 | 1.00 | 1.00 | 1.00 | 1.00 | 1.00 | 1.00 |
| Cand2 | 0.50 | 0.54 | 0.66 | 0.95 | 1.00 | 0.94 | 1.00 | 1.00 | 1.00 | 0.85 | 0.98 | 0.90 |
| Cant1 | 1.10 | 1.15 | 1.07 | 1.09 | 0.54 | 1.09 | 1.11 | 2.72 | 1.20 | 1.03 | 1.25 | 1.06 |
| Cap2 | 1.58 | 1.35 | 1.52 | 1.00 | 1.00 | 1.00 | 1.00 | 1.00 | 1.00 | 0.95 | 0.69 | 0.76 |
| Capn10 | 0.97 | 1.33 | 1.03 | 0.94 | 0.90 | 0.97 | 0.76 | 0.42 | 0.69 | 0.97 | 1.15 | 0.91 |
| Capn12 | 1.00 | 1.00 | 1.00 | 1.00 | 0.16 | 1.00 | 1.00 | 4.20 | 1.00 | 1.00 | 1.00 | 1.00 |
| Capn8 | 1.00 | 1.00 | 1.00 | 1.00 | 1.00 | 1.00 | 5.14 | 2.59 | 7.39 | 0.87 | 0.61 | 0.73 |
| Capn9 | 1.00 | 1.00 | 1.00 | 1.00 | 1.00 | 1.00 | 1.00 | 1.00 | 1.00 | 0.72 | 0.63 | 0.71 |
| Car14 | 1.00 | 1.00 | 1.00 | 0.75 | 8.44 | 0.80 | 0.46 | 1.00 | 0.36 | 1.37 | 0.70 | 0.89 |
| Car15 | 1.65 | 1.54 | 1.22 | 1.26 | 1.40 | 1.03 | 1.00 | 1.00 | 1.00 | 1.08 | 1.95 | 2.42 |
| Car6 | 1.00 | 1.00 | 0.94 | 1.00 | 1.00 | 1.00 | 1.00 | 1.00 | 1.00 | 1.00 | 1.00 | 1.00 |
| Carkd | 1.24 | 1.52 | 0.97 | 1.29 | 1.07 | 1.06 | 0.98 | 1.41 | 1.05 | 1.04 | 1.63 | 1.13 |
| Carm1 | 0.89 | 0.92 | 1.02 | 1.13 | 1.00 | 1.12 | 1.36 | 1.00 | 1.39 | 1.09 | 0.75 | 1.25 |
| Cars | 0.98 | 1.00 | 0.85 | 1.22 | 0.71 | 1.26 | 0.93 | 1.29 | 0.63 | 0.92 | 1.64 | 0.96 |
| Cars2 | 1.08 | 1.32 | 0.94 | 1.44 | 0.58 | 1.09 | 1.22 | 2.41 | 1.06 | 1.08 | 1.33 | 0.85 |
| Casp4 | 1.65 | 1.66 | 1.90 | 1.00 | 1.09 | 1.00 | 1.00 | 1.00 | 1.00 | 1.21 | 1.29 | 1.32 |
| Cast | 1.03 | 1.02 | 1.12 | 1.24 | 0.97 | 1.02 | 1.42 | 0.73 | 1.17 | 1.01 | 1.12 | 1.04 |
| Catsper4 | 1.00 | 1.00 | 1.00 | 1.00 | 0.90 | 1.00 | 1.00 | 1.00 | 1.00 | 1.00 | 1.58 | 0.79 |
| Cav3 | 1.00 | 1.00 | 1.00 | 1.00 | 1.00 | 1.00 | 1.00 | 1.00 | 1.00 | 1.11 | 1.41 | 0.67 |
| Cblb | 1.20 | 1.07 | 1.24 | 0.98 | 1.09 | 0.91 | 1.29 | 1.00 | 1.42 | 0.94 | 0.73 | 1.09 |
| Cbln1 | 1.00 | 1.00 | 1.00 | 1.00 | 1.00 | 1.00 | 1.00 | 1.00 | 1.00 | 1.00 | 1.00 | 1.00 |
| Cbln3 | 1.00 | 1.00 | 1.00 | 1.00 | 1.00 | 1.00 | 1.00 | 1.00 | 1.00 | 0.65 | 0.58 | 0.86 |
| Cbr3 | 1.21 | 1.52 | 1.49 | 1.86 | 0.87 | 1.17 | 1.00 | 3.26 | 1.00 | 1.47 | 2.11 | 1.22 |
| Cbs | 1.00 | 1.00 | 1.00 | 1.84 | 1.78 | 1.75 | 0.93 | 1.22 | 0.98 | 1.73 | 2.63 | 1.82 |
| Cc2d1a | 1.07 | 1.36 | 0.98 | 0.97 | 0.57 | 1.00 | 1.26 | 1.85 | 1.46 | 0.91 | 1.26 | 1.01 |
| Ccbl2 | 1.31 | 1.47 | 1.27 | 1.05 | 1.27 | 0.93 | 1.53 | 1.89 | 1.25 | 1.45 | 1.64 | 1.34 |
| Ccdc101 | 1.05 | 1.00 | 0.79 | 1.42 | 0.99 | 0.89 | 0.77 | 2.02 | 0.69 | 1.17 | 1.73 | 1.14 |
| Ccdc107 | 1.06 | 1.50 | 1.04 | 0.87 | 0.60 | 0.98 | 0.76 | 1.63 | 0.77 | 1.05 | 1.59 | 1.22 |
| Ccdc113 | 1.00 | 1.00 | 1.00 | 1.00 | 1.00 | 1.00 | 1.00 | 1.00 | 1.00 | 1.00 | 1.00 | 1.00 |
| Ccdc12 | 2.44 | 3.18 | 1.85 | 1.57 | 1.91 | 1.48 | 2.06 | 3.74 | 1.78 | 1.88 | 3.65 | 2.07 |
| Ccdc124 | 1.05 | 1.44 | 0.90 | 0.95 | 0.68 | 1.00 | 1.02 | 1.78 | 1.00 | 1.05 | 1.66 | 1.08 |
| Ccdc153 | 1.07 | 0.80 | 0.40 | 1.00 | 1.00 | 1.00 | 1.00 | 1.00 | 1.00 | 1.00 | 1.00 | 1.00 |
| Ccdc163 | 1.29 | 1.75 | 0.97 | 0.98 | 0.39 | 0.95 | 1.00 | 1.54 | 1.00 | 0.64 | 1.45 | 1.23 |
| Ccdc22 | 1.19 | 1.15 | 0.96 | 0.93 | 0.50 | 1.00 | 0.59 | 2.77 | 0.70 | 0.96 | 1.88 | 0.91 |
| Ccdc23 | 1.46 | 1.94 | 1.11 | 0.75 | 0.72 | 0.86 | 0.84 | 0.75 | 0.81 | 1.01 | 1.65 | 0.94 |
| Ccdc28b | 0.94 | 1.26 | 0.87 | 1.07 | 0.60 | 0.88 | 0.73 | 1.58 | 0.61 | 1.31 | 1.61 | 0.90 |
| Ccdc37 | 1.00 | 1.00 | 1.00 | 1.00 | 1.31 | 1.00 | 1.00 | 2.38 | 1.00 | 1.00 | 1.00 | 1.00 |
| Ccdc53 | 1.37 | 1.87 | 0.93 | 0.96 | 0.93 | 0.76 | 0.85 | 1.11 | 1.06 | 0.99 | 1.91 | 1.05 |
| Ccdc59 | 1.04 | 1.00 | 0.91 | 1.01 | 0.90 | 1.07 | 1.11 | 1.50 | 1.17 | 1.03 | 1.20 | 1.12 |
| Ccdc85b | 1.01 | 1.22 | 1.02 | 0.67 | 0.46 | 0.92 | 0.68 | 1.91 | 0.95 | 0.77 | 1.40 | 0.93 |
| Ccdc9 | 1.22 | 1.58 | 1.03 | 0.88 | 0.73 | 0.99 | 1.01 | 1.84 | 1.04 | 1.01 | 1.37 | 0.99 |
| Cck | 0.96 | 1.40 | 0.59 | 0.66 | 0.63 | 0.55 | 1.00 | 1.00 | 1.00 | 1.32 | 1.60 | 1.66 |
| Ccl17 | 0.90 | 1.53 | 0.73 | 0.87 | 0.20 | 1.00 | 1.00 | 1.00 | 1.00 | 0.37 | 0.86 | 0.93 |
| Ccl19 | 0.60 | 0.69 | 0.41 | 0.45 | 0.56 | 0.36 | 0.53 | 4.39 | 0.46 | 0.44 | 0.38 | 0.23 |
| Ccl21b | 1.00 | 8.86 | 1.00 | 0.85 | 0.86 | 0.77 | 0.83 | 1.33 | 0.61 | 3.87 | 2.97 | 0.57 |
| Ccl24 | 1.13 | 0.91 | 0.98 | 1.00 | 1.00 | 1.00 | 1.00 | 1.90 | 0.98 | 1.00 | 1.00 | 0.89 |
| Ccl25 | 0.44 | 0.57 | 0.57 | 0.61 | 2.03 | 0.95 | 0.99 | 0.39 | 0.73 | 1.56 | 1.83 | 1.99 |
| Ccl27a | 1.40 | 1.41 | 0.69 | 0.60 | 0.72 | 0.65 | 0.14 | 0.96 | 0.80 | 0.78 | 1.19 | 0.69 |
| Ccl27b | 3.17 | 3.25 | 2.43 | 1.00 | 1.00 | 1.00 | 1.00 | 1.00 | 1.00 | 1.00 | 1.00 | 1.00 |
| Ccl28 | 1.00 | 1.00 | 1.00 | 5.21 | 3.91 | 2.91 | 1.00 | 1.00 | 1.00 | 0.75 | 0.63 | 0.65 |
| Ccl6 | 6.13 | 8.12 | 3.87 | 2.04 | 3.85 | 1.76 | 4.25 | 2.59 | 3.20 | 1.35 | 1.65 | 1.36 |
| Ccl8 | 1.42 | 1.69 | 2.23 | 1.00 | 1.00 | 1.00 | 1.00 | 1.00 | 1.00 | 1.58 | 1.06 | 1.16 |
| Ccl9 | 5.60 | 8.06 | 3.28 | 1.03 | 1.00 | 1.00 | 0.84 | 1.11 | 1.33 | 2.00 | 2.38 | 1.42 |
| Ccm2 | 0.95 | 1.21 | 0.88 | 0.90 | 1.20 | 1.09 | 1.35 | 0.86 | 1.10 | 0.98 | 1.27 | 1.05 |
| Ccrn4l | 0.59 | 0.60 | 0.62 | 1.64 | 3.20 | 1.13 | 0.83 | 0.99 | 0.59 | 1.26 | 1.27 | 0.93 |
| Ccs | 1.08 | 1.75 | 0.98 | 0.88 | 0.87 | 0.92 | 1.02 | 1.13 | 1.04 | 0.84 | 1.61 | 1.11 |
| Cct7 | 0.93 | 1.02 | 0.88 | 1.00 | 0.72 | 0.93 | 1.20 | 1.62 | 1.16 | 1.06 | 1.52 | 1.02 |
| Cd14 | 3.51 | 4.04 | 1.97 | 0.94 | 1.14 | 0.72 | 4.70 | 10.59 | 2.21 | 1.07 | 1.29 | 1.08 |
| Cd164l2 | 1.00 | 1.00 | 1.00 | 1.14 | 0.41 | 1.14 | 1.00 | 1.00 | 1.00 | 1.00 | 2.02 | 1.05 |
| Cd177 | 0.72 | 1.00 | 1.00 | 1.00 | 1.00 | 1.00 | 1.00 | 1.00 | 1.00 | 1.56 | 1.89 | 1.07 |
| Cd209d | 0.27 | 0.67 | 0.64 | 1.00 | 1.00 | 1.00 | 1.00 | 1.00 | 1.00 | 1.00 | 1.00 | 1.00 |
| Cd320 | 1.15 | 1.38 | 1.14 | 1.17 | 1.08 | 0.99 | 0.88 | 1.77 | 0.82 | 1.51 | 1.94 | 1.34 |
| Cd55 | 2.08 | 1.43 | 1.60 | 1.72 | 1.63 | 1.46 | 0.87 | 1.00 | 0.74 | 0.99 | 1.01 | 0.92 |

Fig. 35- 139

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Camkv | 1.00 | 1.00 | 1.00 | 1.00 | 1.00 | 1.00 | 0.91 | 2.22 | 1.01 | 1.00 | 14.77 | 1.00 |
| Camp | 1.00 | 0.72 | 1.00 | 1.00 | 0.54 | 1.00 | 1.00 | 1.00 | 1.00 | 8.08 | 7.53 | 5.10 |
| Cand2 | 0.75 | 0.60 | 0.90 | 0.67 | 1.00 | 0.89 | 1.14 | 1.07 | 1.02 | 0.74 | 0.50 | 0.73 |
| Cant1 | 0.94 | 0.98 | 0.85 | 1.02 | 1.53 | 1.02 | 1.02 | 2.77 | 0.95 | 1.08 | 1.10 | 1.18 |
| Cap2 | 1.22 | 0.83 | 1.23 | 0.89 | 1.00 | 1.14 | 0.73 | 0.65 | 0.82 | 1.00 | 5.27 | 1.00 |
| Capn10 | 0.83 | 1.11 | 0.98 | 0.83 | 1.59 | 0.76 | 1.08 | 1.04 | 0.96 | 1.02 | 1.17 | 1.11 |
| Capn12 | 1.00 | 1.00 | 1.00 | 1.10 | 2.43 | 1.49 | 1.00 | 1.00 | 1.00 | 1.00 | 1.00 | 1.00 |
| Capn8 | 0.56 | 0.56 | 0.32 | 1.00 | 1.00 | 1.00 | 1.15 | 1.00 | 1.00 | 1.00 | 1.00 | 1.00 |
| Capn9 | 0.48 | 0.55 | 0.39 | 1.00 | 1.00 | 1.00 | 1.00 | 1.00 | 1.00 | 1.00 | 1.00 | 1.00 |
| Car14 | 1.35 | 1.20 | 1.52 | 1.03 | 1.00 | 1.00 | 1.00 | 1.00 | 1.00 | 1.00 | 1.00 | 1.00 |
| Car15 | 1.01 | 0.79 | 1.40 | 1.00 | 1.00 | 1.00 | 0.57 | 0.63 | 1.32 | 2.39 | 1.95 | 1.09 |
| Car6 | 1.00 | 1.00 | 1.00 | 1.00 | 1.00 | 1.00 | 1.00 | 1.00 | 1.00 | 1.00 | 1.00 | 1.00 |
| Carkd | 0.98 | 1.09 | 1.09 | 1.41 | 3.87 | 1.19 | 0.90 | 1.35 | 0.85 | 0.96 | 1.30 | 0.87 |
| Carm1 | 1.11 | 1.13 | 1.25 | 1.39 | 0.36 | 1.56 | 1.12 | 1.55 | 1.12 | 0.94 | 0.91 | 0.99 |
| Cars | 1.02 | 0.91 | 0.92 | 0.84 | 1.48 | 1.16 | 0.78 | 2.26 | 0.98 | 0.74 | 1.02 | 0.77 |
| Cars2 | 0.90 | 1.33 | 1.37 | 3.26 | 23.57 | 1.28 | 0.97 | 1.79 | 1.17 | 0.88 | 0.91 | 1.18 |
| Casp4 | 1.45 | 1.26 | 1.00 | 0.92 | 0.52 | 1.05 | 1.00 | 1.00 | 1.00 | 1.62 | 1.26 | 1.31 |
| Cast | 1.04 | 0.94 | 0.94 | 0.91 | 0.68 | 0.69 | 0.94 | 5.42 | 1.00 | 0.90 | 0.76 | 0.93 |
| Catsper4 | 1.00 | 1.00 | 1.00 | 1.00 | 1.81 | 1.00 | 0.94 | 4.93 | 0.93 | 1.00 | 1.00 | 1.00 |
| Cav3 | 0.99 | 1.34 | 1.49 | 1.00 | 1.00 | 1.00 | 1.00 | 1.00 | 1.00 | 1.00 | 1.00 | 1.00 |
| Cblb | 1.13 | 1.13 | 1.12 | 1.45 | 1.60 | 1.01 | 1.25 | 1.76 | 1.15 | 1.12 | 0.88 | 1.03 |
| Cbln1 | 1.00 | 1.00 | 1.00 | 1.00 | 1.00 | 1.42 | 1.07 | 2.29 | 1.05 | 1.00 | 5.29 | 1.00 |
| Cbln3 | 1.00 | 1.00 | 1.00 | 1.00 | 1.00 | 1.00 | 1.00 | 1.00 | 1.00 | 1.00 | 5.12 | 1.00 |
| Cbr3 | 0.84 | 1.07 | 0.78 | 0.75 | 1.87 | 0.66 | 0.74 | 1.25 | 0.89 | 1.08 | 1.93 | 1.01 |
| Cbs | 8.12 | 9.30 | 5.50 | 5.17 | 4.20 | 5.34 | 1.00 | 1.00 | 0.93 | 1.00 | 1.00 | 1.00 |
| Cc2d1a | 1.12 | 1.11 | 0.86 | 1.14 | 1.55 | 0.97 | 0.96 | 1.69 | 1.25 | 0.91 | 1.19 | 1.07 |
| Ccbl2 | 1.05 | 1.58 | 1.27 | 2.64 | 5.19 | 3.26 | 0.89 | 0.87 | 1.08 | 1.13 | 1.34 | 0.93 |
| Ccdc101 | 0.96 | 0.96 | 1.21 | 0.93 | 2.42 | 1.16 | 0.93 | 1.56 | 1.00 | 1.27 | 1.21 | 0.86 |
| Ccdc107 | 1.17 | 1.23 | 1.24 | 1.22 | 2.37 | 1.47 | 0.72 | 2.41 | 0.74 | 1.04 | 1.26 | 1.20 |
| Ccdc113 | 1.00 | 1.00 | 1.00 | 1.44 | 1.00 | 2.46 | 1.08 | 1.64 | 0.97 | 1.00 | 1.00 | 1.00 |
| Ccdc12 | 1.66 | 1.79 | 1.68 | 1.81 | 17.33 | 1.88 | 1.22 | 4.53 | 1.37 | 2.76 | 3.03 | 1.76 |
| Ccdc124 | 0.84 | 0.82 | 0.85 | 0.92 | 1.98 | 1.12 | 0.93 | 2.86 | 1.11 | 0.88 | 1.41 | 0.99 |
| Ccdc153 | 1.00 | 1.00 | 1.00 | 1.10 | 6.56 | 3.81 | 1.00 | 2.42 | 1.00 | 1.00 | 1.00 | 1.00 |
| Ccdc163 | 0.73 | 0.62 | 0.95 | 1.02 | 2.36 | 1.50 | 0.89 | 1.89 | 0.96 | 1.32 | 1.05 | 1.16 |
| Ccdc22 | 0.89 | 1.10 | 1.39 | 1.14 | 0.94 | 0.62 | 1.00 | 6.42 | 1.00 | 0.83 | 0.81 | 0.95 |
| Ccdc23 | 1.20 | 1.08 | 1.16 | 0.97 | 2.03 | 0.87 | 1.09 | 1.48 | 1.13 | 1.05 | 1.47 | 1.04 |
| Ccdc28b | 0.98 | 1.38 | 1.78 | 0.75 | 1.48 | 0.66 | 0.89 | 2.86 | 0.83 | 0.97 | 1.12 | 0.89 |
| Ccdc37 | 1.00 | 1.00 | 1.00 | 1.10 | 2.05 | 1.30 | 1.13 | 2.32 | 0.97 | 1.00 | 1.00 | 1.00 |
| Ccdc53 | 0.99 | 0.93 | 1.13 | 0.83 | 1.90 | 0.91 | 0.88 | 0.86 | 0.89 | 1.20 | 1.38 | 0.82 |
| Ccdc59 | 0.89 | 0.91 | 0.99 | 1.16 | 5.16 | 1.18 | 0.92 | 0.74 | 0.81 | 1.08 | 1.17 | 1.05 |
| Ccdc85b | 0.73 | 0.96 | 0.98 | 0.85 | 1.45 | 0.94 | 1.04 | 4.16 | 1.24 | 0.83 | 1.30 | 1.07 |
| Ccdc9 | 1.06 | 1.16 | 0.86 | 1.17 | 2.24 | 0.97 | 0.98 | 3.19 | 1.10 | 1.01 | 1.40 | 0.95 |
| Cck | 1.00 | 1.00 | 1.00 | 1.00 | 1.00 | 0.35 | 1.32 | 4.91 | 4.20 | 1.00 | 16.12 | 1.00 |
| Ccl17 | 1.00 | 1.00 | 1.00 | 1.00 | 0.58 | 1.00 | 1.26 | 2.58 | 1.35 | 2.62 | 4.57 | 2.42 |
| Ccl19 | 1.00 | 0.68 | 1.00 | 0.37 | 1.28 | 0.57 | 1.00 | 5.54 | 1.00 | 0.22 | 0.28 | 0.23 |
| Ccl21b | 1.67 | 2.53 | 1.00 | 1.00 | 4.12 | 2.60 | 1.53 | 4.05 | 3.01 | 1.00 | 3.82 | 1.00 |
| Ccl24 | 1.00 | 1.00 | 1.00 | 0.60 | 1.23 | 0.75 | 1.00 | 2.66 | 1.00 | 0.47 | 0.39 | 0.88 |
| Ccl25 | 3.28 | 1.73 | 2.61 | 1.17 | 1.00 | 2.03 | 0.86 | 0.56 | 0.57 | 1.06 | 1.31 | 0.90 |
| Ccl27a | 0.92 | 1.20 | 0.84 | 0.58 | 7.48 | 0.83 | 0.67 | 3.44 | 1.15 | 0.51 | 1.14 | 1.03 |
| Ccl27b | 1.00 | 1.00 | 0.97 | 1.00 | 1.72 | 1.00 | 1.43 | 22.29 | 1.15 | 1.00 | 1.00 | 1.00 |
| Ccl28 | 1.18 | 1.28 | 1.36 | 1.79 | 1.32 | 2.93 | 1.46 | 2.22 | 1.58 | 1.11 | 1.00 | 1.00 |
| Ccl6 | 2.19 | 2.69 | 2.03 | 1.58 | 3.65 | 1.27 | 1.00 | 1.00 | 1.26 | 1.44 | 1.71 | 1.32 |
| Ccl8 | 3.72 | 1.63 | 3.01 | 0.39 | 1.11 | 1.31 | 1.00 | 1.00 | 1.00 | 1.00 | 1.00 | 0.17 |
| Ccl9 | 3.73 | 3.81 | 3.28 | 1.44 | 2.56 | 0.89 | 1.00 | 1.00 | 1.00 | 2.05 | 2.13 | 1.14 |
| Ccm2 | 0.91 | 1.01 | 1.24 | 1.01 | 7.15 | 1.11 | 0.69 | 1.08 | 1.00 | 0.88 | 1.15 | 0.98 |
| Ccrn4l | 1.08 | 1.26 | 0.95 | 1.57 | 1.83 | 1.39 | 0.91 | 0.58 | 1.16 | 0.74 | 0.74 | 0.44 |
| Ccs | 0.99 | 1.47 | 0.94 | 0.90 | 4.45 | 1.00 | 0.87 | 0.98 | 0.73 | 0.91 | 1.23 | 1.03 |
| Cct7 | 0.91 | 0.99 | 0.94 | 1.22 | 2.39 | 1.19 | 1.00 | 2.12 | 0.96 | 0.97 | 1.19 | 0.96 |
| Cd14 | 1.97 | 2.46 | 1.51 | 2.01 | 5.98 | 1.06 | 1.53 | 2.49 | 0.98 | 2.53 | 6.42 | 1.74 |
| Cd164l2 | 1.02 | 1.59 | 2.13 | 1.93 | 3.45 | 4.03 | 0.93 | 2.41 | 1.45 | 1.00 | 1.00 | 1.00 |
| Cd177 | 0.79 | 0.89 | 0.95 | 1.00 | 1.00 | 1.00 | 1.00 | 1.91 | 1.00 | 7.16 | 5.24 | 3.03 |
| Cd209d | 1.00 | 1.00 | 1.00 | 0.61 | 7.34 | 1.16 | 1.00 | 1.00 | 1.00 | 0.54 | 0.48 | 0.46 |
| Cd320 | 1.10 | 1.39 | 1.15 | 1.48 | 3.17 | 1.59 | 1.04 | 1.76 | 0.97 | 1.41 | 1.34 | 1.12 |
| Cd55 | 1.00 | 0.97 | 0.93 | 1.37 | 0.75 | 1.11 | 0.96 | 1.46 | 1.18 | 0.81 | 0.49 | 0.77 |

Fig. 35- 140

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Camkv | 1.00 | 1.00 | 1.00 | 1.02 | 0.95 | 0.97 | 1.00 | 1.00 | 1.00 | 1.00 | 1.00 | 1.00 |
| Camp | 1.00 | 1.00 | 1.00 | 1.00 | 0.37 | 1.00 | 1.00 | 3.40 | 1.00 | 1.65 | 1.04 | 0.92 |
| Cand2 | 1.00 | 1.00 | 1.00 | 0.55 | 0.65 | 0.49 | 0.81 | 0.80 | 1.23 | 1.00 | 0.92 | 1.00 |
| Cant1 | 0.91 | 0.93 | 0.95 | 1.08 | 0.86 | 0.99 | 1.03 | 5.74 | 0.99 | 2.68 | 1.11 | 1.07 |
| Cap2 | 1.00 | 1.00 | 1.00 | 1.03 | 0.90 | 0.96 | 1.13 | 0.53 | 1.68 | 1.00 | 1.00 | 1.00 |
| Capn10 | 1.31 | 1.11 | 0.92 | 0.97 | 8.95 | 0.95 | 0.93 | 1.13 | 0.91 | 1.17 | 1.40 | 1.36 |
| Capn12 | 1.00 | 1.00 | 1.00 | 1.00 | 0.37 | 1.00 | 1.58 | 11.74 | 0.93 | 1.00 | 1.00 | 1.00 |
| Capn8 | 1.00 | 1.00 | 1.00 | 1.00 | 1.00 | 1.00 | 1.00 | 1.00 | 1.00 | 1.00 | 1.00 | 1.00 |
| Capn9 | 1.00 | 1.00 | 1.00 | 1.00 | 1.00 | 1.00 | 1.00 | 6.25 | 1.00 | 1.00 | 1.00 | 1.00 |
| Car14 | 1.00 | 1.00 | 1.00 | 1.79 | 1.00 | 0.88 | 2.04 | 1.00 | 2.21 | 1.00 | 1.00 | 1.00 |
| Car15 | 1.00 | 1.00 | 1.00 | 1.36 | 5.71 | 1.39 | 1.26 | 2.16 | 1.00 | 3.22 | 1.66 | 0.98 |
| Car6 | 1.00 | 1.00 | 1.00 | 1.00 | 1.00 | 1.00 | 1.42 | 8.00 | 0.75 | 1.00 | 1.00 | 1.00 |
| Carkd | 1.31 | 1.30 | 1.08 | 1.10 | 0.89 | 1.12 | 1.04 | 4.86 | 0.87 | 2.11 | 1.19 | 0.93 |
| Carm1 | 1.15 | 1.09 | 1.60 | 1.10 | 1.55 | 1.10 | 1.02 | 0.07 | 1.01 | 0.11 | 0.75 | 0.85 |
| Cars | 1.37 | 1.93 | 1.25 | 0.94 | 0.97 | 0.95 | 0.80 | 6.73 | 0.88 | 2.68 | 1.15 | 0.99 |
| Cars2 | 0.91 | 1.00 | 0.77 | 1.17 | 1.30 | 1.33 | 1.10 | 8.99 | 0.85 | 2.91 | 1.08 | 1.12 |
| Casp4 | 1.00 | 1.00 | 1.00 | 1.00 | 1.00 | 1.00 | 1.57 | 6.12 | 1.09 | 3.06 | 1.86 | 2.00 |
| Cast | 1.00 | 1.00 | 1.00 | 0.94 | 1.00 | 1.02 | 0.83 | 0.61 | 0.95 | 0.76 | 0.95 | 0.90 |
| Catsper4 | 1.00 | 1.00 | 1.00 | 1.00 | 1.00 | 1.00 | 1.00 | 11.53 | 1.00 | 1.00 | 1.00 | 1.00 |
| Cav3 | 1.00 | 1.00 | 1.00 | 1.00 | 1.00 | 1.00 | 1.51 | 6.99 | 1.87 | 1.00 | 1.00 | 1.00 |
| Cblb | 1.51 | 1.35 | 0.98 | 0.95 | 1.25 | 0.97 | 1.11 | 0.92 | 1.60 | 1.02 | 1.19 | 1.00 |
| Cbln1 | 1.00 | 1.00 | 1.00 | 0.93 | 0.70 | 0.89 | 1.00 | 1.00 | 1.00 | 1.00 | 0.84 | 1.00 |
| Cbln3 | 1.00 | 1.00 | 1.00 | 0.85 | 0.49 | 0.84 | 1.00 | 1.00 | 1.00 | 1.00 | 1.00 | 1.00 |
| Cbr3 | 1.00 | 1.00 | 1.00 | 1.02 | 1.47 | 1.20 | 0.92 | 3.28 | 0.69 | 5.63 | 2.41 | 1.92 |
| Cbs | 1.59 | 1.56 | 1.20 | 1.15 | 1.19 | 1.16 | 0.38 | 0.88 | 0.37 | 1.00 | 1.00 | 1.00 |
| Cc2d1a | 1.14 | 1.00 | 1.00 | 1.05 | 0.85 | 1.13 | 1.16 | 5.35 | 0.93 | 3.18 | 1.02 | 1.38 |
| Ccbl2 | 0.58 | 0.53 | 0.57 | 1.03 | 1.41 | 1.54 | 0.92 | 0.80 | 1.30 | 1.10 | 1.00 | 1.26 |
| Ccdc101 | 1.55 | 1.22 | 0.57 | 0.75 | 0.53 | 0.66 | 1.21 | 5.51 | 1.04 | 1.82 | 1.15 | 0.83 |
| Ccdc107 | 1.33 | 1.29 | 2.10 | 1.46 | 1.11 | 1.24 | 1.34 | 21.34 | 1.12 | 3.33 | 1.39 | 1.22 |
| Ccdc113 | 1.00 | 1.00 | 1.00 | 1.01 | 1.57 | 0.81 | 1.77 | 6.11 | 0.36 | 1.00 | 1.00 | 1.00 |
| Ccdc12 | 1.67 | 1.40 | 1.58 | 1.67 | 15.53 | 1.69 | 2.28 | 22.25 | 1.35 | 8.48 | 3.14 | 2.63 |
| Ccdc124 | 1.49 | 1.52 | 0.93 | 1.16 | 0.91 | 1.03 | 1.19 | 13.44 | 0.83 | 3.17 | 1.32 | 1.20 |
| Ccdc153 | 1.00 | 1.00 | 1.00 | 0.97 | 0.88 | 1.12 | 1.00 | 1.00 | 1.00 | 1.00 | 1.00 | 1.00 |
| Ccdc163 | 1.00 | 1.00 | 1.00 | 1.00 | 2.94 | 1.00 | 1.00 | 6.62 | 1.00 | 2.20 | 1.85 | 1.77 |
| Ccdc22 | 1.38 | 0.66 | 1.05 | 1.12 | 0.89 | 1.01 | 1.25 | 15.44 | 0.96 | 3.55 | 1.10 | 0.91 |
| Ccdc23 | 0.61 | 1.39 | 0.60 | 1.06 | 1.01 | 1.12 | 1.03 | 2.77 | 0.82 | 1.72 | 1.11 | 1.21 |
| Ccdc28b | 2.65 | 1.65 | 1.11 | 1.26 | 1.14 | 1.03 | 1.13 | 9.73 | 1.01 | 2.84 | 1.62 | 1.31 |
| Ccdc37 | 1.00 | 1.00 | 1.00 | 1.00 | 1.03 | 0.93 | 1.00 | 5.55 | 1.00 | 1.00 | 1.00 | 1.00 |
| Ccdc53 | 0.77 | 0.82 | 0.70 | 1.13 | 0.76 | 0.85 | 1.10 | 3.91 | 0.99 | 2.94 | 1.23 | 1.04 |
| Ccdc59 | 1.16 | 0.41 | 0.91 | 0.96 | 0.60 | 0.99 | 0.96 | 1.88 | 1.03 | 1.39 | 0.84 | 1.10 |
| Ccdc85b | 0.74 | 0.94 | 1.15 | 1.17 | 0.90 | 1.06 | 0.97 | 14.26 | 0.85 | 3.19 | 1.14 | 0.92 |
| Ccdc9 | 1.16 | 1.09 | 1.25 | 0.91 | 0.94 | 0.90 | 1.09 | 2.38 | 0.98 | 3.44 | 1.48 | 0.96 |
| Cck | 1.00 | 1.00 | 1.00 | 1.20 | 0.88 | 1.06 | 0.64 | 3.77 | 1.00 | 1.00 | 1.00 | 1.00 |
| Ccl17 | 1.00 | 1.00 | 1.00 | 1.64 | 0.77 | 0.38 | 0.37 | 13.20 | 1.03 | 1.06 | 1.00 | 1.00 |
| Ccl19 | 1.00 | 1.00 | 0.42 | 9.43 | 12.67 | 8.92 | 10.42 | 87.91 | 7.63 | 1.08 | 1.00 | 1.00 |
| Ccl21b | 0.72 | 0.97 | 1.00 | 2.40 | 5.73 | 3.10 | 0.81 | 74.23 | 4.29 | 1.00 | 1.00 | 1.00 |
| Ccl24 | 1.00 | 1.00 | 1.00 | 1.00 | 0.22 | 1.00 | 0.92 | 14.20 | 0.90 | 1.00 | 1.00 | 1.00 |
| Ccl25 | 1.10 | 1.00 | 1.00 | 0.94 | 5.58 | 1.18 | 1.21 | 2.29 | 1.07 | 0.86 | 1.45 | 0.85 |
| Ccl27a | 0.88 | 0.93 | 0.90 | 1.41 | 1.75 | 1.36 | 1.98 | 14.17 | 1.53 | 2.56 | 1.34 | 1.02 |
| Ccl27b | 1.00 | 1.00 | 1.00 | 1.00 | 20.26 | 1.00 | 4.69 | 120.76 | 11.93 | 1.00 | 1.00 | 1.00 |
| Ccl28 | 1.00 | 1.00 | 1.00 | 1.80 | 1.00 | 2.05 | 1.89 | 1.00 | 2.50 | 1.00 | 1.00 | 1.00 |
| Ccl6 | 1.18 | 5.05 | 1.56 | 1.49 | 0.31 | 1.63 | 2.19 | 4.68 | 3.19 | 1.26 | 1.59 | 1.40 |
| Ccl8 | 1.00 | 1.00 | 1.00 | 1.00 | 1.00 | 1.00 | 1.10 | 2.86 | 0.97 | 0.84 | 1.00 | 1.00 |
| Ccl9 | 1.19 | 1.45 | 1.00 | 1.00 | 1.00 | 1.00 | 2.47 | 10.26 | 3.64 | 2.13 | 2.22 | 1.60 |
| Ccm2 | 1.63 | 1.60 | 1.41 | 1.11 | 1.34 | 1.11 | 1.42 | 4.20 | 1.08 | 1.77 | 1.09 | 1.17 |
| Ccrn4l | 2.54 | 6.91 | 1.57 | 1.13 | 0.92 | 1.07 | 1.30 | 1.43 | 0.92 | 0.80 | 0.64 | 0.77 |
| Ccs | 1.27 | 1.46 | 1.06 | 1.32 | 1.20 | 1.06 | 1.35 | 4.95 | 1.12 | 2.03 | 0.95 | 0.99 |
| Cct7 | 1.04 | 1.14 | 1.21 | 1.02 | 0.98 | 1.01 | 1.16 | 5.19 | 0.96 | 1.87 | 0.99 | 1.00 |
| Cd14 | 1.22 | 3.40 | 1.10 | 1.59 | 0.64 | 1.40 | 4.01 | 9.07 | 3.18 | 5.52 | 6.39 | 2.95 |
| Cd164l2 | 1.00 | 1.00 | 1.09 | 1.05 | 0.38 | 1.20 | 1.30 | 9.84 | 1.82 | 1.00 | 1.00 | 1.00 |
| Cd177 | 1.00 | 1.00 | 1.00 | 1.00 | 1.00 | 1.00 | 1.00 | 1.00 | 1.00 | 2.51 | 1.52 | 1.31 |
| Cd209d | 1.00 | 1.00 | 1.00 | 1.00 | 1.00 | 1.00 | 0.81 | 10.08 | 0.93 | 2.28 | 1.08 | 1.00 |
| Cd320 | 1.05 | 1.08 | 0.88 | 0.99 | 0.63 | 0.72 | 1.51 | 7.30 | 1.42 | 1.77 | 0.70 | 0.68 |
| Cd55 | 1.00 | 1.00 | 0.85 | 1.32 | 1.00 | 1.01 | 1.15 | 0.10 | 1.27 | 0.33 | 0.59 | 0.73 |

Fig. 35-141

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Cd5l | 1.00 | 1.00 | 1.00 | 1.00 | 1.00 | 1.00 | 1.00 | 1.00 | 1.00 | 1.00 | 1.00 | 1.00 |
| Cd63 | 1.43 | 0.73 | 0.99 | 0.48 | 5.95 | 1.76 | 0.83 | 0.81 | 1.19 | 1.73 | 1.82 | 0.94 |
| Cd72 | 1.00 | 0.10 | 1.00 | 1.00 | 1.82 | 1.00 | 1.00 | 1.00 | 1.00 | 7.65 | 3.37 | 1.08 |
| Cd82 | 3.39 | 3.11 | 2.17 | 1.83 | 6.64 | 2.73 | 0.78 | 0.91 | 0.79 | 1.42 | 1.53 | 0.99 |
| Cda | 1.00 | 0.23 | 0.70 | 1.00 | 1.00 | 1.00 | 1.33 | 1.30 | 0.57 | 1.78 | 3.37 | 1.00 |
| Cdc26 | 1.69 | 0.78 | 0.98 | 1.03 | 7.50 | 1.05 | 0.82 | 0.99 | 0.96 | 2.71 | 3.22 | 0.90 |
| Cdc34 | 1.35 | 0.65 | 0.86 | 0.25 | 6.91 | 0.93 | 0.74 | 0.67 | 0.79 | 3.06 | 4.72 | 1.08 |
| Cdc37 | 0.78 | 0.48 | 0.62 | 0.45 | 5.09 | 1.04 | 0.88 | 0.78 | 0.81 | 2.18 | 2.91 | 1.13 |
| Cdc42ep5 | 1.90 | 0.49 | 0.94 | 0.50 | 5.18 | 0.85 | 0.87 | 0.64 | 0.83 | 1.05 | 1.35 | 0.74 |
| Cdh16 | 1.00 | 1.00 | 1.00 | 1.00 | 1.00 | 1.00 | 0.85 | 1.01 | 1.61 | 1.80 | 1.33 | 0.65 |
| Cdk10 | 1.12 | 0.56 | 0.75 | 0.73 | 6.53 | 0.86 | 1.00 | 0.95 | 0.69 | 1.52 | 2.32 | 1.02 |
| Cdk11b | 1.24 | 0.64 | 1.05 | 0.65 | 4.62 | 1.09 | 1.11 | 1.12 | 1.09 | 2.29 | 3.05 | 1.02 |
| Cdk20 | 0.89 | 1.04 | 0.89 | 1.81 | 6.44 | 1.08 | 2.01 | 1.42 | 0.86 | 2.05 | 1.32 | 1.10 |
| Cdk5r2 | 1.00 | 1.00 | 1.00 | 1.00 | 0.12 | 1.00 | 1.00 | 1.00 | 1.00 | 1.00 | 1.00 | 1.00 |
| Cdk5rap3 | 0.88 | 0.57 | 0.74 | 0.52 | 9.11 | 1.19 | 1.00 | 0.82 | 0.93 | 2.07 | 3.17 | 0.95 |
| Cdkn1a | 5.32 | 6.38 | 7.91 | 1.14 | 2.63 | 2.15 | 2.73 | 3.10 | 2.46 | 4.00 | 5.13 | 3.53 |
| Cdo1 | 2.04 | 2.90 | 4.28 | 1.61 | 2.22 | 1.44 | 9.84 | 6.27 | 4.40 | 1.53 | 1.33 | 1.20 |
| Cdpf1 | 1.45 | 1.07 | 1.21 | 3.99 | 21.45 | 4.43 | 1.62 | 1.47 | 0.87 | 0.90 | 1.88 | 1.18 |
| Ceacam12 | 1.00 | 1.00 | 1.00 | 1.00 | 1.00 | 1.00 | 1.00 | 1.00 | 1.00 | 1.00 | 1.00 | 1.00 |
| Cebpd | 3.00 | 4.59 | 4.31 | 2.64 | 3.55 | 2.02 | 2.05 | 1.63 | 1.59 | 0.42 | 0.93 | 1.34 |
| Cebpe | 1.00 | 1.00 | 1.00 | 1.00 | 1.00 | 1.00 | 1.00 | 1.00 | 1.00 | 0.92 | 0.97 | 0.80 |
| Cel | 1.00 | 1.00 | 1.00 | 1.00 | 1.00 | 1.00 | 1.00 | 1.00 | 1.00 | 1.00 | 1.00 | 1.66 |
| Cela1 | 1.00 | 1.00 | 1.00 | 1.15 | 5.01 | 1.28 | 1.00 | 1.40 | 2.30 | 2.41 | 4.13 | 1.76 |
| Cela2a | 1.00 | 1.00 | 1.00 | 1.00 | 1.00 | 1.00 | 1.00 | 1.00 | 1.00 | 1.00 | 1.00 | 2.41 |
| Cela3b | 1.00 | 1.00 | 1.00 | 1.00 | 1.00 | 1.00 | 1.00 | 1.00 | 1.00 | 1.00 | 1.00 | 1.32 |
| Celf4 | 1.00 | 1.00 | 1.00 | 1.00 | 0.13 | 1.00 | 1.00 | 1.00 | 1.00 | 1.00 | 1.00 | 1.00 |
| Celf5 | 1.00 | 1.00 | 1.00 | 1.00 | 0.31 | 1.00 | 1.00 | 1.00 | 1.00 | 1.00 | 1.00 | 1.00 |
| Cend1 | 1.00 | 1.00 | 1.02 | 0.57 | 1.10 | 0.76 | 1.01 | 0.70 | 0.67 | 1.00 | 2.64 | 1.00 |
| Cenpo | 0.93 | 1.64 | 1.43 | 1.48 | 25.87 | 4.51 | 0.86 | 0.77 | 1.06 | 0.93 | 1.68 | 1.01 |
| Cenpv | 1.21 | 0.64 | 0.98 | 0.52 | 6.63 | 1.24 | 0.91 | 0.61 | 0.79 | 1.80 | 2.39 | 1.03 |
| Cep63 | 0.59 | 0.38 | 0.52 | 0.39 | 2.99 | 0.68 | 0.87 | 0.82 | 0.78 | 2.75 | 2.55 | 0.86 |
| Cep89 | 0.82 | 0.78 | 0.91 | 1.26 | 7.14 | 1.38 | 0.99 | 0.98 | 0.89 | 2.70 | 2.96 | 0.77 |
| Cers4 | 1.17 | 0.59 | 1.14 | 1.05 | 3.55 | 1.58 | 0.65 | 0.68 | 0.84 | 1.90 | 2.06 | 0.82 |
| Ces1d | 0.75 | 0.79 | 0.78 | 0.40 | 2.95 | 0.59 | 0.41 | 0.45 | 0.39 | 2.03 | 3.14 | 1.10 |
| Ces2h | 1.00 | 1.00 | 1.00 | 1.00 | 1.00 | 1.00 | 1.00 | 1.00 | 1.00 | 1.00 | 1.00 | 1.00 |
| Cetn1 | 1.00 | 1.00 | 1.00 | 1.00 | 1.00 | 1.00 | 1.00 | 1.00 | 1.00 | 1.00 | 1.00 | 1.00 |
| Cfb | 1.36 | 0.96 | 2.00 | 1.10 | 4.01 | 1.87 | 1.00 | 1.00 | 1.67 | 1.59 | 3.73 | 1.06 |
| Cfd | 1.61 | 1.38 | 2.87 | 0.44 | 17.57 | 4.11 | 1.06 | 2.18 | 5.97 | 0.91 | 3.11 | 1.70 |
| Cfdp1 | 1.20 | 0.85 | 1.14 | 1.00 | 3.13 | 1.04 | 1.00 | 0.93 | 0.89 | 1.00 | 1.54 | 0.97 |
| Cfp | 2.31 | 0.68 | 1.52 | 0.57 | 4.51 | 1.07 | 0.99 | 1.08 | 1.49 | 2.92 | 3.24 | 1.04 |
| Cgref1 | 2.49 | 1.58 | 1.57 | 1.00 | 0.98 | 1.00 | 1.15 | 0.70 | 1.36 | 2.45 | 1.26 | 0.97 |
| Chac1 | 1.35 | 2.20 | 1.32 | 3.87 | 3.76 | 5.38 | 3.28 | 2.45 | 1.17 | 1.20 | 0.60 | 1.09 |
| Chaf1b | 1.00 | 1.00 | 1.00 | 1.00 | 1.38 | 1.00 | 1.00 | 1.00 | 1.00 | 2.63 | 3.28 | 0.84 |
| Chchd1 | 1.22 | 0.60 | 0.90 | 0.93 | 7.56 | 0.79 | 0.98 | 0.81 | 0.87 | 1.98 | 3.32 | 0.98 |
| Chchd10 | 1.29 | 0.73 | 0.88 | 0.38 | 5.76 | 1.32 | 1.26 | 0.81 | 0.78 | 2.38 | 2.62 | 0.94 |
| Chchd2 | 1.26 | 0.71 | 0.87 | 0.39 | 5.14 | 1.09 | 0.91 | 0.83 | 0.84 | 1.66 | 2.49 | 0.93 |
| Chchd6 | 1.04 | 0.70 | 1.00 | 0.35 | 6.33 | 1.07 | 1.06 | 1.20 | 1.04 | 2.01 | 3.01 | 0.93 |
| Chchd7 | 1.54 | 0.72 | 0.81 | 0.31 | 7.97 | 1.07 | 1.70 | 0.93 | 1.13 | 2.16 | 2.89 | 0.98 |
| Chga | 1.00 | 1.00 | 1.00 | 1.00 | 0.21 | 1.00 | 1.00 | 1.00 | 1.00 | 1.00 | 1.00 | 1.00 |
| Chgb | 1.00 | 1.00 | 1.00 | 1.00 | 0.08 | 1.00 | 1.00 | 1.00 | 1.00 | 1.00 | 1.00 | 1.00 |
| Chia1 | 0.91 | 1.00 | 1.00 | 1.00 | 1.00 | 1.00 | 1.00 | 1.00 | 1.00 | 1.27 | 3.22 | 1.48 |
| Chic2 | 1.72 | 1.40 | 1.49 | 1.24 | 1.05 | 1.16 | 0.99 | 1.34 | 1.13 | 0.46 | 0.80 | 1.10 |
| Chil1 | 1.00 | 1.00 | 1.00 | 1.00 | 1.00 | 1.00 | 1.02 | 0.85 | 2.27 | 0.91 | 1.75 | 1.16 |
| Chil3 | 1.00 | 1.00 | 1.00 | 1.00 | 1.00 | 1.00 | 1.00 | 1.00 | 1.00 | 2.21 | 4.74 | 2.00 |
| Chil4 | 1.00 | 1.00 | 1.00 | 1.00 | 1.00 | 1.00 | 1.00 | 1.00 | 1.00 | 0.83 | 1.00 | 1.14 |
| Chkb | 1.25 | 0.56 | 1.31 | 0.58 | 5.30 | 1.00 | 0.84 | 0.72 | 0.88 | 2.77 | 4.25 | 1.04 |
| Chmp2a | 1.26 | 0.73 | 0.91 | 0.48 | 5.71 | 0.91 | 1.03 | 0.89 | 0.81 | 2.22 | 2.40 | 1.03 |
| Chmp3 | 1.10 | 1.57 | 1.07 | 0.88 | 0.80 | 0.85 | 0.81 | 0.79 | 0.85 | 0.67 | 0.63 | 0.91 |
| Chn1 | 1.22 | 1.00 | 1.00 | 0.42 | 0.11 | 0.59 | 1.03 | 1.08 | 0.96 | 0.22 | 0.53 | 0.77 |
| Chrne | 0.82 | 0.54 | 0.60 | 1.00 | 1.00 | 1.00 | 1.00 | 1.00 | 1.00 | 1.00 | 1.00 | 1.00 |
| Chst2 | 1.00 | 1.00 | 1.00 | 1.19 | 0.46 | 1.15 | 1.00 | 1.00 | 0.94 | 0.38 | 0.30 | 0.78 |
| Churc1 | 1.26 | 0.87 | 0.98 | 0.50 | 4.96 | 0.95 | 0.98 | 0.82 | 0.77 | 2.66 | 2.07 | 0.79 |
| Cib1 | 1.10 | 0.64 | 1.13 | 0.29 | 6.00 | 0.99 | 1.19 | 0.77 | 0.83 | 2.14 | 2.53 | 1.02 |
| Cib3 | 1.00 | 1.00 | 1.00 | 1.00 | 1.00 | 1.00 | 1.00 | 1.00 | 0.77 | 1.00 | 1.24 | 1.00 |

Fig. 35- 142

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Cd5l | 6.09 | 7.63 | 9.82 | 1.00 | 1.00 | 1.00 | 0.61 | 0.67 | 0.76 | 1.00 | 1.00 | 1.00 |
| Cd63 | 2.06 | 2.10 | 1.71 | 0.83 | 0.62 | 0.78 | 1.00 | 2.99 | 1.03 | 1.04 | 1.42 | 1.05 |
| Cd72 | 1.47 | 2.30 | 3.15 | 1.00 | 0.43 | 1.00 | 1.00 | 4.82 | 1.00 | 1.04 | 0.67 | 1.43 |
| Cd82 | 1.28 | 1.38 | 1.28 | 0.88 | 0.87 | 0.94 | 0.93 | 1.23 | 0.96 | 0.92 | 1.11 | 0.95 |
| Cda | 1.00 | 1.00 | 1.00 | 0.85 | 0.74 | 0.89 | 1.02 | 0.63 | 0.94 | 0.91 | 1.53 | 1.05 |
| Cdc26 | 1.18 | 1.47 | 0.87 | 0.92 | 0.66 | 0.71 | 1.22 | 2.18 | 0.99 | 1.15 | 1.65 | 0.95 |
| Cdc34 | 1.24 | 1.53 | 0.93 | 1.02 | 0.60 | 1.16 | 1.13 | 2.31 | 1.13 | 1.24 | 1.71 | 1.02 |
| Cdc37 | 1.17 | 1.44 | 1.17 | 0.89 | 0.76 | 1.07 | 1.02 | 1.29 | 0.94 | 1.03 | 1.70 | 1.14 |
| Cdc42ep5 | 2.68 | 1.60 | 1.01 | 1.04 | 0.96 | 0.99 | 5.52 | 6.14 | 3.94 | 1.13 | 1.60 | 1.10 |
| Cdh16 | 1.00 | 1.00 | 1.00 | 1.06 | 0.79 | 1.05 | 1.00 | 1.00 | 1.00 | 1.00 | 1.00 | 1.00 |
| Cdk10 | 1.30 | 1.76 | 1.00 | 0.81 | 0.96 | 1.05 | 0.83 | 1.11 | 0.73 | 0.85 | 1.55 | 1.03 |
| Cdk11b | 1.17 | 1.13 | 0.92 | 1.05 | 0.61 | 0.97 | 1.09 | 1.81 | 0.97 | 0.99 | 1.25 | 0.97 |
| Cdk20 | 0.83 | 1.06 | 0.80 | 1.22 | 2.21 | 0.74 | 0.68 | 1.22 | 0.93 | 0.68 | 1.19 | 0.76 |
| Cdk5r2 | 1.00 | 1.00 | 1.00 | 1.00 | 1.00 | 1.00 | 1.00 | 1.00 | 1.00 | 1.44 | 1.14 | 1.47 |
| Cdk5rap3 | 1.43 | 1.79 | 0.97 | 0.92 | 0.72 | 0.86 | 1.08 | 1.78 | 1.17 | 1.01 | 1.77 | 1.19 |
| Cdkn1a | 1.44 | 1.47 | 1.25 | 4.80 | 5.92 | 2.77 | 8.96 | 9.73 | 8.40 | 1.07 | 1.23 | 1.02 |
| Cdo1 | 3.01 | 2.62 | 1.25 | 1.20 | 0.95 | 0.95 | 1.17 | 1.89 | 1.13 | 1.18 | 1.19 | 1.01 |
| Cdpf1 | 1.03 | 1.55 | 0.98 | 1.10 | 1.41 | 0.89 | 0.83 | 1.06 | 0.55 | 1.06 | 1.62 | 1.02 |
| Ceacam12 | 1.00 | 1.00 | 1.00 | 1.00 | 1.00 | 1.00 | 1.00 | 1.00 | 1.00 | 5.23 | 7.63 | 6.47 |
| Cebpd | 7.84 | 6.98 | 2.35 | 4.12 | 10.97 | 1.69 | 3.01 | 0.88 | 2.30 | 1.30 | 1.74 | 1.25 |
| Cebpe | 0.68 | 1.00 | 1.00 | 1.00 | 1.00 | 1.00 | 1.00 | 1.00 | 1.00 | 1.00 | 1.00 | 1.00 |
| Cel | 1.00 | 1.00 | 1.38 | 1.00 | 1.00 | 0.87 | 1.00 | 1.00 | 0.94 | 0.34 | 1.50 | 23.94 |
| Cela1 | 1.88 | 2.33 | 1.73 | 0.73 | 0.82 | 0.98 | 0.92 | 1.51 | 0.62 | 0.67 | 2.31 | 3.71 |
| Cela2a | 1.00 | 1.00 | 2.68 | 1.00 | 1.00 | 0.95 | 1.00 | 1.00 | 0.87 | 0.52 | 3.09 | 35.16 |
| Cela3b | 1.00 | 1.00 | 1.00 | 1.00 | 1.00 | 0.87 | 1.00 | 1.00 | 0.74 | 0.43 | 3.09 | 23.07 |
| Celf4 | 1.00 | 1.00 | 1.00 | 1.00 | 1.00 | 1.00 | 1.00 | 1.00 | 1.00 | 1.52 | 1.06 | 1.26 |
| Celf5 | 0.99 | 1.00 | 1.00 | 1.00 | 1.00 | 1.00 | 1.00 | 1.00 | 1.00 | 1.03 | 1.00 | 1.14 |
| Cend1 | 0.78 | 1.00 | 0.69 | 1.00 | 1.52 | 1.00 | 4.34 | 31.73 | 1.00 | 0.86 | 1.40 | 1.26 |
| Cenpo | 0.92 | 0.99 | 0.95 | 1.01 | 0.64 | 0.76 | 1.00 | 1.00 | 1.00 | 1.13 | 1.19 | 0.97 |
| Cenpv | 1.07 | 1.01 | 0.70 | 0.94 | 0.90 | 1.00 | 1.01 | 1.22 | 1.12 | 1.22 | 1.79 | 1.08 |
| Cep63 | 1.40 | 1.42 | 1.08 | 0.92 | 0.64 | 1.18 | 1.15 | 2.90 | 0.94 | 0.87 | 1.38 | 1.07 |
| Cep89 | 0.99 | 1.32 | 1.02 | 1.12 | 0.77 | 1.21 | 1.07 | 2.32 | 1.41 | 1.05 | 1.91 | 1.03 |
| Cers4 | 1.94 | 2.37 | 1.11 | 0.77 | 0.55 | 1.09 | 0.90 | 1.04 | 1.00 | 1.06 | 1.50 | 1.15 |
| Ces1d | 0.76 | 1.03 | 0.49 | 0.48 | 0.51 | 0.56 | 0.20 | 0.42 | 0.51 | 1.00 | 1.54 | 0.93 |
| Ces2h | 1.00 | 1.00 | 1.00 | 25.96 | 2.75 | 14.09 | 10.81 | 2.42 | 18.76 | 4.16 | 1.36 | 3.79 |
| Cetn1 | 1.00 | 1.00 | 1.00 | 1.00 | 1.00 | 1.00 | 1.00 | 1.00 | 1.00 | 1.00 | 1.00 | 1.00 |
| Cfb | 1.96 | 1.57 | 2.49 | 0.88 | 0.51 | 0.87 | 0.70 | 1.36 | 0.81 | 1.18 | 1.08 | 1.09 |
| Cfd | 1.00 | 2.03 | 1.07 | 0.45 | 0.80 | 1.82 | 1.05 | 2.08 | 2.23 | 1.36 | 6.22 | 2.00 |
| Cfdp1 | 1.04 | 1.14 | 0.88 | 0.88 | 0.90 | 0.98 | 1.09 | 0.81 | 1.05 | 1.07 | 1.53 | 1.22 |
| Cfp | 2.05 | 2.21 | 2.28 | 1.14 | 0.73 | 1.03 | 1.00 | 2.92 | 1.22 | 0.85 | 1.61 | 0.93 |
| Cgref1 | 1.00 | 1.00 | 1.00 | 1.13 | 1.06 | 1.01 | 10.37 | 3.73 | 7.31 | 1.15 | 1.51 | 0.99 |
| Chac1 | 1.48 | 1.18 | 1.52 | 6.06 | 1.88 | 0.89 | 1.04 | 1.00 | 0.59 | 2.26 | 2.13 | 1.42 |
| Chaf1b | 0.66 | 0.86 | 0.52 | 0.59 | 0.66 | 0.95 | 1.14 | 14.08 | 1.00 | 1.19 | 1.67 | 0.99 |
| Chchd1 | 1.00 | 1.48 | 0.78 | 0.95 | 0.67 | 0.79 | 0.88 | 1.21 | 0.87 | 1.01 | 1.58 | 1.07 |
| Chchd10 | 1.17 | 1.43 | 0.81 | 0.87 | 0.71 | 1.06 | 1.01 | 1.87 | 0.95 | 1.02 | 1.48 | 1.02 |
| Chchd2 | 1.08 | 1.40 | 0.91 | 0.85 | 0.78 | 0.98 | 1.09 | 1.08 | 0.95 | 1.03 | 1.62 | 1.02 |
| Chchd6 | 0.72 | 1.21 | 0.84 | 0.66 | 0.55 | 0.72 | 0.58 | 0.77 | 0.82 | 1.80 | 1.83 | 0.78 |
| Chchd7 | 1.06 | 1.31 | 1.22 | 0.99 | 0.90 | 1.36 | 1.46 | 2.92 | 1.20 | 1.28 | 1.59 | 1.14 |
| Chga | 1.41 | 2.73 | 0.54 | 1.00 | 1.00 | 1.00 | 1.00 | 1.00 | 1.00 | 1.39 | 1.77 | 1.18 |
| Chgb | 1.14 | 1.00 | 3.50 | 1.00 | 1.00 | 1.00 | 1.00 | 1.00 | 1.00 | 1.79 | 1.98 | 1.70 |
| Chia1 | 1.06 | 1.00 | 1.00 | 1.09 | 1.00 | 0.70 | 1.19 | 3.41 | 1.47 | 1.00 | 1.00 | 0.88 |
| Chic2 | 0.82 | 1.14 | 1.06 | 0.98 | 2.77 | 1.00 | 1.56 | 0.97 | 1.59 | 1.03 | 1.09 | 1.08 |
| Chil1 | 0.48 | 0.93 | 0.96 | 1.00 | 1.00 | 1.00 | 1.00 | 1.00 | 1.00 | 0.77 | 0.55 | 0.64 |
| Chil3 | 0.30 | 1.00 | 1.00 | 1.00 | 1.00 | 1.00 | 1.00 | 1.00 | 1.00 | 1.00 | 1.00 | 1.00 |
| Chil4 | 1.00 | 1.00 | 1.00 | 1.00 | 1.00 | 1.00 | 1.00 | 1.00 | 1.00 | 1.00 | 1.00 | 1.00 |
| Chkb | 1.23 | 1.58 | 1.18 | 0.78 | 0.60 | 1.10 | 1.85 | 2.68 | 1.54 | 0.99 | 1.10 | 0.97 |
| Chmp2a | 1.20 | 1.33 | 1.07 | 0.83 | 0.59 | 0.82 | 1.13 | 1.60 | 0.81 | 0.99 | 1.53 | 1.07 |
| Chmp3 | 1.00 | 0.96 | 1.15 | 0.81 | 1.48 | 0.87 | 0.65 | 0.50 | 0.59 | 0.80 | 0.84 | 0.83 |
| Chn1 | 1.00 | 1.00 | 1.00 | 0.83 | 1.69 | 1.10 | 1.00 | 1.00 | 1.00 | 1.28 | 0.84 | 0.87 |
| Chrne | 1.00 | 1.00 | 1.00 | 1.00 | 1.00 | 1.00 | 1.00 | 1.00 | 1.00 | 1.00 | 1.00 | 1.00 |
| Chst2 | 0.82 | 0.85 | 1.06 | 1.27 | 1.07 | 1.17 | 1.00 | 1.00 | 1.00 | 0.79 | 0.69 | 0.86 |
| Churc1 | 1.45 | 1.89 | 0.95 | 0.91 | 0.57 | 0.91 | 1.21 | 1.70 | 0.89 | 0.90 | 1.60 | 1.15 |
| Cib1 | 1.24 | 1.36 | 0.78 | 0.98 | 0.78 | 0.95 | 1.05 | 1.26 | 0.86 | 1.12 | 1.64 | 1.06 |
| Cib3 | 1.46 | 1.00 | 0.91 | 1.00 | 1.00 | 1.00 | 1.00 | 1.00 | 1.00 | 1.71 | 2.55 | 1.19 |

Fig. 35- 143

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Cd5l | 1.00 | 1.00 | 1.00 | 1.00 | 1.00 | 1.00 | 1.00 | 1.00 | 1.00 | 0.50 | 0.72 | 0.46 |
| Cd63 | 0.87 | 1.04 | 0.84 | 0.95 | 1.24 | 1.07 | 1.09 | 1.10 | 0.82 | 1.05 | 1.16 | 0.70 |
| Cd72 | 1.02 | 1.00 | 1.00 | 1.00 | 8.76 | 0.77 | 1.00 | 4.68 | 1.00 | 0.84 | 0.67 | 0.80 |
| Cd82 | 0.82 | 0.82 | 0.82 | 1.94 | 7.51 | 1.98 | 0.91 | 1.03 | 0.85 | 0.73 | 0.86 | 0.76 |
| Cda | 1.83 | 0.96 | 1.30 | 0.72 | 5.39 | 1.50 | 1.00 | 1.26 | 1.00 | 1.00 | 1.00 | 1.00 |
| Cdc26 | 1.09 | 0.95 | 0.93 | 0.97 | 2.80 | 1.14 | 0.86 | 2.54 | 0.83 | 1.18 | 1.57 | 0.89 |
| Cdc34 | 0.89 | 0.95 | 1.02 | 1.01 | 2.40 | 1.29 | 0.81 | 5.32 | 1.05 | 1.11 | 1.37 | 0.87 |
| Cdc37 | 1.13 | 1.26 | 1.09 | 1.06 | 2.91 | 1.18 | 1.03 | 1.86 | 1.04 | 1.10 | 1.55 | 1.24 |
| Cdc42ep5 | 0.95 | 1.31 | 0.83 | 3.09 | 5.27 | 1.04 | 0.65 | 0.79 | 1.26 | 0.89 | 1.28 | 0.83 |
| Cdh16 | 1.00 | 1.00 | 1.00 | 1.45 | 6.60 | 3.52 | 1.00 | 1.00 | 1.00 | 1.00 | 1.00 | 1.00 |
| Cdk10 | 0.89 | 1.03 | 1.23 | 0.78 | 2.37 | 1.16 | 0.89 | 1.48 | 1.02 | 1.18 | 1.21 | 0.89 |
| Cdk11b | 1.08 | 1.07 | 0.89 | 1.02 | 2.58 | 1.20 | 1.09 | 2.60 | 1.05 | 1.05 | 1.13 | 0.99 |
| Cdk20 | 0.86 | 0.60 | 0.82 | 1.42 | 2.67 | 0.76 | 0.94 | 1.77 | 1.09 | 1.01 | 1.51 | 0.99 |
| Cdk5r2 | 1.34 | 1.19 | 1.14 | 1.00 | 1.00 | 1.00 | 1.00 | 1.00 | 1.00 | 1.00 | 12.92 | 1.00 |
| Cdk5rap3 | 1.20 | 1.00 | 1.12 | 0.93 | 1.79 | 0.87 | 1.00 | 2.46 | 1.06 | 1.09 | 1.39 | 1.04 |
| Cdkn1a | 0.89 | 0.94 | 0.67 | 6.17 | 12.87 | 4.29 | 0.95 | 1.34 | 1.00 | 2.61 | 2.90 | 1.30 |
| Cdo1 | 1.36 | 1.39 | 1.97 | 1.16 | 2.55 | 1.71 | 1.72 | 1.64 | 1.41 | 1.60 | 3.53 | 1.51 |
| Cdpf1 | 1.10 | 1.20 | 1.22 | 1.04 | 8.32 | 0.96 | 0.93 | 0.74 | 0.91 | 1.20 | 1.18 | 1.12 |
| Ceacam12 | 1.00 | 1.00 | 1.00 | 1.00 | 1.00 | 1.00 | 1.00 | 1.00 | 1.00 | 1.00 | 1.00 | 1.00 |
| Cebpd | 2.16 | 3.34 | 2.03 | 1.65 | 1.02 | 1.38 | 1.11 | 0.59 | 1.24 | 1.74 | 2.71 | 1.92 |
| Cebpe | 1.00 | 1.00 | 1.00 | 1.00 | 1.00 | 1.00 | 1.00 | 1.00 | 1.00 | 6.81 | 3.22 | 1.85 |
| Cel | 22.61 | 1.31 | 2.14 | 1.00 | 1.00 | 0.71 | 1.00 | 1.34 | 1.65 | 1.14 | 6.81 | 0.60 |
| Cela1 | 2.44 | 2.01 | 3.09 | 1.77 | 3.57 | 0.77 | 1.00 | 2.53 | 0.89 | 0.90 | 4.87 | 0.66 |
| Cela2a | 50.20 | 1.92 | 3.18 | 1.00 | 1.00 | 0.77 | 1.00 | 1.43 | 1.26 | 2.37 | 15.22 | 0.80 |
| Cela3b | 31.52 | 2.50 | 2.84 | 1.00 | 1.00 | 0.79 | 1.00 | 1.77 | 1.69 | 1.70 | 14.92 | 0.97 |
| Celf4 | 0.94 | 0.93 | 0.91 | 1.12 | 1.00 | 1.15 | 0.88 | 1.40 | 0.97 | 0.92 | 8.30 | 0.68 |
| Celf5 | 1.00 | 1.00 | 1.00 | 1.00 | 1.00 | 1.00 | 1.07 | 1.61 | 1.09 | 1.00 | 6.06 | 1.00 |
| Cend1 | 0.90 | 1.09 | 1.12 | 1.00 | 1.00 | 1.25 | 1.00 | 1.00 | 1.00 | 1.00 | 25.03 | 1.00 |
| Cenpo | 1.04 | 0.97 | 1.04 | 0.89 | 4.33 | 0.95 | 0.94 | 0.62 | 1.18 | 1.09 | 1.07 | 1.00 |
| Cenpv | 0.98 | 0.79 | 1.00 | 1.08 | 2.99 | 1.33 | 0.91 | 1.24 | 0.94 | 0.71 | 1.31 | 0.69 |
| Cep63 | 1.03 | 1.15 | 0.86 | 1.11 | 3.15 | 1.24 | 0.85 | 2.67 | 0.87 | 1.21 | 1.51 | 1.44 |
| Cep89 | 0.88 | 0.82 | 0.85 | 0.94 | 2.20 | 1.50 | 1.02 | 2.48 | 1.06 | 1.01 | 1.14 | 0.61 |
| Cers4 | 0.98 | 1.06 | 1.06 | 0.83 | 2.05 | 1.01 | 1.00 | 1.00 | 1.00 | 0.82 | 0.81 | 0.99 |
| Ces1d | 0.71 | 0.85 | 0.96 | 0.50 | 1.76 | 0.89 | 0.60 | 0.90 | 0.57 | 1.00 | 1.00 | 1.00 |
| Ces2h | 1.00 | 1.00 | 1.16 | 1.00 | 1.00 | 1.00 | 1.00 | 6.83 | 1.00 | 1.00 | 1.00 | 1.00 |
| Cetn1 | 1.00 | 1.00 | 1.00 | 3.80 | 1.00 | 1.00 | 0.87 | 0.76 | 0.90 | 1.00 | 1.00 | 1.00 |
| Cfb | 2.59 | 2.26 | 2.10 | 1.03 | 2.37 | 0.84 | 1.00 | 1.00 | 1.00 | 1.28 | 1.23 | 1.20 |
| Cfd | 1.42 | 1.95 | 2.15 | 0.85 | 3.29 | 2.57 | 1.24 | 4.76 | 1.39 | 0.60 | 3.43 | 1.80 |
| Cfdp1 | 0.86 | 0.72 | 0.99 | 1.15 | 5.72 | 1.21 | 0.96 | 1.03 | 0.98 | 1.25 | 1.23 | 1.02 |
| Cfp | 1.24 | 1.82 | 1.78 | 0.96 | 1.94 | 1.05 | 1.00 | 2.97 | 0.87 | 0.98 | 1.61 | 1.04 |
| Cgref1 | 0.79 | 0.66 | 0.96 | 1.15 | 0.89 | 1.01 | 1.00 | 1.00 | 1.00 | 1.00 | 1.68 | 1.05 |
| Chac1 | 2.07 | 2.38 | 1.75 | 4.96 | 3.89 | 4.07 | 0.90 | 0.95 | 0.84 | 1.20 | 2.98 | 0.86 |
| Chaf1b | 0.46 | 0.66 | 0.63 | 1.00 | 1.14 | 0.74 | 1.08 | 5.07 | 1.11 | 0.62 | 0.90 | 0.57 |
| Chchd1 | 0.86 | 1.09 | 0.97 | 1.15 | 2.38 | 1.12 | 0.89 | 1.88 | 0.86 | 1.23 | 1.35 | 1.03 |
| Chchd10 | 0.98 | 1.25 | 1.13 | 1.57 | 4.04 | 3.25 | 0.82 | 1.94 | 0.89 | 0.90 | 1.53 | 0.69 |
| Chchd2 | 0.97 | 1.08 | 0.86 | 1.04 | 4.46 | 1.15 | 0.85 | 1.25 | 0.97 | 1.15 | 1.23 | 0.94 |
| Chchd6 | 1.29 | 1.76 | 1.00 | 1.02 | 1.86 | 1.00 | 0.93 | 2.68 | 1.03 | 0.84 | 1.29 | 0.97 |
| Chchd7 | 1.16 | 1.74 | 1.73 | 1.10 | 4.43 | 0.92 | 0.87 | 2.41 | 0.89 | 1.03 | 1.05 | 0.85 |
| Chga | 1.16 | 1.63 | 1.27 | 1.00 | 1.00 | 1.00 | 0.58 | 0.40 | 0.78 | 1.00 | 9.48 | 1.00 |
| Chgb | 1.20 | 1.54 | 1.14 | 1.00 | 1.00 | 1.00 | 1.19 | 1.71 | 1.01 | 1.00 | 20.91 | 1.00 |
| Chia1 | 1.17 | 1.50 | 1.46 | 0.82 | 1.01 | 0.47 | 1.08 | 1.00 | 0.56 | 1.00 | 1.00 | 1.08 |
| Chic2 | 1.05 | 1.27 | 1.12 | 1.82 | 6.16 | 1.23 | 0.84 | 0.53 | 1.05 | 1.01 | 0.90 | 0.93 |
| Chil1 | 1.26 | 1.00 | 1.27 | 1.00 | 1.00 | 1.00 | 1.00 | 1.00 | 1.00 | 5.18 | 2.61 | 1.29 |
| Chil3 | 1.00 | 1.00 | 1.00 | 1.00 | 1.00 | 1.00 | 1.00 | 1.03 | 1.00 | 28.15 | 14.07 | 9.63 |
| Chil4 | 1.00 | 8.62 | 50.55 | 1.00 | 1.00 | 1.00 | 1.00 | 1.00 | 1.00 | 1.00 | 1.00 | 1.00 |
| Chkb | 1.21 | 1.41 | 1.17 | 1.09 | 4.27 | 1.17 | 1.11 | 2.38 | 1.14 | 1.14 | 1.20 | 1.10 |
| Chmp2a | 0.87 | 0.91 | 0.87 | 1.01 | 2.22 | 0.89 | 0.94 | 2.70 | 1.06 | 0.94 | 1.08 | 0.88 |
| Chmp3 | 0.75 | 0.70 | 0.78 | 0.83 | 0.41 | 0.93 | 0.90 | 0.71 | 0.95 | 0.92 | 0.87 | 0.98 |
| Chn1 | 0.71 | 0.86 | 1.15 | 0.70 | 0.95 | 0.80 | 1.21 | 1.21 | 0.89 | 1.00 | 20.76 | 1.00 |
| Chrne | 1.00 | 1.00 | 1.00 | 1.00 | 1.00 | 1.00 | 1.06 | 2.13 | 1.21 | 1.00 | 1.00 | 1.00 |
| Chst2 | 0.98 | 1.17 | 1.54 | 1.69 | 1.00 | 1.74 | 1.00 | 1.00 | 1.00 | 0.44 | 0.85 | 0.56 |
| Churc1 | 1.15 | 1.08 | 1.00 | 0.92 | 2.79 | 1.12 | 0.85 | 4.19 | 0.96 | 1.01 | 1.33 | 0.89 |
| Cib1 | 0.76 | 1.00 | 0.77 | 1.16 | 4.11 | 1.21 | 0.83 | 1.28 | 1.07 | 1.10 | 1.26 | 0.83 |
| Cib3 | 1.00 | 1.00 | 1.00 | 1.00 | 1.00 | 1.00 | 1.00 | 1.00 | 1.00 | 1.00 | 1.00 | 1.00 |

Fig. 35- 144

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Cd5l | 1.00 | 1.00 | 1.00 | 1.00 | 1.00 | 1.00 | 1.00 | 1.00 | 1.00 | 0.38 | 0.82 | 0.17 |
| Cd63 | 0.94 | 0.66 | 1.11 | 1.09 | 1.01 | 1.21 | 1.32 | 3.08 | 1.10 | 2.00 | 1.17 | 1.37 |
| Cd72 | 1.00 | 1.00 | 1.00 | 1.00 | 1.50 | 1.00 | 0.80 | 17.77 | 1.15 | 1.50 | 0.77 | 1.02 |
| Cd82 | 0.74 | 0.82 | 0.71 | 1.02 | 1.05 | 1.05 | 0.98 | 1.52 | 0.73 | 0.99 | 0.95 | 0.94 |
| Cda | 1.00 | 1.00 | 1.00 | 0.79 | 0.88 | 0.83 | 1.00 | 1.55 | 1.00 | 1.00 | 1.00 | 1.00 |
| Cdc26 | 1.20 | 0.78 | 1.38 | 0.97 | 0.75 | 1.30 | 1.15 | 10.00 | 0.93 | 2.89 | 1.26 | 1.13 |
| Cdc34 | 1.13 | 1.13 | 1.00 | 1.25 | 0.93 | 1.08 | 1.56 | 13.03 | 1.06 | 2.87 | 1.06 | 1.07 |
| Cdc37 | 1.04 | 1.31 | 1.08 | 1.20 | 1.04 | 1.06 | 1.02 | 4.05 | 0.83 | 2.56 | 1.17 | 1.20 |
| Cdc42ep5 | 1.41 | 1.68 | 1.03 | 0.64 | 1.09 | 1.67 | 1.07 | 2.76 | 0.83 | 1.00 | 1.20 | 1.16 |
| Cdh16 | 1.00 | 1.00 | 1.00 | 1.00 | 1.00 | 1.00 | 1.00 | 1.00 | 1.00 | 1.00 | 1.00 | 1.00 |
| Cdk10 | 0.96 | 0.87 | 0.70 | 1.04 | 1.23 | 1.05 | 1.10 | 6.35 | 0.95 | 2.58 | 1.15 | 1.18 |
| Cdk11b | 0.87 | 1.21 | 1.71 | 1.03 | 0.87 | 1.03 | 1.18 | 5.75 | 1.13 | 2.64 | 1.30 | 0.93 |
| Cdk20 | 1.00 | 1.00 | 1.00 | 0.87 | 1.09 | 1.11 | 1.80 | 2.66 | 1.03 | 1.81 | 1.01 | 1.07 |
| Cdk5r2 | 1.00 | 1.00 | 1.00 | 1.17 | 0.85 | 1.08 | 1.00 | 1.00 | 1.00 | 1.00 | 1.00 | 1.00 |
| Cdk5rap3 | 0.83 | 1.10 | 1.01 | 1.08 | 0.92 | 1.01 | 1.11 | 9.29 | 0.97 | 2.97 | 1.25 | 1.09 |
| Cdkn1a | 12.90 | 11.38 | 2.38 | 2.10 | 1.72 | 1.81 | 2.22 | 2.99 | 1.72 | 1.20 | 1.22 | 0.99 |
| Cdo1 | 0.62 | 1.05 | 0.79 | 1.15 | 0.95 | 1.21 | 2.69 | 5.22 | 2.05 | 1.00 | 0.70 | 1.06 |
| Cdpf1 | 0.99 | 0.73 | 0.79 | 1.09 | 1.02 | 1.02 | 1.12 | 2.63 | 0.81 | 1.02 | 1.03 | 1.00 |
| Ceacam12 | 1.00 | 1.00 | 1.00 | 1.00 | 1.00 | 1.00 | 1.00 | 1.00 | 1.00 | 1.00 | 1.00 | 1.00 |
| Cebpd | 2.62 | 4.79 | 1.21 | 1.81 | 1.00 | 1.49 | 2.51 | 0.98 | 2.36 | 0.94 | 1.29 | 1.34 |
| Cebpe | 1.00 | 1.00 | 1.00 | 1.00 | 1.00 | 1.00 | 1.00 | 1.00 | 1.00 | 1.80 | 1.15 | 1.24 |
| Cel | 0.70 | 0.66 | 0.76 | 1.00 | 1.00 | 0.67 | 1.00 | 1.00 | 1.01 | 1.00 | 0.43 | 0.98 |
| Cela1 | 1.32 | 1.33 | 1.28 | 0.90 | 1.31 | 0.62 | 0.85 | 7.72 | 0.88 | 1.15 | 0.59 | 1.00 |
| Cela2a | 1.26 | 1.21 | 1.11 | 1.00 | 1.00 | 0.73 | 0.84 | 1.80 | 0.82 | 1.00 | 0.17 | 0.78 |
| Cela3b | 1.17 | 1.13 | 1.00 | 1.00 | 2.60 | 0.83 | 1.00 | 3.43 | 0.71 | 1.00 | 1.00 | 1.00 |
| Celf4 | 1.00 | 1.00 | 1.00 | 1.04 | 1.53 | 1.00 | 1.00 | 1.00 | 1.00 | 1.00 | 1.00 | 1.00 |
| Celf5 | 1.00 | 1.00 | 1.00 | 1.01 | 0.96 | 1.01 | 1.00 | 1.00 | 1.00 | 1.00 | 1.00 | 1.00 |
| Cend1 | 1.00 | 1.00 | 1.00 | 1.12 | 0.94 | 1.08 | 1.00 | 1.26 | 1.00 | 1.00 | 1.00 | 1.00 |
| Cenpo | 1.00 | 1.00 | 1.00 | 0.77 | 1.02 | 0.89 | 1.09 | 2.31 | 0.84 | 0.99 | 0.99 | 1.02 |
| Cenpv | 1.54 | 0.36 | 1.11 | 0.95 | 0.78 | 1.04 | 1.44 | 2.63 | 1.01 | 1.06 | 0.66 | 0.90 |
| Cep63 | 0.87 | 1.04 | 1.00 | 1.05 | 1.85 | 1.00 | 1.35 | 7.39 | 1.10 | 3.64 | 1.19 | 1.25 |
| Cep89 | 0.53 | 1.00 | 0.69 | 1.08 | 1.40 | 0.86 | 1.07 | 8.06 | 1.09 | 2.31 | 1.05 | 0.69 |
| Cers4 | 0.84 | 0.64 | 1.06 | 0.87 | 0.88 | 0.99 | 1.72 | 6.19 | 1.41 | 1.49 | 0.89 | 0.85 |
| Ces1d | 0.26 | 0.36 | 0.34 | 1.00 | 1.00 | 1.00 | 1.28 | 6.39 | 1.69 | 1.00 | 1.00 | 1.00 |
| Ces2h | 1.00 | 1.00 | 1.00 | 1.00 | 1.00 | 1.00 | 1.00 | 1.00 | 1.00 | 1.00 | 1.00 | 1.00 |
| Cetn1 | 1.00 | 1.00 | 1.00 | 1.00 | 1.00 | 1.00 | 5.22 | 1.00 | 1.00 | 1.00 | 1.00 | 1.00 |
| Cfb | 1.00 | 1.00 | 1.00 | 1.00 | 1.00 | 1.00 | 1.36 | 6.75 | 1.33 | 1.00 | 1.00 | 1.00 |
| Cfd | 0.35 | 0.80 | 0.79 | 1.00 | 0.31 | 4.34 | 2.89 | 44.04 | 4.82 | 2.67 | 0.67 | 1.00 |
| Cfdp1 | 0.75 | 1.00 | 1.03 | 1.08 | 0.63 | 1.19 | 0.90 | 1.99 | 1.00 | 1.17 | 0.95 | 0.92 |
| Cfp | 0.70 | 1.17 | 1.17 | 1.05 | 0.77 | 1.11 | 1.34 | 8.29 | 1.21 | 2.62 | 1.19 | 1.07 |
| Cgref1 | 1.38 | 1.49 | 0.94 | 1.11 | 1.23 | 1.01 | 1.23 | 2.06 | 1.08 | 1.00 | 1.00 | 1.00 |
| Chac1 | 6.86 | 11.36 | 0.31 | 1.44 | 0.42 | 1.12 | 2.20 | 0.82 | 1.18 | 1.24 | 2.72 | 1.69 |
| Chaf1b | 1.00 | 1.00 | 1.00 | 1.00 | 1.45 | 1.00 | 1.07 | 4.50 | 0.64 | 1.29 | 0.87 | 0.88 |
| Chchd1 | 0.94 | 0.73 | 0.73 | 1.11 | 0.95 | 1.03 | 0.98 | 9.60 | 1.02 | 2.86 | 1.19 | 1.18 |
| Chchd10 | 0.57 | 0.64 | 0.58 | 1.16 | 0.98 | 1.12 | 1.63 | 9.83 | 1.16 | 1.12 | 0.75 | 0.99 |
| Chchd2 | 0.94 | 0.91 | 0.88 | 0.98 | 1.09 | 1.05 | 1.21 | 4.38 | 0.99 | 2.04 | 1.16 | 1.14 |
| Chchd6 | 1.63 | 1.00 | 0.56 | 1.06 | 0.90 | 0.95 | 1.64 | 7.67 | 1.21 | 1.52 | 0.62 | 0.65 |
| Chchd7 | 0.85 | 0.87 | 0.66 | 1.49 | 0.76 | 0.94 | 1.46 | 10.04 | 1.12 | 2.36 | 1.33 | 1.49 |
| Chga | 0.43 | 0.52 | 0.68 | 0.99 | 1.02 | 0.88 | 0.83 | 1.19 | 0.77 | 1.00 | 1.00 | 1.00 |
| Chgb | 0.61 | 0.50 | 1.22 | 1.24 | 1.07 | 1.01 | 1.00 | 1.00 | 1.00 | 1.00 | 1.00 | 1.00 |
| Chia1 | 1.00 | 1.00 | 0.33 | 1.00 | 0.85 | 0.44 | 1.00 | 7.52 | 0.88 | 1.73 | 1.00 | 1.00 |
| Chic2 | 1.54 | 1.51 | 1.10 | 0.80 | 1.00 | 0.97 | 1.01 | 0.40 | 1.01 | 0.80 | 1.17 | 1.17 |
| Chil1 | 1.00 | 1.00 | 1.00 | 1.09 | 0.58 | 1.10 | 0.70 | 1.03 | 0.56 | 1.38 | 1.38 | 1.18 |
| Chil3 | 1.00 | 1.00 | 1.00 | 1.00 | 1.00 | 1.00 | 1.00 | 1.00 | 1.00 | 5.11 | 4.16 | 3.24 |
| Chil4 | 1.00 | 1.00 | 1.00 | 1.00 | 1.00 | 1.00 | 1.00 | 1.00 | 1.00 | 0.47 | 3.65 | 3.20 |
| Chkb | 1.06 | 1.14 | 1.28 | 1.10 | 1.01 | 1.04 | 1.31 | 7.03 | 1.35 | 3.72 | 1.36 | 1.10 |
| Chmp2a | 0.92 | 0.92 | 0.85 | 1.16 | 0.85 | 0.93 | 1.13 | 7.64 | 0.88 | 2.13 | 1.22 | 1.07 |
| Chmp3 | 0.75 | 0.73 | 0.72 | 0.81 | 5.44 | 0.83 | 0.70 | 0.49 | 0.80 | 0.83 | 0.94 | 0.96 |
| Chn1 | 1.00 | 1.00 | 1.00 | 1.13 | 0.87 | 1.06 | 1.18 | 1.00 | 1.00 | 1.00 | 1.00 | 1.00 |
| Chrne | 1.00 | 1.00 | 1.00 | 1.00 | 1.00 | 1.00 | 1.84 | 5.86 | 1.79 | 1.00 | 1.00 | 1.00 |
| Chst2 | 1.77 | 1.57 | 1.59 | 1.28 | 8.84 | 1.18 | 0.60 | 0.82 | 0.67 | 1.00 | 1.00 | 1.00 |
| Churc1 | 1.18 | 1.32 | 1.50 | 1.32 | 0.79 | 1.00 | 1.65 | 6.25 | 0.89 | 2.20 | 1.11 | 1.28 |
| Cib1 | 0.80 | 0.78 | 1.39 | 1.01 | 0.51 | 1.32 | 1.00 | 6.02 | 0.99 | 2.17 | 1.77 | 1.51 |
| Cib3 | 1.00 | 1.00 | 1.00 | 1.00 | 1.00 | 1.00 | 1.31 | 8.56 | 1.79 | 1.00 | 1.00 | 1.00 |

Fig. 35- 145

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Cidea | 3.13 | 6.34 | 8.21 | 0.42 | 2.88 | 0.97 | 0.93 | 0.66 | 0.88 | 3.43 | 3.65 | 1.13 |
| Cidec | 2.09 | 3.50 | 3.82 | 0.86 | 1.58 | 1.54 | 1.42 | 1.52 | 7.43 | 1.01 | 1.44 | 1.20 |
| Cisd2 | 0.78 | 0.83 | 0.61 | 0.90 | 0.82 | 0.76 | 0.74 | 0.90 | 0.79 | 0.60 | 0.72 | 0.93 |
| Cisd3 | 1.02 | 0.58 | 0.96 | 0.37 | 5.71 | 1.09 | 0.94 | 0.76 | 0.88 | 1.55 | 3.03 | 1.04 |
| Cited1 | 0.54 | 0.46 | 1.00 | 1.00 | 3.48 | 1.00 | 1.00 | 0.70 | 0.72 | 1.00 | 1.11 | 1.00 |
| Ckb | 0.70 | 0.45 | 0.84 | 0.31 | 5.94 | 1.40 | 0.72 | 0.58 | 0.68 | 1.61 | 2.31 | 0.69 |
| Ckm | 1.17 | 0.72 | 0.91 | 0.85 | 7.29 | 1.13 | 1.11 | 0.89 | 0.82 | 2.40 | 3.32 | 0.78 |
| Ckmt1 | 1.00 | 1.00 | 1.00 | 1.00 | 0.21 | 1.00 | 1.00 | 1.00 | 1.00 | 1.39 | 1.43 | 1.34 |
| Clca3 | 1.00 | 1.00 | 1.00 | 1.00 | 1.00 | 1.00 | 1.00 | 1.00 | 1.00 | 1.00 | 1.92 | 4.73 |
| Cldn10 | 1.00 | 1.00 | 1.00 | 5.11 | 4.50 | 2.17 | 1.00 | 1.00 | 1.00 | 1.50 | 2.43 | 1.78 |
| Cldn11 | 1.00 | 1.00 | 1.00 | 1.00 | 0.16 | 1.00 | 1.00 | 1.00 | 1.00 | 1.00 | 1.00 | 1.00 |
| Cldn15 | 1.11 | 0.70 | 0.89 | 1.49 | 4.42 | 1.72 | 1.13 | 0.97 | 1.33 | 2.32 | 2.49 | 1.40 |
| Cldn3 | 1.00 | 1.00 | 1.00 | 1.00 | 1.00 | 1.00 | 1.00 | 1.00 | 1.00 | 1.64 | 2.35 | 1.05 |
| Cldn5 | 0.87 | 0.29 | 0.77 | 1.63 | 12.50 | 1.80 | 1.15 | 0.72 | 0.85 | 4.02 | 4.60 | 0.99 |
| Cldn7 | 1.00 | 1.00 | 0.96 | 1.00 | 1.00 | 1.00 | 1.00 | 1.00 | 1.00 | 2.67 | 5.06 | 1.23 |
| Clec10a | 2.52 | 0.86 | 2.31 | 1.44 | 9.26 | 1.76 | 0.63 | 0.68 | 1.38 | 1.41 | 2.40 | 1.76 |
| Clec12b | 1.00 | 1.00 | 1.00 | 1.34 | 1.00 | 1.00 | 1.13 | 1.49 | 1.62 | 5.94 | 10.14 | 7.53 |
| Clec1b | 1.00 | 1.00 | 1.00 | 1.00 | 1.00 | 1.00 | 1.00 | 1.00 | 1.07 | 1.28 | 1.87 | 0.74 |
| Clec2i | 1.00 | 1.00 | 1.00 | 1.00 | 0.46 | 1.00 | 1.00 | 1.00 | 1.00 | 1.00 | 1.00 | 1.00 |
| Clec4d | 1.00 | 1.00 | 1.00 | 1.00 | 1.00 | 1.00 | 2.52 | 1.83 | 2.29 | 3.80 | 4.03 | 0.96 |
| Clint1 | 1.18 | 1.81 | 1.17 | 1.77 | 1.04 | 1.17 | 1.32 | 1.32 | 1.16 | 1.26 | 0.74 | 0.97 |
| Clpp | 1.34 | 0.47 | 0.94 | 0.22 | 10.95 | 0.93 | 1.01 | 0.76 | 0.78 | 5.05 | 5.99 | 1.10 |
| Clps | 1.44 | 1.00 | 1.00 | 7.48 | 1.00 | 1.00 | 1.00 | 1.00 | 1.00 | 0.04 | 1.00 | 1.93 |
| Clstn3 | 1.00 | 1.60 | 3.03 | 0.93 | 0.57 | 1.41 | 1.00 | 1.00 | 1.83 | 1.00 | 1.00 | 1.00 |
| Cma1 | 1.74 | 0.41 | 1.13 | 2.74 | 7.92 | 1.71 | 1.00 | 1.00 | 1.33 | 3.14 | 4.44 | 1.00 |
| Cmc1 | 0.86 | 0.60 | 0.83 | 0.77 | 10.34 | 1.40 | 1.02 | 1.08 | 0.68 | 2.20 | 2.87 | 1.25 |
| Cmc2 | 0.75 | 0.55 | 0.73 | 0.34 | 7.41 | 0.69 | 1.03 | 0.79 | 0.88 | 2.45 | 3.61 | 1.03 |
| Cmtm2b | 1.00 | 1.00 | 1.00 | 1.00 | 1.00 | 1.00 | 1.00 | 1.00 | 1.00 | 1.44 | 1.00 | 1.00 |
| Cmtm7 | 1.57 | 0.79 | 1.25 | 0.67 | 6.31 | 1.38 | 0.98 | 0.82 | 1.02 | 1.23 | 1.53 | 0.81 |
| Cnfn | 1.00 | 1.00 | 1.00 | 1.00 | 1.00 | 1.00 | 1.00 | 1.00 | 1.00 | 1.00 | 1.00 | 1.00 |
| Cnih2 | 1.00 | 1.00 | 1.00 | 1.00 | 0.40 | 1.00 | 1.00 | 1.00 | 1.00 | 1.67 | 1.25 | 1.00 |
| Cnksr3 | 1.40 | 5.03 | 2.45 | 1.65 | 0.84 | 1.17 | 1.66 | 1.92 | 1.04 | 0.63 | 0.74 | 1.01 |
| Cnot10 | 1.11 | 0.60 | 1.07 | 0.48 | 3.59 | 1.20 | 1.14 | 1.07 | 0.98 | 2.49 | 3.36 | 1.01 |
| Cnot11 | 1.03 | 0.63 | 0.81 | 1.19 | 3.22 | 0.96 | 1.00 | 0.82 | 0.92 | 2.99 | 3.45 | 1.11 |
| Cntd1 | 1.00 | 0.31 | 1.00 | 1.00 | 3.02 | 1.00 | 1.00 | 1.00 | 1.00 | 5.87 | 5.20 | 1.10 |
| Cntn1 | 1.84 | 1.00 | 1.32 | 1.00 | 0.29 | 1.00 | 1.00 | 1.00 | 1.00 | 1.00 | 0.98 | 0.58 |
| Cntnap1 | 1.00 | 1.00 | 1.00 | 0.31 | 0.18 | 0.45 | 1.00 | 1.00 | 1.00 | 1.00 | 1.00 | 0.85 |
| Cntrl | 1.48 | 1.35 | 0.94 | 1.40 | 1.00 | 1.28 | 1.27 | 1.07 | 1.30 | 1.06 | 1.26 | 1.04 |
| Col7a1 | 1.00 | 0.71 | 1.00 | 1.00 | 1.73 | 1.00 | 1.00 | 1.00 | 1.00 | 3.22 | 3.16 | 1.00 |
| Commd6 | 1.04 | 0.76 | 0.99 | 0.75 | 2.98 | 0.83 | 0.89 | 0.84 | 0.85 | 1.30 | 1.50 | 1.02 |
| Comtd1 | 1.91 | 1.06 | 1.55 | 0.22 | 3.72 | 0.66 | 1.44 | 1.05 | 1.01 | 1.49 | 2.40 | 0.95 |
| Cops3 | 1.01 | 0.63 | 0.85 | 0.68 | 3.34 | 0.84 | 1.16 | 1.14 | 0.90 | 4.27 | 3.64 | 0.93 |
| Cops6 | 1.23 | 0.42 | 0.91 | 0.30 | 13.62 | 0.96 | 0.88 | 0.85 | 0.88 | 4.05 | 5.66 | 0.94 |
| Copz1 | 1.13 | 0.77 | 0.89 | 0.68 | 3.52 | 0.85 | 0.95 | 0.90 | 0.81 | 2.28 | 2.57 | 0.87 |
| Copz2 | 0.98 | 0.55 | 0.89 | 0.43 | 6.81 | 0.97 | 0.79 | 0.71 | 0.92 | 1.28 | 2.20 | 0.72 |
| Coq6 | 0.93 | 0.68 | 0.88 | 0.31 | 1.68 | 0.84 | 1.04 | 0.95 | 0.96 | 1.05 | 1.22 | 1.11 |
| Coro2b | 2.23 | 2.29 | 2.42 | 1.99 | 1.06 | 2.31 | 1.95 | 2.15 | 1.90 | 0.85 | 0.83 | 1.15 |
| Coro6 | 1.03 | 5.48 | 1.28 | 0.45 | 0.28 | 1.25 | 1.19 | 1.25 | 1.04 | 1.00 | 0.64 | 1.26 |
| Cort | 1.00 | 1.00 | 1.00 | 1.00 | 1.08 | 1.00 | 1.00 | 1.00 | 1.00 | 1.38 | 1.76 | 1.00 |
| Cox17 | 1.08 | 0.74 | 0.68 | 0.39 | 5.33 | 0.92 | 1.19 | 0.84 | 0.81 | 1.26 | 2.57 | 1.23 |
| Cox20 | 0.97 | 0.57 | 1.04 | 0.77 | 3.72 | 0.94 | 0.75 | 0.92 | 0.93 | 1.58 | 1.91 | 0.99 |
| Cox4i1 | 1.05 | 0.62 | 0.80 | 0.22 | 5.90 | 0.93 | 0.96 | 0.83 | 0.76 | 1.58 | 2.99 | 0.92 |
| Cox4i2 | 0.90 | 0.34 | 0.83 | 0.39 | 7.93 | 0.85 | 0.78 | 0.86 | 0.63 | 2.09 | 3.09 | 0.99 |
| Cox5b | 0.91 | 0.39 | 0.62 | 0.14 | 6.50 | 0.78 | 1.18 | 0.82 | 0.73 | 2.24 | 3.77 | 1.11 |
| Cox6a1 | 1.41 | 0.93 | 1.33 | 0.36 | 7.08 | 1.05 | 1.04 | 0.73 | 0.97 | 1.72 | 3.15 | 0.97 |
| Cox6a2 | 0.98 | 0.40 | 0.73 | 0.79 | 6.71 | 0.64 | 0.91 | 0.76 | 0.76 | 3.53 | 5.57 | 1.12 |
| Cox6b1 | 1.15 | 0.53 | 0.81 | 0.47 | 6.84 | 0.84 | 0.96 | 0.81 | 0.79 | 2.20 | 3.38 | 0.82 |
| Cox6b2 | 1.00 | 0.43 | 1.00 | 0.15 | 3.57 | 0.33 | 0.40 | 0.49 | 0.57 | 1.76 | 3.38 | 0.87 |
| Cox7a1 | 0.93 | 0.55 | 0.83 | 0.22 | 10.82 | 0.81 | 1.26 | 0.89 | 0.92 | 4.49 | 8.39 | 1.11 |
| Cox7a2 | 1.19 | 0.50 | 0.85 | 0.23 | 8.55 | 0.99 | 0.83 | 0.75 | 0.80 | 2.12 | 3.85 | 0.91 |
| Cox7b | 0.90 | 0.69 | 0.86 | 0.23 | 3.61 | 0.82 | 0.90 | 0.85 | 0.75 | 0.99 | 1.90 | 0.81 |
| Cox7c | 1.04 | 0.77 | 0.79 | 0.19 | 2.03 | 0.92 | 0.88 | 0.94 | 0.87 | 1.06 | 1.24 | 0.89 |
| Cox8b | 1.05 | 0.54 | 0.77 | 0.43 | 6.19 | 0.76 | 0.96 | 0.80 | 0.76 | 1.61 | 2.39 | 0.93 |
| Cox8c | 1.00 | 1.00 | 1.00 | 1.00 | 1.00 | 1.00 | 1.00 | 1.00 | 1.00 | 1.00 | 1.00 | 1.00 |

Fig. 35- 146

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Cidea | 0.27 | 1.05 | 0.16 | 0.59 | 0.59 | 1.31 | 1.00 | 1.00 | 1.00 | 1.00 | 1.94 | 0.72 |
| Cidec | 1.15 | 2.02 | 1.32 | 0.95 | 1.67 | 1.86 | 43.45 | 22.07 | 32.66 | 1.80 | 2.20 | 1.53 |
| Cisd2 | 0.85 | 0.83 | 0.84 | 0.82 | 1.07 | 0.90 | 0.77 | 0.52 | 0.91 | 0.93 | 0.94 | 0.91 |
| Cisd3 | 0.89 | 1.13 | 0.67 | 0.65 | 0.62 | 0.66 | 0.86 | 0.74 | 0.67 | 0.85 | 1.49 | 1.03 |
| Cited1 | 1.00 | 1.00 | 0.91 | 1.00 | 0.31 | 1.00 | 1.00 | 1.00 | 1.00 | 1.00 | 1.03 | 1.03 |
| Ckb | 0.80 | 1.06 | 0.84 | 0.64 | 0.49 | 0.64 | 0.75 | 1.81 | 0.82 | 0.89 | 1.34 | 0.89 |
| Ckm | 0.54 | 0.31 | 0.94 | 1.00 | 0.62 | 1.00 | 1.00 | 1.28 | 1.00 | 0.95 | 1.37 | 0.99 |
| Ckmt1 | 0.98 | 0.89 | 0.89 | 0.91 | 1.18 | 0.99 | 1.00 | 1.00 | 1.00 | 1.09 | 1.25 | 1.05 |
| Clca3 | 1.00 | 1.00 | 1.00 | 1.00 | 1.00 | 1.00 | 1.00 | 1.00 | 1.00 | 1.05 | 0.59 | 0.76 |
| Cldn10 | 1.82 | 1.00 | 1.00 | 0.93 | 1.00 | 0.94 | 1.00 | 1.00 | 1.00 | 1.05 | 2.76 | 0.90 |
| Cldn11 | 1.00 | 1.00 | 2.01 | 0.80 | 1.00 | 0.88 | 1.00 | 1.00 | 1.00 | 1.00 | 1.00 | 1.00 |
| Cldn15 | 2.99 | 2.69 | 2.33 | 1.31 | 1.15 | 1.16 | 2.26 | 7.38 | 1.75 | 0.96 | 1.13 | 0.92 |
| Cldn3 | 2.86 | 2.60 | 2.56 | 1.58 | 1.68 | 1.94 | 0.68 | 0.72 | 0.83 | 1.25 | 1.71 | 1.25 |
| Cldn5 | 2.54 | 2.67 | 1.28 | 0.91 | 0.59 | 1.06 | 0.40 | 1.14 | 0.41 | 0.67 | 0.97 | 0.69 |
| Cldn7 | 1.66 | 2.10 | 1.43 | 0.77 | 0.55 | 1.13 | 1.00 | 1.00 | 1.00 | 1.10 | 1.48 | 1.13 |
| Clec10a | 1.88 | 2.18 | 1.86 | 1.00 | 0.90 | 1.42 | 1.00 | 1.00 | 1.00 | 1.15 | 1.56 | 1.68 |
| Clec12b | 1.00 | 1.00 | 1.00 | 1.00 | 1.00 | 1.00 | 1.00 | 1.00 | 1.00 | 1.00 | 1.00 | 1.00 |
| Clec1b | 7.24 | 6.15 | 6.21 | 1.00 | 1.00 | 1.00 | 1.18 | 1.17 | 0.93 | 1.00 | 1.00 | 1.00 |
| Clec2i | 1.00 | 1.00 | 1.00 | 1.00 | 1.00 | 1.00 | 1.00 | 1.00 | 1.00 | 1.00 | 1.00 | 1.00 |
| Clec4d | 1.00 | 1.00 | 1.01 | 1.00 | 1.00 | 1.00 | 1.00 | 1.00 | 1.00 | 1.00 | 1.66 | 1.00 |
| Clint1 | 1.01 | 0.99 | 1.22 | 1.18 | 1.37 | 1.08 | 1.35 | 1.51 | 1.29 | 1.17 | 0.97 | 1.13 |
| Clpp | 1.28 | 1.57 | 1.18 | 0.81 | 0.47 | 0.98 | 1.09 | 4.29 | 1.05 | 0.76 | 1.46 | 0.75 |
| Clps | 0.95 | 1.00 | 1.78 | 0.88 | 0.14 | 0.86 | 1.33 | 0.81 | 0.77 | 0.43 | 1.88 | 10.05 |
| Clstn3 | 0.70 | 1.59 | 0.89 | 1.00 | 1.00 | 1.00 | 3.51 | 1.00 | 2.71 | 1.00 | 1.00 | 1.00 |
| Cma1 | 1.33 | 0.38 | 0.48 | 1.00 | 1.00 | 1.00 | 1.00 | 1.00 | 1.00 | 2.74 | 2.35 | 2.07 |
| Cmc1 | 0.96 | 1.45 | 1.09 | 0.94 | 0.53 | 0.86 | 1.06 | 1.48 | 0.95 | 1.25 | 1.73 | 1.13 |
| Cmc2 | 1.03 | 1.43 | 0.77 | 0.80 | 0.56 | 0.69 | 0.91 | 1.99 | 0.58 | 0.99 | 1.39 | 0.75 |
| Cmtm2b | 1.00 | 1.00 | 1.00 | 1.00 | 1.00 | 1.00 | 1.00 | 1.00 | 1.00 | 1.00 | 1.00 | 1.00 |
| Cmtm7 | 0.92 | 1.12 | 0.91 | 0.57 | 0.82 | 0.94 | 1.24 | 1.69 | 0.87 | 0.93 | 1.42 | 0.84 |
| Cnfn | 1.15 | 1.00 | 1.00 | 1.00 | 1.00 | 1.00 | 1.00 | 1.00 | 1.00 | 1.00 | 1.00 | 1.00 |
| Cnih2 | 1.32 | 1.91 | 0.72 | 1.00 | 1.76 | 1.00 | 1.00 | 3.39 | 1.00 | 1.38 | 2.10 | 0.88 |
| Cnksr3 | 1.61 | 1.31 | 1.61 | 1.07 | 1.97 | 1.12 | 0.98 | 1.00 | 1.05 | 1.40 | 1.21 | 1.44 |
| Cnot10 | 0.92 | 0.97 | 0.86 | 1.12 | 0.57 | 1.02 | 0.92 | 2.51 | 0.94 | 0.93 | 1.19 | 1.03 |
| Cnot11 | 0.96 | 1.11 | 0.96 | 1.02 | 0.71 | 0.98 | 1.25 | 2.79 | 0.92 | 1.02 | 1.29 | 0.91 |
| Cntd1 | 1.15 | 1.05 | 0.83 | 1.27 | 0.60 | 0.69 | 1.00 | 0.54 | 1.00 | 1.10 | 0.83 | 1.36 |
| Cntn1 | 1.00 | 1.00 | 1.00 | 1.00 | 1.00 | 1.00 | 1.00 | 1.00 | 1.00 | 0.97 | 0.78 | 1.31 |
| Cntnap1 | 1.30 | 1.06 | 1.33 | 1.00 | 1.00 | 1.00 | 5.02 | 1.82 | 7.46 | 0.74 | 0.74 | 1.07 |
| Cntrl | 0.78 | 0.69 | 0.82 | 1.29 | 1.13 | 1.09 | 4.48 | 5.21 | 3.93 | 0.92 | 0.89 | 0.98 |
| Col7a1 | 1.00 | 1.00 | 0.95 | 1.00 | 0.72 | 1.00 | 1.00 | 1.00 | 1.00 | 1.00 | 1.00 | 1.00 |
| Commd6 | 1.13 | 1.62 | 1.07 | 0.94 | 0.81 | 0.89 | 0.98 | 0.96 | 0.91 | 0.93 | 1.46 | 1.23 |
| Comtd1 | 0.88 | 1.02 | 0.95 | 1.18 | 0.64 | 1.24 | 0.99 | 1.37 | 0.71 | 1.27 | 1.61 | 1.18 |
| Cops3 | 0.78 | 0.77 | 0.89 | 1.04 | 0.56 | 0.88 | 1.12 | 2.07 | 1.01 | 1.00 | 1.41 | 1.17 |
| Cops6 | 1.19 | 1.31 | 0.98 | 0.90 | 0.49 | 0.94 | 1.17 | 2.68 | 0.85 | 0.98 | 1.89 | 1.03 |
| Copz1 | 1.13 | 1.31 | 0.96 | 0.91 | 0.53 | 0.88 | 0.85 | 1.58 | 0.77 | 0.97 | 1.40 | 0.99 |
| Copz2 | 1.91 | 1.23 | 1.08 | 0.72 | 0.70 | 0.77 | 1.09 | 1.19 | 0.88 | 0.78 | 1.63 | 1.11 |
| Coq6 | 0.73 | 1.06 | 0.67 | 1.07 | 0.76 | 0.88 | 1.22 | 1.11 | 1.35 | 1.12 | 1.11 | 1.13 |
| Coro2b | 5.19 | 4.77 | 7.88 | 1.20 | 0.95 | 1.40 | 1.00 | 1.00 | 1.00 | 1.36 | 1.02 | 0.99 |
| Coro6 | 1.00 | 1.00 | 1.09 | 1.27 | 1.00 | 1.64 | 1.00 | 1.00 | 1.00 | 1.00 | 1.00 | 1.00 |
| Cort | 0.66 | 1.34 | 1.19 | 1.00 | 1.00 | 1.00 | 1.00 | 1.00 | 1.00 | 1.00 | 1.00 | 1.00 |
| Cox17 | 0.88 | 1.17 | 0.83 | 0.85 | 0.88 | 1.12 | 1.22 | 0.92 | 0.79 | 1.12 | 1.74 | 1.37 |
| Cox20 | 0.94 | 0.91 | 0.90 | 0.65 | 0.63 | 0.76 | 0.82 | 1.18 | 1.04 | 0.84 | 1.75 | 1.09 |
| Cox4i1 | 1.21 | 1.69 | 0.87 | 0.82 | 0.77 | 0.77 | 0.95 | 1.12 | 0.83 | 1.01 | 1.72 | 1.00 |
| Cox4i2 | 1.00 | 1.90 | 1.38 | 1.04 | 0.86 | 1.44 | 1.00 | 1.00 | 1.00 | 1.00 | 0.91 | 1.10 |
| Cox5b | 1.15 | 1.65 | 0.96 | 0.84 | 0.57 | 1.09 | 1.05 | 2.23 | 0.98 | 0.85 | 1.65 | 0.83 |
| Cox6a1 | 1.02 | 1.38 | 0.81 | 0.81 | 0.77 | 0.78 | 0.96 | 1.40 | 0.82 | 1.09 | 1.90 | 1.05 |
| Cox6a2 | 0.60 | 0.39 | 0.59 | 1.00 | 1.11 | 1.00 | 1.00 | 1.00 | 1.00 | 1.00 | 1.28 | 1.00 |
| Cox6b1 | 1.14 | 1.29 | 0.91 | 0.82 | 0.58 | 0.70 | 0.88 | 1.64 | 0.77 | 1.06 | 1.93 | 0.96 |
| Cox6b2 | 1.00 | 1.74 | 1.38 | 0.32 | 0.30 | 0.42 | 2.09 | 2.34 | 1.72 | 0.69 | 2.24 | 0.66 |
| Cox7a1 | 1.00 | 1.00 | 0.35 | 0.65 | 0.26 | 0.41 | 1.00 | 7.43 | 1.00 | 2.59 | 1.56 | 0.82 |
| Cox7a2 | 1.13 | 1.51 | 0.67 | 0.85 | 0.64 | 0.86 | 0.93 | 1.71 | 0.81 | 1.04 | 2.13 | 1.03 |
| Cox7b | 0.96 | 1.18 | 0.81 | 0.81 | 0.91 | 0.72 | 0.93 | 0.88 | 0.85 | 1.07 | 1.63 | 0.97 |
| Cox7c | 0.80 | 1.75 | 0.80 | 0.80 | 1.27 | 0.89 | 0.90 | 0.46 | 0.96 | 0.90 | 1.74 | 1.05 |
| Cox8b | 0.23 | 1.09 | 0.15 | 0.54 | 0.45 | 0.75 | 1.00 | 1.00 | 1.00 | 1.85 | 2.98 | 1.00 |
| Cox8c | 1.00 | 1.00 | 1.00 | 1.00 | 1.00 | 1.00 | 1.00 | 1.00 | 1.00 | 1.00 | 1.00 | 1.00 |

Fig. 35- 147

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Cidea | 0.89 | 1.86 | 1.60 | 0.80 | 4.83 | 0.72 | 0.83 | 1.01 | 0.96 | 1.00 | 1.00 | 1.00 |
| Cidec | 0.80 | 0.99 | 0.92 | 1.31 | 2.05 | 1.62 | 1.59 | 1.00 | 0.66 | 1.00 | 1.02 | 1.34 |
| Cisd2 | 0.93 | 0.89 | 0.81 | 0.84 | 0.88 | 0.90 | 1.10 | 0.48 | 0.95 | 0.96 | 0.87 | 0.80 |
| Cisd3 | 0.91 | 0.72 | 0.65 | 1.48 | 8.87 | 1.60 | 0.64 | 1.43 | 1.68 | 1.00 | 0.86 | 1.01 |
| Cited1 | 1.00 | 1.00 | 1.00 | 1.26 | 0.09 | 0.23 | 0.96 | 2.54 | 1.02 | 1.14 | 1.31 | 1.00 |
| Ckb | 1.10 | 1.31 | 1.20 | 0.87 | 1.38 | 1.25 | 0.48 | 1.74 | 0.81 | 0.53 | 2.38 | 0.65 |
| Ckm | 2.42 | 1.55 | 2.26 | 1.00 | 0.27 | 0.43 | 1.00 | 0.83 | 1.00 | 0.87 | 0.67 | 0.49 |
| Ckmt1 | 0.83 | 0.92 | 0.60 | 1.00 | 1.00 | 1.68 | 1.00 | 1.00 | 1.00 | 1.00 | 8.33 | 1.00 |
| Clca3 | 4.00 | 4.17 | 5.13 | 1.00 | 1.00 | 1.00 | 1.00 | 1.00 | 1.00 | 1.00 | 1.00 | 1.00 |
| Cldn10 | 1.00 | 1.00 | 1.66 | 1.58 | 2.42 | 2.43 | 1.00 | 1.00 | 0.82 | 1.00 | 4.70 | 1.00 |
| Cldn11 | 1.00 | 1.00 | 1.00 | 1.55 | 1.00 | 3.42 | 0.94 | 0.52 | 1.05 | 1.00 | 9.67 | 1.00 |
| Cldn15 | 2.00 | 1.46 | 2.22 | 1.44 | 2.32 | 1.57 | 1.00 | 1.00 | 1.00 | 1.75 | 1.82 | 1.95 |
| Cldn3 | 3.51 | 1.80 | 4.32 | 1.69 | 4.38 | 0.81 | 0.96 | 2.92 | 1.18 | 1.00 | 1.00 | 1.00 |
| Cldn5 | 0.72 | 0.98 | 1.24 | 0.95 | 1.28 | 0.83 | 1.00 | 3.55 | 0.98 | 0.70 | 0.96 | 0.71 |
| Cldn7 | 2.88 | 2.07 | 3.37 | 1.25 | 3.32 | 1.92 | 1.00 | 1.30 | 1.00 | 1.00 | 1.00 | 1.00 |
| Clec10a | 0.99 | 1.49 | 1.17 | 0.93 | 2.98 | 1.00 | 1.00 | 1.17 | 1.00 | 1.05 | 1.05 | 1.17 |
| Clec12b | 1.00 | 1.00 | 1.00 | 1.00 | 1.00 | 1.00 | 0.97 | 0.77 | 0.86 | 1.00 | 1.00 | 1.00 |
| Clec1b | 1.00 | 1.00 | 1.00 | 1.00 | 1.00 | 1.00 | 1.00 | 1.00 | 1.00 | 2.61 | 3.29 | 2.32 |
| Clec2l | 1.00 | 1.11 | 1.00 | 1.00 | 1.00 | 1.11 | 1.00 | 1.00 | 1.00 | 0.44 | 1.05 | 0.46 |
| Clec4d | 1.00 | 1.43 | 1.00 | 1.89 | 7.99 | 1.81 | 1.00 | 1.00 | 1.00 | 1.54 | 1.50 | 1.45 |
| Clint1 | 1.09 | 1.07 | 0.93 | 1.38 | 0.95 | 1.06 | 1.03 | 2.78 | 0.96 | 1.06 | 0.85 | 0.94 |
| Clpp | 0.91 | 1.14 | 0.97 | 0.98 | 1.68 | 1.21 | 0.76 | 4.63 | 0.75 | 0.97 | 1.52 | 1.04 |
| Clps | 1.49 | 1.97 | 2.00 | 1.36 | 0.76 | 0.65 | 1.58 | 2.09 | 0.87 | 2.54 | 7.46 | 1.02 |
| Clstn3 | 1.03 | 1.00 | 1.00 | 4.67 | 1.55 | 3.43 | 1.01 | 1.00 | 0.98 | 1.00 | 10.39 | 1.00 |
| Cma1 | 0.90 | 0.91 | 1.30 | 3.26 | 4.02 | 2.13 | 1.00 | 1.00 | 1.00 | 1.00 | 1.00 | 1.00 |
| Cmc1 | 1.26 | 0.89 | 1.20 | 0.78 | 3.54 | 1.14 | 0.49 | 2.10 | 0.80 | 1.03 | 1.02 | 1.04 |
| Cmc2 | 0.64 | 1.05 | 0.65 | 0.73 | 1.37 | 0.62 | 1.00 | 3.17 | 1.05 | 1.11 | 1.62 | 0.85 |
| Cmtm2b | 1.00 | 1.00 | 1.00 | 2.09 | 9.30 | 1.00 | 0.78 | 3.96 | 0.82 | 1.00 | 1.00 | 1.00 |
| Cmtm7 | 1.03 | 0.92 | 0.91 | 0.99 | 3.49 | 1.14 | 0.79 | 0.95 | 0.90 | 1.05 | 0.92 | 0.95 |
| Cnfn | 0.95 | 1.41 | 1.30 | 1.00 | 1.00 | 1.00 | 1.00 | 1.00 | 1.00 | 1.00 | 1.00 | 1.00 |
| Cnih2 | 1.00 | 1.00 | 1.00 | 1.00 | 1.00 | 1.41 | 1.05 | 0.71 | 1.44 | 0.96 | 9.50 | 1.00 |
| Cnksr3 | 1.20 | 1.26 | 1.01 | 1.26 | 1.00 | 1.29 | 1.15 | 3.05 | 1.12 | 1.58 | 1.18 | 1.43 |
| Cnot10 | 0.98 | 1.04 | 1.00 | 0.95 | 1.43 | 1.00 | 1.19 | 2.62 | 1.15 | 0.91 | 1.22 | 1.14 |
| Cnot11 | 1.10 | 1.24 | 1.09 | 1.28 | 1.46 | 1.09 | 1.01 | 1.44 | 0.92 | 1.15 | 1.18 | 1.09 |
| Cntd1 | 1.00 | 0.96 | 1.26 | 1.02 | 2.20 | 1.00 | 1.04 | 0.94 | 0.93 | 1.41 | 0.95 | 0.91 |
| Cntn1 | 1.00 | 1.00 | 1.00 | 1.00 | 1.00 | 1.00 | 1.00 | 1.00 | 1.00 | 1.00 | 6.53 | 1.00 |
| Cntnap1 | 0.99 | 0.82 | 0.94 | 0.65 | 1.00 | 1.09 | 1.00 | 1.00 | 1.00 | 1.00 | 3.87 | 0.61 |
| Cntrl | 0.94 | 1.03 | 0.82 | 0.90 | 0.68 | 0.87 | 1.02 | 1.06 | 1.17 | 1.07 | 0.83 | 1.15 |
| Col7a1 | 1.00 | 1.06 | 0.98 | 1.00 | 1.00 | 1.00 | 1.00 | 1.10 | 1.00 | 1.53 | 1.62 | 1.54 |
| Commd6 | 1.03 | 0.96 | 0.96 | 0.94 | 6.62 | 0.97 | 1.32 | 1.51 | 1.02 | 1.27 | 1.01 | 0.90 |
| Comtd1 | 0.89 | 0.86 | 0.86 | 0.82 | 6.62 | 1.12 | 0.61 | 1.49 | 0.99 | 0.93 | 0.96 | 0.79 |
| Cops3 | 1.04 | 0.88 | 0.92 | 0.89 | 1.15 | 1.01 | 0.97 | 2.86 | 0.96 | 1.14 | 1.17 | 1.06 |
| Cops6 | 0.85 | 0.95 | 0.92 | 0.97 | 1.60 | 1.05 | 0.87 | 4.45 | 0.92 | 1.08 | 1.32 | 0.94 |
| Copz1 | 0.95 | 0.93 | 0.99 | 0.98 | 1.67 | 1.07 | 1.02 | 2.51 | 0.93 | 1.08 | 1.10 | 0.93 |
| Copz2 | 0.90 | 1.03 | 2.07 | 0.67 | 2.57 | 0.75 | 0.84 | 1.35 | 0.94 | 1.27 | 1.14 | 0.82 |
| Coq6 | 0.87 | 0.91 | 1.06 | 0.77 | 1.25 | 1.13 | 1.07 | 0.56 | 1.33 | 1.02 | 1.07 | 0.78 |
| Coro2b | 1.17 | 1.16 | 0.99 | 2.54 | 2.43 | 3.26 | 1.04 | 3.61 | 1.35 | 1.44 | 5.56 | 1.74 |
| Coro6 | 1.11 | 0.85 | 1.49 | 0.77 | 1.00 | 0.89 | 1.00 | 1.00 | 1.00 | 1.34 | 1.07 | 1.00 |
| Cort | 1.00 | 1.00 | 1.00 | 1.00 | 1.00 | 1.00 | 1.00 | 2.53 | 1.00 | 1.46 | 2.06 | 1.73 |
| Cox17 | 1.11 | 1.13 | 1.10 | 0.85 | 6.35 | 0.75 | 1.14 | 1.03 | 0.80 | 0.83 | 1.28 | 0.84 |
| Cox20 | 1.10 | 0.94 | 1.09 | 0.62 | 2.90 | 0.81 | 0.97 | 1.07 | 0.96 | 0.92 | 0.95 | 1.22 |
| Cox4i1 | 0.94 | 1.05 | 0.95 | 0.74 | 2.67 | 0.89 | 0.89 | 1.51 | 0.95 | 1.05 | 1.38 | 0.96 |
| Cox4i2 | 0.86 | 1.00 | 1.10 | 0.55 | 1.92 | 0.83 | 1.00 | 0.60 | 1.00 | 1.00 | 1.00 | 1.01 |
| Cox5b | 0.77 | 0.88 | 1.05 | 0.73 | 2.60 | 0.88 | 0.84 | 2.53 | 1.08 | 0.89 | 1.50 | 1.21 |
| Cox6a1 | 1.00 | 1.20 | 0.97 | 0.79 | 2.97 | 0.86 | 0.96 | 1.50 | 0.86 | 0.88 | 1.30 | 0.90 |
| Cox6a2 | 1.71 | 1.62 | 2.10 | 1.00 | 1.00 | 1.00 | 1.00 | 1.00 | 1.00 | 0.73 | 0.78 | 0.69 |
| Cox6b1 | 0.86 | 1.00 | 0.87 | 0.82 | 2.14 | 0.79 | 1.05 | 2.04 | 0.89 | 0.95 | 1.29 | 0.90 |
| Cox6b2 | 0.50 | 0.78 | 2.06 | 0.94 | 1.98 | 1.62 | 0.98 | 2.25 | 1.05 | 0.95 | 0.85 | 0.58 |
| Cox7a1 | 0.64 | 1.37 | 0.82 | 1.00 | 1.06 | 1.00 | 1.00 | 2.99 | 1.00 | 1.00 | 1.00 | 1.00 |
| Cox7a2 | 0.99 | 0.97 | 0.80 | 0.76 | 2.64 | 0.93 | 0.93 | 2.02 | 1.00 | 1.21 | 1.15 | 1.02 |
| Cox7b | 0.88 | 0.98 | 0.93 | 0.72 | 5.32 | 0.95 | 0.93 | 0.51 | 0.68 | 0.99 | 1.42 | 0.98 |
| Cox7c | 0.78 | 0.98 | 0.80 | 0.83 | 15.07 | 0.84 | 1.06 | 0.70 | 0.91 | 1.21 | 1.50 | 0.93 |
| Cox8b | 3.46 | 1.17 | 2.02 | 0.75 | 2.95 | 0.52 | 1.00 | 1.00 | 1.00 | 1.81 | 1.25 | 1.00 |
| Cox8c | 1.00 | 1.00 | 1.00 | 3.14 | 1.77 | 1.00 | 0.96 | 1.57 | 0.95 | 1.00 | 1.00 | 1.00 |

Fig. 35- 148

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Cidea | 1.00 | 1.00 | 1.00 | 1.21 | 5.63 | 1.28 | 1.65 | 3.66 | 1.14 | 1.00 | 1.00 | 1.00 |
| Cidec | 0.58 | 1.16 | 0.49 | 1.00 | 1.00 | 1.74 | 4.31 | 5.71 | 4.01 | 1.00 | 1.00 | 1.00 |
| Cisd2 | 1.06 | 1.06 | 0.79 | 1.04 | 8.69 | 0.99 | 0.80 | 0.46 | 0.93 | 0.68 | 0.87 | 0.86 |
| Cisd3 | 2.63 | 2.45 | 1.68 | 1.37 | 0.89 | 0.94 | 0.97 | 6.84 | 0.51 | 1.82 | 1.59 | 0.83 |
| Cited1 | 1.00 | 1.00 | 1.00 | 2.73 | 0.76 | 1.34 | 2.27 | 16.43 | 1.13 | 1.00 | 1.00 | 1.00 |
| Ckb | 1.00 | 1.00 | 1.51 | 1.08 | 0.83 | 1.04 | 0.97 | 7.46 | 0.76 | 1.80 | 0.90 | 1.32 |
| Ckm | 1.00 | 1.00 | 1.00 | 1.00 | 0.40 | 1.00 | 2.00 | 12.01 | 2.31 | 3.17 | 1.25 | 1.20 |
| Ckmt1 | 1.00 | 1.00 | 1.00 | 1.13 | 1.08 | 1.06 | 0.75 | 0.82 | 0.70 | 1.00 | 1.00 | 1.00 |
| Clca3 | 1.00 | 1.00 | 1.00 | 1.00 | 1.00 | 1.00 | 0.45 | 0.55 | 0.53 | 1.00 | 1.00 | 1.00 |
| Cldn10 | 0.67 | 0.54 | 0.71 | 1.08 | 2.64 | 1.05 | 1.19 | 0.91 | 1.44 | 1.00 | 1.00 | 1.00 |
| Cldn11 | 1.00 | 1.00 | 1.00 | 1.08 | 0.87 | 1.07 | 1.09 | 1.00 | 1.00 | 1.00 | 1.00 | 1.00 |
| Cldn15 | 1.45 | 1.28 | 2.15 | 1.00 | 1.00 | 1.00 | 2.72 | 6.38 | 3.44 | 1.71 | 1.10 | 1.20 |
| Cldn3 | 1.30 | 1.06 | 0.87 | 1.00 | 0.65 | 0.77 | 4.47 | 5.70 | 2.28 | 1.00 | 1.00 | 1.00 |
| Cldn5 | 0.72 | 1.00 | 0.46 | 1.23 | 0.86 | 0.95 | 1.08 | 15.35 | 1.32 | 1.58 | 0.68 | 0.69 |
| Cldn7 | 1.78 | 1.21 | 0.94 | 1.00 | 1.00 | 1.00 | 1.00 | 1.00 | 1.00 | 1.00 | 1.00 | 1.00 |
| Clec10a | 1.00 | 1.00 | 1.98 | 1.00 | 0.98 | 1.07 | 1.10 | 5.70 | 1.00 | 3.30 | 1.81 | 2.01 |
| Clec12b | 1.00 | 1.00 | 1.00 | 1.00 | 1.00 | 1.00 | 0.29 | 0.65 | 0.73 | 1.00 | 1.00 | 1.00 |
| Clec1b | 1.00 | 1.00 | 1.00 | 1.00 | 1.01 | 1.00 | 1.00 | 1.00 | 1.00 | 3.16 | 1.59 | 3.59 |
| Clec2i | 1.00 | 1.00 | 1.00 | 1.14 | 1.04 | 1.01 | 1.27 | 5.20 | 0.96 | 1.00 | 1.00 | 1.00 |
| Clec4d | 1.00 | 1.00 | 1.00 | 1.00 | 1.00 | 1.00 | 4.53 | 12.74 | 2.32 | 5.20 | 3.15 | 2.17 |
| Clint1 | 1.28 | 1.13 | 0.98 | 1.04 | 6.49 | 1.06 | 0.98 | 0.40 | 1.02 | 0.66 | 1.02 | 0.98 |
| Clpp | 1.25 | 1.09 | 0.93 | 1.19 | 0.85 | 0.98 | 1.29 | 30.14 | 0.94 | 4.00 | 1.04 | 1.00 |
| Clps | 0.99 | 0.94 | 0.95 | 1.06 | 0.18 | 0.54 | 0.88 | 24.47 | 1.09 | 2.87 | 1.02 | 1.11 |
| Clstn3 | 1.00 | 1.00 | 1.00 | 1.19 | 0.79 | 1.07 | 1.64 | 0.32 | 1.42 | 1.00 | 0.66 | 0.77 |
| Cma1 | 1.00 | 1.00 | 1.00 | 1.00 | 1.00 | 1.00 | 1.68 | 9.85 | 1.75 | 1.73 | 1.00 | 1.00 |
| Cmc1 | 0.93 | 0.60 | 0.59 | 1.13 | 0.80 | 1.18 | 0.90 | 10.63 | 0.97 | 2.33 | 1.38 | 2.13 |
| Cmc2 | 1.00 | 0.68 | 1.00 | 1.29 | 0.78 | 1.11 | 1.25 | 9.10 | 0.56 | 2.48 | 0.87 | 0.91 |
| Cmtm2b | 1.00 | 1.00 | 1.00 | 1.00 | 0.78 | 1.00 | 2.53 | 1.00 | 1.00 | 1.00 | 1.00 | 1.00 |
| Cmtm7 | 1.12 | 2.15 | 1.19 | 0.75 | 2.72 | 0.83 | 1.19 | 4.00 | 1.21 | 2.02 | 1.23 | 1.22 |
| Cnfn | 1.00 | 1.00 | 1.00 | 1.00 | 1.00 | 1.00 | 1.05 | 28.51 | 0.75 | 1.00 | 1.00 | 1.00 |
| Cnih2 | 1.00 | 1.00 | 1.00 | 1.26 | 1.51 | 1.15 | 1.85 | 1.07 | 1.16 | 1.00 | 1.00 | 1.00 |
| Cnksr3 | 1.49 | 1.17 | 1.37 | 1.09 | 1.08 | 1.12 | 1.20 | 0.28 | 1.25 | 0.92 | 1.14 | 1.61 |
| Cnot10 | 0.85 | 0.92 | 0.88 | 1.02 | 1.36 | 0.99 | 0.97 | 6.48 | 1.01 | 2.16 | 1.07 | 0.89 |
| Cnot11 | 1.16 | 1.53 | 1.18 | 1.01 | 0.90 | 0.96 | 1.41 | 7.11 | 1.47 | 2.13 | 1.31 | 0.88 |
| Cntd1 | 1.00 | 1.00 | 1.00 | 0.98 | 2.06 | 0.81 | 1.00 | 5.08 | 1.09 | 2.29 | 1.17 | 0.86 |
| Cntn1 | 1.00 | 1.00 | 1.00 | 1.00 | 0.85 | 0.95 | 1.00 | 1.00 | 1.00 | 1.00 | 1.00 | 1.00 |
| Cntnap1 | 1.00 | 1.00 | 1.00 | 1.02 | 0.77 | 1.01 | 1.00 | 1.00 | 0.79 | 1.00 | 1.00 | 1.00 |
| Cntrl | 1.00 | 1.00 | 1.00 | 0.58 | 1.89 | 0.84 | 0.95 | 0.53 | 0.95 | 1.37 | 1.27 | 1.03 |
| Col7a1 | 1.17 | 1.73 | 1.38 | 1.00 | 0.95 | 1.00 | 0.86 | 8.67 | 0.90 | 1.00 | 1.00 | 1.00 |
| Commd6 | 1.09 | 0.80 | 0.79 | 0.94 | 1.46 | 1.27 | 0.82 | 3.43 | 0.97 | 1.85 | 1.08 | 1.09 |
| Comtd1 | 1.07 | 1.00 | 1.72 | 1.13 | 0.82 | 1.09 | 0.66 | 6.44 | 0.79 | 2.10 | 1.17 | 1.29 |
| Cops3 | 0.79 | 0.95 | 0.87 | 0.99 | 1.30 | 0.98 | 0.93 | 9.05 | 1.07 | 2.36 | 0.95 | 0.89 |
| Cops6 | 0.83 | 1.02 | 1.11 | 1.07 | 0.78 | 0.97 | 1.08 | 23.84 | 0.89 | 3.77 | 1.15 | 1.06 |
| Copz1 | 0.78 | 0.74 | 0.78 | 0.98 | 0.83 | 0.97 | 1.05 | 7.57 | 0.90 | 2.23 | 1.23 | 1.22 |
| Copz2 | 1.11 | 1.12 | 0.93 | 0.82 | 3.60 | 0.84 | 1.09 | 7.24 | 0.81 | 1.58 | 1.00 | 1.00 |
| Coq6 | 1.00 | 1.00 | 1.10 | 0.95 | 7.96 | 1.11 | 1.26 | 2.84 | 1.11 | 1.08 | 1.17 | 1.04 |
| Coro2b | 1.00 | 1.00 | 1.59 | 1.25 | 0.95 | 1.23 | 1.85 | 0.50 | 2.62 | 1.00 | 1.00 | 1.00 |
| Coro6 | 1.00 | 1.00 | 1.00 | 0.85 | 0.69 | 1.04 | 0.97 | 0.32 | 1.21 | 1.00 | 1.00 | 1.00 |
| Cort | 1.00 | 1.00 | 1.00 | 0.72 | 0.70 | 0.86 | 1.00 | 11.62 | 1.09 | 3.03 | 1.53 | 1.02 |
| Cox17 | 1.13 | 0.57 | 0.97 | 1.03 | 1.29 | 0.95 | 1.32 | 4.82 | 0.82 | 1.65 | 1.21 | 1.06 |
| Cox20 | 0.52 | 0.96 | 0.67 | 0.74 | 28.92 | 1.14 | 0.98 | 3.68 | 1.08 | 2.78 | 1.23 | 1.18 |
| Cox4i1 | 0.92 | 0.97 | 0.97 | 1.06 | 0.95 | 0.99 | 1.26 | 7.38 | 0.99 | 2.23 | 1.10 | 1.10 |
| Cox4i2 | 1.00 | 1.00 | 1.00 | 1.55 | 0.47 | 1.83 | 1.60 | 13.42 | 1.49 | 1.47 | 1.00 | 1.00 |
| Cox5b | 0.54 | 1.04 | 1.98 | 1.22 | 1.09 | 0.99 | 0.95 | 9.08 | 0.91 | 3.07 | 0.96 | 1.00 |
| Cox6a1 | 0.99 | 0.87 | 0.92 | 1.15 | 0.94 | 1.00 | 1.41 | 7.18 | 0.94 | 2.56 | 1.15 | 1.24 |
| Cox6a2 | 1.00 | 1.00 | 1.00 | 0.70 | 0.32 | 0.96 | 1.86 | 16.93 | 1.54 | 2.50 | 0.80 | 1.08 |
| Cox6b1 | 0.96 | 1.24 | 0.88 | 1.19 | 0.93 | 1.03 | 1.12 | 10.20 | 0.97 | 2.88 | 1.05 | 1.20 |
| Cox6b2 | 1.00 | 1.00 | 1.00 | 0.58 | 1.45 | 0.42 | 2.62 | 17.42 | 1.03 | 2.78 | 1.00 | 0.89 |
| Cox7a1 | 1.00 | 1.00 | 1.00 | 1.00 | 6.01 | 1.00 | 0.84 | 38.35 | 1.86 | 1.00 | 1.00 | 1.00 |
| Cox7a2 | 0.90 | 1.14 | 1.07 | 0.97 | 0.96 | 1.07 | 1.25 | 10.28 | 1.08 | 3.11 | 1.25 | 1.28 |
| Cox7b | 0.81 | 1.30 | 1.07 | 1.01 | 2.70 | 1.04 | 1.17 | 2.69 | 0.97 | 1.65 | 1.07 | 1.11 |
| Cox7c | 0.54 | 0.79 | 0.94 | 0.96 | 0.82 | 1.15 | 1.04 | 1.45 | 0.94 | 1.35 | 1.10 | 1.13 |
| Cox8b | 1.00 | 1.00 | 1.00 | 1.57 | 1.06 | 0.65 | 1.39 | 12.21 | 1.47 | 1.00 | 1.00 | 1.00 |
| Cox8c | 1.00 | 1.00 | 1.00 | 1.00 | 1.00 | 1.00 | 5.53 | 1.00 | 1.00 | 1.00 | 1.00 | 1.00 |

Fig. 35- 149

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Cpa1 | 1.00 | 1.00 | 1.00 | 1.00 | 1.00 | 1.00 | 1.00 | 1.00 | 1.00 | 1.00 | 1.00 | 1.87 |
| Cpa2 | 1.00 | 1.00 | 1.00 | 1.00 | 1.00 | 1.00 | 1.00 | 1.00 | 1.00 | 1.00 | 1.00 | 1.00 |
| Cpb1 | 1.00 | 1.00 | 1.00 | 1.00 | 1.00 | 1.00 | 1.00 | 1.00 | 1.00 | 1.00 | 1.00 | 1.15 |
| Cpe | 0.70 | 0.62 | 0.63 | 1.08 | 0.41 | 1.41 | 0.91 | 0.77 | 0.80 | 1.58 | 1.68 | 1.05 |
| Cplx1 | 1.00 | 1.00 | 1.00 | 1.00 | 0.04 | 1.00 | 1.00 | 1.00 | 1.00 | 1.00 | 1.00 | 1.00 |
| Cplx2 | 1.00 | 1.00 | 1.00 | 0.83 | 0.05 | 1.00 | 0.68 | 0.76 | 0.66 | 1.47 | 1.07 | 0.78 |
| Cpsf3l | 1.10 | 0.48 | 0.98 | 0.67 | 5.04 | 1.19 | 1.12 | 0.90 | 0.98 | 1.64 | 2.72 | 0.92 |
| Cpsf4 | 1.13 | 0.80 | 1.19 | 0.56 | 3.85 | 1.10 | 1.43 | 0.85 | 1.03 | 1.38 | 2.01 | 0.96 |
| Cpsf4l | 1.00 | 1.00 | 1.00 | 1.00 | 3.25 | 1.17 | 1.00 | 1.00 | 1.00 | 1.48 | 1.00 | 1.00 |
| Cpt1c | 1.00 | 1.00 | 1.00 | 1.00 | 0.66 | 1.00 | 1.00 | 0.87 | 0.73 | 1.68 | 1.57 | 0.53 |
| Cpxm1 | 0.51 | 0.20 | 0.45 | 0.49 | 3.09 | 0.44 | 0.45 | 0.38 | 0.36 | 2.39 | 3.43 | 0.61 |
| Crabp1 | 1.00 | 1.00 | 1.00 | 1.00 | 1.00 | 1.00 | 1.00 | 1.00 | 1.00 | 1.00 | 1.00 | 1.00 |
| Crip1 | 1.62 | 0.68 | 2.22 | 0.27 | 10.06 | 1.34 | 0.85 | 0.59 | 0.77 | 1.91 | 3.98 | 1.07 |
| Crisp2 | 1.00 | 1.00 | 1.00 | 1.00 | 1.00 | 1.00 | 1.00 | 1.00 | 1.00 | 1.00 | 1.00 | 1.00 |
| Cris1 | 0.98 | 0.75 | 0.90 | 0.83 | 5.18 | 1.10 | 0.81 | 0.80 | 0.84 | 1.11 | 1.54 | 0.88 |
| Crmp1 | 1.00 | 1.00 | 1.00 | 1.00 | 0.26 | 1.00 | 1.00 | 1.00 | 1.00 | 1.00 | 1.00 | 1.00 |
| Crnde | 1.00 | 0.84 | 1.00 | 1.00 | 1.56 | 1.00 | 1.01 | 1.32 | 0.71 | 1.49 | 2.72 | 0.82 |
| Cryaa | 1.00 | 1.00 | 1.00 | 1.00 | 1.00 | 1.00 | 1.00 | 1.00 | 1.00 | 1.48 | 1.51 | 0.55 |
| Cryba4 | 1.00 | 0.46 | 1.00 | 1.00 | 1.25 | 1.00 | 1.05 | 0.82 | 0.69 | 7.14 | 3.94 | 1.00 |
| Crybb3 | 1.00 | 0.48 | 0.96 | 0.51 | 6.95 | 1.00 | 1.85 | 0.78 | 0.86 | 5.27 | 4.67 | 0.52 |
| Crygn | 1.00 | 1.00 | 1.00 | 1.00 | 2.07 | 1.00 | 1.00 | 1.00 | 1.00 | 2.01 | 5.40 | 1.88 |
| Crym | 0.67 | 0.48 | 0.40 | 1.00 | 0.58 | 1.00 | 1.00 | 1.00 | 1.00 | 0.54 | 0.57 | 0.96 |
| Cspg5 | 1.00 | 1.00 | 1.00 | 1.00 | 0.27 | 1.00 | 1.00 | 1.00 | 1.00 | 1.00 | 1.00 | 1.00 |
| Csrnp1 | 6.20 | 12.70 | 3.75 | 1.07 | 1.04 | 1.25 | 2.32 | 3.06 | 1.66 | 1.14 | 1.81 | 1.90 |
| Csrp2 | 1.81 | 1.54 | 2.02 | 0.35 | 5.52 | 0.76 | 1.04 | 0.85 | 1.06 | 2.01 | 3.41 | 1.35 |
| Csrp3 | 2.90 | 0.76 | 1.78 | 0.80 | 2.55 | 0.67 | 1.32 | 1.20 | 1.24 | 1.17 | 2.07 | 0.81 |
| Cst3 | 1.32 | 0.74 | 0.95 | 0.43 | 4.15 | 0.97 | 1.19 | 0.86 | 0.90 | 1.45 | 1.76 | 0.87 |
| Cst6 | 1.03 | 0.65 | 1.02 | 1.00 | 1.00 | 1.00 | 1.00 | 1.00 | 0.75 | 1.00 | 1.00 | 1.00 |
| Csta1 | 1.00 | 1.00 | 1.00 | 1.00 | 1.00 | 1.00 | 1.00 | 1.00 | 1.00 | 1.00 | 1.00 | 1.00 |
| Ctc1 | 0.82 | 0.42 | 0.91 | 1.72 | 4.28 | 0.98 | 1.04 | 1.07 | 0.88 | 2.57 | 2.78 | 0.94 |
| Ctcflos | 1.00 | 1.00 | 1.90 | 1.18 | 1.06 | 1.84 | 1.00 | 1.00 | 1.00 | 1.00 | 1.00 | 1.00 |
| Ctdnep1 | 1.03 | 0.59 | 0.86 | 0.35 | 2.97 | 0.80 | 0.89 | 0.70 | 0.85 | 2.38 | 2.83 | 0.92 |
| Ctgf | 2.06 | 2.62 | 1.78 | 1.09 | 2.61 | 3.05 | 6.47 | 5.56 | 3.89 | 0.65 | 0.75 | 1.05 |
| Ctla2a | 1.52 | 0.78 | 1.16 | 0.86 | 6.13 | 1.33 | 1.81 | 1.57 | 1.18 | 2.19 | 3.38 | 1.35 |
| Ctla2b | 1.08 | 1.09 | 1.39 | 1.11 | 3.09 | 2.07 | 1.29 | 1.96 | 1.03 | 0.93 | 2.18 | 1.44 |
| Ctrb1 | 1.00 | 1.00 | 1.00 | 2.33 | 1.00 | 1.00 | 1.00 | 1.00 | 1.79 | 1.00 | 1.00 | 3.24 |
| Ctrc | 1.00 | 1.00 | 1.00 | 1.00 | 1.00 | 1.00 | 1.00 | 1.00 | 1.00 | 1.00 | 1.00 | 1.00 |
| Ctrl | 1.00 | 1.00 | 1.00 | 1.00 | 1.00 | 1.00 | 1.00 | 1.00 | 1.00 | 1.28 | 1.00 | 1.02 |
| Ctsa | 1.10 | 0.48 | 1.00 | 0.61 | 7.05 | 1.25 | 0.92 | 0.88 | 0.90 | 1.31 | 2.41 | 0.81 |
| Ctsd | 1.64 | 0.90 | 1.29 | 0.52 | 4.93 | 1.02 | 1.02 | 0.90 | 0.97 | 2.26 | 3.39 | 1.08 |
| Ctsg | 1.00 | 1.00 | 1.00 | 1.00 | 1.00 | 1.00 | 1.00 | 1.00 | 1.00 | 1.00 | 1.00 | 1.00 |
| Ctsh | 1.57 | 1.02 | 1.16 | 0.69 | 6.39 | 1.20 | 0.82 | 0.61 | 0.76 | 1.52 | 2.81 | 1.50 |
| Ctsl | 1.85 | 3.13 | 2.32 | 2.53 | 6.47 | 1.87 | 2.29 | 2.01 | 1.33 | 0.98 | 1.31 | 1.32 |
| Ctsz | 1.65 | 0.84 | 1.49 | 0.32 | 5.15 | 1.40 | 1.17 | 0.98 | 1.27 | 2.12 | 3.17 | 1.02 |
| Ctu2 | 2.32 | 1.65 | 1.18 | 0.30 | 5.56 | 1.36 | 1.13 | 0.80 | 0.88 | 1.12 | 2.58 | 1.09 |
| Ctxn1 | 1.00 | 1.00 | 1.00 | 0.26 | 0.12 | 0.75 | 1.12 | 0.56 | 1.28 | 1.41 | 1.43 | 0.97 |
| Ctxn3 | 1.36 | 2.49 | 2.72 | 1.09 | 1.28 | 2.40 | 0.79 | 0.75 | 0.64 | 1.00 | 1.00 | 1.00 |
| Cuedc2 | 0.95 | 0.44 | 0.81 | 0.28 | 9.56 | 0.92 | 0.92 | 0.70 | 0.78 | 2.86 | 3.50 | 0.96 |
| Cuta | 1.19 | 0.56 | 0.73 | 0.29 | 5.13 | 0.98 | 0.77 | 0.79 | 0.92 | 2.00 | 2.62 | 1.05 |
| Cutc | 1.05 | 0.77 | 0.78 | 1.38 | 5.55 | 1.32 | 0.80 | 0.88 | 0.69 | 0.95 | 1.58 | 0.75 |
| Cuzd1 | 1.12 | 0.93 | 0.87 | 1.00 | 1.00 | 1.00 | 1.00 | 0.89 | 1.00 | 1.00 | 1.00 | 1.00 |
| Cx3cl1 | 1.00 | 1.00 | 0.78 | 1.19 | 0.05 | 0.87 | 1.16 | 1.09 | 1.62 | 0.74 | 0.67 | 1.01 |
| Cxcl13 | 10.60 | 12.76 | 6.10 | 10.04 | 4.41 | 5.78 | 1.00 | 0.97 | 4.94 | 0.33 | 0.59 | 3.13 |
| Cyb5rl | 1.40 | 0.68 | 0.95 | 0.45 | 4.31 | 1.02 | 1.41 | 0.90 | 1.25 | 3.63 | 4.22 | 1.29 |
| Cyba | 1.33 | 0.71 | 1.32 | 1.29 | 9.77 | 1.57 | 0.57 | 0.70 | 0.85 | 1.62 | 2.90 | 1.00 |
| Cyp17a1 | 1.00 | 1.00 | 1.00 | 1.00 | 1.00 | 1.00 | 1.00 | 1.00 | 1.00 | 1.00 | 1.00 | 1.00 |
| Cyp1b1 | 3.72 | 1.97 | 3.34 | 8.45 | 0.57 | 1.93 | 2.09 | 2.66 | 2.46 | 1.00 | 1.00 | 1.15 |
| Cyp24a1 | 1.00 | 1.00 | 1.00 | 1.00 | 1.00 | 1.00 | 1.00 | 1.00 | 1.00 | 1.00 | 1.00 | 1.00 |
| Cyp26b1 | 2.13 | 4.27 | 1.16 | 4.85 | 4.95 | 1.54 | 4.42 | 11.71 | 1.06 | 4.16 | 3.44 | 1.77 |
| Cyp27b1 | 1.00 | 1.00 | 1.00 | 1.00 | 1.00 | 1.00 | 1.00 | 1.00 | 1.00 | 1.00 | 1.00 | 1.00 |
| Cyp2b10 | 3.51 | 3.85 | 4.83 | 2.58 | 15.01 | 6.90 | 1.40 | 1.14 | 1.01 | 1.36 | 2.28 | 1.41 |
| Cyp2e1 | 1.38 | 2.10 | 4.31 | 1.49 | 3.62 | 3.74 | 1.50 | 0.36 | 3.76 | 0.57 | 0.81 | 0.87 |
| Cyp2s1 | 1.00 | 1.00 | 1.00 | 1.00 | 1.00 | 1.00 | 1.00 | 1.00 | 1.76 | 3.31 | 2.75 | 1.13 |
| Cyp4a10 | 1.00 | 1.00 | 1.00 | 3.85 | 2.31 | 2.83 | 2.61 | 0.41 | 1.00 | 0.46 | 1.00 | 1.00 |

Fig. 35- 150

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Cpa1 | 1.00 | 1.00 | 1.43 | 1.00 | 1.00 | 0.80 | 1.00 | 1.00 | 0.63 | 0.36 | 2.15 | 27.97 |
| Cpa2 | 1.00 | 1.00 | 1.00 | 1.00 | 1.00 | 0.87 | 1.00 | 1.00 | 1.00 | 0.46 | 3.13 | 20.18 |
| Cpb1 | 1.00 | 1.00 | 1.18 | 1.00 | 1.00 | 1.00 | 1.00 | 1.00 | 1.29 | 0.53 | 2.55 | 21.68 |
| Cpe | 1.93 | 1.82 | 1.03 | 2.44 | 1.74 | 1.83 | 1.00 | 1.14 | 1.00 | 1.10 | 1.23 | 1.15 |
| Cplx1 | 1.00 | 1.00 | 1.00 | 1.00 | 1.00 | 1.00 | 1.00 | 1.00 | 1.00 | 1.27 | 1.48 | 1.13 |
| Cplx2 | 1.11 | 0.87 | 1.21 | 0.79 | 0.48 | 0.80 | 1.00 | 1.00 | 1.00 | 0.85 | 0.71 | 0.94 |
| Cpsf3l | 0.88 | 1.00 | 0.78 | 0.93 | 0.69 | 1.03 | 0.96 | 1.43 | 0.94 | 1.01 | 1.26 | 0.95 |
| Cpsf4 | 0.96 | 1.42 | 0.89 | 1.06 | 0.86 | 1.05 | 0.94 | 1.28 | 1.17 | 0.97 | 1.28 | 1.15 |
| Cpsf4l | 1.15 | 1.14 | 1.11 | 0.84 | 0.91 | 0.84 | 1.31 | 1.15 | 1.06 | 1.00 | 1.00 | 1.00 |
| Cpt1c | 1.00 | 1.00 | 0.72 | 1.00 | 0.44 | 1.00 | 1.00 | 1.00 | 1.00 | 0.58 | 0.73 | 0.56 |
| Cpxm1 | 1.14 | 0.97 | 1.06 | 1.00 | 0.52 | 0.89 | 1.00 | 1.64 | 1.00 | 1.00 | 0.66 | 0.69 |
| Crabp1 | 0.53 | 1.34 | 0.64 | 1.00 | 1.00 | 1.00 | 1.00 | 1.00 | 1.00 | 0.57 | 1.74 | 1.28 |
| Crip1 | 0.77 | 1.13 | 0.94 | 0.70 | 0.58 | 0.79 | 1.00 | 0.47 | 1.00 | 0.93 | 1.10 | 0.93 |
| Crisp2 | 1.00 | 1.00 | 1.00 | 1.00 | 1.00 | 1.00 | 1.00 | 1.00 | 1.00 | 1.00 | 1.00 | 1.00 |
| Crls1 | 1.01 | 1.16 | 0.67 | 1.03 | 0.99 | 0.96 | 1.01 | 1.16 | 1.03 | 1.05 | 1.33 | 1.10 |
| Crmp1 | 0.59 | 0.78 | 0.92 | 1.00 | 1.00 | 1.00 | 1.00 | 1.00 | 1.00 | 1.65 | 1.50 | 1.20 |
| Crnde | 1.00 | 1.25 | 1.00 | 1.00 | 0.70 | 0.96 | 1.00 | 1.00 | 1.00 | 1.00 | 1.00 | 1.00 |
| Cryaa | 2.27 | 1.04 | 0.96 | 5.92 | 8.08 | 6.08 | 1.00 | 1.00 | 1.00 | 1.00 | 1.00 | 1.00 |
| Cryba4 | 1.99 | 2.39 | 1.32 | 1.00 | 1.00 | 1.00 | 1.00 | 1.00 | 1.00 | 1.00 | 1.00 | 1.00 |
| Crybb3 | 1.40 | 0.73 | 1.12 | 1.00 | 0.54 | 1.00 | 1.00 | 2.64 | 1.00 | 1.03 | 3.69 | 0.97 |
| Crygn | 1.00 | 1.00 | 1.00 | 1.00 | 1.00 | 1.00 | 1.00 | 1.00 | 1.00 | 1.00 | 1.00 | 1.00 |
| Crym | 1.00 | 1.00 | 1.00 | 0.82 | 1.10 | 0.83 | 1.00 | 1.00 | 1.00 | 1.00 | 1.14 | 0.70 |
| Cspg5 | 1.00 | 1.00 | 1.00 | 1.00 | 1.00 | 1.00 | 1.00 | 1.00 | 1.00 | 1.00 | 1.00 | 1.00 |
| Csrnp1 | 0.85 | 0.80 | 0.95 | 1.33 | 4.12 | 1.45 | 1.13 | 2.87 | 1.54 | 0.97 | 1.40 | 0.92 |
| Csrp2 | 2.75 | 2.30 | 1.30 | 1.03 | 0.87 | 0.94 | 0.96 | 1.47 | 0.90 | 1.02 | 1.73 | 1.00 |
| Csrp3 | 1.00 | 1.00 | 1.00 | 1.00 | 1.00 | 1.00 | 1.94 | 2.38 | 1.73 | 1.00 | 1.00 | 1.00 |
| Cst3 | 1.52 | 1.65 | 1.25 | 1.06 | 0.77 | 1.20 | 1.13 | 1.70 | 1.13 | 1.07 | 1.58 | 1.16 |
| Cst6 | 1.11 | 0.97 | 0.72 | 1.00 | 1.00 | 1.00 | 1.00 | 1.00 | 1.00 | 1.00 | 1.00 | 0.47 |
| Csta1 | 1.00 | 1.00 | 1.00 | 1.00 | 1.00 | 1.00 | 1.00 | 1.00 | 1.00 | 1.00 | 1.00 | 1.00 |
| Ctc1 | 0.79 | 1.01 | 0.81 | 0.76 | 0.52 | 0.86 | 1.12 | 1.56 | 0.83 | 0.95 | 1.20 | 0.93 |
| Ctcflos | 1.00 | 1.00 | 1.11 | 1.23 | 1.00 | 1.00 | 5.77 | 4.35 | 5.37 | 1.00 | 1.00 | 1.00 |
| Ctdnep1 | 1.11 | 1.33 | 1.07 | 0.97 | 0.71 | 1.00 | 0.95 | 2.04 | 1.00 | 0.96 | 1.41 | 0.98 |
| Ctgf | 3.12 | 3.05 | 1.65 | 0.96 | 0.99 | 1.17 | 2.00 | 1.03 | 2.39 | 0.84 | 0.77 | 0.95 |
| Ctla2a | 2.93 | 2.32 | 1.34 | 1.41 | 0.76 | 1.30 | 2.61 | 4.88 | 1.73 | 1.93 | 3.26 | 1.50 |
| Ctla2b | 5.36 | 4.08 | 2.20 | 1.18 | 1.10 | 1.08 | 1.14 | 0.90 | 1.20 | 1.61 | 2.47 | 1.71 |
| Ctrb1 | 1.00 | 1.44 | 1.83 | 1.00 | 1.05 | 0.79 | 1.00 | 2.04 | 0.78 | 0.48 | 2.68 | 34.25 |
| Ctrc | 1.00 | 1.00 | 1.00 | 1.00 | 1.00 | 1.00 | 1.00 | 1.00 | 1.00 | 0.34 | 2.45 | 28.48 |
| Ctrl | 1.00 | 1.00 | 1.25 | 1.00 | 1.00 | 1.67 | 1.00 | 1.00 | 0.62 | 0.43 | 2.35 | 29.18 |
| Ctsa | 1.60 | 1.92 | 1.41 | 1.04 | 1.01 | 1.15 | 1.00 | 1.10 | 1.17 | 1.13 | 1.50 | 1.05 |
| Ctsd | 2.29 | 2.43 | 1.78 | 1.15 | 0.90 | 1.15 | 1.07 | 1.78 | 0.98 | 1.11 | 1.63 | 1.09 |
| Ctsg | 1.00 | 1.00 | 1.00 | 1.00 | 1.00 | 1.00 | 1.00 | 1.00 | 1.00 | 1.00 | 1.00 | 1.00 |
| Ctsh | 2.42 | 2.14 | 2.07 | 1.01 | 1.17 | 0.99 | 0.70 | 0.65 | 0.77 | 0.83 | 1.53 | 1.07 |
| Ctsl | 1.28 | 1.31 | 1.08 | 2.34 | 3.56 | 1.09 | 2.64 | 1.89 | 2.29 | 1.30 | 1.46 | 1.08 |
| Ctsz | 1.99 | 2.06 | 1.53 | 1.06 | 0.79 | 1.16 | 0.95 | 1.74 | 1.03 | 1.03 | 1.57 | 1.13 |
| Ctu2 | 0.91 | 1.14 | 0.85 | 0.80 | 1.58 | 0.99 | 1.19 | 1.77 | 0.94 | 1.16 | 1.59 | 1.05 |
| Ctxn1 | 0.79 | 1.01 | 0.74 | 0.86 | 0.58 | 0.79 | 0.86 | 1.09 | 0.97 | 0.78 | 0.88 | 1.02 |
| Ctxn3 | 1.46 | 1.00 | 1.01 | 2.01 | 2.29 | 1.06 | 1.00 | 1.00 | 1.00 | 1.13 | 1.07 | 1.30 |
| Cuedc2 | 1.13 | 1.46 | 0.96 | 0.79 | 0.46 | 0.61 | 0.85 | 2.10 | 0.87 | 0.97 | 1.44 | 0.88 |
| Cuta | 1.04 | 1.33 | 0.90 | 0.70 | 0.58 | 0.79 | 0.60 | 1.42 | 0.75 | 0.83 | 1.45 | 0.89 |
| Cutc | 1.31 | 1.53 | 1.13 | 1.12 | 0.97 | 1.02 | 1.26 | 0.30 | 1.12 | 0.88 | 1.44 | 1.02 |
| Cuzd1 | 1.00 | 1.00 | 1.00 | 1.00 | 1.00 | 1.00 | 1.00 | 1.00 | 1.00 | 0.55 | 3.47 | 5.45 |
| Cx3cl1 | 1.29 | 0.97 | 1.32 | 0.66 | 0.60 | 0.74 | 1.00 | 1.00 | 1.00 | 0.78 | 0.61 | 0.82 |
| Cxcl13 | 3.84 | 3.81 | 3.07 | 1.00 | 1.00 | 1.00 | 1.00 | 1.00 | 3.15 | 1.78 | 1.95 | 1.48 |
| Cyb5rl | 0.93 | 0.97 | 1.07 | 0.67 | 0.52 | 0.87 | 0.90 | 1.75 | 0.94 | 1.02 | 1.03 | 0.86 |
| Cyba | 1.38 | 1.86 | 1.32 | 0.83 | 0.83 | 1.01 | 0.79 | 0.73 | 1.12 | 0.90 | 1.29 | 0.92 |
| Cyp17a1 | 1.00 | 1.00 | 1.00 | 1.00 | 1.00 | 1.00 | 7.34 | 6.24 | 7.99 | 1.00 | 1.00 | 1.00 |
| Cyp1b1 | 1.27 | 0.83 | 1.20 | 0.69 | 1.18 | 0.97 | 1.00 | 1.00 | 1.00 | 1.00 | 1.00 | 1.00 |
| Cyp24a1 | 1.00 | 1.00 | 1.00 | 5.04 | 2.92 | 3.29 | 1.00 | 1.00 | 1.00 | 1.00 | 1.00 | 1.00 |
| Cyp26b1 | 0.34 | 0.49 | 0.74 | 1.54 | 2.28 | 1.16 | 1.40 | 3.23 | 1.21 | 1.77 | 2.13 | 0.80 |
| Cyp27b1 | 1.00 | 1.00 | 1.00 | 4.45 | 3.03 | 5.57 | 1.00 | 1.00 | 1.00 | 1.00 | 1.00 | 1.00 |
| Cyp2b10 | 1.60 | 4.67 | 1.14 | 8.96 | 10.25 | 1.87 | 14.57 | 23.55 | 6.32 | 1.00 | 1.00 | 1.00 |
| Cyp2e1 | 1.18 | 1.30 | 1.53 | 2.86 | 2.21 | 1.87 | 1.14 | 1.17 | 1.28 | 2.16 | 5.28 | 2.21 |
| Cyp2s1 | 1.52 | 1.05 | 1.44 | 0.95 | 0.73 | 1.05 | 1.00 | 1.00 | 1.00 | 0.99 | 1.01 | 1.03 |
| Cyp4a10 | 6.71 | 1.00 | 1.00 | 0.87 | 0.92 | 0.79 | 1.45 | 0.89 | 1.79 | 1.01 | 1.00 | 1.15 |

Fig. 35- 151

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Cpa1 | 39.54 | 1.51 | 2.33 | 1.00 | 1.00 | 0.82 | 1.00 | 2.24 | 1.64 | 2.73 | 7.51 | 0.73 |
| Cpa2 | 10.14 | 1.91 | 2.94 | 1.00 | 1.00 | 0.72 | 1.00 | 1.00 | 0.90 | 1.07 | 9.71 | 0.78 |
| Cpb1 | 34.22 | 1.87 | 3.05 | 1.00 | 1.00 | 0.91 | 1.00 | 1.00 | 0.99 | 3.12 | 9.17 | 0.83 |
| Cpe | 1.23 | 1.33 | 1.48 | 1.39 | 2.13 | 1.55 | 0.84 | 1.29 | 0.85 | 1.42 | 12.42 | 0.92 |
| Cplx1 | 0.94 | 1.32 | 1.45 | 1.00 | 1.00 | 0.82 | 1.84 | 1.28 | 1.66 | 1.00 | 38.62 | 1.00 |
| Cplx2 | 0.80 | 0.76 | 0.71 | 0.90 | 0.45 | 0.99 | 1.00 | 1.00 | 1.00 | 0.68 | 5.75 | 0.98 |
| Cpsf3l | 1.05 | 0.79 | 1.23 | 0.91 | 2.49 | 0.87 | 0.84 | 1.92 | 1.10 | 1.10 | 1.02 | 0.85 |
| Cpsf4 | 0.95 | 1.21 | 0.97 | 0.91 | 2.58 | 1.17 | 0.85 | 1.14 | 0.95 | 1.11 | 1.27 | 0.92 |
| Cpsf4l | 1.00 | 1.00 | 1.00 | 1.00 | 1.00 | 1.00 | 1.08 | 1.28 | 0.83 | 1.00 | 1.00 | 1.00 |
| Cpt1c | 1.00 | 1.00 | 1.03 | 0.51 | 1.63 | 0.71 | 0.89 | 2.55 | 0.85 | 1.00 | 2.67 | 0.79 |
| Cpxm1 | 0.60 | 0.45 | 0.56 | 0.63 | 1.36 | 0.67 | 1.01 | 5.34 | 1.13 | 0.53 | 0.57 | 0.38 |
| Crabp1 | 1.00 | 1.00 | 1.00 | 1.09 | 2.05 | 2.97 | 1.02 | 0.96 | 1.16 | 1.00 | 1.00 | 1.00 |
| Crip1 | 0.74 | 0.73 | 0.85 | 1.20 | 2.08 | 1.05 | 1.00 | 2.83 | 1.00 | 0.63 | 0.85 | 0.61 |
| Crisp2 | 1.00 | 1.00 | 1.00 | 2.77 | 1.39 | 1.00 | 1.01 | 0.82 | 1.06 | 1.00 | 1.00 | 1.00 |
| Cris1 | 0.89 | 1.01 | 0.88 | 1.81 | 7.00 | 2.03 | 0.97 | 1.23 | 0.92 | 1.18 | 1.36 | 0.86 |
| Crmp1 | 1.00 | 1.00 | 1.00 | 1.00 | 1.00 | 1.00 | 0.95 | 1.32 | 1.08 | 0.96 | 5.28 | 1.16 |
| Crnde | 1.24 | 0.91 | 0.59 | 1.00 | 1.00 | 1.00 | 0.78 | 1.52 | 0.79 | 1.00 | 1.00 | 1.00 |
| Cryaa | 1.00 | 1.00 | 1.00 | 1.00 | 1.00 | 1.00 | 1.00 | 1.00 | 1.00 | 1.00 | 1.00 | 1.00 |
| Cryba4 | 1.00 | 1.00 | 1.00 | 1.00 | 1.00 | 1.00 | 1.00 | 2.63 | 1.00 | 1.78 | 3.53 | 1.40 |
| Crybb3 | 1.14 | 2.13 | 1.58 | 1.00 | 3.41 | 1.00 | 1.00 | 2.87 | 1.00 | 1.00 | 1.00 | 1.00 |
| Crygn | 1.00 | 1.00 | 1.00 | 1.48 | 4.35 | 1.05 | 1.00 | 1.00 | 1.00 | 1.00 | 1.00 | 1.00 |
| Crym | 1.00 | 1.00 | 1.00 | 1.00 | 1.00 | 1.00 | 1.00 | 1.00 | 1.00 | 1.00 | 3.33 | 1.00 |
| Cspg5 | 1.00 | 1.00 | 1.00 | 1.00 | 1.00 | 1.00 | 1.00 | 1.00 | 0.90 | 1.00 | 6.57 | 1.00 |
| Csrnp1 | 1.27 | 1.76 | 1.02 | 1.65 | 0.71 | 1.82 | 0.95 | 0.88 | 1.13 | 1.23 | 1.18 | 1.22 |
| Csrp2 | 1.07 | 1.05 | 0.92 | 1.84 | 2.87 | 2.43 | 1.32 | 1.49 | 1.04 | 1.48 | 1.71 | 1.17 |
| Csrp3 | 5.27 | 1.96 | 2.08 | 1.00 | 1.00 | 1.00 | 1.00 | 1.00 | 1.00 | 1.00 | 1.00 | 1.00 |
| Cst3 | 1.02 | 1.25 | 1.16 | 0.94 | 2.23 | 0.81 | 0.79 | 1.85 | 0.85 | 0.86 | 1.17 | 0.89 |
| Cst6 | 0.73 | 1.28 | 1.49 | 0.71 | 1.89 | 0.89 | 1.00 | 1.00 | 1.00 | 1.00 | 1.00 | 1.00 |
| Csta1 | 1.03 | 0.95 | 1.66 | 1.00 | 1.00 | 1.00 | 1.00 | 1.00 | 1.00 | 1.00 | 1.00 | 1.00 |
| Ctc1 | 0.99 | 0.85 | 1.02 | 0.80 | 0.94 | 0.80 | 1.04 | 2.84 | 1.07 | 1.11 | 1.02 | 1.00 |
| Ctcflos | 1.00 | 1.00 | 1.00 | 1.96 | 0.60 | 2.20 | 1.00 | 1.00 | 1.00 | 1.00 | 1.00 | 1.00 |
| Ctdnep1 | 0.98 | 0.97 | 1.06 | 0.97 | 2.28 | 1.04 | 0.96 | 2.87 | 1.13 | 0.96 | 1.02 | 0.92 |
| Ctgf | 1.45 | 1.75 | 1.10 | 2.10 | 2.75 | 1.82 | 1.40 | 0.90 | 1.46 | 1.65 | 1.83 | 1.96 |
| Ctla2a | 2.13 | 2.00 | 2.03 | 2.12 | 7.62 | 1.90 | 1.00 | 2.54 | 1.42 | 1.43 | 1.34 | 1.07 |
| Ctla2b | 2.46 | 3.05 | 1.30 | 1.51 | 1.27 | 1.53 | 1.00 | 1.00 | 1.00 | 1.41 | 1.48 | 1.25 |
| Ctrb1 | 227.96 | 2.19 | 2.83 | 1.00 | 1.00 | 0.82 | 1.00 | 4.14 | 1.17 | 3.59 | 11.27 | 0.75 |
| Ctrc | 9.52 | 2.09 | 2.23 | 1.00 | 1.00 | 0.86 | 1.00 | 1.00 | 1.00 | 1.00 | 10.26 | 1.03 |
| Ctrl | 21.82 | 1.69 | 2.78 | 1.00 | 1.00 | 0.97 | 1.00 | 1.02 | 1.09 | 1.63 | 7.30 | 0.66 |
| Ctsa | 1.16 | 1.23 | 1.12 | 0.79 | 2.91 | 0.70 | 0.64 | 1.18 | 0.79 | 1.04 | 1.26 | 0.96 |
| Ctsd | 0.99 | 1.12 | 0.99 | 0.80 | 1.40 | 0.56 | 0.98 | 2.11 | 0.90 | 1.26 | 1.77 | 1.00 |
| Ctsg | 1.00 | 1.00 | 1.00 | 1.00 | 1.00 | 1.00 | 1.00 | 1.00 | 1.00 | 6.28 | 4.50 | 3.11 |
| Ctsh | 1.16 | 0.85 | 1.20 | 1.00 | 3.00 | 1.13 | 1.18 | 0.79 | 0.77 | 0.94 | 1.11 | 0.92 |
| Ctsl | 1.29 | 1.28 | 1.15 | 2.39 | 1.77 | 0.89 | 0.98 | 0.40 | 0.97 | 2.09 | 2.42 | 1.47 |
| Ctsz | 0.93 | 0.94 | 0.96 | 1.05 | 2.15 | 0.82 | 0.64 | 1.55 | 0.76 | 1.16 | 1.47 | 1.06 |
| Ctu2 | 1.08 | 0.89 | 0.98 | 0.94 | 8.78 | 1.39 | 0.90 | 0.52 | 1.12 | 0.88 | 1.07 | 0.82 |
| Ctxn1 | 0.90 | 0.95 | 1.19 | 1.31 | 3.04 | 2.68 | 0.94 | 1.01 | 0.96 | 1.18 | 12.86 | 0.87 |
| Ctxn3 | 1.62 | 1.29 | 1.13 | 2.34 | 1.00 | 2.68 | 1.00 | 1.00 | 1.00 | 1.00 | 1.00 | 1.00 |
| Cuedc2 | 1.04 | 1.07 | 1.34 | 0.66 | 1.46 | 0.87 | 0.63 | 3.78 | 1.02 | 1.01 | 1.36 | 0.95 |
| Cuta | 0.94 | 1.06 | 0.90 | 0.66 | 1.65 | 0.98 | 0.82 | 2.41 | 0.82 | 0.89 | 1.07 | 0.85 |
| Cutc | 0.96 | 1.39 | 0.80 | 1.20 | 0.92 | 1.15 | 0.95 | 0.37 | 0.82 | 1.35 | 1.32 | 0.96 |
| Cuzd1 | 1.95 | 1.72 | 3.62 | 2.10 | 18.93 | 0.19 | 1.36 | 1.70 | 0.94 | 1.00 | 2.52 | 1.00 |
| Cx3cl1 | 0.86 | 0.93 | 0.78 | 1.72 | 0.92 | 2.17 | 0.80 | 1.00 | 0.86 | 0.89 | 13.09 | 0.86 |
| Cxcl13 | 6.26 | 2.26 | 4.22 | 1.43 | 1.00 | 4.73 | 1.00 | 1.00 | 1.00 | 0.80 | 0.68 | 0.77 |
| Cyb5rl | 0.86 | 0.82 | 1.24 | 0.74 | 1.33 | 0.73 | 1.04 | 4.48 | 1.24 | 0.99 | 0.89 | 0.94 |
| Cyba | 0.91 | 1.01 | 1.00 | 0.91 | 3.08 | 0.69 | 0.64 | 1.73 | 0.86 | 1.04 | 1.24 | 0.81 |
| Cyp17a1 | 1.00 | 1.00 | 1.00 | 0.41 | 1.00 | 0.63 | 0.71 | 0.30 | 0.40 | 1.00 | 1.00 | 1.00 |
| Cyp1b1 | 2.38 | 2.46 | 1.61 | 3.23 | 0.26 | 1.76 | 1.00 | 1.93 | 1.28 | 1.16 | 0.78 | 1.29 |
| Cyp24a1 | 1.00 | 1.00 | 1.00 | 1.00 | 1.00 | 1.00 | 1.00 | 1.00 | 1.00 | 1.00 | 1.00 | 1.00 |
| Cyp26b1 | 3.24 | 5.74 | 1.22 | 1.59 | 1.28 | 1.42 | 0.81 | 0.78 | 0.88 | 1.27 | 2.21 | 1.32 |
| Cyp27b1 | 0.59 | 0.49 | 0.81 | 1.00 | 1.00 | 1.00 | 1.00 | 1.00 | 1.00 | 1.00 | 1.00 | 1.00 |
| Cyp2b10 | 3.42 | 5.48 | 2.73 | 26.69 | 17.65 | 25.32 | 1.00 | 1.00 | 1.00 | 1.04 | 1.00 | 1.00 |
| Cyp2e1 | 1.53 | 1.83 | 3.83 | 0.78 | 1.90 | 2.65 | 0.85 | 4.67 | 0.80 | 0.68 | 4.12 | 2.42 |
| Cyp2s1 | 1.13 | 1.51 | 1.01 | 0.94 | 1.19 | 1.19 | 1.12 | 1.98 | 1.04 | 0.83 | 0.79 | 1.19 |
| Cyp4a10 | 2.01 | 2.71 | 3.49 | 0.89 | 1.00 | 1.00 | 1.00 | 1.00 | 1.00 | 1.00 | 1.00 | 1.00 |

Fig. 35- 152

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Cpa1 | 0.87 | 0.75 | 0.78 | 1.00 | 1.00 | 0.67 | 1.00 | 1.00 | 0.97 | 1.00 | 0.86 | 1.16 |
| Cpa2 | 1.03 | 1.13 | 1.04 | 0.78 | 0.38 | 1.21 | 1.00 | 1.00 | 1.00 | 1.00 | 1.00 | 1.00 |
| Cpb1 | 1.15 | 1.12 | 1.16 | 1.00 | 0.59 | 0.64 | 1.00 | 1.00 | 0.72 | 1.00 | 1.00 | 1.56 |
| Cpe | 0.76 | 0.69 | 1.09 | 1.14 | 1.18 | 1.06 | 1.32 | 3.59 | 1.20 | 1.00 | 1.00 | 1.00 |
| Cplx1 | 1.00 | 1.00 | 1.00 | 1.08 | 1.08 | 1.01 | 1.00 | 1.00 | 1.00 | 1.00 | 1.00 | 1.00 |
| Cplx2 | 0.83 | 0.95 | 1.00 | 1.19 | 1.07 | 1.03 | 0.78 | 1.16 | 0.99 | 0.88 | 0.45 | 0.65 |
| Cpsf3l | 0.84 | 0.81 | 0.95 | 0.99 | 1.11 | 0.93 | 0.95 | 5.40 | 0.90 | 1.90 | 1.14 | 1.13 |
| Cpsf4 | 0.85 | 0.64 | 0.67 | 0.97 | 1.67 | 0.86 | 1.38 | 5.27 | 1.06 | 1.84 | 1.21 | 1.20 |
| Cpsf4l | 1.00 | 1.00 | 1.00 | 1.00 | 2.19 | 1.00 | 1.36 | 7.94 | 1.16 | 1.00 | 1.00 | 1.00 |
| Cpt1c | 1.00 | 1.00 | 1.00 | 1.00 | 0.81 | 0.94 | 0.85 | 5.09 | 0.63 | 1.00 | 1.00 | 1.00 |
| Cpxm1 | 1.00 | 1.00 | 1.00 | 0.71 | 0.70 | 1.16 | 1.04 | 19.97 | 1.18 | 1.32 | 1.00 | 1.00 |
| Crabp1 | 1.00 | 1.00 | 1.00 | 0.85 | 6.45 | 1.10 | 1.63 | 0.83 | 0.84 | 1.00 | 1.00 | 1.00 |
| Crip1 | 0.68 | 1.00 | 1.41 | 0.74 | 1.41 | 0.84 | 1.55 | 8.80 | 0.96 | 1.92 | 0.73 | 0.88 |
| Crisp2 | 1.00 | 1.00 | 1.00 | 1.00 | 1.00 | 1.00 | 10.56 | 1.00 | 1.00 | 1.00 | 1.00 | 1.00 |
| Cris1 | 1.17 | 1.04 | 1.08 | 1.07 | 1.39 | 1.06 | 1.23 | 3.75 | 0.87 | 1.30 | 0.97 | 1.28 |
| Crmp1 | 1.00 | 1.00 | 1.00 | 1.05 | 1.26 | 0.93 | 1.00 | 1.00 | 1.00 | 1.00 | 1.00 | 1.00 |
| Crnde | 1.00 | 1.00 | 1.00 | 1.00 | 5.11 | 1.00 | 1.62 | 5.97 | 1.03 | 1.00 | 1.00 | 1.00 |
| Cryaa | 1.00 | 1.00 | 1.00 | 1.00 | 1.20 | 1.00 | 0.87 | 1.00 | 0.74 | 1.00 | 1.00 | 1.00 |
| Cryba4 | 1.00 | 1.00 | 1.00 | 1.00 | 0.47 | 1.17 | 1.22 | 15.05 | 1.09 | 3.33 | 2.22 | 1.69 |
| Crybb3 | 1.00 | 1.00 | 1.00 | 1.00 | 0.50 | 1.00 | 1.42 | 14.02 | 1.04 | 1.00 | 1.00 | 1.00 |
| Crygn | 1.00 | 1.00 | 1.00 | 1.00 | 0.47 | 1.00 | 2.21 | 23.37 | 1.12 | 1.00 | 1.00 | 1.00 |
| Crym | 1.00 | 1.00 | 1.00 | 1.21 | 7.50 | 1.08 | 1.49 | 2.93 | 1.05 | 1.00 | 1.00 | 1.00 |
| Cspg5 | 1.00 | 1.00 | 1.00 | 0.94 | 0.82 | 0.94 | 0.92 | 1.32 | 0.70 | 1.00 | 1.00 | 1.00 |
| Csrnp1 | 1.13 | 2.16 | 1.36 | 1.26 | 2.27 | 1.11 | 1.58 | 0.75 | 1.18 | 0.60 | 1.22 | 1.27 |
| Csrp2 | 0.85 | 1.12 | 0.84 | 0.76 | 1.04 | 1.00 | 1.03 | 11.21 | 1.64 | 2.39 | 1.03 | 1.21 |
| Csrp3 | 1.00 | 1.00 | 1.00 | 1.00 | 1.00 | 1.00 | 1.49 | 4.36 | 1.74 | 2.25 | 2.17 | 0.63 |
| Cst3 | 1.02 | 1.29 | 0.98 | 1.05 | 0.85 | 1.05 | 1.21 | 6.02 | 1.13 | 2.44 | 1.44 | 1.26 |
| Cst6 | 1.00 | 1.00 | 1.00 | 1.00 | 1.07 | 1.00 | 1.61 | 11.87 | 0.71 | 1.00 | 1.00 | 1.00 |
| Csta1 | 1.00 | 1.00 | 1.00 | 1.00 | 1.00 | 1.00 | 0.72 | 6.76 | 0.76 | 1.00 | 1.00 | 1.00 |
| Ctc1 | 1.00 | 1.00 | 1.00 | 0.83 | 0.80 | 0.95 | 1.06 | 6.54 | 1.05 | 2.61 | 0.98 | 0.94 |
| Ctcflos | 1.00 | 1.00 | 1.00 | 1.00 | 1.00 | 1.00 | 1.00 | 1.00 | 1.00 | 1.00 | 1.00 | 1.00 |
| Ctdnep1 | 0.68 | 0.91 | 0.73 | 1.14 | 1.07 | 1.01 | 1.26 | 10.29 | 1.11 | 2.54 | 1.23 | 1.18 |
| Ctgf | 2.83 | 4.90 | 2.59 | 2.19 | 1.31 | 1.59 | 1.70 | 1.71 | 1.95 | 1.09 | 3.44 | 1.92 |
| Ctla2a | 1.00 | 1.00 | 1.00 | 1.82 | 3.05 | 1.20 | 2.97 | 14.57 | 2.91 | 2.47 | 1.73 | 1.90 |
| Ctla2b | 1.00 | 1.00 | 1.00 | 1.00 | 1.00 | 1.00 | 2.64 | 5.24 | 3.64 | 1.43 | 1.43 | 1.85 |
| Ctrb1 | 1.15 | 1.05 | 0.90 | 1.11 | 0.25 | 0.69 | 0.30 | 6.27 | 1.01 | 1.00 | 0.71 | 1.08 |
| Ctrc | 0.86 | 0.92 | 0.86 | 1.00 | 1.00 | 1.00 | 1.00 | 1.00 | 1.00 | 1.00 | 1.00 | 1.00 |
| Ctrl | 1.01 | 0.88 | 0.92 | 1.00 | 4.73 | 0.86 | 1.00 | 2.78 | 1.09 | 1.00 | 0.63 | 0.94 |
| Ctsa | 0.78 | 0.83 | 0.78 | 1.09 | 0.78 | 1.01 | 1.03 | 4.45 | 0.85 | 2.31 | 1.32 | 1.13 |
| Ctsd | 0.78 | 0.84 | 0.81 | 1.28 | 1.09 | 1.22 | 1.27 | 7.32 | 0.91 | 2.79 | 1.42 | 1.20 |
| Ctsg | 1.00 | 1.00 | 1.00 | 1.00 | 1.00 | 1.00 | 1.00 | 1.00 | 1.22 | 1.02 | 1.19 | 1.29 |
| Ctsh | 1.00 | 1.00 | 1.28 | 1.09 | 0.85 | 0.90 | 0.98 | 2.61 | 0.90 | 2.16 | 1.30 | 1.13 |
| Ctsl | 1.06 | 1.23 | 1.04 | 1.10 | 0.57 | 1.05 | 1.27 | 0.75 | 1.28 | 1.02 | 1.45 | 1.27 |
| Ctsz | 0.94 | 1.05 | 0.90 | 1.19 | 1.37 | 1.15 | 1.40 | 8.89 | 1.23 | 2.95 | 1.25 | 1.19 |
| Ctu2 | 1.44 | 1.00 | 1.11 | 1.24 | 1.67 | 1.12 | 1.26 | 1.88 | 1.01 | 1.14 | 1.05 | 1.34 |
| Ctxn1 | 1.00 | 1.00 | 1.00 | 1.07 | 1.16 | 1.06 | 1.04 | 0.53 | 0.99 | 2.41 | 0.92 | 1.12 |
| Ctxn3 | 1.00 | 1.00 | 1.00 | 1.25 | 0.94 | 1.26 | 6.27 | 4.92 | 6.70 | 1.00 | 1.00 | 1.00 |
| Cuedc2 | 0.73 | 0.94 | 0.89 | 1.00 | 0.96 | 0.99 | 1.36 | 15.70 | 0.87 | 3.37 | 1.10 | 1.29 |
| Cuta | 0.51 | 0.60 | 0.96 | 1.40 | 1.11 | 0.98 | 1.16 | 8.00 | 0.87 | 2.57 | 1.14 | 1.13 |
| Cutc | 0.52 | 0.49 | 0.72 | 1.06 | 1.56 | 1.21 | 0.87 | 2.49 | 0.93 | 1.09 | 1.22 | 1.16 |
| Cuzd1 | 1.37 | 1.56 | 1.15 | 1.00 | 1.00 | 1.00 | 1.00 | 1.00 | 1.00 | 1.00 | 1.00 | 1.00 |
| Cx3cl1 | 1.00 | 1.00 | 1.00 | 1.11 | 1.57 | 1.06 | 0.65 | 0.25 | 0.60 | 1.00 | 1.00 | 1.00 |
| Cxcl13 | 0.19 | 0.90 | 0.63 | 1.00 | 1.00 | 1.00 | 1.22 | 0.79 | 0.99 | 1.00 | 1.00 | 1.00 |
| Cyb5rl | 0.56 | 1.00 | 0.82 | 0.92 | 1.29 | 1.13 | 1.16 | 6.74 | 1.26 | 1.84 | 0.78 | 0.74 |
| Cyba | 1.10 | 0.76 | 0.75 | 0.80 | 0.57 | 1.62 | 1.39 | 10.25 | 1.17 | 3.71 | 1.58 | 1.42 |
| Cyp17a1 | 1.00 | 1.00 | 1.00 | 1.00 | 1.00 | 1.00 | 1.89 | 1.77 | 0.99 | 1.00 | 1.00 | 1.00 |
| Cyp1b1 | 0.99 | 1.00 | 1.09 | 1.10 | 1.00 | 1.11 | 1.71 | 0.23 | 1.71 | 1.00 | 1.00 | 1.00 |
| Cyp24a1 | 1.00 | 1.00 | 1.00 | 1.00 | 1.00 | 1.00 | 1.00 | 1.00 | 1.00 | 1.00 | 1.00 | 1.00 |
| Cyp26b1 | 2.34 | 3.39 | 1.00 | 1.47 | 0.44 | 1.19 | 1.45 | 0.90 | 1.41 | 1.00 | 1.00 | 1.00 |
| Cyp27b1 | 1.00 | 1.00 | 1.00 | 1.00 | 1.00 | 1.00 | 1.00 | 1.00 | 1.00 | 1.00 | 1.00 | 1.00 |
| Cyp2b10 | 1.00 | 1.00 | 1.00 | 1.00 | 1.00 | 1.00 | 1.81 | 2.69 | 1.46 | 1.00 | 1.00 | 1.00 |
| Cyp2e1 | 0.28 | 0.81 | 0.83 | 0.43 | 1.00 | 1.85 | 5.86 | 25.89 | 5.75 | 1.00 | 1.00 | 1.00 |
| Cyp2s1 | 1.00 | 1.00 | 1.00 | 0.98 | 0.85 | 0.85 | 1.24 | 5.25 | 1.11 | 1.00 | 1.00 | 1.00 |
| Cyp4a10 | 1.00 | 1.00 | 1.00 | 1.00 | 1.00 | 1.00 | 1.00 | 1.00 | 1.00 | 1.00 | 1.00 | 1.00 |

Fig. 35- 153

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Cyp4a14 | 1.00 | 1.00 | 1.00 | 1.00 | 1.41 | 1.00 | 3.77 | 0.30 | 1.00 | 0.21 | 1.00 | 1.00 |
| Cyp4f13 | 0.74 | 0.53 | 0.99 | 0.45 | 6.52 | 1.18 | 1.24 | 0.92 | 0.97 | 4.05 | 4.63 | 0.95 |
| Cyp4f15 | 1.00 | 1.00 | 1.00 | 1.00 | 1.00 | 1.00 | 1.00 | 1.00 | 1.00 | 2.77 | 5.01 | 1.37 |
| Cyp51 | 1.67 | 1.37 | 1.50 | 2.64 | 4.16 | 1.60 | 1.76 | 1.62 | 0.89 | 2.27 | 1.83 | 1.39 |
| Cypt12 | 1.00 | 1.00 | 1.00 | 1.00 | 1.00 | 1.00 | 1.00 | 1.00 | 1.00 | 1.00 | 1.00 | 1.00 |
| Cys1 | 0.53 | 0.38 | 0.53 | 0.62 | 2.00 | 0.59 | 0.59 | 0.68 | 0.57 | 1.13 | 1.40 | 0.54 |
| Cytl1 | 1.92 | 2.18 | 2.48 | 1.40 | 6.30 | 1.81 | 0.97 | 0.87 | 1.05 | 1.95 | 2.21 | 1.15 |
| D17H6S53E | 0.82 | 0.47 | 0.96 | 0.56 | 3.82 | 0.97 | 0.67 | 0.56 | 0.87 | 3.86 | 3.65 | 1.13 |
| D19Bwg1357e | 1.47 | 0.76 | 1.16 | 0.89 | 6.73 | 1.15 | 1.01 | 1.10 | 0.87 | 2.46 | 2.50 | 0.94 |
| D230025D16Rik | 4.04 | 5.66 | 3.92 | 1.57 | 1.46 | 1.69 | 3.87 | 3.57 | 1.23 | 0.35 | 0.64 | 1.16 |
| D2Wsu81e | 0.92 | 0.47 | 0.90 | 0.46 | 6.50 | 0.88 | 1.01 | 0.96 | 1.04 | 2.73 | 3.87 | 1.27 |
| D330041H03Rik | 0.88 | 0.62 | 0.99 | 0.43 | 4.84 | 0.83 | 0.82 | 0.62 | 0.80 | 1.05 | 2.04 | 0.76 |
| D330050I16Rik | 0.74 | 0.53 | 1.10 | 0.98 | 1.73 | 1.13 | 1.86 | 1.47 | 1.58 | 2.14 | 2.29 | 1.23 |
| D3Bwg0562e | 1.00 | 1.00 | 1.00 | 1.00 | 0.27 | 0.64 | 1.00 | 1.00 | 1.00 | 1.00 | 1.00 | 1.00 |
| D8Ertd738e | 1.38 | 1.07 | 1.05 | 0.49 | 3.68 | 1.16 | 1.00 | 0.90 | 0.84 | 1.14 | 2.07 | 1.07 |
| Dancr | 1.52 | 0.83 | 1.52 | 0.60 | 2.41 | 1.46 | 0.76 | 0.46 | 1.10 | 0.41 | 1.14 | 0.89 |
| Dao | 1.00 | 1.00 | 1.00 | 1.00 | 1.00 | 1.00 | 1.00 | 1.00 | 1.00 | 1.00 | 1.00 | 1.00 |
| Dap3 | 0.97 | 0.52 | 0.97 | 0.29 | 6.24 | 1.00 | 1.15 | 0.92 | 0.96 | 2.51 | 3.55 | 1.03 |
| Dapk3 | 1.27 | 0.60 | 1.07 | 0.30 | 7.12 | 1.04 | 1.01 | 0.89 | 1.06 | 3.44 | 3.85 | 1.06 |
| Dapp1 | 1.30 | 1.00 | 1.93 | 1.00 | 1.00 | 1.00 | 1.62 | 1.96 | 1.26 | 1.22 | 1.18 | 1.20 |
| Dbi | 1.15 | 0.64 | 1.18 | 0.22 | 4.95 | 0.80 | 0.85 | 0.70 | 0.78 | 1.94 | 3.18 | 1.06 |
| Dbil5 | 1.00 | 0.57 | 1.16 | 0.93 | 5.96 | 1.39 | 1.45 | 0.65 | 1.00 | 3.10 | 1.08 | 1.00 |
| Dclk1 | 1.00 | 1.00 | 1.00 | 1.00 | 0.12 | 1.00 | 1.00 | 1.00 | 1.00 | 1.00 | 1.00 | 1.00 |
| Dcps | 1.05 | 1.05 | 0.94 | 0.90 | 4.68 | 1.16 | 1.90 | 1.38 | 1.44 | 1.64 | 2.34 | 1.00 |
| Dctn2 | 1.31 | 0.69 | 0.99 | 0.57 | 6.21 | 1.11 | 1.09 | 0.92 | 1.02 | 1.78 | 2.41 | 0.94 |
| Dctn3 | 4.43 | 2.07 | 3.41 | 1.32 | 32.22 | 4.25 | 3.77 | 3.78 | 3.35 | 6.45 | 11.58 | 2.89 |
| Dctpp1 | 0.98 | 0.49 | 0.81 | 0.43 | 5.42 | 0.80 | 0.76 | 0.75 | 0.80 | 1.59 | 2.40 | 0.91 |
| Dcun1d5 | 1.40 | 0.64 | 1.05 | 0.65 | 4.73 | 1.08 | 1.02 | 1.10 | 1.18 | 2.41 | 3.52 | 0.96 |
| Dcxr | 0.77 | 0.31 | 0.62 | 0.16 | 10.84 | 0.98 | 0.94 | 0.81 | 0.75 | 3.48 | 5.09 | 1.17 |
| Ddb1 | 1.52 | 0.97 | 1.47 | 0.80 | 5.64 | 1.08 | 1.43 | 1.31 | 1.15 | 2.43 | 3.24 | 1.03 |
| Ddi2 | 1.30 | 1.00 | 2.19 | 2.01 | 0.43 | 0.84 | 5.73 | 6.15 | 4.57 | 1.00 | 1.00 | 1.68 |
| Ddit3 | 1.27 | 0.41 | 0.65 | 0.20 | 2.27 | 0.74 | 0.78 | 0.72 | 0.59 | 1.97 | 3.14 | 0.90 |
| Ddit4 | 2.93 | 7.00 | 5.98 | 5.10 | 5.80 | 6.66 | 2.37 | 2.81 | 1.52 | 2.02 | 3.27 | 4.61 |
| Ddn | 1.00 | 1.00 | 1.00 | 1.00 | 0.05 | 1.00 | 1.00 | 1.00 | 1.00 | 1.00 | 1.00 | 1.00 |
| Ddx47 | 1.06 | 0.92 | 0.86 | 0.30 | 2.12 | 1.01 | 1.16 | 0.80 | 0.73 | 0.70 | 1.23 | 0.85 |
| Ddx49 | 1.03 | 0.71 | 0.97 | 0.32 | 3.63 | 0.86 | 1.18 | 1.07 | 0.79 | 4.03 | 2.32 | 0.99 |
| Ddx56 | 1.57 | 0.92 | 1.44 | 0.59 | 5.78 | 1.16 | 1.02 | 1.43 | 1.15 | 3.05 | 3.53 | 1.01 |
| Decr1 | 0.67 | 0.60 | 0.76 | 0.63 | 2.75 | 0.74 | 0.68 | 0.75 | 0.67 | 2.99 | 2.08 | 1.08 |
| Dedd2 | 1.87 | 1.44 | 1.36 | 0.81 | 4.87 | 1.09 | 1.05 | 0.89 | 0.92 | 2.09 | 2.35 | 1.15 |
| Defa-rs1 | 1.00 | 1.00 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 | 1.00 | 1.00 |
| Defa17 | 1.00 | 1.00 | 1.00 | 1.00 | 1.00 | 1.00 | 1.00 | 1.00 | 1.00 | 1.00 | 1.00 | 1.00 |
| Defa23 | 1.00 | 1.00 | 1.00 | 1.00 | 1.00 | 1.00 | 1.00 | 1.00 | 1.00 | 1.00 | 1.00 | 1.00 |
| Defa24 | 1.00 | 1.00 | 1.00 | 1.00 | 1.00 | 1.00 | 1.00 | 1.00 | 1.00 | 1.00 | 1.00 | 1.00 |
| Defa3 | 1.00 | 1.00 | 1.00 | 1.00 | 1.00 | 1.00 | 1.00 | 1.00 | 1.00 | 1.00 | 1.00 | 1.00 |
| Defb1 | 1.00 | 1.00 | 1.00 | 1.00 | 1.00 | 1.00 | 1.00 | 1.00 | 1.00 | 1.00 | 1.00 | 1.00 |
| Defb11 | 1.00 | 1.00 | 1.00 | 1.00 | 1.00 | 1.00 | 1.00 | 1.00 | 1.00 | 1.00 | 1.00 | 1.00 |
| Defb14 | 1.00 | 1.00 | 1.00 | 1.00 | 1.00 | 1.00 | 1.00 | 1.00 | 1.00 | 1.00 | 1.00 | 1.00 |
| Defb2 | 1.00 | 1.00 | 1.00 | 1.00 | 1.00 | 1.00 | 1.00 | 1.00 | 1.00 | 1.00 | 1.00 | 1.00 |
| Defb22 | 1.00 | 1.00 | 1.00 | 1.00 | 1.00 | 1.00 | 1.00 | 1.00 | 1.00 | 1.00 | 1.00 | 1.00 |
| Defb25 | 1.00 | 1.49 | 1.00 | 2.00 | 1.00 | 1.00 | 1.00 | 1.00 | 1.00 | 5.13 | 1.00 | 1.00 |
| Defb28 | 1.00 | 1.00 | 1.00 | 1.00 | 1.00 | 1.00 | 1.00 | 1.00 | 1.00 | 1.00 | 1.00 | 1.00 |
| Defb36 | 1.00 | 1.00 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 | 1.00 | 1.00 |
| Defb40 | 1.00 | 1.00 | 1.00 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 | 1.73 | 1.00 | 1.00 |
| Defb6 | 1.00 | 1.00 | 1.00 | 1.00 | 1.00 | 1.00 | 1.00 | 1.00 | 1.00 | 1.00 | 1.00 | 1.00 |
| Degs2 | 1.00 | 1.00 | 1.00 | 0.54 | 0.49 | 0.71 | 0.73 | 0.47 | 0.70 | 0.40 | 0.18 | 0.77 |
| Dennd4a | 1.00 | 1.00 | 1.00 | 7.46 | 1.16 | 2.03 | 1.15 | 1.30 | 1.16 | 0.75 | 0.69 | 1.19 |
| Deptor | 0.43 | 0.99 | 0.51 | 5.02 | 0.70 | 1.05 | 0.62 | 0.69 | 0.78 | 0.31 | 0.44 | 1.02 |
| Derl2 | 0.94 | 0.79 | 1.10 | 0.99 | 5.15 | 0.86 | 1.00 | 0.83 | 0.87 | 1.93 | 2.13 | 0.98 |
| Derl3 | 1.00 | 1.00 | 1.00 | 3.45 | 1.03 | 1.62 | 1.00 | 1.00 | 1.00 | 0.91 | 0.76 | 1.29 |
| Des | 1.49 | 0.84 | 1.02 | 0.65 | 6.42 | 1.04 | 1.37 | 1.23 | 1.30 | 1.85 | 2.29 | 1.03 |

Fig. 35- 154

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Cyp4a14 | 12.06 | 0.98 | 1.00 | 0.91 | 0.70 | 0.89 | 1.30 | 1.16 | 1.67 | 1.26 | 1.00 | 1.11 |
| Cyp4f13 | 1.13 | 1.42 | 1.40 | 1.13 | 0.54 | 1.08 | 0.97 | 2.23 | 0.93 | 1.09 | 1.37 | 1.24 |
| Cyp4f15 | 1.00 | 1.00 | 1.00 | 1.00 | 1.00 | 1.00 | 1.32 | 1.47 | 1.47 | 1.00 | 1.00 | 1.00 |
| Cyp51 | 1.00 | 0.90 | 0.73 | 1.44 | 1.24 | 1.50 | 1.54 | 1.52 | 0.96 | 1.46 | 1.00 | 1.00 |
| Cypt12 | 1.00 | 1.00 | 1.00 | 1.00 | 1.00 | 1.00 | 1.00 | 1.00 | 1.00 | 1.00 | 1.00 | 1.00 |
| Cys1 | 1.00 | 1.39 | 0.75 | 0.58 | 0.46 | 0.70 | 0.54 | 0.46 | 0.60 | 0.60 | 0.69 | 0.44 |
| Cytl1 | 2.86 | 1.98 | 1.03 | 1.43 | 1.17 | 1.04 | 1.00 | 1.00 | 1.00 | 2.04 | 2.73 | 1.85 |
| D17H6S53E | 0.89 | 0.92 | 0.97 | 0.90 | 0.63 | 0.89 | 1.17 | 4.23 | 1.72 | 1.04 | 1.20 | 1.01 |
| D19Bwg1357e | 1.10 | 0.98 | 1.11 | 1.11 | 0.89 | 0.86 | 1.23 | 2.66 | 1.35 | 0.79 | 1.13 | 1.11 |
| D230025D16Rik | 1.29 | 1.45 | 1.23 | 1.94 | 2.16 | 1.22 | 1.17 | 0.15 | 0.89 | 1.22 | 0.98 | 1.05 |
| D2Wsu81e | 1.07 | 1.32 | 0.91 | 1.34 | 0.87 | 1.13 | 0.95 | 1.42 | 0.64 | 0.96 | 1.38 | 0.92 |
| D330041H03Rik | 1.63 | 1.53 | 0.97 | 0.45 | 1.05 | 0.38 | 0.68 | 0.45 | 0.08 | 0.74 | 2.04 | 1.57 |
| D330050I16Rik | 1.32 | 1.15 | 1.01 | 1.21 | 0.53 | 1.76 | 1.20 | 0.90 | 0.60 | 1.11 | 1.34 | 0.85 |
| D3Bwg0562e | 0.86 | 0.56 | 1.25 | 1.19 | 1.00 | 1.00 | 1.00 | 1.00 | 1.00 | 1.00 | 1.00 | 1.00 |
| D8Ertd738e | 1.11 | 1.65 | 0.99 | 0.89 | 0.97 | 0.83 | 1.09 | 1.01 | 0.94 | 1.29 | 1.52 | 1.05 |
| Dancr | 0.85 | 0.97 | 0.99 | 0.71 | 0.63 | 0.91 | 0.42 | 0.36 | 0.68 | 0.83 | 1.18 | 0.90 |
| Dao | 1.00 | 1.00 | 1.00 | 0.95 | 1.09 | 0.94 | 1.00 | 1.00 | 1.00 | 1.00 | 1.00 | 1.00 |
| Dap3 | 0.93 | 1.15 | 0.84 | 0.90 | 0.62 | 0.89 | 1.00 | 1.98 | 1.04 | 0.98 | 1.43 | 0.90 |
| Dapk3 | 1.17 | 1.47 | 1.24 | 1.12 | 0.52 | 1.06 | 1.08 | 2.45 | 1.08 | 1.06 | 1.36 | 0.96 |
| Dapp1 | 1.07 | 0.99 | 1.21 | 1.17 | 1.00 | 1.14 | 1.00 | 1.00 | 1.00 | 1.63 | 0.98 | 1.48 |
| Dbi | 0.89 | 1.41 | 0.79 | 0.77 | 0.65 | 0.92 | 1.19 | 1.29 | 0.93 | 0.95 | 1.58 | 1.05 |
| Dbil5 | 1.27 | 0.83 | 1.00 | 1.15 | 0.81 | 0.93 | 1.03 | 1.36 | 0.75 | 1.69 | 2.27 | 1.49 |
| Dclk1 | 0.73 | 0.47 | 0.69 | 1.00 | 1.00 | 1.00 | 1.00 | 1.00 | 1.00 | 0.78 | 0.64 | 0.94 |
| Dcps | 1.05 | 1.40 | 0.92 | 1.09 | 1.83 | 1.30 | 1.02 | 1.10 | 1.38 | 0.91 | 1.58 | 0.99 |
| Dctn2 | 1.27 | 1.54 | 1.09 | 1.07 | 0.83 | 0.95 | 1.19 | 1.79 | 0.91 | 1.07 | 1.36 | 1.02 |
| Dctn3 | 4.22 | 5.31 | 3.35 | 3.18 | 2.79 | 3.45 | 5.16 | 5.38 | 3.33 | 3.37 | 5.77 | 3.61 |
| Dctpp1 | 0.94 | 0.99 | 0.72 | 0.71 | 0.60 | 0.75 | 0.75 | 1.07 | 0.83 | 0.81 | 1.61 | 0.93 |
| Dcun1d5 | 0.97 | 1.18 | 0.90 | 1.00 | 0.94 | 1.04 | 1.13 | 1.70 | 1.00 | 0.97 | 1.73 | 1.17 |
| Dcxr | 1.24 | 1.60 | 1.37 | 1.03 | 0.60 | 0.96 | 0.68 | 1.63 | 0.70 | 0.79 | 1.28 | 0.78 |
| Ddb1 | 1.00 | 1.08 | 0.97 | 1.12 | 0.74 | 1.04 | 1.21 | 1.89 | 1.16 | 1.04 | 1.34 | 1.03 |
| Ddi2 | 0.53 | 0.46 | 1.09 | 1.70 | 1.00 | 1.55 | 1.05 | 1.00 | 1.50 | 0.83 | 0.87 | 0.67 |
| Ddit3 | 1.16 | 1.37 | 1.04 | 0.92 | 0.75 | 0.75 | 0.69 | 1.50 | 1.07 | 1.13 | 1.41 | 0.88 |
| Ddit4 | 1.94 | 3.31 | 2.40 | 6.30 | 11.71 | 3.49 | 19.12 | 34.94 | 10.46 | 2.12 | 2.36 | 1.61 |
| Ddn | 1.00 | 1.00 | 1.00 | 0.91 | 1.00 | 0.97 | 1.00 | 1.00 | 1.00 | 1.00 | 1.00 | 1.00 |
| Ddx47 | 0.96 | 1.16 | 0.83 | 1.07 | 0.93 | 0.88 | 0.87 | 0.74 | 0.87 | 0.83 | 1.25 | 0.86 |
| Ddx49 | 0.95 | 1.29 | 1.02 | 1.11 | 0.50 | 1.17 | 1.23 | 4.66 | 1.12 | 1.42 | 1.39 | 1.20 |
| Ddx56 | 1.03 | 0.79 | 0.87 | 0.93 | 0.66 | 1.02 | 0.98 | 2.73 | 1.23 | 0.96 | 1.32 | 1.07 |
| Decr1 | 0.97 | 1.07 | 0.92 | 0.71 | 0.37 | 0.77 | 1.08 | 2.90 | 0.94 | 0.89 | 1.04 | 1.06 |
| Dedd2 | 1.29 | 1.40 | 1.22 | 1.27 | 1.20 | 1.22 | 1.16 | 1.78 | 1.05 | 1.16 | 1.46 | 1.16 |
| Defa-rs1 | 1.38 | 1.17 | 1.00 | 1.00 | 1.00 | 1.00 | 1.00 | 2.83 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 | 1.00 | 1.00 |
| Defa17 | 2.19 | 1.00 | 1.00 | 1.00 | 1.00 | 1.00 | 1.00 | 1.00 | 1.00 | 1.00 | 1.00 | 3.16 |
| Defa23 | 1.00 | 1.00 | 1.00 | 1.00 | 1.00 | 1.00 | 1.00 | 1.00 | 1.00 | 1.00 | 1.00 | 1.00 |
| Defa24 | 1.18 | 1.00 | 1.00 | 1.00 | 1.00 | 1.00 | 1.00 | 1.00 | 1.00 | 1.00 | 1.00 | 7.04 |
| Defa3 | 1.71 | 1.00 | 1.00 | 1.00 | 1.00 | 1.00 | 1.00 | 1.00 | 1.00 | 1.00 | 1.00 | 2.54 |
| Defb1 | 13.75 | 16.29 | 6.37 | 1.01 | 1.33 | 1.06 | 0.89 | 0.67 | 0.31 | 1.00 | 1.00 | 1.00 |
| Defb11 | 1.00 | 1.00 | 1.00 | 0.84 | 0.11 | 1.00 | 1.00 | 1.00 | 1.00 | 1.00 | 1.00 | 1.00 |
| Defb14 | 1.00 | 1.00 | 1.00 | 1.00 | 1.00 | 1.00 | 1.00 | 1.00 | 1.00 | 1.00 | 1.00 | 1.00 |
| Defb2 | 1.00 | 1.00 | 1.00 | 0.29 | 0.09 | 0.90 | 1.00 | 1.00 | 1.00 | 1.00 | 1.00 | 1.00 |
| Defb22 | 1.00 | 1.00 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.00 | 1.00 | 1.00 | 1.00 | 0.50 | 1.00 | 1.00 | 1.01 | 1.00 |
| Defb28 | 1.00 | 1.00 | 1.00 | 1.00 | 1.05 | 1.00 | 1.00 | 1.00 | 1.00 | 1.00 | 1.00 | 1.00 |
| Defb36 | 1.00 | 1.00 | 1.00 | 1.00 | 1.17 | 0.49 | 1.00 | 1.00 | 1.00 | 1.00 | 1.05 | 1.00 |
| Defb37 | 1.00 | 1.00 | 1.00 | 1.00 | 1.00 | 1.00 | 1.00 | 1.00 | 1.00 | 0.83 | 0.41 | 0.67 |
| Defb39 | 1.00 | 1.00 | 1.00 | 1.00 | 1.00 | 1.00 | 1.00 | 1.00 | 1.00 | 1.00 | 1.00 | 1.00 |
| Defb40 | 1.00 | 1.00 | 1.00 | 1.00 | 1.00 | 1.00 | 1.00 | 1.00 | 1.00 | 1.00 | 0.80 | 1.00 |
| Defb45 | 1.00 | 1.00 | 1.00 | 1.00 | 1.00 | 1.00 | 1.00 | 1.00 | 1.00 | 1.03 | 7.51 | 1.68 |
| Defb6 | 0.93 | 0.62 | 0.41 | 1.00 | 1.00 | 1.00 | 1.00 | 1.00 | 1.00 | 1.00 | 1.00 | 0.50 |
| Degs2 | 0.96 | 0.94 | 1.14 | 0.92 | 0.79 | 1.04 | 1.00 | 1.00 | 1.00 | 1.14 | 1.40 | 1.21 |
| Dennd4a | 1.21 | 0.93 | 1.20 | 1.20 | 1.00 | 0.89 | 2.21 | 1.89 | 2.01 | 1.26 | 0.76 | 1.17 |
| Deptor | 1.38 | 1.03 | 0.95 | 0.89 | 1.34 | 0.85 | 0.56 | 0.34 | 0.62 | 0.99 | 0.79 | 0.87 |
| Derl2 | 0.93 | 0.97 | 0.97 | 1.01 | 0.78 | 1.02 | 0.82 | 1.31 | 0.73 | 0.90 | 1.14 | 0.89 |
| Derl3 | 2.20 | 3.22 | 2.23 | 0.74 | 1.00 | 0.90 | 0.75 | 1.00 | 0.93 | 0.97 | 1.25 | 1.14 |
| Des | 1.40 | 1.08 | 0.86 | 0.92 | 0.71 | 0.92 | 1.05 | 1.83 | 0.97 | 1.04 | 1.40 | 1.13 |

Fig. 35- 155

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Cyp4a14 | 2.02 | 3.43 | 2.60 | 0.47 | 1.00 | 1.00 | 1.00 | 1.00 | 1.00 | 1.00 | 1.32 | 1.00 |
| Cyp4f13 | 1.34 | 1.20 | 1.56 | 1.16 | 4.38 | 1.26 | 0.97 | 4.00 | 0.83 | 1.12 | 1.54 | 1.17 |
| Cyp4f15 | 1.00 | 1.00 | 1.00 | 1.00 | 1.00 | 1.00 | 1.00 | 1.00 | 1.00 | 1.00 | 1.00 | 1.00 |
| Cyp51 | 0.75 | 0.77 | 0.64 | 4.44 | 8.42 | 2.33 | 0.98 | 1.95 | 0.94 | 1.15 | 1.30 | 1.01 |
| Cypt12 | 1.00 | 1.00 | 1.00 | 6.15 | 3.06 | 1.33 | 0.85 | 1.46 | 1.02 | 1.00 | 1.00 | 1.00 |
| Cys1 | 0.53 | 0.73 | 0.68 | 0.71 | 1.63 | 0.74 | 1.00 | 1.02 | 0.94 | 0.64 | 0.94 | 0.67 |
| Cytl1 | 2.60 | 1.46 | 2.52 | 2.76 | 6.13 | 2.04 | 1.07 | 1.28 | 0.79 | 0.78 | 1.35 | 1.20 |
| D17H6S53E | 0.81 | 0.91 | 0.80 | 0.92 | 2.58 | 1.05 | 1.32 | 4.70 | 0.92 | 0.91 | 0.94 | 0.84 |
| D19Bwg1357e | 0.90 | 0.85 | 0.95 | 2.06 | 3.62 | 1.76 | 1.10 | 2.21 | 1.28 | 1.12 | 0.99 | 1.06 |
| D230025D16Rik | 1.42 | 1.62 | 1.25 | 1.67 | 1.08 | 1.61 | 0.95 | 1.05 | 0.83 | 1.41 | 1.23 | 1.06 |
| D2Wsu81e | 0.97 | 1.07 | 1.05 | 1.07 | 2.79 | 0.99 | 0.92 | 1.50 | 0.95 | 1.30 | 1.21 | 0.93 |
| D330041H03Rik | 1.10 | 0.92 | 1.83 | 0.86 | 7.39 | 1.44 | 1.18 | 1.22 | 1.02 | 1.39 | 1.44 | 0.94 |
| D330050I16Rik | 0.94 | 1.51 | 1.13 | 1.39 | 1.10 | 0.87 | 1.00 | 2.61 | 1.13 | 1.79 | 1.57 | 0.90 |
| D3Bwg0562e | 1.00 | 1.00 | 1.00 | 1.00 | 1.00 | 0.68 | 0.74 | 1.00 | 0.90 | 1.00 | 5.36 | 1.00 |
| D8Ertd738e | 1.04 | 1.07 | 0.96 | 1.26 | 7.61 | 1.22 | 0.96 | 0.78 | 0.92 | 1.24 | 1.27 | 0.94 |
| Dancr | 0.71 | 0.88 | 1.03 | 1.25 | 3.29 | 1.25 | 0.92 | 0.30 | 0.91 | 1.29 | 1.47 | 0.93 |
| Dao | 1.00 | 1.00 | 1.00 | 1.28 | 5.36 | 3.25 | 1.00 | 1.00 | 1.00 | 1.00 | 1.00 | 1.00 |
| Dap3 | 0.94 | 1.23 | 0.88 | 0.84 | 1.48 | 0.91 | 0.93 | 2.91 | 1.02 | 0.92 | 1.23 | 0.96 |
| Dapk3 | 0.89 | 1.21 | 0.85 | 1.03 | 2.18 | 0.93 | 0.96 | 6.28 | 1.18 | 0.86 | 1.37 | 0.97 |
| Dapp1 | 1.34 | 1.18 | 1.54 | 1.25 | 1.37 | 1.28 | 6.49 | 11.74 | 6.12 | 1.22 | 0.90 | 1.14 |
| Dbi | 0.73 | 0.83 | 0.91 | 0.58 | 2.04 | 0.68 | 1.05 | 1.51 | 0.81 | 1.34 | 1.36 | 1.03 |
| Dbil5 | 1.03 | 1.35 | 0.62 | 3.65 | 6.69 | 1.16 | 0.93 | 1.03 | 0.96 | 1.00 | 1.68 | 1.27 |
| Dclk1 | 1.11 | 0.84 | 1.01 | 0.75 | 1.00 | 0.45 | 1.00 | 5.93 | 1.08 | 0.53 | 1.11 | 0.57 |
| Dcps | 1.02 | 1.04 | 1.10 | 1.10 | 8.83 | 1.16 | 0.89 | 1.66 | 0.87 | 0.93 | 1.13 | 1.05 |
| Dctn2 | 1.01 | 1.01 | 0.99 | 1.06 | 2.68 | 1.04 | 0.98 | 1.68 | 1.10 | 1.13 | 1.38 | 0.90 |
| Dctn3 | 3.59 | 3.15 | 3.30 | 3.75 | 18.65 | 3.70 | 3.83 | 7.59 | 4.16 | 3.93 | 3.95 | 2.87 |
| Dctpp1 | 0.93 | 0.83 | 0.91 | 0.78 | 3.53 | 0.84 | 0.91 | 1.24 | 1.19 | 1.49 | 1.51 | 0.97 |
| Dcun1d5 | 0.78 | 1.15 | 0.99 | 1.17 | 2.50 | 1.15 | 0.87 | 1.85 | 1.23 | 1.18 | 1.39 | 0.91 |
| Dcxr | 1.33 | 1.13 | 1.34 | 0.59 | 1.48 | 1.01 | 0.99 | 3.70 | 0.85 | 1.40 | 1.12 | 0.90 |
| Ddb1 | 1.00 | 0.93 | 0.89 | 1.10 | 2.54 | 0.92 | 1.18 | 2.27 | 1.03 | 0.98 | 1.13 | 0.97 |
| Ddi2 | 0.97 | 0.88 | 0.55 | 2.86 | 0.45 | 1.11 | 1.55 | 1.00 | 1.26 | 0.84 | 0.33 | 1.20 |
| Ddit3 | 0.84 | 1.02 | 1.02 | 0.67 | 1.25 | 0.64 | 0.94 | 1.95 | 0.92 | 0.96 | 1.27 | 0.93 |
| Ddit4 | 2.75 | 4.34 | 1.97 | 3.66 | 2.59 | 4.34 | 1.03 | 0.88 | 1.14 | 1.75 | 2.75 | 2.56 |
| Ddn | 1.00 | 1.00 | 1.00 | 1.00 | 1.00 | 0.55 | 1.00 | 1.00 | 1.00 | 0.94 | 28.90 | 0.98 |
| Ddx47 | 0.75 | 0.92 | 0.87 | 0.90 | 5.10 | 1.04 | 0.72 | 0.53 | 0.74 | 1.00 | 1.03 | 0.79 |
| Ddx49 | 0.71 | 1.16 | 0.79 | 1.29 | 1.05 | 1.00 | 1.01 | 5.41 | 0.93 | 1.21 | 1.32 | 0.99 |
| Ddx56 | 0.90 | 0.71 | 0.83 | 1.07 | 2.69 | 1.05 | 0.98 | 2.57 | 1.09 | 0.95 | 1.13 | 1.21 |
| Decr1 | 0.76 | 0.71 | 1.02 | 0.68 | 0.99 | 0.56 | 1.01 | 3.58 | 0.79 | 0.98 | 0.84 | 0.97 |
| Dedd2 | 1.20 | 1.31 | 0.88 | 2.28 | 6.33 | 1.42 | 1.05 | 1.69 | 1.14 | 0.97 | 1.20 | 0.95 |
| Defa-rs1 | 3.00 | 1.00 | 1.81 | 1.00 | 1.00 | 1.00 | 7.41 | 53.92 | 8.22 | 1.00 | 1.00 | 1.00 |
| Defa-rs7 | 1.00 | 1.00 | 5.05 | 1.00 | 1.00 | 1.00 | 1.00 | 1.00 | 1.00 | 1.00 | 1.00 | 1.00 |
| Defa17 | 14.07 | 3.83 | 14.34 | 1.00 | 1.00 | 1.00 | 4.66 | 2.50 | 1.38 | 1.00 | 1.00 | 1.00 |
| Defa23 | 9.78 | 2.19 | 3.79 | 1.00 | 1.00 | 1.00 | 2.87 | 53.15 | 1.15 | 1.00 | 1.00 | 1.00 |
| Defa24 | 21.10 | 1.36 | 23.54 | 1.00 | 1.00 | 1.00 | 1.00 | 1.82 | 1.07 | 1.00 | 1.00 | 1.00 |
| Defa3 | 12.72 | 1.51 | 15.23 | 1.00 | 1.00 | 1.00 | 1.17 | 3.13 | 1.66 | 1.00 | 1.00 | 1.00 |
| Defb1 | 1.09 | 1.96 | 1.42 | 1.00 | 1.00 | 0.30 | 1.00 | 1.00 | 1.00 | 1.00 | 1.00 | 1.00 |
| Defb11 | 1.00 | 1.00 | 1.00 | 1.00 | 7.58 | 0.08 | 0.16 | 0.12 | 0.29 | 1.00 | 1.00 | 1.00 |
| Defb14 | 1.32 | 1.36 | 3.71 | 1.00 | 1.00 | 1.00 | 8.58 | 5.82 | 5.11 | 1.00 | 1.00 | 1.00 |
| Defb2 | 1.00 | 1.00 | 1.00 | 1.00 | 1.00 | 0.07 | 1.00 | 1.00 | 1.00 | 1.00 | 1.00 | 1.00 |
| Defb22 | 1.00 | 1.00 | 1.00 | 1.00 | 23.59 | 0.01 | 1.00 | 1.00 | 1.00 | 1.00 | 1.00 | 1.00 |
| Defb25 | 1.00 | 1.00 | 0.43 | 0.12 | 1.00 | 1.00 | 1.00 | 1.00 | 1.00 | 1.00 | 0.93 | 1.00 |
| Defb28 | 1.00 | 1.00 | 1.00 | 1.00 | 125.02 | 0.02 | 1.00 | 1.32 | 1.00 | 1.00 | 1.00 | 1.00 |
| Defb36 | 1.00 | 1.00 | 1.00 | 0.41 | 5.64 | 2.53 | 0.75 | 1.61 | 1.04 | 1.00 | 1.00 | 1.00 |
| Defb37 | 1.00 | 1.00 | 1.00 | 1.00 | 29.54 | 0.09 | 1.00 | 1.00 | 1.00 | 1.00 | 1.00 | 1.00 |
| Defb39 | 1.00 | 1.00 | 1.00 | 1.00 | 9.81 | 0.25 | 1.00 | 1.00 | 1.00 | 1.00 | 1.00 | 1.00 |
| Defb40 | 1.00 | 1.00 | 1.00 | 1.00 | 20.16 | 0.14 | 1.00 | 1.00 | 1.00 | 1.00 | 1.00 | 1.00 |
| Defb45 | 1.00 | 1.00 | 1.00 | 1.00 | 1.00 | 1.00 | 1.44 | 17.29 | 1.47 | 1.00 | 1.00 | 1.00 |
| Defb6 | 1.00 | 1.00 | 1.00 | 1.00 | 1.00 | 1.00 | 1.00 | 1.00 | 1.00 | 1.00 | 1.00 | 1.00 |
| Degs2 | 0.82 | 0.87 | 0.73 | 0.94 | 2.14 | 1.02 | 1.20 | 1.00 | 0.90 | 0.95 | 0.72 | 1.01 |
| Dennd4a | 1.45 | 1.41 | 1.22 | 1.97 | 0.62 | 1.22 | 1.11 | 1.00 | 1.18 | 1.18 | 0.90 | 1.23 |
| Deptor | 0.78 | 0.76 | 0.66 | 1.11 | 0.21 | 0.31 | 0.86 | 1.00 | 0.82 | 0.78 | 0.58 | 0.84 |
| Derl2 | 0.86 | 0.88 | 0.90 | 1.01 | 3.37 | 1.00 | 0.98 | 2.39 | 1.01 | 1.05 | 0.83 | 0.96 |
| Derl3 | 1.03 | 0.94 | 2.25 | 6.91 | 1.67 | 2.45 | 0.92 | 0.29 | 0.99 | 1.40 | 1.30 | 1.63 |
| Des | 1.19 | 1.41 | 1.27 | 1.72 | 2.12 | 1.62 | 0.88 | 1.28 | 1.20 | 0.82 | 0.83 | 0.74 |

Fig. 35- 156

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Cyp4a14 | 1.00 | 1.00 | 1.00 | 0.74 | 1.00 | 1.00 | 1.00 | 1.00 | 1.00 | 1.00 | 1.00 | 1.00 |
| Cyp4f13 | 0.76 | 0.73 | 1.10 | 0.69 | 0.92 | 1.18 | 1.23 | 14.32 | 0.95 | 4.14 | 1.75 | 1.45 |
| Cyp4f15 | 1.00 | 1.10 | 1.58 | 1.47 | 4.27 | 1.33 | 1.00 | 1.00 | 1.00 | 1.00 | 1.00 | 1.00 |
| Cyp51 | 1.00 | 1.00 | 1.00 | 1.06 | 0.55 | 0.92 | 1.20 | 2.31 | 1.06 | 1.90 | 1.03 | 2.05 |
| Cypt12 | 1.00 | 1.00 | 1.00 | 1.00 | 1.00 | 1.00 | 1.85 | 1.00 | 1.00 | 1.00 | 1.00 | 1.00 |
| Cys1 | 0.66 | 0.87 | 0.69 | 0.97 | 1.12 | 0.86 | 0.84 | 5.07 | 0.94 | 1.00 | 1.00 | 1.00 |
| Cytl1 | 0.83 | 1.28 | 1.53 | 1.36 | 2.35 | 1.05 | 1.72 | 3.92 | 1.11 | 1.00 | 1.00 | 1.00 |
| D17H6S53E | 1.03 | 1.24 | 1.58 | 1.03 | 0.89 | 1.07 | 1.23 | 11.67 | 0.94 | 2.59 | 1.01 | 1.17 |
| D19Bwg1357e | 1.33 | 0.73 | 0.66 | 0.82 | 1.27 | 0.94 | 1.02 | 4.52 | 1.00 | 2.14 | 0.86 | 1.04 |
| D230025D16Rik | 1.50 | 1.50 | 1.72 | 0.99 | 1.00 | 0.93 | 1.59 | 0.05 | 1.37 | 0.84 | 1.75 | 1.31 |
| D2Wsu81e | 0.82 | 0.53 | 0.76 | 1.11 | 0.82 | 1.15 | 1.15 | 4.43 | 0.84 | 2.00 | 1.16 | 1.09 |
| D330041H03Rik | 1.07 | 0.98 | 1.04 | 1.21 | 1.06 | 1.04 | 1.27 | 4.68 | 0.93 | 1.89 | 1.28 | 1.56 |
| D330050I16Rik | 1.00 | 1.00 | 1.00 | 1.29 | 0.66 | 0.71 | 1.08 | 5.30 | 1.10 | 1.94 | 1.88 | 0.51 |
| D3Bwg0562e | 1.00 | 1.00 | 1.00 | 0.94 | 1.30 | 0.86 | 1.00 | 1.00 | 1.00 | 1.00 | 1.00 | 1.00 |
| D8Ertd738e | 1.18 | 1.03 | 1.23 | 1.18 | 1.84 | 1.08 | 1.10 | 2.98 | 1.05 | 1.78 | 1.33 | 1.32 |
| Dancr | 1.33 | 1.40 | 0.77 | 0.94 | 5.93 | 0.93 | 1.01 | 1.93 | 1.08 | 1.18 | 0.85 | 1.22 |
| Dao | 1.00 | 1.00 | 1.00 | 0.97 | 0.60 | 0.82 | 1.00 | 1.00 | 1.00 | 1.00 | 1.00 | 1.00 |
| Dap3 | 1.11 | 0.96 | 1.00 | 1.05 | 1.12 | 1.05 | 0.85 | 9.52 | 0.99 | 2.58 | 1.09 | 0.99 |
| Dapk3 | 0.76 | 1.20 | 0.84 | 1.06 | 0.95 | 0.97 | 1.32 | 14.22 | 0.95 | 3.19 | 1.07 | 1.11 |
| Dapp1 | 1.00 | 1.00 | 1.00 | 1.47 | 1.00 | 1.44 | 1.22 | 2.17 | 1.16 | 1.33 | 1.23 | 1.32 |
| Dbi | 1.34 | 0.90 | 0.82 | 1.13 | 0.96 | 1.08 | 1.03 | 5.45 | 0.83 | 3.20 | 1.48 | 1.60 |
| Dbil5 | 1.00 | 0.59 | 1.00 | 1.12 | 0.58 | 0.86 | 6.61 | 3.85 | 0.45 | 1.45 | 1.00 | 1.00 |
| Dclk1 | 1.00 | 1.00 | 1.00 | 1.08 | 0.97 | 1.00 | 0.76 | 1.45 | 0.88 | 1.00 | 1.00 | 1.00 |
| Dcps | 0.63 | 1.13 | 1.03 | 1.00 | 3.17 | 1.27 | 1.07 | 3.00 | 0.82 | 1.58 | 1.11 | 1.20 |
| Dctn2 | 1.09 | 1.10 | 1.05 | 1.13 | 1.05 | 1.03 | 1.25 | 5.99 | 0.93 | 2.25 | 1.27 | 1.05 |
| Dctn3 | 3.76 | 2.91 | 2.96 | 3.41 | 2.60 | 3.03 | 4.27 | 36.38 | 2.61 | 9.13 | 4.19 | 4.21 |
| Dctpp1 | 0.72 | 0.76 | 0.90 | 1.05 | 0.70 | 1.12 | 0.92 | 5.34 | 0.71 | 2.11 | 1.03 | 1.27 |
| Dcun1d5 | 1.12 | 1.29 | 0.73 | 1.11 | 1.44 | 1.17 | 1.03 | 5.97 | 1.21 | 2.90 | 1.33 | 1.01 |
| Dcxr | 0.79 | 0.70 | 0.46 | 0.75 | 1.04 | 1.36 | 1.08 | 15.28 | 0.76 | 2.63 | 1.20 | 1.45 |
| Ddb1 | 1.33 | 1.14 | 1.20 | 1.07 | 1.06 | 0.97 | 1.16 | 6.91 | 1.03 | 2.26 | 0.95 | 0.94 |
| Ddi2 | 1.71 | 1.11 | 1.32 | 0.63 | 1.00 | 0.72 | 0.58 | 0.22 | 1.25 | 1.00 | 0.87 | 0.45 |
| Ddit3 | 0.75 | 1.35 | 0.60 | 1.10 | 1.24 | 1.03 | 1.28 | 6.67 | 0.86 | 2.79 | 1.51 | 0.89 |
| Ddit4 | 4.63 | 8.68 | 3.30 | 1.66 | 1.69 | 1.69 | 3.75 | 1.66 | 3.83 | 1.98 | 5.83 | 3.40 |
| Ddn | 1.00 | 1.00 | 1.00 | 1.01 | 1.14 | 1.01 | 0.96 | 1.00 | 1.17 | 1.00 | 1.00 | 1.00 |
| Ddx47 | 0.87 | 0.95 | 0.78 | 0.94 | 1.03 | 0.87 | 1.00 | 1.22 | 1.05 | 1.29 | 1.04 | 0.93 |
| Ddx49 | 1.00 | 1.27 | 0.88 | 0.91 | 0.95 | 1.03 | 1.21 | 16.94 | 0.98 | 2.58 | 1.28 | 1.06 |
| Ddx56 | 0.89 | 0.93 | 1.03 | 0.97 | 0.88 | 1.04 | 0.96 | 7.29 | 0.94 | 2.25 | 0.85 | 0.91 |
| Decr1 | 0.57 | 0.50 | 0.59 | 0.97 | 0.74 | 0.95 | 1.22 | 8.86 | 1.44 | 1.39 | 1.03 | 1.51 |
| Dedd2 | 1.50 | 1.68 | 1.45 | 0.97 | 1.13 | 1.03 | 1.17 | 2.31 | 0.91 | 1.60 | 1.34 | 1.00 |
| Defa-rs1 | 1.00 | 1.00 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 | 1.00 | 1.00 |
| Defa17 | 1.00 | 1.00 | 1.00 | 1.00 | 1.00 | 1.00 | 1.00 | 1.00 | 1.00 | 1.00 | 1.00 | 1.00 |
| Defa23 | 1.00 | 1.00 | 1.00 | 1.00 | 1.00 | 1.00 | 1.00 | 1.00 | 1.00 | 1.00 | 1.00 | 1.00 |
| Defa24 | 1.00 | 1.00 | 1.00 | 1.00 | 1.00 | 1.00 | 1.00 | 1.00 | 1.00 | 1.00 | 1.00 | 1.00 |
| Defa3 | 1.00 | 1.00 | 1.00 | 1.00 | 1.00 | 1.00 | 1.00 | 1.00 | 1.00 | 1.00 | 1.00 | 1.00 |
| Defb1 | 7.62 | 2.51 | 1.39 | 1.00 | 1.00 | 1.00 | 1.58 | 5.23 | 1.40 | 1.00 | 1.00 | 1.00 |
| Defb11 | 1.00 | 1.00 | 1.00 | 1.00 | 1.00 | 1.00 | 1.00 | 1.00 | 1.00 | 1.00 | 1.00 | 1.00 |
| Defb14 | 1.00 | 1.00 | 1.00 | 1.00 | 1.00 | 1.00 | 3.34 | 25.78 | 3.95 | 1.00 | 1.00 | 1.00 |
| Defb2 | 1.00 | 1.00 | 1.00 | 1.00 | 1.00 | 1.00 | 3.72 | 24.25 | 2.19 | 1.00 | 1.00 | 1.00 |
| Defb22 | 1.00 | 1.00 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.00 | 1.00 | 1.00 | 1.00 | 13.55 | 1.00 | 1.00 | 1.00 | 1.00 |
| Defb28 | 1.00 | 1.00 | 1.00 | 1.00 | 1.00 | 1.00 | 1.00 | 1.00 | 1.00 | 1.00 | 1.00 | 1.00 |
| Defb36 | 1.00 | 1.00 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 | 1.00 | 1.00 |
| Defb40 | 1.00 | 1.00 | 1.00 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 | 1.00 | 1.00 | 1.00 |
| Defb6 | 1.00 | 1.00 | 1.00 | 1.00 | 1.00 | 1.00 | 1.06 | 9.96 | 0.47 | 1.00 | 1.00 | 1.00 |
| Degs2 | 1.00 | 1.00 | 1.00 | 1.32 | 0.39 | 1.02 | 2.08 | 7.45 | 0.93 | 0.32 | 0.95 | 1.10 |
| Dennd4a | 0.94 | 1.00 | 1.00 | 0.84 | 0.96 | 1.00 | 0.99 | 0.33 | 1.26 | 0.51 | 1.10 | 0.80 |
| Deptor | 0.88 | 0.79 | 0.85 | 0.75 | 1.00 | 0.75 | 0.99 | 0.14 | 1.27 | 1.00 | 1.82 | 1.44 |
| Derl2 | 0.93 | 0.66 | 0.94 | 0.93 | 1.08 | 1.07 | 0.88 | 2.87 | 0.95 | 1.70 | 1.13 | 1.09 |
| Derl3 | 0.83 | 0.60 | 0.66 | 1.00 | 1.00 | 1.85 | 1.00 | 1.00 | 1.00 | 1.02 | 1.13 | 1.82 |
| Des | 1.03 | 1.00 | 1.69 | 0.87 | 0.71 | 1.08 | 1.83 | 9.01 | 1.75 | 1.00 | 1.00 | 1.00 |

Fig. 35- 157

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Dgat1 | 1.09 | 0.69 | 1.43 | 0.29 | 5.07 | 1.11 | 1.09 | 0.71 | 1.09 | 2.39 | 4.59 | 1.11 |
| Dhrs13 | 1.00 | 0.43 | 0.72 | 0.65 | 3.42 | 1.28 | 1.14 | 0.76 | 1.17 | 2.91 | 2.49 | 1.48 |
| Dhrs7c | 0.74 | 0.50 | 0.47 | 1.00 | 2.60 | 0.65 | 0.92 | 0.89 | 0.68 | 4.04 | 4.19 | 0.65 |
| Dhrsx | 1.24 | 1.14 | 1.17 | 0.32 | 6.74 | 1.17 | 1.39 | 0.91 | 1.03 | 2.64 | 3.04 | 0.97 |
| Dhx58 | 1.00 | 1.00 | 1.00 | 0.50 | 3.37 | 1.24 | 1.05 | 1.00 | 1.63 | 2.72 | 2.81 | 1.22 |
| Dio3os | 0.89 | 0.77 | 1.64 | 1.00 | 1.00 | 1.00 | 1.00 | 1.00 | 1.00 | 3.57 | 4.27 | 1.50 |
| Diras1 | 1.00 | 1.00 | 1.00 | 1.00 | 0.28 | 1.00 | 1.00 | 1.00 | 1.00 | 1.00 | 1.00 | 1.00 |
| Disp2 | 1.00 | 1.00 | 1.00 | 1.00 | 0.16 | 1.00 | 1.00 | 1.00 | 1.00 | 1.00 | 1.00 | 1.00 |
| Dlgap1 | 1.00 | 1.00 | 1.00 | 1.00 | 0.20 | 1.00 | 1.00 | 1.00 | 1.27 | 1.00 | 1.00 | 1.00 |
| Dlgap3 | 1.00 | 1.00 | 1.00 | 1.00 | 0.25 | 1.00 | 1.00 | 1.00 | 1.00 | 1.00 | 1.00 | 1.00 |
| Dlgap4 | 1.08 | 0.80 | 1.04 | 1.18 | 3.47 | 1.08 | 0.91 | 0.92 | 0.99 | 1.78 | 2.01 | 0.91 |
| Dmap1 | 0.87 | 0.99 | 0.90 | 0.41 | 2.02 | 0.97 | 1.35 | 0.96 | 0.91 | 1.49 | 1.90 | 1.08 |
| Dmbt1 | 1.00 | 1.00 | 1.00 | 1.00 | 1.00 | 1.00 | 1.00 | 1.00 | 1.00 | 1.00 | 1.00 | 1.00 |
| Dmkn | 1.19 | 1.00 | 1.00 | 1.00 | 1.10 | 1.00 | 1.00 | 1.00 | 1.00 | 1.61 | 3.22 | 1.93 |
| Dnaaf1 | 1.00 | 1.00 | 1.00 | 1.00 | 6.10 | 1.00 | 1.00 | 1.00 | 1.00 | 3.64 | 5.95 | 1.25 |
| Dnajb12 | 0.86 | 1.23 | 1.05 | 1.27 | 1.53 | 1.37 | 1.44 | 1.41 | 1.21 | 1.17 | 1.45 | 1.28 |
| Dnajb14 | 1.00 | 1.39 | 1.00 | 0.65 | 3.90 | 1.35 | 1.65 | 1.30 | 2.07 | 2.60 | 3.40 | 1.19 |
| Dnajb2 | 1.79 | 1.09 | 1.57 | 1.01 | 7.42 | 1.27 | 1.56 | 1.21 | 1.08 | 3.02 | 3.59 | 1.15 |
| Dnajc11 | 1.05 | 0.64 | 0.88 | 0.28 | 2.26 | 0.71 | 0.84 | 0.87 | 0.85 | 2.76 | 2.62 | 1.07 |
| Dnajc15 | 1.16 | 0.47 | 0.86 | 0.21 | 11.66 | 0.94 | 0.89 | 0.88 | 0.67 | 3.52 | 5.29 | 0.94 |
| Dnajc17 | 1.00 | 0.34 | 1.00 | 0.63 | 6.02 | 1.00 | 1.00 | 1.00 | 1.00 | 3.14 | 9.28 | 1.00 |
| Dnajc19 | 0.75 | 0.47 | 0.53 | 0.16 | 4.69 | 0.87 | 0.81 | 0.53 | 0.69 | 3.35 | 3.97 | 0.73 |
| Dnajc22 | 1.00 | 1.00 | 1.00 | 1.19 | 1.18 | 0.81 | 1.00 | 1.00 | 1.00 | 1.00 | 1.00 | 1.00 |
| Dnajc9 | 0.66 | 0.74 | 0.69 | 1.12 | 1.12 | 1.01 | 0.75 | 0.91 | 0.80 | 0.76 | 0.64 | 0.80 |
| Dnase2a | 0.89 | 0.43 | 1.09 | 0.92 | 15.85 | 1.26 | 0.81 | 0.91 | 1.01 | 5.99 | 7.90 | 1.21 |
| Dner | 1.00 | 1.00 | 1.00 | 1.00 | 0.23 | 1.00 | 1.00 | 1.00 | 1.00 | 1.00 | 1.00 | 1.00 |
| Dnph1 | 0.59 | 0.56 | 0.60 | 1.00 | 1.67 | 1.00 | 1.26 | 1.38 | 1.37 | 1.93 | 1.64 | 1.00 |
| Dnttip1 | 1.79 | 1.13 | 0.87 | 0.86 | 5.68 | 1.86 | 1.13 | 0.96 | 0.92 | 1.11 | 2.23 | 1.14 |
| Doc2b | 1.97 | 2.16 | 2.70 | 6.74 | 0.98 | 3.23 | 3.31 | 3.08 | 1.44 | 3.32 | 3.91 | 9.88 |
| Doc2g | 1.00 | 0.48 | 0.69 | 0.55 | 2.18 | 1.00 | 0.81 | 0.74 | 0.79 | 1.76 | 2.32 | 0.40 |
| Dpagt1 | 0.94 | 0.77 | 1.08 | 0.63 | 3.47 | 1.24 | 1.03 | 0.80 | 1.08 | 1.87 | 2.11 | 1.00 |
| Dpcd | 1.03 | 0.56 | 1.05 | 0.38 | 7.33 | 0.77 | 1.01 | 0.74 | 0.77 | 3.10 | 4.52 | 0.83 |
| Dpep1 | 2.33 | 1.39 | 2.21 | 1.00 | 7.29 | 2.20 | 1.47 | 1.44 | 1.17 | 3.97 | 2.96 | 1.50 |
| Dph1 | 1.01 | 1.00 | 1.90 | 0.43 | 1.14 | 1.06 | 0.84 | 1.83 | 1.00 | 1.00 | 1.00 | 1.26 |
| Dph5 | 1.07 | 1.00 | 0.90 | 0.46 | 5.34 | 1.26 | 1.12 | 0.74 | 1.10 | 2.55 | 2.17 | 1.08 |
| Dpm3 | 0.65 | 0.57 | 0.94 | 0.24 | 6.39 | 0.71 | 0.93 | 0.50 | 0.74 | 1.31 | 2.73 | 0.98 |
| Dpp6 | 1.00 | 1.00 | 1.00 | 1.00 | 0.35 | 1.00 | 1.00 | 1.00 | 1.00 | 1.00 | 1.00 | 1.00 |
| Dpp7 | 2.61 | 0.92 | 1.97 | 0.82 | 5.84 | 2.31 | 1.58 | 1.01 | 1.82 | 3.26 | 4.19 | 1.72 |
| Dpy30 | 0.94 | 0.80 | 0.81 | 0.41 | 2.35 | 0.73 | 0.77 | 0.82 | 0.77 | 0.92 | 1.64 | 0.92 |
| Drap1 | 1.20 | 0.62 | 0.90 | 0.45 | 6.84 | 0.83 | 1.01 | 0.85 | 0.85 | 2.17 | 3.38 | 0.94 |
| Dreh | 1.00 | 1.00 | 1.00 | 1.00 | 1.00 | 1.00 | 1.00 | 1.00 | 1.00 | 1.00 | 1.00 | 1.00 |
| Drosha | 0.96 | 0.56 | 1.07 | 0.90 | 2.10 | 1.24 | 1.27 | 1.42 | 1.31 | 2.07 | 2.49 | 0.99 |
| Dtnb | 1.51 | 2.05 | 1.37 | 1.00 | 2.16 | 1.00 | 1.45 | 1.08 | 1.82 | 2.85 | 3.97 | 1.16 |
| Dus1l | 0.87 | 0.58 | 1.01 | 0.45 | 5.07 | 0.91 | 0.77 | 0.97 | 0.98 | 2.52 | 4.03 | 0.86 |
| Dus2 | 1.00 | 0.89 | 0.78 | 0.61 | 4.89 | 1.13 | 0.82 | 0.50 | 0.81 | 1.69 | 1.60 | 1.11 |
| Dusp1 | 2.07 | 3.74 | 1.36 | 0.89 | 0.34 | 0.80 | 1.49 | 1.47 | 1.18 | 1.37 | 1.45 | 1.90 |
| Dusp22 | 0.90 | 0.64 | 0.92 | 1.38 | 3.96 | 1.14 | 0.93 | 0.87 | 0.83 | 0.91 | 1.27 | 0.87 |
| Dusp26 | 0.76 | 0.70 | 0.89 | 0.53 | 0.55 | 1.10 | 1.32 | 1.12 | 1.47 | 1.00 | 0.84 | 1.18 |
| Dym | 1.24 | 0.67 | 1.04 | 0.61 | 4.91 | 1.26 | 1.21 | 1.14 | 0.96 | 2.36 | 3.63 | 1.19 |
| Dync1h1 | 1.29 | 0.90 | 1.48 | 0.89 | 3.99 | 1.23 | 1.33 | 1.48 | 1.35 | 2.83 | 2.64 | 1.09 |
| Dync1li1 | 1.30 | 5.52 | 1.38 | 2.08 | 0.15 | 1.27 | 1.58 | 1.67 | 1.22 | 0.80 | 0.14 | 1.00 |
| Dynlrb1 | 1.20 | 0.65 | 0.92 | 0.41 | 4.60 | 0.85 | 0.91 | 0.80 | 0.86 | 2.08 | 2.76 | 0.88 |
| Dynlt1c | 1.13 | 1.17 | 0.85 | 0.55 | 2.56 | 1.12 | 0.81 | 0.61 | 0.77 | 0.53 | 0.97 | 0.76 |
| Dzank1 | 1.00 | 1.00 | 1.00 | 1.00 | 0.27 | 1.00 | 1.00 | 1.00 | 1.00 | 1.00 | 0.91 | 1.07 |
| E030018B13Rik | 1.00 | 1.00 | 1.00 | 2.10 | 9.62 | 9.81 | 1.00 | 1.00 | 1.00 | 1.00 | 1.00 | 1.00 |
| E030030I06Rik | 1.00 | 1.00 | 1.00 | 0.62 | 6.38 | 0.90 | 1.00 | 1.00 | 1.00 | 2.01 | 1.63 | 1.26 |
| E030044B06Rik | 1.00 | 1.00 | 1.00 | 1.00 | 1.00 | 1.00 | 1.00 | 1.00 | 1.00 | 3.14 | 7.45 | 0.84 |
| E130012A19Rik | 0.94 | 0.75 | 1.07 | 1.00 | 4.92 | 1.00 | 1.43 | 1.66 | 0.78 | 4.60 | 5.66 | 1.65 |
| E130201H02Rik | 1.09 | 5.51 | 0.95 | 1.27 | 0.04 | 0.78 | 0.91 | 1.01 | 0.85 | 1.00 | 0.07 | 0.98 |
| E230008N13Rik | 1.00 | 1.00 | 1.00 | 1.00 | 1.00 | 1.00 | 1.00 | 1.00 | 1.00 | 5.16 | 2.49 | 1.30 |
| E530011L22Rik | 1.00 | 1.00 | 1.00 | 1.00 | 1.00 | 1.00 | 0.72 | 0.98 | 1.15 | 4.20 | 1.73 | 0.72 |
| Eapp | 1.10 | 0.83 | 1.24 | 0.63 | 7.23 | 0.95 | 1.27 | 1.22 | 1.03 | 2.29 | 3.43 | 1.10 |
| Ear1 | 1.00 | 1.00 | 1.00 | 1.00 | 1.00 | 1.00 | 1.00 | 1.00 | 1.00 | 0.47 | 0.82 | 0.99 |
| Ear3 | 1.00 | 1.00 | 1.00 | 1.00 | 1.00 | 1.00 | 1.00 | 1.00 | 1.00 | 1.00 | 1.00 | 1.00 |

Fig. 35- 158

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Dgat1 | 1.24 | 1.62 | 1.17 | 0.66 | 0.51 | 1.10 | 1.34 | 1.93 | 1.14 | 0.79 | 1.27 | 0.98 |
| Dhrs13 | 1.01 | 0.74 | 0.70 | 0.89 | 0.48 | 0.89 | 0.99 | 1.88 | 1.22 | 1.07 | 1.50 | 1.22 |
| Dhrs7c | 1.00 | 1.00 | 1.00 | 1.00 | 1.00 | 1.00 | 1.00 | 1.00 | 1.00 | 1.00 | 1.00 | 1.00 |
| Dhrsx | 1.27 | 1.46 | 0.95 | 0.94 | 0.69 | 1.22 | 1.26 | 2.39 | 1.15 | 1.24 | 1.63 | 1.18 |
| Dhx58 | 2.27 | 2.01 | 1.97 | 1.12 | 1.54 | 1.03 | 1.48 | 2.04 | 3.43 | 3.42 | 2.83 | 1.91 |
| Dio3os | 1.00 | 1.09 | 0.92 | 4.78 | 3.55 | 1.98 | 0.29 | 0.51 | 0.48 | 0.66 | 0.90 | 0.69 |
| Diras1 | 1.00 | 1.00 | 1.00 | 1.00 | 1.00 | 1.00 | 1.00 | 1.00 | 1.00 | 1.00 | 1.00 | 1.00 |
| Disp2 | 1.00 | 1.00 | 1.00 | 1.00 | 1.00 | 1.00 | 1.00 | 1.00 | 1.00 | 1.14 | 0.88 | 1.17 |
| Dlgap1 | 1.00 | 1.00 | 1.00 | 1.00 | 1.00 | 1.00 | 1.00 | 1.00 | 1.00 | 1.00 | 1.00 | 1.00 |
| Dlgap3 | 1.00 | 1.00 | 1.00 | 1.00 | 1.00 | 1.00 | 1.00 | 1.00 | 1.00 | 1.00 | 1.00 | 1.00 |
| Dlgap4 | 1.10 | 1.11 | 1.09 | 0.95 | 0.98 | 1.12 | 1.18 | 1.68 | 1.08 | 0.94 | 1.15 | 1.05 |
| Dmap1 | 1.13 | 1.36 | 0.92 | 1.03 | 0.92 | 1.01 | 0.94 | 1.25 | 1.03 | 1.01 | 1.39 | 0.96 |
| Dmbt1 | 1.00 | 1.00 | 4.62 | 1.00 | 1.00 | 1.00 | 1.00 | 1.00 | 1.00 | 1.02 | 0.92 | 0.90 |
| Dmkn | 0.80 | 0.60 | 0.64 | 1.00 | 1.00 | 1.00 | 1.00 | 1.00 | 1.00 | 1.06 | 1.30 | 0.34 |
| Dnaaf1 | 1.00 | 1.00 | 1.00 | 1.00 | 0.37 | 1.00 | 1.00 | 4.30 | 1.00 | 1.00 | 1.00 | 1.00 |
| Dnajb12 | 0.87 | 0.84 | 1.09 | 1.26 | 1.60 | 1.28 | 1.36 | 1.31 | 1.34 | 1.07 | 0.76 | 1.05 |
| Dnajb14 | 1.07 | 0.84 | 0.88 | 1.79 | 0.84 | 1.20 | 1.18 | 3.91 | 1.07 | 1.56 | 1.65 | 0.96 |
| Dnajb2 | 1.45 | 1.75 | 1.26 | 1.00 | 0.67 | 0.89 | 1.27 | 3.65 | 1.01 | 0.90 | 1.46 | 1.14 |
| Dnajc11 | 0.94 | 1.16 | 0.80 | 0.94 | 0.56 | 0.90 | 0.96 | 2.23 | 0.84 | 0.89 | 1.36 | 0.99 |
| Dnajc15 | 1.53 | 1.26 | 1.05 | 0.85 | 0.79 | 0.86 | 1.44 | 1.69 | 0.73 | 0.63 | 1.80 | 0.87 |
| Dnajc17 | 0.97 | 2.71 | 0.94 | 1.00 | 0.66 | 1.00 | 1.00 | 4.44 | 1.00 | 1.00 | 1.41 | 1.30 |
| Dnajc19 | 0.99 | 0.69 | 0.88 | 0.89 | 0.47 | 1.10 | 0.74 | 1.32 | 0.60 | 0.87 | 1.28 | 0.81 |
| Dnajc22 | 1.00 | 1.00 | 1.00 | 1.27 | 1.39 | 1.10 | 0.90 | 1.16 | 1.03 | 0.89 | 0.88 | 0.94 |
| Dnajc9 | 0.67 | 0.75 | 0.69 | 0.85 | 0.91 | 0.78 | 1.26 | 0.53 | 0.63 | 0.88 | 1.18 | 1.10 |
| Dnase2a | 2.47 | 2.40 | 1.69 | 0.96 | 0.42 | 1.02 | 0.53 | 2.68 | 0.73 | 0.95 | 1.22 | 1.09 |
| Dner | 1.00 | 1.00 | 1.00 | 1.00 | 1.00 | 1.00 | 1.00 | 1.00 | 1.00 | 1.04 | 1.14 | 1.45 |
| Dnph1 | 0.45 | 0.43 | 0.44 | 0.90 | 0.76 | 0.81 | 0.62 | 0.45 | 0.57 | 1.69 | 1.24 | 1.46 |
| Dnttip1 | 1.33 | 1.65 | 1.06 | 0.95 | 1.05 | 0.83 | 1.16 | 1.46 | 1.01 | 1.00 | 1.83 | 1.13 |
| Doc2b | 4.89 | 3.37 | 3.34 | 1.00 | 1.00 | 1.00 | 1.00 | 1.00 | 1.00 | 1.28 | 0.91 | 1.38 |
| Doc2g | 1.09 | 1.16 | 0.86 | 0.63 | 0.53 | 1.18 | 1.00 | 1.06 | 0.81 | 0.77 | 1.68 | 1.29 |
| Dpagt1 | 1.13 | 1.17 | 1.06 | 1.03 | 0.57 | 1.11 | 1.07 | 2.33 | 1.13 | 0.98 | 1.36 | 1.10 |
| Dpcd | 1.25 | 1.72 | 0.90 | 0.73 | 0.56 | 0.81 | 1.78 | 2.24 | 0.73 | 1.12 | 1.65 | 1.03 |
| Dpep1 | 7.47 | 4.90 | 2.56 | 1.21 | 0.83 | 1.14 | 3.23 | 8.33 | 1.14 | 1.32 | 1.62 | 1.27 |
| Dph1 | 0.82 | 1.01 | 1.39 | 1.12 | 2.15 | 1.25 | 1.46 | 5.14 | 1.01 | 0.76 | 1.00 | 1.27 |
| Dph5 | 1.41 | 0.99 | 0.78 | 0.75 | 1.10 | 0.92 | 1.23 | 1.87 | 1.06 | 0.90 | 1.30 | 1.14 |
| Dpm3 | 1.26 | 1.76 | 0.86 | 0.62 | 0.59 | 0.85 | 0.72 | 0.67 | 0.85 | 0.96 | 1.51 | 1.04 |
| Dpp6 | 1.01 | 0.46 | 0.55 | 1.00 | 1.00 | 1.00 | 1.00 | 1.00 | 1.00 | 1.03 | 0.97 | 1.19 |
| Dpp7 | 3.65 | 3.27 | 2.87 | 2.00 | 1.41 | 2.18 | 1.71 | 2.10 | 2.03 | 2.42 | 2.86 | 1.71 |
| Dpy30 | 1.04 | 1.11 | 0.84 | 0.86 | 0.80 | 0.77 | 1.14 | 0.45 | 1.24 | 1.09 | 1.64 | 1.16 |
| Drap1 | 0.92 | 1.19 | 0.85 | 0.91 | 0.61 | 0.83 | 0.90 | 1.36 | 0.82 | 1.08 | 1.68 | 1.03 |
| Dreh | 1.00 | 1.00 | 1.00 | 1.00 | 1.00 | 1.00 | 7.75 | 2.02 | 5.56 | 1.00 | 1.00 | 1.00 |
| Drosha | 0.75 | 0.73 | 0.94 | 1.31 | 0.57 | 1.28 | 1.39 | 1.78 | 1.13 | 1.01 | 0.92 | 0.95 |
| Dtnb | 0.98 | 1.20 | 1.04 | 1.23 | 0.70 | 1.17 | 1.47 | 2.83 | 1.23 | 0.64 | 1.02 | 0.57 |
| Dus1l | 0.92 | 1.26 | 0.87 | 0.96 | 0.68 | 1.12 | 1.01 | 1.36 | 0.86 | 1.00 | 1.42 | 0.96 |
| Dus2 | 1.28 | 1.59 | 0.84 | 1.01 | 0.98 | 0.91 | 1.54 | 0.94 | 1.03 | 0.68 | 1.46 | 0.96 |
| Dusp1 | 1.83 | 1.86 | 1.39 | 2.05 | 6.83 | 1.73 | 2.14 | 1.38 | 1.16 | 1.32 | 1.80 | 1.01 |
| Dusp22 | 0.91 | 0.82 | 1.12 | 0.87 | 0.91 | 0.90 | 0.88 | 0.73 | 1.05 | 1.03 | 1.50 | 1.20 |
| Dusp26 | 1.00 | 1.00 | 1.03 | 1.00 | 0.64 | 1.00 | 1.00 | 1.00 | 1.00 | 1.54 | 1.80 | 1.53 |
| Dym | 1.54 | 1.59 | 1.19 | 1.06 | 0.83 | 1.10 | 1.34 | 1.80 | 1.00 | 1.13 | 1.48 | 1.10 |
| Dync1h1 | 0.98 | 0.96 | 1.02 | 1.41 | 0.75 | 1.30 | 1.23 | 2.59 | 1.34 | 1.06 | 1.10 | 0.95 |
| Dync1li1 | 0.80 | 0.76 | 0.91 | 1.02 | 1.00 | 0.84 | 1.41 | 1.00 | 1.32 | 1.25 | 0.87 | 1.00 |
| Dynlrb1 | 0.99 | 1.37 | 0.85 | 0.80 | 0.61 | 0.94 | 1.04 | 1.86 | 1.00 | 1.18 | 1.67 | 1.01 |
| Dynlt1c | 0.97 | 1.21 | 0.74 | 0.60 | 3.22 | 0.65 | 1.07 | 0.14 | 0.96 | 0.91 | 1.36 | 0.97 |
| Dzank1 | 1.00 | 1.00 | 1.00 | 0.70 | 1.00 | 0.86 | 1.00 | 1.00 | 1.00 | 1.00 | 1.00 | 1.00 |
| E030018B13Rik | 1.00 | 1.00 | 1.00 | 1.00 | 1.00 | 1.00 | 17.68 | 17.67 | 13.64 | 1.00 | 1.00 | 1.00 |
| E030030I06Rik | 0.83 | 1.04 | 0.80 | 1.50 | 0.75 | 1.44 | 1.28 | 1.39 | 1.05 | 1.34 | 1.54 | 0.70 |
| E030044B06Rik | 1.00 | 1.00 | 1.00 | 1.00 | 1.00 | 1.00 | 1.00 | 1.00 | 1.00 | 1.00 | 1.00 | 1.00 |
| E130012A19Rik | 1.48 | 1.59 | 1.42 | 0.85 | 0.68 | 0.98 | 1.05 | 6.79 | 0.64 | 1.55 | 2.71 | 1.17 |
| E130201H02Rik | 0.63 | 0.62 | 0.81 | 1.72 | 1.00 | 1.62 | 0.91 | 1.00 | 0.96 | 1.02 | 0.54 | 0.81 |
| E230008N13Rik | 1.00 | 1.00 | 1.00 | 1.00 | 1.00 | 1.00 | 1.00 | 1.00 | 1.00 | 1.00 | 1.00 | 1.00 |
| E530011L22Rik | 1.04 | 1.00 | 1.54 | 1.00 | 0.49 | 1.00 | 1.00 | 2.13 | 1.00 | 1.00 | 1.00 | 0.97 |
| Eapp | 1.06 | 1.22 | 0.97 | 1.25 | 0.94 | 0.98 | 1.23 | 2.15 | 0.99 | 1.11 | 1.88 | 1.02 |
| Ear1 | 0.22 | 0.69 | 0.82 | 1.00 | 1.00 | 1.00 | 1.00 | 1.00 | 1.00 | 1.00 | 1.00 | 1.00 |
| Ear3 | 0.63 | 0.26 | 1.00 | 1.00 | 1.00 | 1.00 | 1.00 | 1.00 | 1.82 | 1.00 | 1.00 | 1.00 |

Fig. 35- 159

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Dgat1 | 0.80 | 1.06 | 0.89 | 0.66 | 3.33 | 1.36 | 0.89 | 1.95 | 1.19 | 1.57 | 1.54 | 1.13 |
| Dhrs13 | 0.73 | 0.55 | 0.79 | 1.16 | 3.44 | 1.34 | 0.87 | 2.37 | 0.76 | 0.87 | 1.01 | 0.85 |
| Dhrs7c | 1.00 | 1.00 | 1.00 | 1.00 | 1.00 | 1.00 | 1.00 | 1.00 | 1.00 | 1.00 | 1.00 | 1.00 |
| Dhrsx | 1.12 | 1.30 | 1.11 | 1.37 | 2.92 | 1.23 | 0.90 | 3.87 | 1.06 | 1.11 | 1.47 | 1.04 |
| Dhx58 | 3.47 | 5.77 | 4.08 | 1.10 | 0.74 | 1.04 | 0.94 | 1.69 | 1.03 | 2.98 | 2.43 | 1.64 |
| Dio3os | 1.00 | 1.00 | 1.00 | 1.31 | 6.82 | 2.28 | 1.00 | 1.00 | 1.00 | 1.00 | 1.00 | 1.00 |
| Diras1 | 1.00 | 1.00 | 1.00 | 1.00 | 1.00 | 1.00 | 0.98 | 1.72 | 1.37 | 1.00 | 7.30 | 1.00 |
| Disp2 | 1.05 | 1.15 | 1.06 | 0.38 | 0.36 | 0.31 | 1.00 | 1.00 | 1.00 | 1.00 | 10.78 | 1.00 |
| Dlgap1 | 0.11 | 0.10 | 0.09 | 1.00 | 1.00 | 1.01 | 0.95 | 1.00 | 1.00 | 1.00 | 9.23 | 1.00 |
| Dlgap3 | 1.00 | 1.00 | 1.00 | 1.00 | 1.00 | 1.00 | 1.00 | 2.47 | 1.10 | 1.00 | 8.55 | 1.00 |
| Dlgap4 | 1.01 | 1.13 | 1.14 | 0.93 | 1.77 | 0.99 | 0.76 | 2.03 | 1.06 | 0.89 | 1.09 | 0.95 |
| Dmap1 | 1.10 | 1.05 | 1.25 | 0.94 | 5.37 | 0.89 | 1.11 | 1.53 | 1.01 | 1.13 | 1.37 | 1.04 |
| Dmbt1 | 1.94 | 1.56 | 1.87 | 1.00 | 1.00 | 1.00 | 1.00 | 1.00 | 1.00 | 1.00 | 5.05 | 1.03 |
| Dmkn | 0.94 | 1.14 | 1.44 | 1.49 | 3.52 | 2.28 | 1.38 | 0.32 | 0.91 | 1.00 | 1.00 | 1.00 |
| Dnaaf1 | 1.00 | 1.00 | 1.00 | 2.07 | 1.95 | 1.94 | 1.03 | 2.18 | 1.05 | 1.00 | 1.00 | 1.00 |
| Dnajb12 | 1.24 | 1.30 | 1.03 | 1.51 | 1.46 | 1.18 | 1.09 | 0.85 | 0.96 | 1.10 | 0.89 | 1.09 |
| Dnajb14 | 0.72 | 1.11 | 0.66 | 1.44 | 2.15 | 1.08 | 1.03 | 3.20 | 1.02 | 0.84 | 0.81 | 0.77 |
| Dnajb2 | 0.91 | 1.08 | 0.90 | 1.67 | 2.31 | 1.54 | 0.91 | 2.87 | 0.93 | 0.80 | 1.10 | 0.73 |
| Dnajc11 | 0.82 | 0.88 | 0.96 | 1.00 | 2.23 | 1.16 | 0.79 | 3.73 | 0.90 | 0.98 | 1.18 | 0.96 |
| Dnajc15 | 1.28 | 1.11 | 0.86 | 0.64 | 2.19 | 0.78 | 0.93 | 2.28 | 1.02 | 0.78 | 1.35 | 1.05 |
| Dnajc17 | 1.00 | 1.00 | 1.00 | 1.00 | 1.63 | 1.01 | 0.73 | 4.88 | 1.63 | 1.00 | 1.08 | 0.94 |
| Dnajc19 | 0.84 | 0.71 | 1.17 | 0.75 | 1.77 | 0.84 | 1.33 | 3.53 | 0.77 | 0.92 | 0.81 | 1.24 |
| Dnajc22 | 0.85 | 0.89 | 0.58 | 1.47 | 1.00 | 3.03 | 0.96 | 5.35 | 1.21 | 1.00 | 1.00 | 1.00 |
| Dnajc9 | 0.77 | 0.74 | 0.87 | 1.11 | 2.96 | 0.98 | 0.83 | 1.38 | 0.86 | 0.91 | 0.88 | 0.85 |
| Dnase2a | 0.95 | 1.12 | 1.17 | 0.79 | 0.65 | 0.65 | 0.92 | 7.17 | 0.53 | 0.86 | 1.27 | 0.83 |
| Dner | 1.00 | 0.93 | 1.00 | 1.00 | 1.00 | 1.00 | 1.00 | 1.00 | 1.00 | 1.00 | 6.88 | 1.00 |
| Dnph1 | 0.60 | 0.56 | 0.74 | 1.00 | 1.00 | 1.05 | 1.07 | 1.51 | 0.84 | 0.83 | 0.75 | 0.69 |
| Dnttip1 | 0.78 | 1.31 | 1.15 | 0.99 | 3.04 | 1.14 | 0.80 | 0.81 | 0.82 | 1.03 | 1.32 | 0.83 |
| Doc2b | 1.59 | 1.89 | 1.61 | 1.54 | 1.00 | 1.62 | 0.79 | 1.00 | 0.59 | 1.00 | 1.80 | 1.00 |
| Doc2g | 1.62 | 0.76 | 1.05 | 0.99 | 1.00 | 0.94 | 1.00 | 1.55 | 1.00 | 1.70 | 2.44 | 1.24 |
| Dpagt1 | 0.91 | 0.87 | 0.82 | 1.00 | 2.43 | 0.88 | 1.10 | 1.91 | 0.94 | 1.03 | 0.95 | 0.98 |
| Dpcd | 0.97 | 1.11 | 0.95 | 0.81 | 3.33 | 1.09 | 0.87 | 2.73 | 0.92 | 1.16 | 1.30 | 0.83 |
| Dpep1 | 2.26 | 3.14 | 2.85 | 1.16 | 2.96 | 1.14 | 1.19 | 3.86 | 0.96 | 2.81 | 3.60 | 2.71 |
| Dph1 | 0.78 | 1.36 | 1.33 | 1.43 | 9.26 | 1.41 | 0.78 | 1.91 | 1.20 | 1.20 | 1.22 | 0.88 |
| Dph5 | 0.85 | 1.00 | 0.90 | 1.27 | 1.21 | 0.89 | 0.68 | 1.02 | 1.50 | 1.34 | 1.28 | 1.17 |
| Dpm3 | 0.81 | 1.44 | 1.06 | 0.74 | 1.83 | 0.86 | 0.79 | 1.64 | 0.82 | 0.99 | 1.24 | 0.94 |
| Dpp6 | 1.00 | 1.00 | 1.00 | 1.00 | 1.00 | 1.00 | 1.00 | 1.71 | 0.94 | 1.00 | 6.01 | 1.00 |
| Dpp7 | 2.86 | 2.44 | 2.60 | 1.54 | 1.36 | 1.79 | 1.64 | 2.85 | 1.63 | 1.66 | 1.97 | 1.74 |
| Dpy30 | 0.85 | 0.78 | 1.02 | 0.72 | 7.02 | 1.20 | 1.19 | 0.83 | 1.37 | 1.11 | 1.19 | 0.88 |
| Drap1 | 0.82 | 1.24 | 1.07 | 0.93 | 2.61 | 1.09 | 0.86 | 2.09 | 0.98 | 1.05 | 1.61 | 0.84 |
| Dreh | 1.00 | 1.00 | 1.00 | 1.00 | 1.00 | 1.00 | 1.00 | 1.00 | 1.00 | 1.00 | 1.00 | 1.00 |
| Drosha | 1.09 | 1.01 | 0.82 | 1.28 | 2.19 | 0.96 | 1.23 | 2.50 | 1.09 | 0.91 | 0.97 | 1.03 |
| Dtnb | 0.81 | 1.07 | 1.00 | 1.55 | 5.88 | 1.72 | 1.05 | 3.52 | 1.16 | 0.82 | 1.46 | 0.94 |
| Dus1l | 0.82 | 0.83 | 0.86 | 1.25 | 2.85 | 1.31 | 1.11 | 2.35 | 1.24 | 1.03 | 1.37 | 0.93 |
| Dus2 | 0.68 | 0.65 | 0.89 | 0.82 | 1.25 | 1.22 | 0.93 | 1.41 | 0.76 | 0.84 | 1.20 | 1.00 |
| Dusp1 | 1.70 | 2.93 | 1.14 | 1.66 | 0.92 | 1.17 | 1.02 | 1.58 | 1.33 | 2.15 | 3.95 | 1.64 |
| Dusp22 | 0.90 | 1.10 | 1.35 | 1.01 | 10.78 | 1.08 | 0.88 | 0.50 | 0.82 | 1.05 | 1.10 | 1.15 |
| Dusp26 | 2.42 | 2.66 | 2.85 | 0.78 | 1.68 | 0.88 | 1.00 | 1.00 | 1.00 | 0.78 | 3.68 | 0.75 |
| Dym | 1.11 | 1.28 | 0.99 | 0.90 | 2.48 | 1.07 | 0.90 | 1.64 | 0.99 | 1.13 | 1.31 | 0.89 |
| Dync1h1 | 1.06 | 1.08 | 0.83 | 1.33 | 1.30 | 0.98 | 1.34 | 2.51 | 1.22 | 0.96 | 1.11 | 1.16 |
| Dync1li1 | 1.04 | 0.97 | 0.97 | 1.17 | 1.00 | 1.06 | 1.25 | 1.00 | 0.95 | 0.91 | 0.88 | 0.99 |
| Dynlrb1 | 0.90 | 1.06 | 1.21 | 0.76 | 2.30 | 0.97 | 0.89 | 2.61 | 1.19 | 0.96 | 1.36 | 0.89 |
| Dynlt1c | 0.79 | 0.61 | 0.75 | 1.04 | 5.75 | 0.80 | 0.86 | 0.01 | 0.79 | 0.90 | 0.88 | 0.73 |
| Dzank1 | 1.00 | 1.00 | 1.00 | 1.12 | 1.00 | 1.05 | 1.10 | 1.00 | 1.08 | 1.00 | 6.29 | 1.00 |
| E030018B13Rik | 1.00 | 1.00 | 1.00 | 0.69 | 1.00 | 2.80 | 1.00 | 1.00 | 1.00 | 1.00 | 1.00 | 1.00 |
| E030030I06Rik | 1.03 | 0.72 | 1.11 | 1.46 | 1.18 | 1.02 | 1.00 | 1.49 | 1.00 | 1.24 | 1.25 | 1.81 |
| E030044B06Rik | 1.00 | 1.00 | 1.00 | 1.00 | 1.00 | 1.00 | 1.00 | 2.40 | 1.00 | 1.00 | 1.00 | 1.00 |
| E130012A19Rik | 0.45 | 0.57 | 0.42 | 2.47 | 12.87 | 1.34 | 1.00 | 3.91 | 0.96 | 1.18 | 2.00 | 1.22 |
| E130201H02Rik | 0.97 | 0.85 | 0.81 | 1.47 | 0.26 | 1.12 | 1.03 | 1.64 | 1.11 | 1.07 | 0.86 | 0.96 |
| E230008N13Rik | 1.00 | 1.00 | 1.00 | 1.00 | 1.00 | 1.00 | 1.43 | 4.35 | 1.12 | 1.00 | 1.00 | 1.00 |
| E530011L22Rik | 1.00 | 1.00 | 1.00 | 1.00 | 0.86 | 1.00 | 0.92 | 2.20 | 1.10 | 1.00 | 1.00 | 1.00 |
| Eapp | 1.03 | 1.19 | 1.03 | 1.46 | 4.64 | 1.35 | 1.11 | 1.87 | 0.86 | 1.07 | 1.19 | 0.93 |
| Ear1 | 1.00 | 1.00 | 1.00 | 1.00 | 1.00 | 1.00 | 1.00 | 1.00 | 1.00 | 4.23 | 6.08 | 2.33 |
| Ear3 | 1.00 | 1.00 | 1.00 | 1.73 | 1.00 | 0.17 | 1.00 | 1.00 | 1.00 | 8.88 | 0.14 | 1.00 |

Fig. 35- 160

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Dgat1 | 0.81 | 1.00 | 1.49 | 1.22 | 0.55 | 1.06 | 1.55 | 9.24 | 1.30 | 4.19 | 2.06 | 1.66 |
| Dhrs13 | 1.36 | 1.45 | 1.01 | 0.99 | 0.73 | 1.15 | 0.89 | 5.82 | 0.76 | 1.36 | 0.95 | 1.04 |
| Dhrs7c | 1.00 | 1.00 | 1.00 | 1.00 | 1.00 | 1.00 | 2.62 | 18.15 | 2.58 | 1.00 | 1.00 | 1.00 |
| Dhrsx | 1.19 | 0.93 | 1.27 | 1.01 | 0.74 | 1.35 | 1.32 | 4.45 | 0.94 | 1.91 | 1.08 | 1.20 |
| Dhx58 | 1.00 | 1.00 | 1.00 | 1.00 | 0.69 | 1.00 | 1.08 | 2.21 | 0.99 | 4.13 | 2.54 | 2.09 |
| Dio3os | 1.00 | 1.00 | 1.00 | 1.00 | 2.25 | 1.00 | 1.80 | 10.33 | 2.39 | 1.00 | 1.00 | 1.00 |
| Diras1 | 1.00 | 1.00 | 1.00 | 1.12 | 0.98 | 1.03 | 1.00 | 1.00 | 1.00 | 1.00 | 1.00 | 1.00 |
| Disp2 | 1.00 | 1.00 | 1.00 | 1.04 | 0.49 | 1.05 | 1.00 | 1.00 | 1.00 | 1.00 | 1.00 | 1.00 |
| Dlgap1 | 1.00 | 1.00 | 1.00 | 0.94 | 0.74 | 0.91 | 1.35 | 1.78 | 1.66 | 1.00 | 1.00 | 1.00 |
| Dlgap3 | 1.26 | 1.26 | 0.78 | 1.12 | 1.13 | 1.12 | 1.00 | 1.00 | 1.00 | 1.00 | 1.00 | 1.00 |
| Dlgap4 | 1.33 | 0.87 | 1.42 | 1.12 | 1.10 | 1.06 | 1.09 | 5.62 | 0.92 | 2.41 | 1.18 | 1.07 |
| Dmap1 | 0.96 | 1.05 | 0.80 | 1.09 | 1.15 | 1.07 | 1.11 | 3.56 | 0.84 | 1.57 | 1.25 | 1.00 |
| Dmbt1 | 1.98 | 2.74 | 1.83 | 1.00 | 1.00 | 1.00 | 1.00 | 1.00 | 1.00 | 1.00 | 1.00 | 1.00 |
| Dmkn | 1.00 | 1.00 | 1.00 | 0.67 | 0.13 | 1.28 | 1.11 | 5.92 | 0.66 | 1.00 | 1.70 | 1.17 |
| Dnaaf1 | 1.00 | 1.00 | 1.00 | 1.00 | 0.74 | 1.00 | 3.22 | 32.10 | 1.00 | 2.69 | 1.00 | 1.00 |
| Dnajb12 | 1.42 | 1.07 | 0.92 | 0.98 | 6.77 | 0.94 | 1.20 | 1.34 | 1.18 | 1.62 | 1.21 | 0.90 |
| Dnajb14 | 1.00 | 1.11 | 1.00 | 0.57 | 0.21 | 1.01 | 1.63 | 11.39 | 1.10 | 3.26 | 1.53 | 1.41 |
| Dnajb2 | 1.06 | 1.07 | 1.15 | 1.07 | 0.83 | 1.01 | 1.00 | 5.31 | 0.78 | 1.70 | 1.02 | 0.89 |
| Dnajc11 | 1.24 | 0.84 | 0.75 | 1.19 | 0.92 | 1.01 | 1.08 | 10.60 | 1.11 | 1.57 | 0.83 | 0.78 |
| Dnajc15 | 1.48 | 1.06 | 1.48 | 1.19 | 0.96 | 1.24 | 1.55 | 20.37 | 0.85 | 3.77 | 1.43 | 1.04 |
| Dnajc17 | 1.00 | 1.00 | 1.00 | 1.00 | 1.25 | 1.00 | 1.00 | 24.91 | 1.02 | 5.91 | 1.00 | 1.00 |
| Dnajc19 | 0.63 | 0.53 | 1.48 | 0.91 | 1.86 | 0.68 | 1.36 | 11.25 | 1.18 | 5.37 | 1.36 | 1.02 |
| Dnajc22 | 0.73 | 0.71 | 0.63 | 1.00 | 1.00 | 1.00 | 1.41 | 2.10 | 0.92 | 1.00 | 1.00 | 1.00 |
| Dnajc9 | 0.72 | 0.69 | 0.53 | 1.06 | 5.97 | 0.97 | 0.89 | 0.59 | 0.82 | 0.61 | 0.84 | 0.86 |
| Dnase2a | 0.74 | 0.72 | 0.73 | 1.07 | 0.73 | 1.20 | 1.24 | 21.64 | 0.84 | 3.57 | 1.19 | 0.80 |
| Dner | 1.00 | 1.00 | 1.00 | 1.06 | 1.08 | 1.06 | 1.00 | 1.00 | 1.00 | 1.00 | 1.00 | 1.00 |
| Dnph1 | 1.04 | 0.95 | 1.00 | 1.06 | 7.95 | 1.34 | 0.46 | 0.58 | 0.56 | 1.63 | 0.85 | 0.71 |
| Dnttip1 | 1.32 | 1.24 | 1.83 | 0.96 | 0.90 | 1.00 | 1.15 | 2.22 | 0.79 | 1.69 | 1.11 | 1.12 |
| Doc2b | 1.00 | 1.00 | 1.00 | 1.21 | 1.33 | 1.06 | 1.97 | 0.73 | 2.59 | 1.00 | 1.00 | 1.00 |
| Doc2g | 1.00 | 1.00 | 1.00 | 0.81 | 1.05 | 0.73 | 1.45 | 5.73 | 1.37 | 2.55 | 0.95 | 0.99 |
| Dpagt1 | 1.03 | 0.71 | 0.85 | 1.07 | 0.57 | 0.96 | 1.00 | 6.47 | 0.97 | 1.98 | 0.91 | 1.16 |
| Dpcd | 0.89 | 0.86 | 1.16 | 1.22 | 0.98 | 1.08 | 0.84 | 11.59 | 0.92 | 4.26 | 1.79 | 1.09 |
| Dpep1 | 1.15 | 1.72 | 1.57 | 1.00 | 0.59 | 1.00 | 2.30 | 12.56 | 2.15 | 1.00 | 1.02 | 1.39 |
| Dph1 | 2.41 | 0.84 | 1.04 | 1.03 | 1.00 | 0.80 | 1.08 | 3.83 | 1.07 | 1.00 | 0.98 | 0.64 |
| Dph5 | 0.98 | 1.00 | 1.35 | 0.83 | 0.71 | 0.78 | 0.99 | 5.97 | 0.95 | 2.07 | 1.10 | 1.20 |
| Dpm3 | 1.18 | 0.90 | 0.77 | 1.30 | 0.97 | 1.21 | 1.30 | 6.79 | 0.93 | 2.63 | 1.08 | 1.19 |
| Dpp6 | 1.00 | 1.00 | 1.00 | 1.09 | 0.86 | 1.03 | 1.00 | 1.00 | 1.00 | 1.00 | 1.00 | 1.00 |
| Dpp7 | 3.34 | 1.81 | 2.30 | 1.71 | 1.37 | 1.66 | 1.49 | 4.85 | 1.41 | 4.82 | 2.89 | 2.25 |
| Dpy30 | 0.91 | 0.78 | 1.22 | 0.78 | 1.88 | 0.91 | 1.16 | 1.36 | 0.78 | 1.54 | 1.07 | 1.31 |
| Drap1 | 1.25 | 0.80 | 0.89 | 1.09 | 1.22 | 1.16 | 1.30 | 9.39 | 1.02 | 2.53 | 1.30 | 1.16 |
| Dreh | 1.00 | 1.00 | 1.00 | 1.00 | 1.00 | 1.00 | 1.00 | 1.00 | 1.00 | 1.00 | 1.00 | 1.00 |
| Drosha | 1.00 | 1.00 | 1.00 | 1.30 | 1.16 | 1.21 | 0.98 | 5.24 | 1.20 | 2.21 | 0.98 | 0.95 |
| Dtnb | 0.97 | 0.52 | 0.88 | 1.06 | 0.91 | 1.09 | 1.25 | 9.97 | 0.99 | 3.41 | 1.07 | 0.91 |
| Dus1l | 1.41 | 0.62 | 1.31 | 1.41 | 0.88 | 1.05 | 1.12 | 8.76 | 0.86 | 2.74 | 0.97 | 0.99 |
| Dus2 | 1.00 | 1.00 | 1.00 | 1.51 | 0.77 | 0.91 | 1.21 | 6.00 | 0.95 | 1.67 | 0.79 | 1.03 |
| Dusp1 | 1.69 | 3.98 | 2.69 | 1.46 | 1.41 | 1.37 | 1.37 | 0.50 | 1.28 | 1.83 | 4.72 | 1.88 |
| Dusp22 | 1.62 | 1.90 | 1.05 | 0.96 | 0.43 | 1.05 | 0.82 | 1.55 | 0.75 | 1.06 | 0.89 | 0.93 |
| Dusp26 | 1.58 | 1.84 | 2.87 | 1.19 | 0.80 | 1.03 | 2.24 | 5.07 | 2.97 | 1.00 | 1.00 | 1.00 |
| Dym | 0.91 | 0.80 | 0.84 | 1.03 | 0.77 | 0.99 | 1.23 | 7.08 | 1.09 | 2.27 | 1.29 | 1.04 |
| Dync1h1 | 1.03 | 1.15 | 1.21 | 0.91 | 0.94 | 0.98 | 1.09 | 5.57 | 1.07 | 2.34 | 1.10 | 0.97 |
| Dync1li1 | 1.09 | 1.37 | 0.95 | 1.01 | 1.00 | 1.09 | 0.75 | 0.07 | 0.88 | 0.24 | 1.21 | 1.11 |
| Dynlrb1 | 0.63 | 1.06 | 0.94 | 1.06 | 0.92 | 1.10 | 1.22 | 7.42 | 0.94 | 2.47 | 1.26 | 1.21 |
| Dynlt1c | 1.06 | 0.60 | 0.79 | 0.84 | 1.00 | 0.89 | 1.08 | 0.33 | 1.15 | 1.10 | 1.15 | 1.18 |
| Dzank1 | 1.00 | 1.00 | 1.00 | 0.96 | 0.86 | 0.97 | 1.00 | 1.00 | 1.00 | 1.00 | 1.00 | 1.00 |
| E030018B13Rik | 1.00 | 1.00 | 1.00 | 1.00 | 1.00 | 1.00 | 1.00 | 1.00 | 1.00 | 1.00 | 1.00 | 1.00 |
| E030030I06Rik | 0.88 | 1.00 | 1.00 | 1.00 | 1.00 | 1.00 | 1.93 | 7.96 | 1.31 | 3.61 | 1.29 | 1.82 |
| E030044B06Rik | 1.00 | 1.00 | 1.00 | 1.00 | 1.00 | 1.00 | 1.00 | 5.62 | 1.00 | 1.00 | 1.00 | 1.00 |
| E130012A19Rik | 1.00 | 1.00 | 1.00 | 1.12 | 0.88 | 0.96 | 1.13 | 10.85 | 0.98 | 3.27 | 1.26 | 0.98 |
| E130201H02Rik | 0.64 | 1.14 | 1.18 | 0.91 | 0.94 | 1.41 | 1.73 | 0.09 | 1.20 | 0.19 | 0.84 | 0.83 |
| E230008N13Rik | 1.00 | 1.00 | 1.00 | 1.00 | 1.00 | 1.00 | 1.00 | 1.00 | 1.00 | 2.64 | 1.00 | 1.00 |
| E530011L22Rik | 1.00 | 1.00 | 1.00 | 1.04 | 0.87 | 1.05 | 1.00 | 10.15 | 0.96 | 1.00 | 1.00 | 1.00 |
| Eapp | 1.19 | 0.76 | 0.72 | 1.19 | 1.44 | 0.80 | 0.93 | 7.69 | 0.95 | 2.56 | 1.04 | 1.24 |
| Ear1 | 1.00 | 1.00 | 1.00 | 1.00 | 0.91 | 1.00 | 1.00 | 1.00 | 1.00 | 0.63 | 0.65 | 1.04 |
| Ear3 | 0.99 | 1.00 | 1.00 | 1.00 | 1.00 | 1.00 | 1.00 | 1.00 | 1.00 | 1.00 | 1.00 | 1.00 |

Fig. 35- 161

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ear6 | 1.00 | 1.00 | 1.00 | 1.00 | 1.00 | 1.00 | 1.00 | 1.00 | 1.00 | 1.00 | 0.82 | 1.00 |
| Ebi3 | 1.00 | 1.00 | 1.00 | 1.00 | 1.20 | 1.00 | 1.00 | 1.00 | 1.00 | 1.26 | 1.67 | 0.49 |
| Ebp | 1.14 | 0.58 | 0.85 | 0.47 | 5.40 | 0.92 | 0.88 | 0.84 | 0.88 | 2.11 | 2.85 | 0.94 |
| Ebpl | 0.63 | 0.35 | 0.88 | 0.98 | 6.31 | 0.86 | 0.66 | 0.34 | 0.52 | 1.88 | 2.99 | 0.81 |
| Echdc2 | 0.94 | 0.53 | 0.81 | 0.68 | 5.36 | 1.53 | 0.74 | 0.71 | 0.80 | 0.90 | 1.64 | 0.97 |
| Eci2 | 1.11 | 0.76 | 1.07 | 0.57 | 4.17 | 0.98 | 0.90 | 0.88 | 0.85 | 1.56 | 2.78 | 1.31 |
| Ecscr | 0.97 | 0.47 | 0.81 | 0.36 | 4.65 | 0.79 | 0.85 | 0.71 | 1.11 | 1.59 | 1.85 | 0.69 |
| Eddm3b | 1.00 | 1.00 | 1.00 | 1.00 | 1.00 | 1.00 | 1.00 | 1.00 | 1.00 | 1.00 | 1.00 | 1.00 |
| Edf1 | 1.41 | 0.63 | 1.00 | 0.28 | 10.02 | 1.04 | 0.96 | 0.79 | 0.98 | 2.32 | 3.24 | 0.97 |
| Eef1a2 | 1.02 | 0.74 | 0.91 | 1.27 | 0.29 | 1.13 | 1.07 | 1.01 | 0.87 | 2.90 | 1.67 | 0.72 |
| Eef1d | 1.22 | 0.52 | 0.99 | 0.36 | 11.50 | 1.29 | 0.90 | 0.82 | 0.79 | 2.92 | 3.99 | 1.00 |
| Eef1g | 1.30 | 0.67 | 0.86 | 0.40 | 4.87 | 1.03 | 0.87 | 0.83 | 1.01 | 2.14 | 2.59 | 0.93 |
| Efcab2 | 0.51 | 1.00 | 0.75 | 1.00 | 1.00 | 1.11 | 1.01 | 1.41 | 0.86 | 1.78 | 1.00 | 1.23 |
| Efcab4a | 1.45 | 0.66 | 1.21 | 0.72 | 6.41 | 1.64 | 0.84 | 0.96 | 1.14 | 1.60 | 1.97 | 1.08 |
| Efemp1 | 1.45 | 0.76 | 1.57 | 1.11 | 5.45 | 1.11 | 0.90 | 1.02 | 1.20 | 1.89 | 2.23 | 0.89 |
| Efemp2 | 1.01 | 0.55 | 1.10 | 0.38 | 5.46 | 0.84 | 1.15 | 0.46 | 0.98 | 2.32 | 2.77 | 0.83 |
| Egfbp2 | 3.41 | 1.00 | 4.87 | 1.00 | 1.00 | 1.00 | 1.09 | 6.67 | 0.39 | 1.00 | 1.00 | 1.00 |
| Egfl7 | 0.98 | 0.43 | 0.78 | 0.39 | 7.00 | 0.93 | 1.06 | 0.75 | 0.93 | 2.67 | 3.30 | 1.04 |
| Egln2 | 1.34 | 0.93 | 0.95 | 0.79 | 9.61 | 1.41 | 1.32 | 1.12 | 1.09 | 2.44 | 3.31 | 1.12 |
| Egln3 | 4.50 | 5.74 | 3.47 | 1.22 | 1.00 | 1.75 | 0.66 | 0.64 | 0.62 | 1.60 | 1.09 | 1.01 |
| Egr1 | 5.05 | 4.45 | 2.56 | 4.46 | 0.35 | 3.34 | 2.80 | 2.32 | 2.39 | 0.81 | 0.92 | 1.33 |
| Ehhadh | 1.38 | 2.90 | 2.17 | 3.63 | 0.76 | 2.75 | 0.68 | 0.47 | 0.66 | 0.57 | 0.53 | 1.16 |
| Eif2b2 | 1.19 | 0.68 | 0.97 | 0.26 | 5.89 | 1.00 | 1.39 | 0.90 | 1.04 | 3.78 | 4.91 | 1.14 |
| Eif2b4 | 1.36 | 0.67 | 1.23 | 0.33 | 6.51 | 1.06 | 1.04 | 0.75 | 0.97 | 2.66 | 3.77 | 1.02 |
| Eif3b | 1.27 | 0.67 | 1.07 | 0.66 | 6.33 | 1.11 | 1.21 | 1.23 | 1.11 | 2.76 | 3.89 | 1.20 |
| Eif3d | 1.29 | 0.90 | 1.07 | 0.40 | 6.21 | 1.32 | 1.03 | 1.14 | 0.94 | 2.13 | 3.02 | 0.93 |
| Eif3f | 1.23 | 0.61 | 1.00 | 0.53 | 6.39 | 1.22 | 1.31 | 0.85 | 0.94 | 3.63 | 3.83 | 0.90 |
| Eif3h | 1.25 | 0.69 | 0.95 | 0.50 | 4.40 | 1.14 | 0.99 | 0.97 | 0.96 | 1.66 | 2.23 | 1.02 |
| Eif3j1 | 1.00 | 1.00 | 17.72 | 1.00 | 17.26 | 1.00 | 1.00 | 1.00 | 1.00 | 1.00 | 1.00 | 1.00 |
| Eif3j2 | 0.98 | 1.29 | 0.52 | 1.57 | 0.09 | 1.41 | 1.11 | 1.33 | 1.19 | 1.33 | 0.96 | 1.20 |
| Eif3k | 0.96 | 0.71 | 1.01 | 0.19 | 3.11 | 1.06 | 1.17 | 1.00 | 0.87 | 1.74 | 2.04 | 0.91 |
| Eif3m | 0.87 | 0.52 | 1.22 | 0.38 | 4.75 | 1.51 | 1.04 | 0.90 | 0.90 | 2.04 | 2.37 | 0.96 |
| Eif4e2 | 1.13 | 0.91 | 0.98 | 0.61 | 5.01 | 0.93 | 1.01 | 1.07 | 0.93 | 2.43 | 2.66 | 1.10 |
| Eif4ebp1 | 1.90 | 1.59 | 2.06 | 0.61 | 5.50 | 1.24 | 1.45 | 1.18 | 1.07 | 1.54 | 2.49 | 1.00 |
| Eif4ebp3 | 2.09 | 1.01 | 1.58 | 1.63 | 13.22 | 1.26 | 1.14 | 0.58 | 0.72 | 1.85 | 2.86 | 0.77 |
| Eif6 | 1.32 | 0.72 | 1.02 | 0.42 | 5.92 | 1.09 | 1.10 | 0.97 | 1.05 | 2.71 | 3.40 | 0.97 |
| Elane | 1.00 | 1.00 | 1.00 | 1.00 | 1.47 | 1.00 | 1.00 | 1.00 | 1.00 | 1.63 | 3.48 | 1.00 |
| Elavl3 | 1.00 | 1.00 | 1.00 | 1.00 | 0.24 | 1.00 | 1.00 | 1.00 | 1.00 | 1.00 | 1.00 | 1.00 |
| Elk4 | 1.53 | 1.06 | 3.42 | 9.06 | 0.61 | 1.33 | 1.25 | 2.97 | 2.30 | 1.00 | 1.00 | 1.39 |
| Elmod1 | 1.00 | 1.00 | 1.00 | 1.68 | 0.17 | 1.08 | 1.00 | 1.00 | 1.00 | 1.00 | 0.51 | 1.19 |
| Elovl3 | 1.73 | 0.90 | 8.24 | 0.36 | 0.85 | 1.52 | 1.00 | 1.00 | 2.47 | 1.00 | 1.00 | 1.00 |
| Elp6 | 1.29 | 0.87 | 1.09 | 2.48 | 20.00 | 1.41 | 0.96 | 0.83 | 0.63 | 1.28 | 1.72 | 0.91 |
| Emc9 | 0.74 | 0.48 | 0.66 | 0.18 | 3.26 | 0.78 | 0.89 | 0.76 | 0.72 | 1.30 | 2.00 | 1.24 |
| Emd | 1.22 | 0.82 | 0.81 | 1.28 | 3.52 | 1.40 | 0.99 | 0.78 | 0.91 | 1.05 | 1.72 | 1.00 |
| Emp3 | 0.80 | 0.39 | 1.24 | 0.28 | 2.79 | 0.61 | 0.76 | 0.73 | 0.88 | 1.68 | 1.91 | 0.86 |
| Endog | 1.06 | 0.61 | 0.95 | 0.30 | 5.49 | 0.91 | 1.27 | 0.84 | 0.86 | 2.92 | 3.76 | 0.99 |
| Engase | 0.47 | 0.39 | 0.77 | 0.53 | 3.99 | 0.75 | 1.04 | 0.65 | 0.87 | 2.24 | 2.46 | 0.95 |
| Enho | 1.70 | 1.04 | 0.98 | 0.71 | 0.75 | 0.88 | 0.80 | 0.68 | 0.59 | 2.31 | 3.11 | 1.63 |
| Eno2 | 1.12 | 0.50 | 1.07 | 1.00 | 0.07 | 1.27 | 0.80 | 0.71 | 1.06 | 1.56 | 1.61 | 0.77 |
| Eno3 | 0.88 | 0.77 | 0.70 | 0.96 | 1.98 | 0.95 | 0.87 | 0.75 | 0.68 | 1.72 | 1.43 | 0.82 |
| Enpp1 | 1.00 | 1.00 | 1.00 | 1.00 | 1.00 | 1.00 | 1.51 | 1.01 | 1.40 | 2.73 | 2.51 | 0.94 |
| Epdr1 | 0.87 | 1.84 | 0.90 | 1.48 | 0.20 | 1.27 | 1.32 | 1.33 | 1.26 | 0.89 | 0.76 | 1.09 |
| Ephx2 | 0.91 | 0.77 | 1.31 | 0.85 | 4.59 | 1.03 | 0.74 | 0.76 | 0.79 | 1.46 | 2.01 | 1.06 |
| Epn1 | 0.99 | 0.57 | 0.75 | 0.45 | 3.00 | 0.91 | 1.05 | 0.92 | 0.96 | 2.17 | 2.78 | 0.92 |
| Eri3 | 1.18 | 0.72 | 0.91 | 0.43 | 3.32 | 0.92 | 0.98 | 0.85 | 0.74 | 1.58 | 2.27 | 0.88 |
| Ern1 | 0.75 | 1.00 | 1.43 | 9.06 | 0.86 | 1.62 | 2.08 | 4.03 | 2.16 | 1.00 | 1.00 | 1.58 |
| Ero1lb | 1.11 | 1.00 | 1.00 | 2.30 | 2.34 | 2.05 | 1.99 | 1.57 | 1.50 | 4.50 | 5.27 | 3.30 |
| Erp27 | 1.00 | 1.00 | 1.00 | 1.00 | 1.00 | 1.00 | 1.00 | 1.00 | 1.00 | 1.00 | 1.91 | 1.00 |
| Errfi1 | 3.81 | 5.93 | 3.29 | 4.79 | 3.41 | 2.06 | 1.73 | 2.58 | 1.70 | 1.49 | 1.84 | 1.93 |
| Esd | 1.57 | 0.87 | 0.82 | 0.69 | 5.81 | 1.22 | 1.19 | 0.91 | 1.03 | 1.81 | 2.21 | 0.88 |
| Esm1 | 1.00 | 1.00 | 1.00 | 1.00 | 1.00 | 1.00 | 1.00 | 1.00 | 0.98 | 6.65 | 6.67 | 2.60 |
| Espn | 1.00 | 1.00 | 1.00 | 1.00 | 1.00 | 1.00 | 1.00 | 0.68 | 0.70 | 2.83 | 1.39 | 1.03 |
| Etfb | 0.92 | 0.40 | 0.76 | 0.28 | 8.99 | 0.73 | 0.84 | 0.76 | 0.76 | 3.31 | 4.49 | 1.04 |
| Etnppl | 1.00 | 1.00 | 1.00 | 1.00 | 1.00 | 1.00 | 1.00 | 1.00 | 1.00 | 1.00 | 1.00 | 1.00 |

Fig. 35- 162

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ear6 | 0.35 | 1.00 | 1.00 | 1.00 | 1.00 | 1.00 | 1.00 | 1.00 | 1.00 | 1.00 | 1.00 | 1.00 |
| Ebi3 | 0.90 | 1.55 | 1.25 | 1.00 | 0.94 | 1.00 | 1.00 | 2.40 | 1.00 | 1.38 | 1.73 | 0.69 |
| Ebp | 1.13 | 1.40 | 0.99 | 1.01 | 0.77 | 1.11 | 0.93 | 1.75 | 0.79 | 1.17 | 1.68 | 1.23 |
| Ebpl | 1.48 | 1.76 | 1.15 | 0.87 | 0.54 | 0.96 | 0.51 | 0.91 | 0.74 | 0.87 | 1.29 | 1.05 |
| Echdc2 | 2.21 | 1.89 | 1.45 | 0.86 | 0.97 | 0.98 | 0.89 | 0.81 | 0.91 | 0.79 | 1.38 | 0.95 |
| Eci2 | 1.25 | 1.64 | 1.13 | 0.99 | 1.04 | 1.01 | 1.09 | 0.97 | 0.99 | 1.06 | 1.27 | 1.17 |
| Ecscr | 2.32 | 1.74 | 1.10 | 1.00 | 0.52 | 0.37 | 1.00 | 1.59 | 1.00 | 0.91 | 1.77 | 1.11 |
| Eddm3b | 1.00 | 1.00 | 1.00 | 10.46 | 6.43 | 6.27 | 1.00 | 1.00 | 1.00 | 1.00 | 1.00 | 1.00 |
| Edf1 | 0.99 | 1.64 | 0.88 | 0.81 | 0.65 | 0.90 | 1.06 | 1.78 | 0.97 | 0.97 | 1.64 | 1.09 |
| Eef1a2 | 1.00 | 1.00 | 1.00 | 1.00 | 1.00 | 1.00 | 1.00 | 1.00 | 1.00 | 1.11 | 0.99 | 1.02 |
| Eef1d | 1.23 | 1.47 | 1.06 | 0.92 | 0.55 | 0.82 | 0.98 | 2.22 | 0.97 | 0.85 | 1.87 | 1.01 |
| Eef1g | 1.03 | 1.25 | 0.99 | 0.93 | 0.66 | 0.84 | 1.01 | 2.31 | 1.13 | 1.05 | 1.52 | 1.12 |
| Efcab2 | 1.00 | 0.94 | 1.36 | 0.95 | 1.00 | 1.07 | 1.00 | 1.00 | 1.00 | 0.52 | 0.88 | 0.68 |
| Efcab4a | 2.21 | 1.60 | 1.38 | 0.75 | 0.51 | 1.18 | 0.92 | 1.41 | 0.90 | 0.88 | 1.23 | 1.21 |
| Efemp1 | 2.45 | 1.93 | 1.28 | 0.69 | 0.41 | 0.84 | 1.51 | 4.42 | 0.80 | 1.02 | 1.09 | 0.94 |
| Efemp2 | 2.18 | 2.61 | 1.56 | 0.85 | 0.37 | 0.69 | 1.00 | 4.19 | 1.00 | 0.75 | 1.27 | 0.88 |
| Egfbp2 | 2.86 | 1.00 | 2.10 | 1.00 | 1.00 | 1.00 | 1.00 | 1.00 | 1.00 | 1.00 | 1.00 | 1.00 |
| Egfl7 | 1.81 | 1.66 | 1.05 | 0.95 | 0.50 | 0.86 | 1.01 | 1.91 | 0.94 | 0.94 | 1.22 | 0.98 |
| Egln2 | 1.25 | 1.42 | 1.21 | 1.16 | 0.87 | 1.15 | 1.20 | 2.28 | 1.05 | 1.03 | 1.32 | 1.04 |
| Egln3 | 1.22 | 1.11 | 1.13 | 0.72 | 0.84 | 0.98 | 1.17 | 3.40 | 1.55 | 0.75 | 0.71 | 0.83 |
| Egr1 | 1.01 | 0.94 | 1.30 | 1.34 | 1.00 | 0.75 | 5.26 | 0.79 | 1.22 | 1.46 | 3.24 | 1.22 |
| Ehhadh | 1.05 | 0.90 | 0.91 | 1.22 | 1.97 | 1.19 | 1.12 | 0.43 | 1.02 | 1.06 | 0.76 | 1.06 |
| Eif2b2 | 1.10 | 1.63 | 1.07 | 1.15 | 0.59 | 0.99 | 1.28 | 3.55 | 1.14 | 1.08 | 1.62 | 0.99 |
| Eif2b4 | 1.15 | 1.20 | 0.87 | 1.21 | 0.68 | 0.98 | 1.70 | 3.32 | 1.35 | 0.95 | 1.63 | 1.03 |
| Eif3b | 0.90 | 0.93 | 0.90 | 1.22 | 0.72 | 1.15 | 1.24 | 2.50 | 1.12 | 0.97 | 1.39 | 1.06 |
| Eif3d | 1.21 | 1.27 | 0.99 | 1.13 | 0.72 | 0.91 | 1.31 | 2.27 | 1.17 | 1.09 | 1.63 | 1.05 |
| Eif3f | 1.17 | 1.64 | 1.18 | 0.95 | 0.54 | 1.17 | 1.16 | 2.94 | 1.06 | 1.01 | 1.35 | 1.04 |
| Eif3h | 1.16 | 1.39 | 1.03 | 1.00 | 0.91 | 1.03 | 0.90 | 1.10 | 1.01 | 0.99 | 1.46 | 1.06 |
| Eif3j1 | 1.00 | 1.00 | 1.00 | 1.00 | 1.00 | 1.00 | 1.00 | 1.00 | 1.00 | 1.00 | 1.00 | 1.00 |
| Eif3j2 | 0.86 | 0.87 | 0.90 | 1.20 | 1.17 | 0.92 | 1.15 | 0.89 | 1.21 | 1.07 | 1.11 | 1.09 |
| Eif3k | 1.35 | 1.50 | 1.11 | 1.00 | 0.57 | 0.96 | 1.63 | 1.56 | 1.03 | 0.90 | 1.43 | 1.05 |
| Eif3m | 1.45 | 1.47 | 1.03 | 1.15 | 0.89 | 1.02 | 1.14 | 1.61 | 0.97 | 0.97 | 1.37 | 1.05 |
| Eif4e2 | 0.93 | 0.93 | 0.99 | 0.88 | 0.68 | 0.94 | 0.89 | 2.01 | 0.96 | 1.03 | 1.34 | 1.06 |
| Eif4ebp1 | 1.33 | 1.81 | 1.12 | 1.77 | 1.44 | 1.55 | 1.19 | 1.74 | 0.98 | 1.49 | 2.22 | 1.62 |
| Eif4ebp3 | 1.27 | 1.38 | 0.92 | 7.64 | 9.87 | 3.19 | 7.02 | 9.69 | 4.06 | 1.15 | 1.83 | 1.23 |
| Eif6 | 1.03 | 1.27 | 0.94 | 0.99 | 0.57 | 0.95 | 1.26 | 2.53 | 1.18 | 1.14 | 1.77 | 1.22 |
| Elane | 0.26 | 0.74 | 1.00 | 1.00 | 1.00 | 1.00 | 1.00 | 1.00 | 1.00 | 1.00 | 1.00 | 1.00 |
| Elavl3 | 1.00 | 1.00 | 1.00 | 1.00 | 1.00 | 1.00 | 1.00 | 1.00 | 1.00 | 0.92 | 1.00 | 1.15 |
| Elk4 | 0.58 | 0.67 | 0.95 | 1.47 | 1.00 | 1.57 | 1.37 | 1.00 | 1.29 | 1.05 | 0.51 | 0.85 |
| Elmod1 | 1.00 | 1.00 | 1.00 | 1.00 | 1.00 | 1.00 | 1.00 | 1.00 | 1.00 | 1.78 | 1.99 | 1.87 |
| Elovl3 | 0.14 | 0.41 | 0.23 | 1.00 | 1.00 | 1.31 | 4.66 | 6.75 | 4.31 | 1.00 | 1.00 | 1.00 |
| Elp6 | 1.38 | 1.70 | 0.97 | 1.26 | 0.77 | 0.95 | 1.56 | 0.88 | 1.11 | 1.55 | 1.62 | 1.40 |
| Emc9 | 1.43 | 1.09 | 1.38 | 0.80 | 0.59 | 0.85 | 1.07 | 0.88 | 0.89 | 0.88 | 1.25 | 1.36 |
| Emd | 1.02 | 1.11 | 0.92 | 1.13 | 1.17 | 0.90 | 1.43 | 2.60 | 1.02 | 1.05 | 1.37 | 1.06 |
| Emp3 | 1.08 | 1.46 | 1.04 | 0.68 | 0.49 | 0.75 | 1.04 | 1.27 | 1.02 | 0.84 | 1.22 | 0.82 |
| Endog | 1.48 | 1.63 | 1.12 | 1.30 | 1.01 | 1.34 | 1.21 | 2.11 | 0.99 | 0.89 | 1.42 | 0.94 |
| Engase | 0.85 | 0.90 | 0.79 | 1.02 | 0.48 | 0.87 | 0.92 | 2.00 | 1.03 | 0.91 | 1.27 | 0.99 |
| Enho | 6.56 | 7.42 | 4.70 | 0.89 | 0.81 | 0.63 | 0.78 | 0.79 | 1.27 | 0.95 | 1.26 | 0.81 |
| Eno2 | 0.77 | 0.73 | 0.70 | 1.00 | 0.69 | 1.00 | 1.00 | 1.00 | 1.00 | 0.80 | 1.04 | 1.06 |
| Eno3 | 1.27 | 1.59 | 1.21 | 0.57 | 0.46 | 0.92 | 1.22 | 1.49 | 0.83 | 0.54 | 0.58 | 0.49 |
| Enpp1 | 2.55 | 2.66 | 2.31 | 1.39 | 1.04 | 1.32 | 0.70 | 0.97 | 1.10 | 1.56 | 2.36 | 1.45 |
| Epdr1 | 1.03 | 0.45 | 0.70 | 0.46 | 1.25 | 0.68 | 1.00 | 1.00 | 1.00 | 1.81 | 1.42 | 1.96 |
| Ephx2 | 0.95 | 1.15 | 0.55 | 0.89 | 0.68 | 0.79 | 1.11 | 1.08 | 1.07 | 1.00 | 1.57 | 1.04 |
| Epn1 | 1.04 | 1.21 | 1.04 | 0.88 | 0.66 | 0.98 | 0.91 | 1.59 | 0.81 | 0.95 | 1.21 | 1.02 |
| Eri3 | 1.14 | 1.58 | 1.09 | 0.90 | 0.63 | 0.77 | 1.08 | 1.29 | 0.96 | 0.84 | 1.34 | 0.98 |
| Ern1 | 0.59 | 0.26 | 0.97 | 1.42 | 1.00 | 1.42 | 0.89 | 1.00 | 0.95 | 1.02 | 0.32 | 0.94 |
| Ero1lb | 1.96 | 1.47 | 1.95 | 3.62 | 2.67 | 3.88 | 4.00 | 6.27 | 4.05 | 4.77 | 5.15 | 4.81 |
| Erp27 | 2.06 | 1.67 | 1.07 | 1.00 | 1.00 | 1.00 | 3.39 | 19.89 | 2.32 | 0.67 | 1.03 | 2.19 |
| Errfi1 | 6.15 | 4.41 | 2.59 | 1.58 | 2.46 | 1.52 | 0.95 | 0.73 | 1.07 | 1.33 | 1.42 | 1.06 |
| Esd | 1.44 | 1.40 | 1.02 | 0.87 | 0.72 | 0.91 | 0.70 | 1.11 | 0.69 | 1.05 | 1.70 | 1.11 |
| Esm1 | 1.00 | 1.00 | 1.00 | 1.02 | 0.90 | 0.92 | 1.00 | 1.00 | 1.00 | 0.98 | 0.68 | 0.57 |
| Espn | 1.26 | 1.65 | 0.90 | 1.53 | 0.73 | 1.47 | 1.00 | 1.00 | 1.00 | 1.07 | 0.96 | 1.01 |
| Etfb | 1.22 | 1.34 | 0.82 | 0.83 | 0.44 | 0.80 | 0.98 | 2.62 | 0.91 | 0.99 | 1.55 | 1.04 |
| Etnppl | 1.00 | 1.00 | 1.00 | 2.09 | 1.95 | 1.50 | 3.02 | 20.69 | 0.80 | 1.00 | 0.90 | 0.91 |

Fig. 35- 163

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ear6 | 1.00 | 1.00 | 1.00 | 1.00 | 1.00 | 1.00 | 1.00 | 1.00 | 1.00 | 5.21 | 4.44 | 1.20 |
| Ebi3 | 1.00 | 1.00 | 1.00 | 1.14 | 1.31 | 0.86 | 1.00 | 3.11 | 1.00 | 0.76 | 0.85 | 0.95 |
| Ebp | 1.00 | 0.94 | 0.93 | 1.08 | 3.37 | 0.97 | 0.76 | 1.80 | 0.93 | 1.03 | 1.19 | 1.00 |
| Ebpl | 0.79 | 0.64 | 0.75 | 0.39 | 2.00 | 0.71 | 0.71 | 1.98 | 0.71 | 1.05 | 1.15 | 0.98 |
| Echdc2 | 1.31 | 1.32 | 1.15 | 1.54 | 13.39 | 1.47 | 0.53 | 1.07 | 0.69 | 0.83 | 1.47 | 0.91 |
| Eci2 | 1.03 | 1.26 | 1.61 | 0.91 | 2.73 | 1.07 | 0.67 | 0.84 | 0.72 | 1.26 | 1.64 | 1.26 |
| Ecscr | 1.53 | 0.77 | 1.20 | 1.42 | 3.89 | 1.67 | 1.00 | 1.47 | 1.00 | 0.77 | 0.86 | 0.68 |
| Eddm3b | 1.00 | 1.00 | 1.00 | 3.80 | 1.00 | 0.99 | 1.00 | 1.00 | 1.00 | 1.00 | 1.00 | 1.00 |
| Edf1 | 1.03 | 0.95 | 0.88 | 0.93 | 2.92 | 1.16 | 0.98 | 2.40 | 1.15 | 0.93 | 1.37 | 0.85 |
| Eef1a2 | 2.27 | 1.28 | 2.61 | 1.00 | 1.00 | 1.00 | 1.00 | 1.00 | 1.00 | 1.00 | 37.16 | 1.00 |
| Eef1d | 0.96 | 0.97 | 0.98 | 1.24 | 2.24 | 1.21 | 0.94 | 2.97 | 1.08 | 1.02 | 1.30 | 0.91 |
| Eef1g | 0.92 | 0.96 | 1.06 | 0.97 | 2.88 | 1.12 | 0.91 | 2.53 | 1.09 | 1.25 | 1.36 | 1.03 |
| Efcab2 | 0.84 | 0.90 | 1.00 | 0.83 | 1.00 | 0.72 | 1.21 | 6.09 | 1.06 | 1.43 | 1.50 | 1.58 |
| Efcab4a | 0.89 | 0.86 | 0.96 | 0.97 | 3.83 | 1.17 | 1.00 | 1.32 | 1.10 | 0.58 | 1.13 | 0.85 |
| Efemp1 | 1.04 | 0.90 | 1.47 | 0.84 | 1.90 | 1.04 | 0.59 | 1.80 | 0.83 | 0.63 | 0.98 | 1.55 |
| Efemp2 | 0.76 | 0.67 | 0.95 | 0.88 | 1.65 | 0.89 | 0.89 | 3.27 | 0.69 | 0.78 | 0.93 | 0.83 |
| Egfbp2 | 1.00 | 1.00 | 1.00 | 1.00 | 1.00 | 1.00 | 1.89 | 4.31 | 1.81 | 1.00 | 1.00 | 1.00 |
| Egfl7 | 0.88 | 1.25 | 1.23 | 1.12 | 2.23 | 1.21 | 0.77 | 2.92 | 0.92 | 0.97 | 1.20 | 0.82 |
| Egln2 | 1.08 | 1.36 | 1.06 | 1.91 | 4.90 | 1.34 | 1.01 | 2.33 | 1.15 | 1.60 | 2.30 | 1.55 |
| Egln3 | 0.60 | 0.62 | 0.56 | 0.48 | 0.69 | 1.72 | 1.00 | 1.00 | 1.00 | 0.57 | 0.44 | 0.42 |
| Egr1 | 1.06 | 1.13 | 0.99 | 1.65 | 0.35 | 1.32 | 0.54 | 1.00 | 1.16 | 0.59 | 0.72 | 0.71 |
| Ehhadh | 0.82 | 0.83 | 0.83 | 17.66 | 3.23 | 6.90 | 0.72 | 1.00 | 0.79 | 1.17 | 0.81 | 1.19 |
| Eif2b2 | 1.05 | 1.11 | 1.06 | 1.02 | 1.40 | 1.14 | 0.90 | 4.31 | 1.03 | 1.11 | 1.26 | 1.07 |
| Eif2b4 | 0.96 | 1.04 | 0.95 | 1.01 | 2.28 | 0.94 | 0.95 | 3.22 | 1.05 | 1.15 | 1.22 | 1.00 |
| Eif3b | 0.97 | 0.94 | 0.82 | 1.32 | 2.74 | 1.26 | 1.07 | 2.70 | 1.05 | 1.05 | 1.08 | 1.00 |
| Eif3d | 0.82 | 0.98 | 0.87 | 1.13 | 2.81 | 1.30 | 0.99 | 2.17 | 0.97 | 1.02 | 1.22 | 0.92 |
| Eif3f | 1.01 | 1.27 | 1.14 | 0.99 | 1.98 | 1.17 | 0.92 | 3.99 | 1.07 | 1.08 | 1.29 | 0.98 |
| Eif3h | 1.05 | 1.09 | 1.13 | 1.05 | 5.48 | 1.09 | 1.00 | 1.44 | 1.11 | 1.21 | 1.26 | 1.06 |
| Eif3j1 | 1.00 | 1.00 | 0.12 | 1.00 | 1.00 | 1.00 | 1.00 | 1.00 | 1.00 | 1.00 | 1.00 | 1.00 |
| Eif3j2 | 1.14 | 0.86 | 9.59 | 1.60 | 2.96 | 1.40 | 0.88 | 2.00 | 1.02 | 1.02 | 1.08 | 0.91 |
| Eif3k | 1.06 | 1.19 | 1.10 | 1.00 | 1.68 | 1.14 | 0.91 | 1.63 | 0.88 | 1.17 | 1.08 | 0.93 |
| Eif3m | 1.01 | 1.30 | 1.17 | 0.64 | 7.46 | 1.19 | 0.76 | 1.91 | 0.93 | 1.51 | 0.99 | 1.26 |
| Eif4e2 | 0.86 | 0.85 | 0.97 | 0.89 | 2.96 | 1.00 | 1.02 | 1.86 | 0.94 | 0.99 | 0.94 | 0.96 |
| Eif4ebp1 | 0.96 | 1.23 | 1.18 | 0.91 | 3.06 | 0.99 | 1.10 | 2.26 | 1.22 | 1.20 | 1.58 | 1.24 |
| Eif4ebp3 | 1.42 | 1.18 | 1.39 | 4.67 | 14.14 | 3.53 | 0.89 | 1.77 | 0.96 | 1.14 | 1.25 | 0.95 |
| Eif6 | 0.93 | 1.01 | 0.81 | 1.16 | 2.88 | 1.06 | 1.02 | 3.19 | 1.00 | 1.06 | 1.22 | 1.01 |
| Elane | 1.00 | 1.00 | 1.00 | 0.72 | 0.47 | 3.61 | 1.00 | 1.00 | 1.00 | 12.25 | 12.57 | 7.53 |
| Elavl3 | 1.00 | 1.00 | 1.00 | 1.00 | 1.00 | 1.00 | 1.04 | 1.00 | 0.88 | 1.00 | 6.76 | 1.00 |
| Elk4 | 0.98 | 1.20 | 0.48 | 4.01 | 0.28 | 0.72 | 1.00 | 1.00 | 1.00 | 0.98 | 0.51 | 1.57 |
| Elmod1 | 1.08 | 1.17 | 1.22 | 1.52 | 1.00 | 3.27 | 1.00 | 1.00 | 1.00 | 1.00 | 7.63 | 1.00 |
| Elovl3 | 1.00 | 1.00 | 1.00 | 5.39 | 2.23 | 3.20 | 1.25 | 1.00 | 1.13 | 1.00 | 1.00 | 1.00 |
| Elp6 | 0.48 | 0.49 | 0.57 | 0.86 | 2.26 | 0.60 | 0.56 | 1.09 | 0.75 | 1.52 | 1.47 | 0.84 |
| Emc9 | 1.13 | 1.69 | 2.14 | 0.30 | 0.91 | 0.42 | 0.86 | 1.67 | 0.59 | 0.98 | 1.09 | 0.99 |
| Emd | 1.09 | 1.26 | 1.06 | 1.43 | 7.33 | 1.29 | 0.83 | 1.14 | 0.89 | 1.00 | 1.07 | 0.88 |
| Emp3 | 0.97 | 1.09 | 1.27 | 0.96 | 1.79 | 0.84 | 1.16 | 1.78 | 1.12 | 0.77 | 0.74 | 0.80 |
| Endog | 1.01 | 1.28 | 1.16 | 1.34 | 5.27 | 1.58 | 0.58 | 0.59 | 1.51 | 1.27 | 1.59 | 1.07 |
| Engase | 0.91 | 0.90 | 0.93 | 0.71 | 1.52 | 0.87 | 1.00 | 3.91 | 1.45 | 1.02 | 0.98 | 0.92 |
| Enho | 1.03 | 1.25 | 0.88 | 1.10 | 1.60 | 1.04 | 0.62 | 1.49 | 1.34 | 1.09 | 2.82 | 1.10 |
| Eno2 | 1.05 | 1.03 | 1.28 | 0.85 | 1.10 | 0.92 | 1.00 | 1.00 | 1.00 | 0.51 | 8.10 | 0.72 |
| Eno3 | 2.02 | 1.35 | 1.81 | 0.81 | 1.08 | 1.11 | 0.90 | 2.43 | 1.05 | 0.99 | 0.93 | 1.00 |
| Enpp1 | 1.17 | 0.75 | 1.04 | 0.88 | 1.00 | 0.70 | 1.00 | 1.00 | 1.00 | 0.97 | 1.45 | 1.02 |
| Epdr1 | 1.78 | 1.89 | 1.50 | 1.23 | 1.00 | 0.83 | 1.00 | 1.00 | 1.00 | 1.74 | 3.91 | 1.00 |
| Ephx2 | 1.43 | 1.60 | 1.40 | 0.99 | 3.07 | 1.13 | 1.00 | 1.19 | 1.00 | 0.61 | 0.87 | 0.73 |
| Epn1 | 0.98 | 1.17 | 0.97 | 0.94 | 2.08 | 1.03 | 0.79 | 1.93 | 0.84 | 0.88 | 1.12 | 0.93 |
| Eri3 | 1.17 | 1.08 | 1.34 | 0.81 | 1.55 | 0.87 | 0.88 | 1.71 | 1.06 | 0.95 | 1.43 | 0.96 |
| Ern1 | 1.08 | 1.13 | 0.64 | 1.87 | 1.00 | 0.65 | 1.11 | 1.00 | 1.22 | 0.78 | 0.26 | 1.36 |
| Ero1lb | 6.91 | 4.64 | 5.56 | 2.89 | 1.00 | 2.24 | 2.98 | 6.76 | 2.90 | 4.62 | 3.52 | 3.85 |
| Erp27 | 1.00 | 1.00 | 3.04 | 1.00 | 0.78 | 1.00 | 1.00 | 1.00 | 1.00 | 0.90 | 2.69 | 0.92 |
| Errfi1 | 1.94 | 2.38 | 1.17 | 8.39 | 13.91 | 3.51 | 1.16 | 1.08 | 1.15 | 2.09 | 2.60 | 2.45 |
| Esd | 0.74 | 0.72 | 0.72 | 2.12 | 3.78 | 1.30 | 0.82 | 1.91 | 0.72 | 1.10 | 1.29 | 0.99 |
| Esm1 | 1.00 | 0.87 | 0.60 | 1.02 | 1.00 | 1.07 | 1.00 | 1.00 | 1.00 | 0.69 | 0.50 | 0.62 |
| Espn | 0.59 | 0.66 | 0.56 | 1.33 | 3.04 | 1.79 | 0.91 | 2.90 | 1.06 | 0.59 | 0.66 | 1.06 |
| Etfb | 0.86 | 0.88 | 0.83 | 0.71 | 1.47 | 1.08 | 1.17 | 4.01 | 1.03 | 1.02 | 1.04 | 0.74 |
| Etnppl | 0.92 | 3.06 | 1.01 | 1.00 | 1.00 | 1.00 | 1.00 | 1.00 | 1.00 | 1.00 | 1.00 | 1.00 |

Fig. 35- 164

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ear6 | 1.00 | 1.00 | 1.00 | 1.00 | 1.00 | 1.00 | 1.00 | 1.00 | 1.00 | 1.02 | 1.02 | 1.40 |
| Ebi3 | 1.00 | 1.00 | 1.00 | 1.00 | 0.40 | 1.00 | 1.22 | 12.95 | 0.64 | 2.38 | 1.25 | 1.16 |
| Ebp | 1.63 | 1.25 | 0.83 | 1.06 | 0.73 | 0.91 | 1.21 | 7.51 | 0.84 | 2.86 | 1.24 | 1.26 |
| Ebpl | 1.00 | 1.00 | 1.00 | 1.09 | 0.99 | 1.03 | 0.82 | 7.45 | 0.79 | 2.97 | 1.32 | 1.14 |
| Echdc2 | 0.70 | 1.04 | 1.20 | 1.30 | 6.20 | 1.37 | 1.13 | 3.25 | 1.02 | 1.00 | 1.00 | 1.00 |
| Eci2 | 0.83 | 0.61 | 0.81 | 1.09 | 0.95 | 1.16 | 1.99 | 5.09 | 1.73 | 1.80 | 1.14 | 1.00 |
| Ecscr | 1.00 | 1.00 | 1.00 | 1.00 | 1.22 | 1.00 | 0.95 | 12.68 | 1.48 | 1.00 | 1.00 | 1.00 |
| Eddm3b | 1.00 | 1.00 | 1.00 | 1.00 | 1.00 | 1.00 | 1.00 | 1.00 | 1.00 | 1.00 | 1.00 | 1.00 |
| Edf1 | 1.34 | 1.02 | 1.00 | 1.14 | 0.94 | 1.04 | 1.07 | 9.85 | 0.79 | 3.81 | 1.01 | 1.32 |
| Eef1a2 | 1.00 | 1.00 | 1.00 | 1.07 | 0.78 | 0.99 | 1.58 | 6.22 | 2.27 | 1.00 | 1.00 | 1.00 |
| Eef1d | 0.68 | 0.87 | 1.06 | 1.05 | 1.17 | 1.01 | 1.21 | 14.74 | 0.85 | 2.26 | 0.86 | 0.91 |
| Eef1g | 0.96 | 1.02 | 0.93 | 1.04 | 1.04 | 1.02 | 1.00 | 6.59 | 0.79 | 2.03 | 0.94 | 1.01 |
| Efcab2 | 1.00 | 1.00 | 1.00 | 1.00 | 0.34 | 0.97 | 1.01 | 1.00 | 1.93 | 1.00 | 1.00 | 1.00 |
| Efcab4a | 0.67 | 0.49 | 0.83 | 1.31 | 3.06 | 0.93 | 1.17 | 3.46 | 1.05 | 2.34 | 1.34 | 1.69 |
| Efemp1 | 0.54 | 0.90 | 1.45 | 0.66 | 0.60 | 0.77 | 1.12 | 6.02 | 1.24 | 1.00 | 1.00 | 1.00 |
| Efemp2 | 1.00 | 1.00 | 1.00 | 0.85 | 0.74 | 0.86 | 0.82 | 12.01 | 1.08 | 1.00 | 1.00 | 1.00 |
| Egfbp2 | 0.61 | 1.00 | 1.31 | 1.00 | 3.01 | 1.00 | 1.00 | 3.15 | 1.00 | 2.83 | 1.00 | 1.00 |
| Egfl7 | 0.77 | 0.83 | 0.75 | 1.12 | 0.86 | 1.24 | 1.17 | 6.98 | 1.08 | 2.38 | 0.56 | 0.88 |
| Egln2 | 1.29 | 1.27 | 1.25 | 1.11 | 1.28 | 1.06 | 1.85 | 6.21 | 1.35 | 2.82 | 1.55 | 1.08 |
| Egln3 | 1.00 | 1.00 | 1.00 | 0.99 | 1.16 | 1.21 | 0.97 | 1.14 | 0.69 | 1.13 | 1.11 | 1.30 |
| Egr1 | 1.00 | 3.19 | 1.00 | 1.41 | 2.35 | 1.02 | 0.47 | 0.14 | 0.65 | 0.67 | 0.60 | 0.95 |
| Ehhadh | 0.64 | 0.42 | 0.61 | 0.99 | 1.00 | 1.22 | 0.87 | 0.20 | 1.24 | 0.64 | 0.89 | 0.84 |
| Eif2b2 | 1.24 | 1.33 | 0.82 | 1.03 | 0.91 | 1.14 | 1.27 | 10.94 | 0.88 | 3.60 | 1.26 | 1.20 |
| Eif2b4 | 0.78 | 0.88 | 1.13 | 1.12 | 0.94 | 1.01 | 1.24 | 12.09 | 0.94 | 2.68 | 0.90 | 0.96 |
| Eif3b | 0.93 | 1.04 | 1.06 | 1.01 | 1.11 | 1.04 | 1.04 | 7.57 | 0.87 | 2.12 | 0.81 | 0.82 |
| Eif3d | 0.92 | 0.94 | 1.12 | 1.18 | 0.83 | 1.04 | 1.10 | 7.00 | 0.90 | 2.27 | 0.97 | 0.94 |
| Eif3f | 1.02 | 0.81 | 1.01 | 1.00 | 0.83 | 1.00 | 1.15 | 13.30 | 0.93 | 3.24 | 1.22 | 1.14 |
| Eif3h | 0.94 | 0.89 | 1.06 | 1.00 | 1.15 | 0.97 | 1.04 | 4.96 | 0.95 | 2.15 | 1.11 | 1.10 |
| Eif3j1 | 1.00 | 1.00 | 1.00 | 1.00 | 1.00 | 1.00 | 1.00 | 1.00 | 1.00 | 1.00 | 1.00 | 1.00 |
| Eif3j2 | 1.23 | 1.31 | 1.22 | 1.05 | 0.47 | 1.19 | 0.82 | 0.82 | 1.07 | 0.58 | 0.88 | 0.98 |
| Eif3k | 0.78 | 0.78 | 0.95 | 1.14 | 1.03 | 1.05 | 1.18 | 5.29 | 0.92 | 1.55 | 1.16 | 1.09 |
| Eif3m | 1.23 | 1.39 | 1.34 | 1.34 | 0.94 | 1.06 | 1.12 | 5.00 | 0.89 | 1.61 | 1.01 | 1.01 |
| Eif4e2 | 1.41 | 1.08 | 0.95 | 1.05 | 0.67 | 0.97 | 0.96 | 5.65 | 0.98 | 2.36 | 1.07 | 0.98 |
| Eif4ebp1 | 1.11 | 0.98 | 0.82 | 0.61 | 0.54 | 0.83 | 1.38 | 4.24 | 1.24 | 1.95 | 1.38 | 1.19 |
| Eif4ebp3 | 0.66 | 0.67 | 1.52 | 0.83 | 0.82 | 1.24 | 1.09 | 5.99 | 0.94 | 1.94 | 1.15 | 0.99 |
| Eif6 | 1.08 | 1.13 | 0.98 | 1.06 | 1.06 | 1.11 | 1.22 | 9.02 | 0.85 | 2.26 | 1.07 | 0.94 |
| Elane | 1.00 | 1.00 | 1.00 | 1.00 | 0.93 | 1.00 | 1.00 | 1.00 | 1.00 | 2.84 | 1.26 | 1.54 |
| Elavl3 | 1.00 | 1.00 | 1.00 | 0.98 | 1.10 | 0.96 | 1.00 | 1.00 | 1.00 | 1.00 | 1.00 | 1.00 |
| Elk4 | 1.00 | 1.00 | 1.00 | 0.75 | 1.00 | 0.90 | 0.96 | 0.51 | 1.28 | 1.00 | 0.76 | 0.73 |
| Elmod1 | 1.00 | 1.00 | 1.00 | 1.07 | 4.01 | 1.08 | 0.89 | 0.10 | 0.88 | 1.00 | 1.00 | 1.00 |
| Elovl3 | 1.00 | 1.00 | 1.00 | 1.00 | 1.00 | 1.00 | 1.88 | 2.71 | 1.38 | 1.00 | 1.00 | 1.00 |
| Elp6 | 1.00 | 1.00 | 1.00 | 1.18 | 1.64 | 1.04 | 0.97 | 2.78 | 0.82 | 1.92 | 1.15 | 1.05 |
| Emc9 | 0.65 | 0.88 | 0.76 | 1.19 | 1.12 | 1.02 | 1.45 | 6.69 | 1.17 | 2.02 | 0.87 | 1.24 |
| Emd | 1.20 | 1.27 | 0.84 | 1.28 | 1.17 | 1.04 | 1.16 | 1.52 | 0.84 | 1.36 | 1.08 | 1.02 |
| Emp3 | 1.00 | 1.27 | 0.69 | 1.21 | 0.69 | 1.61 | 1.38 | 5.89 | 1.08 | 2.79 | 1.25 | 1.27 |
| Endog | 0.77 | 0.55 | 0.80 | 1.38 | 1.06 | 1.07 | 1.48 | 3.65 | 1.04 | 1.79 | 1.60 | 1.04 |
| Engase | 0.99 | 0.85 | 0.78 | 1.05 | 0.72 | 1.03 | 0.91 | 5.14 | 0.93 | 1.83 | 0.97 | 0.90 |
| Enho | 0.44 | 1.19 | 0.22 | 1.09 | 0.99 | 0.97 | 1.52 | 3.93 | 1.59 | 1.88 | 1.46 | 1.11 |
| Eno2 | 1.00 | 1.00 | 1.00 | 1.03 | 0.94 | 0.99 | 0.76 | 2.58 | 0.93 | 1.00 | 1.00 | 1.00 |
| Eno3 | 0.70 | 1.13 | 0.82 | 0.81 | 0.72 | 1.04 | 1.71 | 7.68 | 1.57 | 1.16 | 0.87 | 0.91 |
| Enpp1 | 1.87 | 1.32 | 1.14 | 1.00 | 1.09 | 1.00 | 2.23 | 8.73 | 2.50 | 2.62 | 1.29 | 1.06 |
| Epdr1 | 1.00 | 1.00 | 1.00 | 1.12 | 1.22 | 1.06 | 1.93 | 0.30 | 2.62 | 2.19 | 12.60 | 12.81 |
| Ephx2 | 0.94 | 1.00 | 0.95 | 1.16 | 0.80 | 0.92 | 2.22 | 11.11 | 1.96 | 1.00 | 1.00 | 1.00 |
| Epn1 | 0.96 | 0.91 | 0.98 | 1.03 | 1.00 | 0.96 | 1.15 | 5.15 | 1.00 | 2.06 | 1.10 | 1.01 |
| Eri3 | 0.85 | 1.13 | 0.90 | 1.07 | 0.96 | 1.03 | 1.41 | 5.39 | 1.06 | 1.75 | 1.03 | 1.23 |
| Ern1 | 1.16 | 1.04 | 1.39 | 0.68 | 1.00 | 0.86 | 0.78 | 0.30 | 1.32 | 1.00 | 0.52 | 0.49 |
| Ero1b | 4.51 | 4.42 | 4.18 | 4.03 | 4.63 | 3.69 | 3.44 | 1.82 | 2.60 | 7.56 | 4.15 | 4.49 |
| Erp27 | 1.06 | 1.19 | 1.17 | 1.00 | 1.00 | 1.00 | 1.00 | 4.26 | 1.00 | 4.27 | 1.57 | 1.23 |
| Errfi1 | 3.08 | 5.55 | 2.14 | 1.40 | 0.72 | 1.22 | 2.39 | 1.26 | 2.52 | 0.79 | 1.79 | 1.02 |
| Esd | 0.65 | 0.74 | 0.85 | 1.07 | 0.71 | 1.01 | 1.10 | 8.14 | 1.07 | 1.74 | 1.08 | 1.07 |
| Esm1 | 1.00 | 1.00 | 1.00 | 1.00 | 1.00 | 1.00 | 1.00 | 1.00 | 1.00 | 0.85 | 0.36 | 0.93 |
| Espn | 1.17 | 0.69 | 0.40 | 0.88 | 9.62 | 0.88 | 2.78 | 0.49 | 1.44 | 1.00 | 1.00 | 1.00 |
| Etfb | 0.85 | 0.71 | 0.85 | 1.10 | 0.84 | 0.94 | 1.37 | 28.38 | 1.03 | 3.55 | 1.02 | 1.15 |
| Etnppl | 1.00 | 1.00 | 1.00 | 1.51 | 1.24 | 1.37 | 1.00 | 1.00 | 1.00 | 1.00 | 1.00 | 1.00 |

Fig. 35- 165

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Etohd2 | 1.23 | 0.93 | 0.73 | 1.65 | 6.01 | 1.73 | 1.14 | 0.64 | 0.76 | 1.75 | 2.00 | 0.86 |
| Etohi1 | 1.71 | 1.10 | 2.69 | 2.96 | 3.11 | 2.69 | 0.36 | 0.62 | 0.66 | 15.50 | 0.74 | 0.78 |
| Eva1a | 1.46 | 1.00 | 1.69 | 7.00 | 7.75 | 5.67 | 1.51 | 1.49 | 1.17 | 0.84 | 0.76 | 0.62 |
| Eva1c | 1.12 | 1.21 | 1.00 | 1.80 | 21.13 | 2.44 | 1.17 | 1.20 | 0.97 | 2.92 | 3.87 | 1.13 |
| Exoc7 | 0.60 | 0.50 | 0.82 | 0.51 | 1.68 | 0.84 | 1.10 | 0.93 | 0.97 | 3.37 | 1.96 | 0.82 |
| Extl1 | 0.87 | 0.76 | 0.79 | 4.49 | 11.99 | 20.81 | 0.95 | 1.03 | 0.92 | 1.53 | 1.23 | 1.29 |
| Ezh2 | 1.00 | 1.11 | 1.00 | 2.24 | 5.49 | 1.08 | 0.75 | 1.40 | 1.09 | 1.49 | 1.49 | 0.70 |
| F13a1 | 1.98 | 1.60 | 2.23 | 2.21 | 1.28 | 1.71 | 1.28 | 1.37 | 2.17 | 1.86 | 1.21 | 1.77 |
| F3 | 1.14 | 3.16 | 0.98 | 5.22 | 1.43 | 1.61 | 1.16 | 1.13 | 1.00 | 0.36 | 0.80 | 2.37 |
| Fabp3 | 0.46 | 0.29 | 0.63 | 0.11 | 1.57 | 0.37 | 0.63 | 0.59 | 0.64 | 1.35 | 1.68 | 0.61 |
| Fabp6 | 1.00 | 1.00 | 1.00 | 1.00 | 1.00 | 1.00 | 1.00 | 1.00 | 1.00 | 1.00 | 1.00 | 1.00 |
| Fabp9 | 1.00 | 1.00 | 1.00 | 1.00 | 1.00 | 1.00 | 1.00 | 1.00 | 1.00 | 1.00 | 1.00 | 1.00 |
| Fads2 | 1.00 | 1.00 | 1.00 | 0.75 | 0.48 | 0.84 | 1.29 | 1.50 | 1.03 | 5.07 | 0.55 | 1.11 |
| Fads6 | 0.76 | 1.00 | 1.03 | 1.00 | 1.00 | 1.00 | 1.00 | 1.00 | 1.06 | 1.00 | 1.00 | 1.00 |
| Faf1 | 1.35 | 0.78 | 1.25 | 0.84 | 6.03 | 1.21 | 1.23 | 1.18 | 1.19 | 2.87 | 2.83 | 1.10 |
| Fah | 2.07 | 0.87 | 1.61 | 0.43 | 10.63 | 1.42 | 1.89 | 1.71 | 1.39 | 5.40 | 7.08 | 1.51 |
| Fahd2a | 0.95 | 0.66 | 0.73 | 0.41 | 2.66 | 0.72 | 1.03 | 0.96 | 0.92 | 2.08 | 1.91 | 1.21 |
| Faim2 | 1.00 | 1.00 | 1.00 | 1.00 | 0.13 | 1.00 | 1.00 | 1.00 | 1.00 | 1.34 | 1.31 | 0.88 |
| Faim3 | 1.00 | 1.00 | 1.00 | 1.00 | 1.00 | 1.00 | 1.00 | 1.00 | 1.00 | 0.58 | 0.46 | 0.47 |
| Fam107a | 2.16 | 3.07 | 2.69 | 4.87 | 1.96 | 5.19 | 1.95 | 2.65 | 2.36 | 2.53 | 4.04 | 3.50 |
| Fam131b | 0.75 | 0.55 | 0.65 | 1.00 | 0.29 | 1.00 | 1.00 | 1.00 | 1.00 | 1.00 | 1.00 | 1.00 |
| Fam132a | 1.07 | 0.51 | 0.68 | 0.75 | 3.16 | 0.86 | 1.34 | 0.97 | 0.89 | 2.02 | 1.72 | 0.98 |
| Fam134b | 2.78 | 3.11 | 3.12 | 5.85 | 3.35 | 2.79 | 1.69 | 2.11 | 1.35 | 1.40 | 1.89 | 1.56 |
| Fam151a | 1.00 | 1.25 | 1.00 | 1.00 | 16.09 | 1.00 | 1.00 | 1.00 | 1.00 | 1.00 | 1.05 | 1.00 |
| Fam163b | 1.00 | 1.00 | 1.00 | 1.00 | 0.21 | 1.71 | 1.00 | 1.00 | 1.00 | 1.00 | 1.00 | 1.00 |
| Fam167b | 2.72 | 2.16 | 2.06 | 1.43 | 3.78 | 2.04 | 1.28 | 0.91 | 1.65 | 0.31 | 0.37 | 0.52 |
| Fam171b | 1.00 | 1.00 | 1.00 | 1.00 | 0.29 | 1.00 | 1.00 | 1.00 | 1.00 | 1.00 | 1.00 | 1.00 |
| Fam173a | 1.32 | 0.55 | 0.73 | 0.30 | 4.45 | 0.92 | 0.85 | 0.69 | 0.92 | 2.21 | 3.25 | 0.90 |
| Fam195a | 0.79 | 0.43 | 0.85 | 0.22 | 7.64 | 0.74 | 0.98 | 0.87 | 0.72 | 2.40 | 6.73 | 1.11 |
| Fam195b | 2.62 | 1.40 | 2.05 | 2.25 | 25.69 | 2.67 | 1.63 | 1.42 | 1.64 | 5.44 | 7.30 | 2.09 |
| Fam19a5 | 1.12 | 0.70 | 0.57 | 0.93 | 0.67 | 1.22 | 0.77 | 0.66 | 0.63 | 1.00 | 1.00 | 0.96 |
| Fam21 | 1.27 | 1.52 | 1.02 | 0.99 | 1.27 | 0.90 | 0.88 | 0.87 | 0.79 | 1.33 | 1.00 | 0.89 |
| Fam212a | 0.64 | 0.21 | 0.63 | 0.28 | 1.46 | 0.48 | 0.61 | 0.40 | 0.51 | 0.39 | 0.82 | 0.69 |
| Fam213b | 1.64 | 0.68 | 0.87 | 0.38 | 7.69 | 0.98 | 1.03 | 0.66 | 0.67 | 2.17 | 2.25 | 0.93 |
| Fam214a | 2.44 | 5.69 | 2.48 | 3.30 | 0.57 | 1.98 | 3.31 | 3.64 | 1.80 | 0.32 | 0.48 | 1.18 |
| Fam219aos | 1.10 | 9.00 | 1.04 | 1.17 | 0.11 | 1.09 | 1.70 | 0.87 | 1.23 | 0.50 | 0.08 | 0.87 |
| Fam222a | 1.00 | 1.00 | 1.00 | 2.39 | 2.12 | 0.83 | 1.36 | 2.26 | 0.77 | 1.32 | 1.80 | 0.79 |
| Fam229a | 1.00 | 1.00 | 1.00 | 1.00 | 1.61 | 1.00 | 1.00 | 1.00 | 1.00 | 4.86 | 2.63 | 1.00 |
| Fam229b | 2.17 | 1.19 | 1.13 | 0.27 | 2.60 | 0.95 | 0.97 | 1.10 | 0.86 | 1.02 | 2.59 | 1.21 |
| Fam24a | 1.00 | 1.00 | 1.00 | 1.00 | 1.00 | 1.00 | 1.00 | 1.00 | 1.00 | 1.00 | 1.00 | 1.00 |
| Fam25c | 1.11 | 1.00 | 1.00 | 1.00 | 1.00 | 1.00 | 1.00 | 1.00 | 1.00 | 1.00 | 1.00 | 1.00 |
| Fam49a | 1.19 | 1.13 | 1.28 | 5.99 | 0.73 | 1.08 | 1.40 | 1.50 | 1.47 | 1.01 | 0.73 | 1.21 |
| Fam53b | 0.66 | 0.79 | 0.85 | 0.57 | 0.48 | 0.58 | 0.80 | 0.76 | 0.84 | 1.51 | 1.63 | 1.02 |
| Fam57b | 0.82 | 0.91 | 0.69 | 0.82 | 1.42 | 1.14 | 1.49 | 1.17 | 1.13 | 0.54 | 0.37 | 0.64 |
| Fam69b | 0.66 | 0.46 | 0.57 | 0.15 | 0.35 | 0.73 | 0.51 | 0.43 | 0.59 | 0.41 | 1.17 | 1.22 |
| Fam83a | 1.00 | 1.00 | 1.00 | 1.00 | 1.00 | 1.56 | 1.00 | 1.00 | 1.00 | 1.00 | 1.00 | 1.00 |
| Fam92b | 1.00 | 1.00 | 1.00 | 1.00 | 1.00 | 1.00 | 1.00 | 1.00 | 1.00 | 5.76 | 4.91 | 1.54 |
| Fam96b | 1.71 | 0.87 | 0.99 | 0.22 | 4.51 | 0.83 | 1.10 | 0.80 | 0.83 | 1.41 | 2.60 | 0.89 |
| Fam98c | 0.89 | 0.58 | 0.75 | 0.85 | 10.15 | 1.00 | 0.96 | 0.83 | 0.76 | 2.48 | 3.96 | 0.92 |
| Fasn | 2.08 | 2.61 | 4.96 | 0.80 | 5.84 | 0.93 | 0.80 | 0.76 | 1.07 | 3.42 | 3.78 | 1.24 |
| Fau | 1.33 | 0.53 | 0.87 | 0.20 | 15.23 | 1.28 | 1.19 | 0.68 | 0.95 | 3.54 | 4.94 | 0.90 |
| Fbll1 | 1.00 | 1.00 | 1.00 | 1.00 | 0.51 | 1.00 | 1.00 | 1.00 | 1.00 | 1.00 | 1.00 | 1.00 |
| Fbxl16 | 0.98 | 1.00 | 0.95 | 1.00 | 0.05 | 1.00 | 1.31 | 1.17 | 1.00 | 1.00 | 0.52 | 1.18 |
| Fbxl22 | 4.06 | 1.33 | 1.23 | 0.86 | 7.87 | 1.00 | 1.04 | 0.65 | 0.67 | 1.38 | 2.15 | 0.91 |
| Fbxo31 | 2.19 | 1.87 | 1.85 | 2.91 | 16.57 | 4.29 | 1.94 | 1.80 | 1.38 | 2.53 | 3.22 | 1.45 |
| Fbxo7 | 1.08 | 1.21 | 1.12 | 1.00 | 2.30 | 1.34 | 1.17 | 1.31 | 0.99 | 0.75 | 1.21 | 1.13 |
| Fbxw4 | 1.32 | 0.67 | 0.85 | 0.89 | 5.96 | 1.14 | 1.40 | 1.19 | 0.94 | 1.65 | 2.06 | 0.99 |
| Fbxw5 | 0.79 | 0.56 | 0.72 | 0.32 | 1.86 | 0.62 | 0.72 | 0.72 | 0.68 | 2.27 | 2.42 | 0.82 |
| Fcer1g | 2.65 | 1.43 | 2.77 | 1.08 | 7.77 | 1.65 | 1.22 | 1.05 | 1.81 | 1.27 | 2.26 | 1.27 |
| Fcf1 | 1.00 | 0.63 | 1.09 | 0.18 | 3.86 | 0.84 | 0.57 | 0.63 | 0.82 | 3.69 | 3.68 | 1.42 |
| Fcgbp | 1.00 | 1.00 | 1.00 | 1.00 | 1.00 | 1.00 | 1.00 | 1.00 | 1.00 | 1.64 | 1.35 | 1.39 |
| Fcgr3 | 5.93 | 2.48 | 3.45 | 2.21 | 1.79 | 2.23 | 1.99 | 2.00 | 2.41 | 0.61 | 1.63 | 1.41 |
| Fcgr4 | 1.00 | 1.00 | 1.78 | 1.00 | 1.54 | 1.07 | 1.00 | 1.00 | 2.62 | 2.65 | 3.82 | 2.04 |
| Fcna | 1.81 | 0.85 | 3.05 | 1.29 | 10.21 | 1.78 | 1.15 | 1.38 | 1.80 | 2.72 | 6.02 | 0.94 |

Fig. 35- 166

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Etohd2 | 1.67 | 1.69 | 1.04 | 0.73 | 0.86 | 1.07 | 0.69 | 0.93 | 0.85 | 0.93 | 1.70 | 1.53 |
| Etohi1 | 1.55 | 1.37 | 1.92 | 1.91 | 2.95 | 1.80 | 0.39 | 3.42 | 0.31 | 2.54 | 1.34 | 1.90 |
| Eva1a | 2.13 | 1.17 | 1.46 | 1.34 | 2.46 | 1.14 | 1.11 | 1.20 | 1.71 | 0.65 | 0.45 | 0.79 |
| Eva1c | 2.96 | 3.74 | 1.10 | 1.31 | 1.23 | 1.67 | 1.00 | 1.00 | 1.00 | 1.67 | 1.70 | 1.99 |
| Exoc7 | 0.83 | 0.90 | 0.92 | 0.99 | 0.62 | 0.94 | 0.93 | 1.59 | 0.93 | 0.96 | 0.87 | 0.90 |
| Extl1 | 0.88 | 0.75 | 0.96 | 1.77 | 1.28 | 0.98 | 1.29 | 1.59 | 0.88 | 1.00 | 1.00 | 1.00 |
| Ezh2 | 0.50 | 0.56 | 0.55 | 0.78 | 0.77 | 0.76 | 1.00 | 1.00 | 1.00 | 0.93 | 0.93 | 1.00 |
| F13a1 | 0.72 | 0.69 | 0.77 | 1.00 | 1.00 | 1.00 | 1.00 | 1.00 | 1.00 | 1.65 | 1.55 | 1.82 |
| F3 | 5.17 | 3.61 | 2.33 | 0.75 | 2.39 | 0.97 | 0.69 | 1.00 | 0.99 | 1.00 | 0.88 | 1.01 |
| Fabp3 | 0.38 | 0.86 | 0.07 | 0.58 | 0.52 | 0.79 | 1.00 | 1.00 | 1.00 | 1.00 | 1.33 | 1.00 |
| Fabp6 | 1.69 | 0.51 | 1.14 | 1.00 | 1.00 | 1.00 | 1.00 | 1.00 | 1.00 | 0.39 | 1.48 | 6.56 |
| Fabp9 | 2.31 | 1.00 | 1.00 | 1.00 | 1.00 | 1.00 | 1.00 | 1.17 | 1.00 | 1.00 | 1.00 | 1.00 |
| Fads2 | 1.01 | 0.42 | 0.79 | 1.31 | 0.38 | 1.36 | 0.99 | 2.79 | 1.23 | 1.09 | 0.58 | 0.91 |
| Fads6 | 1.00 | 1.00 | 1.46 | 0.87 | 0.89 | 1.06 | 0.78 | 3.78 | 1.36 | 1.00 | 1.00 | 1.00 |
| Faf1 | 0.87 | 1.03 | 0.92 | 1.23 | 0.82 | 1.06 | 1.65 | 2.44 | 1.28 | 1.06 | 1.53 | 1.05 |
| Fah | 2.46 | 1.77 | 1.07 | 1.19 | 0.64 | 1.01 | 0.96 | 2.23 | 0.91 | 2.06 | 1.73 | 1.09 |
| Fahd2a | 1.10 | 1.09 | 1.06 | 0.82 | 0.46 | 0.85 | 0.75 | 1.64 | 0.77 | 0.97 | 1.15 | 1.05 |
| Faim2 | 1.00 | 1.00 | 1.00 | 1.00 | 1.00 | 1.00 | 1.00 | 1.00 | 1.00 | 0.95 | 1.27 | 0.97 |
| Faim3 | 3.15 | 3.04 | 5.60 | 1.00 | 1.00 | 1.00 | 1.00 | 1.00 | 1.00 | 0.80 | 0.67 | 0.83 |
| Fam107a | 2.81 | 2.80 | 1.25 | 1.00 | 1.02 | 1.07 | 7.16 | 12.86 | 3.84 | 2.17 | 1.84 | 2.04 |
| Fam131b | 1.00 | 1.00 | 1.00 | 1.00 | 1.00 | 1.00 | 1.00 | 1.00 | 1.00 | 1.01 | 1.00 | 1.00 |
| Fam132a | 1.19 | 1.11 | 0.78 | 1.08 | 0.73 | 1.43 | 1.00 | 1.00 | 1.00 | 1.27 | 1.74 | 1.24 |
| Fam134b | 1.16 | 1.08 | 1.47 | 1.71 | 2.25 | 1.34 | 3.77 | 5.47 | 2.62 | 1.27 | 1.21 | 1.28 |
| Fam151a | 1.00 | 1.00 | 1.00 | 0.88 | 0.80 | 0.97 | 1.00 | 0.77 | 1.00 | 1.00 | 1.00 | 1.00 |
| Fam163b | 0.32 | 0.28 | 0.42 | 1.00 | 1.00 | 1.00 | 1.00 | 1.00 | 1.00 | 1.00 | 1.00 | 1.00 |
| Fam167b | 1.91 | 2.31 | 1.37 | 0.88 | 0.99 | 0.91 | 0.97 | 1.53 | 0.77 | 0.93 | 1.00 | 1.01 |
| Fam171b | 1.00 | 1.00 | 1.00 | 1.00 | 1.00 | 1.00 | 1.00 | 1.00 | 1.00 | 0.77 | 1.00 | 0.76 |
| Fam173a | 1.09 | 1.61 | 0.91 | 0.94 | 0.66 | 0.96 | 0.93 | 1.19 | 0.73 | 0.84 | 1.52 | 1.03 |
| Fam195a | 1.32 | 1.71 | 0.52 | 0.84 | 0.55 | 0.86 | 1.02 | 1.58 | 0.84 | 1.16 | 1.72 | 1.46 |
| Fam195b | 2.28 | 3.03 | 1.72 | 2.07 | 1.17 | 1.89 | 2.91 | 9.15 | 4.63 | 2.55 | 4.03 | 2.21 |
| Fam19a5 | 1.67 | 0.87 | 1.17 | 1.11 | 1.51 | 0.84 | 1.00 | 1.00 | 0.48 | 1.17 | 1.12 | 1.01 |
| Fam21 | 1.34 | 1.36 | 1.38 | 1.12 | 1.68 | 1.06 | 1.75 | 1.96 | 1.81 | 1.12 | 1.24 | 1.04 |
| Fam212a | 1.01 | 0.93 | 1.40 | 0.49 | 0.52 | 0.49 | 1.00 | 2.21 | 1.00 | 1.14 | 1.17 | 1.27 |
| Fam213b | 0.91 | 1.32 | 1.06 | 0.90 | 0.72 | 1.32 | 0.19 | 1.01 | 0.39 | 0.95 | 1.35 | 1.22 |
| Fam214a | 1.30 | 1.19 | 1.41 | 1.59 | 2.33 | 1.54 | 1.19 | 0.64 | 1.97 | 1.05 | 0.81 | 0.92 |
| Fam219aos | 1.13 | 1.08 | 1.60 | 1.28 | 1.00 | 1.30 | 1.93 | 1.00 | 1.16 | 1.48 | 1.16 | 1.51 |
| Fam222a | 0.68 | 1.20 | 0.95 | 0.64 | 0.66 | 0.94 | 5.10 | 3.32 | 2.33 | 0.84 | 0.68 | 0.88 |
| Fam229a | 1.00 | 1.00 | 1.00 | 1.00 | 1.06 | 1.00 | 1.00 | 2.84 | 1.00 | 1.00 | 1.00 | 1.00 |
| Fam229b | 1.27 | 1.73 | 0.83 | 1.15 | 0.70 | 0.62 | 1.00 | 1.00 | 1.00 | 0.76 | 0.64 | 1.03 |
| Fam24a | 1.00 | 0.85 | 1.00 | 1.00 | 1.00 | 1.00 | 1.00 | 1.00 | 1.00 | 1.00 | 1.00 | 1.00 |
| Fam25c | 0.96 | 1.27 | 0.79 | 1.04 | 0.56 | 1.01 | 0.81 | 3.25 | 0.74 | 1.00 | 1.00 | 1.00 |
| Fam49a | 0.86 | 0.71 | 1.23 | 0.92 | 1.00 | 1.32 | 1.00 | 1.00 | 1.18 | 1.23 | 0.86 | 1.12 |
| Fam53b | 0.74 | 0.73 | 1.02 | 1.02 | 0.93 | 1.05 | 2.65 | 5.42 | 2.02 | 0.91 | 0.71 | 0.92 |
| Fam57b | 1.00 | 1.00 | 1.00 | 0.90 | 0.97 | 1.96 | 1.00 | 1.00 | 1.00 | 0.91 | 0.92 | 0.75 |
| Fam69b | 5.09 | 5.26 | 0.92 | 1.49 | 0.62 | 0.72 | 1.00 | 1.00 | 1.00 | 0.98 | 0.96 | 0.77 |
| Fam83a | 1.00 | 1.00 | 1.64 | 1.00 | 1.00 | 1.00 | 1.00 | 1.00 | 1.00 | 1.00 | 1.00 | 1.00 |
| Fam92b | 1.00 | 1.00 | 1.00 | 1.00 | 1.00 | 1.00 | 1.00 | 1.00 | 1.00 | 1.00 | 1.00 | 1.00 |
| Fam96b | 1.04 | 1.25 | 0.97 | 0.87 | 0.55 | 0.86 | 1.11 | 1.07 | 1.09 | 1.32 | 1.65 | 1.12 |
| Fam98c | 1.11 | 1.59 | 1.13 | 1.25 | 1.01 | 0.98 | 1.19 | 1.40 | 0.83 | 0.86 | 1.38 | 1.03 |
| Fasn | 0.68 | 0.80 | 0.68 | 0.97 | 0.54 | 1.03 | 0.85 | 1.64 | 0.90 | 1.04 | 0.98 | 0.90 |
| Fau | 1.52 | 1.84 | 1.17 | 0.71 | 0.49 | 0.70 | 1.02 | 2.27 | 0.93 | 0.97 | 1.78 | 0.98 |
| Fbll1 | 1.00 | 1.00 | 1.00 | 1.00 | 1.00 | 1.00 | 1.00 | 1.00 | 1.00 | 1.00 | 1.00 | 1.00 |
| Fbxl16 | 1.00 | 1.00 | 1.00 | 1.38 | 1.00 | 1.20 | 1.00 | 1.00 | 1.00 | 1.10 | 0.85 | 1.06 |
| Fbxl22 | 1.98 | 2.27 | 2.12 | 1.00 | 0.85 | 1.00 | 1.00 | 1.34 | 1.00 | 1.11 | 1.11 | 0.83 |
| Fbxo31 | 1.37 | 1.56 | 1.30 | 1.34 | 1.13 | 1.24 | 1.93 | 3.39 | 1.78 | 1.18 | 1.25 | 1.18 |
| Fbxo7 | 1.31 | 1.42 | 1.02 | 1.06 | 1.21 | 0.92 | 1.22 | 0.74 | 1.31 | 1.13 | 1.44 | 1.04 |
| Fbxw4 | 1.24 | 1.64 | 1.09 | 0.90 | 1.04 | 1.06 | 1.44 | 1.38 | 1.15 | 0.99 | 1.37 | 1.04 |
| Fbxw5 | 0.88 | 1.07 | 0.81 | 0.73 | 0.50 | 0.75 | 0.97 | 2.75 | 0.81 | 0.80 | 0.94 | 0.88 |
| Fcer1g | 3.93 | 3.78 | 3.14 | 1.79 | 0.72 | 1.97 | 1.60 | 2.29 | 1.70 | 1.79 | 1.70 | 1.39 |
| Fcf1 | 1.39 | 1.33 | 1.03 | 0.70 | 0.63 | 1.54 | 1.00 | 1.03 | 1.11 | 1.00 | 1.13 | 1.58 |
| Fcgbp | 0.84 | 0.57 | 0.93 | 1.45 | 0.93 | 1.07 | 1.00 | 1.00 | 1.00 | 0.90 | 0.45 | 0.72 |
| Fcgr3 | 3.29 | 2.98 | 3.27 | 1.90 | 3.54 | 2.13 | 1.37 | 0.98 | 1.05 | 1.91 | 2.46 | 1.71 |
| Fcgr4 | 4.16 | 4.34 | 6.76 | 1.67 | 4.22 | 2.38 | 3.51 | 4.21 | 3.00 | 2.48 | 4.38 | 2.30 |
| Fcna | 3.43 | 4.23 | 1.81 | 1.00 | 1.00 | 1.00 | 0.93 | 1.11 | 0.92 | 1.08 | 1.94 | 0.80 |

Fig. 35-167

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Etohd2 | 1.92 | 1.13 | 1.26 | 1.01 | 4.02 | 1.70 | 0.86 | 1.34 | 0.92 | 1.12 | 1.10 | 0.83 |
| Etohi1 | 2.61 | 1.57 | 1.75 | 0.83 | 0.44 | 0.60 | 1.05 | 1.68 | 1.00 | 2.21 | 1.96 | 4.10 |
| Eva1a | 0.80 | 0.71 | 0.86 | 1.32 | 1.73 | 1.47 | 0.91 | 1.00 | 1.00 | 0.35 | 0.48 | 0.42 |
| Eva1c | 2.77 | 1.90 | 1.30 | 2.47 | 7.29 | 2.66 | 0.98 | 2.02 | 1.18 | 1.05 | 1.59 | 1.21 |
| Exoc7 | 0.83 | 0.89 | 0.71 | 0.91 | 2.13 | 0.78 | 1.02 | 3.86 | 0.95 | 0.88 | 0.87 | 0.94 |
| Extl1 | 1.40 | 2.11 | 1.44 | 1.00 | 1.00 | 1.00 | 1.00 | 1.00 | 1.00 | 0.89 | 1.09 | 0.91 |
| Ezh2 | 0.70 | 0.80 | 0.68 | 2.42 | 1.31 | 1.04 | 1.20 | 0.68 | 1.05 | 0.79 | 0.69 | 0.73 |
| F13a1 | 1.59 | 1.26 | 1.65 | 1.23 | 0.55 | 1.40 | 1.45 | 0.99 | 0.88 | 5.24 | 1.55 | 1.89 |
| F3 | 1.42 | 1.41 | 1.10 | 0.65 | 0.16 | 0.64 | 0.90 | 1.00 | 1.19 | 0.76 | 0.96 | 0.68 |
| Fabp3 | 0.84 | 0.99 | 0.86 | 0.42 | 1.00 | 1.00 | 1.02 | 1.23 | 0.85 | 1.00 | 1.93 | 1.00 |
| Fabp6 | 1.00 | 1.00 | 1.00 | 1.00 | 1.00 | 1.00 | 1.00 | 1.00 | 1.00 | 1.00 | 1.00 | 1.00 |
| Fabp9 | 1.00 | 1.00 | 1.00 | 3.19 | 1.49 | 1.20 | 0.90 | 1.14 | 0.92 | 1.00 | 1.00 | 1.00 |
| Fads2 | 1.57 | 0.95 | 1.24 | 1.44 | 0.60 | 1.10 | 1.02 | 5.75 | 0.76 | 1.20 | 1.32 | 0.87 |
| Fads6 | 0.95 | 1.12 | 0.70 | 1.00 | 1.00 | 0.98 | 0.77 | 5.35 | 1.13 | 1.00 | 1.13 | 1.00 |
| Faf1 | 1.03 | 1.08 | 1.05 | 1.11 | 2.67 | 1.16 | 1.07 | 2.05 | 0.97 | 1.13 | 1.11 | 0.85 |
| Fah | 1.29 | 1.58 | 1.26 | 1.67 | 3.65 | 1.10 | 0.91 | 2.69 | 0.77 | 1.08 | 1.84 | 1.72 |
| Fahd2a | 0.97 | 0.75 | 1.14 | 0.70 | 1.20 | 0.59 | 0.99 | 3.10 | 0.99 | 0.69 | 1.04 | 0.83 |
| Faim2 | 1.07 | 1.00 | 1.37 | 1.00 | 1.00 | 0.79 | 1.00 | 1.00 | 1.00 | 1.00 | 11.09 | 1.00 |
| Faim3 | 1.00 | 1.00 | 1.00 | 1.00 | 1.00 | 1.49 | 1.00 | 1.79 | 1.00 | 0.92 | 0.80 | 1.01 |
| Fam107a | 3.89 | 3.81 | 3.89 | 2.56 | 5.22 | 2.41 | 0.99 | 1.00 | 0.99 | 2.76 | 5.12 | 2.61 |
| Fam131b | 1.00 | 1.00 | 1.00 | 1.00 | 1.00 | 1.00 | 1.46 | 1.98 | 1.30 | 1.00 | 5.38 | 1.00 |
| Fam132a | 0.72 | 0.85 | 1.00 | 1.30 | 5.23 | 1.57 | 1.31 | 2.92 | 1.03 | 0.85 | 1.23 | 0.54 |
| Fam134b | 2.03 | 2.16 | 1.66 | 5.02 | 5.51 | 2.43 | 0.77 | 0.86 | 0.93 | 1.10 | 0.81 | 0.89 |
| Fam151a | 1.00 | 1.00 | 1.00 | 1.00 | 1.00 | 1.00 | 1.00 | 1.37 | 1.00 | 1.00 | 1.00 | 1.00 |
| Fam163b | 1.00 | 1.00 | 1.00 | 1.00 | 1.00 | 1.00 | 1.00 | 1.00 | 1.00 | 1.00 | 6.54 | 1.00 |
| Fam167b | 0.86 | 0.95 | 1.24 | 1.85 | 4.02 | 2.10 | 1.00 | 0.88 | 1.00 | 1.27 | 1.42 | 1.14 |
| Fam171b | 1.00 | 1.30 | 1.00 | 1.00 | 1.00 | 1.00 | 1.00 | 1.00 | 1.00 | 1.00 | 6.68 | 1.00 |
| Fam173a | 0.87 | 1.15 | 1.07 | 0.71 | 1.92 | 0.90 | 0.83 | 2.40 | 0.94 | 0.79 | 1.21 | 0.93 |
| Fam195a | 0.88 | 1.25 | 1.13 | 0.54 | 1.54 | 0.90 | 0.60 | 2.67 | 0.96 | 1.27 | 1.42 | 0.93 |
| Fam195b | 2.33 | 2.91 | 2.85 | 2.53 | 4.50 | 2.08 | 0.70 | 2.73 | 0.81 | 1.89 | 2.55 | 1.60 |
| Fam19a5 | 1.30 | 1.07 | 1.22 | 0.97 | 1.64 | 1.33 | 1.00 | 1.00 | 1.06 | 1.00 | 6.84 | 1.00 |
| Fam21 | 1.62 | 1.54 | 1.25 | 1.16 | 1.28 | 0.98 | 0.84 | 1.02 | 0.88 | 1.30 | 1.38 | 1.17 |
| Fam212a | 0.79 | 0.75 | 1.02 | 0.81 | 2.43 | 0.94 | 1.00 | 1.38 | 1.00 | 1.02 | 1.16 | 0.71 |
| Fam213b | 0.64 | 1.26 | 1.12 | 0.62 | 1.04 | 0.71 | 1.00 | 1.60 | 1.00 | 0.40 | 1.01 | 0.60 |
| Fam214a | 1.16 | 1.28 | 1.32 | 0.80 | 0.17 | 1.15 | 1.07 | 0.48 | 0.89 | 1.76 | 1.32 | 2.10 |
| Fam219aos | 1.29 | 1.19 | 1.22 | 1.01 | 0.45 | 1.07 | 0.83 | 1.07 | 1.01 | 1.24 | 1.69 | 1.62 |
| Fam222a | 1.10 | 1.59 | 1.62 | 3.60 | 1.00 | 2.48 | 0.85 | 1.27 | 1.11 | 1.17 | 2.14 | 1.06 |
| Fam229a | 1.00 | 1.00 | 1.00 | 0.57 | 8.81 | 1.17 | 0.81 | 3.80 | 1.11 | 1.00 | 1.00 | 1.00 |
| Fam229b | 1.49 | 0.95 | 1.11 | 1.78 | 2.21 | 0.84 | 0.95 | 0.75 | 0.91 | 2.58 | 2.14 | 0.84 |
| Fam24a | 1.00 | 1.00 | 1.00 | 1.00 | 6.24 | 1.00 | 1.06 | 3.04 | 0.89 | 1.00 | 1.00 | 1.00 |
| Fam25c | 0.84 | 0.97 | 1.15 | 1.00 | 1.00 | 1.00 | 1.00 | 1.00 | 1.00 | 1.00 | 1.00 | 1.00 |
| Fam49a | 1.11 | 1.34 | 1.20 | 1.29 | 1.25 | 0.77 | 1.00 | 1.00 | 1.00 | 0.92 | 0.69 | 0.94 |
| Fam53b | 0.98 | 1.13 | 0.82 | 0.78 | 0.61 | 0.64 | 0.94 | 1.30 | 1.10 | 0.78 | 0.65 | 0.91 |
| Fam57b | 1.20 | 1.26 | 1.53 | 0.93 | 4.08 | 0.75 | 0.90 | 1.52 | 0.72 | 1.00 | 5.68 | 1.00 |
| Fam69b | 0.63 | 0.65 | 0.70 | 0.69 | 1.00 | 0.83 | 1.13 | 0.44 | 0.89 | 0.78 | 2.38 | 0.52 |
| Fam83a | 1.17 | 1.25 | 2.23 | 0.52 | 1.00 | 1.18 | 1.21 | 5.48 | 2.00 | 1.00 | 1.00 | 1.00 |
| Fam92b | 1.00 | 1.00 | 1.00 | 1.00 | 1.91 | 1.00 | 0.87 | 4.03 | 0.79 | 1.00 | 1.00 | 1.00 |
| Fam96b | 1.21 | 1.12 | 0.91 | 0.85 | 1.12 | 0.98 | 1.03 | 0.76 | 1.23 | 0.96 | 1.41 | 0.99 |
| Fam98c | 1.25 | 1.15 | 1.14 | 0.90 | 3.13 | 1.19 | 0.93 | 2.14 | 1.00 | 0.98 | 1.21 | 1.09 |
| Fasn | 0.76 | 0.83 | 0.73 | 0.66 | 1.59 | 0.80 | 1.05 | 3.49 | 1.03 | 1.00 | 1.23 | 1.16 |
| Fau | 0.89 | 1.18 | 1.16 | 0.86 | 2.36 | 1.30 | 0.75 | 3.86 | 0.92 | 1.30 | 1.31 | 0.99 |
| Fbll1 | 1.00 | 1.00 | 1.00 | 1.00 | 1.00 | 1.00 | 0.55 | 1.21 | 1.00 | 1.00 | 2.49 | 1.00 |
| Fbxl16 | 1.16 | 1.46 | 1.24 | 1.00 | 1.00 | 0.93 | 0.92 | 1.00 | 1.11 | 1.00 | 33.83 | 1.37 |
| Fbxl22 | 0.80 | 0.69 | 1.21 | 2.77 | 1.29 | 2.18 | 1.00 | 1.24 | 1.00 | 1.70 | 1.96 | 1.07 |
| Fbxo31 | 1.58 | 1.82 | 1.65 | 3.31 | 15.99 | 4.71 | 1.10 | 1.75 | 0.97 | 1.32 | 1.88 | 1.40 |
| Fbxo7 | 0.97 | 1.00 | 1.09 | 0.85 | 1.81 | 1.05 | 0.80 | 0.45 | 0.94 | 0.81 | 1.04 | 0.92 |
| Fbxw4 | 1.04 | 1.26 | 1.47 | 1.07 | 4.24 | 1.32 | 0.87 | 1.31 | 0.81 | 1.10 | 1.24 | 0.85 |
| Fbxw5 | 0.85 | 0.92 | 0.97 | 0.71 | 1.68 | 0.83 | 0.56 | 2.09 | 0.59 | 0.82 | 1.00 | 0.80 |
| Fcer1g | 2.18 | 1.38 | 2.00 | 1.17 | 6.00 | 1.10 | 0.36 | 0.75 | 0.65 | 1.60 | 1.88 | 1.38 |
| Fcf1 | 1.00 | 1.00 | 1.39 | 1.00 | 1.00 | 1.01 | 1.00 | 4.66 | 1.24 | 1.36 | 0.77 | 1.45 |
| Fcgbp | 9.33 | 3.06 | 7.46 | 1.00 | 1.00 | 1.00 | 1.00 | 1.00 | 1.00 | 1.00 | 1.00 | 1.00 |
| Fcgr3 | 1.82 | 1.92 | 2.09 | 1.50 | 1.06 | 1.15 | 1.40 | 0.37 | 1.48 | 1.57 | 1.68 | 1.47 |
| Fcgr4 | 2.38 | 1.54 | 2.01 | 3.87 | 2.98 | 3.15 | 1.00 | 1.00 | 1.00 | 2.23 | 2.86 | 2.21 |
| Fcna | 1.10 | 0.97 | 0.84 | 0.72 | 1.80 | 0.85 | 1.00 | 1.00 | 1.00 | 0.97 | 2.11 | 0.94 |

Fig. 35- 168

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Etohd2 | 1.06 | 0.74 | 1.33 | 0.74 | 0.64 | 1.24 | 1.65 | 4.99 | 1.10 | 1.45 | 1.36 | 1.30 |
| Etohi1 | 1.00 | 1.00 | 1.00 | 1.92 | 1.48 | 2.27 | 0.97 | 3.13 | 1.32 | 1.00 | 3.06 | 3.48 |
| Eva1a | 1.00 | 1.00 | 1.00 | 0.98 | 0.79 | 0.91 | 0.81 | 0.68 | 0.72 | 1.00 | 1.00 | 1.00 |
| Eva1c | 1.00 | 1.00 | 1.00 | 1.27 | 1.65 | 1.41 | 1.62 | 8.39 | 1.20 | 1.00 | 1.00 | 1.00 |
| Exoc7 | 1.00 | 1.00 | 1.10 | 0.96 | 0.71 | 1.01 | 0.88 | 5.88 | 0.91 | 2.46 | 1.09 | 0.92 |
| Extl1 | 0.97 | 1.06 | 0.73 | 0.86 | 1.07 | 0.94 | 0.78 | 1.23 | 0.88 | 1.00 | 1.00 | 1.00 |
| Ezh2 | 1.00 | 1.00 | 1.00 | 1.08 | 1.42 | 1.20 | 1.05 | 1.45 | 0.78 | 1.20 | 0.83 | 0.88 |
| F13a1 | 1.13 | 1.22 | 2.04 | 1.15 | 1.00 | 1.15 | 1.25 | 1.09 | 1.70 | 1.22 | 1.56 | 1.47 |
| F3 | 1.00 | 1.00 | 1.00 | 1.17 | 1.00 | 1.14 | 0.64 | 0.10 | 0.56 | 1.00 | 1.00 | 1.00 |
| Fabp3 | 1.00 | 1.00 | 1.00 | 0.81 | 0.96 | 0.80 | 1.08 | 5.76 | 1.20 | 1.00 | 1.00 | 1.00 |
| Fabp6 | 1.00 | 1.00 | 1.00 | 1.00 | 1.00 | 1.00 | 0.58 | 5.08 | 0.66 | 1.00 | 1.00 | 1.00 |
| Fabp9 | 1.00 | 1.00 | 1.00 | 1.00 | 1.00 | 1.00 | 13.10 | 1.00 | 1.00 | 1.00 | 1.00 | 1.00 |
| Fads2 | 0.97 | 1.72 | 1.57 | 0.97 | 0.56 | 0.86 | 0.63 | 1.00 | 0.96 | 1.00 | 0.63 | 0.68 |
| Fads6 | 0.75 | 1.22 | 0.71 | 0.76 | 0.14 | 0.81 | 0.69 | 1.00 | 1.12 | 1.00 | 1.00 | 1.00 |
| Faf1 | 0.95 | 0.95 | 1.21 | 1.04 | 0.77 | 1.00 | 0.98 | 4.58 | 0.88 | 2.25 | 1.06 | 1.09 |
| Fah | 2.01 | 2.05 | 0.83 | 1.47 | 1.00 | 1.04 | 1.67 | 16.20 | 1.08 | 6.15 | 2.12 | 1.54 |
| Fahd2a | 0.61 | 0.84 | 1.13 | 0.96 | 0.66 | 0.97 | 1.17 | 8.04 | 0.73 | 2.00 | 0.85 | 1.16 |
| Faim2 | 1.00 | 1.00 | 1.00 | 1.12 | 0.83 | 1.08 | 0.85 | 2.71 | 0.84 | 1.00 | 1.00 | 1.00 |
| Faim3 | 1.00 | 1.00 | 1.00 | 1.00 | 1.00 | 1.00 | 1.00 | 1.00 | 1.00 | 0.92 | 0.78 | 0.93 |
| Fam107a | 2.64 | 2.33 | 1.68 | 1.34 | 1.35 | 1.33 | 1.79 | 2.56 | 2.00 | 1.00 | 1.00 | 1.00 |
| Fam131b | 1.00 | 1.00 | 1.00 | 1.02 | 0.71 | 0.93 | 1.00 | 1.00 | 1.00 | 1.00 | 1.00 | 1.00 |
| Fam132a | 0.43 | 0.41 | 0.68 | 0.73 | 0.87 | 1.02 | 0.95 | 3.31 | 0.83 | 1.03 | 0.73 | 0.88 |
| Fam134b | 1.60 | 1.75 | 1.48 | 1.06 | 1.00 | 1.07 | 1.25 | 0.98 | 1.36 | 1.22 | 1.39 | 1.19 |
| Fam151a | 1.00 | 1.00 | 1.00 | 1.00 | 1.00 | 1.00 | 1.00 | 1.00 | 1.00 | 1.00 | 1.00 | 1.00 |
| Fam163b | 1.00 | 1.00 | 1.00 | 0.87 | 1.58 | 0.90 | 1.00 | 1.00 | 1.00 | 1.00 | 1.00 | 1.00 |
| Fam167b | 0.67 | 1.32 | 1.00 | 1.00 | 0.21 | 1.27 | 1.30 | 5.80 | 1.21 | 0.67 | 0.68 | 0.97 |
| Fam171b | 1.00 | 1.00 | 1.00 | 0.78 | 0.42 | 0.87 | 1.00 | 1.00 | 1.00 | 1.00 | 1.00 | 1.00 |
| Fam173a | 0.73 | 0.92 | 1.03 | 1.05 | 0.80 | 1.00 | 1.16 | 8.14 | 0.90 | 3.50 | 1.13 | 1.04 |
| Fam195a | 0.64 | 0.48 | 0.60 | 1.06 | 1.28 | 1.36 | 1.61 | 9.90 | 0.81 | 2.00 | 0.99 | 0.77 |
| Fam195b | 1.73 | 1.79 | 1.74 | 2.08 | 1.53 | 2.05 | 2.40 | 28.05 | 1.70 | 7.02 | 3.10 | 2.64 |
| Fam19a5 | 1.00 | 1.00 | 1.00 | 1.15 | 2.20 | 1.08 | 0.71 | 0.47 | 1.02 | 1.00 | 1.00 | 1.00 |
| Fam21 | 1.46 | 1.42 | 1.10 | 1.15 | 5.26 | 1.24 | 1.28 | 1.04 | 1.28 | 1.72 | 1.78 | 1.41 |
| Fam212a | 1.00 | 1.00 | 1.00 | 0.82 | 6.41 | 1.04 | 1.04 | 2.59 | 0.91 | 1.13 | 1.02 | 0.98 |
| Fam213b | 0.76 | 1.00 | 0.61 | 1.08 | 0.99 | 1.06 | 0.77 | 11.68 | 0.65 | 1.95 | 1.06 | 0.98 |
| Fam214a | 0.74 | 1.20 | 1.25 | 1.03 | 0.71 | 1.08 | 0.90 | 0.12 | 0.94 | 0.62 | 1.24 | 1.18 |
| Fam219aos | 1.00 | 1.00 | 1.00 | 1.21 | 1.00 | 1.09 | 1.16 | 0.09 | 1.33 | 1.00 | 1.92 | 1.39 |
| Fam222a | 1.00 | 1.00 | 1.00 | 0.83 | 1.00 | 1.09 | 1.00 | 1.00 | 1.00 | 1.00 | 1.00 | 1.00 |
| Fam229a | 1.00 | 1.00 | 1.00 | 1.00 | 0.17 | 1.00 | 1.45 | 8.29 | 1.00 | 1.85 | 1.00 | 0.63 |
| Fam229b | 1.00 | 1.00 | 1.00 | 1.53 | 1.76 | 1.28 | 3.71 | 9.33 | 1.09 | 1.73 | 1.00 | 1.00 |
| Fam24a | 1.00 | 1.00 | 1.00 | 0.89 | 1.00 | 1.16 | 1.00 | 4.50 | 1.00 | 1.00 | 1.00 | 1.00 |
| Fam25c | 1.00 | 1.00 | 1.00 | 1.00 | 1.00 | 1.00 | 0.97 | 42.18 | 0.70 | 1.00 | 1.00 | 1.00 |
| Fam49a | 1.00 | 1.00 | 1.00 | 0.88 | 1.30 | 0.91 | 1.05 | 1.22 | 1.19 | 0.57 | 0.69 | 0.88 |
| Fam53b | 0.93 | 0.73 | 0.63 | 0.93 | 1.42 | 0.90 | 0.96 | 1.18 | 1.13 | 0.91 | 0.75 | 0.70 |
| Fam57b | 1.24 | 1.00 | 1.25 | 1.07 | 0.71 | 1.02 | 2.01 | 1.93 | 1.47 | 1.00 | 1.00 | 1.00 |
| Fam69b | 1.00 | 1.00 | 1.00 | 1.18 | 1.26 | 1.05 | 0.72 | 0.98 | 0.84 | 1.43 | 0.97 | 1.53 |
| Fam83a | 1.00 | 1.00 | 1.00 | 1.00 | 1.00 | 1.00 | 1.88 | 4.60 | 1.62 | 1.00 | 1.00 | 1.00 |
| Fam92b | 1.00 | 1.00 | 1.00 | 1.00 | 0.69 | 1.00 | 1.00 | 1.00 | 1.00 | 1.00 | 1.00 | 1.00 |
| Fam96b | 1.30 | 1.34 | 1.10 | 1.50 | 1.61 | 0.99 | 0.75 | 6.22 | 0.95 | 2.03 | 0.99 | 0.98 |
| Fam98c | 1.11 | 0.69 | 0.95 | 1.14 | 0.76 | 1.03 | 1.15 | 5.96 | 0.90 | 2.13 | 1.60 | 0.79 |
| Fasn | 1.40 | 1.10 | 1.39 | 0.92 | 0.84 | 0.91 | 1.13 | 6.98 | 1.07 | 2.25 | 0.85 | 0.85 |
| Fau | 0.86 | 0.88 | 1.01 | 1.20 | 0.83 | 1.09 | 1.13 | 21.78 | 0.88 | 4.31 | 1.41 | 1.18 |
| Fbll1 | 1.00 | 1.00 | 1.00 | 1.34 | 6.17 | 1.44 | 1.00 | 1.00 | 1.00 | 1.00 | 1.00 | 1.00 |
| Fbxl16 | 0.74 | 0.75 | 0.95 | 0.96 | 0.61 | 0.96 | 1.08 | 1.00 | 1.02 | 1.00 | 1.00 | 1.00 |
| Fbxl22 | 1.00 | 1.00 | 1.00 | 1.29 | 0.54 | 1.11 | 1.00 | 6.05 | 1.00 | 3.98 | 1.52 | 2.16 |
| Fbxo31 | 1.02 | 0.78 | 0.76 | 1.16 | 1.06 | 1.08 | 1.79 | 4.51 | 1.55 | 2.75 | 2.03 | 1.39 |
| Fbxo7 | 1.11 | 0.70 | 0.67 | 1.29 | 5.31 | 1.04 | 1.18 | 0.85 | 1.18 | 0.96 | 0.96 | 0.94 |
| Fbxw4 | 1.06 | 0.87 | 0.88 | 1.00 | 0.98 | 0.96 | 1.26 | 4.22 | 1.04 | 1.81 | 1.20 | 0.85 |
| Fbxw5 | 0.79 | 0.72 | 0.80 | 0.92 | 0.85 | 0.85 | 1.10 | 6.09 | 0.82 | 2.10 | 0.88 | 0.92 |
| Fcer1g | 1.45 | 1.92 | 1.18 | 1.55 | 13.25 | 1.84 | 2.10 | 2.65 | 2.07 | 2.68 | 2.28 | 2.10 |
| Fcf1 | 1.00 | 1.00 | 1.00 | 1.00 | 0.17 | 1.00 | 1.33 | 7.11 | 1.15 | 3.05 | 1.30 | 1.36 |
| Fcgbp | 1.00 | 1.00 | 1.00 | 1.00 | 1.00 | 1.00 | 1.08 | 1.97 | 1.33 | 1.00 | 1.00 | 1.00 |
| Fcgr3 | 1.41 | 2.02 | 1.72 | 1.94 | 4.37 | 1.77 | 2.38 | 1.75 | 2.46 | 1.65 | 2.39 | 2.23 |
| Fcgr4 | 1.00 | 1.00 | 1.00 | 1.00 | 1.00 | 1.00 | 1.55 | 6.25 | 2.13 | 3.63 | 3.56 | 2.59 |
| Fcna | 0.42 | 0.89 | 0.68 | 1.00 | 0.73 | 1.00 | 1.98 | 9.32 | 2.18 | 1.38 | 0.63 | 0.76 |

Fig. 35- 169

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Fcnb | 1.00 | 1.00 | 1.00 | 1.00 | 1.00 | 1.00 | 1.00 | 1.00 | 1.00 | 1.00 | 1.00 | 1.00 |
| Fdft1 | 1.73 | 0.79 | 1.14 | 1.25 | 15.77 | 2.58 | 1.26 | 1.20 | 0.63 | 2.87 | 4.01 | 1.27 |
| Fdps | 1.23 | 0.47 | 0.92 | 0.26 | 7.30 | 0.78 | 1.03 | 0.60 | 1.09 | 4.19 | 7.85 | 1.35 |
| Fdx1l | 1.34 | 0.74 | 0.97 | 0.39 | 4.79 | 0.84 | 0.83 | 0.83 | 0.87 | 1.80 | 2.89 | 1.07 |
| Fdxr | 0.60 | 0.34 | 0.81 | 0.48 | 5.79 | 0.82 | 0.90 | 0.80 | 1.03 | 3.05 | 3.02 | 1.04 |
| Fech | 0.78 | 0.80 | 0.72 | 0.60 | 1.73 | 0.73 | 0.86 | 0.83 | 0.75 | 8.50 | 4.82 | 1.11 |
| Fes | 1.07 | 1.11 | 1.42 | 0.51 | 3.52 | 1.26 | 0.96 | 0.91 | 1.09 | 1.71 | 2.18 | 0.99 |
| Fez1 | 3.61 | 1.22 | 2.56 | 1.35 | 0.23 | 1.88 | 1.00 | 1.10 | 1.52 | 1.00 | 1.00 | 1.74 |
| Fga | 1.00 | 1.00 | 1.00 | 3.18 | 1.55 | 1.00 | 1.54 | 0.63 | 1.00 | 1.00 | 1.00 | 1.00 |
| Fgb | 1.00 | 1.00 | 1.00 | 1.00 | 0.93 | 1.00 | 1.93 | 0.68 | 1.00 | 0.66 | 1.00 | 1.00 |
| Fgf21 | 1.00 | 1.00 | 1.00 | 1.00 | 1.00 | 0.77 | 1.00 | 1.00 | 1.00 | 1.00 | 1.00 | 1.00 |
| Fgfr2 | 1.00 | 1.00 | 1.00 | 11.37 | 9.44 | 6.19 | 1.00 | 1.00 | 1.00 | 0.64 | 0.78 | 0.87 |
| Fggy | 1.65 | 1.59 | 1.36 | 1.14 | 2.76 | 2.02 | 1.80 | 1.42 | 0.98 | 2.63 | 2.05 | 1.15 |
| Fh1 | 1.09 | 1.13 | 0.99 | 0.76 | 2.17 | 1.07 | 1.04 | 1.05 | 0.87 | 1.50 | 1.39 | 1.06 |
| Fhad1 | 1.00 | 1.00 | 1.00 | 1.00 | 1.00 | 1.00 | 1.00 | 1.00 | 1.00 | 5.43 | 2.37 | 1.09 |
| Fhit | 1.00 | 1.00 | 1.00 | 0.47 | 2.55 | 0.78 | 1.00 | 1.00 | 1.00 | 2.26 | 1.91 | 0.83 |
| Fhl3 | 2.74 | 2.00 | 2.25 | 3.01 | 8.08 | 3.49 | 0.85 | 0.99 | 1.24 | 2.64 | 2.66 | 1.48 |
| Fhl4 | 1.00 | 1.00 | 1.38 | 1.00 | 1.00 | 1.00 | 1.10 | 1.03 | 1.00 | 1.00 | 1.00 | 1.00 |
| Fis1 | 1.21 | 0.74 | 0.80 | 0.36 | 5.59 | 1.00 | 0.88 | 0.70 | 0.81 | 1.84 | 3.08 | 0.95 |
| Fkbp11 | 1.00 | 0.69 | 1.00 | 1.00 | 1.12 | 1.00 | 0.99 | 0.48 | 0.96 | 1.50 | 2.47 | 0.66 |
| Fkbp2 | 1.18 | 0.38 | 1.07 | 0.41 | 7.91 | 0.91 | 0.78 | 0.71 | 0.82 | 3.00 | 3.87 | 0.96 |
| Fkbp5 | 2.22 | 3.70 | 2.38 | 1.70 | 7.51 | 6.11 | 2.27 | 3.28 | 2.97 | 2.28 | 4.62 | 3.83 |
| Fkbpl | 1.41 | 0.93 | 1.39 | 0.62 | 3.56 | 0.76 | 1.31 | 1.16 | 0.73 | 2.54 | 2.67 | 1.32 |
| Flt3l | 1.37 | 0.33 | 0.79 | 0.27 | 6.94 | 0.90 | 0.87 | 0.63 | 0.71 | 2.06 | 2.55 | 0.82 |
| Flywch2 | 0.44 | 0.50 | 0.40 | 0.41 | 5.26 | 1.41 | 0.50 | 1.10 | 0.82 | 1.29 | 2.17 | 1.10 |
| Fmn2 | 1.00 | 1.00 | 1.00 | 1.00 | 1.00 | 1.00 | 1.00 | 1.00 | 1.00 | 1.00 | 1.00 | 1.00 |
| Fmo2 | 0.68 | 1.01 | 0.93 | 5.03 | 0.11 | 1.45 | 1.43 | 1.93 | 1.57 | 0.56 | 0.11 | 1.02 |
| Fn3k | 1.46 | 0.74 | 0.66 | 1.08 | 8.17 | 0.90 | 1.14 | 1.10 | 0.66 | 1.50 | 2.33 | 0.95 |
| Folr1 | 1.00 | 1.00 | 1.00 | 1.00 | 1.00 | 1.00 | 1.00 | 1.00 | 1.00 | 1.00 | 1.00 | 1.00 |
| Fos | 12.05 | 22.78 | 8.20 | 2.05 | 0.90 | 5.79 | 4.01 | 3.26 | 2.64 | 0.81 | 0.94 | 1.84 |
| Fosl2 | 5.52 | 11.18 | 3.11 | 7.26 | 2.91 | 1.96 | 2.80 | 3.33 | 1.90 | 1.39 | 1.42 | 1.22 |
| Foxo3 | 1.00 | 1.00 | 2.47 | 6.48 | 1.45 | 1.46 | 1.85 | 4.43 | 1.49 | 1.00 | 0.82 | 1.28 |
| Frg1 | 1.03 | 0.82 | 0.89 | 1.32 | 4.18 | 0.91 | 1.07 | 0.98 | 0.88 | 2.62 | 1.80 | 0.90 |
| Frrs1 | 1.00 | 1.00 | 1.00 | 0.47 | 4.12 | 1.12 | 1.00 | 1.00 | 1.00 | 3.82 | 4.21 | 1.03 |
| Frrs1l | 1.00 | 1.00 | 1.00 | 1.00 | 0.31 | 1.00 | 1.00 | 1.00 | 1.00 | 1.00 | 1.00 | 1.00 |
| Fst | 1.56 | 3.03 | 1.17 | 10.33 | 10.90 | 4.71 | 1.00 | 1.29 | 1.13 | 0.35 | 0.65 | 0.96 |
| Fth1 | 1.51 | 0.77 | 0.98 | 0.27 | 6.59 | 1.03 | 1.19 | 0.94 | 0.79 | 2.67 | 3.81 | 1.06 |
| Ftsj1 | 1.24 | 0.78 | 0.99 | 0.86 | 7.51 | 1.26 | 1.10 | 0.76 | 1.11 | 1.94 | 2.84 | 1.04 |
| Ftsj2 | 0.94 | 0.44 | 0.81 | 0.27 | 2.20 | 0.69 | 0.87 | 0.66 | 0.77 | 2.03 | 2.25 | 1.06 |
| Fuca1 | 0.87 | 0.56 | 0.84 | 0.38 | 2.85 | 0.88 | 1.17 | 0.94 | 0.96 | 3.04 | 2.59 | 0.94 |
| Fuom | 0.96 | 0.25 | 0.57 | 0.13 | 14.50 | 0.71 | 1.00 | 0.50 | 0.74 | 4.34 | 8.27 | 1.00 |
| Fus | 1.14 | 0.88 | 1.14 | 0.83 | 2.11 | 1.40 | 1.13 | 1.25 | 1.31 | 0.89 | 1.09 | 0.99 |
| Fxn | 0.96 | 0.46 | 0.69 | 0.45 | 6.54 | 1.24 | 1.34 | 1.16 | 1.05 | 2.84 | 3.40 | 1.00 |
| Fxyd1 | 1.24 | 0.35 | 0.92 | 0.22 | 28.09 | 1.37 | 0.83 | 0.86 | 0.92 | 4.06 | 4.92 | 0.79 |
| Fxyd2 | 2.63 | 0.57 | 1.58 | 0.73 | 10.56 | 1.50 | 0.67 | 0.87 | 0.57 | 2.44 | 3.54 | 1.16 |
| Fxyd3 | 1.00 | 1.00 | 1.00 | 1.00 | 1.00 | 1.00 | 1.00 | 1.00 | 1.00 | 0.47 | 11.05 | 1.00 |
| Fxyd5 | 3.37 | 1.07 | 1.28 | 1.00 | 8.80 | 1.55 | 1.39 | 1.23 | 1.19 | 1.99 | 3.32 | 0.91 |
| Fxyd7 | 0.85 | 0.39 | 0.61 | 1.11 | 8.40 | 1.38 | 0.74 | 0.62 | 1.04 | 1.24 | 1.91 | 0.95 |
| Gabarapl2 | 1.13 | 1.12 | 0.89 | 0.89 | 1.86 | 0.98 | 0.85 | 0.91 | 0.85 | 1.22 | 1.25 | 1.00 |
| Gabra1 | 1.00 | 1.00 | 1.00 | 1.00 | 0.15 | 1.00 | 1.00 | 1.00 | 1.00 | 1.00 | 1.00 | 1.00 |
| Gabra3 | 1.00 | 1.00 | 1.00 | 1.00 | 0.42 | 1.00 | 1.63 | 1.64 | 1.97 | 1.00 | 1.00 | 3.14 |
| Gabrb3 | 1.00 | 1.00 | 1.00 | 1.00 | 0.27 | 1.00 | 1.00 | 1.00 | 1.00 | 1.00 | 1.00 | 1.00 |
| Gabrq | 1.00 | 1.00 | 1.00 | 1.00 | 1.00 | 1.00 | 1.00 | 1.00 | 1.00 | 1.00 | 1.00 | 1.00 |
| Gad1 | 1.00 | 1.00 | 1.00 | 1.00 | 0.16 | 1.00 | 1.00 | 1.00 | 1.00 | 1.00 | 1.00 | 1.00 |
| Gad2 | 1.00 | 1.00 | 1.00 | 1.00 | 0.28 | 1.00 | 1.00 | 1.00 | 1.00 | 1.00 | 1.00 | 1.00 |
| Gadd45b | 1.62 | 1.11 | 0.76 | 5.33 | 6.60 | 2.97 | 2.08 | 1.70 | 0.95 | 0.88 | 1.30 | 1.16 |
| Gadd45g | 2.47 | 1.70 | 1.28 | 0.88 | 22.06 | 2.26 | 1.56 | 1.01 | 0.86 | 3.59 | 8.29 | 1.45 |
| Gadd45gip1 | 1.10 | 0.60 | 0.80 | 0.51 | 5.56 | 0.78 | 0.94 | 0.76 | 0.85 | 1.82 | 2.38 | 1.02 |
| Galns | 1.38 | 0.50 | 1.00 | 1.20 | 2.90 | 1.00 | 0.94 | 1.09 | 1.07 | 2.14 | 2.58 | 0.92 |
| Galt | 0.45 | 0.50 | 0.65 | 0.35 | 5.23 | 1.29 | 0.96 | 0.79 | 0.76 | 5.79 | 4.94 | 1.71 |
| Gap43 | 1.00 | 1.00 | 1.00 | 1.00 | 0.08 | 1.00 | 1.00 | 1.00 | 1.00 | 0.16 | 0.17 | 0.83 |
| Gapdhs | 1.00 | 1.00 | 1.00 | 1.00 | 1.00 | 1.00 | 1.00 | 1.00 | 1.00 | 1.00 | 1.00 | 1.00 |
| Gar1 | 1.10 | 0.83 | 1.16 | 0.57 | 6.87 | 1.17 | 1.45 | 0.98 | 1.01 | 1.51 | 2.26 | 0.70 |
| Gas1 | 1.10 | 1.35 | 1.02 | 5.25 | 1.66 | 1.79 | 0.89 | 0.98 | 0.99 | 0.43 | 0.39 | 0.74 |

Fig. 35- 170

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Fcnb | 1.00 | 1.00 | 1.00 | 1.00 | 1.00 | 1.00 | 1.00 | 1.00 | 1.00 | 1.00 | 1.00 | 1.00 |
| Fdft1 | 1.20 | 1.11 | 0.86 | 1.30 | 1.12 | 1.12 | 0.46 | 0.58 | 0.55 | 1.32 | 1.69 | 1.10 |
| Fdps | 0.89 | 1.18 | 0.68 | 0.68 | 0.64 | 0.72 | 1.47 | 3.20 | 0.96 | 1.28 | 1.87 | 1.00 |
| Fdx1l | 1.06 | 1.47 | 0.96 | 1.36 | 0.79 | 0.93 | 0.93 | 1.31 | 0.78 | 1.12 | 1.87 | 1.17 |
| Fdxr | 1.01 | 1.26 | 1.01 | 0.64 | 0.48 | 1.15 | 1.07 | 2.23 | 0.98 | 0.79 | 1.61 | 1.03 |
| Fech | 1.15 | 1.18 | 1.18 | 1.06 | 0.92 | 1.05 | 0.61 | 2.84 | 0.63 | 0.86 | 0.99 | 0.90 |
| Fes | 1.77 | 1.63 | 1.57 | 1.37 | 0.63 | 0.93 | 1.56 | 2.17 | 1.26 | 1.17 | 1.20 | 0.93 |
| Fez1 | 1.00 | 1.00 | 1.00 | 1.00 | 1.00 | 1.00 | 1.00 | 1.00 | 1.00 | 2.99 | 1.36 | 3.51 |
| Fga | 4.30 | 1.00 | 0.96 | 3.92 | 5.61 | 1.84 | 1.18 | 0.73 | 1.37 | 1.00 | 1.00 | 1.00 |
| Fgb | 5.27 | 1.00 | 0.63 | 1.00 | 1.00 | 1.00 | 1.46 | 0.55 | 1.37 | 1.00 | 1.00 | 1.00 |
| Fgf21 | 1.31 | 1.13 | 1.08 | 1.00 | 1.00 | 1.00 | 3.25 | 0.77 | 1.32 | 1.00 | 1.00 | 1.00 |
| Fgfr2 | 2.20 | 1.94 | 1.96 | 0.91 | 1.89 | 0.90 | 1.21 | 0.61 | 1.05 | 0.97 | 0.98 | 1.09 |
| Fggy | 1.23 | 1.88 | 1.74 | 0.77 | 0.74 | 0.79 | 0.66 | 1.29 | 0.88 | 1.10 | 1.29 | 1.12 |
| Fh1 | 0.77 | 0.77 | 0.70 | 1.35 | 1.20 | 0.90 | 2.73 | 5.26 | 1.61 | 1.04 | 1.18 | 0.95 |
| Fhad1 | 1.00 | 1.00 | 1.00 | 1.00 | 1.00 | 1.00 | 1.00 | 1.67 | 1.00 | 1.00 | 1.00 | 1.00 |
| Fhit | 0.95 | 1.02 | 0.92 | 0.86 | 0.89 | 0.77 | 1.00 | 1.00 | 1.00 | 0.67 | 1.13 | 0.56 |
| Fhl3 | 1.76 | 2.17 | 1.71 | 0.60 | 0.43 | 0.66 | 1.00 | 1.00 | 1.00 | 1.05 | 0.98 | 1.34 |
| Fhl4 | 1.00 | 1.00 | 1.00 | 1.00 | 1.00 | 1.00 | 1.00 | 1.00 | 1.00 | 1.00 | 1.00 | 1.00 |
| Fis1 | 1.20 | 1.60 | 1.12 | 1.05 | 0.83 | 0.97 | 0.89 | 1.05 | 0.88 | 0.90 | 1.54 | 1.05 |
| Fkbp11 | 1.00 | 1.67 | 1.25 | 0.33 | 0.60 | 0.87 | 1.35 | 0.99 | 1.30 | 0.63 | 1.72 | 1.78 |
| Fkbp2 | 1.08 | 1.49 | 1.00 | 0.70 | 0.48 | 0.82 | 0.86 | 2.15 | 0.81 | 0.99 | 1.64 | 1.10 |
| Fkbp5 | 1.69 | 2.34 | 1.56 | 1.99 | 3.04 | 1.38 | 1.50 | 1.93 | 2.19 | 1.94 | 2.75 | 2.04 |
| Fkbpl | 1.43 | 1.77 | 1.47 | 0.90 | 0.91 | 0.97 | 1.01 | 3.21 | 1.14 | 0.87 | 1.78 | 1.30 |
| Flt3l | 0.99 | 1.00 | 1.01 | 1.42 | 0.38 | 0.63 | 0.61 | 1.83 | 0.96 | 0.70 | 1.65 | 0.77 |
| Flywch2 | 1.59 | 3.02 | 1.74 | 0.91 | 0.71 | 0.80 | 1.00 | 1.00 | 1.00 | 0.97 | 1.51 | 1.02 |
| Fmn2 | 1.00 | 1.00 | 1.00 | 1.00 | 1.00 | 1.00 | 6.34 | 1.00 | 7.09 | 1.00 | 1.00 | 1.00 |
| Fmo2 | 2.29 | 1.54 | 1.44 | 1.01 | 1.37 | 1.09 | 1.07 | 1.00 | 0.77 | 0.96 | 0.58 | 0.92 |
| Fn3k | 0.95 | 1.24 | 0.73 | 0.83 | 0.58 | 0.77 | 0.35 | 0.54 | 0.37 | 0.74 | 1.66 | 0.58 |
| Folr1 | 1.00 | 1.00 | 1.00 | 1.02 | 0.90 | 0.98 | 1.00 | 1.00 | 1.00 | 1.00 | 1.00 | 1.00 |
| Fos | 2.43 | 3.01 | 1.46 | 1.56 | 1.00 | 1.00 | 2.23 | 1.00 | 2.45 | 1.13 | 1.83 | 1.10 |
| Fosl2 | 2.81 | 1.96 | 2.64 | 1.98 | 2.92 | 1.31 | 3.02 | 1.95 | 2.19 | 1.05 | 0.72 | 0.88 |
| Foxo3 | 0.51 | 0.30 | 0.85 | 2.41 | 2.22 | 2.14 | 1.68 | 1.00 | 1.35 | 1.09 | 0.38 | 0.67 |
| Frg1 | 1.13 | 1.12 | 0.95 | 0.81 | 0.65 | 1.00 | 1.52 | 2.31 | 1.14 | 1.01 | 1.31 | 0.84 |
| Frrs1 | 1.13 | 0.75 | 1.05 | 1.34 | 0.79 | 1.38 | 0.70 | 2.79 | 1.00 | 1.03 | 1.74 | 1.09 |
| Frrs1l | 1.00 | 1.00 | 1.00 | 1.00 | 1.00 | 1.00 | 1.00 | 1.00 | 1.00 | 1.00 | 1.00 | 1.00 |
| Fst | 2.61 | 1.55 | 1.13 | 0.60 | 1.03 | 0.83 | 5.48 | 1.00 | 1.27 | 2.05 | 2.05 | 1.64 |
| Fth1 | 1.47 | 1.73 | 1.28 | 1.27 | 0.86 | 1.38 | 0.95 | 1.59 | 0.87 | 1.28 | 1.95 | 1.12 |
| Ftsj1 | 1.13 | 1.33 | 0.91 | 1.14 | 0.82 | 0.98 | 1.04 | 1.44 | 1.00 | 0.95 | 1.30 | 1.32 |
| Ftsj2 | 1.19 | 1.21 | 0.87 | 0.88 | 0.54 | 1.10 | 0.57 | 1.24 | 0.86 | 0.94 | 1.10 | 0.91 |
| Fuca1 | 1.30 | 1.35 | 1.08 | 1.11 | 0.61 | 1.15 | 0.78 | 2.10 | 0.73 | 1.09 | 1.33 | 1.05 |
| Fuom | 1.87 | 2.02 | 1.01 | 0.69 | 0.52 | 0.61 | 0.88 | 2.56 | 0.74 | 1.29 | 2.00 | 0.91 |
| Fus | 0.98 | 1.05 | 0.87 | 1.06 | 0.88 | 1.03 | 1.80 | 1.01 | 1.56 | 1.12 | 1.34 | 1.11 |
| Fxn | 0.62 | 0.79 | 0.54 | 1.23 | 0.67 | 1.13 | 0.90 | 2.16 | 1.32 | 0.89 | 1.01 | 0.99 |
| Fxyd1 | 1.12 | 1.66 | 2.27 | 0.72 | 0.37 | 0.77 | 1.39 | 2.67 | 1.15 | 1.32 | 2.29 | 1.33 |
| Fxyd2 | 1.26 | 1.87 | 1.25 | 0.79 | 0.71 | 0.84 | 1.00 | 2.83 | 1.00 | 2.10 | 2.77 | 2.12 |
| Fxyd3 | 0.73 | 1.01 | 0.50 | 1.00 | 1.00 | 1.00 | 1.00 | 1.00 | 1.00 | 1.00 | 6.55 | 1.13 |
| Fxyd5 | 1.23 | 1.50 | 1.02 | 1.39 | 0.65 | 0.69 | 1.00 | 2.14 | 0.79 | 0.70 | 1.67 | 1.03 |
| Fxyd7 | 1.00 | 1.32 | 0.64 | 1.00 | 0.35 | 1.00 | 1.00 | 1.38 | 1.00 | 0.51 | 2.18 | 0.91 |
| Gabarapl2 | 1.04 | 1.17 | 1.00 | 0.88 | 1.20 | 1.08 | 1.26 | 1.12 | 1.02 | 1.18 | 1.42 | 1.02 |
| Gabra1 | 1.00 | 1.00 | 1.00 | 1.00 | 1.00 | 1.00 | 1.00 | 1.00 | 1.00 | 1.00 | 1.00 | 1.00 |
| Gabra3 | 1.00 | 1.00 | 1.00 | 2.80 | 1.00 | 3.51 | 1.07 | 1.00 | 1.00 | 1.36 | 1.00 | 1.59 |
| Gabrb3 | 1.00 | 1.00 | 1.00 | 0.35 | 0.30 | 0.31 | 1.00 | 1.00 | 1.00 | 1.00 | 1.00 | 1.00 |
| Gabrq | 1.00 | 1.00 | 1.00 | 1.00 | 1.00 | 1.00 | 1.00 | 1.00 | 1.00 | 1.00 | 1.00 | 1.00 |
| Gad1 | 1.00 | 1.00 | 1.00 | 1.00 | 1.00 | 1.00 | 1.00 | 1.00 | 1.00 | 1.00 | 1.00 | 1.00 |
| Gad2 | 1.00 | 1.00 | 1.00 | 1.00 | 1.00 | 1.00 | 1.00 | 1.00 | 1.00 | 0.94 | 1.00 | 1.00 |
| Gadd45b | 1.04 | 0.97 | 1.15 | 1.74 | 1.63 | 1.75 | 3.77 | 2.18 | 3.08 | 0.83 | 1.14 | 1.05 |
| Gadd45g | 5.35 | 6.46 | 2.26 | 2.13 | 2.70 | 2.03 | 3.87 | 17.04 | 4.14 | 1.42 | 2.12 | 1.04 |
| Gadd45gip1 | 1.08 | 1.25 | 0.92 | 0.90 | 0.63 | 0.86 | 0.86 | 1.51 | 0.75 | 0.90 | 1.35 | 1.02 |
| Galns | 1.21 | 1.37 | 1.45 | 1.33 | 0.94 | 1.18 | 0.84 | 2.20 | 0.99 | 0.98 | 1.15 | 0.94 |
| Galt | 2.88 | 3.57 | 2.63 | 1.11 | 0.99 | 1.23 | 0.93 | 1.86 | 1.06 | 1.40 | 1.84 | 1.39 |
| Gap43 | 1.00 | 1.00 | 1.00 | 1.00 | 1.00 | 1.00 | 1.00 | 1.00 | 1.00 | 0.91 | 1.30 | 1.17 |
| Gapdhs | 1.00 | 1.00 | 1.00 | 1.00 | 1.00 | 1.00 | 1.00 | 1.00 | 1.00 | 1.00 | 1.00 | 1.00 |
| Gar1 | 0.90 | 0.90 | 0.78 | 0.79 | 1.07 | 0.88 | 1.26 | 0.89 | 1.14 | 0.99 | 1.46 | 0.91 |
| Gas1 | 1.98 | 1.43 | 1.20 | 1.01 | 2.74 | 1.15 | 0.31 | 0.73 | 0.69 | 0.65 | 0.55 | 0.68 |

Fig. 35- 171

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Fcnb | 1.00 | 1.00 | 1.00 | 1.00 | 1.00 | 1.00 | 1.00 | 1.00 | 1.00 | 5.47 | 3.11 | 2.53 |
| Fdft1 | 0.90 | 0.99 | 0.97 | 0.37 | 1.44 | 0.74 | 0.99 | 1.79 | 0.93 | 0.95 | 1.46 | 1.05 |
| Fdps | 0.91 | 0.87 | 0.82 | 1.15 | 5.70 | 0.95 | 0.79 | 2.98 | 0.92 | 0.71 | 1.16 | 0.59 |
| Fdx1l | 1.08 | 1.07 | 1.01 | 0.81 | 4.14 | 0.90 | 0.90 | 1.31 | 1.22 | 1.01 | 1.49 | 0.95 |
| Fdxr | 0.93 | 1.00 | 1.04 | 0.68 | 1.01 | 0.80 | 0.62 | 2.05 | 0.85 | 0.91 | 1.09 | 0.90 |
| Fech | 0.75 | 0.92 | 0.95 | 0.69 | 1.49 | 0.80 | 1.08 | 5.97 | 0.94 | 0.64 | 0.65 | 0.42 |
| Fes | 1.51 | 1.91 | 1.84 | 1.00 | 2.49 | 0.82 | 1.00 | 1.00 | 1.00 | 0.89 | 0.83 | 0.94 |
| Fez1 | 1.19 | 1.34 | 1.63 | 2.92 | 1.00 | 3.52 | 0.96 | 0.76 | 0.88 | 1.00 | 9.25 | 1.00 |
| Fga | 2.60 | 4.24 | 1.68 | 7.04 | 1.00 | 1.32 | 1.00 | 1.00 | 1.00 | 1.00 | 1.00 | 1.00 |
| Fgb | 2.06 | 3.87 | 1.85 | 1.00 | 1.00 | 1.00 | 1.00 | 1.00 | 1.13 | 1.00 | 1.00 | 1.00 |
| Fgf21 | 1.00 | 1.00 | 1.00 | 2.51 | 1.00 | 1.16 | 1.49 | 0.72 | 1.58 | 1.00 | 1.00 | 1.00 |
| Fgfr2 | 0.95 | 0.92 | 1.19 | 1.71 | 0.76 | 2.40 | 0.65 | 1.00 | 0.62 | 0.90 | 1.50 | 0.84 |
| Fggy | 1.07 | 0.99 | 1.54 | 0.65 | 0.99 | 0.79 | 1.29 | 1.74 | 0.79 | 0.95 | 1.30 | 1.42 |
| Fh1 | 0.96 | 1.05 | 0.84 | 0.97 | 2.87 | 0.84 | 1.07 | 1.26 | 1.15 | 0.84 | 0.84 | 0.65 |
| Fhad1 | 1.00 | 1.00 | 1.00 | 1.00 | 1.00 | 1.00 | 1.16 | 2.89 | 1.13 | 1.00 | 1.00 | 1.00 |
| Fhit | 1.00 | 1.18 | 1.00 | 0.36 | 1.13 | 1.11 | 1.32 | 1.22 | 1.31 | 1.81 | 2.62 | 1.16 |
| Fhl3 | 1.98 | 1.04 | 1.78 | 2.19 | 4.17 | 2.19 | 1.21 | 2.36 | 1.32 | 1.62 | 1.62 | 1.52 |
| Fhl4 | 1.00 | 1.00 | 1.00 | 3.36 | 1.00 | 1.19 | 1.01 | 0.71 | 0.99 | 1.00 | 1.00 | 1.00 |
| Fis1 | 0.98 | 0.95 | 1.05 | 1.29 | 4.98 | 1.03 | 0.98 | 1.47 | 0.96 | 0.91 | 1.18 | 0.85 |
| Fkbp11 | 1.29 | 0.83 | 1.23 | 0.68 | 1.49 | 1.09 | 1.00 | 4.54 | 1.00 | 2.14 | 1.30 | 1.97 |
| Fkbp2 | 1.08 | 1.32 | 1.10 | 0.89 | 1.93 | 1.05 | 0.99 | 3.64 | 1.00 | 0.93 | 1.13 | 0.93 |
| Fkbp5 | 1.98 | 3.36 | 2.32 | 1.78 | 3.08 | 2.58 | 1.11 | 0.98 | 0.92 | 2.69 | 3.49 | 3.20 |
| Fkbpl | 1.37 | 1.31 | 0.99 | 1.10 | 3.15 | 0.94 | 1.00 | 2.82 | 1.00 | 1.09 | 1.34 | 1.18 |
| Flt3l | 1.05 | 1.01 | 1.06 | 1.02 | 2.03 | 1.10 | 1.00 | 3.29 | 1.00 | 0.91 | 0.94 | 1.00 |
| Flywch2 | 1.50 | 1.01 | 2.33 | 0.61 | 5.89 | 1.01 | 0.77 | 1.28 | 0.91 | 1.74 | 2.00 | 0.84 |
| Fmn2 | 1.00 | 1.00 | 1.00 | 1.00 | 1.00 | 1.00 | 1.00 | 1.00 | 1.00 | 1.00 | 1.24 | 1.00 |
| Fmo2 | 1.58 | 1.70 | 1.64 | 1.79 | 0.23 | 1.36 | 0.87 | 1.00 | 1.03 | 1.24 | 0.80 | 2.30 |
| Fn3k | 0.99 | 0.76 | 0.90 | 0.52 | 1.97 | 1.34 | 1.00 | 1.07 | 1.00 | 0.40 | 0.68 | 0.25 |
| Folr1 | 1.35 | 1.71 | 0.94 | 1.91 | 1.16 | 3.19 | 0.60 | 1.43 | 0.67 | 1.00 | 1.00 | 1.00 |
| Fos | 0.99 | 0.98 | 1.03 | 2.86 | 0.53 | 0.72 | 1.00 | 1.00 | 1.00 | 2.15 | 3.25 | 1.55 |
| Fosl2 | 0.95 | 1.11 | 0.73 | 3.61 | 2.07 | 1.99 | 1.54 | 1.00 | 1.14 | 2.40 | 1.99 | 2.31 |
| Foxo3 | 1.22 | 1.49 | 0.72 | 3.10 | 0.20 | 0.55 | 1.08 | 0.90 | 1.34 | 0.73 | 0.46 | 1.12 |
| Frg1 | 0.98 | 1.11 | 1.01 | 0.91 | 6.06 | 0.90 | 0.75 | 1.67 | 0.99 | 1.04 | 1.05 | 1.04 |
| Frrs1 | 0.87 | 0.91 | 0.79 | 1.28 | 2.03 | 0.64 | 1.00 | 1.00 | 1.00 | 1.38 | 0.94 | 1.40 |
| Frrs1l | 1.00 | 1.00 | 1.00 | 1.00 | 1.00 | 1.00 | 1.00 | 1.00 | 1.00 | 1.00 | 5.11 | 1.00 |
| Fst | 1.41 | 1.72 | 1.40 | 1.62 | 1.00 | 1.21 | 1.00 | 1.00 | 1.00 | 1.00 | 1.00 | 1.00 |
| Fth1 | 1.23 | 1.45 | 1.30 | 0.85 | 2.29 | 0.73 | 0.87 | 1.75 | 0.82 | 0.98 | 1.42 | 0.87 |
| Ftsj1 | 0.85 | 1.23 | 0.97 | 1.25 | 3.23 | 1.07 | 1.00 | 2.04 | 1.00 | 1.30 | 1.20 | 1.07 |
| Ftsj2 | 0.82 | 0.88 | 0.87 | 0.58 | 0.97 | 0.75 | 0.90 | 2.08 | 0.68 | 1.00 | 1.19 | 1.08 |
| Fuca1 | 0.92 | 1.14 | 0.77 | 0.89 | 1.73 | 0.89 | 0.93 | 3.44 | 0.96 | 0.87 | 0.94 | 0.78 |
| Fuom | 0.90 | 1.53 | 0.89 | 0.71 | 2.39 | 1.29 | 1.00 | 1.00 | 1.00 | 1.00 | 1.00 | 1.00 |
| Fus | 1.14 | 1.03 | 1.05 | 1.15 | 6.45 | 1.26 | 1.15 | 0.69 | 1.12 | 1.06 | 1.00 | 1.01 |
| Fxn | 1.36 | 0.88 | 0.95 | 1.05 | 3.32 | 1.30 | 0.55 | 0.96 | 0.47 | 1.45 | 1.42 | 1.12 |
| Fxyd1 | 0.99 | 0.82 | 1.23 | 0.77 | 3.18 | 1.53 | 0.65 | 4.06 | 0.58 | 1.00 | 2.56 | 0.99 |
| Fxyd2 | 1.00 | 1.00 | 1.23 | 1.36 | 1.29 | 1.12 | 0.73 | 1.72 | 1.14 | 0.87 | 1.06 | 0.46 |
| Fxyd3 | 0.86 | 1.13 | 0.83 | 1.00 | 3.50 | 1.00 | 1.00 | 1.00 | 1.00 | 1.00 | 1.00 | 1.00 |
| Fxyd5 | 1.13 | 1.34 | 1.24 | 1.66 | 4.15 | 1.60 | 0.96 | 2.04 | 0.99 | 0.96 | 1.00 | 0.76 |
| Fxyd7 | 0.54 | 0.76 | 0.91 | 1.48 | 2.97 | 3.03 | 1.00 | 1.35 | 1.00 | 1.00 | 5.11 | 1.00 |
| Gabarapl2 | 1.11 | 0.98 | 1.13 | 1.03 | 5.83 | 1.10 | 1.00 | 0.62 | 0.94 | 0.83 | 0.93 | 0.76 |
| Gabra1 | 1.00 | 1.00 | 1.00 | 1.00 | 1.00 | 1.00 | 0.86 | 1.00 | 1.00 | 1.00 | 9.30 | 1.00 |
| Gabra3 | 1.00 | 1.00 | 1.00 | 10.37 | 1.00 | 10.37 | 1.00 | 1.00 | 1.00 | 12.33 | 12.42 | 10.63 |
| Gabrb3 | 1.00 | 1.00 | 1.00 | 1.00 | 1.00 | 1.00 | 1.00 | 1.00 | 1.00 | 1.00 | 5.31 | 1.00 |
| Gabrq | 1.00 | 1.00 | 1.00 | 1.00 | 1.00 | 1.00 | 1.00 | 1.00 | 1.00 | 10.21 | 6.60 | 8.03 |
| Gad1 | 1.00 | 1.00 | 1.00 | 1.00 | 1.00 | 1.00 | 1.00 | 1.00 | 1.00 | 1.00 | 11.56 | 1.00 |
| Gad2 | 1.00 | 1.00 | 1.00 | 1.00 | 1.00 | 1.00 | 1.00 | 1.00 | 1.00 | 1.00 | 5.80 | 1.00 |
| Gadd45b | 0.82 | 1.20 | 1.10 | 2.16 | 3.29 | 1.45 | 0.80 | 0.50 | 0.80 | 0.94 | 0.99 | 1.01 |
| Gadd45g | 1.50 | 2.40 | 1.37 | 5.62 | 45.51 | 5.13 | 0.90 | 1.77 | 1.16 | 1.49 | 1.65 | 0.93 |
| Gadd45gip1 | 0.86 | 1.09 | 1.00 | 0.96 | 1.95 | 1.16 | 0.79 | 2.08 | 0.95 | 0.97 | 1.24 | 0.84 |
| Galns | 0.66 | 0.71 | 0.87 | 1.00 | 1.67 | 1.13 | 0.85 | 1.39 | 0.89 | 1.20 | 1.31 | 1.22 |
| Galt | 1.36 | 1.34 | 1.10 | 1.73 | 2.73 | 2.08 | 1.00 | 1.85 | 0.87 | 2.77 | 3.38 | 2.86 |
| Gap43 | 1.09 | 0.80 | 0.91 | 1.00 | 1.00 | 0.86 | 1.00 | 2.12 | 1.00 | 1.00 | 17.28 | 1.00 |
| Gapdhs | 1.00 | 1.00 | 1.00 | 2.39 | 3.66 | 1.00 | 0.87 | 2.14 | 1.02 | 1.00 | 1.00 | 1.00 |
| Gar1 | 1.03 | 0.76 | 0.94 | 1.23 | 3.87 | 1.29 | 0.97 | 0.92 | 1.13 | 1.25 | 1.24 | 1.07 |
| Gas1 | 0.73 | 0.87 | 0.98 | 1.25 | 0.42 | 0.90 | 0.80 | 1.00 | 0.91 | 1.45 | 1.23 | 1.91 |

Fig. 35- 172

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Fcnb | 1.00 | 1.00 | 1.00 | 1.00 | 1.00 | 1.00 | 1.00 | 1.00 | 1.00 | 1.10 | 1.30 | 1.36 |
| Fdft1 | 0.74 | 0.43 | 0.63 | 1.13 | 1.07 | 1.03 | 0.91 | 4.25 | 0.69 | 2.48 | 1.42 | 1.57 |
| Fdps | 1.00 | 1.65 | 1.00 | 0.77 | 0.99 | 0.85 | 0.90 | 11.44 | 0.55 | 5.21 | 2.09 | 2.71 |
| Fdx1l | 0.88 | 0.76 | 0.90 | 1.18 | 1.13 | 0.92 | 1.13 | 6.34 | 0.90 | 2.45 | 0.98 | 0.95 |
| Fdxr | 1.16 | 1.31 | 0.82 | 1.11 | 1.05 | 1.04 | 1.10 | 11.02 | 0.77 | 2.98 | 1.30 | 1.29 |
| Fech | 0.85 | 0.86 | 0.79 | 0.79 | 1.27 | 0.86 | 0.95 | 5.17 | 1.05 | 2.74 | 1.35 | 1.33 |
| Fes | 1.00 | 1.00 | 1.00 | 1.00 | 1.36 | 1.00 | 1.46 | 6.81 | 1.61 | 2.80 | 1.32 | 0.99 |
| Fez1 | 1.00 | 1.00 | 1.00 | 1.06 | 1.25 | 1.00 | 2.14 | 1.00 | 2.37 | 1.00 | 1.00 | 1.00 |
| Fga | 1.00 | 1.00 | 1.00 | 1.00 | 1.00 | 1.00 | 4.33 | 1.04 | 1.26 | 1.00 | 1.00 | 1.00 |
| Fgb | 1.00 | 1.00 | 1.00 | 1.00 | 1.00 | 1.00 | 1.00 | 1.00 | 1.00 | 1.00 | 1.00 | 1.00 |
| Fgf21 | 1.14 | 5.91 | 0.24 | 1.00 | 1.00 | 1.00 | 1.00 | 1.00 | 1.00 | 1.00 | 1.00 | 1.00 |
| Fgfr2 | 1.00 | 1.00 | 1.00 | 0.79 | 0.84 | 0.75 | 1.01 | 0.68 | 1.19 | 1.00 | 1.00 | 1.00 |
| Fggy | 1.00 | 1.00 | 1.00 | 1.72 | 0.73 | 1.31 | 0.81 | 5.64 | 1.82 | 1.00 | 1.05 | 1.30 |
| Fh1 | 1.11 | 1.25 | 1.20 | 1.09 | 2.76 | 0.98 | 0.99 | 1.94 | 0.98 | 0.70 | 0.60 | 0.79 |
| Fhad1 | 1.00 | 1.00 | 1.00 | 1.00 | 0.59 | 1.00 | 1.00 | 1.00 | 1.00 | 1.00 | 1.00 | 1.00 |
| Fhit | 1.00 | 1.00 | 1.00 | 0.69 | 1.69 | 0.90 | 1.54 | 9.87 | 0.95 | 0.99 | 0.72 | 0.87 |
| Fhl3 | 1.00 | 1.00 | 1.00 | 1.00 | 0.82 | 1.00 | 1.58 | 3.73 | 1.44 | 2.38 | 1.68 | 1.81 |
| Fhl4 | 1.00 | 1.00 | 1.00 | 1.00 | 1.00 | 1.00 | 13.21 | 1.00 | 1.13 | 1.00 | 1.00 | 1.00 |
| Fis1 | 1.47 | 0.87 | 0.97 | 1.08 | 1.16 | 1.08 | 1.25 | 6.15 | 1.11 | 2.90 | 1.55 | 1.31 |
| Fkbp11 | 0.54 | 0.80 | 0.81 | 1.00 | 0.52 | 1.00 | 0.77 | 9.10 | 0.65 | 2.21 | 0.86 | 1.39 |
| Fkbp2 | 1.03 | 0.91 | 0.82 | 1.28 | 0.87 | 1.04 | 1.37 | 17.63 | 0.90 | 3.17 | 0.92 | 1.12 |
| Fkbp5 | 1.54 | 3.07 | 2.15 | 1.67 | 2.65 | 1.75 | 2.39 | 2.69 | 2.08 | 2.31 | 3.32 | 2.50 |
| Fkbpl | 0.83 | 0.83 | 0.87 | 1.21 | 1.13 | 1.17 | 1.55 | 7.75 | 0.93 | 3.20 | 1.73 | 1.66 |
| Flt3l | 1.00 | 0.84 | 1.00 | 0.91 | 0.46 | 0.72 | 0.65 | 9.57 | 0.69 | 3.22 | 1.42 | 1.04 |
| Flywch2 | 1.00 | 1.00 | 1.00 | 0.81 | 0.97 | 1.14 | 1.08 | 2.51 | 0.99 | 1.87 | 1.17 | 1.00 |
| Fmn2 | 1.00 | 1.00 | 1.00 | 1.02 | 1.00 | 0.87 | 1.00 | 1.00 | 1.00 | 1.00 | 1.00 | 1.00 |
| Fmo2 | 1.29 | 1.57 | 1.93 | 0.64 | 1.00 | 0.55 | 1.04 | 0.06 | 1.23 | 1.00 | 1.00 | 1.00 |
| Fn3k | 0.35 | 0.40 | 0.62 | 1.14 | 1.07 | 0.93 | 0.55 | 4.49 | 0.59 | 1.41 | 0.77 | 0.79 |
| Folr1 | 1.00 | 1.00 | 1.00 | 1.05 | 0.70 | 1.05 | 1.58 | 5.20 | 1.01 | 1.00 | 1.00 | 1.00 |
| Fos | 1.00 | 1.00 | 1.00 | 1.96 | 1.62 | 1.46 | 0.41 | 0.11 | 0.62 | 1.56 | 5.24 | 2.63 |
| Fosl2 | 1.46 | 1.28 | 1.00 | 1.40 | 1.05 | 1.18 | 1.44 | 0.72 | 1.51 | 0.96 | 1.14 | 0.98 |
| Foxo3 | 2.14 | 1.77 | 1.78 | 0.73 | 0.87 | 0.89 | 1.11 | 0.28 | 1.28 | 0.65 | 0.62 | 0.40 |
| Frg1 | 1.50 | 1.00 | 1.16 | 1.10 | 1.98 | 0.90 | 1.20 | 6.36 | 0.97 | 2.18 | 1.40 | 0.97 |
| Frrs1 | 1.00 | 1.00 | 1.00 | 1.00 | 0.81 | 1.00 | 1.01 | 17.98 | 1.19 | 4.46 | 1.30 | 1.06 |
| Frrs1l | 1.00 | 1.00 | 1.00 | 0.72 | 0.38 | 0.82 | 1.00 | 1.00 | 1.00 | 1.00 | 1.00 | 1.00 |
| Fst | 1.00 | 1.00 | 1.00 | 1.02 | 1.00 | 0.92 | 1.16 | 0.11 | 1.19 | 1.00 | 1.00 | 1.00 |
| Fth1 | 1.11 | 1.11 | 1.02 | 1.15 | 1.01 | 1.12 | 1.26 | 10.87 | 1.18 | 2.43 | 1.11 | 1.16 |
| Ftsj1 | 1.00 | 1.00 | 1.00 | 1.15 | 0.85 | 0.86 | 0.89 | 5.36 | 0.83 | 2.03 | 0.96 | 0.93 |
| Ftsj2 | 0.52 | 0.45 | 0.62 | 1.34 | 0.85 | 1.19 | 0.90 | 6.51 | 0.77 | 2.06 | 1.06 | 1.01 |
| Fuca1 | 0.95 | 0.80 | 0.82 | 1.21 | 1.00 | 1.10 | 1.04 | 8.09 | 0.91 | 2.67 | 1.24 | 1.03 |
| Fuom | 1.25 | 0.97 | 1.66 | 1.75 | 1.00 | 1.12 | 1.16 | 23.49 | 1.01 | 1.63 | 1.00 | 1.00 |
| Fus | 0.81 | 0.83 | 0.58 | 1.17 | 1.14 | 1.09 | 0.94 | 0.67 | 0.82 | 1.04 | 0.94 | 0.80 |
| Fxn | 1.00 | 1.11 | 1.13 | 0.88 | 0.72 | 0.88 | 1.56 | 9.00 | 0.79 | 1.67 | 0.97 | 1.16 |
| Fxyd1 | 0.81 | 1.82 | 1.75 | 1.43 | 0.80 | 1.52 | 1.44 | 40.75 | 1.68 | 1.00 | 1.00 | 1.00 |
| Fxyd2 | 1.00 | 1.00 | 1.49 | 1.07 | 0.39 | 0.76 | 1.09 | 13.34 | 1.22 | 1.00 | 1.00 | 1.00 |
| Fxyd3 | 3.63 | 3.79 | 4.76 | 1.00 | 1.00 | 1.00 | 0.96 | 23.74 | 0.83 | 1.00 | 1.00 | 1.00 |
| Fxyd5 | 1.00 | 1.00 | 1.00 | 0.82 | 0.72 | 1.01 | 1.55 | 10.80 | 1.25 | 4.52 | 1.82 | 1.39 |
| Fxyd7 | 1.00 | 1.00 | 1.00 | 0.92 | 0.79 | 0.93 | 0.92 | 6.15 | 1.13 | 1.17 | 1.00 | 1.00 |
| Gabarapl2 | 0.95 | 1.02 | 0.96 | 1.07 | 1.27 | 1.04 | 0.85 | 1.21 | 0.88 | 0.91 | 1.05 | 1.01 |
| Gabra1 | 1.00 | 1.00 | 1.00 | 0.99 | 1.12 | 0.92 | 1.00 | 1.00 | 1.00 | 1.00 | 1.00 | 1.00 |
| Gabra3 | 1.00 | 1.00 | 1.00 | 1.04 | 0.35 | 0.96 | 1.00 | 1.00 | 1.00 | 1.00 | 1.00 | 1.00 |
| Gabrb3 | 1.00 | 1.00 | 1.00 | 1.00 | 0.96 | 0.98 | 1.00 | 1.00 | 1.00 | 1.00 | 1.00 | 1.00 |
| Gabrq | 1.00 | 1.00 | 1.00 | 1.20 | 0.84 | 1.13 | 1.00 | 1.00 | 1.00 | 1.00 | 1.00 | 1.00 |
| Gad1 | 1.00 | 1.00 | 1.00 | 1.06 | 0.94 | 0.96 | 1.00 | 1.00 | 1.00 | 1.00 | 1.00 | 1.00 |
| Gad2 | 1.00 | 1.00 | 1.00 | 1.00 | 2.00 | 0.98 | 1.00 | 1.00 | 1.00 | 1.00 | 1.00 | 1.00 |
| Gadd45b | 1.11 | 2.79 | 2.33 | 1.04 | 1.52 | 0.98 | 1.41 | 1.39 | 0.94 | 1.29 | 0.92 | 1.42 |
| Gadd45g | 2.96 | 6.26 | 1.80 | 1.35 | 1.39 | 1.07 | 5.94 | 39.65 | 3.32 | 3.11 | 1.82 | 1.33 |
| Gadd45gip1 | 0.92 | 0.75 | 1.00 | 1.13 | 1.00 | 1.07 | 1.09 | 7.60 | 0.85 | 1.96 | 0.94 | 1.03 |
| Galns | 1.00 | 1.00 | 1.00 | 1.29 | 0.68 | 1.25 | 1.29 | 5.31 | 1.02 | 2.20 | 1.25 | 1.20 |
| Galt | 1.47 | 1.18 | 0.98 | 0.69 | 0.94 | 0.76 | 1.23 | 6.17 | 1.39 | 9.95 | 3.58 | 3.42 |
| Gap43 | 1.00 | 1.00 | 1.00 | 1.17 | 0.35 | 1.06 | 0.99 | 0.40 | 0.99 | 1.00 | 1.00 | 1.00 |
| Gapdhs | 1.00 | 1.00 | 1.00 | 1.00 | 0.90 | 1.00 | 5.18 | 10.79 | 0.87 | 1.00 | 1.00 | 1.00 |
| Gar1 | 0.64 | 0.53 | 0.70 | 1.05 | 1.59 | 1.19 | 0.95 | 3.02 | 0.82 | 1.26 | 0.71 | 0.86 |
| Gas1 | 0.62 | 0.69 | 1.04 | 0.99 | 1.00 | 0.95 | 0.80 | 0.12 | 0.86 | 1.00 | 1.00 | 1.00 |

Fig. 35- 173

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Gatad2b | 0.74 | 1.00 | 1.47 | 3.04 | 0.51 | 1.50 | 3.50 | 5.44 | 2.53 | 1.00 | 1.00 | 1.44 |
| Gatsl3 | 1.26 | 0.55 | 1.35 | 1.20 | 15.71 | 1.52 | 1.27 | 0.97 | 1.04 | 2.43 | 3.47 | 0.98 |
| Gba | 0.89 | 0.91 | 1.08 | 0.39 | 1.85 | 0.78 | 1.17 | 0.83 | 1.46 | 2.54 | 1.99 | 0.89 |
| Gbp11 | 1.00 | 1.00 | 1.00 | 5.95 | 5.47 | 2.42 | 1.00 | 1.00 | 1.00 | 1.00 | 1.00 | 1.00 |
| Gcat | 0.86 | 0.37 | 0.69 | 0.42 | 7.20 | 1.18 | 0.86 | 0.89 | 0.82 | 4.00 | 6.38 | 1.14 |
| Gchfr | 1.54 | 1.61 | 2.49 | 0.27 | 15.41 | 1.24 | 1.05 | 0.83 | 0.73 | 1.77 | 3.68 | 0.86 |
| Gcn1l1 | 0.96 | 0.63 | 1.23 | 0.71 | 4.03 | 1.04 | 1.50 | 1.42 | 1.24 | 2.58 | 3.55 | 0.93 |
| Gdf1 | 0.30 | 0.07 | 0.24 | 1.00 | 0.54 | 1.00 | 0.81 | 1.00 | 1.00 | 1.68 | 0.83 | 0.61 |
| Gdf15 | 1.00 | 1.00 | 1.00 | 1.00 | 1.00 | 1.00 | 2.25 | 1.66 | 2.59 | 0.42 | 0.60 | 1.94 |
| Gdpd3 | 2.58 | 1.20 | 1.89 | 0.96 | 12.75 | 2.58 | 2.01 | 1.61 | 1.33 | 3.27 | 3.55 | 1.21 |
| Gdpd5 | 0.49 | 0.37 | 0.39 | 1.15 | 4.08 | 1.49 | 0.31 | 0.26 | 0.37 | 1.39 | 1.74 | 0.67 |
| Gemin7 | 1.30 | 1.03 | 1.11 | 0.53 | 3.28 | 0.94 | 0.97 | 0.76 | 0.90 | 1.68 | 1.75 | 0.95 |
| Gfer | 1.62 | 0.94 | 1.23 | 0.81 | 5.90 | 1.45 | 1.57 | 1.26 | 1.20 | 2.02 | 2.34 | 0.91 |
| Gfod2 | 0.83 | 0.66 | 0.81 | 0.59 | 1.68 | 0.87 | 0.96 | 0.71 | 1.09 | 0.86 | 1.32 | 1.00 |
| Ggct | 0.59 | 0.36 | 0.57 | 1.45 | 5.81 | 1.79 | 0.64 | 0.46 | 0.53 | 1.63 | 2.33 | 0.92 |
| Ggnbp1 | 1.20 | 0.64 | 0.95 | 0.47 | 6.91 | 0.81 | 0.82 | 0.91 | 0.76 | 3.47 | 3.65 | 1.13 |
| Ggt1 | 1.00 | 1.00 | 1.00 | 1.00 | 1.00 | 1.00 | 1.00 | 1.00 | 1.00 | 5.42 | 4.29 | 1.32 |
| Ggt5 | 1.15 | 0.68 | 1.21 | 0.87 | 4.52 | 1.51 | 0.92 | 0.80 | 1.09 | 3.22 | 4.17 | 1.77 |
| Gins4 | 0.98 | 0.84 | 0.78 | 0.40 | 1.84 | 0.76 | 0.83 | 0.85 | 0.78 | 0.61 | 0.88 | 0.70 |
| Gjb4 | 1.00 | 1.00 | 1.00 | 1.00 | 1.00 | 1.00 | 1.00 | 1.00 | 1.00 | 1.00 | 1.00 | 1.00 |
| Gk2 | 1.00 | 1.00 | 1.00 | 0.37 | 0.11 | 0.69 | 1.00 | 1.00 | 1.11 | 1.00 | 1.00 | 1.00 |
| Glb1 | 1.20 | 0.73 | 1.45 | 0.89 | 5.78 | 1.43 | 1.09 | 1.00 | 1.02 | 2.21 | 3.01 | 1.26 |
| Glmn | 0.64 | 0.38 | 0.80 | 1.02 | 3.28 | 0.58 | 0.67 | 0.78 | 1.30 | 2.93 | 1.58 | 1.00 |
| Glo1 | 1.21 | 0.81 | 1.02 | 1.30 | 5.12 | 1.35 | 0.97 | 0.94 | 1.01 | 1.69 | 1.85 | 1.19 |
| Glod5 | 1.00 | 1.00 | 1.00 | 1.00 | 5.04 | 1.00 | 1.00 | 1.00 | 1.00 | 1.21 | 1.00 | 1.00 |
| Glrb | 1.00 | 1.00 | 1.00 | 1.00 | 0.17 | 1.00 | 1.00 | 1.00 | 1.00 | 1.00 | 1.00 | 1.00 |
| Glrx3 | 1.24 | 0.72 | 0.98 | 0.58 | 12.20 | 1.83 | 0.74 | 0.92 | 0.71 | 2.02 | 2.79 | 0.83 |
| Glul | 1.84 | 2.37 | 2.05 | 1.22 | 2.17 | 1.38 | 1.54 | 1.72 | 1.25 | 2.02 | 1.94 | 1.44 |
| Gm10012 | 1.13 | 0.53 | 0.70 | 1.93 | 7.27 | 0.88 | 0.60 | 0.79 | 0.73 | 1.67 | 3.56 | 0.99 |
| Gm10094 | 2.09 | 0.85 | 0.76 | 0.23 | 10.74 | 0.88 | 1.06 | 0.73 | 0.62 | 1.06 | 3.54 | 1.61 |
| Gm10318 | 1.00 | 1.00 | 1.00 | 1.00 | 1.00 | 1.00 | 1.00 | 1.00 | 1.00 | 1.00 | 1.00 | 1.00 |
| Gm10334 | 1.00 | 1.00 | 1.00 | 1.00 | 1.00 | 1.00 | 1.00 | 1.00 | 1.00 | 1.00 | 1.00 | 1.00 |
| Gm10409 | 1.00 | 1.00 | 1.00 | 1.00 | 1.07 | 1.00 | 1.89 | 1.66 | 1.07 | 1.00 | 1.00 | 1.00 |
| Gm10451 | 1.00 | 1.00 | 1.00 | 1.00 | 1.00 | 1.00 | 1.00 | 1.00 | 1.00 | 1.00 | 1.00 | 1.00 |
| Gm10591 | 0.54 | 1.00 | 1.00 | 0.81 | 1.00 | 1.00 | 0.85 | 1.46 | 0.71 | 0.09 | 0.04 | 0.45 |
| Gm10638 | 2.56 | 2.76 | 2.28 | 0.20 | 1.15 | 0.72 | 1.30 | 0.99 | 1.58 | 1.34 | 1.79 | 1.15 |
| Gm10754 | 1.00 | 1.00 | 1.00 | 1.00 | 1.00 | 1.00 | 1.00 | 1.00 | 1.00 | 1.00 | 1.00 | 1.00 |
| Gm11517 | 1.46 | 0.47 | 1.06 | 0.44 | 2.84 | 0.69 | 0.41 | 0.78 | 0.68 | 1.41 | 2.96 | 1.65 |
| Gm11627 | 1.00 | 1.00 | 1.00 | 1.00 | 1.00 | 1.00 | 0.62 | 1.00 | 1.00 | 0.51 | 0.52 | 1.00 |
| Gm11974 | 1.91 | 0.56 | 0.70 | 0.73 | 10.07 | 2.27 | 1.68 | 0.87 | 1.31 | 4.03 | 3.88 | 1.39 |
| Gm12191 | 1.00 | 1.00 | 1.00 | 1.00 | 1.00 | 1.00 | 1.00 | 1.00 | 1.00 | 6.96 | 1.00 | 1.00 |
| Gm13139 | 1.00 | 0.87 | 1.00 | 0.64 | 5.62 | 0.58 | 1.01 | 1.25 | 0.92 | 1.74 | 2.55 | 0.94 |
| Gm13298 | 1.05 | 1.00 | 1.00 | 1.13 | 1.00 | 1.02 | 1.03 | 1.02 | 1.00 | 1.00 | 1.50 | 4.42 |
| Gm13305 | 11.80 | 43.03 | 9.95 | 5.35 | 53.19 | 5.65 | 6.60 | 5.99 | 6.30 | 263.76 | 69.27 | 6.83 |
| Gm13306 | 2.87 | 5.35 | 1.97 | 2.03 | 3.36 | 3.38 | 3.19 | 3.36 | 2.20 | 2.20 | 2.92 | 3.16 |
| Gm13308 | 1.00 | 1.00 | 1.00 | 1.00 | 1.00 | 1.42 | 1.47 | 1.00 | 0.52 | 1.00 | 1.00 | 2.60 |
| Gm13363 | 0.29 | 1.00 | 1.25 | 1.00 | 1.00 | 1.00 | 5.75 | 21.17 | 6.51 | 1.00 | 1.00 | 1.00 |
| Gm13547 | 1.00 | 1.00 | 1.00 | 1.00 | 1.00 | 1.00 | 1.00 | 1.00 | 1.00 | 1.00 | 1.00 | 1.00 |
| Gm13826 | 1.28 | 0.82 | 0.95 | 0.31 | 5.11 | 1.23 | 0.99 | 0.85 | 0.91 | 1.13 | 2.14 | 0.92 |
| Gm13889 | 10.50 | 3.60 | 4.95 | 4.90 | 13.76 | 1.02 | 1.19 | 0.85 | 1.99 | 0.32 | 0.58 | 0.79 |
| Gm14288 | 1.02 | 0.60 | 1.00 | 4.22 | 5.86 | 3.32 | 0.81 | 2.02 | 1.83 | 3.05 | 1.72 | 1.49 |
| Gm14378 | 0.54 | 0.58 | 0.45 | 0.44 | 1.43 | 1.33 | 0.95 | 1.04 | 0.72 | 2.66 | 1.21 | 0.65 |
| Gm14391 | 1.00 | 1.00 | 1.00 | 1.48 | 3.95 | 1.31 | 1.20 | 1.15 | 1.00 | 3.97 | 6.44 | 1.42 |
| Gm14446 | 1.00 | 1.00 | 1.00 | 1.00 | 1.00 | 1.00 | 1.02 | 1.18 | 1.04 | 0.64 | 0.61 | 1.50 |
| Gm14461 | 18.10 | 19.12 | 20.38 | 1.00 | 1.00 | 1.00 | 1.00 | 1.00 | 1.00 | 1.00 | 1.00 | 1.00 |
| Gm15133 | 1.00 | 1.00 | 1.00 | 1.00 | 1.00 | 1.00 | 1.00 | 1.00 | 1.00 | 1.08 | 1.91 | 1.00 |
| Gm15284 | 1.00 | 1.00 | 1.00 | 1.00 | 1.00 | 1.00 | 1.00 | 1.00 | 1.00 | 1.00 | 1.00 | 1.00 |
| Gm15417 | 0.85 | 0.52 | 0.68 | 0.26 | 4.16 | 0.75 | 0.74 | 0.57 | 0.68 | 2.85 | 3.67 | 1.19 |
| Gm15421 | 1.35 | 1.28 | 1.08 | 3.92 | 5.61 | 1.13 | 0.78 | 1.05 | 0.95 | 0.65 | 1.50 | 0.83 |
| Gm15471 | 1.00 | 1.00 | 1.00 | 1.82 | 26.88 | 3.66 | 1.00 | 1.00 | 1.00 | 1.00 | 1.00 | 1.00 |
| Gm15772 | 1.91 | 0.76 | 1.17 | 0.44 | 4.85 | 1.04 | 0.96 | 0.90 | 0.92 | 2.19 | 2.02 | 0.86 |
| Gm15850 | 1.00 | 1.00 | 1.00 | 1.00 | 1.00 | 1.00 | 1.00 | 1.00 | 1.00 | 1.00 | 1.00 | 1.00 |
| Gm16062 | 1.80 | 0.81 | 1.46 | 0.69 | 6.46 | 2.02 | 1.03 | 0.83 | 1.19 | 1.52 | 3.39 | 0.81 |
| Gm16381 | 1.31 | 1.12 | 0.88 | 0.85 | 3.38 | 0.88 | 0.73 | 0.81 | 0.71 | 0.85 | 1.76 | 0.95 |

Fig. 35- 174

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Gatad2b | 0.26 | 0.18 | 0.75 | 1.98 | 1.00 | 1.42 | 1.60 | 1.00 | 1.27 | 0.81 | 0.79 | 0.87 |
| Gatsl3 | 0.92 | 1.27 | 1.00 | 1.50 | 1.19 | 1.79 | 0.79 | 2.11 | 0.98 | 0.64 | 1.59 | 0.98 |
| Gba | 1.24 | 1.31 | 1.45 | 1.05 | 0.75 | 1.07 | 0.88 | 2.75 | 0.88 | 1.04 | 1.19 | 0.97 |
| Gbp11 | 0.96 | 0.82 | 1.07 | 1.00 | 1.00 | 1.00 | 1.66 | 1.04 | 0.56 | 1.00 | 1.00 | 1.00 |
| Gcat | 0.96 | 1.06 | 0.87 | 0.80 | 0.56 | 0.91 | 0.85 | 1.99 | 0.87 | 1.02 | 1.37 | 1.52 |
| Gchfr | 0.57 | 1.06 | 0.44 | 0.84 | 0.64 | 0.94 | 0.71 | 1.49 | 0.71 | 1.33 | 1.90 | 1.44 |
| Gcn1l1 | 0.74 | 0.81 | 0.84 | 1.21 | 0.66 | 1.13 | 0.87 | 1.53 | 1.28 | 0.97 | 0.99 | 0.90 |
| Gdf1 | 1.00 | 1.00 | 1.00 | 1.00 | 0.74 | 1.00 | 1.00 | 1.00 | 1.00 | 1.00 | 1.60 | 1.12 |
| Gdf15 | 4.54 | 2.65 | 2.44 | 1.66 | 3.53 | 1.57 | 5.63 | 0.59 | 2.70 | 1.27 | 2.59 | 1.08 |
| Gdpd3 | 2.65 | 3.46 | 2.52 | 1.68 | 1.58 | 2.00 | 5.90 | 4.31 | 4.36 | 2.93 | 2.82 | 1.86 |
| Gdpd5 | 5.68 | 5.24 | 4.54 | 1.26 | 0.86 | 0.97 | 1.00 | 1.00 | 1.00 | 1.01 | 1.13 | 1.14 |
| Gemin7 | 1.10 | 1.37 | 1.04 | 1.00 | 1.00 | 1.01 | 1.26 | 1.54 | 0.96 | 1.01 | 1.38 | 0.98 |
| Gfer | 0.80 | 1.09 | 0.98 | 1.46 | 0.94 | 1.19 | 1.07 | 1.33 | 0.96 | 0.94 | 1.39 | 1.08 |
| Gfod2 | 0.88 | 0.88 | 0.87 | 0.96 | 0.66 | 1.20 | 1.43 | 0.72 | 1.55 | 1.09 | 1.22 | 1.15 |
| Ggct | 1.22 | 1.16 | 1.30 | 1.54 | 1.10 | 1.12 | 1.01 | 1.97 | 0.77 | 0.77 | 1.86 | 1.57 |
| Ggnbp1 | 1.63 | 1.06 | 1.08 | 0.72 | 0.43 | 0.85 | 0.67 | 1.55 | 0.91 | 0.77 | 1.07 | 0.95 |
| Ggt1 | 0.98 | 1.24 | 1.00 | 1.10 | 0.60 | 1.03 | 1.00 | 1.00 | 1.00 | 0.94 | 1.54 | 1.55 |
| Ggt5 | 1.55 | 1.21 | 1.02 | 1.45 | 0.74 | 1.26 | 1.10 | 3.37 | 1.33 | 1.11 | 1.12 | 1.17 |
| Gins4 | 0.76 | 0.95 | 0.69 | 0.71 | 0.65 | 0.63 | 0.67 | 0.64 | 0.70 | 0.70 | 1.26 | 0.86 |
| Gjb4 | 1.00 | 1.00 | 1.00 | 1.00 | 1.00 | 1.00 | 1.00 | 1.00 | 1.00 | 0.86 | 0.86 | 0.76 |
| Gk2 | 1.00 | 1.00 | 1.00 | 0.98 | 1.00 | 0.87 | 1.31 | 1.00 | 1.35 | 0.96 | 1.00 | 0.65 |
| Glb1 | 1.74 | 1.89 | 1.66 | 2.91 | 2.63 | 2.54 | 1.35 | 1.39 | 1.27 | 2.22 | 2.69 | 2.00 |
| Glmn | 0.68 | 0.56 | 1.17 | 0.91 | 0.58 | 0.85 | 1.00 | 3.97 | 1.00 | 1.27 | 1.13 | 0.76 |
| Glo1 | 1.08 | 1.20 | 1.08 | 1.07 | 0.75 | 1.12 | 0.70 | 0.94 | 0.74 | 1.14 | 1.31 | 1.26 |
| Glod5 | 1.00 | 1.00 | 1.00 | 0.80 | 0.88 | 0.67 | 1.00 | 1.00 | 1.00 | 1.04 | 1.52 | 0.90 |
| Glrb | 4.86 | 4.19 | 5.68 | 1.00 | 1.00 | 1.00 | 1.00 | 1.00 | 1.00 | 1.00 | 1.00 | 1.00 |
| Glrx3 | 1.08 | 1.52 | 1.02 | 0.88 | 0.83 | 1.08 | 0.78 | 1.30 | 0.84 | 0.75 | 1.74 | 0.96 |
| Glul | 2.49 | 2.59 | 1.84 | 1.51 | 1.65 | 1.14 | 1.14 | 1.61 | 1.82 | 0.97 | 0.97 | 1.10 |
| Gm10012 | 1.11 | 1.24 | 0.83 | 0.77 | 0.79 | 0.56 | 0.85 | 1.04 | 0.75 | 1.23 | 1.92 | 1.13 |
| Gm10094 | 0.62 | 2.65 | 0.99 | 1.48 | 0.97 | 0.58 | 0.54 | 1.10 | 0.93 | 0.72 | 1.68 | 0.89 |
| Gm10318 | 1.00 | 1.00 | 1.00 | 1.00 | 1.00 | 1.00 | 1.00 | 1.00 | 1.00 | 1.00 | 1.00 | 1.00 |
| Gm10334 | 1.00 | 1.00 | 1.00 | 1.00 | 1.00 | 1.00 | 1.00 | 1.00 | 1.00 | 1.41 | 1.00 | 1.30 |
| Gm10409 | 1.96 | 1.45 | 2.22 | 1.00 | 1.00 | 1.00 | 1.00 | 1.00 | 1.00 | 1.00 | 1.00 | 1.00 |
| Gm10451 | 1.37 | 1.82 | 2.42 | 0.95 | 1.00 | 1.08 | 1.00 | 1.00 | 1.43 | 1.08 | 1.00 | 2.43 |
| Gm10591 | 2.66 | 2.56 | 2.35 | 1.00 | 1.00 | 1.00 | 1.00 | 1.00 | 1.00 | 0.71 | 0.88 | 0.96 |
| Gm10638 | 3.77 | 2.34 | 1.57 | 1.63 | 1.70 | 1.80 | 1.00 | 1.00 | 1.00 | 1.03 | 2.01 | 1.92 |
| Gm10754 | 1.00 | 1.00 | 1.00 | 1.00 | 1.00 | 1.00 | 1.00 | 1.00 | 1.00 | 1.00 | 1.00 | 1.00 |
| Gm11517 | 1.62 | 1.95 | 0.71 | 1.46 | 2.76 | 1.57 | 1.00 | 1.00 | 1.00 | 1.00 | 2.31 | 1.00 |
| Gm11627 | 1.00 | 1.00 | 1.00 | 1.00 | 1.00 | 1.00 | 1.00 | 1.00 | 1.00 | 0.83 | 1.06 | 0.74 |
| Gm11974 | 1.10 | 1.54 | 0.95 | 1.28 | 0.75 | 0.64 | 1.63 | 2.60 | 1.19 | 1.04 | 1.13 | 1.97 |
| Gm12191 | 1.00 | 1.00 | 1.00 | 1.00 | 0.15 | 1.00 | 1.00 | 1.95 | 1.00 | 1.00 | 1.00 | 1.00 |
| Gm13139 | 0.55 | 1.15 | 0.62 | 0.80 | 0.90 | 1.16 | 1.00 | 1.00 | 1.00 | 1.04 | 1.26 | 0.98 |
| Gm13298 | 4.21 | 2.37 | 3.68 | 1.53 | 1.00 | 1.86 | 1.00 | 1.00 | 1.00 | 2.48 | 1.57 | 2.28 |
| Gm13305 | 29.40 | 17.02 | 18.37 | 6.16 | 92.11 | 6.19 | 10.41 | 232.23 | 7.93 | 6.48 | 10.50 | 6.34 |
| Gm13306 | 7.42 | 9.88 | 5.05 | 2.92 | 0.64 | 2.51 | 1.35 | 0.38 | 1.81 | 3.00 | 4.27 | 3.53 |
| Gm13308 | 2.18 | 3.04 | 3.47 | 1.00 | 1.00 | 1.08 | 1.04 | 1.00 | 1.04 | 1.00 | 1.00 | 1.89 |
| Gm13363 | 0.37 | 0.29 | 1.00 | 1.00 | 1.00 | 1.00 | 1.00 | 1.00 | 1.00 | 0.81 | 1.00 | 1.00 |
| Gm13547 | 1.00 | 1.00 | 1.00 | 1.00 | 1.00 | 1.00 | 1.00 | 1.00 | 1.00 | 1.00 | 1.00 | 1.00 |
| Gm13826 | 1.32 | 1.77 | 1.04 | 0.93 | 0.91 | 0.93 | 0.97 | 0.94 | 1.07 | 1.06 | 1.80 | 1.11 |
| Gm13889 | 1.13 | 0.99 | 0.87 | 0.84 | 0.92 | 0.85 | 1.04 | 0.53 | 1.22 | 0.91 | 0.98 | 1.01 |
| Gm14288 | 0.69 | 2.11 | 2.59 | 1.52 | 3.42 | 1.00 | 1.02 | 3.65 | 0.69 | 2.42 | 2.31 | 0.85 |
| Gm14378 | 1.11 | 1.67 | 1.21 | 0.87 | 0.79 | 1.05 | 1.19 | 2.34 | 1.06 | 0.85 | 0.81 | 1.05 |
| Gm14391 | 5.52 | 7.08 | 3.36 | 2.60 | 4.79 | 1.68 | 1.00 | 1.00 | 1.00 | 4.66 | 7.44 | 1.94 |
| Gm14446 | 5.15 | 6.56 | 7.16 | 1.02 | 0.68 | 1.43 | 1.00 | 1.00 | 1.00 | 3.61 | 1.81 | 1.59 |
| Gm14461 | 1.25 | 1.00 | 1.00 | 1.00 | 1.00 | 1.00 | 1.00 | 1.00 | 1.00 | 1.00 | 1.00 | 1.00 |
| Gm15133 | 1.83 | 1.76 | 1.00 | 1.00 | 1.00 | 1.00 | 1.00 | 1.00 | 1.00 | 1.83 | 4.52 | 1.06 |
| Gm15284 | 2.13 | 2.06 | 1.00 | 1.00 | 1.00 | 1.00 | 1.00 | 1.00 | 1.00 | 1.00 | 1.00 | 1.38 |
| Gm15417 | 1.25 | 1.08 | 1.11 | 0.70 | 0.84 | 1.11 | 0.98 | 1.66 | 1.10 | 0.62 | 1.15 | 1.11 |
| Gm15421 | 1.19 | 1.52 | 1.12 | 0.94 | 1.27 | 0.77 | 1.03 | 0.75 | 1.07 | 0.96 | 1.78 | 0.94 |
| Gm15471 | 1.16 | 0.45 | 0.71 | 1.00 | 0.69 | 1.00 | 1.00 | 1.00 | 1.00 | 1.00 | 1.00 | 1.00 |
| Gm15772 | 1.27 | 1.60 | 1.04 | 0.91 | 0.68 | 0.94 | 0.71 | 1.92 | 1.08 | 1.02 | 1.54 | 1.14 |
| Gm15850 | 1.00 | 1.00 | 1.00 | 1.00 | 1.00 | 1.00 | 1.00 | 1.00 | 1.00 | 1.00 | 1.00 | 1.00 |
| Gm16062 | 1.36 | 1.64 | 1.00 | 1.35 | 1.11 | 0.74 | 0.88 | 1.20 | 0.68 | 1.52 | 1.58 | 1.31 |
| Gm16381 | 0.93 | 1.25 | 0.89 | 0.96 | 1.30 | 0.81 | 1.07 | 0.46 | 0.93 | 1.01 | 1.84 | 1.16 |

Fig. 35- 175

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Gatad2b | 1.01 | 0.97 | 0.58 | 1.89 | 0.36 | 0.53 | 1.59 | 1.00 | 1.00 | 0.75 | 0.38 | 1.23 |
| Gatsl3 | 0.87 | 1.39 | 1.32 | 0.87 | 1.51 | 0.88 | 0.59 | 2.25 | 0.92 | 1.08 | 1.92 | 0.96 |
| Gba | 0.89 | 1.04 | 0.91 | 0.88 | 1.32 | 0.87 | 0.68 | 2.66 | 0.66 | 0.89 | 0.99 | 0.91 |
| Gbp11 | 1.00 | 1.00 | 1.00 | 0.77 | 1.00 | 1.00 | 1.00 | 1.00 | 1.00 | 0.99 | 0.91 | 0.90 |
| Gcat | 1.19 | 0.94 | 1.29 | 1.12 | 2.97 | 1.15 | 1.00 | 2.47 | 0.73 | 1.00 | 1.62 | 1.01 |
| Gchfr | 1.10 | 1.00 | 1.19 | 0.63 | 2.51 | 1.35 | 0.78 | 2.99 | 1.06 | 1.94 | 2.03 | 1.51 |
| Gcn1l1 | 0.93 | 1.03 | 0.82 | 1.17 | 1.68 | 1.06 | 1.13 | 3.24 | 1.21 | 1.05 | 0.98 | 1.11 |
| Gdf1 | 1.03 | 1.00 | 1.79 | 0.70 | 1.00 | 1.48 | 1.00 | 1.74 | 1.00 | 0.71 | 4.82 | 1.00 |
| Gdf15 | 1.00 | 1.00 | 1.00 | 1.08 | 1.00 | 0.83 | 1.41 | 1.00 | 1.00 | 0.94 | 1.61 | 0.81 |
| Gdpd3 | 1.95 | 1.77 | 2.32 | 1.53 | 6.45 | 1.11 | 1.00 | 2.02 | 1.38 | 1.98 | 2.09 | 1.99 |
| Gdpd5 | 0.27 | 0.26 | 0.30 | 0.64 | 3.88 | 0.76 | 0.32 | 0.23 | 0.24 | 1.47 | 1.47 | 1.56 |
| Gemin7 | 0.96 | 0.98 | 1.01 | 0.85 | 2.67 | 0.92 | 0.76 | 1.86 | 1.18 | 1.02 | 1.05 | 0.95 |
| Gfer | 0.98 | 0.88 | 0.92 | 1.07 | 1.32 | 1.51 | 0.86 | 2.37 | 1.03 | 1.18 | 1.18 | 1.01 |
| Gfod2 | 1.13 | 0.97 | 1.14 | 0.77 | 1.54 | 1.10 | 0.95 | 1.06 | 1.00 | 0.79 | 1.04 | 0.99 |
| Ggct | 1.22 | 1.17 | 1.30 | 1.58 | 7.27 | 0.92 | 1.07 | 1.75 | 0.98 | 1.10 | 1.24 | 1.10 |
| Ggnbp1 | 0.74 | 1.39 | 1.26 | 1.70 | 4.59 | 1.51 | 1.01 | 2.73 | 1.06 | 1.06 | 0.91 | 0.65 |
| Ggt1 | 2.33 | 1.00 | 3.09 | 1.18 | 3.75 | 2.56 | 1.00 | 4.22 | 1.00 | 0.73 | 0.89 | 1.00 |
| Ggt5 | 1.50 | 1.51 | 1.55 | 0.98 | 1.73 | 0.97 | 1.00 | 1.76 | 1.00 | 0.90 | 0.85 | 0.95 |
| Gins4 | 0.84 | 0.95 | 0.97 | 0.61 | 2.01 | 0.57 | 1.01 | 1.19 | 1.20 | 0.84 | 0.88 | 0.70 |
| Gjb4 | 0.99 | 1.10 | 0.91 | 1.00 | 1.00 | 1.00 | 1.00 | 1.00 | 1.00 | 1.00 | 1.00 | 1.00 |
| Gk2 | 0.91 | 0.69 | 0.70 | 3.93 | 1.10 | 1.31 | 1.08 | 0.94 | 1.01 | 1.00 | 1.00 | 1.00 |
| Glb1 | 1.92 | 1.95 | 2.12 | 1.04 | 3.94 | 1.22 | 1.48 | 2.28 | 1.64 | 1.69 | 1.58 | 1.73 |
| Glmn | 0.72 | 0.81 | 0.86 | 0.96 | 1.54 | 1.17 | 0.92 | 2.66 | 0.94 | 1.12 | 0.95 | 1.04 |
| Glo1 | 1.11 | 1.04 | 1.37 | 2.97 | 11.51 | 2.97 | 1.03 | 1.49 | 1.08 | 1.15 | 1.05 | 1.22 |
| Glod5 | 1.45 | 1.20 | 1.37 | 1.00 | 1.00 | 1.00 | 1.00 | 1.00 | 1.00 | 1.00 | 1.00 | 1.00 |
| Glrb | 1.00 | 1.00 | 1.00 | 1.00 | 1.00 | 1.00 | 1.00 | 1.00 | 1.00 | 1.00 | 8.89 | 1.00 |
| Glrx3 | 0.90 | 0.88 | 1.05 | 1.23 | 4.50 | 1.68 | 0.92 | 1.79 | 1.00 | 1.09 | 1.18 | 0.84 |
| Glul | 1.60 | 2.11 | 1.62 | 0.99 | 2.76 | 1.58 | 0.93 | 1.16 | 0.95 | 1.41 | 1.81 | 1.23 |
| Gm10012 | 0.77 | 0.97 | 0.88 | 0.61 | 3.00 | 0.94 | 0.91 | 1.05 | 1.12 | 1.57 | 1.33 | 1.00 |
| Gm10094 | 1.12 | 1.08 | 1.16 | 0.85 | 2.45 | 1.05 | 0.96 | 1.41 | 0.98 | 0.76 | 1.01 | 0.75 |
| Gm10318 | 1.00 | 1.00 | 1.00 | 1.00 | 1.00 | 1.00 | 1.00 | 1.00 | 1.00 | 1.00 | 1.00 | 1.00 |
| Gm10334 | 1.26 | 1.20 | 10.80 | 1.00 | 1.00 | 1.00 | 1.00 | 1.00 | 1.00 | 1.00 | 1.00 | 1.00 |
| Gm10409 | 1.00 | 1.00 | 1.00 | 6.39 | 2.00 | 4.93 | 1.04 | 1.53 | 0.87 | 1.28 | 2.09 | 1.28 |
| Gm10451 | 1.42 | 0.96 | 1.32 | 1.64 | 1.00 | 0.52 | 1.51 | 1.00 | 2.66 | 1.35 | 0.94 | 5.46 |
| Gm10591 | 0.84 | 0.68 | 0.89 | 0.79 | 1.00 | 1.16 | 1.00 | 1.00 | 1.00 | 1.54 | 1.53 | 1.29 |
| Gm10638 | 0.94 | 1.00 | 1.15 | 1.54 | 3.85 | 0.91 | 0.77 | 1.14 | 1.05 | 1.00 | 1.00 | 1.00 |
| Gm10754 | 1.00 | 1.00 | 1.00 | 1.00 | 1.00 | 1.00 | 1.00 | 5.29 | 1.00 | 1.00 | 1.00 | 1.00 |
| Gm11517 | 1.00 | 1.00 | 1.00 | 1.33 | 0.51 | 1.98 | 1.00 | 1.20 | 0.95 | 1.24 | 1.41 | 1.64 |
| Gm11627 | 1.16 | 0.95 | 2.31 | 1.00 | 1.00 | 0.82 | 1.00 | 1.00 | 1.00 | 1.00 | 1.00 | 1.00 |
| Gm11974 | 0.83 | 1.18 | 0.82 | 1.29 | 0.41 | 2.02 | 1.58 | 6.11 | 0.90 | 1.52 | 1.42 | 1.14 |
| Gm12191 | 1.00 | 1.00 | 1.00 | 1.00 | 1.76 | 1.00 | 1.00 | 1.00 | 1.00 | 1.00 | 1.00 | 1.00 |
| Gm13139 | 0.65 | 0.63 | 0.99 | 1.24 | 1.00 | 0.76 | 1.75 | 1.23 | 0.95 | 1.29 | 1.25 | 1.54 |
| Gm13298 | 1.86 | 2.21 | 1.69 | 3.58 | 1.00 | 3.47 | 3.71 | 1.58 | 2.89 | 3.14 | 3.40 | 3.96 |
| Gm13305 | 5.68 | 6.92 | 5.07 | 7.89 | 123.88 | 7.41 | 1.00 | 7.60 | 1.00 | 9.14 | 12.07 | 7.07 |
| Gm13306 | 3.07 | 2.70 | 2.80 | 3.24 | 1.00 | 4.53 | 4.11 | 14.33 | 7.13 | 2.56 | 5.15 | 4.40 |
| Gm13308 | 1.00 | 1.00 | 1.10 | 0.99 | 1.00 | 2.06 | 12.59 | 35.16 | 5.33 | 1.00 | 1.50 | 1.59 |
| Gm13363 | 1.63 | 1.00 | 1.00 | 1.00 | 0.13 | 1.00 | 1.13 | 6.27 | 0.97 | 1.03 | 1.08 | 1.17 |
| Gm13547 | 1.00 | 1.00 | 1.00 | 1.00 | 1.00 | 1.00 | 0.77 | 5.64 | 0.91 | 1.00 | 1.00 | 1.00 |
| Gm13826 | 1.06 | 1.14 | 1.21 | 1.10 | 4.52 | 1.29 | 1.17 | 1.27 | 1.13 | 1.22 | 1.48 | 1.12 |
| Gm13889 | 1.34 | 1.75 | 1.44 | 1.36 | 2.86 | 1.60 | 0.95 | 0.29 | 1.02 | 0.77 | 0.77 | 0.62 |
| Gm14288 | 3.21 | 1.07 | 3.31 | 3.48 | 0.95 | 1.02 | 1.00 | 0.50 | 1.00 | 1.00 | 1.22 | 1.00 |
| Gm14378 | 0.81 | 1.79 | 1.10 | 0.91 | 1.36 | 1.67 | 0.72 | 2.20 | 1.06 | 0.93 | 0.98 | 1.13 |
| Gm14391 | 1.26 | 1.07 | 1.15 | 1.43 | 1.35 | 1.47 | 1.00 | 1.00 | 1.00 | 2.76 | 6.26 | 1.75 |
| Gm14446 | 28.27 | 51.52 | 13.96 | 1.00 | 1.00 | 0.79 | 1.00 | 1.00 | 1.00 | 3.82 | 2.03 | 2.66 |
| Gm14461 | 1.00 | 1.00 | 1.00 | 1.00 | 1.00 | 1.00 | 1.00 | 1.00 | 1.00 | 1.00 | 1.00 | 1.00 |
| Gm15133 | 1.00 | 1.00 | 1.00 | 1.00 | 1.00 | 1.00 | 1.00 | 1.00 | 1.00 | 4.99 | 6.11 | 1.61 |
| Gm15284 | 3.47 | 2.41 | 5.70 | 1.00 | 1.00 | 1.00 | 3.20 | 3.38 | 1.00 | 1.00 | 1.00 | 1.00 |
| Gm15417 | 1.23 | 1.06 | 1.23 | 0.46 | 1.04 | 0.97 | 1.00 | 3.83 | 1.57 | 0.93 | 0.95 | 1.79 |
| Gm15421 | 0.97 | 0.90 | 0.88 | 1.03 | 2.93 | 1.11 | 1.02 | 0.44 | 1.08 | 1.25 | 1.48 | 1.11 |
| Gm15471 | 1.00 | 1.00 | 1.00 | 1.00 | 1.00 | 1.00 | 1.00 | 1.00 | 1.00 | 1.00 | 1.19 | 1.00 |
| Gm15772 | 0.90 | 1.04 | 1.12 | 0.80 | 2.00 | 1.19 | 0.97 | 2.17 | 0.98 | 1.28 | 1.43 | 1.20 |
| Gm15850 | 1.00 | 1.00 | 1.00 | 1.00 | 1.00 | 1.00 | 0.92 | 8.11 | 1.42 | 1.00 | 1.00 | 1.00 |
| Gm16062 | 0.76 | 2.17 | 1.30 | 1.43 | 8.20 | 1.33 | 1.29 | 1.16 | 1.04 | 1.62 | 1.40 | 1.40 |
| Gm16381 | 0.97 | 1.01 | 0.89 | 0.96 | 12.57 | 1.16 | 0.95 | 0.40 | 1.01 | 1.06 | 1.33 | 1.07 |

Fig. 35- 176

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Gatad2b | 1.00 | 1.00 | 1.00 | 0.87 | 1.00 | 0.80 | 0.44 | 0.96 | 0.92 | 1.00 | 0.48 | 0.42 |
| Gatsl3 | 1.00 | 1.00 | 1.00 | 0.95 | 1.23 | 1.14 | 1.06 | 5.81 | 0.77 | 3.00 | 1.60 | 0.71 |
| Gba | 1.02 | 0.96 | 0.96 | 0.91 | 0.73 | 1.15 | 0.87 | 5.71 | 0.76 | 1.74 | 1.26 | 1.02 |
| Gbp11 | 1.00 | 1.00 | 1.00 | 1.00 | 1.00 | 1.00 | 1.00 | 1.00 | 1.00 | 1.00 | 1.00 | 1.00 |
| Gcat | 1.06 | 1.45 | 1.00 | 1.06 | 1.25 | 1.10 | 0.75 | 6.79 | 0.42 | 1.35 | 1.00 | 1.00 |
| Gchfr | 1.00 | 1.00 | 1.00 | 1.65 | 0.71 | 1.14 | 1.57 | 28.55 | 1.08 | 3.29 | 1.00 | 1.81 |
| Gcn1l1 | 1.50 | 1.32 | 1.75 | 1.03 | 1.02 | 1.04 | 1.08 | 6.57 | 1.02 | 2.10 | 0.72 | 0.61 |
| Gdf1 | 1.00 | 1.00 | 1.00 | 1.39 | 0.80 | 1.25 | 1.65 | 6.86 | 0.89 | 1.00 | 1.00 | 1.00 |
| Gdf15 | 1.00 | 1.00 | 1.00 | 1.00 | 1.00 | 1.00 | 1.00 | 1.00 | 1.00 | 1.02 | 1.87 | 1.38 |
| Gdpd3 | 1.78 | 1.00 | 1.25 | 2.71 | 9.55 | 1.90 | 2.19 | 9.83 | 2.32 | 5.16 | 2.06 | 2.40 |
| Gdpd5 | 0.16 | 0.12 | 0.13 | 0.35 | 0.13 | 0.44 | 2.67 | 7.76 | 1.96 | 8.02 | 4.00 | 3.85 |
| Gemin7 | 1.06 | 0.92 | 0.98 | 1.08 | 1.14 | 1.17 | 0.97 | 5.19 | 0.88 | 1.45 | 1.21 | 1.08 |
| Gfer | 1.11 | 1.41 | 1.14 | 0.85 | 1.05 | 0.94 | 1.10 | 3.24 | 1.13 | 1.65 | 0.80 | 0.96 |
| Gfod2 | 1.31 | 1.19 | 1.26 | 0.90 | 5.39 | 1.03 | 0.90 | 1.94 | 0.72 | 0.82 | 0.60 | 1.09 |
| Ggct | 0.90 | 0.81 | 1.00 | 1.20 | 0.75 | 0.97 | 0.60 | 4.01 | 0.45 | 1.63 | 1.73 | 1.27 |
| Ggnbp1 | 0.65 | 0.81 | 0.87 | 0.80 | 1.03 | 0.94 | 1.74 | 6.72 | 1.27 | 3.17 | 1.86 | 1.26 |
| Ggt1 | 0.84 | 0.97 | 1.07 | 1.00 | 1.70 | 1.00 | 1.00 | 4.05 | 1.00 | 1.84 | 1.00 | 1.00 |
| Ggt5 | 1.00 | 1.00 | 1.00 | 1.00 | 0.84 | 1.07 | 1.20 | 8.63 | 1.33 | 4.77 | 2.14 | 1.69 |
| Gins4 | 1.08 | 1.46 | 1.12 | 1.13 | 13.04 | 1.30 | 0.87 | 0.80 | 0.87 | 0.94 | 0.88 | 0.89 |
| Gjb4 | 1.00 | 1.00 | 1.00 | 1.00 | 1.00 | 1.00 | 1.06 | 5.06 | 0.74 | 1.00 | 1.00 | 1.00 |
| Gk2 | 1.00 | 1.00 | 1.00 | 1.00 | 1.00 | 1.00 | 6.03 | 1.00 | 1.00 | 1.00 | 1.00 | 1.00 |
| Glb1 | 1.28 | 1.46 | 1.13 | 1.46 | 2.78 | 1.48 | 1.60 | 4.70 | 1.54 | 3.02 | 1.66 | 2.03 |
| Glmn | 1.00 | 1.00 | 1.00 | 0.94 | 0.75 | 0.68 | 0.85 | 6.59 | 1.02 | 1.05 | 0.81 | 1.00 |
| Glo1 | 0.93 | 0.78 | 1.07 | 1.20 | 0.88 | 1.20 | 1.03 | 3.25 | 1.07 | 2.08 | 1.21 | 1.47 |
| Glod5 | 1.00 | 1.00 | 1.00 | 1.00 | 1.00 | 1.00 | 1.00 | 1.00 | 1.00 | 1.00 | 1.00 | 1.00 |
| Glrb | 1.00 | 1.00 | 1.00 | 1.04 | 2.57 | 1.00 | 1.01 | 1.00 | 1.03 | 1.00 | 1.00 | 1.00 |
| Glrx3 | 0.84 | 0.87 | 0.88 | 0.91 | 0.92 | 1.10 | 1.13 | 7.67 | 1.03 | 2.24 | 1.23 | 0.92 |
| Glul | 3.28 | 7.56 | 7.50 | 1.17 | 1.07 | 1.07 | 1.68 | 2.15 | 2.04 | 1.46 | 1.54 | 1.23 |
| Gm10012 | 0.89 | 1.94 | 0.82 | 1.10 | 1.31 | 1.24 | 0.95 | 7.91 | 0.87 | 2.76 | 0.84 | 0.97 |
| Gm10094 | 1.70 | 3.41 | 1.68 | 1.00 | 5.63 | 1.00 | 1.48 | 3.38 | 0.81 | 1.64 | 1.01 | 0.86 |
| Gm10318 | 1.00 | 1.00 | 1.00 | 1.00 | 1.00 | 1.00 | 6.21 | 0.81 | 0.93 | 1.00 | 1.00 | 1.00 |
| Gm10334 | 1.27 | 1.84 | 1.17 | 1.00 | 0.15 | 1.00 | 1.00 | 1.00 | 1.00 | 1.00 | 1.00 | 1.00 |
| Gm10409 | 1.00 | 1.00 | 1.00 | 1.32 | 2.17 | 1.90 | 1.00 | 1.00 | 1.00 | 1.00 | 1.00 | 1.00 |
| Gm10451 | 1.00 | 1.00 | 1.00 | 1.09 | 1.00 | 1.00 | 1.00 | 1.00 | 1.00 | 1.00 | 1.47 | 1.00 |
| Gm10591 | 1.00 | 1.00 | 0.89 | 1.00 | 1.00 | 1.00 | 7.77 | 0.17 | 1.15 | 1.00 | 1.00 | 1.00 |
| Gm10638 | 1.00 | 1.00 | 1.00 | 1.09 | 5.00 | 0.85 | 1.86 | 3.58 | 0.97 | 1.00 | 1.00 | 1.00 |
| Gm10754 | 1.00 | 1.00 | 1.00 | 1.00 | 1.00 | 1.00 | 1.00 | 1.00 | 1.00 | 1.00 | 1.00 | 1.00 |
| Gm11517 | 1.00 | 1.00 | 1.00 | 1.00 | 15.90 | 0.92 | 1.69 | 3.98 | 1.91 | 0.57 | 1.33 | 1.00 |
| Gm11627 | 1.00 | 1.00 | 1.00 | 2.49 | 7.67 | 1.13 | 1.00 | 1.00 | 1.00 | 1.00 | 1.00 | 1.00 |
| Gm11974 | 0.87 | 2.39 | 1.15 | 1.15 | 2.01 | 1.10 | 1.09 | 10.21 | 0.89 | 3.76 | 0.87 | 1.35 |
| Gm12191 | 1.00 | 1.00 | 1.00 | 1.00 | 0.41 | 1.00 | 1.00 | 14.11 | 1.00 | 1.00 | 1.00 | 1.00 |
| Gm13139 | 1.00 | 1.00 | 1.00 | 0.73 | 0.95 | 1.58 | 0.71 | 2.11 | 0.89 | 1.23 | 0.64 | 1.05 |
| Gm13298 | 1.00 | 1.00 | 1.00 | 5.06 | 1.00 | 6.11 | 5.04 | 1.22 | 8.07 | 1.00 | 1.00 | 1.00 |
| Gm13305 | 6.17 | 3.70 | 3.66 | 1.00 | 171.82 | 1.00 | 12.10 | 244.13 | 1.26 | 14.73 | 3.31 | 1.00 |
| Gm13306 | 1.00 | 1.00 | 1.00 | 4.87 | 9.05 | 5.98 | 8.12 | 116.40 | 13.45 | 1.38 | 2.24 | 1.06 |
| Gm13308 | 1.00 | 1.00 | 1.00 | 4.02 | 11.97 | 5.66 | 5.18 | 15.70 | 5.95 | 1.00 | 1.00 | 1.25 |
| Gm13363 | 1.00 | 1.00 | 1.00 | 0.27 | 1.00 | 0.94 | 0.18 | 0.33 | 1.00 | 1.00 | 0.52 | 0.98 |
| Gm13547 | 1.00 | 1.00 | 1.00 | 1.00 | 1.00 | 1.00 | 1.00 | 1.00 | 1.00 | 1.00 | 1.00 | 1.00 |
| Gm13826 | 0.86 | 0.99 | 0.92 | 1.20 | 1.26 | 1.06 | 1.21 | 3.95 | 0.90 | 2.02 | 1.17 | 1.14 |
| Gm13889 | 1.00 | 1.00 | 0.90 | 1.14 | 0.70 | 1.15 | 1.90 | 0.39 | 0.93 | 1.00 | 1.00 | 1.00 |
| Gm14288 | 1.00 | 0.85 | 1.00 | 1.48 | 2.58 | 1.47 | 1.06 | 6.82 | 1.37 | 2.14 | 1.49 | 1.00 |
| Gm14378 | 1.00 | 1.00 | 1.00 | 0.85 | 0.86 | 1.17 | 2.01 | 5.26 | 1.82 | 1.01 | 1.61 | 1.48 |
| Gm14391 | 1.00 | 1.00 | 1.00 | 0.47 | 1.00 | 1.37 | 5.48 | 9.03 | 4.08 | 1.64 | 1.82 | 1.00 |
| Gm14446 | 1.00 | 1.00 | 1.00 | 1.24 | 1.05 | 1.07 | 1.00 | 1.00 | 1.00 | 1.00 | 1.86 | 1.99 |
| Gm14461 | 1.00 | 1.00 | 1.00 | 1.00 | 1.00 | 1.00 | 1.00 | 1.00 | 1.00 | 1.00 | 1.00 | 1.00 |
| Gm15133 | 1.00 | 1.00 | 1.00 | 1.00 | 1.00 | 1.00 | 1.00 | 4.26 | 1.00 | 3.50 | 1.38 | 1.00 |
| Gm15284 | 1.00 | 1.00 | 1.00 | 1.00 | 1.00 | 1.00 | 1.00 | 1.00 | 1.00 | 1.00 | 1.00 | 1.00 |
| Gm15417 | 0.58 | 1.05 | 1.32 | 0.88 | 1.39 | 1.46 | 1.20 | 13.44 | 1.14 | 4.70 | 1.36 | 1.52 |
| Gm15421 | 0.78 | 1.28 | 0.98 | 1.21 | 1.34 | 1.06 | 0.95 | 1.73 | 0.87 | 1.40 | 1.15 | 1.10 |
| Gm15471 | 1.00 | 1.00 | 1.00 | 1.00 | 1.00 | 1.00 | 1.00 | 1.00 | 1.18 | 1.60 | 1.00 | 1.00 |
| Gm15772 | 0.93 | 1.07 | 1.08 | 1.10 | 0.89 | 1.11 | 1.77 | 6.66 | 0.81 | 1.82 | 1.20 | 1.01 |
| Gm15850 | 1.00 | 1.00 | 1.00 | 1.00 | 1.00 | 1.00 | 1.00 | 1.00 | 1.00 | 1.00 | 1.00 | 1.00 |
| Gm16062 | 0.51 | 1.41 | 2.81 | 1.62 | 40.74 | 0.98 | 0.97 | 5.04 | 1.06 | 2.60 | 1.27 | 1.10 |
| Gm16381 | 0.91 | 1.34 | 1.16 | 1.13 | 1.34 | 1.14 | 1.39 | 1.64 | 0.99 | 1.49 | 1.49 | 1.32 |

Fig. 35- 177

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Gm166 | 0.77 | 0.39 | 0.65 | 0.34 | 2.29 | 0.63 | 1.01 | 1.14 | 0.93 | 4.63 | 5.26 | 1.39 |
| Gm1673 | 1.00 | 0.97 | 1.00 | 1.00 | 3.70 | 1.00 | 1.00 | 1.00 | 0.64 | 1.85 | 6.10 | 0.76 |
| Gm16740 | 1.41 | 0.63 | 1.25 | 1.20 | 11.41 | 1.47 | 1.61 | 2.02 | 1.29 | 3.03 | 4.23 | 0.99 |
| Gm17757 | 1.00 | 1.00 | 1.00 | 1.00 | 1.00 | 1.00 | 1.00 | 1.44 | 1.15 | 1.00 | 1.00 | 1.68 |
| Gm1943 | 1.15 | 1.40 | 1.20 | 0.92 | 0.66 | 0.83 | 1.15 | 1.19 | 0.92 | 0.34 | 0.61 | 1.05 |
| Gm1966 | 1.00 | 1.00 | 1.00 | 1.00 | 1.00 | 1.00 | 1.00 | 1.00 | 1.00 | 1.00 | 1.00 | 1.00 |
| Gm2002 | 1.00 | 1.00 | 1.00 | 1.00 | 1.88 | 1.00 | 1.00 | 1.00 | 1.00 | 4.87 | 2.57 | 1.48 |
| Gm20604 | 2.40 | 1.00 | 0.90 | 0.62 | 0.19 | 1.17 | 1.87 | 5.33 | 1.28 | 1.00 | 0.83 | 1.06 |
| Gm2083 | 10.86 | 6.46 | 1.00 | 3.02 | 7.15 | 1.97 | 19.06 | 0.35 | 2.01 | 0.05 | 1.83 | 2.16 |
| Gm20878 | 1.00 | 1.53 | 1.00 | 1.00 | 7.44 | 1.00 | 1.00 | 1.00 | 1.00 | 18.37 | 15.93 | 1.00 |
| Gm21586 | 1.00 | 1.00 | 1.00 | 1.00 | 3.31 | 1.00 | 1.00 | 1.07 | 1.00 | 6.33 | 4.75 | 1.00 |
| Gm2663 | 1.00 | 1.00 | 1.00 | 1.00 | 1.00 | 1.00 | 1.00 | 1.00 | 1.00 | 1.00 | 1.00 | 1.00 |
| Gm2696 | 1.00 | 1.00 | 1.00 | 1.00 | 1.00 | 1.00 | 1.00 | 1.00 | 1.00 | 1.00 | 1.00 | 1.00 |
| Gm2897 | 1.00 | 1.00 | 1.00 | 1.00 | 1.00 | 1.00 | 1.26 | 1.61 | 1.03 | 1.00 | 1.00 | 1.00 |
| Gm2913 | 1.00 | 1.00 | 1.00 | 1.00 | 1.00 | 1.00 | 1.00 | 1.00 | 1.00 | 1.00 | 1.00 | 1.00 |
| Gm3219 | 1.29 | 0.49 | 1.02 | 1.18 | 12.67 | 1.06 | 0.72 | 0.65 | 0.94 | 2.15 | 3.34 | 0.84 |
| Gm3417 | 1.00 | 1.00 | 1.00 | 1.41 | 6.18 | 3.14 | 1.00 | 1.00 | 1.00 | 3.19 | 2.27 | 2.35 |
| Gm3500 | 1.00 | 1.00 | 1.00 | 1.00 | 1.00 | 1.00 | 1.33 | 1.67 | 1.08 | 1.00 | 1.00 | 0.87 |
| Gm3696 | 1.00 | 1.00 | 1.00 | 1.00 | 1.00 | 1.00 | 1.47 | 1.31 | 1.00 | 1.00 | 1.00 | 1.00 |
| Gm3893 | 1.00 | 1.00 | 1.00 | 1.00 | 1.00 | 1.00 | 1.00 | 1.00 | 1.00 | 2.28 | 1.82 | 2.53 |
| Gm4013 | 1.13 | 0.37 | 1.06 | 0.57 | 5.30 | 0.44 | 1.13 | 0.65 | 0.92 | 0.99 | 1.41 | 1.40 |
| Gm4070 | 1.00 | 1.00 | 1.00 | 2.21 | 1.00 | 1.63 | 1.67 | 1.93 | 2.34 | 1.92 | 1.40 | 1.90 |
| Gm4951 | 1.00 | 1.00 | 1.00 | 1.00 | 1.00 | 1.00 | 1.00 | 1.00 | 1.00 | 1.00 | 1.00 | 2.25 |
| Gm5 | 1.00 | 1.00 | 1.00 | 1.00 | 1.00 | 1.00 | 1.00 | 1.00 | 1.00 | 1.00 | 1.00 | 1.00 |
| Gm525 | 1.00 | 1.00 | 1.00 | 1.00 | 1.09 | 1.00 | 1.00 | 1.00 | 1.00 | 1.00 | 1.00 | 1.00 |
| Gm5441 | 1.00 | 1.00 | 1.00 | 1.00 | 1.00 | 1.00 | 1.00 | 1.00 | 1.00 | 1.00 | 1.00 | 1.00 |
| Gm5483 | 1.00 | 1.00 | 1.00 | 1.00 | 1.00 | 1.00 | 1.00 | 1.00 | 1.00 | 5.88 | 2.08 | 1.00 |
| Gm5512 | 1.54 | 1.28 | 1.59 | 0.81 | 1.67 | 0.79 | 2.33 | 2.63 | 1.86 | 1.46 | 1.61 | 1.09 |
| Gm561 | 0.99 | 0.78 | 0.99 | 0.73 | 2.80 | 1.20 | 0.89 | 0.97 | 0.85 | 0.49 | 1.78 | 1.15 |
| Gm5617 | 1.39 | 0.80 | 1.11 | 0.39 | 7.65 | 1.26 | 1.23 | 0.77 | 0.89 | 1.63 | 3.25 | 0.95 |
| Gm5627 | 1.00 | 1.00 | 1.00 | 2.61 | 1.20 | 14.84 | 1.00 | 1.00 | 1.00 | 1.00 | 1.00 | 1.00 |
| Gm5741 | 1.00 | 1.00 | 1.00 | 1.00 | 1.00 | 1.00 | 1.00 | 0.94 | 1.00 | 1.00 | 2.16 | 1.00 |
| Gm5771 | 1.00 | 1.00 | 1.00 | 1.00 | 1.00 | 1.00 | 1.00 | 1.00 | 1.00 | 1.00 | 1.00 | 1.00 |
| Gm6251 | 1.32 | 0.92 | 1.01 | 0.78 | 5.55 | 1.11 | 0.83 | 0.80 | 0.89 | 1.54 | 2.20 | 0.89 |
| Gm6537 | 1.00 | 1.00 | 1.00 | 1.00 | 1.00 | 1.00 | 1.00 | 1.00 | 1.00 | 1.00 | 1.00 | 1.00 |
| Gm6568 | 1.64 | 2.10 | 1.40 | 5.63 | 0.03 | 1.23 | 1.22 | 1.97 | 1.16 | 1.00 | 0.50 | 1.16 |
| Gm6607 | 1.00 | 0.83 | 1.00 | 1.00 | 4.90 | 1.00 | 1.00 | 1.00 | 1.00 | 1.67 | 3.73 | 1.00 |
| Gm6644 | 0.94 | 0.40 | 0.36 | 0.21 | 3.50 | 0.35 | 0.61 | 0.64 | 0.55 | 2.08 | 4.46 | 1.18 |
| Gm6654 | 1.40 | 0.63 | 1.12 | 0.35 | 6.21 | 1.11 | 1.15 | 0.80 | 0.81 | 1.80 | 2.62 | 0.99 |
| Gm694 | 1.00 | 1.12 | 1.31 | 0.86 | 2.38 | 0.94 | 0.62 | 0.63 | 1.34 | 1.00 | 1.00 | 1.00 |
| Gm7325 | 3.79 | 13.89 | 2.35 | 1.00 | 1.00 | 1.00 | 1.00 | 1.00 | 1.00 | 1.00 | 1.00 | 1.00 |
| Gm7334 | 3.43 | 1.00 | 1.68 | 46.25 | 23.86 | 2.60 | 8.25 | 0.49 | 0.95 | 0.32 | 0.71 | 1.24 |
| Gm7367 | 1.17 | 1.76 | 0.81 | 2.08 | 1.31 | 0.89 | 1.32 | 1.56 | 1.15 | 0.02 | 1.11 | 0.88 |
| Gm766 | 1.00 | 1.00 | 1.00 | 1.00 | 1.00 | 1.00 | 1.00 | 1.00 | 1.00 | 1.00 | 1.00 | 1.00 |
| Gm8909 | 2.34 | 1.00 | 3.19 | 1.25 | 0.30 | 0.92 | 2.48 | 1.94 | 3.00 | 0.58 | 0.45 | 2.43 |
| Gm8979 | 1.00 | 1.00 | 1.00 | 1.00 | 1.00 | 1.00 | 1.00 | 1.58 | 1.03 | 1.00 | 1.00 | 2.35 |
| Gm8989 | 1.41 | 1.00 | 1.07 | 3.95 | 1.00 | 3.68 | 5.05 | 4.80 | 4.60 | 1.00 | 1.00 | 12.41 |
| Gmds | 1.00 | 0.88 | 1.00 | 1.07 | 6.42 | 1.41 | 0.82 | 0.94 | 0.90 | 2.65 | 3.91 | 1.00 |
| Gmfg | 1.00 | 0.95 | 1.00 | 1.00 | 1.73 | 1.00 | 1.00 | 1.00 | 1.00 | 5.15 | 6.68 | 0.71 |
| Gmppa | 0.95 | 0.46 | 0.72 | 0.46 | 7.04 | 1.08 | 1.00 | 0.85 | 0.97 | 2.40 | 3.72 | 1.08 |
| Gmppb | 0.67 | 0.36 | 0.80 | 0.21 | 5.33 | 0.66 | 0.84 | 0.39 | 0.77 | 1.72 | 3.10 | 0.87 |
| Gmpr | 0.57 | 0.38 | 0.48 | 0.85 | 9.29 | 1.55 | 0.69 | 0.55 | 0.62 | 1.49 | 2.65 | 0.93 |
| Gnao1 | 1.93 | 1.92 | 1.46 | 0.64 | 0.20 | 0.72 | 1.39 | 1.60 | 1.57 | 0.92 | 0.76 | 1.12 |
| Gng3 | 1.00 | 1.00 | 1.00 | 0.91 | 0.26 | 0.65 | 1.00 | 1.00 | 1.00 | 1.00 | 1.00 | 1.00 |
| Gng7 | 1.00 | 1.00 | 1.00 | 0.66 | 0.12 | 0.47 | 1.00 | 0.87 | 0.78 | 0.83 | 0.64 | 0.78 |
| Gngt2 | 3.30 | 0.93 | 2.37 | 0.31 | 11.75 | 1.00 | 1.23 | 0.94 | 1.20 | 2.78 | 4.54 | 1.20 |
| Gnl1 | 0.95 | 0.64 | 0.85 | 0.47 | 5.08 | 1.01 | 0.93 | 0.76 | 0.94 | 3.11 | 3.10 | 0.97 |
| Gnmt | 2.16 | 1.18 | 1.13 | 0.52 | 23.15 | 2.17 | 0.78 | 0.62 | 0.66 | 3.88 | 6.18 | 1.75 |
| Gnpnat1 | 0.85 | 0.72 | 0.82 | 3.23 | 2.35 | 1.12 | 0.77 | 0.81 | 0.79 | 1.07 | 0.87 | 0.96 |
| Gnrh1 | 1.00 | 1.25 | 1.00 | 1.00 | 1.70 | 1.00 | 0.72 | 1.00 | 1.00 | 2.22 | 1.45 | 2.17 |
| Gon4l | 0.87 | 0.62 | 1.05 | 1.36 | 3.25 | 1.02 | 0.86 | 1.03 | 1.44 | 3.06 | 2.83 | 1.11 |
| Got1 | 2.17 | 2.29 | 1.54 | 0.56 | 0.70 | 1.31 | 1.22 | 1.34 | 1.06 | 1.23 | 1.32 | 1.19 |
| Gp1bb | 1.05 | 0.62 | 1.00 | 1.00 | 2.52 | 1.00 | 1.64 | 1.45 | 1.06 | 2.65 | 3.76 | 1.13 |
| Gp2 | 1.00 | 1.00 | 1.00 | 1.00 | 1.00 | 1.00 | 1.00 | 1.00 | 1.00 | 1.00 | 1.38 | 1.00 |

Fig. 35- 178

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Gm166 | 1.28 | 1.42 | 0.85 | 0.79 | 0.55 | 0.95 | 0.77 | 0.41 | 0.73 | 1.12 | 1.34 | 1.05 |
| Gm1673 | 1.68 | 3.92 | 1.73 | 1.00 | 0.73 | 1.00 | 1.00 | 4.10 | 1.00 | 1.00 | 1.46 | 1.00 |
| Gm16740 | 1.51 | 2.86 | 1.01 | 1.15 | 0.59 | 1.05 | 1.41 | 4.07 | 1.16 | 1.05 | 1.37 | 0.74 |
| Gm17757 | 2.73 | 6.54 | 2.99 | 1.00 | 1.00 | 1.00 | 1.00 | 1.00 | 1.00 | 1.00 | 1.00 | 1.00 |
| Gm1943 | 0.82 | 0.94 | 0.92 | 1.11 | 0.94 | 0.91 | 0.81 | 0.49 | 0.99 | 0.92 | 0.88 | 1.03 |
| Gm1966 | 1.00 | 1.00 | 1.00 | 1.00 | 1.00 | 1.00 | 1.00 | 1.00 | 1.00 | 1.00 | 1.00 | 1.00 |
| Gm2002 | 2.51 | 2.90 | 2.04 | 1.00 | 2.19 | 1.00 | 1.00 | 2.72 | 1.00 | 1.00 | 1.00 | 1.00 |
| Gm20604 | 0.94 | 0.92 | 0.72 | 1.34 | 1.00 | 1.12 | 0.76 | 1.00 | 0.85 | 0.77 | 0.44 | 0.99 |
| Gm2083 | 19.46 | 1.61 | 2.85 | 1.42 | 0.40 | 0.86 | 3.72 | 3.04 | 2.77 | 5.40 | 1.35 | 3.06 |
| Gm20878 | 1.00 | 1.00 | 1.00 | 0.98 | 0.55 | 1.00 | 1.00 | 2.48 | 1.00 | 1.00 | 1.00 | 1.00 |
| Gm21586 | 1.00 | 1.00 | 1.00 | 1.00 | 0.43 | 1.00 | 1.00 | 1.25 | 1.00 | 1.00 | 1.00 | 1.00 |
| Gm2663 | 1.00 | 1.00 | 1.00 | 1.00 | 1.00 | 1.00 | 1.00 | 1.00 | 1.00 | 1.00 | 4.18 | 1.00 |
| Gm2696 | 1.00 | 1.00 | 1.00 | 1.00 | 1.00 | 1.00 | 1.00 | 1.00 | 1.00 | 1.00 | 1.00 | 1.00 |
| Gm2897 | 3.08 | 3.50 | 3.61 | 1.00 | 1.00 | 1.00 | 1.00 | 1.00 | 1.00 | 1.44 | 1.61 | 1.39 |
| Gm2913 | 1.00 | 1.00 | 1.00 | 1.00 | 1.00 | 1.00 | 1.00 | 1.00 | 1.00 | 1.00 | 1.00 | 1.00 |
| Gm3219 | 1.19 | 1.58 | 0.88 | 1.62 | 0.95 | 0.75 | 0.64 | 1.17 | 0.71 | 0.81 | 1.60 | 0.84 |
| Gm3417 | 1.30 | 1.00 | 1.00 | 0.69 | 0.60 | 1.51 | 1.20 | 1.00 | 1.00 | 1.24 | 1.39 | 2.06 |
| Gm3500 | 4.95 | 2.72 | 2.97 | 1.00 | 1.00 | 1.00 | 1.00 | 1.00 | 1.00 | 2.39 | 2.47 | 1.43 |
| Gm3696 | 2.74 | 3.72 | 3.03 | 1.00 | 1.00 | 1.00 | 1.00 | 1.00 | 1.00 | 1.15 | 1.23 | 1.47 |
| Gm3893 | 1.47 | 1.15 | 1.29 | 1.34 | 1.00 | 1.03 | 1.29 | 1.00 | 1.43 | 1.00 | 1.00 | 1.00 |
| Gm4013 | 1.68 | 1.51 | 0.53 | 0.65 | 1.14 | 0.70 | 0.67 | 0.37 | 0.54 | 1.09 | 1.35 | 0.95 |
| Gm4070 | 9.97 | 5.20 | 7.45 | 1.29 | 1.00 | 1.70 | 1.00 | 1.00 | 1.00 | 4.30 | 3.40 | 4.42 |
| Gm4951 | 2.52 | 1.18 | 3.62 | 1.00 | 1.00 | 1.00 | 6.97 | 1.00 | 7.90 | 1.00 | 1.00 | 1.00 |
| Gm5 | 1.00 | 1.00 | 1.00 | 1.00 | 1.00 | 1.00 | 1.00 | 1.00 | 1.00 | 1.00 | 1.00 | 1.00 |
| Gm525 | 1.88 | 2.18 | 0.96 | 1.00 | 1.00 | 1.00 | 1.00 | 1.00 | 1.00 | 1.00 | 1.00 | 1.00 |
| Gm5441 | 9.43 | 5.66 | 1.71 | 1.00 | 1.00 | 1.00 | 1.00 | 1.00 | 1.00 | 1.00 | 1.00 | 1.00 |
| Gm5483 | 1.00 | 1.00 | 1.00 | 1.00 | 1.00 | 1.00 | 1.00 | 1.00 | 1.00 | 1.00 | 1.00 | 1.00 |
| Gm5512 | 1.23 | 1.19 | 1.15 | 1.16 | 1.12 | 1.01 | 1.07 | 1.27 | 0.88 | 0.79 | 1.03 | 0.70 |
| Gm561 | 1.11 | 1.06 | 0.86 | 0.87 | 1.09 | 0.75 | 0.92 | 0.64 | 1.08 | 0.95 | 1.92 | 1.03 |
| Gm5617 | 1.23 | 1.93 | 1.34 | 0.68 | 0.58 | 0.89 | 0.65 | 1.06 | 0.84 | 0.87 | 1.58 | 0.92 |
| Gm5627 | 1.00 | 1.00 | 1.00 | 1.00 | 1.00 | 1.00 | 1.00 | 1.00 | 1.00 | 1.00 | 1.00 | 1.00 |
| Gm5741 | 1.00 | 1.80 | 1.00 | 0.78 | 1.46 | 1.00 | 0.97 | 0.61 | 1.54 | 1.00 | 0.77 | 1.03 |
| Gm5771 | 1.00 | 1.00 | 1.00 | 1.00 | 1.00 | 1.00 | 1.00 | 1.00 | 1.00 | 0.61 | 1.05 | 1.78 |
| Gm6251 | 1.16 | 1.46 | 0.99 | 0.92 | 0.82 | 0.75 | 0.90 | 1.41 | 0.92 | 0.92 | 1.57 | 1.06 |
| Gm6537 | 1.00 | 1.00 | 1.00 | 1.00 | 1.00 | 1.00 | 1.00 | 1.00 | 1.00 | 1.00 | 1.00 | 1.00 |
| Gm6568 | 0.86 | 0.90 | 1.03 | 1.09 | 1.00 | 1.24 | 1.04 | 1.00 | 0.99 | 1.11 | 0.44 | 1.15 |
| Gm6607 | 2.30 | 1.44 | 1.13 | 1.00 | 0.79 | 1.00 | 1.00 | 1.13 | 1.00 | 0.99 | 1.88 | 1.00 |
| Gm6644 | 0.77 | 1.00 | 0.64 | 0.37 | 0.65 | 0.78 | 1.61 | 5.04 | 2.48 | 0.76 | 1.10 | 0.31 |
| Gm6654 | 1.03 | 1.53 | 1.11 | 0.62 | 0.55 | 0.90 | 0.94 | 1.56 | 1.13 | 1.04 | 1.81 | 0.98 |
| Gm694 | 1.00 | 1.00 | 1.00 | 1.00 | 1.00 | 1.00 | 1.00 | 1.00 | 1.00 | 1.00 | 1.00 | 1.00 |
| Gm7325 | 1.24 | 1.19 | 1.00 | 0.66 | 0.36 | 0.44 | 1.00 | 1.00 | 1.00 | 1.00 | 1.00 | 1.00 |
| Gm7334 | 5.27 | 1.30 | 1.14 | 1.34 | 1.03 | 3.71 | 1.00 | 1.00 | 1.00 | 0.49 | 1.04 | 3.67 |
| Gm7367 | 0.85 | 1.09 | 0.82 | 1.44 | 74.49 | 1.30 | 1.49 | 0.26 | 0.69 | 1.53 | 1.80 | 1.47 |
| Gm766 | 1.00 | 1.00 | 1.00 | 1.00 | 1.00 | 1.00 | 1.00 | 1.00 | 1.00 | 1.00 | 1.00 | 1.00 |
| Gm8909 | 0.84 | 0.68 | 0.49 | 2.11 | 1.00 | 2.30 | 2.64 | 1.00 | 3.48 | 0.90 | 0.77 | 0.66 |
| Gm8979 | 3.23 | 1.71 | 6.44 | 1.00 | 1.00 | 1.00 | 1.00 | 1.00 | 1.00 | 5.57 | 0.92 | 5.43 |
| Gm8989 | 23.17 | 23.79 | 24.24 | 2.04 | 1.00 | 2.70 | 1.00 | 1.00 | 1.00 | 5.60 | 5.84 | 5.64 |
| Gmds | 0.98 | 1.10 | 0.81 | 0.74 | 0.59 | 1.01 | 1.00 | 1.00 | 1.00 | 1.04 | 1.69 | 1.13 |
| Gmfg | 1.11 | 1.06 | 0.91 | 1.00 | 0.39 | 1.00 | 1.00 | 6.73 | 1.00 | 1.00 | 2.85 | 0.91 |
| Gmppa | 1.28 | 1.54 | 1.62 | 0.93 | 0.60 | 0.97 | 0.96 | 2.29 | 0.93 | 0.99 | 1.41 | 1.03 |
| Gmppb | 1.02 | 1.50 | 0.93 | 0.93 | 0.70 | 0.95 | 0.70 | 1.53 | 0.79 | 0.78 | 1.25 | 0.83 |
| Gmpr | 0.91 | 1.21 | 0.89 | 0.71 | 0.62 | 0.71 | 1.00 | 0.73 | 1.00 | 0.64 | 1.00 | 0.56 |
| Gnao1 | 1.00 | 1.00 | 0.74 | 1.32 | 1.00 | 1.16 | 1.00 | 1.06 | 1.00 | 1.12 | 0.95 | 1.12 |
| Gng3 | 1.00 | 1.00 | 1.00 | 1.00 | 1.00 | 1.00 | 1.00 | 1.00 | 1.00 | 1.02 | 1.27 | 1.04 |
| Gng7 | 0.84 | 0.98 | 1.11 | 1.00 | 1.00 | 1.00 | 1.00 | 1.00 | 1.00 | 0.78 | 0.93 | 0.84 |
| Gngt2 | 1.17 | 1.23 | 1.28 | 1.94 | 0.64 | 1.22 | 1.26 | 3.15 | 2.38 | 0.63 | 1.50 | 1.07 |
| Gnl1 | 1.13 | 1.35 | 1.06 | 0.98 | 0.61 | 0.93 | 1.38 | 3.39 | 1.07 | 0.90 | 1.43 | 0.92 |
| Gnmt | 2.61 | 1.74 | 0.80 | 1.17 | 0.79 | 1.01 | 0.94 | 3.06 | 1.02 | 0.63 | 2.02 | 1.00 |
| Gnpnat1 | 1.15 | 1.10 | 1.02 | 1.19 | 1.14 | 1.14 | 1.31 | 1.21 | 1.19 | 1.06 | 1.16 | 1.04 |
| Gnrh1 | 0.58 | 1.68 | 2.14 | 1.00 | 0.84 | 1.00 | 1.00 | 1.00 | 1.00 | 1.00 | 2.49 | 1.00 |
| Gon4l | 0.81 | 0.77 | 0.87 | 1.20 | 0.57 | 1.04 | 1.05 | 2.02 | 1.21 | 0.90 | 0.98 | 0.91 |
| Got1 | 1.08 | 1.21 | 1.16 | 1.24 | 1.91 | 0.95 | 4.96 | 10.30 | 4.95 | 1.05 | 1.18 | 1.07 |
| Gp1bb | 1.00 | 1.00 | 1.00 | 1.00 | 0.43 | 1.00 | 1.00 | 1.65 | 1.00 | 1.12 | 1.59 | 1.13 |
| Gp2 | 2.77 | 1.70 | 1.52 | 0.93 | 0.61 | 0.84 | 1.00 | 1.00 | 1.00 | 0.40 | 1.98 | 10.05 |

Fig. 35- 179

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Gm166 | 1.52 | 1.36 | 0.79 | 1.15 | 3.86 | 1.07 | 0.91 | 4.86 | 1.10 | 1.09 | 1.20 | 1.10 |
| Gm1673 | 1.00 | 1.00 | 1.00 | 0.55 | 3.84 | 1.60 | 0.89 | 3.29 | 0.91 | 1.00 | 1.40 | 1.00 |
| Gm16740 | 1.53 | 0.79 | 2.07 | 1.06 | 9.84 | 1.68 | 1.03 | 2.41 | 1.59 | 1.43 | 1.44 | 1.26 |
| Gm17757 | 1.00 | 1.00 | 1.00 | 1.17 | 1.00 | 1.00 | 1.00 | 1.00 | 1.00 | 2.70 | 1.88 | 2.13 |
| Gm1943 | 0.95 | 1.15 | 1.06 | 1.19 | 1.74 | 1.16 | 0.93 | 1.24 | 1.13 | 1.01 | 0.97 | 0.98 |
| Gm1966 | 1.00 | 1.00 | 1.00 | 1.00 | 1.00 | 1.00 | 1.00 | 1.00 | 1.00 | 4.18 | 2.13 | 6.56 |
| Gm2002 | 1.00 | 1.00 | 1.00 | 1.00 | 1.17 | 1.19 | 1.81 | 18.73 | 2.59 | 1.00 | 1.00 | 1.00 |
| Gm20604 | 1.46 | 1.22 | 0.91 | 1.23 | 1.00 | 1.19 | 1.00 | 0.39 | 1.23 | 0.76 | 0.64 | 1.06 |
| Gm2083 | 4.42 | 12.43 | 9.78 | 0.91 | 2.48 | 0.73 | 0.60 | 3.64 | 0.82 | 1.00 | 18.73 | 1.32 |
| Gm20878 | 1.00 | 1.00 | 1.00 | 1.00 | 7.60 | 1.00 | 0.13 | 12.88 | 0.50 | 1.00 | 1.00 | 1.00 |
| Gm21586 | 1.00 | 1.00 | 1.00 | 1.00 | 2.79 | 1.00 | 1.00 | 11.38 | 0.65 | 1.00 | 1.00 | 1.00 |
| Gm2663 | 1.00 | 1.38 | 2.08 | 1.00 | 1.00 | 1.00 | 1.00 | 1.00 | 1.00 | 1.00 | 4.92 | 1.00 |
| Gm2696 | 1.00 | 1.00 | 1.00 | 1.00 | 1.00 | 1.00 | 1.00 | 1.00 | 1.00 | 1.00 | 1.00 | 1.00 |
| Gm2897 | 1.00 | 1.00 | 1.00 | 6.43 | 1.37 | 4.96 | 1.72 | 3.61 | 1.73 | 2.58 | 2.60 | 2.91 |
| Gm2913 | 1.00 | 1.00 | 1.00 | 1.00 | 1.00 | 1.00 | 1.00 | 15.31 | 13.28 | 1.00 | 1.00 | 1.00 |
| Gm3219 | 1.09 | 1.11 | 1.14 | 0.87 | 4.37 | 1.00 | 0.91 | 1.93 | 1.00 | 1.17 | 1.32 | 1.07 |
| Gm3417 | 1.07 | 1.00 | 1.00 | 4.14 | 2.78 | 1.88 | 1.30 | 1.54 | 1.47 | 2.03 | 1.50 | 1.88 |
| Gm3500 | 1.00 | 1.00 | 1.00 | 4.66 | 2.17 | 5.88 | 1.97 | 3.61 | 1.46 | 2.10 | 1.14 | 2.46 |
| Gm3696 | 1.00 | 1.00 | 1.00 | 6.22 | 1.00 | 3.70 | 3.74 | 6.05 | 3.15 | 1.98 | 2.24 | 2.62 |
| Gm3893 | 1.00 | 1.00 | 1.00 | 1.00 | 1.00 | 1.00 | 3.46 | 4.29 | 3.08 | 3.09 | 2.32 | 4.29 |
| Gm4013 | 0.75 | 1.32 | 0.95 | 0.76 | 0.25 | 0.88 | 1.00 | 1.02 | 0.93 | 0.63 | 0.87 | 1.64 |
| Gm4070 | 1.03 | 1.00 | 1.00 | 0.96 | 0.54 | 1.13 | 1.00 | 1.00 | 1.00 | 2.48 | 0.96 | 1.96 |
| Gm4951 | 1.07 | 1.83 | 1.00 | 1.00 | 1.00 | 1.46 | 1.00 | 1.00 | 1.00 | 3.81 | 1.78 | 3.35 |
| Gm5 | 1.00 | 1.00 | 1.00 | 1.00 | 1.00 | 1.00 | 1.00 | 1.00 | 1.00 | 1.00 | 1.00 | 1.00 |
| Gm525 | 1.00 | 1.00 | 1.00 | 1.00 | 0.70 | 1.00 | 2.01 | 2.53 | 1.14 | 1.00 | 1.00 | 1.00 |
| Gm5441 | 1.00 | 1.00 | 1.00 | 1.00 | 1.00 | 1.00 | 1.00 | 1.00 | 1.00 | 1.00 | 1.00 | 1.00 |
| Gm5483 | 1.00 | 1.00 | 1.00 | 1.00 | 1.00 | 1.00 | 1.00 | 1.00 | 1.00 | 1.00 | 1.00 | 1.00 |
| Gm5512 | 0.98 | 1.01 | 1.08 | 0.72 | 6.43 | 0.93 | 1.18 | 1.25 | 1.16 | 1.24 | 1.46 | 1.13 |
| Gm561 | 1.38 | 1.05 | 0.88 | 0.68 | 12.91 | 1.07 | 0.78 | 0.55 | 0.58 | 1.16 | 1.22 | 1.21 |
| Gm5617 | 1.10 | 1.57 | 1.08 | 0.86 | 3.33 | 1.08 | 0.91 | 1.64 | 1.00 | 1.03 | 1.37 | 1.04 |
| Gm5627 | 1.00 | 1.00 | 1.00 | 1.92 | 1.00 | 1.18 | 0.33 | 1.17 | 0.59 | 1.00 | 1.00 | 1.00 |
| Gm5741 | 1.00 | 1.00 | 1.00 | 1.00 | 1.00 | 1.00 | 1.00 | 1.80 | 1.00 | 1.00 | 1.00 | 0.59 |
| Gm5771 | 1.02 | 1.00 | 5.45 | 1.00 | 1.00 | 1.00 | 1.00 | 1.00 | 1.00 | 1.00 | 1.00 | 1.00 |
| Gm6251 | 0.89 | 0.94 | 0.98 | 1.02 | 3.81 | 1.14 | 0.85 | 1.70 | 0.88 | 1.36 | 1.56 | 1.19 |
| Gm6537 | 1.00 | 1.00 | 1.00 | 1.00 | 1.00 | 1.00 | 1.00 | 1.00 | 1.00 | 1.00 | 1.00 | 1.00 |
| Gm6568 | 0.98 | 1.03 | 0.86 | 1.44 | 1.00 | 1.19 | 0.90 | 0.22 | 1.05 | 0.88 | 0.79 | 1.02 |
| Gm6607 | 1.00 | 1.15 | 1.00 | 0.86 | 1.00 | 1.00 | 1.38 | 0.62 | 1.69 | 1.74 | 1.76 | 0.82 |
| Gm6644 | 0.42 | 1.02 | 0.34 | 2.99 | 5.44 | 0.85 | 0.44 | 0.84 | 0.34 | 0.56 | 0.20 | 0.13 |
| Gm6654 | 0.97 | 1.10 | 1.03 | 0.90 | 1.69 | 1.07 | 0.75 | 2.09 | 1.17 | 1.42 | 1.42 | 1.13 |
| Gm694 | 1.00 | 1.00 | 1.00 | 0.83 | 1.00 | 1.00 | 1.00 | 1.00 | 1.00 | 1.00 | 1.00 | 1.00 |
| Gm7325 | 1.00 | 1.00 | 1.00 | 1.00 | 1.00 | 1.00 | 0.54 | 0.59 | 0.62 | 1.00 | 1.00 | 1.00 |
| Gm7334 | 3.36 | 1.04 | 1.33 | 4.50 | 1.00 | 7.42 | 0.90 | 0.77 | 1.40 | 1.09 | 1.48 | 1.96 |
| Gm7367 | 1.92 | 1.89 | 1.23 | 1.43 | 1.00 | 1.30 | 1.08 | 0.03 | 0.70 | 0.99 | 1.23 | 1.04 |
| Gm766 | 5.60 | 1.61 | 6.17 | 1.00 | 1.00 | 1.00 | 1.00 | 1.00 | 1.00 | 1.00 | 1.00 | 1.00 |
| Gm8909 | 3.83 | 5.06 | 2.52 | 3.94 | 1.00 | 2.20 | 1.03 | 1.00 | 1.00 | 2.37 | 2.02 | 1.68 |
| Gm8979 | 1.22 | 1.00 | 1.00 | 1.00 | 1.00 | 1.00 | 1.00 | 1.00 | 1.00 | 3.47 | 0.81 | 3.23 |
| Gm8989 | 1.60 | 1.26 | 2.25 | 4.68 | 1.00 | 5.70 | 1.00 | 1.00 | 1.00 | 18.34 | 9.90 | 15.69 |
| Gmds | 0.83 | 0.86 | 0.76 | 0.95 | 0.65 | 0.93 | 1.33 | 2.02 | 1.32 | 1.74 | 1.71 | 1.16 |
| Gmfg | 1.00 | 0.81 | 1.00 | 1.00 | 0.94 | 0.72 | 1.00 | 7.37 | 1.00 | 1.56 | 1.48 | 1.42 |
| Gmppa | 0.90 | 1.03 | 1.01 | 1.01 | 1.56 | 0.94 | 0.88 | 3.05 | 0.79 | 1.05 | 1.10 | 1.00 |
| Gmppb | 0.77 | 0.86 | 0.72 | 0.97 | 2.57 | 0.82 | 1.25 | 2.59 | 1.15 | 1.12 | 1.21 | 0.86 |
| Gmpr | 1.08 | 1.36 | 1.01 | 0.70 | 1.76 | 0.79 | 0.69 | 0.90 | 0.69 | 0.78 | 1.18 | 0.46 |
| Gnao1 | 1.02 | 0.95 | 1.03 | 1.52 | 0.73 | 0.89 | 1.27 | 1.06 | 1.17 | 2.02 | 19.71 | 2.31 |
| Gng3 | 1.73 | 1.20 | 1.71 | 0.66 | 0.63 | 0.95 | 1.17 | 1.43 | 1.15 | 1.00 | 6.81 | 1.00 |
| Gng7 | 0.85 | 1.40 | 1.18 | 0.41 | 1.00 | 0.74 | 0.92 | 1.00 | 1.31 | 1.13 | 6.18 | 1.51 |
| Gngt2 | 2.34 | 1.32 | 1.10 | 2.01 | 3.05 | 1.82 | 1.00 | 2.88 | 1.00 | 0.79 | 1.27 | 0.67 |
| Gnl1 | 0.97 | 1.15 | 1.13 | 0.90 | 1.57 | 0.83 | 0.93 | 3.36 | 1.05 | 1.00 | 1.44 | 0.97 |
| Gnmt | 1.67 | 2.30 | 1.97 | 0.98 | 2.55 | 1.27 | 0.58 | 2.08 | 0.62 | 1.36 | 2.59 | 0.47 |
| Gnpnat1 | 1.34 | 1.05 | 1.07 | 2.35 | 7.78 | 2.22 | 0.77 | 1.31 | 0.86 | 1.13 | 0.95 | 1.04 |
| Gnrh1 | 1.00 | 1.00 | 1.00 | 1.00 | 1.00 | 1.11 | 1.00 | 0.86 | 1.00 | 1.38 | 2.61 | 0.67 |
| Gon4l | 0.97 | 0.94 | 0.90 | 1.07 | 1.89 | 0.97 | 1.19 | 2.77 | 1.15 | 0.93 | 0.96 | 1.07 |
| Got1 | 1.41 | 1.54 | 1.02 | 1.50 | 1.18 | 1.30 | 1.08 | 1.29 | 0.99 | 1.44 | 2.09 | 1.20 |
| Gp1bb | 0.94 | 1.38 | 1.50 | 1.38 | 3.87 | 0.96 | 1.21 | 2.14 | 1.42 | 1.13 | 1.48 | 0.64 |
| Gp2 | 6.88 | 1.59 | 2.06 | 1.00 | 1.00 | 1.00 | 1.00 | 1.00 | 1.00 | 0.64 | 2.54 | 0.55 |

Fig. 35- 180

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Gm166 | 1.00 | 1.00 | 1.00 | 1.03 | 0.67 | 0.88 | 1.31 | 4.57 | 0.83 | 3.48 | 1.39 | 0.97 |
| Gm1673 | 1.00 | 1.00 | 1.00 | 1.09 | 1.05 | 1.30 | 1.00 | 5.40 | 1.00 | 4.88 | 0.68 | 1.00 |
| Gm16740 | 0.73 | 1.37 | 0.62 | 0.62 | 2.21 | 0.62 | 1.87 | 12.80 | 1.83 | 4.49 | 0.91 | 0.89 |
| Gm17757 | 1.00 | 1.00 | 1.00 | 1.00 | 1.00 | 1.00 | 1.00 | 1.00 | 1.00 | 1.00 | 4.27 | 1.89 |
| Gm1943 | 1.45 | 1.06 | 0.95 | 1.23 | 6.71 | 0.96 | 0.92 | 0.46 | 0.95 | 0.66 | 0.80 | 0.92 |
| Gm1966 | 1.00 | 1.00 | 1.00 | 1.00 | 1.00 | 1.00 | 1.00 | 1.00 | 1.00 | 1.00 | 1.19 | 1.05 |
| Gm2002 | 1.00 | 1.00 | 1.00 | 1.39 | 22.02 | 2.50 | 12.86 | 80.98 | 17.51 | 1.00 | 1.00 | 1.00 |
| Gm20604 | 1.00 | 1.00 | 1.00 | 0.84 | 1.00 | 0.95 | 0.76 | 0.36 | 0.63 | 0.44 | 0.71 | 0.84 |
| Gm2083 | 1.00 | 1.00 | 0.52 | 0.23 | 1.00 | 0.74 | 1.00 | 1.73 | 1.18 | 0.86 | 1.00 | 1.00 |
| Gm20878 | 1.00 | 1.00 | 1.00 | 1.00 | 2.31 | 1.00 | 1.00 | 79.44 | 1.87 | 5.46 | 1.00 | 1.00 |
| Gm21586 | 1.00 | 1.00 | 1.00 | 1.00 | 2.99 | 1.00 | 1.00 | 25.31 | 1.00 | 1.00 | 1.00 | 1.00 |
| Gm2663 | 3.36 | 19.47 | 0.38 | 1.00 | 1.00 | 1.00 | 1.00 | 1.00 | 1.00 | 1.00 | 1.00 | 1.00 |
| Gm2696 | 1.00 | 1.00 | 1.00 | 1.00 | 1.00 | 1.00 | 6.21 | 1.03 | 0.85 | 1.00 | 1.00 | 1.00 |
| Gm2897 | 1.00 | 1.00 | 1.00 | 3.70 | 1.54 | 4.20 | 1.00 | 1.00 | 1.00 | 1.00 | 1.00 | 1.00 |
| Gm2913 | 1.00 | 1.00 | 1.00 | 1.00 | 1.00 | 1.00 | 1.00 | 1.00 | 1.00 | 1.00 | 1.00 | 1.00 |
| Gm3219 | 2.44 | 2.15 | 1.23 | 1.05 | 0.80 | 0.89 | 0.87 | 6.92 | 0.79 | 3.15 | 1.30 | 1.22 |
| Gm3417 | 1.00 | 1.09 | 1.00 | 0.72 | 0.55 | 1.09 | 3.75 | 5.47 | 1.24 | 0.86 | 1.16 | 0.96 |
| Gm3500 | 1.00 | 1.00 | 1.00 | 4.48 | 2.68 | 2.82 | 1.00 | 1.00 | 1.00 | 1.00 | 1.00 | 1.00 |
| Gm3696 | 1.00 | 1.00 | 1.00 | 4.76 | 1.68 | 3.23 | 1.00 | 1.00 | 1.00 | 1.00 | 1.00 | 1.00 |
| Gm3893 | 1.00 | 1.00 | 1.00 | 10.03 | 4.05 | 10.49 | 3.15 | 3.05 | 3.64 | 1.00 | 1.00 | 1.00 |
| Gm4013 | 1.21 | 0.85 | 0.54 | 1.00 | 3.53 | 0.75 | 1.63 | 3.97 | 0.84 | 2.18 | 1.00 | 0.91 |
| Gm4070 | 1.00 | 1.00 | 1.00 | 1.00 | 1.00 | 1.00 | 1.00 | 1.00 | 1.00 | 3.99 | 3.73 | 3.18 |
| Gm4951 | 1.00 | 1.00 | 1.00 | 1.00 | 1.00 | 1.00 | 1.00 | 1.00 | 1.00 | 1.00 | 1.00 | 1.00 |
| Gm5 | 1.00 | 1.00 | 1.00 | 1.00 | 7.71 | 0.90 | 1.00 | 1.00 | 1.00 | 1.00 | 1.00 | 1.00 |
| Gm525 | 1.00 | 1.00 | 1.00 | 1.00 | 1.00 | 1.00 | 1.00 | 7.86 | 0.61 | 1.00 | 1.00 | 1.00 |
| Gm5441 | 1.00 | 1.00 | 1.00 | 1.00 | 1.00 | 1.00 | 1.00 | 1.00 | 1.00 | 1.00 | 1.09 | 1.00 |
| Gm5483 | 1.00 | 1.00 | 1.00 | 1.00 | 1.00 | 1.00 | 1.00 | 1.00 | 1.00 | 4.37 | 1.64 | 2.01 |
| Gm5512 | 1.24 | 1.34 | 1.36 | 1.04 | 1.37 | 0.98 | 0.86 | 2.30 | 0.87 | 1.16 | 0.71 | 1.17 |
| Gm561 | 0.74 | 1.02 | 1.06 | 1.13 | 1.43 | 0.92 | 0.90 | 3.76 | 0.96 | 1.35 | 1.37 | 0.82 |
| Gm5617 | 0.93 | 1.04 | 0.80 | 0.96 | 1.18 | 1.27 | 2.47 | 7.77 | 0.93 | 3.31 | 2.04 | 1.42 |
| Gm5627 | 1.00 | 1.00 | 1.00 | 1.00 | 1.00 | 1.00 | 0.71 | 0.61 | 1.70 | 1.00 | 1.00 | 1.00 |
| Gm5741 | 1.00 | 1.00 | 1.00 | 0.71 | 9.25 | 0.30 | 2.38 | 9.20 | 1.36 | 1.00 | 0.50 | 1.00 |
| Gm5771 | 0.99 | 1.15 | 0.57 | 1.00 | 1.00 | 1.00 | 1.00 | 1.00 | 1.00 | 1.00 | 1.00 | 1.00 |
| Gm6251 | 0.74 | 0.80 | 0.82 | 1.12 | 1.30 | 1.00 | 1.04 | 5.12 | 0.86 | 1.78 | 1.05 | 0.96 |
| Gm6537 | 1.00 | 1.00 | 1.00 | 0.94 | 0.79 | 1.29 | 1.91 | 9.14 | 1.91 | 1.00 | 1.00 | 1.00 |
| Gm6568 | 0.66 | 0.61 | 0.78 | 0.99 | 1.00 | 1.07 | 1.37 | 0.24 | 1.20 | 0.64 | 0.76 | 1.21 |
| Gm6607 | 1.74 | 0.96 | 1.00 | 1.06 | 2.37 | 1.00 | 1.52 | 6.17 | 0.87 | 1.33 | 2.25 | 0.43 |
| Gm6644 | 1.00 | 0.60 | 0.78 | 1.46 | 0.88 | 0.42 | 0.24 | 11.87 | 0.14 | 1.50 | 0.18 | 0.92 |
| Gm6654 | 0.95 | 0.75 | 0.95 | 1.07 | 0.86 | 0.88 | 0.86 | 7.07 | 0.74 | 2.32 | 0.91 | 1.14 |
| Gm694 | 1.00 | 1.00 | 1.00 | 1.42 | 5.44 | 1.16 | 1.00 | 1.81 | 1.00 | 1.00 | 1.00 | 1.00 |
| Gm7325 | 1.00 | 1.00 | 1.00 | 1.00 | 1.00 | 1.00 | 1.46 | 1.04 | 1.00 | 1.00 | 1.00 | 1.00 |
| Gm7334 | 1.04 | 1.12 | 0.91 | 1.30 | 1.00 | 0.32 | 1.02 | 0.13 | 0.98 | 0.50 | 0.84 | 0.92 |
| Gm7367 | 0.60 | 1.22 | 1.04 | 1.32 | 1.00 | 1.01 | 1.17 | 0.02 | 1.31 | 0.93 | 1.47 | 1.22 |
| Gm766 | 1.00 | 1.00 | 1.00 | 1.00 | 1.00 | 1.00 | 1.00 | 1.00 | 1.00 | 1.00 | 1.00 | 1.00 |
| Gm8909 | 1.00 | 1.50 | 1.33 | 1.00 | 1.00 | 1.00 | 4.63 | 0.35 | 2.75 | 0.48 | 3.68 | 2.25 |
| Gm8979 | 1.00 | 1.00 | 1.00 | 1.00 | 1.00 | 1.00 | 1.00 | 1.00 | 1.00 | 1.00 | 2.32 | 1.67 |
| Gm8989 | 1.00 | 1.00 | 1.00 | 1.00 | 1.00 | 1.00 | 1.53 | 1.00 | 1.51 | 1.00 | 17.67 | 16.15 |
| Gmds | 1.51 | 1.32 | 1.29 | 1.38 | 0.82 | 1.24 | 2.17 | 8.36 | 1.15 | 3.44 | 1.48 | 1.20 |
| Gmfg | 1.00 | 1.00 | 1.00 | 1.00 | 2.81 | 1.00 | 1.00 | 29.31 | 1.16 | 7.25 | 1.38 | 1.49 |
| Gmppa | 0.99 | 1.06 | 1.00 | 1.04 | 1.03 | 1.07 | 1.25 | 11.75 | 0.93 | 3.53 | 1.58 | 1.13 |
| Gmppb | 1.15 | 1.19 | 0.88 | 1.49 | 1.61 | 1.22 | 1.08 | 5.98 | 0.81 | 2.77 | 0.96 | 1.05 |
| Gmpr | 1.00 | 1.00 | 1.00 | 1.00 | 1.40 | 0.82 | 1.13 | 4.01 | 1.06 | 1.02 | 0.99 | 1.12 |
| Gnao1 | 1.00 | 1.00 | 1.00 | 1.03 | 0.63 | 0.95 | 1.38 | 0.82 | 1.27 | 1.00 | 1.00 | 1.00 |
| Gng3 | 1.00 | 1.00 | 1.00 | 1.09 | 0.87 | 1.07 | 0.91 | 1.45 | 1.75 | 1.00 | 1.00 | 1.00 |
| Gng7 | 1.00 | 1.00 | 1.00 | 0.98 | 0.95 | 0.94 | 0.65 | 0.38 | 0.78 | 1.00 | 1.00 | 0.91 |
| Gngt2 | 1.00 | 1.00 | 1.00 | 1.14 | 0.53 | 0.60 | 0.79 | 14.19 | 1.84 | 2.91 | 1.08 | 0.80 |
| Gnl1 | 0.78 | 0.92 | 0.89 | 1.03 | 0.91 | 1.00 | 1.23 | 8.60 | 0.92 | 3.76 | 1.46 | 1.32 |
| Gnmt | 0.83 | 1.01 | 0.75 | 0.78 | 0.84 | 0.93 | 2.12 | 26.55 | 1.37 | 4.18 | 1.00 | 1.23 |
| Gnpnat1 | 1.31 | 1.13 | 1.08 | 1.00 | 0.41 | 1.20 | 0.90 | 1.34 | 1.09 | 1.22 | 0.96 | 1.01 |
| Gnrh1 | 1.00 | 1.00 | 1.00 | 1.00 | 1.00 | 1.09 | 1.69 | 3.55 | 1.38 | 5.39 | 2.16 | 1.51 |
| Gon4l | 0.97 | 1.03 | 0.92 | 0.99 | 0.98 | 0.97 | 1.01 | 6.21 | 1.11 | 2.06 | 1.02 | 0.79 |
| Got1 | 2.30 | 3.57 | 1.69 | 1.08 | 1.21 | 1.02 | 1.43 | 1.34 | 1.37 | 1.46 | 2.11 | 1.52 |
| Gp1bb | 1.00 | 1.00 | 1.00 | 1.27 | 0.98 | 1.00 | 1.48 | 10.16 | 0.86 | 4.65 | 1.17 | 1.84 |
| Gp2 | 0.94 | 1.02 | 0.88 | 1.00 | 1.00 | 1.00 | 1.00 | 1.00 | 1.00 | 1.00 | 1.00 | 1.00 |

Fig. 35- 181

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Gpaa1 | 1.04 | 0.63 | 0.86 | 0.26 | 2.52 | 0.83 | 0.92 | 0.70 | 0.85 | 1.86 | 2.20 | 0.93 |
| Gpank1 | 1.03 | 0.65 | 0.98 | 1.26 | 7.20 | 1.36 | 0.98 | 0.98 | 0.74 | 2.39 | 2.31 | 0.91 |
| Gpatch3 | 1.13 | 0.53 | 1.24 | 0.65 | 3.03 | 0.86 | 1.13 | 1.24 | 1.04 | 3.58 | 3.30 | 1.08 |
| Gpcpd1 | 0.95 | 1.07 | 0.76 | 2.13 | 2.63 | 1.73 | 0.97 | 1.09 | 0.65 | 1.54 | 0.98 | 0.93 |
| Gpi1 | 1.09 | 0.62 | 0.86 | 0.37 | 7.27 | 1.11 | 1.01 | 0.88 | 0.84 | 2.63 | 3.57 | 1.02 |
| Gpihbp1 | 1.24 | 0.66 | 1.14 | 0.71 | 11.99 | 1.42 | 1.16 | 1.17 | 1.07 | 3.10 | 5.92 | 1.51 |
| Gpm6a | 0.75 | 1.00 | 0.92 | 1.00 | 0.04 | 1.00 | 0.54 | 0.93 | 1.56 | 0.29 | 0.41 | 1.01 |
| Gpn1 | 1.01 | 0.47 | 0.81 | 0.60 | 6.95 | 1.03 | 1.01 | 1.08 | 0.92 | 2.14 | 3.11 | 0.90 |
| Gpnmb | 1.70 | 1.37 | 1.50 | 1.16 | 0.45 | 1.61 | 1.00 | 1.11 | 1.21 | 1.20 | 1.03 | 1.12 |
| Gpr137b-ps | 1.13 | 1.11 | 1.81 | 4.39 | 3.49 | 3.41 | 3.08 | 3.40 | 4.05 | 5.01 | 5.32 | 3.94 |
| Gpr37l1 | 1.00 | 1.00 | 1.00 | 1.15 | 0.11 | 1.04 | 0.70 | 1.11 | 1.39 | 1.00 | 1.00 | 1.00 |
| Gpr4 | 1.17 | 0.80 | 0.77 | 0.65 | 1.63 | 1.17 | 1.35 | 0.93 | 0.98 | 0.85 | 0.85 | 0.93 |
| Gpr64 | 1.52 | 1.00 | 1.73 | 10.14 | 2.57 | 6.38 | 1.00 | 1.00 | 1.00 | 1.00 | 0.84 | 0.55 |
| Gpr89 | 0.94 | 0.92 | 1.32 | 0.57 | 5.65 | 0.91 | 1.04 | 1.19 | 0.99 | 1.73 | 2.83 | 1.35 |
| Gpr97 | 1.00 | 1.00 | 1.00 | 1.00 | 1.44 | 1.00 | 1.50 | 1.53 | 1.00 | 2.09 | 3.27 | 4.57 |
| Gprc5a | 3.47 | 2.19 | 4.19 | 0.86 | 0.24 | 0.66 | 5.31 | 4.57 | 2.81 | 0.33 | 0.45 | 1.44 |
| Gpsm3 | 1.88 | 0.76 | 1.88 | 0.98 | 6.11 | 1.41 | 1.01 | 0.78 | 1.03 | 1.66 | 2.00 | 0.92 |
| Gpx1 | 2.27 | 1.64 | 1.59 | 1.78 | 16.99 | 2.68 | 1.48 | 1.13 | 1.17 | 1.44 | 2.09 | 1.00 |
| Gpx3 | 1.44 | 0.74 | 0.93 | 1.14 | 7.60 | 2.16 | 1.53 | 1.26 | 1.43 | 2.51 | 2.87 | 1.29 |
| Gpx4 | 1.31 | 0.49 | 1.01 | 0.25 | 13.48 | 0.81 | 1.00 | 0.75 | 0.86 | 4.02 | 6.42 | 1.17 |
| Gramd3 | 11.88 | 10.61 | 8.16 | 2.97 | 5.22 | 4.34 | 3.48 | 3.90 | 3.90 | 4.22 | 2.00 | 1.49 |
| Grcc10 | 1.22 | 0.55 | 0.85 | 0.27 | 9.50 | 0.89 | 0.93 | 0.75 | 0.70 | 2.37 | 3.57 | 1.08 |
| Grhpr | 0.93 | 0.53 | 0.89 | 0.53 | 10.88 | 1.09 | 1.36 | 0.89 | 0.96 | 2.03 | 3.87 | 0.78 |
| Gria1 | 1.00 | 1.00 | 1.00 | 1.00 | 0.18 | 1.00 | 1.00 | 1.00 | 1.00 | 1.21 | 0.95 | 1.01 |
| Gria2 | 1.00 | 1.00 | 1.00 | 1.00 | 0.18 | 1.00 | 1.00 | 1.00 | 1.00 | 1.00 | 1.00 | 1.00 |
| Grin1 | 1.00 | 1.00 | 1.00 | 1.00 | 0.18 | 1.00 | 1.00 | 1.00 | 1.00 | 1.00 | 1.00 | 1.00 |
| Grpel2 | 1.39 | 1.64 | 1.38 | 1.24 | 0.64 | 1.17 | 0.92 | 1.37 | 1.23 | 1.86 | 1.25 | 1.75 |
| Grrp1 | 1.56 | 0.91 | 1.05 | 0.67 | 3.50 | 0.89 | 1.46 | 0.84 | 1.47 | 1.69 | 2.15 | 1.09 |
| Gsg1 | 1.00 | 1.00 | 1.00 | 1.00 | 1.00 | 1.00 | 1.00 | 1.00 | 1.00 | 2.07 | 1.00 | 1.00 |
| Gskip | 0.51 | 1.01 | 0.75 | 0.78 | 0.82 | 0.85 | 0.85 | 0.96 | 0.89 | 1.07 | 1.06 | 0.86 |
| Gsn | 1.47 | 0.85 | 1.25 | 0.87 | 5.50 | 1.17 | 0.97 | 0.96 | 0.99 | 1.56 | 2.04 | 1.05 |
| Gss | 1.20 | 0.86 | 0.86 | 0.59 | 4.30 | 0.80 | 1.37 | 1.08 | 1.05 | 1.51 | 2.42 | 1.06 |
| Gsta3 | 1.00 | 1.02 | 1.00 | 1.00 | 9.96 | 1.00 | 0.61 | 0.77 | 0.78 | 1.37 | 2.08 | 1.11 |
| Gstk1 | 0.86 | 0.41 | 0.66 | 0.34 | 5.65 | 1.07 | 1.06 | 0.87 | 0.80 | 2.44 | 2.88 | 0.94 |
| Gstm2 | 1.49 | 0.72 | 1.03 | 1.75 | 5.24 | 1.80 | 1.00 | 1.05 | 0.94 | 0.59 | 1.18 | 1.11 |
| Gstm5 | 1.17 | 0.76 | 0.89 | 0.33 | 5.30 | 1.00 | 0.90 | 0.60 | 0.86 | 1.21 | 2.48 | 1.65 |
| Gstm6 | 1.00 | 1.00 | 1.00 | 1.00 | 1.00 | 1.00 | 0.49 | 1.69 | 1.01 | 0.88 | 0.62 | 0.76 |
| Gstm7 | 1.17 | 0.46 | 0.62 | 0.55 | 2.73 | 1.25 | 0.83 | 0.92 | 0.68 | 2.12 | 2.26 | 0.99 |
| Gstp1 | 1.37 | 0.46 | 0.89 | 0.34 | 12.83 | 1.07 | 0.74 | 0.77 | 0.86 | 2.30 | 4.41 | 1.03 |
| Gstp2 | 1.37 | 0.44 | 0.80 | 0.36 | 12.64 | 1.07 | 0.92 | 0.65 | 0.92 | 2.27 | 4.57 | 1.00 |
| Gstt2 | 0.36 | 0.30 | 0.93 | 0.39 | 6.58 | 1.26 | 0.51 | 0.39 | 0.81 | 1.96 | 2.30 | 1.03 |
| Gtf2b | 1.24 | 1.35 | 0.74 | 1.02 | 1.57 | 1.24 | 1.31 | 1.38 | 1.01 | 0.55 | 0.88 | 0.90 |
| Gtf2f2 | 1.19 | 0.83 | 0.98 | 0.80 | 4.53 | 1.58 | 0.92 | 0.83 | 0.88 | 2.36 | 2.05 | 1.46 |
| Gtf2h4 | 0.89 | 0.38 | 0.94 | 0.64 | 5.79 | 0.87 | 0.98 | 1.14 | 1.15 | 1.76 | 3.62 | 1.02 |
| Gtf2h5 | 1.06 | 0.67 | 0.97 | 0.41 | 6.10 | 0.96 | 1.04 | 0.96 | 0.81 | 1.90 | 2.24 | 0.96 |
| Gtf3c6 | 0.62 | 0.38 | 0.76 | 0.64 | 6.34 | 0.68 | 0.90 | 1.08 | 0.82 | 3.23 | 4.95 | 1.03 |
| Gtl3 | 1.29 | 0.55 | 0.84 | 0.63 | 3.21 | 1.04 | 0.86 | 0.66 | 0.85 | 1.18 | 1.54 | 0.98 |
| Gtpbp6 | 1.13 | 0.73 | 1.13 | 0.36 | 4.70 | 1.16 | 1.19 | 0.88 | 1.34 | 1.54 | 1.87 | 0.94 |
| Guca1a | 1.00 | 1.00 | 1.00 | 1.00 | 2.34 | 1.00 | 1.00 | 1.00 | 1.00 | 5.48 | 8.04 | 1.00 |
| Guca2a | 1.00 | 1.00 | 0.29 | 1.00 | 1.00 | 1.00 | 1.00 | 1.00 | 1.00 | 1.02 | 1.00 | 1.00 |
| Guca2b | 1.00 | 1.00 | 1.00 | 1.00 | 1.00 | 1.00 | 1.00 | 1.00 | 1.00 | 1.00 | 1.00 | 1.00 |
| Gusb | 1.72 | 0.78 | 1.43 | 2.27 | 7.32 | 1.47 | 1.41 | 1.23 | 1.28 | 1.52 | 1.86 | 1.03 |
| Gxylt2 | 1.00 | 1.00 | 1.00 | 1.00 | 1.00 | 1.00 | 1.00 | 1.00 | 0.98 | 1.00 | 1.00 | 1.00 |
| Gys2 | 1.00 | 1.00 | 1.00 | 1.45 | 3.00 | 1.99 | 1.00 | 1.00 | 1.00 | 1.00 | 1.00 | 1.00 |
| Gzmm | 0.98 | 0.35 | 0.54 | 1.00 | 1.82 | 1.00 | 0.89 | 0.76 | 0.61 | 1.58 | 2.35 | 1.20 |
| H13 | 1.06 | 0.80 | 1.06 | 0.55 | 4.20 | 1.03 | 0.96 | 0.83 | 1.00 | 2.12 | 2.64 | 1.03 |
| H1fx | 1.32 | 0.97 | 0.65 | 0.60 | 4.44 | 0.76 | 1.21 | 0.58 | 0.68 | 2.02 | 3.00 | 0.73 |
| H2-Bl | 1.00 | 1.00 | 1.00 | 0.27 | 0.41 | 0.23 | 1.00 | 1.00 | 1.00 | 1.00 | 0.56 | 1.05 |
| H2-D1 | 1.95 | 2.03 | 1.64 | 0.80 | 4.99 | 1.23 | 1.60 | 1.29 | 1.68 | 3.00 | 1.86 | 0.97 |
| H2-Ea-ps | 3.22 | 1.05 | 8.10 | 1.95 | 1.00 | 6.07 | 1.86 | 1.64 | 6.00 | 1.33 | 6.78 | 115.83 |
| H2-K2 | 1.90 | 2.08 | 3.23 | 3.08 | 2.10 | 3.02 | 3.09 | 3.97 | 3.23 | 1.60 | 1.60 | 1.67 |
| H2-Ke2 | 1.34 | 0.58 | 1.16 | 0.53 | 11.43 | 1.06 | 1.50 | 1.04 | 1.33 | 4.80 | 6.21 | 1.17 |
| H2-Ke6 | 0.82 | 0.43 | 0.95 | 0.27 | 6.30 | 1.15 | 0.85 | 0.66 | 0.64 | 2.41 | 2.40 | 0.84 |
| H2-Q1 | 5.64 | 3.48 | 9.24 | 3.73 | 1.19 | 4.96 | 5.03 | 5.77 | 5.85 | 0.35 | 0.62 | 2.91 |

Fig. 35- 182

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Gpaa1 | 0.93 | 1.04 | 0.85 | 0.85 | 0.72 | 0.84 | 0.78 | 1.58 | 0.93 | 1.13 | 1.27 | 1.01 |
| Gpank1 | 1.11 | 1.43 | 0.97 | 1.42 | 0.94 | 1.16 | 0.89 | 2.13 | 1.06 | 1.00 | 1.73 | 0.99 |
| Gpatch3 | 1.24 | 1.50 | 0.98 | 1.01 | 0.57 | 1.08 | 1.48 | 4.29 | 0.85 | 1.16 | 1.52 | 1.18 |
| Gpcpd1 | 0.80 | 0.86 | 0.87 | 0.92 | 1.03 | 0.74 | 3.80 | 8.30 | 4.12 | 0.88 | 0.77 | 0.96 |
| Gpi1 | 1.21 | 1.76 | 1.10 | 0.88 | 0.72 | 0.88 | 0.98 | 1.59 | 0.80 | 0.96 | 1.50 | 1.00 |
| Gpihbp1 | 4.83 | 6.36 | 1.88 | 1.51 | 1.01 | 1.01 | 1.17 | 1.74 | 0.99 | 1.29 | 2.31 | 1.28 |
| Gpm6a | 1.02 | 0.82 | 0.61 | 0.88 | 1.46 | 0.83 | 1.00 | 1.00 | 1.00 | 0.51 | 0.90 | 0.64 |
| Gpn1 | 1.03 | 1.34 | 0.88 | 1.15 | 0.79 | 0.85 | 0.91 | 1.47 | 0.74 | 0.91 | 1.83 | 1.10 |
| Gpnmb | 2.75 | 1.82 | 6.90 | 1.00 | 1.00 | 1.00 | 1.00 | 1.00 | 1.00 | 0.76 | 0.68 | 1.05 |
| Gpr137b-ps | 3.94 | 3.87 | 4.30 | 1.60 | 2.93 | 1.73 | 1.00 | 1.00 | 1.00 | 2.52 | 2.89 | 2.98 |
| Gpr37l1 | 1.00 | 1.00 | 1.00 | 1.00 | 1.00 | 1.00 | 1.00 | 1.00 | 1.00 | 1.02 | 1.02 | 0.88 |
| Gpr4 | 0.89 | 0.88 | 1.04 | 1.07 | 1.34 | 1.04 | 0.78 | 1.00 | 1.16 | 1.01 | 0.84 | 0.86 |
| Gpr64 | 2.72 | 2.26 | 2.33 | 1.00 | 1.00 | 1.00 | 1.00 | 1.00 | 1.00 | 1.00 | 1.00 | 1.00 |
| Gpr89 | 1.19 | 1.26 | 1.16 | 0.96 | 0.70 | 1.00 | 0.87 | 1.29 | 0.95 | 0.94 | 1.68 | 1.02 |
| Gpr97 | 6.12 | 5.53 | 5.27 | 1.25 | 1.00 | 1.50 | 3.35 | 1.81 | 2.83 | 1.06 | 2.15 | 2.25 |
| Gprc5a | 2.15 | 2.33 | 2.04 | 1.55 | 1.00 | 0.89 | 8.30 | 2.08 | 5.26 | 1.75 | 1.88 | 1.54 |
| Gpsm3 | 0.97 | 1.25 | 0.85 | 0.71 | 0.77 | 0.84 | 0.87 | 1.64 | 0.93 | 0.89 | 1.14 | 0.92 |
| Gpx1 | 1.53 | 1.83 | 1.41 | 1.49 | 1.34 | 1.34 | 0.93 | 1.09 | 0.83 | 1.06 | 1.43 | 1.05 |
| Gpx3 | 5.62 | 4.55 | 3.09 | 1.37 | 1.07 | 1.44 | 1.41 | 1.99 | 1.75 | 1.21 | 1.72 | 1.29 |
| Gpx4 | 1.08 | 1.38 | 1.00 | 0.83 | 0.45 | 0.96 | 1.00 | 2.24 | 1.08 | 1.02 | 1.67 | 0.97 |
| Gramd3 | 3.77 | 3.73 | 2.51 | 2.92 | 3.27 | 2.98 | 2.40 | 22.73 | 2.91 | 2.78 | 2.91 | 2.81 |
| Grcc10 | 1.09 | 1.40 | 0.91 | 0.76 | 0.59 | 0.88 | 0.71 | 1.35 | 0.76 | 0.90 | 1.46 | 1.05 |
| Grhpr | 0.93 | 1.27 | 1.02 | 1.16 | 0.78 | 1.09 | 1.32 | 2.40 | 1.17 | 1.13 | 1.59 | 0.85 |
| Gria1 | 1.00 | 1.00 | 1.00 | 1.00 | 1.00 | 1.00 | 1.00 | 1.00 | 1.00 | 1.00 | 1.00 | 1.00 |
| Gria2 | 1.00 | 1.00 | 1.00 | 1.00 | 1.00 | 1.00 | 1.00 | 1.00 | 1.00 | 1.00 | 1.00 | 1.00 |
| Grin1 | 1.00 | 1.00 | 1.00 | 1.00 | 1.00 | 1.00 | 1.00 | 1.00 | 1.00 | 1.00 | 1.00 | 0.73 |
| Grpel2 | 0.74 | 0.61 | 0.81 | 4.26 | 8.28 | 3.71 | 1.27 | 1.01 | 1.63 | 1.36 | 1.07 | 1.31 |
| Grrp1 | 1.84 | 1.90 | 1.21 | 0.92 | 1.00 | 1.15 | 1.00 | 1.00 | 1.00 | 1.37 | 1.81 | 1.09 |
| Gsg1 | 1.00 | 1.00 | 1.00 | 1.00 | 1.00 | 1.00 | 1.00 | 2.88 | 1.00 | 1.00 | 1.00 | 1.00 |
| Gskip | 1.04 | 1.03 | 1.09 | 1.29 | 2.38 | 1.15 | 1.08 | 1.24 | 1.63 | 0.95 | 0.95 | 1.16 |
| Gsn | 2.35 | 1.97 | 1.15 | 1.04 | 0.85 | 1.14 | 0.72 | 0.87 | 1.00 | 1.03 | 1.45 | 1.05 |
| Gss | 1.28 | 1.32 | 0.84 | 0.77 | 0.64 | 0.88 | 0.82 | 1.09 | 0.79 | 1.04 | 1.57 | 0.98 |
| Gsta3 | 2.51 | 4.28 | 1.16 | 0.77 | 0.72 | 0.67 | 0.35 | 0.39 | 0.56 | 0.74 | 1.90 | 0.76 |
| Gstk1 | 1.29 | 1.64 | 0.77 | 0.76 | 0.63 | 0.99 | 0.91 | 1.73 | 0.97 | 1.07 | 1.61 | 0.94 |
| Gstm2 | 2.69 | 2.12 | 1.75 | 1.45 | 0.86 | 1.17 | 1.94 | 0.77 | 1.11 | 1.62 | 2.34 | 1.83 |
| Gstm5 | 1.07 | 1.63 | 1.10 | 0.79 | 0.68 | 0.77 | 0.93 | 1.90 | 2.14 | 1.38 | 1.57 | 0.90 |
| Gstm6 | 0.69 | 0.99 | 1.29 | 0.76 | 0.83 | 0.78 | 0.80 | 0.77 | 0.74 | 1.24 | 1.83 | 1.17 |
| Gstm7 | 1.90 | 2.90 | 1.20 | 1.01 | 0.50 | 0.78 | 0.92 | 1.41 | 1.02 | 0.99 | 1.63 | 0.93 |
| Gstp1 | 1.22 | 1.47 | 1.21 | 0.88 | 0.73 | 0.84 | 0.82 | 1.70 | 1.02 | 1.00 | 1.67 | 1.04 |
| Gstp2 | 1.42 | 1.81 | 0.92 | 1.06 | 0.71 | 0.88 | 0.82 | 1.72 | 1.02 | 0.91 | 1.97 | 1.06 |
| Gstt2 | 0.88 | 1.25 | 0.94 | 1.09 | 0.73 | 1.00 | 1.05 | 1.86 | 1.06 | 0.97 | 1.42 | 1.02 |
| Gtf2b | 0.91 | 1.01 | 0.88 | 0.90 | 2.07 | 1.00 | 1.96 | 0.85 | 1.35 | 0.95 | 1.49 | 1.22 |
| Gtf2f2 | 1.20 | 1.15 | 0.95 | 0.99 | 0.72 | 1.17 | 1.03 | 2.67 | 0.88 | 1.42 | 1.39 | 1.17 |
| Gtf2h4 | 0.63 | 0.99 | 0.60 | 1.01 | 0.59 | 1.12 | 1.00 | 1.68 | 1.17 | 0.86 | 1.20 | 1.21 |
| Gtf2h5 | 1.06 | 1.29 | 0.87 | 0.89 | 0.63 | 0.88 | 1.24 | 1.75 | 0.84 | 0.86 | 1.42 | 0.98 |
| Gtf3c6 | 0.89 | 0.89 | 0.94 | 1.05 | 0.57 | 0.94 | 1.16 | 1.73 | 0.83 | 0.93 | 1.16 | 0.88 |
| Gtl3 | 1.03 | 1.05 | 0.97 | 0.76 | 0.83 | 0.88 | 0.72 | 0.44 | 0.59 | 0.97 | 1.40 | 1.21 |
| Gtpbp6 | 1.04 | 1.58 | 1.10 | 0.86 | 0.60 | 1.22 | 2.26 | 1.44 | 0.84 | 0.88 | 1.49 | 1.02 |
| Guca1a | 1.00 | 1.00 | 1.10 | 1.00 | 0.40 | 1.00 | 0.94 | 2.02 | 0.63 | 1.40 | 1.76 | 0.99 |
| Guca2a | 2.09 | 1.29 | 4.85 | 0.80 | 0.41 | 0.62 | 1.00 | 1.00 | 1.00 | 1.11 | 2.11 | 1.32 |
| Guca2b | 3.51 | 2.73 | 2.02 | 1.11 | 1.30 | 1.03 | 1.00 | 1.00 | 1.00 | 0.74 | 1.37 | 1.23 |
| Gusb | 1.63 | 1.61 | 1.52 | 3.68 | 2.15 | 2.24 | 0.87 | 1.41 | 0.72 | 0.92 | 1.12 | 0.86 |
| Gxylt2 | 1.00 | 1.00 | 0.88 | 6.10 | 1.06 | 3.82 | 1.00 | 1.00 | 1.00 | 1.00 | 1.00 | 1.00 |
| Gys2 | 1.00 | 1.00 | 1.00 | 2.50 | 2.88 | 2.17 | 1.95 | 1.87 | 1.65 | 1.00 | 1.00 | 1.00 |
| Gzmm | 1.19 | 1.00 | 1.00 | 1.00 | 0.98 | 1.00 | 1.00 | 1.00 | 1.00 | 1.00 | 1.00 | 1.00 |
| H13 | 0.95 | 1.13 | 0.96 | 1.04 | 0.69 | 1.06 | 0.84 | 1.87 | 0.82 | 0.90 | 1.26 | 1.08 |
| H1fx | 0.51 | 0.97 | 0.43 | 0.83 | 0.65 | 0.68 | 1.00 | 2.74 | 1.17 | 1.00 | 1.41 | 0.94 |
| H2-Bl | 0.10 | 0.07 | 0.06 | 1.40 | 1.88 | 1.62 | 1.86 | 2.32 | 1.99 | 0.53 | 0.51 | 0.40 |
| H2-D1 | 1.04 | 1.13 | 0.92 | 1.37 | 2.15 | 1.10 | 1.68 | 2.66 | 1.55 | 1.18 | 1.42 | 0.93 |
| H2-Ea-ps | 338.84 | 338.58 | 438.60 | 8.65 | 1.31 | 23.66 | 1.76 | 1.00 | 4.53 | 46.96 | 53.41 | 66.57 |
| H2-K2 | 0.36 | 0.38 | 0.34 | 1.98 | 2.27 | 2.84 | 2.29 | 0.46 | 2.42 | 1.40 | 1.91 | 1.48 |
| H2-Ke2 | 1.14 | 1.64 | 1.14 | 0.92 | 0.56 | 0.95 | 0.98 | 2.72 | 0.97 | 1.30 | 1.86 | 1.40 |
| H2-Ke6 | 0.84 | 1.20 | 0.87 | 0.81 | 0.50 | 0.95 | 0.72 | 1.57 | 0.79 | 0.79 | 1.12 | 0.88 |
| H2-Q1 | 0.47 | 0.48 | 0.48 | 2.46 | 1.69 | 2.44 | 3.97 | 0.30 | 3.97 | 1.33 | 1.20 | 1.29 |

Fig. 35- 183

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Gpaa1 | 0.91 | 1.10 | 0.91 | 1.01 | 3.46 | 1.04 | 0.99 | 1.84 | 1.00 | 0.84 | 1.00 | 0.99 |
| Gpank1 | 1.20 | 1.45 | 1.36 | 1.27 | 2.55 | 1.04 | 1.22 | 2.48 | 1.22 | 1.22 | 1.26 | 0.93 |
| Gpatch3 | 1.19 | 1.13 | 1.14 | 1.44 | 1.56 | 0.86 | 0.90 | 4.42 | 0.94 | 1.24 | 1.14 | 0.81 |
| Gpcpd1 | 0.98 | 1.03 | 0.91 | 1.85 | 4.78 | 2.54 | 0.83 | 1.25 | 0.83 | 0.94 | 0.72 | 0.93 |
| Gpi1 | 0.93 | 0.95 | 0.87 | 0.83 | 2.87 | 1.00 | 0.86 | 2.23 | 1.05 | 1.21 | 1.51 | 1.06 |
| Gpihbp1 | 2.12 | 2.74 | 2.07 | 1.09 | 3.65 | 1.24 | 1.00 | 1.16 | 1.00 | 1.49 | 1.99 | 1.23 |
| Gpm6a | 0.68 | 0.56 | 0.60 | 1.19 | 0.60 | 1.48 | 1.00 | 1.00 | 1.00 | 0.89 | 13.22 | 1.42 |
| Gpn1 | 1.17 | 0.77 | 1.19 | 0.89 | 4.95 | 1.13 | 1.21 | 2.07 | 0.93 | 1.25 | 1.28 | 0.96 |
| Gpnmb | 1.18 | 1.48 | 1.28 | 0.79 | 0.60 | 0.19 | 1.00 | 1.00 | 1.00 | 1.00 | 1.00 | 1.00 |
| Gpr137b-ps | 2.48 | 4.06 | 3.66 | 1.96 | 1.28 | 1.35 | 1.34 | 1.00 | 1.79 | 1.77 | 2.01 | 2.07 |
| Gpr37l1 | 1.14 | 1.95 | 1.43 | 1.00 | 1.00 | 1.73 | 1.00 | 1.00 | 1.00 | 1.00 | 14.71 | 1.00 |
| Gpr4 | 1.16 | 1.10 | 1.09 | 1.00 | 2.62 | 1.10 | 1.09 | 0.85 | 0.69 | 0.55 | 0.44 | 0.86 |
| Gpr64 | 1.01 | 1.04 | 0.80 | 1.62 | 0.64 | 2.88 | 1.00 | 1.00 | 1.00 | 1.97 | 1.58 | 1.83 |
| Gpr89 | 1.31 | 1.37 | 1.12 | 1.13 | 4.79 | 1.27 | 1.10 | 1.58 | 1.20 | 1.32 | 0.99 | 1.06 |
| Gpr97 | 1.00 | 1.00 | 1.00 | 5.99 | 1.63 | 4.91 | 1.00 | 1.00 | 1.00 | 4.65 | 3.16 | 1.57 |
| Gprc5a | 1.23 | 1.36 | 0.95 | 3.46 | 1.03 | 3.45 | 1.35 | 1.00 | 1.09 | 1.26 | 1.59 | 1.00 |
| Gpsm3 | 0.84 | 0.81 | 1.09 | 0.88 | 2.53 | 0.80 | 2.52 | 3.62 | 1.26 | 1.00 | 0.97 | 0.98 |
| Gpx1 | 1.07 | 1.17 | 0.96 | 1.83 | 4.85 | 1.50 | 1.06 | 1.39 | 0.86 | 0.60 | 0.79 | 0.50 |
| Gpx3 | 1.21 | 1.46 | 1.41 | 1.66 | 4.58 | 1.99 | 1.19 | 2.49 | 0.85 | 2.18 | 2.72 | 2.38 |
| Gpx4 | 0.77 | 1.16 | 0.90 | 0.84 | 1.74 | 0.71 | 0.90 | 4.44 | 0.99 | 0.88 | 1.41 | 0.83 |
| Gramd3 | 2.14 | 2.18 | 2.51 | 2.23 | 6.00 | 2.61 | 1.98 | 7.98 | 1.78 | 2.36 | 2.21 | 1.88 |
| Grcc10 | 1.07 | 1.45 | 1.22 | 0.74 | 2.02 | 0.87 | 0.82 | 2.39 | 0.93 | 0.84 | 1.18 | 0.89 |
| Grhpr | 1.39 | 1.49 | 1.18 | 0.74 | 1.88 | 1.19 | 1.02 | 2.22 | 0.60 | 0.81 | 1.51 | 0.87 |
| Gria1 | 1.00 | 1.00 | 1.00 | 1.88 | 1.00 | 2.62 | 1.14 | 1.00 | 1.17 | 1.00 | 8.95 | 1.00 |
| Gria2 | 1.00 | 1.00 | 1.00 | 1.00 | 1.00 | 1.00 | 1.00 | 1.00 | 1.00 | 1.00 | 10.10 | 1.00 |
| Grin1 | 1.00 | 1.00 | 1.00 | 1.00 | 1.00 | 1.00 | 1.00 | 1.00 | 1.00 | 1.00 | 9.17 | 1.00 |
| Grpel2 | 1.13 | 1.12 | 1.02 | 0.94 | 1.00 | 1.01 | 1.23 | 1.00 | 1.15 | 0.97 | 0.69 | 1.01 |
| Grrp1 | 1.13 | 1.62 | 1.13 | 1.01 | 1.84 | 1.04 | 0.74 | 1.52 | 0.81 | 1.17 | 1.16 | 1.00 |
| Gsg1 | 1.00 | 1.00 | 1.00 | 6.23 | 1.99 | 1.14 | 0.93 | 0.97 | 1.02 | 1.00 | 1.00 | 1.00 |
| Gskip | 0.97 | 0.83 | 0.97 | 0.78 | 1.64 | 0.81 | 0.72 | 1.31 | 0.75 | 1.00 | 1.05 | 0.93 |
| Gsn | 1.18 | 1.33 | 1.18 | 0.70 | 1.92 | 0.79 | 1.23 | 1.35 | 1.23 | 1.08 | 1.17 | 1.00 |
| Gss | 0.71 | 0.75 | 0.71 | 0.87 | 3.24 | 1.16 | 0.99 | 1.53 | 1.24 | 1.04 | 1.06 | 0.88 |
| Gsta3 | 0.77 | 1.12 | 0.92 | 1.03 | 11.25 | 0.86 | 0.69 | 0.77 | 0.61 | 0.97 | 1.74 | 0.79 |
| Gstk1 | 1.09 | 1.14 | 1.17 | 0.69 | 1.04 | 0.66 | 1.34 | 2.98 | 0.62 | 1.78 | 0.95 | 0.74 |
| Gstm2 | 1.69 | 1.64 | 1.94 | 1.08 | 1.14 | 0.99 | 0.83 | 0.36 | 0.64 | 1.07 | 1.44 | 0.90 |
| Gstm5 | 1.09 | 1.14 | 1.41 | 1.07 | 6.52 | 1.68 | 0.95 | 1.15 | 1.03 | 0.87 | 1.37 | 0.89 |
| Gstm6 | 0.87 | 1.20 | 1.36 | 0.88 | 5.39 | 0.99 | 0.77 | 0.76 | 0.75 | 1.00 | 1.00 | 1.00 |
| Gstm7 | 1.35 | 1.47 | 1.38 | 0.99 | 7.15 | 1.03 | 0.98 | 1.80 | 0.93 | 2.00 | 1.88 | 1.29 |
| Gstp1 | 0.83 | 1.16 | 1.05 | 0.79 | 3.36 | 1.06 | 0.96 | 2.35 | 0.81 | 1.13 | 1.36 | 1.01 |
| Gstp2 | 0.84 | 1.03 | 0.92 | 0.91 | 4.00 | 0.92 | 0.89 | 2.12 | 1.09 | 1.03 | 1.23 | 0.98 |
| Gstt2 | 0.86 | 1.00 | 0.92 | 0.78 | 1.93 | 0.93 | 0.98 | 1.83 | 0.91 | 1.07 | 1.20 | 0.92 |
| Gtf2b | 1.04 | 0.95 | 1.07 | 1.27 | 0.49 | 1.07 | 0.92 | 0.44 | 1.01 | 1.12 | 1.05 | 0.94 |
| Gtf2f2 | 0.89 | 0.84 | 0.83 | 1.20 | 2.83 | 1.33 | 0.87 | 3.33 | 1.02 | 1.19 | 1.28 | 0.85 |
| Gtf2h4 | 1.06 | 1.13 | 0.79 | 0.67 | 5.87 | 0.92 | 0.76 | 2.22 | 1.09 | 1.01 | 1.04 | 1.15 |
| Gtf2h5 | 0.99 | 0.83 | 0.73 | 0.95 | 2.79 | 0.86 | 0.85 | 2.34 | 0.76 | 1.07 | 1.31 | 1.13 |
| Gtf3c6 | 0.89 | 0.72 | 0.80 | 1.01 | 1.55 | 0.82 | 1.04 | 2.80 | 0.63 | 1.03 | 0.80 | 0.94 |
| Gtl3 | 0.98 | 0.97 | 1.00 | 0.95 | 5.08 | 1.03 | 1.07 | 0.75 | 0.90 | 1.02 | 1.22 | 1.01 |
| Gtpbp6 | 0.93 | 2.34 | 1.10 | 1.28 | 8.39 | 1.16 | 1.16 | 1.32 | 1.20 | 0.94 | 1.52 | 1.16 |
| Guca1a | 1.38 | 0.87 | 1.18 | 1.00 | 1.28 | 0.51 | 1.37 | 10.35 | 1.14 | 1.00 | 1.55 | 1.68 |
| Guca2a | 0.58 | 1.81 | 0.66 | 1.00 | 1.00 | 1.00 | 1.00 | 1.23 | 1.00 | 1.00 | 1.00 | 1.00 |
| Guca2b | 3.71 | 2.37 | 8.75 | 1.00 | 1.00 | 0.83 | 1.00 | 1.00 | 1.00 | 1.00 | 1.00 | 1.43 |
| Gusb | 0.83 | 0.87 | 0.85 | 0.87 | 2.45 | 0.59 | 0.93 | 1.42 | 0.85 | 1.08 | 1.13 | 0.98 |
| Gxylt2 | 1.00 | 1.00 | 1.00 | 0.68 | 1.00 | 0.55 | 0.83 | 1.47 | 1.05 | 1.00 | 1.00 | 1.00 |
| Gys2 | 1.00 | 1.00 | 1.00 | 7.73 | 1.73 | 2.16 | 1.00 | 1.00 | 1.00 | 1.00 | 1.00 | 1.00 |
| Gzmm | 1.00 | 1.00 | 0.98 | 1.00 | 1.23 | 1.00 | 1.00 | 1.99 | 1.00 | 1.72 | 2.59 | 2.53 |
| H13 | 0.91 | 0.97 | 0.89 | 1.17 | 3.00 | 0.99 | 0.86 | 2.01 | 0.91 | 1.02 | 1.09 | 1.15 |
| H1fx | 0.89 | 0.63 | 1.29 | 0.58 | 1.12 | 0.64 | 0.88 | 3.10 | 1.05 | 0.77 | 2.87 | 0.62 |
| H2-Bl | 1.92 | 1.05 | 0.68 | 2.69 | 1.00 | 1.82 | 1.00 | 1.00 | 1.00 | 1.51 | 1.03 | 1.22 |
| H2-D1 | 1.15 | 1.26 | 1.01 | 0.85 | 3.40 | 0.82 | 1.10 | 6.23 | 1.31 | 0.95 | 0.98 | 0.71 |
| H2-Ea-ps | 14.16 | 7.45 | 17.81 | 47.25 | 1.00 | 68.24 | 1.00 | 1.00 | 1.01 | 794.62 | 480.05 | 669.40 |
| H2-K2 | 2.16 | 1.51 | 1.33 | 2.64 | 2.24 | 2.53 | 1.00 | 1.00 | 1.00 | 1.50 | 1.40 | 1.36 |
| H2-Ke2 | 0.99 | 1.31 | 1.03 | 1.04 | 1.78 | 1.13 | 0.87 | 4.79 | 0.90 | 1.03 | 1.23 | 1.18 |
| H2-Ke6 | 1.07 | 1.34 | 1.30 | 0.79 | 1.91 | 0.91 | 0.88 | 3.29 | 0.65 | 0.76 | 1.01 | 0.86 |
| H2-Q1 | 3.33 | 3.41 | 2.80 | 4.85 | 0.51 | 4.04 | 1.35 | 1.00 | 1.40 | 2.45 | 2.07 | 2.03 |

Fig. 35- 184

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Gpaa1 | 1.01 | 1.41 | 0.90 | 1.30 | 1.01 | 1.11 | 1.22 | 5.10 | 0.86 | 1.66 | 0.88 | 1.02 |
| Gpank1 | 1.19 | 0.94 | 0.93 | 1.51 | 1.57 | 1.35 | 1.25 | 7.37 | 1.19 | 1.91 | 1.33 | 1.07 |
| Gpatch3 | 1.00 | 1.00 | 1.00 | 0.98 | 1.05 | 1.16 | 1.12 | 5.36 | 1.05 | 2.81 | 1.45 | 1.04 |
| Gpcpd1 | 1.03 | 1.50 | 0.92 | 0.85 | 0.62 | 0.93 | 0.87 | 1.34 | 0.94 | 0.83 | 1.03 | 0.88 |
| Gpi1 | 0.86 | 0.66 | 0.80 | 1.10 | 0.93 | 1.08 | 1.18 | 7.82 | 0.98 | 4.13 | 1.85 | 1.50 |
| Gpihbp1 | 1.27 | 2.52 | 1.49 | 1.00 | 1.20 | 1.00 | 4.46 | 29.90 | 3.02 | 0.89 | 1.00 | 1.00 |
| Gpm6a | 0.86 | 1.00 | 1.00 | 0.97 | 1.24 | 0.93 | 0.61 | 0.42 | 1.13 | 1.00 | 1.00 | 0.83 |
| Gpn1 | 0.64 | 0.70 | 0.60 | 1.50 | 1.08 | 1.00 | 1.24 | 6.91 | 0.93 | 2.08 | 1.25 | 1.02 |
| Gpnmb | 1.00 | 1.00 | 1.00 | 1.00 | 1.00 | 1.00 | 1.34 | 0.26 | 0.81 | 1.00 | 1.00 | 1.00 |
| Gpr137b-ps | 1.00 | 1.00 | 1.00 | 2.04 | 2.33 | 3.63 | 2.54 | 3.25 | 3.08 | 5.56 | 3.25 | 3.54 |
| Gpr37l1 | 1.00 | 1.00 | 1.00 | 0.97 | 0.87 | 0.94 | 1.26 | 1.00 | 1.09 | 1.00 | 1.00 | 1.00 |
| Gpr4 | 1.00 | 1.00 | 1.00 | 0.94 | 5.04 | 0.92 | 1.15 | 2.21 | 1.50 | 1.00 | 1.00 | 1.00 |
| Gpr64 | 1.00 | 1.00 | 1.00 | 1.00 | 1.00 | 1.00 | 1.25 | 0.40 | 1.40 | 1.00 | 1.00 | 1.00 |
| Gpr89 | 1.33 | 1.23 | 0.71 | 1.17 | 0.95 | 1.07 | 1.16 | 6.90 | 0.81 | 1.92 | 1.39 | 1.41 |
| Gpr97 | 1.00 | 1.00 | 1.00 | 1.00 | 1.00 | 1.00 | 3.54 | 1.00 | 2.82 | 1.53 | 1.78 | 1.63 |
| Gprc5a | 1.69 | 1.18 | 1.00 | 1.00 | 1.00 | 1.00 | 2.81 | 1.00 | 2.85 | 1.00 | 1.00 | 1.00 |
| Gpsm3 | 1.00 | 1.00 | 1.22 | 1.09 | 0.75 | 1.16 | 1.31 | 5.24 | 1.17 | 2.45 | 1.52 | 1.30 |
| Gpx1 | 0.80 | 0.96 | 0.70 | 1.31 | 0.79 | 1.14 | 1.46 | 4.78 | 1.03 | 1.36 | 1.08 | 0.97 |
| Gpx3 | 1.50 | 1.87 | 1.53 | 1.35 | 1.11 | 1.55 | 2.29 | 12.55 | 1.64 | 3.05 | 1.80 | 2.24 |
| Gpx4 | 0.96 | 0.71 | 0.82 | 1.21 | 0.83 | 1.03 | 1.77 | 29.18 | 1.12 | 4.16 | 1.42 | 1.24 |
| Gramd3 | 2.73 | 2.34 | 2.92 | 2.05 | 6.89 | 2.49 | 1.86 | 3.87 | 2.03 | 2.03 | 2.87 | 1.76 |
| Grcc10 | 0.68 | 0.81 | 0.79 | 1.17 | 0.85 | 1.00 | 1.17 | 13.11 | 0.86 | 3.22 | 1.28 | 1.36 |
| Grhpr | 0.84 | 1.21 | 1.01 | 1.17 | 1.10 | 1.03 | 0.79 | 8.88 | 0.79 | 2.74 | 0.72 | 1.17 |
| Gria1 | 1.00 | 1.00 | 1.00 | 1.10 | 1.19 | 1.02 | 0.73 | 1.53 | 1.33 | 1.00 | 1.00 | 1.00 |
| Gria2 | 1.00 | 1.00 | 1.00 | 0.86 | 1.12 | 0.89 | 1.00 | 1.00 | 1.00 | 1.00 | 1.00 | 1.00 |
| Grin1 | 1.00 | 1.00 | 1.00 | 1.08 | 0.88 | 1.05 | 1.00 | 1.00 | 1.00 | 1.00 | 1.00 | 1.00 |
| Grpel2 | 1.51 | 1.42 | 1.69 | 1.37 | 3.29 | 1.14 | 0.90 | 0.62 | 0.90 | 0.76 | 0.69 | 0.93 |
| Grrp1 | 1.35 | 1.00 | 1.33 | 1.86 | 6.80 | 1.25 | 1.23 | 2.56 | 1.16 | 1.00 | 1.00 | 1.00 |
| Gsg1 | 1.00 | 1.00 | 1.00 | 1.00 | 1.00 | 1.00 | 12.87 | 1.00 | 1.00 | 1.00 | 1.00 | 1.00 |
| Gskip | 1.11 | 1.11 | 0.94 | 1.25 | 5.81 | 1.22 | 0.94 | 1.24 | 0.90 | 1.05 | 0.96 | 1.05 |
| Gsn | 1.31 | 1.74 | 1.74 | 0.95 | 0.79 | 0.96 | 1.43 | 5.09 | 1.20 | 2.15 | 1.23 | 1.20 |
| Gss | 0.87 | 0.95 | 1.06 | 1.05 | 0.63 | 0.88 | 1.06 | 6.05 | 0.91 | 2.16 | 1.46 | 0.74 |
| Gsta3 | 0.55 | 0.44 | 0.74 | 1.00 | 1.45 | 1.00 | 2.72 | 7.17 | 1.81 | 1.00 | 1.00 | 1.00 |
| Gstk1 | 0.98 | 0.92 | 0.71 | 1.08 | 0.98 | 1.25 | 1.46 | 10.89 | 1.13 | 1.54 | 1.30 | 1.16 |
| Gstm2 | 0.43 | 0.45 | 0.46 | 1.81 | 0.19 | 1.44 | 1.82 | 1.57 | 1.35 | 1.00 | 1.00 | 1.00 |
| Gstm5 | 0.37 | 0.62 | 0.77 | 1.17 | 0.99 | 1.02 | 1.65 | 4.27 | 0.94 | 1.60 | 1.57 | 1.35 |
| Gstm6 | 0.42 | 0.77 | 0.69 | 0.81 | 1.69 | 0.90 | 1.36 | 1.37 | 0.82 | 1.00 | 1.00 | 1.00 |
| Gstm7 | 0.44 | 0.54 | 0.42 | 1.29 | 0.93 | 1.13 | 1.91 | 3.87 | 1.24 | 3.46 | 2.85 | 2.10 |
| Gstp1 | 0.83 | 0.64 | 0.90 | 1.14 | 0.87 | 0.93 | 1.32 | 13.93 | 1.32 | 3.33 | 1.29 | 1.20 |
| Gstp2 | 0.70 | 0.74 | 0.81 | 0.91 | 0.89 | 1.04 | 1.31 | 13.97 | 1.10 | 3.31 | 1.37 | 1.23 |
| Gstt2 | 1.07 | 0.68 | 0.79 | 0.98 | 1.13 | 0.67 | 1.15 | 7.44 | 1.17 | 1.44 | 0.64 | 0.78 |
| Gtf2b | 0.84 | 0.92 | 0.82 | 0.80 | 6.56 | 0.84 | 1.10 | 0.71 | 1.05 | 0.88 | 1.14 | 1.31 |
| Gtf2f2 | 1.00 | 0.81 | 0.88 | 1.26 | 0.57 | 1.05 | 0.98 | 5.67 | 0.77 | 2.34 | 1.26 | 1.25 |
| Gtf2h4 | 1.00 | 1.00 | 1.00 | 0.88 | 0.94 | 1.45 | 1.00 | 10.03 | 1.07 | 3.78 | 1.10 | 1.13 |
| Gtf2h5 | 0.87 | 0.46 | 0.93 | 1.05 | 0.82 | 1.08 | 1.09 | 5.07 | 1.02 | 2.39 | 1.14 | 1.13 |
| Gtf3c6 | 0.75 | 0.95 | 1.31 | 0.99 | 0.86 | 0.84 | 0.73 | 9.29 | 0.92 | 3.15 | 1.07 | 1.10 |
| Gtl3 | 1.03 | 0.77 | 0.59 | 1.04 | 1.37 | 1.01 | 0.99 | 1.88 | 0.84 | 1.19 | 0.98 | 0.92 |
| Gtpbp6 | 1.00 | 1.00 | 1.00 | 1.75 | 0.74 | 1.11 | 2.15 | 3.46 | 0.98 | 2.26 | 1.32 | 1.06 |
| Guca1a | 1.00 | 1.00 | 1.00 | 1.00 | 0.74 | 1.00 | 1.50 | 60.56 | 1.29 | 11.44 | 1.20 | 2.66 |
| Guca2a | 1.00 | 1.00 | 1.00 | 1.00 | 1.00 | 1.00 | 0.81 | 7.61 | 0.95 | 1.00 | 1.00 | 1.00 |
| Guca2b | 1.00 | 1.00 | 1.00 | 1.00 | 1.00 | 1.00 | 1.02 | 1.00 | 1.00 | 1.00 | 1.00 | 1.00 |
| Gusb | 1.34 | 1.37 | 1.09 | 1.01 | 1.82 | 1.27 | 0.99 | 3.25 | 0.94 | 1.89 | 1.57 | 1.25 |
| Gxylt2 | 1.00 | 1.00 | 1.00 | 1.00 | 1.00 | 1.00 | 0.61 | 0.80 | 0.71 | 1.00 | 1.00 | 1.00 |
| Gys2 | 1.00 | 1.00 | 1.00 | 1.00 | 1.00 | 1.00 | 1.00 | 1.00 | 1.00 | 1.00 | 1.00 | 1.00 |
| Gzmm | 1.00 | 1.00 | 1.00 | 1.00 | 1.71 | 0.90 | 5.34 | 33.06 | 2.24 | 1.01 | 1.00 | 1.60 |
| H13 | 1.02 | 0.87 | 0.94 | 1.06 | 0.98 | 0.96 | 1.25 | 5.93 | 0.95 | 2.69 | 1.21 | 1.08 |
| H1fx | 1.00 | 1.00 | 1.00 | 1.03 | 0.80 | 1.10 | 1.08 | 6.79 | 0.78 | 1.80 | 0.98 | 0.82 |
| H2-Bl | 1.00 | 1.00 | 1.00 | 3.42 | 1.35 | 6.31 | 1.81 | 1.00 | 0.59 | 1.00 | 1.68 | 1.47 |
| H2-D1 | 1.10 | 1.18 | 1.03 | 0.71 | 1.66 | 0.78 | 1.60 | 4.64 | 0.93 | 1.74 | 1.38 | 1.12 |
| H2-Ea-ps | 1.00 | 2.90 | 6.15 | 1.00 | 1.00 | 1.00 | 68.46 | 1.00 | 78.49 | 11.18 | 90.44 | 93.14 |
| H2-K2 | 1.00 | 1.00 | 1.36 | 1.00 | 1.00 | 1.00 | 5.08 | 1.80 | 2.22 | 1.74 | 1.96 | 1.41 |
| H2-Ke2 | 1.40 | 1.60 | 1.26 | 1.16 | 0.86 | 1.05 | 1.50 | 20.84 | 1.11 | 3.58 | 1.13 | 1.09 |
| H2-Ke6 | 0.63 | 0.99 | 0.54 | 0.88 | 0.56 | 0.58 | 1.24 | 9.18 | 1.08 | 2.49 | 1.04 | 1.11 |
| H2-Q1 | 2.57 | 3.39 | 2.37 | 0.92 | 1.00 | 0.88 | 7.00 | 0.26 | 3.03 | 0.61 | 2.72 | 2.27 |

Fig. 35- 185

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| H2-Q10 | 3.37 | 5.04 | 6.62 | 91.09 | 336.27 | 100.83 | 4.42 | 3.52 | 6.83 | 10.26 | 5.20 | 3.74 |
| H2-T22 | 1.72 | 2.13 | 1.97 | 5.09 | 0.13 | 1.03 | 2.33 | 1.43 | 2.66 | 0.73 | 0.11 | 2.98 |
| H2afb1 | 1.00 | 1.00 | 1.00 | 1.00 | 1.00 | 1.00 | 1.00 | 1.00 | 1.00 | 1.00 | 1.00 | 1.00 |
| H2afj | 1.24 | 0.61 | 1.05 | 0.27 | 13.38 | 1.13 | 1.45 | 0.77 | 0.96 | 2.40 | 4.64 | 1.03 |
| H2afv | 0.82 | 0.75 | 0.84 | 0.52 | 2.72 | 0.86 | 0.92 | 0.71 | 0.73 | 0.81 | 1.24 | 0.97 |
| H60c | 1.00 | 1.00 | 1.00 | 1.00 | 1.00 | 1.00 | 1.00 | 1.00 | 1.00 | 1.00 | 1.00 | 1.00 |
| Hadha | 0.90 | 0.46 | 0.88 | 0.38 | 3.83 | 0.91 | 0.77 | 0.71 | 0.68 | 2.24 | 3.08 | 1.02 |
| Haghl | 1.16 | 0.80 | 0.32 | 0.42 | 1.01 | 1.45 | 0.77 | 0.68 | 0.80 | 3.99 | 5.16 | 1.07 |
| Hal | 1.41 | 1.10 | 1.75 | 3.88 | 24.43 | 3.58 | 1.00 | 1.00 | 1.42 | 1.00 | 1.00 | 1.00 |
| Hamp | 1.00 | 2.26 | 1.00 | 1.82 | 5.23 | 1.00 | 0.68 | 0.14 | 0.58 | 0.50 | 2.70 | 0.63 |
| Hamp2 | 1.10 | 1.00 | 1.00 | 2.43 | 21.26 | 1.00 | 1.00 | 1.00 | 1.00 | 1.44 | 1.61 | 1.00 |
| Hapln4 | 1.00 | 1.00 | 1.00 | 1.00 | 0.23 | 0.96 | 1.00 | 1.00 | 1.00 | 1.00 | 1.00 | 1.00 |
| Haus7 | 1.32 | 0.50 | 0.65 | 0.44 | 7.88 | 0.96 | 0.96 | 0.64 | 0.90 | 3.40 | 3.99 | 1.02 |
| Haus8 | 1.00 | 1.26 | 1.00 | 0.81 | 2.44 | 0.63 | 1.20 | 1.50 | 1.04 | 1.55 | 1.93 | 0.70 |
| Hax1 | 1.15 | 0.85 | 0.94 | 0.33 | 1.81 | 0.86 | 1.07 | 1.04 | 0.95 | 1.39 | 1.49 | 1.12 |
| Hba-a1 | 1.43 | 0.66 | 1.32 | 0.43 | 5.14 | 1.14 | 0.38 | 0.62 | 0.26 | 2.97 | 3.98 | 1.23 |
| Hba-a2 | 0.25 | 0.31 | 1.05 | 0.09 | 22.47 | 1.38 | 0.66 | 0.48 | 0.25 | 8.75 | 10.01 | 0.69 |
| Hbb-b1 | 1.05 | 0.58 | 1.11 | 0.29 | 7.08 | 1.16 | 0.51 | 0.66 | 0.29 | 2.85 | 4.19 | 1.19 |
| Hbb-bs | 0.50 | 0.40 | 3.12 | 0.18 | 19.72 | 0.84 | 0.69 | 0.40 | 0.38 | 10.47 | 12.39 | 0.92 |
| Hbb-bt | 1.05 | 0.87 | 1.26 | 0.34 | 3.58 | 1.19 | 0.50 | 0.70 | 0.33 | 1.47 | 2.25 | 1.14 |
| Hbs1l | 1.12 | 0.62 | 0.95 | 1.14 | 6.45 | 1.23 | 1.05 | 1.17 | 0.90 | 1.96 | 3.14 | 1.06 |
| Hcfc1r1 | 1.17 | 0.62 | 0.98 | 0.55 | 4.86 | 0.89 | 0.88 | 0.82 | 0.87 | 1.69 | 2.20 | 0.89 |
| Hcls1 | 0.74 | 0.70 | 1.42 | 0.76 | 10.16 | 2.17 | 1.38 | 1.26 | 1.48 | 2.51 | 2.52 | 0.88 |
| Hcn2 | 0.96 | 1.12 | 1.01 | 0.46 | 0.72 | 1.35 | 1.88 | 1.31 | 1.12 | 1.50 | 1.38 | 1.00 |
| Hcrtr1 | 1.00 | 1.00 | 1.00 | 1.00 | 1.00 | 1.00 | 1.00 | 1.00 | 1.00 | 1.00 | 1.00 | 1.00 |
| Hcst | 1.00 | 1.00 | 1.00 | 1.00 | 2.57 | 1.00 | 1.00 | 1.00 | 1.00 | 3.14 | 3.02 | 1.34 |
| Hdac10 | 1.01 | 0.62 | 0.85 | 0.64 | 1.90 | 1.01 | 1.02 | 0.88 | 0.93 | 1.02 | 0.88 | 0.94 |
| Hddc2 | 1.07 | 0.44 | 0.73 | 0.55 | 14.81 | 1.20 | 0.83 | 1.04 | 1.16 | 2.76 | 6.39 | 0.89 |
| Hdgfrp2 | 1.29 | 0.76 | 1.05 | 0.83 | 4.65 | 1.11 | 1.28 | 1.53 | 1.10 | 2.24 | 2.54 | 1.03 |
| Hebp2 | 1.00 | 1.00 | 1.00 | 0.55 | 1.24 | 1.50 | 1.00 | 1.00 | 1.00 | 1.00 | 1.00 | 1.00 |
| Hexa | 1.24 | 0.63 | 1.08 | 0.64 | 6.59 | 1.50 | 1.31 | 1.05 | 1.14 | 2.18 | 3.56 | 0.98 |
| Hgd | 1.00 | 1.00 | 1.00 | 1.36 | 14.76 | 1.35 | 1.00 | 1.00 | 1.00 | 1.00 | 1.00 | 1.00 |
| Hgf | 1.00 | 1.00 | 1.00 | 1.00 | 1.00 | 1.00 | 1.00 | 1.00 | 1.00 | 1.00 | 1.00 | 0.58 |
| Hgs | 1.72 | 0.88 | 1.45 | 0.78 | 6.24 | 1.17 | 1.62 | 1.05 | 1.19 | 2.20 | 2.89 | 1.03 |
| Hhatl | 1.18 | 0.66 | 0.83 | 1.00 | 1.06 | 1.00 | 0.98 | 0.80 | 0.74 | 4.59 | 2.43 | 0.74 |
| Higd1b | 1.07 | 0.82 | 1.43 | 0.57 | 2.51 | 0.96 | 1.67 | 1.09 | 1.40 | 1.22 | 1.57 | 1.03 |
| Hilpda | 1.45 | 1.01 | 0.67 | 2.27 | 1.22 | 1.34 | 0.67 | 0.61 | 0.97 | 0.17 | 0.37 | 1.33 |
| Hils1 | 0.43 | 1.00 | 1.38 | 1.00 | 1.00 | 1.00 | 0.64 | 2.88 | 1.20 | 1.00 | 1.00 | 1.00 |
| Hint1 | 1.20 | 0.85 | 0.98 | 0.48 | 4.24 | 1.23 | 1.03 | 0.78 | 0.87 | 0.98 | 1.66 | 1.02 |
| Hint2 | 0.55 | 0.17 | 0.26 | 0.15 | 7.86 | 0.73 | 0.55 | 0.53 | 0.51 | 2.47 | 2.76 | 0.86 |
| Hip1r | 2.14 | 1.31 | 1.73 | 1.51 | 8.21 | 0.92 | 1.06 | 1.03 | 0.88 | 2.46 | 2.37 | 1.13 |
| Hipk2 | 0.69 | 1.00 | 1.14 | 0.46 | 0.57 | 0.34 | 2.06 | 2.76 | 5.30 | 1.00 | 1.00 | 1.48 |
| Hist1h1c | 1.23 | 7.16 | 1.20 | 2.75 | 0.10 | 1.41 | 2.88 | 2.95 | 1.60 | 0.12 | 0.11 | 1.59 |
| Hist1h2ah | 1.00 | 1.00 | 1.00 | 1.00 | 1.01 | 1.00 | 1.00 | 1.00 | 1.00 | 1.00 | 1.00 | 1.00 |
| Hist1h2ai | 1.00 | 1.00 | 1.00 | 0.46 | 0.89 | 1.00 | 1.00 | 1.20 | 1.00 | 1.00 | 1.00 | 1.02 |
| Hist1h2ba | 1.02 | 1.90 | 1.35 | 1.01 | 0.83 | 1.25 | 2.14 | 1.86 | 1.22 | 0.35 | 1.16 | 1.60 |
| Hist1h2bc | 1.17 | 1.37 | 1.05 | 0.64 | 1.28 | 1.25 | 1.66 | 1.54 | 1.29 | 0.79 | 1.50 | 1.63 |
| Hist1h2be | 1.29 | 4.62 | 0.96 | 0.42 | 0.61 | 1.37 | 1.78 | 1.83 | 1.11 | 0.30 | 0.34 | 1.53 |
| Hist1h2bg | 1.32 | 2.18 | 1.17 | 0.50 | 0.31 | 1.05 | 2.46 | 1.19 | 1.12 | 0.17 | 0.41 | 1.51 |
| Hist1h2bj | 1.25 | 2.41 | 0.91 | 0.89 | 0.44 | 1.67 | 2.35 | 2.03 | 0.81 | 0.29 | 0.91 | 2.38 |
| Hist1h4a | 2.07 | 0.79 | 1.78 | 0.18 | 7.81 | 0.89 | 0.89 | 1.08 | 1.64 | 5.50 | 4.51 | 1.87 |
| Hist1h4b | 0.88 | 0.86 | 2.05 | 0.11 | 7.34 | 0.78 | 2.19 | 1.04 | 0.71 | 5.19 | 5.38 | 1.00 |
| Hist1h4c | 2.06 | 0.92 | 2.37 | 0.10 | 14.15 | 1.84 | 2.37 | 1.12 | 1.48 | 4.19 | 5.15 | 1.49 |
| Hist1h4f | 2.33 | 0.57 | 3.05 | 0.15 | 4.96 | 0.78 | 0.61 | 2.94 | 1.00 | 1.00 | 1.11 | 1.00 |
| Hist1h4h | 1.30 | 0.69 | 1.23 | 0.21 | 7.30 | 0.91 | 1.24 | 0.71 | 0.75 | 2.15 | 4.57 | 1.13 |
| Hist1h4i | 3.90 | 5.46 | 3.43 | 0.59 | 2.52 | 2.01 | 6.32 | 10.42 | 6.11 | 0.89 | 2.25 | 3.99 |
| Hist1h4j | 1.35 | 0.90 | 1.35 | 0.14 | 10.25 | 0.75 | 1.44 | 0.77 | 0.57 | 4.32 | 8.98 | 1.28 |
| Hist1h4k | 1.94 | 0.58 | 0.99 | 0.21 | 14.24 | 0.67 | 1.46 | 0.69 | 0.75 | 6.12 | 7.05 | 2.95 |
| Hist1h4n | 10.08 | 3.74 | 6.86 | 0.20 | 6.95 | 1.67 | 4.91 | 3.95 | 1.14 | 1.00 | 2.70 | 1.19 |
| Hist2h2aa1 | 1.27 | 0.71 | 1.02 | 0.34 | 5.24 | 0.97 | 1.53 | 0.92 | 0.95 | 1.66 | 3.35 | 1.45 |
| Hist2h2aa2 | 1.82 | 1.00 | 1.33 | 1.95 | 0.79 | 0.83 | 1.87 | 3.71 | 0.39 | 1.00 | 1.00 | 1.01 |
| Hist2h2ac | 1.25 | 0.72 | 1.85 | 0.66 | 6.06 | 1.25 | 2.14 | 0.74 | 1.06 | 0.86 | 2.29 | 1.45 |
| Hist2h3c1 | 1.26 | 3.13 | 9.01 | 1.00 | 1.00 | 1.00 | 1.00 | 1.00 | 1.00 | 1.00 | 1.00 | 0.83 |
| Hmg20b | 1.07 | 0.58 | 0.91 | 0.41 | 6.56 | 0.93 | 0.90 | 0.72 | 0.86 | 2.36 | 3.25 | 1.01 |

Fig. 35- 186

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| H2-Q10 | 1.66 | 1.36 | 1.62 | 2.69 | 1.49 | 4.68 | 2.75 | 2.91 | 2.27 | 3.15 | 4.60 | 3.35 |
| H2-T22 | 0.61 | 0.49 | 1.33 | 1.70 | 1.00 | 2.55 | 1.66 | 1.00 | 1.41 | 1.19 | 1.03 | 1.11 |
| H2afb1 | 1.00 | 1.00 | 1.00 | 1.00 | 1.00 | 1.00 | 1.00 | 1.00 | 1.00 | 1.00 | 1.00 | 1.00 |
| H2afj | 0.99 | 1.26 | 0.86 | 0.85 | 0.64 | 1.12 | 1.14 | 1.78 | 0.98 | 0.80 | 1.24 | 0.89 |
| H2afv | 0.91 | 1.13 | 0.74 | 0.91 | 1.18 | 0.78 | 1.00 | 0.62 | 0.71 | 1.00 | 1.58 | 0.94 |
| H60c | 1.00 | 1.00 | 1.00 | 1.00 | 1.00 | 1.00 | 1.00 | 1.00 | 1.00 | 1.00 | 1.00 | 1.00 |
| Hadha | 1.06 | 1.11 | 0.87 | 0.78 | 0.55 | 0.93 | 0.94 | 1.35 | 0.86 | 1.02 | 1.27 | 1.13 |
| Haghl | 0.90 | 1.00 | 1.15 | 0.94 | 0.18 | 0.68 | 0.91 | 2.15 | 0.89 | 0.54 | 1.03 | 1.04 |
| Hal | 1.24 | 1.55 | 1.26 | 1.00 | 1.00 | 1.00 | 1.14 | 1.30 | 0.86 | 1.00 | 1.08 | 1.15 |
| Hamp | 4.10 | 3.07 | 0.75 | 1.00 | 1.00 | 0.86 | 1.61 | 1.35 | 1.50 | 1.00 | 0.87 | 1.00 |
| Hamp2 | 1.47 | 1.00 | 1.00 | 1.00 | 1.00 | 1.00 | 0.05 | 0.08 | 0.33 | 0.77 | 1.17 | 1.29 |
| Hapln4 | 1.00 | 1.00 | 1.00 | 1.00 | 1.00 | 1.00 | 0.84 | 1.00 | 0.94 | 1.00 | 1.00 | 1.00 |
| Haus7 | 1.01 | 1.54 | 0.88 | 0.56 | 0.60 | 0.57 | 1.05 | 1.82 | 0.49 | 0.79 | 1.42 | 0.69 |
| Haus8 | 0.60 | 0.76 | 0.70 | 0.97 | 0.63 | 1.00 | 1.00 | 1.14 | 1.65 | 0.84 | 1.29 | 0.74 |
| Hax1 | 1.13 | 0.85 | 0.99 | 0.93 | 0.81 | 0.86 | 1.16 | 1.08 | 0.90 | 1.03 | 1.28 | 1.13 |
| Hba-a1 | 0.71 | 1.65 | 0.60 | 0.43 | 0.50 | 0.47 | 0.63 | 1.95 | 0.70 | 1.46 | 1.20 | 0.38 |
| Hba-a2 | 1.62 | 0.57 | 1.48 | 0.06 | 0.23 | 0.65 | 42.71 | 3.79 | 0.83 | 0.05 | 32.12 | 2.03 |
| Hbb-b1 | 0.95 | 1.48 | 0.72 | 0.43 | 0.52 | 0.58 | 0.92 | 2.18 | 0.64 | 1.12 | 1.92 | 0.85 |
| Hbb-bs | 0.84 | 0.14 | 0.42 | 1.00 | 0.18 | 0.12 | 1.00 | 1.97 | 33.76 | 1.00 | 7.93 | 0.11 |
| Hbb-bt | 1.02 | 1.57 | 0.65 | 0.48 | 0.64 | 0.50 | 0.77 | 1.04 | 0.74 | 0.90 | 1.99 | 0.75 |
| Hbs1l | 1.03 | 1.16 | 0.96 | 1.21 | 0.97 | 1.20 | 1.42 | 1.89 | 1.24 | 1.15 | 1.60 | 1.07 |
| Hcfc1r1 | 1.34 | 1.64 | 1.05 | 0.73 | 0.75 | 0.81 | 0.75 | 1.25 | 0.85 | 1.09 | 1.48 | 1.04 |
| Hcls1 | 1.09 | 1.40 | 1.03 | 0.90 | 0.97 | 0.99 | 1.00 | 1.61 | 0.82 | 0.78 | 1.14 | 1.14 |
| Hcn2 | 1.00 | 1.00 | 1.00 | 1.47 | 2.38 | 1.79 | 1.00 | 1.00 | 1.00 | 1.15 | 1.07 | 0.94 |
| Hcrtr1 | 1.00 | 1.00 | 1.00 | 1.00 | 1.00 | 1.00 | 1.00 | 1.00 | 1.00 | 1.00 | 1.00 | 1.00 |
| Hcst | 1.08 | 1.44 | 1.32 | 1.00 | 0.45 | 0.86 | 1.00 | 0.59 | 1.00 | 0.72 | 1.78 | 0.40 |
| Hdac10 | 1.06 | 0.91 | 0.87 | 0.88 | 0.68 | 0.94 | 1.23 | 1.37 | 1.03 | 0.96 | 1.00 | 1.05 |
| Hddc2 | 1.54 | 1.46 | 0.70 | 0.50 | 0.47 | 0.89 | 1.00 | 1.63 | 1.00 | 1.17 | 1.82 | 0.96 |
| Hdgfrp2 | 1.09 | 1.10 | 1.00 | 1.07 | 1.05 | 1.04 | 1.12 | 1.51 | 1.15 | 1.08 | 1.30 | 1.16 |
| Hebp2 | 1.39 | 1.55 | 1.07 | 1.00 | 0.86 | 1.00 | 1.00 | 1.00 | 1.00 | 2.79 | 5.54 | 3.74 |
| Hexa | 1.79 | 2.04 | 1.70 | 1.21 | 0.94 | 1.55 | 1.22 | 1.48 | 0.99 | 1.16 | 1.46 | 1.07 |
| Hgd | 1.00 | 1.00 | 1.00 | 1.21 | 1.08 | 1.10 | 1.84 | 2.86 | 1.43 | 1.00 | 1.00 | 1.00 |
| Hgf | 1.00 | 1.00 | 1.01 | 1.00 | 1.00 | 1.00 | 2.12 | 1.00 | 1.44 | 0.95 | 1.00 | 1.00 |
| Hgs | 1.06 | 1.30 | 1.14 | 1.27 | 0.77 | 1.04 | 1.37 | 2.03 | 1.40 | 1.06 | 1.46 | 1.03 |
| Hhatl | 1.00 | 1.00 | 1.00 | 0.84 | 0.79 | 1.02 | 1.00 | 1.00 | 1.00 | 1.34 | 1.73 | 1.21 |
| Higd1b | 1.30 | 2.46 | 1.11 | 0.91 | 1.37 | 1.01 | 1.00 | 1.00 | 1.00 | 0.95 | 1.00 | 1.00 |
| Hilpda | 1.17 | 1.11 | 1.06 | 1.31 | 1.51 | 0.87 | 1.92 | 2.41 | 1.82 | 1.05 | 1.32 | 1.15 |
| Hils1 | 1.00 | 1.00 | 1.00 | 1.00 | 1.00 | 1.00 | 1.00 | 1.00 | 1.00 | 1.00 | 1.00 | 1.00 |
| Hint1 | 1.11 | 1.33 | 1.01 | 1.06 | 1.23 | 0.99 | 1.04 | 0.70 | 1.03 | 1.07 | 1.75 | 1.12 |
| Hint2 | 0.69 | 1.44 | 0.64 | 0.47 | 0.35 | 0.49 | 0.47 | 1.45 | 0.60 | 0.66 | 1.21 | 0.62 |
| Hip1r | 1.83 | 1.69 | 1.55 | 1.15 | 0.96 | 1.18 | 3.17 | 6.60 | 1.80 | 1.06 | 1.38 | 1.11 |
| Hipk2 | 0.69 | 1.00 | 1.51 | 2.43 | 1.00 | 2.24 | 0.53 | 1.00 | 0.97 | 0.97 | 0.89 | 0.59 |
| Hist1h1c | 2.25 | 2.56 | 1.63 | 1.77 | 3.51 | 1.37 | 4.30 | 8.37 | 2.08 | 1.07 | 0.84 | 0.96 |
| Hist1h2ah | 0.56 | 2.07 | 0.48 | 1.00 | 1.00 | 1.50 | 1.00 | 1.00 | 1.00 | 1.00 | 1.00 | 1.00 |
| Hist1h2ai | 1.16 | 0.52 | 0.31 | 1.00 | 1.00 | 1.00 | 1.00 | 1.00 | 1.00 | 1.00 | 1.13 | 1.10 |
| Hist1h2ba | 2.06 | 1.74 | 2.35 | 1.43 | 8.22 | 2.21 | 1.33 | 0.31 | 1.60 | 1.63 | 3.73 | 1.42 |
| Hist1h2bc | 1.66 | 1.75 | 1.36 | 1.36 | 1.91 | 1.38 | 1.51 | 0.79 | 1.12 | 1.69 | 2.11 | 1.39 |
| Hist1h2be | 1.26 | 1.00 | 1.18 | 1.21 | 8.93 | 1.28 | 1.50 | 1.00 | 1.48 | 1.52 | 1.78 | 1.27 |
| Hist1h2bg | 1.29 | 1.41 | 1.29 | 1.27 | 9.38 | 1.45 | 0.98 | 0.69 | 1.28 | 2.14 | 1.72 | 1.25 |
| Hist1h2bj | 0.91 | 0.46 | 0.42 | 1.43 | 6.93 | 1.39 | 1.58 | 0.70 | 0.92 | 1.19 | 1.99 | 1.20 |
| Hist1h4a | 1.03 | 1.00 | 0.68 | 1.19 | 0.98 | 1.94 | 1.00 | 3.37 | 1.00 | 1.00 | 2.10 | 1.34 |
| Hist1h4b | 0.81 | 0.48 | 0.47 | 1.00 | 0.82 | 1.17 | 1.00 | 2.06 | 1.00 | 1.00 | 2.45 | 0.62 |
| Hist1h4c | 2.73 | 1.44 | 0.83 | 2.97 | 1.06 | 1.90 | 1.00 | 3.90 | 1.00 | 0.69 | 1.02 | 1.03 |
| Hist1h4f | 0.67 | 0.79 | 1.00 | 1.00 | 1.00 | 1.00 | 1.00 | 0.73 | 1.00 | 1.00 | 1.00 | 1.00 |
| Hist1h4h | 1.65 | 0.91 | 0.81 | 1.01 | 0.88 | 1.60 | 3.23 | 2.89 | 2.31 | 1.36 | 1.67 | 0.91 |
| Hist1h4i | 0.94 | 0.87 | 0.66 | 3.79 | 2.43 | 2.42 | 1.72 | 0.45 | 2.16 | 1.91 | 2.20 | 1.43 |
| Hist1h4j | 0.84 | 3.59 | 0.50 | 1.32 | 0.77 | 1.87 | 3.52 | 3.04 | 1.70 | 0.93 | 1.82 | 1.20 |
| Hist1h4k | 1.05 | 0.51 | 1.94 | 0.65 | 0.82 | 3.27 | 1.00 | 5.01 | 1.00 | 1.04 | 1.38 | 1.09 |
| Hist1h4n | 0.69 | 0.96 | 0.50 | 3.12 | 0.74 | 2.84 | 1.00 | 0.93 | 0.93 | 2.86 | 1.92 | 1.04 |
| Hist2h2aa1 | 1.80 | 2.12 | 1.49 | 1.42 | 1.39 | 1.90 | 1.34 | 0.99 | 1.34 | 1.10 | 1.62 | 1.40 |
| Hist2h2aa2 | 1.76 | 1.38 | 4.16 | 2.02 | 1.00 | 6.08 | 1.00 | 1.00 | 1.00 | 1.14 | 2.06 | 1.18 |
| Hist2h2ac | 1.68 | 1.20 | 1.77 | 3.61 | 2.42 | 1.65 | 2.33 | 0.22 | 1.91 | 1.45 | 1.71 | 1.99 |
| Hist2h3c1 | 1.00 | 1.00 | 1.00 | 0.58 | 1.00 | 1.00 | 1.00 | 1.00 | 1.00 | 1.00 | 3.83 | 1.00 |
| Hmg20b | 1.13 | 1.46 | 0.96 | 0.91 | 0.64 | 1.08 | 0.90 | 1.69 | 0.86 | 0.97 | 1.35 | 1.06 |

Fig. 35- 187

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| H2-Q10 | 5.27 | 3.69 | 4.48 | 6.24 | 7.41 | 6.53 | 1.00 | 1.00 | 1.00 | 2.35 | 1.89 | 1.83 |
| H2-T22 | 1.05 | 1.09 | 1.27 | 1.06 | 0.14 | 1.32 | 0.46 | 1.00 | 0.58 | 1.17 | 0.87 | 1.53 |
| H2afb1 | 1.00 | 1.00 | 1.00 | 2.55 | 1.39 | 1.00 | 0.79 | 1.01 | 0.85 | 1.00 | 1.00 | 1.00 |
| H2afj | 0.79 | 0.98 | 0.81 | 1.08 | 2.37 | 1.01 | 0.80 | 2.43 | 0.82 | 0.89 | 1.29 | 0.93 |
| H2afv | 1.20 | 1.15 | 1.36 | 0.87 | 6.25 | 1.07 | 0.95 | 0.62 | 0.73 | 1.08 | 1.25 | 1.07 |
| H60c | 6.57 | 6.50 | 5.24 | 1.00 | 1.00 | 1.00 | 1.00 | 1.00 | 1.00 | 1.00 | 1.00 | 1.00 |
| Hadha | 0.86 | 0.84 | 0.98 | 0.93 | 2.56 | 1.01 | 0.95 | 1.87 | 0.89 | 0.99 | 1.21 | 0.97 |
| Haghl | 0.54 | 0.80 | 0.71 | 0.91 | 0.73 | 0.80 | 0.75 | 5.75 | 0.99 | 0.93 | 1.00 | 0.96 |
| Hal | 1.00 | 1.00 | 1.00 | 2.59 | 2.73 | 1.24 | 0.67 | 1.11 | 0.69 | 1.00 | 1.00 | 1.00 |
| Hamp | 0.70 | 0.90 | 0.40 | 1.00 | 1.00 | 1.00 | 1.00 | 1.00 | 1.00 | 1.00 | 1.00 | 1.00 |
| Hamp2 | 2.02 | 2.22 | 1.55 | 1.00 | 1.00 | 1.00 | 1.00 | 1.00 | 1.00 | 1.00 | 1.00 | 1.00 |
| Hapln4 | 1.00 | 1.00 | 1.00 | 1.00 | 1.00 | 1.00 | 1.00 | 1.00 | 1.00 | 1.00 | 6.64 | 1.00 |
| Haus7 | 0.58 | 0.74 | 0.83 | 0.87 | 2.37 | 0.91 | 0.78 | 3.02 | 0.97 | 0.95 | 1.00 | 0.80 |
| Haus8 | 0.58 | 0.50 | 0.58 | 0.71 | 1.00 | 0.76 | 0.98 | 1.54 | 1.14 | 0.53 | 0.75 | 0.62 |
| Hax1 | 0.85 | 1.00 | 0.95 | 1.02 | 1.56 | 1.10 | 1.08 | 1.57 | 0.98 | 0.96 | 1.04 | 1.00 |
| Hba-a1 | 1.13 | 1.48 | 2.08 | 0.80 | 5.45 | 0.98 | 0.83 | 2.26 | 0.69 | 0.40 | 0.41 | 0.18 |
| Hba-a2 | 1.00 | 0.79 | 0.39 | 0.37 | 1.13 | 0.72 | 1.00 | 3.16 | 1.00 | 0.40 | 0.34 | 0.20 |
| Hbb-b1 | 1.45 | 1.21 | 1.15 | 0.76 | 3.00 | 0.93 | 0.85 | 2.24 | 0.89 | 0.41 | 0.40 | 0.20 |
| Hbb-bs | 1.00 | 1.00 | 2.23 | 0.86 | 1.47 | 1.59 | 1.00 | 0.18 | 1.00 | 0.33 | 0.30 | 0.23 |
| Hbb-bt | 1.27 | 1.16 | 1.23 | 0.78 | 1.17 | 0.99 | 0.68 | 0.67 | 0.65 | 0.43 | 0.39 | 0.20 |
| Hbs1l | 1.11 | 0.87 | 1.13 | 1.17 | 2.32 | 1.00 | 1.03 | 1.51 | 1.04 | 1.14 | 1.20 | 1.01 |
| Hcfc1r1 | 0.90 | 0.95 | 1.04 | 0.58 | 2.02 | 0.70 | 0.95 | 1.67 | 1.00 | 1.13 | 1.39 | 0.82 |
| Hcls1 | 0.84 | 1.23 | 1.34 | 1.15 | 3.04 | 1.06 | 1.00 | 1.82 | 1.00 | 1.15 | 1.32 | 0.99 |
| Hcn2 | 0.72 | 1.10 | 0.83 | 0.71 | 1.00 | 0.71 | 1.00 | 1.00 | 1.00 | 1.00 | 6.04 | 1.00 |
| Hcrtr1 | 1.00 | 1.00 | 1.00 | 2.62 | 1.00 | 1.16 | 1.00 | 1.00 | 1.00 | 1.00 | 1.00 | 1.00 |
| Hcst | 1.00 | 1.00 | 0.74 | 0.64 | 0.78 | 0.64 | 1.00 | 1.00 | 1.00 | 0.93 | 1.20 | 0.67 |
| Hdac10 | 1.02 | 1.03 | 1.09 | 1.03 | 0.76 | 1.01 | 0.88 | 1.00 | 0.93 | 0.88 | 0.78 | 0.92 |
| Hddc2 | 0.91 | 1.37 | 1.15 | 0.87 | 2.00 | 0.91 | 0.70 | 4.89 | 0.55 | 1.00 | 1.51 | 0.89 |
| Hdgfrp2 | 1.19 | 1.22 | 1.15 | 1.06 | 2.26 | 1.19 | 0.95 | 1.84 | 1.05 | 0.94 | 1.31 | 0.90 |
| Hebp2 | 1.42 | 1.74 | 1.55 | 1.00 | 1.00 | 1.00 | 1.51 | 1.05 | 1.83 | 1.00 | 1.00 | 1.00 |
| Hexa | 1.10 | 1.18 | 1.06 | 0.92 | 1.96 | 0.83 | 0.97 | 2.14 | 1.00 | 1.05 | 1.33 | 0.99 |
| Hgd | 1.00 | 1.00 | 1.00 | 2.11 | 5.01 | 1.00 | 1.00 | 1.66 | 1.00 | 1.00 | 1.00 | 1.00 |
| Hgf | 0.83 | 0.62 | 1.00 | 1.00 | 1.00 | 1.00 | 1.00 | 5.27 | 1.00 | 1.00 | 1.00 | 1.00 |
| Hgs | 0.99 | 1.00 | 0.78 | 1.37 | 4.52 | 1.30 | 0.98 | 1.98 | 1.05 | 0.99 | 1.11 | 1.01 |
| Hhatl | 1.46 | 2.32 | 1.25 | 1.00 | 1.00 | 1.00 | 1.02 | 2.46 | 0.91 | 1.00 | 1.00 | 1.00 |
| Higd1b | 1.33 | 1.09 | 1.00 | 1.17 | 5.97 | 1.13 | 0.99 | 1.00 | 1.00 | 1.00 | 1.00 | 1.00 |
| Hilpda | 0.85 | 0.93 | 0.92 | 4.26 | 5.14 | 1.86 | 0.99 | 0.23 | 1.11 | 1.02 | 1.47 | 1.03 |
| Hils1 | 1.00 | 1.00 | 1.00 | 3.89 | 5.50 | 1.10 | 0.87 | 1.33 | 1.03 | 1.00 | 1.00 | 1.00 |
| Hint1 | 1.00 | 1.12 | 1.03 | 1.20 | 6.16 | 1.32 | 0.94 | 0.63 | 0.99 | 1.15 | 1.33 | 0.98 |
| Hint2 | 0.95 | 1.09 | 0.83 | 0.43 | 1.24 | 0.62 | 0.98 | 2.92 | 0.45 | 0.50 | 0.83 | 0.89 |
| Hip1r | 1.05 | 1.20 | 0.97 | 1.16 | 2.30 | 1.36 | 1.15 | 2.56 | 0.97 | 1.22 | 1.18 | 1.15 |
| Hipk2 | 0.89 | 0.95 | 0.34 | 0.80 | 0.08 | 0.30 | 0.92 | 1.00 | 1.06 | 0.72 | 1.04 | 1.10 |
| Hist1h1c | 1.26 | 1.71 | 0.99 | 2.27 | 0.05 | 1.20 | 1.11 | 3.18 | 1.07 | 1.27 | 1.19 | 0.93 |
| Hist1h2ah | 1.00 | 1.00 | 1.00 | 1.00 | 0.89 | 1.00 | 1.18 | 0.85 | 0.88 | 1.00 | 1.03 | 1.00 |
| Hist1h2ai | 0.95 | 1.00 | 1.00 | 1.00 | 1.00 | 0.56 | 1.09 | 2.83 | 1.93 | 1.00 | 1.00 | 1.00 |
| Hist1h2ba | 0.95 | 1.30 | 1.88 | 1.15 | 1.00 | 0.57 | 1.09 | 1.24 | 1.38 | 1.06 | 1.08 | 2.10 |
| Hist1h2bc | 1.42 | 1.49 | 1.18 | 1.28 | 1.29 | 0.78 | 0.92 | 0.42 | 1.03 | 1.38 | 2.39 | 1.17 |
| Hist1h2be | 1.50 | 1.18 | 1.31 | 1.25 | 0.17 | 0.68 | 1.22 | 0.35 | 0.85 | 3.05 | 1.71 | 0.92 |
| Hist1h2bg | 1.27 | 1.11 | 1.30 | 1.22 | 0.75 | 0.65 | 0.94 | 0.60 | 0.85 | 0.96 | 1.27 | 1.09 |
| Hist1h2bj | 2.26 | 1.52 | 1.19 | 1.24 | 0.44 | 0.87 | 0.72 | 0.46 | 0.68 | 1.22 | 0.90 | 0.81 |
| Hist1h4a | 1.48 | 1.00 | 1.46 | 0.76 | 0.51 | 1.24 | 1.00 | 0.42 | 1.21 | 1.00 | 0.71 | 0.51 |
| Hist1h4b | 1.00 | 1.00 | 1.00 | 0.82 | 0.87 | 0.82 | 0.40 | 1.34 | 1.48 | 1.00 | 1.30 | 1.00 |
| Hist1h4c | 2.90 | 0.91 | 1.00 | 0.63 | 0.45 | 0.87 | 1.10 | 1.22 | 2.09 | 1.00 | 1.00 | 1.59 |
| Hist1h4f | 1.00 | 1.00 | 1.00 | 1.07 | 1.22 | 0.50 | 2.56 | 1.51 | 0.84 | 1.00 | 1.00 | 1.00 |
| Hist1h4h | 1.63 | 3.63 | 1.67 | 0.73 | 1.28 | 0.49 | 0.76 | 0.97 | 0.95 | 1.12 | 2.28 | 1.07 |
| Hist1h4i | 1.64 | 2.45 | 2.73 | 3.05 | 0.49 | 1.29 | 0.75 | 0.98 | 2.11 | 1.00 | 1.51 | 0.57 |
| Hist1h4j | 3.07 | 1.17 | 1.78 | 0.42 | 0.80 | 0.40 | 0.58 | 0.67 | 1.16 | 1.47 | 2.95 | 0.89 |
| Hist1h4k | 1.16 | 1.00 | 0.62 | 1.24 | 2.08 | 0.64 | 1.28 | 0.90 | 1.01 | 0.87 | 1.01 | 1.48 |
| Hist1h4n | 2.31 | 1.96 | 1.46 | 0.92 | 0.07 | 0.70 | 1.46 | 0.67 | 1.51 | 3.76 | 0.61 | 1.28 |
| Hist2h2aa1 | 1.21 | 1.70 | 1.52 | 0.78 | 1.75 | 0.52 | 0.85 | 1.16 | 1.03 | 1.20 | 1.26 | 1.22 |
| Hist2h2aa2 | 4.78 | 6.55 | 1.11 | 1.19 | 1.00 | 1.00 | 0.84 | 0.02 | 1.01 | 0.17 | 3.00 | 0.85 |
| Hist2h2ac | 2.11 | 2.51 | 1.85 | 0.69 | 2.30 | 0.56 | 1.19 | 0.57 | 0.94 | 0.87 | 0.74 | 1.00 |
| Hist2h3c1 | 7.95 | 1.00 | 0.24 | 1.00 | 1.00 | 0.29 | 4.40 | 1.00 | 4.32 | 1.54 | 1.00 | 1.92 |
| Hmg20b | 1.19 | 1.33 | 1.21 | 0.90 | 2.01 | 0.94 | 0.92 | 2.37 | 1.00 | 1.04 | 1.18 | 0.88 |

Fig. 35- 188

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| H2-Q10 | 1.00 | 1.00 | 1.38 | 1.00 | 1.00 | 1.00 | 4.50 | 6.90 | 3.93 | 60.58 | 17.15 | 12.66 |
| H2-T22 | 0.39 | 1.26 | 0.50 | 1.73 | 1.00 | 1.35 | 0.96 | 0.05 | 0.80 | 0.24 | 1.31 | 1.67 |
| H2afb1 | 1.00 | 1.05 | 1.00 | 1.00 | 1.00 | 1.00 | 5.50 | 4.05 | 0.86 | 1.00 | 1.00 | 1.00 |
| H2afj | 1.31 | 1.00 | 1.07 | 1.13 | 0.85 | 1.06 | 1.23 | 13.02 | 0.91 | 3.80 | 1.18 | 1.04 |
| H2afv | 0.64 | 0.77 | 0.66 | 0.93 | 0.43 | 1.07 | 1.18 | 1.54 | 0.92 | 1.40 | 1.26 | 1.15 |
| H60c | 1.00 | 1.00 | 1.00 | 1.00 | 1.00 | 1.00 | 13.53 | 1.00 | 9.61 | 1.00 | 1.00 | 1.00 |
| Hadha | 0.75 | 0.73 | 0.90 | 1.02 | 0.94 | 1.04 | 1.80 | 9.92 | 1.62 | 2.34 | 1.05 | 1.07 |
| Haghl | 1.00 | 1.00 | 0.76 | 1.01 | 0.88 | 1.01 | 1.38 | 26.25 | 0.67 | 7.59 | 0.94 | 1.04 |
| Hal | 1.00 | 1.00 | 1.00 | 1.00 | 1.00 | 1.00 | 0.73 | 1.50 | 0.44 | 1.97 | 1.38 | 1.25 |
| Hamp | 1.00 | 1.00 | 1.00 | 1.00 | 1.00 | 1.00 | 1.00 | 1.00 | 1.00 | 1.00 | 1.00 | 1.00 |
| Hamp2 | 0.88 | 0.57 | 0.83 | 1.00 | 1.00 | 1.00 | 1.00 | 1.17 | 1.67 | 1.00 | 1.00 | 1.00 |
| Hapln4 | 1.00 | 1.00 | 1.00 | 1.09 | 1.17 | 1.04 | 1.00 | 1.00 | 1.00 | 1.00 | 1.00 | 1.00 |
| Haus7 | 0.81 | 0.55 | 0.60 | 1.07 | 0.86 | 0.90 | 1.07 | 16.52 | 0.85 | 2.50 | 1.05 | 0.98 |
| Haus8 | 1.00 | 1.00 | 1.00 | 1.16 | 6.19 | 1.06 | 1.06 | 1.12 | 0.57 | 1.53 | 1.06 | 0.90 |
| Hax1 | 1.22 | 1.08 | 1.20 | 0.95 | 6.45 | 0.99 | 0.79 | 1.67 | 1.01 | 1.58 | 0.95 | 1.00 |
| Hba-a1 | 0.68 | 0.77 | 0.20 | 0.95 | 3.01 | 0.48 | 1.67 | 14.80 | 11.56 | 1.71 | 1.14 | 0.95 |
| Hba-a2 | 1.00 | 1.00 | 35.35 | 1.00 | 0.35 | 0.84 | 4.97 | 14.33 | 3.40 | 4.34 | 1.46 | 1.07 |
| Hbb-b1 | 0.65 | 0.74 | 0.88 | 0.82 | 0.83 | 0.48 | 1.47 | 3.66 | 9.44 | 1.64 | 1.07 | 0.90 |
| Hbb-bs | 1.00 | 1.00 | 0.94 | 8.14 | 0.93 | 1.73 | 47.89 | 171.39 | 10.69 | 5.23 | 1.30 | 0.92 |
| Hbb-bt | 0.68 | 0.63 | 0.89 | 1.15 | 0.70 | 0.49 | 1.63 | 2.61 | 10.51 | 1.05 | 1.06 | 0.91 |
| Hbs1l | 0.88 | 1.17 | 1.05 | 1.02 | 0.94 | 0.91 | 1.08 | 4.97 | 1.08 | 2.20 | 1.16 | 1.16 |
| Hcfc1r1 | 0.87 | 1.07 | 0.78 | 1.03 | 0.95 | 1.04 | 1.20 | 5.95 | 0.89 | 2.53 | 1.71 | 1.33 |
| Hcls1 | 1.00 | 1.00 | 1.14 | 0.95 | 1.48 | 1.21 | 1.16 | 8.41 | 1.22 | 2.76 | 1.47 | 1.22 |
| Hcn2 | 1.00 | 1.00 | 1.00 | 1.04 | 0.94 | 1.05 | 1.00 | 1.00 | 1.00 | 1.00 | 1.00 | 1.00 |
| Hcrtr1 | 1.00 | 1.00 | 1.00 | 1.07 | 5.67 | 1.40 | 1.00 | 1.46 | 1.00 | 1.00 | 1.00 | 1.00 |
| Hcst | 1.00 | 1.00 | 1.00 | 1.00 | 1.00 | 1.00 | 1.90 | 12.75 | 0.76 | 3.56 | 1.74 | 1.20 |
| Hdac10 | 0.87 | 1.12 | 1.00 | 1.10 | 5.47 | 0.93 | 1.10 | 0.88 | 0.97 | 1.00 | 0.74 | 0.79 |
| Hddc2 | 0.87 | 0.56 | 0.50 | 0.73 | 0.88 | 1.12 | 0.89 | 20.06 | 0.79 | 3.01 | 1.77 | 1.08 |
| Hdgfrp2 | 0.85 | 0.83 | 0.84 | 1.00 | 0.79 | 1.02 | 1.36 | 5.61 | 1.12 | 2.18 | 1.21 | 0.94 |
| Hebp2 | 1.00 | 1.00 | 1.00 | 1.77 | 0.64 | 2.06 | 0.84 | 1.29 | 0.67 | 1.00 | 1.00 | 1.00 |
| Hexa | 0.73 | 0.42 | 0.83 | 1.09 | 0.78 | 1.17 | 1.28 | 8.11 | 1.18 | 3.54 | 1.49 | 1.20 |
| Hgd | 1.00 | 1.00 | 1.00 | 1.00 | 1.00 | 1.00 | 1.00 | 1.52 | 1.00 | 1.00 | 1.00 | 1.00 |
| Hgf | 1.00 | 1.00 | 1.00 | 1.00 | 1.00 | 1.00 | 1.00 | 1.00 | 1.00 | 1.00 | 0.81 | 1.33 |
| Hgs | 1.12 | 1.04 | 0.81 | 1.26 | 1.00 | 1.04 | 1.14 | 5.51 | 0.99 | 2.59 | 1.32 | 1.11 |
| Hhatl | 1.00 | 1.00 | 1.00 | 1.20 | 0.99 | 1.11 | 2.24 | 7.63 | 2.07 | 1.00 | 1.00 | 1.00 |
| Higd1b | 1.00 | 1.00 | 1.00 | 0.87 | 1.74 | 1.30 | 1.66 | 2.04 | 1.45 | 1.00 | 1.00 | 1.00 |
| Hilpda | 0.84 | 0.73 | 1.23 | 0.95 | 1.00 | 1.06 | 3.34 | 0.50 | 1.70 | 0.65 | 1.41 | 1.01 |
| Hils1 | 1.00 | 1.00 | 1.00 | 1.00 | 1.00 | 1.00 | 3.88 | 1.00 | 1.00 | 1.00 | 1.00 | 1.00 |
| Hint1 | 1.08 | 0.94 | 0.94 | 1.17 | 1.36 | 1.07 | 1.11 | 2.31 | 1.02 | 1.43 | 1.01 | 0.99 |
| Hint2 | 0.53 | 0.39 | 0.66 | 0.43 | 0.54 | 0.61 | 0.72 | 16.28 | 0.64 | 2.11 | 0.88 | 0.64 |
| Hip1r | 1.25 | 1.14 | 1.23 | 1.12 | 1.05 | 1.03 | 1.13 | 3.83 | 1.00 | 2.05 | 1.48 | 1.08 |
| Hipk2 | 1.00 | 1.00 | 1.00 | 0.54 | 1.00 | 0.61 | 0.76 | 0.71 | 0.87 | 0.76 | 0.73 | 0.77 |
| Hist1h1c | 0.57 | 0.58 | 0.36 | 1.35 | 0.93 | 1.26 | 1.15 | 0.20 | 1.26 | 0.87 | 1.69 | 1.24 |
| Hist1h2ah | 1.00 | 1.00 | 1.00 | 1.00 | 2.56 | 1.00 | 1.00 | 5.90 | 1.76 | 2.07 | 1.27 | 0.92 |
| Hist1h2ai | 1.00 | 1.00 | 1.00 | 1.00 | 6.96 | 1.00 | 1.13 | 3.94 | 0.79 | 2.26 | 0.80 | 0.94 |
| Hist1h2ba | 1.00 | 1.07 | 1.00 | 1.32 | 1.00 | 1.55 | 2.15 | 1.19 | 1.70 | 0.71 | 1.56 | 0.63 |
| Hist1h2bc | 0.52 | 0.79 | 0.82 | 1.13 | 7.38 | 1.11 | 1.35 | 0.86 | 1.48 | 1.06 | 2.12 | 1.68 |
| Hist1h2be | 1.17 | 0.95 | 0.61 | 2.16 | 1.77 | 0.90 | 1.43 | 2.48 | 1.64 | 0.53 | 1.04 | 1.40 |
| Hist1h2bg | 1.11 | 0.53 | 1.52 | 1.17 | 1.00 | 1.31 | 1.50 | 0.27 | 0.90 | 1.03 | 1.29 | 1.37 |
| Hist1h2bj | 1.00 | 1.00 | 0.69 | 0.51 | 0.28 | 1.22 | 1.23 | 1.98 | 0.87 | 0.78 | 0.83 | 0.59 |
| Hist1h4a | 1.00 | 1.00 | 1.00 | 1.00 | 1.41 | 1.00 | 1.54 | 6.60 | 3.09 | 0.62 | 1.80 | 1.89 |
| Hist1h4b | 1.00 | 1.00 | 1.00 | 1.00 | 1.41 | 1.00 | 1.00 | 8.38 | 1.00 | 2.03 | 1.05 | 1.01 |
| Hist1h4c | 1.00 | 1.00 | 1.00 | 1.38 | 2.21 | 1.14 | 1.00 | 8.84 | 1.00 | 1.39 | 2.40 | 1.18 |
| Hist1h4f | 1.00 | 1.00 | 1.00 | 1.00 | 1.00 | 1.00 | 1.00 | 7.94 | 1.00 | 1.01 | 0.84 | 0.60 |
| Hist1h4h | 0.35 | 0.54 | 1.01 | 1.55 | 0.79 | 1.66 | 2.20 | 15.04 | 1.16 | 2.73 | 1.68 | 1.08 |
| Hist1h4i | 1.13 | 1.00 | 0.78 | 2.34 | 3.30 | 2.50 | 0.64 | 2.59 | 0.97 | 0.57 | 0.53 | 0.55 |
| Hist1h4j | 1.00 | 1.00 | 1.00 | 1.00 | 0.19 | 1.72 | 1.76 | 18.10 | 1.09 | 2.62 | 1.65 | 0.90 |
| Hist1h4k | 1.00 | 1.00 | 1.00 | 1.00 | 1.51 | 0.73 | 1.05 | 4.51 | 1.00 | 1.60 | 0.80 | 1.41 |
| Hist1h4n | 1.00 | 1.00 | 1.06 | 1.00 | 0.28 | 1.51 | 1.00 | 0.92 | 0.76 | 1.89 | 1.27 | 1.22 |
| Hist2h2aa1 | 0.76 | 0.82 | 0.72 | 1.21 | 1.26 | 1.00 | 1.72 | 6.50 | 1.39 | 2.46 | 1.61 | 1.43 |
| Hist2h2aa2 | 4.54 | 0.41 | 0.96 | 0.57 | 1.00 | 1.31 | 1.40 | 0.15 | 1.09 | 0.80 | 0.32 | 0.76 |
| Hist2h2ac | 0.87 | 0.38 | 0.94 | 1.00 | 0.53 | 0.77 | 1.54 | 2.29 | 1.20 | 2.49 | 1.58 | 1.55 |
| Hist2h3c1 | 1.00 | 1.00 | 1.00 | 1.00 | 1.00 | 1.41 | 1.00 | 1.00 | 0.47 | 1.00 | 1.00 | 1.00 |
| Hmg20b | 1.63 | 1.39 | 0.92 | 0.87 | 0.68 | 0.92 | 0.96 | 7.53 | 0.90 | 2.88 | 1.38 | 1.15 |

Fig. 35- 189

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Hmga1-rs1 | 3.86 | 0.95 | 0.91 | 1.13 | 5.50 | 2.06 | 0.96 | 0.75 | 0.88 | 2.26 | 1.76 | 1.03 |
| Hmgb4 | 1.00 | 1.00 | 1.00 | 1.00 | 1.00 | 1.00 | 1.00 | 1.00 | 1.00 | 1.57 | 1.00 | 1.00 |
| Hmgcl | 1.05 | 0.49 | 0.83 | 0.60 | 7.23 | 1.17 | 1.00 | 0.82 | 0.91 | 2.06 | 3.33 | 1.22 |
| Hmgcs2 | 1.19 | 1.31 | 1.32 | 3.91 | 6.79 | 11.20 | 0.72 | 0.58 | 0.51 | 0.99 | 1.18 | 1.85 |
| Hmgn1 | 1.12 | 0.84 | 1.10 | 0.75 | 3.78 | 1.23 | 0.83 | 0.77 | 0.90 | 1.07 | 1.54 | 0.84 |
| Hmox1 | 3.64 | 7.94 | 2.81 | 1.47 | 0.94 | 2.66 | 3.83 | 3.66 | 2.73 | 0.12 | 0.38 | 1.35 |
| Hnrnpa1 | 1.59 | 0.80 | 1.12 | 0.79 | 6.16 | 2.19 | 0.88 | 0.38 | 1.13 | 2.16 | 3.47 | 0.63 |
| Homer3 | 1.33 | 0.31 | 0.81 | 0.66 | 5.61 | 1.21 | 0.95 | 0.71 | 1.07 | 1.99 | 1.81 | 0.81 |
| Hoxb7 | 0.91 | 0.56 | 1.12 | 1.14 | 2.15 | 2.07 | 1.00 | 1.00 | 1.00 | 1.34 | 1.37 | 0.81 |
| Hp | 2.24 | 2.47 | 4.17 | 0.27 | 3.94 | 0.94 | 2.38 | 0.52 | 3.92 | 2.14 | 3.40 | 1.18 |
| Hpca | 1.00 | 1.00 | 1.00 | 1.00 | 0.04 | 1.00 | 1.00 | 1.00 | 1.00 | 1.00 | 1.00 | 1.00 |
| Hpcal4 | 1.00 | 1.00 | 1.00 | 0.58 | 0.05 | 0.68 | 1.00 | 1.00 | 1.00 | 0.73 | 0.47 | 0.45 |
| Hpd | 1.00 | 1.04 | 1.00 | 0.50 | 10.72 | 2.04 | 1.61 | 1.00 | 1.00 | 0.19 | 1.00 | 1.00 |
| Hpgd | 1.85 | 3.35 | 3.47 | 1.54 | 0.59 | 0.62 | 1.03 | 0.67 | 0.95 | 0.34 | 0.50 | 1.36 |
| Hps1 | 1.00 | 0.87 | 1.00 | 0.97 | 6.97 | 2.24 | 1.00 | 1.00 | 1.00 | 1.38 | 2.54 | 0.84 |
| Hr | 1.45 | 2.06 | 0.82 | 6.50 | 10.81 | 5.81 | 1.59 | 1.46 | 1.23 | 1.67 | 2.28 | 1.07 |
| Hras | 1.07 | 0.55 | 0.75 | 0.21 | 5.35 | 0.89 | 0.89 | 0.80 | 0.83 | 2.32 | 3.56 | 0.99 |
| Hrasls5 | 1.00 | 1.00 | 1.00 | 1.00 | 1.00 | 1.00 | 1.00 | 1.00 | 1.00 | 1.00 | 1.00 | 1.00 |
| Hrct1 | 1.01 | 0.35 | 0.85 | 0.57 | 7.26 | 1.10 | 0.94 | 0.84 | 0.89 | 1.76 | 2.13 | 0.81 |
| Hrsp12 | 1.12 | 1.02 | 0.94 | 1.26 | 1.30 | 1.49 | 1.12 | 1.28 | 0.95 | 0.63 | 1.29 | 1.73 |
| Hsd17b10 | 1.02 | 0.69 | 1.08 | 0.78 | 8.54 | 2.96 | 0.90 | 0.83 | 0.85 | 1.30 | 2.16 | 1.06 |
| Hsd17b11 | 1.23 | 0.94 | 1.04 | 1.05 | 3.47 | 1.31 | 0.83 | 0.88 | 0.86 | 1.96 | 2.04 | 1.07 |
| Hsd17b7 | 0.83 | 2.15 | 1.55 | 1.22 | 0.33 | 0.85 | 4.17 | 4.88 | 5.08 | 1.00 | 1.09 | 2.40 |
| Hspa1a | 5.67 | 2.63 | 6.75 | 6.17 | 1.04 | 1.17 | 3.77 | 3.48 | 4.70 | 0.59 | 0.64 | 1.04 |
| Hspa1b | 3.96 | 2.42 | 5.73 | 4.28 | 0.45 | 1.11 | 1.51 | 1.76 | 2.45 | 0.50 | 0.47 | 0.89 |
| Hspa2 | 1.93 | 2.97 | 1.71 | 0.90 | 0.52 | 0.80 | 1.25 | 0.90 | 0.86 | 1.02 | 0.87 | 0.70 |
| Hspb1 | 2.69 | 2.42 | 2.63 | 1.55 | 6.79 | 2.31 | 2.02 | 1.43 | 1.87 | 0.89 | 1.70 | 1.27 |
| Hspb11 | 1.96 | 0.45 | 0.73 | 0.48 | 5.90 | 1.56 | 1.08 | 1.30 | 1.08 | 0.96 | 1.16 | 0.89 |
| Hspb2 | 1.38 | 0.61 | 0.86 | 0.34 | 5.59 | 0.58 | 0.99 | 0.77 | 0.99 | 1.92 | 2.46 | 0.91 |
| Hspb3 | 0.90 | 0.48 | 0.69 | 1.00 | 2.08 | 1.00 | 0.46 | 0.54 | 0.71 | 1.00 | 1.00 | 1.00 |
| Hspb9 | 1.00 | 1.00 | 1.00 | 1.00 | 1.00 | 1.00 | 1.00 | 1.00 | 1.00 | 4.37 | 1.33 | 1.00 |
| Hspbp1 | 1.38 | 1.00 | 1.15 | 0.34 | 2.41 | 0.87 | 1.06 | 0.92 | 1.14 | 2.78 | 3.48 | 1.20 |
| Htatip2 | 1.71 | 1.13 | 1.48 | 0.71 | 4.57 | 0.98 | 0.97 | 0.78 | 0.84 | 2.01 | 2.25 | 1.06 |
| Htr5b | 1.00 | 1.00 | 1.00 | 1.00 | 1.00 | 1.00 | 1.00 | 1.00 | 1.00 | 1.00 | 1.00 | 1.00 |
| Htra3 | 1.81 | 1.54 | 1.48 | 2.64 | 5.13 | 2.05 | 1.12 | 0.92 | 1.02 | 1.46 | 1.62 | 1.38 |
| Hyi | 0.90 | 0.48 | 1.79 | 1.03 | 6.03 | 1.23 | 1.33 | 0.84 | 0.78 | 1.44 | 1.45 | 0.85 |
| Hyls1 | 0.80 | 1.10 | 1.22 | 5.44 | 4.51 | 1.72 | 0.94 | 0.72 | 0.63 | 1.66 | 0.97 | 1.29 |
| I830012O16Rik | 0.57 | 1.02 | 0.60 | 2.73 | 1.00 | 2.01 | 2.61 | 1.68 | 2.21 | 0.39 | 0.37 | 1.18 |
| Icam2 | 1.02 | 0.52 | 0.93 | 0.50 | 2.52 | 0.92 | 0.91 | 0.69 | 0.72 | 1.34 | 1.60 | 0.85 |
| Ict1 | 1.47 | 0.58 | 0.82 | 0.30 | 6.00 | 0.75 | 0.84 | 0.84 | 0.69 | 2.00 | 3.29 | 0.89 |
| Idnk | 0.90 | 0.52 | 1.15 | 1.09 | 5.64 | 1.01 | 0.87 | 0.91 | 0.82 | 1.76 | 2.12 | 1.05 |
| Ier2 | 1.71 | 1.75 | 1.16 | 1.17 | 6.07 | 1.71 | 1.37 | 0.79 | 1.21 | 1.31 | 1.74 | 1.11 |
| Ier5 | 2.39 | 6.56 | 2.35 | 1.92 | 1.10 | 1.18 | 1.55 | 1.79 | 1.48 | 0.43 | 0.32 | 0.99 |
| Ier5l | 1.08 | 0.52 | 0.88 | 1.11 | 8.78 | 0.60 | 0.77 | 0.61 | 0.88 | 1.30 | 1.40 | 0.88 |
| Ifi203 | 0.70 | 0.70 | 1.27 | 1.94 | 0.78 | 1.04 | 0.71 | 0.65 | 0.87 | 2.95 | 2.83 | 7.38 |
| Ifi204 | 1.25 | 1.90 | 1.26 | 1.11 | 0.67 | 1.15 | 0.98 | 1.27 | 1.22 | 11.38 | 12.43 | 11.67 |
| Ifi205 | 3.82 | 2.56 | 4.20 | 6.04 | 1.52 | 2.31 | 8.86 | 5.47 | 2.96 | 0.36 | 0.26 | 0.62 |
| Ifi27 | 1.78 | 1.08 | 1.45 | 0.29 | 3.73 | 0.72 | 1.59 | 1.96 | 2.15 | 2.25 | 4.05 | 1.71 |
| Ifi27l2a | 0.98 | 0.58 | 1.10 | 0.39 | 5.19 | 0.53 | 7.72 | 3.34 | 6.74 | 5.01 | 11.32 | 3.02 |
| Ifi35 | 2.29 | 1.01 | 1.38 | 0.71 | 9.67 | 1.16 | 1.17 | 1.22 | 1.18 | 2.67 | 3.27 | 1.20 |
| Ifi44 | 1.00 | 1.00 | 1.00 | 1.15 | 1.00 | 1.00 | 2.34 | 1.88 | 1.87 | 1.70 | 2.13 | 2.77 |
| Ifi47 | 2.02 | 2.55 | 1.40 | 2.38 | 3.75 | 2.61 | 2.12 | 1.44 | 2.61 | 0.97 | 1.00 | 1.39 |
| Ifit1 | 1.18 | 1.66 | 1.66 | 2.68 | 2.34 | 1.86 | 4.02 | 4.72 | 5.51 | 5.15 | 4.19 | 3.32 |
| Ifit3 | 1.55 | 2.24 | 1.23 | 5.76 | 4.35 | 2.70 | 2.88 | 2.01 | 2.58 | 0.85 | 0.94 | 1.51 |
| Ifitm2 | 1.53 | 1.39 | 1.21 | 0.61 | 0.64 | 0.94 | 1.33 | 1.03 | 1.07 | 0.52 | 0.51 | 1.02 |
| Ifrd1 | 3.88 | 6.33 | 1.77 | 3.80 | 1.12 | 1.40 | 2.57 | 2.62 | 1.24 | 0.63 | 0.77 | 1.44 |
| Ift22 | 1.15 | 0.48 | 1.12 | 0.58 | 5.33 | 0.98 | 0.98 | 0.78 | 1.09 | 2.38 | 2.95 | 1.02 |
| Ift27 | 0.61 | 0.30 | 0.56 | 0.43 | 6.66 | 1.18 | 1.07 | 0.51 | 0.65 | 3.17 | 2.71 | 1.18 |
| Ift43 | 1.62 | 0.71 | 0.74 | 0.95 | 5.42 | 0.63 | 0.78 | 0.78 | 0.77 | 0.80 | 1.59 | 0.97 |
| Ift46 | 1.04 | 0.59 | 1.12 | 0.58 | 10.21 | 1.06 | 1.40 | 1.08 | 0.90 | 2.83 | 4.35 | 0.98 |
| Igfbp1 | 1.00 | 1.00 | 1.00 | 1.00 | 1.00 | 1.00 | 2.06 | 1.00 | 1.00 | 1.00 | 1.00 | 1.00 |
| Igfbp2 | 1.00 | 1.00 | 1.00 | 1.00 | 1.31 | 1.00 | 1.29 | 0.52 | 1.00 | 3.00 | 3.56 | 1.59 |
| Igf1r1 | 1.22 | 0.57 | 1.04 | 0.44 | 2.84 | 0.78 | 0.87 | 0.57 | 0.83 | 1.56 | 1.90 | 0.81 |
| Igj | 1.00 | 1.00 | 1.54 | 1.00 | 1.00 | 1.00 | 1.00 | 1.00 | 1.00 | 0.32 | 1.24 | 1.08 |

Fig. 35- 190

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Hmga1-rs1 | 0.65 | 0.96 | 0.73 | 1.10 | 0.71 | 0.70 | 1.88 | 1.92 | 1.76 | 1.40 | 1.13 | 0.94 |
| Hmgb4 | 1.00 | 1.00 | 1.00 | 1.00 | 1.00 | 1.00 | 1.00 | 1.00 | 1.00 | 1.00 | 1.00 | 1.00 |
| Hmgcl | 1.41 | 1.79 | 1.20 | 0.90 | 0.67 | 0.92 | 0.85 | 1.07 | 0.86 | 1.18 | 1.73 | 1.24 |
| Hmgcs2 | 2.07 | 1.48 | 1.64 | 0.46 | 0.50 | 0.62 | 0.98 | 0.55 | 1.02 | 1.19 | 1.22 | 1.41 |
| Hmgn1 | 1.01 | 1.06 | 0.92 | 0.80 | 0.80 | 0.77 | 0.99 | 0.79 | 0.89 | 0.77 | 1.27 | 0.97 |
| Hmox1 | 2.97 | 3.38 | 2.46 | 6.65 | 11.03 | 2.49 | 1.33 | 0.36 | 1.40 | 1.79 | 1.49 | 1.17 |
| Hnrnpa1 | 0.42 | 0.55 | 0.87 | 0.88 | 1.36 | 1.29 | 0.37 | 2.40 | 3.14 | 0.91 | 1.05 | 0.67 |
| Homer3 | 0.88 | 0.96 | 0.81 | 0.92 | 0.61 | 0.81 | 1.00 | 2.95 | 0.86 | 0.68 | 1.15 | 0.72 |
| Hoxb7 | 1.00 | 1.00 | 1.00 | 0.79 | 0.93 | 0.98 | 1.00 | 1.00 | 1.00 | 1.31 | 1.77 | 1.17 |
| Hp | 0.85 | 1.55 | 1.41 | 0.73 | 0.44 | 1.39 | 1.14 | 1.43 | 1.20 | 1.34 | 2.97 | 1.84 |
| Hpca | 1.01 | 1.05 | 1.00 | 1.00 | 1.00 | 1.00 | 1.00 | 1.00 | 1.00 | 0.70 | 1.24 | 1.34 |
| Hpcal4 | 1.00 | 1.00 | 1.00 | 1.01 | 1.00 | 1.00 | 1.00 | 1.00 | 1.00 | 1.04 | 0.78 | 1.04 |
| Hpd | 3.23 | 1.02 | 1.00 | 2.91 | 2.21 | 1.20 | 1.30 | 2.17 | 1.54 | 1.06 | 1.59 | 1.14 |
| Hpgd | 9.31 | 7.84 | 6.14 | 0.58 | 0.52 | 0.70 | 0.67 | 0.15 | 0.74 | 1.14 | 1.23 | 1.14 |
| Hps1 | 1.03 | 1.16 | 0.85 | 0.79 | 0.44 | 0.72 | 1.18 | 0.99 | 0.97 | 0.93 | 1.02 | 0.84 |
| Hr | 1.50 | 0.94 | 0.95 | 1.49 | 1.00 | 1.50 | 1.00 | 1.00 | 1.00 | 1.01 | 1.14 | 0.91 |
| Hras | 1.17 | 1.42 | 0.92 | 1.01 | 0.65 | 0.95 | 0.72 | 1.38 | 0.72 | 1.12 | 1.82 | 1.13 |
| Hrasls5 | 1.00 | 1.00 | 1.00 | 1.00 | 1.00 | 1.00 | 1.00 | 1.00 | 1.00 | 1.00 | 1.00 | 1.00 |
| Hrct1 | 1.45 | 2.42 | 1.01 | 1.08 | 0.44 | 0.94 | 1.00 | 1.56 | 1.00 | 1.04 | 1.41 | 0.95 |
| Hrsp12 | 1.30 | 1.61 | 1.47 | 1.34 | 2.17 | 1.25 | 0.86 | 0.38 | 0.79 | 1.87 | 2.33 | 2.06 |
| Hsd17b10 | 1.13 | 1.46 | 1.05 | 0.81 | 0.81 | 0.79 | 2.46 | 2.52 | 2.96 | 1.04 | 1.50 | 0.92 |
| Hsd17b11 | 1.59 | 1.72 | 1.23 | 1.50 | 1.30 | 1.18 | 0.71 | 0.99 | 0.87 | 1.06 | 1.39 | 1.12 |
| Hsd17b7 | 0.61 | 0.40 | 0.71 | 0.86 | 1.06 | 0.85 | 1.53 | 1.24 | 1.55 | 1.26 | 0.71 | 1.03 |
| Hspa1a | 2.15 | 1.87 | 2.01 | 1.00 | 1.18 | 1.38 | 2.52 | 1.00 | 3.30 | 1.29 | 0.87 | 1.22 |
| Hspa1b | 1.23 | 1.20 | 1.38 | 0.68 | 0.72 | 1.22 | 1.96 | 0.94 | 2.56 | 1.11 | 0.82 | 1.07 |
| Hspa2 | 1.07 | 1.42 | 1.02 | 0.73 | 0.49 | 0.83 | 1.67 | 5.46 | 1.26 | 1.03 | 0.81 | 0.82 |
| Hspb1 | 3.23 | 3.36 | 1.84 | 1.07 | 1.47 | 1.38 | 3.32 | 2.07 | 2.47 | 1.20 | 1.57 | 1.81 |
| Hspb11 | 0.91 | 1.09 | 0.67 | 1.08 | 1.73 | 0.78 | 0.61 | 0.42 | 1.07 | 0.68 | 1.51 | 1.66 |
| Hspb2 | 2.20 | 1.66 | 0.69 | 0.71 | 0.36 | 0.76 | 1.00 | 1.91 | 1.00 | 1.08 | 1.38 | 0.68 |
| Hspb3 | 0.69 | 0.77 | 0.92 | 1.00 | 1.00 | 1.00 | 1.00 | 1.00 | 1.00 | 1.00 | 1.00 | 1.00 |
| Hspb9 | 1.00 | 0.66 | 1.00 | 1.02 | 1.00 | 1.81 | 1.00 | 1.27 | 1.00 | 1.00 | 1.00 | 1.12 |
| Hspbp1 | 1.12 | 1.24 | 0.99 | 0.94 | 0.96 | 0.96 | 1.24 | 3.02 | 0.96 | 1.07 | 1.33 | 1.22 |
| Htatip2 | 1.44 | 1.55 | 1.16 | 1.52 | 1.13 | 1.50 | 0.99 | 1.69 | 1.22 | 1.10 | 1.40 | 1.20 |
| Htr5b | 1.00 | 1.00 | 1.00 | 1.00 | 1.00 | 1.00 | 1.00 | 1.00 | 1.00 | 1.00 | 1.00 | 1.00 |
| Htra3 | 3.00 | 2.34 | 1.34 | 1.00 | 1.00 | 1.00 | 1.40 | 1.19 | 1.70 | 1.27 | 1.58 | 1.50 |
| Hyi | 1.44 | 1.76 | 1.37 | 0.82 | 0.59 | 0.96 | 0.50 | 1.26 | 0.53 | 1.16 | 1.76 | 1.09 |
| Hyls1 | 0.73 | 0.93 | 0.89 | 1.44 | 1.15 | 1.17 | 0.89 | 1.00 | 1.02 | 1.02 | 0.80 | 1.26 |
| I830012O16Rik | 1.35 | 1.35 | 1.37 | 1.96 | 2.62 | 2.48 | 1.70 | 1.00 | 2.38 | 2.62 | 1.26 | 1.07 |
| Icam2 | 0.89 | 1.11 | 0.83 | 1.03 | 0.91 | 0.89 | 0.54 | 0.38 | 0.43 | 0.76 | 1.43 | 1.14 |
| Ict1 | 1.00 | 1.45 | 0.85 | 0.74 | 0.68 | 0.94 | 0.79 | 1.13 | 0.90 | 0.89 | 1.75 | 0.94 |
| Idnk | 1.18 | 1.67 | 0.96 | 0.97 | 1.10 | 0.83 | 0.73 | 0.92 | 0.82 | 1.07 | 1.73 | 1.09 |
| Ier2 | 1.25 | 1.43 | 1.24 | 1.21 | 1.50 | 1.39 | 1.12 | 1.20 | 0.77 | 1.01 | 1.75 | 1.04 |
| Ier5 | 0.78 | 0.74 | 1.08 | 1.05 | 1.42 | 1.21 | 0.63 | 1.00 | 0.84 | 1.37 | 1.53 | 1.23 |
| Ier5l | 1.20 | 1.15 | 1.30 | 1.03 | 0.95 | 1.51 | 0.92 | 0.81 | 0.71 | 0.51 | 0.76 | 0.81 |
| Ifi203 | 2.26 | 2.04 | 2.12 | 2.80 | 0.90 | 1.98 | 1.75 | 1.00 | 1.80 | 2.20 | 1.80 | 2.03 |
| Ifi204 | 3.31 | 3.26 | 3.24 | 1.00 | 1.00 | 1.00 | 1.21 | 1.00 | 1.66 | 2.27 | 2.62 | 2.55 |
| Ifi205 | 1.09 | 1.00 | 1.25 | 1.00 | 1.00 | 1.00 | 1.00 | 1.00 | 1.00 | 1.69 | 1.07 | 1.18 |
| Ifi27 | 2.05 | 2.37 | 1.31 | 1.80 | 1.51 | 1.65 | 5.14 | 5.87 | 6.35 | 1.89 | 2.81 | 1.54 |
| Ifi27l2a | 2.14 | 2.11 | 0.97 | 1.50 | 3.03 | 2.40 | 2.70 | 8.68 | 4.82 | 4.79 | 6.78 | 4.36 |
| Ifi35 | 1.30 | 1.53 | 1.23 | 1.18 | 0.89 | 0.97 | 1.04 | 1.55 | 1.19 | 1.19 | 1.81 | 1.15 |
| Ifi44 | 2.14 | 1.73 | 1.80 | 2.02 | 1.78 | 2.09 | 1.00 | 1.00 | 1.00 | 7.58 | 5.73 | 3.70 |
| Ifi47 | 1.26 | 1.22 | 1.26 | 1.83 | 1.56 | 2.68 | 1.21 | 0.39 | 1.24 | 2.19 | 1.53 | 1.40 |
| Ifit1 | 1.37 | 1.15 | 1.73 | 4.67 | 3.48 | 4.53 | 1.84 | 1.13 | 2.84 | 6.67 | 4.47 | 2.97 |
| Ifit3 | 1.83 | 1.77 | 1.50 | 2.07 | 2.47 | 2.43 | 1.48 | 1.18 | 3.53 | 2.63 | 1.84 | 1.37 |
| Ifitm2 | 1.72 | 1.58 | 1.50 | 0.75 | 1.06 | 0.75 | 1.06 | 0.53 | 0.94 | 1.14 | 1.35 | 1.17 |
| Ifrd1 | 1.11 | 0.93 | 0.96 | 1.76 | 3.77 | 1.52 | 2.12 | 0.84 | 1.91 | 1.39 | 1.43 | 1.22 |
| Ift22 | 1.35 | 1.19 | 0.83 | 1.22 | 0.60 | 1.03 | 1.34 | 1.21 | 0.84 | 0.97 | 1.12 | 1.12 |
| Ift27 | 1.07 | 1.35 | 1.06 | 0.68 | 0.48 | 0.92 | 0.42 | 1.42 | 1.05 | 1.01 | 1.49 | 1.23 |
| Ift43 | 2.61 | 2.32 | 1.09 | 0.99 | 1.50 | 0.62 | 0.63 | 0.50 | 1.00 | 1.30 | 1.49 | 1.17 |
| Ift46 | 1.65 | 1.80 | 1.17 | 1.15 | 0.72 | 1.01 | 1.16 | 1.84 | 0.93 | 1.21 | 1.77 | 1.05 |
| Igfbp1 | 5.75 | 1.00 | 1.00 | 11.31 | 18.01 | 4.89 | 38.05 | 56.53 | 19.20 | 1.00 | 1.00 | 1.00 |
| Igfbp2 | 2.54 | 1.97 | 1.53 | 0.38 | 0.61 | 0.94 | 1.06 | 3.04 | 1.71 | 0.91 | 1.08 | 0.99 |
| Igf1r1 | 1.42 | 1.79 | 1.00 | 0.70 | 0.85 | 1.09 | 0.89 | 2.15 | 1.03 | 1.02 | 1.12 | 0.97 |
| Igj | 2.90 | 1.84 | 1.43 | 1.97 | 1.19 | 0.64 | 1.00 | 1.00 | 1.69 | 0.70 | 0.96 | 0.74 |

Fig. 35- 191

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Hmga1-rs1 | 0.84 | 1.17 | 1.38 | 1.67 | 2.99 | 1.11 | 1.23 | 1.82 | 1.00 | 1.23 | 1.37 | 0.91 |
| Hmgb4 | 1.00 | 1.00 | 1.00 | 5.85 | 4.68 | 1.22 | 0.91 | 1.23 | 1.02 | 1.00 | 1.00 | 1.00 |
| Hmgcl | 0.91 | 1.12 | 0.93 | 1.01 | 3.40 | 1.30 | 0.79 | 1.71 | 1.17 | 1.08 | 1.43 | 1.06 |
| Hmgcs2 | 1.27 | 1.39 | 2.09 | 2.09 | 2.44 | 1.53 | 0.82 | 0.44 | 0.71 | 1.06 | 1.03 | 1.27 |
| Hmgn1 | 0.72 | 0.79 | 0.89 | 1.17 | 5.41 | 1.32 | 0.86 | 0.79 | 0.80 | 1.16 | 1.27 | 1.01 |
| Hmox1 | 1.18 | 1.20 | 1.06 | 1.77 | 0.23 | 1.19 | 1.17 | 0.28 | 0.80 | 0.58 | 0.68 | 0.53 |
| Hnrnpa1 | 0.95 | 0.65 | 1.69 | 1.68 | 2.62 | 1.10 | 0.93 | 2.40 | 1.00 | 0.94 | 0.73 | 1.39 |
| Homer3 | 0.79 | 0.87 | 0.88 | 0.82 | 2.73 | 1.02 | 1.09 | 2.51 | 1.21 | 0.94 | 1.28 | 0.92 |
| Hoxb7 | 0.79 | 0.92 | 0.97 | 1.03 | 7.20 | 1.37 | 1.05 | 1.95 | 1.00 | 0.89 | 0.73 | 0.80 |
| Hp | 1.34 | 1.83 | 2.14 | 0.42 | 1.32 | 0.76 | 0.86 | 3.02 | 1.59 | 5.54 | 3.69 | 3.10 |
| Hpca | 0.84 | 1.07 | 0.79 | 0.39 | 2.01 | 0.78 | 0.98 | 0.80 | 1.14 | 1.00 | 52.38 | 1.00 |
| Hpcal4 | 1.00 | 1.00 | 1.00 | 1.00 | 1.00 | 1.00 | 1.11 | 0.97 | 1.01 | 1.00 | 23.78 | 1.00 |
| Hpd | 2.30 | 2.64 | 1.35 | 0.88 | 2.31 | 1.00 | 1.00 | 1.59 | 1.00 | 1.00 | 1.06 | 1.00 |
| Hpgd | 1.69 | 1.99 | 1.55 | 0.64 | 0.26 | 0.56 | 1.06 | 0.34 | 1.00 | 1.09 | 1.12 | 1.05 |
| Hps1 | 0.94 | 0.83 | 0.84 | 0.84 | 4.42 | 0.70 | 1.33 | 1.41 | 1.13 | 0.92 | 1.11 | 0.94 |
| Hr | 0.83 | 1.06 | 0.92 | 4.33 | 2.62 | 2.17 | 1.05 | 1.00 | 1.09 | 1.85 | 3.10 | 1.15 |
| Hras | 0.77 | 1.07 | 0.86 | 1.03 | 2.03 | 1.11 | 0.90 | 2.62 | 0.84 | 0.75 | 1.37 | 0.91 |
| Hrasls5 | 1.00 | 1.00 | 1.00 | 2.34 | 4.69 | 1.12 | 0.91 | 2.09 | 1.05 | 1.00 | 1.00 | 1.00 |
| Hrct1 | 1.04 | 1.41 | 1.02 | 0.78 | 0.89 | 0.69 | 0.89 | 4.28 | 1.94 | 1.74 | 1.58 | 1.03 |
| Hrsp12 | 2.33 | 2.73 | 2.11 | 0.96 | 0.51 | 1.27 | 0.71 | 0.62 | 1.20 | 1.84 | 1.78 | 2.10 |
| Hsd17b10 | 0.92 | 1.11 | 1.06 | 0.81 | 3.48 | 1.83 | 0.64 | 1.19 | 0.54 | 0.92 | 1.41 | 1.19 |
| Hsd17b11 | 0.77 | 0.75 | 0.75 | 1.09 | 2.91 | 1.28 | 0.99 | 1.68 | 0.76 | 1.20 | 1.07 | 1.03 |
| Hsd17b7 | 0.82 | 0.83 | 0.76 | 1.33 | 1.00 | 1.16 | 0.94 | 1.00 | 1.06 | 1.34 | 0.94 | 1.18 |
| Hspa1a | 1.31 | 1.34 | 1.21 | 3.02 | 1.02 | 1.13 | 1.76 | 1.19 | 2.77 | 1.32 | 1.02 | 1.40 |
| Hspa1b | 0.75 | 1.02 | 0.85 | 1.98 | 1.00 | 0.90 | 0.24 | 0.88 | 0.27 | 0.65 | 0.97 | 0.77 |
| Hspa2 | 1.18 | 1.35 | 1.23 | 1.27 | 1.52 | 1.02 | 1.10 | 0.86 | 1.03 | 0.94 | 1.29 | 0.85 |
| Hspb1 | 1.32 | 1.79 | 1.59 | 2.79 | 7.37 | 1.44 | 1.00 | 0.66 | 1.13 | 2.76 | 2.58 | 2.26 |
| Hspb11 | 0.72 | 1.18 | 1.46 | 0.51 | 1.00 | 1.62 | 0.85 | 0.75 | 0.79 | 0.56 | 0.98 | 0.78 |
| Hspb2 | 1.60 | 1.22 | 1.26 | 0.95 | 1.32 | 1.21 | 1.04 | 1.55 | 0.61 | 1.48 | 1.12 | 1.38 |
| Hspb3 | 1.00 | 1.00 | 1.00 | 1.00 | 1.00 | 1.00 | 1.00 | 1.00 | 1.00 | 1.00 | 1.00 | 1.00 |
| Hspb9 | 1.00 | 1.00 | 0.89 | 3.30 | 7.07 | 1.18 | 0.87 | 1.79 | 0.98 | 1.00 | 1.12 | 1.00 |
| Hspbp1 | 0.96 | 0.94 | 1.01 | 1.19 | 5.45 | 1.06 | 0.92 | 3.08 | 0.98 | 0.98 | 1.21 | 0.97 |
| Htatip2 | 1.06 | 1.20 | 1.07 | 0.86 | 1.73 | 0.84 | 0.91 | 2.02 | 0.88 | 0.94 | 1.24 | 0.87 |
| Htr5b | 1.00 | 1.00 | 1.00 | 1.00 | 1.00 | 1.00 | 0.09 | 0.32 | 0.10 | 1.00 | 1.00 | 1.00 |
| Htra3 | 1.73 | 1.89 | 2.40 | 1.10 | 1.27 | 0.60 | 0.94 | 0.60 | 0.77 | 1.27 | 1.60 | 1.27 |
| Hyi | 0.79 | 1.02 | 1.41 | 0.62 | 9.07 | 0.82 | 1.22 | 1.68 | 0.73 | 0.85 | 1.15 | 1.07 |
| Hyls1 | 0.76 | 0.84 | 1.53 | 1.13 | 1.00 | 1.18 | 0.89 | 0.78 | 0.91 | 1.04 | 1.05 | 1.07 |
| I830012O16Rik | 2.70 | 3.31 | 2.46 | 1.78 | 1.00 | 1.30 | 1.00 | 1.00 | 1.00 | 7.43 | 3.62 | 2.88 |
| Icam2 | 1.24 | 1.54 | 1.42 | 1.02 | 2.38 | 1.30 | 1.00 | 1.01 | 1.35 | 1.11 | 1.08 | 1.04 |
| Ict1 | 0.78 | 1.04 | 0.95 | 0.83 | 3.34 | 1.14 | 0.69 | 1.90 | 0.86 | 0.92 | 1.09 | 0.81 |
| Idnk | 1.44 | 1.03 | 1.00 | 0.64 | 1.55 | 0.85 | 1.09 | 1.41 | 0.78 | 0.98 | 1.26 | 1.06 |
| Ier2 | 0.97 | 1.22 | 0.90 | 1.48 | 2.65 | 1.37 | 0.80 | 0.92 | 1.17 | 0.95 | 1.02 | 0.95 |
| Ier5 | 0.91 | 0.92 | 1.00 | 1.18 | 0.53 | 1.16 | 1.01 | 0.24 | 1.03 | 0.88 | 0.69 | 0.91 |
| Ier5l | 0.55 | 0.64 | 0.87 | 0.94 | 1.98 | 0.95 | 1.36 | 2.66 | 1.16 | 0.75 | 0.94 | 0.85 |
| Ifi203 | 1.51 | 1.29 | 1.50 | 2.65 | 1.00 | 2.79 | 1.00 | 1.00 | 1.00 | 2.48 | 1.48 | 2.25 |
| Ifi204 | 2.34 | 2.67 | 2.55 | 1.11 | 0.36 | 0.83 | 1.37 | 1.00 | 1.11 | 0.56 | 0.36 | 0.54 |
| Ifi205 | 2.41 | 3.09 | 1.31 | 2.24 | 0.50 | 1.80 | 1.00 | 1.00 | 1.00 | 0.31 | 0.22 | 0.51 |
| Ifi27 | 2.75 | 4.49 | 3.45 | 0.76 | 2.60 | 0.81 | 0.66 | 1.02 | 1.10 | 3.18 | 2.99 | 2.26 |
| Ifi27l2a | 2.94 | 5.07 | 2.84 | 0.27 | 1.15 | 0.50 | 2.07 | 1.45 | 2.52 | 7.92 | 6.66 | 5.07 |
| Ifi35 | 1.45 | 2.06 | 1.56 | 1.06 | 2.56 | 1.06 | 1.41 | 1.60 | 0.93 | 1.24 | 1.41 | 1.11 |
| Ifi44 | 3.57 | 4.95 | 2.73 | 1.22 | 1.00 | 1.24 | 1.00 | 1.00 | 1.00 | 4.78 | 2.88 | 2.49 |
| Ifi47 | 4.72 | 6.13 | 4.36 | 1.48 | 3.59 | 1.58 | 1.00 | 1.00 | 1.00 | 1.37 | 1.07 | 1.01 |
| Ifit1 | 12.88 | 19.83 | 6.28 | 3.77 | 0.96 | 2.76 | 1.00 | 1.00 | 1.00 | 9.97 | 4.34 | 5.35 |
| Ifit3 | 3.24 | 3.40 | 2.05 | 1.53 | 0.64 | 1.16 | 1.18 | 1.00 | 1.37 | 7.36 | 4.29 | 3.27 |
| Ifitm2 | 1.06 | 1.25 | 1.42 | 1.03 | 1.27 | 1.10 | 0.65 | 0.30 | 0.70 | 1.24 | 1.48 | 1.14 |
| Ifrd1 | 1.24 | 1.29 | 0.90 | 1.29 | 0.29 | 1.28 | 0.99 | 0.27 | 1.18 | 1.27 | 1.19 | 0.94 |
| Ift22 | 0.91 | 0.94 | 1.20 | 0.61 | 2.50 | 0.75 | 1.07 | 2.58 | 1.01 | 1.00 | 1.03 | 0.84 |
| Ift27 | 1.39 | 1.21 | 1.14 | 0.93 | 1.34 | 0.90 | 1.01 | 3.40 | 1.09 | 1.12 | 1.23 | 0.89 |
| Ift43 | 1.13 | 1.10 | 1.24 | 1.17 | 0.38 | 1.40 | 0.87 | 0.49 | 0.79 | 0.90 | 1.59 | 1.46 |
| Ift46 | 1.28 | 1.29 | 1.32 | 1.12 | 3.43 | 0.93 | 0.94 | 2.58 | 0.92 | 1.19 | 1.49 | 1.20 |
| Igfbp1 | 3.56 | 8.10 | 1.00 | 1.97 | 1.15 | 3.92 | 1.00 | 1.00 | 1.00 | 1.00 | 1.21 | 1.00 |
| Igfbp2 | 1.41 | 1.82 | 1.28 | 1.14 | 2.95 | 1.77 | 0.76 | 2.17 | 1.03 | 0.64 | 1.62 | 0.47 |
| Igflr1 | 1.05 | 1.07 | 1.26 | 0.88 | 5.63 | 0.96 | 0.52 | 1.22 | 1.10 | 1.05 | 1.19 | 1.00 |
| Igj | 23.28 | 1.00 | 5.23 | 0.93 | 1.50 | 1.99 | 1.00 | 1.00 | 1.00 | 0.74 | 0.66 | 0.83 |

Fig. 35- 192

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Hmga1-rs1 | 0.57 | 1.00 | 0.66 | 0.92 | 0.87 | 0.57 | 1.20 | 2.50 | 0.90 | 1.01 | 1.04 | 1.03 |
| Hmgb4 | 1.00 | 1.00 | 1.00 | 1.00 | 1.00 | 1.00 | 2.91 | 2.23 | 1.00 | 1.00 | 1.00 | 1.00 |
| Hmgcl | 0.85 | 0.99 | 0.69 | 1.06 | 1.50 | 1.07 | 1.30 | 8.54 | 1.24 | 2.62 | 1.73 | 1.21 |
| Hmgcs2 | 0.84 | 0.94 | 1.16 | 1.07 | 1.21 | 1.78 | 4.18 | 4.27 | 6.66 | 1.00 | 1.00 | 1.00 |
| Hmgn1 | 0.70 | 0.49 | 0.71 | 1.00 | 1.35 | 0.90 | 0.86 | 2.25 | 0.82 | 1.22 | 0.81 | 0.90 |
| Hmox1 | 1.80 | 1.90 | 1.68 | 1.46 | 1.00 | 1.23 | 0.96 | 0.11 | 0.80 | 0.25 | 0.62 | 0.93 |
| Hnrnpa1 | 1.49 | 0.94 | 1.44 | 0.88 | 1.24 | 1.10 | 2.42 | 5.79 | 0.87 | 2.11 | 0.86 | 0.97 |
| Homer3 | 1.00 | 1.00 | 1.83 | 1.10 | 0.86 | 1.10 | 1.23 | 6.86 | 0.93 | 2.56 | 0.89 | 1.16 |
| Hoxb7 | 1.00 | 1.00 | 1.00 | 1.00 | 1.00 | 1.00 | 1.00 | 1.00 | 1.00 | 1.00 | 1.00 | 1.00 |
| Hp | 1.43 | 1.00 | 0.58 | 0.51 | 1.07 | 1.84 | 1.47 | 10.91 | 1.65 | 4.49 | 2.75 | 1.90 |
| Hpca | 1.00 | 1.00 | 1.00 | 1.13 | 1.00 | 1.10 | 1.00 | 0.76 | 0.84 | 1.00 | 1.00 | 1.00 |
| Hpcal4 | 1.00 | 1.00 | 1.00 | 1.00 | 1.10 | 0.95 | 1.00 | 1.00 | 1.00 | 1.00 | 1.00 | 1.00 |
| Hpd | 1.00 | 1.00 | 1.00 | 1.00 | 1.00 | 1.00 | 1.00 | 1.00 | 1.00 | 1.00 | 1.00 | 1.00 |
| Hpgd | 4.43 | 5.13 | 1.65 | 0.93 | 0.68 | 0.93 | 1.82 | 0.45 | 2.26 | 0.46 | 0.35 | 0.56 |
| Hps1 | 1.00 | 1.00 | 0.99 | 1.39 | 1.49 | 1.02 | 0.74 | 4.05 | 0.84 | 2.68 | 1.41 | 1.37 |
| Hr | 1.00 | 1.00 | 1.00 | 1.34 | 1.31 | 1.29 | 1.31 | 1.24 | 1.09 | 1.00 | 1.00 | 1.00 |
| Hras | 0.87 | 1.11 | 1.43 | 1.14 | 0.90 | 1.02 | 0.96 | 6.02 | 0.72 | 1.93 | 0.90 | 1.00 |
| Hrasls5 | 1.00 | 1.00 | 1.00 | 1.00 | 1.00 | 1.00 | 6.83 | 1.00 | 1.00 | 1.00 | 1.00 | 1.00 |
| Hrct1 | 1.00 | 1.00 | 0.95 | 2.06 | 0.29 | 0.86 | 1.18 | 11.89 | 1.10 | 1.00 | 1.00 | 1.00 |
| Hrsp12 | 1.20 | 1.00 | 1.28 | 1.52 | 18.21 | 1.61 | 1.04 | 1.16 | 1.47 | 1.28 | 1.47 | 1.83 |
| Hsd17b10 | 0.90 | 0.85 | 0.94 | 1.17 | 1.48 | 1.10 | 1.45 | 4.54 | 1.04 | 1.87 | 1.14 | 1.15 |
| Hsd17b11 | 1.36 | 1.29 | 1.42 | 1.11 | 1.27 | 1.11 | 1.44 | 5.39 | 1.60 | 2.10 | 1.32 | 1.25 |
| Hsd17b7 | 1.00 | 1.00 | 1.00 | 1.45 | 1.00 | 1.40 | 1.51 | 0.38 | 1.36 | 1.00 | 1.24 | 1.62 |
| Hspa1a | 1.00 | 1.00 | 1.00 | 1.27 | 0.22 | 1.05 | 0.85 | 0.36 | 0.86 | 1.00 | 1.00 | 1.22 |
| Hspa1b | 1.00 | 1.24 | 1.06 | 0.80 | 1.00 | 0.75 | 0.65 | 0.16 | 0.65 | 1.04 | 1.00 | 1.68 |
| Hspa2 | 1.00 | 1.00 | 1.00 | 0.96 | 1.27 | 0.88 | 1.01 | 0.82 | 0.91 | 0.34 | 0.75 | 0.89 |
| Hspb1 | 2.09 | 3.32 | 0.93 | 2.05 | 9.28 | 1.26 | 1.37 | 2.55 | 0.97 | 1.00 | 1.00 | 1.00 |
| Hspb11 | 1.00 | 1.00 | 1.00 | 0.35 | 7.94 | 0.91 | 0.55 | 0.53 | 0.76 | 0.64 | 2.34 | 1.59 |
| Hspb2 | 1.00 | 1.00 | 1.00 | 0.78 | 0.63 | 1.12 | 1.68 | 16.04 | 1.14 | 1.00 | 1.00 | 1.00 |
| Hspb3 | 0.86 | 0.89 | 1.00 | 1.20 | 0.59 | 1.05 | 1.44 | 13.02 | 1.55 | 1.00 | 1.00 | 1.00 |
| Hspb9 | 1.00 | 1.01 | 1.00 | 1.00 | 1.01 | 1.00 | 11.53 | 1.00 | 1.00 | 1.00 | 0.98 | 1.00 |
| Hspbp1 | 1.60 | 1.53 | 1.03 | 1.10 | 1.96 | 1.04 | 1.34 | 7.38 | 0.98 | 1.59 | 0.89 | 0.94 |
| Htatip2 | 1.12 | 1.04 | 0.91 | 1.38 | 1.21 | 1.02 | 0.82 | 5.20 | 0.80 | 1.95 | 1.12 | 1.04 |
| Htr5b | 10.49 | 9.13 | 9.75 | 1.80 | 1.00 | 1.84 | 1.00 | 1.00 | 1.00 | 1.00 | 1.00 | 1.00 |
| Htra3 | 0.85 | 1.42 | 1.52 | 1.28 | 2.51 | 1.14 | 2.07 | 3.34 | 1.61 | 1.00 | 1.00 | 1.00 |
| Hyi | 1.87 | 0.54 | 0.99 | 1.04 | 2.17 | 1.38 | 1.24 | 4.60 | 1.03 | 2.24 | 0.69 | 0.49 |
| Hyls1 | 0.96 | 1.14 | 1.00 | 0.89 | 1.71 | 0.82 | 0.85 | 1.13 | 0.79 | 1.18 | 0.89 | 1.05 |
| I830012O16Rik | 1.00 | 1.00 | 1.00 | 0.82 | 0.40 | 1.38 | 1.08 | 1.00 | 0.86 | 1.24 | 3.46 | 3.94 |
| Icam2 | 0.73 | 1.00 | 1.31 | 0.79 | 0.30 | 0.90 | 1.41 | 7.95 | 1.55 | 1.83 | 1.28 | 1.25 |
| Ict1 | 1.11 | 0.69 | 0.88 | 0.95 | 1.93 | 1.05 | 0.86 | 7.06 | 0.85 | 2.59 | 1.10 | 1.08 |
| Idnk | 1.01 | 1.35 | 0.93 | 0.97 | 1.05 | 1.27 | 0.96 | 4.01 | 0.99 | 2.27 | 1.49 | 1.27 |
| Ier2 | 1.67 | 2.19 | 1.45 | 1.17 | 0.72 | 1.07 | 1.06 | 2.12 | 0.79 | 1.67 | 1.42 | 1.16 |
| Ier5 | 1.00 | 0.98 | 0.80 | 1.05 | 1.12 | 0.97 | 0.83 | 0.38 | 0.76 | 0.44 | 0.98 | 1.01 |
| Ier5l | 1.00 | 1.00 | 1.00 | 0.75 | 0.99 | 0.90 | 0.81 | 2.02 | 0.71 | 1.04 | 1.04 | 1.00 |
| Ifi203 | 1.00 | 1.00 | 1.00 | 1.00 | 1.00 | 1.00 | 1.21 | 0.91 | 1.30 | 1.72 | 2.11 | 2.58 |
| Ifi204 | 1.00 | 1.00 | 1.00 | 1.00 | 1.00 | 1.00 | 2.64 | 1.21 | 3.07 | 1.10 | 1.00 | 1.05 |
| Ifi205 | 1.54 | 1.81 | 1.77 | 1.00 | 1.00 | 1.00 | 12.68 | 2.12 | 11.13 | 0.27 | 0.20 | 0.26 |
| Ifi27 | 2.37 | 1.48 | 1.83 | 1.16 | 2.00 | 1.48 | 1.43 | 7.37 | 1.26 | 16.64 | 8.40 | 6.30 |
| Ifi27l2a | 0.94 | 2.22 | 1.22 | 1.47 | 13.25 | 1.79 | 1.46 | 13.71 | 1.14 | 203.66 | 47.59 | 58.02 |
| Ifi35 | 0.84 | 0.85 | 0.89 | 1.04 | 0.42 | 1.07 | 1.34 | 8.46 | 1.08 | 3.41 | 1.54 | 1.46 |
| Ifi44 | 1.00 | 1.00 | 1.00 | 1.00 | 1.00 | 1.00 | 1.00 | 1.00 | 1.00 | 1.56 | 1.11 | 1.00 |
| Ifi47 | 1.00 | 1.00 | 1.00 | 1.00 | 1.00 | 1.00 | 2.24 | 1.00 | 2.13 | 1.35 | 1.41 | 1.33 |
| Ifit1 | 1.00 | 1.00 | 1.00 | 1.80 | 0.85 | 1.76 | 1.00 | 1.00 | 1.00 | 4.02 | 3.19 | 3.98 |
| Ifit3 | 1.00 | 1.00 | 1.00 | 1.52 | 5.42 | 1.64 | 1.51 | 0.72 | 1.36 | 4.90 | 8.60 | 8.79 |
| Ifitm2 | 1.13 | 1.73 | 1.43 | 1.22 | 7.25 | 1.48 | 1.22 | 0.45 | 0.99 | 0.38 | 0.58 | 0.57 |
| Ifrd1 | 0.55 | 0.65 | 0.58 | 1.10 | 1.18 | 0.92 | 1.20 | 0.22 | 1.13 | 0.38 | 0.92 | 0.97 |
| Ift22 | 0.94 | 1.14 | 0.82 | 1.13 | 0.71 | 1.02 | 1.25 | 13.54 | 0.70 | 1.99 | 0.79 | 1.06 |
| Ift27 | 0.82 | 0.81 | 0.69 | 1.37 | 0.83 | 0.94 | 0.97 | 11.71 | 1.00 | 2.44 | 0.83 | 1.21 |
| Ift43 | 1.00 | 1.00 | 1.00 | 0.76 | 3.40 | 1.01 | 1.20 | 1.97 | 1.13 | 1.00 | 1.00 | 1.00 |
| Ift46 | 1.23 | 1.93 | 1.53 | 1.44 | 1.02 | 0.93 | 1.27 | 12.87 | 0.98 | 3.31 | 1.18 | 1.29 |
| Igfbp1 | 1.00 | 1.00 | 1.00 | 1.00 | 1.29 | 1.00 | 1.00 | 1.00 | 1.00 | 1.00 | 1.00 | 1.00 |
| Igfbp2 | 1.00 | 1.00 | 1.00 | 1.09 | 0.97 | 0.98 | 1.15 | 6.18 | 0.94 | 1.00 | 1.00 | 1.00 |
| Igf1r1 | 1.05 | 1.65 | 0.95 | 1.28 | 1.28 | 0.97 | 1.17 | 5.23 | 1.00 | 2.03 | 1.21 | 1.03 |
| Igj | 0.54 | 1.00 | 0.84 | 1.00 | 1.00 | 1.00 | 1.00 | 1.00 | 1.00 | 0.40 | 0.67 | 0.72 |

Fig. 35- 193

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Igtp | 1.17 | 0.96 | 1.16 | 2.20 | 0.76 | 1.25 | 1.25 | 1.22 | 1.69 | 0.80 | 0.65 | 1.75 |
| Ikbke | 1.00 | 0.87 | 1.00 | 1.00 | 1.54 | 1.00 | 1.00 | 1.00 | 1.00 | 2.02 | 3.00 | 0.80 |
| Il11ra1 | 1.45 | 0.51 | 1.29 | 0.41 | 5.75 | 0.92 | 1.07 | 0.82 | 0.87 | 2.93 | 3.31 | 1.21 |
| Il11ra2 | 1.17 | 1.72 | 1.83 | 0.89 | 2.44 | 1.00 | 1.70 | 1.04 | 1.00 | 7.63 | 10.45 | 2.86 |
| Il17b | 1.00 | 1.00 | 1.00 | 1.00 | 1.00 | 1.00 | 1.00 | 1.00 | 1.00 | 1.55 | 1.56 | 1.00 |
| Il17rc | 1.14 | 0.63 | 1.14 | 0.47 | 6.70 | 1.02 | 1.51 | 1.33 | 1.15 | 1.48 | 2.55 | 1.04 |
| Il18 | 1.00 | 0.80 | 1.00 | 1.00 | 2.10 | 1.00 | 1.00 | 1.00 | 1.15 | 0.85 | 1.60 | 0.92 |
| Il1r2 | 2.55 | 1.33 | 1.17 | 1.35 | 3.14 | 1.00 | 1.00 | 1.00 | 1.00 | 17.18 | 15.25 | 4.25 |
| Il3ra | 1.00 | 0.91 | 1.00 | 0.40 | 2.57 | 1.13 | 0.88 | 0.71 | 0.86 | 1.80 | 1.76 | 0.82 |
| Il5ra | 1.00 | 1.00 | 1.00 | 1.00 | 1.00 | 1.00 | 1.00 | 1.00 | 1.00 | 1.00 | 1.00 | 1.00 |
| Il6ra | 2.50 | 1.13 | 5.05 | 10.91 | 1.13 | 5.49 | 2.22 | 3.79 | 2.30 | 1.20 | 0.33 | 1.38 |
| Ilf2 | 1.46 | 1.07 | 1.18 | 1.06 | 4.85 | 1.55 | 1.20 | 0.99 | 0.93 | 1.41 | 1.99 | 0.90 |
| Ilkap | 1.66 | 0.61 | 1.01 | 0.26 | 9.84 | 1.02 | 1.29 | 0.88 | 1.03 | 3.05 | 3.73 | 0.91 |
| Immp1l | 1.30 | 0.73 | 0.99 | 0.53 | 6.17 | 1.07 | 1.10 | 1.18 | 0.61 | 2.03 | 2.68 | 1.29 |
| Immp2l | 1.44 | 1.13 | 0.79 | 0.66 | 5.23 | 0.98 | 1.02 | 0.92 | 0.77 | 1.13 | 1.48 | 0.90 |
| Impdh1 | 1.42 | 0.86 | 0.97 | 3.02 | 7.12 | 3.94 | 0.77 | 0.71 | 0.84 | 0.27 | 0.42 | 0.77 |
| Ina | 1.00 | 1.00 | 1.00 | 1.00 | 0.15 | 1.00 | 1.00 | 1.00 | 1.00 | 1.00 | 1.00 | 1.00 |
| Inca1 | 1.17 | 1.09 | 1.50 | 2.51 | 7.49 | 1.86 | 1.00 | 0.88 | 1.00 | 1.04 | 2.71 | 1.00 |
| Inmt | 1.92 | 1.52 | 1.99 | 1.59 | 6.50 | 2.58 | 0.60 | 0.59 | 0.57 | 0.65 | 1.02 | 0.96 |
| Ino80b | 1.16 | 0.92 | 0.79 | 0.78 | 3.71 | 1.20 | 1.40 | 1.04 | 1.06 | 0.80 | 1.55 | 0.86 |
| Inpp5a | 0.79 | 0.51 | 0.62 | 0.64 | 3.60 | 1.06 | 0.85 | 0.89 | 0.87 | 2.77 | 2.63 | 0.98 |
| Ins2 | 1.00 | 1.00 | 1.00 | 1.00 | 1.00 | 1.00 | 1.00 | 1.00 | 1.00 | 1.00 | 1.00 | 1.00 |
| Insig2 | 0.88 | 2.07 | 0.89 | 0.77 | 0.28 | 0.89 | 0.89 | 0.93 | 0.89 | 0.45 | 0.28 | 1.05 |
| Insl3 | 2.20 | 0.65 | 0.92 | 0.25 | 3.72 | 0.84 | 0.88 | 0.47 | 0.91 | 1.08 | 1.69 | 0.88 |
| Ints1 | 0.90 | 0.53 | 0.93 | 0.45 | 2.11 | 0.75 | 1.27 | 1.37 | 1.16 | 2.91 | 3.09 | 0.91 |
| Ints3 | 1.83 | 0.79 | 1.17 | 1.12 | 6.51 | 1.18 | 1.78 | 1.93 | 1.33 | 2.26 | 3.03 | 1.06 |
| Ipo5 | 1.01 | 0.77 | 0.90 | 0.70 | 3.91 | 1.01 | 0.90 | 0.88 | 0.85 | 2.93 | 2.44 | 1.01 |
| Iqcj | 1.00 | 1.00 | 1.00 | 1.00 | 1.00 | 1.00 | 1.00 | 1.00 | 1.00 | 1.00 | 1.00 | 1.00 |
| Iqck | 1.00 | 0.83 | 1.00 | 1.55 | 1.76 | 0.88 | 1.00 | 1.00 | 1.00 | 1.24 | 1.31 | 1.06 |
| Irf4 | 5.05 | 4.69 | 3.91 | 28.05 | 33.46 | 9.57 | 1.00 | 1.00 | 1.00 | 0.91 | 0.68 | 0.92 |
| Irf7 | 2.13 | 1.61 | 3.04 | 2.77 | 4.16 | 2.68 | 2.91 | 4.53 | 6.37 | 2.21 | 2.10 | 2.53 |
| Irgc1 | 1.00 | 1.00 | 1.00 | 1.00 | 1.00 | 1.00 | 1.00 | 1.00 | 1.00 | 2.27 | 1.86 | 1.00 |
| Irs2 | 2.60 | 1.00 | 2.35 | 6.71 | 0.05 | 2.27 | 6.55 | 17.50 | 3.81 | 1.00 | 1.00 | 1.29 |
| Isg15 | 1.62 | 2.00 | 2.78 | 1.41 | 6.63 | 3.95 | 2.48 | 1.47 | 3.41 | 1.60 | 2.32 | 2.80 |
| Isoc2a | 1.04 | 0.81 | 1.07 | 0.38 | 5.28 | 0.93 | 0.93 | 0.97 | 0.93 | 1.96 | 3.09 | 1.06 |
| Isoc2b | 4.44 | 1.24 | 2.30 | 0.41 | 6.31 | 0.89 | 1.47 | 0.92 | 1.10 | 1.52 | 1.74 | 0.75 |
| Isyna1 | 1.59 | 0.61 | 1.49 | 1.29 | 5.96 | 2.36 | 1.20 | 0.96 | 0.90 | 1.42 | 1.61 | 1.06 |
| Itga11 | 0.80 | 1.00 | 0.90 | 1.00 | 1.00 | 1.00 | 0.93 | 0.95 | 1.00 | 1.00 | 1.00 | 1.00 |
| Itga2b | 1.00 | 1.00 | 1.00 | 1.00 | 1.48 | 1.00 | 1.00 | 1.00 | 1.32 | 3.24 | 3.51 | 1.42 |
| Itgb1bp2 | 0.79 | 0.48 | 0.59 | 1.00 | 2.22 | 0.61 | 0.80 | 0.77 | 0.65 | 1.63 | 2.37 | 0.98 |
| Itgb5 | 0.83 | 0.58 | 0.94 | 0.99 | 5.28 | 1.40 | 1.67 | 1.65 | 1.42 | 1.56 | 1.98 | 1.07 |
| Itih4 | 1.00 | 1.00 | 1.00 | 1.00 | 1.00 | 1.00 | 0.91 | 0.65 | 0.65 | 1.32 | 1.59 | 0.82 |
| Itih5 | 0.68 | 0.76 | 1.00 | 5.56 | 1.43 | 1.91 | 0.62 | 0.67 | 0.75 | 1.78 | 1.03 | 1.15 |
| Itln1 | 1.00 | 1.00 | 1.00 | 1.00 | 1.00 | 1.00 | 1.00 | 1.00 | 1.00 | 7.02 | 12.93 | 5.96 |
| Itm2a | 0.63 | 0.92 | 0.64 | 1.03 | 1.22 | 0.79 | 0.74 | 0.57 | 0.52 | 1.46 | 1.26 | 1.01 |
| Itpka | 1.00 | 1.00 | 1.00 | 0.41 | 0.52 | 0.73 | 1.00 | 1.00 | 1.00 | 0.93 | 1.48 | 1.00 |
| Izumo4 | 0.99 | 0.79 | 0.61 | 0.58 | 9.30 | 0.45 | 1.26 | 0.82 | 1.32 | 1.54 | 2.91 | 1.29 |
| Jmjd8 | 1.00 | 0.57 | 0.84 | 0.42 | 3.65 | 0.89 | 0.86 | 0.87 | 0.77 | 2.25 | 2.48 | 0.89 |
| Josd2 | 1.55 | 0.57 | 0.91 | 0.32 | 6.40 | 0.95 | 1.32 | 0.82 | 1.07 | 2.41 | 3.96 | 1.21 |
| Jph3 | 1.00 | 1.00 | 1.00 | 1.00 | 0.24 | 1.00 | 1.00 | 1.00 | 1.00 | 1.00 | 1.00 | 1.00 |
| Jph4 | 1.00 | 1.00 | 1.00 | 1.00 | 0.18 | 1.00 | 1.00 | 1.00 | 1.00 | 1.00 | 1.00 | 1.00 |
| Jsrp1 | 1.14 | 0.50 | 0.79 | 1.59 | 9.71 | 1.30 | 0.96 | 0.78 | 1.62 | 1.00 | 1.00 | 1.00 |
| Junb | 6.20 | 7.53 | 2.66 | 1.00 | 0.79 | 1.42 | 1.83 | 1.32 | 1.95 | 0.89 | 0.84 | 1.17 |
| Kap | 1.00 | 9.41 | 1.00 | 1.00 | 3.28 | 1.00 | 1.00 | 1.02 | 1.00 | 2.74 | 1.00 | 1.00 |
| Kbtbd3 | 0.88 | 0.53 | 0.61 | 0.74 | 3.46 | 0.77 | 0.51 | 0.61 | 0.74 | 2.81 | 2.79 | 0.83 |
| Kcnc1 | 1.31 | 1.52 | 0.97 | 1.00 | 0.20 | 1.00 | 1.00 | 0.76 | 0.55 | 1.00 | 1.00 | 1.00 |
| Kcnj11 | 1.15 | 1.39 | 1.19 | 0.73 | 0.40 | 1.17 | 0.98 | 0.91 | 1.03 | 1.39 | 1.19 | 0.83 |
| Kcnj4 | 1.00 | 1.00 | 1.00 | 1.00 | 0.23 | 1.00 | 1.16 | 0.85 | 0.68 | 1.00 | 1.00 | 1.00 |
| Kcnk1 | 2.79 | 2.60 | 6.68 | 1.00 | 0.26 | 1.00 | 1.00 | 1.00 | 1.00 | 1.71 | 1.83 | 1.76 |
| Kcnk3 | 3.15 | 2.58 | 8.40 | 0.69 | 0.73 | 1.48 | 0.89 | 0.85 | 0.91 | 1.05 | 0.84 | 1.09 |
| Kcnk7 | 1.00 | 1.00 | 1.00 | 1.00 | 1.00 | 1.00 | 1.00 | 1.00 | 1.00 | 0.70 | 2.34 | 1.27 |
| Kcnq2 | 1.00 | 1.00 | 1.00 | 1.00 | 0.32 | 1.00 | 1.00 | 1.00 | 1.00 | 1.00 | 1.00 | 1.00 |
| Kdelr2 | 1.16 | 1.36 | 0.99 | 1.12 | 1.38 | 1.12 | 0.79 | 0.75 | 0.98 | 0.50 | 0.61 | 0.97 |
| Kdm7a | 0.92 | 2.28 | 1.18 | 8.20 | 1.13 | 2.46 | 1.26 | 1.49 | 1.27 | 0.68 | 0.37 | 1.09 |

Fig. 35- 194

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Igtp | 1.45 | 1.47 | 1.45 | 1.22 | 2.12 | 1.17 | 0.72 | 0.18 | 1.17 | 1.67 | 0.87 | 1.34 |
| Ikbke | 1.17 | 1.20 | 1.14 | 1.00 | 0.46 | 1.10 | 1.37 | 2.21 | 1.46 | 1.04 | 1.47 | 1.05 |
| Il11ra1 | 2.72 | 2.57 | 1.40 | 0.88 | 0.42 | 1.08 | 1.66 | 3.23 | 1.51 | 0.82 | 1.24 | 1.14 |
| Il11ra2 | 8.51 | 6.96 | 4.42 | 1.30 | 2.88 | 1.88 | 1.00 | 2.44 | 1.00 | 1.00 | 1.53 | 1.00 |
| Il17b | 1.00 | 1.00 | 1.36 | 1.00 | 1.00 | 1.00 | 1.00 | 1.00 | 1.00 | 1.00 | 1.00 | 1.00 |
| Il17rc | 1.21 | 1.40 | 1.17 | 1.04 | 0.88 | 1.31 | 1.65 | 1.72 | 1.58 | 1.28 | 1.69 | 1.27 |
| Il18 | 2.11 | 2.11 | 2.22 | 0.89 | 2.01 | 1.06 | 0.36 | 0.19 | 0.62 | 0.91 | 1.20 | 0.83 |
| Il1r2 | 1.38 | 0.97 | 1.00 | 1.00 | 1.00 | 1.00 | 1.00 | 1.85 | 1.00 | 1.00 | 1.00 | 1.00 |
| Il3ra | 1.21 | 1.50 | 1.43 | 1.00 | 0.50 | 1.00 | 1.00 | 0.69 | 1.00 | 1.17 | 0.72 | 0.79 |
| Il5ra | 1.55 | 1.12 | 1.11 | 1.00 | 1.00 | 1.00 | 1.00 | 1.00 | 1.00 | 1.00 | 1.00 | 1.00 |
| Il6ra | 0.83 | 0.51 | 1.84 | 1.96 | 1.00 | 1.87 | 0.90 | 2.74 | 1.13 | 1.51 | 0.40 | 1.21 |
| Ilf2 | 0.99 | 1.16 | 0.91 | 1.07 | 0.94 | 0.86 | 0.98 | 1.56 | 0.92 | 1.02 | 1.47 | 1.05 |
| Ilkap | 1.23 | 1.38 | 0.91 | 1.09 | 0.62 | 0.94 | 0.86 | 2.18 | 0.93 | 0.79 | 1.70 | 0.95 |
| Immp1l | 1.25 | 1.56 | 1.35 | 0.73 | 1.02 | 0.87 | 0.67 | 1.84 | 0.85 | 0.61 | 1.98 | 1.19 |
| Immp2l | 1.20 | 1.32 | 1.15 | 0.81 | 0.80 | 0.72 | 1.20 | 1.27 | 0.89 | 0.91 | 1.33 | 1.42 |
| Impdh1 | 0.72 | 1.01 | 0.76 | 0.84 | 1.57 | 0.89 | 1.18 | 1.00 | 1.18 | 1.03 | 1.25 | 1.20 |
| Ina | 1.00 | 1.00 | 1.00 | 1.00 | 1.00 | 1.00 | 1.00 | 1.00 | 1.00 | 1.11 | 1.00 | 0.88 |
| Inca1 | 1.06 | 1.89 | 2.11 | 0.88 | 0.92 | 0.70 | 1.81 | 1.63 | 1.77 | 0.81 | 1.30 | 0.76 |
| Inmt | 5.96 | 4.79 | 1.97 | 0.63 | 0.99 | 0.74 | 0.02 | 0.04 | 0.09 | 0.84 | 1.80 | 1.20 |
| Ino80b | 1.17 | 1.75 | 0.99 | 1.01 | 1.17 | 1.17 | 0.73 | 0.56 | 0.77 | 1.08 | 1.40 | 1.09 |
| Inpp5a | 1.38 | 1.59 | 1.20 | 1.00 | 0.71 | 1.13 | 0.99 | 2.74 | 0.86 | 1.06 | 1.40 | 1.15 |
| Ins2 | 1.00 | 1.40 | 1.00 | 1.00 | 0.49 | 1.00 | 1.00 | 1.90 | 1.00 | 0.36 | 1.00 | 1.00 |
| Insig2 | 1.10 | 0.85 | 0.97 | 1.06 | 2.46 | 0.99 | 13.60 | 7.98 | 10.04 | 1.29 | 0.99 | 1.23 |
| Insl3 | 1.81 | 1.87 | 1.51 | 0.96 | 0.79 | 1.15 | 2.37 | 1.13 | 1.14 | 1.01 | 1.28 | 1.08 |
| Ints1 | 0.73 | 0.77 | 0.84 | 0.93 | 0.53 | 1.10 | 1.02 | 1.65 | 1.17 | 0.98 | 0.93 | 0.89 |
| Ints3 | 0.91 | 0.99 | 0.96 | 1.20 | 0.72 | 1.02 | 1.14 | 2.64 | 1.05 | 1.01 | 1.37 | 0.86 |
| Ipo5 | 0.67 | 0.72 | 0.78 | 0.96 | 0.58 | 0.93 | 1.08 | 3.18 | 1.10 | 1.00 | 1.19 | 0.97 |
| Iqcj | 1.00 | 1.00 | 1.00 | 1.00 | 1.00 | 1.00 | 1.00 | 1.00 | 1.00 | 1.00 | 1.00 | 1.00 |
| Iqck | 1.00 | 1.50 | 1.13 | 1.00 | 0.60 | 1.00 | 1.00 | 1.00 | 1.00 | 1.00 | 1.12 | 1.00 |
| Irf4 | 1.15 | 1.40 | 1.56 | 1.00 | 1.00 | 1.00 | 1.00 | 1.00 | 1.00 | 1.01 | 1.30 | 0.96 |
| Irf7 | 2.05 | 2.08 | 2.14 | 7.16 | 8.53 | 5.61 | 2.34 | 1.89 | 4.53 | 4.72 | 3.67 | 2.61 |
| Irgc1 | 1.00 | 1.00 | 1.00 | 1.00 | 1.00 | 1.00 | 1.00 | 1.67 | 1.00 | 1.00 | 1.00 | 1.00 |
| Irs2 | 0.68 | 0.38 | 1.47 | 2.55 | 1.00 | 2.33 | 2.09 | 1.00 | 2.80 | 1.41 | 0.17 | 1.28 |
| Isg15 | 1.61 | 2.23 | 1.57 | 3.82 | 12.03 | 2.77 | 1.00 | 0.22 | 2.60 | 10.34 | 6.57 | 2.84 |
| Isoc2a | 1.11 | 1.89 | 1.16 | 0.49 | 0.57 | 0.61 | 0.87 | 1.12 | 0.94 | 0.78 | 1.60 | 1.07 |
| Isoc2b | 0.69 | 0.65 | 0.69 | 0.44 | 0.32 | 0.43 | 0.28 | 0.20 | 0.27 | 0.39 | 0.58 | 0.51 |
| Isyna1 | 1.12 | 1.22 | 1.09 | 0.91 | 0.98 | 0.95 | 1.40 | 2.23 | 1.25 | 1.06 | 1.22 | 0.96 |
| Itga11 | 1.00 | 1.12 | 1.83 | 1.00 | 1.00 | 1.00 | 1.00 | 1.00 | 1.00 | 1.26 | 0.75 | 0.90 |
| Itga2b | 1.00 | 1.00 | 1.00 | 1.00 | 0.42 | 1.00 | 1.00 | 1.89 | 1.00 | 1.00 | 1.00 | 1.00 |
| Itgb1bp2 | 1.00 | 1.00 | 1.00 | 1.00 | 1.00 | 1.00 | 1.00 | 1.00 | 1.00 | 1.00 | 1.00 | 1.00 |
| Itgb5 | 1.80 | 1.60 | 1.81 | 1.00 | 0.79 | 1.01 | 0.93 | 1.02 | 1.04 | 1.04 | 1.19 | 0.97 |
| Itih4 | 1.00 | 1.00 | 1.00 | 1.00 | 1.00 | 1.00 | 0.87 | 1.34 | 0.99 | 1.00 | 1.00 | 1.00 |
| Itih5 | 1.45 | 1.00 | 1.28 | 1.44 | 1.75 | 1.57 | 1.92 | 1.00 | 1.80 | 1.04 | 0.78 | 0.97 |
| Itln1 | 1.38 | 0.91 | 1.71 | 1.00 | 1.00 | 1.00 | 1.00 | 1.00 | 1.00 | 0.25 | 0.08 | 0.07 |
| Itm2a | 0.62 | 0.83 | 0.76 | 0.50 | 0.59 | 0.78 | 1.00 | 1.00 | 1.00 | 0.80 | 1.03 | 1.10 |
| Itpka | 0.97 | 0.98 | 0.55 | 1.00 | 1.00 | 1.04 | 0.57 | 0.67 | 0.61 | 0.86 | 1.07 | 0.88 |
| Izumo4 | 1.19 | 1.33 | 1.21 | 1.09 | 0.72 | 1.19 | 0.71 | 0.97 | 0.71 | 0.71 | 1.57 | 1.57 |
| Jmjd8 | 1.09 | 1.18 | 0.98 | 0.83 | 0.66 | 0.94 | 0.83 | 1.78 | 0.78 | 0.94 | 1.29 | 1.02 |
| Josd2 | 1.37 | 1.45 | 1.18 | 0.97 | 0.51 | 1.01 | 1.39 | 2.31 | 1.38 | 1.20 | 1.55 | 1.12 |
| Jph3 | 1.00 | 1.00 | 1.00 | 1.00 | 1.00 | 1.00 | 1.00 | 1.00 | 1.00 | 1.28 | 1.00 | 1.07 |
| Jph4 | 1.00 | 1.00 | 1.00 | 1.00 | 1.00 | 1.00 | 1.00 | 1.00 | 1.00 | 1.20 | 0.83 | 1.06 |
| Jsrp1 | 1.00 | 1.00 | 1.00 | 1.00 | 1.00 | 1.00 | 1.00 | 1.00 | 1.00 | 1.00 | 1.00 | 1.00 |
| Junb | 1.12 | 1.21 | 1.26 | 1.21 | 1.55 | 1.25 | 2.07 | 2.45 | 1.86 | 1.15 | 1.47 | 1.21 |
| Kap | 5.20 | 0.88 | 1.00 | 1.50 | 1.18 | 1.31 | 0.69 | 2.45 | 1.31 | 3.42 | 13.28 | 2.38 |
| Kbtbd3 | 1.05 | 1.36 | 0.77 | 0.80 | 0.76 | 0.96 | 1.00 | 1.35 | 1.00 | 0.85 | 1.37 | 0.54 |
| Kcnc1 | 1.00 | 1.00 | 1.00 | 1.00 | 1.00 | 1.00 | 1.00 | 1.00 | 1.00 | 1.00 | 1.00 | 1.00 |
| Kcnj11 | 0.84 | 0.68 | 1.00 | 1.00 | 1.00 | 1.00 | 1.00 | 1.00 | 1.00 | 1.82 | 1.89 | 2.10 |
| Kcnj4 | 1.00 | 1.00 | 1.00 | 1.00 | 1.00 | 1.00 | 1.00 | 1.00 | 1.00 | 1.00 | 1.00 | 1.00 |
| Kcnk1 | 4.23 | 3.38 | 2.36 | 1.46 | 1.10 | 1.65 | 4.33 | 1.44 | 4.07 | 1.12 | 1.15 | 1.11 |
| Kcnk3 | 0.32 | 0.85 | 0.45 | 1.00 | 1.00 | 1.14 | 1.00 | 1.00 | 1.00 | 1.11 | 1.11 | 1.19 |
| Kcnk7 | 1.00 | 1.00 | 1.00 | 1.00 | 1.00 | 1.00 | 1.00 | 1.00 | 1.00 | 0.99 | 1.34 | 1.00 |
| Kcnq2 | 1.00 | 1.00 | 1.00 | 1.00 | 1.00 | 1.00 | 1.00 | 1.00 | 1.00 | 1.00 | 1.00 | 1.11 |
| Kdelr2 | 1.22 | 1.26 | 1.12 | 0.89 | 0.96 | 0.83 | 1.03 | 0.84 | 1.15 | 0.98 | 1.12 | 1.03 |
| Kdm7a | 0.92 | 0.72 | 1.24 | 1.45 | 1.00 | 1.06 | 1.27 | 1.00 | 0.90 | 1.29 | 0.88 | 1.14 |

Fig. 35- 195

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Igtp | 5.71 | 5.02 | 6.95 | 1.32 | 1.00 | 1.44 | 1.02 | 1.00 | 1.00 | 1.46 | 1.01 | 1.02 |
| Ikbke | 0.88 | 0.82 | 1.13 | 0.78 | 1.02 | 0.83 | 1.00 | 1.73 | 1.00 | 0.79 | 0.84 | 0.88 |
| Il11ra1 | 0.87 | 1.10 | 0.98 | 1.25 | 2.48 | 1.25 | 1.02 | 5.48 | 1.08 | 1.13 | 1.51 | 1.35 |
| Il11ra2 | 1.32 | 1.10 | 1.47 | 1.87 | 2.75 | 2.58 | 6.56 | 27.91 | 9.41 | 1.51 | 1.90 | 2.03 |
| Il17b | 1.00 | 1.00 | 1.00 | 1.00 | 1.00 | 1.00 | 1.00 | 1.00 | 1.00 | 1.00 | 1.00 | 1.00 |
| Il17rc | 0.90 | 1.18 | 1.08 | 0.82 | 1.82 | 0.93 | 1.00 | 1.15 | 1.12 | 0.90 | 1.02 | 0.77 |
| Il18 | 0.93 | 1.06 | 0.87 | 0.68 | 0.32 | 1.12 | 1.00 | 0.62 | 1.00 | 0.86 | 1.15 | 0.93 |
| Il1r2 | 1.65 | 1.81 | 1.50 | 1.00 | 1.00 | 1.00 | 1.00 | 1.00 | 1.00 | 5.11 | 3.75 | 2.26 |
| Il3ra | 1.00 | 1.00 | 1.00 | 1.21 | 1.69 | 0.73 | 0.80 | 2.80 | 1.03 | 0.85 | 1.01 | 0.64 |
| Il5ra | 1.00 | 1.00 | 1.00 | 1.00 | 1.00 | 1.00 | 1.00 | 1.00 | 1.00 | 1.66 | 1.25 | 5.69 |
| Il6ra | 1.41 | 1.80 | 1.04 | 1.96 | 0.26 | 1.70 | 1.30 | 1.00 | 1.26 | 0.82 | 0.48 | 1.08 |
| Ilf2 | 0.93 | 1.04 | 1.09 | 1.40 | 7.32 | 1.42 | 1.05 | 1.22 | 1.00 | 1.10 | 1.44 | 0.98 |
| Ilkap | 0.80 | 1.05 | 1.39 | 1.41 | 3.53 | 1.41 | 1.08 | 2.59 | 1.05 | 1.25 | 1.41 | 1.06 |
| Immp1l | 0.61 | 1.10 | 1.15 | 1.13 | 5.58 | 0.77 | 0.74 | 1.69 | 1.02 | 1.68 | 1.52 | 1.59 |
| Immp2l | 1.61 | 0.38 | 1.94 | 0.48 | 3.40 | 0.91 | 0.92 | 0.93 | 0.97 | 1.37 | 1.73 | 1.83 |
| Impdh1 | 1.17 | 1.10 | 1.05 | 0.97 | 0.91 | 1.08 | 0.78 | 0.45 | 0.66 | 0.85 | 1.12 | 0.87 |
| Ina | 1.65 | 1.42 | 1.05 | 1.00 | 1.00 | 1.00 | 1.00 | 1.00 | 1.00 | 1.00 | 10.82 | 1.00 |
| Inca1 | 1.00 | 2.20 | 1.00 | 1.22 | 5.48 | 1.60 | 0.85 | 0.82 | 0.85 | 1.10 | 1.40 | 1.69 |
| Inmt | 1.31 | 1.50 | 2.17 | 1.04 | 2.95 | 1.01 | 1.00 | 1.00 | 1.00 | 1.36 | 2.33 | 1.92 |
| Ino80b | 1.42 | 1.09 | 1.39 | 1.06 | 5.97 | 1.17 | 0.88 | 0.82 | 1.01 | 0.94 | 1.37 | 0.97 |
| Inpp5a | 1.07 | 1.25 | 1.10 | 1.13 | 2.17 | 1.14 | 0.75 | 2.41 | 0.82 | 1.27 | 1.47 | 1.17 |
| Ins2 | 1.00 | 1.00 | 4.59 | 1.00 | 1.00 | 1.00 | 1.00 | 1.71 | 0.88 | 1.00 | 1.07 | 1.00 |
| Insig2 | 0.82 | 0.86 | 0.78 | 1.53 | 0.77 | 1.28 | 1.08 | 0.99 | 1.06 | 1.09 | 0.83 | 1.03 |
| Insl3 | 0.82 | 1.38 | 1.13 | 0.23 | 2.87 | 1.16 | 0.65 | 0.59 | 0.78 | 1.01 | 1.04 | 0.88 |
| Ints1 | 0.75 | 0.81 | 0.66 | 0.90 | 1.20 | 0.78 | 1.31 | 3.46 | 1.29 | 0.88 | 0.96 | 1.06 |
| Ints3 | 0.97 | 1.05 | 0.84 | 1.48 | 2.53 | 1.27 | 1.24 | 3.25 | 1.06 | 0.94 | 1.03 | 1.03 |
| Ipo5 | 0.88 | 0.84 | 0.93 | 0.96 | 1.68 | 1.11 | 1.03 | 2.99 | 1.01 | 1.05 | 1.06 | 0.95 |
| Iqcj | 1.00 | 1.00 | 1.00 | 1.00 | 1.00 | 1.00 | 1.00 | 7.00 | 1.00 | 1.00 | 1.00 | 1.00 |
| Iqck | 1.00 | 1.00 | 1.00 | 0.99 | 1.00 | 1.19 | 0.97 | 1.85 | 0.85 | 1.00 | 1.15 | 1.00 |
| Irf4 | 2.24 | 1.94 | 1.00 | 3.83 | 4.62 | 10.39 | 1.00 | 1.00 | 1.00 | 1.02 | 0.63 | 1.15 |
| Irf7 | 16.43 | 20.86 | 12.03 | 1.44 | 2.42 | 1.71 | 1.00 | 1.00 | 1.44 | 3.12 | 2.26 | 2.49 |
| Irgc1 | 1.00 | 1.00 | 1.00 | 3.45 | 3.42 | 1.00 | 0.91 | 1.74 | 1.13 | 0.94 | 1.49 | 0.76 |
| Irs2 | 1.41 | 1.66 | 0.75 | 1.80 | 0.14 | 1.16 | 1.46 | 1.00 | 1.12 | 1.24 | 0.81 | 1.35 |
| Isg15 | 45.47 | 49.76 | 33.72 | 3.02 | 1.15 | 2.71 | 1.00 | 1.00 | 1.05 | 2.73 | 1.75 | 1.22 |
| Isoc2a | 1.05 | 1.17 | 1.23 | 0.76 | 3.23 | 1.00 | 0.86 | 2.25 | 1.17 | 0.95 | 1.21 | 1.01 |
| Isoc2b | 0.35 | 0.30 | 0.43 | 0.72 | 2.04 | 0.55 | 0.32 | 1.50 | 0.41 | 0.59 | 0.69 | 0.62 |
| Isyna1 | 1.54 | 1.54 | 1.15 | 1.13 | 3.61 | 1.21 | 1.03 | 1.07 | 1.15 | 1.00 | 1.11 | 1.05 |
| Itga11 | 1.07 | 1.26 | 0.93 | 0.62 | 1.00 | 0.65 | 3.80 | 6.25 | 4.23 | 1.33 | 1.11 | 1.20 |
| Itga2b | 1.00 | 1.00 | 1.00 | 1.00 | 1.05 | 1.00 | 1.00 | 1.51 | 1.00 | 1.44 | 1.05 | 0.75 |
| Itgb1bp2 | 1.11 | 1.01 | 1.00 | 1.00 | 0.93 | 1.00 | 1.00 | 1.00 | 1.00 | 1.00 | 1.07 | 1.00 |
| Itgb5 | 1.11 | 1.20 | 1.08 | 0.95 | 1.51 | 0.70 | 0.85 | 1.83 | 1.10 | 1.01 | 1.31 | 1.06 |
| Itih4 | 1.35 | 1.00 | 1.00 | 1.00 | 1.00 | 1.00 | 1.00 | 1.00 | 1.00 | 1.00 | 1.00 | 1.00 |
| Itih5 | 1.43 | 1.61 | 1.51 | 0.59 | 0.18 | 0.53 | 0.62 | 1.00 | 0.77 | 1.21 | 0.73 | 1.14 |
| Itln1 | 9.01 | 8.77 | 53.26 | 1.00 | 1.00 | 1.00 | 1.00 | 1.74 | 1.00 | 0.30 | 0.42 | 0.19 |
| Itm2a | 0.76 | 0.81 | 1.05 | 0.98 | 5.08 | 1.46 | 0.67 | 0.75 | 0.91 | 0.81 | 0.99 | 0.82 |
| Itpka | 0.93 | 0.96 | 0.80 | 0.48 | 1.00 | 1.41 | 1.08 | 0.86 | 1.50 | 1.00 | 5.56 | 1.00 |
| Izumo4 | 0.90 | 1.54 | 1.45 | 0.79 | 2.23 | 1.03 | 0.93 | 1.24 | 1.16 | 0.93 | 0.99 | 0.82 |
| Jmjd8 | 0.98 | 1.02 | 1.02 | 0.79 | 3.01 | 0.86 | 0.76 | 2.17 | 0.78 | 1.09 | 1.14 | 1.08 |
| Josd2 | 1.16 | 1.33 | 1.05 | 0.99 | 3.04 | 1.03 | 1.02 | 3.16 | 1.01 | 0.56 | 0.72 | 0.47 |
| Jph3 | 1.00 | 1.00 | 1.00 | 1.00 | 1.00 | 1.00 | 0.93 | 1.06 | 1.09 | 1.00 | 7.49 | 1.00 |
| Jph4 | 0.79 | 0.72 | 1.07 | 1.00 | 1.00 | 1.07 | 1.48 | 0.94 | 1.13 | 1.00 | 9.91 | 1.00 |
| Jsrp1 | 1.93 | 1.19 | 2.15 | 1.00 | 1.00 | 1.00 | 0.66 | 2.81 | 0.51 | 1.00 | 1.00 | 1.00 |
| Junb | 0.97 | 1.21 | 0.84 | 1.33 | 1.14 | 1.27 | 0.76 | 1.07 | 1.02 | 0.91 | 1.03 | 0.96 |
| Kap | 0.76 | 1.00 | 0.66 | 0.38 | 0.30 | 2.53 | 0.66 | 11.75 | 0.32 | 1.00 | 1.52 | 1.06 |
| Kbtbd3 | 0.73 | 0.81 | 1.45 | 0.63 | 1.76 | 0.72 | 0.77 | 2.33 | 0.94 | 1.18 | 1.26 | 0.94 |
| Kcnc1 | 1.00 | 1.00 | 1.00 | 1.00 | 1.00 | 1.00 | 0.99 | 1.13 | 1.30 | 1.00 | 7.46 | 1.00 |
| Kcnj11 | 1.45 | 1.27 | 1.45 | 1.00 | 1.00 | 1.00 | 1.00 | 1.00 | 1.00 | 1.00 | 2.30 | 1.00 |
| Kcnj4 | 1.00 | 1.00 | 1.00 | 1.00 | 1.00 | 1.00 | 1.00 | 1.00 | 1.00 | 1.00 | 5.54 | 1.00 |
| Kcnk1 | 0.85 | 0.81 | 0.83 | 1.65 | 2.44 | 1.97 | 0.99 | 0.71 | 0.63 | 1.00 | 5.93 | 1.00 |
| Kcnk3 | 1.08 | 1.46 | 1.06 | 1.63 | 1.97 | 2.31 | 0.57 | 1.00 | 0.54 | 0.54 | 0.77 | 0.75 |
| Kcnk7 | 1.14 | 1.91 | 1.00 | 1.00 | 1.00 | 1.00 | 0.88 | 1.46 | 1.06 | 1.00 | 1.00 | 1.00 |
| Kcnq2 | 1.00 | 1.00 | 1.00 | 1.00 | 1.00 | 1.00 | 0.62 | 1.00 | 0.34 | 1.00 | 5.26 | 1.00 |
| Kdelr2 | 0.83 | 0.75 | 0.91 | 0.99 | 0.56 | 1.15 | 0.80 | 0.79 | 0.98 | 1.06 | 1.10 | 0.95 |
| Kdm7a | 1.08 | 0.98 | 0.86 | 1.55 | 0.55 | 1.53 | 1.11 | 1.79 | 1.00 | 1.16 | 0.79 | 1.30 |

Fig. 35- 196

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Igtp | 1.00 | 1.00 | 1.00 | 1.38 | 1.00 | 1.39 | 1.58 | 0.46 | 1.27 | 1.36 | 2.60 | 2.13 |
| Ikbke | 1.00 | 1.00 | 1.00 | 1.00 | 0.36 | 1.00 | 0.89 | 10.31 | 0.89 | 4.15 | 1.59 | 1.37 |
| Il11ra1 | 0.57 | 0.44 | 0.69 | 0.58 | 0.75 | 0.79 | 1.82 | 23.91 | 1.74 | 2.05 | 0.80 | 0.65 |
| Il11ra2 | 1.00 | 1.00 | 1.00 | 4.67 | 11.17 | 5.72 | 43.71 | 95.46 | 15.05 | 1.00 | 1.00 | 1.48 |
| Il17b | 1.00 | 1.00 | 1.00 | 1.00 | 0.26 | 1.00 | 1.79 | 11.30 | 2.40 | 1.00 | 1.00 | 1.00 |
| Il17rc | 1.56 | 1.26 | 0.98 | 1.00 | 0.87 | 1.15 | 1.04 | 4.56 | 0.71 | 1.00 | 1.00 | 1.00 |
| Il18 | 1.00 | 1.00 | 1.00 | 1.10 | 11.92 | 0.99 | 0.69 | 1.28 | 0.62 | 1.55 | 0.69 | 1.40 |
| Il1r2 | 1.00 | 1.00 | 1.00 | 1.00 | 1.00 | 1.00 | 1.57 | 8.33 | 1.47 | 12.67 | 8.14 | 4.65 |
| Il3ra | 1.00 | 1.00 | 1.00 | 1.00 | 1.77 | 1.00 | 1.01 | 7.05 | 0.92 | 2.37 | 1.14 | 1.23 |
| Il5ra | 1.00 | 1.00 | 1.00 | 1.00 | 1.00 | 1.00 | 1.00 | 1.00 | 1.00 | 1.15 | 0.89 | 1.80 |
| Il6ra | 1.43 | 1.41 | 1.91 | 0.99 | 1.00 | 0.92 | 1.12 | 0.06 | 1.49 | 0.60 | 0.88 | 0.67 |
| Ilf2 | 0.70 | 1.25 | 0.69 | 1.15 | 0.82 | 1.02 | 1.01 | 2.77 | 0.97 | 1.55 | 1.01 | 1.03 |
| Ilkap | 0.87 | 1.14 | 0.66 | 0.93 | 0.82 | 1.07 | 1.09 | 10.09 | 1.08 | 2.61 | 1.20 | 1.02 |
| Immp1l | 0.86 | 0.80 | 1.00 | 0.77 | 2.49 | 1.23 | 1.03 | 14.18 | 1.28 | 2.67 | 1.74 | 1.04 |
| Immp2l | 1.05 | 0.99 | 1.15 | 1.21 | 3.19 | 1.40 | 1.02 | 1.00 | 1.12 | 1.31 | 1.00 | 1.00 |
| Impdh1 | 1.31 | 1.34 | 1.13 | 1.01 | 0.48 | 1.09 | 1.16 | 0.77 | 0.94 | 0.95 | 1.01 | 1.00 |
| Ina | 1.00 | 1.00 | 1.00 | 1.15 | 0.36 | 1.11 | 1.33 | 1.00 | 1.31 | 1.00 | 1.00 | 1.00 |
| Inca1 | 1.05 | 0.84 | 1.02 | 0.81 | 0.44 | 0.99 | 1.06 | 3.20 | 1.07 | 1.98 | 1.00 | 1.00 |
| Inmt | 1.05 | 1.70 | 1.82 | 0.79 | 1.56 | 0.53 | 0.99 | 2.56 | 1.61 | 1.00 | 1.00 | 1.00 |
| Ino80b | 1.19 | 1.01 | 0.89 | 1.41 | 2.11 | 1.07 | 1.22 | 1.53 | 0.93 | 1.63 | 1.29 | 1.08 |
| Inpp5a | 1.40 | 1.87 | 1.11 | 1.12 | 0.99 | 1.10 | 0.92 | 7.38 | 0.96 | 2.83 | 1.77 | 1.49 |
| Ins2 | 0.67 | 0.63 | 0.99 | 1.00 | 6.90 | 1.00 | 1.00 | 1.00 | 1.00 | 1.00 | 1.00 | 1.00 |
| Insig2 | 1.64 | 1.41 | 1.50 | 1.04 | 1.00 | 0.96 | 0.92 | 0.11 | 1.03 | 0.55 | 1.16 | 0.92 |
| Insl3 | 0.82 | 1.57 | 0.47 | 0.78 | 1.46 | 3.02 | 2.44 | 5.20 | 1.67 | 3.12 | 1.84 | 1.33 |
| Ints1 | 1.00 | 1.00 | 1.00 | 0.95 | 1.05 | 1.05 | 0.94 | 7.01 | 0.93 | 2.54 | 0.91 | 0.76 |
| Ints3 | 1.17 | 1.18 | 1.42 | 0.93 | 0.87 | 1.08 | 0.96 | 6.32 | 0.90 | 2.26 | 0.98 | 0.88 |
| Ipo5 | 1.01 | 1.08 | 1.12 | 1.07 | 0.85 | 1.03 | 1.02 | 6.56 | 0.87 | 1.41 | 0.69 | 0.87 |
| Iqcj | 1.00 | 1.00 | 1.00 | 1.00 | 1.00 | 1.00 | 1.00 | 1.00 | 1.00 | 1.00 | 1.00 | 1.00 |
| Iqck | 1.00 | 1.00 | 1.00 | 0.59 | 10.24 | 1.12 | 1.06 | 1.00 | 1.00 | 1.00 | 1.00 | 1.00 |
| Irf4 | 1.00 | 1.00 | 1.00 | 1.00 | 1.00 | 1.00 | 6.58 | 4.54 | 1.61 | 0.72 | 0.76 | 1.11 |
| Irf7 | 1.00 | 1.00 | 1.00 | 1.00 | 0.59 | 1.51 | 1.10 | 1.69 | 0.96 | 5.32 | 3.97 | 3.27 |
| Irgc1 | 1.00 | 1.00 | 1.00 | 1.00 | 1.00 | 1.00 | 6.61 | 1.00 | 1.00 | 1.19 | 1.00 | 1.00 |
| Irs2 | 2.12 | 3.00 | 1.66 | 1.18 | 1.00 | 1.13 | 1.91 | 0.39 | 2.31 | 1.00 | 0.79 | 0.54 |
| Isg15 | 1.00 | 1.00 | 1.00 | 1.11 | 2.23 | 1.91 | 3.10 | 0.31 | 2.25 | 4.67 | 3.71 | 3.53 |
| Isoc2a | 0.78 | 0.86 | 0.81 | 1.18 | 0.75 | 1.05 | 1.52 | 3.27 | 1.03 | 2.51 | 1.18 | 1.18 |
| Isoc2b | 0.25 | 0.38 | 0.18 | 1.36 | 0.79 | 0.99 | 1.53 | 9.13 | 0.63 | 6.65 | 2.59 | 2.10 |
| Isyna1 | 1.90 | 1.84 | 1.94 | 1.07 | 1.08 | 1.03 | 1.12 | 2.24 | 0.92 | 1.15 | 0.99 | 0.96 |
| Itga11 | 1.00 | 1.00 | 1.00 | 1.00 | 1.00 | 1.33 | 0.98 | 1.00 | 1.06 | 1.00 | 1.00 | 1.00 |
| Itga2b | 1.00 | 1.00 | 1.00 | 1.00 | 0.81 | 1.00 | 2.01 | 7.78 | 1.72 | 2.88 | 1.01 | 1.25 |
| Itgb1bp2 | 1.00 | 1.00 | 1.00 | 1.00 | 0.39 | 1.00 | 1.16 | 18.40 | 1.75 | 1.00 | 1.00 | 1.00 |
| Itgb5 | 1.42 | 0.98 | 1.14 | 1.09 | 1.11 | 1.06 | 0.99 | 2.94 | 0.82 | 2.18 | 0.68 | 0.84 |
| Itih4 | 1.00 | 6.20 | 2.03 | 1.00 | 1.00 | 1.00 | 1.00 | 1.00 | 1.00 | 1.00 | 1.00 | 1.00 |
| Itih5 | 1.01 | 1.28 | 1.00 | 0.94 | 0.94 | 0.97 | 1.04 | 0.50 | 1.81 | 1.00 | 0.69 | 0.99 |
| Itln1 | 1.00 | 1.00 | 1.00 | 1.00 | 1.00 | 1.00 | 0.31 | 1.33 | 0.43 | 0.38 | 0.48 | 0.33 |
| Itm2a | 1.10 | 1.00 | 1.00 | 0.73 | 0.68 | 0.76 | 0.85 | 1.58 | 0.94 | 0.79 | 1.02 | 1.23 |
| Itpka | 0.59 | 0.43 | 0.62 | 1.02 | 0.64 | 1.02 | 0.90 | 0.95 | 0.66 | 1.00 | 1.00 | 1.00 |
| Izumo4 | 0.73 | 0.80 | 0.71 | 0.99 | 0.71 | 0.88 | 1.82 | 6.93 | 0.87 | 3.38 | 1.07 | 1.38 |
| Jmjd8 | 0.90 | 0.82 | 0.71 | 1.23 | 1.01 | 1.07 | 1.13 | 7.76 | 0.90 | 2.35 | 1.09 | 1.09 |
| Josd2 | 0.91 | 1.22 | 0.82 | 1.40 | 0.67 | 0.84 | 1.10 | 11.28 | 0.82 | 2.05 | 0.98 | 0.99 |
| Jph3 | 1.00 | 1.00 | 1.00 | 1.06 | 0.90 | 0.98 | 1.00 | 1.00 | 1.00 | 1.33 | 0.74 | 0.77 |
| Jph4 | 1.00 | 1.00 | 1.00 | 0.98 | 0.84 | 0.95 | 1.00 | 1.00 | 1.00 | 1.00 | 1.00 | 1.00 |
| Jsrp1 | 1.00 | 1.00 | 1.00 | 1.10 | 0.84 | 0.96 | 1.98 | 36.99 | 2.05 | 1.00 | 1.00 | 1.00 |
| Junb | 3.14 | 2.50 | 1.58 | 1.27 | 1.36 | 1.20 | 1.02 | 0.37 | 0.85 | 0.60 | 1.40 | 1.19 |
| Kap | 3.64 | 1.00 | 1.39 | 1.00 | 7.54 | 2.30 | 1.00 | 1.00 | 1.09 | 1.00 | 1.00 | 1.00 |
| Kbtbd3 | 1.00 | 1.00 | 1.00 | 0.84 | 1.06 | 0.80 | 1.07 | 7.33 | 0.77 | 3.60 | 1.02 | 1.14 |
| Kcnc1 | 1.00 | 1.00 | 1.00 | 0.93 | 0.92 | 0.94 | 1.76 | 1.02 | 2.36 | 1.00 | 1.00 | 1.00 |
| Kcnj11 | 1.00 | 1.00 | 1.00 | 1.45 | 5.10 | 1.39 | 1.63 | 1.11 | 1.81 | 1.00 | 1.00 | 1.00 |
| Kcnj4 | 1.00 | 1.00 | 1.00 | 0.95 | 1.00 | 0.89 | 1.00 | 1.00 | 1.00 | 1.00 | 1.00 | 1.00 |
| Kcnk1 | 0.70 | 0.70 | 0.82 | 1.55 | 1.32 | 1.51 | 1.50 | 3.08 | 1.37 | 1.00 | 1.00 | 1.00 |
| Kcnk3 | 1.00 | 1.00 | 1.00 | 1.07 | 1.17 | 1.03 | 1.00 | 1.00 | 1.00 | 1.00 | 1.00 | 1.00 |
| Kcnk7 | 1.00 | 1.00 | 1.00 | 1.00 | 1.61 | 1.00 | 1.20 | 5.11 | 0.68 | 1.00 | 1.00 | 1.00 |
| Kcnq2 | 1.00 | 1.00 | 1.00 | 0.95 | 1.00 | 0.98 | 1.00 | 1.00 | 1.00 | 1.00 | 1.00 | 1.00 |
| Kdelr2 | 1.01 | 0.93 | 0.80 | 0.99 | 5.28 | 1.03 | 0.88 | 0.75 | 0.88 | 1.02 | 1.14 | 1.23 |
| Kdm7a | 1.32 | 1.29 | 1.00 | 0.86 | 1.22 | 0.90 | 1.03 | 0.24 | 1.18 | 0.48 | 1.09 | 0.94 |

Fig. 35- 197

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Khk | 0.91 | 0.59 | 0.65 | 0.31 | 7.24 | 1.18 | 1.17 | 0.89 | 0.90 | 1.85 | 3.37 | 1.16 |
| Kif1a | 1.00 | 1.00 | 1.00 | 1.00 | 0.11 | 1.00 | 1.00 | 1.00 | 1.00 | 1.00 | 1.12 | 2.19 |
| Kif5a | 1.00 | 1.00 | 1.00 | 1.00 | 0.04 | 1.00 | 1.00 | 1.00 | 1.00 | 1.00 | 1.00 | 0.74 |
| Kif5c | 1.00 | 1.00 | 1.00 | 1.00 | 0.12 | 1.00 | 1.00 | 1.00 | 1.00 | 1.00 | 1.00 | 1.00 |
| Kiss1 | 1.12 | 0.35 | 1.00 | 1.00 | 1.00 | 1.00 | 1.00 | 1.00 | 1.00 | 2.49 | 1.98 | 1.00 |
| Klhdc3 | 0.97 | 0.47 | 0.75 | 0.44 | 6.02 | 0.89 | 0.81 | 0.70 | 0.79 | 2.88 | 4.31 | 1.00 |
| Klhdc4 | 1.47 | 0.85 | 1.00 | 0.35 | 4.94 | 0.83 | 1.18 | 1.06 | 1.04 | 2.55 | 3.53 | 1.06 |
| Klhl30 | 3.69 | 4.44 | 2.70 | 1.00 | 1.00 | 2.10 | 0.58 | 0.61 | 0.55 | 1.00 | 1.00 | 0.72 |
| Klhl33 | 0.71 | 1.72 | 1.11 | 1.00 | 1.00 | 1.52 | 4.93 | 7.33 | 1.90 | 1.00 | 1.00 | 1.88 |
| Klk13 | 1.00 | 1.00 | 1.00 | 1.00 | 1.00 | 1.00 | 1.00 | 1.00 | 1.00 | 1.73 | 1.56 | 1.11 |
| Klk1b26 | 1.88 | 10.94 | 1.00 | 1.00 | 1.00 | 1.00 | 1.00 | 0.61 | 4.49 | 1.00 | 1.00 | 1.00 |
| Klk6 | 1.00 | 1.00 | 1.00 | 1.00 | 1.00 | 1.00 | 1.00 | 1.00 | 1.00 | 1.00 | 1.00 | 1.00 |
| Klk8 | 1.00 | 0.68 | 1.02 | 1.00 | 3.28 | 1.00 | 0.70 | 0.53 | 0.69 | 2.48 | 2.47 | 0.59 |
| Klra17 | 1.00 | 1.00 | 1.00 | 1.00 | 1.00 | 1.00 | 1.00 | 1.00 | 1.00 | 2.88 | 2.16 | 1.00 |
| Klra3 | 1.00 | 1.00 | 1.00 | 1.00 | 1.00 | 1.00 | 1.00 | 1.00 | 1.00 | 4.08 | 2.82 | 2.02 |
| Klra5 | 1.00 | 1.00 | 1.00 | 1.00 | 1.00 | 1.00 | 1.00 | 1.00 | 1.00 | 1.00 | 1.00 | 1.00 |
| Kncn | 1.00 | 1.00 | 1.00 | 1.00 | 1.00 | 1.00 | 1.00 | 1.00 | 1.00 | 1.00 | 1.00 | 1.00 |
| Kng2 | 1.00 | 1.00 | 1.00 | 0.74 | 4.20 | 0.84 | 1.00 | 1.00 | 1.00 | 1.00 | 1.00 | 1.00 |
| Kptn | 0.85 | 0.57 | 1.11 | 0.38 | 4.87 | 0.60 | 0.93 | 0.69 | 0.75 | 2.03 | 2.69 | 0.94 |
| Kri1 | 0.93 | 0.86 | 1.05 | 0.52 | 0.75 | 0.79 | 0.90 | 1.47 | 1.03 | 3.42 | 0.44 | 1.16 |
| Krt19 | 0.43 | 1.00 | 0.58 | 1.00 | 1.00 | 1.00 | 1.00 | 1.00 | 1.70 | 2.48 | 3.66 | 1.87 |
| Krt32 | 1.00 | 1.00 | 1.00 | 1.00 | 1.00 | 1.00 | 1.00 | 1.00 | 1.00 | 1.00 | 1.00 | 1.00 |
| Krt33b | 1.00 | 1.00 | 1.00 | 1.00 | 1.00 | 1.00 | 1.00 | 1.00 | 1.00 | 1.00 | 1.00 | 1.00 |
| Krt79 | 1.00 | 1.00 | 1.00 | 0.23 | 1.88 | 0.86 | 1.00 | 1.00 | 1.00 | 3.59 | 6.52 | 2.43 |
| Krtap10-10 | 1.00 | 1.00 | 1.00 | 1.00 | 1.00 | 1.00 | 1.00 | 1.00 | 1.00 | 1.00 | 1.00 | 1.00 |
| Krtap22-2 | 1.00 | 1.00 | 1.00 | 1.00 | 1.00 | 1.00 | 1.00 | 1.00 | 1.00 | 1.00 | 1.00 | 1.00 |
| Krtap3-2 | 1.00 | 1.00 | 1.00 | 1.00 | 1.00 | 1.00 | 1.00 | 1.00 | 1.00 | 1.00 | 1.00 | 1.00 |
| Krtap5-1 | 1.00 | 1.00 | 1.00 | 1.00 | 1.00 | 1.00 | 1.00 | 1.00 | 1.00 | 1.00 | 1.00 | 1.00 |
| Krtap5-2 | 1.00 | 1.00 | 1.00 | 1.00 | 1.00 | 1.00 | 1.00 | 1.00 | 1.00 | 1.00 | 1.00 | 1.00 |
| Krtdap | 1.00 | 1.00 | 1.00 | 1.00 | 1.00 | 1.00 | 1.00 | 1.00 | 1.00 | 1.00 | 1.00 | 1.00 |
| LOC100038947 | 1.00 | 1.00 | 1.00 | 1.00 | 1.00 | 1.00 | 1.00 | 1.00 | 1.00 | 0.45 | 0.51 | 0.78 |
| LOC100504703 | 0.69 | 0.38 | 1.42 | 0.36 | 6.64 | 0.47 | 0.64 | 0.43 | 0.97 | 1.36 | 2.76 | 0.43 |
| LOC100861615 | 1.00 | 1.00 | 1.00 | 1.00 | 1.00 | 1.00 | 1.70 | 1.90 | 1.38 | 1.00 | 1.00 | 1.00 |
| LOC100861978 | 1.01 | 1.38 | 1.00 | 1.00 | 2.04 | 1.38 | 1.09 | 1.65 | 1.57 | 6.05 | 1.56 | 3.34 |
| LOC101669761 | 1.90 | 1.20 | 1.39 | 0.47 | 7.07 | 1.37 | 1.09 | 1.04 | 1.08 | 1.90 | 3.85 | 2.37 |
| LOC102632423 | 1.00 | 1.00 | 1.00 | 1.00 | 1.00 | 1.00 | 1.00 | 1.00 | 1.00 | 1.00 | 1.00 | 1.00 |
| Lama3 | 1.00 | 1.00 | 1.00 | 1.00 | 1.00 | 1.00 | 1.00 | 1.00 | 1.00 | 0.87 | 0.65 | 1.37 |
| Lama4 | 0.89 | 0.41 | 0.93 | 0.70 | 2.00 | 0.54 | 0.84 | 0.79 | 1.02 | 1.53 | 1.77 | 0.94 |
| Lamc2 | 3.05 | 1.67 | 2.32 | 9.27 | 12.75 | 2.82 | 1.13 | 1.29 | 1.02 | 1.03 | 1.38 | 1.19 |
| Lamp5 | 1.00 | 1.00 | 1.00 | 1.00 | 0.30 | 1.00 | 1.00 | 1.00 | 1.00 | 1.00 | 1.00 | 1.00 |
| Lamtor2 | 0.90 | 0.64 | 0.94 | 0.31 | 4.89 | 0.93 | 1.11 | 1.08 | 0.89 | 1.64 | 2.44 | 1.07 |
| Lamtor3 | 1.77 | 2.61 | 1.27 | 1.62 | 2.46 | 1.69 | 1.19 | 1.14 | 1.26 | 2.35 | 1.58 | 1.36 |
| Lamtor4 | 1.22 | 0.54 | 0.80 | 0.38 | 10.58 | 0.93 | 0.95 | 0.72 | 0.78 | 2.17 | 3.47 | 1.01 |
| Lars | 1.13 | 0.68 | 1.07 | 0.41 | 4.11 | 0.90 | 0.93 | 0.92 | 0.90 | 1.98 | 3.05 | 0.89 |
| Lars2 | 1.13 | 0.18 | 0.76 | 0.74 | 1.22 | 0.87 | 0.92 | 1.43 | 0.91 | 4.74 | 1.72 | 0.80 |
| Lat | 1.00 | 1.00 | 1.00 | 1.00 | 1.00 | 1.00 | 1.00 | 1.00 | 1.00 | 2.04 | 2.89 | 0.87 |
| Lbp | 1.67 | 0.69 | 0.89 | 1.24 | 3.42 | 1.22 | 1.63 | 1.09 | 1.17 | 1.44 | 2.88 | 1.17 |
| Lce1f | 1.00 | 1.00 | 1.00 | 1.00 | 1.00 | 1.00 | 1.00 | 1.00 | 1.00 | 1.00 | 1.00 | 1.00 |
| Lce1g | 1.00 | 1.00 | 1.00 | 1.00 | 1.00 | 1.00 | 1.00 | 1.00 | 1.00 | 1.00 | 1.00 | 1.00 |
| Lce1j | 1.00 | 1.00 | 1.00 | 1.00 | 1.00 | 1.00 | 1.00 | 1.00 | 1.00 | 1.00 | 1.00 | 1.00 |
| Lce1m | 1.00 | 1.00 | 1.00 | 1.00 | 1.00 | 1.00 | 1.00 | 1.00 | 1.00 | 1.00 | 1.00 | 1.00 |
| Lce3c | 1.00 | 1.00 | 1.00 | 1.00 | 1.00 | 1.00 | 1.00 | 1.00 | 1.00 | 1.00 | 1.00 | 1.00 |
| Lce3d | 1.00 | 1.00 | 1.00 | 1.00 | 1.00 | 1.00 | 1.00 | 1.00 | 1.00 | 1.00 | 1.00 | 1.00 |
| Lce3f | 1.00 | 1.00 | 1.00 | 1.00 | 1.00 | 1.00 | 1.00 | 1.00 | 1.00 | 1.00 | 1.00 | 1.00 |
| Lcmt1 | 0.96 | 0.65 | 0.77 | 0.32 | 3.33 | 0.85 | 0.87 | 0.88 | 0.67 | 2.43 | 2.44 | 1.01 |
| Lcn2 | 7.55 | 19.24 | 4.59 | 1.31 | 2.14 | 1.68 | 3.63 | 2.81 | 5.58 | 0.94 | 2.02 | 1.11 |
| Ldhal6b | 1.00 | 1.00 | 1.00 | 1.00 | 1.00 | 1.00 | 1.00 | 1.00 | 1.00 | 1.00 | 1.00 | 1.00 |
| Ldhb | 0.77 | 0.37 | 0.71 | 0.33 | 3.09 | 0.81 | 1.04 | 1.01 | 0.92 | 1.05 | 2.11 | 1.52 |
| Ldhc | 1.00 | 1.00 | 1.00 | 1.00 | 1.00 | 1.00 | 1.00 | 1.00 | 1.00 | 1.09 | 1.00 | 1.00 |
| Ldlr | 2.55 | 1.49 | 1.19 | 0.25 | 0.21 | 0.80 | 0.79 | 1.03 | 1.04 | 2.23 | 1.87 | 1.24 |
| Leng1 | 1.35 | 0.67 | 0.92 | 0.57 | 2.69 | 0.94 | 0.99 | 0.80 | 0.86 | 1.60 | 2.42 | 1.15 |
| Lepr | 1.23 | 1.00 | 0.82 | 1.00 | 1.00 | 1.00 | 0.77 | 1.09 | 0.83 | 0.87 | 0.74 | 1.08 |
| Lgals1 | 1.87 | 0.76 | 1.01 | 0.23 | 8.15 | 0.56 | 0.97 | 0.71 | 0.91 | 1.68 | 2.55 | 0.65 |
| Lgals4 | 0.72 | 0.50 | 0.78 | 0.52 | 2.84 | 0.93 | 0.31 | 0.24 | 0.33 | 2.25 | 2.71 | 1.02 |

Fig. 35- 198

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Khk | 1.13 | 2.46 | 1.27 | 0.74 | 0.65 | 0.69 | 0.48 | 0.63 | 0.52 | 0.95 | 1.50 | 0.98 |
| Kif1a | 1.00 | 0.90 | 1.42 | 1.00 | 1.00 | 1.00 | 1.00 | 1.00 | 1.00 | 1.43 | 0.90 | 1.13 |
| Kif5a | 0.73 | 0.80 | 0.95 | 1.21 | 1.37 | 1.47 | 1.00 | 1.00 | 0.87 | 0.98 | 0.97 | 1.05 |
| Kif5c | 1.31 | 0.96 | 1.44 | 1.00 | 1.00 | 1.00 | 1.00 | 1.00 | 1.00 | 0.99 | 0.83 | 1.48 |
| Kiss1 | 1.00 | 1.00 | 1.00 | 1.00 | 0.63 | 1.00 | 1.02 | 12.69 | 1.00 | 1.00 | 1.23 | 1.04 |
| Klhdc3 | 1.21 | 1.48 | 1.03 | 1.01 | 0.74 | 0.94 | 1.31 | 2.25 | 1.07 | 0.93 | 1.61 | 1.11 |
| Klhdc4 | 0.96 | 1.16 | 0.80 | 0.98 | 0.82 | 0.90 | 1.32 | 2.38 | 1.05 | 1.02 | 1.66 | 1.15 |
| Klhl30 | 1.00 | 1.00 | 1.00 | 1.00 | 1.00 | 1.00 | 1.00 | 1.00 | 1.00 | 0.92 | 0.68 | 0.85 |
| Klhl33 | 1.08 | 1.00 | 1.02 | 1.00 | 1.00 | 1.00 | 1.00 | 1.00 | 1.00 | 1.75 | 1.00 | 1.45 |
| Klk13 | 1.00 | 1.00 | 1.00 | 1.00 | 1.00 | 1.00 | 1.00 | 1.00 | 1.00 | 1.00 | 1.00 | 1.00 |
| Klk1b26 | 0.43 | 3.33 | 0.75 | 1.00 | 1.00 | 1.00 | 1.00 | 1.00 | 1.00 | 1.00 | 1.00 | 1.00 |
| Klk6 | 1.00 | 1.00 | 1.00 | 1.00 | 1.00 | 1.00 | 1.00 | 1.00 | 1.00 | 1.00 | 1.00 | 1.00 |
| Klk8 | 1.16 | 1.50 | 1.08 | 1.00 | 0.43 | 1.00 | 1.00 | 1.01 | 1.00 | 1.00 | 0.92 | 1.00 |
| Klra17 | 1.00 | 0.86 | 0.94 | 1.00 | 1.00 | 1.00 | 1.00 | 1.15 | 1.00 | 1.00 | 1.00 | 1.00 |
| Klra3 | 4.02 | 5.51 | 4.43 | 1.00 | 1.00 | 1.00 | 1.00 | 1.00 | 1.00 | 1.00 | 1.00 | 1.00 |
| Klra5 | 5.05 | 5.01 | 4.94 | 1.00 | 1.00 | 1.00 | 1.00 | 1.00 | 1.00 | 1.00 | 1.00 | 1.00 |
| Kncn | 1.00 | 1.00 | 1.00 | 1.00 | 1.00 | 1.00 | 1.00 | 1.00 | 1.00 | 1.00 | 1.00 | 1.00 |
| Kng2 | 1.00 | 1.00 | 1.00 | 0.90 | 0.59 | 0.89 | 0.77 | 1.59 | 0.96 | 1.00 | 1.00 | 1.00 |
| Kptn | 1.39 | 1.35 | 0.93 | 0.93 | 0.60 | 0.94 | 0.72 | 1.32 | 0.74 | 1.28 | 1.69 | 1.11 |
| Kri1 | 0.95 | 0.96 | 0.98 | 0.97 | 0.07 | 0.86 | 1.00 | 10.55 | 0.92 | 0.94 | 0.79 | 1.25 |
| Krt19 | 2.31 | 1.11 | 2.07 | 0.84 | 0.56 | 0.76 | 1.00 | 1.78 | 1.00 | 0.87 | 1.18 | 0.94 |
| Krt32 | 1.00 | 1.00 | 1.00 | 1.00 | 1.00 | 1.00 | 1.00 | 1.00 | 1.00 | 1.00 | 1.00 | 1.00 |
| Krt33b | 1.00 | 1.00 | 1.00 | 1.00 | 1.00 | 1.00 | 1.00 | 1.00 | 1.00 | 1.00 | 1.00 | 1.00 |
| Krt79 | 0.78 | 0.44 | 0.39 | 1.00 | 1.00 | 1.00 | 1.00 | 1.00 | 1.00 | 1.00 | 1.00 | 0.42 |
| Krtap10-10 | 1.00 | 1.00 | 1.00 | 1.00 | 1.00 | 1.00 | 1.00 | 1.00 | 1.00 | 1.00 | 1.00 | 1.00 |
| Krtap22-2 | 1.00 | 1.00 | 1.00 | 1.00 | 1.00 | 1.00 | 1.00 | 1.00 | 1.00 | 1.00 | 1.00 | 1.00 |
| Krtap3-2 | 1.00 | 1.00 | 1.00 | 1.00 | 1.00 | 1.00 | 1.00 | 1.00 | 1.00 | 1.00 | 1.00 | 1.00 |
| Krtap5-1 | 1.00 | 1.00 | 1.00 | 1.00 | 1.00 | 1.00 | 1.00 | 1.00 | 1.00 | 1.00 | 1.00 | 1.00 |
| Krtap5-2 | 1.00 | 1.00 | 1.00 | 1.00 | 1.00 | 1.00 | 1.00 | 1.00 | 1.00 | 1.00 | 1.00 | 1.00 |
| Krtdap | 1.06 | 2.78 | 0.53 | 1.00 | 1.00 | 1.00 | 1.00 | 1.00 | 1.00 | 1.00 | 1.00 | 0.41 |
| LOC100038947 | 1.00 | 1.00 | 1.00 | 1.00 | 1.00 | 1.00 | 1.00 | 1.00 | 1.00 | 1.00 | 1.00 | 1.00 |
| LOC100504703 | 2.01 | 7.90 | 1.30 | 1.15 | 1.13 | 0.86 | 0.51 | 1.48 | 0.68 | 0.56 | 1.28 | 1.10 |
| LOC100861615 | 3.40 | 3.66 | 3.77 | 1.00 | 0.40 | 1.00 | 1.00 | 1.00 | 1.00 | 1.11 | 1.19 | 1.10 |
| LOC100861978 | 4.63 | 6.97 | 2.16 | 1.23 | 1.83 | 1.58 | 1.07 | 1.36 | 1.00 | 1.75 | 1.48 | 1.00 |
| LOC101669761 | 1.86 | 2.61 | 2.27 | 1.19 | 1.77 | 1.33 | 1.21 | 1.19 | 1.31 | 1.66 | 2.74 | 1.53 |
| LOC102632423 | 1.00 | 1.00 | 1.00 | 1.00 | 1.00 | 1.00 | 1.00 | 1.00 | 1.00 | 1.00 | 1.00 | 1.00 |
| Lama3 | 1.61 | 1.35 | 1.97 | 7.03 | 1.17 | 4.43 | 1.00 | 1.00 | 1.00 | 0.96 | 0.72 | 0.91 |
| Lama4 | 1.11 | 0.87 | 0.89 | 1.00 | 0.79 | 1.00 | 1.00 | 1.00 | 1.00 | 0.82 | 0.76 | 0.84 |
| Lamc2 | 1.39 | 1.19 | 1.62 | 0.94 | 0.84 | 1.03 | 1.00 | 1.00 | 1.00 | 0.91 | 0.87 | 0.83 |
| Lamp5 | 1.00 | 1.00 | 1.00 | 1.00 | 1.00 | 1.00 | 1.00 | 1.00 | 1.00 | 1.00 | 1.00 | 1.00 |
| Lamtor2 | 0.99 | 1.28 | 0.77 | 0.80 | 0.60 | 0.96 | 0.89 | 1.40 | 0.76 | 0.97 | 1.46 | 0.97 |
| Lamtor3 | 1.27 | 1.43 | 1.35 | 1.53 | 14.50 | 1.78 | 1.15 | 5.51 | 1.62 | 1.50 | 1.88 | 1.64 |
| Lamtor4 | 1.21 | 2.31 | 1.15 | 0.72 | 0.59 | 0.81 | 0.84 | 1.77 | 0.82 | 1.14 | 1.77 | 1.05 |
| Lars | 0.97 | 1.15 | 0.97 | 0.99 | 0.72 | 0.84 | 1.07 | 1.39 | 0.83 | 0.93 | 1.29 | 0.95 |
| Lars2 | 1.04 | 1.21 | 1.15 | 0.57 | 0.92 | 1.43 | 0.48 | 18.54 | 1.19 | 1.74 | 1.20 | 0.70 |
| Lat | 0.93 | 1.32 | 0.88 | 1.00 | 1.00 | 1.00 | 1.00 | 1.63 | 1.00 | 1.00 | 1.29 | 1.27 |
| Lbp | 3.07 | 3.69 | 2.21 | 1.32 | 1.49 | 1.03 | 1.12 | 0.81 | 1.57 | 1.04 | 1.61 | 0.99 |
| Lce1f | 0.89 | 1.00 | 1.00 | 1.00 | 1.00 | 1.00 | 1.00 | 1.00 | 1.00 | 1.00 | 1.00 | 0.84 |
| Lce1g | 1.00 | 1.00 | 1.00 | 1.00 | 1.00 | 1.00 | 1.00 | 1.00 | 1.00 | 1.00 | 1.00 | 1.00 |
| Lce1j | 1.00 | 1.00 | 1.00 | 1.00 | 1.00 | 1.00 | 1.00 | 1.00 | 1.00 | 1.00 | 1.00 | 1.00 |
| Lce1m | 1.00 | 1.00 | 1.00 | 1.00 | 1.00 | 1.00 | 1.00 | 1.00 | 1.00 | 1.00 | 1.00 | 0.98 |
| Lce3c | 1.00 | 1.00 | 1.00 | 1.00 | 1.00 | 1.00 | 1.00 | 1.00 | 1.00 | 1.00 | 1.00 | 1.00 |
| Lce3d | 1.00 | 1.00 | 1.00 | 1.00 | 1.00 | 1.00 | 1.00 | 1.00 | 1.00 | 1.00 | 1.00 | 1.00 |
| Lce3f | 1.00 | 1.00 | 1.00 | 1.00 | 1.00 | 1.00 | 1.00 | 1.00 | 1.00 | 1.00 | 1.00 | 1.00 |
| Lcmt1 | 0.94 | 1.25 | 1.03 | 0.73 | 0.57 | 0.97 | 0.55 | 1.32 | 1.05 | 1.11 | 1.53 | 1.09 |
| Lcn2 | 0.75 | 1.58 | 3.55 | 1.12 | 2.24 | 0.84 | 10.80 | 6.20 | 5.91 | 1.76 | 3.62 | 1.44 |
| Ldhal6b | 1.00 | 1.00 | 1.00 | 1.00 | 1.00 | 1.00 | 1.00 | 1.00 | 1.00 | 1.00 | 1.00 | 1.00 |
| Ldhb | 0.98 | 1.22 | 0.82 | 0.99 | 0.86 | 0.98 | 0.74 | 0.42 | 0.41 | 0.81 | 1.15 | 0.79 |
| Ldhc | 1.00 | 1.00 | 1.00 | 1.00 | 1.00 | 1.00 | 1.00 | 1.00 | 1.00 | 1.00 | 1.00 | 1.00 |
| Ldlr | 0.53 | 0.54 | 0.66 | 1.36 | 1.57 | 1.35 | 0.49 | 1.11 | 0.76 | 1.52 | 0.90 | 1.06 |
| Leng1 | 1.16 | 1.22 | 1.03 | 1.06 | 0.95 | 0.99 | 0.85 | 0.78 | 0.83 | 1.09 | 1.42 | 1.09 |
| Lepr | 1.92 | 1.29 | 1.21 | 1.33 | 1.00 | 1.20 | 38.76 | 9.39 | 8.72 | 1.19 | 1.00 | 1.05 |
| Lgals1 | 0.65 | 0.84 | 0.63 | 0.88 | 0.61 | 0.86 | 1.00 | 1.16 | 0.60 | 0.90 | 1.32 | 0.82 |
| Lgals4 | 1.73 | 1.62 | 1.83 | 0.60 | 0.42 | 0.94 | 0.86 | 1.33 | 1.09 | 1.03 | 1.54 | 1.11 |

Fig. 35- 199

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Khk | 1.17 | 1.29 | 1.25 | 0.74 | 1.18 | 1.05 | 1.02 | 1.66 | 0.96 | 1.12 | 1.30 | 0.88 |
| Kif1a | 1.21 | 1.18 | 1.12 | 1.46 | 1.00 | 1.46 | 1.03 | 1.56 | 1.17 | 1.00 | 14.95 | 0.83 |
| Kif5a | 1.29 | 1.15 | 1.03 | 0.95 | 1.00 | 0.71 | 1.24 | 1.00 | 1.02 | 0.72 | 27.63 | 0.78 |
| Kif5c | 0.88 | 0.82 | 0.73 | 1.00 | 1.00 | 0.70 | 0.86 | 1.25 | 0.92 | 1.00 | 14.33 | 1.00 |
| Kiss1 | 1.00 | 1.00 | 1.00 | 2.59 | 13.05 | 1.73 | 0.64 | 4.10 | 0.48 | 1.00 | 1.00 | 1.00 |
| Klhdc3 | 1.18 | 1.36 | 1.17 | 1.13 | 2.49 | 0.99 | 0.95 | 2.87 | 1.04 | 1.02 | 1.49 | 0.94 |
| Klhdc4 | 0.95 | 0.91 | 0.85 | 1.06 | 1.69 | 0.98 | 1.06 | 2.29 | 1.05 | 1.10 | 1.25 | 0.96 |
| Klhl30 | 1.07 | 1.00 | 1.21 | 1.00 | 1.00 | 1.00 | 1.00 | 1.00 | 1.00 | 1.00 | 1.00 | 1.00 |
| Klhl33 | 3.77 | 2.44 | 2.50 | 1.44 | 1.00 | 1.12 | 1.00 | 1.00 | 1.00 | 1.24 | 1.47 | 1.74 |
| Klk13 | 1.23 | 1.92 | 1.59 | 1.00 | 1.00 | 1.00 | 1.00 | 1.00 | 1.00 | 1.00 | 1.00 | 1.00 |
| Klk1b26 | 1.00 | 1.00 | 1.00 | 1.00 | 1.00 | 1.00 | 0.57 | 2.40 | 1.03 | 1.00 | 1.00 | 1.00 |
| Klk6 | 2.84 | 2.65 | 2.49 | 1.00 | 1.00 | 1.00 | 1.00 | 1.00 | 1.00 | 1.00 | 1.00 | 1.00 |
| Klk8 | 0.88 | 1.19 | 1.20 | 1.14 | 1.72 | 1.71 | 1.00 | 1.00 | 1.00 | 0.99 | 1.19 | 0.96 |
| Klra17 | 1.00 | 1.00 | 1.00 | 1.00 | 1.00 | 1.00 | 1.00 | 1.00 | 1.00 | 0.65 | 0.35 | 0.86 |
| Klra3 | 1.00 | 1.00 | 1.00 | 1.00 | 1.00 | 1.00 | 1.00 | 1.00 | 1.00 | 2.65 | 3.96 | 2.76 |
| Klra5 | 1.00 | 1.00 | 1.00 | 1.00 | 1.00 | 1.00 | 0.68 | 0.60 | 0.80 | 1.00 | 1.00 | 1.00 |
| Kncn | 1.00 | 1.00 | 1.00 | 1.00 | 1.00 | 1.00 | 1.00 | 7.41 | 1.00 | 1.00 | 1.00 | 1.00 |
| Kng2 | 1.00 | 1.00 | 1.00 | 1.00 | 1.00 | 0.91 | 1.00 | 1.26 | 1.00 | 1.00 | 1.00 | 1.00 |
| Kptn | 1.23 | 1.07 | 0.94 | 0.64 | 2.13 | 0.80 | 0.96 | 2.33 | 1.13 | 0.75 | 1.09 | 0.82 |
| Kri1 | 0.66 | 1.09 | 0.72 | 1.29 | 3.58 | 0.96 | 0.81 | 5.33 | 1.07 | 0.98 | 0.90 | 1.13 |
| Krt19 | 0.74 | 0.77 | 0.60 | 1.73 | 1.25 | 2.21 | 1.00 | 1.00 | 1.00 | 1.08 | 1.05 | 1.36 |
| Krt32 | 1.00 | 1.00 | 1.00 | 1.00 | 1.00 | 1.00 | 1.00 | 1.00 | 1.00 | 1.00 | 1.00 | 1.00 |
| Krt33b | 1.00 | 1.00 | 1.00 | 1.00 | 1.00 | 1.00 | 1.00 | 1.00 | 1.00 | 1.00 | 1.00 | 1.00 |
| Krt79 | 0.36 | 0.43 | 0.47 | 0.77 | 2.00 | 0.82 | 1.00 | 1.00 | 1.00 | 1.00 | 1.00 | 1.00 |
| Krtap10-10 | 1.00 | 1.00 | 1.00 | 1.00 | 1.00 | 1.00 | 1.00 | 1.00 | 1.00 | 1.00 | 1.00 | 1.00 |
| Krtap22-2 | 1.00 | 1.00 | 1.00 | 1.00 | 1.00 | 1.00 | 1.00 | 1.00 | 1.00 | 1.00 | 1.00 | 1.00 |
| Krtap3-2 | 2.76 | 5.09 | 2.43 | 1.00 | 1.00 | 1.00 | 1.00 | 1.00 | 1.00 | 1.00 | 1.00 | 1.00 |
| Krtap5-1 | 1.00 | 1.00 | 1.00 | 1.00 | 1.00 | 1.00 | 1.00 | 1.00 | 1.00 | 1.00 | 1.00 | 1.00 |
| Krtap5-2 | 1.00 | 1.00 | 1.00 | 1.00 | 1.00 | 1.00 | 1.00 | 1.00 | 1.00 | 1.00 | 1.00 | 1.00 |
| Krtdap | 0.90 | 1.20 | 1.52 | 1.00 | 0.21 | 1.76 | 1.00 | 1.00 | 1.00 | 1.00 | 1.00 | 1.00 |
| LOC100038947 | 1.00 | 1.00 | 1.00 | 1.00 | 1.00 | 0.49 | 9.95 | 6.82 | 9.46 | 0.53 | 0.39 | 0.51 |
| LOC100504703 | 1.61 | 1.17 | 1.09 | 0.76 | 3.48 | 0.82 | 1.00 | 0.84 | 1.00 | 1.93 | 1.79 | 1.34 |
| LOC100861615 | 1.00 | 1.00 | 1.00 | 5.32 | 1.00 | 5.28 | 1.89 | 3.49 | 2.07 | 2.93 | 2.72 | 3.33 |
| LOC100861978 | 1.00 | 1.17 | 1.44 | 2.49 | 1.00 | 2.09 | 5.10 | 14.43 | 4.55 | 1.58 | 2.39 | 1.37 |
| LOC101669761 | 1.58 | 1.89 | 1.66 | 1.48 | 5.51 | 1.42 | 1.30 | 0.99 | 1.30 | 1.82 | 2.41 | 1.45 |
| LOC102632423 | 1.00 | 1.00 | 1.00 | 1.00 | 1.00 | 1.00 | 1.64 | 8.25 | 1.03 | 1.00 | 1.00 | 1.00 |
| Lama3 | 0.37 | 0.50 | 0.43 | 1.00 | 1.00 | 1.00 | 1.00 | 1.00 | 1.00 | 1.00 | 1.00 | 1.00 |
| Lama4 | 0.94 | 0.85 | 0.98 | 0.68 | 0.65 | 0.55 | 1.00 | 1.00 | 1.00 | 1.00 | 1.00 | 1.00 |
| Lamc2 | 0.68 | 0.64 | 0.42 | 2.96 | 1.51 | 2.36 | 1.00 | 1.00 | 1.00 | 1.00 | 1.00 | 1.00 |
| Lamp5 | 1.00 | 1.00 | 1.00 | 1.00 | 1.00 | 1.00 | 1.00 | 1.49 | 1.00 | 1.00 | 6.18 | 1.00 |
| Lamtor2 | 1.12 | 0.95 | 0.90 | 0.80 | 1.29 | 0.78 | 0.80 | 1.96 | 0.66 | 0.92 | 1.28 | 0.77 |
| Lamtor3 | 1.74 | 1.33 | 1.68 | 1.76 | 4.50 | 1.48 | 1.72 | 1.80 | 1.60 | 1.12 | 1.12 | 1.14 |
| Lamtor4 | 1.03 | 0.90 | 1.04 | 0.64 | 2.05 | 0.71 | 1.18 | 2.62 | 0.96 | 0.97 | 1.23 | 0.91 |
| Lars | 0.99 | 0.86 | 1.05 | 0.95 | 1.65 | 0.83 | 1.22 | 1.99 | 0.95 | 1.00 | 1.07 | 0.99 |
| Lars2 | 0.46 | 1.27 | 1.12 | 1.14 | 0.07 | 1.36 | 0.74 | 4.64 | 1.29 | 0.60 | 0.55 | 0.67 |
| Lat | 1.00 | 1.00 | 1.00 | 1.00 | 1.00 | 0.88 | 1.00 | 1.00 | 1.00 | 0.85 | 1.11 | 0.91 |
| Lbp | 1.39 | 1.37 | 1.25 | 1.26 | 5.50 | 0.95 | 0.83 | 0.68 | 0.82 | 1.18 | 1.48 | 0.73 |
| Lce1f | 1.24 | 1.63 | 1.34 | 1.00 | 1.00 | 1.00 | 1.00 | 1.00 | 1.00 | 1.00 | 1.00 | 1.00 |
| Lce1g | 1.18 | 1.73 | 1.45 | 1.00 | 1.00 | 1.00 | 1.00 | 1.00 | 1.00 | 1.00 | 1.00 | 1.00 |
| Lce1j | 1.14 | 1.43 | 1.23 | 1.00 | 1.00 | 1.00 | 1.00 | 1.00 | 1.00 | 1.00 | 1.00 | 1.00 |
| Lce1m | 1.18 | 1.71 | 1.55 | 1.00 | 1.00 | 10.34 | 1.00 | 1.00 | 1.00 | 1.00 | 1.00 | 1.00 |
| Lce3c | 1.07 | 1.39 | 1.52 | 1.00 | 1.00 | 1.00 | 1.00 | 1.00 | 1.00 | 1.00 | 1.00 | 1.00 |
| Lce3d | 0.71 | 1.65 | 1.49 | 1.00 | 1.00 | 1.00 | 1.00 | 1.00 | 1.00 | 1.00 | 1.00 | 1.00 |
| Lce3f | 1.28 | 1.64 | 1.59 | 1.00 | 1.00 | 1.00 | 1.00 | 1.00 | 1.00 | 1.00 | 1.00 | 1.00 |
| Lcmt1 | 0.94 | 1.14 | 0.98 | 0.69 | 1.97 | 0.75 | 0.90 | 2.41 | 1.20 | 1.20 | 1.16 | 1.05 |
| Lcn2 | 3.95 | 3.85 | 3.45 | 1.78 | 9.06 | 4.09 | 1.28 | 0.89 | 0.82 | 14.98 | 7.61 | 5.98 |
| Ldhal6b | 1.00 | 1.00 | 1.00 | 2.28 | 1.00 | 1.00 | 0.97 | 0.85 | 0.98 | 1.00 | 1.00 | 0.96 |
| Ldhb | 1.95 | 2.25 | 1.96 | 0.41 | 1.10 | 0.30 | 0.89 | 0.47 | 0.94 | 1.55 | 7.40 | 1.24 |
| Ldhc | 1.00 | 1.00 | 1.00 | 3.01 | 1.26 | 1.88 | 0.95 | 1.36 | 0.94 | 1.00 | 1.00 | 1.00 |
| Ldlr | 0.85 | 0.96 | 0.81 | 1.15 | 1.00 | 1.85 | 0.67 | 1.00 | 0.80 | 1.19 | 0.70 | 0.99 |
| Leng1 | 1.08 | 1.41 | 1.22 | 0.89 | 2.97 | 1.23 | 0.92 | 1.44 | 1.03 | 0.94 | 1.07 | 1.15 |
| Lepr | 2.25 | 1.72 | 1.70 | 10.46 | 1.00 | 2.10 | 1.00 | 1.00 | 1.00 | 1.16 | 1.13 | 1.25 |
| Lgals1 | 0.76 | 0.71 | 0.89 | 0.53 | 1.11 | 0.38 | 0.80 | 2.44 | 0.88 | 0.72 | 0.85 | 0.81 |
| Lgals4 | 0.70 | 0.66 | 0.72 | 1.10 | 4.72 | 1.41 | 1.01 | 1.32 | 0.79 | 1.32 | 1.21 | 1.28 |

Fig. 35- 200

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Khk | 0.69 | 0.70 | 0.82 | 1.16 | 0.80 | 1.18 | 1.26 | 4.40 | 1.04 | 2.81 | 1.74 | 1.11 |
| Kif1a | 1.00 | 1.00 | 1.00 | 1.06 | 1.38 | 1.04 | 1.14 | 1.00 | 1.26 | 1.00 | 1.00 | 1.00 |
| Kif5a | 1.00 | 1.00 | 1.00 | 1.01 | 1.03 | 0.98 | 1.09 | 0.64 | 1.09 | 1.00 | 1.00 | 1.00 |
| Kif5c | 1.00 | 1.00 | 1.00 | 1.05 | 1.10 | 0.97 | 1.00 | 1.00 | 1.00 | 1.00 | 1.00 | 1.00 |
| Kiss1 | 1.00 | 1.00 | 1.00 | 1.00 | 0.77 | 1.00 | 1.00 | 1.00 | 1.00 | 1.00 | 1.00 | 1.00 |
| Klhdc3 | 1.39 | 1.26 | 1.12 | 1.02 | 0.94 | 1.00 | 1.47 | 13.43 | 1.16 | 3.02 | 1.15 | 1.17 |
| Klhdc4 | 0.84 | 1.00 | 0.93 | 1.13 | 0.86 | 1.02 | 1.27 | 8.05 | 1.01 | 2.70 | 0.89 | 0.96 |
| Klhl30 | 1.00 | 1.00 | 1.00 | 1.00 | 1.52 | 1.00 | 2.90 | 1.87 | 5.63 | 1.00 | 1.00 | 1.00 |
| Klhl33 | 1.00 | 1.00 | 1.00 | 1.44 | 0.29 | 1.37 | 2.79 | 0.60 | 3.68 | 1.00 | 1.00 | 1.00 |
| Klk13 | 1.00 | 1.00 | 1.00 | 1.00 | 1.00 | 1.00 | 0.94 | 11.35 | 0.97 | 1.00 | 1.00 | 1.00 |
| Klk1b26 | 7.82 | 3.58 | 1.99 | 1.00 | 1.00 | 1.00 | 1.00 | 1.00 | 1.00 | 1.00 | 1.00 | 1.00 |
| Klk6 | 1.00 | 1.00 | 1.00 | 1.10 | 0.94 | 0.89 | 1.76 | 5.50 | 0.86 | 1.00 | 1.00 | 1.00 |
| Klk8 | 1.00 | 1.00 | 1.00 | 1.19 | 0.93 | 1.99 | 1.09 | 14.76 | 0.66 | 3.55 | 2.70 | 1.08 |
| Klra17 | 1.00 | 1.00 | 1.00 | 1.00 | 1.00 | 1.00 | 0.55 | 1.00 | 1.00 | 14.36 | 7.38 | 4.92 |
| Klra3 | 1.00 | 1.00 | 1.00 | 1.00 | 1.00 | 1.00 | 1.00 | 1.00 | 1.00 | 2.16 | 1.97 | 1.10 |
| Klra5 | 1.00 | 1.00 | 1.00 | 1.00 | 1.00 | 1.00 | 1.00 | 1.00 | 1.00 | 1.00 | 1.00 | 1.00 |
| Kncn | 1.00 | 1.00 | 1.00 | 1.00 | 1.00 | 1.00 | 1.00 | 1.28 | 1.00 | 1.00 | 1.00 | 1.00 |
| Kng2 | 1.50 | 1.00 | 1.00 | 1.00 | 1.00 | 1.00 | 1.08 | 6.54 | 0.98 | 1.00 | 1.00 | 1.00 |
| Kptn | 0.97 | 1.01 | 1.00 | 0.80 | 0.81 | 0.83 | 0.88 | 7.39 | 0.68 | 2.47 | 1.24 | 1.26 |
| Kri1 | 1.00 | 1.00 | 1.08 | 0.91 | 1.08 | 1.07 | 1.41 | 2.31 | 0.96 | 1.24 | 0.91 | 0.91 |
| Krt19 | 1.41 | 1.06 | 1.07 | 1.00 | 0.65 | 1.00 | 1.08 | 5.34 | 1.71 | 1.00 | 1.00 | 1.00 |
| Krt32 | 1.00 | 1.00 | 1.00 | 1.00 | 1.00 | 1.00 | 1.66 | 5.00 | 1.22 | 1.00 | 1.00 | 1.00 |
| Krt33b | 1.00 | 1.00 | 1.00 | 1.00 | 1.64 | 1.00 | 2.59 | 5.90 | 0.92 | 1.00 | 1.00 | 1.00 |
| Krt79 | 1.00 | 1.00 | 1.00 | 1.00 | 1.00 | 1.00 | 1.21 | 2.40 | 0.79 | 1.00 | 1.00 | 1.00 |
| Krtap10-10 | 1.00 | 1.00 | 1.00 | 1.00 | 1.00 | 1.00 | 5.06 | 3.72 | 0.96 | 1.00 | 1.00 | 1.00 |
| Krtap22-2 | 1.00 | 1.00 | 1.00 | 1.00 | 1.00 | 1.00 | 1.37 | 11.09 | 0.56 | 1.00 | 1.00 | 1.00 |
| Krtap3-2 | 1.00 | 1.00 | 1.00 | 1.00 | 1.00 | 1.00 | 1.31 | 1.98 | 1.01 | 1.00 | 1.00 | 1.00 |
| Krtap5-1 | 1.00 | 1.00 | 1.00 | 1.00 | 1.00 | 1.00 | 5.50 | 0.11 | 0.87 | 1.00 | 1.00 | 1.00 |
| Krtap5-2 | 1.00 | 1.00 | 1.00 | 1.00 | 1.00 | 1.00 | 6.23 | 0.39 | 1.05 | 1.00 | 1.00 | 1.00 |
| Krtdap | 1.00 | 1.00 | 1.00 | 1.00 | 1.00 | 1.00 | 0.94 | 17.56 | 0.62 | 1.00 | 1.00 | 1.00 |
| LOC100038947 | 1.00 | 1.00 | 1.00 | 1.00 | 1.00 | 1.00 | 1.00 | 1.00 | 1.00 | 0.57 | 1.02 | 1.01 |
| LOC100504703 | 0.86 | 0.65 | 0.56 | 1.90 | 2.07 | 0.65 | 1.79 | 3.45 | 0.85 | 4.10 | 1.05 | 1.88 |
| LOC100861615 | 1.00 | 1.00 | 1.00 | 4.81 | 1.00 | 3.90 | 1.00 | 1.00 | 1.00 | 1.00 | 1.00 | 1.00 |
| LOC100861978 | 1.00 | 1.00 | 1.00 | 3.72 | 35.40 | 3.80 | 11.78 | 82.33 | 16.22 | 1.00 | 1.00 | 1.00 |
| LOC101669761 | 1.81 | 2.93 | 1.32 | 1.59 | 1.66 | 1.50 | 2.46 | 6.52 | 1.50 | 2.56 | 1.70 | 2.33 |
| LOC102632423 | 1.00 | 1.00 | 1.00 | 1.00 | 1.00 | 1.00 | 1.00 | 1.00 | 1.00 | 1.00 | 1.00 | 1.00 |
| Lama3 | 1.00 | 1.00 | 1.00 | 1.00 | 1.00 | 1.00 | 0.67 | 0.23 | 1.02 | 1.00 | 1.00 | 1.00 |
| Lama4 | 1.00 | 1.00 | 1.00 | 1.00 | 1.27 | 1.00 | 1.13 | 5.33 | 1.33 | 1.00 | 1.00 | 1.00 |
| Lamc2 | 1.00 | 1.00 | 1.00 | 1.13 | 0.91 | 1.00 | 0.87 | 1.27 | 1.08 | 1.00 | 1.00 | 1.00 |
| Lamp5 | 1.00 | 1.00 | 1.00 | 1.38 | 1.09 | 1.21 | 1.00 | 1.00 | 1.00 | 1.00 | 1.00 | 1.00 |
| Lamtor2 | 0.71 | 0.67 | 0.75 | 1.07 | 1.29 | 0.97 | 0.95 | 7.40 | 1.02 | 2.77 | 1.34 | 1.16 |
| Lamtor3 | 2.05 | 1.37 | 3.01 | 1.83 | 15.56 | 1.62 | 1.55 | 1.69 | 1.46 | 1.45 | 1.36 | 1.63 |
| Lamtor4 | 1.13 | 0.79 | 0.94 | 1.15 | 0.89 | 0.93 | 1.18 | 10.81 | 0.89 | 4.32 | 1.47 | 1.37 |
| Lars | 0.89 | 1.32 | 0.98 | 0.90 | 1.11 | 1.01 | 1.09 | 7.43 | 0.85 | 2.18 | 0.92 | 0.83 |
| Lars2 | 1.34 | 1.45 | 1.71 | 1.40 | 0.46 | 0.98 | 0.83 | 47.78 | 0.95 | 0.44 | 1.27 | 1.57 |
| Lat | 1.00 | 1.00 | 1.00 | 1.00 | 2.34 | 1.00 | 1.59 | 6.06 | 1.30 | 3.45 | 1.50 | 1.13 |
| Lbp | 1.00 | 1.00 | 1.00 | 1.01 | 0.57 | 1.00 | 1.45 | 2.31 | 1.31 | 1.91 | 1.47 | 1.40 |
| Lce1f | 1.00 | 1.00 | 1.00 | 1.00 | 1.00 | 1.00 | 0.96 | 5.64 | 0.72 | 1.00 | 1.00 | 1.00 |
| Lce1g | 1.00 | 1.00 | 1.00 | 1.00 | 1.51 | 1.00 | 1.18 | 6.12 | 0.81 | 1.00 | 1.00 | 1.00 |
| Lce1j | 1.00 | 1.00 | 1.00 | 1.00 | 1.00 | 1.00 | 1.52 | 6.24 | 0.98 | 1.00 | 1.00 | 1.00 |
| Lce1m | 1.00 | 1.00 | 1.00 | 1.00 | 1.00 | 1.00 | 1.16 | 2.54 | 0.98 | 1.00 | 1.00 | 1.00 |
| Lce3c | 1.00 | 1.00 | 1.00 | 1.00 | 1.00 | 1.00 | 0.90 | 13.00 | 1.00 | 1.00 | 1.00 | 1.00 |
| Lce3d | 1.00 | 1.00 | 1.00 | 1.00 | 1.00 | 1.00 | 0.51 | 14.68 | 0.55 | 1.00 | 1.00 | 1.00 |
| Lce3f | 1.00 | 1.00 | 1.00 | 1.00 | 1.00 | 1.00 | 0.92 | 5.42 | 0.77 | 1.00 | 1.00 | 1.00 |
| Lcmt1 | 0.95 | 1.34 | 1.14 | 1.19 | 1.12 | 1.09 | 1.07 | 8.41 | 0.89 | 2.63 | 1.28 | 1.32 |
| Lcn2 | 1.49 | 2.46 | 1.74 | 1.00 | 1.00 | 1.00 | 1.66 | 2.46 | 1.63 | 2.28 | 1.73 | 1.52 |
| Ldhal6b | 1.00 | 1.00 | 1.00 | 1.00 | 1.00 | 1.00 | 6.28 | 1.00 | 1.00 | 1.00 | 1.00 | 1.00 |
| Ldhb | 0.80 | 0.91 | 0.86 | 1.10 | 0.96 | 1.10 | 1.66 | 3.29 | 1.31 | 2.78 | 2.58 | 1.89 |
| Ldhc | 1.00 | 1.00 | 1.00 | 1.00 | 0.80 | 1.00 | 11.98 | 1.00 | 1.00 | 3.91 | 1.06 | 1.59 |
| Ldlr | 1.00 | 1.00 | 1.00 | 0.95 | 0.71 | 0.92 | 0.77 | 0.97 | 0.81 | 2.87 | 4.61 | 6.30 |
| Leng1 | 1.09 | 1.08 | 0.88 | 1.05 | 0.76 | 1.14 | 1.08 | 5.65 | 1.00 | 2.44 | 1.07 | 1.22 |
| Lepr | 1.00 | 1.00 | 1.00 | 0.76 | 1.00 | 1.00 | 1.32 | 0.38 | 1.65 | 1.00 | 1.00 | 1.01 |
| Lgals1 | 0.74 | 0.66 | 0.76 | 0.93 | 0.91 | 1.22 | 0.96 | 15.51 | 0.94 | 3.64 | 0.92 | 1.02 |
| Lgals4 | 0.40 | 0.48 | 0.81 | 0.83 | 3.05 | 0.82 | 1.37 | 6.77 | 1.33 | 2.84 | 1.79 | 1.12 |

Fig. 35- 201

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Lgals7 | 1.00 | 1.00 | 1.00 | 1.00 | 1.00 | 1.00 | 1.00 | 1.00 | 1.00 | 0.41 | 1.00 | 1.00 |
| Lgi3 | 1.00 | 1.00 | 1.00 | 1.00 | 0.29 | 1.00 | 1.51 | 0.87 | 0.92 | 2.00 | 2.14 | 0.99 |
| Lgi4 | 1.12 | 0.73 | 0.92 | 1.47 | 2.61 | 1.82 | 1.40 | 1.28 | 1.50 | 2.08 | 1.73 | 0.65 |
| Lhb | 1.00 | 0.71 | 1.00 | 1.00 | 1.00 | 1.00 | 1.00 | 1.00 | 1.00 | 1.81 | 2.81 | 1.24 |
| Lhx1os | 1.00 | 1.00 | 1.00 | 1.00 | 1.00 | 1.00 | 1.00 | 1.00 | 1.00 | 1.00 | 1.00 | 1.00 |
| Lifr | 1.09 | 2.19 | 1.15 | 5.09 | 2.47 | 1.65 | 1.28 | 1.34 | 1.14 | 0.96 | 0.51 | 1.00 |
| Lig1 | 1.00 | 0.92 | 1.00 | 1.00 | 1.53 | 1.00 | 1.00 | 1.00 | 1.00 | 2.78 | 2.66 | 0.69 |
| Lipe | 0.89 | 0.76 | 1.45 | 0.45 | 1.28 | 1.08 | 0.94 | 0.77 | 1.02 | 1.46 | 1.53 | 1.22 |
| Liph | 1.04 | 0.61 | 0.70 | 1.57 | 9.02 | 1.27 | 0.75 | 0.75 | 0.65 | 2.14 | 2.80 | 1.15 |
| Lmbr1l | 2.10 | 1.10 | 1.21 | 0.77 | 8.48 | 1.32 | 1.26 | 1.05 | 1.18 | 2.45 | 2.66 | 1.10 |
| Lmcd1 | 0.92 | 0.67 | 0.91 | 0.87 | 2.27 | 0.71 | 1.71 | 1.64 | 1.12 | 2.51 | 2.82 | 2.09 |
| Lmf1 | 1.04 | 0.80 | 1.12 | 0.38 | 2.09 | 0.87 | 1.16 | 0.90 | 0.96 | 1.89 | 2.20 | 1.05 |
| Lmod2 | 1.76 | 3.00 | 1.72 | 3.42 | 0.36 | 1.20 | 2.67 | 3.47 | 1.51 | 1.69 | 0.99 | 1.20 |
| Lmtk3 | 1.00 | 1.00 | 1.00 | 1.00 | 0.35 | 1.00 | 1.00 | 1.00 | 1.00 | 1.00 | 1.00 | 1.00 |
| Lor | 1.00 | 0.77 | 1.00 | 1.42 | 2.94 | 1.36 | 1.00 | 1.46 | 1.00 | 0.30 | 1.00 | 1.00 |
| Lox | 2.63 | 4.17 | 2.43 | 6.02 | 1.87 | 1.55 | 4.61 | 4.80 | 3.55 | 1.99 | 1.86 | 2.64 |
| Lpcat3 | 1.03 | 0.83 | 0.96 | 0.51 | 1.68 | 0.96 | 0.69 | 0.58 | 0.67 | 0.94 | 1.57 | 0.99 |
| Lpin2 | 3.14 | 3.81 | 5.38 | 1.34 | 0.68 | 0.92 | 1.46 | 1.46 | 1.45 | 1.16 | 1.23 | 1.40 |
| Lrch4 | 1.08 | 0.89 | 1.06 | 1.08 | 9.08 | 0.72 | 2.39 | 1.32 | 1.27 | 2.79 | 37.68 | 1.00 |
| Lrp11 | 1.29 | 1.00 | 1.43 | 1.37 | 0.19 | 1.30 | 2.11 | 1.83 | 1.68 | 1.00 | 1.00 | 2.42 |
| Lrrc10 | 1.00 | 1.00 | 1.00 | 1.00 | 1.00 | 1.00 | 1.64 | 2.18 | 1.17 | 3.13 | 7.35 | 0.90 |
| Lrrc20 | 0.90 | 5.96 | 0.95 | 1.26 | 0.10 | 0.95 | 1.16 | 1.16 | 0.92 | 1.00 | 0.39 | 1.27 |
| Lrrc27 | 1.00 | 1.00 | 1.00 | 1.73 | 1.93 | 1.10 | 0.57 | 0.55 | 0.45 | 1.77 | 1.81 | 1.35 |
| Lrrc30 | 2.18 | 2.20 | 2.48 | 2.53 | 5.60 | 4.27 | 1.00 | 1.00 | 1.00 | 1.00 | 1.00 | 1.00 |
| Lrrc46 | 1.00 | 1.00 | 1.00 | 1.00 | 1.00 | 1.00 | 1.00 | 1.00 | 1.00 | 2.34 | 2.57 | 1.15 |
| Lrrc4b | 1.00 | 1.00 | 1.00 | 1.00 | 0.16 | 1.00 | 0.30 | 0.31 | 0.39 | 0.75 | 0.65 | 0.82 |
| Lrrc51 | 0.95 | 0.89 | 1.15 | 0.55 | 6.46 | 1.29 | 1.14 | 0.99 | 0.88 | 2.37 | 3.00 | 0.93 |
| Lrrc73 | 1.00 | 1.00 | 1.00 | 0.63 | 1.26 | 1.00 | 1.00 | 1.00 | 1.00 | 4.28 | 5.62 | 1.42 |
| Lrrc74 | 1.00 | 1.00 | 1.00 | 1.00 | 1.00 | 1.00 | 1.00 | 1.00 | 1.00 | 1.00 | 1.00 | 1.00 |
| Lrrn2 | 1.00 | 1.00 | 1.00 | 1.00 | 0.26 | 1.00 | 0.57 | 0.55 | 0.65 | 1.00 | 1.00 | 1.00 |
| Lrwd1 | 1.21 | 0.65 | 0.97 | 0.35 | 4.26 | 1.42 | 1.19 | 0.94 | 0.96 | 1.87 | 2.58 | 0.81 |
| Lsm14a | 1.14 | 1.50 | 1.02 | 1.59 | 0.46 | 1.08 | 0.99 | 1.07 | 1.01 | 0.72 | 0.49 | 1.00 |
| Lsm2 | 1.33 | 0.68 | 0.94 | 0.42 | 3.99 | 0.67 | 0.69 | 0.69 | 0.90 | 1.89 | 2.60 | 0.70 |
| Lsm4 | 1.33 | 0.72 | 0.96 | 0.29 | 8.81 | 0.95 | 1.04 | 0.59 | 0.79 | 1.55 | 3.40 | 0.93 |
| Lsm5 | 0.65 | 0.36 | 0.59 | 1.00 | 11.86 | 1.00 | 0.34 | 1.08 | 0.77 | 3.27 | 6.49 | 0.76 |
| Lsm7 | 1.11 | 0.48 | 0.96 | 0.22 | 7.32 | 0.97 | 0.87 | 1.03 | 0.91 | 1.90 | 3.67 | 0.79 |
| Lsm8 | 1.00 | 1.09 | 0.82 | 0.87 | 1.21 | 0.80 | 0.86 | 0.84 | 0.91 | 0.51 | 0.82 | 1.01 |
| Lsp1 | 1.09 | 0.91 | 0.99 | 0.99 | 8.29 | 1.40 | 1.61 | 1.44 | 1.24 | 1.05 | 1.69 | 0.77 |
| Lst1 | 1.00 | 0.57 | 1.06 | 0.45 | 2.82 | 0.75 | 1.13 | 0.96 | 0.53 | 2.15 | 1.82 | 0.66 |
| Lta4h | 1.09 | 0.34 | 0.77 | 1.30 | 5.19 | 1.41 | 0.99 | 0.81 | 1.01 | 2.53 | 2.41 | 0.84 |
| Ltc4s | 1.23 | 0.51 | 2.12 | 0.23 | 11.55 | 1.09 | 2.17 | 2.34 | 1.51 | 3.28 | 6.67 | 1.40 |
| Ltf | 1.00 | 1.00 | 1.00 | 1.00 | 1.00 | 1.00 | 1.00 | 1.00 | 1.00 | 1.98 | 3.12 | 1.55 |
| Lxn | 1.00 | 1.00 | 0.92 | 1.46 | 1.09 | 0.82 | 0.68 | 0.54 | 0.52 | 0.20 | 0.39 | 0.81 |
| Ly6a | 2.14 | 1.37 | 1.53 | 1.04 | 2.35 | 1.49 | 1.21 | 0.92 | 1.73 | 0.95 | 1.11 | 1.27 |
| Ly6d | 1.00 | 1.00 | 1.00 | 1.00 | 1.00 | 1.00 | 1.00 | 1.00 | 1.00 | 0.47 | 0.50 | 0.70 |
| Ly6g6c | 1.00 | 1.00 | 1.00 | 1.00 | 1.00 | 1.00 | 1.00 | 1.00 | 1.00 | 0.95 | 2.09 | 1.27 |
| Ly6g6d | 1.00 | 0.42 | 1.00 | 0.64 | 1.00 | 1.00 | 1.00 | 1.00 | 1.00 | 0.50 | 1.33 | 0.39 |
| Ly6h | 1.00 | 1.00 | 1.00 | 1.00 | 0.13 | 1.00 | 1.00 | 1.00 | 1.00 | 1.00 | 1.02 | 1.00 |
| Lypd2 | 1.00 | 0.32 | 1.00 | 1.00 | 1.00 | 1.00 | 1.00 | 1.00 | 1.00 | 1.74 | 3.40 | 0.78 |
| Lypd8 | 0.74 | 1.00 | 0.15 | 1.00 | 1.00 | 1.00 | 1.00 | 1.00 | 1.00 | 0.57 | 1.00 | 1.00 |
| Lyve1 | 1.53 | 2.15 | 1.85 | 5.07 | 0.78 | 1.48 | 1.47 | 2.44 | 1.80 | 2.36 | 1.39 | 2.11 |
| Lyz1 | 3.14 | 1.10 | 3.16 | 0.66 | 3.18 | 0.79 | 1.58 | 1.33 | 2.43 | 0.73 | 0.91 | 0.99 |
| Mad2l2 | 0.99 | 0.59 | 0.68 | 0.69 | 5.49 | 1.34 | 1.02 | 0.74 | 1.41 | 2.16 | 3.17 | 1.05 |
| Mafb | 1.04 | 2.23 | 0.55 | 0.76 | 0.57 | 1.33 | 1.18 | 1.23 | 1.17 | 0.80 | 0.93 | 1.21 |
| Maff | 13.40 | 51.23 | 9.35 | 7.08 | 1.45 | 3.22 | 3.71 | 3.72 | 2.53 | 0.61 | 0.57 | 2.25 |
| Mag | 1.00 | 1.00 | 1.00 | 1.00 | 0.22 | 1.00 | 1.00 | 1.00 | 1.00 | 1.16 | 0.98 | 0.78 |
| Magohb | 1.97 | 1.23 | 0.76 | 2.15 | 5.54 | 1.80 | 1.96 | 0.95 | 0.99 | 2.59 | 4.43 | 1.47 |
| Mal2 | 1.00 | 1.00 | 1.00 | 1.54 | 0.37 | 1.05 | 1.00 | 1.00 | 1.00 | 1.38 | 1.50 | 1.44 |
| Malat1 | 1.16 | 1.71 | 1.37 | 1.22 | 0.69 | 1.01 | 1.38 | 2.43 | 1.60 | 2.68 | 1.07 | 1.22 |
| Malsu1 | 1.23 | 0.89 | 1.04 | 0.48 | 5.56 | 1.02 | 1.27 | 0.88 | 0.94 | 1.80 | 3.43 | 1.31 |
| Man2c1 | 0.86 | 0.53 | 1.00 | 0.63 | 3.00 | 0.88 | 1.16 | 1.01 | 1.05 | 2.78 | 2.72 | 1.05 |
| Map1a | 1.41 | 1.18 | 1.92 | 1.00 | 0.08 | 1.14 | 1.70 | 1.68 | 2.72 | 3.00 | 1.37 | 1.30 |
| Map1b | 1.79 | 1.85 | 1.86 | 1.00 | 0.12 | 1.00 | 1.14 | 1.26 | 1.34 | 0.95 | 0.70 | 0.95 |
| Map1lc3a | 2.13 | 1.12 | 1.65 | 0.37 | 4.65 | 0.92 | 1.02 | 0.81 | 0.82 | 2.17 | 2.68 | 0.89 |

Fig. 35- 202

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Lgals7 | 1.23 | 0.75 | 0.46 | 1.00 | 1.00 | 1.00 | 1.00 | 1.00 | 1.00 | 1.00 | 1.00 | 0.29 |
| Lgi3 | 1.00 | 1.00 | 1.00 | 1.00 | 1.00 | 1.00 | 1.00 | 1.00 | 1.00 | 1.00 | 1.00 | 1.00 |
| Lgi4 | 2.37 | 1.25 | 1.34 | 1.00 | 1.00 | 1.00 | 1.00 | 1.00 | 1.00 | 1.34 | 1.35 | 1.25 |
| Lhb | 1.00 | 1.00 | 1.00 | 1.00 | 1.00 | 1.00 | 1.00 | 1.00 | 1.00 | 1.00 | 1.00 | 1.00 |
| Lhx1os | 1.00 | 1.00 | 1.00 | 1.00 | 0.90 | 0.83 | 1.00 | 1.00 | 1.00 | 1.00 | 1.00 | 1.00 |
| Lifr | 2.37 | 2.04 | 2.44 | 1.44 | 1.22 | 1.31 | 1.19 | 1.66 | 1.27 | 1.12 | 0.90 | 1.30 |
| Lig1 | 0.39 | 0.57 | 0.63 | 0.95 | 0.22 | 1.00 | 1.00 | 1.00 | 1.00 | 1.33 | 1.31 | 1.07 |
| Lipe | 0.79 | 0.94 | 0.70 | 0.91 | 0.77 | 1.34 | 0.78 | 1.33 | 1.08 | 1.16 | 1.05 | 1.24 |
| Liph | 1.40 | 1.60 | 1.13 | 1.00 | 0.77 | 0.90 | 1.06 | 1.43 | 1.07 | 1.08 | 1.58 | 1.07 |
| Lmbr1l | 1.07 | 1.45 | 1.02 | 1.39 | 1.02 | 1.52 | 1.11 | 4.18 | 0.75 | 1.09 | 1.43 | 1.06 |
| Lmcd1 | 2.47 | 1.27 | 0.92 | 1.58 | 1.45 | 1.31 | 1.00 | 1.00 | 1.00 | 1.32 | 1.45 | 1.44 |
| Lmf1 | 1.09 | 1.07 | 1.01 | 0.93 | 0.62 | 0.87 | 1.22 | 1.71 | 1.02 | 1.23 | 1.36 | 0.88 |
| Lmod2 | 1.00 | 1.00 | 1.00 | 1.00 | 1.00 | 1.00 | 1.54 | 1.00 | 1.85 | 1.00 | 1.00 | 1.00 |
| Lmtk3 | 1.00 | 1.00 | 1.00 | 1.00 | 0.95 | 1.11 | 1.00 | 1.00 | 1.00 | 1.00 | 1.00 | 1.00 |
| Lor | 0.58 | 0.68 | 1.00 | 1.00 | 1.00 | 0.79 | 1.23 | 1.47 | 1.01 | 1.00 | 1.00 | 0.30 |
| Lox | 4.33 | 2.95 | 2.55 | 3.96 | 2.78 | 4.43 | 1.00 | 1.00 | 1.00 | 2.08 | 1.57 | 1.81 |
| Lpcat3 | 1.26 | 1.56 | 1.18 | 0.89 | 0.93 | 0.92 | 1.07 | 0.79 | 1.05 | 1.04 | 1.28 | 1.15 |
| Lpin2 | 0.82 | 0.79 | 0.94 | 0.79 | 0.71 | 1.01 | 1.46 | 1.14 | 1.45 | 1.22 | 0.98 | 1.03 |
| Lrch4 | 0.83 | 0.81 | 0.77 | 1.36 | 0.80 | 2.19 | 1.08 | 1.54 | 1.00 | 0.51 | 1.00 | 1.00 |
| Lrp11 | 1.10 | 0.59 | 0.96 | 1.66 | 1.84 | 1.29 | 1.59 | 1.00 | 1.60 | 1.85 | 1.02 | 1.49 |
| Lrrc10 | 1.00 | 1.00 | 1.00 | 1.00 | 1.00 | 1.00 | 1.00 | 1.00 | 1.00 | 1.00 | 1.00 | 1.00 |
| Lrrc20 | 0.59 | 0.58 | 0.82 | 1.21 | 1.00 | 0.84 | 1.06 | 1.00 | 1.39 | 1.01 | 0.76 | 1.24 |
| Lrrc27 | 0.73 | 0.78 | 0.77 | 1.00 | 1.00 | 1.00 | 1.00 | 1.00 | 1.00 | 1.08 | 1.00 | 1.00 |
| Lrrc30 | 1.00 | 1.00 | 1.00 | 1.00 | 1.00 | 1.00 | 1.00 | 1.00 | 1.00 | 1.00 | 1.00 | 1.00 |
| Lrrc46 | 1.00 | 1.00 | 1.00 | 0.67 | 1.08 | 0.84 | 1.00 | 0.58 | 0.99 | 1.00 | 1.49 | 1.00 |
| Lrrc4b | 1.00 | 1.00 | 1.00 | 1.00 | 1.00 | 1.00 | 1.00 | 1.00 | 1.00 | 1.29 | 1.06 | 0.62 |
| Lrrc51 | 1.31 | 2.50 | 0.98 | 0.73 | 0.63 | 0.87 | 0.43 | 0.69 | 0.46 | 1.01 | 1.22 | 1.09 |
| Lrrc73 | 1.96 | 2.27 | 0.76 | 1.00 | 1.49 | 1.00 | 1.00 | 1.19 | 1.00 | 1.00 | 1.13 | 1.00 |
| Lrrc74 | 1.00 | 1.00 | 1.00 | 1.00 | 1.00 | 1.00 | 1.00 | 1.00 | 1.00 | 1.00 | 1.00 | 1.00 |
| Lrrn2 | 1.00 | 1.00 | 1.00 | 1.00 | 1.00 | 1.00 | 1.00 | 1.00 | 1.00 | 1.06 | 0.72 | 1.17 |
| Lrwd1 | 0.92 | 0.99 | 0.87 | 1.02 | 0.81 | 1.03 | 0.77 | 1.05 | 1.06 | 0.99 | 1.22 | 0.91 |
| Lsm14a | 0.78 | 0.75 | 0.93 | 0.93 | 0.97 | 1.01 | 1.10 | 1.14 | 1.01 | 0.97 | 0.91 | 1.02 |
| Lsm2 | 0.63 | 0.84 | 0.65 | 0.83 | 0.48 | 0.86 | 1.00 | 1.08 | 0.91 | 0.85 | 1.60 | 0.89 |
| Lsm4 | 0.88 | 1.25 | 0.73 | 0.95 | 0.77 | 0.80 | 1.62 | 1.42 | 1.09 | 1.06 | 1.96 | 1.07 |
| Lsm5 | 2.00 | 1.47 | 0.86 | 0.84 | 1.00 | 1.00 | 1.01 | 1.13 | 1.00 | 0.55 | 3.48 | 1.00 |
| Lsm7 | 1.07 | 1.12 | 0.76 | 0.47 | 0.52 | 0.69 | 0.99 | 1.40 | 1.06 | 0.94 | 1.89 | 1.03 |
| Lsm8 | 0.90 | 0.91 | 0.80 | 0.94 | 1.09 | 0.84 | 1.28 | 0.38 | 0.93 | 0.99 | 1.66 | 0.92 |
| Lsp1 | 0.98 | 1.14 | 0.96 | 0.49 | 0.34 | 0.55 | 1.00 | 0.79 | 1.00 | 0.79 | 1.17 | 0.95 |
| Lst1 | 2.03 | 1.62 | 1.27 | 1.00 | 0.49 | 1.03 | 1.00 | 1.15 | 0.66 | 0.92 | 1.91 | 0.80 |
| Lta4h | 0.87 | 0.93 | 0.81 | 0.87 | 0.63 | 1.10 | 1.20 | 2.34 | 1.07 | 0.94 | 1.02 | 0.78 |
| Ltc4s | 1.84 | 1.82 | 1.20 | 0.53 | 0.42 | 0.55 | 1.00 | 2.50 | 1.00 | 1.84 | 3.04 | 1.05 |
| Ltf | 0.17 | 1.07 | 0.54 | 1.00 | 1.00 | 1.00 | 1.00 | 1.00 | 1.00 | 1.00 | 1.00 | 1.00 |
| Lxn | 0.64 | 0.74 | 0.76 | 0.77 | 0.61 | 0.67 | 1.00 | 1.00 | 1.00 | 1.06 | 0.94 | 1.04 |
| Ly6a | 2.06 | 1.96 | 1.65 | 0.96 | 1.28 | 1.23 | 15.01 | 7.91 | 20.45 | 1.63 | 1.42 | 1.26 |
| Ly6d | 0.89 | 0.94 | 0.74 | 0.80 | 0.38 | 1.03 | 1.75 | 4.85 | 5.49 | 1.00 | 1.52 | 0.41 |
| Ly6g6c | 0.59 | 0.51 | 0.99 | 1.00 | 1.00 | 1.00 | 1.00 | 1.00 | 1.00 | 3.33 | 5.13 | 2.72 |
| Ly6g6d | 1.87 | 1.00 | 1.00 | 0.55 | 0.36 | 0.47 | 1.00 | 0.80 | 1.00 | 0.75 | 2.13 | 0.94 |
| Ly6h | 1.48 | 1.10 | 1.45 | 1.00 | 1.00 | 1.00 | 1.00 | 1.00 | 1.00 | 1.00 | 1.63 | 1.00 |
| Lypd2 | 0.62 | 0.75 | 0.38 | 1.40 | 0.45 | 1.39 | 1.00 | 1.00 | 1.00 | 1.00 | 1.00 | 1.00 |
| Lypd8 | 5.63 | 2.53 | 4.50 | 1.00 | 0.97 | 1.77 | 1.00 | 1.15 | 0.89 | 1.33 | 1.60 | 1.14 |
| Lyve1 | 1.94 | 2.73 | 1.79 | 1.00 | 1.00 | 1.00 | 1.32 | 1.00 | 2.77 | 1.23 | 1.31 | 1.23 |
| Lyz1 | 2.28 | 2.80 | 2.41 | 1.00 | 1.00 | 1.00 | 1.00 | 1.00 | 1.00 | 1.86 | 2.41 | 1.50 |
| Mad2l2 | 1.65 | 2.24 | 1.58 | 0.98 | 1.89 | 0.90 | 1.30 | 2.63 | 1.49 | 0.82 | 1.75 | 1.52 |
| Mafb | 1.43 | 1.40 | 1.87 | 3.25 | 7.66 | 1.74 | 0.60 | 0.41 | 0.57 | 1.02 | 0.88 | 1.05 |
| Maff | 1.58 | 1.57 | 1.13 | 2.18 | 1.04 | 1.32 | 1.94 | 1.00 | 1.08 | 1.24 | 1.35 | 1.27 |
| Mag | 1.00 | 1.00 | 1.00 | 1.00 | 1.00 | 1.00 | 1.00 | 1.00 | 1.00 | 1.00 | 1.00 | 1.00 |
| Magohb | 2.03 | 2.81 | 1.80 | 0.78 | 1.37 | 1.80 | 1.00 | 1.22 | 1.41 | 1.68 | 3.13 | 1.76 |
| Mal2 | 1.24 | 1.32 | 1.72 | 1.30 | 0.89 | 1.09 | 1.06 | 0.69 | 1.07 | 1.27 | 1.24 | 1.28 |
| Malat1 | 0.53 | 0.40 | 0.79 | 1.25 | 1.11 | 1.50 | 1.12 | 3.96 | 1.04 | 1.12 | 0.94 | 0.85 |
| Malsu1 | 1.24 | 1.88 | 0.93 | 1.03 | 0.97 | 1.16 | 1.24 | 1.30 | 1.03 | 1.42 | 1.76 | 1.09 |
| Man2c1 | 1.03 | 1.09 | 1.07 | 0.90 | 0.59 | 0.97 | 1.19 | 2.49 | 1.09 | 0.89 | 1.08 | 1.02 |
| Map1a | 0.98 | 1.00 | 1.00 | 1.00 | 1.00 | 1.00 | 1.00 | 1.00 | 1.00 | 1.08 | 0.72 | 1.00 |
| Map1b | 1.31 | 0.76 | 1.04 | 1.00 | 1.00 | 1.00 | 1.00 | 1.00 | 1.00 | 1.12 | 0.75 | 0.91 |
| Map1lc3a | 1.34 | 1.57 | 1.05 | 1.03 | 0.67 | 1.07 | 1.06 | 2.07 | 0.90 | 1.04 | 1.62 | 1.17 |

Fig. 35- 203

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Lgals7 | 0.88 | 1.23 | 1.31 | 2.57 | 4.80 | 2.67 | 1.00 | 2.59 | 1.59 | 1.00 | 1.00 | 1.00 |
| Lgi3 | 1.00 | 1.00 | 1.00 | 1.05 | 1.87 | 1.24 | 1.00 | 1.00 | 1.00 | 1.00 | 5.87 | 1.00 |
| Lgi4 | 1.34 | 1.30 | 1.18 | 1.71 | 1.60 | 0.97 | 1.17 | 3.55 | 0.97 | 1.14 | 2.63 | 1.34 |
| Lhb | 1.00 | 1.00 | 1.00 | 3.34 | 4.68 | 5.66 | 0.83 | 2.20 | 1.14 | 1.00 | 1.00 | 1.00 |
| Lhx1os | 1.00 | 1.00 | 1.00 | 1.00 | 1.00 | 1.00 | 1.00 | 1.00 | 1.00 | 1.00 | 1.00 | 1.00 |
| Lifr | 1.44 | 1.51 | 1.32 | 0.96 | 0.15 | 0.88 | 0.95 | 1.19 | 0.88 | 1.07 | 0.73 | 1.29 |
| Lig1 | 0.50 | 0.41 | 0.62 | 0.90 | 1.81 | 1.07 | 1.14 | 2.94 | 1.09 | 0.74 | 0.83 | 0.65 |
| Lipe | 1.30 | 1.17 | 1.28 | 0.49 | 0.63 | 0.91 | 0.90 | 3.77 | 1.00 | 1.34 | 1.41 | 1.19 |
| Liph | 0.86 | 1.04 | 0.90 | 1.18 | 3.40 | 1.27 | 0.84 | 1.38 | 0.85 | 1.32 | 1.58 | 1.10 |
| Lmbr1l | 1.32 | 1.37 | 1.34 | 1.24 | 2.12 | 1.16 | 0.95 | 3.20 | 1.05 | 1.00 | 1.30 | 0.97 |
| Lmcd1 | 1.57 | 1.78 | 1.47 | 1.31 | 2.69 | 1.11 | 1.22 | 1.93 | 0.97 | 1.03 | 1.25 | 0.92 |
| Lmf1 | 1.11 | 1.14 | 1.09 | 0.87 | 2.63 | 0.96 | 1.00 | 2.05 | 1.10 | 1.07 | 1.15 | 1.39 |
| Lmod2 | 5.45 | 2.33 | 3.55 | 1.00 | 1.00 | 1.00 | 1.00 | 1.00 | 1.00 | 1.00 | 1.00 | 1.00 |
| Lmtk3 | 1.00 | 1.00 | 1.00 | 1.00 | 1.00 | 1.00 | 1.04 | 1.16 | 1.12 | 1.41 | 6.65 | 1.68 |
| Lor | 1.09 | 1.48 | 1.34 | 1.00 | 1.00 | 7.18 | 1.00 | 1.00 | 1.07 | 1.00 | 1.00 | 0.66 |
| Lox | 3.20 | 3.09 | 2.09 | 2.21 | 0.79 | 0.87 | 1.00 | 1.00 | 1.00 | 5.94 | 4.90 | 2.97 |
| Lpcat3 | 0.92 | 0.94 | 0.98 | 0.96 | 1.76 | 1.12 | 0.83 | 0.75 | 0.97 | 0.87 | 0.90 | 0.75 |
| Lpin2 | 1.31 | 1.58 | 1.28 | 1.19 | 0.54 | 1.09 | 0.97 | 0.70 | 0.89 | 0.98 | 0.79 | 0.98 |
| Lrch4 | 1.58 | 2.88 | 0.27 | 1.00 | 5.37 | 1.00 | 1.19 | 1.05 | 0.98 | 0.73 | 1.19 | 1.01 |
| Lrp11 | 1.11 | 1.35 | 1.46 | 0.92 | 1.00 | 0.72 | 1.32 | 0.90 | 1.11 | 1.46 | 7.51 | 1.02 |
| Lrrc10 | 1.00 | 1.00 | 1.00 | 1.00 | 1.00 | 1.00 | 1.00 | 1.00 | 1.00 | 1.00 | 1.00 | 1.00 |
| Lrrc20 | 0.96 | 0.98 | 0.84 | 1.54 | 1.00 | 0.74 | 0.97 | 1.00 | 0.86 | 0.85 | 0.68 | 0.96 |
| Lrrc27 | 1.00 | 1.02 | 1.00 | 1.98 | 1.00 | 1.49 | 1.23 | 1.49 | 1.22 | 1.00 | 1.52 | 1.00 |
| Lrrc30 | 1.00 | 1.00 | 1.00 | 1.00 | 1.00 | 1.00 | 1.00 | 1.00 | 1.00 | 1.00 | 1.00 | 1.00 |
| Lrrc46 | 1.00 | 1.00 | 1.00 | 2.12 | 1.37 | 2.50 | 1.02 | 0.93 | 0.94 | 1.00 | 1.00 | 1.00 |
| Lrrc4b | 0.93 | 1.00 | 1.00 | 1.00 | 1.00 | 1.00 | 1.00 | 1.00 | 1.00 | 1.00 | 9.75 | 1.00 |
| Lrrc51 | 0.92 | 0.99 | 1.28 | 1.39 | 3.16 | 1.59 | 0.90 | 2.29 | 0.98 | 1.36 | 1.17 | 0.99 |
| Lrrc73 | 1.00 | 1.00 | 1.15 | 1.54 | 2.36 | 1.45 | 0.95 | 2.40 | 1.00 | 1.00 | 3.23 | 1.00 |
| Lrrc74 | 1.00 | 1.00 | 1.00 | 1.00 | 1.00 | 1.00 | 1.29 | 5.11 | 1.30 | 1.00 | 1.00 | 1.00 |
| Lrrn2 | 1.22 | 1.19 | 1.22 | 0.78 | 1.00 | 0.52 | 1.00 | 1.00 | 1.00 | 1.00 | 6.09 | 1.00 |
| Lrwd1 | 1.13 | 1.15 | 0.96 | 1.28 | 3.47 | 0.85 | 1.06 | 2.27 | 1.17 | 0.81 | 1.03 | 0.91 |
| Lsm14a | 1.01 | 0.93 | 0.84 | 0.97 | 0.28 | 1.12 | 1.07 | 1.26 | 1.02 | 1.04 | 0.83 | 1.03 |
| Lsm2 | 0.76 | 0.77 | 0.64 | 0.82 | 3.15 | 0.87 | 1.05 | 2.19 | 1.04 | 1.15 | 1.04 | 0.81 |
| Lsm4 | 0.95 | 0.77 | 0.98 | 1.53 | 2.75 | 0.96 | 1.00 | 2.09 | 1.07 | 1.08 | 1.47 | 0.99 |
| Lsm5 | 0.46 | 1.18 | 1.10 | 0.98 | 2.58 | 1.24 | 1.00 | 2.87 | 1.02 | 0.83 | 2.34 | 0.84 |
| Lsm7 | 0.69 | 0.79 | 0.97 | 1.02 | 2.22 | 0.80 | 0.97 | 2.26 | 1.12 | 0.91 | 1.23 | 0.74 |
| Lsm8 | 1.01 | 1.07 | 1.08 | 1.01 | 0.36 | 1.05 | 0.91 | 0.41 | 0.74 | 1.11 | 1.02 | 0.83 |
| Lsp1 | 1.14 | 1.09 | 1.08 | 0.59 | 2.85 | 0.78 | 1.00 | 0.62 | 1.00 | 0.86 | 0.80 | 0.94 |
| Lst1 | 0.58 | 0.36 | 0.73 | 0.65 | 0.81 | 1.04 | 1.00 | 3.48 | 0.93 | 0.84 | 0.93 | 0.71 |
| Lta4h | 0.94 | 1.08 | 1.06 | 1.40 | 1.23 | 1.09 | 1.21 | 2.39 | 1.08 | 0.97 | 1.07 | 1.04 |
| Ltc4s | 1.16 | 0.76 | 1.25 | 0.83 | 1.62 | 0.92 | 0.60 | 3.98 | 1.14 | 0.89 | 0.81 | 0.42 |
| Ltf | 1.28 | 0.82 | 1.44 | 1.00 | 1.00 | 0.37 | 1.00 | 1.00 | 1.00 | 15.53 | 9.87 | 11.03 |
| Lxn | 0.56 | 0.59 | 0.41 | 0.92 | 2.29 | 0.79 | 0.83 | 0.55 | 1.05 | 0.80 | 0.86 | 0.43 |
| Ly6a | 2.24 | 1.95 | 1.83 | 1.67 | 3.50 | 2.02 | 2.89 | 1.26 | 1.30 | 3.11 | 2.18 | 1.45 |
| Ly6d | 0.76 | 1.03 | 0.90 | 1.00 | 1.40 | 2.52 | 1.00 | 1.00 | 1.35 | 1.59 | 1.50 | 1.22 |
| Ly6g6c | 0.78 | 1.02 | 1.24 | 1.00 | 1.00 | 1.82 | 0.82 | 1.17 | 0.80 | 1.83 | 2.14 | 0.83 |
| Ly6g6d | 0.37 | 0.81 | 0.68 | 0.87 | 2.30 | 0.43 | 1.00 | 0.81 | 1.00 | 2.46 | 0.98 | 1.11 |
| Ly6h | 1.00 | 0.99 | 1.00 | 0.76 | 4.12 | 1.42 | 1.00 | 1.00 | 1.00 | 1.00 | 12.43 | 1.00 |
| Lypd2 | 0.89 | 0.95 | 1.00 | 1.00 | 1.00 | 1.00 | 1.00 | 1.00 | 1.00 | 1.00 | 1.00 | 1.00 |
| Lypd8 | 1.91 | 2.74 | 1.61 | 1.00 | 0.87 | 0.59 | 0.69 | 0.41 | 1.02 | 1.00 | 1.00 | 1.22 |
| Lyve1 | 1.72 | 2.05 | 1.66 | 1.54 | 0.64 | 1.46 | 1.00 | 1.00 | 1.00 | 1.36 | 1.31 | 1.00 |
| Lyz1 | 9.40 | 1.05 | 8.61 | 0.51 | 0.83 | 0.48 | 1.00 | 1.00 | 1.00 | 1.21 | 1.50 | 1.66 |
| Mad2l2 | 1.12 | 2.92 | 1.68 | 1.22 | 3.93 | 1.18 | 1.02 | 1.67 | 1.39 | 1.50 | 1.28 | 0.89 |
| Mafb | 1.14 | 1.11 | 1.25 | 0.97 | 0.36 | 0.71 | 0.86 | 0.92 | 1.04 | 0.66 | 0.82 | 0.86 |
| Maff | 1.44 | 1.69 | 1.12 | 3.34 | 1.27 | 2.41 | 1.08 | 1.00 | 0.81 | 1.27 | 1.16 | 0.82 |
| Mag | 1.00 | 1.00 | 1.00 | 1.00 | 1.00 | 1.00 | 0.99 | 0.80 | 1.11 | 0.74 | 5.95 | 0.58 |
| Magohb | 1.33 | 1.19 | 1.40 | 1.43 | 1.51 | 1.69 | 1.25 | 1.05 | 1.58 | 4.40 | 3.09 | 3.14 |
| Mal2 | 1.11 | 0.91 | 0.88 | 1.38 | 0.99 | 1.14 | 1.00 | 1.00 | 1.00 | 1.00 | 6.85 | 1.00 |
| Malat1 | 0.86 | 1.00 | 0.62 | 1.73 | 0.12 | 0.72 | 0.73 | 5.39 | 0.99 | 1.03 | 0.52 | 1.16 |
| Malsu1 | 1.35 | 1.09 | 0.96 | 1.21 | 4.18 | 1.13 | 0.79 | 1.90 | 1.00 | 1.23 | 1.66 | 1.28 |
| Man2c1 | 1.05 | 1.04 | 0.99 | 1.03 | 1.94 | 0.99 | 0.95 | 2.76 | 1.04 | 0.98 | 1.16 | 1.00 |
| Map1a | 1.15 | 1.27 | 1.17 | 1.15 | 0.92 | 0.88 | 1.54 | 1.81 | 1.22 | 0.72 | 8.61 | 0.84 |
| Map1b | 1.06 | 0.99 | 0.93 | 1.93 | 0.42 | 1.65 | 1.38 | 1.00 | 1.20 | 1.09 | 12.29 | 1.00 |
| Map1lc3a | 1.13 | 1.57 | 1.26 | 0.83 | 2.44 | 0.71 | 0.94 | 2.44 | 0.95 | 0.97 | 2.07 | 0.90 |

Fig. 35- 204

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Lgals7 | 1.00 | 1.00 | 1.00 | 1.00 | 5.57 | 1.00 | 1.11 | 5.28 | 0.69 | 1.00 | 1.00 | 1.00 |
| Lgi3 | 1.00 | 1.00 | 1.00 | 1.21 | 1.06 | 1.12 | 1.00 | 2.17 | 1.06 | 1.00 | 1.00 | 1.00 |
| Lgi4 | 1.21 | 1.00 | 1.16 | 0.98 | 1.21 | 1.00 | 1.30 | 8.10 | 1.13 | 1.00 | 1.00 | 1.00 |
| Lhb | 1.00 | 1.00 | 1.00 | 1.00 | 1.21 | 1.00 | 1.48 | 2.82 | 1.00 | 1.00 | 1.00 | 1.00 |
| Lhx1os | 1.00 | 1.00 | 1.00 | 1.32 | 5.67 | 1.67 | 1.00 | 1.00 | 1.00 | 1.00 | 1.00 | 1.00 |
| Lifr | 1.55 | 1.51 | 1.71 | 1.05 | 1.00 | 1.09 | 1.28 | 0.28 | 1.61 | 1.45 | 2.36 | 2.22 |
| Lig1 | 1.00 | 1.00 | 1.00 | 0.84 | 0.87 | 0.78 | 0.63 | 6.83 | 0.58 | 1.75 | 0.78 | 0.73 |
| Lipe | 0.99 | 1.21 | 1.22 | 0.97 | 1.07 | 1.17 | 1.44 | 5.81 | 1.29 | 2.34 | 1.52 | 1.21 |
| Liph | 1.10 | 1.16 | 0.89 | 1.18 | 1.25 | 0.99 | 0.99 | 5.05 | 0.81 | 2.43 | 1.06 | 1.05 |
| Lmbr1l | 1.82 | 1.83 | 1.09 | 0.93 | 0.61 | 0.98 | 1.55 | 9.50 | 1.22 | 2.43 | 1.52 | 1.08 |
| Lmcd1 | 1.00 | 1.00 | 1.00 | 1.18 | 6.46 | 1.88 | 1.06 | 1.68 | 1.18 | 0.70 | 0.46 | 1.04 |
| Lmf1 | 1.05 | 1.10 | 0.77 | 1.19 | 0.73 | 1.07 | 1.71 | 6.57 | 1.18 | 2.19 | 1.37 | 0.92 |
| Lmod2 | 1.00 | 1.00 | 1.00 | 1.00 | 1.00 | 1.00 | 1.72 | 0.32 | 2.19 | 1.00 | 1.00 | 1.00 |
| Lmtk3 | 1.00 | 1.00 | 1.00 | 1.02 | 0.44 | 1.12 | 1.43 | 1.00 | 1.45 | 1.00 | 1.00 | 1.00 |
| Lor | 1.11 | 1.00 | 0.58 | 1.53 | 1.33 | 1.15 | 1.09 | 2.38 | 0.71 | 1.00 | 1.00 | 1.00 |
| Lox | 2.86 | 2.63 | 1.11 | 1.00 | 1.00 | 1.00 | 2.07 | 1.10 | 2.84 | 1.00 | 1.00 | 1.00 |
| Lpcat3 | 1.19 | 0.80 | 0.83 | 0.99 | 6.27 | 1.09 | 1.06 | 0.85 | 1.01 | 1.11 | 0.84 | 0.94 |
| Lpin2 | 2.46 | 3.26 | 2.67 | 1.04 | 0.65 | 1.00 | 1.00 | 0.77 | 1.14 | 0.85 | 1.01 | 1.02 |
| Lrch4 | 1.00 | 1.31 | 1.00 | 1.39 | 1.94 | 0.84 | 1.00 | 13.98 | 1.00 | 9.84 | 1.62 | 0.98 |
| Lrp11 | 1.00 | 1.00 | 1.00 | 1.11 | 0.72 | 1.05 | 1.35 | 1.00 | 1.77 | 1.00 | 1.00 | 1.00 |
| Lrrc10 | 1.00 | 1.00 | 1.00 | 1.00 | 1.00 | 1.00 | 1.00 | 1.00 | 1.00 | 1.00 | 1.00 | 1.00 |
| Lrrc20 | 1.00 | 1.00 | 1.00 | 1.03 | 1.00 | 1.04 | 0.73 | 0.09 | 0.79 | 0.56 | 0.62 | 0.74 |
| Lrrc27 | 1.00 | 1.00 | 1.00 | 1.17 | 7.16 | 1.25 | 2.59 | 1.94 | 1.51 | 1.00 | 1.00 | 1.00 |
| Lrrc30 | 1.00 | 1.00 | 1.00 | 1.00 | 1.00 | 1.00 | 1.68 | 2.61 | 3.38 | 1.00 | 1.00 | 1.00 |
| Lrrc46 | 1.00 | 1.00 | 1.00 | 1.00 | 0.27 | 1.00 | 6.39 | 1.95 | 1.00 | 1.00 | 1.00 | 1.00 |
| Lrrc4b | 1.00 | 1.00 | 1.00 | 0.98 | 1.14 | 1.01 | 1.00 | 1.00 | 1.00 | 1.00 | 1.00 | 1.00 |
| Lrrc51 | 0.39 | 0.81 | 0.34 | 0.71 | 1.00 | 0.80 | 2.12 | 3.76 | 0.90 | 1.46 | 1.35 | 1.15 |
| Lrrc73 | 1.00 | 1.00 | 1.00 | 1.24 | 0.95 | 1.09 | 1.84 | 9.90 | 0.61 | 1.00 | 1.00 | 1.00 |
| Lrrc74 | 1.00 | 1.00 | 1.00 | 1.00 | 1.00 | 1.00 | 1.00 | 1.00 | 1.00 | 1.00 | 1.00 | 1.00 |
| Lrrn2 | 1.00 | 1.00 | 1.00 | 1.11 | 1.35 | 1.10 | 1.00 | 1.00 | 1.00 | 1.00 | 1.00 | 1.00 |
| Lrwd1 | 1.00 | 1.00 | 1.00 | 0.91 | 1.75 | 0.81 | 1.00 | 5.31 | 0.87 | 2.09 | 0.89 | 0.96 |
| Lsm14a | 1.04 | 0.73 | 0.91 | 1.06 | 6.04 | 0.89 | 0.80 | 0.15 | 0.98 | 0.52 | 0.98 | 0.99 |
| Lsm2 | 0.72 | 0.32 | 0.89 | 0.89 | 1.74 | 0.98 | 0.90 | 7.47 | 0.79 | 1.78 | 1.11 | 1.07 |
| Lsm4 | 1.31 | 3.51 | 1.17 | 1.45 | 1.00 | 0.88 | 1.15 | 8.36 | 0.79 | 2.74 | 0.94 | 1.13 |
| Lsm5 | 1.00 | 1.00 | 1.00 | 2.06 | 0.06 | 1.00 | 0.78 | 16.59 | 1.06 | 5.17 | 2.05 | 1.03 |
| Lsm7 | 2.43 | 0.44 | 0.73 | 1.16 | 0.96 | 0.99 | 1.08 | 9.23 | 0.86 | 2.44 | 1.05 | 1.18 |
| Lsm8 | 0.51 | 1.81 | 1.53 | 0.99 | 7.73 | 1.07 | 1.15 | 0.94 | 1.01 | 0.91 | 1.04 | 0.96 |
| Lsp1 | 0.89 | 1.00 | 1.09 | 0.60 | 0.98 | 0.90 | 0.94 | 3.33 | 0.89 | 2.28 | 1.43 | 1.16 |
| Lst1 | 1.00 | 1.00 | 1.00 | 0.93 | 0.36 | 1.41 | 0.84 | 29.10 | 0.68 | 4.75 | 1.18 | 1.27 |
| Lta4h | 0.90 | 1.16 | 0.84 | 1.07 | 0.72 | 0.94 | 0.91 | 2.78 | 0.76 | 2.72 | 1.25 | 1.16 |
| Ltc4s | 1.00 | 1.00 | 1.00 | 0.81 | 0.81 | 1.04 | 1.23 | 46.35 | 1.00 | 1.06 | 1.00 | 1.00 |
| Ltf | 1.00 | 1.00 | 1.00 | 1.00 | 1.00 | 1.00 | 1.00 | 1.00 | 1.00 | 1.76 | 1.31 | 1.21 |
| Lxn | 0.70 | 1.20 | 0.93 | 0.89 | 7.32 | 0.80 | 1.07 | 0.90 | 1.01 | 0.93 | 1.04 | 0.86 |
| Ly6a | 1.83 | 2.71 | 1.63 | 1.59 | 2.17 | 1.79 | 1.44 | 2.13 | 1.43 | 2.86 | 3.09 | 4.61 |
| Ly6d | 1.00 | 1.00 | 1.00 | 1.00 | 5.70 | 0.43 | 1.04 | 1.96 | 0.64 | 1.86 | 0.72 | 1.36 |
| Ly6g6c | 1.00 | 1.00 | 1.00 | 1.00 | 1.00 | 1.00 | 1.17 | 1.86 | 0.81 | 1.00 | 1.00 | 1.74 |
| Ly6g6d | 1.00 | 1.00 | 1.00 | 0.59 | 0.06 | 0.96 | 2.57 | 9.09 | 1.48 | 1.00 | 1.00 | 1.31 |
| Ly6h | 1.00 | 1.00 | 1.00 | 1.10 | 1.19 | 1.10 | 1.00 | 4.11 | 1.00 | 1.00 | 1.00 | 1.00 |
| Lypd2 | 1.00 | 1.00 | 1.00 | 1.00 | 16.65 | 1.00 | 1.00 | 15.06 | 0.56 | 1.00 | 1.00 | 1.00 |
| Lypd8 | 1.00 | 1.00 | 0.43 | 1.00 | 1.00 | 0.96 | 1.00 | 3.65 | 1.00 | 1.00 | 1.00 | 1.00 |
| Lyve1 | 1.75 | 1.40 | 1.38 | 1.00 | 1.00 | 1.00 | 1.50 | 0.94 | 2.87 | 1.00 | 0.97 | 1.05 |
| Lyz1 | 1.00 | 1.00 | 1.16 | 1.00 | 0.19 | 1.00 | 1.54 | 1.53 | 1.37 | 1.93 | 1.88 | 2.01 |
| Mad2l2 | 1.52 | 0.82 | 0.90 | 0.90 | 8.91 | 1.15 | 1.56 | 5.65 | 1.37 | 2.42 | 1.94 | 1.11 |
| Mafb | 1.02 | 1.48 | 1.43 | 0.91 | 0.39 | 1.01 | 0.89 | 0.32 | 0.98 | 0.55 | 0.85 | 0.88 |
| Maff | 1.64 | 1.56 | 1.62 | 3.68 | 1.00 | 1.64 | 2.27 | 0.13 | 1.55 | 1.00 | 1.00 | 1.00 |
| Mag | 1.00 | 1.00 | 1.00 | 0.98 | 1.11 | 0.97 | 1.00 | 1.00 | 1.00 | 1.41 | 1.59 | 1.39 |
| Magohb | 1.00 | 1.00 | 1.00 | 2.89 | 5.02 | 1.99 | 1.45 | 9.16 | 2.09 | 2.80 | 2.15 | 1.46 |
| Mal2 | 1.40 | 1.55 | 1.00 | 1.19 | 0.91 | 1.14 | 1.00 | 1.47 | 0.95 | 1.00 | 1.00 | 1.00 |
| Malat1 | 1.08 | 1.93 | 1.82 | 0.90 | 0.48 | 0.92 | 0.75 | 0.53 | 0.93 | 0.45 | 0.74 | 0.75 |
| Malsu1 | 0.95 | 0.75 | 0.75 | 1.27 | 1.47 | 1.05 | 1.53 | 7.03 | 1.04 | 2.04 | 1.71 | 1.04 |
| Man2c1 | 1.18 | 0.90 | 0.87 | 1.10 | 1.12 | 0.92 | 1.18 | 6.00 | 1.07 | 1.95 | 0.93 | 0.91 |
| Map1a | 1.00 | 1.00 | 1.00 | 0.86 | 0.84 | 0.96 | 0.69 | 1.69 | 1.17 | 1.00 | 1.00 | 1.00 |
| Map1b | 1.00 | 1.00 | 1.00 | 0.93 | 0.86 | 0.98 | 0.98 | 0.46 | 1.38 | 1.00 | 1.00 | 1.00 |
| Map1lc3a | 1.50 | 1.93 | 1.18 | 1.16 | 0.87 | 1.03 | 1.47 | 8.22 | 0.89 | 3.35 | 1.58 | 1.12 |

Fig. 35- 205

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Map2 | 1.00 | 1.00 | 1.00 | 1.00 | 0.10 | 1.00 | 0.96 | 1.35 | 0.95 | 0.69 | 0.34 | 1.41 |
| Map2k2 | 1.25 | 0.57 | 0.83 | 0.26 | 4.28 | 0.82 | 1.00 | 0.81 | 0.90 | 3.78 | 3.63 | 1.05 |
| Map3k6 | 2.79 | 5.04 | 3.34 | 4.28 | 4.94 | 2.93 | 2.36 | 3.02 | 2.53 | 1.33 | 1.97 | 1.94 |
| Map6 | 1.12 | 1.00 | 1.02 | 1.00 | 0.20 | 1.10 | 0.96 | 0.96 | 0.95 | 0.46 | 0.62 | 1.16 |
| Mapk12 | 0.89 | 0.54 | 0.77 | 0.71 | 4.00 | 0.80 | 0.85 | 0.79 | 0.89 | 1.35 | 1.92 | 0.78 |
| Mapk13 | 1.00 | 1.00 | 1.00 | 1.00 | 5.31 | 1.00 | 1.00 | 1.00 | 1.00 | 4.18 | 7.43 | 1.30 |
| Mapk8ip2 | 1.00 | 1.00 | 1.00 | 1.00 | 0.22 | 1.00 | 1.00 | 1.00 | 1.00 | 1.00 | 1.00 | 1.00 |
| Mapt | 0.92 | 1.09 | 1.09 | 0.67 | 0.19 | 0.67 | 0.92 | 0.95 | 0.85 | 0.75 | 0.42 | 0.90 |
| Marc1 | 1.56 | 1.52 | 1.00 | 6.03 | 36.12 | 3.68 | 1.00 | 1.00 | 1.00 | 1.33 | 1.00 | 1.00 |
| Marc2 | 1.11 | 0.93 | 0.92 | 0.79 | 5.79 | 1.34 | 1.16 | 0.78 | 0.94 | 1.72 | 1.79 | 0.94 |
| March7 | 0.84 | 1.00 | 1.20 | 5.14 | 0.20 | 1.24 | 1.16 | 1.55 | 1.16 | 1.00 | 0.41 | 0.99 |
| Marco | 1.00 | 1.00 | 1.00 | 1.00 | 1.00 | 1.00 | 1.00 | 1.00 | 1.00 | 8.54 | 10.37 | 2.38 |
| Mars | 0.93 | 0.55 | 0.85 | 0.48 | 4.00 | 1.08 | 1.12 | 1.14 | 1.24 | 3.52 | 3.23 | 1.01 |
| Mat1a | 1.00 | 1.00 | 1.00 | 1.00 | 1.09 | 1.00 | 4.90 | 0.53 | 1.00 | 0.82 | 2.12 | 1.00 |
| Matk | 1.00 | 1.00 | 1.00 | 1.00 | 0.43 | 1.00 | 1.00 | 1.00 | 1.00 | 1.59 | 3.27 | 0.86 |
| Mb | 1.18 | 0.49 | 0.87 | 1.07 | 4.52 | 0.83 | 0.92 | 0.86 | 0.78 | 2.25 | 3.14 | 0.63 |
| Mbd1 | 1.09 | 1.21 | 1.15 | 1.06 | 2.06 | 1.43 | 1.35 | 1.53 | 1.07 | 2.14 | 2.88 | 1.46 |
| Mbp | 1.08 | 1.30 | 1.54 | 1.69 | 0.17 | 1.52 | 0.87 | 0.97 | 1.16 | 0.86 | 1.04 | 1.05 |
| Mc2r | 1.22 | 1.00 | 1.44 | 2.68 | 4.60 | 2.80 | 1.00 | 1.00 | 1.00 | 1.00 | 1.00 | 1.00 |
| Mc5r | 1.25 | 1.00 | 1.04 | 19.02 | 14.37 | 23.75 | 1.00 | 1.00 | 1.00 | 1.00 | 1.00 | 1.00 |
| Mcee | 0.88 | 0.77 | 0.67 | 0.76 | 1.24 | 1.20 | 0.84 | 0.80 | 0.73 | 0.53 | 0.95 | 0.97 |
| Mchr1 | 1.00 | 1.00 | 0.63 | 1.00 | 1.00 | 1.00 | 1.00 | 1.00 | 1.00 | 1.00 | 1.16 | 1.43 |
| Mcpt4 | 0.96 | 0.35 | 0.95 | 0.94 | 3.23 | 1.73 | 1.00 | 0.95 | 1.00 | 5.14 | 6.09 | 1.35 |
| Mcrs1 | 1.48 | 0.55 | 0.99 | 0.41 | 7.41 | 0.68 | 0.66 | 0.63 | 0.92 | 1.92 | 3.95 | 1.08 |
| Mcts1 | 1.27 | 0.83 | 0.98 | 0.40 | 3.48 | 0.87 | 0.92 | 0.97 | 0.96 | 1.04 | 1.70 | 0.87 |
| Mdp1 | 0.93 | 0.40 | 0.64 | 0.69 | 4.64 | 0.81 | 0.85 | 0.78 | 0.74 | 2.09 | 2.48 | 0.95 |
| Mecr | 1.20 | 0.61 | 0.93 | 0.42 | 4.99 | 0.79 | 1.06 | 0.92 | 1.09 | 1.48 | 3.15 | 0.81 |
| Med18 | 1.03 | 1.81 | 1.36 | 4.85 | 5.80 | 2.06 | 1.34 | 1.64 | 0.77 | 0.30 | 0.43 | 0.92 |
| Med29 | 1.08 | 0.54 | 0.87 | 0.40 | 6.88 | 1.18 | 0.96 | 0.78 | 1.05 | 2.62 | 3.24 | 0.97 |
| Med9os | 0.98 | 1.62 | 1.07 | 1.00 | 2.72 | 0.85 | 1.74 | 1.56 | 0.89 | 7.06 | 4.25 | 1.00 |
| Mef2b | 1.00 | 0.36 | 1.08 | 0.55 | 3.31 | 1.01 | 1.30 | 0.43 | 1.31 | 2.32 | 3.85 | 0.89 |
| Meg3 | 0.78 | 0.67 | 1.02 | 0.51 | 0.37 | 0.62 | 0.70 | 0.65 | 0.95 | 1.57 | 2.66 | 1.00 |
| Meig1 | 1.00 | 1.00 | 1.00 | 1.00 | 1.00 | 1.00 | 0.39 | 0.31 | 0.35 | 2.62 | 3.26 | 0.96 |
| Meis3 | 1.00 | 0.46 | 1.00 | 1.00 | 2.11 | 1.00 | 1.14 | 1.55 | 1.24 | 1.85 | 2.68 | 0.98 |
| Mepce | 1.11 | 0.75 | 1.09 | 0.86 | 3.25 | 1.12 | 1.05 | 0.99 | 1.11 | 2.45 | 2.79 | 1.12 |
| Mest | 1.00 | 1.00 | 1.00 | 1.00 | 1.00 | 1.00 | 1.04 | 1.31 | 1.49 | 2.14 | 0.47 | 0.96 |
| Metap1d | 0.79 | 0.49 | 1.00 | 0.49 | 6.67 | 0.80 | 0.93 | 0.73 | 0.70 | 2.01 | 3.28 | 0.85 |
| Metrn | 1.08 | 0.55 | 0.71 | 0.40 | 2.59 | 0.52 | 1.06 | 0.80 | 0.79 | 2.24 | 3.20 | 1.13 |
| Metrnl | 1.52 | 0.58 | 1.31 | 0.79 | 3.14 | 0.88 | 1.39 | 0.81 | 0.91 | 0.67 | 0.83 | 0.89 |
| Mettl10 | 0.66 | 1.04 | 0.82 | 0.76 | 0.89 | 0.73 | 0.62 | 0.78 | 0.62 | 0.68 | 0.44 | 0.81 |
| Mettl7b | 1.00 | 1.00 | 0.91 | 1.00 | 1.13 | 1.00 | 1.04 | 0.94 | 1.00 | 0.53 | 1.00 | 1.00 |
| Mfge8 | 1.31 | 0.69 | 1.21 | 0.59 | 7.77 | 1.35 | 1.31 | 1.11 | 1.12 | 2.39 | 2.60 | 0.83 |
| Mfsd2a | 1.00 | 1.28 | 1.00 | 0.51 | 2.77 | 3.80 | 1.00 | 1.00 | 1.00 | 2.14 | 5.33 | 1.68 |
| Mfsd6l | 1.00 | 1.00 | 1.00 | 1.00 | 1.00 | 1.00 | 1.00 | 1.00 | 1.00 | 3.31 | 4.06 | 1.19 |
| Mgmt | 1.75 | 1.20 | 1.02 | 0.55 | 7.18 | 0.79 | 0.90 | 0.95 | 1.37 | 2.47 | 3.44 | 0.76 |
| Mgp | 1.81 | 0.97 | 1.34 | 0.46 | 4.15 | 0.92 | 1.39 | 1.16 | 1.60 | 0.83 | 1.68 | 0.97 |
| Mgst2 | 1.00 | 0.76 | 1.00 | 0.57 | 4.76 | 0.42 | 1.00 | 1.00 | 1.00 | 1.75 | 2.85 | 1.26 |
| Mgst3 | 1.22 | 0.56 | 0.81 | 0.11 | 5.95 | 0.74 | 0.93 | 0.79 | 0.76 | 1.75 | 3.10 | 0.93 |
| Mia | 1.00 | 1.00 | 1.00 | 1.00 | 1.00 | 1.00 | 1.00 | 1.00 | 1.00 | 4.06 | 2.39 | 1.59 |
| Miat | 1.00 | 1.00 | 1.00 | 1.00 | 0.19 | 1.00 | 1.00 | 1.00 | 1.00 | 1.00 | 1.00 | 1.00 |
| Mical1 | 0.93 | 0.83 | 1.27 | 0.65 | 2.38 | 1.02 | 1.23 | 1.24 | 1.20 | 1.81 | 2.08 | 1.10 |
| Micall1 | 1.31 | 2.14 | 1.49 | 1.43 | 0.46 | 0.95 | 0.85 | 0.97 | 1.02 | 0.76 | 0.48 | 1.32 |
| Mif | 1.32 | 0.71 | 1.05 | 0.27 | 7.12 | 1.51 | 0.97 | 0.83 | 0.92 | 2.11 | 2.71 | 0.84 |
| Mif4gd | 1.15 | 1.17 | 1.18 | 0.83 | 1.51 | 1.35 | 0.86 | 0.80 | 0.80 | 0.70 | 0.99 | 1.06 |
| Miip | 0.57 | 0.38 | 0.67 | 1.40 | 9.86 | 0.94 | 1.25 | 1.33 | 0.87 | 3.96 | 4.36 | 1.08 |
| Minos1 | 0.95 | 0.50 | 0.70 | 0.31 | 6.74 | 0.68 | 0.77 | 0.80 | 0.74 | 2.27 | 3.11 | 0.91 |
| Mir10a | 1.00 | 1.00 | 1.00 | 1.00 | 1.00 | 1.00 | 1.00 | 1.00 | 1.00 | 1.00 | 1.00 | 27.05 |
| Mir1291 | 1.00 | 1.00 | 1.00 | 1.00 | 1.00 | 1.00 | 13.95 | 1.00 | 0.05 | 1.00 | 1.00 | 1.00 |
| Mir142b | 1.00 | 1.00 | 1.00 | 1.00 | 1.00 | 1.00 | 1.00 | 1.00 | 1.00 | 0.02 | 2.07 | 0.03 |
| Mir1957b | 1.00 | 1.00 | 1.00 | 1.00 | 1.00 | 1.00 | 1.00 | 1.00 | 1.00 | 1.00 | 1.00 | 1.00 |
| Mir210 | 1.00 | 1.00 | 1.00 | 1.00 | 1.00 | 1.00 | 1.00 | 1.00 | 1.00 | 1.00 | 1.00 | 1.00 |
| Mir214 | 1.00 | 59.28 | 1.00 | 0.08 | 1.00 | 1.00 | 1.00 | 1.00 | 1.00 | 0.05 | 1.00 | 1.00 |
| Mir22hg | 1.18 | 2.19 | 0.88 | 1.40 | 0.60 | 0.73 | 1.14 | 1.29 | 1.07 | 0.64 | 0.68 | 1.33 |
| Mir365-2 | 1.00 | 1.00 | 1.00 | 87.61 | 1.00 | 1.00 | 1.00 | 1.00 | 1.00 | 1.00 | 1.00 | 1.00 |

Fig. 35- 206

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Map2 | 1.46 | 1.05 | 1.38 | 1.26 | 1.00 | 1.00 | 1.00 | 1.00 | 1.00 | 1.31 | 0.94 | 1.15 |
| Map2k2 | 0.99 | 1.14 | 0.97 | 0.93 | 0.54 | 1.04 | 1.13 | 3.28 | 1.09 | 1.05 | 1.28 | 1.02 |
| Map3k6 | 3.50 | 3.51 | 2.73 | 2.20 | 1.89 | 2.35 | 2.93 | 1.56 | 1.29 | 1.69 | 1.70 | 1.43 |
| Map6 | 1.00 | 1.04 | 1.00 | 1.00 | 1.00 | 0.87 | 1.00 | 1.00 | 1.00 | 1.16 | 0.89 | 1.16 |
| Mapk12 | 1.64 | 1.86 | 1.18 | 0.78 | 0.66 | 0.74 | 0.69 | 1.14 | 1.05 | 0.61 | 1.23 | 0.68 |
| Mapk13 | 1.45 | 2.19 | 1.28 | 1.80 | 0.83 | 1.21 | 1.00 | 3.45 | 1.00 | 0.82 | 1.29 | 0.91 |
| Mapk8ip2 | 1.00 | 1.00 | 1.00 | 1.00 | 1.00 | 1.00 | 1.00 | 1.00 | 1.00 | 0.91 | 0.94 | 0.96 |
| Mapt | 1.00 | 1.00 | 1.00 | 1.03 | 1.10 | 1.04 | 1.03 | 1.00 | 1.39 | 1.00 | 0.87 | 1.10 |
| Marc1 | 2.08 | 1.80 | 1.39 | 0.61 | 0.38 | 0.50 | 1.43 | 1.90 | 1.43 | 1.00 | 1.00 | 1.00 |
| Marc2 | 1.23 | 1.31 | 1.07 | 1.14 | 0.94 | 1.16 | 1.04 | 1.56 | 1.08 | 0.96 | 1.29 | 0.87 |
| March7 | 0.58 | 0.46 | 0.85 | 1.47 | 1.00 | 1.01 | 1.28 | 1.00 | 1.15 | 1.19 | 0.46 | 0.91 |
| Marco | 1.00 | 1.00 | 1.00 | 1.00 | 1.00 | 1.00 | 1.00 | 8.63 | 1.00 | 1.00 | 1.00 | 1.00 |
| Mars | 0.87 | 0.92 | 0.90 | 1.18 | 0.57 | 0.98 | 1.08 | 2.58 | 0.71 | 1.02 | 1.08 | 1.01 |
| Mat1a | 14.40 | 1.57 | 1.00 | 1.00 | 1.00 | 1.00 | 2.13 | 2.76 | 1.68 | 1.38 | 2.37 | 1.00 |
| Matk | 1.39 | 1.40 | 1.23 | 1.00 | 0.39 | 1.00 | 1.00 | 1.19 | 1.00 | 0.73 | 0.85 | 0.74 |
| Mb | 1.05 | 0.70 | 0.67 | 1.00 | 1.00 | 1.00 | 1.00 | 1.00 | 1.00 | 1.00 | 1.00 | 0.20 |
| Mbd1 | 0.99 | 1.24 | 1.03 | 1.37 | 1.97 | 1.04 | 1.28 | 1.18 | 0.99 | 1.20 | 1.23 | 0.93 |
| Mbp | 0.59 | 0.59 | 0.66 | 1.13 | 0.85 | 1.27 | 1.39 | 1.99 | 2.41 | 1.00 | 0.83 | 0.89 |
| Mc2r | 1.00 | 1.00 | 1.00 | 1.00 | 1.00 | 1.00 | 1.00 | 1.00 | 1.00 | 1.00 | 1.00 | 1.00 |
| Mc5r | 1.00 | 1.00 | 1.00 | 1.00 | 1.00 | 1.00 | 1.00 | 1.00 | 1.00 | 1.00 | 1.00 | 1.00 |
| Mcee | 1.07 | 1.29 | 0.84 | 0.86 | 1.32 | 0.81 | 0.84 | 0.44 | 0.74 | 0.85 | 1.17 | 0.95 |
| Mchr1 | 1.73 | 1.12 | 1.00 | 4.28 | 5.04 | 1.63 | 1.00 | 1.00 | 1.00 | 0.96 | 1.18 | 0.69 |
| Mcpt4 | 0.29 | 0.33 | 0.24 | 1.00 | 1.00 | 1.00 | 1.00 | 1.00 | 1.00 | 2.05 | 2.35 | 1.14 |
| Mcrs1 | 1.43 | 1.73 | 0.89 | 0.97 | 0.70 | 0.71 | 0.95 | 1.90 | 1.13 | 0.94 | 1.75 | 1.12 |
| Mcts1 | 1.14 | 1.44 | 0.91 | 0.79 | 0.60 | 0.84 | 0.72 | 0.82 | 0.78 | 1.16 | 1.96 | 0.99 |
| Mdp1 | 1.10 | 1.31 | 0.94 | 0.87 | 0.66 | 0.88 | 0.70 | 1.40 | 0.85 | 1.06 | 1.70 | 1.01 |
| Mecr | 0.69 | 1.30 | 0.62 | 1.05 | 0.68 | 0.92 | 1.13 | 1.64 | 1.12 | 0.87 | 1.40 | 0.80 |
| Med18 | 0.96 | 1.16 | 0.86 | 2.79 | 7.36 | 2.16 | 1.91 | 1.31 | 1.96 | 0.87 | 0.74 | 0.89 |
| Med29 | 0.99 | 1.70 | 0.96 | 0.95 | 0.53 | 0.88 | 1.18 | 2.95 | 0.82 | 0.85 | 1.28 | 0.89 |
| Med9os | 1.00 | 1.00 | 1.00 | 0.91 | 0.38 | 0.51 | 1.00 | 1.00 | 1.00 | 1.00 | 1.00 | 1.00 |
| Mef2b | 1.20 | 1.75 | 0.96 | 1.00 | 1.00 | 1.00 | 1.00 | 1.00 | 1.00 | 1.00 | 1.28 | 0.67 |
| Meg3 | 1.47 | 0.95 | 0.84 | 1.00 | 1.00 | 1.00 | 0.80 | 0.96 | 0.66 | 0.85 | 1.07 | 0.94 |
| Meig1 | 1.00 | 1.00 | 1.00 | 1.00 | 0.70 | 1.00 | 1.00 | 2.88 | 1.00 | 1.00 | 1.00 | 1.00 |
| Meis3 | 1.16 | 1.40 | 0.82 | 1.00 | 0.74 | 0.71 | 1.00 | 1.70 | 1.00 | 0.77 | 1.37 | 0.98 |
| Mepce | 0.94 | 0.95 | 0.99 | 1.00 | 0.58 | 0.97 | 0.81 | 1.43 | 0.92 | 0.90 | 1.06 | 0.99 |
| Mest | 1.00 | 1.00 | 1.00 | 1.00 | 1.00 | 1.00 | 1.00 | 1.00 | 1.00 | 0.83 | 1.50 | 1.94 |
| Metap1d | 1.01 | 1.36 | 0.83 | 0.79 | 0.56 | 0.92 | 0.85 | 1.74 | 0.73 | 0.93 | 1.46 | 0.92 |
| Metrn | 0.67 | 0.94 | 0.69 | 0.68 | 0.44 | 0.97 | 0.58 | 1.15 | 0.66 | 1.03 | 1.43 | 0.70 |
| Metrnl | 1.33 | 1.41 | 1.41 | 0.78 | 1.18 | 0.73 | 1.08 | 1.47 | 0.89 | 1.17 | 1.49 | 1.07 |
| Mettl10 | 1.14 | 0.93 | 0.87 | 0.60 | 0.84 | 0.74 | 0.82 | 0.91 | 0.76 | 1.07 | 1.30 | 1.06 |
| Mettl7b | 2.12 | 1.00 | 1.00 | 0.73 | 0.49 | 0.83 | 1.09 | 1.54 | 1.05 | 0.84 | 1.16 | 0.98 |
| Mfge8 | 1.33 | 1.49 | 1.23 | 1.16 | 0.67 | 1.12 | 0.82 | 2.57 | 1.04 | 0.89 | 1.39 | 1.06 |
| Mfsd2a | 1.10 | 0.95 | 1.00 | 2.27 | 2.05 | 0.34 | 1.40 | 0.94 | 1.05 | 1.00 | 1.00 | 1.00 |
| Mfsd6l | 1.00 | 1.00 | 1.00 | 0.95 | 0.46 | 1.00 | 1.00 | 1.00 | 1.00 | 1.24 | 1.54 | 1.19 |
| Mgmt | 1.58 | 0.99 | 1.02 | 1.48 | 1.35 | 1.89 | 1.01 | 1.73 | 1.55 | 1.43 | 1.69 | 1.16 |
| Mgp | 2.12 | 2.14 | 1.14 | 0.78 | 1.08 | 0.60 | 0.98 | 0.81 | 0.43 | 1.00 | 1.54 | 0.94 |
| Mgst2 | 1.16 | 1.52 | 0.85 | 1.00 | 1.60 | 1.00 | 1.00 | 1.00 | 1.00 | 1.13 | 1.84 | 1.17 |
| Mgst3 | 1.13 | 1.83 | 0.68 | 0.71 | 0.63 | 0.77 | 0.34 | 0.26 | 0.43 | 1.02 | 1.78 | 1.04 |
| Mia | 1.02 | 1.00 | 1.00 | 1.00 | 0.66 | 1.17 | 1.00 | 1.00 | 1.00 | 1.03 | 1.69 | 0.79 |
| Miat | 1.00 | 1.00 | 1.33 | 1.00 | 1.00 | 1.00 | 1.00 | 1.00 | 1.00 | 0.85 | 0.71 | 0.89 |
| Mical1 | 0.92 | 0.85 | 0.95 | 1.00 | 0.58 | 1.01 | 1.00 | 1.00 | 1.00 | 1.17 | 0.96 | 1.07 |
| Micall1 | 0.87 | 0.68 | 1.20 | 1.16 | 1.09 | 1.19 | 0.98 | 2.61 | 1.11 | 0.97 | 0.77 | 0.94 |
| Mif | 0.90 | 1.15 | 0.83 | 0.83 | 0.63 | 0.98 | 0.63 | 1.43 | 0.69 | 1.08 | 1.37 | 1.20 |
| Mif4gd | 1.02 | 1.08 | 0.89 | 1.24 | 1.76 | 1.09 | 0.73 | 0.60 | 0.76 | 0.89 | 1.12 | 0.94 |
| Miip | 1.28 | 1.40 | 1.33 | 0.96 | 0.54 | 1.13 | 0.77 | 3.10 | 1.00 | 1.41 | 1.80 | 1.07 |
| Minos1 | 1.28 | 1.61 | 0.93 | 0.82 | 0.58 | 0.82 | 1.00 | 1.67 | 0.89 | 1.08 | 1.51 | 0.97 |
| Mir10a | 1.00 | 1.00 | 1.00 | 1.00 | 1.00 | 1.00 | 1.00 | 1.00 | 1.00 | 1.00 | 1.00 | 1.00 |
| Mir1291 | 1.00 | 0.03 | 0.74 | 1.00 | 1.00 | 1.00 | 1.00 | 1.00 | 1.00 | 1.00 | 1.00 | 0.05 |
| Mir142b | 1.23 | 0.57 | 0.83 | 1.00 | 1.00 | 1.00 | 1.00 | 1.00 | 1.00 | 64.74 | 1.00 | 1.00 |
| Mir1957b | 1.00 | 0.21 | 1.00 | 1.00 | 1.00 | 1.00 | 1.00 | 1.00 | 0.56 | 1.00 | 1.00 | 1.00 |
| Mir210 | 1.00 | 1.00 | 1.00 | 1.00 | 1.00 | 1.00 | 1.00 | 1.00 | 1.00 | 115.37 | 1.00 | 1.00 |
| Mir214 | 1.00 | 1.00 | 1.00 | 1.00 | 1.00 | 1.00 | 1.00 | 1.00 | 1.00 | 1.00 | 1.00 | 1.00 |
| Mir22hg | 1.39 | 1.43 | 1.06 | 1.17 | 1.69 | 0.92 | 0.83 | 0.44 | 0.73 | 1.09 | 1.11 | 1.14 |
| Mir365-2 | 1.00 | 1.00 | 1.00 | 1.00 | 1.00 | 1.00 | 1.00 | 1.00 | 1.00 | 1.00 | 1.00 | 1.00 |

Fig. 35- 207

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Map2 | 1.16 | 1.31 | 1.21 | 1.00 | 1.00 | 1.00 | 1.12 | 0.50 | 0.97 | 1.00 | 16.51 | 1.00 |
| Map2k2 | 0.99 | 1.15 | 0.96 | 0.99 | 2.10 | 1.02 | 0.89 | 4.61 | 1.07 | 1.01 | 1.11 | 0.89 |
| Map3k6 | 2.11 | 2.61 | 2.22 | 3.43 | 1.79 | 2.47 | 1.00 | 1.00 | 1.00 | 2.60 | 4.10 | 3.00 |
| Map6 | 0.84 | 1.08 | 1.16 | 0.56 | 1.43 | 0.51 | 1.07 | 1.60 | 0.97 | 1.00 | 5.18 | 0.78 |
| Mapk12 | 0.73 | 0.89 | 1.56 | 0.62 | 1.08 | 0.89 | 1.00 | 1.00 | 1.00 | 0.84 | 0.81 | 0.72 |
| Mapk13 | 0.83 | 0.98 | 0.84 | 1.13 | 5.30 | 2.43 | 1.00 | 4.51 | 1.00 | 1.18 | 1.00 | 1.00 |
| Mapk8ip2 | 1.23 | 1.09 | 1.00 | 1.00 | 1.00 | 1.00 | 1.10 | 1.16 | 1.02 | 1.00 | 7.34 | 1.00 |
| Mapt | 1.42 | 1.64 | 1.50 | 0.77 | 1.00 | 0.94 | 1.16 | 1.18 | 0.99 | 0.76 | 10.17 | 1.21 |
| Marc1 | 1.43 | 1.06 | 1.00 | 4.53 | 18.97 | 1.02 | 1.00 | 1.00 | 1.00 | 1.00 | 1.00 | 1.00 |
| Marc2 | 1.07 | 1.11 | 1.09 | 1.03 | 5.12 | 1.00 | 0.74 | 1.61 | 0.86 | 1.08 | 1.20 | 1.01 |
| March7 | 1.14 | 1.09 | 0.80 | 1.33 | 0.47 | 0.76 | 1.29 | 0.67 | 1.08 | 0.99 | 0.53 | 0.99 |
| Marco | 1.00 | 1.00 | 1.00 | 1.00 | 1.34 | 1.00 | 1.00 | 1.00 | 1.00 | 0.72 | 1.52 | 0.80 |
| Mars | 1.05 | 0.98 | 0.93 | 0.99 | 2.16 | 1.02 | 1.04 | 3.06 | 1.04 | 0.94 | 1.02 | 0.95 |
| Mat1a | 2.70 | 9.05 | 2.34 | 0.78 | 1.00 | 1.00 | 1.00 | 1.00 | 1.00 | 1.00 | 2.71 | 1.00 |
| Matk | 1.00 | 1.00 | 1.30 | 0.62 | 0.65 | 0.40 | 1.01 | 4.05 | 1.00 | 0.93 | 1.35 | 1.07 |
| Mb | 2.02 | 0.78 | 1.95 | 1.00 | 0.66 | 0.44 | 1.00 | 1.53 | 1.00 | 1.00 | 1.00 | 1.00 |
| Mbd1 | 1.04 | 1.20 | 0.90 | 2.61 | 7.57 | 1.50 | 1.00 | 0.79 | 0.98 | 1.20 | 1.44 | 1.16 |
| Mbp | 0.94 | 0.90 | 0.81 | 0.93 | 0.75 | 1.04 | 2.64 | 2.42 | 1.60 | 0.70 | 5.67 | 0.72 |
| Mc2r | 1.00 | 1.00 | 1.00 | 2.98 | 5.98 | 2.96 | 1.00 | 1.00 | 1.00 | 1.00 | 1.00 | 1.00 |
| Mc5r | 1.00 | 1.00 | 1.00 | 11.19 | 1.00 | 6.24 | 1.00 | 1.00 | 1.00 | 1.00 | 1.00 | 1.00 |
| Mcee | 1.03 | 0.99 | 1.03 | 0.85 | 2.47 | 0.99 | 0.94 | 0.18 | 0.62 | 1.27 | 1.11 | 0.97 |
| Mchr1 | 1.35 | 1.86 | 1.73 | 1.00 | 1.00 | 1.15 | 1.00 | 1.00 | 1.00 | 1.00 | 1.46 | 1.00 |
| Mcpt4 | 0.64 | 0.47 | 0.91 | 1.30 | 2.59 | 1.07 | 1.00 | 1.00 | 1.00 | 1.00 | 1.00 | 1.00 |
| Mcrs1 | 0.83 | 1.07 | 1.14 | 1.15 | 4.81 | 1.25 | 1.12 | 1.81 | 1.12 | 1.11 | 1.28 | 0.94 |
| Mcts1 | 1.08 | 1.09 | 0.91 | 0.89 | 6.07 | 1.12 | 1.00 | 0.45 | 0.49 | 1.20 | 0.95 | 1.11 |
| Mdp1 | 0.99 | 0.94 | 0.97 | 0.94 | 1.67 | 0.96 | 0.77 | 2.20 | 0.86 | 1.08 | 1.08 | 0.99 |
| Mecr | 0.86 | 0.99 | 0.83 | 0.76 | 2.18 | 0.59 | 1.02 | 2.11 | 0.99 | 0.90 | 1.39 | 0.83 |
| Med18 | 1.00 | 0.87 | 1.26 | 3.93 | 1.45 | 3.33 | 0.97 | 1.22 | 0.87 | 1.17 | 1.05 | 1.01 |
| Med29 | 1.23 | 1.10 | 0.87 | 1.36 | 2.40 | 1.04 | 0.99 | 3.22 | 1.18 | 0.97 | 1.29 | 1.12 |
| Med9os | 1.00 | 1.00 | 1.00 | 0.67 | 0.23 | 1.10 | 0.91 | 2.22 | 0.89 | 1.00 | 1.00 | 1.00 |
| Mef2b | 1.00 | 1.00 | 1.00 | 1.00 | 1.00 | 1.22 | 0.79 | 1.45 | 0.88 | 0.89 | 1.11 | 0.59 |
| Meg3 | 1.02 | 1.14 | 1.09 | 0.84 | 1.38 | 0.78 | 1.19 | 1.08 | 0.55 | 0.22 | 5.86 | 0.45 |
| Meig1 | 1.00 | 1.00 | 1.00 | 2.25 | 5.15 | 0.77 | 0.94 | 1.85 | 0.96 | 1.00 | 1.00 | 1.00 |
| Meis3 | 1.22 | 1.05 | 0.98 | 0.77 | 4.12 | 0.90 | 1.00 | 1.59 | 1.00 | 0.77 | 1.49 | 1.04 |
| Mepce | 0.95 | 0.99 | 1.12 | 1.06 | 2.20 | 1.29 | 1.09 | 2.31 | 1.09 | 1.02 | 1.04 | 1.15 |
| Mest | 1.45 | 1.29 | 1.52 | 0.34 | 0.15 | 0.19 | 1.00 | 1.00 | 1.00 | 1.34 | 0.94 | 1.00 |
| Metap1d | 0.89 | 1.07 | 0.92 | 0.84 | 3.13 | 0.97 | 0.91 | 2.69 | 0.81 | 0.98 | 1.20 | 0.95 |
| Metrn | 0.76 | 1.17 | 0.92 | 0.59 | 1.46 | 0.62 | 1.05 | 3.21 | 1.27 | 0.85 | 1.48 | 0.90 |
| Metrnl | 0.86 | 0.90 | 1.14 | 0.63 | 0.81 | 0.48 | 1.27 | 0.67 | 0.86 | 0.74 | 0.85 | 0.79 |
| Mettl10 | 0.82 | 0.87 | 1.39 | 0.74 | 0.90 | 0.95 | 0.85 | 0.40 | 0.85 | 0.80 | 0.78 | 1.25 |
| Mettl7b | 0.67 | 0.50 | 0.59 | 0.79 | 2.33 | 0.89 | 1.16 | 2.57 | 1.68 | 1.00 | 1.00 | 1.00 |
| Mfge8 | 1.12 | 1.25 | 1.27 | 1.12 | 1.70 | 0.85 | 0.97 | 3.07 | 0.95 | 0.72 | 0.79 | 0.71 |
| Mfsd2a | 0.68 | 0.74 | 0.56 | 10.58 | 1.23 | 1.24 | 0.47 | 0.47 | 0.65 | 1.00 | 1.34 | 1.00 |
| Mfsd6l | 1.54 | 1.14 | 0.64 | 1.48 | 2.36 | 2.65 | 1.02 | 2.13 | 1.04 | 1.00 | 1.00 | 1.00 |
| Mgmt | 1.48 | 1.05 | 0.97 | 0.59 | 1.15 | 0.69 | 0.70 | 1.93 | 0.41 | 1.23 | 1.52 | 1.23 |
| Mgp | 1.16 | 1.57 | 1.58 | 1.97 | 6.57 | 1.58 | 1.52 | 1.97 | 1.93 | 1.79 | 2.72 | 1.72 |
| Mgst2 | 0.74 | 0.84 | 0.85 | 0.13 | 1.30 | 0.86 | 1.24 | 2.44 | 1.47 | 1.58 | 1.25 | 0.83 |
| Mgst3 | 0.67 | 0.71 | 0.75 | 0.22 | 1.01 | 0.42 | 1.15 | 1.53 | 1.32 | 0.33 | 1.05 | 0.32 |
| Mia | 1.01 | 1.32 | 1.71 | 1.33 | 7.09 | 2.73 | 1.00 | 1.00 | 1.00 | 1.00 | 1.00 | 1.00 |
| Miat | 1.00 | 1.00 | 1.00 | 1.00 | 1.00 | 1.00 | 1.63 | 1.67 | 1.49 | 1.00 | 9.08 | 1.00 |
| Mical1 | 1.29 | 1.18 | 1.64 | 1.42 | 5.75 | 1.17 | 1.00 | 1.00 | 1.00 | 0.82 | 0.71 | 0.87 |
| Micall1 | 1.04 | 1.11 | 0.91 | 1.36 | 0.76 | 1.31 | 1.09 | 5.78 | 1.17 | 0.92 | 0.74 | 1.02 |
| Mif | 0.77 | 0.82 | 1.07 | 0.85 | 3.23 | 1.26 | 0.84 | 2.24 | 1.05 | 1.39 | 1.45 | 0.99 |
| Mif4gd | 1.08 | 1.01 | 1.27 | 1.28 | 5.11 | 1.61 | 0.93 | 0.40 | 1.03 | 0.96 | 0.83 | 0.80 |
| Miip | 1.52 | 1.01 | 1.06 | 0.78 | 1.95 | 0.97 | 1.11 | 4.44 | 1.11 | 1.25 | 1.65 | 1.37 |
| Minos1 | 0.97 | 1.03 | 0.91 | 0.97 | 2.49 | 1.04 | 0.84 | 2.16 | 1.00 | 1.27 | 1.48 | 1.04 |
| Mir10a | 1.00 | 1.00 | 1.00 | 1.00 | 1.00 | 1.00 | 1.00 | 1.00 | 1.00 | 0.00 | 1.00 | 1.00 |
| Mir1291 | 1.00 | 1.00 | 1.00 | 1.00 | 1.00 | 0.07 | 1.00 | 1.00 | 0.05 | 1.00 | 65.60 | 36.62 |
| Mir142b | 1.00 | 1.00 | 1.00 | 1.00 | 1.00 | 0.03 | 1.00 | 1.00 | 0.04 | 0.57 | 2.00 | 0.78 |
| Mir1957b | 1.00 | 1.00 | 6.57 | 1.00 | 1.00 | 1.00 | 1.00 | 1.00 | 1.00 | 1.00 | 1.00 | 1.00 |
| Mir210 | 1.00 | 1.00 | 1.00 | 1.00 | 1.00 | 1.00 | 1.00 | 1.00 | 1.00 | 1.00 | 1.00 | 1.00 |
| Mir214 | 1.00 | 1.00 | 1.00 | 112.87 | 1.00 | 1.00 | 1.00 | 97.33 | 1.00 | 62.09 | 51.02 | 1.00 |
| Mir22hg | 1.11 | 1.05 | 1.00 | 1.43 | 0.70 | 0.96 | 0.75 | 0.60 | 0.95 | 1.01 | 0.91 | 0.74 |
| Mir365-2 | 1.00 | 1.00 | 1.00 | 1.00 | 1.00 | 1.00 | 1.00 | 1.00 | 1.00 | 1.00 | 1.00 | 1.00 |

Fig. 35- 208

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Map2 | 1.28 | 1.40 | 1.60 | 0.99 | 0.91 | 1.03 | 0.59 | 0.11 | 0.55 | 1.00 | 1.00 | 1.00 |
| Map2k2 | 1.30 | 1.08 | 1.06 | 0.90 | 0.68 | 1.06 | 1.18 | 8.12 | 0.93 | 2.57 | 1.20 | 0.97 |
| Map3k6 | 1.24 | 1.12 | 1.15 | 2.29 | 1.00 | 2.41 | 1.81 | 1.25 | 1.77 | 1.00 | 1.56 | 1.49 |
| Map6 | 1.00 | 1.00 | 1.00 | 1.08 | 0.76 | 1.02 | 0.63 | 0.30 | 0.63 | 1.00 | 1.00 | 1.00 |
| Mapk12 | 1.08 | 1.10 | 0.84 | 0.95 | 0.69 | 1.04 | 1.25 | 6.44 | 1.21 | 0.78 | 0.74 | 0.48 |
| Mapk13 | 1.62 | 2.23 | 1.94 | 1.00 | 0.72 | 1.00 | 1.32 | 17.22 | 0.79 | 3.49 | 1.07 | 0.96 |
| Mapk8ip2 | 1.00 | 1.00 | 1.00 | 0.99 | 1.23 | 0.99 | 1.00 | 1.00 | 1.00 | 1.00 | 1.00 | 1.00 |
| Mapt | 1.00 | 1.00 | 1.00 | 1.02 | 1.18 | 1.00 | 1.13 | 0.99 | 1.14 | 1.00 | 1.00 | 1.00 |
| Marc1 | 1.00 | 1.00 | 1.00 | 1.00 | 1.00 | 1.00 | 1.00 | 1.00 | 1.00 | 1.00 | 1.00 | 1.00 |
| Marc2 | 0.85 | 0.75 | 1.06 | 0.92 | 0.72 | 1.15 | 1.11 | 3.25 | 1.00 | 1.31 | 1.00 | 0.94 |
| March7 | 1.32 | 1.21 | 1.19 | 0.86 | 1.00 | 0.89 | 0.67 | 0.06 | 0.83 | 0.51 | 0.91 | 0.74 |
| Marco | 1.00 | 1.00 | 0.47 | 1.00 | 1.00 | 1.00 | 1.00 | 1.00 | 1.00 | 1.00 | 1.00 | 0.13 |
| Mars | 1.32 | 1.02 | 1.12 | 0.97 | 1.03 | 1.00 | 0.94 | 7.42 | 0.97 | 2.42 | 1.00 | 0.89 |
| Mat1a | 4.52 | 7.46 | 0.72 | 1.00 | 1.00 | 1.00 | 1.00 | 1.00 | 1.00 | 1.00 | 1.00 | 1.00 |
| Matk | 1.00 | 1.00 | 1.00 | 0.99 | 0.80 | 0.99 | 0.91 | 12.49 | 1.00 | 4.00 | 1.21 | 1.10 |
| Mb | 1.00 | 1.00 | 1.00 | 1.05 | 0.24 | 1.57 | 1.57 | 9.65 | 1.41 | 1.00 | 1.00 | 0.40 |
| Mbd1 | 1.84 | 2.11 | 1.32 | 0.96 | 2.07 | 1.19 | 1.89 | 2.53 | 1.23 | 1.05 | 1.08 | 1.00 |
| Mbp | 0.80 | 1.03 | 0.86 | 0.85 | 0.76 | 0.80 | 1.75 | 1.00 | 1.43 | 0.66 | 0.86 | 0.75 |
| Mc2r | 1.00 | 1.00 | 1.00 | 1.00 | 1.00 | 1.00 | 2.37 | 3.19 | 2.60 | 1.00 | 1.00 | 1.00 |
| Mc5r | 1.00 | 1.00 | 1.00 | 1.00 | 1.00 | 1.00 | 1.73 | 0.66 | 2.87 | 1.00 | 1.00 | 1.00 |
| Mcee | 0.50 | 0.52 | 0.60 | 0.86 | 7.06 | 0.93 | 0.98 | 1.11 | 0.95 | 1.36 | 1.20 | 1.26 |
| Mchr1 | 1.00 | 1.00 | 1.00 | 1.19 | 1.13 | 1.11 | 1.00 | 1.00 | 1.00 | 1.00 | 1.00 | 1.00 |
| Mcpt4 | 1.00 | 1.00 | 1.00 | 1.00 | 1.00 | 1.00 | 1.29 | 5.14 | 1.23 | 1.00 | 1.00 | 1.00 |
| Mcrs1 | 2.45 | 0.69 | 1.11 | 1.03 | 1.04 | 0.92 | 1.15 | 7.28 | 1.11 | 3.19 | 1.25 | 1.02 |
| Mcts1 | 0.70 | 0.73 | 0.66 | 1.16 | 0.76 | 1.14 | 0.87 | 2.94 | 1.02 | 1.72 | 1.10 | 1.38 |
| Mdp1 | 1.40 | 1.05 | 0.77 | 1.08 | 1.23 | 1.13 | 0.92 | 7.66 | 0.82 | 2.25 | 1.23 | 1.02 |
| Mecr | 0.90 | 1.14 | 1.14 | 1.05 | 0.97 | 0.83 | 1.15 | 6.50 | 0.83 | 2.03 | 0.79 | 0.95 |
| Med18 | 1.00 | 1.00 | 1.00 | 0.94 | 1.80 | 1.15 | 0.84 | 0.79 | 0.95 | 0.81 | 0.83 | 1.01 |
| Med29 | 1.36 | 1.19 | 0.83 | 1.47 | 0.94 | 0.96 | 1.33 | 6.29 | 0.90 | 1.88 | 0.96 | 0.95 |
| Med9os | 1.00 | 1.00 | 1.00 | 0.92 | 11.56 | 1.00 | 1.57 | 2.23 | 1.00 | 1.00 | 1.00 | 1.00 |
| Mef2b | 1.00 | 1.00 | 1.00 | 1.00 | 1.85 | 1.00 | 1.15 | 5.57 | 1.32 | 1.72 | 1.04 | 1.18 |
| Meg3 | 0.72 | 0.76 | 1.30 | 0.73 | 0.93 | 0.88 | 1.00 | 3.92 | 0.66 | 4.01 | 1.00 | 1.00 |
| Meig1 | 1.00 | 1.00 | 1.00 | 1.00 | 0.28 | 0.87 | 6.28 | 2.14 | 1.00 | 1.00 | 1.00 | 1.00 |
| Meis3 | 0.75 | 1.17 | 1.31 | 1.02 | 0.83 | 1.11 | 1.80 | 6.01 | 1.02 | 1.46 | 1.00 | 1.00 |
| Mepce | 1.12 | 1.16 | 1.01 | 1.05 | 0.94 | 1.03 | 1.21 | 6.30 | 1.10 | 2.30 | 0.97 | 0.96 |
| Mest | 1.00 | 1.00 | 1.00 | 0.93 | 1.05 | 0.92 | 0.71 | 5.81 | 0.71 | 1.00 | 0.85 | 1.00 |
| Metap1d | 0.64 | 0.93 | 0.50 | 0.49 | 1.37 | 0.91 | 1.04 | 9.55 | 0.92 | 2.58 | 1.00 | 1.06 |
| Metrn | 0.69 | 1.07 | 0.74 | 1.16 | 0.86 | 1.01 | 1.22 | 9.78 | 0.99 | 2.53 | 1.04 | 1.01 |
| Metrnl | 0.98 | 1.00 | 0.71 | 1.13 | 6.02 | 0.94 | 1.10 | 1.31 | 0.74 | 1.12 | 0.92 | 0.98 |
| Mettl10 | 0.74 | 1.05 | 1.22 | 1.11 | 5.04 | 0.89 | 0.66 | 0.68 | 0.76 | 0.79 | 1.10 | 0.76 |
| Mettl7b | 1.00 | 1.00 | 1.00 | 1.00 | 1.00 | 1.00 | 1.44 | 5.28 | 1.01 | 1.00 | 1.00 | 1.00 |
| Mfge8 | 0.98 | 1.68 | 0.97 | 0.98 | 0.82 | 0.85 | 1.08 | 10.34 | 0.97 | 2.95 | 1.28 | 0.99 |
| Mfsd2a | 1.00 | 1.00 | 1.00 | 1.43 | 2.48 | 1.34 | 1.80 | 2.80 | 1.34 | 1.00 | 1.00 | 1.00 |
| Mfsd6l | 1.18 | 1.24 | 1.00 | 1.00 | 1.00 | 1.00 | 1.03 | 6.59 | 1.40 | 2.48 | 0.71 | 1.31 |
| Mgmt | 1.12 | 0.61 | 0.81 | 1.00 | 2.40 | 1.58 | 1.29 | 9.45 | 0.67 | 3.91 | 0.72 | 0.61 |
| Mgp | 0.97 | 2.49 | 1.41 | 1.02 | 1.82 | 1.06 | 2.11 | 6.73 | 2.58 | 0.85 | 1.00 | 0.63 |
| Mgst2 | 1.00 | 1.00 | 1.00 | 1.00 | 0.63 | 1.00 | 1.17 | 7.68 | 0.88 | 3.50 | 1.78 | 1.48 |
| Mgst3 | 0.58 | 0.60 | 0.57 | 0.89 | 0.80 | 1.03 | 1.45 | 10.21 | 1.10 | 2.12 | 0.95 | 1.09 |
| Mia | 0.51 | 1.18 | 0.94 | 1.38 | 2.29 | 1.29 | 1.46 | 3.54 | 1.04 | 1.00 | 1.00 | 1.00 |
| Miat | 1.00 | 1.00 | 1.00 | 0.72 | 1.29 | 0.83 | 0.84 | 1.00 | 1.50 | 1.00 | 1.00 | 1.00 |
| Mical1 | 1.00 | 1.00 | 1.00 | 1.36 | 3.08 | 1.21 | 0.98 | 2.83 | 1.09 | 2.21 | 0.88 | 1.00 |
| Micall1 | 1.71 | 2.10 | 1.17 | 0.92 | 0.84 | 0.86 | 0.94 | 0.21 | 1.09 | 0.65 | 0.93 | 1.00 |
| Mif | 0.60 | 0.71 | 0.76 | 1.09 | 1.02 | 1.03 | 1.01 | 5.49 | 0.74 | 2.35 | 0.93 | 1.17 |
| Mif4gd | 1.40 | 0.99 | 0.91 | 0.93 | 0.99 | 1.08 | 1.21 | 0.58 | 0.89 | 0.75 | 0.95 | 1.06 |
| Miip | 0.97 | 0.58 | 1.02 | 0.81 | 0.95 | 1.19 | 1.54 | 10.21 | 1.12 | 4.19 | 1.55 | 1.25 |
| Minos1 | 0.92 | 1.26 | 0.92 | 1.01 | 1.10 | 1.08 | 1.23 | 5.00 | 1.20 | 2.49 | 1.22 | 1.11 |
| Mir10a | 1.00 | 1.00 | 1.00 | 1.00 | 1.00 | 1.00 | 1.00 | 1.00 | 1.00 | 1.00 | 1.00 | 1.00 |
| Mir1291 | 1.00 | 1.00 | 1.00 | 1.00 | 1.00 | 1.00 | 1.00 | 1.00 | 1.00 | 1.00 | 41.40 | 0.05 |
| Mir142b | 1.00 | 1.00 | 1.00 | 1.00 | 1.00 | 1.00 | 46.12 | 0.04 | 0.06 | 1.38 | 1.58 | 1.19 |
| Mir1957b | 1.00 | 1.00 | 1.00 | 1.00 | 1.00 | 1.00 | 1.00 | 1.00 | 1.00 | 1.00 | 1.00 | 1.00 |
| Mir210 | 1.00 | 1.00 | 1.00 | 1.00 | 1.00 | 1.00 | 1.00 | 1.00 | 1.00 | 1.00 | 1.00 | 1.00 |
| Mir214 | 1.00 | 1.00 | 1.00 | 1.00 | 1.00 | 1.00 | 1.00 | 1.00 | 1.00 | 1.00 | 1.00 | 1.00 |
| Mir22hg | 3.60 | 6.04 | 1.61 | 1.11 | 1.33 | 0.98 | 1.25 | 0.35 | 1.10 | 0.38 | 0.96 | 1.07 |
| Mir365-2 | 1.00 | 1.00 | 1.00 | 1.00 | 1.00 | 1.00 | 1.00 | 1.00 | 0.02 | 1.00 | 1.00 | 1.00 |

Fig. 35- 209

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Mir466i | 1.00 | 22.09 | 1.00 | 1.00 | 1.00 | 1.00 | 1.00 | 1.00 | 1.00 | 1.00 | 1.00 | 1.00 |
| Mir6236 | 0.83 | 0.52 | 0.34 | 11.24 | 1.39 | 2.45 | 0.43 | 0.47 | 1.14 | 12.43 | 2.79 | 2.42 |
| Mir6340 | 11.71 | 1.00 | 0.64 | 0.12 | 1.00 | 1.00 | 1.00 | 1.00 | 1.00 | 1.00 | 1.00 | 1.00 |
| Mir6357 | 1.00 | 1.00 | 1.00 | 1.00 | 1.00 | 1.00 | 1.00 | 1.00 | 1.00 | 1.00 | 1.00 | 1.00 |
| Mir6418 | 1.00 | 1.00 | 1.00 | 1.00 | 1.00 | 1.00 | 1.00 | 1.00 | 1.00 | 1.00 | 1.00 | 1.00 |
| Mir6538 | 1.00 | 1.00 | 1.00 | 112.12 | 1.00 | 1.00 | 1.00 | 1.00 | 1.00 | 1.00 | 1.00 | 1.00 |
| Mir682 | 1.00 | 1.00 | 0.00 | 1.99 | 10030 | 1.00 | 1.00 | 1.00 | 1.00 | 2.26 | 11.53 | 1.00 |
| Mir6992 | 1.00 | 1.00 | 1.00 | 1.00 | 1.00 | 1.00 | 1.00 | 1.00 | 1.00 | 1.00 | 1.00 | 30.58 |
| Mir7-1 | 1.00 | 1.00 | 1.00 | 0.06 | 1.00 | 1.00 | 1.00 | 1.00 | 1.00 | 1.00 | 1.00 | 35.02 |
| Mir703 | 1.59 | 0.47 | 1.00 | 0.02 | 535.10 | 0.00 | 31.12 | 0.01 | 2.28 | 1.73 | 2.48 | 0.81 |
| Mir719 | 29.05 | 1.00 | 1.00 | 1.00 | 1.00 | 1.00 | 1.00 | 1.00 | 1.00 | 1.00 | 1.00 | 1.00 |
| Mir760 | 1.00 | 1.00 | 1.00 | 1.00 | 1.00 | 16.69 | 1.00 | 1.00 | 1.00 | 1.00 | 1.00 | 1.00 |
| Mir8091 | 1.00 | 1.00 | 5.23 | 1.00 | 1.00 | 1.00 | 1.00 | 1.00 | 1.00 | 1.00 | 1.00 | 1.00 |
| Mir8093 | 1.00 | 1.00 | 1.00 | 1.00 | 1.00 | 1.00 | 1.00 | 1.00 | 1.00 | 1.00 | 1.00 | 1.00 |
| Mir8094 | 1.00 | 1.00 | 5.15 | 0.03 | 0.83 | 81.51 | 71.24 | 103.12 | 1.14 | 0.02 | 0.02 | 0.94 |
| Mir8097 | 1.00 | 0.02 | 1.00 | 0.32 | 141.90 | 1.00 | 1.00 | 1.00 | 0.19 | 4.15 | 22.15 | 1.00 |
| Mir8098 | 1.00 | 1.00 | 1.00 | 1.00 | 1.00 | 1.94 | 1.00 | 1.00 | 3.70 | 1.00 | 1.00 | 1.00 |
| Mir8099-1 | 1.00 | 1.00 | 1.00 | 1.00 | 1.00 | 1.00 | 1.00 | 1.00 | 1.00 | 1.00 | 1.00 | 6.93 |
| Mir8102 | 9.50 | 1.00 | 1.00 | 1.00 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 1.00 | 1.00 | 1.00 | 1.00 | 1.00 | 1.00 | 1.00 |
| Mir8112 | 1.00 | 1.00 | 0.12 | 0.16 | 1.00 | 16.27 | 0.44 | 1.00 | 2.28 | 1.00 | 1.00 | 0.40 |
| Mir8113 | 1.00 | 1.00 | 1.00 | 1.00 | 1.00 | 1.00 | 1.00 | 1.00 | 1.00 | 1.00 | 1.00 | 0.13 |
| Mir8114 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 1.00 | 1.00 | 1.00 | 1.00 | 1.00 | 1.00 |
| Mkl1 | 0.88 | 0.50 | 0.66 | 0.92 | 2.67 | 0.81 | 1.06 | 1.24 | 1.06 | 2.58 | 2.42 | 1.00 |
| Mlf1 | 1.92 | 1.03 | 0.79 | 1.51 | 4.96 | 1.11 | 0.56 | 0.50 | 0.44 | 1.20 | 2.21 | 0.92 |
| Mlkl | 1.00 | 1.00 | 1.00 | 0.91 | 2.12 | 0.80 | 0.97 | 0.69 | 1.77 | 3.06 | 2.13 | 1.12 |
| Mlx | 1.13 | 0.93 | 0.87 | 0.56 | 0.86 | 0.75 | 0.97 | 0.86 | 0.91 | 0.77 | 0.93 | 1.08 |
| Mmd2 | 1.00 | 1.00 | 1.00 | 0.39 | 0.42 | 1.01 | 1.00 | 1.00 | 1.00 | 1.00 | 1.00 | 1.00 |
| Mmp12 | 1.00 | 1.00 | 1.00 | 1.00 | 1.00 | 1.00 | 1.00 | 1.00 | 1.00 | 1.00 | 1.48 | 1.00 |
| Mmp23 | 0.75 | 0.38 | 1.15 | 0.44 | 3.58 | 0.72 | 0.92 | 0.83 | 0.82 | 2.17 | 2.27 | 0.87 |
| Mmp3 | 1.00 | 1.60 | 1.15 | 2.71 | 5.01 | 3.57 | 10.42 | 11.12 | 15.48 | 8.40 | 16.64 | 9.22 |
| Mmp7 | 1.00 | 1.00 | 1.00 | 1.00 | 1.00 | 1.00 | 1.00 | 1.00 | 1.00 | 1.00 | 1.00 | 1.00 |
| Mmp8 | 1.00 | 1.00 | 1.00 | 1.00 | 1.00 | 1.00 | 1.00 | 1.00 | 1.00 | 7.57 | 4.87 | 4.56 |
| Mms19 | 1.24 | 0.59 | 1.35 | 0.72 | 6.84 | 1.08 | 1.09 | 1.01 | 0.93 | 2.00 | 2.89 | 0.85 |
| Mnd1 | 1.00 | 1.38 | 0.77 | 0.39 | 9.07 | 1.53 | 1.00 | 1.00 | 1.00 | 1.15 | 2.33 | 1.00 |
| Mnda | 2.90 | 4.39 | 2.52 | 2.62 | 2.13 | 1.67 | 2.02 | 2.75 | 1.91 | 0.25 | 0.15 | 0.28 |
| Moap1 | 0.49 | 0.96 | 0.59 | 3.66 | 3.35 | 1.00 | 0.53 | 0.34 | 0.45 | 0.81 | 0.89 | 0.65 |
| Mobp | 1.00 | 1.00 | 1.00 | 1.00 | 0.15 | 1.00 | 1.00 | 1.00 | 1.00 | 1.00 | 1.00 | 1.00 |
| Mon1a | 1.12 | 0.87 | 0.90 | 0.60 | 2.46 | 0.91 | 1.42 | 1.24 | 1.26 | 2.90 | 2.52 | 1.14 |
| Morn3 | 1.00 | 1.00 | 1.00 | 1.00 | 1.00 | 1.00 | 1.00 | 1.00 | 1.00 | 3.01 | 2.66 | 1.00 |
| Mospd1 | 1.13 | 1.12 | 1.04 | 2.89 | 2.65 | 1.34 | 1.54 | 1.80 | 0.97 | 1.17 | 1.14 | 0.96 |
| Mpc1 | 0.99 | 1.32 | 0.79 | 0.63 | 0.84 | 0.83 | 0.74 | 0.92 | 0.76 | 0.32 | 0.56 | 0.94 |
| Mpc2 | 1.20 | 0.69 | 0.81 | 0.33 | 3.59 | 0.76 | 1.19 | 0.88 | 0.79 | 1.49 | 1.77 | 0.88 |
| Mpnd | 0.95 | 0.62 | 1.07 | 0.38 | 2.84 | 0.95 | 1.34 | 1.14 | 0.87 | 3.32 | 2.12 | 1.04 |
| Mpo | 1.00 | 1.00 | 1.00 | 1.00 | 1.00 | 1.00 | 1.00 | 1.00 | 1.00 | 1.00 | 1.00 | 1.00 |
| Mpp3 | 0.98 | 0.72 | 0.65 | 1.00 | 1.76 | 1.00 | 0.70 | 0.72 | 0.77 | 3.95 | 6.59 | 1.51 |
| Mpp7 | 1.00 | 1.00 | 1.00 | 2.65 | 0.53 | 1.27 | 3.76 | 5.25 | 3.31 | 0.73 | 0.60 | 1.00 |
| Mpped1 | 1.00 | 1.00 | 1.00 | 1.00 | 0.25 | 1.00 | 1.00 | 1.00 | 1.00 | 1.00 | 1.00 | 1.00 |
| Mpv17l2 | 1.41 | 0.52 | 0.76 | 0.45 | 11.10 | 0.94 | 0.97 | 0.92 | 1.08 | 4.14 | 6.70 | 1.18 |
| Mpzl2 | 2.97 | 2.95 | 2.42 | 4.14 | 1.49 | 2.48 | 1.06 | 1.32 | 1.36 | 0.61 | 1.11 | 1.23 |
| Mrap | 2.59 | 6.72 | 4.68 | 0.54 | 3.36 | 1.18 | 0.83 | 0.81 | 1.18 | 0.61 | 1.91 | 0.91 |
| Mrap2 | 1.41 | 1.89 | 2.09 | 2.73 | 7.38 | 3.18 | 39.40 | 24.46 | 22.31 | 32.16 | 38.85 | 14.28 |
| Mrgprg | 5.58 | 2.28 | 4.51 | 3.67 | 1.91 | 3.39 | 1.00 | 1.00 | 1.00 | 1.00 | 1.00 | 1.00 |
| Mri1 | 0.81 | 0.66 | 0.73 | 0.76 | 3.38 | 0.72 | 0.96 | 0.77 | 0.86 | 2.26 | 1.53 | 0.98 |
| Mroh1 | 1.50 | 0.61 | 1.26 | 0.53 | 1.89 | 0.98 | 1.31 | 1.13 | 1.10 | 3.08 | 2.79 | 1.08 |
| Mrpl11 | 0.96 | 0.53 | 0.96 | 0.52 | 8.57 | 0.90 | 0.80 | 0.96 | 0.82 | 2.71 | 3.76 | 1.12 |
| Mrpl12 | 1.05 | 0.51 | 0.80 | 0.25 | 5.58 | 0.70 | 0.82 | 0.88 | 0.77 | 2.48 | 3.57 | 0.94 |
| Mrpl13 | 1.37 | 0.51 | 0.97 | 0.40 | 6.30 | 0.72 | 1.23 | 1.05 | 0.82 | 2.01 | 3.06 | 0.85 |
| Mrpl14 | 1.92 | 0.94 | 1.25 | 0.69 | 9.23 | 1.20 | 1.19 | 1.09 | 1.02 | 2.38 | 3.90 | 1.20 |
| Mrpl2 | 1.05 | 0.59 | 0.78 | 0.21 | 4.19 | 0.92 | 1.28 | 0.78 | 0.83 | 2.63 | 2.76 | 0.96 |
| Mrpl22 | 1.42 | 0.74 | 0.81 | 0.28 | 2.76 | 1.07 | 0.96 | 0.54 | 0.53 | 0.78 | 1.46 | 0.69 |
| Mrpl23 | 1.16 | 0.41 | 0.81 | 0.44 | 15.43 | 0.94 | 0.86 | 0.80 | 0.86 | 3.29 | 5.50 | 0.78 |
| Mrpl24 | 1.35 | 0.78 | 1.03 | 0.63 | 4.55 | 0.91 | 1.02 | 0.92 | 0.88 | 3.27 | 2.62 | 1.11 |

Fig. 35- 210

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Mir466i | 1.00 | 1.00 | 1.00 | 1.00 | 1.00 | 1.00 | 1.00 | 1.00 | 1.00 | 1.00 | 1.00 | 1.00 |
| Mir6236 | 0.62 | 4.32 | 0.75 | 0.79 | 1.87 | 3.67 | 0.06 | 13.45 | 2.88 | 1.91 | 0.72 | 1.26 |
| Mir6340 | 1.00 | 1.00 | 0.06 | 1.00 | 1.00 | 0.15 | 1.00 | 1.00 | 1.00 | 1.00 | 1.00 | 0.03 |
| Mir6357 | 0.01 | 1.00 | 43.01 | 0.00 | 1.00 | 44.91 | 1.00 | 1.00 | 1.00 | 1.00 | 1.00 | 1.00 |
| Mir6418 | 1.00 | 1.00 | 0.05 | 1.00 | 1.00 | 1.00 | 1.00 | 1.00 | 1.00 | 0.01 | 1.00 | 1.00 |
| Mir6538 | 1.00 | 1.00 | 1.00 | 1.00 | 1.00 | 1.00 | 1.00 | 1.00 | 1.00 | 1.00 | 1.00 | 1.00 |
| Mir682 | 1.00 | 1.00 | 0.36 | 1.00 | 1.33 | 1.00 | 1.00 | 0.00 | 1.00 | 1.00 | 1.10 | 0.00 |
| Mir6992 | 1.00 | 1.00 | 1.00 | 1.00 | 1.00 | 1.00 | 1.00 | 1.00 | 1.00 | 1.00 | 1.00 | 1.00 |
| Mir7-1 | 0.01 | 1.00 | 0.01 | 1.00 | 1.00 | 1.00 | 1.00 | 1.00 | 1.00 | 152.78 | 1.00 | 1.00 |
| Mir703 | 236.46 | 5.12 | 1.22 | 0.01 | 0.57 | 0.01 | 0.89 | 0.72 | 0.58 | 3.83 | 2.47 | 6.36 |
| Mir719 | 1.00 | 1.00 | 1.00 | 1.00 | 1.00 | 1.00 | 1.00 | 1.00 | 1.00 | 1.00 | 1.00 | 1.00 |
| Mir760 | 1.00 | 1.00 | 1.00 | 1.00 | 1.00 | 1.00 | 1.00 | 1.00 | 1.00 | 1.00 | 1.00 | 1.00 |
| Mir8091 | 0.10 | 1.00 | 1.00 | 1.00 | 1.00 | 1.00 | 1.00 | 1.00 | 1.00 | 1.00 | 1.00 | 1.00 |
| Mir8093 | 1.00 | 1.00 | 1.00 | 17.41 | 1.00 | 1.00 | 1.00 | 1.00 | 0.20 | 1.00 | 1.00 | 1.00 |
| Mir8094 | 1.31 | 1.70 | 0.54 | 72.88 | 24.42 | 2.42 | 48.06 | 1.00 | 1.00 | 1.00 | 0.74 | 0.76 |
| Mir8097 | 1.00 | 1.00 | 1.00 | 1.00 | 0.62 | 1.00 | 1.00 | 7.72 | 1.00 | 1.00 | 1.00 | 1.00 |
| Mir8098 | 1.41 | 1.00 | 4.14 | 1.00 | 1.00 | 1.00 | 1.00 | 1.00 | 2.07 | 1.00 | 1.00 | 4.48 |
| Mir8099-1 | 0.03 | 15.34 | 7.13 | 32.26 | 1.00 | 0.13 | 1.00 | 1.00 | 0.12 | 1.00 | 2.18 | 12.49 |
| Mir8102 | 7.75 | 7.77 | 1.00 | 1.00 | 1.00 | 5.45 | 1.00 | 1.00 | 1.00 | 1.00 | 1.00 | 1.00 |
| Mir8104 | 1.00 | 1.00 | 1.00 | 1.00 | 1.00 | 70.50 | 1.00 | 1.00 | 1.00 | 1.00 | 1.00 | 1.00 |
| Mir8112 | 0.07 | 1.00 | 0.07 | 1.00 | 1.00 | 1.00 | 17.21 | 1.00 | 7.77 | 0.05 | 1.00 | 0.12 |
| Mir8113 | 0.26 | 3.48 | 1.71 | 1.00 | 1.00 | 1.00 | 1.00 | 1.00 | 1.00 | 1.00 | 1.00 | 1.00 |
| Mir8114 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 1.00 | 1.00 | 1.00 | 1.00 | 1.00 | 1.00 |
| Mkl1 | 0.86 | 0.93 | 1.06 | 0.88 | 0.56 | 0.94 | 1.30 | 4.11 | 1.14 | 0.93 | 0.94 | 0.98 |
| Mlf1 | 1.00 | 1.00 | 1.00 | 1.00 | 1.00 | 1.00 | 1.00 | 1.98 | 1.00 | 1.00 | 1.00 | 1.00 |
| Mlkl | 1.06 | 1.13 | 1.82 | 1.00 | 1.55 | 1.00 | 1.00 | 3.33 | 1.41 | 1.43 | 1.45 | 1.01 |
| Mlx | 0.89 | 0.91 | 0.95 | 0.97 | 1.18 | 0.93 | 0.83 | 0.72 | 0.88 | 0.99 | 1.12 | 1.02 |
| Mmd2 | 1.00 | 1.00 | 1.00 | 1.00 | 1.00 | 1.00 | 0.62 | 0.59 | 0.85 | 1.00 | 1.00 | 1.00 |
| Mmp12 | 1.00 | 1.00 | 7.23 | 1.00 | 1.00 | 1.00 | 1.00 | 1.00 | 1.00 | 1.00 | 1.00 | 1.00 |
| Mmp23 | 1.13 | 1.10 | 0.76 | 0.89 | 0.62 | 0.65 | 1.00 | 1.00 | 1.00 | 0.47 | 0.68 | 0.88 |
| Mmp3 | 1.83 | 2.30 | 1.93 | 1.00 | 1.00 | 1.00 | 1.00 | 1.00 | 1.00 | 1.00 | 1.10 | 1.00 |
| Mmp7 | 5.14 | 6.18 | 5.46 | 1.00 | 1.00 | 1.00 | 1.00 | 1.00 | 1.00 | 3.38 | 3.36 | 1.27 |
| Mmp8 | 0.45 | 1.00 | 1.00 | 1.00 | 1.00 | 1.00 | 1.00 | 1.00 | 1.00 | 1.00 | 1.00 | 1.00 |
| Mms19 | 1.12 | 1.33 | 0.95 | 1.00 | 0.74 | 1.02 | 0.87 | 1.26 | 1.00 | 1.13 | 1.48 | 1.07 |
| Mnd1 | 0.86 | 1.25 | 1.04 | 1.00 | 0.53 | 1.00 | 0.80 | 0.40 | 0.94 | 1.00 | 1.00 | 0.89 |
| Mnda | 0.52 | 0.57 | 0.66 | 1.00 | 1.00 | 1.00 | 1.00 | 1.00 | 1.00 | 0.43 | 0.57 | 0.50 |
| Moap1 | 0.70 | 0.65 | 1.17 | 0.57 | 0.68 | 1.00 | 1.27 | 1.00 | 1.00 | 1.71 | 5.71 | 1.00 |
| Mobp | 1.00 | 1.00 | 1.00 | 1.00 | 1.00 | 1.00 | 1.00 | 1.00 | 1.00 | 1.00 | 1.00 | 1.00 |
| Mon1a | 1.13 | 1.21 | 1.03 | 1.10 | 0.61 | 1.29 | 0.99 | 2.42 | 0.97 | 1.08 | 1.39 | 1.16 |
| Morn3 | 1.00 | 1.00 | 1.00 | 1.00 | 1.00 | 1.00 | 1.00 | 1.00 | 1.00 | 1.00 | 1.00 | 1.00 |
| Mospd1 | 1.00 | 1.06 | 1.04 | 1.59 | 0.99 | 1.09 | 0.89 | 1.32 | 0.84 | 1.05 | 0.97 | 1.12 |
| Mpc1 | 1.01 | 1.13 | 0.81 | 0.98 | 2.02 | 0.97 | 0.98 | 0.35 | 0.80 | 1.12 | 1.21 | 1.16 |
| Mpc2 | 1.01 | 1.38 | 0.76 | 0.75 | 0.85 | 1.08 | 1.22 | 1.64 | 1.05 | 0.82 | 1.29 | 0.87 |
| Mpnd | 0.81 | 1.08 | 0.87 | 0.93 | 0.51 | 1.27 | 0.91 | 2.98 | 0.84 | 1.21 | 1.13 | 0.95 |
| Mpo | 0.23 | 0.62 | 1.00 | 1.00 | 1.00 | 1.00 | 1.00 | 1.00 | 1.00 | 1.00 | 1.00 | 1.00 |
| Mpp3 | 1.00 | 1.00 | 1.00 | 1.00 | 1.00 | 1.00 | 1.00 | 1.00 | 1.00 | 1.01 | 1.05 | 1.21 |
| Mpp7 | 0.75 | 0.69 | 0.85 | 1.38 | 1.34 | 1.20 | 1.63 | 1.00 | 1.39 | 1.05 | 0.89 | 0.87 |
| Mpped1 | 1.00 | 1.00 | 1.00 | 1.50 | 1.13 | 1.11 | 1.00 | 1.00 | 1.00 | 1.00 | 1.00 | 1.00 |
| Mpv17l2 | 1.32 | 1.75 | 0.92 | 0.88 | 0.55 | 0.98 | 0.83 | 2.41 | 0.90 | 1.09 | 2.02 | 1.21 |
| Mpzl2 | 1.12 | 0.95 | 1.12 | 0.97 | 1.19 | 0.91 | 1.77 | 2.80 | 1.00 | 0.94 | 0.71 | 0.86 |
| Mrap | 1.85 | 2.63 | 1.07 | 1.10 | 0.63 | 1.31 | 1.68 | 1.04 | 1.27 | 1.14 | 3.48 | 1.00 |
| Mrap2 | 3.88 | 3.97 | 3.41 | 3.19 | 6.88 | 4.13 | 16.52 | 42.30 | 12.95 | 3.22 | 5.82 | 2.89 |
| Mrgprg | 1.60 | 1.53 | 1.43 | 1.00 | 1.00 | 1.00 | 1.00 | 1.00 | 1.00 | 1.00 | 1.00 | 1.00 |
| Mri1 | 0.96 | 0.98 | 1.05 | 0.84 | 0.59 | 1.00 | 1.10 | 1.67 | 0.81 | 1.22 | 1.29 | 0.97 |
| Mroh1 | 1.09 | 1.16 | 1.30 | 0.99 | 0.49 | 0.99 | 0.72 | 1.28 | 0.79 | 0.97 | 0.84 | 0.93 |
| Mrpl11 | 1.11 | 1.55 | 0.88 | 0.80 | 0.52 | 0.95 | 1.35 | 1.79 | 0.73 | 1.17 | 1.71 | 0.86 |
| Mrpl12 | 1.04 | 1.12 | 0.79 | 0.87 | 0.59 | 0.82 | 0.85 | 1.75 | 0.81 | 0.93 | 1.50 | 0.93 |
| Mrpl13 | 1.11 | 1.23 | 0.85 | 0.81 | 0.60 | 0.69 | 1.35 | 1.96 | 0.78 | 1.09 | 1.60 | 1.03 |
| Mrpl14 | 1.58 | 1.92 | 1.30 | 1.28 | 1.07 | 1.25 | 1.10 | 1.52 | 0.86 | 1.38 | 1.89 | 1.28 |
| Mrpl2 | 1.09 | 1.37 | 0.80 | 0.88 | 0.60 | 0.84 | 0.84 | 1.46 | 0.82 | 1.09 | 1.40 | 0.99 |
| Mrpl22 | 1.03 | 1.66 | 1.08 | 0.59 | 1.05 | 0.80 | 1.10 | 0.46 | 0.96 | 0.78 | 1.66 | 1.16 |
| Mrpl23 | 1.56 | 1.52 | 0.88 | 0.57 | 0.38 | 0.66 | 0.78 | 2.14 | 1.08 | 1.25 | 1.61 | 0.96 |
| Mrpl24 | 1.09 | 1.42 | 1.15 | 0.85 | 0.56 | 0.93 | 1.08 | 3.24 | 1.09 | 0.96 | 1.48 | 1.01 |

Fig. 35- 211

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Mir466i | 1.00 | 1.00 | 1.00 | 1.00 | 1.00 | 1.00 | 1.00 | 1.00 | 1.00 | 1.00 | 0.04 | 1.00 |
| Mir6236 | 0.51 | 0.85 | 1.01 | 3.74 | 0.06 | 1.70 | 0.43 | 3.69 | 1.18 | 0.67 | 0.42 | 0.59 |
| Mir6340 | 1.00 | 1.00 | 1.00 | 1.00 | 0.02 | 0.05 | 1.00 | 0.02 | 1.00 | 1.00 | 1.00 | 1.00 |
| Mir6357 | 1.00 | 228.02 | 1.00 | 1.00 | 1.00 | 1.00 | 1.00 | 1.00 | 1.00 | 1.00 | 1.00 | 1.00 |
| Mir6418 | 1.00 | 1.00 | 1.00 | 1.00 | 1.00 | 1.00 | 1.00 | 1.00 | 1.00 | 1.00 | 1.00 | 1.00 |
| Mir6538 | 1.00 | 1.00 | 1.00 | 1.00 | 1.00 | 1.00 | 1.00 | 1.00 | 1.00 | 1.00 | 1.00 | 1.00 |
| Mir682 | 0.00 | 1.00 | 1.00 | 1.00 | 0.00 | 0.00 | 20735 | 7.55 | 1.00 | 5574 | 0.44 | 7073 |
| Mir6992 | 1.00 | 1.00 | 1.00 | 1.00 | 1.00 | 1.00 | 1.00 | 1.00 | 1.00 | 1.00 | 1.00 | 1.00 |
| Mir7-1 | 1.00 | 1.00 | 1.00 | 1.00 | 1.00 | 1.00 | 1.00 | 1.00 | 1.00 | 1.00 | 0.01 | 0.02 |
| Mir703 | 1.22 | 0.01 | 1.96 | 0.00 | 2.05 | 1.23 | 1.00 | 0.24 | 1.00 | 0.00 | 3.14 | 0.00 |
| Mir719 | 1.00 | 1.00 | 1.00 | 1.00 | 1.00 | 1.00 | 1.00 | 1.00 | 1.00 | 1.00 | 0.10 | 1.00 |
| Mir760 | 1.00 | 1.00 | 1.00 | 0.03 | 1.00 | 1.00 | 48.35 | 1.00 | 16.80 | 1.00 | 1.00 | 1.00 |
| Mir8091 | 1.00 | 1.00 | 1.00 | 1.00 | 1.00 | 0.22 | 1.00 | 1.00 | 1.00 | 1.00 | 1.00 | 5.15 |
| Mir8093 | 1.00 | 1.00 | 1.00 | 1.00 | 1.00 | 1.00 | 1.00 | 1.00 | 6.21 | 1.00 | 1.00 | 1.00 |
| Mir8094 | 0.01 | 46.84 | 1.00 | 0.03 | 1.00 | 1.23 | 0.02 | 1.00 | 0.05 | 1.89 | 1.17 | 3.10 |
| Mir8097 | 1.00 | 1.00 | 1.00 | 1.00 | 1.00 | 1.00 | 1.00 | 10.88 | 1.00 | 1.00 | 1.00 | 1.00 |
| Mir8098 | 1.00 | 1.00 | 1.00 | 12.67 | 1.00 | 1.00 | 1.00 | 1.00 | 1.00 | 1.00 | 4.19 | 0.28 |
| Mir8099-1 | 1.00 | 1.00 | 2.02 | 1.00 | 1.00 | 0.13 | 0.05 | 1.00 | 10.08 | 1.00 | 15.18 | 27.74 |
| Mir8102 | 1.00 | 1.00 | 1.00 | 1.00 | 1.00 | 1.00 | 0.10 | 1.00 | 1.00 | 1.00 | 1.00 | 1.00 |
| Mir8104 | 1.00 | 1.00 | 1.00 | 1.00 | 1.00 | 1.00 | 1.00 | 1.00 | 1.00 | 1.00 | 1.00 | 1.00 |
| Mir8112 | 1.00 | 1.00 | 1.00 | 1.00 | 1.00 | 0.51 | 1.22 | 1.00 | 0.49 | 1.00 | 11.86 | 1.78 |
| Mir8113 | 1.00 | 1.00 | 0.13 | 1.00 | 1.00 | 1.00 | 1.00 | 1.00 | 1.00 | 1.00 | 0.06 | 0.89 |
| Mir8114 | 108.07 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 95.51 | 422.48 | 1.00 | 1.00 | 1.00 | 1.00 | 1.00 | 1.00 | 222.71 | 1.00 |
| Mkl1 | 0.89 | 0.85 | 0.85 | 1.11 | 1.72 | 0.91 | 1.09 | 2.73 | 1.18 | 1.01 | 0.91 | 1.08 |
| Mlf1 | 1.00 | 1.00 | 1.00 | 1.40 | 1.57 | 2.42 | 0.89 | 1.45 | 0.96 | 1.00 | 1.00 | 1.00 |
| Mlkl | 0.74 | 0.74 | 1.03 | 0.93 | 2.56 | 0.90 | 0.77 | 2.33 | 0.67 | 1.00 | 1.02 | 1.04 |
| Mlx | 0.84 | 0.76 | 0.88 | 0.96 | 3.35 | 1.62 | 0.95 | 0.58 | 1.11 | 0.95 | 0.88 | 0.94 |
| Mmd2 | 1.00 | 1.00 | 1.00 | 1.36 | 1.35 | 2.53 | 1.02 | 0.96 | 0.85 | 1.00 | 5.98 | 1.00 |
| Mmp12 | 0.41 | 0.38 | 0.71 | 0.14 | 1.00 | 0.03 | 1.00 | 1.00 | 1.00 | 0.68 | 0.98 | 1.00 |
| Mmp23 | 0.56 | 0.42 | 1.06 | 0.85 | 2.39 | 0.88 | 1.00 | 1.75 | 1.00 | 0.72 | 0.92 | 0.91 |
| Mmp3 | 0.74 | 0.56 | 1.00 | 3.97 | 1.00 | 4.50 | 1.00 | 1.00 | 1.00 | 1.68 | 2.89 | 1.35 |
| Mmp7 | 1.00 | 1.00 | 1.00 | 1.94 | 4.56 | 3.60 | 1.00 | 1.00 | 1.00 | 1.00 | 1.00 | 1.00 |
| Mmp8 | 1.00 | 1.00 | 1.00 | 1.00 | 1.00 | 1.00 | 1.00 | 1.00 | 1.00 | 14.73 | 7.11 | 8.32 |
| Mms19 | 1.32 | 1.04 | 1.06 | 0.84 | 2.37 | 1.01 | 0.89 | 1.49 | 1.07 | 1.00 | 1.07 | 1.04 |
| Mnd1 | 1.00 | 1.00 | 1.00 | 0.70 | 2.01 | 0.60 | 0.93 | 1.12 | 1.66 | 1.00 | 1.00 | 1.00 |
| Mnda | 1.29 | 1.89 | 1.00 | 1.40 | 1.73 | 1.20 | 1.00 | 1.00 | 1.00 | 0.15 | 0.13 | 0.22 |
| Moap1 | 1.00 | 0.55 | 1.00 | 0.75 | 1.00 | 0.93 | 0.94 | 0.81 | 0.65 | 1.03 | 2.22 | 1.00 |
| Mobp | 1.00 | 1.00 | 1.00 | 1.00 | 1.00 | 1.00 | 1.00 | 1.00 | 1.00 | 1.00 | 13.02 | 1.00 |
| Mon1a | 0.98 | 1.08 | 0.85 | 1.25 | 1.60 | 1.23 | 0.82 | 3.20 | 0.98 | 1.20 | 0.99 | 1.27 |
| Morn3 | 1.00 | 1.00 | 1.00 | 1.58 | 1.00 | 1.00 | 1.02 | 2.02 | 1.05 | 1.00 | 1.00 | 1.00 |
| Mospd1 | 1.41 | 1.22 | 1.29 | 1.81 | 7.29 | 1.40 | 1.01 | 0.94 | 0.65 | 0.99 | 0.86 | 1.01 |
| Mpc1 | 1.02 | 1.01 | 1.02 | 0.64 | 2.77 | 0.88 | 0.84 | 0.20 | 0.91 | 0.97 | 1.25 | 0.85 |
| Mpc2 | 1.09 | 1.10 | 0.92 | 0.94 | 3.60 | 1.09 | 0.97 | 1.30 | 1.04 | 0.90 | 1.28 | 0.72 |
| Mpnd | 0.96 | 1.31 | 1.18 | 0.68 | 1.23 | 0.71 | 0.80 | 3.92 | 0.80 | 0.86 | 1.09 | 0.97 |
| Mpo | 1.00 | 1.00 | 1.00 | 1.00 | 1.00 | 1.00 | 1.00 | 1.14 | 0.91 | 9.93 | 9.75 | 7.76 |
| Mpp3 | 0.81 | 0.67 | 0.65 | 1.16 | 2.21 | 1.20 | 0.84 | 1.67 | 1.09 | 0.68 | 0.98 | 0.83 |
| Mpp7 | 0.82 | 0.77 | 0.97 | 0.48 | 0.43 | 0.36 | 0.96 | 1.00 | 1.00 | 0.84 | 1.00 | 1.00 |
| Mpped1 | 1.00 | 1.00 | 1.00 | 1.00 | 1.00 | 1.00 | 1.39 | 1.00 | 1.19 | 1.00 | 6.04 | 1.00 |
| Mpv17l2 | 1.15 | 1.41 | 0.96 | 1.26 | 2.57 | 1.21 | 0.91 | 2.85 | 0.57 | 0.99 | 1.50 | 0.95 |
| Mpzl2 | 1.08 | 1.22 | 0.92 | 2.92 | 1.72 | 5.45 | 2.10 | 1.18 | 2.28 | 0.88 | 0.94 | 1.00 |
| Mrap | 1.50 | 3.73 | 1.00 | 2.33 | 8.21 | 1.57 | 0.76 | 0.60 | 0.43 | 1.12 | 1.21 | 1.59 |
| Mrap2 | 4.85 | 7.05 | 3.19 | 19.89 | 10.53 | 19.44 | 1.07 | 1.56 | 1.22 | 19.03 | 24.35 | 15.47 |
| Mrgprg | 1.00 | 1.00 | 1.00 | 3.24 | 1.00 | 5.36 | 1.00 | 1.00 | 1.00 | 1.00 | 1.00 | 1.00 |
| Mri1 | 0.92 | 1.34 | 0.85 | 0.70 | 2.78 | 1.00 | 0.89 | 1.35 | 0.68 | 0.90 | 1.03 | 1.07 |
| Mroh1 | 1.11 | 1.20 | 0.75 | 1.05 | 1.94 | 0.87 | 1.24 | 2.15 | 1.11 | 1.00 | 1.05 | 1.13 |
| Mrpl11 | 0.90 | 1.25 | 0.86 | 0.85 | 2.91 | 1.06 | 0.93 | 2.94 | 0.98 | 1.26 | 1.39 | 0.88 |
| Mrpl12 | 0.85 | 0.82 | 0.85 | 0.65 | 1.81 | 0.85 | 1.04 | 2.36 | 1.10 | 1.09 | 1.37 | 0.97 |
| Mrpl13 | 1.07 | 0.86 | 0.87 | 0.84 | 2.44 | 0.97 | 0.93 | 1.95 | 1.02 | 1.29 | 1.15 | 0.93 |
| Mrpl14 | 1.20 | 1.32 | 1.14 | 1.27 | 6.09 | 1.36 | 1.89 | 2.67 | 1.36 | 1.23 | 1.63 | 1.12 |
| Mrpl2 | 0.92 | 1.07 | 0.97 | 0.73 | 2.69 | 0.90 | 0.89 | 2.53 | 1.12 | 1.22 | 1.10 | 1.05 |
| Mrpl22 | 0.61 | 0.93 | 1.05 | 0.73 | 3.13 | 0.95 | 0.99 | 0.68 | 1.07 | 1.13 | 2.02 | 1.14 |
| Mrpl23 | 0.94 | 0.90 | 0.91 | 0.54 | 1.80 | 1.25 | 0.65 | 2.65 | 1.21 | 2.42 | 1.56 | 1.12 |
| Mrpl24 | 1.02 | 1.02 | 1.11 | 1.25 | 1.93 | 1.06 | 0.98 | 3.48 | 0.94 | 1.16 | 1.27 | 1.22 |

Fig. 35- 212

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Mir466i | 1.00 | 1.00 | 1.00 | 1.00 | 1.00 | 1.00 | 1.00 | 1.00 | 1.00 | 1.00 | 1.00 | 1.00 |
| Mir6236 | 2.10 | 1.45 | 1.13 | 1.56 | 0.86 | 1.66 | 1.85 | 31.36 | 2.10 | 0.25 | 2.55 | 2.09 |
| Mir6340 | 0.03 | 1.00 | 0.21 | 1.00 | 1.00 | 1.00 | 1.00 | 1.00 | 1.00 | 1.00 | 0.09 | 1.00 |
| Mir6357 | 1.00 | 1.00 | 1.00 | 1.00 | 1.00 | 1.00 | 1.00 | 0.02 | 1.00 | 1.00 | 1.00 | 0.98 |
| Mir6418 | 1.00 | 1.00 | 1.00 | 1.00 | 1.00 | 1.00 | 1.00 | 1.00 | 1.00 | 1.00 | 0.02 | 17.18 |
| Mir6538 | 1.00 | 1.00 | 1.00 | 1.00 | 1.00 | 1.00 | 1.00 | 1.00 | 1.00 | 1.00 | 1.00 | 1.00 |
| Mir682 | 1.00 | 2455 | 916.59 | 1.00 | 20899 | 1.00 | 0.00 | 68.60 | 0.58 | 29633 | 1.00 | 2216 |
| Mir6992 | 1.00 | 1.00 | 1.00 | 1.00 | 1.00 | 1.00 | 1.00 | 1.00 | 1.00 | 1.00 | 1.00 | 1.00 |
| Mir7-1 | 1.00 | 1.00 | 1.00 | 1.00 | 1.00 | 1.00 | 1.00 | 1.00 | 1.00 | 1.00 | 1.00 | 2.24 |
| Mir703 | 0.26 | 1.00 | 0.52 | 1.00 | 2.61 | 1.64 | 1.75 | 5.71 | 0.64 | 1.29 | 0.59 | 1.00 |
| Mir719 | 1.00 | 1.00 | 1.00 | 1.00 | 1.00 | 1.00 | 1.00 | 1.00 | 1.00 | 1.00 | 0.05 | 1.00 |
| Mir760 | 1.00 | 1.00 | 1.00 | 1.00 | 1.00 | 1.00 | 1.00 | 1.00 | 1.00 | 1.00 | 1.00 | 1.00 |
| Mir8091 | 1.00 | 1.00 | 1.00 | 1.00 | 1.00 | 1.00 | 1.00 | 1.00 | 1.00 | 1.00 | 1.00 | 1.00 |
| Mir8093 | 1.00 | 1.00 | 1.00 | 1.00 | 1.00 | 1.00 | 0.08 | 1.00 | 1.00 | 1.00 | 1.00 | 1.00 |
| Mir8094 | 1.00 | 1.00 | 1.00 | 1.00 | 1.00 | 2.52 | 114.06 | 0.03 | 0.43 | 92.00 | 4.67 | 1.79 |
| Mir8097 | 1.00 | 1.00 | 1.00 | 1.00 | 97.86 | 1.00 | 1.00 | 103.87 | 1.00 | 13.06 | 1.00 | 1.00 |
| Mir8098 | 1.00 | 1.00 | 1.00 | 1.00 | 1.00 | 0.15 | 1.00 | 1.00 | 0.51 | 1.00 | 10.08 | 1.00 |
| Mir8099-1 | 1.00 | 1.00 | 1.00 | 1.00 | 1.00 | 1.00 | 17.36 | 0.04 | 0.38 | 1.00 | 19.21 | 19.06 |
| Mir8102 | 1.00 | 1.00 | 1.00 | 1.00 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 0.02 | 1.00 | 1.00 | 1.00 | 1.00 | 1.00 | 114.24 |
| Mir8112 | 15.76 | 1.00 | 1.00 | 0.05 | 1.00 | 1.00 | 1.00 | 1.00 | 0.16 | 1.00 | 1.00 | 6.08 |
| Mir8113 | 1.00 | 1.00 | 1.00 | 1.00 | 1.00 | 1.00 | 1.00 | 1.00 | 1.00 | 1.00 | 1.00 | 6.72 |
| Mir8114 | 1.00 | 1.00 | 1.00 | 1.00 | 1.00 | 1.00 | 1.00 | 1.00 | 31.50 | 1.00 | 1.00 | 1.00 |
| Mirlet7d | 1.00 | 1.00 | 1.00 | 1.00 | 1.00 | 0.01 | 1.00 | 1.00 | 1.00 | 1.00 | 1.00 | 1.00 |
| Mkl1 | 1.15 | 1.00 | 1.00 | 1.11 | 1.09 | 1.15 | 1.12 | 5.12 | 1.03 | 2.23 | 1.06 | 1.12 |
| Mlf1 | 1.00 | 1.00 | 1.00 | 1.00 | 3.63 | 1.00 | 2.17 | 5.68 | 0.81 | 1.00 | 1.00 | 1.00 |
| Mlkl | 1.00 | 1.00 | 1.00 | 1.00 | 0.32 | 1.00 | 1.00 | 5.11 | 1.00 | 2.60 | 0.99 | 1.06 |
| Mlx | 1.18 | 1.15 | 1.15 | 1.18 | 6.84 | 1.06 | 1.01 | 0.95 | 0.93 | 0.74 | 1.09 | 1.35 |
| Mmd2 | 1.00 | 1.00 | 1.00 | 0.98 | 1.21 | 1.00 | 1.00 | 1.00 | 1.00 | 1.00 | 1.00 | 1.00 |
| Mmp12 | 1.00 | 1.00 | 1.00 | 1.00 | 1.00 | 1.00 | 1.00 | 1.00 | 1.00 | 1.00 | 1.00 | 1.00 |
| Mmp23 | 1.00 | 1.00 | 1.00 | 1.13 | 0.34 | 1.38 | 0.73 | 7.31 | 0.76 | 1.00 | 1.00 | 1.00 |
| Mmp3 | 1.00 | 1.00 | 1.00 | 1.00 | 1.00 | 1.00 | 0.72 | 1.69 | 0.61 | 1.00 | 1.00 | 1.00 |
| Mmp7 | 1.00 | 2.11 | 1.00 | 1.00 | 1.00 | 1.00 | 1.00 | 1.00 | 1.00 | 1.00 | 1.00 | 1.00 |
| Mmp8 | 1.00 | 1.00 | 1.00 | 1.00 | 1.00 | 1.00 | 1.00 | 1.00 | 1.00 | 1.99 | 2.91 | 2.02 |
| Mms19 | 1.08 | 0.85 | 0.89 | 0.93 | 1.12 | 0.98 | 0.99 | 5.91 | 0.99 | 2.81 | 1.18 | 1.22 |
| Mnd1 | 1.00 | 1.00 | 1.00 | 1.00 | 1.00 | 1.00 | 0.82 | 3.17 | 0.62 | 1.06 | 0.79 | 0.82 |
| Mnda | 1.00 | 1.00 | 1.00 | 1.00 | 1.00 | 1.00 | 8.95 | 7.76 | 5.36 | 0.16 | 0.10 | 0.14 |
| Moap1 | 1.00 | 1.00 | 1.00 | 1.49 | 1.50 | 1.53 | 1.00 | 2.20 | 1.42 | 1.04 | 1.00 | 1.47 |
| Mobp | 1.00 | 1.00 | 1.00 | 1.10 | 1.56 | 1.02 | 1.00 | 1.00 | 1.00 | 1.00 | 1.00 | 1.00 |
| Mon1a | 1.29 | 1.40 | 1.12 | 1.21 | 0.80 | 1.08 | 1.23 | 7.33 | 1.05 | 2.49 | 1.27 | 1.07 |
| Morn3 | 1.00 | 1.00 | 1.00 | 1.00 | 1.75 | 1.00 | 2.22 | 6.83 | 1.00 | 1.00 | 1.00 | 1.00 |
| Mospd1 | 1.21 | 1.15 | 1.22 | 0.99 | 0.52 | 0.93 | 1.09 | 1.43 | 1.12 | 1.00 | 1.09 | 0.93 |
| Mpc1 | 0.99 | 0.63 | 0.73 | 1.10 | 8.46 | 0.97 | 1.18 | 0.38 | 1.27 | 0.63 | 1.16 | 1.21 |
| Mpc2 | 1.90 | 2.00 | 1.65 | 1.05 | 0.72 | 1.05 | 1.26 | 5.80 | 1.28 | 2.22 | 1.10 | 1.19 |
| Mpnd | 0.92 | 0.78 | 0.84 | 1.26 | 0.82 | 1.01 | 1.09 | 7.80 | 0.87 | 2.48 | 1.33 | 1.11 |
| Mpo | 1.00 | 1.00 | 1.00 | 1.00 | 1.00 | 1.00 | 1.00 | 1.08 | 1.00 | 1.76 | 1.15 | 1.26 |
| Mpp3 | 1.00 | 1.00 | 1.00 | 1.14 | 1.02 | 1.06 | 1.00 | 2.11 | 1.00 | 1.00 | 1.00 | 1.00 |
| Mpp7 | 1.16 | 1.27 | 1.00 | 0.93 | 1.00 | 1.15 | 0.83 | 0.51 | 0.72 | 0.81 | 1.07 | 1.09 |
| Mpped1 | 1.00 | 1.00 | 1.00 | 1.16 | 0.93 | 1.04 | 1.00 | 1.00 | 1.00 | 1.00 | 1.00 | 1.00 |
| Mpv17l2 | 1.52 | 1.07 | 0.95 | 1.39 | 0.76 | 1.08 | 1.23 | 16.57 | 0.85 | 3.63 | 1.21 | 1.15 |
| Mpzl2 | 1.14 | 2.06 | 0.94 | 1.34 | 1.00 | 1.08 | 0.74 | 0.29 | 0.74 | 1.00 | 1.00 | 1.00 |
| Mrap | 1.00 | 1.00 | 1.00 | 1.00 | 0.37 | 1.00 | 11.86 | 17.19 | 2.48 | 1.49 | 1.40 | 0.60 |
| Mrap2 | 1.21 | 1.12 | 1.46 | 2.00 | 1.52 | 1.86 | 1.00 | 3.39 | 1.00 | 1.00 | 1.00 | 1.00 |
| Mrgprg | 1.00 | 1.00 | 1.00 | 1.00 | 1.00 | 1.00 | 1.00 | 2.06 | 1.00 | 1.00 | 1.00 | 1.00 |
| Mri1 | 1.53 | 0.91 | 0.98 | 1.15 | 5.74 | 1.04 | 0.99 | 1.83 | 0.93 | 1.46 | 0.86 | 0.80 |
| Mroh1 | 0.96 | 1.00 | 0.93 | 1.09 | 1.25 | 1.12 | 0.90 | 5.14 | 1.02 | 2.24 | 1.20 | 0.94 |
| Mrpl11 | 1.08 | 1.45 | 0.76 | 1.12 | 0.87 | 1.11 | 1.17 | 13.42 | 1.13 | 2.95 | 0.99 | 0.96 |
| Mrpl12 | 0.92 | 1.04 | 0.99 | 1.22 | 0.95 | 0.97 | 1.14 | 9.44 | 0.83 | 2.27 | 0.75 | 0.90 |
| Mrpl13 | 0.94 | 1.19 | 0.97 | 1.03 | 0.95 | 1.21 | 1.01 | 10.12 | 0.72 | 2.64 | 0.92 | 0.87 |
| Mrpl14 | 1.21 | 0.83 | 0.87 | 2.15 | 1.70 | 1.70 | 1.90 | 12.39 | 1.35 | 2.51 | 1.09 | 0.98 |
| Mrpl2 | 1.11 | 0.59 | 0.90 | 1.24 | 1.00 | 1.20 | 1.10 | 7.31 | 0.99 | 2.14 | 0.93 | 0.99 |
| Mrpl22 | 1.63 | 0.66 | 0.51 | 1.55 | 12.01 | 0.97 | 1.62 | 2.34 | 0.79 | 1.49 | 1.14 | 1.02 |
| Mrpl23 | 0.77 | 0.96 | 1.67 | 1.31 | 0.83 | 1.31 | 1.74 | 28.99 | 1.05 | 4.33 | 1.06 | 1.14 |
| Mrpl24 | 0.99 | 0.78 | 1.14 | 1.12 | 1.02 | 1.04 | 1.06 | 7.68 | 1.00 | 2.05 | 1.16 | 1.17 |

Fig. 35- 213

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Mrpl27 | 1.21 | 0.75 | 0.85 | 0.54 | 4.11 | 0.80 | 0.85 | 0.78 | 0.71 | 1.40 | 2.20 | 0.85 |
| Mrpl28 | 1.17 | 0.53 | 0.83 | 0.33 | 5.08 | 0.73 | 0.92 | 0.82 | 0.79 | 2.00 | 2.59 | 1.06 |
| Mrpl30 | 1.22 | 0.53 | 0.87 | 0.28 | 8.29 | 0.88 | 0.93 | 0.87 | 0.83 | 2.23 | 4.34 | 0.90 |
| Mrpl32 | 1.21 | 1.19 | 0.93 | 1.07 | 1.22 | 0.86 | 0.90 | 1.09 | 0.69 | 0.44 | 0.83 | 1.05 |
| Mrpl33 | 1.19 | 0.61 | 0.89 | 0.45 | 6.94 | 0.92 | 0.92 | 1.05 | 0.83 | 1.29 | 2.69 | 0.86 |
| Mrpl38 | 1.27 | 0.78 | 1.05 | 0.59 | 3.80 | 1.08 | 1.02 | 0.98 | 0.91 | 1.97 | 2.78 | 0.95 |
| Mrpl4 | 1.31 | 0.61 | 0.96 | 0.31 | 5.13 | 0.87 | 0.97 | 0.87 | 0.93 | 1.75 | 2.97 | 1.01 |
| Mrpl41 | 2.47 | 2.25 | 1.27 | 1.08 | 6.06 | 0.82 | 0.91 | 0.83 | 0.74 | 2.65 | 3.10 | 1.38 |
| Mrpl46 | 1.17 | 0.52 | 0.95 | 0.44 | 6.52 | 1.00 | 0.86 | 1.03 | 0.77 | 3.08 | 3.79 | 0.93 |
| Mrpl47 | 1.17 | 0.71 | 1.05 | 0.55 | 4.65 | 0.75 | 0.71 | 0.72 | 0.75 | 1.89 | 2.71 | 1.18 |
| Mrpl48 | 1.06 | 0.50 | 0.70 | 0.34 | 7.71 | 0.90 | 0.72 | 0.80 | 0.92 | 1.97 | 3.36 | 0.85 |
| Mrpl52 | 1.32 | 0.37 | 0.68 | 0.35 | 16.71 | 1.13 | 0.94 | 0.56 | 0.78 | 3.76 | 6.54 | 0.94 |
| Mrpl54 | 1.42 | 0.79 | 0.99 | 0.40 | 8.20 | 1.01 | 1.09 | 0.77 | 0.93 | 2.10 | 3.57 | 1.04 |
| Mrps10 | 1.05 | 0.92 | 0.78 | 0.92 | 2.04 | 0.94 | 1.17 | 0.83 | 0.81 | 0.80 | 1.49 | 0.88 |
| Mrps11 | 1.46 | 0.56 | 0.81 | 0.30 | 8.15 | 0.75 | 0.89 | 0.81 | 0.72 | 2.34 | 3.84 | 0.71 |
| Mrps12 | 1.16 | 0.59 | 0.95 | 0.40 | 5.97 | 0.94 | 0.93 | 0.81 | 0.83 | 1.98 | 3.14 | 1.03 |
| Mrps15 | 1.05 | 0.50 | 0.93 | 0.43 | 7.91 | 0.87 | 1.18 | 0.87 | 0.81 | 3.31 | 3.65 | 0.79 |
| Mrps16 | 0.90 | 0.44 | 0.75 | 0.37 | 6.26 | 0.79 | 0.75 | 0.73 | 0.78 | 1.91 | 3.54 | 1.02 |
| Mrps18a | 1.24 | 0.65 | 0.89 | 0.40 | 8.29 | 0.81 | 0.94 | 0.94 | 0.72 | 2.41 | 3.80 | 1.02 |
| Mrps18c | 1.10 | 0.29 | 0.69 | 0.19 | 12.11 | 0.54 | 0.90 | 0.87 | 0.97 | 3.30 | 3.36 | 1.19 |
| Mrps21 | 1.28 | 0.66 | 0.77 | 0.35 | 4.54 | 0.79 | 0.90 | 0.84 | 0.78 | 1.43 | 2.38 | 0.88 |
| Mrps24 | 1.15 | 0.55 | 0.80 | 0.38 | 7.64 | 0.73 | 0.82 | 0.77 | 0.75 | 2.20 | 3.74 | 0.92 |
| Mrps26 | 1.19 | 0.62 | 0.86 | 0.56 | 5.44 | 1.04 | 1.05 | 0.85 | 0.93 | 1.70 | 2.42 | 0.98 |
| Mrps6 | 0.94 | 0.75 | 1.24 | 0.63 | 2.51 | 0.75 | 1.02 | 0.85 | 0.85 | 1.67 | 2.32 | 0.81 |
| Mrto4 | 1.44 | 0.58 | 0.93 | 0.38 | 6.49 | 1.00 | 0.96 | 0.66 | 0.82 | 1.90 | 3.28 | 1.04 |
| Ms4a7 | 1.00 | 0.71 | 1.00 | 1.00 | 1.08 | 1.00 | 1.00 | 1.20 | 1.41 | 0.75 | 1.15 | 1.00 |
| Ms4a8a | 1.12 | 1.71 | 1.00 | 1.00 | 1.41 | 1.00 | 1.20 | 1.47 | 1.00 | 4.95 | 8.27 | 2.39 |
| Msrb1 | 1.21 | 0.73 | 0.83 | 0.39 | 8.93 | 1.21 | 1.33 | 1.10 | 1.05 | 3.03 | 4.47 | 1.13 |
| Msrb2 | 1.02 | 0.82 | 1.05 | 0.44 | 1.84 | 0.78 | 1.03 | 0.97 | 0.80 | 0.77 | 1.30 | 0.75 |
| Mst1 | 1.00 | 1.00 | 1.00 | 1.00 | 1.00 | 1.00 | 1.00 | 1.00 | 1.00 | 1.00 | 1.18 | 1.00 |
| Mstn | 1.43 | 6.18 | 1.23 | 1.00 | 1.00 | 1.00 | 1.00 | 1.00 | 1.00 | 1.00 | 1.00 | 1.00 |
| Msto1 | 1.17 | 0.61 | 1.10 | 0.28 | 8.17 | 0.97 | 0.85 | 0.75 | 0.84 | 0.39 | 2.02 | 1.14 |
| Mt1 | 11.98 | 9.75 | 5.42 | 0.22 | 20.62 | 2.57 | 1.87 | 1.42 | 1.68 | 3.03 | 7.87 | 1.45 |
| Mt2 | 17.49 | 12.79 | 8.25 | 0.72 | 32.32 | 2.94 | 2.34 | 2.37 | 3.00 | 3.46 | 11.70 | 1.95 |
| Mt3 | 4.98 | 1.01 | 1.53 | 1.00 | 0.69 | 1.00 | 0.90 | 1.00 | 1.81 | 4.30 | 2.37 | 1.00 |
| Mthfd2 | 1.72 | 2.93 | 1.55 | 0.68 | 1.00 | 1.23 | 2.07 | 1.73 | 3.14 | 1.33 | 0.77 | 0.97 |
| Mtmr14 | 1.37 | 1.18 | 1.19 | 1.84 | 7.48 | 1.16 | 1.57 | 1.36 | 1.27 | 1.20 | 1.62 | 1.06 |
| Mtmr7 | 1.00 | 0.58 | 1.00 | 1.00 | 3.09 | 1.00 | 1.00 | 1.00 | 1.00 | 1.98 | 4.86 | 0.86 |
| Mttp | 1.34 | 1.00 | 1.05 | 1.97 | 1.23 | 1.83 | 1.41 | 1.15 | 1.16 | 1.00 | 1.00 | 1.00 |
| Mtx1 | 1.33 | 0.63 | 0.74 | 0.31 | 7.14 | 0.88 | 0.95 | 0.75 | 0.72 | 2.34 | 4.17 | 0.90 |
| Muc13 | 1.00 | 1.00 | 1.00 | 1.00 | 1.00 | 1.00 | 1.00 | 1.00 | 1.00 | 1.00 | 1.00 | 1.00 |
| Mup1 | 2.71 | 3.07 | 1.00 | 1.57 | 5.20 | 2.38 | 5.81 | 0.49 | 1.00 | 0.13 | 3.02 | 1.21 |
| Mup10 | 2.35 | 2.36 | 1.00 | 1.00 | 0.75 | 1.00 | 3.40 | 0.48 | 1.00 | 0.44 | 1.00 | 1.00 |
| Mup12 | 3.28 | 2.72 | 1.00 | 1.00 | 1.04 | 1.49 | 8.65 | 0.31 | 1.35 | 0.17 | 1.00 | 1.00 |
| Mup13 | 1.71 | 4.92 | 1.00 | 1.07 | 7.46 | 1.33 | 3.47 | 0.67 | 1.00 | 0.15 | 1.19 | 1.00 |
| Mup15 | 4.91 | 1.45 | 1.00 | 1.76 | 3.69 | 1.74 | 13.08 | 0.32 | 1.89 | 0.02 | 3.14 | 2.51 |
| Mup16 | 1.00 | 1.00 | 1.00 | 1.00 | 1.00 | 1.00 | 1.00 | 1.00 | 1.00 | 1.00 | 1.00 | 1.00 |
| Mup17 | 1.00 | 1.00 | 1.00 | 1.00 | 1.00 | 1.00 | 1.00 | 1.00 | 1.00 | 1.00 | 1.00 | 1.00 |
| Mup2 | 9.94 | 4.15 | 1.00 | 2.97 | 5.46 | 1.27 | 12.04 | 0.27 | 2.35 | 0.04 | 3.03 | 1.73 |
| Mup3 | 1.00 | 0.50 | 1.00 | 1.00 | 2.25 | 0.95 | 2.77 | 0.24 | 1.00 | 0.10 | 1.00 | 1.00 |
| Mup8 | 1.70 | 2.36 | 1.00 | 1.00 | 5.87 | 1.15 | 4.47 | 0.60 | 1.00 | 0.14 | 2.66 | 1.00 |
| Mup9 | 6.89 | 5.37 | 1.00 | 1.23 | 5.47 | 1.75 | 11.64 | 0.49 | 1.69 | 0.16 | 3.14 | 1.29 |
| Musk | 6.60 | 9.47 | 4.55 | 1.00 | 1.00 | 1.00 | 1.00 | 1.00 | 1.00 | 1.00 | 1.00 | 1.00 |
| Mustn1 | 6.05 | 2.07 | 1.71 | 0.95 | 4.64 | 2.07 | 1.13 | 0.86 | 1.29 | 0.78 | 0.96 | 0.85 |
| Mvb12a | 0.93 | 0.43 | 0.98 | 0.26 | 9.10 | 0.89 | 0.97 | 0.87 | 1.03 | 2.94 | 4.08 | 1.07 |
| Mx1 | 1.00 | 1.00 | 1.00 | 1.00 | 1.00 | 1.00 | 1.00 | 1.00 | 1.00 | 1.00 | 1.20 | 1.65 |
| Mx2 | 1.00 | 1.00 | 1.00 | 1.00 | 1.70 | 1.00 | 1.00 | 1.00 | 1.00 | 2.81 | 2.76 | 1.37 |
| Mybpc2 | 1.38 | 1.32 | 1.55 | 2.59 | 3.21 | 1.89 | 2.17 | 1.96 | 2.10 | 1.00 | 1.00 | 1.00 |
| Mycl | 1.41 | 1.00 | 1.57 | 8.57 | 4.71 | 8.13 | 1.00 | 1.00 | 1.00 | 0.40 | 0.32 | 0.92 |
| Myeov2 | 1.35 | 0.48 | 0.80 | 0.27 | 15.14 | 1.00 | 0.91 | 0.80 | 0.76 | 3.13 | 5.49 | 0.98 |
| Myh1 | 0.93 | 0.43 | 1.27 | 0.72 | 4.76 | 0.81 | 1.00 | 1.00 | 1.00 | 1.00 | 1.00 | 1.00 |
| Myl10 | 0.98 | 0.42 | 0.83 | 1.00 | 1.00 | 1.00 | 1.00 | 1.00 | 1.00 | 1.00 | 1.00 | 1.00 |
| Myl2 | 1.61 | 0.13 | 0.93 | 1.00 | 1.72 | 0.69 | 0.68 | 0.64 | 0.62 | 1.52 | 1.11 | 1.00 |
| Myl3 | 1.18 | 0.21 | 1.01 | 0.60 | 1.75 | 0.33 | 0.97 | 0.87 | 0.81 | 7.95 | 10.30 | 3.81 |

Fig. 35- 214

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Mrpl27 | 1.18 | 1.53 | 1.03 | 0.86 | 0.79 | 0.86 | 0.70 | 0.80 | 0.88 | 1.11 | 1.71 | 1.02 |
| Mrpl28 | 1.12 | 1.37 | 0.81 | 0.95 | 0.73 | 0.90 | 0.86 | 1.16 | 0.74 | 0.89 | 1.46 | 1.10 |
| Mrpl30 | 1.16 | 1.83 | 1.04 | 0.79 | 0.69 | 0.77 | 1.10 | 1.84 | 0.94 | 0.98 | 1.94 | 1.08 |
| Mrpl32 | 1.04 | 1.15 | 0.98 | 0.98 | 1.67 | 0.95 | 1.09 | 0.44 | 1.14 | 1.15 | 1.26 | 1.02 |
| Mrpl33 | 1.06 | 1.36 | 0.88 | 0.69 | 0.74 | 0.84 | 1.11 | 0.85 | 0.97 | 1.03 | 1.62 | 1.05 |
| Mrpl38 | 1.11 | 1.36 | 0.97 | 0.94 | 0.77 | 0.85 | 1.22 | 1.46 | 0.86 | 0.90 | 1.29 | 0.91 |
| Mrpl4 | 1.31 | 1.56 | 0.88 | 0.82 | 0.75 | 0.98 | 0.89 | 0.88 | 0.88 | 1.13 | 1.62 | 0.97 |
| Mrpl41 | 1.25 | 1.52 | 1.07 | 0.77 | 1.50 | 0.78 | 0.97 | 1.97 | 0.91 | 1.05 | 1.49 | 0.86 |
| Mrpl46 | 1.09 | 1.41 | 0.84 | 1.06 | 0.60 | 0.95 | 1.03 | 2.19 | 0.80 | 1.14 | 1.50 | 1.07 |
| Mrpl47 | 1.33 | 1.37 | 1.00 | 0.63 | 0.67 | 0.67 | 0.98 | 1.72 | 0.85 | 0.86 | 1.30 | 0.83 |
| Mrpl48 | 1.15 | 1.73 | 1.00 | 0.71 | 0.60 | 0.69 | 0.82 | 1.13 | 0.89 | 0.94 | 1.71 | 1.04 |
| Mrpl52 | 1.22 | 1.40 | 0.93 | 0.44 | 0.50 | 0.77 | 1.09 | 2.45 | 1.03 | 0.85 | 2.30 | 0.93 |
| Mrpl54 | 1.23 | 1.81 | 0.91 | 0.81 | 0.84 | 0.84 | 1.46 | 2.40 | 1.24 | 1.12 | 1.86 | 1.03 |
| Mrps10 | 0.86 | 1.33 | 0.76 | 1.00 | 1.14 | 0.93 | 0.90 | 0.43 | 0.73 | 0.86 | 1.68 | 1.03 |
| Mrps11 | 1.05 | 1.58 | 0.80 | 0.82 | 0.60 | 0.80 | 1.06 | 1.87 | 1.04 | 0.95 | 1.40 | 1.04 |
| Mrps12 | 1.07 | 1.71 | 0.98 | 0.91 | 0.76 | 0.97 | 1.07 | 1.35 | 1.00 | 0.94 | 1.69 | 0.99 |
| Mrps15 | 1.10 | 1.59 | 0.76 | 0.75 | 0.46 | 0.91 | 1.27 | 2.85 | 0.88 | 1.15 | 1.75 | 0.79 |
| Mrps16 | 1.35 | 1.52 | 0.93 | 0.70 | 0.54 | 0.75 | 0.86 | 1.38 | 0.84 | 0.84 | 1.67 | 0.86 |
| Mrps18a | 1.15 | 1.31 | 0.89 | 0.88 | 0.65 | 0.83 | 1.23 | 1.82 | 0.73 | 1.07 | 1.85 | 1.14 |
| Mrps18c | 1.40 | 1.58 | 0.91 | 1.02 | 0.52 | 1.14 | 0.69 | 2.20 | 0.79 | 0.72 | 1.54 | 0.83 |
| Mrps21 | 0.94 | 1.34 | 0.84 | 0.66 | 0.75 | 0.91 | 0.90 | 0.74 | 0.70 | 0.99 | 1.70 | 0.99 |
| Mrps24 | 1.18 | 1.45 | 1.01 | 0.89 | 0.70 | 0.85 | 0.87 | 1.58 | 0.99 | 0.97 | 1.79 | 1.06 |
| Mrps26 | 1.00 | 1.22 | 0.94 | 0.84 | 0.80 | 0.92 | 1.04 | 1.41 | 0.96 | 0.94 | 1.62 | 0.98 |
| Mrps6 | 1.40 | 1.47 | 1.08 | 0.83 | 0.72 | 0.83 | 0.99 | 1.03 | 0.66 | 0.94 | 1.32 | 1.18 |
| Mrto4 | 1.09 | 1.20 | 0.81 | 0.85 | 0.63 | 1.20 | 0.88 | 1.29 | 1.00 | 1.06 | 1.46 | 0.83 |
| Ms4a7 | 2.82 | 3.16 | 1.83 | 1.00 | 1.00 | 1.00 | 1.00 | 1.00 | 1.00 | 1.43 | 1.86 | 1.16 |
| Ms4a8a | 1.00 | 1.03 | 2.32 | 1.00 | 1.00 | 1.00 | 1.54 | 8.20 | 1.64 | 1.21 | 1.73 | 1.15 |
| Msrb1 | 1.75 | 2.05 | 1.12 | 1.32 | 1.02 | 1.08 | 0.60 | 1.15 | 0.70 | 1.02 | 1.97 | 1.22 |
| Msrb2 | 1.35 | 1.51 | 1.05 | 0.97 | 1.08 | 0.90 | 0.93 | 0.75 | 1.02 | 1.04 | 1.38 | 0.85 |
| Mst1 | 0.95 | 1.12 | 0.97 | 1.00 | 1.00 | 1.00 | 0.88 | 1.66 | 0.94 | 1.00 | 1.00 | 1.00 |
| Mstn | 1.00 | 1.00 | 1.00 | 1.00 | 1.00 | 1.00 | 1.00 | 1.00 | 1.00 | 1.00 | 1.00 | 1.00 |
| Msto1 | 1.58 | 1.55 | 0.86 | 1.08 | 1.27 | 0.88 | 1.09 | 1.03 | 1.21 | 1.07 | 1.62 | 1.22 |
| Mt1 | 4.56 | 5.12 | 2.16 | 0.86 | 1.18 | 1.05 | 2.07 | 2.80 | 1.93 | 1.91 | 4.61 | 1.85 |
| Mt2 | 3.10 | 4.00 | 2.41 | 1.24 | 1.23 | 1.27 | 2.41 | 2.93 | 2.08 | 2.48 | 6.06 | 2.34 |
| Mt3 | 1.11 | 1.00 | 1.00 | 1.00 | 2.03 | 1.00 | 1.00 | 1.00 | 1.00 | 1.68 | 3.31 | 1.08 |
| Mthfd2 | 0.74 | 0.73 | 0.77 | 1.62 | 0.74 | 0.96 | 1.00 | 1.00 | 1.00 | 0.85 | 1.26 | 1.02 |
| Mtmr14 | 1.07 | 1.40 | 0.93 | 1.01 | 1.19 | 0.93 | 0.97 | 1.01 | 0.92 | 1.09 | 1.58 | 1.15 |
| Mtmr7 | 0.78 | 1.12 | 1.00 | 1.17 | 0.96 | 1.07 | 0.82 | 1.06 | 0.70 | 1.05 | 2.66 | 0.79 |
| Mttp | 1.71 | 1.07 | 0.70 | 0.62 | 0.42 | 0.70 | 1.72 | 0.97 | 1.37 | 1.39 | 1.21 | 1.76 |
| Mtx1 | 1.26 | 1.90 | 0.88 | 0.83 | 0.55 | 0.92 | 1.18 | 1.61 | 0.81 | 1.11 | 1.49 | 0.96 |
| Muc13 | 2.46 | 2.30 | 2.40 | 1.00 | 1.00 | 1.00 | 1.00 | 1.00 | 1.00 | 1.15 | 1.05 | 1.06 |
| Mup1 | 17.09 | 1.15 | 2.38 | 1.00 | 0.47 | 1.37 | 2.89 | 2.63 | 2.46 | 1.96 | 1.09 | 1.84 |
| Mup10 | 7.27 | 1.00 | 1.01 | 1.00 | 1.00 | 0.69 | 2.74 | 1.21 | 2.42 | 1.65 | 1.00 | 1.00 |
| Mup12 | 11.62 | 1.94 | 1.39 | 1.17 | 1.00 | 1.00 | 2.17 | 1.37 | 1.98 | 3.87 | 1.00 | 2.30 |
| Mup13 | 8.07 | 1.56 | 2.25 | 1.00 | 1.00 | 0.93 | 3.01 | 2.27 | 2.40 | 1.00 | 1.00 | 1.34 |
| Mup15 | 15.11 | 1.92 | 3.20 | 0.89 | 0.88 | 1.15 | 2.63 | 2.04 | 2.27 | 5.36 | 3.21 | 1.97 |
| Mup16 | 1.00 | 1.00 | 1.00 | 1.00 | 1.00 | 1.00 | 3.94 | 8.07 | 2.69 | 1.00 | 1.00 | 1.00 |
| Mup17 | 1.00 | 1.00 | 1.00 | 1.00 | 1.00 | 1.00 | 3.04 | 1.37 | 2.09 | 1.00 | 1.00 | 1.00 |
| Mup2 | 13.84 | 1.30 | 2.61 | 1.26 | 0.40 | 0.96 | 3.25 | 2.34 | 2.53 | 3.50 | 2.37 | 4.41 |
| Mup3 | 6.61 | 1.13 | 0.58 | 1.00 | 1.00 | 1.00 | 1.00 | 0.86 | 0.97 | 1.28 | 1.00 | 1.00 |
| Mup8 | 12.86 | 1.41 | 1.53 | 1.00 | 0.63 | 1.00 | 3.18 | 2.56 | 2.60 | 1.48 | 1.14 | 1.00 |
| Mup9 | 17.58 | 2.04 | 1.30 | 1.63 | 0.72 | 1.62 | 4.44 | 4.31 | 3.15 | 4.83 | 1.14 | 1.98 |
| Musk | 1.00 | 1.00 | 1.00 | 1.00 | 1.00 | 1.00 | 1.00 | 1.00 | 1.00 | 1.59 | 1.00 | 0.99 |
| Mustn1 | 2.60 | 2.20 | 1.82 | 0.75 | 1.09 | 1.14 | 3.13 | 1.23 | 2.47 | 1.09 | 1.33 | 1.15 |
| Mvb12a | 1.42 | 1.64 | 1.16 | 0.89 | 0.58 | 0.95 | 0.95 | 1.73 | 0.74 | 1.06 | 1.84 | 1.19 |
| Mx1 | 1.79 | 2.17 | 2.89 | 1.00 | 1.00 | 1.00 | 1.00 | 1.00 | 1.00 | 2.26 | 1.32 | 1.32 |
| Mx2 | 4.03 | 3.48 | 2.65 | 1.00 | 1.82 | 1.00 | 1.69 | 0.53 | 1.87 | 1.54 | 1.79 | 1.00 |
| Mybpc2 | 1.00 | 1.00 | 1.00 | 1.00 | 1.00 | 1.00 | 1.00 | 1.00 | 1.00 | 1.00 | 1.00 | 1.00 |
| Mycl | 1.49 | 1.09 | 1.56 | 1.21 | 1.00 | 0.92 | 1.73 | 1.24 | 1.72 | 0.81 | 0.80 | 1.04 |
| Myeov2 | 1.28 | 1.57 | 1.03 | 0.95 | 0.59 | 1.02 | 1.10 | 2.27 | 0.86 | 1.04 | 2.16 | 1.17 |
| Myh1 | 1.00 | 1.00 | 1.00 | 1.00 | 1.00 | 1.00 | 1.00 | 1.00 | 1.00 | 1.00 | 1.00 | 0.85 |
| Myl10 | 1.47 | 1.13 | 1.24 | 1.00 | 1.00 | 1.00 | 1.00 | 1.00 | 1.00 | 1.00 | 1.00 | 1.00 |
| Myl2 | 1.00 | 1.00 | 1.00 | 1.00 | 1.00 | 1.00 | 1.00 | 1.00 | 1.00 | 1.00 | 1.00 | 1.00 |
| Myl3 | 1.00 | 1.00 | 1.00 | 1.00 | 1.00 | 1.00 | 1.00 | 1.00 | 1.00 | 1.00 | 1.00 | 0.85 |

Fig. 35- 215

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Mrpl27 | 1.09 | 0.92 | 0.94 | 0.85 | 2.34 | 0.95 | 0.90 | 1.46 | 0.77 | 1.07 | 1.24 | 0.88 |
| Mrpl28 | 0.84 | 0.92 | 0.87 | 0.71 | 2.23 | 0.69 | 1.07 | 1.92 | 0.86 | 0.97 | 1.30 | 0.80 |
| Mrpl30 | 1.10 | 1.03 | 1.21 | 0.88 | 2.68 | 1.13 | 0.99 | 2.02 | 0.92 | 1.30 | 1.57 | 1.12 |
| Mrpl32 | 1.07 | 1.15 | 0.82 | 1.05 | 1.26 | 1.15 | 1.01 | 0.40 | 0.92 | 1.24 | 1.03 | 1.06 |
| Mrpl33 | 0.96 | 0.91 | 1.00 | 0.87 | 3.03 | 1.00 | 0.85 | 1.18 | 0.90 | 1.26 | 1.22 | 1.05 |
| Mrpl38 | 0.86 | 1.24 | 0.98 | 1.06 | 5.05 | 1.23 | 1.06 | 1.94 | 1.04 | 0.97 | 1.12 | 0.85 |
| Mrpl4 | 0.85 | 1.02 | 1.09 | 0.84 | 3.22 | 0.96 | 0.88 | 1.68 | 0.75 | 1.12 | 1.25 | 0.96 |
| Mrpl41 | 1.01 | 1.00 | 0.89 | 1.28 | 12.67 | 1.37 | 0.59 | 0.95 | 0.59 | 1.12 | 1.37 | 0.91 |
| Mrpl46 | 1.02 | 1.24 | 1.06 | 1.08 | 4.21 | 1.06 | 0.98 | 2.82 | 1.02 | 1.09 | 1.44 | 0.89 |
| Mrpl47 | 1.09 | 0.76 | 1.48 | 0.67 | 2.39 | 1.41 | 1.02 | 2.17 | 0.98 | 1.15 | 1.21 | 0.95 |
| Mrpl48 | 0.87 | 1.03 | 0.99 | 0.77 | 2.90 | 0.96 | 0.83 | 2.29 | 1.29 | 1.11 | 1.00 | 0.92 |
| Mrpl52 | 1.03 | 0.83 | 1.05 | 1.33 | 1.33 | 1.06 | 0.89 | 4.59 | 0.78 | 0.91 | 1.24 | 1.13 |
| Mrpl54 | 1.04 | 1.00 | 1.05 | 1.34 | 3.06 | 0.88 | 0.84 | 2.18 | 1.02 | 1.16 | 1.29 | 1.05 |
| Mrps10 | 1.05 | 0.72 | 0.86 | 0.92 | 6.65 | 1.00 | 0.89 | 0.70 | 0.92 | 1.12 | 1.21 | 0.95 |
| Mrps11 | 1.09 | 0.92 | 1.03 | 0.80 | 1.93 | 0.94 | 0.93 | 3.14 | 0.94 | 0.92 | 1.49 | 0.52 |
| Mrps12 | 0.94 | 1.02 | 1.06 | 0.93 | 4.42 | 0.90 | 0.93 | 1.65 | 1.14 | 1.00 | 1.35 | 0.88 |
| Mrps15 | 0.85 | 1.09 | 0.70 | 0.81 | 1.28 | 0.92 | 0.81 | 3.54 | 1.22 | 1.08 | 0.97 | 0.98 |
| Mrps16 | 0.94 | 0.89 | 0.86 | 0.71 | 2.16 | 0.97 | 1.02 | 2.05 | 0.88 | 1.07 | 1.19 | 0.96 |
| Mrps18a | 1.02 | 1.09 | 0.98 | 1.20 | 3.82 | 1.82 | 0.89 | 2.34 | 0.99 | 1.15 | 1.50 | 0.89 |
| Mrps18c | 1.27 | 1.00 | 0.26 | 0.57 | 4.93 | 0.51 | 1.00 | 1.71 | 0.71 | 1.00 | 2.17 | 1.06 |
| Mrps21 | 0.90 | 0.99 | 0.92 | 0.75 | 2.85 | 1.02 | 0.63 | 1.23 | 0.78 | 1.02 | 1.26 | 0.80 |
| Mrps24 | 0.86 | 0.89 | 0.93 | 0.79 | 2.12 | 1.04 | 0.71 | 2.14 | 0.87 | 1.08 | 1.54 | 1.03 |
| Mrps26 | 0.84 | 0.81 | 0.91 | 0.96 | 2.85 | 1.15 | 0.94 | 1.79 | 1.04 | 1.29 | 1.39 | 1.12 |
| Mrps6 | 0.94 | 1.19 | 1.09 | 0.75 | 1.24 | 0.55 | 0.80 | 1.58 | 0.78 | 1.09 | 1.17 | 0.95 |
| Mrto4 | 1.01 | 0.87 | 1.15 | 1.11 | 3.07 | 1.01 | 1.02 | 2.06 | 1.12 | 1.15 | 1.53 | 0.91 |
| Ms4a7 | 1.29 | 0.60 | 0.75 | 1.02 | 1.61 | 0.81 | 1.00 | 1.93 | 1.00 | 2.18 | 1.24 | 0.98 |
| Ms4a8a | 0.88 | 0.87 | 0.72 | 2.14 | 12.95 | 1.01 | 1.00 | 1.00 | 1.00 | 0.99 | 1.22 | 1.17 |
| Msrb1 | 1.05 | 1.45 | 1.22 | 0.62 | 1.46 | 0.86 | 0.60 | 2.45 | 0.68 | 1.14 | 1.26 | 0.87 |
| Msrb2 | 0.99 | 1.12 | 1.09 | 0.72 | 5.31 | 0.84 | 1.41 | 1.51 | 0.99 | 1.06 | 1.71 | 1.00 |
| Mst1 | 1.00 | 1.00 | 1.00 | 1.00 | 1.00 | 1.00 | 1.00 | 1.00 | 1.00 | 1.00 | 1.00 | 1.00 |
| Mstn | 1.00 | 1.00 | 1.00 | 1.00 | 1.00 | 1.00 | 1.00 | 1.00 | 1.00 | 1.00 | 1.00 | 1.00 |
| Msto1 | 0.97 | 1.30 | 0.94 | 1.17 | 1.48 | 1.10 | 0.84 | 2.04 | 0.96 | 0.93 | 1.31 | 0.82 |
| Mt1 | 1.52 | 2.26 | 1.62 | 4.03 | 19.37 | 2.97 | 0.96 | 0.99 | 0.97 | 1.92 | 3.35 | 1.20 |
| Mt2 | 1.59 | 2.48 | 1.80 | 5.39 | 38.16 | 3.94 | 0.91 | 1.29 | 0.97 | 3.97 | 4.75 | 1.02 |
| Mt3 | 1.00 | 1.00 | 1.88 | 0.66 | 1.64 | 2.36 | 1.00 | 2.73 | 0.61 | 1.00 | 10.68 | 1.00 |
| Mthfd2 | 1.08 | 1.00 | 1.33 | 1.02 | 1.43 | 0.56 | 1.03 | 1.23 | 0.98 | 0.73 | 0.63 | 0.73 |
| Mtmr14 | 0.90 | 1.39 | 1.12 | 1.15 | 6.43 | 1.23 | 1.03 | 1.04 | 0.95 | 1.03 | 1.12 | 0.93 |
| Mtmr7 | 0.74 | 0.71 | 0.98 | 1.00 | 1.00 | 1.00 | 1.00 | 0.69 | 1.00 | 1.00 | 2.78 | 1.00 |
| Mttp | 5.39 | 2.33 | 3.99 | 1.28 | 1.00 | 1.65 | 0.92 | 0.73 | 0.97 | 1.17 | 0.95 | 1.00 |
| Mtx1 | 1.00 | 0.91 | 0.83 | 0.83 | 2.57 | 0.94 | 0.99 | 2.82 | 1.09 | 0.96 | 1.15 | 0.89 |
| Muc13 | 5.94 | 3.62 | 5.54 | 1.00 | 1.00 | 1.00 | 1.00 | 1.00 | 1.00 | 1.32 | 0.82 | 0.70 |
| Mup1 | 3.95 | 10.29 | 5.03 | 0.81 | 2.25 | 1.29 | 1.00 | 1.66 | 1.00 | 1.00 | 4.82 | 1.00 |
| Mup10 | 4.36 | 9.20 | 6.36 | 1.00 | 1.00 | 1.10 | 1.00 | 1.00 | 1.00 | 1.00 | 2.07 | 1.00 |
| Mup12 | 3.51 | 6.92 | 5.11 | 0.79 | 1.00 | 1.38 | 0.60 | 1.00 | 0.97 | 1.00 | 4.40 | 0.85 |
| Mup13 | 3.56 | 8.92 | 8.20 | 0.82 | 1.00 | 1.00 | 1.00 | 1.00 | 1.00 | 1.00 | 2.74 | 1.00 |
| Mup15 | 3.56 | 8.49 | 8.03 | 0.77 | 3.59 | 1.86 | 0.93 | 5.65 | 0.63 | 1.00 | 10.60 | 1.22 |
| Mup16 | 1.00 | 1.00 | 1.00 | 1.00 | 1.00 | 1.00 | 1.00 | 1.00 | 1.00 | 1.00 | 1.00 | 1.00 |
| Mup17 | 1.00 | 1.00 | 11.21 | 1.00 | 1.00 | 1.00 | 1.37 | 1.00 | 1.00 | 1.00 | 1.00 | 1.00 |
| Mup2 | 3.72 | 8.21 | 8.15 | 0.85 | 0.89 | 1.34 | 1.00 | 1.63 | 0.73 | 1.00 | 12.04 | 0.77 |
| Mup3 | 1.80 | 4.36 | 3.02 | 0.75 | 1.00 | 1.00 | 1.00 | 1.10 | 1.00 | 1.00 | 1.06 | 1.00 |
| Mup8 | 5.64 | 12.68 | 9.29 | 1.00 | 2.37 | 1.00 | 1.00 | 1.00 | 1.00 | 1.00 | 3.40 | 1.00 |
| Mup9 | 4.41 | 8.79 | 6.01 | 1.85 | 1.99 | 1.01 | 1.63 | 1.82 | 0.96 | 1.00 | 9.92 | 1.11 |
| Musk | 1.56 | 1.19 | 1.01 | 1.00 | 1.00 | 1.00 | 1.00 | 1.00 | 1.00 | 1.00 | 1.00 | 1.00 |
| Mustn1 | 0.91 | 1.02 | 1.08 | 1.36 | 2.91 | 1.15 | 1.00 | 0.69 | 1.09 | 1.29 | 1.48 | 1.02 |
| Mvb12a | 0.92 | 0.95 | 1.06 | 0.64 | 0.85 | 1.08 | 0.69 | 3.59 | 1.11 | 0.95 | 1.16 | 0.81 |
| Mx1 | 3.85 | 5.39 | 3.54 | 1.08 | 1.00 | 1.27 | 1.12 | 1.00 | 0.96 | 6.14 | 4.58 | 3.58 |
| Mx2 | 1.92 | 2.49 | 1.10 | 1.38 | 1.00 | 1.00 | 1.00 | 1.78 | 1.00 | 6.58 | 5.81 | 3.38 |
| Mybpc2 | 1.00 | 1.00 | 1.25 | 1.00 | 1.00 | 1.00 | 1.00 | 1.00 | 1.00 | 1.55 | 1.45 | 1.72 |
| Mycl | 0.83 | 0.73 | 1.13 | 2.09 | 0.70 | 2.10 | 1.00 | 1.00 | 1.00 | 0.53 | 0.43 | 0.72 |
| Myeov2 | 0.92 | 1.05 | 1.03 | 0.65 | 2.47 | 0.77 | 0.87 | 3.06 | 0.89 | 1.18 | 1.43 | 0.92 |
| Myh1 | 4.17 | 1.53 | 2.41 | 1.00 | 1.00 | 1.00 | 1.00 | 1.04 | 1.00 | 1.00 | 1.00 | 1.00 |
| Myl10 | 1.00 | 1.00 | 1.00 | 1.00 | 1.00 | 1.00 | 0.93 | 1.42 | 0.76 | 1.00 | 1.00 | 1.00 |
| Myl2 | 1.00 | 1.00 | 1.00 | 1.00 | 1.00 | 1.00 | 1.00 | 1.89 | 1.00 | 1.00 | 1.00 | 1.00 |
| Myl3 | 2.36 | 1.37 | 2.10 | 1.00 | 1.00 | 1.00 | 1.00 | 1.79 | 1.00 | 1.00 | 1.00 | 1.00 |

Fig. 35- 216

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Mrpl27 | 0.90 | 0.86 | 0.87 | 1.24 | 1.25 | 1.10 | 1.23 | 5.11 | 1.00 | 1.74 | 1.11 | 0.97 |
| Mrpl28 | 0.80 | 0.67 | 0.79 | 1.05 | 0.99 | 1.15 | 1.05 | 6.60 | 0.93 | 2.12 | 1.01 | 1.03 |
| Mrpl30 | 1.05 | 0.89 | 0.99 | 1.08 | 1.26 | 1.09 | 1.25 | 9.69 | 0.91 | 3.12 | 1.20 | 1.26 |
| Mrpl32 | 0.78 | 0.78 | 0.69 | 0.93 | 7.51 | 1.03 | 1.05 | 0.83 | 1.15 | 1.03 | 1.42 | 1.12 |
| Mrpl33 | 1.00 | 0.92 | 0.91 | 0.98 | 2.09 | 0.83 | 1.15 | 6.95 | 1.10 | 2.79 | 1.22 | 1.22 |
| Mrpl38 | 1.24 | 0.94 | 0.98 | 0.86 | 0.93 | 1.06 | 1.27 | 4.98 | 1.00 | 1.74 | 0.90 | 1.04 |
| Mrpl4 | 1.15 | 1.37 | 1.22 | 1.17 | 1.32 | 1.04 | 1.31 | 6.93 | 1.07 | 2.60 | 1.12 | 1.19 |
| Mrpl41 | 1.32 | 1.09 | 1.09 | 0.92 | 2.48 | 0.88 | 1.30 | 4.29 | 1.07 | 1.95 | 1.04 | 1.14 |
| Mrpl46 | 1.59 | 0.93 | 0.80 | 1.16 | 0.90 | 1.02 | 1.00 | 9.23 | 0.95 | 2.54 | 1.51 | 1.01 |
| Mrpl47 | 0.53 | 1.16 | 0.80 | 0.65 | 1.07 | 0.75 | 0.93 | 8.71 | 0.79 | 2.13 | 0.82 | 0.65 |
| Mrpl48 | 1.15 | 1.02 | 0.98 | 0.95 | 0.77 | 1.00 | 1.08 | 11.38 | 0.92 | 2.69 | 1.11 | 1.16 |
| Mrpl52 | 1.73 | 1.39 | 0.61 | 1.67 | 0.95 | 1.04 | 1.37 | 30.30 | 0.98 | 3.87 | 0.68 | 0.97 |
| Mrpl54 | 0.73 | 1.48 | 1.18 | 1.00 | 1.03 | 1.13 | 1.15 | 11.79 | 0.84 | 3.24 | 0.98 | 1.36 |
| Mrps10 | 0.95 | 0.70 | 0.76 | 1.21 | 0.57 | 1.11 | 1.17 | 2.14 | 0.80 | 1.02 | 0.93 | 1.21 |
| Mrps11 | 0.77 | 0.56 | 0.69 | 1.13 | 0.77 | 1.26 | 1.13 | 13.75 | 1.04 | 2.62 | 1.17 | 1.10 |
| Mrps12 | 1.00 | 0.80 | 1.07 | 1.22 | 1.13 | 1.10 | 1.30 | 8.61 | 0.90 | 2.35 | 1.03 | 1.13 |
| Mrps15 | 1.55 | 0.91 | 1.29 | 1.30 | 0.87 | 1.22 | 1.03 | 17.26 | 0.81 | 3.64 | 1.17 | 0.97 |
| Mrps16 | 0.64 | 0.69 | 0.88 | 0.95 | 0.80 | 1.03 | 1.25 | 8.82 | 0.87 | 2.58 | 1.24 | 1.09 |
| Mrps18a | 0.72 | 0.94 | 0.88 | 0.98 | 1.14 | 1.15 | 1.34 | 13.68 | 0.99 | 2.78 | 1.02 | 1.09 |
| Mrps18c | 1.00 | 1.00 | 0.94 | 1.03 | 1.32 | 0.78 | 1.86 | 11.37 | 1.13 | 2.21 | 2.27 | 1.21 |
| Mrps21 | 1.17 | 0.98 | 0.57 | 1.02 | 2.91 | 0.92 | 1.24 | 5.63 | 0.97 | 2.90 | 1.46 | 1.33 |
| Mrps24 | 0.81 | 0.87 | 0.70 | 0.98 | 0.83 | 1.05 | 1.01 | 10.84 | 0.99 | 2.68 | 1.33 | 1.34 |
| Mrps26 | 0.93 | 0.78 | 0.82 | 1.12 | 1.11 | 1.06 | 1.05 | 4.90 | 0.90 | 2.67 | 1.01 | 1.07 |
| Mrps6 | 1.52 | 1.02 | 0.88 | 1.25 | 1.04 | 1.03 | 0.83 | 5.18 | 0.67 | 1.51 | 1.06 | 1.11 |
| Mrto4 | 0.99 | 1.82 | 1.52 | 1.38 | 1.06 | 1.20 | 1.06 | 6.24 | 0.93 | 2.50 | 0.87 | 1.05 |
| Ms4a7 | 1.00 | 1.00 | 1.00 | 1.00 | 1.00 | 1.00 | 1.18 | 5.60 | 0.86 | 2.45 | 1.57 | 0.99 |
| Ms4a8a | 1.00 | 1.00 | 1.00 | 1.00 | 1.00 | 1.00 | 1.00 | 1.47 | 1.00 | 12.05 | 7.21 | 4.68 |
| Msrb1 | 0.97 | 1.00 | 0.95 | 1.16 | 1.05 | 1.16 | 1.07 | 10.42 | 0.95 | 3.99 | 1.71 | 1.40 |
| Msrb2 | 0.84 | 0.52 | 0.95 | 1.14 | 0.50 | 0.92 | 1.50 | 2.65 | 1.29 | 1.17 | 0.97 | 0.89 |
| Mst1 | 1.00 | 1.00 | 1.00 | 1.00 | 1.00 | 1.00 | 1.48 | 5.36 | 1.08 | 1.00 | 1.00 | 0.97 |
| Mstn | 1.00 | 1.00 | 1.00 | 1.00 | 1.00 | 1.00 | 1.16 | 0.84 | 2.71 | 1.00 | 1.00 | 1.00 |
| Msto1 | 1.00 | 1.00 | 1.04 | 1.25 | 1.00 | 1.07 | 1.29 | 3.81 | 0.76 | 2.08 | 1.00 | 1.07 |
| Mt1 | 1.13 | 0.93 | 0.79 | 1.45 | 1.94 | 1.48 | 2.28 | 15.07 | 1.67 | 3.36 | 1.70 | 1.51 |
| Mt2 | 1.23 | 1.10 | 0.83 | 1.39 | 1.44 | 1.35 | 2.99 | 17.14 | 1.73 | 4.83 | 2.60 | 2.03 |
| Mt3 | 1.00 | 1.00 | 1.00 | 1.29 | 0.96 | 1.29 | 2.04 | 40.93 | 1.98 | 1.00 | 1.00 | 1.00 |
| Mthfd2 | 1.13 | 2.08 | 0.79 | 0.99 | 5.73 | 1.24 | 2.09 | 5.05 | 1.73 | 1.21 | 1.03 | 0.88 |
| Mtmr14 | 1.21 | 1.45 | 1.04 | 1.13 | 0.78 | 0.96 | 1.16 | 3.00 | 1.08 | 1.69 | 1.42 | 1.23 |
| Mtmr7 | 1.00 | 1.00 | 1.00 | 1.11 | 0.94 | 1.01 | 0.98 | 21.36 | 1.04 | 3.27 | 1.00 | 1.00 |
| Mttp | 1.00 | 1.00 | 1.00 | 0.84 | 0.41 | 0.81 | 1.30 | 1.27 | 1.11 | 1.00 | 1.00 | 1.00 |
| Mtx1 | 0.72 | 0.89 | 0.89 | 1.02 | 0.91 | 0.83 | 1.13 | 9.74 | 0.98 | 3.18 | 1.56 | 1.27 |
| Muc13 | 1.00 | 1.00 | 1.00 | 1.00 | 1.00 | 1.00 | 1.00 | 1.00 | 1.00 | 0.52 | 1.11 | 0.91 |
| Mup1 | 1.00 | 1.00 | 0.96 | 0.71 | 1.40 | 1.16 | 1.00 | 1.01 | 1.00 | 1.00 | 1.00 | 1.00 |
| Mup10 | 1.00 | 1.00 | 1.00 | 1.00 | 1.00 | 1.16 | 1.00 | 1.00 | 1.00 | 1.00 | 1.00 | 1.00 |
| Mup12 | 1.00 | 1.00 | 0.84 | 0.23 | 1.00 | 1.22 | 1.00 | 1.00 | 1.38 | 1.00 | 1.00 | 1.00 |
| Mup13 | 1.00 | 1.00 | 1.00 | 1.00 | 1.00 | 1.00 | 1.00 | 1.00 | 1.00 | 1.00 | 1.00 | 1.00 |
| Mup15 | 1.00 | 1.00 | 0.97 | 0.27 | 1.00 | 1.08 | 1.00 | 1.00 | 1.12 | 1.00 | 1.00 | 1.00 |
| Mup16 | 1.00 | 1.00 | 1.00 | 1.00 | 1.00 | 1.00 | 1.00 | 1.00 | 1.00 | 1.00 | 1.00 | 1.00 |
| Mup17 | 1.00 | 1.00 | 1.00 | 1.00 | 1.00 | 1.00 | 1.00 | 1.00 | 1.00 | 1.00 | 1.00 | 1.00 |
| Mup2 | 1.00 | 1.00 | 0.59 | 0.51 | 1.00 | 1.27 | 1.00 | 1.14 | 0.81 | 1.00 | 1.00 | 1.00 |
| Mup3 | 1.00 | 1.00 | 1.00 | 0.68 | 1.00 | 1.00 | 1.00 | 1.00 | 1.00 | 0.91 | 1.00 | 1.00 |
| Mup8 | 1.00 | 1.00 | 1.00 | 1.00 | 1.00 | 1.00 | 1.00 | 1.00 | 1.00 | 1.00 | 1.00 | 1.00 |
| Mup9 | 1.00 | 1.00 | 0.69 | 0.65 | 1.00 | 1.66 | 1.00 | 1.00 | 1.99 | 1.00 | 1.00 | 1.00 |
| Musk | 1.00 | 1.00 | 1.00 | 1.00 | 1.00 | 1.00 | 1.28 | 1.85 | 1.58 | 1.00 | 1.00 | 1.00 |
| Mustn1 | 1.00 | 1.00 | 1.00 | 1.05 | 1.71 | 1.02 | 1.67 | 3.72 | 1.60 | 1.00 | 1.00 | 1.05 |
| Mvb12a | 1.01 | 0.59 | 0.89 | 0.82 | 0.84 | 1.37 | 1.09 | 19.68 | 0.93 | 3.43 | 1.79 | 1.67 |
| Mx1 | 1.00 | 1.00 | 1.00 | 1.00 | 1.00 | 1.00 | 1.00 | 1.00 | 1.10 | 2.74 | 4.33 | 3.96 |
| Mx2 | 1.00 | 1.00 | 1.00 | 1.00 | 0.64 | 1.00 | 1.00 | 1.52 | 1.31 | 4.56 | 1.35 | 1.07 |
| Mybpc2 | 1.00 | 1.00 | 1.00 | 1.00 | 1.00 | 1.00 | 1.61 | 5.92 | 3.82 | 1.00 | 0.90 | 1.00 |
| Myci | 1.00 | 1.00 | 1.00 | 1.12 | 1.00 | 1.35 | 0.57 | 0.11 | 0.59 | 0.81 | 1.22 | 1.18 |
| Myeov2 | 0.83 | 0.89 | 0.87 | 1.06 | 1.01 | 1.16 | 1.20 | 24.21 | 1.00 | 3.90 | 1.18 | 1.47 |
| Myh1 | 1.00 | 1.00 | 1.00 | 1.00 | 0.73 | 1.00 | 1.32 | 26.47 | 1.94 | 1.00 | 1.00 | 1.00 |
| Myl10 | 1.00 | 1.00 | 1.00 | 1.00 | 1.00 | 1.00 | 2.06 | 7.05 | 1.29 | 1.00 | 1.00 | 1.00 |
| Myl2 | 1.00 | 1.00 | 1.00 | 1.00 | 3.58 | 1.00 | 1.18 | 21.52 | 0.67 | 2.39 | 1.00 | 1.00 |
| Myl3 | 1.00 | 1.00 | 1.00 | 1.00 | 1.00 | 1.00 | 1.40 | 10.43 | 1.00 | 1.00 | 1.00 | 1.00 |

Fig. 35- 217

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Myl4 | 2.79 | 1.01 | 0.54 | 0.66 | 3.21 | 0.70 | 0.54 | 0.56 | 1.49 | 1.74 | 2.21 | 0.76 |
| Myl6 | 1.38 | 0.72 | 1.06 | 0.26 | 8.10 | 1.08 | 0.92 | 0.75 | 1.07 | 3.51 | 3.72 | 0.94 |
| Mylpf | 1.17 | 0.82 | 0.81 | 0.60 | 5.69 | 1.21 | 0.42 | 1.11 | 0.84 | 1.20 | 2.03 | 1.00 |
| Myo1b | 0.91 | 0.94 | 0.94 | 5.54 | 5.09 | 3.18 | 0.87 | 1.07 | 1.08 | 0.81 | 0.66 | 0.94 |
| Myo9b | 1.13 | 0.67 | 1.40 | 0.97 | 2.96 | 0.92 | 0.95 | 1.05 | 1.25 | 2.32 | 2.76 | 1.10 |
| Myom1 | 0.82 | 0.83 | 0.85 | 0.89 | 1.38 | 0.65 | 1.07 | 1.16 | 1.01 | 1.35 | 1.59 | 0.99 |
| Myzap | 1.11 | 1.30 | 1.50 | 1.66 | 1.96 | 1.71 | 0.95 | 1.03 | 0.96 | 0.54 | 0.57 | 1.21 |
| N6amt2 | 0.96 | 0.67 | 0.64 | 0.42 | 3.61 | 0.83 | 0.74 | 0.59 | 0.64 | 0.93 | 1.96 | 0.76 |
| Naa10 | 0.84 | 0.49 | 0.73 | 0.34 | 10.00 | 1.07 | 0.90 | 0.99 | 0.85 | 2.07 | 3.14 | 0.96 |
| Naa38 | 1.19 | 0.81 | 1.07 | 0.25 | 2.46 | 0.87 | 1.25 | 0.82 | 0.73 | 0.61 | 1.65 | 1.02 |
| Nanos3 | 1.00 | 1.00 | 1.00 | 1.00 | 1.00 | 1.00 | 0.97 | 1.00 | 1.00 | 3.61 | 4.09 | 1.00 |
| Nap1l2 | 1.00 | 1.00 | 1.00 | 1.00 | 0.24 | 1.00 | 1.00 | 1.00 | 1.00 | 1.00 | 1.00 | 1.00 |
| Nap1l5 | 1.00 | 1.00 | 1.00 | 3.46 | 0.46 | 2.81 | 0.81 | 1.44 | 1.17 | 1.00 | 1.53 | 1.78 |
| Napb | 1.40 | 1.48 | 1.59 | 1.98 | 0.10 | 1.30 | 1.46 | 1.09 | 1.14 | 1.00 | 1.00 | 1.14 |
| Napsa | 1.00 | 1.00 | 1.00 | 1.00 | 1.13 | 1.00 | 1.00 | 1.00 | 1.00 | 1.72 | 2.87 | 1.05 |
| Nat9 | 1.16 | 0.51 | 1.14 | 0.48 | 19.34 | 1.27 | 1.08 | 0.89 | 0.74 | 4.29 | 5.63 | 0.85 |
| Ncald | 0.74 | 1.00 | 1.08 | 1.36 | 0.09 | 0.70 | 0.98 | 0.85 | 0.94 | 0.32 | 0.29 | 0.68 |
| Ncam1 | 1.44 | 1.31 | 1.05 | 1.08 | 0.30 | 1.16 | 1.41 | 1.12 | 0.91 | 1.00 | 1.00 | 1.00 |
| Ncf1 | 3.04 | 1.30 | 2.97 | 1.55 | 3.61 | 1.74 | 1.67 | 2.27 | 2.28 | 3.24 | 2.85 | 0.99 |
| Ncs1 | 0.79 | 1.00 | 0.94 | 1.00 | 0.16 | 1.00 | 1.04 | 0.97 | 1.05 | 1.00 | 1.35 | 1.42 |
| Ndrg4 | 0.84 | 1.00 | 1.03 | 1.00 | 0.03 | 1.00 | 0.46 | 0.41 | 0.40 | 1.00 | 0.63 | 0.51 |
| Ndufa10 | 1.06 | 0.72 | 0.87 | 0.48 | 1.70 | 0.89 | 1.03 | 1.07 | 0.80 | 1.11 | 1.51 | 1.02 |
| Ndufa11 | 1.23 | 0.37 | 0.76 | 0.13 | 7.09 | 0.75 | 1.02 | 0.85 | 0.82 | 2.80 | 3.68 | 0.77 |
| Ndufa13 | 1.02 | 0.44 | 0.75 | 0.10 | 9.04 | 0.87 | 0.93 | 0.76 | 0.66 | 2.10 | 3.73 | 0.83 |
| Ndufa2 | 1.07 | 0.41 | 0.80 | 0.23 | 18.87 | 0.85 | 1.00 | 0.78 | 0.77 | 4.18 | 6.64 | 0.98 |
| Ndufa3 | 1.51 | 0.29 | 0.88 | 0.13 | 20.70 | 0.72 | 0.92 | 0.68 | 0.73 | 5.54 | 9.58 | 1.00 |
| Ndufa4 | 1.20 | 0.43 | 0.83 | 0.25 | 12.56 | 0.83 | 0.89 | 0.77 | 0.73 | 3.23 | 4.93 | 1.01 |
| Ndufa4l2 | 1.04 | 0.48 | 1.01 | 0.49 | 7.75 | 1.05 | 0.98 | 0.75 | 0.82 | 1.69 | 3.01 | 0.93 |
| Ndufa5 | 1.18 | 0.39 | 0.83 | 0.23 | 9.06 | 0.88 | 0.91 | 0.78 | 0.71 | 3.37 | 3.75 | 0.94 |
| Ndufa7 | 1.68 | 0.84 | 1.09 | 0.28 | 6.28 | 1.25 | 1.01 | 0.77 | 0.95 | 2.12 | 3.98 | 1.34 |
| Ndufa9 | 1.01 | 0.67 | 0.91 | 0.25 | 3.52 | 0.91 | 1.01 | 0.85 | 0.77 | 1.45 | 2.16 | 0.87 |
| Ndufb10 | 0.92 | 0.62 | 0.77 | 0.24 | 3.62 | 0.76 | 1.06 | 0.84 | 0.74 | 1.64 | 2.02 | 0.84 |
| Ndufb5 | 1.12 | 0.42 | 0.85 | 0.38 | 10.04 | 0.82 | 1.00 | 0.87 | 0.87 | 3.89 | 4.17 | 1.05 |
| Ndufb6 | 1.10 | 0.62 | 0.78 | 0.36 | 3.79 | 0.74 | 1.04 | 0.79 | 0.79 | 1.61 | 2.55 | 0.90 |
| Ndufb7 | 1.04 | 0.48 | 0.81 | 0.19 | 10.19 | 0.79 | 0.97 | 0.76 | 0.74 | 2.80 | 4.57 | 0.97 |
| Ndufc1 | 1.04 | 0.46 | 0.82 | 0.24 | 8.51 | 0.86 | 0.80 | 0.88 | 0.77 | 2.67 | 3.89 | 0.68 |
| Ndufs3 | 1.10 | 0.55 | 0.83 | 0.30 | 6.32 | 0.84 | 0.97 | 0.82 | 0.88 | 1.96 | 2.61 | 1.14 |
| Ndufs6 | 1.23 | 0.38 | 0.81 | 0.14 | 15.41 | 0.86 | 1.07 | 0.86 | 0.79 | 4.76 | 6.40 | 0.94 |
| Ndufs7 | 0.97 | 0.53 | 0.73 | 0.11 | 4.60 | 0.78 | 1.13 | 0.85 | 0.77 | 2.21 | 2.87 | 0.86 |
| Ndufs8 | 1.01 | 0.56 | 0.81 | 0.17 | 4.80 | 0.81 | 1.09 | 0.81 | 0.76 | 1.28 | 2.64 | 0.89 |
| Ndufv1 | 0.90 | 0.65 | 0.79 | 0.31 | 3.22 | 0.90 | 0.97 | 0.89 | 0.81 | 2.40 | 2.35 | 1.00 |
| Ndufv2 | 0.92 | 0.60 | 0.71 | 0.49 | 2.97 | 0.75 | 0.79 | 0.91 | 0.72 | 1.94 | 1.91 | 1.00 |
| Ndufv3 | 1.28 | 0.59 | 0.81 | 0.40 | 9.03 | 0.87 | 0.82 | 0.67 | 0.65 | 3.45 | 4.55 | 1.01 |
| Nefh | 1.00 | 1.00 | 1.00 | 1.00 | 0.30 | 1.00 | 1.00 | 1.00 | 1.00 | 1.00 | 1.00 | 1.00 |
| Nefl | 1.00 | 1.00 | 1.00 | 1.00 | 0.06 | 1.00 | 1.00 | 1.00 | 1.00 | 1.00 | 1.00 | 1.00 |
| Nefm | 1.00 | 1.00 | 1.00 | 1.00 | 0.14 | 1.00 | 1.00 | 1.00 | 1.00 | 1.00 | 1.00 | 1.00 |
| Negr1 | 1.00 | 1.00 | 1.00 | 1.83 | 0.45 | 0.87 | 1.00 | 1.00 | 1.00 | 1.00 | 1.00 | 1.00 |
| Neil2 | 1.13 | 1.75 | 1.19 | 3.03 | 7.01 | 2.09 | 1.82 | 1.34 | 1.22 | 1.60 | 1.66 | 1.73 |
| Nell2 | 1.00 | 1.00 | 1.00 | 1.00 | 0.20 | 1.00 | 1.00 | 1.00 | 1.00 | 1.00 | 1.00 | 1.00 |
| Nenf | 1.19 | 0.45 | 0.80 | 0.42 | 12.19 | 0.96 | 0.94 | 0.73 | 0.79 | 2.86 | 4.41 | 0.88 |
| Nfil3 | 4.55 | 7.72 | 2.05 | 1.42 | 1.74 | 1.42 | 0.98 | 1.04 | 0.97 | 1.07 | 2.59 | 1.57 |
| Nfkbia | 1.78 | 2.86 | 1.35 | 1.50 | 1.10 | 1.77 | 1.38 | 1.71 | 1.06 | 0.59 | 0.64 | 1.38 |
| Nfkbib | 1.01 | 1.07 | 0.99 | 0.45 | 1.29 | 0.80 | 1.31 | 0.94 | 0.99 | 1.02 | 1.22 | 1.06 |
| Nfkbil1 | 1.54 | 1.11 | 1.41 | 1.09 | 6.28 | 1.08 | 1.53 | 1.36 | 1.24 | 1.68 | 2.39 | 1.21 |
| Ngdn | 1.44 | 0.76 | 0.83 | 0.37 | 3.79 | 0.96 | 1.19 | 1.11 | 1.00 | 1.67 | 2.01 | 1.12 |
| Ngef | 1.00 | 1.00 | 1.00 | 1.00 | 0.20 | 1.00 | 1.00 | 1.00 | 1.00 | 0.75 | 1.49 | 1.22 |
| Ngp | 1.31 | 5.11 | 4.99 | 1.60 | 1.00 | 1.00 | 1.00 | 1.00 | 1.00 | 1.56 | 1.52 | 1.01 |
| Nhp2 | 1.58 | 0.76 | 1.48 | 0.52 | 12.78 | 0.93 | 1.24 | 0.84 | 1.21 | 3.21 | 5.55 | 0.97 |
| Nit1 | 0.90 | 0.99 | 1.03 | 0.60 | 2.80 | 1.22 | 1.36 | 1.14 | 1.05 | 1.06 | 1.58 | 1.40 |
| Nkx6-2 | 1.00 | 1.00 | 1.00 | 1.00 | 1.00 | 1.00 | 1.00 | 1.00 | 1.00 | 0.80 | 1.00 | 1.00 |
| Nmb | 1.24 | 0.95 | 0.85 | 0.86 | 5.02 | 1.20 | 0.61 | 0.73 | 0.71 | 1.18 | 2.86 | 0.73 |
| Nme1 | 1.30 | 0.56 | 1.02 | 0.31 | 7.47 | 0.89 | 0.92 | 0.85 | 1.12 | 2.02 | 3.15 | 0.84 |
| Nme2 | 1.33 | 0.46 | 0.90 | 0.28 | 17.69 | 1.05 | 1.02 | 0.81 | 0.82 | 3.80 | 6.00 | 0.85 |
| Nme3 | 0.94 | 0.44 | 0.73 | 0.25 | 7.39 | 1.28 | 0.78 | 0.63 | 0.63 | 1.83 | 2.66 | 1.04 |

Fig. 35-218

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Myl4 | 0.85 | 0.98 | 1.00 | 1.00 | 1.00 | 1.00 | 1.00 | 2.00 | 1.00 | 1.00 | 1.48 | 1.83 |
| Myl6 | 1.28 | 1.48 | 1.13 | 0.85 | 0.49 | 0.77 | 1.03 | 3.18 | 1.11 | 0.93 | 1.52 | 1.01 |
| Mylpf | 0.89 | 1.39 | 0.90 | 1.00 | 1.00 | 1.00 | 1.00 | 1.00 | 1.00 | 1.00 | 1.00 | 0.75 |
| Myo1b | 2.93 | 2.36 | 2.90 | 0.99 | 1.25 | 1.17 | 0.99 | 1.05 | 1.11 | 1.01 | 1.00 | 1.00 |
| Myo9b | 0.86 | 0.90 | 0.97 | 1.32 | 0.67 | 1.09 | 1.10 | 2.24 | 1.44 | 0.99 | 1.20 | 1.04 |
| Myom1 | 1.00 | 1.00 | 0.99 | 1.00 | 0.98 | 1.00 | 3.11 | 5.11 | 3.58 | 0.93 | 1.00 | 0.82 |
| Myzap | 10.36 | 7.95 | 6.31 | 1.01 | 1.00 | 1.62 | 0.72 | 1.00 | 0.92 | 1.10 | 1.36 | 1.17 |
| N6amt2 | 1.21 | 1.43 | 0.87 | 0.91 | 0.63 | 0.80 | 1.35 | 1.85 | 1.39 | 0.75 | 1.59 | 0.87 |
| Naa10 | 0.92 | 1.21 | 0.85 | 0.58 | 0.50 | 0.77 | 0.72 | 1.18 | 0.63 | 0.97 | 1.73 | 1.20 |
| Naa38 | 0.88 | 1.37 | 0.93 | 0.69 | 0.80 | 0.99 | 0.79 | 0.73 | 0.75 | 1.04 | 1.74 | 0.90 |
| Nanos3 | 0.73 | 1.07 | 0.89 | 1.00 | 0.33 | 1.00 | 1.00 | 1.00 | 1.00 | 1.00 | 1.00 | 1.00 |
| Nap1l2 | 1.00 | 1.00 | 1.00 | 1.00 | 1.00 | 1.00 | 1.00 | 1.00 | 1.00 | 1.00 | 1.00 | 1.00 |
| Nap1l5 | 1.27 | 1.02 | 1.48 | 0.70 | 0.67 | 0.60 | 1.00 | 1.00 | 1.00 | 1.58 | 1.25 | 1.41 |
| Napb | 0.83 | 0.54 | 1.03 | 1.31 | 1.00 | 0.93 | 0.97 | 1.00 | 0.89 | 1.06 | 0.54 | 0.91 |
| Napsa | 2.03 | 1.84 | 1.99 | 0.91 | 0.69 | 0.95 | 1.00 | 2.17 | 1.00 | 1.40 | 1.19 | 0.79 |
| Nat9 | 1.76 | 2.24 | 1.38 | 0.90 | 0.56 | 0.91 | 1.02 | 2.68 | 1.12 | 1.08 | 1.69 | 0.97 |
| Ncald | 0.55 | 0.47 | 0.69 | 1.06 | 0.96 | 1.08 | 0.39 | 1.00 | 0.68 | 1.07 | 0.88 | 1.15 |
| Ncam1 | 0.74 | 0.71 | 0.81 | 1.00 | 1.00 | 1.00 | 1.00 | 1.00 | 1.00 | 0.95 | 1.27 | 1.29 |
| Ncf1 | 1.17 | 1.12 | 1.43 | 1.13 | 0.77 | 1.58 | 1.45 | 3.42 | 1.62 | 1.16 | 1.08 | 1.10 |
| Ncs1 | 1.42 | 1.33 | 1.67 | 1.38 | 1.12 | 0.97 | 1.00 | 1.00 | 1.00 | 0.79 | 0.86 | 0.89 |
| Ndrg4 | 0.90 | 0.57 | 0.99 | 0.64 | 1.00 | 0.70 | 1.00 | 1.00 | 1.00 | 0.95 | 0.92 | 1.04 |
| Ndufa10 | 0.92 | 0.90 | 0.82 | 0.86 | 0.96 | 0.90 | 0.83 | 0.76 | 0.88 | 0.98 | 1.13 | 0.93 |
| Ndufa11 | 0.90 | 1.42 | 0.78 | 0.80 | 0.46 | 0.83 | 1.14 | 2.44 | 0.92 | 0.94 | 1.64 | 0.88 |
| Ndufa13 | 1.22 | 1.55 | 0.83 | 0.82 | 0.65 | 0.87 | 0.88 | 1.45 | 0.83 | 0.90 | 1.69 | 0.97 |
| Ndufa2 | 1.19 | 1.49 | 0.86 | 0.87 | 0.47 | 0.80 | 1.05 | 3.14 | 0.89 | 0.92 | 1.85 | 1.03 |
| Ndufa3 | 1.04 | 1.63 | 1.06 | 0.69 | 0.40 | 0.77 | 0.72 | 2.88 | 0.86 | 0.86 | 2.41 | 1.09 |
| Ndufa4 | 1.20 | 1.50 | 0.94 | 0.83 | 0.58 | 0.79 | 0.89 | 2.31 | 0.80 | 1.23 | 2.66 | 0.99 |
| Ndufa4l2 | 0.90 | 1.54 | 0.86 | 0.99 | 0.66 | 0.74 | 0.96 | 0.67 | 0.94 | 0.50 | 1.57 | 0.98 |
| Ndufa5 | 1.22 | 1.12 | 0.90 | 0.70 | 0.46 | 0.80 | 0.98 | 2.34 | 0.97 | 0.93 | 1.75 | 0.96 |
| Ndufa7 | 1.54 | 1.97 | 1.56 | 0.93 | 0.89 | 0.86 | 0.96 | 1.24 | 1.07 | 1.06 | 2.31 | 1.15 |
| Ndufa9 | 0.87 | 1.16 | 0.84 | 0.91 | 0.85 | 0.84 | 0.93 | 1.06 | 0.79 | 1.00 | 1.37 | 0.85 |
| Ndufb10 | 1.10 | 1.42 | 0.97 | 0.82 | 0.63 | 0.85 | 0.77 | 1.23 | 0.67 | 0.90 | 1.51 | 0.88 |
| Ndufb5 | 1.50 | 1.51 | 0.89 | 0.83 | 0.47 | 0.84 | 0.99 | 2.95 | 1.04 | 0.91 | 1.80 | 1.07 |
| Ndufb6 | 0.85 | 1.25 | 0.77 | 0.78 | 0.72 | 0.79 | 0.85 | 1.33 | 0.79 | 0.94 | 1.43 | 0.92 |
| Ndufb7 | 1.06 | 1.68 | 0.77 | 0.80 | 0.54 | 0.84 | 0.81 | 1.80 | 0.85 | 0.95 | 1.65 | 0.96 |
| Ndufc1 | 0.82 | 1.73 | 0.64 | 0.68 | 0.52 | 0.85 | 0.86 | 1.93 | 0.86 | 1.23 | 1.67 | 0.79 |
| Ndufs3 | 0.99 | 1.32 | 0.89 | 0.80 | 0.80 | 0.74 | 1.12 | 1.17 | 0.81 | 1.02 | 1.94 | 0.97 |
| Ndufs6 | 1.02 | 1.46 | 0.88 | 0.81 | 0.43 | 0.97 | 1.02 | 3.02 | 0.99 | 0.96 | 1.85 | 0.90 |
| Ndufs7 | 1.12 | 1.58 | 0.92 | 0.77 | 0.54 | 0.86 | 0.91 | 1.63 | 0.93 | 0.99 | 1.34 | 1.04 |
| Ndufs8 | 1.14 | 1.36 | 0.82 | 0.81 | 0.83 | 0.88 | 0.79 | 0.81 | 0.69 | 1.13 | 1.67 | 1.06 |
| Ndufv1 | 1.00 | 1.31 | 0.88 | 0.97 | 0.70 | 0.95 | 0.91 | 1.92 | 0.86 | 1.00 | 1.40 | 0.92 |
| Ndufv2 | 1.05 | 1.32 | 0.86 | 0.69 | 0.60 | 0.83 | 1.03 | 1.82 | 0.79 | 0.95 | 1.45 | 0.94 |
| Ndufv3 | 1.27 | 1.61 | 0.98 | 0.90 | 1.27 | 0.94 | 0.74 | 2.26 | 0.73 | 1.21 | 2.01 | 1.11 |
| Nefh | 0.95 | 0.47 | 0.73 | 1.00 | 1.00 | 1.00 | 1.00 | 1.00 | 1.00 | 1.00 | 0.84 | 0.78 |
| Nefl | 1.19 | 1.00 | 1.00 | 1.00 | 1.00 | 1.00 | 1.00 | 1.00 | 1.00 | 1.25 | 0.51 | 1.24 |
| Nefm | 0.52 | 0.48 | 0.88 | 1.00 | 1.00 | 1.00 | 1.00 | 1.00 | 1.00 | 1.32 | 1.07 | 1.03 |
| Negr1 | 1.00 | 1.00 | 1.00 | 1.00 | 1.00 | 1.00 | 1.00 | 1.00 | 1.00 | 0.84 | 0.87 | 0.92 |
| Neil2 | 1.58 | 1.36 | 1.64 | 1.69 | 2.10 | 1.99 | 1.14 | 1.34 | 1.00 | 1.04 | 1.19 | 0.66 |
| Nell2 | 1.00 | 1.00 | 1.34 | 1.00 | 1.00 | 1.00 | 1.00 | 1.00 | 1.00 | 1.00 | 0.98 | 1.00 |
| Nenf | 1.91 | 1.82 | 1.09 | 1.03 | 0.57 | 1.04 | 1.46 | 1.98 | 0.97 | 1.02 | 1.55 | 1.04 |
| Nfil3 | 2.53 | 2.33 | 1.76 | 2.28 | 4.98 | 1.60 | 1.26 | 1.01 | 0.88 | 1.74 | 2.00 | 1.81 |
| Nfkbia | 1.00 | 1.17 | 1.02 | 1.47 | 5.92 | 1.33 | 1.44 | 0.57 | 1.33 | 1.30 | 1.29 | 1.12 |
| Nfkbib | 1.17 | 1.40 | 1.17 | 0.97 | 1.81 | 1.04 | 1.22 | 0.69 | 1.08 | 1.11 | 1.26 | 1.07 |
| Nfkbil1 | 1.28 | 1.74 | 1.21 | 1.39 | 1.87 | 1.36 | 1.54 | 1.84 | 1.24 | 1.13 | 1.92 | 1.20 |
| Ngdn | 1.09 | 1.75 | 1.15 | 0.97 | 1.04 | 1.15 | 1.49 | 1.26 | 1.77 | 1.27 | 1.64 | 1.11 |
| Ngef | 1.00 | 1.00 | 1.00 | 0.83 | 1.30 | 0.88 | 0.72 | 0.55 | 0.70 | 1.04 | 1.25 | 0.94 |
| Ngp | 0.06 | 0.22 | 1.20 | 1.00 | 1.00 | 1.00 | 1.00 | 1.00 | 1.00 | 1.00 | 1.00 | 1.00 |
| Nhp2 | 0.90 | 1.23 | 0.75 | 0.93 | 0.57 | 0.94 | 1.33 | 2.93 | 1.07 | 0.94 | 1.84 | 1.17 |
| Nit1 | 1.22 | 1.48 | 1.21 | 1.71 | 1.73 | 1.74 | 1.47 | 1.47 | 1.62 | 1.07 | 1.24 | 1.22 |
| Nkx6-2 | 0.09 | 0.10 | 0.24 | 1.00 | 1.00 | 1.00 | 1.00 | 1.00 | 1.00 | 1.00 | 1.00 | 1.00 |
| Nmb | 0.99 | 1.64 | 0.77 | 1.01 | 1.39 | 0.72 | 1.00 | 0.59 | 1.00 | 0.98 | 2.22 | 1.06 |
| Nme1 | 0.85 | 0.96 | 0.75 | 0.90 | 0.68 | 0.81 | 1.25 | 2.06 | 0.90 | 0.88 | 1.65 | 0.92 |
| Nme2 | 1.17 | 1.58 | 0.93 | 0.90 | 0.57 | 0.98 | 0.86 | 2.81 | 0.86 | 0.92 | 2.04 | 1.06 |
| Nme3 | 1.01 | 1.49 | 1.12 | 1.03 | 0.70 | 1.01 | 0.80 | 0.90 | 0.95 | 0.77 | 1.58 | 1.03 |

Fig. 35- 219

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Myl4 | 1.00 | 1.00 | 1.00 | 1.21 | 1.52 | 0.45 | 0.74 | 1.44 | 0.93 | 1.00 | 1.15 | 0.61 |
| Myl6 | 0.83 | 1.02 | 0.92 | 0.90 | 1.55 | 0.94 | 0.93 | 3.67 | 1.15 | 0.97 | 1.00 | 0.83 |
| Mylpf | 3.05 | 2.30 | 3.19 | 1.00 | 0.97 | 1.00 | 1.00 | 1.00 | 1.00 | 0.81 | 0.84 | 0.64 |
| Myo1b | 1.10 | 1.07 | 1.06 | 1.14 | 0.80 | 1.27 | 1.01 | 1.00 | 0.95 | 1.46 | 1.60 | 1.24 |
| Myo9b | 0.83 | 0.94 | 0.84 | 1.01 | 1.92 | 0.81 | 1.19 | 2.00 | 1.21 | 0.84 | 0.84 | 0.89 |
| Myom1 | 1.32 | 1.52 | 1.39 | 1.36 | 1.32 | 1.42 | 1.00 | 1.00 | 1.00 | 0.87 | 0.68 | 0.62 |
| Myzap | 0.99 | 1.00 | 0.85 | 1.19 | 0.87 | 1.22 | 1.30 | 0.63 | 1.05 | 1.88 | 1.48 | 1.60 |
| N6amt2 | 0.66 | 0.83 | 0.84 | 0.86 | 4.20 | 0.83 | 0.76 | 1.85 | 0.70 | 0.83 | 1.53 | 0.91 |
| Naa10 | 0.86 | 0.94 | 1.10 | 0.88 | 1.92 | 0.96 | 0.81 | 2.13 | 0.74 | 1.02 | 1.14 | 0.82 |
| Naa38 | 0.94 | 0.93 | 1.06 | 0.87 | 17.70 | 0.81 | 0.84 | 0.89 | 0.90 | 0.74 | 1.30 | 0.89 |
| Nanos3 | 1.00 | 1.00 | 1.00 | 1.00 | 0.93 | 1.00 | 0.85 | 4.28 | 0.78 | 1.00 | 1.94 | 1.00 |
| Nap1l2 | 1.00 | 1.00 | 1.00 | 1.00 | 1.00 | 1.00 | 1.00 | 1.00 | 1.00 | 1.00 | 6.81 | 1.00 |
| Nap1l5 | 1.71 | 1.41 | 2.11 | 0.74 | 1.24 | 0.84 | 1.00 | 1.00 | 1.00 | 1.42 | 16.07 | 1.63 |
| Napb | 1.02 | 1.08 | 1.03 | 1.41 | 1.00 | 0.71 | 0.78 | 1.00 | 0.91 | 0.87 | 7.93 | 1.32 |
| Napsa | 1.00 | 1.00 | 1.55 | 1.12 | 7.29 | 1.44 | 1.00 | 2.47 | 1.00 | 1.32 | 1.89 | 1.26 |
| Nat9 | 0.95 | 1.43 | 0.91 | 0.92 | 2.12 | 0.97 | 0.75 | 4.51 | 1.12 | 0.98 | 1.55 | 0.91 |
| Ncald | 1.03 | 0.85 | 1.19 | 1.22 | 0.76 | 1.61 | 1.00 | 1.00 | 1.00 | 0.60 | 6.73 | 0.79 |
| Ncam1 | 1.34 | 1.42 | 1.53 | 1.66 | 1.00 | 1.06 | 1.17 | 1.00 | 1.14 | 1.35 | 6.73 | 1.00 |
| Ncf1 | 2.05 | 2.42 | 2.22 | 1.01 | 1.41 | 0.86 | 1.00 | 2.82 | 1.14 | 1.02 | 0.71 | 1.00 |
| Ncs1 | 0.67 | 1.02 | 1.01 | 1.12 | 1.00 | 1.34 | 1.49 | 1.14 | 1.15 | 0.72 | 6.33 | 1.10 |
| Ndrg4 | 2.40 | 2.81 | 1.70 | 0.67 | 0.82 | 0.50 | 1.15 | 0.96 | 1.08 | 1.00 | 60.34 | 1.00 |
| Ndufa10 | 1.01 | 1.04 | 0.97 | 0.68 | 1.18 | 0.82 | 0.89 | 0.88 | 0.97 | 0.97 | 1.20 | 0.98 |
| Ndufa11 | 0.93 | 1.09 | 0.85 | 0.64 | 1.81 | 0.81 | 0.71 | 3.77 | 0.96 | 1.03 | 1.48 | 0.72 |
| Ndufa13 | 0.93 | 1.17 | 0.89 | 0.81 | 3.08 | 0.71 | 0.86 | 1.88 | 0.90 | 1.15 | 1.34 | 0.97 |
| Ndufa2 | 0.99 | 1.09 | 0.97 | 0.86 | 1.43 | 0.84 | 0.98 | 5.48 | 0.96 | 1.14 | 1.32 | 0.85 |
| Ndufa3 | 0.81 | 0.91 | 1.09 | 0.57 | 1.12 | 0.81 | 1.42 | 6.10 | 0.79 | 1.03 | 1.46 | 0.74 |
| Ndufa4 | 0.88 | 1.04 | 1.02 | 0.71 | 2.09 | 0.70 | 0.74 | 3.16 | 0.96 | 0.99 | 1.34 | 1.02 |
| Ndufa4l2 | 0.71 | 1.11 | 1.22 | 0.66 | 1.69 | 1.05 | 0.94 | 1.93 | 1.10 | 0.82 | 1.48 | 0.45 |
| Ndufa5 | 0.93 | 0.81 | 1.02 | 0.79 | 1.34 | 0.87 | 0.99 | 3.86 | 1.05 | 0.78 | 1.82 | 0.82 |
| Ndufa7 | 1.48 | 1.54 | 1.49 | 1.04 | 5.42 | 1.15 | 1.06 | 1.38 | 1.06 | 1.31 | 1.54 | 1.09 |
| Ndufa9 | 1.02 | 0.87 | 0.87 | 0.70 | 2.30 | 0.77 | 0.96 | 1.45 | 1.06 | 0.86 | 1.15 | 0.77 |
| Ndufb10 | 0.98 | 1.05 | 0.92 | 0.66 | 1.85 | 0.94 | 0.99 | 1.74 | 0.98 | 1.05 | 1.36 | 0.82 |
| Ndufb5 | 0.95 | 0.95 | 1.05 | 0.83 | 1.65 | 0.92 | 1.06 | 4.76 | 0.98 | 0.87 | 1.55 | 1.01 |
| Ndufb6 | 0.86 | 1.03 | 0.83 | 0.74 | 2.43 | 0.77 | 1.01 | 1.35 | 1.18 | 0.93 | 1.39 | 1.12 |
| Ndufb7 | 0.94 | 1.14 | 0.89 | 0.83 | 1.54 | 0.84 | 0.97 | 3.22 | 0.98 | 0.97 | 1.26 | 0.79 |
| Ndufc1 | 1.45 | 1.01 | 1.13 | 0.69 | 2.77 | 0.91 | 1.01 | 2.47 | 1.09 | 1.21 | 1.42 | 1.03 |
| Ndufs3 | 1.08 | 1.24 | 1.03 | 0.90 | 3.74 | 1.07 | 0.95 | 1.60 | 0.89 | 1.15 | 1.79 | 0.99 |
| Ndufs6 | 0.92 | 0.90 | 0.99 | 0.84 | 1.73 | 0.80 | 0.76 | 5.65 | 0.81 | 1.27 | 1.26 | 1.24 |
| Ndufs7 | 0.88 | 1.12 | 0.91 | 0.80 | 2.60 | 1.07 | 0.77 | 2.75 | 1.03 | 1.02 | 1.37 | 0.80 |
| Ndufs8 | 0.98 | 1.16 | 0.83 | 0.78 | 3.03 | 1.07 | 0.86 | 0.94 | 0.60 | 1.07 | 1.50 | 0.94 |
| Ndufv1 | 0.93 | 1.03 | 0.93 | 0.77 | 1.59 | 0.72 | 0.94 | 2.59 | 0.95 | 0.98 | 1.25 | 0.84 |
| Ndufv2 | 0.90 | 0.88 | 0.95 | 0.85 | 1.95 | 0.93 | 0.85 | 1.95 | 1.09 | 1.07 | 1.23 | 0.83 |
| Ndufv3 | 0.94 | 1.18 | 1.00 | 0.68 | 4.46 | 0.81 | 0.82 | 3.47 | 0.88 | 1.21 | 1.51 | 1.04 |
| Nefh | 1.00 | 1.00 | 1.00 | 1.00 | 1.00 | 1.00 | 1.10 | 1.00 | 0.99 | 0.91 | 5.21 | 1.01 |
| Nefl | 0.96 | 1.77 | 1.21 | 1.00 | 1.00 | 1.00 | 1.00 | 1.00 | 1.00 | 1.00 | 26.68 | 1.00 |
| Nefm | 1.46 | 1.24 | 0.88 | 1.00 | 1.00 | 1.00 | 1.00 | 1.00 | 1.00 | 1.00 | 13.66 | 1.00 |
| Negr1 | 1.00 | 1.00 | 1.00 | 0.60 | 0.21 | 0.87 | 1.00 | 1.00 | 1.00 | 1.00 | 5.32 | 1.00 |
| Neil2 | 1.36 | 1.44 | 1.24 | 0.65 | 1.95 | 0.93 | 1.00 | 1.00 | 1.00 | 1.28 | 1.63 | 1.79 |
| Nell2 | 1.00 | 1.00 | 1.00 | 1.00 | 1.00 | 1.00 | 1.01 | 0.48 | 0.96 | 1.00 | 7.30 | 1.00 |
| Nenf | 1.01 | 1.29 | 1.35 | 0.64 | 1.63 | 0.76 | 1.00 | 3.84 | 0.81 | 0.84 | 1.23 | 0.80 |
| Nfil3 | 2.89 | 3.30 | 1.59 | 12.75 | 4.85 | 2.66 | 1.11 | 1.79 | 1.50 | 2.09 | 2.33 | 1.29 |
| Nfkbia | 1.40 | 1.63 | 1.36 | 1.73 | 0.96 | 1.60 | 1.12 | 0.35 | 1.19 | 1.02 | 0.94 | 0.91 |
| Nfkbib | 1.24 | 1.14 | 1.01 | 1.68 | 2.54 | 1.21 | 1.03 | 0.44 | 1.04 | 1.11 | 1.18 | 1.05 |
| Nfkbil1 | 1.39 | 1.49 | 1.21 | 1.49 | 4.31 | 1.38 | 0.78 | 0.82 | 0.90 | 1.26 | 1.77 | 1.21 |
| Ngdn | 1.05 | 1.23 | 0.81 | 1.26 | 6.22 | 1.35 | 1.17 | 1.58 | 1.05 | 0.98 | 1.32 | 1.03 |
| Ngef | 1.04 | 1.05 | 0.94 | 1.21 | 1.00 | 2.01 | 1.00 | 1.00 | 1.00 | 1.00 | 7.69 | 1.00 |
| Ngp | 1.00 | 0.81 | 1.00 | 0.41 | 0.33 | 1.00 | 1.00 | 1.00 | 1.00 | 14.89 | 10.57 | 8.21 |
| Nhp2 | 0.89 | 0.93 | 1.05 | 1.42 | 2.89 | 1.46 | 0.83 | 3.26 | 0.98 | 1.22 | 1.55 | 1.06 |
| Nit1 | 1.72 | 1.67 | 1.69 | 1.30 | 5.94 | 1.08 | 1.01 | 0.42 | 0.91 | 1.13 | 0.98 | 1.11 |
| Nkx6-2 | 0.91 | 1.18 | 0.80 | 1.00 | 1.46 | 1.00 | 1.15 | 1.99 | 1.25 | 3.38 | 6.34 | 3.33 |
| Nmb | 1.22 | 1.73 | 1.92 | 1.62 | 5.43 | 1.16 | 0.85 | 0.98 | 0.76 | 1.88 | 2.05 | 1.36 |
| Nme1 | 0.90 | 0.62 | 0.85 | 1.30 | 2.00 | 1.03 | 0.77 | 2.46 | 0.83 | 1.17 | 1.27 | 0.96 |
| Nme2 | 0.97 | 1.00 | 0.99 | 0.96 | 2.22 | 1.04 | 0.81 | 3.73 | 0.67 | 1.21 | 1.60 | 1.08 |
| Nme3 | 0.81 | 1.00 | 1.06 | 0.72 | 1.58 | 1.18 | 0.72 | 2.12 | 1.10 | 0.93 | 1.27 | 0.90 |

Fig. 35- 220

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Myl4 | 1.00 | 1.00 | 1.00 | 1.17 | 0.76 | 1.02 | 0.94 | 6.10 | 1.37 | 0.91 | 0.82 | 0.74 |
| Myl6 | 1.52 | 1.13 | 1.02 | 0.97 | 0.73 | 1.22 | 0.99 | 20.62 | 0.99 | 3.86 | 1.59 | 1.33 |
| Mylpf | 1.00 | 1.00 | 1.00 | 1.00 | 1.00 | 1.00 | 1.78 | 5.73 | 2.03 | 2.16 | 1.00 | 1.61 |
| Myo1b | 1.12 | 1.33 | 1.15 | 0.87 | 0.97 | 0.87 | 0.87 | 0.76 | 0.88 | 1.00 | 1.00 | 1.00 |
| Myo9b | 1.14 | 0.79 | 1.04 | 0.85 | 0.78 | 0.91 | 0.96 | 5.32 | 1.03 | 2.56 | 1.05 | 1.02 |
| Myom1 | 1.00 | 1.00 | 1.00 | 1.00 | 1.00 | 1.00 | 1.21 | 2.19 | 1.42 | 1.00 | 1.00 | 1.00 |
| Myzap | 1.52 | 0.93 | 1.04 | 1.00 | 1.00 | 1.00 | 1.17 | 0.88 | 0.89 | 1.01 | 1.02 | 1.52 |
| N6amt2 | 1.00 | 0.88 | 0.89 | 1.25 | 1.13 | 1.28 | 0.78 | 5.13 | 0.58 | 1.99 | 0.88 | 1.05 |
| Naa10 | 0.73 | 0.98 | 0.56 | 1.10 | 1.06 | 0.96 | 1.06 | 12.79 | 0.82 | 2.89 | 0.97 | 1.14 |
| Naa38 | 0.90 | 0.60 | 1.30 | 1.16 | 1.95 | 1.15 | 1.37 | 2.64 | 0.83 | 1.69 | 1.19 | 0.94 |
| Nanos3 | 1.00 | 1.00 | 1.00 | 1.16 | 1.66 | 0.71 | 1.21 | 7.36 | 0.84 | 5.04 | 1.00 | 1.00 |
| Nap1l2 | 1.00 | 1.00 | 1.00 | 1.10 | 1.10 | 1.06 | 1.00 | 1.00 | 1.00 | 1.00 | 1.00 | 1.00 |
| Nap1l5 | 1.00 | 1.00 | 1.00 | 1.15 | 1.06 | 1.10 | 1.00 | 1.00 | 1.00 | 1.00 | 1.00 | 1.00 |
| Napb | 1.00 | 1.00 | 1.00 | 0.97 | 2.67 | 0.96 | 1.18 | 0.48 | 1.53 | 1.00 | 1.00 | 1.00 |
| Napsa | 1.00 | 1.00 | 1.00 | 1.00 | 1.77 | 1.00 | 0.81 | 6.91 | 0.74 | 3.33 | 1.52 | 1.29 |
| Nat9 | 1.08 | 1.05 | 0.63 | 1.26 | 0.88 | 0.94 | 1.40 | 26.80 | 1.02 | 5.03 | 1.79 | 0.99 |
| Ncald | 1.00 | 1.00 | 1.00 | 1.09 | 0.99 | 1.01 | 0.99 | 0.93 | 0.96 | 1.00 | 1.00 | 0.98 |
| Ncam1 | 1.00 | 1.00 | 1.00 | 1.03 | 0.90 | 1.03 | 1.17 | 0.90 | 1.44 | 1.82 | 1.58 | 1.45 |
| Ncf1 | 1.00 | 1.00 | 1.00 | 1.40 | 1.33 | 1.46 | 1.63 | 8.74 | 1.61 | 2.55 | 1.50 | 1.34 |
| Ncs1 | 1.00 | 1.00 | 1.00 | 1.06 | 0.99 | 1.02 | 0.87 | 0.37 | 0.93 | 1.00 | 1.00 | 1.00 |
| Ndrg4 | 1.00 | 1.00 | 1.00 | 1.06 | 1.03 | 0.95 | 0.50 | 0.48 | 0.65 | 1.00 | 1.00 | 1.00 |
| Ndufa10 | 0.94 | 1.06 | 1.08 | 1.05 | 7.61 | 1.13 | 1.14 | 1.23 | 1.02 | 1.04 | 0.90 | 0.92 |
| Ndufa11 | 0.73 | 1.46 | 0.80 | 1.03 | 0.64 | 1.11 | 1.20 | 14.29 | 0.77 | 2.98 | 1.13 | 1.27 |
| Ndufa13 | 0.96 | 1.05 | 0.69 | 0.97 | 0.84 | 1.02 | 1.40 | 13.18 | 1.17 | 3.67 | 1.13 | 1.21 |
| Ndufa2 | 0.77 | 1.17 | 0.92 | 1.09 | 0.79 | 1.03 | 1.06 | 47.78 | 1.05 | 4.74 | 1.35 | 1.16 |
| Ndufa3 | 1.15 | 1.72 | 1.29 | 0.96 | 0.77 | 1.31 | 1.42 | 53.40 | 1.14 | 8.72 | 1.11 | 1.53 |
| Ndufa4 | 1.39 | 0.98 | 1.35 | 1.22 | 0.95 | 0.92 | 1.15 | 21.12 | 0.97 | 3.75 | 1.34 | 1.08 |
| Ndufa4l2 | 1.00 | 0.95 | 0.80 | 0.98 | 0.95 | 1.21 | 0.66 | 2.32 | 0.49 | 1.00 | 1.00 | 1.00 |
| Ndufa5 | 1.13 | 0.63 | 1.07 | 0.91 | 0.88 | 1.08 | 1.55 | 15.42 | 0.93 | 3.00 | 1.14 | 0.96 |
| Ndufa7 | 1.47 | 1.11 | 0.93 | 1.18 | 1.67 | 1.41 | 1.81 | 5.68 | 1.18 | 3.25 | 1.59 | 1.45 |
| Ndufa9 | 1.30 | 0.89 | 0.58 | 0.94 | 6.64 | 0.94 | 1.19 | 4.29 | 0.87 | 1.94 | 1.02 | 1.17 |
| Ndufb10 | 0.80 | 0.82 | 0.82 | 1.25 | 0.99 | 1.04 | 1.17 | 5.96 | 0.86 | 1.63 | 1.00 | 1.13 |
| Ndufb5 | 0.65 | 1.28 | 0.82 | 1.08 | 0.80 | 0.98 | 0.91 | 22.32 | 1.01 | 3.62 | 1.15 | 1.32 |
| Ndufb6 | 1.25 | 0.89 | 1.18 | 1.42 | 1.21 | 1.21 | 1.24 | 5.36 | 0.98 | 2.08 | 1.10 | 1.11 |
| Ndufb7 | 1.19 | 1.15 | 1.03 | 1.27 | 0.92 | 1.15 | 1.40 | 22.21 | 0.98 | 3.88 | 1.24 | 1.09 |
| Ndufc1 | 0.63 | 0.86 | 0.68 | 1.51 | 1.11 | 1.13 | 1.41 | 12.34 | 0.81 | 3.42 | 0.88 | 1.21 |
| Ndufs3 | 0.83 | 0.85 | 0.84 | 1.09 | 1.26 | 1.01 | 1.16 | 7.41 | 0.96 | 2.91 | 1.02 | 0.99 |
| Ndufs6 | 0.98 | 1.20 | 0.98 | 0.98 | 0.74 | 1.16 | 1.39 | 36.74 | 0.90 | 4.73 | 1.12 | 1.05 |
| Ndufs7 | 0.97 | 0.71 | 0.70 | 1.26 | 0.88 | 1.09 | 1.88 | 9.60 | 0.98 | 2.33 | 1.17 | 1.23 |
| Ndufs8 | 0.90 | 0.70 | 0.91 | 1.15 | 1.19 | 1.13 | 1.28 | 8.59 | 0.86 | 2.12 | 1.27 | 1.16 |
| Ndufv1 | 1.07 | 1.11 | 1.11 | 1.19 | 0.87 | 1.01 | 1.24 | 5.45 | 0.99 | 1.52 | 0.92 | 0.98 |
| Ndufv2 | 0.74 | 1.10 | 1.06 | 1.06 | 0.76 | 1.08 | 1.36 | 5.83 | 1.14 | 1.31 | 1.20 | 1.07 |
| Ndufv3 | 0.76 | 0.74 | 0.97 | 1.36 | 2.09 | 1.04 | 1.36 | 15.01 | 1.06 | 4.62 | 1.53 | 1.38 |
| Nefh | 1.00 | 1.00 | 1.00 | 1.14 | 0.92 | 0.97 | 1.00 | 1.00 | 1.00 | 1.00 | 1.00 | 1.00 |
| Nefl | 1.00 | 1.00 | 1.00 | 1.12 | 0.52 | 1.03 | 1.00 | 1.00 | 1.00 | 1.00 | 1.00 | 1.00 |
| Nefm | 1.00 | 1.00 | 1.00 | 1.23 | 1.00 | 1.02 | 1.00 | 1.00 | 1.00 | 1.00 | 1.00 | 1.00 |
| Negr1 | 1.00 | 1.00 | 1.00 | 1.01 | 0.98 | 0.91 | 1.00 | 1.00 | 1.00 | 1.00 | 1.00 | 1.00 |
| Neil2 | 1.00 | 1.00 | 1.00 | 0.90 | 1.22 | 0.95 | 0.95 | 2.16 | 1.15 | 1.00 | 1.00 | 1.00 |
| Nell2 | 1.00 | 1.00 | 1.00 | 1.23 | 1.14 | 1.09 | 1.38 | 1.00 | 1.00 | 1.00 | 1.00 | 1.00 |
| Nenf | 0.65 | 1.07 | 1.14 | 0.94 | 0.89 | 1.01 | 1.39 | 29.66 | 1.13 | 3.54 | 1.01 | 0.94 |
| Nfil3 | 4.10 | 9.34 | 1.24 | 1.54 | 4.90 | 1.31 | 2.67 | 2.08 | 1.79 | 1.17 | 1.86 | 1.29 |
| Nfkbia | 2.05 | 2.61 | 1.82 | 1.30 | 2.06 | 1.24 | 1.49 | 0.24 | 1.30 | 0.89 | 2.40 | 1.40 |
| Nfkbib | 1.33 | 0.83 | 0.99 | 1.01 | 5.03 | 0.97 | 1.13 | 1.12 | 0.93 | 0.90 | 1.42 | 1.20 |
| Nfkbil1 | 0.85 | 0.81 | 0.90 | 1.29 | 1.75 | 1.19 | 1.70 | 3.30 | 1.22 | 2.61 | 2.06 | 1.36 |
| Ngdn | 1.12 | 1.35 | 0.63 | 0.88 | 0.59 | 1.19 | 1.42 | 3.15 | 0.87 | 1.73 | 1.22 | 1.41 |
| Ngef | 0.78 | 0.52 | 1.02 | 1.04 | 0.83 | 0.93 | 0.84 | 0.31 | 0.91 | 1.00 | 1.00 | 1.00 |
| Ngp | 1.00 | 1.00 | 1.00 | 1.00 | 0.30 | 1.00 | 1.00 | 5.09 | 1.00 | 1.38 | 1.56 | 1.41 |
| Nhp2 | 0.99 | 1.64 | 1.06 | 1.27 | 1.10 | 1.09 | 0.91 | 13.45 | 0.73 | 3.04 | 1.04 | 1.01 |
| Nit1 | 1.80 | 1.36 | 1.34 | 1.28 | 1.00 | 1.24 | 1.13 | 1.28 | 1.08 | 1.24 | 1.10 | 1.29 |
| Nkx6-2 | 1.00 | 1.00 | 1.00 | 0.69 | 0.77 | 0.82 | 1.00 | 1.00 | 1.00 | 1.00 | 1.00 | 1.00 |
| Nmb | 0.63 | 0.88 | 0.53 | 0.82 | 0.69 | 1.11 | 1.13 | 9.62 | 1.45 | 2.47 | 1.65 | 1.52 |
| Nme1 | 1.19 | 1.28 | 1.13 | 1.07 | 0.92 | 1.01 | 1.06 | 11.54 | 0.77 | 2.27 | 0.74 | 0.85 |
| Nme2 | 0.89 | 0.88 | 1.14 | 1.12 | 0.70 | 1.09 | 1.01 | 31.22 | 0.90 | 5.42 | 1.10 | 1.06 |
| Nme3 | 0.90 | 0.77 | 0.96 | 1.19 | 1.02 | 1.03 | 1.28 | 8.86 | 0.88 | 1.81 | 0.88 | 1.01 |

Fig. 35- 221

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Nme5 | 1.00 | 0.62 | 0.96 | 1.00 | 1.00 | 1.00 | 0.74 | 1.45 | 0.80 | 1.35 | 1.90 | 0.71 |
| Nme7 | 1.00 | 1.00 | 1.00 | 0.61 | 1.40 | 1.12 | 1.63 | 1.15 | 1.23 | 2.42 | 2.20 | 1.07 |
| Nmi | 0.93 | 0.83 | 1.01 | 1.06 | 6.56 | 0.94 | 0.81 | 0.75 | 0.78 | 1.95 | 1.96 | 0.97 |
| Nnat | 0.17 | 0.10 | 0.07 | 0.19 | 0.07 | 0.11 | 1.00 | 0.68 | 0.58 | 0.53 | 0.44 | 0.74 |
| Nnmt | 1.30 | 2.34 | 1.34 | 0.25 | 4.33 | 0.59 | 1.95 | 0.42 | 1.01 | 0.87 | 2.00 | 0.73 |
| Nob1 | 1.33 | 0.91 | 1.05 | 0.75 | 4.37 | 1.36 | 0.91 | 0.88 | 0.86 | 1.75 | 2.04 | 0.99 |
| Noc2l | 1.19 | 0.72 | 1.20 | 0.86 | 4.25 | 1.65 | 1.11 | 1.07 | 1.23 | 0.57 | 2.17 | 1.09 |
| Nol12 | 1.33 | 0.54 | 0.91 | 0.61 | 8.44 | 0.82 | 1.08 | 1.01 | 0.93 | 3.17 | 5.17 | 1.04 |
| Nol7 | 0.94 | 0.65 | 0.73 | 0.56 | 1.76 | 0.71 | 0.92 | 0.94 | 0.91 | 1.32 | 1.33 | 0.83 |
| Nop16 | 1.31 | 0.68 | 1.01 | 0.90 | 6.71 | 1.18 | 1.05 | 1.04 | 1.18 | 1.69 | 2.59 | 1.07 |
| Npas2 | 1.00 | 1.00 | 1.00 | 2.88 | 1.40 | 1.00 | 1.24 | 1.37 | 1.00 | 1.00 | 1.00 | 1.00 |
| Npc1 | 13.52 | 13.86 | 17.15 | 4.16 | 4.56 | 2.89 | 0.51 | 0.47 | 0.37 | 2.89 | 1.65 | 1.27 |
| Npcd | 0.90 | 1.00 | 1.00 | 1.30 | 0.10 | 1.00 | 0.69 | 0.66 | 0.53 | 0.93 | 1.05 | 1.99 |
| Npdc1 | 1.39 | 0.83 | 1.17 | 0.49 | 4.15 | 1.22 | 1.23 | 1.05 | 1.11 | 2.06 | 2.69 | 0.95 |
| Npff | 1.19 | 0.58 | 0.78 | 0.89 | 6.12 | 1.24 | 0.92 | 0.56 | 0.87 | 3.16 | 2.11 | 0.82 |
| Npl | 1.00 | 1.00 | 0.94 | 1.00 | 1.00 | 1.00 | 1.00 | 1.00 | 1.00 | 1.00 | 0.83 | 1.27 |
| Npm3 | 0.84 | 0.46 | 0.63 | 1.50 | 19.16 | 1.33 | 0.45 | 0.85 | 0.49 | 4.01 | 4.02 | 1.06 |
| Nppb | 1.00 | 1.00 | 1.00 | 1.00 | 1.00 | 1.00 | 5.16 | 6.86 | 5.06 | 1.00 | 1.00 | 1.00 |
| Npr1 | 1.02 | 0.81 | 1.37 | 1.08 | 5.86 | 1.68 | 1.18 | 1.13 | 1.23 | 1.86 | 1.93 | 1.01 |
| Nptx1 | 1.00 | 1.00 | 1.00 | 1.00 | 0.15 | 1.00 | 1.00 | 1.00 | 1.00 | 0.43 | 0.41 | 0.92 |
| Nptxr | 1.00 | 1.00 | 1.00 | 1.00 | 0.16 | 1.35 | 1.37 | 1.22 | 1.54 | 1.00 | 1.00 | 0.58 |
| Nr1h3 | 1.02 | 0.56 | 1.16 | 0.35 | 5.04 | 0.92 | 0.99 | 1.14 | 1.05 | 2.17 | 2.83 | 0.88 |
| Nr1h4 | 1.00 | 1.00 | 1.00 | 1.00 | 1.00 | 1.00 | 1.00 | 1.00 | 1.00 | 1.00 | 1.00 | 1.00 |
| Nr2c2ap | 1.71 | 0.56 | 1.10 | 0.72 | 8.71 | 0.68 | 0.78 | 0.84 | 0.95 | 2.54 | 3.21 | 1.12 |
| Nr4a1 | 0.99 | 2.80 | 0.44 | 3.97 | 1.50 | 6.82 | 3.01 | 4.85 | 3.33 | 1.05 | 2.79 | 1.10 |
| Nr4a2 | 1.00 | 1.00 | 1.00 | 3.61 | 0.23 | 1.27 | 1.00 | 1.00 | 1.00 | 1.00 | 1.00 | 1.24 |
| Nr4a3 | 3.92 | 1.00 | 1.00 | 26.08 | 0.80 | 9.33 | 4.91 | 5.48 | 5.87 | 1.00 | 1.00 | 4.82 |
| Nrbp1 | 1.15 | 0.63 | 0.95 | 0.73 | 5.11 | 1.06 | 1.12 | 0.93 | 0.87 | 2.44 | 3.14 | 1.00 |
| Nrg4 | 0.70 | 1.00 | 1.15 | 0.45 | 0.88 | 1.20 | 0.73 | 1.20 | 1.03 | 1.16 | 1.00 | 0.84 |
| Nrsn1 | 1.00 | 1.00 | 1.00 | 1.00 | 0.10 | 1.00 | 1.00 | 1.00 | 1.00 | 1.00 | 1.00 | 1.00 |
| Nrsn2 | 1.00 | 1.00 | 1.00 | 1.00 | 0.15 | 1.00 | 1.00 | 1.00 | 1.00 | 1.00 | 1.00 | 1.00 |
| Nrtn | 1.45 | 0.76 | 1.21 | 0.26 | 11.01 | 0.75 | 1.18 | 0.65 | 0.79 | 3.86 | 7.14 | 1.32 |
| Nrxn1 | 1.00 | 1.00 | 1.00 | 1.00 | 0.34 | 1.00 | 1.00 | 1.00 | 1.00 | 1.00 | 1.00 | 1.00 |
| Nsg1 | 1.19 | 1.00 | 1.28 | 1.46 | 0.08 | 0.51 | 1.15 | 0.70 | 0.81 | 0.70 | 0.64 | 0.94 |
| Nsmce1 | 1.67 | 0.99 | 0.95 | 0.48 | 5.79 | 1.03 | 1.03 | 0.79 | 0.80 | 1.91 | 1.89 | 0.82 |
| Nsun5 | 1.37 | 0.87 | 0.86 | 0.41 | 5.72 | 1.29 | 1.28 | 0.68 | 0.69 | 1.97 | 2.73 | 0.87 |
| Nt5c | 1.37 | 0.52 | 1.16 | 0.89 | 11.60 | 0.88 | 1.13 | 1.06 | 1.03 | 2.37 | 4.28 | 0.99 |
| Nt5dc2 | 1.00 | 1.00 | 1.00 | 0.54 | 3.06 | 1.00 | 1.16 | 0.79 | 0.81 | 1.34 | 1.96 | 1.04 |
| Ntan1 | 0.94 | 0.53 | 0.83 | 1.33 | 6.32 | 0.72 | 0.66 | 0.84 | 0.85 | 1.83 | 2.49 | 0.88 |
| Nthl1 | 0.89 | 0.43 | 0.95 | 0.62 | 5.55 | 0.75 | 0.81 | 0.75 | 1.03 | 2.60 | 2.44 | 0.98 |
| Ntm | 1.00 | 1.00 | 1.00 | 1.00 | 0.21 | 1.00 | 1.00 | 1.00 | 1.00 | 1.00 | 1.00 | 1.00 |
| Ntmt1 | 2.24 | 1.08 | 0.96 | 0.40 | 3.32 | 0.92 | 0.79 | 0.71 | 0.77 | 1.37 | 2.05 | 0.90 |
| Ntn5 | 1.00 | 1.00 | 1.00 | 1.00 | 1.00 | 1.00 | 1.00 | 1.00 | 1.00 | 1.37 | 3.25 | 0.91 |
| Ntrk2 | 0.82 | 1.00 | 1.77 | 1.31 | 1.12 | 1.10 | 1.00 | 1.00 | 1.00 | 0.66 | 0.62 | 0.82 |
| Ntsr2 | 2.50 | 1.27 | 1.34 | 0.60 | 0.22 | 0.79 | 0.44 | 0.24 | 0.35 | 1.00 | 1.00 | 1.00 |
| Nubp2 | 1.22 | 1.08 | 0.94 | 0.30 | 1.22 | 0.76 | 0.93 | 0.78 | 0.93 | 0.96 | 1.38 | 1.03 |
| Nubpl | 1.93 | 0.52 | 0.66 | 0.53 | 9.39 | 0.81 | 1.70 | 0.99 | 1.09 | 1.69 | 2.51 | 1.13 |
| Nudt1 | 1.43 | 0.67 | 0.73 | 0.51 | 2.94 | 0.76 | 1.00 | 0.61 | 0.53 | 1.55 | 2.65 | 0.81 |
| Nudt14 | 1.66 | 0.66 | 1.01 | 0.33 | 4.86 | 0.98 | 1.04 | 0.82 | 1.01 | 1.87 | 2.27 | 0.92 |
| Nudt18 | 1.36 | 1.71 | 1.12 | 2.98 | 13.15 | 3.13 | 1.32 | 1.25 | 1.22 | 1.46 | 1.78 | 1.21 |
| Nudt8 | 1.00 | 0.39 | 0.76 | 0.31 | 5.67 | 0.86 | 1.00 | 0.81 | 0.85 | 1.86 | 2.27 | 1.04 |
| Nufip1 | 1.42 | 1.01 | 1.47 | 1.41 | 2.40 | 1.06 | 1.53 | 1.32 | 1.19 | 2.01 | 2.59 | 0.92 |
| Nupr1l | 1.00 | 1.00 | 1.00 | 2.31 | 9.09 | 3.34 | 1.89 | 1.30 | 1.58 | 1.26 | 1.66 | 1.56 |
| Nxn | 1.84 | 1.26 | 1.11 | 1.59 | 7.79 | 2.15 | 1.65 | 1.49 | 1.18 | 2.07 | 2.30 | 1.18 |
| Oas1a | 1.00 | 1.00 | 1.00 | 1.00 | 1.89 | 1.00 | 1.39 | 1.50 | 2.13 | 8.54 | 6.42 | 4.72 |
| Oas1c | 1.00 | 1.00 | 1.00 | 1.00 | 1.93 | 1.00 | 1.00 | 1.00 | 1.19 | 2.15 | 1.84 | 1.34 |
| Oas1g | 1.00 | 1.00 | 1.00 | 1.00 | 1.02 | 1.00 | 1.00 | 1.00 | 1.00 | 6.33 | 4.69 | 2.11 |
| Oas2 | 1.00 | 1.00 | 1.24 | 1.59 | 1.24 | 2.71 | 8.89 | 8.82 | 12.78 | 1.35 | 1.91 | 5.21 |
| Oas3 | 1.00 | 1.00 | 1.00 | 1.00 | 1.00 | 1.00 | 1.00 | 1.00 | 1.00 | 1.44 | 1.32 | 1.00 |
| Oasl1 | 1.00 | 1.00 | 1.00 | 1.05 | 2.23 | 1.12 | 1.70 | 1.09 | 1.91 | 1.83 | 1.78 | 1.28 |
| Oasl2 | 1.11 | 1.36 | 1.97 | 2.62 | 1.00 | 2.81 | 2.70 | 2.26 | 3.51 | 1.90 | 1.10 | 2.67 |
| Oaz1-ps | 1.00 | 1.00 | 4.14 | 0.01 | 1.00 | 1.86 | 1.00 | 1.00 | 8.57 | 1.00 | 1.00 | 1.89 |
| Oaz3 | 1.00 | 1.00 | 1.00 | 1.00 | 1.00 | 1.00 | 1.00 | 1.00 | 1.00 | 1.93 | 1.16 | 1.00 |
| Obp2a | 1.00 | 1.00 | 1.00 | 1.00 | 1.00 | 1.00 | 1.00 | 1.00 | 1.00 | 1.00 | 1.00 | 1.00 |

Fig. 35- 222

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Nme5 | 1.00 | 0.90 | 1.00 | 0.76 | 0.81 | 0.58 | 1.00 | 1.00 | 1.00 | 1.00 | 0.87 | 1.00 |
| Nme7 | 1.13 | 1.14 | 1.02 | 0.97 | 0.24 | 0.80 | 1.14 | 0.46 | 0.84 | 1.00 | 1.22 | 0.88 |
| Nmi | 1.17 | 1.40 | 1.00 | 1.45 | 0.94 | 0.99 | 0.96 | 0.93 | 1.52 | 1.27 | 1.94 | 0.97 |
| Nnat | 0.55 | 0.62 | 0.11 | 1.00 | 1.00 | 1.48 | 1.00 | 1.00 | 1.44 | 0.86 | 0.87 | 0.67 |
| Nnmt | 0.85 | 1.30 | 0.77 | 1.00 | 0.45 | 1.00 | 19.53 | 177.21 | 14.15 | 0.89 | 1.83 | 1.00 |
| Nob1 | 1.22 | 1.16 | 1.02 | 1.07 | 0.87 | 1.05 | 1.19 | 3.20 | 1.29 | 1.02 | 1.43 | 1.24 |
| Noc2l | 0.89 | 1.06 | 0.92 | 1.21 | 4.05 | 1.05 | 1.60 | 0.31 | 1.44 | 1.04 | 1.38 | 1.04 |
| Nol12 | 1.10 | 1.21 | 0.95 | 1.41 | 0.49 | 1.00 | 1.13 | 3.32 | 1.07 | 0.98 | 1.78 | 1.06 |
| Nol7 | 0.89 | 1.03 | 0.78 | 0.75 | 0.72 | 0.89 | 0.77 | 0.80 | 0.90 | 0.95 | 1.19 | 1.05 |
| Nop16 | 1.04 | 1.35 | 0.93 | 0.56 | 0.46 | 0.52 | 1.03 | 1.13 | 0.74 | 0.93 | 1.57 | 1.19 |
| Npas2 | 1.71 | 1.76 | 1.45 | 1.45 | 1.00 | 1.18 | 1.00 | 1.00 | 1.00 | 1.64 | 1.35 | 1.46 |
| Npc1 | 1.72 | 1.50 | 1.76 | 0.99 | 0.63 | 0.92 | 0.96 | 1.58 | 1.19 | 1.46 | 1.36 | 1.48 |
| Npcd | 2.51 | 2.05 | 2.03 | 1.03 | 1.03 | 0.88 | 1.00 | 1.00 | 1.00 | 1.28 | 1.37 | 1.13 |
| Npdc1 | 1.73 | 1.63 | 1.23 | 1.17 | 1.01 | 1.41 | 0.74 | 1.47 | 0.99 | 1.21 | 1.63 | 1.16 |
| Npff | 1.45 | 1.60 | 1.15 | 1.09 | 0.43 | 0.77 | 1.05 | 0.57 | 0.96 | 0.74 | 1.22 | 1.56 |
| Npl | 1.66 | 1.58 | 1.30 | 1.55 | 5.03 | 0.94 | 1.00 | 1.00 | 1.00 | 0.99 | 0.91 | 1.00 |
| Npm3 | 0.93 | 1.18 | 1.24 | 0.90 | 0.70 | 0.53 | 2.27 | 2.88 | 1.01 | 1.24 | 1.72 | 1.41 |
| Nppb | 1.00 | 1.00 | 1.00 | 1.00 | 1.00 | 1.00 | 1.00 | 1.00 | 1.00 | 1.00 | 1.00 | 1.00 |
| Npr1 | 1.58 | 1.55 | 1.76 | 1.02 | 0.85 | 1.46 | 0.90 | 1.50 | 0.90 | 1.30 | 1.24 | 0.96 |
| Nptx1 | 1.00 | 1.00 | 1.00 | 1.00 | 1.00 | 1.00 | 1.00 | 1.00 | 1.00 | 1.00 | 1.00 | 1.00 |
| Nptxr | 1.00 | 1.00 | 1.00 | 1.00 | 1.00 | 1.42 | 1.00 | 1.00 | 1.00 | 1.00 | 1.00 | 1.01 |
| Nr1h3 | 2.14 | 2.01 | 1.41 | 1.14 | 0.64 | 1.05 | 1.15 | 1.97 | 0.92 | 0.82 | 1.28 | 0.87 |
| Nr1h4 | 4.43 | 3.61 | 3.43 | 1.03 | 1.63 | 0.97 | 0.60 | 0.32 | 0.80 | 1.04 | 1.28 | 1.03 |
| Nr2c2ap | 1.44 | 1.51 | 1.12 | 1.09 | 0.76 | 0.91 | 0.68 | 2.20 | 1.26 | 0.98 | 1.85 | 1.02 |
| Nr4a1 | 1.98 | 2.14 | 2.18 | 1.55 | 1.88 | 1.51 | 2.69 | 1.27 | 1.45 | 0.99 | 2.01 | 1.55 |
| Nr4a2 | 0.84 | 0.50 | 0.80 | 1.00 | 1.00 | 1.00 | 1.00 | 1.00 | 1.00 | 1.08 | 1.00 | 1.00 |
| Nr4a3 | 0.41 | 0.45 | 1.60 | 1.00 | 1.00 | 1.00 | 1.00 | 1.00 | 1.00 | 1.00 | 1.00 | 1.00 |
| Nrbp1 | 0.94 | 1.14 | 0.97 | 1.20 | 0.85 | 0.99 | 1.12 | 2.78 | 0.99 | 1.08 | 1.44 | 1.05 |
| Nrg4 | 0.66 | 0.87 | 0.74 | 1.06 | 0.76 | 0.96 | 7.38 | 17.89 | 3.84 | 0.72 | 0.65 | 0.95 |
| Nrsn1 | 1.00 | 1.00 | 1.00 | 1.00 | 1.00 | 1.00 | 1.00 | 1.00 | 1.00 | 1.22 | 1.63 | 1.27 |
| Nrsn2 | 1.00 | 1.00 | 1.00 | 1.00 | 1.00 | 1.00 | 1.00 | 1.00 | 1.00 | 1.16 | 1.54 | 1.44 |
| Nrtn | 1.85 | 2.76 | 1.35 | 1.20 | 0.78 | 1.41 | 0.92 | 1.45 | 0.65 | 0.85 | 1.60 | 1.28 |
| Nrxn1 | 1.00 | 1.00 | 1.00 | 1.00 | 1.00 | 1.00 | 1.00 | 1.00 | 1.00 | 1.00 | 1.00 | 1.00 |
| Nsg1 | 0.61 | 0.36 | 0.48 | 0.72 | 1.00 | 0.56 | 1.00 | 1.00 | 1.00 | 1.22 | 0.87 | 0.94 |
| Nsmce1 | 1.06 | 1.15 | 0.76 | 0.76 | 0.42 | 0.78 | 1.51 | 3.16 | 1.27 | 1.01 | 1.70 | 0.87 |
| Nsun5 | 1.10 | 1.72 | 0.97 | 1.13 | 0.76 | 1.04 | 0.95 | 1.60 | 1.02 | 1.01 | 2.35 | 1.29 |
| Nt5c | 1.15 | 1.51 | 1.05 | 0.91 | 0.61 | 0.99 | 1.06 | 1.78 | 0.90 | 0.85 | 1.72 | 1.02 |
| Nt5dc2 | 0.45 | 0.83 | 0.58 | 0.82 | 0.59 | 0.91 | 0.45 | 0.74 | 0.66 | 1.00 | 1.70 | 1.14 |
| Ntan1 | 1.34 | 1.36 | 1.02 | 0.64 | 0.63 | 0.56 | 1.02 | 0.97 | 0.86 | 0.82 | 1.18 | 0.97 |
| Nthl1 | 1.34 | 1.52 | 1.57 | 0.92 | 0.56 | 0.86 | 0.50 | 0.68 | 0.41 | 0.91 | 2.15 | 1.13 |
| Ntm | 1.00 | 1.00 | 1.00 | 1.00 | 1.00 | 1.00 | 1.21 | 1.00 | 1.00 | 1.00 | 1.00 | 1.00 |
| Ntmt1 | 1.22 | 1.54 | 0.96 | 0.95 | 1.04 | 1.21 | 1.40 | 1.50 | 1.24 | 0.95 | 1.36 | 0.93 |
| Ntn5 | 0.75 | 0.90 | 1.00 | 1.00 | 1.00 | 1.00 | 1.00 | 1.00 | 1.00 | 1.00 | 1.00 | 1.00 |
| Ntrk2 | 1.04 | 0.68 | 0.71 | 1.00 | 1.00 | 1.00 | 1.00 | 1.00 | 0.49 | 1.00 | 1.00 | 1.00 |
| Ntsr2 | 1.00 | 1.00 | 1.00 | 1.00 | 1.00 | 1.00 | 1.00 | 1.00 | 1.00 | 1.00 | 1.00 | 1.00 |
| Nubp2 | 1.14 | 1.27 | 1.04 | 0.96 | 1.01 | 0.96 | 0.83 | 0.55 | 0.86 | 0.91 | 1.32 | 1.03 |
| Nubpl | 1.31 | 1.04 | 1.47 | 0.87 | 0.60 | 0.86 | 0.79 | 1.59 | 1.30 | 1.34 | 1.60 | 0.65 |
| Nudt1 | 1.13 | 1.32 | 0.87 | 0.73 | 0.63 | 0.64 | 1.06 | 1.36 | 0.94 | 0.95 | 1.45 | 0.88 |
| Nudt14 | 1.73 | 2.18 | 1.36 | 0.96 | 0.77 | 0.82 | 0.84 | 1.46 | 0.99 | 0.85 | 1.45 | 1.09 |
| Nudt18 | 1.63 | 1.78 | 1.32 | 0.95 | 0.83 | 1.03 | 2.79 | 3.21 | 2.50 | 1.07 | 1.49 | 1.13 |
| Nudt8 | 0.98 | 1.03 | 1.01 | 0.98 | 0.67 | 1.08 | 0.89 | 1.26 | 0.84 | 0.80 | 1.20 | 1.03 |
| Nufip1 | 1.07 | 1.10 | 0.90 | 1.24 | 0.96 | 1.30 | 1.31 | 2.14 | 1.07 | 1.29 | 1.50 | 1.16 |
| Nupr1l | 1.90 | 1.74 | 2.22 | 0.85 | 1.67 | 1.03 | 0.95 | 4.25 | 0.85 | 1.57 | 1.35 | 0.75 |
| Nxn | 1.46 | 1.48 | 1.29 | 1.13 | 1.07 | 0.98 | 1.03 | 1.65 | 1.00 | 0.92 | 1.48 | 1.10 |
| Oas1a | 2.60 | 2.46 | 2.46 | 1.33 | 2.12 | 1.82 | 1.15 | 5.35 | 1.07 | 2.47 | 2.36 | 1.85 |
| Oas1c | 1.58 | 1.61 | 1.40 | 1.15 | 1.00 | 1.62 | 1.00 | 1.45 | 1.00 | 1.37 | 1.76 | 1.07 |
| Oas1g | 1.62 | 2.23 | 2.48 | 1.00 | 2.34 | 1.27 | 1.00 | 2.49 | 1.00 | 2.42 | 2.94 | 1.89 |
| Oas2 | 1.93 | 1.70 | 2.75 | 1.56 | 1.00 | 2.07 | 1.00 | 1.00 | 1.00 | 14.60 | 8.90 | 8.19 |
| Oas3 | 1.94 | 1.70 | 2.71 | 1.00 | 1.00 | 1.00 | 1.00 | 1.00 | 1.00 | 8.46 | 6.99 | 5.02 |
| Oasl1 | 2.00 | 2.55 | 2.58 | 1.75 | 2.25 | 2.82 | 2.41 | 1.99 | 3.08 | 2.86 | 2.27 | 1.82 |
| Oasl2 | 1.44 | 1.22 | 1.37 | 3.31 | 2.10 | 3.21 | 1.00 | 1.00 | 1.08 | 8.48 | 5.23 | 3.80 |
| Oaz1-ps | 1.00 | 1.00 | 0.55 | 1.00 | 1.00 | 1.24 | 4.47 | 1.00 | 1.11 | 1.00 | 1.00 | 1.99 |
| Oaz3 | 0.83 | 0.75 | 0.76 | 1.00 | 1.00 | 1.00 | 1.00 | 1.00 | 1.00 | 1.00 | 1.00 | 1.00 |
| Obp2a | 1.00 | 1.00 | 1.00 | 1.00 | 1.00 | 1.00 | 7.96 | 6.63 | 2.81 | 1.00 | 1.00 | 1.00 |

Fig. 35- 223

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Nme5 | 1.00 | 1.00 | 1.00 | 1.24 | 1.29 | 3.13 | 0.92 | 0.95 | 0.87 | 1.00 | 1.00 | 1.00 |
| Nme7 | 0.84 | 0.64 | 0.98 | 0.52 | 1.00 | 0.80 | 1.09 | 0.83 | 0.98 | 1.21 | 1.25 | 1.24 |
| Nmi | 1.21 | 1.08 | 1.19 | 0.72 | 1.62 | 0.98 | 1.00 | 1.22 | 1.00 | 1.19 | 1.50 | 1.19 |
| Nnat | 0.67 | 0.77 | 0.45 | 0.04 | 0.04 | 0.05 | 1.00 | 1.00 | 1.62 | 0.39 | 7.38 | 0.94 |
| Nnmt | 1.06 | 2.01 | 0.83 | 1.49 | 17.77 | 0.74 | 1.00 | 1.03 | 1.00 | 1.00 | 1.00 | 1.00 |
| Nob1 | 0.98 | 1.16 | 1.21 | 1.25 | 7.34 | 1.47 | 0.90 | 1.57 | 1.04 | 1.27 | 1.37 | 1.17 |
| Noc2l | 0.88 | 0.89 | 0.97 | 1.33 | 0.30 | 1.29 | 1.29 | 1.54 | 0.78 | 1.19 | 1.23 | 1.24 |
| Nol12 | 0.99 | 0.99 | 0.93 | 0.98 | 1.60 | 0.98 | 0.91 | 4.13 | 1.07 | 0.90 | 1.15 | 1.04 |
| Nol7 | 1.13 | 0.80 | 0.84 | 0.81 | 6.93 | 0.88 | 1.05 | 1.88 | 1.14 | 0.97 | 1.00 | 0.98 |
| Nop16 | 0.94 | 0.84 | 1.14 | 1.03 | 3.17 | 1.29 | 0.75 | 1.93 | 0.78 | 1.33 | 1.27 | 1.12 |
| Npas2 | 2.48 | 2.55 | 1.95 | 14.69 | 1.00 | 4.90 | 1.00 | 1.00 | 1.00 | 1.00 | 1.04 | 1.00 |
| Npc1 | 1.39 | 1.26 | 1.23 | 1.98 | 1.98 | 1.93 | 0.80 | 1.20 | 0.68 | 1.12 | 1.03 | 1.21 |
| Npcd | 1.16 | 0.62 | 1.35 | 1.00 | 1.00 | 2.24 | 1.11 | 1.53 | 1.04 | 0.68 | 7.91 | 1.98 |
| Npdc1 | 1.14 | 1.31 | 1.25 | 0.87 | 2.80 | 0.86 | 0.77 | 1.37 | 0.85 | 0.94 | 1.39 | 0.77 |
| Npff | 0.91 | 1.75 | 1.06 | 0.88 | 2.80 | 1.57 | 0.82 | 1.73 | 1.00 | 1.49 | 1.72 | 1.32 |
| Npl | 1.00 | 0.88 | 1.00 | 1.19 | 1.00 | 1.57 | 1.22 | 0.34 | 1.02 | 0.92 | 0.88 | 0.52 |
| Npm3 | 0.69 | 1.07 | 1.52 | 1.65 | 10.89 | 1.65 | 0.99 | 2.29 | 0.97 | 1.10 | 1.66 | 0.86 |
| Nppb | 1.00 | 1.00 | 1.00 | 1.00 | 1.00 | 1.00 | 1.00 | 1.00 | 1.00 | 1.00 | 1.00 | 1.00 |
| Npr1 | 1.01 | 1.30 | 1.33 | 2.14 | 4.26 | 1.60 | 0.93 | 1.70 | 0.94 | 1.05 | 0.97 | 0.91 |
| Nptx1 | 1.00 | 1.00 | 0.89 | 1.00 | 1.00 | 1.00 | 1.00 | 1.00 | 1.00 | 1.00 | 10.34 | 1.00 |
| Nptxr | 0.78 | 1.87 | 0.83 | 2.53 | 1.00 | 0.70 | 1.00 | 1.00 | 1.00 | 1.30 | 11.84 | 0.66 |
| Nr1h3 | 1.14 | 1.25 | 1.43 | 0.94 | 2.79 | 1.03 | 1.01 | 3.19 | 1.10 | 0.67 | 0.85 | 0.69 |
| Nr1h4 | 1.44 | 1.67 | 1.28 | 1.37 | 1.00 | 1.00 | 1.00 | 1.00 | 1.00 | 2.57 | 1.67 | 1.69 |
| Nr2c2ap | 0.85 | 0.99 | 1.02 | 1.48 | 1.62 | 1.16 | 0.77 | 3.54 | 0.83 | 1.29 | 1.44 | 1.12 |
| Nr4a1 | 2.42 | 3.60 | 1.35 | 2.17 | 1.30 | 2.46 | 1.04 | 1.34 | 1.15 | 0.54 | 0.57 | 0.65 |
| Nr4a2 | 1.11 | 1.41 | 0.86 | 1.00 | 1.00 | 1.00 | 1.00 | 1.00 | 1.00 | 0.98 | 1.48 | 1.00 |
| Nr4a3 | 1.89 | 3.01 | 0.99 | 19.21 | 1.00 | 4.38 | 1.11 | 1.46 | 1.27 | 0.87 | 1.00 | 0.93 |
| Nrbp1 | 1.18 | 1.16 | 1.03 | 1.09 | 2.16 | 1.09 | 1.04 | 2.57 | 0.97 | 1.11 | 1.09 | 0.92 |
| Nrg4 | 1.20 | 2.62 | 1.33 | 0.35 | 0.21 | 0.63 | 1.00 | 1.00 | 1.00 | 1.01 | 0.94 | 0.86 |
| Nrsn1 | 1.72 | 1.34 | 1.33 | 1.00 | 1.00 | 1.00 | 1.00 | 1.00 | 1.00 | 1.00 | 20.51 | 1.00 |
| Nrsn2 | 1.00 | 1.00 | 1.10 | 1.00 | 1.00 | 1.00 | 1.00 | 1.00 | 1.00 | 1.00 | 10.11 | 1.00 |
| Nrtn | 1.22 | 1.77 | 1.17 | 1.47 | 9.78 | 2.31 | 1.08 | 4.14 | 1.04 | 1.00 | 1.00 | 1.00 |
| Nrxn1 | 1.00 | 1.00 | 1.00 | 1.00 | 1.00 | 1.00 | 1.10 | 1.82 | 1.17 | 1.00 | 5.27 | 1.00 |
| Nsg1 | 1.02 | 1.19 | 1.25 | 0.99 | 0.55 | 0.85 | 1.05 | 1.03 | 0.87 | 0.95 | 9.35 | 1.15 |
| Nsmce1 | 0.95 | 0.92 | 1.09 | 1.18 | 1.95 | 1.16 | 0.95 | 1.98 | 1.02 | 0.85 | 1.10 | 1.00 |
| Nsun5 | 0.91 | 0.89 | 1.30 | 1.10 | 3.65 | 1.37 | 1.19 | 1.84 | 0.78 | 1.29 | 1.46 | 1.13 |
| Nt5c | 0.89 | 0.97 | 0.80 | 0.92 | 2.18 | 0.80 | 0.77 | 2.83 | 1.01 | 1.12 | 1.22 | 1.07 |
| Nt5dc2 | 0.52 | 0.78 | 1.06 | 0.65 | 0.87 | 0.91 | 0.99 | 1.30 | 1.13 | 1.09 | 1.63 | 0.79 |
| Ntan1 | 0.99 | 0.91 | 0.98 | 0.67 | 2.82 | 0.74 | 1.31 | 2.01 | 0.77 | 1.08 | 1.36 | 0.88 |
| Nthl1 | 1.52 | 0.50 | 0.90 | 0.62 | 1.76 | 0.66 | 0.76 | 3.48 | 1.06 | 1.09 | 1.68 | 1.34 |
| Ntm | 1.00 | 1.00 | 1.00 | 1.00 | 1.00 | 1.00 | 1.55 | 3.79 | 2.59 | 1.00 | 7.11 | 0.98 |
| Ntmt1 | 1.01 | 0.97 | 1.01 | 1.11 | 13.01 | 0.98 | 0.91 | 1.44 | 1.02 | 1.11 | 1.47 | 1.00 |
| Ntn5 | 1.00 | 1.00 | 1.00 | 1.00 | 1.00 | 1.00 | 2.48 | 5.06 | 2.71 | 0.98 | 0.70 | 0.51 |
| Ntrk2 | 1.00 | 1.00 | 1.00 | 0.80 | 0.76 | 0.75 | 0.74 | 1.00 | 1.00 | 1.00 | 9.75 | 1.00 |
| Ntsr2 | 1.00 | 1.00 | 1.00 | 0.38 | 1.00 | 0.32 | 1.00 | 1.00 | 1.00 | 1.00 | 7.23 | 1.00 |
| Nubp2 | 0.94 | 0.94 | 1.00 | 1.17 | 7.52 | 0.91 | 0.94 | 0.64 | 0.97 | 1.04 | 1.25 | 0.87 |
| Nubpl | 1.14 | 1.00 | 1.00 | 0.75 | 2.24 | 0.72 | 1.14 | 1.74 | 0.78 | 1.09 | 1.30 | 1.00 |
| Nudt1 | 0.92 | 0.70 | 0.74 | 0.88 | 7.24 | 0.67 | 1.01 | 2.00 | 1.09 | 1.14 | 1.43 | 0.99 |
| Nudt14 | 0.71 | 0.98 | 0.83 | 1.14 | 1.72 | 1.07 | 0.90 | 1.36 | 0.92 | 0.93 | 1.46 | 1.07 |
| Nudt18 | 1.16 | 1.14 | 1.26 | 2.82 | 4.75 | 1.90 | 0.95 | 1.11 | 0.97 | 1.16 | 1.32 | 0.96 |
| Nudt8 | 0.85 | 0.96 | 0.96 | 0.55 | 1.52 | 0.84 | 0.68 | 1.76 | 1.55 | 0.99 | 1.34 | 0.91 |
| Nufip1 | 1.23 | 1.42 | 1.39 | 1.39 | 1.62 | 1.17 | 1.24 | 2.18 | 0.79 | 1.41 | 1.26 | 1.16 |
| Nupr1l | 1.68 | 1.19 | 1.34 | 1.11 | 1.00 | 1.10 | 0.90 | 0.49 | 0.96 | 1.22 | 1.46 | 0.72 |
| Nxn | 0.99 | 0.88 | 1.00 | 1.68 | 4.57 | 1.56 | 1.02 | 1.73 | 1.16 | 1.07 | 1.37 | 0.99 |
| Oas1a | 6.64 | 15.27 | 6.59 | 2.64 | 3.50 | 3.76 | 1.00 | 1.00 | 1.00 | 10.77 | 8.78 | 8.54 |
| Oas1c | 1.90 | 2.45 | 2.24 | 1.25 | 1.53 | 1.02 | 1.00 | 1.00 | 1.00 | 1.25 | 1.26 | 1.28 |
| Oas1g | 12.84 | 12.73 | 6.93 | 1.47 | 1.65 | 1.79 | 1.00 | 1.00 | 1.00 | 3.12 | 3.21 | 2.77 |
| Oas2 | 14.87 | 20.60 | 14.73 | 4.94 | 1.00 | 5.92 | 1.00 | 1.00 | 1.00 | 10.28 | 5.61 | 5.41 |
| Oas3 | 4.35 | 5.32 | 2.75 | 1.00 | 1.00 | 1.00 | 1.00 | 1.00 | 1.00 | 7.75 | 3.33 | 3.71 |
| Oasl1 | 1.01 | 1.43 | 0.74 | 2.61 | 1.00 | 2.89 | 1.00 | 1.00 | 1.00 | 11.15 | 10.43 | 6.55 |
| Oasl2 | 14.09 | 20.06 | 12.19 | 3.20 | 1.14 | 3.38 | 1.03 | 1.00 | 1.41 | 4.32 | 2.42 | 3.72 |
| Oaz1-ps | 0.31 | 1.00 | 0.03 | 12.69 | 1.00 | 0.20 | 1.00 | 1.00 | 0.21 | 1.00 | 1.00 | 0.95 |
| Oaz3 | 1.00 | 1.00 | 1.00 | 3.02 | 3.56 | 1.24 | 0.92 | 1.78 | 0.98 | 1.00 | 1.00 | 1.00 |
| Obp2a | 13.41 | 20.77 | 8.62 | 1.00 | 1.00 | 1.00 | 1.00 | 1.00 | 1.00 | 1.00 | 1.00 | 1.00 |

Fig. 35- 224

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Nme5 | 1.00 | 1.00 | 1.00 | 1.19 | 11.98 | 1.28 | 1.32 | 4.03 | 1.00 | 1.00 | 1.00 | 1.00 |
| Nme7 | 1.00 | 1.00 | 1.00 | 1.12 | 0.78 | 0.91 | 0.93 | 5.51 | 0.81 | 2.47 | 1.23 | 1.28 |
| Nmi | 1.00 | 1.00 | 1.00 | 1.00 | 0.49 | 1.00 | 1.20 | 8.68 | 0.93 | 2.34 | 1.16 | 1.40 |
| Nnat | 0.70 | 1.00 | 0.38 | 1.25 | 1.17 | 1.17 | 0.59 | 0.62 | 0.36 | 1.00 | 1.00 | 0.42 |
| Nnmt | 1.00 | 1.00 | 1.00 | 1.00 | 0.06 | 1.00 | 3.47 | 20.83 | 1.30 | 1.00 | 1.00 | 1.00 |
| Nob1 | 0.72 | 0.89 | 1.12 | 1.04 | 1.04 | 0.93 | 0.97 | 3.49 | 0.99 | 1.49 | 0.89 | 1.01 |
| Noc2l | 1.09 | 0.83 | 1.00 | 1.00 | 6.52 | 0.97 | 1.08 | 1.64 | 0.94 | 1.04 | 1.02 | 0.89 |
| Nol12 | 1.31 | 1.74 | 1.26 | 1.17 | 0.97 | 0.93 | 0.99 | 12.86 | 0.77 | 3.21 | 1.12 | 1.10 |
| Nol7 | 0.89 | 0.69 | 0.89 | 0.86 | 0.80 | 0.93 | 0.84 | 3.12 | 0.94 | 1.39 | 0.99 | 0.93 |
| Nop16 | 1.29 | 1.27 | 1.23 | 1.10 | 1.48 | 0.99 | 0.96 | 4.69 | 0.86 | 1.41 | 0.95 | 0.94 |
| Npas2 | 1.00 | 1.00 | 1.00 | 1.17 | 0.90 | 1.20 | 1.23 | 0.59 | 1.83 | 1.00 | 1.00 | 1.00 |
| Npc1 | 1.30 | 1.19 | 0.91 | 0.97 | 0.75 | 0.91 | 1.58 | 3.52 | 1.74 | 1.44 | 1.05 | 1.13 |
| Npcd | 1.00 | 1.00 | 1.00 | 1.37 | 1.11 | 1.13 | 0.78 | 1.02 | 0.91 | 1.00 | 1.00 | 1.00 |
| Npdc1 | 1.67 | 1.69 | 1.39 | 1.20 | 1.10 | 1.05 | 1.21 | 7.15 | 0.99 | 1.00 | 1.00 | 1.00 |
| Npff | 1.03 | 1.00 | 1.00 | 0.86 | 0.31 | 1.79 | 1.17 | 7.60 | 0.88 | 2.48 | 1.68 | 1.15 |
| Npl | 1.00 | 1.00 | 1.00 | 0.90 | 1.00 | 1.14 | 0.42 | 0.24 | 0.35 | 0.54 | 1.06 | 2.20 |
| Npm3 | 0.70 | 1.00 | 1.01 | 1.00 | 5.53 | 1.00 | 1.34 | 8.31 | 0.85 | 2.87 | 1.17 | 0.83 |
| Nppb | 1.00 | 1.00 | 1.00 | 1.00 | 1.00 | 1.00 | 1.00 | 1.00 | 1.00 | 1.00 | 1.00 | 1.00 |
| Npr1 | 1.00 | 1.00 | 1.00 | 1.02 | 0.45 | 1.16 | 1.29 | 4.72 | 1.62 | 1.00 | 1.00 | 1.00 |
| Nptx1 | 1.00 | 1.00 | 1.00 | 1.14 | 1.22 | 1.06 | 1.18 | 0.80 | 0.86 | 1.00 | 1.00 | 1.00 |
| Nptxr | 1.00 | 1.00 | 1.00 | 0.67 | 0.18 | 0.92 | 1.15 | 1.00 | 1.00 | 1.00 | 1.00 | 1.00 |
| Nr1h3 | 2.47 | 2.68 | 2.61 | 1.90 | 0.99 | 1.06 | 1.54 | 16.26 | 1.23 | 2.20 | 0.68 | 0.69 |
| Nr1h4 | 0.64 | 0.93 | 0.97 | 1.00 | 1.00 | 1.00 | 11.01 | 1.00 | 6.07 | 1.00 | 1.00 | 1.00 |
| Nr2c2ap | 1.08 | 1.00 | 1.19 | 0.96 | 1.15 | 1.06 | 1.33 | 7.32 | 1.03 | 2.80 | 1.38 | 1.03 |
| Nr4a1 | 1.31 | 8.76 | 1.00 | 1.40 | 0.81 | 1.31 | 1.94 | 0.80 | 1.23 | 0.28 | 0.63 | 0.63 |
| Nr4a2 | 1.75 | 7.02 | 1.27 | 1.12 | 1.00 | 1.07 | 1.33 | 0.77 | 1.54 | 1.00 | 1.00 | 1.00 |
| Nr4a3 | 1.00 | 1.00 | 1.00 | 0.97 | 1.00 | 0.89 | 1.45 | 1.00 | 1.00 | 1.00 | 1.00 | 1.00 |
| Nrbp1 | 1.34 | 1.02 | 0.90 | 1.09 | 0.99 | 1.05 | 1.08 | 5.96 | 1.06 | 2.24 | 1.29 | 1.08 |
| Nrg4 | 1.00 | 1.00 | 1.00 | 1.16 | 0.53 | 0.91 | 1.43 | 0.69 | 1.31 | 1.29 | 0.99 | 1.33 |
| Nrsn1 | 1.00 | 1.00 | 1.00 | 1.13 | 1.27 | 1.06 | 1.00 | 1.00 | 1.00 | 1.00 | 1.00 | 1.00 |
| Nrsn2 | 1.00 | 1.00 | 1.00 | 1.09 | 1.04 | 1.11 | 1.00 | 1.00 | 1.00 | 1.00 | 1.00 | 1.00 |
| Nrtn | 1.23 | 1.96 | 1.10 | 1.27 | 0.97 | 1.74 | 1.60 | 19.63 | 0.84 | 1.00 | 1.00 | 1.00 |
| Nrxn1 | 1.00 | 1.00 | 1.00 | 0.85 | 0.83 | 0.95 | 1.00 | 1.00 | 1.00 | 1.00 | 1.00 | 1.00 |
| Nsg1 | 0.86 | 0.37 | 0.52 | 1.08 | 1.03 | 1.03 | 1.09 | 0.46 | 0.98 | 1.00 | 1.00 | 1.00 |
| Nsmce1 | 1.00 | 1.00 | 0.95 | 1.51 | 1.50 | 1.25 | 1.10 | 5.02 | 0.78 | 1.35 | 0.94 | 1.00 |
| Nsun5 | 1.04 | 1.03 | 1.14 | 1.34 | 0.90 | 1.03 | 1.18 | 7.13 | 1.09 | 2.10 | 1.02 | 1.24 |
| Nt5c | 1.17 | 2.70 | 1.06 | 1.09 | 0.99 | 0.96 | 0.97 | 13.23 | 0.77 | 3.38 | 1.46 | 1.29 |
| Nt5dc2 | 1.00 | 1.00 | 1.00 | 1.01 | 1.10 | 0.49 | 0.91 | 5.59 | 0.81 | 2.95 | 1.15 | 1.38 |
| Ntan1 | 0.94 | 0.55 | 1.21 | 0.92 | 0.88 | 0.93 | 0.94 | 7.10 | 0.84 | 2.63 | 1.44 | 1.38 |
| Nthl1 | 0.89 | 1.13 | 0.96 | 1.41 | 0.85 | 0.96 | 1.31 | 8.77 | 0.94 | 2.35 | 1.20 | 0.76 |
| Ntm | 1.00 | 1.00 | 1.00 | 0.97 | 0.80 | 0.93 | 1.00 | 1.00 | 1.00 | 1.00 | 1.00 | 1.00 |
| Ntmt1 | 1.88 | 1.87 | 1.05 | 1.07 | 1.75 | 0.97 | 1.53 | 4.96 | 0.98 | 1.73 | 1.00 | 0.96 |
| Ntn5 | 1.00 | 1.00 | 1.00 | 1.05 | 0.68 | 0.82 | 1.00 | 1.71 | 1.00 | 1.00 | 1.00 | 1.00 |
| Ntrk2 | 1.00 | 1.00 | 1.00 | 0.95 | 1.40 | 0.99 | 0.85 | 0.47 | 1.09 | 1.00 | 1.00 | 1.00 |
| Ntsr2 | 1.00 | 1.00 | 1.00 | 0.87 | 0.73 | 0.86 | 1.00 | 1.00 | 1.00 | 1.00 | 1.00 | 1.00 |
| Nubp2 | 1.17 | 1.03 | 1.13 | 1.21 | 1.56 | 1.02 | 1.24 | 1.50 | 0.96 | 1.04 | 0.95 | 0.97 |
| Nubpl | 1.00 | 1.00 | 1.00 | 1.00 | 0.47 | 0.95 | 1.00 | 8.40 | 0.90 | 1.33 | 1.00 | 1.00 |
| Nudt1 | 1.00 | 1.00 | 0.75 | 1.77 | 1.47 | 0.88 | 1.17 | 10.11 | 1.12 | 1.92 | 0.77 | 0.98 |
| Nudt14 | 1.00 | 1.43 | 0.64 | 1.05 | 1.04 | 0.98 | 1.10 | 6.07 | 0.86 | 2.53 | 1.28 | 0.95 |
| Nudt18 | 1.08 | 1.06 | 0.93 | 1.20 | 1.16 | 1.11 | 1.39 | 3.34 | 0.89 | 1.51 | 1.52 | 1.29 |
| Nudt8 | 1.40 | 0.95 | 0.75 | 0.91 | 1.01 | 0.96 | 1.30 | 4.78 | 1.03 | 2.42 | 1.15 | 1.08 |
| Nufip1 | 1.10 | 1.00 | 1.00 | 1.03 | 0.70 | 1.09 | 1.05 | 5.27 | 1.09 | 2.21 | 1.23 | 0.91 |
| Nupr1l | 1.16 | 0.52 | 0.54 | 0.92 | 4.02 | 1.00 | 2.16 | 4.48 | 0.97 | 1.61 | 1.00 | 1.18 |
| Nxn | 1.88 | 1.48 | 1.02 | 1.12 | 0.72 | 1.08 | 0.80 | 2.86 | 0.86 | 2.13 | 1.30 | 1.26 |
| Oas1a | 1.00 | 1.00 | 1.00 | 1.00 | 1.00 | 1.00 | 1.00 | 1.49 | 1.00 | 18.76 | 12.15 | 12.55 |
| Oas1c | 1.00 | 1.00 | 1.00 | 1.00 | 4.88 | 1.00 | 0.85 | 4.72 | 0.62 | 5.65 | 2.53 | 2.78 |
| Oas1g | 1.00 | 1.00 | 1.00 | 1.00 | 1.00 | 1.00 | 1.00 | 1.68 | 1.00 | 12.61 | 5.62 | 4.75 |
| Oas2 | 1.00 | 1.00 | 1.00 | 1.00 | 1.00 | 1.00 | 1.00 | 1.00 | 1.00 | 7.53 | 13.19 | 12.56 |
| Oas3 | 1.00 | 1.00 | 1.00 | 1.00 | 1.00 | 1.00 | 1.00 | 1.00 | 1.00 | 22.42 | 17.73 | 15.23 |
| Oasl1 | 1.00 | 1.00 | 1.00 | 1.00 | 1.00 | 1.00 | 1.00 | 1.00 | 1.00 | 6.80 | 7.96 | 5.99 |
| Oasl2 | 1.00 | 1.00 | 1.00 | 1.22 | 1.00 | 2.42 | 1.21 | 1.00 | 1.50 | 12.30 | 17.44 | 17.93 |
| Oaz1-ps | 1.00 | 1.10 | 1.00 | 1.00 | 1.00 | 0.61 | 1.00 | 1.00 | 1.00 | 1.00 | 1.00 | 0.38 |
| Oaz3 | 1.00 | 1.00 | 1.00 | 0.96 | 1.00 | 0.75 | 9.90 | 3.31 | 1.00 | 1.00 | 1.00 | 1.00 |
| Obp2a | 1.00 | 1.00 | 1.00 | 1.00 | 1.00 | 1.00 | 1.00 | 1.00 | 1.00 | 1.00 | 1.00 | 1.00 |

Fig. 35- 225

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Ocel1 | 1.61 | 1.03 | 1.15 | 0.64 | 3.02 | 0.96 | 1.37 | 0.90 | 0.93 | 1.73 | 1.78 | 0.85 |
| Ocm | 1.00 | 1.00 | 1.00 | 1.00 | 1.00 | 1.00 | 1.00 | 1.00 | 1.00 | 1.00 | 1.00 | 1.00 |
| Odf1 | 1.00 | 1.00 | 1.00 | 1.00 | 1.00 | 1.00 | 1.00 | 1.00 | 1.00 | 1.00 | 1.00 | 1.00 |
| Odf3l2 | 3.21 | 5.36 | 1.14 | 1.00 | 2.65 | 1.00 | 1.00 | 1.00 | 1.00 | 1.00 | 1.00 | 1.00 |
| Ogfod2 | 1.14 | 0.48 | 0.74 | 0.50 | 7.77 | 0.87 | 1.22 | 0.94 | 0.92 | 2.41 | 3.20 | 0.98 |
| Ogfod3 | 0.88 | 0.63 | 0.85 | 0.31 | 3.61 | 1.25 | 0.87 | 0.90 | 0.71 | 1.18 | 2.19 | 1.00 |
| Ogfr | 1.24 | 0.83 | 1.00 | 0.94 | 6.94 | 1.23 | 1.06 | 1.00 | 1.09 | 2.40 | 2.72 | 1.06 |
| Ogfrl1 | 1.04 | 1.49 | 0.93 | 1.50 | 0.78 | 0.95 | 1.38 | 1.54 | 1.45 | 6.90 | 2.77 | 1.35 |
| Olfm1 | 3.37 | 0.82 | 1.85 | 0.71 | 0.06 | 0.99 | 0.69 | 0.68 | 0.82 | 0.54 | 0.78 | 0.75 |
| Olfm4 | 1.00 | 1.00 | 1.00 | 1.00 | 1.00 | 1.00 | 1.00 | 1.00 | 1.00 | 1.00 | 1.00 | 1.00 |
| Olfml2b | 0.91 | 0.58 | 1.21 | 0.69 | 0.48 | 0.72 | 0.53 | 0.42 | 0.63 | 1.04 | 0.89 | 0.93 |
| Olig1 | 1.00 | 1.00 | 1.00 | 0.88 | 0.72 | 0.43 | 1.00 | 1.00 | 1.00 | 1.00 | 1.00 | 1.00 |
| Omg | 1.00 | 1.00 | 1.00 | 1.00 | 0.20 | 1.00 | 1.00 | 1.00 | 1.00 | 1.00 | 1.00 | 1.00 |
| Orai2 | 1.47 | 1.00 | 1.10 | 1.00 | 0.60 | 1.00 | 1.34 | 1.00 | 1.75 | 0.73 | 0.71 | 1.17 |
| Orm1 | 4.04 | 9.71 | 2.92 | 0.48 | 9.51 | 1.30 | 1.00 | 1.00 | 1.00 | 7.35 | 6.42 | 1.14 |
| Orm2 | 1.70 | 4.07 | 1.01 | 0.28 | 19.10 | 3.08 | 1.00 | 1.00 | 1.00 | 5.91 | 6.55 | 0.65 |
| Orm3 | 1.00 | 5.58 | 1.00 | 0.35 | 22.28 | 1.97 | 1.89 | 1.00 | 1.00 | 2.55 | 4.40 | 0.59 |
| Osgep | 1.14 | 0.77 | 1.04 | 0.32 | 4.04 | 0.66 | 0.94 | 1.00 | 0.70 | 1.93 | 1.82 | 0.99 |
| Osr2 | 1.34 | 1.67 | 1.50 | 2.17 | 6.56 | 0.95 | 1.00 | 1.00 | 1.00 | 1.00 | 1.00 | 1.00 |
| Otos | 1.00 | 1.00 | 1.00 | 1.00 | 1.00 | 1.00 | 1.00 | 1.00 | 1.00 | 1.00 | 1.00 | 1.00 |
| Otud1 | 3.00 | 8.38 | 3.73 | 2.37 | 0.31 | 1.06 | 2.69 | 4.77 | 1.63 | 0.30 | 0.28 | 0.90 |
| Otulin | 1.91 | 0.91 | 1.14 | 0.46 | 5.24 | 0.95 | 1.85 | 1.85 | 1.31 | 1.46 | 2.21 | 0.85 |
| P2rx5 | 1.20 | 0.87 | 1.41 | 0.52 | 3.93 | 0.63 | 1.37 | 1.55 | 1.21 | 3.30 | 3.77 | 1.58 |
| P2rx6 | 0.93 | 0.54 | 0.80 | 0.36 | 1.91 | 0.70 | 0.80 | 0.52 | 0.63 | 1.71 | 1.93 | 1.03 |
| Pacsin3 | 1.01 | 0.75 | 0.93 | 0.93 | 6.74 | 1.39 | 0.89 | 0.88 | 1.01 | 1.94 | 2.71 | 1.19 |
| Padi1 | 1.00 | 1.00 | 1.00 | 1.00 | 1.00 | 1.00 | 1.00 | 1.00 | 1.00 | 1.00 | 1.00 | 1.00 |
| Padi3 | 1.00 | 1.00 | 1.00 | 1.00 | 1.00 | 1.00 | 1.00 | 1.00 | 1.00 | 1.00 | 1.00 | 1.00 |
| Paf1 | 1.38 | 0.96 | 1.10 | 0.38 | 5.16 | 1.27 | 0.96 | 0.88 | 0.96 | 1.42 | 2.28 | 0.96 |
| Pah | 1.00 | 1.00 | 1.00 | 1.00 | 1.00 | 1.00 | 0.50 | 0.68 | 0.74 | 1.00 | 1.00 | 1.00 |
| Palm | 1.15 | 0.55 | 0.89 | 0.69 | 3.64 | 0.90 | 0.95 | 0.73 | 0.81 | 2.69 | 2.21 | 0.83 |
| Pam16 | 1.58 | 0.69 | 0.81 | 0.24 | 8.87 | 1.31 | 1.37 | 0.85 | 1.01 | 1.90 | 2.16 | 1.96 |
| Panx2 | 1.00 | 1.00 | 1.00 | 1.00 | 0.29 | 1.00 | 1.00 | 1.00 | 0.56 | 1.00 | 1.00 | 1.00 |
| Paox | 1.90 | 1.95 | 2.07 | 1.59 | 6.86 | 1.77 | 1.70 | 1.14 | 1.71 | 6.48 | 5.58 | 1.82 |
| Papl | 1.00 | 1.00 | 1.00 | 1.00 | 1.00 | 1.00 | 1.00 | 1.00 | 1.00 | 1.00 | 1.00 | 1.00 |
| Paqr6 | 1.00 | 1.00 | 1.00 | 1.94 | 7.35 | 1.00 | 1.61 | 1.00 | 0.97 | 1.34 | 1.24 | 0.89 |
| Pard6a | 1.21 | 0.93 | 1.09 | 0.47 | 2.85 | 0.89 | 1.10 | 0.88 | 0.86 | 1.50 | 2.39 | 0.71 |
| Park7 | 1.26 | 0.68 | 0.72 | 0.41 | 7.61 | 1.05 | 0.89 | 0.68 | 0.78 | 1.82 | 2.92 | 0.93 |
| Parl | 1.08 | 0.51 | 0.93 | 0.35 | 3.97 | 0.86 | 1.04 | 0.77 | 0.83 | 2.48 | 3.31 | 1.11 |
| Parp6 | 1.17 | 0.66 | 0.95 | 0.95 | 4.71 | 0.89 | 1.30 | 1.28 | 1.10 | 2.23 | 4.02 | 0.84 |
| Pbld1 | 0.82 | 1.00 | 2.15 | 3.77 | 3.44 | 5.59 | 2.00 | 1.87 | 2.50 | 1.72 | 2.64 | 1.73 |
| Pbx4 | 1.00 | 1.00 | 1.00 | 1.00 | 1.02 | 1.00 | 1.00 | 1.00 | 1.00 | 1.75 | 2.36 | 1.00 |
| Pcbd2 | 0.56 | 0.72 | 1.37 | 0.26 | 4.41 | 0.93 | 0.95 | 0.99 | 0.96 | 1.11 | 1.45 | 0.80 |
| Pcdhga10 | 1.00 | 1.00 | 1.00 | 1.00 | 0.56 | 1.07 | 0.73 | 0.73 | 0.68 | 0.95 | 0.30 | 0.82 |
| Pcdhgc3 | 0.58 | 1.46 | 1.27 | 0.69 | 0.10 | 0.74 | 1.03 | 1.05 | 1.12 | 0.77 | 0.14 | 0.85 |
| Pcdhgc5 | 1.00 | 1.00 | 1.00 | 1.00 | 0.22 | 1.00 | 1.00 | 1.00 | 1.00 | 1.00 | 2.19 | 1.00 |
| Pck1 | 1.26 | 3.05 | 3.09 | 0.79 | 0.26 | 1.00 | 4.29 | 0.64 | 6.01 | 0.61 | 1.56 | 1.30 |
| Pck2 | 1.17 | 0.78 | 1.24 | 1.57 | 7.18 | 1.81 | 1.14 | 1.20 | 0.86 | 2.13 | 2.46 | 1.08 |
| Pcp4 | 1.09 | 0.97 | 0.89 | 1.00 | 0.03 | 1.00 | 0.20 | 0.31 | 0.38 | 0.98 | 3.89 | 1.14 |
| Pcsk1n | 1.00 | 1.00 | 1.00 | 1.00 | 0.08 | 1.00 | 1.00 | 1.00 | 1.00 | 1.04 | 1.00 | 1.00 |
| Pcsk2 | 1.00 | 1.00 | 1.00 | 1.00 | 0.21 | 1.00 | 1.00 | 1.00 | 1.00 | 1.00 | 1.00 | 1.00 |
| Pcyt2 | 0.88 | 0.54 | 0.84 | 0.28 | 3.71 | 0.80 | 1.18 | 0.89 | 0.97 | 2.07 | 3.16 | 1.06 |
| Pdcd5 | 1.45 | 0.55 | 0.85 | 0.18 | 4.50 | 1.10 | 1.33 | 0.91 | 0.78 | 3.85 | 3.57 | 0.98 |
| Pddc1 | 0.96 | 0.47 | 0.90 | 1.02 | 8.07 | 1.24 | 0.80 | 0.82 | 0.79 | 2.61 | 2.49 | 0.98 |
| Pde4b | 1.68 | 2.91 | 1.21 | 2.10 | 0.55 | 0.87 | 0.99 | 1.11 | 0.96 | 0.72 | 1.12 | 1.44 |
| Pde4d | 1.07 | 1.62 | 0.98 | 2.47 | 1.79 | 2.03 | 1.14 | 1.42 | 1.03 | 1.04 | 1.26 | 1.14 |
| Pde6h | 1.00 | 1.00 | 1.00 | 1.00 | 1.00 | 1.00 | 1.00 | 1.00 | 1.00 | 1.79 | 1.00 | 1.00 |
| Pde9a | 1.00 | 0.97 | 1.00 | 1.00 | 2.50 | 1.00 | 1.00 | 1.00 | 1.00 | 3.45 | 3.68 | 1.22 |
| Pdia2 | 1.00 | 1.00 | 1.00 | 1.00 | 1.00 | 1.00 | 1.00 | 1.00 | 1.00 | 1.00 | 1.00 | 1.00 |
| Pdia6 | 1.58 | 1.11 | 1.27 | 1.26 | 6.02 | 1.64 | 1.03 | 0.97 | 1.24 | 1.15 | 2.12 | 1.27 |
| Pdk4 | 1.11 | 2.09 | 1.64 | 3.00 | 0.41 | 1.62 | 1.23 | 1.26 | 1.32 | 1.05 | 0.99 | 2.34 |
| Pdlim1 | 1.19 | 0.66 | 0.73 | 0.95 | 1.89 | 1.11 | 0.87 | 0.70 | 0.74 | 0.73 | 0.98 | 0.88 |
| Pdlim2 | 0.79 | 0.80 | 1.41 | 0.82 | 3.28 | 1.39 | 0.80 | 0.51 | 0.98 | 1.20 | 1.67 | 1.16 |
| Pdlim7 | 1.26 | 0.73 | 0.82 | 0.72 | 3.58 | 1.40 | 1.34 | 0.87 | 1.09 | 1.91 | 2.11 | 0.97 |
| Pdrg1 | 1.14 | 0.75 | 0.94 | 0.48 | 4.47 | 1.02 | 0.96 | 0.85 | 0.85 | 1.81 | 2.10 | 0.96 |

Fig. 35- 226

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Ocel1 | 1.13 | 1.44 | 1.11 | 1.23 | 0.83 | 1.25 | 1.09 | 1.83 | 0.72 | 1.14 | 1.43 | 1.04 |
| Ocm | 1.00 | 1.00 | 1.00 | 1.00 | 1.00 | 1.00 | 1.00 | 1.00 | 1.00 | 1.00 | 1.00 | 1.00 |
| Odf1 | 1.00 | 1.00 | 1.00 | 1.00 | 1.00 | 1.00 | 1.00 | 1.00 | 1.00 | 1.00 | 1.00 | 1.00 |
| Odf3l2 | 1.76 | 1.23 | 1.00 | 1.00 | 1.00 | 1.00 | 1.00 | 1.00 | 1.00 | 1.00 | 1.00 | 1.00 |
| Ogfod2 | 1.27 | 1.61 | 0.88 | 1.07 | 0.58 | 1.01 | 0.87 | 2.73 | 0.79 | 0.95 | 1.63 | 0.95 |
| Ogfod3 | 1.33 | 1.97 | 1.38 | 1.01 | 0.77 | 0.99 | 0.83 | 0.33 | 0.85 | 1.16 | 1.46 | 0.77 |
| Ogfr | 1.20 | 1.62 | 1.09 | 1.06 | 0.82 | 0.98 | 1.21 | 1.75 | 1.22 | 1.21 | 1.79 | 1.19 |
| Ogfrl1 | 1.53 | 1.14 | 1.28 | 1.17 | 5.40 | 1.29 | 0.70 | 6.40 | 0.49 | 1.02 | 1.49 | 1.20 |
| Olfm1 | 1.22 | 0.85 | 1.18 | 1.11 | 0.92 | 0.93 | 1.29 | 1.95 | 0.93 | 1.09 | 1.12 | 1.14 |
| Olfm4 | 0.76 | 0.39 | 1.26 | 0.59 | 1.00 | 1.01 | 1.00 | 1.00 | 1.00 | 1.00 | 1.00 | 1.00 |
| Olfml2b | 0.97 | 0.63 | 0.76 | 0.70 | 1.00 | 0.63 | 1.00 | 1.00 | 1.00 | 1.08 | 0.69 | 1.17 |
| Olig1 | 1.00 | 1.00 | 1.00 | 1.00 | 1.00 | 1.00 | 2.23 | 11.49 | 1.00 | 1.00 | 1.00 | 1.00 |
| Omg | 1.40 | 1.26 | 1.00 | 1.00 | 1.00 | 1.00 | 1.00 | 1.00 | 1.00 | 1.19 | 1.07 | 1.00 |
| Orai2 | 0.68 | 0.64 | 0.92 | 0.82 | 1.00 | 1.23 | 1.00 | 1.00 | 1.00 | 1.02 | 0.64 | 0.84 |
| Orm1 | 2.28 | 1.00 | 0.91 | 1.00 | 1.00 | 1.00 | 2.77 | 8.86 | 2.72 | 1.00 | 1.00 | 1.00 |
| Orm2 | 1.77 | 0.91 | 1.54 | 1.00 | 1.00 | 1.00 | 5.63 | 13.53 | 2.23 | 1.00 | 1.00 | 1.00 |
| Orm3 | 1.00 | 1.00 | 1.00 | 1.00 | 1.00 | 1.00 | 6.47 | 129.14 | 4.28 | 1.00 | 1.00 | 1.00 |
| Osgep | 0.94 | 1.13 | 0.92 | 0.83 | 0.65 | 0.84 | 1.00 | 0.52 | 0.78 | 1.11 | 0.97 | 1.00 |
| Osr2 | 0.46 | 0.24 | 0.46 | 1.34 | 1.34 | 1.55 | 1.00 | 1.00 | 1.00 | 1.11 | 1.08 | 1.14 |
| Otos | 0.84 | 2.08 | 1.13 | 1.00 | 1.00 | 1.00 | 1.00 | 1.00 | 1.00 | 1.00 | 1.00 | 1.00 |
| Otud1 | 0.99 | 1.15 | 0.93 | 1.40 | 1.00 | 1.47 | 0.97 | 1.00 | 1.50 | 1.06 | 0.87 | 1.08 |
| Otulin | 1.31 | 1.46 | 1.05 | 0.96 | 0.87 | 0.98 | 1.05 | 1.71 | 0.87 | 1.01 | 1.78 | 1.11 |
| P2rx5 | 1.00 | 1.00 | 1.00 | 0.91 | 0.46 | 0.69 | 1.00 | 1.00 | 1.00 | 1.00 | 1.35 | 1.00 |
| P2rx6 | 1.82 | 2.57 | 1.69 | 1.00 | 1.44 | 1.00 | 1.00 | 1.00 | 1.00 | 0.63 | 1.34 | 0.85 |
| Pacsin3 | 1.68 | 1.69 | 1.32 | 0.92 | 1.13 | 0.95 | 0.95 | 0.87 | 1.03 | 0.81 | 1.15 | 0.86 |
| Padi1 | 1.22 | 1.00 | 1.00 | 1.00 | 1.00 | 1.00 | 1.00 | 1.00 | 1.00 | 1.00 | 1.00 | 1.00 |
| Padi3 | 1.19 | 1.31 | 1.00 | 1.00 | 1.00 | 1.00 | 1.00 | 1.00 | 1.00 | 1.00 | 1.00 | 1.00 |
| Paf1 | 1.17 | 1.36 | 0.97 | 0.76 | 0.84 | 0.92 | 0.87 | 0.90 | 0.94 | 0.87 | 1.40 | 0.98 |
| Pah | 1.31 | 1.00 | 1.00 | 1.08 | 1.77 | 0.92 | 1.07 | 0.82 | 0.76 | 1.00 | 1.00 | 1.00 |
| Palm | 0.77 | 1.09 | 0.79 | 0.71 | 0.42 | 0.92 | 1.00 | 2.34 | 1.03 | 0.79 | 1.23 | 0.94 |
| Pam16 | 0.77 | 1.04 | 1.43 | 0.75 | 0.60 | 0.74 | 1.90 | 3.35 | 1.12 | 1.31 | 2.29 | 0.95 |
| Panx2 | 1.00 | 1.00 | 1.00 | 1.00 | 1.00 | 1.00 | 1.00 | 1.00 | 1.00 | 1.00 | 1.00 | 1.00 |
| Paox | 1.89 | 1.99 | 2.05 | 1.59 | 8.20 | 1.92 | 2.20 | 8.74 | 1.28 | 1.33 | 1.87 | 1.35 |
| Papl | 1.00 | 1.00 | 1.00 | 1.00 | 1.00 | 1.00 | 1.00 | 1.00 | 1.00 | 1.00 | 1.00 | 1.00 |
| Paqr6 | 1.00 | 1.00 | 1.00 | 1.00 | 1.35 | 1.00 | 1.00 | 1.00 | 1.00 | 1.00 | 1.32 | 0.95 |
| Pard6a | 1.12 | 1.51 | 0.93 | 1.14 | 0.95 | 0.92 | 1.16 | 0.60 | 1.37 | 0.81 | 1.24 | 0.88 |
| Park7 | 1.18 | 1.63 | 0.94 | 0.92 | 0.78 | 0.97 | 1.13 | 1.67 | 1.00 | 0.97 | 1.77 | 1.31 |
| Parl | 1.25 | 1.30 | 0.96 | 0.92 | 0.60 | 0.86 | 0.97 | 1.27 | 0.93 | 1.01 | 1.44 | 1.03 |
| Parp6 | 0.97 | 1.06 | 0.85 | 1.21 | 0.80 | 1.11 | 0.85 | 1.55 | 0.77 | 1.06 | 1.21 | 0.96 |
| Pbld1 | 1.68 | 1.06 | 1.00 | 1.23 | 1.12 | 1.23 | 0.80 | 0.55 | 1.04 | 1.23 | 1.17 | 1.37 |
| Pbx4 | 1.14 | 1.41 | 1.21 | 1.00 | 0.48 | 1.00 | 1.00 | 1.00 | 1.00 | 1.00 | 1.00 | 1.00 |
| Pcbd2 | 1.12 | 1.60 | 0.77 | 0.74 | 0.73 | 0.95 | 1.16 | 0.76 | 0.69 | 0.87 | 1.41 | 1.12 |
| Pcdhga10 | 1.18 | 0.90 | 1.14 | 1.00 | 1.00 | 1.00 | 1.00 | 1.00 | 1.00 | 0.73 | 0.83 | 0.72 |
| Pcdhgc3 | 1.33 | 0.90 | 1.51 | 0.95 | 1.00 | 0.92 | 1.12 | 1.00 | 0.97 | 1.10 | 0.66 | 1.01 |
| Pcdhgc5 | 1.00 | 1.00 | 1.00 | 1.00 | 1.00 | 1.00 | 1.00 | 1.00 | 1.00 | 1.00 | 0.88 | 1.34 |
| Pck1 | 0.66 | 0.73 | 0.56 | 1.41 | 2.93 | 1.31 | 1.32 | 0.48 | 1.40 | 1.27 | 1.46 | 1.60 |
| Pck2 | 1.88 | 2.61 | 1.45 | 0.96 | 0.76 | 0.91 | 1.30 | 1.50 | 1.16 | 1.05 | 1.35 | 1.01 |
| Pcp4 | 2.25 | 0.46 | 0.32 | 0.60 | 1.04 | 0.51 | 1.00 | 1.00 | 1.00 | 0.92 | 1.54 | 0.92 |
| Pcsk1n | 1.00 | 1.00 | 1.00 | 1.00 | 1.00 | 1.00 | 1.00 | 1.00 | 1.00 | 1.37 | 1.75 | 1.36 |
| Pcsk2 | 1.00 | 1.00 | 1.00 | 1.00 | 1.00 | 1.00 | 1.00 | 1.00 | 1.00 | 1.34 | 1.50 | 0.94 |
| Pcyt2 | 1.28 | 1.53 | 0.91 | 0.92 | 0.72 | 1.01 | 0.86 | 1.04 | 0.93 | 1.05 | 1.40 | 1.08 |
| Pdcd5 | 1.27 | 1.18 | 0.69 | 0.58 | 0.70 | 1.74 | 1.81 | 2.69 | 1.13 | 1.21 | 1.33 | 1.11 |
| Pddc1 | 1.20 | 1.48 | 1.13 | 0.96 | 0.72 | 0.96 | 1.65 | 3.30 | 1.19 | 0.82 | 1.39 | 0.93 |
| Pde4b | 0.96 | 0.82 | 1.14 | 0.85 | 0.80 | 1.11 | 0.58 | 1.00 | 0.83 | 0.97 | 0.86 | 1.08 |
| Pde4d | 0.88 | 0.80 | 0.89 | 1.16 | 0.97 | 1.24 | 1.23 | 1.00 | 1.66 | 1.09 | 0.96 | 1.04 |
| Pde6h | 1.00 | 1.00 | 1.00 | 1.00 | 1.00 | 1.00 | 7.94 | 34.75 | 5.93 | 1.00 | 1.00 | 1.00 |
| Pde9a | 1.00 | 1.00 | 1.00 | 0.89 | 0.90 | 0.95 | 0.73 | 0.53 | 0.54 | 1.17 | 2.01 | 1.07 |
| Pdia2 | 1.00 | 1.00 | 1.00 | 1.00 | 1.00 | 1.00 | 1.00 | 1.00 | 1.00 | 0.38 | 2.84 | 5.10 |
| Pdia6 | 1.41 | 1.45 | 1.33 | 1.09 | 1.43 | 1.39 | 0.96 | 0.83 | 1.25 | 1.27 | 1.65 | 1.41 |
| Pdk4 | 4.90 | 3.44 | 2.23 | 2.32 | 4.80 | 1.92 | 11.67 | 1.84 | 5.46 | 1.74 | 1.36 | 1.92 |
| Pdlim1 | 1.26 | 1.15 | 0.94 | 0.84 | 0.90 | 0.44 | 4.00 | 1.61 | 1.66 | 1.26 | 1.55 | 1.23 |
| Pdlim2 | 0.96 | 1.12 | 1.00 | 1.12 | 1.14 | 1.29 | 1.00 | 1.00 | 1.12 | 1.14 | 1.55 | 1.06 |
| Pdlim7 | 1.45 | 1.68 | 1.36 | 0.86 | 0.93 | 0.95 | 0.67 | 1.25 | 1.02 | 1.03 | 1.44 | 1.09 |
| Pdrg1 | 1.13 | 1.45 | 1.07 | 1.20 | 0.69 | 0.85 | 0.69 | 0.75 | 0.55 | 0.91 | 1.48 | 1.16 |

Fig. 35- 227

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Ocel1 | 1.15 | 1.05 | 0.89 | 1.31 | 2.11 | 0.90 | 0.82 | 1.61 | 1.02 | 0.94 | 1.17 | 0.98 |
| Ocm | 1.00 | 1.00 | 1.00 | 1.00 | 1.00 | 1.00 | 1.00 | 1.00 | 1.00 | 1.00 | 1.00 | 1.00 |
| Odf1 | 1.00 | 1.00 | 1.00 | 3.54 | 1.34 | 0.82 | 0.97 | 0.71 | 1.00 | 1.00 | 1.00 | 1.00 |
| Odf3l2 | 1.00 | 1.00 | 1.00 | 1.00 | 1.00 | 1.00 | 1.00 | 1.00 | 1.00 | 1.00 | 1.00 | 1.00 |
| Ogfod2 | 0.99 | 1.22 | 1.11 | 1.00 | 1.53 | 0.90 | 1.07 | 3.48 | 1.05 | 1.10 | 1.44 | 1.07 |
| Ogfod3 | 0.76 | 1.41 | 1.30 | 0.87 | 5.85 | 1.19 | 0.59 | 1.37 | 1.13 | 1.32 | 1.36 | 0.91 |
| Ogfr | 1.26 | 1.63 | 1.18 | 1.01 | 1.75 | 1.10 | 0.93 | 2.25 | 0.97 | 1.23 | 1.40 | 1.06 |
| Ogfrl1 | 1.41 | 1.07 | 1.47 | 0.78 | 5.93 | 0.82 | 1.00 | 1.00 | 1.00 | 1.02 | 1.11 | 1.00 |
| Olfm1 | 1.20 | 1.33 | 1.56 | 1.32 | 1.67 | 0.61 | 0.77 | 0.75 | 0.70 | 0.60 | 5.13 | 0.78 |
| Olfm4 | 1.30 | 1.19 | 1.01 | 1.00 | 1.00 | 1.00 | 1.00 | 1.00 | 1.00 | 5.08 | 1.15 | 2.05 |
| Olfml2b | 0.98 | 0.88 | 0.90 | 0.99 | 0.58 | 1.05 | 0.76 | 0.78 | 0.86 | 0.61 | 0.46 | 0.57 |
| Olig1 | 1.00 | 1.00 | 1.00 | 1.00 | 1.00 | 1.00 | 0.68 | 0.99 | 0.68 | 1.00 | 8.59 | 1.00 |
| Omg | 1.00 | 1.00 | 1.00 | 1.00 | 1.00 | 1.00 | 1.00 | 1.00 | 1.00 | 1.00 | 8.24 | 1.00 |
| Orai2 | 0.86 | 0.77 | 0.84 | 1.04 | 1.00 | 1.47 | 0.92 | 0.88 | 1.13 | 0.86 | 0.62 | 1.05 |
| Orm1 | 1.26 | 1.00 | 1.00 | 0.62 | 1.30 | 0.36 | 1.00 | 1.00 | 1.00 | 1.00 | 1.00 | 1.00 |
| Orm2 | 1.00 | 1.00 | 1.00 | 1.05 | 1.63 | 0.75 | 1.00 | 1.00 | 1.00 | 1.25 | 0.73 | 0.95 |
| Orm3 | 1.00 | 1.00 | 1.00 | 0.95 | 2.22 | 0.84 | 1.00 | 1.00 | 1.00 | 1.00 | 1.00 | 1.00 |
| Osgep | 0.87 | 1.01 | 1.04 | 0.81 | 0.95 | 0.80 | 0.91 | 2.35 | 0.86 | 0.79 | 1.42 | 1.11 |
| Osr2 | 1.00 | 1.00 | 1.00 | 1.03 | 1.00 | 1.00 | 1.17 | 0.65 | 1.18 | 1.00 | 1.00 | 1.00 |
| Otos | 1.00 | 1.00 | 1.00 | 1.00 | 1.26 | 1.00 | 1.00 | 1.00 | 1.00 | 1.00 | 1.00 | 1.00 |
| Otud1 | 1.03 | 1.19 | 1.02 | 1.12 | 0.83 | 1.09 | 0.71 | 0.93 | 1.07 | 1.27 | 0.84 | 1.15 |
| Otulin | 1.11 | 1.27 | 1.06 | 0.96 | 2.20 | 1.08 | 1.12 | 1.87 | 0.99 | 1.35 | 1.51 | 1.12 |
| P2rx5 | 1.00 | 1.00 | 1.00 | 0.69 | 0.51 | 0.51 | 0.79 | 2.55 | 1.00 | 1.00 | 1.00 | 1.00 |
| P2rx6 | 0.87 | 0.66 | 1.29 | 0.71 | 1.51 | 0.99 | 1.00 | 1.91 | 0.85 | 1.00 | 1.00 | 1.00 |
| Pacsin3 | 1.13 | 1.07 | 1.09 | 0.86 | 1.30 | 1.08 | 0.64 | 1.38 | 1.27 | 1.38 | 1.51 | 0.96 |
| Padi1 | 0.99 | 1.28 | 1.27 | 1.00 | 1.00 | 1.00 | 1.00 | 1.00 | 1.00 | 1.00 | 1.00 | 1.00 |
| Padi3 | 1.00 | 1.00 | 1.00 | 1.00 | 1.00 | 1.00 | 1.03 | 2.36 | 1.10 | 1.00 | 1.00 | 1.00 |
| Paf1 | 1.11 | 1.15 | 1.16 | 1.10 | 2.57 | 1.07 | 1.05 | 1.27 | 0.92 | 1.11 | 1.33 | 1.07 |
| Pah | 1.05 | 1.82 | 1.46 | 5.90 | 1.00 | 1.86 | 1.00 | 1.00 | 1.00 | 1.00 | 1.00 | 1.00 |
| Palm | 0.87 | 1.05 | 1.14 | 0.65 | 0.83 | 0.71 | 0.91 | 4.11 | 1.07 | 0.92 | 1.63 | 1.02 |
| Pam16 | 1.05 | 1.61 | 0.84 | 0.61 | 3.25 | 1.75 | 1.11 | 1.69 | 0.88 | 1.04 | 1.01 | 2.00 |
| Panx2 | 1.00 | 1.00 | 1.00 | 1.00 | 1.00 | 1.00 | 1.37 | 1.60 | 0.97 | 1.00 | 5.02 | 1.00 |
| Paox | 0.99 | 0.97 | 0.89 | 2.56 | 11.85 | 2.94 | 1.01 | 1.64 | 1.85 | 1.50 | 1.99 | 1.44 |
| Papl | 0.85 | 1.31 | 0.96 | 1.00 | 1.00 | 1.00 | 0.67 | 3.66 | 1.00 | 1.00 | 1.00 | 1.00 |
| Paqr6 | 1.01 | 1.00 | 0.98 | 1.00 | 1.00 | 1.00 | 0.61 | 0.44 | 0.66 | 1.00 | 1.53 | 0.76 |
| Pard6a | 0.99 | 1.49 | 1.00 | 1.05 | 1.63 | 0.83 | 1.19 | 1.37 | 0.99 | 0.99 | 1.38 | 0.94 |
| Park7 | 1.04 | 1.16 | 1.12 | 0.89 | 3.13 | 1.04 | 1.27 | 2.18 | 1.13 | 1.04 | 1.42 | 0.94 |
| Parl | 0.84 | 0.94 | 0.87 | 0.88 | 5.18 | 1.16 | 0.85 | 1.46 | 0.95 | 1.46 | 1.46 | 0.81 |
| Parp6 | 0.92 | 1.16 | 0.93 | 1.11 | 2.84 | 1.24 | 0.84 | 2.22 | 1.17 | 1.03 | 1.32 | 1.14 |
| Pbld1 | 1.59 | 1.90 | 2.17 | 1.18 | 1.00 | 1.18 | 1.00 | 1.00 | 1.00 | 1.00 | 1.00 | 1.00 |
| Pbx4 | 1.00 | 1.00 | 0.90 | 1.00 | 1.00 | 1.00 | 1.03 | 2.52 | 1.05 | 1.63 | 1.30 | 1.49 |
| Pcbd2 | 1.06 | 1.67 | 1.12 | 1.32 | 11.27 | 0.63 | 0.75 | 0.60 | 0.28 | 1.16 | 0.89 | 1.08 |
| Pcdhga10 | 1.20 | 0.91 | 0.93 | 0.96 | 1.00 | 1.08 | 1.00 | 1.00 | 1.00 | 1.00 | 1.11 | 0.98 |
| Pcdhgc3 | 0.97 | 1.00 | 1.10 | 0.75 | 0.19 | 0.97 | 0.94 | 1.00 | 0.86 | 0.91 | 1.02 | 1.11 |
| Pcdhgc5 | 1.00 | 1.00 | 1.00 | 1.00 | 1.00 | 1.00 | 1.05 | 1.00 | 1.07 | 1.00 | 5.03 | 1.00 |
| Pck1 | 1.54 | 1.40 | 2.66 | 0.37 | 0.07 | 0.81 | 1.18 | 1.00 | 0.67 | 1.12 | 2.12 | 1.38 |
| Pck2 | 1.24 | 1.29 | 1.37 | 0.83 | 1.52 | 0.96 | 0.92 | 1.67 | 0.92 | 1.09 | 1.07 | 1.01 |
| Pcp4 | 1.47 | 1.26 | 1.12 | 0.75 | 0.70 | 0.12 | 1.00 | 1.00 | 1.00 | 0.65 | 16.77 | 2.05 |
| Pcsk1n | 1.03 | 1.65 | 1.67 | 1.24 | 4.09 | 1.69 | 0.89 | 2.48 | 1.22 | 1.00 | 19.05 | 1.00 |
| Pcsk2 | 1.42 | 1.30 | 1.53 | 1.00 | 1.00 | 1.00 | 0.67 | 1.00 | 1.02 | 1.00 | 8.04 | 1.00 |
| Pcyt2 | 1.04 | 1.15 | 1.00 | 1.00 | 4.56 | 1.27 | 0.90 | 1.36 | 0.96 | 1.03 | 1.39 | 1.05 |
| Pdcd5 | 0.80 | 0.88 | 1.27 | 0.82 | 13.57 | 0.97 | 0.91 | 2.95 | 1.19 | 1.04 | 1.33 | 0.84 |
| Pddc1 | 0.90 | 0.99 | 0.99 | 0.72 | 1.77 | 1.08 | 1.02 | 3.67 | 0.87 | 0.92 | 1.16 | 0.96 |
| Pde4b | 1.31 | 1.62 | 0.99 | 0.99 | 0.43 | 1.05 | 1.10 | 0.76 | 1.03 | 1.29 | 1.03 | 1.12 |
| Pde4d | 1.57 | 1.50 | 1.17 | 9.75 | 5.81 | 6.62 | 1.04 | 1.00 | 0.95 | 1.27 | 1.08 | 0.79 |
| Pde6h | 1.00 | 1.00 | 1.00 | 1.00 | 1.00 | 1.00 | 1.00 | 1.00 | 1.00 | 1.00 | 1.00 | 1.00 |
| Pde9a | 0.86 | 1.00 | 1.00 | 0.92 | 2.23 | 1.31 | 1.00 | 2.07 | 1.00 | 1.00 | 1.00 | 1.00 |
| Pdia2 | 1.35 | 1.66 | 1.47 | 1.00 | 1.00 | 1.00 | 1.00 | 1.00 | 1.00 | 1.00 | 1.79 | 1.00 |
| Pdia6 | 1.22 | 1.01 | 1.17 | 1.46 | 3.67 | 1.24 | 1.06 | 1.00 | 0.96 | 1.64 | 1.51 | 1.38 |
| Pdk4 | 2.18 | 2.61 | 3.34 | 6.84 | 1.32 | 3.00 | 1.03 | 1.00 | 0.86 | 2.12 | 2.27 | 2.70 |
| Pdlim1 | 1.05 | 1.32 | 1.03 | 1.84 | 3.53 | 1.69 | 1.13 | 2.76 | 1.16 | 0.99 | 1.02 | 0.86 |
| Pdlim2 | 0.61 | 0.83 | 1.01 | 0.97 | 5.86 | 1.02 | 0.59 | 0.65 | 1.04 | 0.91 | 0.95 | 0.91 |
| Pdlim7 | 1.03 | 1.27 | 1.03 | 1.28 | 3.05 | 0.95 | 1.00 | 1.25 | 0.94 | 1.35 | 1.06 | 1.01 |
| Pdrg1 | 1.15 | 1.28 | 1.11 | 0.85 | 2.31 | 0.88 | 0.87 | 2.40 | 0.90 | 1.10 | 1.35 | 1.24 |

Fig. 35- 228

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Ocel1 | 1.14 | 1.22 | 0.87 | 1.19 | 0.84 | 0.99 | 1.49 | 5.15 | 0.96 | 1.88 | 1.47 | 1.12 |
| Ocm | 1.00 | 1.00 | 1.00 | 1.00 | 1.00 | 1.00 | 1.87 | 10.49 | 1.00 | 1.00 | 1.00 | 1.00 |
| Odf1 | 1.00 | 1.00 | 1.00 | 1.00 | 1.00 | 1.00 | 15.35 | 1.00 | 1.00 | 1.00 | 1.00 | 1.00 |
| Odf3l2 | 1.00 | 1.00 | 1.00 | 1.00 | 1.07 | 1.00 | 1.21 | 3.60 | 1.07 | 1.00 | 1.00 | 1.00 |
| Ogfod2 | 1.03 | 1.11 | 0.81 | 1.10 | 0.93 | 0.96 | 1.02 | 3.70 | 0.96 | 2.44 | 1.02 | 1.07 |
| Ogfod3 | 0.56 | 0.72 | 0.89 | 1.01 | 1.21 | 1.14 | 1.37 | 4.74 | 1.01 | 1.67 | 0.84 | 0.92 |
| Ogfr | 1.24 | 1.31 | 1.01 | 1.12 | 1.14 | 0.99 | 1.14 | 6.43 | 1.14 | 2.97 | 1.55 | 1.16 |
| Ogfrl1 | 0.92 | 1.24 | 0.59 | 1.28 | 63.46 | 1.27 | 0.92 | 4.72 | 1.56 | 2.60 | 1.38 | 1.34 |
| Olfm1 | 1.00 | 1.00 | 1.00 | 1.03 | 1.39 | 1.01 | 0.79 | 0.64 | 0.96 | 0.82 | 1.06 | 0.89 |
| Olfm4 | 1.00 | 1.00 | 1.00 | 1.00 | 1.00 | 1.00 | 1.00 | 1.00 | 1.00 | 0.09 | 1.24 | 1.01 |
| Olfml2b | 1.00 | 1.00 | 1.00 | 1.44 | 2.11 | 1.10 | 0.86 | 0.66 | 1.17 | 10.13 | 22.16 | 22.22 |
| Olig1 | 1.00 | 1.00 | 1.00 | 1.30 | 1.02 | 1.28 | 0.91 | 1.00 | 0.60 | 1.00 | 1.00 | 1.00 |
| Omg | 1.00 | 1.00 | 1.00 | 1.00 | 0.59 | 1.00 | 1.00 | 1.00 | 1.00 | 1.00 | 1.51 | 1.00 |
| Orai2 | 0.86 | 0.88 | 1.19 | 1.09 | 5.39 | 1.02 | 0.62 | 0.17 | 0.80 | 0.94 | 0.98 | 0.96 |
| Orm1 | 1.00 | 1.00 | 1.00 | 1.00 | 1.00 | 1.00 | 1.30 | 22.09 | 0.81 | 5.37 | 2.39 | 1.84 |
| Orm2 | 1.00 | 1.00 | 1.00 | 1.00 | 1.00 | 1.00 | 0.89 | 48.30 | 0.86 | 3.06 | 0.73 | 0.95 |
| Orm3 | 1.00 | 1.00 | 1.00 | 1.00 | 1.55 | 1.00 | 1.00 | 9.58 | 1.00 | 1.00 | 1.00 | 1.00 |
| Osgep | 0.94 | 1.00 | 0.79 | 0.73 | 1.57 | 0.80 | 1.35 | 5.44 | 1.17 | 2.92 | 0.93 | 0.94 |
| Osr2 | 1.00 | 1.00 | 1.00 | 1.00 | 1.00 | 1.00 | 1.97 | 0.95 | 1.89 | 1.00 | 1.00 | 1.00 |
| Otos | 1.00 | 1.00 | 1.00 | 1.00 | 0.11 | 1.00 | 2.94 | 111.90 | 1.35 | 2.94 | 0.77 | 1.57 |
| Otud1 | 0.85 | 0.78 | 0.87 | 1.01 | 1.00 | 0.96 | 0.87 | 0.05 | 0.98 | 0.25 | 0.99 | 0.94 |
| Otulin | 1.02 | 0.67 | 0.77 | 1.22 | 0.99 | 0.97 | 1.20 | 5.62 | 1.01 | 2.27 | 1.17 | 1.15 |
| P2rx5 | 1.00 | 1.00 | 1.00 | 1.04 | 0.75 | 1.07 | 1.70 | 6.30 | 1.31 | 1.00 | 1.00 | 1.00 |
| P2rx6 | 1.00 | 1.00 | 1.00 | 0.90 | 1.20 | 0.97 | 0.77 | 5.22 | 1.13 | 1.00 | 1.00 | 1.00 |
| Pacsin3 | 1.19 | 0.98 | 1.06 | 1.10 | 0.72 | 0.80 | 1.12 | 4.02 | 1.09 | 1.00 | 1.00 | 1.00 |
| Padi1 | 1.00 | 0.91 | 0.48 | 1.00 | 1.00 | 1.00 | 1.00 | 5.04 | 0.82 | 1.00 | 1.00 | 1.00 |
| Padi3 | 1.00 | 1.00 | 1.00 | 1.00 | 1.00 | 1.00 | 1.00 | 10.31 | 1.01 | 1.00 | 1.00 | 1.00 |
| Paf1 | 1.21 | 1.23 | 1.12 | 1.12 | 1.35 | 1.02 | 1.18 | 3.78 | 0.98 | 2.20 | 1.13 | 1.06 |
| Pah | 1.32 | 1.25 | 1.02 | 1.00 | 1.00 | 1.00 | 1.00 | 1.00 | 1.00 | 1.00 | 1.00 | 1.00 |
| Palm | 1.16 | 1.13 | 1.00 | 1.07 | 0.81 | 0.99 | 0.96 | 8.10 | 0.90 | 3.39 | 1.48 | 1.13 |
| Pam16 | 1.00 | 1.00 | 1.00 | 0.55 | 0.31 | 0.70 | 1.13 | 10.46 | 1.28 | 1.76 | 1.20 | 0.47 |
| Panx2 | 1.00 | 1.00 | 1.00 | 1.04 | 1.16 | 1.08 | 1.00 | 1.00 | 1.00 | 1.00 | 1.00 | 1.00 |
| Paox | 1.64 | 1.72 | 1.40 | 1.49 | 4.20 | 1.55 | 1.38 | 3.11 | 1.46 | 7.57 | 1.89 | 1.78 |
| Papl | 1.00 | 1.00 | 1.00 | 1.00 | 1.55 | 1.00 | 0.74 | 11.68 | 0.62 | 1.00 | 1.00 | 1.00 |
| Paqr6 | 1.00 | 1.00 | 1.00 | 0.92 | 1.61 | 0.91 | 1.44 | 5.37 | 1.15 | 1.00 | 1.00 | 1.00 |
| Pard6a | 1.00 | 1.00 | 1.00 | 1.12 | 1.55 | 1.04 | 2.64 | 5.06 | 0.94 | 2.23 | 1.49 | 1.40 |
| Park7 | 0.74 | 0.69 | 1.34 | 1.14 | 0.97 | 1.15 | 1.38 | 8.88 | 1.11 | 2.56 | 1.17 | 1.07 |
| Parl | 0.85 | 0.66 | 1.12 | 1.03 | 1.19 | 0.92 | 0.84 | 5.14 | 0.87 | 2.78 | 1.27 | 0.99 |
| Parp6 | 0.98 | 1.00 | 1.20 | 0.93 | 1.02 | 1.03 | 1.26 | 7.19 | 1.16 | 3.66 | 1.26 | 1.31 |
| Pbld1 | 0.79 | 0.77 | 1.12 | 1.00 | 1.00 | 1.00 | 1.00 | 1.00 | 1.07 | 1.00 | 1.11 | 1.48 |
| Pbx4 | 1.00 | 1.00 | 1.00 | 0.76 | 0.46 | 1.15 | 1.55 | 7.44 | 1.43 | 3.21 | 0.91 | 0.90 |
| Pcbd2 | 0.37 | 0.32 | 0.94 | 1.24 | 0.76 | 1.27 | 1.25 | 3.73 | 1.02 | 1.95 | 0.99 | 1.11 |
| Pcdhga10 | 1.00 | 1.00 | 1.00 | 1.10 | 5.88 | 0.86 | 1.07 | 0.50 | 0.95 | 1.00 | 1.00 | 1.00 |
| Pcdhgc3 | 0.81 | 0.60 | 1.10 | 0.95 | 5.14 | 0.96 | 0.71 | 0.04 | 1.01 | 1.00 | 1.00 | 1.00 |
| Pcdhgc5 | 1.00 | 1.00 | 1.00 | 1.12 | 0.39 | 1.03 | 1.00 | 1.00 | 1.00 | 1.00 | 1.00 | 1.00 |
| Pck1 | 0.52 | 0.95 | 0.76 | 0.77 | 1.00 | 2.03 | 3.86 | 0.50 | 3.12 | 1.00 | 1.00 | 1.00 |
| Pck2 | 1.21 | 1.37 | 0.83 | 1.14 | 0.81 | 0.93 | 0.98 | 5.43 | 1.24 | 1.79 | 1.05 | 0.99 |
| Pcp4 | 1.00 | 1.00 | 1.00 | 1.13 | 1.00 | 1.03 | 1.19 | 2.08 | 1.00 | 1.00 | 1.00 | 1.00 |
| Pcsk1n | 0.75 | 0.68 | 1.03 | 1.10 | 0.94 | 1.07 | 1.00 | 1.69 | 1.00 | 1.00 | 1.00 | 1.00 |
| Pcsk2 | 0.53 | 0.57 | 1.02 | 1.03 | 1.20 | 0.98 | 1.00 | 1.00 | 1.00 | 1.00 | 1.00 | 1.00 |
| Pcyt2 | 1.08 | 0.88 | 1.00 | 1.05 | 0.83 | 0.98 | 1.13 | 5.70 | 0.86 | 2.94 | 1.70 | 1.37 |
| Pdcd5 | 0.87 | 0.32 | 1.57 | 1.19 | 0.77 | 1.39 | 1.18 | 8.52 | 1.02 | 2.62 | 1.00 | 0.98 |
| Pddc1 | 0.53 | 0.50 | 0.53 | 0.94 | 0.76 | 1.13 | 1.08 | 8.09 | 0.91 | 2.02 | 1.26 | 1.25 |
| Pde4b | 1.00 | 1.00 | 1.00 | 1.05 | 5.08 | 1.06 | 1.53 | 0.73 | 1.38 | 0.92 | 1.19 | 0.87 |
| Pde4d | 1.00 | 1.00 | 1.00 | 1.03 | 1.39 | 0.99 | 2.22 | 1.95 | 2.79 | 0.81 | 0.83 | 1.04 |
| Pde6h | 1.00 | 1.00 | 1.00 | 1.00 | 1.00 | 1.00 | 1.00 | 1.00 | 1.00 | 1.00 | 1.00 | 1.00 |
| Pde9a | 1.00 | 1.00 | 1.00 | 1.14 | 0.75 | 1.42 | 1.25 | 6.04 | 1.00 | 1.00 | 1.00 | 1.00 |
| Pdia2 | 0.71 | 0.80 | 0.78 | 1.00 | 1.00 | 1.00 | 1.00 | 1.00 | 1.00 | 0.66 | 0.57 | 0.82 |
| Pdia6 | 0.89 | 0.77 | 0.84 | 1.34 | 1.03 | 1.17 | 1.42 | 2.53 | 1.06 | 2.45 | 1.34 | 1.27 |
| Pdk4 | 1.62 | 1.72 | 1.84 | 1.15 | 1.00 | 1.37 | 2.85 | 0.45 | 5.29 | 1.00 | 1.00 | 1.00 |
| Pdlim1 | 1.60 | 1.26 | 0.87 | 1.53 | 5.49 | 1.00 | 0.83 | 0.45 | 0.94 | 0.72 | 0.94 | 1.03 |
| Pdlim2 | 1.32 | 1.04 | 1.29 | 1.04 | 1.01 | 0.73 | 0.79 | 1.13 | 0.71 | 1.81 | 1.11 | 1.35 |
| Pdlim7 | 1.00 | 1.00 | 1.23 | 1.02 | 0.96 | 1.03 | 2.31 | 6.25 | 1.46 | 2.02 | 1.27 | 1.54 |
| Pdrg1 | 0.73 | 0.45 | 0.63 | 1.17 | 1.05 | 0.99 | 1.09 | 5.25 | 0.72 | 1.61 | 1.06 | 0.95 |

Fig. 35- 229

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Pdzd9 | 1.00 | 0.22 | 1.00 | 1.00 | 6.22 | 1.00 | 0.74 | 0.70 | 1.00 | 1.00 | 1.23 | 1.00 |
| Pdzk1ip1 | 1.00 | 1.00 | 1.00 | 1.00 | 1.00 | 1.00 | 1.00 | 1.00 | 1.00 | 2.62 | 2.86 | 1.11 |
| Peg3 | 1.39 | 1.00 | 4.50 | 10.56 | 0.12 | 7.95 | 1.44 | 1.64 | 1.94 | 1.00 | 1.00 | 2.19 |
| Peg3os | 1.75 | 1.00 | 3.07 | 28.39 | 0.18 | 6.85 | 0.65 | 0.97 | 0.61 | 1.00 | 1.00 | 1.33 |
| Pemt | 2.02 | 0.80 | 0.63 | 0.28 | 7.10 | 0.88 | 1.14 | 0.71 | 1.00 | 1.78 | 2.20 | 0.58 |
| Penk | 1.17 | 1.73 | 1.26 | 1.69 | 0.36 | 1.93 | 1.16 | 0.90 | 0.82 | 0.48 | 0.51 | 1.30 |
| Perp | 5.31 | 4.56 | 6.98 | 2.09 | 1.85 | 1.46 | 1.00 | 0.90 | 0.90 | 1.23 | 1.57 | 1.04 |
| Pet100 | 1.02 | 0.48 | 0.82 | 0.36 | 7.58 | 0.74 | 1.01 | 1.08 | 0.70 | 3.35 | 3.76 | 1.06 |
| Pet112 | 1.14 | 0.71 | 1.16 | 0.53 | 3.94 | 0.78 | 0.94 | 0.96 | 0.88 | 2.27 | 1.92 | 0.73 |
| Pex11g | 1.13 | 0.81 | 0.77 | 0.42 | 4.91 | 0.91 | 0.95 | 0.79 | 0.84 | 1.35 | 2.90 | 1.17 |
| Pex16 | 0.86 | 0.58 | 1.09 | 0.25 | 6.51 | 1.15 | 1.22 | 0.97 | 0.99 | 2.91 | 3.94 | 0.72 |
| Pex5l | 1.00 | 1.00 | 1.00 | 1.00 | 0.27 | 1.00 | 1.00 | 1.00 | 1.00 | 1.00 | 1.00 | 1.00 |
| Pex6 | 1.07 | 0.57 | 1.27 | 0.53 | 6.85 | 1.22 | 1.09 | 1.09 | 0.87 | 3.68 | 3.60 | 0.95 |
| Pfdn1 | 1.16 | 0.65 | 0.87 | 0.29 | 5.47 | 0.91 | 1.11 | 0.93 | 0.79 | 1.41 | 2.39 | 0.91 |
| Pfdn2 | 1.32 | 1.39 | 1.09 | 0.52 | 1.66 | 0.94 | 0.85 | 0.81 | 0.95 | 0.52 | 1.12 | 0.92 |
| Pfdn5 | 1.12 | 0.44 | 0.97 | 0.24 | 18.33 | 0.98 | 0.86 | 0.62 | 0.75 | 3.20 | 6.50 | 0.84 |
| Pfkfb3 | 1.89 | 2.44 | 2.54 | 0.79 | 0.36 | 1.78 | 1.31 | 1.51 | 1.51 | 2.03 | 1.18 | 1.14 |
| Pfn3 | 1.00 | 1.00 | 1.00 | 1.00 | 1.00 | 1.00 | 1.00 | 1.00 | 1.00 | 1.58 | 1.00 | 1.00 |
| Pgam2 | 0.79 | 0.42 | 0.59 | 0.61 | 2.82 | 0.60 | 1.00 | 0.85 | 0.79 | 4.63 | 3.65 | 0.81 |
| Pgbd5 | 1.00 | 1.00 | 1.00 | 1.00 | 0.24 | 1.00 | 1.00 | 1.00 | 1.00 | 1.00 | 1.00 | 1.00 |
| Pgc | 0.74 | 1.00 | 1.00 | 3.06 | 1.00 | 1.00 | 1.00 | 1.00 | 1.00 | 0.02 | 0.89 | 0.80 |
| Pgf | 1.93 | 0.50 | 0.75 | 0.84 | 3.95 | 1.00 | 1.02 | 1.08 | 1.22 | 2.36 | 3.49 | 1.45 |
| Pgk2 | 1.00 | 1.00 | 1.00 | 1.00 | 1.00 | 1.00 | 1.00 | 1.00 | 1.00 | 1.00 | 1.00 | 1.00 |
| Pgls | 1.25 | 0.65 | 1.13 | 0.29 | 8.44 | 0.93 | 1.16 | 0.72 | 0.87 | 2.91 | 4.55 | 0.88 |
| Pglyrp1 | 1.97 | 2.14 | 2.51 | 1.09 | 2.54 | 1.25 | 1.44 | 0.50 | 0.72 | 2.77 | 3.21 | 0.97 |
| Pgp | 0.86 | 0.58 | 0.78 | 0.50 | 5.80 | 1.20 | 1.21 | 1.06 | 1.09 | 3.31 | 2.89 | 1.13 |
| Phactr1 | 0.88 | 1.00 | 1.00 | 1.07 | 0.13 | 0.76 | 1.21 | 1.63 | 1.19 | 0.66 | 0.66 | 1.14 |
| Phax | 1.15 | 0.96 | 1.24 | 0.83 | 4.65 | 1.39 | 1.22 | 1.13 | 0.95 | 1.95 | 1.93 | 1.04 |
| Phb | 1.05 | 0.63 | 0.86 | 0.27 | 4.91 | 0.72 | 1.03 | 0.85 | 0.89 | 2.16 | 3.25 | 0.92 |
| Phf11c | 1.44 | 1.00 | 1.00 | 24.60 | 23.79 | 1.00 | 2.59 | 2.44 | 1.03 | 1.00 | 1.54 | 1.37 |
| Phf7 | 1.11 | 1.01 | 0.98 | 1.48 | 5.64 | 1.10 | 1.23 | 1.15 | 0.94 | 1.37 | 2.10 | 0.91 |
| Phkg2 | 1.22 | 0.71 | 1.41 | 0.56 | 2.42 | 0.93 | 1.16 | 0.76 | 0.80 | 0.05 | 0.92 | 0.93 |
| Phpt1 | 1.20 | 0.86 | 1.04 | 0.40 | 3.46 | 0.84 | 1.01 | 0.79 | 0.74 | 1.44 | 1.96 | 1.00 |
| Phyh | 1.04 | 1.01 | 0.89 | 1.01 | 1.29 | 0.87 | 0.91 | 0.93 | 0.82 | 0.80 | 0.74 | 0.89 |
| Phyhd1 | 2.95 | 1.48 | 1.47 | 1.05 | 5.91 | 1.93 | 1.55 | 1.30 | 1.13 | 1.77 | 3.03 | 1.44 |
| Phyhipl | 1.00 | 3.12 | 1.00 | 1.00 | 0.19 | 1.00 | 1.00 | 1.00 | 1.00 | 0.36 | 1.19 | 1.00 |
| Pigb | 1.00 | 0.36 | 1.27 | 1.00 | 33.99 | 0.81 | 1.41 | 1.12 | 1.18 | 16.68 | 20.48 | 1.32 |
| Pigr | 1.00 | 1.00 | 1.00 | 1.00 | 1.00 | 1.00 | 1.00 | 1.00 | 1.00 | 1.34 | 2.41 | 1.04 |
| Pigu | 1.50 | 0.87 | 1.14 | 0.44 | 4.83 | 0.98 | 0.85 | 0.84 | 0.70 | 1.34 | 2.27 | 0.84 |
| Pigx | 0.60 | 0.32 | 0.74 | 0.88 | 4.09 | 1.11 | 0.97 | 0.79 | 0.71 | 1.86 | 2.51 | 0.71 |
| Pigyl | 0.93 | 0.51 | 0.71 | 0.34 | 3.51 | 0.75 | 0.78 | 0.68 | 0.70 | 1.95 | 3.69 | 1.16 |
| Pih1d1 | 1.19 | 0.60 | 0.87 | 0.25 | 4.07 | 0.79 | 1.34 | 0.80 | 1.12 | 1.94 | 1.88 | 1.14 |
| Pilra | 1.00 | 1.00 | 1.00 | 1.00 | 1.00 | 1.00 | 1.00 | 1.00 | 1.00 | 1.36 | 1.42 | 1.02 |
| Pin4 | 1.07 | 0.29 | 1.56 | 0.27 | 24.81 | 1.95 | 0.94 | 1.49 | 0.46 | 3.89 | 4.61 | 0.94 |
| Pinlyp | 1.00 | 1.00 | 1.00 | 1.00 | 1.00 | 1.00 | 1.00 | 1.00 | 1.00 | 1.00 | 1.00 | 1.00 |
| Pir | 2.07 | 1.15 | 1.82 | 1.43 | 5.53 | 1.40 | 1.17 | 1.03 | 1.18 | 0.91 | 1.30 | 0.87 |
| Pkdcc | 0.49 | 0.45 | 0.57 | 2.98 | 5.36 | 1.37 | 0.77 | 0.73 | 0.87 | 0.59 | 0.82 | 1.13 |
| Pkig | 1.04 | 0.55 | 0.69 | 1.25 | 7.95 | 2.52 | 0.79 | 0.77 | 0.76 | 2.03 | 2.11 | 0.97 |
| Pkn1 | 1.00 | 0.61 | 1.65 | 0.69 | 5.20 | 0.89 | 1.34 | 1.53 | 1.36 | 3.39 | 3.79 | 1.13 |
| Pla2g12a | 1.62 | 1.00 | 1.23 | 0.56 | 5.06 | 1.61 | 1.02 | 1.24 | 1.18 | 2.62 | 3.62 | 1.38 |
| Pla2g1b | 0.98 | 1.00 | 1.00 | 1.89 | 1.00 | 1.00 | 1.00 | 1.00 | 1.00 | 0.54 | 1.89 | 1.33 |
| Pla2g2d | 1.66 | 1.66 | 2.27 | 9.53 | 6.05 | 6.30 | 0.77 | 0.56 | 0.69 | 1.00 | 0.88 | 0.92 |
| Plac9a | 0.85 | 0.43 | 1.46 | 0.34 | 22.72 | 1.00 | 0.54 | 1.00 | 1.00 | 3.66 | 6.35 | 1.00 |
| Plaur | 1.00 | 1.00 | 1.00 | 1.09 | 1.00 | 1.00 | 1.23 | 1.24 | 1.12 | 0.50 | 0.90 | 1.16 |
| Plb1 | 0.80 | 1.59 | 1.26 | 1.00 | 1.00 | 1.00 | 1.00 | 0.77 | 1.08 | 0.81 | 1.81 | 1.22 |
| Pld4 | 1.67 | 0.68 | 1.83 | 0.66 | 6.10 | 1.39 | 0.87 | 0.83 | 1.28 | 2.03 | 2.38 | 0.73 |
| Plekhb1 | 0.78 | 0.94 | 0.68 | 0.87 | 0.23 | 0.59 | 0.83 | 0.92 | 0.73 | 0.64 | 0.74 | 0.98 |
| Plekhf1 | 0.93 | 0.98 | 0.79 | 0.25 | 0.40 | 0.66 | 0.69 | 0.68 | 0.67 | 0.42 | 0.66 | 0.98 |
| Plekhg1 | 1.24 | 1.00 | 1.00 | 5.83 | 0.53 | 1.74 | 2.11 | 2.74 | 1.86 | 1.00 | 0.44 | 1.35 |
| Plekhm2 | 1.37 | 1.06 | 1.37 | 2.20 | 5.47 | 2.01 | 1.06 | 1.19 | 0.99 | 1.73 | 2.20 | 1.10 |
| Plin5 | 0.82 | 0.79 | 1.37 | 0.38 | 1.88 | 1.36 | 0.77 | 0.75 | 0.88 | 1.47 | 1.87 | 1.35 |
| Plk3 | 1.33 | 1.00 | 1.14 | 3.27 | 1.82 | 3.53 | 1.09 | 0.90 | 1.48 | 0.60 | 0.79 | 1.61 |
| Plp1 | 1.23 | 0.76 | 1.42 | 2.08 | 0.08 | 1.55 | 1.34 | 1.05 | 1.11 | 2.13 | 1.35 | 1.05 |
| Plrg1 | 1.15 | 0.93 | 1.15 | 0.60 | 3.65 | 0.99 | 1.19 | 1.00 | 1.06 | 1.56 | 2.51 | 1.04 |

Fig. 35- 230

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Pdzd9 | 1.00 | 1.00 | 1.00 | 1.00 | 0.50 | 1.00 | 1.00 | 0.96 | 1.00 | 1.00 | 1.00 | 1.00 |
| Pdzk1ip1 | 1.35 | 0.98 | 1.17 | 1.08 | 0.72 | 1.19 | 1.00 | 1.17 | 1.00 | 0.98 | 1.78 | 1.01 |
| Peg3 | 1.00 | 1.00 | 1.07 | 2.46 | 1.00 | 2.92 | 3.38 | 1.00 | 1.99 | 1.79 | 1.00 | 1.06 |
| Peg3os | 1.00 | 1.00 | 1.16 | 2.36 | 1.00 | 1.58 | 4.86 | 1.00 | 1.27 | 0.94 | 1.00 | 1.57 |
| Pemt | 1.20 | 1.29 | 1.06 | 1.00 | 0.29 | 0.97 | 0.73 | 1.10 | 0.79 | 0.74 | 1.76 | 0.70 |
| Penk | 5.02 | 3.22 | 1.92 | 3.95 | 1.76 | 2.40 | 1.00 | 1.00 | 1.00 | 1.19 | 1.74 | 1.42 |
| Perp | 1.92 | 1.68 | 1.76 | 1.10 | 1.20 | 1.19 | 0.93 | 0.58 | 0.83 | 1.08 | 1.10 | 1.04 |
| Pet100 | 0.98 | 1.80 | 1.17 | 0.75 | 0.48 | 0.73 | 0.65 | 2.44 | 1.12 | 1.31 | 1.70 | 0.99 |
| Pet112 | 1.11 | 1.10 | 0.90 | 0.93 | 0.72 | 1.09 | 0.67 | 1.20 | 0.79 | 0.95 | 1.15 | 1.06 |
| Pex11g | 1.61 | 1.94 | 1.11 | 0.73 | 0.70 | 0.83 | 1.05 | 1.34 | 1.07 | 1.00 | 1.15 | 0.99 |
| Pex16 | 1.25 | 1.64 | 0.95 | 1.36 | 0.53 | 1.00 | 1.58 | 3.72 | 1.49 | 1.26 | 1.54 | 1.07 |
| Pex5l | 1.00 | 1.00 | 1.00 | 1.00 | 1.00 | 1.00 | 1.00 | 1.00 | 1.00 | 1.56 | 1.64 | 1.18 |
| Pex6 | 1.21 | 1.33 | 1.03 | 1.03 | 0.59 | 1.16 | 1.33 | 3.08 | 1.25 | 1.04 | 1.33 | 1.09 |
| Pfdn1 | 1.17 | 1.52 | 0.81 | 1.01 | 0.71 | 0.98 | 0.83 | 0.94 | 0.81 | 1.05 | 1.56 | 0.99 |
| Pfdn2 | 0.99 | 1.16 | 0.90 | 1.25 | 2.18 | 1.03 | 0.89 | 0.26 | 0.84 | 1.02 | 1.44 | 0.93 |
| Pfdn5 | 1.92 | 2.34 | 1.15 | 0.84 | 0.51 | 0.99 | 0.91 | 2.16 | 1.04 | 0.85 | 2.15 | 0.92 |
| Pfkfb3 | 0.90 | 0.75 | 1.08 | 1.32 | 0.95 | 0.81 | 3.39 | 7.07 | 2.01 | 0.97 | 0.73 | 0.97 |
| Pfn3 | 1.00 | 1.00 | 1.00 | 0.41 | 1.17 | 0.52 | 1.00 | 1.10 | 1.00 | 1.00 | 1.00 | 1.00 |
| Pgam2 | 0.99 | 1.10 | 1.07 | 0.95 | 0.52 | 1.01 | 1.35 | 1.94 | 0.85 | 1.46 | 0.56 | 0.81 |
| Pgbd5 | 1.00 | 1.00 | 1.00 | 1.00 | 1.00 | 1.00 | 1.00 | 1.00 | 1.00 | 0.81 | 0.80 | 0.93 |
| Pgc | 0.95 | 0.81 | 1.00 | 1.23 | 0.53 | 1.00 | 1.42 | 1.31 | 0.89 | 1.00 | 1.00 | 0.97 |
| Pgf | 3.21 | 2.80 | 1.51 | 1.00 | 0.49 | 1.00 | 1.00 | 1.00 | 1.00 | 0.68 | 1.39 | 1.55 |
| Pgk2 | 1.00 | 1.00 | 1.00 | 1.00 | 1.00 | 1.00 | 1.00 | 1.00 | 1.00 | 1.00 | 1.00 | 1.00 |
| Pgls | 0.98 | 1.25 | 0.93 | 0.79 | 0.54 | 1.08 | 1.01 | 2.05 | 0.99 | 1.05 | 1.54 | 1.07 |
| Pglyrp1 | 1.35 | 2.23 | 1.57 | 1.00 | 0.99 | 1.00 | 1.00 | 1.00 | 1.00 | 1.31 | 1.80 | 1.25 |
| Pgp | 0.93 | 1.02 | 0.98 | 1.12 | 0.74 | 1.18 | 0.78 | 2.36 | 0.82 | 1.03 | 1.46 | 1.02 |
| Phactr1 | 1.00 | 1.00 | 0.79 | 1.11 | 1.96 | 0.90 | 1.00 | 1.00 | 1.00 | 0.99 | 0.73 | 0.83 |
| Phax | 1.18 | 1.30 | 1.06 | 1.37 | 1.09 | 1.16 | 1.19 | 2.08 | 1.24 | 0.99 | 1.40 | 1.01 |
| Phb | 1.06 | 1.45 | 0.76 | 0.90 | 0.67 | 1.00 | 1.04 | 1.66 | 1.04 | 0.92 | 1.56 | 1.01 |
| Phf11c | 2.41 | 2.13 | 1.85 | 0.71 | 0.71 | 0.95 | 9.04 | 4.63 | 1.24 | 0.50 | 1.97 | 0.94 |
| Phf7 | 1.14 | 1.63 | 1.11 | 1.02 | 1.13 | 0.94 | 0.98 | 1.25 | 0.57 | 0.81 | 1.23 | 1.09 |
| Phkg2 | 1.11 | 1.46 | 0.96 | 0.98 | 16.78 | 1.09 | 1.18 | 1.61 | 0.95 | 0.99 | 1.39 | 1.00 |
| Phpt1 | 1.18 | 1.44 | 0.94 | 0.64 | 0.54 | 0.61 | 0.90 | 0.78 | 0.83 | 0.93 | 1.46 | 0.96 |
| Phyh | 1.28 | 1.50 | 0.86 | 1.18 | 1.72 | 0.97 | 1.22 | 0.67 | 1.35 | 0.88 | 1.18 | 0.93 |
| Phyhd1 | 2.10 | 2.06 | 1.52 | 1.22 | 1.17 | 1.13 | 0.88 | 0.99 | 0.81 | 1.16 | 1.56 | 1.03 |
| Phyhipl | 1.00 | 1.00 | 1.00 | 0.85 | 1.30 | 0.76 | 1.00 | 1.00 | 1.00 | 1.00 | 1.09 | 1.00 |
| Pigb | 0.78 | 0.77 | 1.10 | 0.80 | 0.38 | 1.33 | 0.78 | 4.64 | 1.06 | 0.86 | 0.69 | 0.91 |
| Pigr | 2.43 | 2.03 | 2.30 | 0.52 | 0.43 | 0.60 | 0.93 | 1.41 | 1.13 | 0.96 | 0.89 | 0.89 |
| Pigu | 1.08 | 1.24 | 0.97 | 0.67 | 0.66 | 0.86 | 0.91 | 1.03 | 0.87 | 1.04 | 1.32 | 0.96 |
| Pigx | 0.98 | 1.14 | 0.99 | 1.04 | 0.68 | 1.04 | 1.07 | 2.32 | 1.54 | 1.08 | 1.31 | 1.04 |
| Pigyl | 1.61 | 2.01 | 1.25 | 0.92 | 0.82 | 0.96 | 0.53 | 0.63 | 0.59 | 1.19 | 1.86 | 1.31 |
| Pih1d1 | 1.07 | 0.98 | 1.05 | 0.94 | 0.53 | 1.01 | 0.86 | 1.94 | 0.93 | 0.93 | 1.46 | 0.78 |
| Pilra | 0.72 | 1.63 | 1.95 | 1.00 | 1.00 | 1.00 | 1.00 | 1.13 | 1.00 | 1.00 | 1.00 | 1.00 |
| Pin4 | 2.11 | 1.75 | 0.42 | 0.53 | 0.54 | 0.88 | 1.45 | 1.09 | 1.09 | 0.99 | 1.47 | 1.33 |
| Pinlyp | 1.22 | 1.11 | 0.77 | 1.00 | 1.00 | 1.00 | 1.00 | 1.00 | 1.00 | 1.00 | 1.00 | 1.00 |
| Pir | 2.05 | 3.33 | 2.27 | 1.00 | 1.23 | 1.00 | 1.36 | 1.47 | 1.23 | 1.58 | 1.37 | 0.67 |
| Pkdcc | 1.21 | 1.01 | 1.01 | 1.13 | 1.23 | 1.21 | 0.77 | 0.47 | 0.97 | 1.02 | 1.17 | 1.08 |
| Pkig | 1.56 | 1.41 | 1.31 | 0.77 | 0.70 | 0.98 | 1.37 | 2.18 | 1.21 | 1.01 | 1.55 | 1.22 |
| Pkn1 | 0.93 | 0.95 | 1.04 | 1.15 | 0.67 | 1.22 | 1.02 | 2.97 | 1.16 | 0.99 | 1.16 | 0.88 |
| Pla2g12a | 1.13 | 1.29 | 0.77 | 1.03 | 0.68 | 1.02 | 0.77 | 1.26 | 0.93 | 0.78 | 1.20 | 1.11 |
| Pla2g1b | 0.73 | 1.53 | 0.98 | 1.03 | 0.27 | 1.06 | 1.33 | 1.97 | 0.96 | 0.51 | 2.49 | 6.16 |
| Pla2g2d | 1.45 | 1.61 | 1.69 | 1.00 | 1.00 | 1.00 | 1.00 | 1.00 | 1.00 | 1.14 | 0.68 | 0.75 |
| Plac9a | 1.00 | 1.19 | 1.00 | 3.03 | 0.66 | 1.00 | 1.00 | 4.34 | 1.00 | 2.58 | 2.80 | 2.89 |
| Plaur | 2.87 | 7.19 | 2.18 | 0.82 | 0.87 | 1.32 | 1.00 | 1.00 | 1.00 | 1.13 | 1.01 | 0.78 |
| Plb1 | 1.30 | 1.25 | 1.14 | 1.00 | 1.00 | 1.00 | 1.00 | 1.00 | 1.00 | 1.00 | 1.00 | 1.00 |
| Pld4 | 1.77 | 1.81 | 1.67 | 1.23 | 0.86 | 1.14 | 1.31 | 1.52 | 0.88 | 1.13 | 1.26 | 1.12 |
| Plekhb1 | 0.52 | 0.60 | 0.67 | 0.67 | 0.80 | 0.54 | 0.30 | 0.26 | 0.30 | 0.66 | 0.88 | 0.66 |
| Plekhf1 | 1.88 | 1.31 | 1.27 | 1.14 | 1.30 | 1.06 | 0.44 | 0.33 | 0.60 | 1.21 | 1.06 | 1.05 |
| Plekhg1 | 1.25 | 0.84 | 1.72 | 1.09 | 1.00 | 1.08 | 1.00 | 1.00 | 0.91 | 2.05 | 1.23 | 2.11 |
| Plekhm2 | 1.26 | 1.22 | 1.33 | 1.81 | 1.43 | 1.63 | 1.20 | 2.08 | 1.24 | 0.94 | 1.11 | 0.95 |
| Plin5 | 0.39 | 0.95 | 0.48 | 1.00 | 0.79 | 1.09 | 1.97 | 4.40 | 2.26 | 1.00 | 1.00 | 1.00 |
| Plk3 | 1.19 | 1.31 | 1.65 | 4.10 | 7.56 | 1.96 | 1.87 | 0.65 | 2.05 | 2.07 | 3.26 | 1.84 |
| Plp1 | 1.56 | 1.02 | 1.25 | 0.91 | 1.00 | 0.99 | 1.00 | 1.00 | 1.00 | 1.06 | 0.92 | 1.02 |
| Plrg1 | 1.08 | 1.03 | 0.90 | 1.16 | 0.72 | 1.04 | 1.05 | 1.18 | 1.02 | 1.11 | 1.47 | 0.96 |

Fig. 35- 231

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Pdzd9 | 1.00 | 1.00 | 1.00 | 1.30 | 2.25 | 1.00 | 0.99 | 0.55 | 0.97 | 1.00 | 1.00 | 1.00 |
| Pdzk1ip1 | 1.12 | 1.22 | 1.21 | 3.66 | 9.47 | 2.10 | 1.10 | 2.32 | 0.93 | 0.74 | 0.81 | 0.45 |
| Peg3 | 1.73 | 1.55 | 1.07 | 5.21 | 0.44 | 1.40 | 1.00 | 1.00 | 1.00 | 1.76 | 6.75 | 1.78 |
| Peg3os | 2.65 | 0.88 | 2.99 | 5.31 | 0.53 | 1.69 | 1.00 | 1.00 | 1.00 | 2.13 | 3.80 | 0.91 |
| Pemt | 0.73 | 0.81 | 1.28 | 0.59 | 2.48 | 0.82 | 1.07 | 2.16 | 1.29 | 0.60 | 0.62 | 0.89 |
| Penk | 1.69 | 1.89 | 2.26 | 1.15 | 2.02 | 1.41 | 0.93 | 0.22 | 0.97 | 1.49 | 6.35 | 1.55 |
| Perp | 0.96 | 1.09 | 1.07 | 1.71 | 2.84 | 3.28 | 0.95 | 1.25 | 1.07 | 1.00 | 1.71 | 1.00 |
| Pet100 | 0.82 | 0.98 | 1.00 | 1.16 | 2.91 | 1.05 | 0.71 | 4.99 | 1.32 | 0.61 | 1.48 | 1.17 |
| Pet112 | 0.94 | 1.05 | 1.21 | 0.81 | 1.72 | 0.86 | 1.09 | 2.20 | 1.19 | 0.96 | 1.07 | 1.05 |
| Pex11g | 0.71 | 0.83 | 0.70 | 1.13 | 1.58 | 0.86 | 0.90 | 1.33 | 0.99 | 0.77 | 1.17 | 1.21 |
| Pex16 | 1.03 | 1.39 | 0.94 | 0.84 | 1.78 | 1.29 | 1.05 | 3.48 | 1.12 | 0.65 | 1.34 | 0.93 |
| Pex5l | 1.10 | 1.63 | 0.93 | 1.00 | 1.00 | 1.00 | 0.96 | 3.04 | 1.14 | 1.19 | 6.74 | 1.35 |
| Pex6 | 1.07 | 1.18 | 1.14 | 1.10 | 2.32 | 1.24 | 1.09 | 4.16 | 1.17 | 0.90 | 1.12 | 1.08 |
| Pfdn1 | 0.81 | 0.88 | 0.90 | 0.95 | 2.88 | 0.85 | 0.99 | 1.57 | 1.00 | 0.99 | 1.34 | 0.88 |
| Pfdn2 | 0.97 | 1.01 | 0.92 | 1.14 | 1.21 | 1.03 | 0.98 | 0.41 | 0.80 | 1.12 | 0.91 | 0.89 |
| Pfdn5 | 1.19 | 1.11 | 1.08 | 1.02 | 2.14 | 0.98 | 0.80 | 3.61 | 1.14 | 1.18 | 1.32 | 0.89 |
| Pfkfb3 | 1.24 | 1.09 | 1.07 | 0.52 | 0.97 | 1.35 | 1.02 | 1.48 | 1.03 | 0.99 | 0.66 | 1.01 |
| Pfn3 | 1.00 | 1.00 | 1.00 | 2.75 | 3.67 | 1.00 | 0.96 | 2.71 | 1.14 | 1.00 | 1.00 | 1.00 |
| Pgam2 | 1.94 | 1.21 | 1.87 | 1.88 | 3.32 | 0.80 | 0.92 | 4.68 | 0.99 | 1.60 | 1.40 | 1.18 |
| Pgbd5 | 1.33 | 1.09 | 1.14 | 1.00 | 1.00 | 1.00 | 1.16 | 0.49 | 0.79 | 1.11 | 5.95 | 1.00 |
| Pgc | 1.18 | 1.50 | 1.57 | 1.58 | 0.72 | 0.51 | 1.47 | 1.00 | 0.85 | 1.00 | 1.00 | 1.07 |
| Pgf | 0.67 | 1.39 | 2.15 | 1.86 | 5.10 | 1.33 | 0.73 | 1.38 | 0.57 | 0.57 | 0.41 | 0.65 |
| Pgk2 | 1.00 | 1.00 | 1.00 | 3.18 | 1.00 | 1.00 | 0.95 | 0.27 | 0.93 | 1.00 | 1.00 | 1.00 |
| Pgls | 1.07 | 1.34 | 1.10 | 0.73 | 2.01 | 0.88 | 0.75 | 3.11 | 0.96 | 1.02 | 1.49 | 1.05 |
| Pglyrp1 | 1.61 | 1.30 | 1.93 | 2.19 | 2.63 | 1.93 | 1.00 | 1.00 | 1.00 | 1.57 | 1.16 | 0.92 |
| Pgp | 0.94 | 1.02 | 0.93 | 1.38 | 2.52 | 1.38 | 0.95 | 3.25 | 1.05 | 0.94 | 1.17 | 1.00 |
| Phactr1 | 0.83 | 0.96 | 0.90 | 0.92 | 1.00 | 0.65 | 1.13 | 1.22 | 1.09 | 0.95 | 9.85 | 1.21 |
| Phax | 0.98 | 1.12 | 1.08 | 1.17 | 2.43 | 1.34 | 1.07 | 2.26 | 1.07 | 1.06 | 1.13 | 0.91 |
| Phb | 0.80 | 0.90 | 0.90 | 0.72 | 2.01 | 0.82 | 0.90 | 2.10 | 0.83 | 1.02 | 1.59 | 0.96 |
| Phf11c | 1.11 | 1.00 | 1.00 | 19.87 | 2.15 | 4.78 | 1.00 | 1.00 | 0.91 | 1.45 | 1.74 | 1.85 |
| Phf7 | 0.87 | 1.41 | 0.97 | 1.63 | 1.76 | 1.10 | 0.97 | 1.21 | 1.03 | 1.25 | 1.41 | 1.15 |
| Phkg2 | 1.17 | 1.29 | 1.23 | 1.26 | 0.36 | 0.87 | 0.97 | 0.94 | 1.00 | 1.10 | 1.42 | 1.09 |
| Phpt1 | 1.00 | 1.40 | 1.05 | 0.93 | 15.68 | 1.25 | 1.01 | 1.10 | 0.87 | 0.86 | 1.33 | 1.00 |
| Phyh | 1.21 | 1.27 | 1.06 | 0.85 | 1.78 | 1.08 | 0.63 | 0.22 | 0.85 | 1.16 | 1.12 | 1.06 |
| Phyhd1 | 1.14 | 1.32 | 1.46 | 1.44 | 3.59 | 1.49 | 1.00 | 0.91 | 1.00 | 1.86 | 2.18 | 1.58 |
| Phyhipl | 1.74 | 2.28 | 1.50 | 1.63 | 1.00 | 1.10 | 1.02 | 0.33 | 0.98 | 1.00 | 7.72 | 1.00 |
| Pigb | 0.70 | 0.56 | 0.86 | 1.00 | 4.50 | 0.69 | 1.00 | 8.51 | 1.00 | 1.06 | 0.75 | 1.29 |
| Pigr | 5.12 | 2.54 | 3.66 | 1.36 | 1.00 | 1.18 | 1.00 | 1.00 | 1.00 | 1.00 | 1.00 | 1.00 |
| Pigu | 0.97 | 0.95 | 0.89 | 0.98 | 2.47 | 0.86 | 0.81 | 1.73 | 1.00 | 1.11 | 1.30 | 1.06 |
| Pigx | 0.79 | 1.08 | 0.91 | 0.90 | 1.91 | 1.02 | 1.00 | 2.72 | 1.13 | 0.89 | 1.13 | 1.16 |
| Pigyl | 1.27 | 1.30 | 1.35 | 0.85 | 1.98 | 0.92 | 1.64 | 1.67 | 1.20 | 1.35 | 1.64 | 1.17 |
| Pih1d1 | 1.10 | 0.90 | 0.94 | 0.76 | 0.91 | 0.83 | 0.90 | 2.43 | 1.05 | 0.69 | 1.04 | 0.87 |
| Pilra | 1.00 | 1.00 | 1.00 | 1.00 | 0.70 | 1.00 | 0.83 | 1.04 | 0.74 | 0.80 | 1.06 | 1.04 |
| Pin4 | 0.76 | 0.51 | 1.18 | 1.34 | 3.73 | 1.38 | 0.60 | 2.76 | 0.71 | 1.16 | 2.08 | 1.94 |
| Pinlyp | 1.17 | 1.00 | 1.20 | 1.00 | 2.31 | 1.00 | 0.82 | 1.67 | 0.64 | 1.00 | 1.00 | 1.00 |
| Pir | 0.69 | 0.85 | 0.78 | 1.04 | 2.88 | 1.27 | 1.00 | 0.92 | 1.00 | 0.58 | 0.88 | 1.00 |
| Pkdcc | 1.09 | 0.94 | 1.25 | 0.97 | 1.65 | 1.67 | 0.78 | 0.44 | 0.84 | 0.97 | 1.21 | 1.03 |
| Pkig | 0.94 | 1.01 | 1.09 | 0.88 | 1.97 | 0.92 | 0.97 | 2.00 | 0.98 | 1.56 | 1.88 | 1.54 |
| Pkn1 | 0.92 | 1.00 | 0.70 | 1.11 | 1.60 | 0.94 | 1.04 | 3.07 | 1.26 | 0.97 | 0.98 | 1.16 |
| Pla2g12a | 0.87 | 0.84 | 0.79 | 1.11 | 3.08 | 1.45 | 0.95 | 1.74 | 0.85 | 1.44 | 1.44 | 1.08 |
| Pla2g1b | 1.47 | 1.87 | 2.13 | 1.60 | 1.07 | 0.80 | 1.78 | 2.15 | 0.61 | 1.09 | 6.34 | 1.34 |
| Pla2g2d | 1.06 | 0.53 | 1.35 | 2.14 | 1.35 | 2.40 | 1.00 | 1.00 | 1.00 | 0.68 | 0.77 | 0.67 |
| Plac9a | 3.60 | 1.32 | 1.00 | 0.72 | 1.39 | 0.61 | 0.99 | 7.35 | 1.85 | 3.92 | 5.08 | 0.61 |
| Plaur | 0.83 | 0.57 | 0.51 | 1.46 | 1.00 | 1.14 | 1.00 | 1.00 | 1.00 | 1.30 | 2.02 | 0.79 |
| Plb1 | 1.00 | 1.00 | 1.00 | 1.00 | 1.42 | 1.00 | 0.91 | 1.38 | 0.86 | 1.00 | 1.00 | 1.00 |
| Pld4 | 1.55 | 0.76 | 2.06 | 0.71 | 2.43 | 0.88 | 1.15 | 1.77 | 1.53 | 0.92 | 0.99 | 0.94 |
| Plekhb1 | 0.98 | 0.94 | 1.20 | 0.97 | 1.27 | 1.55 | 0.65 | 0.26 | 0.69 | 0.81 | 18.49 | 0.74 |
| Plekhf1 | 1.08 | 1.43 | 1.42 | 1.05 | 0.69 | 1.32 | 0.88 | 0.74 | 1.06 | 1.08 | 1.23 | 1.17 |
| Plekhg1 | 1.32 | 1.10 | 1.17 | 1.42 | 0.53 | 1.06 | 1.28 | 1.00 | 0.93 | 1.12 | 0.82 | 1.02 |
| Plekhm2 | 1.09 | 1.35 | 1.00 | 2.20 | 5.56 | 1.25 | 1.04 | 1.27 | 1.08 | 0.88 | 1.11 | 1.01 |
| Plin5 | 0.91 | 0.88 | 1.19 | 1.55 | 3.08 | 1.50 | 1.00 | 1.20 | 0.70 | 1.00 | 1.26 | 1.00 |
| Plk3 | 1.25 | 1.59 | 1.16 | 2.37 | 0.64 | 3.10 | 1.00 | 1.00 | 1.00 | 0.80 | 0.79 | 0.83 |
| Plp1 | 1.23 | 1.23 | 1.04 | 1.15 | 0.72 | 1.44 | 0.94 | 1.23 | 1.07 | 1.23 | 20.74 | 0.90 |
| Plrg1 | 1.07 | 0.87 | 0.91 | 1.15 | 6.56 | 1.21 | 1.26 | 1.94 | 0.91 | 1.02 | 1.24 | 1.01 |

Fig. 35- 232

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Pdzd9 | 1.00 | 1.00 | 1.00 | 1.00 | 1.53 | 1.00 | 1.94 | 1.23 | 1.00 | 1.00 | 1.00 | 1.00 |
| Pdzk1ip1 | 0.73 | 1.00 | 0.72 | 1.00 | 2.46 | 1.00 | 0.95 | 7.36 | 0.66 | 1.67 | 0.83 | 0.97 |
| Peg3 | 1.00 | 1.00 | 1.00 | 0.78 | 0.44 | 0.90 | 1.62 | 0.92 | 3.75 | 1.00 | 1.00 | 1.00 |
| Peg3os | 1.00 | 1.00 | 1.00 | 1.10 | 1.00 | 1.07 | 1.35 | 0.48 | 4.54 | 1.00 | 1.00 | 1.00 |
| Pemt | 1.00 | 1.00 | 1.00 | 1.00 | 7.38 | 1.17 | 1.62 | 1.83 | 0.96 | 2.34 | 0.77 | 0.96 |
| Penk | 0.81 | 1.31 | 1.11 | 1.24 | 3.11 | 1.22 | 1.36 | 0.41 | 1.32 | 1.00 | 1.00 | 1.03 |
| Perp | 1.57 | 1.38 | 1.05 | 1.27 | 2.58 | 1.24 | 0.77 | 0.77 | 0.70 | 1.20 | 0.68 | 1.66 |
| Pet100 | 1.00 | 1.00 | 1.15 | 0.92 | 0.66 | 0.97 | 1.16 | 14.62 | 0.93 | 3.94 | 1.39 | 1.25 |
| Pet112 | 1.00 | 0.80 | 1.00 | 1.01 | 0.67 | 0.76 | 1.13 | 6.31 | 1.39 | 2.41 | 0.92 | 1.06 |
| Pex11g | 0.98 | 0.73 | 0.87 | 1.30 | 1.00 | 1.08 | 1.85 | 6.14 | 1.27 | 2.43 | 1.70 | 1.41 |
| Pex16 | 1.55 | 1.00 | 0.61 | 1.40 | 1.03 | 0.82 | 1.44 | 9.15 | 1.02 | 3.10 | 1.22 | 0.99 |
| Pex5l | 1.00 | 1.00 | 1.00 | 0.99 | 0.95 | 1.05 | 1.99 | 0.99 | 1.40 | 1.00 | 1.00 | 1.00 |
| Pex6 | 1.15 | 0.80 | 1.05 | 0.95 | 0.91 | 1.01 | 1.46 | 10.97 | 1.15 | 3.57 | 1.37 | 0.97 |
| Pfdn1 | 1.07 | 0.79 | 0.97 | 1.25 | 0.97 | 1.05 | 1.30 | 5.85 | 0.88 | 2.08 | 0.96 | 1.10 |
| Pfdn2 | 1.13 | 0.96 | 0.63 | 1.02 | 11.39 | 1.00 | 1.00 | 0.52 | 1.09 | 0.83 | 0.71 | 0.80 |
| Pfdn5 | 1.19 | 1.01 | 0.89 | 0.99 | 1.01 | 1.07 | 1.40 | 30.27 | 1.09 | 5.19 | 1.51 | 1.08 |
| Pfkfb3 | 0.92 | 1.30 | 2.51 | 1.10 | 1.21 | 1.01 | 1.42 | 2.03 | 1.91 | 1.18 | 0.98 | 1.08 |
| Pfn3 | 1.00 | 1.00 | 1.00 | 1.00 | 5.31 | 1.00 | 1.00 | 1.00 | 1.00 | 1.00 | 1.00 | 1.00 |
| Pgam2 | 1.00 | 1.52 | 1.00 | 1.64 | 0.92 | 0.79 | 1.88 | 18.65 | 1.68 | 0.69 | 1.29 | 1.33 |
| Pgbd5 | 1.00 | 1.00 | 1.00 | 1.11 | 1.31 | 1.03 | 1.00 | 1.00 | 1.00 | 1.00 | 1.00 | 1.00 |
| Pgc | 8.42 | 1.00 | 0.30 | 1.00 | 0.77 | 0.37 | 1.00 | 20.49 | 1.15 | 3.32 | 0.85 | 1.00 |
| Pgf | 2.61 | 2.80 | 1.50 | 1.23 | 0.82 | 0.98 | 1.00 | 5.39 | 1.00 | 1.00 | 1.00 | 1.00 |
| Pgk2 | 1.00 | 1.00 | 1.00 | 1.00 | 1.00 | 1.00 | 8.64 | 1.00 | 1.00 | 1.00 | 1.00 | 1.00 |
| Pgls | 1.05 | 1.04 | 0.96 | 1.09 | 1.11 | 1.09 | 1.28 | 15.15 | 0.92 | 3.01 | 1.19 | 1.04 |
| Pglyrp1 | 1.00 | 1.00 | 1.00 | 1.18 | 0.76 | 1.32 | 2.07 | 13.68 | 2.48 | 3.31 | 1.69 | 1.44 |
| Pgp | 1.23 | 1.47 | 1.57 | 1.10 | 0.83 | 1.02 | 2.41 | 11.72 | 1.15 | 1.95 | 0.99 | 0.88 |
| Phactr1 | 1.00 | 1.00 | 1.00 | 1.03 | 1.51 | 0.99 | 1.62 | 0.56 | 1.43 | 1.00 | 1.00 | 1.00 |
| Phax | 1.04 | 0.89 | 1.11 | 1.10 | 1.20 | 0.98 | 0.93 | 5.58 | 1.02 | 1.84 | 1.07 | 1.05 |
| Phb | 0.75 | 0.90 | 1.01 | 1.21 | 0.84 | 0.96 | 1.08 | 8.18 | 0.86 | 2.47 | 0.85 | 0.90 |
| Phf11c | 1.00 | 1.00 | 1.00 | 1.00 | 1.00 | 1.00 | 1.37 | 0.89 | 1.12 | 1.71 | 1.10 | 1.46 |
| Phf7 | 1.04 | 1.13 | 0.93 | 0.90 | 0.45 | 0.97 | 2.02 | 4.70 | 0.97 | 2.25 | 1.27 | 1.43 |
| Phkg2 | 0.59 | 1.24 | 1.28 | 1.06 | 1.62 | 1.10 | 1.46 | 3.67 | 1.21 | 1.63 | 1.41 | 1.22 |
| Phpt1 | 0.70 | 0.63 | 0.78 | 1.45 | 1.13 | 1.02 | 1.03 | 2.41 | 0.80 | 2.59 | 1.16 | 1.19 |
| Phyh | 1.12 | 1.79 | 1.20 | 0.98 | 9.65 | 1.06 | 1.03 | 1.41 | 1.06 | 1.23 | 1.73 | 1.40 |
| Phyhd1 | 0.87 | 1.00 | 1.00 | 1.50 | 1.21 | 1.89 | 2.44 | 4.97 | 1.34 | 2.02 | 1.63 | 2.19 |
| Phyhipl | 1.00 | 1.00 | 1.00 | 1.04 | 0.94 | 1.07 | 1.94 | 1.00 | 1.00 | 1.00 | 1.00 | 1.00 |
| Pigb | 0.79 | 1.16 | 0.56 | 0.91 | 0.81 | 0.94 | 0.50 | 45.83 | 0.87 | 5.56 | 0.68 | 0.91 |
| Pigr | 1.04 | 1.09 | 1.40 | 1.00 | 1.00 | 1.00 | 1.16 | 1.26 | 1.00 | 1.00 | 1.00 | 1.00 |
| Pigu | 0.78 | 0.78 | 0.87 | 0.98 | 0.70 | 1.00 | 1.19 | 7.29 | 0.82 | 3.16 | 0.94 | 0.94 |
| Pigx | 1.00 | 0.70 | 0.86 | 1.14 | 1.25 | 0.92 | 1.18 | 7.37 | 0.97 | 2.79 | 1.19 | 1.12 |
| Pigyl | 0.67 | 0.96 | 0.69 | 1.38 | 1.30 | 1.17 | 1.85 | 6.96 | 1.33 | 2.50 | 1.72 | 1.86 |
| Pih1d1 | 0.88 | 0.76 | 1.24 | 1.04 | 1.08 | 1.02 | 1.14 | 6.49 | 0.86 | 3.09 | 0.90 | 1.00 |
| Pilra | 1.00 | 1.00 | 1.00 | 1.00 | 4.81 | 1.00 | 1.00 | 6.56 | 1.00 | 1.37 | 1.00 | 1.05 |
| Pin4 | 1.00 | 1.00 | 1.00 | 1.85 | 1.78 | 1.39 | 0.72 | 26.66 | 1.00 | 3.89 | 0.63 | 1.36 |
| Pinlyp | 1.00 | 1.00 | 1.00 | 1.00 | 1.00 | 1.00 | 1.07 | 5.19 | 0.73 | 1.00 | 1.00 | 1.00 |
| Pir | 1.00 | 1.00 | 1.00 | 1.12 | 0.37 | 1.37 | 1.18 | 3.45 | 0.92 | 1.13 | 1.38 | 1.15 |
| Pkdcc | 0.74 | 1.66 | 0.83 | 1.37 | 0.39 | 0.97 | 1.01 | 0.94 | 1.17 | 1.00 | 1.33 | 0.84 |
| Pkig | 1.00 | 1.79 | 1.22 | 1.00 | 0.75 | 0.96 | 1.16 | 7.32 | 0.93 | 1.66 | 1.14 | 1.08 |
| Pkn1 | 1.22 | 1.05 | 1.21 | 1.00 | 1.00 | 0.89 | 1.36 | 7.02 | 1.41 | 4.44 | 1.36 | 1.02 |
| Pla2g12a | 1.17 | 1.08 | 0.87 | 1.11 | 1.01 | 1.16 | 1.41 | 6.53 | 1.27 | 1.17 | 0.66 | 0.80 |
| Pla2g1b | 0.91 | 0.98 | 0.81 | 1.00 | 2.51 | 0.51 | 1.00 | 6.73 | 1.49 | 3.38 | 0.90 | 1.00 |
| Pla2g2d | 1.00 | 1.00 | 0.79 | 1.00 | 1.00 | 1.00 | 1.62 | 1.64 | 1.00 | 1.00 | 1.63 | 0.56 |
| Plac9a | 1.00 | 1.00 | 0.58 | 1.00 | 0.97 | 2.29 | 0.45 | 100.10 | 0.36 | 1.00 | 1.00 | 1.00 |
| Plaur | 1.00 | 1.00 | 1.00 | 1.00 | 1.00 | 1.00 | 4.69 | 1.57 | 2.19 | 0.77 | 1.48 | 1.25 |
| Plb1 | 1.00 | 1.00 | 1.00 | 1.00 | 3.15 | 1.00 | 1.57 | 15.58 | 0.95 | 1.00 | 1.00 | 1.00 |
| Pld4 | 1.00 | 1.00 | 0.95 | 0.89 | 0.56 | 0.88 | 1.74 | 9.23 | 1.66 | 2.92 | 1.28 | 1.21 |
| Plekhb1 | 0.88 | 0.78 | 0.79 | 0.97 | 1.07 | 0.90 | 1.64 | 0.62 | 1.53 | 1.00 | 1.00 | 1.00 |
| Plekhf1 | 0.73 | 0.82 | 0.56 | 1.36 | 6.95 | 1.20 | 1.05 | 1.04 | 1.18 | 0.86 | 0.88 | 1.27 |
| Plekhg1 | 1.00 | 1.00 | 1.00 | 0.96 | 1.00 | 0.93 | 0.95 | 0.15 | 1.02 | 1.00 | 4.63 | 3.49 |
| Plekhm2 | 1.57 | 0.99 | 1.20 | 1.10 | 1.16 | 1.00 | 1.36 | 2.46 | 1.21 | 1.75 | 1.08 | 0.89 |
| Plin5 | 0.65 | 0.64 | 0.36 | 1.00 | 1.00 | 1.00 | 2.91 | 8.83 | 2.56 | 1.10 | 1.29 | 1.00 |
| Plk3 | 1.00 | 1.00 | 1.00 | 1.21 | 1.00 | 1.11 | 1.31 | 0.25 | 1.04 | 0.69 | 1.93 | 1.35 |
| Plp1 | 1.00 | 1.00 | 1.00 | 1.00 | 0.85 | 0.98 | 1.70 | 1.53 | 1.34 | 1.00 | 1.00 | 1.00 |
| Plrg1 | 0.71 | 0.90 | 1.41 | 1.21 | 0.86 | 1.06 | 0.86 | 3.68 | 0.74 | 1.76 | 0.99 | 1.32 |

Fig. 35- 233

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Plvap | 1.79 | 1.59 | 1.42 | 0.69 | 0.86 | 1.17 | 0.95 | 0.65 | 1.25 | 1.41 | 2.96 | 6.66 |
| Pmaip1 | 1.00 | 1.00 | 1.00 | 1.17 | 1.00 | 1.00 | 1.35 | 1.40 | 1.00 | 2.15 | 1.65 | 2.32 |
| Pmf1 | 1.28 | 0.83 | 1.11 | 0.31 | 3.86 | 0.98 | 1.00 | 0.78 | 1.13 | 1.47 | 2.62 | 0.77 |
| Pmm1 | 2.29 | 0.77 | 1.34 | 0.94 | 22.45 | 1.99 | 2.16 | 1.45 | 1.31 | 1.95 | 3.15 | 0.98 |
| Pmvk | 1.08 | 0.98 | 0.98 | 0.60 | 5.86 | 0.86 | 1.19 | 0.82 | 0.88 | 3.10 | 7.40 | 2.26 |
| Pnlip | 1.00 | 1.00 | 1.00 | 1.08 | 1.00 | 1.00 | 1.00 | 1.00 | 1.00 | 1.00 | 1.00 | 1.41 |
| Pnliprp1 | 1.00 | 1.00 | 1.00 | 1.00 | 1.00 | 1.00 | 1.00 | 1.00 | 1.00 | 1.00 | 1.00 | 1.00 |
| Pnliprp2 | 1.00 | 1.00 | 1.00 | 1.00 | 1.00 | 1.00 | 1.00 | 1.00 | 1.00 | 1.00 | 1.00 | 1.00 |
| Pnpla7 | 1.83 | 1.35 | 1.76 | 4.15 | 20.94 | 3.12 | 3.43 | 2.94 | 1.94 | 2.29 | 3.53 | 1.57 |
| Poc1a | 1.00 | 1.00 | 1.00 | 0.24 | 1.03 | 0.54 | 1.00 | 1.00 | 0.57 | 2.92 | 5.12 | 2.10 |
| Pofut2 | 1.17 | 0.99 | 1.02 | 0.63 | 1.06 | 0.97 | 0.93 | 0.79 | 0.94 | 1.33 | 1.07 | 0.96 |
| Pold2 | 0.94 | 0.58 | 0.96 | 0.72 | 4.24 | 1.24 | 0.83 | 0.83 | 1.00 | 2.60 | 2.56 | 0.86 |
| Pole3 | 0.82 | 0.68 | 0.68 | 0.51 | 6.26 | 0.80 | 1.21 | 1.07 | 0.84 | 2.99 | 3.77 | 1.06 |
| Pole4 | 1.00 | 0.84 | 0.70 | 0.93 | 1.45 | 0.68 | 0.72 | 0.90 | 0.81 | 1.34 | 1.29 | 0.87 |
| Polr2c | 1.05 | 0.99 | 0.89 | 0.59 | 2.84 | 1.11 | 0.87 | 0.72 | 0.95 | 0.98 | 1.88 | 1.11 |
| Polr2e | 1.00 | 0.59 | 0.97 | 0.24 | 7.63 | 1.06 | 0.97 | 0.80 | 0.84 | 2.18 | 3.82 | 1.00 |
| Polr2f | 1.60 | 0.52 | 0.94 | 0.21 | 6.69 | 0.95 | 1.28 | 0.92 | 0.58 | 1.47 | 3.28 | 0.92 |
| Polr2l | 1.28 | 0.51 | 0.97 | 0.29 | 10.22 | 1.13 | 1.01 | 0.87 | 0.75 | 2.25 | 3.27 | 1.02 |
| Pomc | 1.00 | 0.79 | 1.00 | 0.35 | 8.65 | 0.59 | 1.73 | 0.86 | 1.07 | 1.45 | 3.65 | 1.65 |
| Pomp | 1.51 | 0.79 | 0.90 | 0.32 | 5.32 | 1.02 | 0.88 | 0.84 | 0.83 | 1.91 | 2.98 | 1.10 |
| Pop5 | 1.23 | 0.54 | 1.01 | 0.39 | 8.66 | 0.85 | 1.06 | 0.76 | 0.78 | 2.11 | 3.66 | 1.03 |
| Por | 1.33 | 1.07 | 1.41 | 0.54 | 3.72 | 1.30 | 1.29 | 1.12 | 0.89 | 2.03 | 3.51 | 1.10 |
| Ppa1 | 1.63 | 0.84 | 1.06 | 0.37 | 2.34 | 0.82 | 1.17 | 1.01 | 0.75 | 1.14 | 3.12 | 1.25 |
| Ppa2 | 0.93 | 0.49 | 0.82 | 0.51 | 6.88 | 1.04 | 0.91 | 0.75 | 0.72 | 1.68 | 2.19 | 1.03 |
| Ppan | 1.17 | 0.61 | 1.08 | 0.66 | 6.78 | 1.21 | 1.23 | 0.98 | 1.31 | 2.04 | 3.45 | 1.34 |
| Ppargc1a | 6.33 | 3.95 | 1.76 | 3.16 | 0.73 | 1.91 | 0.83 | 1.54 | 0.96 | 1.00 | 1.00 | 0.88 |
| Ppcdc | 1.25 | 0.87 | 0.81 | 0.54 | 2.06 | 0.73 | 0.86 | 0.65 | 0.93 | 1.50 | 1.13 | 0.86 |
| Ppdpf | 0.13 | 0.07 | 0.19 | 0.12 | 2.09 | 0.35 | 0.25 | 0.21 | 0.33 | 0.57 | 0.90 | 0.34 |
| Ppie | 1.04 | 0.58 | 1.12 | 0.44 | 11.44 | 1.09 | 0.92 | 0.70 | 0.84 | 2.46 | 3.95 | 0.78 |
| Ppih | 1.00 | 0.83 | 1.00 | 0.62 | 3.03 | 1.00 | 1.01 | 1.27 | 1.28 | 3.05 | 2.93 | 1.34 |
| Ppil2 | 1.11 | 0.58 | 0.94 | 0.61 | 8.67 | 1.12 | 0.97 | 1.00 | 0.87 | 2.18 | 3.17 | 0.94 |
| Ppil6 | 1.00 | 1.00 | 1.00 | 1.00 | 1.00 | 1.00 | 0.68 | 1.00 | 0.68 | 2.15 | 2.44 | 1.12 |
| Ppm1e | 1.00 | 1.00 | 1.00 | 1.00 | 0.30 | 1.00 | 5.38 | 7.65 | 4.49 | 1.00 | 1.00 | 1.00 |
| Ppox | 1.26 | 0.95 | 1.81 | 0.91 | 4.02 | 0.83 | 1.21 | 1.34 | 1.34 | 5.30 | 4.61 | 1.33 |
| Ppp1ca | 1.04 | 0.72 | 0.84 | 0.61 | 3.67 | 1.11 | 0.95 | 0.91 | 0.82 | 2.11 | 2.00 | 0.96 |
| Ppp1r11 | 1.37 | 1.08 | 1.14 | 0.73 | 2.51 | 1.04 | 1.22 | 0.95 | 0.95 | 1.25 | 1.54 | 1.17 |
| Ppp1r12c | 1.44 | 0.96 | 1.68 | 0.85 | 5.28 | 1.43 | 1.56 | 1.52 | 1.53 | 2.17 | 2.81 | 1.07 |
| Ppp1r14d | 1.00 | 1.00 | 1.00 | 1.00 | 1.00 | 1.00 | 1.00 | 1.00 | 1.00 | 2.66 | 5.49 | 1.29 |
| Ppp1r1b | 1.00 | 1.00 | 1.00 | 1.00 | 0.07 | 1.00 | 0.31 | 0.41 | 1.06 | 1.59 | 1.84 | 1.73 |
| Ppp1r27 | 1.08 | 0.50 | 1.11 | 1.00 | 1.00 | 1.00 | 1.00 | 1.00 | 1.00 | 1.00 | 1.00 | 1.00 |
| Ppp1r3g | 1.00 | 1.00 | 1.00 | 4.94 | 15.27 | 3.61 | 1.87 | 1.37 | 0.85 | 1.00 | 1.00 | 1.00 |
| Ppp2r2c | 1.00 | 1.00 | 1.00 | 1.00 | 0.09 | 1.00 | 1.00 | 1.00 | 1.00 | 1.00 | 1.00 | 1.17 |
| Ppp2r2d | 1.41 | 1.23 | 1.22 | 1.42 | 4.85 | 1.53 | 0.95 | 1.00 | 1.06 | 1.91 | 2.00 | 0.97 |
| Ppp2r3d | 1.24 | 0.69 | 1.19 | 0.34 | 6.29 | 0.91 | 0.63 | 0.70 | 0.63 | 2.72 | 2.79 | 0.75 |
| Ppp4c | 1.25 | 0.62 | 1.14 | 0.46 | 7.50 | 1.12 | 0.99 | 0.79 | 1.02 | 2.11 | 3.88 | 0.94 |
| Pqbp1 | 0.74 | 0.59 | 0.70 | 0.45 | 2.72 | 0.93 | 0.79 | 0.64 | 0.70 | 1.30 | 1.71 | 0.88 |
| Prap1 | 0.87 | 1.00 | 2.38 | 1.00 | 1.00 | 2.51 | 2.79 | 1.00 | 1.40 | 1.00 | 1.00 | 1.00 |
| Prdx2 | 0.95 | 0.52 | 0.77 | 0.40 | 5.19 | 0.87 | 0.83 | 0.79 | 0.76 | 1.29 | 2.30 | 0.85 |
| Prg2 | 1.00 | 1.00 | 1.00 | 1.00 | 1.00 | 1.00 | 1.00 | 1.00 | 1.00 | 1.26 | 1.53 | 0.73 |
| Prg4 | 4.67 | 3.35 | 4.55 | 8.55 | 8.08 | 4.86 | 1.55 | 1.88 | 2.76 | 1.56 | 7.38 | 1.05 |
| Prima1 | 0.73 | 1.22 | 0.94 | 1.00 | 1.00 | 1.00 | 1.00 | 1.00 | 1.00 | 1.00 | 1.00 | 1.00 |
| Prkab2 | 0.71 | 2.57 | 0.85 | 6.89 | 0.44 | 1.73 | 1.36 | 1.61 | 1.36 | 1.00 | 0.57 | 1.03 |
| Prkar2b | 0.69 | 1.03 | 1.38 | 0.79 | 0.34 | 0.74 | 1.05 | 1.26 | 2.10 | 0.81 | 0.97 | 1.07 |
| Prkcg | 0.88 | 0.67 | 1.00 | 0.54 | 0.30 | 1.00 | 0.75 | 0.65 | 0.77 | 1.36 | 1.21 | 0.80 |
| Prkcsh | 1.29 | 0.83 | 1.02 | 0.44 | 6.15 | 1.02 | 1.16 | 1.12 | 1.01 | 2.02 | 3.90 | 1.06 |
| Prkcz | 1.00 | 0.76 | 1.03 | 1.00 | 0.41 | 1.00 | 0.96 | 1.00 | 0.91 | 3.78 | 3.17 | 1.24 |
| Prkrip1 | 1.03 | 0.71 | 1.00 | 0.55 | 5.96 | 1.15 | 1.28 | 1.42 | 0.92 | 1.68 | 2.81 | 0.97 |
| Prm1 | 1.00 | 1.10 | 1.00 | 1.00 | 1.88 | 1.00 | 2.58 | 1.00 | 1.00 | 14.01 | 1.00 | 1.00 |
| Prm2 | 1.00 | 2.48 | 1.00 | 1.00 | 1.02 | 1.00 | 1.43 | 2.02 | 1.00 | 17.89 | 2.49 | 1.00 |
| Prm3 | 1.00 | 1.07 | 1.00 | 1.00 | 1.00 | 1.00 | 1.00 | 1.00 | 1.00 | 6.02 | 1.00 | 1.00 |
| Prmt5 | 1.01 | 0.65 | 0.95 | 0.76 | 3.53 | 0.99 | 1.06 | 1.06 | 1.02 | 3.58 | 2.81 | 0.82 |
| Procr | 2.56 | 2.41 | 2.09 | 2.92 | 1.91 | 1.94 | 1.14 | 1.07 | 1.21 | 0.72 | 0.91 | 1.42 |
| Prol1 | 1.00 | 1.00 | 1.00 | 1.00 | 1.00 | 1.00 | 1.00 | 1.00 | 1.00 | 1.00 | 1.00 | 1.00 |
| Proser2 | 1.00 | 1.00 | 1.00 | 1.46 | 6.08 | 1.23 | 2.29 | 2.45 | 1.85 | 2.68 | 3.22 | 1.40 |

Fig. 35- 234

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Plvap | 1.50 | 1.22 | 1.00 | 1.04 | 1.22 | 1.14 | 1.94 | 1.37 | 2.03 | 0.92 | 1.17 | 1.16 |
| Pmaip1 | 1.37 | 1.14 | 1.60 | 1.28 | 1.75 | 1.27 | 1.00 | 1.00 | 1.00 | 1.42 | 1.13 | 1.02 |
| Pmf1 | 0.77 | 1.19 | 0.73 | 0.74 | 0.75 | 1.07 | 1.21 | 1.22 | 0.75 | 1.26 | 1.53 | 0.99 |
| Pmm1 | 1.65 | 2.03 | 0.93 | 1.36 | 1.06 | 0.95 | 1.56 | 2.70 | 1.92 | 1.11 | 2.10 | 1.24 |
| Pmvk | 1.15 | 1.64 | 0.99 | 0.98 | 0.99 | 1.11 | 1.06 | 1.66 | 0.75 | 1.14 | 1.71 | 0.97 |
| Pnlip | 1.00 | 1.00 | 1.91 | 1.00 | 1.00 | 1.51 | 1.00 | 1.00 | 0.80 | 0.72 | 4.43 | 45.34 |
| Pnliprp1 | 1.00 | 1.00 | 1.00 | 1.00 | 1.00 | 0.97 | 1.00 | 1.00 | 1.07 | 0.25 | 1.61 | 19.07 |
| Pnliprp2 | 1.00 | 1.00 | 1.00 | 1.00 | 1.00 | 1.00 | 1.00 | 1.00 | 1.00 | 0.52 | 2.84 | 15.00 |
| Pnpla7 | 1.42 | 1.64 | 1.32 | 1.66 | 1.62 | 1.57 | 2.03 | 2.17 | 1.31 | 1.09 | 1.43 | 1.19 |
| Poc1a | 0.48 | 0.85 | 0.75 | 0.86 | 0.74 | 0.60 | 1.00 | 1.00 | 0.91 | 1.37 | 1.14 | 0.99 |
| Pofut2 | 1.13 | 1.15 | 1.04 | 0.97 | 0.82 | 0.99 | 1.17 | 1.96 | 1.08 | 1.05 | 1.18 | 0.95 |
| Pold2 | 0.46 | 0.73 | 0.58 | 0.46 | 0.34 | 0.82 | 0.90 | 1.68 | 0.43 | 1.06 | 1.32 | 1.05 |
| Pole3 | 0.72 | 0.86 | 0.90 | 0.87 | 0.46 | 0.85 | 0.95 | 1.85 | 0.74 | 1.38 | 1.22 | 0.78 |
| Pole4 | 0.64 | 0.68 | 0.72 | 0.96 | 0.76 | 0.87 | 3.00 | 4.44 | 1.70 | 0.94 | 0.87 | 0.82 |
| Polr2c | 1.03 | 1.31 | 0.82 | 0.83 | 1.03 | 0.98 | 1.21 | 0.87 | 0.87 | 1.06 | 1.57 | 1.14 |
| Polr2e | 1.07 | 1.39 | 1.06 | 0.74 | 0.59 | 1.02 | 0.92 | 1.77 | 1.03 | 0.95 | 1.79 | 1.11 |
| Polr2f | 1.47 | 1.27 | 0.59 | 0.62 | 0.80 | 0.83 | 0.78 | 1.67 | 1.35 | 1.69 | 2.02 | 1.25 |
| Polr2l | 1.03 | 1.24 | 0.86 | 0.92 | 0.60 | 1.06 | 0.97 | 1.92 | 1.08 | 0.96 | 1.68 | 1.04 |
| Pomc | 0.81 | 1.29 | 0.67 | 0.92 | 0.44 | 0.48 | 1.00 | 2.05 | 1.00 | 1.00 | 1.35 | 1.00 |
| Pomp | 1.13 | 1.31 | 0.92 | 1.03 | 0.75 | 0.97 | 1.16 | 1.42 | 0.97 | 1.00 | 1.57 | 1.02 |
| Pop5 | 1.10 | 1.38 | 0.97 | 0.80 | 0.60 | 0.86 | 0.76 | 1.69 | 0.87 | 0.91 | 1.78 | 1.19 |
| Por | 2.59 | 3.16 | 1.58 | 0.94 | 0.87 | 1.00 | 1.61 | 1.54 | 1.46 | 1.14 | 1.40 | 1.09 |
| Ppa1 | 1.00 | 1.15 | 0.98 | 0.89 | 0.94 | 0.80 | 1.50 | 1.07 | 1.44 | 0.93 | 1.45 | 0.89 |
| Ppa2 | 1.06 | 1.07 | 0.88 | 0.95 | 0.80 | 0.98 | 1.03 | 1.55 | 0.86 | 1.05 | 1.68 | 1.05 |
| Ppan | 1.21 | 1.63 | 0.90 | 1.02 | 0.82 | 1.03 | 1.19 | 1.30 | 1.28 | 0.98 | 1.65 | 1.42 |
| Ppargc1a | 1.00 | 1.00 | 1.04 | 1.19 | 1.05 | 1.19 | 3.68 | 1.22 | 1.34 | 1.13 | 0.80 | 0.91 |
| Ppcdc | 1.10 | 1.34 | 1.04 | 0.70 | 0.53 | 0.60 | 0.93 | 1.41 | 0.90 | 0.81 | 1.14 | 1.02 |
| Ppdpf | 0.34 | 0.53 | 0.35 | 0.27 | 0.17 | 0.27 | 0.25 | 0.36 | 0.27 | 0.42 | 0.65 | 0.46 |
| Ppie | 1.33 | 1.34 | 0.98 | 0.78 | 0.49 | 0.93 | 0.59 | 1.71 | 0.98 | 1.00 | 1.74 | 1.08 |
| Ppih | 1.09 | 1.93 | 0.95 | 1.01 | 0.99 | 1.13 | 1.00 | 1.34 | 1.00 | 1.11 | 2.21 | 1.17 |
| Ppil2 | 1.15 | 1.45 | 1.05 | 1.00 | 0.73 | 1.09 | 0.91 | 1.92 | 0.93 | 1.05 | 1.49 | 0.99 |
| Ppil6 | 1.73 | 1.54 | 1.00 | 1.17 | 0.85 | 1.31 | 1.00 | 1.00 | 1.00 | 1.02 | 1.18 | 1.00 |
| Ppm1e | 0.78 | 0.62 | 0.98 | 1.00 | 1.00 | 1.00 | 1.00 | 1.00 | 1.00 | 1.00 | 0.64 | 1.04 |
| Ppox | 1.54 | 1.55 | 1.41 | 0.99 | 0.51 | 1.06 | 0.60 | 2.92 | 1.13 | 0.91 | 1.41 | 1.03 |
| Ppp1ca | 0.86 | 1.07 | 0.91 | 0.91 | 0.58 | 0.94 | 0.90 | 1.86 | 0.88 | 1.05 | 1.40 | 1.07 |
| Ppp1r11 | 1.04 | 1.29 | 1.12 | 1.07 | 1.11 | 0.90 | 1.42 | 1.16 | 0.99 | 1.17 | 1.67 | 1.17 |
| Ppp1r12c | 1.35 | 1.75 | 1.17 | 1.25 | 0.95 | 1.15 | 1.72 | 2.03 | 1.42 | 1.32 | 1.93 | 1.35 |
| Ppp1r14d | 1.81 | 1.00 | 1.00 | 0.55 | 1.09 | 1.28 | 1.00 | 1.00 | 1.00 | 1.28 | 1.77 | 1.15 |
| Ppp1r1b | 0.67 | 0.75 | 0.65 | 0.71 | 0.99 | 0.78 | 0.36 | 0.26 | 0.42 | 0.99 | 1.18 | 1.04 |
| Ppp1r27 | 1.13 | 0.54 | 1.00 | 1.00 | 1.00 | 1.00 | 1.00 | 1.00 | 1.00 | 1.00 | 1.00 | 1.00 |
| Ppp1r3g | 1.00 | 1.49 | 1.00 | 1.00 | 1.00 | 1.00 | 18.29 | 20.31 | 7.19 | 1.00 | 1.00 | 1.00 |
| Ppp2r2c | 1.00 | 1.00 | 1.00 | 1.00 | 1.00 | 1.00 | 1.00 | 1.00 | 1.00 | 1.02 | 1.00 | 1.30 |
| Ppp2r2d | 1.03 | 1.13 | 0.86 | 1.03 | 0.88 | 1.02 | 1.56 | 2.40 | 1.55 | 1.03 | 1.23 | 0.99 |
| Ppp2r3d | 1.09 | 1.22 | 0.92 | 1.04 | 0.50 | 0.78 | 1.06 | 3.41 | 1.00 | 1.03 | 1.41 | 1.05 |
| Ppp4c | 1.10 | 1.39 | 0.99 | 1.10 | 0.70 | 0.99 | 1.19 | 1.56 | 1.07 | 1.06 | 1.71 | 1.18 |
| Pqbp1 | 1.06 | 1.30 | 0.96 | 0.91 | 0.96 | 0.93 | 1.09 | 0.92 | 0.89 | 0.88 | 1.43 | 1.13 |
| Prap1 | 2.69 | 3.33 | 1.00 | 1.00 | 0.72 | 1.00 | 1.00 | 1.00 | 1.00 | 1.44 | 5.19 | 1.83 |
| Prdx2 | 1.18 | 1.39 | 0.98 | 0.80 | 0.83 | 0.82 | 0.77 | 0.91 | 0.84 | 0.82 | 1.40 | 0.87 |
| Prg2 | 0.22 | 0.70 | 0.77 | 1.00 | 1.00 | 1.00 | 1.00 | 1.00 | 1.00 | 1.00 | 1.00 | 1.00 |
| Prg4 | 1.49 | 1.39 | 1.69 | 1.00 | 1.34 | 1.00 | 2.91 | 4.77 | 2.61 | 1.07 | 1.92 | 1.00 |
| Prima1 | 1.00 | 1.00 | 1.00 | 1.58 | 1.53 | 1.38 | 1.00 | 1.00 | 1.00 | 0.91 | 1.00 | 1.00 |
| Prkab2 | 0.72 | 0.49 | 1.15 | 1.01 | 1.00 | 1.17 | 1.33 | 1.00 | 1.29 | 0.90 | 0.40 | 0.95 |
| Prkar2b | 0.49 | 0.49 | 0.38 | 0.87 | 1.00 | 1.13 | 1.00 | 1.00 | 1.00 | 0.91 | 0.80 | 0.91 |
| Prkcg | 1.00 | 1.00 | 1.00 | 1.00 | 1.00 | 1.00 | 1.00 | 1.00 | 1.00 | 0.73 | 0.91 | 0.79 |
| Prkcsh | 1.29 | 1.50 | 0.96 | 1.05 | 0.78 | 1.01 | 1.50 | 1.86 | 1.29 | 1.20 | 1.60 | 1.11 |
| Prkcz | 1.14 | 1.12 | 1.03 | 1.03 | 0.76 | 1.32 | 1.54 | 6.02 | 1.96 | 1.08 | 1.26 | 1.06 |
| Prkrip1 | 1.16 | 1.28 | 0.96 | 1.09 | 1.12 | 1.03 | 1.22 | 1.54 | 1.11 | 1.22 | 1.45 | 1.15 |
| Prm1 | 1.12 | 0.77 | 0.62 | 1.62 | 3.50 | 1.13 | 1.26 | 14.79 | 2.10 | 1.00 | 1.00 | 0.53 |
| Prm2 | 1.00 | 2.20 | 1.00 | 1.36 | 1.23 | 0.79 | 0.99 | 10.08 | 1.43 | 1.00 | 2.26 | 0.47 |
| Prm3 | 1.00 | 1.00 | 1.00 | 1.00 | 1.51 | 1.00 | 1.00 | 4.99 | 1.00 | 1.00 | 1.00 | 1.00 |
| Prmt5 | 0.80 | 0.94 | 0.88 | 0.80 | 0.56 | 1.02 | 1.10 | 3.32 | 0.80 | 0.84 | 1.14 | 1.04 |
| Procr | 1.67 | 1.09 | 1.16 | 0.93 | 1.39 | 0.91 | 1.00 | 1.00 | 1.00 | 0.91 | 1.21 | 1.17 |
| Prol1 | 1.00 | 1.00 | 0.22 | 1.00 | 1.00 | 1.00 | 1.00 | 1.00 | 1.00 | 1.00 | 1.00 | 1.00 |
| Proser2 | 2.23 | 2.00 | 1.83 | 1.27 | 1.74 | 1.12 | 1.11 | 1.78 | 1.11 | 0.93 | 1.12 | 1.10 |

Fig. 35- 235

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Plvap | 1.09 | 1.32 | 1.32 | 1.21 | 1.13 | 1.08 | 0.98 | 1.00 | 0.51 | 0.84 | 0.92 | 0.84 |
| Pmaip1 | 1.28 | 1.60 | 1.00 | 1.78 | 1.00 | 1.48 | 1.25 | 1.00 | 1.14 | 0.70 | 0.50 | 0.79 |
| Pmf1 | 1.06 | 0.68 | 1.05 | 0.93 | 4.39 | 0.90 | 1.61 | 1.97 | 1.50 | 1.10 | 1.60 | 0.90 |
| Pmm1 | 1.13 | 1.31 | 1.40 | 2.97 | 8.83 | 2.36 | 0.77 | 2.02 | 0.94 | 1.35 | 2.27 | 1.06 |
| Pmvk | 1.15 | 1.20 | 0.93 | 4.01 | 28.83 | 1.59 | 0.83 | 3.52 | 1.02 | 1.29 | 1.35 | 0.87 |
| Pnlip | 75.11 | 3.40 | 4.86 | 1.00 | 1.00 | 0.79 | 1.00 | 2.59 | 1.17 | 4.45 | 14.23 | 1.02 |
| Pnliprp1 | 0.54 | 0.44 | 1.25 | 1.00 | 1.00 | 0.68 | 1.00 | 2.00 | 2.10 | 1.28 | 3.92 | 0.47 |
| Pnliprp2 | 0.24 | 0.24 | 1.16 | 1.00 | 1.00 | 1.00 | 1.00 | 1.00 | 1.00 | 1.00 | 6.26 | 1.00 |
| Pnpla7 | 1.48 | 2.00 | 1.34 | 3.51 | 8.53 | 2.12 | 1.18 | 1.18 | 1.35 | 1.46 | 1.78 | 1.44 |
| Poc1a | 1.22 | 1.00 | 0.70 | 1.00 | 1.00 | 1.00 | 0.83 | 0.56 | 0.92 | 0.81 | 1.33 | 0.85 |
| Pofut2 | 1.07 | 1.06 | 1.13 | 1.10 | 2.18 | 1.11 | 0.96 | 2.43 | 0.93 | 1.09 | 1.15 | 0.98 |
| Pold2 | 0.61 | 0.81 | 0.84 | 0.88 | 1.62 | 1.00 | 1.07 | 2.31 | 1.03 | 0.86 | 1.04 | 0.95 |
| Pole3 | 0.90 | 0.93 | 0.87 | 0.96 | 1.11 | 1.00 | 0.93 | 3.00 | 0.93 | 1.07 | 0.78 | 0.74 |
| Pole4 | 0.89 | 0.78 | 0.80 | 1.38 | 5.21 | 1.65 | 1.27 | 2.42 | 0.97 | 1.01 | 0.87 | 0.97 |
| Polr2c | 0.98 | 1.03 | 0.96 | 1.26 | 5.84 | 1.21 | 0.79 | 0.35 | 0.86 | 0.96 | 1.26 | 1.01 |
| Polr2e | 0.99 | 0.98 | 1.11 | 0.86 | 3.10 | 0.96 | 0.86 | 2.33 | 1.00 | 1.04 | 1.41 | 0.92 |
| Polr2f | 0.83 | 1.33 | 1.13 | 1.18 | 3.16 | 0.72 | 1.68 | 1.58 | 1.04 | 0.95 | 1.43 | 1.11 |
| Polr2l | 0.90 | 1.09 | 0.90 | 0.95 | 2.51 | 1.11 | 0.96 | 2.32 | 0.82 | 1.18 | 1.15 | 0.97 |
| Pomc | 0.91 | 1.00 | 1.00 | 0.87 | 0.57 | 0.63 | 0.69 | 1.17 | 0.97 | 0.73 | 2.37 | 0.82 |
| Pomp | 0.88 | 0.94 | 0.91 | 0.89 | 2.34 | 0.97 | 0.89 | 1.55 | 0.97 | 1.06 | 1.19 | 0.93 |
| Pop5 | 1.01 | 0.79 | 1.12 | 0.80 | 2.30 | 1.40 | 1.07 | 2.14 | 1.05 | 1.20 | 1.16 | 0.84 |
| Por | 1.62 | 2.35 | 1.09 | 0.95 | 2.49 | 1.25 | 0.70 | 0.95 | 0.69 | 1.06 | 1.50 | 0.98 |
| Ppa1 | 0.68 | 0.62 | 0.66 | 0.80 | 5.71 | 1.83 | 1.14 | 1.34 | 1.14 | 1.37 | 1.33 | 1.13 |
| Ppa2 | 0.94 | 0.95 | 1.07 | 0.77 | 2.71 | 0.88 | 0.66 | 2.44 | 1.00 | 1.03 | 1.97 | 0.97 |
| Ppan | 1.05 | 0.86 | 1.05 | 1.36 | 3.98 | 1.29 | 0.81 | 1.28 | 0.75 | 1.28 | 1.59 | 1.23 |
| Ppargc1a | 1.89 | 1.81 | 1.47 | 0.90 | 1.00 | 1.00 | 1.00 | 1.00 | 1.00 | 1.00 | 1.28 | 1.00 |
| Ppcdc | 0.85 | 1.15 | 1.11 | 0.74 | 1.65 | 1.09 | 0.82 | 1.39 | 0.87 | 1.23 | 1.33 | 1.11 |
| Ppdpf | 0.37 | 0.33 | 0.43 | 0.33 | 0.92 | 0.33 | 0.39 | 0.36 | 0.36 | 0.33 | 0.45 | 0.35 |
| Ppie | 1.17 | 0.90 | 1.02 | 1.08 | 2.77 | 1.24 | 0.96 | 2.97 | 0.76 | 1.07 | 1.31 | 0.94 |
| Ppih | 1.12 | 0.64 | 0.87 | 1.02 | 2.56 | 1.12 | 2.03 | 7.13 | 1.72 | 0.72 | 1.23 | 1.34 |
| Ppil2 | 0.96 | 1.12 | 1.09 | 0.97 | 2.15 | 1.05 | 1.01 | 2.82 | 0.98 | 0.95 | 1.18 | 0.96 |
| Ppil6 | 1.00 | 1.07 | 1.00 | 1.57 | 0.64 | 3.13 | 1.13 | 0.92 | 0.89 | 1.00 | 1.00 | 1.00 |
| Ppm1e | 1.54 | 1.69 | 1.32 | 1.00 | 1.00 | 1.00 | 0.92 | 1.00 | 0.93 | 0.65 | 2.05 | 0.82 |
| Ppox | 1.24 | 1.23 | 1.60 | 1.04 | 2.95 | 1.42 | 1.23 | 3.73 | 1.38 | 1.15 | 1.04 | 1.38 |
| Ppp1ca | 0.82 | 0.84 | 0.84 | 0.88 | 1.72 | 1.04 | 0.73 | 2.22 | 0.81 | 0.92 | 1.07 | 0.91 |
| Ppp1r11 | 1.05 | 1.12 | 1.29 | 1.53 | 5.39 | 1.34 | 0.74 | 0.78 | 0.72 | 1.10 | 1.10 | 0.96 |
| Ppp1r12c | 1.65 | 1.87 | 1.90 | 1.30 | 3.11 | 1.22 | 1.14 | 1.93 | 1.11 | 1.19 | 1.59 | 1.24 |
| Ppp1r14d | 1.60 | 1.04 | 1.44 | 1.00 | 1.00 | 1.00 | 1.00 | 1.00 | 1.00 | 1.00 | 1.00 | 1.00 |
| Ppp1r1b | 0.92 | 1.17 | 1.26 | 1.36 | 0.92 | 2.70 | 0.66 | 1.54 | 1.16 | 1.00 | 18.10 | 1.00 |
| Ppp1r27 | 1.00 | 1.00 | 1.00 | 1.00 | 1.00 | 1.00 | 1.13 | 1.66 | 1.44 | 1.00 | 1.00 | 1.00 |
| Ppp1r3g | 1.00 | 1.00 | 1.00 | 14.30 | 23.94 | 6.92 | 1.00 | 1.00 | 1.00 | 1.00 | 1.00 | 1.00 |
| Ppp2r2c | 1.83 | 1.28 | 1.06 | 1.00 | 1.00 | 1.21 | 1.00 | 1.00 | 1.00 | 1.00 | 16.58 | 1.00 |
| Ppp2r2d | 0.89 | 1.07 | 1.07 | 1.63 | 5.71 | 1.43 | 1.06 | 1.65 | 0.98 | 1.13 | 1.25 | 0.99 |
| Ppp2r3d | 1.09 | 1.23 | 0.89 | 0.64 | 3.53 | 0.96 | 1.10 | 4.51 | 1.22 | 1.03 | 1.35 | 0.87 |
| Ppp4c | 0.99 | 1.08 | 0.84 | 1.20 | 5.30 | 1.13 | 0.99 | 2.20 | 1.06 | 1.04 | 1.24 | 0.95 |
| Pqbp1 | 1.00 | 1.19 | 1.08 | 0.79 | 5.53 | 0.91 | 0.95 | 1.00 | 0.95 | 1.13 | 1.17 | 0.98 |
| Prap1 | 49.33 | 5.82 | 64.55 | 1.00 | 1.00 | 1.00 | 1.00 | 1.00 | 1.00 | 1.00 | 1.00 | 1.00 |
| Prdx2 | 0.85 | 0.96 | 0.89 | 0.63 | 2.17 | 0.73 | 0.84 | 1.26 | 0.83 | 0.52 | 0.69 | 0.42 |
| Prg2 | 1.00 | 1.00 | 1.00 | 1.00 | 1.00 | 1.00 | 1.00 | 1.00 | 1.00 | 5.04 | 4.83 | 1.46 |
| Prg4 | 4.33 | 2.48 | 1.68 | 2.36 | 2.63 | 2.18 | 1.19 | 1.00 | 1.00 | 1.42 | 2.10 | 1.55 |
| Prima1 | 0.79 | 0.80 | 0.74 | 1.00 | 1.00 | 1.00 | 0.60 | 0.93 | 1.15 | 1.00 | 1.00 | 1.00 |
| Prkab2 | 1.03 | 1.25 | 1.08 | 4.23 | 1.73 | 1.63 | 1.08 | 1.37 | 1.04 | 0.88 | 0.52 | 1.00 |
| Prkar2b | 0.93 | 0.98 | 1.10 | 0.36 | 0.26 | 0.40 | 0.64 | 0.61 | 0.53 | 1.32 | 1.00 | 0.82 |
| Prkcg | 1.04 | 1.13 | 1.03 | 0.75 | 1.00 | 0.89 | 1.00 | 1.00 | 1.00 | 0.44 | 5.63 | 0.87 |
| Prkcsh | 1.00 | 1.01 | 0.92 | 1.15 | 2.41 | 1.08 | 1.01 | 2.10 | 1.06 | 1.08 | 1.23 | 1.05 |
| Prkcz | 0.90 | 1.15 | 1.15 | 1.15 | 1.33 | 1.39 | 1.05 | 5.05 | 1.07 | 0.94 | 2.79 | 1.06 |
| Prkrip1 | 0.89 | 1.19 | 1.16 | 1.15 | 4.08 | 1.05 | 0.88 | 1.71 | 1.05 | 1.28 | 1.30 | 0.98 |
| Prm1 | 1.54 | 1.00 | 0.62 | 3.34 | 46.33 | 1.05 | 0.77 | 1.25 | 1.11 | 5.75 | 0.82 | 4.27 |
| Prm2 | 0.93 | 1.00 | 0.93 | 3.89 | 5.43 | 1.37 | 0.88 | 1.74 | 1.08 | 3.75 | 0.80 | 1.74 |
| Prm3 | 1.00 | 1.00 | 1.00 | 2.30 | 27.37 | 1.00 | 0.84 | 3.26 | 0.92 | 1.00 | 1.08 | 1.00 |
| Prmt5 | 0.99 | 0.74 | 0.89 | 0.88 | 1.35 | 0.93 | 1.00 | 3.75 | 1.05 | 0.93 | 1.15 | 1.04 |
| Procr | 1.05 | 1.06 | 1.21 | 1.54 | 0.90 | 2.05 | 1.17 | 1.00 | 1.00 | 0.75 | 0.70 | 0.92 |
| Prol1 | 1.00 | 1.00 | 1.00 | 1.00 | 1.00 | 1.00 | 1.00 | 1.00 | 1.00 | 1.00 | 1.00 | 1.00 |
| Proser2 | 1.00 | 1.22 | 0.99 | 2.04 | 1.25 | 1.48 | 0.96 | 1.12 | 0.91 | 0.97 | 0.80 | 0.72 |

Fig. 35- 236

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Plvap | 1.10 | 1.37 | 1.51 | 1.03 | 2.15 | 1.07 | 1.21 | 1.40 | 1.40 | 0.39 | 0.75 | 1.02 |
| Pmaip1 | 1.00 | 1.00 | 1.00 | 1.95 | 7.15 | 2.05 | 0.98 | 0.57 | 1.23 | 0.79 | 1.02 | 1.24 |
| Pmf1 | 1.00 | 1.00 | 0.70 | 1.13 | 11.55 | 1.26 | 1.41 | 6.89 | 1.19 | 2.15 | 1.17 | 1.21 |
| Pmm1 | 0.87 | 0.58 | 1.22 | 1.22 | 1.16 | 1.07 | 1.37 | 9.71 | 1.05 | 2.52 | 1.16 | 1.00 |
| Pmvk | 1.13 | 0.68 | 0.69 | 1.26 | 1.06 | 1.04 | 1.15 | 4.41 | 0.84 | 1.87 | 0.96 | 1.34 |
| Pnlip | 1.68 | 1.82 | 1.91 | 1.01 | 1.00 | 0.63 | 0.72 | 1.54 | 0.91 | 1.00 | 0.31 | 0.78 |
| Pnliprp1 | 0.60 | 0.60 | 0.60 | 1.00 | 1.00 | 1.00 | 1.00 | 1.00 | 0.95 | 1.00 | 1.00 | 1.00 |
| Pnliprp2 | 1.16 | 1.23 | 1.12 | 1.00 | 1.00 | 1.00 | 1.00 | 1.00 | 1.00 | 1.00 | 1.00 | 1.00 |
| Pnpla7 | 0.96 | 0.89 | 1.19 | 1.40 | 4.40 | 1.19 | 2.12 | 4.99 | 1.65 | 2.70 | 1.65 | 1.18 |
| Poc1a | 1.00 | 1.00 | 1.00 | 1.00 | 1.00 | 1.00 | 0.95 | 1.22 | 1.80 | 1.54 | 0.77 | 0.95 |
| Pofut2 | 1.05 | 1.23 | 0.93 | 1.10 | 1.30 | 1.14 | 1.18 | 5.40 | 1.01 | 1.25 | 1.10 | 1.04 |
| Pold2 | 1.63 | 0.91 | 0.63 | 1.25 | 1.48 | 0.88 | 0.78 | 5.37 | 0.80 | 1.55 | 0.68 | 0.89 |
| Pole3 | 1.20 | 0.96 | 1.09 | 0.84 | 1.65 | 0.98 | 1.08 | 5.89 | 0.88 | 2.66 | 0.79 | 0.86 |
| Pole4 | 0.85 | 1.57 | 0.98 | 0.97 | 1.32 | 0.73 | 1.11 | 3.66 | 0.96 | 1.05 | 0.78 | 0.94 |
| Polr2c | 0.99 | 1.24 | 1.13 | 1.09 | 1.16 | 1.26 | 1.11 | 2.11 | 1.11 | 1.03 | 1.16 | 1.07 |
| Polr2e | 0.97 | 0.81 | 0.65 | 0.94 | 1.16 | 1.10 | 1.07 | 8.39 | 0.81 | 3.09 | 1.07 | 1.19 |
| Polr2f | 0.81 | 0.70 | 0.90 | 0.74 | 1.35 | 1.05 | 1.12 | 3.30 | 0.83 | 2.10 | 0.89 | 0.94 |
| Polr2l | 1.01 | 1.20 | 1.18 | 1.01 | 0.97 | 1.09 | 1.00 | 6.55 | 1.03 | 2.61 | 1.20 | 1.04 |
| Pomc | 1.00 | 1.00 | 1.00 | 0.85 | 0.51 | 1.02 | 1.00 | 1.00 | 1.00 | 1.12 | 1.00 | 1.34 |
| Pomp | 0.71 | 1.09 | 1.40 | 1.12 | 1.07 | 1.09 | 1.06 | 6.44 | 0.92 | 1.99 | 1.10 | 1.07 |
| Pop5 | 0.69 | 0.79 | 0.92 | 1.05 | 0.89 | 0.85 | 1.09 | 12.27 | 0.94 | 2.68 | 0.99 | 0.92 |
| Por | 3.96 | 4.93 | 1.87 | 1.18 | 1.19 | 1.04 | 2.67 | 5.53 | 1.73 | 1.77 | 1.33 | 1.20 |
| Ppa1 | 0.78 | 0.84 | 0.89 | 1.07 | 0.92 | 1.00 | 1.36 | 2.73 | 1.19 | 1.33 | 0.77 | 0.88 |
| Ppa2 | 1.20 | 1.47 | 0.72 | 1.31 | 1.31 | 1.15 | 0.94 | 6.48 | 0.83 | 1.96 | 1.17 | 1.15 |
| Ppan | 1.23 | 1.25 | 1.24 | 1.69 | 1.08 | 1.30 | 1.10 | 5.55 | 0.97 | 1.78 | 0.76 | 0.92 |
| Ppargc1a | 1.39 | 1.00 | 1.00 | 0.99 | 1.38 | 0.95 | 2.76 | 1.65 | 2.37 | 1.00 | 1.00 | 1.00 |
| Ppcdc | 0.97 | 0.67 | 0.57 | 1.00 | 0.91 | 0.96 | 1.18 | 5.09 | 1.09 | 1.62 | 1.17 | 0.99 |
| Ppdpf | 0.41 | 0.17 | 0.30 | 0.31 | 0.33 | 0.38 | 0.40 | 5.47 | 0.34 | 1.00 | 0.37 | 0.55 |
| Ppie | 0.87 | 1.79 | 0.69 | 1.27 | 1.10 | 1.20 | 1.18 | 10.75 | 0.88 | 2.81 | 1.08 | 1.03 |
| Ppih | 1.00 | 1.00 | 1.00 | 1.20 | 13.22 | 1.18 | 1.23 | 15.16 | 1.21 | 4.15 | 1.09 | 1.16 |
| Ppil2 | 1.61 | 0.73 | 0.66 | 1.04 | 1.12 | 1.00 | 0.98 | 9.16 | 1.00 | 3.05 | 1.25 | 1.23 |
| Ppil6 | 1.00 | 1.00 | 1.00 | 0.95 | 1.00 | 0.95 | 1.84 | 8.40 | 2.40 | 1.00 | 1.00 | 1.00 |
| Ppm1e | 1.00 | 1.00 | 1.00 | 1.02 | 0.68 | 1.02 | 1.00 | 1.00 | 1.00 | 0.55 | 0.57 | 0.74 |
| Ppox | 0.57 | 0.67 | 1.26 | 1.48 | 2.37 | 1.62 | 1.18 | 5.19 | 0.90 | 3.55 | 1.21 | 1.24 |
| Ppp1ca | 1.13 | 0.81 | 0.93 | 1.08 | 1.00 | 1.01 | 0.93 | 5.13 | 0.84 | 1.75 | 1.22 | 1.20 |
| Ppp1r11 | 0.77 | 1.00 | 0.94 | 1.15 | 1.12 | 1.12 | 1.27 | 1.78 | 1.04 | 1.89 | 1.26 | 1.30 |
| Ppp1r12c | 1.56 | 1.24 | 1.56 | 1.20 | 0.96 | 1.16 | 1.87 | 7.22 | 1.59 | 3.02 | 1.65 | 1.59 |
| Ppp1r14d | 1.00 | 1.00 | 1.00 | 1.00 | 1.00 | 1.00 | 1.00 | 2.86 | 1.00 | 1.00 | 1.00 | 1.00 |
| Ppp1r1b | 0.43 | 0.34 | 0.66 | 1.06 | 1.78 | 1.05 | 1.30 | 0.80 | 1.12 | 1.00 | 1.00 | 1.00 |
| Ppp1r27 | 1.00 | 1.00 | 1.00 | 1.00 | 1.00 | 1.00 | 1.24 | 5.73 | 1.36 | 1.00 | 1.00 | 1.00 |
| Ppp1r3g | 1.00 | 1.00 | 1.00 | 0.94 | 0.41 | 0.98 | 1.00 | 1.00 | 1.00 | 1.00 | 1.00 | 1.00 |
| Ppp2r2c | 1.00 | 1.00 | 1.00 | 0.97 | 0.51 | 0.94 | 0.67 | 0.70 | 1.13 | 1.00 | 1.00 | 1.00 |
| Ppp2r2d | 1.39 | 1.36 | 1.01 | 1.01 | 1.13 | 1.06 | 1.23 | 3.76 | 1.36 | 1.49 | 1.16 | 0.98 |
| Ppp2r3d | 1.00 | 1.00 | 1.00 | 1.08 | 1.04 | 0.85 | 1.11 | 5.33 | 0.92 | 3.64 | 1.36 | 1.25 |
| Ppp4c | 0.84 | 1.02 | 0.85 | 1.11 | 1.00 | 1.05 | 1.19 | 6.43 | 0.97 | 2.92 | 1.47 | 1.17 |
| Pqbp1 | 1.35 | 1.11 | 0.96 | 1.13 | 1.49 | 1.05 | 1.03 | 2.00 | 0.90 | 1.73 | 1.00 | 1.05 |
| Prap1 | 1.00 | 1.00 | 1.00 | 1.00 | 1.00 | 1.00 | 1.00 | 1.00 | 1.00 | 1.00 | 1.00 | 1.00 |
| Prdx2 | 0.97 | 0.77 | 1.10 | 1.09 | 1.09 | 0.98 | 0.94 | 5.11 | 0.75 | 1.42 | 0.73 | 0.85 |
| Prg2 | 1.00 | 1.00 | 1.00 | 1.00 | 0.67 | 1.00 | 1.00 | 1.00 | 1.00 | 0.95 | 0.77 | 1.03 |
| Prg4 | 1.00 | 1.00 | 1.00 | 0.45 | 0.30 | 0.54 | 1.81 | 2.57 | 1.34 | 3.53 | 1.77 | 1.01 |
| Prima1 | 1.00 | 1.00 | 1.00 | 0.91 | 7.04 | 1.23 | 1.02 | 1.00 | 1.58 | 1.00 | 1.00 | 1.00 |
| Prkab2 | 1.00 | 1.00 | 1.00 | 0.94 | 1.06 | 0.91 | 0.75 | 0.13 | 1.02 | 1.00 | 0.63 | 0.78 |
| Prkar2b | 1.00 | 1.00 | 1.00 | 1.09 | 5.03 | 0.95 | 0.73 | 0.36 | 1.05 | 0.67 | 0.83 | 1.02 |
| Prkcg | 1.00 | 1.00 | 1.00 | 1.02 | 1.35 | 0.99 | 1.58 | 2.80 | 1.21 | 1.12 | 0.94 | 0.86 |
| Prkcsh | 0.89 | 0.72 | 0.59 | 1.02 | 1.06 | 1.12 | 1.41 | 10.19 | 1.16 | 2.73 | 1.19 | 1.07 |
| Prkcz | 0.86 | 0.46 | 0.85 | 1.03 | 0.89 | 0.95 | 0.97 | 8.64 | 0.91 | 1.00 | 1.00 | 1.00 |
| Prkrip1 | 1.00 | 1.00 | 0.79 | 0.94 | 1.01 | 1.05 | 1.18 | 3.75 | 1.01 | 2.52 | 0.99 | 1.03 |
| Prm1 | 1.00 | 1.93 | 0.34 | 1.00 | 1.00 | 0.73 | 104.23 | 1.00 | 1.27 | 1.00 | 1.00 | 1.00 |
| Prm2 | 1.00 | 1.13 | 0.60 | 1.00 | 8.72 | 1.22 | 131.76 | 4.01 | 0.76 | 1.00 | 1.00 | 1.00 |
| Prm3 | 1.00 | 0.97 | 1.00 | 1.00 | 4.37 | 1.00 | 9.53 | 2.60 | 1.00 | 1.00 | 1.00 | 1.00 |
| Prmt5 | 0.83 | 0.90 | 0.72 | 1.07 | 0.85 | 0.96 | 1.24 | 6.71 | 0.93 | 2.02 | 0.80 | 0.87 |
| Procr | 5.39 | 7.64 | 5.47 | 1.00 | 1.00 | 1.00 | 2.04 | 0.23 | 1.61 | 1.00 | 1.00 | 1.00 |
| Prol1 | 1.00 | 1.00 | 1.00 | 1.00 | 1.00 | 1.00 | 1.00 | 8.96 | 1.00 | 1.00 | 1.00 | 1.00 |
| Proser2 | 1.60 | 1.91 | 1.54 | 1.18 | 0.88 | 1.23 | 0.96 | 4.04 | 0.89 | 1.00 | 1.00 | 1.25 |

Fig. 35- 237

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Prpf19 | 0.92 | 0.45 | 0.85 | 0.31 | 4.40 | 0.89 | 1.26 | 1.04 | 0.93 | 2.08 | 2.80 | 0.96 |
| Prpf6 | 1.20 | 0.97 | 1.17 | 1.09 | 4.15 | 1.51 | 1.29 | 1.27 | 1.07 | 2.79 | 2.12 | 1.08 |
| Prph | 1.00 | 1.00 | 1.00 | 1.00 | 1.00 | 1.00 | 0.88 | 0.97 | 2.25 | 3.44 | 5.45 | 2.26 |
| Prpsap1 | 1.25 | 0.68 | 1.06 | 0.75 | 5.15 | 1.46 | 1.10 | 1.00 | 0.84 | 1.90 | 2.67 | 0.95 |
| Prr15l | 1.00 | 1.00 | 1.00 | 1.00 | 1.00 | 1.00 | 1.00 | 1.00 | 1.00 | 1.42 | 1.90 | 1.14 |
| Prr22 | 1.00 | 1.00 | 1.00 | 0.46 | 1.14 | 0.87 | 1.00 | 1.00 | 1.00 | 2.03 | 1.15 | 1.00 |
| Prr30 | 1.00 | 1.00 | 1.00 | 1.00 | 1.00 | 1.00 | 1.00 | 1.00 | 1.00 | 1.00 | 1.00 | 1.00 |
| Prss2 | 1.00 | 1.00 | 1.00 | 1.00 | 1.00 | 1.00 | 1.00 | 1.00 | 1.00 | 1.09 | 1.00 | 4.83 |
| Prss22 | 4.48 | 4.33 | 4.37 | 4.73 | 12.10 | 5.04 | 3.93 | 3.17 | 2.91 | 2.00 | 2.50 | 1.96 |
| Prss3 | 1.00 | 1.00 | 1.00 | 1.00 | 1.00 | 1.00 | 1.00 | 1.00 | 1.00 | 1.00 | 1.00 | 1.00 |
| Prss53 | 1.00 | 0.54 | 0.70 | 0.84 | 8.42 | 1.30 | 1.02 | 0.71 | 0.72 | 1.50 | 2.97 | 0.70 |
| Prtn3 | 1.00 | 0.87 | 1.00 | 1.00 | 1.00 | 1.00 | 1.00 | 1.00 | 1.00 | 1.49 | 6.36 | 1.00 |
| Prune2 | 4.46 | 2.10 | 5.53 | 1.00 | 1.00 | 1.00 | 2.25 | 2.19 | 1.68 | 1.00 | 1.00 | 0.94 |
| Psca | 0.05 | 0.82 | 1.00 | 1.00 | 1.00 | 0.50 | 0.33 | 0.66 | 1.05 | 0.04 | 1.52 | 1.00 |
| Psen2 | 1.60 | 0.73 | 1.22 | 0.81 | 5.60 | 1.11 | 1.66 | 1.67 | 0.89 | 2.20 | 3.38 | 1.35 |
| Psenen | 1.36 | 0.61 | 0.83 | 0.45 | 3.69 | 0.75 | 0.99 | 0.64 | 0.71 | 1.42 | 2.54 | 0.93 |
| Psma5 | 1.63 | 0.65 | 1.07 | 0.29 | 5.26 | 0.81 | 1.05 | 0.84 | 1.18 | 2.19 | 3.75 | 1.18 |
| Psma6 | 1.30 | 0.82 | 1.08 | 0.77 | 10.28 | 1.35 | 1.02 | 0.96 | 0.90 | 2.41 | 3.52 | 1.02 |
| Psma7 | 1.67 | 0.66 | 1.14 | 0.44 | 10.71 | 1.07 | 1.14 | 0.82 | 0.91 | 3.90 | 4.16 | 1.06 |
| Psmb1 | 1.20 | 0.73 | 0.91 | 0.30 | 7.19 | 0.92 | 1.04 | 0.86 | 0.88 | 1.80 | 3.26 | 0.97 |
| Psmb10 | 0.87 | 0.40 | 0.92 | 0.39 | 11.49 | 0.87 | 0.88 | 0.89 | 0.83 | 3.74 | 4.65 | 0.98 |
| Psmb3 | 1.49 | 0.98 | 1.07 | 0.20 | 2.60 | 0.77 | 0.99 | 0.92 | 0.77 | 0.77 | 2.10 | 0.98 |
| Psmb6 | 1.24 | 0.56 | 0.88 | 0.25 | 7.76 | 0.86 | 1.08 | 0.76 | 0.84 | 2.67 | 3.59 | 0.88 |
| Psmb7 | 1.33 | 0.66 | 0.95 | 0.31 | 6.17 | 0.83 | 1.04 | 0.87 | 0.79 | 2.19 | 3.71 | 1.03 |
| Psmb8 | 1.47 | 0.64 | 1.17 | 0.53 | 7.13 | 1.51 | 1.15 | 0.76 | 1.37 | 2.31 | 2.83 | 1.00 |
| Psmb9 | 2.17 | 0.70 | 1.88 | 0.72 | 11.62 | 1.44 | 0.82 | 1.06 | 1.35 | 1.53 | 2.05 | 0.96 |
| Psmc1 | 1.25 | 0.84 | 1.06 | 0.50 | 5.64 | 1.25 | 1.10 | 0.91 | 0.89 | 1.73 | 2.74 | 1.16 |
| Psmc2 | 1.26 | 1.03 | 1.20 | 0.40 | 2.95 | 0.91 | 1.12 | 1.07 | 0.95 | 1.71 | 2.23 | 1.07 |
| Psmd12 | 1.35 | 0.82 | 1.17 | 0.73 | 3.94 | 0.93 | 0.99 | 1.00 | 0.96 | 2.74 | 2.73 | 1.01 |
| Psmd13 | 1.45 | 0.71 | 0.94 | 0.26 | 4.55 | 0.96 | 1.03 | 0.98 | 0.92 | 1.82 | 2.88 | 1.04 |
| Psmd2 | 1.28 | 0.74 | 1.13 | 0.64 | 5.48 | 1.05 | 1.12 | 1.12 | 1.07 | 2.62 | 3.80 | 1.13 |
| Psmd4 | 1.45 | 0.65 | 1.15 | 0.51 | 10.69 | 1.15 | 1.21 | 1.05 | 1.01 | 3.82 | 5.09 | 1.15 |
| Psme1 | 1.03 | 0.37 | 0.80 | 0.39 | 5.25 | 0.79 | 0.82 | 0.75 | 0.71 | 1.83 | 3.23 | 0.93 |
| Psmg2 | 1.02 | 0.57 | 0.79 | 0.92 | 5.33 | 0.72 | 0.87 | 0.77 | 0.82 | 2.00 | 1.92 | 0.86 |
| Psmg3 | 1.41 | 0.65 | 0.99 | 0.43 | 6.49 | 0.87 | 0.90 | 0.74 | 0.86 | 1.98 | 2.98 | 0.90 |
| Psors1c2 | 1.00 | 1.00 | 1.00 | 1.00 | 1.00 | 1.00 | 1.00 | 1.00 | 1.00 | 1.00 | 1.00 | 1.00 |
| Pstpip1 | 1.00 | 1.00 | 1.00 | 1.00 | 1.00 | 1.00 | 1.00 | 1.00 | 1.00 | 2.70 | 2.22 | 0.68 |
| Ptgds | 1.00 | 1.00 | 1.61 | 1.00 | 0.05 | 0.53 | 1.04 | 1.23 | 0.74 | 1.45 | 1.52 | 1.00 |
| Ptges3l | 1.41 | 0.73 | 0.89 | 1.73 | 46.13 | 2.57 | 1.08 | 0.82 | 0.94 | 4.35 | 7.81 | 1.56 |
| Ptgis | 1.07 | 0.40 | 1.12 | 0.64 | 4.87 | 1.00 | 0.75 | 0.68 | 1.04 | 3.70 | 3.60 | 0.94 |
| Ptgs1 | 1.62 | 0.67 | 1.32 | 1.32 | 5.24 | 1.56 | 1.24 | 1.32 | 1.19 | 2.86 | 3.62 | 1.47 |
| Pth | 1.00 | 1.00 | 1.00 | 1.00 | 1.00 | 1.00 | 1.00 | 1.00 | 1.00 | 1.00 | 1.00 | 1.00 |
| Pth1r | 1.00 | 0.85 | 1.00 | 0.49 | 10.65 | 1.00 | 1.13 | 0.83 | 1.20 | 2.28 | 2.69 | 1.00 |
| Pth2 | 1.00 | 1.00 | 1.00 | 1.00 | 1.00 | 1.00 | 1.00 | 1.00 | 1.00 | 1.00 | 1.00 | 1.00 |
| Ptpn18 | 1.00 | 0.39 | 1.08 | 0.49 | 8.24 | 0.65 | 0.80 | 0.88 | 0.54 | 2.84 | 3.82 | 0.91 |
| Ptpn5 | 1.00 | 1.00 | 1.00 | 1.00 | 0.22 | 1.00 | 1.00 | 1.00 | 1.00 | 1.00 | 1.00 | 1.00 |
| Ptprn | 1.00 | 1.00 | 1.00 | 1.00 | 0.18 | 1.00 | 1.01 | 0.75 | 0.92 | 0.71 | 1.58 | 0.85 |
| Ptprn2 | 1.00 | 1.00 | 1.00 | 1.00 | 0.24 | 1.15 | 1.44 | 1.42 | 1.08 | 1.00 | 1.00 | 1.00 |
| Pvalb | 1.03 | 0.66 | 0.65 | 2.81 | 7.98 | 1.32 | 0.17 | 0.98 | 0.50 | 1.54 | 1.00 | 1.00 |
| Pvr | 2.57 | 2.99 | 2.12 | 5.91 | 3.47 | 2.31 | 1.35 | 1.28 | 1.19 | 0.85 | 1.00 | 1.50 |
| Pxmp2 | 0.70 | 0.49 | 0.59 | 0.47 | 6.48 | 1.42 | 0.94 | 0.85 | 0.81 | 1.29 | 2.59 | 0.75 |
| Pycrl | 1.79 | 0.88 | 1.06 | 0.39 | 2.90 | 0.90 | 0.97 | 0.77 | 1.09 | 1.34 | 1.63 | 1.05 |
| Pydc3 | 1.00 | 1.00 | 1.00 | 1.00 | 1.00 | 1.00 | 1.00 | 1.00 | 1.00 | 4.12 | 4.98 | 6.27 |
| Pyroxd2 | 0.44 | 0.64 | 0.43 | 3.55 | 5.59 | 4.74 | 0.18 | 0.15 | 0.14 | 0.34 | 0.58 | 0.53 |
| Pyy | 1.00 | 1.00 | 1.00 | 1.00 | 1.00 | 1.00 | 1.00 | 1.00 | 1.00 | 1.00 | 1.00 | 1.00 |
| Qtrt1 | 2.14 | 0.53 | 1.22 | 0.29 | 9.32 | 0.89 | 1.65 | 0.89 | 1.26 | 2.16 | 3.57 | 0.94 |
| Rab10os | 1.24 | 0.70 | 0.96 | 0.58 | 9.11 | 0.96 | 0.70 | 1.11 | 0.84 | 2.20 | 3.75 | 1.38 |
| Rab13 | 1.71 | 0.80 | 1.12 | 0.55 | 2.54 | 1.14 | 1.01 | 0.93 | 0.76 | 1.00 | 1.73 | 1.01 |
| Rab15 | 0.58 | 0.87 | 0.60 | 1.00 | 0.16 | 1.00 | 1.00 | 1.14 | 1.35 | 0.54 | 0.82 | 0.91 |
| Rab17 | 1.00 | 1.00 | 1.00 | 1.00 | 1.73 | 1.00 | 0.71 | 0.50 | 0.76 | 3.12 | 4.39 | 1.07 |
| Rab24 | 1.14 | 0.57 | 1.02 | 0.46 | 5.06 | 0.91 | 1.22 | 0.99 | 0.87 | 2.12 | 2.77 | 0.94 |
| Rab26os | 1.00 | 1.00 | 0.89 | 0.50 | 1.05 | 1.25 | 0.27 | 1.31 | 0.86 | 0.28 | 1.62 | 0.81 |
| Rab30 | 4.12 | 4.95 | 1.84 | 0.92 | 0.73 | 0.69 | 1.33 | 1.41 | 1.12 | 1.00 | 1.06 | 0.97 |
| Rab34 | 1.01 | 0.78 | 1.30 | 0.78 | 5.59 | 1.10 | 0.91 | 0.70 | 1.16 | 1.23 | 2.27 | 1.00 |

Fig. 35- 238

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Prpf19 | 1.04 | 1.10 | 1.03 | 0.99 | 0.68 | 1.00 | 1.24 | 1.93 | 1.13 | 0.88 | 1.37 | 0.97 |
| Prpf6 | 1.12 | 1.00 | 1.16 | 1.11 | 0.86 | 0.97 | 1.29 | 1.95 | 1.08 | 1.01 | 1.06 | 1.09 |
| Prph | 1.06 | 1.30 | 0.69 | 1.00 | 1.00 | 1.00 | 1.00 | 1.73 | 1.00 | 0.87 | 1.39 | 0.96 |
| Prpsap1 | 1.15 | 1.53 | 1.10 | 0.99 | 0.82 | 1.10 | 1.05 | 1.45 | 1.19 | 1.15 | 1.54 | 1.07 |
| Prr15l | 2.99 | 1.80 | 1.53 | 0.85 | 0.79 | 0.80 | 1.00 | 1.09 | 1.00 | 1.04 | 1.41 | 1.06 |
| Prr22 | 1.91 | 1.40 | 1.10 | 1.00 | 0.64 | 1.00 | 1.00 | 1.00 | 1.00 | 1.00 | 1.43 | 0.99 |
| Prr30 | 1.00 | 1.00 | 1.00 | 1.00 | 1.00 | 1.00 | 1.00 | 1.00 | 1.00 | 1.00 | 1.00 | 1.00 |
| Prss2 | 1.05 | 1.58 | 1.22 | 1.00 | 0.85 | 1.29 | 1.00 | 1.00 | 1.00 | 0.47 | 2.85 | 27.78 |
| Prss22 | 3.36 | 4.15 | 2.33 | 2.35 | 3.74 | 2.55 | 3.09 | 3.31 | 2.62 | 2.88 | 3.99 | 2.93 |
| Prss3 | 1.00 | 1.00 | 1.00 | 1.00 | 1.00 | 1.00 | 1.00 | 1.00 | 1.00 | 1.29 | 3.40 | 6.42 |
| Prss53 | 1.01 | 1.00 | 1.00 | 0.84 | 1.00 | 0.77 | 0.97 | 1.11 | 0.88 | 1.00 | 3.03 | 1.00 |
| Prtn3 | 0.34 | 1.00 | 1.00 | 1.00 | 0.77 | 1.00 | 1.00 | 1.00 | 1.00 | 1.00 | 1.00 | 1.00 |
| Prune2 | 1.00 | 1.00 | 1.00 | 1.00 | 1.00 | 1.00 | 1.00 | 1.00 | 1.00 | 1.04 | 0.73 | 0.90 |
| Psca | 1.39 | 0.22 | 1.35 | 0.89 | 0.66 | 0.81 | 0.83 | 2.59 | 1.06 | 0.90 | 1.20 | 0.60 |
| Psen2 | 1.98 | 2.68 | 1.39 | 1.13 | 0.92 | 1.02 | 0.66 | 0.54 | 0.64 | 1.08 | 1.58 | 1.23 |
| Psenen | 1.21 | 1.39 | 1.06 | 0.82 | 0.79 | 0.83 | 0.79 | 1.15 | 0.72 | 1.07 | 1.92 | 1.00 |
| Psma5 | 1.53 | 1.38 | 0.83 | 0.54 | 0.86 | 0.85 | 1.41 | 1.02 | 1.16 | 0.94 | 1.98 | 1.40 |
| Psma6 | 1.05 | 1.28 | 0.90 | 0.94 | 0.67 | 0.88 | 1.25 | 1.92 | 1.13 | 1.18 | 1.73 | 1.02 |
| Psma7 | 1.03 | 1.35 | 0.94 | 0.96 | 0.53 | 0.94 | 1.14 | 3.21 | 1.07 | 1.06 | 1.78 | 1.15 |
| Psmb1 | 1.16 | 1.42 | 0.97 | 0.88 | 0.70 | 0.96 | 1.01 | 1.24 | 0.94 | 0.89 | 1.50 | 0.89 |
| Psmb10 | 1.16 | 1.17 | 0.91 | 0.70 | 0.39 | 0.88 | 0.52 | 1.29 | 0.49 | 1.28 | 1.78 | 1.01 |
| Psmb3 | 1.15 | 1.27 | 0.97 | 0.97 | 0.88 | 0.84 | 0.89 | 1.07 | 0.97 | 1.00 | 1.79 | 1.04 |
| Psmb6 | 1.12 | 1.57 | 0.84 | 0.80 | 0.53 | 0.79 | 0.88 | 1.92 | 0.91 | 0.83 | 1.63 | 1.04 |
| Psmb7 | 1.09 | 1.20 | 0.87 | 1.00 | 0.70 | 0.86 | 1.02 | 1.57 | 0.92 | 1.24 | 1.73 | 1.19 |
| Psmb8 | 1.20 | 1.48 | 1.11 | 0.71 | 1.00 | 1.14 | 1.16 | 2.33 | 1.35 | 1.36 | 1.58 | 1.00 |
| Psmb9 | 0.98 | 1.35 | 1.05 | 0.90 | 1.01 | 0.73 | 2.38 | 0.93 | 1.37 | 1.46 | 1.48 | 1.10 |
| Psmc1 | 1.21 | 1.41 | 1.03 | 1.24 | 0.95 | 1.07 | 1.44 | 1.43 | 1.04 | 1.07 | 1.68 | 1.06 |
| Psmc2 | 1.13 | 1.29 | 1.07 | 1.06 | 1.11 | 1.06 | 1.12 | 1.18 | 1.09 | 1.08 | 1.41 | 1.15 |
| Psmd12 | 1.02 | 1.12 | 0.88 | 1.14 | 0.79 | 1.13 | 1.34 | 2.10 | 1.06 | 0.96 | 1.36 | 0.95 |
| Psmd13 | 1.04 | 1.34 | 0.92 | 0.94 | 0.92 | 0.98 | 1.40 | 1.61 | 1.24 | 0.99 | 1.57 | 0.95 |
| Psmd2 | 1.00 | 1.05 | 0.92 | 1.11 | 0.82 | 1.14 | 1.25 | 1.66 | 1.21 | 0.99 | 1.39 | 1.01 |
| Psmd4 | 1.22 | 1.50 | 0.95 | 1.26 | 0.66 | 1.19 | 1.75 | 4.00 | 1.48 | 1.10 | 1.83 | 1.02 |
| Psme1 | 1.29 | 1.37 | 1.17 | 0.57 | 0.45 | 0.62 | 0.57 | 1.10 | 0.88 | 1.19 | 1.96 | 1.04 |
| Psmg2 | 0.83 | 0.88 | 0.83 | 0.70 | 0.64 | 0.90 | 0.87 | 1.29 | 1.04 | 0.87 | 1.51 | 1.22 |
| Psmg3 | 1.01 | 1.49 | 0.89 | 0.83 | 0.61 | 1.04 | 1.03 | 1.54 | 1.04 | 0.73 | 1.60 | 1.08 |
| Psors1c2 | 0.49 | 0.62 | 0.40 | 1.00 | 0.56 | 1.00 | 1.00 | 1.00 | 1.00 | 1.00 | 1.00 | 1.00 |
| Pstpip1 | 0.75 | 0.89 | 0.68 | 1.00 | 1.01 | 1.00 | 1.00 | 1.00 | 1.00 | 0.96 | 1.00 | 1.00 |
| Ptgds | 1.00 | 1.00 | 1.00 | 0.61 | 0.68 | 0.61 | 0.80 | 1.12 | 1.00 | 1.00 | 1.00 | 1.00 |
| Ptges3l | 1.21 | 1.75 | 0.86 | 0.84 | 0.54 | 1.13 | 1.00 | 1.91 | 1.00 | 0.67 | 1.73 | 1.34 |
| Ptgis | 1.17 | 1.36 | 0.86 | 1.15 | 0.49 | 1.25 | 1.00 | 5.66 | 1.00 | 0.81 | 1.07 | 0.75 |
| Ptgs1 | 1.91 | 1.68 | 1.13 | 0.97 | 0.68 | 0.89 | 0.63 | 1.40 | 0.72 | 1.11 | 1.45 | 1.16 |
| Pth | 9.39 | 24.63 | 3.46 | 1.00 | 1.00 | 1.00 | 1.00 | 1.00 | 1.00 | 1.00 | 1.00 | 1.00 |
| Pth1r | 1.00 | 1.00 | 1.00 | 1.17 | 0.60 | 1.23 | 1.09 | 2.19 | 1.01 | 1.50 | 1.85 | 0.96 |
| Pth2 | 1.00 | 1.00 | 1.00 | 1.00 | 1.00 | 1.00 | 1.00 | 1.00 | 1.00 | 1.00 | 1.00 | 1.00 |
| Ptpn18 | 1.10 | 1.48 | 1.16 | 0.72 | 0.44 | 1.17 | 1.00 | 1.27 | 1.00 | 0.92 | 1.37 | 1.04 |
| Ptpn5 | 1.00 | 1.00 | 1.05 | 1.00 | 1.00 | 1.00 | 1.00 | 1.00 | 1.00 | 0.78 | 0.86 | 1.00 |
| Ptprn | 0.98 | 1.41 | 0.81 | 1.00 | 1.00 | 1.00 | 1.00 | 1.00 | 1.00 | 1.59 | 1.00 | 1.43 |
| Ptprn2 | 0.71 | 0.63 | 0.55 | 1.00 | 1.00 | 1.03 | 1.00 | 1.00 | 1.00 | 1.39 | 1.08 | 1.12 |
| Pvalb | 0.71 | 0.69 | 1.00 | 0.55 | 0.52 | 0.79 | 1.00 | 1.00 | 1.00 | 1.00 | 1.00 | 1.00 |
| Pvr | 0.61 | 0.62 | 0.66 | 1.27 | 2.18 | 1.04 | 3.45 | 1.79 | 2.96 | 1.14 | 1.07 | 1.37 |
| Pxmp2 | 1.74 | 1.31 | 0.81 | 0.92 | 0.83 | 0.83 | 1.04 | 1.18 | 1.04 | 1.41 | 1.32 | 0.77 |
| Pycr1 | 1.21 | 1.12 | 0.91 | 0.90 | 0.83 | 0.89 | 0.69 | 0.68 | 0.69 | 0.74 | 1.33 | 0.93 |
| Pydc3 | 4.83 | 4.37 | 4.23 | 1.00 | 1.00 | 1.00 | 1.00 | 1.00 | 1.00 | 1.00 | 1.00 | 1.00 |
| Pyroxd2 | 1.43 | 1.60 | 1.20 | 1.05 | 1.18 | 1.30 | 0.81 | 0.43 | 0.71 | 0.33 | 0.46 | 0.46 |
| Pyy | 0.84 | 2.56 | 0.73 | 1.00 | 1.00 | 1.00 | 1.00 | 1.00 | 1.00 | 1.19 | 1.87 | 1.30 |
| Qtrt1 | 1.19 | 1.15 | 1.23 | 1.21 | 0.44 | 0.85 | 0.70 | 1.77 | 0.92 | 1.22 | 1.13 | 0.95 |
| Rab10os | 1.48 | 1.73 | 0.96 | 1.01 | 0.64 | 0.77 | 0.70 | 0.92 | 0.89 | 1.29 | 1.73 | 1.37 |
| Rab13 | 2.32 | 1.96 | 1.52 | 0.82 | 0.72 | 0.82 | 0.96 | 0.30 | 0.79 | 0.88 | 1.45 | 1.01 |
| Rab15 | 1.10 | 0.89 | 1.39 | 0.84 | 1.00 | 0.90 | 1.00 | 1.00 | 1.00 | 1.05 | 0.89 | 0.98 |
| Rab17 | 2.32 | 2.54 | 1.80 | 0.98 | 0.62 | 1.04 | 0.64 | 1.76 | 0.82 | 0.96 | 1.67 | 1.07 |
| Rab24 | 1.10 | 1.34 | 0.93 | 0.92 | 0.73 | 1.16 | 0.80 | 1.40 | 0.88 | 0.98 | 1.45 | 1.02 |
| Rab26os | 0.75 | 1.32 | 1.25 | 1.10 | 0.76 | 1.16 | 0.68 | 1.20 | 1.04 | 0.93 | 0.91 | 0.90 |
| Rab30 | 1.69 | 0.93 | 1.09 | 0.77 | 2.11 | 1.73 | 6.36 | 7.39 | 2.63 | 0.98 | 1.15 | 1.43 |
| Rab34 | 3.05 | 2.37 | 1.46 | 0.81 | 0.78 | 0.91 | 1.14 | 1.01 | 1.12 | 0.89 | 1.08 | 1.17 |

Fig. 35- 239

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Prpf19 | 0.89 | 0.85 | 1.03 | 0.85 | 1.95 | 1.11 | 0.81 | 2.43 | 0.88 | 1.05 | 1.27 | 0.99 |
| Prpf6 | 1.03 | 0.85 | 1.01 | 1.63 | 6.46 | 1.36 | 1.13 | 1.82 | 0.88 | 1.09 | 1.04 | 1.02 |
| Prph | 1.52 | 1.08 | 1.64 | 2.16 | 2.42 | 2.38 | 1.00 | 1.61 | 1.00 | 1.64 | 2.81 | 1.68 |
| Prpsap1 | 0.97 | 1.10 | 1.11 | 1.08 | 1.61 | 1.30 | 0.88 | 1.65 | 0.89 | 1.06 | 1.33 | 0.95 |
| Prr15l | 1.14 | 1.29 | 1.10 | 1.24 | 7.61 | 2.39 | 0.75 | 1.14 | 1.04 | 1.00 | 1.00 | 1.00 |
| Prr22 | 1.13 | 1.00 | 0.69 | 1.11 | 1.00 | 1.00 | 1.11 | 1.10 | 1.00 | 1.12 | 1.53 | 1.26 |
| Prr30 | 1.00 | 1.00 | 1.00 | 3.46 | 1.00 | 1.00 | 1.00 | 1.21 | 1.03 | 1.00 | 1.00 | 1.00 |
| Prss2 | 80.50 | 2.04 | 2.56 | 1.00 | 1.00 | 0.97 | 1.00 | 1.32 | 1.07 | 3.66 | 10.55 | 0.49 |
| Prss22 | 2.78 | 3.62 | 3.27 | 5.58 | 11.04 | 3.96 | 1.93 | 1.49 | 2.03 | 2.35 | 3.08 | 2.23 |
| Prss3 | 5.20 | 3.97 | 9.67 | 1.00 | 1.00 | 1.00 | 1.00 | 1.00 | 1.00 | 1.00 | 1.60 | 1.00 |
| Prss53 | 1.00 | 1.00 | 1.35 | 1.00 | 3.04 | 1.16 | 1.00 | 0.99 | 1.00 | 1.00 | 1.83 | 1.01 |
| Prtn3 | 1.00 | 1.00 | 1.00 | 0.32 | 0.78 | 0.94 | 1.00 | 1.00 | 1.00 | 18.09 | 8.49 | 7.70 |
| Prune2 | 1.00 | 0.90 | 1.00 | 1.05 | 0.82 | 0.71 | 1.00 | 1.00 | 1.00 | 1.00 | 1.37 | 1.00 |
| Psca | 0.80 | 0.97 | 0.63 | 0.83 | 0.99 | 0.43 | 0.96 | 1.51 | 0.91 | 1.00 | 1.00 | 0.69 |
| Psen2 | 1.44 | 1.83 | 1.39 | 0.89 | 2.80 | 0.87 | 0.99 | 1.54 | 1.10 | 1.27 | 1.37 | 1.02 |
| Psenen | 1.05 | 1.08 | 1.18 | 0.65 | 9.38 | 0.95 | 0.96 | 1.21 | 0.87 | 0.97 | 1.35 | 0.94 |
| Psma5 | 1.03 | 0.87 | 0.75 | 0.80 | 7.52 | 0.86 | 0.94 | 1.54 | 1.14 | 1.16 | 1.31 | 0.80 |
| Psma6 | 0.94 | 0.95 | 1.02 | 1.60 | 6.07 | 1.53 | 0.81 | 1.76 | 0.91 | 1.09 | 1.42 | 0.85 |
| Psma7 | 0.99 | 0.98 | 0.93 | 1.37 | 3.11 | 1.32 | 0.97 | 3.59 | 0.82 | 0.94 | 1.28 | 1.00 |
| Psmb1 | 0.84 | 0.79 | 0.91 | 1.01 | 4.04 | 1.10 | 0.93 | 1.83 | 1.05 | 0.90 | 1.25 | 0.93 |
| Psmb10 | 1.56 | 1.21 | 1.26 | 0.53 | 1.08 | 0.63 | 1.00 | 5.22 | 0.71 | 0.95 | 1.07 | 0.82 |
| Psmb3 | 0.90 | 1.06 | 0.95 | 1.19 | 6.80 | 1.47 | 1.10 | 1.04 | 1.31 | 0.87 | 1.00 | 0.97 |
| Psmb6 | 0.79 | 0.98 | 1.00 | 0.82 | 3.47 | 1.06 | 0.98 | 2.40 | 1.05 | 0.94 | 1.29 | 0.86 |
| Psmb7 | 0.89 | 0.96 | 0.91 | 0.99 | 3.69 | 0.97 | 1.03 | 2.08 | 1.01 | 0.85 | 1.29 | 0.96 |
| Psmb8 | 2.38 | 1.80 | 3.15 | 0.87 | 3.50 | 1.17 | 1.00 | 4.53 | 1.31 | 0.98 | 1.08 | 0.97 |
| Psmb9 | 2.51 | 2.20 | 2.56 | 0.65 | 3.54 | 1.09 | 1.00 | 1.00 | 1.00 | 1.04 | 1.09 | 0.94 |
| Psmc1 | 0.96 | 1.15 | 1.03 | 1.29 | 5.47 | 1.50 | 1.00 | 1.29 | 1.11 | 1.16 | 1.40 | 0.82 |
| Psmc2 | 0.88 | 1.00 | 1.02 | 1.20 | 5.42 | 1.34 | 0.97 | 1.20 | 0.98 | 0.94 | 1.25 | 0.91 |
| Psmd12 | 1.04 | 0.91 | 0.86 | 1.13 | 3.59 | 1.31 | 1.11 | 2.07 | 0.98 | 0.99 | 1.28 | 0.80 |
| Psmd13 | 0.97 | 0.93 | 0.89 | 1.01 | 2.13 | 1.11 | 0.98 | 1.58 | 0.93 | 0.93 | 1.19 | 0.85 |
| Psmd2 | 0.90 | 0.93 | 0.86 | 1.31 | 2.74 | 1.22 | 1.00 | 2.12 | 1.01 | 0.89 | 1.14 | 0.95 |
| Psmd4 | 1.11 | 1.06 | 1.03 | 1.18 | 3.77 | 1.60 | 0.90 | 4.00 | 1.16 | 1.06 | 1.26 | 1.02 |
| Psme1 | 1.04 | 0.90 | 1.45 | 0.62 | 5.09 | 0.87 | 0.53 | 1.20 | 1.07 | 1.11 | 1.26 | 1.00 |
| Psmg2 | 1.01 | 1.05 | 0.88 | 0.97 | 1.62 | 0.90 | 0.98 | 1.59 | 0.81 | 1.00 | 1.53 | 1.06 |
| Psmg3 | 0.66 | 0.82 | 0.87 | 1.09 | 1.77 | 1.12 | 1.12 | 1.77 | 0.79 | 1.00 | 1.34 | 0.94 |
| Psors1c2 | 0.66 | 2.09 | 1.12 | 1.00 | 1.00 | 1.00 | 0.89 | 2.27 | 0.82 | 1.00 | 1.00 | 1.00 |
| Pstpip1 | 0.69 | 0.97 | 0.62 | 1.00 | 2.44 | 0.94 | 1.00 | 4.69 | 1.03 | 0.93 | 0.96 | 0.93 |
| Ptgds | 1.00 | 1.00 | 1.00 | 0.29 | 12.60 | 0.14 | 0.53 | 0.76 | 0.46 | 1.00 | 25.77 | 1.00 |
| Ptges3l | 0.89 | 1.49 | 0.92 | 0.96 | 2.26 | 0.95 | 0.90 | 2.47 | 0.92 | 0.71 | 1.60 | 0.96 |
| Ptgis | 0.92 | 0.98 | 1.00 | 0.91 | 1.61 | 0.97 | 0.92 | 5.69 | 0.92 | 1.06 | 1.64 | 1.30 |
| Ptgs1 | 1.06 | 1.24 | 1.45 | 0.80 | 1.34 | 0.77 | 1.00 | 1.00 | 1.00 | 0.86 | 1.00 | 0.90 |
| Pth | 1.00 | 1.00 | 1.00 | 1.00 | 1.00 | 1.00 | 1.00 | 1.00 | 1.00 | 1.00 | 1.00 | 1.00 |
| Pth1r | 1.37 | 0.82 | 1.32 | 0.71 | 1.05 | 0.90 | 1.00 | 4.67 | 1.00 | 1.20 | 1.38 | 1.33 |
| Pth2 | 1.00 | 1.00 | 1.00 | 1.00 | 1.00 | 1.00 | 1.02 | 7.15 | 1.10 | 1.00 | 1.00 | 1.00 |
| Ptpn18 | 0.99 | 1.05 | 0.94 | 0.46 | 1.18 | 0.75 | 1.00 | 4.84 | 1.00 | 1.06 | 1.25 | 1.01 |
| Ptpn5 | 1.00 | 1.00 | 1.00 | 1.00 | 1.00 | 1.00 | 1.00 | 1.00 | 1.00 | 1.00 | 6.96 | 0.71 |
| Ptprn | 1.70 | 1.56 | 1.34 | 1.00 | 1.00 | 1.00 | 1.00 | 1.00 | 1.00 | 1.00 | 8.10 | 1.00 |
| Ptprn2 | 1.00 | 0.93 | 0.80 | 1.00 | 1.00 | 1.00 | 1.00 | 1.00 | 1.00 | 1.00 | 6.16 | 1.00 |
| Pvalb | 1.00 | 0.71 | 1.00 | 1.00 | 0.73 | 1.00 | 1.00 | 1.00 | 1.00 | 1.00 | 9.06 | 1.00 |
| Pvr | 1.09 | 1.00 | 1.10 | 2.13 | 0.52 | 1.66 | 1.12 | 0.84 | 0.91 | 0.95 | 0.85 | 0.90 |
| Pxmp2 | 1.54 | 0.98 | 1.28 | 0.46 | 2.97 | 0.96 | 0.82 | 0.55 | 1.00 | 1.27 | 1.59 | 1.25 |
| Pycrl | 0.93 | 1.03 | 0.89 | 1.01 | 5.82 | 1.16 | 0.98 | 0.82 | 0.62 | 1.03 | 1.20 | 1.23 |
| Pydc3 | 1.00 | 1.00 | 1.00 | 1.00 | 1.00 | 1.00 | 1.00 | 1.00 | 1.00 | 4.78 | 3.66 | 3.47 |
| Pyroxd2 | 0.54 | 0.94 | 0.76 | 0.31 | 0.47 | 0.46 | 0.24 | 0.44 | 0.21 | 0.87 | 1.00 | 0.78 |
| Pyy | 2.56 | 1.61 | 3.29 | 1.00 | 1.00 | 1.00 | 0.47 | 2.41 | 0.73 | 1.00 | 1.00 | 1.00 |
| Qtrt1 | 0.89 | 0.82 | 1.17 | 0.98 | 2.84 | 0.82 | 2.44 | 4.83 | 3.00 | 0.83 | 0.98 | 1.04 |
| Rab10os | 1.12 | 1.45 | 1.28 | 1.22 | 6.17 | 1.38 | 0.79 | 1.77 | 1.07 | 1.03 | 1.75 | 1.10 |
| Rab13 | 1.17 | 0.87 | 0.96 | 0.79 | 1.15 | 0.73 | 0.67 | 0.60 | 0.73 | 1.19 | 0.90 | 0.79 |
| Rab15 | 0.74 | 0.87 | 1.13 | 4.59 | 0.93 | 4.96 | 1.00 | 1.00 | 1.00 | 1.36 | 6.61 | 1.08 |
| Rab17 | 1.28 | 1.68 | 1.00 | 1.18 | 2.57 | 1.21 | 1.00 | 2.80 | 1.00 | 0.84 | 1.71 | 1.66 |
| Rab24 | 1.03 | 1.31 | 1.17 | 0.85 | 2.69 | 0.92 | 0.94 | 2.59 | 1.00 | 0.96 | 1.11 | 0.97 |
| Rab26os | 0.86 | 0.70 | 0.54 | 0.56 | 1.00 | 0.87 | 2.21 | 0.60 | 4.02 | 1.04 | 1.24 | 0.77 |
| Rab30 | 1.01 | 1.24 | 1.10 | 0.54 | 1.00 | 0.85 | 1.00 | 1.00 | 0.78 | 2.05 | 2.35 | 1.52 |
| Rab34 | 0.88 | 1.17 | 0.89 | 0.61 | 1.82 | 0.82 | 0.94 | 1.38 | 0.82 | 0.99 | 1.53 | 1.05 |

Fig. 35- 240

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Prpf19 | 1.00 | 0.72 | 0.99 | 1.15 | 0.88 | 1.00 | 1.06 | 5.38 | 1.08 | 2.27 | 0.92 | 0.95 |
| Prpf6 | 0.71 | 0.89 | 1.17 | 1.03 | 1.00 | 1.03 | 1.03 | 4.50 | 0.97 | 1.77 | 1.02 | 0.95 |
| Prph | 1.00 | 1.00 | 1.00 | 1.10 | 1.07 | 0.75 | 1.00 | 2.34 | 1.00 | 1.00 | 1.00 | 1.00 |
| Prpsap1 | 0.85 | 0.76 | 0.78 | 0.94 | 1.06 | 1.18 | 0.97 | 3.49 | 0.83 | 1.85 | 1.25 | 1.06 |
| Prr15l | 0.86 | 1.20 | 0.94 | 1.00 | 1.00 | 1.00 | 0.96 | 2.41 | 0.61 | 1.00 | 1.00 | 1.00 |
| Prr22 | 1.00 | 1.00 | 1.00 | 1.00 | 6.19 | 0.92 | 2.84 | 2.87 | 1.09 | 1.87 | 1.09 | 1.67 |
| Prr30 | 1.00 | 1.00 | 1.00 | 1.00 | 1.00 | 1.00 | 5.17 | 1.00 | 1.00 | 1.00 | 1.00 | 1.00 |
| Prss2 | 1.03 | 1.04 | 0.88 | 1.05 | 1.00 | 0.74 | 0.69 | 4.04 | 0.89 | 0.87 | 0.44 | 1.30 |
| Prss22 | 1.70 | 4.86 | 3.83 | 5.59 | 13.48 | 3.68 | 2.91 | 1.93 | 2.17 | 2.90 | 3.32 | 2.14 |
| Prss3 | 1.28 | 1.75 | 1.05 | 1.00 | 0.20 | 1.00 | 1.00 | 1.00 | 1.00 | 1.00 | 1.00 | 1.00 |
| Prss53 | 0.45 | 0.49 | 0.46 | 1.03 | 1.85 | 1.03 | 0.89 | 4.66 | 0.69 | 4.35 | 1.00 | 1.00 |
| Prtn3 | 1.00 | 1.00 | 1.00 | 1.00 | 1.00 | 0.67 | 1.00 | 1.00 | 1.00 | 3.63 | 1.56 | 1.46 |
| Prune2 | 1.00 | 1.00 | 1.00 | 1.05 | 1.15 | 1.06 | 1.24 | 0.69 | 1.30 | 1.00 | 1.00 | 1.00 |
| Psca | 1.00 | 1.00 | 0.23 | 1.00 | 0.83 | 0.24 | 1.23 | 6.75 | 0.68 | 1.00 | 1.00 | 1.00 |
| Psen2 | 2.00 | 1.68 | 2.10 | 1.54 | 1.42 | 1.13 | 2.27 | 5.74 | 1.72 | 2.10 | 1.19 | 1.16 |
| Psenen | 1.61 | 1.10 | 0.76 | 1.08 | 0.62 | 0.93 | 1.32 | 3.04 | 0.75 | 2.01 | 1.30 | 1.22 |
| Psma5 | 1.02 | 1.00 | 1.00 | 0.93 | 1.05 | 1.02 | 1.06 | 6.94 | 0.88 | 2.50 | 1.11 | 1.17 |
| Psma6 | 1.06 | 1.05 | 0.94 | 0.99 | 1.00 | 1.06 | 1.24 | 7.69 | 0.93 | 2.45 | 1.20 | 1.09 |
| Psma7 | 0.92 | 1.32 | 0.80 | 1.13 | 0.97 | 1.14 | 1.29 | 14.71 | 0.98 | 3.19 | 1.10 | 1.05 |
| Psmb1 | 0.63 | 0.87 | 0.93 | 1.01 | 0.90 | 1.01 | 1.08 | 6.84 | 0.87 | 2.31 | 1.03 | 1.03 |
| Psmb10 | 0.56 | 0.78 | 0.98 | 1.09 | 0.86 | 1.03 | 0.85 | 20.44 | 0.84 | 5.49 | 1.42 | 1.22 |
| Psmb3 | 0.67 | 1.35 | 0.99 | 1.02 | 0.98 | 1.06 | 1.31 | 2.19 | 1.00 | 1.76 | 0.91 | 0.88 |
| Psmb6 | 1.05 | 0.91 | 1.17 | 1.15 | 0.94 | 1.04 | 1.33 | 11.82 | 0.89 | 2.53 | 1.19 | 1.25 |
| Psmb7 | 0.87 | 0.66 | 0.95 | 1.27 | 0.82 | 1.02 | 1.27 | 8.61 | 1.02 | 2.50 | 0.98 | 1.02 |
| Psmb8 | 1.00 | 1.00 | 0.95 | 1.00 | 0.53 | 1.64 | 1.59 | 9.18 | 1.35 | 2.92 | 1.35 | 1.31 |
| Psmb9 | 1.00 | 1.00 | 0.81 | 1.00 | 1.18 | 1.07 | 1.83 | 3.95 | 1.26 | 2.32 | 1.55 | 1.39 |
| Psmc1 | 1.12 | 1.00 | 0.80 | 1.17 | 1.10 | 1.17 | 1.09 | 4.25 | 0.99 | 2.10 | 1.14 | 1.04 |
| Psmc2 | 1.28 | 0.85 | 0.93 | 1.06 | 0.92 | 1.14 | 1.08 | 4.06 | 0.91 | 1.55 | 1.10 | 0.96 |
| Psmd12 | 1.38 | 1.37 | 0.99 | 1.13 | 0.86 | 1.24 | 1.04 | 7.77 | 0.91 | 1.37 | 0.84 | 0.96 |
| Psmd13 | 1.06 | 1.18 | 1.11 | 1.10 | 1.16 | 1.01 | 1.21 | 6.80 | 0.97 | 2.25 | 1.03 | 1.02 |
| Psmd2 | 0.97 | 1.41 | 1.31 | 1.12 | 1.02 | 1.03 | 1.06 | 7.52 | 0.98 | 2.65 | 0.94 | 0.95 |
| Psmd4 | 1.25 | 1.18 | 1.11 | 1.19 | 0.91 | 1.16 | 1.42 | 18.59 | 1.06 | 3.01 | 1.18 | 1.02 |
| Psme1 | 0.99 | 0.91 | 0.76 | 0.96 | 1.33 | 0.93 | 1.39 | 6.13 | 0.95 | 3.19 | 1.45 | 1.52 |
| Psmg2 | 1.01 | 0.68 | 0.75 | 1.03 | 0.85 | 1.16 | 1.01 | 6.09 | 0.88 | 1.65 | 0.76 | 1.05 |
| Psmg3 | 1.02 | 1.08 | 1.12 | 1.10 | 1.02 | 0.95 | 1.16 | 8.46 | 0.73 | 2.25 | 1.12 | 1.00 |
| Psors1c2 | 1.00 | 1.00 | 1.00 | 1.00 | 1.00 | 1.00 | 1.54 | 6.43 | 0.95 | 1.00 | 1.00 | 1.00 |
| Pstpip1 | 1.00 | 1.00 | 1.00 | 1.00 | 0.42 | 1.00 | 0.96 | 16.04 | 0.82 | 4.03 | 1.23 | 1.00 |
| Ptgds | 1.00 | 1.00 | 1.00 | 0.74 | 0.55 | 0.68 | 1.23 | 1.88 | 1.86 | 1.00 | 1.00 | 1.00 |
| Ptges3l | 1.00 | 1.00 | 1.00 | 0.93 | 1.93 | 1.12 | 1.11 | 13.89 | 1.48 | 1.76 | 1.00 | 1.00 |
| Ptgis | 0.97 | 1.00 | 1.24 | 1.04 | 0.83 | 0.92 | 1.25 | 21.95 | 1.07 | 1.00 | 1.00 | 1.00 |
| Ptgs1 | 1.00 | 1.00 | 1.00 | 0.81 | 0.70 | 0.83 | 0.60 | 3.00 | 0.49 | 2.44 | 1.29 | 1.21 |
| Pth | 1.00 | 1.00 | 1.00 | 1.00 | 1.00 | 1.00 | 1.00 | 1.00 | 1.00 | 1.00 | 1.00 | 1.00 |
| Pth1r | 1.00 | 1.00 | 1.00 | 1.01 | 0.68 | 1.32 | 0.90 | 13.47 | 0.98 | 1.00 | 1.00 | 1.00 |
| Pth2 | 1.00 | 1.00 | 1.00 | 1.00 | 1.38 | 1.00 | 1.00 | 1.00 | 1.00 | 1.00 | 1.00 | 1.00 |
| Ptpn18 | 1.35 | 0.99 | 0.89 | 1.00 | 0.26 | 1.00 | 1.38 | 18.93 | 1.22 | 4.19 | 1.48 | 1.37 |
| Ptpn5 | 1.00 | 1.00 | 1.00 | 1.15 | 1.10 | 1.12 | 1.00 | 1.00 | 1.00 | 1.00 | 1.00 | 1.00 |
| Ptprn | 1.00 | 1.00 | 1.00 | 1.25 | 1.46 | 1.16 | 1.00 | 1.00 | 1.00 | 1.00 | 1.00 | 1.00 |
| Ptprn2 | 1.02 | 0.96 | 1.13 | 1.03 | 0.54 | 0.98 | 1.00 | 1.00 | 1.00 | 1.00 | 1.00 | 1.00 |
| Pvalb | 1.00 | 1.00 | 1.00 | 1.11 | 1.10 | 1.00 | 2.14 | 14.32 | 3.07 | 1.74 | 1.00 | 1.00 |
| Pvr | 1.61 | 2.44 | 1.28 | 0.98 | 1.00 | 1.15 | 1.26 | 0.18 | 0.95 | 1.00 | 1.11 | 1.24 |
| Pxmp2 | 0.62 | 0.64 | 0.61 | 0.99 | 1.51 | 1.15 | 2.02 | 3.77 | 1.21 | 2.16 | 1.12 | 0.95 |
| Pycr1 | 0.62 | 1.15 | 0.88 | 1.29 | 0.67 | 0.92 | 0.96 | 3.12 | 0.94 | 1.44 | 0.82 | 0.90 |
| Pydc3 | 1.00 | 1.00 | 1.00 | 1.00 | 1.00 | 1.00 | 1.00 | 1.00 | 1.00 | 2.08 | 3.77 | 3.35 |
| Pyroxd2 | 1.00 | 1.00 | 1.00 | 0.47 | 1.00 | 0.46 | 0.74 | 0.89 | 0.76 | 0.57 | 0.69 | 0.70 |
| Pyy | 0.93 | 0.48 | 0.94 | 1.00 | 2.18 | 1.00 | 0.26 | 10.50 | 0.36 | 1.00 | 1.00 | 1.00 |
| Qtrt1 | 0.80 | 0.98 | 0.89 | 0.90 | 0.45 | 0.80 | 0.68 | 6.06 | 0.58 | 3.25 | 0.64 | 0.87 |
| Rab10os | 1.18 | 1.04 | 0.69 | 0.80 | 2.01 | 0.86 | 1.12 | 10.48 | 0.97 | 3.54 | 1.35 | 1.00 |
| Rab13 | 1.00 | 1.00 | 1.00 | 1.33 | 0.43 | 1.12 | 1.16 | 7.14 | 1.05 | 1.25 | 1.28 | 1.02 |
| Rab15 | 1.00 | 1.00 | 1.00 | 1.11 | 2.10 | 0.99 | 0.81 | 0.24 | 1.02 | 1.00 | 1.54 | 1.00 |
| Rab17 | 1.02 | 1.48 | 1.00 | 1.00 | 0.26 | 1.00 | 0.97 | 17.89 | 1.14 | 4.96 | 1.09 | 1.38 |
| Rab24 | 0.85 | 0.59 | 0.72 | 1.01 | 1.35 | 1.04 | 1.06 | 7.32 | 0.89 | 3.56 | 1.28 | 1.13 |
| Rab26os | 1.00 | 1.45 | 1.15 | 0.74 | 14.87 | 0.97 | 1.12 | 2.05 | 0.83 | 1.07 | 0.92 | 0.84 |
| Rab30 | 1.00 | 1.17 | 1.00 | 0.85 | 2.54 | 0.86 | 0.52 | 0.37 | 0.51 | 0.88 | 1.17 | 0.97 |
| Rab34 | 0.98 | 0.94 | 0.89 | 1.23 | 0.60 | 1.00 | 1.23 | 3.47 | 0.98 | 1.00 | 1.00 | 1.00 |

Fig. 35- 241

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Rab3c | 1.00 | 1.00 | 1.00 | 1.00 | 0.20 | 1.00 | 1.00 | 1.00 | 1.00 | 1.00 | 1.00 | 1.49 |
| Rab40b | 0.92 | 1.02 | 0.53 | 8.91 | 6.57 | 5.91 | 1.29 | 1.36 | 0.93 | 0.67 | 1.11 | 0.94 |
| Rab4b | 1.59 | 1.04 | 0.81 | 1.07 | 5.63 | 1.19 | 1.50 | 1.04 | 1.09 | 1.18 | 2.00 | 1.05 |
| Rab6b | 1.00 | 1.00 | 1.00 | 0.53 | 0.06 | 0.33 | 1.00 | 1.00 | 0.50 | 0.34 | 0.39 | 0.52 |
| Rab7 | 1.08 | 5.53 | 1.37 | 0.72 | 0.03 | 1.01 | 1.08 | 1.51 | 1.29 | 1.00 | 0.10 | 1.10 |
| Rab7l1 | 0.79 | 0.63 | 1.25 | 1.13 | 6.40 | 0.88 | 0.82 | 0.63 | 0.92 | 1.43 | 2.24 | 0.80 |
| Rab9 | 1.23 | 1.41 | 1.16 | 1.71 | 1.36 | 1.28 | 0.98 | 1.00 | 0.85 | 0.83 | 0.70 | 1.00 |
| Rabac1 | 1.39 | 0.62 | 0.85 | 0.53 | 6.57 | 1.01 | 1.02 | 0.76 | 0.90 | 2.21 | 2.94 | 0.95 |
| Rabif | 0.94 | 0.78 | 0.99 | 0.81 | 0.56 | 0.90 | 1.07 | 0.88 | 0.93 | 1.00 | 0.81 | 1.03 |
| Rad9a | 0.98 | 0.41 | 1.29 | 0.65 | 6.80 | 0.88 | 1.08 | 0.57 | 0.84 | 2.32 | 2.15 | 0.82 |
| Rae1 | 1.32 | 0.61 | 1.14 | 0.71 | 8.34 | 1.05 | 1.15 | 1.03 | 0.95 | 2.51 | 3.65 | 0.83 |
| Raet1d | 1.00 | 1.00 | 1.00 | 1.00 | 1.00 | 1.00 | 1.00 | 1.00 | 1.00 | 1.60 | 3.14 | 5.08 |
| Rai2 | 0.92 | 1.72 | 1.26 | 1.10 | 0.42 | 0.92 | 1.03 | 1.01 | 0.87 | 0.50 | 0.53 | 1.08 |
| Ranbp1 | 1.28 | 0.57 | 1.04 | 0.59 | 4.40 | 0.89 | 0.92 | 0.89 | 1.20 | 2.59 | 1.99 | 1.00 |
| Rangrf | 1.49 | 0.47 | 0.90 | 0.39 | 11.88 | 0.56 | 0.92 | 0.60 | 0.90 | 4.95 | 5.66 | 1.08 |
| Rap1gap2 | 1.02 | 1.11 | 1.08 | 18.55 | 1.83 | 3.71 | 0.82 | 0.94 | 0.80 | 1.00 | 0.87 | 0.70 |
| Rarres2 | 1.36 | 1.06 | 1.17 | 0.88 | 1.51 | 0.68 | 0.71 | 0.70 | 1.14 | 0.35 | 0.82 | 0.72 |
| Rasa3 | 2.22 | 3.13 | 1.73 | 5.49 | 3.97 | 3.59 | 1.23 | 1.10 | 1.13 | 0.51 | 0.55 | 1.07 |
| Rasd1 | 1.69 | 3.09 | 1.96 | 1.24 | 2.07 | 1.05 | 1.91 | 2.43 | 1.39 | 0.57 | 2.29 | 2.34 |
| Rasd2 | 0.27 | 0.30 | 0.56 | 0.53 | 0.13 | 0.89 | 0.57 | 0.64 | 0.47 | 1.11 | 0.65 | 1.10 |
| Rasgrf1 | 1.00 | 1.00 | 1.00 | 1.00 | 0.25 | 1.00 | 1.00 | 1.00 | 1.00 | 1.00 | 1.00 | 1.00 |
| Rasip1 | 0.84 | 0.55 | 1.02 | 0.88 | 3.62 | 1.15 | 1.13 | 1.00 | 1.03 | 1.61 | 1.96 | 0.85 |
| Rasl10b | 1.00 | 1.00 | 1.00 | 1.00 | 0.16 | 1.00 | 1.20 | 1.06 | 1.16 | 1.33 | 1.87 | 1.67 |
| Rassf4 | 2.83 | 7.14 | 7.63 | 10.75 | 3.51 | 4.13 | 1.86 | 1.98 | 1.91 | 0.88 | 0.53 | 0.85 |
| Rbakdn | 1.00 | 1.00 | 1.00 | 1.00 | 1.00 | 1.00 | 1.00 | 1.00 | 1.00 | 5.63 | 3.32 | 1.00 |
| Rbfa | 1.24 | 0.67 | 1.11 | 0.56 | 6.72 | 1.21 | 1.47 | 1.21 | 1.17 | 1.90 | 3.12 | 1.18 |
| Rbfox1 | 0.85 | 1.11 | 0.96 | 1.00 | 0.18 | 1.14 | 1.01 | 1.06 | 0.72 | 1.00 | 1.00 | 1.00 |
| Rbfox3 | 1.00 | 1.00 | 1.00 | 1.00 | 0.20 | 1.00 | 1.00 | 1.00 | 1.00 | 0.79 | 0.72 | 1.51 |
| Rbks | 1.65 | 1.50 | 0.95 | 0.45 | 3.84 | 1.33 | 1.13 | 1.30 | 1.22 | 2.11 | 3.17 | 1.37 |
| Rbp1 | 0.99 | 0.53 | 1.16 | 0.84 | 4.74 | 1.00 | 1.07 | 0.74 | 1.19 | 2.23 | 3.02 | 0.86 |
| Rbp2 | 1.00 | 1.00 | 1.00 | 1.00 | 1.00 | 1.00 | 1.00 | 1.00 | 1.00 | 0.97 | 1.91 | 1.00 |
| Rbp7 | 1.00 | 0.80 | 1.20 | 0.58 | 5.68 | 1.04 | 0.77 | 0.80 | 1.06 | 1.60 | 2.47 | 1.00 |
| Rce1 | 1.22 | 0.71 | 1.56 | 0.81 | 5.01 | 1.41 | 0.84 | 0.75 | 0.91 | 1.61 | 2.60 | 0.94 |
| Rdh14 | 1.01 | 1.24 | 0.87 | 0.71 | 0.74 | 0.99 | 1.02 | 1.03 | 0.86 | 0.60 | 0.58 | 0.95 |
| Rdh5 | 1.00 | 0.41 | 1.62 | 0.34 | 3.12 | 1.01 | 0.59 | 0.82 | 0.84 | 1.24 | 2.10 | 0.74 |
| Rdm1 | 0.80 | 0.44 | 0.67 | 0.63 | 7.61 | 1.15 | 0.78 | 0.73 | 0.69 | 2.14 | 2.97 | 0.80 |
| Redrum | 1.00 | 1.00 | 1.00 | 1.00 | 1.00 | 1.00 | 1.00 | 1.00 | 1.00 | 1.00 | 1.00 | 1.00 |
| Reep4 | 2.64 | 1.09 | 1.29 | 3.04 | 5.20 | 1.92 | 1.11 | 0.85 | 1.20 | 0.85 | 1.20 | 0.86 |
| Reg1 | 1.00 | 1.00 | 1.00 | 1.00 | 1.00 | 1.00 | 1.00 | 1.00 | 1.00 | 1.00 | 1.00 | 1.00 |
| Reg2 | 1.00 | 1.00 | 1.00 | 1.00 | 1.00 | 1.00 | 1.00 | 1.00 | 1.00 | 1.00 | 1.00 | 1.00 |
| Reg3a | 1.00 | 1.00 | 1.00 | 1.00 | 1.00 | 1.00 | 1.00 | 1.00 | 1.00 | 1.00 | 1.00 | 1.00 |
| Reg3b | 1.00 | 1.00 | 1.00 | 1.00 | 1.00 | 1.00 | 1.00 | 1.00 | 1.00 | 1.00 | 1.00 | 1.00 |
| Reg3g | 1.00 | 1.00 | 1.00 | 1.00 | 1.00 | 1.00 | 1.00 | 1.00 | 1.00 | 0.51 | 2.07 | 0.48 |
| Relb | 1.06 | 1.08 | 1.34 | 1.32 | 5.61 | 1.38 | 1.00 | 1.02 | 1.18 | 1.68 | 2.04 | 1.04 |
| Rell2 | 1.00 | 1.00 | 1.00 | 1.00 | 0.27 | 1.00 | 1.00 | 1.00 | 1.00 | 1.00 | 1.00 | 1.00 |
| Ren1 | 1.00 | 1.00 | 1.00 | 1.00 | 1.00 | 1.00 | 1.00 | 1.00 | 1.00 | 1.00 | 1.00 | 1.00 |
| Renbp | 1.00 | 1.00 | 1.20 | 0.56 | 2.14 | 1.49 | 1.32 | 0.93 | 1.31 | 2.20 | 1.66 | 1.00 |
| Rerg | 1.00 | 1.00 | 1.00 | 1.00 | 1.00 | 1.00 | 1.87 | 2.06 | 1.80 | 0.50 | 0.26 | 0.79 |
| Rergl | 1.72 | 2.14 | 1.32 | 2.31 | 3.89 | 2.09 | 6.46 | 5.45 | 2.02 | 1.00 | 1.00 | 1.00 |
| Retn | 1.19 | 0.95 | 1.63 | 0.35 | 20.63 | 2.00 | 1.00 | 1.00 | 1.00 | 1.00 | 1.07 | 1.00 |
| Retnla | 1.07 | 0.32 | 1.47 | 0.68 | 5.89 | 1.24 | 0.77 | 0.67 | 1.29 | 3.86 | 4.62 | 1.29 |
| Retnlg | 1.67 | 3.68 | 1.00 | 1.83 | 2.25 | 1.00 | 1.00 | 1.00 | 1.26 | 6.48 | 6.65 | 1.48 |
| Retsat | 0.81 | 0.60 | 1.01 | 0.41 | 1.79 | 0.86 | 0.74 | 0.61 | 0.71 | 1.03 | 1.45 | 0.78 |
| Rfc2 | 1.27 | 0.61 | 0.87 | 0.39 | 7.97 | 0.96 | 1.01 | 0.90 | 0.80 | 2.59 | 3.91 | 0.88 |
| Rfc5 | 1.04 | 0.40 | 0.72 | 0.67 | 3.66 | 0.63 | 0.96 | 0.89 | 0.87 | 1.48 | 2.22 | 1.00 |
| Rgl2 | 1.14 | 0.69 | 1.08 | 0.71 | 3.32 | 0.92 | 1.12 | 0.98 | 1.03 | 2.26 | 2.30 | 1.06 |
| Rgs1 | 1.00 | 1.00 | 1.00 | 1.00 | 1.00 | 1.00 | 1.00 | 1.00 | 1.00 | 1.00 | 1.73 | 1.15 |
| Rgs2 | 7.51 | 11.15 | 7.46 | 2.30 | 4.24 | 2.08 | 0.35 | 0.39 | 0.36 | 0.59 | 1.17 | 0.76 |
| Rgs3 | 0.96 | 1.03 | 0.99 | 1.60 | 5.28 | 1.40 | 0.84 | 0.86 | 0.82 | 1.09 | 0.69 | 0.84 |
| Rgs7bp | 1.00 | 1.00 | 1.00 | 1.00 | 0.29 | 1.00 | 1.00 | 1.15 | 1.00 | 1.00 | 1.00 | 1.00 |
| Rgs8 | 1.00 | 1.00 | 1.00 | 1.00 | 0.23 | 1.00 | 1.00 | 1.00 | 1.00 | 1.00 | 1.00 | 1.00 |
| Rhbdd3 | 1.23 | 0.73 | 0.94 | 0.50 | 4.01 | 0.83 | 0.94 | 0.84 | 0.80 | 2.05 | 2.47 | 1.42 |
| Rhbg | 1.00 | 1.00 | 1.00 | 1.00 | 1.38 | 1.00 | 1.00 | 1.00 | 1.00 | 2.84 | 1.93 | 1.14 |
| Rhobtb3 | 0.94 | 2.90 | 1.06 | 5.06 | 0.32 | 1.24 | 0.90 | 1.00 | 0.80 | 1.00 | 1.00 | 0.79 |

Fig. 35- 242

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Rab3c | 1.00 | 1.00 | 1.00 | 1.00 | 1.00 | 1.00 | 1.00 | 1.00 | 1.00 | 1.44 | 0.96 | 1.12 |
| Rab40b | 1.25 | 2.08 | 1.52 | 0.73 | 1.00 | 1.09 | 1.00 | 1.00 | 1.00 | 0.58 | 1.08 | 0.72 |
| Rab4b | 1.21 | 1.36 | 1.08 | 0.98 | 0.87 | 0.93 | 1.10 | 0.86 | 1.05 | 0.92 | 1.63 | 1.00 |
| Rab6b | 0.22 | 0.27 | 0.22 | 0.88 | 1.05 | 1.06 | 1.00 | 1.00 | 1.00 | 0.92 | 0.56 | 0.73 |
| Rab7 | 0.85 | 0.74 | 1.17 | 0.92 | 1.00 | 1.06 | 0.90 | 1.00 | 0.91 | 0.97 | 0.53 | 1.03 |
| Rab7l1 | 1.15 | 1.49 | 1.05 | 0.77 | 0.68 | 0.97 | 0.79 | 0.98 | 0.80 | 1.07 | 1.37 | 0.89 |
| Rab9 | 1.12 | 1.12 | 0.97 | 1.01 | 1.24 | 1.02 | 1.12 | 1.08 | 1.06 | 1.12 | 1.16 | 1.12 |
| Rabac1 | 1.43 | 2.12 | 1.30 | 0.95 | 0.69 | 1.06 | 0.99 | 1.64 | 0.94 | 1.15 | 1.65 | 1.15 |
| Rabif | 0.80 | 0.79 | 0.91 | 1.10 | 0.93 | 0.99 | 1.10 | 1.08 | 0.87 | 0.98 | 0.92 | 0.92 |
| Rad9a | 0.80 | 0.79 | 0.87 | 0.70 | 0.51 | 0.79 | 0.80 | 1.94 | 1.10 | 0.92 | 1.33 | 1.23 |
| Rae1 | 1.11 | 1.39 | 0.98 | 1.41 | 0.76 | 0.98 | 1.07 | 2.04 | 1.27 | 0.91 | 1.45 | 1.05 |
| Raet1d | 1.00 | 1.00 | 1.00 | 1.00 | 1.00 | 1.00 | 10.34 | 1.00 | 9.20 | 10.38 | 12.51 | 8.16 |
| Rai2 | 7.64 | 4.99 | 3.38 | 1.15 | 1.07 | 1.27 | 1.01 | 1.00 | 1.19 | 0.95 | 0.94 | 1.04 |
| Ranbp1 | 0.59 | 0.60 | 0.56 | 0.86 | 0.59 | 1.01 | 1.17 | 2.47 | 0.95 | 0.76 | 1.46 | 1.12 |
| Rangrf | 1.01 | 1.65 | 1.01 | 0.81 | 0.43 | 1.10 | 1.00 | 5.32 | 1.00 | 1.01 | 3.21 | 0.95 |
| Rap1gap2 | 1.02 | 0.87 | 1.34 | 1.03 | 1.02 | 0.95 | 1.00 | 1.00 | 1.00 | 1.13 | 0.82 | 1.09 |
| Rarres2 | 3.36 | 2.03 | 1.02 | 0.99 | 1.63 | 1.16 | 0.98 | 0.47 | 0.91 | 0.93 | 1.17 | 0.99 |
| Rasa3 | 1.01 | 0.97 | 1.31 | 1.09 | 1.04 | 1.00 | 0.84 | 0.70 | 1.02 | 1.08 | 1.06 | 1.19 |
| Rasd1 | 2.37 | 3.24 | 1.28 | 0.98 | 1.20 | 1.28 | 3.09 | 1.56 | 2.00 | 0.94 | 0.99 | 1.02 |
| Rasd2 | 0.93 | 0.48 | 0.74 | 0.43 | 0.58 | 0.50 | 1.00 | 1.00 | 1.00 | 1.19 | 0.91 | 1.38 |
| Rasgrf1 | 1.00 | 1.00 | 1.00 | 1.00 | 1.00 | 1.00 | 1.00 | 1.00 | 1.00 | 1.00 | 1.00 | 1.00 |
| Rasip1 | 2.12 | 1.79 | 1.39 | 0.96 | 0.59 | 1.17 | 0.80 | 1.55 | 1.09 | 0.79 | 1.28 | 1.05 |
| Rasl10b | 1.00 | 1.00 | 1.00 | 1.00 | 1.00 | 1.00 | 1.42 | 2.09 | 1.58 | 1.33 | 1.40 | 1.11 |
| Rassf4 | 0.99 | 0.78 | 1.36 | 4.38 | 2.39 | 3.32 | 0.26 | 0.76 | 0.29 | 0.96 | 0.69 | 0.98 |
| Rbakdn | 1.00 | 1.00 | 1.00 | 1.00 | 0.72 | 1.00 | 1.00 | 1.00 | 1.00 | 1.00 | 1.00 | 1.00 |
| Rbfa | 1.25 | 1.79 | 1.16 | 1.15 | 0.92 | 1.53 | 1.09 | 1.37 | 1.21 | 1.20 | 1.75 | 1.31 |
| Rbfox1 | 1.94 | 1.13 | 1.59 | 1.00 | 1.00 | 1.00 | 1.00 | 1.00 | 1.00 | 0.96 | 1.00 | 1.00 |
| Rbfox3 | 1.00 | 1.00 | 1.00 | 1.00 | 1.00 | 1.00 | 1.00 | 1.00 | 1.00 | 1.00 | 1.00 | 0.93 |
| Rbks | 0.92 | 1.34 | 1.05 | 1.07 | 1.14 | 0.95 | 1.26 | 0.93 | 0.89 | 1.04 | 1.69 | 1.30 |
| Rbp1 | 1.09 | 1.10 | 0.63 | 2.01 | 2.23 | 1.57 | 0.69 | 1.52 | 1.07 | 1.16 | 1.28 | 0.80 |
| Rbp2 | 1.00 | 1.22 | 1.00 | 1.00 | 1.00 | 1.00 | 1.00 | 1.00 | 1.00 | 1.10 | 1.70 | 1.05 |
| Rbp7 | 2.35 | 2.10 | 1.63 | 1.44 | 2.30 | 1.71 | 1.00 | 1.00 | 1.00 | 1.22 | 2.26 | 1.98 |
| Rce1 | 1.05 | 1.15 | 0.82 | 0.83 | 0.64 | 0.94 | 1.12 | 2.41 | 1.02 | 0.93 | 1.60 | 1.13 |
| Rdh14 | 1.22 | 1.29 | 1.10 | 1.08 | 1.51 | 1.12 | 1.03 | 0.50 | 0.85 | 1.24 | 1.31 | 1.07 |
| Rdh5 | 0.87 | 1.50 | 1.23 | 0.84 | 0.73 | 0.82 | 0.82 | 0.80 | 1.09 | 0.86 | 1.27 | 0.72 |
| Rdm1 | 1.18 | 1.23 | 0.88 | 0.86 | 0.59 | 1.01 | 0.57 | 1.17 | 0.85 | 1.12 | 1.55 | 0.99 |
| Redrum | 1.00 | 1.00 | 1.00 | 1.00 | 1.00 | 1.00 | 1.00 | 1.00 | 1.00 | 1.00 | 1.00 | 1.00 |
| Reep4 | 0.95 | 1.16 | 0.94 | 0.81 | 1.40 | 1.12 | 1.28 | 0.69 | 1.38 | 1.00 | 1.26 | 1.15 |
| Reg1 | 1.93 | 1.00 | 1.00 | 1.00 | 1.00 | 1.00 | 1.00 | 1.00 | 1.08 | 0.96 | 4.90 | 38.48 |
| Reg2 | 1.00 | 1.00 | 1.00 | 1.00 | 1.00 | 1.00 | 1.00 | 1.00 | 1.00 | 30.66 | 18.54 | 14.56 |
| Reg3a | 1.00 | 1.00 | 1.00 | 1.00 | 1.00 | 1.00 | 1.00 | 1.00 | 1.00 | 1.00 | 1.00 | 1.17 |
| Reg3b | 3.63 | 2.55 | 1.00 | 1.00 | 1.00 | 1.00 | 1.00 | 1.00 | 1.00 | 0.90 | 4.75 | 3.47 |
| Reg3g | 2.38 | 2.39 | 1.07 | 1.00 | 1.00 | 1.00 | 1.00 | 1.00 | 1.00 | 1.26 | 3.86 | 6.03 |
| Relb | 1.02 | 1.16 | 1.08 | 1.07 | 0.59 | 0.85 | 1.00 | 0.91 | 1.84 | 1.05 | 1.27 | 0.99 |
| Rell2 | 1.00 | 1.15 | 1.22 | 1.00 | 1.00 | 1.00 | 1.00 | 1.00 | 1.00 | 1.00 | 1.00 | 1.00 |
| Ren1 | 1.01 | 1.00 | 1.00 | 0.45 | 0.43 | 0.51 | 1.00 | 45.80 | 1.00 | 1.00 | 1.00 | 1.00 |
| Renbp | 2.10 | 1.83 | 1.59 | 0.86 | 0.68 | 1.00 | 1.00 | 1.83 | 0.67 | 0.91 | 1.07 | 1.04 |
| Rerg | 1.50 | 1.01 | 1.83 | 0.66 | 1.00 | 1.03 | 3.46 | 1.00 | 3.10 | 0.93 | 0.65 | 0.88 |
| Rergl | 1.00 | 1.20 | 1.00 | 0.98 | 0.84 | 1.90 | 1.00 | 1.00 | 1.00 | 1.07 | 3.81 | 1.36 |
| Retn | 0.49 | 3.00 | 2.06 | 1.00 | 0.41 | 1.00 | 1.00 | 1.00 | 1.00 | 1.00 | 1.00 | 1.00 |
| Retnla | 2.55 | 2.07 | 1.19 | 1.00 | 1.43 | 1.00 | 1.00 | 1.00 | 1.00 | 0.61 | 0.86 | 0.79 |
| Retnlg | 0.15 | 0.49 | 0.75 | 1.00 | 1.00 | 1.00 | 1.00 | 2.00 | 1.00 | 1.00 | 0.86 | 0.75 |
| Retsat | 1.09 | 1.10 | 0.68 | 0.37 | 0.30 | 0.42 | 0.53 | 0.90 | 0.77 | 0.97 | 0.91 | 0.95 |
| Rfc2 | 0.92 | 1.27 | 0.83 | 1.11 | 0.58 | 0.95 | 0.86 | 1.53 | 0.68 | 0.79 | 1.63 | 0.95 |
| Rfc5 | 0.75 | 0.86 | 0.66 | 0.69 | 0.60 | 0.90 | 0.56 | 1.45 | 0.80 | 1.09 | 1.38 | 0.89 |
| Rgl2 | 1.08 | 1.35 | 1.10 | 0.99 | 0.60 | 1.25 | 1.31 | 2.77 | 1.53 | 1.12 | 1.45 | 1.26 |
| Rgs1 | 2.25 | 2.50 | 1.42 | 1.00 | 1.00 | 1.00 | 2.78 | 1.25 | 2.25 | 1.47 | 1.87 | 1.63 |
| Rgs2 | 1.58 | 1.82 | 1.51 | 1.01 | 0.84 | 1.15 | 1.37 | 1.76 | 1.44 | 1.03 | 1.31 | 1.15 |
| Rgs3 | 0.81 | 0.93 | 1.13 | 0.94 | 2.12 | 1.05 | 0.59 | 0.62 | 0.49 | 0.87 | 0.84 | 0.91 |
| Rgs7bp | 1.00 | 1.00 | 1.00 | 1.00 | 1.00 | 1.00 | 1.00 | 1.00 | 1.00 | 1.10 | 0.72 | 0.97 |
| Rgs8 | 1.00 | 1.00 | 1.00 | 1.00 | 1.00 | 1.00 | 1.00 | 1.00 | 1.00 | 1.00 | 1.00 | 1.00 |
| Rhbdd3 | 1.05 | 1.48 | 1.11 | 1.11 | 0.78 | 0.92 | 1.06 | 1.86 | 1.03 | 0.97 | 1.25 | 1.01 |
| Rhbg | 1.00 | 1.00 | 1.00 | 0.89 | 0.46 | 0.83 | 2.20 | 2.50 | 1.29 | 1.15 | 1.13 | 1.01 |
| Rhobtb3 | 2.05 | 1.33 | 1.43 | 1.15 | 1.00 | 1.08 | 0.93 | 1.00 | 1.09 | 0.94 | 0.66 | 1.06 |

Fig. 35- 243

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Rab3c | 1.04 | 1.15 | 0.97 | 1.00 | 1.00 | 1.00 | 1.00 | 1.00 | 1.00 | 1.00 | 7.77 | 1.00 |
| Rab40b | 0.63 | 0.63 | 1.64 | 5.22 | 6.10 | 5.30 | 1.00 | 1.00 | 1.00 | 0.98 | 3.06 | 1.00 |
| Rab4b | 1.14 | 1.20 | 1.07 | 0.87 | 2.09 | 0.93 | 0.92 | 0.74 | 0.95 | 1.30 | 1.71 | 1.15 |
| Rab6b | 0.88 | 0.92 | 0.87 | 0.72 | 1.00 | 0.66 | 1.00 | 1.00 | 1.00 | 0.32 | 8.41 | 0.30 |
| Rab7 | 1.00 | 1.01 | 0.84 | 1.26 | 0.09 | 0.88 | 0.79 | 1.00 | 0.82 | 1.04 | 0.72 | 1.01 |
| Rab7l1 | 0.91 | 1.05 | 0.87 | 0.70 | 0.98 | 0.67 | 1.00 | 1.23 | 0.68 | 0.92 | 0.99 | 0.92 |
| Rab9 | 0.90 | 0.88 | 0.94 | 1.84 | 6.30 | 1.44 | 0.93 | 0.40 | 0.84 | 1.13 | 1.02 | 0.99 |
| Rabac1 | 1.24 | 1.37 | 1.35 | 0.96 | 2.76 | 0.96 | 0.86 | 2.12 | 1.08 | 1.16 | 1.50 | 1.01 |
| Rabif | 0.95 | 0.86 | 1.05 | 0.89 | 0.53 | 0.90 | 0.91 | 1.74 | 0.95 | 1.02 | 0.89 | 0.96 |
| Rad9a | 0.85 | 0.91 | 0.96 | 0.74 | 2.26 | 0.92 | 0.80 | 2.06 | 0.81 | 0.85 | 0.85 | 0.88 |
| Rae1 | 0.91 | 0.97 | 0.94 | 1.08 | 3.09 | 1.35 | 0.97 | 2.30 | 0.95 | 0.96 | 1.18 | 0.96 |
| Raet1d | 2.22 | 3.18 | 2.14 | 1.12 | 1.00 | 1.25 | 1.00 | 1.00 | 1.00 | 1.00 | 1.04 | 1.00 |
| Rai2 | 1.10 | 1.58 | 1.55 | 0.55 | 0.83 | 0.76 | 1.27 | 1.79 | 1.11 | 1.32 | 1.36 | 1.28 |
| Ranbp1 | 0.85 | 0.62 | 0.80 | 1.21 | 2.78 | 1.09 | 0.78 | 2.04 | 0.92 | 0.94 | 1.35 | 0.88 |
| Rangrf | 1.02 | 1.36 | 1.27 | 0.92 | 5.09 | 0.76 | 0.94 | 4.84 | 0.87 | 0.76 | 1.32 | 0.78 |
| Rap1gap2 | 1.17 | 1.30 | 0.92 | 1.13 | 1.00 | 0.56 | 1.46 | 1.00 | 0.95 | 0.69 | 1.06 | 0.89 |
| Rarres2 | 0.84 | 1.14 | 1.13 | 1.15 | 1.24 | 0.76 | 0.68 | 0.41 | 1.18 | 1.00 | 1.17 | 1.20 |
| Rasa3 | 1.42 | 1.52 | 1.61 | 0.88 | 0.58 | 1.20 | 0.82 | 0.99 | 1.03 | 1.24 | 0.95 | 1.09 |
| Rasd1 | 2.41 | 5.79 | 2.26 | 0.70 | 0.60 | 1.46 | 0.93 | 0.24 | 1.01 | 1.70 | 1.75 | 1.32 |
| Rasd2 | 0.69 | 1.05 | 1.18 | 1.42 | 1.74 | 0.98 | 1.13 | 2.11 | 1.19 | 0.51 | 5.75 | 0.74 |
| Rasgrf1 | 1.00 | 1.00 | 1.00 | 1.00 | 1.00 | 1.14 | 1.00 | 1.00 | 1.30 | 1.00 | 5.59 | 1.00 |
| Rasip1 | 1.04 | 1.20 | 1.44 | 1.03 | 1.56 | 1.20 | 1.07 | 1.47 | 0.87 | 0.82 | 0.91 | 0.89 |
| Rasl10b | 2.81 | 3.21 | 2.81 | 2.58 | 1.11 | 2.65 | 0.87 | 1.00 | 0.71 | 1.00 | 9.58 | 1.00 |
| Rassf4 | 0.36 | 0.41 | 0.49 | 1.32 | 0.76 | 0.74 | 1.00 | 1.00 | 1.00 | 0.72 | 0.53 | 1.19 |
| Rbakdn | 1.00 | 1.00 | 1.00 | 2.03 | 1.66 | 1.00 | 0.94 | 2.01 | 1.05 | 1.01 | 1.17 | 1.21 |
| Rbfa | 1.37 | 1.60 | 1.67 | 1.04 | 3.48 | 1.32 | 1.35 | 2.23 | 1.44 | 1.25 | 1.39 | 1.12 |
| Rbfox1 | 1.00 | 1.00 | 1.00 | 1.00 | 1.00 | 1.00 | 1.00 | 1.00 | 1.00 | 1.00 | 8.07 | 1.00 |
| Rbfox3 | 1.00 | 1.00 | 1.00 | 1.53 | 1.00 | 1.33 | 1.00 | 1.00 | 1.00 | 1.57 | 9.82 | 1.07 |
| Rbks | 1.42 | 1.06 | 1.25 | 1.25 | 0.94 | 1.45 | 1.17 | 1.12 | 1.13 | 1.45 | 1.24 | 1.20 |
| Rbp1 | 1.19 | 1.49 | 2.64 | 1.27 | 2.26 | 1.33 | 0.72 | 2.04 | 0.88 | 0.78 | 1.11 | 0.63 |
| Rbp2 | 1.69 | 1.98 | 1.74 | 1.22 | 1.45 | 2.53 | 1.00 | 1.91 | 1.00 | 1.00 | 1.00 | 1.00 |
| Rbp7 | 0.91 | 1.32 | 1.13 | 0.94 | 3.28 | 1.34 | 0.63 | 1.33 | 1.71 | 1.00 | 1.00 | 1.00 |
| Rce1 | 0.79 | 0.93 | 1.00 | 0.92 | 2.39 | 1.06 | 1.02 | 1.44 | 1.14 | 1.26 | 1.20 | 0.92 |
| Rdh14 | 1.11 | 1.08 | 1.05 | 0.99 | 0.93 | 0.90 | 0.94 | 1.23 | 0.92 | 1.22 | 1.11 | 1.11 |
| Rdh5 | 1.17 | 1.19 | 1.10 | 0.99 | 0.74 | 0.96 | 1.00 | 1.00 | 1.00 | 1.20 | 0.91 | 0.95 |
| Rdm1 | 0.98 | 1.01 | 0.87 | 0.56 | 1.84 | 0.99 | 0.72 | 1.62 | 0.91 | 1.09 | 1.13 | 0.94 |
| Redrum | 1.00 | 1.00 | 1.00 | 1.00 | 1.00 | 1.00 | 1.00 | 1.00 | 1.00 | 3.86 | 1.49 | 1.27 |
| Reep4 | 1.02 | 1.09 | 0.96 | 3.59 | 3.29 | 2.11 | 0.92 | 0.64 | 0.89 | 1.03 | 0.91 | 0.96 |
| Reg1 | 21.36 | 2.38 | 5.17 | 1.00 | 1.00 | 1.00 | 1.00 | 1.00 | 0.99 | 2.18 | 11.58 | 0.71 |
| Reg2 | 1.60 | 1.01 | 27.42 | 1.00 | 1.00 | 1.00 | 1.00 | 1.00 | 1.00 | 1.00 | 4.28 | 1.00 |
| Reg3a | 1.00 | 1.00 | 1.00 | 1.00 | 1.00 | 1.00 | 1.00 | 1.00 | 1.00 | 1.00 | 1.00 | 1.00 |
| Reg3b | 2.55 | 1.00 | 4.22 | 1.00 | 1.00 | 1.00 | 1.00 | 1.00 | 1.00 | 1.00 | 1.33 | 1.00 |
| Reg3g | 1.94 | 0.68 | 0.50 | 1.00 | 1.00 | 1.00 | 1.00 | 1.00 | 1.00 | 1.00 | 1.00 | 1.00 |
| Relb | 1.13 | 1.15 | 1.08 | 1.04 | 1.94 | 0.95 | 0.80 | 1.22 | 1.00 | 0.90 | 1.06 | 0.78 |
| Rell2 | 1.00 | 1.00 | 1.00 | 1.00 | 1.00 | 1.00 | 0.70 | 1.00 | 1.22 | 1.65 | 5.09 | 1.27 |
| Ren1 | 1.00 | 1.00 | 1.00 | 1.26 | 0.55 | 0.85 | 1.29 | 2.24 | 0.71 | 1.00 | 1.00 | 1.00 |
| Renbp | 0.71 | 0.75 | 1.10 | 0.74 | 2.14 | 0.79 | 1.00 | 1.16 | 0.89 | 0.79 | 1.19 | 0.87 |
| Rerg | 1.29 | 0.86 | 0.98 | 2.07 | 1.00 | 1.42 | 1.26 | 9.09 | 1.10 | 1.00 | 1.04 | 1.00 |
| Rergl | 1.14 | 1.03 | 1.00 | 11.17 | 2.08 | 5.91 | 1.07 | 1.00 | 1.20 | 1.00 | 1.00 | 1.00 |
| Retn | 1.00 | 1.12 | 1.00 | 0.50 | 2.13 | 1.33 | 1.07 | 2.09 | 1.12 | 1.00 | 1.00 | 1.00 |
| Retnla | 2.07 | 1.17 | 3.53 | 0.38 | 1.19 | 0.49 | 1.00 | 1.66 | 1.00 | 1.00 | 0.71 | 1.01 |
| Retnlg | 1.53 | 0.73 | 1.34 | 0.36 | 1.00 | 0.43 | 1.00 | 1.00 | 1.00 | 3.87 | 2.94 | 2.61 |
| Retsat | 0.86 | 0.92 | 1.01 | 0.62 | 1.07 | 0.75 | 0.93 | 1.70 | 0.74 | 1.30 | 1.39 | 1.15 |
| Rfc2 | 0.76 | 0.92 | 1.13 | 0.99 | 2.05 | 1.18 | 0.95 | 2.26 | 0.94 | 1.08 | 1.33 | 0.80 |
| Rfc5 | 0.94 | 0.67 | 0.60 | 0.59 | 2.34 | 0.90 | 0.91 | 2.01 | 0.91 | 1.20 | 1.10 | 0.90 |
| Rgl2 | 1.18 | 1.58 | 1.22 | 1.06 | 1.93 | 1.14 | 1.09 | 3.42 | 1.22 | 1.07 | 1.06 | 1.08 |
| Rgs1 | 1.68 | 1.48 | 1.82 | 0.22 | 1.00 | 0.14 | 1.00 | 1.00 | 1.00 | 1.64 | 2.37 | 1.19 |
| Rgs2 | 1.18 | 1.43 | 1.81 | 1.09 | 2.60 | 1.74 | 1.40 | 0.99 | 1.11 | 1.05 | 1.22 | 1.04 |
| Rgs3 | 0.87 | 0.90 | 0.86 | 1.24 | 5.71 | 1.21 | 0.92 | 1.25 | 1.03 | 0.67 | 0.65 | 0.79 |
| Rgs7bp | 1.09 | 1.08 | 1.16 | 1.24 | 1.00 | 0.64 | 1.00 | 1.00 | 1.00 | 1.00 | 6.16 | 1.00 |
| Rgs8 | 1.00 | 1.00 | 1.00 | 1.00 | 1.00 | 1.00 | 1.00 | 1.00 | 1.00 | 1.00 | 7.04 | 1.00 |
| Rhbdd3 | 1.23 | 1.07 | 1.21 | 1.03 | 3.13 | 1.06 | 0.97 | 1.97 | 0.98 | 1.01 | 1.50 | 1.01 |
| Rhbg | 0.88 | 1.23 | 1.14 | 2.10 | 5.58 | 2.04 | 1.00 | 2.82 | 0.47 | 1.00 | 1.00 | 1.00 |
| Rhobtb3 | 0.76 | 0.69 | 0.96 | 1.04 | 1.00 | 1.27 | 0.87 | 1.15 | 1.18 | 0.73 | 0.89 | 0.82 |

Fig. 35- 244

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Rab3c | 1.00 | 1.00 | 1.00 | 1.04 | 1.07 | 1.01 | 1.00 | 1.00 | 1.00 | 1.00 | 1.00 | 1.00 |
| Rab40b | 1.00 | 1.00 | 1.00 | 0.98 | 0.32 | 1.12 | 1.13 | 1.19 | 1.07 | 1.00 | 1.00 | 1.00 |
| Rab4b | 1.18 | 1.21 | 0.63 | 1.06 | 1.44 | 1.07 | 1.43 | 1.86 | 1.05 | 2.25 | 1.69 | 1.33 |
| Rab6b | 1.00 | 1.00 | 1.00 | 1.07 | 1.05 | 1.02 | 0.80 | 1.00 | 0.41 | 1.00 | 1.00 | 1.00 |
| Rab7 | 0.65 | 0.87 | 1.63 | 0.87 | 1.00 | 0.92 | 0.76 | 0.03 | 0.94 | 0.17 | 1.03 | 1.19 |
| Rab7l1 | 1.08 | 0.86 | 0.87 | 1.05 | 1.53 | 0.49 | 0.75 | 2.35 | 0.82 | 2.62 | 1.48 | 1.20 |
| Rab9 | 1.12 | 0.91 | 0.94 | 1.04 | 1.52 | 1.10 | 1.07 | 0.72 | 1.05 | 0.94 | 1.16 | 1.19 |
| Rabac1 | 1.04 | 0.99 | 0.95 | 1.32 | 1.20 | 1.05 | 1.59 | 7.39 | 1.11 | 2.82 | 1.59 | 1.22 |
| Rabif | 1.46 | 0.95 | 0.81 | 1.09 | 6.40 | 1.06 | 0.81 | 0.62 | 0.85 | 1.04 | 0.99 | 1.08 |
| Rad9a | 1.00 | 1.00 | 1.00 | 1.06 | 1.11 | 1.07 | 1.21 | 7.28 | 0.88 | 1.83 | 0.96 | 1.23 |
| Rae1 | 1.64 | 1.02 | 1.24 | 0.98 | 0.84 | 1.03 | 1.19 | 8.83 | 1.03 | 2.61 | 1.01 | 1.01 |
| Raet1d | 3.15 | 2.41 | 1.00 | 1.00 | 1.00 | 1.00 | 1.00 | 1.00 | 1.00 | 1.00 | 1.38 | 1.49 |
| Rai2 | 1.08 | 0.94 | 0.87 | 1.08 | 1.00 | 1.19 | 1.23 | 0.72 | 1.47 | 1.00 | 1.00 | 1.00 |
| Ranbp1 | 1.79 | 1.32 | 0.84 | 1.13 | 0.73 | 1.06 | 1.09 | 6.94 | 0.81 | 1.77 | 0.76 | 0.81 |
| Rangrf | 0.58 | 0.96 | 2.58 | 1.10 | 1.02 | 1.40 | 1.19 | 32.22 | 0.76 | 4.91 | 0.79 | 0.52 |
| Rap1gap2 | 0.97 | 0.91 | 0.93 | 0.99 | 0.78 | 0.95 | 1.13 | 0.72 | 1.07 | 0.40 | 1.06 | 0.85 |
| Rarres2 | 0.33 | 1.60 | 0.86 | 0.83 | 5.35 | 0.86 | 1.27 | 0.90 | 1.24 | 1.00 | 1.00 | 1.00 |
| Rasa3 | 1.00 | 1.00 | 0.83 | 0.78 | 0.41 | 0.85 | 1.05 | 0.53 | 1.21 | 0.73 | 1.04 | 1.14 |
| Rasd1 | 1.45 | 1.62 | 1.00 | 1.82 | 1.71 | 1.45 | 2.29 | 1.63 | 2.79 | 1.00 | 1.00 | 1.00 |
| Rasd2 | 1.00 | 1.00 | 1.00 | 1.12 | 1.11 | 1.06 | 0.95 | 2.49 | 1.12 | 1.00 | 1.00 | 1.00 |
| Rasgrf1 | 1.00 | 1.00 | 1.00 | 1.00 | 1.80 | 1.08 | 1.00 | 1.00 | 1.00 | 1.00 | 1.00 | 1.00 |
| Rasip1 | 1.08 | 1.00 | 0.69 | 1.02 | 1.46 | 1.15 | 1.20 | 6.49 | 1.38 | 1.00 | 1.00 | 1.00 |
| Rasl10b | 1.00 | 1.00 | 1.00 | 1.15 | 1.00 | 1.02 | 1.00 | 1.00 | 1.00 | 1.00 | 1.00 | 1.00 |
| Rassf4 | 1.00 | 1.00 | 1.00 | 1.01 | 1.18 | 1.10 | 1.03 | 0.55 | 1.17 | 0.69 | 0.89 | 0.96 |
| Rbakdn | 1.00 | 1.00 | 1.00 | 1.00 | 1.00 | 1.00 | 8.82 | 1.00 | 1.00 | 1.00 | 1.09 | 1.00 |
| Rbfa | 1.70 | 1.42 | 1.16 | 1.23 | 0.99 | 1.19 | 1.58 | 8.72 | 1.41 | 4.13 | 1.87 | 1.67 |
| Rbfox1 | 1.00 | 1.00 | 1.00 | 1.00 | 1.09 | 0.97 | 1.69 | 0.81 | 2.53 | 1.00 | 1.00 | 1.00 |
| Rbfox3 | 1.00 | 1.00 | 1.00 | 1.09 | 1.02 | 1.05 | 1.00 | 1.00 | 1.00 | 1.00 | 1.00 | 1.00 |
| Rbks | 0.93 | 1.31 | 1.00 | 1.00 | 1.00 | 1.09 | 1.59 | 5.01 | 0.59 | 1.71 | 0.95 | 1.08 |
| Rbp1 | 1.00 | 1.00 | 1.00 | 1.11 | 0.64 | 0.87 | 1.28 | 10.63 | 0.67 | 1.95 | 1.00 | 1.00 |
| Rbp2 | 18.35 | 10.99 | 2.19 | 1.00 | 3.69 | 1.00 | 1.00 | 1.00 | 1.02 | 1.00 | 1.00 | 1.00 |
| Rbp7 | 0.80 | 0.77 | 1.28 | 1.00 | 1.00 | 1.00 | 7.03 | 49.67 | 3.63 | 1.00 | 1.00 | 1.00 |
| Rce1 | 1.17 | 0.79 | 0.70 | 0.92 | 0.98 | 1.04 | 1.05 | 4.96 | 0.86 | 1.80 | 1.19 | 1.04 |
| Rdh14 | 1.38 | 1.32 | 0.81 | 1.12 | 8.59 | 1.06 | 1.24 | 0.46 | 1.47 | 0.60 | 1.22 | 1.38 |
| Rdh5 | 1.00 | 1.00 | 1.00 | 1.04 | 1.35 | 0.94 | 1.84 | 5.59 | 1.81 | 1.94 | 1.65 | 1.62 |
| Rdm1 | 0.45 | 0.50 | 0.80 | 1.30 | 5.71 | 0.76 | 1.29 | 4.70 | 0.82 | 2.52 | 1.08 | 1.08 |
| Redrum | 1.00 | 1.00 | 1.00 | 1.00 | 1.00 | 1.00 | 1.00 | 1.00 | 1.00 | 8.19 | 15.60 | 18.75 |
| Reep4 | 1.42 | 1.00 | 0.68 | 0.90 | 2.71 | 1.46 | 1.47 | 1.18 | 1.15 | 0.95 | 1.03 | 0.97 |
| Reg1 | 1.61 | 1.86 | 1.75 | 1.00 | 1.00 | 1.00 | 1.00 | 1.00 | 1.00 | 1.00 | 1.00 | 0.87 |
| Reg2 | 45.50 | 547.92 | 39.32 | 1.00 | 1.00 | 1.00 | 1.00 | 1.00 | 1.00 | 1.00 | 0.46 | 1.00 |
| Reg3a | 1.90 | 108.20 | 5.05 | 1.00 | 1.00 | 1.00 | 1.00 | 1.00 | 1.00 | 1.00 | 1.00 | 1.00 |
| Reg3b | 4.18 | 139.20 | 6.72 | 1.00 | 1.00 | 1.00 | 1.00 | 1.00 | 1.00 | 1.00 | 1.00 | 1.00 |
| Reg3g | 1.11 | 11.14 | 5.50 | 1.00 | 1.00 | 1.00 | 1.00 | 1.00 | 1.00 | 1.00 | 1.00 | 1.00 |
| Relb | 1.19 | 1.00 | 0.94 | 1.20 | 2.88 | 0.93 | 0.83 | 2.17 | 0.83 | 1.80 | 1.35 | 1.23 |
| Rell2 | 1.00 | 1.00 | 1.00 | 1.11 | 1.66 | 1.10 | 1.00 | 0.94 | 1.26 | 1.00 | 1.00 | 1.00 |
| Ren1 | 1.00 | 1.00 | 1.00 | 1.00 | 1.00 | 1.00 | 1.00 | 1.00 | 1.00 | 3.17 | 1.50 | 1.81 |
| Renbp | 1.00 | 1.00 | 1.00 | 0.84 | 0.36 | 1.20 | 1.05 | 8.46 | 1.35 | 1.13 | 0.79 | 1.29 |
| Rerg | 1.00 | 1.00 | 1.00 | 1.29 | 0.46 | 0.98 | 1.04 | 0.21 | 0.88 | 1.00 | 1.00 | 1.00 |
| Rergl | 1.00 | 1.00 | 1.00 | 1.00 | 1.00 | 1.00 | 1.10 | 1.00 | 1.00 | 1.00 | 1.00 | 1.00 |
| Retn | 1.00 | 1.00 | 1.00 | 1.00 | 4.87 | 1.00 | 5.21 | 76.28 | 3.58 | 3.21 | 1.00 | 1.00 |
| Retnla | 0.43 | 0.55 | 1.02 | 1.00 | 1.00 | 1.00 | 0.93 | 20.02 | 2.18 | 2.58 | 1.00 | 1.00 |
| Retnlg | 1.00 | 1.00 | 1.00 | 1.00 | 0.56 | 1.00 | 1.00 | 1.11 | 1.00 | 4.51 | 2.29 | 1.71 |
| Retsat | 0.46 | 0.46 | 0.65 | 0.81 | 1.02 | 0.90 | 1.08 | 6.08 | 1.22 | 1.84 | 0.89 | 1.19 |
| Rfc2 | 0.77 | 0.58 | 1.18 | 0.95 | 0.95 | 0.98 | 1.26 | 12.14 | 0.82 | 3.10 | 0.98 | 1.06 |
| Rfc5 | 1.00 | 0.79 | 0.79 | 1.12 | 1.30 | 1.14 | 0.78 | 5.28 | 0.85 | 1.43 | 0.88 | 0.92 |
| Rgl2 | 1.14 | 1.04 | 1.20 | 1.14 | 0.97 | 1.14 | 1.33 | 6.41 | 1.04 | 3.09 | 1.65 | 1.40 |
| Rgs1 | 1.00 | 1.00 | 1.00 | 1.00 | 1.00 | 1.00 | 2.34 | 1.00 | 1.43 | 1.00 | 6.02 | 1.37 |
| Rgs2 | 1.45 | 3.44 | 1.60 | 1.05 | 0.63 | 0.95 | 1.03 | 1.60 | 0.88 | 1.16 | 1.34 | 1.17 |
| Rgs3 | 1.00 | 1.00 | 1.00 | 0.90 | 1.16 | 0.89 | 1.01 | 1.45 | 0.69 | 1.12 | 0.93 | 1.04 |
| Rgs7bp | 1.00 | 1.00 | 1.00 | 0.94 | 1.57 | 0.95 | 1.14 | 1.00 | 0.93 | 1.00 | 1.00 | 1.00 |
| Rgs8 | 1.00 | 1.00 | 1.00 | 1.02 | 1.24 | 0.98 | 1.00 | 1.00 | 1.00 | 1.00 | 1.00 | 1.00 |
| Rhbdd3 | 0.90 | 1.03 | 0.95 | 1.22 | 1.05 | 1.11 | 1.39 | 5.91 | 1.15 | 1.56 | 0.89 | 0.86 |
| Rhbg | 1.00 | 1.00 | 1.00 | 1.00 | 1.00 | 1.00 | 0.78 | 5.92 | 0.40 | 1.00 | 1.00 | 1.00 |
| Rhobtb3 | 0.80 | 1.10 | 1.00 | 0.84 | 1.00 | 0.87 | 0.80 | 0.44 | 1.48 | 1.00 | 0.60 | 0.75 |

Fig. 35- 245

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Rhou | 1.42 | 0.99 | 1.55 | 4.02 | 13.23 | 1.97 | 2.31 | 2.14 | 1.48 | 2.39 | 3.55 | 1.26 |
| Riiad1 | 1.00 | 0.32 | 1.00 | 1.00 | 1.00 | 1.00 | 1.00 | 1.00 | 1.00 | 4.68 | 5.97 | 0.76 |
| Rit2 | 1.00 | 1.00 | 1.00 | 1.00 | 0.24 | 1.00 | 1.00 | 1.00 | 1.00 | 1.00 | 1.00 | 1.00 |
| Rmnd1 | 1.00 | 1.00 | 1.00 | 1.95 | 1.08 | 6.59 | 1.96 | 2.24 | 1.00 | 1.00 | 1.00 | 1.00 |
| Rmrp | 1.35 | 0.18 | 1.00 | 1.00 | 2.98 | 1.78 | 1.00 | 2.03 | 0.86 | 5.45 | 5.15 | 1.00 |
| Rn4.5s | 2.89 | 0.71 | 1.45 | 0.17 | 14.67 | 1.31 | 7.67 | 0.37 | 0.49 | 1.75 | 3.65 | 0.88 |
| Rn45s | 1.33 | 0.19 | 0.59 | 1.12 | 3.91 | 1.30 | 1.17 | 1.65 | 1.23 | 4.19 | 2.50 | 0.90 |
| Rnase1 | 1.00 | 1.00 | 1.00 | 1.00 | 1.00 | 1.00 | 1.19 | 0.85 | 1.16 | 1.00 | 1.00 | 2.79 |
| Rnase10 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.00 | 1.00 | 1.00 | 1.00 |
| Rnase2a | 2.39 | 1.02 | 0.89 | 1.11 | 2.83 | 2.12 | 1.00 | 1.00 | 1.22 | 3.50 | 1.28 | 3.24 |
| Rnaseh1 | 0.86 | 0.79 | 1.11 | 0.58 | 1.65 | 1.04 | 1.08 | 1.14 | 1.00 | 0.58 | 0.80 | 0.93 |
| Rnaseh2a | 0.91 | 0.56 | 1.94 | 0.35 | 6.10 | 0.99 | 1.10 | 0.80 | 0.94 | 2.36 | 3.43 | 0.80 |
| Rnaseh2b | 0.87 | 0.67 | 1.00 | 0.85 | 3.95 | 0.82 | 0.93 | 0.55 | 0.78 | 2.26 | 1.76 | 0.94 |
| Rnasek | 1.26 | 0.76 | 0.81 | 0.50 | 3.97 | 0.96 | 1.04 | 0.87 | 0.82 | 1.47 | 1.98 | 0.98 |
| Rnaset2a | 1.10 | 0.94 | 0.88 | 0.27 | 3.44 | 0.83 | 0.98 | 1.32 | 1.21 | 1.26 | 1.64 | 1.05 |
| Rnaset2b | 0.92 | 0.63 | 0.88 | 0.30 | 6.55 | 0.73 | 0.99 | 0.59 | 0.69 | 2.00 | 3.90 | 0.89 |
| Rnf112 | 1.00 | 1.00 | 1.00 | 1.00 | 0.13 | 1.00 | 1.00 | 1.00 | 1.00 | 1.00 | 1.00 | 1.00 |
| Rnf125 | 0.99 | 1.00 | 1.00 | 25.64 | 6.34 | 4.37 | 1.58 | 3.56 | 1.15 | 1.00 | 2.13 | 1.24 |
| Rnf185 | 0.98 | 1.14 | 1.02 | 1.16 | 1.43 | 1.11 | 1.09 | 1.05 | 0.92 | 1.24 | 1.21 | 1.15 |
| Rnf208 | 1.00 | 1.00 | 1.00 | 1.00 | 0.14 | 1.00 | 1.00 | 0.97 | 1.09 | 1.53 | 2.55 | 1.05 |
| Rnf25 | 1.13 | 0.65 | 0.79 | 0.64 | 5.44 | 1.06 | 1.09 | 0.84 | 0.90 | 2.21 | 2.74 | 0.98 |
| Rnu11 | 1.00 | 1.00 | 1.00 | 1.00 | 1.00 | 49.12 | 1.00 | 1.00 | 1.00 | 1.00 | 1.00 | 1.00 |
| Rogdi | 1.34 | 0.75 | 0.73 | 0.84 | 11.22 | 1.50 | 1.26 | 1.04 | 0.89 | 2.08 | 3.20 | 0.81 |
| Rom1 | 1.43 | 0.83 | 1.04 | 0.30 | 2.67 | 0.78 | 1.21 | 1.10 | 0.90 | 3.03 | 2.33 | 1.12 |
| Romo1 | 1.02 | 0.55 | 0.91 | 0.11 | 9.30 | 0.93 | 0.90 | 0.74 | 0.85 | 1.94 | 3.47 | 0.87 |
| Ropn1l | 1.00 | 1.00 | 1.00 | 0.72 | 7.00 | 1.03 | 1.00 | 1.00 | 1.00 | 2.86 | 3.38 | 1.36 |
| Rpa2 | 0.79 | 0.65 | 0.78 | 1.98 | 7.54 | 1.49 | 0.89 | 0.69 | 0.92 | 1.35 | 2.02 | 0.84 |
| Rpap3 | 0.91 | 0.83 | 0.80 | 1.08 | 6.98 | 1.19 | 1.11 | 1.17 | 0.96 | 1.52 | 3.46 | 0.81 |
| Rpf2 | 0.90 | 0.85 | 1.00 | 1.32 | 5.33 | 1.16 | 0.56 | 0.83 | 1.08 | 1.78 | 1.99 | 0.97 |
| Rpgrip1 | 1.00 | 0.45 | 1.00 | 1.00 | 1.46 | 1.00 | 1.00 | 1.00 | 1.00 | 3.00 | 2.32 | 1.00 |
| Rph3a | 1.00 | 1.00 | 1.00 | 1.00 | 0.19 | 1.00 | 1.00 | 1.00 | 1.00 | 1.00 | 1.00 | 1.00 |
| Rpl10 | 1.42 | 0.56 | 0.85 | 0.38 | 6.48 | 1.24 | 0.75 | 0.88 | 0.85 | 1.70 | 2.82 | 0.95 |
| Rpl10a | 1.31 | 0.67 | 0.98 | 0.33 | 10.46 | 1.11 | 0.97 | 0.88 | 0.94 | 2.17 | 3.20 | 0.85 |
| Rpl13 | 1.55 | 0.41 | 0.96 | 0.39 | 18.77 | 1.04 | 0.89 | 0.82 | 0.87 | 4.56 | 6.20 | 0.91 |
| Rpl13a | 1.35 | 0.64 | 1.10 | 0.28 | 6.31 | 1.39 | 0.96 | 0.72 | 1.10 | 2.62 | 2.73 | 0.93 |
| Rpl14 | 1.49 | 0.53 | 1.03 | 0.65 | 16.05 | 1.10 | 0.97 | 0.77 | 0.89 | 3.04 | 5.20 | 0.95 |
| Rpl17 | 1.68 | 0.73 | 1.09 | 0.43 | 6.44 | 1.12 | 0.77 | 0.83 | 0.85 | 1.31 | 2.37 | 0.96 |
| Rpl18 | 1.58 | 0.62 | 0.91 | 0.56 | 10.86 | 1.14 | 0.74 | 0.62 | 0.95 | 1.80 | 3.44 | 1.05 |
| Rpl18a | 1.32 | 0.67 | 1.09 | 0.27 | 5.58 | 1.15 | 0.94 | 0.73 | 0.87 | 2.11 | 2.17 | 0.87 |
| Rpl19 | 1.67 | 0.50 | 0.94 | 0.20 | 10.70 | 1.13 | 1.08 | 0.83 | 0.97 | 2.62 | 4.35 | 0.86 |
| Rpl22 | 1.08 | 0.83 | 0.91 | 0.61 | 3.68 | 1.30 | 0.86 | 0.89 | 0.90 | 1.62 | 1.77 | 1.00 |
| Rpl22l1 | 1.20 | 0.88 | 1.12 | 0.87 | 11.99 | 1.72 | 0.77 | 0.92 | 1.12 | 1.55 | 3.21 | 0.80 |
| Rpl23 | 1.33 | 0.64 | 0.96 | 0.48 | 5.37 | 1.27 | 0.89 | 0.61 | 1.09 | 1.88 | 2.55 | 0.94 |
| Rpl24 | 1.17 | 0.54 | 1.04 | 0.30 | 6.72 | 1.02 | 0.99 | 0.59 | 0.91 | 1.65 | 2.91 | 1.01 |
| Rpl27a | 1.63 | 0.78 | 1.14 | 0.47 | 6.18 | 1.19 | 0.94 | 0.83 | 0.87 | 1.64 | 2.33 | 0.92 |
| Rpl28 | 1.53 | 0.55 | 1.50 | 0.17 | 19.40 | 1.50 | 0.87 | 1.14 | 0.89 | 3.14 | 4.76 | 0.90 |
| Rpl31 | 1.03 | 0.61 | 1.01 | 0.19 | 5.17 | 0.88 | 1.10 | 1.02 | 0.85 | 1.58 | 2.73 | 0.93 |
| Rpl31-ps12 | 1.25 | 0.77 | 0.95 | 0.39 | 6.63 | 1.17 | 1.07 | 0.80 | 0.91 | 1.16 | 2.64 | 0.85 |
| Rpl32 | 1.40 | 0.66 | 1.10 | 0.25 | 14.74 | 1.18 | 0.88 | 0.83 | 0.95 | 3.73 | 4.31 | 0.92 |
| Rpl35 | 1.29 | 0.47 | 0.87 | 0.30 | 13.49 | 0.89 | 0.87 | 0.62 | 0.87 | 2.82 | 4.43 | 0.96 |
| Rpl35a | 1.46 | 0.70 | 1.01 | 0.25 | 5.69 | 1.60 | 1.43 | 0.95 | 0.93 | 1.22 | 1.64 | 0.85 |
| Rpl36 | 1.50 | 0.41 | 0.87 | 0.11 | 16.51 | 0.95 | 0.86 | 0.54 | 0.63 | 3.95 | 6.41 | 0.79 |
| Rpl36a | 1.32 | 0.39 | 0.95 | 0.36 | 18.53 | 0.88 | 1.62 | 1.70 | 1.03 | 4.28 | 7.27 | 1.00 |
| Rpl36al | 1.30 | 0.71 | 0.97 | 0.56 | 8.42 | 1.11 | 1.02 | 0.82 | 0.88 | 1.75 | 3.40 | 1.03 |
| Rpl37a | 1.93 | 0.59 | 1.35 | 0.33 | 15.44 | 0.63 | 0.78 | 1.06 | 0.60 | 1.97 | 4.01 | 0.69 |
| Rpl38 | 1.15 | 0.38 | 1.23 | 0.16 | 10.08 | 1.41 | 0.57 | 0.87 | 0.73 | 3.12 | 3.53 | 0.68 |
| Rpl39 | 1.29 | 0.65 | 0.78 | 0.62 | 8.40 | 1.21 | 0.91 | 0.83 | 0.84 | 1.94 | 3.04 | 0.75 |
| Rpl3l | 1.07 | 0.64 | 0.83 | 1.38 | 1.62 | 1.13 | 0.98 | 0.90 | 0.84 | 5.46 | 1.64 | 1.00 |
| Rpl4 | 1.35 | 0.85 | 0.93 | 1.14 | 5.42 | 1.16 | 0.83 | 0.84 | 0.90 | 0.92 | 1.71 | 0.92 |
| Rpl41 | 1.45 | 0.58 | 0.92 | 0.29 | 9.49 | 1.05 | 0.94 | 0.76 | 0.82 | 2.23 | 3.73 | 0.94 |
| Rpl8 | 1.30 | 0.72 | 0.99 | 0.36 | 7.31 | 1.05 | 0.98 | 0.85 | 0.91 | 2.20 | 2.86 | 1.01 |
| Rplp0 | 1.23 | 0.61 | 0.87 | 0.35 | 6.18 | 1.23 | 0.94 | 0.84 | 0.90 | 3.37 | 3.45 | 1.05 |
| Rplp1 | 2.35 | 0.97 | 1.60 | 0.36 | 18.74 | 1.43 | 1.58 | 1.26 | 1.30 | 5.34 | 7.30 | 1.36 |

Fig. 35-246

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Rhou | 2.91 | 2.78 | 2.52 | 1.25 | 1.06 | 1.62 | 1.89 | 1.86 | 1.57 | 1.30 | 1.68 | 1.15 |
| Riiad1 | 1.00 | 1.00 | 1.00 | 1.00 | 1.00 | 1.00 | 1.00 | 1.00 | 1.00 | 1.00 | 1.00 | 1.00 |
| Rit2 | 1.00 | 1.00 | 1.00 | 1.00 | 1.00 | 1.00 | 1.00 | 1.00 | 1.00 | 1.41 | 1.10 | 0.75 |
| Rmnd1 | 1.00 | 0.90 | 1.00 | 1.62 | 1.27 | 1.84 | 1.00 | 0.59 | 1.32 | 0.46 | 1.00 | 1.77 |
| Rmrp | 2.92 | 4.78 | 0.46 | 1.00 | 0.93 | 1.14 | 0.65 | 6.54 | 1.00 | 1.00 | 2.11 | 1.00 |
| Rn4.5s | 1.79 | 2.53 | 0.81 | 0.80 | 0.43 | 1.26 | 1.30 | 1.88 | 1.27 | 2.05 | 2.55 | 1.27 |
| Rn45s | 1.30 | 1.51 | 1.19 | 0.53 | 0.93 | 2.41 | 0.70 | 14.81 | 1.36 | 1.89 | 1.88 | 1.17 |
| Rnase1 | 1.25 | 0.87 | 1.03 | 1.80 | 2.09 | 1.59 | 1.00 | 1.43 | 0.69 | 0.53 | 2.95 | 23.95 |
| Rnase10 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.94 | 1.58 | 1.00 | 0.34 | 1.00 | 1.00 | 1.00 | 1.00 | 1.00 | 1.00 | 1.00 |
| Rnase2a | 11.72 | 3.85 | 2.46 | 1.00 | 1.00 | 1.00 | 2.24 | 1.00 | 1.00 | 1.16 | 1.08 | 0.74 |
| Rnaseh1 | 0.98 | 1.18 | 0.86 | 1.16 | 5.19 | 1.25 | 0.89 | 0.46 | 0.82 | 1.33 | 1.22 | 0.91 |
| Rnaseh2a | 1.16 | 1.44 | 1.14 | 0.80 | 0.48 | 0.93 | 1.17 | 1.37 | 0.78 | 0.96 | 1.39 | 1.13 |
| Rnaseh2b | 0.82 | 0.82 | 0.70 | 0.80 | 0.62 | 0.83 | 1.00 | 1.54 | 0.79 | 0.86 | 1.30 | 0.78 |
| Rnasek | 1.09 | 1.45 | 0.99 | 0.87 | 0.78 | 0.91 | 1.03 | 0.98 | 0.82 | 1.16 | 1.49 | 1.21 |
| Rnaset2a | 1.03 | 1.62 | 1.27 | 0.82 | 109.68 | 0.95 | 0.87 | 0.67 | 0.97 | 1.21 | 1.44 | 0.82 |
| Rnaset2b | 1.38 | 1.73 | 0.89 | 0.74 | 0.53 | 0.99 | 0.60 | 1.15 | 0.64 | 1.05 | 1.52 | 1.19 |
| Rnf112 | 1.00 | 1.00 | 1.00 | 1.00 | 1.00 | 1.00 | 1.00 | 1.00 | 1.00 | 1.00 | 1.00 | 1.00 |
| Rnf125 | 0.54 | 0.41 | 0.79 | 1.19 | 1.00 | 1.00 | 2.22 | 1.46 | 1.77 | 1.44 | 1.00 | 1.47 |
| Rnf185 | 1.04 | 1.12 | 1.05 | 1.06 | 0.94 | 0.94 | 0.98 | 0.98 | 0.86 | 1.00 | 1.03 | 1.08 |
| Rnf208 | 1.29 | 1.37 | 0.83 | 0.70 | 0.49 | 0.81 | 1.00 | 1.00 | 1.00 | 1.47 | 1.17 | 1.21 |
| Rnf25 | 1.30 | 1.57 | 1.02 | 1.17 | 0.80 | 0.98 | 0.87 | 1.69 | 0.86 | 1.11 | 1.52 | 1.16 |
| Rnu11 | 1.00 | 1.00 | 1.00 | 1.00 | 1.00 | 1.00 | 1.00 | 1.00 | 1.00 | 1.00 | 1.00 | 1.00 |
| Rogdi | 1.25 | 1.50 | 1.03 | 0.82 | 0.55 | 0.80 | 2.31 | 2.40 | 1.41 | 1.14 | 1.61 | 0.82 |
| Rom1 | 1.18 | 1.37 | 1.03 | 1.21 | 0.70 | 0.88 | 0.74 | 2.31 | 1.11 | 1.14 | 1.41 | 1.10 |
| Romo1 | 1.24 | 2.59 | 0.86 | 0.74 | 0.58 | 1.00 | 0.93 | 1.30 | 0.84 | 0.89 | 2.07 | 1.03 |
| Ropn1l | 1.00 | 1.00 | 1.00 | 0.85 | 0.32 | 0.59 | 0.42 | 1.13 | 0.44 | 1.00 | 1.00 | 1.00 |
| Rpa2 | 0.85 | 0.98 | 0.58 | 0.67 | 0.78 | 0.72 | 0.79 | 1.38 | 1.18 | 0.79 | 1.41 | 1.04 |
| Rpap3 | 0.96 | 1.10 | 0.94 | 1.13 | 1.23 | 1.13 | 2.26 | 2.84 | 1.35 | 0.72 | 1.76 | 0.75 |
| Rpf2 | 1.04 | 1.25 | 0.69 | 0.92 | 0.78 | 1.02 | 1.14 | 1.40 | 0.84 | 1.36 | 1.50 | 0.74 |
| Rpgrip1 | 1.07 | 1.00 | 1.00 | 1.00 | 1.45 | 1.00 | 1.00 | 3.52 | 1.00 | 1.00 | 1.00 | 1.00 |
| Rph3a | 1.00 | 1.00 | 1.00 | 1.00 | 1.00 | 1.00 | 1.00 | 1.00 | 1.00 | 1.00 | 1.00 | 1.00 |
| Rpl10 | 1.53 | 1.75 | 1.23 | 0.73 | 0.78 | 0.86 | 1.23 | 1.38 | 1.14 | 0.99 | 1.70 | 1.14 |
| Rpl10a | 1.30 | 1.62 | 1.05 | 0.85 | 0.66 | 0.88 | 1.17 | 1.99 | 1.37 | 0.96 | 1.97 | 1.06 |
| Rpl13 | 1.35 | 1.96 | 1.07 | 0.77 | 0.41 | 0.77 | 0.99 | 3.97 | 0.95 | 0.89 | 1.87 | 1.19 |
| Rpl13a | 1.15 | 1.43 | 1.01 | 1.03 | 0.48 | 0.99 | 0.95 | 2.55 | 1.04 | 1.09 | 1.62 | 1.03 |
| Rpl14 | 1.26 | 1.80 | 0.98 | 0.83 | 0.50 | 0.91 | 0.95 | 2.52 | 1.01 | 0.92 | 1.79 | 1.06 |
| Rpl17 | 1.40 | 1.67 | 1.02 | 1.01 | 0.73 | 0.71 | 1.51 | 1.21 | 1.11 | 0.83 | 1.75 | 1.03 |
| Rpl18 | 1.39 | 2.12 | 1.00 | 0.68 | 0.72 | 0.71 | 1.07 | 1.39 | 1.25 | 1.07 | 1.91 | 1.22 |
| Rpl18a | 1.38 | 1.93 | 1.19 | 0.82 | 0.52 | 0.85 | 1.09 | 2.27 | 1.22 | 1.03 | 1.65 | 1.19 |
| Rpl19 | 1.21 | 1.79 | 1.07 | 0.76 | 0.60 | 0.93 | 0.83 | 2.25 | 1.13 | 0.90 | 1.96 | 1.15 |
| Rpl22 | 1.34 | 1.42 | 1.18 | 0.85 | 0.67 | 0.99 | 0.90 | 1.55 | 1.11 | 0.92 | 1.24 | 1.09 |
| Rpl22l1 | 1.45 | 1.77 | 1.05 | 1.14 | 0.77 | 0.85 | 1.04 | 2.03 | 1.03 | 1.17 | 2.15 | 1.02 |
| Rpl23 | 1.46 | 1.62 | 1.13 | 0.80 | 0.65 | 0.89 | 1.10 | 1.66 | 1.24 | 1.03 | 1.66 | 1.14 |
| Rpl24 | 1.46 | 1.93 | 1.04 | 0.73 | 0.55 | 0.77 | 0.92 | 1.58 | 0.81 | 0.93 | 2.30 | 1.03 |
| Rpl27a | 1.43 | 1.64 | 1.15 | 0.94 | 0.74 | 0.81 | 1.20 | 1.55 | 1.18 | 1.10 | 1.70 | 1.00 |
| Rpl28 | 1.39 | 2.29 | 1.23 | 0.70 | 0.44 | 0.77 | 1.83 | 3.50 | 1.17 | 1.15 | 2.17 | 1.21 |
| Rpl31 | 1.12 | 1.40 | 1.14 | 0.73 | 0.83 | 1.13 | 0.75 | 1.61 | 1.03 | 1.16 | 1.75 | 1.07 |
| Rpl31-ps12 | 1.27 | 1.82 | 0.92 | 0.89 | 0.97 | 0.73 | 1.00 | 0.86 | 0.94 | 1.05 | 1.93 | 1.01 |
| Rpl32 | 1.39 | 1.97 | 1.12 | 0.81 | 0.74 | 0.79 | 0.89 | 3.06 | 0.99 | 0.98 | 1.98 | 1.13 |
| Rpl35 | 1.40 | 1.94 | 0.97 | 0.93 | 0.57 | 0.74 | 1.41 | 2.52 | 1.03 | 1.02 | 1.79 | 1.07 |
| Rpl35a | 1.65 | 1.86 | 0.92 | 0.75 | 1.10 | 0.81 | 0.76 | 0.85 | 1.24 | 1.31 | 1.83 | 1.28 |
| Rpl36 | 1.25 | 2.01 | 0.91 | 0.42 | 0.38 | 0.95 | 1.67 | 3.02 | 1.14 | 0.83 | 1.87 | 0.82 |
| Rpl36a | 1.62 | 1.20 | 0.75 | 0.22 | 0.43 | 0.70 | 1.68 | 3.49 | 1.13 | 0.97 | 2.47 | 1.12 |
| Rpl36al | 1.21 | 1.30 | 0.90 | 1.03 | 0.71 | 0.84 | 0.97 | 1.28 | 0.87 | 1.00 | 1.90 | 1.16 |
| Rpl37a | 0.97 | 1.30 | 0.89 | 0.73 | 0.66 | 0.87 | 1.11 | 2.00 | 1.24 | 0.82 | 1.57 | 1.23 |
| Rpl38 | 1.89 | 2.06 | 1.06 | 0.43 | 0.41 | 0.68 | 1.02 | 2.92 | 0.82 | 0.73 | 2.06 | 0.98 |
| Rpl39 | 1.36 | 1.98 | 1.05 | 0.64 | 0.64 | 0.83 | 1.03 | 1.87 | 1.07 | 0.95 | 1.94 | 1.15 |
| Rpl3l | 1.00 | 1.00 | 1.00 | 1.04 | 3.87 | 1.48 | 1.00 | 1.00 | 1.00 | 1.00 | 1.00 | 1.00 |
| Rpl4 | 1.28 | 1.47 | 1.07 | 0.84 | 1.00 | 0.86 | 1.02 | 0.84 | 1.14 | 0.96 | 1.59 | 1.07 |
| Rpl41 | 1.22 | 1.85 | 1.01 | 0.91 | 0.70 | 0.86 | 1.08 | 1.68 | 1.10 | 1.04 | 1.99 | 1.15 |
| Rpl8 | 1.13 | 1.50 | 0.96 | 0.90 | 0.61 | 0.97 | 1.05 | 2.15 | 1.08 | 1.02 | 1.65 | 1.11 |
| Rplp0 | 1.27 | 1.67 | 1.14 | 0.86 | 0.54 | 0.99 | 1.25 | 2.96 | 1.35 | 1.09 | 1.56 | 1.15 |
| Rplp1 | 1.70 | 2.27 | 1.34 | 1.30 | 0.90 | 1.54 | 1.32 | 4.43 | 1.45 | 1.39 | 2.39 | 1.48 |

Fig. 35- 247

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Rhou | 0.91 | 0.96 | 0.84 | 1.41 | 5.97 | 1.92 | 1.04 | 1.32 | 1.00 | 1.80 | 3.58 | 1.15 |
| Riiad1 | 1.00 | 1.00 | 1.00 | 1.00 | 1.00 | 1.00 | 0.99 | 3.26 | 0.87 | 1.00 | 1.00 | 1.00 |
| Rit2 | 1.00 | 1.00 | 1.00 | 1.00 | 1.00 | 1.00 | 1.04 | 1.00 | 1.00 | 1.00 | 6.17 | 1.00 |
| Rmnd1 | 1.00 | 1.00 | 1.00 | 1.00 | 1.00 | 1.00 | 2.16 | 3.37 | 2.09 | 1.00 | 1.00 | 1.71 |
| Rmrp | 1.00 | 1.00 | 1.00 | 1.94 | 0.07 | 2.41 | 0.25 | 5.04 | 1.00 | 1.09 | 0.69 | 0.19 |
| Rn4.5s | 0.76 | 0.48 | 1.39 | 1.05 | 1.71 | 1.26 | 1.44 | 3.63 | 1.05 | 0.44 | 1.43 | 1.04 |
| Rn45s | 0.75 | 1.55 | 1.34 | 1.25 | 0.08 | 1.18 | 0.65 | 5.82 | 1.37 | 0.65 | 0.51 | 0.74 |
| Rnase1 | 2.79 | 1.72 | 3.06 | 1.81 | 0.66 | 0.97 | 1.00 | 2.96 | 0.76 | 3.06 | 11.13 | 0.82 |
| Rnase10 | 1.00 | 1.00 | 1.00 | 0.18 | 1.00 | 1.00 | 5.36 | 1.84 | 5.73 | 1.00 | 1.00 | 1.00 |
| Rnase12 | 1.00 | 1.00 | 1.00 | 1.00 | 12.62 | 0.04 | 1.00 | 1.00 | 1.00 | 2.37 | 6.43 | 6.34 |
| Rnase2a | 1.61 | 2.37 | 8.47 | 1.18 | 1.15 | 2.42 | 1.00 | 1.00 | 1.00 | 1.00 | 1.00 | 1.08 |
| Rnaseh1 | 0.89 | 0.77 | 1.03 | 0.88 | 1.00 | 0.93 | 0.84 | 0.33 | 1.29 | 1.25 | 1.22 | 1.02 |
| Rnaseh2a | 0.88 | 0.88 | 1.12 | 0.94 | 1.36 | 0.91 | 0.94 | 3.09 | 1.12 | 1.01 | 1.23 | 0.96 |
| Rnaseh2b | 0.85 | 0.75 | 0.83 | 0.73 | 0.73 | 0.61 | 1.00 | 2.44 | 1.00 | 1.13 | 1.26 | 0.82 |
| Rnasek | 1.08 | 1.21 | 1.09 | 0.91 | 2.50 | 0.97 | 0.90 | 1.41 | 1.02 | 1.01 | 1.27 | 0.93 |
| Rnaset2a | 0.94 | 1.08 | 1.62 | 0.81 | 10.11 | 1.15 | 1.04 | 1.89 | 0.10 | 0.94 | 1.21 | 0.89 |
| Rnaset2b | 1.22 | 0.99 | 0.88 | 0.74 | 5.05 | 0.94 | 0.47 | 1.26 | 0.87 | 1.00 | 1.27 | 1.05 |
| Rnf112 | 1.00 | 1.00 | 1.00 | 1.00 | 1.00 | 1.00 | 0.97 | 1.29 | 1.22 | 1.00 | 10.48 | 1.00 |
| Rnf125 | 2.20 | 3.18 | 1.00 | 6.58 | 1.69 | 2.18 | 1.18 | 1.14 | 1.09 | 0.73 | 0.33 | 0.66 |
| Rnf185 | 1.08 | 1.08 | 0.90 | 1.93 | 6.02 | 1.71 | 1.05 | 1.06 | 0.90 | 1.10 | 1.00 | 1.03 |
| Rnf208 | 0.92 | 1.12 | 0.87 | 1.08 | 1.33 | 2.44 | 0.78 | 1.69 | 0.90 | 0.77 | 9.98 | 1.07 |
| Rnf25 | 1.01 | 1.11 | 1.37 | 0.99 | 2.89 | 1.15 | 1.00 | 2.15 | 1.01 | 1.25 | 1.35 | 0.92 |
| Rnu11 | 1.00 | 1.00 | 1.00 | 1.00 | 1.00 | 1.00 | 1.00 | 1.00 | 1.00 | 1.00 | 1.00 | 1.00 |
| Rogdi | 1.12 | 1.37 | 1.36 | 1.52 | 2.43 | 1.69 | 0.99 | 2.46 | 0.94 | 0.92 | 1.06 | 0.80 |
| Rom1 | 1.26 | 1.19 | 0.81 | 1.14 | 1.72 | 0.88 | 1.18 | 3.23 | 1.16 | 0.93 | 1.12 | 1.23 |
| Romo1 | 0.79 | 1.76 | 1.12 | 0.75 | 3.06 | 0.88 | 0.88 | 1.72 | 0.98 | 1.16 | 1.21 | 1.00 |
| Ropn1l | 1.00 | 1.00 | 0.90 | 1.24 | 2.68 | 0.58 | 0.90 | 1.09 | 0.97 | 0.93 | 1.04 | 1.00 |
| Rpa2 | 1.04 | 0.60 | 1.13 | 0.79 | 0.80 | 0.66 | 0.97 | 1.23 | 0.86 | 1.13 | 1.17 | 0.84 |
| Rpap3 | 0.98 | 1.22 | 1.01 | 1.02 | 1.17 | 0.84 | 1.43 | 2.34 | 1.35 | 0.96 | 1.40 | 1.35 |
| Rpf2 | 0.80 | 0.79 | 0.76 | 0.95 | 2.16 | 1.31 | 0.88 | 2.89 | 1.13 | 1.07 | 1.38 | 1.06 |
| Rpgrip1 | 1.00 | 1.00 | 1.00 | 1.00 | 1.00 | 1.00 | 1.00 | 0.89 | 0.93 | 0.98 | 0.73 | 1.07 |
| Rph3a | 1.00 | 1.00 | 1.00 | 1.00 | 1.00 | 1.00 | 1.00 | 1.00 | 1.00 | 1.00 | 9.84 | 1.00 |
| Rpl10 | 0.93 | 0.94 | 1.11 | 1.09 | 4.68 | 1.23 | 0.93 | 0.90 | 0.71 | 1.26 | 1.33 | 0.99 |
| Rpl10a | 1.00 | 1.15 | 1.15 | 1.06 | 3.44 | 1.25 | 0.84 | 2.23 | 1.03 | 1.31 | 1.59 | 1.03 |
| Rpl13 | 0.98 | 0.96 | 1.13 | 0.84 | 1.80 | 1.10 | 0.85 | 6.77 | 1.02 | 1.30 | 1.61 | 1.08 |
| Rpl13a | 0.80 | 0.96 | 1.02 | 1.20 | 1.90 | 1.17 | 0.97 | 4.43 | 1.07 | 1.02 | 1.25 | 0.94 |
| Rpl14 | 0.96 | 1.08 | 1.12 | 0.99 | 2.34 | 1.15 | 1.07 | 4.28 | 1.12 | 1.09 | 1.56 | 1.05 |
| Rpl17 | 0.76 | 0.97 | 1.08 | 1.06 | 4.85 | 1.17 | 1.07 | 1.33 | 0.82 | 1.33 | 1.44 | 1.08 |
| Rpl18 | 1.04 | 1.17 | 1.14 | 1.12 | 3.94 | 1.21 | 0.96 | 1.92 | 1.40 | 1.14 | 1.61 | 0.98 |
| Rpl18a | 1.14 | 1.19 | 1.17 | 1.07 | 3.02 | 1.20 | 0.93 | 2.22 | 1.08 | 1.19 | 1.45 | 1.02 |
| Rpl19 | 0.86 | 1.01 | 1.03 | 1.07 | 3.02 | 1.03 | 1.10 | 2.78 | 1.19 | 1.10 | 1.54 | 1.07 |
| Rpl22 | 1.01 | 0.96 | 1.26 | 0.93 | 2.77 | 1.17 | 0.87 | 1.78 | 0.81 | 1.11 | 1.19 | 1.14 |
| Rpl22l1 | 1.20 | 0.95 | 0.93 | 0.86 | 3.79 | 1.51 | 1.22 | 1.61 | 0.93 | 1.29 | 1.60 | 1.08 |
| Rpl23 | 1.12 | 0.98 | 1.24 | 1.17 | 2.50 | 1.15 | 1.08 | 1.80 | 0.86 | 1.35 | 1.49 | 1.10 |
| Rpl24 | 0.80 | 1.23 | 1.13 | 0.73 | 2.46 | 1.00 | 0.83 | 2.09 | 1.01 | 1.35 | 1.63 | 1.07 |
| Rpl27a | 1.09 | 1.08 | 1.17 | 1.02 | 3.36 | 1.16 | 0.74 | 1.86 | 0.95 | 1.23 | 1.41 | 1.09 |
| Rpl28 | 1.79 | 1.11 | 1.58 | 1.02 | 1.30 | 1.31 | 0.48 | 4.88 | 1.50 | 1.42 | 2.10 | 1.19 |
| Rpl31 | 0.82 | 0.99 | 1.04 | 1.17 | 1.96 | 0.96 | 1.30 | 1.91 | 1.04 | 1.14 | 1.35 | 1.03 |
| Rpl31-ps12 | 0.92 | 1.10 | 1.14 | 0.99 | 3.20 | 1.17 | 1.02 | 1.12 | 0.99 | 1.30 | 1.62 | 1.08 |
| Rpl32 | 1.05 | 1.07 | 1.14 | 1.09 | 3.48 | 1.21 | 0.87 | 4.37 | 0.88 | 1.49 | 1.70 | 1.15 |
| Rpl35 | 1.04 | 1.17 | 1.04 | 0.93 | 2.86 | 0.91 | 0.89 | 3.30 | 1.15 | 1.25 | 1.63 | 1.01 |
| Rpl35a | 1.06 | 1.57 | 1.65 | 0.92 | 6.64 | 1.23 | 0.61 | 0.78 | 0.95 | 1.06 | 1.44 | 1.13 |
| Rpl36 | 0.87 | 1.07 | 1.43 | 0.59 | 1.65 | 1.16 | 0.61 | 6.06 | 0.98 | 0.91 | 1.50 | 1.27 |
| Rpl36a | 1.16 | 1.19 | 1.13 | 1.11 | 2.55 | 1.08 | 1.00 | 5.55 | 1.00 | 1.00 | 1.54 | 0.90 |
| Rpl36al | 0.91 | 0.95 | 0.90 | 1.21 | 3.62 | 1.27 | 0.92 | 1.74 | 0.89 | 1.21 | 1.32 | 1.11 |
| Rpl37a | 0.64 | 1.18 | 1.13 | 0.88 | 3.45 | 1.13 | 1.00 | 2.51 | 1.15 | 0.91 | 1.28 | 0.85 |
| Rpl38 | 1.15 | 0.83 | 0.96 | 0.80 | 12.34 | 0.86 | 0.55 | 3.48 | 1.15 | 1.38 | 1.99 | 1.19 |
| Rpl39 | 0.85 | 1.00 | 1.15 | 0.95 | 3.88 | 1.08 | 0.68 | 1.90 | 1.24 | 1.44 | 1.51 | 1.03 |
| Rpl3l | 1.00 | 1.07 | 1.00 | 1.00 | 1.00 | 1.00 | 1.00 | 1.00 | 1.00 | 1.00 | 1.00 | 1.00 |
| Rpl4 | 1.01 | 1.06 | 1.13 | 1.04 | 5.64 | 1.25 | 0.97 | 0.73 | 1.04 | 1.32 | 1.50 | 1.09 |
| Rpl41 | 1.00 | 1.17 | 1.03 | 0.93 | 3.15 | 1.00 | 0.95 | 2.10 | 1.04 | 1.13 | 1.41 | 0.95 |
| Rpl8 | 0.95 | 1.04 | 1.03 | 1.11 | 2.62 | 1.20 | 1.01 | 2.89 | 1.08 | 1.17 | 1.47 | 1.05 |
| Rplp0 | 1.05 | 1.10 | 1.11 | 1.21 | 2.73 | 1.27 | 1.00 | 3.82 | 1.12 | 1.34 | 1.56 | 1.23 |
| Rplp1 | 1.25 | 1.41 | 1.46 | 1.25 | 3.05 | 1.40 | 0.86 | 5.15 | 0.96 | 1.58 | 2.10 | 1.40 |

Fig. 35- 248

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Rhou | 2.23 | 2.36 | 1.62 | 1.23 | 1.36 | 1.11 | 1.13 | 3.38 | 1.01 | 2.26 | 1.22 | 1.32 |
| Riiad1 | 1.00 | 1.00 | 1.00 | 1.00 | 0.07 | 1.00 | 1.00 | 1.00 | 1.00 | 1.00 | 1.00 | 1.00 |
| Rit2 | 1.00 | 1.00 | 1.00 | 1.14 | 0.97 | 1.10 | 1.00 | 1.00 | 1.00 | 1.00 | 1.00 | 1.00 |
| Rmnd1 | 1.00 | 1.00 | 1.00 | 1.00 | 1.00 | 1.00 | 1.00 | 1.00 | 1.00 | 1.00 | 1.00 | 0.70 |
| Rmrp | 1.00 | 1.00 | 1.00 | 1.00 | 0.33 | 1.00 | 0.56 | 141.84 | 1.95 | 0.30 | 1.20 | 1.87 |
| Rn4.5s | 0.41 | 0.15 | 2.26 | 0.93 | 1.27 | 1.16 | 1.10 | 6.98 | 0.78 | 2.55 | 1.35 | 0.87 |
| Rn45s | 2.59 | 2.37 | 2.65 | 1.52 | 0.19 | 1.17 | 0.79 | 49.78 | 0.95 | 0.46 | 1.50 | 1.64 |
| Rnase1 | 1.13 | 1.22 | 1.06 | 1.16 | 1.00 | 0.77 | 0.88 | 0.97 | 0.51 | 1.00 | 0.31 | 1.43 |
| Rnase10 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.50 | 2.71 | 1.00 | 27.54 | 14.18 | 7.82 |
| Rnase2a | 1.00 | 1.00 | 1.00 | 1.00 | 1.00 | 1.00 | 1.00 | 0.35 | 0.78 | 1.28 | 1.40 | 1.20 |
| Rnaseh1 | 1.74 | 1.02 | 1.41 | 0.82 | 0.35 | 0.99 | 1.19 | 1.04 | 1.14 | 0.85 | 0.91 | 0.98 |
| Rnaseh2a | 1.00 | 1.00 | 1.00 | 0.93 | 0.75 | 1.02 | 1.18 | 10.75 | 0.87 | 1.93 | 1.02 | 0.86 |
| Rnaseh2b | 1.00 | 1.00 | 1.00 | 0.94 | 0.67 | 1.06 | 0.61 | 6.25 | 0.89 | 1.97 | 0.90 | 1.47 |
| Rnasek | 0.96 | 1.01 | 0.96 | 1.10 | 0.84 | 1.05 | 1.08 | 5.14 | 0.93 | 2.05 | 1.20 | 1.34 |
| Rnaset2a | 3.13 | 5.43 | 0.75 | 1.86 | 0.68 | 1.10 | 0.43 | 0.28 | 0.93 | 1.86 | 1.10 | 1.14 |
| Rnaset2b | 0.31 | 0.25 | 0.74 | 0.50 | 0.66 | 1.38 | 1.83 | 5.95 | 1.18 | 3.92 | 1.79 | 1.44 |
| Rnf112 | 1.00 | 1.00 | 1.00 | 1.02 | 1.00 | 0.94 | 1.35 | 2.70 | 1.51 | 1.00 | 1.00 | 1.00 |
| Rnf125 | 1.00 | 1.00 | 1.00 | 1.00 | 1.00 | 1.00 | 1.02 | 1.12 | 3.56 | 1.00 | 0.66 | 0.96 |
| Rnf185 | 1.11 | 1.07 | 1.11 | 1.04 | 0.77 | 0.87 | 1.08 | 0.76 | 1.01 | 1.71 | 1.62 | 1.32 |
| Rnf208 | 1.00 | 1.00 | 1.00 | 1.04 | 0.74 | 0.95 | 1.53 | 5.76 | 1.13 | 1.00 | 1.00 | 1.00 |
| Rnf25 | 1.56 | 1.82 | 1.27 | 1.07 | 1.03 | 1.02 | 1.09 | 5.80 | 1.05 | 2.30 | 1.20 | 1.32 |
| Rnu11 | 1.00 | 1.00 | 1.00 | 1.00 | 363.99 | 1.00 | 1.00 | 1.00 | 1.00 | 1.00 | 1.00 | 1.00 |
| Rogdi | 1.10 | 1.32 | 1.03 | 1.16 | 1.04 | 1.07 | 1.15 | 7.62 | 0.95 | 2.77 | 1.36 | 1.01 |
| Rom1 | 1.00 | 1.00 | 1.00 | 1.36 | 0.74 | 0.99 | 1.28 | 7.19 | 1.08 | 2.18 | 1.17 | 1.08 |
| Romo1 | 0.82 | 0.96 | 1.12 | 1.21 | 0.77 | 1.01 | 1.44 | 10.64 | 0.86 | 3.25 | 1.14 | 1.03 |
| Ropn1l | 1.00 | 1.01 | 0.80 | 1.00 | 1.00 | 1.00 | 7.23 | 1.35 | 1.00 | 1.32 | 1.00 | 1.00 |
| Rpa2 | 1.00 | 1.00 | 1.00 | 1.15 | 0.86 | 0.96 | 1.09 | 3.14 | 0.97 | 1.24 | 1.00 | 0.92 |
| Rpap3 | 1.00 | 1.00 | 1.00 | 0.94 | 1.16 | 0.96 | 0.81 | 6.08 | 1.06 | 1.78 | 1.10 | 0.84 |
| Rpf2 | 1.00 | 1.00 | 1.00 | 1.09 | 1.49 | 0.97 | 0.68 | 7.16 | 0.86 | 1.43 | 0.94 | 1.31 |
| Rpgrip1 | 1.00 | 1.00 | 1.00 | 1.00 | 0.12 | 1.00 | 1.00 | 2.59 | 1.00 | 7.39 | 1.00 | 1.00 |
| Rph3a | 1.00 | 1.00 | 1.00 | 1.06 | 1.42 | 1.02 | 1.00 | 1.00 | 1.00 | 1.00 | 1.00 | 1.00 |
| Rpl10 | 0.85 | 0.93 | 0.88 | 1.02 | 1.01 | 1.03 | 1.18 | 5.53 | 0.92 | 2.57 | 1.24 | 1.20 |
| Rpl10a | 0.89 | 1.19 | 1.07 | 0.93 | 1.22 | 0.96 | 1.23 | 10.30 | 0.92 | 2.84 | 1.14 | 1.08 |
| Rpl13 | 0.82 | 0.80 | 0.95 | 0.86 | 0.76 | 0.96 | 1.04 | 41.67 | 0.83 | 5.15 | 1.13 | 1.14 |
| Rpl13a | 0.73 | 0.72 | 0.96 | 1.17 | 0.64 | 0.97 | 0.98 | 19.14 | 0.69 | 2.46 | 1.01 | 1.09 |
| Rpl14 | 0.81 | 0.99 | 0.85 | 1.07 | 0.98 | 0.99 | 1.30 | 30.51 | 0.86 | 3.87 | 1.21 | 1.06 |
| Rpl17 | 0.78 | 1.13 | 0.89 | 1.46 | 1.49 | 0.86 | 1.39 | 5.81 | 0.78 | 2.33 | 1.36 | 0.94 |
| Rpl18 | 0.81 | 1.15 | 0.99 | 1.01 | 1.08 | 0.97 | 1.31 | 7.97 | 0.88 | 3.21 | 1.27 | 1.16 |
| Rpl18a | 0.95 | 0.89 | 0.95 | 1.17 | 0.81 | 1.02 | 1.23 | 6.60 | 0.79 | 2.04 | 1.16 | 1.04 |
| Rpl19 | 0.91 | 0.97 | 1.12 | 0.95 | 0.95 | 0.93 | 1.27 | 14.71 | 0.84 | 3.86 | 1.16 | 1.13 |
| Rpl22 | 0.72 | 0.80 | 0.96 | 1.10 | 1.10 | 1.01 | 1.03 | 5.51 | 0.88 | 2.12 | 1.03 | 1.02 |
| Rpl22l1 | 1.10 | 1.31 | 1.59 | 1.31 | 1.03 | 1.13 | 0.92 | 7.15 | 0.82 | 2.66 | 1.15 | 1.37 |
| Rpl23 | 0.84 | 0.80 | 1.05 | 0.99 | 0.98 | 1.17 | 1.28 | 6.03 | 0.84 | 2.18 | 1.31 | 1.15 |
| Rpl24 | 0.91 | 0.57 | 1.03 | 1.11 | 0.47 | 1.09 | 1.25 | 6.18 | 0.75 | 2.13 | 0.91 | 1.33 |
| Rpl27a | 0.83 | 0.98 | 1.04 | 1.08 | 1.15 | 1.01 | 1.07 | 6.76 | 0.79 | 2.14 | 1.17 | 1.06 |
| Rpl28 | 1.41 | 0.89 | 0.97 | 1.44 | 0.91 | 1.16 | 1.22 | 20.74 | 0.83 | 4.47 | 1.09 | 1.57 |
| Rpl31 | 0.90 | 0.95 | 0.94 | 0.97 | 0.52 | 1.03 | 1.29 | 3.69 | 0.82 | 2.35 | 1.22 | 1.15 |
| Rpl31-ps12 | 0.80 | 0.94 | 0.90 | 1.03 | 1.47 | 1.02 | 0.96 | 4.99 | 0.91 | 2.59 | 1.17 | 1.17 |
| Rpl32 | 0.83 | 0.82 | 1.12 | 0.96 | 1.56 | 1.04 | 1.30 | 18.27 | 0.94 | 3.63 | 1.18 | 1.11 |
| Rpl35 | 0.85 | 0.81 | 0.91 | 1.07 | 0.93 | 1.23 | 1.24 | 22.88 | 0.88 | 3.54 | 1.09 | 1.12 |
| Rpl35a | 1.01 | 1.57 | 1.54 | 1.98 | 1.12 | 0.70 | 0.79 | 2.66 | 0.82 | 1.94 | 1.24 | 0.82 |
| Rpl36 | 0.80 | 0.81 | 1.02 | 1.12 | 0.85 | 1.26 | 1.28 | 30.30 | 0.80 | 5.39 | 0.96 | 1.14 |
| Rpl36a | 0.72 | 0.82 | 1.48 | 1.23 | 0.96 | 0.96 | 1.58 | 47.72 | 1.12 | 6.86 | 0.77 | 0.82 |
| Rpl36al | 0.90 | 1.08 | 1.11 | 1.18 | 1.01 | 1.00 | 1.13 | 8.92 | 0.87 | 2.42 | 1.05 | 1.04 |
| Rpl37a | 0.82 | 1.06 | 1.01 | 1.10 | 0.80 | 0.75 | 0.82 | 14.76 | 0.74 | 2.75 | 1.19 | 1.09 |
| Rpl38 | 1.57 | 0.70 | 1.38 | 0.69 | 0.84 | 1.12 | 2.26 | 14.69 | 0.65 | 3.90 | 1.10 | 0.95 |
| Rpl39 | 0.71 | 0.87 | 1.13 | 0.91 | 0.94 | 1.18 | 0.89 | 8.40 | 0.91 | 2.61 | 1.06 | 1.05 |
| Rpl3l | 1.00 | 1.00 | 1.00 | 1.00 | 1.00 | 1.00 | 2.02 | 15.29 | 2.18 | 1.65 | 1.00 | 1.00 |
| Rpl4 | 0.84 | 0.94 | 0.99 | 0.97 | 1.37 | 1.03 | 1.02 | 3.06 | 0.88 | 1.70 | 1.07 | 1.01 |
| Rpl41 | 0.88 | 0.97 | 0.94 | 1.15 | 1.03 | 1.11 | 1.43 | 9.91 | 0.83 | 2.99 | 1.13 | 1.12 |
| Rpl8 | 0.92 | 0.96 | 0.89 | 1.11 | 0.87 | 0.99 | 1.13 | 9.89 | 0.83 | 2.40 | 1.03 | 0.96 |
| Rplp0 | 0.87 | 0.92 | 0.96 | 1.02 | 0.87 | 1.11 | 1.02 | 9.78 | 0.80 | 2.59 | 1.13 | 1.03 |
| Rplp1 | 1.01 | 1.13 | 1.06 | 1.28 | 1.26 | 1.16 | 1.40 | 25.82 | 0.78 | 4.01 | 1.39 | 1.22 |

Fig. 35- 249

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Rplp2 | 1.73 | 0.70 | 1.03 | 0.13 | 7.79 | 1.15 | 1.19 | 0.87 | 0.85 | 1.27 | 2.62 | 0.81 |
| Rplp2-ps1 | 1.43 | 0.60 | 0.97 | 0.34 | 13.44 | 1.14 | 1.11 | 0.81 | 0.83 | 2.59 | 4.45 | 0.93 |
| Rpp21 | 1.33 | 0.77 | 1.04 | 0.34 | 9.25 | 1.78 | 0.93 | 0.73 | 0.91 | 2.66 | 4.51 | 1.70 |
| Rpp25l | 2.66 | 1.56 | 2.04 | 1.97 | 16.28 | 3.02 | 2.44 | 2.24 | 2.20 | 5.20 | 6.63 | 2.69 |
| Rpp40 | 1.75 | 1.53 | 1.91 | 1.69 | 5.46 | 1.56 | 1.56 | 1.88 | 1.76 | 2.05 | 2.10 | 1.74 |
| Rpph1 | 1.00 | 1.00 | 1.00 | 1.00 | 1.61 | 1.00 | 1.00 | 2.13 | 1.00 | 7.92 | 5.72 | 1.00 |
| Rprl3 | 1.00 | 1.00 | 1.00 | 1.00 | 3.15 | 1.00 | 0.99 | 0.44 | 1.00 | 7.75 | 6.96 | 1.00 |
| Rps12 | 3.16 | 0.84 | 0.58 | 0.06 | 8.93 | 1.19 | 2.42 | 0.95 | 0.66 | 0.63 | 1.34 | 0.86 |
| Rps13 | 1.11 | 0.81 | 0.78 | 0.78 | 5.70 | 0.81 | 0.71 | 0.81 | 0.87 | 0.83 | 1.91 | 0.83 |
| Rps14 | 1.52 | 0.74 | 0.93 | 0.25 | 5.84 | 0.91 | 0.83 | 0.74 | 0.74 | 1.20 | 2.32 | 0.80 |
| Rps15 | 1.37 | 0.61 | 0.92 | 0.30 | 10.94 | 1.13 | 0.97 | 0.78 | 0.89 | 2.05 | 3.83 | 0.87 |
| Rps15a-ps4 | 1.37 | 0.99 | 1.10 | 0.95 | 5.51 | 1.10 | 1.07 | 0.97 | 0.97 | 0.82 | 1.74 | 0.81 |
| Rps15a-ps6 | 1.28 | 0.98 | 1.09 | 0.85 | 5.35 | 1.15 | 0.96 | 0.91 | 0.82 | 0.96 | 1.84 | 0.96 |
| Rps16 | 1.72 | 0.47 | 1.08 | 0.28 | 16.31 | 1.18 | 0.82 | 0.67 | 0.99 | 2.93 | 4.33 | 0.86 |
| Rps18 | 1.00 | 0.78 | 0.67 | 0.22 | 1.44 | 1.00 | 0.72 | 1.89 | 1.15 | 1.04 | 2.70 | 1.00 |
| Rps19 | 1.90 | 0.49 | 1.03 | 0.32 | 9.96 | 0.93 | 0.65 | 0.86 | 0.79 | 1.80 | 3.70 | 0.82 |
| Rps19-ps3 | 1.49 | 0.61 | 0.72 | 0.77 | 5.42 | 1.48 | 1.14 | 0.74 | 1.15 | 0.95 | 1.42 | 0.94 |
| Rps20 | 1.51 | 0.66 | 1.01 | 0.45 | 12.26 | 1.16 | 0.86 | 0.75 | 0.93 | 2.77 | 4.09 | 0.84 |
| Rps24 | 1.26 | 0.74 | 0.95 | 0.52 | 7.07 | 1.19 | 0.79 | 0.89 | 0.82 | 1.95 | 2.59 | 0.92 |
| Rps25 | 1.31 | 0.71 | 1.12 | 0.41 | 5.28 | 1.19 | 0.90 | 0.76 | 0.94 | 0.98 | 2.13 | 0.80 |
| Rps27a | 1.54 | 0.53 | 0.84 | 0.29 | 14.30 | 1.15 | 0.86 | 0.83 | 0.94 | 3.05 | 4.67 | 0.74 |
| Rps27rt | 1.00 | 0.13 | 1.00 | 1.00 | 6.27 | 1.00 | 1.00 | 1.00 | 2.62 | 13.94 | 13.55 | 1.00 |
| Rps29 | 1.67 | 0.65 | 1.60 | 0.12 | 4.77 | 1.05 | 2.25 | 1.30 | 0.36 | 1.79 | 2.60 | 1.17 |
| Rps3 | 1.44 | 0.83 | 1.05 | 0.51 | 5.31 | 1.20 | 0.98 | 0.89 | 0.90 | 1.22 | 2.25 | 0.96 |
| Rps4l | 2.79 | 0.78 | 0.93 | 0.30 | 3.70 | 0.92 | 1.76 | 1.05 | 1.23 | 1.64 | 2.24 | 0.94 |
| Rps4x | 1.29 | 0.63 | 0.95 | 0.44 | 6.40 | 1.09 | 0.84 | 0.81 | 0.85 | 2.15 | 2.60 | 0.78 |
| Rps6 | 1.41 | 0.75 | 1.12 | 0.74 | 7.93 | 1.50 | 0.87 | 0.86 | 0.93 | 1.41 | 2.19 | 0.93 |
| Rps8 | 1.69 | 0.63 | 1.15 | 0.30 | 9.34 | 1.14 | 0.84 | 0.80 | 0.77 | 2.05 | 3.00 | 0.94 |
| Rps9 | 1.23 | 0.55 | 1.04 | 0.44 | 16.50 | 1.16 | 0.94 | 0.79 | 0.82 | 3.57 | 5.10 | 0.93 |
| Rpsa | 1.37 | 0.39 | 1.10 | 0.22 | 20.76 | 1.06 | 0.98 | 0.98 | 1.04 | 6.66 | 8.05 | 0.92 |
| Rpusd3 | 0.72 | 0.48 | 0.68 | 0.56 | 5.81 | 0.99 | 1.02 | 0.83 | 0.71 | 1.66 | 2.21 | 0.91 |
| Rrad | 16.54 | 6.97 | 2.48 | 0.96 | 1.05 | 1.00 | 0.89 | 0.70 | 1.31 | 0.34 | 0.62 | 0.66 |
| Rrp12 | 1.36 | 0.86 | 1.58 | 0.78 | 3.60 | 1.06 | 1.60 | 2.10 | 1.92 | 3.29 | 4.91 | 1.22 |
| Rrp7a | 1.41 | 0.80 | 1.03 | 0.91 | 5.40 | 1.18 | 1.04 | 0.94 | 1.12 | 1.80 | 2.26 | 1.12 |
| Rsad2 | 0.82 | 1.00 | 1.00 | 3.12 | 1.95 | 1.21 | 1.03 | 1.17 | 1.03 | 3.54 | 3.20 | 1.77 |
| Rsbn1 | 0.97 | 1.00 | 1.54 | 5.07 | 0.58 | 1.06 | 1.05 | 2.08 | 1.51 | 1.00 | 0.99 | 0.90 |
| Rsl1d1 | 1.20 | 1.07 | 1.16 | 2.13 | 3.85 | 1.42 | 0.94 | 1.07 | 0.95 | 1.60 | 1.41 | 0.95 |
| Rsph9 | 1.00 | 1.00 | 1.00 | 1.00 | 1.78 | 1.00 | 1.37 | 0.81 | 0.77 | 2.39 | 2.25 | 1.00 |
| Rtcb | 1.20 | 0.88 | 1.07 | 0.67 | 5.14 | 1.08 | 1.22 | 1.23 | 1.13 | 1.74 | 2.52 | 1.17 |
| Rtn1 | 1.00 | 1.00 | 0.94 | 1.00 | 0.03 | 1.00 | 0.81 | 0.50 | 0.77 | 1.23 | 1.06 | 1.13 |
| Rtn2 | 1.06 | 0.60 | 0.77 | 0.81 | 5.39 | 1.07 | 1.07 | 0.87 | 0.79 | 2.42 | 2.86 | 0.92 |
| Rtp4 | 1.62 | 2.32 | 2.71 | 4.55 | 1.12 | 4.14 | 4.00 | 1.58 | 2.72 | 1.21 | 0.95 | 2.56 |
| Rxrg | 0.81 | 0.65 | 0.63 | 0.16 | 0.56 | 0.84 | 0.65 | 0.63 | 0.65 | 1.00 | 1.00 | 1.00 |
| S100a10 | 1.78 | 0.90 | 1.38 | 0.61 | 8.41 | 1.06 | 0.94 | 0.87 | 1.16 | 1.67 | 2.81 | 1.21 |
| S100a13 | 1.69 | 0.59 | 1.39 | 0.56 | 16.47 | 1.11 | 1.06 | 0.89 | 1.05 | 4.25 | 5.87 | 0.98 |
| S100a16 | 1.25 | 0.67 | 0.96 | 0.85 | 7.54 | 1.13 | 0.87 | 0.76 | 0.96 | 2.73 | 3.32 | 1.02 |
| S100a3 | 1.00 | 1.00 | 1.00 | 1.00 | 1.00 | 1.00 | 1.00 | 1.00 | 1.00 | 1.96 | 3.18 | 0.82 |
| S100a4 | 0.89 | 0.44 | 1.30 | 0.71 | 10.30 | 0.63 | 0.59 | 0.37 | 0.90 | 0.72 | 1.12 | 0.62 |
| S100a5 | 1.00 | 0.83 | 1.25 | 1.00 | 1.00 | 1.00 | 1.00 | 1.00 | 1.00 | 1.00 | 1.00 | 1.00 |
| S100a6 | 1.27 | 0.78 | 1.22 | 0.64 | 5.26 | 1.00 | 0.87 | 0.64 | 1.08 | 1.85 | 3.52 | 1.37 |
| S100a8 | 1.66 | 23.70 | 13.11 | 10.66 | 6.21 | 1.00 | 2.74 | 1.74 | 0.98 | 3.13 | 3.31 | 1.46 |
| S100a9 | 1.36 | 17.40 | 18.59 | 4.86 | 4.81 | 1.00 | 1.28 | 1.30 | 1.28 | 2.30 | 2.65 | 1.22 |
| S100b | 0.84 | 0.91 | 1.55 | 0.41 | 0.95 | 0.26 | 0.60 | 0.72 | 0.71 | 2.93 | 2.83 | 0.84 |
| Saa1 | 1.34 | 5.01 | 0.83 | 1.00 | 1.64 | 1.00 | 1.00 | 1.00 | 1.00 | 4.87 | 7.72 | 0.69 |
| Saa2 | 1.33 | 1.90 | 1.00 | 1.00 | 1.02 | 1.00 | 1.00 | 1.00 | 1.00 | 1.00 | 1.67 | 1.00 |
| Saa3 | 1.00 | 1.00 | 1.00 | 1.00 | 1.00 | 1.00 | 1.00 | 1.00 | 3.48 | 2.63 | 13.67 | 0.64 |
| Safb2 | 0.94 | 0.82 | 1.18 | 0.58 | 3.17 | 1.19 | 1.09 | 0.95 | 1.21 | 3.90 | 3.00 | 1.21 |
| Samd11 | 1.00 | 0.45 | 1.00 | 1.00 | 17.31 | 1.00 | 1.00 | 1.00 | 1.00 | 5.07 | 5.04 | 0.95 |
| Samm50 | 1.00 | 0.45 | 0.88 | 0.31 | 7.59 | 0.99 | 1.00 | 0.87 | 0.95 | 2.75 | 3.32 | 0.82 |
| Sap25 | 1.00 | 0.85 | 2.95 | 0.24 | 13.37 | 1.00 | 1.00 | 0.44 | 1.00 | 1.06 | 2.29 | 0.50 |
| Sap30l | 1.15 | 0.70 | 0.96 | 0.54 | 3.92 | 1.01 | 1.05 | 1.02 | 1.07 | 2.15 | 2.59 | 1.06 |
| Sapcd1 | 2.05 | 1.10 | 0.54 | 1.00 | 1.00 | 1.00 | 1.62 | 0.38 | 0.52 | 1.35 | 2.10 | 2.03 |
| Sars | 1.15 | 0.66 | 0.95 | 0.50 | 4.56 | 1.05 | 1.07 | 1.08 | 1.06 | 2.71 | 3.61 | 1.19 |
| Sars2 | 1.30 | 0.65 | 0.71 | 0.30 | 4.00 | 0.52 | 1.06 | 0.98 | 0.93 | 2.98 | 2.99 | 1.18 |

Fig. 35- 250

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Rplp2 | 1.24 | 2.03 | 1.09 | 0.90 | 0.78 | 1.13 | 1.72 | 1.33 | 1.31 | 1.14 | 2.05 | 1.08 |
| Rplp2-ps1 | 1.22 | 1.77 | 0.97 | 0.94 | 0.58 | 0.99 | 1.06 | 2.26 | 1.03 | 1.01 | 1.78 | 1.13 |
| Rpp21 | 1.31 | 2.09 | 1.10 | 0.98 | 1.34 | 0.86 | 0.88 | 0.75 | 0.57 | 1.51 | 1.92 | 1.04 |
| Rpp25l | 2.48 | 3.47 | 2.05 | 2.32 | 1.72 | 1.97 | 1.55 | 3.21 | 1.99 | 2.36 | 3.18 | 2.28 |
| Rpp40 | 1.34 | 1.20 | 1.09 | 1.77 | 2.02 | 1.98 | 1.21 | 1.32 | 0.75 | 1.00 | 1.71 | 1.27 |
| Rpph1 | 0.56 | 2.93 | 2.26 | 1.00 | 1.57 | 2.03 | 1.08 | 19.16 | 1.00 | 1.37 | 0.91 | 1.00 |
| Rprl3 | 2.42 | 1.00 | 1.00 | 3.86 | 1.23 | 1.00 | 1.00 | 9.64 | 1.00 | 1.01 | 3.43 | 1.00 |
| Rps12 | 1.53 | 2.14 | 1.22 | 0.75 | 1.89 | 1.14 | 1.92 | 0.59 | 0.89 | 1.19 | 1.57 | 1.17 |
| Rps13 | 1.13 | 1.39 | 0.99 | 0.70 | 1.09 | 0.81 | 1.18 | 0.58 | 0.95 | 0.87 | 1.64 | 1.08 |
| Rps14 | 1.33 | 1.95 | 1.05 | 0.73 | 0.67 | 0.66 | 0.93 | 0.89 | 0.95 | 0.88 | 1.60 | 0.99 |
| Rps15 | 1.38 | 2.08 | 1.05 | 0.83 | 0.64 | 0.84 | 0.98 | 1.56 | 1.08 | 0.98 | 1.96 | 1.13 |
| Rps15a-ps4 | 1.11 | 1.27 | 0.97 | 1.08 | 1.22 | 0.92 | 1.13 | 0.61 | 1.13 | 0.95 | 1.45 | 1.11 |
| Rps15a-ps6 | 1.26 | 1.49 | 0.99 | 0.89 | 1.02 | 0.75 | 0.99 | 0.77 | 1.13 | 1.00 | 1.79 | 1.11 |
| Rps16 | 1.33 | 1.85 | 1.05 | 0.55 | 0.51 | 1.03 | 0.91 | 2.32 | 1.23 | 0.99 | 2.09 | 1.15 |
| Rps18 | 0.84 | 1.25 | 1.55 | 1.00 | 0.46 | 0.66 | 1.18 | 4.86 | 0.79 | 0.59 | 1.89 | 1.12 |
| Rps19 | 1.31 | 1.95 | 0.94 | 0.68 | 0.64 | 0.84 | 1.06 | 1.32 | 1.15 | 0.90 | 1.92 | 1.14 |
| Rps19-ps3 | 1.12 | 1.56 | 1.01 | 0.61 | 0.90 | 0.65 | 1.20 | 0.90 | 1.02 | 0.80 | 1.91 | 0.93 |
| Rps20 | 1.38 | 1.86 | 1.10 | 0.81 | 0.61 | 0.92 | 0.97 | 2.46 | 1.20 | 0.99 | 2.04 | 1.09 |
| Rps24 | 1.29 | 1.66 | 0.99 | 0.92 | 0.65 | 0.96 | 1.05 | 1.67 | 1.16 | 1.01 | 1.86 | 1.07 |
| Rps25 | 1.23 | 1.77 | 1.00 | 0.94 | 1.12 | 0.83 | 1.03 | 0.52 | 0.94 | 1.04 | 1.71 | 1.06 |
| Rps27a | 1.31 | 1.93 | 1.11 | 0.90 | 0.55 | 0.83 | 0.83 | 1.87 | 1.24 | 1.06 | 2.04 | 1.05 |
| Rps27rt | 1.00 | 1.00 | 3.33 | 1.00 | 0.11 | 1.00 | 1.00 | 4.77 | 1.00 | 1.00 | 1.00 | 1.00 |
| Rps29 | 2.69 | 1.20 | 1.26 | 0.78 | 0.48 | 0.59 | 0.54 | 0.91 | 0.68 | 1.85 | 2.19 | 0.97 |
| Rps3 | 1.27 | 1.63 | 1.16 | 0.93 | 0.89 | 0.96 | 1.10 | 1.02 | 1.10 | 1.09 | 1.92 | 1.20 |
| Rps4l | 1.60 | 1.60 | 1.15 | 1.47 | 0.48 | 0.94 | 0.97 | 1.36 | 0.95 | 1.03 | 1.37 | 1.59 |
| Rps4x | 1.25 | 1.65 | 1.02 | 0.81 | 0.57 | 0.77 | 1.04 | 2.12 | 1.12 | 0.97 | 1.67 | 1.07 |
| Rps6 | 1.29 | 1.56 | 0.98 | 0.85 | 0.79 | 0.80 | 1.03 | 1.03 | 1.06 | 0.91 | 1.69 | 1.07 |
| Rps8 | 1.28 | 1.53 | 0.99 | 0.85 | 0.58 | 0.77 | 1.11 | 1.81 | 1.09 | 0.87 | 1.74 | 0.92 |
| Rps9 | 1.30 | 1.60 | 1.02 | 0.90 | 0.51 | 0.83 | 1.07 | 3.19 | 1.14 | 0.98 | 1.83 | 1.13 |
| Rpsa | 1.29 | 1.69 | 1.04 | 0.92 | 0.33 | 0.90 | 1.25 | 6.80 | 1.32 | 1.00 | 1.83 | 1.01 |
| Rpusd3 | 0.87 | 1.07 | 0.62 | 0.74 | 0.63 | 0.83 | 0.69 | 1.28 | 0.73 | 0.81 | 1.27 | 0.93 |
| Rrad | 1.10 | 1.20 | 1.08 | 0.68 | 0.53 | 1.18 | 1.00 | 1.00 | 1.00 | 0.61 | 0.93 | 1.27 |
| Rrp12 | 1.07 | 0.93 | 0.90 | 1.33 | 0.80 | 0.96 | 1.20 | 2.75 | 1.13 | 0.83 | 1.29 | 0.73 |
| Rrp7a | 1.26 | 1.41 | 1.12 | 0.96 | 0.75 | 0.93 | 1.07 | 1.39 | 1.09 | 1.17 | 1.47 | 1.09 |
| Rsad2 | 1.32 | 1.44 | 2.07 | 0.61 | 0.50 | 0.90 | 1.57 | 1.67 | 1.89 | 4.46 | 2.38 | 2.47 |
| Rsbn1 | 0.44 | 0.29 | 0.67 | 1.35 | 1.00 | 0.83 | 1.26 | 1.00 | 1.36 | 1.15 | 0.55 | 1.13 |
| Rsl1d1 | 1.03 | 0.99 | 0.93 | 0.99 | 0.92 | 0.94 | 1.28 | 2.43 | 1.03 | 0.96 | 1.35 | 1.04 |
| Rsph9 | 2.18 | 1.58 | 1.94 | 0.74 | 0.78 | 0.53 | 1.00 | 1.00 | 1.00 | 0.73 | 1.52 | 0.93 |
| Rtcb | 1.17 | 1.27 | 0.99 | 1.15 | 0.98 | 0.96 | 1.11 | 1.46 | 1.12 | 1.07 | 1.48 | 1.04 |
| Rtn1 | 1.55 | 1.00 | 1.17 | 1.00 | 1.00 | 1.00 | 1.00 | 1.00 | 1.00 | 1.22 | 1.33 | 1.10 |
| Rtn2 | 1.58 | 1.09 | 1.00 | 1.00 | 0.65 | 1.18 | 1.00 | 0.92 | 1.00 | 0.93 | 1.38 | 1.14 |
| Rtp4 | 3.23 | 2.70 | 2.45 | 4.26 | 1.61 | 4.83 | 1.07 | 0.99 | 2.25 | 8.52 | 4.81 | 4.06 |
| Rxrg | 0.54 | 0.64 | 0.68 | 1.00 | 1.00 | 1.00 | 0.66 | 0.76 | 1.24 | 1.00 | 1.00 | 1.00 |
| S100a10 | 1.20 | 1.49 | 1.19 | 1.11 | 0.93 | 0.98 | 5.24 | 6.12 | 6.54 | 1.18 | 2.10 | 1.22 |
| S100a13 | 1.19 | 1.71 | 0.81 | 0.92 | 0.45 | 0.85 | 0.98 | 2.93 | 0.89 | 1.05 | 1.80 | 0.99 |
| S100a16 | 1.10 | 1.11 | 0.85 | 0.74 | 0.59 | 0.75 | 0.72 | 1.27 | 0.72 | 0.97 | 1.43 | 0.96 |
| S100a3 | 1.03 | 0.75 | 0.69 | 1.00 | 1.00 | 1.00 | 1.00 | 1.00 | 1.00 | 1.00 | 1.00 | 1.00 |
| S100a4 | 1.21 | 1.19 | 1.01 | 0.92 | 0.62 | 1.30 | 1.00 | 1.17 | 1.00 | 1.03 | 1.26 | 1.17 |
| S100a5 | 1.00 | 1.00 | 1.00 | 1.00 | 1.00 | 1.00 | 1.00 | 1.00 | 1.00 | 1.00 | 1.00 | 1.00 |
| S100a6 | 1.98 | 1.66 | 1.42 | 0.81 | 0.80 | 0.92 | 1.51 | 2.35 | 0.84 | 0.96 | 1.54 | 0.96 |
| S100a8 | 0.13 | 0.33 | 1.13 | 1.17 | 0.39 | 1.17 | 1.03 | 1.66 | 1.13 | 0.42 | 1.70 | 1.00 |
| S100a9 | 0.08 | 0.34 | 0.93 | 1.00 | 1.45 | 2.26 | 0.88 | 2.53 | 2.00 | 0.43 | 1.00 | 1.00 |
| S100b | 1.00 | 1.00 | 0.46 | 1.00 | 1.00 | 1.00 | 1.00 | 1.00 | 1.00 | 0.72 | 1.34 | 1.09 |
| Saa1 | 1.48 | 1.28 | 1.29 | 1.00 | 0.72 | 1.00 | 3.07 | 4.22 | 2.01 | 1.08 | 1.72 | 1.16 |
| Saa2 | 0.76 | 1.68 | 0.75 | 1.00 | 1.00 | 1.00 | 5.36 | 2.11 | 3.49 | 0.79 | 2.12 | 0.79 |
| Saa3 | 1.00 | 1.24 | 1.10 | 1.00 | 1.00 | 1.00 | 1.38 | 0.61 | 1.78 | 0.80 | 0.83 | 1.00 |
| Safb2 | 0.97 | 0.99 | 1.05 | 0.98 | 0.61 | 1.12 | 1.27 | 3.06 | 1.15 | 0.92 | 1.01 | 0.97 |
| Samd11 | 1.54 | 1.39 | 1.63 | 1.00 | 0.38 | 1.00 | 1.00 | 4.86 | 1.00 | 1.16 | 2.05 | 1.00 |
| Samm50 | 1.13 | 1.24 | 0.86 | 0.82 | 0.55 | 0.83 | 1.38 | 2.95 | 1.03 | 0.78 | 1.36 | 0.88 |
| Sap25 | 1.48 | 3.47 | 0.90 | 1.00 | 0.86 | 1.00 | 1.00 | 0.93 | 1.00 | 1.00 | 3.49 | 1.00 |
| Sap30l | 0.99 | 1.29 | 0.97 | 1.19 | 0.80 | 1.33 | 0.85 | 1.91 | 0.96 | 0.99 | 1.30 | 0.94 |
| Sapcd1 | 0.98 | 1.24 | 0.71 | 1.00 | 0.56 | 1.00 | 1.00 | 1.67 | 1.00 | 1.06 | 2.08 | 2.03 |
| Sars | 1.28 | 1.30 | 1.12 | 1.16 | 0.70 | 1.09 | 1.03 | 1.57 | 0.86 | 0.96 | 1.35 | 0.93 |
| Sars2 | 1.01 | 1.33 | 0.77 | 0.88 | 0.64 | 0.94 | 0.86 | 1.58 | 0.65 | 1.02 | 1.56 | 1.03 |

Fig. 35- 251

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Rplp2 | 1.00 | 1.52 | 1.27 | 1.30 | 3.92 | 1.35 | 0.82 | 1.65 | 1.06 | 0.98 | 1.43 | 1.18 |
| Rplp2-ps1 | 0.99 | 1.09 | 1.08 | 1.15 | 2.94 | 1.37 | 0.88 | 3.20 | 0.96 | 1.16 | 1.46 | 1.01 |
| Rpp21 | 1.39 | 1.87 | 1.07 | 0.44 | 12.73 | 0.94 | 1.24 | 0.98 | 0.88 | 1.39 | 1.81 | 0.96 |
| Rpp25l | 2.22 | 2.31 | 2.33 | 2.39 | 6.16 | 2.43 | 1.66 | 3.43 | 2.07 | 2.31 | 2.85 | 1.93 |
| Rpp40 | 1.19 | 0.90 | 1.48 | 1.59 | 2.55 | 1.58 | 1.26 | 1.17 | 0.91 | 0.91 | 1.38 | 1.02 |
| Rpph1 | 1.00 | 1.00 | 1.00 | 1.00 | 0.11 | 1.00 | 1.00 | 15.43 | 1.00 | 1.14 | 0.81 | 0.09 |
| Rprl3 | 1.14 | 1.21 | 1.00 | 1.00 | 0.07 | 1.36 | 0.28 | 14.18 | 1.65 | 0.87 | 0.75 | 0.22 |
| Rps12 | 0.85 | 1.13 | 1.16 | 0.78 | 0.59 | 0.81 | 1.24 | 0.95 | 1.01 | 0.94 | 2.63 | 1.29 |
| Rps13 | 0.94 | 0.98 | 1.04 | 1.13 | 6.64 | 1.57 | 0.86 | 0.86 | 0.96 | 1.29 | 1.38 | 1.19 |
| Rps14 | 0.92 | 1.07 | 1.03 | 0.82 | 3.00 | 1.05 | 0.90 | 1.33 | 0.88 | 0.97 | 1.21 | 0.95 |
| Rps15 | 0.96 | 1.14 | 1.14 | 0.87 | 2.61 | 1.10 | 1.03 | 2.42 | 1.10 | 1.23 | 1.60 | 1.08 |
| Rps15a-ps4 | 0.94 | 0.91 | 1.00 | 1.10 | 4.83 | 1.09 | 1.13 | 0.63 | 1.14 | 1.24 | 1.52 | 1.16 |
| Rps15a-ps6 | 0.94 | 0.95 | 1.01 | 1.06 | 3.64 | 1.26 | 0.88 | 0.92 | 0.97 | 1.32 | 1.49 | 1.13 |
| Rps16 | 0.94 | 1.05 | 1.18 | 1.10 | 2.67 | 0.94 | 0.61 | 3.04 | 0.90 | 1.22 | 1.62 | 1.06 |
| Rps18 | 1.43 | 1.06 | 0.80 | 1.00 | 2.63 | 2.21 | 0.93 | 6.40 | 1.00 | 1.59 | 3.76 | 1.14 |
| Rps19 | 0.98 | 0.97 | 1.13 | 0.81 | 4.07 | 1.04 | 0.79 | 1.72 | 1.08 | 1.23 | 1.64 | 1.18 |
| Rps19-ps3 | 1.21 | 1.11 | 0.99 | 0.81 | 2.30 | 1.33 | 0.96 | 0.47 | 0.91 | 1.14 | 1.48 | 0.89 |
| Rps20 | 1.07 | 1.11 | 1.20 | 1.02 | 2.49 | 1.19 | 0.91 | 2.83 | 0.92 | 1.38 | 1.56 | 1.04 |
| Rps24 | 1.04 | 1.00 | 1.17 | 0.97 | 3.13 | 1.22 | 0.86 | 2.05 | 0.94 | 1.30 | 1.57 | 1.13 |
| Rps25 | 0.90 | 1.18 | 1.12 | 0.98 | 4.21 | 1.26 | 1.03 | 0.69 | 0.95 | 1.19 | 1.61 | 1.11 |
| Rps27a | 1.14 | 1.06 | 1.05 | 0.79 | 3.56 | 1.20 | 0.95 | 2.73 | 0.85 | 1.31 | 1.56 | 0.99 |
| Rps27rt | 1.00 | 1.00 | 1.00 | 1.00 | 1.09 | 1.00 | 1.00 | 2.53 | 1.00 | 1.00 | 1.00 | 7.78 |
| Rps29 | 0.71 | 0.75 | 1.01 | 0.62 | 2.18 | 0.69 | 1.00 | 1.01 | 0.83 | 0.48 | 0.95 | 1.35 |
| Rps3 | 1.05 | 1.12 | 1.13 | 1.12 | 4.96 | 1.23 | 0.98 | 1.14 | 0.91 | 1.24 | 1.54 | 1.17 |
| Rps4l | 0.96 | 0.94 | 0.96 | 0.98 | 1.38 | 1.09 | 0.93 | 1.85 | 1.07 | 1.31 | 1.06 | 1.59 |
| Rps4x | 0.99 | 1.02 | 1.10 | 0.88 | 2.13 | 1.09 | 0.74 | 2.10 | 0.58 | 1.26 | 1.45 | 1.11 |
| Rps6 | 0.93 | 1.03 | 1.03 | 1.22 | 3.77 | 1.49 | 0.90 | 1.22 | 1.03 | 1.16 | 1.35 | 0.97 |
| Rps8 | 0.90 | 1.08 | 1.19 | 0.86 | 4.05 | 1.29 | 1.04 | 2.43 | 0.97 | 1.21 | 1.46 | 1.00 |
| Rps9 | 1.07 | 1.10 | 1.17 | 1.07 | 2.31 | 1.09 | 0.87 | 4.68 | 0.93 | 1.15 | 1.56 | 1.08 |
| Rpsa | 0.96 | 1.10 | 1.06 | 0.95 | 1.26 | 1.14 | 1.11 | 10.55 | 1.10 | 1.28 | 1.53 | 1.06 |
| Rpusd3 | 1.38 | 0.93 | 1.10 | 0.58 | 0.82 | 0.60 | 0.80 | 1.92 | 0.91 | 0.97 | 0.82 | 0.73 |
| Rrad | 1.08 | 1.49 | 1.36 | 0.78 | 1.00 | 0.97 | 1.00 | 1.00 | 1.00 | 1.00 | 0.92 | 0.86 |
| Rrp12 | 0.93 | 0.92 | 1.07 | 1.41 | 1.68 | 1.07 | 1.26 | 2.51 | 1.04 | 1.20 | 1.00 | 0.98 |
| Rrp7a | 1.00 | 1.05 | 1.03 | 1.11 | 2.22 | 1.21 | 0.82 | 1.68 | 0.91 | 1.21 | 1.30 | 1.15 |
| Rsad2 | 4.28 | 7.71 | 2.26 | 0.97 | 1.40 | 1.21 | 1.00 | 1.00 | 1.00 | 0.78 | 0.54 | 0.35 |
| Rsbn1 | 1.22 | 1.06 | 0.93 | 1.45 | 0.82 | 0.75 | 1.19 | 0.47 | 1.08 | 1.01 | 0.47 | 1.17 |
| Rsl1d1 | 0.97 | 0.99 | 0.91 | 1.30 | 5.78 | 1.38 | 1.00 | 1.78 | 1.04 | 1.25 | 1.23 | 1.02 |
| Rsph9 | 1.24 | 1.38 | 1.37 | 1.23 | 1.22 | 1.98 | 0.91 | 1.66 | 1.09 | 1.00 | 1.89 | 1.39 |
| Rtcb | 0.95 | 0.92 | 1.04 | 1.14 | 3.33 | 1.25 | 1.13 | 1.37 | 1.01 | 1.26 | 1.24 | 1.12 |
| Rtn1 | 2.10 | 1.70 | 1.56 | 0.61 | 1.47 | 0.80 | 0.88 | 1.24 | 1.01 | 0.61 | 7.73 | 0.87 |
| Rtn2 | 1.43 | 1.62 | 1.20 | 0.53 | 1.13 | 0.56 | 1.23 | 3.65 | 1.33 | 1.04 | 2.15 | 0.85 |
| Rtp4 | 11.89 | 16.65 | 13.14 | 3.00 | 0.69 | 5.39 | 1.00 | 1.00 | 1.00 | 6.28 | 4.03 | 4.87 |
| Rxrg | 1.00 | 1.00 | 1.00 | 0.27 | 0.93 | 0.41 | 1.00 | 2.42 | 1.00 | 0.83 | 0.71 | 0.75 |
| S100a10 | 1.27 | 1.30 | 1.40 | 0.96 | 2.44 | 0.89 | 0.85 | 1.28 | 0.89 | 1.14 | 1.13 | 1.03 |
| S100a13 | 0.89 | 0.78 | 0.84 | 0.78 | 1.37 | 0.90 | 1.48 | 5.33 | 0.80 | 1.22 | 1.13 | 0.90 |
| S100a16 | 0.82 | 0.89 | 0.89 | 1.09 | 2.27 | 1.15 | 0.89 | 2.34 | 0.85 | 1.20 | 1.53 | 1.02 |
| S100a3 | 0.58 | 0.92 | 1.24 | 1.00 | 1.00 | 1.00 | 1.00 | 1.00 | 1.00 | 1.00 | 0.90 | 1.00 |
| S100a4 | 1.45 | 1.12 | 1.44 | 0.68 | 1.51 | 0.52 | 1.00 | 2.64 | 1.01 | 0.49 | 0.41 | 0.47 |
| S100a5 | 1.00 | 1.00 | 1.00 | 1.00 | 1.00 | 1.00 | 1.00 | 1.00 | 1.00 | 1.00 | 1.00 | 1.00 |
| S100a6 | 0.60 | 0.65 | 0.52 | 1.29 | 3.59 | 0.97 | 0.91 | 1.03 | 0.81 | 0.82 | 0.94 | 0.89 |
| S100a8 | 2.68 | 0.68 | 1.00 | 0.62 | 0.39 | 0.36 | 1.00 | 0.50 | 1.00 | 11.49 | 6.49 | 4.92 |
| S100a9 | 0.90 | 0.91 | 0.81 | 0.25 | 0.39 | 1.77 | 1.00 | 0.67 | 1.00 | 10.38 | 5.97 | 5.00 |
| S100b | 1.57 | 1.27 | 2.05 | 0.40 | 1.00 | 0.32 | 1.00 | 1.73 | 1.00 | 1.00 | 13.07 | 1.00 |
| Saa1 | 1.00 | 1.00 | 1.00 | 13.50 | 13.08 | 2.34 | 1.09 | 2.46 | 1.09 | 1.00 | 1.00 | 1.00 |
| Saa2 | 1.00 | 1.00 | 1.00 | 15.30 | 10.22 | 3.88 | 1.00 | 1.00 | 1.00 | 1.00 | 1.00 | 1.00 |
| Saa3 | 1.00 | 1.00 | 1.00 | 1.02 | 0.83 | 0.42 | 1.00 | 1.95 | 1.00 | 1.00 | 1.01 | 1.00 |
| Safb2 | 0.99 | 1.08 | 1.05 | 1.42 | 2.23 | 1.24 | 1.48 | 4.66 | 1.49 | 1.10 | 1.00 | 1.18 |
| Samd11 | 1.09 | 1.00 | 1.00 | 1.38 | 6.77 | 2.48 | 0.88 | 2.11 | 1.22 | 0.73 | 0.86 | 0.63 |
| Samm50 | 0.92 | 0.98 | 0.87 | 0.79 | 2.94 | 1.06 | 1.08 | 2.89 | 0.92 | 1.03 | 1.32 | 1.05 |
| Sap25 | 1.00 | 1.12 | 1.00 | 1.00 | 6.25 | 1.86 | 1.00 | 0.90 | 1.28 | 1.06 | 1.52 | 0.77 |
| Sap30l | 0.91 | 1.08 | 1.17 | 1.04 | 1.70 | 0.94 | 0.78 | 1.62 | 0.97 | 1.00 | 1.30 | 0.95 |
| Sapcd1 | 0.72 | 1.73 | 2.11 | 0.69 | 1.44 | 1.52 | 0.62 | 2.58 | 1.50 | 2.04 | 2.23 | 2.26 |
| Sars | 0.97 | 0.98 | 0.96 | 1.21 | 2.97 | 1.08 | 0.95 | 2.35 | 0.81 | 1.08 | 1.22 | 1.00 |
| Sars2 | 1.01 | 1.60 | 0.78 | 0.73 | 3.83 | 0.77 | 1.45 | 3.02 | 0.95 | 1.03 | 1.22 | 0.88 |

Fig. 35- 252

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Rplp2 | 0.52 | 0.81 | 0.85 | 0.87 | 1.03 | 1.47 | 1.55 | 5.32 | 0.77 | 2.23 | 1.18 | 1.07 |
| Rplp2-ps1 | 0.70 | 0.87 | 0.79 | 1.19 | 0.94 | 1.08 | 1.17 | 16.90 | 0.87 | 3.30 | 1.18 | 1.10 |
| Rpp21 | 1.08 | 0.72 | 0.47 | 0.92 | 1.26 | 1.73 | 1.36 | 8.69 | 1.09 | 3.93 | 1.46 | 1.82 |
| Rpp25l | 2.52 | 3.15 | 2.94 | 2.28 | 2.28 | 1.94 | 2.51 | 15.23 | 2.26 | 4.81 | 2.43 | 2.53 |
| Rpp40 | 1.00 | 1.00 | 1.00 | 1.12 | 3.27 | 1.52 | 1.25 | 3.56 | 1.27 | 1.39 | 1.00 | 0.94 |
| Rpph1 | 1.00 | 1.00 | 1.00 | 1.00 | 0.31 | 1.00 | 0.52 | 38.35 | 1.00 | 2.86 | 3.74 | 8.25 |
| Rprl3 | 3.49 | 1.00 | 1.00 | 1.00 | 0.56 | 1.00 | 1.73 | 17.63 | 1.00 | 2.96 | 0.75 | 1.49 |
| Rps12 | 1.21 | 0.96 | 1.97 | 1.00 | 0.91 | 1.15 | 3.18 | 1.27 | 0.77 | 1.27 | 1.07 | 1.00 |
| Rps13 | 0.72 | 0.74 | 1.19 | 1.07 | 1.88 | 0.94 | 1.01 | 3.39 | 0.90 | 1.63 | 1.24 | 1.14 |
| Rps14 | 0.84 | 0.88 | 1.05 | 1.15 | 1.22 | 1.02 | 1.16 | 5.10 | 0.75 | 1.98 | 1.03 | 0.90 |
| Rps15 | 0.79 | 0.97 | 0.98 | 1.06 | 1.08 | 0.96 | 1.23 | 12.01 | 0.86 | 3.35 | 1.28 | 1.16 |
| Rps15a-ps4 | 0.75 | 0.72 | 0.90 | 1.41 | 2.29 | 1.02 | 1.00 | 2.89 | 0.77 | 1.55 | 1.06 | 0.93 |
| Rps15a-ps6 | 0.75 | 0.85 | 0.88 | 1.17 | 1.01 | 0.84 | 0.98 | 3.58 | 0.76 | 1.68 | 1.08 | 0.93 |
| Rps16 | 0.78 | 0.91 | 0.82 | 1.04 | 0.93 | 1.20 | 0.97 | 15.25 | 0.89 | 4.16 | 1.33 | 1.44 |
| Rps18 | 0.70 | 1.58 | 2.15 | 1.00 | 1.10 | 1.00 | 0.80 | 7.11 | 0.83 | 2.89 | 0.85 | 1.07 |
| Rps19 | 0.75 | 0.77 | 0.81 | 0.97 | 0.75 | 1.18 | 1.10 | 11.87 | 0.80 | 3.04 | 1.18 | 1.18 |
| Rps19-ps3 | 0.58 | 1.10 | 0.70 | 1.09 | 0.61 | 0.98 | 1.35 | 2.80 | 0.74 | 1.91 | 0.87 | 1.02 |
| Rps20 | 0.67 | 0.93 | 1.01 | 1.15 | 0.92 | 1.14 | 1.20 | 17.72 | 0.96 | 3.39 | 1.24 | 1.09 |
| Rps24 | 0.84 | 0.89 | 0.89 | 0.96 | 1.11 | 1.06 | 1.26 | 7.95 | 0.84 | 2.65 | 1.20 | 1.18 |
| Rps25 | 0.95 | 0.82 | 0.98 | 0.97 | 2.20 | 1.19 | 1.33 | 2.65 | 0.86 | 2.00 | 1.15 | 1.12 |
| Rps27a | 0.89 | 0.78 | 0.93 | 0.87 | 0.69 | 1.09 | 1.20 | 18.99 | 0.93 | 4.31 | 1.29 | 1.31 |
| Rps27rt | 1.00 | 1.00 | 0.76 | 1.00 | 0.07 | 1.00 | 1.00 | 24.31 | 0.58 | 8.17 | 1.00 | 2.16 |
| Rps29 | 1.00 | 0.72 | 0.78 | 0.49 | 0.78 | 1.60 | 1.44 | 10.98 | 0.76 | 2.72 | 1.20 | 1.94 |
| Rps3 | 0.86 | 0.94 | 1.00 | 1.23 | 1.03 | 1.08 | 1.09 | 3.37 | 0.83 | 1.94 | 1.15 | 1.06 |
| Rps4l | 1.31 | 1.19 | 1.01 | 1.42 | 0.72 | 0.97 | 1.32 | 4.47 | 0.82 | 7.39 | 1.40 | 2.51 |
| Rps4x | 0.77 | 1.01 | 1.05 | 0.97 | 1.00 | 1.05 | 1.04 | 8.03 | 0.82 | 2.15 | 1.13 | 1.02 |
| Rps6 | 0.74 | 0.90 | 0.93 | 1.14 | 1.22 | 1.03 | 0.89 | 4.66 | 0.78 | 1.92 | 0.99 | 0.94 |
| Rps8 | 0.71 | 0.79 | 0.92 | 0.87 | 1.10 | 1.15 | 1.05 | 9.02 | 0.78 | 2.56 | 1.02 | 1.02 |
| Rps9 | 0.78 | 1.01 | 0.95 | 1.09 | 0.88 | 1.09 | 1.05 | 25.07 | 0.87 | 4.35 | 1.27 | 1.13 |
| Rpsa | 0.68 | 0.90 | 1.11 | 0.89 | 0.64 | 0.96 | 1.20 | 62.51 | 0.90 | 6.19 | 1.20 | 1.04 |
| Rpusd3 | 1.00 | 0.80 | 0.54 | 0.55 | 0.56 | 0.64 | 1.03 | 8.41 | 0.83 | 2.32 | 1.05 | 0.41 |
| Rrad | 1.00 | 1.00 | 1.00 | 1.00 | 1.00 | 1.28 | 0.88 | 0.93 | 1.07 | 1.82 | 1.38 | 0.65 |
| Rrp12 | 1.10 | 1.00 | 1.00 | 1.05 | 0.73 | 0.99 | 1.16 | 6.42 | 0.93 | 1.86 | 0.56 | 0.63 |
| Rrp7a | 0.82 | 1.04 | 0.94 | 1.30 | 0.98 | 1.16 | 1.09 | 4.90 | 0.88 | 1.99 | 1.13 | 1.13 |
| Rsad2 | 1.00 | 1.00 | 1.00 | 1.00 | 1.00 | 1.00 | 1.00 | 1.00 | 1.00 | 1.13 | 0.91 | 0.90 |
| Rsbn1 | 1.00 | 1.11 | 1.00 | 1.03 | 1.00 | 0.91 | 0.89 | 0.29 | 1.45 | 1.00 | 1.05 | 0.71 |
| Rsl1d1 | 1.04 | 0.86 | 1.05 | 1.08 | 0.89 | 1.06 | 0.89 | 2.08 | 0.96 | 0.96 | 0.82 | 0.92 |
| Rsph9 | 1.00 | 1.33 | 1.00 | 0.91 | 1.25 | 0.96 | 1.61 | 5.15 | 1.03 | 1.20 | 0.78 | 1.35 |
| Rtcb | 0.80 | 0.69 | 0.87 | 1.11 | 1.34 | 1.01 | 0.97 | 3.66 | 0.91 | 1.92 | 1.16 | 0.98 |
| Rtn1 | 1.00 | 1.00 | 1.00 | 1.10 | 1.22 | 1.07 | 0.94 | 1.20 | 1.07 | 1.00 | 0.91 | 1.00 |
| Rtn2 | 1.00 | 1.00 | 1.00 | 1.08 | 1.06 | 1.06 | 1.73 | 15.59 | 1.90 | 1.00 | 1.00 | 1.00 |
| Rtp4 | 1.00 | 1.00 | 1.00 | 1.29 | 1.00 | 2.49 | 1.46 | 1.09 | 1.97 | 8.47 | 20.94 | 19.89 |
| Rxrg | 1.00 | 1.00 | 1.00 | 0.97 | 2.47 | 1.12 | 1.83 | 5.64 | 1.19 | 1.00 | 1.00 | 1.00 |
| S100a10 | 0.82 | 1.20 | 1.33 | 1.26 | 1.67 | 1.05 | 1.05 | 6.37 | 1.04 | 2.85 | 1.29 | 1.36 |
| S100a13 | 2.39 | 1.34 | 1.67 | 1.13 | 0.65 | 0.82 | 1.49 | 36.88 | 1.13 | 4.77 | 1.49 | 1.43 |
| S100a16 | 0.96 | 0.86 | 0.86 | 0.95 | 0.77 | 0.95 | 1.05 | 7.65 | 0.75 | 0.98 | 0.94 | 1.00 |
| S100a3 | 1.00 | 1.00 | 1.00 | 1.00 | 0.26 | 1.00 | 2.07 | 7.79 | 1.17 | 1.00 | 1.00 | 1.00 |
| S100a4 | 1.00 | 1.00 | 0.47 | 1.48 | 0.94 | 1.73 | 1.21 | 6.51 | 0.96 | 1.83 | 0.72 | 0.84 |
| S100a5 | 1.00 | 1.00 | 1.00 | 2.33 | 32.03 | 0.68 | 1.44 | 1.00 | 1.00 | 1.00 | 1.00 | 1.00 |
| S100a6 | 0.91 | 0.82 | 1.39 | 1.19 | 0.97 | 1.04 | 1.27 | 4.98 | 1.00 | 2.18 | 1.24 | 1.30 |
| S100a8 | 1.08 | 1.00 | 1.00 | 3.44 | 0.19 | 1.00 | 0.18 | 3.34 | 0.72 | 2.36 | 1.62 | 1.46 |
| S100a9 | 1.37 | 1.00 | 1.00 | 1.33 | 0.26 | 1.37 | 0.29 | 1.86 | 0.43 | 2.29 | 1.55 | 1.48 |
| S100b | 1.00 | 1.00 | 1.00 | 1.03 | 0.98 | 0.97 | 1.93 | 3.63 | 1.30 | 1.00 | 1.00 | 1.00 |
| Saa1 | 1.00 | 1.00 | 1.00 | 1.00 | 1.00 | 1.00 | 0.66 | 5.34 | 0.84 | 1.00 | 1.00 | 1.00 |
| Saa2 | 1.00 | 1.00 | 1.00 | 1.00 | 1.00 | 1.00 | 1.00 | 1.00 | 1.00 | 1.00 | 1.00 | 1.00 |
| Saa3 | 1.00 | 1.00 | 1.00 | 1.00 | 1.00 | 1.00 | 1.00 | 9.75 | 1.25 | 17.22 | 1.89 | 1.00 |
| Safb2 | 1.19 | 1.18 | 1.21 | 1.07 | 0.83 | 1.03 | 1.20 | 5.37 | 1.09 | 2.57 | 0.96 | 0.97 |
| Samd11 | 1.00 | 1.00 | 1.00 | 1.16 | 1.06 | 0.96 | 1.19 | 16.74 | 1.23 | 1.40 | 1.37 | 1.05 |
| Samm50 | 0.84 | 0.83 | 1.04 | 1.11 | 0.79 | 1.03 | 1.26 | 11.58 | 0.94 | 2.92 | 1.05 | 1.11 |
| Sap25 | 1.00 | 1.00 | 1.00 | 1.00 | 0.85 | 1.00 | 1.62 | 8.07 | 0.73 | 2.57 | 1.79 | 1.50 |
| Sap30l | 1.48 | 0.86 | 0.96 | 0.81 | 1.11 | 0.95 | 1.14 | 6.16 | 1.09 | 3.23 | 1.66 | 1.16 |
| Sapcd1 | 1.00 | 1.00 | 1.00 | 1.84 | 18.84 | 2.02 | 1.20 | 8.18 | 1.35 | 3.26 | 1.17 | 1.42 |
| Sars | 0.99 | 0.82 | 0.76 | 1.17 | 1.22 | 1.10 | 1.18 | 6.62 | 0.97 | 2.76 | 1.34 | 1.22 |
| Sars2 | 1.00 | 0.93 | 1.00 | 1.30 | 0.57 | 1.04 | 0.74 | 8.00 | 0.64 | 2.57 | 0.98 | 1.15 |

Fig. 35- 253

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Sat1 | 1.87 | 1.62 | 1.72 | 1.77 | 6.89 | 1.10 | 1.25 | 1.72 | 1.36 | 0.99 | 1.59 | 1.01 |
| Sat2 | 0.88 | 0.57 | 0.93 | 0.63 | 5.18 | 0.74 | 1.00 | 0.73 | 0.52 | 0.68 | 1.08 | 0.84 |
| Saysd1 | 1.36 | 0.89 | 1.28 | 0.85 | 5.02 | 1.26 | 1.24 | 1.16 | 1.03 | 1.90 | 2.56 | 0.97 |
| Sbsn | 1.64 | 0.24 | 1.80 | 1.00 | 3.02 | 1.02 | 1.00 | 1.00 | 1.00 | 3.86 | 4.64 | 0.88 |
| Scand1 | 1.33 | 0.57 | 0.96 | 0.80 | 14.78 | 1.23 | 1.23 | 0.66 | 1.01 | 2.44 | 5.01 | 0.89 |
| Scara5 | 1.77 | 1.56 | 1.74 | 2.21 | 1.18 | 1.67 | 1.08 | 1.15 | 1.11 | 0.66 | 0.84 | 1.17 |
| Scarletltr | 1.00 | 1.00 | 1.00 | 1.00 | 1.00 | 1.00 | 1.00 | 1.00 | 1.00 | 2.99 | 8.21 | 2.03 |
| Scarna6 | 1.00 | 1.00 | 1.00 | 1.00 | 2.82 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scd3 | 1.00 | 1.00 | 1.00 | 3.77 | 0.21 | 0.75 | 1.00 | 1.00 | 1.00 | 1.00 | 1.00 | 1.76 |
| Scg2 | 1.00 | 1.00 | 1.00 | 1.00 | 0.09 | 1.00 | 1.00 | 1.00 | 1.00 | 1.00 | 1.00 | 1.00 |
| Scg3 | 0.98 | 1.00 | 1.00 | 1.00 | 0.18 | 1.00 | 1.00 | 1.00 | 1.00 | 1.00 | 1.00 | 1.00 |
| Scgb1a1 | 0.90 | 1.93 | 1.00 | 8.15 | 5.27 | 1.00 | 1.00 | 1.00 | 1.00 | 2.10 | 2.83 | 1.22 |
| Scgb2b27 | 1.00 | 1.00 | 1.00 | 1.00 | 1.00 | 1.00 | 1.00 | 1.00 | 1.00 | 1.00 | 1.00 | 1.00 |
| Scgb3a1 | 1.00 | 1.33 | 1.00 | 1.91 | 4.98 | 1.00 | 1.82 | 0.44 | 2.99 | 2.29 | 6.33 | 0.83 |
| Scgn | 1.00 | 1.00 | 1.00 | 1.00 | 1.00 | 1.00 | 1.00 | 1.00 | 1.00 | 1.00 | 1.00 | 1.00 |
| Scn3b | 1.81 | 1.00 | 1.31 | 1.00 | 0.33 | 1.00 | 1.00 | 1.00 | 0.95 | 0.16 | 0.13 | 0.30 |
| Scn4b | 0.59 | 1.23 | 0.71 | 0.98 | 0.18 | 1.04 | 0.75 | 0.76 | 0.80 | 1.00 | 1.00 | 0.61 |
| Scnm1 | 1.45 | 0.38 | 0.61 | 0.63 | 4.44 | 0.64 | 0.99 | 0.67 | 1.00 | 2.07 | 3.02 | 1.06 |
| Scnn1b | 1.00 | 1.00 | 1.00 | 1.00 | 1.00 | 1.00 | 1.00 | 1.00 | 1.00 | 3.99 | 4.28 | 1.33 |
| Sco2 | 1.28 | 2.01 | 1.19 | 0.39 | 0.88 | 1.12 | 1.54 | 1.13 | 0.94 | 0.09 | 0.47 | 1.30 |
| Scrg1 | 1.00 | 1.00 | 1.00 | 1.00 | 1.00 | 1.00 | 1.00 | 1.00 | 1.00 | 1.00 | 1.67 | 1.00 |
| Scrn1 | 1.00 | 1.00 | 1.00 | 1.00 | 0.31 | 1.00 | 0.64 | 1.12 | 0.95 | 1.53 | 1.20 | 1.35 |
| Scrn2 | 0.81 | 0.60 | 0.65 | 0.44 | 4.28 | 0.65 | 0.73 | 0.80 | 0.86 | 2.13 | 2.21 | 0.98 |
| Scrt1 | 1.00 | 1.00 | 1.00 | 1.00 | 0.26 | 1.00 | 1.00 | 1.00 | 1.00 | 1.00 | 1.00 | 1.00 |
| Sct | 1.00 | 1.00 | 1.00 | 1.00 | 1.00 | 1.00 | 1.00 | 1.00 | 1.00 | 1.00 | 1.00 | 1.00 |
| Sctr | 3.27 | 1.26 | 2.39 | 0.86 | 6.09 | 0.78 | 1.00 | 1.00 | 1.00 | 1.00 | 1.00 | 1.00 |
| Sdc4 | 5.77 | 5.27 | 3.90 | 1.06 | 3.01 | 2.25 | 1.63 | 1.60 | 1.78 | 0.92 | 1.61 | 1.06 |
| Sdcbp2 | 0.94 | 0.61 | 1.00 | 0.50 | 4.88 | 1.89 | 0.90 | 0.96 | 1.20 | 2.14 | 4.52 | 1.10 |
| Sdf2l1 | 1.98 | 2.43 | 1.13 | 1.01 | 3.01 | 2.73 | 1.27 | 0.96 | 1.95 | 0.61 | 0.88 | 1.66 |
| Sdsl | 1.00 | 1.00 | 1.00 | 0.30 | 6.43 | 0.77 | 0.97 | 0.90 | 0.80 | 1.70 | 2.89 | 1.00 |
| Sec61b | 0.22 | 0.21 | 0.28 | 0.17 | 5.19 | 0.33 | 0.31 | 0.25 | 0.38 | 1.79 | 2.77 | 0.56 |
| Sec61g | 1.00 | 0.65 | 1.00 | 1.00 | 4.66 | 1.00 | 1.00 | 1.00 | 1.00 | 1.01 | 4.41 | 1.00 |
| Sectm1b | 1.00 | 1.00 | 1.00 | 1.00 | 1.00 | 1.00 | 1.00 | 1.00 | 1.00 | 1.00 | 1.00 | 1.00 |
| Selenbp1 | 0.69 | 0.37 | 0.91 | 1.11 | 10.90 | 1.13 | 1.29 | 1.17 | 0.95 | 3.15 | 4.41 | 1.46 |
| Selenbp2 | 0.77 | 0.61 | 1.45 | 0.93 | 4.07 | 1.23 | 1.47 | 1.35 | 0.93 | 2.06 | 2.18 | 1.49 |
| Selk | 1.24 | 1.06 | 0.84 | 0.90 | 1.83 | 1.14 | 0.77 | 0.76 | 0.90 | 0.54 | 0.77 | 0.97 |
| Selm | 0.96 | 0.39 | 0.76 | 0.41 | 9.74 | 0.95 | 0.78 | 0.76 | 0.91 | 2.16 | 3.31 | 0.92 |
| Selo | 1.10 | 0.95 | 0.76 | 0.61 | 1.75 | 1.02 | 1.02 | 0.88 | 0.77 | 1.03 | 1.08 | 0.96 |
| Sept1 | 1.00 | 1.00 | 1.00 | 0.48 | 6.89 | 0.78 | 0.91 | 0.74 | 0.79 | 0.66 | 1.41 | 0.79 |
| Sept5 | 1.03 | 0.89 | 1.21 | 1.17 | 0.09 | 1.32 | 1.52 | 0.84 | 1.50 | 0.41 | 0.82 | 1.29 |
| Sepw1 | 1.45 | 0.52 | 0.80 | 0.61 | 16.69 | 1.34 | 0.79 | 0.73 | 0.90 | 2.89 | 4.47 | 0.81 |
| Serf1 | 1.19 | 1.44 | 0.86 | 1.14 | 3.12 | 1.02 | 0.85 | 0.38 | 0.68 | 0.74 | 1.10 | 0.72 |
| Sergef | 1.00 | 0.52 | 0.76 | 0.33 | 8.06 | 0.69 | 1.02 | 0.85 | 0.75 | 3.96 | 5.56 | 1.11 |
| Serhl | 0.87 | 0.61 | 0.99 | 0.51 | 13.89 | 0.92 | 1.34 | 1.07 | 0.79 | 4.39 | 2.61 | 0.90 |
| Serp2 | 1.00 | 1.00 | 1.00 | 1.00 | 0.30 | 1.00 | 1.20 | 0.99 | 1.00 | 1.18 | 0.98 | 1.57 |
| Serpina12 | 1.00 | 1.00 | 1.00 | 0.88 | 2.63 | 1.13 | 1.00 | 1.00 | 1.00 | 1.00 | 1.00 | 1.00 |
| Serpina1a | 1.74 | 1.42 | 1.00 | 0.92 | 0.31 | 0.81 | 7.15 | 0.37 | 3.08 | 0.44 | 0.63 | 1.81 |
| Serpina1b | 2.33 | 2.80 | 2.31 | 0.86 | 0.75 | 0.86 | 10.46 | 0.78 | 2.89 | 0.34 | 1.55 | 1.90 |
| Serpina1c | 2.86 | 1.42 | 1.38 | 0.87 | 0.53 | 1.03 | 9.75 | 0.39 | 3.70 | 0.14 | 0.51 | 2.59 |
| Serpina1d | 1.15 | 1.00 | 1.00 | 0.47 | 0.22 | 0.74 | 5.14 | 0.38 | 1.97 | 0.55 | 0.90 | 1.90 |
| Serpina1e | 1.00 | 1.00 | 1.00 | 0.45 | 0.33 | 0.82 | 3.29 | 0.97 | 1.68 | 1.00 | 0.63 | 1.61 |
| Serpina3a | 1.00 | 1.00 | 1.00 | 1.00 | 1.00 | 1.00 | 1.00 | 1.00 | 1.00 | 1.00 | 1.00 | 1.00 |
| Serpina3g | 1.00 | 1.00 | 1.00 | 1.00 | 1.00 | 1.18 | 1.67 | 1.78 | 2.36 | 1.04 | 0.80 | 1.80 |
| Serpina3k | 3.80 | 2.24 | 1.00 | 8.67 | 2.45 | 1.30 | 10.09 | 0.22 | 1.53 | 0.13 | 1.48 | 4.66 |
| Serpina3m | 2.55 | 1.57 | 1.81 | 3.02 | 2.18 | 1.27 | 4.89 | 2.33 | 8.27 | 3.79 | 5.82 | 8.00 |
| Serpina3n | 6.63 | 6.35 | 3.68 | 4.22 | 2.87 | 2.26 | 4.86 | 4.08 | 5.38 | 2.98 | 4.13 | 3.79 |
| Serpina6 | 1.00 | 1.00 | 1.00 | 1.00 | 1.00 | 1.00 | 1.00 | 1.00 | 1.00 | 1.00 | 1.00 | 1.00 |
| Serpinb1a | 1.16 | 0.59 | 0.69 | 0.89 | 1.00 | 0.74 | 0.74 | 0.39 | 0.52 | 0.77 | 1.20 | 0.75 |
| Serpinb6a | 3.24 | 1.89 | 2.26 | 1.01 | 7.70 | 1.53 | 1.18 | 1.15 | 1.17 | 2.18 | 2.78 | 1.08 |
| Serpinb6b | 1.00 | 1.00 | 1.00 | 1.00 | 1.00 | 1.00 | 0.63 | 0.67 | 0.94 | 1.08 | 1.00 | 1.55 |
| Serpine2 | 1.00 | 0.89 | 0.79 | 1.20 | 0.84 | 1.14 | 1.18 | 0.95 | 1.39 | 0.79 | 0.83 | 0.82 |
| Serping1 | 1.29 | 0.89 | 1.27 | 2.51 | 5.71 | 1.47 | 0.97 | 0.87 | 1.06 | 1.23 | 1.57 | 1.08 |
| Sertad1 | 1.17 | 0.70 | 1.21 | 0.51 | 7.31 | 0.98 | 1.03 | 1.12 | 1.32 | 2.81 | 3.67 | 1.21 |

Fig. 35- 254

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Sat1 | 1.94 | 2.00 | 1.62 | 0.92 | 1.13 | 0.92 | 1.16 | 0.89 | 0.93 | 1.01 | 1.36 | 1.01 |
| Sat2 | 1.38 | 1.25 | 1.32 | 0.83 | 0.86 | 1.14 | 0.72 | 0.65 | 0.60 | 0.80 | 0.58 | 0.94 |
| Saysd1 | 1.11 | 1.61 | 1.13 | 0.96 | 0.85 | 1.02 | 1.15 | 1.76 | 0.95 | 0.96 | 1.46 | 1.12 |
| Sbsn | 0.85 | 0.77 | 0.88 | 0.94 | 0.29 | 0.80 | 1.00 | 1.00 | 1.00 | 0.52 | 0.78 | 0.50 |
| Scand1 | 1.37 | 1.85 | 1.14 | 0.85 | 0.62 | 1.22 | 1.13 | 1.63 | 1.14 | 1.13 | 1.87 | 1.20 |
| Scara5 | 2.09 | 1.19 | 1.15 | 1.00 | 1.00 | 1.00 | 7.77 | 7.24 | 25.66 | 1.33 | 1.65 | 1.55 |
| Scarletltr | 1.00 | 1.00 | 1.00 | 1.00 | 1.00 | 1.00 | 1.00 | 1.00 | 1.00 | 1.00 | 1.29 | 1.00 |
| Scarna6 | 1.00 | 1.00 | 1.00 | 1.00 | 1.98 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scd3 | 1.00 | 1.00 | 0.92 | 0.95 | 1.00 | 1.00 | 0.42 | 1.00 | 0.49 | 1.00 | 1.00 | 0.72 |
| Scg2 | 1.00 | 1.00 | 1.00 | 1.00 | 1.00 | 1.00 | 1.00 | 1.00 | 1.00 | 1.50 | 1.07 | 1.32 |
| Scg3 | 1.00 | 1.00 | 1.00 | 1.00 | 1.00 | 1.00 | 1.00 | 1.00 | 1.00 | 1.35 | 1.53 | 1.02 |
| Scgb1a1 | 0.31 | 1.13 | 0.86 | 1.00 | 0.97 | 1.00 | 1.00 | 1.90 | 1.00 | 2.76 | 1.69 | 1.00 |
| Scgb2b27 | 1.00 | 1.00 | 0.33 | 1.00 | 1.00 | 1.00 | 1.00 | 1.00 | 1.00 | 1.00 | 1.00 | 1.00 |
| Scgb3a1 | 1.18 | 2.66 | 1.24 | 1.00 | 1.00 | 1.00 | 1.00 | 0.79 | 1.00 | 1.00 | 1.86 | 1.37 |
| Scgn | 1.00 | 1.00 | 1.00 | 1.00 | 1.00 | 1.00 | 1.00 | 1.00 | 1.00 | 0.83 | 1.74 | 1.11 |
| Scn3b | 1.00 | 1.00 | 1.00 | 1.00 | 1.00 | 1.00 | 1.00 | 1.00 | 1.00 | 1.41 | 1.00 | 1.01 |
| Scn4b | 0.48 | 0.39 | 0.67 | 0.75 | 1.04 | 0.85 | 1.60 | 1.00 | 1.00 | 1.00 | 1.00 | 1.00 |
| Scnm1 | 1.39 | 1.56 | 0.96 | 1.00 | 0.79 | 0.76 | 1.04 | 0.97 | 1.06 | 0.71 | 1.39 | 0.90 |
| Scnn1b | 1.09 | 1.74 | 2.23 | 0.89 | 0.60 | 1.06 | 1.00 | 1.00 | 1.00 | 1.35 | 2.22 | 1.62 |
| Sco2 | 1.01 | 1.04 | 0.90 | 1.22 | 11.73 | 0.99 | 1.87 | 1.04 | 1.98 | 0.98 | 1.15 | 1.23 |
| Scrg1 | 1.00 | 1.00 | 1.00 | 1.00 | 1.00 | 1.00 | 1.00 | 1.00 | 1.00 | 1.00 | 1.00 | 1.00 |
| Scrn1 | 1.00 | 1.00 | 1.00 | 1.00 | 1.00 | 1.06 | 1.00 | 1.00 | 1.00 | 0.91 | 0.92 | 0.59 |
| Scrn2 | 0.83 | 1.13 | 0.84 | 0.89 | 0.56 | 0.88 | 0.81 | 1.37 | 0.88 | 0.70 | 1.06 | 1.15 |
| Scrt1 | 1.00 | 1.00 | 1.00 | 1.00 | 1.00 | 1.00 | 1.00 | 1.00 | 1.00 | 1.00 | 1.00 | 1.00 |
| Sct | 1.00 | 1.00 | 1.00 | 1.00 | 1.00 | 1.00 | 1.00 | 2.00 | 1.00 | 1.57 | 3.25 | 1.70 |
| Sctr | 1.00 | 1.00 | 1.00 | 1.00 | 1.00 | 1.00 | 1.00 | 1.00 | 1.00 | 1.00 | 1.00 | 1.00 |
| Sdc4 | 2.56 | 2.24 | 1.83 | 1.07 | 1.24 | 1.04 | 1.26 | 1.24 | 0.84 | 1.10 | 1.29 | 1.09 |
| Sdcbp2 | 2.04 | 2.05 | 1.86 | 1.00 | 0.75 | 1.00 | 1.00 | 1.00 | 1.00 | 1.19 | 1.81 | 1.17 |
| Sdf2l1 | 1.06 | 1.20 | 1.37 | 0.87 | 2.76 | 1.63 | 1.29 | 0.45 | 1.10 | 0.96 | 1.26 | 1.15 |
| Sdsl | 1.00 | 1.00 | 1.00 | 1.02 | 0.64 | 0.80 | 2.43 | 8.24 | 2.00 | 0.82 | 1.49 | 1.27 |
| Sec61b | 0.47 | 0.61 | 0.46 | 0.27 | 0.64 | 0.39 | 0.36 | 1.50 | 0.48 | 0.37 | 0.82 | 0.47 |
| Sec61g | 1.27 | 1.00 | 1.79 | 1.00 | 0.51 | 1.00 | 1.00 | 0.99 | 1.00 | 1.00 | 1.60 | 1.19 |
| Sectm1b | 1.79 | 0.87 | 1.52 | 1.61 | 1.76 | 1.59 | 1.00 | 1.00 | 1.00 | 1.21 | 1.08 | 1.07 |
| Selenbp1 | 2.66 | 2.63 | 1.60 | 1.44 | 0.96 | 1.12 | 1.24 | 2.25 | 0.99 | 1.24 | 1.98 | 1.14 |
| Selenbp2 | 1.54 | 1.55 | 1.29 | 1.50 | 1.15 | 1.13 | 4.56 | 5.64 | 2.25 | 1.31 | 1.62 | 1.06 |
| Selk | 1.17 | 1.50 | 1.02 | 0.80 | 1.74 | 0.85 | 1.17 | 0.64 | 1.06 | 1.01 | 1.67 | 1.15 |
| Selm | 1.48 | 2.20 | 1.27 | 1.06 | 0.63 | 1.04 | 1.54 | 2.63 | 1.49 | 1.07 | 1.81 | 1.03 |
| Selo | 1.04 | 1.05 | 1.08 | 0.98 | 1.30 | 1.07 | 0.88 | 0.69 | 0.84 | 1.11 | 1.21 | 1.00 |
| Sept1 | 0.98 | 1.28 | 0.83 | 0.74 | 0.62 | 0.69 | 1.00 | 1.00 | 1.00 | 0.99 | 1.05 | 1.35 |
| Sept5 | 1.17 | 1.50 | 1.53 | 1.00 | 1.00 | 1.00 | 1.00 | 1.00 | 1.00 | 0.96 | 1.05 | 0.97 |
| Sepw1 | 1.23 | 1.80 | 1.09 | 0.73 | 0.55 | 0.84 | 0.82 | 2.16 | 0.81 | 1.02 | 1.87 | 1.03 |
| Serf1 | 0.92 | 0.90 | 0.71 | 0.75 | 0.73 | 0.79 | 0.28 | 0.16 | 0.58 | 1.02 | 1.57 | 0.77 |
| Sergef | 1.39 | 2.03 | 1.19 | 0.67 | 0.40 | 0.82 | 0.86 | 2.35 | 0.77 | 1.17 | 1.93 | 1.04 |
| Serhl | 0.78 | 1.24 | 0.76 | 0.99 | 0.44 | 1.09 | 1.02 | 2.56 | 0.67 | 1.04 | 1.55 | 1.01 |
| Serp2 | 0.62 | 1.76 | 0.93 | 1.00 | 1.04 | 1.00 | 1.00 | 1.00 | 1.00 | 0.98 | 1.32 | 0.57 |
| Serpina12 | 1.00 | 1.00 | 1.00 | 1.00 | 1.00 | 1.00 | 5.32 | 9.88 | 3.63 | 1.00 | 1.00 | 1.00 |
| Serpina1a | 10.34 | 1.67 | 1.65 | 2.15 | 1.57 | 1.95 | 1.38 | 1.49 | 1.26 | 2.97 | 1.38 | 1.90 |
| Serpina1b | 6.42 | 3.42 | 1.85 | 2.19 | 2.75 | 2.27 | 1.41 | 2.33 | 1.30 | 3.58 | 2.25 | 2.33 |
| Serpina1c | 8.56 | 1.86 | 1.30 | 2.37 | 0.71 | 1.72 | 1.36 | 0.92 | 1.24 | 3.09 | 3.42 | 1.78 |
| Serpina1d | 9.18 | 1.79 | 1.84 | 1.93 | 1.00 | 2.17 | 1.24 | 0.43 | 1.16 | 2.05 | 1.42 | 2.03 |
| Serpina1e | 6.38 | 2.89 | 1.59 | 2.48 | 1.00 | 2.16 | 1.44 | 0.24 | 1.26 | 1.00 | 1.00 | 1.37 |
| Serpina3a | 1.00 | 1.00 | 1.00 | 0.27 | 0.16 | 0.39 | 1.56 | 1.54 | 0.98 | 1.00 | 1.00 | 1.00 |
| Serpina3g | 1.54 | 1.66 | 2.52 | 1.00 | 1.00 | 0.61 | 5.62 | 1.00 | 3.02 | 1.11 | 0.81 | 1.08 |
| Serpina3k | 17.69 | 1.96 | 0.87 | 1.36 | 0.77 | 0.96 | 1.83 | 1.71 | 1.27 | 3.38 | 1.80 | 1.63 |
| Serpina3m | 6.56 | 3.51 | 5.05 | 1.00 | 1.00 | 1.00 | 1.87 | 1.15 | 1.37 | 1.17 | 1.08 | 1.95 |
| Serpina3n | 3.53 | 2.99 | 3.11 | 1.56 | 1.02 | 1.07 | 1.82 | 1.47 | 1.62 | 1.96 | 2.24 | 1.49 |
| Serpina6 | 1.00 | 1.00 | 1.00 | 1.20 | 1.00 | 1.00 | 0.04 | 0.08 | 0.09 | 1.00 | 1.00 | 1.00 |
| Serpinb1a | 1.02 | 1.09 | 1.12 | 0.94 | 1.56 | 0.93 | 2.93 | 3.84 | 7.96 | 1.23 | 1.59 | 1.21 |
| Serpinb6a | 2.35 | 2.19 | 1.75 | 1.63 | 1.24 | 1.50 | 0.93 | 1.83 | 1.02 | 1.21 | 1.83 | 1.19 |
| Serpinb6b | 0.93 | 0.89 | 1.20 | 0.87 | 0.74 | 0.90 | 5.33 | 3.54 | 4.26 | 0.83 | 0.68 | 0.74 |
| Serpine2 | 1.84 | 1.62 | 1.41 | 0.73 | 0.88 | 0.86 | 2.56 | 1.67 | 1.52 | 1.01 | 1.02 | 1.03 |
| Serping1 | 2.68 | 1.90 | 1.62 | 1.18 | 1.11 | 1.10 | 1.07 | 0.99 | 1.15 | 1.04 | 1.26 | 1.10 |
| Sertad1 | 1.04 | 1.25 | 1.16 | 0.82 | 0.53 | 1.10 | 1.03 | 2.21 | 0.94 | 1.02 | 1.70 | 1.09 |

Fig. 35- 255

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Sat1 | 1.21 | 1.24 | 1.09 | 2.17 | 4.16 | 1.08 | 0.61 | 0.52 | 0.94 | 1.07 | 1.16 | 1.01 |
| Sat2 | 0.92 | 1.59 | 1.23 | 0.67 | 0.38 | 0.52 | 0.67 | 1.40 | 1.05 | 0.79 | 1.20 | 0.65 |
| Saysd1 | 1.23 | 1.32 | 1.26 | 1.19 | 1.90 | 0.96 | 0.85 | 1.60 | 0.99 | 1.12 | 1.15 | 1.05 |
| Sbsn | 0.95 | 1.30 | 1.16 | 0.48 | 0.38 | 1.17 | 0.99 | 6.76 | 1.17 | 1.02 | 1.14 | 1.11 |
| Scand1 | 0.86 | 1.25 | 1.03 | 1.10 | 2.71 | 1.03 | 0.86 | 3.55 | 1.08 | 1.06 | 1.42 | 1.01 |
| Scara5 | 1.94 | 2.43 | 2.64 | 1.38 | 0.73 | 1.14 | 0.93 | 0.94 | 0.97 | 1.50 | 1.73 | 2.04 |
| Scarletltr | 0.99 | 0.97 | 1.00 | 1.00 | 1.00 | 1.00 | 1.00 | 1.00 | 1.00 | 1.00 | 1.00 | 1.00 |
| Scarna6 | 1.00 | 1.00 | 1.00 | 1.00 | 0.02 | 1.00 | 1.00 | 0.43 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 16.88 |
| Scd3 | 1.00 | 1.00 | 1.00 | 1.64 | 0.48 | 0.47 | 0.83 | 1.00 | 1.01 | 0.79 | 1.00 | 0.85 |
| Scg2 | 1.69 | 1.68 | 1.57 | 1.00 | 1.00 | 1.00 | 1.00 | 1.00 | 1.00 | 1.00 | 16.80 | 1.00 |
| Scg3 | 1.73 | 1.41 | 1.30 | 0.42 | 1.00 | 0.45 | 1.00 | 1.00 | 1.00 | 1.00 | 8.76 | 1.00 |
| Scgb1a1 | 1.34 | 1.37 | 1.66 | 1.00 | 0.27 | 1.00 | 1.00 | 4.57 | 1.00 | 1.03 | 1.27 | 1.00 |
| Scgb2b27 | 1.00 | 1.00 | 1.00 | 1.00 | 1.00 | 1.00 | 1.00 | 1.00 | 1.00 | 1.00 | 1.00 | 1.00 |
| Scgb3a1 | 1.81 | 1.18 | 3.88 | 1.00 | 1.00 | 1.00 | 1.00 | 1.38 | 1.00 | 1.00 | 1.00 | 1.00 |
| Scgn | 0.84 | 0.67 | 0.83 | 1.00 | 1.00 | 1.00 | 1.00 | 8.72 | 1.56 | 1.00 | 1.00 | 1.00 |
| Scn3b | 1.00 | 1.00 | 1.00 | 0.96 | 1.00 | 1.78 | 1.00 | 1.00 | 1.00 | 1.12 | 5.27 | 1.13 |
| Scn4b | 1.21 | 1.41 | 1.50 | 1.53 | 1.00 | 1.56 | 1.00 | 1.00 | 1.00 | 0.75 | 5.97 | 0.73 |
| Scnm1 | 0.75 | 1.19 | 0.76 | 1.08 | 1.59 | 0.98 | 0.91 | 1.84 | 0.93 | 1.16 | 1.20 | 0.91 |
| Scnn1b | 1.34 | 1.57 | 1.27 | 1.00 | 1.00 | 1.00 | 1.00 | 1.00 | 1.00 | 1.00 | 1.00 | 1.00 |
| Sco2 | 1.36 | 1.51 | 1.29 | 1.13 | 1.00 | 1.21 | 0.98 | 0.07 | 0.91 | 1.25 | 1.27 | 1.10 |
| Scrg1 | 1.00 | 1.00 | 1.00 | 1.00 | 1.00 | 1.00 | 1.00 | 1.00 | 1.00 | 1.00 | 1.82 | 1.00 |
| Scrn1 | 1.85 | 0.73 | 0.98 | 0.88 | 1.00 | 0.89 | 1.12 | 1.09 | 0.94 | 1.00 | 5.48 | 1.00 |
| Scrn2 | 0.99 | 0.80 | 1.05 | 0.70 | 1.31 | 1.05 | 0.81 | 2.37 | 1.37 | 1.15 | 1.15 | 1.11 |
| Scrt1 | 1.00 | 1.00 | 1.00 | 1.00 | 1.00 | 1.00 | 0.95 | 2.19 | 1.22 | 1.00 | 5.23 | 1.00 |
| Sct | 1.48 | 1.81 | 1.86 | 1.00 | 1.35 | 1.08 | 1.00 | 5.96 | 1.19 | 1.00 | 1.00 | 1.00 |
| Sctr | 0.69 | 1.03 | 0.72 | 1.05 | 3.36 | 1.33 | 1.00 | 1.00 | 1.00 | 1.00 | 1.00 | 1.00 |
| Sdc4 | 1.19 | 1.22 | 1.04 | 2.20 | 2.73 | 2.93 | 1.07 | 0.68 | 0.94 | 1.16 | 1.12 | 0.91 |
| Sdcbp2 | 0.72 | 0.78 | 0.68 | 1.85 | 4.71 | 1.71 | 0.85 | 1.52 | 0.92 | 1.03 | 1.96 | 1.15 |
| Sdf2l1 | 1.15 | 0.84 | 1.11 | 2.14 | 1.22 | 0.98 | 0.95 | 0.69 | 1.04 | 1.22 | 1.08 | 1.13 |
| Sdsl | 1.32 | 1.23 | 1.19 | 0.58 | 0.80 | 0.34 | 0.94 | 2.84 | 0.83 | 1.00 | 1.00 | 1.00 |
| Sec61b | 0.43 | 0.36 | 0.43 | 0.43 | 5.30 | 0.48 | 0.30 | 1.33 | 0.24 | 0.46 | 0.57 | 0.33 |
| Sec61g | 1.00 | 0.66 | 1.43 | 1.19 | 1.64 | 1.28 | 0.71 | 1.75 | 1.05 | 0.61 | 1.96 | 1.14 |
| Sectm1b | 0.72 | 0.72 | 0.62 | 2.06 | 1.00 | 5.23 | 1.00 | 1.00 | 1.00 | 1.00 | 1.00 | 1.00 |
| Selenbp1 | 1.06 | 1.28 | 1.11 | 0.68 | 1.32 | 0.87 | 1.08 | 2.23 | 0.78 | 0.90 | 1.40 | 1.05 |
| Selenbp2 | 1.23 | 1.58 | 0.98 | 0.75 | 2.34 | 0.95 | 1.37 | 1.63 | 0.75 | 0.81 | 1.08 | 1.07 |
| Selk | 1.03 | 1.04 | 1.01 | 1.02 | 4.53 | 1.10 | 1.03 | 1.83 | 0.95 | 1.04 | 1.12 | 1.04 |
| Selm | 1.13 | 1.30 | 1.51 | 0.93 | 1.83 | 1.17 | 1.04 | 2.76 | 0.90 | 0.91 | 1.45 | 0.75 |
| Selo | 1.27 | 1.24 | 1.06 | 1.01 | 3.82 | 1.08 | 0.98 | 0.46 | 1.06 | 1.01 | 1.32 | 0.94 |
| Sept1 | 1.00 | 1.00 | 1.96 | 0.66 | 1.00 | 1.15 | 1.00 | 1.00 | 1.00 | 0.94 | 1.12 | 1.01 |
| Sept5 | 1.02 | 1.21 | 1.22 | 1.09 | 0.52 | 1.17 | 0.97 | 0.57 | 0.97 | 1.44 | 14.43 | 1.25 |
| Sepw1 | 1.03 | 1.05 | 1.18 | 0.85 | 1.80 | 0.89 | 0.89 | 3.49 | 0.98 | 0.96 | 1.37 | 0.95 |
| Serf1 | 0.91 | 0.48 | 1.30 | 0.87 | 1.45 | 0.55 | 0.95 | 0.65 | 1.02 | 0.87 | 0.66 | 1.92 |
| Sergef | 0.66 | 1.19 | 0.88 | 1.03 | 2.59 | 1.31 | 0.79 | 3.00 | 0.66 | 1.28 | 1.81 | 0.77 |
| Serhl | 1.08 | 0.70 | 1.23 | 0.57 | 1.22 | 1.10 | 0.82 | 0.45 | 1.58 | 0.96 | 0.68 | 1.39 |
| Serp2 | 1.00 | 1.00 | 1.22 | 0.45 | 1.00 | 0.76 | 1.11 | 1.06 | 1.27 | 1.72 | 5.72 | 0.99 |
| Serpina12 | 0.93 | 1.13 | 1.08 | 1.00 | 1.00 | 1.00 | 1.00 | 1.00 | 1.00 | 1.00 | 1.00 | 1.00 |
| Serpina1a | 2.09 | 5.03 | 3.35 | 1.52 | 1.00 | 0.83 | 1.41 | 1.00 | 1.82 | 1.33 | 1.40 | 1.34 |
| Serpina1b | 2.48 | 6.31 | 4.00 | 1.62 | 1.00 | 0.76 | 1.60 | 1.45 | 1.92 | 1.50 | 1.48 | 1.22 |
| Serpina1c | 2.00 | 5.41 | 4.66 | 1.38 | 0.89 | 0.81 | 1.51 | 2.98 | 1.38 | 1.51 | 1.47 | 1.32 |
| Serpina1d | 1.86 | 4.70 | 5.50 | 1.88 | 1.00 | 0.86 | 1.26 | 1.00 | 1.53 | 1.50 | 1.41 | 1.19 |
| Serpina1e | 1.82 | 3.12 | 2.15 | 1.59 | 0.85 | 0.93 | 1.00 | 1.00 | 1.00 | 1.33 | 1.55 | 1.17 |
| Serpina3a | 1.00 | 1.00 | 1.00 | 1.00 | 1.44 | 1.00 | 1.81 | 2.97 | 1.55 | 5.54 | 4.25 | 1.57 |
| Serpina3g | 2.69 | 1.18 | 1.56 | 0.66 | 0.73 | 1.03 | 1.00 | 1.00 | 1.00 | 1.05 | 0.68 | 0.68 |
| Serpina3k | 2.25 | 9.08 | 3.47 | 7.73 | 14.35 | 7.92 | 1.25 | 1.00 | 0.43 | 1.00 | 5.54 | 0.84 |
| Serpina3m | 2.70 | 5.64 | 2.97 | 5.75 | 3.06 | 8.61 | 1.00 | 1.00 | 1.00 | 2.99 | 2.79 | 2.94 |
| Serpina3n | 3.10 | 4.00 | 2.09 | 1.65 | 1.55 | 1.17 | 1.53 | 1.51 | 1.21 | 1.88 | 1.66 | 1.26 |
| Serpina6 | 1.00 | 1.00 | 1.03 | 1.00 | 1.00 | 1.00 | 1.00 | 1.00 | 1.00 | 1.00 | 1.00 | 1.00 |
| Serpinb1a | 0.77 | 0.75 | 0.70 | 0.85 | 0.62 | 0.96 | 0.66 | 0.47 | 0.78 | 1.36 | 1.07 | 1.10 |
| Serpinb6a | 0.89 | 1.01 | 0.92 | 1.22 | 2.85 | 0.98 | 1.12 | 2.01 | 1.22 | 1.03 | 1.25 | 0.89 |
| Serpinb6b | 2.48 | 1.65 | 1.32 | 2.14 | 1.00 | 2.33 | 1.03 | 1.00 | 1.76 | 0.76 | 0.62 | 0.83 |
| Serpine2 | 1.33 | 1.41 | 1.18 | 1.33 | 2.17 | 0.93 | 0.66 | 1.00 | 0.77 | 3.12 | 6.71 | 3.67 |
| Serping1 | 1.36 | 1.43 | 1.62 | 1.37 | 3.44 | 1.10 | 0.96 | 0.94 | 1.04 | 1.10 | 1.04 | 1.00 |
| Sertad1 | 0.79 | 0.87 | 0.91 | 1.32 | 2.29 | 1.39 | 0.78 | 2.91 | 1.22 | 1.00 | 0.99 | 1.03 |

Fig. 35- 256

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Sat1 | 1.46 | 1.33 | 1.09 | 1.49 | 1.10 | 1.09 | 1.02 | 1.68 | 0.96 | 1.73 | 1.57 | 1.39 |
| Sat2 | 0.50 | 1.05 | 0.79 | 0.68 | 2.89 | 0.98 | 0.77 | 2.87 | 1.29 | 1.00 | 1.00 | 1.00 |
| Saysd1 | 1.72 | 1.75 | 1.72 | 1.28 | 1.03 | 1.12 | 1.45 | 6.33 | 0.81 | 2.29 | 1.33 | 1.03 |
| Sbsn | 0.79 | 1.00 | 1.00 | 0.84 | 0.75 | 1.10 | 0.85 | 6.04 | 0.66 | 1.18 | 1.00 | 1.00 |
| Scand1 | 0.89 | 0.85 | 0.84 | 1.15 | 0.95 | 1.05 | 1.32 | 17.39 | 0.95 | 4.65 | 1.67 | 1.26 |
| Scara5 | 1.13 | 1.57 | 1.44 | 1.00 | 1.00 | 1.00 | 1.46 | 0.89 | 1.50 | 1.00 | 1.00 | 1.00 |
| Scarletltr | 1.00 | 1.00 | 1.00 | 1.00 | 1.00 | 1.00 | 0.98 | 34.40 | 1.00 | 1.00 | 1.00 | 1.00 |
| Scarna6 | 1.00 | 1.00 | 1.00 | 1.00 | 1.00 | 1.58 | 1.00 | 17.48 | 1.23 | 0.55 | 1.00 | 0.68 |
| Scarna8 | 1.00 | 1.00 | 1.00 | 1.00 | 1.00 | 1.00 | 1.00 | 1.00 | 1.00 | 1.00 | 1.00 | 1.00 |
| Scd3 | 1.00 | 1.00 | 1.00 | 1.10 | 1.64 | 1.22 | 3.79 | 5.87 | 4.62 | 1.00 | 1.00 | 1.00 |
| Scg2 | 0.82 | 0.69 | 1.22 | 1.33 | 1.74 | 1.17 | 1.00 | 1.00 | 1.00 | 1.00 | 1.00 | 1.00 |
| Scg3 | 0.76 | 0.63 | 1.45 | 0.99 | 0.87 | 0.98 | 0.89 | 1.35 | 1.00 | 1.00 | 1.00 | 1.00 |
| Scgb1a1 | 1.30 | 1.01 | 1.00 | 1.03 | 0.80 | 1.00 | 1.78 | 11.70 | 1.09 | 2.86 | 0.53 | 0.94 |
| Scgb2b27 | 1.00 | 1.00 | 1.00 | 1.00 | 1.00 | 1.00 | 0.94 | 8.27 | 0.82 | 1.00 | 1.00 | 1.00 |
| Scgb3a1 | 1.00 | 1.00 | 1.00 | 0.92 | 1.00 | 1.00 | 1.00 | 1.00 | 1.00 | 1.00 | 1.00 | 1.00 |
| Scgn | 1.00 | 1.00 | 0.98 | 0.79 | 0.36 | 1.00 | 1.00 | 1.00 | 1.00 | 1.00 | 1.00 | 1.00 |
| Scn3b | 1.00 | 1.00 | 1.00 | 1.07 | 1.18 | 1.07 | 1.03 | 1.00 | 1.00 | 1.00 | 1.00 | 1.00 |
| Scn4b | 0.85 | 1.59 | 0.77 | 0.94 | 1.13 | 1.01 | 1.07 | 0.24 | 1.56 | 1.00 | 1.00 | 1.00 |
| Scnm1 | 0.86 | 1.00 | 1.00 | 0.94 | 0.70 | 0.91 | 1.44 | 8.24 | 1.25 | 2.97 | 1.42 | 1.00 |
| Scnn1b | 1.00 | 1.00 | 1.00 | 1.00 | 1.08 | 1.00 | 1.31 | 10.39 | 0.82 | 1.00 | 1.00 | 1.00 |
| Sco2 | 1.21 | 0.98 | 1.26 | 1.32 | 1.00 | 1.23 | 1.14 | 0.05 | 0.91 | 0.25 | 1.32 | 0.79 |
| Scrg1 | 1.00 | 1.00 | 1.00 | 1.72 | 6.24 | 1.39 | 1.00 | 1.00 | 1.00 | 2.65 | 1.67 | 2.39 |
| Scrn1 | 1.00 | 1.00 | 1.00 | 0.87 | 0.46 | 0.84 | 0.77 | 1.00 | 1.04 | 1.00 | 1.00 | 1.00 |
| Scrn2 | 1.04 | 1.09 | 1.32 | 0.90 | 0.91 | 1.01 | 1.16 | 10.59 | 0.80 | 1.97 | 1.20 | 0.82 |
| Scrt1 | 1.00 | 1.00 | 1.00 | 1.05 | 0.97 | 0.98 | 1.47 | 0.95 | 0.78 | 1.00 | 1.00 | 1.00 |
| Sct | 1.00 | 1.00 | 1.00 | 1.00 | 0.12 | 1.00 | 1.00 | 6.56 | 1.00 | 1.00 | 1.00 | 1.00 |
| Sctr | 1.00 | 1.00 | 1.00 | 1.00 | 1.00 | 1.00 | 1.31 | 4.09 | 1.00 | 1.00 | 1.00 | 1.00 |
| Sdc4 | 1.36 | 1.99 | 1.33 | 1.10 | 1.11 | 1.13 | 1.25 | 1.28 | 1.01 | 1.07 | 0.90 | 1.13 |
| Sdcbp2 | 1.00 | 1.00 | 1.00 | 0.82 | 1.97 | 1.00 | 1.20 | 5.51 | 0.93 | 1.05 | 1.00 | 1.00 |
| Sdf2l1 | 0.93 | 0.93 | 0.82 | 1.31 | 7.93 | 1.12 | 0.90 | 0.56 | 0.59 | 0.82 | 1.07 | 1.15 |
| Sdsl | 1.07 | 0.95 | 1.61 | 1.49 | 0.77 | 1.13 | 1.00 | 1.00 | 1.00 | 1.73 | 0.71 | 0.87 |
| Sec61b | 0.38 | 0.37 | 0.46 | 0.31 | 1.17 | 0.39 | 0.37 | 7.52 | 0.43 | 2.32 | 0.59 | 0.72 |
| Sec61g | 1.00 | 1.00 | 0.95 | 1.00 | 1.03 | 1.00 | 1.00 | 5.10 | 1.17 | 1.82 | 1.12 | 1.03 |
| Sectm1b | 1.00 | 1.00 | 1.00 | 1.00 | 1.00 | 1.00 | 1.68 | 1.52 | 2.00 | 1.00 | 1.00 | 1.00 |
| Selenbp1 | 0.64 | 0.64 | 0.55 | 1.36 | 0.66 | 0.89 | 1.44 | 9.10 | 1.15 | 1.56 | 0.77 | 0.83 |
| Selenbp2 | 0.84 | 1.23 | 0.50 | 1.00 | 0.90 | 1.00 | 1.58 | 2.75 | 0.90 | 0.87 | 0.89 | 0.76 |
| Selk | 1.00 | 0.89 | 1.29 | 1.19 | 6.43 | 1.08 | 1.37 | 0.82 | 1.05 | 0.96 | 1.33 | 1.20 |
| Selm | 0.65 | 1.09 | 0.89 | 1.13 | 0.91 | 1.14 | 1.21 | 16.42 | 1.28 | 3.43 | 1.43 | 1.14 |
| Selo | 1.05 | 0.73 | 0.74 | 1.19 | 5.59 | 0.98 | 1.09 | 0.76 | 0.92 | 1.35 | 1.30 | 1.13 |
| Sept1 | 1.00 | 1.00 | 1.00 | 1.00 | 1.00 | 1.00 | 1.41 | 2.81 | 1.12 | 1.65 | 1.50 | 1.22 |
| Sept5 | 1.00 | 1.00 | 1.00 | 1.03 | 1.03 | 1.02 | 0.93 | 0.10 | 0.75 | 0.93 | 1.18 | 1.07 |
| Sepw1 | 0.84 | 1.11 | 1.08 | 1.06 | 0.89 | 1.06 | 1.36 | 16.80 | 0.85 | 4.09 | 1.36 | 1.39 |
| Serf1 | 0.53 | 0.54 | 0.80 | 0.77 | 6.98 | 1.13 | 1.19 | 0.96 | 0.54 | 0.65 | 0.52 | 1.95 |
| Sergef | 0.77 | 0.77 | 0.70 | 0.88 | 0.79 | 1.02 | 1.13 | 20.86 | 0.89 | 5.05 | 1.32 | 1.10 |
| Serhl | 1.45 | 1.28 | 0.83 | 0.83 | 1.00 | 1.40 | 0.85 | 19.01 | 0.76 | 2.71 | 0.89 | 1.14 |
| Serp2 | 1.00 | 1.00 | 1.00 | 1.12 | 1.14 | 1.04 | 1.00 | 1.11 | 1.00 | 1.00 | 1.00 | 1.00 |
| Serpina12 | 1.00 | 1.00 | 1.00 | 1.00 | 1.00 | 1.00 | 0.99 | 4.43 | 0.63 | 1.00 | 1.00 | 1.00 |
| Serpina1a | 1.00 | 1.00 | 0.77 | 0.54 | 0.84 | 1.19 | 1.00 | 1.00 | 1.00 | 1.00 | 1.00 | 1.00 |
| Serpina1b | 1.00 | 1.00 | 0.69 | 0.30 | 1.00 | 1.07 | 1.63 | 1.00 | 1.91 | 1.00 | 1.00 | 1.00 |
| Serpina1c | 1.00 | 1.00 | 0.84 | 0.29 | 1.00 | 1.33 | 1.00 | 1.00 | 1.64 | 1.00 | 1.00 | 1.00 |
| Serpina1d | 1.00 | 1.00 | 1.00 | 0.49 | 1.00 | 1.00 | 1.00 | 1.00 | 1.18 | 1.00 | 1.00 | 1.00 |
| Serpina1e | 1.00 | 1.00 | 1.00 | 1.00 | 1.00 | 1.00 | 1.00 | 1.00 | 1.00 | 1.00 | 1.00 | 1.00 |
| Serpina3a | 1.00 | 1.00 | 1.00 | 1.00 | 1.00 | 1.00 | 1.00 | 1.00 | 1.00 | 1.00 | 1.00 | 1.00 |
| Serpina3g | 1.00 | 1.00 | 0.83 | 1.00 | 1.00 | 1.00 | 0.90 | 0.41 | 0.82 | 0.90 | 0.94 | 0.91 |
| Serpina3k | 1.00 | 1.00 | 0.75 | 0.32 | 1.00 | 0.94 | 1.00 | 1.26 | 1.13 | 1.00 | 1.00 | 1.00 |
| Serpina3m | 1.00 | 1.00 | 1.00 | 1.00 | 1.00 | 1.52 | 2.17 | 1.00 | 2.79 | 1.00 | 1.00 | 1.00 |
| Serpina3n | 1.28 | 1.96 | 1.57 | 1.61 | 3.26 | 1.39 | 1.56 | 1.38 | 1.69 | 1.00 | 1.48 | 2.07 |
| Serpina6 | 1.86 | 2.04 | 9.90 | 1.00 | 1.00 | 1.00 | 1.00 | 1.00 | 1.00 | 1.00 | 1.00 | 1.00 |
| Serpinb1a | 1.44 | 1.21 | 1.12 | 0.65 | 0.53 | 0.57 | 1.28 | 1.35 | 1.09 | 1.94 | 1.63 | 1.58 |
| Serpinb6a | 1.97 | 1.80 | 2.19 | 1.37 | 1.02 | 1.28 | 1.32 | 7.18 | 1.34 | 2.35 | 1.15 | 1.31 |
| Serpinb6b | 1.00 | 1.00 | 1.00 | 0.85 | 1.00 | 0.75 | 0.96 | 1.00 | 1.00 | 0.64 | 0.91 | 0.78 |
| Serpine2 | 0.84 | 0.97 | 0.82 | 1.03 | 1.07 | 0.99 | 1.23 | 1.51 | 1.40 | 1.98 | 1.97 | 2.04 |
| Serping1 | 0.71 | 1.13 | 1.06 | 1.28 | 2.06 | 1.26 | 1.30 | 2.86 | 1.31 | 0.74 | 0.61 | 1.48 |
| Sertad1 | 1.08 | 1.54 | 1.36 | 0.87 | 0.90 | 1.10 | 1.26 | 13.14 | 0.87 | 2.62 | 1.04 | 1.17 |

Fig. 35- 257

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Sertad3 | 1.02 | 0.75 | 1.08 | 0.83 | 0.99 | 0.83 | 0.84 | 0.68 | 1.18 | 1.49 | 1.59 | 1.22 |
| Sesn1 | 2.82 | 3.76 | 3.75 | 6.68 | 11.04 | 2.53 | 1.95 | 2.36 | 1.04 | 1.27 | 1.31 | 1.43 |
| Setd4 | 1.00 | 0.91 | 1.00 | 0.34 | 5.23 | 1.38 | 0.54 | 1.35 | 0.79 | 2.80 | 2.61 | 1.54 |
| Setd7 | 0.74 | 1.19 | 0.93 | 8.13 | 1.27 | 1.71 | 1.28 | 1.31 | 1.29 | 0.91 | 0.56 | 1.00 |
| Setdb2 | 2.12 | 1.00 | 1.14 | 43.65 | 9.18 | 1.56 | 7.20 | 6.08 | 1.60 | 1.00 | 1.00 | 1.30 |
| Sez6 | 1.00 | 1.00 | 1.00 | 1.00 | 0.32 | 1.00 | 1.00 | 1.00 | 1.00 | 1.00 | 1.00 | 1.00 |
| Sez6l | 1.00 | 1.00 | 1.00 | 1.00 | 0.32 | 1.00 | 1.00 | 1.00 | 1.00 | 1.00 | 1.00 | 1.00 |
| Sez6l2 | 1.00 | 1.00 | 1.00 | 1.00 | 0.17 | 1.00 | 1.00 | 0.95 | 1.12 | 1.00 | 1.00 | 1.00 |
| Sf3a3 | 0.89 | 0.49 | 0.91 | 0.69 | 6.14 | 0.83 | 1.18 | 0.66 | 0.99 | 1.97 | 2.69 | 1.07 |
| Sfn | 0.99 | 0.57 | 0.89 | 0.65 | 2.96 | 1.41 | 1.11 | 0.65 | 0.82 | 3.99 | 4.03 | 1.04 |
| Sfta2 | 1.00 | 1.00 | 1.00 | 1.00 | 1.00 | 1.00 | 1.00 | 1.00 | 1.00 | 2.99 | 5.42 | 1.40 |
| Sftpb | 1.00 | 1.23 | 1.00 | 1.00 | 6.43 | 1.00 | 1.00 | 1.00 | 1.00 | 2.59 | 4.06 | 1.14 |
| Sftpc | 1.26 | 1.00 | 1.00 | 3.39 | 6.30 | 1.00 | 1.00 | 1.00 | 1.00 | 2.14 | 2.89 | 0.88 |
| Sgca | 1.10 | 0.68 | 0.99 | 1.00 | 2.84 | 1.25 | 1.08 | 0.95 | 0.82 | 2.80 | 2.31 | 0.99 |
| Sgk1 | 1.46 | 2.36 | 1.18 | 1.85 | 1.03 | 1.31 | 1.55 | 2.12 | 1.35 | 1.36 | 1.15 | 1.23 |
| Sgk3 | 2.67 | 2.90 | 2.03 | 5.19 | 2.36 | 1.52 | 1.13 | 1.65 | 0.94 | 0.72 | 0.74 | 0.77 |
| Sgsh | 0.80 | 0.73 | 1.27 | 0.65 | 1.18 | 1.04 | 1.39 | 1.15 | 1.23 | 1.10 | 1.17 | 0.89 |
| Sh2d4a | 1.00 | 0.52 | 1.02 | 4.16 | 6.96 | 1.02 | 1.61 | 1.43 | 1.02 | 1.24 | 0.86 | 0.90 |
| Sh2d7 | 1.24 | 0.64 | 0.94 | 0.30 | 7.81 | 1.13 | 1.00 | 1.00 | 1.00 | 1.14 | 1.00 | 1.00 |
| Sh3bgr | 1.22 | 0.85 | 0.84 | 0.65 | 4.88 | 1.75 | 1.11 | 1.11 | 0.94 | 1.14 | 2.72 | 1.02 |
| Sh3gl2 | 1.00 | 1.00 | 1.00 | 1.00 | 0.13 | 1.00 | 1.38 | 1.61 | 1.19 | 0.62 | 0.51 | 0.38 |
| Sh3glb1 | 1.00 | 0.70 | 0.88 | 1.04 | 4.47 | 0.99 | 1.09 | 1.10 | 0.98 | 2.42 | 2.34 | 0.98 |
| Shf | 1.05 | 0.66 | 0.67 | 0.77 | 2.81 | 1.18 | 0.81 | 0.78 | 0.77 | 2.40 | 2.80 | 0.88 |
| Shmt1 | 0.80 | 0.86 | 0.93 | 0.73 | 5.12 | 1.04 | 1.18 | 0.74 | 0.75 | 1.76 | 2.66 | 0.75 |
| Sigirr | 0.92 | 0.28 | 1.16 | 0.33 | 3.20 | 0.89 | 0.76 | 0.68 | 1.07 | 1.96 | 2.29 | 0.88 |
| Sik1 | 7.22 | 23.30 | 5.25 | 2.22 | 0.47 | 1.27 | 3.26 | 3.58 | 1.58 | 1.63 | 1.50 | 1.58 |
| Sil1 | 1.35 | 0.75 | 0.99 | 0.62 | 6.67 | 1.18 | 1.05 | 0.82 | 0.82 | 1.57 | 2.48 | 0.84 |
| Sin3b | 0.98 | 0.75 | 0.95 | 0.38 | 3.68 | 1.23 | 1.21 | 1.13 | 1.02 | 1.75 | 1.81 | 0.96 |
| Sirpb1b | 1.00 | 1.00 | 1.00 | 1.00 | 1.00 | 1.00 | 1.00 | 1.00 | 1.00 | 1.23 | 0.66 | 0.76 |
| Siva1 | 1.40 | 1.02 | 0.92 | 0.38 | 5.20 | 0.98 | 1.24 | 0.97 | 1.01 | 1.83 | 2.44 | 1.11 |
| Slamf9 | 1.00 | 0.32 | 1.00 | 0.94 | 1.98 | 0.71 | 0.44 | 0.35 | 0.72 | 1.98 | 2.48 | 0.68 |
| Slc10a3-ubl4 | 1.00 | 1.00 | 1.00 | 1.00 | 2.21 | 1.00 | 1.00 | 1.00 | 1.00 | 1.00 | 1.00 | 1.00 |
| Slc10a6 | 3.38 | 2.89 | 1.93 | 1.55 | 3.40 | 2.86 | 2.58 | 2.90 | 3.12 | 1.85 | 1.95 | 1.49 |
| Slc11a1 | 1.44 | 1.35 | 1.76 | 0.87 | 3.49 | 1.51 | 1.44 | 0.96 | 1.77 | 1.54 | 1.97 | 0.99 |
| Slc12a5 | 1.00 | 1.00 | 1.00 | 1.00 | 0.15 | 1.00 | 1.00 | 0.74 | 0.65 | 1.00 | 1.00 | 1.08 |
| Slc15a3 | 1.00 | 1.00 | 1.00 | 1.00 | 1.00 | 1.00 | 1.62 | 1.00 | 2.02 | 1.73 | 2.35 | 1.13 |
| Slc16a3 | 1.08 | 0.86 | 0.92 | 0.83 | 2.77 | 0.74 | 0.82 | 0.78 | 1.13 | 3.18 | 2.79 | 1.12 |
| Slc17a7 | 1.00 | 1.00 | 1.00 | 1.00 | 0.06 | 1.00 | 1.95 | 1.72 | 1.43 | 1.03 | 1.40 | 1.14 |
| Slc1a2 | 1.00 | 1.00 | 1.00 | 1.00 | 0.07 | 1.00 | 1.00 | 1.00 | 1.00 | 1.00 | 1.00 | 1.04 |
| Slc22a13b-ps | 1.00 | 1.00 | 1.00 | 1.00 | 1.22 | 1.00 | 1.00 | 0.88 | 1.00 | 1.54 | 1.83 | 1.00 |
| Slc22a18 | 1.00 | 0.98 | 1.00 | 1.00 | 2.77 | 1.00 | 1.00 | 1.00 | 1.00 | 4.17 | 4.81 | 1.07 |
| Slc22a4 | 3.15 | 2.98 | 2.06 | 4.46 | 7.20 | 3.87 | 1.06 | 1.27 | 1.53 | 1.11 | 1.05 | 1.00 |
| Slc24a2 | 1.00 | 1.00 | 1.00 | 1.00 | 0.20 | 1.00 | 1.19 | 0.90 | 0.95 | 1.00 | 1.00 | 1.00 |
| Slc25a14 | 1.00 | 0.57 | 0.86 | 0.80 | 1.59 | 1.00 | 0.89 | 1.23 | 1.19 | 1.66 | 2.12 | 0.76 |
| Slc25a25 | 0.69 | 1.33 | 0.34 | 6.00 | 21.05 | 1.42 | 0.89 | 1.13 | 1.08 | 2.10 | 3.63 | 1.42 |
| Slc25a30 | 2.49 | 1.00 | 2.07 | 9.57 | 0.42 | 1.83 | 2.11 | 2.09 | 1.85 | 1.00 | 1.00 | 1.05 |
| Slc25a32 | 1.51 | 2.28 | 1.45 | 6.75 | 2.71 | 2.05 | 1.23 | 1.76 | 1.35 | 0.77 | 0.59 | 1.00 |
| Slc25a33 | 7.17 | 8.92 | 2.49 | 0.71 | 5.96 | 0.66 | 4.87 | 5.33 | 1.58 | 2.52 | 3.82 | 1.38 |
| Slc25a34 | 0.65 | 0.48 | 0.94 | 0.39 | 1.09 | 0.61 | 0.75 | 0.68 | 0.68 | 2.24 | 2.05 | 1.56 |
| Slc25a39 | 1.13 | 0.69 | 1.02 | 0.48 | 3.38 | 1.01 | 0.90 | 0.76 | 0.77 | 1.33 | 1.90 | 1.04 |
| Slc25a42 | 0.48 | 0.47 | 0.65 | 1.05 | 0.87 | 1.03 | 0.61 | 0.59 | 0.60 | 0.82 | 0.73 | 0.92 |
| Slc26a10 | 0.93 | 0.36 | 1.66 | 0.38 | 2.29 | 0.72 | 0.79 | 0.60 | 0.71 | 1.00 | 1.00 | 1.00 |
| Slc27a4 | 1.18 | 0.70 | 0.90 | 0.48 | 4.05 | 0.88 | 0.93 | 0.74 | 1.02 | 3.47 | 3.21 | 1.06 |
| Slc29a1 | 1.40 | 1.03 | 1.09 | 1.15 | 7.45 | 1.22 | 0.92 | 0.66 | 0.73 | 1.38 | 2.23 | 0.92 |
| Slc32a1 | 1.00 | 1.00 | 1.00 | 1.00 | 0.23 | 1.00 | 1.00 | 1.00 | 1.00 | 1.00 | 1.00 | 1.00 |
| Slc35e4 | 1.22 | 1.20 | 1.06 | 1.46 | 10.83 | 2.40 | 1.56 | 1.15 | 1.50 | 1.73 | 1.53 | 1.19 |
| Slc38a2 | 3.26 | 4.07 | 1.93 | 5.19 | 2.16 | 1.11 | 1.28 | 1.71 | 1.14 | 1.20 | 1.04 | 1.31 |
| Slc39a14 | 13.44 | 19.18 | 9.99 | 3.67 | 4.65 | 2.31 | 0.83 | 0.95 | 0.98 | 1.18 | 1.30 | 1.30 |
| Slc43a1 | 2.48 | 2.15 | 4.04 | 3.69 | 24.63 | 2.04 | 1.27 | 1.39 | 1.02 | 1.11 | 1.93 | 1.07 |
| Slc5a11 | 1.00 | 1.00 | 1.00 | 1.00 | 1.00 | 1.00 | 1.00 | 1.00 | 1.00 | 1.00 | 1.00 | 1.00 |
| Slc6a1 | 1.00 | 1.00 | 1.00 | 1.00 | 0.13 | 1.00 | 1.00 | 1.00 | 1.00 | 1.00 | 1.00 | 1.00 |
| Slc6a11 | 1.00 | 1.00 | 1.00 | 1.00 | 0.30 | 1.00 | 1.00 | 1.00 | 1.00 | 1.00 | 1.00 | 1.00 |
| Slc6a17 | 0.87 | 1.00 | 0.56 | 1.00 | 0.14 | 1.00 | 1.13 | 0.94 | 0.78 | 1.00 | 1.00 | 1.00 |
| Slc7a5 | 0.56 | 1.07 | 0.93 | 1.00 | 0.57 | 1.00 | 1.03 | 1.01 | 1.53 | 0.82 | 0.72 | 1.20 |

Fig. 35- 258

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Sertad3 | 0.99 | 1.19 | 1.03 | 0.93 | 1.41 | 1.13 | 0.52 | 0.95 | 0.80 | 0.90 | 1.46 | 1.05 |
| Sesn1 | 1.59 | 1.71 | 1.43 | 1.66 | 2.64 | 1.16 | 2.72 | 2.67 | 1.07 | 1.38 | 1.47 | 1.33 |
| Setd4 | 1.42 | 1.74 | 0.95 | 1.03 | 0.33 | 1.00 | 0.88 | 2.29 | 0.80 | 1.29 | 1.01 | 0.80 |
| Setd7 | 0.71 | 0.60 | 1.00 | 1.20 | 1.10 | 1.16 | 2.34 | 1.00 | 2.34 | 1.04 | 0.62 | 0.92 |
| Setdb2 | 1.09 | 1.00 | 1.17 | 1.14 | 1.00 | 0.82 | 7.23 | 1.75 | 1.20 | 1.34 | 1.04 | 1.23 |
| Sez6 | 1.00 | 1.00 | 1.00 | 1.00 | 1.00 | 1.00 | 1.00 | 1.00 | 1.00 | 1.00 | 1.00 | 1.00 |
| Sez6l | 1.00 | 1.00 | 1.00 | 1.00 | 1.00 | 1.00 | 1.00 | 1.00 | 1.00 | 1.00 | 1.00 | 1.00 |
| Sez6l2 | 1.39 | 1.00 | 0.98 | 1.00 | 1.00 | 1.00 | 1.00 | 1.00 | 1.00 | 0.90 | 0.94 | 1.36 |
| Sf3a3 | 1.10 | 1.15 | 0.86 | 0.51 | 0.61 | 0.99 | 0.75 | 2.02 | 0.99 | 0.66 | 1.56 | 0.91 |
| Sfn | 1.10 | 1.18 | 1.07 | 0.80 | 0.48 | 1.06 | 1.00 | 2.52 | 1.00 | 1.21 | 2.05 | 1.06 |
| Sfta2 | 1.00 | 1.00 | 1.00 | 1.00 | 0.83 | 1.00 | 1.00 | 1.00 | 1.00 | 1.00 | 1.00 | 1.00 |
| Sftpb | 1.00 | 1.00 | 1.00 | 1.00 | 1.00 | 1.00 | 1.00 | 1.00 | 1.00 | 1.00 | 1.00 | 1.00 |
| Sftpc | 0.19 | 1.00 | 1.00 | 1.00 | 1.00 | 1.00 | 1.00 | 1.00 | 1.00 | 1.00 | 1.00 | 1.00 |
| Sgca | 1.00 | 1.00 | 1.00 | 1.00 | 1.00 | 1.00 | 1.00 | 1.00 | 1.00 | 1.00 | 1.35 | 1.41 |
| Sgk1 | 2.38 | 2.43 | 1.42 | 1.51 | 1.97 | 1.45 | 6.94 | 4.68 | 2.51 | 1.71 | 2.74 | 1.30 |
| Sgk3 | 0.74 | 0.77 | 0.81 | 1.25 | 1.31 | 0.84 | 1.00 | 1.00 | 0.57 | 1.18 | 0.96 | 0.82 |
| Sgsh | 1.22 | 1.20 | 1.49 | 1.00 | 0.68 | 1.05 | 1.00 | 2.13 | 1.08 | 0.89 | 1.07 | 1.03 |
| Sh2d4a | 1.42 | 1.43 | 1.09 | 1.04 | 1.06 | 0.99 | 1.00 | 0.89 | 1.00 | 0.93 | 1.03 | 0.95 |
| Sh2d7 | 1.42 | 1.10 | 0.66 | 1.00 | 1.00 | 1.00 | 1.00 | 1.00 | 1.00 | 0.72 | 0.52 | 1.05 |
| Sh3bgr | 1.00 | 1.00 | 1.00 | 1.00 | 0.77 | 1.00 | 1.00 | 1.00 | 1.00 | 1.03 | 1.68 | 0.95 |
| Sh3gl2 | 1.00 | 1.00 | 1.00 | 0.54 | 0.46 | 0.51 | 1.00 | 1.00 | 1.00 | 0.81 | 0.69 | 0.85 |
| Sh3glb1 | 0.91 | 0.86 | 1.03 | 1.14 | 0.80 | 1.06 | 1.14 | 2.41 | 1.10 | 1.07 | 1.24 | 0.98 |
| Shf | 1.21 | 1.68 | 1.14 | 0.91 | 0.55 | 1.09 | 0.57 | 1.13 | 0.69 | 1.37 | 1.80 | 1.28 |
| Shmt1 | 0.68 | 0.55 | 0.50 | 1.00 | 0.87 | 1.08 | 0.66 | 0.79 | 0.78 | 0.98 | 1.15 | 0.90 |
| Sigirr | 1.26 | 1.43 | 1.03 | 1.11 | 0.72 | 1.04 | 0.83 | 1.35 | 0.82 | 0.95 | 1.22 | 0.98 |
| Sik1 | 1.43 | 1.34 | 1.30 | 0.92 | 1.21 | 1.04 | 2.02 | 2.10 | 1.38 | 1.04 | 1.24 | 0.93 |
| Sil1 | 1.27 | 1.63 | 1.53 | 0.91 | 0.77 | 0.94 | 0.90 | 1.47 | 0.86 | 1.00 | 1.52 | 1.09 |
| Sin3b | 0.81 | 0.99 | 0.80 | 0.94 | 0.99 | 0.95 | 1.02 | 0.93 | 1.09 | 1.05 | 1.56 | 1.11 |
| Sirpb1b | 1.00 | 1.00 | 1.00 | 1.00 | 1.00 | 1.00 | 1.00 | 1.00 | 1.00 | 1.00 | 1.00 | 1.00 |
| Siva1 | 1.44 | 1.00 | 0.89 | 0.86 | 0.61 | 1.13 | 1.29 | 1.52 | 1.41 | 0.75 | 1.24 | 0.85 |
| Slamf9 | 0.91 | 0.86 | 1.22 | 0.31 | 0.14 | 0.22 | 1.00 | 0.65 | 1.00 | 0.54 | 0.55 | 0.85 |
| Slc10a3-ubl4 | 1.00 | 1.00 | 1.00 | 1.00 | 0.77 | 1.00 | 1.00 | 1.00 | 1.00 | 1.00 | 1.00 | 1.00 |
| Slc10a6 | 5.93 | 4.98 | 2.99 | 1.87 | 1.74 | 1.56 | 1.40 | 1.57 | 1.00 | 2.05 | 2.80 | 1.31 |
| Slc11a1 | 3.87 | 2.69 | 2.11 | 1.22 | 0.66 | 1.02 | 1.27 | 1.61 | 0.97 | 1.15 | 1.52 | 1.26 |
| Slc12a5 | 1.00 | 1.00 | 1.00 | 1.00 | 1.00 | 1.00 | 1.00 | 1.00 | 1.00 | 1.00 | 1.00 | 1.00 |
| Slc15a3 | 2.41 | 2.57 | 2.45 | 1.00 | 0.79 | 1.23 | 1.23 | 1.61 | 1.02 | 0.83 | 0.84 | 0.81 |
| Slc16a3 | 1.41 | 1.41 | 1.55 | 1.00 | 0.67 | 1.05 | 1.00 | 2.45 | 1.00 | 0.60 | 0.71 | 0.63 |
| Slc17a7 | 1.00 | 1.00 | 1.00 | 1.00 | 1.00 | 1.00 | 1.00 | 1.00 | 1.00 | 1.00 | 1.00 | 1.00 |
| Slc1a2 | 1.21 | 0.99 | 1.15 | 0.73 | 1.00 | 0.91 | 1.45 | 1.45 | 1.76 | 1.00 | 1.00 | 1.00 |
| Slc22a13b-ps | 1.18 | 1.00 | 1.00 | 0.76 | 0.77 | 1.06 | 1.00 | 1.00 | 1.00 | 1.04 | 1.35 | 1.00 |
| Slc22a18 | 1.90 | 2.07 | 1.49 | 0.98 | 0.61 | 1.02 | 0.69 | 1.96 | 0.69 | 1.16 | 1.46 | 1.18 |
| Slc22a4 | 2.25 | 2.86 | 2.04 | 0.61 | 0.81 | 0.77 | 0.97 | 0.60 | 0.71 | 0.55 | 0.67 | 1.00 |
| Slc24a2 | 1.00 | 1.00 | 1.00 | 1.00 | 1.00 | 1.00 | 1.00 | 1.00 | 1.00 | 1.00 | 1.00 | 1.00 |
| Slc25a14 | 0.82 | 1.81 | 1.16 | 1.15 | 0.84 | 0.63 | 1.00 | 2.25 | 1.00 | 0.78 | 2.07 | 1.09 |
| Slc25a25 | 0.92 | 1.02 | 0.95 | 1.76 | 1.20 | 0.99 | 2.12 | 3.20 | 1.85 | 1.11 | 1.22 | 1.05 |
| Slc25a30 | 0.73 | 0.38 | 1.19 | 1.49 | 1.00 | 1.33 | 1.74 | 1.00 | 1.07 | 1.16 | 1.00 | 0.77 |
| Slc25a32 | 0.83 | 0.66 | 0.93 | 1.51 | 1.19 | 1.35 | 2.08 | 1.95 | 1.81 | 1.23 | 0.97 | 0.99 |
| Slc25a33 | 9.63 | 13.77 | 2.50 | 2.98 | 3.65 | 1.59 | 1.90 | 2.44 | 0.99 | 1.46 | 2.52 | 1.36 |
| Slc25a34 | 0.95 | 1.00 | 0.50 | 0.92 | 0.77 | 1.06 | 1.07 | 1.50 | 1.29 | 1.00 | 1.12 | 1.32 |
| Slc25a39 | 1.36 | 1.72 | 1.05 | 0.83 | 0.93 | 0.88 | 1.15 | 0.97 | 1.07 | 0.97 | 1.38 | 0.99 |
| Slc25a42 | 0.93 | 0.84 | 1.14 | 0.78 | 0.75 | 0.85 | 1.23 | 0.86 | 1.10 | 0.73 | 0.73 | 0.82 |
| Slc26a10 | 1.00 | 1.00 | 1.00 | 1.00 | 0.77 | 1.00 | 1.00 | 1.00 | 1.00 | 1.00 | 1.00 | 1.00 |
| Slc27a4 | 1.00 | 1.03 | 1.06 | 0.98 | 0.54 | 0.98 | 1.50 | 4.33 | 1.05 | 1.02 | 1.26 | 1.11 |
| Slc29a1 | 1.10 | 1.33 | 1.04 | 0.92 | 0.83 | 0.89 | 1.20 | 1.48 | 1.19 | 0.96 | 1.57 | 1.05 |
| Slc32a1 | 1.00 | 1.00 | 1.00 | 1.00 | 1.00 | 1.00 | 1.00 | 1.00 | 1.00 | 1.00 | 1.00 | 1.00 |
| Slc35e4 | 1.64 | 2.04 | 1.33 | 1.56 | 1.02 | 1.37 | 1.00 | 1.00 | 1.00 | 0.96 | 1.22 | 1.04 |
| Slc38a2 | 0.70 | 0.67 | 0.90 | 1.15 | 1.15 | 1.09 | 1.74 | 1.44 | 0.94 | 1.14 | 1.01 | 1.33 |
| Slc39a14 | 0.97 | 0.97 | 1.05 | 0.95 | 1.02 | 0.85 | 1.33 | 1.91 | 0.93 | 0.82 | 0.67 | 0.85 |
| Slc43a1 | 1.85 | 2.07 | 1.13 | 2.08 | 2.29 | 1.91 | 1.51 | 1.76 | 1.02 | 0.94 | 2.16 | 1.33 |
| Slc5a11 | 1.00 | 1.00 | 1.00 | 0.60 | 0.68 | 0.89 | 1.00 | 1.00 | 1.00 | 1.00 | 1.00 | 1.00 |
| Slc6a1 | 1.00 | 1.00 | 1.00 | 1.00 | 1.00 | 1.00 | 1.00 | 1.00 | 1.00 | 1.00 | 1.00 | 1.00 |
| Slc6a11 | 1.00 | 1.00 | 1.00 | 1.00 | 1.00 | 1.00 | 1.00 | 1.00 | 1.00 | 1.00 | 1.00 | 0.99 |
| Slc6a17 | 1.00 | 1.00 | 1.00 | 0.80 | 1.17 | 0.68 | 1.00 | 1.00 | 1.00 | 0.99 | 0.80 | 1.16 |
| Slc7a5 | 0.55 | 0.57 | 0.88 | 1.14 | 1.00 | 1.07 | 5.14 | 1.89 | 3.00 | 1.01 | 1.05 | 0.94 |

Fig. 35- 259

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Sertad3 | 0.99 | 1.22 | 1.26 | 0.78 | 2.59 | 1.10 | 0.79 | 1.05 | 1.28 | 0.84 | 1.08 | 0.87 |
| Sesn1 | 1.89 | 2.41 | 1.77 | 2.50 | 6.29 | 1.41 | 0.82 | 0.63 | 0.82 | 2.42 | 2.79 | 1.80 |
| Setd4 | 0.87 | 1.49 | 0.84 | 0.47 | 2.19 | 1.06 | 1.06 | 2.97 | 1.02 | 1.16 | 1.12 | 1.02 |
| Setd7 | 1.14 | 1.18 | 1.09 | 1.83 | 0.45 | 0.98 | 1.06 | 1.00 | 1.04 | 1.07 | 0.76 | 1.30 |
| Setdb2 | 1.31 | 1.10 | 1.04 | 13.51 | 1.50 | 1.89 | 1.26 | 1.00 | 0.90 | 1.57 | 1.45 | 1.34 |
| Sez6 | 1.00 | 0.91 | 1.00 | 1.00 | 1.00 | 0.89 | 0.92 | 1.00 | 0.78 | 1.00 | 5.13 | 1.00 |
| Sez6l | 1.00 | 1.00 | 1.00 | 1.00 | 1.00 | 1.00 | 1.22 | 2.53 | 0.85 | 1.00 | 5.02 | 1.00 |
| Sez6l2 | 0.85 | 1.39 | 1.06 | 1.47 | 1.23 | 1.43 | 0.94 | 1.50 | 1.02 | 0.75 | 9.63 | 0.97 |
| Sf3a3 | 1.12 | 1.00 | 0.99 | 0.85 | 2.34 | 1.30 | 1.31 | 2.38 | 0.88 | 1.23 | 1.21 | 0.94 |
| Sfn | 0.77 | 0.81 | 0.76 | 0.59 | 1.00 | 1.69 | 1.00 | 4.11 | 1.06 | 1.01 | 1.30 | 1.07 |
| Sfta2 | 0.67 | 0.88 | 0.58 | 1.00 | 0.43 | 1.00 | 1.00 | 1.00 | 1.00 | 1.00 | 1.00 | 1.00 |
| Sftpb | 1.00 | 1.00 | 1.00 | 1.00 | 1.00 | 1.00 | 2.38 | 27.85 | 2.73 | 1.00 | 1.00 | 1.00 |
| Sftpc | 1.00 | 1.30 | 1.00 | 1.00 | 0.23 | 1.00 | 1.00 | 2.63 | 1.00 | 1.00 | 1.62 | 1.00 |
| Sgca | 1.00 | 1.00 | 1.43 | 1.00 | 1.00 | 1.00 | 1.67 | 2.79 | 1.79 | 1.00 | 1.00 | 1.00 |
| Sgk1 | 2.26 | 3.20 | 2.03 | 1.79 | 1.56 | 2.00 | 1.07 | 0.78 | 0.91 | 1.40 | 1.51 | 1.14 |
| Sgk3 | 1.31 | 1.17 | 1.04 | 1.62 | 1.00 | 0.79 | 1.14 | 0.64 | 0.79 | 2.12 | 1.85 | 1.35 |
| Sgsh | 0.91 | 0.94 | 0.88 | 0.79 | 1.09 | 0.81 | 0.89 | 1.65 | 0.95 | 0.96 | 0.87 | 1.07 |
| Sh2d4a | 0.77 | 0.69 | 0.65 | 0.91 | 1.00 | 0.66 | 0.97 | 2.85 | 1.11 | 1.13 | 0.56 | 0.69 |
| Sh2d7 | 1.36 | 0.88 | 1.34 | 0.33 | 1.04 | 0.74 | 2.18 | 1.10 | 1.46 | 1.00 | 1.00 | 1.00 |
| Sh3bgr | 0.93 | 1.47 | 1.65 | 2.20 | 1.00 | 1.66 | 1.00 | 1.00 | 1.00 | 0.81 | 1.57 | 1.03 |
| Sh3gl2 | 0.61 | 0.54 | 0.61 | 1.54 | 1.14 | 2.21 | 0.94 | 1.25 | 0.84 | 1.00 | 12.19 | 1.00 |
| Sh3glb1 | 1.01 | 0.96 | 0.99 | 0.77 | 1.88 | 0.88 | 0.97 | 2.64 | 1.02 | 0.85 | 0.84 | 0.86 |
| Shf | 0.87 | 1.19 | 1.58 | 0.63 | 1.26 | 0.76 | 0.86 | 2.53 | 0.71 | 0.68 | 1.44 | 0.87 |
| Shmt1 | 0.93 | 0.82 | 0.81 | 0.65 | 2.23 | 0.70 | 0.94 | 1.47 | 0.83 | 1.17 | 1.43 | 0.98 |
| Sigirr | 0.97 | 0.96 | 0.77 | 1.00 | 3.68 | 1.07 | 1.40 | 3.39 | 1.22 | 0.92 | 0.93 | 0.95 |
| Sik1 | 1.30 | 1.71 | 1.16 | 1.53 | 0.59 | 1.29 | 0.73 | 0.91 | 1.18 | 1.27 | 1.59 | 1.50 |
| Sil1 | 0.97 | 0.96 | 1.10 | 0.99 | 2.95 | 1.12 | 0.90 | 1.83 | 1.00 | 1.02 | 1.39 | 1.05 |
| Sin3b | 0.97 | 1.16 | 1.00 | 1.04 | 7.00 | 0.96 | 0.92 | 1.21 | 0.97 | 1.20 | 1.43 | 1.00 |
| Sirpb1b | 1.00 | 1.00 | 1.00 | 1.00 | 1.00 | 0.66 | 8.99 | 8.99 | 7.77 | 1.07 | 0.46 | 0.93 |
| Siva1 | 0.89 | 0.64 | 1.24 | 1.07 | 3.34 | 0.97 | 0.69 | 1.85 | 0.91 | 0.77 | 1.28 | 0.83 |
| Slamf9 | 0.58 | 0.44 | 0.54 | 0.50 | 0.59 | 0.35 | 0.89 | 3.34 | 1.03 | 0.46 | 0.45 | 0.74 |
| Slc10a3-ubl4 | 1.00 | 1.00 | 1.00 | 1.00 | 3.75 | 1.00 | 1.26 | 0.95 | 0.94 | 1.00 | 1.00 | 1.00 |
| Slc10a6 | 1.56 | 1.85 | 1.80 | 4.81 | 6.59 | 3.64 | 1.11 | 1.00 | 1.00 | 3.37 | 3.30 | 2.29 |
| Slc11a1 | 1.32 | 1.19 | 1.20 | 1.04 | 1.64 | 0.72 | 1.00 | 2.35 | 1.00 | 0.91 | 1.35 | 0.90 |
| Slc12a5 | 1.00 | 1.00 | 1.00 | 1.16 | 1.00 | 1.14 | 1.06 | 1.32 | 1.05 | 1.00 | 10.72 | 1.00 |
| Slc15a3 | 1.35 | 0.88 | 1.27 | 1.42 | 1.00 | 0.45 | 1.00 | 1.00 | 1.00 | 0.85 | 0.79 | 0.82 |
| Slc16a3 | 0.63 | 0.67 | 0.49 | 1.03 | 1.04 | 1.44 | 1.02 | 2.89 | 0.64 | 1.30 | 0.92 | 0.78 |
| Slc17a7 | 1.00 | 1.00 | 1.00 | 1.00 | 1.00 | 0.96 | 0.81 | 1.58 | 0.95 | 1.00 | 29.30 | 1.00 |
| Slc1a2 | 1.33 | 1.43 | 1.29 | 1.00 | 1.00 | 1.00 | 1.04 | 0.36 | 1.03 | 0.44 | 6.26 | 0.69 |
| Slc22a13b-ps | 1.03 | 1.00 | 1.00 | 1.00 | 1.00 | 1.00 | 1.00 | 1.00 | 1.00 | 1.00 | 1.43 | 1.00 |
| Slc22a18 | 0.81 | 0.84 | 0.70 | 0.54 | 1.64 | 0.98 | 1.15 | 3.78 | 1.26 | 1.00 | 1.00 | 1.00 |
| Slc22a4 | 1.00 | 1.00 | 1.00 | 1.47 | 3.21 | 1.03 | 1.13 | 0.79 | 0.96 | 0.40 | 0.43 | 0.29 |
| Slc24a2 | 1.00 | 1.00 | 1.00 | 1.00 | 1.00 | 1.00 | 1.00 | 1.00 | 1.00 | 1.00 | 8.20 | 1.00 |
| Slc25a14 | 0.64 | 0.92 | 0.68 | 0.82 | 2.16 | 1.12 | 1.08 | 1.84 | 0.72 | 0.89 | 1.36 | 1.72 |
| Slc25a25 | 1.16 | 1.56 | 0.90 | 5.62 | 14.16 | 3.26 | 1.20 | 1.56 | 0.98 | 0.79 | 0.94 | 0.99 |
| Slc25a30 | 1.04 | 1.04 | 0.86 | 7.68 | 0.76 | 2.22 | 1.31 | 1.43 | 1.09 | 1.08 | 0.51 | 1.18 |
| Slc25a32 | 1.17 | 1.12 | 0.84 | 2.04 | 0.85 | 1.07 | 1.28 | 1.00 | 0.97 | 1.11 | 0.81 | 1.19 |
| Slc25a33 | 1.07 | 1.43 | 1.12 | 3.22 | 13.50 | 1.80 | 1.03 | 1.34 | 1.05 | 1.22 | 1.76 | 0.76 |
| Slc25a34 | 1.23 | 1.34 | 1.26 | 5.14 | 4.94 | 4.95 | 0.66 | 0.63 | 0.62 | 1.30 | 1.91 | 1.36 |
| Slc25a39 | 1.11 | 1.22 | 1.11 | 1.07 | 5.73 | 1.19 | 0.89 | 1.01 | 0.99 | 0.61 | 0.79 | 0.54 |
| Slc25a42 | 0.80 | 0.83 | 1.07 | 5.95 | 7.16 | 3.47 | 0.88 | 0.97 | 0.68 | 0.70 | 0.67 | 0.84 |
| Slc26a10 | 1.00 | 1.00 | 1.00 | 0.44 | 1.31 | 0.70 | 1.03 | 5.46 | 1.08 | 1.00 | 0.88 | 0.91 |
| Slc27a4 | 0.82 | 0.82 | 0.80 | 0.96 | 2.00 | 1.03 | 0.93 | 4.06 | 0.80 | 0.97 | 1.32 | 1.08 |
| Slc29a1 | 0.95 | 1.21 | 1.45 | 0.92 | 1.80 | 1.01 | 0.71 | 0.75 | 0.73 | 1.15 | 1.61 | 1.05 |
| Slc32a1 | 1.00 | 1.00 | 1.00 | 1.00 | 1.00 | 1.00 | 1.00 | 1.00 | 1.00 | 1.00 | 7.37 | 1.00 |
| Slc35e4 | 1.31 | 1.75 | 1.16 | 1.39 | 2.26 | 1.01 | 1.00 | 1.00 | 1.00 | 0.89 | 1.62 | 0.89 |
| Slc38a2 | 1.05 | 1.09 | 1.07 | 4.38 | 2.79 | 2.96 | 0.94 | 0.99 | 0.82 | 1.10 | 0.77 | 1.14 |
| Slc39a14 | 1.14 | 1.03 | 1.06 | 3.03 | 5.15 | 1.65 | 0.89 | 0.84 | 1.00 | 1.07 | 0.97 | 1.17 |
| Slc43a1 | 1.22 | 2.17 | 1.56 | 1.78 | 5.27 | 2.34 | 1.00 | 1.00 | 1.00 | 0.47 | 0.52 | 0.28 |
| Slc5a11 | 1.00 | 1.00 | 1.00 | 1.00 | 1.00 | 1.00 | 1.00 | 1.00 | 1.00 | 1.00 | 1.00 | 1.00 |
| Slc6a1 | 0.69 | 0.52 | 0.53 | 1.00 | 1.00 | 1.00 | 1.00 | 1.00 | 1.00 | 1.00 | 13.14 | 1.00 |
| Slc6a11 | 0.38 | 0.38 | 0.50 | 1.00 | 1.00 | 1.00 | 1.00 | 1.00 | 1.00 | 1.00 | 5.77 | 1.00 |
| Slc6a17 | 1.62 | 1.84 | 1.22 | 1.70 | 1.00 | 2.47 | 1.00 | 1.00 | 1.00 | 1.00 | 12.00 | 1.00 |
| Slc7a5 | 1.21 | 1.39 | 1.47 | 0.85 | 1.00 | 1.65 | 1.00 | 0.50 | 0.86 | 0.75 | 0.73 | 0.69 |

Fig. 35- 260

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Sertad3 | 1.35 | 1.55 | 0.95 | 1.22 | 10.94 | 1.07 | 0.85 | 2.02 | 0.90 | 1.24 | 1.16 | 1.11 |
| Sesn1 | 1.68 | 2.07 | 1.91 | 1.05 | 1.11 | 1.06 | 1.77 | 1.25 | 1.93 | 1.08 | 1.46 | 1.09 |
| Setd4 | 1.00 | 1.00 | 1.00 | 0.98 | 1.97 | 1.26 | 1.85 | 6.62 | 1.17 | 2.23 | 1.05 | 1.24 |
| Setd7 | 1.16 | 0.98 | 1.40 | 0.96 | 2.01 | 1.03 | 0.86 | 0.16 | 1.22 | 0.75 | 0.98 | 0.85 |
| Setdb2 | 1.00 | 1.00 | 1.00 | 0.94 | 1.00 | 1.47 | 1.12 | 0.54 | 1.10 | 0.75 | 0.84 | 0.98 |
| Sez6 | 1.00 | 1.00 | 1.00 | 0.97 | 0.94 | 0.99 | 1.00 | 1.00 | 1.00 | 1.00 | 1.00 | 1.00 |
| Sez6l | 1.00 | 1.00 | 1.00 | 1.04 | 1.58 | 1.02 | 1.00 | 1.00 | 1.00 | 1.00 | 1.00 | 1.00 |
| Sez6l2 | 1.00 | 1.00 | 1.00 | 1.10 | 0.78 | 1.08 | 1.31 | 3.39 | 1.06 | 1.00 | 1.00 | 1.00 |
| Sf3a3 | 0.75 | 0.74 | 0.84 | 1.06 | 0.93 | 1.17 | 0.82 | 7.24 | 0.78 | 2.06 | 1.09 | 1.11 |
| Sfn | 1.00 | 1.00 | 1.00 | 1.00 | 1.21 | 1.39 | 0.69 | 5.23 | 0.48 | 2.37 | 1.90 | 1.24 |
| Sfta2 | 1.00 | 1.00 | 1.00 | 1.00 | 1.00 | 1.00 | 1.00 | 1.42 | 1.00 | 1.00 | 1.00 | 1.00 |
| Sftpb | 1.00 | 1.00 | 1.00 | 1.00 | 0.92 | 1.00 | 1.00 | 1.15 | 1.00 | 3.32 | 1.26 | 1.00 |
| Sftpc | 1.00 | 1.00 | 1.00 | 1.00 | 0.78 | 1.00 | 1.08 | 8.89 | 1.00 | 4.01 | 0.94 | 0.70 |
| Sgca | 1.00 | 1.00 | 1.00 | 1.00 | 1.00 | 1.00 | 1.71 | 8.57 | 1.95 | 1.00 | 1.00 | 1.00 |
| Sgk1 | 0.91 | 1.47 | 1.25 | 1.23 | 0.77 | 1.04 | 2.46 | 1.11 | 2.29 | 0.83 | 1.57 | 1.55 |
| Sgk3 | 1.00 | 1.00 | 1.00 | 1.58 | 1.65 | 1.18 | 0.96 | 0.52 | 0.98 | 0.77 | 1.07 | 1.07 |
| Sgsh | 1.00 | 1.00 | 0.77 | 1.04 | 0.88 | 1.11 | 1.01 | 6.05 | 0.98 | 1.62 | 1.09 | 1.10 |
| Sh2d4a | 1.02 | 0.83 | 0.90 | 1.00 | 1.00 | 1.00 | 0.63 | 1.69 | 0.72 | 0.55 | 0.54 | 0.68 |
| Sh2d7 | 1.00 | 1.00 | 1.00 | 1.00 | 1.00 | 1.00 | 1.00 | 7.61 | 1.14 | 1.00 | 1.00 | 1.00 |
| Sh3bgr | 1.00 | 1.00 | 1.00 | 1.24 | 2.65 | 0.69 | 1.88 | 5.44 | 1.30 | 2.75 | 1.25 | 1.00 |
| Sh3gl2 | 1.00 | 1.00 | 1.00 | 0.99 | 0.64 | 0.96 | 0.53 | 1.01 | 0.56 | 1.00 | 1.00 | 1.00 |
| Sh3glb1 | 0.88 | 1.04 | 0.89 | 0.87 | 0.86 | 0.86 | 1.11 | 6.73 | 1.13 | 1.94 | 0.97 | 1.00 |
| Shf | 1.00 | 1.00 | 1.00 | 1.02 | 0.78 | 0.92 | 0.82 | 7.09 | 0.80 | 1.26 | 0.74 | 1.09 |
| Shmt1 | 1.00 | 0.92 | 1.18 | 1.06 | 0.50 | 1.21 | 0.89 | 3.58 | 0.90 | 1.38 | 0.62 | 1.06 |
| Sigirr | 0.93 | 0.56 | 1.07 | 1.00 | 0.33 | 1.00 | 1.26 | 5.80 | 1.17 | 2.30 | 0.95 | 1.08 |
| Sik1 | 0.98 | 1.92 | 0.84 | 1.29 | 0.94 | 1.31 | 1.42 | 0.44 | 1.25 | 0.55 | 1.27 | 0.94 |
| Sil1 | 0.63 | 0.69 | 0.70 | 0.99 | 0.84 | 1.02 | 1.13 | 7.84 | 0.99 | 2.29 | 1.07 | 1.12 |
| Sin3b | 0.93 | 0.98 | 0.95 | 1.02 | 1.06 | 0.92 | 1.20 | 2.89 | 0.96 | 1.63 | 1.17 | 1.22 |
| Sirpb1b | 1.00 | 1.00 | 1.00 | 1.00 | 1.00 | 1.00 | 1.00 | 1.00 | 1.00 | 1.54 | 1.75 | 1.53 |
| Siva1 | 0.50 | 0.75 | 0.85 | 0.91 | 0.62 | 1.06 | 1.06 | 3.91 | 0.89 | 2.22 | 1.18 | 1.11 |
| Slamf9 | 1.00 | 1.00 | 1.00 | 1.00 | 0.24 | 1.00 | 0.88 | 9.79 | 1.09 | 1.22 | 0.85 | 1.81 |
| Slc10a3-ubl4 | 1.00 | 1.00 | 1.00 | 1.00 | 1.00 | 1.00 | 1.00 | 5.30 | 1.00 | 1.00 | 1.00 | 1.00 |
| Slc10a6 | 1.09 | 1.00 | 1.00 | 1.00 | 1.00 | 1.00 | 1.55 | 2.48 | 1.44 | 1.00 | 1.00 | 1.00 |
| Slc11a1 | 1.00 | 1.00 | 1.00 | 1.00 | 0.79 | 1.20 | 1.51 | 5.77 | 2.08 | 2.00 | 1.24 | 1.17 |
| Slc12a5 | 1.00 | 1.00 | 1.00 | 1.00 | 1.24 | 0.99 | 1.00 | 1.00 | 1.00 | 1.00 | 1.00 | 1.00 |
| Slc15a3 | 1.00 | 1.00 | 1.00 | 1.00 | 0.68 | 1.13 | 1.17 | 6.41 | 1.41 | 3.04 | 1.57 | 1.05 |
| Slc16a3 | 1.00 | 1.00 | 1.00 | 1.18 | 0.86 | 0.95 | 1.73 | 8.03 | 1.58 | 2.24 | 1.40 | 1.14 |
| Slc17a7 | 1.00 | 1.00 | 1.00 | 1.10 | 0.85 | 0.99 | 1.00 | 1.00 | 1.00 | 1.00 | 1.00 | 1.00 |
| Slc1a2 | 1.00 | 1.00 | 1.00 | 0.85 | 0.83 | 0.94 | 1.20 | 1.00 | 1.00 | 1.00 | 1.00 | 1.00 |
| Slc22a13b-ps | 1.00 | 1.00 | 1.00 | 0.78 | 2.85 | 1.00 | 1.00 | 7.25 | 1.00 | 2.60 | 1.36 | 1.70 |
| Slc22a18 | 1.40 | 1.33 | 1.06 | 1.00 | 2.89 | 1.00 | 2.81 | 11.32 | 0.95 | 1.42 | 1.00 | 1.00 |
| Slc22a4 | 1.00 | 1.00 | 1.00 | 0.96 | 0.86 | 1.01 | 0.80 | 0.88 | 0.90 | 0.66 | 0.96 | 0.69 |
| Slc24a2 | 1.00 | 1.00 | 1.00 | 0.84 | 0.35 | 0.86 | 1.00 | 1.00 | 1.00 | 1.00 | 1.00 | 1.00 |
| Slc25a14 | 1.00 | 1.00 | 1.00 | 1.09 | 1.09 | 1.20 | 1.03 | 5.32 | 0.99 | 3.75 | 2.01 | 1.14 |
| Slc25a25 | 1.12 | 1.74 | 1.14 | 1.24 | 1.25 | 1.07 | 2.32 | 3.72 | 0.95 | 1.12 | 0.97 | 1.00 |
| Slc25a30 | 1.00 | 1.00 | 1.00 | 0.73 | 1.00 | 1.23 | 1.01 | 0.56 | 0.76 | 1.00 | 0.69 | 0.64 |
| Slc25a32 | 1.90 | 1.38 | 1.26 | 0.95 | 1.00 | 0.79 | 0.88 | 0.19 | 1.26 | 0.53 | 0.85 | 0.86 |
| Slc25a33 | 1.46 | 2.30 | 1.28 | 1.19 | 1.40 | 1.04 | 5.24 | 9.96 | 3.97 | 0.93 | 0.71 | 0.66 |
| Slc25a34 | 0.59 | 0.40 | 0.67 | 1.20 | 0.65 | 1.13 | 1.85 | 2.97 | 2.27 | 1.00 | 1.00 | 1.00 |
| Slc25a39 | 1.02 | 0.90 | 0.98 | 1.05 | 1.21 | 1.07 | 1.39 | 3.52 | 0.87 | 1.39 | 1.14 | 1.05 |
| Slc25a42 | 0.48 | 0.37 | 0.63 | 0.85 | 0.92 | 0.91 | 1.10 | 0.66 | 1.21 | 0.67 | 0.71 | 0.69 |
| Slc26a10 | 1.00 | 1.00 | 1.00 | 1.00 | 0.29 | 1.00 | 1.00 | 1.00 | 1.00 | 1.00 | 1.00 | 1.00 |
| Slc27a4 | 1.33 | 0.99 | 1.17 | 1.13 | 0.85 | 1.03 | 1.51 | 10.27 | 1.04 | 3.64 | 1.74 | 1.16 |
| Slc29a1 | 0.97 | 0.78 | 0.94 | 0.92 | 1.45 | 1.07 | 1.35 | 2.51 | 1.03 | 1.17 | 0.93 | 1.08 |
| Slc32a1 | 1.00 | 1.00 | 1.00 | 1.10 | 1.55 | 1.06 | 1.00 | 1.00 | 1.00 | 1.00 | 1.12 | 1.34 |
| Slc35e4 | 1.05 | 1.00 | 1.00 | 1.24 | 0.70 | 1.06 | 1.08 | 1.47 | 0.77 | 1.38 | 1.44 | 1.23 |
| Slc38a2 | 1.51 | 1.69 | 1.21 | 1.14 | 2.22 | 1.16 | 1.19 | 0.66 | 1.29 | 0.88 | 1.12 | 1.12 |
| Slc39a14 | 1.10 | 1.08 | 1.01 | 1.07 | 0.48 | 1.01 | 1.32 | 0.98 | 1.71 | 1.00 | 1.54 | 1.12 |
| Slc43a1 | 1.00 | 1.00 | 1.00 | 1.00 | 1.00 | 1.00 | 3.27 | 15.81 | 2.99 | 0.95 | 0.72 | 0.78 |
| Slc5a11 | 1.00 | 1.00 | 1.00 | 1.00 | 1.00 | 1.00 | 1.11 | 7.17 | 0.86 | 1.00 | 1.00 | 1.00 |
| Slc6a1 | 1.00 | 1.00 | 1.00 | 1.07 | 1.47 | 1.01 | 1.00 | 1.00 | 1.00 | 1.00 | 1.00 | 1.00 |
| Slc6a11 | 1.00 | 1.00 | 1.00 | 0.84 | 1.00 | 0.81 | 1.00 | 1.00 | 1.00 | 1.00 | 1.00 | 1.00 |
| Slc6a17 | 1.00 | 1.00 | 1.00 | 1.09 | 0.98 | 1.00 | 0.96 | 0.63 | 1.30 | 1.00 | 1.00 | 1.00 |
| Slc7a5 | 1.08 | 1.64 | 0.78 | 1.06 | 1.81 | 0.99 | 1.61 | 0.87 | 1.61 | 0.62 | 0.73 | 0.75 |

Fig. 35- 261

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Slc7a8 | 1.66 | 4.73 | 1.68 | 3.60 | 2.40 | 8.31 | 2.53 | 2.38 | 1.79 | 1.16 | 1.07 | 1.87 |
| Slc8a2 | 1.00 | 1.00 | 1.00 | 1.00 | 0.19 | 1.00 | 1.00 | 1.00 | 1.09 | 1.00 | 1.00 | 1.00 |
| Slc8b1 | 1.69 | 1.30 | 1.68 | 3.03 | 9.09 | 2.02 | 1.45 | 1.28 | 1.08 | 1.61 | 1.47 | 1.22 |
| Slco1a4 | 1.00 | 1.00 | 1.00 | 13.63 | 7.38 | 1.04 | 1.07 | 1.00 | 1.00 | 1.00 | 1.00 | 1.00 |
| Slfn2 | 3.18 | 1.60 | 3.18 | 2.41 | 9.34 | 2.24 | 2.08 | 1.44 | 1.71 | 3.04 | 2.66 | 1.21 |
| Slfn4 | 1.00 | 1.00 | 1.00 | 1.00 | 1.00 | 1.00 | 1.00 | 1.00 | 1.00 | 1.00 | 1.00 | 4.39 |
| Slfn5 | 0.67 | 1.51 | 0.94 | 1.32 | 0.36 | 0.83 | 0.99 | 1.09 | 1.17 | 0.48 | 0.30 | 1.01 |
| Slirp | 1.67 | 0.50 | 1.19 | 0.40 | 12.82 | 0.94 | 1.10 | 0.97 | 0.98 | 2.39 | 3.88 | 0.79 |
| Sln | 9.29 | 10.10 | 8.80 | 1.00 | 0.96 | 0.45 | 0.48 | 0.46 | 1.05 | 1.33 | 1.66 | 0.76 |
| Slpi | 1.00 | 1.00 | 1.00 | 1.00 | 1.00 | 1.00 | 1.00 | 1.00 | 1.00 | 1.62 | 4.28 | 1.19 |
| Slurp1 | 1.00 | 1.00 | 1.00 | 1.00 | 1.00 | 1.00 | 1.00 | 1.00 | 1.00 | 0.15 | 0.58 | 0.44 |
| Smagp | 1.39 | 0.74 | 1.32 | 0.54 | 5.09 | 1.07 | 0.85 | 0.70 | 0.87 | 1.37 | 2.16 | 1.03 |
| Smap1 | 1.25 | 1.91 | 1.12 | 1.07 | 0.65 | 1.00 | 1.47 | 1.17 | 0.96 | 0.45 | 0.56 | 0.99 |
| Smarcal1 | 1.01 | 0.57 | 1.23 | 0.98 | 3.62 | 0.82 | 0.95 | 0.99 | 1.02 | 4.01 | 3.89 | 1.11 |
| Smarcd2 | 0.86 | 0.51 | 0.89 | 1.10 | 4.99 | 0.96 | 0.81 | 0.78 | 0.75 | 1.97 | 1.91 | 0.88 |
| Smarcd3 | 1.26 | 0.92 | 1.02 | 0.34 | 3.11 | 0.95 | 0.98 | 1.05 | 0.80 | 3.29 | 2.59 | 0.89 |
| Smcp | 1.00 | 1.00 | 1.00 | 1.00 | 1.00 | 1.00 | 1.00 | 1.00 | 1.00 | 1.43 | 1.00 | 1.00 |
| Smg9 | 1.06 | 0.62 | 0.91 | 0.43 | 4.58 | 0.91 | 0.90 | 0.86 | 0.84 | 2.41 | 3.09 | 0.86 |
| Smim1 | 1.11 | 0.27 | 1.52 | 0.56 | 6.03 | 0.57 | 1.02 | 1.46 | 1.25 | 1.61 | 1.88 | 1.21 |
| Smim20 | 1.01 | 0.56 | 0.71 | 0.41 | 4.60 | 0.78 | 1.04 | 0.89 | 0.72 | 1.52 | 2.45 | 0.97 |
| Smim22 | 1.00 | 1.00 | 1.00 | 1.00 | 1.00 | 1.00 | 1.00 | 1.00 | 1.00 | 2.74 | 5.13 | 1.09 |
| Smim23 | 1.00 | 1.00 | 1.00 | 1.00 | 1.00 | 1.00 | 1.00 | 1.00 | 1.00 | 1.38 | 1.00 | 1.00 |
| Smim24 | 1.00 | 1.00 | 1.00 | 0.70 | 0.78 | 1.09 | 1.98 | 1.02 | 0.47 | 1.00 | 0.65 | 0.98 |
| Smpd2 | 0.95 | 0.54 | 0.87 | 0.53 | 7.28 | 1.39 | 0.82 | 0.75 | 0.84 | 2.24 | 3.06 | 0.92 |
| Smpd5 | 1.00 | 0.22 | 1.00 | 0.18 | 30.79 | 0.72 | 1.00 | 0.96 | 1.00 | 2.11 | 4.66 | 0.85 |
| Snap25 | 1.00 | 1.00 | 1.00 | 1.00 | 0.01 | 1.00 | 1.00 | 1.00 | 1.00 | 1.00 | 1.00 | 1.00 |
| Snap91 | 1.00 | 1.00 | 1.00 | 1.00 | 0.23 | 1.00 | 0.86 | 1.10 | 1.50 | 1.00 | 1.00 | 1.00 |
| Sncb | 1.00 | 1.00 | 1.00 | 1.00 | 0.10 | 1.00 | 1.00 | 1.00 | 1.00 | 1.00 | 1.00 | 1.00 |
| Snf8 | 1.15 | 0.34 | 0.88 | 0.30 | 18.32 | 1.08 | 1.09 | 0.57 | 0.84 | 4.79 | 6.69 | 1.20 |
| Snhg11 | 1.00 | 1.00 | 1.00 | 2.19 | 0.06 | 1.28 | 1.00 | 1.00 | 1.51 | 1.10 | 1.10 | 0.87 |
| Snhg12 | 2.71 | 1.39 | 2.41 | 1.31 | 6.27 | 1.67 | 1.75 | 1.88 | 1.13 | 2.18 | 2.92 | 0.80 |
| Snhg3 | 1.66 | 1.54 | 1.28 | 3.29 | 6.54 | 1.96 | 0.79 | 0.63 | 0.86 | 0.43 | 0.79 | 0.57 |
| Snhg5 | 1.52 | 1.52 | 1.21 | 1.45 | 7.11 | 1.51 | 1.46 | 1.78 | 0.91 | 1.59 | 1.75 | 0.82 |
| Snhg9 | 1.00 | 1.00 | 1.00 | 1.00 | 1.00 | 1.00 | 1.00 | 1.00 | 1.00 | 1.00 | 1.00 | 1.00 |
| Snora15 | 1.00 | 1.00 | 1.00 | 1.00 | 1.00 | 1.00 | 1.00 | 1.00 | 1.00 | 1.00 | 1.00 | 1.00 |
| Snora16a | 1.00 | 1.00 | 5.92 | 8.00 | 1.29 | 1.00 | 13.36 | 1.00 | 7.17 | 1.00 | 1.00 | 4.42 |
| Snora17 | 1.00 | 1.00 | 1.00 | 1.00 | 0.11 | 1.00 | 1.00 | 1.00 | 1.14 | 21.79 | 1.00 | 0.15 |
| Snora21 | 1.00 | 0.10 | 1.00 | 1.00 | 1.00 | 1.00 | 1.00 | 1.00 | 1.00 | 1.00 | 1.00 | 1.00 |
| Snora23 | 0.39 | 1.00 | 1.00 | 1.00 | 1.00 | 0.48 | 1.00 | 1.00 | 1.00 | 1.00 | 1.00 | 1.00 |
| Snora28 | 1.00 | 1.00 | 13.14 | 1.00 | 1.00 | 1.00 | 1.00 | 1.00 | 1.00 | 1.00 | 1.00 | 1.00 |
| Snora3 | 1.00 | 1.00 | 1.00 | 1.00 | 1.00 | 1.00 | 1.00 | 1.00 | 0.07 | 1.00 | 1.00 | 1.00 |
| Snora31 | 1.00 | 1.00 | 1.00 | 1.00 | 1.00 | 1.00 | 0.02 | 1.00 | 1.00 | 1.00 | 1.00 | 0.04 |
| Snora33 | 1.00 | 1.00 | 1.00 | 1.00 | 1.00 | 1.00 | 1.00 | 1.00 | 1.00 | 1.00 | 1.00 | 1.00 |
| Snora34 | 1.00 | 1.00 | 16.28 | 1.00 | 1.00 | 0.81 | 1.00 | 1.00 | 1.00 | 1.00 | 1.00 | 1.00 |
| Snora41 | 1.00 | 1.00 | 1.00 | 0.11 | 1.00 | 0.03 | 1.00 | 1.00 | 1.00 | 1.00 | 1.00 | 39.10 |
| Snora43 | 1.00 | 1.00 | 1.00 | 0.11 | 0.16 | 0.07 | 0.23 | 1.00 | 0.09 | 1.00 | 0.21 | 0.80 |
| Snora44 | 79.25 | 1.00 | 1.00 | 1.00 | 1.00 | 1.00 | 1.00 | 1.00 | 1.00 | 1.00 | 1.00 | 1.00 |
| Snora52 | 1.00 | 1.00 | 6.46 | 0.36 | 1.00 | 0.12 | 4.88 | 1.00 | 7.83 | 1.00 | 1.00 | 4.84 |
| Snora62 | 1.00 | 1.00 | 1.00 | 1.00 | 1.00 | 1.00 | 1.00 | 1.00 | 1.00 | 1.00 | 1.00 | 1.00 |
| Snora64 | 1.00 | 0.04 | 1.00 | 1.90 | 0.04 | 2.44 | 27.76 | 0.02 | 0.05 | 1.00 | 1.00 | 1.00 |
| Snora65 | 1.00 | 1.00 | 1.00 | 0.08 | 0.04 | 1.00 | 0.42 | 47.28 | 1.14 | 1.00 | 0.05 | 12.60 |
| Snora69 | 1.00 | 1.00 | 1.00 | 0.20 | 1.00 | 1.00 | 1.00 | 1.00 | 1.00 | 1.00 | 1.00 | 1.00 |
| Snora70 | 0.05 | 2.64 | 1.00 | 0.29 | 0.02 | 0.82 | 6.28 | 1.00 | 1.00 | 0.13 | 1.00 | 0.03 |
| Snora74a | 1.00 | 1.00 | 1.00 | 1.00 | 0.82 | 1.00 | 0.56 | 2.55 | 1.00 | 1.00 | 1.00 | 1.00 |
| Snora75 | 1.00 | 1.00 | 1.00 | 1.00 | 1.00 | 1.00 | 1.00 | 1.00 | 1.00 | 1.00 | 1.00 | 1.00 |
| Snora78 | 1.00 | 1.00 | 1.00 | 0.71 | 8.54 | 1.00 | 4.21 | 1.00 | 0.33 | 0.23 | 5.96 | 1.00 |
| Snora7a | 1.00 | 1.00 | 1.00 | 0.15 | 1.00 | 1.00 | 0.07 | 1.00 | 0.11 | 1.00 | 0.04 | 0.80 |
| Snora81 | 3.77 | 1.00 | 1.00 | 0.28 | 4.05 | 0.83 | 1.74 | 1.00 | 2.93 | 1.00 | 1.00 | 1.18 |
| Snord15a | 1.00 | 1.00 | 1.00 | 1.00 | 1.00 | 1.00 | 1.00 | 1.00 | 1.00 | 1.00 | 1.00 | 1.00 |
| Snord15b | 0.12 | 1.00 | 1.00 | 0.52 | 1.00 | 1.00 | 1.00 | 1.00 | 1.14 | 18.33 | 1.00 | 3.09 |
| Snord17 | 1.00 | 1.00 | 1.00 | 1.00 | 1.00 | 1.00 | 0.78 | 1.80 | 1.00 | 8.66 | 1.00 | 1.00 |
| Snord22 | 19.73 | 46.43 | 0.43 | 0.04 | 16.52 | 1.00 | 0.22 | 0.05 | 11.72 | 1.00 | 0.47 | 29.38 |
| Snord7 | 1.00 | 1.00 | 1.00 | 1.00 | 1.00 | 1.00 | 1.00 | 1.00 | 1.00 | 1.00 | 1.00 | 1.00 |
| Snph | 0.89 | 1.00 | 0.74 | 1.00 | 0.17 | 1.00 | 1.00 | 1.00 | 1.00 | 1.00 | 1.00 | 1.00 |

Fig. 35- 262

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Slc7a8 | 2.80 | 2.52 | 2.02 | 1.38 | 2.60 | 1.34 | 0.65 | 1.00 | 0.82 | 1.25 | 1.52 | 1.47 |
| Slc8a2 | 0.94 | 0.82 | 1.00 | 1.00 | 1.00 | 1.00 | 1.00 | 1.00 | 1.00 | 0.86 | 0.61 | 0.92 |
| Slc8b1 | 1.81 | 1.97 | 1.56 | 1.75 | 1.38 | 1.34 | 1.37 | 1.19 | 1.45 | 0.96 | 1.36 | 1.05 |
| Slco1a4 | 1.00 | 1.00 | 1.00 | 6.12 | 2.74 | 1.48 | 0.22 | 0.20 | 0.17 | 1.00 | 1.00 | 1.00 |
| Slfn2 | 1.40 | 1.62 | 1.31 | 2.74 | 1.82 | 2.21 | 2.88 | 4.58 | 1.20 | 2.73 | 2.66 | 2.24 |
| Slfn4 | 1.00 | 1.00 | 1.00 | 1.00 | 1.00 | 1.00 | 1.00 | 1.00 | 1.00 | 4.70 | 3.39 | 3.67 |
| Slfn5 | 1.20 | 0.98 | 1.47 | 1.00 | 1.51 | 1.06 | 1.10 | 1.00 | 1.62 | 1.55 | 1.05 | 1.26 |
| Slirp | 1.08 | 1.31 | 0.85 | 0.82 | 0.58 | 0.88 | 2.07 | 2.14 | 0.79 | 1.44 | 1.72 | 0.97 |
| Sln | 1.66 | 0.87 | 1.00 | 1.00 | 1.00 | 1.00 | 1.00 | 1.00 | 1.00 | 1.00 | 1.79 | 0.60 |
| Slpi | 1.36 | 2.15 | 2.16 | 1.00 | 0.28 | 1.00 | 1.00 | 3.55 | 1.00 | 0.92 | 1.90 | 1.22 |
| Slurp1 | 0.86 | 1.00 | 1.00 | 1.00 | 1.00 | 1.00 | 1.00 | 1.00 | 1.00 | 1.00 | 1.00 | 1.00 |
| Smagp | 1.77 | 1.77 | 1.59 | 0.77 | 0.74 | 0.77 | 0.88 | 0.89 | 0.91 | 0.98 | 1.54 | 0.98 |
| Smap1 | 1.03 | 1.01 | 1.05 | 1.24 | 6.65 | 0.93 | 1.26 | 0.29 | 0.95 | 1.23 | 1.22 | 1.08 |
| Smarcal1 | 0.95 | 0.93 | 0.89 | 1.01 | 0.51 | 0.94 | 0.71 | 2.00 | 0.99 | 0.82 | 0.94 | 0.96 |
| Smarcd2 | 0.89 | 1.04 | 0.82 | 0.87 | 0.65 | 0.90 | 0.78 | 1.54 | 0.92 | 0.92 | 1.25 | 0.97 |
| Smarcd3 | 1.59 | 0.85 | 1.29 | 0.75 | 0.30 | 0.96 | 1.00 | 1.00 | 1.00 | 1.28 | 0.97 | 0.99 |
| Smcp | 1.00 | 1.00 | 1.00 | 0.99 | 1.57 | 1.58 | 1.25 | 1.00 | 1.00 | 1.00 | 1.00 | 1.00 |
| Smg9 | 1.04 | 1.30 | 0.90 | 0.92 | 0.55 | 0.71 | 1.05 | 2.13 | 0.83 | 1.11 | 1.81 | 1.09 |
| Smim1 | 2.27 | 2.65 | 1.97 | 1.16 | 0.95 | 0.96 | 1.00 | 1.26 | 0.99 | 0.90 | 1.13 | 1.61 |
| Smim20 | 1.42 | 1.87 | 1.05 | 0.96 | 0.76 | 1.01 | 1.14 | 1.62 | 1.21 | 1.14 | 2.03 | 1.00 |
| Smim22 | 1.64 | 1.32 | 1.21 | 0.48 | 0.43 | 1.29 | 1.00 | 4.92 | 1.00 | 1.07 | 1.74 | 1.03 |
| Smim23 | 1.00 | 1.00 | 1.00 | 1.00 | 1.00 | 1.00 | 1.00 | 1.00 | 1.00 | 1.00 | 1.00 | 1.00 |
| Smim24 | 1.76 | 1.33 | 1.37 | 0.77 | 2.70 | 0.86 | 1.00 | 1.00 | 1.00 | 0.74 | 0.91 | 0.84 |
| Smpd2 | 1.33 | 1.74 | 0.95 | 1.14 | 0.86 | 0.94 | 0.91 | 1.58 | 0.79 | 0.99 | 1.58 | 0.99 |
| Smpd5 | 0.98 | 1.42 | 1.33 | 1.00 | 0.40 | 1.12 | 1.00 | 3.67 | 1.00 | 1.00 | 1.12 | 0.92 |
| Snap25 | 1.00 | 1.00 | 1.00 | 1.00 | 1.00 | 1.00 | 1.00 | 1.35 | 1.00 | 1.17 | 1.12 | 1.24 |
| Snap91 | 0.27 | 0.33 | 0.58 | 1.00 | 1.00 | 1.00 | 1.00 | 1.00 | 1.00 | 1.11 | 1.00 | 0.98 |
| Sncb | 1.00 | 1.00 | 1.00 | 1.00 | 1.00 | 1.00 | 1.00 | 1.00 | 1.00 | 1.00 | 1.21 | 1.00 |
| Snf8 | 1.26 | 1.79 | 0.91 | 0.74 | 0.45 | 0.87 | 1.12 | 3.56 | 0.83 | 0.89 | 1.84 | 1.02 |
| Snhg11 | 1.77 | 1.31 | 1.65 | 2.88 | 2.07 | 2.99 | 2.07 | 1.66 | 1.81 | 0.94 | 0.98 | 1.02 |
| Snhg12 | 1.28 | 1.18 | 1.31 | 1.25 | 0.89 | 1.26 | 1.25 | 2.34 | 1.25 | 1.06 | 1.20 | 1.10 |
| Snhg3 | 1.03 | 1.52 | 0.87 | 0.94 | 1.61 | 0.75 | 1.87 | 0.55 | 2.22 | 0.96 | 1.60 | 0.89 |
| Snhg5 | 1.07 | 1.03 | 0.90 | 1.46 | 1.33 | 0.89 | 1.41 | 2.19 | 1.68 | 1.03 | 1.72 | 1.03 |
| Snhg9 | 1.00 | 1.00 | 1.00 | 1.00 | 1.00 | 1.00 | 1.00 | 1.00 | 1.00 | 1.00 | 1.00 | 1.00 |
| Snora15 | 1.00 | 1.00 | 1.00 | 1.00 | 1.00 | 1.00 | 1.00 | 1.00 | 1.00 | 1.00 | 1.00 | 1.00 |
| Snora16a | 0.99 | 0.44 | 5.38 | 4.63 | 1.00 | 1.24 | 0.94 | 60.44 | 0.19 | 1.00 | 1.00 | 2.51 |
| Snora17 | 1.00 | 1.00 | 1.53 | 1.00 | 1.00 | 1.00 | 1.00 | 1.00 | 1.00 | 1.00 | 1.00 | 1.00 |
| Snora21 | 1.00 | 1.00 | 1.00 | 1.00 | 1.00 | 1.00 | 1.00 | 1.00 | 1.00 | 1.00 | 1.00 | 1.00 |
| Snora23 | 1.00 | 1.00 | 1.00 | 1.00 | 1.00 | 1.00 | 2.66 | 1.00 | 1.00 | 1.00 | 1.00 | 1.00 |
| Snora28 | 1.00 | 1.00 | 1.00 | 1.00 | 1.00 | 1.00 | 68.16 | 1.00 | 1.00 | 1.00 | 1.00 | 0.07 |
| Snora3 | 0.78 | 1.00 | 0.07 | 1.00 | 1.00 | 1.00 | 1.00 | 1.00 | 1.00 | 1.00 | 1.00 | 1.00 |
| Snora31 | 108.55 | 0.86 | 21.49 | 1.00 | 1.00 | 1.00 | 1.00 | 1.00 | 1.00 | 1.00 | 1.00 | 1.00 |
| Snora33 | 147.50 | 0.01 | 1.00 | 1.00 | 1.00 | 1.00 | 1.00 | 1.00 | 0.01 | 1.00 | 1.00 | 1.00 |
| Snora34 | 0.01 | 1.00 | 12.68 | 1.00 | 1.00 | 0.07 | 43.85 | 1.00 | 1.00 | 1.00 | 1.00 | 1.00 |
| Snora41 | 48.53 | 1.00 | 19.44 | 1.00 | 1.00 | 1.00 | 1.00 | 1.00 | 1.00 | 1.00 | 1.00 | 1.00 |
| Snora43 | 0.10 | 1.31 | 1.54 | 1.00 | 1.00 | 1.00 | 1.00 | 1.00 | 1.00 | 0.08 | 8.11 | 14.00 |
| Snora44 | 1.00 | 1.00 | 13.70 | 1.00 | 1.00 | 1.00 | 1.00 | 1.00 | 1.00 | 1.00 | 1.00 | 1.00 |
| Snora52 | 1.00 | 0.04 | 10.10 | 1.00 | 1.00 | 6.71 | 0.06 | 1.00 | 1.00 | 1.00 | 1.00 | 8.71 |
| Snora62 | 1.00 | 1.00 | 1.00 | 1.00 | 1.00 | 1.00 | 1.00 | 1.00 | 0.13 | 1.00 | 14.83 | 1.00 |
| Snora64 | 0.02 | 0.03 | 0.74 | 1.00 | 1.00 | 1.00 | 95.98 | 0.04 | 1.00 | 1.00 | 2.14 | 24.56 |
| Snora65 | 0.39 | 0.86 | 1.49 | 66.29 | 1.00 | 1.00 | 1.00 | 1.00 | 1.00 | 0.02 | 0.03 | 22.68 |
| Snora69 | 1.00 | 21.97 | 0.75 | 1.00 | 1.00 | 1.00 | 1.00 | 1.00 | 1.00 | 0.01 | 1.00 | 0.07 |
| Snora70 | 0.06 | 3.48 | 0.95 | 28.15 | 1.00 | 0.62 | 0.93 | 1.00 | 1.00 | 0.05 | 69.67 | 11.19 |
| Snora74a | 1.00 | 1.39 | 1.00 | 1.00 | 1.24 | 1.00 | 1.00 | 1.00 | 0.90 | 1.00 | 1.00 | 1.59 |
| Snora75 | 1.00 | 1.72 | 0.05 | 1.00 | 1.00 | 1.00 | 1.00 | 1.00 | 1.00 | 1.00 | 1.00 | 1.00 |
| Snora78 | 3.81 | 0.89 | 0.17 | 1.48 | 0.48 | 0.42 | 1.00 | 1.00 | 1.00 | 1.00 | 1.00 | 0.33 |
| Snora7a | 0.06 | 0.06 | 0.12 | 1.00 | 1.00 | 1.00 | 1.00 | 1.00 | 1.15 | 1.00 | 1.00 | 1.00 |
| Snora81 | 1.01 | 0.13 | 1.59 | 1.47 | 1.00 | 2.50 | 4.38 | 8.22 | 2.30 | 0.47 | 3.23 | 0.62 |
| Snord15a | 1.00 | 1.00 | 1.00 | 1.00 | 1.00 | 1.00 | 1.00 | 1.00 | 1.00 | 1.00 | 1.00 | 1.00 |
| Snord15b | 11.86 | 0.15 | 13.15 | 1.00 | 0.04 | 1.00 | 1.00 | 33.18 | 1.00 | 1.00 | 2.25 | 5.55 |
| Snord17 | 0.28 | 9.65 | 1.49 | 1.00 | 0.78 | 1.00 | 1.00 | 27.78 | 1.00 | 0.37 | 1.00 | 1.00 |
| Snord22 | 48.41 | 32.82 | 1.89 | 1.00 | 37.00 | 0.25 | 1.00 | 83.27 | 4.61 | 50.71 | 0.73 | 0.10 |
| Snord7 | 1.00 | 697.71 | 1.00 | 1.00 | 1.00 | 1.00 | 1.00 | 1.00 | 1.00 | 1.00 | 1.00 | 1.00 |
| Snph | 1.00 | 1.00 | 1.00 | 1.00 | 1.00 | 1.00 | 1.00 | 1.00 | 1.00 | 0.88 | 0.71 | 0.86 |

Fig. 35- 263

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Slc7a8 | 1.59 | 2.01 | 1.42 | 7.97 | 8.54 | 4.11 | 1.03 | 0.36 | 0.79 | 1.01 | 1.30 | 1.07 |
| Slc8a2 | 1.25 | 0.87 | 1.26 | 1.00 | 1.00 | 1.00 | 1.06 | 1.07 | 1.10 | 1.00 | 7.08 | 0.84 |
| Slc8b1 | 1.38 | 1.73 | 1.63 | 1.59 | 2.64 | 1.26 | 0.64 | 2.56 | 1.08 | 0.85 | 1.02 | 0.76 |
| Slco1a4 | 1.00 | 1.00 | 1.00 | 3.07 | 1.00 | 1.00 | 0.95 | 1.00 | 0.96 | 1.00 | 1.34 | 1.00 |
| Slfn2 | 3.48 | 3.68 | 3.35 | 1.94 | 3.39 | 1.29 | 1.00 | 1.78 | 1.00 | 1.84 | 1.56 | 1.48 |
| Slfn4 | 10.63 | 27.28 | 7.86 | 1.00 | 1.00 | 1.00 | 1.00 | 1.00 | 1.00 | 5.11 | 1.67 | 4.99 |
| Slfn5 | 1.21 | 1.08 | 1.25 | 0.83 | 0.29 | 0.76 | 1.46 | 1.31 | 0.93 | 2.55 | 1.48 | 2.04 |
| Slirp | 0.56 | 0.63 | 1.13 | 0.87 | 1.20 | 0.90 | 1.04 | 2.96 | 0.87 | 0.91 | 0.96 | 0.82 |
| Sln | 4.43 | 1.91 | 2.49 | 1.00 | 1.00 | 1.00 | 0.69 | 1.75 | 1.18 | 2.11 | 2.81 | 2.54 |
| Slpi | 1.32 | 1.24 | 1.69 | 2.31 | 7.31 | 3.43 | 1.00 | 2.18 | 1.00 | 1.27 | 1.23 | 0.35 |
| Slurp1 | 0.52 | 0.62 | 0.73 | 1.00 | 1.00 | 1.00 | 1.00 | 1.00 | 1.00 | 1.00 | 1.00 | 1.00 |
| Smagp | 0.92 | 1.14 | 1.01 | 0.87 | 3.05 | 0.95 | 0.55 | 0.97 | 0.92 | 1.13 | 1.45 | 1.04 |
| Smap1 | 1.00 | 1.05 | 1.00 | 0.98 | 0.49 | 0.93 | 1.03 | 0.62 | 0.95 | 0.96 | 0.86 | 0.72 |
| Smarcal1 | 0.89 | 0.80 | 0.85 | 0.95 | 1.58 | 0.95 | 1.11 | 4.40 | 1.03 | 0.93 | 1.02 | 1.06 |
| Smarcd2 | 0.92 | 1.06 | 1.06 | 0.69 | 2.52 | 1.11 | 0.98 | 2.48 | 0.91 | 1.06 | 1.03 | 0.99 |
| Smarcd3 | 0.87 | 1.10 | 1.06 | 0.88 | 2.93 | 0.74 | 1.00 | 3.06 | 0.64 | 0.86 | 1.86 | 0.62 |
| Smcp | 1.04 | 1.00 | 0.76 | 3.89 | 3.63 | 1.29 | 0.96 | 0.54 | 0.96 | 1.00 | 1.00 | 1.00 |
| Smg9 | 0.82 | 1.20 | 0.90 | 0.92 | 2.81 | 0.93 | 0.85 | 2.37 | 1.09 | 0.90 | 1.27 | 0.81 |
| Smim1 | 1.29 | 1.34 | 1.80 | 0.82 | 3.69 | 1.15 | 1.20 | 1.63 | 1.25 | 0.93 | 1.16 | 0.85 |
| Smim20 | 1.07 | 1.06 | 0.94 | 0.62 | 1.97 | 0.92 | 1.06 | 1.60 | 0.97 | 1.27 | 1.81 | 1.13 |
| Smim22 | 0.84 | 0.87 | 0.92 | 0.77 | 12.30 | 1.80 | 1.00 | 2.21 | 1.00 | 1.00 | 1.00 | 1.00 |
| Smim23 | 1.00 | 1.00 | 1.00 | 1.77 | 8.38 | 1.00 | 0.88 | 8.13 | 1.27 | 1.00 | 1.00 | 1.00 |
| Smim24 | 0.76 | 0.95 | 0.73 | 1.28 | 1.00 | 1.52 | 1.00 | 0.13 | 0.93 | 1.95 | 1.18 | 1.66 |
| Smpd2 | 1.11 | 1.11 | 1.19 | 0.90 | 2.04 | 0.96 | 0.96 | 1.79 | 0.99 | 1.16 | 1.28 | 1.05 |
| Smpd5 | 1.00 | 1.00 | 1.00 | 0.81 | 8.95 | 0.55 | 0.92 | 1.95 | 1.10 | 0.60 | 0.87 | 0.62 |
| Snap25 | 1.33 | 1.67 | 1.50 | 1.00 | 0.90 | 1.91 | 1.00 | 1.00 | 1.00 | 1.00 | 126.62 | 1.00 |
| Snap91 | 1.00 | 1.00 | 1.00 | 1.00 | 1.00 | 1.00 | 1.00 | 1.00 | 1.00 | 1.00 | 7.54 | 1.00 |
| Sncb | 1.00 | 1.00 | 1.00 | 1.00 | 1.00 | 1.00 | 1.00 | 2.00 | 1.00 | 1.00 | 16.06 | 1.00 |
| Snf8 | 0.97 | 1.38 | 1.23 | 0.98 | 1.89 | 0.92 | 0.92 | 5.37 | 0.86 | 1.15 | 1.60 | 1.00 |
| Snhg11 | 1.62 | 1.69 | 1.87 | 0.63 | 1.40 | 0.97 | 1.55 | 1.08 | 0.76 | 1.00 | 53.13 | 1.16 |
| Snhg12 | 1.16 | 1.10 | 1.21 | 1.56 | 8.91 | 2.20 | 0.66 | 1.51 | 0.91 | 1.38 | 1.62 | 1.10 |
| Snhg3 | 0.95 | 0.68 | 1.01 | 2.19 | 18.71 | 1.85 | 0.87 | 0.44 | 0.95 | 1.38 | 1.54 | 1.24 |
| Snhg5 | 0.94 | 0.93 | 1.09 | 1.54 | 14.40 | 1.92 | 0.92 | 0.67 | 0.92 | 1.30 | 1.11 | 0.91 |
| Snhg9 | 1.00 | 1.00 | 1.00 | 1.00 | 1.00 | 1.00 | 2.56 | 5.33 | 0.57 | 1.00 | 1.00 | 1.00 |
| Snora15 | 1.00 | 1.00 | 1.00 | 1.00 | 0.00 | 1.00 | 1.00 | 1.00 | 1.00 | 1.00 | 1.00 | 1.00 |
| Snora16a | 1.00 | 0.08 | 5.82 | 1.00 | 0.01 | 1.02 | 0.09 | 1.00 | 1.00 | 0.07 | 1.74 | 4.46 |
| Snora17 | 1.00 | 32.05 | 1.00 | 1.00 | 1.00 | 6.25 | 1.00 | 1.00 | 1.00 | 1.00 | 0.08 | 0.89 |
| Snora21 | 1.00 | 1.00 | 8.44 | 23.25 | 1.00 | 1.00 | 1.00 | 10.69 | 9.54 | 0.04 | 14.23 | 1.00 |
| Snora23 | 1.00 | 1.00 | 1.00 | 1.00 | 0.06 | 1.00 | 1.00 | 1.00 | 1.00 | 1.00 | 1.00 | 1.00 |
| Snora28 | 1.00 | 1.00 | 1.00 | 0.04 | 1.00 | 0.09 | 1.00 | 1.00 | 1.00 | 1.00 | 1.00 | 0.89 |
| Snora3 | 1.00 | 1.00 | 1.00 | 1.00 | 1.00 | 1.00 | 1.00 | 1.00 | 1.00 | 1.00 | 1.00 | 14.52 |
| Snora31 | 1.00 | 1.00 | 0.04 | 1.00 | 0.00 | 1.00 | 1.00 | 1.00 | 1.00 | 1.00 | 1.00 | 1.00 |
| Snora33 | 1.00 | 1.00 | 1.00 | 1.00 | 1.00 | 1.00 | 1.00 | 1.00 | 1.00 | 1.00 | 1.00 | 74.78 |
| Snora34 | 51.45 | 1.00 | 1.00 | 52.42 | 1.00 | 14.36 | 1.00 | 1.00 | 1.00 | 0.02 | 1.00 | 1.78 |
| Snora41 | 85.43 | 1.00 | 1.00 | 1.00 | 1.00 | 0.05 | 1.00 | 1.00 | 1.00 | 84.54 | 0.02 | 1.00 |
| Snora43 | 1.00 | 1.00 | 1.03 | 1.00 | 0.64 | 9.23 | 1.00 | 1.00 | 5.72 | 1.00 | 7.78 | 30.90 |
| Snora44 | 1.00 | 1.00 | 1.00 | 1.00 | 0.00 | 1.00 | 1.00 | 1.00 | 1.00 | 1.00 | 32.77 | 1.78 |
| Snora52 | 1.00 | 1.00 | 0.51 | 1.00 | 0.04 | 5.70 | 0.04 | 1.00 | 1.00 | 1.00 | 0.09 | 0.45 |
| Snora62 | 1.00 | 1.00 | 1.00 | 1.00 | 1.00 | 1.00 | 1.00 | 1.00 | 1.00 | 1.00 | 1.00 | 1.00 |
| Snora64 | 0.01 | 1.00 | 0.03 | 57.74 | 0.00 | 1.54 | 1.00 | 1.00 | 0.03 | 0.02 | 32.77 | 0.44 |
| Snora65 | 0.02 | 1.00 | 1.00 | 1.52 | 1.00 | 0.07 | 1.00 | 1.00 | 36.24 | 1.89 | 1.72 | 0.03 |
| Snora69 | 1.00 | 1.00 | 0.08 | 1.00 | 1.00 | 1.00 | 1.00 | 1.00 | 1.00 | 35.01 | 0.02 | 1.00 |
| Snora70 | 88.17 | 0.03 | 0.17 | 0.03 | 0.01 | 6.13 | 0.06 | 1.00 | 0.11 | 2.77 | 0.29 | 1.11 |
| Snora74a | 1.00 | 2.13 | 0.82 | 1.00 | 0.03 | 1.00 | 1.00 | 1.00 | 1.35 | 1.00 | 1.43 | 0.78 |
| Snora75 | 1.00 | 1.00 | 1.00 | 1.00 | 1.00 | 1.00 | 1.00 | 1.00 | 1.00 | 1.00 | 35.97 | 1.00 |
| Snora78 | 5.96 | 1.00 | 11.65 | 0.70 | 0.00 | 0.51 | 5.46 | 0.48 | 3.95 | 0.30 | 0.58 | 5.52 |
| Snora7a | 0.05 | 1.00 | 1.00 | 1.00 | 0.00 | 7.24 | 1.00 | 1.00 | 1.00 | 1.00 | 0.06 | 1.00 |
| Snora81 | 1.15 | 0.16 | 1.05 | 0.32 | 0.19 | 1.01 | 0.27 | 13.41 | 2.61 | 0.18 | 0.88 | 0.79 |
| Snord15a | 1.00 | 1.00 | 1.00 | 1.00 | 0.01 | 1.00 | 1.00 | 38.88 | 1.00 | 1.00 | 1.00 | 1.00 |
| Snord15b | 1.00 | 8.59 | 1.00 | 0.16 | 0.07 | 0.28 | 8.91 | 24.09 | 1.00 | 8.42 | 0.07 | 0.89 |
| Snord17 | 1.00 | 1.00 | 1.00 | 1.23 | 0.11 | 1.00 | 0.89 | 10.64 | 1.00 | 0.62 | 0.63 | 0.53 |
| Snord22 | 0.04 | 0.05 | 0.11 | 0.06 | 0.14 | 8.52 | 1.00 | 1.28 | 1.00 | 76.65 | 0.35 | 1.19 |
| Snord7 | 1.00 | 1.00 | 1.00 | 1.00 | 1.00 | 1.00 | 1.00 | 1.00 | 1.00 | 1.00 | 1.00 | 1.00 |
| Snph | 0.81 | 0.87 | 1.29 | 1.00 | 1.00 | 1.00 | 1.00 | 1.00 | 1.00 | 1.00 | 9.75 | 1.00 |

Fig. 35- 264

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Slc7a8 | 1.34 | 1.61 | 1.16 | 0.92 | 1.04 | 0.97 | 2.25 | 0.54 | 1.66 | 0.65 | 0.99 | 1.10 |
| Slc8a2 | 1.00 | 1.00 | 1.00 | 0.99 | 0.58 | 0.99 | 1.00 | 1.00 | 1.00 | 1.00 | 1.00 | 1.00 |
| Slc8b1 | 1.41 | 1.32 | 1.31 | 1.31 | 3.44 | 1.15 | 1.43 | 1.66 | 1.33 | 1.66 | 1.44 | 1.09 |
| Slco1a4 | 1.00 | 1.00 | 1.00 | 1.10 | 1.23 | 1.11 | 1.00 | 1.00 | 1.00 | 1.00 | 1.00 | 1.00 |
| Slfn2 | 1.00 | 1.06 | 2.27 | 1.78 | 0.94 | 1.71 | 1.70 | 7.44 | 1.82 | 3.72 | 2.34 | 1.68 |
| Slfn4 | 1.00 | 1.00 | 1.00 | 1.00 | 1.00 | 1.00 | 1.00 | 1.00 | 1.00 | 0.93 | 1.69 | 1.84 |
| Slfn5 | 0.72 | 1.10 | 1.58 | 0.93 | 0.95 | 0.91 | 1.49 | 0.43 | 1.55 | 2.47 | 7.79 | 9.25 |
| Slirp | 2.47 | 0.86 | 1.00 | 1.27 | 0.69 | 0.79 | 1.08 | 17.00 | 0.76 | 3.26 | 1.07 | 1.34 |
| Sln | 1.00 | 1.00 | 1.00 | 0.92 | 4.12 | 0.78 | 1.09 | 1.57 | 1.05 | 1.00 | 1.00 | 1.00 |
| Slpi | 1.37 | 3.31 | 2.10 | 1.00 | 1.60 | 1.00 | 1.03 | 4.50 | 0.56 | 2.58 | 1.54 | 1.41 |
| Slurp1 | 1.00 | 1.00 | 1.00 | 1.00 | 1.00 | 1.00 | 0.90 | 5.04 | 0.54 | 1.00 | 1.00 | 1.00 |
| Smagp | 1.42 | 1.37 | 0.85 | 0.61 | 0.39 | 0.83 | 1.14 | 3.28 | 0.89 | 2.02 | 1.49 | 1.29 |
| Smap1 | 1.33 | 0.97 | 1.00 | 1.11 | 1.98 | 0.94 | 0.99 | 0.36 | 0.94 | 0.53 | 0.91 | 0.96 |
| Smarcal1 | 1.00 | 1.00 | 1.00 | 0.95 | 0.85 | 1.04 | 0.82 | 12.68 | 1.05 | 3.37 | 1.03 | 0.94 |
| Smarcd2 | 0.87 | 0.94 | 0.89 | 0.95 | 0.87 | 0.92 | 1.05 | 6.37 | 1.11 | 1.87 | 1.15 | 1.07 |
| Smarcd3 | 1.00 | 1.00 | 1.00 | 1.02 | 0.72 | 0.97 | 0.92 | 13.69 | 1.67 | 1.00 | 1.00 | 1.00 |
| Smcp | 1.00 | 0.92 | 1.00 | 1.00 | 1.00 | 1.36 | 34.00 | 1.84 | 1.00 | 1.00 | 1.00 | 1.00 |
| Smg9 | 0.81 | 1.00 | 1.10 | 1.22 | 0.79 | 1.03 | 1.33 | 8.48 | 1.07 | 3.03 | 1.24 | 1.05 |
| Smim1 | 1.13 | 1.04 | 0.98 | 1.21 | 1.38 | 1.29 | 1.16 | 9.54 | 1.12 | 2.17 | 0.71 | 0.88 |
| Smim20 | 1.20 | 1.24 | 0.87 | 1.07 | 1.09 | 1.03 | 1.16 | 6.63 | 0.99 | 2.68 | 1.69 | 1.36 |
| Smim22 | 1.21 | 3.27 | 1.00 | 1.00 | 0.57 | 1.00 | 1.00 | 1.00 | 1.00 | 1.00 | 1.00 | 1.00 |
| Smim23 | 1.00 | 1.00 | 1.00 | 1.00 | 1.00 | 1.00 | 1.00 | 1.49 | 1.00 | 1.00 | 1.00 | 1.00 |
| Smim24 | 0.22 | 0.14 | 0.19 | 1.00 | 1.00 | 0.91 | 8.18 | 1.00 | 1.53 | 0.86 | 1.73 | 1.40 |
| Smpd2 | 1.08 | 0.93 | 0.89 | 0.96 | 0.90 | 0.93 | 2.16 | 13.72 | 1.49 | 3.07 | 1.36 | 1.32 |
| Smpd5 | 1.00 | 1.00 | 1.00 | 1.00 | 0.66 | 1.00 | 1.26 | 13.97 | 1.01 | 1.21 | 0.61 | 0.94 |
| Snap25 | 1.00 | 1.00 | 1.00 | 1.10 | 1.48 | 1.08 | 1.00 | 1.31 | 1.00 | 1.00 | 1.00 | 1.00 |
| Snap91 | 1.00 | 1.00 | 1.00 | 1.04 | 0.99 | 1.02 | 0.70 | 1.78 | 1.09 | 1.00 | 1.00 | 1.00 |
| Sncb | 1.00 | 1.00 | 1.00 | 1.08 | 0.86 | 1.00 | 1.00 | 1.48 | 1.00 | 1.00 | 1.00 | 1.00 |
| Snf8 | 1.21 | 0.56 | 0.82 | 1.15 | 1.04 | 0.92 | 1.11 | 37.46 | 0.89 | 5.65 | 1.17 | 1.19 |
| Snhg11 | 1.00 | 1.00 | 1.19 | 0.83 | 1.03 | 0.94 | 0.80 | 1.40 | 0.93 | 1.00 | 1.00 | 1.00 |
| Snhg12 | 0.95 | 0.81 | 1.08 | 1.14 | 1.01 | 0.86 | 0.88 | 4.45 | 1.09 | 1.82 | 0.68 | 1.00 |
| Snhg3 | 0.68 | 0.56 | 1.43 | 1.17 | 1.00 | 1.08 | 1.20 | 0.71 | 0.84 | 0.59 | 0.71 | 0.75 |
| Snhg5 | 0.73 | 1.08 | 1.23 | 1.09 | 0.74 | 0.95 | 0.89 | 2.00 | 1.15 | 1.11 | 0.74 | 0.67 |
| Snhg9 | 1.00 | 1.00 | 1.00 | 1.00 | 1.00 | 1.00 | 1.00 | 1.00 | 1.00 | 1.00 | 1.00 | 1.00 |
| Snora15 | 1.00 | 1.00 | 1.00 | 1.00 | 1.00 | 1.00 | 1.00 | 1.00 | 1.00 | 1.00 | 45.43 | 1.00 |
| Snora16a | 1.00 | 1.00 | 17.79 | 1.00 | 1.00 | 9.58 | 20.37 | 1.00 | 1.41 | 1.00 | 1.00 | 1.49 |
| Snora17 | 1.00 | 1.00 | 1.00 | 1.00 | 1.00 | 1.00 | 1.00 | 0.14 | 0.17 | 1.00 | 1.00 | 0.74 |
| Snora21 | 1.00 | 1.00 | 1.00 | 1.00 | 1.00 | 1.00 | 32.51 | 1.00 | 1.00 | 1.00 | 1.00 | 1.00 |
| Snora23 | 1.00 | 1.00 | 1.00 | 1.00 | 1.00 | 1.00 | 1.00 | 7.12 | 0.76 | 1.00 | 1.20 | 1.00 |
| Snora28 | 1.00 | 1.00 | 1.00 | 1.00 | 1.00 | 0.08 | 1.00 | 1.00 | 13.00 | 1.00 | 1.00 | 1.00 |
| Snora3 | 1.00 | 1.00 | 1.00 | 1.00 | 1.00 | 1.00 | 1.00 | 1.00 | 1.00 | 1.00 | 1.00 | 1.00 |
| Snora31 | 1.00 | 1.00 | 1.00 | 1.00 | 1.00 | 1.00 | 1.00 | 1.00 | 27.84 | 1.00 | 1.00 | 1.00 |
| Snora33 | 1.00 | 1.00 | 1.00 | 1.00 | 1.00 | 1.00 | 1.00 | 1.00 | 1.00 | 1.00 | 1.00 | 116.26 |
| Snora34 | 1.00 | 1.00 | 1.00 | 0.02 | 1.00 | 0.06 | 1.00 | 1.00 | 1.00 | 1.00 | 1.00 | 1.00 |
| Snora41 | 1.00 | 1.00 | 24.67 | 1.00 | 1.00 | 1.00 | 1.00 | 1.00 | 100.56 | 0.02 | 1.00 | 41.35 |
| Snora43 | 1.00 | 1.00 | 1.00 | 1.00 | 1.00 | 1.69 | 1.49 | 0.10 | 0.38 | 0.15 | 29.48 | 0.74 |
| Snora44 | 1.00 | 1.00 | 1.00 | 1.00 | 1.00 | 1.00 | 1.00 | 1.00 | 1.00 | 1.00 | 1.00 | 1.00 |
| Snora52 | 1.00 | 1.00 | 1.00 | 1.00 | 1.00 | 1.00 | 11.35 | 0.05 | 1.00 | 1.00 | 0.09 | 0.74 |
| Snora62 | 1.00 | 1.00 | 1.00 | 1.00 | 1.00 | 1.00 | 16.25 | 1.00 | 1.00 | 0.08 | 1.00 | 1.00 |
| Snora64 | 1.00 | 1.00 | 1.00 | 0.02 | 1.00 | 0.83 | 0.02 | 0.03 | 2.31 | 1.00 | 0.01 | 1.00 |
| Snora65 | 1.00 | 1.00 | 1.00 | 1.00 | 1.00 | 0.83 | 1.00 | 0.06 | 0.07 | 1.00 | 0.59 | 0.01 |
| Snora69 | 1.00 | 0.02 | 1.00 | 1.00 | 1.00 | 0.08 | 1.00 | 0.08 | 1.00 | 1.00 | 1.00 | 0.75 |
| Snora70 | 1.00 | 1.00 | 1.00 | 1.00 | 1.00 | 1.00 | 15.25 | 0.04 | 0.16 | 1.00 | 1.19 | 1.49 |
| Snora74a | 1.00 | 1.00 | 1.00 | 1.00 | 1.00 | 1.00 | 0.53 | 39.59 | 1.00 | 0.82 | 1.00 | 2.01 |
| Snora75 | 1.00 | 1.00 | 1.00 | 1.00 | 1.00 | 1.00 | 1.00 | 1.00 | 1.00 | 1.00 | 1.00 | 1.00 |
| Snora78 | 1.00 | 1.00 | 1.00 | 1.00 | 34.66 | 2.29 | 2.35 | 21.17 | 1.67 | 7.47 | 2.39 | 1.49 |
| Snora7a | 1.00 | 1.00 | 1.00 | 1.00 | 1.00 | 0.06 | 1.00 | 1.00 | 1.00 | 1.00 | 1.00 | 1.00 |
| Snora81 | 0.82 | 1.02 | 4.97 | 0.71 | 1.00 | 0.85 | 1.58 | 1.80 | 1.00 | 1.00 | 0.17 | 0.25 |
| Snord15a | 1.00 | 1.00 | 1.00 | 1.00 | 1.00 | 1.00 | 1.00 | 1.00 | 1.00 | 0.07 | 1.00 | 3.07 |
| Snord15b | 1.00 | 1.00 | 1.00 | 1.00 | 1.00 | 1.00 | 0.38 | 97.14 | 1.12 | 1.00 | 1.00 | 13.58 |
| Snord17 | 1.00 | 1.00 | 1.00 | 1.00 | 1.00 | 1.00 | 1.00 | 14.64 | 1.00 | 2.08 | 5.38 | 2.61 |
| Snord22 | 21.64 | 1.00 | 1.00 | 1.16 | 1.00 | 1.00 | 0.35 | 7.34 | 1.14 | 0.53 | 0.06 | 2.23 |
| Snord7 | 1.00 | 1.00 | 1.00 | 1.00 | 1.00 | 1.00 | 1.00 | 1.00 | 1.00 | 1.00 | 1.00 | 1.00 |
| Snph | 1.00 | 1.00 | 1.00 | 1.10 | 1.24 | 1.06 | 1.00 | 1.00 | 1.00 | 1.00 | 1.00 | 1.00 |

Fig. 35- 265

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Snrnp25 | 0.72 | 0.56 | 0.83 | 0.37 | 3.91 | 0.82 | 0.97 | 0.99 | 0.62 | 2.17 | 3.29 | 1.09 |
| Snrnp27 | 1.04 | 0.60 | 0.72 | 0.83 | 5.32 | 0.89 | 0.81 | 0.65 | 0.91 | 1.65 | 2.17 | 0.95 |
| Snrpa1 | 1.94 | 0.78 | 0.92 | 0.79 | 6.50 | 1.13 | 1.06 | 0.85 | 1.17 | 1.70 | 3.06 | 0.91 |
| Snrpb | 1.17 | 0.62 | 0.74 | 0.44 | 5.57 | 0.93 | 1.02 | 0.75 | 0.88 | 2.03 | 2.86 | 0.92 |
| Snrpc | 1.20 | 0.60 | 1.10 | 0.69 | 5.34 | 0.78 | 0.91 | 0.64 | 0.56 | 1.95 | 2.42 | 1.10 |
| Snrpd2 | 1.18 | 0.47 | 0.89 | 0.34 | 14.48 | 0.86 | 0.85 | 0.61 | 0.85 | 3.00 | 5.18 | 0.91 |
| Snrpe | 1.58 | 0.69 | 0.70 | 0.40 | 6.60 | 1.35 | 0.91 | 0.81 | 0.82 | 1.81 | 2.39 | 0.78 |
| Snrpf | 1.00 | 0.56 | 0.95 | 0.23 | 1.96 | 1.04 | 1.00 | 1.00 | 0.92 | 1.20 | 1.20 | 0.47 |
| Snrpg | 1.29 | 0.28 | 0.86 | 0.11 | 7.49 | 1.25 | 0.96 | 0.68 | 0.69 | 2.41 | 4.07 | 0.76 |
| Snrpn | 0.98 | 0.72 | 0.67 | 0.37 | 0.27 | 0.85 | 1.25 | 1.28 | 0.86 | 1.39 | 0.76 | 1.02 |
| Snurf | 1.43 | 1.06 | 1.42 | 1.00 | 1.06 | 1.00 | 0.80 | 0.84 | 1.35 | 1.37 | 1.00 | 1.09 |
| Snx17 | 1.28 | 0.74 | 1.01 | 0.56 | 3.95 | 0.94 | 0.83 | 0.88 | 0.93 | 1.98 | 2.08 | 0.92 |
| Snx20 | 1.00 | 1.00 | 1.00 | 1.00 | 1.10 | 1.00 | 1.00 | 1.00 | 1.34 | 1.32 | 1.18 | 0.98 |
| Soat1 | 1.88 | 1.61 | 1.78 | 1.28 | 1.00 | 1.00 | 1.09 | 1.33 | 1.25 | 1.08 | 0.96 | 0.94 |
| Soat2 | 1.00 | 1.00 | 1.00 | 1.00 | 1.00 | 1.00 | 1.00 | 1.00 | 1.00 | 5.35 | 3.33 | 1.00 |
| Socs2 | 2.42 | 1.86 | 0.73 | 3.03 | 3.53 | 2.08 | 0.42 | 0.40 | 0.41 | 0.75 | 0.76 | 0.99 |
| Sod1 | 1.67 | 0.68 | 1.21 | 0.22 | 12.42 | 1.19 | 1.15 | 0.84 | 0.88 | 3.78 | 3.80 | 1.04 |
| Sod3 | 1.47 | 1.01 | 0.94 | 0.42 | 0.55 | 0.71 | 1.30 | 0.92 | 1.12 | 0.51 | 0.53 | 0.75 |
| Sox11 | 1.00 | 1.00 | 1.00 | 1.00 | 1.00 | 1.00 | 1.00 | 1.00 | 1.00 | 1.00 | 1.00 | 1.00 |
| Sox4 | 3.44 | 1.00 | 3.25 | 41.63 | 1.69 | 2.87 | 1.05 | 1.56 | 1.20 | 1.00 | 0.94 | 1.06 |
| Sp110 | 1.38 | 0.87 | 1.63 | 0.69 | 5.69 | 1.64 | 1.20 | 0.81 | 1.12 | 1.45 | 1.80 | 0.93 |
| Spa17 | 1.06 | 0.50 | 0.64 | 0.52 | 7.82 | 1.11 | 0.48 | 0.47 | 0.44 | 3.18 | 4.16 | 0.93 |
| Spag11a | 1.00 | 1.00 | 1.00 | 1.00 | 1.00 | 1.00 | 1.00 | 1.00 | 1.00 | 1.09 | 1.00 | 1.00 |
| Spata24 | 1.48 | 0.71 | 0.58 | 0.77 | 3.86 | 0.79 | 0.84 | 0.48 | 1.15 | 2.59 | 3.08 | 1.01 |
| Spata3 | 1.00 | 1.00 | 1.00 | 1.00 | 1.00 | 1.00 | 1.00 | 1.00 | 1.00 | 1.00 | 1.00 | 1.00 |
| Spc24 | 1.00 | 0.40 | 0.80 | 1.00 | 1.00 | 1.00 | 1.19 | 1.01 | 0.91 | 1.32 | 3.25 | 1.27 |
| Spem1 | 1.00 | 1.00 | 1.00 | 1.00 | 1.00 | 1.00 | 1.00 | 1.00 | 1.00 | 4.55 | 1.00 | 1.00 |
| Spg7 | 0.87 | 0.51 | 0.76 | 0.40 | 3.98 | 0.82 | 0.90 | 1.00 | 0.94 | 3.71 | 4.21 | 0.98 |
| Sphk1 | 3.21 | 3.41 | 1.00 | 1.00 | 1.15 | 1.00 | 3.11 | 2.38 | 2.49 | 1.55 | 2.06 | 1.49 |
| Spink3 | 1.00 | 1.00 | 1.00 | 1.00 | 1.00 | 1.00 | 1.00 | 1.00 | 1.00 | 1.00 | 1.00 | 1.00 |
| Spink6 | 1.00 | 1.00 | 1.00 | 1.00 | 1.00 | 1.00 | 1.00 | 1.00 | 1.00 | 1.00 | 1.00 | 1.00 |
| Spink8 | 1.00 | 1.00 | 1.00 | 1.00 | 1.00 | 1.00 | 1.00 | 1.00 | 1.00 | 1.00 | 1.00 | 1.00 |
| Spint3 | 1.00 | 1.00 | 1.00 | 1.00 | 1.00 | 1.00 | 1.00 | 1.00 | 1.00 | 1.00 | 1.00 | 1.00 |
| Spock1 | 1.00 | 1.00 | 1.00 | 1.00 | 0.21 | 1.00 | 1.00 | 1.00 | 1.00 | 1.00 | 1.00 | 1.00 |
| Spock2 | 1.31 | 1.59 | 2.64 | 4.15 | 0.07 | 2.48 | 2.16 | 3.38 | 2.57 | 1.69 | 1.13 | 1.32 |
| Spp1 | 2.23 | 2.73 | 1.90 | 1.00 | 0.38 | 1.16 | 1.00 | 1.56 | 2.14 | 0.38 | 0.51 | 0.82 |
| Sprn | 1.00 | 1.00 | 1.00 | 1.00 | 0.24 | 1.00 | 0.54 | 0.66 | 0.72 | 1.00 | 1.00 | 1.00 |
| Sprr2i | 1.00 | 1.00 | 1.00 | 1.00 | 1.00 | 1.00 | 1.00 | 1.00 | 1.00 | 1.00 | 1.00 | 1.00 |
| Spsb1 | 4.72 | 4.78 | 4.57 | 4.17 | 4.54 | 2.25 | 1.93 | 2.09 | 0.88 | 2.06 | 1.95 | 1.36 |
| Spsb4 | 1.00 | 1.00 | 1.00 | 1.00 | 1.00 | 1.00 | 0.59 | 0.70 | 0.94 | 1.00 | 1.00 | 1.00 |
| Spt1 | 1.00 | 1.00 | 1.00 | 1.00 | 1.00 | 1.00 | 0.81 | 0.91 | 1.00 | 1.00 | 1.00 | 1.00 |
| Sptbn2 | 1.00 | 1.00 | 1.00 | 1.00 | 0.20 | 1.00 | 1.00 | 1.00 | 1.00 | 1.68 | 1.45 | 1.05 |
| Spz1 | 1.00 | 1.00 | 1.00 | 1.00 | 1.00 | 1.00 | 1.00 | 1.00 | 1.00 | 1.00 | 1.00 | 1.00 |
| Srcin1 | 1.00 | 1.00 | 1.00 | 1.00 | 0.28 | 1.00 | 1.00 | 1.00 | 1.00 | 1.56 | 1.47 | 0.95 |
| Srm | 1.27 | 1.23 | 1.24 | 0.50 | 3.62 | 1.26 | 1.05 | 1.16 | 1.23 | 1.32 | 1.64 | 0.86 |
| Srp19 | 1.13 | 1.43 | 0.95 | 0.59 | 1.86 | 1.13 | 0.78 | 0.81 | 0.84 | 0.67 | 1.14 | 1.06 |
| Srp54c | 0.77 | 1.66 | 1.21 | 0.90 | 2.76 | 1.81 | 0.53 | 0.48 | 0.18 | 1.00 | 1.33 | 1.15 |
| Srp9 | 0.86 | 0.81 | 0.72 | 0.52 | 2.12 | 1.00 | 0.94 | 0.86 | 0.82 | 0.79 | 1.33 | 0.96 |
| Srpk3 | 0.97 | 0.43 | 0.71 | 1.00 | 1.00 | 1.00 | 0.84 | 0.95 | 0.80 | 0.95 | 0.86 | 0.57 |
| Srrd | 2.35 | 4.53 | 0.78 | 0.71 | 6.11 | 1.37 | 1.30 | 1.06 | 1.01 | 0.65 | 1.18 | 0.99 |
| Ssbp4 | 0.76 | 0.49 | 0.55 | 0.51 | 7.30 | 1.10 | 1.27 | 0.83 | 0.96 | 1.58 | 3.18 | 0.83 |
| Ssna1 | 1.00 | 0.68 | 0.77 | 0.81 | 5.99 | 0.93 | 0.97 | 0.72 | 0.90 | 1.76 | 2.90 | 1.08 |
| Ssr4 | 1.50 | 0.71 | 0.89 | 0.22 | 2.76 | 1.03 | 1.36 | 0.81 | 1.17 | 1.37 | 2.53 | 0.93 |
| Sssca1 | 1.42 | 0.62 | 0.79 | 0.21 | 4.75 | 0.77 | 1.25 | 0.74 | 0.78 | 2.44 | 3.52 | 1.34 |
| Sst | 1.00 | 1.00 | 1.00 | 1.00 | 0.05 | 1.00 | 1.00 | 1.00 | 1.00 | 0.64 | 1.00 | 1.00 |
| St14 | 1.00 | 1.00 | 1.00 | 1.00 | 1.00 | 1.00 | 1.00 | 1.00 | 1.00 | 2.34 | 3.26 | 1.12 |
| St3gal3 | 1.28 | 0.82 | 1.01 | 0.38 | 2.60 | 0.73 | 1.08 | 0.84 | 0.76 | 2.39 | 2.84 | 1.12 |
| St6galnac2 | 1.42 | 0.99 | 1.88 | 0.28 | 2.15 | 0.74 | 0.96 | 0.90 | 0.92 | 2.25 | 2.29 | 1.28 |
| Stard10 | 1.10 | 0.50 | 0.82 | 0.43 | 9.11 | 1.14 | 0.96 | 0.83 | 1.02 | 2.63 | 3.81 | 1.00 |
| Stbd1 | 1.34 | 1.54 | 1.41 | 2.23 | 2.25 | 1.72 | 26.24 | 26.14 | 27.87 | 2.60 | 3.82 | 3.04 |
| Stfa1 | 1.00 | 1.00 | 1.00 | 1.00 | 1.00 | 1.00 | 1.00 | 1.00 | 1.00 | 4.21 | 3.44 | 1.00 |
| Stfa2l1 | 1.00 | 1.00 | 1.00 | 1.00 | 1.00 | 1.00 | 1.00 | 1.00 | 1.00 | 1.32 | 5.10 | 1.27 |
| Stfa3 | 1.00 | 1.00 | 1.00 | 1.00 | 1.00 | 1.00 | 1.00 | 1.00 | 1.00 | 1.97 | 1.00 | 1.00 |
| Stk19 | 1.98 | 0.64 | 0.86 | 0.23 | 5.22 | 0.46 | 1.36 | 0.93 | 1.07 | 2.73 | 4.12 | 0.96 |

Fig. 35-266

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Snrnp25 | 0.80 | 1.10 | 0.95 | 0.64 | 0.50 | 0.75 | 1.00 | 1.67 | 0.70 | 0.85 | 1.55 | 0.72 |
| Snrnp27 | 1.07 | 1.18 | 0.88 | 0.89 | 0.67 | 0.85 | 0.96 | 1.57 | 0.86 | 0.88 | 1.83 | 0.94 |
| Snrpa1 | 0.82 | 1.06 | 0.70 | 0.87 | 0.65 | 0.72 | 1.50 | 1.74 | 1.35 | 1.00 | 1.37 | 0.88 |
| Snrpb | 0.93 | 1.19 | 0.82 | 0.80 | 0.59 | 0.86 | 0.93 | 1.60 | 0.85 | 0.96 | 1.51 | 0.94 |
| Snrpc | 1.10 | 1.18 | 0.81 | 0.81 | 0.73 | 1.44 | 0.96 | 1.43 | 1.07 | 1.21 | 1.59 | 1.02 |
| Snrpd2 | 0.97 | 1.41 | 0.78 | 0.67 | 0.42 | 0.79 | 0.85 | 2.36 | 0.95 | 0.89 | 1.88 | 1.03 |
| Snrpe | 1.12 | 1.31 | 0.76 | 1.02 | 0.65 | 0.79 | 1.09 | 1.08 | 0.96 | 0.88 | 1.81 | 0.98 |
| Snrpf | 0.77 | 1.11 | 0.79 | 1.00 | 0.19 | 0.89 | 1.00 | 1.00 | 1.00 | 0.64 | 1.28 | 1.03 |
| Snrpg | 1.17 | 2.04 | 0.97 | 0.84 | 0.48 | 0.80 | 1.42 | 1.25 | 0.83 | 1.90 | 2.31 | 1.15 |
| Snrpn | 0.82 | 1.00 | 1.28 | 1.20 | 1.16 | 0.95 | 0.93 | 1.00 | 0.81 | 1.33 | 1.20 | 0.88 |
| Snurf | 1.00 | 1.00 | 1.00 | 1.00 | 1.15 | 0.95 | 1.00 | 1.00 | 1.00 | 1.16 | 1.10 | 1.10 |
| Snx17 | 1.05 | 1.35 | 0.92 | 0.82 | 0.62 | 0.88 | 1.27 | 2.53 | 1.21 | 0.88 | 1.36 | 0.99 |
| Snx20 | 1.53 | 1.94 | 1.50 | 1.00 | 1.00 | 1.07 | 1.00 | 1.00 | 1.00 | 1.15 | 1.48 | 1.25 |
| Soat1 | 0.94 | 0.93 | 1.39 | 1.16 | 1.22 | 1.16 | 1.06 | 1.00 | 1.23 | 1.05 | 1.04 | 1.20 |
| Soat2 | 1.73 | 1.01 | 1.29 | 1.00 | 1.00 | 1.00 | 0.38 | 1.01 | 0.54 | 1.00 | 1.00 | 1.00 |
| Socs2 | 1.51 | 1.11 | 1.02 | 1.37 | 2.55 | 1.14 | 0.66 | 3.70 | 0.34 | 1.17 | 1.16 | 1.20 |
| Sod1 | 1.26 | 1.53 | 1.09 | 1.01 | 0.54 | 1.05 | 0.98 | 2.99 | 0.92 | 0.96 | 1.83 | 1.10 |
| Sod3 | 1.04 | 0.95 | 0.79 | 0.88 | 1.02 | 1.03 | 1.34 | 1.14 | 1.58 | 0.86 | 0.93 | 0.96 |
| Sox11 | 1.00 | 1.00 | 1.00 | 1.00 | 1.00 | 1.00 | 1.00 | 1.00 | 1.00 | 1.00 | 1.00 | 1.00 |
| Sox4 | 0.53 | 0.33 | 0.95 | 2.45 | 1.00 | 1.26 | 1.00 | 1.00 | 1.00 | 1.04 | 0.25 | 0.93 |
| Sp110 | 1.16 | 1.27 | 0.99 | 1.00 | 0.72 | 1.41 | 1.00 | 0.69 | 0.94 | 1.45 | 1.72 | 1.14 |
| Spa17 | 1.37 | 1.07 | 1.00 | 0.50 | 0.43 | 0.48 | 1.00 | 5.12 | 1.00 | 1.00 | 2.04 | 1.00 |
| Spag11a | 1.00 | 1.00 | 1.00 | 1.00 | 1.00 | 1.00 | 1.00 | 1.00 | 1.00 | 1.00 | 1.00 | 1.00 |
| Spata24 | 0.77 | 2.07 | 0.92 | 0.84 | 0.78 | 1.08 | 2.40 | 3.43 | 3.95 | 0.55 | 1.41 | 1.82 |
| Spata3 | 1.00 | 1.00 | 1.00 | 1.00 | 1.00 | 1.00 | 1.00 | 1.00 | 1.00 | 1.00 | 1.00 | 1.00 |
| Spc24 | 0.68 | 1.22 | 0.75 | 1.90 | 0.29 | 1.64 | 0.85 | 1.16 | 0.85 | 1.66 | 2.23 | 1.57 |
| Spem1 | 1.00 | 1.00 | 1.00 | 1.00 | 1.00 | 1.00 | 1.00 | 1.00 | 1.00 | 1.00 | 1.00 | 1.00 |
| Spg7 | 0.91 | 1.17 | 0.90 | 0.96 | 0.60 | 1.01 | 1.05 | 2.38 | 0.85 | 1.09 | 1.36 | 1.01 |
| Sphk1 | 0.89 | 0.92 | 0.95 | 1.18 | 1.83 | 1.14 | 1.00 | 1.00 | 1.00 | 1.31 | 1.42 | 0.78 |
| Spink3 | 1.00 | 1.00 | 1.00 | 1.08 | 0.70 | 1.05 | 1.00 | 1.05 | 1.00 | 0.99 | 1.51 | 1.07 |
| Spink6 | 1.00 | 1.00 | 1.00 | 1.00 | 1.00 | 1.00 | 1.00 | 1.00 | 1.00 | 1.00 | 1.00 | 1.00 |
| Spink8 | 1.37 | 8.31 | 1.00 | 2.05 | 1.26 | 1.87 | 1.00 | 1.00 | 1.00 | 1.00 | 1.00 | 1.00 |
| Spint3 | 1.00 | 1.00 | 1.00 | 1.00 | 1.00 | 1.00 | 1.00 | 1.00 | 1.00 | 1.00 | 1.00 | 1.00 |
| Spock1 | 1.29 | 1.00 | 1.77 | 1.00 | 1.00 | 1.00 | 1.00 | 1.00 | 1.00 | 1.00 | 1.00 | 1.00 |
| Spock2 | 1.15 | 0.71 | 1.45 | 1.41 | 1.00 | 1.33 | 1.00 | 1.00 | 1.00 | 1.61 | 0.63 | 1.18 |
| Spp1 | 1.53 | 5.55 | 12.06 | 0.68 | 1.13 | 0.41 | 0.64 | 0.67 | 0.77 | 0.85 | 1.00 | 1.30 |
| Sprn | 1.00 | 1.00 | 1.00 | 1.00 | 1.00 | 1.00 | 1.00 | 1.00 | 1.00 | 1.58 | 1.00 | 1.00 |
| Sprr2i | 0.62 | 0.78 | 1.00 | 1.00 | 1.00 | 1.00 | 1.00 | 1.00 | 1.00 | 1.00 | 1.00 | 1.00 |
| Spsb1 | 1.31 | 1.21 | 1.22 | 1.93 | 2.30 | 1.50 | 1.35 | 1.00 | 1.43 | 1.84 | 1.45 | 1.34 |
| Spsb4 | 0.60 | 0.46 | 0.52 | 0.81 | 0.74 | 0.99 | 0.21 | 0.16 | 0.53 | 3.23 | 4.29 | 8.29 |
| Spt1 | 0.87 | 0.84 | 0.02 | 1.00 | 1.00 | 1.00 | 0.98 | 1.00 | 1.00 | 1.00 | 1.00 | 1.00 |
| Sptbn2 | 1.00 | 1.00 | 1.00 | 1.20 | 0.81 | 1.21 | 0.88 | 1.50 | 0.93 | 1.01 | 0.74 | 0.81 |
| Spz1 | 1.00 | 1.00 | 1.00 | 1.00 | 1.00 | 1.00 | 1.00 | 1.00 | 1.00 | 1.00 | 1.00 | 1.00 |
| Srcin1 | 1.00 | 1.00 | 1.00 | 1.07 | 0.67 | 1.45 | 1.00 | 1.00 | 1.00 | 1.00 | 1.00 | 1.00 |
| Srm | 0.79 | 0.72 | 0.83 | 0.86 | 0.87 | 1.07 | 1.04 | 1.18 | 1.03 | 0.95 | 1.25 | 1.09 |
| Srp19 | 1.10 | 1.49 | 0.92 | 0.91 | 1.76 | 0.84 | 0.93 | 0.76 | 1.34 | 0.94 | 1.48 | 1.03 |
| Srp54c | 1.12 | 1.66 | 1.44 | 0.85 | 1.88 | 0.78 | 1.53 | 1.08 | 1.00 | 0.74 | 1.94 | 1.26 |
| Srp9 | 1.49 | 1.78 | 1.16 | 0.87 | 1.36 | 1.08 | 0.83 | 0.78 | 0.90 | 0.89 | 1.30 | 1.03 |
| Srpk3 | 1.00 | 1.00 | 1.00 | 1.00 | 1.00 | 1.00 | 1.00 | 1.00 | 1.00 | 0.82 | 0.99 | 0.77 |
| Srrd | 1.10 | 1.24 | 0.90 | 1.38 | 1.05 | 1.00 | 1.33 | 3.14 | 1.42 | 0.78 | 1.31 | 0.93 |
| Ssbp4 | 0.82 | 1.27 | 1.14 | 0.71 | 0.66 | 1.00 | 1.00 | 1.70 | 1.00 | 0.89 | 1.29 | 1.05 |
| Ssna1 | 0.89 | 1.22 | 0.69 | 0.91 | 0.59 | 0.77 | 1.03 | 1.36 | 1.00 | 0.97 | 1.71 | 1.05 |
| Ssr4 | 1.10 | 1.70 | 1.11 | 0.81 | 0.81 | 1.05 | 1.45 | 1.22 | 0.98 | 0.77 | 1.38 | 1.10 |
| Sssca1 | 1.06 | 1.55 | 1.12 | 0.77 | 0.58 | 0.90 | 1.04 | 1.96 | 1.15 | 0.84 | 1.45 | 0.86 |
| Sst | 2.16 | 1.82 | 0.51 | 1.00 | 1.00 | 1.00 | 1.00 | 1.00 | 1.00 | 0.76 | 1.06 | 0.69 |
| St14 | 1.57 | 1.60 | 1.81 | 1.09 | 0.80 | 1.02 | 1.00 | 1.00 | 1.00 | 1.16 | 1.52 | 1.12 |
| St3gal3 | 0.86 | 1.12 | 0.82 | 0.91 | 0.55 | 1.01 | 0.79 | 1.79 | 0.92 | 1.19 | 1.51 | 1.15 |
| St6galnac2 | 2.40 | 2.34 | 1.68 | 1.01 | 0.82 | 1.22 | 1.12 | 3.53 | 0.95 | 1.04 | 1.43 | 1.22 |
| Stard10 | 2.12 | 2.04 | 1.38 | 1.12 | 0.69 | 1.15 | 1.01 | 1.91 | 1.03 | 1.03 | 1.59 | 1.09 |
| Stbd1 | 3.55 | 3.85 | 3.41 | 2.07 | 1.80 | 1.41 | 1.26 | 1.06 | 1.48 | 1.88 | 1.83 | 1.79 |
| Stfa1 | 1.00 | 1.00 | 1.00 | 1.00 | 1.00 | 1.00 | 1.00 | 1.00 | 1.00 | 1.00 | 1.00 | 1.00 |
| Stfa2l1 | 1.00 | 1.00 | 1.00 | 1.00 | 1.00 | 1.00 | 1.00 | 1.00 | 1.00 | 1.00 | 1.00 | 1.00 |
| Stfa3 | 1.00 | 1.00 | 1.00 | 1.00 | 1.00 | 1.00 | 1.00 | 1.00 | 1.00 | 1.00 | 1.00 | 1.00 |
| Stk19 | 1.47 | 2.09 | 1.01 | 1.08 | 0.51 | 0.74 | 0.56 | 1.24 | 0.70 | 0.90 | 2.16 | 0.94 |

Fig. 35- 267

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Snrnp25 | 0.82 | 1.41 | 0.84 | 0.78 | 0.59 | 0.72 | 1.08 | 2.57 | 0.91 | 0.74 | 0.92 | 0.78 |
| Snrnp27 | 1.02 | 0.95 | 1.18 | 1.03 | 4.63 | 1.16 | 0.88 | 1.48 | 1.07 | 0.90 | 1.34 | 0.86 |
| Snrpa1 | 1.01 | 0.56 | 0.72 | 1.01 | 4.49 | 1.27 | 0.86 | 1.16 | 0.73 | 1.12 | 1.45 | 1.03 |
| Snrpb | 0.93 | 0.96 | 0.99 | 1.00 | 2.46 | 1.02 | 0.98 | 2.57 | 0.94 | 0.96 | 1.22 | 0.98 |
| Snrpc | 1.25 | 0.94 | 0.60 | 1.04 | 2.79 | 0.72 | 1.03 | 1.50 | 0.95 | 1.01 | 1.27 | 1.04 |
| Snrpd2 | 0.87 | 0.91 | 1.05 | 0.95 | 1.80 | 0.95 | 0.91 | 3.93 | 1.02 | 1.10 | 1.53 | 0.97 |
| Snrpe | 0.98 | 0.90 | 1.00 | 0.93 | 4.03 | 1.02 | 1.01 | 1.60 | 0.91 | 1.19 | 1.19 | 0.97 |
| Snrpf | 0.68 | 0.55 | 0.81 | 0.99 | 1.12 | 1.54 | 0.91 | 4.14 | 0.80 | 0.92 | 1.24 | 0.71 |
| Snrpg | 1.27 | 0.57 | 0.93 | 1.00 | 4.11 | 1.13 | 1.10 | 2.28 | 0.96 | 1.00 | 1.52 | 1.01 |
| Snrpn | 1.09 | 1.64 | 1.04 | 0.65 | 1.00 | 0.70 | 0.76 | 0.96 | 0.79 | 1.00 | 7.80 | 1.00 |
| Snurf | 1.00 | 1.00 | 1.35 | 1.00 | 1.00 | 0.62 | 1.00 | 1.00 | 1.00 | 1.00 | 1.42 | 1.00 |
| Snx17 | 0.92 | 0.87 | 1.01 | 0.96 | 1.67 | 1.02 | 1.19 | 2.15 | 0.91 | 1.05 | 1.15 | 1.00 |
| Snx20 | 1.51 | 1.52 | 1.75 | 1.06 | 1.73 | 0.60 | 1.00 | 1.00 | 1.00 | 1.00 | 0.99 | 1.05 |
| Soat1 | 1.29 | 1.17 | 1.60 | 2.00 | 5.67 | 0.99 | 0.82 | 0.75 | 0.68 | 0.94 | 0.86 | 1.00 |
| Soat2 | 0.78 | 1.02 | 0.70 | 1.00 | 1.00 | 1.00 | 1.00 | 1.00 | 1.00 | 1.09 | 1.04 | 0.71 |
| Socs2 | 1.30 | 1.45 | 1.07 | 1.73 | 4.83 | 1.20 | 1.01 | 1.00 | 1.15 | 0.75 | 0.64 | 0.71 |
| Sod1 | 0.86 | 1.14 | 0.85 | 1.10 | 2.64 | 1.26 | 0.78 | 4.00 | 0.95 | 0.88 | 1.39 | 0.80 |
| Sod3 | 0.94 | 1.00 | 1.26 | 0.73 | 0.65 | 0.53 | 0.74 | 0.50 | 0.77 | 0.53 | 0.50 | 0.44 |
| Sox11 | 1.00 | 1.00 | 1.00 | 1.00 | 1.00 | 1.00 | 1.00 | 1.00 | 1.00 | 1.00 | 1.00 | 12.98 |
| Sox4 | 0.97 | 0.74 | 0.76 | 4.66 | 1.02 | 1.05 | 1.07 | 1.00 | 1.10 | 0.92 | 0.88 | 1.56 |
| Sp110 | 1.45 | 1.28 | 2.32 | 0.95 | 2.07 | 1.20 | 1.00 | 1.29 | 1.00 | 1.06 | 1.00 | 0.92 |
| Spa17 | 1.61 | 1.00 | 1.00 | 1.91 | 8.98 | 1.67 | 0.88 | 2.93 | 1.04 | 1.00 | 1.51 | 1.00 |
| Spag11a | 1.00 | 1.00 | 1.00 | 1.00 | 8.31 | 0.25 | 1.00 | 1.15 | 1.00 | 1.00 | 1.00 | 1.00 |
| Spata24 | 0.66 | 1.19 | 1.16 | 1.31 | 4.53 | 0.85 | 0.85 | 2.04 | 1.02 | 1.24 | 1.01 | 0.96 |
| Spata3 | 1.00 | 1.00 | 1.00 | 3.84 | 1.00 | 0.90 | 0.96 | 0.71 | 1.01 | 1.00 | 1.00 | 1.00 |
| Spc24 | 0.83 | 0.61 | 0.70 | 1.00 | 0.49 | 1.00 | 1.31 | 3.26 | 1.32 | 1.50 | 1.26 | 0.57 |
| Spem1 | 1.00 | 1.00 | 1.00 | 4.17 | 4.76 | 1.00 | 0.95 | 2.45 | 1.04 | 1.00 | 1.00 | 1.00 |
| Spg7 | 0.91 | 1.08 | 0.82 | 0.71 | 1.20 | 0.63 | 1.05 | 3.97 | 1.08 | 0.85 | 1.26 | 0.92 |
| Sphk1 | 1.56 | 1.88 | 1.34 | 4.16 | 5.94 | 1.87 | 0.74 | 0.55 | 1.20 | 1.07 | 1.32 | 0.79 |
| Spink3 | 1.00 | 1.18 | 5.83 | 1.00 | 3.82 | 1.00 | 1.00 | 1.00 | 1.00 | 1.00 | 1.00 | 1.00 |
| Spink6 | 1.00 | 1.00 | 1.00 | 1.00 | 1.00 | 1.00 | 1.00 | 1.00 | 1.00 | 1.00 | 1.00 | 1.00 |
| Spink8 | 1.00 | 1.00 | 1.00 | 1.00 | 9.07 | 0.01 | 1.75 | 8.16 | 1.34 | 1.00 | 1.00 | 1.00 |
| Spint3 | 1.00 | 1.00 | 1.00 | 1.00 | 11.48 | 0.04 | 1.08 | 0.59 | 1.24 | 1.00 | 1.00 | 1.00 |
| Spock1 | 1.00 | 1.00 | 1.00 | 1.00 | 1.00 | 1.00 | 1.00 | 1.00 | 1.00 | 1.00 | 7.60 | 1.00 |
| Spock2 | 1.43 | 2.55 | 1.90 | 1.61 | 0.57 | 1.97 | 1.14 | 1.95 | 1.05 | 1.07 | 6.12 | 1.11 |
| Spp1 | 1.23 | 0.77 | 0.98 | 0.77 | 0.41 | 0.65 | 0.71 | 1.00 | 1.00 | 1.00 | 2.31 | 0.35 |
| Sprn | 1.00 | 1.00 | 1.00 | 1.40 | 1.00 | 0.90 | 1.00 | 1.00 | 1.00 | 1.00 | 6.76 | 1.00 |
| Sprr2i | 1.06 | 1.44 | 1.70 | 1.00 | 1.00 | 1.00 | 1.00 | 1.00 | 1.00 | 1.00 | 1.00 | 1.00 |
| Spsb1 | 2.64 | 3.19 | 1.66 | 5.70 | 5.89 | 3.07 | 1.06 | 1.48 | 1.03 | 1.44 | 1.35 | 1.06 |
| Spsb4 | 1.00 | 1.00 | 1.00 | 1.00 | 1.00 | 1.16 | 1.00 | 1.00 | 1.00 | 1.00 | 1.00 | 1.00 |
| Spt1 | 1.00 | 1.00 | 1.00 | 1.00 | 1.00 | 1.00 | 1.00 | 1.00 | 1.00 | 1.00 | 1.00 | 1.00 |
| Sptbn2 | 0.90 | 1.18 | 0.94 | 1.00 | 1.00 | 1.00 | 1.04 | 1.00 | 1.12 | 1.00 | 8.62 | 1.00 |
| Spz1 | 1.00 | 1.00 | 1.00 | 3.65 | 1.00 | 1.00 | 0.97 | 0.51 | 0.99 | 1.00 | 1.00 | 1.00 |
| Srcin1 | 0.65 | 1.07 | 1.15 | 1.35 | 1.00 | 1.33 | 0.89 | 1.30 | 1.15 | 1.00 | 5.02 | 1.00 |
| Srm | 1.18 | 0.65 | 0.89 | 1.30 | 6.91 | 1.20 | 0.85 | 1.39 | 1.01 | 1.27 | 1.22 | 1.07 |
| Srp19 | 0.74 | 0.91 | 1.17 | 1.19 | 7.78 | 1.23 | 0.96 | 0.54 | 0.88 | 1.05 | 1.29 | 0.95 |
| Srp54c | 1.27 | 1.03 | 2.13 | 1.03 | 0.69 | 1.46 | 1.55 | 0.50 | 1.46 | 1.47 | 1.91 | 0.38 |
| Srp9 | 1.03 | 1.00 | 1.09 | 1.02 | 6.32 | 0.95 | 0.88 | 0.89 | 1.02 | 1.22 | 1.64 | 1.17 |
| Srpk3 | 1.00 | 1.00 | 1.00 | 1.00 | 1.00 | 1.00 | 1.00 | 1.00 | 1.00 | 0.71 | 0.49 | 0.63 |
| Srrd | 0.93 | 1.58 | 1.33 | 0.65 | 6.42 | 0.99 | 0.98 | 1.34 | 1.06 | 1.10 | 1.39 | 0.73 |
| Ssbp4 | 1.05 | 1.19 | 1.32 | 0.70 | 1.70 | 0.92 | 0.84 | 1.85 | 0.94 | 0.89 | 1.23 | 0.90 |
| Ssna1 | 1.10 | 0.91 | 1.01 | 1.09 | 2.58 | 1.14 | 1.05 | 2.12 | 0.98 | 0.95 | 1.25 | 1.02 |
| Ssr4 | 0.97 | 0.98 | 1.02 | 0.99 | 7.13 | 1.13 | 1.00 | 1.06 | 0.96 | 1.01 | 1.28 | 1.16 |
| Sssca1 | 1.23 | 0.95 | 0.96 | 0.98 | 1.49 | 0.88 | 0.99 | 3.31 | 0.92 | 0.88 | 1.09 | 1.15 |
| Sst | 1.20 | 1.54 | 1.38 | 1.00 | 1.00 | 1.06 | 1.00 | 1.00 | 1.00 | 1.00 | 28.60 | 1.00 |
| St14 | 1.00 | 1.03 | 0.87 | 1.41 | 2.18 | 1.94 | 1.00 | 1.00 | 1.00 | 1.01 | 1.14 | 1.05 |
| St3gal3 | 1.29 | 1.03 | 1.15 | 0.78 | 0.99 | 0.90 | 1.02 | 2.43 | 1.28 | 0.92 | 1.27 | 0.80 |
| St6galnac2 | 1.08 | 1.21 | 1.18 | 1.33 | 4.30 | 1.39 | 0.93 | 1.67 | 0.95 | 0.95 | 0.97 | 0.85 |
| Stard10 | 0.93 | 1.03 | 0.86 | 1.15 | 3.83 | 1.41 | 0.85 | 2.80 | 1.01 | 1.13 | 1.59 | 0.90 |
| Stbd1 | 1.73 | 1.87 | 1.92 | 3.95 | 2.39 | 4.30 | 1.01 | 0.91 | 1.52 | 9.10 | 8.57 | 9.76 |
| Stfa1 | 1.00 | 1.00 | 1.00 | 1.00 | 1.00 | 1.00 | 1.00 | 4.01 | 1.00 | 1.00 | 1.00 | 1.00 |
| Stfa2l1 | 1.00 | 1.00 | 1.00 | 1.00 | 1.00 | 1.00 | 1.00 | 2.16 | 1.00 | 1.71 | 1.00 | 1.00 |
| Stfa3 | 1.00 | 1.00 | 1.00 | 1.00 | 6.16 | 1.00 | 1.00 | 1.00 | 1.00 | 0.76 | 0.52 | 0.56 |
| Stk19 | 0.91 | 1.03 | 0.85 | 0.66 | 2.26 | 0.75 | 1.05 | 2.86 | 1.21 | 1.07 | 1.67 | 0.87 |

Fig. 35- 268

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Snrnp25 | 1.00 | 0.84 | 1.00 | 0.83 | 0.82 | 1.27 | 0.88 | 7.12 | 0.77 | 2.63 | 1.03 | 0.96 |
| Snrnp27 | 0.97 | 0.57 | 0.60 | 1.03 | 1.40 | 0.96 | 0.85 | 4.05 | 0.78 | 1.96 | 1.01 | 1.19 |
| Snrpa1 | 0.76 | 0.68 | 0.45 | 1.05 | 0.81 | 1.41 | 1.12 | 3.72 | 1.04 | 1.64 | 0.81 | 1.07 |
| Snrpb | 1.01 | 0.90 | 0.97 | 0.96 | 1.33 | 1.00 | 1.08 | 7.23 | 0.90 | 2.08 | 1.12 | 1.22 |
| Snrpc | 1.57 | 0.52 | 0.95 | 1.30 | 1.16 | 0.80 | 0.99 | 7.62 | 0.89 | 2.29 | 1.27 | 0.99 |
| Snrpd2 | 0.81 | 0.89 | 0.90 | 1.05 | 0.89 | 1.05 | 1.47 | 27.27 | 0.91 | 3.72 | 0.99 | 1.08 |
| Snrpe | 0.69 | 0.52 | 0.94 | 1.12 | 0.73 | 1.08 | 1.08 | 3.60 | 0.85 | 2.18 | 0.83 | 0.87 |
| Snrpf | 1.00 | 1.00 | 1.00 | 0.99 | 5.61 | 1.45 | 1.91 | 3.55 | 0.87 | 1.21 | 0.59 | 1.57 |
| Snrpg | 0.86 | 0.72 | 1.71 | 0.94 | 1.51 | 1.24 | 0.89 | 10.91 | 1.04 | 3.33 | 0.80 | 0.91 |
| Snrpn | 1.00 | 1.00 | 1.00 | 1.05 | 1.15 | 0.60 | 1.04 | 1.00 | 1.03 | 1.00 | 1.00 | 1.00 |
| Snurf | 1.00 | 1.00 | 1.00 | 1.02 | 1.15 | 7.62 | 1.00 | 1.00 | 1.00 | 1.00 | 1.00 | 1.00 |
| Snx17 | 1.42 | 1.47 | 1.17 | 1.07 | 0.87 | 1.08 | 1.19 | 5.74 | 0.83 | 1.70 | 1.22 | 1.10 |
| Snx20 | 1.00 | 1.00 | 1.00 | 1.00 | 5.03 | 0.64 | 1.41 | 1.70 | 1.74 | 2.34 | 1.53 | 1.34 |
| Soat1 | 1.00 | 1.00 | 1.00 | 0.91 | 1.05 | 0.87 | 1.07 | 1.06 | 1.37 | 1.29 | 1.35 | 1.17 |
| Soat2 | 1.00 | 1.00 | 1.00 | 1.00 | 1.00 | 1.00 | 1.00 | 6.29 | 1.00 | 3.05 | 1.56 | 0.95 |
| Socs2 | 1.42 | 5.87 | 1.26 | 0.98 | 1.00 | 1.00 | 2.64 | 0.96 | 2.14 | 0.90 | 0.97 | 0.56 |
| Sod1 | 0.88 | 0.97 | 1.10 | 1.07 | 0.73 | 1.15 | 1.67 | 19.95 | 1.16 | 2.35 | 0.87 | 0.90 |
| Sod3 | 0.47 | 1.48 | 0.85 | 1.04 | 6.30 | 1.17 | 1.08 | 0.62 | 0.96 | 1.00 | 1.00 | 1.00 |
| Sox11 | 1.00 | 1.00 | 1.00 | 1.02 | 2.83 | 0.95 | 1.00 | 1.00 | 1.00 | 1.00 | 1.00 | 1.00 |
| Sox4 | 1.06 | 1.00 | 1.00 | 0.65 | 1.00 | 0.91 | 3.46 | 0.29 | 1.91 | 1.00 | 0.59 | 0.56 |
| Sp110 | 1.00 | 1.00 | 1.00 | 1.00 | 0.42 | 1.00 | 1.56 | 5.18 | 1.24 | 2.31 | 1.31 | 1.31 |
| Spa17 | 1.00 | 1.00 | 1.00 | 0.71 | 0.71 | 0.68 | 4.67 | 23.95 | 0.77 | 1.28 | 1.00 | 1.00 |
| Spag11a | 1.00 | 1.00 | 1.00 | 1.00 | 1.00 | 1.00 | 1.00 | 4.70 | 1.00 | 1.00 | 1.00 | 1.00 |
| Spata24 | 1.00 | 1.00 | 1.00 | 0.86 | 0.30 | 1.21 | 2.13 | 7.68 | 1.12 | 1.99 | 0.85 | 0.79 |
| Spata3 | 1.00 | 1.00 | 1.00 | 1.00 | 1.08 | 1.00 | 7.76 | 1.00 | 1.00 | 1.00 | 1.00 | 1.00 |
| Spc24 | 0.87 | 1.00 | 0.86 | 1.00 | 0.89 | 1.17 | 1.07 | 10.11 | 0.82 | 1.67 | 1.34 | 1.34 |
| Spem1 | 1.00 | 1.00 | 1.00 | 1.00 | 1.77 | 1.00 | 7.36 | 1.17 | 1.00 | 1.00 | 1.00 | 1.00 |
| Spg7 | 1.15 | 1.52 | 0.99 | 0.91 | 0.99 | 0.99 | 1.20 | 9.68 | 0.86 | 2.71 | 1.05 | 0.88 |
| Sphk1 | 0.78 | 0.34 | 0.53 | 1.02 | 0.50 | 0.88 | 0.94 | 1.12 | 0.68 | 0.51 | 0.64 | 0.69 |
| Spink3 | 1.12 | 1.21 | 1.20 | 1.00 | 1.00 | 1.00 | 1.00 | 2.46 | 1.00 | 1.00 | 1.00 | 1.00 |
| Spink6 | 1.00 | 1.00 | 1.00 | 1.00 | 1.00 | 1.00 | 2.55 | 17.45 | 2.44 | 1.00 | 1.00 | 1.00 |
| Spink8 | 1.00 | 1.00 | 1.00 | 5.11 | 3.71 | 4.38 | 1.00 | 1.61 | 1.00 | 1.00 | 1.00 | 1.00 |
| Spint3 | 1.00 | 1.00 | 1.00 | 1.00 | 1.00 | 1.00 | 1.00 | 1.00 | 1.00 | 1.00 | 1.00 | 1.00 |
| Spock1 | 1.00 | 1.00 | 1.00 | 1.08 | 1.57 | 1.05 | 1.00 | 1.00 | 1.00 | 1.00 | 1.00 | 1.00 |
| Spock2 | 0.79 | 1.05 | 1.69 | 1.00 | 0.90 | 0.99 | 1.31 | 0.53 | 2.02 | 1.00 | 1.00 | 1.00 |
| Spp1 | 0.61 | 0.86 | 1.21 | 1.49 | 4.82 | 1.17 | 1.66 | 0.47 | 1.18 | 0.72 | 1.74 | 1.71 |
| Sprn | 1.00 | 1.00 | 1.00 | 1.02 | 0.81 | 1.02 | 0.33 | 1.65 | 0.84 | 1.00 | 1.00 | 1.00 |
| Sprr2i | 1.00 | 1.00 | 1.00 | 1.00 | 1.00 | 1.00 | 0.62 | 6.26 | 0.48 | 1.00 | 1.00 | 1.00 |
| Spsb1 | 1.24 | 1.04 | 1.00 | 1.59 | 1.19 | 1.43 | 2.35 | 1.72 | 2.87 | 1.00 | 1.24 | 1.00 |
| Spsb4 | 1.00 | 1.00 | 1.00 | 0.64 | 0.96 | 0.82 | 1.00 | 1.00 | 1.00 | 1.00 | 1.00 | 1.00 |
| Spt1 | 1.00 | 1.00 | 1.00 | 1.00 | 1.00 | 1.00 | 1.00 | 44.20 | 1.00 | 11.05 | 1.00 | 1.00 |
| Sptbn2 | 1.31 | 1.38 | 1.73 | 1.01 | 1.03 | 0.99 | 0.69 | 1.95 | 0.63 | 1.00 | 1.00 | 1.00 |
| Spz1 | 1.00 | 1.00 | 1.00 | 1.00 | 1.00 | 1.00 | 13.83 | 1.00 | 1.00 | 1.00 | 1.00 | 1.00 |
| Srcin1 | 1.00 | 1.00 | 1.00 | 0.90 | 0.80 | 0.91 | 0.69 | 0.71 | 0.62 | 1.00 | 1.00 | 1.00 |
| Srm | 0.91 | 0.84 | 0.93 | 0.97 | 1.46 | 0.95 | 1.06 | 2.09 | 0.79 | 1.12 | 0.64 | 0.73 |
| Srp19 | 0.82 | 0.76 | 0.92 | 1.06 | 3.24 | 1.12 | 1.18 | 0.74 | 0.99 | 1.08 | 1.03 | 1.25 |
| Srp54c | 1.51 | 2.28 | 1.06 | 0.58 | 6.57 | 0.63 | 1.10 | 1.66 | 0.60 | 1.34 | 1.34 | 3.25 |
| Srp9 | 0.66 | 0.57 | 0.81 | 0.93 | 2.47 | 1.06 | 0.90 | 2.12 | 0.87 | 1.49 | 1.09 | 1.05 |
| Srpk3 | 1.00 | 1.00 | 1.00 | 1.01 | 0.99 | 0.70 | 1.83 | 6.94 | 1.74 | 1.44 | 0.56 | 0.74 |
| Srrd | 0.96 | 0.47 | 1.08 | 1.16 | 0.36 | 1.24 | 1.80 | 0.87 | 0.96 | 0.36 | 1.52 | 1.05 |
| Ssbp4 | 1.00 | 1.00 | 1.00 | 1.03 | 0.98 | 0.94 | 0.90 | 6.83 | 0.97 | 3.24 | 1.11 | 1.67 |
| Ssna1 | 1.11 | 0.73 | 1.00 | 1.17 | 0.91 | 1.11 | 1.13 | 6.86 | 0.81 | 2.10 | 1.16 | 1.11 |
| Ssr4 | 0.83 | 1.05 | 0.88 | 1.28 | 2.00 | 1.08 | 1.20 | 5.27 | 1.06 | 2.38 | 1.35 | 1.24 |
| Sssca1 | 1.48 | 0.72 | 0.91 | 1.10 | 0.91 | 0.93 | 1.00 | 7.96 | 0.80 | 2.10 | 1.01 | 0.82 |
| Sst | 0.96 | 0.91 | 1.41 | 1.23 | 1.20 | 1.10 | 1.00 | 1.00 | 1.00 | 1.00 | 1.00 | 1.00 |
| St14 | 1.42 | 1.30 | 1.14 | 1.00 | 1.91 | 1.00 | 0.97 | 5.76 | 0.83 | 2.56 | 1.02 | 0.93 |
| St3gal3 | 1.50 | 0.60 | 1.14 | 1.21 | 0.90 | 1.03 | 1.13 | 9.11 | 1.36 | 2.50 | 1.22 | 1.09 |
| St6galnac2 | 1.30 | 0.65 | 1.07 | 1.57 | 0.94 | 0.98 | 3.38 | 7.56 | 1.76 | 2.06 | 1.63 | 1.50 |
| Stard10 | 0.81 | 0.88 | 0.85 | 1.18 | 0.86 | 1.03 | 1.23 | 12.85 | 0.90 | 2.30 | 0.87 | 0.90 |
| Stbd1 | 2.06 | 2.42 | 2.70 | 1.46 | 1.00 | 1.03 | 1.47 | 1.65 | 1.47 | 1.00 | 1.00 | 1.00 |
| Stfa1 | 1.00 | 1.00 | 1.00 | 1.00 | 1.00 | 1.00 | 0.20 | 4.27 | 0.41 | 5.29 | 2.07 | 1.15 |
| Stfa2l1 | 1.00 | 1.00 | 1.00 | 1.00 | 1.00 | 1.00 | 1.00 | 2.53 | 1.00 | 2.97 | 1.68 | 0.97 |
| Stfa3 | 1.00 | 1.00 | 1.00 | 1.00 | 1.00 | 1.00 | 0.19 | 7.97 | 0.28 | 1.48 | 0.38 | 0.55 |
| Stk19 | 0.64 | 0.95 | 0.77 | 0.98 | 1.17 | 1.08 | 1.46 | 14.86 | 1.03 | 5.28 | 1.70 | 1.44 |

Fig. 35- 269

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Stk39 | 0.88 | 1.00 | 0.94 | 0.90 | 0.66 | 0.72 | 0.67 | 0.76 | 0.82 | 0.61 | 0.55 | 0.88 |
| Stmn2 | 1.40 | 1.38 | 1.50 | 0.84 | 0.28 | 0.92 | 0.67 | 0.72 | 0.57 | 0.48 | 0.62 | 0.73 |
| Stmn3 | 1.00 | 1.00 | 1.00 | 1.00 | 0.07 | 1.00 | 1.00 | 1.00 | 1.00 | 1.18 | 1.00 | 1.00 |
| Stmn4 | 1.00 | 0.71 | 1.00 | 1.00 | 0.16 | 1.00 | 1.00 | 1.00 | 1.00 | 1.00 | 1.00 | 1.00 |
| Ston1 | 1.37 | 1.00 | 2.09 | 6.73 | 0.41 | 1.36 | 2.02 | 4.23 | 2.19 | 1.00 | 0.49 | 1.36 |
| Stx1b | 1.00 | 1.00 | 1.00 | 0.59 | 0.11 | 0.43 | 1.00 | 1.00 | 1.00 | 1.00 | 1.00 | 1.19 |
| Stx4a | 1.02 | 0.56 | 0.85 | 0.29 | 5.48 | 0.83 | 1.01 | 0.81 | 0.91 | 2.79 | 3.74 | 1.03 |
| Stx8 | 1.23 | 0.77 | 1.12 | 0.72 | 9.09 | 0.91 | 1.07 | 1.07 | 0.87 | 2.32 | 2.69 | 0.95 |
| Suclg1 | 0.98 | 0.72 | 0.89 | 0.41 | 3.34 | 0.75 | 1.08 | 0.92 | 0.78 | 1.62 | 2.15 | 0.98 |
| Sugt1 | 0.84 | 0.91 | 0.82 | 0.93 | 8.88 | 1.44 | 1.06 | 1.03 | 0.91 | 1.43 | 2.34 | 1.00 |
| Sult1a1 | 1.17 | 0.78 | 1.08 | 1.32 | 11.79 | 2.01 | 1.44 | 1.49 | 1.46 | 1.99 | 2.45 | 1.45 |
| Sult1e1 | 1.00 | 1.85 | 1.26 | 1.00 | 1.00 | 1.00 | 1.00 | 1.00 | 1.00 | 1.00 | 1.00 | 1.00 |
| Sult2b1 | 1.00 | 1.00 | 1.00 | 1.00 | 1.00 | 1.00 | 1.00 | 1.00 | 1.00 | 12.25 | 13.81 | 1.25 |
| Sult4a1 | 1.00 | 1.00 | 1.00 | 1.00 | 0.10 | 1.00 | 1.00 | 1.00 | 1.00 | 1.00 | 1.00 | 1.00 |
| Sult5a1 | 2.46 | 1.30 | 1.71 | 0.55 | 9.96 | 5.02 | 1.39 | 1.02 | 1.01 | 1.61 | 2.26 | 0.78 |
| Supt16 | 1.12 | 1.28 | 1.12 | 1.16 | 1.55 | 1.01 | 0.93 | 1.00 | 1.10 | 1.11 | 1.12 | 0.91 |
| Supt3 | 1.30 | 1.09 | 0.94 | 0.61 | 6.68 | 1.13 | 1.21 | 0.97 | 1.02 | 1.14 | 1.69 | 0.90 |
| Supt4a | 1.43 | 0.67 | 1.10 | 0.75 | 15.45 | 1.55 | 1.17 | 1.17 | 1.17 | 2.49 | 3.95 | 0.69 |
| Supt5 | 1.09 | 0.72 | 1.05 | 0.55 | 3.73 | 1.33 | 1.11 | 1.02 | 0.93 | 2.42 | 2.71 | 0.93 |
| Sv2b | 1.00 | 1.00 | 1.00 | 1.00 | 0.17 | 1.00 | 1.00 | 1.00 | 1.00 | 1.00 | 1.00 | 1.00 |
| Syce3 | 1.00 | 1.00 | 1.00 | 1.00 | 1.00 | 1.00 | 1.00 | 1.00 | 1.00 | 2.08 | 1.00 | 1.00 |
| Sycn | 1.00 | 1.00 | 1.00 | 1.04 | 1.00 | 1.00 | 1.00 | 1.00 | 1.00 | 1.03 | 1.00 | 3.38 |
| Syde2 | 1.07 | 1.00 | 1.05 | 6.82 | 3.09 | 2.50 | 1.17 | 1.45 | 1.06 | 1.17 | 0.89 | 1.06 |
| Syf2 | 1.23 | 0.84 | 1.00 | 1.04 | 5.35 | 1.26 | 1.01 | 0.98 | 0.97 | 2.84 | 2.55 | 0.98 |
| Sympk | 1.09 | 0.75 | 1.07 | 0.72 | 4.69 | 1.11 | 1.29 | 1.30 | 1.16 | 2.22 | 2.89 | 1.04 |
| Syn1 | 1.00 | 1.00 | 1.00 | 1.00 | 0.08 | 1.00 | 1.00 | 1.00 | 1.00 | 1.00 | 1.00 | 1.00 |
| Syn2 | 1.08 | 1.00 | 0.90 | 3.97 | 0.52 | 3.79 | 3.72 | 3.54 | 2.96 | 2.08 | 1.23 | 1.95 |
| Syngr1 | 0.84 | 0.74 | 0.83 | 0.20 | 1.16 | 0.84 | 1.14 | 0.80 | 0.95 | 1.07 | 1.93 | 0.99 |
| Syngr3 | 1.00 | 1.00 | 1.00 | 1.00 | 0.15 | 1.00 | 1.00 | 1.00 | 1.00 | 1.00 | 1.00 | 1.00 |
| Syp | 1.23 | 1.65 | 1.06 | 0.45 | 0.26 | 0.62 | 0.82 | 1.16 | 0.84 | 1.51 | 1.28 | 0.95 |
| Syt1 | 1.00 | 1.00 | 1.00 | 1.00 | 0.05 | 1.00 | 1.00 | 1.00 | 1.00 | 1.00 | 1.00 | 1.00 |
| Syt13 | 1.00 | 1.00 | 1.00 | 1.00 | 0.23 | 1.00 | 1.00 | 1.00 | 1.00 | 1.00 | 1.00 | 1.00 |
| Syt4 | 1.00 | 1.00 | 1.00 | 1.00 | 0.22 | 1.00 | 1.00 | 1.00 | 1.00 | 1.00 | 1.00 | 1.00 |
| Syt5 | 1.00 | 1.00 | 1.00 | 1.00 | 0.30 | 1.00 | 1.00 | 1.00 | 1.00 | 1.49 | 1.66 | 0.87 |
| Syt7 | 1.00 | 1.00 | 0.98 | 1.20 | 0.29 | 0.96 | 0.76 | 0.70 | 0.71 | 1.65 | 1.20 | 1.12 |
| Sytl1 | 1.00 | 1.00 | 1.00 | 0.38 | 5.25 | 0.64 | 1.00 | 1.00 | 1.00 | 1.99 | 2.42 | 0.96 |
| Sytl3 | 1.00 | 1.00 | 1.00 | 1.00 | 1.00 | 1.00 | 1.00 | 1.00 | 1.00 | 3.40 | 3.45 | 1.14 |
| Tac2 | 1.00 | 1.00 | 1.00 | 1.00 | 1.00 | 1.00 | 1.00 | 1.00 | 1.00 | 1.00 | 1.00 | 1.00 |
| Tagln3 | 1.00 | 1.00 | 1.00 | 1.00 | 0.11 | 1.00 | 1.00 | 1.00 | 1.00 | 1.00 | 1.00 | 1.00 |
| Taldo1 | 1.35 | 0.71 | 0.99 | 0.25 | 4.79 | 0.69 | 0.93 | 0.99 | 0.91 | 2.00 | 2.54 | 0.98 |
| Tat | 1.00 | 1.00 | 1.00 | 1.00 | 1.00 | 1.00 | 2.68 | 1.00 | 1.00 | 1.00 | 1.00 | 1.00 |
| Tbc1d10c | 0.62 | 0.39 | 0.79 | 1.00 | 1.00 | 1.00 | 0.99 | 0.95 | 0.57 | 1.17 | 1.10 | 0.78 |
| Tbc1d17 | 1.12 | 0.58 | 1.19 | 0.75 | 15.72 | 1.21 | 1.27 | 1.22 | 0.92 | 3.81 | 5.09 | 1.03 |
| Tbce | 0.80 | 1.00 | 0.64 | 0.57 | 2.25 | 0.73 | 1.24 | 0.92 | 0.82 | 2.45 | 2.74 | 0.84 |
| Tcap | 0.61 | 0.43 | 0.64 | 0.49 | 6.05 | 0.47 | 0.98 | 0.94 | 0.75 | 3.24 | 4.53 | 0.80 |
| Tceal5 | 0.93 | 0.85 | 0.87 | 1.00 | 0.23 | 1.00 | 1.00 | 1.00 | 1.00 | 0.96 | 1.00 | 1.00 |
| Tceal6 | 0.46 | 1.62 | 0.71 | 1.00 | 0.23 | 1.00 | 1.00 | 1.00 | 1.00 | 1.00 | 1.00 | 1.00 |
| Tceb1 | 0.95 | 0.99 | 0.80 | 0.41 | 2.80 | 0.69 | 0.84 | 0.96 | 0.79 | 1.13 | 1.43 | 0.84 |
| Tceb2 | 1.15 | 0.60 | 0.82 | 0.39 | 8.70 | 0.94 | 1.11 | 0.81 | 0.93 | 2.08 | 3.59 | 0.85 |
| Tcf25 | 1.02 | 0.67 | 1.06 | 0.71 | 4.58 | 1.04 | 1.03 | 0.94 | 0.98 | 2.97 | 2.96 | 1.02 |
| Tcn2 | 1.47 | 1.18 | 1.68 | 1.07 | 5.53 | 2.35 | 1.32 | 1.13 | 1.07 | 2.51 | 3.36 | 1.86 |
| Tcp11 | 1.00 | 1.00 | 1.00 | 1.00 | 1.00 | 1.00 | 1.00 | 1.00 | 1.00 | 1.46 | 1.75 | 1.22 |
| Tcp11l2 | 2.28 | 4.54 | 2.14 | 2.84 | 1.55 | 1.47 | 2.61 | 2.65 | 1.21 | 0.48 | 0.61 | 1.03 |
| Tcte3 | 1.00 | 1.00 | 1.00 | 0.62 | 2.87 | 0.26 | 1.00 | 1.00 | 1.00 | 1.59 | 2.62 | 0.79 |
| Tead1 | 0.84 | 0.92 | 0.71 | 5.13 | 2.23 | 2.07 | 1.09 | 1.33 | 1.15 | 1.35 | 0.93 | 1.22 |
| Tead4 | 1.95 | 1.10 | 1.55 | 5.89 | 3.93 | 2.34 | 1.35 | 1.81 | 1.79 | 0.60 | 1.36 | 1.02 |
| Tecr | 1.90 | 1.02 | 1.23 | 0.18 | 4.06 | 0.85 | 0.78 | 0.69 | 0.59 | 2.09 | 3.01 | 0.91 |
| Tekt1 | 5.42 | 2.32 | 5.87 | 1.00 | 1.00 | 1.00 | 1.00 | 1.00 | 1.00 | 2.60 | 3.23 | 1.13 |
| Tekt2 | 1.00 | 1.00 | 1.00 | 1.00 | 1.00 | 1.00 | 1.00 | 1.00 | 1.00 | 2.45 | 3.72 | 0.86 |
| Tesc | 1.00 | 1.00 | 1.00 | 0.38 | 4.14 | 0.28 | 1.14 | 0.97 | 0.77 | 3.59 | 1.84 | 1.00 |
| Tex264 | 1.45 | 0.88 | 1.13 | 0.48 | 5.52 | 1.16 | 1.27 | 0.92 | 0.97 | 1.91 | 2.77 | 1.04 |
| Tff1 | 0.04 | 0.98 | 1.00 | 3.68 | 0.65 | 0.34 | 0.15 | 0.33 | 1.00 | 0.05 | 1.00 | 1.00 |
| Tff2 | 0.32 | 1.12 | 1.00 | 1.00 | 1.00 | 1.00 | 1.00 | 1.00 | 1.00 | 0.61 | 2.73 | 0.85 |
| Tff3 | 1.00 | 1.00 | 1.00 | 1.00 | 1.00 | 1.00 | 1.00 | 1.00 | 1.00 | 1.00 | 1.00 | 1.00 |

Fig. 35- 270

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Stk39 | 1.19 | 1.17 | 1.55 | 0.97 | 0.93 | 0.98 | 1.00 | 1.00 | 1.00 | 1.04 | 1.20 | 0.99 |
| Stmn2 | 0.75 | 0.98 | 1.00 | 1.00 | 1.00 | 1.00 | 1.00 | 1.00 | 1.00 | 1.23 | 1.22 | 1.03 |
| Stmn3 | 1.00 | 1.00 | 1.00 | 1.00 | 1.00 | 1.00 | 1.00 | 1.00 | 1.00 | 0.68 | 2.04 | 1.26 |
| Stmn4 | 1.00 | 1.00 | 1.00 | 1.00 | 1.00 | 1.00 | 1.00 | 1.00 | 1.00 | 0.97 | 1.49 | 1.47 |
| Ston1 | 1.81 | 1.27 | 2.24 | 2.02 | 1.00 | 1.65 | 1.15 | 1.00 | 2.04 | 1.18 | 0.24 | 1.02 |
| Stx1b | 1.00 | 1.00 | 1.00 | 1.00 | 1.00 | 1.00 | 1.00 | 1.00 | 1.00 | 0.83 | 1.00 | 1.00 |
| Stx4a | 1.12 | 1.23 | 0.95 | 0.99 | 0.63 | 1.09 | 1.53 | 2.02 | 1.24 | 0.98 | 1.51 | 1.02 |
| Stx8 | 1.13 | 1.37 | 0.99 | 0.75 | 0.75 | 1.07 | 1.00 | 1.59 | 1.09 | 0.94 | 1.92 | 1.16 |
| Suclg1 | 1.15 | 1.41 | 0.88 | 0.76 | 0.65 | 0.80 | 0.87 | 1.36 | 0.97 | 1.02 | 1.62 | 1.06 |
| Sugt1 | 1.24 | 1.02 | 1.05 | 0.99 | 0.88 | 1.01 | 1.14 | 0.98 | 0.98 | 1.10 | 1.49 | 1.22 |
| Sult1a1 | 2.21 | 2.76 | 2.01 | 1.12 | 1.27 | 1.16 | 1.40 | 2.25 | 1.88 | 1.25 | 1.94 | 1.23 |
| Sult1e1 | 1.00 | 1.06 | 1.00 | 1.00 | 1.00 | 1.00 | 6.07 | 1.00 | 1.61 | 1.00 | 1.00 | 1.00 |
| Sult2b1 | 1.13 | 1.00 | 1.00 | 1.00 | 1.14 | 1.00 | 1.00 | 1.00 | 1.00 | 0.64 | 1.14 | 0.77 |
| Sult4a1 | 1.00 | 1.00 | 1.00 | 1.00 | 1.00 | 1.00 | 1.00 | 1.00 | 1.00 | 1.40 | 1.39 | 1.34 |
| Sult5a1 | 1.45 | 1.34 | 1.01 | 1.00 | 1.00 | 1.00 | 1.65 | 2.86 | 1.48 | 1.00 | 1.00 | 1.00 |
| Supt16 | 0.70 | 0.75 | 0.75 | 0.97 | 0.88 | 0.99 | 1.08 | 0.43 | 0.96 | 0.92 | 1.07 | 0.96 |
| Supt3 | 1.08 | 1.16 | 1.09 | 0.73 | 0.58 | 1.03 | 1.13 | 0.32 | 0.93 | 1.40 | 2.36 | 1.07 |
| Supt4a | 1.35 | 1.86 | 0.97 | 1.58 | 1.01 | 1.35 | 0.76 | 2.38 | 1.14 | 1.01 | 2.00 | 0.95 |
| Supt5 | 0.94 | 1.15 | 0.96 | 1.13 | 0.87 | 1.08 | 1.36 | 2.23 | 1.20 | 1.08 | 1.26 | 1.02 |
| Sv2b | 2.26 | 1.00 | 0.88 | 1.00 | 1.00 | 1.00 | 1.00 | 1.00 | 1.00 | 1.06 | 1.00 | 1.00 |
| Syce3 | 1.00 | 1.00 | 1.00 | 1.00 | 1.00 | 1.00 | 1.00 | 5.77 | 1.36 | 0.93 | 1.13 | 1.19 |
| Sycn | 1.00 | 1.30 | 1.57 | 2.75 | 1.77 | 1.04 | 1.00 | 1.00 | 0.77 | 0.80 | 1.78 | 1.70 |
| Syde2 | 1.05 | 1.14 | 0.96 | 1.05 | 1.74 | 1.17 | 1.13 | 1.00 | 1.20 | 1.53 | 0.90 | 1.10 |
| Syf2 | 1.25 | 1.37 | 1.00 | 1.05 | 0.69 | 0.86 | 1.00 | 1.97 | 0.84 | 1.13 | 1.61 | 1.01 |
| Sympk | 0.87 | 0.96 | 0.95 | 1.10 | 0.77 | 1.15 | 1.35 | 2.20 | 1.18 | 1.11 | 1.21 | 1.01 |
| Syn1 | 1.00 | 1.00 | 1.00 | 1.00 | 1.00 | 1.00 | 1.00 | 1.00 | 1.00 | 1.32 | 0.95 | 1.42 |
| Syn2 | 1.00 | 1.55 | 1.09 | 1.31 | 1.46 | 1.46 | 1.00 | 1.00 | 1.00 | 2.88 | 2.84 | 3.49 |
| Syngr1 | 0.54 | 0.74 | 0.78 | 0.60 | 0.66 | 0.83 | 1.00 | 1.00 | 1.00 | 0.87 | 0.82 | 1.04 |
| Syngr3 | 1.00 | 1.00 | 1.00 | 1.00 | 1.00 | 1.00 | 1.00 | 1.00 | 1.00 | 1.27 | 1.35 | 1.09 |
| Syp | 1.31 | 1.81 | 1.08 | 1.22 | 0.79 | 0.94 | 1.00 | 1.78 | 1.07 | 1.15 | 1.46 | 1.34 |
| Syt1 | 1.15 | 0.65 | 1.25 | 1.00 | 1.00 | 1.00 | 0.93 | 1.00 | 1.15 | 1.20 | 0.82 | 1.30 |
| Syt13 | 0.86 | 1.01 | 0.73 | 1.00 | 1.00 | 1.00 | 1.00 | 1.00 | 1.00 | 0.83 | 0.90 | 0.79 |
| Syt4 | 1.00 | 1.00 | 1.00 | 1.00 | 1.00 | 1.00 | 1.00 | 1.00 | 1.00 | 1.06 | 1.09 | 1.12 |
| Syt5 | 1.00 | 1.00 | 1.00 | 1.00 | 1.00 | 1.00 | 1.00 | 1.00 | 1.00 | 1.33 | 1.52 | 1.46 |
| Syt7 | 1.18 | 0.97 | 1.00 | 1.00 | 1.00 | 1.00 | 1.00 | 1.00 | 1.00 | 0.98 | 0.85 | 0.91 |
| Sytl1 | 1.43 | 1.84 | 1.07 | 1.00 | 0.67 | 0.77 | 1.00 | 3.65 | 1.27 | 0.78 | 1.48 | 0.94 |
| Sytl3 | 4.19 | 6.35 | 2.39 | 1.00 | 1.40 | 1.00 | 1.00 | 1.00 | 1.00 | 1.00 | 1.00 | 1.00 |
| Tac2 | 1.00 | 1.00 | 1.00 | 1.00 | 1.00 | 1.00 | 1.00 | 1.00 | 1.00 | 1.00 | 1.00 | 1.00 |
| Tagln3 | 1.00 | 1.00 | 1.00 | 1.00 | 1.00 | 1.00 | 1.00 | 1.00 | 1.00 | 0.82 | 1.28 | 1.37 |
| Taldo1 | 0.95 | 1.31 | 0.90 | 0.89 | 0.79 | 1.02 | 1.28 | 1.54 | 1.15 | 1.01 | 1.49 | 1.06 |
| Tat | 8.14 | 1.00 | 1.00 | 1.00 | 1.00 | 1.00 | 3.41 | 2.47 | 3.57 | 1.08 | 1.04 | 0.94 |
| Tbc1d10c | 0.90 | 1.07 | 0.93 | 1.00 | 0.85 | 1.00 | 1.00 | 1.00 | 1.00 | 0.92 | 1.07 | 1.14 |
| Tbc1d17 | 1.34 | 1.88 | 1.00 | 1.05 | 0.68 | 1.12 | 1.18 | 3.01 | 1.11 | 0.95 | 1.50 | 1.08 |
| Tbce | 1.06 | 1.00 | 1.01 | 0.94 | 0.93 | 1.03 | 1.03 | 1.59 | 1.38 | 1.05 | 1.36 | 0.98 |
| Tcap | 0.42 | 0.38 | 0.38 | 1.00 | 0.89 | 1.00 | 1.00 | 1.00 | 1.00 | 0.55 | 0.96 | 0.72 |
| Tceal5 | 1.09 | 1.00 | 1.00 | 1.00 | 1.00 | 1.00 | 1.00 | 1.00 | 1.00 | 0.84 | 1.13 | 1.64 |
| Tceal6 | 1.00 | 1.00 | 1.00 | 1.00 | 1.00 | 1.00 | 1.00 | 1.00 | 1.00 | 0.87 | 1.31 | 0.83 |
| Tceb1 | 0.79 | 0.89 | 0.78 | 0.87 | 0.67 | 0.76 | 1.06 | 0.75 | 0.95 | 0.91 | 1.38 | 0.99 |
| Tceb2 | 1.19 | 1.38 | 0.90 | 0.90 | 0.70 | 0.95 | 0.88 | 1.84 | 0.90 | 1.13 | 2.04 | 0.99 |
| Tcf25 | 1.14 | 1.17 | 1.17 | 1.12 | 0.60 | 1.08 | 1.10 | 3.32 | 1.11 | 0.95 | 1.20 | 0.94 |
| Tcn2 | 2.61 | 2.56 | 2.09 | 1.11 | 1.05 | 1.16 | 0.92 | 1.05 | 0.86 | 1.11 | 1.48 | 1.17 |
| Tcp11 | 0.95 | 1.41 | 0.81 | 1.00 | 1.00 | 1.00 | 1.00 | 1.00 | 1.00 | 1.00 | 1.00 | 1.00 |
| Tcp11l2 | 1.21 | 1.09 | 1.26 | 1.59 | 5.36 | 1.36 | 1.65 | 0.64 | 0.98 | 1.17 | 1.15 | 1.24 |
| Tcte3 | 1.00 | 1.00 | 1.00 | 1.77 | 1.57 | 0.48 | 1.00 | 1.00 | 1.00 | 1.00 | 1.61 | 0.67 |
| Tead1 | 1.52 | 1.21 | 1.45 | 1.20 | 0.85 | 0.99 | 2.41 | 1.34 | 0.95 | 1.04 | 0.62 | 0.86 |
| Tead4 | 1.00 | 1.00 | 1.00 | 1.00 | 1.00 | 1.00 | 1.00 | 1.00 | 1.00 | 0.65 | 1.00 | 0.68 |
| Tecr | 1.20 | 1.66 | 1.03 | 0.67 | 0.69 | 0.85 | 1.06 | 1.21 | 0.87 | 1.03 | 1.47 | 1.03 |
| Tekt1 | 1.00 | 1.00 | 1.00 | 1.00 | 1.00 | 1.00 | 1.00 | 1.00 | 1.00 | 1.00 | 1.00 | 1.00 |
| Tekt2 | 1.00 | 1.21 | 1.35 | 1.00 | 1.00 | 1.00 | 1.00 | 1.00 | 1.00 | 1.01 | 1.24 | 1.18 |
| Tesc | 0.55 | 0.82 | 0.54 | 0.74 | 0.49 | 0.89 | 1.00 | 1.00 | 1.00 | 1.24 | 1.85 | 1.54 |
| Tex264 | 1.49 | 1.78 | 1.16 | 1.02 | 0.88 | 1.04 | 0.80 | 0.97 | 0.80 | 1.06 | 1.82 | 1.12 |
| Tff1 | 0.98 | 0.02 | 1.54 | 0.66 | 0.43 | 1.47 | 0.60 | 0.77 | 0.79 | 0.10 | 0.12 | 0.86 |
| Tff2 | 1.00 | 0.18 | 1.08 | 1.00 | 1.00 | 0.83 | 1.00 | 5.16 | 0.93 | 0.37 | 1.47 | 8.09 |
| Tff3 | 0.99 | 2.71 | 3.14 | 1.00 | 1.00 | 1.00 | 2.32 | 7.67 | 3.95 | 1.32 | 2.03 | 1.40 |

Fig. 35- 271

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Stk39 | 1.01 | 1.07 | 0.84 | 0.76 | 1.02 | 0.68 | 1.01 | 1.85 | 1.03 | 1.29 | 1.91 | 1.07 |
| Stmn2 | 1.20 | 1.60 | 1.49 | 0.97 | 3.66 | 1.29 | 1.00 | 1.00 | 1.00 | 0.69 | 6.64 | 0.87 |
| Stmn3 | 1.02 | 1.31 | 1.57 | 1.00 | 1.00 | 1.00 | 1.00 | 1.00 | 1.00 | 1.00 | 21.49 | 1.00 |
| Stmn4 | 1.00 | 1.00 | 1.00 | 1.00 | 1.35 | 1.00 | 1.00 | 1.08 | 1.00 | 1.00 | 9.83 | 1.00 |
| Ston1 | 1.72 | 1.78 | 1.39 | 1.86 | 0.49 | 1.01 | 0.71 | 1.25 | 0.47 | 2.32 | 1.19 | 3.67 |
| Stx1b | 1.00 | 1.00 | 1.00 | 0.48 | 1.00 | 0.74 | 1.00 | 1.00 | 1.00 | 1.00 | 9.11 | 1.00 |
| Stx4a | 1.05 | 1.03 | 1.04 | 0.83 | 2.24 | 0.92 | 0.71 | 3.00 | 0.64 | 0.99 | 1.27 | 1.01 |
| Stx8 | 0.93 | 0.82 | 0.79 | 1.02 | 2.03 | 0.86 | 0.98 | 1.92 | 1.01 | 1.06 | 1.53 | 0.90 |
| Suclg1 | 0.75 | 0.70 | 0.69 | 0.64 | 2.40 | 0.69 | 1.54 | 2.66 | 1.45 | 1.05 | 1.53 | 0.98 |
| Sugt1 | 0.96 | 0.97 | 1.11 | 1.03 | 4.91 | 1.02 | 0.94 | 1.29 | 0.98 | 1.13 | 1.17 | 0.95 |
| Sult1a1 | 2.79 | 2.99 | 2.39 | 0.75 | 3.24 | 0.83 | 0.79 | 1.77 | 0.65 | 1.44 | 2.49 | 1.79 |
| Sult1e1 | 1.00 | 1.00 | 1.22 | 1.07 | 0.80 | 0.78 | 1.42 | 0.20 | 0.46 | 1.00 | 1.00 | 1.00 |
| Sult2b1 | 0.82 | 0.82 | 0.78 | 1.00 | 1.00 | 1.00 | 0.64 | 1.61 | 0.49 | 1.00 | 1.00 | 1.00 |
| Sult4a1 | 1.30 | 1.29 | 1.10 | 1.00 | 1.00 | 1.00 | 2.03 | 0.92 | 1.75 | 1.00 | 17.82 | 1.00 |
| Sult5a1 | 1.00 | 1.00 | 1.00 | 1.75 | 4.79 | 1.72 | 1.00 | 1.24 | 1.00 | 1.00 | 1.00 | 1.00 |
| Supt16 | 0.95 | 0.85 | 0.88 | 0.98 | 2.10 | 1.10 | 1.02 | 1.46 | 0.99 | 0.91 | 0.86 | 0.96 |
| Supt3 | 0.85 | 1.28 | 1.10 | 0.87 | 0.75 | 1.00 | 0.89 | 1.85 | 1.00 | 0.61 | 0.94 | 0.67 |
| Supt4a | 1.68 | 1.07 | 1.19 | 1.25 | 5.39 | 1.12 | 0.37 | 2.87 | 1.04 | 1.00 | 1.47 | 0.93 |
| Supt5 | 1.03 | 1.01 | 1.02 | 1.29 | 2.54 | 1.09 | 1.12 | 2.24 | 1.07 | 1.05 | 1.08 | 1.01 |
| Sv2b | 0.85 | 0.78 | 1.58 | 1.00 | 1.00 | 1.00 | 1.00 | 1.00 | 1.00 | 1.00 | 9.22 | 1.00 |
| Syce3 | 1.00 | 1.00 | 1.00 | 1.00 | 2.13 | 1.00 | 0.89 | 2.73 | 1.02 | 1.00 | 1.00 | 1.00 |
| Sycn | 25.52 | 1.78 | 2.20 | 1.00 | 1.00 | 0.73 | 1.00 | 2.72 | 0.81 | 4.49 | 10.68 | 0.61 |
| Syde2 | 1.18 | 1.32 | 1.19 | 1.09 | 1.17 | 1.39 | 1.02 | 1.00 | 1.00 | 1.77 | 1.11 | 1.00 |
| Syf2 | 1.20 | 1.21 | 1.11 | 1.01 | 2.07 | 1.12 | 0.95 | 2.39 | 0.98 | 1.09 | 1.27 | 1.03 |
| Sympk | 1.14 | 1.23 | 0.92 | 1.24 | 2.92 | 1.25 | 0.93 | 2.27 | 1.12 | 0.95 | 1.28 | 1.08 |
| Syn1 | 1.73 | 0.96 | 1.89 | 1.00 | 1.00 | 1.00 | 1.00 | 1.00 | 1.00 | 1.00 | 19.75 | 1.00 |
| Syn2 | 1.60 | 1.73 | 1.76 | 1.55 | 0.86 | 1.45 | 1.69 | 3.25 | 2.32 | 1.00 | 14.75 | 1.00 |
| Syngr1 | 0.72 | 0.87 | 0.71 | 1.13 | 1.00 | 0.44 | 0.68 | 2.23 | 0.84 | 0.45 | 12.74 | 0.57 |
| Syngr3 | 1.90 | 1.17 | 1.77 | 1.00 | 1.00 | 1.00 | 1.00 | 1.00 | 1.00 | 1.00 | 10.25 | 1.00 |
| Syp | 1.72 | 1.41 | 1.28 | 0.61 | 0.67 | 0.33 | 1.00 | 1.00 | 1.00 | 1.17 | 11.39 | 0.91 |
| Syt1 | 1.31 | 1.22 | 1.43 | 1.00 | 1.00 | 1.00 | 1.00 | 1.00 | 1.00 | 0.61 | 12.38 | 0.62 |
| Syt13 | 0.60 | 0.53 | 0.68 | 1.00 | 1.00 | 1.00 | 0.62 | 1.00 | 0.43 | 1.03 | 7.91 | 1.00 |
| Syt4 | 1.11 | 1.66 | 1.00 | 1.00 | 1.00 | 1.00 | 1.00 | 1.00 | 1.00 | 1.00 | 6.72 | 1.00 |
| Syt5 | 1.42 | 1.48 | 1.18 | 1.14 | 1.00 | 1.29 | 3.64 | 4.05 | 3.33 | 1.00 | 5.12 | 1.00 |
| Syt7 | 1.46 | 1.77 | 1.34 | 0.79 | 0.79 | 0.86 | 1.04 | 0.79 | 0.82 | 1.00 | 7.06 | 1.00 |
| Sytl1 | 0.88 | 1.15 | 0.93 | 1.60 | 1.00 | 1.52 | 1.00 | 2.66 | 1.00 | 0.83 | 0.97 | 1.16 |
| Sytl3 | 1.00 | 1.00 | 1.00 | 1.00 | 1.00 | 1.00 | 1.00 | 1.43 | 1.00 | 2.62 | 1.97 | 1.95 |
| Tac2 | 1.00 | 1.00 | 1.00 | 1.00 | 1.00 | 1.00 | 1.00 | 1.00 | 1.00 | 1.00 | 1.00 | 0.67 |
| Tagln3 | 1.42 | 1.68 | 1.16 | 1.00 | 1.00 | 1.00 | 1.00 | 1.00 | 1.00 | 1.00 | 15.37 | 1.00 |
| Taldo1 | 0.88 | 0.96 | 0.85 | 0.80 | 3.23 | 0.90 | 0.87 | 1.72 | 0.73 | 0.91 | 1.10 | 0.80 |
| Tat | 2.59 | 7.25 | 1.31 | 7.06 | 1.00 | 1.00 | 1.00 | 1.00 | 1.00 | 1.00 | 1.15 | 1.00 |
| Tbc1d10c | 1.25 | 0.87 | 1.63 | 0.55 | 0.77 | 1.72 | 1.00 | 1.57 | 1.00 | 0.92 | 0.91 | 0.99 |
| Tbc1d17 | 1.13 | 1.42 | 1.32 | 1.02 | 2.85 | 0.96 | 0.93 | 4.03 | 1.15 | 1.18 | 1.42 | 1.17 |
| Tbce | 0.98 | 1.41 | 0.98 | 0.76 | 2.58 | 1.33 | 1.20 | 4.45 | 1.00 | 1.25 | 1.16 | 0.81 |
| Tcap | 2.52 | 1.30 | 2.09 | 1.70 | 0.33 | 1.00 | 1.00 | 1.68 | 1.00 | 1.00 | 0.95 | 1.09 |
| Tceal5 | 0.54 | 0.78 | 1.10 | 0.92 | 1.00 | 2.36 | 1.00 | 1.00 | 1.00 | 1.00 | 5.85 | 1.00 |
| Tceal6 | 0.47 | 0.68 | 0.82 | 1.00 | 1.00 | 1.00 | 1.00 | 1.00 | 0.70 | 1.00 | 7.54 | 1.00 |
| Tceb1 | 1.01 | 0.96 | 0.95 | 0.87 | 6.22 | 0.88 | 1.05 | 1.27 | 1.06 | 0.85 | 0.93 | 0.91 |
| Tceb2 | 0.90 | 0.87 | 1.07 | 0.98 | 2.52 | 0.94 | 0.97 | 2.77 | 1.02 | 0.85 | 1.31 | 0.91 |
| Tcf25 | 1.06 | 1.08 | 0.98 | 1.09 | 1.86 | 1.03 | 0.93 | 3.08 | 0.88 | 1.19 | 1.18 | 1.09 |
| Tcn2 | 1.41 | 1.40 | 1.31 | 1.90 | 5.04 | 2.12 | 0.89 | 0.96 | 0.75 | 1.52 | 1.93 | 1.32 |
| Tcp11 | 1.00 | 1.00 | 1.00 | 2.74 | 0.82 | 1.88 | 0.97 | 0.79 | 1.05 | 1.00 | 1.00 | 1.00 |
| Tcp11l2 | 1.68 | 1.77 | 1.65 | 1.97 | 1.02 | 1.45 | 0.97 | 0.48 | 0.87 | 1.25 | 1.01 | 1.25 |
| Tcte3 | 1.00 | 1.00 | 1.00 | 2.34 | 1.00 | 1.06 | 0.76 | 5.79 | 0.74 | 0.91 | 1.51 | 0.51 |
| Tead1 | 1.09 | 1.09 | 1.00 | 1.53 | 0.71 | 1.28 | 1.22 | 1.00 | 1.06 | 0.88 | 0.76 | 1.06 |
| Tead4 | 1.61 | 1.33 | 1.04 | 6.74 | 2.70 | 4.30 | 1.00 | 1.00 | 1.00 | 1.00 | 1.00 | 1.00 |
| Tecr | 0.97 | 1.27 | 1.03 | 0.76 | 4.82 | 0.88 | 0.88 | 1.70 | 1.19 | 0.92 | 1.47 | 0.81 |
| Tekt1 | 1.00 | 1.00 | 1.00 | 1.73 | 5.66 | 3.81 | 1.04 | 1.96 | 0.95 | 1.00 | 1.00 | 1.00 |
| Tekt2 | 1.00 | 1.00 | 1.06 | 1.60 | 1.35 | 1.64 | 1.16 | 1.98 | 1.04 | 1.30 | 1.28 | 0.90 |
| Tesc | 0.86 | 1.02 | 0.83 | 0.78 | 2.43 | 2.60 | 0.69 | 2.73 | 0.92 | 0.92 | 1.34 | 0.65 |
| Tex264 | 1.17 | 1.27 | 1.20 | 0.94 | 4.15 | 1.10 | 0.86 | 1.51 | 0.93 | 1.10 | 1.45 | 1.14 |
| Tff1 | 0.74 | 1.01 | 0.67 | 0.54 | 0.75 | 0.48 | 1.81 | 1.00 | 1.01 | 1.00 | 1.00 | 1.18 |
| Tff2 | 0.96 | 1.00 | 1.08 | 1.44 | 1.00 | 0.54 | 1.21 | 1.00 | 1.35 | 1.00 | 3.32 | 1.00 |
| Tff3 | 4.69 | 4.36 | 7.56 | 1.00 | 1.00 | 1.00 | 1.00 | 1.00 | 1.00 | 1.00 | 1.00 | 1.00 |

Fig. 35- 272

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Stk39 | 1.03 | 1.05 | 0.65 | 1.05 | 5.12 | 1.07 | 1.32 | 0.43 | 0.95 | 3.26 | 1.51 | 1.69 |
| Stmn2 | 1.00 | 1.00 | 1.00 | 1.15 | 0.98 | 1.07 | 0.56 | 0.85 | 1.02 | 1.00 | 1.00 | 1.00 |
| Stmn3 | 1.00 | 1.00 | 1.00 | 1.07 | 1.10 | 1.03 | 2.06 | 3.13 | 1.00 | 1.00 | 1.00 | 1.00 |
| Stmn4 | 1.00 | 1.00 | 1.00 | 0.97 | 0.80 | 0.98 | 1.00 | 3.02 | 1.00 | 1.00 | 1.00 | 1.00 |
| Ston1 | 1.00 | 1.00 | 1.00 | 1.21 | 1.00 | 1.20 | 1.10 | 0.20 | 1.84 | 1.00 | 1.86 | 1.03 |
| Stx1b | 1.00 | 1.00 | 1.00 | 0.92 | 0.80 | 0.86 | 0.83 | 1.00 | 1.23 | 1.00 | 1.00 | 1.00 |
| Stx4a | 0.68 | 1.02 | 1.58 | 1.14 | 0.99 | 1.07 | 0.78 | 8.80 | 0.83 | 3.11 | 1.24 | 1.16 |
| Stx8 | 1.00 | 1.00 | 1.00 | 1.18 | 1.86 | 0.89 | 1.21 | 6.12 | 1.14 | 2.65 | 1.45 | 1.24 |
| Suclg1 | 0.78 | 0.88 | 0.70 | 1.01 | 1.16 | 0.99 | 1.03 | 5.78 | 1.14 | 1.92 | 1.20 | 1.10 |
| Sugt1 | 1.00 | 0.91 | 1.34 | 0.93 | 0.41 | 0.95 | 0.95 | 3.27 | 0.96 | 2.11 | 0.95 | 1.13 |
| Sult1a1 | 2.18 | 5.61 | 1.90 | 1.68 | 1.74 | 1.41 | 1.25 | 9.45 | 1.55 | 3.33 | 2.92 | 1.95 |
| Sult1e1 | 1.00 | 1.00 | 1.00 | 1.00 | 1.00 | 1.00 | 1.31 | 1.00 | 1.00 | 1.00 | 1.00 | 1.00 |
| Sult2b1 | 1.00 | 1.00 | 1.00 | 1.96 | 1.20 | 1.84 | 1.03 | 11.68 | 0.64 | 1.00 | 1.00 | 1.00 |
| Sult4a1 | 1.00 | 1.00 | 1.00 | 1.09 | 1.25 | 1.03 | 1.30 | 1.08 | 1.07 | 1.00 | 1.00 | 1.00 |
| Sult5a1 | 1.00 | 1.00 | 1.00 | 1.00 | 0.32 | 1.00 | 1.17 | 5.07 | 0.98 | 1.00 | 1.00 | 1.00 |
| Supt16 | 0.93 | 1.19 | 1.00 | 1.00 | 9.79 | 1.03 | 0.86 | 0.84 | 0.85 | 0.68 | 0.82 | 0.84 |
| Supt3 | 1.00 | 1.00 | 0.92 | 0.67 | 0.41 | 0.98 | 1.40 | 2.45 | 1.30 | 1.87 | 1.23 | 0.94 |
| Supt4a | 1.68 | 1.34 | 1.20 | 1.04 | 0.70 | 1.02 | 1.24 | 15.81 | 0.94 | 3.53 | 1.31 | 1.20 |
| Supt5 | 0.88 | 0.94 | 0.98 | 1.19 | 0.89 | 1.13 | 1.24 | 5.40 | 0.99 | 2.19 | 1.21 | 0.99 |
| Sv2b | 1.00 | 1.00 | 1.00 | 0.99 | 1.23 | 0.97 | 1.00 | 1.00 | 1.00 | 1.00 | 1.00 | 1.00 |
| Syce3 | 1.00 | 1.00 | 1.00 | 1.00 | 1.00 | 1.00 | 1.00 | 1.00 | 1.00 | 1.00 | 1.00 | 1.00 |
| Sycn | 0.82 | 0.84 | 0.83 | 1.38 | 1.00 | 0.69 | 0.58 | 1.00 | 0.83 | 1.00 | 0.23 | 1.37 |
| Syde2 | 1.00 | 1.00 | 1.00 | 0.94 | 1.00 | 1.11 | 1.46 | 1.20 | 2.08 | 1.00 | 1.00 | 1.00 |
| Syf2 | 1.01 | 1.19 | 0.89 | 1.15 | 0.87 | 1.12 | 1.39 | 7.79 | 1.17 | 2.20 | 1.31 | 1.00 |
| Sympk | 1.37 | 1.09 | 1.15 | 1.10 | 0.87 | 1.02 | 1.25 | 5.37 | 1.08 | 2.28 | 1.08 | 0.86 |
| Syn1 | 1.00 | 1.00 | 1.00 | 1.10 | 0.88 | 1.03 | 1.00 | 1.83 | 1.00 | 1.00 | 1.00 | 1.00 |
| Syn2 | 3.46 | 2.59 | 1.50 | 1.07 | 1.22 | 1.03 | 1.43 | 1.52 | 1.33 | 1.00 | 1.00 | 1.00 |
| Syngr1 | 0.75 | 1.00 | 0.82 | 1.07 | 0.96 | 1.00 | 1.32 | 2.34 | 0.93 | 0.70 | 0.70 | 0.90 |
| Syngr3 | 1.00 | 1.00 | 1.00 | 1.13 | 0.76 | 1.09 | 1.00 | 1.00 | 1.00 | 1.00 | 1.00 | 1.00 |
| Syp | 0.57 | 0.78 | 0.58 | 1.13 | 1.08 | 1.03 | 1.03 | 0.96 | 1.14 | 2.53 | 0.99 | 0.99 |
| Syt1 | 1.00 | 1.00 | 1.00 | 1.01 | 0.88 | 0.96 | 1.00 | 1.00 | 1.00 | 1.00 | 1.00 | 1.00 |
| Syt13 | 0.53 | 0.47 | 0.79 | 1.21 | 1.34 | 1.05 | 0.61 | 0.45 | 0.83 | 1.00 | 1.00 | 1.00 |
| Syt4 | 1.00 | 1.00 | 1.00 | 1.01 | 0.93 | 1.02 | 1.00 | 1.00 | 1.00 | 1.00 | 1.00 | 1.00 |
| Syt5 | 1.00 | 1.00 | 1.00 | 1.05 | 1.25 | 1.01 | 1.00 | 1.00 | 1.00 | 1.00 | 1.00 | 1.00 |
| Syt7 | 1.00 | 1.00 | 1.00 | 0.95 | 1.19 | 0.95 | 1.00 | 1.00 | 1.00 | 1.00 | 1.00 | 1.00 |
| Sytl1 | 0.86 | 0.80 | 1.03 | 1.00 | 1.13 | 1.01 | 1.05 | 6.20 | 0.83 | 3.02 | 1.11 | 1.07 |
| Sytl3 | 1.00 | 1.00 | 1.00 | 1.00 | 0.59 | 1.00 | 2.00 | 8.77 | 1.72 | 6.21 | 1.88 | 1.36 |
| Tac2 | 1.00 | 1.00 | 1.00 | 0.95 | 7.62 | 1.12 | 1.00 | 1.00 | 1.00 | 1.62 | 1.15 | 1.39 |
| Tagln3 | 1.00 | 1.00 | 1.00 | 1.15 | 1.12 | 1.09 | 1.00 | 1.00 | 1.00 | 1.00 | 1.00 | 1.00 |
| Taldo1 | 1.05 | 1.36 | 1.04 | 1.03 | 0.78 | 1.05 | 1.44 | 8.72 | 1.05 | 2.65 | 1.31 | 1.27 |
| Tat | 1.00 | 1.00 | 1.00 | 1.00 | 1.00 | 1.00 | 1.32 | 1.00 | 1.00 | 1.00 | 1.00 | 1.00 |
| Tbc1d10c | 1.00 | 1.00 | 0.74 | 1.10 | 2.65 | 1.12 | 0.82 | 7.18 | 1.04 | 2.01 | 1.23 | 1.13 |
| Tbc1d17 | 0.96 | 0.70 | 0.80 | 1.12 | 0.88 | 1.07 | 1.51 | 21.63 | 1.30 | 4.53 | 1.69 | 1.05 |
| Tbce | 1.00 | 1.00 | 1.00 | 0.88 | 5.26 | 0.96 | 1.12 | 2.20 | 1.13 | 2.00 | 1.37 | 1.06 |
| Tcap | 1.00 | 1.00 | 1.00 | 0.75 | 1.12 | 0.90 | 2.04 | 20.79 | 1.81 | 2.12 | 1.00 | 1.00 |
| Tceal5 | 1.00 | 1.00 | 1.00 | 1.28 | 1.68 | 1.05 | 1.50 | 1.74 | 1.34 | 1.00 | 1.00 | 1.00 |
| Tceal6 | 1.00 | 1.00 | 1.00 | 1.17 | 1.10 | 0.98 | 1.00 | 1.00 | 1.00 | 1.00 | 1.00 | 1.00 |
| Tceb1 | 1.20 | 1.32 | 0.91 | 0.91 | 0.72 | 1.11 | 0.80 | 1.98 | 0.99 | 1.26 | 1.00 | 1.10 |
| Tceb2 | 0.81 | 0.93 | 0.98 | 1.18 | 1.08 | 1.08 | 1.26 | 11.71 | 0.88 | 2.81 | 1.19 | 1.14 |
| Tcf25 | 0.88 | 0.87 | 1.01 | 1.05 | 0.82 | 1.02 | 1.16 | 6.24 | 1.16 | 2.67 | 1.26 | 1.10 |
| Tcn2 | 0.99 | 1.10 | 1.19 | 1.17 | 1.91 | 1.20 | 1.71 | 4.03 | 1.52 | 2.44 | 1.96 | 1.45 |
| Tcp11 | 1.00 | 1.00 | 1.00 | 1.00 | 1.00 | 1.00 | 12.63 | 2.59 | 1.00 | 1.00 | 1.00 | 1.00 |
| Tcp11l2 | 1.73 | 2.60 | 1.94 | 1.07 | 0.36 | 0.99 | 1.72 | 0.40 | 1.50 | 0.57 | 1.07 | 0.93 |
| Tcte3 | 1.00 | 0.89 | 1.00 | 1.00 | 0.49 | 1.00 | 3.73 | 3.98 | 0.98 | 0.72 | 0.58 | 0.77 |
| Tead1 | 1.36 | 1.48 | 1.03 | 0.96 | 1.20 | 0.91 | 1.30 | 1.04 | 1.25 | 1.00 | 1.00 | 1.00 |
| Tead4 | 1.00 | 1.00 | 1.00 | 1.00 | 1.00 | 1.00 | 0.81 | 0.53 | 0.95 | 1.00 | 1.00 | 1.00 |
| Tecr | 0.81 | 0.79 | 0.62 | 1.08 | 0.86 | 1.17 | 1.66 | 6.13 | 1.02 | 3.75 | 1.44 | 1.44 |
| Tekt1 | 1.00 | 1.00 | 1.00 | 0.90 | 1.60 | 1.25 | 2.36 | 1.00 | 1.00 | 1.00 | 1.00 | 1.00 |
| Tekt2 | 1.00 | 1.00 | 1.00 | 0.95 | 2.81 | 1.04 | 1.32 | 5.19 | 0.90 | 1.00 | 1.00 | 1.00 |
| Tesc | 1.00 | 1.00 | 1.00 | 1.11 | 1.07 | 1.14 | 0.67 | 6.87 | 0.42 | 1.89 | 0.70 | 1.16 |
| Tex264 | 1.37 | 1.13 | 0.93 | 1.22 | 1.16 | 1.02 | 1.26 | 5.50 | 0.79 | 2.57 | 1.28 | 1.60 |
| Tff1 | 1.00 | 1.00 | 0.21 | 1.00 | 2.20 | 0.32 | 1.00 | 9.74 | 0.96 | 0.70 | 1.54 | 1.00 |
| Tff2 | 0.81 | 0.90 | 0.77 | 1.00 | 0.12 | 0.45 | 1.00 | 1.00 | 1.13 | 1.00 | 1.00 | 1.00 |
| Tff3 | 1.00 | 1.00 | 1.00 | 1.00 | 1.00 | 1.00 | 1.00 | 1.00 | 1.00 | 1.00 | 1.00 | 1.00 |

Fig. 35- 273

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Tgif1 | 3.38 | 5.25 | 3.17 | 6.59 | 2.07 | 1.40 | 0.99 | 0.88 | 1.22 | 0.92 | 0.77 | 1.03 |
| Tgoln2 | 1.00 | 1.00 | 1.00 | 1.00 | 65.96 | 1.00 | 1.65 | 1.00 | 5.31 | 20.49 | 3.32 | 1.00 |
| Tgtp1 | 1.30 | 1.00 | 2.24 | 6.89 | 2.34 | 1.96 | 4.05 | 2.23 | 1.75 | 1.10 | 1.06 | 1.27 |
| Tgtp2 | 1.74 | 1.03 | 2.23 | 6.12 | 1.70 | 1.99 | 4.20 | 2.45 | 2.46 | 1.00 | 0.75 | 1.16 |
| Thap3 | 0.96 | 0.47 | 0.68 | 1.16 | 10.14 | 1.35 | 0.77 | 0.69 | 0.83 | 1.61 | 2.58 | 0.96 |
| Thap7 | 1.19 | 0.83 | 0.88 | 0.50 | 5.45 | 1.23 | 0.97 | 0.84 | 0.88 | 1.63 | 2.23 | 1.24 |
| Thbs1 | 1.41 | 4.39 | 1.25 | 5.63 | 1.00 | 2.38 | 1.65 | 2.46 | 4.34 | 0.48 | 0.56 | 2.40 |
| Thrsp | 1.28 | 1.18 | 1.34 | 0.16 | 1.68 | 0.58 | 1.06 | 0.89 | 0.80 | 2.08 | 1.87 | 1.08 |
| Tigit | 1.00 | 1.00 | 1.00 | 1.00 | 1.00 | 1.00 | 1.00 | 1.00 | 1.00 | 1.00 | 1.00 | 1.04 |
| Timm10b | 1.18 | 0.57 | 0.85 | 0.20 | 3.41 | 0.65 | 0.97 | 0.64 | 0.72 | 1.67 | 2.84 | 0.88 |
| Timm13 | 1.26 | 0.51 | 0.99 | 0.18 | 12.36 | 0.79 | 1.02 | 0.75 | 0.79 | 3.39 | 5.32 | 0.98 |
| Timm44 | 0.94 | 0.81 | 0.77 | 0.40 | 2.13 | 0.83 | 1.01 | 0.90 | 0.77 | 1.00 | 1.45 | 0.82 |
| Timm50 | 1.14 | 0.58 | 0.97 | 0.32 | 5.68 | 0.98 | 1.13 | 0.94 | 0.88 | 2.08 | 2.93 | 0.96 |
| Timp1 | 3.47 | 1.94 | 1.52 | 1.00 | 2.80 | 1.00 | 1.22 | 0.93 | 2.42 | 3.31 | 6.19 | 1.70 |
| Tlcd2 | 0.98 | 0.40 | 0.63 | 0.54 | 4.30 | 0.74 | 0.74 | 0.73 | 0.85 | 1.39 | 1.67 | 0.68 |
| Tma16 | 1.31 | 1.18 | 0.87 | 1.13 | 7.12 | 1.85 | 1.86 | 0.97 | 0.75 | 1.13 | 1.23 | 1.17 |
| Tmc6 | 1.60 | 0.97 | 1.33 | 0.51 | 5.18 | 1.07 | 1.34 | 1.39 | 0.99 | 3.93 | 4.90 | 1.11 |
| Tmco2 | 1.00 | 1.00 | 1.00 | 1.00 | 1.00 | 1.00 | 1.00 | 1.00 | 1.00 | 1.48 | 1.00 | 1.00 |
| Tmed3 | 0.95 | 0.55 | 0.86 | 0.74 | 5.13 | 1.02 | 0.87 | 0.80 | 1.02 | 2.66 | 2.65 | 0.95 |
| Tmem107 | 1.00 | 0.38 | 0.95 | 1.00 | 1.16 | 1.00 | 0.74 | 0.50 | 0.85 | 2.38 | 3.24 | 1.19 |
| Tmem120a | 0.94 | 0.44 | 1.20 | 0.18 | 9.80 | 1.04 | 1.39 | 1.47 | 1.34 | 5.36 | 12.98 | 0.84 |
| Tmem130 | 1.00 | 1.00 | 1.00 | 1.00 | 0.13 | 1.00 | 1.00 | 1.00 | 1.00 | 1.00 | 1.00 | 1.00 |
| Tmem140 | 3.12 | 2.87 | 2.45 | 1.02 | 0.78 | 1.65 | 3.12 | 3.51 | 1.63 | 0.41 | 0.42 | 1.35 |
| Tmem141 | 1.48 | 0.64 | 0.86 | 0.53 | 8.19 | 0.76 | 0.88 | 0.81 | 0.70 | 2.57 | 3.46 | 0.84 |
| Tmem147 | 1.11 | 0.69 | 0.85 | 0.17 | 2.97 | 0.84 | 1.19 | 0.97 | 0.86 | 1.29 | 2.61 | 1.05 |
| Tmem14c | 1.42 | 0.90 | 0.90 | 0.33 | 2.83 | 0.65 | 1.08 | 1.00 | 0.79 | 1.21 | 1.95 | 1.17 |
| Tmem151a | 1.00 | 1.00 | 1.00 | 1.00 | 0.17 | 1.00 | 1.30 | 1.01 | 1.69 | 1.24 | 1.79 | 1.26 |
| Tmem160 | 1.23 | 0.47 | 0.82 | 0.26 | 11.61 | 0.75 | 0.97 | 0.77 | 0.86 | 2.95 | 4.84 | 0.92 |
| Tmem167b | 1.10 | 4.01 | 1.05 | 1.90 | 2.42 | 1.00 | 1.03 | 1.25 | 1.02 | 14.91 | 3.72 | 1.22 |
| Tmem179 | 1.00 | 1.00 | 1.00 | 0.23 | 0.15 | 0.38 | 0.46 | 0.68 | 0.53 | 1.00 | 1.00 | 1.00 |
| Tmem179b | 1.23 | 1.21 | 1.57 | 0.85 | 4.83 | 1.10 | 0.98 | 0.70 | 1.14 | 1.11 | 2.08 | 0.80 |
| Tmem198b | 1.08 | 0.81 | 0.88 | 1.35 | 5.82 | 1.02 | 0.85 | 0.69 | 0.82 | 1.42 | 2.33 | 1.00 |
| Tmem205 | 1.76 | 0.86 | 1.59 | 0.59 | 12.17 | 1.40 | 1.16 | 1.01 | 1.06 | 2.49 | 4.25 | 1.17 |
| Tmem208 | 1.26 | 0.83 | 0.98 | 0.23 | 4.84 | 0.79 | 0.98 | 0.87 | 0.98 | 1.55 | 2.40 | 0.98 |
| Tmem25 | 0.48 | 0.49 | 0.42 | 0.60 | 0.33 | 0.53 | 0.64 | 0.61 | 0.52 | 1.00 | 0.93 | 0.58 |
| Tmem252 | 2.77 | 3.27 | 2.16 | 1.98 | 1.55 | 1.17 | 2.11 | 1.18 | 1.61 | 1.62 | 1.84 | 2.59 |
| Tmem254c | 1.00 | 1.00 | 1.00 | 1.52 | 0.21 | 0.97 | 0.95 | 1.74 | 1.00 | 1.00 | 1.00 | 0.92 |
| Tmem256 | 1.04 | 0.43 | 0.73 | 0.61 | 12.00 | 0.77 | 0.82 | 0.75 | 0.77 | 2.54 | 4.45 | 0.93 |
| Tmem258 | 1.54 | 0.80 | 1.01 | 0.20 | 1.87 | 0.60 | 0.91 | 0.95 | 0.98 | 0.41 | 1.04 | 1.12 |
| Tmem259 | 1.15 | 0.65 | 0.97 | 0.66 | 5.71 | 1.00 | 1.10 | 0.89 | 0.93 | 1.89 | 3.20 | 1.06 |
| Tmem37 | 2.99 | 2.05 | 2.43 | 0.39 | 4.06 | 0.95 | 0.89 | 0.94 | 0.96 | 3.77 | 5.28 | 1.57 |
| Tmem40 | 1.00 | 0.65 | 1.00 | 1.00 | 1.00 | 1.00 | 1.00 | 1.22 | 1.00 | 3.78 | 6.62 | 1.29 |
| Tmem50a | 1.93 | 1.60 | 1.44 | 1.67 | 7.05 | 1.56 | 1.37 | 1.44 | 1.08 | 1.24 | 1.63 | 1.05 |
| Tmem56 | 0.85 | 1.46 | 1.01 | 5.59 | 0.83 | 2.81 | 1.00 | 1.00 | 1.00 | 0.66 | 0.90 | 1.41 |
| Tmem59l | 1.00 | 1.00 | 1.00 | 1.00 | 0.13 | 1.00 | 1.00 | 1.00 | 1.00 | 2.07 | 3.43 | 0.80 |
| Tmem82 | 1.11 | 1.10 | 1.00 | 0.49 | 3.11 | 0.84 | 0.55 | 0.58 | 0.43 | 3.22 | 4.41 | 1.22 |
| Tmem86b | 2.36 | 2.73 | 2.17 | 0.92 | 1.54 | 2.04 | 1.18 | 1.71 | 1.41 | 1.17 | 1.03 | 1.31 |
| Tmem88 | 1.11 | 0.58 | 0.97 | 0.87 | 5.47 | 1.32 | 0.96 | 0.92 | 0.81 | 0.86 | 1.29 | 0.74 |
| Tmod1 | 1.14 | 1.30 | 1.06 | 2.53 | 5.94 | 1.20 | 0.96 | 1.10 | 0.85 | 1.34 | 1.50 | 1.18 |
| Tmod2 | 1.00 | 1.00 | 1.00 | 1.00 | 0.26 | 1.00 | 0.98 | 0.94 | 1.14 | 1.15 | 0.73 | 0.94 |
| Tmod4 | 0.95 | 0.76 | 0.80 | 0.98 | 1.81 | 1.03 | 0.56 | 0.44 | 0.48 | 1.00 | 1.00 | 1.00 |
| Tmprss2 | 1.00 | 1.00 | 1.00 | 1.00 | 1.00 | 1.00 | 1.00 | 1.00 | 1.00 | 1.23 | 1.27 | 1.33 |
| Tmsb10 | 0.98 | 0.42 | 0.78 | 0.31 | 3.15 | 0.73 | 0.68 | 0.57 | 0.89 | 1.38 | 2.22 | 0.70 |
| Tmsb15b1 | 1.00 | 0.44 | 1.00 | 1.00 | 1.00 | 1.00 | 1.00 | 1.00 | 1.00 | 1.62 | 0.95 | 0.71 |
| Tmsb15b2 | 1.00 | 1.14 | 1.00 | 1.00 | 1.00 | 1.00 | 1.00 | 1.00 | 1.00 | 2.25 | 1.09 | 1.00 |
| Tmsb4x | 1.21 | 0.70 | 0.98 | 1.07 | 5.87 | 1.11 | 0.89 | 0.89 | 1.04 | 1.11 | 1.71 | 0.92 |
| Tmub1 | 1.29 | 0.82 | 0.93 | 0.57 | 3.19 | 0.96 | 0.86 | 0.92 | 0.87 | 2.49 | 2.65 | 1.07 |
| Tnfrsf1b | 2.66 | 1.82 | 1.64 | 11.69 | 15.84 | 8.36 | 1.28 | 1.32 | 1.63 | 1.29 | 0.93 | 0.90 |
| Tnfsf13 | 1.07 | 0.62 | 1.18 | 1.36 | 4.51 | 1.20 | 1.06 | 1.76 | 0.96 | 1.30 | 1.77 | 0.89 |
| Tnmd | 0.53 | 0.77 | 0.50 | 1.00 | 1.00 | 1.00 | 1.00 | 1.00 | 1.00 | 1.00 | 1.00 | 1.00 |
| Tnnc1 | 2.21 | 0.57 | 2.42 | 0.91 | 4.46 | 0.85 | 0.90 | 0.84 | 0.85 | 3.66 | 6.58 | 0.94 |
| Tnnc2 | 1.27 | 0.52 | 0.83 | 0.67 | 17.40 | 1.11 | 0.15 | 0.74 | 1.52 | 2.90 | 1.70 | 1.00 |
| Tnni1 | 2.02 | 0.43 | 1.55 | 1.00 | 1.29 | 0.74 | 0.81 | 1.00 | 1.30 | 1.00 | 1.00 | 1.00 |
| Tnni2 | 1.40 | 0.65 | 0.96 | 0.77 | 15.47 | 1.11 | 0.17 | 1.04 | 0.65 | 2.41 | 2.58 | 1.10 |

Fig. 35- 274

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Tgif1 | 1.23 | 1.23 | 1.12 | 1.45 | 2.05 | 1.10 | 2.08 | 0.97 | 1.51 | 1.03 | 1.00 | 1.20 |
| Tgoln2 | 1.00 | 1.00 | 1.00 | 10.35 | 0.45 | 2.65 | 0.92 | 2.94 | 1.49 | 29.80 | 1.00 | 1.00 |
| Tgtp1 | 1.65 | 1.27 | 1.77 | 3.69 | 1.69 | 1.33 | 1.78 | 1.00 | 1.05 | 1.86 | 0.53 | 1.22 |
| Tgtp2 | 1.87 | 1.33 | 1.84 | 3.50 | 1.64 | 1.66 | 1.47 | 1.00 | 1.36 | 1.23 | 0.46 | 1.40 |
| Thap3 | 1.55 | 1.71 | 1.00 | 0.85 | 0.79 | 0.93 | 1.29 | 0.90 | 1.06 | 1.07 | 1.83 | 1.07 |
| Thap7 | 1.07 | 1.33 | 0.93 | 1.04 | 0.73 | 1.18 | 1.20 | 1.69 | 1.08 | 1.06 | 1.58 | 1.15 |
| Thbs1 | 1.79 | 1.16 | 1.14 | 0.77 | 1.00 | 0.87 | 1.00 | 1.00 | 1.00 | 1.30 | 1.02 | 1.32 |
| Thrsp | 0.37 | 0.46 | 0.15 | 1.15 | 1.23 | 1.05 | 0.19 | 0.34 | 0.11 | 1.30 | 1.49 | 0.99 |
| Tigit | 7.72 | 3.91 | 2.57 | 1.00 | 1.00 | 1.00 | 1.00 | 1.00 | 1.00 | 0.62 | 1.04 | 0.91 |
| Timm10b | 0.88 | 1.01 | 0.82 | 0.73 | 0.59 | 0.98 | 0.84 | 1.14 | 0.80 | 0.86 | 1.31 | 0.84 |
| Timm13 | 1.03 | 1.41 | 0.93 | 0.78 | 0.49 | 0.90 | 0.85 | 2.78 | 0.93 | 0.90 | 1.70 | 0.97 |
| Timm44 | 1.19 | 1.26 | 0.94 | 0.74 | 0.95 | 0.91 | 0.76 | 0.86 | 0.76 | 1.07 | 1.39 | 0.92 |
| Timm50 | 0.69 | 1.05 | 0.73 | 1.07 | 0.68 | 1.12 | 1.04 | 2.39 | 1.06 | 1.25 | 1.46 | 1.03 |
| Timp1 | 0.65 | 0.75 | 1.86 | 1.00 | 0.35 | 1.00 | 1.00 | 1.00 | 1.00 | 1.00 | 1.37 | 1.09 |
| Tlcd2 | 1.12 | 1.77 | 0.99 | 1.35 | 1.09 | 1.22 | 1.14 | 1.73 | 1.02 | 1.21 | 1.44 | 0.91 |
| Tma16 | 0.87 | 1.01 | 1.07 | 0.96 | 1.03 | 1.23 | 1.43 | 1.51 | 1.20 | 0.98 | 1.30 | 1.10 |
| Tmc6 | 0.82 | 0.88 | 0.91 | 1.28 | 0.63 | 1.12 | 0.68 | 2.15 | 0.95 | 1.16 | 1.37 | 0.99 |
| Tmco2 | 1.00 | 1.00 | 1.00 | 1.00 | 1.00 | 1.00 | 1.00 | 1.00 | 1.00 | 1.00 | 1.00 | 1.00 |
| Tmed3 | 1.47 | 1.63 | 1.15 | 0.97 | 0.60 | 0.97 | 1.29 | 4.30 | 1.39 | 1.03 | 1.48 | 1.00 |
| Tmem107 | 1.46 | 1.07 | 0.91 | 0.59 | 0.52 | 0.64 | 1.00 | 1.00 | 1.00 | 0.85 | 1.33 | 1.14 |
| Tmem120a | 1.40 | 1.87 | 1.07 | 0.83 | 0.46 | 0.98 | 1.71 | 4.29 | 1.85 | 0.90 | 1.84 | 0.99 |
| Tmem130 | 1.00 | 1.00 | 1.00 | 1.00 | 1.00 | 1.00 | 1.00 | 1.00 | 1.00 | 1.51 | 1.36 | 1.29 |
| Tmem140 | 2.17 | 2.37 | 1.96 | 1.48 | 20.90 | 1.67 | 1.29 | 0.34 | 1.27 | 1.10 | 1.12 | 0.93 |
| Tmem141 | 2.85 | 2.22 | 1.27 | 0.75 | 0.47 | 0.74 | 0.81 | 1.41 | 0.56 | 1.10 | 1.37 | 1.40 |
| Tmem147 | 1.02 | 1.53 | 0.82 | 0.82 | 0.67 | 1.02 | 0.89 | 1.60 | 0.82 | 1.10 | 1.57 | 0.96 |
| Tmem14c | 1.19 | 1.49 | 0.86 | 0.95 | 0.95 | 0.92 | 0.79 | 0.74 | 0.67 | 1.05 | 1.68 | 1.01 |
| Tmem151a | 0.89 | 1.00 | 0.94 | 0.88 | 0.73 | 0.82 | 1.00 | 1.00 | 1.00 | 1.09 | 1.86 | 1.05 |
| Tmem160 | 1.09 | 1.94 | 1.17 | 1.09 | 0.61 | 0.99 | 0.76 | 1.99 | 0.90 | 0.90 | 1.86 | 1.05 |
| Tmem167b | 1.00 | 1.03 | 1.01 | 1.59 | 7.77 | 1.54 | 1.12 | 16.30 | 1.15 | 0.99 | 1.23 | 0.98 |
| Tmem179 | 1.00 | 1.00 | 1.00 | 1.00 | 1.00 | 1.00 | 1.00 | 1.00 | 1.00 | 1.13 | 1.58 | 1.08 |
| Tmem179b | 1.05 | 1.52 | 1.09 | 1.13 | 1.12 | 0.84 | 1.18 | 0.79 | 1.12 | 1.13 | 1.65 | 0.99 |
| Tmem198b | 0.97 | 1.22 | 1.08 | 0.83 | 0.78 | 1.03 | 0.82 | 0.34 | 0.60 | 1.06 | 0.95 | 0.97 |
| Tmem205 | 2.51 | 3.14 | 1.17 | 1.24 | 0.84 | 1.15 | 1.06 | 1.61 | 1.04 | 1.10 | 1.99 | 1.02 |
| Tmem208 | 1.21 | 1.68 | 1.05 | 0.78 | 0.78 | 1.08 | 0.97 | 1.11 | 1.38 | 1.08 | 1.84 | 1.13 |
| Tmem25 | 1.00 | 1.00 | 1.00 | 0.61 | 0.80 | 0.80 | 0.59 | 0.40 | 0.74 | 0.76 | 0.76 | 0.96 |
| Tmem252 | 4.44 | 7.40 | 3.11 | 4.99 | 7.10 | 2.14 | 1.00 | 1.00 | 1.00 | 4.47 | 1.85 | 6.38 |
| Tmem254c | 6.14 | 2.24 | 1.26 | 2.21 | 1.00 | 1.62 | 0.96 | 1.00 | 0.11 | 7.74 | 0.14 | 0.39 |
| Tmem256 | 0.95 | 1.22 | 0.78 | 0.80 | 0.52 | 0.75 | 0.62 | 1.62 | 0.72 | 1.55 | 1.53 | 1.81 |
| Tmem258 | 0.95 | 1.14 | 0.97 | 0.83 | 1.14 | 0.80 | 1.08 | 0.33 | 0.68 | 0.89 | 2.06 | 1.01 |
| Tmem259 | 1.03 | 1.38 | 0.97 | 0.99 | 0.85 | 1.24 | 1.22 | 1.39 | 1.15 | 1.03 | 1.32 | 1.05 |
| Tmem37 | 3.62 | 3.46 | 1.78 | 2.49 | 1.68 | 1.61 | 1.02 | 1.50 | 0.82 | 1.13 | 1.69 | 1.06 |
| Tmem40 | 1.20 | 3.19 | 0.98 | 1.00 | 0.42 | 1.00 | 1.00 | 1.00 | 1.00 | 1.00 | 1.37 | 1.39 |
| Tmem50a | 1.51 | 1.80 | 1.13 | 1.22 | 1.36 | 1.22 | 0.65 | 0.69 | 0.53 | 1.19 | 1.71 | 1.27 |
| Tmem56 | 1.00 | 1.00 | 1.00 | 1.58 | 1.93 | 1.34 | 2.00 | 0.97 | 1.88 | 0.97 | 0.57 | 0.95 |
| Tmem59l | 1.00 | 1.00 | 1.00 | 1.00 | 1.00 | 1.00 | 1.00 | 1.00 | 1.00 | 1.00 | 2.03 | 1.36 |
| Tmem82 | 1.00 | 1.14 | 1.00 | 0.90 | 0.53 | 0.94 | 1.53 | 3.68 | 1.37 | 0.88 | 1.33 | 1.15 |
| Tmem86b | 1.70 | 1.37 | 1.45 | 1.31 | 1.13 | 1.08 | 1.07 | 1.77 | 0.73 | 1.51 | 1.40 | 1.87 |
| Tmem88 | 2.49 | 2.02 | 1.19 | 0.69 | 0.66 | 0.87 | 0.62 | 1.03 | 0.83 | 0.74 | 1.90 | 1.18 |
| Tmod1 | 2.32 | 2.04 | 1.64 | 1.16 | 0.48 | 1.07 | 1.00 | 2.60 | 1.00 | 1.17 | 1.81 | 0.99 |
| Tmod2 | 1.00 | 1.00 | 1.00 | 1.00 | 1.00 | 1.00 | 1.00 | 1.00 | 1.00 | 1.12 | 0.76 | 1.06 |
| Tmod4 | 1.00 | 1.00 | 1.00 | 1.00 | 1.00 | 1.00 | 1.00 | 1.00 | 1.00 | 1.00 | 1.00 | 1.00 |
| Tmprss2 | 2.74 | 1.74 | 1.93 | 1.25 | 1.53 | 1.08 | 6.32 | 6.10 | 3.43 | 1.07 | 1.15 | 1.07 |
| Tmsb10 | 0.91 | 1.46 | 1.02 | 0.61 | 0.55 | 0.91 | 1.39 | 0.94 | 1.66 | 1.07 | 1.73 | 1.02 |
| Tmsb15b1 | 2.24 | 1.64 | 1.11 | 1.45 | 0.56 | 0.59 | 1.00 | 2.97 | 1.00 | 0.78 | 2.26 | 1.09 |
| Tmsb15b2 | 2.85 | 0.42 | 1.00 | 1.63 | 0.95 | 1.00 | 1.00 | 1.00 | 1.00 | 1.00 | 0.42 | 1.00 |
| Tmsb4x | 1.24 | 1.30 | 1.11 | 0.87 | 0.82 | 0.91 | 0.74 | 0.81 | 0.75 | 0.84 | 1.35 | 0.95 |
| Tmub1 | 1.11 | 1.35 | 1.11 | 0.82 | 0.61 | 0.97 | 1.00 | 2.20 | 0.99 | 1.17 | 1.45 | 1.06 |
| Tnfrsf1b | 1.15 | 1.12 | 1.54 | 1.90 | 1.25 | 0.97 | 2.54 | 3.64 | 1.45 | 1.23 | 1.17 | 1.06 |
| Tnfsf13 | 2.79 | 2.22 | 1.99 | 0.90 | 0.79 | 1.00 | 1.35 | 1.09 | 1.04 | 1.08 | 1.10 | 0.90 |
| Tnmd | 1.00 | 6.90 | 1.00 | 1.00 | 1.00 | 1.00 | 1.00 | 1.00 | 1.00 | 1.00 | 1.00 | 1.00 |
| Tnnc1 | 1.00 | 1.00 | 1.00 | 0.64 | 0.50 | 0.83 | 1.00 | 1.52 | 1.00 | 1.00 | 1.00 | 1.00 |
| Tnnc2 | 0.45 | 0.44 | 1.00 | 1.00 | 0.61 | 1.00 | 1.00 | 2.69 | 1.00 | 1.00 | 1.00 | 0.79 |
| Tnni1 | 1.00 | 1.00 | 0.87 | 1.00 | 1.00 | 1.00 | 1.00 | 1.00 | 1.00 | 0.67 | 1.21 | 0.97 |
| Tnni2 | 0.74 | 0.81 | 0.99 | 1.00 | 1.00 | 1.00 | 1.00 | 1.97 | 1.00 | 1.00 | 2.14 | 0.57 |

Fig. 35- 275

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Tgif1 | 1.15 | 1.12 | 1.10 | 1.51 | 0.60 | 1.20 | 1.00 | 0.43 | 0.92 | 1.27 | 1.40 | 1.36 |
| Tgoln2 | 0.95 | 1.32 | 0.07 | 1.00 | 9.35 | 1.00 | 1.63 | 3.52 | 4.54 | 1.00 | 1.00 | 1.00 |
| Tgtp1 | 3.07 | 1.03 | 2.59 | 1.46 | 0.72 | 1.34 | 1.00 | 1.00 | 1.00 | 1.00 | 0.59 | 0.73 |
| Tgtp2 | 3.47 | 1.51 | 3.20 | 1.19 | 1.00 | 1.35 | 1.00 | 1.00 | 1.00 | 1.08 | 0.61 | 0.77 |
| Thap3 | 1.22 | 1.26 | 1.38 | 1.10 | 1.83 | 1.12 | 0.74 | 1.90 | 1.21 | 1.05 | 1.46 | 1.03 |
| Thap7 | 0.97 | 1.17 | 1.20 | 1.10 | 3.18 | 1.12 | 0.82 | 1.65 | 1.01 | 1.05 | 1.30 | 0.91 |
| Thbs1 | 3.06 | 2.92 | 1.16 | 0.59 | 0.09 | 0.37 | 1.58 | 1.00 | 1.14 | 1.48 | 0.89 | 0.91 |
| Thrsp | 0.86 | 0.96 | 1.01 | 0.18 | 0.57 | 0.35 | 0.78 | 1.50 | 0.39 | 2.58 | 2.23 | 1.86 |
| Tigit | 1.47 | 1.00 | 1.00 | 1.00 | 1.00 | 1.67 | 1.00 | 1.00 | 1.00 | 1.20 | 0.94 | 0.91 |
| Timm10b | 0.79 | 0.77 | 0.88 | 0.70 | 1.49 | 0.71 | 0.85 | 1.89 | 0.94 | 0.91 | 0.97 | 0.90 |
| Timm13 | 0.99 | 0.93 | 0.82 | 0.97 | 1.73 | 1.05 | 0.97 | 4.72 | 1.00 | 0.99 | 1.41 | 0.85 |
| Timm44 | 0.92 | 1.11 | 0.98 | 0.83 | 5.36 | 1.01 | 0.91 | 0.81 | 1.02 | 1.06 | 1.15 | 1.01 |
| Timm50 | 0.75 | 1.07 | 0.97 | 0.88 | 1.95 | 0.91 | 0.94 | 2.59 | 1.08 | 1.08 | 1.15 | 0.75 |
| Timp1 | 1.09 | 0.63 | 0.42 | 1.70 | 2.35 | 1.47 | 0.76 | 2.54 | 0.53 | 0.70 | 1.43 | 0.56 |
| Tlcd2 | 0.80 | 0.82 | 0.84 | 0.72 | 3.20 | 0.71 | 0.97 | 1.86 | 0.89 | 0.85 | 1.22 | 1.00 |
| Tma16 | 1.71 | 0.91 | 0.95 | 3.03 | 8.64 | 2.36 | 1.05 | 1.08 | 0.91 | 1.32 | 1.57 | 0.73 |
| Tmc6 | 1.09 | 1.03 | 0.69 | 1.00 | 1.91 | 1.20 | 1.04 | 3.58 | 1.10 | 0.79 | 0.75 | 0.85 |
| Tmco2 | 1.00 | 1.00 | 1.00 | 5.21 | 1.53 | 1.00 | 0.85 | 1.38 | 1.00 | 1.00 | 1.00 | 1.00 |
| Tmed3 | 1.04 | 1.02 | 1.26 | 0.97 | 1.64 | 0.85 | 1.08 | 3.53 | 0.89 | 1.07 | 1.19 | 1.05 |
| Tmem107 | 0.93 | 0.73 | 0.93 | 1.04 | 2.08 | 1.37 | 1.14 | 1.80 | 0.99 | 1.20 | 1.27 | 0.52 |
| Tmem120a | 0.92 | 1.35 | 0.84 | 0.39 | 0.69 | 0.76 | 0.83 | 4.49 | 0.93 | 1.26 | 1.60 | 0.94 |
| Tmem130 | 1.19 | 0.99 | 1.76 | 1.00 | 1.00 | 1.00 | 1.04 | 0.85 | 0.89 | 1.00 | 11.19 | 1.00 |
| Tmem140 | 1.43 | 1.36 | 1.33 | 2.41 | 1.50 | 1.38 | 1.13 | 1.00 | 1.73 | 1.05 | 1.10 | 0.95 |
| Tmem141 | 0.89 | 0.97 | 1.05 | 0.68 | 0.53 | 0.65 | 0.68 | 2.39 | 0.77 | 0.73 | 1.12 | 0.62 |
| Tmem147 | 0.99 | 1.04 | 0.99 | 0.77 | 3.11 | 1.22 | 0.90 | 1.28 | 0.80 | 1.07 | 1.45 | 1.13 |
| Tmem14c | 0.94 | 1.07 | 0.90 | 0.82 | 5.33 | 1.01 | 0.91 | 0.81 | 0.96 | 0.73 | 1.02 | 0.69 |
| Tmem151a | 0.89 | 1.03 | 0.78 | 1.37 | 1.00 | 1.20 | 1.00 | 1.00 | 1.00 | 1.00 | 8.80 | 1.00 |
| Tmem160 | 1.20 | 1.55 | 1.41 | 0.74 | 1.94 | 0.67 | 1.67 | 4.45 | 0.43 | 1.09 | 1.20 | 0.87 |
| Tmem167b | 0.93 | 0.87 | 0.95 | 1.11 | 8.91 | 1.09 | 0.78 | 7.48 | 0.82 | 1.00 | 1.02 | 1.01 |
| Tmem179 | 1.43 | 1.00 | 1.25 | 0.04 | 0.24 | 0.19 | 1.11 | 2.43 | 0.94 | 1.00 | 7.72 | 1.00 |
| Tmem179b | 1.02 | 0.89 | 1.03 | 0.95 | 8.54 | 1.17 | 1.03 | 0.68 | 0.86 | 1.04 | 1.17 | 0.88 |
| Tmem198b | 1.15 | 1.11 | 1.18 | 0.95 | 3.03 | 1.04 | 0.92 | 0.83 | 0.96 | 1.07 | 1.17 | 0.98 |
| Tmem205 | 1.26 | 1.34 | 1.39 | 0.76 | 2.55 | 0.97 | 0.95 | 2.22 | 1.21 | 0.94 | 1.82 | 0.95 |
| Tmem208 | 1.00 | 0.98 | 1.13 | 1.52 | 19.46 | 1.10 | 1.20 | 1.46 | 0.99 | 0.98 | 1.11 | 0.90 |
| Tmem25 | 0.75 | 0.64 | 0.91 | 1.28 | 1.00 | 1.89 | 0.67 | 1.00 | 0.75 | 1.00 | 3.48 | 1.00 |
| Tmem252 | 5.51 | 4.88 | 4.12 | 2.82 | 1.00 | 2.55 | 1.00 | 1.00 | 1.00 | 1.53 | 1.00 | 1.00 |
| Tmem254c | 0.72 | 3.92 | 1.13 | 0.22 | 1.00 | 0.33 | 1.40 | 1.00 | 0.78 | 0.36 | 1.45 | 0.57 |
| Tmem256 | 0.86 | 0.84 | 1.26 | 0.65 | 3.50 | 0.71 | 0.51 | 2.41 | 0.78 | 1.06 | 1.08 | 0.62 |
| Tmem258 | 0.57 | 0.95 | 0.82 | 0.97 | 1.28 | 1.21 | 1.14 | 0.30 | 0.91 | 1.26 | 1.21 | 1.09 |
| Tmem259 | 1.07 | 1.41 | 1.15 | 1.06 | 2.84 | 1.11 | 1.01 | 1.93 | 1.09 | 0.89 | 1.21 | 0.95 |
| Tmem37 | 1.04 | 1.20 | 0.97 | 2.00 | 2.72 | 1.39 | 1.02 | 2.95 | 1.05 | 1.19 | 1.70 | 0.93 |
| Tmem40 | 0.99 | 0.95 | 1.16 | 1.00 | 2.33 | 1.00 | 1.00 | 2.00 | 1.00 | 1.58 | 1.70 | 0.69 |
| Tmem50a | 1.21 | 1.31 | 1.32 | 1.44 | 3.49 | 1.23 | 0.88 | 0.96 | 1.09 | 1.30 | 1.57 | 1.13 |
| Tmem56 | 0.95 | 0.87 | 0.88 | 0.77 | 0.50 | 2.63 | 0.89 | 1.06 | 0.97 | 0.50 | 1.64 | 0.80 |
| Tmem59l | 1.00 | 1.13 | 1.06 | 1.00 | 1.00 | 1.00 | 1.02 | 1.49 | 0.97 | 1.00 | 11.64 | 1.00 |
| Tmem82 | 0.82 | 1.80 | 1.66 | 3.19 | 11.10 | 2.82 | 0.95 | 2.81 | 0.96 | 0.90 | 1.68 | 1.37 |
| Tmem86b | 1.55 | 1.72 | 1.40 | 2.74 | 1.63 | 3.17 | 1.58 | 1.64 | 1.36 | 0.74 | 0.93 | 0.90 |
| Tmem88 | 1.27 | 1.21 | 1.47 | 0.98 | 3.49 | 1.13 | 0.69 | 2.04 | 1.21 | 0.91 | 1.07 | 0.69 |
| Tmod1 | 1.82 | 1.45 | 1.95 | 1.14 | 2.80 | 1.60 | 0.91 | 1.73 | 0.97 | 0.48 | 0.87 | 0.28 |
| Tmod2 | 1.09 | 1.19 | 1.11 | 0.86 | 1.00 | 0.79 | 1.18 | 0.81 | 0.98 | 1.00 | 6.86 | 1.00 |
| Tmod4 | 1.00 | 1.00 | 1.00 | 1.00 | 1.00 | 1.00 | 0.68 | 0.97 | 1.42 | 1.00 | 1.00 | 1.00 |
| Tmprss2 | 1.04 | 1.22 | 1.04 | 1.16 | 1.00 | 1.40 | 1.00 | 1.00 | 1.00 | 1.00 | 1.00 | 1.00 |
| Tmsb10 | 0.66 | 0.64 | 0.59 | 0.71 | 1.35 | 0.54 | 0.89 | 0.97 | 1.01 | 0.70 | 0.99 | 0.82 |
| Tmsb15b1 | 1.00 | 1.00 | 1.00 | 0.46 | 0.46 | 0.47 | 0.65 | 1.31 | 1.02 | 2.23 | 2.20 | 0.84 |
| Tmsb15b2 | 1.31 | 1.00 | 1.00 | 0.98 | 1.00 | 0.91 | 0.73 | 1.05 | 0.93 | 1.65 | 2.43 | 1.07 |
| Tmsb4x | 0.80 | 0.82 | 0.77 | 0.87 | 2.48 | 0.86 | 0.84 | 0.99 | 0.87 | 0.91 | 0.99 | 0.88 |
| Tmub1 | 0.88 | 1.30 | 1.14 | 1.00 | 1.20 | 1.07 | 1.08 | 2.35 | 1.03 | 1.04 | 1.27 | 1.02 |
| Tnfrsf1b | 0.78 | 0.78 | 0.72 | 2.30 | 2.71 | 1.18 | 1.00 | 1.00 | 0.83 | 0.87 | 0.72 | 0.85 |
| Tnfsf13 | 0.93 | 1.16 | 1.72 | 0.90 | 4.86 | 0.97 | 0.74 | 1.28 | 1.03 | 0.92 | 1.08 | 0.89 |
| Tnmd | 1.00 | 1.00 | 1.00 | 0.93 | 1.00 | 1.00 | 1.00 | 1.00 | 1.00 | 1.00 | 1.00 | 1.00 |
| Tnnc1 | 1.00 | 1.00 | 1.00 | 1.00 | 1.00 | 0.94 | 1.00 | 1.00 | 1.00 | 1.00 | 1.00 | 1.00 |
| Tnnc2 | 4.12 | 2.37 | 2.87 | 1.00 | 0.38 | 0.66 | 1.00 | 4.99 | 0.86 | 1.00 | 1.00 | 1.00 |
| Tnni1 | 0.67 | 0.62 | 0.62 | 1.00 | 1.00 | 1.00 | 1.00 | 0.78 | 1.00 | 1.00 | 1.00 | 1.00 |
| Tnni2 | 1.13 | 1.10 | 1.52 | 1.00 | 3.93 | 1.00 | 1.00 | 1.00 | 1.00 | 1.04 | 1.06 | 0.69 |

Fig. 35- 276

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Tgif1 | 1.24 | 1.89 | 1.30 | 1.06 | 1.00 | 0.96 | 1.06 | 0.46 | 1.07 | 0.62 | 1.43 | 1.30 |
| Tgoln2 | 3.94 | 1.28 | 1.25 | 0.31 | 1.54 | 1.00 | 1.00 | 9.81 | 1.00 | 1.00 | 1.00 | 1.00 |
| Tgtp1 | 1.00 | 1.00 | 1.00 | 1.00 | 1.00 | 1.00 | 1.00 | 1.00 | 1.00 | 1.19 | 1.53 | 1.32 |
| Tgtp2 | 1.00 | 1.00 | 1.00 | 1.00 | 1.00 | 1.00 | 1.00 | 1.00 | 1.07 | 1.06 | 1.25 | 1.31 |
| Thap3 | 1.23 | 1.27 | 0.88 | 1.24 | 1.44 | 0.92 | 1.37 | 6.84 | 1.13 | 3.41 | 1.56 | 1.35 |
| Thap7 | 1.30 | 1.09 | 0.73 | 1.34 | 1.43 | 1.03 | 1.12 | 5.56 | 0.92 | 2.17 | 1.24 | 1.14 |
| Thbs1 | 2.27 | 4.14 | 1.73 | 1.00 | 1.00 | 1.00 | 0.94 | 0.05 | 1.13 | 0.50 | 2.23 | 1.53 |
| Thrsp | 1.11 | 1.27 | 0.85 | 1.10 | 1.04 | 0.93 | 1.91 | 13.52 | 1.41 | 1.00 | 1.00 | 1.00 |
| Tigit | 1.00 | 1.00 | 1.00 | 1.00 | 1.00 | 1.00 | 1.00 | 1.00 | 1.00 | 1.00 | 2.47 | 1.24 |
| Timm10b | 0.98 | 0.80 | 1.12 | 0.84 | 0.74 | 0.90 | 0.99 | 8.51 | 0.86 | 2.18 | 0.97 | 1.21 |
| Timm13 | 0.86 | 1.07 | 0.97 | 1.07 | 0.82 | 1.04 | 1.26 | 27.16 | 0.95 | 3.76 | 1.01 | 1.11 |
| Timm44 | 0.91 | 0.80 | 0.94 | 0.95 | 0.76 | 1.05 | 1.11 | 2.16 | 1.06 | 1.72 | 1.06 | 0.95 |
| Timm50 | 1.38 | 0.95 | 0.93 | 1.12 | 0.78 | 1.08 | 1.26 | 9.47 | 0.82 | 1.98 | 0.85 | 0.89 |
| Timp1 | 1.00 | 1.00 | 1.00 | 1.00 | 0.68 | 1.00 | 1.46 | 36.63 | 1.09 | 1.00 | 1.00 | 1.00 |
| Tlcd2 | 1.00 | 1.44 | 1.00 | 1.00 | 0.90 | 1.00 | 1.58 | 8.44 | 1.17 | 2.83 | 1.19 | 1.42 |
| Tma16 | 0.82 | 0.72 | 0.83 | 1.67 | 3.94 | 1.56 | 0.88 | 1.01 | 0.84 | 1.37 | 0.95 | 1.10 |
| Tmc6 | 1.02 | 0.88 | 1.25 | 1.00 | 1.30 | 1.10 | 0.96 | 10.00 | 1.24 | 2.65 | 0.88 | 0.77 |
| Tmco2 | 1.00 | 1.00 | 1.00 | 1.00 | 1.00 | 1.00 | 1.93 | 1.00 | 1.00 | 1.00 | 1.00 | 1.00 |
| Tmed3 | 0.79 | 0.83 | 0.79 | 1.19 | 0.71 | 1.05 | 1.08 | 10.93 | 0.87 | 2.89 | 1.27 | 1.28 |
| Tmem107 | 1.00 | 1.00 | 1.00 | 1.21 | 0.79 | 1.03 | 1.05 | 5.97 | 0.62 | 1.66 | 1.08 | 1.17 |
| Tmem120a | 1.29 | 1.09 | 1.22 | 1.17 | 0.91 | 1.03 | 1.58 | 66.81 | 1.01 | 5.70 | 1.60 | 1.52 |
| Tmem130 | 1.00 | 1.00 | 1.00 | 1.14 | 1.28 | 1.06 | 1.00 | 1.00 | 1.00 | 1.00 | 1.00 | 1.00 |
| Tmem140 | 1.37 | 1.15 | 2.03 | 1.00 | 1.00 | 1.00 | 2.66 | 0.15 | 2.30 | 0.21 | 1.00 | 1.32 |
| Tmem141 | 1.00 | 0.75 | 0.80 | 1.08 | 0.72 | 1.09 | 0.67 | 13.72 | 0.64 | 3.34 | 0.85 | 1.17 |
| Tmem147 | 1.31 | 0.96 | 1.12 | 1.07 | 1.14 | 1.07 | 1.45 | 5.75 | 0.88 | 1.64 | 1.23 | 1.02 |
| Tmem14c | 1.20 | 1.06 | 0.68 | 1.22 | 1.11 | 1.08 | 1.06 | 3.53 | 0.95 | 1.18 | 0.93 | 0.96 |
| Tmem151a | 1.00 | 1.00 | 1.00 | 1.15 | 0.93 | 1.00 | 1.02 | 2.37 | 0.91 | 1.00 | 1.00 | 1.00 |
| Tmem160 | 1.02 | 1.45 | 0.96 | 0.95 | 0.89 | 1.04 | 1.34 | 20.56 | 1.01 | 5.44 | 1.56 | 1.20 |
| Tmem167b | 1.46 | 0.99 | 1.10 | 1.14 | 14.37 | 1.04 | 0.96 | 5.39 | 1.08 | 2.35 | 1.15 | 1.15 |
| Tmem179 | 1.00 | 1.00 | 1.00 | 1.10 | 1.08 | 1.04 | 0.94 | 0.86 | 0.88 | 1.00 | 1.00 | 1.00 |
| Tmem179b | 0.87 | 0.88 | 0.77 | 0.68 | 12.70 | 1.24 | 1.14 | 3.36 | 1.01 | 2.05 | 1.51 | 1.16 |
| Tmem198b | 0.61 | 0.69 | 0.82 | 0.71 | 0.84 | 0.93 | 1.07 | 2.02 | 0.96 | 1.69 | 1.69 | 1.44 |
| Tmem205 | 1.06 | 1.29 | 0.95 | 1.40 | 1.05 | 1.32 | 1.32 | 17.79 | 1.03 | 4.59 | 2.48 | 1.51 |
| Tmem208 | 0.89 | 0.66 | 1.05 | 1.24 | 0.42 | 1.09 | 0.97 | 4.11 | 0.91 | 2.21 | 1.08 | 1.07 |
| Tmem25 | 1.00 | 1.00 | 1.00 | 1.06 | 7.31 | 1.06 | 1.22 | 1.00 | 0.97 | 1.00 | 1.00 | 1.00 |
| Tmem252 | 1.00 | 1.00 | 1.00 | 1.64 | 1.00 | 1.31 | 3.88 | 0.81 | 4.94 | 1.00 | 1.00 | 1.00 |
| Tmem254c | 1.00 | 0.76 | 0.50 | 0.50 | 1.00 | 0.50 | 0.51 | 0.14 | 0.65 | 0.51 | 1.00 | 1.00 |
| Tmem256 | 0.68 | 1.51 | 2.25 | 1.19 | 0.90 | 1.49 | 1.46 | 18.53 | 0.93 | 3.54 | 1.34 | 1.61 |
| Tmem258 | 0.71 | 0.79 | 1.00 | 1.92 | 7.70 | 0.96 | 2.25 | 1.19 | 0.90 | 1.22 | 1.17 | 1.32 |
| Tmem259 | 1.23 | 1.09 | 1.01 | 1.08 | 1.08 | 1.08 | 1.31 | 5.82 | 1.01 | 2.13 | 1.24 | 1.02 |
| Tmem37 | 1.45 | 3.08 | 1.87 | 1.20 | 0.61 | 1.47 | 3.92 | 24.85 | 4.02 | 2.45 | 2.79 | 2.21 |
| Tmem40 | 1.00 | 1.00 | 1.00 | 2.52 | 22.86 | 3.01 | 0.90 | 14.78 | 0.66 | 6.39 | 2.12 | 2.38 |
| Tmem50a | 1.15 | 0.93 | 1.12 | 1.13 | 1.04 | 1.06 | 1.28 | 2.56 | 1.09 | 1.83 | 1.57 | 1.19 |
| Tmem56 | 1.60 | 1.11 | 0.81 | 0.99 | 0.56 | 1.00 | 1.40 | 0.77 | 1.51 | 0.42 | 0.51 | 0.61 |
| Tmem59l | 1.00 | 1.00 | 1.00 | 1.06 | 0.93 | 1.01 | 1.00 | 1.00 | 1.00 | 1.00 | 1.00 | 1.00 |
| Tmem82 | 1.00 | 1.00 | 1.08 | 1.00 | 1.29 | 1.00 | 2.59 | 11.97 | 2.33 | 1.28 | 1.00 | 1.00 |
| Tmem86b | 1.35 | 1.69 | 1.71 | 1.32 | 7.65 | 1.29 | 1.87 | 3.49 | 0.99 | 0.86 | 0.76 | 0.92 |
| Tmem88 | 1.00 | 1.00 | 1.26 | 1.55 | 0.61 | 0.79 | 1.21 | 1.89 | 1.35 | 1.00 | 1.00 | 1.00 |
| Tmod1 | 1.00 | 1.00 | 1.00 | 0.96 | 0.64 | 1.00 | 1.69 | 5.21 | 1.83 | 0.85 | 0.86 | 0.83 |
| Tmod2 | 1.00 | 1.00 | 1.00 | 0.91 | 0.80 | 0.95 | 1.02 | 0.79 | 1.51 | 1.00 | 1.00 | 1.00 |
| Tmod4 | 1.00 | 1.00 | 1.00 | 1.00 | 1.00 | 1.00 | 2.14 | 5.56 | 1.80 | 1.00 | 1.00 | 1.00 |
| Tmprss2 | 1.63 | 2.05 | 1.11 | 1.00 | 1.00 | 1.00 | 1.06 | 1.00 | 1.00 | 1.00 | 1.00 | 1.00 |
| Tmsb10 | 1.04 | 0.96 | 0.88 | 1.00 | 1.28 | 1.06 | 1.25 | 7.38 | 0.83 | 3.18 | 1.05 | 1.23 |
| Tmsb15b1 | 1.00 | 1.00 | 1.00 | 0.46 | 1.27 | 1.26 | 0.90 | 6.21 | 0.87 | 4.14 | 0.75 | 2.42 |
| Tmsb15b2 | 1.00 | 1.00 | 1.00 | 2.06 | 0.54 | 1.09 | 1.56 | 3.95 | 1.69 | 8.55 | 1.64 | 1.46 |
| Tmsb4x | 1.02 | 1.08 | 0.96 | 1.21 | 1.16 | 1.12 | 0.83 | 3.23 | 0.75 | 2.17 | 1.42 | 1.29 |
| Tmub1 | 1.09 | 1.06 | 1.12 | 1.12 | 0.99 | 0.99 | 1.54 | 8.14 | 1.00 | 2.53 | 1.47 | 1.41 |
| Tnfrsf1b | 1.00 | 1.00 | 1.00 | 0.76 | 1.00 | 1.01 | 1.32 | 1.74 | 1.67 | 1.29 | 1.03 | 1.02 |
| Tnfsf13 | 1.00 | 1.00 | 1.00 | 0.68 | 0.43 | 0.90 | 1.07 | 5.13 | 1.05 | 2.04 | 1.25 | 1.21 |
| Tnmd | 1.00 | 1.00 | 1.00 | 1.00 | 1.00 | 1.00 | 0.88 | 0.64 | 1.14 | 1.00 | 1.00 | 1.00 |
| Tnnc1 | 1.00 | 1.00 | 1.00 | 0.91 | 0.77 | 1.28 | 1.05 | 16.89 | 1.22 | 2.78 | 1.00 | 0.97 |
| Tnnc2 | 1.00 | 1.00 | 1.00 | 1.00 | 0.69 | 1.00 | 2.10 | 37.16 | 1.93 | 1.00 | 1.00 | 1.00 |
| Tnni1 | 1.00 | 1.00 | 1.00 | 1.00 | 0.20 | 1.00 | 1.31 | 8.21 | 0.96 | 1.00 | 1.00 | 1.00 |
| Tnni2 | 1.00 | 1.00 | 1.00 | 1.00 | 0.99 | 1.00 | 1.90 | 30.77 | 2.03 | 3.17 | 1.30 | 1.97 |

Fig. 35- 277

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Tnni3 | 1.00 | 0.84 | 1.00 | 1.00 | 1.81 | 1.00 | 0.89 | 0.87 | 0.80 | 4.50 | 5.70 | 0.84 |
| Tnnt1 | 2.27 | 0.35 | 1.29 | 0.62 | 3.84 | 0.63 | 1.38 | 0.90 | 1.18 | 3.56 | 6.41 | 1.51 |
| Tnnt2 | 1.00 | 1.31 | 1.00 | 1.00 | 1.76 | 1.00 | 1.04 | 0.95 | 0.91 | 2.73 | 4.37 | 0.74 |
| Tnnt3 | 1.29 | 0.67 | 0.86 | 1.16 | 9.78 | 1.19 | 0.20 | 0.86 | 0.81 | 1.78 | 2.80 | 1.00 |
| Tnp1 | 1.00 | 1.00 | 1.00 | 1.00 | 1.00 | 1.00 | 1.00 | 1.00 | 1.00 | 9.36 | 1.00 | 1.00 |
| Tnp2 | 1.00 | 1.69 | 1.00 | 1.00 | 1.00 | 1.00 | 1.45 | 1.17 | 1.00 | 19.82 | 1.53 | 1.00 |
| Tnxb | 0.87 | 0.56 | 1.18 | 0.62 | 2.29 | 0.81 | 0.78 | 0.87 | 1.11 | 1.59 | 1.86 | 0.67 |
| Tomm6 | 0.99 | 0.48 | 0.86 | 0.34 | 6.10 | 0.91 | 0.69 | 0.61 | 0.77 | 1.71 | 2.26 | 0.69 |
| Top1mt | 1.30 | 0.43 | 0.72 | 0.64 | 5.72 | 1.44 | 1.03 | 0.95 | 1.05 | 4.00 | 2.99 | 0.80 |
| Toporsos | 1.53 | 0.67 | 0.93 | 0.39 | 9.32 | 1.47 | 1.04 | 0.65 | 0.90 | 1.51 | 2.84 | 1.11 |
| Tpd52l1 | 0.75 | 0.86 | 0.66 | 0.97 | 1.69 | 0.99 | 1.04 | 1.16 | 1.29 | 0.80 | 0.80 | 0.93 |
| Tpgs1 | 1.31 | 0.71 | 0.75 | 0.26 | 4.81 | 0.94 | 1.45 | 0.92 | 1.00 | 1.70 | 2.99 | 1.05 |
| Tppp | 0.88 | 1.09 | 1.59 | 1.25 | 0.16 | 1.14 | 0.81 | 0.93 | 0.92 | 1.01 | 0.59 | 1.18 |
| Tppp3 | 1.69 | 1.19 | 1.02 | 1.57 | 6.60 | 2.16 | 0.97 | 0.83 | 1.07 | 0.93 | 1.78 | 1.02 |
| Tpsab1 | 2.20 | 0.70 | 0.80 | 0.91 | 1.09 | 1.33 | 1.00 | 1.00 | 1.00 | 1.00 | 1.00 | 1.00 |
| Tpsg1 | 1.00 | 1.00 | 1.00 | 1.00 | 1.00 | 1.00 | 1.00 | 1.00 | 1.00 | 1.00 | 1.00 | 1.00 |
| Tpt1 | 1.47 | 0.73 | 1.02 | 0.38 | 5.34 | 1.38 | 1.04 | 0.97 | 0.92 | 2.05 | 2.14 | 0.85 |
| Trafd1 | 1.72 | 1.55 | 1.46 | 2.79 | 7.48 | 2.58 | 2.03 | 1.80 | 1.31 | 0.77 | 1.37 | 1.21 |
| Trank1 | 1.00 | 1.00 | 1.00 | 1.00 | 0.31 | 1.00 | 1.00 | 1.00 | 1.00 | 1.00 | 1.00 | 1.00 |
| Trappc2l | 1.28 | 0.62 | 1.23 | 0.31 | 5.92 | 0.81 | 0.98 | 0.79 | 0.74 | 2.30 | 3.31 | 1.12 |
| Trappc6a | 1.59 | 0.53 | 0.98 | 0.54 | 18.25 | 1.11 | 0.76 | 0.55 | 0.54 | 2.29 | 3.91 | 0.87 |
| Trim12a | 3.56 | 3.89 | 3.42 | 5.12 | 8.33 | 3.54 | 8.41 | 8.17 | 7.71 | 28.65 | 25.81 | 20.77 |
| Trim29 | 1.00 | 1.00 | 1.00 | 1.00 | 1.00 | 1.00 | 1.00 | 1.00 | 1.00 | 1.24 | 5.13 | 2.00 |
| Trim30a | 1.43 | 1.00 | 2.13 | 3.97 | 1.50 | 2.00 | 2.21 | 2.03 | 2.24 | 2.48 | 1.01 | 1.85 |
| Trim30b | 1.00 | 1.00 | 1.00 | 1.00 | 1.00 | 1.00 | 1.00 | 1.00 | 1.00 | 2.72 | 2.74 | 1.81 |
| Trim30d | 1.00 | 1.00 | 1.00 | 1.01 | 1.00 | 1.00 | 1.32 | 1.62 | 2.02 | 1.00 | 1.05 | 6.43 |
| Trim34a | 2.06 | 1.08 | 2.25 | 5.06 | 1.00 | 4.36 | 6.38 | 5.80 | 4.76 | 3.58 | 4.56 | 9.27 |
| Trim54 | 1.46 | 1.24 | 1.19 | 1.74 | 4.80 | 1.71 | 1.04 | 0.93 | 1.01 | 2.16 | 2.39 | 0.69 |
| Trim63 | 2.53 | 2.21 | 3.90 | 34.59 | 45.14 | 10.65 | 3.96 | 4.76 | 1.50 | 9.12 | 5.48 | 1.47 |
| Trim9 | 1.00 | 1.00 | 1.00 | 1.00 | 0.27 | 1.00 | 1.00 | 1.00 | 1.00 | 1.00 | 1.00 | 1.00 |
| Trmt1 | 1.40 | 0.77 | 1.16 | 0.62 | 4.42 | 1.37 | 1.28 | 0.99 | 1.19 | 3.06 | 2.74 | 1.00 |
| Trmu | 1.06 | 0.49 | 0.95 | 0.46 | 6.46 | 1.06 | 0.93 | 0.92 | 0.81 | 2.54 | 3.53 | 0.82 |
| Trnau1ap | 0.72 | 0.54 | 1.05 | 0.54 | 9.17 | 1.29 | 0.89 | 0.78 | 0.78 | 2.81 | 3.65 | 0.88 |
| Trnp1 | 1.00 | 1.00 | 1.40 | 1.00 | 0.16 | 1.00 | 1.83 | 1.80 | 1.36 | 1.26 | 1.42 | 1.11 |
| Tro | 1.00 | 1.00 | 1.00 | 1.00 | 0.33 | 1.00 | 1.00 | 1.00 | 1.00 | 1.20 | 1.09 | 1.00 |
| Trp53inp1 | 3.00 | 5.69 | 2.40 | 13.60 | 4.14 | 5.11 | 2.82 | 4.16 | 1.82 | 1.32 | 0.98 | 1.73 |
| Trub2 | 0.71 | 0.52 | 0.77 | 0.54 | 3.45 | 1.01 | 0.90 | 1.09 | 0.98 | 2.63 | 2.67 | 0.96 |
| Try10 | 1.00 | 1.00 | 1.00 | 1.00 | 1.00 | 1.00 | 1.00 | 1.00 | 1.00 | 1.00 | 1.00 | 1.00 |
| Try4 | 1.00 | 1.00 | 1.00 | 1.00 | 1.00 | 1.00 | 1.00 | 1.00 | 1.00 | 1.00 | 1.00 | 5.02 |
| Try5 | 1.00 | 1.00 | 1.00 | 1.13 | 1.00 | 1.00 | 1.00 | 1.00 | 1.00 | 1.00 | 1.00 | 4.85 |
| Tsacc | 0.85 | 0.77 | 0.81 | 0.33 | 13.32 | 1.57 | 1.06 | 1.44 | 0.97 | 1.86 | 3.80 | 1.58 |
| Tsc2 | 1.00 | 0.58 | 0.97 | 0.82 | 4.16 | 0.90 | 1.14 | 0.99 | 0.91 | 2.14 | 3.29 | 0.90 |
| Tsc22d3 | 2.08 | 1.67 | 1.62 | 2.79 | 9.05 | 2.34 | 1.16 | 1.31 | 1.15 | 2.79 | 2.22 | 1.21 |
| Tspan11 | 1.00 | 1.00 | 1.00 | 1.00 | 1.00 | 1.00 | 1.00 | 1.00 | 1.00 | 3.09 | 3.72 | 1.40 |
| Tspan17 | 1.85 | 0.84 | 1.22 | 0.34 | 4.62 | 0.70 | 1.48 | 1.32 | 1.14 | 2.30 | 2.96 | 0.97 |
| Tspan2os | 1.00 | 1.00 | 1.00 | 1.00 | 1.00 | 1.00 | 1.00 | 1.00 | 1.00 | 7.84 | 7.49 | 1.00 |
| Tspan8 | 1.36 | 0.83 | 0.98 | 1.00 | 1.14 | 1.00 | 1.00 | 1.00 | 1.00 | 0.96 | 1.14 | 0.86 |
| Tspo | 1.85 | 1.24 | 1.35 | 0.48 | 5.38 | 1.06 | 1.08 | 0.83 | 1.16 | 1.16 | 1.92 | 1.00 |
| Tssc1 | 0.91 | 0.87 | 1.17 | 0.42 | 1.67 | 0.69 | 1.16 | 1.08 | 1.22 | 1.61 | 1.65 | 1.12 |
| Tssc4 | 1.15 | 0.89 | 0.85 | 0.39 | 3.93 | 1.07 | 0.97 | 0.81 | 0.99 | 2.12 | 2.20 | 1.13 |
| Tsta3 | 1.11 | 0.62 | 0.77 | 0.24 | 8.20 | 0.98 | 1.21 | 0.84 | 1.08 | 2.69 | 3.88 | 1.25 |
| Ttc27 | 1.19 | 0.67 | 1.14 | 0.70 | 3.39 | 0.85 | 0.76 | 1.19 | 0.81 | 1.90 | 2.66 | 0.78 |
| Ttc36 | 1.00 | 0.38 | 1.00 | 0.63 | 13.81 | 0.63 | 1.00 | 0.99 | 1.00 | 4.16 | 7.47 | 1.11 |
| Ttc39c | 1.65 | 1.09 | 1.41 | 1.00 | 2.90 | 1.00 | 1.52 | 1.16 | 1.11 | 3.09 | 6.96 | 2.20 |
| Ttc9b | 1.00 | 1.00 | 1.00 | 1.00 | 0.29 | 1.00 | 1.00 | 1.00 | 1.00 | 1.00 | 1.00 | 1.00 |
| Ttll7 | 2.29 | 5.55 | 2.24 | 2.40 | 0.34 | 2.00 | 2.52 | 3.81 | 3.08 | 1.00 | 0.56 | 2.23 |
| Ttr | 1.00 | 0.87 | 1.00 | 1.00 | 0.06 | 0.81 | 3.36 | 0.42 | 2.07 | 0.15 | 1.00 | 1.00 |
| Ttyh1 | 1.77 | 1.88 | 2.22 | 1.41 | 0.13 | 0.92 | 0.86 | 1.02 | 1.00 | 1.00 | 1.24 | 1.00 |
| Tub | 1.00 | 1.00 | 1.00 | 1.00 | 0.33 | 1.00 | 1.00 | 1.00 | 1.00 | 1.00 | 1.00 | 1.00 |
| Tuba3a | 1.00 | 1.00 | 1.00 | 1.00 | 1.00 | 1.00 | 1.00 | 1.00 | 1.00 | 1.00 | 1.00 | 1.00 |
| Tuba3b | 1.00 | 1.00 | 1.00 | 1.00 | 1.00 | 1.00 | 1.00 | 1.00 | 1.00 | 1.12 | 1.00 | 1.00 |
| Tuba8 | 0.94 | 0.71 | 0.77 | 0.41 | 1.91 | 0.67 | 0.71 | 0.83 | 0.84 | 2.01 | 2.61 | 1.12 |
| Tubb2a | 2.04 | 2.01 | 1.27 | 0.80 | 0.49 | 1.50 | 1.62 | 1.44 | 1.60 | 0.47 | 0.53 | 0.81 |
| Tubb2a-ps2 | 2.09 | 1.00 | 1.00 | 2.24 | 0.19 | 1.04 | 1.25 | 2.48 | 2.23 | 1.00 | 0.49 | 1.20 |

Fig. 35- 278

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Tnni3 | 1.50 | 1.44 | 1.26 | 1.00 | 1.00 | 1.00 | 1.00 | 1.00 | 1.00 | 1.00 | 1.00 | 1.00 |
| Tnnt1 | 1.47 | 1.21 | 1.75 | 1.00 | 0.38 | 1.00 | 1.00 | 1.39 | 1.00 | 1.00 | 1.00 | 1.00 |
| Tnnt2 | 0.85 | 0.59 | 0.83 | 1.00 | 1.00 | 1.00 | 1.00 | 0.95 | 1.00 | 0.86 | 1.18 | 0.61 |
| Tnnt3 | 0.64 | 0.73 | 1.07 | 1.00 | 1.00 | 1.00 | 1.00 | 1.00 | 1.00 | 1.00 | 1.00 | 0.34 |
| Tnp1 | 1.00 | 1.00 | 1.00 | 1.04 | 2.57 | 1.94 | 0.74 | 8.80 | 0.53 | 1.00 | 1.00 | 0.45 |
| Tnp2 | 0.93 | 1.30 | 1.00 | 1.12 | 2.00 | 1.23 | 2.67 | 15.18 | 1.39 | 1.00 | 1.15 | 0.56 |
| Tnxb | 0.93 | 0.70 | 0.88 | 0.88 | 0.39 | 0.75 | 1.00 | 3.04 | 1.00 | 0.82 | 0.82 | 0.76 |
| Tomm6 | 0.84 | 1.09 | 0.79 | 0.80 | 0.53 | 0.73 | 0.76 | 1.20 | 0.72 | 0.82 | 1.29 | 0.81 |
| Top1mt | 1.45 | 1.13 | 1.21 | 1.01 | 0.54 | 0.86 | 0.74 | 1.42 | 1.08 | 1.02 | 1.05 | 0.99 |
| Toporsos | 1.10 | 1.68 | 1.08 | 0.77 | 0.67 | 1.06 | 0.71 | 1.13 | 1.02 | 1.77 | 1.83 | 0.95 |
| Tpd52l1 | 2.17 | 1.90 | 2.54 | 1.25 | 1.26 | 1.31 | 0.63 | 0.39 | 0.65 | 1.45 | 1.57 | 1.52 |
| Tpgs1 | 1.43 | 1.75 | 1.16 | 0.95 | 0.96 | 1.18 | 1.24 | 1.35 | 1.15 | 1.06 | 1.84 | 1.08 |
| Tppp | 0.87 | 0.66 | 0.95 | 0.72 | 1.00 | 0.88 | 0.51 | 1.00 | 0.65 | 1.09 | 0.66 | 1.19 |
| Tppp3 | 2.43 | 2.53 | 1.06 | 2.31 | 1.37 | 1.14 | 1.84 | 3.53 | 1.00 | 1.26 | 1.82 | 1.39 |
| Tpsab1 | 1.11 | 0.36 | 0.11 | 1.00 | 1.00 | 1.00 | 1.00 | 1.00 | 1.00 | 5.67 | 4.72 | 3.25 |
| Tpsg1 | 1.00 | 1.00 | 1.00 | 1.00 | 1.00 | 1.00 | 1.00 | 1.00 | 1.00 | 1.43 | 1.60 | 1.46 |
| Tpt1 | 1.42 | 1.63 | 1.15 | 1.17 | 0.85 | 1.12 | 1.17 | 1.62 | 1.10 | 1.04 | 1.55 | 1.08 |
| Trafd1 | 1.52 | 1.46 | 1.38 | 1.54 | 2.19 | 1.23 | 1.12 | 0.82 | 1.20 | 1.31 | 1.41 | 1.21 |
| Trank1 | 1.00 | 1.00 | 1.00 | 1.00 | 1.00 | 1.00 | 1.00 | 1.00 | 1.00 | 1.00 | 1.00 | 1.00 |
| Trappc2l | 1.33 | 1.32 | 1.20 | 0.93 | 0.55 | 0.89 | 1.38 | 1.87 | 0.79 | 1.29 | 1.68 | 1.16 |
| Trappc6a | 1.55 | 1.54 | 1.06 | 0.73 | 0.57 | 0.84 | 1.18 | 1.87 | 0.90 | 0.96 | 1.70 | 1.13 |
| Trim12a | 85.68 | 90.58 | 76.54 | 3.98 | 5.82 | 4.76 | 3.78 | 1.72 | 3.03 | 22.83 | 29.89 | 19.99 |
| Trim29 | 2.46 | 2.16 | 2.09 | 1.00 | 1.00 | 1.00 | 1.00 | 1.00 | 1.00 | 1.00 | 1.00 | 0.91 |
| Trim30a | 1.69 | 1.45 | 2.09 | 2.08 | 1.21 | 1.97 | 1.88 | 1.02 | 1.90 | 5.74 | 3.27 | 2.86 |
| Trim30b | 1.19 | 1.39 | 1.30 | 1.00 | 1.00 | 1.00 | 1.00 | 1.00 | 1.00 | 1.00 | 1.00 | 1.00 |
| Trim30d | 9.81 | 8.88 | 12.93 | 1.00 | 1.00 | 1.00 | 1.67 | 1.00 | 1.79 | 20.44 | 12.47 | 14.82 |
| Trim34a | 10.72 | 10.31 | 11.37 | 5.25 | 1.00 | 3.85 | 2.74 | 1.00 | 3.75 | 5.89 | 14.50 | 5.10 |
| Trim54 | 1.00 | 1.00 | 1.00 | 1.00 | 1.00 | 1.00 | 1.00 | 1.00 | 1.00 | 1.00 | 1.00 | 1.00 |
| Trim63 | 2.03 | 2.13 | 2.07 | 2.59 | 1.41 | 1.20 | 1.11 | 1.00 | 1.00 | 1.00 | 1.00 | 1.00 |
| Trim9 | 1.00 | 1.00 | 1.00 | 1.00 | 1.00 | 1.00 | 1.00 | 1.00 | 1.00 | 1.00 | 1.00 | 1.00 |
| Trmt1 | 1.14 | 1.32 | 1.20 | 1.06 | 0.70 | 1.00 | 1.39 | 3.19 | 1.21 | 1.06 | 1.24 | 0.84 |
| Trmu | 0.95 | 1.79 | 0.91 | 0.80 | 0.50 | 0.93 | 1.27 | 1.88 | 0.65 | 0.91 | 1.36 | 1.06 |
| Trnau1ap | 1.09 | 1.52 | 1.07 | 0.69 | 0.48 | 0.95 | 0.90 | 2.01 | 0.72 | 0.95 | 1.38 | 1.03 |
| Trnp1 | 4.44 | 3.81 | 1.94 | 1.00 | 1.00 | 0.96 | 1.00 | 1.00 | 1.00 | 1.22 | 1.48 | 1.22 |
| Tro | 1.00 | 1.00 | 1.00 | 1.00 | 1.00 | 1.00 | 1.00 | 1.00 | 1.00 | 1.00 | 1.00 | 1.00 |
| Trp53inp1 | 0.86 | 0.77 | 1.00 | 3.78 | 3.56 | 1.99 | 7.76 | 5.71 | 2.28 | 1.32 | 0.97 | 1.21 |
| Trub2 | 0.86 | 0.95 | 0.85 | 0.86 | 0.47 | 0.98 | 1.39 | 2.14 | 1.10 | 0.86 | 0.95 | 1.06 |
| Try10 | 1.00 | 1.00 | 1.00 | 1.00 | 1.00 | 1.00 | 1.00 | 1.00 | 1.00 | 1.10 | 8.45 | 11.68 |
| Try4 | 1.00 | 1.50 | 4.08 | 1.00 | 1.00 | 0.81 | 1.00 | 2.93 | 1.16 | 0.48 | 2.98 | 30.36 |
| Try5 | 1.00 | 1.06 | 1.39 | 1.00 | 0.92 | 1.23 | 1.00 | 2.37 | 0.61 | 0.43 | 2.54 | 25.54 |
| Tsacc | 1.68 | 1.10 | 0.89 | 1.29 | 0.45 | 0.74 | 0.69 | 1.25 | 0.82 | 1.77 | 2.46 | 1.19 |
| Tsc2 | 1.00 | 1.14 | 0.99 | 0.98 | 0.63 | 1.03 | 0.74 | 1.78 | 0.78 | 1.11 | 1.35 | 0.97 |
| Tsc22d3 | 2.57 | 3.69 | 2.55 | 1.62 | 1.23 | 1.37 | 1.58 | 3.21 | 1.31 | 1.53 | 2.15 | 1.56 |
| Tspan11 | 1.00 | 1.00 | 1.00 | 1.00 | 1.00 | 1.00 | 1.00 | 1.00 | 1.00 | 1.00 | 1.00 | 1.00 |
| Tspan17 | 1.60 | 1.74 | 1.43 | 1.41 | 0.80 | 1.12 | 1.00 | 3.43 | 1.86 | 1.13 | 1.62 | 1.15 |
| Tspan2os | 1.00 | 1.00 | 1.00 | 1.00 | 1.00 | 1.00 | 1.00 | 1.00 | 1.00 | 1.00 | 1.00 | 1.00 |
| Tspan8 | 1.19 | 1.00 | 1.20 | 0.81 | 0.96 | 0.85 | 1.00 | 1.00 | 1.00 | 1.20 | 1.67 | 1.23 |
| Tspo | 1.12 | 1.51 | 0.96 | 1.06 | 1.02 | 1.24 | 1.19 | 1.12 | 1.09 | 1.00 | 1.56 | 1.13 |
| Tssc1 | 3.09 | 6.07 | 2.57 | 1.23 | 1.18 | 0.84 | 1.11 | 1.10 | 0.81 | 1.07 | 1.55 | 1.17 |
| Tssc4 | 0.99 | 1.21 | 0.91 | 0.93 | 0.60 | 0.78 | 1.18 | 2.36 | 1.19 | 0.94 | 1.64 | 1.09 |
| Tsta3 | 1.21 | 1.38 | 1.06 | 0.90 | 0.72 | 0.82 | 1.13 | 1.98 | 1.10 | 1.09 | 1.98 | 1.17 |
| Ttc27 | 1.03 | 0.78 | 0.84 | 1.08 | 0.47 | 0.77 | 0.88 | 1.95 | 1.09 | 0.93 | 1.12 | 1.09 |
| Ttc36 | 2.08 | 0.89 | 0.90 | 0.83 | 0.53 | 0.89 | 0.68 | 1.38 | 0.76 | 0.62 | 1.66 | 0.46 |
| Ttc39c | 2.13 | 2.37 | 1.33 | 1.44 | 1.49 | 1.27 | 0.71 | 0.77 | 0.57 | 2.19 | 1.93 | 1.27 |
| Ttc9b | 1.00 | 1.00 | 1.00 | 1.00 | 1.00 | 1.00 | 1.00 | 1.00 | 1.00 | 1.00 | 1.00 | 1.00 |
| Ttll7 | 1.00 | 1.00 | 1.00 | 1.26 | 1.00 | 1.00 | 1.00 | 1.00 | 1.00 | 1.85 | 1.03 | 1.74 |
| Ttr | 3.07 | 1.37 | 0.65 | 1.11 | 0.98 | 1.20 | 0.52 | 0.49 | 0.43 | 0.55 | 1.20 | 0.89 |
| Ttyh1 | 0.74 | 1.13 | 1.18 | 1.00 | 1.00 | 1.00 | 1.00 | 1.00 | 1.00 | 1.29 | 1.34 | 1.16 |
| Tub | 1.00 | 1.00 | 1.00 | 1.00 | 1.00 | 1.00 | 1.00 | 1.00 | 1.00 | 1.00 | 1.00 | 0.99 |
| Tuba3a | 0.87 | 0.57 | 0.90 | 1.00 | 1.00 | 1.00 | 1.00 | 1.00 | 1.00 | 1.00 | 1.00 | 1.00 |
| Tuba3b | 1.00 | 1.00 | 1.00 | 1.00 | 1.00 | 1.00 | 1.00 | 1.00 | 1.00 | 1.00 | 1.00 | 1.00 |
| Tuba8 | 1.23 | 1.38 | 1.48 | 1.42 | 1.83 | 1.18 | 0.96 | 4.04 | 1.50 | 1.00 | 1.00 | 1.00 |
| Tubb2a | 0.72 | 0.83 | 0.63 | 1.03 | 1.39 | 0.90 | 4.01 | 1.27 | 6.58 | 1.17 | 1.17 | 1.00 |
| Tubb2a-ps2 | 0.49 | 0.56 | 0.75 | 1.33 | 0.89 | 0.63 | 1.71 | 1.00 | 5.63 | 1.04 | 0.86 | 1.27 |

Fig. 35- 279

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Tnni3 | 1.10 | 1.37 | 1.08 | 1.00 | 3.28 | 1.23 | 1.01 | 4.97 | 1.40 | 1.05 | 2.18 | 0.74 |
| Tnnt1 | 1.00 | 1.00 | 1.00 | 1.00 | 2.14 | 1.00 | 1.00 | 1.98 | 1.00 | 1.00 | 1.39 | 1.00 |
| Tnnt2 | 1.00 | 1.00 | 1.00 | 1.00 | 1.16 | 1.84 | 1.00 | 4.12 | 0.77 | 1.00 | 1.09 | 1.00 |
| Tnnt3 | 2.58 | 1.38 | 2.36 | 1.00 | 1.00 | 1.00 | 1.00 | 1.00 | 1.00 | 0.95 | 1.05 | 1.00 |
| Tnp1 | 0.70 | 1.00 | 1.46 | 4.28 | 36.39 | 1.35 | 0.75 | 1.16 | 0.90 | 2.72 | 0.80 | 1.78 |
| Tnp2 | 3.32 | 1.00 | 0.93 | 4.26 | 14.89 | 2.11 | 0.79 | 2.12 | 1.02 | 4.00 | 0.62 | 2.80 |
| Tnxb | 0.97 | 1.16 | 0.99 | 0.88 | 0.81 | 0.74 | 1.00 | 1.34 | 1.00 | 0.52 | 0.60 | 0.91 |
| Tomm6 | 0.81 | 0.82 | 0.91 | 0.81 | 2.73 | 0.92 | 0.73 | 1.63 | 0.73 | 0.83 | 1.02 | 0.73 |
| Top1mt | 0.90 | 1.05 | 0.87 | 0.79 | 1.36 | 1.29 | 0.96 | 5.42 | 1.31 | 1.35 | 1.07 | 1.05 |
| Toporsos | 1.34 | 1.12 | 1.54 | 0.71 | 1.57 | 0.83 | 1.24 | 1.33 | 0.85 | 0.96 | 1.42 | 1.05 |
| Tpd52l1 | 1.14 | 1.02 | 1.57 | 1.16 | 1.00 | 2.13 | 0.70 | 0.43 | 1.07 | 1.00 | 1.82 | 1.00 |
| Tpgs1 | 1.14 | 1.37 | 1.24 | 0.95 | 2.63 | 0.89 | 0.86 | 1.72 | 1.05 | 0.93 | 1.33 | 0.92 |
| Tppp | 1.58 | 1.69 | 1.27 | 0.69 | 0.52 | 0.84 | 1.08 | 1.00 | 0.89 | 0.73 | 5.57 | 0.97 |
| Tppp3 | 2.01 | 2.16 | 2.05 | 1.96 | 4.03 | 1.54 | 1.06 | 0.79 | 1.04 | 1.12 | 2.70 | 0.64 |
| Tpsab1 | 1.41 | 1.17 | 1.83 | 2.20 | 5.13 | 1.75 | 1.00 | 1.00 | 1.00 | 1.00 | 1.00 | 1.00 |
| Tpsg1 | 1.00 | 1.00 | 1.00 | 1.00 | 1.00 | 1.00 | 1.00 | 9.95 | 1.00 | 1.00 | 1.00 | 1.00 |
| Tpt1 | 1.09 | 1.26 | 1.17 | 1.25 | 4.62 | 1.26 | 0.93 | 1.37 | 0.88 | 1.23 | 1.41 | 1.14 |
| Trafd1 | 1.38 | 1.68 | 1.37 | 2.29 | 1.27 | 1.82 | 1.00 | 0.50 | 1.02 | 1.17 | 1.05 | 1.08 |
| Trank1 | 1.00 | 1.00 | 1.00 | 1.02 | 1.00 | 1.12 | 1.00 | 0.65 | 0.89 | 1.00 | 5.19 | 1.00 |
| Trappc2l | 0.82 | 1.13 | 1.06 | 0.94 | 2.83 | 0.97 | 0.71 | 2.13 | 1.13 | 1.14 | 1.40 | 1.13 |
| Trappc6a | 1.02 | 0.93 | 1.02 | 0.87 | 2.38 | 1.07 | 0.63 | 2.57 | 1.20 | 1.19 | 1.51 | 0.95 |
| Trim12a | 7.59 | 8.14 | 7.29 | 8.20 | 1.06 | 11.36 | 1.60 | 1.96 | 1.53 | 83.25 | 82.36 | 88.86 |
| Trim29 | 0.78 | 1.20 | 0.99 | 2.56 | 1.37 | 1.86 | 1.00 | 1.00 | 1.00 | 1.00 | 1.00 | 1.00 |
| Trim30a | 4.83 | 5.99 | 3.69 | 1.85 | 2.88 | 1.47 | 1.05 | 1.00 | 1.00 | 2.77 | 1.52 | 2.20 |
| Trim30b | 1.00 | 1.00 | 1.00 | 1.00 | 1.00 | 1.00 | 1.00 | 1.00 | 1.00 | 11.16 | 8.87 | 10.36 |
| Trim30d | 3.70 | 4.72 | 3.85 | 3.52 | 1.00 | 3.53 | 1.00 | 1.00 | 1.00 | 34.19 | 16.28 | 21.37 |
| Trim34a | 5.17 | 6.67 | 6.75 | 6.62 | 1.00 | 6.47 | 2.27 | 1.00 | 1.96 | 27.73 | 21.47 | 17.60 |
| Trim54 | 1.28 | 1.03 | 1.00 | 1.00 | 1.00 | 1.00 | 0.87 | 4.59 | 0.84 | 1.00 | 1.00 | 1.00 |
| Trim63 | 2.27 | 1.83 | 1.00 | 2.18 | 1.00 | 1.00 | 1.00 | 1.00 | 1.00 | 0.81 | 0.89 | 1.00 |
| Trim9 | 1.00 | 1.00 | 1.00 | 1.00 | 1.00 | 1.00 | 1.00 | 1.00 | 1.00 | 1.00 | 5.41 | 1.00 |
| Trmt1 | 0.98 | 1.14 | 1.01 | 1.25 | 1.55 | 1.28 | 1.01 | 3.00 | 1.25 | 1.08 | 1.39 | 1.15 |
| Trmu | 1.14 | 0.94 | 0.90 | 1.50 | 2.66 | 1.17 | 1.76 | 2.56 | 0.65 | 0.98 | 1.31 | 0.84 |
| Trnau1ap | 0.78 | 0.90 | 1.21 | 1.28 | 3.07 | 1.27 | 0.76 | 2.75 | 0.75 | 0.93 | 1.22 | 0.89 |
| Trnp1 | 1.08 | 1.68 | 1.99 | 0.62 | 1.24 | 0.99 | 1.00 | 1.00 | 0.99 | 3.72 | 12.27 | 2.51 |
| Tro | 1.00 | 1.00 | 1.00 | 1.00 | 1.00 | 1.00 | 1.00 | 1.00 | 1.11 | 1.00 | 5.41 | 1.00 |
| Trp53inp1 | 2.67 | 3.01 | 1.50 | 14.75 | 7.12 | 6.47 | 1.10 | 0.90 | 0.95 | 1.74 | 1.16 | 1.76 |
| Trub2 | 0.75 | 0.94 | 0.87 | 0.91 | 2.07 | 1.13 | 0.87 | 2.69 | 1.06 | 0.98 | 0.91 | 0.93 |
| Try10 | 1.60 | 2.27 | 2.59 | 1.00 | 1.00 | 1.00 | 1.00 | 1.00 | 1.00 | 1.00 | 5.95 | 1.00 |
| Try4 | 4.07 | 2.12 | 2.31 | 1.00 | 1.00 | 0.85 | 0.77 | 2.12 | 0.99 | 2.93 | 13.17 | 0.71 |
| Try5 | 6.20 | 1.86 | 1.93 | 1.00 | 1.00 | 0.66 | 1.04 | 2.39 | 1.06 | 3.17 | 15.01 | 0.64 |
| Tsacc | 0.93 | 1.70 | 0.91 | 1.54 | 1.58 | 0.84 | 1.00 | 2.09 | 0.89 | 1.39 | 1.48 | 1.52 |
| Tsc2 | 1.16 | 1.06 | 1.06 | 0.78 | 2.82 | 0.91 | 1.14 | 2.03 | 1.16 | 1.02 | 1.27 | 0.93 |
| Tsc22d3 | 2.09 | 2.62 | 1.88 | 2.85 | 5.60 | 1.85 | 1.41 | 3.04 | 1.14 | 1.90 | 2.46 | 1.97 |
| Tspan11 | 1.00 | 1.00 | 1.00 | 0.73 | 0.86 | 1.39 | 1.00 | 1.00 | 1.00 | 1.00 | 1.00 | 1.00 |
| Tspan17 | 1.10 | 1.26 | 1.16 | 0.58 | 1.13 | 0.40 | 0.81 | 1.90 | 0.89 | 1.13 | 1.67 | 1.05 |
| Tspan2os | 1.00 | 1.00 | 1.00 | 1.00 | 1.00 | 1.00 | 1.00 | 1.00 | 1.00 | 1.00 | 1.00 | 1.00 |
| Tspan8 | 0.89 | 0.89 | 0.85 | 1.00 | 1.00 | 1.00 | 1.00 | 1.57 | 1.00 | 0.35 | 0.49 | 0.57 |
| Tspo | 0.87 | 1.08 | 0.83 | 0.79 | 2.23 | 0.88 | 1.01 | 1.38 | 1.03 | 0.97 | 1.19 | 0.86 |
| Tssc1 | 0.77 | 0.86 | 0.81 | 0.86 | 1.17 | 0.94 | 0.87 | 1.29 | 1.12 | 1.17 | 1.25 | 1.10 |
| Tssc4 | 1.16 | 0.99 | 1.00 | 1.43 | 2.33 | 1.16 | 0.95 | 2.17 | 1.00 | 1.09 | 1.36 | 0.98 |
| Tsta3 | 0.99 | 0.98 | 0.90 | 0.98 | 2.16 | 0.87 | 1.04 | 2.38 | 1.07 | 1.22 | 1.09 | 0.92 |
| Ttc27 | 0.79 | 0.81 | 1.20 | 1.02 | 3.43 | 1.23 | 1.17 | 2.89 | 0.94 | 0.91 | 0.82 | 1.10 |
| Ttc36 | 0.81 | 1.39 | 0.88 | 0.75 | 0.93 | 3.37 | 0.77 | 3.91 | 0.59 | 1.00 | 1.02 | 0.72 |
| Ttc39c | 1.41 | 0.84 | 1.51 | 1.32 | 5.05 | 0.89 | 1.08 | 1.29 | 1.01 | 1.32 | 2.38 | 0.79 |
| Ttc9b | 1.00 | 1.00 | 1.00 | 1.00 | 1.00 | 1.00 | 0.97 | 2.58 | 1.03 | 1.00 | 7.73 | 1.00 |
| Ttll7 | 1.59 | 1.50 | 1.10 | 2.38 | 1.00 | 2.28 | 1.25 | 0.46 | 1.12 | 1.68 | 4.36 | 1.28 |
| Ttr | 2.48 | 3.36 | 2.77 | 0.63 | 0.52 | 1.93 | 1.00 | 1.00 | 1.00 | 1.00 | 43.75 | 1.00 |
| Ttyh1 | 2.00 | 2.20 | 1.42 | 1.32 | 1.00 | 0.84 | 0.96 | 1.79 | 0.97 | 1.10 | 9.08 | 1.00 |
| Tub | 1.00 | 1.00 | 1.00 | 1.00 | 1.00 | 1.00 | 1.10 | 0.77 | 1.00 | 1.00 | 5.10 | 1.00 |
| Tuba3a | 1.00 | 1.00 | 1.00 | 2.49 | 1.33 | 1.73 | 1.03 | 1.07 | 1.04 | 1.00 | 1.00 | 1.00 |
| Tuba3b | 1.00 | 1.00 | 1.00 | 2.52 | 2.18 | 1.46 | 1.03 | 2.01 | 1.04 | 1.00 | 1.00 | 1.00 |
| Tuba8 | 1.07 | 1.01 | 1.08 | 1.19 | 0.46 | 5.14 | 0.79 | 1.61 | 1.01 | 1.53 | 1.95 | 0.76 |
| Tubb2a | 0.90 | 1.01 | 1.04 | 1.63 | 0.97 | 1.34 | 0.86 | 0.39 | 0.82 | 0.90 | 1.56 | 0.86 |
| Tubb2a-ps2 | 1.27 | 1.15 | 0.85 | 0.99 | 0.72 | 0.79 | 1.00 | 1.00 | 1.15 | 0.68 | 1.37 | 1.20 |

Fig. 35- 280

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Tnni3 | 1.00 | 1.00 | 1.00 | 1.00 | 0.15 | 1.00 | 1.62 | 26.86 | 1.22 | 1.48 | 1.00 | 1.00 |
| Tnnt1 | 1.00 | 1.00 | 1.00 | 0.88 | 1.04 | 0.82 | 1.04 | 26.37 | 1.50 | 6.83 | 2.03 | 2.89 |
| Tnnt2 | 1.00 | 1.00 | 1.00 | 1.00 | 1.44 | 1.01 | 2.95 | 17.87 | 1.62 | 1.00 | 1.00 | 1.00 |
| Tnnt3 | 1.00 | 1.00 | 1.00 | 1.00 | 0.17 | 1.00 | 2.44 | 13.53 | 2.05 | 4.73 | 1.00 | 1.00 |
| Tnp1 | 1.00 | 1.07 | 0.75 | 1.00 | 3.40 | 0.52 | 28.17 | 1.00 | 1.74 | 1.00 | 1.00 | 1.00 |
| Tnp2 | 1.00 | 1.68 | 0.43 | 1.00 | 5.73 | 0.72 | 48.51 | 7.61 | 0.87 | 1.00 | 1.00 | 1.00 |
| Tnxb | 0.67 | 1.00 | 1.29 | 1.00 | 0.42 | 1.00 | 1.13 | 6.25 | 1.26 | 1.00 | 1.00 | 1.00 |
| Tomm6 | 0.60 | 0.72 | 0.78 | 0.99 | 0.74 | 0.91 | 1.01 | 8.71 | 0.72 | 2.25 | 0.98 | 0.89 |
| Top1mt | 1.00 | 1.00 | 1.00 | 1.01 | 0.61 | 1.13 | 0.81 | 11.40 | 0.86 | 1.58 | 1.00 | 0.98 |
| Toporsos | 0.65 | 0.77 | 0.64 | 0.66 | 3.58 | 1.01 | 1.52 | 7.53 | 1.33 | 2.13 | 1.04 | 0.84 |
| Tpd52l1 | 0.94 | 1.07 | 0.98 | 1.29 | 7.52 | 1.05 | 1.26 | 0.96 | 1.18 | 1.00 | 1.00 | 1.00 |
| Tpgs1 | 1.44 | 1.20 | 0.88 | 1.16 | 1.07 | 1.06 | 1.33 | 8.69 | 0.98 | 2.65 | 1.55 | 1.28 |
| Tppp | 0.52 | 0.59 | 0.56 | 0.95 | 0.58 | 0.89 | 0.62 | 0.13 | 0.71 | 1.00 | 0.84 | 0.77 |
| Tppp3 | 1.74 | 2.08 | 2.09 | 1.21 | 1.16 | 1.08 | 1.99 | 2.10 | 1.37 | 0.68 | 0.60 | 0.66 |
| Tpsab1 | 1.00 | 1.00 | 1.00 | 1.00 | 1.00 | 1.00 | 1.68 | 3.01 | 1.58 | 1.00 | 1.00 | 1.00 |
| Tpsg1 | 1.00 | 1.00 | 1.00 | 1.00 | 0.13 | 1.00 | 1.86 | 6.75 | 2.04 | 1.00 | 1.00 | 1.00 |
| Tpt1 | 0.77 | 0.77 | 0.84 | 1.03 | 1.03 | 0.99 | 1.20 | 4.06 | 0.82 | 2.02 | 1.10 | 0.97 |
| Trafd1 | 0.93 | 1.52 | 1.33 | 1.01 | 1.93 | 1.09 | 1.26 | 0.77 | 1.21 | 1.61 | 1.46 | 1.48 |
| Trank1 | 1.00 | 1.00 | 1.00 | 0.84 | 0.39 | 0.90 | 1.00 | 1.00 | 1.00 | 1.00 | 1.00 | 1.00 |
| Trappc2l | 0.60 | 0.51 | 1.51 | 1.11 | 0.72 | 1.12 | 1.27 | 6.84 | 1.07 | 3.26 | 1.48 | 1.33 |
| Trappc6a | 0.70 | 0.72 | 1.06 | 0.84 | 0.91 | 1.19 | 1.28 | 14.90 | 0.84 | 3.04 | 1.31 | 1.08 |
| Trim12a | 1.00 | 1.00 | 1.00 | 1.00 | 1.99 | 1.34 | 6.64 | 8.26 | 7.05 | 54.09 | 39.89 | 33.98 |
| Trim29 | 1.00 | 1.00 | 1.00 | 1.00 | 1.00 | 1.00 | 1.10 | 1.33 | 0.91 | 1.00 | 1.00 | 1.00 |
| Trim30a | 1.00 | 1.00 | 1.00 | 1.00 | 1.00 | 1.00 | 1.85 | 1.00 | 1.56 | 2.96 | 3.10 | 3.20 |
| Trim30b | 1.00 | 1.00 | 1.00 | 1.00 | 1.00 | 1.00 | 1.00 | 1.00 | 1.00 | 11.83 | 5.75 | 5.04 |
| Trim30d | 1.00 | 1.00 | 1.00 | 1.00 | 1.00 | 1.00 | 1.00 | 1.00 | 1.00 | 2.96 | 11.32 | 10.25 |
| Trim34a | 1.00 | 1.00 | 1.00 | 1.00 | 1.00 | 1.00 | 8.20 | 1.00 | 10.50 | 7.70 | 22.34 | 20.97 |
| Trim54 | 1.00 | 1.00 | 1.00 | 1.00 | 0.42 | 1.00 | 2.75 | 8.50 | 2.61 | 1.00 | 1.00 | 1.00 |
| Trim63 | 1.00 | 1.00 | 1.00 | 1.00 | 1.19 | 1.00 | 3.66 | 21.29 | 6.11 | 1.00 | 1.00 | 1.00 |
| Trim9 | 1.00 | 1.00 | 1.00 | 1.08 | 1.71 | 1.00 | 1.00 | 1.00 | 1.00 | 1.00 | 1.00 | 1.00 |
| Trmt1 | 0.94 | 0.77 | 1.16 | 1.01 | 1.26 | 1.24 | 1.06 | 5.72 | 0.96 | 2.31 | 0.84 | 0.92 |
| Trmu | 0.66 | 1.39 | 0.81 | 1.04 | 0.80 | 1.22 | 0.89 | 9.27 | 0.93 | 2.09 | 1.57 | 0.86 |
| Trnau1ap | 0.49 | 0.68 | 0.79 | 0.78 | 0.89 | 1.05 | 0.97 | 10.14 | 0.96 | 3.01 | 1.19 | 1.36 |
| Trnp1 | 1.00 | 1.00 | 1.00 | 1.14 | 1.06 | 1.09 | 1.01 | 1.12 | 0.86 | 3.37 | 6.60 | 2.26 |
| Tro | 1.00 | 1.00 | 1.00 | 0.99 | 0.99 | 1.04 | 1.00 | 1.00 | 1.00 | 1.00 | 1.00 | 1.00 |
| Trp53inp1 | 5.23 | 10.11 | 2.77 | 1.19 | 1.00 | 1.14 | 2.18 | 0.90 | 3.00 | 0.77 | 1.70 | 1.13 |
| Trub2 | 1.51 | 1.57 | 1.06 | 0.93 | 0.89 | 0.95 | 1.01 | 5.68 | 1.01 | 2.16 | 1.02 | 0.94 |
| Try10 | 2.41 | 1.65 | 1.19 | 1.00 | 1.00 | 1.00 | 1.00 | 1.00 | 1.00 | 1.00 | 1.00 | 1.00 |
| Try4 | 1.01 | 1.08 | 0.78 | 1.70 | 1.00 | 0.69 | 0.50 | 3.68 | 0.95 | 1.00 | 1.63 | 1.16 |
| Try5 | 0.88 | 0.99 | 0.58 | 0.67 | 1.00 | 0.48 | 1.00 | 5.77 | 1.02 | 1.00 | 1.56 | 1.02 |
| Tsacc | 1.00 | 1.50 | 1.61 | 1.00 | 1.21 | 0.70 | 2.84 | 13.17 | 0.95 | 6.54 | 1.40 | 0.76 |
| Tsc2 | 0.99 | 0.80 | 0.87 | 1.08 | 0.93 | 1.12 | 1.12 | 13.26 | 0.89 | 2.67 | 1.11 | 1.02 |
| Tsc22d3 | 1.61 | 2.77 | 1.71 | 1.17 | 1.02 | 1.11 | 1.67 | 7.36 | 2.21 | 2.45 | 2.68 | 1.94 |
| Tspan11 | 1.00 | 1.00 | 1.00 | 1.27 | 1.24 | 1.22 | 1.08 | 6.30 | 1.82 | 1.00 | 1.00 | 1.00 |
| Tspan17 | 1.28 | 1.00 | 0.95 | 1.08 | 0.73 | 0.99 | 1.14 | 6.21 | 1.03 | 6.01 | 2.18 | 2.67 |
| Tspan2os | 1.00 | 1.00 | 1.00 | 1.00 | 2.18 | 1.00 | 1.00 | 1.00 | 1.00 | 1.00 | 1.00 | 1.00 |
| Tspan8 | 1.00 | 1.00 | 1.00 | 1.00 | 0.45 | 1.00 | 1.14 | 5.53 | 1.10 | 1.08 | 1.06 | 0.92 |
| Tspo | 1.02 | 1.33 | 1.11 | 1.48 | 0.87 | 1.28 | 1.11 | 3.53 | 0.98 | 2.01 | 1.21 | 1.23 |
| Tssc1 | 0.75 | 1.23 | 1.24 | 1.16 | 1.52 | 1.03 | 1.20 | 2.51 | 0.87 | 1.49 | 1.07 | 0.96 |
| Tssc4 | 1.01 | 1.47 | 0.86 | 1.25 | 0.88 | 1.13 | 1.24 | 5.55 | 0.89 | 1.66 | 0.90 | 0.94 |
| Tsta3 | 1.00 | 1.13 | 0.98 | 1.12 | 1.38 | 0.70 | 1.40 | 8.23 | 1.06 | 2.84 | 1.31 | 1.42 |
| Ttc27 | 1.00 | 1.00 | 1.00 | 1.25 | 1.46 | 1.33 | 1.18 | 11.69 | 0.87 | 2.31 | 0.76 | 0.92 |
| Ttc36 | 1.49 | 1.10 | 1.00 | 1.00 | 3.10 | 1.15 | 0.99 | 23.89 | 0.86 | 1.38 | 1.00 | 1.00 |
| Ttc39c | 1.00 | 1.00 | 1.00 | 1.17 | 1.44 | 1.05 | 1.19 | 2.34 | 0.80 | 4.17 | 2.50 | 2.07 |
| Ttc9b | 1.00 | 1.00 | 1.00 | 1.08 | 0.95 | 0.90 | 1.00 | 1.00 | 1.00 | 1.00 | 1.00 | 1.00 |
| Ttll7 | 1.00 | 1.00 | 1.00 | 0.97 | 1.00 | 1.00 | 0.83 | 0.77 | 1.49 | 1.00 | 1.00 | 1.00 |
| Ttr | 0.70 | 0.84 | 1.20 | 1.03 | 0.94 | 0.94 | 2.36 | 3.21 | 1.26 | 1.00 | 1.00 | 1.00 |
| Ttyh1 | 0.93 | 1.00 | 1.16 | 1.12 | 0.91 | 1.07 | 1.05 | 1.02 | 1.10 | 1.00 | 1.00 | 1.00 |
| Tub | 1.00 | 1.00 | 1.00 | 0.91 | 1.25 | 0.94 | 1.00 | 1.00 | 1.00 | 1.00 | 1.00 | 1.00 |
| Tuba3a | 1.00 | 1.00 | 1.00 | 1.00 | 1.00 | 1.00 | 12.51 | 1.00 | 1.00 | 1.00 | 1.00 | 1.00 |
| Tuba3b | 1.00 | 1.00 | 1.00 | 1.00 | 1.00 | 1.00 | 8.35 | 1.00 | 1.00 | 1.00 | 1.00 | 1.00 |
| Tuba8 | 1.00 | 1.00 | 1.00 | 1.20 | 0.76 | 1.05 | 0.90 | 2.52 | 0.59 | 2.02 | 1.02 | 1.24 |
| Tubb2a | 1.67 | 2.02 | 0.99 | 1.12 | 1.50 | 1.04 | 1.86 | 0.45 | 0.97 | 0.62 | 0.79 | 0.86 |
| Tubb2a-ps2 | 1.00 | 1.00 | 1.00 | 1.09 | 1.00 | 0.99 | 1.47 | 0.20 | 1.19 | 0.44 | 0.48 | 0.41 |

Fig. 35- 281

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Tubb2b | 2.12 | 2.91 | 1.30 | 0.67 | 0.23 | 1.93 | 1.68 | 1.27 | 1.71 | 0.26 | 0.23 | 0.86 |
| Tubb3 | 1.00 | 1.00 | 1.00 | 1.00 | 0.07 | 1.00 | 1.00 | 1.00 | 1.04 | 1.00 | 1.00 | 1.00 |
| Tubb4a | 0.88 | 1.00 | 1.00 | 0.37 | 0.03 | 0.67 | 0.46 | 0.40 | 0.57 | 0.38 | 0.16 | 0.24 |
| Tufm | 1.32 | 0.50 | 0.88 | 0.22 | 8.69 | 0.87 | 0.97 | 0.81 | 0.78 | 2.25 | 4.27 | 0.79 |
| Txn1 | 1.48 | 0.87 | 0.92 | 0.85 | 7.72 | 1.28 | 0.67 | 0.83 | 0.81 | 1.72 | 2.91 | 1.09 |
| Txndc17 | 1.29 | 0.69 | 0.84 | 0.53 | 7.88 | 0.97 | 0.91 | 0.83 | 0.84 | 1.47 | 2.45 | 1.03 |
| Tyk2 | 2.40 | 1.75 | 2.78 | 4.16 | 2.96 | 5.47 | 6.75 | 5.56 | 5.50 | 5.44 | 7.03 | 9.13 |
| U2af1 | 1.65 | 0.62 | 1.16 | 0.50 | 17.70 | 1.85 | 1.36 | 1.66 | 0.89 | 2.65 | 3.42 | 1.14 |
| Uap1 | 1.48 | 1.50 | 1.47 | 2.83 | 5.67 | 1.82 | 1.05 | 1.24 | 1.34 | 1.50 | 1.66 | 1.35 |
| Uba52 | 1.16 | 0.53 | 0.88 | 0.21 | 10.06 | 0.98 | 0.97 | 0.80 | 0.79 | 2.11 | 3.91 | 0.90 |
| Ubald2 | 0.92 | 0.44 | 0.77 | 0.70 | 15.25 | 2.51 | 2.10 | 0.91 | 0.96 | 3.89 | 5.74 | 1.11 |
| Ube2a | 1.08 | 1.02 | 0.97 | 1.01 | 2.99 | 1.28 | 0.95 | 0.99 | 0.92 | 1.12 | 1.44 | 1.05 |
| Ube2c | 1.00 | 1.00 | 1.00 | 1.00 | 1.92 | 1.00 | 1.00 | 1.00 | 1.00 | 2.41 | 6.97 | 0.99 |
| Ube2cbp | 1.45 | 1.24 | 1.03 | 1.00 | 1.00 | 1.00 | 1.00 | 1.00 | 1.00 | 1.00 | 1.00 | 1.00 |
| Ube2h | 1.14 | 1.24 | 0.96 | 1.62 | 1.23 | 1.01 | 1.25 | 1.40 | 0.97 | 0.85 | 0.62 | 0.98 |
| Ube2l6 | 1.30 | 1.08 | 1.28 | 3.36 | 7.63 | 2.25 | 0.90 | 0.99 | 0.71 | 1.94 | 1.70 | 1.32 |
| Ube2m | 1.17 | 0.63 | 0.88 | 0.44 | 4.48 | 0.83 | 1.01 | 0.89 | 0.85 | 1.96 | 2.64 | 0.87 |
| Ube2ql1 | 1.00 | 1.00 | 1.00 | 0.81 | 0.23 | 0.54 | 1.77 | 1.50 | 1.18 | 1.00 | 1.00 | 1.00 |
| Ube2s | 1.38 | 0.64 | 0.82 | 0.77 | 6.63 | 1.05 | 1.04 | 0.78 | 0.78 | 1.51 | 2.29 | 0.92 |
| Ubl5 | 1.13 | 0.57 | 0.74 | 0.48 | 5.65 | 1.12 | 1.08 | 1.31 | 1.08 | 2.78 | 2.87 | 1.30 |
| Ubxn1 | 1.41 | 0.74 | 1.01 | 0.48 | 6.14 | 1.30 | 0.90 | 0.85 | 0.98 | 1.83 | 2.87 | 1.07 |
| Ubxn11 | 1.00 | 1.00 | 1.00 | 1.00 | 1.44 | 1.00 | 1.00 | 1.00 | 1.00 | 4.48 | 6.66 | 0.91 |
| Ubxn6 | 1.32 | 0.69 | 1.15 | 0.42 | 5.40 | 1.04 | 1.08 | 0.99 | 0.90 | 1.98 | 3.17 | 1.06 |
| Uchl1 | 2.19 | 1.71 | 2.02 | 1.00 | 0.18 | 1.00 | 1.51 | 1.11 | 1.19 | 4.99 | 7.27 | 1.39 |
| Uchl3 | 1.82 | 2.86 | 1.80 | 0.23 | 5.37 | 1.16 | 0.65 | 0.76 | 0.57 | 8.04 | 7.25 | 2.10 |
| Ucma | 1.00 | 1.00 | 1.00 | 1.00 | 1.00 | 1.00 | 1.00 | 1.00 | 1.00 | 1.00 | 1.00 | 1.00 |
| Ucp1 | 4.94 | 9.20 | 7.17 | 0.24 | 1.62 | 0.59 | 1.00 | 1.00 | 8.44 | 1.00 | 1.54 | 1.00 |
| Ucp2 | 2.45 | 1.52 | 1.89 | 1.73 | 8.86 | 3.82 | 1.43 | 1.31 | 1.49 | 1.51 | 1.92 | 1.35 |
| Ufc1 | 1.51 | 0.93 | 1.12 | 0.70 | 8.07 | 0.90 | 0.98 | 0.94 | 1.05 | 2.28 | 3.48 | 1.05 |
| Ugdh | 1.43 | 3.48 | 1.19 | 5.68 | 3.15 | 1.81 | 0.87 | 0.88 | 1.13 | 0.29 | 0.55 | 0.90 |
| Umps | 0.91 | 1.28 | 0.91 | 3.58 | 6.15 | 1.51 | 1.15 | 1.14 | 0.95 | 1.68 | 1.30 | 0.92 |
| Upp1 | 1.00 | 1.00 | 1.00 | 0.95 | 4.67 | 1.12 | 1.95 | 0.77 | 2.15 | 2.07 | 2.27 | 1.35 |
| Upp2 | 1.00 | 1.00 | 1.00 | 1.00 | 1.00 | 1.00 | 1.00 | 1.00 | 1.00 | 1.00 | 1.00 | 1.00 |
| Uqcc2 | 1.21 | 0.58 | 0.73 | 0.48 | 5.52 | 0.82 | 1.03 | 0.79 | 0.80 | 2.65 | 2.91 | 0.98 |
| Uqcr10 | 1.18 | 0.56 | 0.88 | 0.21 | 8.17 | 0.95 | 1.22 | 0.92 | 0.81 | 2.17 | 3.65 | 1.08 |
| Uqcr11 | 1.21 | 0.40 | 0.70 | 0.13 | 8.62 | 0.78 | 0.85 | 0.71 | 0.75 | 2.32 | 4.03 | 1.00 |
| Uqcrc1 | 0.93 | 0.54 | 0.81 | 0.26 | 3.27 | 0.80 | 1.05 | 0.94 | 0.84 | 2.54 | 2.38 | 0.97 |
| Uqcrh | 1.03 | 0.48 | 0.83 | 0.30 | 8.19 | 0.86 | 0.91 | 0.78 | 0.78 | 2.71 | 4.25 | 0.88 |
| Uqcrq | 1.10 | 0.59 | 0.78 | 0.23 | 5.95 | 0.86 | 1.15 | 0.85 | 0.80 | 2.10 | 2.95 | 1.05 |
| Urah | 1.00 | 1.00 | 1.00 | 1.00 | 1.00 | 1.00 | 0.86 | 0.93 | 0.91 | 1.60 | 2.83 | 1.31 |
| Urod | 1.18 | 0.60 | 0.96 | 0.25 | 4.09 | 0.94 | 1.07 | 0.93 | 0.81 | 2.31 | 2.61 | 0.99 |
| Use1 | 1.28 | 0.49 | 0.92 | 0.24 | 9.85 | 1.02 | 1.02 | 0.80 | 1.00 | 2.82 | 4.01 | 0.93 |
| Usp18 | 1.10 | 2.36 | 1.12 | 1.87 | 2.78 | 1.64 | 2.03 | 1.54 | 2.28 | 2.82 | 3.56 | 2.90 |
| Usp3 | 2.23 | 1.28 | 1.77 | 1.58 | 6.72 | 1.10 | 1.35 | 1.17 | 1.14 | 2.92 | 3.26 | 0.92 |
| Usp4 | 1.12 | 0.77 | 1.00 | 0.78 | 4.21 | 0.91 | 1.01 | 0.89 | 0.99 | 2.53 | 2.52 | 1.02 |
| Usp54 | 1.49 | 2.77 | 1.78 | 6.42 | 1.34 | 1.63 | 1.66 | 2.12 | 1.21 | 0.47 | 0.48 | 1.45 |
| Utf1 | 1.00 | 1.00 | 1.00 | 1.00 | 1.00 | 1.00 | 1.00 | 1.00 | 1.00 | 1.00 | 1.00 | 1.00 |
| Utp11l | 1.68 | 1.02 | 1.40 | 1.40 | 5.05 | 1.55 | 0.69 | 0.86 | 0.76 | 0.61 | 1.05 | 1.09 |
| Vamp3 | 0.92 | 0.99 | 0.78 | 0.61 | 0.66 | 0.73 | 0.74 | 0.85 | 0.74 | 0.68 | 0.68 | 0.97 |
| Vamp5 | 1.64 | 0.79 | 1.00 | 1.17 | 12.00 | 1.25 | 0.76 | 0.59 | 0.66 | 1.18 | 1.62 | 1.07 |
| Vamp8 | 1.05 | 0.50 | 0.77 | 0.34 | 10.00 | 0.89 | 0.75 | 0.62 | 0.67 | 3.96 | 5.32 | 1.15 |
| Vars2 | 0.85 | 0.40 | 0.72 | 0.52 | 4.01 | 0.78 | 1.27 | 1.09 | 1.00 | 3.19 | 3.10 | 1.12 |
| Vaultrc5 | 1.00 | 0.49 | 1.00 | 1.00 | 2.41 | 1.00 | 1.00 | 1.00 | 1.00 | 3.00 | 6.32 | 1.00 |
| Vax1 | 1.00 | 1.00 | 1.00 | 1.00 | 1.00 | 1.00 | 1.00 | 1.00 | 1.00 | 1.00 | 1.00 | 1.00 |
| Vcpkmt | 2.40 | 0.66 | 0.93 | 0.61 | 2.72 | 0.91 | 0.96 | 0.89 | 0.80 | 1.24 | 1.81 | 1.05 |
| Vdr | 1.00 | 1.00 | 1.00 | 1.54 | 1.67 | 1.00 | 1.00 | 1.00 | 1.00 | 2.45 | 2.98 | 1.80 |
| Vezt | 1.24 | 0.72 | 0.97 | 1.01 | 4.12 | 1.21 | 0.86 | 0.77 | 0.81 | 2.50 | 2.64 | 1.07 |
| Vgf | 1.00 | 1.00 | 1.00 | 1.00 | 0.14 | 1.00 | 1.00 | 1.00 | 1.00 | 1.00 | 1.00 | 1.00 |
| Vgll4 | 0.60 | 1.00 | 1.14 | 1.22 | 0.07 | 0.68 | 0.86 | 1.48 | 1.27 | 1.00 | 0.68 | 1.16 |
| Vnn1 | 3.37 | 1.63 | 4.98 | 8.40 | 14.86 | 6.83 | 1.00 | 1.00 | 1.00 | 3.26 | 3.18 | 1.65 |
| Vpreb3 | 1.00 | 1.00 | 1.00 | 1.64 | 8.12 | 2.78 | 1.00 | 1.00 | 1.00 | 1.11 | 2.02 | 0.73 |
| Vps16 | 0.78 | 0.52 | 1.11 | 0.59 | 5.54 | 1.05 | 0.96 | 1.02 | 0.96 | 2.62 | 3.02 | 1.01 |
| Vps28 | 1.27 | 0.53 | 0.75 | 0.23 | 5.77 | 1.08 | 0.89 | 0.60 | 0.70 | 1.71 | 2.82 | 0.84 |
| Vps36 | 0.86 | 0.85 | 1.35 | 0.84 | 4.36 | 0.92 | 0.91 | 0.88 | 0.90 | 2.33 | 2.73 | 1.02 |

Fig. 35- 282

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Tubb2b | 0.84 | 0.99 | 0.85 | 1.19 | 1.25 | 0.97 | 3.87 | 0.96 | 6.27 | 1.33 | 1.40 | 1.20 |
| Tubb3 | 0.55 | 0.60 | 0.66 | 1.00 | 1.00 | 1.00 | 1.00 | 1.00 | 1.00 | 0.99 | 1.30 | 1.11 |
| Tubb4a | 1.01 | 0.72 | 0.96 | 1.00 | 1.00 | 1.00 | 1.00 | 1.00 | 1.00 | 0.95 | 1.09 | 1.11 |
| Tufm | 0.94 | 1.27 | 0.97 | 0.87 | 0.70 | 0.98 | 0.93 | 1.55 | 0.99 | 1.05 | 1.71 | 1.03 |
| Txn1 | 0.99 | 1.32 | 0.94 | 0.82 | 0.85 | 0.76 | 0.90 | 0.87 | 0.84 | 1.04 | 1.78 | 1.07 |
| Txndc17 | 1.32 | 1.73 | 1.09 | 0.96 | 0.91 | 0.92 | 1.16 | 0.90 | 0.92 | 1.08 | 1.69 | 1.23 |
| Tyk2 | 9.67 | 11.00 | 12.66 | 4.83 | 2.74 | 5.36 | 5.27 | 1.88 | 4.76 | 8.18 | 11.53 | 7.65 |
| U2af1 | 1.08 | 1.47 | 0.68 | 0.70 | 0.69 | 0.81 | 1.49 | 3.11 | 1.08 | 1.02 | 2.58 | 1.19 |
| Uap1 | 1.12 | 0.97 | 1.08 | 0.92 | 0.84 | 0.78 | 0.98 | 0.86 | 1.04 | 0.98 | 1.20 | 0.99 |
| Uba52 | 1.36 | 1.89 | 1.04 | 0.91 | 0.69 | 0.88 | 0.90 | 1.44 | 0.95 | 1.02 | 1.88 | 1.02 |
| Ubald2 | 0.82 | 1.51 | 0.72 | 1.79 | 0.96 | 1.18 | 0.88 | 1.91 | 2.54 | 0.78 | 2.09 | 0.87 |
| Ube2a | 0.86 | 0.88 | 1.01 | 0.93 | 0.96 | 0.96 | 0.93 | 0.93 | 1.08 | 0.97 | 1.23 | 1.21 |
| Ube2c | 0.55 | 0.81 | 0.45 | 1.00 | 0.45 | 1.00 | 1.00 | 1.31 | 1.00 | 0.91 | 1.87 | 1.11 |
| Ube2cbp | 0.87 | 0.99 | 1.07 | 1.00 | 1.23 | 1.00 | 1.74 | 0.81 | 1.06 | 1.19 | 1.06 | 1.18 |
| Ube2h | 0.99 | 0.97 | 1.15 | 0.92 | 1.52 | 1.04 | 1.19 | 1.12 | 1.01 | 1.09 | 0.90 | 1.05 |
| Ube2l6 | 1.23 | 1.27 | 1.28 | 0.79 | 0.54 | 1.41 | 0.85 | 0.48 | 0.76 | 1.64 | 1.56 | 1.20 |
| Ube2m | 0.89 | 1.17 | 0.98 | 0.91 | 0.65 | 0.88 | 1.02 | 2.02 | 0.84 | 1.01 | 1.56 | 0.92 |
| Ube2ql1 | 0.94 | 0.98 | 1.17 | 2.29 | 1.19 | 1.41 | 0.84 | 1.00 | 0.77 | 1.00 | 1.00 | 1.00 |
| Ube2s | 0.84 | 1.23 | 0.68 | 0.59 | 0.57 | 0.54 | 1.52 | 1.62 | 0.75 | 1.07 | 1.98 | 1.07 |
| Ubl5 | 0.58 | 0.51 | 0.71 | 1.12 | 0.69 | 1.10 | 1.71 | 1.96 | 1.28 | 1.24 | 1.58 | 1.16 |
| Ubxn1 | 1.10 | 1.45 | 0.91 | 0.94 | 0.87 | 0.93 | 1.13 | 1.52 | 1.20 | 1.05 | 1.70 | 1.29 |
| Ubxn11 | 0.72 | 1.16 | 0.75 | 1.00 | 0.63 | 1.00 | 1.00 | 1.58 | 1.00 | 1.00 | 1.00 | 1.00 |
| Ubxn6 | 1.25 | 1.61 | 1.14 | 1.01 | 0.75 | 0.98 | 1.06 | 1.89 | 1.06 | 1.21 | 1.60 | 1.11 |
| Uchl1 | 0.88 | 1.87 | 0.77 | 1.71 | 0.87 | 1.23 | 1.00 | 1.92 | 1.00 | 1.11 | 2.05 | 1.08 |
| Uchl3 | 2.58 | 6.14 | 4.74 | 0.71 | 1.37 | 1.01 | 0.47 | 0.60 | 0.46 | 1.07 | 1.81 | 1.77 |
| Ucma | 1.86 | 2.91 | 2.24 | 1.00 | 1.00 | 1.00 | 1.00 | 1.00 | 1.00 | 1.00 | 1.00 | 1.00 |
| Ucp1 | 0.08 | 0.37 | 0.06 | 1.00 | 0.47 | 0.71 | 1.00 | 1.00 | 1.00 | 1.00 | 1.00 | 1.00 |
| Ucp2 | 1.25 | 1.53 | 1.20 | 1.05 | 1.02 | 1.02 | 1.51 | 1.79 | 1.33 | 1.04 | 1.28 | 1.04 |
| Ufc1 | 1.55 | 1.98 | 1.17 | 0.82 | 1.05 | 0.90 | 0.89 | 1.46 | 0.96 | 0.97 | 1.84 | 1.16 |
| Ugdh | 1.01 | 1.11 | 1.10 | 1.07 | 1.49 | 1.12 | 1.28 | 0.78 | 1.45 | 0.94 | 1.00 | 0.89 |
| Umps | 0.69 | 0.63 | 0.68 | 1.07 | 1.01 | 1.05 | 0.63 | 1.11 | 0.73 | 1.11 | 0.97 | 1.19 |
| Upp1 | 2.39 | 1.98 | 1.18 | 1.23 | 0.84 | 0.93 | 1.00 | 3.06 | 1.00 | 4.93 | 4.55 | 2.08 |
| Upp2 | 1.00 | 1.00 | 1.00 | 2.96 | 6.59 | 2.40 | 0.69 | 0.61 | 0.54 | 1.00 | 1.00 | 1.00 |
| Uqcc2 | 1.11 | 1.63 | 0.87 | 0.99 | 0.68 | 1.02 | 0.81 | 1.11 | 0.68 | 0.59 | 1.43 | 0.90 |
| Uqcr10 | 1.05 | 1.51 | 0.79 | 0.83 | 0.67 | 0.80 | 0.98 | 1.52 | 0.87 | 1.03 | 1.86 | 1.07 |
| Uqcr11 | 1.05 | 2.01 | 0.70 | 0.68 | 0.51 | 0.72 | 0.81 | 1.64 | 0.83 | 1.02 | 1.74 | 1.03 |
| Uqcrc1 | 0.91 | 1.15 | 0.85 | 0.88 | 0.58 | 0.88 | 0.96 | 1.82 | 0.89 | 0.98 | 1.16 | 0.88 |
| Uqcrh | 1.37 | 1.62 | 1.05 | 0.81 | 0.60 | 0.81 | 0.89 | 1.86 | 0.86 | 1.00 | 1.89 | 0.98 |
| Uqcrq | 0.92 | 1.15 | 0.65 | 0.80 | 0.65 | 0.95 | 0.93 | 1.64 | 0.78 | 1.09 | 1.58 | 0.98 |
| Urah | 2.14 | 2.12 | 1.30 | 4.15 | 2.52 | 3.40 | 0.94 | 1.52 | 0.88 | 1.20 | 1.84 | 1.54 |
| Urod | 0.96 | 1.47 | 1.02 | 0.82 | 0.63 | 0.92 | 0.77 | 1.49 | 0.76 | 1.04 | 1.33 | 0.88 |
| Use1 | 1.66 | 1.82 | 1.16 | 0.98 | 0.56 | 0.93 | 1.10 | 2.08 | 1.14 | 1.07 | 1.73 | 1.06 |
| Usp18 | 2.67 | 2.84 | 2.07 | 1.78 | 1.78 | 1.83 | 5.01 | 14.94 | 3.84 | 5.04 | 6.70 | 2.40 |
| Usp3 | 1.25 | 1.44 | 1.10 | 1.20 | 0.74 | 1.18 | 1.33 | 3.35 | 1.32 | 1.28 | 1.23 | 1.06 |
| Usp4 | 0.93 | 1.02 | 0.90 | 1.17 | 0.72 | 1.01 | 0.92 | 2.43 | 0.89 | 0.98 | 1.32 | 1.01 |
| Usp54 | 3.38 | 2.52 | 2.18 | 1.25 | 1.00 | 1.21 | 1.79 | 1.00 | 1.54 | 1.23 | 0.98 | 1.01 |
| Utf1 | 1.50 | 1.51 | 1.28 | 1.00 | 1.00 | 1.00 | 1.00 | 1.00 | 1.00 | 1.00 | 1.00 | 1.00 |
| Utp11l | 0.88 | 0.87 | 0.72 | 0.79 | 0.88 | 0.71 | 0.54 | 0.51 | 0.87 | 0.71 | 1.06 | 1.16 |
| Vamp3 | 1.15 | 1.24 | 1.00 | 0.94 | 1.13 | 0.83 | 1.00 | 1.04 | 0.86 | 1.17 | 1.33 | 1.12 |
| Vamp5 | 1.51 | 1.37 | 1.06 | 0.72 | 0.37 | 0.65 | 0.68 | 0.37 | 0.57 | 0.90 | 1.40 | 1.13 |
| Vamp8 | 1.65 | 2.08 | 1.12 | 0.86 | 0.60 | 0.78 | 0.86 | 2.40 | 0.78 | 1.04 | 2.12 | 1.07 |
| Vars2 | 0.91 | 0.95 | 0.83 | 1.03 | 0.60 | 1.06 | 0.78 | 3.11 | 0.72 | 1.00 | 1.01 | 1.09 |
| Vaultrc5 | 1.00 | 1.27 | 1.00 | 1.00 | 1.99 | 1.00 | 1.00 | 1.00 | 1.00 | 1.00 | 1.08 | 0.94 |
| Vax1 | 1.00 | 1.00 | 1.00 | 1.00 | 1.00 | 1.00 | 1.00 | 1.00 | 1.00 | 1.00 | 1.00 | 1.00 |
| Vcpkmt | 0.98 | 1.13 | 0.92 | 1.10 | 0.82 | 1.16 | 1.36 | 0.83 | 1.06 | 1.43 | 1.10 | 0.95 |
| Vdr | 1.05 | 0.97 | 1.03 | 0.98 | 1.11 | 1.13 | 1.00 | 1.00 | 1.00 | 0.98 | 0.93 | 0.93 |
| Vezt | 1.02 | 1.23 | 0.94 | 1.43 | 0.76 | 1.10 | 0.87 | 1.61 | 0.62 | 0.83 | 0.99 | 0.96 |
| Vgf | 0.99 | 0.74 | 1.00 | 1.00 | 1.00 | 1.00 | 1.00 | 1.00 | 1.00 | 1.17 | 1.77 | 1.68 |
| Vgll4 | 0.60 | 0.49 | 1.08 | 1.10 | 1.00 | 1.47 | 0.82 | 1.00 | 1.03 | 1.08 | 0.33 | 1.11 |
| Vnn1 | 2.25 | 1.81 | 2.36 | 1.30 | 0.86 | 1.42 | 1.31 | 0.98 | 1.04 | 1.28 | 0.98 | 1.33 |
| Vpreb3 | 1.01 | 1.47 | 1.48 | 1.00 | 1.00 | 1.00 | 1.00 | 0.75 | 1.02 | 1.07 | 0.92 | 0.91 |
| Vps16 | 1.13 | 1.18 | 1.01 | 1.05 | 0.80 | 1.25 | 1.02 | 1.77 | 0.92 | 1.06 | 1.50 | 0.99 |
| Vps28 | 1.23 | 1.52 | 1.03 | 0.93 | 0.83 | 0.93 | 0.95 | 1.30 | 0.91 | 0.78 | 1.79 | 1.18 |
| Vps36 | 0.79 | 0.69 | 0.99 | 1.24 | 1.43 | 1.20 | 2.48 | 2.95 | 1.08 | 0.91 | 1.29 | 0.93 |

Fig. 35- 283

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Tubb2b | 1.08 | 1.10 | 1.05 | 1.59 | 1.43 | 1.24 | 0.69 | 0.83 | 0.95 | 0.92 | 1.82 | 1.12 |
| Tubb3 | 1.31 | 1.38 | 1.40 | 1.00 | 1.00 | 1.00 | 0.87 | 0.15 | 1.11 | 1.10 | 28.47 | 0.78 |
| Tubb4a | 1.41 | 1.62 | 1.77 | 0.57 | 0.51 | 0.77 | 1.00 | 1.00 | 1.00 | 0.78 | 25.99 | 0.87 |
| Tufm | 0.81 | 0.92 | 0.72 | 0.76 | 2.01 | 0.87 | 0.96 | 2.27 | 0.94 | 1.07 | 1.24 | 0.90 |
| Txn1 | 0.91 | 0.88 | 1.04 | 0.76 | 2.74 | 0.89 | 0.55 | 0.61 | 1.11 | 1.02 | 1.26 | 0.81 |
| Txndc17 | 1.06 | 0.97 | 1.14 | 0.84 | 2.52 | 0.85 | 0.72 | 1.14 | 0.80 | 0.96 | 1.08 | 0.86 |
| Tyk2 | 5.93 | 8.02 | 5.02 | 8.24 | 1.00 | 6.50 | 6.08 | 2.32 | 5.15 | 12.29 | 12.89 | 10.75 |
| U2af1 | 1.17 | 0.77 | 0.94 | 1.45 | 3.67 | 1.46 | 1.13 | 2.56 | 0.66 | 1.03 | 2.12 | 1.01 |
| Uap1 | 1.27 | 1.36 | 1.22 | 5.17 | 10.58 | 3.49 | 1.29 | 0.70 | 1.09 | 1.14 | 1.19 | 1.16 |
| Uba52 | 0.95 | 1.09 | 1.05 | 0.84 | 2.77 | 0.97 | 0.89 | 2.27 | 1.05 | 1.20 | 1.60 | 1.03 |
| Ubald2 | 0.97 | 1.93 | 1.46 | 0.95 | 2.67 | 1.04 | 0.50 | 3.96 | 1.72 | 0.96 | 1.20 | 0.66 |
| Ube2a | 0.89 | 0.90 | 0.82 | 1.30 | 6.73 | 1.34 | 0.98 | 0.93 | 0.92 | 1.03 | 0.94 | 0.94 |
| Ube2c | 0.48 | 0.41 | 0.53 | 0.91 | 1.72 | 0.58 | 0.79 | 1.81 | 0.96 | 0.59 | 0.73 | 0.43 |
| Ube2cbp | 1.00 | 0.98 | 1.00 | 1.00 | 1.00 | 1.00 | 1.02 | 1.20 | 1.00 | 1.20 | 1.98 | 1.08 |
| Ube2h | 1.00 | 1.11 | 1.09 | 0.96 | 0.74 | 1.05 | 1.14 | 0.86 | 1.02 | 0.96 | 0.84 | 1.14 |
| Ube2l6 | 1.84 | 2.25 | 2.12 | 1.18 | 1.10 | 1.26 | 0.91 | 1.44 | 0.84 | 0.57 | 0.44 | 0.35 |
| Ube2m | 0.96 | 1.03 | 0.93 | 0.85 | 1.67 | 1.05 | 0.98 | 1.97 | 1.04 | 0.99 | 1.16 | 0.85 |
| Ube2ql1 | 1.00 | 1.00 | 1.00 | 1.00 | 1.00 | 1.00 | 1.00 | 1.00 | 1.00 | 1.00 | 11.26 | 1.00 |
| Ube2s | 0.77 | 0.92 | 1.06 | 1.00 | 3.16 | 1.13 | 0.87 | 1.51 | 1.04 | 0.81 | 1.13 | 0.90 |
| Ubl5 | 1.10 | 0.88 | 0.96 | 1.34 | 2.01 | 1.24 | 1.28 | 1.72 | 1.22 | 1.16 | 0.79 | 1.55 |
| Ubxn1 | 1.14 | 1.37 | 1.07 | 1.12 | 3.76 | 1.22 | 1.00 | 1.58 | 0.97 | 0.97 | 1.26 | 0.94 |
| Ubxn11 | 1.00 | 1.00 | 1.00 | 1.90 | 4.01 | 1.88 | 0.96 | 4.39 | 1.00 | 0.64 | 0.92 | 0.88 |
| Ubxn6 | 1.14 | 1.28 | 1.17 | 1.08 | 2.55 | 1.09 | 0.94 | 2.09 | 1.06 | 1.06 | 1.43 | 1.05 |
| Uchl1 | 1.77 | 1.85 | 1.38 | 0.90 | 1.16 | 0.78 | 0.77 | 2.55 | 0.96 | 1.00 | 18.84 | 1.00 |
| Uchl3 | 0.48 | 0.43 | 0.66 | 1.42 | 7.24 | 2.28 | 0.77 | 0.75 | 0.74 | 1.97 | 3.46 | 2.74 |
| Ucma | 1.00 | 1.00 | 1.00 | 1.00 | 1.00 | 1.00 | 1.00 | 1.00 | 1.00 | 1.00 | 1.00 | 1.00 |
| Ucp1 | 1.00 | 1.00 | 1.00 | 1.00 | 2.02 | 0.26 | 1.00 | 1.00 | 1.00 | 1.00 | 1.00 | 1.00 |
| Ucp2 | 0.68 | 0.73 | 0.73 | 1.50 | 3.68 | 1.39 | 0.84 | 1.49 | 0.91 | 0.85 | 1.06 | 0.82 |
| Ufc1 | 0.98 | 0.93 | 1.03 | 0.92 | 6.23 | 0.99 | 1.21 | 2.03 | 1.20 | 1.17 | 1.44 | 1.14 |
| Ugdh | 0.86 | 0.91 | 0.83 | 2.79 | 2.56 | 1.57 | 0.92 | 1.00 | 0.78 | 1.26 | 1.07 | 1.07 |
| Umps | 0.81 | 0.76 | 0.74 | 1.76 | 3.48 | 1.35 | 1.11 | 1.80 | 0.98 | 0.88 | 0.74 | 0.89 |
| Upp1 | 1.12 | 1.44 | 0.78 | 2.16 | 3.87 | 2.42 | 1.00 | 1.06 | 1.00 | 1.00 | 1.17 | 1.00 |
| Upp2 | 1.18 | 1.00 | 1.00 | 1.00 | 1.00 | 1.00 | 1.00 | 1.00 | 1.00 | 1.00 | 1.00 | 1.00 |
| Uqcc2 | 1.14 | 0.77 | 0.82 | 0.85 | 2.30 | 0.91 | 0.73 | 2.50 | 1.13 | 1.06 | 1.19 | 1.23 |
| Uqcr10 | 0.96 | 0.98 | 0.98 | 0.90 | 3.15 | 0.94 | 0.90 | 2.14 | 0.94 | 1.10 | 1.54 | 1.03 |
| Uqcr11 | 0.89 | 1.26 | 0.82 | 0.57 | 1.53 | 0.66 | 0.87 | 2.47 | 0.89 | 1.27 | 1.45 | 0.73 |
| Uqcrc1 | 0.97 | 1.13 | 0.89 | 0.69 | 2.19 | 0.71 | 0.97 | 2.52 | 0.98 | 0.93 | 1.29 | 0.98 |
| Uqcrh | 1.05 | 1.04 | 0.98 | 0.81 | 3.20 | 0.98 | 0.89 | 2.45 | 0.89 | 1.03 | 1.21 | 0.98 |
| Uqcrq | 1.02 | 1.21 | 1.04 | 0.82 | 2.08 | 0.77 | 0.94 | 3.01 | 1.00 | 1.10 | 1.37 | 0.83 |
| Urah | 1.02 | 0.96 | 1.34 | 1.00 | 1.00 | 1.00 | 1.00 | 1.00 | 1.00 | 1.00 | 1.00 | 1.00 |
| Urod | 1.15 | 1.34 | 1.01 | 0.62 | 1.82 | 1.01 | 0.85 | 2.66 | 1.02 | 0.60 | 0.75 | 0.56 |
| Use1 | 0.99 | 1.37 | 1.18 | 0.98 | 2.00 | 1.12 | 0.87 | 3.03 | 1.11 | 1.09 | 1.39 | 0.92 |
| Usp18 | 6.58 | 11.69 | 5.70 | 2.64 | 1.82 | 3.12 | 1.00 | 1.00 | 1.00 | 6.77 | 4.68 | 6.26 |
| Usp3 | 1.10 | 1.20 | 1.14 | 1.74 | 3.20 | 1.60 | 0.99 | 2.25 | 1.32 | 1.67 | 1.45 | 1.52 |
| Usp4 | 1.04 | 0.90 | 0.97 | 1.07 | 1.87 | 0.98 | 1.11 | 3.23 | 1.08 | 0.90 | 0.87 | 0.87 |
| Usp54 | 1.23 | 1.42 | 1.24 | 3.66 | 0.78 | 1.74 | 1.10 | 0.62 | 0.98 | 1.30 | 1.38 | 1.11 |
| Utf1 | 1.00 | 1.00 | 1.00 | 1.00 | 1.00 | 1.00 | 6.56 | 3.48 | 7.53 | 0.89 | 1.00 | 0.69 |
| Utp11l | 0.87 | 0.69 | 0.82 | 0.84 | 4.93 | 1.01 | 0.86 | 0.84 | 0.92 | 0.90 | 1.12 | 0.83 |
| Vamp3 | 0.94 | 0.97 | 0.94 | 0.86 | 0.69 | 0.89 | 1.06 | 0.72 | 1.04 | 1.11 | 1.04 | 1.06 |
| Vamp5 | 0.94 | 0.86 | 0.79 | 1.18 | 1.80 | 1.19 | 0.64 | 0.71 | 0.60 | 0.71 | 0.63 | 0.55 |
| Vamp8 | 0.99 | 1.10 | 0.95 | 1.25 | 2.66 | 1.09 | 0.83 | 2.72 | 0.80 | 0.91 | 1.19 | 0.83 |
| Vars2 | 0.87 | 0.94 | 0.60 | 0.86 | 0.89 | 0.84 | 2.61 | 14.33 | 2.68 | 1.16 | 1.30 | 1.09 |
| Vaultrc5 | 1.00 | 1.00 | 1.00 | 1.00 | 0.04 | 1.00 | 1.00 | 2.47 | 1.00 | 0.55 | 2.07 | 1.00 |
| Vax1 | 1.00 | 1.00 | 1.00 | 1.00 | 1.00 | 1.00 | 1.00 | 5.95 | 1.14 | 1.00 | 1.00 | 1.00 |
| Vcpkmt | 0.88 | 0.76 | 0.80 | 0.81 | 1.00 | 0.87 | 1.39 | 0.62 | 1.13 | 1.24 | 1.15 | 1.02 |
| Vdr | 2.66 | 1.46 | 2.96 | 7.04 | 12.91 | 2.91 | 1.07 | 1.29 | 1.13 | 1.49 | 1.24 | 0.81 |
| Vezt | 0.86 | 0.81 | 0.88 | 0.82 | 1.03 | 0.90 | 0.92 | 3.41 | 0.97 | 1.07 | 1.16 | 1.12 |
| Vgf | 3.10 | 6.63 | 1.54 | 1.00 | 1.00 | 1.00 | 0.89 | 1.00 | 1.54 | 1.00 | 13.31 | 1.00 |
| Vgll4 | 0.94 | 0.99 | 1.20 | 1.40 | 0.43 | 1.30 | 2.76 | 6.76 | 2.45 | 1.05 | 0.56 | 1.29 |
| Vnn1 | 1.32 | 1.22 | 1.31 | 2.65 | 3.47 | 3.73 | 0.40 | 0.25 | 0.49 | 1.00 | 1.00 | 1.00 |
| Vpreb3 | 1.00 | 1.00 | 1.00 | 1.34 | 1.00 | 1.84 | 0.44 | 1.17 | 1.95 | 1.06 | 1.10 | 0.85 |
| Vps16 | 1.13 | 1.21 | 0.98 | 0.90 | 2.56 | 1.08 | 1.04 | 2.38 | 1.10 | 1.01 | 1.05 | 1.01 |
| Vps28 | 0.94 | 1.16 | 1.19 | 0.64 | 3.07 | 1.07 | 0.97 | 1.36 | 0.99 | 1.02 | 1.40 | 0.87 |
| Vps36 | 0.78 | 1.14 | 1.10 | 1.23 | 4.23 | 1.08 | 0.75 | 1.88 | 0.78 | 1.44 | 1.06 | 1.16 |

Fig. 35- 284

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Tubb2b | 1.00 | 1.00 | 1.00 | 1.28 | 0.81 | 1.16 | 2.32 | 0.92 | 1.12 | 0.58 | 0.93 | 0.83 |
| Tubb3 | 1.00 | 1.00 | 1.00 | 1.09 | 0.51 | 1.06 | 0.99 | 0.27 | 0.92 | 1.00 | 1.00 | 0.48 |
| Tubb4a | 1.00 | 1.00 | 1.00 | 1.06 | 0.83 | 0.98 | 0.88 | 0.55 | 1.19 | 1.00 | 1.00 | 1.00 |
| Tufm | 0.74 | 0.72 | 1.66 | 1.26 | 1.08 | 0.97 | 1.37 | 16.59 | 0.88 | 3.01 | 0.89 | 0.93 |
| Txn1 | 1.86 | 1.05 | 0.84 | 0.95 | 1.39 | 1.01 | 1.09 | 3.57 | 0.90 | 2.57 | 1.35 | 1.34 |
| Txndc17 | 0.94 | 0.81 | 1.00 | 1.16 | 0.92 | 1.34 | 0.86 | 4.72 | 0.81 | 2.66 | 1.42 | 1.49 |
| Tyk2 | 1.69 | 1.86 | 1.78 | 4.09 | 1.31 | 3.62 | 12.03 | 5.84 | 8.47 | 8.22 | 13.76 | 13.82 |
| U2af1 | 1.14 | 0.95 | 0.63 | 0.91 | 1.00 | 1.21 | 1.27 | 10.26 | 1.01 | 3.10 | 1.22 | 0.98 |
| Uap1 | 1.17 | 1.35 | 1.16 | 0.98 | 1.42 | 1.11 | 1.42 | 2.92 | 1.45 | 1.18 | 1.02 | 1.13 |
| Uba52 | 0.83 | 0.82 | 0.94 | 1.02 | 1.12 | 1.03 | 1.14 | 12.08 | 0.93 | 2.95 | 1.17 | 1.11 |
| Ubald2 | 4.33 | 1.20 | 1.22 | 0.90 | 0.94 | 1.46 | 1.90 | 18.10 | 0.86 | 5.75 | 1.35 | 0.95 |
| Ube2a | 1.24 | 1.22 | 0.88 | 1.02 | 0.54 | 1.11 | 0.95 | 2.74 | 0.98 | 1.34 | 1.04 | 1.14 |
| Ube2c | 1.00 | 1.00 | 1.00 | 1.00 | 0.39 | 1.00 | 0.67 | 2.46 | 0.77 | 1.56 | 1.08 | 0.89 |
| Ube2cbp | 1.00 | 1.00 | 1.00 | 1.00 | 1.12 | 0.77 | 0.92 | 6.09 | 1.05 | 1.00 | 0.97 | 1.00 |
| Ube2h | 0.95 | 0.97 | 1.06 | 1.04 | 5.08 | 1.02 | 1.09 | 0.82 | 1.07 | 0.66 | 0.94 | 0.90 |
| Ube2l6 | 0.99 | 1.00 | 1.73 | 0.93 | 1.36 | 0.63 | 1.47 | 1.93 | 1.25 | 0.88 | 1.03 | 1.00 |
| Ube2m | 1.17 | 1.05 | 1.10 | 1.13 | 1.01 | 1.01 | 1.24 | 5.00 | 0.99 | 1.96 | 1.14 | 0.96 |
| Ube2ql1 | 1.00 | 1.00 | 1.00 | 1.11 | 0.97 | 1.02 | 1.23 | 1.00 | 1.22 | 1.00 | 1.00 | 1.00 |
| Ube2s | 1.09 | 1.14 | 0.68 | 1.09 | 1.04 | 1.04 | 1.40 | 4.55 | 0.89 | 1.86 | 1.03 | 0.99 |
| Ubl5 | 0.74 | 1.09 | 1.35 | 0.80 | 1.08 | 1.12 | 1.08 | 6.47 | 1.10 | 2.18 | 1.05 | 1.11 |
| Ubxn1 | 0.98 | 0.97 | 1.08 | 1.00 | 0.91 | 1.06 | 1.32 | 5.73 | 1.08 | 2.13 | 1.23 | 1.07 |
| Ubxn11 | 1.00 | 1.00 | 1.00 | 1.18 | 1.29 | 0.90 | 1.01 | 5.67 | 1.00 | 3.48 | 1.00 | 1.25 |
| Ubxn6 | 1.25 | 1.16 | 0.97 | 1.13 | 0.94 | 1.10 | 1.23 | 8.99 | 1.00 | 2.61 | 1.64 | 1.23 |
| Uchl1 | 1.00 | 1.00 | 1.00 | 1.13 | 0.94 | 1.14 | 2.82 | 15.36 | 1.71 | 2.56 | 0.86 | 1.60 |
| Uchl3 | 0.57 | 0.60 | 0.88 | 0.66 | 0.86 | 0.69 | 1.16 | 6.48 | 1.72 | 5.64 | 2.83 | 3.25 |
| Ucma | 1.00 | 1.00 | 1.00 | 1.04 | 2.67 | 0.78 | 1.31 | 8.15 | 0.96 | 1.00 | 1.00 | 1.00 |
| Ucp1 | 1.00 | 1.00 | 1.00 | 1.00 | 0.68 | 1.00 | 1.00 | 1.73 | 1.00 | 1.00 | 1.00 | 1.00 |
| Ucp2 | 1.59 | 2.14 | 1.04 | 1.90 | 1.28 | 1.55 | 2.02 | 3.76 | 1.90 | 1.10 | 1.03 | 1.04 |
| Ufc1 | 0.83 | 0.90 | 0.70 | 1.32 | 1.52 | 1.17 | 0.88 | 7.18 | 0.92 | 2.78 | 1.23 | 1.15 |
| Ugdh | 0.87 | 1.15 | 0.68 | 0.95 | 0.40 | 1.00 | 1.03 | 0.49 | 1.19 | 0.78 | 1.14 | 1.10 |
| Umps | 0.97 | 0.94 | 0.93 | 1.23 | 1.47 | 1.00 | 0.69 | 3.20 | 0.71 | 1.12 | 0.64 | 0.82 |
| Upp1 | 1.00 | 1.00 | 1.00 | 1.00 | 1.41 | 1.00 | 1.00 | 5.29 | 1.06 | 2.01 | 1.00 | 1.00 |
| Upp2 | 0.59 | 0.67 | 0.71 | 0.88 | 1.00 | 0.95 | 1.00 | 1.00 | 1.00 | 1.00 | 1.00 | 1.00 |
| Uqcc2 | 1.01 | 1.92 | 0.86 | 0.96 | 1.02 | 1.11 | 2.09 | 11.22 | 0.84 | 2.09 | 0.95 | 0.86 |
| Uqcr10 | 0.63 | 0.71 | 0.84 | 1.04 | 0.99 | 1.08 | 1.12 | 10.44 | 0.92 | 2.72 | 1.01 | 1.26 |
| Uqcr11 | 0.72 | 0.51 | 0.86 | 1.18 | 0.90 | 1.06 | 1.24 | 17.56 | 0.79 | 3.10 | 1.02 | 0.98 |
| Uqcrc1 | 0.69 | 0.87 | 0.82 | 1.00 | 0.85 | 1.07 | 1.10 | 6.61 | 0.89 | 1.94 | 0.93 | 0.96 |
| Uqcrh | 0.84 | 0.86 | 1.02 | 1.01 | 0.91 | 1.05 | 1.14 | 11.19 | 0.87 | 3.02 | 1.23 | 0.98 |
| Uqcrq | 1.00 | 1.47 | 0.98 | 1.22 | 0.85 | 1.08 | 1.50 | 11.41 | 0.96 | 2.46 | 1.13 | 1.12 |
| Urah | 1.05 | 0.80 | 0.85 | 1.00 | 3.76 | 1.00 | 0.99 | 6.55 | 0.68 | 1.00 | 1.00 | 1.00 |
| Urod | 0.95 | 0.69 | 0.80 | 1.19 | 0.80 | 1.16 | 1.02 | 9.28 | 1.13 | 1.66 | 0.84 | 0.77 |
| Use1 | 1.16 | 0.84 | 0.75 | 1.20 | 0.97 | 0.95 | 1.43 | 14.74 | 0.92 | 3.29 | 1.21 | 1.06 |
| Usp18 | 1.00 | 1.00 | 1.00 | 1.00 | 1.00 | 1.00 | 1.00 | 1.70 | 1.00 | 6.41 | 2.97 | 3.89 |
| Usp3 | 1.15 | 1.21 | 1.45 | 1.05 | 0.90 | 0.96 | 1.07 | 7.42 | 1.06 | 3.73 | 1.52 | 1.12 |
| Usp4 | 1.06 | 1.12 | 1.01 | 0.99 | 0.87 | 0.94 | 0.95 | 6.39 | 0.82 | 1.89 | 1.09 | 1.00 |
| Usp54 | 2.18 | 2.06 | 1.26 | 1.01 | 1.00 | 1.03 | 1.41 | 0.19 | 1.49 | 1.00 | 1.14 | 0.90 |
| Utf1 | 1.00 | 1.00 | 1.00 | 1.00 | 1.00 | 1.00 | 1.00 | 1.00 | 1.00 | 1.00 | 1.00 | 1.00 |
| Utp11l | 0.82 | 0.44 | 0.85 | 0.84 | 0.24 | 0.92 | 0.62 | 1.14 | 0.73 | 0.74 | 0.47 | 0.77 |
| Vamp3 | 0.89 | 0.96 | 0.94 | 0.99 | 7.66 | 1.08 | 0.98 | 0.48 | 0.97 | 1.00 | 1.53 | 1.30 |
| Vamp5 | 1.00 | 1.00 | 1.27 | 0.90 | 0.38 | 0.85 | 1.12 | 5.31 | 0.81 | 2.09 | 1.10 | 1.13 |
| Vamp8 | 1.34 | 1.38 | 1.32 | 0.73 | 0.60 | 0.92 | 1.52 | 19.79 | 1.06 | 3.58 | 1.28 | 1.06 |
| Vars2 | 1.00 | 1.00 | 1.00 | 1.12 | 0.57 | 0.89 | 1.24 | 14.57 | 0.87 | 2.94 | 0.91 | 0.82 |
| Vaultrc5 | 1.00 | 1.00 | 1.00 | 1.00 | 0.38 | 1.00 | 1.00 | 3.38 | 1.24 | 1.59 | 1.00 | 1.00 |
| Vax1 | 1.00 | 1.00 | 1.00 | 1.00 | 1.12 | 1.21 | 1.00 | 1.00 | 1.00 | 1.00 | 1.00 | 1.00 |
| Vcpkmt | 1.04 | 1.12 | 1.05 | 1.10 | 5.55 | 1.10 | 1.04 | 1.12 | 0.85 | 1.67 | 0.97 | 1.10 |
| Vdr | 1.00 | 1.00 | 1.00 | 1.00 | 1.00 | 1.00 | 1.31 | 1.47 | 1.09 | 1.00 | 1.00 | 1.00 |
| Vezt | 1.16 | 0.86 | 0.90 | 0.84 | 0.99 | 1.02 | 0.99 | 9.70 | 1.00 | 1.60 | 1.17 | 0.82 |
| Vgf | 1.00 | 1.00 | 1.00 | 1.63 | 1.91 | 1.41 | 1.00 | 1.00 | 1.00 | 1.00 | 1.00 | 1.00 |
| Vgll4 | 1.00 | 1.08 | 0.95 | 0.64 | 1.00 | 0.71 | 0.77 | 0.15 | 0.91 | 1.00 | 0.95 | 0.54 |
| Vnn1 | 1.00 | 1.00 | 1.00 | 1.00 | 3.38 | 1.00 | 2.77 | 5.26 | 3.48 | 1.00 | 1.00 | 1.00 |
| Vpreb3 | 0.47 | 1.00 | 0.28 | 1.00 | 1.00 | 1.00 | 1.16 | 2.25 | 1.00 | 0.95 | 0.73 | 1.09 |
| Vps16 | 0.85 | 1.00 | 1.35 | 0.97 | 1.20 | 0.79 | 0.99 | 6.95 | 1.15 | 2.63 | 1.25 | 1.15 |
| Vps28 | 1.05 | 1.07 | 0.87 | 1.02 | 1.10 | 1.15 | 1.40 | 7.25 | 0.96 | 3.01 | 1.31 | 1.18 |
| Vps36 | 0.77 | 1.29 | 0.94 | 0.50 | 5.20 | 1.22 | 0.93 | 3.06 | 0.95 | 3.03 | 0.90 | 1.13 |

Fig. 35- 285

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Vps45 | 1.09 | 0.49 | 0.60 | 0.35 | 5.80 | 0.91 | 0.67 | 1.02 | 1.19 | 4.27 | 5.17 | 0.90 |
| Vps53 | 0.98 | 0.52 | 1.02 | 0.59 | 3.41 | 1.04 | 0.90 | 0.74 | 0.91 | 2.10 | 2.69 | 1.08 |
| Vps8 | 1.17 | 0.60 | 0.91 | 0.63 | 4.50 | 0.92 | 0.82 | 0.84 | 0.71 | 1.66 | 2.34 | 0.96 |
| Vsig8 | 1.00 | 1.00 | 1.00 | 1.00 | 1.00 | 1.00 | 1.00 | 1.00 | 1.00 | 1.15 | 3.07 | 1.00 |
| Vsnl1 | 1.00 | 1.00 | 1.00 | 1.00 | 0.06 | 1.00 | 1.00 | 1.00 | 1.00 | 0.57 | 0.54 | 0.73 |
| Wasf1 | 1.00 | 1.00 | 1.00 | 1.00 | 0.17 | 1.00 | 1.00 | 1.00 | 1.00 | 1.00 | 1.00 | 1.00 |
| Wbscr22 | 1.06 | 0.71 | 1.10 | 0.97 | 4.86 | 1.00 | 0.84 | 0.94 | 0.96 | 1.51 | 2.58 | 0.94 |
| Wdr34 | 0.88 | 0.56 | 1.28 | 0.67 | 3.93 | 0.96 | 0.98 | 0.74 | 0.95 | 4.02 | 3.49 | 0.88 |
| Wdr65 | 1.00 | 1.00 | 1.00 | 1.00 | 1.00 | 1.00 | 1.00 | 1.00 | 1.00 | 2.86 | 4.72 | 1.46 |
| Wdr74 | 1.31 | 0.52 | 1.16 | 0.78 | 9.92 | 1.29 | 1.38 | 1.16 | 1.01 | 3.80 | 4.17 | 1.28 |
| Wdr83 | 0.86 | 0.62 | 0.81 | 0.25 | 3.43 | 0.89 | 0.96 | 1.18 | 0.88 | 1.26 | 2.16 | 0.96 |
| Wdr83os | 1.37 | 0.88 | 0.84 | 0.54 | 3.42 | 0.95 | 0.90 | 0.72 | 0.97 | 0.92 | 2.01 | 0.91 |
| Wdr92 | 0.73 | 0.55 | 0.64 | 0.86 | 2.57 | 0.96 | 0.97 | 1.12 | 0.99 | 2.71 | 3.02 | 1.33 |
| Wdr95 | 1.00 | 1.00 | 1.00 | 1.00 | 1.00 | 1.00 | 1.00 | 1.00 | 1.00 | 2.57 | 5.24 | 1.00 |
| Wfdc10 | 1.00 | 1.00 | 1.00 | 1.00 | 1.00 | 1.00 | 1.00 | 1.00 | 1.00 | 2.36 | 2.67 | 1.11 |
| Wfdc12 | 1.00 | 1.00 | 1.00 | 1.00 | 1.00 | 1.00 | 1.00 | 1.00 | 1.00 | 3.86 | 5.60 | 1.15 |
| Wfdc13 | 1.00 | 1.00 | 1.00 | 1.00 | 1.00 | 1.00 | 1.00 | 1.00 | 1.00 | 1.00 | 1.08 | 1.00 |
| Wfdc15b | 1.00 | 1.00 | 1.00 | 1.00 | 1.00 | 1.00 | 1.00 | 1.00 | 1.00 | 1.00 | 1.00 | 1.00 |
| Wfdc17 | 2.19 | 0.38 | 1.42 | 0.71 | 4.41 | 1.17 | 1.38 | 1.12 | 1.29 | 2.48 | 2.67 | 0.76 |
| Wfdc18 | 1.00 | 1.00 | 1.00 | 1.00 | 1.00 | 1.00 | 1.00 | 1.00 | 1.00 | 1.00 | 1.00 | 1.00 |
| Wfdc2 | 1.00 | 1.00 | 1.00 | 1.00 | 2.69 | 1.00 | 1.00 | 1.00 | 1.00 | 3.34 | 4.47 | 1.06 |
| Wfdc3 | 1.00 | 1.00 | 1.00 | 1.00 | 1.00 | 1.00 | 1.00 | 1.00 | 1.00 | 1.88 | 1.72 | 1.00 |
| Wfikkn1 | 1.00 | 1.00 | 1.00 | 1.00 | 2.16 | 1.00 | 1.00 | 1.00 | 1.00 | 3.87 | 4.80 | 1.00 |
| Wibg | 1.12 | 1.17 | 0.94 | 0.81 | 2.42 | 1.07 | 0.82 | 0.86 | 0.84 | 0.63 | 1.27 | 0.92 |
| Wif1 | 0.38 | 0.51 | 0.54 | 1.00 | 1.00 | 1.00 | 0.11 | 0.10 | 0.12 | 28.21 | 33.36 | 42.02 |
| Wipf3 | 1.07 | 0.61 | 0.72 | 4.61 | 0.78 | 1.36 | 0.82 | 0.94 | 0.63 | 1.07 | 1.09 | 1.07 |
| Wnt11 | 2.08 | 1.83 | 1.34 | 1.44 | 6.79 | 2.10 | 2.13 | 1.35 | 1.23 | 0.99 | 1.91 | 1.25 |
| Wrap53 | 1.03 | 0.47 | 0.89 | 0.46 | 3.53 | 0.68 | 1.00 | 0.92 | 0.91 | 2.37 | 3.85 | 1.00 |
| Xaf1 | 1.23 | 1.01 | 1.52 | 1.44 | 5.86 | 1.72 | 1.53 | 1.14 | 1.70 | 2.77 | 2.19 | 1.54 |
| Xlr4c | 1.00 | 1.00 | 1.00 | 1.00 | 1.00 | 1.00 | 1.00 | 1.00 | 1.00 | 5.43 | 2.67 | 1.24 |
| Xpnpep1 | 1.13 | 0.85 | 1.18 | 0.88 | 5.71 | 1.18 | 1.06 | 1.17 | 1.03 | 2.79 | 3.01 | 1.13 |
| Xrcc1 | 0.93 | 0.66 | 0.95 | 1.33 | 5.19 | 1.33 | 1.25 | 1.24 | 1.09 | 4.41 | 2.51 | 1.06 |
| Ybx2 | 0.86 | 0.95 | 1.18 | 0.74 | 1.70 | 0.90 | 1.13 | 0.84 | 0.83 | 1.00 | 1.20 | 1.00 |
| Yif1b | 1.22 | 0.58 | 0.95 | 0.18 | 4.30 | 0.83 | 1.33 | 0.82 | 0.84 | 1.21 | 2.75 | 0.87 |
| Yipf1 | 1.78 | 0.62 | 0.95 | 0.59 | 3.20 | 1.14 | 0.94 | 1.03 | 0.95 | 1.62 | 2.20 | 0.89 |
| Yipf2 | 0.91 | 0.93 | 1.25 | 0.85 | 3.95 | 0.90 | 0.74 | 0.67 | 1.10 | 1.22 | 1.47 | 1.07 |
| Ypel3 | 1.13 | 0.75 | 1.02 | 0.73 | 5.49 | 1.29 | 1.38 | 1.06 | 1.07 | 1.28 | 1.99 | 1.03 |
| Zap70 | 1.00 | 1.22 | 1.00 | 1.00 | 1.00 | 1.00 | 1.00 | 1.00 | 1.00 | 1.56 | 2.93 | 0.97 |
| Zbp1 | 1.00 | 1.00 | 1.00 | 1.39 | 2.19 | 1.00 | 1.00 | 1.00 | 1.97 | 2.40 | 2.17 | 1.39 |
| Zbtb16 | 0.84 | 1.78 | 1.58 | 6.22 | 0.42 | 2.25 | 1.70 | 4.59 | 2.42 | 1.77 | 0.65 | 2.36 |
| Zbtb22 | 0.77 | 1.05 | 0.87 | 0.65 | 0.77 | 0.92 | 1.09 | 0.90 | 0.97 | 0.83 | 0.80 | 1.12 |
| Zbtb38 | 0.62 | 1.00 | 1.11 | 5.07 | 0.63 | 0.97 | 1.98 | 3.45 | 2.10 | 1.00 | 1.00 | 1.14 |
| Zbtb8b | 1.00 | 1.00 | 1.00 | 1.00 | 1.00 | 1.00 | 1.00 | 1.00 | 1.00 | 1.00 | 1.00 | 1.00 |
| Zbtb8os | 1.33 | 0.66 | 0.57 | 0.40 | 13.82 | 1.42 | 0.74 | 1.48 | 1.11 | 3.75 | 5.18 | 1.24 |
| Zcchc12 | 1.00 | 1.00 | 1.00 | 1.00 | 0.25 | 1.00 | 1.00 | 1.00 | 1.00 | 1.00 | 1.00 | 1.00 |
| Zcchc17 | 0.98 | 0.53 | 0.66 | 0.44 | 3.90 | 0.97 | 0.73 | 0.83 | 0.86 | 2.11 | 3.14 | 0.91 |
| Zcwpw1 | 1.00 | 1.00 | 1.00 | 1.21 | 9.02 | 1.00 | 1.00 | 1.00 | 1.00 | 1.00 | 1.00 | 1.00 |
| Zeb2os | 1.00 | 0.54 | 0.94 | 1.29 | 7.01 | 1.34 | 1.12 | 0.54 | 0.82 | 2.49 | 1.47 | 0.88 |
| Zfand2b | 1.68 | 0.91 | 1.30 | 0.47 | 21.03 | 1.53 | 1.15 | 0.75 | 0.82 | 2.43 | 4.45 | 0.98 |
| Zfp36 | 2.41 | 7.06 | 2.09 | 1.87 | 0.28 | 1.84 | 1.33 | 1.58 | 1.31 | 0.36 | 0.31 | 1.25 |
| Zfp365 | 1.00 | 1.00 | 1.00 | 1.00 | 0.13 | 1.00 | 1.00 | 1.00 | 1.00 | 1.01 | 0.92 | 1.30 |
| Zfp429 | 1.65 | 1.00 | 1.00 | 1.90 | 1.00 | 1.33 | 1.91 | 1.56 | 1.31 | 1.41 | 1.91 | 4.79 |
| Zfp524 | 1.06 | 0.62 | 0.94 | 0.66 | 6.62 | 0.97 | 1.06 | 0.66 | 1.08 | 2.29 | 2.42 | 0.96 |
| Zfp57 | 1.00 | 1.00 | 1.00 | 1.84 | 1.56 | 1.00 | 2.03 | 1.96 | 3.62 | 4.48 | 4.22 | 2.20 |
| Zfp580 | 0.98 | 0.77 | 0.80 | 0.48 | 1.60 | 0.82 | 1.21 | 0.81 | 0.67 | 0.55 | 1.02 | 0.90 |
| Zfp593 | 1.25 | 0.83 | 1.26 | 0.82 | 6.62 | 1.43 | 1.59 | 2.05 | 2.00 | 2.03 | 1.90 | 1.23 |
| Zfp637 | 1.06 | 0.89 | 0.80 | 1.97 | 5.08 | 1.36 | 0.93 | 0.89 | 0.93 | 0.77 | 1.33 | 0.99 |
| Zfp688 | 0.96 | 0.47 | 1.37 | 0.45 | 7.12 | 1.09 | 1.26 | 1.18 | 1.41 | 2.41 | 2.88 | 0.96 |
| Zfp771 | 1.59 | 0.95 | 1.27 | 0.46 | 6.36 | 1.17 | 1.84 | 1.11 | 1.15 | 1.86 | 3.05 | 1.06 |
| Zfp809 | 0.90 | 0.88 | 1.57 | 0.78 | 2.88 | 1.00 | 1.98 | 2.46 | 2.32 | 5.77 | 9.16 | 1.74 |
| Zfp821 | 0.87 | 0.77 | 0.88 | 1.06 | 7.44 | 1.46 | 1.23 | 1.15 | 0.98 | 1.61 | 2.09 | 1.05 |
| Zfp97 | 2.21 | 1.48 | 3.00 | 1.52 | 1.00 | 1.83 | 7.37 | 5.76 | 3.16 | 1.00 | 0.88 | 3.42 |
| Zfpl1 | 1.00 | 0.62 | 1.22 | 0.89 | 6.42 | 1.27 | 1.16 | 0.97 | 0.84 | 1.54 | 2.47 | 0.92 |
| Zg16 | 1.00 | 1.00 | 0.69 | 1.00 | 1.00 | 1.07 | 1.00 | 1.00 | 1.00 | 1.00 | 1.00 | 1.95 |

Fig. 35- 286

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Vps45 | 1.01 | 1.03 | 0.85 | 1.15 | 0.40 | 0.83 | 1.00 | 2.24 | 0.98 | 1.05 | 1.46 | 0.76 |
| Vps53 | 1.08 | 1.10 | 1.12 | 1.13 | 0.71 | 0.98 | 1.19 | 1.69 | 0.99 | 0.92 | 1.27 | 1.07 |
| Vps8 | 1.36 | 1.43 | 1.09 | 0.81 | 0.83 | 0.89 | 1.00 | 1.37 | 1.00 | 0.95 | 1.29 | 0.91 |
| Vsig8 | 2.39 | 2.43 | 1.86 | 1.00 | 1.60 | 1.00 | 1.00 | 1.00 | 1.00 | 0.74 | 1.80 | 1.00 |
| Vsnl1 | 1.01 | 0.67 | 0.68 | 1.00 | 1.00 | 1.00 | 1.00 | 1.00 | 1.00 | 1.00 | 1.00 | 1.00 |
| Wasf1 | 1.42 | 1.29 | 1.11 | 1.05 | 1.00 | 0.69 | 1.00 | 1.00 | 1.00 | 0.88 | 0.93 | 1.14 |
| Wbscr22 | 0.98 | 1.34 | 0.78 | 0.99 | 0.83 | 1.14 | 0.81 | 1.06 | 1.13 | 0.85 | 1.45 | 1.17 |
| Wdr34 | 1.16 | 1.78 | 1.13 | 0.78 | 0.54 | 0.93 | 1.46 | 2.46 | 1.34 | 0.93 | 1.46 | 1.02 |
| Wdr65 | 1.00 | 1.00 | 1.00 | 1.00 | 1.00 | 1.00 | 1.00 | 1.00 | 1.00 | 1.00 | 1.00 | 1.00 |
| Wdr74 | 1.00 | 1.34 | 1.00 | 1.04 | 0.58 | 0.82 | 1.22 | 2.47 | 0.78 | 0.71 | 1.29 | 0.98 |
| Wdr83 | 0.97 | 1.27 | 0.89 | 0.62 | 0.79 | 0.85 | 1.23 | 1.10 | 0.85 | 0.93 | 1.45 | 1.16 |
| Wdr83os | 0.95 | 1.49 | 0.84 | 0.73 | 0.81 | 0.89 | 0.99 | 0.51 | 0.86 | 0.78 | 1.67 | 1.03 |
| Wdr92 | 1.10 | 1.13 | 0.91 | 0.98 | 0.56 | 0.88 | 2.22 | 1.88 | 1.10 | 1.21 | 1.16 | 0.89 |
| Wdr95 | 1.00 | 1.00 | 1.00 | 1.00 | 1.00 | 1.00 | 1.00 | 1.00 | 1.00 | 1.00 | 1.00 | 1.00 |
| Wfdc10 | 1.00 | 1.00 | 1.00 | 1.00 | 1.00 | 1.00 | 1.00 | 1.00 | 1.00 | 1.00 | 1.00 | 1.00 |
| Wfdc12 | 1.04 | 1.00 | 1.00 | 1.00 | 1.00 | 1.00 | 1.00 | 6.34 | 1.00 | 1.00 | 1.00 | 1.00 |
| Wfdc13 | 1.00 | 1.00 | 1.00 | 1.00 | 1.00 | 1.00 | 1.00 | 1.00 | 1.00 | 1.00 | 1.00 | 1.00 |
| Wfdc15b | 1.00 | 1.00 | 1.00 | 0.68 | 0.81 | 0.76 | 1.00 | 1.11 | 1.00 | 1.00 | 1.00 | 1.00 |
| Wfdc17 | 6.53 | 4.77 | 3.30 | 1.00 | 0.24 | 1.00 | 0.37 | 0.87 | 0.64 | 0.98 | 2.05 | 1.39 |
| Wfdc18 | 1.36 | 1.53 | 0.96 | 1.00 | 1.00 | 1.00 | 1.00 | 1.00 | 1.00 | 0.52 | 2.56 | 1.54 |
| Wfdc2 | 2.29 | 3.42 | 1.36 | 0.76 | 0.52 | 0.79 | 0.87 | 1.11 | 0.47 | 0.76 | 1.31 | 0.90 |
| Wfdc3 | 1.00 | 1.00 | 1.00 | 1.00 | 1.00 | 1.00 | 1.00 | 1.75 | 1.00 | 1.00 | 1.00 | 1.00 |
| Wfikkn1 | 1.77 | 1.90 | 0.85 | 1.00 | 0.71 | 1.00 | 1.00 | 3.16 | 1.00 | 1.46 | 1.96 | 1.30 |
| Wibg | 1.10 | 1.38 | 0.88 | 1.04 | 1.10 | 0.81 | 0.95 | 0.59 | 0.99 | 0.98 | 1.46 | 0.97 |
| Wif1 | 1.00 | 1.00 | 1.00 | 1.00 | 0.76 | 1.00 | 1.00 | 1.00 | 1.00 | 1.25 | 1.13 | 1.33 |
| Wipf3 | 0.80 | 0.84 | 1.08 | 1.38 | 1.38 | 1.43 | 0.77 | 0.84 | 1.16 | 0.87 | 0.65 | 0.94 |
| Wnt11 | 1.31 | 1.35 | 1.35 | 0.92 | 1.00 | 1.00 | 1.00 | 1.00 | 1.00 | 1.05 | 1.29 | 1.00 |
| Wrap53 | 0.88 | 1.26 | 0.99 | 1.10 | 0.57 | 1.11 | 0.90 | 1.64 | 1.05 | 0.81 | 1.01 | 1.02 |
| Xaf1 | 2.64 | 2.25 | 2.06 | 1.60 | 2.16 | 1.44 | 1.00 | 1.71 | 1.00 | 2.52 | 3.72 | 1.93 |
| Xlr4c | 1.38 | 1.58 | 1.31 | 1.00 | 1.00 | 1.00 | 1.00 | 1.00 | 1.00 | 1.02 | 1.00 | 1.00 |
| Xpnpep1 | 1.10 | 1.22 | 1.13 | 1.08 | 0.78 | 0.90 | 1.14 | 2.48 | 1.15 | 1.11 | 1.48 | 0.95 |
| Xrcc1 | 0.86 | 1.17 | 0.95 | 1.25 | 0.69 | 1.08 | 1.09 | 3.43 | 1.08 | 0.97 | 1.00 | 0.91 |
| Ybx2 | 0.54 | 0.65 | 0.56 | 0.93 | 0.80 | 1.26 | 1.00 | 1.00 | 1.00 | 0.99 | 1.34 | 0.95 |
| Yif1b | 1.09 | 1.64 | 0.99 | 0.89 | 0.84 | 1.05 | 0.98 | 1.00 | 0.80 | 1.37 | 1.00 | 0.93 |
| Yipf1 | 1.17 | 1.42 | 1.08 | 1.06 | 0.63 | 1.00 | 1.03 | 1.38 | 0.81 | 1.00 | 1.40 | 1.08 |
| Yipf2 | 1.21 | 1.37 | 1.05 | 0.85 | 0.83 | 0.94 | 0.85 | 0.98 | 0.89 | 1.05 | 1.49 | 1.03 |
| Ypel3 | 1.26 | 1.76 | 1.06 | 1.35 | 1.56 | 1.58 | 1.13 | 0.98 | 1.15 | 1.05 | 1.51 | 1.14 |
| Zap70 | 1.10 | 1.38 | 1.03 | 1.00 | 1.00 | 1.00 | 1.16 | 2.85 | 2.08 | 1.00 | 1.61 | 0.98 |
| Zbp1 | 2.05 | 2.01 | 2.57 | 1.00 | 1.00 | 1.00 | 1.17 | 1.56 | 2.50 | 4.17 | 3.76 | 1.91 |
| Zbtb16 | 3.93 | 1.36 | 5.60 | 2.67 | 1.00 | 3.99 | 1.45 | 1.00 | 2.65 | 1.50 | 0.45 | 1.73 |
| Zbtb22 | 0.94 | 0.92 | 1.00 | 0.95 | 2.00 | 1.12 | 1.01 | 0.78 | 1.01 | 1.16 | 1.05 | 1.05 |
| Zbtb38 | 0.35 | 0.23 | 0.95 | 1.70 | 1.00 | 1.75 | 1.13 | 1.00 | 1.23 | 1.17 | 0.41 | 0.87 |
| Zbtb8b | 4.07 | 5.04 | 3.45 | 1.00 | 1.00 | 1.00 | 1.00 | 1.00 | 1.00 | 1.00 | 1.00 | 1.00 |
| Zbtb8os | 1.19 | 1.12 | 0.98 | 0.86 | 0.64 | 0.62 | 0.82 | 2.40 | 1.12 | 1.10 | 1.72 | 1.54 |
| Zcchc12 | 0.95 | 1.20 | 1.11 | 1.00 | 1.00 | 1.00 | 1.00 | 1.00 | 1.00 | 0.99 | 0.75 | 0.91 |
| Zcchc17 | 0.96 | 1.39 | 1.06 | 0.87 | 0.63 | 0.82 | 1.42 | 2.55 | 1.15 | 0.96 | 1.56 | 1.18 |
| Zcwpw1 | 1.00 | 0.86 | 0.72 | 1.00 | 0.34 | 1.00 | 1.00 | 0.92 | 1.00 | 1.00 | 1.00 | 1.00 |
| Zeb2os | 1.51 | 1.79 | 2.17 | 0.65 | 0.48 | 0.73 | 1.00 | 1.00 | 1.00 | 1.00 | 1.11 | 1.00 |
| Zfand2b | 1.16 | 1.73 | 1.16 | 0.94 | 0.76 | 0.97 | 1.34 | 2.38 | 1.29 | 1.30 | 1.84 | 1.08 |
| Zfp36 | 0.83 | 0.82 | 1.05 | 1.51 | 3.06 | 1.25 | 1.21 | 0.43 | 1.02 | 1.10 | 1.10 | 1.09 |
| Zfp365 | 1.27 | 0.86 | 1.70 | 0.82 | 1.00 | 0.56 | 1.00 | 1.00 | 1.00 | 0.75 | 0.89 | 0.97 |
| Zfp429 | 11.16 | 10.34 | 10.63 | 2.45 | 1.00 | 2.67 | 1.00 | 1.00 | 1.00 | 7.19 | 6.13 | 6.19 |
| Zfp524 | 1.07 | 1.31 | 0.96 | 1.01 | 0.55 | 0.84 | 0.74 | 1.96 | 0.91 | 0.87 | 1.17 | 0.83 |
| Zfp57 | 18.14 | 18.41 | 10.02 | 2.06 | 1.36 | 1.82 | 1.40 | 4.72 | 1.58 | 0.96 | 0.81 | 0.86 |
| Zfp580 | 0.71 | 1.06 | 0.65 | 0.66 | 0.63 | 0.82 | 0.90 | 0.61 | 1.50 | 0.97 | 1.01 | 1.04 |
| Zfp593 | 1.16 | 1.55 | 0.93 | 1.29 | 0.81 | 0.79 | 1.23 | 1.60 | 0.97 | 1.04 | 1.28 | 1.18 |
| Zfp637 | 1.20 | 1.47 | 1.07 | 1.07 | 0.99 | 0.92 | 0.78 | 0.81 | 0.92 | 1.01 | 1.33 | 0.88 |
| Zfp688 | 1.09 | 1.75 | 0.82 | 1.06 | 0.75 | 0.92 | 0.98 | 2.12 | 0.75 | 1.11 | 1.83 | 1.02 |
| Zfp771 | 2.00 | 2.58 | 1.50 | 1.27 | 1.18 | 1.40 | 1.20 | 1.38 | 1.07 | 0.96 | 1.66 | 1.03 |
| Zfp809 | 0.88 | 0.81 | 1.03 | 1.36 | 1.39 | 1.25 | 0.97 | 2.08 | 0.66 | 1.00 | 1.34 | 1.05 |
| Zfp821 | 1.24 | 1.38 | 0.90 | 1.10 | 1.02 | 0.97 | 0.64 | 1.91 | 1.18 | 0.91 | 1.61 | 1.01 |
| Zfp97 | 4.18 | 3.62 | 4.52 | 2.14 | 1.00 | 2.05 | 1.59 | 1.00 | 1.24 | 3.18 | 3.21 | 2.19 |
| Zfpl1 | 1.23 | 1.50 | 1.19 | 0.86 | 0.85 | 0.88 | 1.06 | 1.54 | 0.94 | 1.06 | 1.49 | 1.04 |
| Zg16 | 1.87 | 1.43 | 5.85 | 1.00 | 0.72 | 0.85 | 1.00 | 2.09 | 0.70 | 1.53 | 2.61 | 1.85 |

Fig. 35- 287

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Vps45 | 0.71 | 0.76 | 0.78 | 0.77 | 2.08 | 0.78 | 0.99 | 4.74 | 1.23 | 0.86 | 1.11 | 0.78 |
| Vps53 | 1.06 | 0.92 | 0.85 | 0.73 | 1.22 | 1.04 | 0.99 | 2.11 | 1.10 | 0.93 | 1.18 | 0.96 |
| Vps8 | 1.00 | 0.91 | 0.79 | 0.77 | 1.92 | 0.75 | 0.95 | 1.65 | 0.85 | 1.35 | 1.17 | 1.06 |
| Vsig8 | 1.01 | 1.53 | 1.45 | 1.00 | 1.00 | 0.73 | 0.65 | 1.27 | 1.11 | 1.00 | 1.00 | 1.00 |
| Vsnl1 | 1.00 | 0.96 | 1.03 | 1.00 | 1.00 | 1.00 | 1.00 | 1.00 | 1.00 | 1.00 | 31.18 | 1.00 |
| Wasf1 | 1.00 | 1.05 | 1.39 | 0.51 | 1.00 | 0.68 | 1.04 | 0.69 | 0.86 | 1.19 | 6.02 | 0.63 |
| Wbscr22 | 0.98 | 1.02 | 0.86 | 0.85 | 4.39 | 1.18 | 0.93 | 1.32 | 1.14 | 1.04 | 1.33 | 0.93 |
| Wdr34 | 1.16 | 1.44 | 0.87 | 1.16 | 1.16 | 1.20 | 1.07 | 4.55 | 1.06 | 1.14 | 1.42 | 0.80 |
| Wdr65 | 1.00 | 1.00 | 1.00 | 1.00 | 1.00 | 1.00 | 1.27 | 2.12 | 1.27 | 1.00 | 1.00 | 1.00 |
| Wdr74 | 1.01 | 0.95 | 1.24 | 1.25 | 3.33 | 1.22 | 0.95 | 2.51 | 0.93 | 1.18 | 1.31 | 1.08 |
| Wdr83 | 1.08 | 1.08 | 0.81 | 0.90 | 5.73 | 1.01 | 1.26 | 1.66 | 0.95 | 1.06 | 1.42 | 1.39 |
| Wdr83os | 0.98 | 1.00 | 0.93 | 0.89 | 13.26 | 0.94 | 0.93 | 0.83 | 0.91 | 1.08 | 1.09 | 0.77 |
| Wdr92 | 1.07 | 0.79 | 1.15 | 3.49 | 1.20 | 1.87 | 0.96 | 2.63 | 0.99 | 1.14 | 1.03 | 1.08 |
| Wdr95 | 1.00 | 1.00 | 1.00 | 0.93 | 5.36 | 1.44 | 1.00 | 1.61 | 1.00 | 1.00 | 1.00 | 1.00 |
| Wfdc10 | 1.00 | 1.22 | 1.00 | 0.46 | 29.56 | 0.01 | 1.17 | 1.62 | 1.30 | 1.00 | 1.00 | 1.00 |
| Wfdc12 | 1.81 | 2.22 | 2.32 | 2.06 | 4.26 | 1.00 | 1.00 | 1.00 | 1.00 | 1.00 | 1.00 | 1.00 |
| Wfdc13 | 1.00 | 1.00 | 1.00 | 1.00 | 5.30 | 0.01 | 1.00 | 1.00 | 1.00 | 1.00 | 1.00 | 1.00 |
| Wfdc15b | 0.93 | 1.00 | 1.10 | 1.00 | 7.25 | 0.03 | 1.00 | 1.00 | 1.00 | 1.00 | 1.00 | 1.00 |
| Wfdc17 | 1.49 | 1.18 | 0.77 | 0.72 | 2.34 | 1.09 | 0.78 | 1.34 | 1.01 | 1.23 | 0.80 | 1.86 |
| Wfdc18 | 1.00 | 3.53 | 3.09 | 1.00 | 1.00 | 1.00 | 1.00 | 1.00 | 1.00 | 1.00 | 1.00 | 1.00 |
| Wfdc2 | 1.65 | 1.54 | 1.68 | 1.27 | 2.50 | 2.12 | 1.00 | 1.79 | 1.00 | 1.00 | 1.00 | 1.00 |
| Wfdc3 | 1.00 | 1.00 | 1.00 | 1.00 | 1.00 | 1.00 | 0.91 | 2.12 | 0.64 | 1.00 | 1.00 | 1.00 |
| Wfikkn1 | 1.37 | 1.53 | 1.14 | 1.00 | 1.00 | 1.00 | 1.20 | 2.37 | 1.00 | 1.10 | 2.55 | 0.68 |
| Wibg | 1.01 | 1.08 | 0.96 | 1.12 | 10.17 | 1.22 | 0.93 | 0.49 | 1.01 | 1.17 | 1.41 | 1.00 |
| Wif1 | 1.00 | 1.00 | 1.00 | 1.00 | 1.00 | 1.00 | 1.01 | 1.00 | 1.00 | 1.42 | 1.75 | 1.04 |
| Wipf3 | 1.06 | 1.24 | 1.05 | 1.31 | 1.10 | 1.86 | 1.18 | 0.88 | 1.04 | 1.93 | 7.44 | 2.45 |
| Wnt11 | 0.95 | 1.20 | 0.86 | 1.83 | 1.11 | 0.86 | 1.00 | 1.00 | 1.00 | 0.90 | 1.17 | 0.92 |
| Wrap53 | 0.86 | 0.62 | 0.97 | 0.87 | 2.51 | 1.30 | 1.38 | 3.70 | 1.05 | 1.05 | 1.04 | 0.86 |
| Xaf1 | 3.15 | 4.54 | 3.60 | 1.09 | 1.82 | 1.59 | 1.46 | 2.80 | 1.25 | 3.45 | 2.56 | 2.27 |
| Xlr4c | 1.18 | 1.00 | 1.00 | 1.00 | 1.00 | 1.00 | 0.99 | 1.52 | 1.00 | 1.40 | 1.20 | 1.25 |
| Xpnpep1 | 0.80 | 0.79 | 0.78 | 1.14 | 2.40 | 1.08 | 1.15 | 2.36 | 0.97 | 1.02 | 1.00 | 0.81 |
| Xrcc1 | 0.84 | 1.01 | 0.90 | 0.74 | 1.49 | 0.98 | 1.01 | 4.66 | 1.18 | 1.12 | 1.33 | 1.04 |
| Ybx2 | 1.10 | 1.58 | 1.18 | 1.60 | 0.85 | 0.98 | 0.93 | 0.88 | 1.09 | 1.00 | 1.00 | 1.00 |
| Yif1b | 1.27 | 1.02 | 0.97 | 0.97 | 6.46 | 0.96 | 0.79 | 1.43 | 0.95 | 1.22 | 1.80 | 0.84 |
| Yipf1 | 0.82 | 0.86 | 0.93 | 0.69 | 2.88 | 0.88 | 1.17 | 1.87 | 0.97 | 1.23 | 1.12 | 1.00 |
| Yipf2 | 1.01 | 0.87 | 1.03 | 0.80 | 3.16 | 0.90 | 1.02 | 1.18 | 0.87 | 0.87 | 0.95 | 1.04 |
| Ypel3 | 1.32 | 1.50 | 1.66 | 1.35 | 3.13 | 1.44 | 1.01 | 0.96 | 1.07 | 1.13 | 1.34 | 1.09 |
| Zap70 | 1.00 | 1.00 | 1.00 | 1.00 | 1.00 | 0.76 | 1.40 | 2.88 | 0.71 | 0.77 | 0.87 | 0.84 |
| Zbp1 | 3.29 | 5.75 | 3.75 | 2.30 | 1.94 | 2.54 | 1.00 | 1.00 | 1.00 | 2.49 | 1.67 | 1.90 |
| Zbtb16 | 2.03 | 2.98 | 2.80 | 2.17 | 0.33 | 2.19 | 1.67 | 1.00 | 1.65 | 2.29 | 1.50 | 5.73 |
| Zbtb22 | 1.13 | 1.17 | 0.87 | 1.11 | 0.50 | 1.06 | 1.01 | 0.87 | 0.98 | 0.99 | 0.92 | 0.92 |
| Zbtb38 | 1.18 | 1.00 | 0.73 | 1.37 | 0.19 | 0.28 | 1.68 | 1.00 | 1.16 | 0.97 | 0.46 | 1.43 |
| Zbtb8b | 1.00 | 1.00 | 1.00 | 1.00 | 1.00 | 1.00 | 1.08 | 1.00 | 0.85 | 1.00 | 1.00 | 1.00 |
| Zbtb8os | 0.83 | 0.75 | 1.13 | 0.81 | 1.13 | 1.01 | 0.69 | 3.94 | 1.06 | 1.05 | 1.43 | 1.15 |
| Zcchc12 | 1.30 | 1.14 | 1.32 | 1.00 | 1.00 | 1.00 | 0.89 | 1.00 | 1.29 | 1.00 | 7.38 | 1.00 |
| Zcchc17 | 0.77 | 1.17 | 0.93 | 1.05 | 1.80 | 1.04 | 1.22 | 2.84 | 0.85 | 1.02 | 1.47 | 1.00 |
| Zcwpw1 | 1.00 | 1.00 | 1.00 | 0.64 | 3.02 | 0.69 | 1.08 | 2.70 | 1.39 | 2.08 | 1.01 | 2.04 |
| Zeb2os | 1.00 | 1.00 | 1.31 | 0.80 | 0.83 | 0.58 | 1.00 | 1.00 | 1.00 | 1.00 | 1.33 | 0.83 |
| Zfand2b | 1.26 | 1.07 | 1.14 | 1.55 | 6.51 | 1.52 | 1.00 | 1.80 | 0.66 | 0.87 | 1.44 | 1.00 |
| Zfp36 | 1.48 | 1.75 | 1.15 | 1.41 | 0.13 | 1.36 | 0.97 | 1.00 | 1.35 | 1.00 | 0.71 | 0.99 |
| Zfp365 | 1.00 | 1.03 | 1.00 | 1.00 | 1.00 | 0.88 | 1.00 | 1.00 | 1.00 | 1.18 | 9.88 | 2.78 |
| Zfp429 | 4.23 | 3.38 | 3.51 | 3.44 | 1.00 | 2.81 | 1.02 | 1.00 | 1.00 | 15.34 | 13.64 | 14.30 |
| Zfp524 | 1.02 | 1.00 | 0.93 | 0.91 | 1.86 | 1.14 | 0.97 | 2.56 | 1.14 | 0.81 | 0.94 | 0.85 |
| Zfp57 | 1.74 | 1.13 | 0.86 | 2.94 | 5.26 | 2.46 | 0.69 | 1.06 | 0.62 | 3.07 | 2.62 | 2.36 |
| Zfp580 | 0.80 | 0.83 | 0.99 | 0.80 | 5.08 | 0.88 | 0.82 | 0.33 | 0.65 | 0.99 | 1.32 | 0.75 |
| Zfp593 | 0.88 | 0.96 | 1.06 | 1.31 | 1.91 | 1.12 | 0.93 | 1.86 | 1.00 | 1.13 | 1.14 | 1.12 |
| Zfp637 | 1.04 | 1.18 | 1.18 | 1.23 | 2.03 | 1.21 | 0.93 | 0.86 | 0.67 | 1.18 | 1.43 | 1.05 |
| Zfp688 | 1.12 | 1.12 | 1.06 | 0.81 | 2.13 | 0.87 | 0.87 | 2.34 | 0.97 | 1.01 | 1.22 | 1.10 |
| Zfp771 | 1.26 | 1.46 | 1.26 | 1.38 | 3.20 | 1.26 | 0.80 | 1.77 | 0.94 | 1.28 | 1.65 | 0.93 |
| Zfp809 | 1.98 | 1.53 | 1.16 | 1.20 | 2.16 | 0.98 | 0.98 | 2.28 | 0.68 | 1.22 | 0.97 | 1.45 |
| Zfp821 | 0.97 | 1.25 | 0.94 | 1.09 | 8.94 | 1.29 | 0.95 | 1.59 | 1.01 | 1.33 | 1.52 | 1.16 |
| Zfp97 | 3.06 | 2.49 | 2.34 | 3.42 | 1.07 | 3.60 | 2.69 | 1.00 | 1.82 | 6.26 | 4.51 | 6.52 |
| Zfpl1 | 0.93 | 1.03 | 0.94 | 0.96 | 3.10 | 1.02 | 0.85 | 1.39 | 1.00 | 1.10 | 1.27 | 0.95 |
| Zg16 | 24.41 | 3.86 | 3.36 | 1.00 | 1.00 | 0.63 | 1.00 | 3.37 | 0.99 | 6.95 | 10.08 | 1.07 |

Fig. 35- 288

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Vps45 | 1.00 | 1.00 | 1.00 | 1.12 | 0.83 | 0.95 | 1.37 | 14.94 | 0.80 | 2.66 | 0.81 | 0.79 |
| Vps53 | 0.98 | 1.24 | 1.00 | 1.08 | 0.81 | 1.05 | 1.07 | 6.37 | 0.84 | 2.53 | 1.12 | 1.07 |
| Vps8 | 1.00 | 1.00 | 1.00 | 0.95 | 1.03 | 0.88 | 0.99 | 7.11 | 1.00 | 2.32 | 1.34 | 0.83 |
| Vsig8 | 1.00 | 1.00 | 1.00 | 1.00 | 0.22 | 1.00 | 4.00 | 12.96 | 1.22 | 1.00 | 1.00 | 1.00 |
| Vsnl1 | 1.00 | 1.00 | 1.00 | 1.14 | 1.28 | 1.05 | 1.00 | 1.00 | 1.00 | 1.00 | 1.00 | 1.00 |
| Wasf1 | 1.00 | 1.00 | 1.00 | 1.06 | 1.48 | 0.98 | 0.93 | 1.94 | 1.00 | 1.00 | 1.00 | 1.00 |
| Wbscr22 | 1.22 | 1.55 | 1.36 | 1.07 | 0.92 | 1.15 | 0.83 | 5.21 | 0.83 | 1.69 | 1.16 | 1.17 |
| Wdr34 | 0.82 | 0.75 | 0.85 | 0.99 | 0.75 | 0.91 | 1.09 | 9.94 | 0.90 | 1.55 | 0.83 | 0.73 |
| Wdr65 | 1.00 | 1.00 | 1.00 | 1.00 | 0.77 | 1.00 | 0.77 | 7.63 | 0.57 | 1.00 | 1.00 | 1.00 |
| Wdr74 | 1.39 | 0.88 | 1.06 | 1.31 | 0.77 | 0.94 | 1.23 | 12.57 | 0.98 | 2.17 | 0.79 | 1.07 |
| Wdr83 | 1.00 | 0.67 | 1.08 | 0.97 | 1.29 | 0.91 | 1.12 | 5.96 | 0.82 | 2.14 | 1.09 | 0.86 |
| Wdr83os | 0.87 | 1.07 | 0.66 | 1.17 | 1.08 | 1.11 | 1.55 | 2.69 | 0.89 | 1.99 | 1.04 | 1.22 |
| Wdr92 | 0.53 | 0.70 | 0.61 | 0.85 | 0.56 | 0.94 | 1.24 | 5.40 | 1.23 | 1.93 | 0.99 | 1.13 |
| Wdr95 | 1.00 | 1.00 | 1.00 | 1.00 | 0.35 | 1.00 | 1.00 | 2.22 | 1.00 | 2.10 | 1.00 | 1.00 |
| Wfdc10 | 1.00 | 1.00 | 1.00 | 1.00 | 1.00 | 1.00 | 1.08 | 1.00 | 1.00 | 1.00 | 1.00 | 1.00 |
| Wfdc12 | 1.00 | 1.00 | 1.00 | 1.00 | 3.02 | 1.00 | 0.47 | 19.27 | 1.64 | 1.00 | 1.00 | 1.00 |
| Wfdc13 | 1.00 | 1.00 | 1.00 | 1.00 | 1.00 | 1.00 | 1.00 | 1.00 | 1.00 | 1.00 | 1.00 | 1.00 |
| Wfdc15b | 1.32 | 1.51 | 1.00 | 1.00 | 1.00 | 1.00 | 1.00 | 1.00 | 1.00 | 1.00 | 1.00 | 1.00 |
| Wfdc17 | 0.74 | 1.00 | 1.19 | 1.00 | 0.32 | 1.00 | 0.84 | 8.98 | 1.10 | 3.85 | 0.94 | 1.12 |
| Wfdc18 | 1.00 | 1.00 | 1.00 | 1.00 | 0.33 | 1.00 | 1.00 | 8.82 | 1.36 | 1.00 | 1.00 | 1.00 |
| Wfdc2 | 1.00 | 1.00 | 1.00 | 1.00 | 1.22 | 1.00 | 0.39 | 10.26 | 0.56 | 1.00 | 1.00 | 1.00 |
| Wfdc3 | 1.00 | 1.00 | 1.00 | 1.00 | 2.89 | 1.00 | 3.48 | 8.20 | 1.66 | 1.00 | 1.00 | 1.00 |
| Wfikkn1 | 1.00 | 1.00 | 1.00 | 1.00 | 2.33 | 1.00 | 1.75 | 5.73 | 1.94 | 1.74 | 1.76 | 1.00 |
| Wibg | 1.24 | 0.75 | 0.82 | 1.11 | 14.60 | 1.14 | 1.33 | 1.17 | 1.17 | 1.16 | 1.35 | 1.05 |
| Wif1 | 1.00 | 1.00 | 1.00 | 1.39 | 1.00 | 1.00 | 0.80 | 0.85 | 0.76 | 1.00 | 1.00 | 1.00 |
| Wipf3 | 1.00 | 1.00 | 1.00 | 1.26 | 2.03 | 1.18 | 0.98 | 0.88 | 1.15 | 1.00 | 1.00 | 1.00 |
| Wnt11 | 1.00 | 1.00 | 0.56 | 1.00 | 1.00 | 1.00 | 1.55 | 1.58 | 1.11 | 1.00 | 1.00 | 1.00 |
| Wrap53 | 1.00 | 1.00 | 1.00 | 1.10 | 0.74 | 1.02 | 1.24 | 7.15 | 0.83 | 2.30 | 1.02 | 0.94 |
| Xaf1 | 1.00 | 1.00 | 1.00 | 1.15 | 0.94 | 1.20 | 2.07 | 5.96 | 1.93 | 8.23 | 5.45 | 4.00 |
| Xlr4c | 1.00 | 1.00 | 1.00 | 1.00 | 1.00 | 1.00 | 1.00 | 6.08 | 1.00 | 3.72 | 2.65 | 1.61 |
| Xpnpep1 | 1.73 | 1.79 | 0.88 | 1.05 | 1.02 | 1.08 | 1.34 | 7.40 | 0.86 | 1.70 | 0.91 | 1.07 |
| Xrcc1 | 0.88 | 1.00 | 0.87 | 0.78 | 0.78 | 1.01 | 1.35 | 8.05 | 1.01 | 2.33 | 1.12 | 1.01 |
| Ybx2 | 1.00 | 1.00 | 1.00 | 0.94 | 0.94 | 1.33 | 11.71 | 1.00 | 0.80 | 1.00 | 1.00 | 1.00 |
| Yif1b | 0.76 | 1.35 | 0.76 | 0.93 | 0.78 | 1.00 | 1.25 | 5.29 | 0.92 | 2.74 | 0.87 | 0.96 |
| Yipf1 | 1.41 | 1.32 | 0.98 | 1.22 | 1.33 | 0.98 | 1.20 | 5.17 | 0.92 | 2.62 | 1.22 | 1.18 |
| Yipf2 | 1.14 | 0.67 | 0.83 | 0.94 | 0.87 | 0.94 | 0.86 | 5.03 | 0.80 | 1.22 | 1.21 | 1.33 |
| Ypel3 | 1.41 | 1.21 | 1.49 | 1.13 | 1.01 | 1.07 | 1.28 | 2.79 | 1.12 | 1.85 | 1.65 | 1.29 |
| Zap70 | 1.00 | 1.00 | 1.00 | 1.00 | 0.41 | 1.98 | 1.00 | 8.50 | 1.39 | 2.54 | 1.70 | 0.90 |
| Zbp1 | 1.00 | 1.00 | 1.00 | 1.00 | 1.00 | 1.00 | 1.00 | 1.00 | 1.00 | 5.57 | 3.68 | 3.81 |
| Zbtb16 | 2.05 | 1.38 | 3.02 | 1.07 | 1.00 | 1.37 | 1.35 | 0.14 | 2.10 | 1.00 | 2.01 | 0.85 |
| Zbtb22 | 0.77 | 0.65 | 1.06 | 1.11 | 5.76 | 1.16 | 0.92 | 0.24 | 0.87 | 0.78 | 1.03 | 0.88 |
| Zbtb38 | 1.00 | 1.00 | 1.00 | 0.75 | 1.00 | 0.88 | 0.99 | 1.00 | 1.83 | 1.00 | 0.79 | 0.75 |
| Zbtb8b | 1.00 | 1.00 | 1.00 | 0.84 | 0.41 | 1.03 | 1.00 | 1.00 | 1.00 | 1.00 | 1.00 | 1.00 |
| Zbtb8os | 0.96 | 1.14 | 1.35 | 0.91 | 0.83 | 1.48 | 0.85 | 13.78 | 0.58 | 4.64 | 0.79 | 0.86 |
| Zcchc12 | 1.00 | 1.00 | 1.00 | 1.11 | 2.80 | 1.09 | 1.00 | 1.00 | 1.00 | 1.00 | 1.00 | 1.00 |
| Zcchc17 | 0.81 | 0.85 | 0.83 | 1.24 | 0.89 | 1.05 | 1.38 | 6.89 | 0.84 | 2.25 | 0.94 | 1.03 |
| Zcwpw1 | 1.00 | 1.00 | 1.00 | 1.17 | 0.90 | 0.97 | 1.11 | 8.71 | 1.07 | 1.00 | 1.00 | 1.00 |
| Zeb2os | 1.00 | 1.00 | 1.00 | 1.60 | 0.71 | 1.06 | 0.90 | 5.55 | 0.58 | 1.74 | 1.02 | 1.06 |
| Zfand2b | 1.33 | 0.95 | 1.22 | 0.94 | 0.76 | 1.04 | 1.34 | 13.16 | 0.99 | 3.93 | 1.70 | 1.34 |
| Zfp36 | 2.04 | 2.93 | 1.29 | 1.72 | 1.00 | 1.23 | 1.39 | 0.11 | 1.17 | 0.33 | 1.11 | 1.23 |
| Zfp365 | 1.00 | 1.00 | 1.00 | 0.93 | 0.76 | 0.95 | 0.64 | 0.51 | 0.87 | 1.00 | 1.00 | 1.00 |
| Zfp429 | 1.00 | 1.00 | 1.00 | 1.00 | 1.00 | 1.00 | 2.26 | 1.00 | 1.89 | 2.65 | 6.69 | 5.42 |
| Zfp524 | 0.69 | 0.71 | 0.74 | 1.09 | 0.52 | 0.87 | 1.11 | 9.00 | 0.81 | 2.28 | 1.16 | 1.01 |
| Zfp57 | 1.00 | 1.00 | 1.00 | 0.75 | 1.10 | 0.72 | 1.67 | 2.54 | 1.00 | 1.00 | 1.00 | 1.00 |
| Zfp580 | 1.00 | 1.10 | 1.28 | 1.00 | 1.24 | 0.92 | 0.87 | 2.63 | 0.90 | 0.84 | 0.95 | 1.30 |
| Zfp593 | 0.98 | 1.28 | 1.37 | 0.90 | 1.07 | 0.96 | 0.96 | 3.53 | 0.83 | 1.55 | 0.65 | 0.97 |
| Zfp637 | 0.87 | 1.07 | 1.18 | 1.08 | 1.52 | 1.01 | 1.26 | 1.80 | 1.08 | 1.06 | 1.27 | 1.33 |
| Zfp688 | 1.06 | 1.35 | 0.70 | 0.97 | 0.98 | 1.06 | 1.21 | 8.24 | 1.11 | 2.74 | 1.32 | 1.08 |
| Zfp771 | 1.22 | 1.48 | 1.07 | 1.11 | 1.12 | 1.13 | 1.35 | 5.88 | 1.20 | 2.36 | 1.35 | 1.18 |
| Zfp809 | 2.57 | 1.89 | 1.98 | 0.83 | 4.36 | 1.09 | 1.26 | 8.58 | 1.29 | 2.33 | 1.02 | 1.17 |
| Zfp821 | 1.86 | 1.93 | 1.22 | 0.89 | 1.02 | 0.99 | 1.27 | 5.83 | 1.04 | 2.07 | 1.34 | 1.11 |
| Zfp97 | 1.00 | 1.00 | 1.00 | 1.96 | 1.00 | 1.07 | 1.71 | 0.82 | 2.39 | 1.00 | 1.35 | 1.36 |
| Zfpl1 | 0.68 | 0.62 | 0.65 | 1.27 | 1.26 | 0.85 | 1.17 | 4.13 | 0.95 | 2.63 | 1.63 | 1.23 |
| Zg16 | 1.08 | 1.09 | 1.11 | 1.60 | 1.00 | 0.63 | 0.70 | 1.40 | 0.67 | 0.91 | 0.52 | 0.86 |

Fig. 35- 289

| Gene Name | Skeletal muscle | | | Brown fat | | | Heart | | | Lung | | |
|---|---|---|---|---|---|---|---|---|---|---|---|---|
| | E | M | L | E | M | L | E | M | L | E | M | L |
| Zim1 | 1.84 | 1.00 | 1.00 | 2.03 | 1.00 | 1.00 | 1.00 | 1.00 | 1.00 | 1.00 | 1.00 | 1.00 |
| Zkscan6 | 2.40 | 2.49 | 1.96 | 2.08 | 3.77 | 1.44 | 1.25 | 1.40 | 1.15 | 1.71 | 1.43 | 1.11 |
| Znrd1 | 2.02 | 0.64 | 0.82 | 0.68 | 5.75 | 0.93 | 0.70 | 0.79 | 1.30 | 1.71 | 2.52 | 1.08 |
| Znrd1as | 0.97 | 0.63 | 0.84 | 1.84 | 5.04 | 1.14 | 0.83 | 0.88 | 0.74 | 1.37 | 1.70 | 1.01 |
| Znrf4 | 1.00 | 1.00 | 1.00 | 1.00 | 1.00 | 1.00 | 1.00 | 1.00 | 1.00 | 3.12 | 1.00 | 1.00 |
| Zpr1 | 1.71 | 0.69 | 1.32 | 1.55 | 26.47 | 1.44 | 1.62 | 1.27 | 1.24 | 4.07 | 4.64 | 1.01 |
| a | 1.00 | 1.00 | 1.00 | 1.00 | 1.00 | 1.00 | 1.00 | 1.00 | 1.00 | 1.00 | 1.00 | 1.00 |

Fig. 35- 290

| Gene Name | Thymus | | | Kidney | | | Liver | | | Colon | | |
|---|---|---|---|---|---|---|---|---|---|---|---|---|
| | E | M | L | E | M | L | E | M | L | E | M | L |
| Zim1 | 1.00 | 1.00 | 1.00 | 1.65 | 1.00 | 1.00 | 1.00 | 1.00 | 1.00 | 1.00 | 1.00 | 1.00 |
| Zkscan6 | 1.18 | 1.32 | 1.06 | 1.09 | 0.96 | 0.94 | 1.24 | 1.69 | 1.02 | 1.15 | 1.24 | 0.97 |
| Znrd1 | 1.18 | 1.60 | 1.01 | 0.75 | 0.76 | 0.91 | 0.57 | 0.98 | 1.02 | 1.03 | 1.50 | 0.89 |
| Znrd1as | 1.37 | 1.67 | 1.19 | 1.09 | 1.17 | 0.99 | 1.20 | 0.99 | 1.02 | 1.31 | 1.47 | 1.08 |
| Znrf4 | 1.00 | 1.00 | 1.00 | 1.00 | 1.00 | 1.00 | 1.00 | 1.35 | 1.00 | 1.00 | 1.00 | 1.00 |
| Zpr1 | 1.22 | 1.37 | 0.95 | 1.18 | 0.83 | 1.27 | 0.86 | 3.22 | 1.22 | 1.15 | 1.75 | 1.18 |
| a | 1.29 | 1.73 | 1.02 | 1.00 | 1.00 | 1.00 | 1.00 | 1.00 | 1.00 | 1.00 | 1.00 | 1.00 |

Fig. 35- 291

| Gene Name | Stomach | | | Adipose tissue | | | Testis | | | Spleen | | |
|---|---|---|---|---|---|---|---|---|---|---|---|---|
| | E | M | L | E | M | L | E | M | L | E | M | L |
| Zim1 | 1.00 | 1.00 | 1.00 | 6.54 | 1.00 | 1.84 | 1.00 | 1.00 | 1.00 | 1.00 | 1.00 | 1.00 |
| Zkscan6 | 1.06 | 1.43 | 0.96 | 1.19 | 6.22 | 1.49 | 1.00 | 1.68 | 0.97 | 1.14 | 1.13 | 1.11 |
| Znrd1 | 1.07 | 0.99 | 0.95 | 1.27 | 17.67 | 1.24 | 1.06 | 1.15 | 0.95 | 1.44 | 1.33 | 1.13 |
| Znrd1as | 0.84 | 1.01 | 1.22 | 1.28 | 6.79 | 1.13 | 0.91 | 1.02 | 0.90 | 1.30 | 1.47 | 1.27 |
| Znrf4 | 1.00 | 1.00 | 1.00 | 4.12 | 5.07 | 1.00 | 0.89 | 3.91 | 1.08 | 1.00 | 1.00 | 1.00 |
| Zpr1 | 1.08 | 1.13 | 1.00 | 2.93 | 6.18 | 2.54 | 0.94 | 4.09 | 1.00 | 1.27 | 1.40 | 1.06 |
| a | 1.00 | 1.00 | 1.00 | 1.00 | 1.00 | 1.00 | 0.94 | 1.00 | 1.56 | 1.00 | 1.00 | 1.00 |

Fig. 35- 292

| Gene Name | Pancreas | | | Brain | | | Ear | | | Bone marrow | | |
|---|---|---|---|---|---|---|---|---|---|---|---|---|
| | E | M | L | E | M | L | E | M | L | E | M | L |
| Zim1 | 1.00 | 1.00 | 1.00 | 0.60 | 1.00 | 0.75 | 1.00 | 1.00 | 1.00 | 1.00 | 1.00 | 1.00 |
| Zkscan6 | 0.82 | 1.04 | 1.03 | 0.94 | 0.65 | 0.95 | 1.02 | 2.63 | 0.93 | 1.52 | 1.35 | 1.33 |
| Znrd1 | 1.47 | 0.90 | 1.01 | 0.95 | 3.74 | 1.01 | 1.15 | 4.38 | 0.95 | 2.11 | 1.48 | 1.23 |
| Znrd1as | 0.65 | 0.66 | 0.90 | 1.29 | 0.77 | 1.07 | 1.24 | 3.47 | 0.83 | 1.99 | 1.20 | 0.98 |
| Znrf4 | 1.00 | 1.00 | 1.00 | 1.00 | 1.00 | 1.00 | 5.42 | 1.00 | 1.00 | 1.00 | 1.00 | 1.00 |
| Zpr1 | 0.94 | 0.87 | 1.00 | 1.04 | 0.77 | 0.98 | 1.31 | 15.18 | 1.03 | 3.45 | 1.31 | 1.06 |
| a | 1.00 | 1.00 | 1.00 | 1.00 | 1.00 | 1.00 | 1.91 | 7.85 | 2.29 | 1.00 | 1.00 | 1.00 |

Fig. 36 - 1

| Line No. | Group No. | | | | | Sub-Groups | Gene Name |
|---|---|---|---|---|---|---|---|
| 1 | 3 | 4 | 5 | 6 | 7 | VII-2 | Acta1 |
| 2 | 3 | 4 | 5 | 6 | 7 | VII-2 | Atp6v0c-ps2 |
| 3 | 3 | 4 | 5 | 6 | 7 | VII-2 | Bglap |
| 4 | 3 | 4 | 5 | 6 | 7 | VII-2 | Bglap2 |
| 5 | 3 | 4 | 5 | 6 | 7 | VII-2 | Camp |
| 6 | 3 | 4 | 5 | 6 | 7 | VII-2 | Clarr |
| 7 | 3 | 4 | 5 | 6 | 7 | VII-2 | Ckm |
| 8 | 3 | 4 | 5 | 6 | 7 | VII-2 | Cypt7 |
| 9 | 3 | 4 | 5 | 6 | 7 | VII-2 | D330041H03Rik |
| 10 | 3 | 4 | 5 | 6 | 7 | VII-2 | Dbp |
| 11 | 3 | 4 | 5 | 6 | 7 | VII-2 | Gm10488 |
| 12 | 3 | 4 | 5 | 6 | 7 | VII-2 | Gm1987 |
| 13 | 3 | 4 | 5 | 6 | 7 | VII-2 | Gm4836 |
| 14 | 3 | 4 | 5 | 6 | 7 | VII-2 | Gm5424 |
| 15 | 3 | 4 | 5 | 6 | 7 | VII-2 | Gm7334 |
| 16 | 3 | 4 | 5 | 6 | 7 | VII-2 | H2-Q8 |
| 17 | 3 | 4 | 5 | 6 | 7 | VII-2 | Hba-a2 |
| 18 | 3 | 4 | 5 | 6 | 7 | VII-2 | Hbb-b1 |
| 19 | 3 | 4 | 5 | 6 | 7 | VII-2 | Hist1h4m |
| 20 | 3 | 4 | 5 | 6 | 7 | VII-2 | Hist2h2aa2 |
| 21 | 3 | 4 | 5 | 6 | 7 | VII-2 | Hist2h3c1 |
| 22 | 3 | 4 | 5 | 6 | 7 | VII-2 | Ibsp |
| 23 | 3 | 4 | 5 | 6 | 7 | VII-2 | Mir1192 |
| 24 | 3 | 4 | 5 | 6 | 7 | VII-2 | Mir1199 |
| 25 | 3 | 4 | 5 | 6 | 7 | VII-2 | Mir1946a |
| 26 | 3 | 4 | 5 | 6 | 7 | VII-2 | Mir1966 |
| 27 | 3 | 4 | 5 | 6 | 7 | VII-2 | Mir3473g |
| 28 | 3 | 4 | 5 | 6 | 7 | VII-2 | Mir3535 |
| 29 | 3 | 4 | 5 | 6 | 7 | VII-2 | Mir466i |
| 30 | 3 | 4 | 5 | 6 | 7 | VII-2 | Mir6345 |
| 31 | 3 | 4 | 5 | 6 | 7 | VII-2 | Mir6390 |
| 32 | 3 | 4 | 5 | 6 | 7 | VII-2 | Mir6403 |
| 33 | 3 | 4 | 5 | 6 | 7 | VII-2 | Mir6418 |
| 34 | 3 | 4 | 5 | 6 | 7 | VII-2 | Mir6537 |
| 35 | 3 | 4 | 5 | 6 | 7 | VII-2 | Mir683-2 |
| 36 | 3 | 4 | 5 | 6 | 7 | VII-2 | Mir692-2b |
| 37 | 3 | 4 | 5 | 6 | 7 | VII-2 | Mir697 |
| 38 | 3 | 4 | 5 | 6 | 7 | VII-2 | Mir6981 |
| 39 | 3 | 4 | 5 | 6 | 7 | VII-2 | Mir8113 |
| 40 | 3 | 4 | 5 | 6 | 7 | VII-2 | Mir8118 |
| 41 | 3 | 4 | 5 | 6 | 7 | VII-2 | Mup17 |
| 42 | 3 | 4 | 5 | 6 | 7 | VII-2 | Ngp |
| 43 | 3 | 4 | 5 | 6 | 7 | VII-2 | Pate4 |
| 44 | 3 | 4 | 5 | 6 | 7 | VII-2 | Ppbp |
| 45 | 3 | 4 | 5 | 6 | 7 | VII-2 | Ppp1r3g |
| 46 | 3 | 4 | 5 | 6 | 7 | VII-2 | Pvalb |
| 47 | 3 | 4 | 5 | 6 | 7 | VII-2 | Retnlg |
| 48 | 3 | 4 | 5 | 6 | 7 | VII-2 | Rnaset2a |
| 49 | 3 | 4 | 5 | 6 | 7 | VII-2 | Rpph1 |
| 50 | 3 | 4 | 5 | 6 | 7 | VII-2 | Rps29 |
| 51 | 3 | 4 | 5 | 6 | 7 | VII-2 | S100a8 |
| 52 | 3 | 4 | 5 | 6 | 7 | VII-2 | S100a9 |
| 53 | 3 | 4 | 5 | 6 | 7 | VII-2 | Saa2 |
| 54 | 3 | 4 | 5 | 6 | 7 | VII-2 | Scarna3a |
| 55 | 3 | 4 | 5 | 6 | 7 | VII-2 | Snora15 |
| 56 | 3 | 4 | 5 | 6 | 7 | VII-2 | Snora23 |
| 57 | 3 | 4 | 5 | 6 | 7 | VII-2 | Snora68 |
| 58 | 3 | 4 | 5 | 6 | 7 | VII-2 | Snora74a |
| 59 | 3 | 4 | 5 | 6 | 7 | VII-2 | Snord17 |
| 60 | 3 | 4 | 5 | 6 | 7 | VII-2 | Snurf |
| 61 | 3 | 4 | 5 | 6 | 7 | VII-2 | Srp54c |
| 62 | 3 | 4 | 5 | 6 | 7 | VII-2 | Svs1 |
| 63 | 3 | 4 | 5 | 6 | 7 | VII-2 | Svs2 |
| 64 | 3 | 4 | 5 | 6 | 7 | VII-2 | Svs4 |
| 65 | 3 | 4 | 5 | 6 | 7 | VII-2 | Svs5 |
| 66 | 3 | 4 | 5 | 6 | 7 | VII-2 | Svs6 |
| 67 | 3 | 4 | 5 | 6 | 7 | VII-2 | Tcap |
| 68 | 3 | 4 | 5 | 6 | 7 | VII-2 | Tmem254c |
| 69 | 3 | 4 | 5 | 6 | 7 | VII-2 | Tnnc2 |
| 70 | 3 | 4 | 5 | 6 | 7 | VII-2 | Tnni2 |
| 71 | 3 | 4 | 5 | 6 | 7 | VII-2 | Usmg5 |
| 72 | 3 | 4 | 5 | 6 | 7 | VII-1 | 1810019D21Rik |
| 73 | 3 | 4 | 5 | 6 | 7 | VII-1 | 1810064F22Rik |
| 74 | 3 | 4 | 5 | 6 | 7 | VII-1 | 2010003K11Rik |
| 75 | 3 | 4 | 5 | 6 | 7 | VII-1 | 2210010C04Rik |
| 76 | 3 | 4 | 5 | 6 | 7 | VII-1 | 2310057J18Rik |
| 77 | 3 | 4 | 5 | 6 | 7 | VII-1 | 2810459M11Rik |
| 78 | 3 | 4 | 5 | 6 | 7 | VII-1 | 5830403L16Rik |
| 79 | 3 | 4 | 5 | 6 | 7 | VII-1 | 9230104L09Rik |
| 80 | 3 | 4 | 5 | 6 | 7 | VII-1 | 9230110F15Rik |
| 81 | 3 | 4 | 5 | 6 | 7 | VII-1 | A730008H23Rik |
| 82 | 3 | 4 | 5 | 6 | 7 | VII-1 | AI747448 |
| 83 | 3 | 4 | 5 | 6 | 7 | VII-1 | AU015791 |
| 84 | 3 | 4 | 5 | 6 | 7 | VII-1 | AW112010 |
| 85 | 3 | 4 | 5 | 6 | 7 | VII-1 | AY761185 |
| 86 | 3 | 4 | 5 | 6 | 7 | VII-1 | Acaa1b |
| 87 | 3 | 4 | 5 | 6 | 7 | VII-1 | Acpp |
| 88 | 3 | 4 | 5 | 6 | 7 | VII-1 | Actg2 |
| 89 | 3 | 4 | 5 | 6 | 7 | VII-1 | Adam28 |
| 90 | 3 | 4 | 5 | 6 | 7 | VII-1 | Adam7 |
| 91 | 3 | 4 | 5 | 6 | 7 | VII-1 | Ago2 |
| 92 | 3 | 4 | 5 | 6 | 7 | VII-1 | Ahsg |
| 93 | 3 | 4 | 5 | 6 | 7 | VII-1 | Akp3 |
| 94 | 3 | 4 | 5 | 6 | 7 | VII-1 | Alb |
| 95 | 3 | 4 | 5 | 6 | 7 | VII-1 | Aldob |
| 96 | 3 | 4 | 5 | 6 | 7 | VII-1 | Aldoc |
| 97 | 3 | 4 | 5 | 6 | 7 | VII-1 | Alox15 |
| 98 | 3 | 4 | 5 | 6 | 7 | VII-1 | Alpi |
| 99 | 3 | 4 | 5 | 6 | 7 | VII-1 | Ambp |
| 100 | 3 | 4 | 5 | 6 | 7 | VII-1 | Amd1 |
| 101 | 3 | 4 | 5 | 6 | 7 | VII-1 | Amy1 |
| 102 | 3 | 4 | 5 | 6 | 7 | VII-1 | Amy2a5 |
| 103 | 3 | 4 | 5 | 6 | 7 | VII-1 | Amy2b |
| 104 | 3 | 4 | 5 | 6 | 7 | VII-1 | Ang4 |
| 105 | 3 | 4 | 5 | 6 | 7 | VII-1 | Ap1s2 |
| 106 | 3 | 4 | 5 | 6 | 7 | VII-1 | Apoa1 |
| 107 | 3 | 4 | 5 | 6 | 7 | VII-1 | Apoa2 |
| 108 | 3 | 4 | 5 | 6 | 7 | VII-1 | Apoa5 |
| 109 | 3 | 4 | 5 | 6 | 7 | VII-1 | Apoc1 |
| 110 | 3 | 4 | 5 | 6 | 7 | VII-1 | Apoc3 |
| 111 | 3 | 4 | 5 | 6 | 7 | VII-1 | Apoc4 |
| 112 | 3 | 4 | 5 | 6 | 7 | VII-1 | Apoe |
| 113 | 3 | 4 | 5 | 6 | 7 | VII-1 | Apoh |
| 114 | 3 | 4 | 5 | 6 | 7 | VII-1 | Asb11 |
| 115 | 3 | 4 | 5 | 6 | 7 | VII-1 | Azgp1 |
| 116 | 3 | 4 | 5 | 6 | 7 | VII-1 | B4galnt2 |
| 117 | 3 | 4 | 5 | 6 | 7 | VII-1 | B9d1 |
| 118 | 3 | 4 | 5 | 6 | 7 | VII-1 | Bcl2l15 |
| 119 | 3 | 4 | 5 | 6 | 7 | VII-1 | Bex2 |
| 120 | 3 | 4 | 5 | 6 | 7 | VII-1 | Bex4 |
| 121 | 3 | 4 | 5 | 6 | 7 | VII-1 | Bglap3 |
| 122 | 3 | 4 | 5 | 6 | 7 | VII-1 | Bhmt |
| 123 | 3 | 4 | 5 | 6 | 7 | VII-1 | Bsph1 |
| 124 | 3 | 4 | 5 | 6 | 7 | VII-1 | Bspry |
| 125 | 3 | 4 | 5 | 6 | 7 | VII-1 | Btg3 |
| 126 | 3 | 4 | 5 | 6 | 7 | VII-1 | C4b |
| 127 | 3 | 4 | 5 | 6 | 7 | VII-1 | C4bp |
| 128 | 3 | 4 | 5 | 6 | 7 | VII-1 | Cbl |
| 129 | 3 | 4 | 5 | 6 | 7 | VII-1 | Ccl12 |
| 130 | 3 | 4 | 5 | 6 | 7 | VII-1 | Ccl21b |
| 131 | 3 | 4 | 5 | 6 | 7 | VII-1 | Ccl25 |
| 132 | 3 | 4 | 5 | 6 | 7 | VII-1 | Ccl27b |
| 133 | 3 | 4 | 5 | 6 | 7 | VII-1 | Ccno |
| 134 | 3 | 4 | 5 | 6 | 7 | VII-1 | Ccnt1 |
| 135 | 3 | 4 | 5 | 6 | 7 | VII-1 | Cdh1 |
| 136 | 3 | 4 | 5 | 6 | 7 | VII-1 | Cdh16 |
| 137 | 3 | 4 | 5 | 6 | 7 | VII-1 | Cdh17 |
| 138 | 3 | 4 | 5 | 6 | 7 | VII-1 | Cdk6 |
| 139 | 3 | 4 | 5 | 6 | 7 | VII-1 | Cdkl5 |
| 140 | 3 | 4 | 5 | 6 | 7 | VII-1 | Cdo1 |
| 141 | 3 | 4 | 5 | 6 | 7 | VII-1 | Ceacam10 |
| 142 | 3 | 4 | 5 | 6 | 7 | VII-1 | Cel |
| 143 | 3 | 4 | 5 | 6 | 7 | VII-1 | Cela1 |
| 144 | 3 | 4 | 5 | 6 | 7 | VII-1 | Cela2a |
| 145 | 3 | 4 | 5 | 6 | 7 | VII-1 | Cela3b |
| 146 | 3 | 4 | 5 | 6 | 7 | VII-1 | Ces5a |
| 147 | 3 | 4 | 5 | 6 | 7 | VII-1 | Cfd |
| 148 | 3 | 4 | 5 | 6 | 7 | VII-1 | Chga |
| 149 | 3 | 4 | 5 | 6 | 7 | VII-1 | Chrm2 |
| 150 | 3 | 4 | 5 | 6 | 7 | VII-1 | Chrna7 |
| 151 | 3 | 4 | 5 | 6 | 7 | VII-1 | Cited4 |
| 152 | 3 | 4 | 5 | 6 | 7 | VII-1 | Ckmt1 |
| 153 | 3 | 4 | 5 | 6 | 7 | VII-1 | Clca3 |
| 154 | 3 | 4 | 5 | 6 | 7 | VII-1 | Cldn2 |
| 155 | 3 | 4 | 5 | 6 | 7 | VII-1 | Cldn3 |
| 156 | 3 | 4 | 5 | 6 | 7 | VII-1 | Cldn4 |
| 157 | 3 | 4 | 5 | 6 | 7 | VII-1 | Cldn7 |
| 158 | 3 | 4 | 5 | 6 | 7 | VII-1 | Cldn8 |
| 159 | 3 | 4 | 5 | 6 | 7 | VII-1 | Clec2h |
| 160 | 3 | 4 | 5 | 6 | 7 | VII-1 | Clec7a |
| 161 | 3 | 4 | 5 | 6 | 7 | VII-1 | Clps |
| 162 | 3 | 4 | 5 | 6 | 7 | VII-1 | Clpsl2 |
| 163 | 3 | 4 | 5 | 6 | 7 | VII-1 | Clu |
| 164 | 3 | 4 | 5 | 6 | 7 | VII-1 | Cpa1 |
| 165 | 3 | 4 | 5 | 6 | 7 | VII-1 | Cpa2 |
| 166 | 3 | 4 | 5 | 6 | 7 | VII-1 | Cpb1 |
| 167 | 3 | 4 | 5 | 6 | 7 | VII-1 | Crisp1 |
| 168 | 3 | 4 | 5 | 6 | 7 | VII-1 | Crisp4 |
| 169 | 3 | 4 | 5 | 6 | 7 | VII-1 | Cryba4 |
| 170 | 3 | 4 | 5 | 6 | 7 | VII-1 | Cst11 |
| 171 | 3 | 4 | 5 | 6 | 7 | VII-1 | Cst12 |
| 172 | 3 | 4 | 5 | 6 | 7 | VII-1 | Cst8 |
| 173 | 3 | 4 | 5 | 6 | 7 | VII-1 | Ctrb1 |
| 174 | 3 | 4 | 5 | 6 | 7 | VII-1 | Ctrc |
| 175 | 3 | 4 | 5 | 6 | 7 | VII-1 | Ctrl |
| 176 | 3 | 4 | 5 | 6 | 7 | VII-1 | Cuzd1 |
| 177 | 3 | 4 | 5 | 6 | 7 | VII-1 | Cxcl10 |
| 178 | 3 | 4 | 5 | 6 | 7 | VII-1 | Cxcl13 |
| 179 | 3 | 4 | 5 | 6 | 7 | VII-1 | Cxcl9 |
| 180 | 3 | 4 | 5 | 6 | 7 | VII-1 | Cyb561 |
| 181 | 3 | 4 | 5 | 6 | 7 | VII-1 | Cyp2d9 |
| 182 | 3 | 4 | 5 | 6 | 7 | VII-1 | Cyp2e1 |
| 183 | 3 | 4 | 5 | 6 | 7 | VII-1 | Cyp3a11 |
| 184 | 3 | 4 | 5 | 6 | 7 | VII-1 | Cyp4a10 |
| 185 | 3 | 4 | 5 | 6 | 7 | VII-1 | Cyp4a14 |
| 186 | 3 | 4 | 5 | 6 | 7 | VII-1 | D108wg1379e |
| 187 | 3 | 4 | 5 | 6 | 7 | VII-1 | D730048I06Rik |
| 188 | 3 | 4 | 5 | 6 | 7 | VII-1 | Ddi2 |
| 189 | 3 | 4 | 5 | 6 | 7 | VII-1 | Ddit4l |
| 190 | 3 | 4 | 5 | 6 | 7 | VII-1 | Defa-rs1 |

Fig. 36 - 2

| | | | | | | | |
|---|---|---|---|---|---|---|---|
| 191 | 3 | 4 | 5 | 6 | 7 | VII-1 | Defa-rs7 |
| 192 | 3 | 4 | 5 | 6 | 7 | VII-1 | Defa17 |
| 193 | 3 | 4 | 5 | 6 | 7 | VII-1 | Defa23 |
| 194 | 3 | 4 | 5 | 6 | 7 | VII-1 | Defa24 |
| 195 | 3 | 4 | 5 | 6 | 7 | VII-1 | Defa3 |
| 196 | 3 | 4 | 5 | 6 | 7 | VII-1 | Defa4 |
| 197 | 3 | 4 | 5 | 6 | 7 | VII-1 | Defb1 |
| 198 | 3 | 4 | 5 | 6 | 7 | VII-1 | Defb12 |
| 199 | 3 | 4 | 5 | 6 | 7 | VII-1 | Defb15 |
| 200 | 3 | 4 | 5 | 6 | 7 | VII-1 | Defb18 |
| 201 | 3 | 4 | 5 | 6 | 7 | VII-1 | Defb2 |
| 202 | 3 | 4 | 5 | 6 | 7 | VII-1 | Defb20 |
| 203 | 3 | 4 | 5 | 6 | 7 | VII-1 | Defb21 |
| 204 | 3 | 4 | 5 | 6 | 7 | VII-1 | Defb25 |
| 205 | 3 | 4 | 5 | 6 | 7 | VII-1 | Defb30 |
| 206 | 3 | 4 | 5 | 6 | 7 | VII-1 | Defb37 |
| 207 | 3 | 4 | 5 | 6 | 7 | VII-1 | Defb39 |
| 208 | 3 | 4 | 5 | 6 | 7 | VII-1 | Defb41 |
| 209 | 3 | 4 | 5 | 6 | 7 | VII-1 | Defb42 |
| 210 | 3 | 4 | 5 | 6 | 7 | VII-1 | Defb45 |
| 211 | 3 | 4 | 5 | 6 | 7 | VII-1 | Defb47 |
| 212 | 3 | 4 | 5 | 6 | 7 | VII-1 | Defb48 |
| 213 | 3 | 4 | 5 | 6 | 7 | VII-1 | Dmbt1 |
| 214 | 3 | 4 | 5 | 6 | 7 | VII-1 | Dnajb14 |
| 215 | 3 | 4 | 5 | 6 | 7 | VII-1 | Dsp |
| 216 | 3 | 4 | 5 | 6 | 7 | VII-1 | Eddm3b |
| 217 | 3 | 4 | 5 | 6 | 7 | VII-1 | Efcab4b |
| 218 | 3 | 4 | 5 | 6 | 7 | VII-1 | Egr1 |
| 219 | 3 | 4 | 5 | 6 | 7 | VII-1 | Egr2 |
| 220 | 3 | 4 | 5 | 6 | 7 | VII-1 | Ehf |
| 221 | 3 | 4 | 5 | 6 | 7 | VII-1 | Ehhadh |
| 222 | 3 | 4 | 5 | 6 | 7 | VII-1 | Eif3j1 |
| 223 | 3 | 4 | 5 | 6 | 7 | VII-1 | Eif3j2 |
| 224 | 3 | 4 | 5 | 6 | 7 | VII-1 | Eif3 |
| 225 | 3 | 4 | 5 | 6 | 7 | VII-1 | Emx2 |
| 226 | 3 | 4 | 5 | 6 | 7 | VII-1 | Enpp1 |
| 227 | 3 | 4 | 5 | 6 | 7 | VII-1 | Epcam |
| 228 | 3 | 4 | 5 | 6 | 7 | VII-1 | Eppin |
| 229 | 3 | 4 | 5 | 6 | 7 | VII-1 | Faah |
| 230 | 3 | 4 | 5 | 6 | 7 | VII-1 | Fabp1 |
| 231 | 3 | 4 | 5 | 6 | 7 | VII-1 | Fam84a |
| 232 | 3 | 4 | 5 | 6 | 7 | VII-1 | Fbxl18 |
| 233 | 3 | 4 | 5 | 6 | 7 | VII-1 | Fga |
| 234 | 3 | 4 | 5 | 6 | 7 | VII-1 | Fgb |
| 235 | 3 | 4 | 5 | 6 | 7 | VII-1 | Fgg |
| 236 | 3 | 4 | 5 | 6 | 7 | VII-1 | Folr1 |
| 237 | 3 | 4 | 5 | 6 | 7 | VII-1 | Foxn3 |
| 238 | 3 | 4 | 5 | 6 | 7 | VII-1 | Gal3st4 |
| 239 | 3 | 4 | 5 | 6 | 7 | VII-1 | Galnt12 |
| 240 | 3 | 4 | 5 | 6 | 7 | VII-1 | Gamt |
| 241 | 3 | 4 | 5 | 6 | 7 | VII-1 | Gatad2b |
| 242 | 3 | 4 | 5 | 6 | 7 | VII-1 | Gbp10 |
| 243 | 3 | 4 | 5 | 6 | 7 | VII-1 | Gbp2 |
| 244 | 3 | 4 | 5 | 6 | 7 | VII-1 | Gbp3 |
| 245 | 3 | 4 | 5 | 6 | 7 | VII-1 | Gbp5 |
| 246 | 3 | 4 | 5 | 6 | 7 | VII-1 | Gbp6 |
| 247 | 3 | 4 | 5 | 6 | 7 | VII-1 | Gbp7 |
| 248 | 3 | 4 | 5 | 6 | 7 | VII-1 | Gc |
| 249 | 3 | 4 | 5 | 6 | 7 | VII-1 | Gcnt4 |
| 250 | 3 | 4 | 5 | 6 | 7 | VII-1 | Gfra1 |
| 251 | 3 | 4 | 5 | 6 | 7 | VII-1 | Ggt1 |
| 252 | 3 | 4 | 5 | 6 | 7 | VII-1 | Gjb3 |
| 253 | 3 | 4 | 5 | 6 | 7 | VII-1 | Glra1 |
| 254 | 3 | 4 | 5 | 6 | 7 | VII-1 | Gm10104 |
| 255 | 3 | 4 | 5 | 6 | 7 | VII-1 | Gm10230 |
| 256 | 3 | 4 | 5 | 6 | 7 | VII-1 | Gm1110 |
| 257 | 3 | 4 | 5 | 6 | 7 | VII-1 | Gm12250 |
| 258 | 3 | 4 | 5 | 6 | 7 | VII-1 | Gm13363 |
| 259 | 3 | 4 | 5 | 6 | 7 | VII-1 | Gm14475 |
| 260 | 3 | 4 | 5 | 6 | 7 | VII-1 | Gm14851 |
| 261 | 3 | 4 | 5 | 6 | 7 | VII-1 | Gm15284 |
| 262 | 3 | 4 | 5 | 6 | 7 | VII-1 | Gm15386 |
| 263 | 3 | 4 | 5 | 6 | 7 | VII-1 | Gm17727 |
| 264 | 3 | 4 | 5 | 6 | 7 | VII-1 | Gm20604 |
| 265 | 3 | 4 | 5 | 6 | 7 | VII-1 | Gm2083 |
| 266 | 3 | 4 | 5 | 6 | 7 | VII-1 | Gm20878 |
| 267 | 3 | 4 | 5 | 6 | 7 | VII-1 | Gm21498 |
| 268 | 3 | 4 | 5 | 6 | 7 | VII-1 | Gm266 |
| 269 | 3 | 4 | 5 | 6 | 7 | VII-1 | Gm4759 |
| 270 | 3 | 4 | 5 | 6 | 7 | VII-1 | Gm4846 |
| 271 | 3 | 4 | 5 | 6 | 7 | VII-1 | Gm5531 |
| 272 | 3 | 4 | 5 | 6 | 7 | VII-1 | Gm5916 |
| 273 | 3 | 4 | 5 | 6 | 7 | VII-1 | Gm6040 |
| 274 | 3 | 4 | 5 | 6 | 7 | VII-1 | Gm6792 |
| 275 | 3 | 4 | 5 | 6 | 7 | VII-1 | Gm6793 |
| 276 | 3 | 4 | 5 | 6 | 7 | VII-1 | Gm766 |
| 277 | 3 | 4 | 5 | 6 | 7 | VII-1 | Gnmt |
| 278 | 3 | 4 | 5 | 6 | 7 | VII-1 | Gp2 |
| 279 | 3 | 4 | 5 | 6 | 7 | VII-1 | Gpr26 |
| 280 | 3 | 4 | 5 | 6 | 7 | VII-1 | Gpx5 |
| 281 | 3 | 4 | 5 | 6 | 7 | VII-1 | Gstm6 |
| 282 | 3 | 4 | 5 | 6 | 7 | VII-1 | Gstm7 |
| 283 | 3 | 4 | 5 | 6 | 7 | VII-1 | Guca2a |
| 284 | 3 | 4 | 5 | 6 | 7 | VII-1 | H2-Q7 |
| 285 | 3 | 4 | 5 | 6 | 7 | VII-1 | H2-T9 |
| 286 | 3 | 4 | 5 | 6 | 7 | VII-1 | Hba-a1 |
| 287 | 3 | 4 | 5 | 6 | 7 | VII-1 | Hbb-bs |
| 288 | 3 | 4 | 5 | 6 | 7 | VII-1 | Hcar1 |
| 289 | 3 | 4 | 5 | 6 | 7 | VII-1 | Hipk2 |
| 290 | 3 | 4 | 5 | 6 | 7 | VII-1 | Hist1h4i |
| 291 | 3 | 4 | 5 | 6 | 7 | VII-1 | Hist2h2bb |
| 292 | 3 | 4 | 5 | 6 | 7 | VII-1 | Hist2h3c2 |
| 293 | 3 | 4 | 5 | 6 | 7 | VII-1 | Hmbox1 |
| 294 | 3 | 4 | 5 | 6 | 7 | VII-1 | Hmgcs2 |
| 295 | 3 | 4 | 5 | 6 | 7 | VII-1 | Hoxa6 |
| 296 | 3 | 4 | 5 | 6 | 7 | VII-1 | Hpx |
| 297 | 3 | 4 | 5 | 6 | 7 | VII-1 | Hs6st3 |
| 298 | 3 | 4 | 5 | 6 | 7 | VII-1 | Hsd3b5 |
| 299 | 3 | 4 | 5 | 6 | 7 | VII-1 | Iapp |
| 300 | 3 | 4 | 5 | 6 | 7 | VII-1 | Icam2 |
| 301 | 3 | 4 | 5 | 6 | 7 | VII-1 | Ido1 |
| 302 | 3 | 4 | 5 | 6 | 7 | VII-1 | Ifi47 |
| 303 | 3 | 4 | 5 | 6 | 7 | VII-1 | Ifit1 |
| 304 | 3 | 4 | 5 | 6 | 7 | VII-1 | Igfbp2 |
| 305 | 3 | 4 | 5 | 6 | 7 | VII-1 | Igfbp4 |
| 306 | 3 | 4 | 5 | 6 | 7 | VII-1 | Igtp |
| 307 | 3 | 4 | 5 | 6 | 7 | VII-1 | Iigp1 |
| 308 | 3 | 4 | 5 | 6 | 7 | VII-1 | Ins2 |
| 309 | 3 | 4 | 5 | 6 | 7 | VII-1 | Irgm2 |
| 310 | 3 | 4 | 5 | 6 | 7 | VII-1 | Kap |
| 311 | 3 | 4 | 5 | 6 | 7 | VII-1 | Kcna3 |
| 312 | 3 | 4 | 5 | 6 | 7 | VII-1 | Kcnk1 |
| 313 | 3 | 4 | 5 | 6 | 7 | VII-1 | Kcnk9 |
| 314 | 3 | 4 | 5 | 6 | 7 | VII-1 | Klf7 |
| 315 | 3 | 4 | 5 | 6 | 7 | VII-1 | Klk1 |
| 316 | 3 | 4 | 5 | 6 | 7 | VII-1 | Krt18 |
| 317 | 3 | 4 | 5 | 6 | 7 | VII-1 | Krt5 |
| 318 | 3 | 4 | 5 | 6 | 7 | VII-1 | Lars2 |
| 319 | 3 | 4 | 5 | 6 | 7 | VII-1 | Lcn10 |
| 320 | 3 | 4 | 5 | 6 | 7 | VII-1 | Lcn12 |
| 321 | 3 | 4 | 5 | 6 | 7 | VII-1 | Lcn2 |
| 322 | 3 | 4 | 5 | 6 | 7 | VII-1 | Lcn5 |
| 323 | 3 | 4 | 5 | 6 | 7 | VII-1 | Lcn6 |
| 324 | 3 | 4 | 5 | 6 | 7 | VII-1 | Lcn8 |
| 325 | 3 | 4 | 5 | 6 | 7 | VII-1 | Lcn9 |
| 326 | 3 | 4 | 5 | 6 | 7 | VII-1 | Lgals6 |
| 327 | 3 | 4 | 5 | 6 | 7 | VII-1 | Lingo1 |
| 328 | 3 | 4 | 5 | 6 | 7 | VII-1 | Lmbrd2 |
| 329 | 3 | 4 | 5 | 6 | 7 | VII-1 | Lnpep |
| 330 | 3 | 4 | 5 | 6 | 7 | VII-1 | Lrcol1 |
| 331 | 3 | 4 | 5 | 6 | 7 | VII-1 | Ltf |
| 332 | 3 | 4 | 5 | 6 | 7 | VII-1 | Ly6g5b |
| 333 | 3 | 4 | 5 | 6 | 7 | VII-1 | Ly6g5c |
| 334 | 3 | 4 | 5 | 6 | 7 | VII-1 | Lypd8 |
| 335 | 3 | 4 | 5 | 6 | 7 | VII-1 | Mal |
| 336 | 3 | 4 | 5 | 6 | 7 | VII-1 | Mat1a |
| 337 | 3 | 4 | 5 | 6 | 7 | VII-1 | Mbnl3 |
| 338 | 3 | 4 | 5 | 6 | 7 | VII-1 | Mgat5 |
| 339 | 3 | 4 | 5 | 6 | 7 | VII-1 | Mgst1 |
| 340 | 3 | 4 | 5 | 6 | 7 | VII-1 | Mib1 |
| 341 | 3 | 4 | 5 | 6 | 7 | VII-1 | Mir10a |
| 342 | 3 | 4 | 5 | 6 | 7 | VII-1 | Mir1291 |
| 343 | 3 | 4 | 5 | 6 | 7 | VII-1 | Mir142b |
| 344 | 3 | 4 | 5 | 6 | 7 | VII-1 | Mir1668 |
| 345 | 3 | 4 | 5 | 6 | 7 | VII-1 | Mir1938 |
| 346 | 3 | 4 | 5 | 6 | 7 | VII-1 | Mir1957b |
| 347 | 3 | 4 | 5 | 6 | 7 | VII-1 | Mir214 |
| 348 | 3 | 4 | 5 | 6 | 7 | VII-1 | Mir365-2 |
| 349 | 3 | 4 | 5 | 6 | 7 | VII-1 | Mir486 |
| 350 | 3 | 4 | 5 | 6 | 7 | VII-1 | Mir546 |
| 351 | 3 | 4 | 5 | 6 | 7 | VII-1 | Mir6236 |
| 352 | 3 | 4 | 5 | 6 | 7 | VII-1 | Mir6244 |
| 353 | 3 | 4 | 5 | 6 | 7 | VII-1 | Mir6338 |
| 354 | 3 | 4 | 5 | 6 | 7 | VII-1 | Mir6340 |
| 355 | 3 | 4 | 5 | 6 | 7 | VII-1 | Mir6357 |
| 356 | 3 | 4 | 5 | 6 | 7 | VII-1 | Mir6363 |
| 357 | 3 | 4 | 5 | 6 | 7 | VII-1 | Mir6516 |
| 358 | 3 | 4 | 5 | 6 | 7 | VII-1 | Mir682 |
| 359 | 3 | 4 | 5 | 6 | 7 | VII-1 | Mir6992 |
| 360 | 3 | 4 | 5 | 6 | 7 | VII-1 | Mir7-1 |
| 361 | 3 | 4 | 5 | 6 | 7 | VII-1 | Mir703 |
| 362 | 3 | 4 | 5 | 6 | 7 | VII-1 | Mir719 |
| 363 | 3 | 4 | 5 | 6 | 7 | VII-1 | Mir760 |
| 364 | 3 | 4 | 5 | 6 | 7 | VII-1 | Mir8091 |
| 365 | 3 | 4 | 5 | 6 | 7 | VII-1 | Mir8093 |
| 366 | 3 | 4 | 5 | 6 | 7 | VII-1 | Mir8094 |
| 367 | 3 | 4 | 5 | 6 | 7 | VII-1 | Mir8096 |
| 368 | 3 | 4 | 5 | 6 | 7 | VII-1 | Mir8097 |
| 369 | 3 | 4 | 5 | 6 | 7 | VII-1 | Mir8098 |
| 370 | 3 | 4 | 5 | 6 | 7 | VII-1 | Mir8099-1 |
| 371 | 3 | 4 | 5 | 6 | 7 | VII-1 | Mir8102 |
| 372 | 3 | 4 | 5 | 6 | 7 | VII-1 | Mir8103 |
| 373 | 3 | 4 | 5 | 6 | 7 | VII-1 | Mir8104 |
| 374 | 3 | 4 | 5 | 6 | 7 | VII-1 | Mir8112 |
| 375 | 3 | 4 | 5 | 6 | 7 | VII-1 | Mir8114 |
| 376 | 3 | 4 | 5 | 6 | 7 | VII-1 | Mir96 |
| 377 | 3 | 4 | 5 | 6 | 7 | VII-1 | Mirlet7d |
| 378 | 3 | 4 | 5 | 6 | 7 | VII-1 | Mt3 |
| 379 | 3 | 4 | 5 | 6 | 7 | VII-1 | Mttp |
| 380 | 3 | 4 | 5 | 6 | 7 | VII-1 | Muc13 |
| 381 | 3 | 4 | 5 | 6 | 7 | VII-1 | Muc15 |
| 382 | 3 | 4 | 5 | 6 | 7 | VII-1 | Muc5b |

Fig. 36 - 3

| | | | | | | | |
|---|---|---|---|---|---|---|---|
| 383 | 3 | 4 | 5 | 6 | 7 | VII-1 | Mup1 |
| 384 | 3 | 4 | 5 | 6 | 7 | VII-1 | Mup10 |
| 385 | 3 | 4 | 5 | 6 | 7 | VII-1 | Mup12 |
| 386 | 3 | 4 | 5 | 6 | 7 | VII-1 | Mup13 |
| 387 | 3 | 4 | 5 | 6 | 7 | VII-1 | Mup14 |
| 388 | 3 | 4 | 5 | 6 | 7 | VII-1 | Mup15 |
| 389 | 3 | 4 | 5 | 6 | 7 | VII-1 | Mup2 |
| 390 | 3 | 4 | 5 | 6 | 7 | VII-1 | Mup3 |
| 391 | 3 | 4 | 5 | 6 | 7 | VII-1 | Mup8 |
| 392 | 3 | 4 | 5 | 6 | 7 | VII-1 | Mup9 |
| 393 | 3 | 4 | 5 | 6 | 7 | VII-1 | Ndufa3 |
| 394 | 3 | 4 | 5 | 6 | 7 | VII-1 | Npcd |
| 395 | 3 | 4 | 5 | 6 | 7 | VII-1 | Nr4a1 |
| 396 | 3 | 4 | 5 | 6 | 7 | VII-1 | Nxpe2 |
| 397 | 3 | 4 | 5 | 6 | 7 | VII-1 | OTTMUSG00000016609 |
| 398 | 3 | 4 | 5 | 6 | 7 | VII-1 | Oasl2 |
| 399 | 3 | 4 | 5 | 6 | 7 | VII-1 | Oaz1-ps |
| 400 | 3 | 4 | 5 | 6 | 7 | VII-1 | Ovch2 |
| 401 | 3 | 4 | 5 | 6 | 7 | VII-1 | Padi2 |
| 402 | 3 | 4 | 5 | 6 | 7 | VII-1 | Pax8 |
| 403 | 3 | 4 | 5 | 6 | 7 | VII-1 | Pck1 |
| 404 | 3 | 4 | 5 | 6 | 7 | VII-1 | Pdzk1 |
| 405 | 3 | 4 | 5 | 6 | 7 | VII-1 | Pdzk1ip1 |
| 406 | 3 | 4 | 5 | 6 | 7 | VII-1 | Phgr1 |
| 407 | 3 | 4 | 5 | 6 | 7 | VII-1 | Pira4 |
| 408 | 3 | 4 | 5 | 6 | 7 | VII-1 | Pla2g1b |
| 409 | 3 | 4 | 5 | 6 | 7 | VII-1 | Pnlip |
| 410 | 3 | 4 | 5 | 6 | 7 | VII-1 | Pnliprp1 |
| 411 | 3 | 4 | 5 | 6 | 7 | VII-1 | Pnliprp2 |
| 412 | 3 | 4 | 5 | 6 | 7 | VII-1 | Pou3f3 |
| 413 | 3 | 4 | 5 | 6 | 7 | VII-1 | Ppp1r12b |
| 414 | 3 | 4 | 5 | 6 | 7 | VII-1 | Prap1 |
| 415 | 3 | 4 | 5 | 6 | 7 | VII-1 | Prg4 |
| 416 | 3 | 4 | 5 | 6 | 7 | VII-1 | Prom2 |
| 417 | 3 | 4 | 5 | 6 | 7 | VII-1 | Prss2 |
| 418 | 3 | 4 | 5 | 6 | 7 | VII-1 | Prss8 |
| 419 | 3 | 4 | 5 | 6 | 7 | VII-1 | Ptgds |
| 420 | 3 | 4 | 5 | 6 | 7 | VII-1 | Rab11fip4 |
| 421 | 3 | 4 | 5 | 6 | 7 | VII-1 | Rab25 |
| 422 | 3 | 4 | 5 | 6 | 7 | VII-1 | Rbm11 |
| 423 | 3 | 4 | 5 | 6 | 7 | VII-1 | Rbp4 |
| 424 | 3 | 4 | 5 | 6 | 7 | VII-1 | Reg1 |
| 425 | 3 | 4 | 5 | 6 | 7 | VII-1 | Reg2 |
| 426 | 3 | 4 | 5 | 6 | 7 | VII-1 | Reg3a |
| 427 | 3 | 4 | 5 | 6 | 7 | VII-1 | Reg3b |
| 428 | 3 | 4 | 5 | 6 | 7 | VII-1 | Reg3d |
| 429 | 3 | 4 | 5 | 6 | 7 | VII-1 | Reg3g |
| 430 | 3 | 4 | 5 | 6 | 7 | VII-1 | Rhcg |
| 431 | 3 | 4 | 5 | 6 | 7 | VII-1 | Rmrp |
| 432 | 3 | 4 | 5 | 6 | 7 | VII-1 | Rnase1 |
| 433 | 3 | 4 | 5 | 6 | 7 | VII-1 | Rnase10 |
| 434 | 3 | 4 | 5 | 6 | 7 | VII-1 | Rnase12 |
| 435 | 3 | 4 | 5 | 6 | 7 | VII-1 | Rnase13 |
| 436 | 3 | 4 | 5 | 6 | 7 | VII-1 | Rnase4 |
| 437 | 3 | 4 | 5 | 6 | 7 | VII-1 | Rnase9 |
| 438 | 3 | 4 | 5 | 6 | 7 | VII-1 | Rnf186 |
| 439 | 3 | 4 | 5 | 6 | 7 | VII-1 | Rnu11 |
| 440 | 3 | 4 | 5 | 6 | 7 | VII-1 | Rps18 |
| 441 | 3 | 4 | 5 | 6 | 7 | VII-1 | Rtp4 |
| 442 | 3 | 4 | 5 | 6 | 7 | VII-1 | S100g |
| 443 | 3 | 4 | 5 | 6 | 7 | VII-1 | Saa3 |
| 444 | 3 | 4 | 5 | 6 | 7 | VII-1 | Scarna3b |
| 445 | 3 | 4 | 5 | 6 | 7 | VII-1 | Scarna8 |
| 446 | 3 | 4 | 5 | 6 | 7 | VII-1 | Scgb1a1 |
| 447 | 3 | 4 | 5 | 6 | 7 | VII-1 | Scube1 |
| 448 | 3 | 4 | 5 | 6 | 7 | VII-1 | Sdc3 |
| 449 | 3 | 4 | 5 | 6 | 7 | VII-1 | Serinc2 |
| 450 | 3 | 4 | 5 | 6 | 7 | VII-1 | Serpina1a |
| 451 | 3 | 4 | 5 | 6 | 7 | VII-1 | Serpina1b |
| 452 | 3 | 4 | 5 | 6 | 7 | VII-1 | Serpina1c |
| 453 | 3 | 4 | 5 | 6 | 7 | VII-1 | Serpina1d |
| 454 | 3 | 4 | 5 | 6 | 7 | VII-1 | Serpina1e |
| 455 | 3 | 4 | 5 | 6 | 7 | VII-1 | Serpina1f |
| 456 | 3 | 4 | 5 | 6 | 7 | VII-1 | Serpina3k |
| 457 | 3 | 4 | 5 | 6 | 7 | VII-1 | Serpina3n |
| 458 | 3 | 4 | 5 | 6 | 7 | VII-1 | Serpinb2 |
| 459 | 3 | 4 | 5 | 6 | 7 | VII-1 | Slc17a9 |
| 460 | 3 | 4 | 5 | 6 | 7 | VII-1 | Slc1a1 |
| 461 | 3 | 4 | 5 | 6 | 7 | VII-1 | Slc27a2 |
| 462 | 3 | 4 | 5 | 6 | 7 | VII-1 | Slc35f2 |
| 463 | 3 | 4 | 5 | 6 | 7 | VII-1 | Slc38a5 |
| 464 | 3 | 4 | 5 | 6 | 7 | VII-1 | Slc9a7 |
| 465 | 3 | 4 | 5 | 6 | 7 | VII-1 | Snora16a |
| 466 | 3 | 4 | 5 | 6 | 7 | VII-1 | Snora17 |
| 467 | 3 | 4 | 5 | 6 | 7 | VII-1 | Snora21 |
| 468 | 3 | 4 | 5 | 6 | 7 | VII-1 | Snora28 |
| 469 | 3 | 4 | 5 | 6 | 7 | VII-1 | Snora2b |
| 470 | 3 | 4 | 5 | 6 | 7 | VII-1 | Snora3 |
| 471 | 3 | 4 | 5 | 6 | 7 | VII-1 | Snora30 |
| 472 | 3 | 4 | 5 | 6 | 7 | VII-1 | Snora31 |
| 473 | 3 | 4 | 5 | 6 | 7 | VII-1 | Snora33 |
| 474 | 3 | 4 | 5 | 6 | 7 | VII-1 | Snora34 |
| 475 | 3 | 4 | 5 | 6 | 7 | VII-1 | Snora36b |
| 476 | 3 | 4 | 5 | 6 | 7 | VII-1 | Snora41 |
| 477 | 3 | 4 | 5 | 6 | 7 | VII-1 | Snora43 |
| 478 | 3 | 4 | 5 | 6 | 7 | VII-1 | Snora44 |

| | | | | | | | |
|---|---|---|---|---|---|---|---|
| 479 | 3 | 4 | 5 | 6 | 7 | VII-1 | Snora52 |
| 480 | 3 | 4 | 5 | 6 | 7 | VII-1 | Snora5c |
| 481 | 3 | 4 | 5 | 6 | 7 | VII-1 | Snora62 |
| 482 | 3 | 4 | 5 | 6 | 7 | VII-1 | Snora64 |
| 483 | 3 | 4 | 5 | 6 | 7 | VII-1 | Snora65 |
| 484 | 3 | 4 | 5 | 6 | 7 | VII-1 | Snora69 |
| 485 | 3 | 4 | 5 | 6 | 7 | VII-1 | Snora70 |
| 486 | 3 | 4 | 5 | 6 | 7 | VII-1 | Snora75 |
| 487 | 3 | 4 | 5 | 6 | 7 | VII-1 | Snora78 |
| 488 | 3 | 4 | 5 | 6 | 7 | VII-1 | Snora7a |
| 489 | 3 | 4 | 5 | 6 | 7 | VII-1 | Snora81 |
| 490 | 3 | 4 | 5 | 6 | 7 | VII-1 | Snord15a |
| 491 | 3 | 4 | 5 | 6 | 7 | VII-1 | Snord15b |
| 492 | 3 | 4 | 5 | 6 | 7 | VII-1 | Snord22 |
| 493 | 3 | 4 | 5 | 6 | 7 | VII-1 | Spag11a |
| 494 | 3 | 4 | 5 | 6 | 7 | VII-1 | Spag11b |
| 495 | 3 | 4 | 5 | 6 | 7 | VII-1 | Spin2c |
| 496 | 3 | 4 | 5 | 6 | 7 | VII-1 | Spink11 |
| 497 | 3 | 4 | 5 | 6 | 7 | VII-1 | Spink12 |
| 498 | 3 | 4 | 5 | 6 | 7 | VII-1 | Spink2 |
| 499 | 3 | 4 | 5 | 6 | 7 | VII-1 | Spink5 |
| 500 | 3 | 4 | 5 | 6 | 7 | VII-1 | Spink8 |
| 501 | 3 | 4 | 5 | 6 | 7 | VII-1 | Spint1 |
| 502 | 3 | 4 | 5 | 6 | 7 | VII-1 | Spock1 |
| 503 | 3 | 4 | 5 | 6 | 7 | VII-1 | Srd5a2 |
| 504 | 3 | 4 | 5 | 6 | 7 | VII-1 | St6gal1 |
| 505 | 3 | 4 | 5 | 6 | 7 | VII-1 | Susd4 |
| 506 | 3 | 4 | 5 | 6 | 7 | VII-1 | Sv2c |
| 507 | 3 | 4 | 5 | 6 | 7 | VII-1 | Sycn |
| 508 | 3 | 4 | 5 | 6 | 7 | VII-1 | Syt14 |
| 509 | 3 | 4 | 5 | 6 | 7 | VII-1 | Tacstd2 |
| 510 | 3 | 4 | 5 | 6 | 7 | VII-1 | Tat |
| 511 | 3 | 4 | 5 | 6 | 7 | VII-1 | Tceal3 |
| 512 | 3 | 4 | 5 | 6 | 7 | VII-1 | Tcf7 |
| 513 | 3 | 4 | 5 | 6 | 7 | VII-1 | Teddm1 |
| 514 | 3 | 4 | 5 | 6 | 7 | VII-1 | Tff2 |
| 515 | 3 | 4 | 5 | 6 | 7 | VII-1 | Tff3 |
| 516 | 3 | 4 | 5 | 6 | 7 | VII-1 | Tgif2lx2 |
| 517 | 3 | 4 | 5 | 6 | 7 | VII-1 | Tgoln2 |
| 518 | 3 | 4 | 5 | 6 | 7 | VII-1 | Tgtp1 |
| 519 | 3 | 4 | 5 | 6 | 7 | VII-1 | Tgtp2 |
| 520 | 3 | 4 | 5 | 6 | 7 | VII-1 | Tm4sf20 |
| 521 | 3 | 4 | 5 | 6 | 7 | VII-1 | Tmem150c |
| 522 | 3 | 4 | 5 | 6 | 7 | VII-1 | Tmem178b |
| 523 | 3 | 4 | 5 | 6 | 7 | VII-1 | Tmem27 |
| 524 | 3 | 4 | 5 | 6 | 7 | VII-1 | Tox3 |
| 525 | 3 | 4 | 5 | 6 | 7 | VII-1 | Tpd52l1 |
| 526 | 3 | 4 | 5 | 6 | 7 | VII-1 | Trf |
| 527 | 3 | 4 | 5 | 6 | 7 | VII-1 | Trim56 |
| 528 | 3 | 4 | 5 | 6 | 7 | VII-1 | Try10 |
| 529 | 3 | 4 | 5 | 6 | 7 | VII-1 | Try4 |
| 530 | 3 | 4 | 5 | 6 | 7 | VII-1 | Try5 |
| 531 | 3 | 4 | 5 | 6 | 7 | VII-1 | Ttr |
| 532 | 3 | 4 | 5 | 6 | 7 | VII-1 | Ucp1 |
| 533 | 3 | 4 | 5 | 6 | 7 | VII-1 | Uhrnk1 |
| 534 | 3 | 4 | 5 | 6 | 7 | VII-1 | Vasn |
| 535 | 3 | 4 | 5 | 6 | 7 | VII-1 | Vip |
| 536 | 3 | 4 | 5 | 6 | 7 | VII-1 | Vtn |
| 537 | 3 | 4 | 5 | 6 | 7 | VII-1 | Wfdc10 |
| 538 | 3 | 4 | 5 | 6 | 7 | VII-1 | Wfdc11 |
| 539 | 3 | 4 | 5 | 6 | 7 | VII-1 | Wfdc15b |
| 540 | 3 | 4 | 5 | 6 | 7 | VII-1 | Wfdc2 |
| 541 | 3 | 4 | 5 | 6 | 7 | VII-1 | Wfdc6a |
| 542 | 3 | 4 | 5 | 6 | 7 | VII-1 | Wfdc6b |
| 543 | 3 | 4 | 5 | 6 | 7 | VII-1 | Wfdc8 |
| 544 | 3 | 4 | 5 | 6 | 7 | VII-1 | Wfdc9 |
| 545 | 3 | 4 | 5 | 6 | 7 | VII-1 | Wwc1 |
| 546 | 3 | 4 | 5 | 6 | 7 | VII-1 | Xkrx |
| 547 | 3 | 4 | 5 | 6 | 7 | VII-1 | Zbed6 |
| 548 | 3 | 4 | 5 | 6 | 7 | VII-1 | Zbp1 |
| 549 | 3 | 4 | 5 | 6 | 7 | VII-1 | Zfp369 |
| 550 | 3 | 4 | 5 | 6 | 7 | VII-1 | Zfp648 |
| 551 | 3 | 4 | 5 | 6 | 7 | VII-1 | Zg16 |
| 552 | 3 | 4 | 5 | 6 | | VI-2 | 0610040B10Rik |
| 553 | 3 | 4 | 5 | 6 | | VI-2 | 1010001N08Rik |
| 554 | 3 | 4 | 5 | 6 | | VI-2 | 1110020A21Rik |
| 555 | 3 | 4 | 5 | 6 | | VI-2 | 1190002F15Rik |
| 556 | 3 | 4 | 5 | 6 | | VI-2 | 1500012F01Rik |
| 557 | 3 | 4 | 5 | 6 | | VI-2 | 1500015O10Rik |
| 558 | 3 | 4 | 5 | 6 | | VI-2 | 1600002K03Rik |
| 559 | 3 | 4 | 5 | 6 | | VI-2 | 1700009C05Rik |
| 560 | 3 | 4 | 5 | 6 | | VI-2 | 1700012L04Rik |
| 561 | 3 | 4 | 5 | 6 | | VI-2 | 1700018L02Rik |
| 562 | 3 | 4 | 5 | 6 | | VI-2 | 1700023F06Rik |
| 563 | 3 | 4 | 5 | 6 | | VI-2 | 1700023L04Rik |
| 564 | 3 | 4 | 5 | 6 | | VI-2 | 1700028P15Rik |
| 565 | 3 | 4 | 5 | 6 | | VI-2 | 1700037H04Rik |
| 566 | 3 | 4 | 5 | 6 | | VI-2 | 1700041C23Rik |
| 567 | 3 | 4 | 5 | 6 | | VI-2 | 1700045H11Rik |
| 568 | 3 | 4 | 5 | 6 | | VI-2 | 1700047A11Rik |
| 569 | 3 | 4 | 5 | 6 | | VI-2 | 1700060C20Rik |
| 570 | 3 | 4 | 5 | 6 | | VI-2 | 1700084E18Rik |
| 571 | 3 | 4 | 5 | 6 | | VI-2 | 1700095B10Rik |
| 572 | 3 | 4 | 5 | 6 | | VI-2 | 1700101I11Rik |
| 573 | 3 | 4 | 5 | 6 | | VI-2 | 1810022K09Rik |
| 574 | 3 | 4 | 5 | 6 | | VI-2 | 1810044D09Rik |

Fig. 36 - 4

| | | | | | | |
|---|---|---|---|---|---|---|
| 575 | 3 | 4 | 5 | 6 | VI-2 | 1810062G17Rik |
| 576 | 3 | 4 | 5 | 6 | VI-2 | 2010106E10Rik |
| 577 | 3 | 4 | 5 | 6 | VI-2 | 2210013O21Rik |
| 578 | 3 | 4 | 5 | 6 | VI-2 | 2310001H17Rik |
| 579 | 3 | 4 | 5 | 6 | VI-2 | 2310002D06Rik |
| 580 | 3 | 4 | 5 | 6 | VI-2 | 2310009B15Rik |
| 581 | 3 | 4 | 5 | 6 | VI-2 | 2310015B20Rik |
| 582 | 3 | 4 | 5 | 6 | VI-2 | 2310040G24Rik |
| 583 | 3 | 4 | 5 | 6 | VI-2 | 2310045N01Rik |
| 584 | 3 | 4 | 5 | 6 | VI-2 | 2310047M10Rik |
| 585 | 3 | 4 | 5 | 6 | VI-2 | 2410006H16Rik |
| 586 | 3 | 4 | 5 | 6 | VI-2 | 2410141K09Rik |
| 587 | 3 | 4 | 5 | 6 | VI-2 | 2610002J02Rik |
| 588 | 3 | 4 | 5 | 6 | VI-2 | 2610016A17Rik |
| 589 | 3 | 4 | 5 | 6 | VI-2 | 2610203C22Rik |
| 590 | 3 | 4 | 5 | 6 | VI-2 | 2810403D21Rik |
| 591 | 3 | 4 | 5 | 6 | VI-2 | 2900009J06Rik |
| 592 | 3 | 4 | 5 | 6 | VI-2 | 2900076A07Rik |
| 593 | 3 | 4 | 5 | 6 | VI-2 | 3110009E18Rik |
| 594 | 3 | 4 | 5 | 6 | VI-2 | 3110039M20Rik |
| 595 | 3 | 4 | 5 | 6 | VI-2 | 3110070M22Rik |
| 596 | 3 | 4 | 5 | 6 | VI-2 | 4833411C07Rik |
| 597 | 3 | 4 | 5 | 6 | VI-2 | 4921509C19Rik |
| 598 | 3 | 4 | 5 | 6 | VI-2 | 4930429F24Rik |
| 599 | 3 | 4 | 5 | 6 | VI-2 | 4930430J02Rik |
| 600 | 3 | 4 | 5 | 6 | VI-2 | 4930453N24Rik |
| 601 | 3 | 4 | 5 | 6 | VI-2 | 4930456L15Rik |
| 602 | 3 | 4 | 5 | 6 | VI-2 | 4930474M22Rik |
| 603 | 3 | 4 | 5 | 6 | VI-2 | 4930520O04Rik |
| 604 | 3 | 4 | 5 | 6 | VI-2 | 4930562F07Rik |
| 605 | 3 | 4 | 5 | 6 | VI-2 | 4930578N18Rik |
| 606 | 3 | 4 | 5 | 6 | VI-2 | 4931403E22Rik |
| 607 | 3 | 4 | 5 | 6 | VI-2 | 4931408D14Rik |
| 608 | 3 | 4 | 5 | 6 | VI-2 | 4931428L18Rik |
| 609 | 3 | 4 | 5 | 6 | VI-2 | 4933439K11Rik |
| 610 | 3 | 4 | 5 | 6 | VI-2 | 5031434O11Rik |
| 611 | 3 | 4 | 5 | 6 | VI-2 | 5730416F02Rik |
| 612 | 3 | 4 | 5 | 6 | VI-2 | 9030619P08Rik |
| 613 | 3 | 4 | 5 | 6 | VI-2 | 9330159M07Rik |
| 614 | 3 | 4 | 5 | 6 | VI-2 | 9530003J23Rik |
| 615 | 3 | 4 | 5 | 6 | VI-2 | 9530026P05Rik |
| 616 | 3 | 4 | 5 | 6 | VI-2 | A330069E16Rik |
| 617 | 3 | 4 | 5 | 6 | VI-2 | A630023P12Rik |
| 618 | 3 | 4 | 5 | 6 | VI-2 | A730085K08Rik |
| 619 | 3 | 4 | 5 | 6 | VI-2 | AA474331 |
| 620 | 3 | 4 | 5 | 6 | VI-2 | AI507597 |
| 621 | 3 | 4 | 5 | 6 | VI-2 | Abhd15 |
| 622 | 3 | 4 | 5 | 6 | VI-2 | Acmsd |
| 623 | 3 | 4 | 5 | 6 | VI-2 | Acot7 |
| 624 | 3 | 4 | 5 | 6 | VI-2 | Acss3 |
| 625 | 3 | 4 | 5 | 6 | VI-2 | Acvr2b |
| 626 | 3 | 4 | 5 | 6 | VI-2 | Acyp2 |
| 627 | 3 | 4 | 5 | 6 | VI-2 | Alas1 |
| 628 | 3 | 4 | 5 | 6 | VI-2 | Alox8 |
| 629 | 3 | 4 | 5 | 6 | VI-2 | Amd2 |
| 630 | 3 | 4 | 5 | 6 | VI-2 | Ank1 |
| 631 | 3 | 4 | 5 | 6 | VI-2 | Ankrd2 |
| 632 | 3 | 4 | 5 | 6 | VI-2 | Ankrd37 |
| 633 | 3 | 4 | 5 | 6 | VI-2 | Ap3s1 |
| 634 | 3 | 4 | 5 | 6 | VI-2 | Apoo |
| 635 | 3 | 4 | 5 | 6 | VI-2 | Apopt1 |
| 636 | 3 | 4 | 5 | 6 | VI-2 | Arhgap26 |
| 637 | 3 | 4 | 5 | 6 | VI-2 | Asb17os |
| 638 | 3 | 4 | 5 | 6 | VI-2 | Asgr1 |
| 639 | 3 | 4 | 5 | 6 | VI-2 | Asun |
| 640 | 3 | 4 | 5 | 6 | VI-2 | Atf5 |
| 641 | 3 | 4 | 5 | 6 | VI-2 | Atg10 |
| 642 | 3 | 4 | 5 | 6 | VI-2 | Atg4a |
| 643 | 3 | 4 | 5 | 6 | VI-2 | Atoh8 |
| 644 | 3 | 4 | 5 | 6 | VI-2 | Atox1 |
| 645 | 3 | 4 | 5 | 6 | VI-2 | Atp2a1 |
| 646 | 3 | 4 | 5 | 6 | VI-2 | Auh |
| 647 | 3 | 4 | 5 | 6 | VI-2 | Azin1 |
| 648 | 3 | 4 | 5 | 6 | VI-2 | B9d2 |
| 649 | 3 | 4 | 5 | 6 | VI-2 | Bach1 |
| 650 | 3 | 4 | 5 | 6 | VI-2 | Batf3 |
| 651 | 3 | 4 | 5 | 6 | VI-2 | Bgn |
| 652 | 3 | 4 | 5 | 6 | VI-2 | Bik |
| 653 | 3 | 4 | 5 | 6 | VI-2 | Blvrb |
| 654 | 3 | 4 | 5 | 6 | VI-2 | Bmp2 |
| 655 | 3 | 4 | 5 | 6 | VI-2 | Bmper |
| 656 | 3 | 4 | 5 | 6 | VI-2 | Bnc1 |
| 657 | 3 | 4 | 5 | 6 | VI-2 | Brpf3 |
| 658 | 3 | 4 | 5 | 6 | VI-2 | Bsdc1 |
| 659 | 3 | 4 | 5 | 6 | VI-2 | C130083M11Rik |
| 660 | 3 | 4 | 5 | 6 | VI-2 | C530008M17Rik |
| 661 | 3 | 4 | 5 | 6 | VI-2 | C920006O11Rik |
| 662 | 3 | 4 | 5 | 6 | VI-2 | Camk1 |
| 663 | 3 | 4 | 5 | 6 | VI-2 | Car7 |
| 664 | 3 | 4 | 5 | 6 | VI-2 | Cbr4 |
| 665 | 3 | 4 | 5 | 6 | VI-2 | Ccdc170 |
| 666 | 3 | 4 | 5 | 6 | VI-2 | Ccl11 |
| 667 | 3 | 4 | 5 | 6 | VI-2 | Ccl17 |
| 668 | 3 | 4 | 5 | 6 | VI-2 | Ccl19 |
| 669 | 3 | 4 | 5 | 6 | VI-2 | Ccl3 |
| 670 | 3 | 4 | 5 | 6 | VI-2 | Ccl6 |
| 671 | 3 | 4 | 5 | 6 | VI-2 | Ccna2 |
| 672 | 3 | 4 | 5 | 6 | VI-2 | Cd209d |
| 673 | 3 | 4 | 5 | 6 | VI-2 | Cd247 |
| 674 | 3 | 4 | 5 | 6 | VI-2 | Cd274 |
| 675 | 3 | 4 | 5 | 6 | VI-2 | Cd302 |
| 676 | 3 | 4 | 5 | 6 | VI-2 | Cd59a |
| 677 | 3 | 4 | 5 | 6 | VI-2 | Cd7 |
| 678 | 3 | 4 | 5 | 6 | VI-2 | Cdkn2b |
| 679 | 3 | 4 | 5 | 6 | VI-2 | Cds2 |
| 680 | 3 | 4 | 5 | 6 | VI-2 | Cep192 |
| 681 | 3 | 4 | 5 | 6 | VI-2 | Cfhr2 |
| 682 | 3 | 4 | 5 | 6 | VI-2 | Chac1 |
| 683 | 3 | 4 | 5 | 6 | VI-2 | Chchd7 |
| 684 | 3 | 4 | 5 | 6 | VI-2 | Chic2 |
| 685 | 3 | 4 | 5 | 6 | VI-2 | Chil3 |
| 686 | 3 | 4 | 5 | 6 | VI-2 | Chml |
| 687 | 3 | 4 | 5 | 6 | VI-2 | Chmp2a |
| 688 | 3 | 4 | 5 | 6 | VI-2 | Chp2 |
| 689 | 3 | 4 | 5 | 6 | VI-2 | Chrdl2 |
| 690 | 3 | 4 | 5 | 6 | VI-2 | Chrna9 |
| 691 | 3 | 4 | 5 | 6 | VI-2 | Cir1 |
| 692 | 3 | 4 | 5 | 6 | VI-2 | Cklf |
| 693 | 3 | 4 | 5 | 6 | VI-2 | Clec3a |
| 694 | 3 | 4 | 5 | 6 | VI-2 | Clip2 |
| 695 | 3 | 4 | 5 | 6 | VI-2 | Cmas |
| 696 | 3 | 4 | 5 | 6 | VI-2 | Cmbl |
| 697 | 3 | 4 | 5 | 6 | VI-2 | Cnksr3 |
| 698 | 3 | 4 | 5 | 6 | VI-2 | Cnp |
| 699 | 3 | 4 | 5 | 6 | VI-2 | Cnr2 |
| 700 | 3 | 4 | 5 | 6 | VI-2 | Cnst |
| 701 | 3 | 4 | 5 | 6 | VI-2 | Col4a3 |
| 702 | 3 | 4 | 5 | 6 | VI-2 | Cort |
| 703 | 3 | 4 | 5 | 6 | VI-2 | Cox17 |
| 704 | 3 | 4 | 5 | 6 | VI-2 | Cox7a1 |
| 705 | 3 | 4 | 5 | 6 | VI-2 | Cox7a2 |
| 706 | 3 | 4 | 5 | 6 | VI-2 | Cpne3 |
| 707 | 3 | 4 | 5 | 6 | VI-2 | Crip2 |
| 708 | 3 | 4 | 5 | 6 | VI-2 | Crybb1 |
| 709 | 3 | 4 | 5 | 6 | VI-2 | Csgalnact1 |
| 710 | 3 | 4 | 5 | 6 | VI-2 | Cttn |
| 711 | 3 | 4 | 5 | 6 | VI-2 | Cxcl12 |
| 712 | 3 | 4 | 5 | 6 | VI-2 | Cyp26b1 |
| 713 | 3 | 4 | 5 | 6 | VI-2 | Cyp27b1 |
| 714 | 3 | 4 | 5 | 6 | VI-2 | Cyp2c67 |
| 715 | 3 | 4 | 5 | 6 | VI-2 | Cyp2j9 |
| 716 | 3 | 4 | 5 | 6 | VI-2 | Cyp4b1-ps2 |
| 717 | 3 | 4 | 5 | 6 | VI-2 | D130020L05Rik |
| 718 | 3 | 4 | 5 | 6 | VI-2 | D430020J02Rik |
| 719 | 3 | 4 | 5 | 6 | VI-2 | D630023F18Rik |
| 720 | 3 | 4 | 5 | 6 | VI-2 | D630033O11Rik |
| 721 | 3 | 4 | 5 | 6 | VI-2 | D830046C22Rik |
| 722 | 3 | 4 | 5 | 6 | VI-2 | Dancr |
| 723 | 3 | 4 | 5 | 6 | VI-2 | Dbil5 |
| 724 | 3 | 4 | 5 | 6 | VI-2 | Dctpp1 |
| 725 | 3 | 4 | 5 | 6 | VI-2 | Ddit3 |
| 726 | 3 | 4 | 5 | 6 | VI-2 | Dear1 |
| 727 | 3 | 4 | 5 | 6 | VI-2 | Defa2 |
| 728 | 3 | 4 | 5 | 6 | VI-2 | Dhcr24 |
| 729 | 3 | 4 | 5 | 6 | VI-2 | Dhrs11 |
| 730 | 3 | 4 | 5 | 6 | VI-2 | Dleu2 |
| 731 | 3 | 4 | 5 | 6 | VI-2 | Dmtn |
| 732 | 3 | 4 | 5 | 6 | VI-2 | Dnph1 |
| 733 | 3 | 4 | 5 | 6 | VI-2 | Dnttip1 |
| 734 | 3 | 4 | 5 | 6 | VI-2 | Doc2b |
| 735 | 3 | 4 | 5 | 6 | VI-2 | Dok1 |
| 736 | 3 | 4 | 5 | 6 | VI-2 | Dok3 |
| 737 | 3 | 4 | 5 | 6 | VI-2 | Drp2 |
| 738 | 3 | 4 | 5 | 6 | VI-2 | Dusp5 |
| 739 | 3 | 4 | 5 | 6 | VI-2 | Dym |
| 740 | 3 | 4 | 5 | 6 | VI-2 | Dynlrb1 |
| 741 | 3 | 4 | 5 | 6 | VI-2 | E030003E18Rik |
| 742 | 3 | 4 | 5 | 6 | VI-2 | E030030I06Rik |
| 743 | 3 | 4 | 5 | 6 | VI-2 | E130018N17Rik |
| 744 | 3 | 4 | 5 | 6 | VI-2 | E130201H02Rik |
| 745 | 3 | 4 | 5 | 6 | VI-2 | E230016M11Rik |
| 746 | 3 | 4 | 5 | 6 | VI-2 | E2f2 |
| 747 | 3 | 4 | 5 | 6 | VI-2 | Ear1 |
| 748 | 3 | 4 | 5 | 6 | VI-2 | Ear10 |
| 749 | 3 | 4 | 5 | 6 | VI-2 | Ear2 |
| 750 | 3 | 4 | 5 | 6 | VI-2 | Ebp |
| 751 | 3 | 4 | 5 | 6 | VI-2 | Echdc3 |
| 752 | 3 | 4 | 5 | 6 | VI-2 | Eci3 |
| 753 | 3 | 4 | 5 | 6 | VI-2 | Edn1 |
| 754 | 3 | 4 | 5 | 6 | VI-2 | Eif1b |
| 755 | 3 | 4 | 5 | 6 | VI-2 | Epb4.1 |
| 756 | 3 | 4 | 5 | 6 | VI-2 | Epb4.2 |
| 757 | 3 | 4 | 5 | 6 | VI-2 | Esm1 |
| 758 | 3 | 4 | 5 | 6 | VI-2 | Eya3 |
| 759 | 3 | 4 | 5 | 6 | VI-2 | F2rl2 |
| 760 | 3 | 4 | 5 | 6 | VI-2 | F830002L21Rik |
| 761 | 3 | 4 | 5 | 6 | VI-2 | Fam129a |
| 762 | 3 | 4 | 5 | 6 | VI-2 | Fam13a |
| 763 | 3 | 4 | 5 | 6 | VI-2 | Fam174b |
| 764 | 3 | 4 | 5 | 6 | VI-2 | Fam180a |
| 765 | 3 | 4 | 5 | 6 | VI-2 | Fam210b |
| 766 | 3 | 4 | 5 | 6 | VI-2 | Fam213a |

Fig. 36 - 5

| | | | | | | | |
|---|---|---|---|---|---|---|---|
| 767 | 3 | 4 | 5 | 6 | | VI-2 | Fam53b |
| 768 | 3 | 4 | 5 | 6 | | VI-2 | Fam63a |
| 769 | 3 | 4 | 5 | 6 | | VI-2 | Fancl |
| 770 | 3 | 4 | 5 | 6 | | VI-2 | Fars2 |
| 771 | 3 | 4 | 5 | 6 | | VI-2 | Fasl |
| 772 | 3 | 4 | 5 | 6 | | VI-2 | Fbl |
| 773 | 3 | 4 | 5 | 6 | | VI-2 | Fbxo9 |
| 774 | 3 | 4 | 5 | 6 | | VI-2 | Fech |
| 775 | 3 | 4 | 5 | 6 | | VI-2 | Fermt3 |
| 776 | 3 | 4 | 5 | 6 | | VI-2 | Fetub |
| 777 | 3 | 4 | 5 | 6 | | VI-2 | Fev |
| 778 | 3 | 4 | 5 | 6 | | VI-2 | Fgf18 |
| 779 | 3 | 4 | 5 | 6 | | VI-2 | Fmo2 |
| 780 | 3 | 4 | 5 | 6 | | VI-2 | Foxo4 |
| 781 | 3 | 4 | 5 | 6 | | VI-2 | Fxyd3 |
| 782 | 3 | 4 | 5 | 6 | | VI-2 | G530011O06Rik |
| 783 | 3 | 4 | 5 | 6 | | VI-2 | G6bos |
| 784 | 3 | 4 | 5 | 6 | | VI-2 | Gadd45g |
| 785 | 3 | 4 | 5 | 6 | | VI-2 | Galnt1 |
| 786 | 3 | 4 | 5 | 6 | | VI-2 | Gata1 |
| 787 | 3 | 4 | 5 | 6 | | VI-2 | Gata2 |
| 788 | 3 | 4 | 5 | 6 | | VI-2 | Gclm |
| 789 | 3 | 4 | 5 | 6 | | VI-2 | Gcsam |
| 790 | 3 | 4 | 5 | 6 | | VI-2 | Gdpd3 |
| 791 | 3 | 4 | 5 | 6 | | VI-2 | Gemin7 |
| 792 | 3 | 4 | 5 | 6 | | VI-2 | Gfi1b |
| 793 | 3 | 4 | 5 | 6 | | VI-2 | Gh |
| 794 | 3 | 4 | 5 | 6 | | VI-2 | Gja4 |
| 795 | 3 | 4 | 5 | 6 | | VI-2 | Gjb5 |
| 796 | 3 | 4 | 5 | 6 | | VI-2 | Gkn2 |
| 797 | 3 | 4 | 5 | 6 | | VI-2 | Glb1 |
| 798 | 3 | 4 | 5 | 6 | | VI-2 | Glis3 |
| 799 | 3 | 4 | 5 | 6 | | VI-2 | Gm10094 |
| 800 | 3 | 4 | 5 | 6 | | VI-2 | Gm10228 |
| 801 | 3 | 4 | 5 | 6 | | VI-2 | Gm10229 |
| 802 | 3 | 4 | 5 | 6 | | VI-2 | Gm10324 |
| 803 | 3 | 4 | 5 | 6 | | VI-2 | Gm10486 |
| 804 | 3 | 4 | 5 | 6 | | VI-2 | Gm10487 |
| 805 | 3 | 4 | 5 | 6 | | VI-2 | Gm10509 |
| 806 | 3 | 4 | 5 | 6 | | VI-2 | Gm10591 |
| 807 | 3 | 4 | 5 | 6 | | VI-2 | Gm11110 |
| 808 | 3 | 4 | 5 | 6 | | VI-2 | Gm11837 |
| 809 | 3 | 4 | 5 | 6 | | VI-2 | Gm13306 |
| 810 | 3 | 4 | 5 | 6 | | VI-2 | Gm14005 |
| 811 | 3 | 4 | 5 | 6 | | VI-2 | Gm14207 |
| 812 | 3 | 4 | 5 | 6 | | VI-2 | Gm14393 |
| 813 | 3 | 4 | 5 | 6 | | VI-2 | Gm14819 |
| 814 | 3 | 4 | 5 | 6 | | VI-2 | Gm15319 |
| 815 | 3 | 4 | 5 | 6 | | VI-2 | Gm15441 |
| 816 | 3 | 4 | 5 | 6 | | VI-2 | Gm166 |
| 817 | 3 | 4 | 5 | 6 | | VI-2 | Gm1673 |
| 818 | 3 | 4 | 5 | 6 | | VI-2 | Gm17455 |
| 819 | 3 | 4 | 5 | 6 | | VI-2 | Gm20324 |
| 820 | 3 | 4 | 5 | 6 | | VI-2 | Gm20748 |
| 821 | 3 | 4 | 5 | 6 | | VI-2 | Gm21119 |
| 822 | 3 | 4 | 5 | 6 | | VI-2 | Gm21541 |
| 823 | 3 | 4 | 5 | 6 | | VI-2 | Gm3086 |
| 824 | 3 | 4 | 5 | 6 | | VI-2 | Gm3258 |
| 825 | 3 | 4 | 5 | 6 | | VI-2 | Gm4285 |
| 826 | 3 | 4 | 5 | 6 | | VI-2 | Gm4532 |
| 827 | 3 | 4 | 5 | 6 | | VI-2 | Gm5088 |
| 828 | 3 | 4 | 5 | 6 | | VI-2 | Gm5416 |
| 829 | 3 | 4 | 5 | 6 | | VI-2 | Gm5801 |
| 830 | 3 | 4 | 5 | 6 | | VI-2 | Gm6524 |
| 831 | 3 | 4 | 5 | 6 | | VI-2 | Gm6525 |
| 832 | 3 | 4 | 5 | 6 | | VI-2 | Gm6634 |
| 833 | 3 | 4 | 5 | 6 | | VI-2 | Gm6654 |
| 834 | 3 | 4 | 5 | 6 | | VI-2 | Gm694 |
| 835 | 3 | 4 | 5 | 6 | | VI-2 | Gm867 |
| 836 | 3 | 4 | 5 | 6 | | VI-2 | Gm904 |
| 837 | 3 | 4 | 5 | 6 | | VI-2 | Gm9895 |
| 838 | 3 | 4 | 5 | 6 | | VI-2 | Gm9961 |
| 839 | 3 | 4 | 5 | 6 | | VI-2 | Gmds |
| 840 | 3 | 4 | 5 | 6 | | VI-2 | Gmnn |
| 841 | 3 | 4 | 5 | 6 | | VI-2 | Gng11 |
| 842 | 3 | 4 | 5 | 6 | | VI-2 | Gp1ba |
| 843 | 3 | 4 | 5 | 6 | | VI-2 | Gp6 |
| 844 | 3 | 4 | 5 | 6 | | VI-2 | Gpc1 |
| 845 | 3 | 4 | 5 | 6 | | VI-2 | Gpc3 |
| 846 | 3 | 4 | 5 | 6 | | VI-2 | Gpm6a |
| 847 | 3 | 4 | 5 | 6 | | VI-2 | Gpr137b-ps |
| 848 | 3 | 4 | 5 | 6 | | VI-2 | Gpr4 |
| 849 | 3 | 4 | 5 | 6 | | VI-2 | Gpx1 |
| 850 | 3 | 4 | 5 | 6 | | VI-2 | Grp |
| 851 | 3 | 4 | 5 | 6 | | VI-2 | Grpr |
| 852 | 3 | 4 | 5 | 6 | | VI-2 | Gsn |
| 853 | 3 | 4 | 5 | 6 | | VI-2 | Gsta4 |
| 854 | 3 | 4 | 5 | 6 | | VI-2 | Gstm2 |
| 855 | 3 | 4 | 5 | 6 | | VI-2 | Gstt1 |
| 856 | 3 | 4 | 5 | 6 | | VI-2 | Gvin1 |
| 857 | 3 | 4 | 5 | 6 | | VI-2 | Gypa |
| 858 | 3 | 4 | 5 | 6 | | VI-2 | H2-M9 |
| 859 | 3 | 4 | 5 | 6 | | VI-2 | H2-Ob |
| 860 | 3 | 4 | 5 | 6 | | VI-2 | H2-T22 |
| 861 | 3 | 4 | 5 | 6 | | VI-2 | H2-T23 |
| 862 | 3 | 4 | 5 | 6 | | VI-2 | Haus1 |
| 863 | 3 | 4 | 5 | 6 | | VI-2 | Hdac5 |
| 864 | 3 | 4 | 5 | 6 | | VI-2 | Hddc2 |
| 865 | 3 | 4 | 5 | 6 | | VI-2 | Hexim2 |
| 866 | 3 | 4 | 5 | 6 | | VI-2 | Hey1 |
| 867 | 3 | 4 | 5 | 6 | | VI-2 | Higd2a |
| 868 | 3 | 4 | 5 | 6 | | VI-2 | Hint2 |
| 869 | 3 | 4 | 5 | 6 | | VI-2 | Hist1h2ab |
| 870 | 3 | 4 | 5 | 6 | | VI-2 | Hist1h2ac |
| 871 | 3 | 4 | 5 | 6 | | VI-2 | Hist1h2af |
| 872 | 3 | 4 | 5 | 6 | | VI-2 | Hist1h2ag |
| 873 | 3 | 4 | 5 | 6 | | VI-2 | Hist1h2an |
| 874 | 3 | 4 | 5 | 6 | | VI-2 | Hist1h2ao |
| 875 | 3 | 4 | 5 | 6 | | VI-2 | Hist1h2ap |
| 876 | 3 | 4 | 5 | 6 | | VI-2 | Hist1h2bb |
| 877 | 3 | 4 | 5 | 6 | | VI-2 | Hist1h2bl |
| 878 | 3 | 4 | 5 | 6 | | VI-2 | Hist1h2bm |
| 879 | 3 | 4 | 5 | 6 | | VI-2 | Hist1h3a |
| 880 | 3 | 4 | 5 | 6 | | VI-2 | Hist1h3b |
| 881 | 3 | 4 | 5 | 6 | | VI-2 | Hist1h3d |
| 882 | 3 | 4 | 5 | 6 | | VI-2 | Hist1h3h |
| 883 | 3 | 4 | 5 | 6 | | VI-2 | Hist1h4c |
| 884 | 3 | 4 | 5 | 6 | | VI-2 | Hist3h2a |
| 885 | 3 | 4 | 5 | 6 | | VI-2 | Hmga1-rs1 |
| 886 | 3 | 4 | 5 | 6 | | VI-2 | Hmgn3 |
| 887 | 3 | 4 | 5 | 6 | | VI-2 | Hspb1 |
| 888 | 3 | 4 | 5 | 6 | | VI-2 | Htr3a |
| 889 | 3 | 4 | 5 | 6 | | VI-2 | Hyi |
| 890 | 3 | 4 | 5 | 6 | | VI-2 | I830077J02Rik |
| 891 | 3 | 4 | 5 | 6 | | VI-2 | Ica1 |
| 892 | 3 | 4 | 5 | 6 | | VI-2 | Ifi203 |
| 893 | 3 | 4 | 5 | 6 | | VI-2 | Il1a |
| 894 | 3 | 4 | 5 | 6 | | VI-2 | Il1rn |
| 895 | 3 | 4 | 5 | 6 | | VI-2 | Il22 |
| 896 | 3 | 4 | 5 | 6 | | VI-2 | Il22ra2 |
| 897 | 3 | 4 | 5 | 6 | | VI-2 | Il4i1 |
| 898 | 3 | 4 | 5 | 6 | | VI-2 | Inf2 |
| 899 | 3 | 4 | 5 | 6 | | VI-2 | Insc |
| 900 | 3 | 4 | 5 | 6 | | VI-2 | Iqck |
| 901 | 3 | 4 | 5 | 6 | | VI-2 | Irak1 |
| 902 | 3 | 4 | 5 | 6 | | VI-2 | Itga2b |
| 903 | 3 | 4 | 5 | 6 | | VI-2 | Itgb1bp1 |
| 904 | 3 | 4 | 5 | 6 | | VI-2 | Itgb1bp2 |
| 905 | 3 | 4 | 5 | 6 | | VI-2 | Itgb5 |
| 906 | 3 | 4 | 5 | 6 | | VI-2 | Itpkb |
| 907 | 3 | 4 | 5 | 6 | | VI-2 | Izumo4 |
| 908 | 3 | 4 | 5 | 6 | | VI-2 | Josd2 |
| 909 | 3 | 4 | 5 | 6 | | VI-2 | Kansl1l |
| 910 | 3 | 4 | 5 | 6 | | VI-2 | Kcnf1 |
| 911 | 3 | 4 | 5 | 6 | | VI-2 | Kcnmb4os1 |
| 912 | 3 | 4 | 5 | 6 | | VI-2 | Klk10 |
| 913 | 3 | 4 | 5 | 6 | | VI-2 | Klra13-ps |
| 914 | 3 | 4 | 5 | 6 | | VI-2 | Klra7 |
| 915 | 3 | 4 | 5 | 6 | | VI-2 | Klra8 |
| 916 | 3 | 4 | 5 | 6 | | VI-2 | Klrd1 |
| 917 | 3 | 4 | 5 | 6 | | VI-2 | Kpna2 |
| 918 | 3 | 4 | 5 | 6 | | VI-2 | Krt76 |
| 919 | 3 | 4 | 5 | 6 | | VI-2 | Krtap1-5 |
| 920 | 3 | 4 | 5 | 6 | | VI-2 | Krtap15 |
| 921 | 3 | 4 | 5 | 6 | | VI-2 | Krtap16-3 |
| 922 | 3 | 4 | 5 | 6 | | VI-2 | Krtap19-3 |
| 923 | 3 | 4 | 5 | 6 | | VI-2 | Krtap19-5 |
| 924 | 3 | 4 | 5 | 6 | | VI-2 | Krtap2-4 |
| 925 | 3 | 4 | 5 | 6 | | VI-2 | Krtap22-2 |
| 926 | 3 | 4 | 5 | 6 | | VI-2 | Krtap4-1 |
| 927 | 3 | 4 | 5 | 6 | | VI-2 | Krtap6-1 |
| 928 | 3 | 4 | 5 | 6 | | VI-2 | Krtap6-5 |
| 929 | 3 | 4 | 5 | 6 | | VI-2 | Krtap7-1 |
| 930 | 3 | 4 | 5 | 6 | | VI-2 | LOC106740 |
| 931 | 3 | 4 | 5 | 6 | | VI-2 | Larp1b |
| 932 | 3 | 4 | 5 | 6 | | VI-2 | Lbx2 |
| 933 | 3 | 4 | 5 | 6 | | VI-2 | Lce3f |
| 934 | 3 | 4 | 5 | 6 | | VI-2 | Lgals1 |
| 935 | 3 | 4 | 5 | 6 | | VI-2 | Lhfp |
| 936 | 3 | 4 | 5 | 6 | | VI-2 | Lmo2 |
| 937 | 3 | 4 | 5 | 6 | | VI-2 | Loh12cr1 |
| 938 | 3 | 4 | 5 | 6 | | VI-2 | Lpar4 |
| 939 | 3 | 4 | 5 | 6 | | VI-2 | Lpl |
| 940 | 3 | 4 | 5 | 6 | | VI-2 | Lrif1 |
| 941 | 3 | 4 | 5 | 6 | | VI-2 | Lrrc28 |
| 942 | 3 | 4 | 5 | 6 | | VI-2 | Lrrfip2 |
| 943 | 3 | 4 | 5 | 6 | | VI-2 | Lsm3 |
| 944 | 3 | 4 | 5 | 6 | | VI-2 | Lsm4 |
| 945 | 3 | 4 | 5 | 6 | | VI-2 | Lsm5 |
| 946 | 3 | 4 | 5 | 6 | | VI-2 | Ly6g6c |
| 947 | 3 | 4 | 5 | 6 | | VI-2 | Ly6g6d |
| 948 | 3 | 4 | 5 | 6 | | VI-2 | Ly6i |
| 949 | 3 | 4 | 5 | 6 | | VI-2 | Lysmd3 |
| 950 | 3 | 4 | 5 | 6 | | VI-2 | Lzts1 |
| 951 | 3 | 4 | 5 | 6 | | VI-2 | Maff |
| 952 | 3 | 4 | 5 | 6 | | VI-2 | Mageb1 |
| 953 | 3 | 4 | 5 | 6 | | VI-2 | Magoh |
| 954 | 3 | 4 | 5 | 6 | | VI-2 | Magohb |
| 955 | 3 | 4 | 5 | 6 | | VI-2 | Mamdc2 |
| 956 | 3 | 4 | 5 | 6 | | VI-2 | March5 |
| 957 | 3 | 4 | 5 | 6 | | VI-2 | Marco |
| 958 | 3 | 4 | 5 | 6 | | VI-2 | Mb |

Fig. 36 - 6

| | | | | | | | |
|---|---|---|---|---|---|---|---|
| 959 | 3 | 4 | 5 | 6 | | VI-2 | Mcpt4 |
| 960 | 3 | 4 | 5 | 6 | | VI-2 | Meig1 |
| 961 | 3 | 4 | 5 | 6 | | VI-2 | Mfsd4 |
| 962 | 3 | 4 | 5 | 6 | | VI-2 | Mgarp |
| 963 | 3 | 4 | 5 | 6 | | VI-2 | Mgmt |
| 964 | 3 | 4 | 5 | 6 | | VI-2 | Mgp |
| 965 | 3 | 4 | 5 | 6 | | VI-2 | Mien1 |
| 966 | 3 | 4 | 5 | 6 | | VI-2 | Mink1 |
| 967 | 3 | 4 | 5 | 6 | | VI-2 | Mira |
| 968 | 3 | 4 | 5 | 6 | | VI-2 | Mirlet7bhg |
| 969 | 3 | 4 | 5 | 6 | | VI-2 | Mmp12 |
| 970 | 3 | 4 | 5 | 6 | | VI-2 | Mmp13 |
| 971 | 3 | 4 | 5 | 6 | | VI-2 | Morn2 |
| 972 | 3 | 4 | 5 | 6 | | VI-2 | Mpp1 |
| 973 | 3 | 4 | 5 | 6 | | VI-2 | Mpst |
| 974 | 3 | 4 | 5 | 6 | | VI-2 | Mr1 |
| 975 | 3 | 4 | 5 | 6 | | VI-2 | Mrpl20 |
| 976 | 3 | 4 | 5 | 6 | | VI-2 | Mrpl3 |
| 977 | 3 | 4 | 5 | 6 | | VI-2 | Mrps10 |
| 978 | 3 | 4 | 5 | 6 | | VI-2 | Mrps21 |
| 979 | 3 | 4 | 5 | 6 | | VI-2 | Mrps6 |
| 980 | 3 | 4 | 5 | 6 | | VI-2 | Msc |
| 981 | 3 | 4 | 5 | 6 | | VI-2 | Msln |
| 982 | 3 | 4 | 5 | 6 | | VI-2 | Msto1 |
| 983 | 3 | 4 | 5 | 6 | | VI-2 | Mt2 |
| 984 | 3 | 4 | 5 | 6 | | VI-2 | Mta3 |
| 985 | 3 | 4 | 5 | 6 | | VI-2 | Mtmr14 |
| 986 | 3 | 4 | 5 | 6 | | VI-2 | Mtss1 |
| 987 | 3 | 4 | 5 | 6 | | VI-2 | Mtx2 |
| 988 | 3 | 4 | 5 | 6 | | VI-2 | Mup11 |
| 989 | 3 | 4 | 5 | 6 | | VI-2 | Musk |
| 990 | 3 | 4 | 5 | 6 | | VI-2 | Mustn1 |
| 991 | 3 | 4 | 5 | 6 | | VI-2 | Myh6 |
| 992 | 3 | 4 | 5 | 6 | | VI-2 | Myh7 |
| 993 | 3 | 4 | 5 | 6 | | VI-2 | Myl4 |
| 994 | 3 | 4 | 5 | 6 | | VI-2 | Mzb1 |
| 995 | 3 | 4 | 5 | 6 | | VI-2 | Nck2 |
| 996 | 3 | 4 | 5 | 6 | | VI-2 | Ncoa4 |
| 997 | 3 | 4 | 5 | 6 | | VI-2 | Ndufaf5 |
| 998 | 3 | 4 | 5 | 6 | | VI-2 | Ndufb5 |
| 999 | 3 | 4 | 5 | 6 | | VI-2 | Necab2 |
| 1000 | 3 | 4 | 5 | 6 | | VI-2 | Neu2 |
| 1001 | 3 | 4 | 5 | 6 | | VI-2 | Nhs |
| 1002 | 3 | 4 | 5 | 6 | | VI-2 | Nipal |
| 1003 | 3 | 4 | 5 | 6 | | VI-2 | Nmral1 |
| 1004 | 3 | 4 | 5 | 6 | | VI-2 | Npb |
| 1005 | 3 | 4 | 5 | 6 | | VI-2 | Npw |
| 1006 | 3 | 4 | 5 | 6 | | VI-2 | Nr1d1 |
| 1007 | 3 | 4 | 5 | 6 | | VI-2 | Nr1d2 |
| 1008 | 3 | 4 | 5 | 6 | | VI-2 | Nrarp |
| 1009 | 3 | 4 | 5 | 6 | | VI-2 | Ntn5 |
| 1010 | 3 | 4 | 5 | 6 | | VI-2 | Nuak2 |
| 1011 | 3 | 4 | 5 | 6 | | VI-2 | Nudt2 |
| 1012 | 3 | 4 | 5 | 6 | | VI-2 | Nudt6 |
| 1013 | 3 | 4 | 5 | 6 | | VI-2 | Nupr1l |
| 1014 | 3 | 4 | 5 | 6 | | VI-2 | Nusap1 |
| 1015 | 3 | 4 | 5 | 6 | | VI-2 | Nutf2-ps1 |
| 1016 | 3 | 4 | 5 | 6 | | VI-2 | Oas1e |
| 1017 | 3 | 4 | 5 | 6 | | VI-2 | Obp2a |
| 1018 | 3 | 4 | 5 | 6 | | VI-2 | Optn |
| 1019 | 3 | 4 | 5 | 6 | | VI-2 | Ormdl3 |
| 1020 | 3 | 4 | 5 | 6 | | VI-2 | Otud7b |
| 1021 | 3 | 4 | 5 | 6 | | VI-2 | P2ry1 |
| 1022 | 3 | 4 | 5 | 6 | | VI-2 | Pabpc1 |
| 1023 | 3 | 4 | 5 | 6 | | VI-2 | Pabpc4 |
| 1024 | 3 | 4 | 5 | 6 | | VI-2 | Pam16 |
| 1025 | 3 | 4 | 5 | 6 | | VI-2 | Pamr1 |
| 1026 | 3 | 4 | 5 | 6 | | VI-2 | Pcdhgb6 |
| 1027 | 3 | 4 | 5 | 6 | | VI-2 | Pck2 |
| 1028 | 3 | 4 | 5 | 6 | | VI-2 | Pdcd5 |
| 1029 | 3 | 4 | 5 | 6 | | VI-2 | Pde6h |
| 1030 | 3 | 4 | 5 | 6 | | VI-2 | Pdlim1 |
| 1031 | 3 | 4 | 5 | 6 | | VI-2 | Peg10 |
| 1032 | 3 | 4 | 5 | 6 | | VI-2 | Per2 |
| 1033 | 3 | 4 | 5 | 6 | | VI-2 | Per3 |
| 1034 | 3 | 4 | 5 | 6 | | VI-2 | Pfdn2 |
| 1035 | 3 | 4 | 5 | 6 | | VI-2 | Pgc |
| 1036 | 3 | 4 | 5 | 6 | | VI-2 | Pglyrp1 |
| 1037 | 3 | 4 | 5 | 6 | | VI-2 | Phtf1os |
| 1038 | 3 | 4 | 5 | 6 | | VI-2 | Pik3c2g |
| 1039 | 3 | 4 | 5 | 6 | | VI-2 | Pik3ip1 |
| 1040 | 3 | 4 | 5 | 6 | | VI-2 | Pin4 |
| 1041 | 3 | 4 | 5 | 6 | | VI-2 | Pira1 |
| 1042 | 3 | 4 | 5 | 6 | | VI-2 | Pitx3 |
| 1043 | 3 | 4 | 5 | 6 | | VI-2 | Pklg |
| 1044 | 3 | 4 | 5 | 6 | | VI-2 | Pla2g10os |
| 1045 | 3 | 4 | 5 | 6 | | VI-2 | Pla2g2d |
| 1046 | 3 | 4 | 5 | 6 | | VI-2 | Pla2g4b |
| 1047 | 3 | 4 | 5 | 6 | | VI-2 | Plekho1 |
| 1048 | 3 | 4 | 5 | 6 | | VI-2 | Pnmt |
| 1049 | 3 | 4 | 5 | 6 | | VI-2 | Pnpo |
| 1050 | 3 | 4 | 5 | 6 | | VI-2 | Polb |
| 1051 | 3 | 4 | 5 | 6 | | VI-2 | Polr2f |
| 1052 | 3 | 4 | 5 | 6 | | VI-2 | Pop7 |
| 1053 | 3 | 4 | 5 | 6 | | VI-2 | Poteg |
| 1054 | 3 | 4 | 5 | 6 | | VI-2 | Ppap2b |
| 1055 | 3 | 4 | 5 | 6 | | VI-2 | Ppic |
| 1056 | 3 | 4 | 5 | 6 | | VI-2 | Ppif |
| 1057 | 3 | 4 | 5 | 6 | | VI-2 | Ppil3 |
| 1058 | 3 | 4 | 5 | 6 | | VI-2 | Ppp1cb |
| 1059 | 3 | 4 | 5 | 6 | | VI-2 | Ppp1r14a |
| 1060 | 3 | 4 | 5 | 6 | | VI-2 | Ppp1r15a |
| 1061 | 3 | 4 | 5 | 6 | | VI-2 | Ppp1r2-ps3 |
| 1062 | 3 | 4 | 5 | 6 | | VI-2 | Ppp1r27 |
| 1063 | 3 | 4 | 5 | 6 | | VI-2 | Ppp3cc |
| 1064 | 3 | 4 | 5 | 6 | | VI-2 | Pram1 |
| 1065 | 3 | 4 | 5 | 6 | | VI-2 | Prlr |
| 1066 | 3 | 4 | 5 | 6 | | VI-2 | Prok1 |
| 1067 | 3 | 4 | 5 | 6 | | VI-2 | Prokr1 |
| 1068 | 3 | 4 | 5 | 6 | | VI-2 | Prr24 |
| 1069 | 3 | 4 | 5 | 6 | | VI-2 | Prss53 |
| 1070 | 3 | 4 | 5 | 6 | | VI-2 | Pter |
| 1071 | 3 | 4 | 5 | 6 | | VI-2 | Ptges3l |
| 1072 | 3 | 4 | 5 | 6 | | VI-2 | Ptgfr |
| 1073 | 3 | 4 | 5 | 6 | | VI-2 | Ptpla |
| 1074 | 3 | 4 | 5 | 6 | | VI-2 | Ptprcap |
| 1075 | 3 | 4 | 5 | 6 | | VI-2 | Ptpru |
| 1076 | 3 | 4 | 5 | 6 | | VI-2 | Pxdc1 |
| 1077 | 3 | 4 | 5 | 6 | | VI-2 | Pyroxd1 |
| 1078 | 3 | 4 | 5 | 6 | | VI-2 | Qprt |
| 1079 | 3 | 4 | 5 | 6 | | VI-2 | Rab22a |
| 1080 | 3 | 4 | 5 | 6 | | VI-2 | Rad23a |
| 1081 | 3 | 4 | 5 | 6 | | VI-2 | Ranbp10 |
| 1082 | 3 | 4 | 5 | 6 | | VI-2 | Rarres2 |
| 1083 | 3 | 4 | 5 | 6 | | VI-2 | Rasgrp2 |
| 1084 | 3 | 4 | 5 | 6 | | VI-2 | Rasgrp3 |
| 1085 | 3 | 4 | 5 | 6 | | VI-2 | Rb1 |
| 1086 | 3 | 4 | 5 | 6 | | VI-2 | Rcan2 |
| 1087 | 3 | 4 | 5 | 6 | | VI-2 | Redrum |
| 1088 | 3 | 4 | 5 | 6 | | VI-2 | Ren2 |
| 1089 | 3 | 4 | 5 | 6 | | VI-2 | Rexo2 |
| 1090 | 3 | 4 | 5 | 6 | | VI-2 | Rgcc |
| 1091 | 3 | 4 | 5 | 6 | | VI-2 | Rgs2 |
| 1092 | 3 | 4 | 5 | 6 | | VI-2 | Rgs5 |
| 1093 | 3 | 4 | 5 | 6 | | VI-2 | Rhno1 |
| 1094 | 3 | 4 | 5 | 6 | | VI-2 | Rhox5 |
| 1095 | 3 | 4 | 5 | 6 | | VI-2 | Ritp |
| 1096 | 3 | 4 | 5 | 6 | | VI-2 | Ripply2 |
| 1097 | 3 | 4 | 5 | 6 | | VI-2 | Ripply3 |
| 1098 | 3 | 4 | 5 | 6 | | VI-2 | Rnase2a |
| 1099 | 3 | 4 | 5 | 6 | | VI-2 | Rnf10 |
| 1100 | 3 | 4 | 5 | 6 | | VI-2 | Rnf11 |
| 1101 | 3 | 4 | 5 | 6 | | VI-2 | Rpl29 |
| 1102 | 3 | 4 | 5 | 6 | | VI-2 | Rpl31-ps12 |
| 1103 | 3 | 4 | 5 | 6 | | VI-2 | Rpl35a |
| 1104 | 3 | 4 | 5 | 6 | | VI-2 | Rps11 |
| 1105 | 3 | 4 | 5 | 6 | | VI-2 | Rps19-ps3 |
| 1106 | 3 | 4 | 5 | 6 | | VI-2 | Rps27l |
| 1107 | 3 | 4 | 5 | 6 | | VI-2 | Rps27rt |
| 1108 | 3 | 4 | 5 | 6 | | VI-2 | Rps28 |
| 1109 | 3 | 4 | 5 | 6 | | VI-2 | Rpusd3 |
| 1110 | 3 | 4 | 5 | 6 | | VI-2 | Rras |
| 1111 | 3 | 4 | 5 | 6 | | VI-2 | Rundc3a |
| 1112 | 3 | 4 | 5 | 6 | | VI-2 | S1pr4 |
| 1113 | 3 | 4 | 5 | 6 | | VI-2 | Samm50 |
| 1114 | 3 | 4 | 5 | 6 | | VI-2 | Sap25 |
| 1115 | 3 | 4 | 5 | 6 | | VI-2 | Sap30l |
| 1116 | 3 | 4 | 5 | 6 | | VI-2 | Sat2 |
| 1117 | 3 | 4 | 5 | 6 | | VI-2 | Scg3 |
| 1118 | 3 | 4 | 5 | 6 | | VI-2 | Scn1b |
| 1119 | 3 | 4 | 5 | 6 | | VI-2 | Sdf2l1 |
| 1120 | 3 | 4 | 5 | 6 | | VI-2 | Sec1 |
| 1121 | 3 | 4 | 5 | 6 | | VI-2 | Sec13 |
| 1122 | 3 | 4 | 5 | 6 | | VI-2 | Sec61g |
| 1123 | 3 | 4 | 5 | 6 | | VI-2 | Selk |
| 1124 | 3 | 4 | 5 | 6 | | VI-2 | Sept1 |
| 1125 | 3 | 4 | 5 | 6 | | VI-2 | Serf1 |
| 1126 | 3 | 4 | 5 | 6 | | VI-2 | Serpina10 |
| 1127 | 3 | 4 | 5 | 6 | | VI-2 | Serpinb1c |
| 1128 | 3 | 4 | 5 | 6 | | VI-2 | Serpinb9b |
| 1129 | 3 | 4 | 5 | 6 | | VI-2 | Sh2b3 |
| 1130 | 3 | 4 | 5 | 6 | | VI-2 | Shroom4 |
| 1131 | 3 | 4 | 5 | 6 | | VI-2 | Sirt3 |
| 1132 | 3 | 4 | 5 | 6 | | VI-2 | Siva1 |
| 1133 | 3 | 4 | 5 | 6 | | VI-2 | Skap2 |
| 1134 | 3 | 4 | 5 | 6 | | VI-2 | Slamf9 |
| 1135 | 3 | 4 | 5 | 6 | | VI-2 | Slc10a3-ubl4 |
| 1136 | 3 | 4 | 5 | 6 | | VI-2 | Slc16a5 |
| 1137 | 3 | 4 | 5 | 6 | | VI-2 | Slc24a5 |
| 1138 | 3 | 4 | 5 | 6 | | VI-2 | Slc25a34 |
| 1139 | 3 | 4 | 5 | 6 | | VI-2 | Slc25a4 |
| 1140 | 3 | 4 | 5 | 6 | | VI-2 | Slc25a51 |
| 1141 | 3 | 4 | 5 | 6 | | VI-2 | Slc35g2 |
| 1142 | 3 | 4 | 5 | 6 | | VI-2 | Slc38a1 |
| 1143 | 3 | 4 | 5 | 6 | | VI-2 | Slc39a4 |
| 1144 | 3 | 4 | 5 | 6 | | VI-2 | Slc44a1 |
| 1145 | 3 | 4 | 5 | 6 | | VI-2 | Slc4a1 |
| 1146 | 3 | 4 | 5 | 6 | | VI-2 | Slc6a4 |
| 1147 | 3 | 4 | 5 | 6 | | VI-2 | Slc7a8 |
| 1148 | 3 | 4 | 5 | 6 | | VI-2 | Slirp |
| 1149 | 3 | 4 | 5 | 6 | | VI-2 | Slpi |
| 1150 | 3 | 4 | 5 | 6 | | VI-2 | Smap1 |

Fig. 36 - 7

| | | | | | | |
|---|---|---|---|---|---|---|
| 1151 | 3 | 4 | 5 | 6 | VI-2 | Smim18 |
| 1152 | 3 | 4 | 5 | 6 | VI-2 | Smtn |
| 1153 | 3 | 4 | 5 | 6 | VI-2 | Snhg10 |
| 1154 | 3 | 4 | 5 | 6 | VI-2 | Snhg3 |
| 1155 | 3 | 4 | 5 | 6 | VI-2 | Snhg6 |
| 1156 | 3 | 4 | 5 | 6 | VI-2 | Snhg8 |
| 1157 | 3 | 4 | 5 | 6 | VI-2 | Snn |
| 1158 | 3 | 4 | 5 | 6 | VI-2 | Snrnp27 |
| 1159 | 3 | 4 | 5 | 6 | VI-2 | Snrpe |
| 1160 | 3 | 4 | 5 | 6 | VI-2 | Snrpf |
| 1161 | 3 | 4 | 5 | 6 | VI-2 | Snrpg |
| 1162 | 3 | 4 | 5 | 6 | VI-2 | Sntb1 |
| 1163 | 3 | 4 | 5 | 6 | VI-2 | Snx15 |
| 1164 | 3 | 4 | 5 | 6 | VI-2 | Snx5 |
| 1165 | 3 | 4 | 5 | 6 | VI-2 | Sp5 |
| 1166 | 3 | 4 | 5 | 6 | VI-2 | Sparc |
| 1167 | 3 | 4 | 5 | 6 | VI-2 | Spcs1 |
| 1168 | 3 | 4 | 5 | 6 | VI-2 | Specc1 |
| 1169 | 3 | 4 | 5 | 6 | VI-2 | Speer7-ps1 |
| 1170 | 3 | 4 | 5 | 6 | VI-2 | Sprr1a |
| 1171 | 3 | 4 | 5 | 6 | VI-2 | Sprr2k |
| 1172 | 3 | 4 | 5 | 6 | VI-2 | Srfbp1 |
| 1173 | 3 | 4 | 5 | 6 | VI-2 | Srms |
| 1174 | 3 | 4 | 5 | 6 | VI-2 | St3gal1 |
| 1175 | 3 | 4 | 5 | 6 | VI-2 | St7 |
| 1176 | 3 | 4 | 5 | 6 | VI-2 | Ston2 |
| 1177 | 3 | 4 | 5 | 6 | VI-2 | Suit1a1 |
| 1178 | 3 | 4 | 5 | 6 | VI-2 | Sva |
| 1179 | 3 | 4 | 5 | 6 | VI-2 | Svs3a |
| 1180 | 3 | 4 | 5 | 6 | VI-2 | Svs3b |
| 1181 | 3 | 4 | 5 | 6 | VI-2 | Swi5 |
| 1182 | 3 | 4 | 5 | 6 | VI-2 | Sytl5 |
| 1183 | 3 | 4 | 5 | 6 | VI-2 | Tac2 |
| 1184 | 3 | 4 | 5 | 6 | VI-2 | Taf10 |
| 1185 | 3 | 4 | 5 | 6 | VI-2 | Tbc1d22a |
| 1186 | 3 | 4 | 5 | 6 | VI-2 | Tbc1d24 |
| 1187 | 3 | 4 | 5 | 6 | VI-2 | Tbcb |
| 1188 | 3 | 4 | 5 | 6 | VI-2 | Tbxas1 |
| 1189 | 3 | 4 | 5 | 6 | VI-2 | Tef |
| 1190 | 3 | 4 | 5 | 6 | VI-2 | Tefm |
| 1191 | 3 | 4 | 5 | 6 | VI-2 | Tfdp2 |
| 1192 | 3 | 4 | 5 | 6 | VI-2 | Tff1 |
| 1193 | 3 | 4 | 5 | 6 | VI-2 | Tgif2lx1 |
| 1194 | 3 | 4 | 5 | 6 | VI-2 | Thbs1 |
| 1195 | 3 | 4 | 5 | 6 | VI-2 | Thpo |
| 1196 | 3 | 4 | 5 | 6 | VI-2 | Tldc2 |
| 1197 | 3 | 4 | 5 | 6 | VI-2 | Tmcc2 |
| 1198 | 3 | 4 | 5 | 6 | VI-2 | Tmem126b |
| 1199 | 3 | 4 | 5 | 6 | VI-2 | Tmem128 |
| 1200 | 3 | 4 | 5 | 6 | VI-2 | Tmem14a |
| 1201 | 3 | 4 | 5 | 6 | VI-2 | Tmem151a |
| 1202 | 3 | 4 | 5 | 6 | VI-2 | Tmem233 |
| 1203 | 3 | 4 | 5 | 6 | VI-2 | Tmem258 |
| 1204 | 3 | 4 | 5 | 6 | VI-2 | Tmem29 |
| 1205 | 3 | 4 | 5 | 6 | VI-2 | Tmem40 |
| 1206 | 3 | 4 | 5 | 6 | VI-2 | Tmem86b |
| 1207 | 3 | 4 | 5 | 6 | VI-2 | Tmem91 |
| 1208 | 3 | 4 | 5 | 6 | VI-2 | Tmie |
| 1209 | 3 | 4 | 5 | 6 | VI-2 | Tmod1 |
| 1210 | 3 | 4 | 5 | 6 | VI-2 | Tmtc3 |
| 1211 | 3 | 4 | 5 | 6 | VI-2 | Tnfrsf18 |
| 1212 | 3 | 4 | 5 | 6 | VI-2 | Tnik |
| 1213 | 3 | 4 | 5 | 6 | VI-2 | Tnnc1 |
| 1214 | 3 | 4 | 5 | 6 | VI-2 | Tnp1 |
| 1215 | 3 | 4 | 5 | 6 | VI-2 | Tpm1 |
| 1216 | 3 | 4 | 5 | 6 | VI-2 | Tpm2 |
| 1217 | 3 | 4 | 5 | 6 | VI-2 | Treml1 |
| 1218 | 3 | 4 | 5 | 6 | VI-2 | Trib3 |
| 1219 | 3 | 4 | 5 | 6 | VI-2 | Trim10 |
| 1220 | 3 | 4 | 5 | 6 | VI-2 | Trim58 |
| 1221 | 3 | 4 | 5 | 6 | VI-2 | Tspo2 |
| 1222 | 3 | 4 | 5 | 6 | VI-2 | Ttc28 |
| 1223 | 3 | 4 | 5 | 6 | VI-2 | Tuba4a |
| 1224 | 3 | 4 | 5 | 6 | VI-2 | Tuba8 |
| 1225 | 3 | 4 | 5 | 6 | VI-2 | Tubb1 |
| 1226 | 3 | 4 | 5 | 6 | VI-2 | Tubb2a |
| 1227 | 3 | 4 | 5 | 6 | VI-2 | Tubb2b |
| 1228 | 3 | 4 | 5 | 6 | VI-2 | Tusc1 |
| 1229 | 3 | 4 | 5 | 6 | VI-2 | Tyrobp |
| 1230 | 3 | 4 | 5 | 6 | VI-2 | U2af1 |
| 1231 | 3 | 4 | 5 | 6 | VI-2 | Ube2b |
| 1232 | 3 | 4 | 5 | 6 | VI-2 | Ube2cbp |
| 1233 | 3 | 4 | 5 | 6 | VI-2 | Ube2o |
| 1234 | 3 | 4 | 5 | 6 | VI-2 | Ubl5 |
| 1235 | 3 | 4 | 5 | 6 | VI-2 | Ubl7 |
| 1236 | 3 | 4 | 5 | 6 | VI-2 | Ugt1a1 |
| 1237 | 3 | 4 | 5 | 6 | VI-2 | Unc93a |
| 1238 | 3 | 4 | 5 | 6 | VI-2 | Ung |
| 1239 | 3 | 4 | 5 | 6 | VI-2 | Upk3b |
| 1240 | 3 | 4 | 5 | 6 | VI-2 | Upp2 |
| 1241 | 3 | 4 | 5 | 6 | VI-2 | Urod |
| 1242 | 3 | 4 | 5 | 6 | VI-2 | Usb1 |
| 1243 | 3 | 4 | 5 | 6 | VI-2 | Usp2 |
| 1244 | 3 | 4 | 5 | 6 | VI-2 | Usp49 |
| 1245 | 3 | 4 | 5 | 6 | VI-2 | Vcl |
| 1246 | 3 | 4 | 5 | 6 | VI-2 | Vmn2r68 |
| 1247 | 3 | 4 | 5 | 6 | VI-2 | Vwf |
| 1248 | 3 | 4 | 5 | 6 | VI-2 | Wbscr27 |
| 1249 | 3 | 4 | 5 | 6 | VI-2 | Wdfy1 |
| 1250 | 3 | 4 | 5 | 6 | VI-2 | Xaf1 |
| 1251 | 3 | 4 | 5 | 6 | VI-2 | Xlr3c |
| 1252 | 3 | 4 | 5 | 6 | VI-2 | Ybx3 |
| 1253 | 3 | 4 | 5 | 6 | VI-2 | Ypel3 |
| 1254 | 3 | 4 | 5 | 6 | VI-2 | Ypel4 |
| 1255 | 3 | 4 | 5 | 6 | VI-2 | Zbtb20 |
| 1256 | 3 | 4 | 5 | 6 | VI-2 | Zbtb8a |
| 1257 | 3 | 4 | 5 | 6 | VI-2 | Zc3h13 |
| 1258 | 3 | 4 | 5 | 6 | VI-2 | Zc3h15 |
| 1259 | 3 | 4 | 5 | 6 | VI-2 | Zc3hav1 |
| 1260 | 3 | 4 | 5 | 6 | VI-2 | Zcchc17 |
| 1261 | 3 | 4 | 5 | 6 | VI-2 | Zeb2os |
| 1262 | 3 | 4 | 5 | 6 | VI-2 | Zfhx2os |
| 1263 | 3 | 4 | 5 | 6 | VI-2 | Zfp389 |
| 1264 | 3 | 4 | 5 | 6 | VI-2 | Zfp472 |
| 1265 | 3 | 4 | 5 | 6 | VI-2 | Zfp652os |
| 1266 | 3 | 4 | 5 | 6 | VI-2 | Zfp72 |
| 1267 | 3 | 4 | 5 | 6 | VI-2 | Zfp758 |
| 1268 | 3 | 4 | 5 | 6 | VI-2 | Zgpat |
| 1269 | 3 | 4 | 5 | 6 | VI-2 | Zgrf1 |
| 1270 | 3 | 4 | 5 | 6 | VI-2 | Znrd1as |
| 1271 | 3 | 4 | 5 | 6 | VI-2 | Zranb3 |
| 1272 | 3 | 4 | 5 | 6 | VI-1 | 0610005C13Rik |
| 1273 | 3 | 4 | 5 | 6 | VI-1 | 0610040F04Rik |
| 1274 | 3 | 4 | 5 | 6 | VI-1 | 0610040J01Rik |
| 1275 | 3 | 4 | 5 | 6 | VI-1 | 1100001G20Rik |
| 1276 | 3 | 4 | 5 | 6 | VI-1 | 1110006O24Rik |
| 1277 | 3 | 4 | 5 | 6 | VI-1 | 1110017D15Rik |
| 1278 | 3 | 4 | 5 | 6 | VI-1 | 1190005I06Rik |
| 1279 | 3 | 4 | 5 | 6 | VI-1 | 1500004A13Rik |
| 1280 | 3 | 4 | 5 | 6 | VI-1 | 1500011B03Rik |
| 1281 | 3 | 4 | 5 | 6 | VI-1 | 1600014C10Rik |
| 1282 | 3 | 4 | 5 | 6 | VI-1 | 1600014C23Rik |
| 1283 | 3 | 4 | 5 | 6 | VI-1 | 1600020E01Rik |
| 1284 | 3 | 4 | 5 | 6 | VI-1 | 1600029I14Rik |
| 1285 | 3 | 4 | 5 | 6 | VI-1 | 1700001C02Rik |
| 1286 | 3 | 4 | 5 | 6 | VI-1 | 1700001J11Rik |
| 1287 | 3 | 4 | 5 | 6 | VI-1 | 1700003D09Rik |
| 1288 | 3 | 4 | 5 | 6 | VI-1 | 1700007K13Rik |
| 1289 | 3 | 4 | 5 | 6 | VI-1 | 1700007L15Rik |
| 1290 | 3 | 4 | 5 | 6 | VI-1 | 1700009P17Rik |
| 1291 | 3 | 4 | 5 | 6 | VI-1 | 1700010K23Rik |
| 1292 | 3 | 4 | 5 | 6 | VI-1 | 1700011H14Rik |
| 1293 | 3 | 4 | 5 | 6 | VI-1 | 1700013F07Rik |
| 1294 | 3 | 4 | 5 | 6 | VI-1 | 1700016K19Rik |
| 1295 | 3 | 4 | 5 | 6 | VI-1 | 1700019G17Rik |
| 1296 | 3 | 4 | 5 | 6 | VI-1 | 1700020D05Rik |
| 1297 | 3 | 4 | 5 | 6 | VI-1 | 1700020I14Rik |
| 1298 | 3 | 4 | 5 | 6 | VI-1 | 1700024F13Rik |
| 1299 | 3 | 4 | 5 | 6 | VI-1 | 1700024G13Rik |
| 1300 | 3 | 4 | 5 | 6 | VI-1 | 1700028B04Rik |
| 1301 | 3 | 4 | 5 | 6 | VI-1 | 1700029I15Rik |
| 1302 | 3 | 4 | 5 | 6 | VI-1 | 1700030A11Rik |
| 1303 | 3 | 4 | 5 | 6 | VI-1 | 1700048M11Rik |
| 1304 | 3 | 4 | 5 | 6 | VI-1 | 1700054K19Rik |
| 1305 | 3 | 4 | 5 | 6 | VI-1 | 1700071M16Rik |
| 1306 | 3 | 4 | 5 | 6 | VI-1 | 1700088E04Rik |
| 1307 | 3 | 4 | 5 | 6 | VI-1 | 1700109G15Rik |
| 1308 | 3 | 4 | 5 | 6 | VI-1 | 1700112E06Rik |
| 1309 | 3 | 4 | 5 | 6 | VI-1 | 1700120K04Rik |
| 1310 | 3 | 4 | 5 | 6 | VI-1 | 1700124L16Rik |
| 1311 | 3 | 4 | 5 | 6 | VI-1 | 1810009A15Rik |
| 1312 | 3 | 4 | 5 | 6 | VI-1 | 1810009J06Rik |
| 1313 | 3 | 4 | 5 | 6 | VI-1 | 2010204K13Rik |
| 1314 | 3 | 4 | 5 | 6 | VI-1 | 2010300C02Rik |
| 1315 | 3 | 4 | 5 | 6 | VI-1 | 2210018M11Rik |
| 1316 | 3 | 4 | 5 | 6 | VI-1 | 2210409D07Rik |
| 1317 | 3 | 4 | 5 | 6 | VI-1 | 2210416O15Rik |
| 1318 | 3 | 4 | 5 | 6 | VI-1 | 2310001K24Rik |
| 1319 | 3 | 4 | 5 | 6 | VI-1 | 2310007L24Rik |
| 1320 | 3 | 4 | 5 | 6 | VI-1 | 2310010J17Rik |
| 1321 | 3 | 4 | 5 | 6 | VI-1 | 2310014L17Rik |
| 1322 | 3 | 4 | 5 | 6 | VI-1 | 2310030G06Rik |
| 1323 | 3 | 4 | 5 | 6 | VI-1 | 2310034G01Rik |
| 1324 | 3 | 4 | 5 | 6 | VI-1 | 2310081J21Rik |
| 1325 | 3 | 4 | 5 | 6 | VI-1 | 2410004N09Rik |
| 1326 | 3 | 4 | 5 | 6 | VI-1 | 2410004P03Rik |
| 1327 | 3 | 4 | 5 | 6 | VI-1 | 2410021H03Rik |
| 1328 | 3 | 4 | 5 | 6 | VI-1 | 2410131K14Rik |
| 1329 | 3 | 4 | 5 | 6 | VI-1 | 2610005L07Rik |
| 1330 | 3 | 4 | 5 | 6 | VI-1 | 2610018G03Rik |
| 1331 | 3 | 4 | 5 | 6 | VI-1 | 2610524H06Rik |
| 1332 | 3 | 4 | 5 | 6 | VI-1 | 2610528A11Rik |
| 1333 | 3 | 4 | 5 | 6 | VI-1 | 2610528J11Rik |
| 1334 | 3 | 4 | 5 | 6 | VI-1 | 2810008D09Rik |
| 1335 | 3 | 4 | 5 | 6 | VI-1 | 2810410L24Rik |
| 1336 | 3 | 4 | 5 | 6 | VI-1 | 2900055J20Rik |
| 1337 | 3 | 4 | 5 | 6 | VI-1 | 2900092D14Rik |
| 1338 | 3 | 4 | 5 | 6 | VI-1 | 3000002C10Rik |
| 1339 | 3 | 4 | 5 | 6 | VI-1 | 3110001I22Rik |
| 1340 | 3 | 4 | 5 | 6 | VI-1 | 3110021N24Rik |
| 1341 | 3 | 4 | 5 | 6 | VI-1 | 3300005D01Rik |
| 1342 | 3 | 4 | 5 | 6 | VI-1 | 3830403N18Rik |

Fig. 36 - 8

| | | | | | | | |
|---|---|---|---|---|---|---|---|
| 1343 | 3 | 4 | 5 | 6 | | VI-1 | 3830408C21Rik |
| 1344 | 3 | 4 | 5 | 6 | | VI-1 | 3930402G23Rik |
| 1345 | 3 | 4 | 5 | 6 | | VI-1 | 4732416N19Rik |
| 1346 | 3 | 4 | 5 | 6 | | VI-1 | 4732471J01Rik |
| 1347 | 3 | 4 | 5 | 6 | | VI-1 | 4833417C18Rik |
| 1348 | 3 | 4 | 5 | 6 | | VI-1 | 4921533I20Rik |
| 1349 | 3 | 4 | 5 | 6 | | VI-1 | 4922502H24Rik |
| 1350 | 3 | 4 | 5 | 6 | | VI-1 | 4930426D05Rik |
| 1351 | 3 | 4 | 5 | 6 | | VI-1 | 4930451C15Rik |
| 1352 | 3 | 4 | 5 | 6 | | VI-1 | 4930455C13Rik |
| 1353 | 3 | 4 | 5 | 6 | | VI-1 | 4930459L07Rik |
| 1354 | 3 | 4 | 5 | 6 | | VI-1 | 4930503L19Rik |
| 1355 | 3 | 4 | 5 | 6 | | VI-1 | 4930529K09Rik |
| 1356 | 3 | 4 | 5 | 6 | | VI-1 | 4930529L06Rik |
| 1357 | 3 | 4 | 5 | 6 | | VI-1 | 4930539E08Rik |
| 1358 | 3 | 4 | 5 | 6 | | VI-1 | 4930539J05Rik |
| 1359 | 3 | 4 | 5 | 6 | | VI-1 | 4930547E14Rik |
| 1360 | 3 | 4 | 5 | 6 | | VI-1 | 4930549G23Rik |
| 1361 | 3 | 4 | 5 | 6 | | VI-1 | 4930567J20Rik |
| 1362 | 3 | 4 | 5 | 6 | | VI-1 | 4930571O06Rik |
| 1363 | 3 | 4 | 5 | 6 | | VI-1 | 4931408C20Rik |
| 1364 | 3 | 4 | 5 | 6 | | VI-1 | 4931428F04Rik |
| 1365 | 3 | 4 | 5 | 6 | | VI-1 | 4932438A13Rik |
| 1366 | 3 | 4 | 5 | 6 | | VI-1 | 4933409K07Rik |
| 1367 | 3 | 4 | 5 | 6 | | VI-1 | 4933411K16Rik |
| 1368 | 3 | 4 | 5 | 6 | | VI-1 | 4933431E20Rik |
| 1369 | 3 | 4 | 5 | 6 | | VI-1 | 5033403H07Rik |
| 1370 | 3 | 4 | 5 | 6 | | VI-1 | 5330426P16Rik |
| 1371 | 3 | 4 | 5 | 6 | | VI-1 | 5430416N02Rik |
| 1372 | 3 | 4 | 5 | 6 | | VI-1 | 5430435G22Rik |
| 1373 | 3 | 4 | 5 | 6 | | VI-1 | 5730408K05Rik |
| 1374 | 3 | 4 | 5 | 6 | | VI-1 | 5830415F09Rik |
| 1375 | 3 | 4 | 5 | 6 | | VI-1 | 5830418K08Rik |
| 1376 | 3 | 4 | 5 | 6 | | VI-1 | 5830454E08Rik |
| 1377 | 3 | 4 | 5 | 6 | | VI-1 | 6230400D17Rik |
| 1378 | 3 | 4 | 5 | 6 | | VI-1 | 6330403K07Rik |
| 1379 | 3 | 4 | 5 | 6 | | VI-1 | 6330418K02Rik |
| 1380 | 3 | 4 | 5 | 6 | | VI-1 | 6430571L13Rik |
| 1381 | 3 | 4 | 5 | 6 | | VI-1 | 6530402F18Rik |
| 1382 | 3 | 4 | 5 | 6 | | VI-1 | 8030462N17Rik |
| 1383 | 3 | 4 | 5 | 6 | | VI-1 | 8430408G23Rik |
| 1384 | 3 | 4 | 5 | 6 | | VI-1 | 8430426J06Rik |
| 1385 | 3 | 4 | 5 | 6 | | VI-1 | 8430427H17Rik |
| 1386 | 3 | 4 | 5 | 6 | | VI-1 | 9230116L04Rik |
| 1387 | 3 | 4 | 5 | 6 | | VI-1 | 9330117O12Rik |
| 1388 | 3 | 4 | 5 | 6 | | VI-1 | 9330162O12Rik |
| 1389 | 3 | 4 | 5 | 6 | | VI-1 | 9430037G07Rik |
| 1390 | 3 | 4 | 5 | 6 | | VI-1 | 9430038I01Rik |
| 1391 | 3 | 4 | 5 | 6 | | VI-1 | 9930111J21Rik1 |
| 1392 | 3 | 4 | 5 | 6 | | VI-1 | 9930111J21Rik2 |
| 1393 | 3 | 4 | 5 | 6 | | VI-1 | A1cf |
| 1394 | 3 | 4 | 5 | 6 | | VI-1 | A230065H16Rik |
| 1395 | 3 | 4 | 5 | 6 | | VI-1 | A330040F15Rik |
| 1396 | 3 | 4 | 5 | 6 | | VI-1 | A330074K22Rik |
| 1397 | 3 | 4 | 5 | 6 | | VI-1 | A430078G23Rik |
| 1398 | 3 | 4 | 5 | 6 | | VI-1 | A630007B06Rik |
| 1399 | 3 | 4 | 5 | 6 | | VI-1 | A930001C03Rik |
| 1400 | 3 | 4 | 5 | 6 | | VI-1 | A930006K02Rik |
| 1401 | 3 | 4 | 5 | 6 | | VI-1 | A930013F10Rik |
| 1402 | 3 | 4 | 5 | 6 | | VI-1 | AA414768 |
| 1403 | 3 | 4 | 5 | 6 | | VI-1 | AA465934 |
| 1404 | 3 | 4 | 5 | 6 | | VI-1 | AA467197 |
| 1405 | 3 | 4 | 5 | 6 | | VI-1 | AB124611 |
| 1406 | 3 | 4 | 5 | 6 | | VI-1 | AF529169 |
| 1407 | 3 | 4 | 5 | 6 | | VI-1 | AI314278 |
| 1408 | 3 | 4 | 5 | 6 | | VI-1 | AI317395 |
| 1409 | 3 | 4 | 5 | 6 | | VI-1 | AI662270 |
| 1410 | 3 | 4 | 5 | 6 | | VI-1 | AU040972 |
| 1411 | 3 | 4 | 5 | 6 | | VI-1 | AY074887 |
| 1412 | 3 | 4 | 5 | 6 | | VI-1 | AY761184 |
| 1413 | 3 | 4 | 5 | 6 | | VI-1 | Aadac |
| 1414 | 3 | 4 | 5 | 6 | | VI-1 | Aarsd1 |
| 1415 | 3 | 4 | 5 | 6 | | VI-1 | Abca12 |
| 1416 | 3 | 4 | 5 | 6 | | VI-1 | Abca13 |
| 1417 | 3 | 4 | 5 | 6 | | VI-1 | Abca2 |
| 1418 | 3 | 4 | 5 | 6 | | VI-1 | Abcg5 |
| 1419 | 3 | 4 | 5 | 6 | | VI-1 | Abhd11os |
| 1420 | 3 | 4 | 5 | 6 | | VI-1 | Abhd2 |
| 1421 | 3 | 4 | 5 | 6 | | VI-1 | Abra |
| 1422 | 3 | 4 | 5 | 6 | | VI-1 | Acaa2 |
| 1423 | 3 | 4 | 5 | 6 | | VI-1 | Ace |
| 1424 | 3 | 4 | 5 | 6 | | VI-1 | Ackr3 |
| 1425 | 3 | 4 | 5 | 6 | | VI-1 | Acly |
| 1426 | 3 | 4 | 5 | 6 | | VI-1 | Acot1 |
| 1427 | 3 | 4 | 5 | 6 | | VI-1 | Acox1 |
| 1428 | 3 | 4 | 5 | 6 | | VI-1 | Acp5 |
| 1429 | 3 | 4 | 5 | 6 | | VI-1 | Acsbg1 |
| 1430 | 3 | 4 | 5 | 6 | | VI-1 | Acsm3 |
| 1431 | 3 | 4 | 5 | 6 | | VI-1 | Acss2os |
| 1432 | 3 | 4 | 5 | 6 | | VI-1 | Acta2 |
| 1433 | 3 | 4 | 5 | 6 | | VI-1 | Actc1 |
| 1434 | 3 | 4 | 5 | 6 | | VI-1 | Actn3 |
| 1435 | 3 | 4 | 5 | 6 | | VI-1 | Adamts15 |
| 1436 | 3 | 4 | 5 | 6 | | VI-1 | Adamts4 |
| 1437 | 3 | 4 | 5 | 6 | | VI-1 | Adat3 |
| 1438 | 3 | 4 | 5 | 6 | | VI-1 | Adcy1 |
| 1439 | 3 | 4 | 5 | 6 | | VI-1 | Adcy8 |
| 1440 | 3 | 4 | 5 | 6 | | VI-1 | Adh1 |
| 1441 | 3 | 4 | 5 | 6 | | VI-1 | Adig |
| 1442 | 3 | 4 | 5 | 6 | | VI-1 | Adipoq |
| 1443 | 3 | 4 | 5 | 6 | | VI-1 | Adprhl1 |
| 1444 | 3 | 4 | 5 | 6 | | VI-1 | Adra1a |
| 1445 | 3 | 4 | 5 | 6 | | VI-1 | Adra2c |
| 1446 | 3 | 4 | 5 | 6 | | VI-1 | Adrb1 |
| 1447 | 3 | 4 | 5 | 6 | | VI-1 | Adrb3 |
| 1448 | 3 | 4 | 5 | 6 | | VI-1 | Aff2 |
| 1449 | 3 | 4 | 5 | 6 | | VI-1 | Ago3 |
| 1450 | 3 | 4 | 5 | 6 | | VI-1 | Agpat2 |
| 1451 | 3 | 4 | 5 | 6 | | VI-1 | Agr2 |
| 1452 | 3 | 4 | 5 | 6 | | VI-1 | Agt |
| 1453 | 3 | 4 | 5 | 6 | | VI-1 | Ahnak |
| 1454 | 3 | 4 | 5 | 6 | | VI-1 | Aif1 |
| 1455 | 3 | 4 | 5 | 6 | | VI-1 | Aim1l |
| 1456 | 3 | 4 | 5 | 6 | | VI-1 | Ak4 |
| 1457 | 3 | 4 | 5 | 6 | | VI-1 | Ak7 |
| 1458 | 3 | 4 | 5 | 6 | | VI-1 | Akap9 |
| 1459 | 3 | 4 | 5 | 6 | | VI-1 | Akr1b3 |
| 1460 | 3 | 4 | 5 | 6 | | VI-1 | Akr1c19 |
| 1461 | 3 | 4 | 5 | 6 | | VI-1 | Alad |
| 1462 | 3 | 4 | 5 | 6 | | VI-1 | Alg10b |
| 1463 | 3 | 4 | 5 | 6 | | VI-1 | Alkbh7 |
| 1464 | 3 | 4 | 5 | 6 | | VI-1 | Alkbh8 |
| 1465 | 3 | 4 | 5 | 6 | | VI-1 | Alms1 |
| 1466 | 3 | 4 | 5 | 6 | | VI-1 | Alox12 |
| 1467 | 3 | 4 | 5 | 6 | | VI-1 | Alox5 |
| 1468 | 3 | 4 | 5 | 6 | | VI-1 | Alpl |
| 1469 | 3 | 4 | 5 | 6 | | VI-1 | Amer1 |
| 1470 | 3 | 4 | 5 | 6 | | VI-1 | Amer2 |
| 1471 | 3 | 4 | 5 | 6 | | VI-1 | Ammecr1 |
| 1472 | 3 | 4 | 5 | 6 | | VI-1 | Amot |
| 1473 | 3 | 4 | 5 | 6 | | VI-1 | Amt |
| 1474 | 3 | 4 | 5 | 6 | | VI-1 | Amy2a2 |
| 1475 | 3 | 4 | 5 | 6 | | VI-1 | Ang |
| 1476 | 3 | 4 | 5 | 6 | | VI-1 | Ankhd1 |
| 1477 | 3 | 4 | 5 | 6 | | VI-1 | Ankrd11 |
| 1478 | 3 | 4 | 5 | 6 | | VI-1 | Ankrd12 |
| 1479 | 3 | 4 | 5 | 6 | | VI-1 | Ankrd22 |
| 1480 | 3 | 4 | 5 | 6 | | VI-1 | Ankrd34c |
| 1481 | 3 | 4 | 5 | 6 | | VI-1 | Ankrd52 |
| 1482 | 3 | 4 | 5 | 6 | | VI-1 | Anks4b |
| 1483 | 3 | 4 | 5 | 6 | | VI-1 | Anxa1 |
| 1484 | 3 | 4 | 5 | 6 | | VI-1 | Ap1m1 |
| 1485 | 3 | 4 | 5 | 6 | | VI-1 | Ap1m2 |
| 1486 | 3 | 4 | 5 | 6 | | VI-1 | Ap1s3 |
| 1487 | 3 | 4 | 5 | 6 | | VI-1 | Ap2s1 |
| 1488 | 3 | 4 | 5 | 6 | | VI-1 | Apoa4 |
| 1489 | 3 | 4 | 5 | 6 | | VI-1 | Apob |
| 1490 | 3 | 4 | 5 | 6 | | VI-1 | Apobec1 |
| 1491 | 3 | 4 | 5 | 6 | | VI-1 | Apoc2 |
| 1492 | 3 | 4 | 5 | 6 | | VI-1 | Apof |
| 1493 | 3 | 4 | 5 | 6 | | VI-1 | Apol6 |
| 1494 | 3 | 4 | 5 | 6 | | VI-1 | Apol9a |
| 1495 | 3 | 4 | 5 | 6 | | VI-1 | Apol9b |
| 1496 | 3 | 4 | 5 | 6 | | VI-1 | Apold1 |
| 1497 | 3 | 4 | 5 | 6 | | VI-1 | Apon |
| 1498 | 3 | 4 | 5 | 6 | | VI-1 | App |
| 1499 | 3 | 4 | 5 | 6 | | VI-1 | Appbp2 |
| 1500 | 3 | 4 | 5 | 6 | | VI-1 | Aqp11 |
| 1501 | 3 | 4 | 5 | 6 | | VI-1 | Aqp4 |
| 1502 | 3 | 4 | 5 | 6 | | VI-1 | Aqp8 |
| 1503 | 3 | 4 | 5 | 6 | | VI-1 | Aqp9 |
| 1504 | 3 | 4 | 5 | 6 | | VI-1 | Ar |
| 1505 | 3 | 4 | 5 | 6 | | VI-1 | Arc |
| 1506 | 3 | 4 | 5 | 6 | | VI-1 | Arg1 |
| 1507 | 3 | 4 | 5 | 6 | | VI-1 | Arg2 |
| 1508 | 3 | 4 | 5 | 6 | | VI-1 | Arhgap5 |
| 1509 | 3 | 4 | 5 | 6 | | VI-1 | Arhgap9 |
| 1510 | 3 | 4 | 5 | 6 | | VI-1 | Arhgdib |
| 1511 | 3 | 4 | 5 | 6 | | VI-1 | Arhgef16 |
| 1512 | 3 | 4 | 5 | 6 | | VI-1 | Arhgef37 |
| 1513 | 3 | 4 | 5 | 6 | | VI-1 | Arid5b |
| 1514 | 3 | 4 | 5 | 6 | | VI-1 | Arl1 |
| 1515 | 3 | 4 | 5 | 6 | | VI-1 | Arl2bp |
| 1516 | 3 | 4 | 5 | 6 | | VI-1 | Arl4c |
| 1517 | 3 | 4 | 5 | 6 | | VI-1 | Arl5b |
| 1518 | 3 | 4 | 5 | 6 | | VI-1 | Armcx6 |
| 1519 | 3 | 4 | 5 | 6 | | VI-1 | Arnt2 |
| 1520 | 3 | 4 | 5 | 6 | | VI-1 | Arntl |
| 1521 | 3 | 4 | 5 | 6 | | VI-1 | Arrdc3 |
| 1522 | 3 | 4 | 5 | 6 | | VI-1 | Arrdc5 |
| 1523 | 3 | 4 | 5 | 6 | | VI-1 | Arsi |
| 1524 | 3 | 4 | 5 | 6 | | VI-1 | Arxes2 |
| 1525 | 3 | 4 | 5 | 6 | | VI-1 | Asb2 |
| 1526 | 3 | 4 | 5 | 6 | | VI-1 | Ascl4 |
| 1527 | 3 | 4 | 5 | 6 | | VI-1 | Asf1b |
| 1528 | 3 | 4 | 5 | 6 | | VI-1 | Ash1l |
| 1529 | 3 | 4 | 5 | 6 | | VI-1 | Ass1 |
| 1530 | 3 | 4 | 5 | 6 | | VI-1 | Asxl3 |
| 1531 | 3 | 4 | 5 | 6 | | VI-1 | Atad3aos |
| 1532 | 3 | 4 | 5 | 6 | | VI-1 | Atcay |
| 1533 | 3 | 4 | 5 | 6 | | VI-1 | Atf3 |
| 1534 | 3 | 4 | 5 | 6 | | VI-1 | Atf7 |

Fig. 36 - 9

| | | | | | | |
|---|---|---|---|---|---|---|
| 1535 | 3 | 4 | 5 | 6 | VI-1 | Atf7ip |
| 1536 | 3 | 4 | 5 | 6 | VI-1 | Atp10b |
| 1537 | 3 | 4 | 5 | 6 | VI-1 | Atp1b1 |
| 1538 | 3 | 4 | 5 | 6 | VI-1 | Atp5k |
| 1539 | 3 | 4 | 5 | 6 | VI-1 | Atp6v0a4 |
| 1540 | 3 | 4 | 5 | 6 | VI-1 | Atp7b |
| 1541 | 3 | 4 | 5 | 6 | VI-1 | Atp8a2 |
| 1542 | 3 | 4 | 5 | 6 | VI-1 | Axin2 |
| 1543 | 3 | 4 | 5 | 6 | VI-1 | B230209E15Rik |
| 1544 | 3 | 4 | 5 | 6 | VI-1 | B3galt2 |
| 1545 | 3 | 4 | 5 | 6 | VI-1 | B3gnt7 |
| 1546 | 3 | 4 | 5 | 6 | VI-1 | B4galnt3 |
| 1547 | 3 | 4 | 5 | 6 | VI-1 | B930041F14Rik |
| 1548 | 3 | 4 | 5 | 6 | VI-1 | BC005561 |
| 1549 | 3 | 4 | 5 | 6 | VI-1 | BC018473 |
| 1550 | 3 | 4 | 5 | 6 | VI-1 | BC018507 |
| 1551 | 3 | 4 | 5 | 6 | VI-1 | BC021614 |
| 1552 | 3 | 4 | 5 | 6 | VI-1 | BC021891 |
| 1553 | 3 | 4 | 5 | 6 | VI-1 | BC030499 |
| 1554 | 3 | 4 | 5 | 6 | VI-1 | BC033916 |
| 1555 | 3 | 4 | 5 | 6 | VI-1 | BC051019 |
| 1556 | 3 | 4 | 5 | 6 | VI-1 | BC064078 |
| 1557 | 3 | 4 | 5 | 6 | VI-1 | BC068281 |
| 1558 | 3 | 4 | 5 | 6 | VI-1 | BC100530 |
| 1559 | 3 | 4 | 5 | 6 | VI-1 | Bahcc1 |
| 1560 | 3 | 4 | 5 | 6 | VI-1 | Banp |
| 1561 | 3 | 4 | 5 | 6 | VI-1 | Basp1 |
| 1562 | 3 | 4 | 5 | 6 | VI-1 | Batf2 |
| 1563 | 3 | 4 | 5 | 6 | VI-1 | Bax |
| 1564 | 3 | 4 | 5 | 6 | VI-1 | Baz1a |
| 1565 | 3 | 4 | 5 | 6 | VI-1 | Bbox1 |
| 1566 | 3 | 4 | 5 | 6 | VI-1 | Bcl2a1a |
| 1567 | 3 | 4 | 5 | 6 | VI-1 | Bcl2a1b |
| 1568 | 3 | 4 | 5 | 6 | VI-1 | Bcl2a1d |
| 1569 | 3 | 4 | 5 | 6 | VI-1 | Bcl3 |
| 1570 | 3 | 4 | 5 | 6 | VI-1 | Bcl6 |
| 1571 | 3 | 4 | 5 | 6 | VI-1 | Bcl6b |
| 1572 | 3 | 4 | 5 | 6 | VI-1 | Bcl9l |
| 1573 | 3 | 4 | 5 | 6 | VI-1 | Bcorl1 |
| 1574 | 3 | 4 | 5 | 6 | VI-1 | Bdh1 |
| 1575 | 3 | 4 | 5 | 6 | VI-1 | Bdkrb2 |
| 1576 | 3 | 4 | 5 | 6 | VI-1 | Bend4 |
| 1577 | 3 | 4 | 5 | 6 | VI-1 | Bex1 |
| 1578 | 3 | 4 | 5 | 6 | VI-1 | Bhlhe41 |
| 1579 | 3 | 4 | 5 | 6 | VI-1 | Birc6 |
| 1580 | 3 | 4 | 5 | 6 | VI-1 | Bmp3 |
| 1581 | 3 | 4 | 5 | 6 | VI-1 | Bmp7 |
| 1582 | 3 | 4 | 5 | 6 | VI-1 | Bmp8a |
| 1583 | 3 | 4 | 5 | 6 | VI-1 | Bmpr1b |
| 1584 | 3 | 4 | 5 | 6 | VI-1 | Bmyc |
| 1585 | 3 | 4 | 5 | 6 | VI-1 | Bod1l |
| 1586 | 3 | 4 | 5 | 6 | VI-1 | Bola2 |
| 1587 | 3 | 4 | 5 | 6 | VI-1 | Bola3 |
| 1588 | 3 | 4 | 5 | 6 | VI-1 | Bpi |
| 1589 | 3 | 4 | 5 | 6 | VI-1 | Bpifa1 |
| 1590 | 3 | 4 | 5 | 6 | VI-1 | Bpifb1 |
| 1591 | 3 | 4 | 5 | 6 | VI-1 | Bptf |
| 1592 | 3 | 4 | 5 | 6 | VI-1 | Bst2 |
| 1593 | 3 | 4 | 5 | 6 | VI-1 | Btbd7 |
| 1594 | 3 | 4 | 5 | 6 | VI-1 | Btnl4 |
| 1595 | 3 | 4 | 5 | 6 | VI-1 | Btnl9 |
| 1596 | 3 | 4 | 5 | 6 | VI-1 | C030018K13Rik |
| 1597 | 3 | 4 | 5 | 6 | VI-1 | C1galt1 |
| 1598 | 3 | 4 | 5 | 6 | VI-1 | C1qa |
| 1599 | 3 | 4 | 5 | 6 | VI-1 | C1qb |
| 1600 | 3 | 4 | 5 | 6 | VI-1 | C1qc |
| 1601 | 3 | 4 | 5 | 6 | VI-1 | C3 |
| 1602 | 3 | 4 | 5 | 6 | VI-1 | C330013E15Rik |
| 1603 | 3 | 4 | 5 | 6 | VI-1 | C3ar1 |
| 1604 | 3 | 4 | 5 | 6 | VI-1 | C78339 |
| 1605 | 3 | 4 | 5 | 6 | VI-1 | Cacna1d |
| 1606 | 3 | 4 | 5 | 6 | VI-1 | Cacna1e |
| 1607 | 3 | 4 | 5 | 6 | VI-1 | Cacna1h |
| 1608 | 3 | 4 | 5 | 6 | VI-1 | Cad |
| 1609 | 3 | 4 | 5 | 6 | VI-1 | Calml3 |
| 1610 | 3 | 4 | 5 | 6 | VI-1 | Calml4 |
| 1611 | 3 | 4 | 5 | 6 | VI-1 | Caln1 |
| 1612 | 3 | 4 | 5 | 6 | VI-1 | Camsap3 |
| 1613 | 3 | 4 | 5 | 6 | VI-1 | Cand2 |
| 1614 | 3 | 4 | 5 | 6 | VI-1 | Capn12 |
| 1615 | 3 | 4 | 5 | 6 | VI-1 | Capn15 |
| 1616 | 3 | 4 | 5 | 6 | VI-1 | Capn3 |
| 1617 | 3 | 4 | 5 | 6 | VI-1 | Capn5 |
| 1618 | 3 | 4 | 5 | 6 | VI-1 | Capsl |
| 1619 | 3 | 4 | 5 | 6 | VI-1 | Car1 |
| 1620 | 3 | 4 | 5 | 6 | VI-1 | Car12 |
| 1621 | 3 | 4 | 5 | 6 | VI-1 | Car2 |
| 1622 | 3 | 4 | 5 | 6 | VI-1 | Car3 |
| 1623 | 3 | 4 | 5 | 6 | VI-1 | Car4 |
| 1624 | 3 | 4 | 5 | 6 | VI-1 | Car5b |
| 1625 | 3 | 4 | 5 | 6 | VI-1 | Cartpt |
| 1626 | 3 | 4 | 5 | 6 | VI-1 | Casc5 |
| 1627 | 3 | 4 | 5 | 6 | VI-1 | Casp4 |
| 1628 | 3 | 4 | 5 | 6 | VI-1 | Casq1 |
| 1629 | 3 | 4 | 5 | 6 | VI-1 | Catip |
| 1630 | 3 | 4 | 5 | 6 | VI-1 | Cbr2 |
| 1631 | 3 | 4 | 5 | 6 | VI-1 | Ccdc108 |
| 1632 | 3 | 4 | 5 | 6 | VI-1 | Ccdc114 |
| 1633 | 3 | 4 | 5 | 6 | VI-1 | Ccdc120 |
| 1634 | 3 | 4 | 5 | 6 | VI-1 | Ccdc152 |
| 1635 | 3 | 4 | 5 | 6 | VI-1 | Ccdc153 |
| 1636 | 3 | 4 | 5 | 6 | VI-1 | Ccdc159 |
| 1637 | 3 | 4 | 5 | 6 | VI-1 | Ccdc23 |
| 1638 | 3 | 4 | 5 | 6 | VI-1 | Ccdc40 |
| 1639 | 3 | 4 | 5 | 6 | VI-1 | Ccdc57 |
| 1640 | 3 | 4 | 5 | 6 | VI-1 | Ccdc64 |
| 1641 | 3 | 4 | 5 | 6 | VI-1 | Ccdc69 |
| 1642 | 3 | 4 | 5 | 6 | VI-1 | Ccdc85c |
| 1643 | 3 | 4 | 5 | 6 | VI-1 | Ccdc88c |
| 1644 | 3 | 4 | 5 | 6 | VI-1 | Ccdc92 |
| 1645 | 3 | 4 | 5 | 6 | VI-1 | Ccl2 |
| 1646 | 3 | 4 | 5 | 6 | VI-1 | Ccl21c |
| 1647 | 3 | 4 | 5 | 6 | VI-1 | Ccl28 |
| 1648 | 3 | 4 | 5 | 6 | VI-1 | Ccl5 |
| 1649 | 3 | 4 | 5 | 6 | VI-1 | Ccl7 |
| 1650 | 3 | 4 | 5 | 6 | VI-1 | Ccl8 |
| 1651 | 3 | 4 | 5 | 6 | VI-1 | Ccl9 |
| 1652 | 3 | 4 | 5 | 6 | VI-1 | Ccpg1os |
| 1653 | 3 | 4 | 5 | 6 | VI-1 | Ccr2 |
| 1654 | 3 | 4 | 5 | 6 | VI-1 | Ccr5 |
| 1655 | 3 | 4 | 5 | 6 | VI-1 | Ccrn4l |
| 1656 | 3 | 4 | 5 | 6 | VI-1 | Cd14 |
| 1657 | 3 | 4 | 5 | 6 | VI-1 | Cd164l2 |
| 1658 | 3 | 4 | 5 | 6 | VI-1 | Cd177 |
| 1659 | 3 | 4 | 5 | 6 | VI-1 | Cd180 |
| 1660 | 3 | 4 | 5 | 6 | VI-1 | Cd1d1 |
| 1661 | 3 | 4 | 5 | 6 | VI-1 | Cd24a |
| 1662 | 3 | 4 | 5 | 6 | VI-1 | Cd300lh |
| 1663 | 3 | 4 | 5 | 6 | VI-1 | Cd33 |
| 1664 | 3 | 4 | 5 | 6 | VI-1 | Cd47 |
| 1665 | 3 | 4 | 5 | 6 | VI-1 | Cd48 |
| 1666 | 3 | 4 | 5 | 6 | VI-1 | Cd52 |
| 1667 | 3 | 4 | 5 | 6 | VI-1 | Cd53 |
| 1668 | 3 | 4 | 5 | 6 | VI-1 | Cd59b |
| 1669 | 3 | 4 | 5 | 6 | VI-1 | Cd5l |
| 1670 | 3 | 4 | 5 | 6 | VI-1 | Cd72 |
| 1671 | 3 | 4 | 5 | 6 | VI-1 | Cd74 |
| 1672 | 3 | 4 | 5 | 6 | VI-1 | Cd86 |
| 1673 | 3 | 4 | 5 | 6 | VI-1 | Cd9 |
| 1674 | 3 | 4 | 5 | 6 | VI-1 | Cd93 |
| 1675 | 3 | 4 | 5 | 6 | VI-1 | Cda |
| 1676 | 3 | 4 | 5 | 6 | VI-1 | Cdc42ep5 |
| 1677 | 3 | 4 | 5 | 6 | VI-1 | Cdcp1 |
| 1678 | 3 | 4 | 5 | 6 | VI-1 | Cdh12 |
| 1679 | 3 | 4 | 5 | 6 | VI-1 | Cdh3 |
| 1680 | 3 | 4 | 5 | 6 | VI-1 | Cdh6 |
| 1681 | 3 | 4 | 5 | 6 | VI-1 | Cdhr2 |
| 1682 | 3 | 4 | 5 | 6 | VI-1 | Cdhr3 |
| 1683 | 3 | 4 | 5 | 6 | VI-1 | Cdhr5 |
| 1684 | 3 | 4 | 5 | 6 | VI-1 | Cdkl4 |
| 1685 | 3 | 4 | 5 | 6 | VI-1 | Cdkn1a |
| 1686 | 3 | 4 | 5 | 6 | VI-1 | Cds1 |
| 1687 | 3 | 4 | 5 | 6 | VI-1 | Cdsn |
| 1688 | 3 | 4 | 5 | 6 | VI-1 | Ceacam1 |
| 1689 | 3 | 4 | 5 | 6 | VI-1 | Ceacam2 |
| 1690 | 3 | 4 | 5 | 6 | VI-1 | Cebpb |
| 1691 | 3 | 4 | 5 | 6 | VI-1 | Cebpe |
| 1692 | 3 | 4 | 5 | 6 | VI-1 | Celsr1 |
| 1693 | 3 | 4 | 5 | 6 | VI-1 | Celsr2 |
| 1694 | 3 | 4 | 5 | 6 | VI-1 | Cenpp |
| 1695 | 3 | 4 | 5 | 6 | VI-1 | Cep170 |
| 1696 | 3 | 4 | 5 | 6 | VI-1 | Cep350 |
| 1697 | 3 | 4 | 5 | 6 | VI-1 | Cep44 |
| 1698 | 3 | 4 | 5 | 6 | VI-1 | Cep85l |
| 1699 | 3 | 4 | 5 | 6 | VI-1 | Cers1 |
| 1700 | 3 | 4 | 5 | 6 | VI-1 | Cers6 |
| 1701 | 3 | 4 | 5 | 6 | VI-1 | Ces1c |
| 1702 | 3 | 4 | 5 | 6 | VI-1 | Ces1d |
| 1703 | 3 | 4 | 5 | 6 | VI-1 | Ces2e |
| 1704 | 3 | 4 | 5 | 6 | VI-1 | Ces3a |
| 1705 | 3 | 4 | 5 | 6 | VI-1 | Cfb |
| 1706 | 3 | 4 | 5 | 6 | VI-1 | Cfh |
| 1707 | 3 | 4 | 5 | 6 | VI-1 | Cfi |
| 1708 | 3 | 4 | 5 | 6 | VI-1 | Cfp |
| 1709 | 3 | 4 | 5 | 6 | VI-1 | Cftr |
| 1710 | 3 | 4 | 5 | 6 | VI-1 | Cgn |
| 1711 | 3 | 4 | 5 | 6 | VI-1 | Cgref1 |
| 1712 | 3 | 4 | 5 | 6 | VI-1 | Ch25h |
| 1713 | 3 | 4 | 5 | 6 | VI-1 | Chad |
| 1714 | 3 | 4 | 5 | 6 | VI-1 | Chia1 |
| 1715 | 3 | 4 | 5 | 6 | VI-1 | Chmp4c |
| 1716 | 3 | 4 | 5 | 6 | VI-1 | Chst1 |
| 1717 | 3 | 4 | 5 | 6 | VI-1 | Chst3 |
| 1718 | 3 | 4 | 5 | 6 | VI-1 | Chst8 |
| 1719 | 3 | 4 | 5 | 6 | VI-1 | Cib2 |
| 1720 | 3 | 4 | 5 | 6 | VI-1 | Cidea |
| 1721 | 3 | 4 | 5 | 6 | VI-1 | Cideb |
| 1722 | 3 | 4 | 5 | 6 | VI-1 | Cidec |
| 1723 | 3 | 4 | 5 | 6 | VI-1 | Ciita |
| 1724 | 3 | 4 | 5 | 6 | VI-1 | Cish |
| 1725 | 3 | 4 | 5 | 6 | VI-1 | Cir |
| 1726 | 3 | 4 | 5 | 6 | VI-1 | Cited1 |

Fig. 36 - 10

| | | | | | | | |
|---|---|---|---|---|---|---|---|
| 1727 | 3 | 4 | 5 | 6 | | VI-1 | Cks1b |
| 1728 | 3 | 4 | 5 | 6 | | VI-1 | Clca4 |
| 1729 | 3 | 4 | 5 | 6 | | VI-1 | Clcf1 |
| 1730 | 3 | 4 | 5 | 6 | | VI-1 | Clcn5 |
| 1731 | 3 | 4 | 5 | 6 | | VI-1 | Cldn1 |
| 1732 | 3 | 4 | 5 | 6 | | VI-1 | Cldn10 |
| 1733 | 3 | 4 | 5 | 6 | | VI-1 | Cldn15 |
| 1734 | 3 | 4 | 5 | 6 | | VI-1 | Cldn20 |
| 1735 | 3 | 4 | 5 | 6 | | VI-1 | Cldn22 |
| 1736 | 3 | 4 | 5 | 6 | | VI-1 | Cldn24 |
| 1737 | 3 | 4 | 5 | 6 | | VI-1 | Cldn6 |
| 1738 | 3 | 4 | 5 | 6 | | VI-1 | Cldn9 |
| 1739 | 3 | 4 | 5 | 6 | | VI-1 | Clec3b |
| 1740 | 3 | 4 | 5 | 6 | | VI-1 | Clec4e |
| 1741 | 3 | 4 | 5 | 6 | | VI-1 | Clic6 |
| 1742 | 3 | 4 | 5 | 6 | | VI-1 | Clk3 |
| 1743 | 3 | 4 | 5 | 6 | | VI-1 | Clrn3 |
| 1744 | 3 | 4 | 5 | 6 | | VI-1 | Cmah |
| 1745 | 3 | 4 | 5 | 6 | | VI-1 | Cmklr1 |
| 1746 | 3 | 4 | 5 | 6 | | VI-1 | Cmpk2 |
| 1747 | 3 | 4 | 5 | 6 | | VI-1 | Cndp1 |
| 1748 | 3 | 4 | 5 | 6 | | VI-1 | Cndp2 |
| 1749 | 3 | 4 | 5 | 6 | | VI-1 | Cnksr2 |
| 1750 | 3 | 4 | 5 | 6 | | VI-1 | Cnn1 |
| 1751 | 3 | 4 | 5 | 6 | | VI-1 | Cnot1 |
| 1752 | 3 | 4 | 5 | 6 | | VI-1 | Cntf |
| 1753 | 3 | 4 | 5 | 6 | | VI-1 | Cntnap5a |
| 1754 | 3 | 4 | 5 | 6 | | VI-1 | Cntnap5b |
| 1755 | 3 | 4 | 5 | 6 | | VI-1 | Col1a1 |
| 1756 | 3 | 4 | 5 | 6 | | VI-1 | Col1a2 |
| 1757 | 3 | 4 | 5 | 6 | | VI-1 | Col23a1 |
| 1758 | 3 | 4 | 5 | 6 | | VI-1 | Col3a1 |
| 1759 | 3 | 4 | 5 | 6 | | VI-1 | Col6a1 |
| 1760 | 3 | 4 | 5 | 6 | | VI-1 | Col6a4 |
| 1761 | 3 | 4 | 5 | 6 | | VI-1 | Comt |
| 1762 | 3 | 4 | 5 | 6 | | VI-1 | Cops3 |
| 1763 | 3 | 4 | 5 | 6 | | VI-1 | Cox6a2 |
| 1764 | 3 | 4 | 5 | 6 | | VI-1 | Cox6b2 |
| 1765 | 3 | 4 | 5 | 6 | | VI-1 | Cox8b |
| 1766 | 3 | 4 | 5 | 6 | | VI-1 | Cpne5 |
| 1767 | 3 | 4 | 5 | 6 | | VI-1 | Cps1 |
| 1768 | 3 | 4 | 5 | 6 | | VI-1 | Cpt1a |
| 1769 | 3 | 4 | 5 | 6 | | VI-1 | Crabp1 |
| 1770 | 3 | 4 | 5 | 6 | | VI-1 | Crb3 |
| 1771 | 3 | 4 | 5 | 6 | | VI-1 | Creb3l2 |
| 1772 | 3 | 4 | 5 | 6 | | VI-1 | Creb3l3 |
| 1773 | 3 | 4 | 5 | 6 | | VI-1 | Crebbp |
| 1774 | 3 | 4 | 5 | 6 | | VI-1 | Crip1 |
| 1775 | 3 | 4 | 5 | 6 | | VI-1 | Crip3 |
| 1776 | 3 | 4 | 5 | 6 | | VI-1 | Crocc |
| 1777 | 3 | 4 | 5 | 6 | | VI-1 | Crp |
| 1778 | 3 | 4 | 5 | 6 | | VI-1 | Crtam |
| 1779 | 3 | 4 | 5 | 6 | | VI-1 | Cryga |
| 1780 | 3 | 4 | 5 | 6 | | VI-1 | Csdc2 |
| 1781 | 3 | 4 | 5 | 6 | | VI-1 | Csf2rb |
| 1782 | 3 | 4 | 5 | 6 | | VI-1 | Csf2rb2 |
| 1783 | 3 | 4 | 5 | 6 | | VI-1 | Csf3r |
| 1784 | 3 | 4 | 5 | 6 | | VI-1 | Cstad |
| 1785 | 3 | 4 | 5 | 6 | | VI-1 | Cth |
| 1786 | 3 | 4 | 5 | 6 | | VI-1 | Cthrc1 |
| 1787 | 3 | 4 | 5 | 6 | | VI-1 | Ctrcos |
| 1788 | 3 | 4 | 5 | 6 | | VI-1 | Ctsc |
| 1789 | 3 | 4 | 5 | 6 | | VI-1 | Ctsg |
| 1790 | 3 | 4 | 5 | 6 | | VI-1 | Ctsl |
| 1791 | 3 | 4 | 5 | 6 | | VI-1 | Ctss |
| 1792 | 3 | 4 | 5 | 6 | | VI-1 | Ctxn1 |
| 1793 | 3 | 4 | 5 | 6 | | VI-1 | Ctxn3 |
| 1794 | 3 | 4 | 5 | 6 | | VI-1 | Cutal |
| 1795 | 3 | 4 | 5 | 6 | | VI-1 | Cx3cl1 |
| 1796 | 3 | 4 | 5 | 6 | | VI-1 | Cxcl16 |
| 1797 | 3 | 4 | 5 | 6 | | VI-1 | Cxcl5 |
| 1798 | 3 | 4 | 5 | 6 | | VI-1 | Cxcr2 |
| 1799 | 3 | 4 | 5 | 6 | | VI-1 | Cxcr4 |
| 1800 | 3 | 4 | 5 | 6 | | VI-1 | Cxx1c |
| 1801 | 3 | 4 | 5 | 6 | | VI-1 | Cyba |
| 1802 | 3 | 4 | 5 | 6 | | VI-1 | Cybb |
| 1803 | 3 | 4 | 5 | 6 | | VI-1 | Cybrd1 |
| 1804 | 3 | 4 | 5 | 6 | | VI-1 | Cyp2a5 |
| 1805 | 3 | 4 | 5 | 6 | | VI-1 | Cyp2b10 |
| 1806 | 3 | 4 | 5 | 6 | | VI-1 | Cyp2c29 |
| 1807 | 3 | 4 | 5 | 6 | | VI-1 | Cyp2c70 |
| 1808 | 3 | 4 | 5 | 6 | | VI-1 | Cyp2d10 |
| 1809 | 3 | 4 | 5 | 6 | | VI-1 | Cyp2d26 |
| 1810 | 3 | 4 | 5 | 6 | | VI-1 | Cyp2f2 |
| 1811 | 3 | 4 | 5 | 6 | | VI-1 | Cyp2w1 |
| 1812 | 3 | 4 | 5 | 6 | | VI-1 | Cyp4f15 |
| 1813 | 3 | 4 | 5 | 6 | | VI-1 | Cyp4x1 |
| 1814 | 3 | 4 | 5 | 6 | | VI-1 | Cyp7a1 |
| 1815 | 3 | 4 | 5 | 6 | | VI-1 | Cyp8b1 |
| 1816 | 3 | 4 | 5 | 6 | | VI-1 | Cyr61 |
| 1817 | 3 | 4 | 5 | 6 | | VI-1 | Cyyr1 |
| 1818 | 3 | 4 | 5 | 6 | | VI-1 | D030028A08Rik |
| 1819 | 3 | 4 | 5 | 6 | | VI-1 | D130017N08Rik |
| 1820 | 3 | 4 | 5 | 6 | | VI-1 | D130040H23Rik |
| 1821 | 3 | 4 | 5 | 6 | | VI-1 | D1Pas1 |
| 1822 | 3 | 4 | 5 | 6 | | VI-1 | D430019H16Rik |

| | | | | | | | |
|---|---|---|---|---|---|---|---|
| 1823 | 3 | 4 | 5 | 6 | | VI-1 | D630003M21Rik |
| 1824 | 3 | 4 | 5 | 6 | | VI-1 | D630039A03Rik |
| 1825 | 3 | 4 | 5 | 6 | | VI-1 | D630045J12Rik |
| 1826 | 3 | 4 | 5 | 6 | | VI-1 | D830031N03Rik |
| 1827 | 3 | 4 | 5 | 6 | | VI-1 | D930015M05Rik |
| 1828 | 3 | 4 | 5 | 6 | | VI-1 | D930048N14Rik |
| 1829 | 3 | 4 | 5 | 6 | | VI-1 | Dact2 |
| 1830 | 3 | 4 | 5 | 6 | | VI-1 | Dao |
| 1831 | 3 | 4 | 5 | 6 | | VI-1 | Dapl1 |
| 1832 | 3 | 4 | 5 | 6 | | VI-1 | Dbi |
| 1833 | 3 | 4 | 5 | 6 | | VI-1 | Dbndd1 |
| 1834 | 3 | 4 | 5 | 6 | | VI-1 | Dcdc2a |
| 1835 | 3 | 4 | 5 | 6 | | VI-1 | Dclk3 |
| 1836 | 3 | 4 | 5 | 6 | | VI-1 | Ddost |
| 1837 | 3 | 4 | 5 | 6 | | VI-1 | Ddt |
| 1838 | 3 | 4 | 5 | 6 | | VI-1 | Defa21 |
| 1839 | 3 | 4 | 5 | 6 | | VI-1 | Defb10 |
| 1840 | 3 | 4 | 5 | 6 | | VI-1 | Defb19 |
| 1841 | 3 | 4 | 5 | 6 | | VI-1 | Defb29 |
| 1842 | 3 | 4 | 5 | 6 | | VI-1 | Defb35 |
| 1843 | 3 | 4 | 5 | 6 | | VI-1 | Depdc7 |
| 1844 | 3 | 4 | 5 | 6 | | VI-1 | Derl3 |
| 1845 | 3 | 4 | 5 | 6 | | VI-1 | Des |
| 1846 | 3 | 4 | 5 | 6 | | VI-1 | Det1 |
| 1847 | 3 | 4 | 5 | 6 | | VI-1 | Dgat2 |
| 1848 | 3 | 4 | 5 | 6 | | VI-1 | Dgkh |
| 1849 | 3 | 4 | 5 | 6 | | VI-1 | Dgki |
| 1850 | 3 | 4 | 5 | 6 | | VI-1 | Dhrs9 |
| 1851 | 3 | 4 | 5 | 6 | | VI-1 | Dhtkd1 |
| 1852 | 3 | 4 | 5 | 6 | | VI-1 | Dio2 |
| 1853 | 3 | 4 | 5 | 6 | | VI-1 | Dio3os |
| 1854 | 3 | 4 | 5 | 6 | | VI-1 | Dkkl1 |
| 1855 | 3 | 4 | 5 | 6 | | VI-1 | Dlgap1 |
| 1856 | 3 | 4 | 5 | 6 | | VI-1 | Dlgap2 |
| 1857 | 3 | 4 | 5 | 6 | | VI-1 | Dnaja4 |
| 1858 | 3 | 4 | 5 | 6 | | VI-1 | Dnajb9 |
| 1859 | 3 | 4 | 5 | 6 | | VI-1 | Dnajc10 |
| 1860 | 3 | 4 | 5 | 6 | | VI-1 | Dnajc22 |
| 1861 | 3 | 4 | 5 | 6 | | VI-1 | Dnali1 |
| 1862 | 3 | 4 | 5 | 6 | | VI-1 | Dnase1l2 |
| 1863 | 3 | 4 | 5 | 6 | | VI-1 | Dok6 |
| 1864 | 3 | 4 | 5 | 6 | | VI-1 | Dopey1 |
| 1865 | 3 | 4 | 5 | 6 | | VI-1 | Dot1l |
| 1866 | 3 | 4 | 5 | 6 | | VI-1 | Dpagt1 |
| 1867 | 3 | 4 | 5 | 6 | | VI-1 | Dpf3 |
| 1868 | 3 | 4 | 5 | 6 | | VI-1 | Dph5 |
| 1869 | 3 | 4 | 5 | 6 | | VI-1 | Dpy19l4 |
| 1870 | 3 | 4 | 5 | 6 | | VI-1 | Dsg2 |
| 1871 | 3 | 4 | 5 | 6 | | VI-1 | Dtnb |
| 1872 | 3 | 4 | 5 | 6 | | VI-1 | Dtx1 |
| 1873 | 3 | 4 | 5 | 6 | | VI-1 | Dtx3l |
| 1874 | 3 | 4 | 5 | 6 | | VI-1 | Duox2 |
| 1875 | 3 | 4 | 5 | 6 | | VI-1 | Duoxa2 |
| 1876 | 3 | 4 | 5 | 6 | | VI-1 | Dusp10 |
| 1877 | 3 | 4 | 5 | 6 | | VI-1 | Dusp13 |
| 1878 | 3 | 4 | 5 | 6 | | VI-1 | Dusp14 |
| 1879 | 3 | 4 | 5 | 6 | | VI-1 | Dusp4 |
| 1880 | 3 | 4 | 5 | 6 | | VI-1 | Dydc2 |
| 1881 | 3 | 4 | 5 | 6 | | VI-1 | Dync1h1 |
| 1882 | 3 | 4 | 5 | 6 | | VI-1 | Dynlrb2 |
| 1883 | 3 | 4 | 5 | 6 | | VI-1 | Dynlt1f |
| 1884 | 3 | 4 | 5 | 6 | | VI-1 | Dyrk2 |
| 1885 | 3 | 4 | 5 | 6 | | VI-1 | Dyrk3 |
| 1886 | 3 | 4 | 5 | 6 | | VI-1 | E130102H24Rik |
| 1887 | 3 | 4 | 5 | 6 | | VI-1 | E130310I04Rik |
| 1888 | 3 | 4 | 5 | 6 | | VI-1 | E330009J07Rik |
| 1889 | 3 | 4 | 5 | 6 | | VI-1 | Ear3 |
| 1890 | 3 | 4 | 5 | 6 | | VI-1 | Ednrb |
| 1891 | 3 | 4 | 5 | 6 | | VI-1 | Eef1a2 |
| 1892 | 3 | 4 | 5 | 6 | | VI-1 | Efcc1 |
| 1893 | 3 | 4 | 5 | 6 | | VI-1 | Efhc1 |
| 1894 | 3 | 4 | 5 | 6 | | VI-1 | Efna3 |
| 1895 | 3 | 4 | 5 | 6 | | VI-1 | Efna4 |
| 1896 | 3 | 4 | 5 | 6 | | VI-1 | Egfbp2 |
| 1897 | 3 | 4 | 5 | 6 | | VI-1 | Egfl6 |
| 1898 | 3 | 4 | 5 | 6 | | VI-1 | Eif4ebp2 |
| 1899 | 3 | 4 | 5 | 6 | | VI-1 | Elane |
| 1900 | 3 | 4 | 5 | 6 | | VI-1 | Elfn2 |
| 1901 | 3 | 4 | 5 | 6 | | VI-1 | Elk4 |
| 1902 | 3 | 4 | 5 | 6 | | VI-1 | Elmo3 |
| 1903 | 3 | 4 | 5 | 6 | | VI-1 | Elovl2 |
| 1904 | 3 | 4 | 5 | 6 | | VI-1 | Elovl3 |
| 1905 | 3 | 4 | 5 | 6 | | VI-1 | Elovl4 |
| 1906 | 3 | 4 | 5 | 6 | | VI-1 | Elovl5 |
| 1907 | 3 | 4 | 5 | 6 | | VI-1 | Elovl6 |
| 1908 | 3 | 4 | 5 | 6 | | VI-1 | Emc9 |
| 1909 | 3 | 4 | 5 | 6 | | VI-1 | Emid1 |
| 1910 | 3 | 4 | 5 | 6 | | VI-1 | Emilin2 |
| 1911 | 3 | 4 | 5 | 6 | | VI-1 | Eml6 |
| 1912 | 3 | 4 | 5 | 6 | | VI-1 | Emp3 |
| 1913 | 3 | 4 | 5 | 6 | | VI-1 | Emr1 |
| 1914 | 3 | 4 | 5 | 6 | | VI-1 | Enkur |
| 1915 | 3 | 4 | 5 | 6 | | VI-1 | Eno1 |
| 1916 | 3 | 4 | 5 | 6 | | VI-1 | Epb4.1l4b |
| 1917 | 3 | 4 | 5 | 6 | | VI-1 | Ephb6 |
| 1918 | 3 | 4 | 5 | 6 | | VI-1 | Ephx1 |

Fig. 36 - 11

| | | | | | | | |
|---|---|---|---|---|---|---|---|
| 1919 | 3 | 4 | 5 | 6 | | VI-1 | Epm2a |
| 1920 | 3 | 4 | 5 | 6 | | VI-1 | Eppk1 |
| 1921 | 3 | 4 | 5 | 6 | | VI-1 | Erbb3 |
| 1922 | 3 | 4 | 5 | 6 | | VI-1 | Erich3 |
| 1923 | 3 | 4 | 5 | 6 | | VI-1 | Erich4 |
| 1924 | 3 | 4 | 5 | 6 | | VI-1 | Erich5 |
| 1925 | 3 | 4 | 5 | 6 | | VI-1 | Ern1 |
| 1926 | 3 | 4 | 5 | 6 | | VI-1 | Ern2 |
| 1927 | 3 | 4 | 5 | 6 | | VI-1 | Errfi1 |
| 1928 | 3 | 4 | 5 | 6 | | VI-1 | Espn |
| 1929 | 3 | 4 | 5 | 6 | | VI-1 | Esrp1 |
| 1930 | 3 | 4 | 5 | 6 | | VI-1 | Esrp2 |
| 1931 | 3 | 4 | 5 | 6 | | VI-1 | Etnk2 |
| 1932 | 3 | 4 | 5 | 6 | | VI-1 | Etohd2 |
| 1933 | 3 | 4 | 5 | 6 | | VI-1 | Etohi1 |
| 1934 | 3 | 4 | 5 | 6 | | VI-1 | Ets2 |
| 1935 | 3 | 4 | 5 | 6 | | VI-1 | Etv4 |
| 1936 | 3 | 4 | 5 | 6 | | VI-1 | Etv5 |
| 1937 | 3 | 4 | 5 | 6 | | VI-1 | Evi5l |
| 1938 | 3 | 4 | 5 | 6 | | VI-1 | Exosc6 |
| 1939 | 3 | 4 | 5 | 6 | | VI-1 | Ezr |
| 1940 | 3 | 4 | 5 | 6 | | VI-1 | F10 |
| 1941 | 3 | 4 | 5 | 6 | | VI-1 | F2 |
| 1942 | 3 | 4 | 5 | 6 | | VI-1 | F420014N23Rik |
| 1943 | 3 | 4 | 5 | 6 | | VI-1 | F830016B08Rik |
| 1944 | 3 | 4 | 5 | 6 | | VI-1 | Fabp2 |
| 1945 | 3 | 4 | 5 | 6 | | VI-1 | Fabp4 |
| 1946 | 3 | 4 | 5 | 6 | | VI-1 | Fabp5 |
| 1947 | 3 | 4 | 5 | 6 | | VI-1 | Fads2 |
| 1948 | 3 | 4 | 5 | 6 | | VI-1 | Fads6 |
| 1949 | 3 | 4 | 5 | 6 | | VI-1 | Fam101a |
| 1950 | 3 | 4 | 5 | 6 | | VI-1 | Fam110c |
| 1951 | 3 | 4 | 5 | 6 | | VI-1 | Fam124b |
| 1952 | 3 | 4 | 5 | 6 | | VI-1 | Fam135b |
| 1953 | 3 | 4 | 5 | 6 | | VI-1 | Fam13b |
| 1954 | 3 | 4 | 5 | 6 | | VI-1 | Fam166b |
| 1955 | 3 | 4 | 5 | 6 | | VI-1 | Fam167a |
| 1956 | 3 | 4 | 5 | 6 | | VI-1 | Fam167b |
| 1957 | 3 | 4 | 5 | 6 | | VI-1 | Fam171b |
| 1958 | 3 | 4 | 5 | 6 | | VI-1 | Fam183b |
| 1959 | 3 | 4 | 5 | 6 | | VI-1 | Fam208b |
| 1960 | 3 | 4 | 5 | 6 | | VI-1 | Fam216b |
| 1961 | 3 | 4 | 5 | 6 | | VI-1 | Fam217b |
| 1962 | 3 | 4 | 5 | 6 | | VI-1 | Fam222a |
| 1963 | 3 | 4 | 5 | 6 | | VI-1 | Fam229b |
| 1964 | 3 | 4 | 5 | 6 | | VI-1 | Fam26f |
| 1965 | 3 | 4 | 5 | 6 | | VI-1 | Fam3c |
| 1966 | 3 | 4 | 5 | 6 | | VI-1 | Fam46a |
| 1967 | 3 | 4 | 5 | 6 | | VI-1 | Fam46c |
| 1968 | 3 | 4 | 5 | 6 | | VI-1 | Fam47e |
| 1969 | 3 | 4 | 5 | 6 | | VI-1 | Fam57a |
| 1970 | 3 | 4 | 5 | 6 | | VI-1 | Fam78a |
| 1971 | 3 | 4 | 5 | 6 | | VI-1 | Fam81a |
| 1972 | 3 | 4 | 5 | 6 | | VI-1 | Fam83a |
| 1973 | 3 | 4 | 5 | 6 | | VI-1 | Fam83b |
| 1974 | 3 | 4 | 5 | 6 | | VI-1 | Fam89a |
| 1975 | 3 | 4 | 5 | 6 | | VI-1 | Fan1 |
| 1976 | 3 | 4 | 5 | 6 | | VI-1 | Fanca |
| 1977 | 3 | 4 | 5 | 6 | | VI-1 | Fasn |
| 1978 | 3 | 4 | 5 | 6 | | VI-1 | Fat1 |
| 1979 | 3 | 4 | 5 | 6 | | VI-1 | Fbp1 |
| 1980 | 3 | 4 | 5 | 6 | | VI-1 | Fbp2 |
| 1981 | 3 | 4 | 5 | 6 | | VI-1 | Fbxl21 |
| 1982 | 3 | 4 | 5 | 6 | | VI-1 | Fbxo36 |
| 1983 | 3 | 4 | 5 | 6 | | VI-1 | Fcer1g |
| 1984 | 3 | 4 | 5 | 6 | | VI-1 | Fcf1 |
| 1985 | 3 | 4 | 5 | 6 | | VI-1 | Fcgbp |
| 1986 | 3 | 4 | 5 | 6 | | VI-1 | Fcgr1 |
| 1987 | 3 | 4 | 5 | 6 | | VI-1 | Fcgr2b |
| 1988 | 3 | 4 | 5 | 6 | | VI-1 | Fcgr3 |
| 1989 | 3 | 4 | 5 | 6 | | VI-1 | Fcgr4 |
| 1990 | 3 | 4 | 5 | 6 | | VI-1 | Fcgrt |
| 1991 | 3 | 4 | 5 | 6 | | VI-1 | Fcna |
| 1992 | 3 | 4 | 5 | 6 | | VI-1 | Fcrls |
| 1993 | 3 | 4 | 5 | 6 | | VI-1 | Fem1c |
| 1994 | 3 | 4 | 5 | 6 | | VI-1 | Fermt1 |
| 1995 | 3 | 4 | 5 | 6 | | VI-1 | Fgd1 |
| 1996 | 3 | 4 | 5 | 6 | | VI-1 | Fgd4 |
| 1997 | 3 | 4 | 5 | 6 | | VI-1 | Fgfr1 |
| 1998 | 3 | 4 | 5 | 6 | | VI-1 | Fgfr4 |
| 1999 | 3 | 4 | 5 | 6 | | VI-1 | Fhl1 |
| 2000 | 3 | 4 | 5 | 6 | | VI-1 | Figla |
| 2001 | 3 | 4 | 5 | 6 | | VI-1 | Fitm1 |
| 2002 | 3 | 4 | 5 | 6 | | VI-1 | Fitm2 |
| 2003 | 3 | 4 | 5 | 6 | | VI-1 | Fkbp11 |
| 2004 | 3 | 4 | 5 | 6 | | VI-1 | Fktn |
| 2005 | 3 | 4 | 5 | 6 | | VI-1 | Fmo3 |
| 2006 | 3 | 4 | 5 | 6 | | VI-1 | Fn1 |
| 2007 | 3 | 4 | 5 | 6 | | VI-1 | Fndc5 |
| 2008 | 3 | 4 | 5 | 6 | | VI-1 | Fndc7 |
| 2009 | 3 | 4 | 5 | 6 | | VI-1 | Fndc9 |
| 2010 | 3 | 4 | 5 | 6 | | VI-1 | Folh1 |
| 2011 | 3 | 4 | 5 | 6 | | VI-1 | Folr2 |
| 2012 | 3 | 4 | 5 | 6 | | VI-1 | Fos |
| 2013 | 3 | 4 | 5 | 6 | | VI-1 | Fosb |
| 2014 | 3 | 4 | 5 | 6 | | VI-1 | Foxi1 |
| 2015 | 3 | 4 | 5 | 6 | | VI-1 | Foxj1 |
| 2016 | 3 | 4 | 5 | 6 | | VI-1 | Foxo3 |
| 2017 | 3 | 4 | 5 | 6 | | VI-1 | Frg1 |
| 2018 | 3 | 4 | 5 | 6 | | VI-1 | Frk |
| 2019 | 3 | 4 | 5 | 6 | | VI-1 | Frrs1l |
| 2020 | 3 | 4 | 5 | 6 | | VI-1 | Fstl4 |
| 2021 | 3 | 4 | 5 | 6 | | VI-1 | Fus |
| 2022 | 3 | 4 | 5 | 6 | | VI-1 | Fut1 |
| 2023 | 3 | 4 | 5 | 6 | | VI-1 | Fut4 |
| 2024 | 3 | 4 | 5 | 6 | | VI-1 | Fv1 |
| 2025 | 3 | 4 | 5 | 6 | | VI-1 | Fxyd1 |
| 2026 | 3 | 4 | 5 | 6 | | VI-1 | Fxyd2 |
| 2027 | 3 | 4 | 5 | 6 | | VI-1 | Fxyd7 |
| 2028 | 3 | 4 | 5 | 6 | | VI-1 | Fzd4 |
| 2029 | 3 | 4 | 5 | 6 | | VI-1 | G0s2 |
| 2030 | 3 | 4 | 5 | 6 | | VI-1 | G630025P09Rik |
| 2031 | 3 | 4 | 5 | 6 | | VI-1 | G6pc |
| 2032 | 3 | 4 | 5 | 6 | | VI-1 | Gabbr2 |
| 2033 | 3 | 4 | 5 | 6 | | VI-1 | Gabrb1 |
| 2034 | 3 | 4 | 5 | 6 | | VI-1 | Gadd45gip1 |
| 2035 | 3 | 4 | 5 | 6 | | VI-1 | Galnt14 |
| 2036 | 3 | 4 | 5 | 6 | | VI-1 | Galnt15 |
| 2037 | 3 | 4 | 5 | 6 | | VI-1 | Galnt5 |
| 2038 | 3 | 4 | 5 | 6 | | VI-1 | Gan |
| 2039 | 3 | 4 | 5 | 6 | | VI-1 | Garem |
| 2040 | 3 | 4 | 5 | 6 | | VI-1 | Gbp2b |
| 2041 | 3 | 4 | 5 | 6 | | VI-1 | Gbp4 |
| 2042 | 3 | 4 | 5 | 6 | | VI-1 | Gbp8 |
| 2043 | 3 | 4 | 5 | 6 | | VI-1 | Gbp9 |
| 2044 | 3 | 4 | 5 | 6 | | VI-1 | Gchfr |
| 2045 | 3 | 4 | 5 | 6 | | VI-1 | Gck |
| 2046 | 3 | 4 | 5 | 6 | | VI-1 | Gdf1 |
| 2047 | 3 | 4 | 5 | 6 | | VI-1 | Gdf15 |
| 2048 | 3 | 4 | 5 | 6 | | VI-1 | Gem |
| 2049 | 3 | 4 | 5 | 6 | | VI-1 | Gemin6 |
| 2050 | 3 | 4 | 5 | 6 | | VI-1 | Gfap |
| 2051 | 3 | 4 | 5 | 6 | | VI-1 | Gimap4 |
| 2052 | 3 | 4 | 5 | 6 | | VI-1 | Gipc2 |
| 2053 | 3 | 4 | 5 | 6 | | VI-1 | Gja1 |
| 2054 | 3 | 4 | 5 | 6 | | VI-1 | Gjb1 |
| 2055 | 3 | 4 | 5 | 6 | | VI-1 | Glg1 |
| 2056 | 3 | 4 | 5 | 6 | | VI-1 | Glipr1 |
| 2057 | 3 | 4 | 5 | 6 | | VI-1 | Glipr2 |
| 2058 | 3 | 4 | 5 | 6 | | VI-1 | Glp1r |
| 2059 | 3 | 4 | 5 | 6 | | VI-1 | Glycam1 |
| 2060 | 3 | 4 | 5 | 6 | | VI-1 | Gm10012 |
| 2061 | 3 | 4 | 5 | 6 | | VI-1 | Gm10058 |
| 2062 | 3 | 4 | 5 | 6 | | VI-1 | Gm10096 |
| 2063 | 3 | 4 | 5 | 6 | | VI-1 | Gm10100 |
| 2064 | 3 | 4 | 5 | 6 | | VI-1 | Gm10142 |
| 2065 | 3 | 4 | 5 | 6 | | VI-1 | Gm10147 |
| 2066 | 3 | 4 | 5 | 6 | | VI-1 | Gm10272 |
| 2067 | 3 | 4 | 5 | 6 | | VI-1 | Gm10318 |
| 2068 | 3 | 4 | 5 | 6 | | VI-1 | Gm10319 |
| 2069 | 3 | 4 | 5 | 6 | | VI-1 | Gm10653 |
| 2070 | 3 | 4 | 5 | 6 | | VI-1 | Gm10865 |
| 2071 | 3 | 4 | 5 | 6 | | VI-1 | Gm11128 |
| 2072 | 3 | 4 | 5 | 6 | | VI-1 | Gm1123 |
| 2073 | 3 | 4 | 5 | 6 | | VI-1 | Gm11437 |
| 2074 | 3 | 4 | 5 | 6 | | VI-1 | Gm11517 |
| 2075 | 3 | 4 | 5 | 6 | | VI-1 | Gm11559 |
| 2076 | 3 | 4 | 5 | 6 | | VI-1 | Gm11567 |
| 2077 | 3 | 4 | 5 | 6 | | VI-1 | Gm11570 |
| 2078 | 3 | 4 | 5 | 6 | | VI-1 | Gm11627 |
| 2079 | 3 | 4 | 5 | 6 | | VI-1 | Gm11710 |
| 2080 | 3 | 4 | 5 | 6 | | VI-1 | Gm11974 |
| 2081 | 3 | 4 | 5 | 6 | | VI-1 | Gm12216 |
| 2082 | 3 | 4 | 5 | 6 | | VI-1 | Gm12359 |
| 2083 | 3 | 4 | 5 | 6 | | VI-1 | Gm12942 |
| 2084 | 3 | 4 | 5 | 6 | | VI-1 | Gm13011 |
| 2085 | 3 | 4 | 5 | 6 | | VI-1 | Gm13034 |
| 2086 | 3 | 4 | 5 | 6 | | VI-1 | Gm13304 |
| 2087 | 3 | 4 | 5 | 6 | | VI-1 | Gm13375 |
| 2088 | 3 | 4 | 5 | 6 | | VI-1 | Gm14085 |
| 2089 | 3 | 4 | 5 | 6 | | VI-1 | Gm14288 |
| 2090 | 3 | 4 | 5 | 6 | | VI-1 | Gm14305 |
| 2091 | 3 | 4 | 5 | 6 | | VI-1 | Gm14378 |
| 2092 | 3 | 4 | 5 | 6 | | VI-1 | Gm14391 |
| 2093 | 3 | 4 | 5 | 6 | | VI-1 | Gm14431 |
| 2094 | 3 | 4 | 5 | 6 | | VI-1 | Gm14436 |
| 2095 | 3 | 4 | 5 | 6 | | VI-1 | Gm14440 |
| 2096 | 3 | 4 | 5 | 6 | | VI-1 | Gm14446 |
| 2097 | 3 | 4 | 5 | 6 | | VI-1 | Gm14476 |
| 2098 | 3 | 4 | 5 | 6 | | VI-1 | Gm14479 |
| 2099 | 3 | 4 | 5 | 6 | | VI-1 | Gm14920 |
| 2100 | 3 | 4 | 5 | 6 | | VI-1 | Gm15315 |
| 2101 | 3 | 4 | 5 | 6 | | VI-1 | Gm15408 |
| 2102 | 3 | 4 | 5 | 6 | | VI-1 | Gm15421 |
| 2103 | 3 | 4 | 5 | 6 | | VI-1 | Gm15545 |
| 2104 | 3 | 4 | 5 | 6 | | VI-1 | Gm15706 |
| 2105 | 3 | 4 | 5 | 6 | | VI-1 | Gm1604b |
| 2106 | 3 | 4 | 5 | 6 | | VI-1 | Gm16062 |
| 2107 | 3 | 4 | 5 | 6 | | VI-1 | Gm16576 |
| 2108 | 3 | 4 | 5 | 6 | | VI-1 | Gm16740 |
| 2109 | 3 | 4 | 5 | 6 | | VI-1 | Gm17677 |
| 2110 | 3 | 4 | 5 | 6 | | VI-1 | Gm19402 |

Fig. 36 - 12

| | | | | | | | |
|---|---|---|---|---|---|---|---|
| 2111 | 3 | 4 | 5 | 6 | | VI-1 | Gm1966 |
| 2112 | 3 | 4 | 5 | 6 | | VI-1 | Gm2002 |
| 2113 | 3 | 4 | 5 | 6 | | VI-1 | Gm2011 |
| 2114 | 3 | 4 | 5 | 6 | | VI-1 | Gm20257 |
| 2115 | 3 | 4 | 5 | 6 | | VI-1 | Gm20319 |
| 2116 | 3 | 4 | 5 | 6 | | VI-1 | Gm20823 |
| 2117 | 3 | 4 | 5 | 6 | | VI-1 | Gm2663 |
| 2118 | 3 | 4 | 5 | 6 | | VI-1 | Gm2696 |
| 2119 | 3 | 4 | 5 | 6 | | VI-1 | Gm3285 |
| 2120 | 3 | 4 | 5 | 6 | | VI-1 | Gm3402 |
| 2121 | 3 | 4 | 5 | 6 | | VI-1 | Gm3414 |
| 2122 | 3 | 4 | 5 | 6 | | VI-1 | Gm3415 |
| 2123 | 3 | 4 | 5 | 6 | | VI-1 | Gm3646 |
| 2124 | 3 | 4 | 5 | 6 | | VI-1 | Gm3893 |
| 2125 | 3 | 4 | 5 | 6 | | VI-1 | Gm4013 |
| 2126 | 3 | 4 | 5 | 6 | | VI-1 | Gm4070 |
| 2127 | 3 | 4 | 5 | 6 | | VI-1 | Gm4349 |
| 2128 | 3 | 4 | 5 | 6 | | VI-1 | Gm4841 |
| 2129 | 3 | 4 | 5 | 6 | | VI-1 | Gm4951 |
| 2130 | 3 | 4 | 5 | 6 | | VI-1 | Gm5113 |
| 2131 | 3 | 4 | 5 | 6 | | VI-1 | Gm5124 |
| 2132 | 3 | 4 | 5 | 6 | | VI-1 | Gm5176 |
| 2133 | 3 | 4 | 5 | 6 | | VI-1 | Gm525 |
| 2134 | 3 | 4 | 5 | 6 | | VI-1 | Gm53 |
| 2135 | 3 | 4 | 5 | 6 | | VI-1 | Gm5485 |
| 2136 | 3 | 4 | 5 | 6 | | VI-1 | Gm5547 |
| 2137 | 3 | 4 | 5 | 6 | | VI-1 | Gm5643 |
| 2138 | 3 | 4 | 5 | 6 | | VI-1 | Gm5779 |
| 2139 | 3 | 4 | 5 | 6 | | VI-1 | Gm6034 |
| 2140 | 3 | 4 | 5 | 6 | | VI-1 | Gm608 |
| 2141 | 3 | 4 | 5 | 6 | | VI-1 | Gm6086 |
| 2142 | 3 | 4 | 5 | 6 | | VI-1 | Gm609 |
| 2143 | 3 | 4 | 5 | 6 | | VI-1 | Gm6607 |
| 2144 | 3 | 4 | 5 | 6 | | VI-1 | Gm6644 |
| 2145 | 3 | 4 | 5 | 6 | | VI-1 | Gm7102 |
| 2146 | 3 | 4 | 5 | 6 | | VI-1 | Gm7367 |
| 2147 | 3 | 4 | 5 | 6 | | VI-1 | Gm7861 |
| 2148 | 3 | 4 | 5 | 6 | | VI-1 | Gm8801 |
| 2149 | 3 | 4 | 5 | 6 | | VI-1 | Gm8898 |
| 2150 | 3 | 4 | 5 | 6 | | VI-1 | Gm9733 |
| 2151 | 3 | 4 | 5 | 6 | | VI-1 | Gm9855 |
| 2152 | 3 | 4 | 5 | 6 | | VI-1 | Gng10 |
| 2153 | 3 | 4 | 5 | 6 | | VI-1 | Gngt2 |
| 2154 | 3 | 4 | 5 | 6 | | VI-1 | Golga3 |
| 2155 | 3 | 4 | 5 | 6 | | VI-1 | Golga4 |
| 2156 | 3 | 4 | 5 | 6 | | VI-1 | Golgb1 |
| 2157 | 3 | 4 | 5 | 6 | | VI-1 | Got1 |
| 2158 | 3 | 4 | 5 | 6 | | VI-1 | Got2 |
| 2159 | 3 | 4 | 5 | 6 | | VI-1 | Gp49a |
| 2160 | 3 | 4 | 5 | 6 | | VI-1 | Gpam |
| 2161 | 3 | 4 | 5 | 6 | | VI-1 | Gpc2 |
| 2162 | 3 | 4 | 5 | 6 | | VI-1 | Gpld1 |
| 2163 | 3 | 4 | 5 | 6 | | VI-1 | Gpr114 |
| 2164 | 3 | 4 | 5 | 6 | | VI-1 | Gpr128 |
| 2165 | 3 | 4 | 5 | 6 | | VI-1 | Gpr135 |
| 2166 | 3 | 4 | 5 | 6 | | VI-1 | Gpr137c |
| 2167 | 3 | 4 | 5 | 6 | | VI-1 | Gpr139 |
| 2168 | 3 | 4 | 5 | 6 | | VI-1 | Gpr161 |
| 2169 | 3 | 4 | 5 | 6 | | VI-1 | Gpr165 |
| 2170 | 3 | 4 | 5 | 6 | | VI-1 | Gpr371 |
| 2171 | 3 | 4 | 5 | 6 | | VI-1 | Gpr63 |
| 2172 | 3 | 4 | 5 | 6 | | VI-1 | Gprasp2 |
| 2173 | 3 | 4 | 5 | 6 | | VI-1 | Gprc5a |
| 2174 | 3 | 4 | 5 | 6 | | VI-1 | Gprin3 |
| 2175 | 3 | 4 | 5 | 6 | | VI-1 | Gpt |
| 2176 | 3 | 4 | 5 | 6 | | VI-1 | Gpx3 |
| 2177 | 3 | 4 | 5 | 6 | | VI-1 | Gpx6 |
| 2178 | 3 | 4 | 5 | 6 | | VI-1 | Gramd1b |
| 2179 | 3 | 4 | 5 | 6 | | VI-1 | Grb7 |
| 2180 | 3 | 4 | 5 | 6 | | VI-1 | Greb1 |
| 2181 | 3 | 4 | 5 | 6 | | VI-1 | Grem1 |
| 2182 | 3 | 4 | 5 | 6 | | VI-1 | Grid2 |
| 2183 | 3 | 4 | 5 | 6 | | VI-1 | Grid2ip |
| 2184 | 3 | 4 | 5 | 6 | | VI-1 | Grin2a |
| 2185 | 3 | 4 | 5 | 6 | | VI-1 | Grin2b |
| 2186 | 3 | 4 | 5 | 6 | | VI-1 | Gsg1l |
| 2187 | 3 | 4 | 5 | 6 | | VI-1 | Gspt2 |
| 2188 | 3 | 4 | 5 | 6 | | VI-1 | Gstcd |
| 2189 | 3 | 4 | 5 | 6 | | VI-1 | Gstm1 |
| 2190 | 3 | 4 | 5 | 6 | | VI-1 | Gstm3 |
| 2191 | 3 | 4 | 5 | 6 | | VI-1 | Gstm5 |
| 2192 | 3 | 4 | 5 | 6 | | VI-1 | Gstp1 |
| 2193 | 3 | 4 | 5 | 6 | | VI-1 | Gstz1 |
| 2194 | 3 | 4 | 5 | 6 | | VI-1 | Guca2b |
| 2195 | 3 | 4 | 5 | 6 | | VI-1 | Gucy2c |
| 2196 | 3 | 4 | 5 | 6 | | VI-1 | Gyk |
| 2197 | 3 | 4 | 5 | 6 | | VI-1 | H2-Aa |
| 2198 | 3 | 4 | 5 | 6 | | VI-1 | H2-Ab1 |
| 2199 | 3 | 4 | 5 | 6 | | VI-1 | H2-DMa |
| 2200 | 3 | 4 | 5 | 6 | | VI-1 | H2-DMb2 |
| 2201 | 3 | 4 | 5 | 6 | | VI-1 | H2-Eb1 |
| 2202 | 3 | 4 | 5 | 6 | | VI-1 | H2-K1 |
| 2203 | 3 | 4 | 5 | 6 | | VI-1 | H2-Ke6 |
| 2204 | 3 | 4 | 5 | 6 | | VI-1 | H2-Q10 |
| 2205 | 3 | 4 | 5 | 6 | | VI-1 | H2-Q4 |
| 2206 | 3 | 4 | 5 | 6 | | VI-1 | H2-Q5 |
| 2207 | 3 | 4 | 5 | 6 | | VI-1 | H2-Q6 |
| 2208 | 3 | 4 | 5 | 6 | | VI-1 | H2-Q9 |
| 2209 | 3 | 4 | 5 | 6 | | VI-1 | H2afy3 |
| 2210 | 3 | 4 | 5 | 6 | | VI-1 | H60b |
| 2211 | 3 | 4 | 5 | 6 | | VI-1 | H6pd |
| 2212 | 3 | 4 | 5 | 6 | | VI-1 | Haao |
| 2213 | 3 | 4 | 5 | 6 | | VI-1 | Hamp |
| 2214 | 3 | 4 | 5 | 6 | | VI-1 | Hao2 |
| 2215 | 3 | 4 | 5 | 6 | | VI-1 | Hap1 |
| 2216 | 3 | 4 | 5 | 6 | | VI-1 | Haus6 |
| 2217 | 3 | 4 | 5 | 6 | | VI-1 | Hcar2 |
| 2218 | 3 | 4 | 5 | 6 | | VI-1 | Hck |
| 2219 | 3 | 4 | 5 | 6 | | VI-1 | Hcn4 |
| 2220 | 3 | 4 | 5 | 6 | | VI-1 | Hcst |
| 2221 | 3 | 4 | 5 | 6 | | VI-1 | Hdac11 |
| 2222 | 3 | 4 | 5 | 6 | | VI-1 | Hdac4 |
| 2223 | 3 | 4 | 5 | 6 | | VI-1 | Hdhd3 |
| 2224 | 3 | 4 | 5 | 6 | | VI-1 | Heg1 |
| 2225 | 3 | 4 | 5 | 6 | | VI-1 | Helz |
| 2226 | 3 | 4 | 5 | 6 | | VI-1 | Helz2 |
| 2227 | 3 | 4 | 5 | 6 | | VI-1 | Herc6 |
| 2228 | 3 | 4 | 5 | 6 | | VI-1 | Hhex |
| 2229 | 3 | 4 | 5 | 6 | | VI-1 | Hhipl1 |
| 2230 | 3 | 4 | 5 | 6 | | VI-1 | Hinfp |
| 2231 | 3 | 4 | 5 | 6 | | VI-1 | Hist1h2ad |
| 2232 | 3 | 4 | 5 | 6 | | VI-1 | Hist1h2ae |
| 2233 | 3 | 4 | 5 | 6 | | VI-1 | Hist1h2ai |
| 2234 | 3 | 4 | 5 | 6 | | VI-1 | Hist1h2ba |
| 2235 | 3 | 4 | 5 | 6 | | VI-1 | Hist1h2bc |
| 2236 | 3 | 4 | 5 | 6 | | VI-1 | Hist1h2be |
| 2237 | 3 | 4 | 5 | 6 | | VI-1 | Hist1h2bf |
| 2238 | 3 | 4 | 5 | 6 | | VI-1 | Hist1h2bg |
| 2239 | 3 | 4 | 5 | 6 | | VI-1 | Hist1h2bh |
| 2240 | 3 | 4 | 5 | 6 | | VI-1 | Hist1h2bj |
| 2241 | 3 | 4 | 5 | 6 | | VI-1 | Hist1h2bn |
| 2242 | 3 | 4 | 5 | 6 | | VI-1 | Hist1h2bp |
| 2243 | 3 | 4 | 5 | 6 | | VI-1 | Hist1h3e |
| 2244 | 3 | 4 | 5 | 6 | | VI-1 | Hist1h3i |
| 2245 | 3 | 4 | 5 | 6 | | VI-1 | Hist1h4b |
| 2246 | 3 | 4 | 5 | 6 | | VI-1 | Hist1h4d |
| 2247 | 3 | 4 | 5 | 6 | | VI-1 | Hist1h4j |
| 2248 | 3 | 4 | 5 | 6 | | VI-1 | Hist1h4k |
| 2249 | 3 | 4 | 5 | 6 | | VI-1 | Hist1h4n |
| 2250 | 3 | 4 | 5 | 6 | | VI-1 | Hist2h2ac |
| 2251 | 3 | 4 | 5 | 6 | | VI-1 | Hist2h3b |
| 2252 | 3 | 4 | 5 | 6 | | VI-1 | Hist3h2ba |
| 2253 | 3 | 4 | 5 | 6 | | VI-1 | Hivep1 |
| 2254 | 3 | 4 | 5 | 6 | | VI-1 | Hivep3 |
| 2255 | 3 | 4 | 5 | 6 | | VI-1 | Hk1os |
| 2256 | 3 | 4 | 5 | 6 | | VI-1 | Hmga1 |
| 2257 | 3 | 4 | 5 | 6 | | VI-1 | Hmga2-ps1 |
| 2258 | 3 | 4 | 5 | 6 | | VI-1 | Hmgb3 |
| 2259 | 3 | 4 | 5 | 6 | | VI-1 | Hmgcl |
| 2260 | 3 | 4 | 5 | 6 | | VI-1 | Hmox1 |
| 2261 | 3 | 4 | 5 | 6 | | VI-1 | Hnf1b |
| 2262 | 3 | 4 | 5 | 6 | | VI-1 | Hnf4a |
| 2263 | 3 | 4 | 5 | 6 | | VI-1 | Hnrnpa1 |
| 2264 | 3 | 4 | 5 | 6 | | VI-1 | Hoga1 |
| 2265 | 3 | 4 | 5 | 6 | | VI-1 | Hook1 |
| 2266 | 3 | 4 | 5 | 6 | | VI-1 | Hook2 |
| 2267 | 3 | 4 | 5 | 6 | | VI-1 | Hopx |
| 2268 | 3 | 4 | 5 | 6 | | VI-1 | Hoxb13 |
| 2269 | 3 | 4 | 5 | 6 | | VI-1 | Hoxb6 |
| 2270 | 3 | 4 | 5 | 6 | | VI-1 | Hoxb7 |
| 2271 | 3 | 4 | 5 | 6 | | VI-1 | Hoxb8 |
| 2272 | 3 | 4 | 5 | 6 | | VI-1 | Hoxb9 |
| 2273 | 3 | 4 | 5 | 6 | | VI-1 | Hoxc4 |
| 2274 | 3 | 4 | 5 | 6 | | VI-1 | Hoxd3 |
| 2275 | 3 | 4 | 5 | 6 | | VI-1 | Hoxd4 |
| 2276 | 3 | 4 | 5 | 6 | | VI-1 | Hp |
| 2277 | 3 | 4 | 5 | 6 | | VI-1 | Hpd |
| 2278 | 3 | 4 | 5 | 6 | | VI-1 | Hpdl |
| 2279 | 3 | 4 | 5 | 6 | | VI-1 | Hpn |
| 2280 | 3 | 4 | 5 | 6 | | VI-1 | Hrasls |
| 2281 | 3 | 4 | 5 | 6 | | VI-1 | Hrc |
| 2282 | 3 | 4 | 5 | 6 | | VI-1 | Hrg |
| 2283 | 3 | 4 | 5 | 6 | | VI-1 | Hrh2 |
| 2284 | 3 | 4 | 5 | 6 | | VI-1 | Hs3st3b1 |
| 2285 | 3 | 4 | 5 | 6 | | VI-1 | Hscb |
| 2286 | 3 | 4 | 5 | 6 | | VI-1 | Hsd11b1 |
| 2287 | 3 | 4 | 5 | 6 | | VI-1 | Hsd17b11 |
| 2288 | 3 | 4 | 5 | 6 | | VI-1 | Hsd3b2 |
| 2289 | 3 | 4 | 5 | 6 | | VI-1 | Hsp90b1 |
| 2290 | 3 | 4 | 5 | 6 | | VI-1 | Hspa1a |
| 2291 | 3 | 4 | 5 | 6 | | VI-1 | Hspa1b |
| 2292 | 3 | 4 | 5 | 6 | | VI-1 | Hspa5 |
| 2293 | 3 | 4 | 5 | 6 | | VI-1 | Hspb11 |
| 2294 | 3 | 4 | 5 | 6 | | VI-1 | Hspb2 |
| 2295 | 3 | 4 | 5 | 6 | | VI-1 | Htr2a |
| 2296 | 3 | 4 | 5 | 6 | | VI-1 | Hunk |
| 2297 | 3 | 4 | 5 | 6 | | VI-1 | Hyal1 |
| 2298 | 3 | 4 | 5 | 6 | | VI-1 | I830012O16Rik |
| 2299 | 3 | 4 | 5 | 6 | | VI-1 | Ict1 |
| 2300 | 3 | 4 | 5 | 6 | | VI-1 | Idh1 |
| 2301 | 3 | 4 | 5 | 6 | | VI-1 | Iffo2 |
| 2302 | 3 | 4 | 5 | 6 | | VI-1 | Ifi202b |

Fig. 36 - 13

| | | | | | | |
|---|---|---|---|---|---|---|
| 2303 | 3 | 4 | 5 | 6 | VI-1 | Ifi27l2a |
| 2304 | 3 | 4 | 5 | 6 | VI-1 | Ifi30 |
| 2305 | 3 | 4 | 5 | 6 | VI-1 | Ifi44 |
| 2306 | 3 | 4 | 5 | 6 | VI-1 | Ifit3 |
| 2307 | 3 | 4 | 5 | 6 | VI-1 | Ifitm1 |
| 2308 | 3 | 4 | 5 | 6 | VI-1 | Ifitm3 |
| 2309 | 3 | 4 | 5 | 6 | VI-1 | Ifitm5 |
| 2310 | 3 | 4 | 5 | 6 | VI-1 | Ifitm6 |
| 2311 | 3 | 4 | 5 | 6 | VI-1 | Ifitm7 |
| 2312 | 3 | 4 | 5 | 6 | VI-1 | Igfbp1 |
| 2313 | 3 | 4 | 5 | 6 | VI-1 | Igfbp5 |
| 2314 | 3 | 4 | 5 | 6 | VI-1 | Igsf11 |
| 2315 | 3 | 4 | 5 | 6 | VI-1 | Igsf5 |
| 2316 | 3 | 4 | 5 | 6 | VI-1 | Igsf6 |
| 2317 | 3 | 4 | 5 | 6 | VI-1 | Igsf9b |
| 2318 | 3 | 4 | 5 | 6 | VI-1 | Ihh |
| 2319 | 3 | 4 | 5 | 6 | VI-1 | Il17rb |
| 2320 | 3 | 4 | 5 | 6 | VI-1 | Il18bp |
| 2321 | 3 | 4 | 5 | 6 | VI-1 | Il1b |
| 2322 | 3 | 4 | 5 | 6 | VI-1 | Il1f9 |
| 2323 | 3 | 4 | 5 | 6 | VI-1 | Il1r2 |
| 2324 | 3 | 4 | 5 | 6 | VI-1 | Il1rap |
| 2325 | 3 | 4 | 5 | 6 | VI-1 | Il20rb |
| 2326 | 3 | 4 | 5 | 6 | VI-1 | Il4ra |
| 2327 | 3 | 4 | 5 | 6 | VI-1 | Il6ra |
| 2328 | 3 | 4 | 5 | 6 | VI-1 | Ildr1 |
| 2329 | 3 | 4 | 5 | 6 | VI-1 | Ikap |
| 2330 | 3 | 4 | 5 | 6 | VI-1 | Impad1 |
| 2331 | 3 | 4 | 5 | 6 | VI-1 | Inadl |
| 2332 | 3 | 4 | 5 | 6 | VI-1 | Inha |
| 2333 | 3 | 4 | 5 | 6 | VI-1 | Inhba |
| 2334 | 3 | 4 | 5 | 6 | VI-1 | Inhbb |
| 2335 | 3 | 4 | 5 | 6 | VI-1 | Inmt |
| 2336 | 3 | 4 | 5 | 6 | VI-1 | Ins1 |
| 2337 | 3 | 4 | 5 | 6 | VI-1 | Insig2 |
| 2338 | 3 | 4 | 5 | 6 | VI-1 | Insl5 |
| 2339 | 3 | 4 | 5 | 6 | VI-1 | Insl6 |
| 2340 | 3 | 4 | 5 | 6 | VI-1 | Iqcd |
| 2341 | 3 | 4 | 5 | 6 | VI-1 | Iqcg |
| 2342 | 3 | 4 | 5 | 6 | VI-1 | Irf1 |
| 2343 | 3 | 4 | 5 | 6 | VI-1 | Irf2 |
| 2344 | 3 | 4 | 5 | 6 | VI-1 | Irf4 |
| 2345 | 3 | 4 | 5 | 6 | VI-1 | Irf6 |
| 2346 | 3 | 4 | 5 | 6 | VI-1 | Irf7 |
| 2347 | 3 | 4 | 5 | 6 | VI-1 | Irf8 |
| 2348 | 3 | 4 | 5 | 6 | VI-1 | Irg1 |
| 2349 | 3 | 4 | 5 | 6 | VI-1 | Irgm1 |
| 2350 | 3 | 4 | 5 | 6 | VI-1 | Irs2 |
| 2351 | 3 | 4 | 5 | 6 | VI-1 | Irx2 |
| 2352 | 3 | 4 | 5 | 6 | VI-1 | Isg15 |
| 2353 | 3 | 4 | 5 | 6 | VI-1 | Isg20 |
| 2354 | 3 | 4 | 5 | 6 | VI-1 | Isoc2b |
| 2355 | 3 | 4 | 5 | 6 | VI-1 | Isx |
| 2356 | 3 | 4 | 5 | 6 | VI-1 | Isyna1 |
| 2357 | 3 | 4 | 5 | 6 | VI-1 | Itga1 |
| 2358 | 3 | 4 | 5 | 6 | VI-1 | Itga2 |
| 2359 | 3 | 4 | 5 | 6 | VI-1 | Itgam |
| 2360 | 3 | 4 | 5 | 6 | VI-1 | Itgb2 |
| 2361 | 3 | 4 | 5 | 6 | VI-1 | Itgb6 |
| 2362 | 3 | 4 | 5 | 6 | VI-1 | Itgb8 |
| 2363 | 3 | 4 | 5 | 6 | VI-1 | Itih4 |
| 2364 | 3 | 4 | 5 | 6 | VI-1 | Itln1 |
| 2365 | 3 | 4 | 5 | 6 | VI-1 | Ivd |
| 2366 | 3 | 4 | 5 | 6 | VI-1 | Jak3 |
| 2367 | 3 | 4 | 5 | 6 | VI-1 | Jsrp1 |
| 2368 | 3 | 4 | 5 | 6 | VI-1 | Kazald1 |
| 2369 | 3 | 4 | 5 | 6 | VI-1 | Kcne3 |
| 2370 | 3 | 4 | 5 | 6 | VI-1 | Kcnh3 |
| 2371 | 3 | 4 | 5 | 6 | VI-1 | Kcnh5 |
| 2372 | 3 | 4 | 5 | 6 | VI-1 | Kcnj16 |
| 2373 | 3 | 4 | 5 | 6 | VI-1 | Kcnj2 |
| 2374 | 3 | 4 | 5 | 6 | VI-1 | Kcnj3 |
| 2375 | 3 | 4 | 5 | 6 | VI-1 | Kcnj6 |
| 2376 | 3 | 4 | 5 | 6 | VI-1 | Kcnk3 |
| 2377 | 3 | 4 | 5 | 6 | VI-1 | Kcnk5 |
| 2378 | 3 | 4 | 5 | 6 | VI-1 | Kcnma1 |
| 2379 | 3 | 4 | 5 | 6 | VI-1 | Kcnn3 |
| 2380 | 3 | 4 | 5 | 6 | VI-1 | Kcnq1 |
| 2381 | 3 | 4 | 5 | 6 | VI-1 | Kcnq3 |
| 2382 | 3 | 4 | 5 | 6 | VI-1 | Kctd1 |
| 2383 | 3 | 4 | 5 | 6 | VI-1 | Kctd12b |
| 2384 | 3 | 4 | 5 | 6 | VI-1 | Kctd14 |
| 2385 | 3 | 4 | 5 | 6 | VI-1 | Kctd16 |
| 2386 | 3 | 4 | 5 | 6 | VI-1 | Kdelr3 |
| 2387 | 3 | 4 | 5 | 6 | VI-1 | Kdf1 |
| 2388 | 3 | 4 | 5 | 6 | VI-1 | Keg1 |
| 2389 | 3 | 4 | 5 | 6 | VI-1 | Khk |
| 2390 | 3 | 4 | 5 | 6 | VI-1 | Khnyn |
| 2391 | 3 | 4 | 5 | 6 | VI-1 | Kif13b |
| 2392 | 3 | 4 | 5 | 6 | VI-1 | Kif26b |
| 2393 | 3 | 4 | 5 | 6 | VI-1 | Kirrel3 |
| 2394 | 3 | 4 | 5 | 6 | VI-1 | Kiss1 |
| 2395 | 3 | 4 | 5 | 6 | VI-1 | Kl |
| 2396 | 3 | 4 | 5 | 6 | VI-1 | Klf12 |
| 2397 | 3 | 4 | 5 | 6 | VI-1 | Klf3 |
| 2398 | 3 | 4 | 5 | 6 | VI-1 | Klhdc7a |
| 2399 | 3 | 4 | 5 | 6 | VI-1 | Klhl11 |
| 2400 | 3 | 4 | 5 | 6 | VI-1 | Klhl14 |
| 2401 | 3 | 4 | 5 | 6 | VI-1 | Klhl15 |
| 2402 | 3 | 4 | 5 | 6 | VI-1 | Klhl23 |
| 2403 | 3 | 4 | 5 | 6 | VI-1 | Klhl25 |
| 2404 | 3 | 4 | 5 | 6 | VI-1 | Klhl28 |
| 2405 | 3 | 4 | 5 | 6 | VI-1 | Klhl3 |
| 2406 | 3 | 4 | 5 | 6 | VI-1 | Klhl34 |
| 2407 | 3 | 4 | 5 | 6 | VI-1 | Klhl38 |
| 2408 | 3 | 4 | 5 | 6 | VI-1 | Klhl41 |
| 2409 | 3 | 4 | 5 | 6 | VI-1 | Klhl6 |
| 2410 | 3 | 4 | 5 | 6 | VI-1 | Klk1b26 |
| 2411 | 3 | 4 | 5 | 6 | VI-1 | Klk1b27 |
| 2412 | 3 | 4 | 5 | 6 | VI-1 | Klk1b5 |
| 2413 | 3 | 4 | 5 | 6 | VI-1 | Klra10 |
| 2414 | 3 | 4 | 5 | 6 | VI-1 | Klra17 |
| 2415 | 3 | 4 | 5 | 6 | VI-1 | Klra18 |
| 2416 | 3 | 4 | 5 | 6 | VI-1 | Klra21 |
| 2417 | 3 | 4 | 5 | 6 | VI-1 | Klra23 |
| 2418 | 3 | 4 | 5 | 6 | VI-1 | Klrb1a |
| 2419 | 3 | 4 | 5 | 6 | VI-1 | Klrc3 |
| 2420 | 3 | 4 | 5 | 6 | VI-1 | Klrk1 |
| 2421 | 3 | 4 | 5 | 6 | VI-1 | Kmt2a |
| 2422 | 3 | 4 | 5 | 6 | VI-1 | Kmt2d |
| 2423 | 3 | 4 | 5 | 6 | VI-1 | Kng1 |
| 2424 | 3 | 4 | 5 | 6 | VI-1 | Krt14 |
| 2425 | 3 | 4 | 5 | 6 | VI-1 | Krt15 |
| 2426 | 3 | 4 | 5 | 6 | VI-1 | Krt19 |
| 2427 | 3 | 4 | 5 | 6 | VI-1 | Krt31 |
| 2428 | 3 | 4 | 5 | 6 | VI-1 | Krt7 |
| 2429 | 3 | 4 | 5 | 6 | VI-1 | Krt8 |
| 2430 | 3 | 4 | 5 | 6 | VI-1 | Krtap10-10 |
| 2431 | 3 | 4 | 5 | 6 | VI-1 | Krtap10-4 |
| 2432 | 3 | 4 | 5 | 6 | VI-1 | Krtap11-1 |
| 2433 | 3 | 4 | 5 | 6 | VI-1 | Krtap12-1 |
| 2434 | 3 | 4 | 5 | 6 | VI-1 | Krtap13-1 |
| 2435 | 3 | 4 | 5 | 6 | VI-1 | Krtap26-1 |
| 2436 | 3 | 4 | 5 | 6 | VI-1 | Krtap5-2 |
| 2437 | 3 | 4 | 5 | 6 | VI-1 | Krtap5-5 |
| 2438 | 3 | 4 | 5 | 6 | VI-1 | Ksr2 |
| 2439 | 3 | 4 | 5 | 6 | VI-1 | Ky |
| 2440 | 3 | 4 | 5 | 6 | VI-1 | LOC100503496 |
| 2441 | 3 | 4 | 5 | 6 | VI-1 | LOC100503676 |
| 2442 | 3 | 4 | 5 | 6 | VI-1 | LOC100504703 |
| 2443 | 3 | 4 | 5 | 6 | VI-1 | Lactb2 |
| 2444 | 3 | 4 | 5 | 6 | VI-1 | Lad1 |
| 2445 | 3 | 4 | 5 | 6 | VI-1 | Lancl3 |
| 2446 | 3 | 4 | 5 | 6 | VI-1 | Lat2 |
| 2447 | 3 | 4 | 5 | 6 | VI-1 | Lcat |
| 2448 | 3 | 4 | 5 | 6 | VI-1 | Lcor |
| 2449 | 3 | 4 | 5 | 6 | VI-1 | Ldb3 |
| 2450 | 3 | 4 | 5 | 6 | VI-1 | Ldhd |
| 2451 | 3 | 4 | 5 | 6 | VI-1 | Ldlrad4 |
| 2452 | 3 | 4 | 5 | 6 | VI-1 | Ldoc1l |
| 2453 | 3 | 4 | 5 | 6 | VI-1 | Lect1 |
| 2454 | 3 | 4 | 5 | 6 | VI-1 | Leng9 |
| 2455 | 3 | 4 | 5 | 6 | VI-1 | Lep |
| 2456 | 3 | 4 | 5 | 6 | VI-1 | Lgals2 |
| 2457 | 3 | 4 | 5 | 6 | VI-1 | Lgals3 |
| 2458 | 3 | 4 | 5 | 6 | VI-1 | Lgals3bp |
| 2459 | 3 | 4 | 5 | 6 | VI-1 | Lgals4 |
| 2460 | 3 | 4 | 5 | 6 | VI-1 | Lgi2 |
| 2461 | 3 | 4 | 5 | 6 | VI-1 | Lhx1 |
| 2462 | 3 | 4 | 5 | 6 | VI-1 | Lilrb4 |
| 2463 | 3 | 4 | 5 | 6 | VI-1 | Lin7b |
| 2464 | 3 | 4 | 5 | 6 | VI-1 | Lingo4 |
| 2465 | 3 | 4 | 5 | 6 | VI-1 | Lipg |
| 2466 | 3 | 4 | 5 | 6 | VI-1 | Lipt2 |
| 2467 | 3 | 4 | 5 | 6 | VI-1 | Lmln |
| 2468 | 3 | 4 | 5 | 6 | VI-1 | Lmnb1 |
| 2469 | 3 | 4 | 5 | 6 | VI-1 | Lmo4 |
| 2470 | 3 | 4 | 5 | 6 | VI-1 | Loxl1 |
| 2471 | 3 | 4 | 5 | 6 | VI-1 | Lphn3 |
| 2472 | 3 | 4 | 5 | 6 | VI-1 | Lpxn |
| 2473 | 3 | 4 | 5 | 6 | VI-1 | Lrch4 |
| 2474 | 3 | 4 | 5 | 6 | VI-1 | Lrg1 |
| 2475 | 3 | 4 | 5 | 6 | VI-1 | Lrp2 |
| 2476 | 3 | 4 | 5 | 6 | VI-1 | Lrp4 |
| 2477 | 3 | 4 | 5 | 6 | VI-1 | Lrrc10b |
| 2478 | 3 | 4 | 5 | 6 | VI-1 | Lrrc14b |
| 2479 | 3 | 4 | 5 | 6 | VI-1 | Lrrc23 |
| 2480 | 3 | 4 | 5 | 6 | VI-1 | Lrrc25 |
| 2481 | 3 | 4 | 5 | 6 | VI-1 | Lrrc36 |
| 2482 | 3 | 4 | 5 | 6 | VI-1 | Lrrc38 |
| 2483 | 3 | 4 | 5 | 6 | VI-1 | Lrrc46 |
| 2484 | 3 | 4 | 5 | 6 | VI-1 | Lrrc48 |
| 2485 | 3 | 4 | 5 | 6 | VI-1 | Lrrc4c |
| 2486 | 3 | 4 | 5 | 6 | VI-1 | Lrrc71 |
| 2487 | 3 | 4 | 5 | 6 | VI-1 | Lrrc7 |
| 2488 | 3 | 4 | 5 | 6 | VI-1 | Lrrc8b |
| 2489 | 3 | 4 | 5 | 6 | VI-1 | Lrrc8c |
| 2490 | 3 | 4 | 5 | 6 | VI-1 | Lsamp |
| 2491 | 3 | 4 | 5 | 6 | VI-1 | Lsm7 |
| 2492 | 3 | 4 | 5 | 6 | VI-1 | Lsmem1 |
| 2493 | 3 | 4 | 5 | 6 | VI-1 | Lst1 |
| 2494 | 3 | 4 | 5 | 6 | VI-1 | Ltb4r1 |

Fig. 36 - 14

| | | | | | | | |
|---|---|---|---|---|---|---|---|
| 2495 | 3 | 4 | 5 | 6 | | VI-1 | Ltc4s |
| 2496 | 3 | 4 | 5 | 6 | | VI-1 | Lum |
| 2497 | 3 | 4 | 5 | 6 | | VI-1 | Ly75 |
| 2498 | 3 | 4 | 5 | 6 | | VI-1 | Ly86 |
| 2499 | 3 | 4 | 5 | 6 | | VI-1 | Ly96 |
| 2500 | 3 | 4 | 5 | 6 | | VI-1 | Lypd2 |
| 2501 | 3 | 4 | 5 | 6 | | VI-1 | Lyrm9 |
| 2502 | 3 | 4 | 5 | 6 | | VI-1 | Lyst |
| 2503 | 3 | 4 | 5 | 6 | | VI-1 | Lyz1 |
| 2504 | 3 | 4 | 5 | 6 | | VI-1 | Lyz2 |
| 2505 | 3 | 4 | 5 | 6 | | VI-1 | Lzic |
| 2506 | 3 | 4 | 5 | 6 | | VI-1 | Macf1 |
| 2507 | 3 | 4 | 5 | 6 | | VI-1 | Mafg |
| 2508 | 3 | 4 | 5 | 6 | | VI-1 | Mal2 |
| 2509 | 3 | 4 | 5 | 6 | | VI-1 | Malat1 |
| 2510 | 3 | 4 | 5 | 6 | | VI-1 | Man1a |
| 2511 | 3 | 4 | 5 | 6 | | VI-1 | Man2c1os |
| 2512 | 3 | 4 | 5 | 6 | | VI-1 | Map1b |
| 2513 | 3 | 4 | 5 | 6 | | VI-1 | Map2k3os |
| 2514 | 3 | 4 | 5 | 6 | | VI-1 | Map3k13 |
| 2515 | 3 | 4 | 5 | 6 | | VI-1 | Map3k4 |
| 2516 | 3 | 4 | 5 | 6 | | VI-1 | Mapk13 |
| 2517 | 3 | 4 | 5 | 6 | | VI-1 | Mapk15 |
| 2518 | 3 | 4 | 5 | 6 | | VI-1 | Mapkapk3 |
| 2519 | 3 | 4 | 5 | 6 | | VI-1 | March3 |
| 2520 | 3 | 4 | 5 | 6 | | VI-1 | Marcksl1 |
| 2521 | 3 | 4 | 5 | 6 | | VI-1 | Mars2 |
| 2522 | 3 | 4 | 5 | 6 | | VI-1 | Marveld3 |
| 2523 | 3 | 4 | 5 | 6 | | VI-1 | Mboat1 |
| 2524 | 3 | 4 | 5 | 6 | | VI-1 | Mc5r |
| 2525 | 3 | 4 | 5 | 6 | | VI-1 | Mcemp1 |
| 2526 | 3 | 4 | 5 | 6 | | VI-1 | Mdk |
| 2527 | 3 | 4 | 5 | 6 | | VI-1 | Mdm4 |
| 2528 | 3 | 4 | 5 | 6 | | VI-1 | Med21 |
| 2529 | 3 | 4 | 5 | 6 | | VI-1 | Med9os |
| 2530 | 3 | 4 | 5 | 6 | | VI-1 | Mef2d |
| 2531 | 3 | 4 | 5 | 6 | | VI-1 | Megf9 |
| 2532 | 3 | 4 | 5 | 6 | | VI-1 | Memo1 |
| 2533 | 3 | 4 | 5 | 6 | | VI-1 | Mep1b |
| 2534 | 3 | 4 | 5 | 6 | | VI-1 | Mettl1 |
| 2535 | 3 | 4 | 5 | 6 | | VI-1 | Mettl10 |
| 2536 | 3 | 4 | 5 | 6 | | VI-1 | Mettl4 |
| 2537 | 3 | 4 | 5 | 6 | | VI-1 | Mettl6 |
| 2538 | 3 | 4 | 5 | 6 | | VI-1 | Mettl7b |
| 2539 | 3 | 4 | 5 | 6 | | VI-1 | Mfap3l |
| 2540 | 3 | 4 | 5 | 6 | | VI-1 | Mfap4 |
| 2541 | 3 | 4 | 5 | 6 | | VI-1 | Mfge8 |
| 2542 | 3 | 4 | 5 | 6 | | VI-1 | Mfrp |
| 2543 | 3 | 4 | 5 | 6 | | VI-1 | Mfsd12 |
| 2544 | 3 | 4 | 5 | 6 | | VI-1 | Mfsd2a |
| 2545 | 3 | 4 | 5 | 6 | | VI-1 | Mga |
| 2546 | 3 | 4 | 5 | 6 | | VI-1 | Mgam |
| 2547 | 3 | 4 | 5 | 6 | | VI-1 | Mgst2 |
| 2548 | 3 | 4 | 5 | 6 | | VI-1 | Mgst3 |
| 2549 | 3 | 4 | 5 | 6 | | VI-1 | Mia |
| 2550 | 3 | 4 | 5 | 6 | | VI-1 | Mia2 |
| 2551 | 3 | 4 | 5 | 6 | | VI-1 | Mid1ip1 |
| 2552 | 3 | 4 | 5 | 6 | | VI-1 | Milr1 |
| 2553 | 3 | 4 | 5 | 6 | | VI-1 | Mkin1os |
| 2554 | 3 | 4 | 5 | 6 | | VI-1 | Mlf1 |
| 2555 | 3 | 4 | 5 | 6 | | VI-1 | Mlph |
| 2556 | 3 | 4 | 5 | 6 | | VI-1 | Mmd2 |
| 2557 | 3 | 4 | 5 | 6 | | VI-1 | Mmp2 |
| 2558 | 3 | 4 | 5 | 6 | | VI-1 | Mmp7 |
| 2559 | 3 | 4 | 5 | 6 | | VI-1 | Mnd1-ps |
| 2560 | 3 | 4 | 5 | 6 | | VI-1 | Mns1 |
| 2561 | 3 | 4 | 5 | 6 | | VI-1 | Moap1 |
| 2562 | 3 | 4 | 5 | 6 | | VI-1 | Mob1a |
| 2563 | 3 | 4 | 5 | 6 | | VI-1 | Mob1b |
| 2564 | 3 | 4 | 5 | 6 | | VI-1 | Mogat2 |
| 2565 | 3 | 4 | 5 | 6 | | VI-1 | Morf4l2 |
| 2566 | 3 | 4 | 5 | 6 | | VI-1 | Mpeg1 |
| 2567 | 3 | 4 | 5 | 6 | | VI-1 | Mpo |
| 2568 | 3 | 4 | 5 | 6 | | VI-1 | Mptx1 |
| 2569 | 3 | 4 | 5 | 6 | | VI-1 | Mptx2 |
| 2570 | 3 | 4 | 5 | 6 | | VI-1 | Mpz |
| 2571 | 3 | 4 | 5 | 6 | | VI-1 | Mpzl3 |
| 2572 | 3 | 4 | 5 | 6 | | VI-1 | Mrap |
| 2573 | 3 | 4 | 5 | 6 | | VI-1 | Mrgpra2a |
| 2574 | 3 | 4 | 5 | 6 | | VI-1 | Mrgpra2b |
| 2575 | 3 | 4 | 5 | 6 | | VI-1 | Mrpl21 |
| 2576 | 3 | 4 | 5 | 6 | | VI-1 | Mrpl23 |
| 2577 | 3 | 4 | 5 | 6 | | VI-1 | Mrpl33 |
| 2578 | 3 | 4 | 5 | 6 | | VI-1 | Mrpl52 |
| 2579 | 3 | 4 | 5 | 6 | | VI-1 | Mrps18c |
| 2580 | 3 | 4 | 5 | 6 | | VI-1 | Mrs2 |
| 2581 | 3 | 4 | 5 | 6 | | VI-1 | Ms4a3 |
| 2582 | 3 | 4 | 5 | 6 | | VI-1 | Ms4a6c |
| 2583 | 3 | 4 | 5 | 6 | | VI-1 | Ms4a6d |
| 2584 | 3 | 4 | 5 | 6 | | VI-1 | Ms4a8a |
| 2585 | 3 | 4 | 5 | 6 | | VI-1 | Msr1 |
| 2586 | 3 | 4 | 5 | 6 | | VI-1 | Mt1 |
| 2587 | 3 | 4 | 5 | 6 | | VI-1 | Mtch2 |
| 2588 | 3 | 4 | 5 | 6 | | VI-1 | Mthfd2 |
| 2589 | 3 | 4 | 5 | 6 | | VI-1 | Mthfs |
| 2590 | 3 | 4 | 5 | 6 | | VI-1 | Mtmr9 |
| 2591 | 3 | 4 | 5 | 6 | | VI-1 | Mug1 |
| 2592 | 3 | 4 | 5 | 6 | | VI-1 | Mum1l1 |
| 2593 | 3 | 4 | 5 | 6 | | VI-1 | Mx1 |
| 2594 | 3 | 4 | 5 | 6 | | VI-1 | Mybpc2 |
| 2595 | 3 | 4 | 5 | 6 | | VI-1 | Myf6 |
| 2596 | 3 | 4 | 5 | 6 | | VI-1 | Myh4 |
| 2597 | 3 | 4 | 5 | 6 | | VI-1 | Myl1 |
| 2598 | 3 | 4 | 5 | 6 | | VI-1 | Myl10 |
| 2599 | 3 | 4 | 5 | 6 | | VI-1 | Myl6 |
| 2600 | 3 | 4 | 5 | 6 | | VI-1 | Myl9 |
| 2601 | 3 | 4 | 5 | 6 | | VI-1 | Mylpf |
| 2602 | 3 | 4 | 5 | 6 | | VI-1 | Myo5b |
| 2603 | 3 | 4 | 5 | 6 | | VI-1 | Myocd |
| 2604 | 3 | 4 | 5 | 6 | | VI-1 | Myod1 |
| 2605 | 3 | 4 | 5 | 6 | | VI-1 | Myom2 |
| 2606 | 3 | 4 | 5 | 6 | | VI-1 | Myoz1 |
| 2607 | 3 | 4 | 5 | 6 | | VI-1 | Myoz2 |
| 2608 | 3 | 4 | 5 | 6 | | VI-1 | N4bp2 |
| 2609 | 3 | 4 | 5 | 6 | | VI-1 | Naa10 |
| 2610 | 3 | 4 | 5 | 6 | | VI-1 | Nanos3 |
| 2611 | 3 | 4 | 5 | 6 | | VI-1 | Napsa |
| 2612 | 3 | 4 | 5 | 6 | | VI-1 | Nat8 |
| 2613 | 3 | 4 | 5 | 6 | | VI-1 | Nav2 |
| 2614 | 3 | 4 | 5 | 6 | | VI-1 | Nav3 |
| 2615 | 3 | 4 | 5 | 6 | | VI-1 | Nbeal1 |
| 2616 | 3 | 4 | 5 | 6 | | VI-1 | Ncam2 |
| 2617 | 3 | 4 | 5 | 6 | | VI-1 | Ncmap |
| 2618 | 3 | 4 | 5 | 6 | | VI-1 | Ndrg2 |
| 2619 | 3 | 4 | 5 | 6 | | VI-1 | Ndst1 |
| 2620 | 3 | 4 | 5 | 6 | | VI-1 | Ndst4 |
| 2621 | 3 | 4 | 5 | 6 | | VI-1 | Ndufa5 |
| 2622 | 3 | 4 | 5 | 6 | | VI-1 | Ndufaf2 |
| 2623 | 3 | 4 | 5 | 6 | | VI-1 | Ndufaf6 |
| 2624 | 3 | 4 | 5 | 6 | | VI-1 | Ndufb3 |
| 2625 | 3 | 4 | 5 | 6 | | VI-1 | Ndufs7 |
| 2626 | 3 | 4 | 5 | 6 | | VI-1 | Nebl |
| 2627 | 3 | 4 | 5 | 6 | | VI-1 | Neil3 |
| 2628 | 3 | 4 | 5 | 6 | | VI-1 | Nek1 |
| 2629 | 3 | 4 | 5 | 6 | | VI-1 | Nek4 |
| 2630 | 3 | 4 | 5 | 6 | | VI-1 | Nell1os |
| 2631 | 3 | 4 | 5 | 6 | | VI-1 | Nfam1 |
| 2632 | 3 | 4 | 5 | 6 | | VI-1 | Nfe2l3 |
| 2633 | 3 | 4 | 5 | 6 | | VI-1 | Nfil3 |
| 2634 | 3 | 4 | 5 | 6 | | VI-1 | Ngef |
| 2635 | 3 | 4 | 5 | 6 | | VI-1 | Ngfrap1 |
| 2636 | 3 | 4 | 5 | 6 | | VI-1 | Nhlrc2 |
| 2637 | 3 | 4 | 5 | 6 | | VI-1 | Nhlrc3 |
| 2638 | 3 | 4 | 5 | 6 | | VI-1 | Nhlrc4 |
| 2639 | 3 | 4 | 5 | 6 | | VI-1 | Nicn1 |
| 2640 | 3 | 4 | 5 | 6 | | VI-1 | Nlrc5 |
| 2641 | 3 | 4 | 5 | 6 | | VI-1 | Nlrp12 |
| 2642 | 3 | 4 | 5 | 6 | | VI-1 | Nlrp6 |
| 2643 | 3 | 4 | 5 | 6 | | VI-1 | Nmb |
| 2644 | 3 | 4 | 5 | 6 | | VI-1 | Nme2 |
| 2645 | 3 | 4 | 5 | 6 | | VI-1 | Nme4 |
| 2646 | 3 | 4 | 5 | 6 | | VI-1 | Nme5 |
| 2647 | 3 | 4 | 5 | 6 | | VI-1 | Nnat |
| 2648 | 3 | 4 | 5 | 6 | | VI-1 | Nnmt |
| 2649 | 3 | 4 | 5 | 6 | | VI-1 | Nos1 |
| 2650 | 3 | 4 | 5 | 6 | | VI-1 | Nos1ap |
| 2651 | 3 | 4 | 5 | 6 | | VI-1 | Notum |
| 2652 | 3 | 4 | 5 | 6 | | VI-1 | Npas2 |
| 2653 | 3 | 4 | 5 | 6 | | VI-1 | Npas4 |
| 2654 | 3 | 4 | 5 | 6 | | VI-1 | Nptxr |
| 2655 | 3 | 4 | 5 | 6 | | VI-1 | Npy |
| 2656 | 3 | 4 | 5 | 6 | | VI-1 | Npy4r |
| 2657 | 3 | 4 | 5 | 6 | | VI-1 | Nr2c2 |
| 2658 | 3 | 4 | 5 | 6 | | VI-1 | Nr2c2ap |
| 2659 | 3 | 4 | 5 | 6 | | VI-1 | Nr3c2 |
| 2660 | 3 | 4 | 5 | 6 | | VI-1 | Nr4a2 |
| 2661 | 3 | 4 | 5 | 6 | | VI-1 | Nr4a3 |
| 2662 | 3 | 4 | 5 | 6 | | VI-1 | Nr6a1 |
| 2663 | 3 | 4 | 5 | 6 | | VI-1 | Nrg1 |
| 2664 | 3 | 4 | 5 | 6 | | VI-1 | Nrip1 |
| 2665 | 3 | 4 | 5 | 6 | | VI-1 | Nsun3 |
| 2666 | 3 | 4 | 5 | 6 | | VI-1 | Nt5c1a |
| 2667 | 3 | 4 | 5 | 6 | | VI-1 | Nt5dc2 |
| 2668 | 3 | 4 | 5 | 6 | | VI-1 | Ntf3 |
| 2669 | 3 | 4 | 5 | 6 | | VI-1 | Nthl1 |
| 2670 | 3 | 4 | 5 | 6 | | VI-1 | Nudt7 |
| 2671 | 3 | 4 | 5 | 6 | | VI-1 | Nup43 |
| 2672 | 3 | 4 | 5 | 6 | | VI-1 | Nup62-il4i1 |
| 2673 | 3 | 4 | 5 | 6 | | VI-1 | Nupr1 |
| 2674 | 3 | 4 | 5 | 6 | | VI-1 | Nwd1 |
| 2675 | 3 | 4 | 5 | 6 | | VI-1 | Nxf3 |
| 2676 | 3 | 4 | 5 | 6 | | VI-1 | Nxph4 |
| 2677 | 3 | 4 | 5 | 6 | | VI-1 | Nxt1 |
| 2678 | 3 | 4 | 5 | 6 | | VI-1 | Nvap2 |
| 2679 | 3 | 4 | 5 | 6 | | VI-1 | Oard1 |
| 2680 | 3 | 4 | 5 | 6 | | VI-1 | Oas2 |
| 2681 | 3 | 4 | 5 | 6 | | VI-1 | Oat |
| 2682 | 3 | 4 | 5 | 6 | | VI-1 | Ociad2 |
| 2683 | 3 | 4 | 5 | 6 | | VI-1 | Ocln |
| 2684 | 3 | 4 | 5 | 6 | | VI-1 | Odf3b |
| 2685 | 3 | 4 | 5 | 6 | | VI-1 | Odf3l1 |
| 2686 | 3 | 4 | 5 | 6 | | VI-1 | Olfm4 |

Fig. 36 - 15

| | | | | | | | |
|---|---|---|---|---|---|---|---|
| 2687 | 3 | 4 | 5 | 6 | | VI-1 | Olfr1393 |
| 2688 | 3 | 4 | 5 | 6 | | VI-1 | Olfr787 |
| 2689 | 3 | 4 | 5 | 6 | | VI-1 | Oprd1 |
| 2690 | 3 | 4 | 5 | 6 | | VI-1 | Orai2 |
| 2691 | 3 | 4 | 5 | 6 | | VI-1 | Orm1 |
| 2692 | 3 | 4 | 5 | 6 | | VI-1 | Orm2 |
| 2693 | 3 | 4 | 5 | 6 | | VI-1 | Ormdl2 |
| 2694 | 3 | 4 | 5 | 6 | | VI-1 | Oscp1 |
| 2695 | 3 | 4 | 5 | 6 | | VI-1 | Osgin1 |
| 2696 | 3 | 4 | 5 | 6 | | VI-1 | Osr2 |
| 2697 | 3 | 4 | 5 | 6 | | VI-1 | Ostf1 |
| 2698 | 3 | 4 | 5 | 6 | | VI-1 | Otub2 |
| 2699 | 3 | 4 | 5 | 6 | | VI-1 | Otud1 |
| 2700 | 3 | 4 | 5 | 6 | | VI-1 | Otud3 |
| 2701 | 3 | 4 | 5 | 6 | | VI-1 | P2rx2 |
| 2702 | 3 | 4 | 5 | 6 | | VI-1 | P2ry4 |
| 2703 | 3 | 4 | 5 | 6 | | VI-1 | P4hb |
| 2704 | 3 | 4 | 5 | 6 | | VI-1 | Pacrg |
| 2705 | 3 | 4 | 5 | 6 | | VI-1 | Padi4 |
| 2706 | 3 | 4 | 5 | 6 | | VI-1 | Pafah1b3 |
| 2707 | 3 | 4 | 5 | 6 | | VI-1 | Palld |
| 2708 | 3 | 4 | 5 | 6 | | VI-1 | Paqr3 |
| 2709 | 3 | 4 | 5 | 6 | | VI-1 | Paqr6 |
| 2710 | 3 | 4 | 5 | 6 | | VI-1 | Parm1 |
| 2711 | 3 | 4 | 5 | 6 | | VI-1 | Parp14 |
| 2712 | 3 | 4 | 5 | 6 | | VI-1 | Parp9 |
| 2713 | 3 | 4 | 5 | 6 | | VI-1 | Pax2 |
| 2714 | 3 | 4 | 5 | 6 | | VI-1 | Pcbd1 |
| 2715 | 3 | 4 | 5 | 6 | | VI-1 | Pcdh1 |
| 2716 | 3 | 4 | 5 | 6 | | VI-1 | Pcdh17 |
| 2717 | 3 | 4 | 5 | 6 | | VI-1 | Pcdh7 |
| 2718 | 3 | 4 | 5 | 6 | | VI-1 | Pcdhb16 |
| 2719 | 3 | 4 | 5 | 6 | | VI-1 | Pcnt |
| 2720 | 3 | 4 | 5 | 6 | | VI-1 | Pcolce |
| 2721 | 3 | 4 | 5 | 6 | | VI-1 | Pcsk9 |
| 2722 | 3 | 4 | 5 | 6 | | VI-1 | Pctp |
| 2723 | 3 | 4 | 5 | 6 | | VI-1 | Pdcd11 |
| 2724 | 3 | 4 | 5 | 6 | | VI-1 | Pde3a |
| 2725 | 3 | 4 | 5 | 6 | | VI-1 | Pde7b |
| 2726 | 3 | 4 | 5 | 6 | | VI-1 | Pdia2 |
| 2727 | 3 | 4 | 5 | 6 | | VI-1 | Pdp2 |
| 2728 | 3 | 4 | 5 | 6 | | VI-1 | Pdpr |
| 2729 | 3 | 4 | 5 | 6 | | VI-1 | Pds5a |
| 2730 | 3 | 4 | 5 | 6 | | VI-1 | Pdzd3 |
| 2731 | 3 | 4 | 5 | 6 | | VI-1 | Pebp1 |
| 2732 | 3 | 4 | 5 | 6 | | VI-1 | Peg3 |
| 2733 | 3 | 4 | 5 | 6 | | VI-1 | Peg3os |
| 2734 | 3 | 4 | 5 | 6 | | VI-1 | Pemt |
| 2735 | 3 | 4 | 5 | 6 | | VI-1 | Perp |
| 2736 | 3 | 4 | 5 | 6 | | VI-1 | Pet117 |
| 2737 | 3 | 4 | 5 | 6 | | VI-1 | Pfn3 |
| 2738 | 3 | 4 | 5 | 6 | | VI-1 | Pgam2 |
| 2739 | 3 | 4 | 5 | 6 | | VI-1 | Pgap2 |
| 2740 | 3 | 4 | 5 | 6 | | VI-1 | Pggt1b |
| 2741 | 3 | 4 | 5 | 6 | | VI-1 | Pgrmc1 |
| 2742 | 3 | 4 | 5 | 6 | | VI-1 | Phf11c |
| 2743 | 3 | 4 | 5 | 6 | | VI-1 | Phf6 |
| 2744 | 3 | 4 | 5 | 6 | | VI-1 | Phlda1 |
| 2745 | 3 | 4 | 5 | 6 | | VI-1 | Phospho1 |
| 2746 | 3 | 4 | 5 | 6 | | VI-1 | Phyh |
| 2747 | 3 | 4 | 5 | 6 | | VI-1 | Pigl |
| 2748 | 3 | 4 | 5 | 6 | | VI-1 | Pigr |
| 2749 | 3 | 4 | 5 | 6 | | VI-1 | Pik3ap1 |
| 2750 | 3 | 4 | 5 | 6 | | VI-1 | Pip5k1b |
| 2751 | 3 | 4 | 5 | 6 | | VI-1 | Pipox |
| 2752 | 3 | 4 | 5 | 6 | | VI-1 | Pira11 |
| 2753 | 3 | 4 | 5 | 6 | | VI-1 | Pitx2 |
| 2754 | 3 | 4 | 5 | 6 | | VI-1 | Pja1 |
| 2755 | 3 | 4 | 5 | 6 | | VI-1 | Pkd1 |
| 2756 | 3 | 4 | 5 | 6 | | VI-1 | Pklr |
| 2757 | 3 | 4 | 5 | 6 | | VI-1 | Pkp3 |
| 2758 | 3 | 4 | 5 | 6 | | VI-1 | Pla2g5 |
| 2759 | 3 | 4 | 5 | 6 | | VI-1 | Plac8 |
| 2760 | 3 | 4 | 5 | 6 | | VI-1 | Plac9a |
| 2761 | 3 | 4 | 5 | 6 | | VI-1 | Plac9b |
| 2762 | 3 | 4 | 5 | 6 | | VI-1 | Plcb4 |
| 2763 | 3 | 4 | 5 | 6 | | VI-1 | Plcg1 |
| 2764 | 3 | 4 | 5 | 6 | | VI-1 | Plcxd2 |
| 2765 | 3 | 4 | 5 | 6 | | VI-1 | Plcxd3 |
| 2766 | 3 | 4 | 5 | 6 | | VI-1 | Pld4 |
| 2767 | 3 | 4 | 5 | 6 | | VI-1 | Plec |
| 2768 | 3 | 4 | 5 | 6 | | VI-1 | Plekha6 |
| 2769 | 3 | 4 | 5 | 6 | | VI-1 | Plekhb1 |
| 2770 | 3 | 4 | 5 | 6 | | VI-1 | Plekhh1 |
| 2771 | 3 | 4 | 5 | 6 | | VI-1 | Plet1 |
| 2772 | 3 | 4 | 5 | 6 | | VI-1 | Plg |
| 2773 | 3 | 4 | 5 | 6 | | VI-1 | Plin1 |
| 2774 | 3 | 4 | 5 | 6 | | VI-1 | Plin2 |
| 2775 | 3 | 4 | 5 | 6 | | VI-1 | Plin4 |
| 2776 | 3 | 4 | 5 | 6 | | VI-1 | Plk3 |
| 2777 | 3 | 4 | 5 | 6 | | VI-1 | Pmp22 |
| 2778 | 3 | 4 | 5 | 6 | | VI-1 | Pnpla3 |
| 2779 | 3 | 4 | 5 | 6 | | VI-1 | Polq |
| 2780 | 3 | 4 | 5 | 6 | | VI-1 | Polr2k |
| 2781 | 3 | 4 | 5 | 6 | | VI-1 | Polrmt |
| 2782 | 3 | 4 | 5 | 6 | | VI-1 | Pop5 |
| 2783 | 3 | 4 | 5 | 6 | | VI-1 | Pou2f2 |
| 2784 | 3 | 4 | 5 | 6 | | VI-1 | Pou3f1 |
| 2785 | 3 | 4 | 5 | 6 | | VI-1 | Pou3f3os |
| 2786 | 3 | 4 | 5 | 6 | | VI-1 | Pou3f4 |
| 2787 | 3 | 4 | 5 | 6 | | VI-1 | Ppara |
| 2788 | 3 | 4 | 5 | 6 | | VI-1 | Pparg |
| 2789 | 3 | 4 | 5 | 6 | | VI-1 | Ppargc1a |
| 2790 | 3 | 4 | 5 | 6 | | VI-1 | Ppargc1b |
| 2791 | 3 | 4 | 5 | 6 | | VI-1 | Ppifos |
| 2792 | 3 | 4 | 5 | 6 | | VI-1 | Ppil6 |
| 2793 | 3 | 4 | 5 | 6 | | VI-1 | Ppm1l |
| 2794 | 3 | 4 | 5 | 6 | | VI-1 | Ppp1r10 |
| 2795 | 3 | 4 | 5 | 6 | | VI-1 | Ppp1r12a |
| 2796 | 3 | 4 | 5 | 6 | | VI-1 | Ppp1r14d |
| 2797 | 3 | 4 | 5 | 6 | | VI-1 | Ppp1r1b |
| 2798 | 3 | 4 | 5 | 6 | | VI-1 | Ppp1r36 |
| 2799 | 3 | 4 | 5 | 6 | | VI-1 | Ppp1r3b |
| 2800 | 3 | 4 | 5 | 6 | | VI-1 | Ppp1r3c |
| 2801 | 3 | 4 | 5 | 6 | | VI-1 | Ppp1r3e |
| 2802 | 3 | 4 | 5 | 6 | | VI-1 | Ppp2r2b |
| 2803 | 3 | 4 | 5 | 6 | | VI-1 | Ppy |
| 2804 | 3 | 4 | 5 | 6 | | VI-1 | Prcp |
| 2805 | 3 | 4 | 5 | 6 | | VI-1 | Prdm10 |
| 2806 | 3 | 4 | 5 | 6 | | VI-1 | Prdm11 |
| 2807 | 3 | 4 | 5 | 6 | | VI-1 | Prelid2 |
| 2808 | 3 | 4 | 5 | 6 | | VI-1 | Prkar2b |
| 2809 | 3 | 4 | 5 | 6 | | VI-1 | Prm1 |
| 2810 | 3 | 4 | 5 | 6 | | VI-1 | Prm2 |
| 2811 | 3 | 4 | 5 | 6 | | VI-1 | Prob1 |
| 2812 | 3 | 4 | 5 | 6 | | VI-1 | Prok2 |
| 2813 | 3 | 4 | 5 | 6 | | VI-1 | Prom1 |
| 2814 | 3 | 4 | 5 | 6 | | VI-1 | Prox1 |
| 2815 | 3 | 4 | 5 | 6 | | VI-1 | Prox2 |
| 2816 | 3 | 4 | 5 | 6 | | VI-1 | Prr15 |
| 2817 | 3 | 4 | 5 | 6 | | VI-1 | Prr15l |
| 2818 | 3 | 4 | 5 | 6 | | VI-1 | Prr18 |
| 2819 | 3 | 4 | 5 | 6 | | VI-1 | Prr32 |
| 2820 | 3 | 4 | 5 | 6 | | VI-1 | Prrc2a |
| 2821 | 3 | 4 | 5 | 6 | | VI-1 | Prrc2c |
| 2822 | 3 | 4 | 5 | 6 | | VI-1 | Prrg1 |
| 2823 | 3 | 4 | 5 | 6 | | VI-1 | Prrg4 |
| 2824 | 3 | 4 | 5 | 6 | | VI-1 | Prrt1 |
| 2825 | 3 | 4 | 5 | 6 | | VI-1 | Prss1 |
| 2826 | 3 | 4 | 5 | 6 | | VI-1 | Prss12 |
| 2827 | 3 | 4 | 5 | 6 | | VI-1 | Prss3 |
| 2828 | 3 | 4 | 5 | 6 | | VI-1 | Prss32 |
| 2829 | 3 | 4 | 5 | 6 | | VI-1 | Prss56 |
| 2830 | 3 | 4 | 5 | 6 | | VI-1 | Prss57 |
| 2831 | 3 | 4 | 5 | 6 | | VI-1 | Prtn3 |
| 2832 | 3 | 4 | 5 | 6 | | VI-1 | Psma3 |
| 2833 | 3 | 4 | 5 | 6 | | VI-1 | Psmb10 |
| 2834 | 3 | 4 | 5 | 6 | | VI-1 | Psmb8 |
| 2835 | 3 | 4 | 5 | 6 | | VI-1 | Psmb9 |
| 2836 | 3 | 4 | 5 | 6 | | VI-1 | Psme1 |
| 2837 | 3 | 4 | 5 | 6 | | VI-1 | Pstpip1 |
| 2838 | 3 | 4 | 5 | 6 | | VI-1 | Ptar1 |
| 2839 | 3 | 4 | 5 | 6 | | VI-1 | Ptch1 |
| 2840 | 3 | 4 | 5 | 6 | | VI-1 | Ptch2 |
| 2841 | 3 | 4 | 5 | 6 | | VI-1 | Ptgis |
| 2842 | 3 | 4 | 5 | 6 | | VI-1 | Ptgr1 |
| 2843 | 3 | 4 | 5 | 6 | | VI-1 | Pth1r |
| 2844 | 3 | 4 | 5 | 6 | | VI-1 | Pthlh |
| 2845 | 3 | 4 | 5 | 6 | | VI-1 | Ptpib |
| 2846 | 3 | 4 | 5 | 6 | | VI-1 | Ptpn22 |
| 2847 | 3 | 4 | 5 | 6 | | VI-1 | Ptpn3 |
| 2848 | 3 | 4 | 5 | 6 | | VI-1 | Ptpn4 |
| 2849 | 3 | 4 | 5 | 6 | | VI-1 | Ptpn5 |
| 2850 | 3 | 4 | 5 | 6 | | VI-1 | Ptprf |
| 2851 | 3 | 4 | 5 | 6 | | VI-1 | Ptrh1 |
| 2852 | 3 | 4 | 5 | 6 | | VI-1 | Pura |
| 2853 | 3 | 4 | 5 | 6 | | VI-1 | Pvrl4 |
| 2854 | 3 | 4 | 5 | 6 | | VI-1 | Pycard |
| 2855 | 3 | 4 | 5 | 6 | | VI-1 | Pygo1 |
| 2856 | 3 | 4 | 5 | 6 | | VI-1 | P2p |
| 2857 | 3 | 4 | 5 | 6 | | VI-1 | Rab11fip1 |
| 2858 | 3 | 4 | 5 | 6 | | VI-1 | Rab17 |
| 2859 | 3 | 4 | 5 | 6 | | VI-1 | Rab26os |
| 2860 | 3 | 4 | 5 | 6 | | VI-1 | Rab32 |
| 2861 | 3 | 4 | 5 | 6 | | VI-1 | Rab7 |
| 2862 | 3 | 4 | 5 | 6 | | VI-1 | Rabl2 |
| 2863 | 3 | 4 | 5 | 6 | | VI-1 | Rac2 |
| 2864 | 3 | 4 | 5 | 6 | | VI-1 | Rag1 |
| 2865 | 3 | 4 | 5 | 6 | | VI-1 | Ramp3 |
| 2866 | 3 | 4 | 5 | 6 | | VI-1 | Rangrf |
| 2867 | 3 | 4 | 5 | 6 | | VI-1 | Rap1gap |
| 2868 | 3 | 4 | 5 | 6 | | VI-1 | Rapgef5 |
| 2869 | 3 | 4 | 5 | 6 | | VI-1 | Rarres1 |
| 2870 | 3 | 4 | 5 | 6 | | VI-1 | Rasl10a |
| 2871 | 3 | 4 | 5 | 6 | | VI-1 | Rasl11a |
| 2872 | 3 | 4 | 5 | 6 | | VI-1 | Rassf7 |
| 2873 | 3 | 4 | 5 | 6 | | VI-1 | Rassf8 |
| 2874 | 3 | 4 | 5 | 6 | | VI-1 | Rbfox3 |
| 2875 | 3 | 4 | 5 | 6 | | VI-1 | Rbm14-rbm4 |
| 2876 | 3 | 4 | 5 | 6 | | VI-1 | Rbm15 |
| 2877 | 3 | 4 | 5 | 6 | | VI-1 | Rbm15b |
| 2878 | 3 | 4 | 5 | 6 | | VI-1 | Rbmxl1 |

Fig. 36 - 16

| | | | | | | |
|---|---|---|---|---|---|---|
| 2879 | 3 | 4 | 5 | 6 | VI-1 | Rbp2 |
| 2880 | 3 | 4 | 5 | 6 | VI-1 | Rcor1 |
| 2881 | 3 | 4 | 5 | 6 | VI-1 | Rdh12 |
| 2882 | 3 | 4 | 5 | 6 | VI-1 | Rdh16 |
| 2883 | 3 | 4 | 5 | 6 | VI-1 | Rdh18-ps |
| 2884 | 3 | 4 | 5 | 6 | VI-1 | Rdh7 |
| 2885 | 3 | 4 | 5 | 6 | VI-1 | Reep6 |
| 2886 | 3 | 4 | 5 | 6 | VI-1 | Reg4 |
| 2887 | 3 | 4 | 5 | 6 | VI-1 | Rel |
| 2888 | 3 | 4 | 5 | 6 | VI-1 | Rerg |
| 2889 | 3 | 4 | 5 | 6 | VI-1 | Rergl |
| 2890 | 3 | 4 | 5 | 6 | VI-1 | Rest |
| 2891 | 3 | 4 | 5 | 6 | VI-1 | Retn |
| 2892 | 3 | 4 | 5 | 6 | VI-1 | Retnla |
| 2893 | 3 | 4 | 5 | 6 | VI-1 | Retsat |
| 2894 | 3 | 4 | 5 | 6 | VI-1 | Rgag4 |
| 2895 | 3 | 4 | 5 | 6 | VI-1 | Rgs10 |
| 2896 | 3 | 4 | 5 | 6 | VI-1 | Rgs11 |
| 2897 | 3 | 4 | 5 | 6 | VI-1 | Rgs16 |
| 2898 | 3 | 4 | 5 | 6 | VI-1 | Rgs9 |
| 2899 | 3 | 4 | 5 | 6 | VI-1 | Rhbdl1 |
| 2900 | 3 | 4 | 5 | 6 | VI-1 | Rhebl1 |
| 2901 | 3 | 4 | 5 | 6 | VI-1 | Rhoc |
| 2902 | 3 | 4 | 5 | 6 | VI-1 | Riiad1 |
| 2903 | 3 | 4 | 5 | 6 | VI-1 | Rimbp2 |
| 2904 | 3 | 4 | 5 | 6 | VI-1 | Rims1 |
| 2905 | 3 | 4 | 5 | 6 | VI-1 | Rims3 |
| 2906 | 3 | 4 | 5 | 6 | VI-1 | Rims4 |
| 2907 | 3 | 4 | 5 | 6 | VI-1 | Rmnd1 |
| 2908 | 3 | 4 | 5 | 6 | VI-1 | Rn4.5s |
| 2909 | 3 | 4 | 5 | 6 | VI-1 | Rn45s |
| 2910 | 3 | 4 | 5 | 6 | VI-1 | Rnaset2b |
| 2911 | 3 | 4 | 5 | 6 | VI-1 | Rnf125 |
| 2912 | 3 | 4 | 5 | 6 | VI-1 | Rnf128 |
| 2913 | 3 | 4 | 5 | 6 | VI-1 | Rnf141 |
| 2914 | 3 | 4 | 5 | 6 | VI-1 | Rnf149 |
| 2915 | 3 | 4 | 5 | 6 | VI-1 | Rnf180 |
| 2916 | 3 | 4 | 5 | 6 | VI-1 | Rnf43 |
| 2917 | 3 | 4 | 5 | 6 | VI-1 | Rogdi |
| 2918 | 3 | 4 | 5 | 6 | VI-1 | Romo1 |
| 2919 | 3 | 4 | 5 | 6 | VI-1 | Ror1 |
| 2920 | 3 | 4 | 5 | 6 | VI-1 | Rpa3 |
| 2921 | 3 | 4 | 5 | 6 | VI-1 | Rpl12 |
| 2922 | 3 | 4 | 5 | 6 | VI-1 | Rpl13a |
| 2923 | 3 | 4 | 5 | 6 | VI-1 | Rpl19 |
| 2924 | 3 | 4 | 5 | 6 | VI-1 | Rpl28 |
| 2925 | 3 | 4 | 5 | 6 | VI-1 | Rpl34 |
| 2926 | 3 | 4 | 5 | 6 | VI-1 | Rpl35 |
| 2927 | 3 | 4 | 5 | 6 | VI-1 | Rpl36a |
| 2928 | 3 | 4 | 5 | 6 | VI-1 | Rpl37a |
| 2929 | 3 | 4 | 5 | 6 | VI-1 | Rpl38 |
| 2930 | 3 | 4 | 5 | 6 | VI-1 | Rpl39 |
| 2931 | 3 | 4 | 5 | 6 | VI-1 | Rpl39l |
| 2932 | 3 | 4 | 5 | 6 | VI-1 | Rpl9 |
| 2933 | 3 | 4 | 5 | 6 | VI-1 | Rplp2 |
| 2934 | 3 | 4 | 5 | 6 | VI-1 | Rpp21 |
| 2935 | 3 | 4 | 5 | 6 | VI-1 | Rpri3 |
| 2936 | 3 | 4 | 5 | 6 | VI-1 | Rprm |
| 2937 | 3 | 4 | 5 | 6 | VI-1 | Rprml |
| 2938 | 3 | 4 | 5 | 6 | VI-1 | Rps12 |
| 2939 | 3 | 4 | 5 | 6 | VI-1 | Rps15 |
| 2940 | 3 | 4 | 5 | 6 | VI-1 | Rps15a-ps4 |
| 2941 | 3 | 4 | 5 | 6 | VI-1 | Rps19 |
| 2942 | 3 | 4 | 5 | 6 | VI-1 | Rps27 |
| 2943 | 3 | 4 | 5 | 6 | VI-1 | Rps27a |
| 2944 | 3 | 4 | 5 | 6 | VI-1 | Rps4l |
| 2945 | 3 | 4 | 5 | 6 | VI-1 | Rreb1 |
| 2946 | 3 | 4 | 5 | 6 | VI-1 | Rsad2 |
| 2947 | 3 | 4 | 5 | 6 | VI-1 | Rsc1a1 |
| 2948 | 3 | 4 | 5 | 6 | VI-1 | Rsph1 |
| 2949 | 3 | 4 | 5 | 6 | VI-1 | Rsph4a |
| 2950 | 3 | 4 | 5 | 6 | VI-1 | Rtn2 |
| 2951 | 3 | 4 | 5 | 6 | VI-1 | Rufy4 |
| 2952 | 3 | 4 | 5 | 6 | VI-1 | Runx2 |
| 2953 | 3 | 4 | 5 | 6 | VI-1 | Rxra |
| 2954 | 3 | 4 | 5 | 6 | VI-1 | S100a1 |
| 2955 | 3 | 4 | 5 | 6 | VI-1 | S100a10 |
| 2956 | 3 | 4 | 5 | 6 | VI-1 | S100a13 |
| 2957 | 3 | 4 | 5 | 6 | VI-1 | S100a4 |
| 2958 | 3 | 4 | 5 | 6 | VI-1 | S100a6 |
| 2959 | 3 | 4 | 5 | 6 | VI-1 | S100pbp |
| 2960 | 3 | 4 | 5 | 6 | VI-1 | Saa1 |
| 2961 | 3 | 4 | 5 | 6 | VI-1 | Sall1 |
| 2962 | 3 | 4 | 5 | 6 | VI-1 | Samd10 |
| 2963 | 3 | 4 | 5 | 6 | VI-1 | Samd12 |
| 2964 | 3 | 4 | 5 | 6 | VI-1 | Samd5 |
| 2965 | 3 | 4 | 5 | 6 | VI-1 | Scarna13 |
| 2966 | 3 | 4 | 5 | 6 | VI-1 | Scarna6 |
| 2967 | 3 | 4 | 5 | 6 | VI-1 | Scd1 |
| 2968 | 3 | 4 | 5 | 6 | VI-1 | Scd2 |
| 2969 | 3 | 4 | 5 | 6 | VI-1 | Scgb3a1 |
| 2970 | 3 | 4 | 5 | 6 | VI-1 | Scgb3a2 |
| 2971 | 3 | 4 | 5 | 6 | VI-1 | Scimp |
| 2972 | 3 | 4 | 5 | 6 | VI-1 | Scnn1a |
| 2973 | 3 | 4 | 5 | 6 | VI-1 | Scp2 |
| 2974 | 3 | 4 | 5 | 6 | VI-1 | Scrn2 |
| 2975 | 3 | 4 | 5 | 6 | VI-1 | Sct |
| 2976 | 3 | 4 | 5 | 6 | VI-1 | Scx |
| 2977 | 3 | 4 | 5 | 6 | VI-1 | Sdhc |
| 2978 | 3 | 4 | 5 | 6 | VI-1 | Sec14l2 |
| 2979 | 3 | 4 | 5 | 6 | VI-1 | Sec14l3 |
| 2980 | 3 | 4 | 5 | 6 | VI-1 | Sec14l4 |
| 2981 | 3 | 4 | 5 | 6 | VI-1 | Sec14l5 |
| 2982 | 3 | 4 | 5 | 6 | VI-1 | Sec61b |
| 2983 | 3 | 4 | 5 | 6 | VI-1 | Sectm1a |
| 2984 | 3 | 4 | 5 | 6 | VI-1 | Sectm1b |
| 2985 | 3 | 4 | 5 | 6 | VI-1 | Selenbp2 |
| 2986 | 3 | 4 | 5 | 6 | VI-1 | Selp |
| 2987 | 3 | 4 | 5 | 6 | VI-1 | Sepp1 |
| 2988 | 3 | 4 | 5 | 6 | VI-1 | Sepsecs |
| 2989 | 3 | 4 | 5 | 6 | VI-1 | Sept4 |
| 2990 | 3 | 4 | 5 | 6 | VI-1 | Serpina3c |
| 2991 | 3 | 4 | 5 | 6 | VI-1 | Serpina3m |
| 2992 | 3 | 4 | 5 | 6 | VI-1 | Serpina4-ps1 |
| 2993 | 3 | 4 | 5 | 6 | VI-1 | Serpinb1a |
| 2994 | 3 | 4 | 5 | 6 | VI-1 | Serpinc1 |
| 2995 | 3 | 4 | 5 | 6 | VI-1 | Serpinf1 |
| 2996 | 3 | 4 | 5 | 6 | VI-1 | Serpinf2 |
| 2997 | 3 | 4 | 5 | 6 | VI-1 | Serping1 |
| 2998 | 3 | 4 | 5 | 6 | VI-1 | Serpini2 |
| 2999 | 3 | 4 | 5 | 6 | VI-1 | Sesn3 |
| 3000 | 3 | 4 | 5 | 6 | VI-1 | Setd2 |
| 3001 | 3 | 4 | 5 | 6 | VI-1 | Setdb2 |
| 3002 | 3 | 4 | 5 | 6 | VI-1 | Sfn |
| 3003 | 3 | 4 | 5 | 6 | VI-1 | Sfrp2 |
| 3004 | 3 | 4 | 5 | 6 | VI-1 | Sfta2 |
| 3005 | 3 | 4 | 5 | 6 | VI-1 | Sftpa1 |
| 3006 | 3 | 4 | 5 | 6 | VI-1 | Sftpc |
| 3007 | 3 | 4 | 5 | 6 | VI-1 | Sh3gl2 |
| 3008 | 3 | 4 | 5 | 6 | VI-1 | Sh3pxd2b |
| 3009 | 3 | 4 | 5 | 6 | VI-1 | Shank1 |
| 3010 | 3 | 4 | 5 | 6 | VI-1 | Shank2 |
| 3011 | 3 | 4 | 5 | 6 | VI-1 | Shc3 |
| 3012 | 3 | 4 | 5 | 6 | VI-1 | Shc4 |
| 3013 | 3 | 4 | 5 | 6 | VI-1 | Sik1 |
| 3014 | 3 | 4 | 5 | 6 | VI-1 | Sik2 |
| 3015 | 3 | 4 | 5 | 6 | VI-1 | Sipa1l1 |
| 3016 | 3 | 4 | 5 | 6 | VI-1 | Skil |
| 3017 | 3 | 4 | 5 | 6 | VI-1 | Slc10a1 |
| 3018 | 3 | 4 | 5 | 6 | VI-1 | Slc10a2 |
| 3019 | 3 | 4 | 5 | 6 | VI-1 | Slc10a5 |
| 3020 | 3 | 4 | 5 | 6 | VI-1 | Slc13a1 |
| 3021 | 3 | 4 | 5 | 6 | VI-1 | Slc13a2os |
| 3022 | 3 | 4 | 5 | 6 | VI-1 | Slc15a2 |
| 3023 | 3 | 4 | 5 | 6 | VI-1 | Slc16a11 |
| 3024 | 3 | 4 | 5 | 6 | VI-1 | Slc16a13 |
| 3025 | 3 | 4 | 5 | 6 | VI-1 | Slc16a14 |
| 3026 | 3 | 4 | 5 | 6 | VI-1 | Slc16a7 |
| 3027 | 3 | 4 | 5 | 6 | VI-1 | Slc1a3 |
| 3028 | 3 | 4 | 5 | 6 | VI-1 | Slc25a13 |
| 3029 | 3 | 4 | 5 | 6 | VI-1 | Slc25a25 |
| 3030 | 3 | 4 | 5 | 6 | VI-1 | Slc25a47 |
| 3031 | 3 | 4 | 5 | 6 | VI-1 | Slc26a2 |
| 3032 | 3 | 4 | 5 | 6 | VI-1 | Slc26a3 |
| 3033 | 3 | 4 | 5 | 6 | VI-1 | Slc27a5 |
| 3034 | 3 | 4 | 5 | 6 | VI-1 | Slc28a2 |
| 3035 | 3 | 4 | 5 | 6 | VI-1 | Slc2a6 |
| 3036 | 3 | 4 | 5 | 6 | VI-1 | Slc30a2 |
| 3037 | 3 | 4 | 5 | 6 | VI-1 | Slc30a3 |
| 3038 | 3 | 4 | 5 | 6 | VI-1 | Slc34a1 |
| 3039 | 3 | 4 | 5 | 6 | VI-1 | Slc34a2 |
| 3040 | 3 | 4 | 5 | 6 | VI-1 | Slc35g1 |
| 3041 | 3 | 4 | 5 | 6 | VI-1 | Slc36a2 |
| 3042 | 3 | 4 | 5 | 6 | VI-1 | Slc36a4 |
| 3043 | 3 | 4 | 5 | 6 | VI-1 | Slc37a1 |
| 3044 | 3 | 4 | 5 | 6 | VI-1 | Slc37a4 |
| 3045 | 3 | 4 | 5 | 6 | VI-1 | Slc38a4 |
| 3046 | 3 | 4 | 5 | 6 | VI-1 | Slc39a5 |
| 3047 | 3 | 4 | 5 | 6 | VI-1 | Slc45a3 |
| 3048 | 3 | 4 | 5 | 6 | VI-1 | Slc4a8 |
| 3049 | 3 | 4 | 5 | 6 | VI-1 | Slc6a14 |
| 3050 | 3 | 4 | 5 | 6 | VI-1 | Slc6a5 |
| 3051 | 3 | 4 | 5 | 6 | VI-1 | Slc6a9 |
| 3052 | 3 | 4 | 5 | 6 | VI-1 | Slc7a1 |
| 3053 | 3 | 4 | 5 | 6 | VI-1 | Slc7a15 |
| 3054 | 3 | 4 | 5 | 6 | VI-1 | Slc7a4 |
| 3055 | 3 | 4 | 5 | 6 | VI-1 | Slc7a5 |
| 3056 | 3 | 4 | 5 | 6 | VI-1 | Slc7a9 |
| 3057 | 3 | 4 | 5 | 6 | VI-1 | Slc9a3 |
| 3058 | 3 | 4 | 5 | 6 | VI-1 | Slco4c1 |
| 3059 | 3 | 4 | 5 | 6 | VI-1 | Slfn1 |
| 3060 | 3 | 4 | 5 | 6 | VI-1 | Slfn2 |
| 3061 | 3 | 4 | 5 | 6 | VI-1 | Slfn4 |
| 3062 | 3 | 4 | 5 | 6 | VI-1 | Slfn9 |
| 3063 | 3 | 4 | 5 | 6 | VI-1 | Slitrk3 |
| 3064 | 3 | 4 | 5 | 6 | VI-1 | Sln |
| 3065 | 3 | 4 | 5 | 6 | VI-1 | Six4ip |
| 3066 | 3 | 4 | 5 | 6 | VI-1 | Smad6 |
| 3067 | 3 | 4 | 5 | 6 | VI-1 | Smcp |
| 3068 | 3 | 4 | 5 | 6 | VI-1 | Smim11 |
| 3069 | 3 | 4 | 5 | 6 | VI-1 | Smim20 |
| 3070 | 3 | 4 | 5 | 6 | VI-1 | Smim22 |

Fig. 36 - 17

| | | | | | | | |
|---|---|---|---|---|---|---|---|
| 3071 | 3 | 4 | 5 | 6 | | VI-1 | Smim24 |
| 3072 | 3 | 4 | 5 | 6 | | VI-1 | Smim9 |
| 3073 | 3 | 4 | 5 | 6 | | VI-1 | Smpdl3a |
| 3074 | 3 | 4 | 5 | 6 | | VI-1 | Smpdl3b |
| 3075 | 3 | 4 | 5 | 6 | | VI-1 | Smtnl2 |
| 3076 | 3 | 4 | 5 | 6 | | VI-1 | Snai3 |
| 3077 | 3 | 4 | 5 | 6 | | VI-1 | Snapc3 |
| 3078 | 3 | 4 | 5 | 6 | | VI-1 | Snora24 |
| 3079 | 3 | 4 | 5 | 6 | | VI-1 | Snph |
| 3080 | 3 | 4 | 5 | 6 | | VI-1 | Snrnp35 |
| 3081 | 3 | 4 | 5 | 6 | | VI-1 | Sntb2 |
| 3082 | 3 | 4 | 5 | 6 | | VI-1 | Sntn |
| 3083 | 3 | 4 | 5 | 6 | | VI-1 | Snx29 |
| 3084 | 3 | 4 | 5 | 6 | | VI-1 | Soat2 |
| 3085 | 3 | 4 | 5 | 6 | | VI-1 | Socs3 |
| 3086 | 3 | 4 | 5 | 6 | | VI-1 | Socs4 |
| 3087 | 3 | 4 | 5 | 6 | | VI-1 | Sod1 |
| 3088 | 3 | 4 | 5 | 6 | | VI-1 | Soga1 |
| 3089 | 3 | 4 | 5 | 6 | | VI-1 | Sorcs2 |
| 3090 | 3 | 4 | 5 | 6 | | VI-1 | Sorl1 |
| 3091 | 3 | 4 | 5 | 6 | | VI-1 | Sost |
| 3092 | 3 | 4 | 5 | 6 | | VI-1 | Sox4 |
| 3093 | 3 | 4 | 5 | 6 | | VI-1 | Sox9 |
| 3094 | 3 | 4 | 5 | 6 | | VI-1 | Spa17 |
| 3095 | 3 | 4 | 5 | 6 | | VI-1 | Spaca4 |
| 3096 | 3 | 4 | 5 | 6 | | VI-1 | Spag16 |
| 3097 | 3 | 4 | 5 | 6 | | VI-1 | Spag8 |
| 3098 | 3 | 4 | 5 | 6 | | VI-1 | Spata24 |
| 3099 | 3 | 4 | 5 | 6 | | VI-1 | Spata3 |
| 3100 | 3 | 4 | 5 | 6 | | VI-1 | Spata33 |
| 3101 | 3 | 4 | 5 | 6 | | VI-1 | Spata5l1 |
| 3102 | 3 | 4 | 5 | 6 | | VI-1 | Spen |
| 3103 | 3 | 4 | 5 | 6 | | VI-1 | Spink1 |
| 3104 | 3 | 4 | 5 | 6 | | VI-1 | Spink3 |
| 3105 | 3 | 4 | 5 | 6 | | VI-1 | Spink4 |
| 3106 | 3 | 4 | 5 | 6 | | VI-1 | Spint2 |
| 3107 | 3 | 4 | 5 | 6 | | VI-1 | Spint5 |
| 3108 | 3 | 4 | 5 | 6 | | VI-1 | Spock2 |
| 3109 | 3 | 4 | 5 | 6 | | VI-1 | Spon2 |
| 3110 | 3 | 4 | 5 | 6 | | VI-1 | Spp1 |
| 3111 | 3 | 4 | 5 | 6 | | VI-1 | Sprtn |
| 3112 | 3 | 4 | 5 | 6 | | VI-1 | Srp19 |
| 3113 | 3 | 4 | 5 | 6 | | VI-1 | Srrm2 |
| 3114 | 3 | 4 | 5 | 6 | | VI-1 | Ss18l1 |
| 3115 | 3 | 4 | 5 | 6 | | VI-1 | Ssh1 |
| 3116 | 3 | 4 | 5 | 6 | | VI-1 | Sstr4 |
| 3117 | 3 | 4 | 5 | 6 | | VI-1 | St14 |
| 3118 | 3 | 4 | 5 | 6 | | VI-1 | St6galnac6 |
| 3119 | 3 | 4 | 5 | 6 | | VI-1 | Stard10 |
| 3120 | 3 | 4 | 5 | 6 | | VI-1 | Stard4 |
| 3121 | 3 | 4 | 5 | 6 | | VI-1 | Stat1 |
| 3122 | 3 | 4 | 5 | 6 | | VI-1 | Stbd1 |
| 3123 | 3 | 4 | 5 | 6 | | VI-1 | Stc1 |
| 3124 | 3 | 4 | 5 | 6 | | VI-1 | Steap4 |
| 3125 | 3 | 4 | 5 | 6 | | VI-1 | Stfa1 |
| 3126 | 3 | 4 | 5 | 6 | | VI-1 | Stfa2 |
| 3127 | 3 | 4 | 5 | 6 | | VI-1 | Stfa2l1 |
| 3128 | 3 | 4 | 5 | 6 | | VI-1 | Stk32c |
| 3129 | 3 | 4 | 5 | 6 | | VI-1 | Stmn1 |
| 3130 | 3 | 4 | 5 | 6 | | VI-1 | Ston1 |
| 3131 | 3 | 4 | 5 | 6 | | VI-1 | Strn |
| 3132 | 3 | 4 | 5 | 6 | | VI-1 | Stx1b |
| 3133 | 3 | 4 | 5 | 6 | | VI-1 | Suox |
| 3134 | 3 | 4 | 5 | 6 | | VI-1 | Susd3 |
| 3135 | 3 | 4 | 5 | 6 | | VI-1 | Sval1 |
| 3136 | 3 | 4 | 5 | 6 | | VI-1 | Syce2 |
| 3137 | 3 | 4 | 5 | 6 | | VI-1 | Sycp3 |
| 3138 | 3 | 4 | 5 | 6 | | VI-1 | Syne2 |
| 3139 | 3 | 4 | 5 | 6 | | VI-1 | Syne3 |
| 3140 | 3 | 4 | 5 | 6 | | VI-1 | Syngap1 |
| 3141 | 3 | 4 | 5 | 6 | | VI-1 | Sypl2 |
| 3142 | 3 | 4 | 5 | 6 | | VI-1 | Syt10 |
| 3143 | 3 | 4 | 5 | 6 | | VI-1 | Syt14 |
| 3144 | 3 | 4 | 5 | 6 | | VI-1 | Syt2 |
| 3145 | 3 | 4 | 5 | 6 | | VI-1 | Taf6l |
| 3146 | 3 | 4 | 5 | 6 | | VI-1 | Tap1 |
| 3147 | 3 | 4 | 5 | 6 | | VI-1 | Tbc1d8 |
| 3148 | 3 | 4 | 5 | 6 | | VI-1 | Tbc1d9 |
| 3149 | 3 | 4 | 5 | 6 | | VI-1 | Tbck |
| 3150 | 3 | 4 | 5 | 6 | | VI-1 | Tbl1x |
| 3151 | 3 | 4 | 5 | 6 | | VI-1 | Tbx2 |
| 3152 | 3 | 4 | 5 | 6 | | VI-1 | Tcea2 |
| 3153 | 3 | 4 | 5 | 6 | | VI-1 | Tceal5 |
| 3154 | 3 | 4 | 5 | 6 | | VI-1 | Tcf19 |
| 3155 | 3 | 4 | 5 | 6 | | VI-1 | Tchh |
| 3156 | 3 | 4 | 5 | 6 | | VI-1 | Tcn2 |
| 3157 | 3 | 4 | 5 | 6 | | VI-1 | Tcp11l1 |
| 3158 | 3 | 4 | 5 | 6 | | VI-1 | Tcte1 |
| 3159 | 3 | 4 | 5 | 6 | | VI-1 | Tctex1d2 |
| 3160 | 3 | 4 | 5 | 6 | | VI-1 | Tctex1d4 |
| 3161 | 3 | 4 | 5 | 6 | | VI-1 | Tdg |
| 3162 | 3 | 4 | 5 | 6 | | VI-1 | Tdh |
| 3163 | 3 | 4 | 5 | 6 | | VI-1 | Tdo2 |
| 3164 | 3 | 4 | 5 | 6 | | VI-1 | Tead4 |
| 3165 | 3 | 4 | 5 | 6 | | VI-1 | Tekt1 |
| 3166 | 3 | 4 | 5 | 6 | | VI-1 | Tenm1 |
| 3167 | 3 | 4 | 5 | 6 | | VI-1 | Tenm4 |
| 3168 | 3 | 4 | 5 | 6 | | VI-1 | Terc |
| 3169 | 3 | 4 | 5 | 6 | | VI-1 | Tesc |
| 3170 | 3 | 4 | 5 | 6 | | VI-1 | Tescl |
| 3171 | 3 | 4 | 5 | 6 | | VI-1 | Tex9 |
| 3172 | 3 | 4 | 5 | 6 | | VI-1 | Tfap2b |
| 3173 | 3 | 4 | 5 | 6 | | VI-1 | Tfcp2l1 |
| 3174 | 3 | 4 | 5 | 6 | | VI-1 | Tfrc |
| 3175 | 3 | 4 | 5 | 6 | | VI-1 | Tgfbi |
| 3176 | 3 | 4 | 5 | 6 | | VI-1 | Tgm1 |
| 3177 | 3 | 4 | 5 | 6 | | VI-1 | Them6 |
| 3178 | 3 | 4 | 5 | 6 | | VI-1 | Themis2 |
| 3179 | 3 | 4 | 5 | 6 | | VI-1 | Timd4 |
| 3180 | 3 | 4 | 5 | 6 | | VI-1 | Timm9 |
| 3181 | 3 | 4 | 5 | 6 | | VI-1 | Timp1 |
| 3182 | 3 | 4 | 5 | 6 | | VI-1 | Timp2 |
| 3183 | 3 | 4 | 5 | 6 | | VI-1 | Tinag |
| 3184 | 3 | 4 | 5 | 6 | | VI-1 | Tle2 |
| 3185 | 3 | 4 | 5 | 6 | | VI-1 | Tlr12 |
| 3186 | 3 | 4 | 5 | 6 | | VI-1 | Tlr13 |
| 3187 | 3 | 4 | 5 | 6 | | VI-1 | Tlr2 |
| 3188 | 3 | 4 | 5 | 6 | | VI-1 | Tlr8 |
| 3189 | 3 | 4 | 5 | 6 | | VI-1 | Tlr9 |
| 3190 | 3 | 4 | 5 | 6 | | VI-1 | Tm4sf4 |
| 3191 | 3 | 4 | 5 | 6 | | VI-1 | Tm6sf2 |
| 3192 | 3 | 4 | 5 | 6 | | VI-1 | Tm7sf2 |
| 3193 | 3 | 4 | 5 | 6 | | VI-1 | Tmc4 |
| 3194 | 3 | 4 | 5 | 6 | | VI-1 | Tmc5 |
| 3195 | 3 | 4 | 5 | 6 | | VI-1 | Tmed3 |
| 3196 | 3 | 4 | 5 | 6 | | VI-1 | Tmed6 |
| 3197 | 3 | 4 | 5 | 6 | | VI-1 | Tmem107 |
| 3198 | 3 | 4 | 5 | 6 | | VI-1 | Tmem120a |
| 3199 | 3 | 4 | 5 | 6 | | VI-1 | Tmem132b |
| 3200 | 3 | 4 | 5 | 6 | | VI-1 | Tmem139 |
| 3201 | 3 | 4 | 5 | 6 | | VI-1 | Tmem160 |
| 3202 | 3 | 4 | 5 | 6 | | VI-1 | Tmem180 |
| 3203 | 3 | 4 | 5 | 6 | | VI-1 | Tmem182 |
| 3204 | 3 | 4 | 5 | 6 | | VI-1 | Tmem184a |
| 3205 | 3 | 4 | 5 | 6 | | VI-1 | Tmem196 |
| 3206 | 3 | 4 | 5 | 6 | | VI-1 | Tmem205 |
| 3207 | 3 | 4 | 5 | 6 | | VI-1 | Tmem212 |
| 3208 | 3 | 4 | 5 | 6 | | VI-1 | Tmem213 |
| 3209 | 3 | 4 | 5 | 6 | | VI-1 | Tmem221 |
| 3210 | 3 | 4 | 5 | 6 | | VI-1 | Tmem245 |
| 3211 | 3 | 4 | 5 | 6 | | VI-1 | Tmem25 |
| 3212 | 3 | 4 | 5 | 6 | | VI-1 | Tmem252 |
| 3213 | 3 | 4 | 5 | 6 | | VI-1 | Tmem253 |
| 3214 | 3 | 4 | 5 | 6 | | VI-1 | Tmem256 |
| 3215 | 3 | 4 | 5 | 6 | | VI-1 | Tmem28 |
| 3216 | 3 | 4 | 5 | 6 | | VI-1 | Tmem30b |
| 3217 | 3 | 4 | 5 | 6 | | VI-1 | Tmem45b |
| 3218 | 3 | 4 | 5 | 6 | | VI-1 | Tmem51 |
| 3219 | 3 | 4 | 5 | 6 | | VI-1 | Tmem52 |
| 3220 | 3 | 4 | 5 | 6 | | VI-1 | Tmem53 |
| 3221 | 3 | 4 | 5 | 6 | | VI-1 | Tmem72 |
| 3222 | 3 | 4 | 5 | 6 | | VI-1 | Tmem74 |
| 3223 | 3 | 4 | 5 | 6 | | VI-1 | Tmsb15b1 |
| 3224 | 3 | 4 | 5 | 6 | | VI-1 | Tmsb15b2 |
| 3225 | 3 | 4 | 5 | 6 | | VI-1 | Tmsb15l |
| 3226 | 3 | 4 | 5 | 6 | | VI-1 | Tnfaip2 |
| 3227 | 3 | 4 | 5 | 6 | | VI-1 | Tnfrsf14 |
| 3228 | 3 | 4 | 5 | 6 | | VI-1 | Tnfrsf25 |
| 3229 | 3 | 4 | 5 | 6 | | VI-1 | Tnfsf10 |
| 3230 | 3 | 4 | 5 | 6 | | VI-1 | Tnfsf14 |
| 3231 | 3 | 4 | 5 | 6 | | VI-1 | Tnk1 |
| 3232 | 3 | 4 | 5 | 6 | | VI-1 | Tnks |
| 3233 | 3 | 4 | 5 | 6 | | VI-1 | Tnnt3 |
| 3234 | 3 | 4 | 5 | 6 | | VI-1 | Tnp2 |
| 3235 | 3 | 4 | 5 | 6 | | VI-1 | Tnpo1 |
| 3236 | 3 | 4 | 5 | 6 | | VI-1 | Tnr |
| 3237 | 3 | 4 | 5 | 6 | | VI-1 | Tnrc18 |
| 3238 | 3 | 4 | 5 | 6 | | VI-1 | Tomt |
| 3239 | 3 | 4 | 5 | 6 | | VI-1 | Toporsos |
| 3240 | 3 | 4 | 5 | 6 | | VI-1 | Tox2 |
| 3241 | 3 | 4 | 5 | 6 | | VI-1 | Tph2 |
| 3242 | 3 | 4 | 5 | 6 | | VI-1 | Tppp3 |
| 3243 | 3 | 4 | 5 | 6 | | VI-1 | Tra2b |
| 3244 | 3 | 4 | 5 | 6 | | VI-1 | Tradd |
| 3245 | 3 | 4 | 5 | 6 | | VI-1 | Trank1 |
| 3246 | 3 | 4 | 5 | 6 | | VI-1 | Trem2 |
| 3247 | 3 | 4 | 5 | 6 | | VI-1 | Trex1 |
| 3248 | 3 | 4 | 5 | 6 | | VI-1 | Trim30a |
| 3249 | 3 | 4 | 5 | 6 | | VI-1 | Trim30b |
| 3250 | 3 | 4 | 5 | 6 | | VI-1 | Trim31 |
| 3251 | 3 | 4 | 5 | 6 | | VI-1 | Trim65 |
| 3252 | 3 | 4 | 5 | 6 | | VI-1 | Trim7 |
| 3253 | 3 | 4 | 5 | 6 | | VI-1 | Trip11 |
| 3254 | 3 | 4 | 5 | 6 | | VI-1 | Trmt61b |
| 3255 | 3 | 4 | 5 | 6 | | VI-1 | Trp53i11 |
| 3256 | 3 | 4 | 5 | 6 | | VI-1 | Trpc5 |
| 3257 | 3 | 4 | 5 | 6 | | VI-1 | Trpm3 |
| 3258 | 3 | 4 | 5 | 6 | | VI-1 | Trpv3 |
| 3259 | 3 | 4 | 5 | 6 | | VI-1 | Tsacc |
| 3260 | 3 | 4 | 5 | 6 | | VI-1 | Tsfm |
| 3261 | 3 | 4 | 5 | 6 | | VI-1 | Tspan1 |
| 3262 | 3 | 4 | 5 | 6 | | VI-1 | Tspo |

Fig. 36 - 18

| | | | | | | | |
|---|---|---|---|---|---|---|---|
| 3263 | 3 | 4 | 5 | 6 | | VI-1 | Tspyl1 |
| 3264 | 3 | 4 | 5 | 6 | | VI-1 | Tsr3 |
| 3265 | 3 | 4 | 5 | 6 | | VI-1 | Ttc16 |
| 3266 | 3 | 4 | 5 | 6 | | VI-1 | Ttc25 |
| 3267 | 3 | 4 | 5 | 6 | | VI-1 | Ttc36 |
| 3268 | 3 | 4 | 5 | 6 | | VI-1 | Ttc37 |
| 3269 | 3 | 4 | 5 | 6 | | VI-1 | Ttll3 |
| 3270 | 3 | 4 | 5 | 6 | | VI-1 | Ttll4 |
| 3271 | 3 | 4 | 5 | 6 | | VI-1 | Tubb2a-ps2 |
| 3272 | 3 | 4 | 5 | 6 | | VI-1 | Ubald2 |
| 3273 | 3 | 4 | 5 | 6 | | VI-1 | Ubap1l |
| 3274 | 3 | 4 | 5 | 6 | | VI-1 | Ubd |
| 3275 | 3 | 4 | 5 | 6 | | VI-1 | Ube2l6 |
| 3276 | 3 | 4 | 5 | 6 | | VI-1 | Ube3a |
| 3277 | 3 | 4 | 5 | 6 | | VI-1 | Ubxn10 |
| 3278 | 3 | 4 | 5 | 6 | | VI-1 | Ubxn2b |
| 3279 | 3 | 4 | 5 | 6 | | VI-1 | Ucp3 |
| 3280 | 3 | 4 | 5 | 6 | | VI-1 | Ugdh |
| 3281 | 3 | 4 | 5 | 6 | | VI-1 | Ugt3a2 |
| 3282 | 3 | 4 | 5 | 6 | | VI-1 | Ulbp1 |
| 3283 | 3 | 4 | 5 | 6 | | VI-1 | Umod |
| 3284 | 3 | 4 | 5 | 6 | | VI-1 | Unc5cl |
| 3285 | 3 | 4 | 5 | 6 | | VI-1 | Unc93b1 |
| 3286 | 3 | 4 | 5 | 6 | | VI-1 | Upk1a |
| 3287 | 3 | 4 | 5 | 6 | | VI-1 | Uprt |
| 3288 | 3 | 4 | 5 | 6 | | VI-1 | Uqcc2 |
| 3289 | 3 | 4 | 5 | 6 | | VI-1 | Uqcr11 |
| 3290 | 3 | 4 | 5 | 6 | | VI-1 | Uqcrb |
| 3291 | 3 | 4 | 5 | 6 | | VI-1 | Usp18 |
| 3292 | 3 | 4 | 5 | 6 | | VI-1 | Usp31 |
| 3293 | 3 | 4 | 5 | 6 | | VI-1 | Usp34 |
| 3294 | 3 | 4 | 5 | 6 | | VI-1 | Usp53 |
| 3295 | 3 | 4 | 5 | 6 | | VI-1 | Utf1 |
| 3296 | 3 | 4 | 5 | 6 | | VI-1 | Utp14b |
| 3297 | 3 | 4 | 5 | 6 | | VI-1 | Vamp8 |
| 3298 | 3 | 4 | 5 | 6 | | VI-1 | Vangl2 |
| 3299 | 3 | 4 | 5 | 6 | | VI-1 | Vax2 |
| 3300 | 3 | 4 | 5 | 6 | | VI-1 | Vbp1 |
| 3301 | 3 | 4 | 5 | 6 | | VI-1 | Vgll4 |
| 3302 | 3 | 4 | 5 | 6 | | VI-1 | Vil1 |
| 3303 | 3 | 4 | 5 | 6 | | VI-1 | Vim |
| 3304 | 3 | 4 | 5 | 6 | | VI-1 | Vkorc1 |
| 3305 | 3 | 4 | 5 | 6 | | VI-1 | Vps13c |
| 3306 | 3 | 4 | 5 | 6 | | VI-1 | Vsig8 |
| 3307 | 3 | 4 | 5 | 6 | | VI-1 | Vstm2b |
| 3308 | 3 | 4 | 5 | 6 | | VI-1 | Vwa2 |
| 3309 | 3 | 4 | 5 | 6 | | VI-1 | Wapal |
| 3310 | 3 | 4 | 5 | 6 | | VI-1 | Wasf3 |
| 3311 | 3 | 4 | 5 | 6 | | VI-1 | Wdfy2 |
| 3312 | 3 | 4 | 5 | 6 | | VI-1 | Wdfy4 |
| 3313 | 3 | 4 | 5 | 6 | | VI-1 | Wdr52 |
| 3314 | 3 | 4 | 5 | 6 | | VI-1 | Wdr78 |
| 3315 | 3 | 4 | 5 | 6 | | VI-1 | Wdr83os |
| 3316 | 3 | 4 | 5 | 6 | | VI-1 | Wdr89 |
| 3317 | 3 | 4 | 5 | 6 | | VI-1 | Wfdc16 |
| 3318 | 3 | 4 | 5 | 6 | | VI-1 | Wfdc17 |
| 3319 | 3 | 4 | 5 | 6 | | VI-1 | Wfdc18 |
| 3320 | 3 | 4 | 5 | 6 | | VI-1 | Wif1 |
| 3321 | 3 | 4 | 5 | 6 | | VI-1 | Wnk2 |
| 3322 | 3 | 4 | 5 | 6 | | VI-1 | Wnk4 |
| 3323 | 3 | 4 | 5 | 6 | | VI-1 | Wnt2b |
| 3324 | 3 | 4 | 5 | 6 | | VI-1 | Wnt5b |
| 3325 | 3 | 4 | 5 | 6 | | VI-1 | Wwc2 |
| 3326 | 3 | 4 | 5 | 6 | | VI-1 | Xcl1 |
| 3327 | 3 | 4 | 5 | 6 | | VI-1 | Xkr4 |
| 3328 | 3 | 4 | 5 | 6 | | VI-1 | Xkr7 |
| 3329 | 3 | 4 | 5 | 6 | | VI-1 | Xlr3a |
| 3330 | 3 | 4 | 5 | 6 | | VI-1 | Xlr3b |
| 3331 | 3 | 4 | 5 | 6 | | VI-1 | Xpnpep3 |
| 3332 | 3 | 4 | 5 | 6 | | VI-1 | Xpo4 |
| 3333 | 3 | 4 | 5 | 6 | | VI-1 | Xrn1 |
| 3334 | 3 | 4 | 5 | 6 | | VI-1 | Xylb |
| 3335 | 3 | 4 | 5 | 6 | | VI-1 | Xylt1 |
| 3336 | 3 | 4 | 5 | 6 | | VI-1 | Ylpm1 |
| 3337 | 3 | 4 | 5 | 6 | | VI-1 | Yod1 |
| 3338 | 3 | 4 | 5 | 6 | | VI-1 | Zan |
| 3339 | 3 | 4 | 5 | 6 | | VI-1 | Zap70 |
| 3340 | 3 | 4 | 5 | 6 | | VI-1 | Zbtb16 |
| 3341 | 3 | 4 | 5 | 6 | | VI-1 | Zbtb32 |
| 3342 | 3 | 4 | 5 | 6 | | VI-1 | Zbtb37 |
| 3343 | 3 | 4 | 5 | 6 | | VI-1 | Zbtb38 |
| 3344 | 3 | 4 | 5 | 6 | | VI-1 | Zc2hc1c |
| 3345 | 3 | 4 | 5 | 6 | | VI-1 | Zc3h12b |
| 3346 | 3 | 4 | 5 | 6 | | VI-1 | Zc3h12c |
| 3347 | 3 | 4 | 5 | 6 | | VI-1 | Zdhhc23 |
| 3348 | 3 | 4 | 5 | 6 | | VI-1 | Zdhhc4 |
| 3349 | 3 | 4 | 5 | 6 | | VI-1 | Zfl2 |
| 3350 | 3 | 4 | 5 | 6 | | VI-1 | Zfa-ps |
| 3351 | 3 | 4 | 5 | 6 | | VI-1 | Zfhx3 |
| 3352 | 3 | 4 | 5 | 6 | | VI-1 | Zfhx4 |
| 3353 | 3 | 4 | 5 | 6 | | VI-1 | Zfp109 |
| 3354 | 3 | 4 | 5 | 6 | | VI-1 | Zfp13 |
| 3355 | 3 | 4 | 5 | 6 | | VI-1 | Zfp169 |
| 3356 | 3 | 4 | 5 | 6 | | VI-1 | Zfp185 |
| 3357 | 3 | 4 | 5 | 6 | | VI-1 | Zfp324 |
| 3358 | 3 | 4 | 5 | 6 | | VI-1 | Zfp36l1 |

| | | | | | | | |
|---|---|---|---|---|---|---|---|
| 3359 | 3 | 4 | 5 | 6 | | VI-1 | Zfp382 |
| 3360 | 3 | 4 | 5 | 6 | | VI-1 | Zfp398 |
| 3361 | 3 | 4 | 5 | 6 | | VI-1 | Zfp407 |
| 3362 | 3 | 4 | 5 | 6 | | VI-1 | Zfp442 |
| 3363 | 3 | 4 | 5 | 6 | | VI-1 | Zfp526 |
| 3364 | 3 | 4 | 5 | 6 | | VI-1 | Zfp536 |
| 3365 | 3 | 4 | 5 | 6 | | VI-1 | Zfp551 |
| 3366 | 3 | 4 | 5 | 6 | | VI-1 | Zfp618 |
| 3367 | 3 | 4 | 5 | 6 | | VI-1 | Zfp652 |
| 3368 | 3 | 4 | 5 | 6 | | VI-1 | Zfp704 |
| 3369 | 3 | 4 | 5 | 6 | | VI-1 | Zfp750 |
| 3370 | 3 | 4 | 5 | 6 | | VI-1 | Zfp931 |
| 3371 | 3 | 4 | 5 | 6 | | VI-1 | Zfp933 |
| 3372 | 3 | 4 | 5 | 6 | | VI-1 | Zhx3 |
| 3373 | 3 | 4 | 5 | 6 | | VI-1 | Zim1 |
| 3374 | 3 | 4 | 5 | 6 | | VI-1 | Zkscan16 |
| 3375 | 3 | 4 | 5 | 6 | | VI-1 | Zkscan2 |
| 3376 | 3 | 4 | 5 | 6 | | VI-1 | Zkscan7 |
| 3377 | 3 | 4 | 5 | 6 | | VI-1 | Zmat1 |
| 3378 | 3 | 4 | 5 | 6 | | VI-1 | Zmynd10 |
| 3379 | 3 | 4 | 5 | | | V-2 | 0610007P14Rik |
| 3380 | 3 | 4 | 5 | | | V-2 | 0610043K17Rik |
| 3381 | 3 | 4 | 5 | | | V-2 | 1110001J03Rik |
| 3382 | 3 | 4 | 5 | | | V-2 | 1110004E09Rik |
| 3383 | 3 | 4 | 5 | | | V-2 | 1110004F10Rik |
| 3384 | 3 | 4 | 5 | | | V-2 | 1110008F13Rik |
| 3385 | 3 | 4 | 5 | | | V-2 | 1110008P14Rik |
| 3386 | 3 | 4 | 5 | | | V-2 | 1110028F11Rik |
| 3387 | 3 | 4 | 5 | | | V-2 | 1110038B12Rik |
| 3388 | 3 | 4 | 5 | | | V-2 | 1110054M08Rik |
| 3389 | 3 | 4 | 5 | | | V-2 | 1110058L19Rik |
| 3390 | 3 | 4 | 5 | | | V-2 | 1110059E24Rik |
| 3391 | 3 | 4 | 5 | | | V-2 | 1110059G10Rik |
| 3392 | 3 | 4 | 5 | | | V-2 | 1500009L16Rik |
| 3393 | 3 | 4 | 5 | | | V-2 | 1500011K16Rik |
| 3394 | 3 | 4 | 5 | | | V-2 | 1500015A07Rik |
| 3395 | 3 | 4 | 5 | | | V-2 | 1700001L05Rik |
| 3396 | 3 | 4 | 5 | | | V-2 | 1700003C15Rik |
| 3397 | 3 | 4 | 5 | | | V-2 | 1700003F12Rik |
| 3398 | 3 | 4 | 5 | | | V-2 | 1700008O03Rik |
| 3399 | 3 | 4 | 5 | | | V-2 | 1700020L24Rik |
| 3400 | 3 | 4 | 5 | | | V-2 | 1700021F05Rik |
| 3401 | 3 | 4 | 5 | | | V-2 | 1700022A22Rik |
| 3402 | 3 | 4 | 5 | | | V-2 | 1700028J19Rik |
| 3403 | 3 | 4 | 5 | | | V-2 | 1700030N03Rik |
| 3404 | 3 | 4 | 5 | | | V-2 | 1700031F05Rik |
| 3405 | 3 | 4 | 5 | | | V-2 | 1700034H15Rik |
| 3406 | 3 | 4 | 5 | | | V-2 | 1700040L02Rik |
| 3407 | 3 | 4 | 5 | | | V-2 | 1700044C05Rik |
| 3408 | 3 | 4 | 5 | | | V-2 | 1700048O20Rik |
| 3409 | 3 | 4 | 5 | | | V-2 | 1700052N19Rik |
| 3410 | 3 | 4 | 5 | | | V-2 | 1700054M17Rik |
| 3411 | 3 | 4 | 5 | | | V-2 | 1700065D16Rik |
| 3412 | 3 | 4 | 5 | | | V-2 | 1700066O22Rik |
| 3413 | 3 | 4 | 5 | | | V-2 | 1700092K14Rik |
| 3414 | 3 | 4 | 5 | | | V-2 | 1700096F18Rik |
| 3415 | 3 | 4 | 5 | | | V-2 | 1700123K08Rik |
| 3416 | 3 | 4 | 5 | | | V-2 | 1810008I18Rik |
| 3417 | 3 | 4 | 5 | | | V-2 | 1810010H24Rik |
| 3418 | 3 | 4 | 5 | | | V-2 | 1810011H11Rik |
| 3419 | 3 | 4 | 5 | | | V-2 | 1810013A23Rik |
| 3420 | 3 | 4 | 5 | | | V-2 | 1810021B22Rik |
| 3421 | 3 | 4 | 5 | | | V-2 | 1810024B03Rik |
| 3422 | 3 | 4 | 5 | | | V-2 | 1810037I17Rik |
| 3423 | 3 | 4 | 5 | | | V-2 | 1810062O18Rik |
| 3424 | 3 | 4 | 5 | | | V-2 | 2010010A06Rik |
| 3425 | 3 | 4 | 5 | | | V-2 | 2010107E04Rik |
| 3426 | 3 | 4 | 5 | | | V-2 | 2010111I01Rik |
| 3427 | 3 | 4 | 5 | | | V-2 | 2010320M18Rik |
| 3428 | 3 | 4 | 5 | | | V-2 | 2200002D01Rik |
| 3429 | 3 | 4 | 5 | | | V-2 | 2210011C24Rik |
| 3430 | 3 | 4 | 5 | | | V-2 | 2300005B03Rik |
| 3431 | 3 | 4 | 5 | | | V-2 | 2300009A05Rik |
| 3432 | 3 | 4 | 5 | | | V-2 | 2310002L09Rik |
| 3433 | 3 | 4 | 5 | | | V-2 | 2310009A05Rik |
| 3434 | 3 | 4 | 5 | | | V-2 | 2310015A10Rik |
| 3435 | 3 | 4 | 5 | | | V-2 | 2310033P09Rik |
| 3436 | 3 | 4 | 5 | | | V-2 | 2310039H08Rik |
| 3437 | 3 | 4 | 5 | | | V-2 | 2310061I04Rik |
| 3438 | 3 | 4 | 5 | | | V-2 | 2310061J03Rik |
| 3439 | 3 | 4 | 5 | | | V-2 | 2410004B18Rik |
| 3440 | 3 | 4 | 5 | | | V-2 | 2410137M14Rik |
| 3441 | 3 | 4 | 5 | | | V-2 | 2500004C02Rik |
| 3442 | 3 | 4 | 5 | | | V-2 | 2510009E07Rik |
| 3443 | 3 | 4 | 5 | | | V-2 | 2610002M06Rik |
| 3444 | 3 | 4 | 5 | | | V-2 | 2610044O15Rik8 |
| 3445 | 3 | 4 | 5 | | | V-2 | 2610203C20Rik |
| 3446 | 3 | 4 | 5 | | | V-2 | 2610507B11Rik |
| 3447 | 3 | 4 | 5 | | | V-2 | 2700049A03Rik |
| 3448 | 3 | 4 | 5 | | | V-2 | 2700094K13Rik |
| 3449 | 3 | 4 | 5 | | | V-2 | 2810013P06Rik |
| 3450 | 3 | 4 | 5 | | | V-2 | 2810408A11Rik |
| 3451 | 3 | 4 | 5 | | | V-2 | 2810428I15Rik |
| 3452 | 3 | 4 | 5 | | | V-2 | 2810454H06Rik |
| 3453 | 3 | 4 | 5 | | | V-2 | 2810468N07Rik |
| 3454 | 3 | 4 | 5 | | | V-2 | 2900008C10Rik |

Fig. 36 - 19

| | | | | | | | |
|---|---|---|---|---|---|---|---|
| 3455 | 3 | 4 | 5 | | V-2 | 2900056M20Rik |
| 3456 | 3 | 4 | 5 | | V-2 | 3110043O21Rik |
| 3457 | 3 | 4 | 5 | | V-2 | 3110056K07Rik |
| 3458 | 3 | 4 | 5 | | V-2 | 3110082J24Rik |
| 3459 | 3 | 4 | 5 | | V-2 | 4632415L05Rik |
| 3460 | 3 | 4 | 5 | | V-2 | 4831440E17Rik |
| 3461 | 3 | 4 | 5 | | V-2 | 4833403J15Rik |
| 3462 | 3 | 4 | 5 | | V-2 | 4833412C05Rik |
| 3463 | 3 | 4 | 5 | | V-2 | 4833418N02Rik |
| 3464 | 3 | 4 | 5 | | V-2 | 4833419F23Rik |
| 3465 | 3 | 4 | 5 | | V-2 | 4833420G17Rik |
| 3466 | 3 | 4 | 5 | | V-2 | 4833424O15Rik |
| 3467 | 3 | 4 | 5 | | V-2 | 4833439L19Rik |
| 3468 | 3 | 4 | 5 | | V-2 | 4930401O10Rik |
| 3469 | 3 | 4 | 5 | | V-2 | 4930402F06Rik |
| 3470 | 3 | 4 | 5 | | V-2 | 4930405D11Rik |
| 3471 | 3 | 4 | 5 | | V-2 | 4930405L22Rik |
| 3472 | 3 | 4 | 5 | | V-2 | 4930412C18Rik |
| 3473 | 3 | 4 | 5 | | V-2 | 4930423M02Rik |
| 3474 | 3 | 4 | 5 | | V-2 | 4930430F08Rik |
| 3475 | 3 | 4 | 5 | | V-2 | 4930442J19Rik |
| 3476 | 3 | 4 | 5 | | V-2 | 4930444F02Rik |
| 3477 | 3 | 4 | 5 | | V-2 | 4930447N08Rik |
| 3478 | 3 | 4 | 5 | | V-2 | 4930448J06Rik |
| 3479 | 3 | 4 | 5 | | V-2 | 4930467E23Rik |
| 3480 | 3 | 4 | 5 | | V-2 | 4930486L24Rik |
| 3481 | 3 | 4 | 5 | | V-2 | 4930487D11Rik |
| 3482 | 3 | 4 | 5 | | V-2 | 4930518P08Rik |
| 3483 | 3 | 4 | 5 | | V-2 | 4930529C04Rik |
| 3484 | 3 | 4 | 5 | | V-2 | 4930529M08Rik |
| 3485 | 3 | 4 | 5 | | V-2 | 4930556M19Rik |
| 3486 | 3 | 4 | 5 | | V-2 | 4930570G19Rik |
| 3487 | 3 | 4 | 5 | | V-2 | 4930573O16Rik |
| 3488 | 3 | 4 | 5 | | V-2 | 4930577N17Rik |
| 3489 | 3 | 4 | 5 | | V-2 | 4930578M01Rik |
| 3490 | 3 | 4 | 5 | | V-2 | 4930581F22Rik |
| 3491 | 3 | 4 | 5 | | V-2 | 4930592A05Rik |
| 3492 | 3 | 4 | 5 | | V-2 | 4931430N09Rik |
| 3493 | 3 | 4 | 5 | | V-2 | 4931431C16Rik |
| 3494 | 3 | 4 | 5 | | V-2 | 4932411E22Rik |
| 3495 | 3 | 4 | 5 | | V-2 | 4932413F04Rik |
| 3496 | 3 | 4 | 5 | | V-2 | 4932435O22Rik |
| 3497 | 3 | 4 | 5 | | V-2 | 4933406C10Rik |
| 3498 | 3 | 4 | 5 | | V-2 | 4933411K20Rik |
| 3499 | 3 | 4 | 5 | | V-2 | 4933417E11Rik |
| 3500 | 3 | 4 | 5 | | V-2 | 4933422H20Rik |
| 3501 | 3 | 4 | 5 | | V-2 | 4933438K21Rik |
| 3502 | 3 | 4 | 5 | | V-2 | 4933439C10Rik |
| 3503 | 3 | 4 | 5 | | V-2 | 5033406O09Rik |
| 3504 | 3 | 4 | 5 | | V-2 | 5430405H02Rik |
| 3505 | 3 | 4 | 5 | | V-2 | 5430416O09Rik |
| 3506 | 3 | 4 | 5 | | V-2 | 5430417L22Rik |
| 3507 | 3 | 4 | 5 | | V-2 | 5430427M07Rik |
| 3508 | 3 | 4 | 5 | | V-2 | 5430437J10Rik |
| 3509 | 3 | 4 | 5 | | V-2 | 5730409E04Rik |
| 3510 | 3 | 4 | 5 | | V-2 | 5730480H06Rik |
| 3511 | 3 | 4 | 5 | | V-2 | 5830428M24Rik |
| 3512 | 3 | 4 | 5 | | V-2 | 5930430L01Rik |
| 3513 | 3 | 4 | 5 | | V-2 | 6030443J06Rik |
| 3514 | 3 | 4 | 5 | | V-2 | 6330549D23Rik |
| 3515 | 3 | 4 | 5 | | V-2 | 6430411K18Rik |
| 3516 | 3 | 4 | 5 | | V-2 | 6430503K07Rik |
| 3517 | 3 | 4 | 5 | | V-2 | 6430548M08Rik |
| 3518 | 3 | 4 | 5 | | V-2 | 6820408C15Rik |
| 3519 | 3 | 4 | 5 | | V-2 | 6820431F20Rik |
| 3520 | 3 | 4 | 5 | | V-2 | 7420461P10Rik |
| 3521 | 3 | 4 | 5 | | V-2 | 9130008F23Rik |
| 3522 | 3 | 4 | 5 | | V-2 | 9130019O22Rik |
| 3523 | 3 | 4 | 5 | | V-2 | 9130230L23Rik |
| 3524 | 3 | 4 | 5 | | V-2 | 9230110C19Rik |
| 3525 | 3 | 4 | 5 | | V-2 | 9330159F19Rik |
| 3526 | 3 | 4 | 5 | | V-2 | 9430083A17Rik |
| 3527 | 3 | 4 | 5 | | V-2 | 9430091E24Rik |
| 3528 | 3 | 4 | 5 | | V-2 | 9530077C05Rik |
| 3529 | 3 | 4 | 5 | | V-2 | A230108P19Rik |
| 3530 | 3 | 4 | 5 | | V-2 | A330041J22Rik |
| 3531 | 3 | 4 | 5 | | V-2 | A330076C08Rik |
| 3532 | 3 | 4 | 5 | | V-2 | A430033K04Rik |
| 3533 | 3 | 4 | 5 | | V-2 | A430035B10Rik |
| 3534 | 3 | 4 | 5 | | V-2 | A4galt |
| 3535 | 3 | 4 | 5 | | V-2 | A530053G22Rik |
| 3536 | 3 | 4 | 5 | | V-2 | A630033H20Rik |
| 3537 | 3 | 4 | 5 | | V-2 | A630072M18Rik |
| 3538 | 3 | 4 | 5 | | V-2 | A630077J23Rik |
| 3539 | 3 | 4 | 5 | | V-2 | A730017C20Rik |
| 3540 | 3 | 4 | 5 | | V-2 | A930001A20Rik |
| 3541 | 3 | 4 | 5 | | V-2 | A930003O13Rik |
| 3542 | 3 | 4 | 5 | | V-2 | A930004D18Rik |
| 3543 | 3 | 4 | 5 | | V-2 | A930018P22Rik |
| 3544 | 3 | 4 | 5 | | V-2 | AA543186 |
| 3545 | 3 | 4 | 5 | | V-2 | AA986860 |
| 3546 | 3 | 4 | 5 | | V-2 | AA987161 |
| 3547 | 3 | 4 | 5 | | V-2 | AI427809 |
| 3548 | 3 | 4 | 5 | | V-2 | AI450353 |
| 3549 | 3 | 4 | 5 | | V-2 | AI462493 |
| 3550 | 3 | 4 | 5 | | V-2 | AI504432 |
| 3551 | 3 | 4 | 5 | | V-2 | AI607873 |
| 3552 | 3 | 4 | 5 | | V-2 | AI854703 |
| 3553 | 3 | 4 | 5 | | V-2 | AW549877 |
| 3554 | 3 | 4 | 5 | | V-2 | Aamdc |
| 3555 | 3 | 4 | 5 | | V-2 | Aard |
| 3556 | 3 | 4 | 5 | | V-2 | Aarf |
| 3557 | 3 | 4 | 5 | | V-2 | Abca14 |
| 3558 | 3 | 4 | 5 | | V-2 | Abca5 |
| 3559 | 3 | 4 | 5 | | V-2 | Abca8a |
| 3560 | 3 | 4 | 5 | | V-2 | Abca9 |
| 3561 | 3 | 4 | 5 | | V-2 | Abcd2 |
| 3562 | 3 | 4 | 5 | | V-2 | Abcg1 |
| 3563 | 3 | 4 | 5 | | V-2 | Abhd11 |
| 3564 | 3 | 4 | 5 | | V-2 | Abhd12b |
| 3565 | 3 | 4 | 5 | | V-2 | Abhd14a |
| 3566 | 3 | 4 | 5 | | V-2 | Abhd17a |
| 3567 | 3 | 4 | 5 | | V-2 | Abhd4 |
| 3568 | 3 | 4 | 5 | | V-2 | Abhd6 |
| 3569 | 3 | 4 | 5 | | V-2 | Abi3 |
| 3570 | 3 | 4 | 5 | | V-2 | Ablim1 |
| 3571 | 3 | 4 | 5 | | V-2 | Abtb1 |
| 3572 | 3 | 4 | 5 | | V-2 | Acad12 |
| 3573 | 3 | 4 | 5 | | V-2 | Acadl |
| 3574 | 3 | 4 | 5 | | V-2 | Acap2 |
| 3575 | 3 | 4 | 5 | | V-2 | Acbd4 |
| 3576 | 3 | 4 | 5 | | V-2 | Accs |
| 3577 | 3 | 4 | 5 | | V-2 | Acin1 |
| 3578 | 3 | 4 | 5 | | V-2 | Ackr2 |
| 3579 | 3 | 4 | 5 | | V-2 | Acot10 |
| 3580 | 3 | 4 | 5 | | V-2 | Acot3 |
| 3581 | 3 | 4 | 5 | | V-2 | Acot4 |
| 3582 | 3 | 4 | 5 | | V-2 | Acox2 |
| 3583 | 3 | 4 | 5 | | V-2 | Acr |
| 3584 | 3 | 4 | 5 | | V-2 | Acsl4 |
| 3585 | 3 | 4 | 5 | | V-2 | Actl6b |
| 3586 | 3 | 4 | 5 | | V-2 | Actr6 |
| 3587 | 3 | 4 | 5 | | V-2 | Ada |
| 3588 | 3 | 4 | 5 | | V-2 | Adam33 |
| 3589 | 3 | 4 | 5 | | V-2 | Adarb1 |
| 3590 | 3 | 4 | 5 | | V-2 | Adck5 |
| 3591 | 3 | 4 | 5 | | V-2 | Adcy6 |
| 3592 | 3 | 4 | 5 | | V-2 | Adcy9 |
| 3593 | 3 | 4 | 5 | | V-2 | Adipor1 |
| 3594 | 3 | 4 | 5 | | V-2 | Adm2 |
| 3595 | 3 | 4 | 5 | | V-2 | Adprm |
| 3596 | 3 | 4 | 5 | | V-2 | Adra1d |
| 3597 | 3 | 4 | 5 | | V-2 | Adra2a |
| 3598 | 3 | 4 | 5 | | V-2 | Adrbk1 |
| 3599 | 3 | 4 | 5 | | V-2 | Aes |
| 3600 | 3 | 4 | 5 | | V-2 | Afm |
| 3601 | 3 | 4 | 5 | | V-2 | Agk |
| 3602 | 3 | 4 | 5 | | V-2 | Ahsa1 |
| 3603 | 3 | 4 | 5 | | V-2 | Ahsa2 |
| 3604 | 3 | 4 | 5 | | V-2 | Ak3 |
| 3605 | 3 | 4 | 5 | | V-2 | Akap2 |
| 3606 | 3 | 4 | 5 | | V-2 | Akr1b7 |
| 3607 | 3 | 4 | 5 | | V-2 | Akr1e1 |
| 3608 | 3 | 4 | 5 | | V-2 | Akt2 |
| 3609 | 3 | 4 | 5 | | V-2 | Alas2 |
| 3610 | 3 | 4 | 5 | | V-2 | Aldh1a1 |
| 3611 | 3 | 4 | 5 | | V-2 | Aldh1a2 |
| 3612 | 3 | 4 | 5 | | V-2 | Aldh1a3 |
| 3613 | 3 | 4 | 5 | | V-2 | Aldh2 |
| 3614 | 3 | 4 | 5 | | V-2 | Aldh6a1 |
| 3615 | 3 | 4 | 5 | | V-2 | Aldh7a1 |
| 3616 | 3 | 4 | 5 | | V-2 | Aldoart1 |
| 3617 | 3 | 4 | 5 | | V-2 | Alg5 |
| 3618 | 3 | 4 | 5 | | V-2 | Alkbh3 |
| 3619 | 3 | 4 | 5 | | V-2 | Alkbh5 |
| 3620 | 3 | 4 | 5 | | V-2 | Alkbh6 |
| 3621 | 3 | 4 | 5 | | V-2 | Alpk2 |
| 3622 | 3 | 4 | 5 | | V-2 | Als2cl |
| 3623 | 3 | 4 | 5 | | V-2 | Als2cr12 |
| 3624 | 3 | 4 | 5 | | V-2 | Amacr |
| 3625 | 3 | 4 | 5 | | V-2 | Amica1 |
| 3626 | 3 | 4 | 5 | | V-2 | Amigo2 |
| 3627 | 3 | 4 | 5 | | V-2 | Amph |
| 3628 | 3 | 4 | 5 | | V-2 | Anapc13 |
| 3629 | 3 | 4 | 5 | | V-2 | Anapc15 |
| 3630 | 3 | 4 | 5 | | V-2 | Angpt1 |
| 3631 | 3 | 4 | 5 | | V-2 | Angptl7 |
| 3632 | 3 | 4 | 5 | | V-2 | Ankar |
| 3633 | 3 | 4 | 5 | | V-2 | Ankmy2 |
| 3634 | 3 | 4 | 5 | | V-2 | Ankrd28 |
| 3635 | 3 | 4 | 5 | | V-2 | Ankrd29 |
| 3636 | 3 | 4 | 5 | | V-2 | Ankrd35 |
| 3637 | 3 | 4 | 5 | | V-2 | Ankzf1 |
| 3638 | 3 | 4 | 5 | | V-2 | Ano2 |
| 3639 | 3 | 4 | 5 | | V-2 | Anp32b |
| 3640 | 3 | 4 | 5 | | V-2 | Anp32e |
| 3641 | 3 | 4 | 5 | | V-2 | Antxr1 |
| 3642 | 3 | 4 | 5 | | V-2 | Anxa3 |
| 3643 | 3 | 4 | 5 | | V-2 | Anxa5 |
| 3644 | 3 | 4 | 5 | | V-2 | Ap5s1 |
| 3645 | 3 | 4 | 5 | | V-2 | Apcdd1 |
| 3646 | 3 | 4 | 5 | | V-2 | Aplf |

Fig. 36 - 20

| | | | | | | | |
|---|---|---|---|---|---|---|---|
| 3647 | 3 | 4 | 5 | | | V-2 | Apobec3 |
| 3648 | 3 | 4 | 5 | | | V-2 | Apol8 |
| 3649 | 3 | 4 | 5 | | | V-2 | Aqp1 |
| 3650 | 3 | 4 | 5 | | | V-2 | Aqp3 |
| 3651 | 3 | 4 | 5 | | | V-2 | Aqp7 |
| 3652 | 3 | 4 | 5 | | | V-2 | Arf3 |
| 3653 | 3 | 4 | 5 | | | V-2 | Arf5 |
| 3654 | 3 | 4 | 5 | | | V-2 | Arfgef2 |
| 3655 | 3 | 4 | 5 | | | V-2 | Arhgap10 |
| 3656 | 3 | 4 | 5 | | | V-2 | Arhgap21 |
| 3657 | 3 | 4 | 5 | | | V-2 | Arhgap25 |
| 3658 | 3 | 4 | 5 | | | V-2 | Arhgap42 |
| 3659 | 3 | 4 | 5 | | | V-2 | Arhgap8 |
| 3660 | 3 | 4 | 5 | | | V-2 | Arhgef25 |
| 3661 | 3 | 4 | 5 | | | V-2 | Arhgef39 |
| 3662 | 3 | 4 | 5 | | | V-2 | Arid2 |
| 3663 | 3 | 4 | 5 | | | V-2 | Arih2 |
| 3664 | 3 | 4 | 5 | | | V-2 | Arl1 |
| 3665 | 3 | 4 | 5 | | | V-2 | Arl9 |
| 3666 | 3 | 4 | 5 | | | V-2 | Armc12 |
| 3667 | 3 | 4 | 5 | | | V-2 | Arpc3 |
| 3668 | 3 | 4 | 5 | | | V-2 | Arpc4 |
| 3669 | 3 | 4 | 5 | | | V-2 | Arpc5l |
| 3670 | 3 | 4 | 5 | | | V-2 | Arpp21 |
| 3671 | 3 | 4 | 5 | | | V-2 | Arrb1 |
| 3672 | 3 | 4 | 5 | | | V-2 | Art1 |
| 3673 | 3 | 4 | 5 | | | V-2 | Artn |
| 3674 | 3 | 4 | 5 | | | V-2 | Asap1 |
| 3675 | 3 | 4 | 5 | | | V-2 | Asb17 |
| 3676 | 3 | 4 | 5 | | | V-2 | Ash2l |
| 3677 | 3 | 4 | 5 | | | V-2 | Asphd2 |
| 3678 | 3 | 4 | 5 | | | V-2 | Atad2 |
| 3679 | 3 | 4 | 5 | | | V-2 | Atf4 |
| 3680 | 3 | 4 | 5 | | | V-2 | Atg12 |
| 3681 | 3 | 4 | 5 | | | V-2 | Atl1 |
| 3682 | 3 | 4 | 5 | | | V-2 | Atoh7 |
| 3683 | 3 | 4 | 5 | | | V-2 | Atp10d |
| 3684 | 3 | 4 | 5 | | | V-2 | Atp11c |
| 3685 | 3 | 4 | 5 | | | V-2 | Atp12a |
| 3686 | 3 | 4 | 5 | | | V-2 | Atp5b |
| 3687 | 3 | 4 | 5 | | | V-2 | Atp5e |
| 3688 | 3 | 4 | 5 | | | V-2 | Atp5s |
| 3689 | 3 | 4 | 5 | | | V-2 | Atp6v0a2 |
| 3690 | 3 | 4 | 5 | | | V-2 | Atp6v0b |
| 3691 | 3 | 4 | 5 | | | V-2 | Atp6v0e |
| 3692 | 3 | 4 | 5 | | | V-2 | Atp6v1c2 |
| 3693 | 3 | 4 | 5 | | | V-2 | Atp6v1d |
| 3694 | 3 | 4 | 5 | | | V-2 | Atp6v1g1 |
| 3695 | 3 | 4 | 5 | | | V-2 | Atp8a1 |
| 3696 | 3 | 4 | 5 | | | V-2 | Atxn7l1 |
| 3697 | 3 | 4 | 5 | | | V-2 | Atxn7l3 |
| 3698 | 3 | 4 | 5 | | | V-2 | Aup1 |
| 3699 | 3 | 4 | 5 | | | V-2 | Aurkaip1 |
| 3700 | 3 | 4 | 5 | | | V-2 | Aven |
| 3701 | 3 | 4 | 5 | | | V-2 | Avp |
| 3702 | 3 | 4 | 5 | | | V-2 | B230216G23Rik |
| 3703 | 3 | 4 | 5 | | | V-2 | B230217C12Rik |
| 3704 | 3 | 4 | 5 | | | V-2 | B330016D10Rik |
| 3705 | 3 | 4 | 5 | | | V-2 | B3galt1 |
| 3706 | 3 | 4 | 5 | | | V-2 | B3gat2 |
| 3707 | 3 | 4 | 5 | | | V-2 | B3gnt8 |
| 3708 | 3 | 4 | 5 | | | V-2 | B3gnt9 |
| 3709 | 3 | 4 | 5 | | | V-2 | B4galnt1 |
| 3710 | 3 | 4 | 5 | | | V-2 | B630005N14Rik |
| 3711 | 3 | 4 | 5 | | | V-2 | B630019K06Rik |
| 3712 | 3 | 4 | 5 | | | V-2 | B830017H08Rik |
| 3713 | 3 | 4 | 5 | | | V-2 | B930003M22Rik |
| 3714 | 3 | 4 | 5 | | | V-2 | BB123696 |
| 3715 | 3 | 4 | 5 | | | V-2 | BC002163 |
| 3716 | 3 | 4 | 5 | | | V-2 | BC020402 |
| 3717 | 3 | 4 | 5 | | | V-2 | BC024978 |
| 3718 | 3 | 4 | 5 | | | V-2 | BC031181 |
| 3719 | 3 | 4 | 5 | | | V-2 | BC031361 |
| 3720 | 3 | 4 | 5 | | | V-2 | Bach2 |
| 3721 | 3 | 4 | 5 | | | V-2 | Bag1 |
| 3722 | 3 | 4 | 5 | | | V-2 | Bag4 |
| 3723 | 3 | 4 | 5 | | | V-2 | Bak1 |
| 3724 | 3 | 4 | 5 | | | V-2 | Bbc3 |
| 3725 | 3 | 4 | 5 | | | V-2 | Bbip1 |
| 3726 | 3 | 4 | 5 | | | V-2 | Bbs2 |
| 3727 | 3 | 4 | 5 | | | V-2 | Bbs5 |
| 3728 | 3 | 4 | 5 | | | V-2 | Bcap31 |
| 3729 | 3 | 4 | 5 | | | V-2 | Bcas3 |
| 3730 | 3 | 4 | 5 | | | V-2 | Bccip |
| 3731 | 3 | 4 | 5 | | | V-2 | Bche |
| 3732 | 3 | 4 | 5 | | | V-2 | Bckdhb |
| 3733 | 3 | 4 | 5 | | | V-2 | Bcl11a |
| 3734 | 3 | 4 | 5 | | | V-2 | Bcl2l11 |
| 3735 | 3 | 4 | 5 | | | V-2 | Bcl2l12 |
| 3736 | 3 | 4 | 5 | | | V-2 | Bcl2l13 |
| 3737 | 3 | 4 | 5 | | | V-2 | Bcl7a |
| 3738 | 3 | 4 | 5 | | | V-2 | Bcl7c |
| 3739 | 3 | 4 | 5 | | | V-2 | Bcl9 |
| 3740 | 3 | 4 | 5 | | | V-2 | Bco2 |
| 3741 | 3 | 4 | 5 | | | V-2 | Bdkrb1 |
| 3742 | 3 | 4 | 5 | | | V-2 | Bean1 |
| 3743 | 3 | 4 | 5 | | | V-2 | Becn1 |
| 3744 | 3 | 4 | 5 | | | V-2 | Best2 |
| 3745 | 3 | 4 | 5 | | | V-2 | Bet1l |
| 3746 | 3 | 4 | 5 | | | V-2 | Bfsp1 |
| 3747 | 3 | 4 | 5 | | | V-2 | Bfsp2 |
| 3748 | 3 | 4 | 5 | | | V-2 | Bicc1 |
| 3749 | 3 | 4 | 5 | | | V-2 | Bicd1 |
| 3750 | 3 | 4 | 5 | | | V-2 | Bin1 |
| 3751 | 3 | 4 | 5 | | | V-2 | Birc2 |
| 3752 | 3 | 4 | 5 | | | V-2 | Blm |
| 3753 | 3 | 4 | 5 | | | V-2 | Bloc1s2 |
| 3754 | 3 | 4 | 5 | | | V-2 | Blvra |
| 3755 | 3 | 4 | 5 | | | V-2 | Bmf |
| 3756 | 3 | 4 | 5 | | | V-2 | Bmp10 |
| 3757 | 3 | 4 | 5 | | | V-2 | Bmp4 |
| 3758 | 3 | 4 | 5 | | | V-2 | Bmx |
| 3759 | 3 | 4 | 5 | | | V-2 | Bnip1 |
| 3760 | 3 | 4 | 5 | | | V-2 | Bnip3 |
| 3761 | 3 | 4 | 5 | | | V-2 | Bnip3l |
| 3762 | 3 | 4 | 5 | | | V-2 | Bnipl |
| 3763 | 3 | 4 | 5 | | | V-2 | Boc |
| 3764 | 3 | 4 | 5 | | | V-2 | Boll |
| 3765 | 3 | 4 | 5 | | | V-2 | Bora |
| 3766 | 3 | 4 | 5 | | | V-2 | Bpgm |
| 3767 | 3 | 4 | 5 | | | V-2 | Brat1 |
| 3768 | 3 | 4 | 5 | | | V-2 | Bre |
| 3769 | 3 | 4 | 5 | | | V-2 | Bri3 |
| 3770 | 3 | 4 | 5 | | | V-2 | Bricd5 |
| 3771 | 3 | 4 | 5 | | | V-2 | Brip1 |
| 3772 | 3 | 4 | 5 | | | V-2 | Brox |
| 3773 | 3 | 4 | 5 | | | V-2 | Btaf1 |
| 3774 | 3 | 4 | 5 | | | V-2 | Btbd19 |
| 3775 | 3 | 4 | 5 | | | V-2 | Btbd2 |
| 3776 | 3 | 4 | 5 | | | V-2 | Btbd8 |
| 3777 | 3 | 4 | 5 | | | V-2 | Btf3 |
| 3778 | 3 | 4 | 5 | | | V-2 | Btnl1a1 |
| 3779 | 3 | 4 | 5 | | | V-2 | Bud31 |
| 3780 | 3 | 4 | 5 | | | V-2 | C030046E11Rik |
| 3781 | 3 | 4 | 5 | | | V-2 | C130036L24Rik |
| 3782 | 3 | 4 | 5 | | | V-2 | C1d |
| 3783 | 3 | 4 | 5 | | | V-2 | C1ql4 |
| 3784 | 3 | 4 | 5 | | | V-2 | C1qtnf7 |
| 3785 | 3 | 4 | 5 | | | V-2 | C1ra |
| 3786 | 3 | 4 | 5 | | | V-2 | C230004F18Rik |
| 3787 | 3 | 4 | 5 | | | V-2 | C230035I16Rik |
| 3788 | 3 | 4 | 5 | | | V-2 | C5ar2 |
| 3789 | 3 | 4 | 5 | | | V-2 | C730002L08Rik |
| 3790 | 3 | 4 | 5 | | | V-2 | C730036E19Rik |
| 3791 | 3 | 4 | 5 | | | V-2 | Cabp4 |
| 3792 | 3 | 4 | 5 | | | V-2 | Cadm4 |
| 3793 | 3 | 4 | 5 | | | V-2 | Calb2 |
| 3794 | 3 | 4 | 5 | | | V-2 | Calcrl |
| 3795 | 3 | 4 | 5 | | | V-2 | Cald1 |
| 3796 | 3 | 4 | 5 | | | V-2 | Calm2 |
| 3797 | 3 | 4 | 5 | | | V-2 | Camk2n1 |
| 3798 | 3 | 4 | 5 | | | V-2 | Camk2n2 |
| 3799 | 3 | 4 | 5 | | | V-2 | Camsap2 |
| 3800 | 3 | 4 | 5 | | | V-2 | Cap1 |
| 3801 | 3 | 4 | 5 | | | V-2 | Capg |
| 3802 | 3 | 4 | 5 | | | V-2 | Capn2 |
| 3803 | 3 | 4 | 5 | | | V-2 | Capn6 |
| 3804 | 3 | 4 | 5 | | | V-2 | Car13 |
| 3805 | 3 | 4 | 5 | | | V-2 | Car9 |
| 3806 | 3 | 4 | 5 | | | V-2 | Card6 |
| 3807 | 3 | 4 | 5 | | | V-2 | Carhsp1 |
| 3808 | 3 | 4 | 5 | | | V-2 | Carm1 |
| 3809 | 3 | 4 | 5 | | | V-2 | Casp3 |
| 3810 | 3 | 4 | 5 | | | V-2 | Casp6 |
| 3811 | 3 | 4 | 5 | | | V-2 | Casr |
| 3812 | 3 | 4 | 5 | | | V-2 | Cass4 |
| 3813 | 3 | 4 | 5 | | | V-2 | Cast |
| 3814 | 3 | 4 | 5 | | | V-2 | Cat |
| 3815 | 3 | 4 | 5 | | | V-2 | Catsper2 |
| 3816 | 3 | 4 | 5 | | | V-2 | Cav1 |
| 3817 | 3 | 4 | 5 | | | V-2 | Cbfb |
| 3818 | 3 | 4 | 5 | | | V-2 | Cbln2 |
| 3819 | 3 | 4 | 5 | | | V-2 | Cbwd1 |
| 3820 | 3 | 4 | 5 | | | V-2 | Cbx2 |
| 3821 | 3 | 4 | 5 | | | V-2 | Ccbe1 |
| 3822 | 3 | 4 | 5 | | | V-2 | Ccbl2 |
| 3823 | 3 | 4 | 5 | | | V-2 | Ccdc174 |
| 3824 | 3 | 4 | 5 | | | V-2 | Ccdc181 |
| 3825 | 3 | 4 | 5 | | | V-2 | Ccdc22 |
| 3826 | 3 | 4 | 5 | | | V-2 | Ccdc28a |
| 3827 | 3 | 4 | 5 | | | V-2 | Ccdc3 |
| 3828 | 3 | 4 | 5 | | | V-2 | Ccdc59 |
| 3829 | 3 | 4 | 5 | | | V-2 | Ccdc7 |
| 3830 | 3 | 4 | 5 | | | V-2 | Ccdc85a |
| 3831 | 3 | 4 | 5 | | | V-2 | Ccdc88a |
| 3832 | 3 | 4 | 5 | | | V-2 | Ccdc90b |
| 3833 | 3 | 4 | 5 | | | V-2 | Ccdc97 |
| 3834 | 3 | 4 | 5 | | | V-2 | Ccm2l |
| 3835 | 3 | 4 | 5 | | | V-2 | Ccnb3 |
| 3836 | 3 | 4 | 5 | | | V-2 | Ccndbp1 |
| 3837 | 3 | 4 | 5 | | | V-2 | Ccnf |
| 3838 | 3 | 4 | 5 | | | V-2 | Ccng1 |

Fig. 36 - 21

| | | | | | | | |
|---|---|---|---|---|---|---|---|
| 3839 | 3 | 4 | 5 | | V-2 | Ccni | |
| 3840 | 3 | 4 | 5 | | V-2 | Ccr3 | |
| 3841 | 3 | 4 | 5 | | V-2 | Ccrl2 | |
| 3842 | 3 | 4 | 5 | | V-2 | Cct6a | |
| 3843 | 3 | 4 | 5 | | V-2 | Cct7 | |
| 3844 | 3 | 4 | 5 | | V-2 | Cd109 | |
| 3845 | 3 | 4 | 5 | | V-2 | Cd151 | |
| 3846 | 3 | 4 | 5 | | V-2 | Cd163 | |
| 3847 | 3 | 4 | 5 | | V-2 | Cd163l1 | |
| 3848 | 3 | 4 | 5 | | V-2 | Cd19 | |
| 3849 | 3 | 4 | 5 | | V-2 | Cd1d2 | |
| 3850 | 3 | 4 | 5 | | V-2 | Cd207 | |
| 3851 | 3 | 4 | 5 | | V-2 | Cd209b | |
| 3852 | 3 | 4 | 5 | | V-2 | Cd209c | |
| 3853 | 3 | 4 | 5 | | V-2 | Cd226 | |
| 3854 | 3 | 4 | 5 | | V-2 | Cd248 | |
| 3855 | 3 | 4 | 5 | | V-2 | Cd3g | |
| 3856 | 3 | 4 | 5 | | V-2 | Cd44 | |
| 3857 | 3 | 4 | 5 | | V-2 | Cd55 | |
| 3858 | 3 | 4 | 5 | | V-2 | Cd79a | |
| 3859 | 3 | 4 | 5 | | V-2 | Cd82 | |
| 3860 | 3 | 4 | 5 | | V-2 | Cdc16 | |
| 3861 | 3 | 4 | 5 | | V-2 | Cdc25a | |
| 3862 | 3 | 4 | 5 | | V-2 | Cdc34 | |
| 3863 | 3 | 4 | 5 | | V-2 | Cdc37 | |
| 3864 | 3 | 4 | 5 | | V-2 | Cdc45 | |
| 3865 | 3 | 4 | 5 | | V-2 | Cdca7 | |
| 3866 | 3 | 4 | 5 | | V-2 | Cdh19 | |
| 3867 | 3 | 4 | 5 | | V-2 | Cdipt | |
| 3868 | 3 | 4 | 5 | | V-2 | Cdk13 | |
| 3869 | 3 | 4 | 5 | | V-2 | Cdk14 | |
| 3870 | 3 | 4 | 5 | | V-2 | Cdk20 | |
| 3871 | 3 | 4 | 5 | | V-2 | Cdk5rap1 | |
| 3872 | 3 | 4 | 5 | | V-2 | Cdk5rap3 | |
| 3873 | 3 | 4 | 5 | | V-2 | Cdk9 | |
| 3874 | 3 | 4 | 5 | | V-2 | Cdkn1c | |
| 3875 | 3 | 4 | 5 | | V-2 | Cdkn2d | |
| 3876 | 3 | 4 | 5 | | V-2 | Cdyl | |
| 3877 | 3 | 4 | 5 | | V-2 | Cebpd | |
| 3878 | 3 | 4 | 5 | | V-2 | Cebpzos | |
| 3879 | 3 | 4 | 5 | | V-2 | Celf2 | |
| 3880 | 3 | 4 | 5 | | V-2 | Celf4 | |
| 3881 | 3 | 4 | 5 | | V-2 | Celf6 | |
| 3882 | 3 | 4 | 5 | | V-2 | Cenpk | |
| 3883 | 3 | 4 | 5 | | V-2 | Cenpl | |
| 3884 | 3 | 4 | 5 | | V-2 | Cenpm | |
| 3885 | 3 | 4 | 5 | | V-2 | Cenpo | |
| 3886 | 3 | 4 | 5 | | V-2 | Cenpv | |
| 3887 | 3 | 4 | 5 | | V-2 | Cenpw | |
| 3888 | 3 | 4 | 5 | | V-2 | Cep57 | |
| 3889 | 3 | 4 | 5 | | V-2 | Cep57l1 | |
| 3890 | 3 | 4 | 5 | | V-2 | Cep68 | |
| 3891 | 3 | 4 | 5 | | V-2 | Cep97 | |
| 3892 | 3 | 4 | 5 | | V-2 | Cerk | |
| 3893 | 3 | 4 | 5 | | V-2 | Cerkl | |
| 3894 | 3 | 4 | 5 | | V-2 | Cers5 | |
| 3895 | 3 | 4 | 5 | | V-2 | Ces2g | |
| 3896 | 3 | 4 | 5 | | V-2 | Cetn2 | |
| 3897 | 3 | 4 | 5 | | V-2 | Cflar | |
| 3898 | 3 | 4 | 5 | | V-2 | Cgrrf1 | |
| 3899 | 3 | 4 | 5 | | V-2 | Chac2 | |
| 3900 | 3 | 4 | 5 | | V-2 | Chchd3 | |
| 3901 | 3 | 4 | 5 | | V-2 | Chchd4 | |
| 3902 | 3 | 4 | 5 | | V-2 | Chchd5 | |
| 3903 | 3 | 4 | 5 | | V-2 | Chd3 | |
| 3904 | 3 | 4 | 5 | | V-2 | Chmp1b | |
| 3905 | 3 | 4 | 5 | | V-2 | Chmp5 | |
| 3906 | 3 | 4 | 5 | | V-2 | Chp1 | |
| 3907 | 3 | 4 | 5 | | V-2 | Chrdl1 | |
| 3908 | 3 | 4 | 5 | | V-2 | Chst15 | |
| 3909 | 3 | 4 | 5 | | V-2 | Chst7 | |
| 3910 | 3 | 4 | 5 | | V-2 | Chst9 | |
| 3911 | 3 | 4 | 5 | | V-2 | Cirbp | |
| 3912 | 3 | 4 | 5 | | V-2 | Ckb | |
| 3913 | 3 | 4 | 5 | | V-2 | Clca1 | |
| 3914 | 3 | 4 | 5 | | V-2 | Clcc1 | |
| 3915 | 3 | 4 | 5 | | V-2 | Clcn2 | |
| 3916 | 3 | 4 | 5 | | V-2 | Clcn3 | |
| 3917 | 3 | 4 | 5 | | V-2 | Cldn11 | |
| 3918 | 3 | 4 | 5 | | V-2 | Cldn25 | |
| 3919 | 3 | 4 | 5 | | V-2 | Cldn26 | |
| 3920 | 3 | 4 | 5 | | V-2 | Clec11a | |
| 3921 | 3 | 4 | 5 | | V-2 | Clec1a | |
| 3922 | 3 | 4 | 5 | | V-2 | Clec1b | |
| 3923 | 3 | 4 | 5 | | V-2 | Clec2g | |
| 3924 | 3 | 4 | 5 | | V-2 | Clec2i | |
| 3925 | 3 | 4 | 5 | | V-2 | Clic4 | |
| 3926 | 3 | 4 | 5 | | V-2 | Clic5 | |
| 3927 | 3 | 4 | 5 | | V-2 | Clip1 | |
| 3928 | 3 | 4 | 5 | | V-2 | Clk2 | |
| 3929 | 3 | 4 | 5 | | V-2 | Cln3 | |
| 3930 | 3 | 4 | 5 | | V-2 | Clstn3 | |
| 3931 | 3 | 4 | 5 | | V-2 | Cluap1 | |
| 3932 | 3 | 4 | 5 | | V-2 | Cma1 | |
| 3933 | 3 | 4 | 5 | | V-2 | Cml3 | |
| 3934 | 3 | 4 | 5 | | V-2 | Cnbp | |
| 3935 | 3 | 4 | 5 | | V-2 | Cnih1 | |
| 3936 | 3 | 4 | 5 | | V-2 | Cnih2 | |
| 3937 | 3 | 4 | 5 | | V-2 | Cnn2 | |
| 3938 | 3 | 4 | 5 | | V-2 | Cntn3 | |
| 3939 | 3 | 4 | 5 | | V-2 | Coa3 | |
| 3940 | 3 | 4 | 5 | | V-2 | Coa5 | |
| 3941 | 3 | 4 | 5 | | V-2 | Cobll1 | |
| 3942 | 3 | 4 | 5 | | V-2 | Cog5 | |
| 3943 | 3 | 4 | 5 | | V-2 | Coil | |
| 3944 | 3 | 4 | 5 | | V-2 | Col5a1 | |
| 3945 | 3 | 4 | 5 | | V-2 | Col7a1 | |
| 3946 | 3 | 4 | 5 | | V-2 | Col9a2 | |
| 3947 | 3 | 4 | 5 | | V-2 | Colgalt2 | |
| 3948 | 3 | 4 | 5 | | V-2 | Commd1 | |
| 3949 | 3 | 4 | 5 | | V-2 | Commd3 | |
| 3950 | 3 | 4 | 5 | | V-2 | Comtd1 | |
| 3951 | 3 | 4 | 5 | | V-2 | Cops6 | |
| 3952 | 3 | 4 | 5 | | V-2 | Cox14 | |
| 3953 | 3 | 4 | 5 | | V-2 | Cox16 | |
| 3954 | 3 | 4 | 5 | | V-2 | Cox6b1 | |
| 3955 | 3 | 4 | 5 | | V-2 | Cox7a2l | |
| 3956 | 3 | 4 | 5 | | V-2 | Cox7b | |
| 3957 | 3 | 4 | 5 | | V-2 | Cox7c | |
| 3958 | 3 | 4 | 5 | | V-2 | Cox8a | |
| 3959 | 3 | 4 | 5 | | V-2 | Cpa3 | |
| 3960 | 3 | 4 | 5 | | V-2 | Cpa6 | |
| 3961 | 3 | 4 | 5 | | V-2 | Cplx2 | |
| 3962 | 3 | 4 | 5 | | V-2 | Cplx3 | |
| 3963 | 3 | 4 | 5 | | V-2 | Cpne1 | |
| 3964 | 3 | 4 | 5 | | V-2 | Cpne2 | |
| 3965 | 3 | 4 | 5 | | V-2 | Cpsf4 | |
| 3966 | 3 | 4 | 5 | | V-2 | Cpt1b | |
| 3967 | 3 | 4 | 5 | | V-2 | Crb1 | |
| 3968 | 3 | 4 | 5 | | V-2 | Crebzf | |
| 3969 | 3 | 4 | 5 | | V-2 | Creg1 | |
| 3970 | 3 | 4 | 5 | | V-2 | Crhbp | |
| 3971 | 3 | 4 | 5 | | V-2 | Crhr1 | |
| 3972 | 3 | 4 | 5 | | V-2 | Crim1 | |
| 3973 | 3 | 4 | 5 | | V-2 | Cript | |
| 3974 | 3 | 4 | 5 | | V-2 | Crispld1 | |
| 3975 | 3 | 4 | 5 | | V-2 | Crlf1 | |
| 3976 | 3 | 4 | 5 | | V-2 | Crls1 | |
| 3977 | 3 | 4 | 5 | | V-2 | Crnde | |
| 3978 | 3 | 4 | 5 | | V-2 | Cry2 | |
| 3979 | 3 | 4 | 5 | | V-2 | Cryaa | |
| 3980 | 3 | 4 | 5 | | V-2 | Crybb3 | |
| 3981 | 3 | 4 | 5 | | V-2 | Crybg3 | |
| 3982 | 3 | 4 | 5 | | V-2 | Crym | |
| 3983 | 3 | 4 | 5 | | V-2 | Cryzl1 | |
| 3984 | 3 | 4 | 5 | | V-2 | Csad | |
| 3985 | 3 | 4 | 5 | | V-2 | Csgalnact2 | |
| 3986 | 3 | 4 | 5 | | V-2 | Csnk1d | |
| 3987 | 3 | 4 | 5 | | V-2 | Csnk1e | |
| 3988 | 3 | 4 | 5 | | V-2 | Cspg5 | |
| 3989 | 3 | 4 | 5 | | V-2 | Csprs | |
| 3990 | 3 | 4 | 5 | | V-2 | Csrnp1 | |
| 3991 | 3 | 4 | 5 | | V-2 | Csrp1 | |
| 3992 | 3 | 4 | 5 | | V-2 | Cstf1 | |
| 3993 | 3 | 4 | 5 | | V-2 | Ctbs | |
| 3994 | 3 | 4 | 5 | | V-2 | Ctdsp2 | |
| 3995 | 3 | 4 | 5 | | V-2 | Ctgf | |
| 3996 | 3 | 4 | 5 | | V-2 | Ctla2a | |
| 3997 | 3 | 4 | 5 | | V-2 | Ctps2 | |
| 3998 | 3 | 4 | 5 | | V-2 | Ctsb | |
| 3999 | 3 | 4 | 5 | | V-2 | Ctse | |
| 4000 | 3 | 4 | 5 | | V-2 | Ctsf | |
| 4001 | 3 | 4 | 5 | | V-2 | Ctsw | |
| 4002 | 3 | 4 | 5 | | V-2 | Cuedc1 | |
| 4003 | 3 | 4 | 5 | | V-2 | Cul4a | |
| 4004 | 3 | 4 | 5 | | V-2 | Cuta | |
| 4005 | 3 | 4 | 5 | | V-2 | Cux1 | |
| 4006 | 3 | 4 | 5 | | V-2 | Cwf19l1 | |
| 4007 | 3 | 4 | 5 | | V-2 | Cxx1a | |
| 4008 | 3 | 4 | 5 | | V-2 | Cxxc4 | |
| 4009 | 3 | 4 | 5 | | V-2 | Cyb561a3 | |
| 4010 | 3 | 4 | 5 | | V-2 | Cyb5r1 | |
| 4011 | 3 | 4 | 5 | | V-2 | Cyfip2 | |
| 4012 | 3 | 4 | 5 | | V-2 | Cyhr1 | |
| 4013 | 3 | 4 | 5 | | V-2 | Cyp1b1 | |
| 4014 | 3 | 4 | 5 | | V-2 | Cyp2a22 | |
| 4015 | 3 | 4 | 5 | | V-2 | Cyp2a4 | |
| 4016 | 3 | 4 | 5 | | V-2 | Cyp2b19 | |
| 4017 | 3 | 4 | 5 | | V-2 | Cyp2b9 | |
| 4018 | 3 | 4 | 5 | | V-2 | Cyp2c40 | |
| 4019 | 3 | 4 | 5 | | V-2 | Cyp2c68 | |
| 4020 | 3 | 4 | 5 | | V-2 | Cyp2d22 | |
| 4021 | 3 | 4 | 5 | | V-2 | Cyp39a1 | |
| 4022 | 3 | 4 | 5 | | V-2 | Cyp46a1 | |
| 4023 | 3 | 4 | 5 | | V-2 | Cyp4a31 | |
| 4024 | 3 | 4 | 5 | | V-2 | Cyp4a32 | |
| 4025 | 3 | 4 | 5 | | V-2 | Cyp4b1 | |
| 4026 | 3 | 4 | 5 | | V-2 | Cyp4f16 | |
| 4027 | 3 | 4 | 5 | | V-2 | Cyp4f18 | |
| 4028 | 3 | 4 | 5 | | V-2 | Cys1 | |
| 4029 | 3 | 4 | 5 | | V-2 | Cystm1 | |
| 4030 | 3 | 4 | 5 | | V-2 | Cytl1 | |

Fig. 36 - 22

| | | | | | | |
|---|---|---|---|---|---|---|
| 4031 | 3 | 4 | 5 | | V-2 | D030040B21Rik |
| 4032 | 3 | 4 | 5 | | V-2 | D230025D16Rik |
| 4033 | 3 | 4 | 5 | | V-2 | D330050L16Rik |
| 4034 | 3 | 4 | 5 | | V-2 | D5Ertd579e |
| 4035 | 3 | 4 | 5 | | V-2 | D5Ertd605e |
| 4036 | 3 | 4 | 5 | | V-2 | D630032N06Rik |
| 4037 | 3 | 4 | 5 | | V-2 | D6Ertd474e |
| 4038 | 3 | 4 | 5 | | V-2 | D730001G18Rik |
| 4039 | 3 | 4 | 5 | | V-2 | D7Ertd715e |
| 4040 | 3 | 4 | 5 | | V-2 | D830026I12Rik |
| 4041 | 3 | 4 | 5 | | V-2 | D930016D06Rik |
| 4042 | 3 | 4 | 5 | | V-2 | Dapk2 |
| 4043 | 3 | 4 | 5 | | V-2 | Dapk3 |
| 4044 | 3 | 4 | 5 | | V-2 | Dazap2 |
| 4045 | 3 | 4 | 5 | | V-2 | Dbr1 |
| 4046 | 3 | 4 | 5 | | V-2 | Dcaf12 |
| 4047 | 3 | 4 | 5 | | V-2 | Dcakd |
| 4048 | 3 | 4 | 5 | | V-2 | Dclk1 |
| 4049 | 3 | 4 | 5 | | V-2 | Dclk2 |
| 4050 | 3 | 4 | 5 | | V-2 | Dclre1b |
| 4051 | 3 | 4 | 5 | | V-2 | Dcps |
| 4052 | 3 | 4 | 5 | | V-2 | Dcstamp |
| 4053 | 3 | 4 | 5 | | V-2 | Dct |
| 4054 | 3 | 4 | 5 | | V-2 | Dcun1d1 |
| 4055 | 3 | 4 | 5 | | V-2 | Dcun1d3 |
| 4056 | 3 | 4 | 5 | | V-2 | Dcun1d5 |
| 4057 | 3 | 4 | 5 | | V-2 | Ddb2 |
| 4058 | 3 | 4 | 5 | | V-2 | Ddit4 |
| 4059 | 3 | 4 | 5 | | V-2 | Ddx17 |
| 4060 | 3 | 4 | 5 | | V-2 | Ddx39 |
| 4061 | 3 | 4 | 5 | | V-2 | Ddx39b |
| 4062 | 3 | 4 | 5 | | V-2 | Ddx3y |
| 4063 | 3 | 4 | 5 | | V-2 | Defa20 |
| 4064 | 3 | 4 | 5 | | V-2 | Defa22 |
| 4065 | 3 | 4 | 5 | | V-2 | Defa6 |
| 4066 | 3 | 4 | 5 | | V-2 | Defb4 |
| 4067 | 3 | 4 | 5 | | V-2 | Dennd2a |
| 4068 | 3 | 4 | 5 | | V-2 | Dennd5a |
| 4069 | 3 | 4 | 5 | | V-2 | Dennd5b |
| 4070 | 3 | 4 | 5 | | V-2 | Derl1 |
| 4071 | 3 | 4 | 5 | | V-2 | Dgke |
| 4072 | 3 | 4 | 5 | | V-2 | Dgkz |
| 4073 | 3 | 4 | 5 | | V-2 | Dhrs13 |
| 4074 | 3 | 4 | 5 | | V-2 | Dhrs4 |
| 4075 | 3 | 4 | 5 | | V-2 | Dhrs7c |
| 4076 | 3 | 4 | 5 | | V-2 | Diap3 |
| 4077 | 3 | 4 | 5 | | V-2 | Dimt1 |
| 4078 | 3 | 4 | 5 | | V-2 | Dis3l2 |
| 4079 | 3 | 4 | 5 | | V-2 | Dkk2 |
| 4080 | 3 | 4 | 5 | | V-2 | Dlec1 |
| 4081 | 3 | 4 | 5 | | V-2 | Dleu7 |
| 4082 | 3 | 4 | 5 | | V-2 | Dlgap4 |
| 4083 | 3 | 4 | 5 | | V-2 | Dlx6os1 |
| 4084 | 3 | 4 | 5 | | V-2 | Dmap1 |
| 4085 | 3 | 4 | 5 | | V-2 | Dmpk |
| 4086 | 3 | 4 | 5 | | V-2 | Dmrta1 |
| 4087 | 3 | 4 | 5 | | V-2 | Dmrta2 |
| 4088 | 3 | 4 | 5 | | V-2 | Dmxl1 |
| 4089 | 3 | 4 | 5 | | V-2 | Dnah10 |
| 4090 | 3 | 4 | 5 | | V-2 | Dnah17 |
| 4091 | 3 | 4 | 5 | | V-2 | Dnah6 |
| 4092 | 3 | 4 | 5 | | V-2 | Dnah7a |
| 4093 | 3 | 4 | 5 | | V-2 | Dnajb2 |
| 4094 | 3 | 4 | 5 | | V-2 | Dnajb4 |
| 4095 | 3 | 4 | 5 | | V-2 | Dnajb6 |
| 4096 | 3 | 4 | 5 | | V-2 | Dnajc14 |
| 4097 | 3 | 4 | 5 | | V-2 | Dnajc19 |
| 4098 | 3 | 4 | 5 | | V-2 | Dnajc2 |
| 4099 | 3 | 4 | 5 | | V-2 | Dnajc25 |
| 4100 | 3 | 4 | 5 | | V-2 | Dnajc6 |
| 4101 | 3 | 4 | 5 | | V-2 | Dnajc7 |
| 4102 | 3 | 4 | 5 | | V-2 | Dnajc8 |
| 4103 | 3 | 4 | 5 | | V-2 | Dnase2a |
| 4104 | 3 | 4 | 5 | | V-2 | Dntt |
| 4105 | 3 | 4 | 5 | | V-2 | Dock4 |
| 4106 | 3 | 4 | 5 | | V-2 | Dock8 |
| 4107 | 3 | 4 | 5 | | V-2 | Dock9 |
| 4108 | 3 | 4 | 5 | | V-2 | Dok4 |
| 4109 | 3 | 4 | 5 | | V-2 | Dpcd |
| 4110 | 3 | 4 | 5 | | V-2 | Dph7 |
| 4111 | 3 | 4 | 5 | | V-2 | Dpt |
| 4112 | 3 | 4 | 5 | | V-2 | Dpy30 |
| 4113 | 3 | 4 | 5 | | V-2 | Dpysl2 |
| 4114 | 3 | 4 | 5 | | V-2 | Dr1 |
| 4115 | 3 | 4 | 5 | | V-2 | Dram2 |
| 4116 | 3 | 4 | 5 | | V-2 | Draxin |
| 4117 | 3 | 4 | 5 | | V-2 | Drd1a |
| 4118 | 3 | 4 | 5 | | V-2 | Dse |
| 4119 | 3 | 4 | 5 | | V-2 | Dtx2 |
| 4120 | 3 | 4 | 5 | | V-2 | Dtx3 |
| 4121 | 3 | 4 | 5 | | V-2 | Dtymk |
| 4122 | 3 | 4 | 5 | | V-2 | Dus2 |
| 4123 | 3 | 4 | 5 | | V-2 | Dus4l |
| 4124 | 3 | 4 | 5 | | V-2 | Dusp1 |
| 4125 | 3 | 4 | 5 | | V-2 | Dusp2 |
| 4126 | 3 | 4 | 5 | | V-2 | Dusp7 |
| 4127 | 3 | 4 | 5 | | V-2 | Dut |
| 4128 | 3 | 4 | 5 | | V-2 | Dync2li1 |
| 4129 | 3 | 4 | 5 | | V-2 | Dynll1 |
| 4130 | 3 | 4 | 5 | | V-2 | Dynll2 |
| 4131 | 3 | 4 | 5 | | V-2 | Dynlt1a |
| 4132 | 3 | 4 | 5 | | V-2 | Dynlt3 |
| 4133 | 3 | 4 | 5 | | V-2 | Dyrk1a |
| 4134 | 3 | 4 | 5 | | V-2 | E130307A14Rik |
| 4135 | 3 | 4 | 5 | | V-2 | E130311K13Rik |
| 4136 | 3 | 4 | 5 | | V-2 | E230016K23Rik |
| 4137 | 3 | 4 | 5 | | V-2 | Ear6 |
| 4138 | 3 | 4 | 5 | | V-2 | Ebf1 |
| 4139 | 3 | 4 | 5 | | V-2 | Ebf2 |
| 4140 | 3 | 4 | 5 | | V-2 | Ebf3 |
| 4141 | 3 | 4 | 5 | | V-2 | Ebi3 |
| 4142 | 3 | 4 | 5 | | V-2 | Ecm2 |
| 4143 | 3 | 4 | 5 | | V-2 | Edn3 |
| 4144 | 3 | 4 | 5 | | V-2 | Eef1d |
| 4145 | 3 | 4 | 5 | | V-2 | Eef1e1 |
| 4146 | 3 | 4 | 5 | | V-2 | Efcab7 |
| 4147 | 3 | 4 | 5 | | V-2 | Efcab8 |
| 4148 | 3 | 4 | 5 | | V-2 | Efemp1 |
| 4149 | 3 | 4 | 5 | | V-2 | Efhd1 |
| 4150 | 3 | 4 | 5 | | V-2 | Efna5 |
| 4151 | 3 | 4 | 5 | | V-2 | Egfl7 |
| 4152 | 3 | 4 | 5 | | V-2 | Egfl8 |
| 4153 | 3 | 4 | 5 | | V-2 | Ehd4 |
| 4154 | 3 | 4 | 5 | | V-2 | Eid2 |
| 4155 | 3 | 4 | 5 | | V-2 | Eif1 |
| 4156 | 3 | 4 | 5 | | V-2 | Eif2s2 |
| 4157 | 3 | 4 | 5 | | V-2 | Eif3e |
| 4158 | 3 | 4 | 5 | | V-2 | Eif3h |
| 4159 | 3 | 4 | 5 | | V-2 | Eif3m |
| 4160 | 3 | 4 | 5 | | V-2 | Eif4a1 |
| 4161 | 3 | 4 | 5 | | V-2 | Eif4a3 |
| 4162 | 3 | 4 | 5 | | V-2 | Eif4ebp1 |
| 4163 | 3 | 4 | 5 | | V-2 | Eif5 |
| 4164 | 3 | 4 | 5 | | V-2 | Eif6 |
| 4165 | 3 | 4 | 5 | | V-2 | Elf1 |
| 4166 | 3 | 4 | 5 | | V-2 | Ell2 |
| 4167 | 3 | 4 | 5 | | V-2 | Elmod3 |
| 4168 | 3 | 4 | 5 | | V-2 | Elovl1 |
| 4169 | 3 | 4 | 5 | | V-2 | Elp4 |
| 4170 | 3 | 4 | 5 | | V-2 | Emb |
| 4171 | 3 | 4 | 5 | | V-2 | Emg1 |
| 4172 | 3 | 4 | 5 | | V-2 | Endou |
| 4173 | 3 | 4 | 5 | | V-2 | Enox1 |
| 4174 | 3 | 4 | 5 | | V-2 | Entpd2 |
| 4175 | 3 | 4 | 5 | | V-2 | Epas1 |
| 4176 | 3 | 4 | 5 | | V-2 | Epdr1 |
| 4177 | 3 | 4 | 5 | | V-2 | Epha2 |
| 4178 | 3 | 4 | 5 | | V-2 | Epha7 |
| 4179 | 3 | 4 | 5 | | V-2 | Epn1 |
| 4180 | 3 | 4 | 5 | | V-2 | Erg |
| 4181 | 3 | 4 | 5 | | V-2 | Erh |
| 4182 | 3 | 4 | 5 | | V-2 | Esd |
| 4183 | 3 | 4 | 5 | | V-2 | Etfa |
| 4184 | 3 | 4 | 5 | | V-2 | Etv2 |
| 4185 | 3 | 4 | 5 | | V-2 | Etv3 |
| 4186 | 3 | 4 | 5 | | V-2 | Exd2 |
| 4187 | 3 | 4 | 5 | | V-2 | Exoc6b |
| 4188 | 3 | 4 | 5 | | V-2 | Exosc1 |
| 4189 | 3 | 4 | 5 | | V-2 | Exosc8 |
| 4190 | 3 | 4 | 5 | | V-2 | Exosc9 |
| 4191 | 3 | 4 | 5 | | V-2 | Eya1 |
| 4192 | 3 | 4 | 5 | | V-2 | F11r |
| 4193 | 3 | 4 | 5 | | V-2 | F3 |
| 4194 | 3 | 4 | 5 | | V-2 | Fa2h |
| 4195 | 3 | 4 | 5 | | V-2 | Fabp3 |
| 4196 | 3 | 4 | 5 | | V-2 | Fads3 |
| 4197 | 3 | 4 | 5 | | V-2 | Fahd1 |
| 4198 | 3 | 4 | 5 | | V-2 | Faim |
| 4199 | 3 | 4 | 5 | | V-2 | Faim3 |
| 4200 | 3 | 4 | 5 | | V-2 | Fam102b |
| 4201 | 3 | 4 | 5 | | V-2 | Fam103a1 |
| 4202 | 3 | 4 | 5 | | V-2 | Fam104a |
| 4203 | 3 | 4 | 5 | | V-2 | Fam110b |
| 4204 | 3 | 4 | 5 | | V-2 | Fam120aos |
| 4205 | 3 | 4 | 5 | | V-2 | Fam126a |
| 4206 | 3 | 4 | 5 | | V-2 | Fam132a |
| 4207 | 3 | 4 | 5 | | V-2 | Fam132b |
| 4208 | 3 | 4 | 5 | | V-2 | Fam135a |
| 4209 | 3 | 4 | 5 | | V-2 | Fam13c |
| 4210 | 3 | 4 | 5 | | V-2 | Fam150b |
| 4211 | 3 | 4 | 5 | | V-2 | Fam151b |
| 4212 | 3 | 4 | 5 | | V-2 | Fam159a |
| 4213 | 3 | 4 | 5 | | V-2 | Fam161a |
| 4214 | 3 | 4 | 5 | | V-2 | Fam162a |
| 4215 | 3 | 4 | 5 | | V-2 | Fam173b |
| 4216 | 3 | 4 | 5 | | V-2 | Fam178a |
| 4217 | 3 | 4 | 5 | | V-2 | Fam187b |
| 4218 | 3 | 4 | 5 | | V-2 | Fam195a |
| 4219 | 3 | 4 | 5 | | V-2 | Fam198b |
| 4220 | 3 | 4 | 5 | | V-2 | Fam19a5 |
| 4221 | 3 | 4 | 5 | | V-2 | Fam203a |
| 4222 | 3 | 4 | 5 | | V-2 | Fam20a |

Fig. 36 - 23

| | | | | | | | |
|---|---|---|---|---|---|---|---|
| 4223 | 3 | 4 | 5 | | | V-2 | Fam214a |
| 4224 | 3 | 4 | 5 | | | V-2 | Fam214b |
| 4225 | 3 | 4 | 5 | | | V-2 | Fam219aos |
| 4226 | 3 | 4 | 5 | | | V-2 | Fam219b |
| 4227 | 3 | 4 | 5 | | | V-2 | Fam220a |
| 4228 | 3 | 4 | 5 | | | V-2 | Fam26e |
| 4229 | 3 | 4 | 5 | | | V-2 | Fam32a |
| 4230 | 3 | 4 | 5 | | | V-2 | Fam3b |
| 4231 | 3 | 4 | 5 | | | V-2 | Fam45a |
| 4232 | 3 | 4 | 5 | | | V-2 | Fam46b |
| 4233 | 3 | 4 | 5 | | | V-2 | Fam69a |
| 4234 | 3 | 4 | 5 | | | V-2 | Fam76a |
| 4235 | 3 | 4 | 5 | | | V-2 | Fam83g |
| 4236 | 3 | 4 | 5 | | | V-2 | Fam84b |
| 4237 | 3 | 4 | 5 | | | V-2 | Fam86 |
| 4238 | 3 | 4 | 5 | | | V-2 | Fam96b |
| 4239 | 3 | 4 | 5 | | | V-2 | Fancc |
| 4240 | 3 | 4 | 5 | | | V-2 | Farp1 |
| 4241 | 3 | 4 | 5 | | | V-2 | Fastkd3 |
| 4242 | 3 | 4 | 5 | | | V-2 | Fastkd5 |
| 4243 | 3 | 4 | 5 | | | V-2 | Fbln5 |
| 4244 | 3 | 4 | 5 | | | V-2 | Fbxl12os |
| 4245 | 3 | 4 | 5 | | | V-2 | Fbxl2 |
| 4246 | 3 | 4 | 5 | | | V-2 | Fbxl20 |
| 4247 | 3 | 4 | 5 | | | V-2 | Fbxl4 |
| 4248 | 3 | 4 | 5 | | | V-2 | Fbxl8 |
| 4249 | 3 | 4 | 5 | | | V-2 | Fbxo2 |
| 4250 | 3 | 4 | 5 | | | V-2 | Fbxo24 |
| 4251 | 3 | 4 | 5 | | | V-2 | Fbxo33 |
| 4252 | 3 | 4 | 5 | | | V-2 | Fbxo42 |
| 4253 | 3 | 4 | 5 | | | V-2 | Fbxo5 |
| 4254 | 3 | 4 | 5 | | | V-2 | Fbxo7 |
| 4255 | 3 | 4 | 5 | | | V-2 | Fbxw11 |
| 4256 | 3 | 4 | 5 | | | V-2 | Fbxw2 |
| 4257 | 3 | 4 | 5 | | | V-2 | Fbxw9 |
| 4258 | 3 | 4 | 5 | | | V-2 | Fcamr |
| 4259 | 3 | 4 | 5 | | | V-2 | Fcrl6 |
| 4260 | 3 | 4 | 5 | | | V-2 | Fcrla |
| 4261 | 3 | 4 | 5 | | | V-2 | Fdx1 |
| 4262 | 3 | 4 | 5 | | | V-2 | Fez1 |
| 4263 | 3 | 4 | 5 | | | V-2 | Fez2 |
| 4264 | 3 | 4 | 5 | | | V-2 | Fgf10 |
| 4265 | 3 | 4 | 5 | | | V-2 | Fgf11 |
| 4266 | 3 | 4 | 5 | | | V-2 | Fgf20 |
| 4267 | 3 | 4 | 5 | | | V-2 | Fgf5 |
| 4268 | 3 | 4 | 5 | | | V-2 | Fgf7 |
| 4269 | 3 | 4 | 5 | | | V-2 | Fgfr1op2 |
| 4270 | 3 | 4 | 5 | | | V-2 | Fgfr2 |
| 4271 | 3 | 4 | 5 | | | V-2 | Fgfr3 |
| 4272 | 3 | 4 | 5 | | | V-2 | Fgfrl1 |
| 4273 | 3 | 4 | 5 | | | V-2 | Fggy |
| 4274 | 3 | 4 | 5 | | | V-2 | Fhl2 |
| 4275 | 3 | 4 | 5 | | | V-2 | Fibin |
| 4276 | 3 | 4 | 5 | | | V-2 | Figf |
| 4277 | 3 | 4 | 5 | | | V-2 | Fign |
| 4278 | 3 | 4 | 5 | | | V-2 | Fignl2 |
| 4279 | 3 | 4 | 5 | | | V-2 | Fis1 |
| 4280 | 3 | 4 | 5 | | | V-2 | Fjx1 |
| 4281 | 3 | 4 | 5 | | | V-2 | Fkbp1a |
| 4282 | 3 | 4 | 5 | | | V-2 | Fkbp1b |
| 4283 | 3 | 4 | 5 | | | V-2 | Fkbp3 |
| 4284 | 3 | 4 | 5 | | | V-2 | Fli1 |
| 4285 | 3 | 4 | 5 | | | V-2 | Flrt3 |
| 4286 | 3 | 4 | 5 | | | V-2 | Flt4 |
| 4287 | 3 | 4 | 5 | | | V-2 | Fmnl1 |
| 4288 | 3 | 4 | 5 | | | V-2 | Fmnl2 |
| 4289 | 3 | 4 | 5 | | | V-2 | Fmo1 |
| 4290 | 3 | 4 | 5 | | | V-2 | Fmo5 |
| 4291 | 3 | 4 | 5 | | | V-2 | Fmr1 |
| 4292 | 3 | 4 | 5 | | | V-2 | Fn3k |
| 4293 | 3 | 4 | 5 | | | V-2 | Fnbp1l |
| 4294 | 3 | 4 | 5 | | | V-2 | Fndc4 |
| 4295 | 3 | 4 | 5 | | | V-2 | Fnta |
| 4296 | 3 | 4 | 5 | | | V-2 | Fopnl |
| 4297 | 3 | 4 | 5 | | | V-2 | Foxd3 |
| 4298 | 3 | 4 | 5 | | | V-2 | Foxj2 |
| 4299 | 3 | 4 | 5 | | | V-2 | Foxl1 |
| 4300 | 3 | 4 | 5 | | | V-2 | Foxo6 |
| 4301 | 3 | 4 | 5 | | | V-2 | Foxr1 |
| 4302 | 3 | 4 | 5 | | | V-2 | Frat2 |
| 4303 | 3 | 4 | 5 | | | V-2 | Frem2 |
| 4304 | 3 | 4 | 5 | | | V-2 | Frmd4b |
| 4305 | 3 | 4 | 5 | | | V-2 | Frmd8 |
| 4306 | 3 | 4 | 5 | | | V-2 | Fscb |
| 4307 | 3 | 4 | 5 | | | V-2 | Fscn2 |
| 4308 | 3 | 4 | 5 | | | V-2 | Fth1 |
| 4309 | 3 | 4 | 5 | | | V-2 | Ftl1 |
| 4310 | 3 | 4 | 5 | | | V-2 | Fuz |
| 4311 | 3 | 4 | 5 | | | V-2 | Fzd6 |
| 4312 | 3 | 4 | 5 | | | V-2 | G6b |
| 4313 | 3 | 4 | 5 | | | V-2 | G730013B0SRik |
| 4314 | 3 | 4 | 5 | | | V-2 | Gab1 |
| 4315 | 3 | 4 | 5 | | | V-2 | Gab2 |
| 4316 | 3 | 4 | 5 | | | V-2 | Gabarapl1 |
| 4317 | 3 | 4 | 5 | | | V-2 | Gabarapl2 |
| 4318 | 3 | 4 | 5 | | | V-2 | Gabra1 |
| 4319 | 3 | 4 | 5 | | | V-2 | Gabrr2 |
| 4320 | 3 | 4 | 5 | | | V-2 | Gal3st1 |
| 4321 | 3 | 4 | 5 | | | V-2 | Galk1 |
| 4322 | 3 | 4 | 5 | | | V-2 | Galm |
| 4323 | 3 | 4 | 5 | | | V-2 | Galnt10 |
| 4324 | 3 | 4 | 5 | | | V-2 | Galnt16 |
| 4325 | 3 | 4 | 5 | | | V-2 | Galnt18 |
| 4326 | 3 | 4 | 5 | | | V-2 | Ganc |
| 4327 | 3 | 4 | 5 | | | V-2 | Gap43 |
| 4328 | 3 | 4 | 5 | | | V-2 | Gas1 |
| 4329 | 3 | 4 | 5 | | | V-2 | Gas2l1 |
| 4330 | 3 | 4 | 5 | | | V-2 | Gas6 |
| 4331 | 3 | 4 | 5 | | | V-2 | Gas7 |
| 4332 | 3 | 4 | 5 | | | V-2 | Gata6 |
| 4333 | 3 | 4 | 5 | | | V-2 | Gatm |
| 4334 | 3 | 4 | 5 | | | V-2 | Gbas |
| 4335 | 3 | 4 | 5 | | | V-2 | Gbe1 |
| 4336 | 3 | 4 | 5 | | | V-2 | Gcfc2 |
| 4337 | 3 | 4 | 5 | | | V-2 | Gcnt1 |
| 4338 | 3 | 4 | 5 | | | V-2 | Gda |
| 4339 | 3 | 4 | 5 | | | V-2 | Gdf10 |
| 4340 | 3 | 4 | 5 | | | V-2 | Gdpd2 |
| 4341 | 3 | 4 | 5 | | | V-2 | Gemin8 |
| 4342 | 3 | 4 | 5 | | | V-2 | Gfer |
| 4343 | 3 | 4 | 5 | | | V-2 | Gfm1 |
| 4344 | 3 | 4 | 5 | | | V-2 | Ghitm |
| 4345 | 3 | 4 | 5 | | | V-2 | Ghr |
| 4346 | 3 | 4 | 5 | | | V-2 | Gid8 |
| 4347 | 3 | 4 | 5 | | | V-2 | Gimap1 |
| 4348 | 3 | 4 | 5 | | | V-2 | Gimap7 |
| 4349 | 3 | 4 | 5 | | | V-2 | Ginm1 |
| 4350 | 3 | 4 | 5 | | | V-2 | Gins3 |
| 4351 | 3 | 4 | 5 | | | V-2 | Gins4 |
| 4352 | 3 | 4 | 5 | | | V-2 | Gipc1 |
| 4353 | 3 | 4 | 5 | | | V-2 | Gja5 |
| 4354 | 3 | 4 | 5 | | | V-2 | Glcci1 |
| 4355 | 3 | 4 | 5 | | | V-2 | Glmn |
| 4356 | 3 | 4 | 5 | | | V-2 | Glrx3 |
| 4357 | 3 | 4 | 5 | | | V-2 | Glrx5 |
| 4358 | 3 | 4 | 5 | | | V-2 | Glt1d1 |
| 4359 | 3 | 4 | 5 | | | V-2 | Glul |
| 4360 | 3 | 4 | 5 | | | V-2 | Gm101 |
| 4361 | 3 | 4 | 5 | | | V-2 | Gm10125 |
| 4362 | 3 | 4 | 5 | | | V-2 | Gm10364 |
| 4363 | 3 | 4 | 5 | | | V-2 | Gm10433 |
| 4364 | 3 | 4 | 5 | | | V-2 | Gm10516 |
| 4365 | 3 | 4 | 5 | | | V-2 | Gm10619 |
| 4366 | 3 | 4 | 5 | | | V-2 | Gm10638 |
| 4367 | 3 | 4 | 5 | | | V-2 | Gm10639 |
| 4368 | 3 | 4 | 5 | | | V-2 | Gm10785 |
| 4369 | 3 | 4 | 5 | | | V-2 | Gm10872 |
| 4370 | 3 | 4 | 5 | | | V-2 | Gm11166 |
| 4371 | 3 | 4 | 5 | | | V-2 | Gm11190 |
| 4372 | 3 | 4 | 5 | | | V-2 | Gm11351 |
| 4373 | 3 | 4 | 5 | | | V-2 | Gm11545 |
| 4374 | 3 | 4 | 5 | | | V-2 | Gm11562 |
| 4375 | 3 | 4 | 5 | | | V-2 | Gm11565 |
| 4376 | 3 | 4 | 5 | | | V-2 | Gm11757 |
| 4377 | 3 | 4 | 5 | | | V-2 | Gm12070 |
| 4378 | 3 | 4 | 5 | | | V-2 | Gm12338 |
| 4379 | 3 | 4 | 5 | | | V-2 | Gm12409 |
| 4380 | 3 | 4 | 5 | | | V-2 | Gm12522 |
| 4381 | 3 | 4 | 5 | | | V-2 | Gm12657 |
| 4382 | 3 | 4 | 5 | | | V-2 | Gm13154 |
| 4383 | 3 | 4 | 5 | | | V-2 | Gm13157 |
| 4384 | 3 | 4 | 5 | | | V-2 | Gm13212 |
| 4385 | 3 | 4 | 5 | | | V-2 | Gm13242 |
| 4386 | 3 | 4 | 5 | | | V-2 | Gm13251 |
| 4387 | 3 | 4 | 5 | | | V-2 | Gm13298 |
| 4388 | 3 | 4 | 5 | | | V-2 | Gm13446 |
| 4389 | 3 | 4 | 5 | | | V-2 | Gm13807 |
| 4390 | 3 | 4 | 5 | | | V-2 | Gm13871 |
| 4391 | 3 | 4 | 5 | | | V-2 | Gm14151 |
| 4392 | 3 | 4 | 5 | | | V-2 | Gm14405 |
| 4393 | 3 | 4 | 5 | | | V-2 | Gm14420 |
| 4394 | 3 | 4 | 5 | | | V-2 | Gm15055 |
| 4395 | 3 | 4 | 5 | | | V-2 | Gm15217 |
| 4396 | 3 | 4 | 5 | | | V-2 | Gm15401 |
| 4397 | 3 | 4 | 5 | | | V-2 | Gm15645 |
| 4398 | 3 | 4 | 5 | | | V-2 | Gm15881 |
| 4399 | 3 | 4 | 5 | | | V-2 | Gm16548 |
| 4400 | 3 | 4 | 5 | | | V-2 | Gm16793 |
| 4401 | 3 | 4 | 5 | | | V-2 | Gm16982 |
| 4402 | 3 | 4 | 5 | | | V-2 | Gm17359 |
| 4403 | 3 | 4 | 5 | | | V-2 | Gm17745 |
| 4404 | 3 | 4 | 5 | | | V-2 | Gm19705 |
| 4405 | 3 | 4 | 5 | | | V-2 | Gm19710 |
| 4406 | 3 | 4 | 5 | | | V-2 | Gm20740 |
| 4407 | 3 | 4 | 5 | | | V-2 | Gm21057 |
| 4408 | 3 | 4 | 5 | | | V-2 | Gm21637 |
| 4409 | 3 | 4 | 5 | | | V-2 | Gm2518 |
| 4410 | 3 | 4 | 5 | | | V-2 | Gm2694 |
| 4411 | 3 | 4 | 5 | | | V-2 | Gm364 |
| 4412 | 3 | 4 | 5 | | | V-2 | Gm382 |
| 4413 | 3 | 4 | 5 | | | V-2 | Gm41 |
| 4414 | 3 | 4 | 5 | | | V-2 | Gm4477 |

Fig. 36 - 24

| | | | | | | | |
|---|---|---|---|---|---|---|---|
| 4415 | 3 | 4 | 5 | | | V-2 | Gm4489 |
| 4416 | 3 | 4 | 5 | | | V-2 | Gm4598 |
| 4417 | 3 | 4 | 5 | | | V-2 | Gm4944 |
| 4418 | 3 | 4 | 5 | | | V-2 | Gm5083 |
| 4419 | 3 | 4 | 5 | | | V-2 | Gm5084 |
| 4420 | 3 | 4 | 5 | | | V-2 | Gm5114 |
| 4421 | 3 | 4 | 5 | | | V-2 | Gm5148 |
| 4422 | 3 | 4 | 5 | | | V-2 | Gm527 |
| 4423 | 3 | 4 | 5 | | | V-2 | Gm5294 |
| 4424 | 3 | 4 | 5 | | | V-2 | Gm5409 |
| 4425 | 3 | 4 | 5 | | | V-2 | Gm5460 |
| 4426 | 3 | 4 | 5 | | | V-2 | Gm5592 |
| 4427 | 3 | 4 | 5 | | | V-2 | Gm5617 |
| 4428 | 3 | 4 | 5 | | | V-2 | Gm5941 |
| 4429 | 3 | 4 | 5 | | | V-2 | Gm597 |
| 4430 | 3 | 4 | 5 | | | V-2 | Gm6083 |
| 4431 | 3 | 4 | 5 | | | V-2 | Gm6329 |
| 4432 | 3 | 4 | 5 | | | V-2 | Gm6377 |
| 4433 | 3 | 4 | 5 | | | V-2 | Gm6484 |
| 4434 | 3 | 4 | 5 | | | V-2 | Gm6578 |
| 4435 | 3 | 4 | 5 | | | V-2 | Gm6642 |
| 4436 | 3 | 4 | 5 | | | V-2 | Gm6682 |
| 4437 | 3 | 4 | 5 | | | V-2 | Gm6787 |
| 4438 | 3 | 4 | 5 | | | V-2 | Gm684 |
| 4439 | 3 | 4 | 5 | | | V-2 | Gm7244 |
| 4440 | 3 | 4 | 5 | | | V-2 | Gm7903 |
| 4441 | 3 | 4 | 5 | | | V-2 | Gm826 |
| 4442 | 3 | 4 | 5 | | | V-2 | Gm8363 |
| 4443 | 3 | 4 | 5 | | | V-2 | Gm8765 |
| 4444 | 3 | 4 | 5 | | | V-2 | Gm884 |
| 4445 | 3 | 4 | 5 | | | V-2 | Gm9079 |
| 4446 | 3 | 4 | 5 | | | V-2 | Gm9199 |
| 4447 | 3 | 4 | 5 | | | V-2 | Gm9962 |
| 4448 | 3 | 4 | 5 | | | V-2 | Gm9992 |
| 4449 | 3 | 4 | 5 | | | V-2 | Gmpr |
| 4450 | 3 | 4 | 5 | | | V-2 | Gna13 |
| 4451 | 3 | 4 | 5 | | | V-2 | Gnai1 |
| 4452 | 3 | 4 | 5 | | | V-2 | Gnaq |
| 4453 | 3 | 4 | 5 | | | V-2 | Gnaz |
| 4454 | 3 | 4 | 5 | | | V-2 | Gng12 |
| 4455 | 3 | 4 | 5 | | | V-2 | Gng13 |
| 4456 | 3 | 4 | 5 | | | V-2 | Gng5 |
| 4457 | 3 | 4 | 5 | | | V-2 | Gnl3l |
| 4458 | 3 | 4 | 5 | | | V-2 | Gnpda1 |
| 4459 | 3 | 4 | 5 | | | V-2 | Golga7 |
| 4460 | 3 | 4 | 5 | | | V-2 | Gp5 |
| 4461 | 3 | 4 | 5 | | | V-2 | Gp9 |
| 4462 | 3 | 4 | 5 | | | V-2 | Gpalpp1 |
| 4463 | 3 | 4 | 5 | | | V-2 | Gpatch4 |
| 4464 | 3 | 4 | 5 | | | V-2 | Gpbp1 |
| 4465 | 3 | 4 | 5 | | | V-2 | Gpcpd1 |
| 4466 | 3 | 4 | 5 | | | V-2 | Gpd1l |
| 4467 | 3 | 4 | 5 | | | V-2 | Gper1 |
| 4468 | 3 | 4 | 5 | | | V-2 | Gpihbp1 |
| 4469 | 3 | 4 | 5 | | | V-2 | Gpm6b |
| 4470 | 3 | 4 | 5 | | | V-2 | Gpnmb |
| 4471 | 3 | 4 | 5 | | | V-2 | Gpr1 |
| 4472 | 3 | 4 | 5 | | | V-2 | Gpr146 |
| 4473 | 3 | 4 | 5 | | | V-2 | Gpr157 |
| 4474 | 3 | 4 | 5 | | | V-2 | Gpr18 |
| 4475 | 3 | 4 | 5 | | | V-2 | Gpr19 |
| 4476 | 3 | 4 | 5 | | | V-2 | Gpr3 |
| 4477 | 3 | 4 | 5 | | | V-2 | Gpr56 |
| 4478 | 3 | 4 | 5 | | | V-2 | Gprin2 |
| 4479 | 3 | 4 | 5 | | | V-2 | Gpx4 |
| 4480 | 3 | 4 | 5 | | | V-2 | Gramd2 |
| 4481 | 3 | 4 | 5 | | | V-2 | Grap |
| 4482 | 3 | 4 | 5 | | | V-2 | Grap2 |
| 4483 | 3 | 4 | 5 | | | V-2 | Grasp |
| 4484 | 3 | 4 | 5 | | | V-2 | Grina |
| 4485 | 3 | 4 | 5 | | | V-2 | Grip1os2 |
| 4486 | 3 | 4 | 5 | | | V-2 | Grpel2 |
| 4487 | 3 | 4 | 5 | | | V-2 | Gsdmc3 |
| 4488 | 3 | 4 | 5 | | | V-2 | Gsdmcl1 |
| 4489 | 3 | 4 | 5 | | | V-2 | Gsg2 |
| 4490 | 3 | 4 | 5 | | | V-2 | Gsr |
| 4491 | 3 | 4 | 5 | | | V-2 | Gstt2 |
| 4492 | 3 | 4 | 5 | | | V-2 | Gt(ROSA)26Sor |
| 4493 | 3 | 4 | 5 | | | V-2 | Gtf2a2 |
| 4494 | 3 | 4 | 5 | | | V-2 | Gtf2h2 |
| 4495 | 3 | 4 | 5 | | | V-2 | Gtpbp2 |
| 4496 | 3 | 4 | 5 | | | V-2 | Gucd1 |
| 4497 | 3 | 4 | 5 | | | V-2 | Gypc |
| 4498 | 3 | 4 | 5 | | | V-2 | Gzmk |
| 4499 | 3 | 4 | 5 | | | V-2 | H1f0 |
| 4500 | 3 | 4 | 5 | | | V-2 | H2-Ke2 |
| 4501 | 3 | 4 | 5 | | | V-2 | H2-M5 |
| 4502 | 3 | 4 | 5 | | | V-2 | H2-Oa |
| 4503 | 3 | 4 | 5 | | | V-2 | H2afx |
| 4504 | 3 | 4 | 5 | | | V-2 | H2afy2 |
| 4505 | 3 | 4 | 5 | | | V-2 | H2afz |
| 4506 | 3 | 4 | 5 | | | V-2 | H3f3a |
| 4507 | 3 | 4 | 5 | | | V-2 | Hace1 |
| 4508 | 3 | 4 | 5 | | | V-2 | Hacl1 |
| 4509 | 3 | 4 | 5 | | | V-2 | Hadhb |
| 4510 | 3 | 4 | 5 | | | V-2 | Hagh |
| 4511 | 3 | 4 | 5 | | | V-2 | Hamp2 |
| 4512 | 3 | 4 | 5 | | | V-2 | Hand1 |
| 4513 | 3 | 4 | 5 | | | V-2 | Hapln3 |
| 4514 | 3 | 4 | 5 | | | V-2 | Hat1 |
| 4515 | 3 | 4 | 5 | | | V-2 | Hbb-bt |
| 4516 | 3 | 4 | 5 | | | V-2 | Hbq1a |
| 4517 | 3 | 4 | 5 | | | V-2 | Hbq1b |
| 4518 | 3 | 4 | 5 | | | V-2 | Hcfc1r1 |
| 4519 | 3 | 4 | 5 | | | V-2 | Hcrt |
| 4520 | 3 | 4 | 5 | | | V-2 | Hdac1 |
| 4521 | 3 | 4 | 5 | | | V-2 | Hdac2 |
| 4522 | 3 | 4 | 5 | | | V-2 | Hdac3 |
| 4523 | 3 | 4 | 5 | | | V-2 | Hebp1 |
| 4524 | 3 | 4 | 5 | | | V-2 | Hecw2 |
| 4525 | 3 | 4 | 5 | | | V-2 | Hemgn |
| 4526 | 3 | 4 | 5 | | | V-2 | Hemk1 |
| 4527 | 3 | 4 | 5 | | | V-2 | Herpud2 |
| 4528 | 3 | 4 | 5 | | | V-2 | Hes2 |
| 4529 | 3 | 4 | 5 | | | V-2 | Hes6 |
| 4530 | 3 | 4 | 5 | | | V-2 | Hey2 |
| 4531 | 3 | 4 | 5 | | | V-2 | Hfm1 |
| 4532 | 3 | 4 | 5 | | | V-2 | Hif3a |
| 4533 | 3 | 4 | 5 | | | V-2 | Higd1b |
| 4534 | 3 | 4 | 5 | | | V-2 | Hint1 |
| 4535 | 3 | 4 | 5 | | | V-2 | Hip1 |
| 4536 | 3 | 4 | 5 | | | V-2 | Hipk1 |
| 4537 | 3 | 4 | 5 | | | V-2 | Hist1h1a |
| 4538 | 3 | 4 | 5 | | | V-2 | Hist1h2ah |
| 4539 | 3 | 4 | 5 | | | V-2 | Hist1h2bk |
| 4540 | 3 | 4 | 5 | | | V-2 | Hist1h3c |
| 4541 | 3 | 4 | 5 | | | V-2 | Hist2h2aa1 |
| 4542 | 3 | 4 | 5 | | | V-2 | Hist2h2be |
| 4543 | 3 | 4 | 5 | | | V-2 | Hk1 |
| 4544 | 3 | 4 | 5 | | | V-2 | Hlf |
| 4545 | 3 | 4 | 5 | | | V-2 | Hmbs |
| 4546 | 3 | 4 | 5 | | | V-2 | Hmgb1 |
| 4547 | 3 | 4 | 5 | | | V-2 | Hmgn2 |
| 4548 | 3 | 4 | 5 | | | V-2 | Hnf4aos |
| 4549 | 3 | 4 | 5 | | | V-2 | Hnmt |
| 4550 | 3 | 4 | 5 | | | V-2 | Hnrnph1 |
| 4551 | 3 | 4 | 5 | | | V-2 | Hnrnph3 |
| 4552 | 3 | 4 | 5 | | | V-2 | Homez |
| 4553 | 3 | 4 | 5 | | | V-2 | Hoxa4 |
| 4554 | 3 | 4 | 5 | | | V-2 | Hoxa7 |
| 4555 | 3 | 4 | 5 | | | V-2 | Hoxc8 |
| 4556 | 3 | 4 | 5 | | | V-2 | Hoxd8 |
| 4557 | 3 | 4 | 5 | | | V-2 | Hpcal1 |
| 4558 | 3 | 4 | 5 | | | V-2 | Hpgd |
| 4559 | 3 | 4 | 5 | | | V-2 | Hprt |
| 4560 | 3 | 4 | 5 | | | V-2 | Hps1 |
| 4561 | 3 | 4 | 5 | | | V-2 | Hps6 |
| 4562 | 3 | 4 | 5 | | | V-2 | Hpse |
| 4563 | 3 | 4 | 5 | | | V-2 | Hrsp12 |
| 4564 | 3 | 4 | 5 | | | V-2 | Hs6st1 |
| 4565 | 3 | 4 | 5 | | | V-2 | Hsd11b2 |
| 4566 | 3 | 4 | 5 | | | V-2 | Hsd3b1 |
| 4567 | 3 | 4 | 5 | | | V-2 | Hsh2d |
| 4568 | 3 | 4 | 5 | | | V-2 | Hspa12b |
| 4569 | 3 | 4 | 5 | | | V-2 | Hspa4l |
| 4570 | 3 | 4 | 5 | | | V-2 | Hspb6 |
| 4571 | 3 | 4 | 5 | | | V-2 | Hspb7 |
| 4572 | 3 | 4 | 5 | | | V-2 | Hspb9 |
| 4573 | 3 | 4 | 5 | | | V-2 | Hspbap1 |
| 4574 | 3 | 4 | 5 | | | V-2 | Htr2b |
| 4575 | 3 | 4 | 5 | | | V-2 | Htr6 |
| 4576 | 3 | 4 | 5 | | | V-2 | Htra4 |
| 4577 | 3 | 4 | 5 | | | V-2 | Hyal4 |
| 4578 | 3 | 4 | 5 | | | V-2 | Hyal6 |
| 4579 | 3 | 4 | 5 | | | V-2 | Hydin |
| 4580 | 3 | 4 | 5 | | | V-2 | Hykk |
| 4581 | 3 | 4 | 5 | | | V-2 | Ick |
| 4582 | 3 | 4 | 5 | | | V-2 | Id3 |
| 4583 | 3 | 4 | 5 | | | V-2 | Ier5l |
| 4584 | 3 | 4 | 5 | | | V-2 | Ifi27 |
| 4585 | 3 | 4 | 5 | | | V-2 | Ifi35 |
| 4586 | 3 | 4 | 5 | | | V-2 | Ifngr1 |
| 4587 | 3 | 4 | 5 | | | V-2 | Ifnlr1 |
| 4588 | 3 | 4 | 5 | | | V-2 | Ifrd1 |
| 4589 | 3 | 4 | 5 | | | V-2 | Ift20 |
| 4590 | 3 | 4 | 5 | | | V-2 | Ift22 |
| 4591 | 3 | 4 | 5 | | | V-2 | Ift27 |
| 4592 | 3 | 4 | 5 | | | V-2 | Ift46 |
| 4593 | 3 | 4 | 5 | | | V-2 | Ift81 |
| 4594 | 3 | 4 | 5 | | | V-2 | Igfbp3 |
| 4595 | 3 | 4 | 5 | | | V-2 | Igfbp6 |
| 4596 | 3 | 4 | 5 | | | V-2 | Igip |
| 4597 | 3 | 4 | 5 | | | V-2 | Igll1 |
| 4598 | 3 | 4 | 5 | | | V-2 | Ikbkg |
| 4599 | 3 | 4 | 5 | | | V-2 | Il12a |
| 4600 | 3 | 4 | 5 | | | V-2 | Il15 |
| 4601 | 3 | 4 | 5 | | | V-2 | Il16 |
| 4602 | 3 | 4 | 5 | | | V-2 | Il17rc |
| 4603 | 3 | 4 | 5 | | | V-2 | Il18 |
| 4604 | 3 | 4 | 5 | | | V-2 | Il1r1 |
| 4605 | 3 | 4 | 5 | | | V-2 | Il2ra |
| 4606 | 3 | 4 | 5 | | | V-2 | Il4 |

Fig. 36 - 25

| | | | | | | | |
|---|---|---|---|---|---|---|---|
| 4607 | 3 | 4 | 5 | | V-2 | Ilf2 |
| 4608 | 3 | 4 | 5 | | V-2 | Ilk |
| 4609 | 3 | 4 | 5 | | V-2 | Inhbe |
| 4610 | 3 | 4 | 5 | | V-2 | Ino80b |
| 4611 | 3 | 4 | 5 | | V-2 | Inpp4a |
| 4612 | 3 | 4 | 5 | | V-2 | Inpp5e |
| 4613 | 3 | 4 | 5 | | V-2 | Ints2 |
| 4614 | 3 | 4 | 5 | | V-2 | Ip6k3 |
| 4615 | 3 | 4 | 5 | | V-2 | Ipo11 |
| 4616 | 3 | 4 | 5 | | V-2 | Iqcb1 |
| 4617 | 3 | 4 | 5 | | V-2 | Irak1bp1 |
| 4618 | 3 | 4 | 5 | | V-2 | Irgc1 |
| 4619 | 3 | 4 | 5 | | V-2 | Irx3 |
| 4620 | 3 | 4 | 5 | | V-2 | Irx4 |
| 4621 | 3 | 4 | 5 | | V-2 | Isca1 |
| 4622 | 3 | 4 | 5 | | V-2 | Isca2 |
| 4623 | 3 | 4 | 5 | | V-2 | Islr |
| 4624 | 3 | 4 | 5 | | V-2 | Islr2 |
| 4625 | 3 | 4 | 5 | | V-2 | Ispd |
| 4626 | 3 | 4 | 5 | | V-2 | Itfg2 |
| 4627 | 3 | 4 | 5 | | V-2 | Itga6 |
| 4628 | 3 | 4 | 5 | | V-2 | Itga7 |
| 4629 | 3 | 4 | 5 | | V-2 | Itgav |
| 4630 | 3 | 4 | 5 | | V-2 | Itgax |
| 4631 | 3 | 4 | 5 | | V-2 | Itgb3 |
| 4632 | 3 | 4 | 5 | | V-2 | Itpa |
| 4633 | 3 | 4 | 5 | | V-2 | Itpr1 |
| 4634 | 3 | 4 | 5 | | V-2 | Itsn1 |
| 4635 | 3 | 4 | 5 | | V-2 | Jade1 |
| 4636 | 3 | 4 | 5 | | V-2 | Jade3 |
| 4637 | 3 | 4 | 5 | | V-2 | Jak1 |
| 4638 | 3 | 4 | 5 | | V-2 | Jarid2 |
| 4639 | 3 | 4 | 5 | | V-2 | Jazf1 |
| 4640 | 3 | 4 | 5 | | V-2 | Jund |
| 4641 | 3 | 4 | 5 | | V-2 | Katna1 |
| 4642 | 3 | 4 | 5 | | V-2 | Katnb1 |
| 4643 | 3 | 4 | 5 | | V-2 | Kbtbd12 |
| 4644 | 3 | 4 | 5 | | V-2 | Kcnab1 |
| 4645 | 3 | 4 | 5 | | V-2 | Kcnd3 |
| 4646 | 3 | 4 | 5 | | V-2 | Kcne4 |
| 4647 | 3 | 4 | 5 | | V-2 | Kcnip1 |
| 4648 | 3 | 4 | 5 | | V-2 | Kcnj12 |
| 4649 | 3 | 4 | 5 | | V-2 | Kctd18 |
| 4650 | 3 | 4 | 5 | | V-2 | Kctd4 |
| 4651 | 3 | 4 | 5 | | V-2 | Kdm8 |
| 4652 | 3 | 4 | 5 | | V-2 | Kel |
| 4653 | 3 | 4 | 5 | | V-2 | Kif2a |
| 4654 | 3 | 4 | 5 | | V-2 | Kif4-ps |
| 4655 | 3 | 4 | 5 | | V-2 | Kif5b |
| 4656 | 3 | 4 | 5 | | V-2 | Kifc5b |
| 4657 | 3 | 4 | 5 | | V-2 | Kif8 |
| 4658 | 3 | 4 | 5 | | V-2 | Klc1 |
| 4659 | 3 | 4 | 5 | | V-2 | Klc3 |
| 4660 | 3 | 4 | 5 | | V-2 | Klf10 |
| 4661 | 3 | 4 | 5 | | V-2 | Klf11 |
| 4662 | 3 | 4 | 5 | | V-2 | Klf13 |
| 4663 | 3 | 4 | 5 | | V-2 | Klf15 |
| 4664 | 3 | 4 | 5 | | V-2 | Klf16 |
| 4665 | 3 | 4 | 5 | | V-2 | Klf6 |
| 4666 | 3 | 4 | 5 | | V-2 | Klhdc1 |
| 4667 | 3 | 4 | 5 | | V-2 | Klhdc4 |
| 4668 | 3 | 4 | 5 | | V-2 | Klhdc8b |
| 4669 | 3 | 4 | 5 | | V-2 | Klhdc9 |
| 4670 | 3 | 4 | 5 | | V-2 | Klhl29 |
| 4671 | 3 | 4 | 5 | | V-2 | Klhl4 |
| 4672 | 3 | 4 | 5 | | V-2 | Klhl7 |
| 4673 | 3 | 4 | 5 | | V-2 | Klk14 |
| 4674 | 3 | 4 | 5 | | V-2 | Klk1b4 |
| 4675 | 3 | 4 | 5 | | V-2 | Klk8 |
| 4676 | 3 | 4 | 5 | | V-2 | Klra1 |
| 4677 | 3 | 4 | 5 | | V-2 | Klra5 |
| 4678 | 3 | 4 | 5 | | V-2 | Klrb1b |
| 4679 | 3 | 4 | 5 | | V-2 | Klrc1 |
| 4680 | 3 | 4 | 5 | | V-2 | Klre1 |
| 4681 | 3 | 4 | 5 | | V-2 | Klri1 |
| 4682 | 3 | 4 | 5 | | V-2 | Kpna1 |
| 4683 | 3 | 4 | 5 | | V-2 | Kptn |
| 4684 | 3 | 4 | 5 | | V-2 | Krt10 |
| 4685 | 3 | 4 | 5 | | V-2 | Krt16 |
| 4686 | 3 | 4 | 5 | | V-2 | Krt17 |
| 4687 | 3 | 4 | 5 | | V-2 | Krt84 |
| 4688 | 3 | 4 | 5 | | V-2 | Krtap19-9b |
| 4689 | 3 | 4 | 5 | | V-2 | Krtap21-1 |
| 4690 | 3 | 4 | 5 | | V-2 | Krtap3-1 |
| 4691 | 3 | 4 | 5 | | V-2 | Krtap3-2 |
| 4692 | 3 | 4 | 5 | | V-2 | Krtap4-16 |
| 4693 | 3 | 4 | 5 | | V-2 | Krtap4-6 |
| 4694 | 3 | 4 | 5 | | V-2 | Krtap4-7 |
| 4695 | 3 | 4 | 5 | | V-2 | Krtap6-2 |
| 4696 | 3 | 4 | 5 | | V-2 | Krtap8-1 |
| 4697 | 3 | 4 | 5 | | V-2 | Kxd1 |
| 4698 | 3 | 4 | 5 | | V-2 | Kynu |
| 4699 | 3 | 4 | 5 | | V-2 | LOC100504039 |
| 4700 | 3 | 4 | 5 | | V-2 | LOC100861978 |
| 4701 | 3 | 4 | 5 | | V-2 | LOC101056136 |
| 4702 | 3 | 4 | 5 | | V-2 | LOC102636514 |

| | | | | | | | |
|---|---|---|---|---|---|---|---|
| 4703 | 3 | 4 | 5 | | V-2 | LOC666331 |
| 4704 | 3 | 4 | 5 | | V-2 | Lamc1 |
| 4705 | 3 | 4 | 5 | | V-2 | Lamp3 |
| 4706 | 3 | 4 | 5 | | V-2 | Lamtor3 |
| 4707 | 3 | 4 | 5 | | V-2 | Lamtor5 |
| 4708 | 3 | 4 | 5 | | V-2 | Laptm4b |
| 4709 | 3 | 4 | 5 | | V-2 | Lat |
| 4710 | 3 | 4 | 5 | | V-2 | Lbh |
| 4711 | 3 | 4 | 5 | | V-2 | Lbp |
| 4712 | 3 | 4 | 5 | | V-2 | Lce1c |
| 4713 | 3 | 4 | 5 | | V-2 | Lce3d |
| 4714 | 3 | 4 | 5 | | V-2 | Lce3e |
| 4715 | 3 | 4 | 5 | | V-2 | Lck |
| 4716 | 3 | 4 | 5 | | V-2 | Lcmt2 |
| 4717 | 3 | 4 | 5 | | V-2 | Lcorl |
| 4718 | 3 | 4 | 5 | | V-2 | Ldb2 |
| 4719 | 3 | 4 | 5 | | V-2 | Ldlrap1 |
| 4720 | 3 | 4 | 5 | | V-2 | Leap2 |
| 4721 | 3 | 4 | 5 | | V-2 | Leprel4 |
| 4722 | 3 | 4 | 5 | | V-2 | Letm2 |
| 4723 | 3 | 4 | 5 | | V-2 | Lfng |
| 4724 | 3 | 4 | 5 | | V-2 | Lgr4 |
| 4725 | 3 | 4 | 5 | | V-2 | Lhcgr |
| 4726 | 3 | 4 | 5 | | V-2 | Lhx1os |
| 4727 | 3 | 4 | 5 | | V-2 | Lhx6 |
| 4728 | 3 | 4 | 5 | | V-2 | Lhx8 |
| 4729 | 3 | 4 | 5 | | V-2 | Lhx9 |
| 4730 | 3 | 4 | 5 | | V-2 | Lifr |
| 4731 | 3 | 4 | 5 | | V-2 | Lilra6 |
| 4732 | 3 | 4 | 5 | | V-2 | Lim2 |
| 4733 | 3 | 4 | 5 | | V-2 | Limd2 |
| 4734 | 3 | 4 | 5 | | V-2 | Lims1 |
| 4735 | 3 | 4 | 5 | | V-2 | Lims2 |
| 4736 | 3 | 4 | 5 | | V-2 | Lipt1 |
| 4737 | 3 | 4 | 5 | | V-2 | Litaf |
| 4738 | 3 | 4 | 5 | | V-2 | Lix1l |
| 4739 | 3 | 4 | 5 | | V-2 | Lmcd1 |
| 4740 | 3 | 4 | 5 | | V-2 | Lmna |
| 4741 | 3 | 4 | 5 | | V-2 | Lmtk3 |
| 4742 | 3 | 4 | 5 | | V-2 | Lnx1 |
| 4743 | 3 | 4 | 5 | | V-2 | Lox |
| 4744 | 3 | 4 | 5 | | V-2 | Lpcat1 |
| 4745 | 3 | 4 | 5 | | V-2 | Lpcat4 |
| 4746 | 3 | 4 | 5 | | V-2 | Lphn2 |
| 4747 | 3 | 4 | 5 | | V-2 | Lpin1 |
| 4748 | 3 | 4 | 5 | | V-2 | Lpin2 |
| 4749 | 3 | 4 | 5 | | V-2 | Lpin3 |
| 4750 | 3 | 4 | 5 | | V-2 | Lrch3 |
| 4751 | 3 | 4 | 5 | | V-2 | Lrfn1 |
| 4752 | 3 | 4 | 5 | | V-2 | Lrfn3 |
| 4753 | 3 | 4 | 5 | | V-2 | Lrp11 |
| 4754 | 3 | 4 | 5 | | V-2 | Lrrc1 |
| 4755 | 3 | 4 | 5 | | V-2 | Lrrc16a |
| 4756 | 3 | 4 | 5 | | V-2 | Lrrc24 |
| 4757 | 3 | 4 | 5 | | V-2 | Lrrc29 |
| 4758 | 3 | 4 | 5 | | V-2 | Lrrc30 |
| 4759 | 3 | 4 | 5 | | V-2 | Lrrc39 |
| 4760 | 3 | 4 | 5 | | V-2 | Lrrc51 |
| 4761 | 3 | 4 | 5 | | V-2 | Lrrc57 |
| 4762 | 3 | 4 | 5 | | V-2 | Lrrc9 |
| 4763 | 3 | 4 | 5 | | V-2 | Lrrn3 |
| 4764 | 3 | 4 | 5 | | V-2 | Lrrn4 |
| 4765 | 3 | 4 | 5 | | V-2 | Lrtm2 |
| 4766 | 3 | 4 | 5 | | V-2 | Lsm10 |
| 4767 | 3 | 4 | 5 | | V-2 | Lsm8 |
| 4768 | 3 | 4 | 5 | | V-2 | Ltbp1 |
| 4769 | 3 | 4 | 5 | | V-2 | Ly6g6e |
| 4770 | 3 | 4 | 5 | | V-2 | Ly6g6f |
| 4771 | 3 | 4 | 5 | | V-2 | Ly6h |
| 4772 | 3 | 4 | 5 | | V-2 | Ly6k |
| 4773 | 3 | 4 | 5 | | V-2 | Lyar |
| 4774 | 3 | 4 | 5 | | V-2 | Lynx1 |
| 4775 | 3 | 4 | 5 | | V-2 | Mad2l1bp |
| 4776 | 3 | 4 | 5 | | V-2 | Maf |
| 4777 | 3 | 4 | 5 | | V-2 | Mafk |
| 4778 | 3 | 4 | 5 | | V-2 | Magea4 |
| 4779 | 3 | 4 | 5 | | V-2 | Maged2 |
| 4780 | 3 | 4 | 5 | | V-2 | Mageh1 |
| 4781 | 3 | 4 | 5 | | V-2 | Magi3 |
| 4782 | 3 | 4 | 5 | | V-2 | Mall |
| 4783 | 3 | 4 | 5 | | V-2 | Malsu1 |
| 4784 | 3 | 4 | 5 | | V-2 | Manf |
| 4785 | 3 | 4 | 5 | | V-2 | Mansc1 |
| 4786 | 3 | 4 | 5 | | V-2 | Map1lc3b |
| 4787 | 3 | 4 | 5 | | V-2 | Map2k2 |
| 4788 | 3 | 4 | 5 | | V-2 | Map2k3 |
| 4789 | 3 | 4 | 5 | | V-2 | Map3k12 |
| 4790 | 3 | 4 | 5 | | V-2 | Map3k5 |
| 4791 | 3 | 4 | 5 | | V-2 | Map3k8 |
| 4792 | 3 | 4 | 5 | | V-2 | Mapk1 |
| 4793 | 3 | 4 | 5 | | V-2 | Mapk12 |
| 4794 | 3 | 4 | 5 | | V-2 | Mapk3 |
| 4795 | 3 | 4 | 5 | | V-2 | Mapk6 |
| 4796 | 3 | 4 | 5 | | V-2 | Mapre3 |
| 4797 | 3 | 4 | 5 | | V-2 | Marc1 |
| 4798 | 3 | 4 | 5 | | V-2 | March1 |

Fig. 36 - 26

| | | | | | | | |
|---|---|---|---|---|---|---|---|
| 4799 | 3 | 4 | 5 | | V-2 | March2 |
| 4800 | 3 | 4 | 5 | | V-2 | March8 |
| 4801 | 3 | 4 | 5 | | V-2 | Marcks |
| 4802 | 3 | 4 | 5 | | V-2 | Mast2 |
| 4803 | 3 | 4 | 5 | | V-2 | Mat2b |
| 4804 | 3 | 4 | 5 | | V-2 | Maz |
| 4805 | 3 | 4 | 5 | | V-2 | Mbip |
| 4806 | 3 | 4 | 5 | | V-2 | Mblac1 |
| 4807 | 3 | 4 | 5 | | V-2 | Mblac2 |
| 4808 | 3 | 4 | 5 | | V-2 | Mbnl1 |
| 4809 | 3 | 4 | 5 | | V-2 | Mc4r |
| 4810 | 3 | 4 | 5 | | V-2 | Mcee |
| 4811 | 3 | 4 | 5 | | V-2 | Mcf2 |
| 4812 | 3 | 4 | 5 | | V-2 | Mchr1 |
| 4813 | 3 | 4 | 5 | | V-2 | Mcm3 |
| 4814 | 3 | 4 | 5 | | V-2 | Mcm5 |
| 4815 | 3 | 4 | 5 | | V-2 | Mcm7 |
| 4816 | 3 | 4 | 5 | | V-2 | Mcpt1 |
| 4817 | 3 | 4 | 5 | | V-2 | Mcpt2 |
| 4818 | 3 | 4 | 5 | | V-2 | Mctp1 |
| 4819 | 3 | 4 | 5 | | V-2 | Mcts1 |
| 4820 | 3 | 4 | 5 | | V-2 | Mcur1 |
| 4821 | 3 | 4 | 5 | | V-2 | Mdfi |
| 4822 | 3 | 4 | 5 | | V-2 | Mdfic |
| 4823 | 3 | 4 | 5 | | V-2 | Med10 |
| 4824 | 3 | 4 | 5 | | V-2 | Med12l |
| 4825 | 3 | 4 | 5 | | V-2 | Med13 |
| 4826 | 3 | 4 | 5 | | V-2 | Med15 |
| 4827 | 3 | 4 | 5 | | V-2 | Med20 |
| 4828 | 3 | 4 | 5 | | V-2 | Med29 |
| 4829 | 3 | 4 | 5 | | V-2 | Med6 |
| 4830 | 3 | 4 | 5 | | V-2 | Med8 |
| 4831 | 3 | 4 | 5 | | V-2 | Mef2a |
| 4832 | 3 | 4 | 5 | | V-2 | Mef2c |
| 4833 | 3 | 4 | 5 | | V-2 | Mertk |
| 4834 | 3 | 4 | 5 | | V-2 | Mesdc1 |
| 4835 | 3 | 4 | 5 | | V-2 | Mest |
| 4836 | 3 | 4 | 5 | | V-2 | Metap2 |
| 4837 | 3 | 4 | 5 | | V-2 | Mettl15 |
| 4838 | 3 | 4 | 5 | | V-2 | Mettl17 |
| 4839 | 3 | 4 | 5 | | V-2 | Mettl18 |
| 4840 | 3 | 4 | 5 | | V-2 | Mettl20 |
| 4841 | 3 | 4 | 5 | | V-2 | Mettl24 |
| 4842 | 3 | 4 | 5 | | V-2 | Mettl7a2 |
| 4843 | 3 | 4 | 5 | | V-2 | Mex3d |
| 4844 | 3 | 4 | 5 | | V-2 | Mff |
| 4845 | 3 | 4 | 5 | | V-2 | Mfsd2b |
| 4846 | 3 | 4 | 5 | | V-2 | Mfsd7c |
| 4847 | 3 | 4 | 5 | | V-2 | Micu1 |
| 4848 | 3 | 4 | 5 | | V-2 | Mlip |
| 4849 | 3 | 4 | 5 | | V-2 | Mir22hg |
| 4850 | 3 | 4 | 5 | | V-2 | Mirg |
| 4851 | 3 | 4 | 5 | | V-2 | Mis18a |
| 4852 | 3 | 4 | 5 | | V-2 | Mitf |
| 4853 | 3 | 4 | 5 | | V-2 | Mkrn1 |
| 4854 | 3 | 4 | 5 | | V-2 | Mkrn3 |
| 4855 | 3 | 4 | 5 | | V-2 | Mlh3 |
| 4856 | 3 | 4 | 5 | | V-2 | Mllt10 |
| 4857 | 3 | 4 | 5 | | V-2 | Mllt3 |
| 4858 | 3 | 4 | 5 | | V-2 | Mlxip |
| 4859 | 3 | 4 | 5 | | V-2 | Mmd |
| 4860 | 3 | 4 | 5 | | V-2 | Mme |
| 4861 | 3 | 4 | 5 | | V-2 | Mmp11 |
| 4862 | 3 | 4 | 5 | | V-2 | Mmrn1 |
| 4863 | 3 | 4 | 5 | | V-2 | Mnat1 |
| 4864 | 3 | 4 | 5 | | V-2 | Mnda |
| 4865 | 3 | 4 | 5 | | V-2 | Mndal |
| 4866 | 3 | 4 | 5 | | V-2 | Mnt |
| 4867 | 3 | 4 | 5 | | V-2 | Mob2 |
| 4868 | 3 | 4 | 5 | | V-2 | Morc3 |
| 4869 | 3 | 4 | 5 | | V-2 | Morn1 |
| 4870 | 3 | 4 | 5 | | V-2 | Mospd2 |
| 4871 | 3 | 4 | 5 | | V-2 | Mpc1 |
| 4872 | 3 | 4 | 5 | | V-2 | Mpc2 |
| 4873 | 3 | 4 | 5 | | V-2 | Mpl |
| 4874 | 3 | 4 | 5 | | V-2 | Mpp5 |
| 4875 | 3 | 4 | 5 | | V-2 | Mras |
| 4876 | 3 | 4 | 5 | | V-2 | Mrgprb2 |
| 4877 | 3 | 4 | 5 | | V-2 | Mrgprg |
| 4878 | 3 | 4 | 5 | | V-2 | Mri1 |
| 4879 | 3 | 4 | 5 | | V-2 | Mroh2b |
| 4880 | 3 | 4 | 5 | | V-2 | Mroh5 |
| 4881 | 3 | 4 | 5 | | V-2 | Mrpl13 |
| 4882 | 3 | 4 | 5 | | V-2 | Mrpl14 |
| 4883 | 3 | 4 | 5 | | V-2 | Mrpl15 |
| 4884 | 3 | 4 | 5 | | V-2 | Mrpl24 |
| 4885 | 3 | 4 | 5 | | V-2 | Mrpl30 |
| 4886 | 3 | 4 | 5 | | V-2 | Mrpl38 |
| 4887 | 3 | 4 | 5 | | V-2 | Mrpl41 |
| 4888 | 3 | 4 | 5 | | V-2 | Mrpl43 |
| 4889 | 3 | 4 | 5 | | V-2 | Mrpl45 |
| 4890 | 3 | 4 | 5 | | V-2 | Mrpl47 |
| 4891 | 3 | 4 | 5 | | V-2 | Mrpl54 |
| 4892 | 3 | 4 | 5 | | V-2 | Mrps16 |
| 4893 | 3 | 4 | 5 | | V-2 | Mrps18a |
| 4894 | 3 | 4 | 5 | | V-2 | Mrps18b |
| 4895 | 3 | 4 | 5 | | V-2 | Mrps22 |
| 4896 | 3 | 4 | 5 | | V-2 | Mrps23 |
| 4897 | 3 | 4 | 5 | | V-2 | Mrps24 |
| 4898 | 3 | 4 | 5 | | V-2 | Mrps28 |
| 4899 | 3 | 4 | 5 | | V-2 | Mrrf |
| 4900 | 3 | 4 | 5 | | V-2 | Mrvi1 |
| 4901 | 3 | 4 | 5 | | V-2 | Ms4a4b |
| 4902 | 3 | 4 | 5 | | V-2 | Ms4a4d |
| 4903 | 3 | 4 | 5 | | V-2 | Msl3l2 |
| 4904 | 3 | 4 | 5 | | V-2 | Mt4 |
| 4905 | 3 | 4 | 5 | | V-2 | Mtdh |
| 4906 | 3 | 4 | 5 | | V-2 | Mtfmt |
| 4907 | 3 | 4 | 5 | | V-2 | Mthfd1 |
| 4908 | 3 | 4 | 5 | | V-2 | Mthfd2l |
| 4909 | 3 | 4 | 5 | | V-2 | Mtmr1 |
| 4910 | 3 | 4 | 5 | | V-2 | Mtmr10 |
| 4911 | 3 | 4 | 5 | | V-2 | Mtmr3 |
| 4912 | 3 | 4 | 5 | | V-2 | Murc |
| 4913 | 3 | 4 | 5 | | V-2 | Mvb12b |
| 4914 | 3 | 4 | 5 | | V-2 | Mxi1 |
| 4915 | 3 | 4 | 5 | | V-2 | Mxra8 |
| 4916 | 3 | 4 | 5 | | V-2 | Mybl1 |
| 4917 | 3 | 4 | 5 | | V-2 | Myc |
| 4918 | 3 | 4 | 5 | | V-2 | Mycbp |
| 4919 | 3 | 4 | 5 | | V-2 | Mycl |
| 4920 | 3 | 4 | 5 | | V-2 | Mycn |
| 4921 | 3 | 4 | 5 | | V-2 | Myl6b |
| 4922 | 3 | 4 | 5 | | V-2 | Myl7 |
| 4923 | 3 | 4 | 5 | | V-2 | Mylip |
| 4924 | 3 | 4 | 5 | | V-2 | Mylk |
| 4925 | 3 | 4 | 5 | | V-2 | Mylk3 |
| 4926 | 3 | 4 | 5 | | V-2 | Myo1c |
| 4927 | 3 | 4 | 5 | | V-2 | Myo9a |
| 4928 | 3 | 4 | 5 | | V-2 | Myog |
| 4929 | 3 | 4 | 5 | | V-2 | Myrip |
| 4930 | 3 | 4 | 5 | | V-2 | Mzt1 |
| 4931 | 3 | 4 | 5 | | V-2 | Mzt2 |
| 4932 | 3 | 4 | 5 | | V-2 | N4bp1 |
| 4933 | 3 | 4 | 5 | | V-2 | N4bp2l1 |
| 4934 | 3 | 4 | 5 | | V-2 | Naa20 |
| 4935 | 3 | 4 | 5 | | V-2 | Naa38 |
| 4936 | 3 | 4 | 5 | | V-2 | Nab2 |
| 4937 | 3 | 4 | 5 | | V-2 | Nabp1 |
| 4938 | 3 | 4 | 5 | | V-2 | Naca |
| 4939 | 3 | 4 | 5 | | V-2 | Nadk2 |
| 4940 | 3 | 4 | 5 | | V-2 | Nae1 |
| 4941 | 3 | 4 | 5 | | V-2 | Nagk |
| 4942 | 3 | 4 | 5 | | V-2 | Nagpa |
| 4943 | 3 | 4 | 5 | | V-2 | Naip2 |
| 4944 | 3 | 4 | 5 | | V-2 | Nans |
| 4945 | 3 | 4 | 5 | | V-2 | Napa |
| 4946 | 3 | 4 | 5 | | V-2 | Narg2 |
| 4947 | 3 | 4 | 5 | | V-2 | Nat1 |
| 4948 | 3 | 4 | 5 | | V-2 | Nat2 |
| 4949 | 3 | 4 | 5 | | V-2 | Nbas |
| 4950 | 3 | 4 | 5 | | V-2 | Nccrp1 |
| 4951 | 3 | 4 | 5 | | V-2 | Nceh1 |
| 4952 | 3 | 4 | 5 | | V-2 | Ncf4 |
| 4953 | 3 | 4 | 5 | | V-2 | Nckap1 |
| 4954 | 3 | 4 | 5 | | V-2 | Nckipsd |
| 4955 | 3 | 4 | 5 | | V-2 | Ncoa2 |
| 4956 | 3 | 4 | 5 | | V-2 | Ncoa3 |
| 4957 | 3 | 4 | 5 | | V-2 | Ncoa7 |
| 4958 | 3 | 4 | 5 | | V-2 | Ndc1 |
| 4959 | 3 | 4 | 5 | | V-2 | Ndrg3 |
| 4960 | 3 | 4 | 5 | | V-2 | Ndst2 |
| 4961 | 3 | 4 | 5 | | V-2 | Ndufa13 |
| 4962 | 3 | 4 | 5 | | V-2 | Ndufa4l2 |
| 4963 | 3 | 4 | 5 | | V-2 | Ndufa6 |
| 4964 | 3 | 4 | 5 | | V-2 | Ndufaf3 |
| 4965 | 3 | 4 | 5 | | V-2 | Ndufb10 |
| 4966 | 3 | 4 | 5 | | V-2 | Ndufb11 |
| 4967 | 3 | 4 | 5 | | V-2 | Ndufb4 |
| 4968 | 3 | 4 | 5 | | V-2 | Ndufb6 |
| 4969 | 3 | 4 | 5 | | V-2 | Ndufb8 |
| 4970 | 3 | 4 | 5 | | V-2 | Ndufb9 |
| 4971 | 3 | 4 | 5 | | V-2 | Ndufc2 |
| 4972 | 3 | 4 | 5 | | V-2 | Ndufs4 |
| 4973 | 3 | 4 | 5 | | V-2 | Ndufs8 |
| 4974 | 3 | 4 | 5 | | V-2 | Ndufv2 |
| 4975 | 3 | 4 | 5 | | V-2 | Ndufv3 |
| 4976 | 3 | 4 | 5 | | V-2 | Neat1 |
| 4977 | 3 | 4 | 5 | | V-2 | Nefh |
| 4978 | 3 | 4 | 5 | | V-2 | Nek7 |
| 4979 | 3 | 4 | 5 | | V-2 | Nelfe |
| 4980 | 3 | 4 | 5 | | V-2 | Nepn |
| 4981 | 3 | 4 | 5 | | V-2 | Net1 |
| 4982 | 3 | 4 | 5 | | V-2 | Neurl1b |
| 4983 | 3 | 4 | 5 | | V-2 | Neurl3 |
| 4984 | 3 | 4 | 5 | | V-2 | Nfatc2ip |
| 4985 | 3 | 4 | 5 | | V-2 | Nfe2 |
| 4986 | 3 | 4 | 5 | | V-2 | Nfkbib |
| 4987 | 3 | 4 | 5 | | V-2 | Nfkbil1 |
| 4988 | 3 | 4 | 5 | | V-2 | Nfs1 |
| 4989 | 3 | 4 | 5 | | V-2 | Nfu1 |
| 4990 | 3 | 4 | 5 | | V-2 | Nipal1 |

Fig. 36 - 27

| | | | | | | | |
|---|---|---|---|---|---|---|---|
| 4991 | 3 | 4 | 5 | | V-2 | Nipal3 |
| 4992 | 3 | 4 | 5 | | V-2 | Nipsnap3b |
| 4993 | 3 | 4 | 5 | | V-2 | Nit1 |
| 4994 | 3 | 4 | 5 | | V-2 | Nkain4 |
| 4995 | 3 | 4 | 5 | | V-2 | Nkx2-2 |
| 4996 | 3 | 4 | 5 | | V-2 | Nkx2-4 |
| 4997 | 3 | 4 | 5 | | V-2 | Nlgn2 |
| 4998 | 3 | 4 | 5 | | V-2 | Nlk |
| 4999 | 3 | 4 | 5 | | V-2 | Nlrx1 |
| 5000 | 3 | 4 | 5 | | V-2 | Nme3 |
| 5001 | 3 | 4 | 5 | | V-2 | Nog |
| 5002 | 3 | 4 | 5 | | V-2 | Nol7 |
| 5003 | 3 | 4 | 5 | | V-2 | Nomo1 |
| 5004 | 3 | 4 | 5 | | V-2 | Nop10 |
| 5005 | 3 | 4 | 5 | | V-2 | Nop16 |
| 5006 | 3 | 4 | 5 | | V-2 | Nostrin |
| 5007 | 3 | 4 | 5 | | V-2 | Nov |
| 5008 | 3 | 4 | 5 | | V-2 | Nox4 |
| 5009 | 3 | 4 | 5 | | V-2 | Noxred1 |
| 5010 | 3 | 4 | 5 | | V-2 | Npat |
| 5011 | 3 | 4 | 5 | | V-2 | Npbwr1 |
| 5012 | 3 | 4 | 5 | | V-2 | Npr2 |
| 5013 | 3 | 4 | 5 | | V-2 | Nqo1 |
| 5014 | 3 | 4 | 5 | | V-2 | Nqo2 |
| 5015 | 3 | 4 | 5 | | V-2 | Nr1h2 |
| 5016 | 3 | 4 | 5 | | V-2 | Nr1h3 |
| 5017 | 3 | 4 | 5 | | V-2 | Nr2e3 |
| 5018 | 3 | 4 | 5 | | V-2 | Nr3c1 |
| 5019 | 3 | 4 | 5 | | V-2 | Nradd |
| 5020 | 3 | 4 | 5 | | V-2 | Nrip3 |
| 5021 | 3 | 4 | 5 | | V-2 | Nrp1 |
| 5022 | 3 | 4 | 5 | | V-2 | Nsg1 |
| 5023 | 3 | 4 | 5 | | V-2 | Nsg2 |
| 5024 | 3 | 4 | 5 | | V-2 | Nsmaf |
| 5025 | 3 | 4 | 5 | | V-2 | Nsun6 |
| 5026 | 3 | 4 | 5 | | V-2 | Ntan1 |
| 5027 | 3 | 4 | 5 | | V-2 | Ntsr2 |
| 5028 | 3 | 4 | 5 | | V-2 | Nuak1 |
| 5029 | 3 | 4 | 5 | | V-2 | Nudcd2 |
| 5030 | 3 | 4 | 5 | | V-2 | Nudt16 |
| 5031 | 3 | 4 | 5 | | V-2 | Nudt3 |
| 5032 | 3 | 4 | 5 | | V-2 | Nudt9 |
| 5033 | 3 | 4 | 5 | | V-2 | Nup153 |
| 5034 | 3 | 4 | 5 | | V-2 | Nup210 |
| 5035 | 3 | 4 | 5 | | V-2 | Nup35 |
| 5036 | 3 | 4 | 5 | | V-2 | Nup62 |
| 5037 | 3 | 4 | 5 | | V-2 | Nxph2 |
| 5038 | 3 | 4 | 5 | | V-2 | Nxt2 |
| 5039 | 3 | 4 | 5 | | V-2 | Oaf |
| 5040 | 3 | 4 | 5 | | V-2 | Oas1c |
| 5041 | 3 | 4 | 5 | | V-2 | Oasl1 |
| 5042 | 3 | 4 | 5 | | V-2 | Obfc1 |
| 5043 | 3 | 4 | 5 | | V-2 | Ocel1 |
| 5044 | 3 | 4 | 5 | | V-2 | Ocrl |
| 5045 | 3 | 4 | 5 | | V-2 | Ogdh |
| 5046 | 3 | 4 | 5 | | V-2 | Ogn |
| 5047 | 3 | 4 | 5 | | V-2 | Oip5 |
| 5048 | 3 | 4 | 5 | | V-2 | Oit3 |
| 5049 | 3 | 4 | 5 | | V-2 | Olfml3 |
| 5050 | 3 | 4 | 5 | | V-2 | Olfr1372-ps1 |
| 5051 | 3 | 4 | 5 | | V-2 | Olfr1413 |
| 5052 | 3 | 4 | 5 | | V-2 | Olfr1507 |
| 5053 | 3 | 4 | 5 | | V-2 | Olfr165 |
| 5054 | 3 | 4 | 5 | | V-2 | Olfr287 |
| 5055 | 3 | 4 | 5 | | V-2 | Olfr308 |
| 5056 | 3 | 4 | 5 | | V-2 | Olfr78 |
| 5057 | 3 | 4 | 5 | | V-2 | Olfr920 |
| 5058 | 3 | 4 | 5 | | V-2 | Olfr94 |
| 5059 | 3 | 4 | 5 | | V-2 | Olfr99 |
| 5060 | 3 | 4 | 5 | | V-2 | Olig1 |
| 5061 | 3 | 4 | 5 | | V-2 | Onecut2 |
| 5062 | 3 | 4 | 5 | | V-2 | Orai1 |
| 5063 | 3 | 4 | 5 | | V-2 | Orc5 |
| 5064 | 3 | 4 | 5 | | V-2 | Osbpl1a |
| 5065 | 3 | 4 | 5 | | V-2 | Osbpl5 |
| 5066 | 3 | 4 | 5 | | V-2 | Osbpl8 |
| 5067 | 3 | 4 | 5 | | V-2 | Oscar |
| 5068 | 3 | 4 | 5 | | V-2 | Osgep |
| 5069 | 3 | 4 | 5 | | V-2 | Osgepl1 |
| 5070 | 3 | 4 | 5 | | V-2 | Ost4 |
| 5071 | 3 | 4 | 5 | | V-2 | Otop3 |
| 5072 | 3 | 4 | 5 | | V-2 | Otp |
| 5073 | 3 | 4 | 5 | | V-2 | Otud5 |
| 5074 | 3 | 4 | 5 | | V-2 | Otulin |
| 5075 | 3 | 4 | 5 | | V-2 | Ovol1 |
| 5076 | 3 | 4 | 5 | | V-2 | Oxnad1 |
| 5077 | 3 | 4 | 5 | | V-2 | Oxsm |
| 5078 | 3 | 4 | 5 | | V-2 | P2rx1 |
| 5079 | 3 | 4 | 5 | | V-2 | P2rx3 |
| 5080 | 3 | 4 | 5 | | V-2 | P2ry12 |
| 5081 | 3 | 4 | 5 | | V-2 | P4ha2 |
| 5082 | 3 | 4 | 5 | | V-2 | Pacsin2 |
| 5083 | 3 | 4 | 5 | | V-2 | Paip2 |
| 5084 | 3 | 4 | 5 | | V-2 | Pak1ip1 |
| 5085 | 3 | 4 | 5 | | V-2 | Pak6 |
| 5086 | 3 | 4 | 5 | | V-2 | Palm |
| 5087 | 3 | 4 | 5 | | V-2 | Papd5 |
| 5088 | 3 | 4 | 5 | | V-2 | Papolb |
| 5089 | 3 | 4 | 5 | | V-2 | Pard3b |
| 5090 | 3 | 4 | 5 | | V-2 | Pard6a |
| 5091 | 3 | 4 | 5 | | V-2 | Parl |
| 5092 | 3 | 4 | 5 | | V-2 | Parp16 |
| 5093 | 3 | 4 | 5 | | V-2 | Parp2 |
| 5094 | 3 | 4 | 5 | | V-2 | Parvb |
| 5095 | 3 | 4 | 5 | | V-2 | Parvg |
| 5096 | 3 | 4 | 5 | | V-2 | Patz1 |
| 5097 | 3 | 4 | 5 | | V-2 | Pbld2 |
| 5098 | 3 | 4 | 5 | | V-2 | Pbrm1 |
| 5099 | 3 | 4 | 5 | | V-2 | Pbx4 |
| 5100 | 3 | 4 | 5 | | V-2 | Pcbp3 |
| 5101 | 3 | 4 | 5 | | V-2 | Pcbp4 |
| 5102 | 3 | 4 | 5 | | V-2 | Pcdha4 |
| 5103 | 3 | 4 | 5 | | V-2 | Pcdhga4 |
| 5104 | 3 | 4 | 5 | | V-2 | Pcdhgb1 |
| 5105 | 3 | 4 | 5 | | V-2 | Pcdhgb2 |
| 5106 | 3 | 4 | 5 | | V-2 | Pcgf2 |
| 5107 | 3 | 4 | 5 | | V-2 | Pcif1 |
| 5108 | 3 | 4 | 5 | | V-2 | Pcmt1 |
| 5109 | 3 | 4 | 5 | | V-2 | Pcmtd1 |
| 5110 | 3 | 4 | 5 | | V-2 | Pcolce2 |
| 5111 | 3 | 4 | 5 | | V-2 | Pcp4 |
| 5112 | 3 | 4 | 5 | | V-2 | Pcp4l1 |
| 5113 | 3 | 4 | 5 | | V-2 | Pcsk2 |
| 5114 | 3 | 4 | 5 | | V-2 | Pcsk5 |
| 5115 | 3 | 4 | 5 | | V-2 | Pcyt1b |
| 5116 | 3 | 4 | 5 | | V-2 | Pdcd1 |
| 5117 | 3 | 4 | 5 | | V-2 | Pdcd10 |
| 5118 | 3 | 4 | 5 | | V-2 | Pdcd2 |
| 5119 | 3 | 4 | 5 | | V-2 | Pdcd6 |
| 5120 | 3 | 4 | 5 | | V-2 | Pddc1 |
| 5121 | 3 | 4 | 5 | | V-2 | Pde10a |
| 5122 | 3 | 4 | 5 | | V-2 | Pde1a |
| 5123 | 3 | 4 | 5 | | V-2 | Pde1b |
| 5124 | 3 | 4 | 5 | | V-2 | Pde5a |
| 5125 | 3 | 4 | 5 | | V-2 | Pde9a |
| 5126 | 3 | 4 | 5 | | V-2 | Pdgfa |
| 5127 | 3 | 4 | 5 | | V-2 | Pdia5 |
| 5128 | 3 | 4 | 5 | | V-2 | Pdia6 |
| 5129 | 3 | 4 | 5 | | V-2 | Pdk1 |
| 5130 | 3 | 4 | 5 | | V-2 | Pdk3 |
| 5131 | 3 | 4 | 5 | | V-2 | Pdlim3 |
| 5132 | 3 | 4 | 5 | | V-2 | Pdrg1 |
| 5133 | 3 | 4 | 5 | | V-2 | Pdzd9 |
| 5134 | 3 | 4 | 5 | | V-2 | Pea15a |
| 5135 | 3 | 4 | 5 | | V-2 | Pecam1 |
| 5136 | 3 | 4 | 5 | | V-2 | Pef1 |
| 5137 | 3 | 4 | 5 | | V-2 | Peli3 |
| 5138 | 3 | 4 | 5 | | V-2 | Per1 |
| 5139 | 3 | 4 | 5 | | V-2 | Pet100 |
| 5140 | 3 | 4 | 5 | | V-2 | Pet112 |
| 5141 | 3 | 4 | 5 | | V-2 | Pex11a |
| 5142 | 3 | 4 | 5 | | V-2 | Pex13 |
| 5143 | 3 | 4 | 5 | | V-2 | Pex19 |
| 5144 | 3 | 4 | 5 | | V-2 | Pex3 |
| 5145 | 3 | 4 | 5 | | V-2 | Pfdn1 |
| 5146 | 3 | 4 | 5 | | V-2 | Pgap1 |
| 5147 | 3 | 4 | 5 | | V-2 | Pgm1 |
| 5148 | 3 | 4 | 5 | | V-2 | Pgm2l1 |
| 5149 | 3 | 4 | 5 | | V-2 | Pgm3 |
| 5150 | 3 | 4 | 5 | | V-2 | Phf11b |
| 5151 | 3 | 4 | 5 | | V-2 | Phox2a |
| 5152 | 3 | 4 | 5 | | V-2 | Phpt1 |
| 5153 | 3 | 4 | 5 | | V-2 | Phyhd1 |
| 5154 | 3 | 4 | 5 | | V-2 | Phyhip |
| 5155 | 3 | 4 | 5 | | V-2 | Pi4kb |
| 5156 | 3 | 4 | 5 | | V-2 | Pidd1 |
| 5157 | 3 | 4 | 5 | | V-2 | Piga |
| 5158 | 3 | 4 | 5 | | V-2 | Pigm |
| 5159 | 3 | 4 | 5 | | V-2 | Pigo |
| 5160 | 3 | 4 | 5 | | V-2 | Pigq |
| 5161 | 3 | 4 | 5 | | V-2 | Pik3c2a |
| 5162 | 3 | 4 | 5 | | V-2 | Pik3r1 |
| 5163 | 3 | 4 | 5 | | V-2 | Pim1 |
| 5164 | 3 | 4 | 5 | | V-2 | Pin1rt1 |
| 5165 | 3 | 4 | 5 | | V-2 | Pink1 |
| 5166 | 3 | 4 | 5 | | V-2 | Pip4k2a |
| 5167 | 3 | 4 | 5 | | V-2 | Pithd1 |
| 5168 | 3 | 4 | 5 | | V-2 | Pitrm1 |
| 5169 | 3 | 4 | 5 | | V-2 | Pkd1l3 |
| 5170 | 3 | 4 | 5 | | V-2 | Pkm |
| 5171 | 3 | 4 | 5 | | V-2 | Pkn2 |
| 5172 | 3 | 4 | 5 | | V-2 | Pla1a |
| 5173 | 3 | 4 | 5 | | V-2 | Pla2g12a |
| 5174 | 3 | 4 | 5 | | V-2 | Pla2g16 |
| 5175 | 3 | 4 | 5 | | V-2 | Pla2g4a |
| 5176 | 3 | 4 | 5 | | V-2 | Pla2g6 |
| 5177 | 3 | 4 | 5 | | V-2 | Pla2r1 |
| 5178 | 3 | 4 | 5 | | V-2 | Plagl1 |
| 5179 | 3 | 4 | 5 | | V-2 | Plat |
| 5180 | 3 | 4 | 5 | | V-2 | Plb1 |
| 5181 | 3 | 4 | 5 | | V-2 | Plek |
| 5182 | 3 | 4 | 5 | | V-2 | Plekha2 |

Fig. 36 - 28

| | | | | | | | |
|---|---|---|---|---|---|---|---|
| 5183 | 3 | 4 | 5 | | | V-2 | Plekha4 |
| 5184 | 3 | 4 | 5 | | | V-2 | Plekhg3 |
| 5185 | 3 | 4 | 5 | | | V-2 | Plekhg6 |
| 5186 | 3 | 4 | 5 | | | V-2 | Plekhn1 |
| 5187 | 3 | 4 | 5 | | | V-2 | Plekhs1 |
| 5188 | 3 | 4 | 5 | | | V-2 | Plk5 |
| 5189 | 3 | 4 | 5 | | | V-2 | Pln |
| 5190 | 3 | 4 | 5 | | | V-2 | Plod3 |
| 5191 | 3 | 4 | 5 | | | V-2 | Plp1 |
| 5192 | 3 | 4 | 5 | | | V-2 | Pls1 |
| 5193 | 3 | 4 | 5 | | | V-2 | Plvap |
| 5194 | 3 | 4 | 5 | | | V-2 | Pmvk |
| 5195 | 3 | 4 | 5 | | | V-2 | Pnck |
| 5196 | 3 | 4 | 5 | | | V-2 | Pnp |
| 5197 | 3 | 4 | 5 | | | V-2 | Pnp2 |
| 5198 | 3 | 4 | 5 | | | V-2 | Pnpla2 |
| 5199 | 3 | 4 | 5 | | | V-2 | Pnpla8 |
| 5200 | 3 | 4 | 5 | | | V-2 | Pold4 |
| 5201 | 3 | 4 | 5 | | | V-2 | Pole4 |
| 5202 | 3 | 4 | 5 | | | V-2 | Polg2 |
| 5203 | 3 | 4 | 5 | | | V-2 | Polr1d |
| 5204 | 3 | 4 | 5 | | | V-2 | Polr2c |
| 5205 | 3 | 4 | 5 | | | V-2 | Polr2g |
| 5206 | 3 | 4 | 5 | | | V-2 | Polr3c |
| 5207 | 3 | 4 | 5 | | | V-2 | Polr3d |
| 5208 | 3 | 4 | 5 | | | V-2 | Polr3gl |
| 5209 | 3 | 4 | 5 | | | V-2 | Pom121l2 |
| 5210 | 3 | 4 | 5 | | | V-2 | Pomp |
| 5211 | 3 | 4 | 5 | | | V-2 | Pop4 |
| 5212 | 3 | 4 | 5 | | | V-2 | Popdc3 |
| 5213 | 3 | 4 | 5 | | | V-2 | Pot1b |
| 5214 | 3 | 4 | 5 | | | V-2 | Pou2af1 |
| 5215 | 3 | 4 | 5 | | | V-2 | Ppap2a |
| 5216 | 3 | 4 | 5 | | | V-2 | Ppapdc1a |
| 5217 | 3 | 4 | 5 | | | V-2 | Ppat |
| 5218 | 3 | 4 | 5 | | | V-2 | Ppia |
| 5219 | 3 | 4 | 5 | | | V-2 | Ppid |
| 5220 | 3 | 4 | 5 | | | V-2 | Ppil3 |
| 5221 | 3 | 4 | 5 | | | V-2 | Ppl |
| 5222 | 3 | 4 | 5 | | | V-2 | Ppp1r13l |
| 5223 | 3 | 4 | 5 | | | V-2 | Ppp1r14b |
| 5224 | 3 | 4 | 5 | | | V-2 | Ppp1r16b |
| 5225 | 3 | 4 | 5 | | | V-2 | Ppp1r18 |
| 5226 | 3 | 4 | 5 | | | V-2 | Ppp1r35 |
| 5227 | 3 | 4 | 5 | | | V-2 | Ppp1r3f |
| 5228 | 3 | 4 | 5 | | | V-2 | Ppp2cb |
| 5229 | 3 | 4 | 5 | | | V-2 | Ppp2r2cos |
| 5230 | 3 | 4 | 5 | | | V-2 | Ppp2r3c |
| 5231 | 3 | 4 | 5 | | | V-2 | Ppp2r4 |
| 5232 | 3 | 4 | 5 | | | V-2 | Ppp2r5b |
| 5233 | 3 | 4 | 5 | | | V-2 | Ppp6c |
| 5234 | 3 | 4 | 5 | | | V-2 | Ppp6r1 |
| 5235 | 3 | 4 | 5 | | | V-2 | Ppp6r3 |
| 5236 | 3 | 4 | 5 | | | V-2 | Pqlc1 |
| 5237 | 3 | 4 | 5 | | | V-2 | Pramel1 |
| 5238 | 3 | 4 | 5 | | | V-2 | Prdm14 |
| 5239 | 3 | 4 | 5 | | | V-2 | Prdm5 |
| 5240 | 3 | 4 | 5 | | | V-2 | Prdx4 |
| 5241 | 3 | 4 | 5 | | | V-2 | Prdx6 |
| 5242 | 3 | 4 | 5 | | | V-2 | Prdx6b |
| 5243 | 3 | 4 | 5 | | | V-2 | Prelp |
| 5244 | 3 | 4 | 5 | | | V-2 | Prg2 |
| 5245 | 3 | 4 | 5 | | | V-2 | Prg3 |
| 5246 | 3 | 4 | 5 | | | V-2 | Prim1 |
| 5247 | 3 | 4 | 5 | | | V-2 | Prkab1 |
| 5248 | 3 | 4 | 5 | | | V-2 | Prkab2 |
| 5249 | 3 | 4 | 5 | | | V-2 | Prkar1b |
| 5250 | 3 | 4 | 5 | | | V-2 | Prkcdbp |
| 5251 | 3 | 4 | 5 | | | V-2 | Prkcg |
| 5252 | 3 | 4 | 5 | | | V-2 | Prkcq |
| 5253 | 3 | 4 | 5 | | | V-2 | Prodh |
| 5254 | 3 | 4 | 5 | | | V-2 | Prorsd1 |
| 5255 | 3 | 4 | 5 | | | V-2 | Proser2 |
| 5256 | 3 | 4 | 5 | | | V-2 | Prps1 |
| 5257 | 3 | 4 | 5 | | | V-2 | Prr13 |
| 5258 | 3 | 4 | 5 | | | V-2 | Prr16 |
| 5259 | 3 | 4 | 5 | | | V-2 | Prr3 |
| 5260 | 3 | 4 | 5 | | | V-2 | Prr5l |
| 5261 | 3 | 4 | 5 | | | V-2 | Prr7 |
| 5262 | 3 | 4 | 5 | | | V-2 | Prr9 |
| 5263 | 3 | 4 | 5 | | | V-2 | Prrt4 |
| 5264 | 3 | 4 | 5 | | | V-2 | Prss36 |
| 5265 | 3 | 4 | 5 | | | V-2 | Prx |
| 5266 | 3 | 4 | 5 | | | V-2 | Psma2 |
| 5267 | 3 | 4 | 5 | | | V-2 | Psma4 |
| 5268 | 3 | 4 | 5 | | | V-2 | Psma6 |
| 5269 | 3 | 4 | 5 | | | V-2 | Psmb2 |
| 5270 | 3 | 4 | 5 | | | V-2 | Psmb4 |
| 5271 | 3 | 4 | 5 | | | V-2 | Psmc3ip |
| 5272 | 3 | 4 | 5 | | | V-2 | Psmc6 |
| 5273 | 3 | 4 | 5 | | | V-2 | Psmd10 |
| 5274 | 3 | 4 | 5 | | | V-2 | Psmd14 |
| 5275 | 3 | 4 | 5 | | | V-2 | Psmd4 |
| 5276 | 3 | 4 | 5 | | | V-2 | Psme2b |
| 5277 | 3 | 4 | 5 | | | V-2 | Psme3 |
| 5278 | 3 | 4 | 5 | | | V-2 | Psmf1 |
| 5279 | 3 | 4 | 5 | | | V-2 | Psmg1 |
| 5280 | 3 | 4 | 5 | | | V-2 | Pspn |
| 5281 | 3 | 4 | 5 | | | V-2 | Psrc1 |
| 5282 | 3 | 4 | 5 | | | V-2 | Pstk |
| 5283 | 3 | 4 | 5 | | | V-2 | Ptcd2 |
| 5284 | 3 | 4 | 5 | | | V-2 | Ptges3 |
| 5285 | 3 | 4 | 5 | | | V-2 | Ptgir |
| 5286 | 3 | 4 | 5 | | | V-2 | Ptk2b |
| 5287 | 3 | 4 | 5 | | | V-2 | Ptma |
| 5288 | 3 | 4 | 5 | | | V-2 | Ptp4a3 |
| 5289 | 3 | 4 | 5 | | | V-2 | Ptpmt1 |
| 5290 | 3 | 4 | 5 | | | V-2 | Ptpn1 |
| 5291 | 3 | 4 | 5 | | | V-2 | Ptpn11 |
| 5292 | 3 | 4 | 5 | | | V-2 | Ptpn12 |
| 5293 | 3 | 4 | 5 | | | V-2 | Ptpn13 |
| 5294 | 3 | 4 | 5 | | | V-2 | Ptpn18 |
| 5295 | 3 | 4 | 5 | | | V-2 | Ptpn20 |
| 5296 | 3 | 4 | 5 | | | V-2 | Ptprd |
| 5297 | 3 | 4 | 5 | | | V-2 | Ptprj |
| 5298 | 3 | 4 | 5 | | | V-2 | Ptprk |
| 5299 | 3 | 4 | 5 | | | V-2 | Ptprm |
| 5300 | 3 | 4 | 5 | | | V-2 | Ptprn |
| 5301 | 3 | 4 | 5 | | | V-2 | Ptrf |
| 5302 | 3 | 4 | 5 | | | V-2 | Ptrhd1 |
| 5303 | 3 | 4 | 5 | | | V-2 | Pttg1ip |
| 5304 | 3 | 4 | 5 | | | V-2 | Pus7l |
| 5305 | 3 | 4 | 5 | | | V-2 | Pxmp2 |
| 5306 | 3 | 4 | 5 | | | V-2 | Pycr2 |
| 5307 | 3 | 4 | 5 | | | V-2 | Pygb |
| 5308 | 3 | 4 | 5 | | | V-2 | Pygl |
| 5309 | 3 | 4 | 5 | | | V-2 | Qpct |
| 5310 | 3 | 4 | 5 | | | V-2 | Qsox1 |
| 5311 | 3 | 4 | 5 | | | V-2 | R3hdm1 |
| 5312 | 3 | 4 | 5 | | | V-2 | R3hdml |
| 5313 | 3 | 4 | 5 | | | V-2 | R74862 |
| 5314 | 3 | 4 | 5 | | | V-2 | Rab11a |
| 5315 | 3 | 4 | 5 | | | V-2 | Rab11b |
| 5316 | 3 | 4 | 5 | | | V-2 | Rab11fip2 |
| 5317 | 3 | 4 | 5 | | | V-2 | Rab12 |
| 5318 | 3 | 4 | 5 | | | V-2 | Rab13 |
| 5319 | 3 | 4 | 5 | | | V-2 | Rab27b |
| 5320 | 3 | 4 | 5 | | | V-2 | Rab33a |
| 5321 | 3 | 4 | 5 | | | V-2 | Rab4a |
| 5322 | 3 | 4 | 5 | | | V-2 | Rab5c |
| 5323 | 3 | 4 | 5 | | | V-2 | Rab6a |
| 5324 | 3 | 4 | 5 | | | V-2 | Rab6b |
| 5325 | 3 | 4 | 5 | | | V-2 | Rabac1 |
| 5326 | 3 | 4 | 5 | | | V-2 | Rabgap1l |
| 5327 | 3 | 4 | 5 | | | V-2 | Rabggtb |
| 5328 | 3 | 4 | 5 | | | V-2 | Rabl3 |
| 5329 | 3 | 4 | 5 | | | V-2 | Rad51b |
| 5330 | 3 | 4 | 5 | | | V-2 | Rag2 |
| 5331 | 3 | 4 | 5 | | | V-2 | Rai2 |
| 5332 | 3 | 4 | 5 | | | V-2 | Ralbp1 |
| 5333 | 3 | 4 | 5 | | | V-2 | Raly |
| 5334 | 3 | 4 | 5 | | | V-2 | Ramp1 |
| 5335 | 3 | 4 | 5 | | | V-2 | Ramp2 |
| 5336 | 3 | 4 | 5 | | | V-2 | Ranbp1 |
| 5337 | 3 | 4 | 5 | | | V-2 | Ranbp6 |
| 5338 | 3 | 4 | 5 | | | V-2 | Ranbp9 |
| 5339 | 3 | 4 | 5 | | | V-2 | Rap2a |
| 5340 | 3 | 4 | 5 | | | V-2 | Rapgef4 |
| 5341 | 3 | 4 | 5 | | | V-2 | Rapgef6 |
| 5342 | 3 | 4 | 5 | | | V-2 | Rasa3 |
| 5343 | 3 | 4 | 5 | | | V-2 | Rasgrf2 |
| 5344 | 3 | 4 | 5 | | | V-2 | Rasl11b |
| 5345 | 3 | 4 | 5 | | | V-2 | Rassf10 |
| 5346 | 3 | 4 | 5 | | | V-2 | Rassf5 |
| 5347 | 3 | 4 | 5 | | | V-2 | Rassf6 |
| 5348 | 3 | 4 | 5 | | | V-2 | Rbbp4 |
| 5349 | 3 | 4 | 5 | | | V-2 | Rbm38 |
| 5350 | 3 | 4 | 5 | | | V-2 | Rbm4 |
| 5351 | 3 | 4 | 5 | | | V-2 | Rbm46 |
| 5352 | 3 | 4 | 5 | | | V-2 | Rbmx2 |
| 5353 | 3 | 4 | 5 | | | V-2 | Rbpms |
| 5354 | 3 | 4 | 5 | | | V-2 | Rc3h1 |
| 5355 | 3 | 4 | 5 | | | V-2 | Rchy1 |
| 5356 | 3 | 4 | 5 | | | V-2 | Rcn3 |
| 5357 | 3 | 4 | 5 | | | V-2 | Rcor3 |
| 5358 | 3 | 4 | 5 | | | V-2 | Rdh9 |
| 5359 | 3 | 4 | 5 | | | V-2 | Reep2 |
| 5360 | 3 | 4 | 5 | | | V-2 | Ren1 |
| 5361 | 3 | 4 | 5 | | | V-2 | Rfc4 |
| 5362 | 3 | 4 | 5 | | | V-2 | Rfc5 |
| 5363 | 3 | 4 | 5 | | | V-2 | Rfesd |
| 5364 | 3 | 4 | 5 | | | V-2 | Rffl |
| 5365 | 3 | 4 | 5 | | | V-2 | Rfk |
| 5366 | 3 | 4 | 5 | | | V-2 | Rftn1 |
| 5367 | 3 | 4 | 5 | | | V-2 | Rfx2 |
| 5368 | 3 | 4 | 5 | | | V-2 | Rgp1 |
| 5369 | 3 | 4 | 5 | | | V-2 | Rgs18 |
| 5370 | 3 | 4 | 5 | | | V-2 | Rgs20 |
| 5371 | 3 | 4 | 5 | | | V-2 | Rgs9bp |
| 5372 | 3 | 4 | 5 | | | V-2 | Rhbdd2 |
| 5373 | 3 | 4 | 5 | | | V-2 | Rhbg |
| 5374 | 3 | 4 | 5 | | | V-2 | Rhd |

Fig. 36 - 29

| | | | | | | | |
|---|---|---|---|---|---|---|---|
| 5375 | 3 | 4 | 5 | | | V-2 | Rheb |
| 5376 | 3 | 4 | 5 | | | V-2 | Rhoj |
| 5377 | 3 | 4 | 5 | | | V-2 | Ribc1 |
| 5378 | 3 | 4 | 5 | | | V-2 | Ric8 |
| 5379 | 3 | 4 | 5 | | | V-2 | Rimbp3 |
| 5380 | 3 | 4 | 5 | | | V-2 | Rims2 |
| 5381 | 3 | 4 | 5 | | | V-2 | Rin3 |
| 5382 | 3 | 4 | 5 | | | V-2 | Riok2 |
| 5383 | 3 | 4 | 5 | | | V-2 | Riok3 |
| 5384 | 3 | 4 | 5 | | | V-2 | Ripk3 |
| 5385 | 3 | 4 | 5 | | | V-2 | Ripk4 |
| 5386 | 3 | 4 | 5 | | | V-2 | Rit1 |
| 5387 | 3 | 4 | 5 | | | V-2 | Rmnd5a |
| 5388 | 3 | 4 | 5 | | | V-2 | Rnaseh1 |
| 5389 | 3 | 4 | 5 | | | V-2 | Rnd3 |
| 5390 | 3 | 4 | 5 | | | V-2 | Rnf113a1 |
| 5391 | 3 | 4 | 5 | | | V-2 | Rnf113a2 |
| 5392 | 3 | 4 | 5 | | | V-2 | Rnf114 |
| 5393 | 3 | 4 | 5 | | | V-2 | Rnf115 |
| 5394 | 3 | 4 | 5 | | | V-2 | Rnf138rt1 |
| 5395 | 3 | 4 | 5 | | | V-2 | Rnf14 |
| 5396 | 3 | 4 | 5 | | | V-2 | Rnf144b |
| 5397 | 3 | 4 | 5 | | | V-2 | Rnf166 |
| 5398 | 3 | 4 | 5 | | | V-2 | Rnf181 |
| 5399 | 3 | 4 | 5 | | | V-2 | Rnf187 |
| 5400 | 3 | 4 | 5 | | | V-2 | Rnf19b |
| 5401 | 3 | 4 | 5 | | | V-2 | Rnf207 |
| 5402 | 3 | 4 | 5 | | | V-2 | Rnf223 |
| 5403 | 3 | 4 | 5 | | | V-2 | Rnf25 |
| 5404 | 3 | 4 | 5 | | | V-2 | Rnf38 |
| 5405 | 3 | 4 | 5 | | | V-2 | Rnf5 |
| 5406 | 3 | 4 | 5 | | | V-2 | Rngtt |
| 5407 | 3 | 4 | 5 | | | V-2 | Rnpc3 |
| 5408 | 3 | 4 | 5 | | | V-2 | Robo1 |
| 5409 | 3 | 4 | 5 | | | V-2 | Ror2 |
| 5410 | 3 | 4 | 5 | | | V-2 | Rpa2 |
| 5411 | 3 | 4 | 5 | | | V-2 | Rpe |
| 5412 | 3 | 4 | 5 | | | V-2 | Rpl14-ps1 |
| 5413 | 3 | 4 | 5 | | | V-2 | Rpl15 |
| 5414 | 3 | 4 | 5 | | | V-2 | Rpl17 |
| 5415 | 3 | 4 | 5 | | | V-2 | Rpl21 |
| 5416 | 3 | 4 | 5 | | | V-2 | Rpl22l1 |
| 5417 | 3 | 4 | 5 | | | V-2 | Rpl23a |
| 5418 | 3 | 4 | 5 | | | V-2 | Rpl24 |
| 5419 | 3 | 4 | 5 | | | V-2 | Rpl4 |
| 5420 | 3 | 4 | 5 | | | V-2 | Rpl5 |
| 5421 | 3 | 4 | 5 | | | V-2 | Rpl7 |
| 5422 | 3 | 4 | 5 | | | V-2 | Rpl7a |
| 5423 | 3 | 4 | 5 | | | V-2 | Rpl8 |
| 5424 | 3 | 4 | 5 | | | V-2 | Rpp25l |
| 5425 | 3 | 4 | 5 | | | V-2 | Rps13 |
| 5426 | 3 | 4 | 5 | | | V-2 | Rps16 |
| 5427 | 3 | 4 | 5 | | | V-2 | Rps2 |
| 5428 | 3 | 4 | 5 | | | V-2 | Rps20 |
| 5429 | 3 | 4 | 5 | | | V-2 | Rps6 |
| 5430 | 3 | 4 | 5 | | | V-2 | Rps6ka4 |
| 5431 | 3 | 4 | 5 | | | V-2 | Rps6kb2 |
| 5432 | 3 | 4 | 5 | | | V-2 | Rps7 |
| 5433 | 3 | 4 | 5 | | | V-2 | Rrm2b |
| 5434 | 3 | 4 | 5 | | | V-2 | Rsad1 |
| 5435 | 3 | 4 | 5 | | | V-2 | Rsbn1l |
| 5436 | 3 | 4 | 5 | | | V-2 | Rsf1 |
| 5437 | 3 | 4 | 5 | | | V-2 | Rskan18 |
| 5438 | 3 | 4 | 5 | | | V-2 | Rspo2 |
| 5439 | 3 | 4 | 5 | | | V-2 | Rtca |
| 5440 | 3 | 4 | 5 | | | V-2 | Rtn4 |
| 5441 | 3 | 4 | 5 | | | V-2 | Rtn4ip1 |
| 5442 | 3 | 4 | 5 | | | V-2 | Rtn4rl2 |
| 5443 | 3 | 4 | 5 | | | V-2 | Rubie |
| 5444 | 3 | 4 | 5 | | | V-2 | Rwdd2a |
| 5445 | 3 | 4 | 5 | | | V-2 | Ryk |
| 5446 | 3 | 4 | 5 | | | V-2 | S100a3 |
| 5447 | 3 | 4 | 5 | | | V-2 | S100b |
| 5448 | 3 | 4 | 5 | | | V-2 | Sag |
| 5449 | 3 | 4 | 5 | | | V-2 | Samd14 |
| 5450 | 3 | 4 | 5 | | | V-2 | Samd3 |
| 5451 | 3 | 4 | 5 | | | V-2 | Sap30 |
| 5452 | 3 | 4 | 5 | | | V-2 | Sapcd2 |
| 5453 | 3 | 4 | 5 | | | V-2 | Sarnp |
| 5454 | 3 | 4 | 5 | | | V-2 | Sash1 |
| 5455 | 3 | 4 | 5 | | | V-2 | Sav1 |
| 5456 | 3 | 4 | 5 | | | V-2 | Sbds |
| 5457 | 3 | 4 | 5 | | | V-2 | Sc5d |
| 5458 | 3 | 4 | 5 | | | V-2 | Scamp5 |
| 5459 | 3 | 4 | 5 | | | V-2 | Scel |
| 5460 | 3 | 4 | 5 | | | V-2 | Scg5 |
| 5461 | 3 | 4 | 5 | | | V-2 | Scgb2b17 |
| 5462 | 3 | 4 | 5 | | | V-2 | Scgb2b20 |
| 5463 | 3 | 4 | 5 | | | V-2 | Scgn |
| 5464 | 3 | 4 | 5 | | | V-2 | Schip1 |
| 5465 | 3 | 4 | 5 | | | V-2 | Sck1 |
| 5466 | 3 | 4 | 5 | | | V-2 | Scml4 |
| 5467 | 3 | 4 | 5 | | | V-2 | Scn3b |
| 5468 | 3 | 4 | 5 | | | V-2 | Scoc |
| 5469 | 3 | 4 | 5 | | | V-2 | Sdf2 |
| 5470 | 3 | 4 | 5 | | | V-2 | Sdhaf1 |
| 5471 | 3 | 4 | 5 | | | V-2 | Sdhaf2 |
| 5472 | 3 | 4 | 5 | | | V-2 | Sdhb |
| 5473 | 3 | 4 | 5 | | | V-2 | Sdpr |
| 5474 | 3 | 4 | 5 | | | V-2 | Sdsl |
| 5475 | 3 | 4 | 5 | | | V-2 | Sec31b |
| 5476 | 3 | 4 | 5 | | | V-2 | Sema3d |
| 5477 | 3 | 4 | 5 | | | V-2 | Sema7a |
| 5478 | 3 | 4 | 5 | | | V-2 | Senp7 |
| 5479 | 3 | 4 | 5 | | | V-2 | Sept6 |
| 5480 | 3 | 4 | 5 | | | V-2 | Sept7 |
| 5481 | 3 | 4 | 5 | | | V-2 | Sept8 |
| 5482 | 3 | 4 | 5 | | | V-2 | Sept9 |
| 5483 | 3 | 4 | 5 | | | V-2 | Sepw1 |
| 5484 | 3 | 4 | 5 | | | V-2 | Serbp1 |
| 5485 | 3 | 4 | 5 | | | V-2 | Serf2 |
| 5486 | 3 | 4 | 5 | | | V-2 | Serhl |
| 5487 | 3 | 4 | 5 | | | V-2 | Serinc3 |
| 5488 | 3 | 4 | 5 | | | V-2 | Serinc5 |
| 5489 | 3 | 4 | 5 | | | V-2 | Serpina3a |
| 5490 | 3 | 4 | 5 | | | V-2 | Serpina3i |
| 5491 | 3 | 4 | 5 | | | V-2 | Serpinh6a |
| 5492 | 3 | 4 | 5 | | | V-2 | Serpinb8 |
| 5493 | 3 | 4 | 5 | | | V-2 | Serpine2 |
| 5494 | 3 | 4 | 5 | | | V-2 | Serpine3 |
| 5495 | 3 | 4 | 5 | | | V-2 | Sertad3 |
| 5496 | 3 | 4 | 5 | | | V-2 | Sesn1 |
| 5497 | 3 | 4 | 5 | | | V-2 | Sez6l2 |
| 5498 | 3 | 4 | 5 | | | V-2 | Sf3b6 |
| 5499 | 3 | 4 | 5 | | | V-2 | Sfrp4 |
| 5500 | 3 | 4 | 5 | | | V-2 | Sfrp5 |
| 5501 | 3 | 4 | 5 | | | V-2 | Sfxn3 |
| 5502 | 3 | 4 | 5 | | | V-2 | Sgk1 |
| 5503 | 3 | 4 | 5 | | | V-2 | Sgol2 |
| 5504 | 3 | 4 | 5 | | | V-2 | Sgsm3 |
| 5505 | 3 | 4 | 5 | | | V-2 | Sgta |
| 5506 | 3 | 4 | 5 | | | V-2 | Sh3bgrl |
| 5507 | 3 | 4 | 5 | | | V-2 | Sh3bp4 |
| 5508 | 3 | 4 | 5 | | | V-2 | Sh3gl1 |
| 5509 | 3 | 4 | 5 | | | V-2 | Sh3tc2 |
| 5510 | 3 | 4 | 5 | | | V-2 | Shfm1 |
| 5511 | 3 | 4 | 5 | | | V-2 | Shisa4 |
| 5512 | 3 | 4 | 5 | | | V-2 | Shmt1 |
| 5513 | 3 | 4 | 5 | | | V-2 | Shprh |
| 5514 | 3 | 4 | 5 | | | V-2 | Shroom2 |
| 5515 | 3 | 4 | 5 | | | V-2 | Siah1b |
| 5516 | 3 | 4 | 5 | | | V-2 | Sin3a |
| 5517 | 3 | 4 | 5 | | | V-2 | Sipa1 |
| 5518 | 3 | 4 | 5 | | | V-2 | Sirt2 |
| 5519 | 3 | 4 | 5 | | | V-2 | Sit1 |
| 5520 | 3 | 4 | 5 | | | V-2 | Skint10 |
| 5521 | 3 | 4 | 5 | | | V-2 | Skint11 |
| 5522 | 3 | 4 | 5 | | | V-2 | Skiv2l |
| 5523 | 3 | 4 | 5 | | | V-2 | Skp1a |
| 5524 | 3 | 4 | 5 | | | V-2 | Sla |
| 5525 | 3 | 4 | 5 | | | V-2 | Slain1 |
| 5526 | 3 | 4 | 5 | | | V-2 | Slain2 |
| 5527 | 3 | 4 | 5 | | | V-2 | Slamf1 |
| 5528 | 3 | 4 | 5 | | | V-2 | Slamf6 |
| 5529 | 3 | 4 | 5 | | | V-2 | Slc10a6 |
| 5530 | 3 | 4 | 5 | | | V-2 | Slc14a2 |
| 5531 | 3 | 4 | 5 | | | V-2 | Slc17a1 |
| 5532 | 3 | 4 | 5 | | | V-2 | Slc18a2 |
| 5533 | 3 | 4 | 5 | | | V-2 | Slc18a3 |
| 5534 | 3 | 4 | 5 | | | V-2 | Slc1a4 |
| 5535 | 3 | 4 | 5 | | | V-2 | Slc1a5 |
| 5536 | 3 | 4 | 5 | | | V-2 | Slc20a2 |
| 5537 | 3 | 4 | 5 | | | V-2 | Slc22a1 |
| 5538 | 3 | 4 | 5 | | | V-2 | Slc23a2 |
| 5539 | 3 | 4 | 5 | | | V-2 | Slc23a3 |
| 5540 | 3 | 4 | 5 | | | V-2 | Slc25a16 |
| 5541 | 3 | 4 | 5 | | | V-2 | Slc25a27 |
| 5542 | 3 | 4 | 5 | | | V-2 | Slc25a33 |
| 5543 | 3 | 4 | 5 | | | V-2 | Slc25a37 |
| 5544 | 3 | 4 | 5 | | | V-2 | Slc25a39 |
| 5545 | 3 | 4 | 5 | | | V-2 | Slc25a40 |
| 5546 | 3 | 4 | 5 | | | V-2 | Slc27a1 |
| 5547 | 3 | 4 | 5 | | | V-2 | Slc2a3 |
| 5548 | 3 | 4 | 5 | | | V-2 | Slc2a4 |
| 5549 | 3 | 4 | 5 | | | V-2 | Slc2a5 |
| 5550 | 3 | 4 | 5 | | | V-2 | Slc2a8 |
| 5551 | 3 | 4 | 5 | | | V-2 | Slc30a6 |
| 5552 | 3 | 4 | 5 | | | V-2 | Slc35a3 |
| 5553 | 3 | 4 | 5 | | | V-2 | Slc35b3 |
| 5554 | 3 | 4 | 5 | | | V-2 | Slc35d2 |
| 5555 | 3 | 4 | 5 | | | V-2 | Slc35f6 |
| 5556 | 3 | 4 | 5 | | | V-2 | Slc38a2 |
| 5557 | 3 | 4 | 5 | | | V-2 | Slc39a10 |
| 5558 | 3 | 4 | 5 | | | V-2 | Slc39a8 |
| 5559 | 3 | 4 | 5 | | | V-2 | Slc3a2 |
| 5560 | 3 | 4 | 5 | | | V-2 | Slc43a1 |
| 5561 | 3 | 4 | 5 | | | V-2 | Slc45a4 |
| 5562 | 3 | 4 | 5 | | | V-2 | Slc48a1 |
| 5563 | 3 | 4 | 5 | | | V-2 | Slc4a7 |
| 5564 | 3 | 4 | 5 | | | V-2 | Slc50a1 |
| 5565 | 3 | 4 | 5 | | | V-2 | Slc5a8 |
| 5566 | 3 | 4 | 5 | | | V-2 | Slc6a12 |

Fig. 36 - 30

| | | | | | | | |
|---|---|---|---|---|---|---|---|
| 5567 | 3 | 4 | 5 | | V-2 | Slc6a19os | |
| 5568 | 3 | 4 | 5 | | V-2 | Slc8b1 | |
| 5569 | 3 | 4 | 5 | | V-2 | Slc9a6 | |
| 5570 | 3 | 4 | 5 | | V-2 | Slco1a4 | |
| 5571 | 3 | 4 | 5 | | V-2 | Slco2a1 | |
| 5572 | 3 | 4 | 5 | | V-2 | Slfn14 | |
| 5573 | 3 | 4 | 5 | | V-2 | Slit2 | |
| 5574 | 3 | 4 | 5 | | V-2 | Slmap | |
| 5575 | 3 | 4 | 5 | | V-2 | Slurp1 | |
| 5576 | 3 | 4 | 5 | | V-2 | Smarca1 | |
| 5577 | 3 | 4 | 5 | | V-2 | Smarcd3 | |
| 5578 | 3 | 4 | 5 | | V-2 | Smc1a | |
| 5579 | 3 | 4 | 5 | | V-2 | Smc2os | |
| 5580 | 3 | 4 | 5 | | V-2 | Smdt1 | |
| 5581 | 3 | 4 | 5 | | V-2 | Smim19 | |
| 5582 | 3 | 4 | 5 | | V-2 | Smim4 | |
| 5583 | 3 | 4 | 5 | | V-2 | Smim6 | |
| 5584 | 3 | 4 | 5 | | V-2 | Smim8 | |
| 5585 | 3 | 4 | 5 | | V-2 | Smpd3 | |
| 5586 | 3 | 4 | 5 | | V-2 | Smpd5 | |
| 5587 | 3 | 4 | 5 | | V-2 | Snap23 | |
| 5588 | 3 | 4 | 5 | | V-2 | Snap47 | |
| 5589 | 3 | 4 | 5 | | V-2 | Snapc5 | |
| 5590 | 3 | 4 | 5 | | V-2 | Snapin | |
| 5591 | 3 | 4 | 5 | | V-2 | Sncaip | |
| 5592 | 3 | 4 | 5 | | V-2 | Snhg5 | |
| 5593 | 3 | 4 | 5 | | V-2 | Snhg9 | |
| 5594 | 3 | 4 | 5 | | V-2 | Snrpb2 | |
| 5595 | 3 | 4 | 5 | | V-2 | Snrpc | |
| 5596 | 3 | 4 | 5 | | V-2 | Snrpd1 | |
| 5597 | 3 | 4 | 5 | | V-2 | Snupn | |
| 5598 | 3 | 4 | 5 | | V-2 | Snx10 | |
| 5599 | 3 | 4 | 5 | | V-2 | Snx12 | |
| 5600 | 3 | 4 | 5 | | V-2 | Snx22 | |
| 5601 | 3 | 4 | 5 | | V-2 | Snx3 | |
| 5602 | 3 | 4 | 5 | | V-2 | Snx33 | |
| 5603 | 3 | 4 | 5 | | V-2 | Snx4 | |
| 5604 | 3 | 4 | 5 | | V-2 | Sod2 | |
| 5605 | 3 | 4 | 5 | | V-2 | Sox12 | |
| 5606 | 3 | 4 | 5 | | V-2 | Sox17 | |
| 5607 | 3 | 4 | 5 | | V-2 | Sox18 | |
| 5608 | 3 | 4 | 5 | | V-2 | Sox7 | |
| 5609 | 3 | 4 | 5 | | V-2 | Spaca6 | |
| 5610 | 3 | 4 | 5 | | V-2 | Spag17 | |
| 5611 | 3 | 4 | 5 | | V-2 | Spata22 | |
| 5612 | 3 | 4 | 5 | | V-2 | Spata31d1c | |
| 5613 | 3 | 4 | 5 | | V-2 | Spata7 | |
| 5614 | 3 | 4 | 5 | | V-2 | Spata9 | |
| 5615 | 3 | 4 | 5 | | V-2 | Spc25 | |
| 5616 | 3 | 4 | 5 | | V-2 | Spef1 | |
| 5617 | 3 | 4 | 5 | | V-2 | Spef2 | |
| 5618 | 3 | 4 | 5 | | V-2 | Spice1 | |
| 5619 | 3 | 4 | 5 | | V-2 | Spidr | |
| 5620 | 3 | 4 | 5 | | V-2 | Spin4 | |
| 5621 | 3 | 4 | 5 | | V-2 | Spinkl | |
| 5622 | 3 | 4 | 5 | | V-2 | Spire1 | |
| 5623 | 3 | 4 | 5 | | V-2 | Spn | |
| 5624 | 3 | 4 | 5 | | V-2 | Spop | |
| 5625 | 3 | 4 | 5 | | V-2 | Sprr2f | |
| 5626 | 3 | 4 | 5 | | V-2 | Sprr2g | |
| 5627 | 3 | 4 | 5 | | V-2 | Sprr2h | |
| 5628 | 3 | 4 | 5 | | V-2 | Spry1 | |
| 5629 | 3 | 4 | 5 | | V-2 | Spryd7 | |
| 5630 | 3 | 4 | 5 | | V-2 | Spsb1 | |
| 5631 | 3 | 4 | 5 | | V-2 | Sptssb | |
| 5632 | 3 | 4 | 5 | | V-2 | Src | |
| 5633 | 3 | 4 | 5 | | V-2 | Srcrb4d | |
| 5634 | 3 | 4 | 5 | | V-2 | Srp14 | |
| 5635 | 3 | 4 | 5 | | V-2 | Srp9 | |
| 5636 | 3 | 4 | 5 | | V-2 | Srpk3 | |
| 5637 | 3 | 4 | 5 | | V-2 | Srpx | |
| 5638 | 3 | 4 | 5 | | V-2 | Srrd | |
| 5639 | 3 | 4 | 5 | | V-2 | Srrm4 | |
| 5640 | 3 | 4 | 5 | | V-2 | Srsf11 | |
| 5641 | 3 | 4 | 5 | | V-2 | Srxn1 | |
| 5642 | 3 | 4 | 5 | | V-2 | Ssbp3 | |
| 5643 | 3 | 4 | 5 | | V-2 | Ssna1 | |
| 5644 | 3 | 4 | 5 | | V-2 | Sst | |
| 5645 | 3 | 4 | 5 | | V-2 | Stac2 | |
| 5646 | 3 | 4 | 5 | | V-2 | Stag1 | |
| 5647 | 3 | 4 | 5 | | V-2 | Star | |
| 5648 | 3 | 4 | 5 | | V-2 | Stard3nl | |
| 5649 | 3 | 4 | 5 | | V-2 | Stim1 | |
| 5650 | 3 | 4 | 5 | | V-2 | Stk25 | |
| 5651 | 3 | 4 | 5 | | V-2 | Stk4 | |
| 5652 | 3 | 4 | 5 | | V-2 | Stmn3 | |
| 5653 | 3 | 4 | 5 | | V-2 | Stom | |
| 5654 | 3 | 4 | 5 | | V-2 | Stoml2 | |
| 5655 | 3 | 4 | 5 | | V-2 | Stra13 | |
| 5656 | 3 | 4 | 5 | | V-2 | Stradb | |
| 5657 | 3 | 4 | 5 | | V-2 | Stx18 | |
| 5658 | 3 | 4 | 5 | | V-2 | Stx2 | |
| 5659 | 3 | 4 | 5 | | V-2 | Stx4a | |
| 5660 | 3 | 4 | 5 | | V-2 | Stxbp3b | |
| 5661 | 3 | 4 | 5 | | V-2 | Stxbp6 | |
| 5662 | 3 | 4 | 5 | | V-2 | Styx | |
| 5663 | 3 | 4 | 5 | | V-2 | Sucnr1 | |
| 5664 | 3 | 4 | 5 | | V-2 | Suds3 | |
| 5665 | 3 | 4 | 5 | | V-2 | Sult1b1 | |
| 5666 | 3 | 4 | 5 | | V-2 | Sult2b1 | |
| 5667 | 3 | 4 | 5 | | V-2 | Sumo1 | |
| 5668 | 3 | 4 | 5 | | V-2 | Sumo2 | |
| 5669 | 3 | 4 | 5 | | V-2 | Supt7l | |
| 5670 | 3 | 4 | 5 | | V-2 | Surf1 | |
| 5671 | 3 | 4 | 5 | | V-2 | Susd5 | |
| 5672 | 3 | 4 | 5 | | V-2 | Sv2a | |
| 5673 | 3 | 4 | 5 | | V-2 | Sv2b | |
| 5674 | 3 | 4 | 5 | | V-2 | Syap1 | |
| 5675 | 3 | 4 | 5 | | V-2 | Syde2 | |
| 5676 | 3 | 4 | 5 | | V-2 | Syngr1 | |
| 5677 | 3 | 4 | 5 | | V-2 | Synm | |
| 5678 | 3 | 4 | 5 | | V-2 | Synpo2l | |
| 5679 | 3 | 4 | 5 | | V-2 | Syt3 | |
| 5680 | 3 | 4 | 5 | | V-2 | Syt5 | |
| 5681 | 3 | 4 | 5 | | V-2 | Sytl2 | |
| 5682 | 3 | 4 | 5 | | V-2 | Sytl3 | |
| 5683 | 3 | 4 | 5 | | V-2 | T2 | |
| 5684 | 3 | 4 | 5 | | V-2 | Tab1 | |
| 5685 | 3 | 4 | 5 | | V-2 | Tada1 | |
| 5686 | 3 | 4 | 5 | | V-2 | Tada2a | |
| 5687 | 3 | 4 | 5 | | V-2 | Taf1 | |
| 5688 | 3 | 4 | 5 | | V-2 | Taf13 | |
| 5689 | 3 | 4 | 5 | | V-2 | Taf1d | |
| 5690 | 3 | 4 | 5 | | V-2 | Taf7 | |
| 5691 | 3 | 4 | 5 | | V-2 | Tal1 | |
| 5692 | 3 | 4 | 5 | | V-2 | Tango2 | |
| 5693 | 3 | 4 | 5 | | V-2 | Tank | |
| 5694 | 3 | 4 | 5 | | V-2 | Taok1 | |
| 5695 | 3 | 4 | 5 | | V-2 | Tapbpl | |
| 5696 | 3 | 4 | 5 | | V-2 | Tarm1 | |
| 5697 | 3 | 4 | 5 | | V-2 | Tasp1 | |
| 5698 | 3 | 4 | 5 | | V-2 | Tatdn1 | |
| 5699 | 3 | 4 | 5 | | V-2 | Tax1bp1 | |
| 5700 | 3 | 4 | 5 | | V-2 | Tbc1d10b | |
| 5701 | 3 | 4 | 5 | | V-2 | Tbc1d4 | |
| 5702 | 3 | 4 | 5 | | V-2 | Tbc1d7 | |
| 5703 | 3 | 4 | 5 | | V-2 | Tbca | |
| 5704 | 3 | 4 | 5 | | V-2 | Tbcc | |
| 5705 | 3 | 4 | 5 | | V-2 | Tbx1 | |
| 5706 | 3 | 4 | 5 | | V-2 | Tbx22 | |
| 5707 | 3 | 4 | 5 | | V-2 | Tcea3 | |
| 5708 | 3 | 4 | 5 | | V-2 | Tceal7 | |
| 5709 | 3 | 4 | 5 | | V-2 | Tceb3 | |
| 5710 | 3 | 4 | 5 | | V-2 | Tcf15 | |
| 5711 | 3 | 4 | 5 | | V-2 | Tcf21 | |
| 5712 | 3 | 4 | 5 | | V-2 | Tcf24 | |
| 5713 | 3 | 4 | 5 | | V-2 | Tcf7l2 | |
| 5714 | 3 | 4 | 5 | | V-2 | Tcte3 | |
| 5715 | 3 | 4 | 5 | | V-2 | Tdrd3 | |
| 5716 | 3 | 4 | 5 | | V-2 | Tdrd6 | |
| 5717 | 3 | 4 | 5 | | V-2 | Tdrkh | |
| 5718 | 3 | 4 | 5 | | V-2 | Tead1 | |
| 5719 | 3 | 4 | 5 | | V-2 | Tenc1 | |
| 5720 | 3 | 4 | 5 | | V-2 | Tespa1 | |
| 5721 | 3 | 4 | 5 | | V-2 | Tfap4 | |
| 5722 | 3 | 4 | 5 | | V-2 | Tfb1m | |
| 5723 | 3 | 4 | 5 | | V-2 | Tfpi | |
| 5724 | 3 | 4 | 5 | | V-2 | Tfr2 | |
| 5725 | 3 | 4 | 5 | | V-2 | Tgfb1i1 | |
| 5726 | 3 | 4 | 5 | | V-2 | Thap3 | |
| 5727 | 3 | 4 | 5 | | V-2 | Thap7 | |
| 5728 | 3 | 4 | 5 | | V-2 | Thbd | |
| 5729 | 3 | 4 | 5 | | V-2 | Thbs2 | |
| 5730 | 3 | 4 | 5 | | V-2 | Them5 | |
| 5731 | 3 | 4 | 5 | | V-2 | Thoc6 | |
| 5732 | 3 | 4 | 5 | | V-2 | Thoc7 | |
| 5733 | 3 | 4 | 5 | | V-2 | Thrap3 | |
| 5734 | 3 | 4 | 5 | | V-2 | Thrb | |
| 5735 | 3 | 4 | 5 | | V-2 | Tia1 | |
| 5736 | 3 | 4 | 5 | | V-2 | Ticam2 | |
| 5737 | 3 | 4 | 5 | | V-2 | Timm17a | |
| 5738 | 3 | 4 | 5 | | V-2 | Timm17b | |
| 5739 | 3 | 4 | 5 | | V-2 | Timm21 | |
| 5740 | 3 | 4 | 5 | | V-2 | Timm50 | |
| 5741 | 3 | 4 | 5 | | V-2 | Timp3 | |
| 5742 | 3 | 4 | 5 | | V-2 | Tinagl1 | |
| 5743 | 3 | 4 | 5 | | V-2 | Tiparp | |
| 5744 | 3 | 4 | 5 | | V-2 | Tlcd1 | |
| 5745 | 3 | 4 | 5 | | V-2 | Tldc1 | |
| 5746 | 3 | 4 | 5 | | V-2 | Tln1 | |
| 5747 | 3 | 4 | 5 | | V-2 | Tln2 | |
| 5748 | 3 | 4 | 5 | | V-2 | Tlr3 | |
| 5749 | 3 | 4 | 5 | | V-2 | Tm2d1 | |
| 5750 | 3 | 4 | 5 | | V-2 | Tm2d2 | |
| 5751 | 3 | 4 | 5 | | V-2 | Tma7 | |
| 5752 | 3 | 4 | 5 | | V-2 | Tmbim4 | |
| 5753 | 3 | 4 | 5 | | V-2 | Tmcc3 | |
| 5754 | 3 | 4 | 5 | | V-2 | Tmed1 | |
| 5755 | 3 | 4 | 5 | | V-2 | Tmed5 | |
| 5756 | 3 | 4 | 5 | | V-2 | Tmem100 | |
| 5757 | 3 | 4 | 5 | | V-2 | Tmem101 | |
| 5758 | 3 | 4 | 5 | | V-2 | Tmem11 | |

Fig. 36 - 31

| | | | | | | | |
|---|---|---|---|---|---|---|---|
| 5759 | 3 | 4 | 5 | | V-2 | Tmem119 |
| 5760 | 3 | 4 | 5 | | V-2 | Tmem123 |
| 5761 | 3 | 4 | 5 | | V-2 | Tmem126a |
| 5762 | 3 | 4 | 5 | | V-2 | Tmem134 |
| 5763 | 3 | 4 | 5 | | V-2 | Tmem136 |
| 5764 | 3 | 4 | 5 | | V-2 | Tmem138 |
| 5765 | 3 | 4 | 5 | | V-2 | Tmem140 |
| 5766 | 3 | 4 | 5 | | V-2 | Tmem143 |
| 5767 | 3 | 4 | 5 | | V-2 | Tmem150a |
| 5768 | 3 | 4 | 5 | | V-2 | Tmem158 |
| 5769 | 3 | 4 | 5 | | V-2 | Tmem167b |
| 5770 | 3 | 4 | 5 | | V-2 | Tmem178 |
| 5771 | 3 | 4 | 5 | | V-2 | Tmem183a |
| 5772 | 3 | 4 | 5 | | V-2 | Tmem202 |
| 5773 | 3 | 4 | 5 | | V-2 | Tmem203 |
| 5774 | 3 | 4 | 5 | | V-2 | Tmem208 |
| 5775 | 3 | 4 | 5 | | V-2 | Tmem215 |
| 5776 | 3 | 4 | 5 | | V-2 | Tmem220 |
| 5777 | 3 | 4 | 5 | | V-2 | Tmem223 |
| 5778 | 3 | 4 | 5 | | V-2 | Tmem230 |
| 5779 | 3 | 4 | 5 | | V-2 | Tmem234 |
| 5780 | 3 | 4 | 5 | | V-2 | Tmem238 |
| 5781 | 3 | 4 | 5 | | V-2 | Tmem243 |
| 5782 | 3 | 4 | 5 | | V-2 | Tmem246 |
| 5783 | 3 | 4 | 5 | | V-2 | Tmem255a |
| 5784 | 3 | 4 | 5 | | V-2 | Tmem255b |
| 5785 | 3 | 4 | 5 | | V-2 | Tmem38b |
| 5786 | 3 | 4 | 5 | | V-2 | Tmem41a |
| 5787 | 3 | 4 | 5 | | V-2 | Tmem50a |
| 5788 | 3 | 4 | 5 | | V-2 | Tmem59l |
| 5789 | 3 | 4 | 5 | | V-2 | Tmem60 |
| 5790 | 3 | 4 | 5 | | V-2 | Tmem70 |
| 5791 | 3 | 4 | 5 | | V-2 | Tmem71 |
| 5792 | 3 | 4 | 5 | | V-2 | Tmem80 |
| 5793 | 3 | 4 | 5 | | V-2 | Tmem88 |
| 5794 | 3 | 4 | 5 | | V-2 | Tmem88b |
| 5795 | 3 | 4 | 5 | | V-2 | Tmlhe |
| 5796 | 3 | 4 | 5 | | V-2 | Tmod3 |
| 5797 | 3 | 4 | 5 | | V-2 | Tmsb10 |
| 5798 | 3 | 4 | 5 | | V-2 | Tmsb4x |
| 5799 | 3 | 4 | 5 | | V-2 | Tmtc2 |
| 5800 | 3 | 4 | 5 | | V-2 | Tmtc4 |
| 5801 | 3 | 4 | 5 | | V-2 | Tmx3 |
| 5802 | 3 | 4 | 5 | | V-2 | Tnfrsf12a |
| 5803 | 3 | 4 | 5 | | V-2 | Tnfrsf21 |
| 5804 | 3 | 4 | 5 | | V-2 | Tnfrsf23 |
| 5805 | 3 | 4 | 5 | | V-2 | Tnfsf12 |
| 5806 | 3 | 4 | 5 | | V-2 | Tnni1 |
| 5807 | 3 | 4 | 5 | | V-2 | Tnnt1 |
| 5808 | 3 | 4 | 5 | | V-2 | Tns1 |
| 5809 | 3 | 4 | 5 | | V-2 | Tob1 |
| 5810 | 3 | 4 | 5 | | V-2 | Tob2 |
| 5811 | 3 | 4 | 5 | | V-2 | Tollip |
| 5812 | 3 | 4 | 5 | | V-2 | Tom1 |
| 5813 | 3 | 4 | 5 | | V-2 | Tom1l1 |
| 5814 | 3 | 4 | 5 | | V-2 | Tom1l2 |
| 5815 | 3 | 4 | 5 | | V-2 | Top2b |
| 5816 | 3 | 4 | 5 | | V-2 | Topaz1 |
| 5817 | 3 | 4 | 5 | | V-2 | Toporsl |
| 5818 | 3 | 4 | 5 | | V-2 | Torlaip1 |
| 5819 | 3 | 4 | 5 | | V-2 | Tpgs1 |
| 5820 | 3 | 4 | 5 | | V-2 | Tph1 |
| 5821 | 3 | 4 | 5 | | V-2 | Tpm3 |
| 5822 | 3 | 4 | 5 | | V-2 | Tprgl |
| 5823 | 3 | 4 | 5 | | V-2 | Tpsab1 |
| 5824 | 3 | 4 | 5 | | V-2 | Tpt1 |
| 5825 | 3 | 4 | 5 | | V-2 | Traf7 |
| 5826 | 3 | 4 | 5 | | V-2 | Trak2 |
| 5827 | 3 | 4 | 5 | | V-2 | Tram2 |
| 5828 | 3 | 4 | 5 | | V-2 | Trappc1 |
| 5829 | 3 | 4 | 5 | | V-2 | Trappc12 |
| 5830 | 3 | 4 | 5 | | V-2 | Trappc4 |
| 5831 | 3 | 4 | 5 | | V-2 | Trappc6b |
| 5832 | 3 | 4 | 5 | | V-2 | Trappc9 |
| 5833 | 3 | 4 | 5 | | V-2 | Trdmt1 |
| 5834 | 3 | 4 | 5 | | V-2 | Treml2 |
| 5835 | 3 | 4 | 5 | | V-2 | Triap1 |
| 5836 | 3 | 4 | 5 | | V-2 | Trib1 |
| 5837 | 3 | 4 | 5 | | V-2 | Tril |
| 5838 | 3 | 4 | 5 | | V-2 | Trim13 |
| 5839 | 3 | 4 | 5 | | V-2 | Trim17 |
| 5840 | 3 | 4 | 5 | | V-2 | Trim23 |
| 5841 | 3 | 4 | 5 | | V-2 | Trim34a |
| 5842 | 3 | 4 | 5 | | V-2 | Trim47 |
| 5843 | 3 | 4 | 5 | | V-2 | Trim6 |
| 5844 | 3 | 4 | 5 | | V-2 | Trim62 |
| 5845 | 3 | 4 | 5 | | V-2 | Trip10 |
| 5846 | 3 | 4 | 5 | | V-2 | Trmt1 |
| 5847 | 3 | 4 | 5 | | V-2 | Trmt10b |
| 5848 | 3 | 4 | 5 | | V-2 | Trmt13 |
| 5849 | 3 | 4 | 5 | | V-2 | Trmu |
| 5850 | 3 | 4 | 5 | | V-2 | Trp63 |
| 5851 | 3 | 4 | 5 | | V-2 | Trpc2 |
| 5852 | 3 | 4 | 5 | | V-2 | Trpc6 |
| 5853 | 3 | 4 | 5 | | V-2 | Trpm1 |
| 5854 | 3 | 4 | 5 | | V-2 | Trpv4 |
| 5855 | 3 | 4 | 5 | | V-2 | Tsc1 |
| 5856 | 3 | 4 | 5 | | V-2 | Tsc22d3 |
| 5857 | 3 | 4 | 5 | | V-2 | Tsen15 |
| 5858 | 3 | 4 | 5 | | V-2 | Tsen34 |
| 5859 | 3 | 4 | 5 | | V-2 | Tsg101 |
| 5860 | 3 | 4 | 5 | | V-2 | Tsga10 |
| 5861 | 3 | 4 | 5 | | V-2 | Tshb |
| 5862 | 3 | 4 | 5 | | V-2 | Tsku |
| 5863 | 3 | 4 | 5 | | V-2 | Tslp |
| 5864 | 3 | 4 | 5 | | V-2 | Tspan17 |
| 5865 | 3 | 4 | 5 | | V-2 | Tspan32 |
| 5866 | 3 | 4 | 5 | | V-2 | Tspan6 |
| 5867 | 3 | 4 | 5 | | V-2 | Tspan9 |
| 5868 | 3 | 4 | 5 | | V-2 | Tspyl4 |
| 5869 | 3 | 4 | 5 | | V-2 | Tspyl5 |
| 5870 | 3 | 4 | 5 | | V-2 | Tssk1 |
| 5871 | 3 | 4 | 5 | | V-2 | Tssk4 |
| 5872 | 3 | 4 | 5 | | V-2 | Tstd2 |
| 5873 | 3 | 4 | 5 | | V-2 | Tstd3 |
| 5874 | 3 | 4 | 5 | | V-2 | Ttc14 |
| 5875 | 3 | 4 | 5 | | V-2 | Ttc32 |
| 5876 | 3 | 4 | 5 | | V-2 | Ttc33 |
| 5877 | 3 | 4 | 5 | | V-2 | Ttc8 |
| 5878 | 3 | 4 | 5 | | V-2 | Ttc9c |
| 5879 | 3 | 4 | 5 | | V-2 | Ttl1 |
| 5880 | 3 | 4 | 5 | | V-2 | Ttll11 |
| 5881 | 3 | 4 | 5 | | V-2 | Ttll12 |
| 5882 | 3 | 4 | 5 | | V-2 | Ttpa |
| 5883 | 3 | 4 | 5 | | V-2 | Tuba3a |
| 5884 | 3 | 4 | 5 | | V-2 | Tubb4b |
| 5885 | 3 | 4 | 5 | | V-2 | Tubd1 |
| 5886 | 3 | 4 | 5 | | V-2 | Tubgcp4 |
| 5887 | 3 | 4 | 5 | | V-2 | Tulp3 |
| 5888 | 3 | 4 | 5 | | V-2 | Twf1 |
| 5889 | 3 | 4 | 5 | | V-2 | Twf2 |
| 5890 | 3 | 4 | 5 | | V-2 | Txk |
| 5891 | 3 | 4 | 5 | | V-2 | Txlng |
| 5892 | 3 | 4 | 5 | | V-2 | Txn2 |
| 5893 | 3 | 4 | 5 | | V-2 | Txnl4a |
| 5894 | 3 | 4 | 5 | | V-2 | Tyk2 |
| 5895 | 3 | 4 | 5 | | V-2 | Tymp |
| 5896 | 3 | 4 | 5 | | V-2 | Tysnd1 |
| 5897 | 3 | 4 | 5 | | V-2 | Tvw5 |
| 5898 | 3 | 4 | 5 | | V-2 | Uap1l1 |
| 5899 | 3 | 4 | 5 | | V-2 | Ubac1 |
| 5900 | 3 | 4 | 5 | | V-2 | Ubald1 |
| 5901 | 3 | 4 | 5 | | V-2 | Ubap1 |
| 5902 | 3 | 4 | 5 | | V-2 | Ubb |
| 5903 | 3 | 4 | 5 | | V-2 | Ube2a |
| 5904 | 3 | 4 | 5 | | V-2 | Ube2d1 |
| 5905 | 3 | 4 | 5 | | V-2 | Ube2d3 |
| 5906 | 3 | 4 | 5 | | V-2 | Ube2e2 |
| 5907 | 3 | 4 | 5 | | V-2 | Ube2e3 |
| 5908 | 3 | 4 | 5 | | V-2 | Ube2i |
| 5909 | 3 | 4 | 5 | | V-2 | Ube2m |
| 5910 | 3 | 4 | 5 | | V-2 | Ube2r2 |
| 5911 | 3 | 4 | 5 | | V-2 | Ube2s |
| 5912 | 3 | 4 | 5 | | V-2 | Ube3b |
| 5913 | 3 | 4 | 5 | | V-2 | Ubtd1 |
| 5914 | 3 | 4 | 5 | | V-2 | Uchl4 |
| 5915 | 3 | 4 | 5 | | V-2 | Uchl5 |
| 5916 | 3 | 4 | 5 | | V-2 | Ucma |
| 5917 | 3 | 4 | 5 | | V-2 | Ucn |
| 5918 | 3 | 4 | 5 | | V-2 | Ucp2 |
| 5919 | 3 | 4 | 5 | | V-2 | Uevld |
| 5920 | 3 | 4 | 5 | | V-2 | Ugp2 |
| 5921 | 3 | 4 | 5 | | V-2 | Ugt1a7c |
| 5922 | 3 | 4 | 5 | | V-2 | Ulk3 |
| 5923 | 3 | 4 | 5 | | V-2 | Unc119 |
| 5924 | 3 | 4 | 5 | | V-2 | Unc13d |
| 5925 | 3 | 4 | 5 | | V-2 | Unc45b |
| 5926 | 3 | 4 | 5 | | V-2 | Uqcr10 |
| 5927 | 3 | 4 | 5 | | V-2 | Uqcrc2 |
| 5928 | 3 | 4 | 5 | | V-2 | Uqcrq |
| 5929 | 3 | 4 | 5 | | V-2 | Ush2a |
| 5930 | 3 | 4 | 5 | | V-2 | Usp15 |
| 5931 | 3 | 4 | 5 | | V-2 | Usp19 |
| 5932 | 3 | 4 | 5 | | V-2 | Usp25 |
| 5933 | 3 | 4 | 5 | | V-2 | Usp26 |
| 5934 | 3 | 4 | 5 | | V-2 | Usp32 |
| 5935 | 3 | 4 | 5 | | V-2 | Uvrag |
| 5936 | 3 | 4 | 5 | | V-2 | Vamp5 |
| 5937 | 3 | 4 | 5 | | V-2 | Vcam1 |
| 5938 | 3 | 4 | 5 | | V-2 | Vcpkmt |
| 5939 | 3 | 4 | 5 | | V-2 | Vdac3 |
| 5940 | 3 | 4 | 5 | | V-2 | Vegfb |
| 5941 | 3 | 4 | 5 | | V-2 | Vhl |
| 5942 | 3 | 4 | 5 | | V-2 | Vipr2 |
| 5943 | 3 | 4 | 5 | | V-2 | Vmn1r181 |
| 5944 | 3 | 4 | 5 | | V-2 | Vmn1r19 |
| 5945 | 3 | 4 | 5 | | V-2 | Vmn1r40 |
| 5946 | 3 | 4 | 5 | | V-2 | Vnn1 |
| 5947 | 3 | 4 | 5 | | V-2 | Vnn3 |
| 5948 | 3 | 4 | 5 | | V-2 | Vprbp |
| 5949 | 3 | 4 | 5 | | V-2 | Vpreb2 |
| 5950 | 3 | 4 | 5 | | V-2 | Vps25 |

Fig. 36 - 32

| | | | | | | | |
|---|---|---|---|---|---|---|---|
| 5951 | 3 | 4 | 5 | | V-2 | Vps29 |
| 5952 | 3 | 4 | 5 | | V-2 | Vps37b |
| 5953 | 3 | 4 | 5 | | V-2 | Vps51 |
| 5954 | 3 | 4 | 5 | | V-2 | Vps54 |
| 5955 | 3 | 4 | 5 | | V-2 | Vrk2 |
| 5956 | 3 | 4 | 5 | | V-2 | Vsig4 |
| 5957 | 3 | 4 | 5 | | V-2 | Vti1b |
| 5958 | 3 | 4 | 5 | | V-2 | Wbp1 |
| 5959 | 3 | 4 | 5 | | V-2 | Wbp2 |
| 5960 | 3 | 4 | 5 | | V-2 | Wbp5 |
| 5961 | 3 | 4 | 5 | | V-2 | Wbscr22 |
| 5962 | 3 | 4 | 5 | | V-2 | Wdr13 |
| 5963 | 3 | 4 | 5 | | V-2 | Wdr26 |
| 5964 | 3 | 4 | 5 | | V-2 | Wdr34 |
| 5965 | 3 | 4 | 5 | | V-2 | Wdr46 |
| 5966 | 3 | 4 | 5 | | V-2 | Wdr53 |
| 5967 | 3 | 4 | 5 | | V-2 | Wdr5b |
| 5968 | 3 | 4 | 5 | | V-2 | Wdr7 |
| 5969 | 3 | 4 | 5 | | V-2 | Wdr75 |
| 5970 | 3 | 4 | 5 | | V-2 | Wdyhv1 |
| 5971 | 3 | 4 | 5 | | V-2 | Wee1 |
| 5972 | 3 | 4 | 5 | | V-2 | Wipi1 |
| 5973 | 3 | 4 | 5 | | V-2 | Wnt9a |
| 5974 | 3 | 4 | 5 | | V-2 | Wrn |
| 5975 | 3 | 4 | 5 | | V-2 | Wt1 |
| 5976 | 3 | 4 | 5 | | V-2 | Wwp1 |
| 5977 | 3 | 4 | 5 | | V-2 | Xcr1 |
| 5978 | 3 | 4 | 5 | | V-2 | Xdh |
| 5979 | 3 | 4 | 5 | | V-2 | Xirp1 |
| 5980 | 3 | 4 | 5 | | V-2 | Xlr4a |
| 5981 | 3 | 4 | 5 | | V-2 | Xpa |
| 5982 | 3 | 4 | 5 | | V-2 | Xrcc4 |
| 5983 | 3 | 4 | 5 | | V-2 | Xrcc6 |
| 5984 | 3 | 4 | 5 | | V-2 | Yaf2 |
| 5985 | 3 | 4 | 5 | | V-2 | Yap1 |
| 5986 | 3 | 4 | 5 | | V-2 | Ybey |
| 5987 | 3 | 4 | 5 | | V-2 | Ypel5 |
| 5988 | 3 | 4 | 5 | | V-2 | Ywhah |
| 5989 | 3 | 4 | 5 | | V-2 | Zak |
| 5990 | 3 | 4 | 5 | | V-2 | Zbed3 |
| 5991 | 3 | 4 | 5 | | V-2 | Zbtb25 |
| 5992 | 3 | 4 | 5 | | V-2 | Zbtb33 |
| 5993 | 3 | 4 | 5 | | V-2 | Zbtb34 |
| 5994 | 3 | 4 | 5 | | V-2 | Zbtb49 |
| 5995 | 3 | 4 | 5 | | V-2 | Zbtb8os |
| 5996 | 3 | 4 | 5 | | V-2 | Zcchc14 |
| 5997 | 3 | 4 | 5 | | V-2 | Zcrb1 |
| 5998 | 3 | 4 | 5 | | V-2 | Zcwpw1 |
| 5999 | 3 | 4 | 5 | | V-2 | Zdhhc16 |
| 6000 | 3 | 4 | 5 | | V-2 | Zdhhc2 |
| 6001 | 3 | 4 | 5 | | V-2 | Zdhhc24 |
| 6002 | 3 | 4 | 5 | | V-2 | Zdhhc5 |
| 6003 | 3 | 4 | 5 | | V-2 | Zeb2 |
| 6004 | 3 | 4 | 5 | | V-2 | Zfand1 |
| 6005 | 3 | 4 | 5 | | V-2 | Zfand2b |
| 6006 | 3 | 4 | 5 | | V-2 | Zfand3 |
| 6007 | 3 | 4 | 5 | | V-2 | Zfp101 |
| 6008 | 3 | 4 | 5 | | V-2 | Zfp105 |
| 6009 | 3 | 4 | 5 | | V-2 | Zfp11 |
| 6010 | 3 | 4 | 5 | | V-2 | Zfp119a |
| 6011 | 3 | 4 | 5 | | V-2 | Zfp119b |
| 6012 | 3 | 4 | 5 | | V-2 | Zfp143 |
| 6013 | 3 | 4 | 5 | | V-2 | Zfp2 |
| 6014 | 3 | 4 | 5 | | V-2 | Zfp248 |
| 6015 | 3 | 4 | 5 | | V-2 | Zfp26 |
| 6016 | 3 | 4 | 5 | | V-2 | Zfp273 |
| 6017 | 3 | 4 | 5 | | V-2 | Zfp354c |
| 6018 | 3 | 4 | 5 | | V-2 | Zfp367 |
| 6019 | 3 | 4 | 5 | | V-2 | Zfp39 |
| 6020 | 3 | 4 | 5 | | V-2 | Zfp395 |
| 6021 | 3 | 4 | 5 | | V-2 | Zfp397 |
| 6022 | 3 | 4 | 5 | | V-2 | Zfp445 |
| 6023 | 3 | 4 | 5 | | V-2 | Zfp446 |
| 6024 | 3 | 4 | 5 | | V-2 | Zfp457 |
| 6025 | 3 | 4 | 5 | | V-2 | Zfp51 |
| 6026 | 3 | 4 | 5 | | V-2 | Zfp521 |
| 6027 | 3 | 4 | 5 | | V-2 | Zfp524 |
| 6028 | 3 | 4 | 5 | | V-2 | Zfp563 |
| 6029 | 3 | 4 | 5 | | V-2 | Zfp57 |
| 6030 | 3 | 4 | 5 | | V-2 | Zfp580 |
| 6031 | 3 | 4 | 5 | | V-2 | Zfp59 |
| 6032 | 3 | 4 | 5 | | V-2 | Zfp61 |
| 6033 | 3 | 4 | 5 | | V-2 | Zfp637 |
| 6034 | 3 | 4 | 5 | | V-2 | Zfp65 |
| 6035 | 3 | 4 | 5 | | V-2 | Zfp661 |
| 6036 | 3 | 4 | 5 | | V-2 | Zfp664 |
| 6037 | 3 | 4 | 5 | | V-2 | Zfp688 |
| 6038 | 3 | 4 | 5 | | V-2 | Zfp69 |
| 6039 | 3 | 4 | 5 | | V-2 | Zfp7 |
| 6040 | 3 | 4 | 5 | | V-2 | Zfp715 |
| 6041 | 3 | 4 | 5 | | V-2 | Zfp748 |
| 6042 | 3 | 4 | 5 | | V-2 | Zfp763 |
| 6043 | 3 | 4 | 5 | | V-2 | Zfp775 |
| 6044 | 3 | 4 | 5 | | V-2 | Zfp791 |
| 6045 | 3 | 4 | 5 | | V-2 | Zfp82 |
| 6046 | 3 | 4 | 5 | | V-2 | Zfp85 |

| | | | | | | | |
|---|---|---|---|---|---|---|---|
| 6047 | 3 | 4 | 5 | | V-2 | Zfp90 |
| 6048 | 3 | 4 | 5 | | V-2 | Zfp91 |
| 6049 | 3 | 4 | 5 | | V-2 | Zfp935 |
| 6050 | 3 | 4 | 5 | | V-2 | Zfp938 |
| 6051 | 3 | 4 | 5 | | V-2 | Zfp94 |
| 6052 | 3 | 4 | 5 | | V-2 | Zfp942 |
| 6053 | 3 | 4 | 5 | | V-2 | Zfp945 |
| 6054 | 3 | 4 | 5 | | V-2 | Zfp952 |
| 6055 | 3 | 4 | 5 | | V-2 | Zfp961 |
| 6056 | 3 | 4 | 5 | | V-2 | Zfp97 |
| 6057 | 3 | 4 | 5 | | V-2 | Zfpm2 |
| 6058 | 3 | 4 | 5 | | V-2 | Zfr |
| 6059 | 3 | 4 | 5 | | V-2 | Zfr2 |
| 6060 | 3 | 4 | 5 | | V-2 | Zic1 |
| 6061 | 3 | 4 | 5 | | V-2 | Zim3 |
| 6062 | 3 | 4 | 5 | | V-2 | Zmym2 |
| 6063 | 3 | 4 | 5 | | V-2 | Znf41-ps |
| 6064 | 3 | 4 | 5 | | V-2 | Znrf2 |
| 6065 | 3 | 4 | 5 | | V-2 | Zranb1 |
| 6066 | 3 | 4 | 5 | | V-2 | Zscan25 |
| 6067 | 3 | 4 | 5 | | V-2 | Zswim7 |
| 6068 | 3 | 4 | 5 | | V-2 | Zxdb |
| 6069 | 3 | 4 | 5 | | V-2 | Zyx |
| 6070 | 3 | 4 | 5 | | V-1 | 0610009L18Rik |
| 6071 | 3 | 4 | 5 | | V-1 | 0610010K14Rik |
| 6072 | 3 | 4 | 5 | | V-1 | 0610011F06Rik |
| 6073 | 3 | 4 | 5 | | V-1 | 0610031J06Rik |
| 6074 | 3 | 4 | 5 | | V-1 | 0610031O16Rik |
| 6075 | 3 | 4 | 5 | | V-1 | 0610037L13Rik |
| 6076 | 3 | 4 | 5 | | V-1 | 0610038B21Rik |
| 6077 | 3 | 4 | 5 | | V-1 | 0610039K10Rik |
| 6078 | 3 | 4 | 5 | | V-1 | 1110002L01Rik |
| 6079 | 3 | 4 | 5 | | V-1 | 1110012L19Rik |
| 6080 | 3 | 4 | 5 | | V-1 | 1110019D14Rik |
| 6081 | 3 | 4 | 5 | | V-1 | 1110032A03Rik |
| 6082 | 3 | 4 | 5 | | V-1 | 1110034G24Rik |
| 6083 | 3 | 4 | 5 | | V-1 | 1110038F14Rik |
| 6084 | 3 | 4 | 5 | | V-1 | 1110046J04Rik |
| 6085 | 3 | 4 | 5 | | V-1 | 1110065P20Rik |
| 6086 | 3 | 4 | 5 | | V-1 | 1190007I07Rik |
| 6087 | 3 | 4 | 5 | | V-1 | 1300002E11Rik |
| 6088 | 3 | 4 | 5 | | V-1 | 1500009C09Rik |
| 6089 | 3 | 4 | 5 | | V-1 | 1500017E21Rik |
| 6090 | 3 | 4 | 5 | | V-1 | 1600014K23Rik |
| 6091 | 3 | 4 | 5 | | V-1 | 1600016N20Rik |
| 6092 | 3 | 4 | 5 | | V-1 | 1600025M17Rik |
| 6093 | 3 | 4 | 5 | | V-1 | 1700001J03Rik |
| 6094 | 3 | 4 | 5 | | V-1 | 1700001K23Rik |
| 6095 | 3 | 4 | 5 | | V-1 | 1700001L19Rik |
| 6096 | 3 | 4 | 5 | | V-1 | 1700001O22Rik |
| 6097 | 3 | 4 | 5 | | V-1 | 1700003E16Rik |
| 6098 | 3 | 4 | 5 | | V-1 | 1700003M07Rik |
| 6099 | 3 | 4 | 5 | | V-1 | 1700007G11Rik |
| 6100 | 3 | 4 | 5 | | V-1 | 1700007J10Rik |
| 6101 | 3 | 4 | 5 | | V-1 | 1700009J07Rik |
| 6102 | 3 | 4 | 5 | | V-1 | 1700011A15Rik |
| 6103 | 3 | 4 | 5 | | V-1 | 1700012B09Rik |
| 6104 | 3 | 4 | 5 | | V-1 | 1700012D01Rik |
| 6105 | 3 | 4 | 5 | | V-1 | 1700012D14Rik |
| 6106 | 3 | 4 | 5 | | V-1 | 1700018A04Rik |
| 6107 | 3 | 4 | 5 | | V-1 | 1700018C11Rik |
| 6108 | 3 | 4 | 5 | | V-1 | 1700018G05Rik |
| 6109 | 3 | 4 | 5 | | V-1 | 1700019D03Rik |
| 6110 | 3 | 4 | 5 | | V-1 | 1700019L03Rik |
| 6111 | 3 | 4 | 5 | | V-1 | 1700021F07Rik |
| 6112 | 3 | 4 | 5 | | V-1 | 1700021N21Rik |
| 6113 | 3 | 4 | 5 | | V-1 | 1700026L06Rik |
| 6114 | 3 | 4 | 5 | | V-1 | 1700029J07Rik |
| 6115 | 3 | 4 | 5 | | V-1 | 1700030F04Rik |
| 6116 | 3 | 4 | 5 | | V-1 | 1700037C18Rik |
| 6117 | 3 | 4 | 5 | | V-1 | 1700044K03Rik |
| 6118 | 3 | 4 | 5 | | V-1 | 1700046C09Rik |
| 6119 | 3 | 4 | 5 | | V-1 | 1700049G17Rik |
| 6120 | 3 | 4 | 5 | | V-1 | 1700056E22Rik |
| 6121 | 3 | 4 | 5 | | V-1 | 1700065J18Rik |
| 6122 | 3 | 4 | 5 | | V-1 | 1700066M21Rik |
| 6123 | 3 | 4 | 5 | | V-1 | 1700071K01Rik |
| 6124 | 3 | 4 | 5 | | V-1 | 1700072B07Rik |
| 6125 | 3 | 4 | 5 | | V-1 | 1700086L19Rik |
| 6126 | 3 | 4 | 5 | | V-1 | 1700086O06Rik |
| 6127 | 3 | 4 | 5 | | V-1 | 1700092C10Rik |
| 6128 | 3 | 4 | 5 | | V-1 | 1700092M07Rik |
| 6129 | 3 | 4 | 5 | | V-1 | 1700097N02Rik |
| 6130 | 3 | 4 | 5 | | V-1 | 1700101E01Rik |
| 6131 | 3 | 4 | 5 | | V-1 | 1700102H20Rik |
| 6132 | 3 | 4 | 5 | | V-1 | 1700102P08Rik |
| 6133 | 3 | 4 | 5 | | V-1 | 1700106J16Rik |
| 6134 | 3 | 4 | 5 | | V-1 | 1700109K24Rik |
| 6135 | 3 | 4 | 5 | | V-1 | 1700110K17Rik |
| 6136 | 3 | 4 | 5 | | V-1 | 1700119H24Rik |
| 6137 | 3 | 4 | 5 | | V-1 | 1700120C14Rik |
| 6138 | 3 | 4 | 5 | | V-1 | 1700123M08Rik |
| 6139 | 3 | 4 | 5 | | V-1 | 1700128F08Rik |
| 6140 | 3 | 4 | 5 | | V-1 | 1810010D01Rik |
| 6141 | 3 | 4 | 5 | | V-1 | 1810011O10Rik |
| 6142 | 3 | 4 | 5 | | V-1 | 1810012K16Rik |

Fig. 36 - 33

| | | | | | | | |
|---|---|---|---|---|---|---|---|
| 6143 | 3 | 4 | 5 | | V-1 | 1810014B01Rik |
| 6144 | 3 | 4 | 5 | | V-1 | 1810018F18Rik |
| 6145 | 3 | 4 | 5 | | V-1 | 1810020O05Rik |
| 6146 | 3 | 4 | 5 | | V-1 | 1810026J23Rik |
| 6147 | 3 | 4 | 5 | | V-1 | 1810032O08Rik |
| 6148 | 3 | 4 | 5 | | V-1 | 1810034E14Rik |
| 6149 | 3 | 4 | 5 | | V-1 | 1810041L15Rik |
| 6150 | 3 | 4 | 5 | | V-1 | 1810043H04Rik |
| 6151 | 3 | 4 | 5 | | V-1 | 1810053B23Rik |
| 6152 | 3 | 4 | 5 | | V-1 | 1810058I24Rik |
| 6153 | 3 | 4 | 5 | | V-1 | 2010002M12Rik |
| 6154 | 3 | 4 | 5 | | V-1 | 2010016I18Rik |
| 6155 | 3 | 4 | 5 | | V-1 | 2010107G12Rik |
| 6156 | 3 | 4 | 5 | | V-1 | 2010107G23Rik |
| 6157 | 3 | 4 | 5 | | V-1 | 2010109A12Rik |
| 6158 | 3 | 4 | 5 | | V-1 | 2210404O09Rik |
| 6159 | 3 | 4 | 5 | | V-1 | 2210407C18Rik |
| 6160 | 3 | 4 | 5 | | V-1 | 2210408F21Rik |
| 6161 | 3 | 4 | 5 | | V-1 | 2210408I21Rik |
| 6162 | 3 | 4 | 5 | | V-1 | 2210409E12Rik |
| 6163 | 3 | 4 | 5 | | V-1 | 2210417A02Rik |
| 6164 | 3 | 4 | 5 | | V-1 | 2310015D24Rik |
| 6165 | 3 | 4 | 5 | | V-1 | 2310039L15Rik |
| 6166 | 3 | 4 | 5 | | V-1 | 2310068I16Rik |
| 6167 | 3 | 4 | 5 | | V-1 | 2310069G16Rik |
| 6168 | 3 | 4 | 5 | | V-1 | 2410015M20Rik |
| 6169 | 3 | 4 | 5 | | V-1 | 2410076I21Rik |
| 6170 | 3 | 4 | 5 | | V-1 | 2410089E03Rik |
| 6171 | 3 | 4 | 5 | | V-1 | 2410127L17Rik |
| 6172 | 3 | 4 | 5 | | V-1 | 2510049J12Rik |
| 6173 | 3 | 4 | 5 | | V-1 | 2610020C07Rik |
| 6174 | 3 | 4 | 5 | | V-1 | 2610035D17Rik |
| 6175 | 3 | 4 | 5 | | V-1 | 2610306M01Rik |
| 6176 | 3 | 4 | 5 | | V-1 | 2610318N02Rik |
| 6177 | 3 | 4 | 5 | | V-1 | 2700029M09Rik |
| 6178 | 3 | 4 | 5 | | V-1 | 2700046G09Rik |
| 6179 | 3 | 4 | 5 | | V-1 | 2700062C07Rik |
| 6180 | 3 | 4 | 5 | | V-1 | 2700069I18Rik |
| 6181 | 3 | 4 | 5 | | V-1 | 2700086A05Rik |
| 6182 | 3 | 4 | 5 | | V-1 | 2700097O09Rik |
| 6183 | 3 | 4 | 5 | | V-1 | 2810001G20Rik |
| 6184 | 3 | 4 | 5 | | V-1 | 2810002D19Rik |
| 6185 | 3 | 4 | 5 | | V-1 | 2810029C07Rik |
| 6186 | 3 | 4 | 5 | | V-1 | 2810049E08Rik |
| 6187 | 3 | 4 | 5 | | V-1 | 2810408I11Rik |
| 6188 | 3 | 4 | 5 | | V-1 | 2810474O19Rik |
| 6189 | 3 | 4 | 5 | | V-1 | 2900026A02Rik |
| 6190 | 3 | 4 | 5 | | V-1 | 3010001F23Rik |
| 6191 | 3 | 4 | 5 | | V-1 | 3010026O09Rik |
| 6192 | 3 | 4 | 5 | | V-1 | 3110002H16Rik |
| 6193 | 3 | 4 | 5 | | V-1 | 3110007F17Rik |
| 6194 | 3 | 4 | 5 | | V-1 | 3110040N11Rik |
| 6195 | 3 | 4 | 5 | | V-1 | 3110045C21Rik |
| 6196 | 3 | 4 | 5 | | V-1 | 3110082I17Rik |
| 6197 | 3 | 4 | 5 | | V-1 | 3632454L22Rik |
| 6198 | 3 | 4 | 5 | | V-1 | 4632427E13Rik |
| 6199 | 3 | 4 | 5 | | V-1 | 4632428C04Rik |
| 6200 | 3 | 4 | 5 | | V-1 | 4632434I11Rik |
| 6201 | 3 | 4 | 5 | | V-1 | 4921504A21Rik |
| 6202 | 3 | 4 | 5 | | V-1 | 4921524J17Rik |
| 6203 | 3 | 4 | 5 | | V-1 | 4921531C22Rik |
| 6204 | 3 | 4 | 5 | | V-1 | 4921531P14Rik |
| 6205 | 3 | 4 | 5 | | V-1 | 4930402H24Rik |
| 6206 | 3 | 4 | 5 | | V-1 | 4930404I05Rik |
| 6207 | 3 | 4 | 5 | | V-1 | 4930404N11Rik |
| 6208 | 3 | 4 | 5 | | V-1 | 4930413F20Rik |
| 6209 | 3 | 4 | 5 | | V-1 | 4930415O20Rik |
| 6210 | 3 | 4 | 5 | | V-1 | 4930433B08Rik |
| 6211 | 3 | 4 | 5 | | V-1 | 4930449E18Rik |
| 6212 | 3 | 4 | 5 | | V-1 | 4930461G14Rik |
| 6213 | 3 | 4 | 5 | | V-1 | 4930467K11Rik |
| 6214 | 3 | 4 | 5 | | V-1 | 4930481A15Rik |
| 6215 | 3 | 4 | 5 | | V-1 | 4930502A04Rik |
| 6216 | 3 | 4 | 5 | | V-1 | 4930503E24Rik |
| 6217 | 3 | 4 | 5 | | V-1 | 4930503H13Rik |
| 6218 | 3 | 4 | 5 | | V-1 | 4930506C21Rik |
| 6219 | 3 | 4 | 5 | | V-1 | 4930515G16Rik |
| 6220 | 3 | 4 | 5 | | V-1 | 4930519F09Rik |
| 6221 | 3 | 4 | 5 | | V-1 | 4930519H02Rik |
| 6222 | 3 | 4 | 5 | | V-1 | 4930524N10Rik |
| 6223 | 3 | 4 | 5 | | V-1 | 4930525D18Rik |
| 6224 | 3 | 4 | 5 | | V-1 | 4930526I15Rik |
| 6225 | 3 | 4 | 5 | | V-1 | 4930526L06Rik |
| 6226 | 3 | 4 | 5 | | V-1 | 4930528A17Rik |
| 6227 | 3 | 4 | 5 | | V-1 | 4930532M18Rik |
| 6228 | 3 | 4 | 5 | | V-1 | 4930544M13Rik |
| 6229 | 3 | 4 | 5 | | V-1 | 4930545H06Rik |
| 6230 | 3 | 4 | 5 | | V-1 | 4930565N06Rik |
| 6231 | 3 | 4 | 5 | | V-1 | 4930578C19Rik |
| 6232 | 3 | 4 | 5 | | V-1 | 4930579G18Rik |
| 6233 | 3 | 4 | 5 | | V-1 | 4930579G24Rik |
| 6234 | 3 | 4 | 5 | | V-1 | 4930579K19Rik |
| 6235 | 3 | 4 | 5 | | V-1 | 4930591A17Rik |
| 6236 | 3 | 4 | 5 | | V-1 | 4930594C11Rik |
| 6237 | 3 | 4 | 5 | | V-1 | 4930596I21Rik |
| 6238 | 3 | 4 | 5 | | V-1 | 4931406P16Rik |
| 6239 | 3 | 4 | 5 | | V-1 | 4931414P19Rik |
| 6240 | 3 | 4 | 5 | | V-1 | 4931431B13Rik |
| 6241 | 3 | 4 | 5 | | V-1 | 4931440P22Rik |
| 6242 | 3 | 4 | 5 | | V-1 | 4932418E24Rik |
| 6243 | 3 | 4 | 5 | | V-1 | 4932438H23Rik |
| 6244 | 3 | 4 | 5 | | V-1 | 4932702P03Rik |
| 6245 | 3 | 4 | 5 | | V-1 | 4933402O24Rik |
| 6246 | 3 | 4 | 5 | | V-1 | 4933404O12Rik |
| 6247 | 3 | 4 | 5 | | V-1 | 4933407K13Rik |
| 6248 | 3 | 4 | 5 | | V-1 | 4933409G03Rik |
| 6249 | 3 | 4 | 5 | | V-1 | 4933412E12Rik |
| 6250 | 3 | 4 | 5 | | V-1 | 4933413G19Rik |
| 6251 | 3 | 4 | 5 | | V-1 | 4933417A18Rik |
| 6252 | 3 | 4 | 5 | | V-1 | 4933417D19Rik |
| 6253 | 3 | 4 | 5 | | V-1 | 4933426M11Rik |
| 6254 | 3 | 4 | 5 | | V-1 | 4933428G20Rik |
| 6255 | 3 | 4 | 5 | | V-1 | 4933433G15Rik |
| 6256 | 3 | 4 | 5 | | V-1 | 4933433G19Rik |
| 6257 | 3 | 4 | 5 | | V-1 | 5031439G07Rik |
| 6258 | 3 | 4 | 5 | | V-1 | 5330417C22Rik |
| 6259 | 3 | 4 | 5 | | V-1 | 5430421N21Rik |
| 6260 | 3 | 4 | 5 | | V-1 | 5430425K12Rik |
| 6261 | 3 | 4 | 5 | | V-1 | 5530601H04Rik |
| 6262 | 3 | 4 | 5 | | V-1 | 5830417I10Rik |
| 6263 | 3 | 4 | 5 | | V-1 | 5830432E09Rik |
| 6264 | 3 | 4 | 5 | | V-1 | 5930412G12Rik |
| 6265 | 3 | 4 | 5 | | V-1 | 6030408B16Rik |
| 6266 | 3 | 4 | 5 | | V-1 | 6030419C18Rik |
| 6267 | 3 | 4 | 5 | | V-1 | 6330408A02Rik |
| 6268 | 3 | 4 | 5 | | V-1 | 6330409D20Rik |
| 6269 | 3 | 4 | 5 | | V-1 | 6430573F11Rik |
| 6270 | 3 | 4 | 5 | | V-1 | 6720416L17Rik |
| 6271 | 3 | 4 | 5 | | V-1 | 6720468P15Rik |
| 6272 | 3 | 4 | 5 | | V-1 | 6720483E21Rik |
| 6273 | 3 | 4 | 5 | | V-1 | 9030612E09Rik |
| 6274 | 3 | 4 | 5 | | V-1 | 9030617O03Rik |
| 6275 | 3 | 4 | 5 | | V-1 | 9130204L05Rik |
| 6276 | 3 | 4 | 5 | | V-1 | 9130209A04Rik |
| 6277 | 3 | 4 | 5 | | V-1 | 9130221H12Rik |
| 6278 | 3 | 4 | 5 | | V-1 | 9130401M01Rik |
| 6279 | 3 | 4 | 5 | | V-1 | 9230009I02Rik |
| 6280 | 3 | 4 | 5 | | V-1 | 9230114K14Rik |
| 6281 | 3 | 4 | 5 | | V-1 | 9330102E08Rik |
| 6282 | 3 | 4 | 5 | | V-1 | 9330133O14Rik |
| 6283 | 3 | 4 | 5 | | V-1 | 9330175E14Rik |
| 6284 | 3 | 4 | 5 | | V-1 | 9430008C03Rik |
| 6285 | 3 | 4 | 5 | | V-1 | 9430015G10Rik |
| 6286 | 3 | 4 | 5 | | V-1 | 9430020K01Rik |
| 6287 | 3 | 4 | 5 | | V-1 | 9430041J12Rik |
| 6288 | 3 | 4 | 5 | | V-1 | 9530027J09Rik |
| 6289 | 3 | 4 | 5 | | V-1 | 9530068E07Rik |
| 6290 | 3 | 4 | 5 | | V-1 | 9530080O11Rik |
| 6291 | 3 | 4 | 5 | | V-1 | 9630028B13Rik |
| 6292 | 3 | 4 | 5 | | V-1 | 9830147E19Rik |
| 6293 | 3 | 4 | 5 | | V-1 | 9930021J03Rik |
| 6294 | 3 | 4 | 5 | | V-1 | 9930104L06Rik |
| 6295 | 3 | 4 | 5 | | V-1 | A230050P20Rik |
| 6296 | 3 | 4 | 5 | | V-1 | A230056P14Rik |
| 6297 | 3 | 4 | 5 | | V-1 | A230072C01Rik |
| 6298 | 3 | 4 | 5 | | V-1 | A230073K19Rik |
| 6299 | 3 | 4 | 5 | | V-1 | A230103J11Rik |
| 6300 | 3 | 4 | 5 | | V-1 | A2m |
| 6301 | 3 | 4 | 5 | | V-1 | A330009N23Rik |
| 6302 | 3 | 4 | 5 | | V-1 | A330021E22Rik |
| 6303 | 3 | 4 | 5 | | V-1 | A330070K13Rik |
| 6304 | 3 | 4 | 5 | | V-1 | A330093E20Rik |
| 6305 | 3 | 4 | 5 | | V-1 | A530013C23Rik |
| 6306 | 3 | 4 | 5 | | V-1 | A530054K11Rik |
| 6307 | 3 | 4 | 5 | | V-1 | A530088E08Rik |
| 6308 | 3 | 4 | 5 | | V-1 | A630066F11Rik |
| 6309 | 3 | 4 | 5 | | V-1 | A630089N07Rik |
| 6310 | 3 | 4 | 5 | | V-1 | A730020M07Rik |
| 6311 | 3 | 4 | 5 | | V-1 | A830010M20Rik |
| 6312 | 3 | 4 | 5 | | V-1 | A830018L16Rik |
| 6313 | 3 | 4 | 5 | | V-1 | A830052D11Rik |
| 6314 | 3 | 4 | 5 | | V-1 | A830080D01Rik |
| 6315 | 3 | 4 | 5 | | V-1 | A930005H10Rik |
| 6316 | 3 | 4 | 5 | | V-1 | A930012L18Rik |
| 6317 | 3 | 4 | 5 | | V-1 | A930015D03Rik |
| 6318 | 3 | 4 | 5 | | V-1 | A930016O22Rik |
| 6319 | 3 | 4 | 5 | | V-1 | A930041C12Rik |
| 6320 | 3 | 4 | 5 | | V-1 | AA387883 |
| 6321 | 3 | 4 | 5 | | V-1 | AA413626 |
| 6322 | 3 | 4 | 5 | | V-1 | AF251705 |
| 6323 | 3 | 4 | 5 | | V-1 | AI413582 |
| 6324 | 3 | 4 | 5 | | V-1 | AI463170 |
| 6325 | 3 | 4 | 5 | | V-1 | AI467606 |
| 6326 | 3 | 4 | 5 | | V-1 | AI839979 |
| 6327 | 3 | 4 | 5 | | V-1 | AI987944 |
| 6328 | 3 | 4 | 5 | | V-1 | AK010878 |
| 6329 | 3 | 4 | 5 | | V-1 | AK129341 |
| 6330 | 3 | 4 | 5 | | V-1 | AU021092 |
| 6331 | 3 | 4 | 5 | | V-1 | AU022252 |
| 6332 | 3 | 4 | 5 | | V-1 | AU041133 |
| 6333 | 3 | 4 | 5 | | V-1 | AV039307 |
| 6334 | 3 | 4 | 5 | | V-1 | AV051173 |

Fig. 36 - 34

| | | | | | | | |
|---|---|---|---|---|---|---|---|
| 6335 | 3 | 4 | 5 | | V-1 | AW011738 |
| 6336 | 3 | 4 | 5 | | V-1 | AW495222 |
| 6337 | 3 | 4 | 5 | | V-1 | AW549542 |
| 6338 | 3 | 4 | 5 | | V-1 | AW554918 |
| 6339 | 3 | 4 | 5 | | V-1 | AY358078 |
| 6340 | 3 | 4 | 5 | | V-1 | Aacs |
| 6341 | 3 | 4 | 5 | | V-1 | Aaed1 |
| 6342 | 3 | 4 | 5 | | V-1 | Aak1 |
| 6343 | 3 | 4 | 5 | | V-1 | Aasdh |
| 6344 | 3 | 4 | 5 | | V-1 | Abca3 |
| 6345 | 3 | 4 | 5 | | V-1 | Abca6 |
| 6346 | 3 | 4 | 5 | | V-1 | Abca7 |
| 6347 | 3 | 4 | 5 | | V-1 | Abca8b |
| 6348 | 3 | 4 | 5 | | V-1 | Abcb1a |
| 6349 | 3 | 4 | 5 | | V-1 | Abcb1b |
| 6350 | 3 | 4 | 5 | | V-1 | Abcc10 |
| 6351 | 3 | 4 | 5 | | V-1 | Abcc2 |
| 6352 | 3 | 4 | 5 | | V-1 | Abcc3 |
| 6353 | 3 | 4 | 5 | | V-1 | Abcf1 |
| 6354 | 3 | 4 | 5 | | V-1 | Abhd1 |
| 6355 | 3 | 4 | 5 | | V-1 | Abl2 |
| 6356 | 3 | 4 | 5 | | V-1 | Abraci |
| 6357 | 3 | 4 | 5 | | V-1 | Abtb2 |
| 6358 | 3 | 4 | 5 | | V-1 | Acaa1a |
| 6359 | 3 | 4 | 5 | | V-1 | Acaca |
| 6360 | 3 | 4 | 5 | | V-1 | Acadm |
| 6361 | 3 | 4 | 5 | | V-1 | Acat2 |
| 6362 | 3 | 4 | 5 | | V-1 | Acat3 |
| 6363 | 3 | 4 | 5 | | V-1 | Acer2 |
| 6364 | 3 | 4 | 5 | | V-1 | Ache |
| 6365 | 3 | 4 | 5 | | V-1 | Ackr1 |
| 6366 | 3 | 4 | 5 | | V-1 | Ackr4 |
| 6367 | 3 | 4 | 5 | | V-1 | Acn9 |
| 6368 | 3 | 4 | 5 | | V-1 | Aco1 |
| 6369 | 3 | 4 | 5 | | V-1 | Acot11 |
| 6370 | 3 | 4 | 5 | | V-1 | Acot5 |
| 6371 | 3 | 4 | 5 | | V-1 | Acot6 |
| 6372 | 3 | 4 | 5 | | V-1 | Acot9 |
| 6373 | 3 | 4 | 5 | | V-1 | Acrbp |
| 6374 | 3 | 4 | 5 | | V-1 | Acsf2 |
| 6375 | 3 | 4 | 5 | | V-1 | Acsm1 |
| 6376 | 3 | 4 | 5 | | V-1 | Acsm2 |
| 6377 | 3 | 4 | 5 | | V-1 | Actl10 |
| 6378 | 3 | 4 | 5 | | V-1 | Actn2 |
| 6379 | 3 | 4 | 5 | | V-1 | Actr5 |
| 6380 | 3 | 4 | 5 | | V-1 | Acvr1b |
| 6381 | 3 | 4 | 5 | | V-1 | Acvr1c |
| 6382 | 3 | 4 | 5 | | V-1 | Acvr2a |
| 6383 | 3 | 4 | 5 | | V-1 | Acy1 |
| 6384 | 3 | 4 | 5 | | V-1 | Acyp1 |
| 6385 | 3 | 4 | 5 | | V-1 | Adam11 |
| 6386 | 3 | 4 | 5 | | V-1 | Adam19 |
| 6387 | 3 | 4 | 5 | | V-1 | Adam8 |
| 6388 | 3 | 4 | 5 | | V-1 | Adamdec1 |
| 6389 | 3 | 4 | 5 | | V-1 | Adamts1 |
| 6390 | 3 | 4 | 5 | | V-1 | Adamts5 |
| 6391 | 3 | 4 | 5 | | V-1 | Adamts8 |
| 6392 | 3 | 4 | 5 | | V-1 | Adamts9 |
| 6393 | 3 | 4 | 5 | | V-1 | Adamtsl4 |
| 6394 | 3 | 4 | 5 | | V-1 | Adap1 |
| 6395 | 3 | 4 | 5 | | V-1 | Adap2 |
| 6396 | 3 | 4 | 5 | | V-1 | Adarb2 |
| 6397 | 3 | 4 | 5 | | V-1 | Adat1 |
| 6398 | 3 | 4 | 5 | | V-1 | Adat2 |
| 6399 | 3 | 4 | 5 | | V-1 | Adc |
| 6400 | 3 | 4 | 5 | | V-1 | Adck4 |
| 6401 | 3 | 4 | 5 | | V-1 | Adcy5 |
| 6402 | 3 | 4 | 5 | | V-1 | Adcy7 |
| 6403 | 3 | 4 | 5 | | V-1 | Adcyap1r1 |
| 6404 | 3 | 4 | 5 | | V-1 | Add2 |
| 6405 | 3 | 4 | 5 | | V-1 | Adh4 |
| 6406 | 3 | 4 | 5 | | V-1 | Adh6a |
| 6407 | 3 | 4 | 5 | | V-1 | Adipor2 |
| 6408 | 3 | 4 | 5 | | V-1 | Adk |
| 6409 | 3 | 4 | 5 | | V-1 | Adm |
| 6410 | 3 | 4 | 5 | | V-1 | Adora1 |
| 6411 | 3 | 4 | 5 | | V-1 | Adora2b |
| 6412 | 3 | 4 | 5 | | V-1 | Adprhl2 |
| 6413 | 3 | 4 | 5 | | V-1 | Adra1b |
| 6414 | 3 | 4 | 5 | | V-1 | Adrb2 |
| 6415 | 3 | 4 | 5 | | V-1 | Adrm1 |
| 6416 | 3 | 4 | 5 | | V-1 | Afap1l1 |
| 6417 | 3 | 4 | 5 | | V-1 | Afap1l2 |
| 6418 | 3 | 4 | 5 | | V-1 | Aff1 |
| 6419 | 3 | 4 | 5 | | V-1 | Aff4 |
| 6420 | 3 | 4 | 5 | | V-1 | Aga |
| 6421 | 3 | 4 | 5 | | V-1 | Agbl3 |
| 6422 | 3 | 4 | 5 | | V-1 | Agbl4 |
| 6423 | 3 | 4 | 5 | | V-1 | Agmat |
| 6424 | 3 | 4 | 5 | | V-1 | Agmo |
| 6425 | 3 | 4 | 5 | | V-1 | Agpat9 |
| 6426 | 3 | 4 | 5 | | V-1 | Agrn |
| 6427 | 3 | 4 | 5 | | V-1 | Agrp |
| 6428 | 3 | 4 | 5 | | V-1 | Agtr1a |
| 6429 | 3 | 4 | 5 | | V-1 | Agtr2 |
| 6430 | 3 | 4 | 5 | | V-1 | Ahcy |
| 6431 | 3 | 4 | 5 | | V-1 | Ahdc1 |
| 6432 | 3 | 4 | 5 | | V-1 | Aicda |
| 6433 | 3 | 4 | 5 | | V-1 | Aifm1 |
| 6434 | 3 | 4 | 5 | | V-1 | Aig1 |
| 6435 | 3 | 4 | 5 | | V-1 | Aim2 |
| 6436 | 3 | 4 | 5 | | V-1 | Aip |
| 6437 | 3 | 4 | 5 | | V-1 | Airn |
| 6438 | 3 | 4 | 5 | | V-1 | Ak1 |
| 6439 | 3 | 4 | 5 | | V-1 | Ak6 |
| 6440 | 3 | 4 | 5 | | V-1 | Akap10 |
| 6441 | 3 | 4 | 5 | | V-1 | Akap11 |
| 6442 | 3 | 4 | 5 | | V-1 | Akap12 |
| 6443 | 3 | 4 | 5 | | V-1 | Akap13 |
| 6444 | 3 | 4 | 5 | | V-1 | Akap17b |
| 6445 | 3 | 4 | 5 | | V-1 | Akap6 |
| 6446 | 3 | 4 | 5 | | V-1 | Akap7 |
| 6447 | 3 | 4 | 5 | | V-1 | Akip1 |
| 6448 | 3 | 4 | 5 | | V-1 | Akna |
| 6449 | 3 | 4 | 5 | | V-1 | Akr1b8 |
| 6450 | 3 | 4 | 5 | | V-1 | Akr1c12 |
| 6451 | 3 | 4 | 5 | | V-1 | Akr1c13 |
| 6452 | 3 | 4 | 5 | | V-1 | Akr1c18 |
| 6453 | 3 | 4 | 5 | | V-1 | Akr7a5 |
| 6454 | 3 | 4 | 5 | | V-1 | Akt3 |
| 6455 | 3 | 4 | 5 | | V-1 | Aldh16a1 |
| 6456 | 3 | 4 | 5 | | V-1 | Aldh1a7 |
| 6457 | 3 | 4 | 5 | | V-1 | Aldh1l1 |
| 6458 | 3 | 4 | 5 | | V-1 | Aldh3a2 |
| 6459 | 3 | 4 | 5 | | V-1 | Aldh3b1 |
| 6460 | 3 | 4 | 5 | | V-1 | Aldh5a1 |
| 6461 | 3 | 4 | 5 | | V-1 | Alg1 |
| 6462 | 3 | 4 | 5 | | V-1 | Alg14 |
| 6463 | 3 | 4 | 5 | | V-1 | Alg3 |
| 6464 | 3 | 4 | 5 | | V-1 | Alg8 |
| 6465 | 3 | 4 | 5 | | V-1 | Alg9 |
| 6466 | 3 | 4 | 5 | | V-1 | Alk |
| 6467 | 3 | 4 | 5 | | V-1 | Alkbh2 |
| 6468 | 3 | 4 | 5 | | V-1 | Alox5ap |
| 6469 | 3 | 4 | 5 | | V-1 | Alpk1 |
| 6470 | 3 | 4 | 5 | | V-1 | Alpk3 |
| 6471 | 3 | 4 | 5 | | V-1 | Als2 |
| 6472 | 3 | 4 | 5 | | V-1 | Alyref |
| 6473 | 3 | 4 | 5 | | V-1 | Amdhd2 |
| 6474 | 3 | 4 | 5 | | V-1 | Amer3 |
| 6475 | 3 | 4 | 5 | | V-1 | Amh |
| 6476 | 3 | 4 | 5 | | V-1 | Amigo3 |
| 6477 | 3 | 4 | 5 | | V-1 | Amn |
| 6478 | 3 | 4 | 5 | | V-1 | Amn1 |
| 6479 | 3 | 4 | 5 | | V-1 | Amotl1 |
| 6480 | 3 | 4 | 5 | | V-1 | Ampd1 |
| 6481 | 3 | 4 | 5 | | V-1 | Anapc4 |
| 6482 | 3 | 4 | 5 | | V-1 | Angpt4 |
| 6483 | 3 | 4 | 5 | | V-1 | Angptl1 |
| 6484 | 3 | 4 | 5 | | V-1 | Angptl2 |
| 6485 | 3 | 4 | 5 | | V-1 | Angptl6 |
| 6486 | 3 | 4 | 5 | | V-1 | Ank |
| 6487 | 3 | 4 | 5 | | V-1 | Ank3 |
| 6488 | 3 | 4 | 5 | | V-1 | Ankrd13b |
| 6489 | 3 | 4 | 5 | | V-1 | Ankrd13c |
| 6490 | 3 | 4 | 5 | | V-1 | Ankrd23 |
| 6491 | 3 | 4 | 5 | | V-1 | Ankrd26 |
| 6492 | 3 | 4 | 5 | | V-1 | Ankrd27 |
| 6493 | 3 | 4 | 5 | | V-1 | Ankrd55 |
| 6494 | 3 | 4 | 5 | | V-1 | Ankrd6 |
| 6495 | 3 | 4 | 5 | | V-1 | Ankrd61 |
| 6496 | 3 | 4 | 5 | | V-1 | Ankrd9 |
| 6497 | 3 | 4 | 5 | | V-1 | Anks1 |
| 6498 | 3 | 4 | 5 | | V-1 | Anks3 |
| 6499 | 3 | 4 | 5 | | V-1 | Antxr2 |
| 6500 | 3 | 4 | 5 | | V-1 | Anxa13 |
| 6501 | 3 | 4 | 5 | | V-1 | Anxa2 |
| 6502 | 3 | 4 | 5 | | V-1 | Anxa8 |
| 6503 | 3 | 4 | 5 | | V-1 | Anxa9 |
| 6504 | 3 | 4 | 5 | | V-1 | Aoc2 |
| 6505 | 3 | 4 | 5 | | V-1 | Aoc3 |
| 6506 | 3 | 4 | 5 | | V-1 | Ap1g2 |
| 6507 | 3 | 4 | 5 | | V-1 | Ap1s1 |
| 6508 | 3 | 4 | 5 | | V-1 | Ap2m1 |
| 6509 | 3 | 4 | 5 | | V-1 | Ap4m1 |
| 6510 | 3 | 4 | 5 | | V-1 | Ap5b1 |
| 6511 | 3 | 4 | 5 | | V-1 | Ap5m1 |
| 6512 | 3 | 4 | 5 | | V-1 | Apba1 |
| 6513 | 3 | 4 | 5 | | V-1 | Apbb1ip |
| 6514 | 3 | 4 | 5 | | V-1 | Apc |
| 6515 | 3 | 4 | 5 | | V-1 | Apc2 |
| 6516 | 3 | 4 | 5 | | V-1 | Apcs |
| 6517 | 3 | 4 | 5 | | V-1 | Apex1 |
| 6518 | 3 | 4 | 5 | | V-1 | Apex2 |
| 6519 | 3 | 4 | 5 | | V-1 | Aph1b |
| 6520 | 3 | 4 | 5 | | V-1 | Apip |
| 6521 | 3 | 4 | 5 | | V-1 | Apitd1 |
| 6522 | 3 | 4 | 5 | | V-1 | Apln |
| 6523 | 3 | 4 | 5 | | V-1 | Aplnr |
| 6524 | 3 | 4 | 5 | | V-1 | Apobec2 |
| 6525 | 3 | 4 | 5 | | V-1 | Apod |
| 6526 | 3 | 4 | 5 | | V-1 | Apol11a |

Fig. 36 - 35

| | | | | | | | | | | | | | |
|---|---|---|---|---|---|---|---|---|---|---|---|---|---|
| 6527 | 3 | 4 | 5 | | V-1 | Apol11b | 6623 | 3 | 4 | 5 | | V-1 | Atp6v1g2 |
| 6528 | 3 | 4 | 5 | | V-1 | Apol7a | 6624 | 3 | 4 | 5 | | V-1 | Atp7a |
| 6529 | 3 | 4 | 5 | | V-1 | Apool | 6625 | 3 | 4 | 5 | | V-1 | Atpif1 |
| 6530 | 3 | 4 | 5 | | V-1 | Aprt | 6626 | 3 | 4 | 5 | | V-1 | Atr |
| 6531 | 3 | 4 | 5 | | V-1 | Aqp12 | 6627 | 3 | 4 | 5 | | V-1 | Atraid |
| 6532 | 3 | 4 | 5 | | V-1 | Arap1 | 6628 | 3 | 4 | 5 | | V-1 | Atrn |
| 6533 | 3 | 4 | 5 | | V-1 | Arcn1 | 6629 | 3 | 4 | 5 | | V-1 | Atrx |
| 6534 | 3 | 4 | 5 | | V-1 | Arf2 | 6630 | 3 | 4 | 5 | | V-1 | Atxn1 |
| 6535 | 3 | 4 | 5 | | V-1 | Arf4 | 6631 | 3 | 4 | 5 | | V-1 | Atxn1l |
| 6536 | 3 | 4 | 5 | | V-1 | Arhgap15 | 6632 | 3 | 4 | 5 | | V-1 | Atxn7l2 |
| 6537 | 3 | 4 | 5 | | V-1 | Arhgap18 | 6633 | 3 | 4 | 5 | | V-1 | Aurka |
| 6538 | 3 | 4 | 5 | | V-1 | Arhgap19 | 6634 | 3 | 4 | 5 | | V-1 | Aurkb |
| 6539 | 3 | 4 | 5 | | V-1 | Arhgap20 | 6635 | 3 | 4 | 5 | | V-1 | Auts2 |
| 6540 | 3 | 4 | 5 | | V-1 | Arhgap20os | 6636 | 3 | 4 | 5 | | V-1 | Avpi1 |
| 6541 | 3 | 4 | 5 | | V-1 | Arhgap24 | 6637 | 3 | 4 | 5 | | V-1 | B230208H11Rik |
| 6542 | 3 | 4 | 5 | | V-1 | Arhgap30 | 6638 | 3 | 4 | 5 | | V-1 | B230216N24Rik |
| 6543 | 3 | 4 | 5 | | V-1 | Arhgap31 | 6639 | 3 | 4 | 5 | | V-1 | B230217O12Rik |
| 6544 | 3 | 4 | 5 | | V-1 | Arhgap32 | 6640 | 3 | 4 | 5 | | V-1 | B230219D22Rik |
| 6545 | 3 | 4 | 5 | | V-1 | Arhgap35 | 6641 | 3 | 4 | 5 | | V-1 | B230312C02Rik |
| 6546 | 3 | 4 | 5 | | V-1 | Arhgap39 | 6642 | 3 | 4 | 5 | | V-1 | B2m |
| 6547 | 3 | 4 | 5 | | V-1 | Arhgap4 | 6643 | 3 | 4 | 5 | | V-1 | B3galt5 |
| 6548 | 3 | 4 | 5 | | V-1 | Arhgdig | 6644 | 3 | 4 | 5 | | V-1 | B3galt6 |
| 6549 | 3 | 4 | 5 | | V-1 | Arhgef1 | 6645 | 3 | 4 | 5 | | V-1 | B3gat3 |
| 6550 | 3 | 4 | 5 | | V-1 | Arhgef12 | 6646 | 3 | 4 | 5 | | V-1 | B3gnt2 |
| 6551 | 3 | 4 | 5 | | V-1 | Arhgef19 | 6647 | 3 | 4 | 5 | | V-1 | B3gnt3 |
| 6552 | 3 | 4 | 5 | | V-1 | Arhgef26 | 6648 | 3 | 4 | 5 | | V-1 | B3gntl1 |
| 6553 | 3 | 4 | 5 | | V-1 | Arhgef40 | 6649 | 3 | 4 | 5 | | V-1 | B4galt1 |
| 6554 | 3 | 4 | 5 | | V-1 | Arhgef5 | 6650 | 3 | 4 | 5 | | V-1 | B930059L03Rik |
| 6555 | 3 | 4 | 5 | | V-1 | Arid3a | 6651 | 3 | 4 | 5 | | V-1 | BC005537 |
| 6556 | 3 | 4 | 5 | | V-1 | Arid3b | 6652 | 3 | 4 | 5 | | V-1 | BC005624 |
| 6557 | 3 | 4 | 5 | | V-1 | Arl10 | 6653 | 3 | 4 | 5 | | V-1 | BC005764 |
| 6558 | 3 | 4 | 5 | | V-1 | Arl13b | 6654 | 3 | 4 | 5 | | V-1 | BC017643 |
| 6559 | 3 | 4 | 5 | | V-1 | Arl2 | 6655 | 3 | 4 | 5 | | V-1 | BC021767 |
| 6560 | 3 | 4 | 5 | | V-1 | Arl4d | 6656 | 3 | 4 | 5 | | V-1 | BC022687 |
| 6561 | 3 | 4 | 5 | | V-1 | Arl5c | 6657 | 3 | 4 | 5 | | V-1 | BC025920 |
| 6562 | 3 | 4 | 5 | | V-1 | Arl6 | 6658 | 3 | 4 | 5 | | V-1 | BC026585 |
| 6563 | 3 | 4 | 5 | | V-1 | Arl6ip5 | 6659 | 3 | 4 | 5 | | V-1 | BC028528 |
| 6564 | 3 | 4 | 5 | | V-1 | Arl8a | 6660 | 3 | 4 | 5 | | V-1 | BC029214 |
| 6565 | 3 | 4 | 5 | | V-1 | Armc6 | 6661 | 3 | 4 | 5 | | V-1 | BC029722 |
| 6566 | 3 | 4 | 5 | | V-1 | Armc7 | 6662 | 3 | 4 | 5 | | V-1 | BC037034 |
| 6567 | 3 | 4 | 5 | | V-1 | Armcx1 | 6663 | 3 | 4 | 5 | | V-1 | BC037704 |
| 6568 | 3 | 4 | 5 | | V-1 | Armcx4 | 6664 | 3 | 4 | 5 | | V-1 | BC048507 |
| 6569 | 3 | 4 | 5 | | V-1 | Arntl2 | 6665 | 3 | 4 | 5 | | V-1 | BC048562 |
| 6570 | 3 | 4 | 5 | | V-1 | Arpc1b | 6666 | 3 | 4 | 5 | | V-1 | BC051142 |
| 6571 | 3 | 4 | 5 | | V-1 | Arrb2 | 6667 | 3 | 4 | 5 | | V-1 | BC051226 |
| 6572 | 3 | 4 | 5 | | V-1 | Arrdc1 | 6668 | 3 | 4 | 5 | | V-1 | BC052040 |
| 6573 | 3 | 4 | 5 | | V-1 | Arrdc2 | 6669 | 3 | 4 | 5 | | V-1 | BC053749 |
| 6574 | 3 | 4 | 5 | | V-1 | Arsg | 6670 | 3 | 4 | 5 | | V-1 | BC055324 |
| 6575 | 3 | 4 | 5 | | V-1 | Arv1 | 6671 | 3 | 4 | 5 | | V-1 | Bace1 |
| 6576 | 3 | 4 | 5 | | V-1 | Arxes1 | 6672 | 3 | 4 | 5 | | V-1 | Bag2 |
| 6577 | 3 | 4 | 5 | | V-1 | Asah2 | 6673 | 3 | 4 | 5 | | V-1 | Baiap2l2 |
| 6578 | 3 | 4 | 5 | | V-1 | Asap2 | 6674 | 3 | 4 | 5 | | V-1 | Bambi |
| 6579 | 3 | 4 | 5 | | V-1 | Asap3 | 6675 | 3 | 4 | 5 | | V-1 | Bambi-ps1 |
| 6580 | 3 | 4 | 5 | | V-1 | Asb1 | 6676 | 3 | 4 | 5 | | V-1 | Banf1 |
| 6581 | 3 | 4 | 5 | | V-1 | Asb18 | 6677 | 3 | 4 | 5 | | V-1 | Banf2 |
| 6582 | 3 | 4 | 5 | | V-1 | Asb5 | 6678 | 3 | 4 | 5 | | V-1 | Barx2 |
| 6583 | 3 | 4 | 5 | | V-1 | Ascc1 | 6679 | 3 | 4 | 5 | | V-1 | Baz1b |
| 6584 | 3 | 4 | 5 | | V-1 | Ascc2 | 6680 | 3 | 4 | 5 | | V-1 | Baz2a |
| 6585 | 3 | 4 | 5 | | V-1 | Ascl2 | 6681 | 3 | 4 | 5 | | V-1 | Bbs7 |
| 6586 | 3 | 4 | 5 | | V-1 | Ascl3 | 6682 | 3 | 4 | 5 | | V-1 | Bbx |
| 6587 | 3 | 4 | 5 | | V-1 | Asic1 | 6683 | 3 | 4 | 5 | | V-1 | Bcar3 |
| 6588 | 3 | 4 | 5 | | V-1 | Asl | 6684 | 3 | 4 | 5 | | V-1 | Bcaslos2 |
| 6589 | 3 | 4 | 5 | | V-1 | Aspa | 6685 | 3 | 4 | 5 | | V-1 | Bcas2 |
| 6590 | 3 | 4 | 5 | | V-1 | Asphd1 | 6686 | 3 | 4 | 5 | | V-1 | Bcat1 |
| 6591 | 3 | 4 | 5 | | V-1 | Aspm | 6687 | 3 | 4 | 5 | | V-1 | Bcat2 |
| 6592 | 3 | 4 | 5 | | V-1 | Aspn | 6688 | 3 | 4 | 5 | | V-1 | Bckdha |
| 6593 | 3 | 4 | 5 | | V-1 | Asprv1 | 6689 | 3 | 4 | 5 | | V-1 | Bckdk |
| 6594 | 3 | 4 | 5 | | V-1 | Aste1 | 6690 | 3 | 4 | 5 | | V-1 | Bcl2l1 |
| 6595 | 3 | 4 | 5 | | V-1 | Asxl1 | 6691 | 3 | 4 | 5 | | V-1 | Bcl2l14 |
| 6596 | 3 | 4 | 5 | | V-1 | Asxl2 | 6692 | 3 | 4 | 5 | | V-1 | Bcl7b |
| 6597 | 3 | 4 | 5 | | V-1 | Atad2b | 6693 | 3 | 4 | 5 | | V-1 | Bclaf1 |
| 6598 | 3 | 4 | 5 | | V-1 | Atat1 | 6694 | 3 | 4 | 5 | | V-1 | Bcmo1 |
| 6599 | 3 | 4 | 5 | | V-1 | Atcayos | 6695 | 3 | 4 | 5 | | V-1 | Bcor |
| 6600 | 3 | 4 | 5 | | V-1 | Atg101 | 6696 | 3 | 4 | 5 | | V-1 | Bcs1l |
| 6601 | 3 | 4 | 5 | | V-1 | Atg16l1 | 6697 | 3 | 4 | 5 | | V-1 | Bdh2 |
| 6602 | 3 | 4 | 5 | | V-1 | Atg16l2 | 6698 | 3 | 4 | 5 | | V-1 | Bdp1 |
| 6603 | 3 | 4 | 5 | | V-1 | Atl3 | 6699 | 3 | 4 | 5 | | V-1 | Bend3 |
| 6604 | 3 | 4 | 5 | | V-1 | Atp10a | 6700 | 3 | 4 | 5 | | V-1 | Bend5 |
| 6605 | 3 | 4 | 5 | | V-1 | Atp11a | 6701 | 3 | 4 | 5 | | V-1 | Bend6 |
| 6606 | 3 | 4 | 5 | | V-1 | Atp1a1 | 6702 | 3 | 4 | 5 | | V-1 | Bhlha15 |
| 6607 | 3 | 4 | 5 | | V-1 | Atp1a3 | 6703 | 3 | 4 | 5 | | V-1 | Bhlhe40 |
| 6608 | 3 | 4 | 5 | | V-1 | Atp1a4 | 6704 | 3 | 4 | 5 | | V-1 | Bid |
| 6609 | 3 | 4 | 5 | | V-1 | Atp2a3 | 6705 | 3 | 4 | 5 | | V-1 | Bin2 |
| 6610 | 3 | 4 | 5 | | V-1 | Atp2c2 | 6706 | 3 | 4 | 5 | | V-1 | Bin3 |
| 6611 | 3 | 4 | 5 | | V-1 | Atp5g1 | 6707 | 3 | 4 | 5 | | V-1 | Birc5 |
| 6612 | 3 | 4 | 5 | | V-1 | Atp5g2 | 6708 | 3 | 4 | 5 | | V-1 | Blnk |
| 6613 | 3 | 4 | 5 | | V-1 | Atp5g3 | 6709 | 3 | 4 | 5 | | V-1 | Bloc1s1 |
| 6614 | 3 | 4 | 5 | | V-1 | Atp5h | 6710 | 3 | 4 | 5 | | V-1 | Bloc1s5 |
| 6615 | 3 | 4 | 5 | | V-1 | Atp5j2 | 6711 | 3 | 4 | 5 | | V-1 | Bmp2k |
| 6616 | 3 | 4 | 5 | | V-1 | Atp5l | 6712 | 3 | 4 | 5 | | V-1 | Bmp5 |
| 6617 | 3 | 4 | 5 | | V-1 | Atp5o | 6713 | 3 | 4 | 5 | | V-1 | Bmpr2 |
| 6618 | 3 | 4 | 5 | | V-1 | Atp6ap1l | 6714 | 3 | 4 | 5 | | V-1 | Bola1 |
| 6619 | 3 | 4 | 5 | | V-1 | Atp6v0e2 | 6715 | 3 | 4 | 5 | | V-1 | Bpnt1 |
| 6620 | 3 | 4 | 5 | | V-1 | Atp6v1b1 | 6716 | 3 | 4 | 5 | | V-1 | Brca2 |
| 6621 | 3 | 4 | 5 | | V-1 | Atp6v1e1 | 6717 | 3 | 4 | 5 | | V-1 | Brd4 |
| 6622 | 3 | 4 | 5 | | V-1 | Atp6v1f | 6718 | 3 | 4 | 5 | | V-1 | Brf2 |

Fig. 36 - 36

| | | | | | | | |
|---|---|---|---|---|---|---|---|
| 6719 | 3 | 4 | 5 | | V-1 | Brix1 |
| 6720 | 3 | 4 | 5 | | V-1 | Brk1 |
| 6721 | 3 | 4 | 5 | | V-1 | Brms1 |
| 6722 | 3 | 4 | 5 | | V-1 | Brpf1 |
| 6723 | 3 | 4 | 5 | | V-1 | Brsk1 |
| 6724 | 3 | 4 | 5 | | V-1 | Brsk2 |
| 6725 | 3 | 4 | 5 | | V-1 | Brwd3 |
| 6726 | 3 | 4 | 5 | | V-1 | Bscl2 |
| 6727 | 3 | 4 | 5 | | V-1 | Bsn |
| 6728 | 3 | 4 | 5 | | V-1 | Bst1 |
| 6729 | 3 | 4 | 5 | | V-1 | Btbd10 |
| 6730 | 3 | 4 | 5 | | V-1 | Btg2 |
| 6731 | 3 | 4 | 5 | | V-1 | Btla |
| 6732 | 3 | 4 | 5 | | V-1 | Btnl6 |
| 6733 | 3 | 4 | 5 | | V-1 | Bub1 |
| 6734 | 3 | 4 | 5 | | V-1 | Bysl |
| 6735 | 3 | 4 | 5 | | V-1 | C030013G03Rik |
| 6736 | 3 | 4 | 5 | | V-1 | C030034L19Rik |
| 6737 | 3 | 4 | 5 | | V-1 | C130026I21Rik |
| 6738 | 3 | 4 | 5 | | V-1 | C130046K22Rik |
| 6739 | 3 | 4 | 5 | | V-1 | C130080G10Rik |
| 6740 | 3 | 4 | 5 | | V-1 | C1ql3 |
| 6741 | 3 | 4 | 5 | | V-1 | C1qtnf2 |
| 6742 | 3 | 4 | 5 | | V-1 | C1qtnf3 |
| 6743 | 3 | 4 | 5 | | V-1 | C1qtnf4 |
| 6744 | 3 | 4 | 5 | | V-1 | C1qtnf5 |
| 6745 | 3 | 4 | 5 | | V-1 | C1qtnf6 |
| 6746 | 3 | 4 | 5 | | V-1 | C1qtnf9 |
| 6747 | 3 | 4 | 5 | | V-1 | C1rl |
| 6748 | 3 | 4 | 5 | | V-1 | C1s2 |
| 6749 | 3 | 4 | 5 | | V-1 | C230037L18Rik |
| 6750 | 3 | 4 | 5 | | V-1 | C230091D08Rik |
| 6751 | 3 | 4 | 5 | | V-1 | C2cd2i |
| 6752 | 3 | 4 | 5 | | V-1 | C2cd4a |
| 6753 | 3 | 4 | 5 | | V-1 | C2cd4b |
| 6754 | 3 | 4 | 5 | | V-1 | C330027C09Rik |
| 6755 | 3 | 4 | 5 | | V-1 | C4a |
| 6756 | 3 | 4 | 5 | | V-1 | C4bp-ps1 |
| 6757 | 3 | 4 | 5 | | V-1 | C530044C16Rik |
| 6758 | 3 | 4 | 5 | | V-1 | C5ar1 |
| 6759 | 3 | 4 | 5 | | V-1 | C8g |
| 6760 | 3 | 4 | 5 | | V-1 | C920021L13Rik |
| 6761 | 3 | 4 | 5 | | V-1 | C920025E04Rik |
| 6762 | 3 | 4 | 5 | | V-1 | Caap1 |
| 6763 | 3 | 4 | 5 | | V-1 | Cables1 |
| 6764 | 3 | 4 | 5 | | V-1 | Cabp1 |
| 6765 | 3 | 4 | 5 | | V-1 | Cabp7 |
| 6766 | 3 | 4 | 5 | | V-1 | Cachd1 |
| 6767 | 3 | 4 | 5 | | V-1 | Cacna1c |
| 6768 | 3 | 4 | 5 | | V-1 | Cacna2d2 |
| 6769 | 3 | 4 | 5 | | V-1 | Cacng1 |
| 6770 | 3 | 4 | 5 | | V-1 | Cacng4 |
| 6771 | 3 | 4 | 5 | | V-1 | Cacng7 |
| 6772 | 3 | 4 | 5 | | V-1 | Cactin |
| 6773 | 3 | 4 | 5 | | V-1 | Cadm1 |
| 6774 | 3 | 4 | 5 | | V-1 | Cadps2 |
| 6775 | 3 | 4 | 5 | | V-1 | Calca |
| 6776 | 3 | 4 | 5 | | V-1 | Calcb |
| 6777 | 3 | 4 | 5 | | V-1 | Calhm2 |
| 6778 | 3 | 4 | 5 | | V-1 | Calr |
| 6779 | 3 | 4 | 5 | | V-1 | Calr3 |
| 6780 | 3 | 4 | 5 | | V-1 | Calu |
| 6781 | 3 | 4 | 5 | | V-1 | Camk1d |
| 6782 | 3 | 4 | 5 | | V-1 | Camk1g |
| 6783 | 3 | 4 | 5 | | V-1 | Camk2b |
| 6784 | 3 | 4 | 5 | | V-1 | Camkmt |
| 6785 | 3 | 4 | 5 | | V-1 | Camsap1 |
| 6786 | 3 | 4 | 5 | | V-1 | Canx |
| 6787 | 3 | 4 | 5 | | V-1 | Capn10 |
| 6788 | 3 | 4 | 5 | | V-1 | Capn8 |
| 6789 | 3 | 4 | 5 | | V-1 | Capns1 |
| 6790 | 3 | 4 | 5 | | V-1 | Capns2 |
| 6791 | 3 | 4 | 5 | | V-1 | Card10 |
| 6792 | 3 | 4 | 5 | | V-1 | Card9 |
| 6793 | 3 | 4 | 5 | | V-1 | Cars |
| 6794 | 3 | 4 | 5 | | V-1 | Cars2 |
| 6795 | 3 | 4 | 5 | | V-1 | Casp1 |
| 6796 | 3 | 4 | 5 | | V-1 | Casp8 |
| 6797 | 3 | 4 | 5 | | V-1 | Casp8ap2 |
| 6798 | 3 | 4 | 5 | | V-1 | Catsper4 |
| 6799 | 3 | 4 | 5 | | V-1 | Cav2 |
| 6800 | 3 | 4 | 5 | | V-1 | Cav3 |
| 6801 | 3 | 4 | 5 | | V-1 | Cbr3 |
| 6802 | 3 | 4 | 5 | | V-1 | Cbs |
| 6803 | 3 | 4 | 5 | | V-1 | Cbx4 |
| 6804 | 3 | 4 | 5 | | V-1 | Cbx5 |
| 6805 | 3 | 4 | 5 | | V-1 | Cbx8 |
| 6806 | 3 | 4 | 5 | | V-1 | Ccar1 |
| 6807 | 3 | 4 | 5 | | V-1 | Ccbl1 |
| 6808 | 3 | 4 | 5 | | V-1 | Ccdc101 |
| 6809 | 3 | 4 | 5 | | V-1 | Ccdc102a |
| 6810 | 3 | 4 | 5 | | V-1 | Ccdc104 |
| 6811 | 3 | 4 | 5 | | V-1 | Ccdc107 |
| 6812 | 3 | 4 | 5 | | V-1 | Ccdc109b |
| 6813 | 3 | 4 | 5 | | V-1 | Ccdc113 |
| 6814 | 3 | 4 | 5 | | V-1 | Ccdc12 |
| 6815 | 3 | 4 | 5 | | V-1 | Ccdc121 |
| 6816 | 3 | 4 | 5 | | V-1 | Ccdc122 |
| 6817 | 3 | 4 | 5 | | V-1 | Ccdc124 |
| 6818 | 3 | 4 | 5 | | V-1 | Ccdc125 |
| 6819 | 3 | 4 | 5 | | V-1 | Ccdc134 |
| 6820 | 3 | 4 | 5 | | V-1 | Ccdc135 |
| 6821 | 3 | 4 | 5 | | V-1 | Ccdc137 |
| 6822 | 3 | 4 | 5 | | V-1 | Ccdc142 |
| 6823 | 3 | 4 | 5 | | V-1 | Ccdc155 |
| 6824 | 3 | 4 | 5 | | V-1 | Ccdc157 |
| 6825 | 3 | 4 | 5 | | V-1 | Ccdc160 |
| 6826 | 3 | 4 | 5 | | V-1 | Ccdc162 |
| 6827 | 3 | 4 | 5 | | V-1 | Ccdc163 |
| 6828 | 3 | 4 | 5 | | V-1 | Ccdc166 |
| 6829 | 3 | 4 | 5 | | V-1 | Ccdc167 |
| 6830 | 3 | 4 | 5 | | V-1 | Ccdc17 |
| 6831 | 3 | 4 | 5 | | V-1 | Ccdc173 |
| 6832 | 3 | 4 | 5 | | V-1 | Ccdc19 |
| 6833 | 3 | 4 | 5 | | V-1 | Ccdc24 |
| 6834 | 3 | 4 | 5 | | V-1 | Ccdc28b |
| 6835 | 3 | 4 | 5 | | V-1 | Ccdc30 |
| 6836 | 3 | 4 | 5 | | V-1 | Ccdc37 |
| 6837 | 3 | 4 | 5 | | V-1 | Ccdc38 |
| 6838 | 3 | 4 | 5 | | V-1 | Ccdc42 |
| 6839 | 3 | 4 | 5 | | V-1 | Ccdc51 |
| 6840 | 3 | 4 | 5 | | V-1 | Ccdc53 |
| 6841 | 3 | 4 | 5 | | V-1 | Ccdc55 |
| 6842 | 3 | 4 | 5 | | V-1 | Ccdc58 |
| 6843 | 3 | 4 | 5 | | V-1 | Ccdc71l |
| 6844 | 3 | 4 | 5 | | V-1 | Ccdc73 |
| 6845 | 3 | 4 | 5 | | V-1 | Ccdc8 |
| 6846 | 3 | 4 | 5 | | V-1 | Ccdc84 |
| 6847 | 3 | 4 | 5 | | V-1 | Ccdc86 |
| 6848 | 3 | 4 | 5 | | V-1 | Ccdc88b |
| 6849 | 3 | 4 | 5 | | V-1 | Ccdc89 |
| 6850 | 3 | 4 | 5 | | V-1 | Ccdc9 |
| 6851 | 3 | 4 | 5 | | V-1 | Ccdc93 |
| 6852 | 3 | 4 | 5 | | V-1 | Cck |
| 6853 | 3 | 4 | 5 | | V-1 | Ccl1 |
| 6854 | 3 | 4 | 5 | | V-1 | Ccl20 |
| 6855 | 3 | 4 | 5 | | V-1 | Ccl21a |
| 6856 | 3 | 4 | 5 | | V-1 | Ccl22 |
| 6857 | 3 | 4 | 5 | | V-1 | Ccl24 |
| 6858 | 3 | 4 | 5 | | V-1 | Ccl27a |
| 6859 | 3 | 4 | 5 | | V-1 | Ccl4 |
| 6860 | 3 | 4 | 5 | | V-1 | Ccm2 |
| 6861 | 3 | 4 | 5 | | V-1 | Ccnb1 |
| 6862 | 3 | 4 | 5 | | V-1 | Ccnd1 |
| 6863 | 3 | 4 | 5 | | V-1 | Ccnd2 |
| 6864 | 3 | 4 | 5 | | V-1 | Ccne2 |
| 6865 | 3 | 4 | 5 | | V-1 | Ccnjl |
| 6866 | 3 | 4 | 5 | | V-1 | Ccnl2 |
| 6867 | 3 | 4 | 5 | | V-1 | Ccnt2 |
| 6868 | 3 | 4 | 5 | | V-1 | Ccp110 |
| 6869 | 3 | 4 | 5 | | V-1 | Ccr1 |
| 6870 | 3 | 4 | 5 | | V-1 | Ccr6 |
| 6871 | 3 | 4 | 5 | | V-1 | Ccr7 |
| 6872 | 3 | 4 | 5 | | V-1 | Ccs |
| 6873 | 3 | 4 | 5 | | V-1 | Ccser1 |
| 6874 | 3 | 4 | 5 | | V-1 | Cd101 |
| 6875 | 3 | 4 | 5 | | V-1 | Cd2 |
| 6876 | 3 | 4 | 5 | | V-1 | Cd209a |
| 6877 | 3 | 4 | 5 | | V-1 | Cd209f |
| 6878 | 3 | 4 | 5 | | V-1 | Cd209g |
| 6879 | 3 | 4 | 5 | | V-1 | Cd244 |
| 6880 | 3 | 4 | 5 | | V-1 | Cd27 |
| 6881 | 3 | 4 | 5 | | V-1 | Cd276 |
| 6882 | 3 | 4 | 5 | | V-1 | Cd28 |
| 6883 | 3 | 4 | 5 | | V-1 | Cd300c |
| 6884 | 3 | 4 | 5 | | V-1 | Cd300e |
| 6885 | 3 | 4 | 5 | | V-1 | Cd300ld |
| 6886 | 3 | 4 | 5 | | V-1 | Cd300lf |
| 6887 | 3 | 4 | 5 | | V-1 | Cd36 |
| 6888 | 3 | 4 | 5 | | V-1 | Cd37 |
| 6889 | 3 | 4 | 5 | | V-1 | Cd38 |
| 6890 | 3 | 4 | 5 | | V-1 | Cd3d |
| 6891 | 3 | 4 | 5 | | V-1 | Cd63 |
| 6892 | 3 | 4 | 5 | | V-1 | Cd68 |
| 6893 | 3 | 4 | 5 | | V-1 | Cd69 |
| 6894 | 3 | 4 | 5 | | V-1 | Cd80 |
| 6895 | 3 | 4 | 5 | | V-1 | Cd83 |
| 6896 | 3 | 4 | 5 | | V-1 | Cd84 |
| 6897 | 3 | 4 | 5 | | V-1 | Cdc14a |
| 6898 | 3 | 4 | 5 | | V-1 | Cdc25b |
| 6899 | 3 | 4 | 5 | | V-1 | Cdc25c |
| 6900 | 3 | 4 | 5 | | V-1 | Cdc40 |
| 6901 | 3 | 4 | 5 | | V-1 | Cdc42ep2 |
| 6902 | 3 | 4 | 5 | | V-1 | Cdca3 |
| 6903 | 3 | 4 | 5 | | V-1 | Cdca7l |
| 6904 | 3 | 4 | 5 | | V-1 | Cdh13 |
| 6905 | 3 | 4 | 5 | | V-1 | Cdh24 |
| 6906 | 3 | 4 | 5 | | V-1 | Cdh26 |
| 6907 | 3 | 4 | 5 | | V-1 | Cdh4 |
| 6908 | 3 | 4 | 5 | | V-1 | Cdh5 |
| 6909 | 3 | 4 | 5 | | V-1 | Cdk10 |
| 6910 | 3 | 4 | 5 | | V-1 | Cdk12 |

Fig. 36 - 37

| | | | | | | |
|---|---|---|---|---|---|---|
| 6911 | 3 | 4 | 5 | | V-1 | Cdk2 |
| 6912 | 3 | 4 | 5 | | V-1 | Cdk5rap2 |
| 6913 | 3 | 4 | 5 | | V-1 | Cdk7 |
| 6914 | 3 | 4 | 5 | | V-1 | Cdkl1 |
| 6915 | 3 | 4 | 5 | | V-1 | Cdkl3 |
| 6916 | 3 | 4 | 5 | | V-1 | Cdkn2c |
| 6917 | 3 | 4 | 5 | | V-1 | Cdkn3 |
| 6918 | 3 | 4 | 5 | | V-1 | Cdon |
| 6919 | 3 | 4 | 5 | | V-1 | Cdpf1 |
| 6920 | 3 | 4 | 5 | | V-1 | Cdr2 |
| 6921 | 3 | 4 | 5 | | V-1 | Cdt1 |
| 6922 | 3 | 4 | 5 | | V-1 | Cdx2 |
| 6923 | 3 | 4 | 5 | | V-1 | Ceacam16 |
| 6924 | 3 | 4 | 5 | | V-1 | Cebpa |
| 6925 | 3 | 4 | 5 | | V-1 | Cebpz |
| 6926 | 3 | 4 | 5 | | V-1 | Cecr2 |
| 6927 | 3 | 4 | 5 | | V-1 | Celrr |
| 6928 | 3 | 4 | 5 | | V-1 | Celsr3 |
| 6929 | 3 | 4 | 5 | | V-1 | Cenpa |
| 6930 | 3 | 4 | 5 | | V-1 | Cenpc1 |
| 6931 | 3 | 4 | 5 | | V-1 | Cenpe |
| 6932 | 3 | 4 | 5 | | V-1 | Cenpf |
| 6933 | 3 | 4 | 5 | | V-1 | Cenph |
| 6934 | 3 | 4 | 5 | | V-1 | Cenpj |
| 6935 | 3 | 4 | 5 | | V-1 | Cenpn |
| 6936 | 3 | 4 | 5 | | V-1 | Cenpq |
| 6937 | 3 | 4 | 5 | | V-1 | Cep104 |
| 6938 | 3 | 4 | 5 | | V-1 | Cep131 |
| 6939 | 3 | 4 | 5 | | V-1 | Cep162 |
| 6940 | 3 | 4 | 5 | | V-1 | Cep170b |
| 6941 | 3 | 4 | 5 | | V-1 | Cep250 |
| 6942 | 3 | 4 | 5 | | V-1 | Cep290 |
| 6943 | 3 | 4 | 5 | | V-1 | Cep55 |
| 6944 | 3 | 4 | 5 | | V-1 | Cep78 |
| 6945 | 3 | 4 | 5 | | V-1 | Cep89 |
| 6946 | 3 | 4 | 5 | | V-1 | Ces1b |
| 6947 | 3 | 4 | 5 | | V-1 | Ces1f |
| 6948 | 3 | 4 | 5 | | V-1 | Ces2a |
| 6949 | 3 | 4 | 5 | | V-1 | Ces2c |
| 6950 | 3 | 4 | 5 | | V-1 | Ces2d-ps |
| 6951 | 3 | 4 | 5 | | V-1 | Cetn3 |
| 6952 | 3 | 4 | 5 | | V-1 | Cetn4 |
| 6953 | 3 | 4 | 5 | | V-1 | Cfc1 |
| 6954 | 3 | 4 | 5 | | V-1 | Cfl1 |
| 6955 | 3 | 4 | 5 | | V-1 | Chaf1a |
| 6956 | 3 | 4 | 5 | | V-1 | Chat |
| 6957 | 3 | 4 | 5 | | V-1 | Chchd1 |
| 6958 | 3 | 4 | 5 | | V-1 | Chchd10 |
| 6959 | 3 | 4 | 5 | | V-1 | Chchd2 |
| 6960 | 3 | 4 | 5 | | V-1 | Chchd6 |
| 6961 | 3 | 4 | 5 | | V-1 | Chd1l |
| 6962 | 3 | 4 | 5 | | V-1 | Chd3os |
| 6963 | 3 | 4 | 5 | | V-1 | Chd6 |
| 6964 | 3 | 4 | 5 | | V-1 | Chd7 |
| 6965 | 3 | 4 | 5 | | V-1 | Chd8 |
| 6966 | 3 | 4 | 5 | | V-1 | Chd9 |
| 6967 | 3 | 4 | 5 | | V-1 | Chdh |
| 6968 | 3 | 4 | 5 | | V-1 | Chek1 |
| 6969 | 3 | 4 | 5 | | V-1 | Chek2 |
| 6970 | 3 | 4 | 5 | | V-1 | Chic1 |
| 6971 | 3 | 4 | 5 | | V-1 | Chil1 |
| 6972 | 3 | 4 | 5 | | V-1 | Chka |
| 6973 | 3 | 4 | 5 | | V-1 | Chrm3 |
| 6974 | 3 | 4 | 5 | | V-1 | Chrna1 |
| 6975 | 3 | 4 | 5 | | V-1 | Chrna2 |
| 6976 | 3 | 4 | 5 | | V-1 | Chrna3 |
| 6977 | 3 | 4 | 5 | | V-1 | Chrnb1 |
| 6978 | 3 | 4 | 5 | | V-1 | Chrne |
| 6979 | 3 | 4 | 5 | | V-1 | Chst11 |
| 6980 | 3 | 4 | 5 | | V-1 | Chst5 |
| 6981 | 3 | 4 | 5 | | V-1 | Chsy3 |
| 6982 | 3 | 4 | 5 | | V-1 | Cib1 |
| 6983 | 3 | 4 | 5 | | V-1 | Cib3 |
| 6984 | 3 | 4 | 5 | | V-1 | Cic |
| 6985 | 3 | 4 | 5 | | V-1 | Cisd3 |
| 6986 | 3 | 4 | 5 | | V-1 | Cited2 |
| 6987 | 3 | 4 | 5 | | V-1 | Ckap4 |
| 6988 | 3 | 4 | 5 | | V-1 | Ckmt2 |
| 6989 | 3 | 4 | 5 | | V-1 | Cks2 |
| 6990 | 3 | 4 | 5 | | V-1 | Clasp1 |
| 6991 | 3 | 4 | 5 | | V-1 | Clca2 |
| 6992 | 3 | 4 | 5 | | V-1 | Clcn6 |
| 6993 | 3 | 4 | 5 | | V-1 | Cldn14 |
| 6994 | 3 | 4 | 5 | | V-1 | Clec10a |
| 6995 | 3 | 4 | 5 | | V-1 | Clec2d |
| 6996 | 3 | 4 | 5 | | V-1 | Clec2e |
| 6997 | 3 | 4 | 5 | | V-1 | Clec4a1 |
| 6998 | 3 | 4 | 5 | | V-1 | Clec4a3 |
| 6999 | 3 | 4 | 5 | | V-1 | Clec4d |
| 7000 | 3 | 4 | 5 | | V-1 | Clec5a |
| 7001 | 3 | 4 | 5 | | V-1 | Clgn |
| 7002 | 3 | 4 | 5 | | V-1 | Clic1 |
| 7003 | 3 | 4 | 5 | | V-1 | Clmn |
| 7004 | 3 | 4 | 5 | | V-1 | Clns1a |
| 7005 | 3 | 4 | 5 | | V-1 | Clock |
| 7006 | 3 | 4 | 5 | | V-1 | Clpp |
| 7007 | 3 | 4 | 5 | | V-1 | Clpx |
| 7008 | 3 | 4 | 5 | | V-1 | Clta |
| 7009 | 3 | 4 | 5 | | V-1 | Clybl |
| 7010 | 3 | 4 | 5 | | V-1 | Cma2 |
| 7011 | 3 | 4 | 5 | | V-1 | Cmc1 |
| 7012 | 3 | 4 | 5 | | V-1 | Cml1 |
| 7013 | 3 | 4 | 5 | | V-1 | Cml5 |
| 7014 | 3 | 4 | 5 | | V-1 | Cmss1 |
| 7015 | 3 | 4 | 5 | | V-1 | Cmtm3 |
| 7016 | 3 | 4 | 5 | | V-1 | Cmtm4 |
| 7017 | 3 | 4 | 5 | | V-1 | Cmtm7 |
| 7018 | 3 | 4 | 5 | | V-1 | Cmtm8 |
| 7019 | 3 | 4 | 5 | | V-1 | Cmya5 |
| 7020 | 3 | 4 | 5 | | V-1 | Cnbd2 |
| 7021 | 3 | 4 | 5 | | V-1 | Cnksr1 |
| 7022 | 3 | 4 | 5 | | V-1 | Cnnm2 |
| 7023 | 3 | 4 | 5 | | V-1 | Cnnm4 |
| 7024 | 3 | 4 | 5 | | V-1 | Cnot3 |
| 7025 | 3 | 4 | 5 | | V-1 | Cnot6 |
| 7026 | 3 | 4 | 5 | | V-1 | Cnpy1 |
| 7027 | 3 | 4 | 5 | | V-1 | Cnpy4 |
| 7028 | 3 | 4 | 5 | | V-1 | Cnrip1 |
| 7029 | 3 | 4 | 5 | | V-1 | Cntd1 |
| 7030 | 3 | 4 | 5 | | V-1 | Cntfr |
| 7031 | 3 | 4 | 5 | | V-1 | Cntn1 |
| 7032 | 3 | 4 | 5 | | V-1 | Cntrl |
| 7033 | 3 | 4 | 5 | | V-1 | Coa4 |
| 7034 | 3 | 4 | 5 | | V-1 | Cobl |
| 7035 | 3 | 4 | 5 | | V-1 | Col12a1 |
| 7036 | 3 | 4 | 5 | | V-1 | Col15a1 |
| 7037 | 3 | 4 | 5 | | V-1 | Col16a1 |
| 7038 | 3 | 4 | 5 | | V-1 | Col17a1 |
| 7039 | 3 | 4 | 5 | | V-1 | Col22a1 |
| 7040 | 3 | 4 | 5 | | V-1 | Col27a1 |
| 7041 | 3 | 4 | 5 | | V-1 | Col4a4 |
| 7042 | 3 | 4 | 5 | | V-1 | Col6a2 |
| 7043 | 3 | 4 | 5 | | V-1 | Col6a3 |
| 7044 | 3 | 4 | 5 | | V-1 | Col6a5 |
| 7045 | 3 | 4 | 5 | | V-1 | Col6a6 |
| 7046 | 3 | 4 | 5 | | V-1 | Colec11 |
| 7047 | 3 | 4 | 5 | | V-1 | Colq |
| 7048 | 3 | 4 | 5 | | V-1 | Commd4 |
| 7049 | 3 | 4 | 5 | | V-1 | Cope |
| 7050 | 3 | 4 | 5 | | V-1 | Coprs |
| 7051 | 3 | 4 | 5 | | V-1 | Copz2 |
| 7052 | 3 | 4 | 5 | | V-1 | Coq10a |
| 7053 | 3 | 4 | 5 | | V-1 | Coq10b |
| 7054 | 3 | 4 | 5 | | V-1 | Coq3 |
| 7055 | 3 | 4 | 5 | | V-1 | Coq4 |
| 7056 | 3 | 4 | 5 | | V-1 | Coq7 |
| 7057 | 3 | 4 | 5 | | V-1 | Corin |
| 7058 | 3 | 4 | 5 | | V-1 | Coro1a |
| 7059 | 3 | 4 | 5 | | V-1 | Coro2a |
| 7060 | 3 | 4 | 5 | | V-1 | Coro6 |
| 7061 | 3 | 4 | 5 | | V-1 | Cotl1 |
| 7062 | 3 | 4 | 5 | | V-1 | Cox18 |
| 7063 | 3 | 4 | 5 | | V-1 | Cox4i1 |
| 7064 | 3 | 4 | 5 | | V-1 | Cox4i2 |
| 7065 | 3 | 4 | 5 | | V-1 | Cox5a |
| 7066 | 3 | 4 | 5 | | V-1 | Cox5b |
| 7067 | 3 | 4 | 5 | | V-1 | Cox6a1 |
| 7068 | 3 | 4 | 5 | | V-1 | Cox6c |
| 7069 | 3 | 4 | 5 | | V-1 | Cox7b2 |
| 7070 | 3 | 4 | 5 | | V-1 | Cpd |
| 7071 | 3 | 4 | 5 | | V-1 | Cpeb2 |
| 7072 | 3 | 4 | 5 | | V-1 | Cpeb3 |
| 7073 | 3 | 4 | 5 | | V-1 | Cped1 |
| 7074 | 3 | 4 | 5 | | V-1 | Cpix1 |
| 7075 | 3 | 4 | 5 | | V-1 | Cpix4 |
| 7076 | 3 | 4 | 5 | | V-1 | Cpne8 |
| 7077 | 3 | 4 | 5 | | V-1 | Cpq |
| 7078 | 3 | 4 | 5 | | V-1 | Cpsf1 |
| 7079 | 3 | 4 | 5 | | V-1 | Cpxm1 |
| 7080 | 3 | 4 | 5 | | V-1 | Cradd |
| 7081 | 3 | 4 | 5 | | V-1 | Crcp |
| 7082 | 3 | 4 | 5 | | V-1 | Creb3l1 |
| 7083 | 3 | 4 | 5 | | V-1 | Creb5 |
| 7084 | 3 | 4 | 5 | | V-1 | Crebl2 |
| 7085 | 3 | 4 | 5 | | V-1 | Crebrf |
| 7086 | 3 | 4 | 5 | | V-1 | Creld1 |
| 7087 | 3 | 4 | 5 | | V-1 | Creld2 |
| 7088 | 3 | 4 | 5 | | V-1 | Crh |
| 7089 | 3 | 4 | 5 | | V-1 | Crhr2 |
| 7090 | 3 | 4 | 5 | | V-1 | Crispld2 |
| 7091 | 3 | 4 | 5 | | V-1 | Crkl |
| 7092 | 3 | 4 | 5 | | V-1 | Crlf2 |
| 7093 | 3 | 4 | 5 | | V-1 | Crtac1 |
| 7094 | 3 | 4 | 5 | | V-1 | Cry1 |
| 7095 | 3 | 4 | 5 | | V-1 | Cryab |
| 7096 | 3 | 4 | 5 | | V-1 | Cryge |
| 7097 | 3 | 4 | 5 | | V-1 | Cryl1 |
| 7098 | 3 | 4 | 5 | | V-1 | Cryz |
| 7099 | 3 | 4 | 5 | | V-1 | Csde1 |
| 7100 | 3 | 4 | 5 | | V-1 | Csf1r |
| 7101 | 3 | 4 | 5 | | V-1 | Csf2ra |
| 7102 | 3 | 4 | 5 | | V-1 | Csl |

Fig. 36 - 38

| | | | | | | | |
|---|---|---|---|---|---|---|---|
| 7103 | 3 | 4 | 5 | | V-1 | Csmd1 |
| 7104 | 3 | 4 | 5 | | V-1 | Csmd2 |
| 7105 | 3 | 4 | 5 | | V-1 | Csmd3 |
| 7106 | 3 | 4 | 5 | | V-1 | Csnk1g1 |
| 7107 | 3 | 4 | 5 | | V-1 | Csnk2b |
| 7108 | 3 | 4 | 5 | | V-1 | Cspg4 |
| 7109 | 3 | 4 | 5 | | V-1 | Csrnp2 |
| 7110 | 3 | 4 | 5 | | V-1 | Csrnp3 |
| 7111 | 3 | 4 | 5 | | V-1 | Csrp3 |
| 7112 | 3 | 4 | 5 | | V-1 | Cstf3 |
| 7113 | 3 | 4 | 5 | | V-1 | Ctf1 |
| 7114 | 3 | 4 | 5 | | V-1 | Ctla2b |
| 7115 | 3 | 4 | 5 | | V-1 | Ctla4 |
| 7116 | 3 | 4 | 5 | | V-1 | Ctnnbl1 |
| 7117 | 3 | 4 | 5 | | V-1 | Ctsh |
| 7118 | 3 | 4 | 5 | | V-1 | Ctsk |
| 7119 | 3 | 4 | 5 | | V-1 | Ctsz |
| 7120 | 3 | 4 | 5 | | V-1 | Cttnbp2nl |
| 7121 | 3 | 4 | 5 | | V-1 | Ctu2 |
| 7122 | 3 | 4 | 5 | | V-1 | Cul9 |
| 7123 | 3 | 4 | 5 | | V-1 | Cutc |
| 7124 | 3 | 4 | 5 | | V-1 | Cux2 |
| 7125 | 3 | 4 | 5 | | V-1 | Cx3cr1 |
| 7126 | 3 | 4 | 5 | | V-1 | Cxadr |
| 7127 | 3 | 4 | 5 | | V-1 | Cxcl1 |
| 7128 | 3 | 4 | 5 | | V-1 | Cxcl14 |
| 7129 | 3 | 4 | 5 | | V-1 | Cxcl17 |
| 7130 | 3 | 4 | 5 | | V-1 | Cxcl2 |
| 7131 | 3 | 4 | 5 | | V-1 | Cxcr3 |
| 7132 | 3 | 4 | 5 | | V-1 | Cxcr6 |
| 7133 | 3 | 4 | 5 | | V-1 | Cxx1b |
| 7134 | 3 | 4 | 5 | | V-1 | Cyb561d2 |
| 7135 | 3 | 4 | 5 | | V-1 | Cyb5d1 |
| 7136 | 3 | 4 | 5 | | V-1 | Cyb5r2 |
| 7137 | 3 | 4 | 5 | | V-1 | Cyb5rl |
| 7138 | 3 | 4 | 5 | | V-1 | Cyp11a1 |
| 7139 | 3 | 4 | 5 | | V-1 | Cyp20a1 |
| 7140 | 3 | 4 | 5 | | V-1 | Cyp21a1 |
| 7141 | 3 | 4 | 5 | | V-1 | Cyp26a1 |
| 7142 | 3 | 4 | 5 | | V-1 | Cyp27a1 |
| 7143 | 3 | 4 | 5 | | V-1 | Cyp2c44 |
| 7144 | 3 | 4 | 5 | | V-1 | Cyp2c53-ps |
| 7145 | 3 | 4 | 5 | | V-1 | Cyp2c66 |
| 7146 | 3 | 4 | 5 | | V-1 | Cyp2d37-ps |
| 7147 | 3 | 4 | 5 | | V-1 | Cyp2d40 |
| 7148 | 3 | 4 | 5 | | V-1 | Cyp2j12 |
| 7149 | 3 | 4 | 5 | | V-1 | Cyp2u1 |
| 7150 | 3 | 4 | 5 | | V-1 | Cyp3a13 |
| 7151 | 3 | 4 | 5 | | V-1 | Cyp4f13 |
| 7152 | 3 | 4 | 5 | | V-1 | Cyp4f14 |
| 7153 | 3 | 4 | 5 | | V-1 | Cyp4f17 |
| 7154 | 3 | 4 | 5 | | V-1 | Cyp4f37 |
| 7155 | 3 | 4 | 5 | | V-1 | Cyp51 |
| 7156 | 3 | 4 | 5 | | V-1 | Cyp7b1 |
| 7157 | 3 | 4 | 5 | | V-1 | Cypt14 |
| 7158 | 3 | 4 | 5 | | V-1 | Cysltr1 |
| 7159 | 3 | 4 | 5 | | V-1 | Cyth1 |
| 7160 | 3 | 4 | 5 | | V-1 | Cyth4 |
| 7161 | 3 | 4 | 5 | | V-1 | Cytip |
| 7162 | 3 | 4 | 5 | | V-1 | D030047H15Rik |
| 7163 | 3 | 4 | 5 | | V-1 | D030056L22Rik |
| 7164 | 3 | 4 | 5 | | V-1 | D11Wsu47e |
| 7165 | 3 | 4 | 5 | | V-1 | D130043K22Rik |
| 7166 | 3 | 4 | 5 | | V-1 | D1Ertd622e |
| 7167 | 3 | 4 | 5 | | V-1 | D2Wsu81e |
| 7168 | 3 | 4 | 5 | | V-1 | D2hgdh |
| 7169 | 3 | 4 | 5 | | V-1 | D330023K18Rik |
| 7170 | 3 | 4 | 5 | | V-1 | D3Ertd254e |
| 7171 | 3 | 4 | 5 | | V-1 | D430042O09Rik |
| 7172 | 3 | 4 | 5 | | V-1 | D630024D03Rik |
| 7173 | 3 | 4 | 5 | | V-1 | D630041G03Rik |
| 7174 | 3 | 4 | 5 | | V-1 | D7Ertd143e |
| 7175 | 3 | 4 | 5 | | V-1 | D7Ertd443e |
| 7176 | 3 | 4 | 5 | | V-1 | D830005E20Rik |
| 7177 | 3 | 4 | 5 | | V-1 | D8Ertd738e |
| 7178 | 3 | 4 | 5 | | V-1 | Dach1 |
| 7179 | 3 | 4 | 5 | | V-1 | Dact3 |
| 7180 | 3 | 4 | 5 | | V-1 | Dad1 |
| 7181 | 3 | 4 | 5 | | V-1 | Dag1 |
| 7182 | 3 | 4 | 5 | | V-1 | Dagla |
| 7183 | 3 | 4 | 5 | | V-1 | Dak |
| 7184 | 3 | 4 | 5 | | V-1 | Dand5 |
| 7185 | 3 | 4 | 5 | | V-1 | Dapp1 |
| 7186 | 3 | 4 | 5 | | V-1 | Dcaf10 |
| 7187 | 3 | 4 | 5 | | V-1 | Dcaf17 |
| 7188 | 3 | 4 | 5 | | V-1 | Dcaf6 |
| 7189 | 3 | 4 | 5 | | V-1 | Dcbld1 |
| 7190 | 3 | 4 | 5 | | V-1 | Dcc |
| 7191 | 3 | 4 | 5 | | V-1 | Dcdc2b |
| 7192 | 3 | 4 | 5 | | V-1 | Dchs1 |
| 7193 | 3 | 4 | 5 | | V-1 | Dck |
| 7194 | 3 | 4 | 5 | | V-1 | Dclre1a |
| 7195 | 3 | 4 | 5 | | V-1 | Dcp2 |
| 7196 | 3 | 4 | 5 | | V-1 | Dctd |
| 7197 | 3 | 4 | 5 | | V-1 | Dctn1 |
| 7198 | 3 | 4 | 5 | | V-1 | Dctn3 |
| 7199 | 3 | 4 | 5 | | V-1 | Dcun1d4 |
| 7200 | 3 | 4 | 5 | | V-1 | Dcx |
| 7201 | 3 | 4 | 5 | | V-1 | Dcxr |
| 7202 | 3 | 4 | 5 | | V-1 | Ddah2 |
| 7203 | 3 | 4 | 5 | | V-1 | Ddc |
| 7204 | 3 | 4 | 5 | | V-1 | Ddo |
| 7205 | 3 | 4 | 5 | | V-1 | Ddr2 |
| 7206 | 3 | 4 | 5 | | V-1 | Ddx11 |
| 7207 | 3 | 4 | 5 | | V-1 | Ddx18 |
| 7208 | 3 | 4 | 5 | | V-1 | Ddx31 |
| 7209 | 3 | 4 | 5 | | V-1 | Ddx49 |
| 7210 | 3 | 4 | 5 | | V-1 | Ddx51 |
| 7211 | 3 | 4 | 5 | | V-1 | Ddx55 |
| 7212 | 3 | 4 | 5 | | V-1 | Ddx56 |
| 7213 | 3 | 4 | 5 | | V-1 | Ddx58 |
| 7214 | 3 | 4 | 5 | | V-1 | Deb1 |
| 7215 | 3 | 4 | 5 | | V-1 | Def6 |
| 7216 | 3 | 4 | 5 | | V-1 | Defa5 |
| 7217 | 3 | 4 | 5 | | V-1 | Defb11 |
| 7218 | 3 | 4 | 5 | | V-1 | Defb14 |
| 7219 | 3 | 4 | 5 | | V-1 | Defb26 |
| 7220 | 3 | 4 | 5 | | V-1 | Defb36 |
| 7221 | 3 | 4 | 5 | | V-1 | Defb38 |
| 7222 | 3 | 4 | 5 | | V-1 | Defb43 |
| 7223 | 3 | 4 | 5 | | V-1 | Degs1 |
| 7224 | 3 | 4 | 5 | | V-1 | Dennd3 |
| 7225 | 3 | 4 | 5 | | V-1 | Dennd4c |
| 7226 | 3 | 4 | 5 | | V-1 | Dennd6b |
| 7227 | 3 | 4 | 5 | | V-1 | Depdc1a |
| 7228 | 3 | 4 | 5 | | V-1 | Depdc1b |
| 7229 | 3 | 4 | 5 | | V-1 | Deptor |
| 7230 | 3 | 4 | 5 | | V-1 | Dffa |
| 7231 | 3 | 4 | 5 | | V-1 | Dfna5 |
| 7232 | 3 | 4 | 5 | | V-1 | Dgat1 |
| 7233 | 3 | 4 | 5 | | V-1 | Dgcr6 |
| 7234 | 3 | 4 | 5 | | V-1 | Dgkeos |
| 7235 | 3 | 4 | 5 | | V-1 | Dgkk |
| 7236 | 3 | 4 | 5 | | V-1 | Dgkq |
| 7237 | 3 | 4 | 5 | | V-1 | Dhcr7 |
| 7238 | 3 | 4 | 5 | | V-1 | Dhdh |
| 7239 | 3 | 4 | 5 | | V-1 | Dhh |
| 7240 | 3 | 4 | 5 | | V-1 | Dhrs3 |
| 7241 | 3 | 4 | 5 | | V-1 | Dhrs7 |
| 7242 | 3 | 4 | 5 | | V-1 | Dhrs7b |
| 7243 | 3 | 4 | 5 | | V-1 | Dhx29 |
| 7244 | 3 | 4 | 5 | | V-1 | Dhx34 |
| 7245 | 3 | 4 | 5 | | V-1 | Diap1 |
| 7246 | 3 | 4 | 5 | | V-1 | Diap2 |
| 7247 | 3 | 4 | 5 | | V-1 | Dicer1 |
| 7248 | 3 | 4 | 5 | | V-1 | Dido1 |
| 7249 | 3 | 4 | 5 | | V-1 | Dio1 |
| 7250 | 3 | 4 | 5 | | V-1 | Diras2 |
| 7251 | 3 | 4 | 5 | | V-1 | Disp1 |
| 7252 | 3 | 4 | 5 | | V-1 | Disp2 |
| 7253 | 3 | 4 | 5 | | V-1 | Dixdc1 |
| 7254 | 3 | 4 | 5 | | V-1 | Dkc1 |
| 7255 | 3 | 4 | 5 | | V-1 | Dlg5 |
| 7256 | 3 | 4 | 5 | | V-1 | Dll1 |
| 7257 | 3 | 4 | 5 | | V-1 | Dmkn |
| 7258 | 3 | 4 | 5 | | V-1 | Dmrtb1 |
| 7259 | 3 | 4 | 5 | | V-1 | Dmrtc1a |
| 7260 | 3 | 4 | 5 | | V-1 | Dmrtc1b |
| 7261 | 3 | 4 | 5 | | V-1 | Dmxl2 |
| 7262 | 3 | 4 | 5 | | V-1 | Dna2 |
| 7263 | 3 | 4 | 5 | | V-1 | Dnaaf2 |
| 7264 | 3 | 4 | 5 | | V-1 | Dnaaf3 |
| 7265 | 3 | 4 | 5 | | V-1 | Dnah8 |
| 7266 | 3 | 4 | 5 | | V-1 | Dnaic2 |
| 7267 | 3 | 4 | 5 | | V-1 | Dnaja1 |
| 7268 | 3 | 4 | 5 | | V-1 | Dnajb3 |
| 7269 | 3 | 4 | 5 | | V-1 | Dnajc1 |
| 7270 | 3 | 4 | 5 | | V-1 | Dnajc12 |
| 7271 | 3 | 4 | 5 | | V-1 | Dnajc15 |
| 7272 | 3 | 4 | 5 | | V-1 | Dnajc16 |
| 7273 | 3 | 4 | 5 | | V-1 | Dnajc17 |
| 7274 | 3 | 4 | 5 | | V-1 | Dnajc24 |
| 7275 | 3 | 4 | 5 | | V-1 | Dnajc9 |
| 7276 | 3 | 4 | 5 | | V-1 | Dnal1 |
| 7277 | 3 | 4 | 5 | | V-1 | Dnase1 |
| 7278 | 3 | 4 | 5 | | V-1 | Dnase1l1 |
| 7279 | 3 | 4 | 5 | | V-1 | Dnd1 |
| 7280 | 3 | 4 | 5 | | V-1 | Dnm1l |
| 7281 | 3 | 4 | 5 | | V-1 | Dnmbp |
| 7282 | 3 | 4 | 5 | | V-1 | Dnmt1 |
| 7283 | 3 | 4 | 5 | | V-1 | Dnmt3b |
| 7284 | 3 | 4 | 5 | | V-1 | Dnmt3l |
| 7285 | 3 | 4 | 5 | | V-1 | Doc2a |
| 7286 | 3 | 4 | 5 | | V-1 | Doc2g |
| 7287 | 3 | 4 | 5 | | V-1 | Dohh |
| 7288 | 3 | 4 | 5 | | V-1 | Dok2 |
| 7289 | 3 | 4 | 5 | | V-1 | Dok7 |
| 7290 | 3 | 4 | 5 | | V-1 | Dopey2 |
| 7291 | 3 | 4 | 5 | | V-1 | Dos |
| 7292 | 3 | 4 | 5 | | V-1 | Dpep1 |
| 7293 | 3 | 4 | 5 | | V-1 | Dpep2 |
| 7294 | 3 | 4 | 5 | | V-1 | Dph1 |

Fig. 36 - 39

| | | | | | | | |
|---|---|---|---|---|---|---|---|
| 7295 | 3 | 4 | 5 | | V-1 | Dpm2 |
| 7296 | 3 | 4 | 5 | | V-1 | Dpm3 |
| 7297 | 3 | 4 | 5 | | V-1 | Dpp7 |
| 7298 | 3 | 4 | 5 | | V-1 | Dpp8 |
| 7299 | 3 | 4 | 5 | | V-1 | Dpysl4 |
| 7300 | 3 | 4 | 5 | | V-1 | Drap1 |
| 7301 | 3 | 4 | 5 | | V-1 | Drd2 |
| 7302 | 3 | 4 | 5 | | V-1 | Drd4 |
| 7303 | 3 | 4 | 5 | | V-1 | Dsc2 |
| 7304 | 3 | 4 | 5 | | V-1 | Dscaml1 |
| 7305 | 3 | 4 | 5 | | V-1 | Dscc1 |
| 7306 | 3 | 4 | 5 | | V-1 | Dst |
| 7307 | 3 | 4 | 5 | | V-1 | Dtwd2 |
| 7308 | 3 | 4 | 5 | | V-1 | Dtx4 |
| 7309 | 3 | 4 | 5 | | V-1 | Dupd1 |
| 7310 | 3 | 4 | 5 | | V-1 | Dus1l |
| 7311 | 3 | 4 | 5 | | V-1 | Dusp12 |
| 7312 | 3 | 4 | 5 | | V-1 | Dusp16 |
| 7313 | 3 | 4 | 5 | | V-1 | Dusp19 |
| 7314 | 3 | 4 | 5 | | V-1 | Dusp23 |
| 7315 | 3 | 4 | 5 | | V-1 | Dusp26 |
| 7316 | 3 | 4 | 5 | | V-1 | Dusp8 |
| 7317 | 3 | 4 | 5 | | V-1 | Dvl3 |
| 7318 | 3 | 4 | 5 | | V-1 | Dync1li1 |
| 7319 | 3 | 4 | 5 | | V-1 | Dync2h1 |
| 7320 | 3 | 4 | 5 | | V-1 | Dynlt1b |
| 7321 | 3 | 4 | 5 | | V-1 | Dynlt1c |
| 7322 | 3 | 4 | 5 | | V-1 | Dyrk1b |
| 7323 | 3 | 4 | 5 | | V-1 | Dyx1c1 |
| 7324 | 3 | 4 | 5 | | V-1 | Dzank1 |
| 7325 | 3 | 4 | 5 | | V-1 | Dzip1l |
| 7326 | 3 | 4 | 5 | | V-1 | E030011O05Rik |
| 7327 | 3 | 4 | 5 | | V-1 | E030024N20Rik |
| 7328 | 3 | 4 | 5 | | V-1 | E130012A19Rik |
| 7329 | 3 | 4 | 5 | | V-1 | E130112N10Rik |
| 7330 | 3 | 4 | 5 | | V-1 | E130215H24Rik |
| 7331 | 3 | 4 | 5 | | V-1 | E130308A19Rik |
| 7332 | 3 | 4 | 5 | | V-1 | E130317F20Rik |
| 7333 | 3 | 4 | 5 | | V-1 | E230029C05Rik |
| 7334 | 3 | 4 | 5 | | V-1 | E2f8 |
| 7335 | 3 | 4 | 5 | | V-1 | E430018J23Rik |
| 7336 | 3 | 4 | 5 | | V-1 | Eaf1 |
| 7337 | 3 | 4 | 5 | | V-1 | Ears2 |
| 7338 | 3 | 4 | 5 | | V-1 | Ebag9 |
| 7339 | 3 | 4 | 5 | | V-1 | Ebpl |
| 7340 | 3 | 4 | 5 | | V-1 | Ece2 |
| 7341 | 3 | 4 | 5 | | V-1 | Ech1 |
| 7342 | 3 | 4 | 5 | | V-1 | Echdc1 |
| 7343 | 3 | 4 | 5 | | V-1 | Echdc2 |
| 7344 | 3 | 4 | 5 | | V-1 | Eci1 |
| 7345 | 3 | 4 | 5 | | V-1 | Eci2 |
| 7346 | 3 | 4 | 5 | | V-1 | Ecm1 |
| 7347 | 3 | 4 | 5 | | V-1 | Ecscr |
| 7348 | 3 | 4 | 5 | | V-1 | Ecsit |
| 7349 | 3 | 4 | 5 | | V-1 | Eda |
| 7350 | 3 | 4 | 5 | | V-1 | Eda2r |
| 7351 | 3 | 4 | 5 | | V-1 | Edem1 |
| 7352 | 3 | 4 | 5 | | V-1 | Edf1 |
| 7353 | 3 | 4 | 5 | | V-1 | Edrf1 |
| 7354 | 3 | 4 | 5 | | V-1 | Eed |
| 7355 | 3 | 4 | 5 | | V-1 | Eepd1 |
| 7356 | 3 | 4 | 5 | | V-1 | Efcab1 |
| 7357 | 3 | 4 | 5 | | V-1 | Efcab10 |
| 7358 | 3 | 4 | 5 | | V-1 | Efcab11 |
| 7359 | 3 | 4 | 5 | | V-1 | Efcab12 |
| 7360 | 3 | 4 | 5 | | V-1 | Efcab2 |
| 7361 | 3 | 4 | 5 | | V-1 | Efcab4a |
| 7362 | 3 | 4 | 5 | | V-1 | Efr3b |
| 7363 | 3 | 4 | 5 | | V-1 | Egflam |
| 7364 | 3 | 4 | 5 | | V-1 | Egfr |
| 7365 | 3 | 4 | 5 | | V-1 | Egr3 |
| 7366 | 3 | 4 | 5 | | V-1 | Ehd3 |
| 7367 | 3 | 4 | 5 | | V-1 | Ei24 |
| 7368 | 3 | 4 | 5 | | V-1 | Eid1 |
| 7369 | 3 | 4 | 5 | | V-1 | Eid3 |
| 7370 | 3 | 4 | 5 | | V-1 | Eif1a |
| 7371 | 3 | 4 | 5 | | V-1 | Eif1ax |
| 7372 | 3 | 4 | 5 | | V-1 | Eif2ak4 |
| 7373 | 3 | 4 | 5 | | V-1 | Eif2b2 |
| 7374 | 3 | 4 | 5 | | V-1 | Eif2b3 |
| 7375 | 3 | 4 | 5 | | V-1 | Eif2b4 |
| 7376 | 3 | 4 | 5 | | V-1 | Eif3k |
| 7377 | 3 | 4 | 5 | | V-1 | Eif4ebp3 |
| 7378 | 3 | 4 | 5 | | V-1 | Eif4g1 |
| 7379 | 3 | 4 | 5 | | V-1 | Eifn1 |
| 7380 | 3 | 4 | 5 | | V-1 | Ell3 |
| 7381 | 3 | 4 | 5 | | V-1 | Elmod2 |
| 7382 | 3 | 4 | 5 | | V-1 | Elmsan1 |
| 7383 | 3 | 4 | 5 | | V-1 | Elovl7 |
| 7384 | 3 | 4 | 5 | | V-1 | Elp5 |
| 7385 | 3 | 4 | 5 | | V-1 | Elp6 |
| 7386 | 3 | 4 | 5 | | V-1 | Emc2 |
| 7387 | 3 | 4 | 5 | | V-1 | Emc7 |
| 7388 | 3 | 4 | 5 | | V-1 | Emcn |
| 7389 | 3 | 4 | 5 | | V-1 | Eme1 |
| 7390 | 3 | 4 | 5 | | V-1 | Eme2 |

| | | | | | | | |
|---|---|---|---|---|---|---|---|
| 7391 | 3 | 4 | 5 | | V-1 | Emilin1 |
| 7392 | 3 | 4 | 5 | | V-1 | Eml2 |
| 7393 | 3 | 4 | 5 | | V-1 | Emp1 |
| 7394 | 3 | 4 | 5 | | V-1 | Emr4 |
| 7395 | 3 | 4 | 5 | | V-1 | Enah |
| 7396 | 3 | 4 | 5 | | V-1 | Enc1 |
| 7397 | 3 | 4 | 5 | | V-1 | Endog |
| 7398 | 3 | 4 | 5 | | V-1 | Engase |
| 7399 | 3 | 4 | 5 | | V-1 | Enho |
| 7400 | 3 | 4 | 5 | | V-1 | Enkd1 |
| 7401 | 3 | 4 | 5 | | V-1 | Eno1b |
| 7402 | 3 | 4 | 5 | | V-1 | Eno3 |
| 7403 | 3 | 4 | 5 | | V-1 | Eno4 |
| 7404 | 3 | 4 | 5 | | V-1 | Enoph1 |
| 7405 | 3 | 4 | 5 | | V-1 | Enpep |
| 7406 | 3 | 4 | 5 | | V-1 | Enpp3 |
| 7407 | 3 | 4 | 5 | | V-1 | Enpp5 |
| 7408 | 3 | 4 | 5 | | V-1 | Enpp6 |
| 7409 | 3 | 4 | 5 | | V-1 | Ensa |
| 7410 | 3 | 4 | 5 | | V-1 | Enthd2 |
| 7411 | 3 | 4 | 5 | | V-1 | Entpd5 |
| 7412 | 3 | 4 | 5 | | V-1 | Entpd6 |
| 7413 | 3 | 4 | 5 | | V-1 | Entpd7 |
| 7414 | 3 | 4 | 5 | | V-1 | Entpd8 |
| 7415 | 3 | 4 | 5 | | V-1 | Eomes |
| 7416 | 3 | 4 | 5 | | V-1 | Ep300 |
| 7417 | 3 | 4 | 5 | | V-1 | Epb4.1l1 |
| 7418 | 3 | 4 | 5 | | V-1 | Epb4.1l3 |
| 7419 | 3 | 4 | 5 | | V-1 | Epc1 |
| 7420 | 3 | 4 | 5 | | V-1 | Epg5 |
| 7421 | 3 | 4 | 5 | | V-1 | Epha3 |
| 7422 | 3 | 4 | 5 | | V-1 | Epha6 |
| 7423 | 3 | 4 | 5 | | V-1 | Ephb2 |
| 7424 | 3 | 4 | 5 | | V-1 | Ephx2 |
| 7425 | 3 | 4 | 5 | | V-1 | Ephx4 |
| 7426 | 3 | 4 | 5 | | V-1 | Epm2aip1 |
| 7427 | 3 | 4 | 5 | | V-1 | Epn3 |
| 7428 | 3 | 4 | 5 | | V-1 | Eps8l2 |
| 7429 | 3 | 4 | 5 | | V-1 | Epsti1 |
| 7430 | 3 | 4 | 5 | | V-1 | Erbb2 |
| 7431 | 3 | 4 | 5 | | V-1 | Erbb4 |
| 7432 | 3 | 4 | 5 | | V-1 | Erc1 |
| 7433 | 3 | 4 | 5 | | V-1 | Ercc6 |
| 7434 | 3 | 4 | 5 | | V-1 | Ercc6l |
| 7435 | 3 | 4 | 5 | | V-1 | Ercc8 |
| 7436 | 3 | 4 | 5 | | V-1 | Erdr1 |
| 7437 | 3 | 4 | 5 | | V-1 | Ereg |
| 7438 | 3 | 4 | 5 | | V-1 | Erp27 |
| 7439 | 3 | 4 | 5 | | V-1 | Esam |
| 7440 | 3 | 4 | 5 | | V-1 | Esco1 |
| 7441 | 3 | 4 | 5 | | V-1 | Esco2 |
| 7442 | 3 | 4 | 5 | | V-1 | Espl1 |
| 7443 | 3 | 4 | 5 | | V-1 | Esr1 |
| 7444 | 3 | 4 | 5 | | V-1 | Esrrg |
| 7445 | 3 | 4 | 5 | | V-1 | Esyt3 |
| 7446 | 3 | 4 | 5 | | V-1 | Etaa1 |
| 7447 | 3 | 4 | 5 | | V-1 | Etfb |
| 7448 | 3 | 4 | 5 | | V-1 | Etnppl |
| 7449 | 3 | 4 | 5 | | V-1 | Etv1 |
| 7450 | 3 | 4 | 5 | | V-1 | Eva1a |
| 7451 | 3 | 4 | 5 | | V-1 | Eva1b |
| 7452 | 3 | 4 | 5 | | V-1 | Eva1c |
| 7453 | 3 | 4 | 5 | | V-1 | Evi2a |
| 7454 | 3 | 4 | 5 | | V-1 | Evi2b |
| 7455 | 3 | 4 | 5 | | V-1 | Evpl |
| 7456 | 3 | 4 | 5 | | V-1 | Exd1 |
| 7457 | 3 | 4 | 5 | | V-1 | Exoc3l4 |
| 7458 | 3 | 4 | 5 | | V-1 | Exoc4 |
| 7459 | 3 | 4 | 5 | | V-1 | Exoc6 |
| 7460 | 3 | 4 | 5 | | V-1 | Exoc7 |
| 7461 | 3 | 4 | 5 | | V-1 | Exosc3 |
| 7462 | 3 | 4 | 5 | | V-1 | Exosc4 |
| 7463 | 3 | 4 | 5 | | V-1 | Exosc7 |
| 7464 | 3 | 4 | 5 | | V-1 | Exph5 |
| 7465 | 3 | 4 | 5 | | V-1 | Eya2 |
| 7466 | 3 | 4 | 5 | | V-1 | F13a1 |
| 7467 | 3 | 4 | 5 | | V-1 | F2rl3 |
| 7468 | 3 | 4 | 5 | | V-1 | F5 |
| 7469 | 3 | 4 | 5 | | V-1 | F630028O10Rik |
| 7470 | 3 | 4 | 5 | | V-1 | F730043M19Rik |
| 7471 | 3 | 4 | 5 | | V-1 | F830045P16Rik |
| 7472 | 3 | 4 | 5 | | V-1 | F8a |
| 7473 | 3 | 4 | 5 | | V-1 | Fabp6 |
| 7474 | 3 | 4 | 5 | | V-1 | Fabp7 |
| 7475 | 3 | 4 | 5 | | V-1 | Fahd2a |
| 7476 | 3 | 4 | 5 | | V-1 | Fam102a |
| 7477 | 3 | 4 | 5 | | V-1 | Fam107a |
| 7478 | 3 | 4 | 5 | | V-1 | Fam107b |
| 7479 | 3 | 4 | 5 | | V-1 | Fam109b |
| 7480 | 3 | 4 | 5 | | V-1 | Fam114a1 |
| 7481 | 3 | 4 | 5 | | V-1 | Fam115a |
| 7482 | 3 | 4 | 5 | | V-1 | Fam117a |
| 7483 | 3 | 4 | 5 | | V-1 | Fam118b |
| 7484 | 3 | 4 | 5 | | V-1 | Fam122a |
| 7485 | 3 | 4 | 5 | | V-1 | Fam126b |
| 7486 | 3 | 4 | 5 | | V-1 | Fam131a |

Fig. 36 - 40

| | | | | | | | |
|---|---|---|---|---|---|---|---|
| 7487 | 3 | 4 | 5 | | V-1 | Fam131c | |
| 7488 | 3 | 4 | 5 | | V-1 | Fam134b | |
| 7489 | 3 | 4 | 5 | | V-1 | Fam151a | |
| 7490 | 3 | 4 | 5 | | V-1 | Fam154b | |
| 7491 | 3 | 4 | 5 | | V-1 | Fam160a2 | |
| 7492 | 3 | 4 | 5 | | V-1 | Fam169b | |
| 7493 | 3 | 4 | 5 | | V-1 | Fam175a | |
| 7494 | 3 | 4 | 5 | | V-1 | Fam179a | |
| 7495 | 3 | 4 | 5 | | V-1 | Fam179b | |
| 7496 | 3 | 4 | 5 | | V-1 | Fam181b | |
| 7497 | 3 | 4 | 5 | | V-1 | Fam189b | |
| 7498 | 3 | 4 | 5 | | V-1 | Fam195b | |
| 7499 | 3 | 4 | 5 | | V-1 | Fam199x | |
| 7500 | 3 | 4 | 5 | | V-1 | Fam206a | |
| 7501 | 3 | 4 | 5 | | V-1 | Fam210a | |
| 7502 | 3 | 4 | 5 | | V-1 | Fam212a | |
| 7503 | 3 | 4 | 5 | | V-1 | Fam212b | |
| 7504 | 3 | 4 | 5 | | V-1 | Fam213b | |
| 7505 | 3 | 4 | 5 | | V-1 | Fam216a | |
| 7506 | 3 | 4 | 5 | | V-1 | Fam219a | |
| 7507 | 3 | 4 | 5 | | V-1 | Fam222b | |
| 7508 | 3 | 4 | 5 | | V-1 | Fam228b | |
| 7509 | 3 | 4 | 5 | | V-1 | Fam229a | |
| 7510 | 3 | 4 | 5 | | V-1 | Fam24a | |
| 7511 | 3 | 4 | 5 | | V-1 | Fam49b | |
| 7512 | 3 | 4 | 5 | | V-1 | Fam57b | |
| 7513 | 3 | 4 | 5 | | V-1 | Fam60a | |
| 7514 | 3 | 4 | 5 | | V-1 | Fam64a | |
| 7515 | 3 | 4 | 5 | | V-1 | Fam65b | |
| 7516 | 3 | 4 | 5 | | V-1 | Fam69b | |
| 7517 | 3 | 4 | 5 | | V-1 | Fam71e1 | |
| 7518 | 3 | 4 | 5 | | V-1 | Fam73a | |
| 7519 | 3 | 4 | 5 | | V-1 | Fam83f | |
| 7520 | 3 | 4 | 5 | | V-1 | Fam83h | |
| 7521 | 3 | 4 | 5 | | V-1 | Fam92a | |
| 7522 | 3 | 4 | 5 | | V-1 | Fam92b | |
| 7523 | 3 | 4 | 5 | | V-1 | Fam98b | |
| 7524 | 3 | 4 | 5 | | V-1 | Fam98c | |
| 7525 | 3 | 4 | 5 | | V-1 | Fancd2os | |
| 7526 | 3 | 4 | 5 | | V-1 | Fancf | |
| 7527 | 3 | 4 | 5 | | V-1 | Fanci | |
| 7528 | 3 | 4 | 5 | | V-1 | Fancm | |
| 7529 | 3 | 4 | 5 | | V-1 | Farp2 | |
| 7530 | 3 | 4 | 5 | | V-1 | Fas | |
| 7531 | 3 | 4 | 5 | | V-1 | Fat2 | |
| 7532 | 3 | 4 | 5 | | V-1 | Fat3 | |
| 7533 | 3 | 4 | 5 | | V-1 | Fat4 | |
| 7534 | 3 | 4 | 5 | | V-1 | Fau | |
| 7535 | 3 | 4 | 5 | | V-1 | Faxc | |
| 7536 | 3 | 4 | 5 | | V-1 | Fbf1 | |
| 7537 | 3 | 4 | 5 | | V-1 | Fblim1 | |
| 7538 | 3 | 4 | 5 | | V-1 | Fbln1 | |
| 7539 | 3 | 4 | 5 | | V-1 | Fbln2 | |
| 7540 | 3 | 4 | 5 | | V-1 | Fbxl15 | |
| 7541 | 3 | 4 | 5 | | V-1 | Fbxl19 | |
| 7542 | 3 | 4 | 5 | | V-1 | Fbxl7 | |
| 7543 | 3 | 4 | 5 | | V-1 | Fbxo10 | |
| 7544 | 3 | 4 | 5 | | V-1 | Fbxo15 | |
| 7545 | 3 | 4 | 5 | | V-1 | Fbxo16 | |
| 7546 | 3 | 4 | 5 | | V-1 | Fbxo17 | |
| 7547 | 3 | 4 | 5 | | V-1 | Fbxo18 | |
| 7548 | 3 | 4 | 5 | | V-1 | Fbxo25 | |
| 7549 | 3 | 4 | 5 | | V-1 | Fbxo28 | |
| 7550 | 3 | 4 | 5 | | V-1 | Fbxo40 | |
| 7551 | 3 | 4 | 5 | | V-1 | Fbxo44 | |
| 7552 | 3 | 4 | 5 | | V-1 | Fbxo48 | |
| 7553 | 3 | 4 | 5 | | V-1 | Fbxo6 | |
| 7554 | 3 | 4 | 5 | | V-1 | Fbxw4 | |
| 7555 | 3 | 4 | 5 | | V-1 | Fdps | |
| 7556 | 3 | 4 | 5 | | V-1 | Fen1 | |
| 7557 | 3 | 4 | 5 | | V-1 | Fert2 | |
| 7558 | 3 | 4 | 5 | | V-1 | Fes | |
| 7559 | 3 | 4 | 5 | | V-1 | Ffar4 | |
| 7560 | 3 | 4 | 5 | | V-1 | Fgd2 | |
| 7561 | 3 | 4 | 5 | | V-1 | Fgd3 | |
| 7562 | 3 | 4 | 5 | | V-1 | Fgd6 | |
| 7563 | 3 | 4 | 5 | | V-1 | Fgf2 | |
| 7564 | 3 | 4 | 5 | | V-1 | Fgf22 | |
| 7565 | 3 | 4 | 5 | | V-1 | Fgf3 | |
| 7566 | 3 | 4 | 5 | | V-1 | Fgf6 | |
| 7567 | 3 | 4 | 5 | | V-1 | Fgl1 | |
| 7568 | 3 | 4 | 5 | | V-1 | Fgl2 | |
| 7569 | 3 | 4 | 5 | | V-1 | Fgr | |
| 7570 | 3 | 4 | 5 | | V-1 | Fhit | |
| 7571 | 3 | 4 | 5 | | V-1 | Fhl3 | |
| 7572 | 3 | 4 | 5 | | V-1 | Fibp | |
| 7573 | 3 | 4 | 5 | | V-1 | Filip1 | |
| 7574 | 3 | 4 | 5 | | V-1 | Filip1l | |
| 7575 | 3 | 4 | 5 | | V-1 | Fkbp14 | |
| 7576 | 3 | 4 | 5 | | V-1 | Fkbp2 | |
| 7577 | 3 | 4 | 5 | | V-1 | Fkbp4 | |
| 7578 | 3 | 4 | 5 | | V-1 | Fkbp5 | |
| 7579 | 3 | 4 | 5 | | V-1 | Fkbp7 | |
| 7580 | 3 | 4 | 5 | | V-1 | Fkbp8 | |
| 7581 | 3 | 4 | 5 | | V-1 | Fkbpl | |
| 7582 | 3 | 4 | 5 | | V-1 | Fkrp | |
| 7583 | 3 | 4 | 5 | | V-1 | Flcn | |
| 7584 | 3 | 4 | 5 | | V-1 | Flna | |
| 7585 | 3 | 4 | 5 | | V-1 | Flnb | |
| 7586 | 3 | 4 | 5 | | V-1 | Flnc | |
| 7587 | 3 | 4 | 5 | | V-1 | Flot1 | |
| 7588 | 3 | 4 | 5 | | V-1 | Flrt1 | |
| 7589 | 3 | 4 | 5 | | V-1 | Flrt2 | |
| 7590 | 3 | 4 | 5 | | V-1 | Flt1 | |
| 7591 | 3 | 4 | 5 | | V-1 | Flt3l | |
| 7592 | 3 | 4 | 5 | | V-1 | Flywch1 | |
| 7593 | 3 | 4 | 5 | | V-1 | Flywch2 | |
| 7594 | 3 | 4 | 5 | | V-1 | Fmn1 | |
| 7595 | 3 | 4 | 5 | | V-1 | Fmnl3 | |
| 7596 | 3 | 4 | 5 | | V-1 | Fmo4 | |
| 7597 | 3 | 4 | 5 | | V-1 | Fndc1 | |
| 7598 | 3 | 4 | 5 | | V-1 | Fndc3b | |
| 7599 | 3 | 4 | 5 | | V-1 | Fnip1 | |
| 7600 | 3 | 4 | 5 | | V-1 | Fnip2 | |
| 7601 | 3 | 4 | 5 | | V-1 | Fosl2 | |
| 7602 | 3 | 4 | 5 | | V-1 | Foxd2os | |
| 7603 | 3 | 4 | 5 | | V-1 | Foxd4 | |
| 7604 | 3 | 4 | 5 | | V-1 | Foxk1 | |
| 7605 | 3 | 4 | 5 | | V-1 | Foxo1 | |
| 7606 | 3 | 4 | 5 | | V-1 | Foxp1 | |
| 7607 | 3 | 4 | 5 | | V-1 | Foxq1 | |
| 7608 | 3 | 4 | 5 | | V-1 | Foxred1 | |
| 7609 | 3 | 4 | 5 | | V-1 | Foxred2 | |
| 7610 | 3 | 4 | 5 | | V-1 | Foxs1 | |
| 7611 | 3 | 4 | 5 | | V-1 | Fpgs | |
| 7612 | 3 | 4 | 5 | | V-1 | Fpr1 | |
| 7613 | 3 | 4 | 5 | | V-1 | Fpr2 | |
| 7614 | 3 | 4 | 5 | | V-1 | Fra10ac1 | |
| 7615 | 3 | 4 | 5 | | V-1 | Frat1 | |
| 7616 | 3 | 4 | 5 | | V-1 | Frmd6 | |
| 7617 | 3 | 4 | 5 | | V-1 | Frmd7 | |
| 7618 | 3 | 4 | 5 | | V-1 | Frmpd4 | |
| 7619 | 3 | 4 | 5 | | V-1 | Frs2 | |
| 7620 | 3 | 4 | 5 | | V-1 | Frs3os | |
| 7621 | 3 | 4 | 5 | | V-1 | Fry | |
| 7622 | 3 | 4 | 5 | | V-1 | Fsbp | |
| 7623 | 3 | 4 | 5 | | V-1 | Fscn1 | |
| 7624 | 3 | 4 | 5 | | V-1 | Fstl1 | |
| 7625 | 3 | 4 | 5 | | V-1 | Fstl3 | |
| 7626 | 3 | 4 | 5 | | V-1 | Ftx | |
| 7627 | 3 | 4 | 5 | | V-1 | Fuca1 | |
| 7628 | 3 | 4 | 5 | | V-1 | Fuca2 | |
| 7629 | 3 | 4 | 5 | | V-1 | Fundc2 | |
| 7630 | 3 | 4 | 5 | | V-1 | Furin | |
| 7631 | 3 | 4 | 5 | | V-1 | Fut10 | |
| 7632 | 3 | 4 | 5 | | V-1 | Fxn | |
| 7633 | 3 | 4 | 5 | | V-1 | Fxyd6 | |
| 7634 | 3 | 4 | 5 | | V-1 | Fyb | |
| 7635 | 3 | 4 | 5 | | V-1 | Fyco1 | |
| 7636 | 3 | 4 | 5 | | V-1 | Fyn | |
| 7637 | 3 | 4 | 5 | | V-1 | Fzd3 | |
| 7638 | 3 | 4 | 5 | | V-1 | Fzd5 | |
| 7639 | 3 | 4 | 5 | | V-1 | Fzd9 | |
| 7640 | 3 | 4 | 5 | | V-1 | Fzr1 | |
| 7641 | 3 | 4 | 5 | | V-1 | G630090E17Rik | |
| 7642 | 3 | 4 | 5 | | V-1 | G6pd2 | |
| 7643 | 3 | 4 | 5 | | V-1 | Gabpb2 | |
| 7644 | 3 | 4 | 5 | | V-1 | Gabra4 | |
| 7645 | 3 | 4 | 5 | | V-1 | Gabrg3 | |
| 7646 | 3 | 4 | 5 | | V-1 | Gadd45a | |
| 7647 | 3 | 4 | 5 | | V-1 | Gadd45b | |
| 7648 | 3 | 4 | 5 | | V-1 | Galk2 | |
| 7649 | 3 | 4 | 5 | | V-1 | Galnt3 | |
| 7650 | 3 | 4 | 5 | | V-1 | Galnt4 | |
| 7651 | 3 | 4 | 5 | | V-1 | Galnt7 | |
| 7652 | 3 | 4 | 5 | | V-1 | Galt | |
| 7653 | 3 | 4 | 5 | | V-1 | Gapt | |
| 7654 | 3 | 4 | 5 | | V-1 | Gapvd1 | |
| 7655 | 3 | 4 | 5 | | V-1 | Gar1 | |
| 7656 | 3 | 4 | 5 | | V-1 | Gas2 | |
| 7657 | 3 | 4 | 5 | | V-1 | Gas8 | |
| 7658 | 3 | 4 | 5 | | V-1 | Gatsl2 | |
| 7659 | 3 | 4 | 5 | | V-1 | Gatsl3 | |
| 7660 | 3 | 4 | 5 | | V-1 | Gbgt1 | |
| 7661 | 3 | 4 | 5 | | V-1 | Gbp11 | |
| 7662 | 3 | 4 | 5 | | V-1 | Gca | |
| 7663 | 3 | 4 | 5 | | V-1 | Gcat | |
| 7664 | 3 | 4 | 5 | | V-1 | Gcc1 | |
| 7665 | 3 | 4 | 5 | | V-1 | Gcc2 | |
| 7666 | 3 | 4 | 5 | | V-1 | Gch1 | |
| 7667 | 3 | 4 | 5 | | V-1 | Gcnt1 | |
| 7668 | 3 | 4 | 5 | | V-1 | Gcnt2 | |
| 7669 | 3 | 4 | 5 | | V-1 | Gdap1 | |
| 7670 | 3 | 4 | 5 | | V-1 | Gdap10 | |
| 7671 | 3 | 4 | 5 | | V-1 | Gde1 | |
| 7672 | 3 | 4 | 5 | | V-1 | Gdf11 | |
| 7673 | 3 | 4 | 5 | | V-1 | Gdf5 | |
| 7674 | 3 | 4 | 5 | | V-1 | Gdf6 | |
| 7675 | 3 | 4 | 5 | | V-1 | Gdpd5 | |
| 7676 | 3 | 4 | 5 | | V-1 | Gemin2 | |
| 7677 | 3 | 4 | 5 | | V-1 | Gen1 | |
| 7678 | 3 | 4 | 5 | | V-1 | Gfi1 | |

Fig. 36 - 41

| | | | | | | | |
|---|---|---|---|---|---|---|---|
| 7679 | 3 | 4 | 5 | | | V-1 | Gfod1 |
| 7680 | 3 | 4 | 5 | | | V-1 | Gfod2 |
| 7681 | 3 | 4 | 5 | | | V-1 | Gfpt1 |
| 7682 | 3 | 4 | 5 | | | V-1 | Gfpt2 |
| 7683 | 3 | 4 | 5 | | | V-1 | Gfra4 |
| 7684 | 3 | 4 | 5 | | | V-1 | Ggct |
| 7685 | 3 | 4 | 5 | | | V-1 | Ggh |
| 7686 | 3 | 4 | 5 | | | V-1 | Ggn |
| 7687 | 3 | 4 | 5 | | | V-1 | Ggnbp1 |
| 7688 | 3 | 4 | 5 | | | V-1 | Ggps1 |
| 7689 | 3 | 4 | 5 | | | V-1 | Ggta1 |
| 7690 | 3 | 4 | 5 | | | V-1 | Gimap5 |
| 7691 | 3 | 4 | 5 | | | V-1 | Gimap6 |
| 7692 | 3 | 4 | 5 | | | V-1 | Gins1 |
| 7693 | 3 | 4 | 5 | | | V-1 | Gins2 |
| 7694 | 3 | 4 | 5 | | | V-1 | Gipc3 |
| 7695 | 3 | 4 | 5 | | | V-1 | Gjb2 |
| 7696 | 3 | 4 | 5 | | | V-1 | Gjb4 |
| 7697 | 3 | 4 | 5 | | | V-1 | Gk2 |
| 7698 | 3 | 4 | 5 | | | V-1 | Gk5 |
| 7699 | 3 | 4 | 5 | | | V-1 | Gkn1 |
| 7700 | 3 | 4 | 5 | | | V-1 | Gkn3 |
| 7701 | 3 | 4 | 5 | | | V-1 | Glb1l |
| 7702 | 3 | 4 | 5 | | | V-1 | Gli1 |
| 7703 | 3 | 4 | 5 | | | V-1 | Glra3 |
| 7704 | 3 | 4 | 5 | | | V-1 | Glrx |
| 7705 | 3 | 4 | 5 | | | V-1 | Gls2 |
| 7706 | 3 | 4 | 5 | | | V-1 | Glt28d2 |
| 7707 | 3 | 4 | 5 | | | V-1 | Glt8d1 |
| 7708 | 3 | 4 | 5 | | | V-1 | Gltscr1 |
| 7709 | 3 | 4 | 5 | | | V-1 | Gltscr1l |
| 7710 | 3 | 4 | 5 | | | V-1 | Glud1 |
| 7711 | 3 | 4 | 5 | | | V-1 | Glyctk |
| 7712 | 3 | 4 | 5 | | | V-1 | Gm10046 |
| 7713 | 3 | 4 | 5 | | | V-1 | Gm10334 |
| 7714 | 3 | 4 | 5 | | | V-1 | Gm10416 |
| 7715 | 3 | 4 | 5 | | | V-1 | Gm10421 |
| 7716 | 3 | 4 | 5 | | | V-1 | Gm1045 |
| 7717 | 3 | 4 | 5 | | | V-1 | Gm10451 |
| 7718 | 3 | 4 | 5 | | | V-1 | Gm10560 |
| 7719 | 3 | 4 | 5 | | | V-1 | Gm10584 |
| 7720 | 3 | 4 | 5 | | | V-1 | Gm10658 |
| 7721 | 3 | 4 | 5 | | | V-1 | Gm10845 |
| 7722 | 3 | 4 | 5 | | | V-1 | Gm10941 |
| 7723 | 3 | 4 | 5 | | | V-1 | Gm11127 |
| 7724 | 3 | 4 | 5 | | | V-1 | Gm11240 |
| 7725 | 3 | 4 | 5 | | | V-1 | Gm11568 |
| 7726 | 3 | 4 | 5 | | | V-1 | Gm12060 |
| 7727 | 3 | 4 | 5 | | | V-1 | Gm12298 |
| 7728 | 3 | 4 | 5 | | | V-1 | Gm12992 |
| 7729 | 3 | 4 | 5 | | | V-1 | Gm13139 |
| 7730 | 3 | 4 | 5 | | | V-1 | Gm13152 |
| 7731 | 3 | 4 | 5 | | | V-1 | Gm13305 |
| 7732 | 3 | 4 | 5 | | | V-1 | Gm13308 |
| 7733 | 3 | 4 | 5 | | | V-1 | Gm13498 |
| 7734 | 3 | 4 | 5 | | | V-1 | Gm13826 |
| 7735 | 3 | 4 | 5 | | | V-1 | Gm14137 |
| 7736 | 3 | 4 | 5 | | | V-1 | Gm14295 |
| 7737 | 3 | 4 | 5 | | | V-1 | Gm14326 |
| 7738 | 3 | 4 | 5 | | | V-1 | Gm14347 |
| 7739 | 3 | 4 | 5 | | | V-1 | Gm14403 |
| 7740 | 3 | 4 | 5 | | | V-1 | Gm14511 |
| 7741 | 3 | 4 | 5 | | | V-1 | Gm14625 |
| 7742 | 3 | 4 | 5 | | | V-1 | Gm15056 |
| 7743 | 3 | 4 | 5 | | | V-1 | Gm15093 |
| 7744 | 3 | 4 | 5 | | | V-1 | Gm15114 |
| 7745 | 3 | 4 | 5 | | | V-1 | Gm15127 |
| 7746 | 3 | 4 | 5 | | | V-1 | Gm15308 |
| 7747 | 3 | 4 | 5 | | | V-1 | Gm15328 |
| 7748 | 3 | 4 | 5 | | | V-1 | Gm15348 |
| 7749 | 3 | 4 | 5 | | | V-1 | Gm15350 |
| 7750 | 3 | 4 | 5 | | | V-1 | Gm15417 |
| 7751 | 3 | 4 | 5 | | | V-1 | Gm15471 |
| 7752 | 3 | 4 | 5 | | | V-1 | Gm15698 |
| 7753 | 3 | 4 | 5 | | | V-1 | Gm15772 |
| 7754 | 3 | 4 | 5 | | | V-1 | Gm15787 |
| 7755 | 3 | 4 | 5 | | | V-1 | Gm15800 |
| 7756 | 3 | 4 | 5 | | | V-1 | Gm15915 |
| 7757 | 3 | 4 | 5 | | | V-1 | Gm16023 |
| 7758 | 3 | 4 | 5 | | | V-1 | Gm16381 |
| 7759 | 3 | 4 | 5 | | | V-1 | Gm16386 |
| 7760 | 3 | 4 | 5 | | | V-1 | Gm16405 |
| 7761 | 3 | 4 | 5 | | | V-1 | Gm16551 |
| 7762 | 3 | 4 | 5 | | | V-1 | Gm16617 |
| 7763 | 3 | 4 | 5 | | | V-1 | Gm16675 |
| 7764 | 3 | 4 | 5 | | | V-1 | Gm16701 |
| 7765 | 3 | 4 | 5 | | | V-1 | Gm16845 |
| 7766 | 3 | 4 | 5 | | | V-1 | Gm16861 |
| 7767 | 3 | 4 | 5 | | | V-1 | Gm16894 |
| 7768 | 3 | 4 | 5 | | | V-1 | Gm16973 |
| 7769 | 3 | 4 | 5 | | | V-1 | Gm16998 |
| 7770 | 3 | 4 | 5 | | | V-1 | Gm17296 |
| 7771 | 3 | 4 | 5 | | | V-1 | Gm17757 |
| 7772 | 3 | 4 | 5 | | | V-1 | Gm19345 |
| 7773 | 3 | 4 | 5 | | | V-1 | Gm19461 |
| 7774 | 3 | 4 | 5 | | | V-1 | Gm1968 |
| 7775 | 3 | 4 | 5 | | | V-1 | Gm1976 |
| 7776 | 3 | 4 | 5 | | | V-1 | Gm1995 |
| 7777 | 3 | 4 | 5 | | | V-1 | Gm20063 |
| 7778 | 3 | 4 | 5 | | | V-1 | Gm2012 |
| 7779 | 3 | 4 | 5 | | | V-1 | Gm2027 |
| 7780 | 3 | 4 | 5 | | | V-1 | Gm20337 |
| 7781 | 3 | 4 | 5 | | | V-1 | Gm20554 |
| 7782 | 3 | 4 | 5 | | | V-1 | Gm20753 |
| 7783 | 3 | 4 | 5 | | | V-1 | Gm20857 |
| 7784 | 3 | 4 | 5 | | | V-1 | Gm20858 |
| 7785 | 3 | 4 | 5 | | | V-1 | Gm20939 |
| 7786 | 3 | 4 | 5 | | | V-1 | Gm21002 |
| 7787 | 3 | 4 | 5 | | | V-1 | Gm2115 |
| 7788 | 3 | 4 | 5 | | | V-1 | Gm21586 |
| 7789 | 3 | 4 | 5 | | | V-1 | Gm21949 |
| 7790 | 3 | 4 | 5 | | | V-1 | Gm2382 |
| 7791 | 3 | 4 | 5 | | | V-1 | Gm3143 |
| 7792 | 3 | 4 | 5 | | | V-1 | Gm3336 |
| 7793 | 3 | 4 | 5 | | | V-1 | Gm3409 |
| 7794 | 3 | 4 | 5 | | | V-1 | Gm3417 |
| 7795 | 3 | 4 | 5 | | | V-1 | Gm3604 |
| 7796 | 3 | 4 | 5 | | | V-1 | Gm3776 |
| 7797 | 3 | 4 | 5 | | | V-1 | Gm3985 |
| 7798 | 3 | 4 | 5 | | | V-1 | Gm4832 |
| 7799 | 3 | 4 | 5 | | | V-1 | Gm4925 |
| 7800 | 3 | 4 | 5 | | | V-1 | Gm4956 |
| 7801 | 3 | 4 | 5 | | | V-1 | Gm5065 |
| 7802 | 3 | 4 | 5 | | | V-1 | Gm5069 |
| 7803 | 3 | 4 | 5 | | | V-1 | Gm5086 |
| 7804 | 3 | 4 | 5 | | | V-1 | Gm5089 |
| 7805 | 3 | 4 | 5 | | | V-1 | Gm5105 |
| 7806 | 3 | 4 | 5 | | | V-1 | Gm5132 |
| 7807 | 3 | 4 | 5 | | | V-1 | Gm5150 |
| 7808 | 3 | 4 | 5 | | | V-1 | Gm5168 |
| 7809 | 3 | 4 | 5 | | | V-1 | Gm5431 |
| 7810 | 3 | 4 | 5 | | | V-1 | Gm5434 |
| 7811 | 3 | 4 | 5 | | | V-1 | Gm5512 |
| 7812 | 3 | 4 | 5 | | | V-1 | Gm5538 |
| 7813 | 3 | 4 | 5 | | | V-1 | Gm5577 |
| 7814 | 3 | 4 | 5 | | | V-1 | Gm561 |
| 7815 | 3 | 4 | 5 | | | V-1 | Gm572 |
| 7816 | 3 | 4 | 5 | | | V-1 | Gm5741 |
| 7817 | 3 | 4 | 5 | | | V-1 | Gm5771 |
| 7818 | 3 | 4 | 5 | | | V-1 | Gm5803 |
| 7819 | 3 | 4 | 5 | | | V-1 | Gm5860 |
| 7820 | 3 | 4 | 5 | | | V-1 | Gm6026 |
| 7821 | 3 | 4 | 5 | | | V-1 | Gm6194 |
| 7822 | 3 | 4 | 5 | | | V-1 | Gm6268 |
| 7823 | 3 | 4 | 5 | | | V-1 | Gm6297 |
| 7824 | 3 | 4 | 5 | | | V-1 | Gm6300 |
| 7825 | 3 | 4 | 5 | | | V-1 | Gm6307 |
| 7826 | 3 | 4 | 5 | | | V-1 | Gm6402 |
| 7827 | 3 | 4 | 5 | | | V-1 | Gm6416 |
| 7828 | 3 | 4 | 5 | | | V-1 | Gm648 |
| 7829 | 3 | 4 | 5 | | | V-1 | Gm6537 |
| 7830 | 3 | 4 | 5 | | | V-1 | Gm6568 |
| 7831 | 3 | 4 | 5 | | | V-1 | Gm6614 |
| 7832 | 3 | 4 | 5 | | | V-1 | Gm6623 |
| 7833 | 3 | 4 | 5 | | | V-1 | Gm6710 |
| 7834 | 3 | 4 | 5 | | | V-1 | Gm6890 |
| 7835 | 3 | 4 | 5 | | | V-1 | Gm6927 |
| 7836 | 3 | 4 | 5 | | | V-1 | Gm6981 |
| 7837 | 3 | 4 | 5 | | | V-1 | Gm7030 |
| 7838 | 3 | 4 | 5 | | | V-1 | Gm7104 |
| 7839 | 3 | 4 | 5 | | | V-1 | Gm7609 |
| 7840 | 3 | 4 | 5 | | | V-1 | Gm765 |
| 7841 | 3 | 4 | 5 | | | V-1 | Gm7694 |
| 7842 | 3 | 4 | 5 | | | V-1 | Gm773 |
| 7843 | 3 | 4 | 5 | | | V-1 | Gm7788 |
| 7844 | 3 | 4 | 5 | | | V-1 | Gm7849 |
| 7845 | 3 | 4 | 5 | | | V-1 | Gm8580 |
| 7846 | 3 | 4 | 5 | | | V-1 | Gm8633 |
| 7847 | 3 | 4 | 5 | | | V-1 | Gm8787 |
| 7848 | 3 | 4 | 5 | | | V-1 | Gm8909 |
| 7849 | 3 | 4 | 5 | | | V-1 | Gm8979 |
| 7850 | 3 | 4 | 5 | | | V-1 | Gm8989 |
| 7851 | 3 | 4 | 5 | | | V-1 | Gm906 |
| 7852 | 3 | 4 | 5 | | | V-1 | Gm9776 |
| 7853 | 3 | 4 | 5 | | | V-1 | Gm9833 |
| 7854 | 3 | 4 | 5 | | | V-1 | Gm9866 |
| 7855 | 3 | 4 | 5 | | | V-1 | Gm9958 |
| 7856 | 3 | 4 | 5 | | | V-1 | Gm9994 |
| 7857 | 3 | 4 | 5 | | | V-1 | Gmnc |
| 7858 | 3 | 4 | 5 | | | V-1 | Gmppa |
| 7859 | 3 | 4 | 5 | | | V-1 | Gmppb |
| 7860 | 3 | 4 | 5 | | | V-1 | Gmps |
| 7861 | 3 | 4 | 5 | | | V-1 | Gna12 |
| 7862 | 3 | 4 | 5 | | | V-1 | Gna15 |
| 7863 | 3 | 4 | 5 | | | V-1 | Gnai |
| 7864 | 3 | 4 | 5 | | | V-1 | Gnat1 |
| 7865 | 3 | 4 | 5 | | | V-1 | Gnb1l |
| 7866 | 3 | 4 | 5 | | | V-1 | Gnb5 |
| 7867 | 3 | 4 | 5 | | | V-1 | Gng3 |
| 7868 | 3 | 4 | 5 | | | V-1 | Gng8 |
| 7869 | 3 | 4 | 5 | | | V-1 | Gnpda2 |
| 7870 | 3 | 4 | 5 | | | V-1 | Gnrh1 |

Fig. 36 - 42

| | | | | | | | |
|---|---|---|---|---|---|---|---|
| 7871 | 3 | 4 | 5 | | V-1 | Gns | |
| 7872 | 3 | 4 | 5 | | V-1 | Golm1 | |
| 7873 | 3 | 4 | 5 | | V-1 | Gon4l | |
| 7874 | 3 | 4 | 5 | | V-1 | Gp1bb | |
| 7875 | 3 | 4 | 5 | | V-1 | Gpa33 | |
| 7876 | 3 | 4 | 5 | | V-1 | Gpatch2l | |
| 7877 | 3 | 4 | 5 | | V-1 | Gpc4 | |
| 7878 | 3 | 4 | 5 | | V-1 | Gpd2 | |
| 7879 | 3 | 4 | 5 | | V-1 | Gpn1 | |
| 7880 | 3 | 4 | 5 | | V-1 | Gpn2 | |
| 7881 | 3 | 4 | 5 | | V-1 | Gpr116 | |
| 7882 | 3 | 4 | 5 | | V-1 | Gpr132 | |
| 7883 | 3 | 4 | 5 | | V-1 | Gpr141 | |
| 7884 | 3 | 4 | 5 | | V-1 | Gpr155 | |
| 7885 | 3 | 4 | 5 | | V-1 | Gpr156 | |
| 7886 | 3 | 4 | 5 | | V-1 | Gpr162 | |
| 7887 | 3 | 4 | 5 | | V-1 | Gpr173 | |
| 7888 | 3 | 4 | 5 | | V-1 | Gpr27 | |
| 7889 | 3 | 4 | 5 | | V-1 | Gpr34 | |
| 7890 | 3 | 4 | 5 | | V-1 | Gpr35 | |
| 7891 | 3 | 4 | 5 | | V-1 | Gpr37 | |
| 7892 | 3 | 4 | 5 | | V-1 | Gpr39 | |
| 7893 | 3 | 4 | 5 | | V-1 | Gpr52 | |
| 7894 | 3 | 4 | 5 | | V-1 | Gpr64 | |
| 7895 | 3 | 4 | 5 | | V-1 | Gpr65 | |
| 7896 | 3 | 4 | 5 | | V-1 | Gpr84 | |
| 7897 | 3 | 4 | 5 | | V-1 | Gpr97 | |
| 7898 | 3 | 4 | 5 | | V-1 | Gprasp1 | |
| 7899 | 3 | 4 | 5 | | V-1 | Gprc5c | |
| 7900 | 3 | 4 | 5 | | V-1 | Gpsm3 | |
| 7901 | 3 | 4 | 5 | | V-1 | Gpx7 | |
| 7902 | 3 | 4 | 5 | | V-1 | Gpx8 | |
| 7903 | 3 | 4 | 5 | | V-1 | Grb14 | |
| 7904 | 3 | 4 | 5 | | V-1 | Grcc10 | |
| 7905 | 3 | 4 | 5 | | V-1 | Grhl1 | |
| 7906 | 3 | 4 | 5 | | V-1 | Grhpr | |
| 7907 | 3 | 4 | 5 | | V-1 | Grid1 | |
| 7908 | 3 | 4 | 5 | | V-1 | Grik3 | |
| 7909 | 3 | 4 | 5 | | V-1 | Grin1os | |
| 7910 | 3 | 4 | 5 | | V-1 | Grin2c | |
| 7911 | 3 | 4 | 5 | | V-1 | Grin2d | |
| 7912 | 3 | 4 | 5 | | V-1 | Grin3a | |
| 7913 | 3 | 4 | 5 | | V-1 | Grk4 | |
| 7914 | 3 | 4 | 5 | | V-1 | Grk5 | |
| 7915 | 3 | 4 | 5 | | V-1 | Grn | |
| 7916 | 3 | 4 | 5 | | V-1 | Grrp1 | |
| 7917 | 3 | 4 | 5 | | V-1 | Grtp1 | |
| 7918 | 3 | 4 | 5 | | V-1 | Grwd1 | |
| 7919 | 3 | 4 | 5 | | V-1 | Gsc | |
| 7920 | 3 | 4 | 5 | | V-1 | Gsdma2 | |
| 7921 | 3 | 4 | 5 | | V-1 | Gsdmc4 | |
| 7922 | 3 | 4 | 5 | | V-1 | Gsdmc-ps | |
| 7923 | 3 | 4 | 5 | | V-1 | Gsdmcl2 | |
| 7924 | 3 | 4 | 5 | | V-1 | Gsdmd | |
| 7925 | 3 | 4 | 5 | | V-1 | Gse1 | |
| 7926 | 3 | 4 | 5 | | V-1 | Gsta1 | |
| 7927 | 3 | 4 | 5 | | V-1 | Gsta2 | |
| 7928 | 3 | 4 | 5 | | V-1 | Gsta3 | |
| 7929 | 3 | 4 | 5 | | V-1 | Gstk1 | |
| 7930 | 3 | 4 | 5 | | V-1 | Gsto2 | |
| 7931 | 3 | 4 | 5 | | V-1 | Gstp2 | |
| 7932 | 3 | 4 | 5 | | V-1 | Gstt3 | |
| 7933 | 3 | 4 | 5 | | V-1 | Gtf2f1 | |
| 7934 | 3 | 4 | 5 | | V-1 | Gtf2f2 | |
| 7935 | 3 | 4 | 5 | | V-1 | Gtf2h4 | |
| 7936 | 3 | 4 | 5 | | V-1 | Gtf2h5 | |
| 7937 | 3 | 4 | 5 | | V-1 | Gtf2ird1 | |
| 7938 | 3 | 4 | 5 | | V-1 | Gtf3a | |
| 7939 | 3 | 4 | 5 | | V-1 | Gtf3c3 | |
| 7940 | 3 | 4 | 5 | | V-1 | Gtf3c4 | |
| 7941 | 3 | 4 | 5 | | V-1 | Gtf3c6 | |
| 7942 | 3 | 4 | 5 | | V-1 | Gtpbp6 | |
| 7943 | 3 | 4 | 5 | | V-1 | Gtpbp8 | |
| 7944 | 3 | 4 | 5 | | V-1 | Guca1a | |
| 7945 | 3 | 4 | 5 | | V-1 | Gucy1b3 | |
| 7946 | 3 | 4 | 5 | | V-1 | Guk1 | |
| 7947 | 3 | 4 | 5 | | V-1 | Gulp1 | |
| 7948 | 3 | 4 | 5 | | V-1 | Gusb | |
| 7949 | 3 | 4 | 5 | | V-1 | Gxylt2 | |
| 7950 | 3 | 4 | 5 | | V-1 | Gyg | |
| 7951 | 3 | 4 | 5 | | V-1 | Gzma | |
| 7952 | 3 | 4 | 5 | | V-1 | Gzmb | |
| 7953 | 3 | 4 | 5 | | V-1 | Gzmm | |
| 7954 | 3 | 4 | 5 | | V-1 | H19 | |
| 7955 | 3 | 4 | 5 | | V-1 | H1fx | |
| 7956 | 3 | 4 | 5 | | V-1 | H2-Bl | |
| 7957 | 3 | 4 | 5 | | V-1 | H2-D1 | |
| 7958 | 3 | 4 | 5 | | V-1 | H2-DMb1 | |
| 7959 | 3 | 4 | 5 | | V-1 | H2-Ea-ps | |
| 7960 | 3 | 4 | 5 | | V-1 | H2-K2 | |
| 7961 | 3 | 4 | 5 | | V-1 | H2-M2 | |
| 7962 | 3 | 4 | 5 | | V-1 | H2-M3 | |
| 7963 | 3 | 4 | 5 | | V-1 | H2-Q1 | |
| 7964 | 3 | 4 | 5 | | V-1 | H2-Q2 | |
| 7965 | 3 | 4 | 5 | | V-1 | H2-T24 | |
| 7966 | 3 | 4 | 5 | | V-1 | H2afb3 | |
| 7967 | 3 | 4 | 5 | | V-1 | H2afj | |
| 7968 | 3 | 4 | 5 | | V-1 | H2afv | |
| 7969 | 3 | 4 | 5 | | V-1 | H2afy | |
| 7970 | 3 | 4 | 5 | | V-1 | Hadh | |
| 7971 | 3 | 4 | 5 | | V-1 | Haghl | |
| 7972 | 3 | 4 | 5 | | V-1 | Hal | |
| 7973 | 3 | 4 | 5 | | V-1 | Has1 | |
| 7974 | 3 | 4 | 5 | | V-1 | Has2 | |
| 7975 | 3 | 4 | 5 | | V-1 | Has3 | |
| 7976 | 3 | 4 | 5 | | V-1 | Haus7 | |
| 7977 | 3 | 4 | 5 | | V-1 | Haus8 | |
| 7978 | 3 | 4 | 5 | | V-1 | Havcr2 | |
| 7979 | 3 | 4 | 5 | | V-1 | Hax1 | |
| 7980 | 3 | 4 | 5 | | V-1 | Hccs | |
| 7981 | 3 | 4 | 5 | | V-1 | Hcfc1 | |
| 7982 | 3 | 4 | 5 | | V-1 | Hcfc2 | |
| 7983 | 3 | 4 | 5 | | V-1 | Hcls1 | |
| 7984 | 3 | 4 | 5 | | V-1 | Hcn3 | |
| 7985 | 3 | 4 | 5 | | V-1 | Hdac10 | |
| 7986 | 3 | 4 | 5 | | V-1 | Hdac6 | |
| 7987 | 3 | 4 | 5 | | V-1 | Hdac8 | |
| 7988 | 3 | 4 | 5 | | V-1 | Hdac9 | |
| 7989 | 3 | 4 | 5 | | V-1 | Hdc | |
| 7990 | 3 | 4 | 5 | | V-1 | Hddc3 | |
| 7991 | 3 | 4 | 5 | | V-1 | Heatr1 | |
| 7992 | 3 | 4 | 5 | | V-1 | Heatr5a | |
| 7993 | 3 | 4 | 5 | | V-1 | Heatr5b | |
| 7994 | 3 | 4 | 5 | | V-1 | Hebp2 | |
| 7995 | 3 | 4 | 5 | | V-1 | Heca | |
| 7996 | 3 | 4 | 5 | | V-1 | Hectd1 | |
| 7997 | 3 | 4 | 5 | | V-1 | Helq | |
| 7998 | 3 | 4 | 5 | | V-1 | Heph | |
| 7999 | 3 | 4 | 5 | | V-1 | Herc1 | |
| 8000 | 3 | 4 | 5 | | V-1 | Herc2 | |
| 8001 | 3 | 4 | 5 | | V-1 | Herpud1 | |
| 8002 | 3 | 4 | 5 | | V-1 | Hes1 | |
| 8003 | 3 | 4 | 5 | | V-1 | Hexim1 | |
| 8004 | 3 | 4 | 5 | | V-1 | Heyl | |
| 8005 | 3 | 4 | 5 | | V-1 | Hfe2 | |
| 8006 | 3 | 4 | 5 | | V-1 | Hgf | |
| 8007 | 3 | 4 | 5 | | V-1 | Hgfac | |
| 8008 | 3 | 4 | 5 | | V-1 | Hhatl | |
| 8009 | 3 | 4 | 5 | | V-1 | Hiatl1 | |
| 8010 | 3 | 4 | 5 | | V-1 | Hibch | |
| 8011 | 3 | 4 | 5 | | V-1 | Hic2 | |
| 8012 | 3 | 4 | 5 | | V-1 | Hif1an | |
| 8013 | 3 | 4 | 5 | | V-1 | Hilpda | |
| 8014 | 3 | 4 | 5 | | V-1 | Hint3 | |
| 8015 | 3 | 4 | 5 | | V-1 | Hipk4 | |
| 8016 | 3 | 4 | 5 | | V-1 | Hirip3 | |
| 8017 | 3 | 4 | 5 | | V-1 | Hist1h1c | |
| 8018 | 3 | 4 | 5 | | V-1 | Hist1h1d | |
| 8019 | 3 | 4 | 5 | | V-1 | Hist1h1e | |
| 8020 | 3 | 4 | 5 | | V-1 | Hist1h2aa | |
| 8021 | 3 | 4 | 5 | | V-1 | Hist1h2ak | |
| 8022 | 3 | 4 | 5 | | V-1 | Hist1h2bq | |
| 8023 | 3 | 4 | 5 | | V-1 | Hist1h4a | |
| 8024 | 3 | 4 | 5 | | V-1 | Hist1h4f | |
| 8025 | 3 | 4 | 5 | | V-1 | Hist1h4h | |
| 8026 | 3 | 4 | 5 | | V-1 | Hist2h4 | |
| 8027 | 3 | 4 | 5 | | V-1 | Hist4h4 | |
| 8028 | 3 | 4 | 5 | | V-1 | Hivep2 | |
| 8029 | 3 | 4 | 5 | | V-1 | Hk2 | |
| 8030 | 3 | 4 | 5 | | V-1 | Hk3 | |
| 8031 | 3 | 4 | 5 | | V-1 | Hkdc1 | |
| 8032 | 3 | 4 | 5 | | V-1 | Hlx | |
| 8033 | 3 | 4 | 5 | | V-1 | Hmgcs1 | |
| 8034 | 3 | 4 | 5 | | V-1 | Hmgn1 | |
| 8035 | 3 | 4 | 5 | | V-1 | Hmgxb3 | |
| 8036 | 3 | 4 | 5 | | V-1 | Hmha1 | |
| 8037 | 3 | 4 | 5 | | V-1 | Hn1 | |
| 8038 | 3 | 4 | 5 | | V-1 | Hn1l | |
| 8039 | 3 | 4 | 5 | | V-1 | Hnf1a | |
| 8040 | 3 | 4 | 5 | | V-1 | Hnf4g | |
| 8041 | 3 | 4 | 5 | | V-1 | Hnrnpab | |
| 8042 | 3 | 4 | 5 | | V-1 | Hnrnpul1 | |
| 8043 | 3 | 4 | 5 | | V-1 | Homer1 | |
| 8044 | 3 | 4 | 5 | | V-1 | Homer2 | |
| 8045 | 3 | 4 | 5 | | V-1 | Homer3 | |
| 8046 | 3 | 4 | 5 | | V-1 | Hook3 | |
| 8047 | 3 | 4 | 5 | | V-1 | Hoxa5 | |
| 8048 | 3 | 4 | 5 | | V-1 | Hoxb2 | |
| 8049 | 3 | 4 | 5 | | V-1 | Hoxb3 | |
| 8050 | 3 | 4 | 5 | | V-1 | Hoxd11 | |
| 8051 | 3 | 4 | 5 | | V-1 | Hoxd9 | |
| 8052 | 3 | 4 | 5 | | V-1 | Hpca | |
| 8053 | 3 | 4 | 5 | | V-1 | Hpgds | |
| 8054 | 3 | 4 | 5 | | V-1 | Hps4 | |
| 8055 | 3 | 4 | 5 | | V-1 | Hr | |
| 8056 | 3 | 4 | 5 | | V-1 | Hrct1 | |
| 8057 | 3 | 4 | 5 | | V-1 | Hs3st1 | |
| 8058 | 3 | 4 | 5 | | V-1 | Hs3st3a1 | |
| 8059 | 3 | 4 | 5 | | V-1 | Hs3st5 | |
| 8060 | 3 | 4 | 5 | | V-1 | Hs3st6 | |
| 8061 | 3 | 4 | 5 | | V-1 | Hsbp1l1 | |
| 8062 | 3 | 4 | 5 | | V-1 | Hsd17b12 | |

Fig. 36 - 43

| | | | | | | |
|---|---|---|---|---|---|---|
| 8063 | 3 | 4 | 5 | | V-1 | Hsd17b13 |
| 8064 | 3 | 4 | 5 | | V-1 | Hsd17b14 |
| 8065 | 3 | 4 | 5 | | V-1 | Hsd17b6 |
| 8066 | 3 | 4 | 5 | | V-1 | Hsd17b7 |
| 8067 | 3 | 4 | 5 | | V-1 | Hsd3b6 |
| 8068 | 3 | 4 | 5 | | V-1 | Hsf4 |
| 8069 | 3 | 4 | 5 | | V-1 | Hspa13 |
| 8070 | 3 | 4 | 5 | | V-1 | Hspa2 |
| 8071 | 3 | 4 | 5 | | V-1 | Hspa8 |
| 8072 | 3 | 4 | 5 | | V-1 | Hspb3 |
| 8073 | 3 | 4 | 5 | | V-1 | Hspe1 |
| 8074 | 3 | 4 | 5 | | V-1 | Hsph1 |
| 8075 | 3 | 4 | 5 | | V-1 | Htatip2 |
| 8076 | 3 | 4 | 5 | | V-1 | Htr1b |
| 8077 | 3 | 4 | 5 | | V-1 | Htr1d |
| 8078 | 3 | 4 | 5 | | V-1 | Htr5b |
| 8079 | 3 | 4 | 5 | | V-1 | Htra1 |
| 8080 | 3 | 4 | 5 | | V-1 | Htra3 |
| 8081 | 3 | 4 | 5 | | V-1 | Htt |
| 8082 | 3 | 4 | 5 | | V-1 | Huwe1 |
| 8083 | 3 | 4 | 5 | | V-1 | Hyls1 |
| 8084 | 3 | 4 | 5 | | V-1 | Hypk |
| 8085 | 3 | 4 | 5 | | V-1 | Iah1 |
| 8086 | 3 | 4 | 5 | | V-1 | Icam1 |
| 8087 | 3 | 4 | 5 | | V-1 | Icosl |
| 8088 | 3 | 4 | 5 | | V-1 | Id1 |
| 8089 | 3 | 4 | 5 | | V-1 | Id2 |
| 8090 | 3 | 4 | 5 | | V-1 | Id4 |
| 8091 | 3 | 4 | 5 | | V-1 | Idh3a |
| 8092 | 3 | 4 | 5 | | V-1 | Idi1 |
| 8093 | 3 | 4 | 5 | | V-1 | Ier2 |
| 8094 | 3 | 4 | 5 | | V-1 | Ier3 |
| 8095 | 3 | 4 | 5 | | V-1 | Ier3ip1 |
| 8096 | 3 | 4 | 5 | | V-1 | Ier5 |
| 8097 | 3 | 4 | 5 | | V-1 | Ifi204 |
| 8098 | 3 | 4 | 5 | | V-1 | Ifi27l2b |
| 8099 | 3 | 4 | 5 | | V-1 | Ifih1 |
| 8100 | 3 | 4 | 5 | | V-1 | Ifit2 |
| 8101 | 3 | 4 | 5 | | V-1 | Ifitm2 |
| 8102 | 3 | 4 | 5 | | V-1 | Ifnar2 |
| 8103 | 3 | 4 | 5 | | V-1 | Ifngr2 |
| 8104 | 3 | 4 | 5 | | V-1 | Ifrd2 |
| 8105 | 3 | 4 | 5 | | V-1 | Ift172 |
| 8106 | 3 | 4 | 5 | | V-1 | Ift43 |
| 8107 | 3 | 4 | 5 | | V-1 | Igf1 |
| 8108 | 3 | 4 | 5 | | V-1 | Igf1r |
| 8109 | 3 | 4 | 5 | | V-1 | Igf2r |
| 8110 | 3 | 4 | 5 | | V-1 | Igfals |
| 8111 | 3 | 4 | 5 | | V-1 | Igflr1 |
| 8112 | 3 | 4 | 5 | | V-1 | Iglon5 |
| 8113 | 3 | 4 | 5 | | V-1 | Ikbip |
| 8114 | 3 | 4 | 5 | | V-1 | Ikzf1 |
| 8115 | 3 | 4 | 5 | | V-1 | Ikzf2 |
| 8116 | 3 | 4 | 5 | | V-1 | Ikzf3 |
| 8117 | 3 | 4 | 5 | | V-1 | Ikzf4 |
| 8118 | 3 | 4 | 5 | | V-1 | Ikzf5 |
| 8119 | 3 | 4 | 5 | | V-1 | Il10ra |
| 8120 | 3 | 4 | 5 | | V-1 | Il11ra1 |
| 8121 | 3 | 4 | 5 | | V-1 | Il11ra2 |
| 8122 | 3 | 4 | 5 | | V-1 | Il12rb2 |
| 8123 | 3 | 4 | 5 | | V-1 | Il13ra1 |
| 8124 | 3 | 4 | 5 | | V-1 | Il17rd |
| 8125 | 3 | 4 | 5 | | V-1 | Il17re |
| 8126 | 3 | 4 | 5 | | V-1 | Il18rap |
| 8127 | 3 | 4 | 5 | | V-1 | Il1rapl1 |
| 8128 | 3 | 4 | 5 | | V-1 | Il1rl2 |
| 8129 | 3 | 4 | 5 | | V-1 | Il21r |
| 8130 | 3 | 4 | 5 | | V-1 | Il22ra1 |
| 8131 | 3 | 4 | 5 | | V-1 | Il2rb |
| 8132 | 3 | 4 | 5 | | V-1 | Il2rg |
| 8133 | 3 | 4 | 5 | | V-1 | Il34 |
| 8134 | 3 | 4 | 5 | | V-1 | Il3ra |
| 8135 | 3 | 4 | 5 | | V-1 | Il6st |
| 8136 | 3 | 4 | 5 | | V-1 | Ilvbl |
| 8137 | 3 | 4 | 5 | | V-1 | Immp1l |
| 8138 | 3 | 4 | 5 | | V-1 | Immp2l |
| 8139 | 3 | 4 | 5 | | V-1 | Imp3 |
| 8140 | 3 | 4 | 5 | | V-1 | Impa2 |
| 8141 | 3 | 4 | 5 | | V-1 | Impdh2 |
| 8142 | 3 | 4 | 5 | | V-1 | Inca1 |
| 8143 | 3 | 4 | 5 | | V-1 | Ino80d |
| 8144 | 3 | 4 | 5 | | V-1 | Ino80dos |
| 8145 | 3 | 4 | 5 | | V-1 | Inpp5a |
| 8146 | 3 | 4 | 5 | | V-1 | Inpp5j |
| 8147 | 3 | 4 | 5 | | V-1 | Insl3 |
| 8148 | 3 | 4 | 5 | | V-1 | Ints1 |
| 8149 | 3 | 4 | 5 | | V-1 | Ints6 |
| 8150 | 3 | 4 | 5 | | V-1 | Ints7 |
| 8151 | 3 | 4 | 5 | | V-1 | Ints8 |
| 8152 | 3 | 4 | 5 | | V-1 | Intu |
| 8153 | 3 | 4 | 5 | | V-1 | Ip6k2 |
| 8154 | 3 | 4 | 5 | | V-1 | Ipcef1 |
| 8155 | 3 | 4 | 5 | | V-1 | Ipo13 |
| 8156 | 3 | 4 | 5 | | V-1 | Ipo7 |
| 8157 | 3 | 4 | 5 | | V-1 | Iqce |
| 8158 | 3 | 4 | 5 | | V-1 | Iqcf5 |
| 8159 | 3 | 4 | 5 | | V-1 | Iqgap2 |
| 8160 | 3 | 4 | 5 | | V-1 | Iqsec1 |
| 8161 | 3 | 4 | 5 | | V-1 | Iqsec3 |
| 8162 | 3 | 4 | 5 | | V-1 | Irak2 |
| 8163 | 3 | 4 | 5 | | V-1 | Irf2bpl |
| 8164 | 3 | 4 | 5 | | V-1 | Irf5 |
| 8165 | 3 | 4 | 5 | | V-1 | Irf9 |
| 8166 | 3 | 4 | 5 | | V-1 | Irs1 |
| 8167 | 3 | 4 | 5 | | V-1 | Irs4 |
| 8168 | 3 | 4 | 5 | | V-1 | Iscu |
| 8169 | 3 | 4 | 5 | | V-1 | Isl1 |
| 8170 | 3 | 4 | 5 | | V-1 | Ism1 |
| 8171 | 3 | 4 | 5 | | V-1 | Isoc1 |
| 8172 | 3 | 4 | 5 | | V-1 | Itfg3 |
| 8173 | 3 | 4 | 5 | | V-1 | Itga3 |
| 8174 | 3 | 4 | 5 | | V-1 | Itga4 |
| 8175 | 3 | 4 | 5 | | V-1 | Itga8 |
| 8176 | 3 | 4 | 5 | | V-1 | Itgb3bp |
| 8177 | 3 | 4 | 5 | | V-1 | Itgb7 |
| 8178 | 3 | 4 | 5 | | V-1 | Itih2 |
| 8179 | 3 | 4 | 5 | | V-1 | Itih5 |
| 8180 | 3 | 4 | 5 | | V-1 | Itm2a |
| 8181 | 3 | 4 | 5 | | V-1 | Itpka |
| 8182 | 3 | 4 | 5 | | V-1 | Itpr3 |
| 8183 | 3 | 4 | 5 | | V-1 | Itprip |
| 8184 | 3 | 4 | 5 | | V-1 | Itpripl2 |
| 8185 | 3 | 4 | 5 | | V-1 | Itsn2 |
| 8186 | 3 | 4 | 5 | | V-1 | Iws1 |
| 8187 | 3 | 4 | 5 | | V-1 | Jag2 |
| 8188 | 3 | 4 | 5 | | V-1 | Jdp2 |
| 8189 | 3 | 4 | 5 | | V-1 | Jmjd1c |
| 8190 | 3 | 4 | 5 | | V-1 | Jmjd4 |
| 8191 | 3 | 4 | 5 | | V-1 | Jmjd6 |
| 8192 | 3 | 4 | 5 | | V-1 | Jmjd7 |
| 8193 | 3 | 4 | 5 | | V-1 | Jmy |
| 8194 | 3 | 4 | 5 | | V-1 | Jph2 |
| 8195 | 3 | 4 | 5 | | V-1 | Junb |
| 8196 | 3 | 4 | 5 | | V-1 | Kank3 |
| 8197 | 3 | 4 | 5 | | V-1 | Kank4 |
| 8198 | 3 | 4 | 5 | | V-1 | Kat6a |
| 8199 | 3 | 4 | 5 | | V-1 | Kat8 |
| 8200 | 3 | 4 | 5 | | V-1 | Kbtbd13 |
| 8201 | 3 | 4 | 5 | | V-1 | Kbtbd4 |
| 8202 | 3 | 4 | 5 | | V-1 | Kbtbd8 |
| 8203 | 3 | 4 | 5 | | V-1 | Kcna1 |
| 8204 | 3 | 4 | 5 | | V-1 | Kcna2 |
| 8205 | 3 | 4 | 5 | | V-1 | Kcnb1 |
| 8206 | 3 | 4 | 5 | | V-1 | Kcnb2 |
| 8207 | 3 | 4 | 5 | | V-1 | Kcnc1 |
| 8208 | 3 | 4 | 5 | | V-1 | Kcnc3 |
| 8209 | 3 | 4 | 5 | | V-1 | Kcnd1 |
| 8210 | 3 | 4 | 5 | | V-1 | Kcne1 |
| 8211 | 3 | 4 | 5 | | V-1 | Kcng1 |
| 8212 | 3 | 4 | 5 | | V-1 | Kcng4 |
| 8213 | 3 | 4 | 5 | | V-1 | Kcnh1 |
| 8214 | 3 | 4 | 5 | | V-1 | Kcnh2 |
| 8215 | 3 | 4 | 5 | | V-1 | Kcnip3 |
| 8216 | 3 | 4 | 5 | | V-1 | Kcnj10 |
| 8217 | 3 | 4 | 5 | | V-1 | Kcnj8 |
| 8218 | 3 | 4 | 5 | | V-1 | Kcnk10 |
| 8219 | 3 | 4 | 5 | | V-1 | Kcnk16 |
| 8220 | 3 | 4 | 5 | | V-1 | Kcnk2 |
| 8221 | 3 | 4 | 5 | | V-1 | Kcnk6 |
| 8222 | 3 | 4 | 5 | | V-1 | Kcnmb4 |
| 8223 | 3 | 4 | 5 | | V-1 | Kcnn2 |
| 8224 | 3 | 4 | 5 | | V-1 | Kcnn4 |
| 8225 | 3 | 4 | 5 | | V-1 | Kcnq4 |
| 8226 | 3 | 4 | 5 | | V-1 | Kcnrg |
| 8227 | 3 | 4 | 5 | | V-1 | Kcnt2 |
| 8228 | 3 | 4 | 5 | | V-1 | Kcp |
| 8229 | 3 | 4 | 5 | | V-1 | Kctd11 |
| 8230 | 3 | 4 | 5 | | V-1 | Kctd12 |
| 8231 | 3 | 4 | 5 | | V-1 | Kctd13 |
| 8232 | 3 | 4 | 5 | | V-1 | Kctd15 |
| 8233 | 3 | 4 | 5 | | V-1 | Kctd20 |
| 8234 | 3 | 4 | 5 | | V-1 | Kctd6 |
| 8235 | 3 | 4 | 5 | | V-1 | Kdm3b |
| 8236 | 3 | 4 | 5 | | V-1 | Kdm6a |
| 8237 | 3 | 4 | 5 | | V-1 | Kdm6b |
| 8238 | 3 | 4 | 5 | | V-1 | Kdm7a |
| 8239 | 3 | 4 | 5 | | V-1 | Khdrbs3 |
| 8240 | 3 | 4 | 5 | | V-1 | Kif20b |
| 8241 | 3 | 4 | 5 | | V-1 | Kif21b |
| 8242 | 3 | 4 | 5 | | V-1 | Kif24 |
| 8243 | 3 | 4 | 5 | | V-1 | Kif26a |
| 8244 | 3 | 4 | 5 | | V-1 | Kif2c |
| 8245 | 3 | 4 | 5 | | V-1 | Kif3b |
| 8246 | 3 | 4 | 5 | | V-1 | Kif6 |
| 8247 | 3 | 4 | 5 | | V-1 | Kif9 |
| 8248 | 3 | 4 | 5 | | V-1 | Kifc1 |
| 8249 | 3 | 4 | 5 | | V-1 | Kifc3 |
| 8250 | 3 | 4 | 5 | | V-1 | Kin |
| 8251 | 3 | 4 | 5 | | V-1 | Kirrel |
| 8252 | 3 | 4 | 5 | | V-1 | Kit |
| 8253 | 3 | 4 | 5 | | V-1 | Klf2 |
| 8254 | 3 | 4 | 5 | | V-1 | Klf4 |

Fig. 36 - 44

| | | | | | | | |
|---|---|---|---|---|---|---|---|
| 8255 | 3 | 4 | 5 | | V-1 | Klf5 |
| 8256 | 3 | 4 | 5 | | V-1 | Klf8 |
| 8257 | 3 | 4 | 5 | | V-1 | Klf9 |
| 8258 | 3 | 4 | 5 | | V-1 | Khdc8a |
| 8259 | 3 | 4 | 5 | | V-1 | Klhl24 |
| 8260 | 3 | 4 | 5 | | V-1 | Klhl32 |
| 8261 | 3 | 4 | 5 | | V-1 | Klhl33 |
| 8262 | 3 | 4 | 5 | | V-1 | Klhl35 |
| 8263 | 3 | 4 | 5 | | V-1 | Klk12 |
| 8264 | 3 | 4 | 5 | | V-1 | Klk1b21 |
| 8265 | 3 | 4 | 5 | | V-1 | Klk1b24 |
| 8266 | 3 | 4 | 5 | | V-1 | Klk1b8 |
| 8267 | 3 | 4 | 5 | | V-1 | Klk1b9 |
| 8268 | 3 | 4 | 5 | | V-1 | Klra12 |
| 8269 | 3 | 4 | 5 | | V-1 | Klra14-ps |
| 8270 | 3 | 4 | 5 | | V-1 | Klrb1c |
| 8271 | 3 | 4 | 5 | | V-1 | Klrg1 |
| 8272 | 3 | 4 | 5 | | V-1 | Klrg2 |
| 8273 | 3 | 4 | 5 | | V-1 | Klri2 |
| 8274 | 3 | 4 | 5 | | V-1 | Kmt2b |
| 8275 | 3 | 4 | 5 | | V-1 | Kmt2c |
| 8276 | 3 | 4 | 5 | | V-1 | Kmt2e |
| 8277 | 3 | 4 | 5 | | V-1 | Kndc1 |
| 8278 | 3 | 4 | 5 | | V-1 | Kpna3 |
| 8279 | 3 | 4 | 5 | | V-1 | Krcc1 |
| 8280 | 3 | 4 | 5 | | V-1 | Kri1 |
| 8281 | 3 | 4 | 5 | | V-1 | Krt20 |
| 8282 | 3 | 4 | 5 | | V-1 | Krt23 |
| 8283 | 3 | 4 | 5 | | V-1 | Krt33a |
| 8284 | 3 | 4 | 5 | | V-1 | Krt33b |
| 8285 | 3 | 4 | 5 | | V-1 | Krt34 |
| 8286 | 3 | 4 | 5 | | V-1 | Krt80 |
| 8287 | 3 | 4 | 5 | | V-1 | Krt81 |
| 8288 | 3 | 4 | 5 | | V-1 | Krt86 |
| 8289 | 3 | 4 | 5 | | V-1 | Krtap1-3 |
| 8290 | 3 | 4 | 5 | | V-1 | Krtap17-1 |
| 8291 | 3 | 4 | 5 | | V-1 | Krtap4-8 |
| 8292 | 3 | 4 | 5 | | V-1 | Krtap5-1 |
| 8293 | 3 | 4 | 5 | | V-1 | Krtap5-4 |
| 8294 | 3 | 4 | 5 | | V-1 | Krtap9-1 |
| 8295 | 3 | 4 | 5 | | V-1 | Krtap9-3 |
| 8296 | 3 | 4 | 5 | | V-1 | Krtcap2 |
| 8297 | 3 | 4 | 5 | | V-1 | Ksr1 |
| 8298 | 3 | 4 | 5 | | V-1 | Ktl12 |
| 8299 | 3 | 4 | 5 | | V-1 | L3mbtl1 |
| 8300 | 3 | 4 | 5 | | V-1 | L3mbtl3 |
| 8301 | 3 | 4 | 5 | | V-1 | LOC100038947 |
| 8302 | 3 | 4 | 5 | | V-1 | LOC100504608 |
| 8303 | 3 | 4 | 5 | | V-1 | LOC100862268 |
| 8304 | 3 | 4 | 5 | | V-1 | LOC101055769 |
| 8305 | 3 | 4 | 5 | | V-1 | LOC101056043 |
| 8306 | 3 | 4 | 5 | | V-1 | LOC101669761 |
| 8307 | 3 | 4 | 5 | | V-1 | LOC102631757 |
| 8308 | 3 | 4 | 5 | | V-1 | LOC102634753 |
| 8309 | 3 | 4 | 5 | | V-1 | Lacc1 |
| 8310 | 3 | 4 | 5 | | V-1 | Lace1 |
| 8311 | 3 | 4 | 5 | | V-1 | Lag3 |
| 8312 | 3 | 4 | 5 | | V-1 | Lage3 |
| 8313 | 3 | 4 | 5 | | V-1 | Lair1 |
| 8314 | 3 | 4 | 5 | | V-1 | Lama2 |
| 8315 | 3 | 4 | 5 | | V-1 | Lama5 |
| 8316 | 3 | 4 | 5 | | V-1 | Lamtor2 |
| 8317 | 3 | 4 | 5 | | V-1 | Lamtor4 |
| 8318 | 3 | 4 | 5 | | V-1 | Laptm5 |
| 8319 | 3 | 4 | 5 | | V-1 | Larp4b |
| 8320 | 3 | 4 | 5 | | V-1 | Lax1 |
| 8321 | 3 | 4 | 5 | | V-1 | Layn |
| 8322 | 3 | 4 | 5 | | V-1 | Lca5 |
| 8323 | 3 | 4 | 5 | | V-1 | Lca5l |
| 8324 | 3 | 4 | 5 | | V-1 | Lcmt1 |
| 8325 | 3 | 4 | 5 | | V-1 | Lcp1 |
| 8326 | 3 | 4 | 5 | | V-1 | Lcp2 |
| 8327 | 3 | 4 | 5 | | V-1 | Ldha |
| 8328 | 3 | 4 | 5 | | V-1 | Ldhb |
| 8329 | 3 | 4 | 5 | | V-1 | Ldlr |
| 8330 | 3 | 4 | 5 | | V-1 | Ldlrad3 |
| 8331 | 3 | 4 | 5 | | V-1 | Lef1 |
| 8332 | 3 | 4 | 5 | | V-1 | Lefty1 |
| 8333 | 3 | 4 | 5 | | V-1 | Lekr1 |
| 8334 | 3 | 4 | 5 | | V-1 | Lelp1 |
| 8335 | 3 | 4 | 5 | | V-1 | Lemd1 |
| 8336 | 3 | 4 | 5 | | V-1 | Lenep |
| 8337 | 3 | 4 | 5 | | V-1 | Lepr |
| 8338 | 3 | 4 | 5 | | V-1 | Leprotl1 |
| 8339 | 3 | 4 | 5 | | V-1 | Letmd1 |
| 8340 | 3 | 4 | 5 | | V-1 | Lgals12 |
| 8341 | 3 | 4 | 5 | | V-1 | Lgals7 |
| 8342 | 3 | 4 | 5 | | V-1 | Lgals9 |
| 8343 | 3 | 4 | 5 | | V-1 | Lgalsl |
| 8344 | 3 | 4 | 5 | | V-1 | Lgi3 |
| 8345 | 3 | 4 | 5 | | V-1 | Lgr5 |
| 8346 | 3 | 4 | 5 | | V-1 | Lhb |
| 8347 | 3 | 4 | 5 | | V-1 | Lias |
| 8348 | 3 | 4 | 5 | | V-1 | Lig1 |
| 8349 | 3 | 4 | 5 | | V-1 | Lig4 |
| 8350 | 3 | 4 | 5 | | V-1 | Lilra5 |
| 8351 | 3 | 4 | 5 | | V-1 | Lin28a |
| 8352 | 3 | 4 | 5 | | V-1 | Lin28b |
| 8353 | 3 | 4 | 5 | | V-1 | Lin37 |
| 8354 | 3 | 4 | 5 | | V-1 | Lin7b |
| 8355 | 3 | 4 | 5 | | V-1 | Lin9 |
| 8356 | 3 | 4 | 5 | | V-1 | Lingo2 |
| 8357 | 3 | 4 | 5 | | V-1 | Lingo3 |
| 8358 | 3 | 4 | 5 | | V-1 | Lins |
| 8359 | 3 | 4 | 5 | | V-1 | Lix1 |
| 8360 | 3 | 4 | 5 | | V-1 | Lgl1 |
| 8361 | 3 | 4 | 5 | | V-1 | Lgl2 |
| 8362 | 3 | 4 | 5 | | V-1 | Llph |
| 8363 | 3 | 4 | 5 | | V-1 | Lmbr1l |
| 8364 | 3 | 4 | 5 | | V-1 | Lmnb2 |
| 8365 | 3 | 4 | 5 | | V-1 | Lmo1 |
| 8366 | 3 | 4 | 5 | | V-1 | Lmod2 |
| 8367 | 3 | 4 | 5 | | V-1 | Lmod3 |
| 8368 | 3 | 4 | 5 | | V-1 | Lmtk2 |
| 8369 | 3 | 4 | 5 | | V-1 | Lonrf1 |
| 8370 | 3 | 4 | 5 | | V-1 | Lonrf2 |
| 8371 | 3 | 4 | 5 | | V-1 | Lonrf3 |
| 8372 | 3 | 4 | 5 | | V-1 | Lpar3 |
| 8373 | 3 | 4 | 5 | | V-1 | Lpar5 |
| 8374 | 3 | 4 | 5 | | V-1 | Lpcat2 |
| 8375 | 3 | 4 | 5 | | V-1 | Lpgat1 |
| 8376 | 3 | 4 | 5 | | V-1 | Lpo |
| 8377 | 3 | 4 | 5 | | V-1 | Lpp |
| 8378 | 3 | 4 | 5 | | V-1 | Lrat |
| 8379 | 3 | 4 | 5 | | V-1 | Lrba |
| 8380 | 3 | 4 | 5 | | V-1 | Lrfn4 |
| 8381 | 3 | 4 | 5 | | V-1 | Lrp1 |
| 8382 | 3 | 4 | 5 | | V-1 | Lrr1 |
| 8383 | 3 | 4 | 5 | | V-1 | Lrrc14 |
| 8384 | 3 | 4 | 5 | | V-1 | Lrrc15 |
| 8385 | 3 | 4 | 5 | | V-1 | Lrrc18 |
| 8386 | 3 | 4 | 5 | | V-1 | Lrrc27 |
| 8387 | 3 | 4 | 5 | | V-1 | Lrrc3 |
| 8388 | 3 | 4 | 5 | | V-1 | Lrrc32 |
| 8389 | 3 | 4 | 5 | | V-1 | Lrrc4 |
| 8390 | 3 | 4 | 5 | | V-1 | Lrrc45 |
| 8391 | 3 | 4 | 5 | | V-1 | Lrrc49 |
| 8392 | 3 | 4 | 5 | | V-1 | Lrrc56 |
| 8393 | 3 | 4 | 5 | | V-1 | Lrrc59 |
| 8394 | 3 | 4 | 5 | | V-1 | Lrrc73 |
| 8395 | 3 | 4 | 5 | | V-1 | Lrrc75a |
| 8396 | 3 | 4 | 5 | | V-1 | Lrrfip1 |
| 8397 | 3 | 4 | 5 | | V-1 | Lrrk2 |
| 8398 | 3 | 4 | 5 | | V-1 | Lrrn2 |
| 8399 | 3 | 4 | 5 | | V-1 | Lrwd1 |
| 8400 | 3 | 4 | 5 | | V-1 | Lsm11 |
| 8401 | 3 | 4 | 5 | | V-1 | Lsp1 |
| 8402 | 3 | 4 | 5 | | V-1 | Lsr |
| 8403 | 3 | 4 | 5 | | V-1 | Lss |
| 8404 | 3 | 4 | 5 | | V-1 | Lta4h |
| 8405 | 3 | 4 | 5 | | V-1 | Ltb |
| 8406 | 3 | 4 | 5 | | V-1 | Ltk |
| 8407 | 3 | 4 | 5 | | V-1 | Lurap1 |
| 8408 | 3 | 4 | 5 | | V-1 | Lurap1l |
| 8409 | 3 | 4 | 5 | | V-1 | Luzp1 |
| 8410 | 3 | 4 | 5 | | V-1 | Lxn |
| 8411 | 3 | 4 | 5 | | V-1 | Ly6a |
| 8412 | 3 | 4 | 5 | | V-1 | Ly6c2 |
| 8413 | 3 | 4 | 5 | | V-1 | Ly6d |
| 8414 | 3 | 4 | 5 | | V-1 | Ly6e |
| 8415 | 3 | 4 | 5 | | V-1 | Lyl1 |
| 8416 | 3 | 4 | 5 | | V-1 | Lyrm1 |
| 8417 | 3 | 4 | 5 | | V-1 | Lyrm4 |
| 8418 | 3 | 4 | 5 | | V-1 | Lyrm7os |
| 8419 | 3 | 4 | 5 | | V-1 | Lysmd2 |
| 8420 | 3 | 4 | 5 | | V-1 | Lyzl1 |
| 8421 | 3 | 4 | 5 | | V-1 | Lzts3 |
| 8422 | 3 | 4 | 5 | | V-1 | Macrod1 |
| 8423 | 3 | 4 | 5 | | V-1 | Mad1l1 |
| 8424 | 3 | 4 | 5 | | V-1 | Mad2l2 |
| 8425 | 3 | 4 | 5 | | V-1 | Madd |
| 8426 | 3 | 4 | 5 | | V-1 | Mafb |
| 8427 | 3 | 4 | 5 | | V-1 | Magea5 |
| 8428 | 3 | 4 | 5 | | V-1 | Malt1 |
| 8429 | 3 | 4 | 5 | | V-1 | Maml3 |
| 8430 | 3 | 4 | 5 | | V-1 | Mamld1 |
| 8431 | 3 | 4 | 5 | | V-1 | Mamstr |
| 8432 | 3 | 4 | 5 | | V-1 | Man2a1 |
| 8433 | 3 | 4 | 5 | | V-1 | Man2b1 |
| 8434 | 3 | 4 | 5 | | V-1 | Man2b2 |
| 8435 | 3 | 4 | 5 | | V-1 | Manba |
| 8436 | 3 | 4 | 5 | | V-1 | Mansc4 |
| 8437 | 3 | 4 | 5 | | V-1 | Maoa |
| 8438 | 3 | 4 | 5 | | V-1 | Maob |
| 8439 | 3 | 4 | 5 | | V-1 | Map10 |
| 8440 | 3 | 4 | 5 | | V-1 | Map1a |
| 8441 | 3 | 4 | 5 | | V-1 | Map1lc3a |
| 8442 | 3 | 4 | 5 | | V-1 | Map2k6 |
| 8443 | 3 | 4 | 5 | | V-1 | Map3k11 |
| 8444 | 3 | 4 | 5 | | V-1 | Map3k14 |
| 8445 | 3 | 4 | 5 | | V-1 | Map3k15 |
| 8446 | 3 | 4 | 5 | | V-1 | Map3k19 |
| | | | | | | Map3k2 |

Fig. 36 - 45

| | | | | | | |
|---|---|---|---|---|---|---|
| 8447 | 3 | 4 | 5 | | V-1 | Map3k3 |
| 8448 | 3 | 4 | 5 | | V-1 | Map3k7cl |
| 8449 | 3 | 4 | 5 | | V-1 | Map3k9 |
| 8450 | 3 | 4 | 5 | | V-1 | Map4k1 |
| 8451 | 3 | 4 | 5 | | V-1 | Map7 |
| 8452 | 3 | 4 | 5 | | V-1 | Mapk4 |
| 8453 | 3 | 4 | 5 | | V-1 | Mapt |
| 8454 | 3 | 4 | 5 | | V-1 | March7 |
| 8455 | 3 | 4 | 5 | | V-1 | March9 |
| 8456 | 3 | 4 | 5 | | V-1 | Marcksl1-ps4 |
| 8457 | 3 | 4 | 5 | | V-1 | Marf1 |
| 8458 | 3 | 4 | 5 | | V-1 | Mark4 |
| 8459 | 3 | 4 | 5 | | V-1 | Marveld2 |
| 8460 | 3 | 4 | 5 | | V-1 | Mas1 |
| 8461 | 3 | 4 | 5 | | V-1 | Masp2 |
| 8462 | 3 | 4 | 5 | | V-1 | Mast4 |
| 8463 | 3 | 4 | 5 | | V-1 | Mat2a |
| 8464 | 3 | 4 | 5 | | V-1 | Matk |
| 8465 | 3 | 4 | 5 | | V-1 | Mau2 |
| 8466 | 3 | 4 | 5 | | V-1 | Mbd5 |
| 8467 | 3 | 4 | 5 | | V-1 | Mbnl2 |
| 8468 | 3 | 4 | 5 | | V-1 | Mboat2 |
| 8469 | 3 | 4 | 5 | | V-1 | Mcam |
| 8470 | 3 | 4 | 5 | | V-1 | Mccc1 |
| 8471 | 3 | 4 | 5 | | V-1 | Mcoc2 |
| 8472 | 3 | 4 | 5 | | V-1 | Mcm2 |
| 8473 | 3 | 4 | 5 | | V-1 | Mcm3ap |
| 8474 | 3 | 4 | 5 | | V-1 | Mcm6 |
| 8475 | 3 | 4 | 5 | | V-1 | Mcm9 |
| 8476 | 3 | 4 | 5 | | V-1 | Mcrs1 |
| 8477 | 3 | 4 | 5 | | V-1 | Mcts2 |
| 8478 | 3 | 4 | 5 | | V-1 | Mdc1 |
| 8479 | 3 | 4 | 5 | | V-1 | Mdga1 |
| 8480 | 3 | 4 | 5 | | V-1 | Mdga2 |
| 8481 | 3 | 4 | 5 | | V-1 | Mdn1 |
| 8482 | 3 | 4 | 5 | | V-1 | Mecp2 |
| 8483 | 3 | 4 | 5 | | V-1 | Mecr |
| 8484 | 3 | 4 | 5 | | V-1 | Med1 |
| 8485 | 3 | 4 | 5 | | V-1 | Med11 |
| 8486 | 3 | 4 | 5 | | V-1 | Med12 |
| 8487 | 3 | 4 | 5 | | V-1 | Med13l |
| 8488 | 3 | 4 | 5 | | V-1 | Med18 |
| 8489 | 3 | 4 | 5 | | V-1 | Med19 |
| 8490 | 3 | 4 | 5 | | V-1 | Med27 |
| 8491 | 3 | 4 | 5 | | V-1 | Med28 |
| 8492 | 3 | 4 | 5 | | V-1 | Med31 |
| 8493 | 3 | 4 | 5 | | V-1 | Mefv |
| 8494 | 3 | 4 | 5 | | V-1 | Meg3 |
| 8495 | 3 | 4 | 5 | | V-1 | Meis3 |
| 8496 | 3 | 4 | 5 | | V-1 | Mesp1 |
| 8497 | 3 | 4 | 5 | | V-1 | Met |
| 8498 | 3 | 4 | 5 | | V-1 | Metap1d |
| 8499 | 3 | 4 | 5 | | V-1 | Metrn |
| 8500 | 3 | 4 | 5 | | V-1 | Mettl13 |
| 8501 | 3 | 4 | 5 | | V-1 | Mettl22 |
| 8502 | 3 | 4 | 5 | | V-1 | Mettl3 |
| 8503 | 3 | 4 | 5 | | V-1 | Mettl5 |
| 8504 | 3 | 4 | 5 | | V-1 | Mettl7a2Higd1c |
| 8505 | 3 | 4 | 5 | | V-1 | Mex3a |
| 8506 | 3 | 4 | 5 | | V-1 | Mex3b |
| 8507 | 3 | 4 | 5 | | V-1 | Mfap1a |
| 8508 | 3 | 4 | 5 | | V-1 | Mfap1b |
| 8509 | 3 | 4 | 5 | | V-1 | Mfap2 |
| 8510 | 3 | 4 | 5 | | V-1 | Mfap3 |
| 8511 | 3 | 4 | 5 | | V-1 | Mfap5 |
| 8512 | 3 | 4 | 5 | | V-1 | Mfsd3 |
| 8513 | 3 | 4 | 5 | | V-1 | Mfsd5 |
| 8514 | 3 | 4 | 5 | | V-1 | Mfsd6l |
| 8515 | 3 | 4 | 5 | | V-1 | Mfsd7a |
| 8516 | 3 | 4 | 5 | | V-1 | Mgat1 |
| 8517 | 3 | 4 | 5 | | V-1 | Mgat2 |
| 8518 | 3 | 4 | 5 | | V-1 | Mgat3 |
| 8519 | 3 | 4 | 5 | | V-1 | Mgl2 |
| 8520 | 3 | 4 | 5 | | V-1 | Mgll |
| 8521 | 3 | 4 | 5 | | V-1 | Mia3 |
| 8522 | 3 | 4 | 5 | | V-1 | Miat |
| 8523 | 3 | 4 | 5 | | V-1 | Mical1 |
| 8524 | 3 | 4 | 5 | | V-1 | Mical2 |
| 8525 | 3 | 4 | 5 | | V-1 | Mid1 |
| 8526 | 3 | 4 | 5 | | V-1 | Mid2 |
| 8527 | 3 | 4 | 5 | | V-1 | Midn |
| 8528 | 3 | 4 | 5 | | V-1 | Mif |
| 8529 | 3 | 4 | 5 | | V-1 | Mif4gd |
| 8530 | 3 | 4 | 5 | | V-1 | Minos1 |
| 8531 | 3 | 4 | 5 | | V-1 | Mipol1 |
| 8532 | 3 | 4 | 5 | | V-1 | Mir143hg |
| 8533 | 3 | 4 | 5 | | V-1 | Mir17hg |
| 8534 | 3 | 4 | 5 | | V-1 | Mis12 |
| 8535 | 3 | 4 | 5 | | V-1 | Mis18bp1 |
| 8536 | 3 | 4 | 5 | | V-1 | Misp |
| 8537 | 3 | 4 | 5 | | V-1 | Mitd1 |
| 8538 | 3 | 4 | 5 | | V-1 | Mki67 |
| 8539 | 3 | 4 | 5 | | V-1 | Mkln1 |
| 8540 | 3 | 4 | 5 | | V-1 | Mlana |
| 8541 | 3 | 4 | 5 | | V-1 | Mlec |
| 8542 | 3 | 4 | 5 | | V-1 | Mlkl |
| 8543 | 3 | 4 | 5 | | V-1 | Mllt1 |
| 8544 | 3 | 4 | 5 | | V-1 | Mmadhc |
| 8545 | 3 | 4 | 5 | | V-1 | Mmgt2 |
| 8546 | 3 | 4 | 5 | | V-1 | Mmp10 |
| 8547 | 3 | 4 | 5 | | V-1 | Mmp14 |
| 8548 | 3 | 4 | 5 | | V-1 | Mmp16 |
| 8549 | 3 | 4 | 5 | | V-1 | Mmp17 |
| 8550 | 3 | 4 | 5 | | V-1 | Mmp19 |
| 8551 | 3 | 4 | 5 | | V-1 | Mmp25 |
| 8552 | 3 | 4 | 5 | | V-1 | Mmp28 |
| 8553 | 3 | 4 | 5 | | V-1 | Mmp3 |
| 8554 | 3 | 4 | 5 | | V-1 | Mmp8 |
| 8555 | 3 | 4 | 5 | | V-1 | Mmp9 |
| 8556 | 3 | 4 | 5 | | V-1 | Mms22l |
| 8557 | 3 | 4 | 5 | | V-1 | Mnd1 |
| 8558 | 3 | 4 | 5 | | V-1 | Mob3a |
| 8559 | 3 | 4 | 5 | | V-1 | Mocos |
| 8560 | 3 | 4 | 5 | | V-1 | Mocs1 |
| 8561 | 3 | 4 | 5 | | V-1 | Mocs3 |
| 8562 | 3 | 4 | 5 | | V-1 | Mogat1 |
| 8563 | 3 | 4 | 5 | | V-1 | Mok |
| 8564 | 3 | 4 | 5 | | V-1 | Morn3 |
| 8565 | 3 | 4 | 5 | | V-1 | Morn5 |
| 8566 | 3 | 4 | 5 | | V-1 | Mospd3 |
| 8567 | 3 | 4 | 5 | | V-1 | Mov10 |
| 8568 | 3 | 4 | 5 | | V-1 | Mpdu1 |
| 8569 | 3 | 4 | 5 | | V-1 | Mphosph6 |
| 8570 | 3 | 4 | 5 | | V-1 | Mpnd |
| 8571 | 3 | 4 | 5 | | V-1 | Mpp3 |
| 8572 | 3 | 4 | 5 | | V-1 | Mpp7 |
| 8573 | 3 | 4 | 5 | | V-1 | Mpzl2 |
| 8574 | 3 | 4 | 5 | | V-1 | Mre11a |
| 8575 | 3 | 4 | 5 | | V-1 | Mrgbp |
| 8576 | 3 | 4 | 5 | | V-1 | Mrgprh |
| 8577 | 3 | 4 | 5 | | V-1 | Mroh1 |
| 8578 | 3 | 4 | 5 | | V-1 | Mrpl12 |
| 8579 | 3 | 4 | 5 | | V-1 | Mrpl18 |
| 8580 | 3 | 4 | 5 | | V-1 | Mrpl2 |
| 8581 | 3 | 4 | 5 | | V-1 | Mrpl22 |
| 8582 | 3 | 4 | 5 | | V-1 | Mrpl27 |
| 8583 | 3 | 4 | 5 | | V-1 | Mrpl36 |
| 8584 | 3 | 4 | 5 | | V-1 | Mrpl37 |
| 8585 | 3 | 4 | 5 | | V-1 | Mrpl4 |
| 8586 | 3 | 4 | 5 | | V-1 | Mrpl40 |
| 8587 | 3 | 4 | 5 | | V-1 | Mrpl46 |
| 8588 | 3 | 4 | 5 | | V-1 | Mrpl48 |
| 8589 | 3 | 4 | 5 | | V-1 | Mrpl51 |
| 8590 | 3 | 4 | 5 | | V-1 | Mrpl53 |
| 8591 | 3 | 4 | 5 | | V-1 | Mrpl55 |
| 8592 | 3 | 4 | 5 | | V-1 | Mrps12 |
| 8593 | 3 | 4 | 5 | | V-1 | Mrps15 |
| 8594 | 3 | 4 | 5 | | V-1 | Mrps25 |
| 8595 | 3 | 4 | 5 | | V-1 | Mrps33 |
| 8596 | 3 | 4 | 5 | | V-1 | Mrps35 |
| 8597 | 3 | 4 | 5 | | V-1 | Mrps36 |
| 8598 | 3 | 4 | 5 | | V-1 | Mrps7 |
| 8599 | 3 | 4 | 5 | | V-1 | Mrto4 |
| 8600 | 3 | 4 | 5 | | V-1 | Ms4a4c |
| 8601 | 3 | 4 | 5 | | V-1 | Ms4a6b |
| 8602 | 3 | 4 | 5 | | V-1 | Msantd3 |
| 8603 | 3 | 4 | 5 | | V-1 | Msh2 |
| 8604 | 3 | 4 | 5 | | V-1 | Msh6 |
| 8605 | 3 | 4 | 5 | | V-1 | Msi1 |
| 8606 | 3 | 4 | 5 | | V-1 | Msmo1 |
| 8607 | 3 | 4 | 5 | | V-1 | Msra |
| 8608 | 3 | 4 | 5 | | V-1 | Msrb2 |
| 8609 | 3 | 4 | 5 | | V-1 | Mss51 |
| 8610 | 3 | 4 | 5 | | V-1 | Mst1r |
| 8611 | 3 | 4 | 5 | | V-1 | Msx1os |
| 8612 | 3 | 4 | 5 | | V-1 | Msx2 |
| 8613 | 3 | 4 | 5 | | V-1 | Mtbp |
| 8614 | 3 | 4 | 5 | | V-1 | Mtcl1 |
| 8615 | 3 | 4 | 5 | | V-1 | Mtcp1 |
| 8616 | 3 | 4 | 5 | | V-1 | Mterf1b |
| 8617 | 3 | 4 | 5 | | V-1 | Mterfd1 |
| 8618 | 3 | 4 | 5 | | V-1 | Mterfd3 |
| 8619 | 3 | 4 | 5 | | V-1 | Mtf2 |
| 8620 | 3 | 4 | 5 | | V-1 | Mtfp1 |
| 8621 | 3 | 4 | 5 | | V-1 | Mtfr2 |
| 8622 | 3 | 4 | 5 | | V-1 | Mtg1 |
| 8623 | 3 | 4 | 5 | | V-1 | Mthfr |
| 8624 | 3 | 4 | 5 | | V-1 | Mtif2 |
| 8625 | 3 | 4 | 5 | | V-1 | Mtmr7 |
| 8626 | 3 | 4 | 5 | | V-1 | Mtr |
| 8627 | 3 | 4 | 5 | | V-1 | Mtus1 |
| 8628 | 3 | 4 | 5 | | V-1 | Muc1 |
| 8629 | 3 | 4 | 5 | | V-1 | Muc2 |
| 8630 | 3 | 4 | 5 | | V-1 | Muc4 |
| 8631 | 3 | 4 | 5 | | V-1 | Mucl1 |
| 8632 | 3 | 4 | 5 | | V-1 | Mup19 |
| 8633 | 3 | 4 | 5 | | V-1 | Mup20 |
| 8634 | 3 | 4 | 5 | | V-1 | Mup7 |
| 8635 | 3 | 4 | 5 | | V-1 | Mus81 |
| 8636 | 3 | 4 | 5 | | V-1 | Myb12a |
| 8637 | 3 | 4 | 5 | | V-1 | Mvd |
| 8638 | 3 | 4 | 5 | | V-1 | Mvk |

Fig. 36 - 46

| | | | | | | |
|---|---|---|---|---|---|---|
| 8639 | 3 | 4 | 5 | | V-1 | Mvp |
| 8640 | 3 | 4 | 5 | | V-1 | Mx2 |
| 8641 | 3 | 4 | 5 | | V-1 | Mxd1 |
| 8642 | 3 | 4 | 5 | | V-1 | Mxd4 |
| 8643 | 3 | 4 | 5 | | V-1 | Myadm |
| 8644 | 3 | 4 | 5 | | V-1 | Mybpc1 |
| 8645 | 3 | 4 | 5 | | V-1 | Mycbp2 |
| 8646 | 3 | 4 | 5 | | V-1 | Myct1 |
| 8647 | 3 | 4 | 5 | | V-1 | Myeov2 |
| 8648 | 3 | 4 | 5 | | V-1 | Myh1 |
| 8649 | 3 | 4 | 5 | | V-1 | Myh2 |
| 8650 | 3 | 4 | 5 | | V-1 | Myh8 |
| 8651 | 3 | 4 | 5 | | V-1 | Myh9 |
| 8652 | 3 | 4 | 5 | | V-1 | Myl12a |
| 8653 | 3 | 4 | 5 | | V-1 | Myl2 |
| 8654 | 3 | 4 | 5 | | V-1 | Myl3 |
| 8655 | 3 | 4 | 5 | | V-1 | Mylk2 |
| 8656 | 3 | 4 | 5 | | V-1 | Mylk4 |
| 8657 | 3 | 4 | 5 | | V-1 | Myo16 |
| 8658 | 3 | 4 | 5 | | V-1 | Myo1a |
| 8659 | 3 | 4 | 5 | | V-1 | Myo1g |
| 8660 | 3 | 4 | 5 | | V-1 | Myoc |
| 8661 | 3 | 4 | 5 | | V-1 | Myof |
| 8662 | 3 | 4 | 5 | | V-1 | Myom1 |
| 8663 | 3 | 4 | 5 | | V-1 | Myom3 |
| 8664 | 3 | 4 | 5 | | V-1 | Myot |
| 8665 | 3 | 4 | 5 | | V-1 | Mypn |
| 8666 | 3 | 4 | 5 | | V-1 | Mysm1 |
| 8667 | 3 | 4 | 5 | | V-1 | N28178 |
| 8668 | 3 | 4 | 5 | | V-1 | N4bp2l2 |
| 8669 | 3 | 4 | 5 | | V-1 | N6amt2 |
| 8670 | 3 | 4 | 5 | | V-1 | Naa25 |
| 8671 | 3 | 4 | 5 | | V-1 | Naalad2 |
| 8672 | 3 | 4 | 5 | | V-1 | Naaladl1 |
| 8673 | 3 | 4 | 5 | | V-1 | Nacad |
| 8674 | 3 | 4 | 5 | | V-1 | Nadk |
| 8675 | 3 | 4 | 5 | | V-1 | Naif1 |
| 8676 | 3 | 4 | 5 | | V-1 | Naip1 |
| 8677 | 3 | 4 | 5 | | V-1 | Naip6 |
| 8678 | 3 | 4 | 5 | | V-1 | Nanp |
| 8679 | 3 | 4 | 5 | | V-1 | Nap1l3 |
| 8680 | 3 | 4 | 5 | | V-1 | Nap1l5 |
| 8681 | 3 | 4 | 5 | | V-1 | Napb |
| 8682 | 3 | 4 | 5 | | V-1 | Narf |
| 8683 | 3 | 4 | 5 | | V-1 | Nat14 |
| 8684 | 3 | 4 | 5 | | V-1 | Nat6 |
| 8685 | 3 | 4 | 5 | | V-1 | Nat9 |
| 8686 | 3 | 4 | 5 | | V-1 | Nav1 |
| 8687 | 3 | 4 | 5 | | V-1 | Nbeal2 |
| 8688 | 3 | 4 | 5 | | V-1 | Nbl1 |
| 8689 | 3 | 4 | 5 | | V-1 | Ncald |
| 8690 | 3 | 4 | 5 | | V-1 | Ncam1 |
| 8691 | 3 | 4 | 5 | | V-1 | Ncapg2 |
| 8692 | 3 | 4 | 5 | | V-1 | Ncaph |
| 8693 | 3 | 4 | 5 | | V-1 | Ncaph2 |
| 8694 | 3 | 4 | 5 | | V-1 | Ncbp1 |
| 8695 | 3 | 4 | 5 | | V-1 | Ncbp2 |
| 8696 | 3 | 4 | 5 | | V-1 | Ncf1 |
| 8697 | 3 | 4 | 5 | | V-1 | Ncf2 |
| 8698 | 3 | 4 | 5 | | V-1 | Nck1 |
| 8699 | 3 | 4 | 5 | | V-1 | Nckap1l |
| 8700 | 3 | 4 | 5 | | V-1 | Ncoa6 |
| 8701 | 3 | 4 | 5 | | V-1 | Ncor1 |
| 8702 | 3 | 4 | 5 | | V-1 | Ncor2 |
| 8703 | 3 | 4 | 5 | | V-1 | Ndc80 |
| 8704 | 3 | 4 | 5 | | V-1 | Ndel1 |
| 8705 | 3 | 4 | 5 | | V-1 | Ndfip1 |
| 8706 | 3 | 4 | 5 | | V-1 | Ndnl |
| 8707 | 3 | 4 | 5 | | V-1 | Ndrg1 |
| 8708 | 3 | 4 | 5 | | V-1 | Ndufa1 |
| 8709 | 3 | 4 | 5 | | V-1 | Ndufa11 |
| 8710 | 3 | 4 | 5 | | V-1 | Ndufa12 |
| 8711 | 3 | 4 | 5 | | V-1 | Ndufa2 |
| 8712 | 3 | 4 | 5 | | V-1 | Ndufa4 |
| 8713 | 3 | 4 | 5 | | V-1 | Ndufa7 |
| 8714 | 3 | 4 | 5 | | V-1 | Ndufa8 |
| 8715 | 3 | 4 | 5 | | V-1 | Ndufa9 |
| 8716 | 3 | 4 | 5 | | V-1 | Ndufab1 |
| 8717 | 3 | 4 | 5 | | V-1 | Ndufaf4 |
| 8718 | 3 | 4 | 5 | | V-1 | Ndufb2 |
| 8719 | 3 | 4 | 5 | | V-1 | Ndufb7 |
| 8720 | 3 | 4 | 5 | | V-1 | Ndufc1 |
| 8721 | 3 | 4 | 5 | | V-1 | Ndufs3 |
| 8722 | 3 | 4 | 5 | | V-1 | Ndufs6 |
| 8723 | 3 | 4 | 5 | | V-1 | Necab2 |
| 8724 | 3 | 4 | 5 | | V-1 | Nedd8 |
| 8725 | 3 | 4 | 5 | | V-1 | Nedd9 |
| 8726 | 3 | 4 | 5 | | V-1 | Nefl |
| 8727 | 3 | 4 | 5 | | V-1 | Neil1 |
| 8728 | 3 | 4 | 5 | | V-1 | Neil2 |
| 8729 | 3 | 4 | 5 | | V-1 | Nek2 |
| 8730 | 3 | 4 | 5 | | V-1 | Nek6 |
| 8731 | 3 | 4 | 5 | | V-1 | Nelfa |
| 8732 | 3 | 4 | 5 | | V-1 | Nelfcd |
| 8733 | 3 | 4 | 5 | | V-1 | Nenf |
| 8734 | 3 | 4 | 5 | | V-1 | Nes |
| 8735 | 3 | 4 | 5 | | V-1 | Neurl2 |
| 8736 | 3 | 4 | 5 | | V-1 | Nexn |
| 8737 | 3 | 4 | 5 | | V-1 | Nfat5 |
| 8738 | 3 | 4 | 5 | | V-1 | Nfic |
| 8739 | 3 | 4 | 5 | | V-1 | Nfkbid |
| 8740 | 3 | 4 | 5 | | V-1 | Nfkbie |
| 8741 | 3 | 4 | 5 | | V-1 | Nfkbiz |
| 8742 | 3 | 4 | 5 | | V-1 | Nfxl1 |
| 8743 | 3 | 4 | 5 | | V-1 | Ngb |
| 8744 | 3 | 4 | 5 | | V-1 | Ngdn |
| 8745 | 3 | 4 | 5 | | V-1 | Ngf |
| 8746 | 3 | 4 | 5 | | V-1 | Ngfr |
| 8747 | 3 | 4 | 5 | | V-1 | Nhej1 |
| 8748 | 3 | 4 | 5 | | V-1 | Nhlrc1 |
| 8749 | 3 | 4 | 5 | | V-1 | Nhp2 |
| 8750 | 3 | 4 | 5 | | V-1 | Nhsl1 |
| 8751 | 3 | 4 | 5 | | V-1 | Nhsl2 |
| 8752 | 3 | 4 | 5 | | V-1 | Nid1 |
| 8753 | 3 | 4 | 5 | | V-1 | Nid2 |
| 8754 | 3 | 4 | 5 | | V-1 | Nim1k |
| 8755 | 3 | 4 | 5 | | V-1 | Nin |
| 8756 | 3 | 4 | 5 | | V-1 | Ninj1 |
| 8757 | 3 | 4 | 5 | | V-1 | Nip7 |
| 8758 | 3 | 4 | 5 | | V-1 | Nipbl |
| 8759 | 3 | 4 | 5 | | V-1 | Nipsnap1 |
| 8760 | 3 | 4 | 5 | | V-1 | Nit2 |
| 8761 | 3 | 4 | 5 | | V-1 | Nkap1 |
| 8762 | 3 | 4 | 5 | | V-1 | Nkd1 |
| 8763 | 3 | 4 | 5 | | V-1 | Nkd2 |
| 8764 | 3 | 4 | 5 | | V-1 | Nkg7 |
| 8765 | 3 | 4 | 5 | | V-1 | Nkpd1 |
| 8766 | 3 | 4 | 5 | | V-1 | Nktr |
| 8767 | 3 | 4 | 5 | | V-1 | Nkx2-6 |
| 8768 | 3 | 4 | 5 | | V-1 | Nkx3-2 |
| 8769 | 3 | 4 | 5 | | V-1 | Nle1 |
| 8770 | 3 | 4 | 5 | | V-1 | Nlgn3 |
| 8771 | 3 | 4 | 5 | | V-1 | Nlrc4 |
| 8772 | 3 | 4 | 5 | | V-1 | Nlrp1b |
| 8773 | 3 | 4 | 5 | | V-1 | Nlrp3 |
| 8774 | 3 | 4 | 5 | | V-1 | Nme1 |
| 8775 | 3 | 4 | 5 | | V-1 | Nme6 |
| 8776 | 3 | 4 | 5 | | V-1 | Nme7 |
| 8777 | 3 | 4 | 5 | | V-1 | Nmi |
| 8778 | 3 | 4 | 5 | | V-1 | Nmnat1 |
| 8779 | 3 | 4 | 5 | | V-1 | Nmnat3 |
| 8780 | 3 | 4 | 5 | | V-1 | Nmrk1 |
| 8781 | 3 | 4 | 5 | | V-1 | Nmrk2 |
| 8782 | 3 | 4 | 5 | | V-1 | Noc2l |
| 8783 | 3 | 4 | 5 | | V-1 | Nod2 |
| 8784 | 3 | 4 | 5 | | V-1 | Nol8 |
| 8785 | 3 | 4 | 5 | | V-1 | Nolc1 |
| 8786 | 3 | 4 | 5 | | V-1 | Nono |
| 8787 | 3 | 4 | 5 | | V-1 | Nop2 |
| 8788 | 3 | 4 | 5 | | V-1 | Nos2 |
| 8789 | 3 | 4 | 5 | | V-1 | Nos3 |
| 8790 | 3 | 4 | 5 | | V-1 | Notch2 |
| 8791 | 3 | 4 | 5 | | V-1 | Notch3 |
| 8792 | 3 | 4 | 5 | | V-1 | Notch4 |
| 8793 | 3 | 4 | 5 | | V-1 | Noxa1 |
| 8794 | 3 | 4 | 5 | | V-1 | Npc1l1 |
| 8795 | 3 | 4 | 5 | | V-1 | Npdc1 |
| 8796 | 3 | 4 | 5 | | V-1 | Npff |
| 8797 | 3 | 4 | 5 | | V-1 | Npl |
| 8798 | 3 | 4 | 5 | | V-1 | Npm3 |
| 8799 | 3 | 4 | 5 | | V-1 | Npnt |
| 8800 | 3 | 4 | 5 | | V-1 | Nppa |
| 8801 | 3 | 4 | 5 | | V-1 | Npr3 |
| 8802 | 3 | 4 | 5 | | V-1 | Nprl2 |
| 8803 | 3 | 4 | 5 | | V-1 | Nprl3 |
| 8804 | 3 | 4 | 5 | | V-1 | Npy1r |
| 8805 | 3 | 4 | 5 | | V-1 | Nr0b2 |
| 8806 | 3 | 4 | 5 | | V-1 | Nr5a2 |
| 8807 | 3 | 4 | 5 | | V-1 | Nrap |
| 8808 | 3 | 4 | 5 | | V-1 | Nrep |
| 8809 | 3 | 4 | 5 | | V-1 | Nrf1 |
| 8810 | 3 | 4 | 5 | | V-1 | Nrg4 |
| 8811 | 3 | 4 | 5 | | V-1 | Nrgn |
| 8812 | 3 | 4 | 5 | | V-1 | Nrip2 |
| 8813 | 3 | 4 | 5 | | V-1 | Nrm |
| 8814 | 3 | 4 | 5 | | V-1 | Nrn1l |
| 8815 | 3 | 4 | 5 | | V-1 | Nrp2 |
| 8816 | 3 | 4 | 5 | | V-1 | Nrtn |
| 8817 | 3 | 4 | 5 | | V-1 | Nsd1 |
| 8818 | 3 | 4 | 5 | | V-1 | Nsdhl |
| 8819 | 3 | 4 | 5 | | V-1 | Nsfl1c |
| 8820 | 3 | 4 | 5 | | V-1 | Nsmce1 |
| 8821 | 3 | 4 | 5 | | V-1 | Nsmf |
| 8822 | 3 | 4 | 5 | | V-1 | Nsun5 |
| 8823 | 3 | 4 | 5 | | V-1 | Nt5c |
| 8824 | 3 | 4 | 5 | | V-1 | Nt5c3 |
| 8825 | 3 | 4 | 5 | | V-1 | Nt5dc3 |
| 8826 | 3 | 4 | 5 | | V-1 | Nt5e |
| 8827 | 3 | 4 | 5 | | V-1 | Ntf5 |
| 8828 | 3 | 4 | 5 | | V-1 | Ntm |
| 8829 | 3 | 4 | 5 | | V-1 | Ntn4 |
| 8830 | 3 | 4 | 5 | | V-1 | Ntng2 |

Fig. 36 - 47

| | | | | | | |
|---|---|---|---|---|---|---|
| 8831 | 3 | 4 | 5 | | V-1 | Ntrk2 |
| 8832 | 3 | 4 | 5 | | V-1 | Nubp2 |
| 8833 | 3 | 4 | 5 | | V-1 | Nubpl |
| 8834 | 3 | 4 | 5 | | V-1 | Nucb2 |
| 8835 | 3 | 4 | 5 | | V-1 | Nudc |
| 8836 | 3 | 4 | 5 | | V-1 | Nudt1 |
| 8837 | 3 | 4 | 5 | | V-1 | Nudt10 |
| 8838 | 3 | 4 | 5 | | V-1 | Nudt12 |
| 8839 | 3 | 4 | 5 | | V-1 | Nudt14 |
| 8840 | 3 | 4 | 5 | | V-1 | Nudt15 |
| 8841 | 3 | 4 | 5 | | V-1 | Nudt16l1 |
| 8842 | 3 | 4 | 5 | | V-1 | Nudt17 |
| 8843 | 3 | 4 | 5 | | V-1 | Nudt21 |
| 8844 | 3 | 4 | 5 | | V-1 | Nudt22 |
| 8845 | 3 | 4 | 5 | | V-1 | Nudt8 |
| 8846 | 3 | 4 | 5 | | V-1 | Numa1 |
| 8847 | 3 | 4 | 5 | | V-1 | Nup107 |
| 8848 | 3 | 4 | 5 | | V-1 | Nup210 |
| 8849 | 3 | 4 | 5 | | V-1 | Nup37 |
| 8850 | 3 | 4 | 5 | | V-1 | Nupl1 |
| 8851 | 3 | 4 | 5 | | V-1 | Nutf2 |
| 8852 | 3 | 4 | 5 | | V-1 | Nvl |
| 8853 | 3 | 4 | 5 | | V-1 | Nwd2 |
| 8854 | 3 | 4 | 5 | | V-1 | Nxnl2 |
| 8855 | 3 | 4 | 5 | | V-1 | Nxpe5 |
| 8856 | 3 | 4 | 5 | | V-1 | Nynrin |
| 8857 | 3 | 4 | 5 | | V-1 | Nyx |
| 8858 | 3 | 4 | 5 | | V-1 | Oas1g |
| 8859 | 3 | 4 | 5 | | V-1 | Oas3 |
| 8860 | 3 | 4 | 5 | | V-1 | Obsl1 |
| 8861 | 3 | 4 | 5 | | V-1 | Odc1 |
| 8862 | 3 | 4 | 5 | | V-1 | Odf3 |
| 8863 | 3 | 4 | 5 | | V-1 | Ogdhl |
| 8864 | 3 | 4 | 5 | | V-1 | Ogfod3 |
| 8865 | 3 | 4 | 5 | | V-1 | Oit1 |
| 8866 | 3 | 4 | 5 | | V-1 | Olfml2a |
| 8867 | 3 | 4 | 5 | | V-1 | Olfr13 |
| 8868 | 3 | 4 | 5 | | V-1 | Olfr1396 |
| 8869 | 3 | 4 | 5 | | V-1 | Olfr1420 |
| 8870 | 3 | 4 | 5 | | V-1 | Olfr164 |
| 8871 | 3 | 4 | 5 | | V-1 | Olfr215 |
| 8872 | 3 | 4 | 5 | | V-1 | Olfr325 |
| 8873 | 3 | 4 | 5 | | V-1 | Olfr60 |
| 8874 | 3 | 4 | 5 | | V-1 | Olfr750 |
| 8875 | 3 | 4 | 5 | | V-1 | Olfr761 |
| 8876 | 3 | 4 | 5 | | V-1 | Olr1 |
| 8877 | 3 | 4 | 5 | | V-1 | Omp |
| 8878 | 3 | 4 | 5 | | V-1 | Onecut1 |
| 8879 | 3 | 4 | 5 | | V-1 | Opa3 |
| 8880 | 3 | 4 | 5 | | V-1 | Optc |
| 8881 | 3 | 4 | 5 | | V-1 | Orc6 |
| 8882 | 3 | 4 | 5 | | V-1 | Orm3 |
| 8883 | 3 | 4 | 5 | | V-1 | Osbpl10 |
| 8884 | 3 | 4 | 5 | | V-1 | Osbpl7 |
| 8885 | 3 | 4 | 5 | | V-1 | Osmr |
| 8886 | 3 | 4 | 5 | | V-1 | Osr1 |
| 8887 | 3 | 4 | 5 | | V-1 | Ostc |
| 8888 | 3 | 4 | 5 | | V-1 | Ostn |
| 8889 | 3 | 4 | 5 | | V-1 | Ovgp1 |
| 8890 | 3 | 4 | 5 | | V-1 | Ovol2 |
| 8891 | 3 | 4 | 5 | | V-1 | Oxld1 |
| 8892 | 3 | 4 | 5 | | V-1 | Oxtr |
| 8893 | 3 | 4 | 5 | | V-1 | P2rx6 |
| 8894 | 3 | 4 | 5 | | V-1 | P2rx7 |
| 8895 | 3 | 4 | 5 | | V-1 | P2ry13 |
| 8896 | 3 | 4 | 5 | | V-1 | P2ry2 |
| 8897 | 3 | 4 | 5 | | V-1 | P2ry6 |
| 8898 | 3 | 4 | 5 | | V-1 | P4ha1 |
| 8899 | 3 | 4 | 5 | | V-1 | P4htm |
| 8900 | 3 | 4 | 5 | | V-1 | Pabpc1l |
| 8901 | 3 | 4 | 5 | | V-1 | Pacrgl |
| 8902 | 3 | 4 | 5 | | V-1 | Pacs1 |
| 8903 | 3 | 4 | 5 | | V-1 | Pacsin1 |
| 8904 | 3 | 4 | 5 | | V-1 | Paf1 |
| 8905 | 3 | 4 | 5 | | V-1 | Pafah2 |
| 8906 | 3 | 4 | 5 | | V-1 | Pag1 |
| 8907 | 3 | 4 | 5 | | V-1 | Pah |
| 8908 | 3 | 4 | 5 | | V-1 | Pak4 |
| 8909 | 3 | 4 | 5 | | V-1 | Palm2 |
| 8910 | 3 | 4 | 5 | | V-1 | Palm3 |
| 8911 | 3 | 4 | 5 | | V-1 | Pan2 |
| 8912 | 3 | 4 | 5 | | V-1 | Pank1 |
| 8913 | 3 | 4 | 5 | | V-1 | Pank3 |
| 8914 | 3 | 4 | 5 | | V-1 | Panx1 |
| 8915 | 3 | 4 | 5 | | V-1 | Paox |
| 8916 | 3 | 4 | 5 | | V-1 | Papd4 |
| 8917 | 3 | 4 | 5 | | V-1 | Papln |
| 8918 | 3 | 4 | 5 | | V-1 | Pappa |
| 8919 | 3 | 4 | 5 | | V-1 | Papss2 |
| 8920 | 3 | 4 | 5 | | V-1 | Paqr5 |
| 8921 | 3 | 4 | 5 | | V-1 | Paqr9 |
| 8922 | 3 | 4 | 5 | | V-1 | Pard6b |
| 8923 | 3 | 4 | 5 | | V-1 | Pard6g |
| 8924 | 3 | 4 | 5 | | V-1 | Park2 |
| 8925 | 3 | 4 | 5 | | V-1 | Park7 |
| 8926 | 3 | 4 | 5 | | V-1 | Parp12 |

| | | | | | | |
|---|---|---|---|---|---|---|
| 8927 | 3 | 4 | 5 | | V-1 | Parp8 |
| 8928 | 3 | 4 | 5 | | V-1 | Pawr |
| 8929 | 3 | 4 | 5 | | V-1 | Paxip1 |
| 8930 | 3 | 4 | 5 | | V-1 | Pbk |
| 8931 | 3 | 4 | 5 | | V-1 | Pcbd2 |
| 8932 | 3 | 4 | 5 | | V-1 | Pcca |
| 8933 | 3 | 4 | 5 | | V-1 | Pcdh10 |
| 8934 | 3 | 4 | 5 | | V-1 | Pcdh11x |
| 8935 | 3 | 4 | 5 | | V-1 | Pcdh12 |
| 8936 | 3 | 4 | 5 | | V-1 | Pcdh15 |
| 8937 | 3 | 4 | 5 | | V-1 | Pcdh18 |
| 8938 | 3 | 4 | 5 | | V-1 | Pcdh9 |
| 8939 | 3 | 4 | 5 | | V-1 | Pcdha7 |
| 8940 | 3 | 4 | 5 | | V-1 | Pcdhb11 |
| 8941 | 3 | 4 | 5 | | V-1 | Pcdhb15 |
| 8942 | 3 | 4 | 5 | | V-1 | Pcdhb19 |
| 8943 | 3 | 4 | 5 | | V-1 | Pcdhb22 |
| 8944 | 3 | 4 | 5 | | V-1 | Pcdhb3 |
| 8945 | 3 | 4 | 5 | | V-1 | Pcdhb5 |
| 8946 | 3 | 4 | 5 | | V-1 | Pcdhb8 |
| 8947 | 3 | 4 | 5 | | V-1 | Pcdhga1 |
| 8948 | 3 | 4 | 5 | | V-1 | Pcdhga10 |
| 8949 | 3 | 4 | 5 | | V-1 | Pcdhga11 |
| 8950 | 3 | 4 | 5 | | V-1 | Pcdhga2 |
| 8951 | 3 | 4 | 5 | | V-1 | Pcdhga5 |
| 8952 | 3 | 4 | 5 | | V-1 | Pcdhga8 |
| 8953 | 3 | 4 | 5 | | V-1 | Pcdhgb4 |
| 8954 | 3 | 4 | 5 | | V-1 | Pcdhgb5 |
| 8955 | 3 | 4 | 5 | | V-1 | Pcdhgb7 |
| 8956 | 3 | 4 | 5 | | V-1 | Pcdhgc4 |
| 8957 | 3 | 4 | 5 | | V-1 | Pced1b |
| 8958 | 3 | 4 | 5 | | V-1 | Pcgf1 |
| 8959 | 3 | 4 | 5 | | V-1 | Pcgf3 |
| 8960 | 3 | 4 | 5 | | V-1 | Pcid2 |
| 8961 | 3 | 4 | 5 | | V-1 | Pclo |
| 8962 | 3 | 4 | 5 | | V-1 | Pcnx |
| 8963 | 3 | 4 | 5 | | V-1 | Pcnxl3 |
| 8964 | 3 | 4 | 5 | | V-1 | Pcsk1 |
| 8965 | 3 | 4 | 5 | | V-1 | Pcsk1n |
| 8966 | 3 | 4 | 5 | | V-1 | Pcsk4 |
| 8967 | 3 | 4 | 5 | | V-1 | Pcx |
| 8968 | 3 | 4 | 5 | | V-1 | Pcyox1l |
| 8969 | 3 | 4 | 5 | | V-1 | Pcyt2 |
| 8970 | 3 | 4 | 5 | | V-1 | Pdcd7 |
| 8971 | 3 | 4 | 5 | | V-1 | Pdcl3 |
| 8972 | 3 | 4 | 5 | | V-1 | Pde3b |
| 8973 | 3 | 4 | 5 | | V-1 | Pde4a |
| 8974 | 3 | 4 | 5 | | V-1 | Pde4b |
| 8975 | 3 | 4 | 5 | | V-1 | Pde4c |
| 8976 | 3 | 4 | 5 | | V-1 | Pde4d |
| 8977 | 3 | 4 | 5 | | V-1 | Pde4dip |
| 8978 | 3 | 4 | 5 | | V-1 | Pde6d |
| 8979 | 3 | 4 | 5 | | V-1 | Pde6g |
| 8980 | 3 | 4 | 5 | | V-1 | Pde8a |
| 8981 | 3 | 4 | 5 | | V-1 | Pdgfc |
| 8982 | 3 | 4 | 5 | | V-1 | Pdgfd |
| 8983 | 3 | 4 | 5 | | V-1 | Pdgfrl |
| 8984 | 3 | 4 | 5 | | V-1 | Pdhx |
| 8985 | 3 | 4 | 5 | | V-1 | Pdia3 |
| 8986 | 3 | 4 | 5 | | V-1 | Pdk4 |
| 8987 | 3 | 4 | 5 | | V-1 | Pdlim2 |
| 8988 | 3 | 4 | 5 | | V-1 | Pdlim4 |
| 8989 | 3 | 4 | 5 | | V-1 | Pdlim7 |
| 8990 | 3 | 4 | 5 | | V-1 | Pdpk1 |
| 8991 | 3 | 4 | 5 | | V-1 | Pdss1 |
| 8992 | 3 | 4 | 5 | | V-1 | Pdss2 |
| 8993 | 3 | 4 | 5 | | V-1 | Pdx1 |
| 8994 | 3 | 4 | 5 | | V-1 | Pdxk |
| 8995 | 3 | 4 | 5 | | V-1 | Pdzd11 |
| 8996 | 3 | 4 | 5 | | V-1 | Pdzd7 |
| 8997 | 3 | 4 | 5 | | V-1 | Pdzd8 |
| 8998 | 3 | 4 | 5 | | V-1 | Peak1 |
| 8999 | 3 | 4 | 5 | | V-1 | Pecr |
| 9000 | 3 | 4 | 5 | | V-1 | Pelo |
| 9001 | 3 | 4 | 5 | | V-1 | Penk |
| 9002 | 3 | 4 | 5 | | V-1 | Peo1 |
| 9003 | 3 | 4 | 5 | | V-1 | Perm1 |
| 9004 | 3 | 4 | 5 | | V-1 | Pex1 |
| 9005 | 3 | 4 | 5 | | V-1 | Pex11g |
| 9006 | 3 | 4 | 5 | | V-1 | Pex16 |
| 9007 | 3 | 4 | 5 | | V-1 | Pex7 |
| 9008 | 3 | 4 | 5 | | V-1 | Pf4 |
| 9009 | 3 | 4 | 5 | | V-1 | Pfdn4 |
| 9010 | 3 | 4 | 5 | | V-1 | Pfdn5 |
| 9011 | 3 | 4 | 5 | | V-1 | Pfkfb2 |
| 9012 | 3 | 4 | 5 | | V-1 | Pfkfb4 |
| 9013 | 3 | 4 | 5 | | V-1 | Pfn2 |
| 9014 | 3 | 4 | 5 | | V-1 | Pgap3 |
| 9015 | 3 | 4 | 5 | | V-1 | Pgf |
| 9016 | 3 | 4 | 5 | | V-1 | Pgls |
| 9017 | 3 | 4 | 5 | | V-1 | Pgp |
| 9018 | 3 | 4 | 5 | | V-1 | Pgpep1 |
| 9019 | 3 | 4 | 5 | | V-1 | Phactr2 |
| 9020 | 3 | 4 | 5 | | V-1 | Phb |
| 9021 | 3 | 4 | 5 | | V-1 | Phc3 |
| 9022 | 3 | 4 | 5 | | V-1 | Phf10 |

Fig. 36 - 48

| | | | | | | |
|---|---|---|---|---|---|---|
| 9023 | 3 | 4 | 5 | | V-1 | Phf19 |
| 9024 | 3 | 4 | 5 | | V-1 | Phf5a |
| 9025 | 3 | 4 | 5 | | V-1 | Phgdh |
| 9026 | 3 | 4 | 5 | | V-1 | Phka2 |
| 9027 | 3 | 4 | 5 | | V-1 | Phlda3 |
| 9028 | 3 | 4 | 5 | | V-1 | Phlpp2 |
| 9029 | 3 | 4 | 5 | | V-1 | Pi16 |
| 9030 | 3 | 4 | 5 | | V-1 | Pi4k2b |
| 9031 | 3 | 4 | 5 | | V-1 | Pi4ka |
| 9032 | 3 | 4 | 5 | | V-1 | Pid1 |
| 9033 | 3 | 4 | 5 | | V-1 | Piezo1 |
| 9034 | 3 | 4 | 5 | | V-1 | Pifo |
| 9035 | 3 | 4 | 5 | | V-1 | Pigb |
| 9036 | 3 | 4 | 5 | | V-1 | Pigf |
| 9037 | 3 | 4 | 5 | | V-1 | Pigg |
| 9038 | 3 | 4 | 5 | | V-1 | Pigx |
| 9039 | 3 | 4 | 5 | | V-1 | Pigz |
| 9040 | 3 | 4 | 5 | | V-1 | Pih1d2 |
| 9041 | 3 | 4 | 5 | | V-1 | Pik3cd |
| 9042 | 3 | 4 | 5 | | V-1 | Pik3r3 |
| 9043 | 3 | 4 | 5 | | V-1 | Pilrb1 |
| 9044 | 3 | 4 | 5 | | V-1 | Pilrb2 |
| 9045 | 3 | 4 | 5 | | V-1 | Pinx1 |
| 9046 | 3 | 4 | 5 | | V-1 | Pip5k1a |
| 9047 | 3 | 4 | 5 | | V-1 | Pirb |
| 9048 | 3 | 4 | 5 | | V-1 | Pirt |
| 9049 | 3 | 4 | 5 | | V-1 | Pisd-ps3 |
| 9050 | 3 | 4 | 5 | | V-1 | Pkd2l2 |
| 9051 | 3 | 4 | 5 | | V-1 | Pkdrej |
| 9052 | 3 | 4 | 5 | | V-1 | Pkhd1l1 |
| 9053 | 3 | 4 | 5 | | V-1 | Pkia |
| 9054 | 3 | 4 | 5 | | V-1 | Pkn1 |
| 9055 | 3 | 4 | 5 | | V-1 | Pla2g12b |
| 9056 | 3 | 4 | 5 | | V-1 | Pla2g2e |
| 9057 | 3 | 4 | 5 | | V-1 | Pla2g3 |
| 9058 | 3 | 4 | 5 | | V-1 | Pla2g4c |
| 9059 | 3 | 4 | 5 | | V-1 | Pla2g7 |
| 9060 | 3 | 4 | 5 | | V-1 | Plac8l1 |
| 9061 | 3 | 4 | 5 | | V-1 | Plau |
| 9062 | 3 | 4 | 5 | | V-1 | Plaur |
| 9063 | 3 | 4 | 5 | | V-1 | Plcb1 |
| 9064 | 3 | 4 | 5 | | V-1 | Plcb2 |
| 9065 | 3 | 4 | 5 | | V-1 | Plcd4 |
| 9066 | 3 | 4 | 5 | | V-1 | Plcl1 |
| 9067 | 3 | 4 | 5 | | V-1 | Plcxd1 |
| 9068 | 3 | 4 | 5 | | V-1 | Pld1 |
| 9069 | 3 | 4 | 5 | | V-1 | Pld2 |
| 9070 | 3 | 4 | 5 | | V-1 | Pld3 |
| 9071 | 3 | 4 | 5 | | V-1 | Plek2 |
| 9072 | 3 | 4 | 5 | | V-1 | Plekha3 |
| 9073 | 3 | 4 | 5 | | V-1 | Plekha5 |
| 9074 | 3 | 4 | 5 | | V-1 | Plekha7 |
| 9075 | 3 | 4 | 5 | | V-1 | Plekha8 |
| 9076 | 3 | 4 | 5 | | V-1 | Plekhb2 |
| 9077 | 3 | 4 | 5 | | V-1 | Plekhg1 |
| 9078 | 3 | 4 | 5 | | V-1 | Plekhm3 |
| 9079 | 3 | 4 | 5 | | V-1 | Plekho2 |
| 9080 | 3 | 4 | 5 | | V-1 | Plgrkt |
| 9081 | 3 | 4 | 5 | | V-1 | Plk1 |
| 9082 | 3 | 4 | 5 | | V-1 | Plk2 |
| 9083 | 3 | 4 | 5 | | V-1 | Plk4 |
| 9084 | 3 | 4 | 5 | | V-1 | Pllp |
| 9085 | 3 | 4 | 5 | | V-1 | Plp2 |
| 9086 | 3 | 4 | 5 | | V-1 | Pls3 |
| 9087 | 3 | 4 | 5 | | V-1 | Plscr2 |
| 9088 | 3 | 4 | 5 | | V-1 | Plscr3 |
| 9089 | 3 | 4 | 5 | | V-1 | Pltp |
| 9090 | 3 | 4 | 5 | | V-1 | Plxdc1 |
| 9091 | 3 | 4 | 5 | | V-1 | Plxdc2 |
| 9092 | 3 | 4 | 5 | | V-1 | Plxna1 |
| 9093 | 3 | 4 | 5 | | V-1 | Plxna2 |
| 9094 | 3 | 4 | 5 | | V-1 | Plxna3 |
| 9095 | 3 | 4 | 5 | | V-1 | Plxna4 |
| 9096 | 3 | 4 | 5 | | V-1 | Plxnb1 |
| 9097 | 3 | 4 | 5 | | V-1 | Plxnb2 |
| 9098 | 3 | 4 | 5 | | V-1 | Pm20d1 |
| 9099 | 3 | 4 | 5 | | V-1 | Pm20d2 |
| 9100 | 3 | 4 | 5 | | V-1 | Pmaip1 |
| 9101 | 3 | 4 | 5 | | V-1 | Pmf1 |
| 9102 | 3 | 4 | 5 | | V-1 | Pmm1 |
| 9103 | 3 | 4 | 5 | | V-1 | Pnkd |
| 9104 | 3 | 4 | 5 | | V-1 | Pnma1 |
| 9105 | 3 | 4 | 5 | | V-1 | Pnma2 |
| 9106 | 3 | 4 | 5 | | V-1 | Pnoc |
| 9107 | 3 | 4 | 5 | | V-1 | Pnrc1 |
| 9108 | 3 | 4 | 5 | | V-1 | Poc1a |
| 9109 | 3 | 4 | 5 | | V-1 | Pogk |
| 9110 | 3 | 4 | 5 | | V-1 | Pold2 |
| 9111 | 3 | 4 | 5 | | V-1 | Pole2 |
| 9112 | 3 | 4 | 5 | | V-1 | Pole3 |
| 9113 | 3 | 4 | 5 | | V-1 | Polh |
| 9114 | 3 | 4 | 5 | | V-1 | Polr1a |
| 9115 | 3 | 4 | 5 | | V-1 | Polr1c |
| 9116 | 3 | 4 | 5 | | V-1 | Polr2b |
| 9117 | 3 | 4 | 5 | | V-1 | Polr2e |
| 9118 | 3 | 4 | 5 | | V-1 | Polr2h |
| 9119 | 3 | 4 | 5 | | V-1 | Polr2i |
| 9120 | 3 | 4 | 5 | | V-1 | Polr2j |
| 9121 | 3 | 4 | 5 | | V-1 | Polr2l |
| 9122 | 3 | 4 | 5 | | V-1 | Polr2m |
| 9123 | 3 | 4 | 5 | | V-1 | Pomt2 |
| 9124 | 3 | 4 | 5 | | V-1 | Pop1 |
| 9125 | 3 | 4 | 5 | | V-1 | Por |
| 9126 | 3 | 4 | 5 | | V-1 | Porcn |
| 9127 | 3 | 4 | 5 | | V-1 | Postn |
| 9128 | 3 | 4 | 5 | | V-1 | Pou2f1 |
| 9129 | 3 | 4 | 5 | | V-1 | Ppa1 |
| 9130 | 3 | 4 | 5 | | V-1 | Ppa2 |
| 9131 | 3 | 4 | 5 | | V-1 | Ppan |
| 9132 | 3 | 4 | 5 | | V-1 | Ppap2c |
| 9133 | 3 | 4 | 5 | | V-1 | Ppapdc1b |
| 9134 | 3 | 4 | 5 | | V-1 | Ppapdc3 |
| 9135 | 3 | 4 | 5 | | V-1 | Ppard |
| 9136 | 3 | 4 | 5 | | V-1 | Ppdpf |
| 9137 | 3 | 4 | 5 | | V-1 | Ppfibp2 |
| 9138 | 3 | 4 | 5 | | V-1 | Ppib |
| 9139 | 3 | 4 | 5 | | V-1 | Ppie |
| 9140 | 3 | 4 | 5 | | V-1 | Ppih |
| 9141 | 3 | 4 | 5 | | V-1 | Ppil2 |
| 9142 | 3 | 4 | 5 | | V-1 | Ppm1e |
| 9143 | 3 | 4 | 5 | | V-1 | Ppp1r15b |
| 9144 | 3 | 4 | 5 | | V-1 | Ppp1r26 |
| 9145 | 3 | 4 | 5 | | V-1 | Ppp1r3d |
| 9146 | 3 | 4 | 5 | | V-1 | Ppp1r9a |
| 9147 | 3 | 4 | 5 | | V-1 | Ppp2r2a |
| 9148 | 3 | 4 | 5 | | V-1 | Ppp2r3d |
| 9149 | 3 | 4 | 5 | | V-1 | Ppp4c |
| 9150 | 3 | 4 | 5 | | V-1 | Ppp4r2 |
| 9151 | 3 | 4 | 5 | | V-1 | Pprc1 |
| 9152 | 3 | 4 | 5 | | V-1 | Ppt1 |
| 9153 | 3 | 4 | 5 | | V-1 | Pqbp1 |
| 9154 | 3 | 4 | 5 | | V-1 | Pqlc2 |
| 9155 | 3 | 4 | 5 | | V-1 | Pradc1 |
| 9156 | 3 | 4 | 5 | | V-1 | Prc1 |
| 9157 | 3 | 4 | 5 | | V-1 | Prcc |
| 9158 | 3 | 4 | 5 | | V-1 | Prdm16 |
| 9159 | 3 | 4 | 5 | | V-1 | Prdm2 |
| 9160 | 3 | 4 | 5 | | V-1 | Prdx1 |
| 9161 | 3 | 4 | 5 | | V-1 | Prdx2 |
| 9162 | 3 | 4 | 5 | | V-1 | Prelid1 |
| 9163 | 3 | 4 | 5 | | V-1 | Prepl |
| 9164 | 3 | 4 | 5 | | V-1 | Prex2 |
| 9165 | 3 | 4 | 5 | | V-1 | Prf1 |
| 9166 | 3 | 4 | 5 | | V-1 | Prickle2 |
| 9167 | 3 | 4 | 5 | | V-1 | Prickle4 |
| 9168 | 3 | 4 | 5 | | V-1 | Prim2 |
| 9169 | 3 | 4 | 5 | | V-1 | Prima1 |
| 9170 | 3 | 4 | 5 | | V-1 | Prkar2a |
| 9171 | 3 | 4 | 5 | | V-1 | Prkca |
| 9172 | 3 | 4 | 5 | | V-1 | Prkcb |
| 9173 | 3 | 4 | 5 | | V-1 | Prkcz |
| 9174 | 3 | 4 | 5 | | V-1 | Prkdc |
| 9175 | 3 | 4 | 5 | | V-1 | Prkg1 |
| 9176 | 3 | 4 | 5 | | V-1 | Prkx |
| 9177 | 3 | 4 | 5 | | V-1 | Prmt1 |
| 9178 | 3 | 4 | 5 | | V-1 | Prmt7 |
| 9179 | 3 | 4 | 5 | | V-1 | Prnd |
| 9180 | 3 | 4 | 5 | | V-1 | Prnp |
| 9181 | 3 | 4 | 5 | | V-1 | Proc |
| 9182 | 3 | 4 | 5 | | V-1 | Proca1 |
| 9183 | 3 | 4 | 5 | | V-1 | Procr |
| 9184 | 3 | 4 | 5 | | V-1 | Proser1 |
| 9185 | 3 | 4 | 5 | | V-1 | Prpf4b |
| 9186 | 3 | 4 | 5 | | V-1 | Prpf8 |
| 9187 | 3 | 4 | 5 | | V-1 | Prps2 |
| 9188 | 3 | 4 | 5 | | V-1 | Prr11 |
| 9189 | 3 | 4 | 5 | | V-1 | Prr12 |
| 9190 | 3 | 4 | 5 | | V-1 | Prr14l |
| 9191 | 3 | 4 | 5 | | V-1 | Prr33 |
| 9192 | 3 | 4 | 5 | | V-1 | Prr5 |
| 9193 | 3 | 4 | 5 | | V-1 | Psca |
| 9194 | 3 | 4 | 5 | | V-1 | Psd3 |
| 9195 | 3 | 4 | 5 | | V-1 | Psen2 |
| 9196 | 3 | 4 | 5 | | V-1 | Psenen |
| 9197 | 3 | 4 | 5 | | V-1 | Psg16 |
| 9198 | 3 | 4 | 5 | | V-1 | Psma5 |
| 9199 | 3 | 4 | 5 | | V-1 | Psma7 |
| 9200 | 3 | 4 | 5 | | V-1 | Psmb1 |
| 9201 | 3 | 4 | 5 | | V-1 | Psmb3 |
| 9202 | 3 | 4 | 5 | | V-1 | Psmb5 |
| 9203 | 3 | 4 | 5 | | V-1 | Psmb6 |
| 9204 | 3 | 4 | 5 | | V-1 | Psmb7 |
| 9205 | 3 | 4 | 5 | | V-1 | Psmc1 |
| 9206 | 3 | 4 | 5 | | V-1 | Psmd11 |
| 9207 | 3 | 4 | 5 | | V-1 | Psmd13 |
| 9208 | 3 | 4 | 5 | | V-1 | Psme2 |
| 9209 | 3 | 4 | 5 | | V-1 | Psmg2 |
| 9210 | 3 | 4 | 5 | | V-1 | Psmg4 |
| 9211 | 3 | 4 | 5 | | V-1 | Ptafr |
| 9212 | 3 | 4 | 5 | | V-1 | Ptbp1 |
| 9213 | 3 | 4 | 5 | | V-1 | Ptcd3 |
| 9214 | 3 | 4 | 5 | | V-1 | Ptdss2 |

Fig. 36 - 49

| | | | | | | | |
|---|---|---|---|---|---|---|---|
| 9215 | 3 | 4 | 5 | | V-1 | Ptger1 |
| 9216 | 3 | 4 | 5 | | V-1 | Ptger4 |
| 9217 | 3 | 4 | 5 | | V-1 | Ptges |
| 9218 | 3 | 4 | 5 | | V-1 | Ptk6 |
| 9219 | 3 | 4 | 5 | | V-1 | Ptk7 |
| 9220 | 3 | 4 | 5 | | V-1 | Ptms |
| 9221 | 3 | 4 | 5 | | V-1 | Ptn |
| 9222 | 3 | 4 | 5 | | V-1 | Ptov1 |
| 9223 | 3 | 4 | 5 | | V-1 | Ptplad2 |
| 9224 | 3 | 4 | 5 | | V-1 | Ptpn14 |
| 9225 | 3 | 4 | 5 | | V-1 | Ptpn6 |
| 9226 | 3 | 4 | 5 | | V-1 | Ptpra |
| 9227 | 3 | 4 | 5 | | V-1 | Ptprb |
| 9228 | 3 | 4 | 5 | | V-1 | Ptprc |
| 9229 | 3 | 4 | 5 | | V-1 | Ptprg |
| 9230 | 3 | 4 | 5 | | V-1 | Ptprh |
| 9231 | 3 | 4 | 5 | | V-1 | Ptprr |
| 9232 | 3 | 4 | 5 | | V-1 | Ptprt |
| 9233 | 3 | 4 | 5 | | V-1 | Ptprv |
| 9234 | 3 | 4 | 5 | | V-1 | Ptprz1 |
| 9235 | 3 | 4 | 5 | | V-1 | Pts |
| 9236 | 3 | 4 | 5 | | V-1 | Pttg1 |
| 9237 | 3 | 4 | 5 | | V-1 | Ptx3 |
| 9238 | 3 | 4 | 5 | | V-1 | Pum1 |
| 9239 | 3 | 4 | 5 | | V-1 | Purb |
| 9240 | 3 | 4 | 5 | | V-1 | Purg |
| 9241 | 3 | 4 | 5 | | V-1 | Pus1 |
| 9242 | 3 | 4 | 5 | | V-1 | Pvt1 |
| 9243 | 3 | 4 | 5 | | V-1 | Pwwp2b |
| 9244 | 3 | 4 | 5 | | V-1 | Pxmp4 |
| 9245 | 3 | 4 | 5 | | V-1 | Pycrl |
| 9246 | 3 | 4 | 5 | | V-1 | Pygm |
| 9247 | 3 | 4 | 5 | | V-1 | Pyy |
| 9248 | 3 | 4 | 5 | | V-1 | Qpctl |
| 9249 | 3 | 4 | 5 | | V-1 | Qrsl1 |
| 9250 | 3 | 4 | 5 | | V-1 | Qser1 |
| 9251 | 3 | 4 | 5 | | V-1 | Qsox2 |
| 9252 | 3 | 4 | 5 | | V-1 | Qtrt1 |
| 9253 | 3 | 4 | 5 | | V-1 | Rab1 |
| 9254 | 3 | 4 | 5 | | V-1 | Rab10os |
| 9255 | 3 | 4 | 5 | | V-1 | Rab11fip4os2 |
| 9256 | 3 | 4 | 5 | | V-1 | Rab15 |
| 9257 | 3 | 4 | 5 | | V-1 | Rab20 |
| 9258 | 3 | 4 | 5 | | V-1 | Rab27a |
| 9259 | 3 | 4 | 5 | | V-1 | Rab28 |
| 9260 | 3 | 4 | 5 | | V-1 | Rab30 |
| 9261 | 3 | 4 | 5 | | V-1 | Rab34 |
| 9262 | 3 | 4 | 5 | | V-1 | Rab36 |
| 9263 | 3 | 4 | 5 | | V-1 | Rab3a |
| 9264 | 3 | 4 | 5 | | V-1 | Rab3b |
| 9265 | 3 | 4 | 5 | | V-1 | Rab3c |
| 9266 | 3 | 4 | 5 | | V-1 | Rab3il1 |
| 9267 | 3 | 4 | 5 | | V-1 | Rab3ip |
| 9268 | 3 | 4 | 5 | | V-1 | Rab42 |
| 9269 | 3 | 4 | 5 | | V-1 | Rab43 |
| 9270 | 3 | 4 | 5 | | V-1 | Rab44 |
| 9271 | 3 | 4 | 5 | | V-1 | Rab4b |
| 9272 | 3 | 4 | 5 | | V-1 | Rab7l1 |
| 9273 | 3 | 4 | 5 | | V-1 | Rabggta |
| 9274 | 3 | 4 | 5 | | V-1 | Rabif |
| 9275 | 3 | 4 | 5 | | V-1 | Rac3 |
| 9276 | 3 | 4 | 5 | | V-1 | Rad1 |
| 9277 | 3 | 4 | 5 | | V-1 | Rad17 |
| 9278 | 3 | 4 | 5 | | V-1 | Rad18 |
| 9279 | 3 | 4 | 5 | | V-1 | Rad54l |
| 9280 | 3 | 4 | 5 | | V-1 | Rad54l2 |
| 9281 | 3 | 4 | 5 | | V-1 | Rad9a |
| 9282 | 3 | 4 | 5 | | V-1 | Rad9b |
| 9283 | 3 | 4 | 5 | | V-1 | Rae1 |
| 9284 | 3 | 4 | 5 | | V-1 | Rai1 |
| 9285 | 3 | 4 | 5 | | V-1 | Ralgapa2 |
| 9286 | 3 | 4 | 5 | | V-1 | Ralgapb |
| 9287 | 3 | 4 | 5 | | V-1 | Ranbp2 |
| 9288 | 3 | 4 | 5 | | V-1 | Rapgef3 |
| 9289 | 3 | 4 | 5 | | V-1 | Raph1 |
| 9290 | 3 | 4 | 5 | | V-1 | Rara |
| 9291 | 3 | 4 | 5 | | V-1 | Rarb |
| 9292 | 3 | 4 | 5 | | V-1 | Rars2 |
| 9293 | 3 | 4 | 5 | | V-1 | Rasa2 |
| 9294 | 3 | 4 | 5 | | V-1 | Rasal2 |
| 9295 | 3 | 4 | 5 | | V-1 | Rasal3 |
| 9296 | 3 | 4 | 5 | | V-1 | Rasd1 |
| 9297 | 3 | 4 | 5 | | V-1 | Rasd2 |
| 9298 | 3 | 4 | 5 | | V-1 | Rasgef1b |
| 9299 | 3 | 4 | 5 | | V-1 | Rasgrf1 |
| 9300 | 3 | 4 | 5 | | V-1 | Rasl12 |
| 9301 | 3 | 4 | 5 | | V-1 | Rassf4 |
| 9302 | 3 | 4 | 5 | | V-1 | Rassf9 |
| 9303 | 3 | 4 | 5 | | V-1 | Rb1cc1 |
| 9304 | 3 | 4 | 5 | | V-1 | Rbbp8 |
| 9305 | 3 | 4 | 5 | | V-1 | Rbfa |
| 9306 | 3 | 4 | 5 | | V-1 | Rbks |
| 9307 | 3 | 4 | 5 | | V-1 | Rbm12b1 |
| 9308 | 3 | 4 | 5 | | V-1 | Rbm14 |
| 9309 | 3 | 4 | 5 | | V-1 | Rbm26 |
| 9310 | 3 | 4 | 5 | | V-1 | Rbm3 |

| | | | | | | | |
|---|---|---|---|---|---|---|---|
| 9311 | 3 | 4 | 5 | | V-1 | Rbm33 |
| 9312 | 3 | 4 | 5 | | V-1 | Rbm3os |
| 9313 | 3 | 4 | 5 | | V-1 | Rbm48 |
| 9314 | 3 | 4 | 5 | | V-1 | Rbm6 |
| 9315 | 3 | 4 | 5 | | V-1 | Rbms1 |
| 9316 | 3 | 4 | 5 | | V-1 | Rbp1 |
| 9317 | 3 | 4 | 5 | | V-1 | Rbp7 |
| 9318 | 3 | 4 | 5 | | V-1 | Rbpms2 |
| 9319 | 3 | 4 | 5 | | V-1 | Rbx1 |
| 9320 | 3 | 4 | 5 | | V-1 | Rcn1 |
| 9321 | 3 | 4 | 5 | | V-1 | Rcor2 |
| 9322 | 3 | 4 | 5 | | V-1 | Rdh11 |
| 9323 | 3 | 4 | 5 | | V-1 | Rdh5 |
| 9324 | 3 | 4 | 5 | | V-1 | Reep1 |
| 9325 | 3 | 4 | 5 | | V-1 | Relt |
| 9326 | 3 | 4 | 5 | | V-1 | Rem1 |
| 9327 | 3 | 4 | 5 | | V-1 | Renbp |
| 9328 | 3 | 4 | 5 | | V-1 | Rep15 |
| 9329 | 3 | 4 | 5 | | V-1 | Rere |
| 9330 | 3 | 4 | 5 | | V-1 | Rev1 |
| 9331 | 3 | 4 | 5 | | V-1 | Rev3l |
| 9332 | 3 | 4 | 5 | | V-1 | Rex2 |
| 9333 | 3 | 4 | 5 | | V-1 | Rexo1 |
| 9334 | 3 | 4 | 5 | | V-1 | Rfc3 |
| 9335 | 3 | 4 | 5 | | V-1 | Rfx1 |
| 9336 | 3 | 4 | 5 | | V-1 | Rfx3 |
| 9337 | 3 | 4 | 5 | | V-1 | Rfx7 |
| 9338 | 3 | 4 | 5 | | V-1 | Rfxank |
| 9339 | 3 | 4 | 5 | | V-1 | Rgmb |
| 9340 | 3 | 4 | 5 | | V-1 | Rgn |
| 9341 | 3 | 4 | 5 | | V-1 | Rgs1 |
| 9342 | 3 | 4 | 5 | | V-1 | Rgs19 |
| 9343 | 3 | 4 | 5 | | V-1 | Rgs6 |
| 9344 | 3 | 4 | 5 | | V-1 | Rgs7bp |
| 9345 | 3 | 4 | 5 | | V-1 | Rhbdd1 |
| 9346 | 3 | 4 | 5 | | V-1 | Rhbdd3 |
| 9347 | 3 | 4 | 5 | | V-1 | Rhod |
| 9348 | 3 | 4 | 5 | | V-1 | Rhou |
| 9349 | 3 | 4 | 5 | | V-1 | Rhox3c |
| 9350 | 3 | 4 | 5 | | V-1 | Rhox3e |
| 9351 | 3 | 4 | 5 | | V-1 | Rhox3h |
| 9352 | 3 | 4 | 5 | | V-1 | Rhox4a |
| 9353 | 3 | 4 | 5 | | V-1 | Rhpn1 |
| 9354 | 3 | 4 | 5 | | V-1 | Rictor |
| 9355 | 3 | 4 | 5 | | V-1 | Rif1 |
| 9356 | 3 | 4 | 5 | | V-1 | Riipl1 |
| 9357 | 3 | 4 | 5 | | V-1 | Riipl2 |
| 9358 | 3 | 4 | 5 | | V-1 | Rimkla |
| 9359 | 3 | 4 | 5 | | V-1 | Rint1 |
| 9360 | 3 | 4 | 5 | | V-1 | Riok1 |
| 9361 | 3 | 4 | 5 | | V-1 | Ripk2 |
| 9362 | 3 | 4 | 5 | | V-1 | Rita1 |
| 9363 | 3 | 4 | 5 | | V-1 | Rlf |
| 9364 | 3 | 4 | 5 | | V-1 | Rln3 |
| 9365 | 3 | 4 | 5 | | V-1 | Rltpr |
| 9366 | 3 | 4 | 5 | | V-1 | Rmnd5b |
| 9367 | 3 | 4 | 5 | | V-1 | Rnase6 |
| 9368 | 3 | 4 | 5 | | V-1 | Rnaseh2a |
| 9369 | 3 | 4 | 5 | | V-1 | Rnaseh2b |
| 9370 | 3 | 4 | 5 | | V-1 | Rnaseh2c |
| 9371 | 3 | 4 | 5 | | V-1 | Rnd1 |
| 9372 | 3 | 4 | 5 | | V-1 | Rnd2 |
| 9373 | 3 | 4 | 5 | | V-1 | Rnf121 |
| 9374 | 3 | 4 | 5 | | V-1 | Rnf144a |
| 9375 | 3 | 4 | 5 | | V-1 | Rnf145 |
| 9376 | 3 | 4 | 5 | | V-1 | Rnf151 |
| 9377 | 3 | 4 | 5 | | V-1 | Rnf152 |
| 9378 | 3 | 4 | 5 | | V-1 | Rnf182 |
| 9379 | 3 | 4 | 5 | | V-1 | Rnf19a |
| 9380 | 3 | 4 | 5 | | V-1 | Rnf208 |
| 9381 | 3 | 4 | 5 | | V-1 | Rnf217 |
| 9382 | 3 | 4 | 5 | | V-1 | Rnf24 |
| 9383 | 3 | 4 | 5 | | V-1 | Rnf31 |
| 9384 | 3 | 4 | 5 | | V-1 | Rnf39 |
| 9385 | 3 | 4 | 5 | | V-1 | Rnft1 |
| 9386 | 3 | 4 | 5 | | V-1 | Rnft2 |
| 9387 | 3 | 4 | 5 | | V-1 | Rns |
| 9388 | 3 | 4 | 5 | | V-1 | Rnmtl1 |
| 9389 | 3 | 4 | 5 | | V-1 | Rnpepl1 |
| 9390 | 3 | 4 | 5 | | V-1 | Rora |
| 9391 | 3 | 4 | 5 | | V-1 | Rorc |
| 9392 | 3 | 4 | 5 | | V-1 | Rp2h |
| 9393 | 3 | 4 | 5 | | V-1 | Rpain |
| 9394 | 3 | 4 | 5 | | V-1 | Rpap3 |
| 9395 | 3 | 4 | 5 | | V-1 | Rpf1 |
| 9396 | 3 | 4 | 5 | | V-1 | Rpf2 |
| 9397 | 3 | 4 | 5 | | V-1 | Rph3al |
| 9398 | 3 | 4 | 5 | | V-1 | Rpl10a |
| 9399 | 3 | 4 | 5 | | V-1 | Rpl11 |
| 9400 | 3 | 4 | 5 | | V-1 | Rpl13 |
| 9401 | 3 | 4 | 5 | | V-1 | Rpl14 |
| 9402 | 3 | 4 | 5 | | V-1 | Rpl18 |
| 9403 | 3 | 4 | 5 | | V-1 | Rpl18a |
| 9404 | 3 | 4 | 5 | | V-1 | Rpl27 |
| 9405 | 3 | 4 | 5 | | V-1 | Rpl27a |
| 9406 | 3 | 4 | 5 | | V-1 | Rpl30 |

Fig. 36 - 50

| | | | | | | |
|---|---|---|---|---|---|---|
| 9407 | 3 | 4 | 5 | | V-1 | Rpl31 |
| 9408 | 3 | 4 | 5 | | V-1 | Rpl32 |
| 9409 | 3 | 4 | 5 | | V-1 | Rpl36 |
| 9410 | 3 | 4 | 5 | | V-1 | Rpl36al |
| 9411 | 3 | 4 | 5 | | V-1 | Rpl37 |
| 9412 | 3 | 4 | 5 | | V-1 | Rpl3l |
| 9413 | 3 | 4 | 5 | | V-1 | Rpl41 |
| 9414 | 3 | 4 | 5 | | V-1 | Rplp0 |
| 9415 | 3 | 4 | 5 | | V-1 | Rplp1 |
| 9416 | 3 | 4 | 5 | | V-1 | Rplp2-ps1 |
| 9417 | 3 | 4 | 5 | | V-1 | Rpn2 |
| 9418 | 3 | 4 | 5 | | V-1 | Rpp14 |
| 9419 | 3 | 4 | 5 | | V-1 | Rpp25 |
| 9420 | 3 | 4 | 5 | | V-1 | Rpp30 |
| 9421 | 3 | 4 | 5 | | V-1 | Rpp38 |
| 9422 | 3 | 4 | 5 | | V-1 | Rprd1a |
| 9423 | 3 | 4 | 5 | | V-1 | Rps10 |
| 9424 | 3 | 4 | 5 | | V-1 | Rps14 |
| 9425 | 3 | 4 | 5 | | V-1 | Rps15a |
| 9426 | 3 | 4 | 5 | | V-1 | Rps15a-ps6 |
| 9427 | 3 | 4 | 5 | | V-1 | Rps17 |
| 9428 | 3 | 4 | 5 | | V-1 | Rps19bp1 |
| 9429 | 3 | 4 | 5 | | V-1 | Rps24 |
| 9430 | 3 | 4 | 5 | | V-1 | Rps25 |
| 9431 | 3 | 4 | 5 | | V-1 | Rps3 |
| 9432 | 3 | 4 | 5 | | V-1 | Rps4x |
| 9433 | 3 | 4 | 5 | | V-1 | Rps5 |
| 9434 | 3 | 4 | 5 | | V-1 | Rps8 |
| 9435 | 3 | 4 | 5 | | V-1 | Rps9 |
| 9436 | 3 | 4 | 5 | | V-1 | Rpsa |
| 9437 | 3 | 4 | 5 | | V-1 | Rptoros |
| 9438 | 3 | 4 | 5 | | V-1 | Rpusd2 |
| 9439 | 3 | 4 | 5 | | V-1 | Rrad |
| 9440 | 3 | 4 | 5 | | V-1 | Rragd |
| 9441 | 3 | 4 | 5 | | V-1 | Rrbp1 |
| 9442 | 3 | 4 | 5 | | V-1 | Rrm2 |
| 9443 | 3 | 4 | 5 | | V-1 | Rrn3 |
| 9444 | 3 | 4 | 5 | | V-1 | Rrp1 |
| 9445 | 3 | 4 | 5 | | V-1 | Rrp12 |
| 9446 | 3 | 4 | 5 | | V-1 | Rrp15 |
| 9447 | 3 | 4 | 5 | | V-1 | Rrp1b |
| 9448 | 3 | 4 | 5 | | V-1 | Rrp36 |
| 9449 | 3 | 4 | 5 | | V-1 | Rrp7a |
| 9450 | 3 | 4 | 5 | | V-1 | Rrp8 |
| 9451 | 3 | 4 | 5 | | V-1 | Rrp9 |
| 9452 | 3 | 4 | 5 | | V-1 | Rsbn1 |
| 9453 | 3 | 4 | 5 | | V-1 | Rsl1 |
| 9454 | 3 | 4 | 5 | | V-1 | Rsl24d1 |
| 9455 | 3 | 4 | 5 | | V-1 | Rsph9 |
| 9456 | 3 | 4 | 5 | | V-1 | Rspo1 |
| 9457 | 3 | 4 | 5 | | V-1 | Rspo3 |
| 9458 | 3 | 4 | 5 | | V-1 | Rtdr1 |
| 9459 | 3 | 4 | 5 | | V-1 | Rtfdc1 |
| 9460 | 3 | 4 | 5 | | V-1 | Rtkn |
| 9461 | 3 | 4 | 5 | | V-1 | Rtn4r |
| 9462 | 3 | 4 | 5 | | V-1 | Rtn4rl1 |
| 9463 | 3 | 4 | 5 | | V-1 | Runx1 |
| 9464 | 3 | 4 | 5 | | V-1 | Ruvbl1 |
| 9465 | 3 | 4 | 5 | | V-1 | Rxrg |
| 9466 | 3 | 4 | 5 | | V-1 | Ryr1 |
| 9467 | 3 | 4 | 5 | | V-1 | S100a11 |
| 9468 | 3 | 4 | 5 | | V-1 | S100a16 |
| 9469 | 3 | 4 | 5 | | V-1 | S100a7a |
| 9470 | 3 | 4 | 5 | | V-1 | S1pr5 |
| 9471 | 3 | 4 | 5 | | V-1 | Sac3d1 |
| 9472 | 3 | 4 | 5 | | V-1 | Safb |
| 9473 | 3 | 4 | 5 | | V-1 | Safb2 |
| 9474 | 3 | 4 | 5 | | V-1 | Sall3 |
| 9475 | 3 | 4 | 5 | | V-1 | Samd15 |
| 9476 | 3 | 4 | 5 | | V-1 | Samd4 |
| 9477 | 3 | 4 | 5 | | V-1 | Samd8 |
| 9478 | 3 | 4 | 5 | | V-1 | Samd9l |
| 9479 | 3 | 4 | 5 | | V-1 | Samhd1 |
| 9480 | 3 | 4 | 5 | | V-1 | Samsn1 |
| 9481 | 3 | 4 | 5 | | V-1 | Sap30bp |
| 9482 | 3 | 4 | 5 | | V-1 | Sapcd1 |
| 9483 | 3 | 4 | 5 | | V-1 | Sash3 |
| 9484 | 3 | 4 | 5 | | V-1 | Sat1 |
| 9485 | 3 | 4 | 5 | | V-1 | Sbf2 |
| 9486 | 3 | 4 | 5 | | V-1 | Sbk1 |
| 9487 | 3 | 4 | 5 | | V-1 | Sbno2 |
| 9488 | 3 | 4 | 5 | | V-1 | Sbsn |
| 9489 | 3 | 4 | 5 | | V-1 | Scaf11 |
| 9490 | 3 | 4 | 5 | | V-1 | Scaf4 |
| 9491 | 3 | 4 | 5 | | V-1 | Scai |
| 9492 | 3 | 4 | 5 | | V-1 | Scarb2 |
| 9493 | 3 | 4 | 5 | | V-1 | Scd3 |
| 9494 | 3 | 4 | 5 | | V-1 | Scd4 |
| 9495 | 3 | 4 | 5 | | V-1 | Scgb1b24 |
| 9496 | 3 | 4 | 5 | | V-1 | Scgb2b7 |
| 9497 | 3 | 4 | 5 | | V-1 | Scly |
| 9498 | 3 | 4 | 5 | | V-1 | Scn1a |
| 9499 | 3 | 4 | 5 | | V-1 | Scn2b |
| 9500 | 3 | 4 | 5 | | V-1 | Scn3a |
| 9501 | 3 | 4 | 5 | | V-1 | Scn5a |
| 9502 | 3 | 4 | 5 | | V-1 | Scnm1 |

| | | | | | | |
|---|---|---|---|---|---|---|
| 9503 | 3 | 4 | 5 | | V-1 | Sco2 |
| 9504 | 3 | 4 | 5 | | V-1 | Scpep1os |
| 9505 | 3 | 4 | 5 | | V-1 | Scrib |
| 9506 | 3 | 4 | 5 | | V-1 | Scrn1 |
| 9507 | 3 | 4 | 5 | | V-1 | Scube2 |
| 9508 | 3 | 4 | 5 | | V-1 | Scube3 |
| 9509 | 3 | 4 | 5 | | V-1 | Sdc1 |
| 9510 | 3 | 4 | 5 | | V-1 | Sdc4 |
| 9511 | 3 | 4 | 5 | | V-1 | Sdcbp2 |
| 9512 | 3 | 4 | 5 | | V-1 | Sdccag8 |
| 9513 | 3 | 4 | 5 | | V-1 | Sdr39u1 |
| 9514 | 3 | 4 | 5 | | V-1 | Sec11c |
| 9515 | 3 | 4 | 5 | | V-1 | Sec16a |
| 9516 | 3 | 4 | 5 | | V-1 | Sec61a1 |
| 9517 | 3 | 4 | 5 | | V-1 | Secisbp2 |
| 9518 | 3 | 4 | 5 | | V-1 | Sel1l |
| 9519 | 3 | 4 | 5 | | V-1 | Selenbp1 |
| 9520 | 3 | 4 | 5 | | V-1 | Sell |
| 9521 | 3 | 4 | 5 | | V-1 | Selm |
| 9522 | 3 | 4 | 5 | | V-1 | Selplg |
| 9523 | 3 | 4 | 5 | | V-1 | Sema3b |
| 9524 | 3 | 4 | 5 | | V-1 | Sema3g |
| 9525 | 3 | 4 | 5 | | V-1 | Sema4d |
| 9526 | 3 | 4 | 5 | | V-1 | Sema4g |
| 9527 | 3 | 4 | 5 | | V-1 | Sema5a |
| 9528 | 3 | 4 | 5 | | V-1 | Sema6b |
| 9529 | 3 | 4 | 5 | | V-1 | Sema6c |
| 9530 | 3 | 4 | 5 | | V-1 | Sephs2 |
| 9531 | 3 | 4 | 5 | | V-1 | Sept14 |
| 9532 | 3 | 4 | 5 | | V-1 | Sept3 |
| 9533 | 3 | 4 | 5 | | V-1 | Sept5 |
| 9534 | 3 | 4 | 5 | | V-1 | Sergef |
| 9535 | 3 | 4 | 5 | | V-1 | Serinc1 |
| 9536 | 3 | 4 | 5 | | V-1 | Serpina11 |
| 9537 | 3 | 4 | 5 | | V-1 | Serpina3g |
| 9538 | 3 | 4 | 5 | | V-1 | Serpina3h |
| 9539 | 3 | 4 | 5 | | V-1 | Serpina7 |
| 9540 | 3 | 4 | 5 | | V-1 | Serpinh6b |
| 9541 | 3 | 4 | 5 | | V-1 | Serpinb9 |
| 9542 | 3 | 4 | 5 | | V-1 | Serpind1 |
| 9543 | 3 | 4 | 5 | | V-1 | Serpine1 |
| 9544 | 3 | 4 | 5 | | V-1 | Sertad1 |
| 9545 | 3 | 4 | 5 | | V-1 | Sertad4 |
| 9546 | 3 | 4 | 5 | | V-1 | Sesn2 |
| 9547 | 3 | 4 | 5 | | V-1 | Sestd1 |
| 9548 | 3 | 4 | 5 | | V-1 | Setbp1 |
| 9549 | 3 | 4 | 5 | | V-1 | Setd1a |
| 9550 | 3 | 4 | 5 | | V-1 | Setd1b |
| 9551 | 3 | 4 | 5 | | V-1 | Setd4 |
| 9552 | 3 | 4 | 5 | | V-1 | Setd6 |
| 9553 | 3 | 4 | 5 | | V-1 | Setd7 |
| 9554 | 3 | 4 | 5 | | V-1 | Setmar |
| 9555 | 3 | 4 | 5 | | V-1 | Setx |
| 9556 | 3 | 4 | 5 | | V-1 | Sf3a1 |
| 9557 | 3 | 4 | 5 | | V-1 | Sf3a2 |
| 9558 | 3 | 4 | 5 | | V-1 | Sf3b5 |
| 9559 | 3 | 4 | 5 | | V-1 | Sfi1 |
| 9560 | 3 | 4 | 5 | | V-1 | Sfpq |
| 9561 | 3 | 4 | 5 | | V-1 | Sft2d1 |
| 9562 | 3 | 4 | 5 | | V-1 | Sfxn1 |
| 9563 | 3 | 4 | 5 | | V-1 | Sfxn2 |
| 9564 | 3 | 4 | 5 | | V-1 | Sgcd |
| 9565 | 3 | 4 | 5 | | V-1 | Sgce |
| 9566 | 3 | 4 | 5 | | V-1 | Sgcz |
| 9567 | 3 | 4 | 5 | | V-1 | Sgk3 |
| 9568 | 3 | 4 | 5 | | V-1 | Sgol1 |
| 9569 | 3 | 4 | 5 | | V-1 | Sgsh |
| 9570 | 3 | 4 | 5 | | V-1 | Sgsm2 |
| 9571 | 3 | 4 | 5 | | V-1 | Sgtb |
| 9572 | 3 | 4 | 5 | | V-1 | Sh2b2 |
| 9573 | 3 | 4 | 5 | | V-1 | Sh2d1a |
| 9574 | 3 | 4 | 5 | | V-1 | Sh3bgr |
| 9575 | 3 | 4 | 5 | | V-1 | Sh3bgrl2 |
| 9576 | 3 | 4 | 5 | | V-1 | Sh3bgrl3 |
| 9577 | 3 | 4 | 5 | | V-1 | Sh3glb2 |
| 9578 | 3 | 4 | 5 | | V-1 | Sh3kbp1 |
| 9579 | 3 | 4 | 5 | | V-1 | Sh3pxd2a |
| 9580 | 3 | 4 | 5 | | V-1 | Sh3tc1 |
| 9581 | 3 | 4 | 5 | | V-1 | Sh3yl1 |
| 9582 | 3 | 4 | 5 | | V-1 | Shank3 |
| 9583 | 3 | 4 | 5 | | V-1 | Shb |
| 9584 | 3 | 4 | 5 | | V-1 | Shf |
| 9585 | 3 | 4 | 5 | | V-1 | Shisa2 |
| 9586 | 3 | 4 | 5 | | V-1 | Shisa6 |
| 9587 | 3 | 4 | 5 | | V-1 | Shisa7 |
| 9588 | 3 | 4 | 5 | | V-1 | Shox2 |
| 9589 | 3 | 4 | 5 | | V-1 | Shroom1 |
| 9590 | 3 | 4 | 5 | | V-1 | Shroom3 |
| 9591 | 3 | 4 | 5 | | V-1 | Siah3 |
| 9592 | 3 | 4 | 5 | | V-1 | Sigirr |
| 9593 | 3 | 4 | 5 | | V-1 | Siglece |
| 9594 | 3 | 4 | 5 | | V-1 | Siglecg |
| 9595 | 3 | 4 | 5 | | V-1 | Siglech |
| 9596 | 3 | 4 | 5 | | V-1 | Sigmar1 |
| 9597 | 3 | 4 | 5 | | V-1 | Sik3 |
| 9598 | 3 | 4 | 5 | | V-1 | Simc1 |

Fig. 36 - 51

| | | | | | | | |
|---|---|---|---|---|---|---|---|
| 9599 | 3 | 4 | 5 | | V-1 | Sin3b | |
| 9600 | 3 | 4 | 5 | | V-1 | Sipa1l2 | |
| 9601 | 3 | 4 | 5 | | V-1 | Sipa1l3 | |
| 9602 | 3 | 4 | 5 | | V-1 | Sirpb1a | |
| 9603 | 3 | 4 | 5 | | V-1 | Sirpb1b | |
| 9604 | 3 | 4 | 5 | | V-1 | Sirt5 | |
| 9605 | 3 | 4 | 5 | | V-1 | Sirt6 | |
| 9606 | 3 | 4 | 5 | | V-1 | Sirt7 | |
| 9607 | 3 | 4 | 5 | | V-1 | Skap1 | |
| 9608 | 3 | 4 | 5 | | V-1 | Ski | |
| 9609 | 3 | 4 | 5 | | V-1 | Skida1 | |
| 9610 | 3 | 4 | 5 | | V-1 | Skor1 | |
| 9611 | 3 | 4 | 5 | | V-1 | Skp2 | |
| 9612 | 3 | 4 | 5 | | V-1 | Slamf8 | |
| 9613 | 3 | 4 | 5 | | V-1 | Slbp | |
| 9614 | 3 | 4 | 5 | | V-1 | Slc11a1 | |
| 9615 | 3 | 4 | 5 | | V-1 | Slc13a5 | |
| 9616 | 3 | 4 | 5 | | V-1 | Slc14a1 | |
| 9617 | 3 | 4 | 5 | | V-1 | Slc15a3 | |
| 9618 | 3 | 4 | 5 | | V-1 | Slc16a1 | |
| 9619 | 3 | 4 | 5 | | V-1 | Slc16a10 | |
| 9620 | 3 | 4 | 5 | | V-1 | Slc16a12 | |
| 9621 | 3 | 4 | 5 | | V-1 | Slc16a2 | |
| 9622 | 3 | 4 | 5 | | V-1 | Slc16a3 | |
| 9623 | 3 | 4 | 5 | | V-1 | Slc16a6 | |
| 9624 | 3 | 4 | 5 | | V-1 | Slc16a8 | |
| 9625 | 3 | 4 | 5 | | V-1 | Slc1a2 | |
| 9626 | 3 | 4 | 5 | | V-1 | Slc22a12 | |
| 9627 | 3 | 4 | 5 | | V-1 | Slc22a17 | |
| 9628 | 3 | 4 | 5 | | V-1 | Slc22a18 | |
| 9629 | 3 | 4 | 5 | | V-1 | Slc22a23 | |
| 9630 | 3 | 4 | 5 | | V-1 | Slc22a3 | |
| 9631 | 3 | 4 | 5 | | V-1 | Slc22a7 | |
| 9632 | 3 | 4 | 5 | | V-1 | Slc24a2 | |
| 9633 | 3 | 4 | 5 | | V-1 | Slc24a3 | |
| 9634 | 3 | 4 | 5 | | V-1 | Slc24a4 | |
| 9635 | 3 | 4 | 5 | | V-1 | Slc25a1 | |
| 9636 | 3 | 4 | 5 | | V-1 | Slc25a10 | |
| 9637 | 3 | 4 | 5 | | V-1 | Slc25a15 | |
| 9638 | 3 | 4 | 5 | | V-1 | Slc25a22 | |
| 9639 | 3 | 4 | 5 | | V-1 | Slc25a23 | |
| 9640 | 3 | 4 | 5 | | V-1 | Slc25a24 | |
| 9641 | 3 | 4 | 5 | | V-1 | Slc25a29 | |
| 9642 | 3 | 4 | 5 | | V-1 | Slc25a30 | |
| 9643 | 3 | 4 | 5 | | V-1 | Slc25a32 | |
| 9644 | 3 | 4 | 5 | | V-1 | Slc25a35 | |
| 9645 | 3 | 4 | 5 | | V-1 | Slc25a36 | |
| 9646 | 3 | 4 | 5 | | V-1 | Slc25a42 | |
| 9647 | 3 | 4 | 5 | | V-1 | Slc25a45 | |
| 9648 | 3 | 4 | 5 | | V-1 | Slc25a5 | |
| 9649 | 3 | 4 | 5 | | V-1 | Slc26a1 | |
| 9650 | 3 | 4 | 5 | | V-1 | Slc26a6 | |
| 9651 | 3 | 4 | 5 | | V-1 | Slc27a3 | |
| 9652 | 3 | 4 | 5 | | V-1 | Slc27a6 | |
| 9653 | 3 | 4 | 5 | | V-1 | Slc29a2 | |
| 9654 | 3 | 4 | 5 | | V-1 | Slc29a3 | |
| 9655 | 3 | 4 | 5 | | V-1 | Slc2a12 | |
| 9656 | 3 | 4 | 5 | | V-1 | Slc30a10 | |
| 9657 | 3 | 4 | 5 | | V-1 | Slc30a7 | |
| 9658 | 3 | 4 | 5 | | V-1 | Slc36a1os | |
| 9659 | 3 | 4 | 5 | | V-1 | Slc37a2 | |
| 9660 | 3 | 4 | 5 | | V-1 | Slc38a3 | |
| 9661 | 3 | 4 | 5 | | V-1 | Slc39a1 | |
| 9662 | 3 | 4 | 5 | | V-1 | Slc40a1 | |
| 9663 | 3 | 4 | 5 | | V-1 | Slc41a2 | |
| 9664 | 3 | 4 | 5 | | V-1 | Slc46a1 | |
| 9665 | 3 | 4 | 5 | | V-1 | Slc47a1 | |
| 9666 | 3 | 4 | 5 | | V-1 | Slc47a2 | |
| 9667 | 3 | 4 | 5 | | V-1 | Slc4a4 | |
| 9668 | 3 | 4 | 5 | | V-1 | Slc52a3 | |
| 9669 | 3 | 4 | 5 | | V-1 | Slc5a1 | |
| 9670 | 3 | 4 | 5 | | V-1 | Slc5a3 | |
| 9671 | 3 | 4 | 5 | | V-1 | Slc5a7 | |
| 9672 | 3 | 4 | 5 | | V-1 | Slc6a13 | |
| 9673 | 3 | 4 | 5 | | V-1 | Slc6a17 | |
| 9674 | 3 | 4 | 5 | | V-1 | Slc6a20a | |
| 9675 | 3 | 4 | 5 | | V-1 | Slc6a8 | |
| 9676 | 3 | 4 | 5 | | V-1 | Slc7a10 | |
| 9677 | 3 | 4 | 5 | | V-1 | Slc7a14 | |
| 9678 | 3 | 4 | 5 | | V-1 | Slc7a2 | |
| 9679 | 3 | 4 | 5 | | V-1 | Slc7a3 | |
| 9680 | 3 | 4 | 5 | | V-1 | Slc7a7 | |
| 9681 | 3 | 4 | 5 | | V-1 | Slc8a1 | |
| 9682 | 3 | 4 | 5 | | V-1 | Slc9a2 | |
| 9683 | 3 | 4 | 5 | | V-1 | Slc9a3r1 | |
| 9684 | 3 | 4 | 5 | | V-1 | Slc9a3r2 | |
| 9685 | 3 | 4 | 5 | | V-1 | Slfn3 | |
| 9686 | 3 | 4 | 5 | | V-1 | Slfn5 | |
| 9687 | 3 | 4 | 5 | | V-1 | Slfn5os | |
| 9688 | 3 | 4 | 5 | | V-1 | Slfn8 | |
| 9689 | 3 | 4 | 5 | | V-1 | Slit1 | |
| 9690 | 3 | 4 | 5 | | V-1 | Slit3 | |
| 9691 | 3 | 4 | 5 | | V-1 | Slitrk4 | |
| 9692 | 3 | 4 | 5 | | V-1 | Slitrk6 | |
| 9693 | 3 | 4 | 5 | | V-1 | Slx4 | |
| 9694 | 3 | 4 | 5 | | V-1 | Smad3 | |
| 9695 | 3 | 4 | 5 | | V-1 | Smad7 | |
| 9696 | 3 | 4 | 5 | | V-1 | Smad9 | |
| 9697 | 3 | 4 | 5 | | V-1 | Smagp | |
| 9698 | 3 | 4 | 5 | | V-1 | Smc2 | |
| 9699 | 3 | 4 | 5 | | V-1 | Smco1 | |
| 9700 | 3 | 4 | 5 | | V-1 | Smco4 | |
| 9701 | 3 | 4 | 5 | | V-1 | Smcr8 | |
| 9702 | 3 | 4 | 5 | | V-1 | Smg1 | |
| 9703 | 3 | 4 | 5 | | V-1 | Smim15 | |
| 9704 | 3 | 4 | 5 | | V-1 | Smim3 | |
| 9705 | 3 | 4 | 5 | | V-1 | Smim5 | |
| 9706 | 3 | 4 | 5 | | V-1 | Smn1 | |
| 9707 | 3 | 4 | 5 | | V-1 | Smndc1 | |
| 9708 | 3 | 4 | 5 | | V-1 | Smox | |
| 9709 | 3 | 4 | 5 | | V-1 | Smpx | |
| 9710 | 3 | 4 | 5 | | V-1 | Sms | |
| 9711 | 3 | 4 | 5 | | V-1 | Smyd1 | |
| 9712 | 3 | 4 | 5 | | V-1 | Smyd2 | |
| 9713 | 3 | 4 | 5 | | V-1 | Snai1 | |
| 9714 | 3 | 4 | 5 | | V-1 | Snapc1 | |
| 9715 | 3 | 4 | 5 | | V-1 | Snapc2 | |
| 9716 | 3 | 4 | 5 | | V-1 | Snapc4 | |
| 9717 | 3 | 4 | 5 | | V-1 | Snca | |
| 9718 | 3 | 4 | 5 | | V-1 | Sncg | |
| 9719 | 3 | 4 | 5 | | V-1 | Sned1 | |
| 9720 | 3 | 4 | 5 | | V-1 | Snf8 | |
| 9721 | 3 | 4 | 5 | | V-1 | Snhg12 | |
| 9722 | 3 | 4 | 5 | | V-1 | Snhg18 | |
| 9723 | 3 | 4 | 5 | | V-1 | Snhg4 | |
| 9724 | 3 | 4 | 5 | | V-1 | Snhg7 | |
| 9725 | 3 | 4 | 5 | | V-1 | Snip1 | |
| 9726 | 3 | 4 | 5 | | V-1 | Snrnp200 | |
| 9727 | 3 | 4 | 5 | | V-1 | Snrnp25 | |
| 9728 | 3 | 4 | 5 | | V-1 | Snrnp70 | |
| 9729 | 3 | 4 | 5 | | V-1 | Snrpa1 | |
| 9730 | 3 | 4 | 5 | | V-1 | Snrpb | |
| 9731 | 3 | 4 | 5 | | V-1 | Snrpd2 | |
| 9732 | 3 | 4 | 5 | | V-1 | Snrpd3 | |
| 9733 | 3 | 4 | 5 | | V-1 | Snrpn | |
| 9734 | 3 | 4 | 5 | | V-1 | Snx16 | |
| 9735 | 3 | 4 | 5 | | V-1 | Snx20 | |
| 9736 | 3 | 4 | 5 | | V-1 | Snx27 | |
| 9737 | 3 | 4 | 5 | | V-1 | Snx30 | |
| 9738 | 3 | 4 | 5 | | V-1 | Snx32 | |
| 9739 | 3 | 4 | 5 | | V-1 | Snx7 | |
| 9740 | 3 | 4 | 5 | | V-1 | Snx9 | |
| 9741 | 3 | 4 | 5 | | V-1 | Soat1 | |
| 9742 | 3 | 4 | 5 | | V-1 | Socs1 | |
| 9743 | 3 | 4 | 5 | | V-1 | Socs2 | |
| 9744 | 3 | 4 | 5 | | V-1 | Socs6 | |
| 9745 | 3 | 4 | 5 | | V-1 | Socs7 | |
| 9746 | 3 | 4 | 5 | | V-1 | Son | |
| 9747 | 3 | 4 | 5 | | V-1 | Sostdc1 | |
| 9748 | 3 | 4 | 5 | | V-1 | Sowahb | |
| 9749 | 3 | 4 | 5 | | V-1 | Sowahc | |
| 9750 | 3 | 4 | 5 | | V-1 | Sox10 | |
| 9751 | 3 | 4 | 5 | | V-1 | Sox5 | |
| 9752 | 3 | 4 | 5 | | V-1 | Sox6 | |
| 9753 | 3 | 4 | 5 | | V-1 | Sp1 | |
| 9754 | 3 | 4 | 5 | | V-1 | Sp100 | |
| 9755 | 3 | 4 | 5 | | V-1 | Sp110 | |
| 9756 | 3 | 4 | 5 | | V-1 | Sp140 | |
| 9757 | 3 | 4 | 5 | | V-1 | Sp3 | |
| 9758 | 3 | 4 | 5 | | V-1 | Sp3os | |
| 9759 | 3 | 4 | 5 | | V-1 | Spaca3 | |
| 9760 | 3 | 4 | 5 | | V-1 | Spaca5 | |
| 9761 | 3 | 4 | 5 | | V-1 | Spag5 | |
| 9762 | 3 | 4 | 5 | | V-1 | Spag6 | |
| 9763 | 3 | 4 | 5 | | V-1 | Spag7 | |
| 9764 | 3 | 4 | 5 | | V-1 | Spata13 | |
| 9765 | 3 | 4 | 5 | | V-1 | Spata2l | |
| 9766 | 3 | 4 | 5 | | V-1 | Spata5 | |
| 9767 | 3 | 4 | 5 | | V-1 | Spats2 | |
| 9768 | 3 | 4 | 5 | | V-1 | Spc24 | |
| 9769 | 3 | 4 | 5 | | V-1 | Spdef | |
| 9770 | 3 | 4 | 5 | | V-1 | Speer6-ps1 | |
| 9771 | 3 | 4 | 5 | | V-1 | Speg | |
| 9772 | 3 | 4 | 5 | | V-1 | Spg11 | |
| 9773 | 3 | 4 | 5 | | V-1 | Spg21 | |
| 9774 | 3 | 4 | 5 | | V-1 | Sphkap | |
| 9775 | 3 | 4 | 5 | | V-1 | Spi1 | |
| 9776 | 3 | 4 | 5 | | V-1 | Spib | |
| 9777 | 3 | 4 | 5 | | V-1 | Spic | |
| 9778 | 3 | 4 | 5 | | V-1 | Spint3 | |
| 9779 | 3 | 4 | 5 | | V-1 | Spopl | |
| 9780 | 3 | 4 | 5 | | V-1 | Sppl3 | |
| 9781 | 3 | 4 | 5 | | V-1 | Spred2 | |
| 9782 | 3 | 4 | 5 | | V-1 | Spred3 | |
| 9783 | 3 | 4 | 5 | | V-1 | Sprr1b | |
| 9784 | 3 | 4 | 5 | | V-1 | Sprr2a1 | |
| 9785 | 3 | 4 | 5 | | V-1 | Sprr2a2 | |
| 9786 | 3 | 4 | 5 | | V-1 | Spry4 | |
| 9787 | 3 | 4 | 5 | | V-1 | Spryd4 | |
| 9788 | 3 | 4 | 5 | | V-1 | Spsb2 | |
| 9789 | 3 | 4 | 5 | | V-1 | Spsb3 | |
| 9790 | 3 | 4 | 5 | | V-1 | Spta1 | |

Fig. 36 - 52

| | | | | | | | |
|---|---|---|---|---|---|---|---|
| 9791 | 3 | 4 | 5 | | V-1 | Sptan1 |
| 9792 | 3 | 4 | 5 | | V-1 | Sptb |
| 9793 | 3 | 4 | 5 | | V-1 | Sptbn1 |
| 9794 | 3 | 4 | 5 | | V-1 | Sptlc2 |
| 9795 | 3 | 4 | 5 | | V-1 | Sqle |
| 9796 | 3 | 4 | 5 | | V-1 | Sqrdl |
| 9797 | 3 | 4 | 5 | | V-1 | Sra1 |
| 9798 | 3 | 4 | 5 | | V-1 | Srd5a1 |
| 9799 | 3 | 4 | 5 | | V-1 | Srd5a3 |
| 9800 | 3 | 4 | 5 | | V-1 | Srebf1 |
| 9801 | 3 | 4 | 5 | | V-1 | Srebf2 |
| 9802 | 3 | 4 | 5 | | V-1 | Sreklip1 |
| 9803 | 3 | 4 | 5 | | V-1 | Srgap3 |
| 9804 | 3 | 4 | 5 | | V-1 | Srgn |
| 9805 | 3 | 4 | 5 | | V-1 | Sri |
| 9806 | 3 | 4 | 5 | | V-1 | Srr |
| 9807 | 3 | 4 | 5 | | V-1 | Srsf3 |
| 9808 | 3 | 4 | 5 | | V-1 | Ssbp4 |
| 9809 | 3 | 4 | 5 | | V-1 | Ssc5d |
| 9810 | 3 | 4 | 5 | | V-1 | Ssh2 |
| 9811 | 3 | 4 | 5 | | V-1 | Ssr2 |
| 9812 | 3 | 4 | 5 | | V-1 | Ssr3 |
| 9813 | 3 | 4 | 5 | | V-1 | Ssr4 |
| 9814 | 3 | 4 | 5 | | V-1 | Sssca1 |
| 9815 | 3 | 4 | 5 | | V-1 | Sstr2 |
| 9816 | 3 | 4 | 5 | | V-1 | Sstr5 |
| 9817 | 3 | 4 | 5 | | V-1 | Ssty1 |
| 9818 | 3 | 4 | 5 | | V-1 | Ssu72 |
| 9819 | 3 | 4 | 5 | | V-1 | Ssx2ip |
| 9820 | 3 | 4 | 5 | | V-1 | St3gal2 |
| 9821 | 3 | 4 | 5 | | V-1 | St3gal4 |
| 9822 | 3 | 4 | 5 | | V-1 | St3gal5 |
| 9823 | 3 | 4 | 5 | | V-1 | St6gal2 |
| 9824 | 3 | 4 | 5 | | V-1 | St6galnac3 |
| 9825 | 3 | 4 | 5 | | V-1 | St6galnac5 |
| 9826 | 3 | 4 | 5 | | V-1 | St8sia1 |
| 9827 | 3 | 4 | 5 | | V-1 | St8sia2 |
| 9828 | 3 | 4 | 5 | | V-1 | St8sia4 |
| 9829 | 3 | 4 | 5 | | V-1 | St8sia5 |
| 9830 | 3 | 4 | 5 | | V-1 | Stac |
| 9831 | 3 | 4 | 5 | | V-1 | Stamos |
| 9832 | 3 | 4 | 5 | | V-1 | Stap1 |
| 9833 | 3 | 4 | 5 | | V-1 | Stap2 |
| 9834 | 3 | 4 | 5 | | V-1 | Stard13 |
| 9835 | 3 | 4 | 5 | | V-1 | Stat2 |
| 9836 | 3 | 4 | 5 | | V-1 | Stat4 |
| 9837 | 3 | 4 | 5 | | V-1 | Stc2 |
| 9838 | 3 | 4 | 5 | | V-1 | Steap1 |
| 9839 | 3 | 4 | 5 | | V-1 | Steap3 |
| 9840 | 3 | 4 | 5 | | V-1 | Stfa3 |
| 9841 | 3 | 4 | 5 | | V-1 | Stk17b |
| 9842 | 3 | 4 | 5 | | V-1 | Stk19 |
| 9843 | 3 | 4 | 5 | | V-1 | Stk24 |
| 9844 | 3 | 4 | 5 | | V-1 | Stk3 |
| 9845 | 3 | 4 | 5 | | V-1 | Stk33 |
| 9846 | 3 | 4 | 5 | | V-1 | Stk35 |
| 9847 | 3 | 4 | 5 | | V-1 | Stk38l |
| 9848 | 3 | 4 | 5 | | V-1 | Stoml1 |
| 9849 | 3 | 4 | 5 | | V-1 | Stox1 |
| 9850 | 3 | 4 | 5 | | V-1 | Stox2 |
| 9851 | 3 | 4 | 5 | | V-1 | Strada |
| 9852 | 3 | 4 | 5 | | V-1 | Strbp |
| 9853 | 3 | 4 | 5 | | V-1 | Strip2 |
| 9854 | 3 | 4 | 5 | | V-1 | Stub1 |
| 9855 | 3 | 4 | 5 | | V-1 | Stx11 |
| 9856 | 3 | 4 | 5 | | V-1 | Stx1a |
| 9857 | 3 | 4 | 5 | | V-1 | Stx8 |
| 9858 | 3 | 4 | 5 | | V-1 | Stxbp5l |
| 9859 | 3 | 4 | 5 | | V-1 | Sugp2 |
| 9860 | 3 | 4 | 5 | | V-1 | Sugt1 |
| 9861 | 3 | 4 | 5 | | V-1 | Sult1c2 |
| 9862 | 3 | 4 | 5 | | V-1 | Sult1d1 |
| 9863 | 3 | 4 | 5 | | V-1 | Sult5a1 |
| 9864 | 3 | 4 | 5 | | V-1 | Sun3 |
| 9865 | 3 | 4 | 5 | | V-1 | Sun5 |
| 9866 | 3 | 4 | 5 | | V-1 | Supt20 |
| 9867 | 3 | 4 | 5 | | V-1 | Supt3 |
| 9868 | 3 | 4 | 5 | | V-1 | Supt4a |
| 9869 | 3 | 4 | 5 | | V-1 | Susd2 |
| 9870 | 3 | 4 | 5 | | V-1 | Svep1 |
| 9871 | 3 | 4 | 5 | | V-1 | Svil |
| 9872 | 3 | 4 | 5 | | V-1 | Swsap1 |
| 9873 | 3 | 4 | 5 | | V-1 | Syce1 |
| 9874 | 3 | 4 | 5 | | V-1 | Syce1l |
| 9875 | 3 | 4 | 5 | | V-1 | Syf2 |
| 9876 | 3 | 4 | 5 | | V-1 | Syk |
| 9877 | 3 | 4 | 5 | | V-1 | Syn2 |
| 9878 | 3 | 4 | 5 | | V-1 | Syn3 |
| 9879 | 3 | 4 | 5 | | V-1 | Syngr2 |
| 9880 | 3 | 4 | 5 | | V-1 | Synpo2 |
| 9881 | 3 | 4 | 5 | | V-1 | Syt11 |
| 9882 | 3 | 4 | 5 | | V-1 | Syt17 |
| 9883 | 3 | 4 | 5 | | V-1 | Syt8 |
| 9884 | 3 | 4 | 5 | | V-1 | Szt2 |
| 9885 | 3 | 4 | 5 | | V-1 | Tac1 |
| 9886 | 3 | 4 | 5 | | V-1 | Taco1 |
| 9887 | 3 | 4 | 5 | | V-1 | Taf11 |
| 9888 | 3 | 4 | 5 | | V-1 | Taf12 |
| 9889 | 3 | 4 | 5 | | V-1 | Taf1b |
| 9890 | 3 | 4 | 5 | | V-1 | Taf1c |
| 9891 | 3 | 4 | 5 | | V-1 | Taf4b |
| 9892 | 3 | 4 | 5 | | V-1 | Taf6 |
| 9893 | 3 | 4 | 5 | | V-1 | Tagap1 |
| 9894 | 3 | 4 | 5 | | V-1 | Tagln |
| 9895 | 3 | 4 | 5 | | V-1 | Taldo1 |
| 9896 | 3 | 4 | 5 | | V-1 | Tamm41 |
| 9897 | 3 | 4 | 5 | | V-1 | Tanc2 |
| 9898 | 3 | 4 | 5 | | V-1 | Taok2 |
| 9899 | 3 | 4 | 5 | | V-1 | Tap2 |
| 9900 | 3 | 4 | 5 | | V-1 | Tapbp |
| 9901 | 3 | 4 | 5 | | V-1 | Tarbp2 |
| 9902 | 3 | 4 | 5 | | V-1 | Tas1r3 |
| 9903 | 3 | 4 | 5 | | V-1 | Tatdn3 |
| 9904 | 3 | 4 | 5 | | V-1 | Tbata |
| 9905 | 3 | 4 | 5 | | V-1 | Tbc1d10c |
| 9906 | 3 | 4 | 5 | | V-1 | Tbc1d17 |
| 9907 | 3 | 4 | 5 | | V-1 | Tbc1d20 |
| 9908 | 3 | 4 | 5 | | V-1 | Tbc1d25 |
| 9909 | 3 | 4 | 5 | | V-1 | Tbc1d2b |
| 9910 | 3 | 4 | 5 | | V-1 | Tbc1d30 |
| 9911 | 3 | 4 | 5 | | V-1 | Tbc1d31 |
| 9912 | 3 | 4 | 5 | | V-1 | Tbl2 |
| 9913 | 3 | 4 | 5 | | V-1 | Tbl3 |
| 9914 | 3 | 4 | 5 | | V-1 | Tbx21 |
| 9915 | 3 | 4 | 5 | | V-1 | Tbx3 |
| 9916 | 3 | 4 | 5 | | V-1 | Tbxa2r |
| 9917 | 3 | 4 | 5 | | V-1 | Tcea1 |
| 9918 | 3 | 4 | 5 | | V-1 | Tceal1 |
| 9919 | 3 | 4 | 5 | | V-1 | Tceb1 |
| 9920 | 3 | 4 | 5 | | V-1 | Tceb2 |
| 9921 | 3 | 4 | 5 | | V-1 | Tcf20 |
| 9922 | 3 | 4 | 5 | | V-1 | Tcp11 |
| 9923 | 3 | 4 | 5 | | V-1 | Tcp11l2 |
| 9924 | 3 | 4 | 5 | | V-1 | Tcte2 |
| 9925 | 3 | 4 | 5 | | V-1 | Tctn2 |
| 9926 | 3 | 4 | 5 | | V-1 | Tctn3 |
| 9927 | 3 | 4 | 5 | | V-1 | Tdp1 |
| 9928 | 3 | 4 | 5 | | V-1 | Tead3 |
| 9929 | 3 | 4 | 5 | | V-1 | Tec |
| 9930 | 3 | 4 | 5 | | V-1 | Tecpr1 |
| 9931 | 3 | 4 | 5 | | V-1 | Tecr |
| 9932 | 3 | 4 | 5 | | V-1 | Tekt2 |
| 9933 | 3 | 4 | 5 | | V-1 | Tekt4 |
| 9934 | 3 | 4 | 5 | | V-1 | Telo2 |
| 9935 | 3 | 4 | 5 | | V-1 | Tenm2 |
| 9936 | 3 | 4 | 5 | | V-1 | Tep1 |
| 9937 | 3 | 4 | 5 | | V-1 | Tes |
| 9938 | 3 | 4 | 5 | | V-1 | Tesk2 |
| 9939 | 3 | 4 | 5 | | V-1 | Tet1 |
| 9940 | 3 | 4 | 5 | | V-1 | Tet2 |
| 9941 | 3 | 4 | 5 | | V-1 | Tet3 |
| 9942 | 3 | 4 | 5 | | V-1 | Tex101 |
| 9943 | 3 | 4 | 5 | | V-1 | Tex15 |
| 9944 | 3 | 4 | 5 | | V-1 | Tex33 |
| 9945 | 3 | 4 | 5 | | V-1 | Tfap2a |
| 9946 | 3 | 4 | 5 | | V-1 | Tfec |
| 9947 | 3 | 4 | 5 | | V-1 | Tfpt |
| 9948 | 3 | 4 | 5 | | V-1 | Tgfa |
| 9949 | 3 | 4 | 5 | | V-1 | Tgfb1 |
| 9950 | 3 | 4 | 5 | | V-1 | Tgfb2 |
| 9951 | 3 | 4 | 5 | | V-1 | Tgfbr1 |
| 9952 | 3 | 4 | 5 | | V-1 | Tgfbr2 |
| 9953 | 3 | 4 | 5 | | V-1 | Tgif1 |
| 9954 | 3 | 4 | 5 | | V-1 | Tgm3 |
| 9955 | 3 | 4 | 5 | | V-1 | Tgm4 |
| 9956 | 3 | 4 | 5 | | V-1 | Tgm7 |
| 9957 | 3 | 4 | 5 | | V-1 | Tha1 |
| 9958 | 3 | 4 | 5 | | V-1 | Thada |
| 9959 | 3 | 4 | 5 | | V-1 | Thap2 |
| 9960 | 3 | 4 | 5 | | V-1 | Thnsl1 |
| 9961 | 3 | 4 | 5 | | V-1 | Thnsl2 |
| 9962 | 3 | 4 | 5 | | V-1 | Thra |
| 9963 | 3 | 4 | 5 | | V-1 | Thrsp |
| 9964 | 3 | 4 | 5 | | V-1 | Thsd4 |
| 9965 | 3 | 4 | 5 | | V-1 | Thsd7a |
| 9966 | 3 | 4 | 5 | | V-1 | Thy1 |
| 9967 | 3 | 4 | 5 | | V-1 | Thyn1 |
| 9968 | 3 | 4 | 5 | | V-1 | Tifab |
| 9969 | 3 | 4 | 5 | | V-1 | Tigd2 |
| 9970 | 3 | 4 | 5 | | V-1 | Tigit |
| 9971 | 3 | 4 | 5 | | V-1 | Timm10 |
| 9972 | 3 | 4 | 5 | | V-1 | Timm13 |
| 9973 | 3 | 4 | 5 | | V-1 | Tirap |
| 9974 | 3 | 4 | 5 | | V-1 | Tjp3 |
| 9975 | 3 | 4 | 5 | | V-1 | Tk1 |
| 9976 | 3 | 4 | 5 | | V-1 | Tkt |
| 9977 | 3 | 4 | 5 | | V-1 | Tlcd2 |
| 9978 | 3 | 4 | 5 | | V-1 | Tle6 |
| 9979 | 3 | 4 | 5 | | V-1 | Tlr1 |
| 9980 | 3 | 4 | 5 | | V-1 | Tlr4 |
| 9981 | 3 | 4 | 5 | | V-1 | Tlr5 |
| 9982 | 3 | 4 | 5 | | V-1 | Tlr6 |

Fig. 36 - 53

| | | | | | | | |
|---|---|---|---|---|---|---|---|
| 9983 | 3 | 4 | 5 | | | V-1 | Tlr7 |
| 9984 | 3 | 4 | 5 | | | V-1 | Tm2d3 |
| 9985 | 3 | 4 | 5 | | | V-1 | Tm4sf5 |
| 9986 | 3 | 4 | 5 | | | V-1 | Tm6sf1 |
| 9987 | 3 | 4 | 5 | | | V-1 | Tma16 |
| 9988 | 3 | 4 | 5 | | | V-1 | Tmc6 |
| 9989 | 3 | 4 | 5 | | | V-1 | Tmc7 |
| 9990 | 3 | 4 | 5 | | | V-1 | Tmc8 |
| 9991 | 3 | 4 | 5 | | | V-1 | Tmco5 |
| 9992 | 3 | 4 | 5 | | | V-1 | Tmco6 |
| 9993 | 3 | 4 | 5 | | | V-1 | Tmed11 |
| 9994 | 3 | 4 | 5 | | | V-1 | Tmed8 |
| 9995 | 3 | 4 | 5 | | | V-1 | Tmed9 |
| 9996 | 3 | 4 | 5 | | | V-1 | Tmem102 |
| 9997 | 3 | 4 | 5 | | | V-1 | Tmem106a |
| 9998 | 3 | 4 | 5 | | | V-1 | Tmem116 |
| 9999 | 3 | 4 | 5 | | | V-1 | Tmem132a |
| 10000 | 3 | 4 | 5 | | | V-1 | Tmem132d |
| 10001 | 3 | 4 | 5 | | | V-1 | Tmem141 |
| 10002 | 3 | 4 | 5 | | | V-1 | Tmem144 |
| 10003 | 3 | 4 | 5 | | | V-1 | Tmem14c |
| 10004 | 3 | 4 | 5 | | | V-1 | Tmem161b |
| 10005 | 3 | 4 | 5 | | | V-1 | Tmem164 |
| 10006 | 3 | 4 | 5 | | | V-1 | Tmem17 |
| 10007 | 3 | 4 | 5 | | | V-1 | Tmem170 |
| 10008 | 3 | 4 | 5 | | | V-1 | Tmem171 |
| 10009 | 3 | 4 | 5 | | | V-1 | Tmem173 |
| 10010 | 3 | 4 | 5 | | | V-1 | Tmem176a |
| 10011 | 3 | 4 | 5 | | | V-1 | Tmem176b |
| 10012 | 3 | 4 | 5 | | | V-1 | Tmem179 |
| 10013 | 3 | 4 | 5 | | | V-1 | Tmem179b |
| 10014 | 3 | 4 | 5 | | | V-1 | Tmem181a |
| 10015 | 3 | 4 | 5 | | | V-1 | Tmem190 |
| 10016 | 3 | 4 | 5 | | | V-1 | Tmem191c |
| 10017 | 3 | 4 | 5 | | | V-1 | Tmem192 |
| 10018 | 3 | 4 | 5 | | | V-1 | Tmem198 |
| 10019 | 3 | 4 | 5 | | | V-1 | Tmem2 |
| 10020 | 3 | 4 | 5 | | | V-1 | Tmem200b |
| 10021 | 3 | 4 | 5 | | | V-1 | Tmem210 |
| 10022 | 3 | 4 | 5 | | | V-1 | Tmem216 |
| 10023 | 3 | 4 | 5 | | | V-1 | Tmem218 |
| 10024 | 3 | 4 | 5 | | | V-1 | Tmem222 |
| 10025 | 3 | 4 | 5 | | | V-1 | Tmem229b |
| 10026 | 3 | 4 | 5 | | | V-1 | Tmem231 |
| 10027 | 3 | 4 | 5 | | | V-1 | Tmem237 |
| 10028 | 3 | 4 | 5 | | | V-1 | Tmem239 |
| 10029 | 3 | 4 | 5 | | | V-1 | Tmem240 |
| 10030 | 3 | 4 | 5 | | | V-1 | Tmem241 |
| 10031 | 3 | 4 | 5 | | | V-1 | Tmem247 |
| 10032 | 3 | 4 | 5 | | | V-1 | Tmem254a |
| 10033 | 3 | 4 | 5 | | | V-1 | Tmem254b |
| 10034 | 3 | 4 | 5 | | | V-1 | Tmem261 |
| 10035 | 3 | 4 | 5 | | | V-1 | Tmem263 |
| 10036 | 3 | 4 | 5 | | | V-1 | Tmem37 |
| 10037 | 3 | 4 | 5 | | | V-1 | Tmem39b |
| 10038 | 3 | 4 | 5 | | | V-1 | Tmem42 |
| 10039 | 3 | 4 | 5 | | | V-1 | Tmem47 |
| 10040 | 3 | 4 | 5 | | | V-1 | Tmem51os1 |
| 10041 | 3 | 4 | 5 | | | V-1 | Tmem55a |
| 10042 | 3 | 4 | 5 | | | V-1 | Tmem62 |
| 10043 | 3 | 4 | 5 | | | V-1 | Tmem63a |
| 10044 | 3 | 4 | 5 | | | V-1 | Tmem63c |
| 10045 | 3 | 4 | 5 | | | V-1 | Tmem69 |
| 10046 | 3 | 4 | 5 | | | V-1 | Tmem8 |
| 10047 | 3 | 4 | 5 | | | V-1 | Tmem89 |
| 10048 | 3 | 4 | 5 | | | V-1 | Tmem9 |
| 10049 | 3 | 4 | 5 | | | V-1 | Tmem95 |
| 10050 | 3 | 4 | 5 | | | V-1 | Tmem98 |
| 10051 | 3 | 4 | 5 | | | V-1 | Tmod2 |
| 10052 | 3 | 4 | 5 | | | V-1 | Tmod4 |
| 10053 | 3 | 4 | 5 | | | V-1 | Tmppe |
| 10054 | 3 | 4 | 5 | | | V-1 | Tmprss13 |
| 10055 | 3 | 4 | 5 | | | V-1 | Tmprss2 |
| 10056 | 3 | 4 | 5 | | | V-1 | Tmtc1 |
| 10057 | 3 | 4 | 5 | | | V-1 | Tnc |
| 10058 | 3 | 4 | 5 | | | V-1 | Tnf |
| 10059 | 3 | 4 | 5 | | | V-1 | Tnfaip6 |
| 10060 | 3 | 4 | 5 | | | V-1 | Tnfaip8l1 |
| 10061 | 3 | 4 | 5 | | | V-1 | Tnfaip8l2 |
| 10062 | 3 | 4 | 5 | | | V-1 | Tnfrsf10b |
| 10063 | 3 | 4 | 5 | | | V-1 | Tnfrsf11b |
| 10064 | 3 | 4 | 5 | | | V-1 | Tnfrsf13b |
| 10065 | 3 | 4 | 5 | | | V-1 | Tnfrsf22 |
| 10066 | 3 | 4 | 5 | | | V-1 | Tnfsf13 |
| 10067 | 3 | 4 | 5 | | | V-1 | Tnfsf18 |
| 10068 | 3 | 4 | 5 | | | V-1 | Tnfsf9 |
| 10069 | 3 | 4 | 5 | | | V-1 | Tnip1 |
| 10070 | 3 | 4 | 5 | | | V-1 | Tnk2 |
| 10071 | 3 | 4 | 5 | | | V-1 | Tnk2os |
| 10072 | 3 | 4 | 5 | | | V-1 | Tnmd |
| 10073 | 3 | 4 | 5 | | | V-1 | Tnni3 |
| 10074 | 3 | 4 | 5 | | | V-1 | Tnnt2 |
| 10075 | 3 | 4 | 5 | | | V-1 | Tnrc6a |
| 10076 | 3 | 4 | 5 | | | V-1 | Tnrc6b |
| 10077 | 3 | 4 | 5 | | | V-1 | Tnrc6c |
| 10078 | 3 | 4 | 5 | | | V-1 | Tnxb |
| 10079 | 3 | 4 | 5 | | | V-1 | Tomm6 |
| 10080 | 3 | 4 | 5 | | | V-1 | Tomm6os |
| 10081 | 3 | 4 | 5 | | | V-1 | Tomm7 |
| 10082 | 3 | 4 | 5 | | | V-1 | Top1 |
| 10083 | 3 | 4 | 5 | | | V-1 | Tor3a |
| 10084 | 3 | 4 | 5 | | | V-1 | Tox |
| 10085 | 3 | 4 | 5 | | | V-1 | Tpcn2 |
| 10086 | 3 | 4 | 5 | | | V-1 | Tpd52 |
| 10087 | 3 | 4 | 5 | | | V-1 | Tpm4 |
| 10088 | 3 | 4 | 5 | | | V-1 | Tpmt |
| 10089 | 3 | 4 | 5 | | | V-1 | Tppp |
| 10090 | 3 | 4 | 5 | | | V-1 | Tpr |
| 10091 | 3 | 4 | 5 | | | V-1 | Tpsg1 |
| 10092 | 3 | 4 | 5 | | | V-1 | Tpst2 |
| 10093 | 3 | 4 | 5 | | | V-1 | Tra2a |
| 10094 | 3 | 4 | 5 | | | V-1 | Traf3ip2 |
| 10095 | 3 | 4 | 5 | | | V-1 | Traf5 |
| 10096 | 3 | 4 | 5 | | | V-1 | Traf6 |
| 10097 | 3 | 4 | 5 | | | V-1 | Traip |
| 10098 | 3 | 4 | 5 | | | V-1 | Trappc2 |
| 10099 | 3 | 4 | 5 | | | V-1 | Trappc2l |
| 10100 | 3 | 4 | 5 | | | V-1 | Trappc6a |
| 10101 | 3 | 4 | 5 | | | V-1 | Trem3 |
| 10102 | 3 | 4 | 5 | | | V-1 | Trerf1 |
| 10103 | 3 | 4 | 5 | | | V-1 | Trhr2 |
| 10104 | 3 | 4 | 5 | | | V-1 | Trim12c |
| 10105 | 3 | 4 | 5 | | | V-1 | Trim25 |
| 10106 | 3 | 4 | 5 | | | V-1 | Trim29 |
| 10107 | 3 | 4 | 5 | | | V-1 | Trim3 |
| 10108 | 3 | 4 | 5 | | | V-1 | Trim30d |
| 10109 | 3 | 4 | 5 | | | V-1 | Trim32 |
| 10110 | 3 | 4 | 5 | | | V-1 | Trim34b |
| 10111 | 3 | 4 | 5 | | | V-1 | Trim36 |
| 10112 | 3 | 4 | 5 | | | V-1 | Trim38 |
| 10113 | 3 | 4 | 5 | | | V-1 | Trim50 |
| 10114 | 3 | 4 | 5 | | | V-1 | Trim54 |
| 10115 | 3 | 4 | 5 | | | V-1 | Trim59 |
| 10116 | 3 | 4 | 5 | | | V-1 | Trim63 |
| 10117 | 3 | 4 | 5 | | | V-1 | Trim66 |
| 10118 | 3 | 4 | 5 | | | V-1 | Trim67 |
| 10119 | 3 | 4 | 5 | | | V-1 | Trim68 |
| 10120 | 3 | 4 | 5 | | | V-1 | Trim72 |
| 10121 | 3 | 4 | 5 | | | V-1 | Trio |
| 10122 | 3 | 4 | 5 | | | V-1 | Triqk |
| 10123 | 3 | 4 | 5 | | | V-1 | Trit1 |
| 10124 | 3 | 4 | 5 | | | V-1 | Trmt10c |
| 10125 | 3 | 4 | 5 | | | V-1 | Trmt11 |
| 10126 | 3 | 4 | 5 | | | V-1 | Trmt12 |
| 10127 | 3 | 4 | 5 | | | V-1 | Trmt44 |
| 10128 | 3 | 4 | 5 | | | V-1 | Trmt61a |
| 10129 | 3 | 4 | 5 | | | V-1 | Troap |
| 10130 | 3 | 4 | 5 | | | V-1 | Trp53bp1 |
| 10131 | 3 | 4 | 5 | | | V-1 | Trp53i13 |
| 10132 | 3 | 4 | 5 | | | V-1 | Trp53inp1 |
| 10133 | 3 | 4 | 5 | | | V-1 | Trpc1 |
| 10134 | 3 | 4 | 5 | | | V-1 | Trpm2 |
| 10135 | 3 | 4 | 5 | | | V-1 | Trpm4 |
| 10136 | 3 | 4 | 5 | | | V-1 | Trps1 |
| 10137 | 3 | 4 | 5 | | | V-1 | Trpt1 |
| 10138 | 3 | 4 | 5 | | | V-1 | Trrap |
| 10139 | 3 | 4 | 5 | | | V-1 | Tsc22d1 |
| 10140 | 3 | 4 | 5 | | | V-1 | Tshz1 |
| 10141 | 3 | 4 | 5 | | | V-1 | Tshz2 |
| 10142 | 3 | 4 | 5 | | | V-1 | Tspan11 |
| 10143 | 3 | 4 | 5 | | | V-1 | Tspan18 |
| 10144 | 3 | 4 | 5 | | | V-1 | Tspan33 |
| 10145 | 3 | 4 | 5 | | | V-1 | Tssc4 |
| 10146 | 3 | 4 | 5 | | | V-1 | Tssk6 |
| 10147 | 3 | 4 | 5 | | | V-1 | Tst |
| 10148 | 3 | 4 | 5 | | | V-1 | Tstd1 |
| 10149 | 3 | 4 | 5 | | | V-1 | Ttbk1 |
| 10150 | 3 | 4 | 5 | | | V-1 | Ttbk2 |
| 10151 | 3 | 4 | 5 | | | V-1 | Ttc19 |
| 10152 | 3 | 4 | 5 | | | V-1 | Ttc21a |
| 10153 | 3 | 4 | 5 | | | V-1 | Ttc24 |
| 10154 | 3 | 4 | 5 | | | V-1 | Ttc26 |
| 10155 | 3 | 4 | 5 | | | V-1 | Ttc27 |
| 10156 | 3 | 4 | 5 | | | V-1 | Ttc30a1 |
| 10157 | 3 | 4 | 5 | | | V-1 | Ttc30a2 |
| 10158 | 3 | 4 | 5 | | | V-1 | Ttc34 |
| 10159 | 3 | 4 | 5 | | | V-1 | Ttc39a |
| 10160 | 3 | 4 | 5 | | | V-1 | Ttc39b |
| 10161 | 3 | 4 | 5 | | | V-1 | Ttc9 |
| 10162 | 3 | 4 | 5 | | | V-1 | Ttl2 |
| 10163 | 3 | 4 | 5 | | | V-1 | Ttll1 |
| 10164 | 3 | 4 | 5 | | | V-1 | Ttll10 |
| 10165 | 3 | 4 | 5 | | | V-1 | Ttll7 |
| 10166 | 3 | 4 | 5 | | | V-1 | Ttn |
| 10167 | 3 | 4 | 5 | | | V-1 | Ttyh2 |
| 10168 | 3 | 4 | 5 | | | V-1 | Ttyh3 |
| 10169 | 3 | 4 | 5 | | | V-1 | Tuba1a |
| 10170 | 3 | 4 | 5 | | | V-1 | Tuba1c |
| 10171 | 3 | 4 | 5 | | | V-1 | Tuba3b |
| 10172 | 3 | 4 | 5 | | | V-1 | Tubb6 |
| 10173 | 3 | 4 | 5 | | | V-1 | Tubgcp3 |
| 10174 | 3 | 4 | 5 | | | V-1 | Tubgcp6 |

Fig. 36 - 54

| | | | | | | | |
|---|---|---|---|---|---|---|---|
| 10175 | 3 | 4 | 5 | | V-1 | Tufm |
| 10176 | 3 | 4 | 5 | | V-1 | Tuft1 |
| 10177 | 3 | 4 | 5 | | V-1 | Tulp4 |
| 10178 | 3 | 4 | 5 | | V-1 | Tusc2 |
| 10179 | 3 | 4 | 5 | | V-1 | Tusc3 |
| 10180 | 3 | 4 | 5 | | V-1 | Tusc5 |
| 10181 | 3 | 4 | 5 | | V-1 | Tvp23a |
| 10182 | 3 | 4 | 5 | | V-1 | Twist1 |
| 10183 | 3 | 4 | 5 | | V-1 | Txlna |
| 10184 | 3 | 4 | 5 | | V-1 | Txn1 |
| 10185 | 3 | 4 | 5 | | V-1 | Txndc12 |
| 10186 | 3 | 4 | 5 | | V-1 | Txndc8 |
| 10187 | 3 | 4 | 5 | | V-1 | Txnip |
| 10188 | 3 | 4 | 5 | | V-1 | Txnrd2 |
| 10189 | 3 | 4 | 5 | | V-1 | Txnrd3 |
| 10190 | 3 | 4 | 5 | | V-1 | Tyms-ps |
| 10191 | 3 | 4 | 5 | | V-1 | U2af1l4 |
| 10192 | 3 | 4 | 5 | | V-1 | Uba52 |
| 10193 | 3 | 4 | 5 | | V-1 | Uba6 |
| 10194 | 3 | 4 | 5 | | V-1 | Uba7 |
| 10195 | 3 | 4 | 5 | | V-1 | Ubash3b |
| 10196 | 3 | 4 | 5 | | V-1 | Ubc |
| 10197 | 3 | 4 | 5 | | V-1 | Ube2c |
| 10198 | 3 | 4 | 5 | | V-1 | Ube2f |
| 10199 | 3 | 4 | 5 | | V-1 | Ube2j2 |
| 10200 | 3 | 4 | 5 | | V-1 | Ube2t |
| 10201 | 3 | 4 | 5 | | V-1 | Ube2u |
| 10202 | 3 | 4 | 5 | | V-1 | Ubn2 |
| 10203 | 3 | 4 | 5 | | V-1 | Ubr4 |
| 10204 | 3 | 4 | 5 | | V-1 | Ubr5 |
| 10205 | 3 | 4 | 5 | | V-1 | Ubxn1 |
| 10206 | 3 | 4 | 5 | | V-1 | Ubxn11 |
| 10207 | 3 | 4 | 5 | | V-1 | Ubxn2a |
| 10208 | 3 | 4 | 5 | | V-1 | Uchl1 |
| 10209 | 3 | 4 | 5 | | V-1 | Uchl3 |
| 10210 | 3 | 4 | 5 | | V-1 | Uck2 |
| 10211 | 3 | 4 | 5 | | V-1 | Uckl1os |
| 10212 | 3 | 4 | 5 | | V-1 | Ufsp1 |
| 10213 | 3 | 4 | 5 | | V-1 | Ugt1a6a |
| 10214 | 3 | 4 | 5 | | V-1 | Ugt1a6b |
| 10215 | 3 | 4 | 5 | | V-1 | Ugt2b36 |
| 10216 | 3 | 4 | 5 | | V-1 | Ugt2b37 |
| 10217 | 3 | 4 | 5 | | V-1 | Ugt2b5 |
| 10218 | 3 | 4 | 5 | | V-1 | Uhrf1 |
| 10219 | 3 | 4 | 5 | | V-1 | Uhrf1bp1 |
| 10220 | 3 | 4 | 5 | | V-1 | Umps |
| 10221 | 3 | 4 | 5 | | V-1 | Unc13c |
| 10222 | 3 | 4 | 5 | | V-1 | Unc5c |
| 10223 | 3 | 4 | 5 | | V-1 | Upk1b |
| 10224 | 3 | 4 | 5 | | V-1 | Upp1 |
| 10225 | 3 | 4 | 5 | | V-1 | Uqcrfs1 |
| 10226 | 3 | 4 | 5 | | V-1 | Uqcrh |
| 10227 | 3 | 4 | 5 | | V-1 | Urad |
| 10228 | 3 | 4 | 5 | | V-1 | Urah |
| 10229 | 3 | 4 | 5 | | V-1 | Urb1 |
| 10230 | 3 | 4 | 5 | | V-1 | Urb2 |
| 10231 | 3 | 4 | 5 | | V-1 | Urm1 |
| 10232 | 3 | 4 | 5 | | V-1 | Uros |
| 10233 | 3 | 4 | 5 | | V-1 | Use1 |
| 10234 | 3 | 4 | 5 | | V-1 | Usp11 |
| 10235 | 3 | 4 | 5 | | V-1 | Usp13 |
| 10236 | 3 | 4 | 5 | | V-1 | Usp20 |
| 10237 | 3 | 4 | 5 | | V-1 | Usp29 |
| 10238 | 3 | 4 | 5 | | V-1 | Usp38 |
| 10239 | 3 | 4 | 5 | | V-1 | Usp42 |
| 10240 | 3 | 4 | 5 | | V-1 | Usp51 |
| 10241 | 3 | 4 | 5 | | V-1 | Usp6nl |
| 10242 | 3 | 4 | 5 | | V-1 | Usp9x |
| 10243 | 3 | 4 | 5 | | V-1 | Uspl1 |
| 10244 | 3 | 4 | 5 | | V-1 | Utp11l |
| 10245 | 3 | 4 | 5 | | V-1 | Utp15 |
| 10246 | 3 | 4 | 5 | | V-1 | Utp18 |
| 10247 | 3 | 4 | 5 | | V-1 | Utp20 |
| 10248 | 3 | 4 | 5 | | V-1 | Uts2 |
| 10249 | 3 | 4 | 5 | | V-1 | Uvssa |
| 10250 | 3 | 4 | 5 | | V-1 | Uxs1 |
| 10251 | 3 | 4 | 5 | | V-1 | Vamp1 |
| 10252 | 3 | 4 | 5 | | V-1 | Vamp4 |
| 10253 | 3 | 4 | 5 | | V-1 | Vapa |
| 10254 | 3 | 4 | 5 | | V-1 | Vash1 |
| 10255 | 3 | 4 | 5 | | V-1 | Vav1 |
| 10256 | 3 | 4 | 5 | | V-1 | Vav2 |
| 10257 | 3 | 4 | 5 | | V-1 | Vcan |
| 10258 | 3 | 4 | 5 | | V-1 | Vcpip1 |
| 10259 | 3 | 4 | 5 | | V-1 | Vdac2 |
| 10260 | 3 | 4 | 5 | | V-1 | Vdr |
| 10261 | 3 | 4 | 5 | | V-1 | Vegfc |
| 10262 | 3 | 4 | 5 | | V-1 | Vipas39 |
| 10263 | 3 | 4 | 5 | | V-1 | Vkorc1l1 |
| 10264 | 3 | 4 | 5 | | V-1 | Vopp1 |
| 10265 | 3 | 4 | 5 | | V-1 | Vpreb1 |
| 10266 | 3 | 4 | 5 | | V-1 | Vps13a |
| 10267 | 3 | 4 | 5 | | V-1 | Vps13b |
| 10268 | 3 | 4 | 5 | | V-1 | Vps13d |
| 10269 | 3 | 4 | 5 | | V-1 | Vps18 |
| 10270 | 3 | 4 | 5 | | V-1 | Vps28 |
| 10271 | 3 | 4 | 5 | | V-1 | Vps33b |
| 10272 | 3 | 4 | 5 | | V-1 | Vps36 |
| 10273 | 3 | 4 | 5 | | V-1 | Vps37c |
| 10274 | 3 | 4 | 5 | | V-1 | Vps37d |
| 10275 | 3 | 4 | 5 | | V-1 | Vsig2 |
| 10276 | 3 | 4 | 5 | | V-1 | Vstm5 |
| 10277 | 3 | 4 | 5 | | V-1 | Vta1 |
| 10278 | 3 | 4 | 5 | | V-1 | Wars |
| 10279 | 3 | 4 | 5 | | V-1 | Wars2 |
| 10280 | 3 | 4 | 5 | | V-1 | Wasf2 |
| 10281 | 3 | 4 | 5 | | V-1 | Wbscr16 |
| 10282 | 3 | 4 | 5 | | V-1 | Wdfy3 |
| 10283 | 3 | 4 | 5 | | V-1 | Wdpcp |
| 10284 | 3 | 4 | 5 | | V-1 | Wdr20rt |
| 10285 | 3 | 4 | 5 | | V-1 | Wdr24 |
| 10286 | 3 | 4 | 5 | | V-1 | Wdr25 |
| 10287 | 3 | 4 | 5 | | V-1 | Wdr38 |
| 10288 | 3 | 4 | 5 | | V-1 | Wdr4 |
| 10289 | 3 | 4 | 5 | | V-1 | Wdr54 |
| 10290 | 3 | 4 | 5 | | V-1 | Wdr6 |
| 10291 | 3 | 4 | 5 | | V-1 | Wdr63 |
| 10292 | 3 | 4 | 5 | | V-1 | Wdr73 |
| 10293 | 3 | 4 | 5 | | V-1 | Wdr74 |
| 10294 | 3 | 4 | 5 | | V-1 | Wdr76 |
| 10295 | 3 | 4 | 5 | | V-1 | Wdr8 |
| 10296 | 3 | 4 | 5 | | V-1 | Wdr81 |
| 10297 | 3 | 4 | 5 | | V-1 | Wdr83 |
| 10298 | 3 | 4 | 5 | | V-1 | Wdr90 |
| 10299 | 3 | 4 | 5 | | V-1 | Wfdc1 |
| 10300 | 3 | 4 | 5 | | V-1 | Wfdc3 |
| 10301 | 3 | 4 | 5 | | V-1 | Wfikkn2 |
| 10302 | 3 | 4 | 5 | | V-1 | Whamm |
| 10303 | 3 | 4 | 5 | | V-1 | Whrn |
| 10304 | 3 | 4 | 5 | | V-1 | Whsc1l1 |
| 10305 | 3 | 4 | 5 | | V-1 | Wibg |
| 10306 | 3 | 4 | 5 | | V-1 | Wipf3 |
| 10307 | 3 | 4 | 5 | | V-1 | Wnk1 |
| 10308 | 3 | 4 | 5 | | V-1 | Wnk3 |
| 10309 | 3 | 4 | 5 | | V-1 | Wnt16 |
| 10310 | 3 | 4 | 5 | | V-1 | Wnt3 |
| 10311 | 3 | 4 | 5 | | V-1 | Wnt5a |
| 10312 | 3 | 4 | 5 | | V-1 | Wnt6 |
| 10313 | 3 | 4 | 5 | | V-1 | Wnt7b |
| 10314 | 3 | 4 | 5 | | V-1 | Wrb |
| 10315 | 3 | 4 | 5 | | V-1 | Xbp1 |
| 10316 | 3 | 4 | 5 | | V-1 | Xiap |
| 10317 | 3 | 4 | 5 | | V-1 | Xirp2 |
| 10318 | 3 | 4 | 5 | | V-1 | Xk |
| 10319 | 3 | 4 | 5 | | V-1 | Xlr4b |
| 10320 | 3 | 4 | 5 | | V-1 | Xlr4c |
| 10321 | 3 | 4 | 5 | | V-1 | Xpo5 |
| 10322 | 3 | 4 | 5 | | V-1 | Xpo7 |
| 10323 | 3 | 4 | 5 | | V-1 | Xrcc3 |
| 10324 | 3 | 4 | 5 | | V-1 | Xrcc5 |
| 10325 | 3 | 4 | 5 | | V-1 | Xrcc6bp1 |
| 10326 | 3 | 4 | 5 | | V-1 | Xxylt1 |
| 10327 | 3 | 4 | 5 | | V-1 | Ydjc |
| 10328 | 3 | 4 | 5 | | V-1 | Yeats2 |
| 10329 | 3 | 4 | 5 | | V-1 | Yes1 |
| 10330 | 3 | 4 | 5 | | V-1 | Yipf1 |
| 10331 | 3 | 4 | 5 | | V-1 | Yipf2 |
| 10332 | 3 | 4 | 5 | | V-1 | Ypel1 |
| 10333 | 3 | 4 | 5 | | V-1 | Ypel2 |
| 10334 | 3 | 4 | 5 | | V-1 | Ythdf1 |
| 10335 | 3 | 4 | 5 | | V-1 | Yy2 |
| 10336 | 3 | 4 | 5 | | V-1 | Zbed4 |
| 10337 | 3 | 4 | 5 | | V-1 | Zbtb12 |
| 10338 | 3 | 4 | 5 | | V-1 | Zbtb21 |
| 10339 | 3 | 4 | 5 | | V-1 | Zbtb26 |
| 10340 | 3 | 4 | 5 | | V-1 | Zbtb3 |
| 10341 | 3 | 4 | 5 | | V-1 | Zbtb39 |
| 10342 | 3 | 4 | 5 | | V-1 | Zbtb40 |
| 10343 | 3 | 4 | 5 | | V-1 | Zbtb45 |
| 10344 | 3 | 4 | 5 | | V-1 | Zbtb46 |
| 10345 | 3 | 4 | 5 | | V-1 | Zbtb7a |
| 10346 | 3 | 4 | 5 | | V-1 | Zc3h8 |
| 10347 | 3 | 4 | 5 | | V-1 | Zc3hav1l |
| 10348 | 3 | 4 | 5 | | V-1 | Zcchc11 |
| 10349 | 3 | 4 | 5 | | V-1 | Zcchc16 |
| 10350 | 3 | 4 | 5 | | V-1 | Zcchc5 |
| 10351 | 3 | 4 | 5 | | V-1 | Zcchc6 |
| 10352 | 3 | 4 | 5 | | V-1 | Zdbf2 |
| 10353 | 3 | 4 | 5 | | V-1 | Zdhhc21 |
| 10354 | 3 | 4 | 5 | | V-1 | Zdhhc22 |
| 10355 | 3 | 4 | 5 | | V-1 | Zfat |
| 10356 | 3 | 4 | 5 | | V-1 | Zfc3h1 |
| 10357 | 3 | 4 | 5 | | V-1 | Zfhx2 |
| 10358 | 3 | 4 | 5 | | V-1 | Zfml |
| 10359 | 3 | 4 | 5 | | V-1 | Zfp106 |
| 10360 | 3 | 4 | 5 | | V-1 | Zfp110 |
| 10361 | 3 | 4 | 5 | | V-1 | Zfp111 |
| 10362 | 3 | 4 | 5 | | V-1 | Zfp112 |
| 10363 | 3 | 4 | 5 | | V-1 | Zfp128 |
| 10364 | 3 | 4 | 5 | | V-1 | Zfp131 |
| 10365 | 3 | 4 | 5 | | V-1 | Zfp133-ps |
| 10366 | 3 | 4 | 5 | | V-1 | Zfp142 |

Fig. 36 - 55

| | | | | | | | |
|---|---|---|---|---|---|---|---|
| 10367 | 3 | 4 | 5 | | V-1 | Zfp146 |
| 10368 | 3 | 4 | 5 | | V-1 | Zfp174 |
| 10369 | 3 | 4 | 5 | | V-1 | Zfp217 |
| 10370 | 3 | 4 | 5 | | V-1 | Zfp236 |
| 10371 | 3 | 4 | 5 | | V-1 | Zfp239 |
| 10372 | 3 | 4 | 5 | | V-1 | Zfp260 |
| 10373 | 3 | 4 | 5 | | V-1 | Zfp27 |
| 10374 | 3 | 4 | 5 | | V-1 | Zfp275 |
| 10375 | 3 | 4 | 5 | | V-1 | Zfp277 |
| 10376 | 3 | 4 | 5 | | V-1 | Zfp281 |
| 10377 | 3 | 4 | 5 | | V-1 | Zfp292 |
| 10378 | 3 | 4 | 5 | | V-1 | Zfp296 |
| 10379 | 3 | 4 | 5 | | V-1 | Zfp3 |
| 10380 | 3 | 4 | 5 | | V-1 | Zfp300 |
| 10381 | 3 | 4 | 5 | | V-1 | Zfp318 |
| 10382 | 3 | 4 | 5 | | V-1 | Zfp319 |
| 10383 | 3 | 4 | 5 | | V-1 | Zfp329 |
| 10384 | 3 | 4 | 5 | | V-1 | Zfp334 |
| 10385 | 3 | 4 | 5 | | V-1 | Zfp335 |
| 10386 | 3 | 4 | 5 | | V-1 | Zfp354a |
| 10387 | 3 | 4 | 5 | | V-1 | Zfp36 |
| 10388 | 3 | 4 | 5 | | V-1 | Zfp366 |
| 10389 | 3 | 4 | 5 | | V-1 | Zfp362 |
| 10390 | 3 | 4 | 5 | | V-1 | Zfp40 |
| 10391 | 3 | 4 | 5 | | V-1 | Zfp41 |
| 10392 | 3 | 4 | 5 | | V-1 | Zfp414 |
| 10393 | 3 | 4 | 5 | | V-1 | Zfp418 |
| 10394 | 3 | 4 | 5 | | V-1 | Zfp420 |
| 10395 | 3 | 4 | 5 | | V-1 | Zfp428 |
| 10396 | 3 | 4 | 5 | | V-1 | Zfp449 |
| 10397 | 3 | 4 | 5 | | V-1 | Zfp451 |
| 10398 | 3 | 4 | 5 | | V-1 | Zfp454 |
| 10399 | 3 | 4 | 5 | | V-1 | Zfp455 |
| 10400 | 3 | 4 | 5 | | V-1 | Zfp456 |
| 10401 | 3 | 4 | 5 | | V-1 | Zfp458 |
| 10402 | 3 | 4 | 5 | | V-1 | Zfp462 |
| 10403 | 3 | 4 | 5 | | V-1 | Zfp467 |
| 10404 | 3 | 4 | 5 | | V-1 | Zfp503 |
| 10405 | 3 | 4 | 5 | | V-1 | Zfp507 |
| 10406 | 3 | 4 | 5 | | V-1 | Zfp511 |
| 10407 | 3 | 4 | 5 | | V-1 | Zfp516 |
| 10408 | 3 | 4 | 5 | | V-1 | Zfp518a |
| 10409 | 3 | 4 | 5 | | V-1 | Zfp518b |
| 10410 | 3 | 4 | 5 | | V-1 | Zfp532 |
| 10411 | 3 | 4 | 5 | | V-1 | Zfp534 |
| 10412 | 3 | 4 | 5 | | V-1 | Zfp568 |
| 10413 | 3 | 4 | 5 | | V-1 | Zfp583 |
| 10414 | 3 | 4 | 5 | | V-1 | Zfp592 |
| 10415 | 3 | 4 | 5 | | V-1 | Zfp595 |
| 10416 | 3 | 4 | 5 | | V-1 | Zfp599 |
| 10417 | 3 | 4 | 5 | | V-1 | Zfp607 |
| 10418 | 3 | 4 | 5 | | V-1 | Zfp608 |
| 10419 | 3 | 4 | 5 | | V-1 | Zfp609 |
| 10420 | 3 | 4 | 5 | | V-1 | Zfp619 |
| 10421 | 3 | 4 | 5 | | V-1 | Zfp62 |
| 10422 | 3 | 4 | 5 | | V-1 | Zfp641 |
| 10423 | 3 | 4 | 5 | | V-1 | Zfp646 |
| 10424 | 3 | 4 | 5 | | V-1 | Zfp647 |
| 10425 | 3 | 4 | 5 | | V-1 | Zfp668 |
| 10426 | 3 | 4 | 5 | | V-1 | Zfp687 |
| 10427 | 3 | 4 | 5 | | V-1 | Zfp692 |
| 10428 | 3 | 4 | 5 | | V-1 | Zfp707 |
| 10429 | 3 | 4 | 5 | | V-1 | Zfp708 |
| 10430 | 3 | 4 | 5 | | V-1 | Zfp710 |
| 10431 | 3 | 4 | 5 | | V-1 | Zfp712 |
| 10432 | 3 | 4 | 5 | | V-1 | Zfp738 |
| 10433 | 3 | 4 | 5 | | V-1 | Zfp74 |
| 10434 | 3 | 4 | 5 | | V-1 | Zfp770 |
| 10435 | 3 | 4 | 5 | | V-1 | Zfp771 |
| 10436 | 3 | 4 | 5 | | V-1 | Zfp772 |
| 10437 | 3 | 4 | 5 | | V-1 | Zfp780b |
| 10438 | 3 | 4 | 5 | | V-1 | Zfp799 |
| 10439 | 3 | 4 | 5 | | V-1 | Zfp800 |
| 10440 | 3 | 4 | 5 | | V-1 | Zfp809 |
| 10441 | 3 | 4 | 5 | | V-1 | Zfp81 |
| 10442 | 3 | 4 | 5 | | V-1 | Zfp820 |
| 10443 | 3 | 4 | 5 | | V-1 | Zfp827 |
| 10444 | 3 | 4 | 5 | | V-1 | Zfp831 |
| 10445 | 3 | 4 | 5 | | V-1 | Zfp862-ps |
| 10446 | 3 | 4 | 5 | | V-1 | Zfp866 |
| 10447 | 3 | 4 | 5 | | V-1 | Zfp871 |
| 10448 | 3 | 4 | 5 | | V-1 | Zfp873 |
| 10449 | 3 | 4 | 5 | | V-1 | Zfp879 |
| 10450 | 3 | 4 | 5 | | V-1 | Zfp9 |
| 10451 | 3 | 4 | 5 | | V-1 | Zfp932 |
| 10452 | 3 | 4 | 5 | | V-1 | Zfp934 |
| 10453 | 3 | 4 | 5 | | V-1 | Zfp939 |
| 10454 | 3 | 4 | 5 | | V-1 | Zfp940 |
| 10455 | 3 | 4 | 5 | | V-1 | Zfp948 |
| 10456 | 3 | 4 | 5 | | V-1 | Zfp954 |
| 10457 | 3 | 4 | 5 | | V-1 | Zfp955b |
| 10458 | 3 | 4 | 5 | | V-1 | Zfp956 |
| 10459 | 3 | 4 | 5 | | V-1 | Zfp964 |
| 10460 | 3 | 4 | 5 | | V-1 | Zfpl1 |
| 10461 | 3 | 4 | 5 | | V-1 | Zfpm1 |
| 10462 | 3 | 4 | 5 | | V-1 | Zfyve16 |
| 10463 | 3 | 4 | 5 | | V-1 | Zfyve19 |
| 10464 | 3 | 4 | 5 | | V-1 | Zfyve21 |
| 10465 | 3 | 4 | 5 | | V-1 | Zfyve26 |
| 10466 | 3 | 4 | 5 | | V-1 | Zfyve28 |
| 10467 | 3 | 4 | 5 | | V-1 | Zik1 |
| 10468 | 3 | 4 | 5 | | V-1 | Zkscan1 |
| 10469 | 3 | 4 | 5 | | V-1 | Zkscan8 |
| 10470 | 3 | 4 | 5 | | V-1 | Zmat5 |
| 10471 | 3 | 4 | 5 | | V-1 | Znhit1 |
| 10472 | 3 | 4 | 5 | | V-1 | Znhit3 |
| 10473 | 3 | 4 | 5 | | V-1 | Znrd1 |
| 10474 | 3 | 4 | 5 | | V-1 | Zpld1 |
| 10475 | 3 | 4 | 5 | | V-1 | Zranb2 |
| 10476 | 3 | 4 | 5 | | V-1 | Zscan10 |
| 10477 | 3 | 4 | 5 | | V-1 | Zscan18 |
| 10478 | 3 | 4 | 5 | | V-1 | Zscan20 |
| 10479 | 3 | 4 | 5 | | V-1 | Zscan22 |
| 10480 | 3 | 4 | 5 | | V-1 | Zswim3 |
| 10481 | 3 | 4 | 5 | | V-1 | Zswim5 |
| 10482 | 3 | 4 | 5 | | V-1 | Zswim8 |
| 10483 | 3 | 4 | 5 | | V-1 | Zxda |
| 10484 | 3 | 4 | 5 | | V-1 | Zxdc |
| 10485 | 3 | 4 | 5 | | V-1 | Zyg11a |
| 10486 | 3 | 4 | 5 | | V-1 | Zyg11b |
| 10487 | 3 | 4 | 5 | | V-1 | Zzef1 |
| 10488 | 3 | 4 | 5 | | V-1 | a |
| 10489 | 3 | 4 | 5 | | V-1 | l7Rn6 |
| 10490 | 3 | 4 | | | IV-2 | 1110032F04Rik |
| 10491 | 3 | 4 | | | IV-2 | 1700003G18Rik |
| 10492 | 3 | 4 | | | IV-2 | 1700003L19Rik |
| 10493 | 3 | 4 | | | IV-2 | 1700011B04Rik |
| 10494 | 3 | 4 | | | IV-2 | 1700015F17Rik |
| 10495 | 3 | 4 | | | IV-2 | 1700016L21Rik |
| 10496 | 3 | 4 | | | IV-2 | 1700019B03Rik |
| 10497 | 3 | 4 | | | IV-2 | 1700022H16Rik |
| 10498 | 3 | 4 | | | IV-2 | 1700023F02Rik |
| 10499 | 3 | 4 | | | IV-2 | 1700030M09Rik |
| 10500 | 3 | 4 | | | IV-2 | 1700042B14Rik |
| 10501 | 3 | 4 | | | IV-2 | 1700060C16Rik |
| 10502 | 3 | 4 | | | IV-2 | 1700061I17Rik |
| 10503 | 3 | 4 | | | IV-2 | 1700064M15Rik |
| 10504 | 3 | 4 | | | IV-2 | 1700065L07Rik |
| 10505 | 3 | 4 | | | IV-2 | 1700072O05Rik |
| 10506 | 3 | 4 | | | IV-2 | 1700074P13Rik |
| 10507 | 3 | 4 | | | IV-2 | 1700110I01Rik |
| 10508 | 3 | 4 | | | IV-2 | 1700123L14Rik |
| 10509 | 3 | 4 | | | IV-2 | 1810065E05Rik |
| 10510 | 3 | 4 | | | IV-2 | 2310043O21Rik |
| 10511 | 3 | 4 | | | IV-2 | 2310050C09Rik |
| 10512 | 3 | 4 | | | IV-2 | 2410124H12Rik |
| 10513 | 3 | 4 | | | IV-2 | 2610028H24Rik |
| 10514 | 3 | 4 | | | IV-2 | 3010033K07Rik |
| 10515 | 3 | 4 | | | IV-2 | 4921511H03Rik |
| 10516 | 3 | 4 | | | IV-2 | 4921513I03Rik |
| 10517 | 3 | 4 | | | IV-2 | 4921517D22Rik |
| 10518 | 3 | 4 | | | IV-2 | 4921525O09Rik |
| 10519 | 3 | 4 | | | IV-2 | 4930402F11Rik |
| 10520 | 3 | 4 | | | IV-2 | 4930404A10Rik |
| 10521 | 3 | 4 | | | IV-2 | 4930407I10Rik |
| 10522 | 3 | 4 | | | IV-2 | 4930417O22Rik |
| 10523 | 3 | 4 | | | IV-2 | 4930433I11Rik |
| 10524 | 3 | 4 | | | IV-2 | 4930435E12Rik |
| 10525 | 3 | 4 | | | IV-2 | 4930440C22Rik |
| 10526 | 3 | 4 | | | IV-2 | 4930447A16Rik |
| 10527 | 3 | 4 | | | IV-2 | 4930448K20Rik |
| 10528 | 3 | 4 | | | IV-2 | 4930455F16Rik |
| 10529 | 3 | 4 | | | IV-2 | 4930463O16Rik |
| 10530 | 3 | 4 | | | IV-2 | 4930465K10Rik |
| 10531 | 3 | 4 | | | IV-2 | 4930467D21Rik |
| 10532 | 3 | 4 | | | IV-2 | 4930471G03Rik |
| 10533 | 3 | 4 | | | IV-2 | 4930482G09Rik |
| 10534 | 3 | 4 | | | IV-2 | 4930503E14Rik |
| 10535 | 3 | 4 | | | IV-2 | 4930505A04Rik |
| 10536 | 3 | 4 | | | IV-2 | 4930509J09Rik |
| 10537 | 3 | 4 | | | IV-2 | 4930511A02Rik |
| 10538 | 3 | 4 | | | IV-2 | 4930515L19Rik |
| 10539 | 3 | 4 | | | IV-2 | 4930524O05Rik |
| 10540 | 3 | 4 | | | IV-2 | 4930558J18Rik |
| 10541 | 3 | 4 | | | IV-2 | 4930563D23Rik |
| 10542 | 3 | 4 | | | IV-2 | 4930563F08Rik |
| 10543 | 3 | 4 | | | IV-2 | 4930564D02Rik |
| 10544 | 3 | 4 | | | IV-2 | 4930571K23Rik |
| 10545 | 3 | 4 | | | IV-2 | 4930583K01Rik |
| 10546 | 3 | 4 | | | IV-2 | 4930590J08Rik |
| 10547 | 3 | 4 | | | IV-2 | 4930597G03Rik |
| 10548 | 3 | 4 | | | IV-2 | 4930599N23Rik |
| 10549 | 3 | 4 | | | IV-2 | 4931419H13Rik |
| 10550 | 3 | 4 | | | IV-2 | 4931431F19Rik |
| 10551 | 3 | 4 | | | IV-2 | 4931440L10Rik |
| 10552 | 3 | 4 | | | IV-2 | 4932411N23Rik |
| 10553 | 3 | 4 | | | IV-2 | 4932414N04Rik |
| 10554 | 3 | 4 | | | IV-2 | 4932443I19Rik |
| 10555 | 3 | 4 | | | IV-2 | 4933400F21Rik |
| 10556 | 3 | 4 | | | IV-2 | 4933401D09Rik |
| 10557 | 3 | 4 | | | IV-2 | 4933402N03Rik |
| 10558 | 3 | 4 | | | IV-2 | 4933405O20Rik |

Fig. 36 - 56

| | | | | | | | | | | | | | |
|---|---|---|---|---|---|---|---|---|---|---|---|---|---|
| 10559 | 3 | 4 | | | IV-2 | 4933406K04Rik | 10655 | 3 | 4 | | | IV-2 | Cyp2c38 |
| 10560 | 3 | 4 | | | IV-2 | 4933407E24Rik | 10656 | 3 | 4 | | | IV-2 | Cyp2c39 |
| 10561 | 3 | 4 | | | IV-2 | 4933408N05Rik | 10657 | 3 | 4 | | | IV-2 | Cyp2c54 |
| 10562 | 3 | 4 | | | IV-2 | 4933412E24Rik | 10658 | 3 | 4 | | | IV-2 | Cyp2d34 |
| 10563 | 3 | 4 | | | IV-2 | 4933412O06Rik | 10659 | 3 | 4 | | | IV-2 | Cyp4f41-ps |
| 10564 | 3 | 4 | | | IV-2 | 4933434I20Rik | 10660 | 3 | 4 | | | IV-2 | Cyct8 |
| 10565 | 3 | 4 | | | IV-2 | 4933438B17Rik | 10661 | 3 | 4 | | | IV-2 | D16Ertd519e |
| 10566 | 3 | 4 | | | IV-2 | 4933440J02Rik | 10662 | 3 | 4 | | | IV-2 | D630013N20Rik |
| 10567 | 3 | 4 | | | IV-2 | 5330411J11Rik | 10663 | 3 | 4 | | | IV-2 | D630045M09Rik |
| 10568 | 3 | 4 | | | IV-2 | 5430419D17Rik | 10664 | 3 | 4 | | | IV-2 | D930028M14Rik |
| 10569 | 3 | 4 | | | IV-2 | 5730460C07Rik | 10665 | 3 | 4 | | | IV-2 | Dcaf12l2 |
| 10570 | 3 | 4 | | | IV-2 | 9030625G05Rik | 10666 | 3 | 4 | | | IV-2 | Dcpp1 |
| 10571 | 3 | 4 | | | IV-2 | 9430014N10Rik | 10667 | 3 | 4 | | | IV-2 | Ddx43 |
| 10572 | 3 | 4 | | | IV-2 | 9430060I03Rik | 10668 | 3 | 4 | | | IV-2 | Defb22 |
| 10573 | 3 | 4 | | | IV-2 | 9530091C08Rik | 10669 | 3 | 4 | | | IV-2 | Dlx4 |
| 10574 | 3 | 4 | | | IV-2 | A230009B12Rik | 10670 | 3 | 4 | | | IV-2 | Dusp21 |
| 10575 | 3 | 4 | | | IV-2 | A330048O09Rik | 10671 | 3 | 4 | | | IV-2 | Dux |
| 10576 | 3 | 4 | | | IV-2 | A3galt2 | 10672 | 3 | 4 | | | IV-2 | E030019B13Rik |
| 10577 | 3 | 4 | | | IV-2 | A630010A05Rik | 10673 | 3 | 4 | | | IV-2 | E130218I03Rik |
| 10578 | 3 | 4 | | | IV-2 | A630076J17Rik | 10674 | 3 | 4 | | | IV-2 | E130309F12Rik |
| 10579 | 3 | 4 | | | IV-2 | A730090N16Rik | 10675 | 3 | 4 | | | IV-2 | E230025N22Rik |
| 10580 | 3 | 4 | | | IV-2 | A930007I19Rik | 10676 | 3 | 4 | | | IV-2 | E430016F16Rik |
| 10581 | 3 | 4 | | | IV-2 | AF366264 | 10677 | 3 | 4 | | | IV-2 | Ear7 |
| 10582 | 3 | 4 | | | IV-2 | AI606473 | 10678 | 3 | 4 | | | IV-2 | Enthd1 |
| 10583 | 3 | 4 | | | IV-2 | AU022751 | 10679 | 3 | 4 | | | IV-2 | Etd |
| 10584 | 3 | 4 | | | IV-2 | AU022793 | 10680 | 3 | 4 | | | IV-2 | F9 |
| 10585 | 3 | 4 | | | IV-2 | AW822252 | 10681 | 3 | 4 | | | IV-2 | F930015N05Rik |
| 10586 | 3 | 4 | | | IV-2 | Abca17 | 10682 | 3 | 4 | | | IV-2 | Fam129c |
| 10587 | 3 | 4 | | | IV-2 | Abca4 | 10683 | 3 | 4 | | | IV-2 | Fam154a |
| 10588 | 3 | 4 | | | IV-2 | Acbd7 | 10684 | 3 | 4 | | | IV-2 | Fam186b |
| 10589 | 3 | 4 | | | IV-2 | Actl11 | 10685 | 3 | 4 | | | IV-2 | Fam187a |
| 10590 | 3 | 4 | | | IV-2 | Actrt2 | 10686 | 3 | 4 | | | IV-2 | Fam19a2 |
| 10591 | 3 | 4 | | | IV-2 | Adam20 | 10687 | 3 | 4 | | | IV-2 | Fam221b |
| 10592 | 3 | 4 | | | IV-2 | Adam3 | 10688 | 3 | 4 | | | IV-2 | Fam71a |
| 10593 | 3 | 4 | | | IV-2 | Adamts19 | 10689 | 3 | 4 | | | IV-2 | Fbxo39 |
| 10594 | 3 | 4 | | | IV-2 | Adcy10 | 10690 | 3 | 4 | | | IV-2 | Fbxo47 |
| 10595 | 3 | 4 | | | IV-2 | Agxt | 10691 | 3 | 4 | | | IV-2 | Fer1l5 |
| 10596 | 3 | 4 | | | IV-2 | Aipl1 | 10692 | 3 | 4 | | | IV-2 | Fosl1 |
| 10597 | 3 | 4 | | | IV-2 | Akap4 | 10693 | 3 | 4 | | | IV-2 | Foxe3 |
| 10598 | 3 | 4 | | | IV-2 | Ankmy1 | 10694 | 3 | 4 | | | IV-2 | Foxh1 |
| 10599 | 3 | 4 | | | IV-2 | Asic4 | 10695 | 3 | 4 | | | IV-2 | Fscn3 |
| 10600 | 3 | 4 | | | IV-2 | Atp8b3 | 10696 | 3 | 4 | | | IV-2 | Fstl5 |
| 10601 | 3 | 4 | | | IV-2 | Awat1 | 10697 | 3 | 4 | | | IV-2 | G630093K05Rik |
| 10602 | 3 | 4 | | | IV-2 | Aym1 | 10698 | 3 | 4 | | | IV-2 | Gabrd |
| 10603 | 3 | 4 | | | IV-2 | B130034C11Rik | 10699 | 3 | 4 | | | IV-2 | Galr1 |
| 10604 | 3 | 4 | | | IV-2 | B930018H19Rik | 10700 | 3 | 4 | | | IV-2 | Gdap1l1 |
| 10605 | 3 | 4 | | | IV-2 | BB287469 | 10701 | 3 | 4 | | | IV-2 | Glb1l3 |
| 10606 | 3 | 4 | | | IV-2 | BC024139 | 10702 | 3 | 4 | | | IV-2 | Gm10432 |
| 10607 | 3 | 4 | | | IV-2 | BC048671 | 10703 | 3 | 4 | | | IV-2 | Gm10536 |
| 10608 | 3 | 4 | | | IV-2 | BC048679 | 10704 | 3 | 4 | | | IV-2 | Gm10578 |
| 10609 | 3 | 4 | | | IV-2 | BC051537 | 10705 | 3 | 4 | | | IV-2 | Gm10787 |
| 10610 | 3 | 4 | | | IV-2 | BC061195 | 10706 | 3 | 4 | | | IV-2 | Gm11538 |
| 10611 | 3 | 4 | | | IV-2 | BC117090 | 10707 | 3 | 4 | | | IV-2 | Gm11981 |
| 10612 | 3 | 4 | | | IV-2 | Bcas3os2 | 10708 | 3 | 4 | | | IV-2 | Gm12159 |
| 10613 | 3 | 4 | | | IV-2 | Bcl2l10 | 10709 | 3 | 4 | | | IV-2 | Gm12530 |
| 10614 | 3 | 4 | | | IV-2 | Bhlha9 | 10710 | 3 | 4 | | | IV-2 | Gm136 |
| 10615 | 3 | 4 | | | IV-2 | Brinp3 | 10711 | 3 | 4 | | | IV-2 | Gm14169 |
| 10616 | 3 | 4 | | | IV-2 | Btbd17 | 10712 | 3 | 4 | | | IV-2 | Gm14374 |
| 10617 | 3 | 4 | | | IV-2 | Btbd18 | 10713 | 3 | 4 | | | IV-2 | Gm14461 |
| 10618 | 3 | 4 | | | IV-2 | C030029H02Rik | 10714 | 3 | 4 | | | IV-2 | Gm14482 |
| 10619 | 3 | 4 | | | IV-2 | C1ql2 | 10715 | 3 | 4 | | | IV-2 | Gm14634 |
| 10620 | 3 | 4 | | | IV-2 | C2cd4d | 10716 | 3 | 4 | | | IV-2 | Gm15107 |
| 10621 | 3 | 4 | | | IV-2 | C330024D21Rik | 10717 | 3 | 4 | | | IV-2 | Gm16863 |
| 10622 | 3 | 4 | | | IV-2 | CK137956 | 10718 | 3 | 4 | | | IV-2 | Gm17801 |
| 10623 | 3 | 4 | | | IV-2 | Cacna2d4 | 10719 | 3 | 4 | | | IV-2 | Gm19583 |
| 10624 | 3 | 4 | | | IV-2 | Capn11 | 10720 | 3 | 4 | | | IV-2 | Gm19689 |
| 10625 | 3 | 4 | | | IV-2 | Catsperg2 | 10721 | 3 | 4 | | | IV-2 | Gm1979 |
| 10626 | 3 | 4 | | | IV-2 | Cbln1 | 10722 | 3 | 4 | | | IV-2 | Gm20871 |
| 10627 | 3 | 4 | | | IV-2 | Ccin | 10723 | 3 | 4 | | | IV-2 | Gm2373 |
| 10628 | 3 | 4 | | | IV-2 | Cct6b | 10724 | 3 | 4 | | | IV-2 | Gm2848 |
| 10629 | 3 | 4 | | | IV-2 | Cd46 | 10725 | 3 | 4 | | | IV-2 | Gm2863 |
| 10630 | 3 | 4 | | | IV-2 | Cd79b | 10726 | 3 | 4 | | | IV-2 | Gm4922 |
| 10631 | 3 | 4 | | | IV-2 | Cdh22 | 10727 | 3 | 4 | | | IV-2 | Gm4971 |
| 10632 | 3 | 4 | | | IV-2 | Cdrt4 | 10728 | 3 | 4 | | | IV-2 | Gm5 |
| 10633 | 3 | 4 | | | IV-2 | Cdx1 | 10729 | 3 | 4 | | | IV-2 | Gm5091 |
| 10634 | 3 | 4 | | | IV-2 | Ceacam18 | 10730 | 3 | 4 | | | IV-2 | Gm5111 |
| 10635 | 3 | 4 | | | IV-2 | Ceacam3 | 10731 | 3 | 4 | | | IV-2 | Gm5129 |
| 10636 | 3 | 4 | | | IV-2 | Ces1a | 10732 | 3 | 4 | | | IV-2 | Gm5134 |
| 10637 | 3 | 4 | | | IV-2 | Chrna5 | 10733 | 3 | 4 | | | IV-2 | Gm5142 |
| 10638 | 3 | 4 | | | IV-2 | Cldn17 | 10734 | 3 | 4 | | | IV-2 | Gm5468 |
| 10639 | 3 | 4 | | | IV-2 | Clec2f | 10735 | 3 | 4 | | | IV-2 | Gm5893 |
| 10640 | 3 | 4 | | | IV-2 | Cmtm1 | 10736 | 3 | 4 | | | IV-2 | Gm590 |
| 10641 | 3 | 4 | | | IV-2 | Cngb3 | 10737 | 3 | 4 | | | IV-2 | Gm6460 |
| 10642 | 3 | 4 | | | IV-2 | Cntnap5c | 10738 | 3 | 4 | | | IV-2 | Gm6583 |
| 10643 | 3 | 4 | | | IV-2 | Col9a1 | 10739 | 3 | 4 | | | IV-2 | Gm6760 |
| 10644 | 3 | 4 | | | IV-2 | Cpa4 | 10740 | 3 | 4 | | | IV-2 | Gm6815 |
| 10645 | 3 | 4 | | | IV-2 | Crct1 | 10741 | 3 | 4 | | | IV-2 | Gm6880 |
| 10646 | 3 | 4 | | | IV-2 | Crygb | 10742 | 3 | 4 | | | IV-2 | Gm7008 |
| 10647 | 3 | 4 | | | IV-2 | Cst13 | 10743 | 3 | 4 | | | IV-2 | Gm8096 |
| 10648 | 3 | 4 | | | IV-2 | Ctag2 | 10744 | 3 | 4 | | | IV-2 | Gm9696 |
| 10649 | 3 | 4 | | | IV-2 | Cxcl11 | 10745 | 3 | 4 | | | IV-2 | Gm9731 |
| 10650 | 3 | 4 | | | IV-2 | Cyp1a1 | 10746 | 3 | 4 | | | IV-2 | Gpc5 |
| 10651 | 3 | 4 | | | IV-2 | Cyp24a1 | 10747 | 3 | 4 | | | IV-2 | Gsc2 |
| 10652 | 3 | 4 | | | IV-2 | Cyp2ab1 | 10748 | 3 | 4 | | | IV-2 | Gtsf1l |
| 10653 | 3 | 4 | | | IV-2 | Cyp2b13 | 10749 | 3 | 4 | | | IV-2 | Gzmc |
| 10654 | 3 | 4 | | | IV-2 | Cyp2b23 | 10750 | 3 | 4 | | | IV-2 | H1fnt |

Fig. 36 - 57

| | | | | | | |
|---|---|---|---|---|---|---|
| 10751 | 3 | 4 | | | IV-2 | H2-Eb2 |
| 10752 | 3 | 4 | | | IV-2 | H2-M10.2 |
| 10753 | 3 | 4 | | | IV-2 | Hhipl2 |
| 10754 | 3 | 4 | | | IV-2 | Hist1h1t |
| 10755 | 3 | 4 | | | IV-2 | Hist1h3f |
| 10756 | 3 | 4 | | | IV-2 | Hist1h3g |
| 10757 | 3 | 4 | | | IV-2 | Hoxd13 |
| 10758 | 3 | 4 | | | IV-2 | Hoxd3os1 |
| 10759 | 3 | 4 | | | IV-2 | Hrnr |
| 10760 | 3 | 4 | | | IV-2 | Htr3b |
| 10761 | 3 | 4 | | | IV-2 | I730030J21Rik |
| 10762 | 3 | 4 | | | IV-2 | Idi2 |
| 10763 | 3 | 4 | | | IV-2 | Igj |
| 10764 | 3 | 4 | | | IV-2 | Il13 |
| 10765 | 3 | 4 | | | IV-2 | Il1f10 |
| 10766 | 3 | 4 | | | IV-2 | Il25 |
| 10767 | 3 | 4 | | | IV-2 | Impg2 |
| 10768 | 3 | 4 | | | IV-2 | Ism2 |
| 10769 | 3 | 4 | | | IV-2 | Kcnh8 |
| 10770 | 3 | 4 | | | IV-2 | Kcnj4 |
| 10771 | 3 | 4 | | | IV-2 | Kctd19 |
| 10772 | 3 | 4 | | | IV-2 | Kdm4d |
| 10773 | 3 | 4 | | | IV-2 | Khdrbs2 |
| 10774 | 3 | 4 | | | IV-2 | Kir3dl1 |
| 10775 | 3 | 4 | | | IV-2 | Klk9 |
| 10776 | 3 | 4 | | | IV-2 | Klrc2 |
| 10777 | 3 | 4 | | | IV-2 | Kpna7 |
| 10778 | 3 | 4 | | | IV-2 | Kprp |
| 10779 | 3 | 4 | | | IV-2 | Krt24 |
| 10780 | 3 | 4 | | | IV-2 | Krt42 |
| 10781 | 3 | 4 | | | IV-2 | Krt6a |
| 10782 | 3 | 4 | | | IV-2 | Krt6b |
| 10783 | 3 | 4 | | | IV-2 | Krt9 |
| 10784 | 3 | 4 | | | IV-2 | Krtap16-1 |
| 10785 | 3 | 4 | | | IV-2 | Krtap4-13 |
| 10786 | 3 | 4 | | | IV-2 | L1td1 |
| 10787 | 3 | 4 | | | IV-2 | LOC102632430 |
| 10788 | 3 | 4 | | | IV-2 | Lce1b |
| 10789 | 3 | 4 | | | IV-2 | Lce1d |
| 10790 | 3 | 4 | | | IV-2 | Lce1e |
| 10791 | 3 | 4 | | | IV-2 | Lce1f |
| 10792 | 3 | 4 | | | IV-2 | Lce1g |
| 10793 | 3 | 4 | | | IV-2 | Lce1i |
| 10794 | 3 | 4 | | | IV-2 | Lce1j |
| 10795 | 3 | 4 | | | IV-2 | Lce1k |
| 10796 | 3 | 4 | | | IV-2 | Lce3a |
| 10797 | 3 | 4 | | | IV-2 | Lce6a |
| 10798 | 3 | 4 | | | IV-2 | Ldirad1 |
| 10799 | 3 | 4 | | | IV-2 | Lmx1a |
| 10800 | 3 | 4 | | | IV-2 | Loxhd1 |
| 10801 | 3 | 4 | | | IV-2 | Lrit2 |
| 10802 | 3 | 4 | | | IV-2 | Lrriq4 |
| 10803 | 3 | 4 | | | IV-2 | Magea3 |
| 10804 | 3 | 4 | | | IV-2 | Magea8 |
| 10805 | 3 | 4 | | | IV-2 | Mageb18 |
| 10806 | 3 | 4 | | | IV-2 | Megf11 |
| 10807 | 3 | 4 | | | IV-2 | Mov10l1 |
| 10808 | 3 | 4 | | | IV-2 | Mrgprb3 |
| 10809 | 3 | 4 | | | IV-2 | Mroh2a |
| 10810 | 3 | 4 | | | IV-2 | Mroh4 |
| 10811 | 3 | 4 | | | IV-2 | Mroh8 |
| 10812 | 3 | 4 | | | IV-2 | Mutyh |
| 10813 | 3 | 4 | | | IV-2 | Myf5 |
| 10814 | 3 | 4 | | | IV-2 | Myh13 |
| 10815 | 3 | 4 | | | IV-2 | Myh3 |
| 10816 | 3 | 4 | | | IV-2 | Naa11 |
| 10817 | 3 | 4 | | | IV-2 | Nap1l2 |
| 10818 | 3 | 4 | | | IV-2 | Neurog1 |
| 10819 | 3 | 4 | | | IV-2 | Ninj2 |
| 10820 | 3 | 4 | | | IV-2 | Nlrp5 |
| 10821 | 3 | 4 | | | IV-2 | Npffr1 |
| 10822 | 3 | 4 | | | IV-2 | Npm2 |
| 10823 | 3 | 4 | | | IV-2 | Nppb |
| 10824 | 3 | 4 | | | IV-2 | Nps |
| 10825 | 3 | 4 | | | IV-2 | Npvf |
| 10826 | 3 | 4 | | | IV-2 | Npy5r |
| 10827 | 3 | 4 | | | IV-2 | Nr1i3 |
| 10828 | 3 | 4 | | | IV-2 | Ntrk1 |
| 10829 | 3 | 4 | | | IV-2 | Olfr1090 |
| 10830 | 3 | 4 | | | IV-2 | Olfr1280 |
| 10831 | 3 | 4 | | | IV-2 | Olfr1349 |
| 10832 | 3 | 4 | | | IV-2 | Olfr1495 |
| 10833 | 3 | 4 | | | IV-2 | Olfr199 |
| 10834 | 3 | 4 | | | IV-2 | Olfr212 |
| 10835 | 3 | 4 | | | IV-2 | Olfr303 |
| 10836 | 3 | 4 | | | IV-2 | Olfr31 |
| 10837 | 3 | 4 | | | IV-2 | Olfr432 |
| 10838 | 3 | 4 | | | IV-2 | Olfr520 |
| 10839 | 3 | 4 | | | IV-2 | Olfr523 |
| 10840 | 3 | 4 | | | IV-2 | Olfr732 |
| 10841 | 3 | 4 | | | IV-2 | Olfr788 |
| 10842 | 3 | 4 | | | IV-2 | Olfr994 |
| 10843 | 3 | 4 | | | IV-2 | Olig2 |
| 10844 | 3 | 4 | | | IV-2 | Oosp2 |
| 10845 | 3 | 4 | | | IV-2 | Opn4 |
| 10846 | 3 | 4 | | | IV-2 | Otos |
| 10847 | 3 | 4 | | | IV-2 | Ott |
| 10848 | 3 | 4 | | | IV-2 | Otx2 |
| 10849 | 3 | 4 | | | IV-2 | Oxct2a |
| 10850 | 3 | 4 | | | IV-2 | Oxct2b |
| 10851 | 3 | 4 | | | IV-2 | Oxgr1 |
| 10852 | 3 | 4 | | | IV-2 | Pax1 |
| 10853 | 3 | 4 | | | IV-2 | Pax6 |
| 10854 | 3 | 4 | | | IV-2 | Pbp2 |
| 10855 | 3 | 4 | | | IV-2 | Pcdhgb8 |
| 10856 | 3 | 4 | | | IV-2 | Phactr3 |
| 10857 | 3 | 4 | | | IV-2 | Phex |
| 10858 | 3 | 4 | | | IV-2 | Pitpnm2os1 |
| 10859 | 3 | 4 | | | IV-2 | Plcz1 |
| 10860 | 3 | 4 | | | IV-2 | Pms2 |
| 10861 | 3 | 4 | | | IV-2 | Pnpla5 |
| 10862 | 3 | 4 | | | IV-2 | Pom121l12 |
| 10863 | 3 | 4 | | | IV-2 | Pou5f2 |
| 10864 | 3 | 4 | | | IV-2 | Pou6f2 |
| 10865 | 3 | 4 | | | IV-2 | Ppef1 |
| 10866 | 3 | 4 | | | IV-2 | Ppfia3 |
| 10867 | 3 | 4 | | | IV-2 | Ppp1r17 |
| 10868 | 3 | 4 | | | IV-2 | Ppp1r2-ps7 |
| 10869 | 3 | 4 | | | IV-2 | Ppp3r2 |
| 10870 | 3 | 4 | | | IV-2 | Pramef12 |
| 10871 | 3 | 4 | | | IV-2 | Prl3c1 |
| 10872 | 3 | 4 | | | IV-2 | Prr23a |
| 10873 | 3 | 4 | | | IV-2 | Prrt3 |
| 10874 | 3 | 4 | | | IV-2 | Prss37 |
| 10875 | 3 | 4 | | | IV-2 | Prss40 |
| 10876 | 3 | 4 | | | IV-2 | Prss42 |
| 10877 | 3 | 4 | | | IV-2 | Prss51 |
| 10878 | 3 | 4 | | | IV-2 | Ptgdr |
| 10879 | 3 | 4 | | | IV-2 | Pydc3 |
| 10880 | 3 | 4 | | | IV-2 | Raet1d |
| 10881 | 3 | 4 | | | IV-2 | Raet1e |
| 10882 | 3 | 4 | | | IV-2 | Ralyl |
| 10883 | 3 | 4 | | | IV-2 | Rbm46os |
| 10884 | 3 | 4 | | | IV-2 | Rhag |
| 10885 | 3 | 4 | | | IV-2 | Rhoh |
| 10886 | 3 | 4 | | | IV-2 | Rhox2a |
| 10887 | 3 | 4 | | | IV-2 | Ripply1 |
| 10888 | 3 | 4 | | | IV-2 | Rnf133 |
| 10889 | 3 | 4 | | | IV-2 | Rp1 |
| 10890 | 3 | 4 | | | IV-2 | S100a5 |
| 10891 | 3 | 4 | | | IV-2 | S100z |
| 10892 | 3 | 4 | | | IV-2 | Samt3 |
| 10893 | 3 | 4 | | | IV-2 | Sat1l |
| 10894 | 3 | 4 | | | IV-2 | Scarlettr |
| 10895 | 3 | 4 | | | IV-2 | Scgb1b3 |
| 10896 | 3 | 4 | | | IV-2 | Scgb2b15 |
| 10897 | 3 | 4 | | | IV-2 | Serpina3j |
| 10898 | 3 | 4 | | | IV-2 | Serpinb3c |
| 10899 | 3 | 4 | | | IV-2 | Serpinb6d |
| 10900 | 3 | 4 | | | IV-2 | Sh2d4b |
| 10901 | 3 | 4 | | | IV-2 | Sim1 |
| 10902 | 3 | 4 | | | IV-2 | Six3 |
| 10903 | 3 | 4 | | | IV-2 | Skor2 |
| 10904 | 3 | 4 | | | IV-2 | Slc12a1 |
| 10905 | 3 | 4 | | | IV-2 | Slc22a13 |
| 10906 | 3 | 4 | | | IV-2 | Slc22a20 |
| 10907 | 3 | 4 | | | IV-2 | Slc35f4 |
| 10908 | 3 | 4 | | | IV-2 | Slc36a3 |
| 10909 | 3 | 4 | | | IV-2 | Slc45a2 |
| 10910 | 3 | 4 | | | IV-2 | Slc5a12 |
| 10911 | 3 | 4 | | | IV-2 | Slc6a20b |
| 10912 | 3 | 4 | | | IV-2 | Slc7a12 |
| 10913 | 3 | 4 | | | IV-2 | Slc9c1 |
| 10914 | 3 | 4 | | | IV-2 | Slfnl1 |
| 10915 | 3 | 4 | | | IV-2 | Sly |
| 10916 | 3 | 4 | | | IV-2 | Smok2b |
| 10917 | 3 | 4 | | | IV-2 | Smok3b |
| 10918 | 3 | 4 | | | IV-2 | Smok4a |
| 10919 | 3 | 4 | | | IV-2 | Sowahd |
| 10920 | 3 | 4 | | | IV-2 | Sox1 |
| 10921 | 3 | 4 | | | IV-2 | Sox15 |
| 10922 | 3 | 4 | | | IV-2 | Sox30 |
| 10923 | 3 | 4 | | | IV-2 | Sp9 |
| 10924 | 3 | 4 | | | IV-2 | Spag4 |
| 10925 | 3 | 4 | | | IV-2 | Spata31d1a |
| 10926 | 3 | 4 | | | IV-2 | Spata31d1b |
| 10927 | 3 | 4 | | | IV-2 | Spats1 |
| 10928 | 3 | 4 | | | IV-2 | Sprr2d |
| 10929 | 3 | 4 | | | IV-2 | Sprr3 |
| 10930 | 3 | 4 | | | IV-2 | Ssmem1 |
| 10931 | 3 | 4 | | | IV-2 | Ssxb5 |
| 10932 | 3 | 4 | | | IV-2 | St8sia3os |
| 10933 | 3 | 4 | | | IV-2 | Stpg2 |
| 10934 | 3 | 4 | | | IV-2 | Syngr4 |
| 10935 | 3 | 4 | | | IV-2 | Tbc1d21 |
| 10936 | 3 | 4 | | | IV-2 | Tcam1 |
| 10937 | 3 | 4 | | | IV-2 | Tcerg1l |
| 10938 | 3 | 4 | | | IV-2 | Tcp10b |
| 10939 | 3 | 4 | | | IV-2 | Tcp10c |
| 10940 | 3 | 4 | | | IV-2 | Tcstv1 |
| 10941 | 3 | 4 | | | IV-2 | Tecrl |
| 10942 | 3 | 4 | | | IV-2 | Tectb |

Fig. 36 - 58

| | | | | | | |
|---|---|---|---|---|---|---|
| 10943 | 3 | 4 | | | IV-2 | Tg |
| 10944 | 3 | 4 | | | IV-2 | Tgm5 |
| 10945 | 3 | 4 | | | IV-2 | Tktl2 |
| 10946 | 3 | 4 | | | IV-2 | Tlr11 |
| 10947 | 3 | 4 | | | IV-2 | Tmem207 |
| 10948 | 3 | 4 | | | IV-2 | Tmem235 |
| 10949 | 3 | 4 | | | IV-2 | Tmevpg1 |
| 10950 | 3 | 4 | | | IV-2 | Tmprss11bnl |
| 10951 | 3 | 4 | | | IV-2 | Tmprss11d |
| 10952 | 3 | 4 | | | IV-2 | Tmprss11f |
| 10953 | 3 | 4 | | | IV-2 | Tmprss11g |
| 10954 | 3 | 4 | | | IV-2 | Tnfrsf9 |
| 10955 | 3 | 4 | | | IV-2 | Tnni3k |
| 10956 | 3 | 4 | | | IV-2 | Tpo |
| 10957 | 3 | 4 | | | IV-2 | Trim42 |
| 10958 | 3 | 4 | | | IV-2 | Trim43c |
| 10959 | 3 | 4 | | | IV-2 | Trp53tg5 |
| 10960 | 3 | 4 | | | IV-2 | Ttc29 |
| 10961 | 3 | 4 | | | IV-2 | Ttll13 |
| 10962 | 3 | 4 | | | IV-2 | Ttll8 |
| 10963 | 3 | 4 | | | IV-2 | Txndc2 |
| 10964 | 3 | 4 | | | IV-2 | Ubqln3 |
| 10965 | 3 | 4 | | | IV-2 | Ubqlnl |
| 10966 | 3 | 4 | | | IV-2 | Ugt1a2 |
| 10967 | 3 | 4 | | | IV-2 | Usp50 |
| 10968 | 3 | 4 | | | IV-2 | Veph1 |
| 10969 | 3 | 4 | | | IV-2 | Vmn1r21 |
| 10970 | 3 | 4 | | | IV-2 | Vmn1r53 |
| 10971 | 3 | 4 | | | IV-2 | Vmn1r90 |
| 10972 | 3 | 4 | | | IV-2 | Vmn2r6 |
| 10973 | 3 | 4 | | | IV-2 | Vsx1 |
| 10974 | 3 | 4 | | | IV-2 | Vsx2 |
| 10975 | 3 | 4 | | | IV-2 | Vwa5b1 |
| 10976 | 3 | 4 | | | IV-2 | Wbscr25 |
| 10977 | 3 | 4 | | | IV-2 | Wfdc5 |
| 10978 | 3 | 4 | | | IV-2 | Wisp3 |
| 10979 | 3 | 4 | | | IV-2 | Xlr5c |
| 10980 | 3 | 4 | | | IV-2 | Zcchc13 |
| 10981 | 3 | 4 | | | IV-2 | Zfp42 |
| 10982 | 3 | 4 | | | IV-2 | Zfp541 |
| 10983 | 3 | 4 | | | IV-2 | Zfp735 |
| 10984 | 3 | 4 | | | IV-2 | Zfp936 |
| 10985 | 3 | 4 | | | IV-2 | Zfp957 |
| 10986 | 3 | 4 | | | IV-2 | Zmynd12 |
| 10987 | 3 | 4 | | | IV-1 | 0610009B22Rik |
| 10988 | 3 | 4 | | | IV-1 | 0610009O20Rik |
| 10989 | 3 | 4 | | | IV-1 | 0610010B08Rik |
| 10990 | 3 | 4 | | | IV-1 | 0610010F05Rik |
| 10991 | 3 | 4 | | | IV-1 | 0610012G03Rik |
| 10992 | 3 | 4 | | | IV-1 | 0610030E20Rik |
| 10993 | 3 | 4 | | | IV-1 | 1110007C09Rik |
| 10994 | 3 | 4 | | | IV-1 | 1110008L16Rik |
| 10995 | 3 | 4 | | | IV-1 | 1110015O18Rik |
| 10996 | 3 | 4 | | | IV-1 | 1110025L11Rik |
| 10997 | 3 | 4 | | | IV-1 | 1110037F02Rik |
| 10998 | 3 | 4 | | | IV-1 | 1110051M20Rik |
| 10999 | 3 | 4 | | | IV-1 | 1110057K04Rik |
| 11000 | 3 | 4 | | | IV-1 | 1190002N15Rik |
| 11001 | 3 | 4 | | | IV-1 | 1200014J11Rik |
| 11002 | 3 | 4 | | | IV-1 | 1300002K09Rik |
| 11003 | 3 | 4 | | | IV-1 | 1300017J02Rik |
| 11004 | 3 | 4 | | | IV-1 | 1500015L24Rik |
| 11005 | 3 | 4 | | | IV-1 | 1600002H07Rik |
| 11006 | 3 | 4 | | | IV-1 | 1600010M07Rik |
| 11007 | 3 | 4 | | | IV-1 | 1600012H06Rik |
| 11008 | 3 | 4 | | | IV-1 | 1600023N17Rik |
| 11009 | 3 | 4 | | | IV-1 | 1600027J07Rik |
| 11010 | 3 | 4 | | | IV-1 | 1700001C19Rik |
| 11011 | 3 | 4 | | | IV-1 | 1700001F09Rik |
| 11012 | 3 | 4 | | | IV-1 | 1700001G11Rik |
| 11013 | 3 | 4 | | | IV-1 | 1700001G17Rik |
| 11014 | 3 | 4 | | | IV-1 | 1700001K19Rik |
| 11015 | 3 | 4 | | | IV-1 | 1700001P01Rik |
| 11016 | 3 | 4 | | | IV-1 | 1700003E24Rik |
| 11017 | 3 | 4 | | | IV-1 | 1700003G13Rik |
| 11018 | 3 | 4 | | | IV-1 | 1700003H04Rik |
| 11019 | 3 | 4 | | | IV-1 | 1700003M02Rik |
| 11020 | 3 | 4 | | | IV-1 | 1700003P14Rik |
| 11021 | 3 | 4 | | | IV-1 | 1700006A11Rik |
| 11022 | 3 | 4 | | | IV-1 | 1700006E09Rik |
| 11023 | 3 | 4 | | | IV-1 | 1700006F04Rik |
| 11024 | 3 | 4 | | | IV-1 | 1700006H21Rik |
| 11025 | 3 | 4 | | | IV-1 | 1700007B14Rik |
| 11026 | 3 | 4 | | | IV-1 | 1700007F19Rik |
| 11027 | 3 | 4 | | | IV-1 | 1700007K09Rik |
| 11028 | 3 | 4 | | | IV-1 | 1700007P06Rik |
| 11029 | 3 | 4 | | | IV-1 | 1700008F21Rik |
| 11030 | 3 | 4 | | | IV-1 | 1700008I05Rik |
| 11031 | 3 | 4 | | | IV-1 | 1700008J07Rik |
| 11032 | 3 | 4 | | | IV-1 | 1700008K24Rik |
| 11033 | 3 | 4 | | | IV-1 | 1700008P02Rik |
| 11034 | 3 | 4 | | | IV-1 | 1700009N14Rik |
| 11035 | 3 | 4 | | | IV-1 | 1700010B08Rik |
| 11036 | 3 | 4 | | | IV-1 | 1700010D01Rik |
| 11037 | 3 | 4 | | | IV-1 | 1700010I14Rik |
| 11038 | 3 | 4 | | | IV-1 | 1700010I16Rik |
| 11039 | 3 | 4 | | | IV-1 | 1700011E24Rik |
| 11040 | 3 | 4 | | | IV-1 | 1700011I03Rik |
| 11041 | 3 | 4 | | | IV-1 | 1700011L22Rik |
| 11042 | 3 | 4 | | | IV-1 | 1700011M02Rik |
| 11043 | 3 | 4 | | | IV-1 | 1700012A03Rik |
| 11044 | 3 | 4 | | | IV-1 | 1700012B07Rik |
| 11045 | 3 | 4 | | | IV-1 | 1700012P22Rik |
| 11046 | 3 | 4 | | | IV-1 | 1700013D24Rik |
| 11047 | 3 | 4 | | | IV-1 | 1700013G24Rik |
| 11048 | 3 | 4 | | | IV-1 | 1700013H16Rik |
| 11049 | 3 | 4 | | | IV-1 | 1700015E13Rik |
| 11050 | 3 | 4 | | | IV-1 | 1700015G11Rik |
| 11051 | 3 | 4 | | | IV-1 | 1700016C15Rik |
| 11052 | 3 | 4 | | | IV-1 | 1700016D06Rik |
| 11053 | 3 | 4 | | | IV-1 | 1700016G22Rik |
| 11054 | 3 | 4 | | | IV-1 | 1700016H13Rik |
| 11055 | 3 | 4 | | | IV-1 | 1700016L04Rik |
| 11056 | 3 | 4 | | | IV-1 | 1700016P04Rik |
| 11057 | 3 | 4 | | | IV-1 | 1700017B05Rik |
| 11058 | 3 | 4 | | | IV-1 | 1700017D01Rik |
| 11059 | 3 | 4 | | | IV-1 | 1700017G19Rik |
| 11060 | 3 | 4 | | | IV-1 | 1700017J07Rik |
| 11061 | 3 | 4 | | | IV-1 | 1700017N19Rik |
| 11062 | 3 | 4 | | | IV-1 | 1700018B08Rik |
| 11063 | 3 | 4 | | | IV-1 | 1700018B24Rik |
| 11064 | 3 | 4 | | | IV-1 | 1700018F24Rik |
| 11065 | 3 | 4 | | | IV-1 | 1700019A02Rik |
| 11066 | 3 | 4 | | | IV-1 | 1700019B21Rik |
| 11067 | 3 | 4 | | | IV-1 | 1700019G24Rik |
| 11068 | 3 | 4 | | | IV-1 | 1700019M22Rik |
| 11069 | 3 | 4 | | | IV-1 | 1700019N19Rik |
| 11070 | 3 | 4 | | | IV-1 | 1700019O17Rik |
| 11071 | 3 | 4 | | | IV-1 | 1700020A23Rik |
| 11072 | 3 | 4 | | | IV-1 | 1700020G17Rik |
| 11073 | 3 | 4 | | | IV-1 | 1700020N01Rik |
| 11074 | 3 | 4 | | | IV-1 | 1700020N15Rik |
| 11075 | 3 | 4 | | | IV-1 | 1700020N18Rik |
| 11076 | 3 | 4 | | | IV-1 | 1700021K19Rik |
| 11077 | 3 | 4 | | | IV-1 | 1700022A21Rik |
| 11078 | 3 | 4 | | | IV-1 | 1700022E09Rik |
| 11079 | 3 | 4 | | | IV-1 | 1700022I11Rik |
| 11080 | 3 | 4 | | | IV-1 | 1700023C21Rik |
| 11081 | 3 | 4 | | | IV-1 | 1700023E05Rik |
| 11082 | 3 | 4 | | | IV-1 | 1700024B18Rik |
| 11083 | 3 | 4 | | | IV-1 | 1700024P04Rik |
| 11084 | 3 | 4 | | | IV-1 | 1700024P16Rik |
| 11085 | 3 | 4 | | | IV-1 | 1700025B11Rik |
| 11086 | 3 | 4 | | | IV-1 | 1700025C18Rik |
| 11087 | 3 | 4 | | | IV-1 | 1700025F22Rik |
| 11088 | 3 | 4 | | | IV-1 | 1700025F24Rik |
| 11089 | 3 | 4 | | | IV-1 | 1700025G04Rik |
| 11090 | 3 | 4 | | | IV-1 | 1700025K24Rik |
| 11091 | 3 | 4 | | | IV-1 | 1700025M24Rik |
| 11092 | 3 | 4 | | | IV-1 | 1700025N23Rik |
| 11093 | 3 | 4 | | | IV-1 | 1700026D08Rik |
| 11094 | 3 | 4 | | | IV-1 | 1700026D11Rik |
| 11095 | 3 | 4 | | | IV-1 | 1700026F02Rik |
| 11096 | 3 | 4 | | | IV-1 | 1700027A15Rik |
| 11097 | 3 | 4 | | | IV-1 | 1700027F09Rik |
| 11098 | 3 | 4 | | | IV-1 | 1700027I24Rik |
| 11099 | 3 | 4 | | | IV-1 | 1700028D13Rik |
| 11100 | 3 | 4 | | | IV-1 | 1700028E10Rik |
| 11101 | 3 | 4 | | | IV-1 | 1700028I16Rik |
| 11102 | 3 | 4 | | | IV-1 | 1700028K03Rik |
| 11103 | 3 | 4 | | | IV-1 | 1700028P14Rik |
| 11104 | 3 | 4 | | | IV-1 | 1700029B22Rik |
| 11105 | 3 | 4 | | | IV-1 | 1700029F12Rik |
| 11106 | 3 | 4 | | | IV-1 | 1700029H14Rik |
| 11107 | 3 | 4 | | | IV-1 | 1700029J03Rik |
| 11108 | 3 | 4 | | | IV-1 | 1700029M20Rik |
| 11109 | 3 | 4 | | | IV-1 | 1700029N11Rik |
| 11110 | 3 | 4 | | | IV-1 | 1700029P11Rik |
| 11111 | 3 | 4 | | | IV-1 | 1700030C10Rik |
| 11112 | 3 | 4 | | | IV-1 | 1700030F18Rik |
| 11113 | 3 | 4 | | | IV-1 | 1700030J22Rik |
| 11114 | 3 | 4 | | | IV-1 | 1700030K09Rik |
| 11115 | 3 | 4 | | | IV-1 | 1700030L20Rik |
| 11116 | 3 | 4 | | | IV-1 | 1700030O20Rik |
| 11117 | 3 | 4 | | | IV-1 | 1700031M16Rik |
| 11118 | 3 | 4 | | | IV-1 | 1700031P21Rik |
| 11119 | 3 | 4 | | | IV-1 | 1700034E13Rik |
| 11120 | 3 | 4 | | | IV-1 | 1700034F02Rik |
| 11121 | 3 | 4 | | | IV-1 | 1700034G24Rik |
| 11122 | 3 | 4 | | | IV-1 | 1700034I23Rik |
| 11123 | 3 | 4 | | | IV-1 | 1700034J05Rik |
| 11124 | 3 | 4 | | | IV-1 | 1700034K08Rik |
| 11125 | 3 | 4 | | | IV-1 | 1700034O15Rik |
| 11126 | 3 | 4 | | | IV-1 | 1700034P13Rik |
| 11127 | 3 | 4 | | | IV-1 | 1700036G14Rik |
| 11128 | 3 | 4 | | | IV-1 | 1700039E15Rik |
| 11129 | 3 | 4 | | | IV-1 | 1700039E22Rik |
| 11130 | 3 | 4 | | | IV-1 | 1700041M19Rik |
| 11131 | 3 | 4 | | | IV-1 | 1700042G07Rik |
| 11132 | 3 | 4 | | | IV-1 | 1700042G15Rik |
| 11133 | 3 | 4 | | | IV-1 | 1700042O10Rik |
| 11134 | 3 | 4 | | | IV-1 | 1700047G03Rik |

Fig. 36 - 59

| | | | | | | |
|---|---|---|---|---|---|---|
| 11135 | 3 | 4 | | | IV-1 | 1700047I17Rik2 |
| 11136 | 3 | 4 | | | IV-1 | 1700047L14Rik |
| 11137 | 3 | 4 | | | IV-1 | 1700047M11Rik |
| 11138 | 3 | 4 | | | IV-1 | 1700049E15Rik |
| 11139 | 3 | 4 | | | IV-1 | 1700049I22Rik |
| 11140 | 3 | 4 | | | IV-1 | 1700049L16Rik |
| 11141 | 3 | 4 | | | IV-1 | 1700051A21Rik |
| 11142 | 3 | 4 | | | IV-1 | 1700052I22Rik |
| 11143 | 3 | 4 | | | IV-1 | 1700052K11Rik |
| 11144 | 3 | 4 | | | IV-1 | 1700054A03Rik |
| 11145 | 3 | 4 | | | IV-1 | 1700054O13Rik |
| 11146 | 3 | 4 | | | IV-1 | 1700055C04Rik |
| 11147 | 3 | 4 | | | IV-1 | 1700055N04Rik |
| 11148 | 3 | 4 | | | IV-1 | 1700057G04Rik |
| 11149 | 3 | 4 | | | IV-1 | 1700061F12Rik |
| 11150 | 3 | 4 | | | IV-1 | 1700061G19Rik |
| 11151 | 3 | 4 | | | IV-1 | 1700065I16Rik |
| 11152 | 3 | 4 | | | IV-1 | 1700065J11Rik |
| 11153 | 3 | 4 | | | IV-1 | 1700065O20Rik |
| 11154 | 3 | 4 | | | IV-1 | 1700066B17Rik |
| 11155 | 3 | 4 | | | IV-1 | 1700066B19Rik |
| 11156 | 3 | 4 | | | IV-1 | 1700066N21Rik |
| 11157 | 3 | 4 | | | IV-1 | 1700067G17Rik |
| 11158 | 3 | 4 | | | IV-1 | 1700067K01Rik |
| 11159 | 3 | 4 | | | IV-1 | 1700067P10Rik |
| 11160 | 3 | 4 | | | IV-1 | 1700069I16Rik |
| 11161 | 3 | 4 | | | IV-1 | 1700073E17Rik |
| 11162 | 3 | 4 | | | IV-1 | 1700074H08Rik |
| 11163 | 3 | 4 | | | IV-1 | 1700080E11Rik |
| 11164 | 3 | 4 | | | IV-1 | 1700080N15Rik |
| 11165 | 3 | 4 | | | IV-1 | 1700080O16Rik |
| 11166 | 3 | 4 | | | IV-1 | 1700081H04Rik |
| 11167 | 3 | 4 | | | IV-1 | 1700084C01Rik |
| 11168 | 3 | 4 | | | IV-1 | 1700084J12Rik |
| 11169 | 3 | 4 | | | IV-1 | 1700091H14Rik |
| 11170 | 3 | 4 | | | IV-1 | 1700092C02Rik |
| 11171 | 3 | 4 | | | IV-1 | 1700092E19Rik |
| 11172 | 3 | 4 | | | IV-1 | 1700093K21Rik |
| 11173 | 3 | 4 | | | IV-1 | 1700094D03Rik |
| 11174 | 3 | 4 | | | IV-1 | 1700094J05Rik |
| 11175 | 3 | 4 | | | IV-1 | 1700094M24Rik |
| 11176 | 3 | 4 | | | IV-1 | 1700095A21Rik |
| 11177 | 3 | 4 | | | IV-1 | 1700096J18Rik |
| 11178 | 3 | 4 | | | IV-1 | 1700100L14Rik |
| 11179 | 3 | 4 | | | IV-1 | 1700101O22Rik |
| 11180 | 3 | 4 | | | IV-1 | 1700105P06Rik |
| 11181 | 3 | 4 | | | IV-1 | 1700108F19Rik |
| 11182 | 3 | 4 | | | IV-1 | 1700108J01Rik |
| 11183 | 3 | 4 | | | IV-1 | 1700109G14Rik |
| 11184 | 3 | 4 | | | IV-1 | 1700109H08Rik |
| 11185 | 3 | 4 | | | IV-1 | 1700109I08Rik |
| 11186 | 3 | 4 | | | IV-1 | 1700110C19Rik |
| 11187 | 3 | 4 | | | IV-1 | 1700112J05Rik |
| 11188 | 3 | 4 | | | IV-1 | 1700113A16Rik |
| 11189 | 3 | 4 | | | IV-1 | 1700113H08Rik |
| 11190 | 3 | 4 | | | IV-1 | 1700120E14Rik |
| 11191 | 3 | 4 | | | IV-1 | 1700120G07Rik |
| 11192 | 3 | 4 | | | IV-1 | 1700121N20Rik |
| 11193 | 3 | 4 | | | IV-1 | 1700122O11Rik |
| 11194 | 3 | 4 | | | IV-1 | 1700123I01Rik |
| 11195 | 3 | 4 | | | IV-1 | 1700123O12Rik |
| 11196 | 3 | 4 | | | IV-1 | 1700123O20Rik |
| 11197 | 3 | 4 | | | IV-1 | 1700125G02Rik |
| 11198 | 3 | 4 | | | IV-1 | 1700125G22Rik |
| 11199 | 3 | 4 | | | IV-1 | 1700125H03Rik |
| 11200 | 3 | 4 | | | IV-1 | 1700125H20Rik |
| 11201 | 3 | 4 | | | IV-1 | 1700128A07Rik |
| 11202 | 3 | 4 | | | IV-1 | 1700129C05Rik |
| 11203 | 3 | 4 | | | IV-1 | 1810006J02Rik |
| 11204 | 3 | 4 | | | IV-1 | 1810013L24Rik |
| 11205 | 3 | 4 | | | IV-1 | 1810026B05Rik |
| 11206 | 3 | 4 | | | IV-1 | 1810030O07Rik |
| 11207 | 3 | 4 | | | IV-1 | 1810043G02Rik |
| 11208 | 3 | 4 | | | IV-1 | 1810046K07Rik |
| 11209 | 3 | 4 | | | IV-1 | 1810055G02Rik |
| 11210 | 3 | 4 | | | IV-1 | 2010005H15Rik |
| 11211 | 3 | 4 | | | IV-1 | 2010012O05Rik |
| 11212 | 3 | 4 | | | IV-1 | 2010015L04Rik |
| 11213 | 3 | 4 | | | IV-1 | 2010109I03Rik |
| 11214 | 3 | 4 | | | IV-1 | 2010315B03Rik |
| 11215 | 3 | 4 | | | IV-1 | 2200002J24Rik |
| 11216 | 3 | 4 | | | IV-1 | 2210015D19Rik |
| 11217 | 3 | 4 | | | IV-1 | 2210016F16Rik |
| 11218 | 3 | 4 | | | IV-1 | 2210016L21Rik |
| 11219 | 3 | 4 | | | IV-1 | 2210019I11Rik |
| 11220 | 3 | 4 | | | IV-1 | 2210039B01Rik |
| 11221 | 3 | 4 | | | IV-1 | 2210420H20Rik |
| 11222 | 3 | 4 | | | IV-1 | 2300002M23Rik |
| 11223 | 3 | 4 | | | IV-1 | 2310003J15Rik |
| 11224 | 3 | 4 | | | IV-1 | 2310003H01Rik |
| 11225 | 3 | 4 | | | IV-1 | 2310005G13Rik |
| 11226 | 3 | 4 | | | IV-1 | 2310007B03Rik |
| 11227 | 3 | 4 | | | IV-1 | 2310008N11Rik |
| 11228 | 3 | 4 | | | IV-1 | 2310011J03Rik |
| 11229 | 3 | 4 | | | IV-1 | 2310020H05Rik |
| 11230 | 3 | 4 | | | IV-1 | 2310022A10Rik |
| 11231 | 3 | 4 | | | IV-1 | 2310022B05Rik |
| 11232 | 3 | 4 | | | IV-1 | 2310030A07Rik |
| 11233 | 3 | 4 | | | IV-1 | 2310035C23Rik |
| 11234 | 3 | 4 | | | IV-1 | 2310036O22Rik |
| 11235 | 3 | 4 | | | IV-1 | 2310042E22Rik |
| 11236 | 3 | 4 | | | IV-1 | 2310043L19Rik |
| 11237 | 3 | 4 | | | IV-1 | 2310057M21Rik |
| 11238 | 3 | 4 | | | IV-1 | 2310061N02Rik |
| 11239 | 3 | 4 | | | IV-1 | 2310065F04Rik |
| 11240 | 3 | 4 | | | IV-1 | 2310067B10Rik |
| 11241 | 3 | 4 | | | IV-1 | 2310069B03Rik |
| 11242 | 3 | 4 | | | IV-1 | 2310079G19Rik |
| 11243 | 3 | 4 | | | IV-1 | 2410002F23Rik |
| 11244 | 3 | 4 | | | IV-1 | 2410004I01Rik |
| 11245 | 3 | 4 | | | IV-1 | 2410016O06Rik |
| 11246 | 3 | 4 | | | IV-1 | 2510002D24Rik |
| 11247 | 3 | 4 | | | IV-1 | 2510003E04Rik |
| 11248 | 3 | 4 | | | IV-1 | 2510039O18Rik |
| 11249 | 3 | 4 | | | IV-1 | 2610001J05Rik |
| 11250 | 3 | 4 | | | IV-1 | 2610008E11Rik |
| 11251 | 3 | 4 | | | IV-1 | 2610015P09Rik |
| 11252 | 3 | 4 | | | IV-1 | 2610020H08Rik |
| 11253 | 3 | 4 | | | IV-1 | 2610027K06Rik |
| 11254 | 3 | 4 | | | IV-1 | 2610034B18Rik |
| 11255 | 3 | 4 | | | IV-1 | 2610034M16Rik |
| 11256 | 3 | 4 | | | IV-1 | 2610035F20Rik |
| 11257 | 3 | 4 | | | IV-1 | 2610100L16Rik |
| 11258 | 3 | 4 | | | IV-1 | 2610206C17Rik |
| 11259 | 3 | 4 | | | IV-1 | 2610301B20Rik |
| 11260 | 3 | 4 | | | IV-1 | 2610305D13Rik |
| 11261 | 3 | 4 | | | IV-1 | 2610307P16Rik |
| 11262 | 3 | 4 | | | IV-1 | 2610507I01Rik |
| 11263 | 3 | 4 | | | IV-1 | 2700038G22Rik |
| 11264 | 3 | 4 | | | IV-1 | 2700046A07Rik |
| 11265 | 3 | 4 | | | IV-1 | 2700054A10Rik |
| 11266 | 3 | 4 | | | IV-1 | 2700060E02Rik |
| 11267 | 3 | 4 | | | IV-1 | 2700081O15Rik |
| 11268 | 3 | 4 | | | IV-1 | 2700089E24Rik |
| 11269 | 3 | 4 | | | IV-1 | 2700099C18Rik |
| 11270 | 3 | 4 | | | IV-1 | 2810004N23Rik |
| 11271 | 3 | 4 | | | IV-1 | 2810006K23Rik |
| 11272 | 3 | 4 | | | IV-1 | 2810007J24Rik |
| 11273 | 3 | 4 | | | IV-1 | 2810021J22Rik |
| 11274 | 3 | 4 | | | IV-1 | 2810025M15Rik |
| 11275 | 3 | 4 | | | IV-1 | 2810032G03Rik |
| 11276 | 3 | 4 | | | IV-1 | 2810047C21Rik1 |
| 11277 | 3 | 4 | | | IV-1 | 2810403A07Rik |
| 11278 | 3 | 4 | | | IV-1 | 2810405F15Rik |
| 11279 | 3 | 4 | | | IV-1 | 2810408M09Rik |
| 11280 | 3 | 4 | | | IV-1 | 2810417H13Rik |
| 11281 | 3 | 4 | | | IV-1 | 2810433D01Rik |
| 11282 | 3 | 4 | | | IV-1 | 2810442I21Rik |
| 11283 | 3 | 4 | | | IV-1 | 2900005J15Rik |
| 11284 | 3 | 4 | | | IV-1 | 2900011O08Rik |
| 11285 | 3 | 4 | | | IV-1 | 2900041M22Rik |
| 11286 | 3 | 4 | | | IV-1 | 2900052N01Rik |
| 11287 | 3 | 4 | | | IV-1 | 2900079G21Rik |
| 11288 | 3 | 4 | | | IV-1 | 2900092C05Rik |
| 11289 | 3 | 4 | | | IV-1 | 2900097C17Rik |
| 11290 | 3 | 4 | | | IV-1 | 3110021A11Rik |
| 11291 | 3 | 4 | | | IV-1 | 3110035E14Rik |
| 11292 | 3 | 4 | | | IV-1 | 3110052M02Rik |
| 11293 | 3 | 4 | | | IV-1 | 3110057O12Rik |
| 11294 | 3 | 4 | | | IV-1 | 3110062M04Rik |
| 11295 | 3 | 4 | | | IV-1 | 3110079O15Rik |
| 11296 | 3 | 4 | | | IV-1 | 3110099E03Rik |
| 11297 | 3 | 4 | | | IV-1 | 3300002I08Rik |
| 11298 | 3 | 4 | | | IV-1 | 3425401B19Rik |
| 11299 | 3 | 4 | | | IV-1 | 3632451O06Rik |
| 11300 | 3 | 4 | | | IV-1 | 3830406C13Rik |
| 11301 | 3 | 4 | | | IV-1 | 3830417A13Rik |
| 11302 | 3 | 4 | | | IV-1 | 4430402I18Rik |
| 11303 | 3 | 4 | | | IV-1 | 4631405J19Rik |
| 11304 | 3 | 4 | | | IV-1 | 4632428N05Rik |
| 11305 | 3 | 4 | | | IV-1 | 4732491K20Rik |
| 11306 | 3 | 4 | | | IV-1 | 4833422C13Rik |
| 11307 | 3 | 4 | | | IV-1 | 4833423E24Rik |
| 11308 | 3 | 4 | | | IV-1 | 4833427F10Rik |
| 11309 | 3 | 4 | | | IV-1 | 4833427G06Rik |
| 11310 | 3 | 4 | | | IV-1 | 4921501E09Rik |
| 11311 | 3 | 4 | | | IV-1 | 4921504E06Rik |
| 11312 | 3 | 4 | | | IV-1 | 4921506M07Rik |
| 11313 | 3 | 4 | | | IV-1 | 4921507L20Rik |
| 11314 | 3 | 4 | | | IV-1 | 4921507P07Rik |
| 11315 | 3 | 4 | | | IV-1 | 4921511C20Rik |
| 11316 | 3 | 4 | | | IV-1 | 4921511M17Rik |
| 11317 | 3 | 4 | | | IV-1 | 4921515E04Rik |
| 11318 | 3 | 4 | | | IV-1 | 4921524L21Rik |
| 11319 | 3 | 4 | | | IV-1 | 4921530L21Rik |
| 11320 | 3 | 4 | | | IV-1 | 4921534H16Rik |
| 11321 | 3 | 4 | | | IV-1 | 4921536K21Rik |
| 11322 | 3 | 4 | | | IV-1 | 4921539E11Rik |
| 11323 | 3 | 4 | | | IV-1 | 4922502D21Rik |
| 11324 | 3 | 4 | | | IV-1 | 4930401O12Rik |
| 11325 | 3 | 4 | | | IV-1 | 4930402K13Rik |
| 11326 | 3 | 4 | | | IV-1 | 4930404A05Rik |

Fig. 36 - 60

| | | | | | | |
|---|---|---|---|---|---|---|
| 11327 | 3 | 4 | | | IV-1 | 4930404H11Rik |
| 11328 | 3 | 4 | | | IV-1 | 4930405A10Rik |
| 11329 | 3 | 4 | | | IV-1 | 4930405A21Rik |
| 11330 | 3 | 4 | | | IV-1 | 4930405J17Rik |
| 11331 | 3 | 4 | | | IV-1 | 4930406D18Rik |
| 11332 | 3 | 4 | | | IV-1 | 4930412D23Rik |
| 11333 | 3 | 4 | | | IV-1 | 4930412O13Rik |
| 11334 | 3 | 4 | | | IV-1 | 4930413E15Rik |
| 11335 | 3 | 4 | | | IV-1 | 4930413G21Rik |
| 11336 | 3 | 4 | | | IV-1 | 4930414L22Rik |
| 11337 | 3 | 4 | | | IV-1 | 4930414N06Rik |
| 11338 | 3 | 4 | | | IV-1 | 4930415F15Rik |
| 11339 | 3 | 4 | | | IV-1 | 4930415L06Rik |
| 11340 | 3 | 4 | | | IV-1 | 4930417O13Rik |
| 11341 | 3 | 4 | | | IV-1 | 4930425K10Rik |
| 11342 | 3 | 4 | | | IV-1 | 4930426L09Rik |
| 11343 | 3 | 4 | | | IV-1 | 4930427A07Rik |
| 11344 | 3 | 4 | | | IV-1 | 4930428D18Rik |
| 11345 | 3 | 4 | | | IV-1 | 4930428E07Rik |
| 11346 | 3 | 4 | | | IV-1 | 4930429B21Rik |
| 11347 | 3 | 4 | | | IV-1 | 4930429D17Rik |
| 11348 | 3 | 4 | | | IV-1 | 4930429F11Rik |
| 11349 | 3 | 4 | | | IV-1 | 4930430A15Rik |
| 11350 | 3 | 4 | | | IV-1 | 4930430D24Rik |
| 11351 | 3 | 4 | | | IV-1 | 4930430F21Rik |
| 11352 | 3 | 4 | | | IV-1 | 4930431F12Rik |
| 11353 | 3 | 4 | | | IV-1 | 4930431P03Rik |
| 11354 | 3 | 4 | | | IV-1 | 4930432J09Rik |
| 11355 | 3 | 4 | | | IV-1 | 4930432K21Rik |
| 11356 | 3 | 4 | | | IV-1 | 4930433N12Rik |
| 11357 | 3 | 4 | | | IV-1 | 4930434J06Rik |
| 11358 | 3 | 4 | | | IV-1 | 4930438E09Rik |
| 11359 | 3 | 4 | | | IV-1 | 4930441J16Rik |
| 11360 | 3 | 4 | | | IV-1 | 4930442L01Rik |
| 11361 | 3 | 4 | | | IV-1 | 4930443O20Rik |
| 11362 | 3 | 4 | | | IV-1 | 4930444G20Rik |
| 11363 | 3 | 4 | | | IV-1 | 4930444M15Rik |
| 11364 | 3 | 4 | | | IV-1 | 4930444P10Rik |
| 11365 | 3 | 4 | | | IV-1 | 4930447C04Rik |
| 11366 | 3 | 4 | | | IV-1 | 4930447J18Rik |
| 11367 | 3 | 4 | | | IV-1 | 4930447K03Rik |
| 11368 | 3 | 4 | | | IV-1 | 4930448C13Rik |
| 11369 | 3 | 4 | | | IV-1 | 4930448H16Rik |
| 11370 | 3 | 4 | | | IV-1 | 4930449E01Rik |
| 11371 | 3 | 4 | | | IV-1 | 4930449J24Rik |
| 11372 | 3 | 4 | | | IV-1 | 4930451G09Rik |
| 11373 | 3 | 4 | | | IV-1 | 4930451I11Rik |
| 11374 | 3 | 4 | | | IV-1 | 4930452A19Rik |
| 11375 | 3 | 4 | | | IV-1 | 4930452B06Rik |
| 11376 | 3 | 4 | | | IV-1 | 4930452G13Rik |
| 11377 | 3 | 4 | | | IV-1 | 4930453H23Rik |
| 11378 | 3 | 4 | | | IV-1 | 4930453L07Rik |
| 11379 | 3 | 4 | | | IV-1 | 4930455B14Rik |
| 11380 | 3 | 4 | | | IV-1 | 4930455D15Rik |
| 11381 | 3 | 4 | | | IV-1 | 4930455H04Rik |
| 11382 | 3 | 4 | | | IV-1 | 4930455J16Rik |
| 11383 | 3 | 4 | | | IV-1 | 4930459C07Rik |
| 11384 | 3 | 4 | | | IV-1 | 4930468A15Rik |
| 11385 | 3 | 4 | | | IV-1 | 4930469G21Rik |
| 11386 | 3 | 4 | | | IV-1 | 4930470P17Rik |
| 11387 | 3 | 4 | | | IV-1 | 4930471C04Rik |
| 11388 | 3 | 4 | | | IV-1 | 4930471M09Rik |
| 11389 | 3 | 4 | | | IV-1 | 4930473A02Rik |
| 11390 | 3 | 4 | | | IV-1 | 4930473O22Rik |
| 11391 | 3 | 4 | | | IV-1 | 4930474N05Rik |
| 11392 | 3 | 4 | | | IV-1 | 4930474N09Rik |
| 11393 | 3 | 4 | | | IV-1 | 4930478P22Rik |
| 11394 | 3 | 4 | | | IV-1 | 4930479D17Rik |
| 11395 | 3 | 4 | | | IV-1 | 4930480E11Rik |
| 11396 | 3 | 4 | | | IV-1 | 4930480G23Rik |
| 11397 | 3 | 4 | | | IV-1 | 4930480K15Rik |
| 11398 | 3 | 4 | | | IV-1 | 4930483J18Rik |
| 11399 | 3 | 4 | | | IV-1 | 4930483K19Rik |
| 11400 | 3 | 4 | | | IV-1 | 4930486F22Rik |
| 11401 | 3 | 4 | | | IV-1 | 4930486I03Rik |
| 11402 | 3 | 4 | | | IV-1 | 4930487H11Rik |
| 11403 | 3 | 4 | | | IV-1 | 4930488L21Rik |
| 11404 | 3 | 4 | | | IV-1 | 4930500F04Rik |
| 11405 | 3 | 4 | | | IV-1 | 4930500J02Rik |
| 11406 | 3 | 4 | | | IV-1 | 4930502E09Rik |
| 11407 | 3 | 4 | | | IV-1 | 4930502E18Rik |
| 11408 | 3 | 4 | | | IV-1 | 4930503B20Rik |
| 11409 | 3 | 4 | | | IV-1 | 4930503O07Rik |
| 11410 | 3 | 4 | | | IV-1 | 4930504O13Rik |
| 11411 | 3 | 4 | | | IV-1 | 4930506M07Rik |
| 11412 | 3 | 4 | | | IV-1 | 4930507D05Rik |
| 11413 | 3 | 4 | | | IV-1 | 4930507D10Rik |
| 11414 | 3 | 4 | | | IV-1 | 4930509E16Rik |
| 11415 | 3 | 4 | | | IV-1 | 4930511M06Rik |
| 11416 | 3 | 4 | | | IV-1 | 4930513D17Rik |
| 11417 | 3 | 4 | | | IV-1 | 4930513N10Rik |
| 11418 | 3 | 4 | | | IV-1 | 4930513O06Rik |
| 11419 | 3 | 4 | | | IV-1 | 4930515G01Rik |
| 11420 | 3 | 4 | | | IV-1 | 4930519D14Rik |
| 11421 | 3 | 4 | | | IV-1 | 4930519F16Rik |
| 11422 | 3 | 4 | | | IV-1 | 4930519F24Rik |
| 11423 | 3 | 4 | | | IV-1 | 4930519G04Rik |
| 11424 | 3 | 4 | | | IV-1 | 4930520P13Rik |
| 11425 | 3 | 4 | | | IV-1 | 4930522H14Rik |
| 11426 | 3 | 4 | | | IV-1 | 4930522O17Rik |
| 11427 | 3 | 4 | | | IV-1 | 4930523C07Rik |
| 11428 | 3 | 4 | | | IV-1 | 4930523O13Rik |
| 11429 | 3 | 4 | | | IV-1 | 4930524B15Rik |
| 11430 | 3 | 4 | | | IV-1 | 4930524O08Rik |
| 11431 | 3 | 4 | | | IV-1 | 4930525G20Rik |
| 11432 | 3 | 4 | | | IV-1 | 4930525M21Rik |
| 11433 | 3 | 4 | | | IV-1 | 4930527F14Rik |
| 11434 | 3 | 4 | | | IV-1 | 4930527G23Rik |
| 11435 | 3 | 4 | | | IV-1 | 4930528D03Rik |
| 11436 | 3 | 4 | | | IV-1 | 4930528P14Rik |
| 11437 | 3 | 4 | | | IV-1 | 4930538B01Rik |
| 11438 | 3 | 4 | | | IV-1 | 4930538K18Rik |
| 11439 | 3 | 4 | | | IV-1 | 4930539C22Rik |
| 11440 | 3 | 4 | | | IV-1 | 4930539M17Rik |
| 11441 | 3 | 4 | | | IV-1 | 4930540M03Rik |
| 11442 | 3 | 4 | | | IV-1 | 4930542C21Rik |
| 11443 | 3 | 4 | | | IV-1 | 4930543E12Rik |
| 11444 | 3 | 4 | | | IV-1 | 4930544D05Rik |
| 11445 | 3 | 4 | | | IV-1 | 4930544G11Rik |
| 11446 | 3 | 4 | | | IV-1 | 4930545E07Rik |
| 11447 | 3 | 4 | | | IV-1 | 4930545L23Rik |
| 11448 | 3 | 4 | | | IV-1 | 4930547E08Rik |
| 11449 | 3 | 4 | | | IV-1 | 4930548G14Rik |
| 11450 | 3 | 4 | | | IV-1 | 4930548H24Rik |
| 11451 | 3 | 4 | | | IV-1 | 4930548J01Rik |
| 11452 | 3 | 4 | | | IV-1 | 4930548K13Rik |
| 11453 | 3 | 4 | | | IV-1 | 4930549C01Rik |
| 11454 | 3 | 4 | | | IV-1 | 4930550C14Rik |
| 11455 | 3 | 4 | | | IV-1 | 4930550L24Rik |
| 11456 | 3 | 4 | | | IV-1 | 4930552N02Rik |
| 11457 | 3 | 4 | | | IV-1 | 4930552P12Rik |
| 11458 | 3 | 4 | | | IV-1 | 4930553E22Rik |
| 11459 | 3 | 4 | | | IV-1 | 4930555G01Rik |
| 11460 | 3 | 4 | | | IV-1 | 4930556C24Rik |
| 11461 | 3 | 4 | | | IV-1 | 4930556G01Rik |
| 11462 | 3 | 4 | | | IV-1 | 4930556J02Rik |
| 11463 | 3 | 4 | | | IV-1 | 4930556N09Rik |
| 11464 | 3 | 4 | | | IV-1 | 4930557A04Rik |
| 11465 | 3 | 4 | | | IV-1 | 4930558C23Rik |
| 11466 | 3 | 4 | | | IV-1 | 4930558K02Rik |
| 11467 | 3 | 4 | | | IV-1 | 4930562C15Rik |
| 11468 | 3 | 4 | | | IV-1 | 4930563E22Rik |
| 11469 | 3 | 4 | | | IV-1 | 4930564B18Rik |
| 11470 | 3 | 4 | | | IV-1 | 4930564C03Rik |
| 11471 | 3 | 4 | | | IV-1 | 4930565D16Rik |
| 11472 | 3 | 4 | | | IV-1 | 4930567H17Rik |
| 11473 | 3 | 4 | | | IV-1 | 4930567K20Rik |
| 11474 | 3 | 4 | | | IV-1 | 4930568D16Rik |
| 11475 | 3 | 4 | | | IV-1 | 4930568E12Rik |
| 11476 | 3 | 4 | | | IV-1 | 4930572K03Rik |
| 11477 | 3 | 4 | | | IV-1 | 4930572O03Rik |
| 11478 | 3 | 4 | | | IV-1 | 4930572O13Rik |
| 11479 | 3 | 4 | | | IV-1 | 4930578E11Rik |
| 11480 | 3 | 4 | | | IV-1 | 4930578I06Rik |
| 11481 | 3 | 4 | | | IV-1 | 4930579F01Rik |
| 11482 | 3 | 4 | | | IV-1 | 4930583P06Rik |
| 11483 | 3 | 4 | | | IV-1 | 4930584F24Rik |
| 11484 | 3 | 4 | | | IV-1 | 4930592I03Rik |
| 11485 | 3 | 4 | | | IV-1 | 4930593A02Rik |
| 11486 | 3 | 4 | | | IV-1 | 4930593C16Rik |
| 11487 | 3 | 4 | | | IV-1 | 4930595M18Rik |
| 11488 | 3 | 4 | | | IV-1 | 4930596D02Rik |
| 11489 | 3 | 4 | | | IV-1 | 4930598F16Rik |
| 11490 | 3 | 4 | | | IV-1 | 4931402G19Rik |
| 11491 | 3 | 4 | | | IV-1 | 4931403G20Rik |
| 11492 | 3 | 4 | | | IV-1 | 4931406B18Rik |
| 11493 | 3 | 4 | | | IV-1 | 4931406C07Rik |
| 11494 | 3 | 4 | | | IV-1 | 4931406H21Rik |
| 11495 | 3 | 4 | | | IV-1 | 4931409K22Rik |
| 11496 | 3 | 4 | | | IV-1 | 4931417E11Rik |
| 11497 | 3 | 4 | | | IV-1 | 4931420L22Rik |
| 11498 | 3 | 4 | | | IV-1 | 4931423N10Rik |
| 11499 | 3 | 4 | | | IV-1 | 4931429I11Rik |
| 11500 | 3 | 4 | | | IV-1 | 4931429L15Rik |
| 11501 | 3 | 4 | | | IV-1 | 4931440F15Rik |
| 11502 | 3 | 4 | | | IV-1 | 4931440J10Rik |
| 11503 | 3 | 4 | | | IV-1 | 4932412D23Rik |
| 11504 | 3 | 4 | | | IV-1 | 4932414J04Rik |
| 11505 | 3 | 4 | | | IV-1 | 4932415M13Rik |
| 11506 | 3 | 4 | | | IV-1 | 4932416H05Rik |
| 11507 | 3 | 4 | | | IV-1 | 4932416K20Rik |
| 11508 | 3 | 4 | | | IV-1 | 4932429P05Rik |
| 11509 | 3 | 4 | | | IV-1 | 4933400A11Rik |
| 11510 | 3 | 4 | | | IV-1 | 4933400L20Rik |
| 11511 | 3 | 4 | | | IV-1 | 4933401B06Rik |
| 11512 | 3 | 4 | | | IV-1 | 4933401H06Rik |
| 11513 | 3 | 4 | | | IV-1 | 4933402C06Rik |
| 11514 | 3 | 4 | | | IV-1 | 4933402E13Rik |
| 11515 | 3 | 4 | | | IV-1 | 4933402J07Rik |
| 11516 | 3 | 4 | | | IV-1 | 4933402J10Rik |
| 11517 | 3 | 4 | | | IV-1 | 4933402N22Rik |
| 11518 | 3 | 4 | | | IV-1 | 4933402P03Rik |

Fig. 36 - 61

| | | | | | | |
|---|---|---|---|---|---|---|
| 11519 | 3 | 4 | | | IV-1 | 4933403O08Rik |
| 11520 | 3 | 4 | | | IV-1 | 4933404G15Rik |
| 11521 | 3 | 4 | | | IV-1 | 4933404K08Rik |
| 11522 | 3 | 4 | | | IV-1 | 4933405D12Rik |
| 11523 | 3 | 4 | | | IV-1 | 4933405L10Rik |
| 11524 | 3 | 4 | | | IV-1 | 4933406F09Rik |
| 11525 | 3 | 4 | | | IV-1 | 4933406G16Rik |
| 11526 | 3 | 4 | | | IV-1 | 4933406I18Rik |
| 11527 | 3 | 4 | | | IV-1 | 4933406J08Rik |
| 11528 | 3 | 4 | | | IV-1 | 4933406M09Rik |
| 11529 | 3 | 4 | | | IV-1 | 4933407I05Rik |
| 11530 | 3 | 4 | | | IV-1 | 4933407L21Rik |
| 11531 | 3 | 4 | | | IV-1 | 4933408B17Rik |
| 11532 | 3 | 4 | | | IV-1 | 4933408J17Rik |
| 11533 | 3 | 4 | | | IV-1 | 4933411E08Rik |
| 11534 | 3 | 4 | | | IV-1 | 4933411G06Rik |
| 11535 | 3 | 4 | | | IV-1 | 4933411G11Rik |
| 11536 | 3 | 4 | | | IV-1 | 4933413J09Rik |
| 11537 | 3 | 4 | | | IV-1 | 4933413L06Rik |
| 11538 | 3 | 4 | | | IV-1 | 4933415F23Rik |
| 11539 | 3 | 4 | | | IV-1 | 4933416C03Rik |
| 11540 | 3 | 4 | | | IV-1 | 4933416I08Rik |
| 11541 | 3 | 4 | | | IV-1 | 4933416M06Rik |
| 11542 | 3 | 4 | | | IV-1 | 4933416M07Rik |
| 11543 | 3 | 4 | | | IV-1 | 4933417G07Rik |
| 11544 | 3 | 4 | | | IV-1 | 4933417O13Rik |
| 11545 | 3 | 4 | | | IV-1 | 4933421J07Rik |
| 11546 | 3 | 4 | | | IV-1 | 4933421O10Rik |
| 11547 | 3 | 4 | | | IV-1 | 4933422A05Rik |
| 11548 | 3 | 4 | | | IV-1 | 4933424G06Rik |
| 11549 | 3 | 4 | | | IV-1 | 4933425L06Rik |
| 11550 | 3 | 4 | | | IV-1 | 4933427D06Rik |
| 11551 | 3 | 4 | | | IV-1 | 4933427D14Rik |
| 11552 | 3 | 4 | | | IV-1 | 4933427E11Rik |
| 11553 | 3 | 4 | | | IV-1 | 4933427E13Rik |
| 11554 | 3 | 4 | | | IV-1 | 4933427G17Rik |
| 11555 | 3 | 4 | | | IV-1 | 4933427I22Rik |
| 11556 | 3 | 4 | | | IV-1 | 4933428C19Rik |
| 11557 | 3 | 4 | | | IV-1 | 4933429K18Rik |
| 11558 | 3 | 4 | | | IV-1 | 4933429O19Rik |
| 11559 | 3 | 4 | | | IV-1 | 4933430H16Rik |
| 11560 | 3 | 4 | | | IV-1 | 4933430I17Rik |
| 11561 | 3 | 4 | | | IV-1 | 4933430M04Rik |
| 11562 | 3 | 4 | | | IV-1 | 4933430N04Rik |
| 11563 | 3 | 4 | | | IV-1 | 4933431G14Rik |
| 11564 | 3 | 4 | | | IV-1 | 4933432J09Rik |
| 11565 | 3 | 4 | | | IV-1 | 4933432K03Rik |
| 11566 | 3 | 4 | | | IV-1 | 4933433C11Rik |
| 11567 | 3 | 4 | | | IV-1 | 4933433G08Rik |
| 11568 | 3 | 4 | | | IV-1 | 4933434E20Rik |
| 11569 | 3 | 4 | | | IV-1 | 4933436H12Rik |
| 11570 | 3 | 4 | | | IV-1 | 4933436I01Rik |
| 11571 | 3 | 4 | | | IV-1 | 4933440M02Rik |
| 11572 | 3 | 4 | | | IV-1 | 5031410I06Rik |
| 11573 | 3 | 4 | | | IV-1 | 5031414D18Rik |
| 11574 | 3 | 4 | | | IV-1 | 5031425E22Rik |
| 11575 | 3 | 4 | | | IV-1 | 5031425F14Rik |
| 11576 | 3 | 4 | | | IV-1 | 5033404E19Rik |
| 11577 | 3 | 4 | | | IV-1 | 5133400J02Rik |
| 11578 | 3 | 4 | | | IV-1 | 5330413P13Rik |
| 11579 | 3 | 4 | | | IV-1 | 5330434G04Rik |
| 11580 | 3 | 4 | | | IV-1 | 5430402O13Rik |
| 11581 | 3 | 4 | | | IV-1 | 5430427O19Rik |
| 11582 | 3 | 4 | | | IV-1 | 5730403I07Rik |
| 11583 | 3 | 4 | | | IV-1 | 5730405O15Rik |
| 11584 | 3 | 4 | | | IV-1 | 5730420D15Rik |
| 11585 | 3 | 4 | | | IV-1 | 5730455P16Rik |
| 11586 | 3 | 4 | | | IV-1 | 5730508B09Rik |
| 11587 | 3 | 4 | | | IV-1 | 5730559C18Rik |
| 11588 | 3 | 4 | | | IV-1 | 5830411N06Rik |
| 11589 | 3 | 4 | | | IV-1 | 5830416P10Rik |
| 11590 | 3 | 4 | | | IV-1 | 5830473C10Rik |
| 11591 | 3 | 4 | | | IV-1 | 5930403L14Rik |
| 11592 | 3 | 4 | | | IV-1 | 6030458C11Rik |
| 11593 | 3 | 4 | | | IV-1 | 6030468B19Rik |
| 11594 | 3 | 4 | | | IV-1 | 6330403A02Rik |
| 11595 | 3 | 4 | | | IV-1 | 6330416G13Rik |
| 11596 | 3 | 4 | | | IV-1 | 6330419J24Rik |
| 11597 | 3 | 4 | | | IV-1 | 6430531B16Rik |
| 11598 | 3 | 4 | | | IV-1 | 6430550D23Rik |
| 11599 | 3 | 4 | | | IV-1 | 6430562O15Rik |
| 11600 | 3 | 4 | | | IV-1 | 6430584L05Rik |
| 11601 | 3 | 4 | | | IV-1 | 6430706D22Rik |
| 11602 | 3 | 4 | | | IV-1 | 6430710C18Rik |
| 11603 | 3 | 4 | | | IV-1 | 6720489N17Rik |
| 11604 | 3 | 4 | | | IV-1 | 8030411F24Rik |
| 11605 | 3 | 4 | | | IV-1 | 8430419L09Rik |
| 11606 | 3 | 4 | | | IV-1 | 8430429K09Rik |
| 11607 | 3 | 4 | | | IV-1 | 9030025P20Rik |
| 11608 | 3 | 4 | | | IV-1 | 9030404E10Rik |
| 11609 | 3 | 4 | | | IV-1 | 9030624J02Rik |
| 11610 | 3 | 4 | | | IV-1 | 9130011E15Rik |
| 11611 | 3 | 4 | | | IV-1 | 9130019P16Rik |
| 11612 | 3 | 4 | | | IV-1 | 9130023H24Rik |
| 11613 | 3 | 4 | | | IV-1 | 9130024F11Rik |
| 11614 | 3 | 4 | | | IV-1 | 9130409J23Rik |

| | | | | | | |
|---|---|---|---|---|---|---|
| 11615 | 3 | 4 | | | IV-1 | 9230102O04Rik |
| 11616 | 3 | 4 | | | IV-1 | 9230105E05Rik |
| 11617 | 3 | 4 | | | IV-1 | 9230112J17Rik |
| 11618 | 3 | 4 | | | IV-1 | 9230116N13Rik |
| 11619 | 3 | 4 | | | IV-1 | 9330020H09Rik |
| 11620 | 3 | 4 | | | IV-1 | 9330151L19Rik |
| 11621 | 3 | 4 | | | IV-1 | 9330158H04Rik |
| 11622 | 3 | 4 | | | IV-1 | 9330179D12Rik |
| 11623 | 3 | 4 | | | IV-1 | 9330182L06Rik |
| 11624 | 3 | 4 | | | IV-1 | 9330188P03Rik |
| 11625 | 3 | 4 | | | IV-1 | 9430016H08Rik |
| 11626 | 3 | 4 | | | IV-1 | 9430018G01Rik |
| 11627 | 3 | 4 | | | IV-1 | 9430021M05Rik |
| 11628 | 3 | 4 | | | IV-1 | 9530053A07Rik |
| 11629 | 3 | 4 | | | IV-1 | 9530082P21Rik |
| 11630 | 3 | 4 | | | IV-1 | 9630013A20Rik |
| 11631 | 3 | 4 | | | IV-1 | 9630033F20Rik |
| 11632 | 3 | 4 | | | IV-1 | 9830107B12Rik |
| 11633 | 3 | 4 | | | IV-1 | 9830132P13Rik |
| 11634 | 3 | 4 | | | IV-1 | 9830166K06Rik |
| 11635 | 3 | 4 | | | IV-1 | 9930012K11Rik |
| 11636 | 3 | 4 | | | IV-1 | 9930014A18Rik |
| 11637 | 3 | 4 | | | IV-1 | A130010J15Rik |
| 11638 | 3 | 4 | | | IV-1 | A130077B15Rik |
| 11639 | 3 | 4 | | | IV-1 | A230001M10Rik |
| 11640 | 3 | 4 | | | IV-1 | A230046K03Rik |
| 11641 | 3 | 4 | | | IV-1 | A230057D06Rik |
| 11642 | 3 | 4 | | | IV-1 | A230070E04Rik |
| 11643 | 3 | 4 | | | IV-1 | A230077H06Rik |
| 11644 | 3 | 4 | | | IV-1 | A330023F24Rik |
| 11645 | 3 | 4 | | | IV-1 | A330033J07Rik |
| 11646 | 3 | 4 | | | IV-1 | A330035P11Rik |
| 11647 | 3 | 4 | | | IV-1 | A330049N07Rik |
| 11648 | 3 | 4 | | | IV-1 | A330050F15Rik |
| 11649 | 3 | 4 | | | IV-1 | A330076H08Rik |
| 11650 | 3 | 4 | | | IV-1 | A330102I10Rik |
| 11651 | 3 | 4 | | | IV-1 | A430005L14Rik |
| 11652 | 3 | 4 | | | IV-1 | A430105J19Rik |
| 11653 | 3 | 4 | | | IV-1 | A4gnt |
| 11654 | 3 | 4 | | | IV-1 | A530016L24Rik |
| 11655 | 3 | 4 | | | IV-1 | A530032D15Rik |
| 11656 | 3 | 4 | | | IV-1 | A530050N04Rik |
| 11657 | 3 | 4 | | | IV-1 | A530058N18Rik |
| 11658 | 3 | 4 | | | IV-1 | A530064D06Rik |
| 11659 | 3 | 4 | | | IV-1 | A530099J19Rik |
| 11660 | 3 | 4 | | | IV-1 | A630001G21Rik |
| 11661 | 3 | 4 | | | IV-1 | A630020A06 |
| 11662 | 3 | 4 | | | IV-1 | A630023A22Rik |
| 11663 | 3 | 4 | | | IV-1 | A630095E13Rik |
| 11664 | 3 | 4 | | | IV-1 | A630095N17Rik |
| 11665 | 3 | 4 | | | IV-1 | A730006G06Rik |
| 11666 | 3 | 4 | | | IV-1 | A730017L22Rik |
| 11667 | 3 | 4 | | | IV-1 | A730020E08Rik |
| 11668 | 3 | 4 | | | IV-1 | A730036I17Rik |
| 11669 | 3 | 4 | | | IV-1 | A730046J19Rik |
| 11670 | 3 | 4 | | | IV-1 | A730056A06Rik |
| 11671 | 3 | 4 | | | IV-1 | A730098P11Rik |
| 11672 | 3 | 4 | | | IV-1 | A830082K12Rik |
| 11673 | 3 | 4 | | | IV-1 | A830082N09Rik |
| 11674 | 3 | 4 | | | IV-1 | A930003A15Rik |
| 11675 | 3 | 4 | | | IV-1 | A930009A15Rik |
| 11676 | 3 | 4 | | | IV-1 | A930011O12Rik |
| 11677 | 3 | 4 | | | IV-1 | A930017M01Rik |
| 11678 | 3 | 4 | | | IV-1 | A930024E05Rik |
| 11679 | 3 | 4 | | | IV-1 | AA415398 |
| 11680 | 3 | 4 | | | IV-1 | AB041803 |
| 11681 | 3 | 4 | | | IV-1 | AI115009 |
| 11682 | 3 | 4 | | | IV-1 | AI118078 |
| 11683 | 3 | 4 | | | IV-1 | AI182371 |
| 11684 | 3 | 4 | | | IV-1 | AI197445 |
| 11685 | 3 | 4 | | | IV-1 | AI314180 |
| 11686 | 3 | 4 | | | IV-1 | AI414108 |
| 11687 | 3 | 4 | | | IV-1 | AI429214 |
| 11688 | 3 | 4 | | | IV-1 | AI464131 |
| 11689 | 3 | 4 | | | IV-1 | AI506816 |
| 11690 | 3 | 4 | | | IV-1 | AI593442 |
| 11691 | 3 | 4 | | | IV-1 | AI597479 |
| 11692 | 3 | 4 | | | IV-1 | AI646519 |
| 11693 | 3 | 4 | | | IV-1 | AI661453 |
| 11694 | 3 | 4 | | | IV-1 | AI837181 |
| 11695 | 3 | 4 | | | IV-1 | AI846148 |
| 11696 | 3 | 4 | | | IV-1 | AI847159 |
| 11697 | 3 | 4 | | | IV-1 | AI848285 |
| 11698 | 3 | 4 | | | IV-1 | AI854517 |
| 11699 | 3 | 4 | | | IV-1 | AU015836 |
| 11700 | 3 | 4 | | | IV-1 | AU018091 |
| 11701 | 3 | 4 | | | IV-1 | AU019823 |
| 11702 | 3 | 4 | | | IV-1 | AU022754 |
| 11703 | 3 | 4 | | | IV-1 | AU023762 |
| 11704 | 3 | 4 | | | IV-1 | AU040320 |
| 11705 | 3 | 4 | | | IV-1 | AV320801 |
| 11706 | 3 | 4 | | | IV-1 | AW046200 |
| 11707 | 3 | 4 | | | IV-1 | AW146154 |
| 11708 | 3 | 4 | | | IV-1 | AW209491 |
| 11709 | 3 | 4 | | | IV-1 | AW551984 |
| 11710 | 3 | 4 | | | IV-1 | AY512931 |

Fig. 36 - 62

| | | | | | | |
|---|---|---|---|---|---|---|
| 11711 | 3 | 4 | | | IV-1 | Aaas |
| 11712 | 3 | 4 | | | IV-1 | Aadacl2 |
| 11713 | 3 | 4 | | | IV-1 | Aadacl3 |
| 11714 | 3 | 4 | | | IV-1 | Aadat |
| 11715 | 3 | 4 | | | IV-1 | Aagab |
| 11716 | 3 | 4 | | | IV-1 | Aamp |
| 11717 | 3 | 4 | | | IV-1 | Aanat |
| 11718 | 3 | 4 | | | IV-1 | Aar2 |
| 11719 | 3 | 4 | | | IV-1 | Aars |
| 11720 | 3 | 4 | | | IV-1 | Aars2 |
| 11721 | 3 | 4 | | | IV-1 | Aasdhppt |
| 11722 | 3 | 4 | | | IV-1 | Aass |
| 11723 | 3 | 4 | | | IV-1 | Aatk |
| 11724 | 3 | 4 | | | IV-1 | Abat |
| 11725 | 3 | 4 | | | IV-1 | Abca1 |
| 11726 | 3 | 4 | | | IV-1 | Abca15 |
| 11727 | 3 | 4 | | | IV-1 | Abca16 |
| 11728 | 3 | 4 | | | IV-1 | Abcb10 |
| 11729 | 3 | 4 | | | IV-1 | Abcb11 |
| 11730 | 3 | 4 | | | IV-1 | Abcb4 |
| 11731 | 3 | 4 | | | IV-1 | Abcb6 |
| 11732 | 3 | 4 | | | IV-1 | Abcb7 |
| 11733 | 3 | 4 | | | IV-1 | Abcb8 |
| 11734 | 3 | 4 | | | IV-1 | Abcb9 |
| 11735 | 3 | 4 | | | IV-1 | Abcc1 |
| 11736 | 3 | 4 | | | IV-1 | Abcc12 |
| 11737 | 3 | 4 | | | IV-1 | Abcc4 |
| 11738 | 3 | 4 | | | IV-1 | Abcc5 |
| 11739 | 3 | 4 | | | IV-1 | Abcc6 |
| 11740 | 3 | 4 | | | IV-1 | Abcc8 |
| 11741 | 3 | 4 | | | IV-1 | Abcc9 |
| 11742 | 3 | 4 | | | IV-1 | Abcd1 |
| 11743 | 3 | 4 | | | IV-1 | Abcd3 |
| 11744 | 3 | 4 | | | IV-1 | Abcd4 |
| 11745 | 3 | 4 | | | IV-1 | Abce1 |
| 11746 | 3 | 4 | | | IV-1 | Abcf2 |
| 11747 | 3 | 4 | | | IV-1 | Abcf3 |
| 11748 | 3 | 4 | | | IV-1 | Abcg2 |
| 11749 | 3 | 4 | | | IV-1 | Abcg3 |
| 11750 | 3 | 4 | | | IV-1 | Abcg4 |
| 11751 | 3 | 4 | | | IV-1 | Abcg8 |
| 11752 | 3 | 4 | | | IV-1 | Abhd10 |
| 11753 | 3 | 4 | | | IV-1 | Abhd12 |
| 11754 | 3 | 4 | | | IV-1 | Abhd13 |
| 11755 | 3 | 4 | | | IV-1 | Abhd14b |
| 11756 | 3 | 4 | | | IV-1 | Abhd16a |
| 11757 | 3 | 4 | | | IV-1 | Abhd16b |
| 11758 | 3 | 4 | | | IV-1 | Abhd17b |
| 11759 | 3 | 4 | | | IV-1 | Abhd17c |
| 11760 | 3 | 4 | | | IV-1 | Abhd3 |
| 11761 | 3 | 4 | | | IV-1 | Abhd5 |
| 11762 | 3 | 4 | | | IV-1 | Abhd8 |
| 11763 | 3 | 4 | | | IV-1 | Abi1 |
| 11764 | 3 | 4 | | | IV-1 | Abi2 |
| 11765 | 3 | 4 | | | IV-1 | Abi3bp |
| 11766 | 3 | 4 | | | IV-1 | Abl1 |
| 11767 | 3 | 4 | | | IV-1 | Ablim2 |
| 11768 | 3 | 4 | | | IV-1 | Ablim3 |
| 11769 | 3 | 4 | | | IV-1 | Abo |
| 11770 | 3 | 4 | | | IV-1 | Abr |
| 11771 | 3 | 4 | | | IV-1 | Abt1 |
| 11772 | 3 | 4 | | | IV-1 | Acacb |
| 11773 | 3 | 4 | | | IV-1 | Acad10 |
| 11774 | 3 | 4 | | | IV-1 | Acad11 |
| 11775 | 3 | 4 | | | IV-1 | Acad8 |
| 11776 | 3 | 4 | | | IV-1 | Acad9 |
| 11777 | 3 | 4 | | | IV-1 | Acads |
| 11778 | 3 | 4 | | | IV-1 | Acadsb |
| 11779 | 3 | 4 | | | IV-1 | Acadvl |
| 11780 | 3 | 4 | | | IV-1 | Acan |
| 11781 | 3 | 4 | | | IV-1 | Acap1 |
| 11782 | 3 | 4 | | | IV-1 | Acap3 |
| 11783 | 3 | 4 | | | IV-1 | Acat1 |
| 11784 | 3 | 4 | | | IV-1 | Acbd3 |
| 11785 | 3 | 4 | | | IV-1 | Acbd5 |
| 11786 | 3 | 4 | | | IV-1 | Acbd6 |
| 11787 | 3 | 4 | | | IV-1 | Accs1 |
| 11788 | 3 | 4 | | | IV-1 | Acd |
| 11789 | 3 | 4 | | | IV-1 | Ace2 |
| 11790 | 3 | 4 | | | IV-1 | Ace3 |
| 11791 | 3 | 4 | | | IV-1 | Acer1 |
| 11792 | 3 | 4 | | | IV-1 | Acer3 |
| 11793 | 3 | 4 | | | IV-1 | Acnat1 |
| 11794 | 3 | 4 | | | IV-1 | Acnat2 |
| 11795 | 3 | 4 | | | IV-1 | Aco2 |
| 11796 | 3 | 4 | | | IV-1 | Acot12 |
| 11797 | 3 | 4 | | | IV-1 | Acot13 |
| 11798 | 3 | 4 | | | IV-1 | Acot2 |
| 11799 | 3 | 4 | | | IV-1 | Acot8 |
| 11800 | 3 | 4 | | | IV-1 | Acox3 |
| 11801 | 3 | 4 | | | IV-1 | Acoxl |
| 11802 | 3 | 4 | | | IV-1 | Acp1 |
| 11803 | 3 | 4 | | | IV-1 | Acp2 |
| 11804 | 3 | 4 | | | IV-1 | Acp6 |
| 11805 | 3 | 4 | | | IV-1 | Acpt |
| 11806 | 3 | 4 | | | IV-1 | Acrv1 |
| 11807 | 3 | 4 | | | IV-1 | Acsbg2 |
| 11808 | 3 | 4 | | | IV-1 | Acsf3 |
| 11809 | 3 | 4 | | | IV-1 | Acsl1 |
| 11810 | 3 | 4 | | | IV-1 | Acsl3 |
| 11811 | 3 | 4 | | | IV-1 | Acsl5 |
| 11812 | 3 | 4 | | | IV-1 | Acsl6 |
| 11813 | 3 | 4 | | | IV-1 | Acsm5 |
| 11814 | 3 | 4 | | | IV-1 | Acss1 |
| 11815 | 3 | 4 | | | IV-1 | Acss2 |
| 11816 | 3 | 4 | | | IV-1 | Actb |
| 11817 | 3 | 4 | | | IV-1 | Actg1 |
| 11818 | 3 | 4 | | | IV-1 | Actl6a |
| 11819 | 3 | 4 | | | IV-1 | Actl7a |
| 11820 | 3 | 4 | | | IV-1 | Actl7b |
| 11821 | 3 | 4 | | | IV-1 | Actl9 |
| 11822 | 3 | 4 | | | IV-1 | Actn1 |
| 11823 | 3 | 4 | | | IV-1 | Actn4 |
| 11824 | 3 | 4 | | | IV-1 | Actr10 |
| 11825 | 3 | 4 | | | IV-1 | Actr1a |
| 11826 | 3 | 4 | | | IV-1 | Actr1b |
| 11827 | 3 | 4 | | | IV-1 | Actr2 |
| 11828 | 3 | 4 | | | IV-1 | Actr3 |
| 11829 | 3 | 4 | | | IV-1 | Actr3b |
| 11830 | 3 | 4 | | | IV-1 | Actr8 |
| 11831 | 3 | 4 | | | IV-1 | Actrt1 |
| 11832 | 3 | 4 | | | IV-1 | Actrt3 |
| 11833 | 3 | 4 | | | IV-1 | Acvr1 |
| 11834 | 3 | 4 | | | IV-1 | Acvrl1 |
| 11835 | 3 | 4 | | | IV-1 | Acy3 |
| 11836 | 3 | 4 | | | IV-1 | Adad1 |
| 11837 | 3 | 4 | | | IV-1 | Adad2 |
| 11838 | 3 | 4 | | | IV-1 | Adal |
| 11839 | 3 | 4 | | | IV-1 | Adam10 |
| 11840 | 3 | 4 | | | IV-1 | Adam12 |
| 11841 | 3 | 4 | | | IV-1 | Adam15 |
| 11842 | 3 | 4 | | | IV-1 | Adam17 |
| 11843 | 3 | 4 | | | IV-1 | Adam18 |
| 11844 | 3 | 4 | | | IV-1 | Adam1a |
| 11845 | 3 | 4 | | | IV-1 | Adam1b |
| 11846 | 3 | 4 | | | IV-1 | Adam2 |
| 11847 | 3 | 4 | | | IV-1 | Adam21 |
| 11848 | 3 | 4 | | | IV-1 | Adam22 |
| 11849 | 3 | 4 | | | IV-1 | Adam23 |
| 11850 | 3 | 4 | | | IV-1 | Adam24 |
| 11851 | 3 | 4 | | | IV-1 | Adam25 |
| 11852 | 3 | 4 | | | IV-1 | Adam26a |
| 11853 | 3 | 4 | | | IV-1 | Adam26b |
| 11854 | 3 | 4 | | | IV-1 | Adam29 |
| 11855 | 3 | 4 | | | IV-1 | Adam30 |
| 11856 | 3 | 4 | | | IV-1 | Adam32 |
| 11857 | 3 | 4 | | | IV-1 | Adam34 |
| 11858 | 3 | 4 | | | IV-1 | Adam39 |
| 11859 | 3 | 4 | | | IV-1 | Adam4 |
| 11860 | 3 | 4 | | | IV-1 | Adam5 |
| 11861 | 3 | 4 | | | IV-1 | Adam6a |
| 11862 | 3 | 4 | | | IV-1 | Adam6b |
| 11863 | 3 | 4 | | | IV-1 | Adam9 |
| 11864 | 3 | 4 | | | IV-1 | Adamts10 |
| 11865 | 3 | 4 | | | IV-1 | Adamts12 |
| 11866 | 3 | 4 | | | IV-1 | Adamts13 |
| 11867 | 3 | 4 | | | IV-1 | Adamts14 |
| 11868 | 3 | 4 | | | IV-1 | Adamts16 |
| 11869 | 3 | 4 | | | IV-1 | Adamts17 |
| 11870 | 3 | 4 | | | IV-1 | Adamts18 |
| 11871 | 3 | 4 | | | IV-1 | Adamts2 |
| 11872 | 3 | 4 | | | IV-1 | Adamts20 |
| 11873 | 3 | 4 | | | IV-1 | Adamts3 |
| 11874 | 3 | 4 | | | IV-1 | Adamts6 |
| 11875 | 3 | 4 | | | IV-1 | Adamts7 |
| 11876 | 3 | 4 | | | IV-1 | Adamtsl1 |
| 11877 | 3 | 4 | | | IV-1 | Adamtsl2 |
| 11878 | 3 | 4 | | | IV-1 | Adamtsl3 |
| 11879 | 3 | 4 | | | IV-1 | Adamtsl5 |
| 11880 | 3 | 4 | | | IV-1 | Adar |
| 11881 | 3 | 4 | | | IV-1 | Adck1 |
| 11882 | 3 | 4 | | | IV-1 | Adck2 |
| 11883 | 3 | 4 | | | IV-1 | Adck3 |
| 11884 | 3 | 4 | | | IV-1 | Adcy2 |
| 11885 | 3 | 4 | | | IV-1 | Adcy3 |
| 11886 | 3 | 4 | | | IV-1 | Adcy4 |
| 11887 | 3 | 4 | | | IV-1 | Adcyap1 |
| 11888 | 3 | 4 | | | IV-1 | Add1 |
| 11889 | 3 | 4 | | | IV-1 | Add3 |
| 11890 | 3 | 4 | | | IV-1 | Adgb |
| 11891 | 3 | 4 | | | IV-1 | Adh5 |
| 11892 | 3 | 4 | | | IV-1 | Adh7 |
| 11893 | 3 | 4 | | | IV-1 | Adhfe1 |
| 11894 | 3 | 4 | | | IV-1 | Adi1 |
| 11895 | 3 | 4 | | | IV-1 | Adnp |
| 11896 | 3 | 4 | | | IV-1 | Adnp2 |
| 11897 | 3 | 4 | | | IV-1 | Ado |
| 11898 | 3 | 4 | | | IV-1 | Adora2a |
| 11899 | 3 | 4 | | | IV-1 | Adora3 |
| 11900 | 3 | 4 | | | IV-1 | Adpgk |
| 11901 | 3 | 4 | | | IV-1 | Adprh |
| 11902 | 3 | 4 | | | IV-1 | Adra2b |

Fig. 36 - 63

| | | | | | | |
|---|---|---|---|---|---|---|
| 11903 | 3 | 4 | | | IV-1 | Adrbk2 |
| 11904 | 3 | 4 | | | IV-1 | Adsl |
| 11905 | 3 | 4 | | | IV-1 | Adss |
| 11906 | 3 | 4 | | | IV-1 | Adssl1 |
| 11907 | 3 | 4 | | | IV-1 | Adtrp |
| 11908 | 3 | 4 | | | IV-1 | Aebp1 |
| 11909 | 3 | 4 | | | IV-1 | Aebp2 |
| 11910 | 3 | 4 | | | IV-1 | Aen |
| 11911 | 3 | 4 | | | IV-1 | Afap1 |
| 11912 | 3 | 4 | | | IV-1 | Aff3 |
| 11913 | 3 | 4 | | | IV-1 | Afg3l1 |
| 11914 | 3 | 4 | | | IV-1 | Afg3l2 |
| 11915 | 3 | 4 | | | IV-1 | Afmid |
| 11916 | 3 | 4 | | | IV-1 | Aftph |
| 11917 | 3 | 4 | | | IV-1 | Agap1 |
| 11918 | 3 | 4 | | | IV-1 | Agap2 |
| 11919 | 3 | 4 | | | IV-1 | Agap3 |
| 11920 | 3 | 4 | | | IV-1 | Agbl1 |
| 11921 | 3 | 4 | | | IV-1 | Agbl2 |
| 11922 | 3 | 4 | | | IV-1 | Agbl5 |
| 11923 | 3 | 4 | | | IV-1 | Ager |
| 11924 | 3 | 4 | | | IV-1 | Agfg1 |
| 11925 | 3 | 4 | | | IV-1 | Agfg2 |
| 11926 | 3 | 4 | | | IV-1 | Aggf1 |
| 11927 | 3 | 4 | | | IV-1 | Agl |
| 11928 | 3 | 4 | | | IV-1 | Ago1 |
| 11929 | 3 | 4 | | | IV-1 | Ago4 |
| 11930 | 3 | 4 | | | IV-1 | Agpat1 |
| 11931 | 3 | 4 | | | IV-1 | Agpat3 |
| 11932 | 3 | 4 | | | IV-1 | Agpat4 |
| 11933 | 3 | 4 | | | IV-1 | Agpat5 |
| 11934 | 3 | 4 | | | IV-1 | Agpat6 |
| 11935 | 3 | 4 | | | IV-1 | Agps |
| 11936 | 3 | 4 | | | IV-1 | Agr3 |
| 11937 | 3 | 4 | | | IV-1 | Agtpbp1 |
| 11938 | 3 | 4 | | | IV-1 | Agtr1b |
| 11939 | 3 | 4 | | | IV-1 | Agtrap |
| 11940 | 3 | 4 | | | IV-1 | Agxt2 |
| 11941 | 3 | 4 | | | IV-1 | Ahctf1 |
| 11942 | 3 | 4 | | | IV-1 | Ahcyl1 |
| 11943 | 3 | 4 | | | IV-1 | Ahcyl2 |
| 11944 | 3 | 4 | | | IV-1 | Ahi1 |
| 11945 | 3 | 4 | | | IV-1 | Ahr |
| 11946 | 3 | 4 | | | IV-1 | Ahrr |
| 11947 | 3 | 4 | | | IV-1 | Aida |
| 11948 | 3 | 4 | | | IV-1 | Aif1l |
| 11949 | 3 | 4 | | | IV-1 | Aifm2 |
| 11950 | 3 | 4 | | | IV-1 | Aifm3 |
| 11951 | 3 | 4 | | | IV-1 | Aim1 |
| 11952 | 3 | 4 | | | IV-1 | Aimp1 |
| 11953 | 3 | 4 | | | IV-1 | Aimp2 |
| 11954 | 3 | 4 | | | IV-1 | Ajap1 |
| 11955 | 3 | 4 | | | IV-1 | Ajuba |
| 11956 | 3 | 4 | | | IV-1 | Ak2 |
| 11957 | 3 | 4 | | | IV-1 | Ak5 |
| 11958 | 3 | 4 | | | IV-1 | Ak8 |
| 11959 | 3 | 4 | | | IV-1 | Akap1 |
| 11960 | 3 | 4 | | | IV-1 | Akap14 |
| 11961 | 3 | 4 | | | IV-1 | Akap3 |
| 11962 | 3 | 4 | | | IV-1 | Akap5 |
| 11963 | 3 | 4 | | | IV-1 | Akap8 |
| 11964 | 3 | 4 | | | IV-1 | Akap8l |
| 11965 | 3 | 4 | | | IV-1 | Akirin1 |
| 11966 | 3 | 4 | | | IV-1 | Akirin2 |
| 11967 | 3 | 4 | | | IV-1 | Aknad1 |
| 11968 | 3 | 4 | | | IV-1 | Akr1a1 |
| 11969 | 3 | 4 | | | IV-1 | Akr1b10 |
| 11970 | 3 | 4 | | | IV-1 | Akr1c14 |
| 11971 | 3 | 4 | | | IV-1 | Akr1c20 |
| 11972 | 3 | 4 | | | IV-1 | Akr1c21 |
| 11973 | 3 | 4 | | | IV-1 | Akr1c6 |
| 11974 | 3 | 4 | | | IV-1 | Akr1cl |
| 11975 | 3 | 4 | | | IV-1 | Akr1d1 |
| 11976 | 3 | 4 | | | IV-1 | Akt1 |
| 11977 | 3 | 4 | | | IV-1 | Akt1s1 |
| 11978 | 3 | 4 | | | IV-1 | Aktip |
| 11979 | 3 | 4 | | | IV-1 | Alcam |
| 11980 | 3 | 4 | | | IV-1 | Aldh18a1 |
| 11981 | 3 | 4 | | | IV-1 | Aldh1b1 |
| 11982 | 3 | 4 | | | IV-1 | Aldh1l2 |
| 11983 | 3 | 4 | | | IV-1 | Aldh3a1 |
| 11984 | 3 | 4 | | | IV-1 | Aldh3b2 |
| 11985 | 3 | 4 | | | IV-1 | Aldh4a1 |
| 11986 | 3 | 4 | | | IV-1 | Aldh8a1 |
| 11987 | 3 | 4 | | | IV-1 | Aldh9a1 |
| 11988 | 3 | 4 | | | IV-1 | Aldoa |
| 11989 | 3 | 4 | | | IV-1 | Aldoart2 |
| 11990 | 3 | 4 | | | IV-1 | Alg11 |
| 11991 | 3 | 4 | | | IV-1 | Alg12 |
| 11992 | 3 | 4 | | | IV-1 | Alg13 |
| 11993 | 3 | 4 | | | IV-1 | Alg2 |
| 11994 | 3 | 4 | | | IV-1 | Alg6 |
| 11995 | 3 | 4 | | | IV-1 | Alkbh1 |
| 11996 | 3 | 4 | | | IV-1 | Alkbh4 |
| 11997 | 3 | 4 | | | IV-1 | Allc |
| 11998 | 3 | 4 | | | IV-1 | Alms1-ps2 |
| 11999 | 3 | 4 | | | IV-1 | Alox12b |
| 12000 | 3 | 4 | | | IV-1 | Alox12e |
| 12001 | 3 | 4 | | | IV-1 | Aloxe3 |
| 12002 | 3 | 4 | | | IV-1 | Alppl2 |
| 12003 | 3 | 4 | | | IV-1 | Als2cr11 |
| 12004 | 3 | 4 | | | IV-1 | Alx1 |
| 12005 | 3 | 4 | | | IV-1 | Alx3 |
| 12006 | 3 | 4 | | | IV-1 | Alyref2 |
| 12007 | 3 | 4 | | | IV-1 | Ambra1 |
| 12008 | 3 | 4 | | | IV-1 | Amdhd1 |
| 12009 | 3 | 4 | | | IV-1 | Amfr |
| 12010 | 3 | 4 | | | IV-1 | Amhr2 |
| 12011 | 3 | 4 | | | IV-1 | Amigo1 |
| 12012 | 3 | 4 | | | IV-1 | Ammecr1l |
| 12013 | 3 | 4 | | | IV-1 | Amotl2 |
| 12014 | 3 | 4 | | | IV-1 | Ampd2 |
| 12015 | 3 | 4 | | | IV-1 | Ampd3 |
| 12016 | 3 | 4 | | | IV-1 | Amz1 |
| 12017 | 3 | 4 | | | IV-1 | Amz2 |
| 12018 | 3 | 4 | | | IV-1 | Anapc1 |
| 12019 | 3 | 4 | | | IV-1 | Anapc10 |
| 12020 | 3 | 4 | | | IV-1 | Anapc11 |
| 12021 | 3 | 4 | | | IV-1 | Anapc16 |
| 12022 | 3 | 4 | | | IV-1 | Anapc2 |
| 12023 | 3 | 4 | | | IV-1 | Anapc5 |
| 12024 | 3 | 4 | | | IV-1 | Anapc7 |
| 12025 | 3 | 4 | | | IV-1 | Ang2 |
| 12026 | 3 | 4 | | | IV-1 | Ang3 |
| 12027 | 3 | 4 | | | IV-1 | Angel1 |
| 12028 | 3 | 4 | | | IV-1 | Angel2 |
| 12029 | 3 | 4 | | | IV-1 | Angpt2 |
| 12030 | 3 | 4 | | | IV-1 | Angptl3 |
| 12031 | 3 | 4 | | | IV-1 | Angptl4 |
| 12032 | 3 | 4 | | | IV-1 | Ank2 |
| 12033 | 3 | 4 | | | IV-1 | Ankdd1b |
| 12034 | 3 | 4 | | | IV-1 | Ankef1 |
| 12035 | 3 | 4 | | | IV-1 | Ankfy1 |
| 12036 | 3 | 4 | | | IV-1 | Ankib1 |
| 12037 | 3 | 4 | | | IV-1 | Ankle1 |
| 12038 | 3 | 4 | | | IV-1 | Ankle2 |
| 12039 | 3 | 4 | | | IV-1 | Ankra2 |
| 12040 | 3 | 4 | | | IV-1 | Ankrd1 |
| 12041 | 3 | 4 | | | IV-1 | Ankrd10 |
| 12042 | 3 | 4 | | | IV-1 | Ankrd13a |
| 12043 | 3 | 4 | | | IV-1 | Ankrd13d |
| 12044 | 3 | 4 | | | IV-1 | Ankrd16 |
| 12045 | 3 | 4 | | | IV-1 | Ankrd17 |
| 12046 | 3 | 4 | | | IV-1 | Ankrd24 |
| 12047 | 3 | 4 | | | IV-1 | Ankrd32 |
| 12048 | 3 | 4 | | | IV-1 | Ankrd33b |
| 12049 | 3 | 4 | | | IV-1 | Ankrd34a |
| 12050 | 3 | 4 | | | IV-1 | Ankrd34b |
| 12051 | 3 | 4 | | | IV-1 | Ankrd36 |
| 12052 | 3 | 4 | | | IV-1 | Ankrd39 |
| 12053 | 3 | 4 | | | IV-1 | Ankrd40 |
| 12054 | 3 | 4 | | | IV-1 | Ankrd42 |
| 12055 | 3 | 4 | | | IV-1 | Ankrd44 |
| 12056 | 3 | 4 | | | IV-1 | Ankrd45 |
| 12057 | 3 | 4 | | | IV-1 | Ankrd46 |
| 12058 | 3 | 4 | | | IV-1 | Ankrd49 |
| 12059 | 3 | 4 | | | IV-1 | Ankrd50 |
| 12060 | 3 | 4 | | | IV-1 | Ankrd53 |
| 12061 | 3 | 4 | | | IV-1 | Ankrd54 |
| 12062 | 3 | 4 | | | IV-1 | Ankrd60 |
| 12063 | 3 | 4 | | | IV-1 | Ankrd63 |
| 12064 | 3 | 4 | | | IV-1 | Ankrd66 |
| 12065 | 3 | 4 | | | IV-1 | Ankrd7 |
| 12066 | 3 | 4 | | | IV-1 | Anks1b |
| 12067 | 3 | 4 | | | IV-1 | Anks6 |
| 12068 | 3 | 4 | | | IV-1 | Anln |
| 12069 | 3 | 4 | | | IV-1 | Ano1 |
| 12070 | 3 | 4 | | | IV-1 | Ano10 |
| 12071 | 3 | 4 | | | IV-1 | Ano3 |
| 12072 | 3 | 4 | | | IV-1 | Ano4 |
| 12073 | 3 | 4 | | | IV-1 | Ano5 |
| 12074 | 3 | 4 | | | IV-1 | Ano6 |
| 12075 | 3 | 4 | | | IV-1 | Ano7 |
| 12076 | 3 | 4 | | | IV-1 | Ano8 |
| 12077 | 3 | 4 | | | IV-1 | Ano9 |
| 12078 | 3 | 4 | | | IV-1 | Anp32a |
| 12079 | 3 | 4 | | | IV-1 | Anpep |
| 12080 | 3 | 4 | | | IV-1 | Antxrl |
| 12081 | 3 | 4 | | | IV-1 | Anxa10 |
| 12082 | 3 | 4 | | | IV-1 | Anxa11 |
| 12083 | 3 | 4 | | | IV-1 | Anxa4 |
| 12084 | 3 | 4 | | | IV-1 | Anxa6 |
| 12085 | 3 | 4 | | | IV-1 | Anxa7 |
| 12086 | 3 | 4 | | | IV-1 | Aoah |
| 12087 | 3 | 4 | | | IV-1 | Aoc1 |
| 12088 | 3 | 4 | | | IV-1 | Aox1 |
| 12089 | 3 | 4 | | | IV-1 | Aox3 |
| 12090 | 3 | 4 | | | IV-1 | Aox4 |
| 12091 | 3 | 4 | | | IV-1 | Ap1ar |
| 12092 | 3 | 4 | | | IV-1 | Ap1b1 |
| 12093 | 3 | 4 | | | IV-1 | Ap1g1 |
| 12094 | 3 | 4 | | | IV-1 | Ap2a1 |

Fig. 36 - 64

| | | | | | | |
|---|---|---|---|---|---|---|
| 12095 | 3 | 4 | | | IV-1 | Ap2a2 |
| 12096 | 3 | 4 | | | IV-1 | Ap2b1 |
| 12097 | 3 | 4 | | | IV-1 | Ap3b1 |
| 12098 | 3 | 4 | | | IV-1 | Ap3b2 |
| 12099 | 3 | 4 | | | IV-1 | Ap3d1 |
| 12100 | 3 | 4 | | | IV-1 | Ap3m1 |
| 12101 | 3 | 4 | | | IV-1 | Ap3m2 |
| 12102 | 3 | 4 | | | IV-1 | Ap3s2 |
| 12103 | 3 | 4 | | | IV-1 | Ap4b1 |
| 12104 | 3 | 4 | | | IV-1 | Ap4e1 |
| 12105 | 3 | 4 | | | IV-1 | Ap4s1 |
| 12106 | 3 | 4 | | | IV-1 | Ap5z1 |
| 12107 | 3 | 4 | | | IV-1 | Apaf1 |
| 12108 | 3 | 4 | | | IV-1 | Apba2 |
| 12109 | 3 | 4 | | | IV-1 | Apba3 |
| 12110 | 3 | 4 | | | IV-1 | Apbb1 |
| 12111 | 3 | 4 | | | IV-1 | Apbb2 |
| 12112 | 3 | 4 | | | IV-1 | Apbb3 |
| 12113 | 3 | 4 | | | IV-1 | Apeh |
| 12114 | 3 | 4 | | | IV-1 | Apela |
| 12115 | 3 | 4 | | | IV-1 | Aph1a |
| 12116 | 3 | 4 | | | IV-1 | Aph1c |
| 12117 | 3 | 4 | | | IV-1 | Api5 |
| 12118 | 3 | 4 | | | IV-1 | Aplp1 |
| 12119 | 3 | 4 | | | IV-1 | Aplp2 |
| 12120 | 3 | 4 | | | IV-1 | Apmap |
| 12121 | 3 | 4 | | | IV-1 | Apoa1bp |
| 12122 | 3 | 4 | | | IV-1 | Apobec4 |
| 12123 | 3 | 4 | | | IV-1 | Apobr |
| 12124 | 3 | 4 | | | IV-1 | Apol10a |
| 12125 | 3 | 4 | | | IV-1 | Apol7b |
| 12126 | 3 | 4 | | | IV-1 | Apol7e |
| 12127 | 3 | 4 | | | IV-1 | Apom |
| 12128 | 3 | 4 | | | IV-1 | Appl1 |
| 12129 | 3 | 4 | | | IV-1 | Appl2 |
| 12130 | 3 | 4 | | | IV-1 | Aptx |
| 12131 | 3 | 4 | | | IV-1 | Aqp2 |
| 12132 | 3 | 4 | | | IV-1 | Aqp5 |
| 12133 | 3 | 4 | | | IV-1 | Aqp6 |
| 12134 | 3 | 4 | | | IV-1 | Aqr |
| 12135 | 3 | 4 | | | IV-1 | Araf |
| 12136 | 3 | 4 | | | IV-1 | Arap2 |
| 12137 | 3 | 4 | | | IV-1 | Arap3 |
| 12138 | 3 | 4 | | | IV-1 | Areg |
| 12139 | 3 | 4 | | | IV-1 | Arel1 |
| 12140 | 3 | 4 | | | IV-1 | Arf1 |
| 12141 | 3 | 4 | | | IV-1 | Arf6 |
| 12142 | 3 | 4 | | | IV-1 | Arfgap1 |
| 12143 | 3 | 4 | | | IV-1 | Arfgap2 |
| 12144 | 3 | 4 | | | IV-1 | Arfgap3 |
| 12145 | 3 | 4 | | | IV-1 | Arfgef1 |
| 12146 | 3 | 4 | | | IV-1 | Arfip1 |
| 12147 | 3 | 4 | | | IV-1 | Arfip2 |
| 12148 | 3 | 4 | | | IV-1 | Arfrp1 |
| 12149 | 3 | 4 | | | IV-1 | Arglu1 |
| 12150 | 3 | 4 | | | IV-1 | Arhgap1 |
| 12151 | 3 | 4 | | | IV-1 | Arhgap11a |
| 12152 | 3 | 4 | | | IV-1 | Arhgap12 |
| 12153 | 3 | 4 | | | IV-1 | Arhgap17 |
| 12154 | 3 | 4 | | | IV-1 | Arhgap22 |
| 12155 | 3 | 4 | | | IV-1 | Arhgap23 |
| 12156 | 3 | 4 | | | IV-1 | Arhgap27 |
| 12157 | 3 | 4 | | | IV-1 | Arhgap27os3 |
| 12158 | 3 | 4 | | | IV-1 | Arhgap28 |
| 12159 | 3 | 4 | | | IV-1 | Arhgap29 |
| 12160 | 3 | 4 | | | IV-1 | Arhgap33 |
| 12161 | 3 | 4 | | | IV-1 | Arhgap33os |
| 12162 | 3 | 4 | | | IV-1 | Arhgap36 |
| 12163 | 3 | 4 | | | IV-1 | Arhgap40 |
| 12164 | 3 | 4 | | | IV-1 | Arhgap44 |
| 12165 | 3 | 4 | | | IV-1 | Arhgap6 |
| 12166 | 3 | 4 | | | IV-1 | Arhgdia |
| 12167 | 3 | 4 | | | IV-1 | Arhgef10 |
| 12168 | 3 | 4 | | | IV-1 | Arhgef10l |
| 12169 | 3 | 4 | | | IV-1 | Arhgef11 |
| 12170 | 3 | 4 | | | IV-1 | Arhgef15 |
| 12171 | 3 | 4 | | | IV-1 | Arhgef17 |
| 12172 | 3 | 4 | | | IV-1 | Arhgef18 |
| 12173 | 3 | 4 | | | IV-1 | Arhgef2 |
| 12174 | 3 | 4 | | | IV-1 | Arhgef28 |
| 12175 | 3 | 4 | | | IV-1 | Arhgef3 |
| 12176 | 3 | 4 | | | IV-1 | Arhgef33 |
| 12177 | 3 | 4 | | | IV-1 | Arhgef38 |
| 12178 | 3 | 4 | | | IV-1 | Arhgef4 |
| 12179 | 3 | 4 | | | IV-1 | Arhgef6 |
| 12180 | 3 | 4 | | | IV-1 | Arhgef7 |
| 12181 | 3 | 4 | | | IV-1 | Arhgef9 |
| 12182 | 3 | 4 | | | IV-1 | Arid1a |
| 12183 | 3 | 4 | | | IV-1 | Arid1b |
| 12184 | 3 | 4 | | | IV-1 | Arid4a |
| 12185 | 3 | 4 | | | IV-1 | Arid4b |
| 12186 | 3 | 4 | | | IV-1 | Arid5a |
| 12187 | 3 | 4 | | | IV-1 | Arih1 |
| 12188 | 3 | 4 | | | IV-1 | Arl13a |
| 12189 | 3 | 4 | | | IV-1 | Arl14 |
| 12190 | 3 | 4 | | | IV-1 | Arl14ep |
| 12191 | 3 | 4 | | | IV-1 | Arl14epl |
| 12192 | 3 | 4 | | | IV-1 | Arl15 |
| 12193 | 3 | 4 | | | IV-1 | Arl16 |
| 12194 | 3 | 4 | | | IV-1 | Arl3 |
| 12195 | 3 | 4 | | | IV-1 | Arl4a |
| 12196 | 3 | 4 | | | IV-1 | Arl5a |
| 12197 | 3 | 4 | | | IV-1 | Arl6ip1 |
| 12198 | 3 | 4 | | | IV-1 | Arl6ip4 |
| 12199 | 3 | 4 | | | IV-1 | Arl6ip6 |
| 12200 | 3 | 4 | | | IV-1 | Arl8b |
| 12201 | 3 | 4 | | | IV-1 | Armc1 |
| 12202 | 3 | 4 | | | IV-1 | Armc10 |
| 12203 | 3 | 4 | | | IV-1 | Armc2 |
| 12204 | 3 | 4 | | | IV-1 | Armc3 |
| 12205 | 3 | 4 | | | IV-1 | Armc4 |
| 12206 | 3 | 4 | | | IV-1 | Armc5 |
| 12207 | 3 | 4 | | | IV-1 | Armc8 |
| 12208 | 3 | 4 | | | IV-1 | Armc9 |
| 12209 | 3 | 4 | | | IV-1 | Armcx2 |
| 12210 | 3 | 4 | | | IV-1 | Armcx3 |
| 12211 | 3 | 4 | | | IV-1 | Armcx5 |
| 12212 | 3 | 4 | | | IV-1 | Arnt |
| 12213 | 3 | 4 | | | IV-1 | Arpc1a |
| 12214 | 3 | 4 | | | IV-1 | Arpc2 |
| 12215 | 3 | 4 | | | IV-1 | Arpc5 |
| 12216 | 3 | 4 | | | IV-1 | Arpp19 |
| 12217 | 3 | 4 | | | IV-1 | Arrdc4 |
| 12218 | 3 | 4 | | | IV-1 | Arsa |
| 12219 | 3 | 4 | | | IV-1 | Arsb |
| 12220 | 3 | 4 | | | IV-1 | Arsj |
| 12221 | 3 | 4 | | | IV-1 | Arsk |
| 12222 | 3 | 4 | | | IV-1 | Art2a-ps |
| 12223 | 3 | 4 | | | IV-1 | Art2b |
| 12224 | 3 | 4 | | | IV-1 | Art3 |
| 12225 | 3 | 4 | | | IV-1 | Art4 |
| 12226 | 3 | 4 | | | IV-1 | Art5 |
| 12227 | 3 | 4 | | | IV-1 | Arvcf |
| 12228 | 3 | 4 | | | IV-1 | Arx |
| 12229 | 3 | 4 | | | IV-1 | As3mt |
| 12230 | 3 | 4 | | | IV-1 | Asah1 |
| 12231 | 3 | 4 | | | IV-1 | Asb10 |
| 12232 | 3 | 4 | | | IV-1 | Asb12 |
| 12233 | 3 | 4 | | | IV-1 | Asb13 |
| 12234 | 3 | 4 | | | IV-1 | Asb14 |
| 12235 | 3 | 4 | | | IV-1 | Asb15 |
| 12236 | 3 | 4 | | | IV-1 | Asb16 |
| 12237 | 3 | 4 | | | IV-1 | Asb3 |
| 12238 | 3 | 4 | | | IV-1 | Asb4 |
| 12239 | 3 | 4 | | | IV-1 | Asb6 |
| 12240 | 3 | 4 | | | IV-1 | Asb7 |
| 12241 | 3 | 4 | | | IV-1 | Asb8 |
| 12242 | 3 | 4 | | | IV-1 | Asb9 |
| 12243 | 3 | 4 | | | IV-1 | Ascc3 |
| 12244 | 3 | 4 | | | IV-1 | Ascl1 |
| 12245 | 3 | 4 | | | IV-1 | Asf1a |
| 12246 | 3 | 4 | | | IV-1 | Asgr2 |
| 12247 | 3 | 4 | | | IV-1 | Asic2 |
| 12248 | 3 | 4 | | | IV-1 | Asic3 |
| 12249 | 3 | 4 | | | IV-1 | Asic5 |
| 12250 | 3 | 4 | | | IV-1 | Asna1 |
| 12251 | 3 | 4 | | | IV-1 | Asns |
| 12252 | 3 | 4 | | | IV-1 | Asnsd1 |
| 12253 | 3 | 4 | | | IV-1 | Aspdh |
| 12254 | 3 | 4 | | | IV-1 | Aspg |
| 12255 | 3 | 4 | | | IV-1 | Asph |
| 12256 | 3 | 4 | | | IV-1 | Aspscr1 |
| 12257 | 3 | 4 | | | IV-1 | Asrgl1 |
| 12258 | 3 | 4 | | | IV-1 | Astn1 |
| 12259 | 3 | 4 | | | IV-1 | Astn2 |
| 12260 | 3 | 4 | | | IV-1 | Asz1 |
| 12261 | 3 | 4 | | | IV-1 | Atad1 |
| 12262 | 3 | 4 | | | IV-1 | Atad3a |
| 12263 | 3 | 4 | | | IV-1 | Atad5 |
| 12264 | 3 | 4 | | | IV-1 | Ate1 |
| 12265 | 3 | 4 | | | IV-1 | Atf1 |
| 12266 | 3 | 4 | | | IV-1 | Atf2 |
| 12267 | 3 | 4 | | | IV-1 | Atf6 |
| 12268 | 3 | 4 | | | IV-1 | Atf6b |
| 12269 | 3 | 4 | | | IV-1 | Atf7ip2 |
| 12270 | 3 | 4 | | | IV-1 | Atg13 |
| 12271 | 3 | 4 | | | IV-1 | Atg14 |
| 12272 | 3 | 4 | | | IV-1 | Atg2a |
| 12273 | 3 | 4 | | | IV-1 | Atg2b |
| 12274 | 3 | 4 | | | IV-1 | Atg3 |
| 12275 | 3 | 4 | | | IV-1 | Atg4b |
| 12276 | 3 | 4 | | | IV-1 | Atg4c |
| 12277 | 3 | 4 | | | IV-1 | Atg4d |
| 12278 | 3 | 4 | | | IV-1 | Atg5 |
| 12279 | 3 | 4 | | | IV-1 | Atg7 |
| 12280 | 3 | 4 | | | IV-1 | Atg9a |
| 12281 | 3 | 4 | | | IV-1 | Atg9b |
| 12282 | 3 | 4 | | | IV-1 | Athl1 |
| 12283 | 3 | 4 | | | IV-1 | Atic |
| 12284 | 3 | 4 | | | IV-1 | Atl2 |
| 12285 | 3 | 4 | | | IV-1 | Atm |
| 12286 | 3 | 4 | | | IV-1 | Atmin |

Fig. 36 - 65

| | | | | | | |
|---|---|---|---|---|---|---|
| 12287 | 3 | 4 | | | IV-1 | Atn1 |
| 12288 | 3 | 4 | | | IV-1 | Atoh1 |
| 12289 | 3 | 4 | | | IV-1 | Atp11b |
| 12290 | 3 | 4 | | | IV-1 | Atp13a1 |
| 12291 | 3 | 4 | | | IV-1 | Atp13a2 |
| 12292 | 3 | 4 | | | IV-1 | Atp13a3 |
| 12293 | 3 | 4 | | | IV-1 | Atp13a4 |
| 12294 | 3 | 4 | | | IV-1 | Atp13a5 |
| 12295 | 3 | 4 | | | IV-1 | Atp1a2 |
| 12296 | 3 | 4 | | | IV-1 | Atp1b2 |
| 12297 | 3 | 4 | | | IV-1 | Atp1b3 |
| 12298 | 3 | 4 | | | IV-1 | Atp1b4 |
| 12299 | 3 | 4 | | | IV-1 | Atp2a2 |
| 12300 | 3 | 4 | | | IV-1 | Atp2b1 |
| 12301 | 3 | 4 | | | IV-1 | Atp2b2 |
| 12302 | 3 | 4 | | | IV-1 | Atp2b3 |
| 12303 | 3 | 4 | | | IV-1 | Atp2b4 |
| 12304 | 3 | 4 | | | IV-1 | Atp2c1 |
| 12305 | 3 | 4 | | | IV-1 | Atp4a |
| 12306 | 3 | 4 | | | IV-1 | Atp4b |
| 12307 | 3 | 4 | | | IV-1 | Atp5a1 |
| 12308 | 3 | 4 | | | IV-1 | Atp5c1 |
| 12309 | 3 | 4 | | | IV-1 | Atp5d |
| 12310 | 3 | 4 | | | IV-1 | Atp5f1 |
| 12311 | 3 | 4 | | | IV-1 | Atp5j |
| 12312 | 3 | 4 | | | IV-1 | Atp5sl |
| 12313 | 3 | 4 | | | IV-1 | Atp6ap1 |
| 12314 | 3 | 4 | | | IV-1 | Atp6ap2 |
| 12315 | 3 | 4 | | | IV-1 | Atp6v0a1 |
| 12316 | 3 | 4 | | | IV-1 | Atp6v0c |
| 12317 | 3 | 4 | | | IV-1 | Atp6v0d1 |
| 12318 | 3 | 4 | | | IV-1 | Atp6v0d2 |
| 12319 | 3 | 4 | | | IV-1 | Atp6v1a |
| 12320 | 3 | 4 | | | IV-1 | Atp6v1b2 |
| 12321 | 3 | 4 | | | IV-1 | Atp6v1c1 |
| 12322 | 3 | 4 | | | IV-1 | Atp6v1e2 |
| 12323 | 3 | 4 | | | IV-1 | Atp6v1g3 |
| 12324 | 3 | 4 | | | IV-1 | Atp6v1h |
| 12325 | 3 | 4 | | | IV-1 | Atp8b1 |
| 12326 | 3 | 4 | | | IV-1 | Atp8b2 |
| 12327 | 3 | 4 | | | IV-1 | Atp8b4 |
| 12328 | 3 | 4 | | | IV-1 | Atp8b5 |
| 12329 | 3 | 4 | | | IV-1 | Atp9a |
| 12330 | 3 | 4 | | | IV-1 | Atp9b |
| 12331 | 3 | 4 | | | IV-1 | Atpaf1 |
| 12332 | 3 | 4 | | | IV-1 | Atpaf2 |
| 12333 | 3 | 4 | | | IV-1 | Atrip |
| 12334 | 3 | 4 | | | IV-1 | Atrnl1 |
| 12335 | 3 | 4 | | | IV-1 | Atxn10 |
| 12336 | 3 | 4 | | | IV-1 | Atxn2 |
| 12337 | 3 | 4 | | | IV-1 | Atxn2l |
| 12338 | 3 | 4 | | | IV-1 | Atxn3 |
| 12339 | 3 | 4 | | | IV-1 | Atxn7 |
| 12340 | 3 | 4 | | | IV-1 | Atxn7l3b |
| 12341 | 3 | 4 | | | IV-1 | Aurkc |
| 12342 | 3 | 4 | | | IV-1 | Avil |
| 12343 | 3 | 4 | | | IV-1 | Avl9 |
| 12344 | 3 | 4 | | | IV-1 | Avpr1a |
| 12345 | 3 | 4 | | | IV-1 | Avpr2 |
| 12346 | 3 | 4 | | | IV-1 | Awat2 |
| 12347 | 3 | 4 | | | IV-1 | Axin1 |
| 12348 | 3 | 4 | | | IV-1 | Axl |
| 12349 | 3 | 4 | | | IV-1 | Azi2 |
| 12350 | 3 | 4 | | | IV-1 | B130024G19Rik |
| 12351 | 3 | 4 | | | IV-1 | B230118H07Rik |
| 12352 | 3 | 4 | | | IV-1 | B230119M05Rik |
| 12353 | 3 | 4 | | | IV-1 | B230206H07Rik |
| 12354 | 3 | 4 | | | IV-1 | B3galnt1 |
| 12355 | 3 | 4 | | | IV-1 | B3galnt2 |
| 12356 | 3 | 4 | | | IV-1 | B3galt4 |
| 12357 | 3 | 4 | | | IV-1 | B3gat1 |
| 12358 | 3 | 4 | | | IV-1 | B3glct |
| 12359 | 3 | 4 | | | IV-1 | B3gnt1 |
| 12360 | 3 | 4 | | | IV-1 | B3gnt4 |
| 12361 | 3 | 4 | | | IV-1 | B3gnt5 |
| 12362 | 3 | 4 | | | IV-1 | B3gnt6 |
| 12363 | 3 | 4 | | | IV-1 | B430010I23Rik |
| 12364 | 3 | 4 | | | IV-1 | B430212C06Rik |
| 12365 | 3 | 4 | | | IV-1 | B430306N03Rik |
| 12366 | 3 | 4 | | | IV-1 | B430319G15Rik |
| 12367 | 3 | 4 | | | IV-1 | B4galnt4 |
| 12368 | 3 | 4 | | | IV-1 | B4galt2 |
| 12369 | 3 | 4 | | | IV-1 | B4galt3 |
| 12370 | 3 | 4 | | | IV-1 | B4galt4 |
| 12371 | 3 | 4 | | | IV-1 | B4galt5 |
| 12372 | 3 | 4 | | | IV-1 | B4galt6 |
| 12373 | 3 | 4 | | | IV-1 | B4galt7 |
| 12374 | 3 | 4 | | | IV-1 | B930025P03Rik |
| 12375 | 3 | 4 | | | IV-1 | BB014433 |
| 12376 | 3 | 4 | | | IV-1 | BB019430 |
| 12377 | 3 | 4 | | | IV-1 | BB031773 |
| 12378 | 3 | 4 | | | IV-1 | BC003331 |
| 12379 | 3 | 4 | | | IV-1 | BC003965 |
| 12380 | 3 | 4 | | | IV-1 | BC004004 |
| 12381 | 3 | 4 | | | IV-1 | BC016579 |
| 12382 | 3 | 4 | | | IV-1 | BC017158 |
| 12383 | 3 | 4 | | | IV-1 | BC018242 |
| 12384 | 3 | 4 | | | IV-1 | BC021785 |
| 12385 | 3 | 4 | | | IV-1 | BC023829 |
| 12386 | 3 | 4 | | | IV-1 | BC024386 |
| 12387 | 3 | 4 | | | IV-1 | BC027072 |
| 12388 | 3 | 4 | | | IV-1 | BC027231 |
| 12389 | 3 | 4 | | | IV-1 | BC030307 |
| 12390 | 3 | 4 | | | IV-1 | BC030336 |
| 12391 | 3 | 4 | | | IV-1 | BC030500 |
| 12392 | 3 | 4 | | | IV-1 | BC030867 |
| 12393 | 3 | 4 | | | IV-1 | BC030870 |
| 12394 | 3 | 4 | | | IV-1 | BC035044 |
| 12395 | 3 | 4 | | | IV-1 | BC037032 |
| 12396 | 3 | 4 | | | IV-1 | BC039966 |
| 12397 | 3 | 4 | | | IV-1 | BC048403 |
| 12398 | 3 | 4 | | | IV-1 | BC048502 |
| 12399 | 3 | 4 | | | IV-1 | BC048546 |
| 12400 | 3 | 4 | | | IV-1 | BC048602 |
| 12401 | 3 | 4 | | | IV-1 | BC048609 |
| 12402 | 3 | 4 | | | IV-1 | BC048644 |
| 12403 | 3 | 4 | | | IV-1 | BC049635 |
| 12404 | 3 | 4 | | | IV-1 | BC049715 |
| 12405 | 3 | 4 | | | IV-1 | BC049730 |
| 12406 | 3 | 4 | | | IV-1 | BC049762 |
| 12407 | 3 | 4 | | | IV-1 | BC051628 |
| 12408 | 3 | 4 | | | IV-1 | BC055111 |
| 12409 | 3 | 4 | | | IV-1 | BC061194 |
| 12410 | 3 | 4 | | | IV-1 | BC061237 |
| 12411 | 3 | 4 | | | IV-1 | BC068157 |
| 12412 | 3 | 4 | | | IV-1 | BC089491 |
| 12413 | 3 | 4 | | | IV-1 | BC089597 |
| 12414 | 3 | 4 | | | IV-1 | BC094916 |
| 12415 | 3 | 4 | | | IV-1 | BC100451 |
| 12416 | 3 | 4 | | | IV-1 | BC107364 |
| 12417 | 3 | 4 | | | IV-1 | BC147527 |
| 12418 | 3 | 4 | | | IV-1 | Baalc |
| 12419 | 3 | 4 | | | IV-1 | Baat |
| 12420 | 3 | 4 | | | IV-1 | Babam1 |
| 12421 | 3 | 4 | | | IV-1 | Bace2 |
| 12422 | 3 | 4 | | | IV-1 | Bad |
| 12423 | 3 | 4 | | | IV-1 | Bag3 |
| 12424 | 3 | 4 | | | IV-1 | Bag5 |
| 12425 | 3 | 4 | | | IV-1 | Bag6 |
| 12426 | 3 | 4 | | | IV-1 | Bahd1 |
| 12427 | 3 | 4 | | | IV-1 | Bai1 |
| 12428 | 3 | 4 | | | IV-1 | Bai2 |
| 12429 | 3 | 4 | | | IV-1 | Bai3 |
| 12430 | 3 | 4 | | | IV-1 | Baiap2 |
| 12431 | 3 | 4 | | | IV-1 | Baiap2l1 |
| 12432 | 3 | 4 | | | IV-1 | Baiap3 |
| 12433 | 3 | 4 | | | IV-1 | Bank1 |
| 12434 | 3 | 4 | | | IV-1 | Bap1 |
| 12435 | 3 | 4 | | | IV-1 | Bard1 |
| 12436 | 3 | 4 | | | IV-1 | Barhl1 |
| 12437 | 3 | 4 | | | IV-1 | Barhl2 |
| 12438 | 3 | 4 | | | IV-1 | Barx1 |
| 12439 | 3 | 4 | | | IV-1 | Batf |
| 12440 | 3 | 4 | | | IV-1 | Baz2b |
| 12441 | 3 | 4 | | | IV-1 | Bbs1 |
| 12442 | 3 | 4 | | | IV-1 | Bbs10 |
| 12443 | 3 | 4 | | | IV-1 | Bbs12 |
| 12444 | 3 | 4 | | | IV-1 | Bbs4 |
| 12445 | 3 | 4 | | | IV-1 | Bbs9 |
| 12446 | 3 | 4 | | | IV-1 | Bcam |
| 12447 | 3 | 4 | | | IV-1 | Bcan |
| 12448 | 3 | 4 | | | IV-1 | Bcap29 |
| 12449 | 3 | 4 | | | IV-1 | Bcar1 |
| 12450 | 3 | 4 | | | IV-1 | Bcas1 |
| 12451 | 3 | 4 | | | IV-1 | Bcas3os1 |
| 12452 | 3 | 4 | | | IV-1 | Bcdin3d |
| 12453 | 3 | 4 | | | IV-1 | Bcl10 |
| 12454 | 3 | 4 | | | IV-1 | Bcl11b |
| 12455 | 3 | 4 | | | IV-1 | Bcl2 |
| 12456 | 3 | 4 | | | IV-1 | Bcl2l2 |
| 12457 | 3 | 4 | | | IV-1 | Bcr |
| 12458 | 3 | 4 | | | IV-1 | Bdnf |
| 12459 | 3 | 4 | | | IV-1 | Begain |
| 12460 | 3 | 4 | | | IV-1 | Bend7 |
| 12461 | 3 | 4 | | | IV-1 | Best1 |
| 12462 | 3 | 4 | | | IV-1 | Best3 |
| 12463 | 3 | 4 | | | IV-1 | Bet1 |
| 12464 | 3 | 4 | | | IV-1 | Bex6 |
| 12465 | 3 | 4 | | | IV-1 | Bfar |
| 12466 | 3 | 4 | | | IV-1 | Bhlhb9 |
| 12467 | 3 | 4 | | | IV-1 | Bhlhe22 |
| 12468 | 3 | 4 | | | IV-1 | Bhmt2 |
| 12469 | 3 | 4 | | | IV-1 | Bicd2 |
| 12470 | 3 | 4 | | | IV-1 | Birc3 |
| 12471 | 3 | 4 | | | IV-1 | Bivm |
| 12472 | 3 | 4 | | | IV-1 | Bkcap |
| 12473 | 3 | 4 | | | IV-1 | Blk |
| 12474 | 3 | 4 | | | IV-1 | Blmh |
| 12475 | 3 | 4 | | | IV-1 | Bloc1s3 |
| 12476 | 3 | 4 | | | IV-1 | Bloc1s4 |
| 12477 | 3 | 4 | | | IV-1 | Bloc1s6 |
| 12478 | 3 | 4 | | | IV-1 | Blzf1 |

Fig. 36 - 66

| | | | | | | |
|---|---|---|---|---|---|---|
| 12479 | 3 | 4 | | | IV-1 | Bmi1 |
| 12480 | 3 | 4 | | | IV-1 | Bmp1 |
| 12481 | 3 | 4 | | | IV-1 | Bmp6 |
| 12482 | 3 | 4 | | | IV-1 | Bmp8b |
| 12483 | 3 | 4 | | | IV-1 | Bmpr1a |
| 12484 | 3 | 4 | | | IV-1 | Bms1 |
| 12485 | 3 | 4 | | | IV-1 | Bnc2 |
| 12486 | 3 | 4 | | | IV-1 | Bnip2 |
| 12487 | 3 | 4 | | | IV-1 | Bod1 |
| 12488 | 3 | 4 | | | IV-1 | Bok |
| 12489 | 3 | 4 | | | IV-1 | Bop1 |
| 12490 | 3 | 4 | | | IV-1 | Bphl |
| 12491 | 3 | 4 | | | IV-1 | Bpifa3 |
| 12492 | 3 | 4 | | | IV-1 | Bpifb2 |
| 12493 | 3 | 4 | | | IV-1 | Bpifb5 |
| 12494 | 3 | 4 | | | IV-1 | Bpifc |
| 12495 | 3 | 4 | | | IV-1 | Braf |
| 12496 | 3 | 4 | | | IV-1 | Brap |
| 12497 | 3 | 4 | | | IV-1 | Brca1 |
| 12498 | 3 | 4 | | | IV-1 | Brcc3 |
| 12499 | 3 | 4 | | | IV-1 | Brd1 |
| 12500 | 3 | 4 | | | IV-1 | Brd2 |
| 12501 | 3 | 4 | | | IV-1 | Brd3 |
| 12502 | 3 | 4 | | | IV-1 | Brd7 |
| 12503 | 3 | 4 | | | IV-1 | Brd8 |
| 12504 | 3 | 4 | | | IV-1 | Brd9 |
| 12505 | 3 | 4 | | | IV-1 | Brdt |
| 12506 | 3 | 4 | | | IV-1 | Brf1 |
| 12507 | 3 | 4 | | | IV-1 | Bri3bp |
| 12508 | 3 | 4 | | | IV-1 | Brinp1 |
| 12509 | 3 | 4 | | | IV-1 | Brinp2 |
| 12510 | 3 | 4 | | | IV-1 | Brms1l |
| 12511 | 3 | 4 | | | IV-1 | Brwd1 |
| 12512 | 3 | 4 | | | IV-1 | Bsg |
| 12513 | 3 | 4 | | | IV-1 | Bsnd |
| 12514 | 3 | 4 | | | IV-1 | Btbd1 |
| 12515 | 3 | 4 | | | IV-1 | Btbd11 |
| 12516 | 3 | 4 | | | IV-1 | Btbd16 |
| 12517 | 3 | 4 | | | IV-1 | Btbd3 |
| 12518 | 3 | 4 | | | IV-1 | Btbd6 |
| 12519 | 3 | 4 | | | IV-1 | Btbd9 |
| 12520 | 3 | 4 | | | IV-1 | Btc |
| 12521 | 3 | 4 | | | IV-1 | Btd |
| 12522 | 3 | 4 | | | IV-1 | Btf3l4 |
| 12523 | 3 | 4 | | | IV-1 | Btg1 |
| 12524 | 3 | 4 | | | IV-1 | Btg4 |
| 12525 | 3 | 4 | | | IV-1 | Btk |
| 12526 | 3 | 4 | | | IV-1 | Btnl1 |
| 12527 | 3 | 4 | | | IV-1 | Btnl10 |
| 12528 | 3 | 4 | | | IV-1 | Btnl2 |
| 12529 | 3 | 4 | | | IV-1 | Btnl5-ps |
| 12530 | 3 | 4 | | | IV-1 | Btrc |
| 12531 | 3 | 4 | | | IV-1 | Bub1b |
| 12532 | 3 | 4 | | | IV-1 | Bub3 |
| 12533 | 3 | 4 | | | IV-1 | Bud13 |
| 12534 | 3 | 4 | | | IV-1 | Bves |
| 12535 | 3 | 4 | | | IV-1 | Bzrap1 |
| 12536 | 3 | 4 | | | IV-1 | Bzw1 |
| 12537 | 3 | 4 | | | IV-1 | Bzw2 |
| 12538 | 3 | 4 | | | IV-1 | C030006K11Rik |
| 12539 | 3 | 4 | | | IV-1 | C030016D13Rik |
| 12540 | 3 | 4 | | | IV-1 | C030023E24Rik |
| 12541 | 3 | 4 | | | IV-1 | C030034I22Rik |
| 12542 | 3 | 4 | | | IV-1 | C030037D09Rik |
| 12543 | 3 | 4 | | | IV-1 | C030039L03Rik |
| 12544 | 3 | 4 | | | IV-1 | C130021I20Rik |
| 12545 | 3 | 4 | | | IV-1 | C130026L21Rik |
| 12546 | 3 | 4 | | | IV-1 | C130030K03Rik |
| 12547 | 3 | 4 | | | IV-1 | C130050O18Rik |
| 12548 | 3 | 4 | | | IV-1 | C130074G19Rik |
| 12549 | 3 | 4 | | | IV-1 | C130079G13Rik |
| 12550 | 3 | 4 | | | IV-1 | C1galt1c1 |
| 12551 | 3 | 4 | | | IV-1 | C1qbp |
| 12552 | 3 | 4 | | | IV-1 | C1ql1 |
| 12553 | 3 | 4 | | | IV-1 | C1qtnf1 |
| 12554 | 3 | 4 | | | IV-1 | C1rb |
| 12555 | 3 | 4 | | | IV-1 | C1s1 |
| 12556 | 3 | 4 | | | IV-1 | C2 |
| 12557 | 3 | 4 | | | IV-1 | C230052I12Rik |
| 12558 | 3 | 4 | | | IV-1 | C2cd2 |
| 12559 | 3 | 4 | | | IV-1 | C2cd3 |
| 12560 | 3 | 4 | | | IV-1 | C2cd4c |
| 12561 | 3 | 4 | | | IV-1 | C2cd5 |
| 12562 | 3 | 4 | | | IV-1 | C330006A16Rik |
| 12563 | 3 | 4 | | | IV-1 | C330007P06Rik |
| 12564 | 3 | 4 | | | IV-1 | C330013F16Rik |
| 12565 | 3 | 4 | | | IV-1 | C330018D20Rik |
| 12566 | 3 | 4 | | | IV-1 | C330021F23Rik |
| 12567 | 3 | 4 | | | IV-1 | C330022C24Rik |
| 12568 | 3 | 4 | | | IV-1 | C330046G13Rik |
| 12569 | 3 | 4 | | | IV-1 | C430049B03Rik |
| 12570 | 3 | 4 | | | IV-1 | C530005A16Rik |
| 12571 | 3 | 4 | | | IV-1 | C6 |
| 12572 | 3 | 4 | | | IV-1 | C630043F03Rik |
| 12573 | 3 | 4 | | | IV-1 | C7 |
| 12574 | 3 | 4 | | | IV-1 | C730027H18Rik |
| 12575 | 3 | 4 | | | IV-1 | C77080 |
| 12576 | 3 | 4 | | | IV-1 | C77370 |
| 12577 | 3 | 4 | | | IV-1 | C87436 |
| 12578 | 3 | 4 | | | IV-1 | C8a |
| 12579 | 3 | 4 | | | IV-1 | C8b |
| 12580 | 3 | 4 | | | IV-1 | C9 |
| 12581 | 3 | 4 | | | IV-1 | Cab39 |
| 12582 | 3 | 4 | | | IV-1 | Cab39l |
| 12583 | 3 | 4 | | | IV-1 | Cabin1 |
| 12584 | 3 | 4 | | | IV-1 | Cables2 |
| 12585 | 3 | 4 | | | IV-1 | Cabp2 |
| 12586 | 3 | 4 | | | IV-1 | Cabs1 |
| 12587 | 3 | 4 | | | IV-1 | Cabyr |
| 12588 | 3 | 4 | | | IV-1 | Cacfd1 |
| 12589 | 3 | 4 | | | IV-1 | Cacna1a |
| 12590 | 3 | 4 | | | IV-1 | Cacna1b |
| 12591 | 3 | 4 | | | IV-1 | Cacna1g |
| 12592 | 3 | 4 | | | IV-1 | Cacna1i |
| 12593 | 3 | 4 | | | IV-1 | Cacna1s |
| 12594 | 3 | 4 | | | IV-1 | Cacna2d1 |
| 12595 | 3 | 4 | | | IV-1 | Cacna2d3 |
| 12596 | 3 | 4 | | | IV-1 | Cacnb1 |
| 12597 | 3 | 4 | | | IV-1 | Cacnb2 |
| 12598 | 3 | 4 | | | IV-1 | Cacnb3 |
| 12599 | 3 | 4 | | | IV-1 | Cacnb4 |
| 12600 | 3 | 4 | | | IV-1 | Cacng2 |
| 12601 | 3 | 4 | | | IV-1 | Cacng3 |
| 12602 | 3 | 4 | | | IV-1 | Cacng5 |
| 12603 | 3 | 4 | | | IV-1 | Cacng6 |
| 12604 | 3 | 4 | | | IV-1 | Cacng8 |
| 12605 | 3 | 4 | | | IV-1 | Cacul1 |
| 12606 | 3 | 4 | | | IV-1 | Cacybp |
| 12607 | 3 | 4 | | | IV-1 | Cadm2 |
| 12608 | 3 | 4 | | | IV-1 | Cadm3 |
| 12609 | 3 | 4 | | | IV-1 | Cadps |
| 12610 | 3 | 4 | | | IV-1 | Cage1 |
| 12611 | 3 | 4 | | | IV-1 | Calb1 |
| 12612 | 3 | 4 | | | IV-1 | Calcoco1 |
| 12613 | 3 | 4 | | | IV-1 | Calcr |
| 12614 | 3 | 4 | | | IV-1 | Calm1 |
| 12615 | 3 | 4 | | | IV-1 | Calm3 |
| 12616 | 3 | 4 | | | IV-1 | Calm4 |
| 12617 | 3 | 4 | | | IV-1 | Calm5 |
| 12618 | 3 | 4 | | | IV-1 | Calr4 |
| 12619 | 3 | 4 | | | IV-1 | Caly |
| 12620 | 3 | 4 | | | IV-1 | Camk2a |
| 12621 | 3 | 4 | | | IV-1 | Camk2d |
| 12622 | 3 | 4 | | | IV-1 | Camk2g |
| 12623 | 3 | 4 | | | IV-1 | Camk4 |
| 12624 | 3 | 4 | | | IV-1 | Camkk1 |
| 12625 | 3 | 4 | | | IV-1 | Camkk2 |
| 12626 | 3 | 4 | | | IV-1 | Camkv |
| 12627 | 3 | 4 | | | IV-1 | Caml |
| 12628 | 3 | 4 | | | IV-1 | Camta1 |
| 12629 | 3 | 4 | | | IV-1 | Camta2 |
| 12630 | 3 | 4 | | | IV-1 | Cand1 |
| 12631 | 3 | 4 | | | IV-1 | Cant1 |
| 12632 | 3 | 4 | | | IV-1 | Cap2 |
| 12633 | 3 | 4 | | | IV-1 | Capn1 |
| 12634 | 3 | 4 | | | IV-1 | Capn13 |
| 12635 | 3 | 4 | | | IV-1 | Capn7 |
| 12636 | 3 | 4 | | | IV-1 | Capn9 |
| 12637 | 3 | 4 | | | IV-1 | Caprin1 |
| 12638 | 3 | 4 | | | IV-1 | Caprin2 |
| 12639 | 3 | 4 | | | IV-1 | Caps2 |
| 12640 | 3 | 4 | | | IV-1 | Capza1 |
| 12641 | 3 | 4 | | | IV-1 | Capza2 |
| 12642 | 3 | 4 | | | IV-1 | Capza3 |
| 12643 | 3 | 4 | | | IV-1 | Capzb |
| 12644 | 3 | 4 | | | IV-1 | Car10 |
| 12645 | 3 | 4 | | | IV-1 | Car11 |
| 12646 | 3 | 4 | | | IV-1 | Car14 |
| 12647 | 3 | 4 | | | IV-1 | Car15 |
| 12648 | 3 | 4 | | | IV-1 | Car5a |
| 12649 | 3 | 4 | | | IV-1 | Car6 |
| 12650 | 3 | 4 | | | IV-1 | Car8 |
| 12651 | 3 | 4 | | | IV-1 | Card11 |
| 12652 | 3 | 4 | | | IV-1 | Card14 |
| 12653 | 3 | 4 | | | IV-1 | Carf |
| 12654 | 3 | 4 | | | IV-1 | Carkd |
| 12655 | 3 | 4 | | | IV-1 | Carns1 |
| 12656 | 3 | 4 | | | IV-1 | Casc1 |
| 12657 | 3 | 4 | | | IV-1 | Casc3 |
| 12658 | 3 | 4 | | | IV-1 | Casc4 |
| 12659 | 3 | 4 | | | IV-1 | Casd1 |
| 12660 | 3 | 4 | | | IV-1 | Cask |
| 12661 | 3 | 4 | | | IV-1 | Caskin1 |
| 12662 | 3 | 4 | | | IV-1 | Caskin2 |
| 12663 | 3 | 4 | | | IV-1 | Casp12 |
| 12664 | 3 | 4 | | | IV-1 | Casp14 |
| 12665 | 3 | 4 | | | IV-1 | Casp2 |
| 12666 | 3 | 4 | | | IV-1 | Casp7 |
| 12667 | 3 | 4 | | | IV-1 | Casp9 |
| 12668 | 3 | 4 | | | IV-1 | Casq2 |
| 12669 | 3 | 4 | | | IV-1 | Casz1 |
| 12670 | 3 | 4 | | | IV-1 | Catsper1 |

Fig. 36 - 67

| | | | | | | |
|---|---|---|---|---|---|---|
| 12671 | 3 | 4 | | | IV-1 | Catsper3 |
| 12672 | 3 | 4 | | | IV-1 | Catsperb |
| 12673 | 3 | 4 | | | IV-1 | Catsperd |
| 12674 | 3 | 4 | | | IV-1 | Catsperg1 |
| 12675 | 3 | 4 | | | IV-1 | Cbfa2t2 |
| 12676 | 3 | 4 | | | IV-1 | Cbfa2t3 |
| 12677 | 3 | 4 | | | IV-1 | Cbfb |
| 12678 | 3 | 4 | | | IV-1 | Cblc |
| 12679 | 3 | 4 | | | IV-1 | Cbl1 |
| 12680 | 3 | 4 | | | IV-1 | Cbln3 |
| 12681 | 3 | 4 | | | IV-1 | Cbln4 |
| 12682 | 3 | 4 | | | IV-1 | Cbr1 |
| 12683 | 3 | 4 | | | IV-1 | Cbx1 |
| 12684 | 3 | 4 | | | IV-1 | Cbx3 |
| 12685 | 3 | 4 | | | IV-1 | Cbx6 |
| 12686 | 3 | 4 | | | IV-1 | Cbx7 |
| 12687 | 3 | 4 | | | IV-1 | Cby1 |
| 12688 | 3 | 4 | | | IV-1 | Cc2d1a |
| 12689 | 3 | 4 | | | IV-1 | Cc2d1b |
| 12690 | 3 | 4 | | | IV-1 | Cc2d2a |
| 12691 | 3 | 4 | | | IV-1 | Ccar2 |
| 12692 | 3 | 4 | | | IV-1 | Ccdc103 |
| 12693 | 3 | 4 | | | IV-1 | Ccdc105 |
| 12694 | 3 | 4 | | | IV-1 | Ccdc106 |
| 12695 | 3 | 4 | | | IV-1 | Ccdc11 |
| 12696 | 3 | 4 | | | IV-1 | Ccdc110 |
| 12697 | 3 | 4 | | | IV-1 | Ccdc112 |
| 12698 | 3 | 4 | | | IV-1 | Ccdc115 |
| 12699 | 3 | 4 | | | IV-1 | Ccdc116 |
| 12700 | 3 | 4 | | | IV-1 | Ccdc117 |
| 12701 | 3 | 4 | | | IV-1 | Ccdc126 |
| 12702 | 3 | 4 | | | IV-1 | Ccdc127 |
| 12703 | 3 | 4 | | | IV-1 | Ccdc129 |
| 12704 | 3 | 4 | | | IV-1 | Ccdc13 |
| 12705 | 3 | 4 | | | IV-1 | Ccdc130 |
| 12706 | 3 | 4 | | | IV-1 | Ccdc132 |
| 12707 | 3 | 4 | | | IV-1 | Ccdc136 |
| 12708 | 3 | 4 | | | IV-1 | Ccdc138 |
| 12709 | 3 | 4 | | | IV-1 | Ccdc14 |
| 12710 | 3 | 4 | | | IV-1 | Ccdc141 |
| 12711 | 3 | 4 | | | IV-1 | Ccdc144b |
| 12712 | 3 | 4 | | | IV-1 | Ccdc146 |
| 12713 | 3 | 4 | | | IV-1 | Ccdc147 |
| 12714 | 3 | 4 | | | IV-1 | Ccdc148 |
| 12715 | 3 | 4 | | | IV-1 | Ccdc149 |
| 12716 | 3 | 4 | | | IV-1 | Ccdc15 |
| 12717 | 3 | 4 | | | IV-1 | Ccdc150 |
| 12718 | 3 | 4 | | | IV-1 | Ccdc151 |
| 12719 | 3 | 4 | | | IV-1 | Ccdc154 |
| 12720 | 3 | 4 | | | IV-1 | Ccdc158 |
| 12721 | 3 | 4 | | | IV-1 | Ccdc169 |
| 12722 | 3 | 4 | | | IV-1 | Ccdc171 |
| 12723 | 3 | 4 | | | IV-1 | Ccdc172 |
| 12724 | 3 | 4 | | | IV-1 | Ccdc175 |
| 12725 | 3 | 4 | | | IV-1 | Ccdc176 |
| 12726 | 3 | 4 | | | IV-1 | Ccdc177 |
| 12727 | 3 | 4 | | | IV-1 | Ccdc178 |
| 12728 | 3 | 4 | | | IV-1 | Ccdc18 |
| 12729 | 3 | 4 | | | IV-1 | Ccdc183 |
| 12730 | 3 | 4 | | | IV-1 | Ccdc184 |
| 12731 | 3 | 4 | | | IV-1 | Ccdc185 |
| 12732 | 3 | 4 | | | IV-1 | Ccdc25 |
| 12733 | 3 | 4 | | | IV-1 | Ccdc27 |
| 12734 | 3 | 4 | | | IV-1 | Ccdc32 |
| 12735 | 3 | 4 | | | IV-1 | Ccdc33 |
| 12736 | 3 | 4 | | | IV-1 | Ccdc34 |
| 12737 | 3 | 4 | | | IV-1 | Ccdc34os |
| 12738 | 3 | 4 | | | IV-1 | Ccdc36 |
| 12739 | 3 | 4 | | | IV-1 | Ccdc39 |
| 12740 | 3 | 4 | | | IV-1 | Ccdc42b |
| 12741 | 3 | 4 | | | IV-1 | Ccdc43 |
| 12742 | 3 | 4 | | | IV-1 | Ccdc47 |
| 12743 | 3 | 4 | | | IV-1 | Ccdc50 |
| 12744 | 3 | 4 | | | IV-1 | Ccdc54 |
| 12745 | 3 | 4 | | | IV-1 | Ccdc6 |
| 12746 | 3 | 4 | | | IV-1 | Ccdc60 |
| 12747 | 3 | 4 | | | IV-1 | Ccdc61 |
| 12748 | 3 | 4 | | | IV-1 | Ccdc62 |
| 12749 | 3 | 4 | | | IV-1 | Ccdc63 |
| 12750 | 3 | 4 | | | IV-1 | Ccdc64b |
| 12751 | 3 | 4 | | | IV-1 | Ccdc65 |
| 12752 | 3 | 4 | | | IV-1 | Ccdc66 |
| 12753 | 3 | 4 | | | IV-1 | Ccdc67 |
| 12754 | 3 | 4 | | | IV-1 | Ccdc68 |
| 12755 | 3 | 4 | | | IV-1 | Ccdc70 |
| 12756 | 3 | 4 | | | IV-1 | Ccdc71 |
| 12757 | 3 | 4 | | | IV-1 | Ccdc74a |
| 12758 | 3 | 4 | | | IV-1 | Ccdc77 |
| 12759 | 3 | 4 | | | IV-1 | Ccdc78 |
| 12760 | 3 | 4 | | | IV-1 | Ccdc79 |
| 12761 | 3 | 4 | | | IV-1 | Ccdc80 |
| 12762 | 3 | 4 | | | IV-1 | Ccdc81 |
| 12763 | 3 | 4 | | | IV-1 | Ccdc82 |
| 12764 | 3 | 4 | | | IV-1 | Ccdc83 |
| 12765 | 3 | 4 | | | IV-1 | Ccdc85b |
| 12766 | 3 | 4 | | | IV-1 | Ccdc87 |
| 12767 | 3 | 4 | | | IV-1 | Ccdc91 |
| 12768 | 3 | 4 | | | IV-1 | Ccdc94 |
| 12769 | 3 | 4 | | | IV-1 | Ccdc96 |
| 12770 | 3 | 4 | | | IV-1 | Ccer1 |
| 12771 | 3 | 4 | | | IV-1 | Cchcr1 |
| 12772 | 3 | 4 | | | IV-1 | Cckar |
| 12773 | 3 | 4 | | | IV-1 | Cckbr |
| 12774 | 3 | 4 | | | IV-1 | Ccna1 |
| 12775 | 3 | 4 | | | IV-1 | Ccnb1ip1 |
| 12776 | 3 | 4 | | | IV-1 | Ccnb2 |
| 12777 | 3 | 4 | | | IV-1 | Ccnc |
| 12778 | 3 | 4 | | | IV-1 | Ccnd3 |
| 12779 | 3 | 4 | | | IV-1 | Ccne1 |
| 12780 | 3 | 4 | | | IV-1 | Ccng2 |
| 12781 | 3 | 4 | | | IV-1 | Ccnh |
| 12782 | 3 | 4 | | | IV-1 | Ccnj |
| 12783 | 3 | 4 | | | IV-1 | Ccnk |
| 12784 | 3 | 4 | | | IV-1 | Ccnl1 |
| 12785 | 3 | 4 | | | IV-1 | Ccny |
| 12786 | 3 | 4 | | | IV-1 | Ccnyl1 |
| 12787 | 3 | 4 | | | IV-1 | Ccpg1 |
| 12788 | 3 | 4 | | | IV-1 | Ccr10 |
| 12789 | 3 | 4 | | | IV-1 | Ccrl1 |
| 12790 | 3 | 4 | | | IV-1 | Ccr4 |
| 12791 | 3 | 4 | | | IV-1 | Ccr8 |
| 12792 | 3 | 4 | | | IV-1 | Ccr9 |
| 12793 | 3 | 4 | | | IV-1 | Ccsap |
| 12794 | 3 | 4 | | | IV-1 | Ccser2 |
| 12795 | 3 | 4 | | | IV-1 | Cct2 |
| 12796 | 3 | 4 | | | IV-1 | Cct3 |
| 12797 | 3 | 4 | | | IV-1 | Cct4 |
| 12798 | 3 | 4 | | | IV-1 | Cct5 |
| 12799 | 3 | 4 | | | IV-1 | Cct8 |
| 12800 | 3 | 4 | | | IV-1 | Cct8l1 |
| 12801 | 3 | 4 | | | IV-1 | Ccz1 |
| 12802 | 3 | 4 | | | IV-1 | Cd160 |
| 12803 | 3 | 4 | | | IV-1 | Cd164 |
| 12804 | 3 | 4 | | | IV-1 | Cd200 |
| 12805 | 3 | 4 | | | IV-1 | Cd200r1 |
| 12806 | 3 | 4 | | | IV-1 | Cd200r2 |
| 12807 | 3 | 4 | | | IV-1 | Cd200r3 |
| 12808 | 3 | 4 | | | IV-1 | Cd200r4 |
| 12809 | 3 | 4 | | | IV-1 | Cd209e |
| 12810 | 3 | 4 | | | IV-1 | Cd22 |
| 12811 | 3 | 4 | | | IV-1 | Cd2ap |
| 12812 | 3 | 4 | | | IV-1 | Cd2bp2 |
| 12813 | 3 | 4 | | | IV-1 | Cd300a |
| 12814 | 3 | 4 | | | IV-1 | Cd300lb |
| 12815 | 3 | 4 | | | IV-1 | Cd300lg |
| 12816 | 3 | 4 | | | IV-1 | Cd320 |
| 12817 | 3 | 4 | | | IV-1 | Cd34 |
| 12818 | 3 | 4 | | | IV-1 | Cd3eap |
| 12819 | 3 | 4 | | | IV-1 | Cd4 |
| 12820 | 3 | 4 | | | IV-1 | Cd40 |
| 12821 | 3 | 4 | | | IV-1 | Cd5 |
| 12822 | 3 | 4 | | | IV-1 | Cd70 |
| 12823 | 3 | 4 | | | IV-1 | Cd81 |
| 12824 | 3 | 4 | | | IV-1 | Cd8a |
| 12825 | 3 | 4 | | | IV-1 | Cd8b1 |
| 12826 | 3 | 4 | | | IV-1 | Cd96 |
| 12827 | 3 | 4 | | | IV-1 | Cd97 |
| 12828 | 3 | 4 | | | IV-1 | Cd99l2 |
| 12829 | 3 | 4 | | | IV-1 | Cdadc1 |
| 12830 | 3 | 4 | | | IV-1 | Cdan1 |
| 12831 | 3 | 4 | | | IV-1 | Cdc123 |
| 12832 | 3 | 4 | | | IV-1 | Cdc14b |
| 12833 | 3 | 4 | | | IV-1 | Cdc20 |
| 12834 | 3 | 4 | | | IV-1 | Cdc20b |
| 12835 | 3 | 4 | | | IV-1 | Cdc23 |
| 12836 | 3 | 4 | | | IV-1 | Cdc26 |
| 12837 | 3 | 4 | | | IV-1 | Cdc27 |
| 12838 | 3 | 4 | | | IV-1 | Cdc37l1 |
| 12839 | 3 | 4 | | | IV-1 | Cdc42 |
| 12840 | 3 | 4 | | | IV-1 | Cdc42bpa |
| 12841 | 3 | 4 | | | IV-1 | Cdc42bpb |
| 12842 | 3 | 4 | | | IV-1 | Cdc42bpg |
| 12843 | 3 | 4 | | | IV-1 | Cdc42ep1 |
| 12844 | 3 | 4 | | | IV-1 | Cdc42ep3 |
| 12845 | 3 | 4 | | | IV-1 | Cdc42ep4 |
| 12846 | 3 | 4 | | | IV-1 | Cdc42se1 |
| 12847 | 3 | 4 | | | IV-1 | Cdc42se2 |
| 12848 | 3 | 4 | | | IV-1 | Cdc5l |
| 12849 | 3 | 4 | | | IV-1 | Cdc6 |
| 12850 | 3 | 4 | | | IV-1 | Cdc7 |
| 12851 | 3 | 4 | | | IV-1 | Cdc73 |
| 12852 | 3 | 4 | | | IV-1 | Cdca2 |
| 12853 | 3 | 4 | | | IV-1 | Cdca4 |
| 12854 | 3 | 4 | | | IV-1 | Cdca5 |
| 12855 | 3 | 4 | | | IV-1 | Cdca8 |
| 12856 | 3 | 4 | | | IV-1 | Cdh10 |
| 12857 | 3 | 4 | | | IV-1 | Cdh11 |
| 12858 | 3 | 4 | | | IV-1 | Cdh15 |
| 12859 | 3 | 4 | | | IV-1 | Cdh18 |
| 12860 | 3 | 4 | | | IV-1 | Cdh2 |
| 12861 | 3 | 4 | | | IV-1 | Cdh20 |
| 12862 | 3 | 4 | | | IV-1 | Cdh23 |

Fig. 36 - 68

| | | | | | | |
|---|---|---|---|---|---|---|
| 12863 | 3 | 4 | | | IV-1 | Cdh7 |
| 12864 | 3 | 4 | | | IV-1 | Cdh8 |
| 12865 | 3 | 4 | | | IV-1 | Cdh9 |
| 12866 | 3 | 4 | | | IV-1 | Cdhr1 |
| 12867 | 3 | 4 | | | IV-1 | Cdip1 |
| 12868 | 3 | 4 | | | IV-1 | Cdk1 |
| 12869 | 3 | 4 | | | IV-1 | Cdk11b |
| 12870 | 3 | 4 | | | IV-1 | Cdk16 |
| 12871 | 3 | 4 | | | IV-1 | Cdk17 |
| 12872 | 3 | 4 | | | IV-1 | Cdk18 |
| 12873 | 3 | 4 | | | IV-1 | Cdk19 |
| 12874 | 3 | 4 | | | IV-1 | Cdk2ap1 |
| 12875 | 3 | 4 | | | IV-1 | Cdk2ap2 |
| 12876 | 3 | 4 | | | IV-1 | Cdk3-ps |
| 12877 | 3 | 4 | | | IV-1 | Cdk4 |
| 12878 | 3 | 4 | | | IV-1 | Cdk5 |
| 12879 | 3 | 4 | | | IV-1 | Cdk5r1 |
| 12880 | 3 | 4 | | | IV-1 | Cdk5r2 |
| 12881 | 3 | 4 | | | IV-1 | Cdk8 |
| 12882 | 3 | 4 | | | IV-1 | Cdkal1 |
| 12883 | 3 | 4 | | | IV-1 | Cdkl2 |
| 12884 | 3 | 4 | | | IV-1 | Cdkn1b |
| 12885 | 3 | 4 | | | IV-1 | Cdkn2a |
| 12886 | 3 | 4 | | | IV-1 | Cdkn2aip |
| 12887 | 3 | 4 | | | IV-1 | Cdkn2aipnl |
| 12888 | 3 | 4 | | | IV-1 | Cdnf |
| 12889 | 3 | 4 | | | IV-1 | Cdr1 |
| 12890 | 3 | 4 | | | IV-1 | Cdr2l |
| 12891 | 3 | 4 | | | IV-1 | Cdv3 |
| 12892 | 3 | 4 | | | IV-1 | Cdyl2 |
| 12893 | 3 | 4 | | | IV-1 | Ceacam12 |
| 12894 | 3 | 4 | | | IV-1 | Ceacam19 |
| 12895 | 3 | 4 | | | IV-1 | Ceacam20 |
| 12896 | 3 | 4 | | | IV-1 | Cebpg |
| 12897 | 3 | 4 | | | IV-1 | Cecr5 |
| 12898 | 3 | 4 | | | IV-1 | Cecr6 |
| 12899 | 3 | 4 | | | IV-1 | Celf1 |
| 12900 | 3 | 4 | | | IV-1 | Celf3 |
| 12901 | 3 | 4 | | | IV-1 | Celf5 |
| 12902 | 3 | 4 | | | IV-1 | Cemip |
| 12903 | 3 | 4 | | | IV-1 | Cend1 |
| 12904 | 3 | 4 | | | IV-1 | Cenpb |
| 12905 | 3 | 4 | | | IV-1 | Cenpi |
| 12906 | 3 | 4 | | | IV-1 | Cenpt |
| 12907 | 3 | 4 | | | IV-1 | Cenpu |
| 12908 | 3 | 4 | | | IV-1 | Cep112 |
| 12909 | 3 | 4 | | | IV-1 | Cep120 |
| 12910 | 3 | 4 | | | IV-1 | Cep128 |
| 12911 | 3 | 4 | | | IV-1 | Cep135 |
| 12912 | 3 | 4 | | | IV-1 | Cep152 |
| 12913 | 3 | 4 | | | IV-1 | Cep164 |
| 12914 | 3 | 4 | | | IV-1 | Cep19 |
| 12915 | 3 | 4 | | | IV-1 | Cep41 |
| 12916 | 3 | 4 | | | IV-1 | Cep63 |
| 12917 | 3 | 4 | | | IV-1 | Cep70 |
| 12918 | 3 | 4 | | | IV-1 | Cep72 |
| 12919 | 3 | 4 | | | IV-1 | Cep76 |
| 12920 | 3 | 4 | | | IV-1 | Cep83 |
| 12921 | 3 | 4 | | | IV-1 | Cep83os |
| 12922 | 3 | 4 | | | IV-1 | Cep85 |
| 12923 | 3 | 4 | | | IV-1 | Cep95 |
| 12924 | 3 | 4 | | | IV-1 | Cept1 |
| 12925 | 3 | 4 | | | IV-1 | Cercam |
| 12926 | 3 | 4 | | | IV-1 | Cers2 |
| 12927 | 3 | 4 | | | IV-1 | Cers3 |
| 12928 | 3 | 4 | | | IV-1 | Cers4 |
| 12929 | 3 | 4 | | | IV-1 | Ces1e |
| 12930 | 3 | 4 | | | IV-1 | Ces1g |
| 12931 | 3 | 4 | | | IV-1 | Ces2b |
| 12932 | 3 | 4 | | | IV-1 | Ces2f |
| 12933 | 3 | 4 | | | IV-1 | Ces2h |
| 12934 | 3 | 4 | | | IV-1 | Ces3b |
| 12935 | 3 | 4 | | | IV-1 | Ces4a |
| 12936 | 3 | 4 | | | IV-1 | Cetn1 |
| 12937 | 3 | 4 | | | IV-1 | Cfdp1 |
| 12938 | 3 | 4 | | | IV-1 | Cfhr1 |
| 12939 | 3 | 4 | | | IV-1 | Cfl2 |
| 12940 | 3 | 4 | | | IV-1 | Cggbp1 |
| 12941 | 3 | 4 | | | IV-1 | Cgnl1 |
| 12942 | 3 | 4 | | | IV-1 | Chad |
| 12943 | 3 | 4 | | | IV-1 | Chaf1b |
| 12944 | 3 | 4 | | | IV-1 | Champ1 |
| 12945 | 3 | 4 | | | IV-1 | Chd1 |
| 12946 | 3 | 4 | | | IV-1 | Chd2 |
| 12947 | 3 | 4 | | | IV-1 | Chd4 |
| 12948 | 3 | 4 | | | IV-1 | Chd5 |
| 12949 | 3 | 4 | | | IV-1 | Cherp |
| 12950 | 3 | 4 | | | IV-1 | Chfr |
| 12951 | 3 | 4 | | | IV-1 | Chgb |
| 12952 | 3 | 4 | | | IV-1 | Chid1 |
| 12953 | 3 | 4 | | | IV-1 | Chil4 |
| 12954 | 3 | 4 | | | IV-1 | Chit1 |
| 12955 | 3 | 4 | | | IV-1 | Chkb |
| 12956 | 3 | 4 | | | IV-1 | Chl1 |
| 12957 | 3 | 4 | | | IV-1 | Chm |
| 12958 | 3 | 4 | | | IV-1 | Chmp1a |

| | | | | | | |
|---|---|---|---|---|---|---|
| 12959 | 3 | 4 | | | IV-1 | Chmp2b |
| 12960 | 3 | 4 | | | IV-1 | Chmp3 |
| 12961 | 3 | 4 | | | IV-1 | Chmp4b |
| 12962 | 3 | 4 | | | IV-1 | Chmp6 |
| 12963 | 3 | 4 | | | IV-1 | Chmp7 |
| 12964 | 3 | 4 | | | IV-1 | Chn1 |
| 12965 | 3 | 4 | | | IV-1 | Chn1os3 |
| 12966 | 3 | 4 | | | IV-1 | Chn2 |
| 12967 | 3 | 4 | | | IV-1 | Chodl |
| 12968 | 3 | 4 | | | IV-1 | Chordc1 |
| 12969 | 3 | 4 | | | IV-1 | Chpf |
| 12970 | 3 | 4 | | | IV-1 | Chpf2 |
| 12971 | 3 | 4 | | | IV-1 | Chpt1 |
| 12972 | 3 | 4 | | | IV-1 | Chrac1 |
| 12973 | 3 | 4 | | | IV-1 | Chrd |
| 12974 | 3 | 4 | | | IV-1 | Chrm1 |
| 12975 | 3 | 4 | | | IV-1 | Chrm4 |
| 12976 | 3 | 4 | | | IV-1 | Chrm5 |
| 12977 | 3 | 4 | | | IV-1 | Chrna10 |
| 12978 | 3 | 4 | | | IV-1 | Chrna4 |
| 12979 | 3 | 4 | | | IV-1 | Chrna6 |
| 12980 | 3 | 4 | | | IV-1 | Chrnb2 |
| 12981 | 3 | 4 | | | IV-1 | Chrnb3 |
| 12982 | 3 | 4 | | | IV-1 | Chrnb4 |
| 12983 | 3 | 4 | | | IV-1 | Chrnd |
| 12984 | 3 | 4 | | | IV-1 | Chst10 |
| 12985 | 3 | 4 | | | IV-1 | Chst12 |
| 12986 | 3 | 4 | | | IV-1 | Chst13 |
| 12987 | 3 | 4 | | | IV-1 | Chst14 |
| 12988 | 3 | 4 | | | IV-1 | Chst2 |
| 12989 | 3 | 4 | | | IV-1 | Chst4 |
| 12990 | 3 | 4 | | | IV-1 | Chsy1 |
| 12991 | 3 | 4 | | | IV-1 | Chtf18 |
| 12992 | 3 | 4 | | | IV-1 | Chtf8 |
| 12993 | 3 | 4 | | | IV-1 | Chtop |
| 12994 | 3 | 4 | | | IV-1 | Chuk |
| 12995 | 3 | 4 | | | IV-1 | Churc1 |
| 12996 | 3 | 4 | | | IV-1 | Ciao1 |
| 12997 | 3 | 4 | | | IV-1 | Ciapin1 |
| 12998 | 3 | 4 | | | IV-1 | Cib4 |
| 12999 | 3 | 4 | | | IV-1 | Cilp |
| 13000 | 3 | 4 | | | IV-1 | Cilp2 |
| 13001 | 3 | 4 | | | IV-1 | Cinp |
| 13002 | 3 | 4 | | | IV-1 | Cipc |
| 13003 | 3 | 4 | | | IV-1 | Cirh1a |
| 13004 | 3 | 4 | | | IV-1 | Cisd1 |
| 13005 | 3 | 4 | | | IV-1 | Cisd2 |
| 13006 | 3 | 4 | | | IV-1 | Ciz1 |
| 13007 | 3 | 4 | | | IV-1 | Ckap2 |
| 13008 | 3 | 4 | | | IV-1 | Ckap2l |
| 13009 | 3 | 4 | | | IV-1 | Ckap5 |
| 13010 | 3 | 4 | | | IV-1 | Cks1brt |
| 13011 | 3 | 4 | | | IV-1 | Clasp2 |
| 13012 | 3 | 4 | | | IV-1 | Clasrp |
| 13013 | 3 | 4 | | | IV-1 | Clca5 |
| 13014 | 3 | 4 | | | IV-1 | Clca6 |
| 13015 | 3 | 4 | | | IV-1 | Clcn1 |
| 13016 | 3 | 4 | | | IV-1 | Clcn4-2 |
| 13017 | 3 | 4 | | | IV-1 | Clcn7 |
| 13018 | 3 | 4 | | | IV-1 | Clcnka |
| 13019 | 3 | 4 | | | IV-1 | Clcnkb |
| 13020 | 3 | 4 | | | IV-1 | Cldn12 |
| 13021 | 3 | 4 | | | IV-1 | Cldn13 |
| 13022 | 3 | 4 | | | IV-1 | Cldn16 |
| 13023 | 3 | 4 | | | IV-1 | Cldn18 |
| 13024 | 3 | 4 | | | IV-1 | Cldn19 |
| 13025 | 3 | 4 | | | IV-1 | Cldn23 |
| 13026 | 3 | 4 | | | IV-1 | Cldn5 |
| 13027 | 3 | 4 | | | IV-1 | Cldnd2 |
| 13028 | 3 | 4 | | | IV-1 | Clec12a |
| 13029 | 3 | 4 | | | IV-1 | Clec12b |
| 13030 | 3 | 4 | | | IV-1 | Clec14a |
| 13031 | 3 | 4 | | | IV-1 | Clec16a |
| 13032 | 3 | 4 | | | IV-1 | Clec18a |
| 13033 | 3 | 4 | | | IV-1 | Clec2l |
| 13034 | 3 | 4 | | | IV-1 | Clec4a2 |
| 13035 | 3 | 4 | | | IV-1 | Clec4a4 |
| 13036 | 3 | 4 | | | IV-1 | Clec4b1 |
| 13037 | 3 | 4 | | | IV-1 | Clec4b2 |
| 13038 | 3 | 4 | | | IV-1 | Clec4f |
| 13039 | 3 | 4 | | | IV-1 | Clec4g |
| 13040 | 3 | 4 | | | IV-1 | Clec4n |
| 13041 | 3 | 4 | | | IV-1 | Clec9a |
| 13042 | 3 | 4 | | | IV-1 | Clhc1 |
| 13043 | 3 | 4 | | | IV-1 | Clic3 |
| 13044 | 3 | 4 | | | IV-1 | Clint1 |
| 13045 | 3 | 4 | | | IV-1 | Clip3 |
| 13046 | 3 | 4 | | | IV-1 | Clip4 |
| 13047 | 3 | 4 | | | IV-1 | Clk1 |
| 13048 | 3 | 4 | | | IV-1 | Clk4 |
| 13049 | 3 | 4 | | | IV-1 | Clmp |
| 13050 | 3 | 4 | | | IV-1 | Cln5 |
| 13051 | 3 | 4 | | | IV-1 | Cln6 |
| 13052 | 3 | 4 | | | IV-1 | Cln8 |
| 13053 | 3 | 4 | | | IV-1 | Clnk |
| 13054 | 3 | 4 | | | IV-1 | Clp1 |

Fig. 36 - 69

| | | | | | | |
|---|---|---|---|---|---|---|
| 13055 | 3 | 4 | | | IV-1 | Clpb |
| 13056 | 3 | 4 | | | IV-1 | Clptm1 |
| 13057 | 3 | 4 | | | IV-1 | Clptm1l |
| 13058 | 3 | 4 | | | IV-1 | Clrn1 |
| 13059 | 3 | 4 | | | IV-1 | Clspn |
| 13060 | 3 | 4 | | | IV-1 | Clstn1 |
| 13061 | 3 | 4 | | | IV-1 | Clstn2 |
| 13062 | 3 | 4 | | | IV-1 | Cltb |
| 13063 | 3 | 4 | | | IV-1 | Cltc |
| 13064 | 3 | 4 | | | IV-1 | Cluh |
| 13065 | 3 | 4 | | | IV-1 | Clvs1 |
| 13066 | 3 | 4 | | | IV-1 | Clvs2 |
| 13067 | 3 | 4 | | | IV-1 | Cmc2 |
| 13068 | 3 | 4 | | | IV-1 | Cmip |
| 13069 | 3 | 4 | | | IV-1 | Cml2 |
| 13070 | 3 | 4 | | | IV-1 | Cmpk1 |
| 13071 | 3 | 4 | | | IV-1 | Cmtm2a |
| 13072 | 3 | 4 | | | IV-1 | Cmtm2b |
| 13073 | 3 | 4 | | | IV-1 | Cmtm5 |
| 13074 | 3 | 4 | | | IV-1 | Cmtm6 |
| 13075 | 3 | 4 | | | IV-1 | Cmtr1 |
| 13076 | 3 | 4 | | | IV-1 | Cmtr2 |
| 13077 | 3 | 4 | | | IV-1 | Cnep1r1 |
| 13078 | 3 | 4 | | | IV-1 | Cnfn |
| 13079 | 3 | 4 | | | IV-1 | Cnga2 |
| 13080 | 3 | 4 | | | IV-1 | Cnga3 |
| 13081 | 3 | 4 | | | IV-1 | Cnga4 |
| 13082 | 3 | 4 | | | IV-1 | Cngb1 |
| 13083 | 3 | 4 | | | IV-1 | Cnih3 |
| 13084 | 3 | 4 | | | IV-1 | Cnih4 |
| 13085 | 3 | 4 | | | IV-1 | Cnn3 |
| 13086 | 3 | 4 | | | IV-1 | Cnnm1 |
| 13087 | 3 | 4 | | | IV-1 | Cnnm3 |
| 13088 | 3 | 4 | | | IV-1 | Cnot10 |
| 13089 | 3 | 4 | | | IV-1 | Cnot11 |
| 13090 | 3 | 4 | | | IV-1 | Cnot2 |
| 13091 | 3 | 4 | | | IV-1 | Cnot4 |
| 13092 | 3 | 4 | | | IV-1 | Cnot6l |
| 13093 | 3 | 4 | | | IV-1 | Cnot7 |
| 13094 | 3 | 4 | | | IV-1 | Cnot8 |
| 13095 | 3 | 4 | | | IV-1 | Cnppd1 |
| 13096 | 3 | 4 | | | IV-1 | Cnpy2 |
| 13097 | 3 | 4 | | | IV-1 | Cnpy3 |
| 13098 | 3 | 4 | | | IV-1 | Cnr1 |
| 13099 | 3 | 4 | | | IV-1 | Cntln |
| 13100 | 3 | 4 | | | IV-1 | Cntn2 |
| 13101 | 3 | 4 | | | IV-1 | Cntn4 |
| 13102 | 3 | 4 | | | IV-1 | Cntn5 |
| 13103 | 3 | 4 | | | IV-1 | Cntn6 |
| 13104 | 3 | 4 | | | IV-1 | Cntnap1 |
| 13105 | 3 | 4 | | | IV-1 | Cntnap2 |
| 13106 | 3 | 4 | | | IV-1 | Cntnap3 |
| 13107 | 3 | 4 | | | IV-1 | Cntnap4 |
| 13108 | 3 | 4 | | | IV-1 | Cntrob |
| 13109 | 3 | 4 | | | IV-1 | Coa6 |
| 13110 | 3 | 4 | | | IV-1 | Coa7 |
| 13111 | 3 | 4 | | | IV-1 | Coasy |
| 13112 | 3 | 4 | | | IV-1 | Coch |
| 13113 | 3 | 4 | | | IV-1 | Cog1 |
| 13114 | 3 | 4 | | | IV-1 | Cog2 |
| 13115 | 3 | 4 | | | IV-1 | Cog3 |
| 13116 | 3 | 4 | | | IV-1 | Cog4 |
| 13117 | 3 | 4 | | | IV-1 | Cog6 |
| 13118 | 3 | 4 | | | IV-1 | Cog7 |
| 13119 | 3 | 4 | | | IV-1 | Cog8 |
| 13120 | 3 | 4 | | | IV-1 | Col10a1 |
| 13121 | 3 | 4 | | | IV-1 | Col11a1 |
| 13122 | 3 | 4 | | | IV-1 | Col11a2 |
| 13123 | 3 | 4 | | | IV-1 | Col13a1 |
| 13124 | 3 | 4 | | | IV-1 | Col14a1 |
| 13125 | 3 | 4 | | | IV-1 | Col18a1 |
| 13126 | 3 | 4 | | | IV-1 | Col19a1 |
| 13127 | 3 | 4 | | | IV-1 | Col20a1 |
| 13128 | 3 | 4 | | | IV-1 | Col24a1 |
| 13129 | 3 | 4 | | | IV-1 | Col25a1 |
| 13130 | 3 | 4 | | | IV-1 | Col26a1 |
| 13131 | 3 | 4 | | | IV-1 | Col28a1 |
| 13132 | 3 | 4 | | | IV-1 | Col2a1 |
| 13133 | 3 | 4 | | | IV-1 | Col4a1 |
| 13134 | 3 | 4 | | | IV-1 | Col4a2 |
| 13135 | 3 | 4 | | | IV-1 | Col4a3bp |
| 13136 | 3 | 4 | | | IV-1 | Col4a5 |
| 13137 | 3 | 4 | | | IV-1 | Col4a6 |
| 13138 | 3 | 4 | | | IV-1 | Col5a2 |
| 13139 | 3 | 4 | | | IV-1 | Col5a3 |
| 13140 | 3 | 4 | | | IV-1 | Col8a1 |
| 13141 | 3 | 4 | | | IV-1 | Col8a2 |
| 13142 | 3 | 4 | | | IV-1 | Col9a3 |
| 13143 | 3 | 4 | | | IV-1 | Colec10 |
| 13144 | 3 | 4 | | | IV-1 | Colec12 |
| 13145 | 3 | 4 | | | IV-1 | Commd10 |
| 13146 | 3 | 4 | | | IV-1 | Commd2 |
| 13147 | 3 | 4 | | | IV-1 | Commd5 |
| 13148 | 3 | 4 | | | IV-1 | Commd6 |
| 13149 | 3 | 4 | | | IV-1 | Commd7 |
| 13150 | 3 | 4 | | | IV-1 | Commd8 |
| 13151 | 3 | 4 | | | IV-1 | Commd9 |
| 13152 | 3 | 4 | | | IV-1 | Comp |
| 13153 | 3 | 4 | | | IV-1 | Copa |
| 13154 | 3 | 4 | | | IV-1 | Copb1 |
| 13155 | 3 | 4 | | | IV-1 | Copb2 |
| 13156 | 3 | 4 | | | IV-1 | Copg1 |
| 13157 | 3 | 4 | | | IV-1 | Copg2 |
| 13158 | 3 | 4 | | | IV-1 | Cops2 |
| 13159 | 3 | 4 | | | IV-1 | Cops4 |
| 13160 | 3 | 4 | | | IV-1 | Cops5 |
| 13161 | 3 | 4 | | | IV-1 | Cops7a |
| 13162 | 3 | 4 | | | IV-1 | Cops7b |
| 13163 | 3 | 4 | | | IV-1 | Cops8 |
| 13164 | 3 | 4 | | | IV-1 | Copz1 |
| 13165 | 3 | 4 | | | IV-1 | Coq2 |
| 13166 | 3 | 4 | | | IV-1 | Coq5 |
| 13167 | 3 | 4 | | | IV-1 | Coq6 |
| 13168 | 3 | 4 | | | IV-1 | Coq9 |
| 13169 | 3 | 4 | | | IV-1 | Coro1b |
| 13170 | 3 | 4 | | | IV-1 | Coro1c |
| 13171 | 3 | 4 | | | IV-1 | Coro2b |
| 13172 | 3 | 4 | | | IV-1 | Coro7 |
| 13173 | 3 | 4 | | | IV-1 | Cox10 |
| 13174 | 3 | 4 | | | IV-1 | Cox11 |
| 13175 | 3 | 4 | | | IV-1 | Cox15 |
| 13176 | 3 | 4 | | | IV-1 | Cox19 |
| 13177 | 3 | 4 | | | IV-1 | Cox20 |
| 13178 | 3 | 4 | | | IV-1 | Cox8c |
| 13179 | 3 | 4 | | | IV-1 | Cp |
| 13180 | 3 | 4 | | | IV-1 | Cpa5 |
| 13181 | 3 | 4 | | | IV-1 | Cpb2 |
| 13182 | 3 | 4 | | | IV-1 | Cpe |
| 13183 | 3 | 4 | | | IV-1 | Cpeb1 |
| 13184 | 3 | 4 | | | IV-1 | Cpeb4 |
| 13185 | 3 | 4 | | | IV-1 | Cpm |
| 13186 | 3 | 4 | | | IV-1 | Cpn1 |
| 13187 | 3 | 4 | | | IV-1 | Cpn2 |
| 13188 | 3 | 4 | | | IV-1 | Cpne4 |
| 13189 | 3 | 4 | | | IV-1 | Cpne6 |
| 13190 | 3 | 4 | | | IV-1 | Cpne7 |
| 13191 | 3 | 4 | | | IV-1 | Cpne9 |
| 13192 | 3 | 4 | | | IV-1 | Cpox |
| 13193 | 3 | 4 | | | IV-1 | Cpped1 |
| 13194 | 3 | 4 | | | IV-1 | Cpsf2 |
| 13195 | 3 | 4 | | | IV-1 | Cpsf3 |
| 13196 | 3 | 4 | | | IV-1 | Cpsf3l |
| 13197 | 3 | 4 | | | IV-1 | Cpsf4l |
| 13198 | 3 | 4 | | | IV-1 | Cpsf6 |
| 13199 | 3 | 4 | | | IV-1 | Cpsf7 |
| 13200 | 3 | 4 | | | IV-1 | Cpt1c |
| 13201 | 3 | 4 | | | IV-1 | Cpt2 |
| 13202 | 3 | 4 | | | IV-1 | Cpvl |
| 13203 | 3 | 4 | | | IV-1 | Cpxcr1 |
| 13204 | 3 | 4 | | | IV-1 | Cpxm2 |
| 13205 | 3 | 4 | | | IV-1 | Cpz |
| 13206 | 3 | 4 | | | IV-1 | Cr1l |
| 13207 | 3 | 4 | | | IV-1 | Crabp2 |
| 13208 | 3 | 4 | | | IV-1 | Cramp1l |
| 13209 | 3 | 4 | | | IV-1 | Craf |
| 13210 | 3 | 4 | | | IV-1 | Crb2 |
| 13211 | 3 | 4 | | | IV-1 | Crbn |
| 13212 | 3 | 4 | | | IV-1 | Creb1 |
| 13213 | 3 | 4 | | | IV-1 | Creb3 |
| 13214 | 3 | 4 | | | IV-1 | Creb3l4 |
| 13215 | 3 | 4 | | | IV-1 | Creg2 |
| 13216 | 3 | 4 | | | IV-1 | Crem |
| 13217 | 3 | 4 | | | IV-1 | Crisp2 |
| 13218 | 3 | 4 | | | IV-1 | Crk |
| 13219 | 3 | 4 | | | IV-1 | Crlf3 |
| 13220 | 3 | 4 | | | IV-1 | Crmp1 |
| 13221 | 3 | 4 | | | IV-1 | Crnkl1 |
| 13222 | 3 | 4 | | | IV-1 | Crnn |
| 13223 | 3 | 4 | | | IV-1 | Crot |
| 13224 | 3 | 4 | | | IV-1 | Crtap |
| 13225 | 3 | 4 | | | IV-1 | Crtc1 |
| 13226 | 3 | 4 | | | IV-1 | Crtc2 |
| 13227 | 3 | 4 | | | IV-1 | Crtc3 |
| 13228 | 3 | 4 | | | IV-1 | Crybb2 |
| 13229 | 3 | 4 | | | IV-1 | Cs |
| 13230 | 3 | 4 | | | IV-1 | Cse1l |
| 13231 | 3 | 4 | | | IV-1 | Csf1 |
| 13232 | 3 | 4 | | | IV-1 | Csf2 |
| 13233 | 3 | 4 | | | IV-1 | Csk |
| 13234 | 3 | 4 | | | IV-1 | Csnk1a1 |
| 13235 | 3 | 4 | | | IV-1 | Csnk1g2 |
| 13236 | 3 | 4 | | | IV-1 | Csnk1g3 |
| 13237 | 3 | 4 | | | IV-1 | Csnk2a1 |
| 13238 | 3 | 4 | | | IV-1 | Csnk2a2 |
| 13239 | 3 | 4 | | | IV-1 | Csnka2ip |
| 13240 | 3 | 4 | | | IV-1 | Cspp1 |
| 13241 | 3 | 4 | | | IV-1 | Csrp2 |
| 13242 | 3 | 4 | | | IV-1 | Csrp2bp |
| 13243 | 3 | 4 | | | IV-1 | Cst3 |
| 13244 | 3 | 4 | | | IV-1 | Cst6 |
| 13245 | 3 | 4 | | | IV-1 | Cst7 |
| 13246 | 3 | 4 | | | IV-1 | Cst9 |

Fig. 36 - 70

| | | | | | | |
|---|---|---|---|---|---|---|
| 13247 | 3 | 4 | | | IV-1 | Csta1 |
| 13248 | 3 | 4 | | | IV-1 | Cstb |
| 13249 | 3 | 4 | | | IV-1 | Cstf2 |
| 13250 | 3 | 4 | | | IV-1 | Cstf2t |
| 13251 | 3 | 4 | | | IV-1 | Cstl1 |
| 13252 | 3 | 4 | | | IV-1 | Ctage5 |
| 13253 | 3 | 4 | | | IV-1 | Ctbp1 |
| 13254 | 3 | 4 | | | IV-1 | Ctbp2 |
| 13255 | 3 | 4 | | | IV-1 | Ctc1 |
| 13256 | 3 | 4 | | | IV-1 | Ctcf |
| 13257 | 3 | 4 | | | IV-1 | Ctcfl |
| 13258 | 3 | 4 | | | IV-1 | Ctcflos |
| 13259 | 3 | 4 | | | IV-1 | Ctdnep1 |
| 13260 | 3 | 4 | | | IV-1 | Ctdp1 |
| 13261 | 3 | 4 | | | IV-1 | Ctdsp1 |
| 13262 | 3 | 4 | | | IV-1 | Ctdspl |
| 13263 | 3 | 4 | | | IV-1 | Ctdspl2 |
| 13264 | 3 | 4 | | | IV-1 | Ctif |
| 13265 | 3 | 4 | | | IV-1 | Ctnna1 |
| 13266 | 3 | 4 | | | IV-1 | Ctnna2 |
| 13267 | 3 | 4 | | | IV-1 | Ctnna3 |
| 13268 | 3 | 4 | | | IV-1 | Ctnnal1 |
| 13269 | 3 | 4 | | | IV-1 | Ctnnb1 |
| 13270 | 3 | 4 | | | IV-1 | Ctnnbip1 |
| 13271 | 3 | 4 | | | IV-1 | Ctnnd1 |
| 13272 | 3 | 4 | | | IV-1 | Ctnnd2 |
| 13273 | 3 | 4 | | | IV-1 | Ctns |
| 13274 | 3 | 4 | | | IV-1 | Ctps |
| 13275 | 3 | 4 | | | IV-1 | Ctr9 |
| 13276 | 3 | 4 | | | IV-1 | Ctsa |
| 13277 | 3 | 4 | | | IV-1 | Ctsd |
| 13278 | 3 | 4 | | | IV-1 | Ctso |
| 13279 | 3 | 4 | | | IV-1 | Cttnbp2 |
| 13280 | 3 | 4 | | | IV-1 | Ctu1 |
| 13281 | 3 | 4 | | | IV-1 | Ctxn2 |
| 13282 | 3 | 4 | | | IV-1 | Cubn |
| 13283 | 3 | 4 | | | IV-1 | Cuedc2 |
| 13284 | 3 | 4 | | | IV-1 | Cul1 |
| 13285 | 3 | 4 | | | IV-1 | Cul2 |
| 13286 | 3 | 4 | | | IV-1 | Cul3 |
| 13287 | 3 | 4 | | | IV-1 | Cul4b |
| 13288 | 3 | 4 | | | IV-1 | Cul5 |
| 13289 | 3 | 4 | | | IV-1 | Cul7 |
| 13290 | 3 | 4 | | | IV-1 | Cwc15 |
| 13291 | 3 | 4 | | | IV-1 | Cwc22 |
| 13292 | 3 | 4 | | | IV-1 | Cwc25 |
| 13293 | 3 | 4 | | | IV-1 | Cwc27 |
| 13294 | 3 | 4 | | | IV-1 | Cwf19l2 |
| 13295 | 3 | 4 | | | IV-1 | Cwh43 |
| 13296 | 3 | 4 | | | IV-1 | Cxcl15 |
| 13297 | 3 | 4 | | | IV-1 | Cxcr1 |
| 13298 | 3 | 4 | | | IV-1 | Cxcr5 |
| 13299 | 3 | 4 | | | IV-1 | Cxxc1 |
| 13300 | 3 | 4 | | | IV-1 | Cxxc5 |
| 13301 | 3 | 4 | | | IV-1 | Cyb5 |
| 13302 | 3 | 4 | | | IV-1 | Cyb561d1 |
| 13303 | 3 | 4 | | | IV-1 | Cyb5b |
| 13304 | 3 | 4 | | | IV-1 | Cyb5d2 |
| 13305 | 3 | 4 | | | IV-1 | Cyb5r3 |
| 13306 | 3 | 4 | | | IV-1 | Cyb5r4 |
| 13307 | 3 | 4 | | | IV-1 | Cyc1 |
| 13308 | 3 | 4 | | | IV-1 | Cycs |
| 13309 | 3 | 4 | | | IV-1 | Cyct |
| 13310 | 3 | 4 | | | IV-1 | Cyfip1 |
| 13311 | 3 | 4 | | | IV-1 | Cygb |
| 13312 | 3 | 4 | | | IV-1 | Cylc1 |
| 13313 | 3 | 4 | | | IV-1 | Cylc2 |
| 13314 | 3 | 4 | | | IV-1 | Cyld |
| 13315 | 3 | 4 | | | IV-1 | Cym |
| 13316 | 3 | 4 | | | IV-1 | Cyp17a1 |
| 13317 | 3 | 4 | | | IV-1 | Cyp19a1 |
| 13318 | 3 | 4 | | | IV-1 | Cyp1a2 |
| 13319 | 3 | 4 | | | IV-1 | Cyp2a12 |
| 13320 | 3 | 4 | | | IV-1 | Cyp2c37 |
| 13321 | 3 | 4 | | | IV-1 | Cyp2c50 |
| 13322 | 3 | 4 | | | IV-1 | Cyp2c55 |
| 13323 | 3 | 4 | | | IV-1 | Cyp2c65 |
| 13324 | 3 | 4 | | | IV-1 | Cyp2c69 |
| 13325 | 3 | 4 | | | IV-1 | Cyp2d11 |
| 13326 | 3 | 4 | | | IV-1 | Cyp2d12 |
| 13327 | 3 | 4 | | | IV-1 | Cyp2d13 |
| 13328 | 3 | 4 | | | IV-1 | Cyp2j11 |
| 13329 | 3 | 4 | | | IV-1 | Cyp2j13 |
| 13330 | 3 | 4 | | | IV-1 | Cyp2j5 |
| 13331 | 3 | 4 | | | IV-1 | Cyp2j6 |
| 13332 | 3 | 4 | | | IV-1 | Cyp2j8 |
| 13333 | 3 | 4 | | | IV-1 | Cyp2r1 |
| 13334 | 3 | 4 | | | IV-1 | Cyp2s1 |
| 13335 | 3 | 4 | | | IV-1 | Cyp3a25 |
| 13336 | 3 | 4 | | | IV-1 | Cyp3a41a |
| 13337 | 3 | 4 | | | IV-1 | Cyp3a41b |
| 13338 | 3 | 4 | | | IV-1 | Cyp3a44 |
| 13339 | 3 | 4 | | | IV-1 | Cyp3a57 |
| 13340 | 3 | 4 | | | IV-1 | Cyp3a59 |
| 13341 | 3 | 4 | | | IV-1 | Cyp4a12a |
| 13342 | 3 | 4 | | | IV-1 | Cyp4a12b |
| 13343 | 3 | 4 | | | IV-1 | Cyp4f39 |
| 13344 | 3 | 4 | | | IV-1 | Cyp4f40 |
| 13345 | 3 | 4 | | | IV-1 | Cyp4v3 |
| 13346 | 3 | 4 | | | IV-1 | Cypt1 |
| 13347 | 3 | 4 | | | IV-1 | Cypt12 |
| 13348 | 3 | 4 | | | IV-1 | Cypt15 |
| 13349 | 3 | 4 | | | IV-1 | Cypt2 |
| 13350 | 3 | 4 | | | IV-1 | Cypt3 |
| 13351 | 3 | 4 | | | IV-1 | Cypt4 |
| 13352 | 3 | 4 | | | IV-1 | Cypt9 |
| 13353 | 3 | 4 | | | IV-1 | Cysltr2 |
| 13354 | 3 | 4 | | | IV-1 | Cyth2 |
| 13355 | 3 | 4 | | | IV-1 | Cyth3 |
| 13356 | 3 | 4 | | | IV-1 | D030018L15Rik |
| 13357 | 3 | 4 | | | IV-1 | D030045P18Rik |
| 13358 | 3 | 4 | | | IV-1 | D10Jhu81e |
| 13359 | 3 | 4 | | | IV-1 | D10Wsu102e |
| 13360 | 3 | 4 | | | IV-1 | D15Ertd621e |
| 13361 | 3 | 4 | | | IV-1 | D16Ertd472e |
| 13362 | 3 | 4 | | | IV-1 | D17H6S53E |
| 13363 | 3 | 4 | | | IV-1 | D17Wsu104e |
| 13364 | 3 | 4 | | | IV-1 | D17Wsu92e |
| 13365 | 3 | 4 | | | IV-1 | D19Bwg1357e |
| 13366 | 3 | 4 | | | IV-1 | D330045A20Rik |
| 13367 | 3 | 4 | | | IV-1 | D330050G23Rik |
| 13368 | 3 | 4 | | | IV-1 | D3Bwg0562e |
| 13369 | 3 | 4 | | | IV-1 | D3Ertd751e |
| 13370 | 3 | 4 | | | IV-1 | D430036J16Rik |
| 13371 | 3 | 4 | | | IV-1 | D430041D05Rik |
| 13372 | 3 | 4 | | | IV-1 | D630029K05Rik |
| 13373 | 3 | 4 | | | IV-1 | D6Ertd527e |
| 13374 | 3 | 4 | | | IV-1 | D6Wsu163e |
| 13375 | 3 | 4 | | | IV-1 | D830013O20Rik |
| 13376 | 3 | 4 | | | IV-1 | D830015G02Rik |
| 13377 | 3 | 4 | | | IV-1 | D830030K20Rik |
| 13378 | 3 | 4 | | | IV-1 | D830032E09Rik |
| 13379 | 3 | 4 | | | IV-1 | D8Ertd82e |
| 13380 | 3 | 4 | | | IV-1 | D930015E06Rik |
| 13381 | 3 | 4 | | | IV-1 | D930020B18Rik |
| 13382 | 3 | 4 | | | IV-1 | Daam1 |
| 13383 | 3 | 4 | | | IV-1 | Daam2 |
| 13384 | 3 | 4 | | | IV-1 | Dab1 |
| 13385 | 3 | 4 | | | IV-1 | Dab2 |
| 13386 | 3 | 4 | | | IV-1 | Dab2ip |
| 13387 | 3 | 4 | | | IV-1 | Dach2 |
| 13388 | 3 | 4 | | | IV-1 | Dact1 |
| 13389 | 3 | 4 | | | IV-1 | Daf2 |
| 13390 | 3 | 4 | | | IV-1 | Daglb |
| 13391 | 3 | 4 | | | IV-1 | Dalrd3 |
| 13392 | 3 | 4 | | | IV-1 | Dap |
| 13393 | 3 | 4 | | | IV-1 | Dap3 |
| 13394 | 3 | 4 | | | IV-1 | Dapk1 |
| 13395 | 3 | 4 | | | IV-1 | Dars |
| 13396 | 3 | 4 | | | IV-1 | Dars2 |
| 13397 | 3 | 4 | | | IV-1 | Daw1 |
| 13398 | 3 | 4 | | | IV-1 | Daxx |
| 13399 | 3 | 4 | | | IV-1 | Dazap1 |
| 13400 | 3 | 4 | | | IV-1 | Dazl |
| 13401 | 3 | 4 | | | IV-1 | Dbf4 |
| 13402 | 3 | 4 | | | IV-1 | Dbh |
| 13403 | 3 | 4 | | | IV-1 | Dbn1 |
| 13404 | 3 | 4 | | | IV-1 | Dbndd2 |
| 13405 | 3 | 4 | | | IV-1 | Dbnl |
| 13406 | 3 | 4 | | | IV-1 | Dbpht2 |
| 13407 | 3 | 4 | | | IV-1 | Dbt |
| 13408 | 3 | 4 | | | IV-1 | Dbx2 |
| 13409 | 3 | 4 | | | IV-1 | Dcaf11 |
| 13410 | 3 | 4 | | | IV-1 | Dcaf12l1 |
| 13411 | 3 | 4 | | | IV-1 | Dcaf13 |
| 13412 | 3 | 4 | | | IV-1 | Dcaf15 |
| 13413 | 3 | 4 | | | IV-1 | Dcaf4 |
| 13414 | 3 | 4 | | | IV-1 | Dcaf5 |
| 13415 | 3 | 4 | | | IV-1 | Dcaf7 |
| 13416 | 3 | 4 | | | IV-1 | Dcaf8 |
| 13417 | 3 | 4 | | | IV-1 | Dcbld2 |
| 13418 | 3 | 4 | | | IV-1 | Dcdc2c |
| 13419 | 3 | 4 | | | IV-1 | Dctre1c |
| 13420 | 3 | 4 | | | IV-1 | Dcn |
| 13421 | 3 | 4 | | | IV-1 | Dcp1a |
| 13422 | 3 | 4 | | | IV-1 | Dcp1b |
| 13423 | 3 | 4 | | | IV-1 | Dcst1 |
| 13424 | 3 | 4 | | | IV-1 | Dctn2 |
| 13425 | 3 | 4 | | | IV-1 | Dctn4 |
| 13426 | 3 | 4 | | | IV-1 | Dctn5 |
| 13427 | 3 | 4 | | | IV-1 | Dctn6 |
| 13428 | 3 | 4 | | | IV-1 | Dcun1d2 |
| 13429 | 3 | 4 | | | IV-1 | Dda1 |
| 13430 | 3 | 4 | | | IV-1 | Ddah1 |
| 13431 | 3 | 4 | | | IV-1 | Ddb1 |
| 13432 | 3 | 4 | | | IV-1 | Ddhd1 |
| 13433 | 3 | 4 | | | IV-1 | Ddhd2 |
| 13434 | 3 | 4 | | | IV-1 | Ddi1 |
| 13435 | 3 | 4 | | | IV-1 | Ddn |
| 13436 | 3 | 4 | | | IV-1 | Ddr1 |
| 13437 | 3 | 4 | | | IV-1 | Ddrgk1 |
| 13438 | 3 | 4 | | | IV-1 | Ddx1 |

Fig. 36 - 71

| | | | | | | |
|---|---|---|---|---|---|---|
| 13439 | 3 | 4 | | | IV-1 | Ddx10 |
| 13440 | 3 | 4 | | | IV-1 | Ddx19a |
| 13441 | 3 | 4 | | | IV-1 | Ddx19b |
| 13442 | 3 | 4 | | | IV-1 | Ddx20 |
| 13443 | 3 | 4 | | | IV-1 | Ddx21 |
| 13444 | 3 | 4 | | | IV-1 | Ddx23 |
| 13445 | 3 | 4 | | | IV-1 | Ddx24 |
| 13446 | 3 | 4 | | | IV-1 | Ddx25 |
| 13447 | 3 | 4 | | | IV-1 | Ddx26b |
| 13448 | 3 | 4 | | | IV-1 | Ddx27 |
| 13449 | 3 | 4 | | | IV-1 | Ddx28 |
| 13450 | 3 | 4 | | | IV-1 | Ddx3x |
| 13451 | 3 | 4 | | | IV-1 | Ddx4 |
| 13452 | 3 | 4 | | | IV-1 | Ddx41 |
| 13453 | 3 | 4 | | | IV-1 | Ddx42 |
| 13454 | 3 | 4 | | | IV-1 | Ddx46 |
| 13455 | 3 | 4 | | | IV-1 | Ddx47 |
| 13456 | 3 | 4 | | | IV-1 | Ddx5 |
| 13457 | 3 | 4 | | | IV-1 | Ddx50 |
| 13458 | 3 | 4 | | | IV-1 | Ddx52 |
| 13459 | 3 | 4 | | | IV-1 | Ddx54 |
| 13460 | 3 | 4 | | | IV-1 | Ddx59 |
| 13461 | 3 | 4 | | | IV-1 | Ddx6 |
| 13462 | 3 | 4 | | | IV-1 | Ddx60 |
| 13463 | 3 | 4 | | | IV-1 | Deaf1 |
| 13464 | 3 | 4 | | | IV-1 | Decr1 |
| 13465 | 3 | 4 | | | IV-1 | Decr2 |
| 13466 | 3 | 4 | | | IV-1 | Dedd |
| 13467 | 3 | 4 | | | IV-1 | Dedd2 |
| 13468 | 3 | 4 | | | IV-1 | Def8 |
| 13469 | 3 | 4 | | | IV-1 | Defb23 |
| 13470 | 3 | 4 | | | IV-1 | Defb28 |
| 13471 | 3 | 4 | | | IV-1 | Defb3 |
| 13472 | 3 | 4 | | | IV-1 | Defb33 |
| 13473 | 3 | 4 | | | IV-1 | Defb6 |
| 13474 | 3 | 4 | | | IV-1 | Degs2 |
| 13475 | 3 | 4 | | | IV-1 | Dek |
| 13476 | 3 | 4 | | | IV-1 | Dennd1a |
| 13477 | 3 | 4 | | | IV-1 | Dennd1b |
| 13478 | 3 | 4 | | | IV-1 | Dennd1c |
| 13479 | 3 | 4 | | | IV-1 | Dennd2c |
| 13480 | 3 | 4 | | | IV-1 | Dennd2d |
| 13481 | 3 | 4 | | | IV-1 | Dennd4a |
| 13482 | 3 | 4 | | | IV-1 | Dennd4b |
| 13483 | 3 | 4 | | | IV-1 | Dennd6a |
| 13484 | 3 | 4 | | | IV-1 | Denr |
| 13485 | 3 | 4 | | | IV-1 | Depdc5 |
| 13486 | 3 | 4 | | | IV-1 | Dera |
| 13487 | 3 | 4 | | | IV-1 | Derl2 |
| 13488 | 3 | 4 | | | IV-1 | Desi1 |
| 13489 | 3 | 4 | | | IV-1 | Desi2 |
| 13490 | 3 | 4 | | | IV-1 | Dexi |
| 13491 | 3 | 4 | | | IV-1 | Dffb |
| 13492 | 3 | 4 | | | IV-1 | Dgat2l6 |
| 13493 | 3 | 4 | | | IV-1 | Dgcr14 |
| 13494 | 3 | 4 | | | IV-1 | Dgcr2 |
| 13495 | 3 | 4 | | | IV-1 | Dgcr8 |
| 13496 | 3 | 4 | | | IV-1 | Dgka |
| 13497 | 3 | 4 | | | IV-1 | Dgkh |
| 13498 | 3 | 4 | | | IV-1 | Dgkd |
| 13499 | 3 | 4 | | | IV-1 | Dgkg |
| 13500 | 3 | 4 | | | IV-1 | Dguok |
| 13501 | 3 | 4 | | | IV-1 | Dhdds |
| 13502 | 3 | 4 | | | IV-1 | Dhfr |
| 13503 | 3 | 4 | | | IV-1 | Dhodh |
| 13504 | 3 | 4 | | | IV-1 | Dhps |
| 13505 | 3 | 4 | | | IV-1 | Dhrs1 |
| 13506 | 3 | 4 | | | IV-1 | Dhrsx |
| 13507 | 3 | 4 | | | IV-1 | Dhx15 |
| 13508 | 3 | 4 | | | IV-1 | Dhx16 |
| 13509 | 3 | 4 | | | IV-1 | Dhx30 |
| 13510 | 3 | 4 | | | IV-1 | Dhx32 |
| 13511 | 3 | 4 | | | IV-1 | Dhx33 |
| 13512 | 3 | 4 | | | IV-1 | Dhx35 |
| 13513 | 3 | 4 | | | IV-1 | Dhx36 |
| 13514 | 3 | 4 | | | IV-1 | Dhx37 |
| 13515 | 3 | 4 | | | IV-1 | Dhx38 |
| 13516 | 3 | 4 | | | IV-1 | Dhx40 |
| 13517 | 3 | 4 | | | IV-1 | Dhx57 |
| 13518 | 3 | 4 | | | IV-1 | Dhx58 |
| 13519 | 3 | 4 | | | IV-1 | Dhx8 |
| 13520 | 3 | 4 | | | IV-1 | Dhx9 |
| 13521 | 3 | 4 | | | IV-1 | Diablo |
| 13522 | 3 | 4 | | | IV-1 | Diexf |
| 13523 | 3 | 4 | | | IV-1 | Dio3 |
| 13524 | 3 | 4 | | | IV-1 | Dip2a |
| 13525 | 3 | 4 | | | IV-1 | Dip2b |
| 13526 | 3 | 4 | | | IV-1 | Dip2c |
| 13527 | 3 | 4 | | | IV-1 | Diras1 |
| 13528 | 3 | 4 | | | IV-1 | Dirc2 |
| 13529 | 3 | 4 | | | IV-1 | Dis3 |
| 13530 | 3 | 4 | | | IV-1 | Dis3l |
| 13531 | 3 | 4 | | | IV-1 | Dkk3 |
| 13532 | 3 | 4 | | | IV-1 | Dlat |
| 13533 | 3 | 4 | | | IV-1 | Dlc1 |
| 13534 | 3 | 4 | | | IV-1 | Dld |

| | | | | | | |
|---|---|---|---|---|---|---|
| 13535 | 3 | 4 | | | IV-1 | Dlg1 |
| 13536 | 3 | 4 | | | IV-1 | Dlg2 |
| 13537 | 3 | 4 | | | IV-1 | Dlg3 |
| 13538 | 3 | 4 | | | IV-1 | Dlg4 |
| 13539 | 3 | 4 | | | IV-1 | Dlgap3 |
| 13540 | 3 | 4 | | | IV-1 | Dlgap5 |
| 13541 | 3 | 4 | | | IV-1 | Dlk1 |
| 13542 | 3 | 4 | | | IV-1 | Dlk2 |
| 13543 | 3 | 4 | | | IV-1 | Dll3 |
| 13544 | 3 | 4 | | | IV-1 | Dll4 |
| 13545 | 3 | 4 | | | IV-1 | Dlst |
| 13546 | 3 | 4 | | | IV-1 | Dlx1 |
| 13547 | 3 | 4 | | | IV-1 | Dlx1as |
| 13548 | 3 | 4 | | | IV-1 | Dlx2 |
| 13549 | 3 | 4 | | | IV-1 | Dlx3 |
| 13550 | 3 | 4 | | | IV-1 | Dlx5 |
| 13551 | 3 | 4 | | | IV-1 | Dlx6 |
| 13552 | 3 | 4 | | | IV-1 | Dmbx1 |
| 13553 | 3 | 4 | | | IV-1 | Dmc1 |
| 13554 | 3 | 4 | | | IV-1 | Dmd |
| 13555 | 3 | 4 | | | IV-1 | Dmgdh |
| 13556 | 3 | 4 | | | IV-1 | Dmp1 |
| 13557 | 3 | 4 | | | IV-1 | Dmr |
| 13558 | 3 | 4 | | | IV-1 | Dmrt1 |
| 13559 | 3 | 4 | | | IV-1 | Dmrt2 |
| 13560 | 3 | 4 | | | IV-1 | Dmrt3 |
| 13561 | 3 | 4 | | | IV-1 | Dmrtc1c2 |
| 13562 | 3 | 4 | | | IV-1 | Dmrtc2 |
| 13563 | 3 | 4 | | | IV-1 | Dmtf1 |
| 13564 | 3 | 4 | | | IV-1 | Dmwd |
| 13565 | 3 | 4 | | | IV-1 | Dnaaf1 |
| 13566 | 3 | 4 | | | IV-1 | Dnah1 |
| 13567 | 3 | 4 | | | IV-1 | Dnah11 |
| 13568 | 3 | 4 | | | IV-1 | Dnah2 |
| 13569 | 3 | 4 | | | IV-1 | Dnah5 |
| 13570 | 3 | 4 | | | IV-1 | Dnah7b |
| 13571 | 3 | 4 | | | IV-1 | Dnah9 |
| 13572 | 3 | 4 | | | IV-1 | Dnaic1 |
| 13573 | 3 | 4 | | | IV-1 | Dnaja2 |
| 13574 | 3 | 4 | | | IV-1 | Dnaja3 |
| 13575 | 3 | 4 | | | IV-1 | Dnajb1 |
| 13576 | 3 | 4 | | | IV-1 | Dnajb11 |
| 13577 | 3 | 4 | | | IV-1 | Dnajb12 |
| 13578 | 3 | 4 | | | IV-1 | Dnajb13 |
| 13579 | 3 | 4 | | | IV-1 | Dnajb5 |
| 13580 | 3 | 4 | | | IV-1 | Dnajb7 |
| 13581 | 3 | 4 | | | IV-1 | Dnajb8 |
| 13582 | 3 | 4 | | | IV-1 | Dnajc11 |
| 13583 | 3 | 4 | | | IV-1 | Dnajc13 |
| 13584 | 3 | 4 | | | IV-1 | Dnajc18 |
| 13585 | 3 | 4 | | | IV-1 | Dnajc21 |
| 13586 | 3 | 4 | | | IV-1 | Dnajc27 |
| 13587 | 3 | 4 | | | IV-1 | Dnajc28 |
| 13588 | 3 | 4 | | | IV-1 | Dnajc3 |
| 13589 | 3 | 4 | | | IV-1 | Dnajc30 |
| 13590 | 3 | 4 | | | IV-1 | Dnajc4 |
| 13591 | 3 | 4 | | | IV-1 | Dnajc5 |
| 13592 | 3 | 4 | | | IV-1 | Dnajc5b |
| 13593 | 3 | 4 | | | IV-1 | Dnajc5g |
| 13594 | 3 | 4 | | | IV-1 | Dnal4 |
| 13595 | 3 | 4 | | | IV-1 | Dnase1l3 |
| 13596 | 3 | 4 | | | IV-1 | Dnase2b |
| 13597 | 3 | 4 | | | IV-1 | Dner |
| 13598 | 3 | 4 | | | IV-1 | Dnlz |
| 13599 | 3 | 4 | | | IV-1 | Dnm1 |
| 13600 | 3 | 4 | | | IV-1 | Dnm2 |
| 13601 | 3 | 4 | | | IV-1 | Dnm3 |
| 13602 | 3 | 4 | | | IV-1 | Dnm3os |
| 13603 | 3 | 4 | | | IV-1 | Dnmt3a |
| 13604 | 3 | 4 | | | IV-1 | Dnpep |
| 13605 | 3 | 4 | | | IV-1 | Dnttip2 |
| 13606 | 3 | 4 | | | IV-1 | Dock1 |
| 13607 | 3 | 4 | | | IV-1 | Dock10 |
| 13608 | 3 | 4 | | | IV-1 | Dock11 |
| 13609 | 3 | 4 | | | IV-1 | Dock2 |
| 13610 | 3 | 4 | | | IV-1 | Dock3 |
| 13611 | 3 | 4 | | | IV-1 | Dock5 |
| 13612 | 3 | 4 | | | IV-1 | Dock6 |
| 13613 | 3 | 4 | | | IV-1 | Dock7 |
| 13614 | 3 | 4 | | | IV-1 | Dok5 |
| 13615 | 3 | 4 | | | IV-1 | Dolk |
| 13616 | 3 | 4 | | | IV-1 | Dolpp1 |
| 13617 | 3 | 4 | | | IV-1 | Donson |
| 13618 | 3 | 4 | | | IV-1 | Dpcr1 |
| 13619 | 3 | 4 | | | IV-1 | Dpep3 |
| 13620 | 3 | 4 | | | IV-1 | Dpf1 |
| 13621 | 3 | 4 | | | IV-1 | Dpf2 |
| 13622 | 3 | 4 | | | IV-1 | Dph2 |
| 13623 | 3 | 4 | | | IV-1 | Dph3 |
| 13624 | 3 | 4 | | | IV-1 | Dph6 |
| 13625 | 3 | 4 | | | IV-1 | Dpm1 |
| 13626 | 3 | 4 | | | IV-1 | Dpp10 |
| 13627 | 3 | 4 | | | IV-1 | Dpp3 |
| 13628 | 3 | 4 | | | IV-1 | Dpp4 |
| 13629 | 3 | 4 | | | IV-1 | Dpp6 |
| 13630 | 3 | 4 | | | IV-1 | Dpp9 |

Fig. 36 - 72

| | | | | | | |
|---|---|---|---|---|---|---|
| 13631 | 3 | 4 | | | IV-1 | Dppa4 |
| 13632 | 3 | 4 | | | IV-1 | Dppa5a |
| 13633 | 3 | 4 | | | IV-1 | Dpy19l1 |
| 13634 | 3 | 4 | | | IV-1 | Dpy19l2 |
| 13635 | 3 | 4 | | | IV-1 | Dpy19l3 |
| 13636 | 3 | 4 | | | IV-1 | Dpyd |
| 13637 | 3 | 4 | | | IV-1 | Dpys |
| 13638 | 3 | 4 | | | IV-1 | Dpysl3 |
| 13639 | 3 | 4 | | | IV-1 | Dpysl5 |
| 13640 | 3 | 4 | | | IV-1 | Dqx1 |
| 13641 | 3 | 4 | | | IV-1 | Dram1 |
| 13642 | 3 | 4 | | | IV-1 | Drc1 |
| 13643 | 3 | 4 | | | IV-1 | Drd5 |
| 13644 | 3 | 4 | | | IV-1 | Dreh |
| 13645 | 3 | 4 | | | IV-1 | Drg1 |
| 13646 | 3 | 4 | | | IV-1 | Drg2 |
| 13647 | 3 | 4 | | | IV-1 | Drosha |
| 13648 | 3 | 4 | | | IV-1 | Dsc1 |
| 13649 | 3 | 4 | | | IV-1 | Dsc3 |
| 13650 | 3 | 4 | | | IV-1 | Dscam |
| 13651 | 3 | 4 | | | IV-1 | Dscr3 |
| 13652 | 3 | 4 | | | IV-1 | Dsel |
| 13653 | 3 | 4 | | | IV-1 | Dsg1a |
| 13654 | 3 | 4 | | | IV-1 | Dsg1b |
| 13655 | 3 | 4 | | | IV-1 | Dsg1c |
| 13656 | 3 | 4 | | | IV-1 | Dsg3 |
| 13657 | 3 | 4 | | | IV-1 | Dsn1 |
| 13658 | 3 | 4 | | | IV-1 | Dstn |
| 13659 | 3 | 4 | | | IV-1 | Dstyk |
| 13660 | 3 | 4 | | | IV-1 | Dtd1 |
| 13661 | 3 | 4 | | | IV-1 | Dtd2 |
| 13662 | 3 | 4 | | | IV-1 | Dtl |
| 13663 | 3 | 4 | | | IV-1 | Dtna |
| 13664 | 3 | 4 | | | IV-1 | Dtnbp1 |
| 13665 | 3 | 4 | | | IV-1 | Dtwd1 |
| 13666 | 3 | 4 | | | IV-1 | Duox1 |
| 13667 | 3 | 4 | | | IV-1 | Duoxa1 |
| 13668 | 3 | 4 | | | IV-1 | Dus3l |
| 13669 | 3 | 4 | | | IV-1 | Dusp11 |
| 13670 | 3 | 4 | | | IV-1 | Dusp15 |
| 13671 | 3 | 4 | | | IV-1 | Dusp18 |
| 13672 | 3 | 4 | | | IV-1 | Dusp22 |
| 13673 | 3 | 4 | | | IV-1 | Dusp27 |
| 13674 | 3 | 4 | | | IV-1 | Dusp28 |
| 13675 | 3 | 4 | | | IV-1 | Dusp3 |
| 13676 | 3 | 4 | | | IV-1 | Dusp6 |
| 13677 | 3 | 4 | | | IV-1 | Dusp9 |
| 13678 | 3 | 4 | | | IV-1 | Duxbl2 |
| 13679 | 3 | 4 | | | IV-1 | Dvl1 |
| 13680 | 3 | 4 | | | IV-1 | Dvl2 |
| 13681 | 3 | 4 | | | IV-1 | Dxo |
| 13682 | 3 | 4 | | | IV-1 | Dydc1 |
| 13683 | 3 | 4 | | | IV-1 | Dync1i1 |
| 13684 | 3 | 4 | | | IV-1 | Dync1i2 |
| 13685 | 3 | 4 | | | IV-1 | Dync1li2 |
| 13686 | 3 | 4 | | | IV-1 | Dyrk4 |
| 13687 | 3 | 4 | | | IV-1 | Dysf |
| 13688 | 3 | 4 | | | IV-1 | Dzip1 |
| 13689 | 3 | 4 | | | IV-1 | Dzip3 |
| 13690 | 3 | 4 | | | IV-1 | E030013I19Rik |
| 13691 | 3 | 4 | | | IV-1 | E030018B13Rik |
| 13692 | 3 | 4 | | | IV-1 | E030019B06Rik |
| 13693 | 3 | 4 | | | IV-1 | E130008D07Rik |
| 13694 | 3 | 4 | | | IV-1 | E130114P18Rik |
| 13695 | 3 | 4 | | | IV-1 | E130309D02Rik |
| 13696 | 3 | 4 | | | IV-1 | E130309D14Rik |
| 13697 | 3 | 4 | | | IV-1 | E230008N13Rik |
| 13698 | 3 | 4 | | | IV-1 | E2f1 |
| 13699 | 3 | 4 | | | IV-1 | E2f3 |
| 13700 | 3 | 4 | | | IV-1 | E2f4 |
| 13701 | 3 | 4 | | | IV-1 | E2f5 |
| 13702 | 3 | 4 | | | IV-1 | E2f6 |
| 13703 | 3 | 4 | | | IV-1 | E2f7 |
| 13704 | 3 | 4 | | | IV-1 | E330011O21Rik |
| 13705 | 3 | 4 | | | IV-1 | E330013P04Rik |
| 13706 | 3 | 4 | | | IV-1 | E330020D12Rik |
| 13707 | 3 | 4 | | | IV-1 | E330033B04Rik |
| 13708 | 3 | 4 | | | IV-1 | E330034G19Rik |
| 13709 | 3 | 4 | | | IV-1 | E430025E21Rik |
| 13710 | 3 | 4 | | | IV-1 | E4f1 |
| 13711 | 3 | 4 | | | IV-1 | E530001F21Rik |
| 13712 | 3 | 4 | | | IV-1 | E530011L22Rik |
| 13713 | 3 | 4 | | | IV-1 | EU599041 |
| 13714 | 3 | 4 | | | IV-1 | Eaf2 |
| 13715 | 3 | 4 | | | IV-1 | Eapp |
| 13716 | 3 | 4 | | | IV-1 | Ebf4 |
| 13717 | 3 | 4 | | | IV-1 | Ebna1bp2 |
| 13718 | 3 | 4 | | | IV-1 | Ecd |
| 13719 | 3 | 4 | | | IV-1 | Ece1 |
| 13720 | 3 | 4 | | | IV-1 | Ecel1 |
| 13721 | 3 | 4 | | | IV-1 | Echs1 |
| 13722 | 3 | 4 | | | IV-1 | Ect2 |
| 13723 | 3 | 4 | | | IV-1 | Edar |
| 13724 | 3 | 4 | | | IV-1 | Edaradd |
| 13725 | 3 | 4 | | | IV-1 | Edc3 |
| 13726 | 3 | 4 | | | IV-1 | Edc4 |
| 13727 | 3 | 4 | | | IV-1 | Edem2 |
| 13728 | 3 | 4 | | | IV-1 | Edem3 |
| 13729 | 3 | 4 | | | IV-1 | Edil3 |
| 13730 | 3 | 4 | | | IV-1 | Edn2 |
| 13731 | 3 | 4 | | | IV-1 | Ednra |
| 13732 | 3 | 4 | | | IV-1 | Eea1 |
| 13733 | 3 | 4 | | | IV-1 | Eef1a1 |
| 13734 | 3 | 4 | | | IV-1 | Eef1b2 |
| 13735 | 3 | 4 | | | IV-1 | Eef1g |
| 13736 | 3 | 4 | | | IV-1 | Eef2 |
| 13737 | 3 | 4 | | | IV-1 | Eef2k |
| 13738 | 3 | 4 | | | IV-1 | Eefsec |
| 13739 | 3 | 4 | | | IV-1 | Efcab14 |
| 13740 | 3 | 4 | | | IV-1 | Efcab3 |
| 13741 | 3 | 4 | | | IV-1 | Efcab5 |
| 13742 | 3 | 4 | | | IV-1 | Efcab6 |
| 13743 | 3 | 4 | | | IV-1 | Efcab9 |
| 13744 | 3 | 4 | | | IV-1 | Efemp2 |
| 13745 | 3 | 4 | | | IV-1 | Efhb |
| 13746 | 3 | 4 | | | IV-1 | Efhc2 |
| 13747 | 3 | 4 | | | IV-1 | Efhd2 |
| 13748 | 3 | 4 | | | IV-1 | Efna1 |
| 13749 | 3 | 4 | | | IV-1 | Efna2 |
| 13750 | 3 | 4 | | | IV-1 | Efnb1 |
| 13751 | 3 | 4 | | | IV-1 | Efnb2 |
| 13752 | 3 | 4 | | | IV-1 | Efnb3 |
| 13753 | 3 | 4 | | | IV-1 | Efr3a |
| 13754 | 3 | 4 | | | IV-1 | Efs |
| 13755 | 3 | 4 | | | IV-1 | Eftud1 |
| 13756 | 3 | 4 | | | IV-1 | Eftud2 |
| 13757 | 3 | 4 | | | IV-1 | Egf |
| 13758 | 3 | 4 | | | IV-1 | Egfem1 |
| 13759 | 3 | 4 | | | IV-1 | Egln1 |
| 13760 | 3 | 4 | | | IV-1 | Egln2 |
| 13761 | 3 | 4 | | | IV-1 | Egln3 |
| 13762 | 3 | 4 | | | IV-1 | Egr4 |
| 13763 | 3 | 4 | | | IV-1 | Ehbp1 |
| 13764 | 3 | 4 | | | IV-1 | Ehbp1l1 |
| 13765 | 3 | 4 | | | IV-1 | Ehd1 |
| 13766 | 3 | 4 | | | IV-1 | Ehd2 |
| 13767 | 3 | 4 | | | IV-1 | Ehmt1 |
| 13768 | 3 | 4 | | | IV-1 | Ehmt2 |
| 13769 | 3 | 4 | | | IV-1 | Eid2b |
| 13770 | 3 | 4 | | | IV-1 | Eif1ad |
| 13771 | 3 | 4 | | | IV-1 | Eif2a |
| 13772 | 3 | 4 | | | IV-1 | Eif2ak1 |
| 13773 | 3 | 4 | | | IV-1 | Eif2ak2 |
| 13774 | 3 | 4 | | | IV-1 | Eif2ak3 |
| 13775 | 3 | 4 | | | IV-1 | Eif2b1 |
| 13776 | 3 | 4 | | | IV-1 | Eif2b5 |
| 13777 | 3 | 4 | | | IV-1 | Eif2d |
| 13778 | 3 | 4 | | | IV-1 | Eif2s1 |
| 13779 | 3 | 4 | | | IV-1 | Eif2s3x |
| 13780 | 3 | 4 | | | IV-1 | Eif2s3y |
| 13781 | 3 | 4 | | | IV-1 | Eif3a |
| 13782 | 3 | 4 | | | IV-1 | Eif3b |
| 13783 | 3 | 4 | | | IV-1 | Eif3c |
| 13784 | 3 | 4 | | | IV-1 | Eif3d |
| 13785 | 3 | 4 | | | IV-1 | Eif3f |
| 13786 | 3 | 4 | | | IV-1 | Eif3g |
| 13787 | 3 | 4 | | | IV-1 | Eif3i |
| 13788 | 3 | 4 | | | IV-1 | Eif3j |
| 13789 | 3 | 4 | | | IV-1 | Eif4a2 |
| 13790 | 3 | 4 | | | IV-1 | Eif4b |
| 13791 | 3 | 4 | | | IV-1 | Eif4e |
| 13792 | 3 | 4 | | | IV-1 | Eif4e2 |
| 13793 | 3 | 4 | | | IV-1 | Eif4e3 |
| 13794 | 3 | 4 | | | IV-1 | Eif4enif1 |
| 13795 | 3 | 4 | | | IV-1 | Eif4g2 |
| 13796 | 3 | 4 | | | IV-1 | Eif4g3 |
| 13797 | 3 | 4 | | | IV-1 | Eif4h |
| 13798 | 3 | 4 | | | IV-1 | Eif5a |
| 13799 | 3 | 4 | | | IV-1 | Eif5a2 |
| 13800 | 3 | 4 | | | IV-1 | Eif5b |
| 13801 | 3 | 4 | | | IV-1 | Elac1 |
| 13802 | 3 | 4 | | | IV-1 | Elac2 |
| 13803 | 3 | 4 | | | IV-1 | Elavl1 |
| 13804 | 3 | 4 | | | IV-1 | Elavl2 |
| 13805 | 3 | 4 | | | IV-1 | Elavl3 |
| 13806 | 3 | 4 | | | IV-1 | Elavl4 |
| 13807 | 3 | 4 | | | IV-1 | Elf2 |
| 13808 | 3 | 4 | | | IV-1 | Elf4 |
| 13809 | 3 | 4 | | | IV-1 | Elf5 |
| 13810 | 3 | 4 | | | IV-1 | Elk1 |
| 13811 | 3 | 4 | | | IV-1 | Elk3 |
| 13812 | 3 | 4 | | | IV-1 | Ell |
| 13813 | 3 | 4 | | | IV-1 | Elmo1 |
| 13814 | 3 | 4 | | | IV-1 | Elmo2 |
| 13815 | 3 | 4 | | | IV-1 | Elmod1 |
| 13816 | 3 | 4 | | | IV-1 | Eln |
| 13817 | 3 | 4 | | | IV-1 | Elof1 |
| 13818 | 3 | 4 | | | IV-1 | Elp2 |
| 13819 | 3 | 4 | | | IV-1 | Elp3 |
| 13820 | 3 | 4 | | | IV-1 | Eltd1 |
| 13821 | 3 | 4 | | | IV-1 | Emc1 |
| 13822 | 3 | 4 | | | IV-1 | Emc10 |

Fig. 36 - 73

| | | | | | | |
|---|---|---|---|---|---|---|
| 13823 | 3 | 4 | | | IV-1 | Emc3 |
| 13824 | 3 | 4 | | | IV-1 | Emc4 |
| 13825 | 3 | 4 | | | IV-1 | Emc6 |
| 13826 | 3 | 4 | | | IV-1 | Emc8 |
| 13827 | 3 | 4 | | | IV-1 | Emd |
| 13828 | 3 | 4 | | | IV-1 | Emilin3 |
| 13829 | 3 | 4 | | | IV-1 | Eml1 |
| 13830 | 3 | 4 | | | IV-1 | Eml3 |
| 13831 | 3 | 4 | | | IV-1 | Eml4 |
| 13832 | 3 | 4 | | | IV-1 | Eml5 |
| 13833 | 3 | 4 | | | IV-1 | Emp2 |
| 13834 | 3 | 4 | | | IV-1 | Emx1 |
| 13835 | 3 | 4 | | | IV-1 | Emx2os |
| 13836 | 3 | 4 | | | IV-1 | En1 |
| 13837 | 3 | 4 | | | IV-1 | En2 |
| 13838 | 3 | 4 | | | IV-1 | Endod1 |
| 13839 | 3 | 4 | | | IV-1 | Endov |
| 13840 | 3 | 4 | | | IV-1 | Eng |
| 13841 | 3 | 4 | | | IV-1 | Eno2 |
| 13842 | 3 | 4 | | | IV-1 | Enox2 |
| 13843 | 3 | 4 | | | IV-1 | Enpp2 |
| 13844 | 3 | 4 | | | IV-1 | Enpp4 |
| 13845 | 3 | 4 | | | IV-1 | Entpd1 |
| 13846 | 3 | 4 | | | IV-1 | Entpd3 |
| 13847 | 3 | 4 | | | IV-1 | Entpd4 |
| 13848 | 3 | 4 | | | IV-1 | Env2 |
| 13849 | 3 | 4 | | | IV-1 | Eogt |
| 13850 | 3 | 4 | | | IV-1 | Ep400 |
| 13851 | 3 | 4 | | | IV-1 | Epb4.1l2 |
| 13852 | 3 | 4 | | | IV-1 | Epb4.1l4a |
| 13853 | 3 | 4 | | | IV-1 | Epb4.1l5 |
| 13854 | 3 | 4 | | | IV-1 | Epc2 |
| 13855 | 3 | 4 | | | IV-1 | Epgn |
| 13856 | 3 | 4 | | | IV-1 | Epha1 |
| 13857 | 3 | 4 | | | IV-1 | Epha10 |
| 13858 | 3 | 4 | | | IV-1 | Epha4 |
| 13859 | 3 | 4 | | | IV-1 | Epha5 |
| 13860 | 3 | 4 | | | IV-1 | Epha8 |
| 13861 | 3 | 4 | | | IV-1 | Ephb1 |
| 13862 | 3 | 4 | | | IV-1 | Ephb3 |
| 13863 | 3 | 4 | | | IV-1 | Ephb4 |
| 13864 | 3 | 4 | | | IV-1 | Ephx3 |
| 13865 | 3 | 4 | | | IV-1 | Epn2 |
| 13866 | 3 | 4 | | | IV-1 | Epor |
| 13867 | 3 | 4 | | | IV-1 | Eprs |
| 13868 | 3 | 4 | | | IV-1 | Eps15 |
| 13869 | 3 | 4 | | | IV-1 | Eps15l1 |
| 13870 | 3 | 4 | | | IV-1 | Eps8 |
| 13871 | 3 | 4 | | | IV-1 | Eps8l1 |
| 13872 | 3 | 4 | | | IV-1 | Eps8l3 |
| 13873 | 3 | 4 | | | IV-1 | Ept1 |
| 13874 | 3 | 4 | | | IV-1 | Epx |
| 13875 | 3 | 4 | | | IV-1 | Epyc |
| 13876 | 3 | 4 | | | IV-1 | Eqtn |
| 13877 | 3 | 4 | | | IV-1 | Eral1 |
| 13878 | 3 | 4 | | | IV-1 | Erap1 |
| 13879 | 3 | 4 | | | IV-1 | Erbb2ip |
| 13880 | 3 | 4 | | | IV-1 | Erc2 |
| 13881 | 3 | 4 | | | IV-1 | Ercc1 |
| 13882 | 3 | 4 | | | IV-1 | Ercc2 |
| 13883 | 3 | 4 | | | IV-1 | Ercc3 |
| 13884 | 3 | 4 | | | IV-1 | Ercc4 |
| 13885 | 3 | 4 | | | IV-1 | Ercc5 |
| 13886 | 3 | 4 | | | IV-1 | Ercc6l2 |
| 13887 | 3 | 4 | | | IV-1 | Erf |
| 13888 | 3 | 4 | | | IV-1 | Ergic1 |
| 13889 | 3 | 4 | | | IV-1 | Ergic2 |
| 13890 | 3 | 4 | | | IV-1 | Ergic3 |
| 13891 | 3 | 4 | | | IV-1 | Eri1 |
| 13892 | 3 | 4 | | | IV-1 | Eri2 |
| 13893 | 3 | 4 | | | IV-1 | Eri3 |
| 13894 | 3 | 4 | | | IV-1 | Erich1 |
| 13895 | 3 | 4 | | | IV-1 | Erich2 |
| 13896 | 3 | 4 | | | IV-1 | Erich6 |
| 13897 | 3 | 4 | | | IV-1 | Erlec1 |
| 13898 | 3 | 4 | | | IV-1 | Erlin1 |
| 13899 | 3 | 4 | | | IV-1 | Erlin2 |
| 13900 | 3 | 4 | | | IV-1 | Ermap |
| 13901 | 3 | 4 | | | IV-1 | Ermard |
| 13902 | 3 | 4 | | | IV-1 | Ermn |
| 13903 | 3 | 4 | | | IV-1 | Ermp1 |
| 13904 | 3 | 4 | | | IV-1 | Ero1l |
| 13905 | 3 | 4 | | | IV-1 | Ero1lb |
| 13906 | 3 | 4 | | | IV-1 | Erp29 |
| 13907 | 3 | 4 | | | IV-1 | Erp44 |
| 13908 | 3 | 4 | | | IV-1 | Esf1 |
| 13909 | 3 | 4 | | | IV-1 | Esr2 |
| 13910 | 3 | 4 | | | IV-1 | Esrra |
| 13911 | 3 | 4 | | | IV-1 | Esrrb |
| 13912 | 3 | 4 | | | IV-1 | Esx1 |
| 13913 | 3 | 4 | | | IV-1 | Esyt1 |
| 13914 | 3 | 4 | | | IV-1 | Esyt2 |
| 13915 | 3 | 4 | | | IV-1 | Etf1 |
| 13916 | 3 | 4 | | | IV-1 | Etfdh |
| 13917 | 3 | 4 | | | IV-1 | Ethe1 |
| 13918 | 3 | 4 | | | IV-1 | Eti4 |
| 13919 | 3 | 4 | | | IV-1 | Etnk1 |
| 13920 | 3 | 4 | | | IV-1 | Ets1 |
| 13921 | 3 | 4 | | | IV-1 | Etv6 |
| 13922 | 3 | 4 | | | IV-1 | Evc |
| 13923 | 3 | 4 | | | IV-1 | Evc2 |
| 13924 | 3 | 4 | | | IV-1 | Evi5 |
| 13925 | 3 | 4 | | | IV-1 | Evl |
| 13926 | 3 | 4 | | | IV-1 | Ewsr1 |
| 13927 | 3 | 4 | | | IV-1 | Exo1 |
| 13928 | 3 | 4 | | | IV-1 | Exo5 |
| 13929 | 3 | 4 | | | IV-1 | Exoc1 |
| 13930 | 3 | 4 | | | IV-1 | Exoc2 |
| 13931 | 3 | 4 | | | IV-1 | Exoc3 |
| 13932 | 3 | 4 | | | IV-1 | Exoc3l |
| 13933 | 3 | 4 | | | IV-1 | Exoc5 |
| 13934 | 3 | 4 | | | IV-1 | Exoc8 |
| 13935 | 3 | 4 | | | IV-1 | Exog |
| 13936 | 3 | 4 | | | IV-1 | Exosc10 |
| 13937 | 3 | 4 | | | IV-1 | Exosc2 |
| 13938 | 3 | 4 | | | IV-1 | Exosc5 |
| 13939 | 3 | 4 | | | IV-1 | Ext1 |
| 13940 | 3 | 4 | | | IV-1 | Ext2 |
| 13941 | 3 | 4 | | | IV-1 | Extl1 |
| 13942 | 3 | 4 | | | IV-1 | Extl2 |
| 13943 | 3 | 4 | | | IV-1 | Extl3 |
| 13944 | 3 | 4 | | | IV-1 | Eya4 |
| 13945 | 3 | 4 | | | IV-1 | Ezh1 |
| 13946 | 3 | 4 | | | IV-1 | Ezh2 |
| 13947 | 3 | 4 | | | IV-1 | F11 |
| 13948 | 3 | 4 | | | IV-1 | F12 |
| 13949 | 3 | 4 | | | IV-1 | F13b |
| 13950 | 3 | 4 | | | IV-1 | F2r |
| 13951 | 3 | 4 | | | IV-1 | F2rl1 |
| 13952 | 3 | 4 | | | IV-1 | F630042J09Rik |
| 13953 | 3 | 4 | | | IV-1 | F7 |
| 13954 | 3 | 4 | | | IV-1 | F8 |
| 13955 | 3 | 4 | | | IV-1 | Fabp12 |
| 13956 | 3 | 4 | | | IV-1 | Fabp9 |
| 13957 | 3 | 4 | | | IV-1 | Fadd |
| 13958 | 3 | 4 | | | IV-1 | Fads1 |
| 13959 | 3 | 4 | | | IV-1 | Faf1 |
| 13960 | 3 | 4 | | | IV-1 | Faf2 |
| 13961 | 3 | 4 | | | IV-1 | Fah |
| 13962 | 3 | 4 | | | IV-1 | Faim2 |
| 13963 | 3 | 4 | | | IV-1 | Fam101b |
| 13964 | 3 | 4 | | | IV-1 | Fam105a |
| 13965 | 3 | 4 | | | IV-1 | Fam109a |
| 13966 | 3 | 4 | | | IV-1 | Fam110a |
| 13967 | 3 | 4 | | | IV-1 | Fam111a |
| 13968 | 3 | 4 | | | IV-1 | Fam114a2 |
| 13969 | 3 | 4 | | | IV-1 | Fam115c |
| 13970 | 3 | 4 | | | IV-1 | Fam117b |
| 13971 | 3 | 4 | | | IV-1 | Fam118a |
| 13972 | 3 | 4 | | | IV-1 | Fam120a |
| 13973 | 3 | 4 | | | IV-1 | Fam120b |
| 13974 | 3 | 4 | | | IV-1 | Fam120c |
| 13975 | 3 | 4 | | | IV-1 | Fam122b |
| 13976 | 3 | 4 | | | IV-1 | Fam122c |
| 13977 | 3 | 4 | | | IV-1 | Fam124a |
| 13978 | 3 | 4 | | | IV-1 | Fam129b |
| 13979 | 3 | 4 | | | IV-1 | Fam131b |
| 13980 | 3 | 4 | | | IV-1 | Fam133b |
| 13981 | 3 | 4 | | | IV-1 | Fam134a |
| 13982 | 3 | 4 | | | IV-1 | Fam134c |
| 13983 | 3 | 4 | | | IV-1 | Fam136a |
| 13984 | 3 | 4 | | | IV-1 | Fam149a |
| 13985 | 3 | 4 | | | IV-1 | Fam149b |
| 13986 | 3 | 4 | | | IV-1 | Fam150a |
| 13987 | 3 | 4 | | | IV-1 | Fam155a |
| 13988 | 3 | 4 | | | IV-1 | Fam160a1 |
| 13989 | 3 | 4 | | | IV-1 | Fam160b1 |
| 13990 | 3 | 4 | | | IV-1 | Fam160b2 |
| 13991 | 3 | 4 | | | IV-1 | Fam161b |
| 13992 | 3 | 4 | | | IV-1 | Fam162b |
| 13993 | 3 | 4 | | | IV-1 | Fam163a |
| 13994 | 3 | 4 | | | IV-1 | Fam163b |
| 13995 | 3 | 4 | | | IV-1 | Fam166a |
| 13996 | 3 | 4 | | | IV-1 | Fam168a |
| 13997 | 3 | 4 | | | IV-1 | Fam168b |
| 13998 | 3 | 4 | | | IV-1 | Fam169a |
| 13999 | 3 | 4 | | | IV-1 | Fam170a |
| 14000 | 3 | 4 | | | IV-1 | Fam170b |
| 14001 | 3 | 4 | | | IV-1 | Fam171a1 |
| 14002 | 3 | 4 | | | IV-1 | Fam171a2 |
| 14003 | 3 | 4 | | | IV-1 | Fam172a |
| 14004 | 3 | 4 | | | IV-1 | Fam173a |
| 14005 | 3 | 4 | | | IV-1 | Fam174a |
| 14006 | 3 | 4 | | | IV-1 | Fam175b |
| 14007 | 3 | 4 | | | IV-1 | Fam178b |
| 14008 | 3 | 4 | | | IV-1 | Fam181a |
| 14009 | 3 | 4 | | | IV-1 | Fam184a |
| 14010 | 3 | 4 | | | IV-1 | Fam184b |
| 14011 | 3 | 4 | | | IV-1 | Fam185a |
| 14012 | 3 | 4 | | | IV-1 | Fam188a |
| 14013 | 3 | 4 | | | IV-1 | Fam188b |
| 14014 | 3 | 4 | | | IV-1 | Fam189a1 |

Fig. 36 - 74

| | | | | | | |
|---|---|---|---|---|---|---|
| 14015 | 3 | 4 | | | IV-1 | Fam189a2 |
| 14016 | 3 | 4 | | | IV-1 | Fam192a |
| 14017 | 3 | 4 | | | IV-1 | Fam193a |
| 14018 | 3 | 4 | | | IV-1 | Fam193b |
| 14019 | 3 | 4 | | | IV-1 | Fam196a |
| 14020 | 3 | 4 | | | IV-1 | Fam196b |
| 14021 | 3 | 4 | | | IV-1 | Fam198a |
| 14022 | 3 | 4 | | | IV-1 | Fam19a1 |
| 14023 | 3 | 4 | | | IV-1 | Fam19a3 |
| 14024 | 3 | 4 | | | IV-1 | Fam19a4 |
| 14025 | 3 | 4 | | | IV-1 | Fam204a |
| 14026 | 3 | 4 | | | IV-1 | Fam207a |
| 14027 | 3 | 4 | | | IV-1 | Fam208a |
| 14028 | 3 | 4 | | | IV-1 | Fam209 |
| 14029 | 3 | 4 | | | IV-1 | Fam20b |
| 14030 | 3 | 4 | | | IV-1 | Fam20c |
| 14031 | 3 | 4 | | | IV-1 | Fam21 |
| 14032 | 3 | 4 | | | IV-1 | Fam217a |
| 14033 | 3 | 4 | | | IV-1 | Fam221a |
| 14034 | 3 | 4 | | | IV-1 | Fam227a |
| 14035 | 3 | 4 | | | IV-1 | Fam227b |
| 14036 | 3 | 4 | | | IV-1 | Fam228a |
| 14037 | 3 | 4 | | | IV-1 | Fam25c |
| 14038 | 3 | 4 | | | IV-1 | Fam35a |
| 14039 | 3 | 4 | | | IV-1 | Fam3a |
| 14040 | 3 | 4 | | | IV-1 | Fam43a |
| 14041 | 3 | 4 | | | IV-1 | Fam43b |
| 14042 | 3 | 4 | | | IV-1 | Fam46d |
| 14043 | 3 | 4 | | | IV-1 | Fam47c |
| 14044 | 3 | 4 | | | IV-1 | Fam49a |
| 14045 | 3 | 4 | | | IV-1 | Fam50a |
| 14046 | 3 | 4 | | | IV-1 | Fam50b |
| 14047 | 3 | 4 | | | IV-1 | Fam53a |
| 14048 | 3 | 4 | | | IV-1 | Fam53c |
| 14049 | 3 | 4 | | | IV-1 | Fam58b |
| 14050 | 3 | 4 | | | IV-1 | Fam63b |
| 14051 | 3 | 4 | | | IV-1 | Fam65a |
| 14052 | 3 | 4 | | | IV-1 | Fam65c |
| 14053 | 3 | 4 | | | IV-1 | Fam69c |
| 14054 | 3 | 4 | | | IV-1 | Fam71b |
| 14055 | 3 | 4 | | | IV-1 | Fam71d |
| 14056 | 3 | 4 | | | IV-1 | Fam71e2 |
| 14057 | 3 | 4 | | | IV-1 | Fam71f1 |
| 14058 | 3 | 4 | | | IV-1 | Fam71f2 |
| 14059 | 3 | 4 | | | IV-1 | Fam72a |
| 14060 | 3 | 4 | | | IV-1 | Fam73b |
| 14061 | 3 | 4 | | | IV-1 | Fam76b |
| 14062 | 3 | 4 | | | IV-1 | Fam78b |
| 14063 | 3 | 4 | | | IV-1 | Fam83c |
| 14064 | 3 | 4 | | | IV-1 | Fam83d |
| 14065 | 3 | 4 | | | IV-1 | Fam83e |
| 14066 | 3 | 4 | | | IV-1 | Fam89b |
| 14067 | 3 | 4 | | | IV-1 | Fam96a |
| 14068 | 3 | 4 | | | IV-1 | Fam98a |
| 14069 | 3 | 4 | | | IV-1 | Fancb |
| 14070 | 3 | 4 | | | IV-1 | Fancd2 |
| 14071 | 3 | 4 | | | IV-1 | Fance |
| 14072 | 3 | 4 | | | IV-1 | Fancg |
| 14073 | 3 | 4 | | | IV-1 | Fank1 |
| 14074 | 3 | 4 | | | IV-1 | Fap |
| 14075 | 3 | 4 | | | IV-1 | Far1 |
| 14076 | 3 | 4 | | | IV-1 | Far2 |
| 14077 | 3 | 4 | | | IV-1 | Farsa |
| 14078 | 3 | 4 | | | IV-1 | Farsb |
| 14079 | 3 | 4 | | | IV-1 | Fastk |
| 14080 | 3 | 4 | | | IV-1 | Fastkd1 |
| 14081 | 3 | 4 | | | IV-1 | Fastkd2 |
| 14082 | 3 | 4 | | | IV-1 | Fbll1 |
| 14083 | 3 | 4 | | | IV-1 | Fbln7 |
| 14084 | 3 | 4 | | | IV-1 | Fbn1 |
| 14085 | 3 | 4 | | | IV-1 | Fbn2 |
| 14086 | 3 | 4 | | | IV-1 | Fbrs |
| 14087 | 3 | 4 | | | IV-1 | Fbrsl1 |
| 14088 | 3 | 4 | | | IV-1 | Fbxl12 |
| 14089 | 3 | 4 | | | IV-1 | Fbxl13 |
| 14090 | 3 | 4 | | | IV-1 | Fbxl14 |
| 14091 | 3 | 4 | | | IV-1 | Fbxl16 |
| 14092 | 3 | 4 | | | IV-1 | Fbxl17 |
| 14093 | 3 | 4 | | | IV-1 | Fbxl22 |
| 14094 | 3 | 4 | | | IV-1 | Fbxl3 |
| 14095 | 3 | 4 | | | IV-1 | Fbxl5 |
| 14096 | 3 | 4 | | | IV-1 | Fbxl6 |
| 14097 | 3 | 4 | | | IV-1 | Fbxo11 |
| 14098 | 3 | 4 | | | IV-1 | Fbxo21 |
| 14099 | 3 | 4 | | | IV-1 | Fbxo22 |
| 14100 | 3 | 4 | | | IV-1 | Fbxo27 |
| 14101 | 3 | 4 | | | IV-1 | Fbxo3 |
| 14102 | 3 | 4 | | | IV-1 | Fbxo30 |
| 14103 | 3 | 4 | | | IV-1 | Fbxo31 |
| 14104 | 3 | 4 | | | IV-1 | Fbxo32 |
| 14105 | 3 | 4 | | | IV-1 | Fbxo34 |
| 14106 | 3 | 4 | | | IV-1 | Fbxo38 |
| 14107 | 3 | 4 | | | IV-1 | Fbxo4 |
| 14108 | 3 | 4 | | | IV-1 | Fbxo41 |
| 14109 | 3 | 4 | | | IV-1 | Fbxo43 |
| 14110 | 3 | 4 | | | IV-1 | Fbxo45 |
| 14111 | 3 | 4 | | | IV-1 | Fbxo46 |
| 14112 | 3 | 4 | | | IV-1 | Fbxo8 |
| 14113 | 3 | 4 | | | IV-1 | Fbxw10 |
| 14114 | 3 | 4 | | | IV-1 | Fbxw17 |
| 14115 | 3 | 4 | | | IV-1 | Fbxw5 |
| 14116 | 3 | 4 | | | IV-1 | Fbxw7 |
| 14117 | 3 | 4 | | | IV-1 | Fbxw8 |
| 14118 | 3 | 4 | | | IV-1 | Fcer1a |
| 14119 | 3 | 4 | | | IV-1 | Fcer2a |
| 14120 | 3 | 4 | | | IV-1 | Fcho1 |
| 14121 | 3 | 4 | | | IV-1 | Fcho2 |
| 14122 | 3 | 4 | | | IV-1 | Fchsd1 |
| 14123 | 3 | 4 | | | IV-1 | Fchsd2 |
| 14124 | 3 | 4 | | | IV-1 | Fcnb |
| 14125 | 3 | 4 | | | IV-1 | Fcrl1 |
| 14126 | 3 | 4 | | | IV-1 | Fdft1 |
| 14127 | 3 | 4 | | | IV-1 | Fdxll |
| 14128 | 3 | 4 | | | IV-1 | Fdxacb1 |
| 14129 | 3 | 4 | | | IV-1 | Fdxr |
| 14130 | 3 | 4 | | | IV-1 | Fem1a |
| 14131 | 3 | 4 | | | IV-1 | Fem1b |
| 14132 | 3 | 4 | | | IV-1 | Fendrr |
| 14133 | 3 | 4 | | | IV-1 | Ferl4 |
| 14134 | 3 | 4 | | | IV-1 | Fermt2 |
| 14135 | 3 | 4 | | | IV-1 | Fezf2 |
| 14136 | 3 | 4 | | | IV-1 | Ffar2 |
| 14137 | 3 | 4 | | | IV-1 | Ffar3 |
| 14138 | 3 | 4 | | | IV-1 | Fgd5 |
| 14139 | 3 | 4 | | | IV-1 | Fgf1 |
| 14140 | 3 | 4 | | | IV-1 | Fgf12 |
| 14141 | 3 | 4 | | | IV-1 | Fgf13 |
| 14142 | 3 | 4 | | | IV-1 | Fgf14 |
| 14143 | 3 | 4 | | | IV-1 | Fgf16 |
| 14144 | 3 | 4 | | | IV-1 | Fgf21 |
| 14145 | 3 | 4 | | | IV-1 | Fgf9 |
| 14146 | 3 | 4 | | | IV-1 | Fgfbp1 |
| 14147 | 3 | 4 | | | IV-1 | Fgfbp3 |
| 14148 | 3 | 4 | | | IV-1 | Fgfr1op |
| 14149 | 3 | 4 | | | IV-1 | Fh1 |
| 14150 | 3 | 4 | | | IV-1 | Fhad1 |
| 14151 | 3 | 4 | | | IV-1 | Fhdc1 |
| 14152 | 3 | 4 | | | IV-1 | Fhl4 |
| 14153 | 3 | 4 | | | IV-1 | Fhl5 |
| 14154 | 3 | 4 | | | IV-1 | Fhod1 |
| 14155 | 3 | 4 | | | IV-1 | Fhod3 |
| 14156 | 3 | 4 | | | IV-1 | Fibcd1 |
| 14157 | 3 | 4 | | | IV-1 | Ficd |
| 14158 | 3 | 4 | | | IV-1 | Fig4 |
| 14159 | 3 | 4 | | | IV-1 | Fignl1 |
| 14160 | 3 | 4 | | | IV-1 | Fip1l1 |
| 14161 | 3 | 4 | | | IV-1 | Firre |
| 14162 | 3 | 4 | | | IV-1 | Fiz1 |
| 14163 | 3 | 4 | | | IV-1 | Fkbp10 |
| 14164 | 3 | 4 | | | IV-1 | Fkbp15 |
| 14165 | 3 | 4 | | | IV-1 | Fkbp6 |
| 14166 | 3 | 4 | | | IV-1 | Fkbp9 |
| 14167 | 3 | 4 | | | IV-1 | Flad1 |
| 14168 | 3 | 4 | | | IV-1 | Flg2 |
| 14169 | 3 | 4 | | | IV-1 | Flii |
| 14170 | 3 | 4 | | | IV-1 | Flot2 |
| 14171 | 3 | 4 | | | IV-1 | Flt3 |
| 14172 | 3 | 4 | | | IV-1 | Fmn2 |
| 14173 | 3 | 4 | | | IV-1 | Fmo6 |
| 14174 | 3 | 4 | | | IV-1 | Fmod |
| 14175 | 3 | 4 | | | IV-1 | Fmr1nb |
| 14176 | 3 | 4 | | | IV-1 | Fn3krp |
| 14177 | 3 | 4 | | | IV-1 | Fnbp1 |
| 14178 | 3 | 4 | | | IV-1 | Fnbp4 |
| 14179 | 3 | 4 | | | IV-1 | Fndc3a |
| 14180 | 3 | 4 | | | IV-1 | Fndc8 |
| 14181 | 3 | 4 | | | IV-1 | Fntb |
| 14182 | 3 | 4 | | | IV-1 | Focad |
| 14183 | 3 | 4 | | | IV-1 | Foxa1 |
| 14184 | 3 | 4 | | | IV-1 | Foxa2 |
| 14185 | 3 | 4 | | | IV-1 | Foxa3 |
| 14186 | 3 | 4 | | | IV-1 | Foxb1 |
| 14187 | 3 | 4 | | | IV-1 | Foxc1 |
| 14188 | 3 | 4 | | | IV-1 | Foxc2 |
| 14189 | 3 | 4 | | | IV-1 | Foxd1 |
| 14190 | 3 | 4 | | | IV-1 | Foxd2 |
| 14191 | 3 | 4 | | | IV-1 | Foxf1 |
| 14192 | 3 | 4 | | | IV-1 | Foxf2 |
| 14193 | 3 | 4 | | | IV-1 | Foxg1 |
| 14194 | 3 | 4 | | | IV-1 | Foxj3 |
| 14195 | 3 | 4 | | | IV-1 | Foxk2 |
| 14196 | 3 | 4 | | | IV-1 | Foxl2 |
| 14197 | 3 | 4 | | | IV-1 | Foxl2os |
| 14198 | 3 | 4 | | | IV-1 | Foxm1 |
| 14199 | 3 | 4 | | | IV-1 | Foxn1 |
| 14200 | 3 | 4 | | | IV-1 | Foxn2 |
| 14201 | 3 | 4 | | | IV-1 | Foxp2 |
| 14202 | 3 | 4 | | | IV-1 | Foxp4 |
| 14203 | 3 | 4 | | | IV-1 | Foxr2 |
| 14204 | 3 | 4 | | | IV-1 | Fpgt |
| 14205 | 3 | 4 | | | IV-1 | Fras1 |
| 14206 | 3 | 4 | | | IV-1 | Frem1 |

Fig. 36 - 75

| | | | | | | |
|---|---|---|---|---|---|---|
| 14207 | 3 | 4 | | | IV-1 | Frmd3 |
| 14208 | 3 | 4 | | | IV-1 | Frmd4a |
| 14209 | 3 | 4 | | | IV-1 | Frmd5 |
| 14210 | 3 | 4 | | | IV-1 | Frmpd1 |
| 14211 | 3 | 4 | | | IV-1 | Frrs1 |
| 14212 | 3 | 4 | | | IV-1 | Frs3 |
| 14213 | 3 | 4 | | | IV-1 | Fryl |
| 14214 | 3 | 4 | | | IV-1 | Frzb |
| 14215 | 3 | 4 | | | IV-1 | Fsd1 |
| 14216 | 3 | 4 | | | IV-1 | Fsd1l |
| 14217 | 3 | 4 | | | IV-1 | Fsd2 |
| 14218 | 3 | 4 | | | IV-1 | Fshr |
| 14219 | 3 | 4 | | | IV-1 | Fsip1 |
| 14220 | 3 | 4 | | | IV-1 | Fst |
| 14221 | 3 | 4 | | | IV-1 | Ftcd |
| 14222 | 3 | 4 | | | IV-1 | Fthl17 |
| 14223 | 3 | 4 | | | IV-1 | Ftmt |
| 14224 | 3 | 4 | | | IV-1 | Fto |
| 14225 | 3 | 4 | | | IV-1 | Ftsj1 |
| 14226 | 3 | 4 | | | IV-1 | Ftsj2 |
| 14227 | 3 | 4 | | | IV-1 | Ftsj3 |
| 14228 | 3 | 4 | | | IV-1 | Fubp1 |
| 14229 | 3 | 4 | | | IV-1 | Fubp3 |
| 14230 | 3 | 4 | | | IV-1 | Fuk |
| 14231 | 3 | 4 | | | IV-1 | Fundc1 |
| 14232 | 3 | 4 | | | IV-1 | Fuom |
| 14233 | 3 | 4 | | | IV-1 | Fut11 |
| 14234 | 3 | 4 | | | IV-1 | Fut2 |
| 14235 | 3 | 4 | | | IV-1 | Fut7 |
| 14236 | 3 | 4 | | | IV-1 | Fut8 |
| 14237 | 3 | 4 | | | IV-1 | Fut9 |
| 14238 | 3 | 4 | | | IV-1 | Fxr1 |
| 14239 | 3 | 4 | | | IV-1 | Fxr2 |
| 14240 | 3 | 4 | | | IV-1 | Fxyd4 |
| 14241 | 3 | 4 | | | IV-1 | Fxyd5 |
| 14242 | 3 | 4 | | | IV-1 | Fyttd1 |
| 14243 | 3 | 4 | | | IV-1 | Fzd1 |
| 14244 | 3 | 4 | | | IV-1 | Fzd10 |
| 14245 | 3 | 4 | | | IV-1 | Fzd2 |
| 14246 | 3 | 4 | | | IV-1 | Fzd7 |
| 14247 | 3 | 4 | | | IV-1 | Fzd8 |
| 14248 | 3 | 4 | | | IV-1 | G2e3 |
| 14249 | 3 | 4 | | | IV-1 | G3bp1 |
| 14250 | 3 | 4 | | | IV-1 | G3bp2 |
| 14251 | 3 | 4 | | | IV-1 | G6pc2 |
| 14252 | 3 | 4 | | | IV-1 | G6pc3 |
| 14253 | 3 | 4 | | | IV-1 | G6pdx |
| 14254 | 3 | 4 | | | IV-1 | Gaa |
| 14255 | 3 | 4 | | | IV-1 | Gab3 |
| 14256 | 3 | 4 | | | IV-1 | Gabarap |
| 14257 | 3 | 4 | | | IV-1 | Gabbr1 |
| 14258 | 3 | 4 | | | IV-1 | Gabpa |
| 14259 | 3 | 4 | | | IV-1 | Gabpb1 |
| 14260 | 3 | 4 | | | IV-1 | Gabra2 |
| 14261 | 3 | 4 | | | IV-1 | Gabra3 |
| 14262 | 3 | 4 | | | IV-1 | Gabra5 |
| 14263 | 3 | 4 | | | IV-1 | Gabra6 |
| 14264 | 3 | 4 | | | IV-1 | Gabrb2 |
| 14265 | 3 | 4 | | | IV-1 | Gabrb3 |
| 14266 | 3 | 4 | | | IV-1 | Gabre |
| 14267 | 3 | 4 | | | IV-1 | Gabrg1 |
| 14268 | 3 | 4 | | | IV-1 | Gabrg2 |
| 14269 | 3 | 4 | | | IV-1 | Gabrp |
| 14270 | 3 | 4 | | | IV-1 | Gabrq |
| 14271 | 3 | 4 | | | IV-1 | Gabrr1 |
| 14272 | 3 | 4 | | | IV-1 | Gad1 |
| 14273 | 3 | 4 | | | IV-1 | Gad1os |
| 14274 | 3 | 4 | | | IV-1 | Gad2 |
| 14275 | 3 | 4 | | | IV-1 | Gadl1 |
| 14276 | 3 | 4 | | | IV-1 | Gak |
| 14277 | 3 | 4 | | | IV-1 | Gal |
| 14278 | 3 | 4 | | | IV-1 | Gal3st2 |
| 14279 | 3 | 4 | | | IV-1 | Gal3st3 |
| 14280 | 3 | 4 | | | IV-1 | Galc |
| 14281 | 3 | 4 | | | IV-1 | Gale |
| 14282 | 3 | 4 | | | IV-1 | Galns |
| 14283 | 3 | 4 | | | IV-1 | Galnt11 |
| 14284 | 3 | 4 | | | IV-1 | Galnt13 |
| 14285 | 3 | 4 | | | IV-1 | Galnt2 |
| 14286 | 3 | 4 | | | IV-1 | Galnt6 |
| 14287 | 3 | 4 | | | IV-1 | Galnt9 |
| 14288 | 3 | 4 | | | IV-1 | Galntl5 |
| 14289 | 3 | 4 | | | IV-1 | Galntl6 |
| 14290 | 3 | 4 | | | IV-1 | Galr2 |
| 14291 | 3 | 4 | | | IV-1 | Ganab |
| 14292 | 3 | 4 | | | IV-1 | Gapdh |
| 14293 | 3 | 4 | | | IV-1 | Gapdhs |
| 14294 | 3 | 4 | | | IV-1 | Gareml |
| 14295 | 3 | 4 | | | IV-1 | Garnl3 |
| 14296 | 3 | 4 | | | IV-1 | Gars |
| 14297 | 3 | 4 | | | IV-1 | Gart |
| 14298 | 3 | 4 | | | IV-1 | Gas2l2 |
| 14299 | 3 | 4 | | | IV-1 | Gas2l3 |
| 14300 | 3 | 4 | | | IV-1 | Gas5 |
| 14301 | 3 | 4 | | | IV-1 | Gast |
| 14302 | 3 | 4 | | | IV-1 | Gata3 |
| 14303 | 3 | 4 | | | IV-1 | Gata4 |
| 14304 | 3 | 4 | | | IV-1 | Gata5 |
| 14305 | 3 | 4 | | | IV-1 | Gatad1 |
| 14306 | 3 | 4 | | | IV-1 | Gatad2a |
| 14307 | 3 | 4 | | | IV-1 | Gatc |
| 14308 | 3 | 4 | | | IV-1 | Gba |
| 14309 | 3 | 4 | | | IV-1 | Gba2 |
| 14310 | 3 | 4 | | | IV-1 | Gbf1 |
| 14311 | 3 | 4 | | | IV-1 | Gbx2 |
| 14312 | 3 | 4 | | | IV-1 | Gcdh |
| 14313 | 3 | 4 | | | IV-1 | Gcg |
| 14314 | 3 | 4 | | | IV-1 | Gcgr |
| 14315 | 3 | 4 | | | IV-1 | Gckr |
| 14316 | 3 | 4 | | | IV-1 | Gclc |
| 14317 | 3 | 4 | | | IV-1 | Gcm1 |
| 14318 | 3 | 4 | | | IV-1 | Gcnt3 |
| 14319 | 3 | 4 | | | IV-1 | Gcsh |
| 14320 | 3 | 4 | | | IV-1 | Gdap2 |
| 14321 | 3 | 4 | | | IV-1 | Gdf2 |
| 14322 | 3 | 4 | | | IV-1 | Gdf3 |
| 14323 | 3 | 4 | | | IV-1 | Gdf9 |
| 14324 | 3 | 4 | | | IV-1 | Gdi1 |
| 14325 | 3 | 4 | | | IV-1 | Gdi2 |
| 14326 | 3 | 4 | | | IV-1 | Gdnf |
| 14327 | 3 | 4 | | | IV-1 | Gdpd1 |
| 14328 | 3 | 4 | | | IV-1 | Gdpd4 |
| 14329 | 3 | 4 | | | IV-1 | Gdpgp1 |
| 14330 | 3 | 4 | | | IV-1 | Gemin4 |
| 14331 | 3 | 4 | | | IV-1 | Gemin5 |
| 14332 | 3 | 4 | | | IV-1 | Get4 |
| 14333 | 3 | 4 | | | IV-1 | Gfm2 |
| 14334 | 3 | 4 | | | IV-1 | Gfra2 |
| 14335 | 3 | 4 | | | IV-1 | Gfra3 |
| 14336 | 3 | 4 | | | IV-1 | Gfy |
| 14337 | 3 | 4 | | | IV-1 | Gga1 |
| 14338 | 3 | 4 | | | IV-1 | Gga2 |
| 14339 | 3 | 4 | | | IV-1 | Gga3 |
| 14340 | 3 | 4 | | | IV-1 | Ggact |
| 14341 | 3 | 4 | | | IV-1 | Ggcx |
| 14342 | 3 | 4 | | | IV-1 | Ggnbp2 |
| 14343 | 3 | 4 | | | IV-1 | Ggt5 |
| 14344 | 3 | 4 | | | IV-1 | Ggt6 |
| 14345 | 3 | 4 | | | IV-1 | Ggt7 |
| 14346 | 3 | 4 | | | IV-1 | Ghdc |
| 14347 | 3 | 4 | | | IV-1 | Ghrhr |
| 14348 | 3 | 4 | | | IV-1 | Ghrl |
| 14349 | 3 | 4 | | | IV-1 | Gid4 |
| 14350 | 3 | 4 | | | IV-1 | Gif |
| 14351 | 3 | 4 | | | IV-1 | Gigyf1 |
| 14352 | 3 | 4 | | | IV-1 | Gigyf2 |
| 14353 | 3 | 4 | | | IV-1 | Gimap3 |
| 14354 | 3 | 4 | | | IV-1 | Gimap8 |
| 14355 | 3 | 4 | | | IV-1 | Gimap9 |
| 14356 | 3 | 4 | | | IV-1 | Gin1 |
| 14357 | 3 | 4 | | | IV-1 | Gip |
| 14358 | 3 | 4 | | | IV-1 | Gipr |
| 14359 | 3 | 4 | | | IV-1 | Git1 |
| 14360 | 3 | 4 | | | IV-1 | Git2 |
| 14361 | 3 | 4 | | | IV-1 | Gja3 |
| 14362 | 3 | 4 | | | IV-1 | Gja6 |
| 14363 | 3 | 4 | | | IV-1 | Gjb6 |
| 14364 | 3 | 4 | | | IV-1 | Gjc1 |
| 14365 | 3 | 4 | | | IV-1 | Gjc2 |
| 14366 | 3 | 4 | | | IV-1 | Gjc3 |
| 14367 | 3 | 4 | | | IV-1 | Gjd2 |
| 14368 | 3 | 4 | | | IV-1 | Gjd3 |
| 14369 | 3 | 4 | | | IV-1 | Gkap1 |
| 14370 | 3 | 4 | | | IV-1 | Gla |
| 14371 | 3 | 4 | | | IV-1 | Glb1l2 |
| 14372 | 3 | 4 | | | IV-1 | Glce |
| 14373 | 3 | 4 | | | IV-1 | Gldc |
| 14374 | 3 | 4 | | | IV-1 | Gldn |
| 14375 | 3 | 4 | | | IV-1 | Gldnos |
| 14376 | 3 | 4 | | | IV-1 | Gle1 |
| 14377 | 3 | 4 | | | IV-1 | Gli2 |
| 14378 | 3 | 4 | | | IV-1 | Gli3 |
| 14379 | 3 | 4 | | | IV-1 | Glipr1l1 |
| 14380 | 3 | 4 | | | IV-1 | Glipr1l2 |
| 14381 | 3 | 4 | | | IV-1 | Glis1 |
| 14382 | 3 | 4 | | | IV-1 | Glis2 |
| 14383 | 3 | 4 | | | IV-1 | Glo1 |
| 14384 | 3 | 4 | | | IV-1 | Glod4 |
| 14385 | 3 | 4 | | | IV-1 | Glod5 |
| 14386 | 3 | 4 | | | IV-1 | Glp2r |
| 14387 | 3 | 4 | | | IV-1 | Glra2 |
| 14388 | 3 | 4 | | | IV-1 | Glrb |
| 14389 | 3 | 4 | | | IV-1 | Glrp1 |
| 14390 | 3 | 4 | | | IV-1 | Glrx2 |
| 14391 | 3 | 4 | | | IV-1 | Gls |
| 14392 | 3 | 4 | | | IV-1 | Glt25d1 |
| 14393 | 3 | 4 | | | IV-1 | Glt6d1 |
| 14394 | 3 | 4 | | | IV-1 | Glt8d2 |
| 14395 | 3 | 4 | | | IV-1 | Gltp |
| 14396 | 3 | 4 | | | IV-1 | Gltpd1 |
| 14397 | 3 | 4 | | | IV-1 | Gltpd2 |
| 14398 | 3 | 4 | | | IV-1 | Gltscr2 |

Fig. 36 - 76

| | | | | | | |
|---|---|---|---|---|---|---|
| 14399 | 3 | 4 | | | IV-1 | Glyat |
| 14400 | 3 | 4 | | | IV-1 | Glyr1 |
| 14401 | 3 | 4 | | | IV-1 | Gm10024 |
| 14402 | 3 | 4 | | | IV-1 | Gm10033 |
| 14403 | 3 | 4 | | | IV-1 | Gm10069 |
| 14404 | 3 | 4 | | | IV-1 | Gm10190 |
| 14405 | 3 | 4 | | | IV-1 | Gm10220 |
| 14406 | 3 | 4 | | | IV-1 | Gm10336 |
| 14407 | 3 | 4 | | | IV-1 | Gm10354 |
| 14408 | 3 | 4 | | | IV-1 | Gm10375 |
| 14409 | 3 | 4 | | | IV-1 | Gm10377 |
| 14410 | 3 | 4 | | | IV-1 | Gm10406 |
| 14411 | 3 | 4 | | | IV-1 | Gm10409 |
| 14412 | 3 | 4 | | | IV-1 | Gm10413 |
| 14413 | 3 | 4 | | | IV-1 | Gm10415 |
| 14414 | 3 | 4 | | | IV-1 | Gm10439 |
| 14415 | 3 | 4 | | | IV-1 | Gm10471 |
| 14416 | 3 | 4 | | | IV-1 | Gm10494 |
| 14417 | 3 | 4 | | | IV-1 | Gm10532 |
| 14418 | 3 | 4 | | | IV-1 | Gm10538 |
| 14419 | 3 | 4 | | | IV-1 | Gm10635 |
| 14420 | 3 | 4 | | | IV-1 | Gm10640 |
| 14421 | 3 | 4 | | | IV-1 | Gm10681 |
| 14422 | 3 | 4 | | | IV-1 | Gm10684 |
| 14423 | 3 | 4 | | | IV-1 | Gm10731 |
| 14424 | 3 | 4 | | | IV-1 | Gm10754 |
| 14425 | 3 | 4 | | | IV-1 | Gm10767 |
| 14426 | 3 | 4 | | | IV-1 | Gm10768 |
| 14427 | 3 | 4 | | | IV-1 | Gm10778 |
| 14428 | 3 | 4 | | | IV-1 | Gm10791 |
| 14429 | 3 | 4 | | | IV-1 | Gm10804 |
| 14430 | 3 | 4 | | | IV-1 | Gm10814 |
| 14431 | 3 | 4 | | | IV-1 | Gm10857 |
| 14432 | 3 | 4 | | | IV-1 | Gm10921 |
| 14433 | 3 | 4 | | | IV-1 | Gm10922 |
| 14434 | 3 | 4 | | | IV-1 | Gm11149 |
| 14435 | 3 | 4 | | | IV-1 | Gm11186 |
| 14436 | 3 | 4 | | | IV-1 | Gm11213 |
| 14437 | 3 | 4 | | | IV-1 | Gm1141 |
| 14438 | 3 | 4 | | | IV-1 | Gm11549 |
| 14439 | 3 | 4 | | | IV-1 | Gm11563 |
| 14440 | 3 | 4 | | | IV-1 | Gm11595 |
| 14441 | 3 | 4 | | | IV-1 | Gm11596 |
| 14442 | 3 | 4 | | | IV-1 | Gm11651 |
| 14443 | 3 | 4 | | | IV-1 | Gm11696 |
| 14444 | 3 | 4 | | | IV-1 | Gm11744 |
| 14445 | 3 | 4 | | | IV-1 | Gm11762 |
| 14446 | 3 | 4 | | | IV-1 | Gm11780 |
| 14447 | 3 | 4 | | | IV-1 | Gm11937 |
| 14448 | 3 | 4 | | | IV-1 | Gm11938 |
| 14449 | 3 | 4 | | | IV-1 | Gm11978 |
| 14450 | 3 | 4 | | | IV-1 | Gm11992 |
| 14451 | 3 | 4 | | | IV-1 | Gm12185 |
| 14452 | 3 | 4 | | | IV-1 | Gm12295 |
| 14453 | 3 | 4 | | | IV-1 | Gm12429 |
| 14454 | 3 | 4 | | | IV-1 | Gm12504 |
| 14455 | 3 | 4 | | | IV-1 | Gm12633 |
| 14456 | 3 | 4 | | | IV-1 | Gm12695 |
| 14457 | 3 | 4 | | | IV-1 | Gm12709 |
| 14458 | 3 | 4 | | | IV-1 | Gm128 |
| 14459 | 3 | 4 | | | IV-1 | Gm12888 |
| 14460 | 3 | 4 | | | IV-1 | Gm13003 |
| 14461 | 3 | 4 | | | IV-1 | Gm13051 |
| 14462 | 3 | 4 | | | IV-1 | Gm13124 |
| 14463 | 3 | 4 | | | IV-1 | Gm13177 |
| 14464 | 3 | 4 | | | IV-1 | Gm13178 |
| 14465 | 3 | 4 | | | IV-1 | Gm13238 |
| 14466 | 3 | 4 | | | IV-1 | Gm13247 |
| 14467 | 3 | 4 | | | IV-1 | Gm13293 |
| 14468 | 3 | 4 | | | IV-1 | Gm13315 |
| 14469 | 3 | 4 | | | IV-1 | Gm13539 |
| 14470 | 3 | 4 | | | IV-1 | Gm13546 |
| 14471 | 3 | 4 | | | IV-1 | Gm13547 |
| 14472 | 3 | 4 | | | IV-1 | Gm13629 |
| 14473 | 3 | 4 | | | IV-1 | Gm13710 |
| 14474 | 3 | 4 | | | IV-1 | Gm13889 |
| 14475 | 3 | 4 | | | IV-1 | Gm14023 |
| 14476 | 3 | 4 | | | IV-1 | Gm14057 |
| 14477 | 3 | 4 | | | IV-1 | Gm14164 |
| 14478 | 3 | 4 | | | IV-1 | Gm14204 |
| 14479 | 3 | 4 | | | IV-1 | Gm14308 |
| 14480 | 3 | 4 | | | IV-1 | Gm14322 |
| 14481 | 3 | 4 | | | IV-1 | Gm14325 |
| 14482 | 3 | 4 | | | IV-1 | Gm14327 |
| 14483 | 3 | 4 | | | IV-1 | Gm14351 |
| 14484 | 3 | 4 | | | IV-1 | Gm14379 |
| 14485 | 3 | 4 | | | IV-1 | Gm14474 |
| 14486 | 3 | 4 | | | IV-1 | Gm14477 |
| 14487 | 3 | 4 | | | IV-1 | Gm14478 |
| 14488 | 3 | 4 | | | IV-1 | Gm14483 |
| 14489 | 3 | 4 | | | IV-1 | Gm14484 |
| 14490 | 3 | 4 | | | IV-1 | Gm14499 |
| 14491 | 3 | 4 | | | IV-1 | Gm14501 |
| 14492 | 3 | 4 | | | IV-1 | Gm14525 |
| 14493 | 3 | 4 | | | IV-1 | Gm14685 |
| 14494 | 3 | 4 | | | IV-1 | Gm14725 |
| 14495 | 3 | 4 | | | IV-1 | Gm14781 |
| 14496 | 3 | 4 | | | IV-1 | Gm14827 |
| 14497 | 3 | 4 | | | IV-1 | Gm15097 |
| 14498 | 3 | 4 | | | IV-1 | Gm15104 |
| 14499 | 3 | 4 | | | IV-1 | Gm15140 |
| 14500 | 3 | 4 | | | IV-1 | Gm15179 |
| 14501 | 3 | 4 | | | IV-1 | Gm1527 |
| 14502 | 3 | 4 | | | IV-1 | Gm15292 |
| 14503 | 3 | 4 | | | IV-1 | Gm15412 |
| 14504 | 3 | 4 | | | IV-1 | Gm15446 |
| 14505 | 3 | 4 | | | IV-1 | Gm15455 |
| 14506 | 3 | 4 | | | IV-1 | Gm15612 |
| 14507 | 3 | 4 | | | IV-1 | Gm1564 |
| 14508 | 3 | 4 | | | IV-1 | Gm15663 |
| 14509 | 3 | 4 | | | IV-1 | Gm15708 |
| 14510 | 3 | 4 | | | IV-1 | Gm15760 |
| 14511 | 3 | 4 | | | IV-1 | Gm15816 |
| 14512 | 3 | 4 | | | IV-1 | Gm15850 |
| 14513 | 3 | 4 | | | IV-1 | Gm15987 |
| 14514 | 3 | 4 | | | IV-1 | Gm16039 |
| 14515 | 3 | 4 | | | IV-1 | Gm16063 |
| 14516 | 3 | 4 | | | IV-1 | Gm16130 |
| 14517 | 3 | 4 | | | IV-1 | Gm16157 |
| 14518 | 3 | 4 | | | IV-1 | Gm1631 |
| 14519 | 3 | 4 | | | IV-1 | Gm16325 |
| 14520 | 3 | 4 | | | IV-1 | Gm16390 |
| 14521 | 3 | 4 | | | IV-1 | Gm16404 |
| 14522 | 3 | 4 | | | IV-1 | Gm16430 |
| 14523 | 3 | 4 | | | IV-1 | Gm16432 |
| 14524 | 3 | 4 | | | IV-1 | Gm16445 |
| 14525 | 3 | 4 | | | IV-1 | Gm1647 |
| 14526 | 3 | 4 | | | IV-1 | Gm16501 |
| 14527 | 3 | 4 | | | IV-1 | Gm16515 |
| 14528 | 3 | 4 | | | IV-1 | Gm16523 |
| 14529 | 3 | 4 | | | IV-1 | Gm1653 |
| 14530 | 3 | 4 | | | IV-1 | Gm16532 |
| 14531 | 3 | 4 | | | IV-1 | Gm16596 |
| 14532 | 3 | 4 | | | IV-1 | Gm1661 |
| 14533 | 3 | 4 | | | IV-1 | Gm16677 |
| 14534 | 3 | 4 | | | IV-1 | Gm16702 |
| 14535 | 3 | 4 | | | IV-1 | Gm16712 |
| 14536 | 3 | 4 | | | IV-1 | Gm16880 |
| 14537 | 3 | 4 | | | IV-1 | Gm16897 |
| 14538 | 3 | 4 | | | IV-1 | Gm16907 |
| 14539 | 3 | 4 | | | IV-1 | Gm16938 |
| 14540 | 3 | 4 | | | IV-1 | Gm17019 |
| 14541 | 3 | 4 | | | IV-1 | Gm17066 |
| 14542 | 3 | 4 | | | IV-1 | Gm17644 |
| 14543 | 3 | 4 | | | IV-1 | Gm17746 |
| 14544 | 3 | 4 | | | IV-1 | Gm17762 |
| 14545 | 3 | 4 | | | IV-1 | Gm17769 |
| 14546 | 3 | 4 | | | IV-1 | Gm1821 |
| 14547 | 3 | 4 | | | IV-1 | Gm19277 |
| 14548 | 3 | 4 | | | IV-1 | Gm19395 |
| 14549 | 3 | 4 | | | IV-1 | Gm1943 |
| 14550 | 3 | 4 | | | IV-1 | Gm19522 |
| 14551 | 3 | 4 | | | IV-1 | Gm19557 |
| 14552 | 3 | 4 | | | IV-1 | Gm19897 |
| 14553 | 3 | 4 | | | IV-1 | Gm1993 |
| 14554 | 3 | 4 | | | IV-1 | Gm19990 |
| 14555 | 3 | 4 | | | IV-1 | Gm20268 |
| 14556 | 3 | 4 | | | IV-1 | Gm2030 |
| 14557 | 3 | 4 | | | IV-1 | Gm20300 |
| 14558 | 3 | 4 | | | IV-1 | Gm2042 |
| 14559 | 3 | 4 | | | IV-1 | Gm20594 |
| 14560 | 3 | 4 | | | IV-1 | Gm20605 |
| 14561 | 3 | 4 | | | IV-1 | Gm2061 |
| 14562 | 3 | 4 | | | IV-1 | Gm20611 |
| 14563 | 3 | 4 | | | IV-1 | Gm20736 |
| 14564 | 3 | 4 | | | IV-1 | Gm20738 |
| 14565 | 3 | 4 | | | IV-1 | Gm20743 |
| 14566 | 3 | 4 | | | IV-1 | Gm20747 |
| 14567 | 3 | 4 | | | IV-1 | Gm20751 |
| 14568 | 3 | 4 | | | IV-1 | Gm20752 |
| 14569 | 3 | 4 | | | IV-1 | Gm20754 |
| 14570 | 3 | 4 | | | IV-1 | Gm20806 |
| 14571 | 3 | 4 | | | IV-1 | Gm20809 |
| 14572 | 3 | 4 | | | IV-1 | Gm20815 |
| 14573 | 3 | 4 | | | IV-1 | Gm20822 |
| 14574 | 3 | 4 | | | IV-1 | Gm20826 |
| 14575 | 3 | 4 | | | IV-1 | Gm20831 |
| 14576 | 3 | 4 | | | IV-1 | Gm20854 |
| 14577 | 3 | 4 | | | IV-1 | Gm20865 |
| 14578 | 3 | 4 | | | IV-1 | Gm2087 |
| 14579 | 3 | 4 | | | IV-1 | Gm20877 |
| 14580 | 3 | 4 | | | IV-1 | Gm20917 |
| 14581 | 3 | 4 | | | IV-1 | Gm21221 |
| 14582 | 3 | 4 | | | IV-1 | Gm21269 |
| 14583 | 3 | 4 | | | IV-1 | Gm21283 |
| 14584 | 3 | 4 | | | IV-1 | Gm21284 |
| 14585 | 3 | 4 | | | IV-1 | Gm21671 |
| 14586 | 3 | 4 | | | IV-1 | Gm21693 |
| 14587 | 3 | 4 | | | IV-1 | Gm21708 |
| 14588 | 3 | 4 | | | IV-1 | Gm2176 |
| 14589 | 3 | 4 | | | IV-1 | Gm21943 |
| 14590 | 3 | 4 | | | IV-1 | Gm21950 |

Fig. 36 - 77

| | | | | | | |
|---|---|---|---|---|---|---|
| 14591 | 3 | 4 | | | IV-1 | Gm21951 |
| 14592 | 3 | 4 | | | IV-1 | Gm2762 |
| 14593 | 3 | 4 | | | IV-1 | Gm2799 |
| 14594 | 3 | 4 | | | IV-1 | Gm2825 |
| 14595 | 3 | 4 | | | IV-1 | Gm2897 |
| 14596 | 3 | 4 | | | IV-1 | Gm2927 |
| 14597 | 3 | 4 | | | IV-1 | Gm2933 |
| 14598 | 3 | 4 | | | IV-1 | Gm2a |
| 14599 | 3 | 4 | | | IV-1 | Gm3002 |
| 14600 | 3 | 4 | | | IV-1 | Gm3219 |
| 14601 | 3 | 4 | | | IV-1 | Gm3230 |
| 14602 | 3 | 4 | | | IV-1 | Gm3238 |
| 14603 | 3 | 4 | | | IV-1 | Gm3264 |
| 14604 | 3 | 4 | | | IV-1 | Gm3317 |
| 14605 | 3 | 4 | | | IV-1 | Gm3383 |
| 14606 | 3 | 4 | | | IV-1 | Gm3404 |
| 14607 | 3 | 4 | | | IV-1 | Gm3435 |
| 14608 | 3 | 4 | | | IV-1 | Gm3458 |
| 14609 | 3 | 4 | | | IV-1 | Gm3488 |
| 14610 | 3 | 4 | | | IV-1 | Gm3500 |
| 14611 | 3 | 4 | | | IV-1 | Gm3558 |
| 14612 | 3 | 4 | | | IV-1 | Gm362 |
| 14613 | 3 | 4 | | | IV-1 | Gm3696 |
| 14614 | 3 | 4 | | | IV-1 | Gm3706 |
| 14615 | 3 | 4 | | | IV-1 | Gm3716 |
| 14616 | 3 | 4 | | | IV-1 | Gm3750 |
| 14617 | 3 | 4 | | | IV-1 | Gm3763 |
| 14618 | 3 | 4 | | | IV-1 | Gm4027 |
| 14619 | 3 | 4 | | | IV-1 | Gm4251 |
| 14620 | 3 | 4 | | | IV-1 | Gm4262 |
| 14621 | 3 | 4 | | | IV-1 | Gm436 |
| 14622 | 3 | 4 | | | IV-1 | Gm438 |
| 14623 | 3 | 4 | | | IV-1 | Gm4566 |
| 14624 | 3 | 4 | | | IV-1 | Gm4719 |
| 14625 | 3 | 4 | | | IV-1 | Gm4721 |
| 14626 | 3 | 4 | | | IV-1 | Gm4763 |
| 14627 | 3 | 4 | | | IV-1 | Gm4776 |
| 14628 | 3 | 4 | | | IV-1 | Gm4787 |
| 14629 | 3 | 4 | | | IV-1 | Gm4788 |
| 14630 | 3 | 4 | | | IV-1 | Gm4814 |
| 14631 | 3 | 4 | | | IV-1 | Gm4861 |
| 14632 | 3 | 4 | | | IV-1 | Gm4871 |
| 14633 | 3 | 4 | | | IV-1 | Gm4884 |
| 14634 | 3 | 4 | | | IV-1 | Gm4890 |
| 14635 | 3 | 4 | | | IV-1 | Gm4907 |
| 14636 | 3 | 4 | | | IV-1 | Gm4926 |
| 14637 | 3 | 4 | | | IV-1 | Gm4937 |
| 14638 | 3 | 4 | | | IV-1 | Gm4952 |
| 14639 | 3 | 4 | | | IV-1 | Gm4961 |
| 14640 | 3 | 4 | | | IV-1 | Gm4980 |
| 14641 | 3 | 4 | | | IV-1 | Gm4984 |
| 14642 | 3 | 4 | | | IV-1 | Gm5071 |
| 14643 | 3 | 4 | | | IV-1 | Gm5072 |
| 14644 | 3 | 4 | | | IV-1 | Gm5108 |
| 14645 | 3 | 4 | | | IV-1 | Gm5126 |
| 14646 | 3 | 4 | | | IV-1 | Gm5127 |
| 14647 | 3 | 4 | | | IV-1 | Gm5136 |
| 14648 | 3 | 4 | | | IV-1 | Gm5141 |
| 14649 | 3 | 4 | | | IV-1 | Gm5166 |
| 14650 | 3 | 4 | | | IV-1 | Gm5169 |
| 14651 | 3 | 4 | | | IV-1 | Gm5334 |
| 14652 | 3 | 4 | | | IV-1 | Gm5346 |
| 14653 | 3 | 4 | | | IV-1 | Gm5347 |
| 14654 | 3 | 4 | | | IV-1 | Gm5382 |
| 14655 | 3 | 4 | | | IV-1 | Gm5415 |
| 14656 | 3 | 4 | | | IV-1 | Gm5420 |
| 14657 | 3 | 4 | | | IV-1 | Gm5458 |
| 14658 | 3 | 4 | | | IV-1 | Gm5477 |
| 14659 | 3 | 4 | | | IV-1 | Gm5478 |
| 14660 | 3 | 4 | | | IV-1 | Gm5483 |
| 14661 | 3 | 4 | | | IV-1 | Gm5523 |
| 14662 | 3 | 4 | | | IV-1 | Gm5549 |
| 14663 | 3 | 4 | | | IV-1 | Gm5591 |
| 14664 | 3 | 4 | | | IV-1 | Gm5595 |
| 14665 | 3 | 4 | | | IV-1 | Gm5607 |
| 14666 | 3 | 4 | | | IV-1 | Gm5627 |
| 14667 | 3 | 4 | | | IV-1 | Gm5634 |
| 14668 | 3 | 4 | | | IV-1 | Gm5635 |
| 14669 | 3 | 4 | | | IV-1 | Gm5640 |
| 14670 | 3 | 4 | | | IV-1 | Gm5766 |
| 14671 | 3 | 4 | | | IV-1 | Gm5795 |
| 14672 | 3 | 4 | | | IV-1 | Gm5796 |
| 14673 | 3 | 4 | | | IV-1 | Gm5797 |
| 14674 | 3 | 4 | | | IV-1 | Gm5800 |
| 14675 | 3 | 4 | | | IV-1 | Gm5820 |
| 14676 | 3 | 4 | | | IV-1 | Gm5862 |
| 14677 | 3 | 4 | | | IV-1 | Gm5868 |
| 14678 | 3 | 4 | | | IV-1 | Gm5878 |
| 14679 | 3 | 4 | | | IV-1 | Gm5901 |
| 14680 | 3 | 4 | | | IV-1 | Gm5925 |
| 14681 | 3 | 4 | | | IV-1 | Gm5934 |
| 14682 | 3 | 4 | | | IV-1 | Gm5935 |
| 14683 | 3 | 4 | | | IV-1 | Gm5936 |
| 14684 | 3 | 4 | | | IV-1 | Gm595 |
| 14685 | 3 | 4 | | | IV-1 | Gm6121 |
| 14686 | 3 | 4 | | | IV-1 | Gm614 |
| 14687 | 3 | 4 | | | IV-1 | Gm6225 |
| 14688 | 3 | 4 | | | IV-1 | Gm6251 |
| 14689 | 3 | 4 | | | IV-1 | Gm6277 |
| 14690 | 3 | 4 | | | IV-1 | Gm6289 |
| 14691 | 3 | 4 | | | IV-1 | Gm6370 |
| 14692 | 3 | 4 | | | IV-1 | Gm6408 |
| 14693 | 3 | 4 | | | IV-1 | Gm6432 |
| 14694 | 3 | 4 | | | IV-1 | Gm6455 |
| 14695 | 3 | 4 | | | IV-1 | Gm6548 |
| 14696 | 3 | 4 | | | IV-1 | Gm6559 |
| 14697 | 3 | 4 | | | IV-1 | Gm6567 |
| 14698 | 3 | 4 | | | IV-1 | Gm6588 |
| 14699 | 3 | 4 | | | IV-1 | Gm6639 |
| 14700 | 3 | 4 | | | IV-1 | Gm6756 |
| 14701 | 3 | 4 | | | IV-1 | Gm6812 |
| 14702 | 3 | 4 | | | IV-1 | Gm7073 |
| 14703 | 3 | 4 | | | IV-1 | Gm711 |
| 14704 | 3 | 4 | | | IV-1 | Gm7120 |
| 14705 | 3 | 4 | | | IV-1 | Gm715 |
| 14706 | 3 | 4 | | | IV-1 | Gm7157 |
| 14707 | 3 | 4 | | | IV-1 | Gm7168 |
| 14708 | 3 | 4 | | | IV-1 | Gm732 |
| 14709 | 3 | 4 | | | IV-1 | Gm7325 |
| 14710 | 3 | 4 | | | IV-1 | Gm7361 |
| 14711 | 3 | 4 | | | IV-1 | Gm7444 |
| 14712 | 3 | 4 | | | IV-1 | Gm7904 |
| 14713 | 3 | 4 | | | IV-1 | Gm805 |
| 14714 | 3 | 4 | | | IV-1 | Gm806 |
| 14715 | 3 | 4 | | | IV-1 | Gm8221 |
| 14716 | 3 | 4 | | | IV-1 | Gm8267 |
| 14717 | 3 | 4 | | | IV-1 | Gm853 |
| 14718 | 3 | 4 | | | IV-1 | Gm8615 |
| 14719 | 3 | 4 | | | IV-1 | Gm8883 |
| 14720 | 3 | 4 | | | IV-1 | Gm8994 |
| 14721 | 3 | 4 | | | IV-1 | Gm9 |
| 14722 | 3 | 4 | | | IV-1 | Gm9047 |
| 14723 | 3 | 4 | | | IV-1 | Gm9054 |
| 14724 | 3 | 4 | | | IV-1 | Gm9112 |
| 14725 | 3 | 4 | | | IV-1 | Gm94 |
| 14726 | 3 | 4 | | | IV-1 | Gm973 |
| 14727 | 3 | 4 | | | IV-1 | Gm9758 |
| 14728 | 3 | 4 | | | IV-1 | Gm9839 |
| 14729 | 3 | 4 | | | IV-1 | Gm9899 |
| 14730 | 3 | 4 | | | IV-1 | Gm9926 |
| 14731 | 3 | 4 | | | IV-1 | Gm996 |
| 14732 | 3 | 4 | | | IV-1 | Gm9999 |
| 14733 | 3 | 4 | | | IV-1 | Gmcl1 |
| 14734 | 3 | 4 | | | IV-1 | Gmeb1 |
| 14735 | 3 | 4 | | | IV-1 | Gmeb2 |
| 14736 | 3 | 4 | | | IV-1 | Gmfb |
| 14737 | 3 | 4 | | | IV-1 | Gmfg |
| 14738 | 3 | 4 | | | IV-1 | Gmip |
| 14739 | 3 | 4 | | | IV-1 | Gmi |
| 14740 | 3 | 4 | | | IV-1 | Gmpr2 |
| 14741 | 3 | 4 | | | IV-1 | Gna11 |
| 14742 | 3 | 4 | | | IV-1 | Gna14 |
| 14743 | 3 | 4 | | | IV-1 | Gnai2 |
| 14744 | 3 | 4 | | | IV-1 | Gnai3 |
| 14745 | 3 | 4 | | | IV-1 | Gnao1 |
| 14746 | 3 | 4 | | | IV-1 | Gnas |
| 14747 | 3 | 4 | | | IV-1 | Gnb1 |
| 14748 | 3 | 4 | | | IV-1 | Gnb2 |
| 14749 | 3 | 4 | | | IV-1 | Gnb2l1 |
| 14750 | 3 | 4 | | | IV-1 | Gnb3 |
| 14751 | 3 | 4 | | | IV-1 | Gnb4 |
| 14752 | 3 | 4 | | | IV-1 | Gne |
| 14753 | 3 | 4 | | | IV-1 | Gng2 |
| 14754 | 3 | 4 | | | IV-1 | Gng4 |
| 14755 | 3 | 4 | | | IV-1 | Gng7 |
| 14756 | 3 | 4 | | | IV-1 | Gnl1 |
| 14757 | 3 | 4 | | | IV-1 | Gnl2 |
| 14758 | 3 | 4 | | | IV-1 | Gnl3 |
| 14759 | 3 | 4 | | | IV-1 | Gnpat |
| 14760 | 3 | 4 | | | IV-1 | Gnpnat1 |
| 14761 | 3 | 4 | | | IV-1 | Gnptab |
| 14762 | 3 | 4 | | | IV-1 | Gnptg |
| 14763 | 3 | 4 | | | IV-1 | Golga1 |
| 14764 | 3 | 4 | | | IV-1 | Golga2 |
| 14765 | 3 | 4 | | | IV-1 | Golga5 |
| 14766 | 3 | 4 | | | IV-1 | Golga7b |
| 14767 | 3 | 4 | | | IV-1 | Golim4 |
| 14768 | 3 | 4 | | | IV-1 | Golph3 |
| 14769 | 3 | 4 | | | IV-1 | Golph3l |
| 14770 | 3 | 4 | | | IV-1 | Golt1a |
| 14771 | 3 | 4 | | | IV-1 | Golt1b |
| 14772 | 3 | 4 | | | IV-1 | Gopc |
| 14773 | 3 | 4 | | | IV-1 | Gorab |
| 14774 | 3 | 4 | | | IV-1 | Gorasp1 |
| 14775 | 3 | 4 | | | IV-1 | Gorasp2 |
| 14776 | 3 | 4 | | | IV-1 | Gosr1 |
| 14777 | 3 | 4 | | | IV-1 | Gosr2 |
| 14778 | 3 | 4 | | | IV-1 | Got1l1 |
| 14779 | 3 | 4 | | | IV-1 | Gpaa1 |
| 14780 | 3 | 4 | | | IV-1 | Gpank1 |
| 14781 | 3 | 4 | | | IV-1 | Gpat2 |
| 14782 | 3 | 4 | | | IV-1 | Gpatch1 |

Fig. 36 - 78

| | | | | | | |
|---|---|---|---|---|---|---|
| 14783 | 3 | 4 | | | IV-1 | Gpatch11 |
| 14784 | 3 | 4 | | | IV-1 | Gpatch2 |
| 14785 | 3 | 4 | | | IV-1 | Gpatch3 |
| 14786 | 3 | 4 | | | IV-1 | Gpatch8 |
| 14787 | 3 | 4 | | | IV-1 | Gpbar1 |
| 14788 | 3 | 4 | | | IV-1 | Gpbp1l1 |
| 14789 | 3 | 4 | | | IV-1 | Gpc6 |
| 14790 | 3 | 4 | | | IV-1 | Gpd1 |
| 14791 | 3 | 4 | | | IV-1 | Gpha2 |
| 14792 | 3 | 4 | | | IV-1 | Gphn |
| 14793 | 3 | 4 | | | IV-1 | Gpi1 |
| 14794 | 3 | 4 | | | IV-1 | Gpkow |
| 14795 | 3 | 4 | | | IV-1 | Gpn3 |
| 14796 | 3 | 4 | | | IV-1 | Gpr101 |
| 14797 | 3 | 4 | | | IV-1 | Gpr107 |
| 14798 | 3 | 4 | | | IV-1 | Gpr108 |
| 14799 | 3 | 4 | | | IV-1 | Gpr111 |
| 14800 | 3 | 4 | | | IV-1 | Gpr113 |
| 14801 | 3 | 4 | | | IV-1 | Gpr115 |
| 14802 | 3 | 4 | | | IV-1 | Gpr12 |
| 14803 | 3 | 4 | | | IV-1 | Gpr123 |
| 14804 | 3 | 4 | | | IV-1 | Gpr124 |
| 14805 | 3 | 4 | | | IV-1 | Gpr125 |
| 14806 | 3 | 4 | | | IV-1 | Gpr126 |
| 14807 | 3 | 4 | | | IV-1 | Gpr133 |
| 14808 | 3 | 4 | | | IV-1 | Gpr137 |
| 14809 | 3 | 4 | | | IV-1 | Gpr137b |
| 14810 | 3 | 4 | | | IV-1 | Gpr149 |
| 14811 | 3 | 4 | | | IV-1 | Gpr15 |
| 14812 | 3 | 4 | | | IV-1 | Gpr150 |
| 14813 | 3 | 4 | | | IV-1 | Gpr151 |
| 14814 | 3 | 4 | | | IV-1 | Gpr153 |
| 14815 | 3 | 4 | | | IV-1 | Gpr158 |
| 14816 | 3 | 4 | | | IV-1 | Gpr160 |
| 14817 | 3 | 4 | | | IV-1 | Gpr17 |
| 14818 | 3 | 4 | | | IV-1 | Gpr171 |
| 14819 | 3 | 4 | | | IV-1 | Gpr174 |
| 14820 | 3 | 4 | | | IV-1 | Gpr176 |
| 14821 | 3 | 4 | | | IV-1 | Gpr179 |
| 14822 | 3 | 4 | | | IV-1 | Gpr180 |
| 14823 | 3 | 4 | | | IV-1 | Gpr182 |
| 14824 | 3 | 4 | | | IV-1 | Gpr183 |
| 14825 | 3 | 4 | | | IV-1 | Gpr20 |
| 14826 | 3 | 4 | | | IV-1 | Gpr21 |
| 14827 | 3 | 4 | | | IV-1 | Gpr22 |
| 14828 | 3 | 4 | | | IV-1 | Gpr25 |
| 14829 | 3 | 4 | | | IV-1 | Gpr45 |
| 14830 | 3 | 4 | | | IV-1 | Gpr55 |
| 14831 | 3 | 4 | | | IV-1 | Gpr6 |
| 14832 | 3 | 4 | | | IV-1 | Gpr61 |
| 14833 | 3 | 4 | | | IV-1 | Gpr62 |
| 14834 | 3 | 4 | | | IV-1 | Gpr68 |
| 14835 | 3 | 4 | | | IV-1 | Gpr75 |
| 14836 | 3 | 4 | | | IV-1 | Gpr82 |
| 14837 | 3 | 4 | | | IV-1 | Gpr83 |
| 14838 | 3 | 4 | | | IV-1 | Gpr85 |
| 14839 | 3 | 4 | | | IV-1 | Gpr87 |
| 14840 | 3 | 4 | | | IV-1 | Gpr88 |
| 14841 | 3 | 4 | | | IV-1 | Gpr89 |
| 14842 | 3 | 4 | | | IV-1 | Gpr98 |
| 14843 | 3 | 4 | | | IV-1 | Gprc5b |
| 14844 | 3 | 4 | | | IV-1 | Gprc5d |
| 14845 | 3 | 4 | | | IV-1 | Gprc6a |
| 14846 | 3 | 4 | | | IV-1 | Gprin1 |
| 14847 | 3 | 4 | | | IV-1 | Gps1 |
| 14848 | 3 | 4 | | | IV-1 | Gps2 |
| 14849 | 3 | 4 | | | IV-1 | Gpsm1 |
| 14850 | 3 | 4 | | | IV-1 | Gpsm2 |
| 14851 | 3 | 4 | | | IV-1 | Gpt2 |
| 14852 | 3 | 4 | | | IV-1 | Gpx2 |
| 14853 | 3 | 4 | | | IV-1 | Gpx2-ps1 |
| 14854 | 3 | 4 | | | IV-1 | Gramd1a |
| 14855 | 3 | 4 | | | IV-1 | Gramd1c |
| 14856 | 3 | 4 | | | IV-1 | Gramd3 |
| 14857 | 3 | 4 | | | IV-1 | Gramd4 |
| 14858 | 3 | 4 | | | IV-1 | Grb10 |
| 14859 | 3 | 4 | | | IV-1 | Grb2 |
| 14860 | 3 | 4 | | | IV-1 | Greb1l |
| 14861 | 3 | 4 | | | IV-1 | Grem2 |
| 14862 | 3 | 4 | | | IV-1 | Grhl2 |
| 14863 | 3 | 4 | | | IV-1 | Grhl3 |
| 14864 | 3 | 4 | | | IV-1 | Gria1 |
| 14865 | 3 | 4 | | | IV-1 | Gria2 |
| 14866 | 3 | 4 | | | IV-1 | Gria3 |
| 14867 | 3 | 4 | | | IV-1 | Gria4 |
| 14868 | 3 | 4 | | | IV-1 | Grik1 |
| 14869 | 3 | 4 | | | IV-1 | Grik2 |
| 14870 | 3 | 4 | | | IV-1 | Grik4 |
| 14871 | 3 | 4 | | | IV-1 | Grik5 |
| 14872 | 3 | 4 | | | IV-1 | Grin1 |
| 14873 | 3 | 4 | | | IV-1 | Grin3b |
| 14874 | 3 | 4 | | | IV-1 | Grip1 |
| 14875 | 3 | 4 | | | IV-1 | Grip2 |
| 14876 | 3 | 4 | | | IV-1 | Gripap1 |
| 14877 | 3 | 4 | | | IV-1 | Grk6 |
| 14878 | 3 | 4 | | | IV-1 | Grm1 |

| | | | | | | |
|---|---|---|---|---|---|---|
| 14879 | 3 | 4 | | | IV-1 | Grm2 |
| 14880 | 3 | 4 | | | IV-1 | Grm3 |
| 14881 | 3 | 4 | | | IV-1 | Grm4 |
| 14882 | 3 | 4 | | | IV-1 | Grm5 |
| 14883 | 3 | 4 | | | IV-1 | Grm7 |
| 14884 | 3 | 4 | | | IV-1 | Grm8 |
| 14885 | 3 | 4 | | | IV-1 | Grpel1 |
| 14886 | 3 | 4 | | | IV-1 | Grsf1 |
| 14887 | 3 | 4 | | | IV-1 | Gsap |
| 14888 | 3 | 4 | | | IV-1 | Gsdma |
| 14889 | 3 | 4 | | | IV-1 | Gsdmc |
| 14890 | 3 | 4 | | | IV-1 | Gsdmc2 |
| 14891 | 3 | 4 | | | IV-1 | Gsg1 |
| 14892 | 3 | 4 | | | IV-1 | Gsk3a |
| 14893 | 3 | 4 | | | IV-1 | Gsk3b |
| 14894 | 3 | 4 | | | IV-1 | Gskip |
| 14895 | 3 | 4 | | | IV-1 | Gspt1 |
| 14896 | 3 | 4 | | | IV-1 | Gss |
| 14897 | 3 | 4 | | | IV-1 | Gstm4 |
| 14898 | 3 | 4 | | | IV-1 | Gsto1 |
| 14899 | 3 | 4 | | | IV-1 | Gstt4 |
| 14900 | 3 | 4 | | | IV-1 | Gtdc1 |
| 14901 | 3 | 4 | | | IV-1 | Gtf2a1 |
| 14902 | 3 | 4 | | | IV-1 | Gtf2a1l |
| 14903 | 3 | 4 | | | IV-1 | Gtf2b |
| 14904 | 3 | 4 | | | IV-1 | Gtf2e1 |
| 14905 | 3 | 4 | | | IV-1 | Gtf2e2 |
| 14906 | 3 | 4 | | | IV-1 | Gtf2h1 |
| 14907 | 3 | 4 | | | IV-1 | Gtf2h3 |
| 14908 | 3 | 4 | | | IV-1 | Gtf2i |
| 14909 | 3 | 4 | | | IV-1 | Gtf2ird2 |
| 14910 | 3 | 4 | | | IV-1 | Gtf3c1 |
| 14911 | 3 | 4 | | | IV-1 | Gtf3c2 |
| 14912 | 3 | 4 | | | IV-1 | Gtf3c5 |
| 14913 | 3 | 4 | | | IV-1 | Gtl3 |
| 14914 | 3 | 4 | | | IV-1 | Gtpbp1 |
| 14915 | 3 | 4 | | | IV-1 | Gtpbp10 |
| 14916 | 3 | 4 | | | IV-1 | Gtpbp3 |
| 14917 | 3 | 4 | | | IV-1 | Gtpbp4 |
| 14918 | 3 | 4 | | | IV-1 | Gtse1 |
| 14919 | 3 | 4 | | | IV-1 | Gtsf1 |
| 14920 | 3 | 4 | | | IV-1 | Gucy1a2 |
| 14921 | 3 | 4 | | | IV-1 | Gucy1a3 |
| 14922 | 3 | 4 | | | IV-1 | Gucy2d |
| 14923 | 3 | 4 | | | IV-1 | Guf1 |
| 14924 | 3 | 4 | | | IV-1 | Gulo |
| 14925 | 3 | 4 | | | IV-1 | Gxylt1 |
| 14926 | 3 | 4 | | | IV-1 | Gyk1 |
| 14927 | 3 | 4 | | | IV-1 | Gyltl1b |
| 14928 | 3 | 4 | | | IV-1 | Gys1 |
| 14929 | 3 | 4 | | | IV-1 | Gys2 |
| 14930 | 3 | 4 | | | IV-1 | Gzf1 |
| 14931 | 3 | 4 | | | IV-1 | Gzmn |
| 14932 | 3 | 4 | | | IV-1 | H13 |
| 14933 | 3 | 4 | | | IV-1 | H2-T10 |
| 14934 | 3 | 4 | | | IV-1 | H2-T3 |
| 14935 | 3 | 4 | | | IV-1 | H2afb1 |
| 14936 | 3 | 4 | | | IV-1 | H2bfm |
| 14937 | 3 | 4 | | | IV-1 | H3f3b |
| 14938 | 3 | 4 | | | IV-1 | H60c |
| 14939 | 3 | 4 | | | IV-1 | Habp2 |
| 14940 | 3 | 4 | | | IV-1 | Habp4 |
| 14941 | 3 | 4 | | | IV-1 | Hadha |
| 14942 | 3 | 4 | | | IV-1 | Hand2 |
| 14943 | 3 | 4 | | | IV-1 | Hao1 |
| 14944 | 3 | 4 | | | IV-1 | Hapln1 |
| 14945 | 3 | 4 | | | IV-1 | Hapln2 |
| 14946 | 3 | 4 | | | IV-1 | Hapln4 |
| 14947 | 3 | 4 | | | IV-1 | Harbi1 |
| 14948 | 3 | 4 | | | IV-1 | Hars |
| 14949 | 3 | 4 | | | IV-1 | Hars2 |
| 14950 | 3 | 4 | | | IV-1 | Haus2 |
| 14951 | 3 | 4 | | | IV-1 | Haus3 |
| 14952 | 3 | 4 | | | IV-1 | Haus4 |
| 14953 | 3 | 4 | | | IV-1 | Haus5 |
| 14954 | 3 | 4 | | | IV-1 | Havcr1 |
| 14955 | 3 | 4 | | | IV-1 | Hba-x |
| 14956 | 3 | 4 | | | IV-1 | Hbb-y |
| 14957 | 3 | 4 | | | IV-1 | Hbegf |
| 14958 | 3 | 4 | | | IV-1 | Hbp1 |
| 14959 | 3 | 4 | | | IV-1 | Hbs1l |
| 14960 | 3 | 4 | | | IV-1 | Hc |
| 14961 | 3 | 4 | | | IV-1 | Hcn1 |
| 14962 | 3 | 4 | | | IV-1 | Hcn2 |
| 14963 | 3 | 4 | | | IV-1 | Hcrtr1 |
| 14964 | 3 | 4 | | | IV-1 | Hcrtr2 |
| 14965 | 3 | 4 | | | IV-1 | Hdac7 |
| 14966 | 3 | 4 | | | IV-1 | Hdgf |
| 14967 | 3 | 4 | | | IV-1 | Hdgfl1 |
| 14968 | 3 | 4 | | | IV-1 | Hdgfrp2 |
| 14969 | 3 | 4 | | | IV-1 | Hdgfrp3 |
| 14970 | 3 | 4 | | | IV-1 | Hdhd1a |
| 14971 | 3 | 4 | | | IV-1 | Hdhd2 |
| 14972 | 3 | 4 | | | IV-1 | Hdlbp |
| 14973 | 3 | 4 | | | IV-1 | Hdx |
| 14974 | 3 | 4 | | | IV-1 | Heatr2 |

Fig. 36 - 79

| | | | | | | |
|---|---|---|---|---|---|---|
| 14975 | 3 | 4 | | | IV-1 | Heatr3 |
| 14976 | 3 | 4 | | | IV-1 | Heatr6 |
| 14977 | 3 | 4 | | | IV-1 | Heatr9 |
| 14978 | 3 | 4 | | | IV-1 | Hectd2 |
| 14979 | 3 | 4 | | | IV-1 | Hectd3 |
| 14980 | 3 | 4 | | | IV-1 | Hecw1 |
| 14981 | 3 | 4 | | | IV-1 | Helb |
| 14982 | 3 | 4 | | | IV-1 | Hells |
| 14983 | 3 | 4 | | | IV-1 | Helt |
| 14984 | 3 | 4 | | | IV-1 | Hemt1 |
| 14985 | 3 | 4 | | | IV-1 | Henmt1 |
| 14986 | 3 | 4 | | | IV-1 | Hepacam |
| 14987 | 3 | 4 | | | IV-1 | Hepacam2 |
| 14988 | 3 | 4 | | | IV-1 | Hephl1 |
| 14989 | 3 | 4 | | | IV-1 | Herc3 |
| 14990 | 3 | 4 | | | IV-1 | Herc4 |
| 14991 | 3 | 4 | | | IV-1 | Hes3 |
| 14992 | 3 | 4 | | | IV-1 | Hes5 |
| 14993 | 3 | 4 | | | IV-1 | Hes7 |
| 14994 | 3 | 4 | | | IV-1 | Hexa |
| 14995 | 3 | 4 | | | IV-1 | Hexb |
| 14996 | 3 | 4 | | | IV-1 | Hexdc |
| 14997 | 3 | 4 | | | IV-1 | Hfe |
| 14998 | 3 | 4 | | | IV-1 | Hgd |
| 14999 | 3 | 4 | | | IV-1 | Hgs |
| 15000 | 3 | 4 | | | IV-1 | Hgsnat |
| 15001 | 3 | 4 | | | IV-1 | Hhat |
| 15002 | 3 | 4 | | | IV-1 | Hhip |
| 15003 | 3 | 4 | | | IV-1 | Hiat1 |
| 15004 | 3 | 4 | | | IV-1 | Hibadh |
| 15005 | 3 | 4 | | | IV-1 | Hic1 |
| 15006 | 3 | 4 | | | IV-1 | Hid1 |
| 15007 | 3 | 4 | | | IV-1 | Hif1a |
| 15008 | 3 | 4 | | | IV-1 | Higd1a |
| 15009 | 3 | 4 | | | IV-1 | Hils1 |
| 15010 | 3 | 4 | | | IV-1 | Hip1r |
| 15011 | 3 | 4 | | | IV-1 | Hipk3 |
| 15012 | 3 | 4 | | | IV-1 | Hira |
| 15013 | 3 | 4 | | | IV-1 | Hist1h1b |
| 15014 | 3 | 4 | | | IV-1 | Hist2h2ab |
| 15015 | 3 | 4 | | | IV-1 | Hist3h2bb-ps |
| 15016 | 3 | 4 | | | IV-1 | Hjurp |
| 15017 | 3 | 4 | | | IV-1 | Hlcs |
| 15018 | 3 | 4 | | | IV-1 | Hltf |
| 15019 | 3 | 4 | | | IV-1 | Hmces |
| 15020 | 3 | 4 | | | IV-1 | Hmcn1 |
| 15021 | 3 | 4 | | | IV-1 | Hmg20a |
| 15022 | 3 | 4 | | | IV-1 | Hmg20b |
| 15023 | 3 | 4 | | | IV-1 | Hmga2 |
| 15024 | 3 | 4 | | | IV-1 | Hmgb1-rs17 |
| 15025 | 3 | 4 | | | IV-1 | Hmgb2 |
| 15026 | 3 | 4 | | | IV-1 | Hmgb4 |
| 15027 | 3 | 4 | | | IV-1 | Hmgcll1 |
| 15028 | 3 | 4 | | | IV-1 | Hmgcr |
| 15029 | 3 | 4 | | | IV-1 | Hmgn5 |
| 15030 | 3 | 4 | | | IV-1 | Hmgxb4 |
| 15031 | 3 | 4 | | | IV-1 | Hmmr |
| 15032 | 3 | 4 | | | IV-1 | Hmox2 |
| 15033 | 3 | 4 | | | IV-1 | Hmx1 |
| 15034 | 3 | 4 | | | IV-1 | Hmx2 |
| 15035 | 3 | 4 | | | IV-1 | Hnrnpa0 |
| 15036 | 3 | 4 | | | IV-1 | Hnrnpa2b1 |
| 15037 | 3 | 4 | | | IV-1 | Hnrnpa3 |
| 15038 | 3 | 4 | | | IV-1 | Hnrnpc |
| 15039 | 3 | 4 | | | IV-1 | Hnrnpd |
| 15040 | 3 | 4 | | | IV-1 | Hnrnpdl |
| 15041 | 3 | 4 | | | IV-1 | Hnrnpf |
| 15042 | 3 | 4 | | | IV-1 | Hnrnph2 |
| 15043 | 3 | 4 | | | IV-1 | Hnrnpk |
| 15044 | 3 | 4 | | | IV-1 | Hnrnpl |
| 15045 | 3 | 4 | | | IV-1 | Hnrnpll |
| 15046 | 3 | 4 | | | IV-1 | Hnrnpm |
| 15047 | 3 | 4 | | | IV-1 | Hnrnpr |
| 15048 | 3 | 4 | | | IV-1 | Hnrnpu |
| 15049 | 3 | 4 | | | IV-1 | Hnrnpul2 |
| 15050 | 3 | 4 | | | IV-1 | Hormad1 |
| 15051 | 3 | 4 | | | IV-1 | Hormad2 |
| 15052 | 3 | 4 | | | IV-1 | Hottip |
| 15053 | 3 | 4 | | | IV-1 | Hoxa1 |
| 15054 | 3 | 4 | | | IV-1 | Hoxa10 |
| 15055 | 3 | 4 | | | IV-1 | Hoxa11 |
| 15056 | 3 | 4 | | | IV-1 | Hoxa11os |
| 15057 | 3 | 4 | | | IV-1 | Hoxa13 |
| 15058 | 3 | 4 | | | IV-1 | Hoxa2 |
| 15059 | 3 | 4 | | | IV-1 | Hoxa3 |
| 15060 | 3 | 4 | | | IV-1 | Hoxa9 |
| 15061 | 3 | 4 | | | IV-1 | Hoxb4 |
| 15062 | 3 | 4 | | | IV-1 | Hoxb5 |
| 15063 | 3 | 4 | | | IV-1 | Hoxc10 |
| 15064 | 3 | 4 | | | IV-1 | Hoxc11 |
| 15065 | 3 | 4 | | | IV-1 | Hoxc13 |
| 15066 | 3 | 4 | | | IV-1 | Hoxc5 |
| 15067 | 3 | 4 | | | IV-1 | Hoxc6 |
| 15068 | 3 | 4 | | | IV-1 | Hoxc9 |
| 15069 | 3 | 4 | | | IV-1 | Hoxd10 |
| 15070 | 3 | 4 | | | IV-1 | Hp1bp3 |
| 15071 | 3 | 4 | | | IV-1 | Hpcal4 |
| 15072 | 3 | 4 | | | IV-1 | Hps3 |
| 15073 | 3 | 4 | | | IV-1 | Hps5 |
| 15074 | 3 | 4 | | | IV-1 | Hpse2 |
| 15075 | 3 | 4 | | | IV-1 | Hras |
| 15076 | 3 | 4 | | | IV-1 | Hrasls5 |
| 15077 | 3 | 4 | | | IV-1 | Hrh1 |
| 15078 | 3 | 4 | | | IV-1 | Hrh3 |
| 15079 | 3 | 4 | | | IV-1 | Hrh4 |
| 15080 | 3 | 4 | | | IV-1 | Hrk |
| 15081 | 3 | 4 | | | IV-1 | Hs1bp3 |
| 15082 | 3 | 4 | | | IV-1 | Hs2st1 |
| 15083 | 3 | 4 | | | IV-1 | Hs3st2 |
| 15084 | 3 | 4 | | | IV-1 | Hs3st4 |
| 15085 | 3 | 4 | | | IV-1 | Hs6st2 |
| 15086 | 3 | 4 | | | IV-1 | Hsbp1 |
| 15087 | 3 | 4 | | | IV-1 | Hsd17b1 |
| 15088 | 3 | 4 | | | IV-1 | Hsd17b10 |
| 15089 | 3 | 4 | | | IV-1 | Hsd17b2 |
| 15090 | 3 | 4 | | | IV-1 | Hsd17b3 |
| 15091 | 3 | 4 | | | IV-1 | Hsd17b4 |
| 15092 | 3 | 4 | | | IV-1 | Hsd3b3 |
| 15093 | 3 | 4 | | | IV-1 | Hsd3b4 |
| 15094 | 3 | 4 | | | IV-1 | Hsd3b7 |
| 15095 | 3 | 4 | | | IV-1 | Hsdl1 |
| 15096 | 3 | 4 | | | IV-1 | Hsdl2 |
| 15097 | 3 | 4 | | | IV-1 | Hsf1 |
| 15098 | 3 | 4 | | | IV-1 | Hsf2 |
| 15099 | 3 | 4 | | | IV-1 | Hsf2bp |
| 15100 | 3 | 4 | | | IV-1 | Hsf5 |
| 15101 | 3 | 4 | | | IV-1 | Hsfy2 |
| 15102 | 3 | 4 | | | IV-1 | Hsp90aa1 |
| 15103 | 3 | 4 | | | IV-1 | Hsp90ab1 |
| 15104 | 3 | 4 | | | IV-1 | Hspa12a |
| 15105 | 3 | 4 | | | IV-1 | Hspa14 |
| 15106 | 3 | 4 | | | IV-1 | Hspa1l |
| 15107 | 3 | 4 | | | IV-1 | Hspa4 |
| 15108 | 3 | 4 | | | IV-1 | Hspa9 |
| 15109 | 3 | 4 | | | IV-1 | Hspb8 |
| 15110 | 3 | 4 | | | IV-1 | Hspbp1 |
| 15111 | 3 | 4 | | | IV-1 | Hspd1 |
| 15112 | 3 | 4 | | | IV-1 | Hspg2 |
| 15113 | 3 | 4 | | | IV-1 | Htatsf1 |
| 15114 | 3 | 4 | | | IV-1 | Htr1a |
| 15115 | 3 | 4 | | | IV-1 | Htr2c |
| 15116 | 3 | 4 | | | IV-1 | Htr4 |
| 15117 | 3 | 4 | | | IV-1 | Htr5a |
| 15118 | 3 | 4 | | | IV-1 | Htr7 |
| 15119 | 3 | 4 | | | IV-1 | Htra2 |
| 15120 | 3 | 4 | | | IV-1 | Hus1 |
| 15121 | 3 | 4 | | | IV-1 | Hus1b |
| 15122 | 3 | 4 | | | IV-1 | Hvcn1 |
| 15123 | 3 | 4 | | | IV-1 | Hyal2 |
| 15124 | 3 | 4 | | | IV-1 | Hyal3 |
| 15125 | 3 | 4 | | | IV-1 | Hyal5 |
| 15126 | 3 | 4 | | | IV-1 | Hyou1 |
| 15127 | 3 | 4 | | | IV-1 | Iars |
| 15128 | 3 | 4 | | | IV-1 | Iars2 |
| 15129 | 3 | 4 | | | IV-1 | Iba57 |
| 15130 | 3 | 4 | | | IV-1 | Ibtk |
| 15131 | 3 | 4 | | | IV-1 | Ica1l |
| 15132 | 3 | 4 | | | IV-1 | Icam4 |
| 15133 | 3 | 4 | | | IV-1 | Icam5 |
| 15134 | 3 | 4 | | | IV-1 | Icmt |
| 15135 | 3 | 4 | | | IV-1 | Icos |
| 15136 | 3 | 4 | | | IV-1 | Ide |
| 15137 | 3 | 4 | | | IV-1 | Idh2 |
| 15138 | 3 | 4 | | | IV-1 | Idh3b |
| 15139 | 3 | 4 | | | IV-1 | Idh3g |
| 15140 | 3 | 4 | | | IV-1 | Idnk |
| 15141 | 3 | 4 | | | IV-1 | Ido2 |
| 15142 | 3 | 4 | | | IV-1 | Ids |
| 15143 | 3 | 4 | | | IV-1 | Idua |
| 15144 | 3 | 4 | | | IV-1 | Iffo1 |
| 15145 | 3 | 4 | | | IV-1 | Ifi205 |
| 15146 | 3 | 4 | | | IV-1 | Ifitm10 |
| 15147 | 3 | 4 | | | IV-1 | Ifltd1 |
| 15148 | 3 | 4 | | | IV-1 | Ifnar1 |
| 15149 | 3 | 4 | | | IV-1 | Ift122 |
| 15150 | 3 | 4 | | | IV-1 | Ift140 |
| 15151 | 3 | 4 | | | IV-1 | Ift52 |
| 15152 | 3 | 4 | | | IV-1 | Ift57 |
| 15153 | 3 | 4 | | | IV-1 | Ift74 |
| 15154 | 3 | 4 | | | IV-1 | Ift80 |
| 15155 | 3 | 4 | | | IV-1 | Ift88 |
| 15156 | 3 | 4 | | | IV-1 | Igbp1 |
| 15157 | 3 | 4 | | | IV-1 | Igbp1b |
| 15158 | 3 | 4 | | | IV-1 | Igdcc4 |
| 15159 | 3 | 4 | | | IV-1 | Igf2 |
| 15160 | 3 | 4 | | | IV-1 | Igf2bp1 |
| 15161 | 3 | 4 | | | IV-1 | Igf2bp2 |
| 15162 | 3 | 4 | | | IV-1 | Igf2bp3 |
| 15163 | 3 | 4 | | | IV-1 | Igfbp7 |
| 15164 | 3 | 4 | | | IV-1 | Igfn1 |
| 15165 | 3 | 4 | | | IV-1 | Ighmbp2 |
| 15166 | 3 | 4 | | | IV-1 | Igsf1 |

Fig. 36 - 80

| | | | | | | |
|---|---|---|---|---|---|---|
| 15167 | 3 | 4 | | | IV-1 | Igsf10 |
| 15168 | 3 | 4 | | | IV-1 | Igsf21 |
| 15169 | 3 | 4 | | | IV-1 | Igsf23 |
| 15170 | 3 | 4 | | | IV-1 | Igsf3 |
| 15171 | 3 | 4 | | | IV-1 | Igsf8 |
| 15172 | 3 | 4 | | | IV-1 | Igsf9 |
| 15173 | 3 | 4 | | | IV-1 | Ik |
| 15174 | 3 | 4 | | | IV-1 | Ikbkap |
| 15175 | 3 | 4 | | | IV-1 | Ikbkb |
| 15176 | 3 | 4 | | | IV-1 | Ikbke |
| 15177 | 3 | 4 | | | IV-1 | Il10rb |
| 15178 | 3 | 4 | | | IV-1 | Il11 |
| 15179 | 3 | 4 | | | IV-1 | Il12rb1 |
| 15180 | 3 | 4 | | | IV-1 | Il13ra2 |
| 15181 | 3 | 4 | | | IV-1 | Il15ra |
| 15182 | 3 | 4 | | | IV-1 | Il17b |
| 15183 | 3 | 4 | | | IV-1 | Il17d |
| 15184 | 3 | 4 | | | IV-1 | Il17f |
| 15185 | 3 | 4 | | | IV-1 | Il17ra |
| 15186 | 3 | 4 | | | IV-1 | Il18r1 |
| 15187 | 3 | 4 | | | IV-1 | Il1bos |
| 15188 | 3 | 4 | | | IV-1 | Il1f5 |
| 15189 | 3 | 4 | | | IV-1 | Il1f6 |
| 15190 | 3 | 4 | | | IV-1 | Il1f8 |
| 15191 | 3 | 4 | | | IV-1 | Il1rl1 |
| 15192 | 3 | 4 | | | IV-1 | Il20ra |
| 15193 | 3 | 4 | | | IV-1 | Il21 |
| 15194 | 3 | 4 | | | IV-1 | Il23r |
| 15195 | 3 | 4 | | | IV-1 | Il27 |
| 15196 | 3 | 4 | | | IV-1 | Il27ra |
| 15197 | 3 | 4 | | | IV-1 | Il31 |
| 15198 | 3 | 4 | | | IV-1 | Il31ra |
| 15199 | 3 | 4 | | | IV-1 | Il33 |
| 15200 | 3 | 4 | | | IV-1 | Il5ra |
| 15201 | 3 | 4 | | | IV-1 | Il7 |
| 15202 | 3 | 4 | | | IV-1 | Il7r |
| 15203 | 3 | 4 | | | IV-1 | Ildr2 |
| 15204 | 3 | 4 | | | IV-1 | Ilf3 |
| 15205 | 3 | 4 | | | IV-1 | Iltifb |
| 15206 | 3 | 4 | | | IV-1 | Immt |
| 15207 | 3 | 4 | | | IV-1 | Imp4 |
| 15208 | 3 | 4 | | | IV-1 | Impa1 |
| 15209 | 3 | 4 | | | IV-1 | Impact |
| 15210 | 3 | 4 | | | IV-1 | Impdh1 |
| 15211 | 3 | 4 | | | IV-1 | Ina |
| 15212 | 3 | 4 | | | IV-1 | Incenp |
| 15213 | 3 | 4 | | | IV-1 | Ing1 |
| 15214 | 3 | 4 | | | IV-1 | Ing2 |
| 15215 | 3 | 4 | | | IV-1 | Ing3 |
| 15216 | 3 | 4 | | | IV-1 | Ing4 |
| 15217 | 3 | 4 | | | IV-1 | Ing5 |
| 15218 | 3 | 4 | | | IV-1 | Inhbc |
| 15219 | 3 | 4 | | | IV-1 | Inip |
| 15220 | 3 | 4 | | | IV-1 | Ino80 |
| 15221 | 3 | 4 | | | IV-1 | Ino80c |
| 15222 | 3 | 4 | | | IV-1 | Ino80e |
| 15223 | 3 | 4 | | | IV-1 | Inpp1 |
| 15224 | 3 | 4 | | | IV-1 | Inpp4b |
| 15225 | 3 | 4 | | | IV-1 | Inpp5b |
| 15226 | 3 | 4 | | | IV-1 | Inpp5d |
| 15227 | 3 | 4 | | | IV-1 | Inpp5f |
| 15228 | 3 | 4 | | | IV-1 | Inpp5k |
| 15229 | 3 | 4 | | | IV-1 | Inppl1 |
| 15230 | 3 | 4 | | | IV-1 | Insig1 |
| 15231 | 3 | 4 | | | IV-1 | Insm1 |
| 15232 | 3 | 4 | | | IV-1 | Insr |
| 15233 | 3 | 4 | | | IV-1 | Insrr |
| 15234 | 3 | 4 | | | IV-1 | Ints10 |
| 15235 | 3 | 4 | | | IV-1 | Ints12 |
| 15236 | 3 | 4 | | | IV-1 | Ints3 |
| 15237 | 3 | 4 | | | IV-1 | Ints4 |
| 15238 | 3 | 4 | | | IV-1 | Ints5 |
| 15239 | 3 | 4 | | | IV-1 | Ints9 |
| 15240 | 3 | 4 | | | IV-1 | Invs |
| 15241 | 3 | 4 | | | IV-1 | Ip6k1 |
| 15242 | 3 | 4 | | | IV-1 | Ipmk |
| 15243 | 3 | 4 | | | IV-1 | Ipo4 |
| 15244 | 3 | 4 | | | IV-1 | Ipo5 |
| 15245 | 3 | 4 | | | IV-1 | Ipo8 |
| 15246 | 3 | 4 | | | IV-1 | Ipo9 |
| 15247 | 3 | 4 | | | IV-1 | Ipp |
| 15248 | 3 | 4 | | | IV-1 | Ippk |
| 15249 | 3 | 4 | | | IV-1 | Ipw |
| 15250 | 3 | 4 | | | IV-1 | Iqca |
| 15251 | 3 | 4 | | | IV-1 | Iqcc |
| 15252 | 3 | 4 | | | IV-1 | Iqcf1 |
| 15253 | 3 | 4 | | | IV-1 | Iqcf3 |
| 15254 | 3 | 4 | | | IV-1 | Iqcf4 |
| 15255 | 3 | 4 | | | IV-1 | Iqcf6 |
| 15256 | 3 | 4 | | | IV-1 | Iqch |
| 15257 | 3 | 4 | | | IV-1 | Iqgap1 |
| 15258 | 3 | 4 | | | IV-1 | Iqgap3 |
| 15259 | 3 | 4 | | | IV-1 | Iqsec2 |
| 15260 | 3 | 4 | | | IV-1 | Iqub |
| 15261 | 3 | 4 | | | IV-1 | Irak3 |
| 15262 | 3 | 4 | | | IV-1 | Irak4 |

| | | | | | | |
|---|---|---|---|---|---|---|
| 15263 | 3 | 4 | | | IV-1 | Ireb2 |
| 15264 | 3 | 4 | | | IV-1 | Irf2bp1 |
| 15265 | 3 | 4 | | | IV-1 | Irf2bp2 |
| 15266 | 3 | 4 | | | IV-1 | Irf3 |
| 15267 | 3 | 4 | | | IV-1 | Irgq |
| 15268 | 3 | 4 | | | IV-1 | Irs3 |
| 15269 | 3 | 4 | | | IV-1 | Irx1 |
| 15270 | 3 | 4 | | | IV-1 | Irx5 |
| 15271 | 3 | 4 | | | IV-1 | Isg20l2 |
| 15272 | 3 | 4 | | | IV-1 | Isoc2a |
| 15273 | 3 | 4 | | | IV-1 | Ist1 |
| 15274 | 3 | 4 | | | IV-1 | Isy1 |
| 15275 | 3 | 4 | | | IV-1 | Itch |
| 15276 | 3 | 4 | | | IV-1 | Itfg1 |
| 15277 | 3 | 4 | | | IV-1 | Itga10 |
| 15278 | 3 | 4 | | | IV-1 | Itga11 |
| 15279 | 3 | 4 | | | IV-1 | Itga5 |
| 15280 | 3 | 4 | | | IV-1 | Itga9 |
| 15281 | 3 | 4 | | | IV-1 | Itgad |
| 15282 | 3 | 4 | | | IV-1 | Itgae |
| 15283 | 3 | 4 | | | IV-1 | Itgal |
| 15284 | 3 | 4 | | | IV-1 | Itgb1 |
| 15285 | 3 | 4 | | | IV-1 | Itgb2l |
| 15286 | 3 | 4 | | | IV-1 | Itgb4 |
| 15287 | 3 | 4 | | | IV-1 | Itgbl1 |
| 15288 | 3 | 4 | | | IV-1 | Itih1 |
| 15289 | 3 | 4 | | | IV-1 | Itih3 |
| 15290 | 3 | 4 | | | IV-1 | Itk |
| 15291 | 3 | 4 | | | IV-1 | Itm2b |
| 15292 | 3 | 4 | | | IV-1 | Itm2c |
| 15293 | 3 | 4 | | | IV-1 | Itpk1 |
| 15294 | 3 | 4 | | | IV-1 | Itpkc |
| 15295 | 3 | 4 | | | IV-1 | Itpr2 |
| 15296 | 3 | 4 | | | IV-1 | Itpripl1 |
| 15297 | 3 | 4 | | | IV-1 | Ivd |
| 15298 | 3 | 4 | | | IV-1 | Ivl |
| 15299 | 3 | 4 | | | IV-1 | Ivns1abp |
| 15300 | 3 | 4 | | | IV-1 | Izumo1 |
| 15301 | 3 | 4 | | | IV-1 | Izumo2 |
| 15302 | 3 | 4 | | | IV-1 | Izumo3 |
| 15303 | 3 | 4 | | | IV-1 | Jade2 |
| 15304 | 3 | 4 | | | IV-1 | Jag1 |
| 15305 | 3 | 4 | | | IV-1 | Jagn1 |
| 15306 | 3 | 4 | | | IV-1 | Jak2 |
| 15307 | 3 | 4 | | | IV-1 | Jakmip1 |
| 15308 | 3 | 4 | | | IV-1 | Jakmip2 |
| 15309 | 3 | 4 | | | IV-1 | Jakmip3 |
| 15310 | 3 | 4 | | | IV-1 | Jam2 |
| 15311 | 3 | 4 | | | IV-1 | Jam3 |
| 15312 | 3 | 4 | | | IV-1 | Jkamp |
| 15313 | 3 | 4 | | | IV-1 | Jmjd7-pla2g4b |
| 15314 | 3 | 4 | | | IV-1 | Jmjd8 |
| 15315 | 3 | 4 | | | IV-1 | Josd1 |
| 15316 | 3 | 4 | | | IV-1 | Jph1 |
| 15317 | 3 | 4 | | | IV-1 | Jph3 |
| 15318 | 3 | 4 | | | IV-1 | Jph4 |
| 15319 | 3 | 4 | | | IV-1 | Jpx |
| 15320 | 3 | 4 | | | IV-1 | Jrk |
| 15321 | 3 | 4 | | | IV-1 | Jrkl |
| 15322 | 3 | 4 | | | IV-1 | Jtb |
| 15323 | 3 | 4 | | | IV-1 | Jun |
| 15324 | 3 | 4 | | | IV-1 | Jup |
| 15325 | 3 | 4 | | | IV-1 | Kalrn |
| 15326 | 3 | 4 | | | IV-1 | Kank1 |
| 15327 | 3 | 4 | | | IV-1 | Kank2 |
| 15328 | 3 | 4 | | | IV-1 | Kank4os |
| 15329 | 3 | 4 | | | IV-1 | Kansl1 |
| 15330 | 3 | 4 | | | IV-1 | Kansl2 |
| 15331 | 3 | 4 | | | IV-1 | Kansl3 |
| 15332 | 3 | 4 | | | IV-1 | Kars |
| 15333 | 3 | 4 | | | IV-1 | Kat2a |
| 15334 | 3 | 4 | | | IV-1 | Kat2b |
| 15335 | 3 | 4 | | | IV-1 | Kat5 |
| 15336 | 3 | 4 | | | IV-1 | Kat6b |
| 15337 | 3 | 4 | | | IV-1 | Kat7 |
| 15338 | 3 | 4 | | | IV-1 | Katnal1 |
| 15339 | 3 | 4 | | | IV-1 | Katnal2 |
| 15340 | 3 | 4 | | | IV-1 | Katnb1 |
| 15341 | 3 | 4 | | | IV-1 | Kazn |
| 15342 | 3 | 4 | | | IV-1 | Kbtbd11 |
| 15343 | 3 | 4 | | | IV-1 | Kbtbd2 |
| 15344 | 3 | 4 | | | IV-1 | Kbtbd3 |
| 15345 | 3 | 4 | | | IV-1 | Kbtbd7 |
| 15346 | 3 | 4 | | | IV-1 | Kcmf1 |
| 15347 | 3 | 4 | | | IV-1 | Kcna4 |
| 15348 | 3 | 4 | | | IV-1 | Kcna5 |
| 15349 | 3 | 4 | | | IV-1 | Kcna6 |
| 15350 | 3 | 4 | | | IV-1 | Kcna7 |
| 15351 | 3 | 4 | | | IV-1 | Kcnab2 |
| 15352 | 3 | 4 | | | IV-1 | Kcnab3 |
| 15353 | 3 | 4 | | | IV-1 | Kcnc2 |
| 15354 | 3 | 4 | | | IV-1 | Kcnc4 |
| 15355 | 3 | 4 | | | IV-1 | Kcnd2 |
| 15356 | 3 | 4 | | | IV-1 | Kcnd3os |
| 15357 | 3 | 4 | | | IV-1 | Kcne1l |
| 15358 | 3 | 4 | | | IV-1 | Kcne2 |

Fig. 36 - 81

| | | | | | | |
|---|---|---|---|---|---|---|
| 15359 | 3 | 4 | | | IV-1 | Kcng2 |
| 15360 | 3 | 4 | | | IV-1 | Kcnh4 |
| 15361 | 3 | 4 | | | IV-1 | Kcnh6 |
| 15362 | 3 | 4 | | | IV-1 | Kcnh7 |
| 15363 | 3 | 4 | | | IV-1 | Kcnip2 |
| 15364 | 3 | 4 | | | IV-1 | Kcnip4 |
| 15365 | 3 | 4 | | | IV-1 | Kcnj1 |
| 15366 | 3 | 4 | | | IV-1 | Kcnj11 |
| 15367 | 3 | 4 | | | IV-1 | Kcnj13 |
| 15368 | 3 | 4 | | | IV-1 | Kcnj14 |
| 15369 | 3 | 4 | | | IV-1 | Kcnj15 |
| 15370 | 3 | 4 | | | IV-1 | Kcnj5 |
| 15371 | 3 | 4 | | | IV-1 | Kcnj9 |
| 15372 | 3 | 4 | | | IV-1 | Kcnk12 |
| 15373 | 3 | 4 | | | IV-1 | Kcnk13 |
| 15374 | 3 | 4 | | | IV-1 | Kcnk4 |
| 15375 | 3 | 4 | | | IV-1 | Kcnk7 |
| 15376 | 3 | 4 | | | IV-1 | Kcnmb1 |
| 15377 | 3 | 4 | | | IV-1 | Kcnmb2 |
| 15378 | 3 | 4 | | | IV-1 | Kcnn1 |
| 15379 | 3 | 4 | | | IV-1 | Kcnq2 |
| 15380 | 3 | 4 | | | IV-1 | Kcnq5 |
| 15381 | 3 | 4 | | | IV-1 | Kcns1 |
| 15382 | 3 | 4 | | | IV-1 | Kcns2 |
| 15383 | 3 | 4 | | | IV-1 | Kcns3 |
| 15384 | 3 | 4 | | | IV-1 | Kcnt1 |
| 15385 | 3 | 4 | | | IV-1 | Kcnu1 |
| 15386 | 3 | 4 | | | IV-1 | Kcnv1 |
| 15387 | 3 | 4 | | | IV-1 | Kcnv2 |
| 15388 | 3 | 4 | | | IV-1 | Kctd10 |
| 15389 | 3 | 4 | | | IV-1 | Kctd17 |
| 15390 | 3 | 4 | | | IV-1 | Kctd2 |
| 15391 | 3 | 4 | | | IV-1 | Kctd21 |
| 15392 | 3 | 4 | | | IV-1 | Kctd3 |
| 15393 | 3 | 4 | | | IV-1 | Kctd5 |
| 15394 | 3 | 4 | | | IV-1 | Kctd7 |
| 15395 | 3 | 4 | | | IV-1 | Kctd8 |
| 15396 | 3 | 4 | | | IV-1 | Kctd9 |
| 15397 | 3 | 4 | | | IV-1 | Kdelc1 |
| 15398 | 3 | 4 | | | IV-1 | Kdelc2 |
| 15399 | 3 | 4 | | | IV-1 | Kdelr1 |
| 15400 | 3 | 4 | | | IV-1 | Kdelr2 |
| 15401 | 3 | 4 | | | IV-1 | Kdm1a |
| 15402 | 3 | 4 | | | IV-1 | Kdm1b |
| 15403 | 3 | 4 | | | IV-1 | Kdm2a |
| 15404 | 3 | 4 | | | IV-1 | Kdm2b |
| 15405 | 3 | 4 | | | IV-1 | Kdm3a |
| 15406 | 3 | 4 | | | IV-1 | Kdm4a |
| 15407 | 3 | 4 | | | IV-1 | Kdm4b |
| 15408 | 3 | 4 | | | IV-1 | Kdm4c |
| 15409 | 3 | 4 | | | IV-1 | Kdm5a |
| 15410 | 3 | 4 | | | IV-1 | Kdm5b |
| 15411 | 3 | 4 | | | IV-1 | Kdm5c |
| 15412 | 3 | 4 | | | IV-1 | Kdm5d |
| 15413 | 3 | 4 | | | IV-1 | Kdr |
| 15414 | 3 | 4 | | | IV-1 | Kdsr |
| 15415 | 3 | 4 | | | IV-1 | Keap1 |
| 15416 | 3 | 4 | | | IV-1 | Kera |
| 15417 | 3 | 4 | | | IV-1 | Khdc3 |
| 15418 | 3 | 4 | | | IV-1 | Khdrbs1 |
| 15419 | 3 | 4 | | | IV-1 | Khsrp |
| 15420 | 3 | 4 | | | IV-1 | Kidins220 |
| 15421 | 3 | 4 | | | IV-1 | Kif11 |
| 15422 | 3 | 4 | | | IV-1 | Kif12 |
| 15423 | 3 | 4 | | | IV-1 | Kif13a |
| 15424 | 3 | 4 | | | IV-1 | Kif14 |
| 15425 | 3 | 4 | | | IV-1 | Kif15 |
| 15426 | 3 | 4 | | | IV-1 | Kif16b |
| 15427 | 3 | 4 | | | IV-1 | Kif17 |
| 15428 | 3 | 4 | | | IV-1 | Kif18a |
| 15429 | 3 | 4 | | | IV-1 | Kif18b |
| 15430 | 3 | 4 | | | IV-1 | Kif19a |
| 15431 | 3 | 4 | | | IV-1 | Kif1a |
| 15432 | 3 | 4 | | | IV-1 | Kif1b |
| 15433 | 3 | 4 | | | IV-1 | Kif1c |
| 15434 | 3 | 4 | | | IV-1 | Kif20a |
| 15435 | 3 | 4 | | | IV-1 | Kif21a |
| 15436 | 3 | 4 | | | IV-1 | Kif22 |
| 15437 | 3 | 4 | | | IV-1 | Kif23 |
| 15438 | 3 | 4 | | | IV-1 | Kif27 |
| 15439 | 3 | 4 | | | IV-1 | Kif2b |
| 15440 | 3 | 4 | | | IV-1 | Kif3a |
| 15441 | 3 | 4 | | | IV-1 | Kif3c |
| 15442 | 3 | 4 | | | IV-1 | Kif4 |
| 15443 | 3 | 4 | | | IV-1 | Kif5a |
| 15444 | 3 | 4 | | | IV-1 | Kif5c |
| 15445 | 3 | 4 | | | IV-1 | Kif7 |
| 15446 | 3 | 4 | | | IV-1 | Kifap3 |
| 15447 | 3 | 4 | | | IV-1 | Kifc2 |
| 15448 | 3 | 4 | | | IV-1 | Kirrel2 |
| 15449 | 3 | 4 | | | IV-1 | Kiss1r |
| 15450 | 3 | 4 | | | IV-1 | Kitl |
| 15451 | 3 | 4 | | | IV-1 | Kiz |
| 15452 | 3 | 4 | | | IV-1 | Klc2 |
| 15453 | 3 | 4 | | | IV-1 | Klc4 |
| 15454 | 3 | 4 | | | IV-1 | Klf1 |
| 15455 | 3 | 4 | | | IV-1 | Klf17 |
| 15456 | 3 | 4 | | | IV-1 | Klhdc10 |
| 15457 | 3 | 4 | | | IV-1 | Klhdc2 |
| 15458 | 3 | 4 | | | IV-1 | Klhdc3 |
| 15459 | 3 | 4 | | | IV-1 | Klhl1 |
| 15460 | 3 | 4 | | | IV-1 | Klhl10 |
| 15461 | 3 | 4 | | | IV-1 | Klhl12 |
| 15462 | 3 | 4 | | | IV-1 | Klhl13 |
| 15463 | 3 | 4 | | | IV-1 | Klhl17 |
| 15464 | 3 | 4 | | | IV-1 | Klhl18 |
| 15465 | 3 | 4 | | | IV-1 | Klhl2 |
| 15466 | 3 | 4 | | | IV-1 | Klhl20 |
| 15467 | 3 | 4 | | | IV-1 | Klhl21 |
| 15468 | 3 | 4 | | | IV-1 | Klhl22 |
| 15469 | 3 | 4 | | | IV-1 | Klhl26 |
| 15470 | 3 | 4 | | | IV-1 | Klhl30 |
| 15471 | 3 | 4 | | | IV-1 | Klhl31 |
| 15472 | 3 | 4 | | | IV-1 | Klhl36 |
| 15473 | 3 | 4 | | | IV-1 | Klhl40 |
| 15474 | 3 | 4 | | | IV-1 | Klhl42 |
| 15475 | 3 | 4 | | | IV-1 | Klhl5 |
| 15476 | 3 | 4 | | | IV-1 | Klhl8 |
| 15477 | 3 | 4 | | | IV-1 | Klhl9 |
| 15478 | 3 | 4 | | | IV-1 | Klk11 |
| 15479 | 3 | 4 | | | IV-1 | Klk13 |
| 15480 | 3 | 4 | | | IV-1 | Klk1b11 |
| 15481 | 3 | 4 | | | IV-1 | Klk1b3 |
| 15482 | 3 | 4 | | | IV-1 | Klk1b7-ps |
| 15483 | 3 | 4 | | | IV-1 | Klk5 |
| 15484 | 3 | 4 | | | IV-1 | Klk6 |
| 15485 | 3 | 4 | | | IV-1 | Klk7 |
| 15486 | 3 | 4 | | | IV-1 | Klkb1 |
| 15487 | 3 | 4 | | | IV-1 | Klra2 |
| 15488 | 3 | 4 | | | IV-1 | Klra3 |
| 15489 | 3 | 4 | | | IV-1 | Klra9 |
| 15490 | 3 | 4 | | | IV-1 | Klrb1f |
| 15491 | 3 | 4 | | | IV-1 | Kmo |
| 15492 | 3 | 4 | | | IV-1 | Kng2 |
| 15493 | 3 | 4 | | | IV-1 | Knop1 |
| 15494 | 3 | 4 | | | IV-1 | Knstrn |
| 15495 | 3 | 4 | | | IV-1 | Kntc1 |
| 15496 | 3 | 4 | | | IV-1 | Kpna4 |
| 15497 | 3 | 4 | | | IV-1 | Kpna6 |
| 15498 | 3 | 4 | | | IV-1 | Kpnb1 |
| 15499 | 3 | 4 | | | IV-1 | Kras |
| 15500 | 3 | 4 | | | IV-1 | Krba1 |
| 15501 | 3 | 4 | | | IV-1 | Kremen1 |
| 15502 | 3 | 4 | | | IV-1 | Kremen2 |
| 15503 | 3 | 4 | | | IV-1 | Krit1 |
| 15504 | 3 | 4 | | | IV-1 | Krr1 |
| 15505 | 3 | 4 | | | IV-1 | Krt1 |
| 15506 | 3 | 4 | | | IV-1 | Krt12 |
| 15507 | 3 | 4 | | | IV-1 | Krt13 |
| 15508 | 3 | 4 | | | IV-1 | Krt2 |
| 15509 | 3 | 4 | | | IV-1 | Krt222 |
| 15510 | 3 | 4 | | | IV-1 | Krt25 |
| 15511 | 3 | 4 | | | IV-1 | Krt27 |
| 15512 | 3 | 4 | | | IV-1 | Krt32 |
| 15513 | 3 | 4 | | | IV-1 | Krt35 |
| 15514 | 3 | 4 | | | IV-1 | Krt36 |
| 15515 | 3 | 4 | | | IV-1 | Krt4 |
| 15516 | 3 | 4 | | | IV-1 | Krt71 |
| 15517 | 3 | 4 | | | IV-1 | Krt73 |
| 15518 | 3 | 4 | | | IV-1 | Krt75 |
| 15519 | 3 | 4 | | | IV-1 | Krt77 |
| 15520 | 3 | 4 | | | IV-1 | Krt78 |
| 15521 | 3 | 4 | | | IV-1 | Krt79 |
| 15522 | 3 | 4 | | | IV-1 | Krt83 |
| 15523 | 3 | 4 | | | IV-1 | Krt85 |
| 15524 | 3 | 4 | | | IV-1 | Krtap1-4 |
| 15525 | 3 | 4 | | | IV-1 | Krtap14 |
| 15526 | 3 | 4 | | | IV-1 | Krtap19-4 |
| 15527 | 3 | 4 | | | IV-1 | Krtap3-3 |
| 15528 | 3 | 4 | | | IV-1 | Krtap4-2 |
| 15529 | 3 | 4 | | | IV-1 | Krtap4-9 |
| 15530 | 3 | 4 | | | IV-1 | Krtcap3 |
| 15531 | 3 | 4 | | | IV-1 | Krtdap |
| 15532 | 3 | 4 | | | IV-1 | Ktn1 |
| 15533 | 3 | 4 | | | IV-1 | L1cam |
| 15534 | 3 | 4 | | | IV-1 | L2hgdh |
| 15535 | 3 | 4 | | | IV-1 | L3hypdh |
| 15536 | 3 | 4 | | | IV-1 | L3mbtl2 |
| 15537 | 3 | 4 | | | IV-1 | L3mbtl4 |
| 15538 | 3 | 4 | | | IV-1 | LOC100040786 |
| 15539 | 3 | 4 | | | IV-1 | LOC100048884 |
| 15540 | 3 | 4 | | | IV-1 | LOC100505025 |
| 15541 | 3 | 4 | | | IV-1 | LOC100861615 |
| 15542 | 3 | 4 | | | IV-1 | LOC101056149 |
| 15543 | 3 | 4 | | | IV-1 | LOC102633315 |
| 15544 | 3 | 4 | | | IV-1 | LOC102634401 |
| 15545 | 3 | 4 | | | IV-1 | LOC102635087 |
| 15546 | 3 | 4 | | | IV-1 | LOC381967 |
| 15547 | 3 | 4 | | | IV-1 | Lactb |
| 15548 | 3 | 4 | | | IV-1 | Lama1 |
| 15549 | 3 | 4 | | | IV-1 | Lama3 |
| 15550 | 3 | 4 | | | IV-1 | Lama4 |

Fig. 36 - 82

| | | | | | | |
|---|---|---|---|---|---|---|
| 15551 | 3 | 4 | | | IV-1 | Lamb1 |
| 15552 | 3 | 4 | | | IV-1 | Lamb2 |
| 15553 | 3 | 4 | | | IV-1 | Lamb3 |
| 15554 | 3 | 4 | | | IV-1 | Lamc2 |
| 15555 | 3 | 4 | | | IV-1 | Lamc3 |
| 15556 | 3 | 4 | | | IV-1 | Lamp1 |
| 15557 | 3 | 4 | | | IV-1 | Lamp2 |
| 15558 | 3 | 4 | | | IV-1 | Lamp5 |
| 15559 | 3 | 4 | | | IV-1 | Lamtor1 |
| 15560 | 3 | 4 | | | IV-1 | Lancl1 |
| 15561 | 3 | 4 | | | IV-1 | Lancl2 |
| 15562 | 3 | 4 | | | IV-1 | Lap3 |
| 15563 | 3 | 4 | | | IV-1 | Laptm4a |
| 15564 | 3 | 4 | | | IV-1 | Large |
| 15565 | 3 | 4 | | | IV-1 | Larp1 |
| 15566 | 3 | 4 | | | IV-1 | Larp4 |
| 15567 | 3 | 4 | | | IV-1 | Larp6 |
| 15568 | 3 | 4 | | | IV-1 | Larp7 |
| 15569 | 3 | 4 | | | IV-1 | Lars |
| 15570 | 3 | 4 | | | IV-1 | Las1l |
| 15571 | 3 | 4 | | | IV-1 | Lasp1 |
| 15572 | 3 | 4 | | | IV-1 | Lats1 |
| 15573 | 3 | 4 | | | IV-1 | Lats2 |
| 15574 | 3 | 4 | | | IV-1 | Lbr |
| 15575 | 3 | 4 | | | IV-1 | Lbx1 |
| 15576 | 3 | 4 | | | IV-1 | Lce1a1 |
| 15577 | 3 | 4 | | | IV-1 | Lce1a2 |
| 15578 | 3 | 4 | | | IV-1 | Lce1h |
| 15579 | 3 | 4 | | | IV-1 | Lce1l |
| 15580 | 3 | 4 | | | IV-1 | Lce1m |
| 15581 | 3 | 4 | | | IV-1 | Lce3b |
| 15582 | 3 | 4 | | | IV-1 | Lce3c |
| 15583 | 3 | 4 | | | IV-1 | Lclat1 |
| 15584 | 3 | 4 | | | IV-1 | Lctl |
| 15585 | 3 | 4 | | | IV-1 | Ldb1 |
| 15586 | 3 | 4 | | | IV-1 | Ldhal6b |
| 15587 | 3 | 4 | | | IV-1 | Ldhc |
| 15588 | 3 | 4 | | | IV-1 | Ldoc1 |
| 15589 | 3 | 4 | | | IV-1 | Lect2 |
| 15590 | 3 | 4 | | | IV-1 | Lemd2 |
| 15591 | 3 | 4 | | | IV-1 | Lemd3 |
| 15592 | 3 | 4 | | | IV-1 | Leng1 |
| 15593 | 3 | 4 | | | IV-1 | Leng8 |
| 15594 | 3 | 4 | | | IV-1 | Leo1 |
| 15595 | 3 | 4 | | | IV-1 | Leprel |
| 15596 | 3 | 4 | | | IV-1 | Leprel1 |
| 15597 | 3 | 4 | | | IV-1 | Leprel2 |
| 15598 | 3 | 4 | | | IV-1 | Leprot |
| 15599 | 3 | 4 | | | IV-1 | Letm1 |
| 15600 | 3 | 4 | | | IV-1 | Lgals8 |
| 15601 | 3 | 4 | | | IV-1 | Lgi1 |
| 15602 | 3 | 4 | | | IV-1 | Lgi4 |
| 15603 | 3 | 4 | | | IV-1 | Lgmn |
| 15604 | 3 | 4 | | | IV-1 | Lgr6 |
| 15605 | 3 | 4 | | | IV-1 | Lhfpl1 |
| 15606 | 3 | 4 | | | IV-1 | Lhfpl2 |
| 15607 | 3 | 4 | | | IV-1 | Lhfpl3 |
| 15608 | 3 | 4 | | | IV-1 | Lhfpl4 |
| 15609 | 3 | 4 | | | IV-1 | Lhfpl5 |
| 15610 | 3 | 4 | | | IV-1 | Lhpp |
| 15611 | 3 | 4 | | | IV-1 | Lhx2 |
| 15612 | 3 | 4 | | | IV-1 | Lhx5 |
| 15613 | 3 | 4 | | | IV-1 | Lif |
| 15614 | 3 | 4 | | | IV-1 | Lig3 |
| 15615 | 3 | 4 | | | IV-1 | Lima1 |
| 15616 | 3 | 4 | | | IV-1 | Limch1 |
| 15617 | 3 | 4 | | | IV-1 | Limd1 |
| 15618 | 3 | 4 | | | IV-1 | Lime1 |
| 15619 | 3 | 4 | | | IV-1 | Limk1 |
| 15620 | 3 | 4 | | | IV-1 | Limk2 |
| 15621 | 3 | 4 | | | IV-1 | Lin52 |
| 15622 | 3 | 4 | | | IV-1 | Lin54 |
| 15623 | 3 | 4 | | | IV-1 | Lin7a |
| 15624 | 3 | 4 | | | IV-1 | Lin7c |
| 15625 | 3 | 4 | | | IV-1 | Lincma-cox2 |
| 15626 | 3 | 4 | | | IV-1 | Lipa |
| 15627 | 3 | 4 | | | IV-1 | Lipc |
| 15628 | 3 | 4 | | | IV-1 | Lipe |
| 15629 | 3 | 4 | | | IV-1 | Lipf |
| 15630 | 3 | 4 | | | IV-1 | Liph |
| 15631 | 3 | 4 | | | IV-1 | Lipi |
| 15632 | 3 | 4 | | | IV-1 | Lipk |
| 15633 | 3 | 4 | | | IV-1 | Lipm |
| 15634 | 3 | 4 | | | IV-1 | Lipn |
| 15635 | 3 | 4 | | | IV-1 | Lipo1 |
| 15636 | 3 | 4 | | | IV-1 | Lkaaear1 |
| 15637 | 3 | 4 | | | IV-1 | Lman1 |
| 15638 | 3 | 4 | | | IV-1 | Lman2 |
| 15639 | 3 | 4 | | | IV-1 | Lman2l |
| 15640 | 3 | 4 | | | IV-1 | Lmbr1 |
| 15641 | 3 | 4 | | | IV-1 | Lmbrd1 |
| 15642 | 3 | 4 | | | IV-1 | Lmf1 |
| 15643 | 3 | 4 | | | IV-1 | Lmf2 |
| 15644 | 3 | 4 | | | IV-1 | Lmo3 |
| 15645 | 3 | 4 | | | IV-1 | Lmo7 |
| 15646 | 3 | 4 | | | IV-1 | Lmod1 |
| 15647 | 3 | 4 | | | IV-1 | Lnp |
| 15648 | 3 | 4 | | | IV-1 | Lnx2 |
| 15649 | 3 | 4 | | | IV-1 | Lonp1 |
| 15650 | 3 | 4 | | | IV-1 | Lonp2 |
| 15651 | 3 | 4 | | | IV-1 | Lor |
| 15652 | 3 | 4 | | | IV-1 | Loxl2 |
| 15653 | 3 | 4 | | | IV-1 | Loxl3 |
| 15654 | 3 | 4 | | | IV-1 | Loxl4 |
| 15655 | 3 | 4 | | | IV-1 | Lpar1 |
| 15656 | 3 | 4 | | | IV-1 | Lpar2 |
| 15657 | 3 | 4 | | | IV-1 | Lpar6 |
| 15658 | 3 | 4 | | | IV-1 | Lpcat2b |
| 15659 | 3 | 4 | | | IV-1 | Lpcat3 |
| 15660 | 3 | 4 | | | IV-1 | Lphn1 |
| 15661 | 3 | 4 | | | IV-1 | Lrch1 |
| 15662 | 3 | 4 | | | IV-1 | Lrch2 |
| 15663 | 3 | 4 | | | IV-1 | Lrfn2 |
| 15664 | 3 | 4 | | | IV-1 | Lrfn5 |
| 15665 | 3 | 4 | | | IV-1 | Lrguk |
| 15666 | 3 | 4 | | | IV-1 | Lrig1 |
| 15667 | 3 | 4 | | | IV-1 | Lrig2 |
| 15668 | 3 | 4 | | | IV-1 | Lrig3 |
| 15669 | 3 | 4 | | | IV-1 | Lrit1 |
| 15670 | 3 | 4 | | | IV-1 | Lrmp |
| 15671 | 3 | 4 | | | IV-1 | Lrp10 |
| 15672 | 3 | 4 | | | IV-1 | Lrp12 |
| 15673 | 3 | 4 | | | IV-1 | Lrp1b |
| 15674 | 3 | 4 | | | IV-1 | Lrp2bp |
| 15675 | 3 | 4 | | | IV-1 | Lrp3 |
| 15676 | 3 | 4 | | | IV-1 | Lrp5 |
| 15677 | 3 | 4 | | | IV-1 | Lrp6 |
| 15678 | 3 | 4 | | | IV-1 | Lrp8 |
| 15679 | 3 | 4 | | | IV-1 | Lrpap1 |
| 15680 | 3 | 4 | | | IV-1 | Lrpprc |
| 15681 | 3 | 4 | | | IV-1 | Lrrc10 |
| 15682 | 3 | 4 | | | IV-1 | Lrrc16b |
| 15683 | 3 | 4 | | | IV-1 | Lrrc17 |
| 15684 | 3 | 4 | | | IV-1 | Lrrc19 |
| 15685 | 3 | 4 | | | IV-1 | Lrrc2 |
| 15686 | 3 | 4 | | | IV-1 | Lrrc20 |
| 15687 | 3 | 4 | | | IV-1 | Lrrc26 |
| 15688 | 3 | 4 | | | IV-1 | Lrrc34 |
| 15689 | 3 | 4 | | | IV-1 | Lrrc3b |
| 15690 | 3 | 4 | | | IV-1 | Lrrc40 |
| 15691 | 3 | 4 | | | IV-1 | Lrrc41 |
| 15692 | 3 | 4 | | | IV-1 | Lrrc42 |
| 15693 | 3 | 4 | | | IV-1 | Lrrc43 |
| 15694 | 3 | 4 | | | IV-1 | Lrrc47 |
| 15695 | 3 | 4 | | | IV-1 | Lrrc4b |
| 15696 | 3 | 4 | | | IV-1 | Lrrc52 |
| 15697 | 3 | 4 | | | IV-1 | Lrrc55 |
| 15698 | 3 | 4 | | | IV-1 | Lrrc58 |
| 15699 | 3 | 4 | | | IV-1 | Lrrc6 |
| 15700 | 3 | 4 | | | IV-1 | Lrrc61 |
| 15701 | 3 | 4 | | | IV-1 | Lrrc63 |
| 15702 | 3 | 4 | | | IV-1 | Lrrc66 |
| 15703 | 3 | 4 | | | IV-1 | Lrrc69 |
| 15704 | 3 | 4 | | | IV-1 | Lrrc7 |
| 15705 | 3 | 4 | | | IV-1 | Lrrc72 |
| 15706 | 3 | 4 | | | IV-1 | Lrrc74 |
| 15707 | 3 | 4 | | | IV-1 | Lrrc8a |
| 15708 | 3 | 4 | | | IV-1 | Lrrc8d |
| 15709 | 3 | 4 | | | IV-1 | Lrrc8e |
| 15710 | 3 | 4 | | | IV-1 | Lrrcc1 |
| 15711 | 3 | 4 | | | IV-1 | Lrrd1 |
| 15712 | 3 | 4 | | | IV-1 | Lrriq1 |
| 15713 | 3 | 4 | | | IV-1 | Lrriq3 |
| 15714 | 3 | 4 | | | IV-1 | Lrrk1 |
| 15715 | 3 | 4 | | | IV-1 | Lrm1 |
| 15716 | 3 | 4 | | | IV-1 | Lrrn4cl |
| 15717 | 3 | 4 | | | IV-1 | Lrrtm1 |
| 15718 | 3 | 4 | | | IV-1 | Lrrtm2 |
| 15719 | 3 | 4 | | | IV-1 | Lrrtm3 |
| 15720 | 3 | 4 | | | IV-1 | Lrrtm4 |
| 15721 | 3 | 4 | | | IV-1 | Lrsam1 |
| 15722 | 3 | 4 | | | IV-1 | Lrtm1 |
| 15723 | 3 | 4 | | | IV-1 | Lsg1 |
| 15724 | 3 | 4 | | | IV-1 | Lsm1 |
| 15725 | 3 | 4 | | | IV-1 | Lsm12 |
| 15726 | 3 | 4 | | | IV-1 | Lsm14a |
| 15727 | 3 | 4 | | | IV-1 | Lsm14b |
| 15728 | 3 | 4 | | | IV-1 | Lsm2 |
| 15729 | 3 | 4 | | | IV-1 | Lsm6 |
| 15730 | 3 | 4 | | | IV-1 | Lta |
| 15731 | 3 | 4 | | | IV-1 | Ltb4r2 |
| 15732 | 3 | 4 | | | IV-1 | Ltbp2 |
| 15733 | 3 | 4 | | | IV-1 | Ltbp3 |
| 15734 | 3 | 4 | | | IV-1 | Ltbp4 |
| 15735 | 3 | 4 | | | IV-1 | Ltbr |
| 15736 | 3 | 4 | | | IV-1 | Ltn1 |
| 15737 | 3 | 4 | | | IV-1 | Ltv1 |
| 15738 | 3 | 4 | | | IV-1 | Luc7l |
| 15739 | 3 | 4 | | | IV-1 | Luc7l2 |
| 15740 | 3 | 4 | | | IV-1 | Luc7l3 |
| 15741 | 3 | 4 | | | IV-1 | Luzp2 |
| 15742 | 3 | 4 | | | IV-1 | Luzp4 |

Fig. 36 - 83

| | | | | | | |
|---|---|---|---|---|---|---|
| 15743 | 3 | 4 | | | IV-1 | Ly6c1 |
| 15744 | 3 | 4 | | | IV-1 | Ly6f |
| 15745 | 3 | 4 | | | IV-1 | Ly9 |
| 15746 | 3 | 4 | | | IV-1 | Lyn |
| 15747 | 3 | 4 | | | IV-1 | Lypd1 |
| 15748 | 3 | 4 | | | IV-1 | Lypd3 |
| 15749 | 3 | 4 | | | IV-1 | Lypd4 |
| 15750 | 3 | 4 | | | IV-1 | Lypd5 |
| 15751 | 3 | 4 | | | IV-1 | Lypd6 |
| 15752 | 3 | 4 | | | IV-1 | Lypd6b |
| 15753 | 3 | 4 | | | IV-1 | Lypla1 |
| 15754 | 3 | 4 | | | IV-1 | Lypla2 |
| 15755 | 3 | 4 | | | IV-1 | Lyplal1 |
| 15756 | 3 | 4 | | | IV-1 | Lyrm2 |
| 15757 | 3 | 4 | | | IV-1 | Lyrm5 |
| 15758 | 3 | 4 | | | IV-1 | Lyrm7 |
| 15759 | 3 | 4 | | | IV-1 | Lysmd1 |
| 15760 | 3 | 4 | | | IV-1 | Lysmd4 |
| 15761 | 3 | 4 | | | IV-1 | Lyve1 |
| 15762 | 3 | 4 | | | IV-1 | Lyzl4 |
| 15763 | 3 | 4 | | | IV-1 | Lyzl4os |
| 15764 | 3 | 4 | | | IV-1 | Lyzl6 |
| 15765 | 3 | 4 | | | IV-1 | Lztfl1 |
| 15766 | 3 | 4 | | | IV-1 | Lztr1 |
| 15767 | 3 | 4 | | | IV-1 | Lzts2 |
| 15768 | 3 | 4 | | | IV-1 | M1ap |
| 15769 | 3 | 4 | | | IV-1 | M6pr |
| 15770 | 3 | 4 | | | IV-1 | Maats1 |
| 15771 | 3 | 4 | | | IV-1 | Mab21l1 |
| 15772 | 3 | 4 | | | IV-1 | Mab21l2 |
| 15773 | 3 | 4 | | | IV-1 | Mab21l3 |
| 15774 | 3 | 4 | | | IV-1 | Macc1 |
| 15775 | 3 | 4 | | | IV-1 | Macrod2 |
| 15776 | 3 | 4 | | | IV-1 | Mad2l1 |
| 15777 | 3 | 4 | | | IV-1 | Madcam1 |
| 15778 | 3 | 4 | | | IV-1 | Maea |
| 15779 | 3 | 4 | | | IV-1 | Mael |
| 15780 | 3 | 4 | | | IV-1 | Maf1 |
| 15781 | 3 | 4 | | | IV-1 | Mafa |
| 15782 | 3 | 4 | | | IV-1 | Mag |
| 15783 | 3 | 4 | | | IV-1 | Magea10 |
| 15784 | 3 | 4 | | | IV-1 | Magea6 |
| 15785 | 3 | 4 | | | IV-1 | Mageb16 |
| 15786 | 3 | 4 | | | IV-1 | Mageb2 |
| 15787 | 3 | 4 | | | IV-1 | Mageb3 |
| 15788 | 3 | 4 | | | IV-1 | Mageb4 |
| 15789 | 3 | 4 | | | IV-1 | Mageb5 |
| 15790 | 3 | 4 | | | IV-1 | Maged1 |
| 15791 | 3 | 4 | | | IV-1 | Magee1 |
| 15792 | 3 | 4 | | | IV-1 | Magee2 |
| 15793 | 3 | 4 | | | IV-1 | Magel2 |
| 15794 | 3 | 4 | | | IV-1 | Magi1 |
| 15795 | 3 | 4 | | | IV-1 | Magi2 |
| 15796 | 3 | 4 | | | IV-1 | Magix |
| 15797 | 3 | 4 | | | IV-1 | Magt1 |
| 15798 | 3 | 4 | | | IV-1 | Mak |
| 15799 | 3 | 4 | | | IV-1 | Mak16 |
| 15800 | 3 | 4 | | | IV-1 | Maml1 |
| 15801 | 3 | 4 | | | IV-1 | Maml2 |
| 15802 | 3 | 4 | | | IV-1 | Man1a2 |
| 15803 | 3 | 4 | | | IV-1 | Man1b1 |
| 15804 | 3 | 4 | | | IV-1 | Man1c1 |
| 15805 | 3 | 4 | | | IV-1 | Man2a2 |
| 15806 | 3 | 4 | | | IV-1 | Man2c1 |
| 15807 | 3 | 4 | | | IV-1 | Manba |
| 15808 | 3 | 4 | | | IV-1 | Manea |
| 15809 | 3 | 4 | | | IV-1 | Maneal |
| 15810 | 3 | 4 | | | IV-1 | Map1s |
| 15811 | 3 | 4 | | | IV-1 | Map2 |
| 15812 | 3 | 4 | | | IV-1 | Map2k1 |
| 15813 | 3 | 4 | | | IV-1 | Map2k4 |
| 15814 | 3 | 4 | | | IV-1 | Map2k5 |
| 15815 | 3 | 4 | | | IV-1 | Map2k7 |
| 15816 | 3 | 4 | | | IV-1 | Map3k1 |
| 15817 | 3 | 4 | | | IV-1 | Map3k10 |
| 15818 | 3 | 4 | | | IV-1 | Map3k6 |
| 15819 | 3 | 4 | | | IV-1 | Map3k7 |
| 15820 | 3 | 4 | | | IV-1 | Map4 |
| 15821 | 3 | 4 | | | IV-1 | Map4k2 |
| 15822 | 3 | 4 | | | IV-1 | Map4k3 |
| 15823 | 3 | 4 | | | IV-1 | Map4k4 |
| 15824 | 3 | 4 | | | IV-1 | Map4k5 |
| 15825 | 3 | 4 | | | IV-1 | Map6 |
| 15826 | 3 | 4 | | | IV-1 | Map6d1 |
| 15827 | 3 | 4 | | | IV-1 | Map7d1 |
| 15828 | 3 | 4 | | | IV-1 | Map7d2 |
| 15829 | 3 | 4 | | | IV-1 | Map9 |
| 15830 | 3 | 4 | | | IV-1 | Mapk10 |
| 15831 | 3 | 4 | | | IV-1 | Mapk11 |
| 15832 | 3 | 4 | | | IV-1 | Mapk14 |
| 15833 | 3 | 4 | | | IV-1 | Mapk1ip1 |
| 15834 | 3 | 4 | | | IV-1 | Mapk1ip1l |
| 15835 | 3 | 4 | | | IV-1 | Mapk7 |
| 15836 | 3 | 4 | | | IV-1 | Mapk8 |
| 15837 | 3 | 4 | | | IV-1 | Mapk8ip1 |
| 15838 | 3 | 4 | | | IV-1 | Mapk8ip2 |
| 15839 | 3 | 4 | | | IV-1 | Mapk8ip3 |
| 15840 | 3 | 4 | | | IV-1 | Mapk9 |
| 15841 | 3 | 4 | | | IV-1 | Mapkap1 |
| 15842 | 3 | 4 | | | IV-1 | Mapkapk2 |
| 15843 | 3 | 4 | | | IV-1 | Mapkapk5 |
| 15844 | 3 | 4 | | | IV-1 | Mapkbp1 |
| 15845 | 3 | 4 | | | IV-1 | Mapre1 |
| 15846 | 3 | 4 | | | IV-1 | Mapre2 |
| 15847 | 3 | 4 | | | IV-1 | Marc2 |
| 15848 | 3 | 4 | | | IV-1 | March10 |
| 15849 | 3 | 4 | | | IV-1 | March11 |
| 15850 | 3 | 4 | | | IV-1 | March4 |
| 15851 | 3 | 4 | | | IV-1 | March6 |
| 15852 | 3 | 4 | | | IV-1 | Mark1 |
| 15853 | 3 | 4 | | | IV-1 | Mark2 |
| 15854 | 3 | 4 | | | IV-1 | Mark3 |
| 15855 | 3 | 4 | | | IV-1 | Mars |
| 15856 | 3 | 4 | | | IV-1 | Marveld1 |
| 15857 | 3 | 4 | | | IV-1 | Masp1 |
| 15858 | 3 | 4 | | | IV-1 | Mast1 |
| 15859 | 3 | 4 | | | IV-1 | Mast3 |
| 15860 | 3 | 4 | | | IV-1 | Mastl |
| 15861 | 3 | 4 | | | IV-1 | Matn2 |
| 15862 | 3 | 4 | | | IV-1 | Matn3 |
| 15863 | 3 | 4 | | | IV-1 | Matn4 |
| 15864 | 3 | 4 | | | IV-1 | Matr3 |
| 15865 | 3 | 4 | | | IV-1 | Mavs |
| 15866 | 3 | 4 | | | IV-1 | Max |
| 15867 | 3 | 4 | | | IV-1 | Mb21d1 |
| 15868 | 3 | 4 | | | IV-1 | Mb21d2 |
| 15869 | 3 | 4 | | | IV-1 | Mbd1 |
| 15870 | 3 | 4 | | | IV-1 | Mbd2 |
| 15871 | 3 | 4 | | | IV-1 | Mbd3 |
| 15872 | 3 | 4 | | | IV-1 | Mbd3l1 |
| 15873 | 3 | 4 | | | IV-1 | Mbd4 |
| 15874 | 3 | 4 | | | IV-1 | Mbd6 |
| 15875 | 3 | 4 | | | IV-1 | Mbl1 |
| 15876 | 3 | 4 | | | IV-1 | Mbl2 |
| 15877 | 3 | 4 | | | IV-1 | Mboat4 |
| 15878 | 3 | 4 | | | IV-1 | Mboat7 |
| 15879 | 3 | 4 | | | IV-1 | Mbp |
| 15880 | 3 | 4 | | | IV-1 | Mbtd1 |
| 15881 | 3 | 4 | | | IV-1 | Mbtps1 |
| 15882 | 3 | 4 | | | IV-1 | Mbtps2 |
| 15883 | 3 | 4 | | | IV-1 | Mc2r |
| 15884 | 3 | 4 | | | IV-1 | Mcat |
| 15885 | 3 | 4 | | | IV-1 | Mcc |
| 15886 | 3 | 4 | | | IV-1 | Mcf2l |
| 15887 | 3 | 4 | | | IV-1 | Mcfd2 |
| 15888 | 3 | 4 | | | IV-1 | Mcl1 |
| 15889 | 3 | 4 | | | IV-1 | Mcm10 |
| 15890 | 3 | 4 | | | IV-1 | Mcm4 |
| 15891 | 3 | 4 | | | IV-1 | Mcm8 |
| 15892 | 3 | 4 | | | IV-1 | Mcmbp |
| 15893 | 3 | 4 | | | IV-1 | Mcmdc2 |
| 15894 | 3 | 4 | | | IV-1 | Mcoln1 |
| 15895 | 3 | 4 | | | IV-1 | Mcoln2 |
| 15896 | 3 | 4 | | | IV-1 | Mcoln3 |
| 15897 | 3 | 4 | | | IV-1 | Mcph1 |
| 15898 | 3 | 4 | | | IV-1 | Mcpt-ps1 |
| 15899 | 3 | 4 | | | IV-1 | Mcpt8 |
| 15900 | 3 | 4 | | | IV-1 | Mctp2 |
| 15901 | 3 | 4 | | | IV-1 | Mcu |
| 15902 | 3 | 4 | | | IV-1 | Mdh1 |
| 15903 | 3 | 4 | | | IV-1 | Mdh1b |
| 15904 | 3 | 4 | | | IV-1 | Mdh2 |
| 15905 | 3 | 4 | | | IV-1 | Mdm1 |
| 15906 | 3 | 4 | | | IV-1 | Mdm2 |
| 15907 | 3 | 4 | | | IV-1 | Mdp1 |
| 15908 | 3 | 4 | | | IV-1 | Me1 |
| 15909 | 3 | 4 | | | IV-1 | Me2 |
| 15910 | 3 | 4 | | | IV-1 | Me3 |
| 15911 | 3 | 4 | | | IV-1 | Mea1 |
| 15912 | 3 | 4 | | | IV-1 | Meaf6 |
| 15913 | 3 | 4 | | | IV-1 | Mecom |
| 15914 | 3 | 4 | | | IV-1 | Med14 |
| 15915 | 3 | 4 | | | IV-1 | Med16 |
| 15916 | 3 | 4 | | | IV-1 | Med17 |
| 15917 | 3 | 4 | | | IV-1 | Med22 |
| 15918 | 3 | 4 | | | IV-1 | Med23 |
| 15919 | 3 | 4 | | | IV-1 | Med24 |
| 15920 | 3 | 4 | | | IV-1 | Med25 |
| 15921 | 3 | 4 | | | IV-1 | Med26 |
| 15922 | 3 | 4 | | | IV-1 | Med30 |
| 15923 | 3 | 4 | | | IV-1 | Med4 |
| 15924 | 3 | 4 | | | IV-1 | Med7 |
| 15925 | 3 | 4 | | | IV-1 | Med9 |
| 15926 | 3 | 4 | | | IV-1 | Medag |
| 15927 | 3 | 4 | | | IV-1 | Mef2b |
| 15928 | 3 | 4 | | | IV-1 | Megf10 |
| 15929 | 3 | 4 | | | IV-1 | Megf6 |
| 15930 | 3 | 4 | | | IV-1 | Megf8 |
| 15931 | 3 | 4 | | | IV-1 | Meiob |
| 15932 | 3 | 4 | | | IV-1 | Meis1 |
| 15933 | 3 | 4 | | | IV-1 | Meis2 |
| 15934 | 3 | 4 | | | IV-1 | Meik |

Fig. 36 - 84

| | | | | | | |
|---|---|---|---|---|---|---|
| 15935 | 3 | 4 | | | IV-1 | Men1 |
| 15936 | 3 | 4 | | | IV-1 | Meox1 |
| 15937 | 3 | 4 | | | IV-1 | Meox2 |
| 15938 | 3 | 4 | | | IV-1 | Mep1a |
| 15939 | 3 | 4 | | | IV-1 | Mepce |
| 15940 | 3 | 4 | | | IV-1 | Mesdc2 |
| 15941 | 3 | 4 | | | IV-1 | Mesp2 |
| 15942 | 3 | 4 | | | IV-1 | Metap1 |
| 15943 | 3 | 4 | | | IV-1 | Metrnl |
| 15944 | 3 | 4 | | | IV-1 | Mettl11b |
| 15945 | 3 | 4 | | | IV-1 | Mettl14 |
| 15946 | 3 | 4 | | | IV-1 | Mettl16 |
| 15947 | 3 | 4 | | | IV-1 | Mettl2 |
| 15948 | 3 | 4 | | | IV-1 | Mettl21a |
| 15949 | 3 | 4 | | | IV-1 | Mettl21c |
| 15950 | 3 | 4 | | | IV-1 | Mettl21e |
| 15951 | 3 | 4 | | | IV-1 | Mettl23 |
| 15952 | 3 | 4 | | | IV-1 | Mettl25 |
| 15953 | 3 | 4 | | | IV-1 | Mettl7a1 |
| 15954 | 3 | 4 | | | IV-1 | Mettl8 |
| 15955 | 3 | 4 | | | IV-1 | Mettl9 |
| 15956 | 3 | 4 | | | IV-1 | Mex3c |
| 15957 | 3 | 4 | | | IV-1 | Mfhas1 |
| 15958 | 3 | 4 | | | IV-1 | Mfi2 |
| 15959 | 3 | 4 | | | IV-1 | Mfn1 |
| 15960 | 3 | 4 | | | IV-1 | Mfn2 |
| 15961 | 3 | 4 | | | IV-1 | Mfng |
| 15962 | 3 | 4 | | | IV-1 | Mfsd1 |
| 15963 | 3 | 4 | | | IV-1 | Mfsd10 |
| 15964 | 3 | 4 | | | IV-1 | Mfsd11 |
| 15965 | 3 | 4 | | | IV-1 | Mfsd6 |
| 15966 | 3 | 4 | | | IV-1 | Mfsd7b |
| 15967 | 3 | 4 | | | IV-1 | Mfsd8 |
| 15968 | 3 | 4 | | | IV-1 | Mfsd9 |
| 15969 | 3 | 4 | | | IV-1 | Mgat4a |
| 15970 | 3 | 4 | | | IV-1 | Mgat4b |
| 15971 | 3 | 4 | | | IV-1 | Mgat4c |
| 15972 | 3 | 4 | | | IV-1 | Mgat5b |
| 15973 | 3 | 4 | | | IV-1 | Mgea5 |
| 15974 | 3 | 4 | | | IV-1 | Mgme1 |
| 15975 | 3 | 4 | | | IV-1 | Mgrn1 |
| 15976 | 3 | 4 | | | IV-1 | Mib2 |
| 15977 | 3 | 4 | | | IV-1 | Mical1 |
| 15978 | 3 | 4 | | | IV-1 | Mical2 |
| 15979 | 3 | 4 | | | IV-1 | Mical3 |
| 15980 | 3 | 4 | | | IV-1 | Micalcl |
| 15981 | 3 | 4 | | | IV-1 | Micu2 |
| 15982 | 3 | 4 | | | IV-1 | Micu3 |
| 15983 | 3 | 4 | | | IV-1 | Mief1 |
| 15984 | 3 | 4 | | | IV-1 | Mief2 |
| 15985 | 3 | 4 | | | IV-1 | Mier1 |
| 15986 | 3 | 4 | | | IV-1 | Mier2 |
| 15987 | 3 | 4 | | | IV-1 | Mier3 |
| 15988 | 3 | 4 | | | IV-1 | Mill1 |
| 15989 | 3 | 4 | | | IV-1 | Mill2 |
| 15990 | 3 | 4 | | | IV-1 | Mina |
| 15991 | 3 | 4 | | | IV-1 | Minpp1 |
| 15992 | 3 | 4 | | | IV-1 | Mios |
| 15993 | 3 | 4 | | | IV-1 | Miox |
| 15994 | 3 | 4 | | | IV-1 | Mipep |
| 15995 | 3 | 4 | | | IV-1 | Mkks |
| 15996 | 3 | 4 | | | IV-1 | Mki1 |
| 15997 | 3 | 4 | | | IV-1 | Mki2 |
| 15998 | 3 | 4 | | | IV-1 | Mknk1 |
| 15999 | 3 | 4 | | | IV-1 | Mknk2 |
| 16000 | 3 | 4 | | | IV-1 | Mkrn2 |
| 16001 | 3 | 4 | | | IV-1 | Mks1 |
| 16002 | 3 | 4 | | | IV-1 | Mkx |
| 16003 | 3 | 4 | | | IV-1 | Mlc1 |
| 16004 | 3 | 4 | | | IV-1 | Mlf2 |
| 16005 | 3 | 4 | | | IV-1 | Mlh1 |
| 16006 | 3 | 4 | | | IV-1 | Mlip |
| 16007 | 3 | 4 | | | IV-1 | Mllt11 |
| 16008 | 3 | 4 | | | IV-1 | Mllt4 |
| 16009 | 3 | 4 | | | IV-1 | Mllt6 |
| 16010 | 3 | 4 | | | IV-1 | Mlst8 |
| 16011 | 3 | 4 | | | IV-1 | Mlx |
| 16012 | 3 | 4 | | | IV-1 | Mlxipl |
| 16013 | 3 | 4 | | | IV-1 | Mlycd |
| 16014 | 3 | 4 | | | IV-1 | Mmaa |
| 16015 | 3 | 4 | | | IV-1 | Mmab |
| 16016 | 3 | 4 | | | IV-1 | Mmachc |
| 16017 | 3 | 4 | | | IV-1 | Mmel1 |
| 16018 | 3 | 4 | | | IV-1 | Mmgt1 |
| 16019 | 3 | 4 | | | IV-1 | Mmp15 |
| 16020 | 3 | 4 | | | IV-1 | Mmp23 |
| 16021 | 3 | 4 | | | IV-1 | Mmp24 |
| 16022 | 3 | 4 | | | IV-1 | Mmp27 |
| 16023 | 3 | 4 | | | IV-1 | Mmrn2 |
| 16024 | 3 | 4 | | | IV-1 | Mms19 |
| 16025 | 3 | 4 | | | IV-1 | Mn1 |
| 16026 | 3 | 4 | | | IV-1 | Mnx1 |
| 16027 | 3 | 4 | | | IV-1 | Mob3b |
| 16028 | 3 | 4 | | | IV-1 | Mob3c |
| 16029 | 3 | 4 | | | IV-1 | Mob4 |
| 16030 | 3 | 4 | | | IV-1 | Mobp |
| 16031 | 3 | 4 | | | IV-1 | Mocs2 |
| 16032 | 3 | 4 | | | IV-1 | Mog |
| 16033 | 3 | 4 | | | IV-1 | Mogs |
| 16034 | 3 | 4 | | | IV-1 | Mon1a |
| 16035 | 3 | 4 | | | IV-1 | Mon1b |
| 16036 | 3 | 4 | | | IV-1 | Mon2 |
| 16037 | 3 | 4 | | | IV-1 | Morc1 |
| 16038 | 3 | 4 | | | IV-1 | Morc2a |
| 16039 | 3 | 4 | | | IV-1 | Morc2b |
| 16040 | 3 | 4 | | | IV-1 | Morc4 |
| 16041 | 3 | 4 | | | IV-1 | Morf4l1 |
| 16042 | 3 | 4 | | | IV-1 | Morn4 |
| 16043 | 3 | 4 | | | IV-1 | Mos |
| 16044 | 3 | 4 | | | IV-1 | Mospd1 |
| 16045 | 3 | 4 | | | IV-1 | Mospd4 |
| 16046 | 3 | 4 | | | IV-1 | Moxd1 |
| 16047 | 3 | 4 | | | IV-1 | Mpdz |
| 16048 | 3 | 4 | | | IV-1 | Mpg |
| 16049 | 3 | 4 | | | IV-1 | Mphosph10 |
| 16050 | 3 | 4 | | | IV-1 | Mphosph8 |
| 16051 | 3 | 4 | | | IV-1 | Mphosph9 |
| 16052 | 3 | 4 | | | IV-1 | Mpi |
| 16053 | 3 | 4 | | | IV-1 | Mpikip |
| 16054 | 3 | 4 | | | IV-1 | Mpp2 |
| 16055 | 3 | 4 | | | IV-1 | Mpp4 |
| 16056 | 3 | 4 | | | IV-1 | Mpp6 |
| 16057 | 3 | 4 | | | IV-1 | Mppe1 |
| 16058 | 3 | 4 | | | IV-1 | Mpped1 |
| 16059 | 3 | 4 | | | IV-1 | Mpped2 |
| 16060 | 3 | 4 | | | IV-1 | Mprip |
| 16061 | 3 | 4 | | | IV-1 | Mpv17 |
| 16062 | 3 | 4 | | | IV-1 | Mpv17l |
| 16063 | 3 | 4 | | | IV-1 | Mpv17l2 |
| 16064 | 3 | 4 | | | IV-1 | Mpzl1 |
| 16065 | 3 | 4 | | | IV-1 | Mrap2 |
| 16066 | 3 | 4 | | | IV-1 | Mrc1 |
| 16067 | 3 | 4 | | | IV-1 | Mrc2 |
| 16068 | 3 | 4 | | | IV-1 | Mreg |
| 16069 | 3 | 4 | | | IV-1 | Mrfap1 |
| 16070 | 3 | 4 | | | IV-1 | Mrgprb1 |
| 16071 | 3 | 4 | | | IV-1 | Mrgprb8 |
| 16072 | 3 | 4 | | | IV-1 | Mrgpre |
| 16073 | 3 | 4 | | | IV-1 | Mrgprf |
| 16074 | 3 | 4 | | | IV-1 | Mrgprx2 |
| 16075 | 3 | 4 | | | IV-1 | Mrm1 |
| 16076 | 3 | 4 | | | IV-1 | Mro |
| 16077 | 3 | 4 | | | IV-1 | Mroh6 |
| 16078 | 3 | 4 | | | IV-1 | Mroh7 |
| 16079 | 3 | 4 | | | IV-1 | Mroh9 |
| 16080 | 3 | 4 | | | IV-1 | Mrpl1 |
| 16081 | 3 | 4 | | | IV-1 | Mrpl10 |
| 16082 | 3 | 4 | | | IV-1 | Mrpl11 |
| 16083 | 3 | 4 | | | IV-1 | Mrpl16 |
| 16084 | 3 | 4 | | | IV-1 | Mrpl17 |
| 16085 | 3 | 4 | | | IV-1 | Mrpl19 |
| 16086 | 3 | 4 | | | IV-1 | Mrpl28 |
| 16087 | 3 | 4 | | | IV-1 | Mrpl32 |
| 16088 | 3 | 4 | | | IV-1 | Mrpl34 |
| 16089 | 3 | 4 | | | IV-1 | Mrpl35 |
| 16090 | 3 | 4 | | | IV-1 | Mrpl39 |
| 16091 | 3 | 4 | | | IV-1 | Mrpl42 |
| 16092 | 3 | 4 | | | IV-1 | Mrpl44 |
| 16093 | 3 | 4 | | | IV-1 | Mrpl49 |
| 16094 | 3 | 4 | | | IV-1 | Mrpl50 |
| 16095 | 3 | 4 | | | IV-1 | Mrpl57 |
| 16096 | 3 | 4 | | | IV-1 | Mrpl9 |
| 16097 | 3 | 4 | | | IV-1 | Mrps11 |
| 16098 | 3 | 4 | | | IV-1 | Mrps14 |
| 16099 | 3 | 4 | | | IV-1 | Mrps17 |
| 16100 | 3 | 4 | | | IV-1 | Mrps2 |
| 16101 | 3 | 4 | | | IV-1 | Mrps26 |
| 16102 | 3 | 4 | | | IV-1 | Mrps27 |
| 16103 | 3 | 4 | | | IV-1 | Mrps30 |
| 16104 | 3 | 4 | | | IV-1 | Mrps31 |
| 16105 | 3 | 4 | | | IV-1 | Mrps34 |
| 16106 | 3 | 4 | | | IV-1 | Mrps5 |
| 16107 | 3 | 4 | | | IV-1 | Mrps9 |
| 16108 | 3 | 4 | | | IV-1 | Ms4a10 |
| 16109 | 3 | 4 | | | IV-1 | Ms4a13 |
| 16110 | 3 | 4 | | | IV-1 | Ms4a18 |
| 16111 | 3 | 4 | | | IV-1 | Ms4a2 |
| 16112 | 3 | 4 | | | IV-1 | Ms4a5 |
| 16113 | 3 | 4 | | | IV-1 | Ms4a7 |
| 16114 | 3 | 4 | | | IV-1 | Msantd1 |
| 16115 | 3 | 4 | | | IV-1 | Msantd2 |
| 16116 | 3 | 4 | | | IV-1 | Msantd4 |
| 16117 | 3 | 4 | | | IV-1 | Msh3 |
| 16118 | 3 | 4 | | | IV-1 | Msh4 |
| 16119 | 3 | 4 | | | IV-1 | Msh5 |
| 16120 | 3 | 4 | | | IV-1 | Msi2 |
| 16121 | 3 | 4 | | | IV-1 | Msl1 |
| 16122 | 3 | 4 | | | IV-1 | Msl2 |
| 16123 | 3 | 4 | | | IV-1 | Msl3 |
| 16124 | 3 | 4 | | | IV-1 | Msmp |
| 16125 | 3 | 4 | | | IV-1 | Msn |
| 16126 | 3 | 4 | | | IV-1 | Msrb1 |

Fig. 36 - 85

| | | | | | | |
|---|---|---|---|---|---|---|
| 16127 | 3 | 4 | | | IV-1 | Msrb3 |
| 16128 | 3 | 4 | | | IV-1 | Mst1 |
| 16129 | 3 | 4 | | | IV-1 | Mstn |
| 16130 | 3 | 4 | | | IV-1 | Msx1 |
| 16131 | 3 | 4 | | | IV-1 | Mta1 |
| 16132 | 3 | 4 | | | IV-1 | Mta2 |
| 16133 | 3 | 4 | | | IV-1 | Mtag2 |
| 16134 | 3 | 4 | | | IV-1 | Mtap |
| 16135 | 3 | 4 | | | IV-1 | Mtap7d3 |
| 16136 | 3 | 4 | | | IV-1 | Mtch1 |
| 16137 | 3 | 4 | | | IV-1 | Mterf1a |
| 16138 | 3 | 4 | | | IV-1 | Mterfd2 |
| 16139 | 3 | 4 | | | IV-1 | Mtf1 |
| 16140 | 3 | 4 | | | IV-1 | Mtfr1 |
| 16141 | 3 | 4 | | | IV-1 | Mtfr1l |
| 16142 | 3 | 4 | | | IV-1 | Mtg2 |
| 16143 | 3 | 4 | | | IV-1 | Mthfd1l |
| 16144 | 3 | 4 | | | IV-1 | Mthfsd |
| 16145 | 3 | 4 | | | IV-1 | Mtif3 |
| 16146 | 3 | 4 | | | IV-1 | Mtl5 |
| 16147 | 3 | 4 | | | IV-1 | Mtm1 |
| 16148 | 3 | 4 | | | IV-1 | Mtmr11 |
| 16149 | 3 | 4 | | | IV-1 | Mtmr12 |
| 16150 | 3 | 4 | | | IV-1 | Mtmr2 |
| 16151 | 3 | 4 | | | IV-1 | Mtmr4 |
| 16152 | 3 | 4 | | | IV-1 | Mtmr6 |
| 16153 | 3 | 4 | | | IV-1 | Mtnr1a |
| 16154 | 3 | 4 | | | IV-1 | Mto1 |
| 16155 | 3 | 4 | | | IV-1 | Mtor |
| 16156 | 3 | 4 | | | IV-1 | Mtpap |
| 16157 | 3 | 4 | | | IV-1 | Mtpn |
| 16158 | 3 | 4 | | | IV-1 | Mtrf1 |
| 16159 | 3 | 4 | | | IV-1 | Mtrf1l |
| 16160 | 3 | 4 | | | IV-1 | Mtrr |
| 16161 | 3 | 4 | | | IV-1 | Mtss1l |
| 16162 | 3 | 4 | | | IV-1 | Mturn |
| 16163 | 3 | 4 | | | IV-1 | Mtus2 |
| 16164 | 3 | 4 | | | IV-1 | Mtx1 |
| 16165 | 3 | 4 | | | IV-1 | Mtx3 |
| 16166 | 3 | 4 | | | IV-1 | Muc20 |
| 16167 | 3 | 4 | | | IV-1 | Muc5ac |
| 16168 | 3 | 4 | | | IV-1 | Muc6 |
| 16169 | 3 | 4 | | | IV-1 | Mug-ps1 |
| 16170 | 3 | 4 | | | IV-1 | Mug2 |
| 16171 | 3 | 4 | | | IV-1 | Mul1 |
| 16172 | 3 | 4 | | | IV-1 | Mum1 |
| 16173 | 3 | 4 | | | IV-1 | Mup16 |
| 16174 | 3 | 4 | | | IV-1 | Mup21 |
| 16175 | 3 | 4 | | | IV-1 | Mup5 |
| 16176 | 3 | 4 | | | IV-1 | Mut |
| 16177 | 3 | 4 | | | IV-1 | Mxd3 |
| 16178 | 3 | 4 | | | IV-1 | Mxra7 |
| 16179 | 3 | 4 | | | IV-1 | Myadml2 |
| 16180 | 3 | 4 | | | IV-1 | Myb |
| 16181 | 3 | 4 | | | IV-1 | Mybbp1a |
| 16182 | 3 | 4 | | | IV-1 | Mybl2 |
| 16183 | 3 | 4 | | | IV-1 | Mybpc3 |
| 16184 | 3 | 4 | | | IV-1 | Mybph |
| 16185 | 3 | 4 | | | IV-1 | Mybphl |
| 16186 | 3 | 4 | | | IV-1 | Mychpap |
| 16187 | 3 | 4 | | | IV-1 | Myd88 |
| 16188 | 3 | 4 | | | IV-1 | Myef2 |
| 16189 | 3 | 4 | | | IV-1 | Myg1 |
| 16190 | 3 | 4 | | | IV-1 | Myh10 |
| 16191 | 3 | 4 | | | IV-1 | Myh11 |
| 16192 | 3 | 4 | | | IV-1 | Myh14 |
| 16193 | 3 | 4 | | | IV-1 | Myh15 |
| 16194 | 3 | 4 | | | IV-1 | Myh7b |
| 16195 | 3 | 4 | | | IV-1 | Myl12b |
| 16196 | 3 | 4 | | | IV-1 | Mynn |
| 16197 | 3 | 4 | | | IV-1 | Myo10 |
| 16198 | 3 | 4 | | | IV-1 | Myo15 |
| 16199 | 3 | 4 | | | IV-1 | Myo18a |
| 16200 | 3 | 4 | | | IV-1 | Myo18b |
| 16201 | 3 | 4 | | | IV-1 | Myo19 |
| 16202 | 3 | 4 | | | IV-1 | Myo1b |
| 16203 | 3 | 4 | | | IV-1 | Myo1d |
| 16204 | 3 | 4 | | | IV-1 | Myo1e |
| 16205 | 3 | 4 | | | IV-1 | Myo1f |
| 16206 | 3 | 4 | | | IV-1 | Myo1h |
| 16207 | 3 | 4 | | | IV-1 | Myo3b |
| 16208 | 3 | 4 | | | IV-1 | Myo5a |
| 16209 | 3 | 4 | | | IV-1 | Myo5c |
| 16210 | 3 | 4 | | | IV-1 | Myo6 |
| 16211 | 3 | 4 | | | IV-1 | Myo7a |
| 16212 | 3 | 4 | | | IV-1 | Myo7b |
| 16213 | 3 | 4 | | | IV-1 | Myo9b |
| 16214 | 3 | 4 | | | IV-1 | Myoz3 |
| 16215 | 3 | 4 | | | IV-1 | Mypop |
| 16216 | 3 | 4 | | | IV-1 | Myrf |
| 16217 | 3 | 4 | | | IV-1 | Myt1 |
| 16218 | 3 | 4 | | | IV-1 | Myt1l |
| 16219 | 3 | 4 | | | IV-1 | Myzap |
| 16220 | 3 | 4 | | | IV-1 | Mzf1 |
| 16221 | 3 | 4 | | | IV-1 | N4bp3 |
| 16222 | 3 | 4 | | | IV-1 | N6amt1 |
| 16223 | 3 | 4 | | | IV-1 | Naa15 |
| 16224 | 3 | 4 | | | IV-1 | Naa16 |
| 16225 | 3 | 4 | | | IV-1 | Naa30 |
| 16226 | 3 | 4 | | | IV-1 | Naa35 |
| 16227 | 3 | 4 | | | IV-1 | Naa40 |
| 16228 | 3 | 4 | | | IV-1 | Naa50 |
| 16229 | 3 | 4 | | | IV-1 | Naa60 |
| 16230 | 3 | 4 | | | IV-1 | Naaa |
| 16231 | 3 | 4 | | | IV-1 | Nab1 |
| 16232 | 3 | 4 | | | IV-1 | Nabp2 |
| 16233 | 3 | 4 | | | IV-1 | Nacc1 |
| 16234 | 3 | 4 | | | IV-1 | Nacc2 |
| 16235 | 3 | 4 | | | IV-1 | Nadsyn1 |
| 16236 | 3 | 4 | | | IV-1 | Naf1 |
| 16237 | 3 | 4 | | | IV-1 | Naga |
| 16238 | 3 | 4 | | | IV-1 | Naglu |
| 16239 | 3 | 4 | | | IV-1 | Nags |
| 16240 | 3 | 4 | | | IV-1 | Naip5 |
| 16241 | 3 | 4 | | | IV-1 | Nalcn |
| 16242 | 3 | 4 | | | IV-1 | Nampt |
| 16243 | 3 | 4 | | | IV-1 | Nanos1 |
| 16244 | 3 | 4 | | | IV-1 | Nanos2 |
| 16245 | 3 | 4 | | | IV-1 | Napll1 |
| 16246 | 3 | 4 | | | IV-1 | Napll4 |
| 16247 | 3 | 4 | | | IV-1 | Napepld |
| 16248 | 3 | 4 | | | IV-1 | Napg |
| 16249 | 3 | 4 | | | IV-1 | Naprt1 |
| 16250 | 3 | 4 | | | IV-1 | Narfl |
| 16251 | 3 | 4 | | | IV-1 | Nars |
| 16252 | 3 | 4 | | | IV-1 | Nars2 |
| 16253 | 3 | 4 | | | IV-1 | Nasp |
| 16254 | 3 | 4 | | | IV-1 | Nat10 |
| 16255 | 3 | 4 | | | IV-1 | Nat8l |
| 16256 | 3 | 4 | | | IV-1 | Nbea |
| 16257 | 3 | 4 | | | IV-1 | Nbn |
| 16258 | 3 | 4 | | | IV-1 | Nbr1 |
| 16259 | 3 | 4 | | | IV-1 | Ncan |
| 16260 | 3 | 4 | | | IV-1 | Ncapd2 |
| 16261 | 3 | 4 | | | IV-1 | Ncapd3 |
| 16262 | 3 | 4 | | | IV-1 | Ncapg |
| 16263 | 3 | 4 | | | IV-1 | Ncdn |
| 16264 | 3 | 4 | | | IV-1 | Nckap5 |
| 16265 | 3 | 4 | | | IV-1 | Nckap5l |
| 16266 | 3 | 4 | | | IV-1 | Ncl |
| 16267 | 3 | 4 | | | IV-1 | Ncln |
| 16268 | 3 | 4 | | | IV-1 | Ncoa1 |
| 16269 | 3 | 4 | | | IV-1 | Ncoa5 |
| 16270 | 3 | 4 | | | IV-1 | Ncr1 |
| 16271 | 3 | 4 | | | IV-1 | Ncs1 |
| 16272 | 3 | 4 | | | IV-1 | Ncstn |
| 16273 | 3 | 4 | | | IV-1 | Nctc1 |
| 16274 | 3 | 4 | | | IV-1 | Nde1 |
| 16275 | 3 | 4 | | | IV-1 | Ndfip2 |
| 16276 | 3 | 4 | | | IV-1 | Ndn |
| 16277 | 3 | 4 | | | IV-1 | Ndnl2 |
| 16278 | 3 | 4 | | | IV-1 | Ndor1 |
| 16279 | 3 | 4 | | | IV-1 | Ndp |
| 16280 | 3 | 4 | | | IV-1 | Ndrg4 |
| 16281 | 3 | 4 | | | IV-1 | Ndst3 |
| 16282 | 3 | 4 | | | IV-1 | Ndufa10 |
| 16283 | 3 | 4 | | | IV-1 | Ndufaf1 |
| 16284 | 3 | 4 | | | IV-1 | Ndufaf7 |
| 16285 | 3 | 4 | | | IV-1 | Ndufs1 |
| 16286 | 3 | 4 | | | IV-1 | Ndufs2 |
| 16287 | 3 | 4 | | | IV-1 | Ndufv1 |
| 16288 | 3 | 4 | | | IV-1 | Neb |
| 16289 | 3 | 4 | | | IV-1 | Necab1 |
| 16290 | 3 | 4 | | | IV-1 | Necab3 |
| 16291 | 3 | 4 | | | IV-1 | Necap1 |
| 16292 | 3 | 4 | | | IV-1 | Nedd1 |
| 16293 | 3 | 4 | | | IV-1 | Nedd4 |
| 16294 | 3 | 4 | | | IV-1 | Nedd4l |
| 16295 | 3 | 4 | | | IV-1 | Nefm |
| 16296 | 3 | 4 | | | IV-1 | Negr1 |
| 16297 | 3 | 4 | | | IV-1 | Nek11 |
| 16298 | 3 | 4 | | | IV-1 | Nek3 |
| 16299 | 3 | 4 | | | IV-1 | Nek5 |
| 16300 | 3 | 4 | | | IV-1 | Nek8 |
| 16301 | 3 | 4 | | | IV-1 | Nek9 |
| 16302 | 3 | 4 | | | IV-1 | Nelfb |
| 16303 | 3 | 4 | | | IV-1 | Nell1 |
| 16304 | 3 | 4 | | | IV-1 | Nell2 |
| 16305 | 3 | 4 | | | IV-1 | Nemf |
| 16306 | 3 | 4 | | | IV-1 | Neo1 |
| 16307 | 3 | 4 | | | IV-1 | Nespas |
| 16308 | 3 | 4 | | | IV-1 | Neto1 |
| 16309 | 3 | 4 | | | IV-1 | Neto2 |
| 16310 | 3 | 4 | | | IV-1 | Neu1 |
| 16311 | 3 | 4 | | | IV-1 | Neu3 |
| 16312 | 3 | 4 | | | IV-1 | Neu4 |
| 16313 | 3 | 4 | | | IV-1 | Neurl1a |
| 16314 | 3 | 4 | | | IV-1 | Neurl4 |
| 16315 | 3 | 4 | | | IV-1 | Neurod1 |
| 16316 | 3 | 4 | | | IV-1 | Neurod2 |
| 16317 | 3 | 4 | | | IV-1 | Neurod6 |
| 16318 | 3 | 4 | | | IV-1 | Neurog2 |

Fig. 36 - 86

| | | | | | | |
|---|---|---|---|---|---|---|
| 16319 | 3 | 4 | | | IV-1 | Neurog3 |
| 16320 | 3 | 4 | | | IV-1 | Nf1 |
| 16321 | 3 | 4 | | | IV-1 | Nf2 |
| 16322 | 3 | 4 | | | IV-1 | Nfasc |
| 16323 | 3 | 4 | | | IV-1 | Nfatc1 |
| 16324 | 3 | 4 | | | IV-1 | Nfatc2 |
| 16325 | 3 | 4 | | | IV-1 | Nfatc3 |
| 16326 | 3 | 4 | | | IV-1 | Nfatc4 |
| 16327 | 3 | 4 | | | IV-1 | Nfe2l1 |
| 16328 | 3 | 4 | | | IV-1 | Nfe2l2 |
| 16329 | 3 | 4 | | | IV-1 | Nfia |
| 16330 | 3 | 4 | | | IV-1 | Nfib |
| 16331 | 3 | 4 | | | IV-1 | Nfix |
| 16332 | 3 | 4 | | | IV-1 | Nfkb1 |
| 16333 | 3 | 4 | | | IV-1 | Nfkb2 |
| 16334 | 3 | 4 | | | IV-1 | Nfkbia |
| 16335 | 3 | 4 | | | IV-1 | Nfrkb |
| 16336 | 3 | 4 | | | IV-1 | Nfx1 |
| 16337 | 3 | 4 | | | IV-1 | Nfya |
| 16338 | 3 | 4 | | | IV-1 | Nfyb |
| 16339 | 3 | 4 | | | IV-1 | Nfyc |
| 16340 | 3 | 4 | | | IV-1 | Ngly1 |
| 16341 | 3 | 4 | | | IV-1 | Ngrn |
| 16342 | 3 | 4 | | | IV-1 | Nhlh1 |
| 16343 | 3 | 4 | | | IV-1 | Nhlh2 |
| 16344 | 3 | 4 | | | IV-1 | Nhp2l1 |
| 16345 | 3 | 4 | | | IV-1 | Nif3l1 |
| 16346 | 3 | 4 | | | IV-1 | Nifk |
| 16347 | 3 | 4 | | | IV-1 | Ninl |
| 16348 | 3 | 4 | | | IV-1 | Nipa2 |
| 16349 | 3 | 4 | | | IV-1 | Nipal2 |
| 16350 | 3 | 4 | | | IV-1 | Nipal4 |
| 16351 | 3 | 4 | | | IV-1 | Nipsnap3a |
| 16352 | 3 | 4 | | | IV-1 | Nisch |
| 16353 | 3 | 4 | | | IV-1 | Nkain1 |
| 16354 | 3 | 4 | | | IV-1 | Nkain2 |
| 16355 | 3 | 4 | | | IV-1 | Nkain3 |
| 16356 | 3 | 4 | | | IV-1 | Nkap |
| 16357 | 3 | 4 | | | IV-1 | Nkiras1 |
| 16358 | 3 | 4 | | | IV-1 | Nkiras2 |
| 16359 | 3 | 4 | | | IV-1 | Nkrf |
| 16360 | 3 | 4 | | | IV-1 | Nkx2-1 |
| 16361 | 3 | 4 | | | IV-1 | Nkx2-3 |
| 16362 | 3 | 4 | | | IV-1 | Nkx2-5 |
| 16363 | 3 | 4 | | | IV-1 | Nkx3-1 |
| 16364 | 3 | 4 | | | IV-1 | Nkx6-1 |
| 16365 | 3 | 4 | | | IV-1 | Nkx6-2 |
| 16366 | 3 | 4 | | | IV-1 | Nkx6-3 |
| 16367 | 3 | 4 | | | IV-1 | Nlgn1 |
| 16368 | 3 | 4 | | | IV-1 | Nln |
| 16369 | 3 | 4 | | | IV-1 | Nlrc3 |
| 16370 | 3 | 4 | | | IV-1 | Nlrp10 |
| 16371 | 3 | 4 | | | IV-1 | Nlrp14 |
| 16372 | 3 | 4 | | | IV-1 | Nlrp1a |
| 16373 | 3 | 4 | | | IV-1 | Nlrp4c |
| 16374 | 3 | 4 | | | IV-1 | Nlrp5-ps |
| 16375 | 3 | 4 | | | IV-1 | Nlrp9b |
| 16376 | 3 | 4 | | | IV-1 | Nmbr |
| 16377 | 3 | 4 | | | IV-1 | Nmd3 |
| 16378 | 3 | 4 | | | IV-1 | Nme8 |
| 16379 | 3 | 4 | | | IV-1 | Nme9 |
| 16380 | 3 | 4 | | | IV-1 | Nmnat2 |
| 16381 | 3 | 4 | | | IV-1 | Nmt1 |
| 16382 | 3 | 4 | | | IV-1 | Nmt2 |
| 16383 | 3 | 4 | | | IV-1 | Nmu |
| 16384 | 3 | 4 | | | IV-1 | Nmur1 |
| 16385 | 3 | 4 | | | IV-1 | Nnt |
| 16386 | 3 | 4 | | | IV-1 | Noa1 |
| 16387 | 3 | 4 | | | IV-1 | Nob1 |
| 16388 | 3 | 4 | | | IV-1 | Noc3l |
| 16389 | 3 | 4 | | | IV-1 | Noc4l |
| 16390 | 3 | 4 | | | IV-1 | Nod1 |
| 16391 | 3 | 4 | | | IV-1 | Nol10 |
| 16392 | 3 | 4 | | | IV-1 | Nol11 |
| 16393 | 3 | 4 | | | IV-1 | Nol12 |
| 16394 | 3 | 4 | | | IV-1 | Nol3 |
| 16395 | 3 | 4 | | | IV-1 | Nol4 |
| 16396 | 3 | 4 | | | IV-1 | Nol6 |
| 16397 | 3 | 4 | | | IV-1 | Nol9 |
| 16398 | 3 | 4 | | | IV-1 | Nom1 |
| 16399 | 3 | 4 | | | IV-1 | Nop14 |
| 16400 | 3 | 4 | | | IV-1 | Nop56 |
| 16401 | 3 | 4 | | | IV-1 | Nop58 |
| 16402 | 3 | 4 | | | IV-1 | Nop9 |
| 16403 | 3 | 4 | | | IV-1 | Nosip |
| 16404 | 3 | 4 | | | IV-1 | Notch1 |
| 16405 | 3 | 4 | | | IV-1 | Nova1 |
| 16406 | 3 | 4 | | | IV-1 | Nova2 |
| 16407 | 3 | 4 | | | IV-1 | Nox1 |
| 16408 | 3 | 4 | | | IV-1 | Noxo1 |
| 16409 | 3 | 4 | | | IV-1 | Npas1 |
| 16410 | 3 | 4 | | | IV-1 | Npas3 |
| 16411 | 3 | 4 | | | IV-1 | Npc1 |
| 16412 | 3 | 4 | | | IV-1 | Npc2 |
| 16413 | 3 | 4 | | | IV-1 | Npepl1 |
| 16414 | 3 | 4 | | | IV-1 | Npepps |
| 16415 | 3 | 4 | | | IV-1 | Nphp1 |
| 16416 | 3 | 4 | | | IV-1 | Nphp3 |
| 16417 | 3 | 4 | | | IV-1 | Nphp4 |
| 16418 | 3 | 4 | | | IV-1 | Nphs1 |
| 16419 | 3 | 4 | | | IV-1 | Nphs2 |
| 16420 | 3 | 4 | | | IV-1 | Nploc4 |
| 16421 | 3 | 4 | | | IV-1 | Npm1 |
| 16422 | 3 | 4 | | | IV-1 | Npm3-ps1 |
| 16423 | 3 | 4 | | | IV-1 | Nppc |
| 16424 | 3 | 4 | | | IV-1 | Npr1 |
| 16425 | 3 | 4 | | | IV-1 | Npsr1 |
| 16426 | 3 | 4 | | | IV-1 | Nptn |
| 16427 | 3 | 4 | | | IV-1 | Nptx1 |
| 16428 | 3 | 4 | | | IV-1 | Nptx2 |
| 16429 | 3 | 4 | | | IV-1 | Npy2r |
| 16430 | 3 | 4 | | | IV-1 | Nr0b1 |
| 16431 | 3 | 4 | | | IV-1 | Nr1h4 |
| 16432 | 3 | 4 | | | IV-1 | Nr1h5 |
| 16433 | 3 | 4 | | | IV-1 | Nr1i2 |
| 16434 | 3 | 4 | | | IV-1 | Nr2c1 |
| 16435 | 3 | 4 | | | IV-1 | Nr2e1 |
| 16436 | 3 | 4 | | | IV-1 | Nr2f1 |
| 16437 | 3 | 4 | | | IV-1 | Nr2f2 |
| 16438 | 3 | 4 | | | IV-1 | Nr2f6 |
| 16439 | 3 | 4 | | | IV-1 | Nr5a1 |
| 16440 | 3 | 4 | | | IV-1 | Nras |
| 16441 | 3 | 4 | | | IV-1 | Nrbf2 |
| 16442 | 3 | 4 | | | IV-1 | Nrbp1 |
| 16443 | 3 | 4 | | | IV-1 | Nrbp2 |
| 16444 | 3 | 4 | | | IV-1 | Nrcam |
| 16445 | 3 | 4 | | | IV-1 | Nrd1 |
| 16446 | 3 | 4 | | | IV-1 | Nrde2 |
| 16447 | 3 | 4 | | | IV-1 | Nrg2 |
| 16448 | 3 | 4 | | | IV-1 | Nrg3 |
| 16449 | 3 | 4 | | | IV-1 | Nrg3os |
| 16450 | 3 | 4 | | | IV-1 | Nrn1 |
| 16451 | 3 | 4 | | | IV-1 | Nrros |
| 16452 | 3 | 4 | | | IV-1 | Nrsn1 |
| 16453 | 3 | 4 | | | IV-1 | Nrsn2 |
| 16454 | 3 | 4 | | | IV-1 | Nrxn1 |
| 16455 | 3 | 4 | | | IV-1 | Nrxn2 |
| 16456 | 3 | 4 | | | IV-1 | Nrxn3 |
| 16457 | 3 | 4 | | | IV-1 | Nsa2 |
| 16458 | 3 | 4 | | | IV-1 | Nsf |
| 16459 | 3 | 4 | | | IV-1 | Nsl1 |
| 16460 | 3 | 4 | | | IV-1 | Nsmce2 |
| 16461 | 3 | 4 | | | IV-1 | Nsmce4a |
| 16462 | 3 | 4 | | | IV-1 | Nsun2 |
| 16463 | 3 | 4 | | | IV-1 | Nsun4 |
| 16464 | 3 | 4 | | | IV-1 | Nsun7 |
| 16465 | 3 | 4 | | | IV-1 | Nt5c1b |
| 16466 | 3 | 4 | | | IV-1 | Nt5c2 |
| 16467 | 3 | 4 | | | IV-1 | Nt5c3b |
| 16468 | 3 | 4 | | | IV-1 | Nt5dc1 |
| 16469 | 3 | 4 | | | IV-1 | Nt5m |
| 16470 | 3 | 4 | | | IV-1 | Ntmt1 |
| 16471 | 3 | 4 | | | IV-1 | Ntn1 |
| 16472 | 3 | 4 | | | IV-1 | Ntn3 |
| 16473 | 3 | 4 | | | IV-1 | Ntng1 |
| 16474 | 3 | 4 | | | IV-1 | Ntpcr |
| 16475 | 3 | 4 | | | IV-1 | Ntrk3 |
| 16476 | 3 | 4 | | | IV-1 | Nts |
| 16477 | 3 | 4 | | | IV-1 | Ntsr1 |
| 16478 | 3 | 4 | | | IV-1 | Nub1 |
| 16479 | 3 | 4 | | | IV-1 | Nubp1 |
| 16480 | 3 | 4 | | | IV-1 | Nucb1 |
| 16481 | 3 | 4 | | | IV-1 | Nucks1 |
| 16482 | 3 | 4 | | | IV-1 | Nudcd1 |
| 16483 | 3 | 4 | | | IV-1 | Nudcd3 |
| 16484 | 3 | 4 | | | IV-1 | Nudt11 |
| 16485 | 3 | 4 | | | IV-1 | Nudt13 |
| 16486 | 3 | 4 | | | IV-1 | Nudt18 |
| 16487 | 3 | 4 | | | IV-1 | Nudt19 |
| 16488 | 3 | 4 | | | IV-1 | Nudt4 |
| 16489 | 3 | 4 | | | IV-1 | Nudt5 |
| 16490 | 3 | 4 | | | IV-1 | Nuf2 |
| 16491 | 3 | 4 | | | IV-1 | Nufip1 |
| 16492 | 3 | 4 | | | IV-1 | Nufip2 |
| 16493 | 3 | 4 | | | IV-1 | Nuggc |
| 16494 | 3 | 4 | | | IV-1 | Numb |
| 16495 | 3 | 4 | | | IV-1 | Numbl |
| 16496 | 3 | 4 | | | IV-1 | Nup133 |
| 16497 | 3 | 4 | | | IV-1 | Nup155 |
| 16498 | 3 | 4 | | | IV-1 | Nup160 |
| 16499 | 3 | 4 | | | IV-1 | Nup188 |
| 16500 | 3 | 4 | | | IV-1 | Nup205 |
| 16501 | 3 | 4 | | | IV-1 | Nup214 |
| 16502 | 3 | 4 | | | IV-1 | Nup50 |
| 16503 | 3 | 4 | | | IV-1 | Nup54 |
| 16504 | 3 | 4 | | | IV-1 | Nup62cl |
| 16505 | 3 | 4 | | | IV-1 | Nup85 |
| 16506 | 3 | 4 | | | IV-1 | Nup88 |
| 16507 | 3 | 4 | | | IV-1 | Nup93 |
| 16508 | 3 | 4 | | | IV-1 | Nup98 |
| 16509 | 3 | 4 | | | IV-1 | Nupl2 |
| 16510 | 3 | 4 | | | IV-1 | Nus1 |

Fig. 36 - 87

| | | | | | | |
|---|---|---|---|---|---|---|
| 16511 | 3 | 4 | | | IV-1 | Nutm1 |
| 16512 | 3 | 4 | | | IV-1 | Nxf1 |
| 16513 | 3 | 4 | | | IV-1 | Nxf2 |
| 16514 | 3 | 4 | | | IV-1 | Nxn |
| 16515 | 3 | 4 | | | IV-1 | Nxnl1 |
| 16516 | 3 | 4 | | | IV-1 | Nxpe3 |
| 16517 | 3 | 4 | | | IV-1 | Nxpe4 |
| 16518 | 3 | 4 | | | IV-1 | Nxph1 |
| 16519 | 3 | 4 | | | IV-1 | Nxph3 |
| 16520 | 3 | 4 | | | IV-1 | Nyap1 |
| 16521 | 3 | 4 | | | IV-1 | Oas1a |
| 16522 | 3 | 4 | | | IV-1 | Oas1b |
| 16523 | 3 | 4 | | | IV-1 | Oas1f |
| 16524 | 3 | 4 | | | IV-1 | Oaz1 |
| 16525 | 3 | 4 | | | IV-1 | Oaz2 |
| 16526 | 3 | 4 | | | IV-1 | Oaz3 |
| 16527 | 3 | 4 | | | IV-1 | Obox6 |
| 16528 | 3 | 4 | | | IV-1 | Obscn |
| 16529 | 3 | 4 | | | IV-1 | Oca2 |
| 16530 | 3 | 4 | | | IV-1 | Ociad1 |
| 16531 | 3 | 4 | | | IV-1 | Ocm |
| 16532 | 3 | 4 | | | IV-1 | Ocstamp |
| 16533 | 3 | 4 | | | IV-1 | Odf1 |
| 16534 | 3 | 4 | | | IV-1 | Odf2 |
| 16535 | 3 | 4 | | | IV-1 | Odf2l |
| 16536 | 3 | 4 | | | IV-1 | Odf3l2 |
| 16537 | 3 | 4 | | | IV-1 | Odf4 |
| 16538 | 3 | 4 | | | IV-1 | Ofd1 |
| 16539 | 3 | 4 | | | IV-1 | Ogfod1 |
| 16540 | 3 | 4 | | | IV-1 | Ogfod2 |
| 16541 | 3 | 4 | | | IV-1 | Ogfr |
| 16542 | 3 | 4 | | | IV-1 | Ogfrl1 |
| 16543 | 3 | 4 | | | IV-1 | Ogg1 |
| 16544 | 3 | 4 | | | IV-1 | Ogt |
| 16545 | 3 | 4 | | | IV-1 | Ola1 |
| 16546 | 3 | 4 | | | IV-1 | Olah |
| 16547 | 3 | 4 | | | IV-1 | Olfm1 |
| 16548 | 3 | 4 | | | IV-1 | Olfm2 |
| 16549 | 3 | 4 | | | IV-1 | Olfm3 |
| 16550 | 3 | 4 | | | IV-1 | Olfml1 |
| 16551 | 3 | 4 | | | IV-1 | Olfml2b |
| 16552 | 3 | 4 | | | IV-1 | Olfr111 |
| 16553 | 3 | 4 | | | IV-1 | Olfr112 |
| 16554 | 3 | 4 | | | IV-1 | Olfr1186 |
| 16555 | 3 | 4 | | | IV-1 | Olfr1188 |
| 16556 | 3 | 4 | | | IV-1 | Olfr126 |
| 16557 | 3 | 4 | | | IV-1 | Olfr127 |
| 16558 | 3 | 4 | | | IV-1 | Olfr128 |
| 16559 | 3 | 4 | | | IV-1 | Olfr1344 |
| 16560 | 3 | 4 | | | IV-1 | Olfr1383 |
| 16561 | 3 | 4 | | | IV-1 | Olfr1494 |
| 16562 | 3 | 4 | | | IV-1 | Olfr19 |
| 16563 | 3 | 4 | | | IV-1 | Olfr194 |
| 16564 | 3 | 4 | | | IV-1 | Olfr20 |
| 16565 | 3 | 4 | | | IV-1 | Olfr23 |
| 16566 | 3 | 4 | | | IV-1 | Olfr27 |
| 16567 | 3 | 4 | | | IV-1 | Olfr288 |
| 16568 | 3 | 4 | | | IV-1 | Olfr29-ps1 |
| 16569 | 3 | 4 | | | IV-1 | Olfr30 |
| 16570 | 3 | 4 | | | IV-1 | Olfr357 |
| 16571 | 3 | 4 | | | IV-1 | Olfr360 |
| 16572 | 3 | 4 | | | IV-1 | Olfr419 |
| 16573 | 3 | 4 | | | IV-1 | Olfr433 |
| 16574 | 3 | 4 | | | IV-1 | Olfr558 |
| 16575 | 3 | 4 | | | IV-1 | Olfr639 |
| 16576 | 3 | 4 | | | IV-1 | Olfr701 |
| 16577 | 3 | 4 | | | IV-1 | Olfr733 |
| 16578 | 3 | 4 | | | IV-1 | Olfr872 |
| 16579 | 3 | 4 | | | IV-1 | Olfr874 |
| 16580 | 3 | 4 | | | IV-1 | Olig3 |
| 16581 | 3 | 4 | | | IV-1 | Oma1 |
| 16582 | 3 | 4 | | | IV-1 | Omd |
| 16583 | 3 | 4 | | | IV-1 | Omg |
| 16584 | 3 | 4 | | | IV-1 | Onecut3 |
| 16585 | 3 | 4 | | | IV-1 | Opa1 |
| 16586 | 3 | 4 | | | IV-1 | Opalin |
| 16587 | 3 | 4 | | | IV-1 | Opcml |
| 16588 | 3 | 4 | | | IV-1 | Ophn1 |
| 16589 | 3 | 4 | | | IV-1 | Oplah |
| 16590 | 3 | 4 | | | IV-1 | Opn1mw |
| 16591 | 3 | 4 | | | IV-1 | Opn3 |
| 16592 | 3 | 4 | | | IV-1 | Oprk1 |
| 16593 | 3 | 4 | | | IV-1 | Oprl1 |
| 16594 | 3 | 4 | | | IV-1 | Orai3 |
| 16595 | 3 | 4 | | | IV-1 | Oraov1 |
| 16596 | 3 | 4 | | | IV-1 | Orc1 |
| 16597 | 3 | 4 | | | IV-1 | Orc2 |
| 16598 | 3 | 4 | | | IV-1 | Orc3 |
| 16599 | 3 | 4 | | | IV-1 | Orc4 |
| 16600 | 3 | 4 | | | IV-1 | Ormdl1 |
| 16601 | 3 | 4 | | | IV-1 | Os9 |
| 16602 | 3 | 4 | | | IV-1 | Osbp |
| 16603 | 3 | 4 | | | IV-1 | Osbp2 |
| 16604 | 3 | 4 | | | IV-1 | Osbpl11 |
| 16605 | 3 | 4 | | | IV-1 | Osbpl2 |
| 16606 | 3 | 4 | | | IV-1 | Osbpl3 |
| 16607 | 3 | 4 | | | IV-1 | Osbpl6 |
| 16608 | 3 | 4 | | | IV-1 | Osbpl9 |
| 16609 | 3 | 4 | | | IV-1 | Oser1 |
| 16610 | 3 | 4 | | | IV-1 | Osgin2 |
| 16611 | 3 | 4 | | | IV-1 | Osm |
| 16612 | 3 | 4 | | | IV-1 | Ostm1 |
| 16613 | 3 | 4 | | | IV-1 | Otc |
| 16614 | 3 | 4 | | | IV-1 | Otoa |
| 16615 | 3 | 4 | | | IV-1 | Otof |
| 16616 | 3 | 4 | | | IV-1 | Otop1 |
| 16617 | 3 | 4 | | | IV-1 | Otop2 |
| 16618 | 3 | 4 | | | IV-1 | Otub1 |
| 16619 | 3 | 4 | | | IV-1 | Otud4 |
| 16620 | 3 | 4 | | | IV-1 | Otud6a |
| 16621 | 3 | 4 | | | IV-1 | Otud6b |
| 16622 | 3 | 4 | | | IV-1 | Otud7a |
| 16623 | 3 | 4 | | | IV-1 | Otx1 |
| 16624 | 3 | 4 | | | IV-1 | Ovca2 |
| 16625 | 3 | 4 | | | IV-1 | Oxa1l |
| 16626 | 3 | 4 | | | IV-1 | Oxct1 |
| 16627 | 3 | 4 | | | IV-1 | Oxr1 |
| 16628 | 3 | 4 | | | IV-1 | Oxsr1 |
| 16629 | 3 | 4 | | | IV-1 | Oxt |
| 16630 | 3 | 4 | | | IV-1 | P2rx4 |
| 16631 | 3 | 4 | | | IV-1 | P2rx5 |
| 16632 | 3 | 4 | | | IV-1 | P2ry10 |
| 16633 | 3 | 4 | | | IV-1 | P2ry14 |
| 16634 | 3 | 4 | | | IV-1 | P4ha3 |
| 16635 | 3 | 4 | | | IV-1 | Pa2g4 |
| 16636 | 3 | 4 | | | IV-1 | Pabpc2 |
| 16637 | 3 | 4 | | | IV-1 | Pabpc6 |
| 16638 | 3 | 4 | | | IV-1 | Pabpn1 |
| 16639 | 3 | 4 | | | IV-1 | Pacs2 |
| 16640 | 3 | 4 | | | IV-1 | Pacsin3 |
| 16641 | 3 | 4 | | | IV-1 | Padi1 |
| 16642 | 3 | 4 | | | IV-1 | Padi3 |
| 16643 | 3 | 4 | | | IV-1 | Padi6 |
| 16644 | 3 | 4 | | | IV-1 | Pafah1b1 |
| 16645 | 3 | 4 | | | IV-1 | Pafah1b2 |
| 16646 | 3 | 4 | | | IV-1 | Pagr1a |
| 16647 | 3 | 4 | | | IV-1 | Paics |
| 16648 | 3 | 4 | | | IV-1 | Paip1 |
| 16649 | 3 | 4 | | | IV-1 | Paip2b |
| 16650 | 3 | 4 | | | IV-1 | Pak1 |
| 16651 | 3 | 4 | | | IV-1 | Pak2 |
| 16652 | 3 | 4 | | | IV-1 | Pak3 |
| 16653 | 3 | 4 | | | IV-1 | Pak7 |
| 16654 | 3 | 4 | | | IV-1 | Palb2 |
| 16655 | 3 | 4 | | | IV-1 | Pald1 |
| 16656 | 3 | 4 | | | IV-1 | Palmd |
| 16657 | 3 | 4 | | | IV-1 | Pam |
| 16658 | 3 | 4 | | | IV-1 | Pan3 |
| 16659 | 3 | 4 | | | IV-1 | Pank2 |
| 16660 | 3 | 4 | | | IV-1 | Pank4 |
| 16661 | 3 | 4 | | | IV-1 | Panx2 |
| 16662 | 3 | 4 | | | IV-1 | Panx3 |
| 16663 | 3 | 4 | | | IV-1 | Papd7 |
| 16664 | 3 | 4 | | | IV-1 | Papi |
| 16665 | 3 | 4 | | | IV-1 | Papola |
| 16666 | 3 | 4 | | | IV-1 | Papolg |
| 16667 | 3 | 4 | | | IV-1 | Pappa2 |
| 16668 | 3 | 4 | | | IV-1 | Papss1 |
| 16669 | 3 | 4 | | | IV-1 | Paqr4 |
| 16670 | 3 | 4 | | | IV-1 | Paqr7 |
| 16671 | 3 | 4 | | | IV-1 | Paqr8 |
| 16672 | 3 | 4 | | | IV-1 | Pard3 |
| 16673 | 3 | 4 | | | IV-1 | Parg |
| 16674 | 3 | 4 | | | IV-1 | Parn |
| 16675 | 3 | 4 | | | IV-1 | Parp1 |
| 16676 | 3 | 4 | | | IV-1 | Parp10 |
| 16677 | 3 | 4 | | | IV-1 | Parp11 |
| 16678 | 3 | 4 | | | IV-1 | Parp3 |
| 16679 | 3 | 4 | | | IV-1 | Parp4 |
| 16680 | 3 | 4 | | | IV-1 | Parp6 |
| 16681 | 3 | 4 | | | IV-1 | Parpbp |
| 16682 | 3 | 4 | | | IV-1 | Pars2 |
| 16683 | 3 | 4 | | | IV-1 | Parva |
| 16684 | 3 | 4 | | | IV-1 | Pask |
| 16685 | 3 | 4 | | | IV-1 | Patl1 |
| 16686 | 3 | 4 | | | IV-1 | Pax5 |
| 16687 | 3 | 4 | | | IV-1 | Pax9 |
| 16688 | 3 | 4 | | | IV-1 | Paxbp1 |
| 16689 | 3 | 4 | | | IV-1 | Pbdc1 |
| 16690 | 3 | 4 | | | IV-1 | Pbld1 |
| 16691 | 3 | 4 | | | IV-1 | Pbx1 |
| 16692 | 3 | 4 | | | IV-1 | Pbx2 |
| 16693 | 3 | 4 | | | IV-1 | Pbx3 |
| 16694 | 3 | 4 | | | IV-1 | Pbxip1 |
| 16695 | 3 | 4 | | | IV-1 | Pcbp1 |
| 16696 | 3 | 4 | | | IV-1 | Pcbp2 |
| 16697 | 3 | 4 | | | IV-1 | Pccb |
| 16698 | 3 | 4 | | | IV-1 | Pcdh19 |
| 16699 | 3 | 4 | | | IV-1 | Pcdh20 |
| 16700 | 3 | 4 | | | IV-1 | Pcdh8 |
| 16701 | 3 | 4 | | | IV-1 | Pcdha1 |
| 16702 | 3 | 4 | | | IV-1 | Pcdha10 |

Fig. 36 - 88

| | | | | | | |
|---|---|---|---|---|---|---|
| 16703 | 3 | 4 | | | IV-1 | Pcdha11 |
| 16704 | 3 | 4 | | | IV-1 | Pcdha12 |
| 16705 | 3 | 4 | | | IV-1 | Pcdha2 |
| 16706 | 3 | 4 | | | IV-1 | Pcdha3 |
| 16707 | 3 | 4 | | | IV-1 | Pcdha5 |
| 16708 | 3 | 4 | | | IV-1 | Pcdha6 |
| 16709 | 3 | 4 | | | IV-1 | Pcdha9 |
| 16710 | 3 | 4 | | | IV-1 | Pcdhac1 |
| 16711 | 3 | 4 | | | IV-1 | Pcdhac2 |
| 16712 | 3 | 4 | | | IV-1 | Pcdhb1 |
| 16713 | 3 | 4 | | | IV-1 | Pcdhb10 |
| 16714 | 3 | 4 | | | IV-1 | Pcdhb12 |
| 16715 | 3 | 4 | | | IV-1 | Pcdhb13 |
| 16716 | 3 | 4 | | | IV-1 | Pcdhb14 |
| 16717 | 3 | 4 | | | IV-1 | Pcdhb17 |
| 16718 | 3 | 4 | | | IV-1 | Pcdhb18 |
| 16719 | 3 | 4 | | | IV-1 | Pcdhb2 |
| 16720 | 3 | 4 | | | IV-1 | Pcdhb20 |
| 16721 | 3 | 4 | | | IV-1 | Pcdhb21 |
| 16722 | 3 | 4 | | | IV-1 | Pcdhb4 |
| 16723 | 3 | 4 | | | IV-1 | Pcdhb6 |
| 16724 | 3 | 4 | | | IV-1 | Pcdhb7 |
| 16725 | 3 | 4 | | | IV-1 | Pcdhb9 |
| 16726 | 3 | 4 | | | IV-1 | Pcdhga12 |
| 16727 | 3 | 4 | | | IV-1 | Pcdhga3 |
| 16728 | 3 | 4 | | | IV-1 | Pcdhga6 |
| 16729 | 3 | 4 | | | IV-1 | Pcdhga7 |
| 16730 | 3 | 4 | | | IV-1 | Pcdhga9 |
| 16731 | 3 | 4 | | | IV-1 | Pcdhgc3 |
| 16732 | 3 | 4 | | | IV-1 | Pcdhgc5 |
| 16733 | 3 | 4 | | | IV-1 | Pced1a |
| 16734 | 3 | 4 | | | IV-1 | Pcf11 |
| 16735 | 3 | 4 | | | IV-1 | Pcgf5 |
| 16736 | 3 | 4 | | | IV-1 | Pcgf6 |
| 16737 | 3 | 4 | | | IV-1 | Pcm1 |
| 16738 | 3 | 4 | | | IV-1 | Pcmtd2 |
| 16739 | 3 | 4 | | | IV-1 | Pcna |
| 16740 | 3 | 4 | | | IV-1 | Pcnp |
| 16741 | 3 | 4 | | | IV-1 | Pcnxl2 |
| 16742 | 3 | 4 | | | IV-1 | Pcnxl4 |
| 16743 | 3 | 4 | | | IV-1 | Pcp2 |
| 16744 | 3 | 4 | | | IV-1 | Pcsk2os1 |
| 16745 | 3 | 4 | | | IV-1 | Pcsk6 |
| 16746 | 3 | 4 | | | IV-1 | Pcsk7 |
| 16747 | 3 | 4 | | | IV-1 | Pcyox1 |
| 16748 | 3 | 4 | | | IV-1 | Pcyt1a |
| 16749 | 3 | 4 | | | IV-1 | Pdap1 |
| 16750 | 3 | 4 | | | IV-1 | Pdcd1lg2 |
| 16751 | 3 | 4 | | | IV-1 | Pdcd2l |
| 16752 | 3 | 4 | | | IV-1 | Pdcd4 |
| 16753 | 3 | 4 | | | IV-1 | Pdcd6ip |
| 16754 | 3 | 4 | | | IV-1 | Pdcl |
| 16755 | 3 | 4 | | | IV-1 | Pdcl2 |
| 16756 | 3 | 4 | | | IV-1 | Pde12 |
| 16757 | 3 | 4 | | | IV-1 | Pde1c |
| 16758 | 3 | 4 | | | IV-1 | Pde2a |
| 16759 | 3 | 4 | | | IV-1 | Pde6a |
| 16760 | 3 | 4 | | | IV-1 | Pde7a |
| 16761 | 3 | 4 | | | IV-1 | Pde8b |
| 16762 | 3 | 4 | | | IV-1 | Pdf |
| 16763 | 3 | 4 | | | IV-1 | Pdgfb |
| 16764 | 3 | 4 | | | IV-1 | Pdgfra |
| 16765 | 3 | 4 | | | IV-1 | Pdgfrb |
| 16766 | 3 | 4 | | | IV-1 | Pdha1 |
| 16767 | 3 | 4 | | | IV-1 | Pdha2 |
| 16768 | 3 | 4 | | | IV-1 | Pdhb |
| 16769 | 3 | 4 | | | IV-1 | Pdia4 |
| 16770 | 3 | 4 | | | IV-1 | Pdik1l |
| 16771 | 3 | 4 | | | IV-1 | Pdilt |
| 16772 | 3 | 4 | | | IV-1 | Pdk2 |
| 16773 | 3 | 4 | | | IV-1 | Pdlim5 |
| 16774 | 3 | 4 | | | IV-1 | Pdp1 |
| 16775 | 3 | 4 | | | IV-1 | Pdpn |
| 16776 | 3 | 4 | | | IV-1 | Pds5b |
| 16777 | 3 | 4 | | | IV-1 | Pdxdc1 |
| 16778 | 3 | 4 | | | IV-1 | Pdxp |
| 16779 | 3 | 4 | | | IV-1 | Pdyn |
| 16780 | 3 | 4 | | | IV-1 | Pdzd2 |
| 16781 | 3 | 4 | | | IV-1 | Pdzd4 |
| 16782 | 3 | 4 | | | IV-1 | Pdzrn3 |
| 16783 | 3 | 4 | | | IV-1 | Pdzrn4 |
| 16784 | 3 | 4 | | | IV-1 | Pear1 |
| 16785 | 3 | 4 | | | IV-1 | Pebp4 |
| 16786 | 3 | 4 | | | IV-1 | Peg12 |
| 16787 | 3 | 4 | | | IV-1 | Peg13 |
| 16788 | 3 | 4 | | | IV-1 | Peli1 |
| 16789 | 3 | 4 | | | IV-1 | Peli2 |
| 16790 | 3 | 4 | | | IV-1 | Pelp1 |
| 16791 | 3 | 4 | | | IV-1 | Pepd |
| 16792 | 3 | 4 | | | IV-1 | Pes1 |
| 16793 | 3 | 4 | | | IV-1 | Pet2 |
| 16794 | 3 | 4 | | | IV-1 | Pex10 |
| 16795 | 3 | 4 | | | IV-1 | Pex11b |
| 16796 | 3 | 4 | | | IV-1 | Pex12 |
| 16797 | 3 | 4 | | | IV-1 | Pex14 |
| 16798 | 3 | 4 | | | IV-1 | Pex2 |
| 16799 | 3 | 4 | | | IV-1 | Pex26 |
| 16800 | 3 | 4 | | | IV-1 | Pex5 |
| 16801 | 3 | 4 | | | IV-1 | Pex5l |
| 16802 | 3 | 4 | | | IV-1 | Pex6 |
| 16803 | 3 | 4 | | | IV-1 | Pfas |
| 16804 | 3 | 4 | | | IV-1 | Pfkfb1 |
| 16805 | 3 | 4 | | | IV-1 | Pfkfb3 |
| 16806 | 3 | 4 | | | IV-1 | Pfkl |
| 16807 | 3 | 4 | | | IV-1 | Pfkm |
| 16808 | 3 | 4 | | | IV-1 | Pfkp |
| 16809 | 3 | 4 | | | IV-1 | Pfn1 |
| 16810 | 3 | 4 | | | IV-1 | Pfn4 |
| 16811 | 3 | 4 | | | IV-1 | Pga5 |
| 16812 | 3 | 4 | | | IV-1 | Pgam1 |
| 16813 | 3 | 4 | | | IV-1 | Pgam5 |
| 16814 | 3 | 4 | | | IV-1 | Pgbd1 |
| 16815 | 3 | 4 | | | IV-1 | Pgbd5 |
| 16816 | 3 | 4 | | | IV-1 | Pgd |
| 16817 | 3 | 4 | | | IV-1 | Pgk1 |
| 16818 | 3 | 4 | | | IV-1 | Pgk2 |
| 16819 | 3 | 4 | | | IV-1 | Pglyrp2 |
| 16820 | 3 | 4 | | | IV-1 | Pglyrp4 |
| 16821 | 3 | 4 | | | IV-1 | Pgm2 |
| 16822 | 3 | 4 | | | IV-1 | Pgm5 |
| 16823 | 3 | 4 | | | IV-1 | Pgr |
| 16824 | 3 | 4 | | | IV-1 | Pgrmc2 |
| 16825 | 3 | 4 | | | IV-1 | Pgs1 |
| 16826 | 3 | 4 | | | IV-1 | Phactr1 |
| 16827 | 3 | 4 | | | IV-1 | Phactr4 |
| 16828 | 3 | 4 | | | IV-1 | Phax |
| 16829 | 3 | 4 | | | IV-1 | Phb2 |
| 16830 | 3 | 4 | | | IV-1 | Phc1 |
| 16831 | 3 | 4 | | | IV-1 | Phc2 |
| 16832 | 3 | 4 | | | IV-1 | Phf1 |
| 16833 | 3 | 4 | | | IV-1 | Phf11a |
| 16834 | 3 | 4 | | | IV-1 | Phf11d |
| 16835 | 3 | 4 | | | IV-1 | Phf12 |
| 16836 | 3 | 4 | | | IV-1 | Phf13 |
| 16837 | 3 | 4 | | | IV-1 | Phf14 |
| 16838 | 3 | 4 | | | IV-1 | Phf2 |
| 16839 | 3 | 4 | | | IV-1 | Phf20 |
| 16840 | 3 | 4 | | | IV-1 | Phf20l1 |
| 16841 | 3 | 4 | | | IV-1 | Phf21a |
| 16842 | 3 | 4 | | | IV-1 | Phf21b |
| 16843 | 3 | 4 | | | IV-1 | Phf23 |
| 16844 | 3 | 4 | | | IV-1 | Phf3 |
| 16845 | 3 | 4 | | | IV-1 | Phf7 |
| 16846 | 3 | 4 | | | IV-1 | Phf8 |
| 16847 | 3 | 4 | | | IV-1 | Phip |
| 16848 | 3 | 4 | | | IV-1 | Phka1 |
| 16849 | 3 | 4 | | | IV-1 | Phkb |
| 16850 | 3 | 4 | | | IV-1 | Phkg1 |
| 16851 | 3 | 4 | | | IV-1 | Phkg2 |
| 16852 | 3 | 4 | | | IV-1 | Phlda2 |
| 16853 | 3 | 4 | | | IV-1 | Phldb1 |
| 16854 | 3 | 4 | | | IV-1 | Phldb2 |
| 16855 | 3 | 4 | | | IV-1 | Phldb3 |
| 16856 | 3 | 4 | | | IV-1 | Phlpp1 |
| 16857 | 3 | 4 | | | IV-1 | Phospho2 |
| 16858 | 3 | 4 | | | IV-1 | Phox2b |
| 16859 | 3 | 4 | | | IV-1 | Phrf1 |
| 16860 | 3 | 4 | | | IV-1 | Phtf1 |
| 16861 | 3 | 4 | | | IV-1 | Phtf2 |
| 16862 | 3 | 4 | | | IV-1 | Phyhip1 |
| 16863 | 3 | 4 | | | IV-1 | Phykpl |
| 16864 | 3 | 4 | | | IV-1 | Pi15 |
| 16865 | 3 | 4 | | | IV-1 | Pi4k2a |
| 16866 | 3 | 4 | | | IV-1 | Pianp |
| 16867 | 3 | 4 | | | IV-1 | Pias1 |
| 16868 | 3 | 4 | | | IV-1 | Pias2 |
| 16869 | 3 | 4 | | | IV-1 | Pias3 |
| 16870 | 3 | 4 | | | IV-1 | Pias4 |
| 16871 | 3 | 4 | | | IV-1 | Pibf1 |
| 16872 | 3 | 4 | | | IV-1 | Picalm |
| 16873 | 3 | 4 | | | IV-1 | Pick1 |
| 16874 | 3 | 4 | | | IV-1 | Piezo2 |
| 16875 | 3 | 4 | | | IV-1 | Pif1 |
| 16876 | 3 | 4 | | | IV-1 | Pigc |
| 16877 | 3 | 4 | | | IV-1 | Pigh |
| 16878 | 3 | 4 | | | IV-1 | Pigk |
| 16879 | 3 | 4 | | | IV-1 | Pign |
| 16880 | 3 | 4 | | | IV-1 | Pigo |
| 16881 | 3 | 4 | | | IV-1 | Pigs |
| 16882 | 3 | 4 | | | IV-1 | Pigt |
| 16883 | 3 | 4 | | | IV-1 | Pigu |
| 16884 | 3 | 4 | | | IV-1 | Pigv |
| 16885 | 3 | 4 | | | IV-1 | Pigw |
| 16886 | 3 | 4 | | | IV-1 | Pigyl |
| 16887 | 3 | 4 | | | IV-1 | Pih1d1 |
| 16888 | 3 | 4 | | | IV-1 | Pih1d3 |
| 16889 | 3 | 4 | | | IV-1 | Pik3c2b |
| 16890 | 3 | 4 | | | IV-1 | Pik3c3 |
| 16891 | 3 | 4 | | | IV-1 | Pik3ca |
| 16892 | 3 | 4 | | | IV-1 | Pik3cb |
| 16893 | 3 | 4 | | | IV-1 | Pik3cg |
| 16894 | 3 | 4 | | | IV-1 | Pik3r2 |

Fig. 36 - 89

| | | | | | | |
|---|---|---|---|---|---|---|
| 16895 | 3 | 4 | | | IV-1 | Pik3r4 |
| 16896 | 3 | 4 | | | IV-1 | Pik3r5 |
| 16897 | 3 | 4 | | | IV-1 | Pik3r6 |
| 16898 | 3 | 4 | | | IV-1 | Pikfyve |
| 16899 | 3 | 4 | | | IV-1 | Pilra |
| 16900 | 3 | 4 | | | IV-1 | Pim2 |
| 16901 | 3 | 4 | | | IV-1 | Pim3 |
| 16902 | 3 | 4 | | | IV-1 | Pin1 |
| 16903 | 3 | 4 | | | IV-1 | Pinlyp |
| 16904 | 3 | 4 | | | IV-1 | Pip4k2b |
| 16905 | 3 | 4 | | | IV-1 | Pip4k2c |
| 16906 | 3 | 4 | | | IV-1 | Pip5k1c |
| 16907 | 3 | 4 | | | IV-1 | Pip5kl1 |
| 16908 | 3 | 4 | | | IV-1 | Pir |
| 16909 | 3 | 4 | | | IV-1 | Pira2 |
| 16910 | 3 | 4 | | | IV-1 | Pira6 |
| 16911 | 3 | 4 | | | IV-1 | Pisd |
| 16912 | 3 | 4 | | | IV-1 | Pisd-ps1 |
| 16913 | 3 | 4 | | | IV-1 | Pisd-ps2 |
| 16914 | 3 | 4 | | | IV-1 | Pitpna |
| 16915 | 3 | 4 | | | IV-1 | Pitpnb |
| 16916 | 3 | 4 | | | IV-1 | Pitpnc1 |
| 16917 | 3 | 4 | | | IV-1 | Pitpnm1 |
| 16918 | 3 | 4 | | | IV-1 | Pitpnm2 |
| 16919 | 3 | 4 | | | IV-1 | Pitpnm3 |
| 16920 | 3 | 4 | | | IV-1 | Pitx1 |
| 16921 | 3 | 4 | | | IV-1 | Piwil1 |
| 16922 | 3 | 4 | | | IV-1 | Piwil2 |
| 16923 | 3 | 4 | | | IV-1 | Pja2 |
| 16924 | 3 | 4 | | | IV-1 | Pkd2 |
| 16925 | 3 | 4 | | | IV-1 | Pkd2l1 |
| 16926 | 3 | 4 | | | IV-1 | Pkdcc |
| 16927 | 3 | 4 | | | IV-1 | Pkhd1 |
| 16928 | 3 | 4 | | | IV-1 | Pkib |
| 16929 | 3 | 4 | | | IV-1 | Pkmyt1 |
| 16930 | 3 | 4 | | | IV-1 | Pkn3 |
| 16931 | 3 | 4 | | | IV-1 | Pknox1 |
| 16932 | 3 | 4 | | | IV-1 | Pknox2 |
| 16933 | 3 | 4 | | | IV-1 | Pkp1 |
| 16934 | 3 | 4 | | | IV-1 | Pkp2 |
| 16935 | 3 | 4 | | | IV-1 | Pkp4 |
| 16936 | 3 | 4 | | | IV-1 | Pla2g10 |
| 16937 | 3 | 4 | | | IV-1 | Pla2g15 |
| 16938 | 3 | 4 | | | IV-1 | Pla2g2a |
| 16939 | 3 | 4 | | | IV-1 | Pla2g2c |
| 16940 | 3 | 4 | | | IV-1 | Pla2g2f |
| 16941 | 3 | 4 | | | IV-1 | Pla2g4d |
| 16942 | 3 | 4 | | | IV-1 | Pla2g4e |
| 16943 | 3 | 4 | | | IV-1 | Pla2g4f |
| 16944 | 3 | 4 | | | IV-1 | Plaa |
| 16945 | 3 | 4 | | | IV-1 | Plac1 |
| 16946 | 3 | 4 | | | IV-1 | Plag1 |
| 16947 | 3 | 4 | | | IV-1 | Plagl2 |
| 16948 | 3 | 4 | | | IV-1 | Plbd1 |
| 16949 | 3 | 4 | | | IV-1 | Plbd2 |
| 16950 | 3 | 4 | | | IV-1 | Plcb3 |
| 16951 | 3 | 4 | | | IV-1 | Plcd1 |
| 16952 | 3 | 4 | | | IV-1 | Plcd3 |
| 16953 | 3 | 4 | | | IV-1 | Plce1 |
| 16954 | 3 | 4 | | | IV-1 | Plcg2 |
| 16955 | 3 | 4 | | | IV-1 | Plch1 |
| 16956 | 3 | 4 | | | IV-1 | Plch2 |
| 16957 | 3 | 4 | | | IV-1 | Plcl2 |
| 16958 | 3 | 4 | | | IV-1 | Pld5 |
| 16959 | 3 | 4 | | | IV-1 | Pld6 |
| 16960 | 3 | 4 | | | IV-1 | Pldi |
| 16961 | 3 | 4 | | | IV-1 | Plekha1 |
| 16962 | 3 | 4 | | | IV-1 | Plekhd1 |
| 16963 | 3 | 4 | | | IV-1 | Plekhd1os |
| 16964 | 3 | 4 | | | IV-1 | Plekhf1 |
| 16965 | 3 | 4 | | | IV-1 | Plekhf2 |
| 16966 | 3 | 4 | | | IV-1 | Plekhg2 |
| 16967 | 3 | 4 | | | IV-1 | Plekhg4 |
| 16968 | 3 | 4 | | | IV-1 | Plekhg5 |
| 16969 | 3 | 4 | | | IV-1 | Plekhh2 |
| 16970 | 3 | 4 | | | IV-1 | Plekhh3 |
| 16971 | 3 | 4 | | | IV-1 | Plekhj1 |
| 16972 | 3 | 4 | | | IV-1 | Plekhm1 |
| 16973 | 3 | 4 | | | IV-1 | Plekhm2 |
| 16974 | 3 | 4 | | | IV-1 | Plerlos |
| 16975 | 3 | 4 | | | IV-1 | Plin3 |
| 16976 | 3 | 4 | | | IV-1 | Plin5 |
| 16977 | 3 | 4 | | | IV-1 | Plod1 |
| 16978 | 3 | 4 | | | IV-1 | Plod2 |
| 16979 | 3 | 4 | | | IV-1 | Plrg1 |
| 16980 | 3 | 4 | | | IV-1 | Plscr1 |
| 16981 | 3 | 4 | | | IV-1 | Plscr4 |
| 16982 | 3 | 4 | | | IV-1 | Plxna4os1 |
| 16983 | 3 | 4 | | | IV-1 | Plxnb3 |
| 16984 | 3 | 4 | | | IV-1 | Plxnc1 |
| 16985 | 3 | 4 | | | IV-1 | Plxnd1 |
| 16986 | 3 | 4 | | | IV-1 | Pmch |
| 16987 | 3 | 4 | | | IV-1 | Pmel |
| 16988 | 3 | 4 | | | IV-1 | Pmepa1 |
| 16989 | 3 | 4 | | | IV-1 | Pmfbp1 |
| 16990 | 3 | 4 | | | IV-1 | Pml |
| 16991 | 3 | 4 | | | IV-1 | Pmm2 |
| 16992 | 3 | 4 | | | IV-1 | Pmp2 |
| 16993 | 3 | 4 | | | IV-1 | Pmpca |
| 16994 | 3 | 4 | | | IV-1 | Pmpcb |
| 16995 | 3 | 4 | | | IV-1 | Pms1 |
| 16996 | 3 | 4 | | | IV-1 | Pms2 |
| 16997 | 3 | 4 | | | IV-1 | Pnisr |
| 16998 | 3 | 4 | | | IV-1 | Pnkp |
| 16999 | 3 | 4 | | | IV-1 | Pnldc1 |
| 17000 | 3 | 4 | | | IV-1 | Pnma1 |
| 17001 | 3 | 4 | | | IV-1 | Pnma2 |
| 17002 | 3 | 4 | | | IV-1 | Pnma3 |
| 17003 | 3 | 4 | | | IV-1 | Pnma5 |
| 17004 | 3 | 4 | | | IV-1 | Pnn |
| 17005 | 3 | 4 | | | IV-1 | Pno1 |
| 17006 | 3 | 4 | | | IV-1 | Pnpla1 |
| 17007 | 3 | 4 | | | IV-1 | Pnpla6 |
| 17008 | 3 | 4 | | | IV-1 | Pnpla7 |
| 17009 | 3 | 4 | | | IV-1 | Pnpt1 |
| 17010 | 3 | 4 | | | IV-1 | Pnrc2 |
| 17011 | 3 | 4 | | | IV-1 | Poc1b |
| 17012 | 3 | 4 | | | IV-1 | Poc5 |
| 17013 | 3 | 4 | | | IV-1 | Podn |
| 17014 | 3 | 4 | | | IV-1 | Podnl1 |
| 17015 | 3 | 4 | | | IV-1 | Podxl |
| 17016 | 3 | 4 | | | IV-1 | Podxl2 |
| 17017 | 3 | 4 | | | IV-1 | Pofib |
| 17018 | 3 | 4 | | | IV-1 | Pofut1 |
| 17019 | 3 | 4 | | | IV-1 | Pofut2 |
| 17020 | 3 | 4 | | | IV-1 | Poglut1 |
| 17021 | 3 | 4 | | | IV-1 | Pogz |
| 17022 | 3 | 4 | | | IV-1 | Pola1 |
| 17023 | 3 | 4 | | | IV-1 | Pola2 |
| 17024 | 3 | 4 | | | IV-1 | Pold1 |
| 17025 | 3 | 4 | | | IV-1 | Pold3 |
| 17026 | 3 | 4 | | | IV-1 | Poldip2 |
| 17027 | 3 | 4 | | | IV-1 | Poldip3 |
| 17028 | 3 | 4 | | | IV-1 | Pole |
| 17029 | 3 | 4 | | | IV-1 | Polg |
| 17030 | 3 | 4 | | | IV-1 | Poli |
| 17031 | 3 | 4 | | | IV-1 | Polk |
| 17032 | 3 | 4 | | | IV-1 | Poll |
| 17033 | 3 | 4 | | | IV-1 | Polm |
| 17034 | 3 | 4 | | | IV-1 | Poln |
| 17035 | 3 | 4 | | | IV-1 | Polr1b |
| 17036 | 3 | 4 | | | IV-1 | Polr1e |
| 17037 | 3 | 4 | | | IV-1 | Polr2a |
| 17038 | 3 | 4 | | | IV-1 | Polr2d |
| 17039 | 3 | 4 | | | IV-1 | Polr3a |
| 17040 | 3 | 4 | | | IV-1 | Polr3b |
| 17041 | 3 | 4 | | | IV-1 | Polr3e |
| 17042 | 3 | 4 | | | IV-1 | Polr3f |
| 17043 | 3 | 4 | | | IV-1 | Polr3g |
| 17044 | 3 | 4 | | | IV-1 | Polr3h |
| 17045 | 3 | 4 | | | IV-1 | Polr3k |
| 17046 | 3 | 4 | | | IV-1 | Pom121 |
| 17047 | 3 | 4 | | | IV-1 | Pomc |
| 17048 | 3 | 4 | | | IV-1 | Pomgnt1 |
| 17049 | 3 | 4 | | | IV-1 | Pomgnt2 |
| 17050 | 3 | 4 | | | IV-1 | Pomk |
| 17051 | 3 | 4 | | | IV-1 | Pomt1 |
| 17052 | 3 | 4 | | | IV-1 | Pon1 |
| 17053 | 3 | 4 | | | IV-1 | Pon2 |
| 17054 | 3 | 4 | | | IV-1 | Pon3 |
| 17055 | 3 | 4 | | | IV-1 | Popdc2 |
| 17056 | 3 | 4 | | | IV-1 | Pot1a |
| 17057 | 3 | 4 | | | IV-1 | Pou2f3 |
| 17058 | 3 | 4 | | | IV-1 | Pou3f2 |
| 17059 | 3 | 4 | | | IV-1 | Pou4f1 |
| 17060 | 3 | 4 | | | IV-1 | Pou5f1 |
| 17061 | 3 | 4 | | | IV-1 | Pou6f1 |
| 17062 | 3 | 4 | | | IV-1 | Pp2d1 |
| 17063 | 3 | 4 | | | IV-1 | Ppapdc2 |
| 17064 | 3 | 4 | | | IV-1 | Ppcdc |
| 17065 | 3 | 4 | | | IV-1 | Ppcs |
| 17066 | 3 | 4 | | | IV-1 | Ppfia1 |
| 17067 | 3 | 4 | | | IV-1 | Ppfia2 |
| 17068 | 3 | 4 | | | IV-1 | Ppfia4 |
| 17069 | 3 | 4 | | | IV-1 | Ppfibp1 |
| 17070 | 3 | 4 | | | IV-1 | Pphln1 |
| 17071 | 3 | 4 | | | IV-1 | Ppig |
| 17072 | 3 | 4 | | | IV-1 | Ppil4 |
| 17073 | 3 | 4 | | | IV-1 | Ppip5k1 |
| 17074 | 3 | 4 | | | IV-1 | Ppip5k2 |
| 17075 | 3 | 4 | | | IV-1 | Ppm1a |
| 17076 | 3 | 4 | | | IV-1 | Ppm1b |
| 17077 | 3 | 4 | | | IV-1 | Ppm1d |
| 17078 | 3 | 4 | | | IV-1 | Ppm1f |
| 17079 | 3 | 4 | | | IV-1 | Ppm1g |
| 17080 | 3 | 4 | | | IV-1 | Ppm1h |
| 17081 | 3 | 4 | | | IV-1 | Ppm1j |
| 17082 | 3 | 4 | | | IV-1 | Ppm1k |
| 17083 | 3 | 4 | | | IV-1 | Ppm1m |
| 17084 | 3 | 4 | | | IV-1 | Ppm1n |
| 17085 | 3 | 4 | | | IV-1 | Ppme1 |
| 17086 | 3 | 4 | | | IV-1 | Ppox |

Fig. 36 - 90

| | | | | | | |
|---|---|---|---|---|---|---|
| 17087 | 3 | 4 | | | IV-1 | Ppp1ca |
| 17088 | 3 | 4 | | | IV-1 | Ppp1cc |
| 17089 | 3 | 4 | | | IV-1 | Ppp1r11 |
| 17090 | 3 | 4 | | | IV-1 | Ppp1r12c |
| 17091 | 3 | 4 | | | IV-1 | Ppp1r13b |
| 17092 | 3 | 4 | | | IV-1 | Ppp1r14c |
| 17093 | 3 | 4 | | | IV-1 | Ppp1r16a |
| 17094 | 3 | 4 | | | IV-1 | Ppp1r1a |
| 17095 | 3 | 4 | | | IV-1 | Ppp1r1c |
| 17096 | 3 | 4 | | | IV-1 | Ppp1r2 |
| 17097 | 3 | 4 | | | IV-1 | Ppp1r2-ps9 |
| 17098 | 3 | 4 | | | IV-1 | Ppp1r21 |
| 17099 | 3 | 4 | | | IV-1 | Ppp1r32 |
| 17100 | 3 | 4 | | | IV-1 | Ppp1r37 |
| 17101 | 3 | 4 | | | IV-1 | Ppp1r3a |
| 17102 | 3 | 4 | | | IV-1 | Ppp1r42 |
| 17103 | 3 | 4 | | | IV-1 | Ppp1r7 |
| 17104 | 3 | 4 | | | IV-1 | Ppp1r8 |
| 17105 | 3 | 4 | | | IV-1 | Ppp1r9b |
| 17106 | 3 | 4 | | | IV-1 | Ppp2ca |
| 17107 | 3 | 4 | | | IV-1 | Ppp2r1a |
| 17108 | 3 | 4 | | | IV-1 | Ppp2r1b |
| 17109 | 3 | 4 | | | IV-1 | Ppp2r2c |
| 17110 | 3 | 4 | | | IV-1 | Ppp2r2d |
| 17111 | 3 | 4 | | | IV-1 | Ppp2r3a |
| 17112 | 3 | 4 | | | IV-1 | Ppp2r5a |
| 17113 | 3 | 4 | | | IV-1 | Ppp2r5c |
| 17114 | 3 | 4 | | | IV-1 | Ppp2r5d |
| 17115 | 3 | 4 | | | IV-1 | Ppp2r5e |
| 17116 | 3 | 4 | | | IV-1 | Ppp3ca |
| 17117 | 3 | 4 | | | IV-1 | Ppp3cb |
| 17118 | 3 | 4 | | | IV-1 | Ppp3r1 |
| 17119 | 3 | 4 | | | IV-1 | Ppp4r1 |
| 17120 | 3 | 4 | | | IV-1 | Ppp4r1l-ps |
| 17121 | 3 | 4 | | | IV-1 | Ppp4r4 |
| 17122 | 3 | 4 | | | IV-1 | Ppp5c |
| 17123 | 3 | 4 | | | IV-1 | Ppp6r2 |
| 17124 | 3 | 4 | | | IV-1 | Ppt2 |
| 17125 | 3 | 4 | | | IV-1 | Pptc7 |
| 17126 | 3 | 4 | | | IV-1 | Ppwd1 |
| 17127 | 3 | 4 | | | IV-1 | Pqlc3 |
| 17128 | 3 | 4 | | | IV-1 | Praf2 |
| 17129 | 3 | 4 | | | IV-1 | Prame |
| 17130 | 3 | 4 | | | IV-1 | Pramef8 |
| 17131 | 3 | 4 | | | IV-1 | Pramel3 |
| 17132 | 3 | 4 | | | IV-1 | Prdm1 |
| 17133 | 3 | 4 | | | IV-1 | Prdm15 |
| 17134 | 3 | 4 | | | IV-1 | Prdm4 |
| 17135 | 3 | 4 | | | IV-1 | Prdm6 |
| 17136 | 3 | 4 | | | IV-1 | Prdm8 |
| 17137 | 3 | 4 | | | IV-1 | Prdm9 |
| 17138 | 3 | 4 | | | IV-1 | Prdx3 |
| 17139 | 3 | 4 | | | IV-1 | Prdx5 |
| 17140 | 3 | 4 | | | IV-1 | Preb |
| 17141 | 3 | 4 | | | IV-1 | Prep |
| 17142 | 3 | 4 | | | IV-1 | Prex1 |
| 17143 | 3 | 4 | | | IV-1 | Prickle1 |
| 17144 | 3 | 4 | | | IV-1 | Prickle3 |
| 17145 | 3 | 4 | | | IV-1 | Primpol |
| 17146 | 3 | 4 | | | IV-1 | Prkaa1 |
| 17147 | 3 | 4 | | | IV-1 | Prkaa2 |
| 17148 | 3 | 4 | | | IV-1 | Prkaca |
| 17149 | 3 | 4 | | | IV-1 | Prkacb |
| 17150 | 3 | 4 | | | IV-1 | Prkag1 |
| 17151 | 3 | 4 | | | IV-1 | Prkag2 |
| 17152 | 3 | 4 | | | IV-1 | Prkag2os1 |
| 17153 | 3 | 4 | | | IV-1 | Prkag3 |
| 17154 | 3 | 4 | | | IV-1 | Prkar1a |
| 17155 | 3 | 4 | | | IV-1 | Prkcd |
| 17156 | 3 | 4 | | | IV-1 | Prkce |
| 17157 | 3 | 4 | | | IV-1 | Prkch |
| 17158 | 3 | 4 | | | IV-1 | Prkci |
| 17159 | 3 | 4 | | | IV-1 | Prkcsh |
| 17160 | 3 | 4 | | | IV-1 | Prkd1 |
| 17161 | 3 | 4 | | | IV-1 | Prkd2 |
| 17162 | 3 | 4 | | | IV-1 | Prkd3 |
| 17163 | 3 | 4 | | | IV-1 | Prkg2 |
| 17164 | 3 | 4 | | | IV-1 | Prkra |
| 17165 | 3 | 4 | | | IV-1 | Prkrip1 |
| 17166 | 3 | 4 | | | IV-1 | Prkrir |
| 17167 | 3 | 4 | | | IV-1 | Prm3 |
| 17168 | 3 | 4 | | | IV-1 | Prmt10 |
| 17169 | 3 | 4 | | | IV-1 | Prmt2 |
| 17170 | 3 | 4 | | | IV-1 | Prmt3 |
| 17171 | 3 | 4 | | | IV-1 | Prmt5 |
| 17172 | 3 | 4 | | | IV-1 | Prmt6 |
| 17173 | 3 | 4 | | | IV-1 | Prmt8 |
| 17174 | 3 | 4 | | | IV-1 | Prodh2 |
| 17175 | 3 | 4 | | | IV-1 | Pros1 |
| 17176 | 3 | 4 | | | IV-1 | Prosc |
| 17177 | 3 | 4 | | | IV-1 | Proz |
| 17178 | 3 | 4 | | | IV-1 | Prpf18 |
| 17179 | 3 | 4 | | | IV-1 | Prpf19 |
| 17180 | 3 | 4 | | | IV-1 | Prpf3 |
| 17181 | 3 | 4 | | | IV-1 | Prpf31 |
| 17182 | 3 | 4 | | | IV-1 | Prpf38a |
| 17183 | 3 | 4 | | | IV-1 | Prpf38b |
| 17184 | 3 | 4 | | | IV-1 | Prpf39 |
| 17185 | 3 | 4 | | | IV-1 | Prpf4 |
| 17186 | 3 | 4 | | | IV-1 | Prpf40a |
| 17187 | 3 | 4 | | | IV-1 | Prpf40b |
| 17188 | 3 | 4 | | | IV-1 | Prpf6 |
| 17189 | 3 | 4 | | | IV-1 | Prph |
| 17190 | 3 | 4 | | | IV-1 | Prph2 |
| 17191 | 3 | 4 | | | IV-1 | Prps1l1 |
| 17192 | 3 | 4 | | | IV-1 | Prps1l3 |
| 17193 | 3 | 4 | | | IV-1 | Prpsap1 |
| 17194 | 3 | 4 | | | IV-1 | Prpsap2 |
| 17195 | 3 | 4 | | | IV-1 | Prr14 |
| 17196 | 3 | 4 | | | IV-1 | Prr19 |
| 17197 | 3 | 4 | | | IV-1 | Prr22 |
| 17198 | 3 | 4 | | | IV-1 | Prr27 |
| 17199 | 3 | 4 | | | IV-1 | Prr30 |
| 17200 | 3 | 4 | | | IV-1 | Prrc1 |
| 17201 | 3 | 4 | | | IV-1 | Prrc2b |
| 17202 | 3 | 4 | | | IV-1 | Prrg2 |
| 17203 | 3 | 4 | | | IV-1 | Prrg3 |
| 17204 | 3 | 4 | | | IV-1 | Prrt2 |
| 17205 | 3 | 4 | | | IV-1 | Prrx1 |
| 17206 | 3 | 4 | | | IV-1 | Prrx2 |
| 17207 | 3 | 4 | | | IV-1 | Prss16 |
| 17208 | 3 | 4 | | | IV-1 | Prss21 |
| 17209 | 3 | 4 | | | IV-1 | Prss22 |
| 17210 | 3 | 4 | | | IV-1 | Prss23 |
| 17211 | 3 | 4 | | | IV-1 | Prss27 |
| 17212 | 3 | 4 | | | IV-1 | Prss29 |
| 17213 | 3 | 4 | | | IV-1 | Prss30 |
| 17214 | 3 | 4 | | | IV-1 | Prss34 |
| 17215 | 3 | 4 | | | IV-1 | Prss35 |
| 17216 | 3 | 4 | | | IV-1 | Prss38 |
| 17217 | 3 | 4 | | | IV-1 | Prss39 |
| 17218 | 3 | 4 | | | IV-1 | Prss41 |
| 17219 | 3 | 4 | | | IV-1 | Prss43 |
| 17220 | 3 | 4 | | | IV-1 | Prss44 |
| 17221 | 3 | 4 | | | IV-1 | Prss45 |
| 17222 | 3 | 4 | | | IV-1 | Prss46 |
| 17223 | 3 | 4 | | | IV-1 | Prss48 |
| 17224 | 3 | 4 | | | IV-1 | Prss50 |
| 17225 | 3 | 4 | | | IV-1 | Prss52 |
| 17226 | 3 | 4 | | | IV-1 | Prss54 |
| 17227 | 3 | 4 | | | IV-1 | Prss55 |
| 17228 | 3 | 4 | | | IV-1 | Prss58 |
| 17229 | 3 | 4 | | | IV-1 | Prune |
| 17230 | 3 | 4 | | | IV-1 | Prune2 |
| 17231 | 3 | 4 | | | IV-1 | Psap |
| 17232 | 3 | 4 | | | IV-1 | Psapl1 |
| 17233 | 3 | 4 | | | IV-1 | Psat1 |
| 17234 | 3 | 4 | | | IV-1 | Psd |
| 17235 | 3 | 4 | | | IV-1 | Psd2 |
| 17236 | 3 | 4 | | | IV-1 | Psd4 |
| 17237 | 3 | 4 | | | IV-1 | Psen1 |
| 17238 | 3 | 4 | | | IV-1 | Psg19 |
| 17239 | 3 | 4 | | | IV-1 | Psg29 |
| 17240 | 3 | 4 | | | IV-1 | Psip1 |
| 17241 | 3 | 4 | | | IV-1 | Pskh1 |
| 17242 | 3 | 4 | | | IV-1 | Psma1 |
| 17243 | 3 | 4 | | | IV-1 | Psma8 |
| 17244 | 3 | 4 | | | IV-1 | Psmc2 |
| 17245 | 3 | 4 | | | IV-1 | Psmc3 |
| 17246 | 3 | 4 | | | IV-1 | Psmc4 |
| 17247 | 3 | 4 | | | IV-1 | Psmc5 |
| 17248 | 3 | 4 | | | IV-1 | Psmd1 |
| 17249 | 3 | 4 | | | IV-1 | Psmd12 |
| 17250 | 3 | 4 | | | IV-1 | Psmd2 |
| 17251 | 3 | 4 | | | IV-1 | Psmd3 |
| 17252 | 3 | 4 | | | IV-1 | Psmd5 |
| 17253 | 3 | 4 | | | IV-1 | Psmd6 |
| 17254 | 3 | 4 | | | IV-1 | Psmd7 |
| 17255 | 3 | 4 | | | IV-1 | Psmd8 |
| 17256 | 3 | 4 | | | IV-1 | Psmd9 |
| 17257 | 3 | 4 | | | IV-1 | Psme4 |
| 17258 | 3 | 4 | | | IV-1 | Psmg3 |
| 17259 | 3 | 4 | | | IV-1 | Psors1c2 |
| 17260 | 3 | 4 | | | IV-1 | Pspc1 |
| 17261 | 3 | 4 | | | IV-1 | Psph |
| 17262 | 3 | 4 | | | IV-1 | Pstpip2 |
| 17263 | 3 | 4 | | | IV-1 | Ptbp2 |
| 17264 | 3 | 4 | | | IV-1 | Ptbp3 |
| 17265 | 3 | 4 | | | IV-1 | Ptcd1 |
| 17266 | 3 | 4 | | | IV-1 | Ptchd1 |
| 17267 | 3 | 4 | | | IV-1 | Ptchd2 |
| 17268 | 3 | 4 | | | IV-1 | Ptchd3 |
| 17269 | 3 | 4 | | | IV-1 | Ptchd4 |
| 17270 | 3 | 4 | | | IV-1 | Ptdss1 |
| 17271 | 3 | 4 | | | IV-1 | Pten |
| 17272 | 3 | 4 | | | IV-1 | Ptf1a |
| 17273 | 3 | 4 | | | IV-1 | Ptgdr2 |
| 17274 | 3 | 4 | | | IV-1 | Ptger2 |
| 17275 | 3 | 4 | | | IV-1 | Ptger3 |
| 17276 | 3 | 4 | | | IV-1 | Ptges2 |
| 17277 | 3 | 4 | | | IV-1 | Ptgfrn |
| 17278 | 3 | 4 | | | IV-1 | Ptgr2 |

Fig. 36 - 91

| | | | | | | |
|---|---|---|---|---|---|---|
| 17279 | 3 | 4 | | | IV-1 | Ptgs1 |
| 17280 | 3 | 4 | | | IV-1 | Ptgs2 |
| 17281 | 3 | 4 | | | IV-1 | Pth2 |
| 17282 | 3 | 4 | | | IV-1 | Pth2r |
| 17283 | 3 | 4 | | | IV-1 | Ptk2 |
| 17284 | 3 | 4 | | | IV-1 | Ptp4a1 |
| 17285 | 3 | 4 | | | IV-1 | Ptp4a2 |
| 17286 | 3 | 4 | | | IV-1 | Ptpdc1 |
| 17287 | 3 | 4 | | | IV-1 | Ptplad1 |
| 17288 | 3 | 4 | | | IV-1 | Ptpn2 |
| 17289 | 3 | 4 | | | IV-1 | Ptpn21 |
| 17290 | 3 | 4 | | | IV-1 | Ptpn23 |
| 17291 | 3 | 4 | | | IV-1 | Ptpn7 |
| 17292 | 3 | 4 | | | IV-1 | Ptpn9 |
| 17293 | 3 | 4 | | | IV-1 | Ptpre |
| 17294 | 3 | 4 | | | IV-1 | Ptprn2 |
| 17295 | 3 | 4 | | | IV-1 | Ptpro |
| 17296 | 3 | 4 | | | IV-1 | Ptprq |
| 17297 | 3 | 4 | | | IV-1 | Ptprs |
| 17298 | 3 | 4 | | | IV-1 | Ptrh2 |
| 17299 | 3 | 4 | | | IV-1 | Puf60 |
| 17300 | 3 | 4 | | | IV-1 | Pum2 |
| 17301 | 3 | 4 | | | IV-1 | Pus1 |
| 17302 | 3 | 4 | | | IV-1 | Pus10 |
| 17303 | 3 | 4 | | | IV-1 | Pus3 |
| 17304 | 3 | 4 | | | IV-1 | Pus7 |
| 17305 | 3 | 4 | | | IV-1 | Pvr |
| 17306 | 3 | 4 | | | IV-1 | Pvrl1 |
| 17307 | 3 | 4 | | | IV-1 | Pvrl2 |
| 17308 | 3 | 4 | | | IV-1 | Pvrl3 |
| 17309 | 3 | 4 | | | IV-1 | Pwp1 |
| 17310 | 3 | 4 | | | IV-1 | Pwp2 |
| 17311 | 3 | 4 | | | IV-1 | Pwwp2a |
| 17312 | 3 | 4 | | | IV-1 | Pxdn |
| 17313 | 3 | 4 | | | IV-1 | Pxk |
| 17314 | 3 | 4 | | | IV-1 | Pxn |
| 17315 | 3 | 4 | | | IV-1 | Pxt1 |
| 17316 | 3 | 4 | | | IV-1 | Pxylp1 |
| 17317 | 3 | 4 | | | IV-1 | Pycr1 |
| 17318 | 3 | 4 | | | IV-1 | Pygo2 |
| 17319 | 3 | 4 | | | IV-1 | Pyhin1 |
| 17320 | 3 | 4 | | | IV-1 | Pyroxd2 |
| 17321 | 3 | 4 | | | IV-1 | Pyurf |
| 17322 | 3 | 4 | | | IV-1 | Qars |
| 17323 | 3 | 4 | | | IV-1 | Qdpr |
| 17324 | 3 | 4 | | | IV-1 | Qk |
| 17325 | 3 | 4 | | | IV-1 | Qrfpr |
| 17326 | 3 | 4 | | | IV-1 | Qrich1 |
| 17327 | 3 | 4 | | | IV-1 | Qrich2 |
| 17328 | 3 | 4 | | | IV-1 | Qtrtd1 |
| 17329 | 3 | 4 | | | IV-1 | R3hcc1 |
| 17330 | 3 | 4 | | | IV-1 | R3hcc1l |
| 17331 | 3 | 4 | | | IV-1 | R3hdm2 |
| 17332 | 3 | 4 | | | IV-1 | R3hdm4 |
| 17333 | 3 | 4 | | | IV-1 | Rab10 |
| 17334 | 3 | 4 | | | IV-1 | Rab11fip3 |
| 17335 | 3 | 4 | | | IV-1 | Rab11fip5 |
| 17336 | 3 | 4 | | | IV-1 | Rab14 |
| 17337 | 3 | 4 | | | IV-1 | Rab18 |
| 17338 | 3 | 4 | | | IV-1 | Rab19 |
| 17339 | 3 | 4 | | | IV-1 | Rab1b |
| 17340 | 3 | 4 | | | IV-1 | Rab21 |
| 17341 | 3 | 4 | | | IV-1 | Rab23 |
| 17342 | 3 | 4 | | | IV-1 | Rab24 |
| 17343 | 3 | 4 | | | IV-1 | Rab26 |
| 17344 | 3 | 4 | | | IV-1 | Rab2a |
| 17345 | 3 | 4 | | | IV-1 | Rab2b |
| 17346 | 3 | 4 | | | IV-1 | Rab31 |
| 17347 | 3 | 4 | | | IV-1 | Rab33b |
| 17348 | 3 | 4 | | | IV-1 | Rab35 |
| 17349 | 3 | 4 | | | IV-1 | Rab37 |
| 17350 | 3 | 4 | | | IV-1 | Rab38 |
| 17351 | 3 | 4 | | | IV-1 | Rab39 |
| 17352 | 3 | 4 | | | IV-1 | Rab39b |
| 17353 | 3 | 4 | | | IV-1 | Rab3d |
| 17354 | 3 | 4 | | | IV-1 | Rab3gap1 |
| 17355 | 3 | 4 | | | IV-1 | Rab3gap2 |
| 17356 | 3 | 4 | | | IV-1 | Rab40b |
| 17357 | 3 | 4 | | | IV-1 | Rab40c |
| 17358 | 3 | 4 | | | IV-1 | Rab5a |
| 17359 | 3 | 4 | | | IV-1 | Rab5b |
| 17360 | 3 | 4 | | | IV-1 | Rab8a |
| 17361 | 3 | 4 | | | IV-1 | Rab8b |
| 17362 | 3 | 4 | | | IV-1 | Rab9 |
| 17363 | 3 | 4 | | | IV-1 | Rab9b |
| 17364 | 3 | 4 | | | IV-1 | Rabep1 |
| 17365 | 3 | 4 | | | IV-1 | Rabep2 |
| 17366 | 3 | 4 | | | IV-1 | Rabepk |
| 17367 | 3 | 4 | | | IV-1 | Rabgap1 |
| 17368 | 3 | 4 | | | IV-1 | Rabgef1 |
| 17369 | 3 | 4 | | | IV-1 | Rabl6 |
| 17370 | 3 | 4 | | | IV-1 | Rac1 |
| 17371 | 3 | 4 | | | IV-1 | Racgap1 |
| 17372 | 3 | 4 | | | IV-1 | Rad21 |
| 17373 | 3 | 4 | | | IV-1 | Rad23b |
| 17374 | 3 | 4 | | | IV-1 | Rad50 |
| 17375 | 3 | 4 | | | IV-1 | Rad51 |
| 17376 | 3 | 4 | | | IV-1 | Rad51ap1 |
| 17377 | 3 | 4 | | | IV-1 | Rad51ap2 |
| 17378 | 3 | 4 | | | IV-1 | Rad51c |
| 17379 | 3 | 4 | | | IV-1 | Rad51d |
| 17380 | 3 | 4 | | | IV-1 | Rad52 |
| 17381 | 3 | 4 | | | IV-1 | Rad54b |
| 17382 | 3 | 4 | | | IV-1 | Radil |
| 17383 | 3 | 4 | | | IV-1 | Raet1b |
| 17384 | 3 | 4 | | | IV-1 | Raet1c |
| 17385 | 3 | 4 | | | IV-1 | Raf1 |
| 17386 | 3 | 4 | | | IV-1 | Rai14 |
| 17387 | 3 | 4 | | | IV-1 | Rala |
| 17388 | 3 | 4 | | | IV-1 | Ralb |
| 17389 | 3 | 4 | | | IV-1 | Ralgapa1 |
| 17390 | 3 | 4 | | | IV-1 | Ralgds |
| 17391 | 3 | 4 | | | IV-1 | Ralgps1 |
| 17392 | 3 | 4 | | | IV-1 | Ralgps2 |
| 17393 | 3 | 4 | | | IV-1 | Ran |
| 17394 | 3 | 4 | | | IV-1 | Ranbp17 |
| 17395 | 3 | 4 | | | IV-1 | Ranbp3 |
| 17396 | 3 | 4 | | | IV-1 | Ranbp3l |
| 17397 | 3 | 4 | | | IV-1 | Rangap1 |
| 17398 | 3 | 4 | | | IV-1 | Rap1a |
| 17399 | 3 | 4 | | | IV-1 | Rap1b |
| 17400 | 3 | 4 | | | IV-1 | Rap1gap2 |
| 17401 | 3 | 4 | | | IV-1 | Rap1gds1 |
| 17402 | 3 | 4 | | | IV-1 | Rap2b |
| 17403 | 3 | 4 | | | IV-1 | Rap2c |
| 17404 | 3 | 4 | | | IV-1 | Rapgef1 |
| 17405 | 3 | 4 | | | IV-1 | Rapgef2 |
| 17406 | 3 | 4 | | | IV-1 | Rapgefl1 |
| 17407 | 3 | 4 | | | IV-1 | Rapsn |
| 17408 | 3 | 4 | | | IV-1 | Rarg |
| 17409 | 3 | 4 | | | IV-1 | Rars |
| 17410 | 3 | 4 | | | IV-1 | Rasa1 |
| 17411 | 3 | 4 | | | IV-1 | Rasa4 |
| 17412 | 3 | 4 | | | IV-1 | Rasal1 |
| 17413 | 3 | 4 | | | IV-1 | Rasef |
| 17414 | 3 | 4 | | | IV-1 | Rasgef1a |
| 17415 | 3 | 4 | | | IV-1 | Rasgef1c |
| 17416 | 3 | 4 | | | IV-1 | Rasgrp1 |
| 17417 | 3 | 4 | | | IV-1 | Rasgrp4 |
| 17418 | 3 | 4 | | | IV-1 | Rasip1 |
| 17419 | 3 | 4 | | | IV-1 | Rasl10b |
| 17420 | 3 | 4 | | | IV-1 | Rasl2-9 |
| 17421 | 3 | 4 | | | IV-1 | Rassf1 |
| 17422 | 3 | 4 | | | IV-1 | Rassf2 |
| 17423 | 3 | 4 | | | IV-1 | Rassf3 |
| 17424 | 3 | 4 | | | IV-1 | Raver1 |
| 17425 | 3 | 4 | | | IV-1 | Raver2 |
| 17426 | 3 | 4 | | | IV-1 | Rbak |
| 17427 | 3 | 4 | | | IV-1 | Rbakdn |
| 17428 | 3 | 4 | | | IV-1 | Rbbp5 |
| 17429 | 3 | 4 | | | IV-1 | Rbbp6 |
| 17430 | 3 | 4 | | | IV-1 | Rbbp7 |
| 17431 | 3 | 4 | | | IV-1 | Rbbp8nl |
| 17432 | 3 | 4 | | | IV-1 | Rbbp9 |
| 17433 | 3 | 4 | | | IV-1 | Rbck1 |
| 17434 | 3 | 4 | | | IV-1 | Rbfox1 |
| 17435 | 3 | 4 | | | IV-1 | Rbfox2 |
| 17436 | 3 | 4 | | | IV-1 | Rbl1 |
| 17437 | 3 | 4 | | | IV-1 | Rbl2 |
| 17438 | 3 | 4 | | | IV-1 | Rbm10 |
| 17439 | 3 | 4 | | | IV-1 | Rbm12 |
| 17440 | 3 | 4 | | | IV-1 | Rbm12b2 |
| 17441 | 3 | 4 | | | IV-1 | Rbm17 |
| 17442 | 3 | 4 | | | IV-1 | Rbm18 |
| 17443 | 3 | 4 | | | IV-1 | Rbm19 |
| 17444 | 3 | 4 | | | IV-1 | Rbm20 |
| 17445 | 3 | 4 | | | IV-1 | Rbm22 |
| 17446 | 3 | 4 | | | IV-1 | Rbm24 |
| 17447 | 3 | 4 | | | IV-1 | Rbm25 |
| 17448 | 3 | 4 | | | IV-1 | Rbm27 |
| 17449 | 3 | 4 | | | IV-1 | Rbm28 |
| 17450 | 3 | 4 | | | IV-1 | Rbm3ly |
| 17451 | 3 | 4 | | | IV-1 | Rbm34 |
| 17452 | 3 | 4 | | | IV-1 | Rbm39 |
| 17453 | 3 | 4 | | | IV-1 | Rbm41 |
| 17454 | 3 | 4 | | | IV-1 | Rbm42 |
| 17455 | 3 | 4 | | | IV-1 | Rbm43 |
| 17456 | 3 | 4 | | | IV-1 | Rbm44 |
| 17457 | 3 | 4 | | | IV-1 | Rbm45 |
| 17458 | 3 | 4 | | | IV-1 | Rbm47 |
| 17459 | 3 | 4 | | | IV-1 | Rbm4b |
| 17460 | 3 | 4 | | | IV-1 | Rbm5 |
| 17461 | 3 | 4 | | | IV-1 | Rbm7 |
| 17462 | 3 | 4 | | | IV-1 | Rbm8a |
| 17463 | 3 | 4 | | | IV-1 | Rbms2 |
| 17464 | 3 | 4 | | | IV-1 | Rbms3 |
| 17465 | 3 | 4 | | | IV-1 | Rbmx |
| 17466 | 3 | 4 | | | IV-1 | Rbmxl2 |
| 17467 | 3 | 4 | | | IV-1 | Rbpj |
| 17468 | 3 | 4 | | | IV-1 | Rbpjl |
| 17469 | 3 | 4 | | | IV-1 | Rc3h2 |
| 17470 | 3 | 4 | | | IV-1 | Rcan1 |

Fig. 36 - 92

| | | | | | | |
|---|---|---|---|---|---|---|
| 17471 | 3 | 4 | | | IV-1 | Rcan3 |
| 17472 | 3 | 4 | | | IV-1 | Rcbtb1 |
| 17473 | 3 | 4 | | | IV-1 | Rcbtb2 |
| 17474 | 3 | 4 | | | IV-1 | Rcc1 |
| 17475 | 3 | 4 | | | IV-1 | Rcc2 |
| 17476 | 3 | 4 | | | IV-1 | Rccd1 |
| 17477 | 3 | 4 | | | IV-1 | Rce1 |
| 17478 | 3 | 4 | | | IV-1 | Rcl1 |
| 17479 | 3 | 4 | | | IV-1 | Rcn2 |
| 17480 | 3 | 4 | | | IV-1 | Rcsd1 |
| 17481 | 3 | 4 | | | IV-1 | Rd3 |
| 17482 | 3 | 4 | | | IV-1 | Rd3l |
| 17483 | 3 | 4 | | | IV-1 | Rdh1 |
| 17484 | 3 | 4 | | | IV-1 | Rdh10 |
| 17485 | 3 | 4 | | | IV-1 | Rdh13 |
| 17486 | 3 | 4 | | | IV-1 | Rdh14 |
| 17487 | 3 | 4 | | | IV-1 | Rdh19 |
| 17488 | 3 | 4 | | | IV-1 | Rdm1 |
| 17489 | 3 | 4 | | | IV-1 | Rdx |
| 17490 | 3 | 4 | | | IV-1 | Rec8 |
| 17491 | 3 | 4 | | | IV-1 | Reck |
| 17492 | 3 | 4 | | | IV-1 | Recql |
| 17493 | 3 | 4 | | | IV-1 | Recql4 |
| 17494 | 3 | 4 | | | IV-1 | Recql5 |
| 17495 | 3 | 4 | | | IV-1 | Reep3 |
| 17496 | 3 | 4 | | | IV-1 | Reep4 |
| 17497 | 3 | 4 | | | IV-1 | Reep5 |
| 17498 | 3 | 4 | | | IV-1 | Rela |
| 17499 | 3 | 4 | | | IV-1 | Relb |
| 17500 | 3 | 4 | | | IV-1 | Rell1 |
| 17501 | 3 | 4 | | | IV-1 | Rell2 |
| 17502 | 3 | 4 | | | IV-1 | Reln |
| 17503 | 3 | 4 | | | IV-1 | Rem2 |
| 17504 | 3 | 4 | | | IV-1 | Repin1 |
| 17505 | 3 | 4 | | | IV-1 | Reps1 |
| 17506 | 3 | 4 | | | IV-1 | Reps2 |
| 17507 | 3 | 4 | | | IV-1 | Rer1 |
| 17508 | 3 | 4 | | | IV-1 | Resp18 |
| 17509 | 3 | 4 | | | IV-1 | Ret |
| 17510 | 3 | 4 | | | IV-1 | Retnlb |
| 17511 | 3 | 4 | | | IV-1 | Rexo4 |
| 17512 | 3 | 4 | | | IV-1 | Rfc1 |
| 17513 | 3 | 4 | | | IV-1 | Rfc2 |
| 17514 | 3 | 4 | | | IV-1 | Rfng |
| 17515 | 3 | 4 | | | IV-1 | Rfpl3s |
| 17516 | 3 | 4 | | | IV-1 | Rft1 |
| 17517 | 3 | 4 | | | IV-1 | Rftn2 |
| 17518 | 3 | 4 | | | IV-1 | Rfwd2 |
| 17519 | 3 | 4 | | | IV-1 | Rfwd3 |
| 17520 | 3 | 4 | | | IV-1 | Rfx4 |
| 17521 | 3 | 4 | | | IV-1 | Rfx5 |
| 17522 | 3 | 4 | | | IV-1 | Rfx6 |
| 17523 | 3 | 4 | | | IV-1 | Rfx8 |
| 17524 | 3 | 4 | | | IV-1 | Rfxap |
| 17525 | 3 | 4 | | | IV-1 | Rgag1 |
| 17526 | 3 | 4 | | | IV-1 | Rgl1 |
| 17527 | 3 | 4 | | | IV-1 | Rgl2 |
| 17528 | 3 | 4 | | | IV-1 | Rgl3 |
| 17529 | 3 | 4 | | | IV-1 | Rgma |
| 17530 | 3 | 4 | | | IV-1 | Rgs12 |
| 17531 | 3 | 4 | | | IV-1 | Rgs13 |
| 17532 | 3 | 4 | | | IV-1 | Rgs14 |
| 17533 | 3 | 4 | | | IV-1 | Rgs17 |
| 17534 | 3 | 4 | | | IV-1 | Rgs22 |
| 17535 | 3 | 4 | | | IV-1 | Rgs3 |
| 17536 | 3 | 4 | | | IV-1 | Rgs4 |
| 17537 | 3 | 4 | | | IV-1 | Rgs7 |
| 17538 | 3 | 4 | | | IV-1 | Rgs8 |
| 17539 | 3 | 4 | | | IV-1 | Rgsl1 |
| 17540 | 3 | 4 | | | IV-1 | Rhbdf1 |
| 17541 | 3 | 4 | | | IV-1 | Rhbdf2 |
| 17542 | 3 | 4 | | | IV-1 | Rhbdl2 |
| 17543 | 3 | 4 | | | IV-1 | Rhbdl3 |
| 17544 | 3 | 4 | | | IV-1 | Rho |
| 17545 | 3 | 4 | | | IV-1 | Rhoa |
| 17546 | 3 | 4 | | | IV-1 | Rhob |
| 17547 | 3 | 4 | | | IV-1 | Rhobtb1 |
| 17548 | 3 | 4 | | | IV-1 | Rhobtb2 |
| 17549 | 3 | 4 | | | IV-1 | Rhobtb3 |
| 17550 | 3 | 4 | | | IV-1 | Rhof |
| 17551 | 3 | 4 | | | IV-1 | Rhog |
| 17552 | 3 | 4 | | | IV-1 | Rhoq |
| 17553 | 3 | 4 | | | IV-1 | Rhot1 |
| 17554 | 3 | 4 | | | IV-1 | Rhot2 |
| 17555 | 3 | 4 | | | IV-1 | Rhov |
| 17556 | 3 | 4 | | | IV-1 | Rhox10 |
| 17557 | 3 | 4 | | | IV-1 | Rhox11 |
| 17558 | 3 | 4 | | | IV-1 | Rhox13 |
| 17559 | 3 | 4 | | | IV-1 | Rhox3f |
| 17560 | 3 | 4 | | | IV-1 | Rhox3g |
| 17561 | 3 | 4 | | | IV-1 | Rhox8 |
| 17562 | 3 | 4 | | | IV-1 | Rhpn2 |
| 17563 | 3 | 4 | | | IV-1 | Rian |
| 17564 | 3 | 4 | | | IV-1 | Ribc2 |
| 17565 | 3 | 4 | | | IV-1 | Ric3 |
| 17566 | 3 | 4 | | | IV-1 | Ric8b |
| 17567 | 3 | 4 | | | IV-1 | Rimklb |
| 17568 | 3 | 4 | | | IV-1 | Rin1 |
| 17569 | 3 | 4 | | | IV-1 | Rin2 |
| 17570 | 3 | 4 | | | IV-1 | Ring1 |
| 17571 | 3 | 4 | | | IV-1 | Rinl |
| 17572 | 3 | 4 | | | IV-1 | Ripk1 |
| 17573 | 3 | 4 | | | IV-1 | Rit2 |
| 17574 | 3 | 4 | | | IV-1 | Rlbp1 |
| 17575 | 3 | 4 | | | IV-1 | Rlim |
| 17576 | 3 | 4 | | | IV-1 | Rln1 |
| 17577 | 3 | 4 | | | IV-1 | Rmdn1 |
| 17578 | 3 | 4 | | | IV-1 | Rmdn2 |
| 17579 | 3 | 4 | | | IV-1 | Rmdn3 |
| 17580 | 3 | 4 | | | IV-1 | Rmi1 |
| 17581 | 3 | 4 | | | IV-1 | Rmi2 |
| 17582 | 3 | 4 | | | IV-1 | Rnase2b |
| 17583 | 3 | 4 | | | IV-1 | Rnasek |
| 17584 | 3 | 4 | | | IV-1 | Rnasel |
| 17585 | 3 | 4 | | | IV-1 | Rnf103 |
| 17586 | 3 | 4 | | | IV-1 | Rnf111 |
| 17587 | 3 | 4 | | | IV-1 | Rnf112 |
| 17588 | 3 | 4 | | | IV-1 | Rnf122 |
| 17589 | 3 | 4 | | | IV-1 | Rnf123 |
| 17590 | 3 | 4 | | | IV-1 | Rnf126 |
| 17591 | 3 | 4 | | | IV-1 | Rnf13 |
| 17592 | 3 | 4 | | | IV-1 | Rnf130 |
| 17593 | 3 | 4 | | | IV-1 | Rnf135 |
| 17594 | 3 | 4 | | | IV-1 | Rnf138 |
| 17595 | 3 | 4 | | | IV-1 | Rnf139 |
| 17596 | 3 | 4 | | | IV-1 | Rnf146 |
| 17597 | 3 | 4 | | | IV-1 | Rnf148 |
| 17598 | 3 | 4 | | | IV-1 | Rnf150 |
| 17599 | 3 | 4 | | | IV-1 | Rnf157 |
| 17600 | 3 | 4 | | | IV-1 | Rnf165 |
| 17601 | 3 | 4 | | | IV-1 | Rnf167 |
| 17602 | 3 | 4 | | | IV-1 | Rnf168 |
| 17603 | 3 | 4 | | | IV-1 | Rnf169 |
| 17604 | 3 | 4 | | | IV-1 | Rnf17 |
| 17605 | 3 | 4 | | | IV-1 | Rnf170 |
| 17606 | 3 | 4 | | | IV-1 | Rnf183 |
| 17607 | 3 | 4 | | | IV-1 | Rnf185 |
| 17608 | 3 | 4 | | | IV-1 | Rnf2 |
| 17609 | 3 | 4 | | | IV-1 | Rnf20 |
| 17610 | 3 | 4 | | | IV-1 | Rnf214 |
| 17611 | 3 | 4 | | | IV-1 | Rnf215 |
| 17612 | 3 | 4 | | | IV-1 | Rnf216 |
| 17613 | 3 | 4 | | | IV-1 | Rnf219 |
| 17614 | 3 | 4 | | | IV-1 | Rnf220 |
| 17615 | 3 | 4 | | | IV-1 | Rnf222 |
| 17616 | 3 | 4 | | | IV-1 | Rnf224 |
| 17617 | 3 | 4 | | | IV-1 | Rnf26 |
| 17618 | 3 | 4 | | | IV-1 | Rnf32 |
| 17619 | 3 | 4 | | | IV-1 | Rnf34 |
| 17620 | 3 | 4 | | | IV-1 | Rnf4 |
| 17621 | 3 | 4 | | | IV-1 | Rnf40 |
| 17622 | 3 | 4 | | | IV-1 | Rnf41 |
| 17623 | 3 | 4 | | | IV-1 | Rnf44 |
| 17624 | 3 | 4 | | | IV-1 | Rnf6 |
| 17625 | 3 | 4 | | | IV-1 | Rnf7 |
| 17626 | 3 | 4 | | | IV-1 | Rnf8 |
| 17627 | 3 | 4 | | | IV-1 | Rnh1 |
| 17628 | 3 | 4 | | | IV-1 | Rnmt |
| 17629 | 3 | 4 | | | IV-1 | Rnpep |
| 17630 | 3 | 4 | | | IV-1 | Rnps1 |
| 17631 | 3 | 4 | | | IV-1 | Robo2 |
| 17632 | 3 | 4 | | | IV-1 | Robo3 |
| 17633 | 3 | 4 | | | IV-1 | Robo4 |
| 17634 | 3 | 4 | | | IV-1 | Rock1 |
| 17635 | 3 | 4 | | | IV-1 | Rock2 |
| 17636 | 3 | 4 | | | IV-1 | Rom1 |
| 17637 | 3 | 4 | | | IV-1 | Ropn1 |
| 17638 | 3 | 4 | | | IV-1 | Ropn1l |
| 17639 | 3 | 4 | | | IV-1 | Rorb |
| 17640 | 3 | 4 | | | IV-1 | Ros1 |
| 17641 | 3 | 4 | | | IV-1 | Rp9 |
| 17642 | 3 | 4 | | | IV-1 | Rpa1 |
| 17643 | 3 | 4 | | | IV-1 | Rpap1 |
| 17644 | 3 | 4 | | | IV-1 | Rpap2 |
| 17645 | 3 | 4 | | | IV-1 | Rpgr |
| 17646 | 3 | 4 | | | IV-1 | Rpgrip1 |
| 17647 | 3 | 4 | | | IV-1 | Rpgrip1l |
| 17648 | 3 | 4 | | | IV-1 | Rph3a |
| 17649 | 3 | 4 | | | IV-1 | Rpia |
| 17650 | 3 | 4 | | | IV-1 | Rpl10 |
| 17651 | 3 | 4 | | | IV-1 | Rpl10l |
| 17652 | 3 | 4 | | | IV-1 | Rpl22 |
| 17653 | 3 | 4 | | | IV-1 | Rpl23 |
| 17654 | 3 | 4 | | | IV-1 | Rpl3 |
| 17655 | 3 | 4 | | | IV-1 | Rpl6 |
| 17656 | 3 | 4 | | | IV-1 | Rpl7l1 |
| 17657 | 3 | 4 | | | IV-1 | Rpn1 |
| 17658 | 3 | 4 | | | IV-1 | Rpp40 |
| 17659 | 3 | 4 | | | IV-1 | Rprd1b |
| 17660 | 3 | 4 | | | IV-1 | Rprd2 |
| 17661 | 3 | 4 | | | IV-1 | Rps23 |
| 17662 | 3 | 4 | | | IV-1 | Rps26 |

Fig. 36 - 93

| | | | | | | |
|---|---|---|---|---|---|---|
| 17663 | 3 | 4 | | | IV-1 | Rps3a1 |
| 17664 | 3 | 4 | | | IV-1 | Rps6ka1 |
| 17665 | 3 | 4 | | | IV-1 | Rps6ka2 |
| 17666 | 3 | 4 | | | IV-1 | Rps6ka3 |
| 17667 | 3 | 4 | | | IV-1 | Rps6ka5 |
| 17668 | 3 | 4 | | | IV-1 | Rps6ka6 |
| 17669 | 3 | 4 | | | IV-1 | Rps6kb1 |
| 17670 | 3 | 4 | | | IV-1 | Rps6kc1 |
| 17671 | 3 | 4 | | | IV-1 | Rps6kl1 |
| 17672 | 3 | 4 | | | IV-1 | Rptn |
| 17673 | 3 | 4 | | | IV-1 | Rptor |
| 17674 | 3 | 4 | | | IV-1 | Rpusd1 |
| 17675 | 3 | 4 | | | IV-1 | Rpusd4 |
| 17676 | 3 | 4 | | | IV-1 | Rqcd1 |
| 17677 | 3 | 4 | | | IV-1 | Rraga |
| 17678 | 3 | 4 | | | IV-1 | Rragb |
| 17679 | 3 | 4 | | | IV-1 | Rragc |
| 17680 | 3 | 4 | | | IV-1 | Rras2 |
| 17681 | 3 | 4 | | | IV-1 | Rrm1 |
| 17682 | 3 | 4 | | | IV-1 | Rrnad1 |
| 17683 | 3 | 4 | | | IV-1 | Rrs1 |
| 17684 | 3 | 4 | | | IV-1 | Rsl1d1 |
| 17685 | 3 | 4 | | | IV-1 | Rsph3a |
| 17686 | 3 | 4 | | | IV-1 | Rsph3b |
| 17687 | 3 | 4 | | | IV-1 | Rsph6a |
| 17688 | 3 | 4 | | | IV-1 | Rspry1 |
| 17689 | 3 | 4 | | | IV-1 | Rsrc1 |
| 17690 | 3 | 4 | | | IV-1 | Rsrc2 |
| 17691 | 3 | 4 | | | IV-1 | Rsrp1 |
| 17692 | 3 | 4 | | | IV-1 | Rsu1 |
| 17693 | 3 | 4 | | | IV-1 | Rtbdn |
| 17694 | 3 | 4 | | | IV-1 | Rtcb |
| 17695 | 3 | 4 | | | IV-1 | Rtel1 |
| 17696 | 3 | 4 | | | IV-1 | Rtf1 |
| 17697 | 3 | 4 | | | IV-1 | Rtkn2 |
| 17698 | 3 | 4 | | | IV-1 | Rtl1 |
| 17699 | 3 | 4 | | | IV-1 | Rtn1 |
| 17700 | 3 | 4 | | | IV-1 | Rtn3 |
| 17701 | 3 | 4 | | | IV-1 | Rtp1 |
| 17702 | 3 | 4 | | | IV-1 | Rtp3 |
| 17703 | 3 | 4 | | | IV-1 | Rttn |
| 17704 | 3 | 4 | | | IV-1 | Rufy1 |
| 17705 | 3 | 4 | | | IV-1 | Rufy2 |
| 17706 | 3 | 4 | | | IV-1 | Rufy3 |
| 17707 | 3 | 4 | | | IV-1 | Rundc1 |
| 17708 | 3 | 4 | | | IV-1 | Rundc3b |
| 17709 | 3 | 4 | | | IV-1 | Runx1t1 |
| 17710 | 3 | 4 | | | IV-1 | Runx3 |
| 17711 | 3 | 4 | | | IV-1 | Rusc1 |
| 17712 | 3 | 4 | | | IV-1 | Rusc2 |
| 17713 | 3 | 4 | | | IV-1 | Ruvbl2 |
| 17714 | 3 | 4 | | | IV-1 | Rwdd1 |
| 17715 | 3 | 4 | | | IV-1 | Rwdd2b |
| 17716 | 3 | 4 | | | IV-1 | Rwdd3 |
| 17717 | 3 | 4 | | | IV-1 | Rwdd4a |
| 17718 | 3 | 4 | | | IV-1 | Rxfp1 |
| 17719 | 3 | 4 | | | IV-1 | Rxfp2 |
| 17720 | 3 | 4 | | | IV-1 | Rxfp3 |
| 17721 | 3 | 4 | | | IV-1 | Rxrb |
| 17722 | 3 | 4 | | | IV-1 | Rybp |
| 17723 | 3 | 4 | | | IV-1 | Ryr2 |
| 17724 | 3 | 4 | | | IV-1 | Ryr3 |
| 17725 | 3 | 4 | | | IV-1 | S100a14 |
| 17726 | 3 | 4 | | | IV-1 | S1pr1 |
| 17727 | 3 | 4 | | | IV-1 | S1pr2 |
| 17728 | 3 | 4 | | | IV-1 | S1pr3 |
| 17729 | 3 | 4 | | | IV-1 | Saa4 |
| 17730 | 3 | 4 | | | IV-1 | Saal1 |
| 17731 | 3 | 4 | | | IV-1 | Sacm1l |
| 17732 | 3 | 4 | | | IV-1 | Sae1 |
| 17733 | 3 | 4 | | | IV-1 | Sall2 |
| 17734 | 3 | 4 | | | IV-1 | Sall4 |
| 17735 | 3 | 4 | | | IV-1 | Samd1 |
| 17736 | 3 | 4 | | | IV-1 | Samd11 |
| 17737 | 3 | 4 | | | IV-1 | Samd4b |
| 17738 | 3 | 4 | | | IV-1 | Samd7 |
| 17739 | 3 | 4 | | | IV-1 | Samt2 |
| 17740 | 3 | 4 | | | IV-1 | Samt4 |
| 17741 | 3 | 4 | | | IV-1 | Sap130 |
| 17742 | 3 | 4 | | | IV-1 | Sap18 |
| 17743 | 3 | 4 | | | IV-1 | Sar1a |
| 17744 | 3 | 4 | | | IV-1 | Sar1b |
| 17745 | 3 | 4 | | | IV-1 | Sardh |
| 17746 | 3 | 4 | | | IV-1 | Sarm1 |
| 17747 | 3 | 4 | | | IV-1 | Sars |
| 17748 | 3 | 4 | | | IV-1 | Sars2 |
| 17749 | 3 | 4 | | | IV-1 | Sart1 |
| 17750 | 3 | 4 | | | IV-1 | Sart3 |
| 17751 | 3 | 4 | | | IV-1 | Sass6 |
| 17752 | 3 | 4 | | | IV-1 | Satb1 |
| 17753 | 3 | 4 | | | IV-1 | Satb2 |
| 17754 | 3 | 4 | | | IV-1 | Saysd1 |
| 17755 | 3 | 4 | | | IV-1 | Sbf1 |
| 17756 | 3 | 4 | | | IV-1 | Sbk2 |
| 17757 | 3 | 4 | | | IV-1 | Sbk3 |
| 17758 | 3 | 4 | | | IV-1 | Sbno1 |
| 17759 | 3 | 4 | | | IV-1 | Sbspon |
| 17760 | 3 | 4 | | | IV-1 | Scaf1 |
| 17761 | 3 | 4 | | | IV-1 | Scaf8 |
| 17762 | 3 | 4 | | | IV-1 | Scamp1 |
| 17763 | 3 | 4 | | | IV-1 | Scamp2 |
| 17764 | 3 | 4 | | | IV-1 | Scamp3 |
| 17765 | 3 | 4 | | | IV-1 | Scamp4 |
| 17766 | 3 | 4 | | | IV-1 | Scand1 |
| 17767 | 3 | 4 | | | IV-1 | Scap |
| 17768 | 3 | 4 | | | IV-1 | Scaper |
| 17769 | 3 | 4 | | | IV-1 | Scara3 |
| 17770 | 3 | 4 | | | IV-1 | Scara5 |
| 17771 | 3 | 4 | | | IV-1 | Scarb1 |
| 17772 | 3 | 4 | | | IV-1 | Scarf1 |
| 17773 | 3 | 4 | | | IV-1 | Scarf2 |
| 17774 | 3 | 4 | | | IV-1 | Sccpdh |
| 17775 | 3 | 4 | | | IV-1 | Scfd1 |
| 17776 | 3 | 4 | | | IV-1 | Scfd2 |
| 17777 | 3 | 4 | | | IV-1 | Scg2 |
| 17778 | 3 | 4 | | | IV-1 | Scgb1b27 |
| 17779 | 3 | 4 | | | IV-1 | Scgb1c1 |
| 17780 | 3 | 4 | | | IV-1 | Scgb2b23-ps |
| 17781 | 3 | 4 | | | IV-1 | Scgb2b27 |
| 17782 | 3 | 4 | | | IV-1 | Scin |
| 17783 | 3 | 4 | | | IV-1 | Scmh1 |
| 17784 | 3 | 4 | | | IV-1 | Scml2 |
| 17785 | 3 | 4 | | | IV-1 | Scn2a1 |
| 17786 | 3 | 4 | | | IV-1 | Scn4a |
| 17787 | 3 | 4 | | | IV-1 | Scn4b |
| 17788 | 3 | 4 | | | IV-1 | Scn7a |
| 17789 | 3 | 4 | | | IV-1 | Scn8a |
| 17790 | 3 | 4 | | | IV-1 | Scn9a |
| 17791 | 3 | 4 | | | IV-1 | Scnn1b |
| 17792 | 3 | 4 | | | IV-1 | Scnn1g |
| 17793 | 3 | 4 | | | IV-1 | Sco1 |
| 17794 | 3 | 4 | | | IV-1 | Scp2d1 |
| 17795 | 3 | 4 | | | IV-1 | Scpep1 |
| 17796 | 3 | 4 | | | IV-1 | Scrg1 |
| 17797 | 3 | 4 | | | IV-1 | Scrn3 |
| 17798 | 3 | 4 | | | IV-1 | Scrt1 |
| 17799 | 3 | 4 | | | IV-1 | Scrt2 |
| 17800 | 3 | 4 | | | IV-1 | Sctr |
| 17801 | 3 | 4 | | | IV-1 | Scyl1 |
| 17802 | 3 | 4 | | | IV-1 | Scyl2 |
| 17803 | 3 | 4 | | | IV-1 | Scyl3 |
| 17804 | 3 | 4 | | | IV-1 | Sdad1 |
| 17805 | 3 | 4 | | | IV-1 | Sdc2 |
| 17806 | 3 | 4 | | | IV-1 | Sdcbp |
| 17807 | 3 | 4 | | | IV-1 | Sdccag3 |
| 17808 | 3 | 4 | | | IV-1 | Sde2 |
| 17809 | 3 | 4 | | | IV-1 | Sdf4 |
| 17810 | 3 | 4 | | | IV-1 | Sdha |
| 17811 | 3 | 4 | | | IV-1 | Sdhd |
| 17812 | 3 | 4 | | | IV-1 | Sdk1 |
| 17813 | 3 | 4 | | | IV-1 | Sdk2 |
| 17814 | 3 | 4 | | | IV-1 | Sdr16c5 |
| 17815 | 3 | 4 | | | IV-1 | Sdr16c6 |
| 17816 | 3 | 4 | | | IV-1 | Sdr42e1 |
| 17817 | 3 | 4 | | | IV-1 | Sdr9c7 |
| 17818 | 3 | 4 | | | IV-1 | Sds |
| 17819 | 3 | 4 | | | IV-1 | Sebox |
| 17820 | 3 | 4 | | | IV-1 | Sec11a |
| 17821 | 3 | 4 | | | IV-1 | Sec14l1 |
| 17822 | 3 | 4 | | | IV-1 | Sec16b |
| 17823 | 3 | 4 | | | IV-1 | Sec22a |
| 17824 | 3 | 4 | | | IV-1 | Sec22b |
| 17825 | 3 | 4 | | | IV-1 | Sec22c |
| 17826 | 3 | 4 | | | IV-1 | Sec23a |
| 17827 | 3 | 4 | | | IV-1 | Sec23b |
| 17828 | 3 | 4 | | | IV-1 | Sec23ip |
| 17829 | 3 | 4 | | | IV-1 | Sec24a |
| 17830 | 3 | 4 | | | IV-1 | Sec24b |
| 17831 | 3 | 4 | | | IV-1 | Sec24c |
| 17832 | 3 | 4 | | | IV-1 | Sec24d |
| 17833 | 3 | 4 | | | IV-1 | Sec31a |
| 17834 | 3 | 4 | | | IV-1 | Sec61a2 |
| 17835 | 3 | 4 | | | IV-1 | Sec62 |
| 17836 | 3 | 4 | | | IV-1 | Sec63 |
| 17837 | 3 | 4 | | | IV-1 | Secisbp2l |
| 17838 | 3 | 4 | | | IV-1 | Seh1l |
| 17839 | 3 | 4 | | | IV-1 | Sel1l2 |
| 17840 | 3 | 4 | | | IV-1 | Sel1l3 |
| 17841 | 3 | 4 | | | IV-1 | Selo |
| 17842 | 3 | 4 | | | IV-1 | Selt |
| 17843 | 3 | 4 | | | IV-1 | Sema3a |
| 17844 | 3 | 4 | | | IV-1 | Sema3c |
| 17845 | 3 | 4 | | | IV-1 | Sema3e |
| 17846 | 3 | 4 | | | IV-1 | Sema3f |
| 17847 | 3 | 4 | | | IV-1 | Sema4a |
| 17848 | 3 | 4 | | | IV-1 | Sema4b |
| 17849 | 3 | 4 | | | IV-1 | Sema4c |
| 17850 | 3 | 4 | | | IV-1 | Sema4f |
| 17851 | 3 | 4 | | | IV-1 | Sema5b |
| 17852 | 3 | 4 | | | IV-1 | Sema6a |
| 17853 | 3 | 4 | | | IV-1 | Sema6d |
| 17854 | 3 | 4 | | | IV-1 | Senp1 |

Fig. 36 - 94

| | | | | | | |
|---|---|---|---|---|---|---|
| 17855 | 3 | 4 | | | IV-1 | Senp2 |
| 17856 | 3 | 4 | | | IV-1 | Senp3 |
| 17857 | 3 | 4 | | | IV-1 | Senp5 |
| 17858 | 3 | 4 | | | IV-1 | Senp6 |
| 17859 | 3 | 4 | | | IV-1 | Senp8 |
| 17860 | 3 | 4 | | | IV-1 | Sep15 |
| 17861 | 3 | 4 | | | IV-1 | Sephs1 |
| 17862 | 3 | 4 | | | IV-1 | Sepn1 |
| 17863 | 3 | 4 | | | IV-1 | Sept10 |
| 17864 | 3 | 4 | | | IV-1 | Sept11 |
| 17865 | 3 | 4 | | | IV-1 | Sept12 |
| 17866 | 3 | 4 | | | IV-1 | Sept2 |
| 17867 | 3 | 4 | | | IV-1 | Serac1 |
| 17868 | 3 | 4 | | | IV-1 | Serinc4 |
| 17869 | 3 | 4 | | | IV-1 | Serp1 |
| 17870 | 3 | 4 | | | IV-1 | Serp2 |
| 17871 | 3 | 4 | | | IV-1 | Serpina12 |
| 17872 | 3 | 4 | | | IV-1 | Serpina3b |
| 17873 | 3 | 4 | | | IV-1 | Serpina3f |
| 17874 | 3 | 4 | | | IV-1 | Serpina5 |
| 17875 | 3 | 4 | | | IV-1 | Serpina6 |
| 17876 | 3 | 4 | | | IV-1 | Serpina9 |
| 17877 | 3 | 4 | | | IV-1 | Serpinb10 |
| 17878 | 3 | 4 | | | IV-1 | Serpinb11 |
| 17879 | 3 | 4 | | | IV-1 | Serpinb12 |
| 17880 | 3 | 4 | | | IV-1 | Serpinb13 |
| 17881 | 3 | 4 | | | IV-1 | Serpinb1b |
| 17882 | 3 | 4 | | | IV-1 | Serpinb3a |
| 17883 | 3 | 4 | | | IV-1 | Serpinb3b |
| 17884 | 3 | 4 | | | IV-1 | Serpinb5 |
| 17885 | 3 | 4 | | | IV-1 | Serpinb6c |
| 17886 | 3 | 4 | | | IV-1 | Serpinb7 |
| 17887 | 3 | 4 | | | IV-1 | Serpinh1 |
| 17888 | 3 | 4 | | | IV-1 | Serpini1 |
| 17889 | 3 | 4 | | | IV-1 | Sertad2 |
| 17890 | 3 | 4 | | | IV-1 | Sertm1 |
| 17891 | 3 | 4 | | | IV-1 | Set |
| 17892 | 3 | 4 | | | IV-1 | Setd3 |
| 17893 | 3 | 4 | | | IV-1 | Setd5 |
| 17894 | 3 | 4 | | | IV-1 | Setd8 |
| 17895 | 3 | 4 | | | IV-1 | Setdb1 |
| 17896 | 3 | 4 | | | IV-1 | Sez6 |
| 17897 | 3 | 4 | | | IV-1 | Sez6l |
| 17898 | 3 | 4 | | | IV-1 | Sf1 |
| 17899 | 3 | 4 | | | IV-1 | Sf3a3 |
| 17900 | 3 | 4 | | | IV-1 | Sf3b1 |
| 17901 | 3 | 4 | | | IV-1 | Sf3b2 |
| 17902 | 3 | 4 | | | IV-1 | Sf3b3 |
| 17903 | 3 | 4 | | | IV-1 | Sf3b4 |
| 17904 | 3 | 4 | | | IV-1 | Sfmbt1 |
| 17905 | 3 | 4 | | | IV-1 | Sfmbt2 |
| 17906 | 3 | 4 | | | IV-1 | Sfr1 |
| 17907 | 3 | 4 | | | IV-1 | Sfrp1 |
| 17908 | 3 | 4 | | | IV-1 | Sfswap |
| 17909 | 3 | 4 | | | IV-1 | Sft2d2 |
| 17910 | 3 | 4 | | | IV-1 | Sft2d3 |
| 17911 | 3 | 4 | | | IV-1 | Sftpb |
| 17912 | 3 | 4 | | | IV-1 | Sftpd |
| 17913 | 3 | 4 | | | IV-1 | Sfxn4 |
| 17914 | 3 | 4 | | | IV-1 | Sfxn5 |
| 17915 | 3 | 4 | | | IV-1 | Sgca |
| 17916 | 3 | 4 | | | IV-1 | Sgcb |
| 17917 | 3 | 4 | | | IV-1 | Sgcg |
| 17918 | 3 | 4 | | | IV-1 | Sgip1 |
| 17919 | 3 | 4 | | | IV-1 | Sgk2 |
| 17920 | 3 | 4 | | | IV-1 | Sgms1 |
| 17921 | 3 | 4 | | | IV-1 | Sgms2 |
| 17922 | 3 | 4 | | | IV-1 | Sgpl1 |
| 17923 | 3 | 4 | | | IV-1 | Sgpp1 |
| 17924 | 3 | 4 | | | IV-1 | Sgpp2 |
| 17925 | 3 | 4 | | | IV-1 | Sgsm1 |
| 17926 | 3 | 4 | | | IV-1 | Sh2b1 |
| 17927 | 3 | 4 | | | IV-1 | Sh2d1b1 |
| 17928 | 3 | 4 | | | IV-1 | Sh2d1b2 |
| 17929 | 3 | 4 | | | IV-1 | Sh2d2a |
| 17930 | 3 | 4 | | | IV-1 | Sh2d3c |
| 17931 | 3 | 4 | | | IV-1 | Sh2d4a |
| 17932 | 3 | 4 | | | IV-1 | Sh2d5 |
| 17933 | 3 | 4 | | | IV-1 | Sh2d7 |
| 17934 | 3 | 4 | | | IV-1 | Sh3bp1 |
| 17935 | 3 | 4 | | | IV-1 | Sh3bp2 |
| 17936 | 3 | 4 | | | IV-1 | Sh3bp5 |
| 17937 | 3 | 4 | | | IV-1 | Sh3bp5l |
| 17938 | 3 | 4 | | | IV-1 | Sh3d19 |
| 17939 | 3 | 4 | | | IV-1 | Sh3d21 |
| 17940 | 3 | 4 | | | IV-1 | Sh3gl1 |
| 17941 | 3 | 4 | | | IV-1 | Sh3gl3 |
| 17942 | 3 | 4 | | | IV-1 | Sh3rf1 |
| 17943 | 3 | 4 | | | IV-1 | Sh3rf2 |
| 17944 | 3 | 4 | | | IV-1 | Sh3rf3 |
| 17945 | 3 | 4 | | | IV-1 | Sharpin |
| 17946 | 3 | 4 | | | IV-1 | Shbg |
| 17947 | 3 | 4 | | | IV-1 | Shc1 |
| 17948 | 3 | 4 | | | IV-1 | Shc2 |
| 17949 | 3 | 4 | | | IV-1 | Shcbp1 |
| 17950 | 3 | 4 | | | IV-1 | Shcbp1l |
| 17951 | 3 | 4 | | | IV-1 | Shd |
| 17952 | 3 | 4 | | | IV-1 | She |
| 17953 | 3 | 4 | | | IV-1 | Shh |
| 17954 | 3 | 4 | | | IV-1 | Shisa3 |
| 17955 | 3 | 4 | | | IV-1 | Shisa5 |
| 17956 | 3 | 4 | | | IV-1 | Shisa9 |
| 17957 | 3 | 4 | | | IV-1 | Shkbp1 |
| 17958 | 3 | 4 | | | IV-1 | Shrrt2 |
| 17959 | 3 | 4 | | | IV-1 | Shoc2 |
| 17960 | 3 | 4 | | | IV-1 | Shpk |
| 17961 | 3 | 4 | | | IV-1 | Shq1 |
| 17962 | 3 | 4 | | | IV-1 | Siae |
| 17963 | 3 | 4 | | | IV-1 | Siah1a |
| 17964 | 3 | 4 | | | IV-1 | Siah2 |
| 17965 | 3 | 4 | | | IV-1 | Sidt1 |
| 17966 | 3 | 4 | | | IV-1 | Sidt2 |
| 17967 | 3 | 4 | | | IV-1 | Siglec1 |
| 17968 | 3 | 4 | | | IV-1 | Siglec5 |
| 17969 | 3 | 4 | | | IV-1 | Sike1 |
| 17970 | 3 | 4 | | | IV-1 | Sil1 |
| 17971 | 3 | 4 | | | IV-1 | Sim2 |
| 17972 | 3 | 4 | | | IV-1 | Sirpa |
| 17973 | 3 | 4 | | | IV-1 | Sirt1 |
| 17974 | 3 | 4 | | | IV-1 | Sirt4 |
| 17975 | 3 | 4 | | | IV-1 | Six1 |
| 17976 | 3 | 4 | | | IV-1 | Six2 |
| 17977 | 3 | 4 | | | IV-1 | Six3os1 |
| 17978 | 3 | 4 | | | IV-1 | Six4 |
| 17979 | 3 | 4 | | | IV-1 | Six5 |
| 17980 | 3 | 4 | | | IV-1 | Ska1 |
| 17981 | 3 | 4 | | | IV-1 | Ska2 |
| 17982 | 3 | 4 | | | IV-1 | Ska3 |
| 17983 | 3 | 4 | | | IV-1 | Skint1 |
| 17984 | 3 | 4 | | | IV-1 | Skint2 |
| 17985 | 3 | 4 | | | IV-1 | Skint5 |
| 17986 | 3 | 4 | | | IV-1 | Skint6 |
| 17987 | 3 | 4 | | | IV-1 | Skint8 |
| 17988 | 3 | 4 | | | IV-1 | Skiv2l2 |
| 17989 | 3 | 4 | | | IV-1 | Sla2 |
| 17990 | 3 | 4 | | | IV-1 | Slamf7 |
| 17991 | 3 | 4 | | | IV-1 | Slc10a3 |
| 17992 | 3 | 4 | | | IV-1 | Slc10a4 |
| 17993 | 3 | 4 | | | IV-1 | Slc10a7 |
| 17994 | 3 | 4 | | | IV-1 | Slc11a2 |
| 17995 | 3 | 4 | | | IV-1 | Slc12a2 |
| 17996 | 3 | 4 | | | IV-1 | Slc12a3 |
| 17997 | 3 | 4 | | | IV-1 | Slc12a4 |
| 17998 | 3 | 4 | | | IV-1 | Slc12a5 |
| 17999 | 3 | 4 | | | IV-1 | Slc12a6 |
| 18000 | 3 | 4 | | | IV-1 | Slc12a7 |
| 18001 | 3 | 4 | | | IV-1 | Slc12a8 |
| 18002 | 3 | 4 | | | IV-1 | Slc12a9 |
| 18003 | 3 | 4 | | | IV-1 | Slc13a2 |
| 18004 | 3 | 4 | | | IV-1 | Slc13a3 |
| 18005 | 3 | 4 | | | IV-1 | Slc13a4 |
| 18006 | 3 | 4 | | | IV-1 | Slc15a1 |
| 18007 | 3 | 4 | | | IV-1 | Slc15a4 |
| 18008 | 3 | 4 | | | IV-1 | Slc15a5 |
| 18009 | 3 | 4 | | | IV-1 | Slc16a4 |
| 18010 | 3 | 4 | | | IV-1 | Slc16a9 |
| 18011 | 3 | 4 | | | IV-1 | Slc17a2 |
| 18012 | 3 | 4 | | | IV-1 | Slc17a3 |
| 18013 | 3 | 4 | | | IV-1 | Slc17a4 |
| 18014 | 3 | 4 | | | IV-1 | Slc17a5 |
| 18015 | 3 | 4 | | | IV-1 | Slc17a6 |
| 18016 | 3 | 4 | | | IV-1 | Slc17a7 |
| 18017 | 3 | 4 | | | IV-1 | Slc17a8 |
| 18018 | 3 | 4 | | | IV-1 | Slc18a1 |
| 18019 | 3 | 4 | | | IV-1 | Slc18b1 |
| 18020 | 3 | 4 | | | IV-1 | Slc19a1 |
| 18021 | 3 | 4 | | | IV-1 | Slc19a2 |
| 18022 | 3 | 4 | | | IV-1 | Slc19a3 |
| 18023 | 3 | 4 | | | IV-1 | Slc1a6 |
| 18024 | 3 | 4 | | | IV-1 | Slc20a1 |
| 18025 | 3 | 4 | | | IV-1 | Slc22a13b-ps |
| 18026 | 3 | 4 | | | IV-1 | Slc22a14 |
| 18027 | 3 | 4 | | | IV-1 | Slc22a15 |
| 18028 | 3 | 4 | | | IV-1 | Slc22a16 |
| 18029 | 3 | 4 | | | IV-1 | Slc22a19 |
| 18030 | 3 | 4 | | | IV-1 | Slc22a2 |
| 18031 | 3 | 4 | | | IV-1 | Slc22a21 |
| 18032 | 3 | 4 | | | IV-1 | Slc22a22 |
| 18033 | 3 | 4 | | | IV-1 | Slc22a26 |
| 18034 | 3 | 4 | | | IV-1 | Slc22a28 |
| 18035 | 3 | 4 | | | IV-1 | Slc22a29 |
| 18036 | 3 | 4 | | | IV-1 | Slc22a30 |
| 18037 | 3 | 4 | | | IV-1 | Slc22a4 |
| 18038 | 3 | 4 | | | IV-1 | Slc22a5 |
| 18039 | 3 | 4 | | | IV-1 | Slc22a6 |
| 18040 | 3 | 4 | | | IV-1 | Slc22a8 |
| 18041 | 3 | 4 | | | IV-1 | Slc23a1 |
| 18042 | 3 | 4 | | | IV-1 | Slc25a11 |
| 18043 | 3 | 4 | | | IV-1 | Slc25a12 |
| 18044 | 3 | 4 | | | IV-1 | Slc25a14 |
| 18045 | 3 | 4 | | | IV-1 | Slc25a17 |
| 18046 | 3 | 4 | | | IV-1 | Slc25a18 |

Fig. 36 - 95

| | | | | | | |
|---|---|---|---|---|---|---|
| 18047 | 3 | 4 | | | IV-1 | Slc25a19 |
| 18048 | 3 | 4 | | | IV-1 | Slc25a2 |
| 18049 | 3 | 4 | | | IV-1 | Slc25a20 |
| 18050 | 3 | 4 | | | IV-1 | Slc25a21 |
| 18051 | 3 | 4 | | | IV-1 | Slc25a26 |
| 18052 | 3 | 4 | | | IV-1 | Slc25a28 |
| 18053 | 3 | 4 | | | IV-1 | Slc25a3 |
| 18054 | 3 | 4 | | | IV-1 | Slc25a31 |
| 18055 | 3 | 4 | | | IV-1 | Slc25a38 |
| 18056 | 3 | 4 | | | IV-1 | Slc25a41 |
| 18057 | 3 | 4 | | | IV-1 | Slc25a43 |
| 18058 | 3 | 4 | | | IV-1 | Slc25a44 |
| 18059 | 3 | 4 | | | IV-1 | Slc25a46 |
| 18060 | 3 | 4 | | | IV-1 | Slc25a48 |
| 18061 | 3 | 4 | | | IV-1 | Slc25a53 |
| 18062 | 3 | 4 | | | IV-1 | Slc25a54 |
| 18063 | 3 | 4 | | | IV-1 | Slc26a10 |
| 18064 | 3 | 4 | | | IV-1 | Slc26a11 |
| 18065 | 3 | 4 | | | IV-1 | Slc26a4 |
| 18066 | 3 | 4 | | | IV-1 | Slc26a7 |
| 18067 | 3 | 4 | | | IV-1 | Slc26a8 |
| 18068 | 3 | 4 | | | IV-1 | Slc26a9 |
| 18069 | 3 | 4 | | | IV-1 | Slc27a4 |
| 18070 | 3 | 4 | | | IV-1 | Slc28a1 |
| 18071 | 3 | 4 | | | IV-1 | Slc28a3 |
| 18072 | 3 | 4 | | | IV-1 | Slc29a1 |
| 18073 | 3 | 4 | | | IV-1 | Slc29a4 |
| 18074 | 3 | 4 | | | IV-1 | Slc2a1 |
| 18075 | 3 | 4 | | | IV-1 | Slc2a10 |
| 18076 | 3 | 4 | | | IV-1 | Slc2a13 |
| 18077 | 3 | 4 | | | IV-1 | Slc2a2 |
| 18078 | 3 | 4 | | | IV-1 | Slc2a4rg-ps |
| 18079 | 3 | 4 | | | IV-1 | Slc2a9 |
| 18080 | 3 | 4 | | | IV-1 | Slc30a1 |
| 18081 | 3 | 4 | | | IV-1 | Slc30a4 |
| 18082 | 3 | 4 | | | IV-1 | Slc30a5 |
| 18083 | 3 | 4 | | | IV-1 | Slc30a8 |
| 18084 | 3 | 4 | | | IV-1 | Slc30a9 |
| 18085 | 3 | 4 | | | IV-1 | Slc31a1 |
| 18086 | 3 | 4 | | | IV-1 | Slc31a2 |
| 18087 | 3 | 4 | | | IV-1 | Slc32a1 |
| 18088 | 3 | 4 | | | IV-1 | Slc33a1 |
| 18089 | 3 | 4 | | | IV-1 | Slc34a3 |
| 18090 | 3 | 4 | | | IV-1 | Slc35a1 |
| 18091 | 3 | 4 | | | IV-1 | Slc35a2 |
| 18092 | 3 | 4 | | | IV-1 | Slc35a4 |
| 18093 | 3 | 4 | | | IV-1 | Slc35a5 |
| 18094 | 3 | 4 | | | IV-1 | Slc35b1 |
| 18095 | 3 | 4 | | | IV-1 | Slc35b2 |
| 18096 | 3 | 4 | | | IV-1 | Slc35b4 |
| 18097 | 3 | 4 | | | IV-1 | Slc35c1 |
| 18098 | 3 | 4 | | | IV-1 | Slc35c2 |
| 18099 | 3 | 4 | | | IV-1 | Slc35d1 |
| 18100 | 3 | 4 | | | IV-1 | Slc35d3 |
| 18101 | 3 | 4 | | | IV-1 | Slc35e1 |
| 18102 | 3 | 4 | | | IV-1 | Slc35e2 |
| 18103 | 3 | 4 | | | IV-1 | Slc35e3 |
| 18104 | 3 | 4 | | | IV-1 | Slc35e4 |
| 18105 | 3 | 4 | | | IV-1 | Slc35f1 |
| 18106 | 3 | 4 | | | IV-1 | Slc35f3 |
| 18107 | 3 | 4 | | | IV-1 | Slc35f5 |
| 18108 | 3 | 4 | | | IV-1 | Slc35g3 |
| 18109 | 3 | 4 | | | IV-1 | Slc36a1 |
| 18110 | 3 | 4 | | | IV-1 | Slc37a3 |
| 18111 | 3 | 4 | | | IV-1 | Slc38a10 |
| 18112 | 3 | 4 | | | IV-1 | Slc38a6 |
| 18113 | 3 | 4 | | | IV-1 | Slc38a7 |
| 18114 | 3 | 4 | | | IV-1 | Slc38a9 |
| 18115 | 3 | 4 | | | IV-1 | Slc39a11 |
| 18116 | 3 | 4 | | | IV-1 | Slc39a12 |
| 18117 | 3 | 4 | | | IV-1 | Slc39a13 |
| 18118 | 3 | 4 | | | IV-1 | Slc39a14 |
| 18119 | 3 | 4 | | | IV-1 | Slc39a2 |
| 18120 | 3 | 4 | | | IV-1 | Slc39a3 |
| 18121 | 3 | 4 | | | IV-1 | Slc39a6 |
| 18122 | 3 | 4 | | | IV-1 | Slc39a7 |
| 18123 | 3 | 4 | | | IV-1 | Slc39a9 |
| 18124 | 3 | 4 | | | IV-1 | Slc3a1 |
| 18125 | 3 | 4 | | | IV-1 | Slc41a1 |
| 18126 | 3 | 4 | | | IV-1 | Slc41a3 |
| 18127 | 3 | 4 | | | IV-1 | Slc43a2 |
| 18128 | 3 | 4 | | | IV-1 | Slc43a3 |
| 18129 | 3 | 4 | | | IV-1 | Slc44a2 |
| 18130 | 3 | 4 | | | IV-1 | Slc44a3 |
| 18131 | 3 | 4 | | | IV-1 | Slc44a4 |
| 18132 | 3 | 4 | | | IV-1 | Slc44a5 |
| 18133 | 3 | 4 | | | IV-1 | Slc45a1 |
| 18134 | 3 | 4 | | | IV-1 | Slc46a2 |
| 18135 | 3 | 4 | | | IV-1 | Slc46a3 |
| 18136 | 3 | 4 | | | IV-1 | Slc4a10 |
| 18137 | 3 | 4 | | | IV-1 | Slc4a11 |
| 18138 | 3 | 4 | | | IV-1 | Slc4a1ap |
| 18139 | 3 | 4 | | | IV-1 | Slc4a2 |
| 18140 | 3 | 4 | | | IV-1 | Slc4a3 |
| 18141 | 3 | 4 | | | IV-1 | Slc4a5 |
| 18142 | 3 | 4 | | | IV-1 | Slc4a9 |

| | | | | | | |
|---|---|---|---|---|---|---|
| 18143 | 3 | 4 | | | IV-1 | Slc51a |
| 18144 | 3 | 4 | | | IV-1 | Slc51b |
| 18145 | 3 | 4 | | | IV-1 | Slc52a2 |
| 18146 | 3 | 4 | | | IV-1 | Slc5a10 |
| 18147 | 3 | 4 | | | IV-1 | Slc5a11 |
| 18148 | 3 | 4 | | | IV-1 | Slc5a2 |
| 18149 | 3 | 4 | | | IV-1 | Slc5a4b |
| 18150 | 3 | 4 | | | IV-1 | Slc5a5 |
| 18151 | 3 | 4 | | | IV-1 | Slc5a6 |
| 18152 | 3 | 4 | | | IV-1 | Slc5a9 |
| 18153 | 3 | 4 | | | IV-1 | Slc6a1 |
| 18154 | 3 | 4 | | | IV-1 | Slc6a11 |
| 18155 | 3 | 4 | | | IV-1 | Slc6a15 |
| 18156 | 3 | 4 | | | IV-1 | Slc6a18 |
| 18157 | 3 | 4 | | | IV-1 | Slc6a19 |
| 18158 | 3 | 4 | | | IV-1 | Slc6a2 |
| 18159 | 3 | 4 | | | IV-1 | Slc6a3 |
| 18160 | 3 | 4 | | | IV-1 | Slc6a6 |
| 18161 | 3 | 4 | | | IV-1 | Slc6a7 |
| 18162 | 3 | 4 | | | IV-1 | Slc7a11 |
| 18163 | 3 | 4 | | | IV-1 | Slc7a13 |
| 18164 | 3 | 4 | | | IV-1 | Slc7a6 |
| 18165 | 3 | 4 | | | IV-1 | Slc7a6os |
| 18166 | 3 | 4 | | | IV-1 | Slc8a2 |
| 18167 | 3 | 4 | | | IV-1 | Slc8a3 |
| 18168 | 3 | 4 | | | IV-1 | Slc9a1 |
| 18169 | 3 | 4 | | | IV-1 | Slc9a4 |
| 18170 | 3 | 4 | | | IV-1 | Slc9a5 |
| 18171 | 3 | 4 | | | IV-1 | Slc9a8 |
| 18172 | 3 | 4 | | | IV-1 | Slc9a9 |
| 18173 | 3 | 4 | | | IV-1 | Slc9b1 |
| 18174 | 3 | 4 | | | IV-1 | Slc9b2 |
| 18175 | 3 | 4 | | | IV-1 | Slco1a1 |
| 18176 | 3 | 4 | | | IV-1 | Slco1a6 |
| 18177 | 3 | 4 | | | IV-1 | Slco1b2 |
| 18178 | 3 | 4 | | | IV-1 | Slco1c1 |
| 18179 | 3 | 4 | | | IV-1 | Slco2b1 |
| 18180 | 3 | 4 | | | IV-1 | Slco3a1 |
| 18181 | 3 | 4 | | | IV-1 | Slco4a1 |
| 18182 | 3 | 4 | | | IV-1 | Slco5a1 |
| 18183 | 3 | 4 | | | IV-1 | Slco6b1 |
| 18184 | 3 | 4 | | | IV-1 | Slco6c1 |
| 18185 | 3 | 4 | | | IV-1 | Slco6d1 |
| 18186 | 3 | 4 | | | IV-1 | Slfn10-ps |
| 18187 | 3 | 4 | | | IV-1 | Slitrk1 |
| 18188 | 3 | 4 | | | IV-1 | Slitrk2 |
| 18189 | 3 | 4 | | | IV-1 | Slitrk5 |
| 18190 | 3 | 4 | | | IV-1 | Slk |
| 18191 | 3 | 4 | | | IV-1 | Slmo1 |
| 18192 | 3 | 4 | | | IV-1 | Slmo2 |
| 18193 | 3 | 4 | | | IV-1 | Sltm |
| 18194 | 3 | 4 | | | IV-1 | Slu7 |
| 18195 | 3 | 4 | | | IV-1 | Slx1b |
| 18196 | 3 | 4 | | | IV-1 | Slxl1 |
| 18197 | 3 | 4 | | | IV-1 | Smad1 |
| 18198 | 3 | 4 | | | IV-1 | Smad2 |
| 18199 | 3 | 4 | | | IV-1 | Smad4 |
| 18200 | 3 | 4 | | | IV-1 | Smad5 |
| 18201 | 3 | 4 | | | IV-1 | Smap2 |
| 18202 | 3 | 4 | | | IV-1 | Smarca1 |
| 18203 | 3 | 4 | | | IV-1 | Smarca2 |
| 18204 | 3 | 4 | | | IV-1 | Smarca4 |
| 18205 | 3 | 4 | | | IV-1 | Smarca5 |
| 18206 | 3 | 4 | | | IV-1 | Smarca5-ps |
| 18207 | 3 | 4 | | | IV-1 | Smarcad1 |
| 18208 | 3 | 4 | | | IV-1 | Smarcb1 |
| 18209 | 3 | 4 | | | IV-1 | Smarcc1 |
| 18210 | 3 | 4 | | | IV-1 | Smarcc2 |
| 18211 | 3 | 4 | | | IV-1 | Smarcd1 |
| 18212 | 3 | 4 | | | IV-1 | Smarcd2 |
| 18213 | 3 | 4 | | | IV-1 | Smarce1 |
| 18214 | 3 | 4 | | | IV-1 | Smc1b |
| 18215 | 3 | 4 | | | IV-1 | Smc3 |
| 18216 | 3 | 4 | | | IV-1 | Smc4 |
| 18217 | 3 | 4 | | | IV-1 | Smc5 |
| 18218 | 3 | 4 | | | IV-1 | Smc6 |
| 18219 | 3 | 4 | | | IV-1 | Smchd1 |
| 18220 | 3 | 4 | | | IV-1 | Smco2 |
| 18221 | 3 | 4 | | | IV-1 | Smco3 |
| 18222 | 3 | 4 | | | IV-1 | Smek1 |
| 18223 | 3 | 4 | | | IV-1 | Smek2 |
| 18224 | 3 | 4 | | | IV-1 | Smg5 |
| 18225 | 3 | 4 | | | IV-1 | Smg6 |
| 18226 | 3 | 4 | | | IV-1 | Smg7 |
| 18227 | 3 | 4 | | | IV-1 | Smg8 |
| 18228 | 3 | 4 | | | IV-1 | Smg9 |
| 18229 | 3 | 4 | | | IV-1 | Smim1 |
| 18230 | 3 | 4 | | | IV-1 | Smim12 |
| 18231 | 3 | 4 | | | IV-1 | Smim13 |
| 18232 | 3 | 4 | | | IV-1 | Smim14 |
| 18233 | 3 | 4 | | | IV-1 | Smim23 |
| 18234 | 3 | 4 | | | IV-1 | Smim7 |
| 18235 | 3 | 4 | | | IV-1 | Smlr1 |
| 18236 | 3 | 4 | | | IV-1 | Smo |
| 18237 | 3 | 4 | | | IV-1 | Smoc1 |
| 18238 | 3 | 4 | | | IV-1 | Smoc2 |

Fig. 36 - 96

| | | | | | | |
|---|---|---|---|---|---|---|
| 18239 | 3 | 4 | | | IV-1 | Smok2a |
| 18240 | 3 | 4 | | | IV-1 | Smok3a |
| 18241 | 3 | 4 | | | IV-1 | Smpd1 |
| 18242 | 3 | 4 | | | IV-1 | Smpd2 |
| 18243 | 3 | 4 | | | IV-1 | Smpd4 |
| 18244 | 3 | 4 | | | IV-1 | Smtnl1 |
| 18245 | 3 | 4 | | | IV-1 | Smu1 |
| 18246 | 3 | 4 | | | IV-1 | Smug1 |
| 18247 | 3 | 4 | | | IV-1 | Smurf1 |
| 18248 | 3 | 4 | | | IV-1 | Smurf2 |
| 18249 | 3 | 4 | | | IV-1 | Smyd3 |
| 18250 | 3 | 4 | | | IV-1 | Smyd4 |
| 18251 | 3 | 4 | | | IV-1 | Smyd5 |
| 18252 | 3 | 4 | | | IV-1 | Snai2 |
| 18253 | 3 | 4 | | | IV-1 | Snap25 |
| 18254 | 3 | 4 | | | IV-1 | Snap29 |
| 18255 | 3 | 4 | | | IV-1 | Snap91 |
| 18256 | 3 | 4 | | | IV-1 | Snch |
| 18257 | 3 | 4 | | | IV-1 | Snd1 |
| 18258 | 3 | 4 | | | IV-1 | Snhg11 |
| 18259 | 3 | 4 | | | IV-1 | Snrk |
| 18260 | 3 | 4 | | | IV-1 | Snrnp40 |
| 18261 | 3 | 4 | | | IV-1 | Snrnp48 |
| 18262 | 3 | 4 | | | IV-1 | Snrpa |
| 18263 | 3 | 4 | | | IV-1 | Snta1 |
| 18264 | 3 | 4 | | | IV-1 | Sntg1 |
| 18265 | 3 | 4 | | | IV-1 | Sntg2 |
| 18266 | 3 | 4 | | | IV-1 | Snw1 |
| 18267 | 3 | 4 | | | IV-1 | Snx1 |
| 18268 | 3 | 4 | | | IV-1 | Snx11 |
| 18269 | 3 | 4 | | | IV-1 | Snx13 |
| 18270 | 3 | 4 | | | IV-1 | Snx14 |
| 18271 | 3 | 4 | | | IV-1 | Snx17 |
| 18272 | 3 | 4 | | | IV-1 | Snx18 |
| 18273 | 3 | 4 | | | IV-1 | Snx19 |
| 18274 | 3 | 4 | | | IV-1 | Snx2 |
| 18275 | 3 | 4 | | | IV-1 | Snx21 |
| 18276 | 3 | 4 | | | IV-1 | Snx24 |
| 18277 | 3 | 4 | | | IV-1 | Snx25 |
| 18278 | 3 | 4 | | | IV-1 | Snx31 |
| 18279 | 3 | 4 | | | IV-1 | Snx6 |
| 18280 | 3 | 4 | | | IV-1 | Snx8 |
| 18281 | 3 | 4 | | | IV-1 | Sobp |
| 18282 | 3 | 4 | | | IV-1 | Socs5 |
| 18283 | 3 | 4 | | | IV-1 | Sod3 |
| 18284 | 3 | 4 | | | IV-1 | Soga3 |
| 18285 | 3 | 4 | | | IV-1 | Sohlh1 |
| 18286 | 3 | 4 | | | IV-1 | Sohlh2 |
| 18287 | 3 | 4 | | | IV-1 | Sorbs1 |
| 18288 | 3 | 4 | | | IV-1 | Sorbs2 |
| 18289 | 3 | 4 | | | IV-1 | Sorbs3 |
| 18290 | 3 | 4 | | | IV-1 | Sorcs1 |
| 18291 | 3 | 4 | | | IV-1 | Sorcs3 |
| 18292 | 3 | 4 | | | IV-1 | Sord |
| 18293 | 3 | 4 | | | IV-1 | Sort1 |
| 18294 | 3 | 4 | | | IV-1 | Sos1 |
| 18295 | 3 | 4 | | | IV-1 | Sos2 |
| 18296 | 3 | 4 | | | IV-1 | Sowaha |
| 18297 | 3 | 4 | | | IV-1 | Sox11 |
| 18298 | 3 | 4 | | | IV-1 | Sox13 |
| 18299 | 3 | 4 | | | IV-1 | Sox14 |
| 18300 | 3 | 4 | | | IV-1 | Sox2 |
| 18301 | 3 | 4 | | | IV-1 | Sox21 |
| 18302 | 3 | 4 | | | IV-1 | Sox2ot |
| 18303 | 3 | 4 | | | IV-1 | Sox3 |
| 18304 | 3 | 4 | | | IV-1 | Sox5os3 |
| 18305 | 3 | 4 | | | IV-1 | Sox8 |
| 18306 | 3 | 4 | | | IV-1 | Sp2 |
| 18307 | 3 | 4 | | | IV-1 | Sp4 |
| 18308 | 3 | 4 | | | IV-1 | Sp6 |
| 18309 | 3 | 4 | | | IV-1 | Spaca1 |
| 18310 | 3 | 4 | | | IV-1 | Spaca7 |
| 18311 | 3 | 4 | | | IV-1 | Spag1 |
| 18312 | 3 | 4 | | | IV-1 | Spag9 |
| 18313 | 3 | 4 | | | IV-1 | Spam1 |
| 18314 | 3 | 4 | | | IV-1 | Sparcl1 |
| 18315 | 3 | 4 | | | IV-1 | Spast |
| 18316 | 3 | 4 | | | IV-1 | Spata1 |
| 18317 | 3 | 4 | | | IV-1 | Spata16 |
| 18318 | 3 | 4 | | | IV-1 | Spata17 |
| 18319 | 3 | 4 | | | IV-1 | Spata18 |
| 18320 | 3 | 4 | | | IV-1 | Spata19 |
| 18321 | 3 | 4 | | | IV-1 | Spata2 |
| 18322 | 3 | 4 | | | IV-1 | Spata20 |
| 18323 | 3 | 4 | | | IV-1 | Spata21 |
| 18324 | 3 | 4 | | | IV-1 | Spata25 |
| 18325 | 3 | 4 | | | IV-1 | Spata31 |
| 18326 | 3 | 4 | | | IV-1 | Spata31d1d |
| 18327 | 3 | 4 | | | IV-1 | Spata32 |
| 18328 | 3 | 4 | | | IV-1 | Spata4 |
| 18329 | 3 | 4 | | | IV-1 | Spata45 |
| 18330 | 3 | 4 | | | IV-1 | Spata6 |
| 18331 | 3 | 4 | | | IV-1 | Spatc1 |
| 18332 | 3 | 4 | | | IV-1 | Spatc1l |
| 18333 | 3 | 4 | | | IV-1 | Spats2l |
| 18334 | 3 | 4 | | | IV-1 | Spcs2 |
| 18335 | 3 | 4 | | | IV-1 | Spcs3 |
| 18336 | 3 | 4 | | | IV-1 | Spdl1 |
| 18337 | 3 | 4 | | | IV-1 | Spdya |
| 18338 | 3 | 4 | | | IV-1 | Spdyb |
| 18339 | 3 | 4 | | | IV-1 | Specc1l |
| 18340 | 3 | 4 | | | IV-1 | Speer1-ps1 |
| 18341 | 3 | 4 | | | IV-1 | Speer2 |
| 18342 | 3 | 4 | | | IV-1 | Speer3 |
| 18343 | 3 | 4 | | | IV-1 | Speer4a |
| 18344 | 3 | 4 | | | IV-1 | Speer4b |
| 18345 | 3 | 4 | | | IV-1 | Speer4c |
| 18346 | 3 | 4 | | | IV-1 | Speer4d |
| 18347 | 3 | 4 | | | IV-1 | Speer4e |
| 18348 | 3 | 4 | | | IV-1 | Speer4f |
| 18349 | 3 | 4 | | | IV-1 | Speer5-ps1 |
| 18350 | 3 | 4 | | | IV-1 | Speer9-ps1 |
| 18351 | 3 | 4 | | | IV-1 | Spem1 |
| 18352 | 3 | 4 | | | IV-1 | Spert |
| 18353 | 3 | 4 | | | IV-1 | Spesp1 |
| 18354 | 3 | 4 | | | IV-1 | Spg20 |
| 18355 | 3 | 4 | | | IV-1 | Spg7 |
| 18356 | 3 | 4 | | | IV-1 | Sphk2 |
| 18357 | 3 | 4 | | | IV-1 | Spin1 |
| 18358 | 3 | 4 | | | IV-1 | Spin2d |
| 18359 | 3 | 4 | | | IV-1 | Spink10 |
| 18360 | 3 | 4 | | | IV-1 | Spink6 |
| 18361 | 3 | 4 | | | IV-1 | Spire2 |
| 18362 | 3 | 4 | | | IV-1 | Spn-ps |
| 18363 | 3 | 4 | | | IV-1 | Spns1 |
| 18364 | 3 | 4 | | | IV-1 | Spns2 |
| 18365 | 3 | 4 | | | IV-1 | Spns3 |
| 18366 | 3 | 4 | | | IV-1 | Spo11 |
| 18367 | 3 | 4 | | | IV-1 | Spock3 |
| 18368 | 3 | 4 | | | IV-1 | Spon1 |
| 18369 | 3 | 4 | | | IV-1 | Spp2 |
| 18370 | 3 | 4 | | | IV-1 | Sppl2a |
| 18371 | 3 | 4 | | | IV-1 | Sppl2b |
| 18372 | 3 | 4 | | | IV-1 | Sppl2c |
| 18373 | 3 | 4 | | | IV-1 | Spr |
| 18374 | 3 | 4 | | | IV-1 | Spred1 |
| 18375 | 3 | 4 | | | IV-1 | Sprn |
| 18376 | 3 | 4 | | | IV-1 | Sprr2b |
| 18377 | 3 | 4 | | | IV-1 | Sprr2e |
| 18378 | 3 | 4 | | | IV-1 | Sprr2i |
| 18379 | 3 | 4 | | | IV-1 | Sprr2j-ps |
| 18380 | 3 | 4 | | | IV-1 | Sprr4 |
| 18381 | 3 | 4 | | | IV-1 | Spry2 |
| 18382 | 3 | 4 | | | IV-1 | Spry3 |
| 18383 | 3 | 4 | | | IV-1 | Spryd3 |
| 18384 | 3 | 4 | | | IV-1 | Spsb4 |
| 18385 | 3 | 4 | | | IV-1 | Sptbn2 |
| 18386 | 3 | 4 | | | IV-1 | Sptbn4 |
| 18387 | 3 | 4 | | | IV-1 | Sptlc1 |
| 18388 | 3 | 4 | | | IV-1 | Sptlc3 |
| 18389 | 3 | 4 | | | IV-1 | Sptssa |
| 18390 | 3 | 4 | | | IV-1 | Spty2d1 |
| 18391 | 3 | 4 | | | IV-1 | Spz1 |
| 18392 | 3 | 4 | | | IV-1 | Sqstm1 |
| 18393 | 3 | 4 | | | IV-1 | Srbd1 |
| 18394 | 3 | 4 | | | IV-1 | Srcin1 |
| 18395 | 3 | 4 | | | IV-1 | Srek1 |
| 18396 | 3 | 4 | | | IV-1 | Srf |
| 18397 | 3 | 4 | | | IV-1 | Srgap1 |
| 18398 | 3 | 4 | | | IV-1 | Srgap2 |
| 18399 | 3 | 4 | | | IV-1 | Sri |
| 18400 | 3 | 4 | | | IV-1 | Srm |
| 18401 | 3 | 4 | | | IV-1 | Srp54a |
| 18402 | 3 | 4 | | | IV-1 | Srp54b |
| 18403 | 3 | 4 | | | IV-1 | Srp68 |
| 18404 | 3 | 4 | | | IV-1 | Srp72 |
| 18405 | 3 | 4 | | | IV-1 | Srpk1 |
| 18406 | 3 | 4 | | | IV-1 | Srpk2 |
| 18407 | 3 | 4 | | | IV-1 | Srpr |
| 18408 | 3 | 4 | | | IV-1 | Srprb |
| 18409 | 3 | 4 | | | IV-1 | Srpx2 |
| 18410 | 3 | 4 | | | IV-1 | Srrm1 |
| 18411 | 3 | 4 | | | IV-1 | Srrm3 |
| 18412 | 3 | 4 | | | IV-1 | Srrm4os |
| 18413 | 3 | 4 | | | IV-1 | Srrt |
| 18414 | 3 | 4 | | | IV-1 | Srsf1 |
| 18415 | 3 | 4 | | | IV-1 | Srsf10 |
| 18416 | 3 | 4 | | | IV-1 | Srsf12 |
| 18417 | 3 | 4 | | | IV-1 | Srsf2 |
| 18418 | 3 | 4 | | | IV-1 | Srsf4 |
| 18419 | 3 | 4 | | | IV-1 | Srsf5 |
| 18420 | 3 | 4 | | | IV-1 | Srsf6 |
| 18421 | 3 | 4 | | | IV-1 | Srsf7 |
| 18422 | 3 | 4 | | | IV-1 | Srsf9 |
| 18423 | 3 | 4 | | | IV-1 | Ss18 |
| 18424 | 3 | 4 | | | IV-1 | Ssb |
| 18425 | 3 | 4 | | | IV-1 | Ssbp1 |
| 18426 | 3 | 4 | | | IV-1 | Ssbp2 |
| 18427 | 3 | 4 | | | IV-1 | Ssfa2 |
| 18428 | 3 | 4 | | | IV-1 | Ssh3 |
| 18429 | 3 | 4 | | | IV-1 | Sspn |
| 18430 | 3 | 4 | | | IV-1 | Ssr1 |

Fig. 36 - 97

| | | | | | | |
|---|---|---|---|---|---|---|
| 18431 | 3 | 4 | | | IV-1 | Ssrp1 |
| 18432 | 3 | 4 | | | IV-1 | Sstr1 |
| 18433 | 3 | 4 | | | IV-1 | Sstr3 |
| 18434 | 3 | 4 | | | IV-1 | Ssty2 |
| 18435 | 3 | 4 | | | IV-1 | Ssxb1 |
| 18436 | 3 | 4 | | | IV-1 | Ssxb2 |
| 18437 | 3 | 4 | | | IV-1 | Ssxb6 |
| 18438 | 3 | 4 | | | IV-1 | St13 |
| 18439 | 3 | 4 | | | IV-1 | St18 |
| 18440 | 3 | 4 | | | IV-1 | St3gal3 |
| 18441 | 3 | 4 | | | IV-1 | St3gal6 |
| 18442 | 3 | 4 | | | IV-1 | St5 |
| 18443 | 3 | 4 | | | IV-1 | St6galnac1 |
| 18444 | 3 | 4 | | | IV-1 | St6galnac2 |
| 18445 | 3 | 4 | | | IV-1 | St6galnac4 |
| 18446 | 3 | 4 | | | IV-1 | St7l |
| 18447 | 3 | 4 | | | IV-1 | St8sia3 |
| 18448 | 3 | 4 | | | IV-1 | St8sia6 |
| 18449 | 3 | 4 | | | IV-1 | Stab1 |
| 18450 | 3 | 4 | | | IV-1 | Stab2 |
| 18451 | 3 | 4 | | | IV-1 | Stac3 |
| 18452 | 3 | 4 | | | IV-1 | Stag2 |
| 18453 | 3 | 4 | | | IV-1 | Stag3 |
| 18454 | 3 | 4 | | | IV-1 | Stam |
| 18455 | 3 | 4 | | | IV-1 | Stam2 |
| 18456 | 3 | 4 | | | IV-1 | Stambp |
| 18457 | 3 | 4 | | | IV-1 | Stambpl1 |
| 18458 | 3 | 4 | | | IV-1 | Stard3 |
| 18459 | 3 | 4 | | | IV-1 | Stard5 |
| 18460 | 3 | 4 | | | IV-1 | Stard6 |
| 18461 | 3 | 4 | | | IV-1 | Stard7 |
| 18462 | 3 | 4 | | | IV-1 | Stard8 |
| 18463 | 3 | 4 | | | IV-1 | Stat3 |
| 18464 | 3 | 4 | | | IV-1 | Stat5a |
| 18465 | 3 | 4 | | | IV-1 | Stat5b |
| 18466 | 3 | 4 | | | IV-1 | Stat6 |
| 18467 | 3 | 4 | | | IV-1 | Stau1 |
| 18468 | 3 | 4 | | | IV-1 | Stau2 |
| 18469 | 3 | 4 | | | IV-1 | Steap2 |
| 18470 | 3 | 4 | | | IV-1 | Stil |
| 18471 | 3 | 4 | | | IV-1 | Stim2 |
| 18472 | 3 | 4 | | | IV-1 | Stip1 |
| 18473 | 3 | 4 | | | IV-1 | Stk10 |
| 18474 | 3 | 4 | | | IV-1 | Stk11 |
| 18475 | 3 | 4 | | | IV-1 | Stk11ip |
| 18476 | 3 | 4 | | | IV-1 | Stk16 |
| 18477 | 3 | 4 | | | IV-1 | Stk31 |
| 18478 | 3 | 4 | | | IV-1 | Stk32a |
| 18479 | 3 | 4 | | | IV-1 | Stk32b |
| 18480 | 3 | 4 | | | IV-1 | Stk36 |
| 18481 | 3 | 4 | | | IV-1 | Stk38 |
| 18482 | 3 | 4 | | | IV-1 | Stk39 |
| 18483 | 3 | 4 | | | IV-1 | Stk40 |
| 18484 | 3 | 4 | | | IV-1 | Stmn2 |
| 18485 | 3 | 4 | | | IV-1 | Stmn4 |
| 18486 | 3 | 4 | | | IV-1 | Stmnd1 |
| 18487 | 3 | 4 | | | IV-1 | Stoml3 |
| 18488 | 3 | 4 | | | IV-1 | Stpg1 |
| 18489 | 3 | 4 | | | IV-1 | Stra6 |
| 18490 | 3 | 4 | | | IV-1 | Stra8 |
| 18491 | 3 | 4 | | | IV-1 | Strap |
| 18492 | 3 | 4 | | | IV-1 | Strip1 |
| 18493 | 3 | 4 | | | IV-1 | Strn3 |
| 18494 | 3 | 4 | | | IV-1 | Strn4 |
| 18495 | 3 | 4 | | | IV-1 | Stt3a |
| 18496 | 3 | 4 | | | IV-1 | Stt3b |
| 18497 | 3 | 4 | | | IV-1 | Stx12 |
| 18498 | 3 | 4 | | | IV-1 | Stx16 |
| 18499 | 3 | 4 | | | IV-1 | Stx17 |
| 18500 | 3 | 4 | | | IV-1 | Stx19 |
| 18501 | 3 | 4 | | | IV-1 | Stx3 |
| 18502 | 3 | 4 | | | IV-1 | Stx5a |
| 18503 | 3 | 4 | | | IV-1 | Stx6 |
| 18504 | 3 | 4 | | | IV-1 | Stx7 |
| 18505 | 3 | 4 | | | IV-1 | Stxbp1 |
| 18506 | 3 | 4 | | | IV-1 | Stxbp2 |
| 18507 | 3 | 4 | | | IV-1 | Stxbp3a |
| 18508 | 3 | 4 | | | IV-1 | Stxbp4 |
| 18509 | 3 | 4 | | | IV-1 | Stxbp5 |
| 18510 | 3 | 4 | | | IV-1 | Styk1 |
| 18511 | 3 | 4 | | | IV-1 | Styxl1 |
| 18512 | 3 | 4 | | | IV-1 | Sub1 |
| 18513 | 3 | 4 | | | IV-1 | Sucla2 |
| 18514 | 3 | 4 | | | IV-1 | Suclg1 |
| 18515 | 3 | 4 | | | IV-1 | Suclg2 |
| 18516 | 3 | 4 | | | IV-1 | Suco |
| 18517 | 3 | 4 | | | IV-1 | Sufu |
| 18518 | 3 | 4 | | | IV-1 | Sugct |
| 18519 | 3 | 4 | | | IV-1 | Sugp1 |
| 18520 | 3 | 4 | | | IV-1 | Sulf1 |
| 18521 | 3 | 4 | | | IV-1 | Sulf2 |
| 18522 | 3 | 4 | | | IV-1 | Sult1e1 |
| 18523 | 3 | 4 | | | IV-1 | Sult4a1 |
| 18524 | 3 | 4 | | | IV-1 | Sumf1 |
| 18525 | 3 | 4 | | | IV-1 | Sumf2 |
| 18526 | 3 | 4 | | | IV-1 | Sumo3 |
| 18527 | 3 | 4 | | | IV-1 | Sun1 |
| 18528 | 3 | 4 | | | IV-1 | Sun2 |
| 18529 | 3 | 4 | | | IV-1 | Supt16 |
| 18530 | 3 | 4 | | | IV-1 | Supt5 |
| 18531 | 3 | 4 | | | IV-1 | Supt6 |
| 18532 | 3 | 4 | | | IV-1 | Supv3l1 |
| 18533 | 3 | 4 | | | IV-1 | Surf2 |
| 18534 | 3 | 4 | | | IV-1 | Surf4 |
| 18535 | 3 | 4 | | | IV-1 | Surf6 |
| 18536 | 3 | 4 | | | IV-1 | Susd1 |
| 18537 | 3 | 4 | | | IV-1 | Suv39h1 |
| 18538 | 3 | 4 | | | IV-1 | Suv39h2 |
| 18539 | 3 | 4 | | | IV-1 | Suv420h1 |
| 18540 | 3 | 4 | | | IV-1 | Suv420h2 |
| 18541 | 3 | 4 | | | IV-1 | Suz12 |
| 18542 | 3 | 4 | | | IV-1 | Svip |
| 18543 | 3 | 4 | | | IV-1 | Svop |
| 18544 | 3 | 4 | | | IV-1 | Svopl |
| 18545 | 3 | 4 | | | IV-1 | Swap70 |
| 18546 | 3 | 4 | | | IV-1 | Swt1 |
| 18547 | 3 | 4 | | | IV-1 | Sybu |
| 18548 | 3 | 4 | | | IV-1 | Syce3 |
| 18549 | 3 | 4 | | | IV-1 | Sycp1 |
| 18550 | 3 | 4 | | | IV-1 | Sycp1-ps1 |
| 18551 | 3 | 4 | | | IV-1 | Sycp2 |
| 18552 | 3 | 4 | | | IV-1 | Syde1 |
| 18553 | 3 | 4 | | | IV-1 | Sympk |
| 18554 | 3 | 4 | | | IV-1 | Syn1 |
| 18555 | 3 | 4 | | | IV-1 | Syna |
| 18556 | 3 | 4 | | | IV-1 | Sync |
| 18557 | 3 | 4 | | | IV-1 | Syncrip |
| 18558 | 3 | 4 | | | IV-1 | Syndig1 |
| 18559 | 3 | 4 | | | IV-1 | Syndig1l |
| 18560 | 3 | 4 | | | IV-1 | Syne1 |
| 18561 | 3 | 4 | | | IV-1 | Syne4 |
| 18562 | 3 | 4 | | | IV-1 | Syngr3 |
| 18563 | 3 | 4 | | | IV-1 | Synj1 |
| 18564 | 3 | 4 | | | IV-1 | Synj2 |
| 18565 | 3 | 4 | | | IV-1 | Synj2bp |
| 18566 | 3 | 4 | | | IV-1 | Synpo |
| 18567 | 3 | 4 | | | IV-1 | Synpr |
| 18568 | 3 | 4 | | | IV-1 | Synrg |
| 18569 | 3 | 4 | | | IV-1 | Syp |
| 18570 | 3 | 4 | | | IV-1 | Sypl |
| 18571 | 3 | 4 | | | IV-1 | Sys1 |
| 18572 | 3 | 4 | | | IV-1 | Syt1 |
| 18573 | 3 | 4 | | | IV-1 | Syt12 |
| 18574 | 3 | 4 | | | IV-1 | Syt13 |
| 18575 | 3 | 4 | | | IV-1 | Syt15 |
| 18576 | 3 | 4 | | | IV-1 | Syt16 |
| 18577 | 3 | 4 | | | IV-1 | Syt4 |
| 18578 | 3 | 4 | | | IV-1 | Syt6 |
| 18579 | 3 | 4 | | | IV-1 | Syt7 |
| 18580 | 3 | 4 | | | IV-1 | Syt9 |
| 18581 | 3 | 4 | | | IV-1 | Sytl1 |
| 18582 | 3 | 4 | | | IV-1 | Syvn1 |
| 18583 | 3 | 4 | | | IV-1 | Szrd1 |
| 18584 | 3 | 4 | | | IV-1 | Tab2 |
| 18585 | 3 | 4 | | | IV-1 | Tab3 |
| 18586 | 3 | 4 | | | IV-1 | Tac4 |
| 18587 | 3 | 4 | | | IV-1 | Tacc1 |
| 18588 | 3 | 4 | | | IV-1 | Tacc2 |
| 18589 | 3 | 4 | | | IV-1 | Tacc3 |
| 18590 | 3 | 4 | | | IV-1 | Tacr1 |
| 18591 | 3 | 4 | | | IV-1 | Tacr2 |
| 18592 | 3 | 4 | | | IV-1 | Tacr3 |
| 18593 | 3 | 4 | | | IV-1 | Tada2b |
| 18594 | 3 | 4 | | | IV-1 | Tada3 |
| 18595 | 3 | 4 | | | IV-1 | Taf15 |
| 18596 | 3 | 4 | | | IV-1 | Taf1a |
| 18597 | 3 | 4 | | | IV-1 | Taf2 |
| 18598 | 3 | 4 | | | IV-1 | Taf3 |
| 18599 | 3 | 4 | | | IV-1 | Taf4a |
| 18600 | 3 | 4 | | | IV-1 | Taf5 |
| 18601 | 3 | 4 | | | IV-1 | Taf5l |
| 18602 | 3 | 4 | | | IV-1 | Taf7l |
| 18603 | 3 | 4 | | | IV-1 | Taf8 |
| 18604 | 3 | 4 | | | IV-1 | Taf9 |
| 18605 | 3 | 4 | | | IV-1 | Taf9b |
| 18606 | 3 | 4 | | | IV-1 | Tagap |
| 18607 | 3 | 4 | | | IV-1 | Tagln2 |
| 18608 | 3 | 4 | | | IV-1 | Tagln3 |
| 18609 | 3 | 4 | | | IV-1 | Tal2 |
| 18610 | 3 | 4 | | | IV-1 | Tanc1 |
| 18611 | 3 | 4 | | | IV-1 | Tango6 |
| 18612 | 3 | 4 | | | IV-1 | Taok3 |
| 18613 | 3 | 4 | | | IV-1 | Tapt1 |
| 18614 | 3 | 4 | | | IV-1 | Tardbp |
| 18615 | 3 | 4 | | | IV-1 | Tars |
| 18616 | 3 | 4 | | | IV-1 | Tars2 |
| 18617 | 3 | 4 | | | IV-1 | Tarsl2 |
| 18618 | 3 | 4 | | | IV-1 | Tas1r1 |
| 18619 | 3 | 4 | | | IV-1 | Tatdn2 |
| 18620 | 3 | 4 | | | IV-1 | Tax1bp3 |
| 18621 | 3 | 4 | | | IV-1 | Taz |
| 18622 | 3 | 4 | | | IV-1 | Tbc1d1 |

Fig. 36 - 98

| | | | | | | |
|---|---|---|---|---|---|---|
| 18623 | 3 | 4 | | | IV-1 | Tbc1d10a |
| 18624 | 3 | 4 | | | IV-1 | Tbc1d12 |
| 18625 | 3 | 4 | | | IV-1 | Tbc1d13 |
| 18626 | 3 | 4 | | | IV-1 | Tbc1d14 |
| 18627 | 3 | 4 | | | IV-1 | Tbc1d15 |
| 18628 | 3 | 4 | | | IV-1 | Tbc1d16 |
| 18629 | 3 | 4 | | | IV-1 | Tbc1d19 |
| 18630 | 3 | 4 | | | IV-1 | Tbc1d2 |
| 18631 | 3 | 4 | | | IV-1 | Tbc1d22b |
| 18632 | 3 | 4 | | | IV-1 | Tbc1d23 |
| 18633 | 3 | 4 | | | IV-1 | Tbc1d32 |
| 18634 | 3 | 4 | | | IV-1 | Tbc1d5 |
| 18635 | 3 | 4 | | | IV-1 | Tbc1d8b |
| 18636 | 3 | 4 | | | IV-1 | Tbc1d9b |
| 18637 | 3 | 4 | | | IV-1 | Tbccd1 |
| 18638 | 3 | 4 | | | IV-1 | Tbcd |
| 18639 | 3 | 4 | | | IV-1 | Tbce |
| 18640 | 3 | 4 | | | IV-1 | Tbcel |
| 18641 | 3 | 4 | | | IV-1 | Tbk1 |
| 18642 | 3 | 4 | | | IV-1 | Tbkbp1 |
| 18643 | 3 | 4 | | | IV-1 | Tbl1xr1 |
| 18644 | 3 | 4 | | | IV-1 | Tbp |
| 18645 | 3 | 4 | | | IV-1 | Tbpl1 |
| 18646 | 3 | 4 | | | IV-1 | Tbrl |
| 18647 | 3 | 4 | | | IV-1 | Tbrg1 |
| 18648 | 3 | 4 | | | IV-1 | Tbrg4 |
| 18649 | 3 | 4 | | | IV-1 | Tbx10 |
| 18650 | 3 | 4 | | | IV-1 | Tbx15 |
| 18651 | 3 | 4 | | | IV-1 | Tbx18 |
| 18652 | 3 | 4 | | | IV-1 | Tbx19 |
| 18653 | 3 | 4 | | | IV-1 | Tbx20 |
| 18654 | 3 | 4 | | | IV-1 | Tbx4 |
| 18655 | 3 | 4 | | | IV-1 | Tbx5 |
| 18656 | 3 | 4 | | | IV-1 | Tbx6 |
| 18657 | 3 | 4 | | | IV-1 | Tc2n |
| 18658 | 3 | 4 | | | IV-1 | Tcaim |
| 18659 | 3 | 4 | | | IV-1 | Tceal6 |
| 18660 | 3 | 4 | | | IV-1 | Tceal8 |
| 18661 | 3 | 4 | | | IV-1 | Tceanc |
| 18662 | 3 | 4 | | | IV-1 | Tceanc2 |
| 18663 | 3 | 4 | | | IV-1 | Tcerg1 |
| 18664 | 3 | 4 | | | IV-1 | Tcf12 |
| 18665 | 3 | 4 | | | IV-1 | Tcf23 |
| 18666 | 3 | 4 | | | IV-1 | Tcf25 |
| 18667 | 3 | 4 | | | IV-1 | Tcf3 |
| 18668 | 3 | 4 | | | IV-1 | Tcf4 |
| 18669 | 3 | 4 | | | IV-1 | Tcf7l1 |
| 18670 | 3 | 4 | | | IV-1 | Tcfl5 |
| 18671 | 3 | 4 | | | IV-1 | Tchhl1 |
| 18672 | 3 | 4 | | | IV-1 | Tchp |
| 18673 | 3 | 4 | | | IV-1 | Tcirg1 |
| 18674 | 3 | 4 | | | IV-1 | Tcof1 |
| 18675 | 3 | 4 | | | IV-1 | Tcp1 |
| 18676 | 3 | 4 | | | IV-1 | Tcp10a |
| 18677 | 3 | 4 | | | IV-1 | Tcta |
| 18678 | 3 | 4 | | | IV-1 | Tctex1d1 |
| 18679 | 3 | 4 | | | IV-1 | Tctn1 |
| 18680 | 3 | 4 | | | IV-1 | Tdgf1 |
| 18681 | 3 | 4 | | | IV-1 | Tdp2 |
| 18682 | 3 | 4 | | | IV-1 | Tdrd1 |
| 18683 | 3 | 4 | | | IV-1 | Tdrd12 |
| 18684 | 3 | 4 | | | IV-1 | Tdrd5 |
| 18685 | 3 | 4 | | | IV-1 | Tdrd7 |
| 18686 | 3 | 4 | | | IV-1 | Tdrd9 |
| 18687 | 3 | 4 | | | IV-1 | Tdrp |
| 18688 | 3 | 4 | | | IV-1 | Tead2 |
| 18689 | 3 | 4 | | | IV-1 | Tecpr2 |
| 18690 | 3 | 4 | | | IV-1 | Tek |
| 18691 | 3 | 4 | | | IV-1 | Tekt3 |
| 18692 | 3 | 4 | | | IV-1 | Tekt5 |
| 18693 | 3 | 4 | | | IV-1 | Ten1 |
| 18694 | 3 | 4 | | | IV-1 | Tenm3 |
| 18695 | 3 | 4 | | | IV-1 | Tepp |
| 18696 | 3 | 4 | | | IV-1 | Terf1 |
| 18697 | 3 | 4 | | | IV-1 | Terf2 |
| 18698 | 3 | 4 | | | IV-1 | Terf2ip |
| 18699 | 3 | 4 | | | IV-1 | Tert |
| 18700 | 3 | 4 | | | IV-1 | Tesk1 |
| 18701 | 3 | 4 | | | IV-1 | Tex10 |
| 18702 | 3 | 4 | | | IV-1 | Tex11 |
| 18703 | 3 | 4 | | | IV-1 | Tex12 |
| 18704 | 3 | 4 | | | IV-1 | Tex13 |
| 18705 | 3 | 4 | | | IV-1 | Tex13a |
| 18706 | 3 | 4 | | | IV-1 | Tex14 |
| 18707 | 3 | 4 | | | IV-1 | Tex16 |
| 18708 | 3 | 4 | | | IV-1 | Tex19.1 |
| 18709 | 3 | 4 | | | IV-1 | Tex19.2 |
| 18710 | 3 | 4 | | | IV-1 | Tex2 |
| 18711 | 3 | 4 | | | IV-1 | Tex21 |
| 18712 | 3 | 4 | | | IV-1 | Tex22 |
| 18713 | 3 | 4 | | | IV-1 | Tex24 |
| 18714 | 3 | 4 | | | IV-1 | Tex26 |
| 18715 | 3 | 4 | | | IV-1 | Tex261 |
| 18716 | 3 | 4 | | | IV-1 | Tex264 |
| 18717 | 3 | 4 | | | IV-1 | Tex28 |
| 18718 | 3 | 4 | | | IV-1 | Tex29 |
| 18719 | 3 | 4 | | | IV-1 | Tex30 |
| 18720 | 3 | 4 | | | IV-1 | Tex35 |
| 18721 | 3 | 4 | | | IV-1 | Tex36 |
| 18722 | 3 | 4 | | | IV-1 | Tex37 |
| 18723 | 3 | 4 | | | IV-1 | Tex38 |
| 18724 | 3 | 4 | | | IV-1 | Tex40 |
| 18725 | 3 | 4 | | | IV-1 | Tex43 |
| 18726 | 3 | 4 | | | IV-1 | Tfam |
| 18727 | 3 | 4 | | | IV-1 | Tfap2c |
| 18728 | 3 | 4 | | | IV-1 | Tfap2e |
| 18729 | 3 | 4 | | | IV-1 | Tfb2m |
| 18730 | 3 | 4 | | | IV-1 | Tfcp2 |
| 18731 | 3 | 4 | | | IV-1 | Tfdp1 |
| 18732 | 3 | 4 | | | IV-1 | Tfe3 |
| 18733 | 3 | 4 | | | IV-1 | Tfeb |
| 18734 | 3 | 4 | | | IV-1 | Tfg |
| 18735 | 3 | 4 | | | IV-1 | Tfip11 |
| 18736 | 3 | 4 | | | IV-1 | Tfpi2 |
| 18737 | 3 | 4 | | | IV-1 | Tgds |
| 18738 | 3 | 4 | | | IV-1 | Tgfb3 |
| 18739 | 3 | 4 | | | IV-1 | Tgfbr3 |
| 18740 | 3 | 4 | | | IV-1 | Tgfbrap1 |
| 18741 | 3 | 4 | | | IV-1 | Tgif2 |
| 18742 | 3 | 4 | | | IV-1 | Tgm2 |
| 18743 | 3 | 4 | | | IV-1 | Tgm6 |
| 18744 | 3 | 4 | | | IV-1 | Tgoln1 |
| 18745 | 3 | 4 | | | IV-1 | Tgs1 |
| 18746 | 3 | 4 | | | IV-1 | Th |
| 18747 | 3 | 4 | | | IV-1 | Thap1 |
| 18748 | 3 | 4 | | | IV-1 | Thap11 |
| 18749 | 3 | 4 | | | IV-1 | Thap4 |
| 18750 | 3 | 4 | | | IV-1 | Thap6 |
| 18751 | 3 | 4 | | | IV-1 | Thbs3 |
| 18752 | 3 | 4 | | | IV-1 | Thbs4 |
| 18753 | 3 | 4 | | | IV-1 | Theg |
| 18754 | 3 | 4 | | | IV-1 | Them4 |
| 18755 | 3 | 4 | | | IV-1 | Them7 |
| 18756 | 3 | 4 | | | IV-1 | Themis3 |
| 18757 | 3 | 4 | | | IV-1 | Thg1l |
| 18758 | 3 | 4 | | | IV-1 | Thoc1 |
| 18759 | 3 | 4 | | | IV-1 | Thoc2 |
| 18760 | 3 | 4 | | | IV-1 | Thoc3 |
| 18761 | 3 | 4 | | | IV-1 | Thoc5 |
| 18762 | 3 | 4 | | | IV-1 | Thop1 |
| 18763 | 3 | 4 | | | IV-1 | Thsd1 |
| 18764 | 3 | 4 | | | IV-1 | Thsd7b |
| 18765 | 3 | 4 | | | IV-1 | Thtpa |
| 18766 | 3 | 4 | | | IV-1 | Thumpd1 |
| 18767 | 3 | 4 | | | IV-1 | Thumpd2 |
| 18768 | 3 | 4 | | | IV-1 | Thumpd3 |
| 18769 | 3 | 4 | | | IV-1 | Tial1 |
| 18770 | 3 | 4 | | | IV-1 | Tiam1 |
| 18771 | 3 | 4 | | | IV-1 | Tiam2 |
| 18772 | 3 | 4 | | | IV-1 | Ticam1 |
| 18773 | 3 | 4 | | | IV-1 | Ticrr |
| 18774 | 3 | 4 | | | IV-1 | Tie1 |
| 18775 | 3 | 4 | | | IV-1 | Tifa |
| 18776 | 3 | 4 | | | IV-1 | Tigd3 |
| 18777 | 3 | 4 | | | IV-1 | Tigd4 |
| 18778 | 3 | 4 | | | IV-1 | Tigd5 |
| 18779 | 3 | 4 | | | IV-1 | Timd2 |
| 18780 | 3 | 4 | | | IV-1 | Timeless |
| 18781 | 3 | 4 | | | IV-1 | Timm10b |
| 18782 | 3 | 4 | | | IV-1 | Timm22 |
| 18783 | 3 | 4 | | | IV-1 | Timm23 |
| 18784 | 3 | 4 | | | IV-1 | Timm44 |
| 18785 | 3 | 4 | | | IV-1 | Timm8a1 |
| 18786 | 3 | 4 | | | IV-1 | Timm8a2 |
| 18787 | 3 | 4 | | | IV-1 | Timm8b |
| 18788 | 3 | 4 | | | IV-1 | Timmdc1 |
| 18789 | 3 | 4 | | | IV-1 | Timp4 |
| 18790 | 3 | 4 | | | IV-1 | Tinf2 |
| 18791 | 3 | 4 | | | IV-1 | Tipin |
| 18792 | 3 | 4 | | | IV-1 | Tiprl |
| 18793 | 3 | 4 | | | IV-1 | Tjap1 |
| 18794 | 3 | 4 | | | IV-1 | Tjp1 |
| 18795 | 3 | 4 | | | IV-1 | Tjp2 |
| 18796 | 3 | 4 | | | IV-1 | Tk2 |
| 18797 | 3 | 4 | | | IV-1 | Tktl1 |
| 18798 | 3 | 4 | | | IV-1 | Tle1 |
| 18799 | 3 | 4 | | | IV-1 | Tle3 |
| 18800 | 3 | 4 | | | IV-1 | Tle4 |
| 18801 | 3 | 4 | | | IV-1 | Tlk1 |
| 18802 | 3 | 4 | | | IV-1 | Tlk2 |
| 18803 | 3 | 4 | | | IV-1 | Tll1 |
| 18804 | 3 | 4 | | | IV-1 | Tlx1 |
| 18805 | 3 | 4 | | | IV-1 | Tlx2 |
| 18806 | 3 | 4 | | | IV-1 | Tlx3 |
| 18807 | 3 | 4 | | | IV-1 | Tm4sf1 |
| 18808 | 3 | 4 | | | IV-1 | Tm4sf19 |
| 18809 | 3 | 4 | | | IV-1 | Tm7sf3 |
| 18810 | 3 | 4 | | | IV-1 | Tm9sf1 |
| 18811 | 3 | 4 | | | IV-1 | Tm9sf2 |
| 18812 | 3 | 4 | | | IV-1 | Tm9sf3 |
| 18813 | 3 | 4 | | | IV-1 | Tm9sf4 |
| 18814 | 3 | 4 | | | IV-1 | Tmbim1 |

Fig. 36 - 99

| | | | | | | |
|---|---|---|---|---|---|---|
| 18815 | 3 | 4 | | | IV-1 | Tmbim6 |
| 18816 | 3 | 4 | | | IV-1 | Tmbim7 |
| 18817 | 3 | 4 | | | IV-1 | Tmc1 |
| 18818 | 3 | 4 | | | IV-1 | Tmc3 |
| 18819 | 3 | 4 | | | IV-1 | Tmcc1 |
| 18820 | 3 | 4 | | | IV-1 | Tmco1 |
| 18821 | 3 | 4 | | | IV-1 | Tmco2 |
| 18822 | 3 | 4 | | | IV-1 | Tmco3 |
| 18823 | 3 | 4 | | | IV-1 | Tmco4 |
| 18824 | 3 | 4 | | | IV-1 | Tmco5b |
| 18825 | 3 | 4 | | | IV-1 | Tmed10 |
| 18826 | 3 | 4 | | | IV-1 | Tmed2 |
| 18827 | 3 | 4 | | | IV-1 | Tmed4 |
| 18828 | 3 | 4 | | | IV-1 | Tmed7 |
| 18829 | 3 | 4 | | | IV-1 | Tmeff1 |
| 18830 | 3 | 4 | | | IV-1 | Tmeff2 |
| 18831 | 3 | 4 | | | IV-1 | Tmem104 |
| 18832 | 3 | 4 | | | IV-1 | Tmem106b |
| 18833 | 3 | 4 | | | IV-1 | Tmem106c |
| 18834 | 3 | 4 | | | IV-1 | Tmem108 |
| 18835 | 3 | 4 | | | IV-1 | Tmem109 |
| 18836 | 3 | 4 | | | IV-1 | Tmem110 |
| 18837 | 3 | 4 | | | IV-1 | Tmem115 |
| 18838 | 3 | 4 | | | IV-1 | Tmem117 |
| 18839 | 3 | 4 | | | IV-1 | Tmem120b |
| 18840 | 3 | 4 | | | IV-1 | Tmem121 |
| 18841 | 3 | 4 | | | IV-1 | Tmem125 |
| 18842 | 3 | 4 | | | IV-1 | Tmem127 |
| 18843 | 3 | 4 | | | IV-1 | Tmem129 |
| 18844 | 3 | 4 | | | IV-1 | Tmem130 |
| 18845 | 3 | 4 | | | IV-1 | Tmem131 |
| 18846 | 3 | 4 | | | IV-1 | Tmem132c |
| 18847 | 3 | 4 | | | IV-1 | Tmem132cos |
| 18848 | 3 | 4 | | | IV-1 | Tmem132e |
| 18849 | 3 | 4 | | | IV-1 | Tmem135 |
| 18850 | 3 | 4 | | | IV-1 | Tmem145 |
| 18851 | 3 | 4 | | | IV-1 | Tmem147 |
| 18852 | 3 | 4 | | | IV-1 | Tmem150b |
| 18853 | 3 | 4 | | | IV-1 | Tmem151b |
| 18854 | 3 | 4 | | | IV-1 | Tmem154 |
| 18855 | 3 | 4 | | | IV-1 | Tmem159 |
| 18856 | 3 | 4 | | | IV-1 | Tmem161a |
| 18857 | 3 | 4 | | | IV-1 | Tmem163 |
| 18858 | 3 | 4 | | | IV-1 | Tmem165 |
| 18859 | 3 | 4 | | | IV-1 | Tmem167 |
| 18860 | 3 | 4 | | | IV-1 | Tmem168 |
| 18861 | 3 | 4 | | | IV-1 | Tmem169 |
| 18862 | 3 | 4 | | | IV-1 | Tmem170b |
| 18863 | 3 | 4 | | | IV-1 | Tmem174 |
| 18864 | 3 | 4 | | | IV-1 | Tmem175 |
| 18865 | 3 | 4 | | | IV-1 | Tmem177 |
| 18866 | 3 | 4 | | | IV-1 | Tmem18 |
| 18867 | 3 | 4 | | | IV-1 | Tmem181b-ps |
| 18868 | 3 | 4 | | | IV-1 | Tmem181c-ps |
| 18869 | 3 | 4 | | | IV-1 | Tmem184b |
| 18870 | 3 | 4 | | | IV-1 | Tmem184c |
| 18871 | 3 | 4 | | | IV-1 | Tmem185b |
| 18872 | 3 | 4 | | | IV-1 | Tmem186 |
| 18873 | 3 | 4 | | | IV-1 | Tmem189 |
| 18874 | 3 | 4 | | | IV-1 | Tmem19 |
| 18875 | 3 | 4 | | | IV-1 | Tmem194 |
| 18876 | 3 | 4 | | | IV-1 | Tmem194b |
| 18877 | 3 | 4 | | | IV-1 | Tmem198b |
| 18878 | 3 | 4 | | | IV-1 | Tmem199 |
| 18879 | 3 | 4 | | | IV-1 | Tmem200a |
| 18880 | 3 | 4 | | | IV-1 | Tmem200c |
| 18881 | 3 | 4 | | | IV-1 | Tmem201 |
| 18882 | 3 | 4 | | | IV-1 | Tmem204 |
| 18883 | 3 | 4 | | | IV-1 | Tmem206 |
| 18884 | 3 | 4 | | | IV-1 | Tmem209 |
| 18885 | 3 | 4 | | | IV-1 | Tmem214 |
| 18886 | 3 | 4 | | | IV-1 | Tmem217 |
| 18887 | 3 | 4 | | | IV-1 | Tmem219 |
| 18888 | 3 | 4 | | | IV-1 | Tmem225 |
| 18889 | 3 | 4 | | | IV-1 | Tmem229a |
| 18890 | 3 | 4 | | | IV-1 | Tmem232 |
| 18891 | 3 | 4 | | | IV-1 | Tmem236 |
| 18892 | 3 | 4 | | | IV-1 | Tmem242 |
| 18893 | 3 | 4 | | | IV-1 | Tmem248 |
| 18894 | 3 | 4 | | | IV-1 | Tmem251 |
| 18895 | 3 | 4 | | | IV-1 | Tmem259 |
| 18896 | 3 | 4 | | | IV-1 | Tmem26 |
| 18897 | 3 | 4 | | | IV-1 | Tmem260 |
| 18898 | 3 | 4 | | | IV-1 | Tmem30a |
| 18899 | 3 | 4 | | | IV-1 | Tmem30c |
| 18900 | 3 | 4 | | | IV-1 | Tmem33 |
| 18901 | 3 | 4 | | | IV-1 | Tmem35 |
| 18902 | 3 | 4 | | | IV-1 | Tmem38a |
| 18903 | 3 | 4 | | | IV-1 | Tmem39a |
| 18904 | 3 | 4 | | | IV-1 | Tmem41b |
| 18905 | 3 | 4 | | | IV-1 | Tmem43 |
| 18906 | 3 | 4 | | | IV-1 | Tmem44 |
| 18907 | 3 | 4 | | | IV-1 | Tmem45a |
| 18908 | 3 | 4 | | | IV-1 | Tmem5 |
| 18909 | 3 | 4 | | | IV-1 | Tmem50b |
| 18910 | 3 | 4 | | | IV-1 | Tmem52b |
| 18911 | 3 | 4 | | | IV-1 | Tmem54 |
| 18912 | 3 | 4 | | | IV-1 | Tmem55b |
| 18913 | 3 | 4 | | | IV-1 | Tmem56 |
| 18914 | 3 | 4 | | | IV-1 | Tmem57 |
| 18915 | 3 | 4 | | | IV-1 | Tmem59 |
| 18916 | 3 | 4 | | | IV-1 | Tmem63b |
| 18917 | 3 | 4 | | | IV-1 | Tmem64 |
| 18918 | 3 | 4 | | | IV-1 | Tmem65 |
| 18919 | 3 | 4 | | | IV-1 | Tmem66 |
| 18920 | 3 | 4 | | | IV-1 | Tmem67 |
| 18921 | 3 | 4 | | | IV-1 | Tmem68 |
| 18922 | 3 | 4 | | | IV-1 | Tmem74b |
| 18923 | 3 | 4 | | | IV-1 | Tmem79 |
| 18924 | 3 | 4 | | | IV-1 | Tmem81 |
| 18925 | 3 | 4 | | | IV-1 | Tmem82 |
| 18926 | 3 | 4 | | | IV-1 | Tmem86a |
| 18927 | 3 | 4 | | | IV-1 | Tmem87a |
| 18928 | 3 | 4 | | | IV-1 | Tmem87b |
| 18929 | 3 | 4 | | | IV-1 | Tmem8b |
| 18930 | 3 | 4 | | | IV-1 | Tmem97 |
| 18931 | 3 | 4 | | | IV-1 | Tmem9b |
| 18932 | 3 | 4 | | | IV-1 | Tmf1 |
| 18933 | 3 | 4 | | | IV-1 | Tmigd1 |
| 18934 | 3 | 4 | | | IV-1 | Tmpo |
| 18935 | 3 | 4 | | | IV-1 | Tmprss11a |
| 18936 | 3 | 4 | | | IV-1 | Tmprss11e |
| 18937 | 3 | 4 | | | IV-1 | Tmprss12 |
| 18938 | 3 | 4 | | | IV-1 | Tmprss3 |
| 18939 | 3 | 4 | | | IV-1 | Tmprss4 |
| 18940 | 3 | 4 | | | IV-1 | Tmprss5 |
| 18941 | 3 | 4 | | | IV-1 | Tmprss6 |
| 18942 | 3 | 4 | | | IV-1 | Tmprss7 |
| 18943 | 3 | 4 | | | IV-1 | Tmprss9 |
| 18944 | 3 | 4 | | | IV-1 | Tmsb15a |
| 18945 | 3 | 4 | | | IV-1 | Tmub1 |
| 18946 | 3 | 4 | | | IV-1 | Tmub2 |
| 18947 | 3 | 4 | | | IV-1 | Tmx1 |
| 18948 | 3 | 4 | | | IV-1 | Tmx2 |
| 18949 | 3 | 4 | | | IV-1 | Tmx4 |
| 18950 | 3 | 4 | | | IV-1 | Tnfaip1 |
| 18951 | 3 | 4 | | | IV-1 | Tnfaip3 |
| 18952 | 3 | 4 | | | IV-1 | Tnfaip8 |
| 18953 | 3 | 4 | | | IV-1 | Tnfaip8l3 |
| 18954 | 3 | 4 | | | IV-1 | Tnfrsf11a |
| 18955 | 3 | 4 | | | IV-1 | Tnfrsf13c |
| 18956 | 3 | 4 | | | IV-1 | Tnfrsf19 |
| 18957 | 3 | 4 | | | IV-1 | Tnfrsf1a |
| 18958 | 3 | 4 | | | IV-1 | Tnfrsf1b |
| 18959 | 3 | 4 | | | IV-1 | Tnfrsf26 |
| 18960 | 3 | 4 | | | IV-1 | Tnfrsf4 |
| 18961 | 3 | 4 | | | IV-1 | Tnfrsf8 |
| 18962 | 3 | 4 | | | IV-1 | Tnfsf11 |
| 18963 | 3 | 4 | | | IV-1 | Tnfsf13b |
| 18964 | 3 | 4 | | | IV-1 | Tnfsf15 |
| 18965 | 3 | 4 | | | IV-1 | Tnfsf8 |
| 18966 | 3 | 4 | | | IV-1 | Tnip2 |
| 18967 | 3 | 4 | | | IV-1 | Tnip3 |
| 18968 | 3 | 4 | | | IV-1 | Tnks1bp1 |
| 18969 | 3 | 4 | | | IV-1 | Tnks2 |
| 18970 | 3 | 4 | | | IV-1 | Tnn |
| 18971 | 3 | 4 | | | IV-1 | Tnpo2 |
| 18972 | 3 | 4 | | | IV-1 | Tnpo3 |
| 18973 | 3 | 4 | | | IV-1 | Tns3 |
| 18974 | 3 | 4 | | | IV-1 | Tns4 |
| 18975 | 3 | 4 | | | IV-1 | Toe1 |
| 18976 | 3 | 4 | | | IV-1 | Tomm20 |
| 18977 | 3 | 4 | | | IV-1 | Tomm20l |
| 18978 | 3 | 4 | | | IV-1 | Tomm22 |
| 18979 | 3 | 4 | | | IV-1 | Tomm34 |
| 18980 | 3 | 4 | | | IV-1 | Tomm40 |
| 18981 | 3 | 4 | | | IV-1 | Tomm40l |
| 18982 | 3 | 4 | | | IV-1 | Tomm5 |
| 18983 | 3 | 4 | | | IV-1 | Tomm70a |
| 18984 | 3 | 4 | | | IV-1 | Tonsl |
| 18985 | 3 | 4 | | | IV-1 | Top1mt |
| 18986 | 3 | 4 | | | IV-1 | Top2a |
| 18987 | 3 | 4 | | | IV-1 | Top3a |
| 18988 | 3 | 4 | | | IV-1 | Top3b |
| 18989 | 3 | 4 | | | IV-1 | Topbp1 |
| 18990 | 3 | 4 | | | IV-1 | Topors |
| 18991 | 3 | 4 | | | IV-1 | Tor1a |
| 18992 | 3 | 4 | | | IV-1 | Tor1aip2 |
| 18993 | 3 | 4 | | | IV-1 | Tor1b |
| 18994 | 3 | 4 | | | IV-1 | Tor2a |
| 18995 | 3 | 4 | | | IV-1 | Tor4a |
| 18996 | 3 | 4 | | | IV-1 | Tox4 |
| 18997 | 3 | 4 | | | IV-1 | Tpbg |
| 18998 | 3 | 4 | | | IV-1 | Tpcn1 |
| 18999 | 3 | 4 | | | IV-1 | Tpd52l2 |
| 19000 | 3 | 4 | | | IV-1 | Tpgs2 |
| 19001 | 3 | 4 | | | IV-1 | Tpi1 |
| 19002 | 3 | 4 | | | IV-1 | Tpk1 |
| 19003 | 3 | 4 | | | IV-1 | Tpp1 |
| 19004 | 3 | 4 | | | IV-1 | Tpp2 |
| 19005 | 3 | 4 | | | IV-1 | Tppp2 |
| 19006 | 3 | 4 | | | IV-1 | Tpra1 |

Fig. 36 - 100

| | | | | | | |
|---|---|---|---|---|---|---|
| 19007 | 3 | 4 | | | IV-1 | Tprg |
| 19008 | 3 | 4 | | | IV-1 | Tprkb |
| 19009 | 3 | 4 | | | IV-1 | Tprn |
| 19010 | 3 | 4 | | | IV-1 | Tpsb2 |
| 19011 | 3 | 4 | | | IV-1 | Tpst1 |
| 19012 | 3 | 4 | | | IV-1 | Tpte |
| 19013 | 3 | 4 | | | IV-1 | Tpx2 |
| 19014 | 3 | 4 | | | IV-1 | Trabd |
| 19015 | 3 | 4 | | | IV-1 | Trabd2b |
| 19016 | 3 | 4 | | | IV-1 | Traf1 |
| 19017 | 3 | 4 | | | IV-1 | Traf2 |
| 19018 | 3 | 4 | | | IV-1 | Traf3 |
| 19019 | 3 | 4 | | | IV-1 | Traf3ip1 |
| 19020 | 3 | 4 | | | IV-1 | Traf3ip3 |
| 19021 | 3 | 4 | | | IV-1 | Traf4 |
| 19022 | 3 | 4 | | | IV-1 | Trafd1 |
| 19023 | 3 | 4 | | | IV-1 | Trak1 |
| 19024 | 3 | 4 | | | IV-1 | Tram1 |
| 19025 | 3 | 4 | | | IV-1 | Tram1l1 |
| 19026 | 3 | 4 | | | IV-1 | Trap1 |
| 19027 | 3 | 4 | | | IV-1 | Trap1a |
| 19028 | 3 | 4 | | | IV-1 | Trappc10 |
| 19029 | 3 | 4 | | | IV-1 | Trappc11 |
| 19030 | 3 | 4 | | | IV-1 | Trappc13 |
| 19031 | 3 | 4 | | | IV-1 | Trappc3 |
| 19032 | 3 | 4 | | | IV-1 | Trappc5 |
| 19033 | 3 | 4 | | | IV-1 | Trappc8 |
| 19034 | 3 | 4 | | | IV-1 | Trdn |
| 19035 | 3 | 4 | | | IV-1 | Treh |
| 19036 | 3 | 4 | | | IV-1 | Trem1 |
| 19037 | 3 | 4 | | | IV-1 | Treml4 |
| 19038 | 3 | 4 | | | IV-1 | Trex2 |
| 19039 | 3 | 4 | | | IV-1 | Trh |
| 19040 | 3 | 4 | | | IV-1 | Trhde |
| 19041 | 3 | 4 | | | IV-1 | Trhr |
| 19042 | 3 | 4 | | | IV-1 | Trib2 |
| 19043 | 3 | 4 | | | IV-1 | Trim11 |
| 19044 | 3 | 4 | | | IV-1 | Trim14 |
| 19045 | 3 | 4 | | | IV-1 | Trim15 |
| 19046 | 3 | 4 | | | IV-1 | Trim16 |
| 19047 | 3 | 4 | | | IV-1 | Trim2 |
| 19048 | 3 | 4 | | | IV-1 | Trim21 |
| 19049 | 3 | 4 | | | IV-1 | Trim24 |
| 19050 | 3 | 4 | | | IV-1 | Trim26 |
| 19051 | 3 | 4 | | | IV-1 | Trim27 |
| 19052 | 3 | 4 | | | IV-1 | Trim28 |
| 19053 | 3 | 4 | | | IV-1 | Trim33 |
| 19054 | 3 | 4 | | | IV-1 | Trim35 |
| 19055 | 3 | 4 | | | IV-1 | Trim37 |
| 19056 | 3 | 4 | | | IV-1 | Trim39 |
| 19057 | 3 | 4 | | | IV-1 | Trim40 |
| 19058 | 3 | 4 | | | IV-1 | Trim41 |
| 19059 | 3 | 4 | | | IV-1 | Trim43b |
| 19060 | 3 | 4 | | | IV-1 | Trim44 |
| 19061 | 3 | 4 | | | IV-1 | Trim45 |
| 19062 | 3 | 4 | | | IV-1 | Trim46 |
| 19063 | 3 | 4 | | | IV-1 | Trim52 |
| 19064 | 3 | 4 | | | IV-1 | Trim55 |
| 19065 | 3 | 4 | | | IV-1 | Trim69 |
| 19066 | 3 | 4 | | | IV-1 | Trim71 |
| 19067 | 3 | 4 | | | IV-1 | Trim8 |
| 19068 | 3 | 4 | | | IV-1 | Trim9 |
| 19069 | 3 | 4 | | | IV-1 | Triml1 |
| 19070 | 3 | 4 | | | IV-1 | Triobp |
| 19071 | 3 | 4 | | | IV-1 | Trip12 |
| 19072 | 3 | 4 | | | IV-1 | Trip13 |
| 19073 | 3 | 4 | | | IV-1 | Trip4 |
| 19074 | 3 | 4 | | | IV-1 | Trip6 |
| 19075 | 3 | 4 | | | IV-1 | Trmt10a |
| 19076 | 3 | 4 | | | IV-1 | Trmt112 |
| 19077 | 3 | 4 | | | IV-1 | Trmt1l |
| 19078 | 3 | 4 | | | IV-1 | Trmt2a |
| 19079 | 3 | 4 | | | IV-1 | Trmt2b |
| 19080 | 3 | 4 | | | IV-1 | Trmt5 |
| 19081 | 3 | 4 | | | IV-1 | Trmt6 |
| 19082 | 3 | 4 | | | IV-1 | Trnau1ap |
| 19083 | 3 | 4 | | | IV-1 | Trnp1 |
| 19084 | 3 | 4 | | | IV-1 | Trnt1 |
| 19085 | 3 | 4 | | | IV-1 | Tro |
| 19086 | 3 | 4 | | | IV-1 | Trove2 |
| 19087 | 3 | 4 | | | IV-1 | Trp53 |
| 19088 | 3 | 4 | | | IV-1 | Trp53bp2 |
| 19089 | 3 | 4 | | | IV-1 | Trp53inp2 |
| 19090 | 3 | 4 | | | IV-1 | Trp53rk |
| 19091 | 3 | 4 | | | IV-1 | Trp73 |
| 19092 | 3 | 4 | | | IV-1 | Trpc3 |
| 19093 | 3 | 4 | | | IV-1 | Trpc4 |
| 19094 | 3 | 4 | | | IV-1 | Trpc4ap |
| 19095 | 3 | 4 | | | IV-1 | Trpc5os |
| 19096 | 3 | 4 | | | IV-1 | Trpc7 |
| 19097 | 3 | 4 | | | IV-1 | Trpd52l3 |
| 19098 | 3 | 4 | | | IV-1 | Trpm6 |
| 19099 | 3 | 4 | | | IV-1 | Trpm7 |
| 19100 | 3 | 4 | | | IV-1 | Trpm8 |
| 19101 | 3 | 4 | | | IV-1 | Trpv2 |
| 19102 | 3 | 4 | | | IV-1 | Trpv5 |
| 19103 | 3 | 4 | | | IV-1 | Trpv6 |
| 19104 | 3 | 4 | | | IV-1 | Trub1 |
| 19105 | 3 | 4 | | | IV-1 | Trub2 |
| 19106 | 3 | 4 | | | IV-1 | Tsc2 |
| 19107 | 3 | 4 | | | IV-1 | Tsc22d2 |
| 19108 | 3 | 4 | | | IV-1 | Tsc22d4 |
| 19109 | 3 | 4 | | | IV-1 | Tsen2 |
| 19110 | 3 | 4 | | | IV-1 | Tsen54 |
| 19111 | 3 | 4 | | | IV-1 | Tsga13 |
| 19112 | 3 | 4 | | | IV-1 | Tsga8 |
| 19113 | 3 | 4 | | | IV-1 | Tshr |
| 19114 | 3 | 4 | | | IV-1 | Tshz3 |
| 19115 | 3 | 4 | | | IV-1 | Tsks |
| 19116 | 3 | 4 | | | IV-1 | Tsn |
| 19117 | 3 | 4 | | | IV-1 | Tsnax |
| 19118 | 3 | 4 | | | IV-1 | Tsnaxip1 |
| 19119 | 3 | 4 | | | IV-1 | Tspan10 |
| 19120 | 3 | 4 | | | IV-1 | Tspan12 |
| 19121 | 3 | 4 | | | IV-1 | Tspan13 |
| 19122 | 3 | 4 | | | IV-1 | Tspan14 |
| 19123 | 3 | 4 | | | IV-1 | Tspan15 |
| 19124 | 3 | 4 | | | IV-1 | Tspan2 |
| 19125 | 3 | 4 | | | IV-1 | Tspan3 |
| 19126 | 3 | 4 | | | IV-1 | Tspan31 |
| 19127 | 3 | 4 | | | IV-1 | Tspan4 |
| 19128 | 3 | 4 | | | IV-1 | Tspan5 |
| 19129 | 3 | 4 | | | IV-1 | Tspan7 |
| 19130 | 3 | 4 | | | IV-1 | Tspan8 |
| 19131 | 3 | 4 | | | IV-1 | Tspyl2 |
| 19132 | 3 | 4 | | | IV-1 | Tspyl3 |
| 19133 | 3 | 4 | | | IV-1 | Tsr1 |
| 19134 | 3 | 4 | | | IV-1 | Tsr2 |
| 19135 | 3 | 4 | | | IV-1 | Tssc1 |
| 19136 | 3 | 4 | | | IV-1 | Tssk2 |
| 19137 | 3 | 4 | | | IV-1 | Tssk3 |
| 19138 | 3 | 4 | | | IV-1 | Tssk5 |
| 19139 | 3 | 4 | | | IV-1 | Tsta3 |
| 19140 | 3 | 4 | | | IV-1 | Tsx |
| 19141 | 3 | 4 | | | IV-1 | Ttc1 |
| 19142 | 3 | 4 | | | IV-1 | Ttc12 |
| 19143 | 3 | 4 | | | IV-1 | Ttc13 |
| 19144 | 3 | 4 | | | IV-1 | Ttc17 |
| 19145 | 3 | 4 | | | IV-1 | Ttc18 |
| 19146 | 3 | 4 | | | IV-1 | Ttc21b |
| 19147 | 3 | 4 | | | IV-1 | Ttc22 |
| 19148 | 3 | 4 | | | IV-1 | Ttc23 |
| 19149 | 3 | 4 | | | IV-1 | Ttc23l |
| 19150 | 3 | 4 | | | IV-1 | Ttc3 |
| 19151 | 3 | 4 | | | IV-1 | Ttc30b |
| 19152 | 3 | 4 | | | IV-1 | Ttc38 |
| 19153 | 3 | 4 | | | IV-1 | Ttc39c |
| 19154 | 3 | 4 | | | IV-1 | Ttc39d |
| 19155 | 3 | 4 | | | IV-1 | Ttc4 |
| 19156 | 3 | 4 | | | IV-1 | Ttc5 |
| 19157 | 3 | 4 | | | IV-1 | Ttc7 |
| 19158 | 3 | 4 | | | IV-1 | Ttc7b |
| 19159 | 3 | 4 | | | IV-1 | Ttc9b |
| 19160 | 3 | 4 | | | IV-1 | Ttf1 |
| 19161 | 3 | 4 | | | IV-1 | Ttf2 |
| 19162 | 3 | 4 | | | IV-1 | Ttk |
| 19163 | 3 | 4 | | | IV-1 | Ttl |
| 19164 | 3 | 4 | | | IV-1 | Ttll2 |
| 19165 | 3 | 4 | | | IV-1 | Ttll5 |
| 19166 | 3 | 4 | | | IV-1 | Ttll6 |
| 19167 | 3 | 4 | | | IV-1 | Ttll9 |
| 19168 | 3 | 4 | | | IV-1 | Ttpal |
| 19169 | 3 | 4 | | | IV-1 | Ttyh1 |
| 19170 | 3 | 4 | | | IV-1 | Tub |
| 19171 | 3 | 4 | | | IV-1 | Tuba1b |
| 19172 | 3 | 4 | | | IV-1 | Tubal3 |
| 19173 | 3 | 4 | | | IV-1 | Tubb3 |
| 19174 | 3 | 4 | | | IV-1 | Tubb4a |
| 19175 | 3 | 4 | | | IV-1 | Tubb5 |
| 19176 | 3 | 4 | | | IV-1 | Tube1 |
| 19177 | 3 | 4 | | | IV-1 | Tubg1 |
| 19178 | 3 | 4 | | | IV-1 | Tubg2 |
| 19179 | 3 | 4 | | | IV-1 | Tubgcp2 |
| 19180 | 3 | 4 | | | IV-1 | Tubgcp5 |
| 19181 | 3 | 4 | | | IV-1 | Tug1 |
| 19182 | 3 | 4 | | | IV-1 | Tulp1 |
| 19183 | 3 | 4 | | | IV-1 | Tulp2 |
| 19184 | 3 | 4 | | | IV-1 | Tunar |
| 19185 | 3 | 4 | | | IV-1 | Tut1 |
| 19186 | 3 | 4 | | | IV-1 | Tvp23b |
| 19187 | 3 | 4 | | | IV-1 | Twist2 |
| 19188 | 3 | 4 | | | IV-1 | Twistnb |
| 19189 | 3 | 4 | | | IV-1 | Twsg1 |
| 19190 | 3 | 4 | | | IV-1 | Txlnb |
| 19191 | 3 | 4 | | | IV-1 | Txndc11 |
| 19192 | 3 | 4 | | | IV-1 | Txndc15 |
| 19193 | 3 | 4 | | | IV-1 | Txndc16 |
| 19194 | 3 | 4 | | | IV-1 | Txndc17 |
| 19195 | 3 | 4 | | | IV-1 | Txndc5 |
| 19196 | 3 | 4 | | | IV-1 | Txndc9 |
| 19197 | 3 | 4 | | | IV-1 | Txnl1 |
| 19198 | 3 | 4 | | | IV-1 | Txnl4b |

Fig. 36 - 101

| | | | | | | |
|---|---|---|---|---|---|---|
| 19199 | 3 | 4 | | | IV-1 | Txnrd1 |
| 19200 | 3 | 4 | | | IV-1 | Tyms |
| 19201 | 3 | 4 | | | IV-1 | Tyr |
| 19202 | 3 | 4 | | | IV-1 | Tyro3 |
| 19203 | 3 | 4 | | | IV-1 | Tyrp1 |
| 19204 | 3 | 4 | | | IV-1 | Tyw1 |
| 19205 | 3 | 4 | | | IV-1 | Tyw3 |
| 19206 | 3 | 4 | | | IV-1 | U2af2 |
| 19207 | 3 | 4 | | | IV-1 | U2surp |
| 19208 | 3 | 4 | | | IV-1 | U90926 |
| 19209 | 3 | 4 | | | IV-1 | Uaca |
| 19210 | 3 | 4 | | | IV-1 | Uap1 |
| 19211 | 3 | 4 | | | IV-1 | Uba1 |
| 19212 | 3 | 4 | | | IV-1 | Uba1y |
| 19213 | 3 | 4 | | | IV-1 | Uba2 |
| 19214 | 3 | 4 | | | IV-1 | Uba3 |
| 19215 | 3 | 4 | | | IV-1 | Uba5 |
| 19216 | 3 | 4 | | | IV-1 | Ubac2 |
| 19217 | 3 | 4 | | | IV-1 | Ubap2 |
| 19218 | 3 | 4 | | | IV-1 | Ubap2l |
| 19219 | 3 | 4 | | | IV-1 | Ubash3a |
| 19220 | 3 | 4 | | | IV-1 | Ube2d2a |
| 19221 | 3 | 4 | | | IV-1 | Ube2d2b |
| 19222 | 3 | 4 | | | IV-1 | Ube2dnl |
| 19223 | 3 | 4 | | | IV-1 | Ube2dnl2 |
| 19224 | 3 | 4 | | | IV-1 | Ube2e1 |
| 19225 | 3 | 4 | | | IV-1 | Ube2g1 |
| 19226 | 3 | 4 | | | IV-1 | Ube2g2 |
| 19227 | 3 | 4 | | | IV-1 | Ube2h |
| 19228 | 3 | 4 | | | IV-1 | Ube2j1 |
| 19229 | 3 | 4 | | | IV-1 | Ube2k |
| 19230 | 3 | 4 | | | IV-1 | Ube2l3 |
| 19231 | 3 | 4 | | | IV-1 | Ube2n |
| 19232 | 3 | 4 | | | IV-1 | Ube2q1 |
| 19233 | 3 | 4 | | | IV-1 | Ube2q2 |
| 19234 | 3 | 4 | | | IV-1 | Ube2ql1 |
| 19235 | 3 | 4 | | | IV-1 | Ube2v1 |
| 19236 | 3 | 4 | | | IV-1 | Ube2v2 |
| 19237 | 3 | 4 | | | IV-1 | Ube2w |
| 19238 | 3 | 4 | | | IV-1 | Ube2z |
| 19239 | 3 | 4 | | | IV-1 | Ube3c |
| 19240 | 3 | 4 | | | IV-1 | Ube4a |
| 19241 | 3 | 4 | | | IV-1 | Ube4b |
| 19242 | 3 | 4 | | | IV-1 | Ubfd1 |
| 19243 | 3 | 4 | | | IV-1 | Ubiad1 |
| 19244 | 3 | 4 | | | IV-1 | Ubl3 |
| 19245 | 3 | 4 | | | IV-1 | Ubl4 |
| 19246 | 3 | 4 | | | IV-1 | Ubl4b |
| 19247 | 3 | 4 | | | IV-1 | Ublcp1 |
| 19248 | 3 | 4 | | | IV-1 | Ubn1 |
| 19249 | 3 | 4 | | | IV-1 | Ubox5 |
| 19250 | 3 | 4 | | | IV-1 | Ubp1 |
| 19251 | 3 | 4 | | | IV-1 | Ubqln1 |
| 19252 | 3 | 4 | | | IV-1 | Ubqln2 |
| 19253 | 3 | 4 | | | IV-1 | Ubqln4 |
| 19254 | 3 | 4 | | | IV-1 | Ubr1 |
| 19255 | 3 | 4 | | | IV-1 | Ubr2 |
| 19256 | 3 | 4 | | | IV-1 | Ubr3 |
| 19257 | 3 | 4 | | | IV-1 | Ubr7 |
| 19258 | 3 | 4 | | | IV-1 | Ubtd2 |
| 19259 | 3 | 4 | | | IV-1 | Ubtf |
| 19260 | 3 | 4 | | | IV-1 | Ubxn4 |
| 19261 | 3 | 4 | | | IV-1 | Ubxn6 |
| 19262 | 3 | 4 | | | IV-1 | Ubxn7 |
| 19263 | 3 | 4 | | | IV-1 | Ubxn8 |
| 19264 | 3 | 4 | | | IV-1 | Uck1 |
| 19265 | 3 | 4 | | | IV-1 | Uckl1 |
| 19266 | 3 | 4 | | | IV-1 | Ucn2 |
| 19267 | 3 | 4 | | | IV-1 | Ufc1 |
| 19268 | 3 | 4 | | | IV-1 | Ufd1l |
| 19269 | 3 | 4 | | | IV-1 | Ufl1 |
| 19270 | 3 | 4 | | | IV-1 | Ufm1 |
| 19271 | 3 | 4 | | | IV-1 | Ufsp2 |
| 19272 | 3 | 4 | | | IV-1 | Ugcg |
| 19273 | 3 | 4 | | | IV-1 | Uggt1 |
| 19274 | 3 | 4 | | | IV-1 | Uggt2 |
| 19275 | 3 | 4 | | | IV-1 | Ugt1a10 |
| 19276 | 3 | 4 | | | IV-1 | Ugt1a5 |
| 19277 | 3 | 4 | | | IV-1 | Ugt1a9 |
| 19278 | 3 | 4 | | | IV-1 | Ugt2a3 |
| 19279 | 3 | 4 | | | IV-1 | Ugt2b1 |
| 19280 | 3 | 4 | | | IV-1 | Ugt2b34 |
| 19281 | 3 | 4 | | | IV-1 | Ugt2b35 |
| 19282 | 3 | 4 | | | IV-1 | Ugt2b38 |
| 19283 | 3 | 4 | | | IV-1 | Ugt3a1 |
| 19284 | 3 | 4 | | | IV-1 | Ugt8a |
| 19285 | 3 | 4 | | | IV-1 | Uhrf1bp1l |
| 19286 | 3 | 4 | | | IV-1 | Uhrf2 |
| 19287 | 3 | 4 | | | IV-1 | Uimc1 |
| 19288 | 3 | 4 | | | IV-1 | Ulk1 |
| 19289 | 3 | 4 | | | IV-1 | Ulk2 |
| 19290 | 3 | 4 | | | IV-1 | Ulk4 |
| 19291 | 3 | 4 | | | IV-1 | Unc119b |
| 19292 | 3 | 4 | | | IV-1 | Unc13a |
| 19293 | 3 | 4 | | | IV-1 | Unc13b |
| 19294 | 3 | 4 | | | IV-1 | Unc45a |

| | | | | | | |
|---|---|---|---|---|---|---|
| 19295 | 3 | 4 | | | IV-1 | Unc50 |
| 19296 | 3 | 4 | | | IV-1 | Unc5a |
| 19297 | 3 | 4 | | | IV-1 | Unc5b |
| 19298 | 3 | 4 | | | IV-1 | Unc5d |
| 19299 | 3 | 4 | | | IV-1 | Unc79 |
| 19300 | 3 | 4 | | | IV-1 | Unc80 |
| 19301 | 3 | 4 | | | IV-1 | Uncx |
| 19302 | 3 | 4 | | | IV-1 | Unk |
| 19303 | 3 | 4 | | | IV-1 | Unkl |
| 19304 | 3 | 4 | | | IV-1 | Uox |
| 19305 | 3 | 4 | | | IV-1 | Upb1 |
| 19306 | 3 | 4 | | | IV-1 | Upf1 |
| 19307 | 3 | 4 | | | IV-1 | Upf2 |
| 19308 | 3 | 4 | | | IV-1 | Upf3a |
| 19309 | 3 | 4 | | | IV-1 | Upf3b |
| 19310 | 3 | 4 | | | IV-1 | Upk2 |
| 19311 | 3 | 4 | | | IV-1 | Upk3a |
| 19312 | 3 | 4 | | | IV-1 | Upk3bl |
| 19313 | 3 | 4 | | | IV-1 | Uqcc1 |
| 19314 | 3 | 4 | | | IV-1 | Uqcrc1 |
| 19315 | 3 | 4 | | | IV-1 | Urgcp |
| 19316 | 3 | 4 | | | IV-1 | Uri1 |
| 19317 | 3 | 4 | | | IV-1 | Uroc1 |
| 19318 | 3 | 4 | | | IV-1 | Usf1 |
| 19319 | 3 | 4 | | | IV-1 | Usf2 |
| 19320 | 3 | 4 | | | IV-1 | Ush1c |
| 19321 | 3 | 4 | | | IV-1 | Ush1g |
| 19322 | 3 | 4 | | | IV-1 | Ushbp1 |
| 19323 | 3 | 4 | | | IV-1 | Uso1 |
| 19324 | 3 | 4 | | | IV-1 | Usp1 |
| 19325 | 3 | 4 | | | IV-1 | Usp10 |
| 19326 | 3 | 4 | | | IV-1 | Usp12 |
| 19327 | 3 | 4 | | | IV-1 | Usp14 |
| 19328 | 3 | 4 | | | IV-1 | Usp16 |
| 19329 | 3 | 4 | | | IV-1 | Usp21 |
| 19330 | 3 | 4 | | | IV-1 | Usp22 |
| 19331 | 3 | 4 | | | IV-1 | Usp24 |
| 19332 | 3 | 4 | | | IV-1 | Usp27x |
| 19333 | 3 | 4 | | | IV-1 | Usp28 |
| 19334 | 3 | 4 | | | IV-1 | Usp3 |
| 19335 | 3 | 4 | | | IV-1 | Usp30 |
| 19336 | 3 | 4 | | | IV-1 | Usp33 |
| 19337 | 3 | 4 | | | IV-1 | Usp35 |
| 19338 | 3 | 4 | | | IV-1 | Usp36 |
| 19339 | 3 | 4 | | | IV-1 | Usp37 |
| 19340 | 3 | 4 | | | IV-1 | Usp39 |
| 19341 | 3 | 4 | | | IV-1 | Usp4 |
| 19342 | 3 | 4 | | | IV-1 | Usp40 |
| 19343 | 3 | 4 | | | IV-1 | Usp43 |
| 19344 | 3 | 4 | | | IV-1 | Usp44 |
| 19345 | 3 | 4 | | | IV-1 | Usp45 |
| 19346 | 3 | 4 | | | IV-1 | Usp46 |
| 19347 | 3 | 4 | | | IV-1 | Usp47 |
| 19348 | 3 | 4 | | | IV-1 | Usp48 |
| 19349 | 3 | 4 | | | IV-1 | Usp5 |
| 19350 | 3 | 4 | | | IV-1 | Usp54 |
| 19351 | 3 | 4 | | | IV-1 | Usp7 |
| 19352 | 3 | 4 | | | IV-1 | Usp8 |
| 19353 | 3 | 4 | | | IV-1 | Usp9y |
| 19354 | 3 | 4 | | | IV-1 | Ust |
| 19355 | 3 | 4 | | | IV-1 | Utp14a |
| 19356 | 3 | 4 | | | IV-1 | Utp23 |
| 19357 | 3 | 4 | | | IV-1 | Utp3 |
| 19358 | 3 | 4 | | | IV-1 | Utp6 |
| 19359 | 3 | 4 | | | IV-1 | Utrn |
| 19360 | 3 | 4 | | | IV-1 | Uts2r |
| 19361 | 3 | 4 | | | IV-1 | Uty |
| 19362 | 3 | 4 | | | IV-1 | Uxt |
| 19363 | 3 | 4 | | | IV-1 | V1ra8 |
| 19364 | 3 | 4 | | | IV-1 | Vac14 |
| 19365 | 3 | 4 | | | IV-1 | Vamp2 |
| 19366 | 3 | 4 | | | IV-1 | Vamp3 |
| 19367 | 3 | 4 | | | IV-1 | Vamp7 |
| 19368 | 3 | 4 | | | IV-1 | Vangl1 |
| 19369 | 3 | 4 | | | IV-1 | Vapb |
| 19370 | 3 | 4 | | | IV-1 | Vars |
| 19371 | 3 | 4 | | | IV-1 | Vars2 |
| 19372 | 3 | 4 | | | IV-1 | Vash2 |
| 19373 | 3 | 4 | | | IV-1 | Vasp |
| 19374 | 3 | 4 | | | IV-1 | Vat1 |
| 19375 | 3 | 4 | | | IV-1 | Vat1l |
| 19376 | 3 | 4 | | | IV-1 | Vaultrc5 |
| 19377 | 3 | 4 | | | IV-1 | Vav3 |
| 19378 | 3 | 4 | | | IV-1 | Vax2os |
| 19379 | 3 | 4 | | | IV-1 | Vcp |
| 19380 | 3 | 4 | | | IV-1 | Vdac1 |
| 19381 | 3 | 4 | | | IV-1 | Vegfa |
| 19382 | 3 | 4 | | | IV-1 | Vezf1 |
| 19383 | 3 | 4 | | | IV-1 | Vezt |
| 19384 | 3 | 4 | | | IV-1 | Vgf |
| 19385 | 3 | 4 | | | IV-1 | Vgll2 |
| 19386 | 3 | 4 | | | IV-1 | Vgll3 |
| 19387 | 3 | 4 | | | IV-1 | Vill |
| 19388 | 3 | 4 | | | IV-1 | Vimp |
| 19389 | 3 | 4 | | | IV-1 | Vipr1 |
| 19390 | 3 | 4 | | | IV-1 | Vit |

Fig. 36 - 102

| | | | | | | |
|---|---|---|---|---|---|---|
| 19391 | 3 | 4 | | | IV-1 | Vldlr |
| 19392 | 3 | 4 | | | IV-1 | Vma21 |
| 19393 | 3 | 4 | | | IV-1 | Vmac |
| 19394 | 3 | 4 | | | IV-1 | Vmn1r224 |
| 19395 | 3 | 4 | | | IV-1 | Vmn1r4 |
| 19396 | 3 | 4 | | | IV-1 | Vmn2r-ps11 |
| 19397 | 3 | 4 | | | IV-1 | Vmn2r-ps54 |
| 19398 | 3 | 4 | | | IV-1 | Vmn2r29 |
| 19399 | 3 | 4 | | | IV-1 | Vmn2r4 |
| 19400 | 3 | 4 | | | IV-1 | Vmn2r7 |
| 19401 | 3 | 4 | | | IV-1 | Vmo1 |
| 19402 | 3 | 4 | | | IV-1 | Vmp1 |
| 19403 | 3 | 4 | | | IV-1 | Vpreb3 |
| 19404 | 3 | 4 | | | IV-1 | Vps11 |
| 19405 | 3 | 4 | | | IV-1 | Vps16 |
| 19406 | 3 | 4 | | | IV-1 | Vps26a |
| 19407 | 3 | 4 | | | IV-1 | Vps26b |
| 19408 | 3 | 4 | | | IV-1 | Vps33a |
| 19409 | 3 | 4 | | | IV-1 | Vps35 |
| 19410 | 3 | 4 | | | IV-1 | Vps37a |
| 19411 | 3 | 4 | | | IV-1 | Vps39 |
| 19412 | 3 | 4 | | | IV-1 | Vps41 |
| 19413 | 3 | 4 | | | IV-1 | Vps45 |
| 19414 | 3 | 4 | | | IV-1 | Vps4a |
| 19415 | 3 | 4 | | | IV-1 | Vps4b |
| 19416 | 3 | 4 | | | IV-1 | Vps52 |
| 19417 | 3 | 4 | | | IV-1 | Vps53 |
| 19418 | 3 | 4 | | | IV-1 | Vps72 |
| 19419 | 3 | 4 | | | IV-1 | Vps8 |
| 19420 | 3 | 4 | | | IV-1 | Vps9d1 |
| 19421 | 3 | 4 | | | IV-1 | Vrk1 |
| 19422 | 3 | 4 | | | IV-1 | Vrk3 |
| 19423 | 3 | 4 | | | IV-1 | Vsig1 |
| 19424 | 3 | 4 | | | IV-1 | Vsig10 |
| 19425 | 3 | 4 | | | IV-1 | Vsig10l |
| 19426 | 3 | 4 | | | IV-1 | Vsnl1 |
| 19427 | 3 | 4 | | | IV-1 | Vstm2a |
| 19428 | 3 | 4 | | | IV-1 | Vstm2l |
| 19429 | 3 | 4 | | | IV-1 | Vstm4 |
| 19430 | 3 | 4 | | | IV-1 | Vtcn1 |
| 19431 | 3 | 4 | | | IV-1 | Vti1a |
| 19432 | 3 | 4 | | | IV-1 | Vwa1 |
| 19433 | 3 | 4 | | | IV-1 | Vwa3a |
| 19434 | 3 | 4 | | | IV-1 | Vwa5a |
| 19435 | 3 | 4 | | | IV-1 | Vwa5b2 |
| 19436 | 3 | 4 | | | IV-1 | Vwa7 |
| 19437 | 3 | 4 | | | IV-1 | Vwa8 |
| 19438 | 3 | 4 | | | IV-1 | Vwa9 |
| 19439 | 3 | 4 | | | IV-1 | Vwc2 |
| 19440 | 3 | 4 | | | IV-1 | Vwc2l |
| 19441 | 3 | 4 | | | IV-1 | Vwce |
| 19442 | 3 | 4 | | | IV-1 | Wac |
| 19443 | 3 | 4 | | | IV-1 | Was |
| 19444 | 3 | 4 | | | IV-1 | Wasf1 |
| 19445 | 3 | 4 | | | IV-1 | Wash |
| 19446 | 3 | 4 | | | IV-1 | Wasl |
| 19447 | 3 | 4 | | | IV-1 | Wbp11 |
| 19448 | 3 | 4 | | | IV-1 | Wbp1l |
| 19449 | 3 | 4 | | | IV-1 | Wbp2nl |
| 19450 | 3 | 4 | | | IV-1 | Wbp4 |
| 19451 | 3 | 4 | | | IV-1 | Wbscr17 |
| 19452 | 3 | 4 | | | IV-1 | Wbscr28 |
| 19453 | 3 | 4 | | | IV-1 | Wdhd1 |
| 19454 | 3 | 4 | | | IV-1 | Wdr1 |
| 19455 | 3 | 4 | | | IV-1 | Wdr11 |
| 19456 | 3 | 4 | | | IV-1 | Wdr12 |
| 19457 | 3 | 4 | | | IV-1 | Wdr16 |
| 19458 | 3 | 4 | | | IV-1 | Wdr17 |
| 19459 | 3 | 4 | | | IV-1 | Wdr18 |
| 19460 | 3 | 4 | | | IV-1 | Wdr19 |
| 19461 | 3 | 4 | | | IV-1 | Wdr20 |
| 19462 | 3 | 4 | | | IV-1 | Wdr27 |
| 19463 | 3 | 4 | | | IV-1 | Wdr3 |
| 19464 | 3 | 4 | | | IV-1 | Wdr31 |
| 19465 | 3 | 4 | | | IV-1 | Wdr33 |
| 19466 | 3 | 4 | | | IV-1 | Wdr35 |
| 19467 | 3 | 4 | | | IV-1 | Wdr36 |
| 19468 | 3 | 4 | | | IV-1 | Wdr37 |
| 19469 | 3 | 4 | | | IV-1 | Wdr41 |
| 19470 | 3 | 4 | | | IV-1 | Wdr43 |
| 19471 | 3 | 4 | | | IV-1 | Wdr44 |
| 19472 | 3 | 4 | | | IV-1 | Wdr45 |
| 19473 | 3 | 4 | | | IV-1 | Wdr45b |
| 19474 | 3 | 4 | | | IV-1 | Wdr47 |
| 19475 | 3 | 4 | | | IV-1 | Wdr48 |
| 19476 | 3 | 4 | | | IV-1 | Wdr5 |
| 19477 | 3 | 4 | | | IV-1 | Wdr55 |
| 19478 | 3 | 4 | | | IV-1 | Wdr59 |
| 19479 | 3 | 4 | | | IV-1 | Wdr60 |
| 19480 | 3 | 4 | | | IV-1 | Wdr61 |
| 19481 | 3 | 4 | | | IV-1 | Wdr62 |
| 19482 | 3 | 4 | | | IV-1 | Wdr64 |
| 19483 | 3 | 4 | | | IV-1 | Wdr65 |
| 19484 | 3 | 4 | | | IV-1 | Wdr70 |
| 19485 | 3 | 4 | | | IV-1 | Wdr72 |
| 19486 | 3 | 4 | | | IV-1 | Wdr77 |
| 19487 | 3 | 4 | | | IV-1 | Wdr82 |
| 19488 | 3 | 4 | | | IV-1 | Wdr86 |
| 19489 | 3 | 4 | | | IV-1 | Wdr91 |
| 19490 | 3 | 4 | | | IV-1 | Wdr92 |
| 19491 | 3 | 4 | | | IV-1 | Wdr93 |
| 19492 | 3 | 4 | | | IV-1 | Wdr96 |
| 19493 | 3 | 4 | | | IV-1 | Wdsub1 |
| 19494 | 3 | 4 | | | IV-1 | Wdtc1 |
| 19495 | 3 | 4 | | | IV-1 | Wfdc12 |
| 19496 | 3 | 4 | | | IV-1 | Wfdc13 |
| 19497 | 3 | 4 | | | IV-1 | Wfdc15a |
| 19498 | 3 | 4 | | | IV-1 | Wfikkn1 |
| 19499 | 3 | 4 | | | IV-1 | Wfs1 |
| 19500 | 3 | 4 | | | IV-1 | Whsc1 |
| 19501 | 3 | 4 | | | IV-1 | Wipf1 |
| 19502 | 3 | 4 | | | IV-1 | Wipf2 |
| 19503 | 3 | 4 | | | IV-1 | Wipi2 |
| 19504 | 3 | 4 | | | IV-1 | Wisp1 |
| 19505 | 3 | 4 | | | IV-1 | Wisp2 |
| 19506 | 3 | 4 | | | IV-1 | Wiz |
| 19507 | 3 | 4 | | | IV-1 | Wls |
| 19508 | 3 | 4 | | | IV-1 | Wnt1 |
| 19509 | 3 | 4 | | | IV-1 | Wnt10a |
| 19510 | 3 | 4 | | | IV-1 | Wnt10b |
| 19511 | 3 | 4 | | | IV-1 | Wnt11 |
| 19512 | 3 | 4 | | | IV-1 | Wnt2 |
| 19513 | 3 | 4 | | | IV-1 | Wnt3a |
| 19514 | 3 | 4 | | | IV-1 | Wnt4 |
| 19515 | 3 | 4 | | | IV-1 | Wnt7a |
| 19516 | 3 | 4 | | | IV-1 | Wnt9b |
| 19517 | 3 | 4 | | | IV-1 | Wrap53 |
| 19518 | 3 | 4 | | | IV-1 | Wrnip1 |
| 19519 | 3 | 4 | | | IV-1 | Wsb1 |
| 19520 | 3 | 4 | | | IV-1 | Wsb2 |
| 19521 | 3 | 4 | | | IV-1 | Wscd1 |
| 19522 | 3 | 4 | | | IV-1 | Wscd2 |
| 19523 | 3 | 4 | | | IV-1 | Wt1os |
| 19524 | 3 | 4 | | | IV-1 | Wtap |
| 19525 | 3 | 4 | | | IV-1 | Wtip |
| 19526 | 3 | 4 | | | IV-1 | Wwox |
| 19527 | 3 | 4 | | | IV-1 | Wwp2 |
| 19528 | 3 | 4 | | | IV-1 | Wwtr1 |
| 19529 | 3 | 4 | | | IV-1 | Xab2 |
| 19530 | 3 | 4 | | | IV-1 | Xkr5 |
| 19531 | 3 | 4 | | | IV-1 | Xkr6 |
| 19532 | 3 | 4 | | | IV-1 | Xkr8 |
| 19533 | 3 | 4 | | | IV-1 | Xkr9 |
| 19534 | 3 | 4 | | | IV-1 | Xlr |
| 19535 | 3 | 4 | | | IV-1 | Xndc1 |
| 19536 | 3 | 4 | | | IV-1 | Xpc |
| 19537 | 3 | 4 | | | IV-1 | Xpnpep1 |
| 19538 | 3 | 4 | | | IV-1 | Xpnpep2 |
| 19539 | 3 | 4 | | | IV-1 | Xpo1 |
| 19540 | 3 | 4 | | | IV-1 | Xpo6 |
| 19541 | 3 | 4 | | | IV-1 | Xpot |
| 19542 | 3 | 4 | | | IV-1 | Xpr1 |
| 19543 | 3 | 4 | | | IV-1 | Xrcc1 |
| 19544 | 3 | 4 | | | IV-1 | Xrcc2 |
| 19545 | 3 | 4 | | | IV-1 | Xrn2 |
| 19546 | 3 | 4 | | | IV-1 | Xrra1 |
| 19547 | 3 | 4 | | | IV-1 | Xylt2 |
| 19548 | 3 | 4 | | | IV-1 | Yae1d1 |
| 19549 | 3 | 4 | | | IV-1 | Yars |
| 19550 | 3 | 4 | | | IV-1 | Yars2 |
| 19551 | 3 | 4 | | | IV-1 | Ybx1 |
| 19552 | 3 | 4 | | | IV-1 | Ybx2 |
| 19553 | 3 | 4 | | | IV-1 | Yeats4 |
| 19554 | 3 | 4 | | | IV-1 | Yif1a |
| 19555 | 3 | 4 | | | IV-1 | Yif1b |
| 19556 | 3 | 4 | | | IV-1 | Yipf3 |
| 19557 | 3 | 4 | | | IV-1 | Yipf4 |
| 19558 | 3 | 4 | | | IV-1 | Yipf5 |
| 19559 | 3 | 4 | | | IV-1 | Yipf6 |
| 19560 | 3 | 4 | | | IV-1 | Yipf7 |
| 19561 | 3 | 4 | | | IV-1 | Ykt6 |
| 19562 | 3 | 4 | | | IV-1 | Yme1l1 |
| 19563 | 3 | 4 | | | IV-1 | Yrdc |
| 19564 | 3 | 4 | | | IV-1 | Ythdc1 |
| 19565 | 3 | 4 | | | IV-1 | Ythdc2 |
| 19566 | 3 | 4 | | | IV-1 | Ythdf2 |
| 19567 | 3 | 4 | | | IV-1 | Ythdf3 |
| 19568 | 3 | 4 | | | IV-1 | Ywhab |
| 19569 | 3 | 4 | | | IV-1 | Ywhae |
| 19570 | 3 | 4 | | | IV-1 | Ywhag |
| 19571 | 3 | 4 | | | IV-1 | Ywhaq |
| 19572 | 3 | 4 | | | IV-1 | Ywhaz |
| 19573 | 3 | 4 | | | IV-1 | Yy1 |
| 19574 | 3 | 4 | | | IV-1 | Zadh2 |
| 19575 | 3 | 4 | | | IV-1 | Zbbx |
| 19576 | 3 | 4 | | | IV-1 | Zbed5 |
| 19577 | 3 | 4 | | | IV-1 | Zbtb1 |
| 19578 | 3 | 4 | | | IV-1 | Zbtb10 |
| 19579 | 3 | 4 | | | IV-1 | Zbtb11 |
| 19580 | 3 | 4 | | | IV-1 | Zbtb14 |
| 19581 | 3 | 4 | | | IV-1 | Zbtb17 |
| 19582 | 3 | 4 | | | IV-1 | Zbtb18 |

Fig. 36 - 103

| | | | | | | |
|---|---|---|---|---|---|---|
| 19583 | 3 | 4 | | | IV-1 | Zbtb2 |
| 19584 | 3 | 4 | | | IV-1 | Zbtb22 |
| 19585 | 3 | 4 | | | IV-1 | Zbtb24 |
| 19586 | 3 | 4 | | | IV-1 | Zbtb4 |
| 19587 | 3 | 4 | | | IV-1 | Zbtb41 |
| 19588 | 3 | 4 | | | IV-1 | Zbtb42 |
| 19589 | 3 | 4 | | | IV-1 | Zbtb43 |
| 19590 | 3 | 4 | | | IV-1 | Zbtb44 |
| 19591 | 3 | 4 | | | IV-1 | Zbtb48 |
| 19592 | 3 | 4 | | | IV-1 | Zbtb5 |
| 19593 | 3 | 4 | | | IV-1 | Zbtb6 |
| 19594 | 3 | 4 | | | IV-1 | Zbtb7b |
| 19595 | 3 | 4 | | | IV-1 | Zbtb7c |
| 19596 | 3 | 4 | | | IV-1 | Zbtb8b |
| 19597 | 3 | 4 | | | IV-1 | Zbtb9 |
| 19598 | 3 | 4 | | | IV-1 | Zbtbd6 |
| 19599 | 3 | 4 | | | IV-1 | Zc2hc1a |
| 19600 | 3 | 4 | | | IV-1 | Zc2hc1b |
| 19601 | 3 | 4 | | | IV-1 | Zc3h10 |
| 19602 | 3 | 4 | | | IV-1 | Zc3h11a |
| 19603 | 3 | 4 | | | IV-1 | Zc3h12a |
| 19604 | 3 | 4 | | | IV-1 | Zc3h12d |
| 19605 | 3 | 4 | | | IV-1 | Zc3h14 |
| 19606 | 3 | 4 | | | IV-1 | Zc3h18 |
| 19607 | 3 | 4 | | | IV-1 | Zc3h3 |
| 19608 | 3 | 4 | | | IV-1 | Zc3h4 |
| 19609 | 3 | 4 | | | IV-1 | Zc3h6 |
| 19610 | 3 | 4 | | | IV-1 | Zc3h7a |
| 19611 | 3 | 4 | | | IV-1 | Zc3h7b |
| 19612 | 3 | 4 | | | IV-1 | Zc3hc1 |
| 19613 | 3 | 4 | | | IV-1 | Zc4h2 |
| 19614 | 3 | 4 | | | IV-1 | Zcchc10 |
| 19615 | 3 | 4 | | | IV-1 | Zcchc12 |
| 19616 | 3 | 4 | | | IV-1 | Zcchc18 |
| 19617 | 3 | 4 | | | IV-1 | Zcchc2 |
| 19618 | 3 | 4 | | | IV-1 | Zcchc24 |
| 19619 | 3 | 4 | | | IV-1 | Zcchc3 |
| 19620 | 3 | 4 | | | IV-1 | Zcchc4 |
| 19621 | 3 | 4 | | | IV-1 | Zcchc7 |
| 19622 | 3 | 4 | | | IV-1 | Zcchc8 |
| 19623 | 3 | 4 | | | IV-1 | Zcchc9 |
| 19624 | 3 | 4 | | | IV-1 | Zdhhc1 |
| 19625 | 3 | 4 | | | IV-1 | Zdhhc11 |
| 19626 | 3 | 4 | | | IV-1 | Zdhhc12 |
| 19627 | 3 | 4 | | | IV-1 | Zdhhc13 |
| 19628 | 3 | 4 | | | IV-1 | Zdhhc14 |
| 19629 | 3 | 4 | | | IV-1 | Zdhhc15 |
| 19630 | 3 | 4 | | | IV-1 | Zdhhc17 |
| 19631 | 3 | 4 | | | IV-1 | Zdhhc18 |
| 19632 | 3 | 4 | | | IV-1 | Zdhhc19 |
| 19633 | 3 | 4 | | | IV-1 | Zdhhc20 |
| 19634 | 3 | 4 | | | IV-1 | Zdhhc25 |
| 19635 | 3 | 4 | | | IV-1 | Zdhhc3 |
| 19636 | 3 | 4 | | | IV-1 | Zdhhc6 |
| 19637 | 3 | 4 | | | IV-1 | Zdhhc7 |
| 19638 | 3 | 4 | | | IV-1 | Zdhhc8 |
| 19639 | 3 | 4 | | | IV-1 | Zdhhc9 |
| 19640 | 3 | 4 | | | IV-1 | Zeb1 |
| 19641 | 3 | 4 | | | IV-1 | Zer1 |
| 19642 | 3 | 4 | | | IV-1 | Zfand2a |
| 19643 | 3 | 4 | | | IV-1 | Zfand4 |
| 19644 | 3 | 4 | | | IV-1 | Zfand5 |
| 19645 | 3 | 4 | | | IV-1 | Zfand6 |
| 19646 | 3 | 4 | | | IV-1 | Zfp1 |
| 19647 | 3 | 4 | | | IV-1 | Zfp108 |
| 19648 | 3 | 4 | | | IV-1 | Zfp113 |
| 19649 | 3 | 4 | | | IV-1 | Zfp114 |
| 19650 | 3 | 4 | | | IV-1 | Zfp12 |
| 19651 | 3 | 4 | | | IV-1 | Zfp120 |
| 19652 | 3 | 4 | | | IV-1 | Zfp14 |
| 19653 | 3 | 4 | | | IV-1 | Zfp148 |
| 19654 | 3 | 4 | | | IV-1 | Zfp157 |
| 19655 | 3 | 4 | | | IV-1 | Zfp160 |
| 19656 | 3 | 4 | | | IV-1 | Zfp180 |
| 19657 | 3 | 4 | | | IV-1 | Zfp182 |
| 19658 | 3 | 4 | | | IV-1 | Zfp184 |
| 19659 | 3 | 4 | | | IV-1 | Zfp189 |
| 19660 | 3 | 4 | | | IV-1 | Zfp191 |
| 19661 | 3 | 4 | | | IV-1 | Zfp202 |
| 19662 | 3 | 4 | | | IV-1 | Zfp207 |
| 19663 | 3 | 4 | | | IV-1 | Zfp212 |
| 19664 | 3 | 4 | | | IV-1 | Zfp213 |
| 19665 | 3 | 4 | | | IV-1 | Zfp219 |
| 19666 | 3 | 4 | | | IV-1 | Zfp229 |
| 19667 | 3 | 4 | | | IV-1 | Zfp235 |
| 19668 | 3 | 4 | | | IV-1 | Zfp251 |
| 19669 | 3 | 4 | | | IV-1 | Zfp263 |
| 19670 | 3 | 4 | | | IV-1 | Zfp266 |
| 19671 | 3 | 4 | | | IV-1 | Zfp276 |
| 19672 | 3 | 4 | | | IV-1 | Zfp28 |
| 19673 | 3 | 4 | | | IV-1 | Zfp280b |
| 19674 | 3 | 4 | | | IV-1 | Zfp280c |
| 19675 | 3 | 4 | | | IV-1 | Zfp280d |
| 19676 | 3 | 4 | | | IV-1 | Zfp282 |
| 19677 | 3 | 4 | | | IV-1 | Zfp286 |
| 19678 | 3 | 4 | | | IV-1 | Zfp287 |
| 19679 | 3 | 4 | | | IV-1 | Zfp30 |
| 19680 | 3 | 4 | | | IV-1 | Zfp316 |
| 19681 | 3 | 4 | | | IV-1 | Zfp317 |
| 19682 | 3 | 4 | | | IV-1 | Zfp322a |
| 19683 | 3 | 4 | | | IV-1 | Zfp326 |
| 19684 | 3 | 4 | | | IV-1 | Zfp330 |
| 19685 | 3 | 4 | | | IV-1 | Zfp341 |
| 19686 | 3 | 4 | | | IV-1 | Zfp346 |
| 19687 | 3 | 4 | | | IV-1 | Zfp35 |
| 19688 | 3 | 4 | | | IV-1 | Zfp354b |
| 19689 | 3 | 4 | | | IV-1 | Zfp358 |
| 19690 | 3 | 4 | | | IV-1 | Zfp362 |
| 19691 | 3 | 4 | | | IV-1 | Zfp365 |
| 19692 | 3 | 4 | | | IV-1 | Zfp37 |
| 19693 | 3 | 4 | | | IV-1 | Zfp383 |
| 19694 | 3 | 4 | | | IV-1 | Zfp384 |
| 19695 | 3 | 4 | | | IV-1 | Zfp385a |
| 19696 | 3 | 4 | | | IV-1 | Zfp385b |
| 19697 | 3 | 4 | | | IV-1 | Zfp385c |
| 19698 | 3 | 4 | | | IV-1 | Zfp386 |
| 19699 | 3 | 4 | | | IV-1 | Zfp408 |
| 19700 | 3 | 4 | | | IV-1 | Zfp410 |
| 19701 | 3 | 4 | | | IV-1 | Zfp422 |
| 19702 | 3 | 4 | | | IV-1 | Zfp423 |
| 19703 | 3 | 4 | | | IV-1 | Zfp426 |
| 19704 | 3 | 4 | | | IV-1 | Zfp429 |
| 19705 | 3 | 4 | | | IV-1 | Zfp433 |
| 19706 | 3 | 4 | | | IV-1 | Zfp438 |
| 19707 | 3 | 4 | | | IV-1 | Zfp444 |
| 19708 | 3 | 4 | | | IV-1 | Zfp459 |
| 19709 | 3 | 4 | | | IV-1 | Zfp46 |
| 19710 | 3 | 4 | | | IV-1 | Zfp473 |
| 19711 | 3 | 4 | | | IV-1 | Zfp474 |
| 19712 | 3 | 4 | | | IV-1 | Zfp488 |
| 19713 | 3 | 4 | | | IV-1 | Zfp493 |
| 19714 | 3 | 4 | | | IV-1 | Zfp512 |
| 19715 | 3 | 4 | | | IV-1 | Zfp513 |
| 19716 | 3 | 4 | | | IV-1 | Zfp52 |
| 19717 | 3 | 4 | | | IV-1 | Zfp523 |
| 19718 | 3 | 4 | | | IV-1 | Zfp53 |
| 19719 | 3 | 4 | | | IV-1 | Zfp54 |
| 19720 | 3 | 4 | | | IV-1 | Zfp553 |
| 19721 | 3 | 4 | | | IV-1 | Zfp558 |
| 19722 | 3 | 4 | | | IV-1 | Zfp560 |
| 19723 | 3 | 4 | | | IV-1 | Zfp566 |
| 19724 | 3 | 4 | | | IV-1 | Zfp572 |
| 19725 | 3 | 4 | | | IV-1 | Zfp574 |
| 19726 | 3 | 4 | | | IV-1 | Zfp575 |
| 19727 | 3 | 4 | | | IV-1 | Zfp579 |
| 19728 | 3 | 4 | | | IV-1 | Zfp58 |
| 19729 | 3 | 4 | | | IV-1 | Zfp593 |
| 19730 | 3 | 4 | | | IV-1 | Zfp597 |
| 19731 | 3 | 4 | | | IV-1 | Zfp598 |
| 19732 | 3 | 4 | | | IV-1 | Zfp60 |
| 19733 | 3 | 4 | | | IV-1 | Zfp600 |
| 19734 | 3 | 4 | | | IV-1 | Zfp605 |
| 19735 | 3 | 4 | | | IV-1 | Zfp606 |
| 19736 | 3 | 4 | | | IV-1 | Zfp612 |
| 19737 | 3 | 4 | | | IV-1 | Zfp617 |
| 19738 | 3 | 4 | | | IV-1 | Zfp622 |
| 19739 | 3 | 4 | | | IV-1 | Zfp623 |
| 19740 | 3 | 4 | | | IV-1 | Zfp628 |
| 19741 | 3 | 4 | | | IV-1 | Zfp629 |
| 19742 | 3 | 4 | | | IV-1 | Zfp639 |
| 19743 | 3 | 4 | | | IV-1 | Zfp64 |
| 19744 | 3 | 4 | | | IV-1 | Zfp644 |
| 19745 | 3 | 4 | | | IV-1 | Zfp651 |
| 19746 | 3 | 4 | | | IV-1 | Zfp653 |
| 19747 | 3 | 4 | | | IV-1 | Zfp654 |
| 19748 | 3 | 4 | | | IV-1 | Zfp655 |
| 19749 | 3 | 4 | | | IV-1 | Zfp658 |
| 19750 | 3 | 4 | | | IV-1 | Zfp667 |
| 19751 | 3 | 4 | | | IV-1 | Zfp672 |
| 19752 | 3 | 4 | | | IV-1 | Zfp677 |
| 19753 | 3 | 4 | | | IV-1 | Zfp68 |
| 19754 | 3 | 4 | | | IV-1 | Zfp689 |
| 19755 | 3 | 4 | | | IV-1 | Zfp691 |
| 19756 | 3 | 4 | | | IV-1 | Zfp697 |
| 19757 | 3 | 4 | | | IV-1 | Zfp703 |
| 19758 | 3 | 4 | | | IV-1 | Zfp706 |
| 19759 | 3 | 4 | | | IV-1 | Zfp709 |
| 19760 | 3 | 4 | | | IV-1 | Zfp711 |
| 19761 | 3 | 4 | | | IV-1 | Zfp719 |
| 19762 | 3 | 4 | | | IV-1 | Zfp740 |
| 19763 | 3 | 4 | | | IV-1 | Zfp746 |
| 19764 | 3 | 4 | | | IV-1 | Zfp747 |
| 19765 | 3 | 4 | | | IV-1 | Zfp759 |
| 19766 | 3 | 4 | | | IV-1 | Zfp760 |
| 19767 | 3 | 4 | | | IV-1 | Zfp764 |
| 19768 | 3 | 4 | | | IV-1 | Zfp768 |
| 19769 | 3 | 4 | | | IV-1 | Zfp773 |
| 19770 | 3 | 4 | | | IV-1 | Zfp777 |
| 19771 | 3 | 4 | | | IV-1 | Zfp78 |
| 19772 | 3 | 4 | | | IV-1 | Zfp781 |
| 19773 | 3 | 4 | | | IV-1 | Zfp783 |
| 19774 | 3 | 4 | | | IV-1 | Zfp784 |

Fig. 36 - 104

| | | | | | | | |
|---|---|---|---|---|---|---|---|
| 19775 | 3 | 4 | | | IV-1 | Zfp786 | |
| 19776 | 3 | 4 | | | IV-1 | Zfp787 | |
| 19777 | 3 | 4 | | | IV-1 | Zfp788 | |
| 19778 | 3 | 4 | | | IV-1 | Zfp790 | |
| 19779 | 3 | 4 | | | IV-1 | Zfp804a | |
| 19780 | 3 | 4 | | | IV-1 | Zfp808 | |
| 19781 | 3 | 4 | | | IV-1 | Zfp810 | |
| 19782 | 3 | 4 | | | IV-1 | Zfp811 | |
| 19783 | 3 | 4 | | | IV-1 | Zfp819 | |
| 19784 | 3 | 4 | | | IV-1 | Zfp821 | |
| 19785 | 3 | 4 | | | IV-1 | Zfp825 | |
| 19786 | 3 | 4 | | | IV-1 | Zfp830 | |
| 19787 | 3 | 4 | | | IV-1 | Zfp839 | |
| 19788 | 3 | 4 | | | IV-1 | Zfp84 | |
| 19789 | 3 | 4 | | | IV-1 | Zfp846 | |
| 19790 | 3 | 4 | | | IV-1 | Zfp850 | |
| 19791 | 3 | 4 | | | IV-1 | Zfp85os | |
| 19792 | 3 | 4 | | | IV-1 | Zfp865 | |
| 19793 | 3 | 4 | | | IV-1 | Zfp867 | |
| 19794 | 3 | 4 | | | IV-1 | Zfp868 | |
| 19795 | 3 | 4 | | | IV-1 | Zfp869 | |
| 19796 | 3 | 4 | | | IV-1 | Zfp87 | |
| 19797 | 3 | 4 | | | IV-1 | Zfp870 | |
| 19798 | 3 | 4 | | | IV-1 | Zfp872 | |
| 19799 | 3 | 4 | | | IV-1 | Zfp874a | |
| 19800 | 3 | 4 | | | IV-1 | Zfp874b | |
| 19801 | 3 | 4 | | | IV-1 | Zfp882 | |
| 19802 | 3 | 4 | | | IV-1 | Zfp92 | |
| 19803 | 3 | 4 | | | IV-1 | Zfp93 | |
| 19804 | 3 | 4 | | | IV-1 | Zfp930 | |
| 19805 | 3 | 4 | | | IV-1 | Zfp937 | |
| 19806 | 3 | 4 | | | IV-1 | Zfp941 | |
| 19807 | 3 | 4 | | | IV-1 | Zfp943 | |
| 19808 | 3 | 4 | | | IV-1 | Zfp944 | |
| 19809 | 3 | 4 | | | IV-1 | Zfp946 | |
| 19810 | 3 | 4 | | | IV-1 | Zfp947 | |
| 19811 | 3 | 4 | | | IV-1 | Zfp949 | |
| 19812 | 3 | 4 | | | IV-1 | Zfp951 | |
| 19813 | 3 | 4 | | | IV-1 | Zfp953 | |
| 19814 | 3 | 4 | | | IV-1 | Zfp955a | |
| 19815 | 3 | 4 | | | IV-1 | Zfp958 | |
| 19816 | 3 | 4 | | | IV-1 | Zfp959 | |
| 19817 | 3 | 4 | | | IV-1 | Zfp960 | |
| 19818 | 3 | 4 | | | IV-1 | Zfp963 | |
| 19819 | 3 | 4 | | | IV-1 | Zfx | |
| 19820 | 3 | 4 | | | IV-1 | Zfy1 | |
| 19821 | 3 | 4 | | | IV-1 | Zfy2 | |
| 19822 | 3 | 4 | | | IV-1 | Zfyve1 | |
| 19823 | 3 | 4 | | | IV-1 | Zfyve20 | |
| 19824 | 3 | 4 | | | IV-1 | Zfyve27 | |
| 19825 | 3 | 4 | | | IV-1 | Zfyve9 | |
| 19826 | 3 | 4 | | | IV-1 | Zglp1 | |
| 19827 | 3 | 4 | | | IV-1 | Zhx1 | |
| 19828 | 3 | 4 | | | IV-1 | Zhx2 | |
| 19829 | 3 | 4 | | | IV-1 | Zic2 | |
| 19830 | 3 | 4 | | | IV-1 | Zic3 | |
| 19831 | 3 | 4 | | | IV-1 | Zic4 | |
| 19832 | 3 | 4 | | | IV-1 | Zic5 | |
| 19833 | 3 | 4 | | | IV-1 | Zkscan14 | |
| 19834 | 3 | 4 | | | IV-1 | Zkscan17 | |
| 19835 | 3 | 4 | | | IV-1 | Zkscan3 | |
| 19836 | 3 | 4 | | | IV-1 | Zkscan4 | |
| 19837 | 3 | 4 | | | IV-1 | Zkscan5 | |
| 19838 | 3 | 4 | | | IV-1 | Zkscan6 | |
| 19839 | 3 | 4 | | | IV-1 | Zmat2 | |
| 19840 | 3 | 4 | | | IV-1 | Zmat3 | |
| 19841 | 3 | 4 | | | IV-1 | Zmat4 | |
| 19842 | 3 | 4 | | | IV-1 | Zmiz1 | |
| 19843 | 3 | 4 | | | IV-1 | Zmiz2 | |
| 19844 | 3 | 4 | | | IV-1 | Zmpste24 | |
| 19845 | 3 | 4 | | | IV-1 | Zmym1 | |
| 19846 | 3 | 4 | | | IV-1 | Zmym3 | |
| 19847 | 3 | 4 | | | IV-1 | Zmym4 | |
| 19848 | 3 | 4 | | | IV-1 | Zmym5 | |
| 19849 | 3 | 4 | | | IV-1 | Zmym6 | |
| 19850 | 3 | 4 | | | IV-1 | Zmynd11 | |
| 19851 | 3 | 4 | | | IV-1 | Zmynd15 | |
| 19852 | 3 | 4 | | | IV-1 | Zmynd19 | |
| 19853 | 3 | 4 | | | IV-1 | Zmynd8 | |
| 19854 | 3 | 4 | | | IV-1 | Znf512b | |
| 19855 | 3 | 4 | | | IV-1 | Znfx1 | |
| 19856 | 3 | 4 | | | IV-1 | Znhit2 | |
| 19857 | 3 | 4 | | | IV-1 | Znhit6 | |
| 19858 | 3 | 4 | | | IV-1 | Znrf1 | |
| 19859 | 3 | 4 | | | IV-1 | Znrf3 | |
| 19860 | 3 | 4 | | | IV-1 | Znrf4 | |
| 19861 | 3 | 4 | | | IV-1 | Zp3r | |
| 19862 | 3 | 4 | | | IV-1 | Zpbp | |
| 19863 | 3 | 4 | | | IV-1 | Zpbp2 | |
| 19864 | 3 | 4 | | | IV-1 | Zpr1 | |
| 19865 | 3 | 4 | | | IV-1 | Zrsr1 | |
| 19866 | 3 | 4 | | | IV-1 | Zrsr2 | |
| 19867 | 3 | 4 | | | IV-1 | Zscan12 | |
| 19868 | 3 | 4 | | | IV-1 | Zscan2 | |
| 19869 | 3 | 4 | | | IV-1 | Zscan21 | |
| 19870 | 3 | 4 | | | IV-1 | Zscan26 | |
| 19871 | 3 | 4 | | | IV-1 | Zscan29 | |
| 19872 | 3 | 4 | | | IV-1 | Zscan5b | |
| 19873 | 3 | 4 | | | IV-1 | Zswim1 | |
| 19874 | 3 | 4 | | | IV-1 | Zswim2 | |
| 19875 | 3 | 4 | | | IV-1 | Zswim4 | |
| 19876 | 3 | 4 | | | IV-1 | Zswim6 | |
| 19877 | 3 | 4 | | | IV-1 | Zufsp | |
| 19878 | 3 | 4 | | | IV-1 | Zw10 | |
| 19879 | 3 | 4 | | | IV-1 | Zwilch | |
| 19880 | 3 | 4 | | | IV-1 | Zwint | |
| 19881 | 3 | 4 | | | IV-1 | Zzz3 | |
| 19882 | 3 | | | | | 1110028F18Rik | |
| 19883 | 3 | | | | | 1110036E04Rik | |
| 19884 | 3 | | | | | 1190003K10Rik | |
| 19885 | 3 | | | | | 1500012K07Rik | |
| 19886 | 3 | | | | | 1600002D24Rik | |
| 19887 | 3 | | | | | 1600015I10Rik | |
| 19888 | 3 | | | | | 1600019K03Rik | |
| 19889 | 3 | | | | | 1600029O15Rik | |
| 19890 | 3 | | | | | 1700001D01Rik | |
| 19891 | 3 | | | | | 1700010I02Rik | |
| 19892 | 3 | | | | | 1700012I11Rik | |
| 19893 | 3 | | | | | 1700019E08Rik | |
| 19894 | 3 | | | | | 1700020M21Rik | |
| 19895 | 3 | | | | | 1700027H10Rik | |
| 19896 | 3 | | | | | 1700027J07Rik | |
| 19897 | 3 | | | | | 1700028M03Rik | |
| 19898 | 3 | | | | | 1700031A10Rik | |
| 19899 | 3 | | | | | 1700047E10Rik | |
| 19900 | 3 | | | | | 1700057H15Rik | |
| 19901 | 3 | | | | | 1700063A18Rik | |
| 19902 | 3 | | | | | 1700063D05Rik | |
| 19903 | 3 | | | | | 1700063O14Rik | |
| 19904 | 3 | | | | | 1700064J06Rik | |
| 19905 | 3 | | | | | 1700069P05Rik | |
| 19906 | 3 | | | | | 1700084F23Rik | |
| 19907 | 3 | | | | | 1700085C21Rik | |
| 19908 | 3 | | | | | 1700104L18Rik | |
| 19909 | 3 | | | | | 1700111N16Rik | |
| 19910 | 3 | | | | | 1700112H15Rik | |
| 19911 | 3 | | | | | 1700121L16Rik | |
| 19912 | 3 | | | | | 1700123O21Rik | |
| 19913 | 3 | | | | | 1700126H18Rik | |
| 19914 | 3 | | | | | 1810007C17Rik | |
| 19915 | 3 | | | | | 1810007D17Rik | |
| 19916 | 3 | | | | | 2010001E11Rik | |
| 19917 | 3 | | | | | 2010009K17Rik | |
| 19918 | 3 | | | | | 2010106C02Rik | |
| 19919 | 3 | | | | | 2010308F09Rik | |
| 19920 | 3 | | | | | 2010310C07Rik | |
| 19921 | 3 | | | | | 2210414B05Rik | |
| 19922 | 3 | | | | | 2300003K06Rik | |
| 19923 | 3 | | | | | 2310002F09Rik | |
| 19924 | 3 | | | | | 2310005A03Rik | |
| 19925 | 3 | | | | | 2310005E17Rik | |
| 19926 | 3 | | | | | 2310016D03Rik | |
| 19927 | 3 | | | | | 2310034C09Rik | |
| 19928 | 3 | | | | | 2310034O05Rik | |
| 19929 | 3 | | | | | 2310057N15Rik | |
| 19930 | 3 | | | | | 2410003L11Rik | |
| 19931 | 3 | | | | | 2410007B07Rik | |
| 19932 | 3 | | | | | 2410012E07Rik | |
| 19933 | 3 | | | | | 2410012M07Rik | |
| 19934 | 3 | | | | | 2410017I17Rik | |
| 19935 | 3 | | | | | 2410018L13Rik | |
| 19936 | 3 | | | | | 2410088K16Rik | |
| 19937 | 3 | | | | | 2410114N07Rik | |
| 19938 | 3 | | | | | 2610028E06Rik | |
| 19939 | 3 | | | | | 2610037D02Rik | |
| 19940 | 3 | | | | | 2610207O16Rik | |
| 19941 | 3 | | | | | 2610316D01Rik | |
| 19942 | 3 | | | | | 2700070H01Rik | |
| 19943 | 3 | | | | | 2700089I24Rik | |
| 19944 | 3 | | | | | 2810055G20Rik | |
| 19945 | 3 | | | | | 2810404M03Rik | |
| 19946 | 3 | | | | | 2810429I04Rik | |
| 19947 | 3 | | | | | 2810442N19Rik | |
| 19948 | 3 | | | | | 2810471M01Rik | |
| 19949 | 3 | | | | | 2900057B20Rik | |
| 19950 | 3 | | | | | 2900060B14Rik | |
| 19951 | 3 | | | | | 3100003L05Rik | |
| 19952 | 3 | | | | | 3110009F21Rik | |
| 19953 | 3 | | | | | 3110015C05Rik | |
| 19954 | 3 | | | | | 3110039I08Rik | |
| 19955 | 3 | | | | | 3200001D21Rik | |
| 19956 | 3 | | | | | 4732456N10Rik | |
| 19957 | 3 | | | | | 4732490B19Rik | |
| 19958 | 3 | | | | | 4833428L15Rik | |
| 19959 | 3 | | | | | 4921508D12Rik | |
| 19960 | 3 | | | | | 4921509O07Rik | |
| 19961 | 3 | | | | | 4921511C10Rik | |
| 19962 | 3 | | | | | 4921511I17Rik | |
| 19963 | 3 | | | | | 4921529L05Rik | |
| 19964 | 3 | | | | | 4922502N22Rik | |
| 19965 | 3 | | | | | 4930401C15Rik | |
| 19966 | 3 | | | | | 4930412B13Rik | |

Fig. 36 - 105

| | | | | | | |
|---|---|---|---|---|---|---|
| 19967 | 3 | | | | | 4930413M19Rik |
| 19968 | 3 | | | | | 4930419G24Rik |
| 19969 | 3 | | | | | 4930425O10Rik |
| 19970 | 3 | | | | | 4930428G15Rik |
| 19971 | 3 | | | | | 4930428O21Rik |
| 19972 | 3 | | | | | 4930432M17Rik |
| 19973 | 3 | | | | | 4930440I19Rik |
| 19974 | 3 | | | | | 4930448F12Rik |
| 19975 | 3 | | | | | 4930448J18Rik |
| 19976 | 3 | | | | | 4930452N14Rik |
| 19977 | 3 | | | | | 4930465M20Rik |
| 19978 | 3 | | | | | 4930470H14Rik |
| 19979 | 3 | | | | | 4930474G06Rik |
| 19980 | 3 | | | | | 4930474H20Rik |
| 19981 | 3 | | | | | 4930478L05Rik |
| 19982 | 3 | | | | | 4930480M12Rik |
| 19983 | 3 | | | | | 4930483O08Rik |
| 19984 | 3 | | | | | 4930488B22Rik |
| 19985 | 3 | | | | | 4930500L23Rik |
| 19986 | 3 | | | | | 4930505G20Rik |
| 19987 | 3 | | | | | 4930509X18Rik |
| 19988 | 3 | | | | | 4930511E03Rik |
| 19989 | 3 | | | | | 4930512B01Rik |
| 19990 | 3 | | | | | 4930515B02Rik |
| 19991 | 3 | | | | | 4930515L03Rik |
| 19992 | 3 | | | | | 4930517E11Rik |
| 19993 | 3 | | | | | 4930521E06Rik |
| 19994 | 3 | | | | | 4930524C18Rik |
| 19995 | 3 | | | | | 4930533P14Rik |
| 19996 | 3 | | | | | 4930539N22Rik |
| 19997 | 3 | | | | | 4930542D17Rik |
| 19998 | 3 | | | | | 4930546C10Rik |
| 19999 | 3 | | | | | 4930546K05Rik |
| 20000 | 3 | | | | | 4930554C24Rik |
| 20001 | 3 | | | | | 4930555B11Rik |
| 20002 | 3 | | | | | 4930557J02Rik |
| 20003 | 3 | | | | | 4930558G05Rik |
| 20004 | 3 | | | | | 4930563E18Rik |
| 20005 | 3 | | | | | 4930563M20Rik |
| 20006 | 3 | | | | | 4930567H12Rik |
| 20007 | 3 | | | | | 4930568G15Rik |
| 20008 | 3 | | | | | 4930590L20Rik |
| 20009 | 3 | | | | | 4931412M21 |
| 20010 | 3 | | | | | 4931429P17Rik |
| 20011 | 3 | | | | | 4932441J04Rik |
| 20012 | 3 | | | | | 4933400B14Rik |
| 20013 | 3 | | | | | 4933400C23Rik |
| 20014 | 3 | | | | | 4933402J15Rik |
| 20015 | 3 | | | | | 4933405E24Rik |
| 20016 | 3 | | | | | 4933406D12Rik |
| 20017 | 3 | | | | | 4933406J10Rik |
| 20018 | 3 | | | | | 4933407G14Rik |
| 20019 | 3 | | | | | 4933416E03Rik |
| 20020 | 3 | | | | | 4933424G05Rik |
| 20021 | 3 | | | | | 4933425B07Rik |
| 20022 | 3 | | | | | 4933432G23Rik |
| 20023 | 3 | | | | | 4933432J03Rik |
| 20024 | 3 | | | | | 4933433F19Rik |
| 20025 | 3 | | | | | 4933433H22Rik |
| 20026 | 3 | | | | | 4933436E23Rik |
| 20027 | 3 | | | | | 5031426D15Rik |
| 20028 | 3 | | | | | 5031434C07Rik |
| 20029 | 3 | | | | | 5330439B14Rik |
| 20030 | 3 | | | | | 5430401F13Rik |
| 20031 | 3 | | | | | 5430402E10Rik |
| 20032 | 3 | | | | | 5430403N17Rik |
| 20033 | 3 | | | | | 5430421F17Rik |
| 20034 | 3 | | | | | 5430428K19Rik |
| 20035 | 3 | | | | | 5430434I15Rik |
| 20036 | 3 | | | | | 5430440P10Rik |
| 20037 | 3 | | | | | 5530400C23Rik |
| 20038 | 3 | | | | | 5530401A14Rik |
| 20039 | 3 | | | | | 5730412P04Rik |
| 20040 | 3 | | | | | 5730422E09Rik |
| 20041 | 3 | | | | | 5730435O14Rik |
| 20042 | 3 | | | | | 5730457N03Rik |
| 20043 | 3 | | | | | 5730488B01Rik |
| 20044 | 3 | | | | | 5730507C01Rik |
| 20045 | 3 | | | | | 5730522E02Rik |
| 20046 | 3 | | | | | 5830416I19Rik |
| 20047 | 3 | | | | | 5830418P13Rik |
| 20048 | 3 | | | | | 5830444B04Rik |
| 20049 | 3 | | | | | 5930438M14Rik |
| 20050 | 3 | | | | | 6030407O03Rik |
| 20051 | 3 | | | | | 6030440G07Rik |
| 20052 | 3 | | | | | 6030466F02Rik |
| 20053 | 3 | | | | | 6030469F06Rik |
| 20054 | 3 | | | | | 6030498E09Rik |
| 20055 | 3 | | | | | 6330407A03Rik |
| 20056 | 3 | | | | | 6330410L21Rik |
| 20057 | 3 | | | | | 6330415B21Rik |
| 20058 | 3 | | | | | 6530411M01Rik |
| 20059 | 3 | | | | | 7420426K07Rik |
| 20060 | 3 | | | | | 7420700N18Rik |
| 20061 | 3 | | | | | 7420701O03Rik |
| 20062 | 3 | | | | | 7530416G11Rik |
| 20063 | 3 | | | | | 7630403G23Rik |
| 20064 | 3 | | | | | 8030423F21Rik |
| 20065 | 3 | | | | | 8030423J24Rik |
| 20066 | 3 | | | | | 8030442B05Rik |
| 20067 | 3 | | | | | 8030443G20Rik |
| 20068 | 3 | | | | | 8430422H06Rik |
| 20069 | 3 | | | | | 8430423G03Rik |
| 20070 | 3 | | | | | 8430431K14Rik |
| 20071 | 3 | | | | | 8430436N08Rik |
| 20072 | 3 | | | | | 8430437L04Rik |
| 20073 | 3 | | | | | 9030204H09Rik |
| 20074 | 3 | | | | | 9030624G23Rik |
| 20075 | 3 | | | | | 9130015A21Rik |
| 20076 | 3 | | | | | 9130015L21Rik |
| 20077 | 3 | | | | | 9130221F21Rik |
| 20078 | 3 | | | | | 9130227L01Rik |
| 20079 | 3 | | | | | 9230102K24Rik |
| 20080 | 3 | | | | | 9230112D13Rik |
| 20081 | 3 | | | | | 9330111N05Rik |
| 20082 | 3 | | | | | 9330162B11Rik |
| 20083 | 3 | | | | | 9330175M20Rik |
| 20084 | 3 | | | | | 9330178D15Rik |
| 20085 | 3 | | | | | 9330182O14Rik |
| 20086 | 3 | | | | | 9430007A20Rik |
| 20087 | 3 | | | | | 9430019J16Rik |
| 20088 | 3 | | | | | 9430069I07Rik |
| 20089 | 3 | | | | | 9430076C15Rik |
| 20090 | 3 | | | | | 9530002B09Rik |
| 20091 | 3 | | | | | 9530026F06Rik |
| 20092 | 3 | | | | | 9530036O11Rik |
| 20093 | 3 | | | | | 9530051G07Rik |
| 20094 | 3 | | | | | 9530052E02Rik |
| 20095 | 3 | | | | | 9530059O14Rik |
| 20096 | 3 | | | | | 9630001P10Rik |
| 20097 | 3 | | | | | 9630028H03Rik |
| 20098 | 3 | | | | | 9930111H07Rik |
| 20099 | 3 | | | | | A1bg |
| 20100 | 3 | | | | | A230020J21Rik |
| 20101 | 3 | | | | | A230028O05Rik |
| 20102 | 3 | | | | | A230056J06Rik |
| 20103 | 3 | | | | | A230072E10Rik |
| 20104 | 3 | | | | | A330032B11Rik |
| 20105 | 3 | | | | | A430088P11Rik |
| 20106 | 3 | | | | | A430089I19Rik |
| 20107 | 3 | | | | | A430090L17Rik |
| 20108 | 3 | | | | | A430093F15Rik |
| 20109 | 3 | | | | | A430107P09Rik |
| 20110 | 3 | | | | | A530006G24Rik |
| 20111 | 3 | | | | | A530046M15Rik |
| 20112 | 3 | | | | | A530065N20Rik |
| 20113 | 3 | | | | | A530072M11Rik |
| 20114 | 3 | | | | | A630012P03Rik |
| 20115 | 3 | | | | | A630019I02Rik |
| 20116 | 3 | | | | | A630073D07Rik |
| 20117 | 3 | | | | | A630075F10Rik |
| 20118 | 3 | | | | | A730018C14Rik |
| 20119 | 3 | | | | | A730043L09Rik |
| 20120 | 3 | | | | | A730082K24Rik |
| 20121 | 3 | | | | | A730090H04Rik |
| 20122 | 3 | | | | | A830009L08Rik |
| 20123 | 3 | | | | | A830019L24Rik |
| 20124 | 3 | | | | | A930006I01Rik |
| 20125 | 3 | | | | | A930011G23Rik |
| 20126 | 3 | | | | | A930019D19Rik |
| 20127 | 3 | | | | | AA388235 |
| 20128 | 3 | | | | | AA536875 |
| 20129 | 3 | | | | | AA543401 |
| 20130 | 3 | | | | | AA545190 |
| 20131 | 3 | | | | | AA619741 |
| 20132 | 3 | | | | | AA792892 |
| 20133 | 3 | | | | | AF067061 |
| 20134 | 3 | | | | | AF067063 |
| 20135 | 3 | | | | | AF357355 |
| 20136 | 3 | | | | | AF357359 |
| 20137 | 3 | | | | | AF357399 |
| 20138 | 3 | | | | | AF357425 |
| 20139 | 3 | | | | | AF357426 |
| 20140 | 3 | | | | | AU015228 |
| 20141 | 3 | | | | | AU016765 |
| 20142 | 3 | | | | | AU018829 |
| 20143 | 3 | | | | | AU019990 |
| 20144 | 3 | | | | | AU021063 |
| 20145 | 3 | | | | | AY512915 |
| 20146 | 3 | | | | | Abcb5 |
| 20147 | 3 | | | | | Acsm4 |
| 20148 | 3 | | | | | Actbl2 |
| 20149 | 3 | | | | | Adh6-ps1 |
| 20150 | 3 | | | | | Afp |
| 20151 | 3 | | | | | Aire |
| 20152 | 3 | | | | | Alx4 |
| 20153 | 3 | | | | | Ambn |
| 20154 | 3 | | | | | Amelx |
| 20155 | 3 | | | | | Amtn |
| 20156 | 3 | | | | | Ang5 |
| 20157 | 3 | | | | | Ang6 |
| 20158 | 3 | | | | | Ankfn1 |

Fig. 36 - 106

| | | | | | | | | | | | | | | |
|---|---|---|---|---|---|---|---|---|---|---|---|---|---|---|
| 20159 | 3 | | | | | | Ankk1 | 20255 | 3 | | | | | Cga |
| 20160 | 3 | | | | | | Ankrd33 | 20256 | 3 | | | | | Chil6 |
| 20161 | 3 | | | | | | Ankub1 | 20257 | 3 | | | | | ChkbCpt1b |
| 20162 | 3 | | | | | | Aox2 | 20258 | 3 | | | | | Chrng |
| 20163 | 3 | | | | | | Apol10b | 20259 | 3 | | | | | Cistr-act |
| 20164 | 3 | | | | | | Apol7c | 20260 | 3 | | | | | Clrn2 |
| 20165 | 3 | | | | | | Apol7d | 20261 | 3 | | | | | Cnga1 |
| 20166 | 3 | | | | | | Apoo-ps | 20262 | 3 | | | | | Cphx1 |
| 20167 | 3 | | | | | | Arhgap15os | 20263 | 3 | | | | | Cphx2 |
| 20168 | 3 | | | | | | Arid3c | 20264 | 3 | | | | | Cr2 |
| 20169 | 3 | | | | | | Arr3 | 20265 | 3 | | | | | Crisp3 |
| 20170 | 3 | | | | | | Ascl5 | 20266 | 3 | | | | | Crx |
| 20171 | 3 | | | | | | Asmt | 20267 | 3 | | | | | Crxos |
| 20172 | 3 | | | | | | Astl | 20268 | 3 | | | | | Cryba1 |
| 20173 | 3 | | | | | | Avpr1b | 20269 | 3 | | | | | Cryba2 |
| 20174 | 3 | | | | | | B020004C17Rik | 20270 | 3 | | | | | Crygc |
| 20175 | 3 | | | | | | B020004J07Rik | 20271 | 3 | | | | | Crygd |
| 20176 | 3 | | | | | | B020014A21Rik | 20272 | 3 | | | | | Crygf |
| 20177 | 3 | | | | | | B020018J22Rik | 20273 | 3 | | | | | Crygn |
| 20178 | 3 | | | | | | B020031M17Rik | 20274 | 3 | | | | | Crygs |
| 20179 | 3 | | | | | | B130006D01Rik | 20275 | 3 | | | | | Csf3 |
| 20180 | 3 | | | | | | B230112J18Rik | 20276 | 3 | | | | | Csmd2os |
| 20181 | 3 | | | | | | B230214G05Rik | 20277 | 3 | | | | | Csn1s1 |
| 20182 | 3 | | | | | | B230319C09Rik | 20278 | 3 | | | | | Csn1s2a |
| 20183 | 3 | | | | | | B230323A14Rik | 20279 | 3 | | | | | Csn1s2b |
| 20184 | 3 | | | | | | B930092H01Rik | 20280 | 3 | | | | | Csn2 |
| 20185 | 3 | | | | | | BB283400 | 20281 | 3 | | | | | Csn3 |
| 20186 | 3 | | | | | | BB557941 | 20282 | 3 | | | | | Cst10 |
| 20187 | 3 | | | | | | BC006965 | 20283 | 3 | | | | | Ctf2 |
| 20188 | 3 | | | | | | BC039771 | 20284 | 3 | | | | | Cts3 |
| 20189 | 3 | | | | | | BC049352 | 20285 | 3 | | | | | Cts6 |
| 20190 | 3 | | | | | | BC051665 | 20286 | 3 | | | | | Cts7 |
| 20191 | 3 | | | | | | BC052688 | 20287 | 3 | | | | | Cts8 |
| 20192 | 3 | | | | | | BC053393 | 20288 | 3 | | | | | Cts8-ps |
| 20193 | 3 | | | | | | BC055402 | 20289 | 3 | | | | | Ctsj |
| 20194 | 3 | | | | | | BC061212 | 20290 | 3 | | | | | Ctsll3 |
| 20195 | 3 | | | | | | BC065397 | 20291 | 3 | | | | | Ctsm |
| 20196 | 3 | | | | | | BC080695 | 20292 | 3 | | | | | Ctsq |
| 20197 | 3 | | | | | | Bach2os | 20293 | 3 | | | | | Ctsr |
| 20198 | 3 | | | | | | Bcl | 20294 | 3 | | | | | Cxcl3 |
| 20199 | 3 | | | | | | Bcl2a1c | 20295 | 3 | | | | | Cyp11b1 |
| 20200 | 3 | | | | | | Becn2 | 20296 | 3 | | | | | Cyp11b2 |
| 20201 | 3 | | | | | | Bhlhe23 | 20297 | 3 | | | | | Cyp26c1 |
| 20202 | 3 | | | | | | Birc7 | 20298 | 3 | | | | | Cyp2g1 |
| 20203 | 3 | | | | | | Bmp15 | 20299 | 3 | | | | | Cyp2t4 |
| 20204 | 3 | | | | | | Bpifa2 | 20300 | 3 | | | | | Cyp3a16 |
| 20205 | 3 | | | | | | Bpifa5 | 20301 | 3 | | | | | Cyp4a29 |
| 20206 | 3 | | | | | | Bpifa6 | 20302 | 3 | | | | | Cyp4a30b |
| 20207 | 3 | | | | | | Bpifb3 | 20303 | 3 | | | | | D030024E09Rik |
| 20208 | 3 | | | | | | Bpifb4 | 20304 | 3 | | | | | D030025E07Rik |
| 20209 | 3 | | | | | | Bpifb6 | 20305 | 3 | | | | | D030025P21Rik |
| 20210 | 3 | | | | | | Bpifb9a | 20306 | 3 | | | | | D130009I18Rik |
| 20211 | 3 | | | | | | Bpifb9b | 20307 | 3 | | | | | D130058E03 |
| 20212 | 3 | | | | | | Brs3 | 20308 | 3 | | | | | D14Ertd670e |
| 20213 | 3 | | | | | | Bsph2 | 20309 | 3 | | | | | D17Ertd648e |
| 20214 | 3 | | | | | | Bsx | 20310 | 3 | | | | | D230030E09Rik |
| 20215 | 3 | | | | | | Btn2a2 | 20311 | 3 | | | | | D4Ertd617e |
| 20216 | 3 | | | | | | C030007H22Rik | 20312 | 3 | | | | | D530049I02Rik |
| 20217 | 3 | | | | | | C130060C02Rik | 20313 | 3 | | | | | D5Ertd577e |
| 20218 | 3 | | | | | | C130060K24Rik | 20314 | 3 | | | | | D630010B17Rik |
| 20219 | 3 | | | | | | C130071C03Rik | 20315 | 3 | | | | | D730005E14Rik |
| 20220 | 3 | | | | | | C230024C17Rik | 20316 | 3 | | | | | D730045A05Rik |
| 20221 | 3 | | | | | | C230029M16 | 20317 | 3 | | | | | D730050B12Rik |
| 20222 | 3 | | | | | | C230079O03Rik | 20318 | 3 | | | | | D930007P13Rik |
| 20223 | 3 | | | | | | C330011F03Rik | 20319 | 3 | | | | | D930032P07Rik |
| 20224 | 3 | | | | | | C330024C12Rik | 20320 | 3 | | | | | DQ267100 |
| 20225 | 3 | | | | | | C430002E04Rik | 20321 | 3 | | | | | DQ267101 |
| 20226 | 3 | | | | | | C430002N11Rik | 20322 | 3 | | | | | DQ267102 |
| 20227 | 3 | | | | | | C630028M04Rik | 20323 | 3 | | | | | DXBay18 |
| 20228 | 3 | | | | | | C630031E19Rik | 20324 | 3 | | | | | Dbhos |
| 20229 | 3 | | | | | | C86187 | 20325 | 3 | | | | | Dbx1 |
| 20230 | 3 | | | | | | C86695 | 20326 | 3 | | | | | Dcpp2 |
| 20231 | 3 | | | | | | C87198 | 20327 | 3 | | | | | Dcpp3 |
| 20232 | 3 | | | | | | C87414 | 20328 | 3 | | | | | Defa-ps1 |
| 20233 | 3 | | | | | | C87499 | 20329 | 3 | | | | | Defa-ps12 |
| 20234 | 3 | | | | | | C87977 | 20330 | 3 | | | | | Defa-ps13 |
| 20235 | 3 | | | | | | C920009B18Rik | 20331 | 3 | | | | | Defa25 |
| 20236 | 3 | | | | | | Cabp5 | 20332 | 3 | | | | | Defa26 |
| 20237 | 3 | | | | | | Cacna1f | 20333 | 3 | | | | | Defb13 |
| 20238 | 3 | | | | | | Calcoco2 | 20334 | 3 | | | | | Defb34 |
| 20239 | 3 | | | | | | Calhm1 | 20335 | 3 | | | | | Defb40 |
| 20240 | 3 | | | | | | Ccl26 | 20336 | 3 | | | | | Defb44-ps |
| 20241 | 3 | | | | | | Cd3e | 20337 | 3 | | | | | Defb46 |
| 20242 | 3 | | | | | | Cd40lg | 20338 | 3 | | | | | Defb5 |
| 20243 | 3 | | | | | | Cd6 | 20339 | 3 | | | | | Defb50 |
| 20244 | 3 | | | | | | Cdcp2 | 20340 | 3 | | | | | Defb7 |
| 20245 | 3 | | | | | | Cdk15 | 20341 | 3 | | | | | Defb8 |
| 20246 | 3 | | | | | | Cdx4 | 20342 | 3 | | | | | Defb9 |
| 20247 | 3 | | | | | | Ceacam-ps1 | 20343 | 3 | | | | | Dfnb59 |
| 20248 | 3 | | | | | | Ceacam11 | 20344 | 3 | | | | | Dhrs2 |
| 20249 | 3 | | | | | | Ceacam13 | 20345 | 3 | | | | | Disc1 |
| 20250 | 3 | | | | | | Ceacam14 | 20346 | 3 | | | | | Dkk1 |
| 20251 | 3 | | | | | | Ceacam15 | 20347 | 3 | | | | | Dkk4 |
| 20252 | 3 | | | | | | Ceacam5 | 20348 | 3 | | | | | Dlx6as2 |
| 20253 | 3 | | | | | | Ceacam9 | 20349 | 3 | | | | | Dnmt3aos |
| 20254 | 3 | | | | | | Cer1 | 20350 | 3 | | | | | Doxl2 |

Fig. 36 - 107

| | | | | | | |
|---|---|---|---|---|---|---|
| 20351 | 3 | | | | | Dppa1 |
| 20352 | 3 | | | | | Dppa2 |
| 20353 | 3 | | | | | Dppa3 |
| 20354 | 3 | | | | | Drd3 |
| 20355 | 3 | | | | | Dsg4 |
| 20356 | 3 | | | | | Dspp |
| 20357 | 3 | | | | | Dthd1 |
| 20358 | 3 | | | | | Duxbl1 |
| 20359 | 3 | | | | | Duxbl3 |
| 20360 | 3 | | | | | Dynap |
| 20361 | 3 | | | | | Dytn |
| 20362 | 3 | | | | | E030002O03Rik |
| 20363 | 3 | | | | | E030025P04Rik |
| 20364 | 3 | | | | | E030044B06Rik |
| 20365 | 3 | | | | | E130006D01Rik |
| 20366 | 3 | | | | | E130304I02Rik |
| 20367 | 3 | | | | | E230019M04Rik |
| 20368 | 3 | | | | | E330012B07Rik |
| 20369 | 3 | | | | | E330014E10Rik |
| 20370 | 3 | | | | | E330017A01Rik |
| 20371 | 3 | | | | | E330017L17Rik |
| 20372 | 3 | | | | | E330021D16Rik |
| 20373 | 3 | | | | | E330023G01Rik |
| 20374 | 3 | | | | | Ear14 |
| 20375 | 3 | | | | | Ear4 |
| 20376 | 3 | | | | | Ect2l |
| 20377 | 3 | | | | | Eif4e1b |
| 20378 | 3 | | | | | Enam |
| 20379 | 3 | | | | | Enpp7 |
| 20380 | 3 | | | | | Epo |
| 20381 | 3 | | | | | Eras |
| 20382 | 3 | | | | | Erv3 |
| 20383 | 3 | | | | | Esp1 |
| 20384 | 3 | | | | | Esp15 |
| 20385 | 3 | | | | | Esp16 |
| 20386 | 3 | | | | | Esp18 |
| 20387 | 3 | | | | | Esp23 |
| 20388 | 3 | | | | | Esp24 |
| 20389 | 3 | | | | | Esp3 |
| 20390 | 3 | | | | | Esp31 |
| 20391 | 3 | | | | | Esp34 |
| 20392 | 3 | | | | | Esp36 |
| 20393 | 3 | | | | | Esp38 |
| 20394 | 3 | | | | | Esp4 |
| 20395 | 3 | | | | | Esp5 |
| 20396 | 3 | | | | | Esp6 |
| 20397 | 3 | | | | | Esp6-esp5 |
| 20398 | 3 | | | | | Esp8 |
| 20399 | 3 | | | | | Espnl |
| 20400 | 3 | | | | | Evi2a-evi2b |
| 20401 | 3 | | | | | Evx1 |
| 20402 | 3 | | | | | Evx2 |
| 20403 | 3 | | | | | F630111L10Rik |
| 20404 | 3 | | | | | F630206G17Rik |
| 20405 | 3 | | | | | F730035M05Rik |
| 20406 | 3 | | | | | Fam115e |
| 20407 | 3 | | | | | Fam159b |
| 20408 | 3 | | | | | Fam26d |
| 20409 | 3 | | | | | Fate1 |
| 20410 | 3 | | | | | Fbxw13 |
| 20411 | 3 | | | | | Fbxw14 |
| 20412 | 3 | | | | | Fbxw15 |
| 20413 | 3 | | | | | Fbxw16 |
| 20414 | 3 | | | | | Fbxw18 |
| 20415 | 3 | | | | | Fbxw19 |
| 20416 | 3 | | | | | Fbxw20 |
| 20417 | 3 | | | | | Fbxw21 |
| 20418 | 3 | | | | | Fbxw22 |
| 20419 | 3 | | | | | Fbxw24 |
| 20420 | 3 | | | | | Fbxw26 |
| 20421 | 3 | | | | | Fbxw28 |
| 20422 | 3 | | | | | Fcrl5 |
| 20423 | 3 | | | | | Fcrlb |
| 20424 | 3 | | | | | Ferd3l |
| 20425 | 3 | | | | | Fezf1 |
| 20426 | 3 | | | | | Ffar1 |
| 20427 | 3 | | | | | Fgf15 |
| 20428 | 3 | | | | | Fgf17 |
| 20429 | 3 | | | | | Fgf23 |
| 20430 | 3 | | | | | Fgf4 |
| 20431 | 3 | | | | | Fgf8 |
| 20432 | 3 | | | | | Fhad1os1 |
| 20433 | 3 | | | | | Fmo9 |
| 20434 | 3 | | | | | Fndc3c2 |
| 20435 | 3 | | | | | Fndc3c1 |
| 20436 | 3 | | | | | Foir4 |
| 20437 | 3 | | | | | Foxb2 |
| 20438 | 3 | | | | | Foxe1 |
| 20439 | 3 | | | | | Foxi2 |
| 20440 | 3 | | | | | Foxi3 |
| 20441 | 3 | | | | | Foxn4 |
| 20442 | 3 | | | | | Foxp3 |
| 20443 | 3 | | | | | Fpr-rs3 |
| 20444 | 3 | | | | | Fpr-rs4 |
| 20445 | 3 | | | | | Fpr-rs6 |
| 20446 | 3 | | | | | Fpr3 |
| 20447 | 3 | | | | | Frem3 |
| 20448 | 3 | | | | | Frmpd1os |
| 20449 | 3 | | | | | Frmpd3 |
| 20450 | 3 | | | | | Fshb |
| 20451 | 3 | | | | | Fut4-ps1 |
| 20452 | 3 | | | | | G630055G22Rik |
| 20453 | 3 | | | | | G630071F17Rik |
| 20454 | 3 | | | | | Gabrr3 |
| 20455 | 3 | | | | | Galp |
| 20456 | 3 | | | | | Galr3 |
| 20457 | 3 | | | | | Gata5os |
| 20458 | 3 | | | | | Gbx1 |
| 20459 | 3 | | | | | Gcm2 |
| 20460 | 3 | | | | | Gcnt7 |
| 20461 | 3 | | | | | Gdf7 |
| 20462 | 3 | | | | | Gfral |
| 20463 | 3 | | | | | Ghrh |
| 20464 | 3 | | | | | Ghsr |
| 20465 | 3 | | | | | Gja10 |
| 20466 | 3 | | | | | Gja8 |
| 20467 | 3 | | | | | Gjd4 |
| 20468 | 3 | | | | | Gje1 |
| 20469 | 3 | | | | | Glra4 |
| 20470 | 3 | | | | | Glyatl3 |
| 20471 | 3 | | | | | Gm10007 |
| 20472 | 3 | | | | | Gm10052 |
| 20473 | 3 | | | | | Gm10057 |
| 20474 | 3 | | | | | Gm10081 |
| 20475 | 3 | | | | | Gm10248 |
| 20476 | 3 | | | | | Gm10267 |
| 20477 | 3 | | | | | Gm10280 |
| 20478 | 3 | | | | | Gm10373 |
| 20479 | 3 | | | | | Gm10389 |
| 20480 | 3 | | | | | Gm10390 |
| 20481 | 3 | | | | | Gm10400 |
| 20482 | 3 | | | | | Gm10408 |
| 20483 | 3 | | | | | Gm10436 |
| 20484 | 3 | | | | | Gm10440 |
| 20485 | 3 | | | | | Gm10445 |
| 20486 | 3 | | | | | Gm10466 |
| 20487 | 3 | | | | | Gm10474 |
| 20488 | 3 | | | | | Gm10510 |
| 20489 | 3 | | | | | Gm10512 |
| 20490 | 3 | | | | | Gm10548 |
| 20491 | 3 | | | | | Gm10549 |
| 20492 | 3 | | | | | Gm10556 |
| 20493 | 3 | | | | | Gm10636 |
| 20494 | 3 | | | | | Gm10637 |
| 20495 | 3 | | | | | Gm10649 |
| 20496 | 3 | | | | | Gm10662 |
| 20497 | 3 | | | | | Gm10665 |
| 20498 | 3 | | | | | Gm10666 |
| 20499 | 3 | | | | | Gm10670 |
| 20500 | 3 | | | | | Gm10677 |
| 20501 | 3 | | | | | Gm10696 |
| 20502 | 3 | | | | | Gm10714 |
| 20503 | 3 | | | | | Gm10745 |
| 20504 | 3 | | | | | Gm10782 |
| 20505 | 3 | | | | | Gm10789 |
| 20506 | 3 | | | | | Gm10790 |
| 20507 | 3 | | | | | Gm10823 |
| 20508 | 3 | | | | | Gm10825 |
| 20509 | 3 | | | | | Gm10863 |
| 20510 | 3 | | | | | Gm11201 |
| 20511 | 3 | | | | | Gm11237 |
| 20512 | 3 | | | | | Gm11346 |
| 20513 | 3 | | | | | Gm1140 |
| 20514 | 3 | | | | | Gm11413 |
| 20515 | 3 | | | | | Gm11426 |
| 20516 | 3 | | | | | Gm11468 |
| 20517 | 3 | | | | | Gm11487 |
| 20518 | 3 | | | | | Gm11529 |
| 20519 | 3 | | | | | Gm11541 |
| 20520 | 3 | | | | | Gm11544 |
| 20521 | 3 | | | | | Gm11548 |
| 20522 | 3 | | | | | Gm11554 |
| 20523 | 3 | | | | | Gm11564 |
| 20524 | 3 | | | | | Gm11569 |
| 20525 | 3 | | | | | Gm11747 |
| 20526 | 3 | | | | | Gm11758 |
| 20527 | 3 | | | | | Gm11944 |
| 20528 | 3 | | | | | Gm11961 |
| 20529 | 3 | | | | | Gm11985 |
| 20530 | 3 | | | | | Gm12 |
| 20531 | 3 | | | | | Gm12130 |
| 20532 | 3 | | | | | Gm12169 |
| 20533 | 3 | | | | | Gm12171 |
| 20534 | 3 | | | | | Gm12191 |
| 20535 | 3 | | | | | Gm12238 |
| 20536 | 3 | | | | | Gm12253 |
| 20537 | 3 | | | | | Gm12505 |
| 20538 | 3 | | | | | Gm12603 |
| 20539 | 3 | | | | | Gm12669 |
| 20540 | 3 | | | | | Gm12718 |
| 20541 | 3 | | | | | Gm12789 |
| 20542 | 3 | | | | | Gm12794 |

Fig. 36 - 108

| | | | | | |
|---|---|---|---|---|---|
| 20543 | 3 | | | | Gm12830 |
| 20544 | 3 | | | | Gm12886 |
| 20545 | 3 | | | | Gm12887 |
| 20546 | 3 | | | | Gm13023 |
| 20547 | 3 | | | | Gm13031 |
| 20548 | 3 | | | | Gm13032 |
| 20549 | 3 | | | | Gm13040 |
| 20550 | 3 | | | | Gm13043 |
| 20551 | 3 | | | | Gm13057 |
| 20552 | 3 | | | | Gm13078 |
| 20553 | 3 | | | | Gm13083 |
| 20554 | 3 | | | | Gm13084 |
| 20555 | 3 | | | | Gm13088 |
| 20556 | 3 | | | | Gm13102 |
| 20557 | 3 | | | | Gm13103 |
| 20558 | 3 | | | | Gm13119 |
| 20559 | 3 | | | | Gm13125 |
| 20560 | 3 | | | | Gm13128 |
| 20561 | 3 | | | | Gm1322 |
| 20562 | 3 | | | | Gm13271 |
| 20563 | 3 | | | | Gm13272 |
| 20564 | 3 | | | | Gm13275 |
| 20565 | 3 | | | | Gm13276 |
| 20566 | 3 | | | | Gm13277 |
| 20567 | 3 | | | | Gm13278 |
| 20568 | 3 | | | | Gm13279 |
| 20569 | 3 | | | | Gm13283 |
| 20570 | 3 | | | | Gm13285 |
| 20571 | 3 | | | | Gm13286 |
| 20572 | 3 | | | | Gm13288 |
| 20573 | 3 | | | | Gm13290 |
| 20574 | 3 | | | | Gm13483 |
| 20575 | 3 | | | | Gm13490 |
| 20576 | 3 | | | | Gm13497 |
| 20577 | 3 | | | | Gm13544 |
| 20578 | 3 | | | | Gm13580 |
| 20579 | 3 | | | | Gm13582 |
| 20580 | 3 | | | | Gm13749 |
| 20581 | 3 | | | | Gm13752 |
| 20582 | 3 | | | | Gm13769 |
| 20583 | 3 | | | | Gm13939 |
| 20584 | 3 | | | | Gm13944 |
| 20585 | 3 | | | | Gm14015 |
| 20586 | 3 | | | | Gm14092 |
| 20587 | 3 | | | | Gm14124 |
| 20588 | 3 | | | | Gm14139 |
| 20589 | 3 | | | | Gm14306 |
| 20590 | 3 | | | | Gm14345 |
| 20591 | 3 | | | | Gm14346 |
| 20592 | 3 | | | | Gm14458 |
| 20593 | 3 | | | | Gm14459 |
| 20594 | 3 | | | | Gm14496 |
| 20595 | 3 | | | | Gm14548 |
| 20596 | 3 | | | | Gm14632 |
| 20597 | 3 | | | | Gm14635 |
| 20598 | 3 | | | | Gm14692 |
| 20599 | 3 | | | | Gm14718 |
| 20600 | 3 | | | | Gm14743 |
| 20601 | 3 | | | | Gm14744 |
| 20602 | 3 | | | | Gm14812 |
| 20603 | 3 | | | | Gm14850 |
| 20604 | 3 | | | | Gm14858 |
| 20605 | 3 | | | | Gm15008 |
| 20606 | 3 | | | | Gm15023 |
| 20607 | 3 | | | | Gm15091 |
| 20608 | 3 | | | | Gm15133 |
| 20609 | 3 | | | | Gm15293 |
| 20610 | 3 | | | | Gm15299 |
| 20611 | 3 | | | | Gm15413 |
| 20612 | 3 | | | | Gm1553 |
| 20613 | 3 | | | | Gm156 |
| 20614 | 3 | | | | Gm15679 |
| 20615 | 3 | | | | Gm15713 |
| 20616 | 3 | | | | Gm1587 |
| 20617 | 3 | | | | Gm15880 |
| 20618 | 3 | | | | Gm15910 |
| 20619 | 3 | | | | Gm15941 |
| 20620 | 3 | | | | Gm15997 |
| 20621 | 3 | | | | Gm16287 |
| 20622 | 3 | | | | Gm16291 |
| 20623 | 3 | | | | Gm16294 |
| 20624 | 3 | | | | Gm16336 |
| 20625 | 3 | | | | Gm16367 |
| 20626 | 3 | | | | Gm16451 |
| 20627 | 3 | | | | Gm16497 |
| 20628 | 3 | | | | Gm16796 |
| 20629 | 3 | | | | Gm16833 |
| 20630 | 3 | | | | Gm16853 |
| 20631 | 3 | | | | Gm1715 |
| 20632 | 3 | | | | Gm1720 |
| 20633 | 3 | | | | Gm17252 |
| 20634 | 3 | | | | Gm17365 |
| 20635 | 3 | | | | Gm17660 |
| 20636 | 3 | | | | Gm17689 |
| 20637 | 3 | | | | Gm17751 |
| 20638 | 3 | | | | Gm17821 |
| 20639 | 3 | | | | Gm17830 |
| 20640 | 3 | | | | Gm18409 |
| 20641 | 3 | | | | Gm18853 |
| 20642 | 3 | | | | Gm19276 |
| 20643 | 3 | | | | Gm19299 |
| 20644 | 3 | | | | Gm19303 |
| 20645 | 3 | | | | Gm19424 |
| 20646 | 3 | | | | Gm19434 |
| 20647 | 3 | | | | Gm19466 |
| 20648 | 3 | | | | Gm19510 |
| 20649 | 3 | | | | Gm19589 |
| 20650 | 3 | | | | Gm19619 |
| 20651 | 3 | | | | Gm1965 |
| 20652 | 3 | | | | Gm19668 |
| 20653 | 3 | | | | Gm19757 |
| 20654 | 3 | | | | Gm19782 |
| 20655 | 3 | | | | Gm19784 |
| 20656 | 3 | | | | Gm20098 |
| 20657 | 3 | | | | Gm20110 |
| 20658 | 3 | | | | Gm20125 |
| 20659 | 3 | | | | Gm20139 |
| 20660 | 3 | | | | Gm2016 |
| 20661 | 3 | | | | Gm20172 |
| 20662 | 3 | | | | Gm20187 |
| 20663 | 3 | | | | Gm20199 |
| 20664 | 3 | | | | Gm2022 |
| 20665 | 3 | | | | Gm20356 |
| 20666 | 3 | | | | Gm20362 |
| 20667 | 3 | | | | Gm20556 |
| 20668 | 3 | | | | Gm20597 |
| 20669 | 3 | | | | Gm20735 |
| 20670 | 3 | | | | Gm20741 |
| 20671 | 3 | | | | Gm20744 |
| 20672 | 3 | | | | Gm20745 |
| 20673 | 3 | | | | Gm20750 |
| 20674 | 3 | | | | Gm20755 |
| 20675 | 3 | | | | Gm20756 |
| 20676 | 3 | | | | Gm20757 |
| 20677 | 3 | | | | Gm20758 |
| 20678 | 3 | | | | Gm20759 |
| 20679 | 3 | | | | Gm20765 |
| 20680 | 3 | | | | Gm20767 |
| 20681 | 3 | | | | Gm20816 |
| 20682 | 3 | | | | Gm20867 |
| 20683 | 3 | | | | Gm2109 |
| 20684 | 3 | | | | Gm21276 |
| 20685 | 3 | | | | Gm21293 |
| 20686 | 3 | | | | Gm21304 |
| 20687 | 3 | | | | Gm21312 |
| 20688 | 3 | | | | Gm21319 |
| 20689 | 3 | | | | Gm21944 |
| 20690 | 3 | | | | Gm2381 |
| 20691 | 3 | | | | Gm2447 |
| 20692 | 3 | | | | Gm2516 |
| 20693 | 3 | | | | Gm2721 |
| 20694 | 3 | | | | Gm2837 |
| 20695 | 3 | | | | Gm2913 |
| 20696 | 3 | | | | Gm3020 |
| 20697 | 3 | | | | Gm3139 |
| 20698 | 3 | | | | Gm3259 |
| 20699 | 3 | | | | Gm3279 |
| 20700 | 3 | | | | Gm3286 |
| 20701 | 3 | | | | Gm3428 |
| 20702 | 3 | | | | Gm3434 |
| 20703 | 3 | | | | Gm3701 |
| 20704 | 3 | | | | Gm4133 |
| 20705 | 3 | | | | Gm4175 |
| 20706 | 3 | | | | Gm4201 |
| 20707 | 3 | | | | Gm4214 |
| 20708 | 3 | | | | Gm4216 |
| 20709 | 3 | | | | Gm4224 |
| 20710 | 3 | | | | Gm4265 |
| 20711 | 3 | | | | Gm4278 |
| 20712 | 3 | | | | Gm428 |
| 20713 | 3 | | | | Gm4297 |
| 20714 | 3 | | | | Gm4301 |
| 20715 | 3 | | | | Gm4302 |
| 20716 | 3 | | | | Gm4303 |
| 20717 | 3 | | | | Gm4307 |
| 20718 | 3 | | | | Gm4312 |
| 20719 | 3 | | | | Gm4340 |
| 20720 | 3 | | | | Gm4371 |
| 20721 | 3 | | | | Gm44 |
| 20722 | 3 | | | | Gm4432 |
| 20723 | 3 | | | | Gm4461 |
| 20724 | 3 | | | | Gm4541 |
| 20725 | 3 | | | | Gm4559 |
| 20726 | 3 | | | | Gm4567 |
| 20727 | 3 | | | | Gm4710 |
| 20728 | 3 | | | | Gm4736 |
| 20729 | 3 | | | | Gm4745 |
| 20730 | 3 | | | | Gm4791 |
| 20731 | 3 | | | | Gm4792 |
| 20732 | 3 | | | | Gm4794 |
| 20733 | 3 | | | | Gm4827 |
| 20734 | 3 | | | | Gm4847 |

Fig. 36 - 109

| | | | | | | |
|---|---|---|---|---|---|---|
| 20735 | 3 | | | | | Gm4850 |
| 20736 | 3 | | | | | Gm4858 |
| 20737 | 3 | | | | | Gm4872 |
| 20738 | 3 | | | | | Gm4894 |
| 20739 | 3 | | | | | Gm4906 |
| 20740 | 3 | | | | | Gm4975 |
| 20741 | 3 | | | | | Gm4981 |
| 20742 | 3 | | | | | Gm5039 |
| 20743 | 3 | | | | | Gm5082 |
| 20744 | 3 | | | | | Gm5087 |
| 20745 | 3 | | | | | Gm5095 |
| 20746 | 3 | | | | | Gm5122 |
| 20747 | 3 | | | | | Gm5177 |
| 20748 | 3 | | | | | Gm5414 |
| 20749 | 3 | | | | | Gm5441 |
| 20750 | 3 | | | | | Gm5464 |
| 20751 | 3 | | | | | Gm5475 |
| 20752 | 3 | | | | | Gm5476 |
| 20753 | 3 | | | | | Gm5535 |
| 20754 | 3 | | | | | Gm5544 |
| 20755 | 3 | | | | | Gm5615 |
| 20756 | 3 | | | | | Gm5622 |
| 20757 | 3 | | | | | Gm5662 |
| 20758 | 3 | | | | | Gm5712 |
| 20759 | 3 | | | | | Gm5725 |
| 20760 | 3 | | | | | Gm5726 |
| 20761 | 3 | | | | | Gm5728 |
| 20762 | 3 | | | | | Gm5833 |
| 20763 | 3 | | | | | Gm5885 |
| 20764 | 3 | | | | | Gm5886 |
| 20765 | 3 | | | | | Gm5891 |
| 20766 | 3 | | | | | Gm5938 |
| 20767 | 3 | | | | | Gm6042 |
| 20768 | 3 | | | | | Gm6116 |
| 20769 | 3 | | | | | Gm6150 |
| 20770 | 3 | | | | | Gm6164 |
| 20771 | 3 | | | | | Gm6213 |
| 20772 | 3 | | | | | Gm6249 |
| 20773 | 3 | | | | | Gm6260 |
| 20774 | 3 | | | | | Gm6313 |
| 20775 | 3 | | | | | Gm6367 |
| 20776 | 3 | | | | | Gm6406 |
| 20777 | 3 | | | | | Gm6498 |
| 20778 | 3 | | | | | Gm6592 |
| 20779 | 3 | | | | | Gm6602 |
| 20780 | 3 | | | | | Gm6696 |
| 20781 | 3 | | | | | Gm6763 |
| 20782 | 3 | | | | | Gm6878 |
| 20783 | 3 | | | | | Gm6902 |
| 20784 | 3 | | | | | Gm6904 |
| 20785 | 3 | | | | | Gm6936 |
| 20786 | 3 | | | | | Gm6938 |
| 20787 | 3 | | | | | Gm6994 |
| 20788 | 3 | | | | | Gm7056 |
| 20789 | 3 | | | | | Gm7134 |
| 20790 | 3 | | | | | Gm7173 |
| 20791 | 3 | | | | | Gm7257 |
| 20792 | 3 | | | | | Gm7271 |
| 20793 | 3 | | | | | Gm7337 |
| 20794 | 3 | | | | | Gm7457 |
| 20795 | 3 | | | | | Gm7534 |
| 20796 | 3 | | | | | Gm7538 |
| 20797 | 3 | | | | | Gm7550 |
| 20798 | 3 | | | | | Gm7616 |
| 20799 | 3 | | | | | Gm7714 |
| 20800 | 3 | | | | | Gm7854 |
| 20801 | 3 | | | | | Gm7977 |
| 20802 | 3 | | | | | Gm7978 |
| 20803 | 3 | | | | | Gm813 |
| 20804 | 3 | | | | | Gm815 |
| 20805 | 3 | | | | | Gm8179 |
| 20806 | 3 | | | | | Gm8234 |
| 20807 | 3 | | | | | Gm829 |
| 20808 | 3 | | | | | Gm8298 |
| 20809 | 3 | | | | | Gm8300 |
| 20810 | 3 | | | | | Gm833 |
| 20811 | 3 | | | | | Gm8369 |
| 20812 | 3 | | | | | Gm839 |
| 20813 | 3 | | | | | Gm8439 |
| 20814 | 3 | | | | | Gm8579 |
| 20815 | 3 | | | | | Gm8677 |
| 20816 | 3 | | | | | Gm8693 |
| 20817 | 3 | | | | | Gm8709 |
| 20818 | 3 | | | | | Gm8773 |
| 20819 | 3 | | | | | Gm8817 |
| 20820 | 3 | | | | | Gm8882 |
| 20821 | 3 | | | | | Gm8884 |
| 20822 | 3 | | | | | Gm9125 |
| 20823 | 3 | | | | | Gm9159 |
| 20824 | 3 | | | | | Gm9268 |
| 20825 | 3 | | | | | Gm933 |
| 20826 | 3 | | | | | Gm9376 |
| 20827 | 3 | | | | | Gm9513 |
| 20828 | 3 | | | | | Gm9573 |
| 20829 | 3 | | | | | Gm960 |
| 20830 | 3 | | | | | Gm9767 |
| 20831 | 3 | | | | | Gm9871 |
| 20832 | 3 | | | | | Gm9920 |
| 20833 | 3 | | | | | Gmcl1 |
| 20834 | 3 | | | | | Gnat2 |
| 20835 | 3 | | | | | Gnat3 |
| 20836 | 3 | | | | | Gngt1 |
| 20837 | 3 | | | | | Gnrhr |
| 20838 | 3 | | | | | Gphb5 |
| 20839 | 3 | | | | | Gpr110 |
| 20840 | 3 | | | | | Gpr119 |
| 20841 | 3 | | | | | Gpr142 |
| 20842 | 3 | | | | | Gpr143 |
| 20843 | 3 | | | | | Gpr152 |
| 20844 | 3 | | | | | Gpr31b |
| 20845 | 3 | | | | | Gpr33 |
| 20846 | 3 | | | | | Gpr50 |
| 20847 | 3 | | | | | Grifin |
| 20848 | 3 | | | | | Grk1 |
| 20849 | 3 | | | | | Grm6 |
| 20850 | 3 | | | | | Grxcr1 |
| 20851 | 3 | | | | | Grxcr2 |
| 20852 | 3 | | | | | Gsdma3 |
| 20853 | 3 | | | | | Gsx1 |
| 20854 | 3 | | | | | Gsx2 |
| 20855 | 3 | | | | | Guca1b |
| 20856 | 3 | | | | | Gucy1b2 |
| 20857 | 3 | | | | | Gucy2e |
| 20858 | 3 | | | | | Gucy2f |
| 20859 | 3 | | | | | Gucy2g |
| 20860 | 3 | | | | | Gzmd |
| 20861 | 3 | | | | | Gzme |
| 20862 | 3 | | | | | Gzmf |
| 20863 | 3 | | | | | Gzmg |
| 20864 | 3 | | | | | H1foo |
| 20865 | 3 | | | | | H2-L |
| 20866 | 3 | | | | | H2-M1 |
| 20867 | 3 | | | | | H2-M10.1 |
| 20868 | 3 | | | | | H2-M10.3 |
| 20869 | 3 | | | | | H2-M10.4 |
| 20870 | 3 | | | | | H2-M10.5 |
| 20871 | 3 | | | | | H2-M10.6 |
| 20872 | 3 | | | | | H2-M11 |
| 20873 | 3 | | | | | H2afb2 |
| 20874 | 3 | | | | | Has2os |
| 20875 | 3 | | | | | Hbb-bh1 |
| 20876 | 3 | | | | | Hbb-bh2 |
| 20877 | 3 | | | | | Hesx1 |
| 20878 | 3 | | | | | Hhla1 |
| 20879 | 3 | | | | | Higd1c |
| 20880 | 3 | | | | | Hmx3 |
| 20881 | 3 | | | | | Hotair |
| 20882 | 3 | | | | | Hoxb1 |
| 20883 | 3 | | | | | Hoxc12 |
| 20884 | 3 | | | | | Hoxd1 |
| 20885 | 3 | | | | | Hoxd12 |
| 20886 | 3 | | | | | Hsf3 |
| 20887 | 3 | | | | | Htr1f |
| 20888 | 3 | | | | | I730028E13Rik |
| 20889 | 3 | | | | | Ifi44l |
| 20890 | 3 | | | | | Ifna1 |
| 20891 | 3 | | | | | Ifna11 |
| 20892 | 3 | | | | | Ifna12 |
| 20893 | 3 | | | | | Ifna13 |
| 20894 | 3 | | | | | Ifna14 |
| 20895 | 3 | | | | | Ifna15 |
| 20896 | 3 | | | | | Ifna16 |
| 20897 | 3 | | | | | Ifna2 |
| 20898 | 3 | | | | | Ifna4 |
| 20899 | 3 | | | | | Ifna5 |
| 20900 | 3 | | | | | Ifna6 |
| 20901 | 3 | | | | | Ifna7 |
| 20902 | 3 | | | | | Ifna9 |
| 20903 | 3 | | | | | Ifnab |
| 20904 | 3 | | | | | Ifnb1 |
| 20905 | 3 | | | | | Ifne |
| 20906 | 3 | | | | | Ifng |
| 20907 | 3 | | | | | Ifnk |
| 20908 | 3 | | | | | Ifnl2 |
| 20909 | 3 | | | | | Ifnl3 |
| 20910 | 3 | | | | | Ifnz |
| 20911 | 3 | | | | | Igdcc3 |
| 20912 | 3 | | | | | Igf2os |
| 20913 | 3 | | | | | Igfbpl1 |
| 20914 | 3 | | | | | Igfl3 |
| 20915 | 3 | | | | | Il10 |
| 20916 | 3 | | | | | Il12b |
| 20917 | 3 | | | | | Il17a |
| 20918 | 3 | | | | | Il17c |
| 20919 | 3 | | | | | Il19 |
| 20920 | 3 | | | | | Il1rapl2 |
| 20921 | 3 | | | | | Il2 |
| 20922 | 3 | | | | | Il20 |
| 20923 | 3 | | | | | Il23a |
| 20924 | 3 | | | | | Il24 |
| 20925 | 3 | | | | | Il3 |
| 20926 | 3 | | | | | Il5 |

Fig. 36 - 110

| | | | | | | |
|---|---|---|---|---|---|---|
| 20927 | 3 | | | | | Il6 |
| 20928 | 3 | | | | | Il9 |
| 20929 | 3 | | | | | Il9r |
| 20930 | 3 | | | | | Impg1 |
| 20931 | 3 | | | | | Insm2 |
| 20932 | 3 | | | | | Iqcj |
| 20933 | 3 | | | | | Irx6 |
| 20934 | 3 | | | | | Isl2 |
| 20935 | 3 | | | | | Kcna10 |
| 20936 | 3 | | | | | Kcng3 |
| 20937 | 3 | | | | | Kcnk15 |
| 20938 | 3 | | | | | Kcnk18 |
| 20939 | 3 | | | | | Kcnmb3 |
| 20940 | 3 | | | | | Kcnq1ot1 |
| 20941 | 3 | | | | | Khdc1a |
| 20942 | 3 | | | | | Khdc1b |
| 20943 | 3 | | | | | Khdc1c |
| 20944 | 3 | | | | | Kir3dl2 |
| 20945 | 3 | | | | | Kis2 |
| 20946 | 3 | | | | | Kif14 |
| 20947 | 3 | | | | | Kihdc7b |
| 20948 | 3 | | | | | Klk15 |
| 20949 | 3 | | | | | Klk1b1 |
| 20950 | 3 | | | | | Klk1b16 |
| 20951 | 3 | | | | | Klk1b22 |
| 20952 | 3 | | | | | Klk4 |
| 20953 | 3 | | | | | Klra15 |
| 20954 | 3 | | | | | Klra19 |
| 20955 | 3 | | | | | Klra22 |
| 20956 | 3 | | | | | Klra33 |
| 20957 | 3 | | | | | Klra4 |
| 20958 | 3 | | | | | Klra6 |
| 20959 | 3 | | | | | Klrb1 |
| 20960 | 3 | | | | | Klrb1-ps1 |
| 20961 | 3 | | | | | Kncn |
| 20962 | 3 | | | | | Krt26 |
| 20963 | 3 | | | | | Krt28 |
| 20964 | 3 | | | | | Krt39 |
| 20965 | 3 | | | | | Krt40 |
| 20966 | 3 | | | | | Krt72 |
| 20967 | 3 | | | | | Krt74 |
| 20968 | 3 | | | | | Krt82 |
| 20969 | 3 | | | | | Krtap13 |
| 20970 | 3 | | | | | Krtap19-1 |
| 20971 | 3 | | | | | Krtap20-2 |
| 20972 | 3 | | | | | Krtap24-1 |
| 20973 | 3 | | | | | Krtap27-1 |
| 20974 | 3 | | | | | Krtap31-1 |
| 20975 | 3 | | | | | Krtap31-2 |
| 20976 | 3 | | | | | Krtap5-3 |
| 20977 | 3 | | | | | Krtap9-5 |
| 20978 | 3 | | | | | LOC100043315 |
| 20979 | 3 | | | | | LOC100502896 |
| 20980 | 3 | | | | | LOC100503280 |
| 20981 | 3 | | | | | LOC100862015 |
| 20982 | 3 | | | | | LOC101055863 |
| 20983 | 3 | | | | | LOC101056236 |
| 20984 | 3 | | | | | LOC101243624 |
| 20985 | 3 | | | | | LOC102308570 |
| 20986 | 3 | | | | | LOC102632423 |
| 20987 | 3 | | | | | LOC102633035 |
| 20988 | 3 | | | | | LOC102634101 |
| 20989 | 3 | | | | | LOC102634431 |
| 20990 | 3 | | | | | LOC171588 |
| 20991 | 3 | | | | | Lactbl1 |
| 20992 | 3 | | | | | Lalba |
| 20993 | 3 | | | | | Lao1 |
| 20994 | 3 | | | | | Lcn11 |
| 20995 | 3 | | | | | Lcn3 |
| 20996 | 3 | | | | | Lcn4 |
| 20997 | 3 | | | | | Lct |
| 20998 | 3 | | | | | Ldlrad2 |
| 20999 | 3 | | | | | Lefty2 |
| 21000 | 3 | | | | | Lgsn |
| 21001 | 3 | | | | | Lhx3 |
| 21002 | 3 | | | | | Lhx4 |
| 21003 | 3 | | | | | Lman1l |
| 21004 | 3 | | | | | Lmx1b |
| 21005 | 3 | | | | | Lrit3 |
| 21006 | 3 | | | | | Lyg1 |
| 21007 | 3 | | | | | Lyg2 |
| 21008 | 3 | | | | | Magea1 |
| 21009 | 3 | | | | | Magea2 |
| 21010 | 3 | | | | | Mageb16-ps1 |
| 21011 | 3 | | | | | Mamdc4 |
| 21012 | 3 | | | | | Manr |
| 21013 | 3 | | | | | Matn1 |
| 21014 | 3 | | | | | Mbd3l2 |
| 21015 | 3 | | | | | Mc1r |
| 21016 | 3 | | | | | Mc3r |
| 21017 | 3 | | | | | Mccc1os |
| 21018 | 3 | | | | | Mcidas |
| 21019 | 3 | | | | | Mcpt9 |
| 21020 | 3 | | | | | Mei1 |
| 21021 | 3 | | | | | Mei4 |
| 21022 | 3 | | | | | Mepe |
| 21023 | 3 | | | | | Mettl7a3 |
| 21024 | 3 | | | | | Mlp |
| 21025 | 3 | | | | | Mir100 |
| 21026 | 3 | | | | | Mir101a |
| 21027 | 3 | | | | | Mir101b |
| 21028 | 3 | | | | | Mir101c |
| 21029 | 3 | | | | | Mir103-1 |
| 21030 | 3 | | | | | Mir103-2 |
| 21031 | 3 | | | | | Mir105 |
| 21032 | 3 | | | | | Mir106a |
| 21033 | 3 | | | | | Mir106b |
| 21034 | 3 | | | | | Mir107 |
| 21035 | 3 | | | | | Mir10b |
| 21036 | 3 | | | | | Mir1187 |
| 21037 | 3 | | | | | Mir1188 |
| 21038 | 3 | | | | | Mir1190 |
| 21039 | 3 | | | | | Mir1191 |
| 21040 | 3 | | | | | Mir1191b |
| 21041 | 3 | | | | | Mir1193 |
| 21042 | 3 | | | | | Mir1195 |
| 21043 | 3 | | | | | Mir1197 |
| 21044 | 3 | | | | | Mir1198 |
| 21045 | 3 | | | | | Mir1224 |
| 21046 | 3 | | | | | Mir122a |
| 21047 | 3 | | | | | Mir1231 |
| 21048 | 3 | | | | | Mir1247 |
| 21049 | 3 | | | | | Mir1249 |
| 21050 | 3 | | | | | Mir124a-1 |
| 21051 | 3 | | | | | Mir124a-2 |
| 21052 | 3 | | | | | Mir124a-3 |
| 21053 | 3 | | | | | Mir1251 |
| 21054 | 3 | | | | | Mir1258 |
| 21055 | 3 | | | | | Mir125a |
| 21056 | 3 | | | | | Mir125b-1 |
| 21057 | 3 | | | | | Mir125b-2 |
| 21058 | 3 | | | | | Mir126 |
| 21059 | 3 | | | | | Mir1264 |
| 21060 | 3 | | | | | Mir126b |
| 21061 | 3 | | | | | Mir127 |
| 21062 | 3 | | | | | Mir128-1 |
| 21063 | 3 | | | | | Mir128-2 |
| 21064 | 3 | | | | | Mir129-1 |
| 21065 | 3 | | | | | Mir129-2 |
| 21066 | 3 | | | | | Mir1298 |
| 21067 | 3 | | | | | Mir129b |
| 21068 | 3 | | | | | Mir1306 |
| 21069 | 3 | | | | | Mir130a |
| 21070 | 3 | | | | | Mir130b |
| 21071 | 3 | | | | | Mir130c |
| 21072 | 3 | | | | | Mir132 |
| 21073 | 3 | | | | | Mir133a-1 |
| 21074 | 3 | | | | | Mir133a-2 |
| 21075 | 3 | | | | | Mir133b |
| 21076 | 3 | | | | | Mir133c |
| 21077 | 3 | | | | | Mir134 |
| 21078 | 3 | | | | | Mir135a-1 |
| 21079 | 3 | | | | | Mir135a-2 |
| 21080 | 3 | | | | | Mir135b |
| 21081 | 3 | | | | | Mir136 |
| 21082 | 3 | | | | | Mir137 |
| 21083 | 3 | | | | | Mir138-1 |
| 21084 | 3 | | | | | Mir138-2 |
| 21085 | 3 | | | | | Mir139 |
| 21086 | 3 | | | | | Mir140 |
| 21087 | 3 | | | | | Mir141 |
| 21088 | 3 | | | | | Mir142 |
| 21089 | 3 | | | | | Mir143 |
| 21090 | 3 | | | | | Mir144 |
| 21091 | 3 | | | | | Mir145 |
| 21092 | 3 | | | | | Mir145b |
| 21093 | 3 | | | | | Mir146 |
| 21094 | 3 | | | | | Mir146b |
| 21095 | 3 | | | | | Mir147 |
| 21096 | 3 | | | | | Mir148a |
| 21097 | 3 | | | | | Mir148b |
| 21098 | 3 | | | | | Mir149 |
| 21099 | 3 | | | | | Mir150 |
| 21100 | 3 | | | | | Mir152 |
| 21101 | 3 | | | | | Mir153 |
| 21102 | 3 | | | | | Mir154 |
| 21103 | 3 | | | | | Mir155 |
| 21104 | 3 | | | | | Mir15a |
| 21105 | 3 | | | | | Mir15b |
| 21106 | 3 | | | | | Mir16-1 |
| 21107 | 3 | | | | | Mir16-2 |
| 21108 | 3 | | | | | Mir17 |
| 21109 | 3 | | | | | Mir18 |
| 21110 | 3 | | | | | Mir181a-1 |
| 21111 | 3 | | | | | Mir181a-2 |
| 21112 | 3 | | | | | Mir181b-1 |
| 21113 | 3 | | | | | Mir181b-2 |
| 21114 | 3 | | | | | Mir181c |
| 21115 | 3 | | | | | Mir181d |
| 21116 | 3 | | | | | Mir182 |
| 21117 | 3 | | | | | Mir183 |
| 21118 | 3 | | | | | Mir1839 |

Fig. 36 - 111

| | | | | | |
|---|---|---|---|---|---|
| 21119 | 3 | | | | Mir184 |
| 21120 | 3 | | | | Mir1843 |
| 21121 | 3 | | | | Mir1843b |
| 21122 | 3 | | | | Mir185 |
| 21123 | 3 | | | | Mir186 |
| 21124 | 3 | | | | Mir187 |
| 21125 | 3 | | | | Mir188 |
| 21126 | 3 | | | | Mir1892 |
| 21127 | 3 | | | | Mir1893 |
| 21128 | 3 | | | | Mir1894 |
| 21129 | 3 | | | | Mir1895 |
| 21130 | 3 | | | | Mir1896 |
| 21131 | 3 | | | | Mir1897 |
| 21132 | 3 | | | | Mir1898 |
| 21133 | 3 | | | | Mir1899 |
| 21134 | 3 | | | | Mir18b |
| 21135 | 3 | | | | Mir190 |
| 21136 | 3 | | | | Mir1900 |
| 21137 | 3 | | | | Mir1901 |
| 21138 | 3 | | | | Mir1902 |
| 21139 | 3 | | | | Mir1903 |
| 21140 | 3 | | | | Mir1904 |
| 21141 | 3 | | | | Mir1905 |
| 21142 | 3 | | | | Mir1906-1 |
| 21143 | 3 | | | | Mir1907 |
| 21144 | 3 | | | | Mir190b |
| 21145 | 3 | | | | Mir191 |
| 21146 | 3 | | | | Mir1912 |
| 21147 | 3 | | | | Mir192 |
| 21148 | 3 | | | | Mir1928 |
| 21149 | 3 | | | | Mir1929 |
| 21150 | 3 | | | | Mir193 |
| 21151 | 3 | | | | Mir1930 |
| 21152 | 3 | | | | Mir1931 |
| 21153 | 3 | | | | Mir1932 |
| 21154 | 3 | | | | Mir1933 |
| 21155 | 3 | | | | Mir1934 |
| 21156 | 3 | | | | Mir1936 |
| 21157 | 3 | | | | Mir193b |
| 21158 | 3 | | | | Mir194-1 |
| 21159 | 3 | | | | Mir194-2 |
| 21160 | 3 | | | | Mir1940 |
| 21161 | 3 | | | | Mir1941 |
| 21162 | 3 | | | | Mir1942 |
| 21163 | 3 | | | | Mir1943 |
| 21164 | 3 | | | | Mir1945 |
| 21165 | 3 | | | | Mir1946b |
| 21166 | 3 | | | | Mir1947 |
| 21167 | 3 | | | | Mir1948 |
| 21168 | 3 | | | | Mir1949 |
| 21169 | 3 | | | | Mir195 |
| 21170 | 3 | | | | Mir1950 |
| 21171 | 3 | | | | Mir1951 |
| 21172 | 3 | | | | Mir1952 |
| 21173 | 3 | | | | Mir1953 |
| 21174 | 3 | | | | Mir1954 |
| 21175 | 3 | | | | Mir1955 |
| 21176 | 3 | | | | Mir1956 |
| 21177 | 3 | | | | Mir1957 |
| 21178 | 3 | | | | Mir1958 |
| 21179 | 3 | | | | Mir195b |
| 21180 | 3 | | | | Mir1960 |
| 21181 | 3 | | | | Mir1961 |
| 21182 | 3 | | | | Mir1962 |
| 21183 | 3 | | | | Mir1963 |
| 21184 | 3 | | | | Mir1964 |
| 21185 | 3 | | | | Mir1967 |
| 21186 | 3 | | | | Mir1968 |
| 21187 | 3 | | | | Mir1969 |
| 21188 | 3 | | | | Mir196a-1 |
| 21189 | 3 | | | | Mir196a-2 |
| 21190 | 3 | | | | Mir196b |
| 21191 | 3 | | | | Mir1970 |
| 21192 | 3 | | | | Mir1971 |
| 21193 | 3 | | | | Mir1981 |
| 21194 | 3 | | | | Mir1982 |
| 21195 | 3 | | | | Mir1983 |
| 21196 | 3 | | | | Mir199a-1 |
| 21197 | 3 | | | | Mir199a-2 |
| 21198 | 3 | | | | Mir199b |
| 21199 | 3 | | | | Mir19a |
| 21200 | 3 | | | | Mir19b-1 |
| 21201 | 3 | | | | Mir19b-2 |
| 21202 | 3 | | | | Mir1a-1 |
| 21203 | 3 | | | | Mir1a-2 |
| 21204 | 3 | | | | Mir1b |
| 21205 | 3 | | | | Mir200a |
| 21206 | 3 | | | | Mir200b |
| 21207 | 3 | | | | Mir200c |
| 21208 | 3 | | | | Mir201 |
| 21209 | 3 | | | | Mir202 |
| 21210 | 3 | | | | Mir203 |
| 21211 | 3 | | | | Mir204 |
| 21212 | 3 | | | | Mir205 |
| 21213 | 3 | | | | Mir206 |
| 21214 | 3 | | | | Mir207 |
| 21215 | 3 | | | | Mir208a |
| 21216 | 3 | | | | Mir208b |
| 21217 | 3 | | | | Mir20a |
| 21218 | 3 | | | | Mir20b |
| 21219 | 3 | | | | Mir21 |
| 21220 | 3 | | | | Mir210 |
| 21221 | 3 | | | | Mir211 |
| 21222 | 3 | | | | Mir212 |
| 21223 | 3 | | | | Mir2136 |
| 21224 | 3 | | | | Mir2137 |
| 21225 | 3 | | | | Mir2139 |
| 21226 | 3 | | | | Mir215 |
| 21227 | 3 | | | | Mir216a |
| 21228 | 3 | | | | Mir216b |
| 21229 | 3 | | | | Mir216c |
| 21230 | 3 | | | | Mir217 |
| 21231 | 3 | | | | Mir218-1 |
| 21232 | 3 | | | | Mir218-2 |
| 21233 | 3 | | | | Mir219-1 |
| 21234 | 3 | | | | Mir219-2 |
| 21235 | 3 | | | | Mir219b |
| 21236 | 3 | | | | Mir219c |
| 21237 | 3 | | | | Mir21b |
| 21238 | 3 | | | | Mir21c |
| 21239 | 3 | | | | Mir22 |
| 21240 | 3 | | | | Mir221 |
| 21241 | 3 | | | | Mir222 |
| 21242 | 3 | | | | Mir223 |
| 21243 | 3 | | | | Mir23a |
| 21244 | 3 | | | | Mir23b |
| 21245 | 3 | | | | Mir24-1 |
| 21246 | 3 | | | | Mir24-2 |
| 21247 | 3 | | | | Mir25 |
| 21248 | 3 | | | | Mir26a-1 |
| 21249 | 3 | | | | Mir26a-2 |
| 21250 | 3 | | | | Mir26b |
| 21251 | 3 | | | | Mir27a |
| 21252 | 3 | | | | Mir27b |
| 21253 | 3 | | | | Mir28 |
| 21254 | 3 | | | | Mir2861 |
| 21255 | 3 | | | | Mir28b |
| 21256 | 3 | | | | Mir28c |
| 21257 | 3 | | | | Mir290 |
| 21258 | 3 | | | | Mir290b |
| 21259 | 3 | | | | Mir291a |
| 21260 | 3 | | | | Mir291b |
| 21261 | 3 | | | | Mir292 |
| 21262 | 3 | | | | Mir292b |
| 21263 | 3 | | | | Mir293 |
| 21264 | 3 | | | | Mir294 |
| 21265 | 3 | | | | Mir295 |
| 21266 | 3 | | | | Mir296 |
| 21267 | 3 | | | | Mir297-1 |
| 21268 | 3 | | | | Mir297-2 |
| 21269 | 3 | | | | Mir297a-3 |
| 21270 | 3 | | | | Mir297a-4 |
| 21271 | 3 | | | | Mir297b |
| 21272 | 3 | | | | Mir297c |
| 21273 | 3 | | | | Mir298 |
| 21274 | 3 | | | | Mir299 |
| 21275 | 3 | | | | Mir299b |
| 21276 | 3 | | | | Mir29a |
| 21277 | 3 | | | | Mir29b-1 |
| 21278 | 3 | | | | Mir29b-2 |
| 21279 | 3 | | | | Mir29c |
| 21280 | 3 | | | | Mir300 |
| 21281 | 3 | | | | Mir301 |
| 21282 | 3 | | | | Mir301b |
| 21283 | 3 | | | | Mir302a |
| 21284 | 3 | | | | Mir302b |
| 21285 | 3 | | | | Mir302c |
| 21286 | 3 | | | | Mir302d |
| 21287 | 3 | | | | Mir3057 |
| 21288 | 3 | | | | Mir3058 |
| 21289 | 3 | | | | Mir3059 |
| 21290 | 3 | | | | Mir3060 |
| 21291 | 3 | | | | Mir3061 |
| 21292 | 3 | | | | Mir3062 |
| 21293 | 3 | | | | Mir3063 |
| 21294 | 3 | | | | Mir3064 |
| 21295 | 3 | | | | Mir3065 |
| 21296 | 3 | | | | Mir3066 |
| 21297 | 3 | | | | Mir3067 |
| 21298 | 3 | | | | Mir3068 |
| 21299 | 3 | | | | Mir3069 |
| 21300 | 3 | | | | Mir3070a |
| 21301 | 3 | | | | Mir3070b |
| 21302 | 3 | | | | Mir3071 |
| 21303 | 3 | | | | Mir3072 |
| 21304 | 3 | | | | Mir3073 |
| 21305 | 3 | | | | Mir3073b |
| 21306 | 3 | | | | Mir3074-1 |
| 21307 | 3 | | | | Mir3074-2 |
| 21308 | 3 | | | | Mir3075 |
| 21309 | 3 | | | | Mir3076 |
| 21310 | 3 | | | | Mir3077 |

Fig. 36 - 112

| | | | | | | |
|---|---|---|---|---|---|---|
| 21311 | 3 | | | | | Mir3078 |
| 21312 | 3 | | | | | Mir3079 |
| 21313 | 3 | | | | | Mir3081 |
| 21314 | 3 | | | | | Mir3082 |
| 21315 | 3 | | | | | Mir3083 |
| 21316 | 3 | | | | | Mir3084 |
| 21317 | 3 | | | | | Mir3084-2 |
| 21318 | 3 | | | | | Mir3085 |
| 21319 | 3 | | | | | Mir3086 |
| 21320 | 3 | | | | | Mir3087 |
| 21321 | 3 | | | | | Mir3088 |
| 21322 | 3 | | | | | Mir3089 |
| 21323 | 3 | | | | | Mir3091 |
| 21324 | 3 | | | | | Mir3092 |
| 21325 | 3 | | | | | Mir3093 |
| 21326 | 3 | | | | | Mir3094 |
| 21327 | 3 | | | | | Mir3095 |
| 21328 | 3 | | | | | Mir3097 |
| 21329 | 3 | | | | | Mir3098 |
| 21330 | 3 | | | | | Mir3099 |
| 21331 | 3 | | | | | Mir30a |
| 21332 | 3 | | | | | Mir30b |
| 21333 | 3 | | | | | Mir30c-1 |
| 21334 | 3 | | | | | Mir30c-2 |
| 21335 | 3 | | | | | Mir30d |
| 21336 | 3 | | | | | Mir30f |
| 21337 | 3 | | | | | Mir31 |
| 21338 | 3 | | | | | Mir3100 |
| 21339 | 3 | | | | | Mir3101 |
| 21340 | 3 | | | | | Mir3102 |
| 21341 | 3 | | | | | Mir3103 |
| 21342 | 3 | | | | | Mir3104 |
| 21343 | 3 | | | | | Mir3106 |
| 21344 | 3 | | | | | Mir3107 |
| 21345 | 3 | | | | | Mir3108 |
| 21346 | 3 | | | | | Mir3109 |
| 21347 | 3 | | | | | Mir3110 |
| 21348 | 3 | | | | | Mir3112 |
| 21349 | 3 | | | | | Mir32 |
| 21350 | 3 | | | | | Mir320 |
| 21351 | 3 | | | | | Mir322 |
| 21352 | 3 | | | | | Mir323 |
| 21353 | 3 | | | | | Mir324 |
| 21354 | 3 | | | | | Mir325 |
| 21355 | 3 | | | | | Mir326 |
| 21356 | 3 | | | | | Mir328 |
| 21357 | 3 | | | | | Mir329 |
| 21358 | 3 | | | | | Mir33 |
| 21359 | 3 | | | | | Mir330 |
| 21360 | 3 | | | | | Mir331 |
| 21361 | 3 | | | | | Mir335 |
| 21362 | 3 | | | | | Mir337 |
| 21363 | 3 | | | | | Mir338 |
| 21364 | 3 | | | | | Mir339 |
| 21365 | 3 | | | | | Mir340 |
| 21366 | 3 | | | | | Mir341 |
| 21367 | 3 | | | | | Mir343 |
| 21368 | 3 | | | | | Mir344 |
| 21369 | 3 | | | | | Mir344-2 |
| 21370 | 3 | | | | | Mir344b |
| 21371 | 3 | | | | | Mir344c |
| 21372 | 3 | | | | | Mir344d-1 |
| 21373 | 3 | | | | | Mir344d-2 |
| 21374 | 3 | | | | | Mir344d-3 |
| 21375 | 3 | | | | | Mir344e |
| 21376 | 3 | | | | | Mir344f |
| 21377 | 3 | | | | | Mir344g |
| 21378 | 3 | | | | | Mir344h-1 |
| 21379 | 3 | | | | | Mir344i |
| 21380 | 3 | | | | | Mir345 |
| 21381 | 3 | | | | | Mir346 |
| 21382 | 3 | | | | | Mir3470a |
| 21383 | 3 | | | | | Mir3470b |
| 21384 | 3 | | | | | Mir3471-1 |
| 21385 | 3 | | | | | Mir3473 |
| 21386 | 3 | | | | | Mir3473c |
| 21387 | 3 | | | | | Mir3473d |
| 21388 | 3 | | | | | Mir3473e |
| 21389 | 3 | | | | | Mir3473f |
| 21390 | 3 | | | | | Mir3474 |
| 21391 | 3 | | | | | Mir3475 |
| 21392 | 3 | | | | | Mir34a |
| 21393 | 3 | | | | | Mir34b |
| 21394 | 3 | | | | | Mir34c |
| 21395 | 3 | | | | | Mir350 |
| 21396 | 3 | | | | | Mir351 |
| 21397 | 3 | | | | | Mir3544 |
| 21398 | 3 | | | | | Mir3547 |
| 21399 | 3 | | | | | Mir3569 |
| 21400 | 3 | | | | | Mir3572 |
| 21401 | 3 | | | | | Mir362 |
| 21402 | 3 | | | | | Mir3620 |
| 21403 | 3 | | | | | Mir363 |
| 21404 | 3 | | | | | Mir365-1 |
| 21405 | 3 | | | | | Mir367 |
| 21406 | 3 | | | | | Mir369 |
| 21407 | 3 | | | | | Mir370 |
| 21408 | 3 | | | | | Mir374 |
| 21409 | 3 | | | | | Mir374c |
| 21410 | 3 | | | | | Mir375 |
| 21411 | 3 | | | | | Mir376a |
| 21412 | 3 | | | | | Mir376b |
| 21413 | 3 | | | | | Mir376c |
| 21414 | 3 | | | | | Mir377 |
| 21415 | 3 | | | | | Mir378 |
| 21416 | 3 | | | | | Mir378b |
| 21417 | 3 | | | | | Mir378c |
| 21418 | 3 | | | | | Mir379 |
| 21419 | 3 | | | | | Mir380 |
| 21420 | 3 | | | | | Mir381 |
| 21421 | 3 | | | | | Mir382 |
| 21422 | 3 | | | | | Mir383 |
| 21423 | 3 | | | | | Mir384 |
| 21424 | 3 | | | | | Mir3960 |
| 21425 | 3 | | | | | Mir3962 |
| 21426 | 3 | | | | | Mir3963 |
| 21427 | 3 | | | | | Mir3964 |
| 21428 | 3 | | | | | Mir3965 |
| 21429 | 3 | | | | | Mir3966 |
| 21430 | 3 | | | | | Mir3967 |
| 21431 | 3 | | | | | Mir3968 |
| 21432 | 3 | | | | | Mir3969 |
| 21433 | 3 | | | | | Mir3970 |
| 21434 | 3 | | | | | Mir3971 |
| 21435 | 3 | | | | | Mir409 |
| 21436 | 3 | | | | | Mir410 |
| 21437 | 3 | | | | | Mir411 |
| 21438 | 3 | | | | | Mir412 |
| 21439 | 3 | | | | | Mir421 |
| 21440 | 3 | | | | | Mir423 |
| 21441 | 3 | | | | | Mir425 |
| 21442 | 3 | | | | | Mir429 |
| 21443 | 3 | | | | | Mir431 |
| 21444 | 3 | | | | | Mir432 |
| 21445 | 3 | | | | | Mir433 |
| 21446 | 3 | | | | | Mir434 |
| 21447 | 3 | | | | | Mir448 |
| 21448 | 3 | | | | | Mir449a |
| 21449 | 3 | | | | | Mir449b |
| 21450 | 3 | | | | | Mir449c |
| 21451 | 3 | | | | | Mir450-1 |
| 21452 | 3 | | | | | Mir450-2 |
| 21453 | 3 | | | | | Mir450b |
| 21454 | 3 | | | | | Mir451 |
| 21455 | 3 | | | | | Mir452 |
| 21456 | 3 | | | | | Mir453 |
| 21457 | 3 | | | | | Mir455 |
| 21458 | 3 | | | | | Mir463 |
| 21459 | 3 | | | | | Mir465 |
| 21460 | 3 | | | | | Mir465b-1 |
| 21461 | 3 | | | | | Mir465c-1 |
| 21462 | 3 | | | | | Mir465d |
| 21463 | 3 | | | | | Mir466 |
| 21464 | 3 | | | | | Mir466c |
| 21465 | 3 | | | | | Mir466b-2 |
| 21466 | 3 | | | | | Mir466b-3 |
| 21467 | 3 | | | | | Mir466d |
| 21468 | 3 | | | | | Mir466f-1 |
| 21469 | 3 | | | | | Mir466f-2 |
| 21470 | 3 | | | | | Mir466f-3 |
| 21471 | 3 | | | | | Mir466g |
| 21472 | 3 | | | | | Mir466h |
| 21473 | 3 | | | | | Mir466n |
| 21474 | 3 | | | | | Mir466p |
| 21475 | 3 | | | | | Mir467a-1 |
| 21476 | 3 | | | | | Mir467a-10 |
| 21477 | 3 | | | | | Mir467a-2 |
| 21478 | 3 | | | | | Mir467a-3 |
| 21479 | 3 | | | | | Mir467a-5 |
| 21480 | 3 | | | | | Mir467a-7 |
| 21481 | 3 | | | | | Mir467a-9 |
| 21482 | 3 | | | | | Mir467b |
| 21483 | 3 | | | | | Mir467c |
| 21484 | 3 | | | | | Mir467d |
| 21485 | 3 | | | | | Mir467e |
| 21486 | 3 | | | | | Mir467f |
| 21487 | 3 | | | | | Mir468 |
| 21488 | 3 | | | | | Mir470 |
| 21489 | 3 | | | | | Mir471 |
| 21490 | 3 | | | | | Mir483 |
| 21491 | 3 | | | | | Mir484 |
| 21492 | 3 | | | | | Mir485 |
| 21493 | 3 | | | | | Mir487b |
| 21494 | 3 | | | | | Mir488 |
| 21495 | 3 | | | | | Mir489 |
| 21496 | 3 | | | | | Mir490 |
| 21497 | 3 | | | | | Mir491 |
| 21498 | 3 | | | | | Mir493 |
| 21499 | 3 | | | | | Mir494 |
| 21500 | 3 | | | | | Mir495 |
| 21501 | 3 | | | | | Mir496 |
| 21502 | 3 | | | | | Mir496b |

Fig. 36 - 113

| | | | | | | |
|---|---|---|---|---|---|---|
| 21503 | 3 | | | | | Mir497 |
| 21504 | 3 | | | | | Mir497b |
| 21505 | 3 | | | | | Mir499 |
| 21506 | 3 | | | | | Mir500 |
| 21507 | 3 | | | | | Mir501 |
| 21508 | 3 | | | | | Mir503 |
| 21509 | 3 | | | | | Mir504 |
| 21510 | 3 | | | | | Mir5046 |
| 21511 | 3 | | | | | Mir505 |
| 21512 | 3 | | | | | Mir509 |
| 21513 | 3 | | | | | Mir5098 |
| 21514 | 3 | | | | | Mir5100 |
| 21515 | 3 | | | | | Mir5101 |
| 21516 | 3 | | | | | Mir5103 |
| 21517 | 3 | | | | | Mir5104 |
| 21518 | 3 | | | | | Mir5106 |
| 21519 | 3 | | | | | Mir5107 |
| 21520 | 3 | | | | | Mir5108 |
| 21521 | 3 | | | | | Mir511 |
| 21522 | 3 | | | | | Mir5112 |
| 21523 | 3 | | | | | Mir5113 |
| 21524 | 3 | | | | | Mir5114 |
| 21525 | 3 | | | | | Mir5116 |
| 21526 | 3 | | | | | Mir5119 |
| 21527 | 3 | | | | | Mir5120 |
| 21528 | 3 | | | | | Mir5121 |
| 21529 | 3 | | | | | Mir5122 |
| 21530 | 3 | | | | | Mir5123 |
| 21531 | 3 | | | | | Mir5124 |
| 21532 | 3 | | | | | Mir5125 |
| 21533 | 3 | | | | | Mir5126 |
| 21534 | 3 | | | | | Mir5127 |
| 21535 | 3 | | | | | Mir5128 |
| 21536 | 3 | | | | | Mir5129 |
| 21537 | 3 | | | | | Mir5130 |
| 21538 | 3 | | | | | Mir5131 |
| 21539 | 3 | | | | | Mir5132 |
| 21540 | 3 | | | | | Mir5133 |
| 21541 | 3 | | | | | Mir5134 |
| 21542 | 3 | | | | | Mir5135 |
| 21543 | 3 | | | | | Mir5136 |
| 21544 | 3 | | | | | Mir532 |
| 21545 | 3 | | | | | Mir539 |
| 21546 | 3 | | | | | Mir540 |
| 21547 | 3 | | | | | Mir541 |
| 21548 | 3 | | | | | Mir542 |
| 21549 | 3 | | | | | Mir543 |
| 21550 | 3 | | | | | Mir544 |
| 21551 | 3 | | | | | Mir547 |
| 21552 | 3 | | | | | Mir551b |
| 21553 | 3 | | | | | Mir5615-1 |
| 21554 | 3 | | | | | Mir5615-2 |
| 21555 | 3 | | | | | Mir5616 |
| 21556 | 3 | | | | | Mir5617 |
| 21557 | 3 | | | | | Mir5618 |
| 21558 | 3 | | | | | Mir5619 |
| 21559 | 3 | | | | | Mir5620 |
| 21560 | 3 | | | | | Mir5621 |
| 21561 | 3 | | | | | Mir5622 |
| 21562 | 3 | | | | | Mir5623 |
| 21563 | 3 | | | | | Mir5624 |
| 21564 | 3 | | | | | Mir5625 |
| 21565 | 3 | | | | | Mir5626 |
| 21566 | 3 | | | | | Mir5627 |
| 21567 | 3 | | | | | Mir568 |
| 21568 | 3 | | | | | Mir5709 |
| 21569 | 3 | | | | | Mir5710 |
| 21570 | 3 | | | | | Mir574 |
| 21571 | 3 | | | | | Mir582 |
| 21572 | 3 | | | | | Mir592 |
| 21573 | 3 | | | | | Mir598 |
| 21574 | 3 | | | | | Mir599 |
| 21575 | 3 | | | | | Mir615 |
| 21576 | 3 | | | | | Mir6237 |
| 21577 | 3 | | | | | Mir6238 |
| 21578 | 3 | | | | | Mir6239 |
| 21579 | 3 | | | | | Mir6241 |
| 21580 | 3 | | | | | Mir6335 |
| 21581 | 3 | | | | | Mir6336 |
| 21582 | 3 | | | | | Mir6337 |
| 21583 | 3 | | | | | Mir6339 |
| 21584 | 3 | | | | | Mir6341 |
| 21585 | 3 | | | | | Mir6342 |
| 21586 | 3 | | | | | Mir6343 |
| 21587 | 3 | | | | | Mir6344 |
| 21588 | 3 | | | | | Mir6348 |
| 21589 | 3 | | | | | Mir6349 |
| 21590 | 3 | | | | | Mir6350 |
| 21591 | 3 | | | | | Mir6352 |
| 21592 | 3 | | | | | Mir6353 |
| 21593 | 3 | | | | | Mir6354 |
| 21594 | 3 | | | | | Mir6355 |
| 21595 | 3 | | | | | Mir6356 |
| 21596 | 3 | | | | | Mir6358 |
| 21597 | 3 | | | | | Mir6359 |
| 21598 | 3 | | | | | Mir6360 |
| 21599 | 3 | | | | | Mir6361 |
| 21600 | 3 | | | | | Mir6362 |
| 21601 | 3 | | | | | Mir6364 |
| 21602 | 3 | | | | | Mir6365 |
| 21603 | 3 | | | | | Mir6366 |
| 21604 | 3 | | | | | Mir6367 |
| 21605 | 3 | | | | | Mir6368 |
| 21606 | 3 | | | | | Mir6369 |
| 21607 | 3 | | | | | Mir6370 |
| 21608 | 3 | | | | | Mir6372 |
| 21609 | 3 | | | | | Mir6373 |
| 21610 | 3 | | | | | Mir6374 |
| 21611 | 3 | | | | | Mir6375 |
| 21612 | 3 | | | | | Mir6376 |
| 21613 | 3 | | | | | Mir6378 |
| 21614 | 3 | | | | | Mir6380 |
| 21615 | 3 | | | | | Mir6381 |
| 21616 | 3 | | | | | Mir6382 |
| 21617 | 3 | | | | | Mir6383 |
| 21618 | 3 | | | | | Mir6384 |
| 21619 | 3 | | | | | Mir6385 |
| 21620 | 3 | | | | | Mir6386 |
| 21621 | 3 | | | | | Mir6387 |
| 21622 | 3 | | | | | Mir6388 |
| 21623 | 3 | | | | | Mir6389 |
| 21624 | 3 | | | | | Mir6391 |
| 21625 | 3 | | | | | Mir6392 |
| 21626 | 3 | | | | | Mir6393 |
| 21627 | 3 | | | | | Mir6394 |
| 21628 | 3 | | | | | Mir6395 |
| 21629 | 3 | | | | | Mir6396 |
| 21630 | 3 | | | | | Mir6397 |
| 21631 | 3 | | | | | Mir6398 |
| 21632 | 3 | | | | | Mir6399 |
| 21633 | 3 | | | | | Mir6400 |
| 21634 | 3 | | | | | Mir6401 |
| 21635 | 3 | | | | | Mir6402 |
| 21636 | 3 | | | | | Mir6404 |
| 21637 | 3 | | | | | Mir6405 |
| 21638 | 3 | | | | | Mir6406 |
| 21639 | 3 | | | | | Mir6407 |
| 21640 | 3 | | | | | Mir6408 |
| 21641 | 3 | | | | | Mir6409 |
| 21642 | 3 | | | | | Mir6410 |
| 21643 | 3 | | | | | Mir6411 |
| 21644 | 3 | | | | | Mir6412 |
| 21645 | 3 | | | | | Mir6413 |
| 21646 | 3 | | | | | Mir6414 |
| 21647 | 3 | | | | | Mir6415 |
| 21648 | 3 | | | | | Mir6416 |
| 21649 | 3 | | | | | Mir6417 |
| 21650 | 3 | | | | | Mir6419 |
| 21651 | 3 | | | | | Mir6420 |
| 21652 | 3 | | | | | Mir6481 |
| 21653 | 3 | | | | | Mir653 |
| 21654 | 3 | | | | | Mir6538 |
| 21655 | 3 | | | | | Mir6539 |
| 21656 | 3 | | | | | Mir654 |
| 21657 | 3 | | | | | Mir6540 |
| 21658 | 3 | | | | | Mir6541 |
| 21659 | 3 | | | | | Mir6546 |
| 21660 | 3 | | | | | Mir664 |
| 21661 | 3 | | | | | Mir665 |
| 21662 | 3 | | | | | Mir666 |
| 21663 | 3 | | | | | Mir667 |
| 21664 | 3 | | | | | Mir668 |
| 21665 | 3 | | | | | Mir669a-1 |
| 21666 | 3 | | | | | Mir669a-2 |
| 21667 | 3 | | | | | Mir669a-3 |
| 21668 | 3 | | | | | Mir669a-4 |
| 21669 | 3 | | | | | Mir669b |
| 21670 | 3 | | | | | Mir669c |
| 21671 | 3 | | | | | Mir669e |
| 21672 | 3 | | | | | Mir669g |
| 21673 | 3 | | | | | Mir669h |
| 21674 | 3 | | | | | Mir669i |
| 21675 | 3 | | | | | Mir669j |
| 21676 | 3 | | | | | Mir669k |
| 21677 | 3 | | | | | Mir669m-1 |
| 21678 | 3 | | | | | Mir669m-2 |
| 21679 | 3 | | | | | Mir669p-1 |
| 21680 | 3 | | | | | Mir670 |
| 21681 | 3 | | | | | Mir671 |
| 21682 | 3 | | | | | Mir6715 |
| 21683 | 3 | | | | | Mir672 |
| 21684 | 3 | | | | | Mir673 |
| 21685 | 3 | | | | | Mir674 |
| 21686 | 3 | | | | | Mir675 |
| 21687 | 3 | | | | | Mir676 |
| 21688 | 3 | | | | | Mir6769b |
| 21689 | 3 | | | | | Mir677 |
| 21690 | 3 | | | | | Mir678 |
| 21691 | 3 | | | | | Mir679 |
| 21692 | 3 | | | | | Mir680-2 |
| 21693 | 3 | | | | | Mir680-3 |
| 21694 | 3 | | | | | Mir681 |

Fig. 36 - 114

| | | | | | | | | | | | | |
|---|---|---|---|---|---|---|---|---|---|---|---|---|
| 21695 | 3 | | | | | Mir683-1 | 21791 | 3 | | | | Mir698 |
| 21696 | 3 | | | | | Mir684-1 | 21792 | 3 | | | | Mir6980 |
| 21697 | 3 | | | | | Mir684-2 | 21793 | 3 | | | | Mir6982 |
| 21698 | 3 | | | | | Mir686 | 21794 | 3 | | | | Mir6983 |
| 21699 | 3 | | | | | Mir687 | 21795 | 3 | | | | Mir6984 |
| 21700 | 3 | | | | | Mir688 | 21796 | 3 | | | | Mir6985 |
| 21701 | 3 | | | | | Mir6896 | 21797 | 3 | | | | Mir6986 |
| 21702 | 3 | | | | | Mir6897 | 21798 | 3 | | | | Mir6987 |
| 21703 | 3 | | | | | Mir6898 | 21799 | 3 | | | | Mir6988 |
| 21704 | 3 | | | | | Mir6899 | 21800 | 3 | | | | Mir6989 |
| 21705 | 3 | | | | | Mir690 | 21801 | 3 | | | | Mir6990 |
| 21706 | 3 | | | | | Mir6900 | 21802 | 3 | | | | Mir6991 |
| 21707 | 3 | | | | | Mir6901 | 21803 | 3 | | | | Mir6993 |
| 21708 | 3 | | | | | Mir6902 | 21804 | 3 | | | | Mir6994 |
| 21709 | 3 | | | | | Mir6903 | 21805 | 3 | | | | Mir6995 |
| 21710 | 3 | | | | | Mir6904 | 21806 | 3 | | | | Mir6996 |
| 21711 | 3 | | | | | Mir6905 | 21807 | 3 | | | | Mir6997 |
| 21712 | 3 | | | | | Mir6906 | 21808 | 3 | | | | Mir6998 |
| 21713 | 3 | | | | | Mir6907 | 21809 | 3 | | | | Mir6999 |
| 21714 | 3 | | | | | Mir6908 | 21810 | 3 | | | | Mir7-2 |
| 21715 | 3 | | | | | Mir6909 | 21811 | 3 | | | | Mir700 |
| 21716 | 3 | | | | | Mir691 | 21812 | 3 | | | | Mir7000 |
| 21717 | 3 | | | | | Mir6910 | 21813 | 3 | | | | Mir7001 |
| 21718 | 3 | | | | | Mir6911 | 21814 | 3 | | | | Mir7002 |
| 21719 | 3 | | | | | Mir6912 | 21815 | 3 | | | | Mir7003 |
| 21720 | 3 | | | | | Mir6913 | 21816 | 3 | | | | Mir7004 |
| 21721 | 3 | | | | | Mir6914 | 21817 | 3 | | | | Mir7005 |
| 21722 | 3 | | | | | Mir6915 | 21818 | 3 | | | | Mir7006 |
| 21723 | 3 | | | | | Mir6916 | 21819 | 3 | | | | Mir7007 |
| 21724 | 3 | | | | | Mir6917 | 21820 | 3 | | | | Mir7008 |
| 21725 | 3 | | | | | Mir6918 | 21821 | 3 | | | | Mir7009 |
| 21726 | 3 | | | | | Mir6919 | 21822 | 3 | | | | Mir701 |
| 21727 | 3 | | | | | Mir692-1 | 21823 | 3 | | | | Mir7010 |
| 21728 | 3 | | | | | Mir6920 | 21824 | 3 | | | | Mir7011 |
| 21729 | 3 | | | | | Mir6921 | 21825 | 3 | | | | Mir7012 |
| 21730 | 3 | | | | | Mir6922 | 21826 | 3 | | | | Mir7013 |
| 21731 | 3 | | | | | Mir6923 | 21827 | 3 | | | | Mir7014 |
| 21732 | 3 | | | | | Mir6924 | 21828 | 3 | | | | Mir7015 |
| 21733 | 3 | | | | | Mir6925 | 21829 | 3 | | | | Mir7016 |
| 21734 | 3 | | | | | Mir6926 | 21830 | 3 | | | | Mir7017 |
| 21735 | 3 | | | | | Mir6927 | 21831 | 3 | | | | Mir7018 |
| 21736 | 3 | | | | | Mir6928 | 21832 | 3 | | | | Mir7019 |
| 21737 | 3 | | | | | Mir6929 | 21833 | 3 | | | | Mir702 |
| 21738 | 3 | | | | | Mir693 | 21834 | 3 | | | | Mir7020 |
| 21739 | 3 | | | | | Mir6930 | 21835 | 3 | | | | Mir7021 |
| 21740 | 3 | | | | | Mir6931 | 21836 | 3 | | | | Mir7022 |
| 21741 | 3 | | | | | Mir6932 | 21837 | 3 | | | | Mir7023 |
| 21742 | 3 | | | | | Mir6933 | 21838 | 3 | | | | Mir7024 |
| 21743 | 3 | | | | | Mir6934 | 21839 | 3 | | | | Mir7025 |
| 21744 | 3 | | | | | Mir6935 | 21840 | 3 | | | | Mir7026 |
| 21745 | 3 | | | | | Mir6936 | 21841 | 3 | | | | Mir7027 |
| 21746 | 3 | | | | | Mir6937 | 21842 | 3 | | | | Mir7028 |
| 21747 | 3 | | | | | Mir6938 | 21843 | 3 | | | | Mir7029 |
| 21748 | 3 | | | | | Mir6939 | 21844 | 3 | | | | Mir7030 |
| 21749 | 3 | | | | | Mir694 | 21845 | 3 | | | | Mir7031 |
| 21750 | 3 | | | | | Mir6940 | 21846 | 3 | | | | Mir7032 |
| 21751 | 3 | | | | | Mir6941 | 21847 | 3 | | | | Mir7033 |
| 21752 | 3 | | | | | Mir6942 | 21848 | 3 | | | | Mir7034 |
| 21753 | 3 | | | | | Mir6943 | 21849 | 3 | | | | Mir7035 |
| 21754 | 3 | | | | | Mir6944 | 21850 | 3 | | | | Mir7036 |
| 21755 | 3 | | | | | Mir6945 | 21851 | 3 | | | | Mir7036b |
| 21756 | 3 | | | | | Mir6946 | 21852 | 3 | | | | Mir7037 |
| 21757 | 3 | | | | | Mir6947 | 21853 | 3 | | | | Mir7038 |
| 21758 | 3 | | | | | Mir6948 | 21854 | 3 | | | | Mir7039 |
| 21759 | 3 | | | | | Mir6949 | 21855 | 3 | | | | Mir704 |
| 21760 | 3 | | | | | Mir695 | 21856 | 3 | | | | Mir7040 |
| 21761 | 3 | | | | | Mir6950 | 21857 | 3 | | | | Mir7041 |
| 21762 | 3 | | | | | Mir6951 | 21858 | 3 | | | | Mir7042 |
| 21763 | 3 | | | | | Mir6952 | 21859 | 3 | | | | Mir7043 |
| 21764 | 3 | | | | | Mir6953 | 21860 | 3 | | | | Mir7044 |
| 21765 | 3 | | | | | Mir6954 | 21861 | 3 | | | | Mir7045 |
| 21766 | 3 | | | | | Mir6955 | 21862 | 3 | | | | Mir7046 |
| 21767 | 3 | | | | | Mir6956 | 21863 | 3 | | | | Mir7047 |
| 21768 | 3 | | | | | Mir6957 | 21864 | 3 | | | | Mir7048 |
| 21769 | 3 | | | | | Mir6958 | 21865 | 3 | | | | Mir7049 |
| 21770 | 3 | | | | | Mir6959 | 21866 | 3 | | | | Mir705 |
| 21771 | 3 | | | | | Mir6960 | 21867 | 3 | | | | Mir7050 |
| 21772 | 3 | | | | | Mir6961 | 21868 | 3 | | | | Mir7051 |
| 21773 | 3 | | | | | Mir6962 | 21869 | 3 | | | | Mir7052 |
| 21774 | 3 | | | | | Mir6963 | 21870 | 3 | | | | Mir7053 |
| 21775 | 3 | | | | | Mir6964 | 21871 | 3 | | | | Mir7054 |
| 21776 | 3 | | | | | Mir6965 | 21872 | 3 | | | | Mir7055 |
| 21777 | 3 | | | | | Mir6966 | 21873 | 3 | | | | Mir7056 |
| 21778 | 3 | | | | | Mir6968 | 21874 | 3 | | | | Mir7057 |
| 21779 | 3 | | | | | Mir6969 | 21875 | 3 | | | | Mir7058 |
| 21780 | 3 | | | | | Mir6970 | 21876 | 3 | | | | Mir7059 |
| 21781 | 3 | | | | | Mir6971 | 21877 | 3 | | | | Mir706 |
| 21782 | 3 | | | | | Mir6972 | 21878 | 3 | | | | Mir7060 |
| 21783 | 3 | | | | | Mir6973a | 21879 | 3 | | | | Mir7061 |
| 21784 | 3 | | | | | Mir6973b | 21880 | 3 | | | | Mir7062 |
| 21785 | 3 | | | | | Mir6974 | 21881 | 3 | | | | Mir7063 |
| 21786 | 3 | | | | | Mir6975 | 21882 | 3 | | | | Mir7064 |
| 21787 | 3 | | | | | Mir6976 | 21883 | 3 | | | | Mir7065 |
| 21788 | 3 | | | | | Mir6977 | 21884 | 3 | | | | Mir7066 |
| 21789 | 3 | | | | | Mir6978 | 21885 | 3 | | | | Mir7067 |
| 21790 | 3 | | | | | Mir6979 | 21886 | 3 | | | | Mir7068 |

Fig. 36 - 115

| | | | | | |
|---|---|---|---|---|---|
| 21887 | 3 | | | | Mir7069 |
| 21888 | 3 | | | | Mir707 |
| 21889 | 3 | | | | Mir7070 |
| 21890 | 3 | | | | Mir7071 |
| 21891 | 3 | | | | Mir7072 |
| 21892 | 3 | | | | Mir7073 |
| 21893 | 3 | | | | Mir7074 |
| 21894 | 3 | | | | Mir7075 |
| 21895 | 3 | | | | Mir7076 |
| 21896 | 3 | | | | Mir7077 |
| 21897 | 3 | | | | Mir7078 |
| 21898 | 3 | | | | Mir7079 |
| 21899 | 3 | | | | Mir708 |
| 21900 | 3 | | | | Mir7080 |
| 21901 | 3 | | | | Mir7081 |
| 21902 | 3 | | | | Mir7082 |
| 21903 | 3 | | | | Mir7083 |
| 21904 | 3 | | | | Mir7084 |
| 21905 | 3 | | | | Mir7085 |
| 21906 | 3 | | | | Mir7086 |
| 21907 | 3 | | | | Mir7087 |
| 21908 | 3 | | | | Mir7088 |
| 21909 | 3 | | | | Mir7089 |
| 21910 | 3 | | | | Mir709 |
| 21911 | 3 | | | | Mir7090 |
| 21912 | 3 | | | | Mir7091 |
| 21913 | 3 | | | | Mir7092 |
| 21914 | 3 | | | | Mir7093 |
| 21915 | 3 | | | | Mir7094-1 |
| 21916 | 3 | | | | Mir7094-2 |
| 21917 | 3 | | | | Mir710 |
| 21918 | 3 | | | | Mir711 |
| 21919 | 3 | | | | Mir7115 |
| 21920 | 3 | | | | Mir7117 |
| 21921 | 3 | | | | Mir7118 |
| 21922 | 3 | | | | Mir7119 |
| 21923 | 3 | | | | Mir713 |
| 21924 | 3 | | | | Mir717 |
| 21925 | 3 | | | | Mir718 |
| 21926 | 3 | | | | Mir721 |
| 21927 | 3 | | | | Mir7210 |
| 21928 | 3 | | | | Mir7211 |
| 21929 | 3 | | | | Mir7212 |
| 21930 | 3 | | | | Mir7213 |
| 21931 | 3 | | | | Mir7214 |
| 21932 | 3 | | | | Mir7215 |
| 21933 | 3 | | | | Mir7216 |
| 21934 | 3 | | | | Mir7217 |
| 21935 | 3 | | | | Mir7218 |
| 21936 | 3 | | | | Mir7219 |
| 21937 | 3 | | | | Mir7220 |
| 21938 | 3 | | | | Mir7221 |
| 21939 | 3 | | | | Mir7222 |
| 21940 | 3 | | | | Mir7223 |
| 21941 | 3 | | | | Mir7224 |
| 21942 | 3 | | | | Mir7225 |
| 21943 | 3 | | | | Mir7226 |
| 21944 | 3 | | | | Mir7227 |
| 21945 | 3 | | | | Mir7228 |
| 21946 | 3 | | | | Mir7229 |
| 21947 | 3 | | | | Mir7230 |
| 21948 | 3 | | | | Mir7231 |
| 21949 | 3 | | | | Mir7232 |
| 21950 | 3 | | | | Mir7233 |
| 21951 | 3 | | | | Mir7234 |
| 21952 | 3 | | | | Mir7235 |
| 21953 | 3 | | | | Mir7236 |
| 21954 | 3 | | | | Mir7237 |
| 21955 | 3 | | | | Mir7238 |
| 21956 | 3 | | | | Mir7239 |
| 21957 | 3 | | | | Mir7240 |
| 21958 | 3 | | | | Mir7241 |
| 21959 | 3 | | | | Mir7242 |
| 21960 | 3 | | | | Mir7243 |
| 21961 | 3 | | | | Mir741 |
| 21962 | 3 | | | | Mir742 |
| 21963 | 3 | | | | Mir743 |
| 21964 | 3 | | | | Mir743b |
| 21965 | 3 | | | | Mir744 |
| 21966 | 3 | | | | Mir7578 |
| 21967 | 3 | | | | Mir758 |
| 21968 | 3 | | | | Mir759 |
| 21969 | 3 | | | | Mir761 |
| 21970 | 3 | | | | Mir762 |
| 21971 | 3 | | | | Mir764 |
| 21972 | 3 | | | | Mir7646 |
| 21973 | 3 | | | | Mir7647 |
| 21974 | 3 | | | | Mir7648 |
| 21975 | 3 | | | | Mir7649 |
| 21976 | 3 | | | | Mir7650 |
| 21977 | 3 | | | | Mir7652 |
| 21978 | 3 | | | | Mir7653 |
| 21979 | 3 | | | | Mir7654 |
| 21980 | 3 | | | | Mir7655 |
| 21981 | 3 | | | | Mir7656 |
| 21982 | 3 | | | | Mir7657 |
| 21983 | 3 | | | | Mir7658 |
| 21984 | 3 | | | | Mir7661 |
| 21985 | 3 | | | | Mir7662 |
| 21986 | 3 | | | | Mir7663 |
| 21987 | 3 | | | | Mir7665 |
| 21988 | 3 | | | | Mir7666 |
| 21989 | 3 | | | | Mir7667 |
| 21990 | 3 | | | | Mir7668 |
| 21991 | 3 | | | | Mir7669 |
| 21992 | 3 | | | | Mir767 |
| 21993 | 3 | | | | Mir7670 |
| 21994 | 3 | | | | Mir7671 |
| 21995 | 3 | | | | Mir7672 |
| 21996 | 3 | | | | Mir7673 |
| 21997 | 3 | | | | Mir7674 |
| 21998 | 3 | | | | Mir7675 |
| 21999 | 3 | | | | Mir7676-2 |
| 22000 | 3 | | | | Mir7677 |
| 22001 | 3 | | | | Mir7678 |
| 22002 | 3 | | | | Mir7679 |
| 22003 | 3 | | | | Mir7680 |
| 22004 | 3 | | | | Mir7681 |
| 22005 | 3 | | | | Mir7682 |
| 22006 | 3 | | | | Mir7684 |
| 22007 | 3 | | | | Mir7685 |
| 22008 | 3 | | | | Mir7686 |
| 22009 | 3 | | | | Mir7687 |
| 22010 | 3 | | | | Mir770 |
| 22011 | 3 | | | | Mir7b |
| 22012 | 3 | | | | Mir802 |
| 22013 | 3 | | | | Mir804 |
| 22014 | 3 | | | | Mir8092 |
| 22015 | 3 | | | | Mir8095 |
| 22016 | 3 | | | | Mir8100 |
| 22017 | 3 | | | | Mir8101 |
| 22018 | 3 | | | | Mir8105 |
| 22019 | 3 | | | | Mir8106 |
| 22020 | 3 | | | | Mir8107 |
| 22021 | 3 | | | | Mir8108 |
| 22022 | 3 | | | | Mir8109 |
| 22023 | 3 | | | | Mir8110 |
| 22024 | 3 | | | | Mir8111 |
| 22025 | 3 | | | | Mir8115 |
| 22026 | 3 | | | | Mir8116 |
| 22027 | 3 | | | | Mir8119 |
| 22028 | 3 | | | | Mir8120 |
| 22029 | 3 | | | | Mir871 |
| 22030 | 3 | | | | Mir872 |
| 22031 | 3 | | | | Mir873b |
| 22032 | 3 | | | | Mir874 |
| 22033 | 3 | | | | Mir875 |
| 22034 | 3 | | | | Mir876 |
| 22035 | 3 | | | | Mir877 |
| 22036 | 3 | | | | Mir878 |
| 22037 | 3 | | | | Mir879 |
| 22038 | 3 | | | | Mir880 |
| 22039 | 3 | | | | Mir881 |
| 22040 | 3 | | | | Mir882 |
| 22041 | 3 | | | | Mir883a |
| 22042 | 3 | | | | Mir883b |
| 22043 | 3 | | | | Mir9-1 |
| 22044 | 3 | | | | Mir9-2 |
| 22045 | 3 | | | | Mir9-3 |
| 22046 | 3 | | | | Mir92-1 |
| 22047 | 3 | | | | Mir92-2 |
| 22048 | 3 | | | | Mir92b |
| 22049 | 3 | | | | Mir93 |
| 22050 | 3 | | | | Mir98 |
| 22051 | 3 | | | | Mir99a |
| 22052 | 3 | | | | Mir99b |
| 22053 | 3 | | | | Mirlet7a-1 |
| 22054 | 3 | | | | Mirlet7a-2 |
| 22055 | 3 | | | | Mirlet7b |
| 22056 | 3 | | | | Mirlet7c-1 |
| 22057 | 3 | | | | Mirlet7c-2 |
| 22058 | 3 | | | | Mirlet7e |
| 22059 | 3 | | | | Mirlet7f-1 |
| 22060 | 3 | | | | Mirlet7f-2 |
| 22061 | 3 | | | | Mirlet7g |
| 22062 | 3 | | | | Mirlet7i |
| 22063 | 3 | | | | Mirlet7j |
| 22064 | 3 | | | | Mirlet7k |
| 22065 | 3 | | | | Mixl1 |
| 22066 | 3 | | | | Mmp1a |
| 22067 | 3 | | | | Mmp1b |
| 22068 | 3 | | | | Mmp20 |
| 22069 | 3 | | | | Mmp21 |
| 22070 | 3 | | | | Moxd2 |
| 22071 | 3 | | | | Mrgpra1 |
| 22072 | 3 | | | | Mrgpra3 |
| 22073 | 3 | | | | Mrgpra4 |
| 22074 | 3 | | | | Mrgpra6 |
| 22075 | 3 | | | | Mrgpra9 |
| 22076 | 3 | | | | Mrgprb4 |
| 22077 | 3 | | | | Mrgprb5 |
| 22078 | 3 | | | | Mrgprd |

Fig. 36 - 116

| | | | | | | |
|---|---|---|---|---|---|---|
| 22079 | 3 | | | | | Mrgprx1 |
| 22080 | 3 | | | | | Ms4a1 |
| 22081 | 3 | | | | | Ms4a15 |
| 22082 | 3 | | | | | Msgn1 |
| 22083 | 3 | | | | | Mslnl |
| 22084 | 3 | | | | | Msmb |
| 22085 | 3 | | | | | Msx3 |
| 22086 | 3 | | | | | Mtnr1b |
| 22087 | 3 | | | | | Muc19 |
| 22088 | 3 | | | | | Mup4 |
| 22089 | 3 | | | | | Mup6 |
| 22090 | 3 | | | | | Mvcs |
| 22091 | 3 | | | | | Myo3a |
| 22092 | 3 | | | | | Myrfl |
| 22093 | 3 | | | | | Naip7 |
| 22094 | 3 | | | | | Nanog |
| 22095 | 3 | | | | | Nat3 |
| 22096 | 3 | | | | | Ndufs5 |
| 22097 | 3 | | | | | Nek10 |
| 22098 | 3 | | | | | Neurod4 |
| 22099 | 3 | | | | | Nkx1-1 |
| 22100 | 3 | | | | | Nkx1-2 |
| 22101 | 3 | | | | | Nkx2-2os |
| 22102 | 3 | | | | | Nkx2-9 |
| 22103 | 3 | | | | | Nlrp1c-ps |
| 22104 | 3 | | | | | Nlrp2 |
| 22105 | 3 | | | | | Nlrp4a |
| 22106 | 3 | | | | | Nlrp4b |
| 22107 | 3 | | | | | Nlrp4e |
| 22108 | 3 | | | | | Nlrp4f |
| 22109 | 3 | | | | | Nlrp4g |
| 22110 | 3 | | | | | Nlrp9a |
| 22111 | 3 | | | | | Nlrp9c |
| 22112 | 3 | | | | | Nms |
| 22113 | 3 | | | | | Nmur2 |
| 22114 | 3 | | | | | Nobox |
| 22115 | 3 | | | | | Nodal |
| 22116 | 3 | | | | | Noto |
| 22117 | 3 | | | | | Nox3 |
| 22118 | 3 | | | | | Npffr2 |
| 22119 | 3 | | | | | Nphs1os |
| 22120 | 3 | | | | | Npy6r |
| 22121 | 3 | | | | | Nrk |
| 22122 | 3 | | | | | Nrl |
| 22123 | 3 | | | | | Nron |
| 22124 | 3 | | | | | Nrp |
| 22125 | 3 | | | | | Nxf7 |
| 22126 | 3 | | | | | Oacyl |
| 22127 | 3 | | | | | Oas1d |
| 22128 | 3 | | | | | Oas1h |
| 22129 | 3 | | | | | Obox1 |
| 22130 | 3 | | | | | Obox2 |
| 22131 | 3 | | | | | Obox3 |
| 22132 | 3 | | | | | Obox5 |
| 22133 | 3 | | | | | Obp1a |
| 22134 | 3 | | | | | Obp2b |
| 22135 | 3 | | | | | Oc90 |
| 22136 | 3 | | | | | Odam |
| 22137 | 3 | | | | | Ofcc1 |
| 22138 | 3 | | | | | Olfr1 |
| 22139 | 3 | | | | | Olfr10 |
| 22140 | 3 | | | | | Olfr100 |
| 22141 | 3 | | | | | Olfr1000 |
| 22142 | 3 | | | | | Olfr1002 |
| 22143 | 3 | | | | | Olfr1006 |
| 22144 | 3 | | | | | Olfr1008 |
| 22145 | 3 | | | | | Olfr1009 |
| 22146 | 3 | | | | | Olfr101 |
| 22147 | 3 | | | | | Olfr1010 |
| 22148 | 3 | | | | | Olfr1012 |
| 22149 | 3 | | | | | Olfr1013 |
| 22150 | 3 | | | | | Olfr1014 |
| 22151 | 3 | | | | | Olfr1015 |
| 22152 | 3 | | | | | Olfr1016 |
| 22153 | 3 | | | | | Olfr1018 |
| 22154 | 3 | | | | | Olfr1019 |
| 22155 | 3 | | | | | Olfr102 |
| 22156 | 3 | | | | | Olfr1020 |
| 22157 | 3 | | | | | Olfr1022 |
| 22158 | 3 | | | | | Olfr1023 |
| 22159 | 3 | | | | | Olfr1024 |
| 22160 | 3 | | | | | Olfr1026 |
| 22161 | 3 | | | | | Olfr1028 |
| 22162 | 3 | | | | | Olfr1029 |
| 22163 | 3 | | | | | Olfr103 |
| 22164 | 3 | | | | | Olfr1030 |
| 22165 | 3 | | | | | Olfr1031 |
| 22166 | 3 | | | | | Olfr1032 |
| 22167 | 3 | | | | | Olfr1033 |
| 22168 | 3 | | | | | Olfr1034 |
| 22169 | 3 | | | | | Olfr1036 |
| 22170 | 3 | | | | | Olfr1037 |
| 22171 | 3 | | | | | Olfr1038-ps |
| 22172 | 3 | | | | | Olfr1039 |
| 22173 | 3 | | | | | Olfr1040 |
| 22174 | 3 | | | | | Olfr1042 |
| 22175 | 3 | | | | | Olfr1043 |
| 22176 | 3 | | | | | Olfr1044 |
| 22177 | 3 | | | | | Olfr1045 |
| 22178 | 3 | | | | | Olfr1046 |
| 22179 | 3 | | | | | Olfr1047 |
| 22180 | 3 | | | | | Olfr1048 |
| 22181 | 3 | | | | | Olfr1049 |
| 22182 | 3 | | | | | Olfr1051 |
| 22183 | 3 | | | | | Olfr1052 |
| 22184 | 3 | | | | | Olfr1053 |
| 22185 | 3 | | | | | Olfr1054 |
| 22186 | 3 | | | | | Olfr1055 |
| 22187 | 3 | | | | | Olfr1056 |
| 22188 | 3 | | | | | Olfr1057 |
| 22189 | 3 | | | | | Olfr1058 |
| 22190 | 3 | | | | | Olfr1061 |
| 22191 | 3 | | | | | Olfr1062 |
| 22192 | 3 | | | | | Olfr1065 |
| 22193 | 3 | | | | | Olfr1066 |
| 22194 | 3 | | | | | Olfr107 |
| 22195 | 3 | | | | | Olfr1076 |
| 22196 | 3 | | | | | Olfr1077-ps1 |
| 22197 | 3 | | | | | Olfr1079 |
| 22198 | 3 | | | | | Olfr108 |
| 22199 | 3 | | | | | Olfr1080 |
| 22200 | 3 | | | | | Olfr1082 |
| 22201 | 3 | | | | | Olfr1084 |
| 22202 | 3 | | | | | Olfr1085 |
| 22203 | 3 | | | | | Olfr1086 |
| 22204 | 3 | | | | | Olfr1087 |
| 22205 | 3 | | | | | Olfr1089 |
| 22206 | 3 | | | | | Olfr109 |
| 22207 | 3 | | | | | Olfr1093 |
| 22208 | 3 | | | | | Olfr1094 |
| 22209 | 3 | | | | | Olfr1095 |
| 22210 | 3 | | | | | Olfr1097 |
| 22211 | 3 | | | | | Olfr1098 |
| 22212 | 3 | | | | | Olfr1099 |
| 22213 | 3 | | | | | Olfr11 |
| 22214 | 3 | | | | | Olfr110 |
| 22215 | 3 | | | | | Olfr1100 |
| 22216 | 3 | | | | | Olfr1101 |
| 22217 | 3 | | | | | Olfr1102 |
| 22218 | 3 | | | | | Olfr1104 |
| 22219 | 3 | | | | | Olfr1105 |
| 22220 | 3 | | | | | Olfr1106 |
| 22221 | 3 | | | | | Olfr1107 |
| 22222 | 3 | | | | | Olfr1109 |
| 22223 | 3 | | | | | Olfr1110 |
| 22224 | 3 | | | | | Olfr1111 |
| 22225 | 3 | | | | | Olfr1112 |
| 22226 | 3 | | | | | Olfr1113 |
| 22227 | 3 | | | | | Olfr1115 |
| 22228 | 3 | | | | | Olfr1116-ps |
| 22229 | 3 | | | | | Olfr1118 |
| 22230 | 3 | | | | | Olfr1120 |
| 22231 | 3 | | | | | Olfr1121 |
| 22232 | 3 | | | | | Olfr1122 |
| 22233 | 3 | | | | | Olfr1123 |
| 22234 | 3 | | | | | Olfr1124 |
| 22235 | 3 | | | | | Olfr1126 |
| 22236 | 3 | | | | | Olfr1128 |
| 22237 | 3 | | | | | Olfr1129 |
| 22238 | 3 | | | | | Olfr113 |
| 22239 | 3 | | | | | Olfr1130 |
| 22240 | 3 | | | | | Olfr1131 |
| 22241 | 3 | | | | | Olfr1132 |
| 22242 | 3 | | | | | Olfr1133 |
| 22243 | 3 | | | | | Olfr1134 |
| 22244 | 3 | | | | | Olfr1135 |
| 22245 | 3 | | | | | Olfr1136 |
| 22246 | 3 | | | | | Olfr1137 |
| 22247 | 3 | | | | | Olfr1138 |
| 22248 | 3 | | | | | Olfr114 |
| 22249 | 3 | | | | | Olfr1140 |
| 22250 | 3 | | | | | Olfr1141 |
| 22251 | 3 | | | | | Olfr1143 |
| 22252 | 3 | | | | | Olfr1145 |
| 22253 | 3 | | | | | Olfr1148 |
| 22254 | 3 | | | | | Olfr115 |
| 22255 | 3 | | | | | Olfr1151 |
| 22256 | 3 | | | | | Olfr1152 |
| 22257 | 3 | | | | | Olfr1153 |
| 22258 | 3 | | | | | Olfr1154 |
| 22259 | 3 | | | | | Olfr1155 |
| 22260 | 3 | | | | | Olfr1156 |
| 22261 | 3 | | | | | Olfr1157 |
| 22262 | 3 | | | | | Olfr1158 |
| 22263 | 3 | | | | | Olfr116 |
| 22264 | 3 | | | | | Olfr1160 |
| 22265 | 3 | | | | | Olfr1161 |
| 22266 | 3 | | | | | Olfr1162 |
| 22267 | 3 | | | | | Olfr1163 |
| 22268 | 3 | | | | | Olfr1164 |
| 22269 | 3 | | | | | Olfr1166 |
| 22270 | 3 | | | | | Olfr1167 |

Fig. 36 - 117

| | | | | | |
|---|---|---|---|---|---|
| 22271 | 3 | | | | Olfr1168 |
| 22272 | 3 | | | | Olfr117 |
| 22273 | 3 | | | | Olfr1170 |
| 22274 | 3 | | | | Olfr1173 |
| 22275 | 3 | | | | Olfr1176 |
| 22276 | 3 | | | | Olfr1178 |
| 22277 | 3 | | | | Olfr1179 |
| 22278 | 3 | | | | Olfr118 |
| 22279 | 3 | | | | Olfr1180 |
| 22280 | 3 | | | | Olfr1181 |
| 22281 | 3 | | | | Olfr1182 |
| 22282 | 3 | | | | Olfr1183 |
| 22283 | 3 | | | | Olfr1184 |
| 22284 | 3 | | | | Olfr1189 |
| 22285 | 3 | | | | Olfr119 |
| 22286 | 3 | | | | Olfr1193 |
| 22287 | 3 | | | | Olfr1195 |
| 22288 | 3 | | | | Olfr1196 |
| 22289 | 3 | | | | Olfr1197 |
| 22290 | 3 | | | | Olfr1198 |
| 22291 | 3 | | | | Olfr1199 |
| 22292 | 3 | | | | Olfr12 |
| 22293 | 3 | | | | Olfr120 |
| 22294 | 3 | | | | Olfr1200 |
| 22295 | 3 | | | | Olfr1201 |
| 22296 | 3 | | | | Olfr1202 |
| 22297 | 3 | | | | Olfr1204 |
| 22298 | 3 | | | | Olfr1205 |
| 22299 | 3 | | | | Olfr1206 |
| 22300 | 3 | | | | Olfr1208 |
| 22301 | 3 | | | | Olfr1209 |
| 22302 | 3 | | | | Olfr121 |
| 22303 | 3 | | | | Olfr1211 |
| 22304 | 3 | | | | Olfr1212 |
| 22305 | 3 | | | | Olfr1213 |
| 22306 | 3 | | | | Olfr1214 |
| 22307 | 3 | | | | Olfr1215 |
| 22308 | 3 | | | | Olfr1216 |
| 22309 | 3 | | | | Olfr1217 |
| 22310 | 3 | | | | Olfr1218 |
| 22311 | 3 | | | | Olfr1219 |
| 22312 | 3 | | | | Olfr122 |
| 22313 | 3 | | | | Olfr1220 |
| 22314 | 3 | | | | Olfr1221 |
| 22315 | 3 | | | | Olfr1222 |
| 22316 | 3 | | | | Olfr1223 |
| 22317 | 3 | | | | Olfr1225 |
| 22318 | 3 | | | | Olfr1226 |
| 22319 | 3 | | | | Olfr1228 |
| 22320 | 3 | | | | Olfr1229 |
| 22321 | 3 | | | | Olfr123 |
| 22322 | 3 | | | | Olfr1230 |
| 22323 | 3 | | | | Olfr1231 |
| 22324 | 3 | | | | Olfr1232 |
| 22325 | 3 | | | | Olfr1233 |
| 22326 | 3 | | | | Olfr1234 |
| 22327 | 3 | | | | Olfr1238 |
| 22328 | 3 | | | | Olfr1239 |
| 22329 | 3 | | | | Olfr124 |
| 22330 | 3 | | | | Olfr1240 |
| 22331 | 3 | | | | Olfr1241 |
| 22332 | 3 | | | | Olfr1242 |
| 22333 | 3 | | | | Olfr1243 |
| 22334 | 3 | | | | Olfr1245 |
| 22335 | 3 | | | | Olfr1246 |
| 22336 | 3 | | | | Olfr1247 |
| 22337 | 3 | | | | Olfr1248 |
| 22338 | 3 | | | | Olfr1249 |
| 22339 | 3 | | | | Olfr125 |
| 22340 | 3 | | | | Olfr1250 |
| 22341 | 3 | | | | Olfr1251 |
| 22342 | 3 | | | | Olfr1252 |
| 22343 | 3 | | | | Olfr1253 |
| 22344 | 3 | | | | Olfr1254 |
| 22345 | 3 | | | | Olfr1255 |
| 22346 | 3 | | | | Olfr1256 |
| 22347 | 3 | | | | Olfr1257 |
| 22348 | 3 | | | | Olfr1258 |
| 22349 | 3 | | | | Olfr1259 |
| 22350 | 3 | | | | Olfr1260 |
| 22351 | 3 | | | | Olfr1261 |
| 22352 | 3 | | | | Olfr1262 |
| 22353 | 3 | | | | Olfr1263 |
| 22354 | 3 | | | | Olfr1264 |
| 22355 | 3 | | | | Olfr1265 |
| 22356 | 3 | | | | Olfr1269 |
| 22357 | 3 | | | | Olfr1270 |
| 22358 | 3 | | | | Olfr1271 |
| 22359 | 3 | | | | Olfr1272 |
| 22360 | 3 | | | | Olfr1273-ps |
| 22361 | 3 | | | | Olfr1274-ps |
| 22362 | 3 | | | | Olfr1275 |
| 22363 | 3 | | | | Olfr1276 |
| 22364 | 3 | | | | Olfr1277 |
| 22365 | 3 | | | | Olfr1278 |
| 22366 | 3 | | | | Olfr1279 |
| 22367 | 3 | | | | Olfr1281 |
| 22368 | 3 | | | | Olfr1282 |
| 22369 | 3 | | | | Olfr1283 |
| 22370 | 3 | | | | Olfr1284 |
| 22371 | 3 | | | | Olfr1286 |
| 22372 | 3 | | | | Olfr1287 |
| 22373 | 3 | | | | Olfr1288 |
| 22374 | 3 | | | | Olfr1289 |
| 22375 | 3 | | | | Olfr129 |
| 22376 | 3 | | | | Olfr1290 |
| 22377 | 3 | | | | Olfr1294 |
| 22378 | 3 | | | | Olfr1295 |
| 22379 | 3 | | | | Olfr1297 |
| 22380 | 3 | | | | Olfr1298 |
| 22381 | 3 | | | | Olfr1299 |
| 22382 | 3 | | | | Olfr130 |
| 22383 | 3 | | | | Olfr1300-ps1 |
| 22384 | 3 | | | | Olfr1301 |
| 22385 | 3 | | | | Olfr1302 |
| 22386 | 3 | | | | Olfr1303 |
| 22387 | 3 | | | | Olfr1305 |
| 22388 | 3 | | | | Olfr1306 |
| 22389 | 3 | | | | Olfr1307 |
| 22390 | 3 | | | | Olfr1308 |
| 22391 | 3 | | | | Olfr1309 |
| 22392 | 3 | | | | Olfr131 |
| 22393 | 3 | | | | Olfr1310 |
| 22394 | 3 | | | | Olfr1311 |
| 22395 | 3 | | | | Olfr1312 |
| 22396 | 3 | | | | Olfr1313 |
| 22397 | 3 | | | | Olfr1314 |
| 22398 | 3 | | | | Olfr1316 |
| 22399 | 3 | | | | Olfr1317 |
| 22400 | 3 | | | | Olfr1318 |
| 22401 | 3 | | | | Olfr132 |
| 22402 | 3 | | | | Olfr1320 |
| 22403 | 3 | | | | Olfr1321 |
| 22404 | 3 | | | | Olfr1322 |
| 22405 | 3 | | | | Olfr1323 |
| 22406 | 3 | | | | Olfr1324 |
| 22407 | 3 | | | | Olfr1325 |
| 22408 | 3 | | | | Olfr1328 |
| 22409 | 3 | | | | Olfr1329 |
| 22410 | 3 | | | | Olfr133 |
| 22411 | 3 | | | | Olfr1330 |
| 22412 | 3 | | | | Olfr1331 |
| 22413 | 3 | | | | Olfr1333 |
| 22414 | 3 | | | | Olfr1335 |
| 22415 | 3 | | | | Olfr1336 |
| 22416 | 3 | | | | Olfr1337 |
| 22417 | 3 | | | | Olfr1338 |
| 22418 | 3 | | | | Olfr1339 |
| 22419 | 3 | | | | Olfr134 |
| 22420 | 3 | | | | Olfr1340 |
| 22421 | 3 | | | | Olfr1341 |
| 22422 | 3 | | | | Olfr1342 |
| 22423 | 3 | | | | Olfr1346 |
| 22424 | 3 | | | | Olfr1347 |
| 22425 | 3 | | | | Olfr1348 |
| 22426 | 3 | | | | Olfr135 |
| 22427 | 3 | | | | Olfr1350 |
| 22428 | 3 | | | | Olfr1351 |
| 22429 | 3 | | | | Olfr1352 |
| 22430 | 3 | | | | Olfr1353 |
| 22431 | 3 | | | | Olfr1354 |
| 22432 | 3 | | | | Olfr1355 |
| 22433 | 3 | | | | Olfr1356 |
| 22434 | 3 | | | | Olfr1357 |
| 22435 | 3 | | | | Olfr1359 |
| 22436 | 3 | | | | Olfr136 |
| 22437 | 3 | | | | Olfr1360 |
| 22438 | 3 | | | | Olfr1361 |
| 22439 | 3 | | | | Olfr1362 |
| 22440 | 3 | | | | Olfr1364 |
| 22441 | 3 | | | | Olfr1366 |
| 22442 | 3 | | | | Olfr1367 |
| 22443 | 3 | | | | Olfr1368 |
| 22444 | 3 | | | | Olfr137 |
| 22445 | 3 | | | | Olfr1370 |
| 22446 | 3 | | | | Olfr1371 |
| 22447 | 3 | | | | Olfr1373 |
| 22448 | 3 | | | | Olfr1377 |
| 22449 | 3 | | | | Olfr1378 |
| 22450 | 3 | | | | Olfr138 |
| 22451 | 3 | | | | Olfr1380 |
| 22452 | 3 | | | | Olfr1381 |
| 22453 | 3 | | | | Olfr1382 |
| 22454 | 3 | | | | Olfr1384 |
| 22455 | 3 | | | | Olfr1385 |
| 22456 | 3 | | | | Olfr1386 |
| 22457 | 3 | | | | Olfr1387 |
| 22458 | 3 | | | | Olfr1388 |
| 22459 | 3 | | | | Olfr1389 |
| 22460 | 3 | | | | Olfr139 |
| 22461 | 3 | | | | Olfr1390 |
| 22462 | 3 | | | | Olfr1391 |

Fig. 36 - 118

| | | | | | |
|---|---|---|---|---|---|
| 22463 | 3 | | | | Olfr1392 |
| 22464 | 3 | | | | Olfr1394 |
| 22465 | 3 | | | | Olfr1395 |
| 22466 | 3 | | | | Olfr140 |
| 22467 | 3 | | | | Olfr1402 |
| 22468 | 3 | | | | Olfr1404 |
| 22469 | 3 | | | | Olfr1406 |
| 22470 | 3 | | | | Olfr1408 |
| 22471 | 3 | | | | Olfr141 |
| 22472 | 3 | | | | Olfr1410 |
| 22473 | 3 | | | | Olfr1411 |
| 22474 | 3 | | | | Olfr1412 |
| 22475 | 3 | | | | Olfr1414 |
| 22476 | 3 | | | | Olfr1415 |
| 22477 | 3 | | | | Olfr1416 |
| 22478 | 3 | | | | Olfr1417 |
| 22479 | 3 | | | | Olfr1418 |
| 22480 | 3 | | | | Olfr1419 |
| 22481 | 3 | | | | Olfr142 |
| 22482 | 3 | | | | Olfr1423 |
| 22483 | 3 | | | | Olfr1424 |
| 22484 | 3 | | | | Olfr1425 |
| 22485 | 3 | | | | Olfr1426 |
| 22486 | 3 | | | | Olfr1427 |
| 22487 | 3 | | | | Olfr1428 |
| 22488 | 3 | | | | Olfr143 |
| 22489 | 3 | | | | Olfr1431 |
| 22490 | 3 | | | | Olfr1433 |
| 22491 | 3 | | | | Olfr1434 |
| 22492 | 3 | | | | Olfr1436 |
| 22493 | 3 | | | | Olfr1437 |
| 22494 | 3 | | | | Olfr1440 |
| 22495 | 3 | | | | Olfr1441 |
| 22496 | 3 | | | | Olfr1442 |
| 22497 | 3 | | | | Olfr1443 |
| 22498 | 3 | | | | Olfr1444 |
| 22499 | 3 | | | | Olfr1445 |
| 22500 | 3 | | | | Olfr1446 |
| 22501 | 3 | | | | Olfr1447 |
| 22502 | 3 | | | | Olfr1448 |
| 22503 | 3 | | | | Olfr1449 |
| 22504 | 3 | | | | Olfr145 |
| 22505 | 3 | | | | Olfr1450 |
| 22506 | 3 | | | | Olfr1451 |
| 22507 | 3 | | | | Olfr1453 |
| 22508 | 3 | | | | Olfr1454 |
| 22509 | 3 | | | | Olfr1457 |
| 22510 | 3 | | | | Olfr1459 |
| 22511 | 3 | | | | Olfr146 |
| 22512 | 3 | | | | Olfr1461 |
| 22513 | 3 | | | | Olfr1462 |
| 22514 | 3 | | | | Olfr1463 |
| 22515 | 3 | | | | Olfr1465 |
| 22516 | 3 | | | | Olfr1466 |
| 22517 | 3 | | | | Olfr1467 |
| 22518 | 3 | | | | Olfr1469 |
| 22519 | 3 | | | | Olfr147 |
| 22520 | 3 | | | | Olfr1471 |
| 22521 | 3 | | | | Olfr1472 |
| 22522 | 3 | | | | Olfr1474 |
| 22523 | 3 | | | | Olfr1475 |
| 22524 | 3 | | | | Olfr1477 |
| 22525 | 3 | | | | Olfr148 |
| 22526 | 3 | | | | Olfr1480 |
| 22527 | 3 | | | | Olfr1484 |
| 22528 | 3 | | | | Olfr1487 |
| 22529 | 3 | | | | Olfr1489 |
| 22530 | 3 | | | | Olfr149 |
| 22531 | 3 | | | | Olfr1490 |
| 22532 | 3 | | | | Olfr1491 |
| 22533 | 3 | | | | Olfr1496 |
| 22534 | 3 | | | | Olfr1497 |
| 22535 | 3 | | | | Olfr1499 |
| 22536 | 3 | | | | Olfr15 |
| 22537 | 3 | | | | Olfr150 |
| 22538 | 3 | | | | Olfr1500 |
| 22539 | 3 | | | | Olfr1501 |
| 22540 | 3 | | | | Olfr1502 |
| 22541 | 3 | | | | Olfr1504 |
| 22542 | 3 | | | | Olfr1505 |
| 22543 | 3 | | | | Olfr1506 |
| 22544 | 3 | | | | Olfr1508 |
| 22545 | 3 | | | | Olfr1509 |
| 22546 | 3 | | | | Olfr151 |
| 22547 | 3 | | | | Olfr1510 |
| 22548 | 3 | | | | Olfr1511 |
| 22549 | 3 | | | | Olfr1512 |
| 22550 | 3 | | | | Olfr1513 |
| 22551 | 3 | | | | Olfr152 |
| 22552 | 3 | | | | Olfr153 |
| 22553 | 3 | | | | Olfr1532-ps1 |
| 22554 | 3 | | | | Olfr1535 |
| 22555 | 3 | | | | Olfr1537 |
| 22556 | 3 | | | | Olfr154 |
| 22557 | 3 | | | | Olfr155 |
| 22558 | 3 | | | | Olfr156 |
| 22559 | 3 | | | | Olfr157 |
| 22560 | 3 | | | | Olfr159 |
| 22561 | 3 | | | | Olfr16 |
| 22562 | 3 | | | | Olfr160 |
| 22563 | 3 | | | | Olfr161 |
| 22564 | 3 | | | | Olfr166 |
| 22565 | 3 | | | | Olfr167 |
| 22566 | 3 | | | | Olfr168 |
| 22567 | 3 | | | | Olfr169 |
| 22568 | 3 | | | | Olfr17 |
| 22569 | 3 | | | | Olfr170 |
| 22570 | 3 | | | | Olfr171 |
| 22571 | 3 | | | | Olfr172 |
| 22572 | 3 | | | | Olfr173 |
| 22573 | 3 | | | | Olfr175-ps1 |
| 22574 | 3 | | | | Olfr176 |
| 22575 | 3 | | | | Olfr177 |
| 22576 | 3 | | | | Olfr178 |
| 22577 | 3 | | | | Olfr18 |
| 22578 | 3 | | | | Olfr180 |
| 22579 | 3 | | | | Olfr181 |
| 22580 | 3 | | | | Olfr183 |
| 22581 | 3 | | | | Olfr186 |
| 22582 | 3 | | | | Olfr187 |
| 22583 | 3 | | | | Olfr190 |
| 22584 | 3 | | | | Olfr191 |
| 22585 | 3 | | | | Olfr192 |
| 22586 | 3 | | | | Olfr193 |
| 22587 | 3 | | | | Olfr195 |
| 22588 | 3 | | | | Olfr196 |
| 22589 | 3 | | | | Olfr197 |
| 22590 | 3 | | | | Olfr198 |
| 22591 | 3 | | | | Olfr2 |
| 22592 | 3 | | | | Olfr201 |
| 22593 | 3 | | | | Olfr202 |
| 22594 | 3 | | | | Olfr203 |
| 22595 | 3 | | | | Olfr204 |
| 22596 | 3 | | | | Olfr205 |
| 22597 | 3 | | | | Olfr206 |
| 22598 | 3 | | | | Olfr209 |
| 22599 | 3 | | | | Olfr211 |
| 22600 | 3 | | | | Olfr213 |
| 22601 | 3 | | | | Olfr214 |
| 22602 | 3 | | | | Olfr218 |
| 22603 | 3 | | | | Olfr220 |
| 22604 | 3 | | | | Olfr221 |
| 22605 | 3 | | | | Olfr222 |
| 22606 | 3 | | | | Olfr223 |
| 22607 | 3 | | | | Olfr224 |
| 22608 | 3 | | | | Olfr225 |
| 22609 | 3 | | | | Olfr228 |
| 22610 | 3 | | | | Olfr229 |
| 22611 | 3 | | | | Olfr231 |
| 22612 | 3 | | | | Olfr235 |
| 22613 | 3 | | | | Olfr237-ps1 |
| 22614 | 3 | | | | Olfr239 |
| 22615 | 3 | | | | Olfr24 |
| 22616 | 3 | | | | Olfr242 |
| 22617 | 3 | | | | Olfr243 |
| 22618 | 3 | | | | Olfr247 |
| 22619 | 3 | | | | Olfr248 |
| 22620 | 3 | | | | Olfr25 |
| 22621 | 3 | | | | Olfr259 |
| 22622 | 3 | | | | Olfr26 |
| 22623 | 3 | | | | Olfr262 |
| 22624 | 3 | | | | Olfr263 |
| 22625 | 3 | | | | Olfr266 |
| 22626 | 3 | | | | Olfr267 |
| 22627 | 3 | | | | Olfr270 |
| 22628 | 3 | | | | Olfr272 |
| 22629 | 3 | | | | Olfr273 |
| 22630 | 3 | | | | Olfr275 |
| 22631 | 3 | | | | Olfr279 |
| 22632 | 3 | | | | Olfr281 |
| 22633 | 3 | | | | Olfr282 |
| 22634 | 3 | | | | Olfr283 |
| 22635 | 3 | | | | Olfr284 |
| 22636 | 3 | | | | Olfr285 |
| 22637 | 3 | | | | Olfr286 |
| 22638 | 3 | | | | Olfr290 |
| 22639 | 3 | | | | Olfr291 |
| 22640 | 3 | | | | Olfr292 |
| 22641 | 3 | | | | Olfr293 |
| 22642 | 3 | | | | Olfr294 |
| 22643 | 3 | | | | Olfr295 |
| 22644 | 3 | | | | Olfr297 |
| 22645 | 3 | | | | Olfr298 |
| 22646 | 3 | | | | Olfr299 |
| 22647 | 3 | | | | Olfr3 |
| 22648 | 3 | | | | Olfr301 |
| 22649 | 3 | | | | Olfr304 |
| 22650 | 3 | | | | Olfr305 |
| 22651 | 3 | | | | Olfr307 |
| 22652 | 3 | | | | Olfr309 |
| 22653 | 3 | | | | Olfr310 |
| 22654 | 3 | | | | Olfr311 |

Fig. 36 - 119

| | | | | | |
|---|---|---|---|---|---|
| 22655 | 3 | | | | Olfr312 |
| 22656 | 3 | | | | Olfr313 |
| 22657 | 3 | | | | Olfr314 |
| 22658 | 3 | | | | Olfr315 |
| 22659 | 3 | | | | Olfr316 |
| 22660 | 3 | | | | Olfr317 |
| 22661 | 3 | | | | Olfr318 |
| 22662 | 3 | | | | Olfr319 |
| 22663 | 3 | | | | Olfr32 |
| 22664 | 3 | | | | Olfr320 |
| 22665 | 3 | | | | Olfr322 |
| 22666 | 3 | | | | Olfr323 |
| 22667 | 3 | | | | Olfr324 |
| 22668 | 3 | | | | Olfr328 |
| 22669 | 3 | | | | Olfr329-ps |
| 22670 | 3 | | | | Olfr33 |
| 22671 | 3 | | | | Olfr330 |
| 22672 | 3 | | | | Olfr331 |
| 22673 | 3 | | | | Olfr332 |
| 22674 | 3 | | | | Olfr338 |
| 22675 | 3 | | | | Olfr339 |
| 22676 | 3 | | | | Olfr340 |
| 22677 | 3 | | | | Olfr341 |
| 22678 | 3 | | | | Olfr342 |
| 22679 | 3 | | | | Olfr344 |
| 22680 | 3 | | | | Olfr345 |
| 22681 | 3 | | | | Olfr346 |
| 22682 | 3 | | | | Olfr347 |
| 22683 | 3 | | | | Olfr348 |
| 22684 | 3 | | | | Olfr350 |
| 22685 | 3 | | | | Olfr351 |
| 22686 | 3 | | | | Olfr352 |
| 22687 | 3 | | | | Olfr353 |
| 22688 | 3 | | | | Olfr354 |
| 22689 | 3 | | | | Olfr355 |
| 22690 | 3 | | | | Olfr356 |
| 22691 | 3 | | | | Olfr358 |
| 22692 | 3 | | | | Olfr361 |
| 22693 | 3 | | | | Olfr362 |
| 22694 | 3 | | | | Olfr365 |
| 22695 | 3 | | | | Olfr366 |
| 22696 | 3 | | | | Olfr367-ps |
| 22697 | 3 | | | | Olfr368 |
| 22698 | 3 | | | | Olfr370 |
| 22699 | 3 | | | | Olfr371 |
| 22700 | 3 | | | | Olfr372 |
| 22701 | 3 | | | | Olfr373 |
| 22702 | 3 | | | | Olfr374 |
| 22703 | 3 | | | | Olfr376 |
| 22704 | 3 | | | | Olfr378 |
| 22705 | 3 | | | | Olfr38 |
| 22706 | 3 | | | | Olfr380 |
| 22707 | 3 | | | | Olfr381 |
| 22708 | 3 | | | | Olfr382 |
| 22709 | 3 | | | | Olfr384 |
| 22710 | 3 | | | | Olfr385 |
| 22711 | 3 | | | | Olfr389 |
| 22712 | 3 | | | | Olfr39 |
| 22713 | 3 | | | | Olfr390 |
| 22714 | 3 | | | | Olfr391-ps |
| 22715 | 3 | | | | Olfr392 |
| 22716 | 3 | | | | Olfr393 |
| 22717 | 3 | | | | Olfr394 |
| 22718 | 3 | | | | Olfr395 |
| 22719 | 3 | | | | Olfr397 |
| 22720 | 3 | | | | Olfr398 |
| 22721 | 3 | | | | Olfr399 |
| 22722 | 3 | | | | Olfr401 |
| 22723 | 3 | | | | Olfr402 |
| 22724 | 3 | | | | Olfr403 |
| 22725 | 3 | | | | Olfr406 |
| 22726 | 3 | | | | Olfr410 |
| 22727 | 3 | | | | Olfr411 |
| 22728 | 3 | | | | Olfr412 |
| 22729 | 3 | | | | Olfr414 |
| 22730 | 3 | | | | Olfr417 |
| 22731 | 3 | | | | Olfr418-ps1 |
| 22732 | 3 | | | | Olfr420 |
| 22733 | 3 | | | | Olfr421-ps1 |
| 22734 | 3 | | | | Olfr424 |
| 22735 | 3 | | | | Olfr426 |
| 22736 | 3 | | | | Olfr427 |
| 22737 | 3 | | | | Olfr429 |
| 22738 | 3 | | | | Olfr43 |
| 22739 | 3 | | | | Olfr430 |
| 22740 | 3 | | | | Olfr434 |
| 22741 | 3 | | | | Olfr435 |
| 22742 | 3 | | | | Olfr437 |
| 22743 | 3 | | | | Olfr44 |
| 22744 | 3 | | | | Olfr441 |
| 22745 | 3 | | | | Olfr444 |
| 22746 | 3 | | | | Olfr446 |
| 22747 | 3 | | | | Olfr447 |
| 22748 | 3 | | | | Olfr448 |
| 22749 | 3 | | | | Olfr449 |
| 22750 | 3 | | | | Olfr45 |
| 22751 | 3 | | | | Olfr450 |
| 22752 | 3 | | | | Olfr452 |
| 22753 | 3 | | | | Olfr453 |
| 22754 | 3 | | | | Olfr455 |
| 22755 | 3 | | | | Olfr456 |
| 22756 | 3 | | | | Olfr457 |
| 22757 | 3 | | | | Olfr458 |
| 22758 | 3 | | | | Olfr459 |
| 22759 | 3 | | | | Olfr46 |
| 22760 | 3 | | | | Olfr460 |
| 22761 | 3 | | | | Olfr461 |
| 22762 | 3 | | | | Olfr462 |
| 22763 | 3 | | | | Olfr463 |
| 22764 | 3 | | | | Olfr464 |
| 22765 | 3 | | | | Olfr466 |
| 22766 | 3 | | | | Olfr467 |
| 22767 | 3 | | | | Olfr469 |
| 22768 | 3 | | | | Olfr47 |
| 22769 | 3 | | | | Olfr470 |
| 22770 | 3 | | | | Olfr472 |
| 22771 | 3 | | | | Olfr473 |
| 22772 | 3 | | | | Olfr474 |
| 22773 | 3 | | | | Olfr476 |
| 22774 | 3 | | | | Olfr477 |
| 22775 | 3 | | | | Olfr478 |
| 22776 | 3 | | | | Olfr479 |
| 22777 | 3 | | | | Olfr48 |
| 22778 | 3 | | | | Olfr480 |
| 22779 | 3 | | | | Olfr481 |
| 22780 | 3 | | | | Olfr482 |
| 22781 | 3 | | | | Olfr483 |
| 22782 | 3 | | | | Olfr484 |
| 22783 | 3 | | | | Olfr485 |
| 22784 | 3 | | | | Olfr486 |
| 22785 | 3 | | | | Olfr487 |
| 22786 | 3 | | | | Olfr488 |
| 22787 | 3 | | | | Olfr49 |
| 22788 | 3 | | | | Olfr490 |
| 22789 | 3 | | | | Olfr491 |
| 22790 | 3 | | | | Olfr492 |
| 22791 | 3 | | | | Olfr493 |
| 22792 | 3 | | | | Olfr494 |
| 22793 | 3 | | | | Olfr495 |
| 22794 | 3 | | | | Olfr497 |
| 22795 | 3 | | | | Olfr498 |
| 22796 | 3 | | | | Olfr5 |
| 22797 | 3 | | | | Olfr50 |
| 22798 | 3 | | | | Olfr502 |
| 22799 | 3 | | | | Olfr503 |
| 22800 | 3 | | | | Olfr504 |
| 22801 | 3 | | | | Olfr506 |
| 22802 | 3 | | | | Olfr507 |
| 22803 | 3 | | | | Olfr508 |
| 22804 | 3 | | | | Olfr509 |
| 22805 | 3 | | | | Olfr51 |
| 22806 | 3 | | | | Olfr510 |
| 22807 | 3 | | | | Olfr512 |
| 22808 | 3 | | | | Olfr513 |
| 22809 | 3 | | | | Olfr514 |
| 22810 | 3 | | | | Olfr516 |
| 22811 | 3 | | | | Olfr517 |
| 22812 | 3 | | | | Olfr518 |
| 22813 | 3 | | | | Olfr519 |
| 22814 | 3 | | | | Olfr52 |
| 22815 | 3 | | | | Olfr521 |
| 22816 | 3 | | | | Olfr522 |
| 22817 | 3 | | | | Olfr524 |
| 22818 | 3 | | | | Olfr525 |
| 22819 | 3 | | | | Olfr527 |
| 22820 | 3 | | | | Olfr53 |
| 22821 | 3 | | | | Olfr530 |
| 22822 | 3 | | | | Olfr531 |
| 22823 | 3 | | | | Olfr532 |
| 22824 | 3 | | | | Olfr533 |
| 22825 | 3 | | | | Olfr535 |
| 22826 | 3 | | | | Olfr536 |
| 22827 | 3 | | | | Olfr538 |
| 22828 | 3 | | | | Olfr539 |
| 22829 | 3 | | | | Olfr54 |
| 22830 | 3 | | | | Olfr541 |
| 22831 | 3 | | | | Olfr543 |
| 22832 | 3 | | | | Olfr544 |
| 22833 | 3 | | | | Olfr545 |
| 22834 | 3 | | | | Olfr547 |
| 22835 | 3 | | | | Olfr549 |
| 22836 | 3 | | | | Olfr55 |
| 22837 | 3 | | | | Olfr550 |
| 22838 | 3 | | | | Olfr551 |
| 22839 | 3 | | | | Olfr552 |
| 22840 | 3 | | | | Olfr553 |
| 22841 | 3 | | | | Olfr554 |
| 22842 | 3 | | | | Olfr555 |
| 22843 | 3 | | | | Olfr556 |
| 22844 | 3 | | | | Olfr557 |
| 22845 | 3 | | | | Olfr559 |
| 22846 | 3 | | | | Olfr56 |

Fig. 36 - 120

| | | | | | | |
|---|---|---|---|---|---|---|
| 22847 | 3 | | | | | Olfr560 |
| 22848 | 3 | | | | | Olfr561 |
| 22849 | 3 | | | | | Olfr564 |
| 22850 | 3 | | | | | Olfr566 |
| 22851 | 3 | | | | | Olfr568 |
| 22852 | 3 | | | | | Olfr569 |
| 22853 | 3 | | | | | Olfr57 |
| 22854 | 3 | | | | | Olfr570 |
| 22855 | 3 | | | | | Olfr571 |
| 22856 | 3 | | | | | Olfr572 |
| 22857 | 3 | | | | | Olfr574 |
| 22858 | 3 | | | | | Olfr575 |
| 22859 | 3 | | | | | Olfr576 |
| 22860 | 3 | | | | | Olfr577 |
| 22861 | 3 | | | | | Olfr578 |
| 22862 | 3 | | | | | Olfr58 |
| 22863 | 3 | | | | | Olfr582 |
| 22864 | 3 | | | | | Olfr583 |
| 22865 | 3 | | | | | Olfr584 |
| 22866 | 3 | | | | | Olfr585 |
| 22867 | 3 | | | | | Olfr586 |
| 22868 | 3 | | | | | Olfr589 |
| 22869 | 3 | | | | | Olfr59 |
| 22870 | 3 | | | | | Olfr591 |
| 22871 | 3 | | | | | Olfr592 |
| 22872 | 3 | | | | | Olfr593 |
| 22873 | 3 | | | | | Olfr594 |
| 22874 | 3 | | | | | Olfr596 |
| 22875 | 3 | | | | | Olfr597 |
| 22876 | 3 | | | | | Olfr598 |
| 22877 | 3 | | | | | Olfr599 |
| 22878 | 3 | | | | | Olfr6 |
| 22879 | 3 | | | | | Olfr600 |
| 22880 | 3 | | | | | Olfr601 |
| 22881 | 3 | | | | | Olfr603 |
| 22882 | 3 | | | | | Olfr605 |
| 22883 | 3 | | | | | Olfr606 |
| 22884 | 3 | | | | | Olfr608 |
| 22885 | 3 | | | | | Olfr609 |
| 22886 | 3 | | | | | Olfr61 |
| 22887 | 3 | | | | | Olfr610 |
| 22888 | 3 | | | | | Olfr611 |
| 22889 | 3 | | | | | Olfr612 |
| 22890 | 3 | | | | | Olfr613 |
| 22891 | 3 | | | | | Olfr615 |
| 22892 | 3 | | | | | Olfr616 |
| 22893 | 3 | | | | | Olfr617 |
| 22894 | 3 | | | | | Olfr618 |
| 22895 | 3 | | | | | Olfr619 |
| 22896 | 3 | | | | | Olfr62 |
| 22897 | 3 | | | | | Olfr620 |
| 22898 | 3 | | | | | Olfr622 |
| 22899 | 3 | | | | | Olfr623 |
| 22900 | 3 | | | | | Olfr624 |
| 22901 | 3 | | | | | Olfr628 |
| 22902 | 3 | | | | | Olfr629 |
| 22903 | 3 | | | | | Olfr63 |
| 22904 | 3 | | | | | Olfr630 |
| 22905 | 3 | | | | | Olfr631 |
| 22906 | 3 | | | | | Olfr632 |
| 22907 | 3 | | | | | Olfr633 |
| 22908 | 3 | | | | | Olfr635 |
| 22909 | 3 | | | | | Olfr638 |
| 22910 | 3 | | | | | Olfr64 |
| 22911 | 3 | | | | | Olfr640 |
| 22912 | 3 | | | | | Olfr641 |
| 22913 | 3 | | | | | Olfr642 |
| 22914 | 3 | | | | | Olfr643 |
| 22915 | 3 | | | | | Olfr644 |
| 22916 | 3 | | | | | Olfr645 |
| 22917 | 3 | | | | | Olfr646 |
| 22918 | 3 | | | | | Olfr648 |
| 22919 | 3 | | | | | Olfr649 |
| 22920 | 3 | | | | | Olfr65 |
| 22921 | 3 | | | | | Olfr651 |
| 22922 | 3 | | | | | Olfr652 |
| 22923 | 3 | | | | | Olfr653 |
| 22924 | 3 | | | | | Olfr654 |
| 22925 | 3 | | | | | Olfr655 |
| 22926 | 3 | | | | | Olfr656 |
| 22927 | 3 | | | | | Olfr657 |
| 22928 | 3 | | | | | Olfr658 |
| 22929 | 3 | | | | | Olfr659 |
| 22930 | 3 | | | | | Olfr66 |
| 22931 | 3 | | | | | Olfr661 |
| 22932 | 3 | | | | | Olfr663 |
| 22933 | 3 | | | | | Olfr665 |
| 22934 | 3 | | | | | Olfr666 |
| 22935 | 3 | | | | | Olfr667 |
| 22936 | 3 | | | | | Olfr668 |
| 22937 | 3 | | | | | Olfr669 |
| 22938 | 3 | | | | | Olfr67 |
| 22939 | 3 | | | | | Olfr670 |
| 22940 | 3 | | | | | Olfr671 |
| 22941 | 3 | | | | | Olfr672 |
| 22942 | 3 | | | | | Olfr675 |
| 22943 | 3 | | | | | Olfr676 |
| 22944 | 3 | | | | | Olfr677 |
| 22945 | 3 | | | | | Olfr678 |
| 22946 | 3 | | | | | Olfr679 |
| 22947 | 3 | | | | | Olfr68 |
| 22948 | 3 | | | | | Olfr681 |
| 22949 | 3 | | | | | Olfr683 |
| 22950 | 3 | | | | | Olfr684 |
| 22951 | 3 | | | | | Olfr685 |
| 22952 | 3 | | | | | Olfr686 |
| 22953 | 3 | | | | | Olfr688 |
| 22954 | 3 | | | | | Olfr689 |
| 22955 | 3 | | | | | Olfr69 |
| 22956 | 3 | | | | | Olfr690 |
| 22957 | 3 | | | | | Olfr691 |
| 22958 | 3 | | | | | Olfr692 |
| 22959 | 3 | | | | | Olfr693 |
| 22960 | 3 | | | | | Olfr694 |
| 22961 | 3 | | | | | Olfr695 |
| 22962 | 3 | | | | | Olfr697 |
| 22963 | 3 | | | | | Olfr698 |
| 22964 | 3 | | | | | Olfr699 |
| 22965 | 3 | | | | | Olfr70 |
| 22966 | 3 | | | | | Olfr700 |
| 22967 | 3 | | | | | Olfr702 |
| 22968 | 3 | | | | | Olfr703 |
| 22969 | 3 | | | | | Olfr704 |
| 22970 | 3 | | | | | Olfr705 |
| 22971 | 3 | | | | | Olfr706 |
| 22972 | 3 | | | | | Olfr707 |
| 22973 | 3 | | | | | Olfr71 |
| 22974 | 3 | | | | | Olfr710 |
| 22975 | 3 | | | | | Olfr711 |
| 22976 | 3 | | | | | Olfr713 |
| 22977 | 3 | | | | | Olfr714 |
| 22978 | 3 | | | | | Olfr715 |
| 22979 | 3 | | | | | Olfr716 |
| 22980 | 3 | | | | | Olfr720 |
| 22981 | 3 | | | | | Olfr722 |
| 22982 | 3 | | | | | Olfr723 |
| 22983 | 3 | | | | | Olfr724 |
| 22984 | 3 | | | | | Olfr725 |
| 22985 | 3 | | | | | Olfr726 |
| 22986 | 3 | | | | | Olfr727 |
| 22987 | 3 | | | | | Olfr728 |
| 22988 | 3 | | | | | Olfr729 |
| 22989 | 3 | | | | | Olfr73 |
| 22990 | 3 | | | | | Olfr730 |
| 22991 | 3 | | | | | Olfr731 |
| 22992 | 3 | | | | | Olfr734 |
| 22993 | 3 | | | | | Olfr735 |
| 22994 | 3 | | | | | Olfr736 |
| 22995 | 3 | | | | | Olfr738 |
| 22996 | 3 | | | | | Olfr739 |
| 22997 | 3 | | | | | Olfr74 |
| 22998 | 3 | | | | | Olfr740 |
| 22999 | 3 | | | | | Olfr741 |
| 23000 | 3 | | | | | Olfr742 |
| 23001 | 3 | | | | | Olfr743 |
| 23002 | 3 | | | | | Olfr744 |
| 23003 | 3 | | | | | Olfr745 |
| 23004 | 3 | | | | | Olfr746 |
| 23005 | 3 | | | | | Olfr747 |
| 23006 | 3 | | | | | Olfr748 |
| 23007 | 3 | | | | | Olfr749 |
| 23008 | 3 | | | | | Olfr75-ps1 |
| 23009 | 3 | | | | | Olfr76 |
| 23010 | 3 | | | | | Olfr763 |
| 23011 | 3 | | | | | Olfr765 |
| 23012 | 3 | | | | | Olfr767 |
| 23013 | 3 | | | | | Olfr768 |
| 23014 | 3 | | | | | Olfr769 |
| 23015 | 3 | | | | | Olfr77 |
| 23016 | 3 | | | | | Olfr770 |
| 23017 | 3 | | | | | Olfr771 |
| 23018 | 3 | | | | | Olfr772 |
| 23019 | 3 | | | | | Olfr773 |
| 23020 | 3 | | | | | Olfr774 |
| 23021 | 3 | | | | | Olfr775 |
| 23022 | 3 | | | | | Olfr776 |
| 23023 | 3 | | | | | Olfr777 |
| 23024 | 3 | | | | | Olfr780 |
| 23025 | 3 | | | | | Olfr781 |
| 23026 | 3 | | | | | Olfr782 |
| 23027 | 3 | | | | | Olfr784 |
| 23028 | 3 | | | | | Olfr786 |
| 23029 | 3 | | | | | Olfr790 |
| 23030 | 3 | | | | | Olfr791 |
| 23031 | 3 | | | | | Olfr792 |
| 23032 | 3 | | | | | Olfr794 |
| 23033 | 3 | | | | | Olfr796 |
| 23034 | 3 | | | | | Olfr798 |
| 23035 | 3 | | | | | Olfr799 |
| 23036 | 3 | | | | | Olfr8 |
| 23037 | 3 | | | | | Olfr800 |
| 23038 | 3 | | | | | Olfr801 |

Fig. 36 - 121

| | | | | | | |
|---|---|---|---|---|---|---|
| 23039 | 3 | | | | | Olfr802 |
| 23040 | 3 | | | | | Olfr803 |
| 23041 | 3 | | | | | Olfr804 |
| 23042 | 3 | | | | | Olfr805 |
| 23043 | 3 | | | | | Olfr806 |
| 23044 | 3 | | | | | Olfr807 |
| 23045 | 3 | | | | | Olfr808 |
| 23046 | 3 | | | | | Olfr809 |
| 23047 | 3 | | | | | Olfr810 |
| 23048 | 3 | | | | | Olfr811 |
| 23049 | 3 | | | | | Olfr812 |
| 23050 | 3 | | | | | Olfr813 |
| 23051 | 3 | | | | | Olfr814 |
| 23052 | 3 | | | | | Olfr815 |
| 23053 | 3 | | | | | Olfr816 |
| 23054 | 3 | | | | | Olfr818 |
| 23055 | 3 | | | | | Olfr819 |
| 23056 | 3 | | | | | Olfr820 |
| 23057 | 3 | | | | | Olfr821 |
| 23058 | 3 | | | | | Olfr822 |
| 23059 | 3 | | | | | Olfr823 |
| 23060 | 3 | | | | | Olfr824 |
| 23061 | 3 | | | | | Olfr825 |
| 23062 | 3 | | | | | Olfr826 |
| 23063 | 3 | | | | | Olfr827 |
| 23064 | 3 | | | | | Olfr828 |
| 23065 | 3 | | | | | Olfr829 |
| 23066 | 3 | | | | | Olfr830 |
| 23067 | 3 | | | | | Olfr832 |
| 23068 | 3 | | | | | Olfr834 |
| 23069 | 3 | | | | | Olfr835 |
| 23070 | 3 | | | | | Olfr836 |
| 23071 | 3 | | | | | Olfr837 |
| 23072 | 3 | | | | | Olfr843 |
| 23073 | 3 | | | | | Olfr845 |
| 23074 | 3 | | | | | Olfr846 |
| 23075 | 3 | | | | | Olfr847 |
| 23076 | 3 | | | | | Olfr849 |
| 23077 | 3 | | | | | Olfr850 |
| 23078 | 3 | | | | | Olfr851 |
| 23079 | 3 | | | | | Olfr853 |
| 23080 | 3 | | | | | Olfr854 |
| 23081 | 3 | | | | | Olfr855 |
| 23082 | 3 | | | | | Olfr856-ps1 |
| 23083 | 3 | | | | | Olfr857 |
| 23084 | 3 | | | | | Olfr859 |
| 23085 | 3 | | | | | Olfr860 |
| 23086 | 3 | | | | | Olfr862 |
| 23087 | 3 | | | | | Olfr866 |
| 23088 | 3 | | | | | Olfr867 |
| 23089 | 3 | | | | | Olfr868 |
| 23090 | 3 | | | | | Olfr869 |
| 23091 | 3 | | | | | Olfr870 |
| 23092 | 3 | | | | | Olfr871 |
| 23093 | 3 | | | | | Olfr873 |
| 23094 | 3 | | | | | Olfr875 |
| 23095 | 3 | | | | | Olfr876 |
| 23096 | 3 | | | | | Olfr877 |
| 23097 | 3 | | | | | Olfr878 |
| 23098 | 3 | | | | | Olfr881 |
| 23099 | 3 | | | | | Olfr883 |
| 23100 | 3 | | | | | Olfr884 |
| 23101 | 3 | | | | | Olfr885 |
| 23102 | 3 | | | | | Olfr887 |
| 23103 | 3 | | | | | Olfr888 |
| 23104 | 3 | | | | | Olfr889 |
| 23105 | 3 | | | | | Olfr890 |
| 23106 | 3 | | | | | Olfr891 |
| 23107 | 3 | | | | | Olfr893 |
| 23108 | 3 | | | | | Olfr894 |
| 23109 | 3 | | | | | Olfr895 |
| 23110 | 3 | | | | | Olfr898 |
| 23111 | 3 | | | | | Olfr899 |
| 23112 | 3 | | | | | Olfr9 |
| 23113 | 3 | | | | | Olfr90 |
| 23114 | 3 | | | | | Olfr900 |
| 23115 | 3 | | | | | Olfr901 |
| 23116 | 3 | | | | | Olfr902 |
| 23117 | 3 | | | | | Olfr904 |
| 23118 | 3 | | | | | Olfr905 |
| 23119 | 3 | | | | | Olfr906 |
| 23120 | 3 | | | | | Olfr907 |
| 23121 | 3 | | | | | Olfr908 |
| 23122 | 3 | | | | | Olfr91 |
| 23123 | 3 | | | | | Olfr910 |
| 23124 | 3 | | | | | Olfr911-ps1 |
| 23125 | 3 | | | | | Olfr912 |
| 23126 | 3 | | | | | Olfr913 |
| 23127 | 3 | | | | | Olfr914 |
| 23128 | 3 | | | | | Olfr915 |
| 23129 | 3 | | | | | Olfr916 |
| 23130 | 3 | | | | | Olfr917 |
| 23131 | 3 | | | | | Olfr918 |
| 23132 | 3 | | | | | Olfr919 |
| 23133 | 3 | | | | | Olfr92 |
| 23134 | 3 | | | | | Olfr921 |
| 23135 | 3 | | | | | Olfr922 |
| 23136 | 3 | | | | | Olfr923 |
| 23137 | 3 | | | | | Olfr924 |
| 23138 | 3 | | | | | Olfr926 |
| 23139 | 3 | | | | | Olfr93 |
| 23140 | 3 | | | | | Olfr930 |
| 23141 | 3 | | | | | Olfr933 |
| 23142 | 3 | | | | | Olfr934 |
| 23143 | 3 | | | | | Olfr935 |
| 23144 | 3 | | | | | Olfr936 |
| 23145 | 3 | | | | | Olfr937 |
| 23146 | 3 | | | | | Olfr938 |
| 23147 | 3 | | | | | Olfr943 |
| 23148 | 3 | | | | | Olfr944 |
| 23149 | 3 | | | | | Olfr945 |
| 23150 | 3 | | | | | Olfr947-ps1 |
| 23151 | 3 | | | | | Olfr948 |
| 23152 | 3 | | | | | Olfr95 |
| 23153 | 3 | | | | | Olfr951 |
| 23154 | 3 | | | | | Olfr952 |
| 23155 | 3 | | | | | Olfr954 |
| 23156 | 3 | | | | | Olfr955 |
| 23157 | 3 | | | | | Olfr957 |
| 23158 | 3 | | | | | Olfr958 |
| 23159 | 3 | | | | | Olfr959 |
| 23160 | 3 | | | | | Olfr96 |
| 23161 | 3 | | | | | Olfr960 |
| 23162 | 3 | | | | | Olfr961 |
| 23163 | 3 | | | | | Olfr963 |
| 23164 | 3 | | | | | Olfr965 |
| 23165 | 3 | | | | | Olfr967 |
| 23166 | 3 | | | | | Olfr968 |
| 23167 | 3 | | | | | Olfr969 |
| 23168 | 3 | | | | | Olfr97 |
| 23169 | 3 | | | | | Olfr970 |
| 23170 | 3 | | | | | Olfr971 |
| 23171 | 3 | | | | | Olfr972 |
| 23172 | 3 | | | | | Olfr974 |
| 23173 | 3 | | | | | Olfr975 |
| 23174 | 3 | | | | | Olfr976 |
| 23175 | 3 | | | | | Olfr978 |
| 23176 | 3 | | | | | Olfr979 |
| 23177 | 3 | | | | | Olfr98 |
| 23178 | 3 | | | | | Olfr980 |
| 23179 | 3 | | | | | Olfr981 |
| 23180 | 3 | | | | | Olfr982 |
| 23181 | 3 | | | | | Olfr983 |
| 23182 | 3 | | | | | Olfr984 |
| 23183 | 3 | | | | | Olfr985 |
| 23184 | 3 | | | | | Olfr986 |
| 23185 | 3 | | | | | Olfr987 |
| 23186 | 3 | | | | | Olfr988 |
| 23187 | 3 | | | | | Olfr992 |
| 23188 | 3 | | | | | Olfr993 |
| 23189 | 3 | | | | | Olfr995 |
| 23190 | 3 | | | | | Olfr996 |
| 23191 | 3 | | | | | Olfr998 |
| 23192 | 3 | | | | | Omt2a |
| 23193 | 3 | | | | | Omt2b |
| 23194 | 3 | | | | | Ooep |
| 23195 | 3 | | | | | Oog1 |
| 23196 | 3 | | | | | Oog2 |
| 23197 | 3 | | | | | Oog3 |
| 23198 | 3 | | | | | Oog4 |
| 23199 | 3 | | | | | Oosp1 |
| 23200 | 3 | | | | | Oosp3 |
| 23201 | 3 | | | | | Opn1sw |
| 23202 | 3 | | | | | Opn5 |
| 23203 | 3 | | | | | Oprm1 |
| 23204 | 3 | | | | | Otog |
| 23205 | 3 | | | | | Otogl |
| 23206 | 3 | | | | | Otol1 |
| 23207 | 3 | | | | | Otor |
| 23208 | 3 | | | | | Otx2os1 |
| 23209 | 3 | | | | | Ovol3 |
| 23210 | 3 | | | | | Pabpc4l |
| 23211 | 3 | | | | | Pabpc5 |
| 23212 | 3 | | | | | Pabpn1l |
| 23213 | 3 | | | | | Pate2 |
| 23214 | 3 | | | | | Patl2 |
| 23215 | 3 | | | | | Paupar |
| 23216 | 3 | | | | | Pax3 |
| 23217 | 3 | | | | | Pax4 |
| 23218 | 3 | | | | | Pax6os1 |
| 23219 | 3 | | | | | Pax7 |
| 23220 | 3 | | | | | Pbsn |
| 23221 | 3 | | | | | Pcdha4-g |
| 23222 | 3 | | | | | Pcdha8 |
| 23223 | 3 | | | | | Pcsk2os2 |
| 23224 | 3 | | | | | Pdc |
| 23225 | 3 | | | | | Pde11a |
| 23226 | 3 | | | | | Pde6b |
| 23227 | 3 | | | | | Pde6c |
| 23228 | 3 | | | | | Pdxk-ps |
| 23229 | 3 | | | | | Pea15b |
| 23230 | 3 | | | | | Peril |

Fig. 36 - 122

| | | | | | | |
|---|---|---|---|---|---|---|
| 23231 | 3 | | | | | Pfpl |
| 23232 | 3 | | | | | Pglyrp3 |
| 23233 | 3 | | | | | Pgpep1l |
| 23234 | 3 | | | | | Pgr15l |
| 23235 | 3 | | | | | Phxr4 |
| 23236 | 3 | | | | | Pinc |
| 23237 | 3 | | | | | Pip |
| 23238 | 3 | | | | | Pira7 |
| 23239 | 3 | | | | | Piwil4 |
| 23240 | 3 | | | | | Pkd1l2 |
| 23241 | 3 | | | | | Plscr5 |
| 23242 | 3 | | | | | Pou1f1 |
| 23243 | 3 | | | | | Pou4f2 |
| 23244 | 3 | | | | | Pou4f3 |
| 23245 | 3 | | | | | Ppef2 |
| 23246 | 3 | | | | | Ppp1r3fos |
| 23247 | 3 | | | | | Pramef17 |
| 23248 | 3 | | | | | Pramef25 |
| 23249 | 3 | | | | | Pramef6 |
| 23250 | 3 | | | | | Pramel4 |
| 23251 | 3 | | | | | Pramel5 |
| 23252 | 3 | | | | | Pramel6 |
| 23253 | 3 | | | | | Pramel7 |
| 23254 | 3 | | | | | Prb1 |
| 23255 | 3 | | | | | Prdm12 |
| 23256 | 3 | | | | | Prdm13 |
| 23257 | 3 | | | | | Prh1 |
| 23258 | 3 | | | | | Prl |
| 23259 | 3 | | | | | Prl2a1 |
| 23260 | 3 | | | | | Prl2b1 |
| 23261 | 3 | | | | | Prl2c1 |
| 23262 | 3 | | | | | Prl2c2 |
| 23263 | 3 | | | | | Prl2c3 |
| 23264 | 3 | | | | | Prl2c4 |
| 23265 | 3 | | | | | Prl2c5 |
| 23266 | 3 | | | | | Prl3a1 |
| 23267 | 3 | | | | | Prl3b1 |
| 23268 | 3 | | | | | Prl3d1 |
| 23269 | 3 | | | | | Prl3d2 |
| 23270 | 3 | | | | | Prl3d3 |
| 23271 | 3 | | | | | Prl4a1 |
| 23272 | 3 | | | | | Prl5a1 |
| 23273 | 3 | | | | | Prl6a1 |
| 23274 | 3 | | | | | Prl7a1 |
| 23275 | 3 | | | | | Prl7a2 |
| 23276 | 3 | | | | | Prl7b1 |
| 23277 | 3 | | | | | Prl7c1 |
| 23278 | 3 | | | | | Prl7d1 |
| 23279 | 3 | | | | | Prl8a1 |
| 23280 | 3 | | | | | Prl8a2 |
| 23281 | 3 | | | | | Prl8a6 |
| 23282 | 3 | | | | | Prl8a8 |
| 23283 | 3 | | | | | Prl8a9 |
| 23284 | 3 | | | | | Prlh |
| 23285 | 3 | | | | | Prlhr |
| 23286 | 3 | | | | | Prn |
| 23287 | 3 | | | | | Prokr2 |
| 23288 | 3 | | | | | Prol1 |
| 23289 | 3 | | | | | Prop1 |
| 23290 | 3 | | | | | Prp2 |
| 23291 | 3 | | | | | Prpmp5 |
| 23292 | 3 | | | | | Prrxl1 |
| 23293 | 3 | | | | | Prss28 |
| 23294 | 3 | | | | | Prss33 |
| 23295 | 3 | | | | | Prtg |
| 23296 | 3 | | | | | Psg-ps1 |
| 23297 | 3 | | | | | Psg17 |
| 23298 | 3 | | | | | Psg18 |
| 23299 | 3 | | | | | Psg20 |
| 23300 | 3 | | | | | Psg21 |
| 23301 | 3 | | | | | Psg22 |
| 23302 | 3 | | | | | Psg23 |
| 23303 | 3 | | | | | Psg25 |
| 23304 | 3 | | | | | Psg26 |
| 23305 | 3 | | | | | Psg27 |
| 23306 | 3 | | | | | Psg28 |
| 23307 | 3 | | | | | Psmb11 |
| 23308 | 3 | | | | | Ptcra |
| 23309 | 3 | | | | | Ptgs2os |
| 23310 | 3 | | | | | Pth |
| 23311 | 3 | | | | | Ptprtos |
| 23312 | 3 | | | | | Ptx4 |
| 23313 | 3 | | | | | Pydc4 |
| 23314 | 3 | | | | | Qrfp |
| 23315 | 3 | | | | | Rab11fip4os1 |
| 23316 | 3 | | | | | Rad21l |
| 23317 | 3 | | | | | Raet1a |
| 23318 | 3 | | | | | Raver1-fdx1l |
| 23319 | 3 | | | | | Rax |
| 23320 | 3 | | | | | Rbmy |
| 23321 | 3 | | | | | Rbp3 |
| 23322 | 3 | | | | | Rcvrn |
| 23323 | 3 | | | | | Rdh8 |
| 23324 | 3 | | | | | Rfpl4 |
| 23325 | 3 | | | | | Rfpl4b |
| 23326 | 3 | | | | | Rgr |
| 23327 | 3 | | | | | Rgs21 |
| 23328 | 3 | | | | | Rhox1 |
| 23329 | 3 | | | | | Rhox12 |
| 23330 | 3 | | | | | Rhox2b |
| 23331 | 3 | | | | | Rhox2c |
| 23332 | 3 | | | | | Rhox2d |
| 23333 | 3 | | | | | Rhox2e |
| 23334 | 3 | | | | | Rhox2f |
| 23335 | 3 | | | | | Rhox2g |
| 23336 | 3 | | | | | Rhox2h |
| 23337 | 3 | | | | | Rhox3a |
| 23338 | 3 | | | | | Rhox4b |
| 23339 | 3 | | | | | Rhox4c |
| 23340 | 3 | | | | | Rhox4d |
| 23341 | 3 | | | | | Rhox4e |
| 23342 | 3 | | | | | Rhox4f |
| 23343 | 3 | | | | | Rhox4g |
| 23344 | 3 | | | | | Rhox6 |
| 23345 | 3 | | | | | Rhox7 |
| 23346 | 3 | | | | | Rhox9 |
| 23347 | 3 | | | | | Rmst |
| 23348 | 3 | | | | | Rnase11 |
| 23349 | 3 | | | | | Rnu12 |
| 23350 | 3 | | | | | Rnu6 |
| 23351 | 3 | | | | | Rnu7 |
| 23352 | 3 | | | | | Rnu73b |
| 23353 | 3 | | | | | Rp1l1 |
| 23354 | 3 | | | | | Rpe65 |
| 23355 | 3 | | | | | Rpi26 |
| 23356 | 3 | | | | | Rpl34-ps1 |
| 23357 | 3 | | | | | Rprl1 |
| 23358 | 3 | | | | | Rprl2 |
| 23359 | 3 | | | | | Rps21 |
| 23360 | 3 | | | | | Rrh |
| 23361 | 3 | | | | | Rs1 |
| 23362 | 3 | | | | | Rsg1 |
| 23363 | 3 | | | | | Rspo4 |
| 23364 | 3 | | | | | Rtp2 |
| 23365 | 3 | | | | | Rxfp4 |
| 23366 | 3 | | | | | S100a2 |
| 23367 | 3 | | | | | Sacs |
| 23368 | 3 | | | | | Sbp |
| 23369 | 3 | | | | | Sbpl |
| 23370 | 3 | | | | | Scarna10 |
| 23371 | 3 | | | | | Scarna17 |
| 23372 | 3 | | | | | Scarna2 |
| 23373 | 3 | | | | | Scarna9 |
| 23374 | 3 | | | | | Scgb1b19 |
| 23375 | 3 | | | | | Scgb1b2 |
| 23376 | 3 | | | | | Scgb1b20 |
| 23377 | 3 | | | | | Scgb1b29 |
| 23378 | 3 | | | | | Scgb1b30 |
| 23379 | 3 | | | | | Scgb1b7 |
| 23380 | 3 | | | | | Scgb2b12 |
| 23381 | 3 | | | | | Scgb2b19 |
| 23382 | 3 | | | | | Scgb2b2 |
| 23383 | 3 | | | | | Scgb2b24 |
| 23384 | 3 | | | | | Scgb2b26 |
| 23385 | 3 | | | | | Scgb2b3 |
| 23386 | 3 | | | | | Scn10a |
| 23387 | 3 | | | | | Scn11a |
| 23388 | 3 | | | | | Sele |
| 23389 | 3 | | | | | Serpinb3d |
| 23390 | 3 | | | | | Serpinb6e |
| 23391 | 3 | | | | | Serpinb9c |
| 23392 | 3 | | | | | Serpinb9d |
| 23393 | 3 | | | | | Serpinb9e |
| 23394 | 3 | | | | | Serpinb9f |
| 23395 | 3 | | | | | Serpinb9g |
| 23396 | 3 | | | | | Siglec15 |
| 23397 | 3 | | | | | Sis |
| 23398 | 3 | | | | | Six6 |
| 23399 | 3 | | | | | Skint3 |
| 23400 | 3 | | | | | Skint4 |
| 23401 | 3 | | | | | Skint7 |
| 23402 | 3 | | | | | Skint9 |
| 23403 | 3 | | | | | Slain1os |
| 23404 | 3 | | | | | Slc1a7 |
| 23405 | 3 | | | | | Slc22a27 |
| 23406 | 3 | | | | | Slc24a1 |
| 23407 | 3 | | | | | Slc26a5 |
| 23408 | 3 | | | | | Slc2a7 |
| 23409 | 3 | | | | | Slc38a11 |
| 23410 | 3 | | | | | Slc38a8 |
| 23411 | 3 | | | | | Slc5a4a |
| 23412 | 3 | | | | | Slco1a5 |
| 23413 | 3 | | | | | Slx |
| 23414 | 3 | | | | | Smgc |
| 23415 | 3 | | | | | Smr2 |
| 23416 | 3 | | | | | Smr3a |
| 23417 | 3 | | | | | Snhg1 |
| 23418 | 3 | | | | | Snora19 |
| 23419 | 3 | | | | | Snora20 |
| 23420 | 3 | | | | | Snora26 |
| 23421 | 3 | | | | | Snora35 |
| 23422 | 3 | | | | | Snora47 |

Fig. 36 - 123

| | | | | | | |
|---|---|---|---|---|---|---|
| 23423 | 3 | | | | | Snora61 |
| 23424 | 3 | | | | | Snord100 |
| 23425 | 3 | | | | | Snord104 |
| 23426 | 3 | | | | | Snord11 |
| 23427 | 3 | | | | | Snord110 |
| 23428 | 3 | | | | | Snord111 |
| 23429 | 3 | | | | | Snord116 |
| 23430 | 3 | | | | | Snord116l1 |
| 23431 | 3 | | | | | Snord116l2 |
| 23432 | 3 | | | | | Snord118 |
| 23433 | 3 | | | | | Snord12 |
| 23434 | 3 | | | | | Snord123 |
| 23435 | 3 | | | | | Snord14a |
| 23436 | 3 | | | | | Snord14c |
| 23437 | 3 | | | | | Snord14d |
| 23438 | 3 | | | | | Snord16a |
| 23439 | 3 | | | | | Snord19 |
| 23440 | 3 | | | | | Snord1a |
| 23441 | 3 | | | | | Snord1b |
| 23442 | 3 | | | | | Snord1c |
| 23443 | 3 | | | | | Snord2 |
| 23444 | 3 | | | | | Snord23 |
| 23445 | 3 | | | | | Snord32a |
| 23446 | 3 | | | | | Snord33 |
| 23447 | 3 | | | | | Snord34 |
| 23448 | 3 | | | | | Snord35a |
| 23449 | 3 | | | | | Snord35b |
| 23450 | 3 | | | | | Snord37 |
| 23451 | 3 | | | | | Snord38a |
| 23452 | 3 | | | | | Snord42a |
| 23453 | 3 | | | | | Snord42b |
| 23454 | 3 | | | | | Snord43 |
| 23455 | 3 | | | | | Snord45b |
| 23456 | 3 | | | | | Snord45c |
| 23457 | 3 | | | | | Snord47 |
| 23458 | 3 | | | | | Snord49a |
| 23459 | 3 | | | | | Snord49b |
| 23460 | 3 | | | | | Snord4a |
| 23461 | 3 | | | | | Snord52 |
| 23462 | 3 | | | | | Snord53 |
| 23463 | 3 | | | | | Snord55 |
| 23464 | 3 | | | | | Snord57 |
| 23465 | 3 | | | | | Snord58b |
| 23466 | 3 | | | | | Snord61 |
| 23467 | 3 | | | | | Snord64 |
| 23468 | 3 | | | | | Snord65 |
| 23469 | 3 | | | | | Snord66 |
| 23470 | 3 | | | | | Snord67 |
| 23471 | 3 | | | | | Snord68 |
| 23472 | 3 | | | | | Snord69 |
| 23473 | 3 | | | | | Snord7 |
| 23474 | 3 | | | | | Snord70 |
| 23475 | 3 | | | | | Snord71 |
| 23476 | 3 | | | | | Snord72 |
| 23477 | 3 | | | | | Snord73a |
| 23478 | 3 | | | | | Snord8 |
| 23479 | 3 | | | | | Snord82 |
| 23480 | 3 | | | | | Snord83b |
| 23481 | 3 | | | | | Snord85 |
| 23482 | 3 | | | | | Snord87 |
| 23483 | 3 | | | | | Snord88a |
| 23484 | 3 | | | | | Snord88c |
| 23485 | 3 | | | | | Snord89 |
| 23486 | 3 | | | | | Snord90 |
| 23487 | 3 | | | | | Snord91a |
| 23488 | 3 | | | | | Snord92 |
| 23489 | 3 | | | | | Snord93 |
| 23490 | 3 | | | | | Snord95 |
| 23491 | 3 | | | | | Snord96a |
| 23492 | 3 | | | | | Snord98 |
| 23493 | 3 | | | | | Snord99 |
| 23494 | 3 | | | | | Sorbs2os |
| 23495 | 3 | | | | | Sp7 |
| 23496 | 3 | | | | | Sp8 |
| 23497 | 3 | | | | | Speer8-ps1 |
| 23498 | 3 | | | | | Spin2-ps1 |
| 23499 | 3 | | | | | Spink13 |
| 23500 | 3 | | | | | Spink14 |
| 23501 | 3 | | | | | Spink7 |
| 23502 | 3 | | | | | Spint4 |
| 23503 | 3 | | | | | Spt1 |
| 23504 | 3 | | | | | Sry |
| 23505 | 3 | | | | | Sspo |
| 23506 | 3 | | | | | Ssu2 |
| 23507 | 3 | | | | | Ssx9 |
| 23508 | 3 | | | | | Ssxb10 |
| 23509 | 3 | | | | | Ssxb3 |
| 23510 | 3 | | | | | Ssxb8 |
| 23511 | 3 | | | | | Ssxb9 |
| 23512 | 3 | | | | | Stmn1-rs1 |
| 23513 | 3 | | | | | Strc |
| 23514 | 3 | | | | | Sult1c1 |
| 23515 | 3 | | | | | Sult2a1 |
| 23516 | 3 | | | | | Sult2a2 |
| 23517 | 3 | | | | | Sult2a3 |
| 23518 | 3 | | | | | Sult2a4 |
| 23519 | 3 | | | | | Sult2a5 |
| 23520 | 3 | | | | | Sult2a6 |
| 23521 | 3 | | | | | Sult2a7 |
| 23522 | 3 | | | | | Sult3a1 |
| 23523 | 3 | | | | | Sult6b1 |
| 23524 | 3 | | | | | Sval2 |
| 23525 | 3 | | | | | Sval3 |
| 23526 | 3 | | | | | Synb |
| 23527 | 3 | | | | | T |
| 23528 | 3 | | | | | Taar1 |
| 23529 | 3 | | | | | Taar2 |
| 23530 | 3 | | | | | Taar3 |
| 23531 | 3 | | | | | Taar4 |
| 23532 | 3 | | | | | Taar5 |
| 23533 | 3 | | | | | Taar6 |
| 23534 | 3 | | | | | Taar7a |
| 23535 | 3 | | | | | Taar7b |
| 23536 | 3 | | | | | Taar7d |
| 23537 | 3 | | | | | Taar7e |
| 23538 | 3 | | | | | Taar7f |
| 23539 | 3 | | | | | Taar8a |
| 23540 | 3 | | | | | Taar8b |
| 23541 | 3 | | | | | Taar8c |
| 23542 | 3 | | | | | Taar9 |
| 23543 | 3 | | | | | Tas1r2 |
| 23544 | 3 | | | | | Tas2r102 |
| 23545 | 3 | | | | | Tas2r103 |
| 23546 | 3 | | | | | Tas2r104 |
| 23547 | 3 | | | | | Tas2r105 |
| 23548 | 3 | | | | | Tas2r106 |
| 23549 | 3 | | | | | Tas2r107 |
| 23550 | 3 | | | | | Tas2r108 |
| 23551 | 3 | | | | | Tas2r109 |
| 23552 | 3 | | | | | Tas2r110 |
| 23553 | 3 | | | | | Tas2r113 |
| 23554 | 3 | | | | | Tas2r114 |
| 23555 | 3 | | | | | Tas2r115 |
| 23556 | 3 | | | | | Tas2r116 |
| 23557 | 3 | | | | | Tas2r117 |
| 23558 | 3 | | | | | Tas2r118 |
| 23559 | 3 | | | | | Tas2r119 |
| 23560 | 3 | | | | | Tas2r120 |
| 23561 | 3 | | | | | Tas2r121 |
| 23562 | 3 | | | | | Tas2r122 |
| 23563 | 3 | | | | | Tas2r123 |
| 23564 | 3 | | | | | Tas2r124 |
| 23565 | 3 | | | | | Tas2r125 |
| 23566 | 3 | | | | | Tas2r126 |
| 23567 | 3 | | | | | Tas2r129 |
| 23568 | 3 | | | | | Tas2r130 |
| 23569 | 3 | | | | | Tas2r131 |
| 23570 | 3 | | | | | Tas2r134 |
| 23571 | 3 | | | | | Tas2r135 |
| 23572 | 3 | | | | | Tas2r136 |
| 23573 | 3 | | | | | Tas2r137 |
| 23574 | 3 | | | | | Tas2r138 |
| 23575 | 3 | | | | | Tas2r139 |
| 23576 | 3 | | | | | Tas2r140 |
| 23577 | 3 | | | | | Tas2r143 |
| 23578 | 3 | | | | | Tas2r144 |
| 23579 | 3 | | | | | Tbc1d22bos |
| 23580 | 3 | | | | | Tbpl2 |
| 23581 | 3 | | | | | Tbrg3 |
| 23582 | 3 | | | | | Tbx3os2 |
| 23583 | 3 | | | | | Tcl1 |
| 23584 | 3 | | | | | Tcl1b1 |
| 23585 | 3 | | | | | Tcl1b2 |
| 23586 | 3 | | | | | Tcl1b3 |
| 23587 | 3 | | | | | Tcl1b4 |
| 23588 | 3 | | | | | Tcl1b5 |
| 23589 | 3 | | | | | Tcstv3 |
| 23590 | 3 | | | | | Tdpoz1 |
| 23591 | 3 | | | | | Tdpoz2 |
| 23592 | 3 | | | | | Tdpoz3 |
| 23593 | 3 | | | | | Tdpoz4 |
| 23594 | 3 | | | | | Tdpoz5 |
| 23595 | 3 | | | | | Tecta |
| 23596 | 3 | | | | | Tfap2d |
| 23597 | 3 | | | | | Themis |
| 23598 | 3 | | | | | Tll2 |
| 23599 | 3 | | | | | Tmc2 |
| 23600 | 3 | | | | | Tmem150cos |
| 23601 | 3 | | | | | Tmem211 |
| 23602 | 3 | | | | | Tmem8c |
| 23603 | 3 | | | | | Tmem92 |
| 23604 | 3 | | | | | Tmprss11c |
| 23605 | 3 | | | | | Tmprss15 |
| 23606 | 3 | | | | | Tnfrsf17 |
| 23607 | 3 | | | | | Tnfsf12Tnfsf13 |
| 23608 | 3 | | | | | Tnfsf4 |
| 23609 | 3 | | | | | Tpbpa |
| 23610 | 3 | | | | | Tpbpb |
| 23611 | 3 | | | | | Trappc3l |
| 23612 | 3 | | | | | Trat1 |
| 23613 | 3 | | | | | Trcg1 |
| 23614 | 3 | | | | | Trim12a |

Fig. 36 - 124

| | | | | | | |
|---|---|---|---|---|---|---|
| 23615 | 3 | | | | | Trim30e-ps1 |
| 23616 | 3 | | | | | Trim43a |
| 23617 | 3 | | | | | Trim60 |
| 23618 | 3 | | | | | Trim61 |
| 23619 | 3 | | | | | Trim75 |
| 23620 | 3 | | | | | Triml2 |
| 23621 | 3 | | | | | Trp53cor1 |
| 23622 | 3 | | | | | Trpa1 |
| 23623 | 3 | | | | | Trpm5 |
| 23624 | 3 | | | | | Trpv1 |
| 23625 | 3 | | | | | Tsix |
| 23626 | 3 | | | | | Tspan2os |
| 23627 | 3 | | | | | Tspear |
| 23628 | 3 | | | | | Tspy-ps |
| 23629 | 3 | | | | | Ubtfl1 |
| 23630 | 3 | | | | | Uchl1os |
| 23631 | 3 | | | | | Ucn3 |
| 23632 | 3 | | | | | Ugt2a1 |
| 23633 | 3 | | | | | Ugt2a2 |
| 23634 | 3 | | | | | Umodl1 |
| 23635 | 3 | | | | | Usp17la |
| 23636 | 3 | | | | | Usp17lb |
| 23637 | 3 | | | | | Usp17lc |
| 23638 | 3 | | | | | Usp17ld |
| 23639 | 3 | | | | | Usp17le |
| 23640 | 3 | | | | | Uts2b |
| 23641 | 3 | | | | | V1rd18 |
| 23642 | 3 | | | | | V1rd19 |
| 23643 | 3 | | | | | Vax1 |
| 23644 | 3 | | | | | Vgll1 |
| 23645 | 3 | | | | | Vmn1r-ps103 |
| 23646 | 3 | | | | | Vmn1r-ps79 |
| 23647 | 3 | | | | | Vmn1r1 |
| 23648 | 3 | | | | | Vmn1r10 |
| 23649 | 3 | | | | | Vmn1r100 |
| 23650 | 3 | | | | | Vmn1r101 |
| 23651 | 3 | | | | | Vmn1r103 |
| 23652 | 3 | | | | | Vmn1r104 |
| 23653 | 3 | | | | | Vmn1r107 |
| 23654 | 3 | | | | | Vmn1r11 |
| 23655 | 3 | | | | | Vmn1r112 |
| 23656 | 3 | | | | | Vmn1r113 |
| 23657 | 3 | | | | | Vmn1r114 |
| 23658 | 3 | | | | | Vmn1r115 |
| 23659 | 3 | | | | | Vmn1r116 |
| 23660 | 3 | | | | | Vmn1r117 |
| 23661 | 3 | | | | | Vmn1r118 |
| 23662 | 3 | | | | | Vmn1r119 |
| 23663 | 3 | | | | | Vmn1r12 |
| 23664 | 3 | | | | | Vmn1r120 |
| 23665 | 3 | | | | | Vmn1r121 |
| 23666 | 3 | | | | | Vmn1r122 |
| 23667 | 3 | | | | | Vmn1r123 |
| 23668 | 3 | | | | | Vmn1r124 |
| 23669 | 3 | | | | | Vmn1r125 |
| 23670 | 3 | | | | | Vmn1r126 |
| 23671 | 3 | | | | | Vmn1r127 |
| 23672 | 3 | | | | | Vmn1r128 |
| 23673 | 3 | | | | | Vmn1r129 |
| 23674 | 3 | | | | | Vmn1r13 |
| 23675 | 3 | | | | | Vmn1r130 |
| 23676 | 3 | | | | | Vmn1r132 |
| 23677 | 3 | | | | | Vmn1r135 |
| 23678 | 3 | | | | | Vmn1r137 |
| 23679 | 3 | | | | | Vmn1r138 |
| 23680 | 3 | | | | | Vmn1r139 |
| 23681 | 3 | | | | | Vmn1r14 |
| 23682 | 3 | | | | | Vmn1r142 |
| 23683 | 3 | | | | | Vmn1r148 |
| 23684 | 3 | | | | | Vmn1r15 |
| 23685 | 3 | | | | | Vmn1r151 |
| 23686 | 3 | | | | | Vmn1r152 |
| 23687 | 3 | | | | | Vmn1r157 |
| 23688 | 3 | | | | | Vmn1r158 |
| 23689 | 3 | | | | | Vmn1r159 |
| 23690 | 3 | | | | | Vmn1r16 |
| 23691 | 3 | | | | | Vmn1r160 |
| 23692 | 3 | | | | | Vmn1r163 |
| 23693 | 3 | | | | | Vmn1r165 |
| 23694 | 3 | | | | | Vmn1r166 |
| 23695 | 3 | | | | | Vmn1r167 |
| 23696 | 3 | | | | | Vmn1r168 |
| 23697 | 3 | | | | | Vmn1r169 |
| 23698 | 3 | | | | | Vmn1r17 |
| 23699 | 3 | | | | | Vmn1r170 |
| 23700 | 3 | | | | | Vmn1r171 |
| 23701 | 3 | | | | | Vmn1r172 |
| 23702 | 3 | | | | | Vmn1r173 |
| 23703 | 3 | | | | | Vmn1r174 |
| 23704 | 3 | | | | | Vmn1r175 |
| 23705 | 3 | | | | | Vmn1r176 |
| 23706 | 3 | | | | | Vmn1r177 |
| 23707 | 3 | | | | | Vmn1r178 |
| 23708 | 3 | | | | | Vmn1r179 |
| 23709 | 3 | | | | | Vmn1r18 |
| 23710 | 3 | | | | | Vmn1r180 |
| 23711 | 3 | | | | | Vmn1r183 |
| 23712 | 3 | | | | | Vmn1r184 |
| 23713 | 3 | | | | | Vmn1r185 |
| 23714 | 3 | | | | | Vmn1r186 |
| 23715 | 3 | | | | | Vmn1r187 |
| 23716 | 3 | | | | | Vmn1r188 |
| 23717 | 3 | | | | | Vmn1r189 |
| 23718 | 3 | | | | | Vmn1r191 |
| 23719 | 3 | | | | | Vmn1r192 |
| 23720 | 3 | | | | | Vmn1r193 |
| 23721 | 3 | | | | | Vmn1r194 |
| 23722 | 3 | | | | | Vmn1r195 |
| 23723 | 3 | | | | | Vmn1r196 |
| 23724 | 3 | | | | | Vmn1r197 |
| 23725 | 3 | | | | | Vmn1r198 |
| 23726 | 3 | | | | | Vmn1r199 |
| 23727 | 3 | | | | | Vmn1r2 |
| 23728 | 3 | | | | | Vmn1r20 |
| 23729 | 3 | | | | | Vmn1r200 |
| 23730 | 3 | | | | | Vmn1r201 |
| 23731 | 3 | | | | | Vmn1r202 |
| 23732 | 3 | | | | | Vmn1r203 |
| 23733 | 3 | | | | | Vmn1r204 |
| 23734 | 3 | | | | | Vmn1r205 |
| 23735 | 3 | | | | | Vmn1r206 |
| 23736 | 3 | | | | | Vmn1r207-ps |
| 23737 | 3 | | | | | Vmn1r208 |
| 23738 | 3 | | | | | Vmn1r209 |
| 23739 | 3 | | | | | Vmn1r210 |
| 23740 | 3 | | | | | Vmn1r211 |
| 23741 | 3 | | | | | Vmn1r212 |
| 23742 | 3 | | | | | Vmn1r213 |
| 23743 | 3 | | | | | Vmn1r214 |
| 23744 | 3 | | | | | Vmn1r215 |
| 23745 | 3 | | | | | Vmn1r216 |
| 23746 | 3 | | | | | Vmn1r217 |
| 23747 | 3 | | | | | Vmn1r218 |
| 23748 | 3 | | | | | Vmn1r219 |
| 23749 | 3 | | | | | Vmn1r22 |
| 23750 | 3 | | | | | Vmn1r220 |
| 23751 | 3 | | | | | Vmn1r221 |
| 23752 | 3 | | | | | Vmn1r222 |
| 23753 | 3 | | | | | Vmn1r223 |
| 23754 | 3 | | | | | Vmn1r225 |
| 23755 | 3 | | | | | Vmn1r226 |
| 23756 | 3 | | | | | Vmn1r227 |
| 23757 | 3 | | | | | Vmn1r228 |
| 23758 | 3 | | | | | Vmn1r229 |
| 23759 | 3 | | | | | Vmn1r23 |
| 23760 | 3 | | | | | Vmn1r230 |
| 23761 | 3 | | | | | Vmn1r231 |
| 23762 | 3 | | | | | Vmn1r232 |
| 23763 | 3 | | | | | Vmn1r233 |
| 23764 | 3 | | | | | Vmn1r234 |
| 23765 | 3 | | | | | Vmn1r235 |
| 23766 | 3 | | | | | Vmn1r236 |
| 23767 | 3 | | | | | Vmn1r237 |
| 23768 | 3 | | | | | Vmn1r238 |
| 23769 | 3 | | | | | Vmn1r24 |
| 23770 | 3 | | | | | Vmn1r25 |
| 23771 | 3 | | | | | Vmn1r26 |
| 23772 | 3 | | | | | Vmn1r27 |
| 23773 | 3 | | | | | Vmn1r28 |
| 23774 | 3 | | | | | Vmn1r29 |
| 23775 | 3 | | | | | Vmn1r3 |
| 23776 | 3 | | | | | Vmn1r30 |
| 23777 | 3 | | | | | Vmn1r31 |
| 23778 | 3 | | | | | Vmn1r32 |
| 23779 | 3 | | | | | Vmn1r33 |
| 23780 | 3 | | | | | Vmn1r34 |
| 23781 | 3 | | | | | Vmn1r35 |
| 23782 | 3 | | | | | Vmn1r36 |
| 23783 | 3 | | | | | Vmn1r37 |
| 23784 | 3 | | | | | Vmn1r38 |
| 23785 | 3 | | | | | Vmn1r39 |
| 23786 | 3 | | | | | Vmn1r41 |
| 23787 | 3 | | | | | Vmn1r42 |
| 23788 | 3 | | | | | Vmn1r43 |
| 23789 | 3 | | | | | Vmn1r44 |
| 23790 | 3 | | | | | Vmn1r45 |
| 23791 | 3 | | | | | Vmn1r46 |
| 23792 | 3 | | | | | Vmn1r47 |
| 23793 | 3 | | | | | Vmn1r48 |
| 23794 | 3 | | | | | Vmn1r49 |
| 23795 | 3 | | | | | Vmn1r5 |
| 23796 | 3 | | | | | Vmn1r50 |
| 23797 | 3 | | | | | Vmn1r51 |
| 23798 | 3 | | | | | Vmn1r52 |
| 23799 | 3 | | | | | Vmn1r54 |
| 23800 | 3 | | | | | Vmn1r55 |
| 23801 | 3 | | | | | Vmn1r56 |
| 23802 | 3 | | | | | Vmn1r57 |
| 23803 | 3 | | | | | Vmn1r58 |
| 23804 | 3 | | | | | Vmn1r59 |
| 23805 | 3 | | | | | Vmn1r6 |
| 23806 | 3 | | | | | Vmn1r60 |

Fig. 36 - 125

| | | | | | | |
|---|---|---|---|---|---|---|
| 23807 | 3 | | | | | Vmn1r61 |
| 23808 | 3 | | | | | Vmn1r62 |
| 23809 | 3 | | | | | Vmn1r63 |
| 23810 | 3 | | | | | Vmn1r64 |
| 23811 | 3 | | | | | Vmn1r65 |
| 23812 | 3 | | | | | Vmn1r66 |
| 23813 | 3 | | | | | Vmn1r67 |
| 23814 | 3 | | | | | Vmn1r68 |
| 23815 | 3 | | | | | Vmn1r69 |
| 23816 | 3 | | | | | Vmn1r7 |
| 23817 | 3 | | | | | Vmn1r70 |
| 23818 | 3 | | | | | Vmn1r71 |
| 23819 | 3 | | | | | Vmn1r72 |
| 23820 | 3 | | | | | Vmn1r73 |
| 23821 | 3 | | | | | Vmn1r74 |
| 23822 | 3 | | | | | Vmn1r75 |
| 23823 | 3 | | | | | Vmn1r76 |
| 23824 | 3 | | | | | Vmn1r77 |
| 23825 | 3 | | | | | Vmn1r78 |
| 23826 | 3 | | | | | Vmn1r79 |
| 23827 | 3 | | | | | Vmn1r8 |
| 23828 | 3 | | | | | Vmn1r80 |
| 23829 | 3 | | | | | Vmn1r81 |
| 23830 | 3 | | | | | Vmn1r82 |
| 23831 | 3 | | | | | Vmn1r83 |
| 23832 | 3 | | | | | Vmn1r84 |
| 23833 | 3 | | | | | Vmn1r85 |
| 23834 | 3 | | | | | Vmn1r86 |
| 23835 | 3 | | | | | Vmn1r87 |
| 23836 | 3 | | | | | Vmn1r88 |
| 23837 | 3 | | | | | Vmn1r89 |
| 23838 | 3 | | | | | Vmn1r9 |
| 23839 | 3 | | | | | Vmn1r91 |
| 23840 | 3 | | | | | Vmn1r94 |
| 23841 | 3 | | | | | Vmn1r95 |
| 23842 | 3 | | | | | Vmn2r-ps129 |
| 23843 | 3 | | | | | Vmn2r-ps159 |
| 23844 | 3 | | | | | Vmn2r-ps60 |
| 23845 | 3 | | | | | Vmn2r1 |
| 23846 | 3 | | | | | Vmn2r10 |
| 23847 | 3 | | | | | Vmn2r100 |
| 23848 | 3 | | | | | Vmn2r101 |
| 23849 | 3 | | | | | Vmn2r102 |
| 23850 | 3 | | | | | Vmn2r103 |
| 23851 | 3 | | | | | Vmn2r104 |
| 23852 | 3 | | | | | Vmn2r105 |
| 23853 | 3 | | | | | Vmn2r106 |
| 23854 | 3 | | | | | Vmn2r107 |
| 23855 | 3 | | | | | Vmn2r108 |
| 23856 | 3 | | | | | Vmn2r109 |
| 23857 | 3 | | | | | Vmn2r11 |
| 23858 | 3 | | | | | Vmn2r110 |
| 23859 | 3 | | | | | Vmn2r111 |
| 23860 | 3 | | | | | Vmn2r112 |
| 23861 | 3 | | | | | Vmn2r113 |
| 23862 | 3 | | | | | Vmn2r114 |
| 23863 | 3 | | | | | Vmn2r115 |
| 23864 | 3 | | | | | Vmn2r116 |
| 23865 | 3 | | | | | Vmn2r117 |
| 23866 | 3 | | | | | Vmn2r118 |
| 23867 | 3 | | | | | Vmn2r12 |
| 23868 | 3 | | | | | Vmn2r120 |
| 23869 | 3 | | | | | Vmn2r121 |
| 23870 | 3 | | | | | Vmn2r122 |
| 23871 | 3 | | | | | Vmn2r123 |
| 23872 | 3 | | | | | Vmn2r124 |
| 23873 | 3 | | | | | Vmn2r13 |
| 23874 | 3 | | | | | Vmn2r14 |
| 23875 | 3 | | | | | Vmn2r15 |
| 23876 | 3 | | | | | Vmn2r16 |
| 23877 | 3 | | | | | Vmn2r17 |
| 23878 | 3 | | | | | Vmn2r18 |
| 23879 | 3 | | | | | Vmn2r19 |
| 23880 | 3 | | | | | Vmn2r2 |
| 23881 | 3 | | | | | Vmn2r20 |
| 23882 | 3 | | | | | Vmn2r21 |
| 23883 | 3 | | | | | Vmn2r22 |
| 23884 | 3 | | | | | Vmn2r23 |
| 23885 | 3 | | | | | Vmn2r24 |
| 23886 | 3 | | | | | Vmn2r25 |
| 23887 | 3 | | | | | Vmn2r26 |
| 23888 | 3 | | | | | Vmn2r27 |
| 23889 | 3 | | | | | Vmn2r28 |
| 23890 | 3 | | | | | Vmn2r3 |
| 23891 | 3 | | | | | Vmn2r30 |
| 23892 | 3 | | | | | Vmn2r31 |
| 23893 | 3 | | | | | Vmn2r32 |
| 23894 | 3 | | | | | Vmn2r33 |
| 23895 | 3 | | | | | Vmn2r34 |
| 23896 | 3 | | | | | Vmn2r35 |
| 23897 | 3 | | | | | Vmn2r36 |
| 23898 | 3 | | | | | Vmn2r37 |
| 23899 | 3 | | | | | Vmn2r38 |
| 23900 | 3 | | | | | Vmn2r39 |
| 23901 | 3 | | | | | Vmn2r40 |
| 23902 | 3 | | | | | Vmn2r41 |
| 23903 | 3 | | | | | Vmn2r42 |
| 23904 | 3 | | | | | Vmn2r43 |
| 23905 | 3 | | | | | Vmn2r44 |
| 23906 | 3 | | | | | Vmn2r45 |
| 23907 | 3 | | | | | Vmn2r46 |
| 23908 | 3 | | | | | Vmn2r47 |
| 23909 | 3 | | | | | Vmn2r48 |
| 23910 | 3 | | | | | Vmn2r49 |
| 23911 | 3 | | | | | Vmn2r5 |
| 23912 | 3 | | | | | Vmn2r50 |
| 23913 | 3 | | | | | Vmn2r51 |
| 23914 | 3 | | | | | Vmn2r52 |
| 23915 | 3 | | | | | Vmn2r53 |
| 23916 | 3 | | | | | Vmn2r54 |
| 23917 | 3 | | | | | Vmn2r55 |
| 23918 | 3 | | | | | Vmn2r56 |
| 23919 | 3 | | | | | Vmn2r57 |
| 23920 | 3 | | | | | Vmn2r58 |
| 23921 | 3 | | | | | Vmn2r59 |
| 23922 | 3 | | | | | Vmn2r60 |
| 23923 | 3 | | | | | Vmn2r61 |
| 23924 | 3 | | | | | Vmn2r62 |
| 23925 | 3 | | | | | Vmn2r63 |
| 23926 | 3 | | | | | Vmn2r65 |
| 23927 | 3 | | | | | Vmn2r66 |
| 23928 | 3 | | | | | Vmn2r67 |
| 23929 | 3 | | | | | Vmn2r69 |
| 23930 | 3 | | | | | Vmn2r70 |
| 23931 | 3 | | | | | Vmn2r71 |
| 23932 | 3 | | | | | Vmn2r72 |
| 23933 | 3 | | | | | Vmn2r73 |
| 23934 | 3 | | | | | Vmn2r74 |
| 23935 | 3 | | | | | Vmn2r75 |
| 23936 | 3 | | | | | Vmn2r76 |
| 23937 | 3 | | | | | Vmn2r77 |
| 23938 | 3 | | | | | Vmn2r78 |
| 23939 | 3 | | | | | Vmn2r79 |
| 23940 | 3 | | | | | Vmn2r8 |
| 23941 | 3 | | | | | Vmn2r80 |
| 23942 | 3 | | | | | Vmn2r81 |
| 23943 | 3 | | | | | Vmn2r82 |
| 23944 | 3 | | | | | Vmn2r83 |
| 23945 | 3 | | | | | Vmn2r84 |
| 23946 | 3 | | | | | Vmn2r85 |
| 23947 | 3 | | | | | Vmn2r86 |
| 23948 | 3 | | | | | Vmn2r87 |
| 23949 | 3 | | | | | Vmn2r88 |
| 23950 | 3 | | | | | Vmn2r89 |
| 23951 | 3 | | | | | Vmn2r9 |
| 23952 | 3 | | | | | Vmn2r90 |
| 23953 | 3 | | | | | Vmn2r91 |
| 23954 | 3 | | | | | Vmn2r92 |
| 23955 | 3 | | | | | Vmn2r93 |
| 23956 | 3 | | | | | Vmn2r94 |
| 23957 | 3 | | | | | Vmn2r95 |
| 23958 | 3 | | | | | Vmn2r96 |
| 23959 | 3 | | | | | Vmn2r97 |
| 23960 | 3 | | | | | Vmn2r98 |
| 23961 | 3 | | | | | Vmn2r99 |
| 23962 | 3 | | | | | Vrtn |
| 23963 | 3 | | | | | Vwde |
| 23964 | 3 | | | | | Wap |
| 23965 | 3 | | | | | Wdr95 |
| 23966 | 3 | | | | | Wee2 |
| 23967 | 3 | | | | | Wnt8a |
| 23968 | 3 | | | | | Wnt8b |
| 23969 | 3 | | | | | Xist |
| 23970 | 3 | | | | | Xlr5a |
| 23971 | 3 | | | | | Xlr5b |
| 23972 | 3 | | | | | Xntrpc |
| 23973 | 3 | | | | | Zar1 |
| 23974 | 3 | | | | | Zar1l |
| 23975 | 3 | | | | | Zfp345 |
| 23976 | 3 | | | | | Zfp352 |
| 23977 | 3 | | | | | Zfp363 |
| 23978 | 3 | | | | | Zfp616 |
| 23979 | 3 | | | | | Zfp663 |
| 23980 | 3 | | | | | Zfp804b |
| 23981 | 3 | | | | | Zfp91Cntf |
| 23982 | 3 | | | | | Zp1 |
| 23983 | 3 | | | | | Zp2 |
| 23984 | 3 | | | | | Zp3 |
| 23985 | 3 | | | | | Zp4-ps |
| 23986 | 3 | | | | | Zscan4a |
| 23987 | 3 | | | | | Zscan4b |
| 23988 | 3 | | | | | Zscan4c |
| 23989 | 3 | | | | | Zscan4d |
| 23990 | 3 | | | | | Zscan4e |
| 23991 | 3 | | | | | Zscan4f |

Fig. 37-1

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Acta1 | 0.10 | 1.00 | 1.09 | 0.99 | 1.69 | 1.89 | 1.21 | 1.12 | 0.95 | 1.16 | 1.00 | 1.00 |
| Atp6v0c-ps2 | 1.00 | 1.00 | 1.90 | 0.66 | 1.00 | 0.49 | 1.75 | 0.58 | 0.30 | 0.67 | 1.88 | 0.62 |
| Bglap | 1.00 | 1.00 | 0.14 | 0.25 | 1.00 | 1.00 | 1.00 | 1.00 | 1.00 | 1.00 | 1.00 | 1.00 |
| Bglap2 | 1.00 | 1.00 | 0.16 | 0.55 | 1.00 | 1.00 | 1.00 | 1.00 | 1.00 | 1.00 | 1.00 | 1.00 |
| Camp | 0.31 | 0.15 | 0.12 | 0.28 | 1.00 | 1.00 | 1.00 | 1.00 | 1.11 | 1.02 | 1.00 | 1.00 |
| Ciart | 1.00 | 1.00 | 0.92 | 1.11 | 0.54 | 0.34 | 0.67 | 0.89 | 1.35 | 0.78 | 0.20 | 0.13 |
| Ckm | 0.15 | 1.00 | 1.11 | 0.91 | 2.02 | 1.98 | 0.97 | 0.90 | 0.79 | 1.04 | 1.00 | 1.00 |
| Cypt7 | 1.00 | 1.00 | 1.00 | 1.00 | 1.00 | 1.00 | 1.00 | 1.00 | 1.00 | 1.00 | 1.00 | 1.00 |
| D330041H03Rik | 1.00 | 1.00 | 1.55 | 2.46 | 1.06 | 0.95 | 0.76 | 0.68 | 0.65 | 0.85 | 2.35 | 0.93 |
| Dbp | 1.00 | 1.00 | 0.99 | 1.32 | 0.49 | 0.46 | 0.57 | 0.65 | 0.35 | 0.34 | 0.38 | 0.23 |
| Gm10488 | 1.00 | 1.00 | 1.00 | 1.00 | 1.00 | 1.00 | 1.00 | 1.00 | 1.00 | 1.00 | 1.00 | 1.00 |
| Gm1987 | 1.00 | 1.00 | 1.00 | 1.00 | 1.00 | 1.00 | 1.00 | 1.00 | 1.00 | 1.00 | 1.00 | 1.00 |
| Gm4836 | 1.00 | 1.00 | 1.00 | 1.00 | 1.00 | 1.00 | 1.00 | 1.00 | 1.00 | 1.00 | 1.00 | 1.00 |
| Gm5424 | 1.17 | 1.00 | 1.00 | 1.00 | 1.00 | 1.00 | 1.00 | 1.00 | 1.54 | 1.00 | 0.93 | 0.07 |
| Gm7334 | 1.00 | 1.00 | 0.64 | 2.15 | 1.19 | 1.18 | 0.11 | 1.08 | 1.24 | 0.87 | 0.24 | 0.32 |
| H2-Q8 | 1.00 | 1.00 | 1.00 | 0.45 | 1.00 | 1.00 | 1.00 | 1.00 | 0.65 | 2.09 | 0.43 | 1.00 |
| Hba-a2 | 0.61 | 0.68 | 0.91 | 0.58 | 0.48 | 1.01 | 1.30 | 0.94 | 1.08 | 0.89 | 3.36 | 1.18 |
| Hbb-b1 | 0.63 | 0.64 | 0.49 | 0.43 | 1.09 | 1.25 | 1.13 | 1.50 | 0.84 | 1.09 | 1.28 | 1.08 |
| Hist1h4m | 1.71 | 0.32 | 1.00 | 1.00 | 1.00 | 1.00 | 1.00 | 1.00 | 1.58 | 1.26 | 1.00 | 1.00 |
| Hist2h2aa2 | 1.00 | 1.00 | 1.00 | 1.48 | 1.00 | 4.53 | 1.43 | 0.33 | 0.65 | 2.16 | 0.20 | 1.00 |
| Hist2h3c1 | 1.00 | 1.00 | 0.22 | 0.99 | 1.00 | 1.00 | 3.23 | 1.00 | 0.16 | 0.12 | 2.20 | 0.24 |
| Ibsp | 1.00 | 1.00 | 0.19 | 0.28 | 1.00 | 1.00 | 1.00 | 1.00 | 1.00 | 1.00 | 1.00 | 1.00 |
| Mir1192 | 1.00 | 1.00 | 1.00 | 1.00 | 1.00 | 1.00 | 1.00 | 1.00 | 0.10 | 1.00 | 1.00 | 1.00 |
| Mir1199 | 1.00 | 1.00 | 1.00 | 1.00 | 1.00 | 1.00 | 1.00 | 1.00 | 1.00 | 1.00 | 1.00 | 1.00 |
| Mir1946a | 1.00 | 1.00 | 1.00 | 1.00 | 1.00 | 1.00 | 1.00 | 1.00 | 1.00 | 1.00 | 1.00 | 1.00 |
| Mir1966 | 1.00 | 1.00 | 1.00 | 1.00 | 1.00 | 0.02 | 1.00 | 1.00 | 1.00 | 1.00 | 1.00 | 1.00 |
| Mir3473g | 1.00 | 1.00 | 1.00 | 1.00 | 1.00 | 1.00 | 1.00 | 1.00 | 1.00 | 1.00 | 1.00 | 1.00 |
| Mir3535 | 1.00 | 1.00 | 1.00 | 1.00 | 1.00 | 1.00 | 1.00 | 1.00 | 1.00 | 1.00 | 1.00 | 1.00 |
| Mir466i | 1.00 | 1.00 | 1.00 | 1.00 | 1.00 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 1.00 | 1.00 | 1.00 | 1.00 |
| Mir6390 | 1.00 | 1.00 | 1.00 | 1.00 | 1.00 | 1.00 | 1.00 | 1.00 | 1.00 | 1.00 | 1.00 | 1.00 |
| Mir6403 | 1.00 | 1.00 | 1.00 | 1.00 | 1.00 | 1.00 | 1.00 | 1.00 | 0.17 | 1.00 | 1.00 | 1.00 |
| Mir6418 | 1.00 | 1.00 | 1.00 | 1.00 | 1.00 | 1.00 | 1.00 | 1.00 | 1.00 | 1.00 | 1.00 | 1.00 |
| Mir6537 | 1.00 | 1.00 | 1.00 | 1.00 | 1.00 | 1.00 | 1.00 | 1.00 | 1.00 | 1.00 | 1.00 | 1.00 |
| Mir683-2 | 1.00 | 1.00 | 1.00 | 1.00 | 1.00 | 1.00 | 1.00 | 1.00 | 1.00 | 1.00 | 1.00 | 1.00 |
| Mir692-2b | 1.00 | 1.00 | 1.00 | 1.00 | 1.00 | 1.00 | 1.00 | 1.00 | 1.00 | 1.00 | 1.00 | 1.00 |
| Mir697 | 1.00 | 1.00 | 1.00 | 1.00 | 1.00 | 1.00 | 1.00 | 1.00 | 1.00 | 1.00 | 1.00 | 1.00 |
| Mir6981 | 1.00 | 1.00 | 1.00 | 0.04 | 1.00 | 1.00 | 1.00 | 1.00 | 1.00 | 1.00 | 1.00 | 1.00 |
| Mir8113 | 1.00 | 1.00 | 1.00 | 1.00 | 1.00 | 1.00 | 1.00 | 1.00 | 1.00 | 1.00 | 1.00 | 1.00 |
| Mir8118 | 1.00 | 1.00 | 1.00 | 1.00 | 1.00 | 1.00 | 1.00 | 1.00 | 1.00 | 1.00 | 1.00 | 1.00 |
| Mup17 | 1.00 | 1.00 | 1.00 | 1.00 | 1.00 | 1.00 | 1.00 | 1.00 | 1.00 | 1.00 | 1.00 | 1.00 |
| Ngp | 0.49 | 0.43 | 0.04 | 0.28 | 1.02 | 1.33 | 1.00 | 1.19 | 1.26 | 1.08 | 1.00 | 1.00 |
| Pate4 | 1.00 | 1.00 | 1.00 | 1.00 | 1.00 | 1.00 | 1.00 | 1.00 | 1.00 | 1.00 | 1.00 | 1.00 |
| Ppbp | 0.68 | 0.70 | 0.17 | 0.61 | 1.01 | 1.23 | 0.73 | 1.25 | 0.87 | 1.10 | 1.08 | 0.67 |
| Ppp1r3g | 1.00 | 1.00 | 1.00 | 1.00 | 1.01 | 3.47 | 1.20 | 0.70 | 1.00 | 1.00 | 1.00 | 1.00 |
| Pvalb | 0.13 | 1.00 | 1.10 | 1.11 | 1.78 | 1.99 | 1.00 | 1.00 | 1.00 | 1.00 | 1.12 | 0.92 |
| Retnlg | 0.82 | 0.85 | 0.16 | 0.41 | 0.94 | 0.98 | 2.28 | 1.58 | 1.00 | 1.42 | 1.44 | 1.00 |
| Rnaset2a | 1.78 | 1.14 | 1.28 | 0.73 | 2.78 | 0.43 | 0.84 | 0.71 | 0.89 | 2.11 | 1.20 | 1.52 |
| Rpph1 | 1.00 | 1.00 | 1.00 | 1.00 | 1.00 | 1.00 | 1.00 | 1.00 | 1.00 | 1.00 | 0.84 | 1.00 |
| Rps29 | 0.39 | 0.47 | 0.68 | 0.34 | 0.78 | 0.70 | 0.74 | 0.86 | 0.90 | 0.74 | 1.45 | 0.97 |
| S100a8 | 1.33 | 0.86 | 0.06 | 0.33 | 1.49 | 1.40 | 1.58 | 1.99 | 1.98 | 1.79 | 2.64 | 1.09 |
| S100a9 | 1.41 | 0.98 | 0.06 | 0.28 | 1.77 | 1.91 | 2.00 | 1.22 | 2.03 | 1.95 | 2.77 | 1.99 |
| Saa2 | 1.00 | 1.00 | 1.00 | 1.00 | 1.00 | 1.00 | 1.00 | 1.00 | 1.00 | 1.00 | 1.00 | 1.00 |
| Scarna3a | 1.00 | 1.00 | 1.00 | 1.00 | 1.00 | 1.00 | 1.00 | 1.00 | 1.00 | 1.00 | 1.00 | 1.00 |
| Snora15 | 1.00 | 1.00 | 1.00 | 1.00 | 1.00 | 1.00 | 1.00 | 1.00 | 1.00 | 1.00 | 1.00 | 1.00 |
| Snora23 | 1.00 | 1.00 | 1.00 | 1.00 | 0.15 | 0.24 | 0.31 | 1.00 | 1.00 | 1.00 | 1.00 | 1.42 |
| Snora68 | 1.00 | 1.00 | 1.00 | 1.00 | 0.00 | 1.00 | 1.00 | 1.00 | 1.00 | 1.00 | 1.00 | 1.00 |
| Snora74a | 1.00 | 1.00 | 1.00 | 1.00 | 1.00 | 1.77 | 1.40 | 1.00 | 1.00 | 1.00 | 1.00 | 1.00 |
| Snord17 | 1.00 | 1.00 | 0.82 | 1.00 | 1.00 | 1.00 | 1.00 | 1.00 | 1.72 | 1.00 | 1.00 | 1.00 |
| Snurf | 1.00 | 1.00 | 0.78 | 1.18 | 1.00 | 0.80 | 1.03 | 1.02 | 1.18 | 1.19 | 1.03 | 0.86 |

Fig. 37-2

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Acta1 | 0.83 | 1.32 | 0.80 | 1.05 | 1.29 | 0.94 | 0.63 | 0.92 | 1.07 | 0.74 | 1.00 | 1.00 |
| Atp6v0c-ps2 | 1.05 | 1.39 | 0.33 | 0.14 | 2.52 | 1.05 | 0.22 | 4.96 | 2.67 | 1.27 | 0.92 | 1.19 |
| Bglap | 1.00 | 1.00 | 1.00 | 0.48 | 1.00 | 1.00 | 1.00 | 1.00 | 1.00 | 1.00 | 1.00 | 1.00 |
| Bglap2 | 1.00 | 1.00 | 1.00 | 1.00 | 1.00 | 1.00 | 1.00 | 1.00 | 1.00 | 1.00 | 1.00 | 1.00 |
| Camp | 1.00 | 1.00 | 1.00 | 1.00 | 1.04 | 1.00 | 1.00 | 0.81 | 1.00 | 1.00 | 1.45 | 2.21 |
| Ciart | 0.33 | 0.16 | 0.41 | 0.30 | 1.00 | 0.70 | 1.41 | 1.05 | 1.04 | 0.81 | 1.00 | 1.00 |
| Ckm | 1.00 | 1.66 | 0.94 | 0.83 | 1.15 | 0.93 | 0.99 | 0.91 | 0.92 | 1.05 | 1.00 | 1.00 |
| Cyp17 | 1.00 | 1.00 | 1.00 | 1.00 | 1.00 | 1.00 | 1.00 | 1.00 | 0.13 | 2.05 | 1.00 | 1.00 |
| D330041H03Rik | 0.17 | 1.99 | 0.28 | 1.20 | 0.79 | 1.03 | 1.72 | 0.88 | 2.12 | 0.79 | 0.95 | 0.78 |
| Dbp | 0.43 | 0.10 | 0.61 | 0.20 | 0.37 | 0.41 | 0.68 | 1.18 | 1.06 | 1.02 | 0.58 | 0.31 |
| Gm10488 | 1.00 | 1.00 | 1.00 | 1.00 | 1.00 | 1.00 | 1.00 | 1.00 | 0.09 | 2.62 | 1.00 | 1.00 |
| Gm1987 | 1.00 | 1.00 | 1.00 | 1.00 | 1.00 | 1.00 | 1.00 | 1.00 | 1.00 | 1.00 | 0.03 | 1.00 |
| Gm4836 | 1.00 | 1.00 | 1.00 | 1.00 | 1.00 | 1.00 | 1.00 | 1.00 | 0.14 | 2.13 | 1.00 | 1.00 |
| Gm5424 | 1.23 | 0.46 | 1.00 | 1.00 | 0.77 | 0.64 | 1.00 | 1.00 | 0.51 | 0.37 | 1.02 | 1.59 |
| Gm7334 | 1.00 | 0.98 | 0.33 | 0.39 | 1.02 | 0.66 | 1.45 | 1.62 | 1.10 | 1.42 | 0.42 | 0.89 |
| H2-Q8 | 1.00 | 1.00 | 1.00 | 1.00 | 1.00 | 1.00 | 1.76 | 0.74 | 1.00 | 1.00 | 1.70 | 0.72 |
| Hba-a2 | 0.18 | 0.79 | 0.33 | 1.21 | 0.40 | 2.51 | 0.97 | 0.64 | 1.60 | 0.07 | 1.01 | 0.54 |
| Hbb-b1 | 0.66 | 1.23 | 0.77 | 0.04 | 1.03 | 0.85 | 1.01 | 0.67 | 0.83 | 0.91 | 0.93 | 0.78 |
| Hist1h4m | 1.00 | 1.00 | 1.00 | 1.00 | 1.08 | 1.00 | 1.00 | 1.00 | 1.00 | 1.00 | 0.93 | 2.79 |
| Hist2h2aa2 | 0.44 | 1.00 | 3.72 | 1.81 | 1.00 | 1.39 | 2.52 | 0.74 | 1.45 | 0.49 | 2.48 | 0.65 |
| Hist2h3c1 | 1.00 | 0.31 | 4.72 | 0.53 | 3.89 | 3.69 | 0.20 | 0.93 | 3.17 | 4.25 | 1.00 | 1.86 |
| Ibsp | 1.00 | 1.00 | 1.00 | 1.00 | 1.00 | 1.00 | 1.00 | 1.00 | 1.00 | 1.00 | 1.00 | 1.00 |
| Mir1192 | 1.00 | 1.00 | 1.00 | 1.00 | 1.00 | 1.00 | 1.00 | 1.00 | 1.00 | 1.00 | 1.00 | 1.00 |
| Mir1199 | 1.00 | 1.00 | 1.00 | 1.00 | 1.00 | 1.00 | 1.00 | 1.00 | 1.00 | 1.00 | 0.09 | 1.00 |
| Mir1946a | 1.00 | 1.00 | 1.00 | 1.00 | 1.00 | 1.00 | 1.00 | 1.00 | 0.12 | 1.00 | 1.00 | 1.00 |
| Mir1966 | 1.00 | 1.00 | 1.00 | 1.00 | 1.00 | 1.00 | 1.00 | 1.00 | 1.00 | 1.00 | 1.00 | 1.00 |
| Mir3473g | 1.00 | 1.00 | 1.00 | 0.12 | 1.00 | 1.00 | 1.00 | 1.00 | 1.00 | 1.00 | 1.00 | 1.00 |
| Mir3535 | 1.00 | 1.00 | 1.00 | 1.00 | 1.00 | 1.00 | 1.00 | 1.00 | 1.00 | 1.00 | 1.00 | 0.10 |
| Mir466i | 1.00 | 1.00 | 1.00 | 1.00 | 1.00 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 1.00 | 1.00 | 1.00 | 1.00 | 1.00 | 1.00 |
| Mir6390 | 1.00 | 1.00 | 1.00 | 1.00 | 1.00 | 1.00 | 1.00 | 1.00 | 1.00 | 0.12 | 1.00 | 1.00 |
| Mir6403 | 1.00 | 1.00 | 1.00 | 1.00 | 1.00 | 1.00 | 1.00 | 1.00 | 1.00 | 1.00 | 1.00 | 1.00 |
| Mir6418 | 1.00 | 1.00 | 1.00 | 1.00 | 1.00 | 1.00 | 1.00 | 1.00 | 1.00 | 1.00 | 1.00 | 1.00 |
| Mir6537 | 1.00 | 1.00 | 1.00 | 1.00 | 1.00 | 1.00 | 1.00 | 1.00 | 1.00 | 1.00 | 1.00 | 0.02 |
| Mir683-2 | 1.00 | 1.00 | 1.00 | 1.00 | 1.00 | 1.00 | 1.00 | 1.00 | 1.00 | 0.02 | 1.00 | 1.00 |
| Mir692-2b | 1.00 | 1.00 | 1.00 | 1.00 | 1.00 | 1.00 | 1.00 | 1.00 | 1.00 | 1.00 | 1.00 | 0.02 |
| Mir697 | 1.00 | 1.00 | 1.00 | 1.00 | 1.00 | 1.00 | 1.00 | 1.00 | 1.00 | 1.00 | 1.00 | 1.00 |
| Mir6981 | 1.00 | 1.00 | 1.00 | 1.00 | 1.00 | 1.00 | 1.00 | 1.00 | 1.00 | 1.00 | 1.00 | 1.00 |
| Mir8113 | 1.00 | 1.00 | 1.00 | 1.00 | 1.00 | 0.12 | 1.00 | 1.00 | 1.00 | 1.00 | 1.00 | 1.00 |
| Mir8118 | 0.11 | 1.00 | 1.00 | 1.00 | 1.00 | 1.00 | 1.00 | 1.00 | 1.00 | 1.00 | 1.00 | 1.00 |
| Mup17 | 1.04 | 2.03 | 1.00 | 1.00 | 0.10 | 0.20 | 1.00 | 1.00 | 1.00 | 1.00 | 1.00 | 1.00 |
| Ngp | 1.00 | 1.01 | 1.00 | 0.50 | 1.03 | 0.97 | 1.00 | 0.59 | 1.00 | 1.85 | 1.46 | 2.43 |
| Pate4 | 1.00 | 1.00 | 1.00 | 1.00 | 1.00 | 1.00 | 0.13 | 1.00 | 1.00 | 1.00 | 1.00 | 1.00 |
| Ppbp | 1.00 | 1.18 | 1.00 | 1.00 | 1.03 | 0.82 | 0.66 | 0.99 | 1.00 | 1.00 | 0.85 | 1.05 |
| Ppp1r3g | 3.37 | 0.18 | 1.00 | 1.00 | 1.00 | 1.00 | 1.00 | 1.00 | 1.00 | 1.00 | 1.00 | 1.00 |
| Pvalb | 1.00 | 1.14 | 1.00 | 1.08 | 1.00 | 1.55 | 1.00 | 0.56 | 0.90 | 1.50 | 1.00 | 1.00 |
| Retnlg | 0.62 | 0.58 | 1.00 | 1.00 | 0.57 | 0.83 | 1.05 | 0.68 | 1.00 | 1.00 | 1.02 | 1.30 |
| Rnaset2a | 0.79 | 1.60 | 0.75 | 0.04 | 1.16 | 0.95 | 2.92 | 2.85 | 1.45 | 0.38 | 0.83 | 1.72 |
| Rpph1 | 0.85 | 2.35 | 1.02 | 1.00 | 0.18 | 1.00 | 1.00 | 1.00 | 1.00 | 1.00 | 0.69 | 2.12 |
| Rps29 | 3.40 | 0.65 | 0.78 | 0.14 | 0.98 | 1.01 | 1.38 | 1.12 | 1.19 | 0.57 | 0.86 | 1.02 |
| S100a8 | 1.71 | 1.86 | 0.99 | 0.54 | 0.39 | 1.11 | 1.97 | 0.73 | 0.78 | 1.53 | 1.64 | 2.43 |
| S100a9 | 1.10 | 1.48 | 1.64 | 0.59 | 0.90 | 0.97 | 2.45 | 0.77 | 1.03 | 1.55 | 1.82 | 2.45 |
| Saa2 | 0.17 | 2.74 | 1.22 | 0.91 | 1.00 | 1.00 | 1.00 | 1.00 | 1.00 | 1.00 | 1.00 | 1.00 |
| Scarna3a | 1.00 | 1.00 | 1.00 | 1.00 | 1.00 | 1.00 | 1.00 | 1.00 | 1.00 | 1.00 | 1.00 | 1.00 |
| Snora15 | 1.00 | 1.00 | 0.03 | 1.00 | 1.00 | 1.00 | 1.00 | 1.00 | 1.00 | 1.00 | 1.00 | 1.00 |
| Snora23 | 1.00 | 1.00 | 3.73 | 1.00 | 0.53 | 1.00 | 1.00 | 1.00 | 1.00 | 1.00 | 1.00 | 0.74 |
| Snora68 | 1.00 | 1.00 | 1.00 | 1.00 | 1.00 | 1.00 | 1.00 | 1.00 | 1.00 | 1.00 | 1.00 | 1.00 |
| Snora74a | 1.16 | 1.00 | 0.12 | 1.00 | 0.68 | 1.00 | 1.00 | 1.00 | 1.00 | 1.61 | 1.00 | 1.00 |
| Snord17 | 1.00 | 2.71 | 0.27 | 1.04 | 0.16 | 1.00 | 1.00 | 1.00 | 1.00 | 1.00 | 1.52 | 1.11 |
| Snurf | 1.00 | 1.00 | 0.95 | 1.61 | 0.87 | 1.23 | 1.00 | 1.00 | 1.00 | 1.00 | 1.00 | 1.00 |

Fig. 37- 3

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Acta1 | 0.69 | 1.00 | 0.55 | 0.27 | 1.15 | 1.62 | 0.94 | 0.97 | 0.45 | 1.06 |
| Atp6v0c-ps2 | 1.00 | 1.00 | 0.56 | 0.25 | 0.47 | 1.38 | 0.61 | 1.03 | 1.16 | 0.80 |
| Bglap | 1.00 | 1.00 | 1.00 | 1.00 | 1.00 | 1.00 | 1.00 | 1.00 | 0.30 | 1.26 |
| Bglap2 | 1.00 | 1.00 | 1.00 | 1.00 | 1.00 | 1.00 | 1.37 | 1.39 | 0.47 | 0.90 |
| Camp | 1.00 | 1.00 | 1.00 | 0.73 | 1.00 | 1.00 | 2.52 | 1.00 | 0.76 | 1.07 |
| Ciart | 1.00 | 1.00 | 0.72 | 0.62 | 0.87 | 1.13 | 1.18 | 0.68 | 1.00 | 1.00 |
| Ckm | 0.83 | 1.00 | 0.41 | 0.41 | 1.00 | 1.00 | 0.91 | 1.00 | 1.00 | 0.87 |
| Cypt7 | 1.00 | 1.00 | 1.00 | 1.00 | 1.00 | 1.00 | 1.00 | 1.00 | 1.00 | 1.00 |
| D330041H03Rik | 0.78 | 2.43 | 1.52 | 0.33 | 0.78 | 1.26 | 1.56 | 0.86 | 0.57 | 0.81 |
| Dbp | 1.00 | 1.00 | 0.84 | 0.67 | 0.80 | 0.87 | 0.91 | 0.71 | 1.00 | 0.88 |
| Gm10488 | 1.00 | 1.00 | 1.00 | 1.00 | 1.00 | 1.00 | 1.00 | 1.00 | 1.00 | 1.00 |
| Gm1987 | 1.00 | 1.00 | 1.00 | 1.00 | 1.00 | 1.00 | 1.00 | 1.00 | 1.00 | 1.00 |
| Gm4836 | 1.00 | 1.00 | 1.00 | 1.00 | 1.00 | 1.00 | 1.00 | 1.00 | 1.00 | 1.00 |
| Gm5424 | 1.00 | 1.00 | 3.43 | 0.92 | 3.30 | 1.00 | 1.42 | 1.00 | 2.04 | 2.27 |
| Gm7334 | 0.61 | 0.98 | 4.26 | 0.59 | 0.23 | 0.20 | 2.04 | 0.72 | 2.01 | 1.65 |
| H2-Q8 | 1.00 | 1.00 | 1.00 | 1.00 | 1.00 | 1.00 | 1.00 | 1.00 | 1.93 | 0.13 |
| Hba-a2 | 0.49 | 0.66 | 2.04 | 0.71 | 2.88 | 0.78 | 4.04 | 1.27 | 0.46 | 0.55 |
| Hbb-b1 | 0.84 | 1.16 | 1.24 | 0.80 | 1.43 | 0.99 | 1.31 | 0.94 | 0.56 | 0.65 |
| Hist1h4m | 1.00 | 1.00 | 1.00 | 1.00 | 1.00 | 1.00 | 1.00 | 1.00 | 1.55 | 0.16 |
| Hist2h2aa2 | 1.00 | 1.00 | 1.59 | 1.00 | 2.98 | 1.00 | 0.57 | 0.68 | 0.79 | 0.71 |
| Hist2h3c1 | 1.00 | 1.04 | 1.00 | 1.96 | 1.00 | 2.94 | 0.08 | 0.13 | 1.64 | 0.30 |
| Ibsp | 1.00 | 1.00 | 1.00 | 1.00 | 1.00 | 1.00 | 1.00 | 1.00 | 0.57 | 1.56 |
| Mir1192 | 1.00 | 1.00 | 1.00 | 1.00 | 1.00 | 1.00 | 1.00 | 1.00 | 1.00 | 1.00 |
| Mir1199 | 1.00 | 1.00 | 1.00 | 1.00 | 1.00 | 1.00 | 1.00 | 1.00 | 1.00 | 1.00 |
| Mir1946a | 1.00 | 1.00 | 1.00 | 1.00 | 1.00 | 1.00 | 1.00 | 1.00 | 1.00 | 1.00 |
| Mir1966 | 1.00 | 1.00 | 1.00 | 1.00 | 1.00 | 1.00 | 1.00 | 1.00 | 1.00 | 1.00 |
| Mir3473g | 1.00 | 1.00 | 1.00 | 1.00 | 1.00 | 1.00 | 1.00 | 1.00 | 1.00 | 1.00 |
| Mir3535 | 1.00 | 1.00 | 1.00 | 1.00 | 1.00 | 1.00 | 1.00 | 1.00 | 4.02 | 1.00 |
| Mir466i | 1.00 | 1.00 | 0.08 | 1.00 | 1.00 | 1.00 | 1.00 | 1.00 | 1.00 | 1.00 |
| Mir6345 | 1.00 | 1.00 | 1.00 | 1.00 | 1.00 | 1.00 | 0.10 | 1.00 | 1.00 | 1.00 |
| Mir6390 | 1.00 | 1.00 | 1.00 | 1.00 | 1.00 | 1.00 | 1.00 | 1.00 | 1.00 | 1.00 |
| Mir6403 | 0.11 | 1.00 | 1.00 | 1.00 | 1.00 | 1.00 | 1.00 | 1.00 | 1.00 | 1.00 |
| Mir6418 | 1.00 | 1.00 | 1.00 | 1.00 | 0.04 | 1.00 | 1.00 | 1.00 | 1.00 | 1.00 |
| Mir6537 | 1.00 | 1.00 | 1.00 | 1.00 | 1.00 | 1.00 | 1.00 | 1.00 | 1.00 | 1.00 |
| Mir683-2 | 1.00 | 1.00 | 1.00 | 1.00 | 1.00 | 1.00 | 1.00 | 1.00 | 1.00 | 1.00 |
| Mir692-2b | 1.00 | 1.00 | 1.00 | 1.00 | 1.00 | 1.00 | 1.00 | 1.00 | 1.00 | 1.00 |
| Mir697 | 1.00 | 0.02 | 1.00 | 1.00 | 1.00 | 1.00 | 1.00 | 1.00 | 1.00 | 1.00 |
| Mir6981 | 1.00 | 1.00 | 1.00 | 1.00 | 1.00 | 1.00 | 1.00 | 1.00 | 1.00 | 1.00 |
| Mir8113 | 1.00 | 1.00 | 1.00 | 1.00 | 1.00 | 1.00 | 1.00 | 1.00 | 0.14 | 1.00 |
| Mir8118 | 1.00 | 1.00 | 1.00 | 1.00 | 1.00 | 1.00 | 1.00 | 1.00 | 1.00 | 1.00 |
| Mup17 | 1.00 | 1.00 | 1.00 | 1.00 | 1.00 | 1.00 | 1.00 | 1.00 | 1.00 | 1.00 |
| Ngp | 1.00 | 1.00 | 1.43 | 0.31 | 1.10 | 1.00 | 3.13 | 1.00 | 0.93 | 1.01 |
| Pate4 | 1.00 | 1.00 | 1.00 | 1.00 | 1.00 | 1.00 | 1.00 | 1.00 | 1.00 | 1.00 |
| Ppbp | 1.00 | 1.00 | 1.00 | 1.00 | 1.00 | 1.00 | 1.45 | 1.00 | 0.53 | 0.83 |
| Ppp1r3g | 1.00 | 1.00 | 0.99 | 0.73 | 0.93 | 0.68 | 1.00 | 1.00 | 1.00 | 1.00 |
| Pvalb | 1.46 | 1.00 | 0.95 | 0.56 | 0.98 | 0.94 | 1.13 | 1.00 | 1.00 | 0.87 |
| Retnlg | 1.00 | 1.00 | 1.00 | 0.74 | 1.00 | 1.00 | 1.69 | 1.00 | 0.73 | 0.85 |
| Rnaset2a | 0.25 | 0.15 | 0.95 | 1.27 | 1.11 | 1.59 | 0.74 | 1.82 | 0.90 | 0.83 |
| Rpph1 | 1.00 | 2.16 | 1.00 | 1.00 | 1.00 | 1.00 | 1.00 | 1.00 | 0.48 | 0.95 |
| Rps29 | 1.76 | 0.70 | 0.98 | 0.54 | 1.21 | 1.67 | 1.39 | 0.56 | 0.65 | 1.04 |
| S100a8 | 1.00 | 1.12 | 4.57 | 0.17 | 2.47 | 1.90 | 1.76 | 1.02 | 0.82 | 1.23 |
| S100a9 | 1.22 | 1.48 | 4.90 | 0.28 | 2.89 | 1.44 | 1.94 | 1.34 | 0.87 | 1.16 |
| Saa2 | 1.00 | 0.23 | 1.00 | 1.00 | 1.00 | 1.00 | 1.00 | 1.00 | 1.00 | 1.00 |
| Scarna3a | 1.00 | 1.00 | 1.00 | 1.00 | 1.00 | 1.00 | 1.00 | 1.00 | 0.03 | 1.00 |
| Snora15 | 1.00 | 1.00 | 1.00 | 1.00 | 1.00 | 1.00 | 1.00 | 1.00 | 1.00 | 1.00 |
| Snora23 | 1.00 | 1.00 | 0.64 | 1.00 | 1.50 | 1.30 | 1.00 | 1.00 | 1.55 | 1.97 |
| Snora68 | 1.00 | 1.00 | 1.00 | 1.00 | 0.00 | 1.00 | 1.00 | 1.00 | 1.00 | 1.00 |
| Snora74a | 1.00 | 1.78 | 1.00 | 0.88 | 1.00 | 1.00 | 0.72 | 1.00 | 1.21 | 0.42 |
| Snord17 | 1.00 | 2.61 | 1.00 | 1.00 | 1.69 | 1.00 | 1.00 | 1.00 | 0.49 | 1.11 |
| Snurf | 1.00 | 1.00 | 0.96 | 0.79 | 0.89 | 0.12 | 1.00 | 1.00 | 1.00 | 1.00 |

Fig. 37-4

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Srp54c | 1.00 | 1.00 | 3.35 | 1.14 | 0.69 | 1.18 | 0.17 | 0.96 | 1.18 | 1.23 | 1.11 | 1.08 |
| Svs1 | 1.00 | 1.00 | 1.00 | 1.00 | 1.00 | 1.00 | 1.00 | 1.00 | 1.00 | 1.00 | 1.00 | 1.00 |
| Svs2 | 1.00 | 1.00 | 1.00 | 1.00 | 1.00 | 1.00 | 1.00 | 1.00 | 1.00 | 1.00 | 1.00 | 1.00 |
| Svs4 | 1.00 | 1.00 | 1.00 | 1.00 | 1.00 | 1.00 | 1.00 | 1.00 | 1.00 | 1.00 | 1.00 | 1.00 |
| Svs5 | 1.00 | 1.00 | 1.00 | 1.00 | 1.00 | 1.00 | 1.00 | 1.00 | 1.00 | 1.00 | 1.00 | 1.00 |
| Svs6 | 1.00 | 1.00 | 1.00 | 1.00 | 1.00 | 1.00 | 1.00 | 1.00 | 1.00 | 1.00 | 1.00 | 1.00 |
| Tcap | 0.14 | 1.00 | 1.05 | 0.79 | 1.27 | 1.35 | 0.96 | 0.75 | 0.69 | 0.93 | 0.74 | 1.00 |
| Tmem254c | 1.00 | 1.00 | 1.00 | 1.00 | 0.89 | 1.00 | 1.00 | 1.06 | 0.88 | 1.00 | 3.81 | 0.88 |
| Tnnc2 | 0.14 | 1.00 | 1.13 | 0.98 | 1.75 | 1.79 | 1.00 | 1.00 | 1.00 | 1.00 | 1.00 | 1.00 |
| Tnni2 | 0.16 | 1.00 | 1.09 | 0.93 | 2.07 | 2.08 | 0.78 | 0.78 | 1.00 | 1.04 | 1.00 | 1.00 |
| Usmg5 | 1.00 | 1.15 | 1.71 | 1.00 | 0.63 | 0.95 | 0.81 | 0.65 | 0.34 | 0.89 | 1.06 | 0.71 |
| 1810019D21Rik | 1.00 | 1.00 | 1.00 | 1.00 | 0.68 | 0.91 | 1.00 | 1.00 | 1.05 | 1.06 | 1.14 | 1.00 |
| 1810064F22Rik | 1.00 | 1.00 | 1.00 | 1.00 | 1.00 | 1.00 | 1.00 | 1.00 | 1.27 | 0.62 | 1.00 | 1.00 |
| 2010003K11Rik | 1.00 | 1.00 | 1.00 | 1.00 | 1.00 | 0.83 | 1.00 | 1.00 | 1.00 | 1.00 | 0.98 | 1.08 |
| 2210010C04Rik | 0.77 | 1.00 | 1.00 | 1.00 | 1.00 | 1.00 | 1.00 | 0.67 | 1.00 | 1.00 | 1.00 | 1.00 |
| 2310057J18Rik | 1.00 | 1.00 | 1.00 | 1.00 | 1.00 | 1.00 | 1.00 | 1.00 | 1.00 | 1.00 | 1.00 | 1.00 |
| 2810459M11Rik | 1.00 | 1.00 | 1.00 | 1.00 | 1.00 | 1.00 | 1.00 | 1.00 | 1.00 | 1.00 | 1.00 | 1.00 |
| 5830403L16Rik | 1.00 | 1.00 | 1.00 | 1.00 | 1.00 | 1.00 | 1.00 | 1.00 | 1.00 | 1.00 | 1.00 | 1.00 |
| 9230104L09Rik | 1.00 | 1.00 | 1.00 | 1.00 | 1.00 | 1.00 | 0.84 | 0.76 | 0.79 | 1.18 | 1.00 | 1.00 |
| 9230110F15Rik | 1.00 | 1.00 | 1.00 | 1.00 | 1.00 | 1.00 | 1.00 | 1.00 | 1.00 | 1.00 | 1.00 | 1.00 |
| A730008H23Rik | 1.00 | 1.00 | 1.00 | 1.00 | 1.04 | 0.93 | 1.08 | 1.66 | 2.61 | 1.77 | 1.00 | 1.00 |
| Acaa1b | 5.11 | 1.00 | 1.10 | 0.92 | 1.18 | 0.90 | 0.94 | 0.90 | 0.79 | 1.11 | 0.93 | 0.72 |
| Acpp | 1.00 | 1.00 | 1.00 | 1.00 | 1.00 | 1.00 | 1.00 | 1.00 | 1.43 | 1.13 | 0.80 | 0.74 |
| Actg2 | 1.00 | 1.00 | 1.00 | 1.00 | 1.00 | 1.19 | 1.52 | 1.21 | 1.01 | 1.14 | 1.00 | 1.00 |
| Adam28 | 1.00 | 1.00 | 1.00 | 1.00 | 1.00 | 1.00 | 1.00 | 1.00 | 0.93 | 0.97 | 1.00 | 1.00 |
| Adam7 | 1.00 | 1.00 | 1.00 | 1.00 | 1.00 | 1.00 | 1.00 | 1.00 | 1.00 | 1.00 | 1.00 | 1.00 |
| Ago2 | 1.00 | 1.00 | 0.73 | 0.94 | 1.20 | 1.36 | 1.36 | 1.33 | 1.59 | 1.19 | 0.48 | 1.28 |
| Ahsg | 44.19 | 1.00 | 1.46 | 0.86 | 1.48 | 0.86 | 0.80 | 0.71 | 1.12 | 1.00 | 1.00 | 1.00 |
| AI747448 | 1.00 | 1.00 | 1.00 | 1.00 | 1.00 | 1.00 | 1.00 | 1.00 | 1.00 | 1.00 | 1.00 | 1.00 |
| Akp3 | 1.00 | 1.00 | 1.00 | 1.00 | 1.00 | 1.00 | 1.00 | 1.00 | 1.00 | 1.00 | 1.00 | 1.00 |
| Alb | 105.7 | 1.00 | 2.82 | 1.09 | 1.86 | 0.95 | 1.00 | 1.00 | 1.00 | 1.00 | 1.25 | 1.00 |
| Aldob | 8.09 | 1.00 | 1.00 | 1.00 | 1.00 | 1.00 | 0.82 | 1.39 | 0.95 | 1.00 | 1.08 | 0.93 |
| Aldoc | 1.00 | 1.00 | 1.00 | 1.00 | 1.00 | 1.00 | 1.00 | 1.00 | 1.02 | 1.11 | 1.28 | 0.85 |
| Alox15 | 9.23 | 4.38 | 1.00 | 1.00 | 1.00 | 1.00 | 1.00 | 1.00 | 1.59 | 1.04 | 1.00 | 1.00 |
| Alpi | 1.00 | 1.00 | 1.00 | 1.00 | 1.00 | 1.00 | 1.00 | 1.00 | 1.00 | 1.00 | 1.00 | 1.00 |
| Ambp | 5.14 | 1.00 | 1.00 | 1.00 | 1.00 | 1.00 | 1.00 | 1.00 | 1.00 | 1.00 | 1.00 | 1.00 |
| Amd1 | 1.00 | 1.00 | 0.89 | 2.86 | 1.00 | 1.00 | 1.00 | 2.09 | 1.29 | 5.15 | 1.00 | 1.00 |
| Amy1 | 1.00 | 1.00 | 1.32 | 0.76 | 0.99 | 0.94 | 1.04 | 1.04 | 0.98 | 1.59 | 1.00 | 1.00 |
| Amy2a5 | 0.80 | 7.00 | 1.00 | 1.00 | 0.83 | 0.71 | 1.00 | 0.73 | 1.00 | 1.44 | 1.00 | 0.83 |
| Amy2b | 0.64 | 1.89 | 1.00 | 1.00 | 0.77 | 0.70 | 1.00 | 1.11 | 1.00 | 1.60 | 1.00 | 0.60 |
| Ang4 | 1.00 | 1.00 | 1.00 | 1.00 | 1.00 | 1.00 | 1.00 | 1.00 | 0.76 | 1.04 | 1.00 | 1.00 |
| Ap1s2 | 0.67 | 0.92 | 1.04 | 1.09 | 0.78 | 0.90 | 0.91 | 0.89 | 0.98 | 0.93 | 1.12 | 0.86 |
| Apoa1 | 19.44 | 1.00 | 3.09 | 1.31 | 2.47 | 1.08 | 1.00 | 1.00 | 1.00 | 1.00 | 1.13 | 1.00 |
| Apoa2 | 44.09 | 1.00 | 0.68 | 0.61 | 1.26 | 1.44 | 1.00 | 1.00 | 1.00 | 1.00 | 0.77 | 1.07 |
| Apoa5 | 8.22 | 1.00 | 1.00 | 1.00 | 1.00 | 1.00 | 1.00 | 1.00 | 1.00 | 1.00 | 1.00 | 1.00 |
| Apoc1 | 18.24 | 1.00 | 2.29 | 0.78 | 1.01 | 0.93 | 1.30 | 1.10 | 0.80 | 0.85 | 0.92 | 0.60 |
| Apoc3 | 11.67 | 1.00 | 1.00 | 1.00 | 1.08 | 0.84 | 1.00 | 1.00 | 1.00 | 1.00 | 1.36 | 0.80 |
| Apoc4 | 5.43 | 1.00 | 1.00 | 1.00 | 1.00 | 1.00 | 1.00 | 1.00 | 1.00 | 1.00 | 1.00 | 1.00 |
| Apoe | 12.48 | 1.70 | 1.28 | 0.83 | 0.90 | 0.82 | 0.98 | 0.93 | 0.81 | 1.04 | 1.06 | 0.79 |
| Apoh | 6.48 | 1.00 | 1.00 | 1.00 | 1.00 | 1.00 | 1.00 | 1.00 | 1.00 | 1.00 | 1.27 | 1.27 |
| Asb11 | 1.00 | 1.00 | 1.01 | 0.84 | 2.61 | 1.12 | 0.87 | 0.90 | 0.69 | 1.37 | 0.78 | 1.06 |
| AU015791 | 1.00 | 1.00 | 1.00 | 1.00 | 1.00 | 1.00 | 1.00 | 1.00 | 1.00 | 1.00 | 1.00 | 1.00 |
| AW112010 | 0.43 | 1.40 | 1.45 | 1.17 | 1.00 | 0.90 | 1.10 | 1.03 | 1.12 | 1.02 | 1.10 | 1.12 |
| AY761185 | 1.00 | 1.00 | 1.00 | 1.00 | 1.00 | 1.00 | 1.00 | 1.00 | 1.00 | 1.00 | 1.00 | 1.00 |
| Azgp1 | 7.18 | 1.00 | 1.00 | 1.00 | 1.00 | 1.00 | 1.00 | 1.00 | 1.00 | 1.00 | 1.00 | 1.00 |
| B4galnt2 | 1.00 | 1.00 | 1.00 | 1.00 | 1.00 | 1.00 | 1.00 | 1.00 | 1.00 | 1.00 | 1.00 | 1.00 |
| B9d1 | 1.00 | 1.00 | 0.99 | 0.91 | 1.00 | 1.00 | 1.25 | 1.00 | 1.04 | 1.36 | 0.97 | 0.98 |
| Bcl2l15 | 1.00 | 1.00 | 1.00 | 1.00 | 1.00 | 1.00 | 1.00 | 1.00 | 1.00 | 1.00 | 1.55 | 2.81 |
| Bex2 | 1.00 | 1.00 | 1.00 | 1.00 | 1.00 | 1.00 | 1.00 | 1.00 | 0.79 | 1.07 | 1.00 | 1.08 |
| Bex4 | 1.00 | 1.00 | 0.88 | 0.83 | 1.00 | 1.00 | 0.94 | 1.00 | 0.88 | 0.86 | 0.96 | 1.06 |

Fig. 37-5

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Srp54c | 1.77 | 1.30 | 0.70 | 0.30 | 1.32 | 0.88 | 0.33 | 0.89 | 1.03 | 1.10 | 2.68 | 0.80 |
| Svs1 | 1.00 | 1.00 | 1.00 | 1.00 | 1.00 | 1.00 | 0.18 | 1.00 | 1.00 | 1.00 | 1.00 | 1.00 |
| Svs2 | 1.00 | 1.00 | 1.00 | 1.00 | 1.00 | 1.00 | 0.04 | 1.00 | 1.00 | 1.00 | 1.00 | 1.00 |
| Svs4 | 1.00 | 1.00 | 1.00 | 1.00 | 1.00 | 1.00 | 0.02 | 0.28 | 1.00 | 1.00 | 1.00 | 1.00 |
| Svs5 | 1.00 | 1.00 | 1.00 | 1.00 | 1.00 | 1.00 | 0.02 | 0.26 | 1.11 | 1.17 | 1.00 | 1.00 |
| Svs6 | 1.00 | 1.00 | 1.00 | 1.00 | 1.00 | 1.00 | 0.07 | 0.62 | 0.93 | 0.67 | 1.00 | 1.00 |
| Tcap | 1.00 | 1.00 | 0.78 | 1.35 | 1.51 | 0.61 | 1.00 | 1.11 | 1.00 | 0.97 | 0.73 | 1.00 |
| Tmem254c | 0.53 | 4.02 | 0.08 | 2.26 | 0.56 | 1.00 | 3.60 | 2.54 | 1.38 | 1.00 | 1.00 | 1.00 |
| Tnnc2 | 1.00 | 1.00 | 1.00 | 1.00 | 2.09 | 0.76 | 1.00 | 0.64 | 1.17 | 1.71 | 1.00 | 1.00 |
| Tnni2 | 1.00 | 1.00 | 1.00 | 1.06 | 1.12 | 1.09 | 1.00 | 0.94 | 1.00 | 1.00 | 1.14 | 1.64 |
| Usmg5 | 1.69 | 1.20 | 0.81 | 0.08 | 0.92 | 1.13 | 1.06 | 1.37 | 0.98 | 1.26 | 0.72 | 1.40 |
| 1810019D21Rik | 0.94 | 0.85 | 0.71 | 1.05 | 1.09 | 1.02 | 7.94 | 2.38 | 1.00 | 1.00 | 1.00 | 1.00 |
| 1810064F22Rik | 0.79 | 1.09 | 1.00 | 1.00 | 1.01 | 0.85 | 8.78 | 4.40 | 1.00 | 1.00 | 1.00 | 1.00 |
| 2010003K11Rik | 0.74 | 0.87 | 0.74 | 1.00 | 5.18 | 1.47 | 1.20 | 1.25 | 0.97 | 1.28 | 1.00 | 1.00 |
| 2210010C04Rik | 1.00 | 4.08 | 1.60 | 58.53 | 2.92 | 39.35 | 1.00 | 1.00 | 1.00 | 1.00 | 145.6 | 0.03 |
| 2310057J18Rik | 1.00 | 1.00 | 1.00 | 1.00 | 1.83 | 9.04 | 1.00 | 1.00 | 1.00 | 1.00 | 1.00 | 1.00 |
| 2810459M11Rik | 1.10 | 0.93 | 1.11 | 1.11 | 1.15 | 1.03 | 3.02 | 6.74 | 1.00 | 1.00 | 1.00 | 1.00 |
| 5830403L16Rik | 1.00 | 1.00 | 1.00 | 1.00 | 1.00 | 1.00 | 19.25 | 161.8 | 0.99 | 0.59 | 1.00 | 1.00 |
| 9230104L09Rik | 1.00 | 1.00 | 1.00 | 1.00 | 1.00 | 1.00 | 26.13 | 248.0 | 1.05 | 0.89 | 1.00 | 1.00 |
| 9230110F15Rik | 1.00 | 1.00 | 1.00 | 1.00 | 1.00 | 1.00 | 6.80 | 102.5 | 1.00 | 1.00 | 1.00 | 1.00 |
| A730008H23Rik | 1.76 | 0.28 | 7.23 | 0.80 | 0.71 | 2.65 | 0.81 | 0.85 | 0.12 | 0.96 | 1.09 | 2.81 |
| Acaa1b | 1.01 | 0.99 | 0.84 | 0.93 | 0.96 | 0.89 | 1.00 | 0.72 | 1.36 | 0.60 | 0.70 | 1.30 |
| Acpp | 1.00 | 1.00 | 1.12 | 1.29 | 0.97 | 0.90 | 6.37 | 5.09 | 1.00 | 1.00 | 1.25 | 1.00 |
| Actg2 | 1.00 | 1.00 | 0.82 | 1.14 | 0.85 | 1.06 | 1.93 | 5.06 | 1.08 | 0.88 | 0.92 | 0.82 |
| Adam28 | 1.00 | 1.00 | 1.00 | 1.00 | 1.36 | 1.03 | 5.44 | 49.12 | 1.00 | 1.00 | 1.00 | 1.00 |
| Adam7 | 1.00 | 1.00 | 1.00 | 1.00 | 1.00 | 1.00 | 118.6 | 112.0 | 1.00 | 1.00 | 1.00 | 1.00 |
| Ago2 | 2.44 | 0.35 | 7.58 | 1.06 | 1.02 | 1.06 | 1.09 | 1.08 | 0.32 | 1.08 | 0.98 | 1.32 |
| Ahsg | 0.92 | 0.88 | 1.00 | 0.56 | 0.24 | 0.56 | 1.16 | 3.69 | 0.63 | 1.05 | 1.00 | 1.00 |
| AI747448 | 1.00 | 1.00 | 1.40 | 1.55 | 6.23 | 2.10 | 1.00 | 1.00 | 1.00 | 1.00 | 1.00 | 1.00 |
| Akp3 | 1.00 | 1.00 | 1.00 | 1.00 | 46.77 | 20.68 | 1.00 | 1.00 | 1.00 | 1.00 | 1.00 | 1.00 |
| Alb | 0.97 | 0.87 | 1.00 | 0.79 | 0.12 | 1.16 | 1.57 | 5.73 | 0.57 | 0.90 | 1.00 | 1.00 |
| Aldob | 0.92 | 0.96 | 0.81 | 1.10 | 3.19 | 2.26 | 6.43 | 3.79 | 1.00 | 1.00 | 1.22 | 1.00 |
| Aldoc | 0.90 | 1.49 | 0.74 | 1.04 | 0.69 | 0.98 | 5.04 | 3.74 | 0.97 | 1.27 | 0.73 | 0.77 |
| Alox15 | 1.00 | 1.00 | 1.00 | 1.00 | 0.94 | 0.90 | 0.57 | 1.64 | 1.00 | 1.00 | 1.00 | 1.16 |
| Alpi | 1.00 | 1.00 | 0.94 | 0.90 | 5.06 | 3.83 | 1.00 | 1.00 | 1.00 | 1.00 | 1.00 | 1.00 |
| Ambp | 0.94 | 1.27 | 1.00 | 0.79 | 0.76 | 1.07 | 1.00 | 1.17 | 1.00 | 0.91 | 1.00 | 1.00 |
| Amd1 | 1.00 | 1.00 | 1.00 | 1.00 | 1.00 | 1.00 | 1.00 | 1.00 | 5.93 | 1.00 | 3.27 | 1.00 |
| Amy1 | 0.96 | 0.90 | 1.95 | 4.78 | 2.47 | 1.98 | 0.77 | 0.93 | 1.50 | 1.22 | 15.36 | 0.17 |
| Amy2a5 | 0.40 | 5.28 | 1.84 | 242.2 | 2.68 | 13.12 | 0.70 | 0.89 | 1.00 | 1.00 | 173.6 | 0.03 |
| Amy2b | 0.85 | 1.78 | 2.08 | 73.04 | 2.69 | 12.85 | 0.59 | 0.85 | 1.00 | 1.00 | 100.3 | 0.04 |
| Ang4 | 1.00 | 1.00 | 0.54 | 1.81 | 10.33 | 3.34 | 1.00 | 1.00 | 1.00 | 1.00 | 1.00 | 1.00 |
| Ap1s2 | 0.95 | 1.09 | 0.88 | 0.98 | 0.75 | 1.00 | 7.83 | 3.19 | 0.76 | 1.11 | 0.96 | 0.77 |
| Apoa1 | 0.81 | 1.01 | 0.89 | 0.50 | 1.04 | 1.05 | 1.40 | 8.17 | 0.74 | 1.00 | 1.00 | 1.00 |
| Apoa2 | 0.84 | 1.16 | 1.00 | 1.02 | 0.13 | 0.76 | 2.36 | 11.98 | 1.11 | 0.91 | 1.00 | 1.00 |
| Apoa5 | 0.91 | 0.90 | 1.00 | 1.00 | 0.51 | 1.00 | 1.00 | 1.72 | 1.00 | 1.00 | 1.00 | 1.00 |
| Apoc1 | 0.95 | 1.19 | 0.61 | 0.58 | 0.67 | 0.92 | 0.84 | 0.83 | 1.35 | 0.62 | 0.73 | 0.73 |
| Apoc3 | 0.83 | 1.16 | 1.00 | 1.00 | 1.19 | 1.15 | 0.74 | 0.96 | 1.00 | 1.00 | 1.00 | 1.00 |
| Apoc4 | 0.90 | 1.13 | 1.00 | 1.00 | 0.67 | 1.00 | 0.66 | 0.84 | 1.00 | 1.00 | 1.00 | 1.00 |
| Apoe | 0.90 | 1.15 | 0.92 | 0.80 | 0.86 | 1.07 | 0.96 | 0.85 | 1.57 | 0.93 | 0.96 | 0.81 |
| Apoh | 0.91 | 1.10 | 1.00 | 1.00 | 0.44 | 1.00 | 1.00 | 1.65 | 1.31 | 0.89 | 1.00 | 1.00 |
| Asb11 | 1.00 | 1.00 | 1.10 | 0.75 | 0.82 | 1.86 | 6.20 | 1.00 | 1.00 | 1.00 | 1.00 | 1.00 |
| AU015791 | 1.00 | 1.00 | 0.61 | 1.68 | 1.00 | 1.00 | 3.92 | 9.88 | 1.00 | 1.00 | 1.00 | 1.00 |
| AW112010 | 0.88 | 1.35 | 0.68 | 0.83 | 1.32 | 1.02 | 1.17 | 0.97 | 1.00 | 1.00 | 0.93 | 0.95 |
| AY761185 | 1.00 | 1.00 | 1.00 | 1.00 | 1.00 | 1.00 | 324.2 | 1.00 | 1.00 | 1.41 | 1.00 | 1.00 |
| Azgp1 | 0.97 | 1.01 | 1.00 | 1.00 | 0.53 | 1.00 | 1.00 | 2.45 | 1.00 | 1.00 | 1.00 | 1.00 |
| B4galnt2 | 1.00 | 1.00 | 1.03 | 1.09 | 1.27 | 1.09 | 5.44 | 4.94 | 1.00 | 1.00 | 1.00 | 1.00 |
| B9d1 | 1.00 | 1.00 | 0.86 | 0.90 | 1.03 | 1.24 | 5.55 | 1.55 | 1.59 | 0.92 | 1.13 | 1.00 |
| Bcl2l15 | 1.00 | 1.00 | 0.74 | 1.36 | 2.03 | 1.00 | 5.01 | 9.09 | 0.93 | 0.81 | 0.89 | 1.33 |
| Bex2 | 1.00 | 1.00 | 0.62 | 0.89 | 0.92 | 1.17 | 10.48 | 5.59 | 1.47 | 0.76 | 0.83 | 1.00 |
| Bex4 | 1.00 | 1.00 | 0.79 | 1.52 | 1.00 | 0.81 | 5.42 | 3.11 | 1.10 | 1.04 | 0.85 | 0.96 |

Fig. 37-6

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Srp54c | 1.35 | 1.65 | 0.70 | 0.30 | 1.24 | 1.40 | 4.90 | 0.75 | 0.64 | 0.63 |
| Svs1 | 1.00 | 1.00 | 1.00 | 1.00 | 1.00 | 1.00 | 1.00 | 1.00 | 1.00 | 1.00 |
| Svs2 | 1.00 | 1.00 | 1.00 | 1.00 | 1.00 | 1.00 | 1.00 | 1.00 | 1.00 | 1.00 |
| Svs4 | 1.00 | 1.00 | 1.00 | 1.00 | 1.00 | 1.00 | 1.00 | 1.00 | 1.00 | 1.00 |
| Svs5 | 1.00 | 1.00 | 1.00 | 1.00 | 1.00 | 1.00 | 1.00 | 1.00 | 1.00 | 1.00 |
| Svs6 | 1.00 | 1.00 | 1.00 | 1.00 | 1.00 | 1.00 | 1.00 | 1.00 | 1.00 | 1.00 |
| Tcap | 0.68 | 1.00 | 0.85 | 0.47 | 0.91 | 0.93 | 0.97 | 0.84 | 1.00 | 1.00 |
| Tmem254c | 0.99 | 1.00 | 0.74 | 2.63 | 0.34 | 0.23 | 0.70 | 1.20 | 1.00 | 1.00 |
| Tnnc2 | 0.64 | 1.00 | 0.63 | 0.53 | 1.00 | 1.00 | 1.15 | 0.95 | 1.00 | 1.00 |
| Tnni2 | 1.38 | 1.00 | 0.33 | 0.46 | 1.00 | 1.00 | 1.06 | 0.99 | 0.47 | 1.65 |
| Usmg5 | 1.00 | 2.46 | 0.73 | 0.71 | 1.54 | 1.03 | 3.85 | 0.41 | 1.01 | 0.72 |
| 1810019D21Rik | 0.97 | 0.88 | 1.00 | 1.00 | 1.00 | 1.00 | 0.94 | 0.93 | 1.00 | 1.00 |
| 1810064F22Rik | 1.36 | 0.67 | 1.00 | 1.00 | 1.00 | 1.00 | 1.00 | 1.00 | 1.00 | 1.00 |
| 2010003K11Rik | 1.00 | 1.00 | 1.00 | 1.00 | 1.00 | 1.00 | 0.93 | 0.58 | 1.00 | 1.00 |
| 2210010C04Rik | 0.91 | 1.18 | 1.20 | 1.00 | 1.00 | 1.00 | 0.96 | 1.04 | 1.01 | 1.00 |
| 2310057J18Rik | 1.00 | 1.00 | 1.00 | 1.00 | 1.00 | 1.00 | 1.00 | 1.00 | 1.00 | 1.00 |
| 2810459M11Rik | 1.00 | 1.00 | 1.14 | 1.31 | 1.11 | 1.54 | 1.00 | 1.00 | 1.00 | 1.00 |
| 5830403L16Rik | 1.00 | 1.00 | 1.00 | 1.00 | 1.00 | 1.00 | 1.00 | 1.00 | 1.00 | 1.00 |
| 9230104L09Rik | 1.00 | 1.00 | 1.00 | 1.00 | 1.00 | 1.00 | 1.00 | 1.00 | 1.00 | 1.00 |
| 9230110F15Rik | 1.00 | 1.00 | 1.00 | 1.00 | 1.00 | 1.00 | 1.00 | 1.00 | 1.00 | 1.00 |
| A730008H23Rik | 1.00 | 1.00 | 0.88 | 3.46 | 0.87 | 1.00 | 0.70 | 1.47 | 6.49 | 1.89 |
| Acaa1b | 1.18 | 1.02 | 0.67 | 0.78 | 0.93 | 1.22 | 1.17 | 0.94 | 0.79 | 1.06 |
| Acpp | 0.95 | 0.76 | 1.00 | 1.00 | 1.00 | 1.00 | 0.96 | 1.01 | 1.24 | 1.27 |
| Actg2 | 1.00 | 1.50 | 1.00 | 1.00 | 1.00 | 1.00 | 1.00 | 1.00 | 1.00 | 1.00 |
| Adam28 | 1.00 | 1.00 | 1.00 | 1.00 | 1.00 | 1.00 | 1.00 | 1.00 | 1.00 | 1.00 |
| Adam7 | 1.00 | 1.00 | 1.00 | 1.00 | 1.00 | 1.00 | 1.00 | 1.00 | 1.00 | 1.00 |
| Ago2 | 1.00 | 0.56 | 0.94 | 5.02 | 1.36 | 0.81 | 0.68 | 1.54 | 3.97 | 1.72 |
| Ahsg | 0.82 | 0.67 | 1.00 | 1.00 | 1.00 | 1.00 | 0.89 | 0.15 | 1.00 | 1.26 |
| AI747448 | 1.00 | 1.00 | 1.00 | 1.00 | 1.00 | 1.00 | 1.00 | 1.00 | 1.00 | 1.00 |
| Akp3 | 1.00 | 1.00 | 1.00 | 1.00 | 1.00 | 1.00 | 1.00 | 1.00 | 1.00 | 1.00 |
| Alb | 1.00 | 0.57 | 1.00 | 1.00 | 1.00 | 1.00 | 0.59 | 0.17 | 0.77 | 1.18 |
| Aldob | 0.95 | 1.41 | 0.95 | 0.71 | 0.93 | 1.03 | 1.00 | 0.29 | 1.00 | 1.00 |
| Aldoc | 1.00 | 1.00 | 0.99 | 0.80 | 0.99 | 1.03 | 1.20 | 0.96 | 1.00 | 1.00 |
| Alox15 | 1.00 | 1.00 | 1.00 | 1.00 | 1.00 | 1.00 | 1.00 | 1.00 | 0.83 | 0.57 |
| Alpi | 1.00 | 1.00 | 1.00 | 1.00 | 1.00 | 1.00 | 1.00 | 1.00 | 1.00 | 1.00 |
| Ambp | 0.57 | 0.85 | 1.00 | 1.00 | 1.00 | 1.00 | 1.00 | 1.00 | 1.00 | 1.00 |
| Amd1 | 1.00 | 1.00 | 1.92 | 0.34 | 1.86 | 0.57 | 6.93 | 1.00 | 1.07 | 25.06 |
| Amy1 | 0.89 | 1.14 | 1.23 | 0.78 | 1.21 | 0.96 | 0.78 | 1.04 | 1.00 | 1.00 |
| Amy2a5 | 0.92 | 1.02 | 1.19 | 1.15 | 1.00 | 0.88 | 1.22 | 1.44 | 5.35 | 1.00 |
| Amy2b | 1.03 | 0.96 | 2.10 | 1.26 | 1.00 | 1.14 | 0.93 | 1.36 | 1.38 | 1.00 |
| Ang4 | 1.00 | 1.00 | 1.00 | 1.00 | 1.00 | 1.00 | 0.99 | 1.00 | 1.00 | 1.00 |
| Ap1s2 | 1.00 | 1.00 | 1.06 | 0.85 | 0.98 | 1.01 | 1.25 | 1.01 | 0.97 | 1.17 |
| Apoa1 | 1.11 | 0.80 | 1.40 | 0.84 | 0.64 | 0.93 | 0.47 | 0.09 | 1.00 | 1.07 |
| Apoa2 | 1.00 | 0.91 | 1.00 | 1.00 | 1.00 | 1.00 | 0.76 | 0.08 | 1.00 | 1.01 |
| Apoa5 | 1.00 | 1.00 | 1.00 | 1.00 | 1.00 | 1.00 | 1.00 | 1.00 | 1.00 | 1.00 |
| Apoc1 | 1.00 | 0.49 | 0.64 | 0.82 | 0.94 | 1.62 | 1.06 | 0.86 | 0.44 | 1.11 |
| Apoc3 | 1.00 | 0.63 | 0.94 | 0.53 | 1.00 | 1.00 | 0.88 | 0.42 | 1.00 | 1.00 |
| Apoc4 | 1.00 | 1.00 | 1.00 | 1.00 | 1.00 | 1.00 | 0.66 | 0.57 | 1.00 | 1.00 |
| Apoe | 0.74 | 1.12 | 0.98 | 0.72 | 0.98 | 1.16 | 1.06 | 0.88 | 0.67 | 0.76 |
| Apoh | 1.00 | 1.00 | 1.00 | 1.00 | 1.00 | 1.00 | 1.00 | 0.45 | 1.00 | 1.00 |
| Asb11 | 1.47 | 1.01 | 0.75 | 0.67 | 0.64 | 1.00 | 1.00 | 1.00 | 1.00 | 1.00 |
| AU015791 | 1.00 | 1.00 | 1.00 | 1.00 | 1.00 | 1.00 | 1.00 | 1.00 | 1.00 | 1.00 |
| AW112010 | 0.46 | 1.80 | 1.31 | 1.26 | 1.61 | 2.53 | 1.12 | 9.56 | 0.59 | 1.20 |
| AY761185 | 1.00 | 1.00 | 1.00 | 1.00 | 1.00 | 1.00 | 1.00 | 1.00 | 1.00 | 1.00 |
| Azgp1 | 1.00 | 1.00 | 1.00 | 1.00 | 1.00 | 1.00 | 1.00 | 0.77 | 1.00 | 1.00 |
| B4galnt2 | 1.00 | 1.00 | 1.00 | 1.00 | 1.00 | 1.00 | 0.93 | 1.26 | 1.00 | 1.00 |
| B9d1 | 1.14 | 1.40 | 0.87 | 0.83 | 0.91 | 1.06 | 0.94 | 0.63 | 1.00 | 0.68 |
| Bcl2l15 | 1.00 | 1.00 | 0.90 | 0.82 | 0.98 | 0.78 | 1.00 | 0.89 | 0.40 | 0.86 |
| Bex2 | 0.70 | 1.51 | 1.05 | 0.64 | 0.90 | 0.98 | 1.44 | 1.00 | 1.00 | 1.00 |
| Bex4 | 1.00 | 1.00 | 1.34 | 0.52 | 1.07 | 1.01 | 1.00 | 1.00 | 0.58 | 0.79 |

Fig. 37- 7

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Bglap3 | 1.00 | 1.00 | 1.00 | 1.00 | 1.00 | 1.00 | 1.00 | 1.00 | 1.00 | 1.00 | 1.28 | 0.76 |
| Bhmt | 5.87 | 1.00 | 1.00 | 1.00 | 1.00 | 1.00 | 1.00 | 1.00 | 1.00 | 1.00 | 1.43 | 1.16 |
| Bsph1 | 1.00 | 1.00 | 1.00 | 1.00 | 1.00 | 1.00 | 1.00 | 1.00 | 1.00 | 1.00 | 1.00 | 1.00 |
| Bspry | 1.00 | 1.00 | 1.00 | 1.00 | 1.00 | 1.00 | 1.00 | 1.00 | 0.90 | 0.85 | 1.03 | 1.22 |
| Btg3 | 0.65 | 1.05 | 1.98 | 0.69 | 0.78 | 0.39 | 8.30 | 0.26 | 0.49 | 1.40 | 3.49 | 3.34 |
| C4b | 8.06 | 2.61 | 1.13 | 0.94 | 1.07 | 1.06 | 1.16 | 1.26 | 1.02 | 1.00 | 1.01 | 1.20 |
| C4bp | 1.00 | 1.00 | 1.00 | 1.00 | 1.00 | 1.00 | 1.00 | 1.00 | 1.00 | 1.00 | 1.00 | 1.00 |
| Cbl | 1.00 | 1.00 | 1.00 | 0.95 | 1.09 | 1.56 | 1.78 | 1.29 | 1.77 | 1.12 | 0.66 | 1.00 |
| Ccl12 | 1.00 | 1.00 | 1.00 | 1.00 | 1.00 | 1.00 | 0.42 | 0.54 | 0.95 | 0.66 | 1.00 | 1.00 |
| Ccl21b | 1.00 | 1.00 | 2.54 | 1.08 | 0.35 | 1.33 | 0.30 | 0.37 | 0.49 | 0.27 | 1.11 | 2.42 |
| Ccl25 | 1.00 | 1.00 | 1.04 | 1.85 | 1.26 | 1.00 | 1.00 | 1.00 | 0.77 | 0.79 | 0.86 | 1.30 |
| Ccl27b | 1.00 | 1.00 | 1.00 | 1.00 | 1.00 | 1.00 | 1.00 | 1.00 | 1.00 | 1.00 | 1.00 | 1.00 |
| Ccno | 1.00 | 1.00 | 1.00 | 1.00 | 0.82 | 0.96 | 1.00 | 1.00 | 1.24 | 1.00 | 0.86 | 1.00 |
| Ccnt1 | 1.00 | 1.00 | 0.87 | 1.09 | 1.07 | 1.33 | 1.29 | 1.25 | 1.09 | 1.09 | 0.57 | 1.43 |
| Cdh1 | 1.00 | 1.00 | 1.00 | 1.00 | 1.00 | 1.00 | 1.00 | 1.00 | 0.96 | 0.98 | 0.91 | 1.03 |
| Cdh16 | 1.00 | 1.00 | 1.00 | 1.00 | 1.00 | 1.00 | 1.07 | 1.00 | 1.04 | 1.07 | 1.01 | 1.06 |
| Cdh17 | 1.00 | 1.00 | 1.00 | 1.00 | 1.00 | 1.00 | 1.00 | 1.00 | 1.00 | 1.00 | 1.00 | 1.00 |
| Cdk6 | 1.00 | 1.00 | 0.95 | 1.17 | 1.00 | 1.00 | 1.50 | 0.96 | 1.34 | 1.26 | 1.00 | 1.00 |
| Cdkl5 | 1.00 | 1.00 | 1.00 | 1.00 | 1.00 | 1.00 | 1.00 | 1.00 | 1.48 | 0.88 | 1.00 | 1.00 |
| Cdo1 | 5.46 | 1.00 | 2.44 | 0.64 | 0.91 | 0.84 | 1.26 | 0.99 | 0.89 | 0.91 | 1.20 | 0.98 |
| Ceacam10 | 1.00 | 1.00 | 1.00 | 1.00 | 1.00 | 1.00 | 1.00 | 1.00 | 1.00 | 1.00 | 1.00 | 1.00 |
| Cel | 0.93 | 1.00 | 1.00 | 1.00 | 1.00 | 1.00 | 1.00 | 0.97 | 1.00 | 1.00 | 1.00 | 1.00 |
| Cela1 | 0.63 | 0.75 | 1.00 | 1.00 | 1.00 | 1.00 | 1.00 | 1.36 | 1.66 | 0.88 | 1.25 | 1.17 |
| Cela2a | 0.66 | 1.00 | 1.00 | 1.00 | 1.00 | 1.00 | 1.00 | 0.79 | 1.00 | 1.05 | 1.00 | 1.28 |
| Cela3b | 0.59 | 1.00 | 1.00 | 1.00 | 1.00 | 1.00 | 1.00 | 1.46 | 1.00 | 1.31 | 1.00 | 1.00 |
| Ces5a | 1.00 | 1.00 | 1.00 | 1.00 | 1.00 | 1.00 | 1.00 | 1.00 | 1.00 | 1.00 | 1.00 | 1.00 |
| Cfd | 0.87 | 1.00 | 2.30 | 0.71 | 0.98 | 0.88 | 2.27 | 1.53 | 1.69 | 0.99 | 1.52 | 3.81 |
| Chga | 1.00 | 1.00 | 1.00 | 1.00 | 1.00 | 1.00 | 1.00 | 1.00 | 1.00 | 1.00 | 1.00 | 1.00 |
| Chrm2 | 1.00 | 1.00 | 1.00 | 1.00 | 1.00 | 1.00 | 1.14 | 1.28 | 1.18 | 1.03 | 1.00 | 1.00 |
| Chrna7 | 1.00 | 1.00 | 1.00 | 1.00 | 1.00 | 1.00 | 1.00 | 1.00 | 1.08 | 1.00 | 1.00 | 1.00 |
| Cited4 | 1.00 | 1.00 | 1.26 | 1.69 | 1.00 | 1.00 | 1.25 | 1.18 | 0.85 | 1.03 | 1.08 | 1.34 |
| Ckmt1 | 1.00 | 1.00 | 1.00 | 1.00 | 1.00 | 1.00 | 1.00 | 1.00 | 0.92 | 1.07 | 1.05 | 1.01 |
| Clca3 | 1.00 | 1.00 | 1.00 | 1.00 | 1.00 | 1.00 | 1.00 | 1.00 | 3.10 | 0.71 | 1.00 | 1.00 |
| Cldn2 | 1.00 | 1.00 | 1.00 | 1.00 | 1.00 | 1.00 | 1.00 | 1.00 | 1.16 | 1.06 | 0.93 | 0.92 |
| Cldn3 | 1.00 | 1.00 | 1.00 | 1.00 | 1.00 | 1.00 | 2.18 | 1.00 | 0.88 | 0.90 | 0.98 | 1.28 |
| Cldn4 | 1.00 | 1.00 | 1.00 | 1.00 | 1.00 | 1.00 | 1.00 | 1.00 | 0.93 | 1.09 | 1.05 | 0.82 |
| Cldn7 | 1.00 | 1.00 | 1.00 | 1.00 | 1.00 | 1.00 | 1.00 | 1.00 | 0.99 | 0.92 | 0.90 | 1.16 |
| Cldn8 | 1.00 | 1.00 | 1.00 | 1.00 | 1.00 | 1.00 | 1.00 | 1.00 | 0.97 | 1.10 | 0.95 | 1.00 |
| Clec2h | 1.00 | 1.00 | 1.00 | 1.00 | 1.00 | 1.00 | 1.00 | 1.00 | 1.00 | 1.00 | 1.30 | 0.60 |
| Clec7a | 1.29 | 1.10 | 1.00 | 1.00 | 0.88 | 1.08 | 1.09 | 1.99 | 1.37 | 1.26 | 1.00 | 1.00 |
| Clps | 0.79 | 1.66 | 1.25 | 0.79 | 0.97 | 0.73 | 1.00 | 0.89 | 1.00 | 1.11 | 1.00 | 0.91 |
| Clpsl2 | 1.00 | 1.00 | 1.00 | 1.00 | 1.00 | 1.00 | 1.00 | 1.00 | 1.00 | 1.00 | 1.00 | 1.00 |
| Clu | 0.63 | 0.60 | 1.14 | 1.10 | 1.12 | 0.85 | 0.91 | 0.87 | 0.86 | 0.94 | 1.14 | 1.05 |
| Cpa1 | 0.67 | 1.00 | 1.00 | 1.00 | 1.00 | 1.00 | 1.00 | 0.92 | 1.00 | 1.00 | 1.00 | 1.00 |
| Cpa2 | 1.00 | 1.00 | 1.00 | 1.00 | 1.00 | 1.00 | 1.00 | 1.00 | 1.00 | 1.00 | 1.00 | 1.00 |
| Cpb1 | 0.54 | 1.00 | 1.00 | 1.00 | 1.00 | 1.00 | 1.00 | 1.15 | 1.00 | 1.43 | 1.00 | 1.00 |
| Crisp1 | 1.00 | 1.00 | 1.00 | 1.00 | 1.00 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 | 1.00 | 1.00 | 1.00 |
| Cryba4 | 1.00 | 1.00 | 1.00 | 1.00 | 1.00 | 1.00 | 0.79 | 0.99 | 1.00 | 1.00 | 1.00 | 1.00 |
| Cst11 | 1.00 | 1.00 | 1.00 | 1.00 | 1.00 | 1.00 | 1.00 | 1.00 | 1.00 | 1.00 | 1.00 | 1.00 |
| Cst12 | 1.00 | 1.00 | 1.00 | 1.00 | 1.00 | 1.00 | 1.00 | 1.00 | 1.00 | 1.00 | 1.00 | 1.00 |
| Cst8 | 1.00 | 1.00 | 1.00 | 1.00 | 1.00 | 1.00 | 1.00 | 1.00 | 1.00 | 1.00 | 1.00 | 1.00 |
| Ctrb1 | 0.56 | 4.91 | 1.00 | 1.00 | 1.00 | 1.00 | 1.00 | 0.91 | 1.00 | 0.85 | 1.00 | 0.99 |
| Ctrc | 1.00 | 1.00 | 1.00 | 1.00 | 1.00 | 1.00 | 1.00 | 1.00 | 1.00 | 1.00 | 1.00 | 1.00 |
| Ctrl | 1.00 | 1.00 | 1.00 | 1.00 | 1.00 | 1.00 | 1.00 | 1.00 | 1.00 | 1.02 | 1.00 | 1.00 |
| Cuzd1 | 1.00 | 1.00 | 1.01 | 1.00 | 1.00 | 1.00 | 1.00 | 0.85 | 1.00 | 1.00 | 1.00 | 1.00 |
| Cxcl10 | 1.00 | 1.00 | 1.00 | 1.00 | 1.84 | 1.12 | 1.00 | 1.00 | 1.02 | 1.29 | 1.14 | 1.33 |
| Cxcl13 | 1.13 | 6.96 | 1.07 | 0.93 | 0.93 | 0.83 | 0.75 | 0.95 | 1.58 | 0.82 | 1.00 | 1.00 |
| Cxcl9 | 1.00 | 1.00 | 1.00 | 1.00 | 0.94 | 1.17 | 1.00 | 1.53 | 1.00 | 1.00 | 1.00 | 1.00 |
| Cyb561 | 1.00 | 1.00 | 0.88 | 1.03 | 1.33 | 1.06 | 0.85 | 0.90 | 0.97 | 1.01 | 1.08 | 1.02 |

Fig. 37-8

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Bglap3 | 1.00 | 1.00 | 1.05 | 1.43 | 1.25 | 1.14 | 14.79 | 2.34 | 1.00 | 1.00 | 1 | 1.00 |
| Bhmt | 0.95 | 1.07 | 0.99 | 1.00 | 0.40 | 1.00 | 1.00 | 1.90 | 1.14 | 1.28 | 1.00 | 1.00 |
| Bsph1 | 1.00 | 1.00 | 1.00 | 1.00 | 1.00 | 1.00 | 31.43 | 4.62 | 1.00 | 1.00 | 1.00 | 1.00 |
| Bspry | 1.00 | 1.00 | 1.07 | 0.95 | 1.06 | 1.13 | 6.20 | 3.71 | 1.24 | 0.87 | 1.04 | 1.00 |
| Btg3 | 1.00 | 1.00 | 2.32 | 2.22 | 0.99 | 1.41 | 1.98 | 0.37 | 1.65 | 0.48 | 1.68 | 1.72 |
| C4b | 1.11 | 1.07 | 1.37 | 0.70 | 0.83 | 0.95 | 0.78 | 0.97 | 0.62 | 0.99 | 1.03 | 0.94 |
| C4bp | 0.87 | 1.22 | 0.92 | 0.91 | 0.70 | 0.81 | 94.55 | 9.68 | 1.00 | 1.00 | 1.00 | 1.00 |
| Cbl | 1.07 | 0.90 | 13.38 | 0.97 | 1.15 | 1.17 | 1.01 | 1.18 | 0.77 | 1.07 | 1.01 | 1.38 |
| Ccl12 | 1.00 | 1.00 | 0.93 | 1.72 | 0.63 | 1.20 | 0.48 | 2.59 | 1.00 | 1.00 | 1.00 | 1.00 |
| Ccl21b | 1.00 | 1.00 | 0.69 | 7.58 | 0.22 | 8.49 | 1.00 | 0.92 | 1.20 | 0.87 | 1.98 | 1.00 |
| Ccl25 | 0.72 | 0.97 | 0.86 | 1.16 | 5.12 | 1.99 | 1.25 | 1.17 | 1.22 | 0.86 | 1.43 | 0.81 |
| Ccl27b | 1.00 | 1.00 | 1.00 | 1.00 | 1.00 | 1.00 | 1.00 | 1.00 | 7.01 | 1.27 | 1.00 | 1.00 |
| Ccno | 1.00 | 1.00 | 1.00 | 1.00 | 1.00 | 1.00 | 5.62 | 3.03 | 0.89 | 0.96 | 1.19 | 1.00 |
| Ccnt1 | 1.73 | 0.39 | 9.99 | 1.20 | 1.05 | 1.33 | 1.12 | 0.94 | 0.81 | 1.01 | 0.94 | 1.20 |
| Cdh1 | 1.02 | 1.48 | 0.94 | 1.02 | 1.06 | 1.00 | 7.75 | 5.97 | 1.00 | 1.00 | 1.24 | 0.98 |
| Cdh16 | 1.00 | 1.00 | 1.00 | 1.00 | 1.00 | 1.00 | 8.57 | 3.40 | 1.00 | 1.00 | 1.00 | 1.00 |
| Cdh17 | 1.00 | 1.00 | 0.95 | 1.06 | 7.23 | 3.58 | 1.14 | 1.00 | 1.00 | 1.00 | 1.00 | 0.89 |
| Cdk6 | 1.00 | 0.74 | 3.68 | 0.94 | 0.63 | 1.09 | 1.00 | 1.00 | 0.97 | 0.92 | 0.99 | 1.51 |
| Cdkl5 | 1.00 | 1.00 | 1.00 | 1.00 | 1.12 | 1.07 | 1.00 | 1.00 | 0.91 | 1.07 | 1.00 | 1.00 |
| Cdo1 | 1.04 | 1.04 | 0.87 | 1.02 | 0.83 | 1.08 | 0.66 | 0.85 | 0.80 | 1.19 | 1.57 | 0.64 |
| Ceacam10 | 1.49 | 0.92 | 2.04 | 1.18 | 1.14 | 0.88 | 14.18 | 11.76 | 1.00 | 1.00 | 1.00 | 1.00 |
| Cel | 1.00 | 3.06 | 1.91 | 52.04 | 2.72 | 4.04 | 1.00 | 1.00 | 1.00 | 1.00 | 113.7 | 0.03 |
| Cela1 | 0.83 | 3.83 | 1.10 | 1.60 | 2.88 | 2.22 | 1.09 | 1.54 | 1.00 | 1.00 | 11.90 | 0.24 |
| Cela2a | 0.76 | 5.35 | 1.97 | 63.25 | 3.04 | 63.60 | 1.00 | 1.00 | 1.00 | 1.00 | 155.2 | 0.02 |
| Cela3b | 1.00 | 4.97 | 1.76 | 52.97 | 2.67 | 33.46 | 1.00 | 1.00 | 1.00 | 1.00 | 126.1 | 0.02 |
| Ces5a | 1.00 | 1.00 | 1.00 | 1.00 | 1.00 | 1.00 | 49.51 | 1.00 | 1.77 | 0.75 | 1.00 | 1.00 |
| Cfd | 1.00 | 0.37 | 1.96 | 1.01 | 1.21 | 0.71 | 1.02 | 0.90 | 0.23 | 0.72 | 8.59 | 0.39 |
| Chga | 1.00 | 1.00 | 0.91 | 1.08 | 0.97 | 0.96 | 1.07 | 9.46 | 1.13 | 0.85 | 1.00 | 1.00 |
| Chrm2 | 1.00 | 1.00 | 5.02 | 0.84 | 0.83 | 1.05 | 1.00 | 1.00 | 1.00 | 1.00 | 1.00 | 1.00 |
| Chrna7 | 1.00 | 1.00 | 1.00 | 1.00 | 1.00 | 1.00 | 1.00 | 1.00 | 1.00 | 1.00 | 1.00 | 1.00 |
| Cited4 | 1.00 | 1.00 | 0.88 | 0.93 | 1.04 | 1.10 | 3.17 | 8.43 | 1.20 | 0.89 | 1.17 | 0.95 |
| Ckmt1 | 1.00 | 1.00 | 0.92 | 0.92 | 1.15 | 0.98 | 1.00 | 1.00 | 1.00 | 1.00 | 1.00 | 1.00 |
| Clca3 | 1.00 | 1.00 | 0.91 | 1.14 | 0.92 | 1.17 | 1.00 | 1.00 | 1.00 | 1.00 | 1.00 | 1.00 |
| Cldn2 | 0.77 | 1.27 | 1.04 | 0.98 | 0.94 | 1.30 | 6.71 | 6.59 | 1.00 | 1.00 | 1.00 | 1.00 |
| Cldn3 | 0.81 | 1.22 | 0.95 | 0.91 | 4.21 | 3.47 | 13.38 | 5.73 | 1.42 | 0.75 | 1.00 | 1.00 |
| Cldn4 | 1.00 | 1.00 | 0.76 | 0.99 | 1.28 | 1.05 | 9.20 | 7.40 | 1.00 | 1.00 | 1.00 | 1.00 |
| Cldn7 | 1.00 | 1.00 | 0.94 | 1.08 | 1.63 | 1.59 | 5.51 | 6.55 | 1.13 | 1.00 | 1.00 | 1.00 |
| Cldn8 | 1.00 | 1.00 | 1.01 | 1.64 | 0.89 | 1.10 | 6.80 | 1.77 | 1.00 | 1.00 | 1.00 | 1.00 |
| Clec2h | 1.00 | 1.00 | 0.86 | 0.93 | 8.72 | 2.46 | 1.00 | 1.00 | 1.00 | 1.00 | 1.00 | 1.00 |
| Clec7a | 1.56 | 1.21 | 0.99 | 0.76 | 0.90 | 0.70 | 0.87 | 1.27 | 1.00 | 1.00 | 1.26 | 1.10 |
| Clps | 0.85 | 1.81 | 1.64 | 7.75 | 0.87 | 0.99 | 1.19 | 0.87 | 1.21 | 1.18 | 192.9 | 0.02 |
| Clpsl2 | 1.00 | 1.00 | 1.00 | 1.00 | 1.00 | 1.00 | 84.26 | 47.08 | 1.00 | 1.00 | 1.00 | 1.00 |
| Clu | 0.95 | 1.12 | 0.96 | 0.89 | 0.97 | 0.91 | 19.56 | 1.14 | 1.27 | 0.99 | 1.00 | 0.87 |
| Cpa1 | 1.00 | 3.24 | 1.93 | 48.86 | 2.77 | 32.52 | 1.00 | 1.00 | 1.00 | 1.00 | 118.9 | 0.03 |
| Cpa2 | 1.00 | 1.43 | 1.53 | 14.76 | 2.65 | 9.90 | 1.00 | 1.00 | 1.00 | 1.00 | 36.18 | 0.10 |
| Cpb1 | 1.00 | 5.06 | 1.46 | 73.34 | 2.67 | 49.61 | 1.00 | 1.00 | 1.00 | 1.00 | 128.1 | 0.03 |
| Crisp1 | 1.00 | 1.00 | 1.00 | 1.00 | 1.43 | 0.92 | 6.40 | 25.54 | 1.00 | 3.41 | 1.00 | 1.00 |
| Crisp4 | 1.00 | 1.00 | 1.00 | 1.00 | 1.00 | 1.00 | 5.22 | 3.29 | 1.00 | 1.00 | 1.00 | 1.00 |
| Cryba4 | 1.00 | 1.00 | 1.00 | 1.00 | 1.00 | 1.00 | 25.88 | 11.47 | 1.00 | 1.00 | 0.97 | 0.92 |
| Cst11 | 1.00 | 1.00 | 1.00 | 1.00 | 0.51 | 0.66 | 20.05 | 267.4 | 1.53 | 2.22 | 1.00 | 1.00 |
| Cst12 | 1.00 | 1.00 | 1.00 | 1.00 | 1.00 | 1.00 | 21.70 | 179.1 | 1.14 | 0.96 | 1.00 | 1.00 |
| Cst8 | 1.00 | 1.00 | 1.00 | 1.00 | 1.26 | 0.81 | 4.56 | 43.46 | 1.27 | 0.98 | 1.00 | 1.00 |
| Ctrb1 | 0.41 | 22.95 | 1.84 | 266.2 | 2.60 | 211.5 | 1.00 | 1.00 | 1.00 | 1.00 | 163.1 | 0.02 |
| Ctrc | 1.00 | 1.00 | 1.50 | 12.5 | 3.31 | 9.98 | 1.00 | 1.00 | 1.00 | 1.00 | 47.14 | 0.11 |
| Ctrl | 1.00 | 3.35 | 2.02 | 31.91 | 3.11 | 23.86 | 1.00 | 1.00 | 1.00 | 1.00 | 94.99 | 0.04 |
| Cuzd1 | 1.00 | 1.00 | 1.57 | 3.59 | 2.72 | 2.14 | 19.07 | 8.42 | 0.91 | 1.25 | 4.53 | 0.64 |
| Cxcl10 | 1.59 | 1.09 | 0.92 | 1.40 | 0.87 | 1.01 | 1.14 | 1.15 | 1.00 | 1.00 | 1.74 | 1.01 |
| Cxcl13 | 0.84 | 1.57 | 0.73 | 0.91 | 0.86 | 0.93 | 0.72 | 1.00 | 1.00 | 1.00 | 1.11 | 0.84 |
| Cxcl9 | 0.86 | 1.05 | 0.86 | 0.74 | 1.00 | 1.00 | 1.21 | 1.10 | 1.00 | 1.00 | 1.47 | 2.00 |
| Cyb561 | 0.81 | 1.30 | 0.89 | 1.13 | 1.01 | 0.99 | 5.12 | 1.86 | 1.07 | 1.13 | 1.02 | 1.04 |

Fig. 37- 9

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Bglap3 | 1.97 | 2.14 | 1.00 | 1.00 | 1.00 | 1.00 | 1.06 | 0.95 | 1.00 | 1.00 |
| Bhmt | 1.00 | 1.00 | 1.00 | 1.00 | 1.00 | 1.00 | 1.07 | 0.69 | 1.00 | 1.00 |
| Bsph1 | 1.00 | 1.00 | 1.00 | 1.00 | 1.00 | 1.00 | 1.00 | 1.00 | 1.00 | 1.00 |
| Bspry | 0.67 | 1.31 | 0.82 | 1.55 | 1.31 | 0.89 | 0.86 | 0.90 | 1.00 | 1.00 |
| Btg3 | 2.33 | 1.00 | 0.50 | 1.00 | 3.55 | 5.85 | 0.15 | 3.88 | 0.21 | 0.52 |
| C4b | 1.23 | 0.77 | 1.08 | 1.47 | 1.97 | 2.68 | 1.01 | 1.17 | 1.00 | 1.08 |
| C4bp | 1.00 | 1.00 | 1.00 | 1.00 | 1.00 | 1.00 | 1.00 | 1.00 | 1.00 | 1.00 |
| Cbl | 1.00 | 1.00 | 0.86 | 7.24 | 1.56 | 0.75 | 0.63 | 1.67 | 7.43 | 2.57 |
| Ccl12 | 1.00 | 1.00 | 1.00 | 1.00 | 6.97 | 3.28 | 0.69 | 1.31 | 1.00 | 1.00 |
| Ccl21b | 1.13 | 2.08 | 0.89 | 0.83 | 1.21 | 1.51 | 0.61 | 1.00 | 1.00 | 1.00 |
| Ccl25 | 1.00 | 1.00 | 1.32 | 0.59 | 1.57 | 1.01 | 1.33 | 0.64 | 1.00 | 0.91 |
| Ccl27b | 1.00 | 1.00 | 1.00 | 1.00 | 1.00 | 1.00 | 1.09 | 0.58 | 1.00 | 1.00 |
| Ccno | 1.00 | 1.00 | 1.08 | 1.04 | 1.00 | 1.23 | 1.01 | 1.00 | 0.91 | 0.95 |
| Ccnt1 | 1.00 | 0.94 | 0.87 | 2.60 | 1.34 | 0.91 | 0.81 | 1.17 | 3.18 | 1.68 |
| Cdh1 | 1.07 | 1.10 | 0.96 | 0.89 | 1.18 | 0.71 | 1.00 | 0.99 | 1.01 | 0.84 |
| Cdh16 | 1.00 | 1.00 | 1.00 | 1.00 | 1.00 | 1.00 | 1.00 | 1.00 | 1.00 | 1.00 |
| Cdh17 | 1.00 | 1.00 | 1.00 | 1.00 | 1.00 | 1.00 | 1.00 | 1.00 | 1.00 | 1.00 |
| Cdk6 | 1.00 | 1.00 | 1.00 | 1.00 | 1.00 | 1.00 | 1.00 | 1.27 | 5.27 | 1.77 |
| Cdkl5 | 1.00 | 1.00 | 0.66 | 7.33 | 1.63 | 0.74 | 1.00 | 1.00 | 1.00 | 1.00 |
| Cdo1 | 1.08 | 1.78 | 1.09 | 0.72 | 0.82 | 1.02 | 1.03 | 0.86 | 0.84 | 0.99 |
| Ceacam10 | 1.00 | 1.00 | 1.00 | 1.00 | 1.00 | 1.00 | 1.00 | 1.00 | 1.01 | 1.56 |
| Cel | 0.93 | 1.11 | 1.58 | 1.00 | 1.00 | 1.00 | 1.49 | 1.00 | 1.00 | 1.00 |
| Cela1 | 0.93 | 1.17 | 1.56 | 0.74 | 1.37 | 1.07 | 1.50 | 1.06 | 0.81 | 0.94 |
| Cela2a | 0.96 | 1.13 | 1.31 | 1.00 | 1.00 | 1.00 | 1.15 | 1.19 | 1.00 | 1.00 |
| Cela3b | 0.86 | 1.10 | 1.23 | 1.00 | 1.00 | 1.02 | 1.36 | 0.98 | 1.00 | 1.00 |
| Ces5a | 1.00 | 1.00 | 1.00 | 1.00 | 1.00 | 1.00 | 1.00 | 1.00 | 1.00 | 1.00 |
| Cfd | 0.55 | 0.94 | 1.32 | 1.00 | 1.00 | 1.00 | 1.02 | 1.20 | 0.54 | 0.43 |
| Chga | 1.03 | 0.92 | 1.05 | 0.81 | 0.88 | 0.97 | 0.79 | 0.68 | 1.00 | 1.00 |
| Chrm2 | 1.00 | 1.00 | 0.72 | 4.55 | 1.56 | 0.93 | 1.00 | 1.00 | 1.00 | 1.00 |
| Chrna7 | 1.00 | 1.00 | 0.93 | 5.14 | 1.34 | 1.23 | 1.00 | 1.00 | 1.00 | 1.00 |
| Cited4 | 1.39 | 1.30 | 0.84 | 0.68 | 1.08 | 0.96 | 1.01 | 0.82 | 0.86 | 0.55 |
| Ckmt1 | 0.95 | 5.09 | 0.98 | 0.93 | 0.99 | 0.97 | 1.07 | 1.04 | 1.00 | 1.00 |
| Clca3 | 1.00 | 7.65 | 1.00 | 1.00 | 1.00 | 1.00 | 0.81 | 1.44 | 1.00 | 1.00 |
| Cldn2 | 1.00 | 1.00 | 0.88 | 0.87 | 1.05 | 0.92 | 0.80 | 0.73 | 1.00 | 1.00 |
| Cldn3 | 0.86 | 1.37 | 1.01 | 0.97 | 0.94 | 1.00 | 1.16 | 0.82 | 1.00 | 1.00 |
| Cldn4 | 0.90 | 1.59 | 1.00 | 1.00 | 1.00 | 1.00 | 0.97 | 1.06 | 1.00 | 1.00 |
| Cldn7 | 1.17 | 1.64 | 1.00 | 1.00 | 1.00 | 1.00 | 1.00 | 1.00 | 1.00 | 1.00 |
| Cldn8 | 0.92 | 0.94 | 1.00 | 1.00 | 1.00 | 1.00 | 1.04 | 1.36 | 1.00 | 1.00 |
| Clec2h | 1.00 | 1.00 | 1.00 | 1.00 | 1.00 | 1.00 | 1.00 | 1.00 | 1.00 | 1.00 |
| Clec7a | 1.00 | 1.00 | 1.00 | 1.00 | 1.00 | 1.88 | 1.16 | 7.35 | 1.15 | 1.28 |
| Clps | 0.91 | 1.25 | 1.07 | 1.31 | 0.49 | 0.65 | 0.78 | 1.04 | 0.26 | 1.00 |
| Clpsl2 | 1.00 | 1.00 | 1.00 | 1.00 | 1.00 | 1.00 | 1.00 | 1.00 | 1.00 | 1.00 |
| Clu | 0.90 | 1.03 | 1.11 | 0.83 | 1.03 | 1.14 | 1.08 | 0.91 | 0.58 | 0.77 |
| Cpa1 | 0.85 | 1.12 | 1.05 | 1.00 | 1.00 | 1.00 | 1.23 | 1.00 | 1.00 | 1.00 |
| Cpa2 | 0.86 | 1.10 | 0.76 | 0.91 | 1.00 | 1.15 | 1.00 | 1.00 | 1.00 | 1.00 |
| Cpb1 | 0.97 | 1.10 | 1.53 | 0.96 | 1.00 | 1.00 | 1.18 | 1.28 | 1.00 | 1.00 |
| Crisp1 | 1.00 | 1.00 | 1.00 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 | 1.00 |
| Cryba4 | 1.00 | 1.00 | 1.00 | 1.00 | 1.77 | 1.00 | 1.00 | 1.00 | 0.89 | 1.00 |
| Cst11 | 1.00 | 1.00 | 1.00 | 1.00 | 1.00 | 1.00 | 1.00 | 1.00 | 1.00 | 1.00 |
| Cst12 | 1.00 | 1.00 | 1.00 | 1.00 | 1.00 | 1.00 | 1.00 | 1.00 | 1.00 | 1.00 |
| Cst8 | 1.00 | 1.00 | 1.00 | 1.00 | 1.00 | 1.00 | 1.00 | 1.00 | 1.00 | 1.00 |
| Ctrb1 | 0.85 | 1.13 | 1.61 | 0.88 | 1.00 | 0.85 | 0.99 | 1.11 | 3.24 | 1.00 |
| Ctrc | 0.93 | 1.16 | 1.00 | 1.00 | 1.00 | 1.00 | 1.00 | 1.00 | 1.00 | 1.00 |
| Ctrl | 0.83 | 1.22 | 0.88 | 1.07 | 1.00 | 0.93 | 1.44 | 1.00 | 1.00 | 1.00 |
| Cuzd1 | 0.91 | 1.12 | 1.00 | 1.00 | 1.00 | 1.00 | 1.00 | 1.00 | 1.00 | 1.00 |
| Cxcl10 | 1.00 | 1.00 | 1.00 | 1.00 | 1.09 | 2.75 | 1.17 | 25.94 | 0.77 | 0.78 |
| Cxcl13 | 0.66 | 0.82 | 1.00 | 1.00 | 1.00 | 3.84 | 1.26 | 1.66 | 1.00 | 1.00 |
| Cxcl9 | 1.00 | 1.00 | 1.00 | 1.00 | 1.00 | 1.00 | 1.00 | 30.33 | 1.00 | 1.00 |
| Cyb561 | 1.09 | 1.04 | 1.00 | 0.86 | 0.86 | 1.01 | 1.00 | 0.85 | 1.00 | 0.99 |

Fig. 37-10

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Cyp2d9 | 6.19 | 1.00 | 1.00 | 1.00 | 1.00 | 1.00 | 1.00 | 1.00 | 1.00 | 1.00 | 0.96 | 0.76 |
| Cyp2e1 | 22.51 | 1.00 | 2.34 | 0.93 | 0.86 | 0.76 | 1.55 | 1.24 | 0.92 | 0.89 | 1.04 | 1.04 |
| Cyp3a11 | 11.64 | 1.00 | 1.00 | 1.00 | 1.00 | 1.00 | 1.00 | 1.00 | 1.00 | 1.00 | 1.00 | 1.00 |
| Cyp4a10 | 7.15 | 1.00 | 1.00 | 1.00 | 1.00 | 1.00 | 1.00 | 1.00 | 1.00 | 1.00 | 0.82 | 0.70 |
| Cyp4a14 | 8.68 | 1.00 | 1.00 | 1.00 | 1.00 | 1.00 | 1.00 | 1.00 | 1.00 | 1.00 | 0.73 | 0.76 |
| D10Bwg1379e | 1.00 | 1.00 | 1.00 | 1.00 | 1.00 | 1.00 | 1.00 | 1.00 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 | 1.00 | 1.00 | 1.00 |
| Ddi2 | 1.00 | 1.00 | 0.78 | 0.80 | 0.96 | 1.22 | 1.63 | 1.01 | 1.37 | 1.42 | 0.60 | 1.00 |
| Ddit4l | 1.00 | 1.00 | 1.02 | 1.44 | 1.74 | 1.19 | 1.86 | 1.27 | 0.73 | 0.91 | 1.41 | 1.05 |
| Defa17 | 0.36 | 1.00 | 1.00 | 1.00 | 1.00 | 1.00 | 1.00 | 1.00 | 1.00 | 1.00 | 1.00 | 1.00 |
| Defa23 | 0.68 | 1.00 | 1.00 | 1.00 | 1.00 | 1.00 | 1.00 | 1.00 | 1.00 | 1.00 | 1.00 | 1.00 |
| Defa24 | 0.52 | 1.00 | 1.00 | 1.00 | 1.00 | 1.00 | 1.00 | 1.00 | 1.00 | 1.00 | 1.00 | 1.00 |
| Defa3 | 1.24 | 1.00 | 1.00 | 1.00 | 1.00 | 1.00 | 1.00 | 1.00 | 1.00 | 1.00 | 1.00 | 1.00 |
| Defa4 | 1.00 | 1.00 | 1.00 | 1.00 | 1.00 | 1.00 | 1.00 | 1.00 | 1.00 | 1.00 | 1.00 | 1.00 |
| Defa-rs1 | 1.00 | 1.00 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 | 1.00 | 1.00 |
| Defb1 | 1.00 | 1.00 | 1.00 | 1.00 | 1.00 | 1.00 | 1.00 | 1.00 | 1.00 | 1.00 | 1.15 | 0.87 |
| Defb12 | 1.00 | 1.00 | 1.00 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 | 1.00 | 1.00 | 1.62 |
| Defb2 | 1.00 | 1.00 | 1.00 | 1.00 | 1.00 | 1.00 | 1.00 | 1.00 | 1.00 | 1.00 | 0.55 | 1.44 |
| Defb20 | 1.00 | 1.00 | 1.00 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.00 | 1.00 | 1.00 | 1.00 | 1.00 | 1.00 | 1.00 | 1.00 | 1.00 |
| Defb30 | 1.00 | 1.00 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 | 1.00 | 1.00 | 1.00 |
| Defb42 | 1.00 | 1.00 | 1.00 | 1.00 | 1.43 | 0.98 | 1.00 | 1.00 | 1.00 | 1.00 | 1.57 | 1.13 |
| Defb45 | 1.00 | 1.00 | 1.00 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Dmbt1 | 1.00 | 1.00 | 1.00 | 1.00 | 1.00 | 1.00 | 1.00 | 1.00 | 1.00 | 1.00 | 1.00 | 1.00 |
| Dnajb14 | 1.00 | 1.00 | 1.00 | 0.98 | 0.87 | 1.02 | 1.07 | 0.88 | 1.22 | 1.25 | 0.55 | 1.08 |
| Dsp | 1.00 | 1.00 | 1.00 | 1.00 | 1.00 | 1.00 | 1.07 | 1.04 | 0.94 | 0.96 | 0.80 | 0.93 |
| Eddm3b | 1.00 | 1.00 | 1.00 | 1.00 | 1.00 | 1.00 | 1.00 | 1.00 | 1.00 | 1.00 | 1.17 | 1.16 |
| Efcab4b | 1.00 | 1.00 | 1.00 | 1.00 | 1.00 | 1.00 | 1.00 | 1.00 | 0.90 | 1.18 | 1.00 | 1.00 |
| Egr1 | 1.00 | 1.00 | 1.24 | 5.26 | 0.76 | 0.83 | 0.91 | 0.89 | 0.78 | 1.40 | 0.64 | 1.60 |
| Egr2 | 1.00 | 1.00 | 0.84 | 1.31 | 1.00 | 1.00 | 0.80 | 1.08 | 0.92 | 0.72 | 1.00 | 1.00 |
| Ehf | 1.00 | 1.00 | 1.00 | 1.00 | 1.00 | 1.00 | 1.00 | 1.00 | 1.05 | 0.87 | 1.10 | 0.83 |
| Ehhadh | 5.36 | 1.00 | 1.28 | 0.85 | 1.09 | 1.20 | 0.87 | 1.47 | 0.93 | 0.92 | 0.86 | 0.86 |
| Eif3j1 | 1.00 | 1.00 | 1.00 | 40.35 | 1.00 | 1.00 | 1.00 | 13.81 | 1.00 | 1.00 | 0.09 | 0.10 |
| Eif3j2 | 1.00 | 1.00 | 0.95 | 0.16 | 0.93 | 0.91 | 0.92 | 0.29 | 1.01 | 0.90 | 11.75 | 2.23 |
| Elf3 | 1.00 | 1.00 | 1.00 | 1.00 | 1.00 | 1.00 | 1.00 | 1.00 | 1.00 | 1.06 | 0.93 | 1.06 |
| Emx2 | 1.00 | 1.00 | 1.42 | 0.86 | 1.00 | 1.00 | 1.00 | 1.00 | 1.00 | 1.00 | 1.03 | 0.94 |
| Enpp1 | 1.00 | 1.00 | 1.07 | 0.84 | 1.00 | 1.00 | 0.98 | 1.16 | 1.06 | 0.99 | 0.91 | 0.91 |
| Epcam | 1.00 | 1.00 | 1.00 | 1.00 | 1.00 | 1.00 | 1.00 | 1.00 | 0.87 | 0.98 | 1.15 | 0.98 |
| Eppin | 1.00 | 1.00 | 1.00 | 1.00 | 1.00 | 1.00 | 1.00 | 1.00 | 1.00 | 1.00 | 1.00 | 1.00 |
| Faah | 1.00 | 1.00 | 1.00 | 1.00 | 1.00 | 1.00 | 1.00 | 1.00 | 0.93 | 1.04 | 1.11 | 1.22 |
| Fabp1 | 16.55 | 1.00 | 1.00 | 1.00 | 1.00 | 1.00 | 1.00 | 1.00 | 0.89 | 0.99 | 1.03 | 1.00 |
| Fam84a | 1.00 | 1.00 | 1.00 | 1.00 | 1.00 | 1.00 | 1.00 | 1.01 | 1.14 | 1.00 | 0.95 | 0.86 |
| Fbxl18 | 1.00 | 1.00 | 0.74 | 1.09 | 1.08 | 1.56 | 1.20 | 1.06 | 1.13 | 1.10 | 0.59 | 0.99 |
| Fga | 13.22 | 1.00 | 1.03 | 1.00 | 1.00 | 1.00 | 1.00 | 1.00 | 1.00 | 1.00 | 1.14 | 1.08 |
| Fgb | 15.94 | 1.00 | 1.17 | 1.00 | 1.00 | 1.00 | 1.00 | 1.00 | 1.00 | 1.00 | 1.32 | 0.95 |
| Fgg | 11.62 | 1.00 | 1.00 | 1.00 | 1.00 | 1.00 | 1.00 | 1.00 | 1.00 | 1.00 | 1.34 | 1.00 |
| Folr1 | 1.00 | 1.00 | 1.00 | 1.00 | 1.00 | 1.00 | 1.00 | 1.00 | 1.00 | 1.00 | 1.07 | 0.92 |
| Foxn3 | 1.00 | 1.00 | 0.68 | 0.90 | 1.05 | 1.28 | 1.69 | 1.45 | 1.18 | 1.15 | 0.40 | 1.23 |
| Gal3st4 | 1.00 | 1.00 | 1.00 | 1.00 | 1.00 | 1.00 | 1.00 | 1.00 | 1.26 | 1.13 | 1.00 | 1.00 |
| Galnt12 | 1.00 | 1.00 | 1.00 | 1.00 | 1.00 | 1.00 | 1.00 | 1.00 | 1.05 | 1.07 | 1.00 | 1.00 |
| Gamt | 1.00 | 1.00 | 0.94 | 0.98 | 1.66 | 1.77 | 0.94 | 0.56 | 0.86 | 1.27 | 1.07 | 1.00 |

Fig. 37-11

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Cyp2d9 | 1.03 | 1.00 | 0.99 | 1.08 | 0.74 | 1.00 | 2.81 | 2.27 | 1.00 | 1.00 | 1.00 | 1.00 |
| Cyp2e1 | 0.81 | 0.87 | 1.80 | 1.01 | 0.29 | 0.90 | 0.82 | 0.79 | 0.40 | 0.56 | 4.86 | 0.54 |
| Cyp3a11 | 1.08 | 1.09 | 1.00 | 0.88 | 1.52 | 2.10 | 1.00 | 5.58 | 1.00 | 1.00 | 1.00 | 1.00 |
| Cyp4a10 | 0.93 | 0.64 | 1.00 | 1.00 | 0.43 | 1.00 | 1.82 | 1.69 | 1.00 | 1.00 | 1.00 | 1.00 |
| Cyp4a14 | 0.88 | 0.59 | 1.00 | 1.00 | 0.27 | 1.00 | 1.82 | 2.43 | 1.00 | 1.00 | 1.00 | 1.00 |
| D10Bwg1379e | 1.00 | 1.00 | 2.27 | 1.15 | 1.15 | 1.07 | 1.00 | 1.00 | 0.86 | 1.00 | 1.00 | 1.00 |
| D730048I06Rik | 1.00 | 1.00 | 1.00 | 1.00 | 1.00 | 1.00 | 192.7 | 1.00 | 1.00 | 1.00 | 1.00 | 1.00 |
| Ddi2 | 1.49 | 0.51 | 7.08 | 0.90 | 1.09 | 1.03 | 1.19 | 0.76 | 0.37 | 1.63 | 1.28 | 1.24 |
| Ddit4l | 1.00 | 1.00 | 0.90 | 1.05 | 1.02 | 1.35 | 7.25 | 13.38 | 1.23 | 1.10 | 1.00 | 1.00 |
| Defa17 | 1.00 | 1.00 | 0.58 | 0.93 | 9.94 | 45.94 | 1.00 | 1.00 | 1.21 | 0.68 | 1.00 | 1.00 |
| Defa23 | 1.00 | 1.00 | 0.36 | 1.50 | 0.17 | 17.63 | 1.00 | 1.00 | 1.61 | 2.85 | 1.00 | 1.00 |
| Defa24 | 1.00 | 1.00 | 0.98 | 0.93 | 15.15 | 55.01 | 1.00 | 1.00 | 1.67 | 1.00 | 1.00 | 1.00 |
| Defa3 | 1.00 | 1.00 | 0.81 | 2.69 | 11.71 | 47.49 | 1.00 | 1.00 | 1.38 | 0.73 | 1.00 | 1.00 |
| Defa4 | 1.00 | 1.00 | 1.00 | 0.41 | 16.83 | 1.00 | 1.00 | 1.00 | 1.00 | 1.00 | 1.00 | 1.00 |
| Defa-rs1 | 1.00 | 1.00 | 1.00 | 1.00 | 11.06 | 6.26 | 1.00 | 1.00 | 2.22 | 0.57 | 1.00 | 1.00 |
| Defa-rs7 | 1.00 | 1.00 | 1.00 | 1.00 | 15.28 | 13.35 | 1.00 | 1.00 | 1.00 | 1.00 | 1.00 | 1.00 |
| Defb1 | 1.94 | 1.13 | 0.72 | 2.38 | 0.64 | 1.15 | 5.33 | 3.00 | 1.00 | 1.00 | 1.00 | 1.00 |
| Defb12 | 1.00 | 1.00 | 1.00 | 1.00 | 1.00 | 1.00 | 169.2 | 11.04 | 1.00 | 1.00 | 1.00 | 1.00 |
| Defb15 | 1.00 | 1.00 | 1.00 | 1.00 | 1.00 | 1.00 | 296.6 | 2.64 | 1.65 | 1.00 | 1.00 | 1.00 |
| Defb18 | 1.00 | 1.00 | 1.00 | 1.00 | 1.00 | 1.00 | 124.0 | 47.97 | 1.00 | 1.00 | 1.00 | 1.00 |
| Defb2 | 1.00 | 1.00 | 1.00 | 1.00 | 1.00 | 1.00 | 9.83 | 1.00 | 1.00 | 1.00 | 1.00 | 1.00 |
| Defb20 | 1.00 | 1.00 | 1.00 | 1.00 | 1.00 | 1.00 | 87.55 | 202.1 | 0.69 | 1.00 | 1.00 | 1.00 |
| Defb21 | 1.00 | 1.00 | 1.00 | 1.00 | 1.00 | 1.00 | 34.33 | 1.68 | 2.06 | 0.62 | 1.00 | 1.00 |
| Defb25 | 1.00 | 1.00 | 1.00 | 1.00 | 1.00 | 1.00 | 33.46 | 320.6 | 1.00 | 1.00 | 1.00 | 1.10 |
| Defb30 | 1.00 | 1.00 | 1.00 | 1.00 | 1.00 | 1.00 | 40.42 | 1.00 | 1.26 | 1.11 | 1.00 | 1.00 |
| Defb37 | 1.00 | 1.00 | 0.91 | 2.02 | 1.00 | 1.00 | 6.27 | 1.00 | 1.00 | 1.00 | 1.00 | 1.00 |
| Defb39 | 1.00 | 1.00 | 1.00 | 1.00 | 1.00 | 1.00 | 15.00 | 1.00 | 1.00 | 1.00 | 1.00 | 1.00 |
| Defb41 | 1.00 | 1.00 | 1.00 | 1.00 | 1.00 | 1.00 | 42.31 | 16.04 | 1.53 | 1.13 | 1.00 | 1.00 |
| Defb42 | 1.00 | 1.00 | 1.00 | 1.00 | 1.00 | 1.00 | 235.7 | 126.3 | 1.00 | 1.34 | 1.00 | 1.00 |
| Defb45 | 1.00 | 1.00 | 1.00 | 1.00 | 1.00 | 1.00 | 32.17 | 1.77 | 2.01 | 0.89 | 1.00 | 1.00 |
| Defb47 | 1.00 | 1.00 | 1.00 | 1.00 | 1.00 | 1.00 | 7.52 | 171.6 | 1.00 | 1.00 | 1.00 | 1.00 |
| Defb48 | 1.00 | 1.00 | 1.00 | 1.00 | 1.00 | 1.00 | 39.84 | 288.3 | 1.02 | 1.00 | 1.00 | 1.00 |
| Dmbt1 | 1.00 | 0.92 | 1.14 | 1.11 | 1.53 | 1.32 | 1.00 | 1.00 | 1.00 | 1.00 | 33.29 | 0.09 |
| Dnajb14 | 1.18 | 0.44 | 1.88 | 0.80 | 1.20 | 1.01 | 1.04 | 0.68 | 1.34 | 1.03 | 1.04 | 0.90 |
| Dsp | 1.07 | 0.84 | 1.36 | 1.01 | 0.94 | 0.98 | 7.20 | 5.31 | 1.00 | 1.00 | 1.00 | 1.00 |
| Eddm3b | 1.00 | 1.00 | 1.00 | 1.00 | 1.00 | 1.00 | 36.86 | 6.00 | 1.00 | 1.00 | 1.00 | 1.00 |
| Efcab4b | 1.00 | 1.00 | 7.07 | 0.64 | 0.95 | 1.24 | 1.00 | 1.00 | 1.00 | 1.00 | 1.13 | 1.00 |
| Egr1 | 2.03 | 0.74 | 1.00 | 1.46 | 0.90 | 1.18 | 0.51 | 1.90 | 0.78 | 0.46 | 1.08 | 1.04 |
| Egr2 | 1.00 | 1.00 | 1.25 | 1.00 | 0.80 | 1.18 | 5.64 | 5.44 | 1.00 | 1.00 | 1.42 | 0.98 |
| Ehf | 1.00 | 1.00 | 1.13 | 1.10 | 0.86 | 0.99 | 5.38 | 4.46 | 1.00 | 1.00 | 1.10 | 0.93 |
| Ehhadh | 1.16 | 0.79 | 0.89 | 1.07 | 1.03 | 1.04 | 0.79 | 0.73 | 0.69 | 1.21 | 1.11 | 1.26 |
| Eif3j1 | 1.00 | 1.00 | 1.00 | 1.00 | 1.00 | 1.00 | 0.06 | 1.00 | 1.00 | 11.80 | 0.87 | 0.06 |
| Eif3j2 | 1.01 | 0.84 | 0.85 | 1.29 | 1.05 | 0.91 | 13.98 | 0.79 | 1.27 | 0.09 | 1.06 | 2.37 |
| Elf3 | 1.00 | 1.00 | 0.99 | 1.06 | 1.22 | 0.97 | 9.88 | 4.17 | 1.00 | 1.00 | 1.00 | 1.00 |
| Emx2 | 1.00 | 1.00 | 1.00 | 1.00 | 1.00 | 1.00 | 5.33 | 4.01 | 0.82 | 1.00 | 1.00 | 1.00 |
| Enpp1 | 1.06 | 0.79 | 1.10 | 0.90 | 1.05 | 0.93 | 11.59 | 1.32 | 1.00 | 1.00 | 1.15 | 0.99 |
| Epcam | 1.00 | 1.00 | 0.84 | 0.94 | 1.10 | 1.05 | 7.42 | 6.08 | 1.20 | 0.88 | 1.05 | 1.00 |
| Eppin | 1.00 | 1.00 | 1.00 | 1.00 | 1.00 | 1.00 | 23.17 | 6.99 | 1.29 | 0.94 | 1.00 | 1.00 |
| Faah | 0.90 | 1.09 | 0.81 | 1.00 | 0.95 | 0.99 | 5.68 | 3.51 | 1.03 | 1.00 | 1.05 | 1.04 |
| Fabp1 | 0.76 | 1.14 | 1.00 | 1.00 | 1.98 | 2.01 | 1.33 | 3.34 | 1.00 | 1.00 | 1.00 | 1.00 |
| Fam84a | 1.14 | 1.00 | 1.05 | 1.26 | 1.10 | 1.00 | 2.24 | 6.67 | 0.90 | 0.97 | 1.25 | 0.79 |
| Fbxl18 | 2.13 | 0.63 | 5.65 | 0.99 | 1.13 | 0.95 | 0.90 | 1.27 | 0.74 | 0.83 | 1.07 | 0.89 |
| Fga | 1.07 | 1.33 | 1.00 | 1.00 | 0.27 | 1.00 | 1.19 | 5.25 | 1.00 | 1.00 | 1.00 | 1.00 |
| Fgb | 1.07 | 1.41 | 1.00 | 1.00 | 0.22 | 1.00 | 1.00 | 5.28 | 1.00 | 0.96 | 1.00 | 1.00 |
| Fgg | 1.06 | 1.42 | 1.00 | 1.00 | 0.42 | 1.00 | 1.00 | 3.50 | 1.00 | 1.00 | 1.00 | 1.00 |
| Folr1 | 1.00 | 1.00 | 1.00 | 1.00 | 0.85 | 1.07 | 5.14 | 2.95 | 1.15 | 0.80 | 1.00 | 1.00 |
| Foxn3 | 2.07 | 0.37 | 6.93 | 0.87 | 0.91 | 1.11 | 1.03 | 0.97 | 0.54 | 1.10 | 1.07 | 1.16 |
| Gal3st4 | 1.00 | 1.00 | 0.80 | 1.43 | 0.80 | 0.94 | 6.33 | 1.00 | 1.00 | 1.00 | 1.16 | 0.89 |
| Galnt12 | 1.00 | 1.00 | 0.91 | 1.03 | 1.10 | 1.04 | 6.71 | 1.83 | 0.94 | 1.06 | 0.85 | 0.85 |
| Gamt | 0.71 | 1.34 | 0.64 | 0.75 | 1.02 | 1.37 | 6.60 | 3.22 | 1.36 | 0.89 | 1.43 | 0.57 |

Fig. 37-12

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Cyp2d9 | 1.00 | 1.00 | 1.00 | 1.00 | 1.00 | 1.00 | 1.00 | 1.00 | 1.00 | 1.00 |
| Cyp2e1 | 0.59 | 0.84 | 1.00 | 1.00 | 1.00 | 1.00 | 1.02 | 0.86 | 1.00 | 0.62 |
| Cyp3a11 | 1.00 | 1.00 | 1.00 | 1.00 | 1.00 | 1.00 | 1.00 | 0.25 | 1.00 | 1.00 |
| Cyp4a10 | 1.00 | 1.00 | 1.00 | 1.00 | 1.00 | 1.00 | 1.00 | 0.64 | 1.00 | 1.00 |
| Cyp4a14 | 1.00 | 1.00 | 1.00 | 1.00 | 1.00 | 1.00 | 1.00 | 0.51 | 1.00 | 1.00 |
| D10Bwg1379e | 1.34 | 0.38 | 0.72 | 6.10 | 1.53 | 0.99 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 | 1.00 |
| Ddi2 | 1.85 | 0.30 | 0.73 | 3.76 | 1.09 | 1.13 | 0.63 | 1.59 | 2.80 | 1.55 |
| Ddit4l | 1.00 | 1.00 | 0.84 | 1.00 | 0.98 | 1.11 | 0.78 | 1.10 | 1.00 | 1.00 |
| Defa17 | 0.96 | 1.00 | 1.18 | 1.00 | 1.00 | 1.00 | 0.57 | 1.00 | 1.00 | 1.00 |
| Defa23 | 1.00 | 1.00 | 1.00 | 1.00 | 1.00 | 1.00 | 0.99 | 1.00 | 1.00 | 1.00 |
| Defa24 | 0.78 | 1.00 | 1.04 | 1.00 | 1.00 | 1.00 | 0.86 | 1.00 | 1.00 | 1.00 |
| Defa3 | 1.00 | 1.00 | 1.48 | 1.00 | 1.00 | 1.00 | 1.50 | 1.00 | 1.00 | 1.00 |
| Defa4 | 1.54 | 1.00 | 1.00 | 1.00 | 1.00 | 1.00 | 1.00 | 1.00 | 1.00 | 1.00 |
| Defa-rs1 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 |
| Defb1 | 1.00 | 1.00 | 1.00 | 1.03 | 1.00 | 1.12 | 1.02 | 0.90 | 1.00 | 1.00 |
| Defb12 | 1.00 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 | 1.00 |
| Defb2 | 1.00 | 1.00 | 1.00 | 1.00 | 1.00 | 1.00 | 1.00 | 1.00 | 1.00 | 1.00 |
| Defb20 | 1.00 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.03 | 1.00 | 1.00 | 1.00 | 1.00 | 1.00 | 1.00 |
| Defb30 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 | 1.00 |
| Defb42 | 1.00 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 |
| Dmbt1 | 0.97 | 0.77 | 1.00 | 1.00 | 1.00 | 1.00 | 1.00 | 1.00 | 1.00 | 1.00 |
| Dnajb14 | 1.10 | 1.00 | 0.59 | 5.50 | 1.25 | 0.80 | 0.86 | 1.48 | 1.53 | 1.51 |
| Dsp | 1.01 | 0.76 | 1.00 | 1.03 | 1.00 | 1.00 | 0.90 | 1.07 | 1.00 | 1.00 |
| Eddm3b | 1.00 | 1.00 | 1.00 | 1.00 | 1.00 | 1.00 | 1.00 | 1.00 | 1.00 | 1.00 |
| Efcab4b | 1.00 | 1.00 | 1.00 | 1.00 | 1.00 | 1.00 | 1.00 | 1.00 | 2.63 | 1.72 |
| Egr1 | 0.77 | 1.13 | 1.55 | 1.47 | 1.66 | 1.50 | 0.93 | 0.66 | 0.99 | 0.65 |
| Egr2 | 1.00 | 1.00 | 2.04 | 2.11 | 2.39 | 2.57 | 0.92 | 0.92 | 1.00 | 1.00 |
| Ehf | 1.21 | 0.94 | 1.00 | 1.00 | 1.00 | 1.00 | 0.85 | 0.94 | 1.00 | 1.00 |
| Ehhadh | 0.95 | 0.77 | 0.84 | 1.19 | 0.99 | 0.95 | 0.90 | 0.92 | 1.05 | 0.76 |
| Eif3j1 | 5.99 | 1.00 | 1.00 | 0.10 | 1.00 | 1.00 | 1.00 | 0.08 | 17.14 | 1.00 |
| Eif3j2 | 0.18 | 1.19 | 1.09 | 5.15 | 1.00 | 1.00 | 1.15 | 3.33 | 0.05 | 0.99 |
| Elf3 | 1.22 | 1.58 | 1.00 | 1.00 | 1.00 | 1.00 | 1.00 | 1.00 | 1.00 | 1.00 |
| Emx2 | 1.00 | 1.00 | 0.97 | 1.20 | 1.01 | 0.97 | 1.20 | 0.98 | 1.00 | 1.00 |
| Enpp1 | 1.00 | 1.12 | 1.00 | 1.00 | 0.95 | 1.00 | 1.06 | 0.99 | 0.77 | 0.79 |
| Epcam | 1.08 | 1.81 | 1.00 | 1.00 | 1.00 | 1.00 | 0.99 | 0.90 | 1.00 | 1.00 |
| Eppin | 1.00 | 1.00 | 1.00 | 1.00 | 1.00 | 1.00 | 1.00 | 1.00 | 1.00 | 1.00 |
| Faah | 1.00 | 0.83 | 1.04 | 0.91 | 0.87 | 1.04 | 1.05 | 0.97 | 0.88 | 0.80 |
| Fabp1 | 1.59 | 1.00 | 1.00 | 1.00 | 1.00 | 1.00 | 1.00 | 0.24 | 1.00 | 0.96 |
| Fam84a | 1.00 | 1.00 | 1.09 | 1.00 | 0.94 | 0.94 | 0.78 | 1.01 | 1.00 | 1.00 |
| Fbxl18 | 1.00 | 1.00 | 0.77 | 2.40 | 1.35 | 1.14 | 0.64 | 1.25 | 2.26 | 1.53 |
| Fga | 1.00 | 1.00 | 1.00 | 1.00 | 1.00 | 1.00 | 1.00 | 0.51 | 1.00 | 1.00 |
| Fgb | 1.00 | 1.00 | 1.00 | 1.00 | 1.00 | 1.00 | 1.00 | 0.28 | 1.00 | 1.00 |
| Fgg | 1.00 | 1.00 | 1.00 | 1.00 | 1.00 | 1.00 | 1.00 | 0.29 | 1.00 | 1.00 |
| Folr1 | 1.00 | 1.00 | 0.78 | 0.54 | 0.94 | 0.77 | 0.91 | 0.86 | 1.00 | 1.00 |
| Foxn3 | 1.44 | 0.61 | 0.91 | 3.52 | 1.75 | 0.99 | 0.74 | 1.30 | 3.01 | 2.00 |
| Gal3st4 | 1.00 | 1.00 | 1.10 | 0.93 | 1.09 | 1.19 | 1.01 | 1.00 | 0.93 | 0.80 |
| Galnt12 | 1.00 | 1.00 | 1.00 | 1.00 | 1.02 | 1.00 | 0.93 | 1.08 | 0.63 | 0.89 |
| Gamt | 0.90 | 1.37 | 0.96 | 0.66 | 1.09 | 0.98 | 1.51 | 1.00 | 1.02 | 0.95 |

Fig. 37- 13

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Gatad2b | 1.00 | 1.00 | 0.89 | 0.74 | 1.00 | 1.12 | 1.49 | 1.29 | 1.13 | 0.94 | 0.53 | 1.05 |
| Gbp10 | 1.00 | 1.00 | 1.21 | 1.00 | 1.21 | 1.09 | 1.25 | 1.38 | 1.07 | 1.18 | 1.00 | 1.35 |
| Gbp2 | 2.04 | 1.69 | 0.91 | 1.24 | 1.12 | 1.14 | 1.16 | 1.03 | 1.13 | 1.29 | 1.11 | 0.90 |
| Gbp3 | 1.00 | 1.00 | 1.00 | 1.38 | 0.94 | 1.04 | 0.83 | 1.30 | 1.06 | 1.42 | 0.84 | 0.92 |
| Gbp5 | 1.00 | 1.00 | 0.88 | 1.32 | 1.05 | 1.09 | 0.90 | 1.14 | 1.29 | 1.30 | 1.00 | 1.31 |
| Gbp6 | 1.00 | 1.00 | 1.29 | 1.20 | 1.01 | 1.11 | 1.10 | 1.34 | 1.17 | 1.17 | 1.14 | 1.51 |
| Gbp7 | 1.00 | 1.69 | 0.75 | 1.37 | 0.97 | 1.08 | 0.87 | 1.45 | 1.09 | 1.08 | 0.96 | 1.12 |
| Gc | 6.81 | 1.00 | 1.00 | 1.00 | 1.00 | 1.00 | 1.00 | 1.00 | 1.00 | 1.00 | 0.92 | 0.73 |
| Gcnt4 | 1.00 | 1.00 | 1.00 | 1.00 | 1.00 | 1.00 | 1.00 | 1.00 | 1.00 | 1.00 | 0.82 | 0.97 |
| Gfra1 | 1.00 | 1.00 | 1.11 | 0.99 | 0.85 | 0.59 | 1.15 | 1.23 | 0.88 | 0.90 | 1.21 | 1.16 |
| Ggt1 | 1.00 | 1.00 | 1.00 | 1.00 | 1.00 | 1.00 | 1.00 | 1.00 | 1.00 | 1.00 | 1.04 | 1.06 |
| Gjb3 | 1.00 | 1.00 | 1.00 | 1.00 | 1.00 | 1.00 | 1.00 | 1.00 | 1.02 | 1.17 | 0.86 | 1.00 |
| Glra1 | 1.00 | 1.00 | 1.00 | 1.00 | 1.00 | 1.00 | 1.00 | 1.00 | 1.00 | 1.00 | 1.00 | 1.00 |
| Gm10104 | 1.00 | 1.00 | 1.00 | 1.00 | 1.00 | 1.00 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 | 1.00 | 1.00 | 1.00 |
| Gm12250 | 1.00 | 0.74 | 1.00 | 1.20 | 1.00 | 1.32 | 1.13 | 2.96 | 1.38 | 1.25 | 0.91 | 1.62 |
| Gm13363 | 1.00 | 1.00 | 0.85 | 0.83 | 0.29 | 0.63 | 1.96 | 0.92 | 1.00 | 1.00 | 1.00 | 1.00 |
| Gm14475 | 1.00 | 1.00 | 1.00 | 1.00 | 1.00 | 1.00 | 1.00 | 1.00 | 1.00 | 1.00 | 1.00 | 1.00 |
| Gm14851 | 0.84 | 1.00 | 1.00 | 1.00 | 1.00 | 1.00 | 1.00 | 1.00 | 1.00 | 1.00 | 1.00 | 1.00 |
| Gm15284 | 0.88 | 1.00 | 1.00 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 | 1.00 | 1.00 | 1.00 |
| Gm20604 | 1.00 | 1.00 | 1.00 | 3.67 | 5.18 | 0.48 | 0.81 | 0.65 | 1.05 | 1.33 | 1.08 | 1.86 |
| Gm2083 | 3.19 | 1.00 | 2.24 | 1.55 | 3.06 | 0.81 | 1.00 | 1.00 | 1.00 | 1.00 | 1.00 | 1.00 |
| Gm20878 | 1.00 | 1.00 | 1.00 | 1.00 | 1.00 | 1.00 | 1.00 | 1.00 | 1.00 | 0.85 | 1.00 | 1.00 |
| Gm21498 | 1.00 | 1.00 | 1.00 | 1.00 | 1.00 | 1.00 | 1.00 | 1.00 | 1.00 | 1.00 | 1.00 | 1.00 |
| Gm266 | 1.00 | 1.00 | 1.00 | 1.00 | 1.00 | 1.00 | 1.00 | 1.00 | 1.00 | 1.00 | 0.72 | 1.27 |
| Gm4759 | 1.00 | 1.00 | 1.00 | 1.00 | 1.00 | 1.00 | 1.00 | 1.00 | 1.00 | 1.00 | 1.00 | 1.00 |
| Gm4846 | 1.00 | 1.00 | 1.00 | 1.00 | 1.00 | 1.00 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 | 1.00 | 1.00 | 1.00 |
| Gm5916 | 1.00 | 1.00 | 1.00 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 | 1.00 | 1.00 | 1.00 |
| Gm6792 | 1.00 | 1.00 | 1.00 | 1.00 | 1.00 | 1.00 | 1.00 | 1.00 | 1.00 | 1.00 | 1.00 | 1.00 |
| Gm6793 | 1.00 | 1.00 | 1.00 | 1.00 | 1.00 | 1.00 | 1.00 | 1.00 | 1.00 | 1.00 | 1.00 | 1.00 |
| Gm766 | 1.00 | 1.00 | 1.00 | 1.00 | 1.00 | 1.00 | 1.00 | 1.00 | 1.00 | 1.00 | 1.00 | 1.00 |
| Gnmt | 6.92 | 1.00 | 0.74 | 1.00 | 1.80 | 1.08 | 1.05 | 0.82 | 0.83 | 0.65 | 1.34 | 1.14 |
| Gp2 | 1.00 | 1.00 | 1.00 | 1.00 | 1.00 | 1.00 | 1.00 | 1.00 | 1.00 | 1.00 | 1.12 | 1.66 |
| Gpr26 | 1.00 | 1.00 | 1.00 | 1.00 | 1.00 | 1.00 | 1.00 | 1.00 | 1.00 | 1.00 | 1.00 | 1.00 |
| Gpx5 | 1.00 | 1.00 | 1.00 | 1.00 | 1.00 | 1.00 | 1.00 | 1.00 | 1.00 | 1.00 | 1.00 | 3.02 |
| Gstm6 | 1.00 | 1.00 | 1.00 | 1.00 | 1.00 | 1.00 | 0.71 | 1.03 | 0.65 | 0.99 | 0.83 | 0.94 |
| Gstm7 | 1.00 | 1.00 | 0.98 | 1.36 | 0.83 | 0.92 | 0.92 | 1.00 | 1.03 | 1.28 | 1.16 | 0.83 |
| Guca2a | 1.00 | 1.00 | 1.00 | 1.00 | 1.00 | 1.00 | 1.00 | 1.00 | 1.00 | 1.00 | 0.99 | 0.83 |
| H2-Q7 | 1.25 | 1.06 | 1.26 | 3.07 | 0.99 | 1.48 | 1.17 | 1.71 | 0.92 | 1.54 | 0.74 | 1.67 |
| H2-T9 | 1.00 | 0.97 | 1.68 | 1.00 | 0.32 | 2.65 | 0.82 | 0.80 | 1.17 | 0.55 | 4.38 | 1.01 |
| Hba-a1 | 0.63 | 0.56 | 0.24 | 0.64 | 2.00 | 0.90 | 1.10 | 1.78 | 0.82 | 1.22 | 1.21 | 1.01 |
| Hbb-bs | 0.67 | 0.65 | 1.35 | 2.03 | 0.33 | 0.42 | 0.87 | 0.60 | 1.43 | 0.92 | 1.41 | 1.19 |
| Hcar1 | 1.00 | 1.00 | 1.00 | 1.00 | 0.74 | 6.58 | 1.00 | 1.00 | 1.00 | 1.00 | 1.18 | 1.00 |
| Hipk2 | 0.86 | 0.89 | 0.58 | 0.86 | 1.34 | 1.90 | 1.74 | 1.25 | 1.19 | 1.31 | 0.32 | 1.24 |
| Hist1h4i | 0.66 | 0.62 | 1.12 | 0.74 | 5.17 | 0.74 | 1.23 | 1.08 | 0.79 | 1.28 | 1.23 | 1.14 |
| Hist2h2bb | 0.70 | 0.38 | 1.02 | 0.85 | 3.40 | 0.96 | 2.95 | 0.76 | 1.18 | 0.62 | 1.57 | 1.66 |
| Hist2h3c2 | 1.00 | 0.63 | 2.66 | 1.11 | 0.77 | 0.41 | 0.60 | 0.72 | 1.70 | 6.40 | 0.31 | 5.61 |
| Hmbox1 | 1.00 | 1.00 | 0.51 | 0.92 | 1.12 | 1.25 | 1.99 | 1.59 | 1.55 | 1.25 | 0.66 | 1.00 |
| Hmgcs2 | 11.15 | 1.00 | 0.94 | 0.76 | 0.69 | 0.68 | 0.77 | 0.76 | 0.91 | 1.08 | 0.73 | 0.62 |
| Hoxa6 | 1.00 | 1.00 | 1.00 | 1.00 | 1.08 | 1.13 | 1.00 | 1.00 | 1.00 | 1.00 | 1.07 | 0.51 |
| Hpx | 7.43 | 1.00 | 1.00 | 1.00 | 1.00 | 1.00 | 1.00 | 1.00 | 1.24 | 1.47 | 1.00 | 1.00 |
| Hs6st3 | 1.00 | 1.00 | 1.00 | 1.00 | 1.00 | 1.00 | 1.00 | 1.00 | 1.94 | 1.55 | 1.00 | 1.00 |
| Hsd3b5 | 1.00 | 1.00 | 1.00 | 1.00 | 1.00 | 1.00 | 1.00 | 1.00 | 1.00 | 1.00 | 0.95 | 0.88 |
| Iapp | 1.00 | 1.00 | 1.00 | 1.00 | 1.00 | 1.00 | 1.00 | 1.00 | 1.00 | 1.00 | 1.00 | 1.00 |
| Icam2 | 5.11 | 2.95 | 0.99 | 0.99 | 1.26 | 1.30 | 0.96 | 0.97 | 1.01 | 1.00 | 1.01 | 0.90 |

Fig. 37-14

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Gatad2b | 2.43 | 0.42 | 6.16 | 0.93 | 1.00 | 1.02 | 1.05 | 1.05 | 1.16 | 0.93 | 1.09 | 1.05 |
| Gbp10 | 0.89 | 0.99 | 1.30 | 0.85 | 1.00 | 1.00 | 0.75 | 1.22 | 1.00 | 1.00 | 1.30 | 0.98 |
| Gbp2 | 0.74 | 0.98 | 0.93 | 0.73 | 0.78 | 1.05 | 0.84 | 1.00 | 1.00 | 1.00 | 1.08 | 1.00 |
| Gbp3 | 1.00 | 0.90 | 0.83 | 0.78 | 1.03 | 1.00 | 0.87 | 1.14 | 1.00 | 1.00 | 1.01 | 0.89 |
| Gbp5 | 1.00 | 1.00 | 1.32 | 1.04 | 1.01 | 1.18 | 0.64 | 1.51 | 1.00 | 1.00 | 1.10 | 1.02 |
| Gbp6 | 0.91 | 1.10 | 1.18 | 0.96 | 0.97 | 1.19 | 0.79 | 1.20 | 1.00 | 1.00 | 1.32 | 0.99 |
| Gbp7 | 1.24 | 0.85 | 1.37 | 0.96 | 0.96 | 1.06 | 0.72 | 1.02 | 1.00 | 1.00 | 0.96 | 0.99 |
| Gc | 0.97 | 1.06 | 1.00 | 1.00 | 0.56 | 0.81 | 2.45 | 1.94 | 1.00 | 1.00 | 1.00 | 1.00 |
| Gcnt4 | 0.87 | 0.73 | 1.40 | 1.21 | 1.44 | 1.21 | 1.21 | 7.78 | 0.59 | 1.24 | 1.00 | 1.00 |
| Gfra1 | 1.18 | 0.69 | 1.09 | 0.92 | 0.73 | 0.93 | 20.02 | 2.72 | 0.98 | 1.21 | 1.00 | 1.00 |
| Ggt1 | 1.00 | 1.00 | 0.87 | 0.83 | 3.40 | 1.68 | 8.07 | 4.36 | 1.00 | 1.00 | 1.00 | 1.00 |
| Gjb3 | 1.00 | 1.00 | 0.90 | 0.94 | 0.80 | 1.00 | 5.76 | 3.51 | 1.23 | 0.77 | 1.00 | 1.00 |
| Glra1 | 1.00 | 1.00 | 1.00 | 1.00 | 1.00 | 1.00 | 1.00 | 1.00 | 1.00 | 1.00 | 1.00 | 1.00 |
| Gm10104 | 1.00 | 1.00 | 1.52 | 1.00 | 12.34 | 4.68 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 5.17 | 1.00 | 1.00 |
| Gm1110 | 1.00 | 1.00 | 1.00 | 1.00 | 0.90 | 0.96 | 18.93 | 7.10 | 1.00 | 1.00 | 1.00 | 1.00 |
| Gm12250 | 0.81 | 0.76 | 1.63 | 0.98 | 1.00 | 1.00 | 0.61 | 1.41 | 1.00 | 1.00 | 1.32 | 1.21 |
| Gm13363 | 1.00 | 0.19 | 1.61 | 1.30 | 1.00 | 0.63 | 0.10 | 0.27 | 1.09 | 1.04 | 1.39 | 0.89 |
| Gm14475 | 1.00 | 1.00 | 1.00 | 1.00 | 1.00 | 1.00 | 1.00 | 1.00 | 22.51 | 0.38 | 1.00 | 1.00 |
| Gm14851 | 1.00 | 1.00 | 1.00 | 1.00 | 5.39 | 2.31 | 1.00 | 1.00 | 1.04 | 0.43 | 1.00 | 1.00 |
| Gm15284 | 1.00 | 1.00 | 0.44 | 0.96 | 10.29 | 14.23 | 1.00 | 1.00 | 0.71 | 0.55 | 1.00 | 1.00 |
| Gm15386 | 1.00 | 1.00 | 1.00 | 1.00 | 1.00 | 1.00 | 43.18 | 59.73 | 1.00 | 0.82 | 1.00 | 1.00 |
| Gm17727 | 1.00 | 1.00 | 1.00 | 1.00 | 1.00 | 1.00 | 20.07 | 1.00 | 1.00 | 1.00 | 1.00 | 1.00 |
| Gm20604 | 1.13 | 1.36 | 0.79 | 1.26 | 1.40 | 1.62 | 1.00 | 1.28 | 1.26 | 0.84 | 0.91 | 0.91 |
| Gm2083 | 0.98 | 1.16 | 1.00 | 0.45 | 0.43 | 1.37 | 2.13 | 11.86 | 0.45 | 1.49 | 1.00 | 1.00 |
| Gm20878 | 1.00 | 1.00 | 1.00 | 1.00 | 1.00 | 1.00 | 1.00 | 1.00 | 5.44 | 1.00 | 1.00 | 1.00 |
| Gm21498 | 1.00 | 1.00 | 1.00 | 1.00 | 5.58 | 1.42 | 1.00 | 1.00 | 1.00 | 1.00 | 1.00 | 1.00 |
| Gm266 | 1.00 | 1.00 | 1.00 | 1.00 | 1.00 | 1.00 | 7.95 | 4.62 | 1.00 | 1.00 | 1.00 | 1.00 |
| Gm4759 | 1.00 | 1.00 | 1.00 | 1.00 | 1.00 | 1.00 | 1.00 | 1.00 | 1.00 | 1.00 | 1.16 | 1.61 |
| Gm4846 | 1.00 | 1.00 | 1.00 | 1.00 | 1.00 | 1.00 | 9.65 | 85.25 | 1.00 | 1.00 | 1.00 | 1.00 |
| Gm5531 | 1.00 | 1.00 | 1.00 | 1.00 | 1.00 | 1.00 | 46.92 | 7.24 | 1.00 | 1.00 | 1.00 | 1.00 |
| Gm5916 | 1.00 | 1.00 | 1.00 | 1.00 | 1.00 | 1.00 | 1.00 | 17.99 | 1.00 | 1.00 | 1.00 | 1.00 |
| Gm6040 | 1.00 | 1.00 | 1.00 | 1.00 | 1.00 | 1.00 | 6.98 | 1.00 | 1.00 | 1.00 | 1.00 | 1.00 |
| Gm6792 | 1.00 | 1.00 | 1.00 | 1.00 | 1.00 | 1.00 | 120.4 | 2.26 | 1.00 | 1.00 | 1.00 | 1.00 |
| Gm6793 | 1.00 | 1.00 | 1.00 | 1.00 | 1.00 | 1.00 | 1.00 | 1.00 | 5.78 | 0.79 | 1.00 | 1.00 |
| Gm766 | 1.00 | 1.00 | 1.00 | 1.00 | 18.67 | 10.78 | 1.00 | 1.00 | 1.00 | 1.00 | 1.00 | 1.00 |
| Gnmt | 0.94 | 1.20 | 1.00 | 1.00 | 0.90 | 0.83 | 1.08 | 2.10 | 1.07 | 1.00 | 1.00 | 1.00 |
| Gp2 | 1.00 | 1.00 | 1.69 | 11.26 | 2.40 | 11.77 | 1.00 | 1.00 | 1.00 | 1.00 | 14.47 | 0.18 |
| Gpr26 | 1.00 | 1.00 | 1.00 | 1.00 | 1.00 | 1.00 | 1.00 | 1.00 | 1.00 | 1.00 | 1.00 | 1.00 |
| Gpx5 | 1.00 | 1.00 | 1.00 | 1.00 | 1.00 | 1.00 | 2332 | 1307 | 1.00 | 1.00 | 1.00 | 1.00 |
| Gstm6 | 0.89 | 1.56 | 0.71 | 1.74 | 0.92 | 0.91 | 5.08 | 4.09 | 1.16 | 0.91 | 1.00 | 1.00 |
| Gstm7 | 0.93 | 1.23 | 0.90 | 1.71 | 1.13 | 1.03 | 5.93 | 3.75 | 1.42 | 0.93 | 1.39 | 0.67 |
| Guca2a | 1.00 | 1.00 | 0.68 | 0.99 | 0.98 | 1.62 | 1.00 | 1.00 | 1.00 | 1.00 | 1.00 | 1.00 |
| H2-Q7 | 1.04 | 1.46 | 0.87 | 0.89 | 0.88 | 0.96 | 1.61 | 1.14 | 1.14 | 1.46 | 0.92 | 1.37 |
| H2-T9 | 0.56 | 1.94 | 0.95 | 1.53 | 1.46 | 1.00 | 5.31 | 2.99 | 1.00 | 1.00 | 0.77 | 8.12 |
| Hba-a1 | 0.87 | 1.86 | 7.91 | 0.04 | 1.88 | 0.48 | 0.96 | 0.69 | 1.18 | 1.74 | 0.87 | 0.92 |
| Hbb-bs | 0.68 | 1.30 | 9.56 | 2.78 | 3.01 | 14.06 | 1.08 | 0.54 | 1.57 | 1.00 | 1.10 | 0.52 |
| Hcar1 | 1.00 | 1.00 | 1.17 | 0.74 | 1.03 | 1.13 | 0.88 | 2.15 | 1.00 | 1.00 | 0.82 | 0.87 |
| Hipk2 | 2.09 | 0.48 | 6.25 | 0.92 | 1.21 | 1.03 | 1.12 | 1.32 | 0.78 | 0.96 | 0.83 | 1.24 |
| Hist1h4i | 0.71 | 1.76 | 0.97 | 1.94 | 1.45 | 1.12 | 0.98 | 1.13 | 2.51 | 1.71 | 0.98 | 0.95 |
| Hist2h2bb | 1.00 | 1.00 | 5.12 | 0.63 | 1.02 | 1.25 | 2.79 | 1.32 | 0.32 | 0.66 | 1.14 | 0.85 |
| Hist2h3c2 | 1.21 | 2.35 | 1.44 | 3.51 | 0.79 | 0.98 | 1.90 | 1.08 | 0.69 | 0.48 | 1.15 | 0.37 |
| Hmbox1 | 2.27 | 0.41 | 4.83 | 0.83 | 1.05 | 0.83 | 1.08 | 1.14 | 0.49 | 0.94 | 1.11 | 1.08 |
| Hmgcs2 | 0.97 | 0.94 | 0.86 | 0.96 | 0.82 | 0.82 | 1.44 | 1.31 | 0.92 | 0.96 | 1.07 | 0.73 |
| Hoxa6 | 1.00 | 1.00 | 5.59 | 1.03 | 1.00 | 1.00 | 1.21 | 1.90 | 0.84 | 1.00 | 1.00 | 1.00 |
| Hpx | 0.89 | 1.34 | 1.00 | 1.00 | 0.53 | 1.00 | 1.00 | 1.91 | 1.00 | 1.00 | 1.00 | 1.00 |
| Hs6st3 | 1.00 | 1.00 | 1.00 | 1.00 | 1.00 | 1.00 | 1.00 | 1.00 | 1.00 | 1.00 | 1.00 | 1.00 |
| Hsd3b5 | 0.85 | 6.02 | 1.00 | 1.00 | 1.00 | 1.00 | 1.00 | 1.00 | 1.00 | 1.00 | 1.00 | 1.00 |
| Iapp | 1.00 | 1.00 | 1.00 | 1.00 | 1.95 | 0.97 | 14.07 | 1.00 | 1.00 | 1.00 | 1.00 | 1.00 |
| Icam2 | 1.26 | 1.42 | 0.85 | 1.36 | 0.94 | 0.95 | 0.91 | 0.83 | 1.00 | 1.00 | 0.92 | 0.99 |

Fig. 37-15

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Gatad2b | 1.00 | 0.76 | 0.93 | 5.06 | 1.30 | 0.88 | 0.71 | 1.54 | 2.72 | 1.46 |
| Gbp10 | 1.00 | 1.00 | 1.00 | 1.00 | 1.00 | 1.00 | 0.99 | 8.09 | 1.00 | 1.00 |
| Gbp2 | 1.00 | 1.54 | 1.00 | 0.86 | 1.49 | 1.55 | 1.09 | 11.07 | 1.31 | 1.33 |
| Gbp3 | 1.00 | 1.00 | 1.00 | 1.00 | 1.43 | 2.34 | 0.95 | 5.22 | 1.05 | 1.30 |
| Gbp5 | 1.00 | 1.00 | 1.00 | 1.00 | 1.00 | 1.66 | 1.00 | 8.93 | 1.09 | 1.25 |
| Gbp6 | 1.00 | 1.00 | 1.00 | 1.12 | 1.15 | 1.66 | 1.14 | 6.69 | 1.00 | 1.00 |
| Gbp7 | 1.00 | 1.00 | 1.05 | 1.27 | 1.14 | 1.52 | 0.86 | 5.22 | 1.12 | 1.11 |
| Gc | 1.00 | 1.28 | 1.00 | 1.00 | 1.00 | 1.00 | 1.00 | 0.89 | 1.00 | 1.00 |
| Gcnt4 | 1.00 | 1.00 | 1.08 | 1.50 | 1.16 | 1.05 | 0.94 | 1.11 | 1.00 | 1.00 |
| Gfra1 | 1.00 | 1.10 | 1.02 | 1.34 | 1.06 | 1.01 | 1.12 | 1.02 | 0.97 | 0.78 |
| Ggt1 | 0.93 | 1.03 | 1.00 | 1.00 | 1.00 | 1.00 | 1.00 | 1.00 | 2.33 | 1.00 |
| Gjb3 | 1.00 | 1.00 | 1.00 | 1.00 | 1.00 | 1.00 | 1.12 | 0.94 | 0.95 | 0.98 |
| Glra1 | 1.00 | 1.00 | 0.60 | 5.18 | 1.95 | 1.00 | 1.00 | 1.00 | 1.00 | 1.00 |
| Gm10104 | 1.00 | 1.00 | 1.00 | 1.00 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 | 1.00 |
| Gm12250 | 1.00 | 1.00 | 1.00 | 1.00 | 1.00 | 1.00 | 1.00 | 8.92 | 1.27 | 1.39 |
| Gm13363 | 1.00 | 0.93 | 1.00 | 1.86 | 1.00 | 1.00 | 1.00 | 6.09 | 1.21 | 1.07 |
| Gm14475 | 1.00 | 1.00 | 1.00 | 1.00 | 1.00 | 1.00 | 1.00 | 1.00 | 1.00 | 1.00 |
| Gm14851 | 0.84 | 1.00 | 1.27 | 1.00 | 1.00 | 1.00 | 1.00 | 1.00 | 1.00 | 1.00 |
| Gm15284 | 1.17 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 | 1.00 |
| Gm20604 | 1.00 | 1.00 | 0.87 | 1.50 | 1.34 | 0.38 | 1.09 | 1.04 | 1.20 | 1.05 |
| Gm2083 | 1.00 | 0.59 | 1.00 | 1.00 | 1.00 | 1.00 | 1.00 | 0.04 | 1.00 | 1.71 |
| Gm20878 | 1.00 | 1.00 | 1.00 | 1.00 | 1.00 | 1.00 | 2.42 | 0.61 | 1.00 | 1.00 |
| Gm21498 | 1.81 | 1.00 | 1.18 | 1.00 | 1.00 | 1.00 | 0.88 | 1.00 | 1.00 | 1.00 |
| Gm266 | 1.00 | 1.00 | 0.91 | 0.67 | 0.64 | 0.87 | 1.10 | 1.00 | 1.00 | 1.00 |
| Gm4759 | 1.00 | 1.00 | 1.00 | 1.00 | 1.00 | 1.00 | 1.00 | 1.00 | 6.06 | 2.64 |
| Gm4846 | 1.00 | 1.00 | 1.00 | 1.00 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 | 1.00 |
| Gm5916 | 1.00 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 | 1.00 |
| Gm6792 | 1.00 | 1.00 | 1.00 | 1.00 | 1.00 | 1.00 | 1.00 | 1.00 | 1.00 | 1.00 |
| Gm6793 | 1.00 | 1.00 | 1.00 | 1.00 | 1.00 | 1.00 | 1.00 | 1.00 | 1.00 | 1.00 |
| Gm766 | 1.00 | 1.00 | 1.00 | 1.00 | 1.00 | 1.00 | 1.00 | 1.00 | 1.00 | 1.00 |
| Gnmt | 0.95 | 1.21 | 1.04 | 0.41 | 0.71 | 1.16 | 1.84 | 0.44 | 0.85 | 0.87 |
| Gp2 | 0.95 | 0.95 | 1.00 | 1.00 | 1.00 | 1.00 | 1.00 | 1.00 | 1.00 | 1.00 |
| Gpr26 | 1.00 | 1.00 | 0.69 | 5.24 | 1.37 | 0.88 | 1.00 | 1.00 | 1.00 | 1.00 |
| Gpx5 | 1.00 | 1.00 | 1.00 | 1.00 | 1.00 | 1.00 | 1.00 | 1.00 | 1.00 | 1.00 |
| Gstm6 | 1.00 | 1.00 | 0.95 | 0.57 | 1.14 | 0.92 | 1.23 | 0.76 | 1.00 | 1.00 |
| Gstm7 | 0.89 | 0.83 | 1.09 | 0.75 | 0.98 | 0.94 | 0.96 | 1.00 | 1.00 | 1.00 |
| Guca2a | 1.00 | 7.47 | 1.00 | 1.00 | 1.00 | 1.00 | 1.10 | 1.20 | 1.00 | 1.00 |
| H2-Q7 | 1.00 | 1.00 | 1.00 | 1.08 | 1.06 | 1.90 | 0.68 | 6.79 | 0.96 | 1.28 |
| H2-T9 | 1.00 | 1.00 | 1.00 | 1.00 | 1.00 | 1.00 | 1.18 | 2.27 | 1.00 | 0.73 |
| Hba-a1 | 0.86 | 1.79 | 1.42 | 0.52 | 1.21 | 1.33 | 1.28 | 0.64 | 0.62 | 0.58 |
| Hbb-bs | 1.01 | 0.35 | 3.74 | 0.25 | 0.49 | 1.26 | 1.31 | 0.04 | 0.37 | 0.52 |
| Hcar1 | 1.00 | 1.00 | 0.79 | 1.00 | 1.00 | 1.00 | 1.00 | 1.00 | 1.00 | 1.00 |
| Hipk2 | 1.00 | 0.44 | 0.84 | 7.61 | 1.84 | 1.00 | 0.69 | 1.52 | 2.63 | 1.36 |
| Hist1h4i | 0.43 | 0.93 | 0.53 | 0.77 | 0.99 | 1.08 | 1.40 | 1.78 | 0.64 | 0.80 |
| Hist2h2bb | 1.00 | 1.00 | 0.80 | 1.80 | 1.75 | 1.40 | 0.98 | 1.04 | 1.20 | 0.98 |
| Hist2h3c2 | 1.17 | 0.71 | 0.81 | 0.55 | 0.76 | 0.73 | 3.43 | 7.75 | 0.38 | 1.13 |
| Hmbox1 | 1.08 | 0.53 | 0.68 | 5.87 | 2.00 | 0.96 | 0.62 | 1.60 | 3.81 | 2.45 |
| Hmgcs2 | 0.85 | 0.62 | 1.00 | 0.79 | 0.93 | 1.20 | 0.88 | 0.84 | 1.00 | 1.00 |
| Hoxa6 | 1.00 | 1.00 | 1.00 | 1.00 | 1.00 | 1.00 | 1.00 | 1.00 | 1.00 | 1.00 |
| Hpx | 1.00 | 0.83 | 1.00 | 1.00 | 1.00 | 1.00 | 1.00 | 0.52 | 1.00 | 1.00 |
| Hs6st3 | 1.00 | 1.00 | 0.85 | 5.30 | 1.55 | 0.86 | 1.00 | 1.00 | 1.00 | 1.00 |
| Hsd3b5 | 1.00 | 1.00 | 1.00 | 1.00 | 1.00 | 1.00 | 1.00 | 1.00 | 1.00 | 1.00 |
| Iapp | 0.83 | 1.15 | 1.00 | 1.00 | 1.00 | 1.00 | 1.00 | 1.00 | 1.00 | 1.00 |
| Icam2 | 1.00 | 1.00 | 1.10 | 0.86 | 1.25 | 1.36 | 0.87 | 1.31 | 0.91 | 0.69 |

Fig. 37-16

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Ido1 | 1.00 | 1.00 | 1.00 | 1.00 | 1.00 | 1.00 | 1.00 | 1.00 | 1.00 | 1.00 | 1.00 | 1.00 |
| Ifi47 | 1.02 | 1.09 | 1.23 | 1.38 | 0.92 | 0.99 | 0.75 | 1.18 | 1.13 | 1.18 | 1.41 | 1.33 |
| Ifit1 | 0.48 | 0.78 | 0.86 | 1.38 | 0.80 | 1.01 | 1.21 | 0.83 | 1.00 | 0.80 | 1.23 | 0.78 |
| Igfbp2 | 5.38 | 1.00 | 1.00 | 1.00 | 1.00 | 1.00 | 1.00 | 1.00 | 1.00 | 0.97 | 0.77 | 0.78 |
| Igfbp4 | 5.20 | 1.47 | 1.10 | 0.98 | 1.00 | 0.95 | 0.89 | 0.95 | 0.94 | 0.97 | 1.05 | 0.93 |
| Igtp | 0.58 | 0.59 | 0.96 | 1.58 | 0.98 | 1.62 | 0.92 | 2.06 | 1.08 | 1.18 | 0.88 | 1.82 |
| Iigp1 | 1.00 | 1.00 | 0.92 | 1.79 | 0.85 | 1.23 | 0.98 | 1.46 | 0.84 | 1.26 | 1.08 | 1.42 |
| Ins2 | 1.00 | 1.00 | 1.00 | 1.00 | 1.00 | 1.00 | 1.00 | 1.00 | 1.00 | 1.00 | 1.00 | 1.00 |
| Irgm2 | 1.00 | 0.68 | 0.95 | 1.31 | 1.10 | 1.36 | 1.11 | 2.11 | 1.18 | 1.08 | 0.99 | 1.57 |
| Kap | 1.00 | 3.34 | 1.00 | 1.00 | 1.00 | 1.00 | 0.86 | 0.59 | 1.54 | 0.94 | 1.30 | 1.04 |
| Kcna3 | 1.00 | 1.00 | 1.00 | 1.00 | 1.00 | 1.00 | 1.00 | 1.00 | 1.28 | 1.41 | 1.00 | 1.00 |
| Kcnk1 | 1.00 | 1.00 | 0.91 | 0.95 | 1.00 | 1.00 | 1.00 | 1.00 | 1.11 | 0.83 | 0.92 | 0.99 |
| Kcnk9 | 1.00 | 1.00 | 1.00 | 1.00 | 1.00 | 1.00 | 1.00 | 1.00 | 1.00 | 1.00 | 1.00 | 1.00 |
| Klf7 | 0.50 | 0.59 | 0.85 | 1.11 | 1.03 | 1.76 | 1.60 | 1.18 | 1.27 | 1.24 | 0.88 | 1.00 |
| Klk1 | 1.00 | 1.00 | 1.00 | 1.00 | 1.00 | 1.00 | 1.00 | 1.24 | 1.60 | 0.82 | 1.14 | 1.04 |
| Krt18 | 1.00 | 1.00 | 1.00 | 1.00 | 1.00 | 1.00 | 1.79 | 1.31 | 0.92 | 0.85 | 0.91 | 0.72 |
| Krt5 | 1.00 | 1.00 | 1.00 | 1.00 | 1.00 | 1.00 | 1.00 | 1.00 | 1.15 | 1.00 | 1.00 | 1.00 |
| Lars2 | 0.63 | 0.82 | 0.84 | 0.69 | 1.02 | 1.29 | 1.13 | 0.91 | 1.07 | 1.08 | 0.86 | 0.96 |
| Lcn10 | 1.00 | 1.00 | 1.00 | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 | 1.00 | 1.00 | 1.00 |
| Lcn2 | 1.67 | 0.59 | 0.32 | 0.51 | 1.30 | 1.73 | 0.54 | 0.50 | 0.97 | 0.97 | 0.98 | 0.80 |
| Lcn5 | 1.00 | 1.00 | 1.00 | 1.00 | 1.00 | 1.00 | 1.00 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 | 1.00 | 1.00 | 1.00 |
| Lgals6 | 1.00 | 1.00 | 1.00 | 1.00 | 1.00 | 1.00 | 1.00 | 1.00 | 1.00 | 1.00 | 1.00 | 1.00 |
| Lingo1 | 1.00 | 1.00 | 1.00 | 1.00 | 1.00 | 1.00 | 1.00 | 1.00 | 0.88 | 1.00 | 1.00 | 1.00 |
| Lmbrd2 | 1.00 | 1.00 | 0.93 | 0.85 | 1.00 | 1.00 | 1.03 | 1.24 | 1.16 | 1.30 | 0.82 | 1.38 |
| Lnpep | 1.00 | 1.00 | 0.76 | 0.87 | 1.13 | 1.09 | 1.41 | 1.03 | 1.53 | 0.93 | 0.81 | 0.87 |
| Lrcol1 | 1.00 | 1.00 | 1.00 | 1.00 | 1.00 | 1.00 | 1.00 | 1.00 | 1.00 | 1.00 | 1.00 | 1.00 |
| Ltf | 0.94 | 0.29 | 0.54 | 0.44 | 1.00 | 1.00 | 5.68 | 1.00 | 1.03 | 0.84 | 1.00 | 1.00 |
| Ly6g5b | 1.00 | 1.00 | 1.00 | 1.00 | 1.00 | 1.00 | 1.00 | 1.00 | 1.27 | 1.00 | 1.00 | 1.00 |
| Ly6g5c | 1.00 | 1.00 | 1.00 | 1.00 | 1.00 | 1.00 | 1.00 | 1.00 | 1.00 | 1.00 | 1.00 | 1.00 |
| Lypd8 | 1.00 | 1.00 | 1.00 | 1.36 | 1.00 | 1.00 | 1.00 | 1.00 | 1.00 | 1.00 | 1.00 | 1.00 |
| Mal | 1.00 | 1.00 | 1.08 | 1.05 | 1.37 | 0.72 | 1.05 | 1.26 | 1.10 | 0.94 | 1.08 | 0.96 |
| Mat1a | 15.26 | 1.00 | 1.00 | 1.00 | 1.00 | 1.00 | 1.00 | 1.00 | 0.88 | 0.76 | 1.00 | 1.00 |
| Mbnl3 | 1.00 | 1.00 | 1.00 | 1.00 | 1.00 | 1.00 | 1.00 | 1.00 | 0.91 | 0.88 | 1.00 | 1.00 |
| Mgat5 | 1.00 | 1.00 | 1.00 | 1.00 | 1.00 | 1.01 | 1.37 | 1.64 | 1.52 | 1.26 | 0.74 | 1.00 |
| Mgst1 | 5.24 | 1.39 | 1.45 | 1.00 | 0.94 | 1.11 | 0.78 | 0.94 | 0.98 | 0.92 | 0.93 | 0.75 |
| Mib1 | 1.00 | 1.00 | 0.59 | 0.86 | 1.03 | 1.30 | 1.36 | 0.99 | 1.31 | 1.00 | 0.85 | 1.31 |
| Mir10a | 1.00 | 1.00 | 1.00 | 1.00 | 45.29 | 1.00 | 1.00 | 1.00 | 0.04 | 1.00 | 1.00 | 1.00 |
| Mir1291 | 1.00 | 1.00 | 1.00 | 0.05 | 45.73 | 26.71 | 20.98 | 0.06 | 1.00 | 1.00 | 1.00 | 1.00 |
| Mir142b | 27.05 | 12.21 | 1.00 | 1.00 | 1.00 | 1.00 | 1.00 | 1.00 | 0.06 | 1.00 | 1.00 | 1.00 |
| Mir1668 | 1.00 | 29.23 | 1.00 | 1.00 | 1.00 | 1.00 | 1.00 | 1.00 | 1.00 | 1.00 | 1.00 | 1.00 |
| Mir1938 | 1.00 | 1.00 | 1.00 | 1.00 | 1.00 | 1.00 | 1.00 | 1.00 | 1.00 | 1.00 | 1.00 | 1.00 |
| Mir1957b | 1.00 | 1.00 | 1.00 | 13.06 | 1.00 | 1.00 | 3.87 | 1.00 | 1.00 | 1.00 | 1.00 | 1.00 |
| Mir214 | 1.00 | 1.00 | 1.00 | 1.00 | 1.00 | 1.00 | 1.00 | 1.00 | 1.00 | 1.00 | 34.55 | 1.00 |
| Mir365-2 | 1.00 | 1.00 | 1.00 | 1.00 | 1.00 | 1.00 | 1.00 | 1.00 | 1.00 | 1.00 | 1.00 | 1.00 |
| Mir486 | 1.00 | 1.00 | 1.00 | 8.30 | 1.00 | 1.00 | 1.00 | 1.00 | 1.00 | 1.00 | 1.00 | 1.00 |
| Mir546 | 1.00 | 1.00 | 1.00 | 10.56 | 1.00 | 1.00 | 1.00 | 1.00 | 1.00 | 1.00 | 1.00 | 1.00 |
| Mir6236 | 0.63 | 0.98 | 13.21 | 0.08 | 0.84 | 5.37 | 2.33 | 1.51 | 4.26 | 10.08 | 0.88 | 0.03 |
| Mir6244 | 1.00 | 1.00 | 1.00 | 6.92 | 1.00 | 1.00 | 0.04 | 1.00 | 1.00 | 1.00 | 1.00 | 1.00 |
| Mir6338 | 1.00 | 1.00 | 131.4 | 1.00 | 1.00 | 1.00 | 1.00 | 1.00 | 1.00 | 1.00 | 1.00 | 1.00 |
| Mir6340 | 1.00 | 6.46 | 1.00 | 1.00 | 1.00 | 1.00 | 1.00 | 1.00 | 1.00 | 1.00 | 0.16 | 0.04 |
| Mir6357 | 1.00 | 1.00 | 1.00 | 1.00 | 1.00 | 1.00 | 1.00 | 1.00 | 1.00 | 1.00 | 1.00 | 1.00 |
| Mir6363 | 1.00 | 1.00 | 1.00 | 0.08 | 22.91 | 1.00 | 0.09 | 1.00 | 1.00 | 1.00 | 1.00 | 1.00 |
| Mir6516 | 1.00 | 1.00 | 1.00 | 1.00 | 1.00 | 1.00 | 1.00 | 1.00 | 1.00 | 1.00 | 1.00 | 1.00 |
| Mir682 | 1.00 | 1619 | 1.00 | 0.00 | 1.00 | 1.00 | 1.00 | 1.00 | 1.00 | 1184 | 1.00 | 1225 |
| Mir6992 | 1.00 | 1.00 | 1.00 | 1.00 | 1.00 | 1.00 | 1.00 | 1.00 | 1.00 | 1.00 | 1.00 | 1.00 |
| Mir703 | 1.00 | 1.00 | 0.01 | 1.00 | 3.42 | 0.53 | 0.03 | 0.03 | 0.01 | 0.69 | 41.42 | 0.75 |

Fig. 37-17

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Ido1 | 1.00 | 1.00 | 0.63 | 0.62 | 1.00 | 1.00 | 36.22 | 1.21 | 1.00 | 1.00 | 1.00 | 1.00 |
| Ifi47 | 0.87 | 1.40 | 0.99 | 1.14 | 0.99 | 1.25 | 0.64 | 1.08 | 1.00 | 1.00 | 0.96 | 1.03 |
| Ifit1 | 1.03 | 0.70 | 0.90 | 0.86 | 0.87 | 1.03 | 0.92 | 0.77 | 1.00 | 1.00 | 0.85 | 0.70 |
| Igfbp2 | 0.98 | 0.83 | 0.78 | 1.11 | 1.11 | 1.11 | 2.08 | 3.98 | 1.17 | 0.98 | 1.00 | 1.00 |
| Igfbp4 | 0.90 | 0.95 | 0.96 | 0.99 | 0.84 | 1.03 | 0.82 | 0.94 | 1.20 | 1.10 | 0.88 | 0.89 |
| Igtp | 0.73 | 1.18 | 1.26 | 1.06 | 0.97 | 1.43 | 0.81 | 1.65 | 1.00 | 1.13 | 0.90 | 0.99 |
| Iigp1 | 1.04 | 0.86 | 1.25 | 0.99 | 0.72 | 1.34 | 0.51 | 1.40 | 0.91 | 1.51 | 1.08 | 1.17 |
| Ins2 | 1.00 | 1.00 | 1.00 | 1.00 | 5.23 | 1.00 | 1.00 | 1.00 | 1.00 | 1.00 | 1.00 | 1.00 |
| Irgm2 | 0.86 | 0.93 | 1.27 | 1.23 | 0.88 | 1.15 | 0.65 | 1.23 | 1.00 | 1.00 | 0.80 | 0.96 |
| Kap | 1.00 | 1.00 | 0.69 | 1.00 | 1.00 | 1.00 | 77.52 | 1.47 | 1.00 | 1.00 | 1.09 | 0.84 |
| Kcna3 | 1.00 | 1.00 | 1.00 | 1.00 | 1.00 | 1.00 | 1.00 | 1.00 | 1.00 | 1.00 | 0.99 | 1.34 |
| Kcnk1 | 1.00 | 1.00 | 0.93 | 1.10 | 1.03 | 1.06 | 7.39 | 7.03 | 1.47 | 0.91 | 1.11 | 0.90 |
| Kcnk9 | 1.00 | 1.00 | 1.00 | 1.00 | 1.00 | 1.00 | 1.00 | 1.00 | 1.00 | 1.00 | 1.00 | 1.00 |
| Klf7 | 1.07 | 1.00 | 5.36 | 1.07 | 1.23 | 0.98 | 0.93 | 0.79 | 1.00 | 1.00 | 1.05 | 1.08 |
| Klk1 | 1.00 | 1.01 | 0.80 | 1.07 | 2.10 | 2.01 | 2.08 | 1.00 | 1.13 | 0.70 | 6.39 | 0.28 |
| Krt18 | 0.95 | 1.22 | 0.88 | 0.91 | 1.04 | 0.94 | 5.07 | 3.96 | 1.00 | 1.00 | 1.25 | 1.00 |
| Krt5 | 1.00 | 1.00 | 1.00 | 1.00 | 0.83 | 0.91 | 5.69 | 1.22 | 1.00 | 1.00 | 1.00 | 1.00 |
| Lars2 | 1.12 | 3.83 | 1.08 | 1.14 | 0.19 | 1.06 | 1.12 | 0.96 | 1.42 | 0.98 | 0.90 | 1.02 |
| Lcn10 | 1.00 | 1.00 | 1.00 | 1.00 | 1.00 | 1.00 | 6.37 | 65.65 | 1.00 | 1.00 | 1.00 | 1.00 |
| Lcn12 | 1.00 | 1.00 | 1.00 | 1.00 | 1.00 | 1.00 | 14.17 | 1.26 | 1.00 | 1.00 | 1.00 | 1.00 |
| Lcn2 | 0.45 | 2.92 | 1.18 | 0.63 | 0.56 | 0.89 | 4.31 | 8.99 | 1.37 | 0.71 | 1.44 | 2.15 |
| Lcn5 | 1.00 | 1.00 | 1.00 | 1.00 | 1.00 | 1.00 | 318.7 | 1.38 | 1.00 | 1.00 | 1.00 | 1.00 |
| Lcn6 | 1.00 | 1.00 | 1.00 | 1.00 | 1.00 | 1.00 | 11.03 | 13.63 | 1.00 | 1.00 | 1.00 | 1.00 |
| Lcn8 | 1.00 | 1.00 | 1.00 | 1.00 | 1.00 | 1.00 | 28.15 | 202.5 | 1.00 | 1.00 | 1.00 | 1.00 |
| Lcn9 | 1.00 | 1.00 | 1.00 | 1.00 | 1.00 | 1.00 | 17.33 | 168.0 | 1.00 | 1.00 | 1.00 | 1.00 |
| Lgals6 | 1.00 | 1.00 | 153.2 | 0.01 | 1.00 | 1.00 | 1.00 | 1.00 | 1.00 | 1.00 | 1.00 | 1.00 |
| Lingo1 | 1.00 | 1.00 | 1.00 | 1.00 | 1.00 | 1.00 | 6.75 | 5.66 | 0.78 | 1.19 | 0.88 | 1.13 |
| Lmbrd2 | 2.02 | 0.38 | 5.63 | 0.94 | 1.18 | 1.16 | 1.00 | 1.00 | 0.96 | 1.04 | 0.83 | 0.91 |
| Lnpep | 1.83 | 0.40 | 4.55 | 0.96 | 1.08 | 0.81 | 0.68 | 0.75 | 0.84 | 0.93 | 0.88 | 1.15 |
| Lrcol1 | 1.00 | 1.00 | 1.00 | 1.00 | 1.00 | 1.00 | 25.28 | 1.00 | 1.00 | 1.00 | 1.00 | 1.00 |
| Ltf | 1.00 | 1.00 | 1.00 | 1.00 | 0.82 | 0.81 | 1.00 | 1.00 | 1.00 | 1.00 | 1.52 | 2.49 |
| Ly6g5b | 1.00 | 1.00 | 0.78 | 1.00 | 1.00 | 1.00 | 17.65 | 97.18 | 0.95 | 1.43 | 0.63 | 1.39 |
| Ly6g5c | 1.00 | 1.00 | 1.00 | 1.00 | 1.00 | 1.00 | 14.69 | 51.15 | 1.00 | 1.00 | 1.00 | 1.00 |
| Lypd8 | 1.00 | 1.00 | 0.78 | 1.03 | 1.65 | 1.13 | 86.88 | 1.00 | 1.19 | 0.76 | 1.00 | 1.00 |
| Mal | 1.00 | 1.00 | 0.89 | 1.29 | 1.35 | 0.97 | 7.30 | 3.73 | 0.79 | 1.00 | 0.87 | 1.01 |
| Mat1a | 1.08 | 0.83 | 1.00 | 1.00 | 0.31 | 0.77 | 1.32 | 5.35 | 1.00 | 1.00 | 1.00 | 1.00 |
| Mbnl3 | 1.00 | 1.00 | 1.19 | 1.12 | 1.06 | 0.90 | 6.08 | 0.98 | 1.00 | 1.00 | 1.02 | 1.30 |
| Mgat5 | 1.00 | 1.00 | 5.60 | 0.90 | 0.93 | 0.96 | 0.98 | 1.18 | 0.50 | 1.16 | 0.94 | 0.87 |
| Mgst1 | 0.90 | 1.15 | 0.82 | 1.13 | 0.96 | 0.91 | 0.76 | 0.77 | 0.82 | 1.27 | 1.04 | 0.91 |
| Mib1 | 2.09 | 0.45 | 5.42 | 0.83 | 1.04 | 1.10 | 1.08 | 0.91 | 0.73 | 1.05 | 1.03 | 1.10 |
| Mir10a | 1.00 | 1.00 | 1.00 | 1.00 | 1.00 | 1.00 | 1.00 | 1.00 | 1.00 | 1.00 | 1.00 | 1.00 |
| Mir1291 | 1.00 | 13.30 | 1.00 | 0.04 | 1.00 | 1.00 | 0.06 | 1.00 | 1.00 | 25.19 | 0.01 | 0.04 |
| Mir142b | 1.00 | 1.00 | 1.00 | 1.00 | 1.00 | 1.00 | 1.00 | 1.00 | 1.00 | 1.00 | 1.62 | 0.74 |
| Mir1668 | 1.00 | 1.00 | 1.00 | 1.00 | 1.00 | 1.00 | 1.00 | 1.00 | 1.00 | 1.00 | 1.00 | 1.00 |
| Mir1938 | 1.00 | 1.00 | 1.00 | 1.00 | 1.00 | 1.00 | 1.00 | 1.00 | 1.00 | 1.00 | 1.00 | 223.1 |
| Mir1957b | 1.00 | 1.00 | 1.00 | 1.00 | 1.00 | 1.00 | 1.00 | 1.00 | 1.00 | 1.00 | 1.00 | 1.00 |
| Mir214 | 1.00 | 1.00 | 1.00 | 1.00 | 1.00 | 2.57 | 1.00 | 1.00 | 1.00 | 1.00 | 1.00 | 1.00 |
| Mir365-2 | 1.00 | 1.00 | 1.00 | 1.00 | 1.00 | 1.00 | 36.43 | 1.00 | 1.00 | 1.00 | 1.00 | 1.00 |
| Mir486 | 1.00 | 1.00 | 1.00 | 1.00 | 1.00 | 1.00 | 1.00 | 1.00 | 1.00 | 1.00 | 6.66 | 0.09 |
| Mir546 | 0.04 | 1.00 | 1.00 | 1.00 | 1.00 | 1.00 | 1.00 | 1.00 | 1.00 | 1.00 | 1.00 | 1.00 |
| Mir6236 | 1.09 | 4.76 | 0.43 | 0.06 | 0.10 | 3.86 | 0.09 | 9.23 | 0.55 | 1.39 | 0.75 | 2.98 |
| Mir6244 | 0.07 | 1.00 | 1.00 | 1.00 | 1.00 | 1.00 | 0.21 | 1.00 | 1.00 | 1.00 | 5.96 | 1.00 |
| Mir6338 | 1.00 | 1.00 | 1.00 | 1.00 | 1.00 | 1.00 | 1.00 | 1.00 | 1.00 | 1.00 | 1.00 | 1.00 |
| Mir6340 | 0.04 | 1.00 | 17.55 | 1.00 | 1.00 | 1.00 | 1.00 | 17.77 | 17.33 | 0.01 | 1.00 | 1.00 |
| Mir6357 | 1.00 | 1.00 | 1.00 | 1.00 | 0.02 | 1.00 | 72.62 | 0.01 | 0.06 | 1.00 | 1.00 | 1.00 |
| Mir6363 | 1.00 | 1.00 | 1.00 | 1.00 | 1.00 | 1.00 | 1.00 | 1.00 | 1.00 | 1.00 | 9.67 | 1.00 |
| Mir6516 | 1.00 | 1.00 | 1.00 | 1.00 | 1.00 | 1.00 | 1.00 | 1.00 | 1.00 | 1.00 | 27.13 | 1.00 |
| Mir682 | 1.00 | 1748 | 0.00 | 0.00 | 1.00 | 1.00 | 1.00 | 1.00 | 0.00 | 1.00 | 0.80 | 4060 |
| Mir6992 | 1.00 | 1.00 | 1.00 | 1.00 | 1.00 | 1.00 | 1.00 | 1.00 | 1.00 | 1.00 | 1.00 | 1.00 |
| Mir703 | 1.00 | 1.02 | 0.14 | 0.74 | 1.48 | 2.87 | 1.69 | 0.23 | 58.52 | 0.02 | 2.43 | 3.70 |

Fig. 37-18

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Ido1 | 1.00 | 1.00 | 0.97 | 1.06 | 0.91 | 1.30 | 1.00 | 1.00 | 1.00 | 1.00 |
| Ifi47 | 1.00 | 1.05 | 1.00 | 1.00 | 1.00 | 1.02 | 0.98 | 6.11 | 0.82 | 0.97 |
| Ifit1 | 1.00 | 1.00 | 1.26 | 0.69 | 1.30 | 1.56 | 1.00 | 6.88 | 0.80 | 0.99 |
| Igfbp2 | 1.00 | 1.00 | 0.90 | 0.73 | 0.81 | 0.87 | 1.03 | 0.93 | 1.00 | 1.00 |
| Igfbp4 | 0.76 | 1.05 | 0.96 | 0.79 | 0.91 | 0.99 | 1.03 | 0.92 | 0.95 | 1.02 |
| Igtp | 1.00 | 1.00 | 1.20 | 0.97 | 1.25 | 2.42 | 1.23 | 9.19 | 0.81 | 0.93 |
| Iigp1 | 1.00 | 1.40 | 1.00 | 1.00 | 1.00 | 1.31 | 1.13 | 11.68 | 0.90 | 1.89 |
| Ins2 | 0.91 | 1.29 | 1.00 | 0.95 | 1.73 | 1.00 | 1.00 | 1.00 | 1.00 | 1.00 |
| Irgm2 | 1.00 | 1.00 | 1.00 | 1.00 | 1.00 | 1.31 | 1.07 | 6.14 | 0.95 | 1.07 |
| Kap | 1.00 | 0.83 | 1.00 | 0.94 | 1.01 | 1.06 | 1.00 | 0.91 | 4.20 | 1.00 |
| Kcna3 | 1.00 | 1.00 | 0.66 | 5.03 | 1.45 | 1.06 | 1.00 | 1.00 | 3.68 | 1.68 |
| Kcnk1 | 1.02 | 0.88 | 0.90 | 0.94 | 0.99 | 0.96 | 1.04 | 0.79 | 1.00 | 1.00 |
| Kcnk9 | 1.00 | 1.00 | 0.89 | 5.42 | 1.43 | 0.80 | 1.00 | 1.00 | 1.00 | 1.00 |
| Klf7 | 1.00 | 1.00 | 0.86 | 4.86 | 2.06 | 0.96 | 0.78 | 1.21 | 4.58 | 1.57 |
| Klk1 | 0.93 | 1.09 | 1.00 | 1.00 | 1.00 | 1.00 | 1.00 | 1.33 | 0.83 | 0.47 |
| Krt18 | 0.90 | 0.95 | 1.00 | 0.79 | 0.71 | 0.66 | 1.00 | 1.00 | 1.20 | 0.59 |
| Krt5 | 1.02 | 1.00 | 1.00 | 1.00 | 1.00 | 1.00 | 1.04 | 1.06 | 1.00 | 1.00 |
| Lars2 | 0.82 | 6.31 | 0.83 | 1.26 | 0.85 | 1.06 | 0.81 | 0.86 | 1.37 | 1.05 |
| Lcn10 | 1.00 | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 | 1.00 |
| Lcn2 | 0.45 | 0.82 | 1.00 | 0.73 | 1.85 | 0.84 | 0.82 | 1.25 | 0.85 | 0.92 |
| Lcn5 | 1.00 | 1.00 | 1.00 | 1.00 | 1.00 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 | 1.00 |
| Lgals6 | 1.00 | 1.00 | 0.69 | 1.00 | 1.00 | 1.00 | 1.00 | 1.00 | 1.00 | 1.00 |
| Lingo1 | 1.00 | 1.00 | 1.01 | 1.11 | 0.88 | 0.93 | 0.80 | 0.89 | 1.00 | 1.00 |
| Lmbrd2 | 1.00 | 0.66 | 0.82 | 5.37 | 1.38 | 1.10 | 0.60 | 1.20 | 2.59 | 1.89 |
| Lnpep | 1.00 | 0.44 | 0.92 | 6.29 | 1.66 | 0.77 | 0.59 | 1.65 | 4.74 | 1.95 |
| Lrcol1 | 1.00 | 1.00 | 1.00 | 1.00 | 1.00 | 1.00 | 1.00 | 1.00 | 1.00 | 1.00 |
| Ltf | 1.00 | 1.00 | 1.00 | 1.00 | 1.00 | 1.00 | 1.00 | 1.00 | 1.05 | 1.09 |
| Ly6g5b | 1.00 | 1.00 | 1.11 | 0.90 | 1.00 | 1.00 | 1.20 | 0.82 | 0.83 | 1.22 |
| Ly6g5c | 1.00 | 1.00 | 1.00 | 1.00 | 1.00 | 1.00 | 1.00 | 1.00 | 1.00 | 1.00 |
| Lypd8 | 3.96 | 34.54 | 1.00 | 1.00 | 1.00 | 1.00 | 1.00 | 1.00 | 1.00 | 1.00 |
| Mal | 1.00 | 1.00 | 1.06 | 0.93 | 1.06 | 0.97 | 0.93 | 0.87 | 1.00 | 1.00 |
| Mat1a | 1.17 | 0.76 | 1.00 | 1.00 | 1.00 | 1.00 | 1.00 | 0.52 | 1.00 | 1.00 |
| Mbnl3 | 1.00 | 0.83 | 1.00 | 1.00 | 1.00 | 1.00 | 0.97 | 1.20 | 1.10 | 1.11 |
| Mgat5 | 1.00 | 1.00 | 0.84 | 3.04 | 1.37 | 0.96 | 0.73 | 1.51 | 3.51 | 1.85 |
| Mgst1 | 0.59 | 0.99 | 1.41 | 0.76 | 0.92 | 1.42 | 1.06 | 0.97 | 0.77 | 1.12 |
| Mib1 | 1.74 | 0.46 | 0.86 | 3.83 | 1.44 | 0.80 | 0.80 | 1.01 | 3.05 | 1.64 |
| Mir10a | 1.00 | 1.00 | 1.00 | 1.00 | 1.00 | 1.00 | 1.00 | 1.00 | 1.00 | 1.00 |
| Mir1291 | 1.00 | 1.00 | 0.06 | 22.63 | 0.05 | 15.97 | 1.00 | 1.00 | 1.00 | 1.00 |
| Mir142b | 1.00 | 1.00 | 1.00 | 1.00 | 1.00 | 1.00 | 1.00 | 1.00 | 1.25 | 0.45 |
| Mir1668 | 1.00 | 1.00 | 1.00 | 1.00 | 1.00 | 1.00 | 1.00 | 1.00 | 1.00 | 0.01 |
| Mir1938 | 1.00 | 1.00 | 1.00 | 1.00 | 1.00 | 1.00 | 1.00 | 1.00 | 1.00 | 1.00 |
| Mir1957b | 1.00 | 1.00 | 1.00 | 1.00 | 1.00 | 1.00 | 1.00 | 1.00 | 1.00 | 1.00 |
| Mir214 | 1.00 | 1.00 | 1.00 | 1.00 | 1.00 | 1.00 | 1.00 | 1.00 | 1.00 | 1.00 |
| Mir365-2 | 1.00 | 1.00 | 1.00 | 1.00 | 1.00 | 1.00 | 1.00 | 1.00 | 1.00 | 1.00 |
| Mir486 | 1.00 | 1.00 | 1.00 | 1.00 | 1.00 | 0.10 | 1.00 | 1.00 | 1.00 | 1.00 |
| Mir546 | 1.00 | 1.00 | 1.00 | 1.00 | 1.00 | 1.00 | 1.00 | 1.00 | 1.00 | 1.00 |
| Mir6236 | 1.58 | 5.64 | 1.74 | 14.70 | 0.04 | 51.74 | 47.76 | 0.03 | 0.62 | 2.02 |
| Mir6244 | 1.00 | 1.00 | 1.00 | 1.00 | 1.00 | 1.00 | 1.00 | 1.00 | 1.00 | 1.00 |
| Mir6338 | 1.00 | 1.00 | 1.00 | 1.00 | 1.00 | 1.00 | 1.00 | 1.00 | 1.00 | 1.00 |
| Mir6340 | 1.00 | 1.00 | 53.26 | 1.00 | 1.00 | 24.22 | 1.00 | 1.00 | 1.00 | 33.96 |
| Mir6357 | 1.00 | 1.00 | 0.02 | 1.00 | 1.00 | 1.00 | 0.02 | 1.00 | 1.00 | 0.04 |
| Mir6363 | 1.00 | 1.00 | 1.00 | 1.00 | 13.54 | 1.00 | 1.00 | 0.53 | 1.00 | 1.00 |
| Mir6516 | 1.00 | 1.00 | 1.00 | 1.00 | 1.00 | 1.00 | 1.00 | 1.00 | 1.00 | 1.00 |
| Mir682 | 1.00 | 2549 | 1.00 | 1765 | 1.00 | 1.00 | 2870 | 1.00 | 1.00 | 1.00 |
| Mir6992 | 1.00 | 1.00 | 0.03 | 50.35 | 1.00 | 1.00 | 1.00 | 1.00 | 1.00 | 1.00 |
| Mir703 | 0.39 | 1.12 | 0.03 | 2.40 | 1.00 | 0.01 | 5.10 | 2.32 | 0.36 | 0.68 |

Fig. 37- 19

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Mir7-1 | 1.00 | 1.00 | 1.00 | 1.00 | 1.00 | 1.00 | 1.00 | 1.00 | 1.00 | 1.00 | 1.00 | 1.00 |
| Mir719 | 1.00 | 1.00 | 1.00 | 1.00 | 1.00 | 1.00 | 1.00 | 0.54 | 1.00 | 1.00 | 43.25 | 1.00 |
| Mir760 | 1.00 | 1.00 | 1.00 | 1.00 | 1.00 | 1.00 | 1.00 | 1.00 | 1.00 | 1.00 | 1.00 | 1.00 |
| Mir8091 | 1.00 | 1.00 | 1.00 | 1.00 | 1.00 | 1.00 | 1.00 | 1.00 | 2.79 | 1.00 | 1.00 | 1.00 |
| Mir8093 | 1.00 | 1.00 | 1.00 | 1.00 | 1.00 | 1.00 | 1.00 | 1.00 | 1.00 | 1.00 | 0.08 | 5.23 |
| Mir8094 | 1.00 | 0.08 | 40.20 | 1.00 | 91.50 | 26.75 | 1.30 | 1.00 | 0.36 | 31.21 | 0.83 | 33.06 |
| Mir8096 | 1.00 | 1.00 | 1.00 | 1.00 | 1.00 | 1.00 | 1.00 | 1.00 | 1.00 | 1.00 | 1.00 | 1.00 |
| Mir8097 | 1.00 | 1.00 | 1.00 | 1.00 | 1.00 | 1.00 | 1.00 | 1.00 | 1.00 | 1.00 | 1.00 | 1.00 |
| Mir8098 | 1.00 | 1.00 | 1.00 | 1.00 | 1.23 | 7.65 | 1.00 | 1.00 | 0.49 | 1.00 | 3.27 | 0.27 |
| Mir8099-1 | 1.00 | 1.00 | 0.07 | 0.10 | 1.00 | 13.66 | 1.00 | 1.00 | 12.95 | 1.00 | 0.10 | 1.00 |
| Mir8102 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 1.00 | 1.00 | 1.00 | 1.00 | 13.80 | 1.00 | 1.00 |
| Mir8112 | 1.00 | 1.00 | 1.00 | 1.00 | 0.42 | 1.00 | 1.15 | 0.07 | 1.00 | 0.11 | 0.06 | 6.89 |
| Mir8114 | 1.00 | 1.00 | 1.00 | 1.00 | 40.40 | 1.00 | 1.00 | 1.00 | 1.00 | 1.00 | 1.00 | 1.00 |
| Mir96 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 1.00 | 1.00 | 112.1 | 1.00 | 1.00 | 1.00 |
| Mt3 | 1.00 | 1.00 | 0.48 | 1.00 | 1.00 | 1.00 | 1.00 | 1.00 | 0.96 | 0.94 | 1.00 | 1.00 |
| Mttp | 1.00 | 1.00 | 1.03 | 1.01 | 0.95 | 1.20 | 0.96 | 0.81 | 1.00 | 0.97 | 0.94 | 0.90 |
| Muc13 | 0.71 | 0.68 | 1.00 | 1.00 | 1.00 | 1.00 | 1.00 | 1.00 | 1.00 | 1.00 | 1.00 | 1.00 |
| Muc15 | 1.00 | 1.00 | 1.00 | 1.00 | 1.00 | 1.00 | 1.00 | 1.00 | 1.00 | 1.00 | 1.00 | 1.00 |
| Muc5b | 1.00 | 1.00 | 1.00 | 1.00 | 1.00 | 1.00 | 1.00 | 1.00 | 1.39 | 1.00 | 1.00 | 1.00 |
| Mup1 | 16.60 | 1.00 | 1.00 | 1.00 | 1.00 | 1.00 | 1.00 | 1.00 | 1.00 | 1.00 | 1.00 | 1.00 |
| Mup10 | 12.70 | 1.00 | 1.01 | 1.42 | 1.00 | 1.00 | 1.00 | 1.00 | 1.00 | 1.00 | 1.00 | 1.00 |
| Mup12 | 11.73 | 1.00 | 1.00 | 1.00 | 1.00 | 1.00 | 1.00 | 1.00 | 1.00 | 1.00 | 1.00 | 1.00 |
| Mup13 | 9.99 | 1.00 | 1.00 | 1.00 | 1.00 | 1.00 | 1.00 | 1.00 | 1.00 | 1.00 | 1.00 | 1.00 |
| Mup14 | 5.81 | 1.00 | 1.00 | 1.00 | 1.00 | 1.00 | 1.00 | 1.00 | 1.00 | 1.00 | 1.00 | 1.00 |
| Mup15 | 15.72 | 1.00 | 1.68 | 1.92 | 0.87 | 0.48 | 1.00 | 1.00 | 1.00 | 1.00 | 1.00 | 1.00 |
| Mup2 | 21.56 | 1.00 | 2.98 | 1.12 | 2.78 | 1.74 | 1.00 | 1.00 | 1.00 | 1.00 | 1.00 | 1.00 |
| Mup3 | 15.66 | 1.00 | 1.00 | 1.00 | 1.00 | 1.00 | 1.00 | 1.00 | 1.00 | 1.00 | 1.00 | 1.00 |
| Mup8 | 11.73 | 1.00 | 1.00 | 1.00 | 1.00 | 1.00 | 1.00 | 1.00 | 1.00 | 1.00 | 1.00 | 1.00 |
| Mup9 | 25.72 | 1.00 | 2.40 | 1.72 | 1.51 | 0.66 | 1.00 | 1.00 | 1.00 | 1.00 | 1.00 | 1.00 |
| Ndufa3 | 0.48 | 0.69 | 1.05 | 1.04 | 0.88 | 1.02 | 0.83 | 0.71 | 0.77 | 0.95 | 1.30 | 0.86 |
| Npcd | 1.00 | 1.00 | 1.00 | 1.00 | 1.13 | 1.32 | 1.00 | 1.85 | 0.79 | 0.89 | 1.00 | 1.00 |
| Nr4a1 | 0.70 | 0.97 | 1.42 | 1.22 | 0.76 | 7.99 | 1.17 | 2.48 | 0.51 | 1.56 | 0.75 | 2.27 |
| Nxpe2 | 0.53 | 1.04 | 1.00 | 1.00 | 1.00 | 1.00 | 1.00 | 1.00 | 1.00 | 1.00 | 1.00 | 1.00 |
| Oasl2 | 2.25 | 1.21 | 0.97 | 1.13 | 0.75 | 1.26 | 0.86 | 1.11 | 1.03 | 1.03 | 1.18 | 0.87 |
| Oaz1-ps | 0.50 | 0.00 | 1.00 | 1.00 | 1.00 | 1.00 | 2.96 | 1.00 | 0.14 | 1.00 | 0.06 | 1.00 |
| OTTMUSG00000016609 | 1.00 | 1.00 | 1.00 | 1.00 | 1.00 | 1.00 | 1.00 | 1.00 | 1.00 | 1.00 | 1.00 | 1.00 |
| Ovch2 | 1.00 | 1.00 | 1.00 | 1.00 | 1.00 | 1.00 | 1.00 | 1.00 | 1.00 | 1.00 | 1.00 | 1.00 |
| Padi2 | 1.00 | 1.00 | 0.93 | 1.08 | 1.00 | 1.00 | 1.00 | 1.00 | 1.03 | 1.10 | 1.05 | 1.11 |
| Pax8 | 1.00 | 1.00 | 1.00 | 1.00 | 1.00 | 1.00 | 1.00 | 1.00 | 1.00 | 1.00 | 1.04 | 1.09 |
| Pck1 | 13.81 | 1.00 | 2.82 | 0.55 | 1.04 | 1.16 | 3.80 | 2.64 | 1.17 | 0.78 | 0.85 | 0.81 |
| Pdzk1 | 1.00 | 1.00 | 1.09 | 1.17 | 1.12 | 1.05 | 1.13 | 0.82 | 1.05 | 0.83 | 1.00 | 0.97 |
| Pdzk1ip1 | 1.03 | 0.47 | 1.00 | 1.00 | 1.00 | 1.00 | 1.00 | 1.00 | 1.01 | 1.10 | 1.10 | 0.97 |
| Phgr1 | 0.86 | 1.00 | 1.00 | 1.00 | 1.00 | 1.00 | 1.00 | 1.00 | 1.00 | 1.00 | 1.00 | 1.00 |
| Pira4 | 1.50 | 0.51 | 1.00 | 1.00 | 1.00 | 1.00 | 1.00 | 1.00 | 2.44 | 1.00 | 1.00 | 1.00 |
| Pla2g1b | 0.54 | 1.00 | 1.14 | 0.86 | 0.96 | 0.79 | 1.00 | 1.00 | 0.93 | 0.96 | 1.00 | 1.00 |
| Pnlip | 0.82 | 1.00 | 1.00 | 1.00 | 1.00 | 1.00 | 1.00 | 0.55 | 1.00 | 1.40 | 1.00 | 0.89 |
| Pnliprp1 | 1.00 | 1.00 | 1.00 | 1.00 | 1.00 | 1.00 | 1.00 | 1.00 | 1.00 | 1.00 | 1.00 | 1.00 |
| Pnliprp2 | 1.00 | 1.00 | 1.00 | 1.00 | 1.00 | 1.00 | 1.00 | 1.00 | 1.00 | 1.00 | 1.00 | 1.00 |
| Pou3f3 | 1.00 | 1.00 | 1.00 | 1.00 | 1.00 | 1.00 | 1.00 | 1.00 | 1.00 | 1.00 | 0.96 | 0.88 |
| Ppp1r12b | 1.00 | 1.00 | 0.65 | 0.97 | 1.24 | 0.75 | 1.66 | 1.34 | 1.73 | 1.24 | 1.00 | 1.00 |
| Prap1 | 1.00 | 1.00 | 1.00 | 1.00 | 1.00 | 1.00 | 1.00 | 1.00 | 1.00 | 1.00 | 1.00 | 1.00 |
| Prg4 | 10.19 | 3.45 | 0.43 | 0.85 | 0.92 | 0.73 | 0.80 | 0.72 | 1.68 | 0.86 | 1.00 | 1.00 |
| Prom2 | 1.00 | 1.00 | 1.00 | 1.00 | 1.00 | 1.00 | 1.00 | 1.00 | 0.95 | 1.12 | 1.10 | 1.15 |
| Prss2 | 0.61 | 2.97 | 1.00 | 1.00 | 1.00 | 1.00 | 1.00 | 0.76 | 1.00 | 2.04 | 1.00 | 1.07 |
| Prss8 | 1.00 | 1.00 | 1.00 | 1.00 | 1.00 | 1.00 | 1.00 | 1.00 | 1.02 | 0.84 | 0.99 | 0.84 |
| Ptgds | 1.00 | 1.00 | 1.00 | 1.00 | 1.00 | 1.00 | 0.89 | 1.01 | 1.00 | 1.00 | 1.00 | 1.00 |
| Rab11fip4 | 1.00 | 1.00 | 1.00 | 1.00 | 1.00 | 1.00 | 1.00 | 1.00 | 0.86 | 1.32 | 0.54 | 1.37 |

Fig. 37- 20

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Mir7-1 | 1.00 | 1.00 | 1.00 | 1.00 | 1.00 | 1.00 | 1.00 | 1.00 | 1.00 | 1.00 | 1.00 | 1.00 |
| Mir719 | 1.00 | 1.00 | 1.00 | 1.00 | 55.55 | 1.00 | 0.65 | 1.00 | 1.00 | 1.00 | 18.10 | 1.00 |
| Mir760 | 1.00 | 1.00 | 1.00 | 1.00 | 1.00 | 1.00 | 1.00 | 12.14 | 1.00 | 1.00 | 1.00 | 0.05 |
| Mir8091 | 1.00 | 1.00 | 6.13 | 1.00 | 1.00 | 1.00 | 1.00 | 1.00 | 1.00 | 1.00 | 1.00 | 0.15 |
| Mir8093 | 10.97 | 1.00 | 1.00 | 23.26 | 1.00 | 5.47 | 1.00 | 1.00 | 1.00 | 1.00 | 1.00 | 1.00 |
| Mir8094 | 35.43 | 26.62 | 1.38 | 2.81 | 2.95 | 1.93 | 0.69 | 0.14 | 1.00 | 1.00 | 0.32 | 2.85 |
| Mir8096 | 1.00 | 1.00 | 1.00 | 1.00 | 1.00 | 1.00 | 1.00 | 1.00 | 1.00 | 1.00 | 1.00 | 1.00 |
| Mir8097 | 1.00 | 1.00 | 1.00 | 1.00 | 1.00 | 1.00 | 1.00 | 1.00 | 1.00 | 1.00 | 1.00 | 1.00 |
| Mir8098 | 1.00 | 0.32 | 3.77 | 1.00 | 1.08 | 1.00 | 1.00 | 1.00 | 3.34 | 1.00 | 1.72 | 1.00 |
| Mir8099-1 | 8.99 | 1.00 | 1.00 | 1.00 | 1.00 | 1.00 | 1.00 | 1.00 | 1.00 | 1.39 | 0.12 | 0.03 |
| Mir8102 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 260.2 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 1.00 | 0.00 | 0.04 | 1.00 | 1.00 | 1.00 | 1.00 |
| Mir8112 | 7.26 | 1.00 | 0.78 | 0.10 | 1.00 | 7.19 | 5.01 | 0.06 | 4.98 | 8.34 | 1.00 | 0.75 |
| Mir8114 | 1.00 | 1.00 | 1.00 | 1.00 | 1.00 | 1.00 | 1.00 | 1.00 | 1.00 | 1.00 | 1.00 | 1.00 |
| Mir96 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 67.58 | 1.00 | 1.00 | 1.00 | 1.00 | 1.00 |
| Mt3 | 1.00 | 1.00 | 0.90 | 1.10 | 1.00 | 0.71 | 8.19 | 5.71 | 1.03 | 1.00 | 1.00 | 1.00 |
| Mttp | 1.00 | 0.93 | 0.91 | 1.25 | 5.94 | 3.52 | 1.26 | 0.94 | 1.06 | 1.04 | 1.00 | 1.00 |
| Muc13 | 1.00 | 1.00 | 1.07 | 1.04 | 24.47 | 10.08 | 1.00 | 1.00 | 1.00 | 1.00 | 0.90 | 1.00 |
| Muc15 | 1.00 | 1.00 | 1.00 | 1.00 | 0.82 | 0.94 | 65.12 | 26.22 | 0.93 | 1.31 | 1.00 | 1.00 |
| Muc5b | 1.00 | 1.00 | 1.00 | 1.00 | 1.00 | 1.00 | 13.48 | 1.00 | 1.00 | 1.00 | 1.00 | 1.00 |
| Mup1 | 0.95 | 1.17 | 1.00 | 1.00 | 0.29 | 0.97 | 1.00 | 8.42 | 1.00 | 1.00 | 1.00 | 1.00 |
| Mup10 | 0.94 | 1.18 | 1.00 | 1.00 | 0.51 | 1.28 | 1.00 | 6.65 | 1.00 | 1.00 | 1.00 | 1.00 |
| Mup12 | 0.95 | 1.24 | 1.00 | 1.00 | 0.19 | 0.86 | 1.00 | 7.13 | 1.00 | 1.00 | 1.00 | 1.00 |
| Mup13 | 0.92 | 1.18 | 1.00 | 1.00 | 0.52 | 1.57 | 1.00 | 5.71 | 1.00 | 1.00 | 1.00 | 1.00 |
| Mup14 | 1.83 | 1.46 | 1.00 | 1.00 | 0.76 | 1.00 | 1.00 | 4.74 | 1.00 | 1.00 | 1.00 | 1.00 |
| Mup15 | 0.99 | 1.23 | 1.00 | 1.00 | 0.28 | 0.95 | 1.09 | 12.83 | 1.00 | 0.51 | 1.00 | 1.00 |
| Mup2 | 0.86 | 1.13 | 1.00 | 0.83 | 0.43 | 1.27 | 1.92 | 8.76 | 0.94 | 1.19 | 1.00 | 1.00 |
| Mup3 | 1.00 | 1.26 | 1.00 | 1.00 | 0.21 | 0.87 | 1.00 | 7.35 | 1.00 | 1.00 | 1.00 | 1.00 |
| Mup8 | 0.93 | 1.15 | 1.00 | 1.00 | 0.33 | 1.07 | 1.00 | 5.84 | 1.00 | 1.00 | 1.00 | 1.00 |
| Mup9 | 1.03 | 1.22 | 1.00 | 0.65 | 0.29 | 1.05 | 2.20 | 5.31 | 1.00 | 0.77 | 1.00 | 1.00 |
| Ndufa3 | 0.73 | 0.82 | 0.83 | 0.74 | 1.13 | 1.10 | 1.27 | 1.68 | 2.81 | 0.98 | 1.01 | 0.85 |
| Npcd | 1.00 | 1.00 | 0.62 | 1.03 | 0.60 | 0.49 | 1.32 | 1.63 | 1.24 | 0.80 | 0.78 | 0.73 |
| Nr4a1 | 0.77 | 0.53 | 1.71 | 0.88 | 0.63 | 1.01 | 0.65 | 1.31 | 1.08 | 0.88 | 0.82 | 0.99 |
| Nxpe2 | 0.80 | 1.07 | 0.97 | 1.07 | 1.00 | 1.00 | 8.57 | 1.00 | 1.00 | 1.00 | 0.83 | 1.03 |
| Oasl2 | 0.83 | 0.91 | 0.88 | 0.73 | 1.09 | 1.21 | 0.68 | 0.97 | 0.75 | 1.01 | 1.14 | 0.97 |
| Oaz1-ps | 16.13 | 1.00 | 1.00 | 1.00 | 1.00 | 1.00 | 21.17 | 1.00 | 7.72 | 1.00 | 0.68 | 1.00 |
| OTTMUSG000000 16609 | 1.00 | 1.00 | 1.00 | 1.00 | 0.67 | 0.74 | 1.00 | 1.00 | 1.00 | 1.00 | 1.00 | 1.00 |
| Ovch2 | 1.00 | 1.00 | 1.00 | 1.00 | 1.00 | 1.00 | 1.98 | 14.78 | 1.00 | 1.00 | 1.00 | 1.00 |
| Padi2 | 1.00 | 1.00 | 0.91 | 1.01 | 0.85 | 0.99 | 7.23 | 1.89 | 0.84 | 1.19 | 0.95 | 1.12 |
| Pax8 | 1.00 | 1.00 | 0.82 | 1.02 | 1.00 | 1.00 | 6.39 | 8.33 | 1.00 | 1.00 | 1.00 | 1.00 |
| Pck1 | 0.98 | 0.85 | 0.96 | 0.82 | 0.71 | 0.89 | 0.79 | 0.79 | 0.66 | 1.07 | 2.37 | 0.68 |
| Pdzk1 | 0.86 | 0.96 | 1.17 | 0.78 | 1.29 | 0.91 | 8.61 | 6.45 | 1.18 | 0.99 | 1.16 | 0.94 |
| Pdzk1ip1 | 0.98 | 1.00 | 0.68 | 0.88 | 0.84 | 0.92 | 7.74 | 2.88 | 1.54 | 1.03 | 1.03 | 0.92 |
| Phgr1 | 1.00 | 1.00 | 0.75 | 0.89 | 1.30 | 1.16 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 1.00 |
| Pla2g1b | 0.66 | 1.32 | 1.74 | 6.23 | 0.84 | 1.03 | 1.02 | 0.86 | 1.88 | 1.04 | 35.55 | 0.13 |
| Pnlip | 1.00 | 5.70 | 1.94 | 65.25 | 3.19 | 63.64 | 1.00 | 1.00 | 1.00 | 1.00 | 155.4 | 0.03 |
| Pnliprp1 | 1.00 | 1.76 | 1.86 | 21.91 | 2.08 | 1.69 | 1.00 | 1.00 | 1.00 | 1.00 | 50.63 | 0.06 |
| Pnliprp2 | 1.00 | 1.00 | 2.88 | 5.51 | 1.14 | 0.98 | 1.00 | 1.00 | 1.00 | 1.00 | 12.63 | 0.22 |
| Pou3f3 | 1.00 | 1.00 | 0.92 | 1.44 | 1.00 | 1.00 | 5.02 | 7.86 | 0.93 | 1.00 | 1.00 | 1.00 |
| Ppp1r12b | 1.00 | 1.00 | 6.06 | 0.88 | 0.99 | 0.96 | 1.11 | 0.99 | 0.59 | 1.08 | 0.98 | 1.17 |
| Prap1 | 1.00 | 1.00 | 0.73 | 1.66 | 25.78 | 20.87 | 1.00 | 1.00 | 1.00 | 1.00 | 1.00 | 1.00 |
| Prg4 | 1.07 | 1.12 | 0.88 | 1.00 | 0.66 | 0.76 | 0.56 | 0.94 | 1.00 | 1.00 | 1.44 | 1.12 |
| Prom2 | 1.00 | 1.00 | 1.00 | 1.00 | 0.93 | 1.04 | 27.93 | 3.79 | 1.00 | 1.00 | 1.00 | 1.00 |
| Prss2 | 0.48 | 11.62 | 1.81 | 164.1 | 2.50 | 132.9 | 1.00 | 1.00 | 1.00 | 1.00 | 283.8 | 0.03 |
| Prss8 | 0.98 | 0.78 | 0.83 | 1.02 | 0.97 | 0.95 | 7.29 | 3.24 | 1.00 | 1.00 | 1.00 | 1.00 |
| Ptgds | 1.00 | 1.00 | 1.00 | 1.00 | 0.91 | 0.73 | 20.01 | 2.03 | 1.46 | 0.91 | 1.00 | 1.00 |
| Rab11fip4 | 1.37 | 0.48 | 3.68 | 0.74 | 1.04 | 1.09 | 5.68 | 1.93 | 0.74 | 1.13 | 0.88 | 1.05 |

Fig. 37-21

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Mir7-1 | 1.00 | 1.00 | 1.00 | 1.00 | 1.00 | 1.00 | 1.00 | 54.24 | 2.50 | 0.01 |
| Mir719 | 1.00 | 1.00 | 1.00 | 1.00 | 1.00 | 0.03 | 0.03 | 1.00 | 1.00 | 1.00 |
| Mir760 | 1.00 | 1.00 | 1.00 | 1.00 | 1.00 | 1.00 | 1.00 | 1.00 | 1.00 | 1.00 |
| Mir8091 | 1.00 | 1.00 | 1.00 | 1.00 | 1.00 | 1.00 | 1.00 | 1.00 | 0.22 | 6.89 |
| Mir8093 | 1.00 | 1.00 | 1.00 | 7.06 | 1.00 | 1.00 | 5.68 | 6.61 | 11.88 | 0.18 |
| Mir8094 | 20.57 | 24.70 | 1.15 | 7.09 | 116.7 | 1.54 | 0.28 | 0.03 | 0.62 | 0.06 |
| Mir8096 | 1.00 | 1.00 | 1.00 | 1.00 | 1.00 | 1.00 | 1.00 | 1.00 | 9.78 | 1.00 |
| Mir8097 | 1.00 | 1.00 | 1.00 | 1.00 | 1.00 | 11.13 | 1.00 | 1.00 | 1.00 | 1.00 |
| Mir8098 | 1.00 | 1.00 | 9.16 | 0.13 | 1.00 | 1.00 | 1.00 | 1.00 | 1.00 | 1.00 |
| Mir8099-1 | 0.12 | 1.00 | 0.11 | 11.56 | 1.00 | 16.24 | 0.64 | 1.14 | 1.23 | 1.00 |
| Mir8102 | 1.00 | 1.00 | 1.00 | 1.00 | 1.00 | 1.00 | 5.22 | 1.00 | 1.00 | 1.00 |
| Mir8103 | 1.00 | 1.00 | 1.00 | 1.00 | 1.00 | 1.00 | 1.00 | 1.00 | 1.00 | 1.00 |
| Mir8104 | 349.7 | 1.00 | 107.9 | 1.00 | 1.00 | 1.00 | 1.00 | 1.00 | 1.00 | 1.00 |
| Mir8112 | 1.00 | 1.00 | 1.00 | 18.67 | 1.00 | 0.12 | 1.00 | 17.50 | 7.88 | 1.00 |
| Mir8114 | 1.00 | 1.00 | 1.00 | 1.00 | 1.00 | 1.00 | 1.00 | 1.00 | 1.00 | 1.00 |
| Mir96 | 1.00 | 1.00 | 1.00 | 1.00 | 1.00 | 1.00 | 63.61 | 1.00 | 1.00 | 1.00 |
| Mirlet7d | 1.00 | 1.00 | 128.3 | 1.00 | 1.00 | 1.00 | 1.00 | 1.00 | 1.00 | 1.00 |
| Mt3 | 1.00 | 1.00 | 0.90 | 0.64 | 0.96 | 0.98 | 0.60 | 0.54 | 1.00 | 1.00 |
| Mttp | 1.00 | 1.00 | 0.99 | 1.09 | 0.93 | 0.96 | 1.07 | 1.16 | 1.00 | 1.00 |
| Muc13 | 1.06 | 5.59 | 1.00 | 1.00 | 1.00 | 1.00 | 1.00 | 1.00 | 1.21 | 1.00 |
| Muc15 | 1.00 | 1.00 | 1.00 | 1.00 | 1.00 | 1.00 | 1.00 | 1.31 | 1.00 | 1.00 |
| Muc5b | 1.00 | 1.00 | 1.00 | 1.00 | 1.00 | 1.00 | 1.00 | 1.00 | 1.00 | 1.00 |
| Mup1 | 1.00 | 1.00 | 1.00 | 1.00 | 1.00 | 1.00 | 1.00 | 0.14 | 1.00 | 1.00 |
| Mup10 | 1.00 | 1.00 | 1.00 | 1.00 | 1.00 | 1.00 | 1.00 | 0.19 | 1.00 | 1.00 |
| Mup12 | 1.00 | 1.00 | 1.00 | 1.00 | 1.00 | 1.00 | 1.00 | 0.17 | 1.00 | 1.00 |
| Mup13 | 1.00 | 1.00 | 1.00 | 1.00 | 1.00 | 1.00 | 1.00 | 0.21 | 1.00 | 1.00 |
| Mup14 | 1.00 | 0.97 | 1.00 | 1.00 | 1.00 | 1.00 | 1.00 | 0.51 | 1.00 | 1.00 |
| Mup15 | 1.00 | 0.92 | 1.00 | 1.00 | 1.00 | 1.00 | 1.00 | 0.12 | 1.00 | 2.09 |
| Mup2 | 1.00 | 0.43 | 1.00 | 1.00 | 1.00 | 1.00 | 1.00 | 0.07 | 1.00 | 1.07 |
| Mup3 | 1.00 | 1.00 | 1.00 | 1.00 | 1.00 | 1.00 | 1.00 | 0.16 | 1.00 | 1.00 |
| Mup8 | 1.00 | 1.00 | 1.00 | 1.00 | 1.00 | 1.00 | 1.00 | 0.17 | 1.00 | 1.00 |
| Mup9 | 1.00 | 1.00 | 1.00 | 1.00 | 1.00 | 1.00 | 1.00 | 0.11 | 1.00 | 1.20 |
| Ndufa3 | 0.75 | 6.16 | 1.10 | 0.48 | 0.72 | 0.97 | 1.75 | 0.80 | 0.60 | 0.87 |
| Npcd | 1.00 | 1.00 | 5.92 | 0.57 | 0.62 | 0.96 | 1.29 | 0.96 | 1.00 | 1.00 |
| Nr4a1 | 0.89 | 1.00 | 1.29 | 1.57 | 1.47 | 1.59 | 1.31 | 1.02 | 0.86 | 1.10 |
| Nxpe2 | 1.00 | 1.00 | 1.00 | 1.00 | 1.00 | 1.00 | 1.00 | 1.00 | 0.80 | 0.84 |
| Oasl2 | 1.00 | 1.00 | 1.48 | 0.85 | 1.53 | 3.09 | 0.84 | 8.60 | 1.44 | 1.04 |
| Oaz1-ps | 7.54 | 1.00 | 1.00 | 1.00 | 1.00 | 1.00 | 2.64 | 1.00 | 1.00 | 1.00 |
| OTTMUSG000000 16609 | 1.00 | 1.00 | 0.69 | 6.14 | 1.00 | 1.00 | 1.00 | 1.00 | 1.00 | 1.00 |
| Ovch2 | 1.00 | 1.00 | 1.00 | 1.00 | 1.00 | 1.00 | 1.00 | 1.00 | 1.00 | 1.00 |
| Padi2 | 1.07 | 1.22 | 1.13 | 1.25 | 1.11 | 1.21 | 1.12 | 0.93 | 1.11 | 1.12 |
| Pax8 | 1.00 | 1.00 | 1.00 | 1.00 | 1.00 | 1.00 | 1.00 | 1.00 | 0.83 | 0.83 |
| Pck1 | 0.78 | 1.48 | 1.00 | 1.00 | 1.00 | 1.00 | 1.07 | 0.94 | 1.00 | 0.47 |
| Pdzk1 | 1.00 | 1.00 | 0.99 | 1.73 | 1.02 | 0.97 | 1.11 | 1.20 | 1.01 | 1.00 |
| Pdzk1ip1 | 1.06 | 1.80 | 1.00 | 1.00 | 1.31 | 1.00 | 1.09 | 0.94 | 0.76 | 0.69 |
| Phgr1 | 2.31 | 6.22 | 1.00 | 1.00 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 20.07 | 1.61 |
| Pla2g1b | 0.82 | 1.35 | 1.22 | 1.00 | 1.00 | 1.00 | 0.89 | 1.00 | 0.37 | 0.86 |
| Pnlip | 0.96 | 1.07 | 1.56 | 1.14 | 1.00 | 1.29 | 1.23 | 1.20 | 1.00 | 1.00 |
| Pnliprp1 | 0.86 | 0.98 | 1.00 | 1.00 | 1.00 | 1.00 | 1.00 | 1.00 | 1.00 | 1.00 |
| Pnliprp2 | 0.90 | 0.97 | 1.00 | 1.00 | 1.00 | 1.00 | 1.00 | 1.00 | 1.00 | 1.00 |
| Pou3f3 | 1.00 | 1.00 | 0.97 | 1.06 | 1.02 | 0.98 | 1.01 | 1.23 | 1.00 | 1.00 |
| Ppp1r12b | 1.00 | 1.00 | 0.83 | 4.09 | 1.51 | 0.88 | 0.73 | 1.60 | 1.00 | 1.00 |
| Prap1 | 1.00 | 1.00 | 1.00 | 1.00 | 1.00 | 1.00 | 1.00 | 1.00 | 1.00 | 1.00 |
| Prg4 | 1.00 | 1.00 | 1.15 | 0.87 | 1.06 | 0.72 | 0.86 | 1.03 | 0.76 | 0.99 |
| Prom2 | 1.20 | 1.04 | 1.00 | 1.00 | 1.00 | 1.00 | 1.05 | 0.95 | 1.00 | 1.00 |
| Prss2 | 0.86 | 1.10 | 1.34 | 1.15 | 1.00 | 0.84 | 1.13 | 0.98 | 2.72 | 1.00 |
| Prss8 | 1.23 | 1.22 | 1.00 | 1.00 | 1.00 | 1.00 | 0.96 | 0.95 | 1.00 | 1.00 |
| Ptgds | 1.00 | 1.00 | 1.02 | 0.77 | 0.92 | 0.95 | 1.52 | 1.03 | 1.00 | 1.00 |
| Rab11fip4 | 1.29 | 0.59 | 0.85 | 2.61 | 1.34 | 0.90 | 0.90 | 1.15 | 2.50 | 1.45 |

Fig. 37-22

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Rab25 | 1.00 | 1.00 | 1.00 | 1.00 | 1.00 | 1.00 | 1.00 | 1.00 | 0.86 | 0.88 | 1.28 | 1.05 |
| Rbm11 | 1.00 | 1.00 | 1.00 | 1.00 | 1.00 | 1.00 | 1.00 | 1.00 | 1.00 | 1.00 | 1.00 | 1.32 |
| Rbp4 | 22.27 | 1.00 | 2.50 | 0.96 | 1.22 | 0.90 | 1.42 | 1.20 | 0.80 | 0.76 | 1.14 | 0.59 |
| Reg1 | 0.84 | 1.00 | 1.00 | 1.00 | 1.00 | 1.00 | 1.00 | 1.00 | 1.00 | 1.22 | 1.00 | 0.91 |
| Reg2 | 1.00 | 1.00 | 1.00 | 1.00 | 1.00 | 1.00 | 1.00 | 0.60 | 1.00 | 1.00 | 1.00 | 0.86 |
| Reg3a | 1.00 | 1.00 | 1.00 | 1.00 | 1.00 | 1.00 | 1.00 | 1.00 | 1.00 | 1.00 | 1.00 | 1.00 |
| Reg3b | 1.00 | 1.00 | 1.00 | 1.00 | 1.00 | 1.02 | 1.00 | 1.00 | 1.00 | 1.00 | 1.00 | 1.17 |
| Reg3d | 1.00 | 1.00 | 1.00 | 1.00 | 1.00 | 1.00 | 1.00 | 1.00 | 1.00 | 1.00 | 1.00 | 1.00 |
| Reg3g | 1.00 | 1.00 | 1.00 | 1.00 | 1.00 | 1.00 | 3.10 | 1.65 | 1.06 | 0.91 | 1.00 | 1.00 |
| Rhcg | 1.00 | 1.00 | 1.00 | 1.00 | 1.00 | 1.00 | 1.00 | 1.00 | 1.00 | 1.00 | 1.06 | 1.13 |
| Rmrp | 1.00 | 1.00 | 1.00 | 1.52 | 1.00 | 1.00 | 1.00 | 1.00 | 1.00 | 1.00 | 1.00 | 1.00 |
| Rnase1 | 0.84 | 1.70 | 1.00 | 1.00 | 1.00 | 1.00 | 0.73 | 0.76 | 1.00 | 1.15 | 1.00 | 0.77 |
| Rnase10 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.00 | 1.00 | 1.00 | 1.00 |
| Rnase13 | 1.00 | 1.00 | 0.62 | 1.19 | 1.00 | 1.00 | 1.00 | 1.00 | 1.00 | 1.00 | 1.00 | 1.00 |
| Rnase4 | 6.07 | 1.74 | 1.03 | 1.02 | 0.93 | 0.84 | 0.93 | 1.01 | 0.99 | 0.85 | 1.08 | 0.87 |
| Rnase9 | 1.00 | 1.00 | 1.00 | 1.00 | 1.00 | 1.00 | 1.00 | 1.00 | 1.00 | 1.00 | 1.00 | 1.00 |
| Rnf186 | 1.00 | 1.00 | 1.00 | 1.00 | 1.00 | 1.00 | 1.00 | 1.00 | 1.13 | 0.90 | 1.19 | 0.93 |
| Rnu11 | 1.00 | 1.00 | 1.00 | 1.00 | 1.00 | 1.00 | 1.00 | 1.00 | 1.00 | 1.00 | 1.00 | 1.00 |
| Rps18 | 1.00 | 1.00 | 0.88 | 1.36 | 0.62 | 2.01 | 0.80 | 0.75 | 0.42 | 2.32 | 0.61 | 1.21 |
| Rtp4 | 1.00 | 0.65 | 0.72 | 0.92 | 0.95 | 0.96 | 0.69 | 1.07 | 0.99 | 1.06 | 1.43 | 0.96 |
| S100g | 1.00 | 1.00 | 1.00 | 1.00 | 1.00 | 1.00 | 1.00 | 1.00 | 0.91 | 0.79 | 1.14 | 0.95 |
| Saa3 | 8.87 | 3.64 | 1.00 | 1.00 | 1.00 | 1.00 | 0.80 | 1.04 | 1.19 | 1.07 | 1.00 | 1.00 |
| Scarna3b | 1.00 | 1.00 | 1.00 | 1.00 | 1.00 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scgb1a1 | 1.00 | 5.11 | 1.00 | 1.00 | 1.00 | 1.00 | 4.49 | 1.25 | 1.04 | 1.02 | 1.10 | 1.18 |
| Scube1 | 1.00 | 1.00 | 1.00 | 1.00 | 1.00 | 1.00 | 1.00 | 1.00 | 1.00 | 1.19 | 1.00 | 1.00 |
| Sdc3 | 6.41 | 2.84 | 1.14 | 0.88 | 1.15 | 1.00 | 1.07 | 1.06 | 1.07 | 1.05 | 0.88 | 1.00 |
| Serinc2 | 1.00 | 1.00 | 1.05 | 1.05 | 1.00 | 1.00 | 1.00 | 1.00 | 0.84 | 0.87 | 1.14 | 1.10 |
| Serpina1a | 28.06 | 1.00 | 1.09 | 0.66 | 0.95 | 0.65 | 0.83 | 1.21 | 0.95 | 0.72 | 1.11 | 0.79 |
| Serpina1b | 36.84 | 1.00 | 0.79 | 1.24 | 1.07 | 0.67 | 0.81 | 0.94 | 0.82 | 0.90 | 1.06 | 0.86 |
| Serpina1c | 44.11 | 1.00 | 1.54 | 0.89 | 1.04 | 1.04 | 0.62 | 1.09 | 0.76 | 0.80 | 1.20 | 0.76 |
| Serpina1d | 15.22 | 1.00 | 1.52 | 0.94 | 1.39 | 0.67 | 0.80 | 1.31 | 0.95 | 0.99 | 1.00 | 0.80 |
| Serpina1e | 8.13 | 1.00 | 1.00 | 1.00 | 1.42 | 0.93 | 1.00 | 0.99 | 0.76 | 0.72 | 1.26 | 0.77 |
| Serpina1f | 1.00 | 1.00 | 1.00 | 1.00 | 1.00 | 1.00 | 1.00 | 1.00 | 1.00 | 1.00 | 1.12 | 0.88 |
| Serpina3k | 53.31 | 1.00 | 1.39 | 0.94 | 2.18 | 0.71 | 1.00 | 1.00 | 1.00 | 1.00 | 1.00 | 1.00 |
| Serpina3n | 5.23 | 1.00 | 0.99 | 0.94 | 0.97 | 0.94 | 0.68 | 0.64 | 0.96 | 1.03 | 0.69 | 1.07 |
| Serpinb2 | 3.57 | 6.81 | 1.00 | 1.00 | 1.00 | 1.00 | 1.00 | 1.00 | 1.00 | 1.00 | 1.00 | 1.00 |
| Slc17a9 | 1.00 | 1.00 | 1.00 | 1.00 | 1.00 | 1.00 | 1.00 | 1.00 | 0.96 | 1.20 | 1.00 | 1.00 |
| Slc1a1 | 1.00 | 1.00 | 1.69 | 1.19 | 1.18 | 1.38 | 1.20 | 1.59 | 0.96 | 1.07 | 1.08 | 1.07 |
| Slc27a2 | 5.29 | 1.00 | 1.06 | 1.00 | 0.92 | 0.76 | 0.97 | 1.11 | 1.39 | 1.00 | 0.87 | 0.88 |
| Slc35f2 | 1.00 | 1.00 | 1.00 | 1.00 | 1.00 | 1.00 | 1.00 | 1.00 | 1.00 | 1.00 | 0.98 | 1.05 |
| Slc38a5 | 0.62 | 0.87 | 1.00 | 1.00 | 1.00 | 1.00 | 1.00 | 1.00 | 0.74 | 1.38 | 1.00 | 1.00 |
| Slc9a7 | 1.00 | 1.00 | 1.00 | 1.00 | 1.00 | 1.00 | 1.00 | 1.00 | 1.00 | 1.00 | 1.00 | 1.00 |
| Snora16a | 1.00 | 1.00 | 0.06 | 1.00 | 14.71 | 0.04 | 1.14 | 8.14 | 5.99 | 1.00 | 3.53 | 1.16 |
| Snora17 | 1.00 | 1.00 | 1.00 | 1.00 | 1.00 | 1.00 | 1.00 | 1.00 | 1.40 | 1.00 | 1.00 | 1.00 |
| Snora21 | 1.00 | 1.00 | 1.00 | 1.00 | 1.00 | 1.00 | 1.00 | 1.00 | 1.00 | 1.00 | 1.00 | 1.00 |
| Snora28 | 1.00 | 1.00 | 1.00 | 25.42 | 1.00 | 1.00 | 1.00 | 0.08 | 0.03 | 0.06 | 1.00 | 1.00 |
| Snora2b | 1.00 | 1.00 | 1.00 | 1.00 | 1.00 | 1.00 | 0.04 | 1.00 | 1.00 | 1.00 | 1.00 | 1.00 |
| Snora3 | 1.00 | 1.00 | 1.00 | 1.00 | 1.00 | 1.00 | 1.00 | 1.00 | 1.00 | 1.00 | 1.00 | 1.00 |
| Snora30 | 1.00 | 1.00 | 1.00 | 1.00 | 1.00 | 1.00 | 1.00 | 1.00 | 1.00 | 1.00 | 1.00 | 1.00 |
| Snora31 | 1.00 | 1.00 | 1.00 | 1.00 | 1.00 | 1.00 | 1.00 | 1.00 | 1.00 | 1.00 | 1.00 | 1.00 |
| Snora33 | 1.00 | 1.00 | 1.00 | 1.00 | 1.00 | 1.00 | 1.00 | 110.1 | 0.02 | 0.01 | 1.00 | 3.36 |
| Snora34 | 1.00 | 1.00 | 0.02 | 0.06 | 21.11 | 0.04 | 1.00 | 1.00 | 0.04 | 1.00 | 1.00 | 1.00 |
| Snora36b | 1.00 | 1.00 | 1.00 | 1.00 | 1.00 | 1.00 | 1.00 | 1.00 | 1.00 | 1.00 | 1.00 | 1.00 |
| Snora41 | 1.00 | 1.00 | 1.00 | 1.00 | 0.03 | 0.03 | 1.00 | 1.00 | 0.05 | 1.38 | 1.00 | 1.00 |
| Snora43 | 1.00 | 1.00 | 1.00 | 1.00 | 6.46 | 1.00 | 0.38 | 0.70 | 0.07 | 0.08 | 1.00 | 0.29 |
| Snora44 | 1.00 | 1.00 | 1.00 | 1.00 | 1.00 | 1.00 | 0.06 | 1.00 | 0.08 | 1.00 | 1.00 | 1.00 |
| Snora52 | 1.00 | 1.00 | 7.39 | 1.00 | 8.06 | 0.11 | 0.15 | 0.16 | 1.00 | 1.00 | 1.00 | 0.10 |
| Snora5c | 1.00 | 1.00 | 1.00 | 1.00 | 1.00 | 1.00 | 1.00 | 1.00 | 1.00 | 1.00 | 1.00 | 1.00 |

Fig. 37-23

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Rab25 | 1.00 | 1.00 | 0.81 | 0.97 | 1.06 | 1.01 | 8.41 | 4.16 | 1.00 | 1.00 | 1.00 | 1.00 |
| Rbm11 | 1.00 | 1.00 | 1.00 | 1.00 | 1.00 | 1.00 | 23.67 | 6.47 | 1.05 | 1.21 | 1.00 | 1.00 |
| Rbp4 | 0.91 | 0.95 | 0.60 | 0.92 | 0.57 | 1.09 | 0.86 | 1.00 | 1.95 | 1.12 | 1.01 | 0.67 |
| Reg1 | 1.00 | 3.94 | 1.65 | 58.45 | 2.86 | 24.71 | 1.00 | 1.00 | 1.00 | 1.00 | 89.89 | 0.03 |
| Reg2 | 1.00 | 4.18 | 1.30 | 62.25 | 1.81 | 44.46 | 1.00 | 1.00 | 1.00 | 1.00 | 88.44 | 0.03 |
| Reg3a | 1.00 | 1.00 | 1.46 | 5.42 | 1.73 | 6.58 | 1.00 | 1.00 | 1.00 | 1.00 | 12.66 | 0.23 |
| Reg3b | 1.00 | 1.00 | 0.95 | 0.99 | 3.70 | 54.25 | 1.00 | 1.00 | 1.00 | 1.00 | 19.55 | 0.14 |
| Reg3d | 1.00 | 1.00 | 1.78 | 4.55 | 1.87 | 1.30 | 1.00 | 1.00 | 1.00 | 1.00 | 6.61 | 0.56 |
| Reg3g | 1.00 | 1.00 | 1.01 | 1.28 | 4.11 | 6.37 | 1.00 | 1.00 | 1.00 | 1.00 | 1.00 | 1.00 |
| Rhcg | 1.00 | 1.00 | 1.00 | 1.00 | 1.00 | 1.00 | 21.99 | 1.00 | 0.85 | 0.91 | 1.00 | 1.00 |
| Rmrp | 0.91 | 5.13 | 0.76 | 1.34 | 0.06 | 1.00 | 1.00 | 1.00 | 1.00 | 0.96 | 1.28 | 1.36 |
| Rnase1 | 0.94 | 5.19 | 1.69 | 103.0 | 2.30 | 1.72 | 3.18 | 2.64 | 1.00 | 1.00 | 196.6 | 0.03 |
| Rnase10 | 1.00 | 1.00 | 1.00 | 1.00 | 1.00 | 1.00 | 23.69 | 195.9 | 1.00 | 0.97 | 1.00 | 1.00 |
| Rnase12 | 1.00 | 1.00 | 1.00 | 1.00 | 1.00 | 1.00 | 56.44 | 12.51 | 1.00 | 1.00 | 0.87 | 1.22 |
| Rnase13 | 1.00 | 1.00 | 1.00 | 1.00 | 1.00 | 1.00 | 74.45 | 1.00 | 1.00 | 0.92 | 1.00 | 1.00 |
| Rnase4 | 0.84 | 0.99 | 0.77 | 1.13 | 1.13 | 0.99 | 0.77 | 0.86 | 0.75 | 1.02 | 1.04 | 0.81 |
| Rnase9 | 1.00 | 1.00 | 1.00 | 1.00 | 1.00 | 1.00 | 216.6 | 1.00 | 1.00 | 1.00 | 1.00 | 1.00 |
| Rnf186 | 1.19 | 0.64 | 0.92 | 1.08 | 2.19 | 0.98 | 5.51 | 5.04 | 1.00 | 1.00 | 0.87 | 1.00 |
| Rnu11 | 1.00 | 1.00 | 1.00 | 1.00 | 1.00 | 1.00 | 1.00 | 1.00 | 1.00 | 128.3 | 1.00 | 1.00 |
| Rps18 | 1.80 | 1.25 | 0.88 | 0.32 | 1.11 | 0.89 | 1.43 | 1.46 | 1.00 | 0.98 | 1.03 | 0.93 |
| Rtp4 | 0.71 | 1.11 | 0.81 | 0.85 | 1.24 | 2.05 | 0.74 | 0.93 | 1.00 | 1.00 | 0.94 | 0.76 |
| S100g | 1.00 | 1.00 | 0.72 | 1.86 | 9.54 | 3.36 | 2.15 | 1.00 | 1.00 | 1.00 | 1.00 | 1.00 |
| Saa3 | 0.69 | 0.96 | 1.03 | 0.65 | 0.15 | 1.52 | 0.33 | 1.78 | 1.00 | 1.00 | 1.67 | 2.25 |
| Scarna3b | 1.00 | 1.00 | 1.00 | 1.00 | 1.00 | 10.56 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scgb1a1 | 0.52 | 1.00 | 0.55 | 1.00 | 0.85 | 1.18 | 1.00 | 1.00 | 1.00 | 1.00 | 0.72 | 0.97 |
| Scube1 | 1.00 | 1.00 | 1.24 | 0.89 | 1.03 | 1.12 | 5.32 | 2.06 | 1.00 | 1.00 | 1.13 | 1.11 |
| Sdc3 | 1.19 | 1.09 | 1.19 | 0.98 | 0.83 | 1.15 | 0.97 | 1.15 | 0.82 | 0.90 | 0.92 | 1.17 |
| Serinc2 | 0.89 | 1.23 | 0.94 | 1.05 | 1.16 | 1.08 | 3.67 | 7.72 | 1.28 | 0.83 | 1.05 | 0.98 |
| Serpina1a | 1.04 | 1.04 | 1.07 | 0.56 | 0.22 | 0.87 | 0.89 | 1.55 | 1.12 | 1.13 | 1.30 | 0.92 |
| Serpina1b | 1.03 | 1.06 | 0.83 | 0.55 | 0.28 | 0.78 | 0.73 | 1.28 | 0.77 | 1.03 | 1.09 | 1.01 |
| Serpina1c | 1.00 | 1.11 | 0.92 | 0.72 | 0.15 | 0.60 | 1.00 | 1.90 | 0.74 | 0.87 | 1.03 | 0.95 |
| Serpina1d | 1.05 | 1.04 | 1.00 | 0.62 | 0.24 | 1.00 | 1.00 | 1.75 | 0.76 | 1.00 | 1.13 | 0.85 |
| Serpina1e | 1.09 | 1.08 | 1.00 | 1.00 | 0.58 | 1.00 | 1.39 | 1.11 | 1.00 | 1.00 | 1.11 | 0.86 |
| Serpina1f | 1.00 | 1.00 | 1.00 | 1.00 | 1.00 | 1.00 | 18.72 | 1.00 | 1.00 | 1.00 | 1.00 | 1.00 |
| Serpina3k | 1.02 | 1.10 | 1.00 | 0.82 | 0.10 | 0.84 | 1.04 | 2.83 | 1.00 | 0.67 | 1.00 | 1.00 |
| Serpina3n | 1.01 | 1.09 | 0.93 | 0.85 | 0.67 | 0.96 | 0.73 | 1.14 | 0.96 | 1.01 | 1.11 | 0.83 |
| Serpinb2 | 1.00 | 1.00 | 1.00 | 1.00 | 0.82 | 1.05 | 1.00 | 1.19 | 1.00 | 1.00 | 0.88 | 1.05 |
| Slc17a9 | 0.56 | 1.11 | 0.84 | 1.00 | 1.23 | 1.10 | 4.11 | 5.93 | 1.17 | 0.95 | 0.98 | 1.44 |
| Slc1a1 | 1.00 | 1.00 | 0.83 | 1.17 | 1.00 | 1.00 | 1.16 | 5.46 | 1.00 | 1.00 | 1.00 | 1.00 |
| Slc27a2 | 1.07 | 0.92 | 0.85 | 1.00 | 0.65 | 0.96 | 6.21 | 4.46 | 1.00 | 1.00 | 0.77 | 0.69 |
| Slc35f2 | 1.00 | 1.00 | 0.80 | 1.44 | 1.48 | 1.07 | 5.21 | 3.16 | 0.84 | 1.02 | 1.09 | 0.84 |
| Slc38a5 | 1.00 | 1.00 | 1.00 | 1.00 | 0.91 | 0.87 | 143.1 | 5.16 | 1.47 | 0.76 | 0.93 | 1.16 |
| Slc9a7 | 1.00 | 1.00 | 1.00 | 1.00 | 1.00 | 1.00 | 1.00 | 1.00 | 1.00 | 1.00 | 1.00 | 1.00 |
| Snora16a | 1.00 | 1.00 | 34.66 | 0.06 | 0.65 | 0.97 | 3.62 | 2.79 | 1.00 | 8.13 | 1.23 | 22.47 |
| Snora17 | 1.00 | 1.00 | 1.00 | 1.00 | 8.56 | 0.48 | 1.00 | 1.00 | 1.00 | 1.00 | 0.15 | 0.11 |
| Snora21 | 1.00 | 1.00 | 1.00 | 1.00 | 1.00 | 1.00 | 1.00 | 0.10 | 1.00 | 1.00 | 6.66 | 8.35 |
| Snora28 | 1.00 | 1.00 | 15.45 | 1.00 | 1.00 | 1.00 | 1.00 | 1.00 | 1.00 | 1.00 | 1.00 | 1.00 |
| Snora2b | 1.00 | 1.00 | 1.00 | 1.00 | 1.00 | 1.00 | 1.00 | 1.00 | 1.00 | 1.00 | 1.00 | 1.00 |
| Snora3 | 1.00 | 10.63 | 1.00 | 1.00 | 0.98 | 0.07 | 0.70 | 1.00 | 1.00 | 1.00 | 1.00 | 0.05 |
| Snora30 | 1.00 | 1.00 | 1.00 | 1.00 | 1.00 | 1.00 | 33.37 | 1.00 | 1.00 | 1.00 | 1.00 | 1.00 |
| Snora31 | 1.00 | 1.00 | 1.00 | 1.00 | 1.00 | 0.04 | 36.43 | 44.61 | 1.00 | 1.00 | 1.00 | 1.00 |
| Snora33 | 1.00 | 1.00 | 1.00 | 1.00 | 1.00 | 0.01 | 1.00 | 1.00 | 52.81 | 1.00 | 55.73 | 0.01 |
| Snora34 | 1.00 | 1.00 | 1.00 | 0.04 | 1.00 | 15.92 | 1.00 | 13.09 | 1.00 | 1.00 | 1.00 | 32.05 |
| Snora36b | 1.00 | 1.00 | 1.00 | 1.00 | 1.00 | 1.00 | 1.00 | 20.17 | 1.00 | 1.00 | 1.00 | 24.81 |
| Snora41 | 1.00 | 0.03 | 1.00 | 0.03 | 0.99 | 0.04 | 1.00 | 0.02 | 18.81 | 36.05 | 1.00 | 0.03 |
| Snora43 | 0.18 | 3.93 | 6.13 | 2.17 | 1.00 | 0.10 | 10.66 | 1.40 | 1.00 | 14.29 | 0.10 | 0.15 |
| Snora44 | 1.00 | 1.00 | 20.44 | 1.00 | 1.00 | 1.00 | 1.00 | 1.00 | 1.00 | 1.00 | 1.00 | 1.00 |
| Snora52 | 1.00 | 0.11 | 1.58 | 0.11 | 1.00 | 0.08 | 1.44 | 0.70 | 1.00 | 1.00 | 0.82 | 1.00 |
| Snora5c | 1.00 | 1.00 | 1.00 | 1.00 | 1.00 | 1.00 | 1.00 | 1.00 | 1.00 | 1.00 | 133.8 | 1.00 |

Fig. 37-24

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Rab25 | 0.98 | 1.08 | 1.00 | 1.00 | 1.00 | 1.00 | 1.08 | 0.91 | 1.00 | 1.00 |
| Rbm11 | 1.00 | 1.00 | 0.97 | 1.07 | 0.84 | 1.11 | 1.00 | 1.00 | 1.00 | 1.00 |
| Rbp4 | 0.72 | 1.69 | 1.24 | 0.91 | 0.71 | 0.72 | 1.28 | 0.70 | 1.00 | 1.18 |
| Reg1 | 0.93 | 1.22 | 1.00 | 1.00 | 1.00 | 1.00 | 1.00 | 1.00 | 1.00 | 1.00 |
| Reg2 | 0.80 | 1.20 | 1.00 | 1.01 | 1.00 | 1.00 | 1.20 | 1.24 | 1.04 | 1.00 |
| Reg3a | 0.85 | 1.28 | 1.00 | 1.00 | 1.00 | 1.00 | 1.00 | 1.00 | 1.00 | 1.00 |
| Reg3b | 0.92 | 1.26 | 0.89 | 1.00 | 1.00 | 1.00 | 0.95 | 1.00 | 1.00 | 1.00 |
| Reg3d | 0.91 | 1.28 | 1.00 | 1.00 | 1.00 | 1.00 | 1.00 | 1.00 | 1.00 | 1.00 |
| Reg3g | 1.04 | 1.51 | 1.00 | 1.00 | 1.00 | 1.00 | 1.00 | 1.00 | 1.00 | 1.00 |
| Rhcg | 1.00 | 1.00 | 1.00 | 1.00 | 1.00 | 1.00 | 1.00 | 1.00 | 1.00 | 1.00 |
| Rmrp | 1.00 | 9.14 | 1.00 | 1.00 | 1.00 | 1.00 | 1.00 | 1.00 | 0.57 | 1.00 |
| Rnase1 | 0.85 | 1.14 | 1.80 | 1.17 | 1.31 | 1.14 | 1.08 | 1.01 | 1.01 | 1.00 |
| Rnase10 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.01 | 1.52 |
| Rnase13 | 1.00 | 1.00 | 1.00 | 1.00 | 1.00 | 1.00 | 1.00 | 1.00 | 1.00 | 1.00 |
| Rnase4 | 0.93 | 1.09 | 0.92 | 0.72 | 1.11 | 1.23 | 1.05 | 1.00 | 0.81 | 1.09 |
| Rnase9 | 1.00 | 1.00 | 1.00 | 1.00 | 1.00 | 1.00 | 1.00 | 1.00 | 1.00 | 1.00 |
| Rnf186 | 0.96 | 1.24 | 1.00 | 1.00 | 1.00 | 1.00 | 1.00 | 1.00 | 1.00 | 1.00 |
| Rnu11 | 1.00 | 1.00 | 1.00 | 1.00 | 1.00 | 1.00 | 1.00 | 1.00 | 0.03 | 1.00 |
| Rps18 | 0.75 | 1.69 | 0.82 | 1.28 | 2.88 | 6.41 | 0.90 | 0.66 | 0.91 | 0.68 |
| Rtp4 | 1.00 | 1.00 | 1.25 | 0.78 | 0.88 | 2.00 | 1.14 | 5.50 | 1.16 | 1.01 |
| S100g | 1.00 | 1.00 | 1.00 | 1.00 | 1.00 | 1.00 | 1.00 | 1.00 | 1.00 | 1.00 |
| Saa3 | 0.38 | 1.00 | 1.00 | 1.00 | 1.57 | 8.73 | 0.26 | 1.81 | 1.49 | 1.55 |
| Scarna3b | 1.00 | 1.00 | 1.00 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 39.27 | 1.00 | 0.06 |
| Scgb1a1 | 1.00 | 3.43 | 1.00 | 7.54 | 1.22 | 0.58 | 1.47 | 0.91 | 4.71 | 1.00 |
| Scube1 | 1.00 | 1.00 | 1.11 | 1.40 | 1.01 | 1.02 | 0.96 | 1.01 | 1.00 | 1.00 |
| Sdc3 | 1.00 | 1.00 | 0.96 | 1.20 | 1.01 | 1.04 | 1.00 | 1.26 | 1.17 | 0.90 |
| Serinc2 | 0.80 | 1.31 | 0.95 | 0.72 | 0.83 | 1.06 | 0.91 | 0.83 | 1.00 | 1.00 |
| Serpina1a | 1.00 | 1.00 | 1.00 | 1.00 | 1.04 | 1.00 | 0.61 | 0.41 | 1.00 | 1.00 |
| Serpina1b | 1.00 | 1.00 | 0.89 | 1.03 | 0.76 | 0.72 | 1.01 | 0.54 | 1.00 | 1.00 |
| Serpina1c | 1.00 | 1.00 | 0.86 | 0.69 | 1.20 | 1.13 | 0.45 | 0.23 | 1.00 | 1.37 |
| Serpina1d | 1.00 | 1.00 | 1.00 | 1.00 | 1.00 | 1.00 | 0.96 | 0.55 | 1.00 | 1.00 |
| Serpina1e | 1.00 | 0.96 | 1.00 | 1.00 | 1.00 | 1.00 | 0.90 | 0.95 | 1.00 | 1.00 |
| Serpina1f | 1.00 | 1.00 | 1.00 | 1.00 | 1.00 | 1.00 | 1.00 | 1.00 | 1.00 | 1.00 |
| Serpina3k | 1.00 | 0.51 | 1.00 | 1.00 | 1.00 | 1.00 | 1.00 | 0.13 | 1.00 | 1.02 |
| Serpina3n | 1.05 | 0.87 | 0.98 | 1.04 | 1.39 | 1.71 | 0.93 | 0.99 | 0.99 | 1.42 |
| Serpinb2 | 1.00 | 1.00 | 1.00 | 1.00 | 1.00 | 1.00 | 0.84 | 1.11 | 0.80 | 0.69 |
| Slc17a9 | 1.15 | 1.12 | 1.00 | 1.00 | 1.00 | 1.00 | 1.01 | 0.88 | 1.09 | 0.91 |
| Slc1a1 | 1.00 | 1.00 | 1.02 | 0.93 | 0.93 | 0.97 | 1.35 | 0.99 | 1.00 | 1.00 |
| Slc27a2 | 1.00 | 1.00 | 0.90 | 1.24 | 0.94 | 0.92 | 1.00 | 0.74 | 1.00 | 1.00 |
| Slc35f2 | 1.00 | 1.00 | 1.09 | 1.05 | 0.90 | 0.77 | 1.13 | 0.99 | 1.00 | 1.00 |
| Slc38a5 | 0.81 | 1.43 | 1.00 | 1.00 | 1.13 | 1.21 | 1.00 | 1.00 | 0.62 | 0.78 |
| Slc9a7 | 1.00 | 1.00 | 0.67 | 5.16 | 1.08 | 0.71 | 1.00 | 1.00 | 1.00 | 1.00 |
| Snora16a | 1.00 | 1.00 | 0.17 | 1.00 | 1.00 | 1.57 | 17.82 | 1.69 | 0.61 | 0.03 |
| Snora17 | 1.00 | 1.00 | 7.98 | 1.00 | 1.00 | 1.00 | 14.34 | 0.14 | 1.00 | 1.00 |
| Snora21 | 1.00 | 1.00 | 1.00 | 1.00 | 1.00 | 1.00 | 1.00 | 1.00 | 1.00 | 1.00 |
| Snora28 | 1.00 | 1.00 | 1.00 | 1.00 | 1.00 | 1.00 | 1.00 | 1.00 | 1.00 | 1.00 |
| Snora2b | 1.00 | 1.00 | 1.00 | 1.00 | 1.00 | 25.30 | 1.00 | 1.00 | 1.00 | 1.00 |
| Snora3 | 1.00 | 1.00 | 1.00 | 1.00 | 1.00 | 1.00 | 14.67 | 1.00 | 1.00 | 19.37 |
| Snora30 | 1.00 | 1.00 | 1.00 | 1.00 | 1.00 | 1.00 | 1.00 | 1.00 | 1.00 | 1.00 |
| Snora31 | 1.00 | 1.00 | 1.00 | 1.00 | 1.00 | 1.00 | 1.00 | 33.62 | 1.00 | 0.04 |
| Snora33 | 1.00 | 1.00 | 1.00 | 1.00 | 1.00 | 1.00 | 75.33 | 1.00 | 1.00 | 1.00 |
| Snora34 | 1.00 | 1.00 | 19.25 | 1.00 | 1.00 | 0.03 | 1.00 | 0.06 | 1.00 | 1.00 |
| Snora36b | 1.00 | 1.00 | 1.00 | 1.00 | 1.00 | 1.00 | 1.00 | 1.00 | 1.00 | 1.00 |
| Snora41 | 1.00 | 1.12 | 1.00 | 1.00 | 1.00 | 1.00 | 0.85 | 2.31 | 27.50 | 1.00 |
| Snora43 | 1.00 | 1.00 | 1.00 | 0.19 | 0.19 | 0.17 | 10.44 | 1.13 | 0.22 | 2.65 |
| Snora44 | 1.00 | 1.00 | 1.00 | 1.00 | 1.00 | 0.05 | 1.00 | 1.00 | 1.00 | 1.00 |
| Snora52 | 1.00 | 1.00 | 7.23 | 0.15 | 6.70 | 1.00 | 6.51 | 0.15 | 6.81 | 1.00 |
| Snora5c | 1.00 | 1.00 | 1.00 | 1.00 | 1.00 | 1.00 | 1.00 | 1.00 | 1.00 | 1.00 |

Fig. 37- 25

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Snora62 | 1.00 | 1.00 | 1.00 | 1.00 | 1.00 | 1.00 | 1.00 | 1.00 | 1.00 | 1.00 | 1.00 | 1.00 |
| Snora64 | 1.00 | 1.00 | 20.08 | 0.05 | 1.00 | 53.42 | 1.00 | 3.10 | 5.72 | 1.00 | 0.88 | 1.13 |
| Snora65 | 1.00 | 1.00 | 37.19 | 31.20 | 2.54 | 0.02 | 1.00 | 1.00 | 17.21 | 14.40 | 1.00 | 15.27 |
| Snora69 | 1.00 | 1.00 | 1.00 | 1.00 | 1.00 | 1.00 | 1.00 | 1.00 | 1.00 | 1.00 | 1.00 | 1.00 |
| Snora70 | 1.00 | 1.00 | 0.08 | 7.86 | 0.84 | 0.54 | 0.06 | 11.66 | 1.41 | 1.00 | 1.00 | 1.15 |
| Snora75 | 1.00 | 1.00 | 1.00 | 1.00 | 1.00 | 1.00 | 1.00 | 1.00 | 1.00 | 1.00 | 1.00 | 1.00 |
| Snora78 | 1.00 | 1.83 | 1.00 | 0.33 | 0.12 | 0.26 | 3.28 | 1.00 | 0.48 | 0.71 | 0.44 | 1.00 |
| Snora7a | 1.00 | 1.00 | 1.00 | 1.00 | 1.00 | 12.25 | 1.00 | 1.00 | 1.00 | 1.00 | 8.25 | 1.00 |
| Snora81 | 1.00 | 1.00 | 2.76 | 0.90 | 0.41 | 0.10 | 1.11 | 0.52 | 0.23 | 3.89 | 2.28 | 1.76 |
| Snord15a | 1.00 | 1.00 | 1.00 | 1.00 | 1.00 | 5.52 | 1.00 | 1.00 | 3.75 | 1.00 | 1.00 | 1.00 |
| Snord15b | 1.00 | 1.00 | 1.00 | 1.00 | 0.16 | 1.00 | 1.00 | 1.00 | 1.00 | 1.00 | 1.00 | 1.00 |
| Snord22 | 1.00 | 1.00 | 1.00 | 0.10 | 0.03 | 3.23 | 1.00 | 0.04 | 8.48 | 1.00 | 1.00 | 8.99 |
| Spag11a | 1.00 | 1.00 | 1.00 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 | 1.00 | 1.00 |
| Spin2c | 1.00 | 1.00 | 1.00 | 1.00 | 1.00 | 1.00 | 1.00 | 1.00 | 1.00 | 1.25 | 1.00 | 1.00 |
| Spink11 | 1.00 | 1.00 | 1.00 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 | 1.00 | 1.00 | 1.00 |
| Spink2 | 1.00 | 1.00 | 1.00 | 1.00 | 1.00 | 1.00 | 1.00 | 1.00 | 1.00 | 1.00 | 1.00 | 1.00 |
| Spink5 | 1.00 | 1.00 | 1.00 | 1.00 | 1.00 | 1.00 | 1.00 | 1.00 | 1.00 | 1.00 | 1.00 | 1.00 |
| Spink8 | 1.00 | 1.00 | 1.00 | 1.00 | 1.00 | 1.00 | 1.00 | 1.00 | 1.00 | 1.00 | 1.34 | 1.16 |
| Spint1 | 1.00 | 1.00 | 1.00 | 1.00 | 1.00 | 1.00 | 1.00 | 1.00 | 0.90 | 0.86 | 1.07 | 0.99 |
| Spock1 | 1.00 | 1.00 | 1.00 | 1.00 | 1.00 | 1.00 | 1.00 | 1.00 | 1.00 | 1.00 | 1.00 | 1.00 |
| Srd5a2 | 1.00 | 1.00 | 1.00 | 1.00 | 1.00 | 1.00 | 1.00 | 1.00 | 1.00 | 1.00 | 1.02 | 1.06 |
| St6gal1 | 1.00 | 1.00 | 1.07 | 0.92 | 0.97 | 1.11 | 0.93 | 1.21 | 0.98 | 1.08 | 1.00 | 1.06 |
| Susd4 | 1.00 | 1.00 | 1.00 | 1.00 | 1.00 | 1.00 | 1.00 | 1.00 | 1.26 | 1.15 | 0.73 | 1.53 |
| Sv2c | 1.00 | 1.00 | 1.00 | 1.00 | 1.00 | 1.00 | 1.00 | 1.00 | 1.00 | 1.00 | 1.00 | 1.00 |
| Sycn | 0.70 | 1.61 | 1.00 | 1.00 | 1.00 | 1.00 | 1.00 | 1.08 | 1.00 | 1.34 | 1.54 | 1.14 |
| Sytl4 | 0.77 | 0.63 | 1.00 | 1.00 | 0.86 | 1.04 | 1.11 | 0.99 | 0.94 | 0.93 | 1.07 | 1.15 |
| Tacstd2 | 1.14 | 1.00 | 1.00 | 1.00 | 1.00 | 1.00 | 1.00 | 1.00 | 1.03 | 1.02 | 1.02 | 0.98 |
| Tat | 5.21 | 1.00 | 1.00 | 1.00 | 1.00 | 1.00 | 1.00 | 1.00 | 1.00 | 1.00 | 1.00 | 1.00 |
| Tceal3 | 1.00 | 1.00 | 0.95 | 0.91 | 1.00 | 1.00 | 1.00 | 1.00 | 0.98 | 1.16 | 1.00 | 1.00 |
| Tcf7 | 1.00 | 1.00 | 1.00 | 1.00 | 1.00 | 1.00 | 1.00 | 1.00 | 1.30 | 0.83 | 1.00 | 1.00 |
| Teddm1 | 1.00 | 1.00 | 1.00 | 1.00 | 1.00 | 1.00 | 1.00 | 1.00 | 1.00 | 1.00 | 1.00 | 1.00 |
| Tff2 | 1.00 | 1.00 | 1.00 | 1.00 | 1.00 | 1.00 | 1.00 | 1.00 | 0.84 | 1.76 | 1.00 | 1.00 |
| Tff3 | 1.00 | 1.00 | 1.00 | 1.00 | 1.00 | 1.00 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 1.00 | 1.00 | 1.00 | 1.00 |
| Tgoln2 | 1.00 | 1.00 | 0.42 | 0.69 | 1.00 | 1.00 | 1.44 | 1.19 | 1.00 | 1.00 | 1.00 | 1.00 |
| Tgtp1 | 1.00 | 1.21 | 1.34 | 2.09 | 1.01 | 1.83 | 0.99 | 1.53 | 1.09 | 1.19 | 1.21 | 1.72 |
| Tgtp2 | 0.70 | 1.51 | 1.02 | 1.91 | 1.07 | 1.73 | 0.98 | 1.51 | 1.16 | 1.12 | 1.14 | 1.55 |
| Tm4sf20 | 1.00 | 1.00 | 1.00 | 1.00 | 1.00 | 1.00 | 1.00 | 1.00 | 1.00 | 1.00 | 1.00 | 1.00 |
| Tmem150c | 1.00 | 1.00 | 1.00 | 1.00 | 1.00 | 1.00 | 1.18 | 1.33 | 1.04 | 1.00 | 0.95 | 0.96 |
| Tmem178b | 1.00 | 1.00 | 1.00 | 1.00 | 1.00 | 1.00 | 1.00 | 1.00 | 1.00 | 1.00 | 1.00 | 1.00 |
| Tmem27 | 1.00 | 1.00 | 1.00 | 1.00 | 1.00 | 1.00 | 1.00 | 1.00 | 1.00 | 1.00 | 1.16 | 0.92 |
| Tox3 | 1.00 | 1.00 | 1.00 | 1.00 | 1.00 | 0.93 | 0.87 | 0.99 | 1.09 | 0.95 | 1.13 | 0.76 |
| Tpd52l1 | 1.00 | 1.00 | 1.18 | 0.91 | 0.86 | 1.09 | 0.94 | 0.87 | 1.00 | 1.45 | 1.10 | 0.90 |
| Trf | 7.89 | 1.67 | 1.56 | 1.05 | 0.96 | 0.94 | 1.07 | 1.17 | 0.95 | 1.03 | 1.09 | 1.13 |
| Trim56 | 1.00 | 1.00 | 0.43 | 0.97 | 1.19 | 1.06 | 1.92 | 1.08 | 1.40 | 1.21 | 0.29 | 1.00 |
| Try10 | 1.00 | 1.00 | 1.00 | 1.00 | 1.00 | 1.00 | 1.00 | 1.00 | 1.00 | 1.00 | 1.00 | 1.00 |
| Try4 | 0.58 | 2.35 | 1.00 | 1.00 | 1.00 | 1.00 | 1.00 | 1.01 | 1.00 | 1.29 | 1.00 | 1.25 |
| Try5 | 0.61 | 2.48 | 1.00 | 1.00 | 1.00 | 1.00 | 1.00 | 0.96 | 1.00 | 1.41 | 1.00 | 0.66 |
| Ttr | 12.53 | 1.00 | 1.00 | 1.00 | 1.00 | 1.00 | 1.00 | 1.00 | 1.00 | 1.00 | 1.27 | 0.89 |
| Ucp1 | 1.00 | 1.00 | 5.12 | 0.45 | 1.25 | 1.10 | 10.36 | 4.27 | 1.00 | 1.00 | 1.15 | 1.62 |
| Uhmk1 | 1.00 | 1.00 | 0.59 | 0.92 | 1.10 | 1.46 | 1.63 | 1.35 | 1.47 | 0.99 | 0.45 | 1.20 |
| Vasn | 1.00 | 1.00 | 1.03 | 1.15 | 0.89 | 0.89 | 1.11 | 1.03 | 0.99 | 0.96 | 0.71 | 1.11 |
| Vip | 1.00 | 1.00 | 1.00 | 1.00 | 1.00 | 1.00 | 1.00 | 1.00 | 1.00 | 1.00 | 1.00 | 1.00 |
| Vtn | 6.62 | 1.00 | 0.83 | 1.25 | 1.15 | 1.00 | 0.99 | 1.15 | 0.77 | 0.83 | 1.00 | 1.00 |
| Wfdc10 | 1.00 | 1.00 | 1.00 | 1.00 | 1.00 | 1.00 | 1.00 | 1.00 | 0.94 | 1.05 | 1.00 | 1.00 |
| Wfdc11 | 1.00 | 1.00 | 1.00 | 1.00 | 1.00 | 1.00 | 1.00 | 1.00 | 1.00 | 1.00 | 1.00 | 1.00 |
| Wfdc15b | 1.00 | 1.00 | 1.00 | 1.00 | 1.00 | 1.00 | 1.00 | 1.00 | 1.00 | 1.00 | 1.22 | 0.94 |
| Wfdc2 | 1.00 | 1.00 | 1.00 | 1.00 | 1.00 | 1.00 | 6.60 | 0.92 | 0.87 | 0.94 | 1.26 | 0.94 |

Fig. 37- 26

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Snora62 | 1.00 | 1.00 | 1.00 | 1.00 | 1.00 | 1.00 | 5.81 | 1.00 | 1.00 | 1.00 | 1.00 | 1.00 |
| Snora64 | 1.00 | 0.04 | 1.00 | 1.00 | 0.02 | 0.02 | 1.38 | 0.02 | 1.09 | 1.00 | 0.81 | 34.70 |
| Snora65 | 1.00 | 1.00 | 0.02 | 1.00 | 0.02 | 0.96 | 10.82 | 26.17 | 1.00 | 1.00 | 0.81 | 1.00 |
| Snora69 | 1.00 | 9.29 | 1.00 | 0.06 | 1.00 | 0.08 | 1.00 | 1.00 | 1.00 | 1.00 | 0.09 | 0.06 |
| Snora70 | 0.11 | 12.39 | 0.04 | 0.04 | 1.47 | 2.90 | 0.36 | 1.04 | 1.00 | 1.00 | 2.45 | 0.45 |
| Snora75 | 1.00 | 1.00 | 1.00 | 1.00 | 1.00 | 0.03 | 1.00 | 1.00 | 1.00 | 1.00 | 14.93 | 1.00 |
| Snora78 | 0.46 | 1.00 | 0.42 | 2.51 | 3.88 | 5.52 | 1.00 | 1.41 | 6.25 | 0.18 | 0.38 | 7.97 |
| Snora7a | 1.00 | 1.00 | 0.04 | 1.00 | 1.00 | 7.96 | 1.00 | 1.00 | 1.00 | 1.00 | 1.00 | 15.81 |
| Snora81 | 0.46 | 1.13 | 2.41 | 1.61 | 0.86 | 0.87 | 0.96 | 0.89 | 2.89 | 0.46 | 1.00 | 8.93 |
| Snord15a | 1.00 | 1.00 | 4.45 | 1.34 | 0.22 | 1.00 | 1.00 | 1.00 | 1.00 | 1.00 | 0.29 | 1.00 |
| Snord15b | 1.00 | 1.00 | 0.21 | 0.17 | 0.07 | 1.95 | 1.00 | 1.00 | 1.00 | 1.00 | 0.27 | 0.75 |
| Snord22 | 0.91 | 1.00 | 0.51 | 0.02 | 0.49 | 4.83 | 0.71 | 7.70 | 7.14 | 1.00 | 1.09 | 0.52 |
| Spag11a | 1.00 | 1.00 | 1.00 | 1.00 | 1.00 | 1.00 | 72.00 | 11.84 | 1.00 | 1.00 | 1.00 | 1.00 |
| Spag11b | 1.00 | 1.00 | 1.00 | 1.00 | 1.00 | 1.00 | 797.1 | 481.7 | 1.00 | 1.00 | 1.00 | 1.00 |
| Spin2c | 1.00 | 1.00 | 1.00 | 1.12 | 0.73 | 0.84 | 7.83 | 2.50 | 1.56 | 0.84 | 1.00 | 1.00 |
| Spink11 | 1.00 | 1.00 | 1.00 | 1.00 | 1.00 | 1.00 | 178.4 | 1.00 | 1.00 | 1.00 | 1.00 | 1.00 |
| Spink12 | 1.00 | 1.00 | 1.00 | 1.00 | 1.00 | 1.60 | 49.02 | 1.00 | 1.00 | 1.00 | 1.00 | 1.00 |
| Spink2 | 1.00 | 1.00 | 1.00 | 1.00 | 1.00 | 1.00 | 193.7 | 1.00 | 1.22 | 1.08 | 1.00 | 1.00 |
| Spink5 | 1.00 | 1.00 | 1.00 | 1.00 | 0.87 | 0.95 | 22.31 | 1.00 | 1.00 | 1.00 | 1.00 | 1.00 |
| Spink8 | 1.00 | 1.00 | 1.00 | 1.00 | 1.00 | 1.00 | 324.2 | 6.18 | 1.98 | 2.07 | 1.00 | 1.00 |
| Spint1 | 1.00 | 1.00 | 0.87 | 0.89 | 1.05 | 0.97 | 6.36 | 3.46 | 1.17 | 0.97 | 1.00 | 1.00 |
| Spock1 | 1.00 | 1.00 | 1.09 | 1.00 | 1.00 | 1.00 | 5.73 | 1.00 | 1.00 | 1.00 | 1.00 | 1.00 |
| Srd5a2 | 1.00 | 1.00 | 1.00 | 1.00 | 1.00 | 1.00 | 12.03 | 4.78 | 1.00 | 1.00 | 1.00 | 1.00 |
| St6gal1 | 0.91 | 1.01 | 1.08 | 0.95 | 0.86 | 0.76 | 5.26 | 1.06 | 0.80 | 1.07 | 1.02 | 0.84 |
| Susd4 | 1.03 | 0.77 | 1.00 | 1.00 | 1.00 | 1.00 | 5.54 | 3.71 | 1.00 | 1.00 | 1.00 | 1.00 |
| Sv2c | 1.00 | 1.00 | 1.00 | 1.00 | 1.00 | 1.00 | 1.00 | 1.00 | 1.00 | 1.00 | 1.00 | 1.00 |
| Sycn | 0.40 | 5.74 | 0.79 | 1.16 | 2.79 | 4.25 | 1.00 | 1.00 | 1.00 | 1.00 | 230.9 | 0.04 |
| Sytl4 | 1.00 | 1.00 | 0.90 | 1.11 | 1.09 | 0.95 | 5.55 | 6.08 | 0.94 | 1.09 | 0.99 | 1.11 |
| Tacstd2 | 1.00 | 1.00 | 1.00 | 1.00 | 0.87 | 0.88 | 6.32 | 1.70 | 1.00 | 1.00 | 1.53 | 1.57 |
| Tat | 1.15 | 0.96 | 0.87 | 0.99 | 0.74 | 1.00 | 1.00 | 1.64 | 1.00 | 1.00 | 1.00 | 1.00 |
| Tceal3 | 1.00 | 1.00 | 0.87 | 0.99 | 0.59 | 1.06 | 4.27 | 5.04 | 1.18 | 1.15 | 1.08 | 1.24 |
| Tcf7 | 0.63 | 0.80 | 1.07 | 1.29 | 1.15 | 1.05 | 5.98 | 3.01 | 0.92 | 1.07 | 1.20 | 0.86 |
| Teddm1 | 1.00 | 1.00 | 1.00 | 1.00 | 1.00 | 1.00 | 20.83 | 240.3 | 1.00 | 1.00 | 1.00 | 1.00 |
| Tff2 | 1.00 | 1.00 | 2.51 | 2.84 | 1.20 | 1.26 | 1.00 | 1.00 | 1.00 | 1.00 | 8.45 | 0.38 |
| Tff3 | 1.04 | 1.31 | 0.76 | 1.01 | 4.48 | 1.79 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 30.75 | 0.03 | 1.00 | 1.00 |
| Tgoln2 | 1.71 | 0.20 | 5.29 | 1.00 | 0.39 | 5.97 | 1.00 | 1.00 | 0.26 | 1.43 | 1.00 | 1.00 |
| Tgtp1 | 0.80 | 1.30 | 1.21 | 1.21 | 1.41 | 1.56 | 0.78 | 1.28 | 1.00 | 1.00 | 1.14 | 1.24 |
| Tgtp2 | 1.12 | 1.22 | 1.23 | 1.13 | 1.59 | 1.64 | 0.82 | 1.36 | 1.00 | 1.00 | 1.08 | 1.27 |
| Tm4sf20 | 1.00 | 1.00 | 0.88 | 1.30 | 12.77 | 7.79 | 1.00 | 1.00 | 1.00 | 1.00 | 1.00 | 1.00 |
| Tmem150c | 1.00 | 1.00 | 1.00 | 1.00 | 1.00 | 1.00 | 9.49 | 23.90 | 1.32 | 1.08 | 1.00 | 1.09 |
| Tmem178b | 1.00 | 1.00 | 1.00 | 1.00 | 1.00 | 1.00 | 1.00 | 1.00 | 1.26 | 0.99 | 1.00 | 1.00 |
| Tmem27 | 1.00 | 1.00 | 1.00 | 1.00 | 0.71 | 0.92 | 5.02 | 1.14 | 1.00 | 1.00 | 1.00 | 1.00 |
| Tox3 | 1.00 | 1.00 | 0.91 | 1.17 | 1.08 | 1.04 | 6.35 | 1.00 | 1.00 | 1.00 | 1.00 | 1.00 |
| Tpd52l1 | 1.13 | 1.47 | 0.68 | 1.05 | 1.18 | 1.05 | 3.70 | 6.03 | 1.18 | 1.16 | 1.00 | 1.00 |
| Trf | 0.93 | 1.14 | 1.00 | 0.80 | 0.63 | 1.08 | 0.82 | 0.94 | 0.79 | 1.05 | 0.88 | 0.88 |
| Trim56 | 2.28 | 0.30 | 8.42 | 0.93 | 1.10 | 0.90 | 1.04 | 1.13 | 1.00 | 1.00 | 1.16 | 1.04 |
| Try10 | 1.00 | 1.00 | 1.37 | 1.58 | 1.88 | 1.02 | 1.00 | 1.00 | 1.00 | 1.00 | 5.78 | 0.78 |
| Try4 | 0.51 | 13.39 | 2.06 | 196.4 | 2.68 | 8.20 | 1.00 | 1.00 | 2.53 | 0.83 | 246.0 | 0.02 |
| Try5 | 0.81 | 10.31 | 1.78 | 155.4 | 2.58 | 16.79 | 1.00 | 1.00 | 1.28 | 0.75 | 188.2 | 0.02 |
| Ttr | 0.81 | 1.28 | 0.85 | 0.63 | 1.06 | 0.99 | 1.13 | 3.52 | 1.00 | 1.00 | 1.00 | 1.00 |
| Ucp1 | 1.00 | 1.00 | 1.00 | 1.00 | 1.00 | 1.00 | 1.00 | 1.00 | 1.00 | 1.00 | 1.00 | 1.00 |
| Uhmk1 | 2.67 | 0.24 | 8.28 | 0.91 | 1.18 | 1.14 | 1.06 | 0.97 | 0.45 | 1.07 | 0.88 | 1.16 |
| Vasn | 1.27 | 1.24 | 1.60 | 0.82 | 0.91 | 1.07 | 0.95 | 1.36 | 1.05 | 1.05 | 0.77 | 0.82 |
| Vip | 1.00 | 1.00 | 0.58 | 0.99 | 0.84 | 1.01 | 1.00 | 10.06 | 1.00 | 1.00 | 1.00 | 1.00 |
| Vtn | 0.91 | 1.28 | 1.02 | 0.94 | 0.90 | 1.31 | 0.87 | 0.93 | 1.00 | 1.00 | 1.00 | 1.00 |
| Wfdc10 | 1.00 | 1.00 | 1.00 | 1.00 | 1.10 | 1.00 | 247.3 | 44.36 | 1.46 | 0.99 | 1.00 | 1.00 |
| Wfdc11 | 1.00 | 1.00 | 1.00 | 1.00 | 1.00 | 1.00 | 5.08 | 1.00 | 1.00 | 1.00 | 1.00 | 1.00 |
| Wfdc15b | 1.00 | 1.00 | 1.00 | 1.00 | 1.34 | 1.85 | 13.19 | 5.58 | 1.00 | 1.00 | 1.00 | 1.00 |
| Wfdc2 | 1.11 | 0.91 | 0.80 | 0.80 | 1.16 | 1.00 | 1.54 | 1.12 | 1.00 | 1.00 | 1.00 | 1.00 |

Fig. 37-27

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Snora62 | 1.00 | 1.00 | 1.00 | 1.00 | 1.00 | 1.00 | 1.00 | 1.00 | 1.00 | 1.00 |
| Snora64 | 20.57 | 1.00 | 0.06 | 1.21 | 0.05 | 1.00 | 1.00 | 0.05 | 0.06 | 0.03 |
| Snora65 | 1.00 | 22.85 | 1.17 | 20.91 | 1.01 | 2.31 | 0.43 | 1.00 | 1.00 | 0.34 |
| Snora69 | 1.00 | 1.00 | 1.00 | 1.00 | 1.00 | 1.00 | 0.07 | 1.00 | 1.00 | 1.00 |
| Snora70 | 0.06 | 0.05 | 1.00 | 0.12 | 0.50 | 1.00 | 0.57 | 0.03 | 2.14 | 4.01 |
| Snora75 | 1.00 | 1.00 | 1.00 | 1.00 | 1.00 | 1.00 | 1.00 | 1.00 | 1.00 | 1.00 |
| Snora78 | 1.00 | 1.00 | 3.07 | 1.00 | 0.17 | 1.00 | 0.15 | 3.27 | 1.00 | 0.18 |
| Snora7a | 1.00 | 11.48 | 1.00 | 0.06 | 8.67 | 1.00 | 1.00 | 1.00 | 8.75 | 1.00 |
| Snora81 | 3.17 | 3.39 | 0.35 | 1.07 | 0.49 | 0.80 | 0.85 | 0.44 | 1.89 | 1.84 |
| Snord15a | 1.00 | 1.00 | 1.00 | 1.00 | 1.00 | 1.00 | 1.00 | 1.00 | 0.15 | 1.00 |
| Snord15b | 5.01 | 1.00 | 1.00 | 1.00 | 0.23 | 1.00 | 0.85 | 1.12 | 1.00 | 1.32 |
| Snord22 | 1.00 | 27.01 | 1.00 | 0.03 | 10.30 | 0.03 | 2.13 | 22.95 | 0.61 | 2.68 |
| Spag11a | 1.00 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 |
| Spin2c | 1.00 | 1.00 | 0.87 | 0.64 | 0.92 | 1.23 | 1.11 | 0.94 | 1.00 | 1.00 |
| Spink11 | 1.00 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 | 1.00 |
| Spink2 | 1.00 | 1.00 | 1.00 | 1.00 | 1.00 | 1.00 | 1.00 | 1.00 | 0.77 | 0.78 |
| Spink5 | 1.00 | 1.00 | 1.00 | 1.00 | 1.00 | 1.00 | 0.99 | 1.00 | 1.00 | 1.00 |
| Spink8 | 1.00 | 1.00 | 0.63 | 0.64 | 0.77 | 0.73 | 1.00 | 1.00 | 1.00 | 1.00 |
| Spint1 | 0.90 | 1.02 | 1.00 | 1.00 | 0.86 | 1.19 | 1.08 | 0.96 | 1.00 | 1.00 |
| Spock1 | 1.00 | 1.00 | 0.96 | 1.30 | 0.91 | 0.99 | 1.00 | 1.00 | 1.00 | 1.00 |
| Srd5a2 | 1.00 | 1.00 | 1.00 | 1.00 | 1.00 | 1.00 | 1.00 | 1.00 | 1.00 | 1.00 |
| St6gal1 | 1.00 | 1.00 | 0.94 | 1.03 | 1.21 | 0.97 | 1.00 | 1.05 | 0.99 | 0.96 |
| Susd4 | 1.00 | 1.00 | 0.93 | 1.57 | 1.04 | 1.05 | 0.79 | 1.38 | 1.00 | 1.00 |
| Sv2c | 1.00 | 1.00 | 0.97 | 6.14 | 1.20 | 0.75 | 1.00 | 1.00 | 1.00 | 1.00 |
| Sycn | 0.95 | 1.03 | 1.52 | 1.00 | 1.00 | 1.32 | 1.15 | 1.55 | 1.12 | 1.00 |
| Sytl4 | 1.00 | 1.05 | 1.18 | 1.33 | 1.06 | 0.88 | 1.00 | 1.03 | 0.65 | 0.88 |
| Tacstd2 | 1.00 | 1.00 | 1.00 | 1.00 | 1.00 | 1.00 | 0.99 | 0.98 | 1.03 | 0.97 |
| Tat | 1.00 | 1.00 | 1.00 | 1.00 | 1.00 | 1.00 | 1.00 | 0.67 | 1.00 | 1.00 |
| Tceal3 | 1.00 | 1.00 | 1.01 | 0.67 | 0.88 | 0.97 | 0.61 | 0.90 | 0.84 | 0.65 |
| Tcf7 | 1.00 | 1.00 | 0.81 | 1.26 | 0.86 | 0.88 | 1.07 | 1.02 | 0.85 | 0.97 |
| Teddm1 | 1.00 | 1.00 | 1.00 | 1.00 | 1.00 | 1.00 | 1.00 | 1.00 | 1.00 | 1.00 |
| Tff2 | 1.00 | 1.23 | 1.00 | 1.00 | 1.00 | 1.00 | 1.00 | 1.00 | 1.00 | 1.00 |
| Tff3 | 1.77 | 8.31 | 1.00 | 1.00 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 1.00 | 1.00 |
| Tgoln2 | 1.00 | 0.85 | 1.00 | 1.69 | 1.00 | 1.00 | 1.00 | 1.00 | 3.87 | 1.00 |
| Tgtp1 | 1.00 | 1.04 | 1.00 | 1.00 | 1.00 | 1.06 | 1.00 | 12.95 | 0.92 | 1.05 |
| Tgtp2 | 1.00 | 1.11 | 1.00 | 1.00 | 1.00 | 1.11 | 1.00 | 7.77 | 0.87 | 1.12 |
| Tm4sf20 | 1.00 | 1.68 | 1.00 | 1.00 | 1.00 | 1.00 | 1.00 | 1.00 | 1.00 | 1.00 |
| Tmem150c | 1.00 | 1.00 | 1.00 | 1.18 | 1.05 | 0.96 | 1.00 | 1.04 | 1.00 | 1.00 |
| Tmem178b | 1.00 | 1.00 | 0.77 | 5.66 | 1.49 | 0.96 | 1.00 | 1.00 | 1.00 | 1.00 |
| Tmem27 | 1.14 | 1.61 | 1.00 | 1.00 | 1.00 | 1.00 | 1.00 | 1.00 | 1.00 | 1.00 |
| Tox3 | 1.00 | 1.00 | 0.90 | 1.05 | 0.97 | 1.04 | 1.00 | 1.00 | 1.00 | 1.00 |
| Tpd52l1 | 1.00 | 1.01 | 0.90 | 0.73 | 0.78 | 0.97 | 1.22 | 0.71 | 1.00 | 1.00 |
| Trf | 0.52 | 0.99 | 0.99 | 1.04 | 1.25 | 1.30 | 1.04 | 0.91 | 0.92 | 0.89 |
| Trim56 | 1.00 | 0.80 | 1.04 | 1.44 | 1.52 | 1.00 | 0.52 | 2.07 | 4.18 | 1.55 |
| Try10 | 0.96 | 1.17 | 1.00 | 1.00 | 1.00 | 1.00 | 1.00 | 1.00 | 1.00 | 1.00 |
| Try4 | 0.91 | 1.10 | 1.50 | 1.86 | 1.00 | 1.24 | 1.00 | 1.14 | 2.49 | 1.00 |
| Try5 | 0.89 | 1.07 | 1.86 | 0.86 | 1.00 | 0.95 | 1.13 | 1.47 | 2.48 | 1.00 |
| Ttr | 0.81 | 0.76 | 0.82 | 0.60 | 1.00 | 0.88 | 1.00 | 0.27 | 1.00 | 1.00 |
| Ucp1 | 1.00 | 1.00 | 1.00 | 1.00 | 1.00 | 1.00 | 1.00 | 1.00 | 1.00 | 1.00 |
| Uhmk1 | 1.00 | 1.00 | 0.76 | 5.67 | 1.33 | 0.78 | 0.66 | 1.66 | 4.65 | 2.15 |
| Vasn | 0.95 | 0.94 | 0.94 | 1.32 | 1.04 | 1.00 | 0.94 | 0.94 | 7.35 | 3.46 |
| Vip | 1.00 | 1.20 | 0.91 | 0.64 | 0.82 | 1.06 | 1.00 | 1.00 | 1.00 | 1.00 |
| Vtn | 0.79 | 1.14 | 1.02 | 0.95 | 0.94 | 0.96 | 1.07 | 0.85 | 1.00 | 1.00 |
| Wfdc10 | 1.00 | 1.00 | 1.00 | 1.00 | 1.00 | 1.00 | 1.00 | 1.00 | 1.00 | 1.00 |
| Wfdc11 | 1.00 | 1.00 | 1.00 | 1.00 | 1.00 | 1.00 | 1.00 | 1.00 | 1.00 | 1.00 |
| Wfdc15b | 1.00 | 1.06 | 1.00 | 1.00 | 1.00 | 1.00 | 1.00 | 1.00 | 1.00 | 1.00 |
| Wfdc2 | 1.00 | 1.59 | 1.00 | 1.00 | 0.94 | 1.00 | 1.17 | 0.80 | 1.00 | 1.00 |

Fig. 37- 28

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Wfdc6a | 1.00 | 1.00 | 1.00 | 1.00 | 1.00 | 1.00 | 1.00 | 1.00 | 1.39 | 1.03 | 1.00 | 1.00 |
| Wfdc6b | 1.00 | 1.00 | 1.00 | 1.00 | 1.00 | 1.00 | 1.00 | 1.00 | 0.64 | 0.49 | 1.00 | 1.00 |
| Wfdc8 | 1.00 | 1.00 | 1.00 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 | 1.00 | 1.00 | 1.00 |
| Wwc1 | 1.00 | 1.00 | 1.00 | 1.00 | 1.00 | 1.00 | 1.00 | 1.00 | 0.98 | 1.00 | 0.80 | 1.02 |
| Xkrx | 1.00 | 1.00 | 1.00 | 1.00 | 0.76 | 1.88 | 1.00 | 1.00 | 1.00 | 1.00 | 0.69 | 1.00 |
| Zbed6 | 1.00 | 1.00 | 0.58 | 0.79 | 1.00 | 1.00 | 2.05 | 0.91 | 2.33 | 1.31 | 0.91 | 1.00 |
| Zbp1 | 1.00 | 1.00 | 1.00 | 1.00 | 1.00 | 1.00 | 1.00 | 1.81 | 1.12 | 2.64 | 1.00 | 1.00 |
| Zfp369 | 1.00 | 1.00 | 0.53 | 0.72 | 1.00 | 0.83 | 2.32 | 0.89 | 1.42 | 0.95 | 0.63 | 0.91 |
| Zfp648 | 1.00 | 1.00 | 1.00 | 1.00 | 1.00 | 1.00 | 1.00 | 1.00 | 1.00 | 1.00 | 1.00 | 1.00 |
| Zg16 | 0.81 | 1.00 | 1.00 | 1.00 | 1.00 | 1.28 | 1.00 | 0.72 | 1.00 | 1.30 | 1.00 | 0.89 |
| 4930474H20Rik | 1.00 | 1.00 | 1.00 | 1.00 | 1.00 | 1.00 | 1.00 | 1.00 | 1.00 | 1.00 | 1.00 | 1.00 |
| 5830403L16Rik | 1.00 | 1.00 | 1.00 | 1.00 | 1.00 | 1.00 | 1.00 | 1.00 | 1.00 | 1.00 | 1.00 | 1.00 |
| 9230104L09Rik | 1.00 | 1.00 | 1.00 | 1.00 | 1.00 | 1.00 | 0.84 | 0.76 | 0.79 | 1.18 | 1.00 | 1.00 |
| 9230110F15Rik | 1.00 | 1.00 | 1.00 | 1.00 | 1.00 | 1.00 | 1.00 | 1.00 | 1.00 | 1.00 | 1.00 | 1.00 |
| A730008H23Rik | 1.00 | 1.00 | 1.00 | 1.00 | 1.04 | 0.93 | 1.08 | 1.66 | 2.61 | 1.77 | 1.00 | 1.00 |
| AI747448 | 1.00 | 1.00 | 1.00 | 1.00 | 1.00 | 1.00 | 1.00 | 1.00 | 1.00 | 1.00 | 1.00 | 1.00 |
| AU015791 | 1.00 | 1.00 | 1.00 | 1.00 | 1.00 | 1.00 | 1.00 | 1.00 | 1.00 | 1.00 | 1.00 | 1.00 |
| AW112010 | 0.43 | 1.40 | 1.45 | 1.17 | 1.00 | 0.90 | 1.10 | 1.03 | 1.12 | 1.02 | 1.10 | 1.12 |
| AY761185 | 1.00 | 1.00 | 1.00 | 1.00 | 1.00 | 1.00 | 1.00 | 1.00 | 1.00 | 1.00 | 1.00 | 1.00 |
| Acaa1b | 5.11 | 1.00 | 1.10 | 0.92 | 1.18 | 0.90 | 0.94 | 0.90 | 0.79 | 1.11 | 0.93 | 0.72 |
| Acpp | 1.00 | 1.00 | 1.00 | 1.00 | 1.00 | 1.00 | 1.00 | 1.00 | 1.43 | 1.13 | 0.80 | 0.74 |
| Actg2 | 1.00 | 1.00 | 1.00 | 1.00 | 1.00 | 1.19 | 1.52 | 1.21 | 1.01 | 1.14 | 1.00 | 1.00 |
| Adam28 | 1.00 | 1.00 | 1.00 | 1.00 | 1.00 | 1.00 | 1.00 | 1.00 | 0.93 | 0.97 | 1.00 | 1.00 |
| Adam7 | 1.00 | 1.00 | 1.00 | 1.00 | 1.00 | 1.00 | 1.00 | 1.00 | 1.00 | 1.00 | 1.00 | 1.00 |
| Ago2 | 1.00 | 1.00 | 0.73 | 0.94 | 1.20 | 1.36 | 1.36 | 1.33 | 1.59 | 1.19 | 0.48 | 1.28 |
| Ahsg | 44.19 | 1.00 | 1.46 | 0.86 | 1.48 | 0.86 | 0.80 | 0.71 | 1.12 | 1.00 | 1.00 | 1.00 |
| Akp3 | 1.00 | 1.00 | 1.00 | 1.00 | 1.00 | 1.00 | 1.00 | 1.00 | 1.00 | 1.00 | 1.00 | 1.00 |
| Alb | 106 | 1.00 | 2.82 | 1.09 | 1.86 | 0.95 | 1.00 | 1.00 | 1.00 | 1.00 | 1.25 | 1.00 |
| Aldob | 8.09 | 1.00 | 1.00 | 1.00 | 1.00 | 1.00 | 0.82 | 1.39 | 0.95 | 1.00 | 1.08 | 0.93 |
| Aldoc | 1.00 | 1.00 | 1.00 | 1.00 | 1.00 | 1.00 | 1.00 | 1.00 | 1.02 | 1.11 | 1.28 | 0.85 |
| Alox15 | 9.23 | 4.38 | 1.00 | 1.00 | 1.00 | 1.00 | 1.00 | 1.00 | 1.59 | 1.04 | 1.00 | 1.00 |
| Alpi | 1.00 | 1.00 | 1.00 | 1.00 | 1.00 | 1.00 | 1.00 | 1.00 | 1.00 | 1.00 | 1.00 | 1.00 |
| Ambp | 5.14 | 1.00 | 1.00 | 1.00 | 1.00 | 1.00 | 1.00 | 1.00 | 1.00 | 1.00 | 1.00 | 1.00 |
| Amd1 | 1.00 | 1.00 | 0.89 | 2.86 | 1.00 | 1.00 | 1.00 | 2.09 | 1.29 | 5.15 | 1.00 | 1.00 |
| Amy1 | 1.00 | 1.00 | 1.32 | 0.76 | 0.99 | 0.94 | 1.04 | 1.04 | 0.98 | 1.59 | 1.00 | 1.00 |
| Amy2a5 | 0.80 | 7.00 | 1.00 | 1.00 | 0.83 | 0.71 | 1.00 | 0.73 | 1.00 | 1.44 | 1.00 | 0.83 |
| Amy2b | 0.64 | 1.89 | 1.00 | 1.00 | 0.77 | 0.70 | 1.00 | 1.11 | 1.00 | 1.60 | 1.00 | 0.60 |
| Ang4 | 1.00 | 1.00 | 1.00 | 1.00 | 1.00 | 1.00 | 1.00 | 1.00 | 0.76 | 1.04 | 1.00 | 1.00 |
| Ap1s2 | 0.67 | 0.92 | 1.04 | 1.09 | 0.78 | 0.90 | 0.91 | 0.89 | 0.98 | 0.93 | 1.12 | 0.86 |
| Apoa1 | 19.44 | 1.00 | 3.09 | 1.31 | 2.47 | 1.08 | 1.00 | 1.00 | 1.00 | 1.00 | 1.13 | 1.00 |
| Apoa2 | 44.09 | 1.00 | 0.68 | 0.61 | 1.26 | 1.44 | 1.00 | 1.00 | 1.00 | 1.00 | 0.77 | 1.07 |
| Apoa5 | 8.22 | 1.00 | 1.00 | 1.00 | 1.00 | 1.00 | 1.00 | 1.00 | 1.00 | 1.00 | 1.00 | 1.00 |
| Apoc1 | 18.24 | 1.00 | 2.29 | 0.78 | 1.01 | 0.93 | 1.30 | 1.10 | 0.80 | 0.85 | 0.92 | 0.60 |
| Apoc3 | 11.67 | 1.00 | 1.00 | 1.00 | 1.08 | 0.84 | 1.00 | 1.00 | 1.00 | 1.00 | 1.36 | 0.80 |
| Apoc4 | 5.43 | 1.00 | 1.00 | 1.00 | 1.00 | 1.00 | 1.00 | 1.00 | 1.00 | 1.00 | 1.00 | 1.00 |
| Apoe | 12.48 | 1.70 | 1.28 | 0.83 | 0.90 | 0.82 | 0.98 | 0.93 | 0.81 | 1.04 | 1.06 | 0.79 |
| Apoh | 6.48 | 1.00 | 1.00 | 1.00 | 1.00 | 1.00 | 1.00 | 1.00 | 1.00 | 1.00 | 1.27 | 1.27 |
| Asb11 | 1.00 | 1.00 | 1.01 | 0.84 | 2.61 | 1.12 | 0.87 | 0.90 | 0.69 | 1.37 | 0.78 | 1.06 |
| Azgp1 | 7.18 | 1.00 | 1.00 | 1.00 | 1.00 | 1.00 | 1.00 | 1.00 | 1.00 | 1.00 | 1.00 | 1.00 |
| B4galnt2 | 1.00 | 1.00 | 1.00 | 1.00 | 1.00 | 1.00 | 1.00 | 1.00 | 1.00 | 1.00 | 1.00 | 1.00 |
| B9d1 | 1.00 | 1.00 | 0.99 | 0.91 | 1.00 | 1.00 | 1.25 | 1.00 | 1.04 | 1.36 | 0.97 | 0.98 |
| Bcl2l15 | 1.00 | 1.00 | 1.00 | 1.00 | 1.00 | 1.00 | 1.00 | 1.00 | 1.00 | 1.00 | 1.55 | 2.81 |
| Bex2 | 1.00 | 1.00 | 1.00 | 1.00 | 1.00 | 1.00 | 1.00 | 1.00 | 0.79 | 1.07 | 1.00 | 1.08 |
| Bex4 | 1.00 | 1.00 | 0.88 | 0.83 | 1.00 | 1.00 | 0.94 | 1.00 | 0.88 | 0.86 | 0.96 | 1.06 |
| Bglap3 | 1.00 | 1.00 | 1.00 | 1.00 | 1.00 | 1.00 | 1.00 | 1.00 | 1.00 | 1.00 | 1.28 | 0.76 |
| Bhmt | 5.87 | 1.00 | 1.00 | 1.00 | 1.00 | 1.00 | 1.00 | 1.00 | 1.00 | 1.00 | 1.43 | 1.16 |
| Bsph1 | 1.00 | 1.00 | 1.00 | 1.00 | 1.00 | 1.00 | 1.00 | 1.00 | 1.00 | 1.00 | 1.00 | 1.00 |
| Bspry | 1.00 | 1.00 | 1.00 | 1.00 | 1.00 | 1.00 | 1.00 | 1.00 | 0.90 | 0.85 | 1.03 | 1.22 |
| Btg3 | 0.65 | 1.05 | 1.98 | 0.69 | 0.78 | 0.39 | 8.30 | 0.26 | 0.49 | 1.40 | 3.49 | 3.34 |

Fig. 37- 29

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Wfdc6a | 1.00 | 1.00 | 1.00 | 1.00 | 1.00 | 1.00 | 7.46 | 1.76 | 1.19 | 0.89 | 1.00 | 1.00 |
| Wfdc6b | 1.00 | 1.00 | 1.00 | 1.00 | 1.00 | 1.00 | 15.27 | 1.00 | 1.48 | 1.31 | 1.00 | 1.00 |
| Wfdc8 | 1.00 | 1.00 | 1.00 | 1.00 | 1.00 | 1.00 | 13.55 | 1.00 | 1.00 | 1.00 | 1.00 | 1.00 |
| Wfdc9 | 1.00 | 1.00 | 1.00 | 1.00 | 1.00 | 1.00 | 20.61 | 1.00 | 1.12 | 1.00 | 1.00 | 1.00 |
| Wwc1 | 1.24 | 0.95 | 1.97 | 1.06 | 1.04 | 1.10 | 5.60 | 2.91 | 1.00 | 0.94 | 1.00 | 1.00 |
| Xkrx | 1.00 | 1.00 | 1.00 | 1.00 | 0.84 | 0.82 | 6.09 | 1.00 | 1.00 | 1.00 | 0.78 | 0.81 |
| Zbed6 | 3.25 | 0.19 | 13.22 | 1.01 | 1.02 | 1.10 | 1.00 | 1.00 | 0.32 | 1.22 | 0.87 | 1.50 |
| Zbp1 | 1.30 | 1.23 | 0.85 | 0.93 | 0.98 | 1.00 | 0.80 | 1.00 | 0.99 | 1.00 | 1.38 | 1.12 |
| Zfp369 | 2.07 | 0.37 | 5.51 | 0.79 | 0.81 | 1.02 | 0.87 | 1.00 | 1.00 | 1.00 | 0.82 | 1.66 |
| Zfp648 | 1.00 | 1.00 | 1.00 | 1.00 | 1.00 | 1.00 | 11.09 | 1.82 | 1.00 | 1.00 | 1.00 | 1.00 |
| Zg16 | 1.00 | 4.58 | 0.74 | 1.10 | 2.40 | 1.94 | 1.00 | 1.00 | 1.00 | 1.00 | 53.96 | 0.09 |
| 4930474H20Rik | 1.00 | 1.00 | 1.00 | 1.00 | 1.00 | 1.00 | 1.00 | 1.00 | 1.00 | 1.00 | 1.00 | 1.00 |
| 5830403L16Rik | 1.00 | 1.00 | 1.00 | 1.00 | 1.00 | 1.00 | 19.25 | 162 | 0.99 | 0.59 | 1.00 | 1.00 |
| 9230104L09Rik | 1.00 | 1.00 | 1.00 | 1.00 | 1.00 | 1.00 | 26.13 | 248 | 1.05 | 0.89 | 1.00 | 1.00 |
| 9230110F15Rik | 1.00 | 1.00 | 1.00 | 1.00 | 1.00 | 1.00 | 6.80 | 103 | 1.00 | 1.00 | 1.00 | 1.00 |
| A730008H23Rik | 1.76 | 0.28 | 7.23 | 0.80 | 0.71 | 2.65 | 0.81 | 0.85 | 0.12 | 0.96 | 1.09 | 2.81 |
| AI747448 | 1.00 | 1.00 | 1.40 | 1.55 | 6.23 | 2.10 | 1.00 | 1.00 | 1.00 | 1.00 | 1.00 | 1.00 |
| AU015791 | 1.00 | 1.00 | 0.61 | 1.68 | 1.00 | 1.00 | 3.92 | 9.88 | 1.00 | 1.00 | 1.00 | 1.00 |
| AW112010 | 0.88 | 1.35 | 0.68 | 0.83 | 1.32 | 1.02 | 1.17 | 0.97 | 1.00 | 1.00 | 0.93 | 0.95 |
| AY761185 | 1.00 | 1.00 | 1.00 | 1.00 | 1.00 | 1.00 | 324 | 1.00 | 1.00 | 1.41 | 1.00 | 1.00 |
| Acaa1b | 1.01 | 0.99 | 0.84 | 0.93 | 0.96 | 0.89 | 1.00 | 0.72 | 1.36 | 0.60 | 0.70 | 1.30 |
| Acpp | 1.00 | 1.00 | 1.12 | 1.29 | 0.97 | 0.90 | 6.37 | 5.09 | 1.00 | 1.00 | 1.25 | 1.00 |
| Actg2 | 1.00 | 1.00 | 0.82 | 1.14 | 0.85 | 1.06 | 1.93 | 5.06 | 1.08 | 0.88 | 0.92 | 0.82 |
| Adam28 | 1.00 | 1.00 | 1.00 | 1.00 | 1.36 | 1.03 | 5.44 | 49.12 | 1.00 | 1.00 | 1.00 | 1.00 |
| Adam7 | 1.00 | 1.00 | 1.00 | 1.00 | 1.00 | 1.00 | 119 | 112 | 1.00 | 1.00 | 1.00 | 1.00 |
| Ago2 | 2.44 | 0.35 | 7.58 | 1.06 | 1.02 | 1.06 | 1.09 | 1.08 | 0.32 | 1.08 | 0.98 | 1.32 |
| Ahsg | 0.92 | 0.88 | 1.00 | 0.56 | 0.24 | 0.56 | 1.16 | 3.69 | 0.63 | 1.05 | 1.00 | 1.00 |
| Akp3 | 1.00 | 1.00 | 1.00 | 1.00 | 46.77 | 20.68 | 1.00 | 1.00 | 1.00 | 1.00 | 1.00 | 1.00 |
| Alb | 0.97 | 0.87 | 1.00 | 0.79 | 0.12 | 1.16 | 1.57 | 5.73 | 0.57 | 0.90 | 1.00 | 1.00 |
| Aldob | 0.92 | 0.96 | 0.81 | 1.10 | 3.19 | 2.26 | 6.43 | 3.79 | 1.00 | 1.00 | 1.22 | 1.00 |
| Aldoc | 0.90 | 1.49 | 0.74 | 1.04 | 0.69 | 0.98 | 5.04 | 3.74 | 0.97 | 1.27 | 0.73 | 0.77 |
| Alox15 | 1.00 | 1.00 | 1.00 | 1.00 | 0.94 | 0.90 | 0.57 | 1.64 | 1.00 | 1.00 | 1.00 | 1.16 |
| Alpi | 1.00 | 1.00 | 0.94 | 0.90 | 5.06 | 3.83 | 1.00 | 1.00 | 1.00 | 1.00 | 1.00 | 1.00 |
| Ambp | 0.94 | 1.27 | 1.00 | 0.79 | 0.76 | 1.07 | 1.00 | 1.17 | 1.00 | 0.91 | 1.00 | 1.00 |
| Amd1 | 1.00 | 1.00 | 1.00 | 1.00 | 1.00 | 1.00 | 1.00 | 1.00 | 5.93 | 1.00 | 3.27 | 1.00 |
| Amy1 | 0.96 | 0.90 | 1.95 | 4.78 | 2.47 | 1.98 | 0.77 | 0.93 | 1.50 | 1.22 | 15.36 | 0.17 |
| Amy2a5 | 0.40 | 5.28 | 1.84 | 242 | 2.68 | 13.12 | 0.70 | 0.89 | 1.00 | 1.00 | 174 | 0.03 |
| Amy2b | 0.85 | 1.78 | 2.08 | 73.04 | 2.69 | 12.85 | 0.59 | 0.85 | 1.00 | 1.00 | 100 | 0.04 |
| Ang4 | 1.00 | 1.00 | 0.54 | 1.81 | 10.33 | 3.34 | 1.00 | 1.00 | 1.00 | 1.00 | 1.00 | 1.00 |
| Ap1s2 | 0.95 | 1.09 | 0.88 | 0.98 | 0.75 | 1.00 | 7.83 | 3.19 | 0.76 | 1.11 | 0.96 | 0.77 |
| Apoa1 | 0.81 | 1.01 | 0.89 | 0.50 | 1.04 | 1.05 | 1.40 | 8.17 | 0.74 | 1.00 | 1.00 | 1.00 |
| Apoa2 | 0.84 | 1.16 | 1.00 | 1.02 | 0.13 | 0.76 | 2.36 | 11.98 | 1.11 | 0.91 | 1.00 | 1.00 |
| Apoa5 | 0.91 | 0.90 | 1.00 | 1.00 | 0.51 | 1.00 | 1.00 | 1.72 | 1.00 | 1.00 | 1.00 | 1.00 |
| Apoc1 | 0.95 | 1.19 | 0.61 | 0.58 | 0.67 | 0.92 | 0.84 | 0.83 | 1.35 | 0.62 | 0.73 | 0.73 |
| Apoc3 | 0.83 | 1.16 | 1.00 | 1.00 | 1.19 | 1.15 | 0.74 | 0.96 | 1.00 | 1.00 | 1.00 | 1.00 |
| Apoc4 | 0.90 | 1.13 | 1.00 | 1.00 | 0.67 | 1.00 | 0.66 | 0.84 | 1.00 | 1.00 | 1.00 | 1.00 |
| Apoe | 0.90 | 1.15 | 0.92 | 0.80 | 0.86 | 1.07 | 0.96 | 0.85 | 1.57 | 0.93 | 0.96 | 0.81 |
| Apoh | 0.91 | 1.10 | 1.00 | 1.00 | 0.44 | 1.00 | 1.00 | 1.65 | 1.31 | 0.89 | 1.00 | 1.00 |
| Asb11 | 1.00 | 1.00 | 1.10 | 0.75 | 0.82 | 1.86 | 6.20 | 1.00 | 1.00 | 1.00 | 1.00 | 1.00 |
| Azgp1 | 0.97 | 1.01 | 1.00 | 1.00 | 0.53 | 1.00 | 1.00 | 2.45 | 1.00 | 1.00 | 1.00 | 1.00 |
| B4galnt2 | 1.00 | 1.00 | 1.03 | 1.09 | 1.27 | 1.09 | 5.44 | 4.94 | 1.00 | 1.00 | 1.00 | 1.00 |
| B9d1 | 1.00 | 1.00 | 0.86 | 0.90 | 1.03 | 1.24 | 5.55 | 1.55 | 1.59 | 0.92 | 1.13 | 1.00 |
| Bcl2l15 | 1.00 | 1.00 | 0.74 | 1.36 | 2.03 | 1.00 | 5.01 | 9.09 | 0.93 | 0.81 | 0.89 | 1.33 |
| Bex2 | 1.00 | 1.00 | 0.62 | 0.89 | 0.92 | 1.17 | 10.48 | 5.59 | 1.47 | 0.76 | 0.83 | 1.00 |
| Bex4 | 1.00 | 1.00 | 0.79 | 1.52 | 1.00 | 0.81 | 5.42 | 3.11 | 1.10 | 1.04 | 0.85 | 0.96 |
| Bglap3 | 1.00 | 1.00 | 1.05 | 1.43 | 1.25 | 1.14 | 14.79 | 2.34 | 1.00 | 1.00 | 1.00 | 1.00 |
| Bhmt | 0.95 | 1.07 | 0.99 | 1.00 | 0.40 | 1.00 | 1.00 | 1.90 | 1.14 | 1.28 | 1.00 | 1.00 |
| Bsph1 | 1.00 | 1.00 | 1.00 | 1.00 | 1.00 | 1.00 | 31.43 | 4.62 | 1.00 | 1.00 | 1.00 | 1.00 |
| Bspry | 1.00 | 1.00 | 1.07 | 0.95 | 1.06 | 1.13 | 6.20 | 3.71 | 1.24 | 0.87 | 1.04 | 1.00 |
| Btg3 | 1.00 | 1.00 | 2.32 | 2.22 | 0.99 | 1.41 | 1.98 | 0.37 | 1.65 | 0.48 | 1.68 | 1.72 |

Fig. 37-30

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Wfdc6a | 1.00 | 1.00 | 1.00 | 1.00 | 1.00 | 1.00 | 1.00 | 1.00 | 1.00 | 1.00 |
| Wfdc6b | 1.00 | 1.00 | 1.00 | 1.00 | 1.00 | 1.00 | 1.00 | 1.00 | 1.00 | 1.00 |
| Wfdc8 | 1.00 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 | 1.00 |
| Wwc1 | 1.32 | 1.02 | 0.98 | 1.38 | 1.05 | 0.96 | 1.07 | 1.06 | 1.00 | 1.00 |
| Xkrx | 1.00 | 1.00 | 0.75 | 1.12 | 0.82 | 1.11 | 1.01 | 1.02 | 0.71 | 0.85 |
| Zbed6 | 1.00 | 0.39 | 0.95 | 7.28 | 2.04 | 0.79 | 0.46 | 2.20 | 9.10 | 2.92 |
| Zbp1 | 1.00 | 1.00 | 1.00 | 1.00 | 1.00 | 1.00 | 1.00 | 6.33 | 1.15 | 1.44 |
| Zfp369 | 1.00 | 1.00 | 1.02 | 5.58 | 1.69 | 1.00 | 1.00 | 1.38 | 5.26 | 1.60 |
| Zfp648 | 1.00 | 1.00 | 1.00 | 1.00 | 1.00 | 1.00 | 1.39 | 1.17 | 1.00 | 1.00 |
| Zg16 | 0.80 | 1.13 | 1.96 | 0.59 | 1.00 | 0.84 | 0.67 | 0.95 | 0.92 | 0.51 |
| 4930474H20Rik | 1.00 | 1.00 | 1.00 | 1.00 | 1.00 | 1.00 | 1.00 | 1.00 | 1.00 | 1.00 |
| 5830403L16Rik | 1.00 | 1.00 | 1.00 | 1.00 | 1.00 | 1.00 | 1.00 | 1.00 | 1.00 | 1.00 |
| 9230104L09Rik | 1.00 | 1.00 | 1.00 | 1.00 | 1.00 | 1.00 | 1.00 | 1.00 | 1.00 | 1.00 |
| 9230110F15Rik | 1.00 | 1.00 | 1.00 | 1.00 | 1.00 | 1.00 | 1.00 | 1.00 | 1.00 | 1.00 |
| A730008H23Rik | 1.00 | 1.00 | 0.88 | 3.46 | 0.87 | 1.00 | 0.70 | 1.47 | 6.49 | 1.89 |
| AI747448 | 1.00 | 1.00 | 1.00 | 1.00 | 1.00 | 1.00 | 1.00 | 1.00 | 1.00 | 1.00 |
| AU015791 | 1.00 | 1.00 | 1.00 | 1.00 | 1.00 | 1.00 | 1.00 | 1.00 | 1.00 | 1.00 |
| AW112010 | 0.46 | 1.80 | 1.31 | 1.26 | 1.61 | 2.53 | 1.12 | 9.56 | 0.59 | 1.20 |
| AY761185 | 1.00 | 1.00 | 1.00 | 1.00 | 1.00 | 1.00 | 1.00 | 1.00 | 1.00 | 1.00 |
| Acaa1b | 1.18 | 1.02 | 0.67 | 0.78 | 0.93 | 1.22 | 1.17 | 0.94 | 0.79 | 1.06 |
| Acpp | 0.95 | 0.76 | 1.00 | 1.00 | 1.00 | 1.00 | 0.96 | 1.01 | 1.24 | 1.27 |
| Actg2 | 1.00 | 1.50 | 1.00 | 1.00 | 1.00 | 1.00 | 1.00 | 1.00 | 1.00 | 1.00 |
| Adam28 | 1.00 | 1.00 | 1.00 | 1.00 | 1.00 | 1.00 | 1.00 | 1.00 | 1.00 | 1.00 |
| Adam7 | 1.00 | 1.00 | 1.00 | 1.00 | 1.00 | 1.00 | 1.00 | 1.00 | 1.00 | 1.00 |
| Ago2 | 1.00 | 0.56 | 0.94 | 5.02 | 1.36 | 0.81 | 0.68 | 1.54 | 3.97 | 1.72 |
| Ahsg | 0.82 | 0.67 | 1.00 | 1.00 | 1.00 | 1.00 | 0.89 | 0.15 | 1.00 | 1.26 |
| Akp3 | 1.00 | 1.00 | 1.00 | 1.00 | 1.00 | 1.00 | 1.00 | 1.00 | 1.00 | 1.00 |
| Alb | 1.00 | 0.57 | 1.00 | 1.00 | 1.00 | 1.00 | 0.59 | 0.17 | 0.77 | 1.18 |
| Aldob | 0.95 | 1.41 | 0.95 | 0.71 | 0.93 | 1.03 | 1.00 | 0.29 | 1.00 | 1.00 |
| Aldoc | 1.00 | 1.00 | 0.99 | 0.80 | 0.99 | 1.03 | 1.20 | 0.96 | 1.00 | 1.00 |
| Alox15 | 1.00 | 1.00 | 1.00 | 1.00 | 1.00 | 1.00 | 1.00 | 1.00 | 0.83 | 0.57 |
| Alpi | 1.00 | 1.00 | 1.00 | 1.00 | 1.00 | 1.00 | 1.00 | 1.00 | 1.00 | 1.00 |
| Ambp | 0.57 | 0.85 | 1.00 | 1.00 | 1.00 | 1.00 | 1.00 | 1.00 | 1.00 | 1.00 |
| Amd1 | 1.00 | 1.00 | 1.92 | 0.34 | 1.86 | 0.57 | 6.93 | 1.00 | 1.07 | 25.06 |
| Amy1 | 0.89 | 1.14 | 1.23 | 0.78 | 1.21 | 0.96 | 0.78 | 1.04 | 1.00 | 1.00 |
| Amy2a5 | 0.92 | 1.02 | 1.19 | 1.15 | 1.00 | 0.88 | 1.22 | 1.44 | 5.35 | 1.00 |
| Amy2b | 1.03 | 0.96 | 2.10 | 1.26 | 1.00 | 1.14 | 0.93 | 1.36 | 1.38 | 1.00 |
| Ang4 | 1.00 | 1.00 | 1.00 | 1.00 | 1.00 | 1.00 | 0.99 | 1.00 | 1.00 | 1.00 |
| Ap1s2 | 1.00 | 1.00 | 1.06 | 0.85 | 0.98 | 1.01 | 1.25 | 1.01 | 0.97 | 1.17 |
| Apoa1 | 1.11 | 0.80 | 1.40 | 0.84 | 0.64 | 0.93 | 0.47 | 0.09 | 1.00 | 1.07 |
| Apoa2 | 1.00 | 0.91 | 1.00 | 1.00 | 1.00 | 1.00 | 0.76 | 0.08 | 1.00 | 1.01 |
| Apoa5 | 1.00 | 1.00 | 1.00 | 1.00 | 1.00 | 1.00 | 1.00 | 1.00 | 1.00 | 1.00 |
| Apoc1 | 1.00 | 0.49 | 0.64 | 0.82 | 0.94 | 1.62 | 1.06 | 0.86 | 0.44 | 1.11 |
| Apoc3 | 1.00 | 0.63 | 0.94 | 0.53 | 1.00 | 1.00 | 0.88 | 0.42 | 1.00 | 1.00 |
| Apoc4 | 1.00 | 1.00 | 1.00 | 1.00 | 1.00 | 1.00 | 0.66 | 0.57 | 1.00 | 1.00 |
| Apoe | 0.74 | 1.12 | 0.98 | 0.72 | 0.98 | 1.16 | 1.06 | 0.88 | 0.67 | 0.76 |
| Apoh | 1.00 | 1.00 | 1.00 | 1.00 | 1.00 | 1.00 | 1.00 | 0.45 | 1.00 | 1.00 |
| Asb11 | 1.47 | 1.01 | 0.75 | 0.67 | 0.64 | 1.00 | 1.00 | 1.00 | 1.00 | 1.00 |
| Azgp1 | 1.00 | 1.00 | 1.00 | 1.00 | 1.00 | 1.00 | 1.00 | 0.77 | 1.00 | 1.00 |
| B4galnt2 | 1.00 | 1.00 | 1.00 | 1.00 | 1.00 | 1.00 | 0.93 | 1.26 | 1.00 | 1.00 |
| B9d1 | 1.14 | 1.40 | 0.87 | 0.83 | 0.91 | 1.06 | 0.94 | 0.63 | 1.00 | 0.68 |
| Bcl2l15 | 1.00 | 1.00 | 0.90 | 0.82 | 0.98 | 0.78 | 1.00 | 0.89 | 0.40 | 0.86 |
| Bex2 | 0.70 | 1.51 | 1.05 | 0.64 | 0.90 | 0.98 | 1.44 | 1.00 | 1.00 | 1.00 |
| Bex4 | 1.00 | 1.00 | 1.34 | 0.52 | 1.07 | 1.01 | 1.00 | 1.00 | 0.58 | 0.79 |
| Bglap3 | 1.97 | 2.14 | 1.00 | 1.00 | 1.00 | 1.00 | 1.06 | 0.95 | 1.00 | 1.00 |
| Bhmt | 1.00 | 1.00 | 1.00 | 1.00 | 1.00 | 1.00 | 1.07 | 0.69 | 1.00 | 1.00 |
| Bsph1 | 1.00 | 1.00 | 1.00 | 1.00 | 1.00 | 1.00 | 1.00 | 1.00 | 1.00 | 1.00 |
| Bspry | 0.67 | 1.31 | 0.82 | 1.55 | 1.31 | 0.89 | 0.86 | 0.90 | 1.00 | 1.00 |
| Btg3 | 2.33 | 1.00 | 0.50 | 1.00 | 3.55 | 5.85 | 0.15 | 3.88 | 0.21 | 0.52 |

Fig. 37-31

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| C4b | 8.06 | 2.61 | 1.13 | 0.94 | 1.07 | 1.06 | 1.16 | 1.26 | 1.02 | 1.00 | 1.01 | 1.20 |
| C4bp | 1.00 | 1.00 | 1.00 | 1.00 | 1.00 | 1.00 | 1.00 | 1.00 | 1.00 | 1.00 | 1.00 | 1.00 |
| Cbl | 1.00 | 1.00 | 1.00 | 0.95 | 1.09 | 1.56 | 1.78 | 1.29 | 1.77 | 1.12 | 0.66 | 1.00 |
| Ccl12 | 1.00 | 1.00 | 1.00 | 1.00 | 1.00 | 1.00 | 0.42 | 0.54 | 0.95 | 0.66 | 1.00 | 1.00 |
| Ccl21b | 1.00 | 1.00 | 2.54 | 1.08 | 0.35 | 1.33 | 0.30 | 0.37 | 0.49 | 0.27 | 1.11 | 2.42 |
| Ccl25 | 1.00 | 1.00 | 1.04 | 1.85 | 1.26 | 1.00 | 1.00 | 1.00 | 0.77 | 0.79 | 0.86 | 1.30 |
| Ccl27b | 1.00 | 1.00 | 1.00 | 1.00 | 1.00 | 1.00 | 1.00 | 1.00 | 1.00 | 1.00 | 1.00 | 1.00 |
| Ccno | 1.00 | 1.00 | 1.00 | 1.00 | 0.82 | 0.96 | 1.00 | 1.00 | 1.24 | 1.00 | 0.86 | 1.00 |
| Ccnt1 | 1.00 | 1.00 | 0.87 | 1.09 | 1.07 | 1.33 | 1.29 | 1.25 | 1.09 | 1.09 | 0.57 | 1.43 |
| Cdh1 | 1.00 | 1.00 | 1.00 | 1.00 | 1.00 | 1.00 | 1.00 | 1.00 | 0.96 | 0.98 | 0.91 | 1.03 |
| Cdh16 | 1.00 | 1.00 | 1.00 | 1.00 | 1.00 | 1.00 | 1.07 | 1.00 | 1.04 | 1.07 | 1.01 | 1.06 |
| Cdh17 | 1.00 | 1.00 | 1.00 | 1.00 | 1.00 | 1.00 | 1.00 | 1.00 | 1.00 | 1.00 | 1.00 | 1.00 |
| Cdk6 | 1.00 | 1.00 | 0.95 | 1.17 | 1.00 | 1.00 | 1.50 | 0.96 | 1.34 | 1.26 | 1.00 | 1.00 |
| Cdkl5 | 1.00 | 1.00 | 1.00 | 1.00 | 1.00 | 1.00 | 1.00 | 1.00 | 1.48 | 0.88 | 1.00 | 1.00 |
| Cdo1 | 5.46 | 1.00 | 2.44 | 0.64 | 0.91 | 0.84 | 1.26 | 0.99 | 0.89 | 0.91 | 1.20 | 0.98 |
| Ceacam10 | 1.00 | 1.00 | 1.00 | 1.00 | 1.00 | 1.00 | 1.00 | 1.00 | 1.00 | 1.00 | 1.00 | 1.00 |
| Cel | 0.93 | 1.00 | 1.00 | 1.00 | 1.00 | 1.00 | 1.00 | 0.97 | 1.00 | 1.00 | 1.00 | 1.00 |
| Cela1 | 0.63 | 0.75 | 1.00 | 1.00 | 1.00 | 1.00 | 1.00 | 1.36 | 1.66 | 0.88 | 1.25 | 1.17 |
| Cela2a | 0.66 | 1.00 | 1.00 | 1.00 | 1.00 | 1.00 | 1.00 | 0.79 | 1.00 | 1.05 | 1.00 | 1.28 |
| Cela3b | 0.59 | 1.00 | 1.00 | 1.00 | 1.00 | 1.00 | 1.00 | 1.46 | 1.00 | 1.31 | 1.00 | 1.00 |
| Ces5a | 1.00 | 1.00 | 1.00 | 1.00 | 1.00 | 1.00 | 1.00 | 1.00 | 1.00 | 1.00 | 1.00 | 1.00 |
| Cfd | 0.87 | 1.00 | 2.30 | 0.71 | 0.98 | 0.88 | 2.27 | 1.53 | 1.69 | 0.99 | 1.52 | 3.81 |
| Chga | 1.00 | 1.00 | 1.00 | 1.00 | 1.00 | 1.00 | 1.00 | 1.00 | 1.00 | 1.00 | 1.00 | 1.00 |
| Chrm2 | 1.00 | 1.00 | 1.00 | 1.00 | 1.00 | 1.00 | 1.14 | 1.28 | 1.18 | 1.03 | 1.00 | 1.00 |
| Chrna7 | 1.00 | 1.00 | 1.00 | 1.00 | 1.00 | 1.00 | 1.00 | 1.00 | 1.08 | 1.00 | 1.00 | 1.00 |
| Cited4 | 1.00 | 1.00 | 1.26 | 1.69 | 1.00 | 1.00 | 1.25 | 1.18 | 0.85 | 1.03 | 1.08 | 1.34 |
| Ckmt1 | 1.00 | 1.00 | 1.00 | 1.00 | 1.00 | 1.00 | 1.00 | 1.00 | 0.92 | 1.07 | 1.05 | 1.01 |
| Clca3 | 1.00 | 1.00 | 1.00 | 1.00 | 1.00 | 1.00 | 1.00 | 1.00 | 3.10 | 0.71 | 1.00 | 1.00 |
| Cldn2 | 1.00 | 1.00 | 1.00 | 1.00 | 1.00 | 1.00 | 1.00 | 1.00 | 1.16 | 1.06 | 0.93 | 0.92 |
| Cldn3 | 1.00 | 1.00 | 1.00 | 1.00 | 1.00 | 1.00 | 2.18 | 1.00 | 0.88 | 0.90 | 0.98 | 1.28 |
| Cldn4 | 1.00 | 1.00 | 1.00 | 1.00 | 1.00 | 1.00 | 1.00 | 1.00 | 0.93 | 1.09 | 1.05 | 0.82 |
| Cldn7 | 1.00 | 1.00 | 1.00 | 1.00 | 1.00 | 1.00 | 1.00 | 1.00 | 0.99 | 0.92 | 0.90 | 1.16 |
| Cldn8 | 1.00 | 1.00 | 1.00 | 1.00 | 1.00 | 1.00 | 1.00 | 1.00 | 0.97 | 1.10 | 0.95 | 1.00 |
| Clec2h | 1.00 | 1.00 | 1.00 | 1.00 | 1.00 | 1.00 | 1.00 | 1.00 | 1.00 | 1.00 | 1.30 | 0.60 |
| Clec7a | 1.29 | 1.10 | 1.00 | 1.00 | 0.88 | 1.08 | 1.09 | 1.99 | 1.37 | 1.26 | 1.00 | 1.00 |
| Clps | 0.79 | 1.66 | 1.25 | 0.79 | 0.97 | 0.73 | 1.00 | 0.89 | 1.00 | 1.11 | 1.00 | 0.91 |
| Clpsl2 | 1.00 | 1.00 | 1.00 | 1.00 | 1.00 | 1.00 | 1.00 | 1.00 | 1.00 | 1.00 | 1.00 | 1.00 |
| Clu | 0.63 | 0.60 | 1.14 | 1.10 | 1.12 | 0.85 | 0.91 | 0.87 | 0.86 | 0.94 | 1.14 | 1.05 |
| Cpa1 | 0.67 | 1.00 | 1.00 | 1.00 | 1.00 | 1.00 | 1.00 | 0.92 | 1.00 | 1.00 | 1.00 | 1.00 |
| Cpa2 | 1.00 | 1.00 | 1.00 | 1.00 | 1.00 | 1.00 | 1.00 | 1.00 | 1.00 | 1.00 | 1.00 | 1.00 |
| Cpb1 | 0.54 | 1.00 | 1.00 | 1.00 | 1.00 | 1.00 | 1.00 | 1.15 | 1.00 | 1.43 | 1.00 | 1.00 |
| Crisp1 | 1.00 | 1.00 | 1.00 | 1.00 | 1.00 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 | 1.00 | 1.00 | 1.00 |
| Cryba4 | 1.00 | 1.00 | 1.00 | 1.00 | 1.00 | 1.00 | 0.79 | 0.99 | 1.00 | 1.00 | 1.00 | 1.00 |
| Cst11 | 1.00 | 1.00 | 1.00 | 1.00 | 1.00 | 1.00 | 1.00 | 1.00 | 1.00 | 1.00 | 1.00 | 1.00 |
| Cst12 | 1.00 | 1.00 | 1.00 | 1.00 | 1.00 | 1.00 | 1.00 | 1.00 | 1.00 | 1.00 | 1.00 | 1.00 |
| Cst8 | 1.00 | 1.00 | 1.00 | 1.00 | 1.00 | 1.00 | 1.00 | 1.00 | 1.00 | 1.00 | 1.00 | 1.00 |
| Ctrb1 | 0.56 | 4.91 | 1.00 | 1.00 | 1.00 | 1.00 | 1.00 | 0.91 | 1.00 | 0.85 | 1.00 | 0.99 |
| Ctrc | 1.00 | 1.00 | 1.00 | 1.00 | 1.00 | 1.00 | 1.00 | 1.00 | 1.00 | 1.00 | 1.00 | 1.00 |
| Ctrl | 1.00 | 1.00 | 1.00 | 1.00 | 1.00 | 1.00 | 1.00 | 1.00 | 1.00 | 1.02 | 1.00 | 1.00 |
| Cuzd1 | 1.00 | 1.00 | 1.01 | 1.00 | 1.00 | 1.00 | 1.00 | 0.85 | 1.00 | 1.00 | 1.00 | 1.00 |
| Cxcl10 | 1.00 | 1.00 | 1.00 | 1.00 | 1.84 | 1.12 | 1.00 | 1.00 | 1.02 | 1.29 | 1.14 | 1.33 |
| Cxcl13 | 1.13 | 6.96 | 1.07 | 0.93 | 0.93 | 0.83 | 0.75 | 0.95 | 1.58 | 0.82 | 1.00 | 1.00 |
| Cxcl9 | 1.00 | 1.00 | 1.00 | 1.00 | 0.94 | 1.17 | 1.00 | 1.53 | 1.00 | 1.00 | 1.00 | 1.00 |
| Cyb561 | 1.00 | 1.00 | 0.88 | 1.03 | 1.33 | 1.06 | 0.85 | 0.90 | 0.97 | 1.01 | 1.08 | 1.02 |
| Cyp2d9 | 6.19 | 1.00 | 1.00 | 1.00 | 1.00 | 1.00 | 1.00 | 1.00 | 1.00 | 1.00 | 0.96 | 0.76 |
| Cyp2e1 | 22.51 | 1.00 | 2.34 | 0.93 | 0.86 | 0.76 | 1.55 | 1.24 | 0.92 | 0.89 | 1.04 | 1.04 |
| Cyp3a11 | 11.64 | 1.00 | 1.00 | 1.00 | 1.00 | 1.00 | 1.00 | 1.00 | 1.00 | 1.00 | 1.00 | 1.00 |
| Cyp4a10 | 7.15 | 1.00 | 1.00 | 1.00 | 1.00 | 1.00 | 1.00 | 1.00 | 1.00 | 1.00 | 0.82 | 0.70 |
| Cyp4a14 | 8.68 | 1.00 | 1.00 | 1.00 | 1.00 | 1.00 | 1.00 | 1.00 | 1.00 | 1.00 | 0.73 | 0.76 |

Fig. 37- 32

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| C4b | 1.11 | 1.07 | 1.37 | 0.70 | 0.83 | 0.95 | 0.78 | 0.97 | 0.62 | 0.99 | 1.03 | 0.94 |
| C4bp | 0.87 | 1.22 | 0.92 | 0.91 | 0.70 | 0.81 | 94.55 | 9.68 | 1.00 | 1.00 | 1.00 | 1.00 |
| Cbl | 1.07 | 0.90 | 13.38 | 0.97 | 1.15 | 1.17 | 1.01 | 1.18 | 0.77 | 1.07 | 1.01 | 1.38 |
| Ccl12 | 1.00 | 1.00 | 0.93 | 1.72 | 0.63 | 1.20 | 0.48 | 2.59 | 1.00 | 1.00 | 1.00 | 1.00 |
| Ccl21b | 1.00 | 1.00 | 0.69 | 7.58 | 0.22 | 8.49 | 1.00 | 0.92 | 1.20 | 0.87 | 1.98 | 1.00 |
| Ccl25 | 0.72 | 0.97 | 0.86 | 1.16 | 5.12 | 1.99 | 1.25 | 1.17 | 1.22 | 0.86 | 1.43 | 0.81 |
| Ccl27b | 1.00 | 1.00 | 1.00 | 1.00 | 1.00 | 1.00 | 1.00 | 1.00 | 7.01 | 1.27 | 1.00 | 1.00 |
| Ccno | 1.00 | 1.00 | 1.00 | 1.00 | 1.00 | 1.00 | 5.62 | 3.03 | 0.89 | 0.96 | 1.19 | 1.00 |
| Ccnt1 | 1.73 | 0.39 | 9.99 | 1.20 | 1.05 | 1.33 | 1.12 | 0.94 | 0.81 | 1.01 | 0.94 | 1.20 |
| Cdh1 | 1.02 | 1.48 | 0.94 | 1.02 | 1.06 | 1.00 | 7.75 | 5.97 | 1.00 | 1.00 | 1.24 | 0.98 |
| Cdh16 | 1.00 | 1.00 | 1.00 | 1.00 | 1.00 | 1.00 | 8.57 | 3.40 | 1.00 | 1.00 | 1.00 | 1.00 |
| Cdh17 | 1.00 | 1.00 | 0.95 | 1.06 | 7.23 | 3.58 | 1.14 | 1.00 | 1.00 | 1.00 | 1.00 | 0.89 |
| Cdk6 | 1.00 | 0.74 | 3.68 | 0.94 | 0.63 | 1.09 | 1.00 | 1.00 | 0.97 | 0.92 | 0.99 | 1.51 |
| Cdkl5 | 1.00 | 1.00 | 1.00 | 1.00 | 1.12 | 1.07 | 1.00 | 1.00 | 0.91 | 1.07 | 1.00 | 1.00 |
| Cdo1 | 1.04 | 1.04 | 0.87 | 1.02 | 0.83 | 1.08 | 0.66 | 0.85 | 0.80 | 1.19 | 1.57 | 0.64 |
| Ceacam10 | 1.49 | 0.92 | 2.04 | 1.18 | 1.14 | 0.88 | 14.18 | 11.76 | 1.00 | 1.00 | 1.00 | 1.00 |
| Cel | 1.00 | 3.06 | 1.91 | 52.04 | 2.72 | 4.04 | 1.00 | 1.00 | 1.00 | 1.00 | 114 | 0.03 |
| Cela1 | 0.83 | 3.83 | 1.10 | 1.60 | 2.88 | 2.22 | 1.09 | 1.54 | 1.00 | 1.00 | 11.90 | 0.24 |
| Cela2a | 0.76 | 5.35 | 1.97 | 63.25 | 3.04 | 63.60 | 1.00 | 1.00 | 1.00 | 1.00 | 155 | 0.02 |
| Cela3b | 1.00 | 4.97 | 1.76 | 52.97 | 2.67 | 33.46 | 1.00 | 1.00 | 1.00 | 1.00 | 126 | 0.02 |
| Ces5a | 1.00 | 1.00 | 1.00 | 1.00 | 1.00 | 1.00 | 49.51 | 1.00 | 1.77 | 0.75 | 1.00 | 1.00 |
| Cfd | 1.00 | 0.37 | 1.96 | 1.01 | 1.21 | 0.71 | 1.02 | 0.90 | 0.23 | 0.72 | 8.59 | 0.39 |
| Chga | 1.00 | 1.00 | 0.91 | 1.08 | 0.97 | 0.96 | 1.07 | 9.46 | 1.13 | 0.85 | 1.00 | 1.00 |
| Chrm2 | 1.00 | 1.00 | 5.02 | 0.84 | 0.83 | 1.05 | 1.00 | 1.00 | 1.00 | 1.00 | 1.00 | 1.00 |
| Chrna7 | 1.00 | 1.00 | 1.00 | 1.00 | 1.00 | 1.00 | 1.00 | 1.00 | 1.00 | 1.00 | 1.00 | 1.00 |
| Cited4 | 1.00 | 1.00 | 0.88 | 0.93 | 1.04 | 1.10 | 3.17 | 8.43 | 1.20 | 0.89 | 1.17 | 0.95 |
| Ckmt1 | 1.00 | 1.00 | 0.92 | 0.92 | 1.15 | 0.98 | 1.00 | 1.00 | 1.00 | 1.00 | 1.00 | 1.00 |
| Clca3 | 1.00 | 1.00 | 0.91 | 1.14 | 0.92 | 1.17 | 1.00 | 1.00 | 1.00 | 1.00 | 1.00 | 1.00 |
| Cldn2 | 0.77 | 1.27 | 1.04 | 0.98 | 0.94 | 1.30 | 6.71 | 6.59 | 1.00 | 1.00 | 1.00 | 1.00 |
| Cldn3 | 0.81 | 1.22 | 0.95 | 0.91 | 4.21 | 3.47 | 13.38 | 5.73 | 1.42 | 0.75 | 1.00 | 1.00 |
| Cldn4 | 1.00 | 1.00 | 0.76 | 0.99 | 1.28 | 1.05 | 9.20 | 7.40 | 1.00 | 1.00 | 1.00 | 1.00 |
| Cldn7 | 1.00 | 1.00 | 0.94 | 1.08 | 1.63 | 1.59 | 5.51 | 6.55 | 1.13 | 1.00 | 1.00 | 1.00 |
| Cldn8 | 1.00 | 1.00 | 1.01 | 1.64 | 0.89 | 1.10 | 6.80 | 1.77 | 1.00 | 1.00 | 1.00 | 1.00 |
| Clec2h | 1.00 | 1.00 | 0.86 | 0.93 | 8.72 | 2.46 | 1.00 | 1.00 | 1.00 | 1.00 | 1.00 | 1.00 |
| Clec7a | 1.56 | 1.21 | 0.99 | 0.76 | 0.90 | 0.70 | 0.87 | 1.27 | 1.00 | 1.00 | 1.26 | 1.10 |
| Clps | 0.85 | 1.81 | 1.64 | 7.75 | 0.87 | 0.99 | 1.19 | 0.87 | 1.21 | 1.18 | 193 | 0.02 |
| Clpsl2 | 1.00 | 1.00 | 1.00 | 1.00 | 1.00 | 1.00 | 84.26 | 47.08 | 1.00 | 1.00 | 1.00 | 1.00 |
| Clu | 0.95 | 1.12 | 0.96 | 0.89 | 0.97 | 0.91 | 19.56 | 1.14 | 1.27 | 0.99 | 1.00 | 0.87 |
| Cpa1 | 1.00 | 3.24 | 1.93 | 48.86 | 2.77 | 32.52 | 1.00 | 1.00 | 1.00 | 1.00 | 119 | 0.03 |
| Cpa2 | 1.00 | 1.43 | 1.53 | 14.76 | 2.65 | 9.90 | 1.00 | 1.00 | 1.00 | 1.00 | 36.18 | 0.10 |
| Cpb1 | 1.00 | 5.06 | 1.46 | 73.34 | 2.67 | 49.61 | 1.00 | 1.00 | 1.00 | 1.00 | 128 | 0.03 |
| Crisp1 | 1.00 | 1.00 | 1.00 | 1.00 | 1.43 | 0.92 | 6.40 | 25.54 | 1.00 | 3.41 | 1.00 | 1.00 |
| Crisp4 | 1.00 | 1.00 | 1.00 | 1.00 | 1.00 | 1.00 | 5.22 | 3.29 | 1.00 | 1.00 | 1.00 | 1.00 |
| Cryba4 | 1.00 | 1.00 | 1.00 | 1.00 | 1.00 | 1.00 | 25.88 | 11.47 | 1.00 | 1.00 | 0.97 | 0.92 |
| Cst11 | 1.00 | 1.00 | 1.00 | 1.00 | 0.51 | 0.66 | 20.05 | 267 | 1.53 | 2.22 | 1.00 | 1.00 |
| Cst12 | 1.00 | 1.00 | 1.00 | 1.00 | 1.00 | 1.00 | 21.70 | 179 | 1.14 | 0.96 | 1.00 | 1.00 |
| Cst8 | 1.00 | 1.00 | 1.00 | 1.00 | 1.26 | 0.81 | 4.56 | 43.46 | 1.27 | 0.98 | 1.00 | 1.00 |
| Ctrb1 | 0.41 | 22.95 | 1.84 | 266 | 2.60 | 212 | 1.00 | 1.00 | 1.00 | 1.00 | 163 | 0.02 |
| Ctrc | 1.00 | 1.00 | 1.50 | 12.52 | 3.31 | 9.98 | 1.00 | 1.00 | 1.00 | 1.00 | 47.14 | 0.11 |
| Ctrl | 1.00 | 3.35 | 2.02 | 31.91 | 3.11 | 23.86 | 1.00 | 1.00 | 1.00 | 1.00 | 94.99 | 0.04 |
| Cuzd1 | 1.00 | 1.00 | 1.57 | 3.59 | 2.72 | 2.14 | 19.07 | 8.42 | 0.91 | 1.25 | 4.53 | 0.64 |
| Cxcl10 | 1.59 | 1.09 | 0.92 | 1.40 | 0.87 | 1.01 | 1.14 | 1.15 | 1.00 | 1.00 | 1.74 | 1.01 |
| Cxcl13 | 0.84 | 1.57 | 0.73 | 0.91 | 0.86 | 0.93 | 0.72 | 1.00 | 1.00 | 1.00 | 1.11 | 0.84 |
| Cxcl9 | 0.86 | 1.05 | 0.86 | 0.74 | 1.00 | 1.00 | 1.21 | 1.10 | 1.00 | 1.00 | 1.47 | 2.00 |
| Cyb561 | 0.81 | 1.30 | 0.89 | 1.13 | 1.01 | 0.99 | 5.12 | 1.86 | 1.07 | 1.13 | 1.02 | 1.04 |
| Cyp2d9 | 1.03 | 1.00 | 0.99 | 1.08 | 0.74 | 1.00 | 2.81 | 2.27 | 1.00 | 1.00 | 1.00 | 1.00 |
| Cyp2e1 | 0.81 | 0.87 | 1.80 | 1.01 | 0.29 | 0.90 | 0.82 | 0.79 | 0.40 | 0.56 | 4.86 | 0.54 |
| Cyp3a11 | 1.08 | 1.09 | 1.00 | 0.88 | 1.52 | 2.10 | 1.00 | 5.58 | 1.00 | 1.00 | 1.00 | 1.00 |
| Cyp4a10 | 0.93 | 0.64 | 1.00 | 1.00 | 0.43 | 1.00 | 1.82 | 1.69 | 1.00 | 1.00 | 1.00 | 1.00 |
| Cyp4a14 | 0.88 | 0.59 | 1.00 | 1.00 | 0.27 | 1.00 | 1.82 | 2.43 | 1.00 | 1.00 | 1.00 | 1.00 |

Fig. 37- 33

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| C4b | 1.23 | 0.77 | 1.08 | 1.47 | 1.97 | 2.68 | 1.01 | 1.17 | 1.00 | 1.08 |
| C4bp | 1.00 | 1.00 | 1.00 | 1.00 | 1.00 | 1.00 | 1.00 | 1.00 | 1.00 | 1.00 |
| Cbl | 1.00 | 1.00 | 0.86 | 7.24 | 1.56 | 0.75 | 0.63 | 1.67 | 7.43 | 2.57 |
| Ccl12 | 1.00 | 1.00 | 1.00 | 1.00 | 6.97 | 3.28 | 0.69 | 1.31 | 1.00 | 1.00 |
| Ccl21b | 1.13 | 2.08 | 0.89 | 0.83 | 1.21 | 1.51 | 0.61 | 1.00 | 1.00 | 1.00 |
| Ccl25 | 1.00 | 1.00 | 1.32 | 0.59 | 1.57 | 1.01 | 1.33 | 0.64 | 1.00 | 0.91 |
| Ccl27b | 1.00 | 1.00 | 1.00 | 1.00 | 1.00 | 1.00 | 1.09 | 0.58 | 1.00 | 1.00 |
| Ccno | 1.00 | 1.00 | 1.08 | 1.04 | 1.00 | 1.23 | 1.01 | 1.00 | 0.91 | 0.95 |
| Ccnt1 | 1.00 | 0.94 | 0.87 | 2.60 | 1.34 | 0.91 | 0.81 | 1.17 | 3.18 | 1.68 |
| Cdh1 | 1.07 | 1.10 | 0.96 | 0.89 | 1.18 | 0.71 | 1.00 | 0.99 | 1.01 | 0.84 |
| Cdh16 | 1.00 | 1.00 | 1.00 | 1.00 | 1.00 | 1.00 | 1.00 | 1.00 | 1.00 | 1.00 |
| Cdh17 | 1.00 | 1.00 | 1.00 | 1.00 | 1.00 | 1.00 | 1.00 | 1.00 | 1.00 | 1.00 |
| Cdk6 | 1.00 | 1.00 | 1.00 | 1.00 | 1.00 | 1.00 | 1.00 | 1.27 | 5.27 | 1.77 |
| Cdkl5 | 1.00 | 1.00 | 0.66 | 7.33 | 1.63 | 0.74 | 1.00 | 1.00 | 1.00 | 1.00 |
| Cdo1 | 1.08 | 1.78 | 1.09 | 0.72 | 0.82 | 1.02 | 1.03 | 0.86 | 0.84 | 0.99 |
| Ceacam10 | 1.00 | 1.00 | 1.00 | 1.00 | 1.00 | 1.00 | 1.00 | 1.00 | 1.01 | 1.56 |
| Cel | 0.93 | 1.11 | 1.58 | 1.00 | 1.00 | 1.00 | 1.49 | 1.00 | 1.00 | 1.00 |
| Cela1 | 0.93 | 1.17 | 1.56 | 0.74 | 1.37 | 1.07 | 1.50 | 1.06 | 0.81 | 0.94 |
| Cela2a | 0.96 | 1.13 | 1.31 | 1.00 | 1.00 | 1.00 | 1.15 | 1.19 | 1.00 | 1.00 |
| Cela3b | 0.86 | 1.10 | 1.23 | 1.00 | 1.00 | 1.02 | 1.36 | 0.98 | 1.00 | 1.00 |
| Ces5a | 1.00 | 1.00 | 1.00 | 1.00 | 1.00 | 1.00 | 1.00 | 1.00 | 1.00 | 1.00 |
| Cfd | 0.55 | 0.94 | 1.32 | 1.00 | 1.00 | 1.00 | 1.02 | 1.20 | 0.54 | 0.43 |
| Chga | 1.03 | 0.92 | 1.05 | 0.81 | 0.88 | 0.97 | 0.79 | 0.68 | 1.00 | 1.00 |
| Chrm2 | 1.00 | 1.00 | 0.72 | 4.55 | 1.56 | 0.93 | 1.00 | 1.00 | 1.00 | 1.00 |
| Chrna7 | 1.00 | 1.00 | 0.93 | 5.14 | 1.34 | 1.23 | 1.00 | 1.00 | 1.00 | 1.00 |
| Cited4 | 1.39 | 1.30 | 0.84 | 0.68 | 1.08 | 0.96 | 1.01 | 0.82 | 0.86 | 0.55 |
| Ckmt1 | 0.95 | 5.09 | 0.98 | 0.93 | 0.99 | 0.97 | 1.07 | 1.04 | 1.00 | 1.00 |
| Clca3 | 1.00 | 7.65 | 1.00 | 1.00 | 1.00 | 1.00 | 0.81 | 1.44 | 1.00 | 1.00 |
| Cldn2 | 1.00 | 1.00 | 0.88 | 0.87 | 1.05 | 0.92 | 0.80 | 0.73 | 1.00 | 1.00 |
| Cldn3 | 0.86 | 1.37 | 1.01 | 0.97 | 0.94 | 1.00 | 1.16 | 0.82 | 1.00 | 1.00 |
| Cldn4 | 0.90 | 1.59 | 1.00 | 1.00 | 1.00 | 1.00 | 0.97 | 1.06 | 1.00 | 1.00 |
| Cldn7 | 1.17 | 1.64 | 1.00 | 1.00 | 1.00 | 1.00 | 1.00 | 1.00 | 1.00 | 1.00 |
| Cldn8 | 0.92 | 0.94 | 1.00 | 1.00 | 1.00 | 1.00 | 1.04 | 1.36 | 1.00 | 1.00 |
| Clec2h | 1.00 | 1.00 | 1.00 | 1.00 | 1.00 | 1.00 | 1.00 | 1.00 | 1.00 | 1.00 |
| Clec7a | 1.00 | 1.00 | 1.00 | 1.00 | 1.00 | 1.88 | 1.16 | 7.35 | 1.15 | 1.28 |
| Clps | 0.91 | 1.25 | 1.07 | 1.31 | 0.49 | 0.65 | 0.78 | 1.04 | 0.26 | 1.00 |
| Clpsl2 | 1.00 | 1.00 | 1.00 | 1.00 | 1.00 | 1.00 | 1.00 | 1.00 | 1.00 | 1.00 |
| Clu | 0.90 | 1.03 | 1.11 | 0.83 | 1.03 | 1.14 | 1.08 | 0.91 | 0.58 | 0.77 |
| Cpa1 | 0.85 | 1.12 | 1.05 | 1.00 | 1.00 | 1.00 | 1.23 | 1.00 | 1.00 | 1.00 |
| Cpa2 | 0.86 | 1.10 | 0.76 | 0.91 | 1.00 | 1.15 | 1.00 | 1.00 | 1.00 | 1.00 |
| Cpb1 | 0.97 | 1.10 | 1.53 | 0.96 | 1.00 | 1.00 | 1.18 | 1.28 | 1.00 | 1.00 |
| Crisp1 | 1.00 | 1.00 | 1.00 | 1.00 | 1.00 | 1.00 | 1.00 | 1.00 | 1.00 | 1.00 |
| Crisp4 | 1.00 | 1.00 | 1.00 | 1.00 | 1.00 | 1.00 | 1.00 | 1.00 | 1.00 | 1.00 |
| Cryba4 | 1.00 | 1.00 | 1.00 | 1.00 | 1.77 | 1.00 | 1.00 | 1.00 | 0.89 | 1.00 |
| Cst11 | 1.00 | 1.00 | 1.00 | 1.00 | 1.00 | 1.00 | 1.00 | 1.00 | 1.00 | 1.00 |
| Cst12 | 1.00 | 1.00 | 1.00 | 1.00 | 1.00 | 1.00 | 1.00 | 1.00 | 1.00 | 1.00 |
| Cst8 | 1.00 | 1.00 | 1.00 | 1.00 | 1.00 | 1.00 | 1.00 | 1.00 | 1.00 | 1.00 |
| Ctrb1 | 0.85 | 1.13 | 1.61 | 0.88 | 1.00 | 0.85 | 0.99 | 1.11 | 3.24 | 1.00 |
| Ctrc | 0.93 | 1.16 | 1.00 | 1.00 | 1.00 | 1.00 | 1.00 | 1.00 | 1.00 | 1.00 |
| Ctrl | 0.83 | 1.22 | 0.88 | 1.07 | 1.00 | 0.93 | 1.44 | 1.00 | 1.00 | 1.00 |
| Cuzd1 | 0.91 | 1.12 | 1.00 | 1.00 | 1.00 | 1.00 | 1.00 | 1.00 | 1.00 | 1.00 |
| Cxcl10 | 1.00 | 1.00 | 1.00 | 1.00 | 1.09 | 2.75 | 1.17 | 25.94 | 0.77 | 0.78 |
| Cxcl13 | 0.66 | 0.82 | 1.00 | 1.00 | 1.00 | 3.84 | 1.26 | 1.66 | 1.00 | 1.00 |
| Cxcl9 | 1.00 | 1.00 | 1.00 | 1.00 | 1.00 | 1.00 | 1.00 | 30.33 | 1.00 | 1.00 |
| Cyb561 | 1.09 | 1.04 | 1.00 | 0.86 | 0.86 | 1.01 | 1.00 | 0.85 | 1.00 | 0.99 |
| Cyp2d9 | 1.00 | 1.00 | 1.00 | 1.00 | 1.00 | 1.00 | 1.00 | 1.00 | 1.00 | 1.00 |
| Cyp2e1 | 0.59 | 0.84 | 1.00 | 1.00 | 1.00 | 1.00 | 1.02 | 0.86 | 1.00 | 0.62 |
| Cyp3a11 | 1.00 | 1.00 | 1.00 | 1.00 | 1.00 | 1.00 | 1.00 | 0.25 | 1.00 | 1.00 |
| Cyp4a10 | 1.00 | 1.00 | 1.00 | 1.00 | 1.00 | 1.00 | 1.00 | 0.64 | 1.00 | 1.00 |
| Cyp4a14 | 1.00 | 1.00 | 1.00 | 1.00 | 1.00 | 1.00 | 1.00 | 0.51 | 1.00 | 1.00 |

Fig. 37-34

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| D10Bwg1379e | 1.00 | 1.00 | 1.00 | 1.00 | 1.00 | 1.00 | 1.00 | 1.00 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 | 1.00 | 1.00 | 1.00 |
| Ddi2 | 1.00 | 1.00 | 0.78 | 0.80 | 0.96 | 1.22 | 1.63 | 1.01 | 1.37 | 1.42 | 0.60 | 1.00 |
| Ddit4l | 1.00 | 1.00 | 1.02 | 1.44 | 1.74 | 1.19 | 1.86 | 1.27 | 0.73 | 0.91 | 1.41 | 1.05 |
| Defa-rs1 | 1.00 | 1.00 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 | 1.00 | 1.00 |
| Defa17 | 0.36 | 1.00 | 1.00 | 1.00 | 1.00 | 1.00 | 1.00 | 1.00 | 1.00 | 1.00 | 1.00 | 1.00 |
| Defa23 | 0.68 | 1.00 | 1.00 | 1.00 | 1.00 | 1.00 | 1.00 | 1.00 | 1.00 | 1.00 | 1.00 | 1.00 |
| Defa24 | 0.52 | 1.00 | 1.00 | 1.00 | 1.00 | 1.00 | 1.00 | 1.00 | 1.00 | 1.00 | 1.00 | 1.00 |
| Defa3 | 1.24 | 1.00 | 1.00 | 1.00 | 1.00 | 1.00 | 1.00 | 1.00 | 1.00 | 1.00 | 1.00 | 1.00 |
| Defa4 | 1.00 | 1.00 | 1.00 | 1.00 | 1.00 | 1.00 | 1.00 | 1.00 | 1.00 | 1.00 | 1.00 | 1.00 |
| Defb1 | 1.00 | 1.00 | 1.00 | 1.00 | 1.00 | 1.00 | 1.00 | 1.00 | 1.00 | 1.00 | 1.15 | 0.87 |
| Defb12 | 1.00 | 1.00 | 1.00 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 | 1.00 | 1.00 | 1.62 |
| Defb2 | 1.00 | 1.00 | 1.00 | 1.00 | 1.00 | 1.00 | 1.00 | 1.00 | 1.00 | 1.00 | 0.55 | 1.44 |
| Defb20 | 1.00 | 1.00 | 1.00 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.00 | 1.00 | 1.00 | 1.00 | 1.00 | 1.00 | 1.00 | 1.00 | 1.00 |
| Defb30 | 1.00 | 1.00 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 | 1.00 | 1.00 | 1.00 |
| Defb42 | 1.00 | 1.00 | 1.00 | 1.00 | 1.43 | 0.98 | 1.00 | 1.00 | 1.00 | 1.00 | 1.57 | 1.13 |
| Defb45 | 1.00 | 1.00 | 1.00 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 | 1.00 | 1.00 |
| Dmbt1 | 1.00 | 1.00 | 1.00 | 1.00 | 1.00 | 1.00 | 1.00 | 1.00 | 1.00 | 1.00 | 1.00 | 1.00 |
| Dnajb14 | 1.00 | 1.00 | 1.00 | 0.98 | 0.87 | 1.02 | 1.07 | 0.88 | 1.22 | 1.25 | 0.55 | 1.08 |
| Dsp | 1.00 | 1.00 | 1.00 | 1.00 | 1.00 | 1.00 | 1.07 | 1.04 | 0.94 | 0.96 | 0.80 | 0.93 |
| Eddm3b | 1.00 | 1.00 | 1.00 | 1.00 | 1.00 | 1.00 | 1.00 | 1.00 | 1.00 | 1.00 | 1.17 | 1.16 |
| Efcab4b | 1.00 | 1.00 | 1.00 | 1.00 | 1.00 | 1.00 | 1.00 | 1.00 | 0.90 | 1.18 | 1.00 | 1.00 |
| Egr1 | 1.00 | 1.00 | 1.24 | 5.26 | 0.76 | 0.83 | 0.91 | 0.89 | 0.78 | 1.40 | 0.64 | 1.60 |
| Egr2 | 1.00 | 1.00 | 0.84 | 1.31 | 1.00 | 1.00 | 0.80 | 1.08 | 0.92 | 0.72 | 1.00 | 1.00 |
| Ehf | 1.00 | 1.00 | 1.00 | 1.00 | 1.00 | 1.00 | 1.00 | 1.00 | 1.05 | 0.87 | 1.10 | 0.83 |
| Ehhadh | 5.36 | 1.00 | 1.28 | 0.85 | 1.09 | 1.20 | 0.87 | 1.47 | 0.93 | 0.92 | 0.86 | 0.86 |
| Eif3j1 | 1.00 | 1.00 | 1.00 | 40.35 | 1.00 | 1.00 | 1.00 | 13.81 | 1.00 | 1.00 | 0.09 | 0.10 |
| Eif3j2 | 1.00 | 1.00 | 0.95 | 0.16 | 0.93 | 0.91 | 0.92 | 0.29 | 1.01 | 0.90 | 11.75 | 2.23 |
| Elf3 | 1.00 | 1.00 | 1.00 | 1.00 | 1.00 | 1.00 | 1.00 | 1.00 | 1.00 | 1.06 | 0.93 | 1.06 |
| Emx2 | 1.00 | 1.00 | 1.42 | 0.86 | 1.00 | 1.00 | 1.00 | 1.00 | 1.00 | 1.00 | 1.03 | 0.94 |
| Enpp1 | 1.00 | 1.00 | 1.07 | 0.84 | 1.00 | 1.00 | 0.98 | 1.16 | 1.06 | 0.99 | 0.91 | 0.91 |
| Epcam | 1.00 | 1.00 | 1.00 | 1.00 | 1.00 | 1.00 | 1.00 | 1.00 | 0.87 | 0.98 | 1.15 | 0.98 |
| Eppin | 1.00 | 1.00 | 1.00 | 1.00 | 1.00 | 1.00 | 1.00 | 1.00 | 1.00 | 1.00 | 1.00 | 1.00 |
| Faah | 1.00 | 1.00 | 1.00 | 1.00 | 1.00 | 1.00 | 1.00 | 1.00 | 0.93 | 1.04 | 1.11 | 1.22 |
| Fabp1 | 16.55 | 1.00 | 1.00 | 1.00 | 1.00 | 1.00 | 1.00 | 1.00 | 0.89 | 0.99 | 1.03 | 1.00 |
| Fam84a | 1.00 | 1.00 | 1.00 | 1.00 | 1.00 | 1.00 | 1.00 | 1.01 | 1.14 | 1.00 | 0.95 | 0.86 |
| Fbxl18 | 1.00 | 1.00 | 0.74 | 1.09 | 1.08 | 1.56 | 1.20 | 1.06 | 1.13 | 1.10 | 0.59 | 0.99 |
| Fga | 13.22 | 1.00 | 1.03 | 1.00 | 1.00 | 1.00 | 1.00 | 1.00 | 1.00 | 1.00 | 1.14 | 1.08 |
| Fgb | 15.94 | 1.00 | 1.17 | 1.00 | 1.00 | 1.00 | 1.00 | 1.00 | 1.00 | 1.00 | 1.32 | 0.95 |
| Fgg | 11.62 | 1.00 | 1.00 | 1.00 | 1.00 | 1.00 | 1.00 | 1.00 | 1.00 | 1.00 | 1.34 | 1.00 |
| Folr1 | 1.00 | 1.00 | 1.00 | 1.00 | 1.00 | 1.00 | 1.00 | 1.00 | 1.00 | 1.00 | 1.07 | 0.92 |
| Foxn3 | 1.00 | 1.00 | 0.68 | 0.90 | 1.05 | 1.28 | 1.69 | 1.45 | 1.18 | 1.15 | 0.40 | 1.23 |
| Gal3st4 | 1.00 | 1.00 | 1.00 | 1.00 | 1.00 | 1.00 | 1.00 | 1.00 | 1.26 | 1.13 | 1.00 | 1.00 |
| Galnt12 | 1.00 | 1.00 | 1.00 | 1.00 | 1.00 | 1.00 | 1.00 | 1.00 | 1.05 | 1.07 | 1.00 | 1.00 |
| Gamt | 1.00 | 1.00 | 0.94 | 0.98 | 1.66 | 1.77 | 0.94 | 0.56 | 0.86 | 1.27 | 1.07 | 1.00 |
| Gatad2b | 1.00 | 1.00 | 0.89 | 0.74 | 1.00 | 1.12 | 1.49 | 1.29 | 1.13 | 0.94 | 0.53 | 1.05 |
| Gbp10 | 1.00 | 1.00 | 1.21 | 1.00 | 1.21 | 1.09 | 1.25 | 1.38 | 1.07 | 1.18 | 1.00 | 1.35 |
| Gbp2 | 2.04 | 1.69 | 0.91 | 1.24 | 1.12 | 1.14 | 1.16 | 1.03 | 1.13 | 1.29 | 1.11 | 0.90 |
| Gbp3 | 1.00 | 1.00 | 1.00 | 1.38 | 0.94 | 1.04 | 0.83 | 1.30 | 1.06 | 1.42 | 0.84 | 0.92 |
| Gbp5 | 1.00 | 1.00 | 0.88 | 1.32 | 1.05 | 1.09 | 0.90 | 1.14 | 1.29 | 1.30 | 1.00 | 1.31 |

Fig. 37- 35

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| D10Bwg1379e | 1.00 | 1.00 | 2.27 | 1.15 | 1.15 | 1.07 | 1.00 | 1.00 | 0.86 | 1.00 | 1.00 | 1.00 |
| D730048I06Rik | 1.00 | 1.00 | 1.00 | 1.00 | 1.00 | 1.00 | 193 | 1.00 | 1.00 | 1.00 | 1.00 | 1.00 |
| Ddi2 | 1.49 | 0.51 | 7.08 | 0.90 | 1.09 | 1.03 | 1.19 | 0.76 | 0.37 | 1.63 | 1.28 | 1.24 |
| Ddit4l | 1.00 | 1.00 | 0.90 | 1.05 | 1.02 | 1.35 | 7.25 | 13.38 | 1.23 | 1.10 | 1.00 | 1.00 |
| Defa-rs1 | 1.00 | 1.00 | 1.00 | 1.00 | 11.06 | 6.26 | 1.00 | 1.00 | 2.22 | 0.57 | 1.00 | 1.00 |
| Defa-rs7 | 1.00 | 1.00 | 1.00 | 1.00 | 15.28 | 13.35 | 1.00 | 1.00 | 1.00 | 1.00 | 1.00 | 1.00 |
| Defa17 | 1.00 | 1.00 | 0.58 | 0.93 | 9.94 | 45.94 | 1.00 | 1.00 | 1.21 | 0.68 | 1.00 | 1.00 |
| Defa23 | 1.00 | 1.00 | 0.36 | 1.50 | 0.17 | 17.63 | 1.00 | 1.00 | 1.61 | 2.85 | 1.00 | 1.00 |
| Defa24 | 1.00 | 1.00 | 0.98 | 0.93 | 15.15 | 55.01 | 1.00 | 1.00 | 1.67 | 1.00 | 1.00 | 1.00 |
| Defa3 | 1.00 | 1.00 | 0.81 | 2.69 | 11.71 | 47.49 | 1.00 | 1.00 | 1.38 | 0.73 | 1.00 | 1.00 |
| Defa4 | 1.00 | 1.00 | 1.00 | 0.41 | 16.83 | 1.00 | 1.00 | 1.00 | 1.00 | 1.00 | 1.00 | 1.00 |
| Defb1 | 1.94 | 1.13 | 0.72 | 2.38 | 0.64 | 1.15 | 5.33 | 3.00 | 1.00 | 1.00 | 1.00 | 1.00 |
| Defb12 | 1.00 | 1.00 | 1.00 | 1.00 | 1.00 | 1.00 | 169 | 11.04 | 1.00 | 1.00 | 1.00 | 1.00 |
| Defb15 | 1.00 | 1.00 | 1.00 | 1.00 | 1.00 | 1.00 | 297 | 2.64 | 1.65 | 1.00 | 1.00 | 1.00 |
| Defb18 | 1.00 | 1.00 | 1.00 | 1.00 | 1.00 | 1.00 | 124 | 47.97 | 1.00 | 1.00 | 1.00 | 1.00 |
| Defb2 | 1.00 | 1.00 | 1.00 | 1.00 | 1.00 | 1.00 | 9.83 | 1.00 | 1.00 | 1.00 | 1.00 | 1.00 |
| Defb20 | 1.00 | 1.00 | 1.00 | 1.00 | 1.00 | 1.00 | 87.55 | 202 | 0.69 | 1.00 | 1.00 | 1.00 |
| Defb21 | 1.00 | 1.00 | 1.00 | 1.00 | 1.00 | 1.00 | 34.33 | 1.68 | 2.06 | 0.62 | 1.00 | 1.00 |
| Defb25 | 1.00 | 1.00 | 1.00 | 1.00 | 1.00 | 1.00 | 33.46 | 321 | 1.00 | 1.00 | 1.00 | 1.10 |
| Defb30 | 1.00 | 1.00 | 1.00 | 1.00 | 1.00 | 1.00 | 40.42 | 1.00 | 1.26 | 1.11 | 1.00 | 1.00 |
| Defb37 | 1.00 | 1.00 | 0.91 | 2.02 | 1.00 | 1.00 | 6.27 | 1.00 | 1.00 | 1.00 | 1.00 | 1.00 |
| Defb39 | 1.00 | 1.00 | 1.00 | 1.00 | 1.00 | 1.00 | 15.00 | 1.00 | 1.00 | 1.00 | 1.00 | 1.00 |
| Defb41 | 1.00 | 1.00 | 1.00 | 1.00 | 1.00 | 1.00 | 42.31 | 16.04 | 1.53 | 1.13 | 1.00 | 1.00 |
| Defb42 | 1.00 | 1.00 | 1.00 | 1.00 | 1.00 | 1.00 | 236 | 126 | 1.00 | 1.34 | 1.00 | 1.00 |
| Defb45 | 1.00 | 1.00 | 1.00 | 1.00 | 1.00 | 1.00 | 32.17 | 1.77 | 2.01 | 0.89 | 1.00 | 1.00 |
| Defb47 | 1.00 | 1.00 | 1.00 | 1.00 | 1.00 | 1.00 | 7.52 | 172 | 1.00 | 1.00 | 1.00 | 1.00 |
| Defb48 | 1.00 | 1.00 | 1.00 | 1.00 | 1.00 | 1.00 | 39.84 | 288 | 1.02 | 1.00 | 1.00 | 1.00 |
| Dmbt1 | 1.00 | 0.92 | 1.14 | 1.11 | 1.53 | 1.32 | 1.00 | 1.00 | 1.00 | 1.00 | 33.29 | 0.09 |
| Dnajb14 | 1.18 | 0.44 | 1.88 | 0.80 | 1.20 | 1.01 | 1.04 | 0.68 | 1.34 | 1.03 | 1.04 | 0.90 |
| Dsp | 1.07 | 0.84 | 1.36 | 1.01 | 0.94 | 0.98 | 7.20 | 5.31 | 1.00 | 1.00 | 1.00 | 1.00 |
| Eddm3b | 1.00 | 1.00 | 1.00 | 1.00 | 1.00 | 1.00 | 36.86 | 6.00 | 1.00 | 1.00 | 1.00 | 1.00 |
| Efcab4b | 1.00 | 1.00 | 7.07 | 0.64 | 0.95 | 1.24 | 1.00 | 1.00 | 1.00 | 1.00 | 1.13 | 1.00 |
| Egr1 | 2.03 | 0.74 | 1.00 | 1.46 | 0.90 | 1.18 | 0.51 | 1.90 | 0.78 | 0.46 | 1.08 | 1.04 |
| Egr2 | 1.00 | 1.00 | 1.25 | 1.00 | 0.80 | 1.18 | 5.64 | 5.44 | 1.00 | 1.00 | 1.42 | 0.98 |
| Ehf | 1.00 | 1.00 | 1.13 | 1.10 | 0.86 | 0.99 | 5.38 | 4.46 | 1.00 | 1.00 | 1.10 | 0.93 |
| Ehhadh | 1.16 | 0.79 | 0.89 | 1.07 | 1.03 | 1.04 | 0.79 | 0.73 | 0.69 | 1.21 | 1.11 | 1.26 |
| Eif3j1 | 1.00 | 1.00 | 1.00 | 1.00 | 1.00 | 1.00 | 0.06 | 1.00 | 1.00 | 11.80 | 0.87 | 0.06 |
| Eif3j2 | 1.01 | 0.84 | 0.85 | 1.29 | 1.05 | 0.91 | 13.98 | 0.79 | 1.27 | 0.09 | 1.06 | 2.37 |
| Elf3 | 1.00 | 1.00 | 0.99 | 1.06 | 1.22 | 0.97 | 9.88 | 4.17 | 1.00 | 1.00 | 1.00 | 1.00 |
| Emx2 | 1.00 | 1.00 | 1.00 | 1.00 | 1.00 | 1.00 | 5.33 | 4.01 | 0.82 | 1.00 | 1.00 | 1.00 |
| Enpp1 | 1.06 | 0.79 | 1.10 | 0.90 | 1.05 | 0.93 | 11.59 | 1.32 | 1.00 | 1.00 | 1.15 | 0.99 |
| Epcam | 1.00 | 1.00 | 0.84 | 0.94 | 1.10 | 1.05 | 7.42 | 6.08 | 1.20 | 0.88 | 1.05 | 1.00 |
| Eppin | 1.00 | 1.00 | 1.00 | 1.00 | 1.00 | 1.00 | 23.17 | 6.99 | 1.29 | 0.94 | 1.00 | 1.00 |
| Faah | 0.90 | 1.09 | 0.81 | 1.00 | 0.95 | 0.99 | 5.68 | 3.51 | 1.03 | 1.00 | 1.05 | 1.04 |
| Fabp1 | 0.76 | 1.14 | 1.00 | 1.00 | 1.98 | 2.01 | 1.33 | 3.34 | 1.00 | 1.00 | 1.00 | 1.00 |
| Fam84a | 1.14 | 1.00 | 1.05 | 1.26 | 1.10 | 1.00 | 2.24 | 6.67 | 0.90 | 0.97 | 1.25 | 0.79 |
| Fbxl18 | 2.13 | 0.63 | 5.65 | 0.99 | 1.13 | 0.95 | 0.90 | 1.27 | 0.74 | 0.83 | 1.07 | 0.89 |
| Fga | 1.07 | 1.33 | 1.00 | 1.00 | 0.27 | 1.00 | 1.19 | 5.25 | 1.00 | 1.00 | 1.00 | 1.00 |
| Fgb | 1.07 | 1.41 | 1.00 | 1.00 | 0.22 | 1.00 | 1.00 | 5.28 | 1.00 | 0.96 | 1.00 | 1.00 |
| Fgg | 1.06 | 1.42 | 1.00 | 1.00 | 0.42 | 1.00 | 1.00 | 3.50 | 1.00 | 1.00 | 1.00 | 1.00 |
| Folr1 | 1.00 | 1.00 | 1.00 | 1.00 | 0.85 | 1.07 | 5.14 | 2.95 | 1.15 | 0.80 | 1.00 | 1.00 |
| Foxn3 | 2.07 | 0.37 | 6.93 | 0.87 | 0.91 | 1.11 | 1.03 | 0.97 | 0.54 | 1.10 | 1.07 | 1.16 |
| Gal3st4 | 1.00 | 1.00 | 0.80 | 1.43 | 0.80 | 0.94 | 6.33 | 1.00 | 1.00 | 1.00 | 1.16 | 0.89 |
| Galnt12 | 1.00 | 1.00 | 0.91 | 1.03 | 1.10 | 1.04 | 6.71 | 1.83 | 0.94 | 1.06 | 0.85 | 0.85 |
| Gamt | 0.71 | 1.34 | 0.64 | 0.75 | 1.02 | 1.37 | 6.60 | 3.22 | 1.36 | 0.89 | 1.43 | 0.57 |
| Gatad2b | 2.43 | 0.42 | 6.16 | 0.93 | 1.00 | 1.02 | 1.05 | 1.05 | 1.16 | 0.93 | 1.09 | 1.05 |
| Gbp10 | 0.89 | 0.99 | 1.30 | 0.85 | 1.00 | 1.00 | 0.75 | 1.22 | 1.00 | 1.00 | 1.30 | 0.98 |
| Gbp2 | 0.74 | 0.98 | 0.93 | 0.73 | 0.78 | 1.05 | 0.84 | 1.00 | 1.00 | 1.00 | 1.08 | 1.00 |
| Gbp3 | 1.00 | 0.90 | 0.83 | 0.78 | 1.03 | 1.00 | 0.87 | 1.14 | 1.00 | 1.00 | 1.01 | 0.89 |
| Gbp5 | 1.00 | 1.00 | 1.32 | 1.04 | 1.01 | 1.18 | 0.64 | 1.51 | 1.00 | 1.00 | 1.10 | 1.02 |

Fig. 37- 36

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| D10Bwg1379e | 1.34 | 0.38 | 0.72 | 6.10 | 1.53 | 0.99 | 1.00 | 1.00 | 1.00 | 1.00 |
| D730048I06Rik | 1.00 | 1.00 | 1.00 | 1.00 | 1.00 | 1.00 | 1.00 | 1.00 | 1.00 | 1.00 |
| Ddi2 | 1.85 | 0.30 | 0.73 | 3.76 | 1.09 | 1.13 | 0.63 | 1.59 | 2.80 | 1.55 |
| Ddit4l | 1.00 | 1.00 | 0.84 | 1.00 | 0.98 | 1.11 | 0.78 | 1.10 | 1.00 | 1.00 |
| Defa-rs1 | 1.00 | 1.00 | 1.00 | 1.00 | 1.00 | 1.00 | 1.00 | 1.00 | 1.00 | 1.00 |
| Defa-rs7 | 1.00 | 1.00 | 1.00 | 1.00 | 1.00 | 1.00 | 1.00 | 1.00 | 1.00 | 1.00 |
| Defa17 | 0.96 | 1.00 | 1.18 | 1.00 | 1.00 | 1.00 | 0.57 | 1.00 | 1.00 | 1.00 |
| Defa23 | 1.00 | 1.00 | 1.00 | 1.00 | 1.00 | 1.00 | 0.99 | 1.00 | 1.00 | 1.00 |
| Defa24 | 0.78 | 1.00 | 1.04 | 1.00 | 1.00 | 1.00 | 0.86 | 1.00 | 1.00 | 1.00 |
| Defa3 | 1.00 | 1.00 | 1.48 | 1.00 | 1.00 | 1.00 | 1.50 | 1.00 | 1.00 | 1.00 |
| Defa4 | 1.54 | 1.00 | 1.00 | 1.00 | 1.00 | 1.00 | 1.00 | 1.00 | 1.00 | 1.00 |
| Defb1 | 1.00 | 1.00 | 1.00 | 1.03 | 1.00 | 1.12 | 1.02 | 0.90 | 1.00 | 1.00 |
| Defb12 | 1.00 | 1.00 | 1.00 | 1.00 | 1.00 | 1.00 | 1.00 | 1.00 | 1.00 | 1.00 |
| Defb15 | 1.00 | 1.00 | 1.00 | 1.00 | 1.00 | 1.00 | 1.00 | 1.00 | 1.00 | 1.00 |
| Defb18 | 1.00 | 1.00 | 1.00 | 1.00 | 1.00 | 1.00 | 1.00 | 1.00 | 1.00 | 1.00 |
| Defb2 | 1.00 | 1.00 | 1.00 | 1.00 | 1.00 | 1.00 | 1.00 | 1.00 | 1.00 | 1.00 |
| Defb20 | 1.00 | 1.00 | 1.00 | 1.00 | 1.00 | 1.00 | 1.00 | 1.00 | 1.00 | 1.00 |
| Defb21 | 1.00 | 1.00 | 1.00 | 1.00 | 1.00 | 1.00 | 1.00 | 1.00 | 1.00 | 1.00 |
| Defb25 | 1.00 | 1.00 | 1.00 | 1.03 | 1.00 | 1.00 | 1.00 | 1.00 | 1.00 | 1.00 |
| Defb30 | 1.00 | 1.00 | 1.00 | 1.00 | 1.00 | 1.00 | 1.00 | 1.00 | 1.00 | 1.00 |
| Defb37 | 1.00 | 1.00 | 1.00 | 1.00 | 1.00 | 1.00 | 1.00 | 1.00 | 1.00 | 1.00 |
| Defb39 | 1.00 | 1.00 | 1.00 | 1.00 | 1.00 | 1.00 | 1.00 | 1.00 | 1.00 | 1.00 |
| Defb41 | 1.00 | 1.00 | 1.00 | 1.00 | 1.00 | 1.00 | 1.00 | 1.00 | 1.00 | 1.00 |
| Defb42 | 1.00 | 1.00 | 1.00 | 1.00 | 1.00 | 1.00 | 1.00 | 1.00 | 1.00 | 1.00 |
| Defb45 | 1.00 | 1.00 | 1.00 | 1.00 | 1.00 | 1.00 | 1.00 | 1.00 | 1.00 | 1.00 |
| Defb47 | 1.00 | 1.00 | 1.00 | 1.00 | 1.00 | 1.00 | 1.00 | 1.00 | 1.00 | 1.00 |
| Defb48 | 1.00 | 1.00 | 1.00 | 1.00 | 1.00 | 1.00 | 1.00 | 1.00 | 1.00 | 1.00 |
| Dmbt1 | 0.97 | 0.77 | 1.00 | 1.00 | 1.00 | 1.00 | 1.00 | 1.00 | 1.00 | 1.00 |
| Dnajb14 | 1.10 | 1.00 | 0.59 | 5.50 | 1.25 | 0.80 | 0.86 | 1.48 | 1.53 | 1.51 |
| Dsp | 1.01 | 0.76 | 1.00 | 1.03 | 1.00 | 1.00 | 0.90 | 1.07 | 1.00 | 1.00 |
| Eddm3b | 1.00 | 1.00 | 1.00 | 1.00 | 1.00 | 1.00 | 1.00 | 1.00 | 1.00 | 1.00 |
| Efcab4b | 1.00 | 1.00 | 1.00 | 1.00 | 1.00 | 1.00 | 1.00 | 1.00 | 2.63 | 1.72 |
| Egr1 | 0.77 | 1.13 | 1.55 | 1.47 | 1.66 | 1.50 | 0.93 | 0.66 | 0.99 | 0.65 |
| Egr2 | 1.00 | 1.00 | 2.04 | 2.11 | 2.39 | 2.57 | 0.92 | 0.92 | 1.00 | 1.00 |
| Ehf | 1.21 | 0.94 | 1.00 | 1.00 | 1.00 | 1.00 | 0.85 | 0.94 | 1.00 | 1.00 |
| Ehhadh | 0.95 | 0.77 | 0.84 | 1.19 | 0.99 | 0.95 | 0.90 | 0.92 | 1.05 | 0.76 |
| Eif3j1 | 5.99 | 1.00 | 1.00 | 0.10 | 1.00 | 1.00 | 1.00 | 0.08 | 17.14 | 1.00 |
| Eif3j2 | 0.18 | 1.19 | 1.09 | 5.15 | 1.00 | 1.00 | 1.15 | 3.33 | 0.05 | 0.99 |
| Elf3 | 1.22 | 1.58 | 1.00 | 1.00 | 1.00 | 1.00 | 1.00 | 1.00 | 1.00 | 1.00 |
| Emx2 | 1.00 | 1.00 | 0.97 | 1.20 | 1.01 | 0.97 | 1.20 | 0.98 | 1.00 | 1.00 |
| Enpp1 | 1.00 | 1.12 | 1.00 | 1.00 | 0.95 | 1.00 | 1.06 | 0.99 | 0.77 | 0.79 |
| Epcam | 1.08 | 1.81 | 1.00 | 1.00 | 1.00 | 1.00 | 0.99 | 0.90 | 1.00 | 1.00 |
| Eppin | 1.00 | 1.00 | 1.00 | 1.00 | 1.00 | 1.00 | 1.00 | 1.00 | 1.00 | 1.00 |
| Faah | 1.00 | 0.83 | 1.04 | 0.91 | 0.87 | 1.04 | 1.05 | 0.97 | 0.88 | 0.80 |
| Fabp1 | 1.59 | 1.00 | 1.00 | 1.00 | 1.00 | 1.00 | 1.00 | 0.24 | 1.00 | 0.96 |
| Fam84a | 1.00 | 1.00 | 1.09 | 1.00 | 0.94 | 0.94 | 0.78 | 1.01 | 1.00 | 1.00 |
| Fbxl18 | 1.00 | 1.00 | 0.77 | 2.40 | 1.35 | 1.14 | 0.64 | 1.25 | 2.26 | 1.53 |
| Fga | 1.00 | 1.00 | 1.00 | 1.00 | 1.00 | 1.00 | 1.00 | 0.51 | 1.00 | 1.00 |
| Fgb | 1.00 | 1.00 | 1.00 | 1.00 | 1.00 | 1.00 | 1.00 | 0.28 | 1.00 | 1.00 |
| Fgg | 1.00 | 1.00 | 1.00 | 1.00 | 1.00 | 1.00 | 1.00 | 0.29 | 1.00 | 1.00 |
| Folr1 | 1.00 | 1.00 | 0.78 | 0.54 | 0.94 | 0.77 | 0.91 | 0.86 | 1.00 | 1.00 |
| Foxn3 | 1.44 | 0.61 | 0.91 | 3.52 | 1.75 | 0.99 | 0.74 | 1.30 | 3.01 | 2.00 |
| Gal3st4 | 1.00 | 1.00 | 1.10 | 0.93 | 1.09 | 1.19 | 1.01 | 1.00 | 0.93 | 0.80 |
| Galnt12 | 1.00 | 1.00 | 1.00 | 1.00 | 1.02 | 1.00 | 0.93 | 1.08 | 0.63 | 0.89 |
| Gamt | 0.90 | 1.37 | 0.96 | 0.66 | 1.09 | 0.98 | 1.51 | 1.00 | 1.02 | 0.95 |
| Gatad2b | 1.00 | 0.76 | 0.93 | 5.06 | 1.30 | 0.88 | 0.71 | 1.54 | 2.72 | 1.46 |
| Gbp10 | 1.00 | 1.00 | 1.00 | 1.00 | 1.00 | 1.00 | 0.99 | 8.09 | 1.00 | 1.00 |
| Gbp2 | 1.00 | 1.54 | 1.00 | 0.86 | 1.49 | 1.55 | 1.09 | 11.07 | 1.31 | 1.33 |
| Gbp3 | 1.00 | 1.00 | 1.00 | 1.00 | 1.43 | 2.34 | 0.95 | 5.22 | 1.05 | 1.30 |
| Gbp5 | 1.00 | 1.00 | 1.00 | 1.00 | 1.00 | 1.66 | 1.00 | 8.93 | 1.09 | 1.25 |

Fig. 37- 37

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Gbp6 | 1.00 | 1.00 | 1.29 | 1.20 | 1.01 | 1.11 | 1.10 | 1.34 | 1.17 | 1.17 | 1.14 | 1.51 |
| Gbp7 | 1.00 | 1.69 | 0.75 | 1.37 | 0.97 | 1.08 | 0.87 | 1.45 | 1.09 | 1.08 | 0.96 | 1.12 |
| Gc | 6.81 | 1.00 | 1.00 | 1.00 | 1.00 | 1.00 | 1.00 | 1.00 | 1.00 | 1.00 | 0.92 | 0.73 |
| Gcnt4 | 1.00 | 1.00 | 1.00 | 1.00 | 1.00 | 1.00 | 1.00 | 1.00 | 1.00 | 1.00 | 0.82 | 0.97 |
| Gfra1 | 1.00 | 1.00 | 1.11 | 0.99 | 0.85 | 0.59 | 1.15 | 1.23 | 0.88 | 0.90 | 1.21 | 1.16 |
| Ggt1 | 1.00 | 1.00 | 1.00 | 1.00 | 1.00 | 1.00 | 1.00 | 1.00 | 1.00 | 1.00 | 1.04 | 1.06 |
| Gjb3 | 1.00 | 1.00 | 1.00 | 1.00 | 1.00 | 1.00 | 1.00 | 1.00 | 1.02 | 1.17 | 0.86 | 1.00 |
| Glra1 | 1.00 | 1.00 | 1.00 | 1.00 | 1.00 | 1.00 | 1.00 | 1.00 | 1.00 | 1.00 | 1.00 | 1.00 |
| Gm10104 | 1.00 | 1.00 | 1.00 | 1.00 | 1.00 | 1.00 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 | 1.00 | 1.00 | 1.00 |
| Gm12250 | 1.00 | 0.74 | 1.00 | 1.20 | 1.00 | 1.32 | 1.13 | 2.96 | 1.38 | 1.25 | 0.91 | 1.62 |
| Gm13363 | 1.00 | 1.00 | 0.85 | 0.83 | 0.29 | 0.63 | 1.96 | 0.92 | 1.00 | 1.00 | 1.00 | 1.00 |
| Gm14475 | 1.00 | 1.00 | 1.00 | 1.00 | 1.00 | 1.00 | 1.00 | 1.00 | 1.00 | 1.00 | 1.00 | 1.00 |
| Gm14851 | 0.84 | 1.00 | 1.00 | 1.00 | 1.00 | 1.00 | 1.00 | 1.00 | 1.00 | 1.00 | 1.00 | 1.00 |
| Gm15284 | 0.88 | 1.00 | 1.00 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 | 1.00 | 1.00 | 1.00 |
| Gm20604 | 1.00 | 1.00 | 1.00 | 3.67 | 5.18 | 0.48 | 0.81 | 0.65 | 1.05 | 1.33 | 1.08 | 1.86 |
| Gm2083 | 3.19 | 1.00 | 2.24 | 1.55 | 3.06 | 0.81 | 1.00 | 1.00 | 1.00 | 1.00 | 1.00 | 1.00 |
| Gm20878 | 1.00 | 1.00 | 1.00 | 1.00 | 1.00 | 1.00 | 1.00 | 1.00 | 1.00 | 0.85 | 1.00 | 1.00 |
| Gm21498 | 1.00 | 1.00 | 1.00 | 1.00 | 1.00 | 1.00 | 1.00 | 1.00 | 1.00 | 1.00 | 1.00 | 1.00 |
| Gm266 | 1.00 | 1.00 | 1.00 | 1.00 | 1.00 | 1.00 | 1.00 | 1.00 | 1.00 | 1.00 | 0.72 | 1.27 |
| Gm4759 | 1.00 | 1.00 | 1.00 | 1.00 | 1.00 | 1.00 | 1.00 | 1.00 | 1.00 | 1.00 | 1.00 | 1.00 |
| Gm4846 | 1.00 | 1.00 | 1.00 | 1.00 | 1.00 | 1.00 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 | 1.00 | 1.00 | 1.00 |
| Gm5916 | 1.00 | 1.00 | 1.00 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 | 1.00 | 1.00 | 1.00 |
| Gm6792 | 1.00 | 1.00 | 1.00 | 1.00 | 1.00 | 1.00 | 1.00 | 1.00 | 1.00 | 1.00 | 1.00 | 1.00 |
| Gm6793 | 1.00 | 1.00 | 1.00 | 1.00 | 1.00 | 1.00 | 1.00 | 1.00 | 1.00 | 1.00 | 1.00 | 1.00 |
| Gm766 | 1.00 | 1.00 | 1.00 | 1.00 | 1.00 | 1.00 | 1.00 | 1.00 | 1.00 | 1.00 | 1.00 | 1.00 |
| Gnmt | 6.92 | 1.00 | 0.74 | 1.00 | 1.80 | 1.08 | 1.05 | 0.82 | 0.83 | 0.65 | 1.34 | 1.14 |
| Gp2 | 1.00 | 1.00 | 1.00 | 1.00 | 1.00 | 1.00 | 1.00 | 1.00 | 1.00 | 1.00 | 1.12 | 1.66 |
| Gpr26 | 1.00 | 1.00 | 1.00 | 1.00 | 1.00 | 1.00 | 1.00 | 1.00 | 1.00 | 1.00 | 1.00 | 1.00 |
| Gpx5 | 1.00 | 1.00 | 1.00 | 1.00 | 1.00 | 1.00 | 1.00 | 1.00 | 1.00 | 1.00 | 1.00 | 3.02 |
| Gstm6 | 1.00 | 1.00 | 1.00 | 1.00 | 1.00 | 1.00 | 0.71 | 1.03 | 0.65 | 0.99 | 0.83 | 0.94 |
| Gstm7 | 1.00 | 1.00 | 0.98 | 1.36 | 0.83 | 0.92 | 0.92 | 1.00 | 1.03 | 1.28 | 1.16 | 0.83 |
| Guca2a | 1.00 | 1.00 | 1.00 | 1.00 | 1.00 | 1.00 | 1.00 | 1.00 | 1.00 | 1.00 | 0.99 | 0.83 |
| H2-Q7 | 1.25 | 1.06 | 1.26 | 3.07 | 0.99 | 1.48 | 1.17 | 1.71 | 0.92 | 1.54 | 0.74 | 1.67 |
| H2-T9 | 1.00 | 0.97 | 1.68 | 1.00 | 0.32 | 2.65 | 0.82 | 0.80 | 1.17 | 0.55 | 4.38 | 1.01 |
| Hba-a1 | 0.63 | 0.56 | 0.24 | 0.64 | 2.00 | 0.90 | 1.10 | 1.78 | 0.82 | 1.22 | 1.21 | 1.01 |
| Hbb-bs | 0.67 | 0.65 | 1.35 | 2.03 | 0.33 | 0.42 | 0.87 | 0.60 | 1.43 | 0.92 | 1.41 | 1.19 |
| Hcar1 | 1.00 | 1.00 | 1.00 | 1.00 | 0.74 | 6.58 | 1.00 | 1.00 | 1.00 | 1.00 | 1.18 | 1.00 |
| Hipk2 | 0.86 | 0.89 | 0.58 | 0.86 | 1.34 | 1.90 | 1.74 | 1.25 | 1.19 | 1.31 | 0.32 | 1.24 |
| Hist1h4i | 0.66 | 0.62 | 1.12 | 0.74 | 5.17 | 0.74 | 1.23 | 1.08 | 0.79 | 1.28 | 1.23 | 1.14 |
| Hist2h2bb | 0.70 | 0.38 | 1.02 | 0.85 | 3.40 | 0.96 | 2.95 | 0.76 | 1.18 | 0.62 | 1.57 | 1.66 |
| Hist2h3c2 | 1.00 | 0.63 | 2.66 | 1.11 | 0.77 | 0.41 | 0.60 | 0.72 | 1.70 | 6.40 | 0.31 | 5.61 |
| Hmbox1 | 1.00 | 1.00 | 0.51 | 0.92 | 1.12 | 1.25 | 1.99 | 1.59 | 1.55 | 1.25 | 0.66 | 1.00 |
| Hmgcs2 | 11.15 | 1.00 | 0.94 | 0.76 | 0.69 | 0.68 | 0.77 | 0.76 | 0.91 | 1.08 | 0.73 | 0.62 |
| Hoxa6 | 1.00 | 1.00 | 1.00 | 1.00 | 1.08 | 1.13 | 1.00 | 1.00 | 1.00 | 1.00 | 1.07 | 0.51 |
| Hpx | 7.43 | 1.00 | 1.00 | 1.00 | 1.00 | 1.00 | 1.00 | 1.00 | 1.24 | 1.47 | 1.00 | 1.00 |
| Hs6st3 | 1.00 | 1.00 | 1.00 | 1.00 | 1.00 | 1.00 | 1.00 | 1.00 | 1.94 | 1.55 | 1.00 | 1.00 |
| Hsd3b5 | 1.00 | 1.00 | 1.00 | 1.00 | 1.00 | 1.00 | 1.00 | 1.00 | 1.00 | 1.00 | 0.95 | 0.88 |
| Iapp | 1.00 | 1.00 | 1.00 | 1.00 | 1.00 | 1.00 | 1.00 | 1.00 | 1.00 | 1.00 | 1.00 | 1.00 |
| Icam2 | 5.11 | 2.95 | 0.99 | 0.99 | 1.26 | 1.30 | 0.96 | 0.97 | 1.01 | 1.00 | 1.01 | 0.90 |
| Ido1 | 1.00 | 1.00 | 1.00 | 1.00 | 1.00 | 1.00 | 1.00 | 1.00 | 1.00 | 1.00 | 1.00 | 1.00 |
| Ifi47 | 1.02 | 1.09 | 1.23 | 1.38 | 0.92 | 0.99 | 0.75 | 1.18 | 1.13 | 1.18 | 1.41 | 1.33 |
| Ifit1 | 0.48 | 0.78 | 0.86 | 1.38 | 0.80 | 1.01 | 1.21 | 0.83 | 1.00 | 0.80 | 1.23 | 0.78 |
| Igfbp2 | 5.38 | 1.00 | 1.00 | 1.00 | 1.00 | 1.00 | 1.00 | 1.00 | 1.00 | 0.97 | 0.77 | 0.78 |
| Igfbp4 | 5.20 | 1.47 | 1.10 | 0.98 | 1.00 | 0.95 | 0.89 | 0.95 | 0.94 | 0.97 | 1.05 | 0.93 |

Fig. 37-38

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Gbp6 | 0.91 | 1.10 | 1.18 | 0.96 | 0.97 | 1.19 | 0.79 | 1.20 | 1.00 | 1.00 | 1.32 | 0.99 |
| Gbp7 | 1.24 | 0.85 | 1.37 | 0.96 | 0.96 | 1.06 | 0.72 | 1.02 | 1.00 | 1.00 | 0.96 | 0.99 |
| Gc | 0.97 | 1.06 | 1.00 | 1.00 | 0.56 | 0.81 | 2.45 | 1.94 | 1.00 | 1.00 | 1.00 | 1.00 |
| Gcnt4 | 0.87 | 0.73 | 1.40 | 1.21 | 1.44 | 1.21 | 1.21 | 7.78 | 0.59 | 1.24 | 1.00 | 1.00 |
| Gfra1 | 1.18 | 0.69 | 1.09 | 0.92 | 0.73 | 0.93 | 20.02 | 2.72 | 0.98 | 1.21 | 1.00 | 1.00 |
| Ggt1 | 1.00 | 1.00 | 0.87 | 0.83 | 3.40 | 1.68 | 8.07 | 4.36 | 1.00 | 1.00 | 1.00 | 1.00 |
| Gjb3 | 1.00 | 1.00 | 0.90 | 0.94 | 0.80 | 1.00 | 5.76 | 3.51 | 1.23 | 0.77 | 1.00 | 1.00 |
| Glra1 | 1.00 | 1.00 | 1.00 | 1.00 | 1.00 | 1.00 | 1.00 | 1.00 | 1.00 | 1.00 | 1.00 | 1.00 |
| Gm10104 | 1.00 | 1.00 | 1.52 | 1.00 | 12.34 | 4.68 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 5.17 | 1.00 | 1.00 |
| Gm1110 | 1.00 | 1.00 | 1.00 | 1.00 | 0.90 | 0.96 | 18.93 | 7.10 | 1.00 | 1.00 | 1.00 | 1.00 |
| Gm12250 | 0.81 | 0.76 | 1.63 | 0.98 | 1.00 | 1.00 | 0.61 | 1.41 | 1.00 | 1.00 | 1.32 | 1.21 |
| Gm13363 | 1.00 | 0.19 | 1.61 | 1.30 | 1.00 | 0.63 | 0.10 | 0.27 | 1.09 | 1.04 | 1.39 | 0.89 |
| Gm14475 | 1.00 | 1.00 | 1.00 | 1.00 | 1.00 | 1.00 | 1.00 | 1.00 | 22.51 | 0.38 | 1.00 | 1.00 |
| Gm14851 | 1.00 | 1.00 | 1.00 | 1.00 | 5.39 | 2.31 | 1.00 | 1.00 | 1.04 | 0.43 | 1.00 | 1.00 |
| Gm15284 | 1.00 | 1.00 | 0.44 | 0.96 | 10.29 | 14.23 | 1.00 | 1.00 | 0.71 | 0.55 | 1.00 | 1.00 |
| Gm15386 | 1.00 | 1.00 | 1.00 | 1.00 | 1.00 | 1.00 | 43.18 | 59.73 | 1.00 | 0.82 | 1.00 | 1.00 |
| Gm17727 | 1.00 | 1.00 | 1.00 | 1.00 | 1.00 | 1.00 | 20.07 | 1.00 | 1.00 | 1.00 | 1.00 | 1.00 |
| Gm20604 | 1.13 | 1.36 | 0.79 | 1.26 | 1.40 | 1.62 | 1.00 | 1.28 | 1.26 | 0.84 | 0.91 | 0.91 |
| Gm2083 | 0.98 | 1.16 | 1.00 | 0.45 | 0.43 | 1.37 | 2.13 | 11.86 | 0.45 | 1.49 | 1.00 | 1.00 |
| Gm20878 | 1.00 | 1.00 | 1.00 | 1.00 | 1.00 | 1.00 | 1.00 | 1.00 | 5.44 | 1.00 | 1.00 | 1.00 |
| Gm21498 | 1.00 | 1.00 | 1.00 | 1.00 | 5.58 | 1.42 | 1.00 | 1.00 | 1.00 | 1.00 | 1.00 | 1.00 |
| Gm266 | 1.00 | 1.00 | 1.00 | 1.00 | 1.00 | 1.00 | 7.95 | 4.62 | 1.00 | 1.00 | 1.00 | 1.00 |
| Gm4759 | 1.00 | 1.00 | 1.00 | 1.00 | 1.00 | 1.00 | 1.00 | 1.00 | 1.00 | 1.00 | 1.16 | 1.61 |
| Gm4846 | 1.00 | 1.00 | 1.00 | 1.00 | 1.00 | 1.00 | 9.65 | 85.25 | 1.00 | 1.00 | 1.00 | 1.00 |
| Gm5531 | 1.00 | 1.00 | 1.00 | 1.00 | 1.00 | 1.00 | 46.92 | 7.24 | 1.00 | 1.00 | 1.00 | 1.00 |
| Gm5916 | 1.00 | 1.00 | 1.00 | 1.00 | 1.00 | 1.00 | 1.00 | 17.99 | 1.00 | 1.00 | 1.00 | 1.00 |
| Gm6040 | 1.00 | 1.00 | 1.00 | 1.00 | 1.00 | 1.00 | 6.98 | 1.00 | 1.00 | 1.00 | 1.00 | 1.00 |
| Gm6792 | 1.00 | 1.00 | 1.00 | 1.00 | 1.00 | 1.00 | 120 | 2.26 | 1.00 | 1.00 | 1.00 | 1.00 |
| Gm6793 | 1.00 | 1.00 | 1.00 | 1.00 | 1.00 | 1.00 | 1.00 | 1.00 | 5.78 | 0.79 | 1.00 | 1.00 |
| Gm766 | 1.00 | 1.00 | 1.00 | 1.00 | 18.67 | 10.78 | 1.00 | 1.00 | 1.00 | 1.00 | 1.00 | 1.00 |
| Gnmt | 0.94 | 1.20 | 1.00 | 1.00 | 0.90 | 0.83 | 1.08 | 2.10 | 1.07 | 1.00 | 1.00 | 1.00 |
| Gp2 | 1.00 | 1.00 | 1.69 | 11.26 | 2.40 | 11.77 | 1.00 | 1.00 | 1.00 | 1.00 | 14.47 | 0.18 |
| Gpr26 | 1.00 | 1.00 | 1.00 | 1.00 | 1.00 | 1.00 | 1.00 | 1.00 | 1.00 | 1.00 | 1.00 | 1.00 |
| Gpx5 | 1.00 | 1.00 | 1.00 | 1.00 | 1.00 | 1.00 | 2332 | 1307 | 1.00 | 1.00 | 1.00 | 1.00 |
| Gstm6 | 0.89 | 1.56 | 0.71 | 1.74 | 0.92 | 0.91 | 5.08 | 4.09 | 1.16 | 0.91 | 1.00 | 1.00 |
| Gstm7 | 0.93 | 1.23 | 0.90 | 1.71 | 1.13 | 1.03 | 5.93 | 3.75 | 1.42 | 0.93 | 1.39 | 0.67 |
| Guca2a | 1.00 | 1.00 | 0.68 | 0.99 | 0.98 | 1.62 | 1.00 | 1.00 | 1.00 | 1.00 | 1.00 | 1.00 |
| H2-Q7 | 1.04 | 1.46 | 0.87 | 0.89 | 0.88 | 0.96 | 1.61 | 1.14 | 1.14 | 1.46 | 0.92 | 1.37 |
| H2-T9 | 0.56 | 1.94 | 0.95 | 1.53 | 1.46 | 1.00 | 5.31 | 2.99 | 1.00 | 1.00 | 0.77 | 8.12 |
| Hba-a1 | 0.87 | 1.86 | 7.91 | 0.04 | 1.88 | 0.48 | 0.96 | 0.69 | 1.18 | 1.74 | 0.87 | 0.92 |
| Hbb-bs | 0.68 | 1.30 | 9.56 | 2.78 | 3.01 | 14.06 | 1.08 | 0.54 | 1.57 | 1.00 | 1.10 | 0.52 |
| Hcar1 | 1.00 | 1.00 | 1.17 | 0.74 | 1.03 | 1.13 | 0.88 | 2.15 | 1.00 | 1.00 | 0.82 | 0.87 |
| Hipk2 | 2.09 | 0.48 | 6.25 | 0.92 | 1.21 | 1.03 | 1.12 | 1.32 | 0.78 | 0.96 | 0.83 | 1.24 |
| Hist1h4i | 0.71 | 1.76 | 0.97 | 1.94 | 1.45 | 1.12 | 0.98 | 1.13 | 2.51 | 1.71 | 0.98 | 0.95 |
| Hist2h2bb | 1.00 | 1.00 | 5.12 | 0.63 | 1.02 | 1.25 | 2.79 | 1.32 | 0.32 | 0.66 | 1.14 | 0.85 |
| Hist2h3c2 | 1.21 | 2.35 | 1.44 | 3.51 | 0.79 | 0.98 | 1.90 | 1.08 | 0.69 | 0.48 | 1.15 | 0.37 |
| Hmbox1 | 2.27 | 0.41 | 4.83 | 0.83 | 1.05 | 0.83 | 1.08 | 1.14 | 0.49 | 0.94 | 1.11 | 1.08 |
| Hmgcs2 | 0.97 | 0.94 | 0.86 | 0.96 | 0.82 | 0.82 | 1.44 | 1.31 | 0.92 | 0.96 | 1.07 | 0.73 |
| Hoxa6 | 1.00 | 1.00 | 5.59 | 1.03 | 1.00 | 1.00 | 1.21 | 1.90 | 0.84 | 1.00 | 1.00 | 1.00 |
| Hpx | 0.89 | 1.34 | 1.00 | 1.00 | 0.53 | 1.00 | 1.00 | 1.91 | 1.00 | 1.00 | 1.00 | 1.00 |
| Hs6st3 | 1.00 | 1.00 | 1.00 | 1.00 | 1.00 | 1.00 | 1.00 | 1.00 | 1.00 | 1.00 | 1.00 | 1.00 |
| Hsd3b5 | 0.85 | 6.02 | 1.00 | 1.00 | 1.00 | 1.00 | 1.00 | 1.00 | 1.00 | 1.00 | 1.00 | 1.00 |
| Iapp | 1.00 | 1.00 | 1.00 | 1.00 | 1.95 | 0.97 | 14.07 | 1.00 | 1.00 | 1.00 | 1.00 | 1.00 |
| Icam2 | 1.26 | 1.42 | 0.85 | 1.36 | 0.94 | 0.95 | 0.91 | 0.83 | 1.00 | 1.00 | 0.92 | 0.99 |
| Ido1 | 1.00 | 1.00 | 0.63 | 0.62 | 1.00 | 1.00 | 36.22 | 1.21 | 1.00 | 1.00 | 1.00 | 1.00 |
| Ifi47 | 0.87 | 1.40 | 0.99 | 1.14 | 0.99 | 1.25 | 0.64 | 1.08 | 1.00 | 1.00 | 0.96 | 1.03 |
| Ifit1 | 1.03 | 0.70 | 0.90 | 0.86 | 0.87 | 1.03 | 0.92 | 0.77 | 1.00 | 1.00 | 0.85 | 0.70 |
| Igfbp2 | 0.98 | 0.83 | 0.78 | 1.11 | 1.11 | 1.11 | 2.08 | 3.98 | 1.17 | 0.98 | 1.00 | 1.00 |
| Igfbp4 | 0.90 | 0.95 | 0.96 | 0.99 | 0.84 | 1.03 | 0.82 | 0.94 | 1.20 | 1.10 | 0.88 | 0.89 |

Fig. 37- 39

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Gbp6 | 1.00 | 1.00 | 1.00 | 1.12 | 1.15 | 1.66 | 1.14 | 6.69 | 1.00 | 1.00 |
| Gbp7 | 1.00 | 1.00 | 1.05 | 1.27 | 1.14 | 1.52 | 0.86 | 5.22 | 1.12 | 1.11 |
| Gc | 1.00 | 1.28 | 1.00 | 1.00 | 1.00 | 1.00 | 1.00 | 0.89 | 1.00 | 1.00 |
| Gcnt4 | 1.00 | 1.00 | 1.08 | 1.50 | 1.16 | 1.05 | 0.94 | 1.11 | 1.00 | 1.00 |
| Gfra1 | 1.00 | 1.10 | 1.02 | 1.34 | 1.06 | 1.01 | 1.12 | 1.02 | 0.97 | 0.78 |
| Ggt1 | 0.93 | 1.03 | 1.00 | 1.00 | 1.00 | 1.00 | 1.00 | 1.00 | 2.33 | 1.00 |
| Gjb3 | 1.00 | 1.00 | 1.00 | 1.00 | 1.00 | 1.00 | 1.12 | 0.94 | 0.95 | 0.98 |
| Glra1 | 1.00 | 1.00 | 0.60 | 5.18 | 1.95 | 1.00 | 1.00 | 1.00 | 1.00 | 1.00 |
| Gm10104 | 1.00 | 1.00 | 1.00 | 1.00 | 1.00 | 1.00 | 1.00 | 1.00 | 1.00 | 1.00 |
| Gm10230 | 1.00 | 1.00 | 1.00 | 1.00 | 1.00 | 1.00 | 1.00 | 1.00 | 1.00 | 1.00 |
| Gm1110 | 1.00 | 1.00 | 1.00 | 1.00 | 1.00 | 1.00 | 1.00 | 1.00 | 1.00 | 1.00 |
| Gm12250 | 1.00 | 1.00 | 1.00 | 1.00 | 1.00 | 1.00 | 1.00 | 8.92 | 1.27 | 1.39 |
| Gm13363 | 1.00 | 0.93 | 1.00 | 1.86 | 1.00 | 1.00 | 1.00 | 6.09 | 1.21 | 1.07 |
| Gm14475 | 1.00 | 1.00 | 1.00 | 1.00 | 1.00 | 1.00 | 1.00 | 1.00 | 1.00 | 1.00 |
| Gm14851 | 0.84 | 1.00 | 1.27 | 1.00 | 1.00 | 1.00 | 1.00 | 1.00 | 1.00 | 1.00 |
| Gm15284 | 1.17 | 1.00 | 1.00 | 1.00 | 1.00 | 1.00 | 1.00 | 1.00 | 1.00 | 1.00 |
| Gm15386 | 1.00 | 1.00 | 1.00 | 1.00 | 1.00 | 1.00 | 1.00 | 1.00 | 1.00 | 1.00 |
| Gm17727 | 1.00 | 1.00 | 1.00 | 1.00 | 1.00 | 1.00 | 1.00 | 1.00 | 1.00 | 1.00 |
| Gm20604 | 1.00 | 1.00 | 0.87 | 1.50 | 1.34 | 0.38 | 1.09 | 1.04 | 1.20 | 1.05 |
| Gm2083 | 1.00 | 0.59 | 1.00 | 1.00 | 1.00 | 1.00 | 1.00 | 0.04 | 1.00 | 1.71 |
| Gm20878 | 1.00 | 1.00 | 1.00 | 1.00 | 1.00 | 1.00 | 2.42 | 0.61 | 1.00 | 1.00 |
| Gm21498 | 1.81 | 1.00 | 1.18 | 1.00 | 1.00 | 1.00 | 0.88 | 1.00 | 1.00 | 1.00 |
| Gm266 | 1.00 | 1.00 | 0.91 | 0.67 | 0.64 | 0.87 | 1.10 | 1.00 | 1.00 | 1.00 |
| Gm4759 | 1.00 | 1.00 | 1.00 | 1.00 | 1.00 | 1.00 | 1.00 | 1.00 | 6.06 | 2.64 |
| Gm4846 | 1.00 | 1.00 | 1.00 | 1.00 | 1.00 | 1.00 | 1.00 | 1.00 | 1.00 | 1.00 |
| Gm5531 | 1.00 | 1.00 | 1.00 | 1.00 | 1.00 | 1.00 | 1.00 | 1.00 | 1.00 | 1.00 |
| Gm5916 | 1.00 | 1.00 | 1.00 | 1.00 | 1.00 | 1.00 | 1.00 | 1.00 | 1.00 | 1.00 |
| Gm6040 | 1.00 | 1.00 | 1.00 | 1.00 | 1.00 | 1.00 | 1.00 | 1.00 | 1.00 | 1.00 |
| Gm6792 | 1.00 | 1.00 | 1.00 | 1.00 | 1.00 | 1.00 | 1.00 | 1.00 | 1.00 | 1.00 |
| Gm6793 | 1.00 | 1.00 | 1.00 | 1.00 | 1.00 | 1.00 | 1.00 | 1.00 | 1.00 | 1.00 |
| Gm766 | 1.00 | 1.00 | 1.00 | 1.00 | 1.00 | 1.00 | 1.00 | 1.00 | 1.00 | 1.00 |
| Gnmt | 0.95 | 1.21 | 1.04 | 0.41 | 0.71 | 1.16 | 1.84 | 0.44 | 0.85 | 0.87 |
| Gp2 | 0.95 | 0.95 | 1.00 | 1.00 | 1.00 | 1.00 | 1.00 | 1.00 | 1.00 | 1.00 |
| Gpr26 | 1.00 | 1.00 | 0.69 | 5.24 | 1.37 | 0.88 | 1.00 | 1.00 | 1.00 | 1.00 |
| Gpx5 | 1.00 | 1.00 | 1.00 | 1.00 | 1.00 | 1.00 | 1.00 | 1.00 | 1.00 | 1.00 |
| Gstm6 | 1.00 | 1.00 | 0.95 | 0.57 | 1.14 | 0.92 | 1.23 | 0.76 | 1.00 | 1.00 |
| Gstm7 | 0.89 | 0.83 | 1.09 | 0.75 | 0.98 | 0.94 | 0.96 | 1.00 | 1.00 | 1.00 |
| Guca2a | 1.00 | 7.47 | 1.00 | 1.00 | 1.00 | 1.00 | 1.10 | 1.20 | 1.00 | 1.00 |
| H2-Q7 | 1.00 | 1.00 | 1.00 | 1.08 | 1.06 | 1.90 | 0.68 | 6.79 | 0.96 | 1.28 |
| H2-T9 | 1.00 | 1.00 | 1.00 | 1.00 | 1.00 | 1.00 | 1.18 | 2.27 | 1.00 | 0.73 |
| Hba-a1 | 0.86 | 1.79 | 1.42 | 0.52 | 1.21 | 1.33 | 1.28 | 0.64 | 0.62 | 0.58 |
| Hbb-bs | 1.01 | 0.35 | 3.74 | 0.25 | 0.49 | 1.26 | 1.31 | 0.04 | 0.37 | 0.52 |
| Hcar1 | 1.00 | 1.00 | 0.79 | 1.00 | 1.00 | 1.00 | 1.00 | 1.00 | 1.00 | 1.00 |
| Hipk2 | 1.00 | 0.44 | 0.84 | 7.61 | 1.84 | 1.00 | 0.69 | 1.52 | 2.63 | 1.36 |
| Hist1h4i | 0.43 | 0.93 | 0.53 | 0.77 | 0.99 | 1.08 | 1.40 | 1.78 | 0.64 | 0.80 |
| Hist2h2bb | 1.00 | 1.00 | 0.80 | 1.80 | 1.75 | 1.40 | 0.98 | 1.04 | 1.20 | 0.98 |
| Hist2h3c2 | 1.17 | 0.71 | 0.81 | 0.55 | 0.76 | 0.73 | 3.43 | 7.75 | 0.38 | 1.13 |
| Hmbox1 | 1.08 | 0.53 | 0.68 | 5.87 | 2.00 | 0.96 | 0.62 | 1.60 | 3.81 | 2.45 |
| Hmgcs2 | 0.85 | 0.62 | 1.00 | 0.79 | 0.93 | 1.20 | 0.88 | 0.84 | 1.00 | 1.00 |
| Hoxa6 | 1.00 | 1.00 | 1.00 | 1.00 | 1.00 | 1.00 | 1.00 | 1.00 | 1.00 | 1.00 |
| Hpx | 1.00 | 0.83 | 1.00 | 1.00 | 1.00 | 1.00 | 1.00 | 0.52 | 1.00 | 1.00 |
| Hs6st3 | 1.00 | 1.00 | 0.85 | 5.30 | 1.55 | 0.86 | 1.00 | 1.00 | 1.00 | 1.00 |
| Hsd3b5 | 1.00 | 1.00 | 1.00 | 1.00 | 1.00 | 1.00 | 1.00 | 1.00 | 1.00 | 1.00 |
| Iapp | 0.83 | 1.15 | 1.00 | 1.00 | 1.00 | 1.00 | 1.00 | 1.00 | 1.00 | 1.00 |
| Icam2 | 1.00 | 1.00 | 1.10 | 0.86 | 1.25 | 1.36 | 0.87 | 1.31 | 0.91 | 0.69 |
| Ido1 | 1.00 | 1.00 | 0.97 | 1.06 | 0.91 | 1.30 | 1.00 | 1.00 | 1.00 | 1.00 |
| Ifi47 | 1.00 | 1.05 | 1.00 | 1.00 | 1.00 | 1.02 | 0.98 | 6.11 | 0.82 | 0.97 |
| Ifit1 | 1.00 | 1.00 | 1.26 | 0.69 | 1.30 | 1.56 | 1.00 | 6.88 | 0.80 | 0.99 |
| Igfbp2 | 1.00 | 1.00 | 0.90 | 0.73 | 0.81 | 0.87 | 1.03 | 0.93 | 1.00 | 1.00 |
| Igfbp4 | 0.76 | 1.05 | 0.96 | 0.79 | 0.91 | 0.99 | 1.03 | 0.92 | 0.95 | 1.02 |

Fig. 37- 40

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Igtp | 0.58 | 0.59 | 0.96 | 1.58 | 0.98 | 1.62 | 0.92 | 2.06 | 1.08 | 1.18 | 0.88 | 1.82 |
| Iigp1 | 1.00 | 1.00 | 0.92 | 1.79 | 0.85 | 1.23 | 0.98 | 1.46 | 0.84 | 1.26 | 1.08 | 1.42 |
| Ins2 | 1.00 | 1.00 | 1.00 | 1.00 | 1.00 | 1.00 | 1.00 | 1.00 | 1.00 | 1.00 | 1.00 | 1.00 |
| Irgm2 | 1.00 | 0.68 | 0.95 | 1.31 | 1.10 | 1.36 | 1.11 | 2.11 | 1.18 | 1.08 | 0.99 | 1.57 |
| Kap | 1.00 | 3.34 | 1.00 | 1.00 | 1.00 | 1.00 | 0.86 | 0.59 | 1.54 | 0.94 | 1.30 | 1.04 |
| Kcna3 | 1.00 | 1.00 | 1.00 | 1.00 | 1.00 | 1.00 | 1.00 | 1.00 | 1.28 | 1.41 | 1.00 | 1.00 |
| Kcnk1 | 1.00 | 1.00 | 0.91 | 0.95 | 1.00 | 1.00 | 1.00 | 1.00 | 1.11 | 0.83 | 0.92 | 0.99 |
| Kcnk9 | 1.00 | 1.00 | 1.00 | 1.00 | 1.00 | 1.00 | 1.00 | 1.00 | 1.00 | 1.00 | 1.00 | 1.00 |
| Klf7 | 0.50 | 0.59 | 0.85 | 1.11 | 1.03 | 1.76 | 1.60 | 1.18 | 1.27 | 1.24 | 0.88 | 1.00 |
| Klk1 | 1.00 | 1.00 | 1.00 | 1.00 | 1.00 | 1.00 | 1.00 | 1.24 | 1.60 | 0.82 | 1.14 | 1.04 |
| Krt18 | 1.00 | 1.00 | 1.00 | 1.00 | 1.00 | 1.00 | 1.79 | 1.31 | 0.92 | 0.85 | 0.91 | 0.72 |
| Krt5 | 1.00 | 1.00 | 1.00 | 1.00 | 1.00 | 1.00 | 1.00 | 1.00 | 1.15 | 1.00 | 1.00 | 1.00 |
| Lars2 | 0.63 | 0.82 | 0.84 | 0.69 | 1.02 | 1.29 | 1.13 | 0.91 | 1.07 | 1.08 | 0.86 | 0.96 |
| Lcn10 | 1.00 | 1.00 | 1.00 | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 | 1.00 | 1.00 | 1.00 |
| Lcn2 | 1.67 | 0.59 | 0.32 | 0.51 | 1.30 | 1.73 | 0.54 | 0.50 | 0.97 | 0.97 | 0.98 | 0.80 |
| Lcn5 | 1.00 | 1.00 | 1.00 | 1.00 | 1.00 | 1.00 | 1.00 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 | 1.00 | 1.00 | 1.00 |
| Lgals6 | 1.00 | 1.00 | 1.00 | 1.00 | 1.00 | 1.00 | 1.00 | 1.00 | 1.00 | 1.00 | 1.00 | 1.00 |
| Lingo1 | 1.00 | 1.00 | 1.00 | 1.00 | 1.00 | 1.00 | 1.00 | 1.00 | 0.88 | 1.00 | 1.00 | 1.00 |
| Lmbrd2 | 1.00 | 1.00 | 0.93 | 0.85 | 1.00 | 1.00 | 1.03 | 1.24 | 1.16 | 1.30 | 0.82 | 1.38 |
| Lnpep | 1.00 | 1.00 | 0.76 | 0.87 | 1.13 | 1.09 | 1.41 | 1.03 | 1.53 | 0.93 | 0.81 | 0.87 |
| Lrcol1 | 1.00 | 1.00 | 1.00 | 1.00 | 1.00 | 1.00 | 1.00 | 1.00 | 1.00 | 1.00 | 1.00 | 1.00 |
| Ltf | 0.94 | 0.29 | 0.54 | 0.44 | 1.00 | 1.00 | 5.68 | 1.00 | 1.03 | 0.84 | 1.00 | 1.00 |
| Ly6g5b | 1.00 | 1.00 | 1.00 | 1.00 | 1.00 | 1.00 | 1.00 | 1.00 | 1.27 | 1.00 | 1.00 | 1.00 |
| Ly6g5c | 1.00 | 1.00 | 1.00 | 1.00 | 1.00 | 1.00 | 1.00 | 1.00 | 1.00 | 1.00 | 1.00 | 1.00 |
| Lypd8 | 1.00 | 1.00 | 1.00 | 1.36 | 1.00 | 1.00 | 1.00 | 1.00 | 1.00 | 1.00 | 1.00 | 1.00 |
| Mal | 1.00 | 1.00 | 1.08 | 1.05 | 1.37 | 0.72 | 1.05 | 1.26 | 1.10 | 0.94 | 1.08 | 0.96 |
| Mat1a | 15.26 | 1.00 | 1.00 | 1.00 | 1.00 | 1.00 | 1.00 | 1.00 | 0.88 | 0.76 | 1.00 | 1.00 |
| Mbnl3 | 1.00 | 1.00 | 1.00 | 1.00 | 1.00 | 1.00 | 1.00 | 1.00 | 0.91 | 0.88 | 1.00 | 1.00 |
| Mgat5 | 1.00 | 1.00 | 1.00 | 1.00 | 1.00 | 1.01 | 1.37 | 1.64 | 1.52 | 1.26 | 0.74 | 1.00 |
| Mgst1 | 5.24 | 1.39 | 1.45 | 1.00 | 0.94 | 1.11 | 0.78 | 0.94 | 0.98 | 0.92 | 0.93 | 0.75 |
| Mib1 | 1.00 | 1.00 | 0.59 | 0.86 | 1.03 | 1.30 | 1.36 | 0.99 | 1.31 | 1.00 | 0.85 | 1.31 |
| Mir10a | 1.00 | 1.00 | 1.00 | 1.00 | 45.29 | 1.00 | 1.00 | 1.00 | 0.04 | 1.00 | 1.00 | 1.00 |
| Mir1291 | 1.00 | 1.00 | 1.00 | 0.05 | 45.73 | 26.71 | 20.98 | 0.06 | 1.00 | 1.00 | 1.00 | 1.00 |
| Mir142b | 27.05 | 12.21 | 1.00 | 1.00 | 1.00 | 1.00 | 1.00 | 1.00 | 0.06 | 1.00 | 1.00 | 1.00 |
| Mir1668 | 1.00 | 29.23 | 1.00 | 1.00 | 1.00 | 1.00 | 1.00 | 1.00 | 1.00 | 1.00 | 1.00 | 1.00 |
| Mir1938 | 1.00 | 1.00 | 1.00 | 1.00 | 1.00 | 1.00 | 1.00 | 1.00 | 1.00 | 1.00 | 1.00 | 1.00 |
| Mir1957b | 1.00 | 1.00 | 1.00 | 13.06 | 1.00 | 1.00 | 3.87 | 1.00 | 1.00 | 1.00 | 1.00 | 1.00 |
| Mir214 | 1.00 | 1.00 | 1.00 | 1.00 | 1.00 | 1.00 | 1.00 | 1.00 | 1.00 | 1.00 | 34.55 | 1.00 |
| Mir365-2 | 1.00 | 1.00 | 1.00 | 1.00 | 1.00 | 1.00 | 1.00 | 1.00 | 1.00 | 1.00 | 1.00 | 1.00 |
| Mir486 | 1.00 | 1.00 | 1.00 | 8.30 | 1.00 | 1.00 | 1.00 | 1.00 | 1.00 | 1.00 | 1.00 | 1.00 |
| Mir546 | 1.00 | 1.00 | 1.00 | 10.56 | 1.00 | 1.00 | 1.00 | 1.00 | 1.00 | 1.00 | 1.00 | 1.00 |
| Mir6236 | 0.63 | 0.98 | 13.21 | 0.08 | 0.84 | 5.37 | 2.33 | 1.51 | 4.26 | 10.08 | 0.88 | 0.03 |
| Mir6244 | 1.00 | 1.00 | 1.00 | 6.92 | 1.00 | 1.00 | 0.04 | 1.00 | 1.00 | 1.00 | 1.00 | 1.00 |
| Mir6338 | 1.00 | 1.00 | 131 | 1.00 | 1.00 | 1.00 | 1.00 | 1.00 | 1.00 | 1.00 | 1.00 | 1.00 |
| Mir6340 | 1.00 | 6.46 | 1.00 | 1.00 | 1.00 | 1.00 | 1.00 | 1.00 | 1.00 | 1.00 | 0.16 | 0.04 |
| Mir6357 | 1.00 | 1.00 | 1.00 | 1.00 | 1.00 | 1.00 | 1.00 | 1.00 | 1.00 | 1.00 | 1.00 | 1.00 |
| Mir6363 | 1.00 | 1.00 | 1.00 | 0.08 | 22.91 | 1.00 | 0.09 | 1.00 | 1.00 | 1.00 | 1.00 | 1.00 |
| Mir6516 | 1.00 | 1.00 | 1.00 | 1.00 | 1.00 | 1.00 | 1.00 | 1.00 | 1.00 | 1.00 | 1.00 | 1.00 |
| Mir682 | 1.00 | 1619 | 1.00 | 0.00 | 1.00 | 1.00 | 1.00 | 1.00 | 1.00 | 1184 | 1.00 | 1225 |
| Mir6992 | 1.00 | 1.00 | 1.00 | 1.00 | 1.00 | 1.00 | 1.00 | 1.00 | 1.00 | 1.00 | 1.00 | 1.00 |
| Mir7-1 | 1.00 | 1.00 | 1.00 | 1.00 | 1.00 | 1.00 | 1.00 | 1.00 | 1.00 | 1.00 | 1.00 | 1.00 |
| Mir703 | 1.00 | 1.00 | 0.01 | 1.00 | 3.42 | 0.53 | 0.03 | 0.03 | 0.01 | 0.69 | 41.42 | 0.75 |
| Mir719 | 1.00 | 1.00 | 1.00 | 1.00 | 1.00 | 1.00 | 1.00 | 0.54 | 1.00 | 1.00 | 43.25 | 1.00 |
| Mir760 | 1.00 | 1.00 | 1.00 | 1.00 | 1.00 | 1.00 | 1.00 | 1.00 | 1.00 | 1.00 | 1.00 | 1.00 |
| Mir8091 | 1.00 | 1.00 | 1.00 | 1.00 | 1.00 | 1.00 | 1.00 | 1.00 | 2.79 | 1.00 | 1.00 | 1.00 |
| Mir8093 | 1.00 | 1.00 | 1.00 | 1.00 | 1.00 | 1.00 | 1.00 | 1.00 | 1.00 | 1.00 | 0.08 | 5.23 |

Fig. 37-41

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Igtp | 0.73 | 1.18 | 1.26 | 1.06 | 0.97 | 1.43 | 0.81 | 1.65 | 1.00 | 1.13 | 0.90 | 0.99 |
| Iigp1 | 1.04 | 0.86 | 1.25 | 0.99 | 0.72 | 1.34 | 0.51 | 1.40 | 0.91 | 1.51 | 1.08 | 1.17 |
| Ins2 | 1.00 | 1.00 | 1.00 | 1.00 | 5.23 | 1.00 | 1.00 | 1.00 | 1.00 | 1.00 | 1.00 | 1.00 |
| Irgm2 | 0.86 | 0.93 | 1.27 | 1.23 | 0.88 | 1.15 | 0.65 | 1.23 | 1.00 | 1.00 | 0.80 | 0.96 |
| Kap | 1.00 | 1.00 | 0.69 | 1.00 | 1.00 | 1.00 | 77.52 | 1.47 | 1.00 | 1.00 | 1.09 | 0.84 |
| Kcna3 | 1.00 | 1.00 | 1.00 | 1.00 | 1.00 | 1.00 | 1.00 | 1.00 | 1.00 | 1.00 | 0.99 | 1.34 |
| Kcnk1 | 1.00 | 1.00 | 0.93 | 1.10 | 1.03 | 1.06 | 7.39 | 7.03 | 1.47 | 0.91 | 1.11 | 0.90 |
| Kcnk9 | 1.00 | 1.00 | 1.00 | 1.00 | 1.00 | 1.00 | 1.00 | 1.00 | 1.00 | 1.00 | 1.00 | 1.00 |
| Klf7 | 1.07 | 1.00 | 5.36 | 1.07 | 1.23 | 0.98 | 0.93 | 0.79 | 1.00 | 1.00 | 1.05 | 1.08 |
| Klk1 | 1.00 | 1.01 | 0.80 | 1.07 | 2.10 | 2.01 | 2.08 | 1.00 | 1.13 | 0.70 | 6.39 | 0.28 |
| Krt18 | 0.95 | 1.22 | 0.88 | 0.91 | 1.04 | 0.94 | 5.07 | 3.96 | 1.00 | 1.00 | 1.25 | 1.00 |
| Krt5 | 1.00 | 1.00 | 1.00 | 1.00 | 0.83 | 0.91 | 5.69 | 1.22 | 1.00 | 1.00 | 1.00 | 1.00 |
| Lars2 | 1.12 | 3.83 | 1.08 | 1.14 | 0.19 | 1.06 | 1.12 | 0.96 | 1.42 | 0.98 | 0.90 | 1.02 |
| Lcn10 | 1.00 | 1.00 | 1.00 | 1.00 | 1.00 | 1.00 | 6.37 | 65.65 | 1.00 | 1.00 | 1.00 | 1.00 |
| Lcn12 | 1.00 | 1.00 | 1.00 | 1.00 | 1.00 | 1.00 | 14.17 | 1.26 | 1.00 | 1.00 | 1.00 | 1.00 |
| Lcn2 | 0.45 | 2.92 | 1.18 | 0.63 | 0.56 | 0.89 | 4.31 | 8.99 | 1.37 | 0.71 | 1.44 | 2.15 |
| Lcn5 | 1.00 | 1.00 | 1.00 | 1.00 | 1.00 | 1.00 | 319 | 1.38 | 1.00 | 1.00 | 1.00 | 1.00 |
| Lcn6 | 1.00 | 1.00 | 1.00 | 1.00 | 1.00 | 1.00 | 11.03 | 13.63 | 1.00 | 1.00 | 1.00 | 1.00 |
| Lcn8 | 1.00 | 1.00 | 1.00 | 1.00 | 1.00 | 1.00 | 28.15 | 203 | 1.00 | 1.00 | 1.00 | 1.00 |
| Lcn9 | 1.00 | 1.00 | 1.00 | 1.00 | 1.00 | 1.00 | 17.33 | 168 | 1.00 | 1.00 | 1.00 | 1.00 |
| Lgals6 | 1.00 | 1.00 | 153 | 0.01 | 1.00 | 1.00 | 1.00 | 1.00 | 1.00 | 1.00 | 1.00 | 1.00 |
| Lingo1 | 1.00 | 1.00 | 1.00 | 1.00 | 1.00 | 1.00 | 6.75 | 5.66 | 0.78 | 1.19 | 0.88 | 1.13 |
| Lmbrd2 | 2.02 | 0.38 | 5.63 | 0.94 | 1.18 | 1.16 | 1.00 | 1.00 | 0.96 | 1.04 | 0.83 | 0.91 |
| Lnpep | 1.83 | 0.40 | 4.55 | 0.96 | 1.08 | 0.81 | 0.68 | 0.75 | 0.84 | 0.93 | 0.88 | 1.15 |
| Lrcol1 | 1.00 | 1.00 | 1.00 | 1.00 | 1.00 | 1.00 | 25.28 | 1.00 | 1.00 | 1.00 | 1.00 | 1.00 |
| Ltf | 1.00 | 1.00 | 1.00 | 1.00 | 0.82 | 0.81 | 1.00 | 1.00 | 1.00 | 1.00 | 1.52 | 2.49 |
| Ly6g5b | 1.00 | 1.00 | 0.78 | 1.00 | 1.00 | 1.00 | 17.65 | 97.18 | 0.95 | 1.43 | 0.63 | 1.39 |
| Ly6g5c | 1.00 | 1.00 | 1.00 | 1.00 | 1.00 | 1.00 | 14.69 | 51.15 | 1.00 | 1.00 | 1.00 | 1.00 |
| Lypd8 | 1.00 | 1.00 | 0.78 | 1.03 | 1.65 | 1.13 | 86.88 | 1.00 | 1.19 | 0.76 | 1.00 | 1.00 |
| Mal | 1.00 | 1.00 | 0.89 | 1.29 | 1.35 | 0.97 | 7.30 | 3.73 | 0.79 | 1.00 | 0.87 | 1.01 |
| Mat1a | 1.08 | 0.83 | 1.00 | 1.00 | 0.31 | 0.77 | 1.32 | 5.35 | 1.00 | 1.00 | 1.00 | 1.00 |
| Mbnl3 | 1.00 | 1.00 | 1.19 | 1.12 | 1.06 | 0.90 | 6.08 | 0.98 | 1.00 | 1.00 | 1.02 | 1.30 |
| Mgat5 | 1.00 | 1.00 | 5.60 | 0.90 | 0.93 | 0.96 | 0.98 | 1.18 | 0.50 | 1.16 | 0.94 | 0.87 |
| Mgst1 | 0.90 | 1.15 | 0.82 | 1.13 | 0.96 | 0.91 | 0.76 | 0.77 | 0.82 | 1.27 | 1.04 | 0.91 |
| Mib1 | 2.09 | 0.45 | 5.42 | 0.83 | 1.04 | 1.10 | 1.08 | 0.91 | 0.73 | 1.05 | 1.03 | 1.10 |
| Mir10a | 1.00 | 1.00 | 1.00 | 1.00 | 1.00 | 1.00 | 1.00 | 1.00 | 1.00 | 1.00 | 1.00 | 1.00 |
| Mir1291 | 1.00 | 13.30 | 1.00 | 0.04 | 1.00 | 1.00 | 0.06 | 1.00 | 1.00 | 25.19 | 0.01 | 0.04 |
| Mir142b | 1.00 | 1.00 | 1.00 | 1.00 | 1.00 | 1.00 | 1.00 | 1.00 | 1.00 | 1.00 | 1.62 | 0.74 |
| Mir1668 | 1.00 | 1.00 | 1.00 | 1.00 | 1.00 | 1.00 | 1.00 | 1.00 | 1.00 | 1.00 | 1.00 | 1.00 |
| Mir1938 | 1.00 | 1.00 | 1.00 | 1.00 | 1.00 | 1.00 | 1.00 | 1.00 | 1.00 | 1.00 | 1.00 | 223 |
| Mir1957b | 1.00 | 1.00 | 1.00 | 1.00 | 1.00 | 1.00 | 1.00 | 1.00 | 1.00 | 1.00 | 1.00 | 1.00 |
| Mir214 | 1.00 | 1.00 | 1.00 | 1.00 | 1.00 | 2.57 | 1.00 | 1.00 | 1.00 | 1.00 | 1.00 | 1.00 |
| Mir365-2 | 1.00 | 1.00 | 1.00 | 1.00 | 1.00 | 1.00 | 36.43 | 1.00 | 1.00 | 1.00 | 1.00 | 1.00 |
| Mir486 | 1.00 | 1.00 | 1.00 | 1.00 | 1.00 | 1.00 | 1.00 | 1.00 | 1.00 | 1.00 | 6.66 | 0.09 |
| Mir546 | 0.04 | 1.00 | 1.00 | 1.00 | 1.00 | 1.00 | 1.00 | 1.00 | 1.00 | 1.00 | 1.00 | 1.00 |
| Mir6236 | 1.09 | 4.76 | 0.43 | 0.06 | 0.10 | 3.86 | 0.09 | 9.23 | 0.55 | 1.39 | 0.75 | 2.98 |
| Mir6244 | 0.07 | 1.00 | 1.00 | 1.00 | 1.00 | 1.00 | 0.21 | 1.00 | 1.00 | 1.00 | 5.96 | 1.00 |
| Mir6338 | 1.00 | 1.00 | 1.00 | 1.00 | 1.00 | 1.00 | 1.00 | 1.00 | 1.00 | 1.00 | 1.00 | 1.00 |
| Mir6340 | 0.04 | 1.00 | 17.55 | 1.00 | 1.00 | 1.00 | 1.00 | 17.77 | 17.33 | 0.01 | 1.00 | 1.00 |
| Mir6357 | 1.00 | 1.00 | 1.00 | 1.00 | 0.02 | 1.00 | 72.62 | 0.01 | 0.06 | 1.00 | 1.00 | 1.00 |
| Mir6363 | 1.00 | 1.00 | 1.00 | 1.00 | 1.00 | 1.00 | 1.00 | 1.00 | 1.00 | 1.00 | 9.67 | 1.00 |
| Mir6516 | 1.00 | 1.00 | 1.00 | 1.00 | 1.00 | 1.00 | 1.00 | 1.00 | 1.00 | 1.00 | 27.13 | 1.00 |
| Mir682 | 1.00 | 1748 | 0.00 | 0.00 | 1.00 | 1.00 | 1.00 | 1.00 | 0.00 | 1.00 | 0.80 | 4060 |
| Mir6992 | 1.00 | 1.00 | 1.00 | 1.00 | 1.00 | 1.00 | 1.00 | 1.00 | 1.00 | 1.00 | 1.00 | 1.00 |
| Mir7-1 | 1.00 | 1.00 | 1.00 | 1.00 | 1.00 | 1.00 | 1.00 | 1.00 | 1.00 | 1.00 | 1.00 | 1.00 |
| Mir703 | 1.00 | 1.02 | 0.14 | 0.74 | 1.48 | 2.87 | 1.69 | 0.23 | 58.52 | 0.02 | 2.43 | 3.70 |
| Mir719 | 1.00 | 1.00 | 1.00 | 1.00 | 55.55 | 1.00 | 0.65 | 1.00 | 1.00 | 1.00 | 18.10 | 1.00 |
| Mir760 | 1.00 | 1.00 | 1.00 | 1.00 | 1.00 | 1.00 | 1.00 | 12.14 | 1.00 | 1.00 | 1.00 | 0.05 |
| Mir8091 | 1.00 | 1.00 | 6.13 | 1.00 | 1.00 | 1.00 | 1.00 | 1.00 | 1.00 | 1.00 | 1.00 | 0.15 |
| Mir8093 | 10.97 | 1.00 | 1.00 | 23.26 | 1.00 | 5.47 | 1.00 | 1.00 | 1.00 | 1.00 | 1.00 | 1.00 |

Fig. 37-42

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Igtp | 1.00 | 1.00 | 1.20 | 0.97 | 1.25 | 2.42 | 1.23 | 9.19 | 0.81 | 0.93 |
| Iigp1 | 1.00 | 1.40 | 1.00 | 1.00 | 1.00 | 1.31 | 1.13 | 11.68 | 0.90 | 1.89 |
| Ins2 | 0.91 | 1.29 | 1.00 | 0.95 | 1.73 | 1.00 | 1.00 | 1.00 | 1.00 | 1.00 |
| Irgm2 | 1.00 | 1.00 | 1.00 | 1.00 | 1.00 | 1.31 | 1.07 | 6.14 | 0.95 | 1.07 |
| Kap | 1.00 | 0.83 | 1.00 | 0.94 | 1.01 | 1.06 | 1.00 | 0.91 | 4.20 | 1.00 |
| Kcna3 | 1.00 | 1.00 | 0.66 | 5.03 | 1.45 | 1.06 | 1.00 | 1.00 | 3.68 | 1.68 |
| Kcnk1 | 1.02 | 0.88 | 0.90 | 0.94 | 0.99 | 0.96 | 1.04 | 0.79 | 1.00 | 1.00 |
| Kcnk9 | 1.00 | 1.00 | 0.89 | 5.42 | 1.43 | 0.80 | 1.00 | 1.00 | 1.00 | 1.00 |
| Klf7 | 1.00 | 1.00 | 0.86 | 4.86 | 2.06 | 0.96 | 0.78 | 1.21 | 4.58 | 1.57 |
| Klk1 | 0.93 | 1.09 | 1.00 | 1.00 | 1.00 | 1.00 | 1.00 | 1.33 | 0.83 | 0.47 |
| Krt18 | 0.90 | 0.95 | 1.00 | 0.79 | 0.71 | 0.66 | 1.00 | 1.00 | 1.20 | 0.59 |
| Krt5 | 1.02 | 1.00 | 1.00 | 1.00 | 1.00 | 1.00 | 1.04 | 1.06 | 1.00 | 1.00 |
| Lars2 | 0.82 | 6.31 | 0.83 | 1.26 | 0.85 | 1.06 | 0.81 | 0.86 | 1.37 | 1.05 |
| Lcn10 | 1.00 | 1.00 | 1.00 | 1.00 | 1.00 | 1.00 | 1.00 | 1.00 | 1.00 | 1.00 |
| Lcn12 | 1.00 | 1.00 | 1.00 | 1.00 | 1.00 | 1.00 | 1.00 | 1.00 | 1.00 | 1.00 |
| Lcn2 | 0.45 | 0.82 | 1.00 | 0.73 | 1.85 | 0.84 | 0.82 | 1.25 | 0.85 | 0.92 |
| Lcn5 | 1.00 | 1.00 | 1.00 | 1.00 | 1.00 | 1.00 | 1.00 | 1.00 | 1.00 | 1.00 |
| Lcn6 | 1.00 | 1.00 | 1.00 | 1.00 | 1.00 | 1.00 | 1.00 | 1.00 | 1.00 | 1.00 |
| Lcn8 | 1.00 | 1.00 | 1.00 | 1.00 | 1.00 | 1.00 | 1.00 | 1.00 | 1.00 | 1.00 |
| Lcn9 | 1.00 | 1.00 | 1.00 | 1.00 | 1.00 | 1.00 | 1.00 | 1.00 | 1.00 | 1.00 |
| Lgals6 | 1.00 | 1.00 | 0.69 | 1.00 | 1.00 | 1.00 | 1.00 | 1.00 | 1.00 | 1.00 |
| Lingo1 | 1.00 | 1.00 | 1.01 | 1.11 | 0.88 | 0.93 | 0.80 | 0.89 | 1.00 | 1.00 |
| Lmbrd2 | 1.00 | 0.66 | 0.82 | 5.37 | 1.38 | 1.10 | 0.60 | 1.20 | 2.59 | 1.89 |
| Lnpep | 1.00 | 0.44 | 0.92 | 6.29 | 1.66 | 0.77 | 0.59 | 1.65 | 4.74 | 1.95 |
| Lrcol1 | 1.00 | 1.00 | 1.00 | 1.00 | 1.00 | 1.00 | 1.00 | 1.00 | 1.00 | 1.00 |
| Ltf | 1.00 | 1.00 | 1.00 | 1.00 | 1.00 | 1.00 | 1.00 | 1.00 | 1.05 | 1.09 |
| Ly6g5b | 1.00 | 1.00 | 1.11 | 0.90 | 1.00 | 1.00 | 1.20 | 0.82 | 0.83 | 1.22 |
| Ly6g5c | 1.00 | 1.00 | 1.00 | 1.00 | 1.00 | 1.00 | 1.00 | 1.00 | 1.00 | 1.00 |
| Lypd8 | 3.96 | 34.54 | 1.00 | 1.00 | 1.00 | 1.00 | 1.00 | 1.00 | 1.00 | 1.00 |
| Mal | 1.00 | 1.00 | 1.06 | 0.93 | 1.06 | 0.97 | 0.93 | 0.87 | 1.00 | 1.00 |
| Mat1a | 1.17 | 0.76 | 1.00 | 1.00 | 1.00 | 1.00 | 1.00 | 0.52 | 1.00 | 1.00 |
| Mbnl3 | 1.00 | 0.83 | 1.00 | 1.00 | 1.00 | 1.00 | 0.97 | 1.20 | 1.10 | 1.11 |
| Mgat5 | 1.00 | 1.00 | 0.84 | 3.04 | 1.37 | 0.96 | 0.73 | 1.51 | 3.51 | 1.85 |
| Mgst1 | 0.59 | 0.99 | 1.41 | 0.76 | 0.92 | 1.42 | 1.06 | 0.97 | 0.77 | 1.12 |
| Mib1 | 1.74 | 0.46 | 0.86 | 3.83 | 1.44 | 0.80 | 0.80 | 1.01 | 3.05 | 1.64 |
| Mir10a | 1.00 | 1.00 | 1.00 | 1.00 | 1.00 | 1.00 | 1.00 | 1.00 | 1.00 | 1.00 |
| Mir1291 | 1.00 | 1.00 | 0.06 | 22.63 | 0.05 | 15.97 | 1.00 | 1.00 | 1.00 | 1.00 |
| Mir142b | 1.00 | 1.00 | 1.00 | 1.00 | 1.00 | 1.00 | 1.00 | 1.00 | 1.25 | 0.45 |
| Mir1668 | 1.00 | 1.00 | 1.00 | 1.00 | 1.00 | 1.00 | 1.00 | 1.00 | 1.00 | 0.01 |
| Mir1938 | 1.00 | 1.00 | 1.00 | 1.00 | 1.00 | 1.00 | 1.00 | 1.00 | 1.00 | 1.00 |
| Mir1957b | 1.00 | 1.00 | 1.00 | 1.00 | 1.00 | 1.00 | 1.00 | 1.00 | 1.00 | 1.00 |
| Mir214 | 1.00 | 1.00 | 1.00 | 1.00 | 1.00 | 1.00 | 1.00 | 1.00 | 1.00 | 1.00 |
| Mir365-2 | 1.00 | 1.00 | 1.00 | 1.00 | 1.00 | 1.00 | 1.00 | 1.00 | 1.00 | 1.00 |
| Mir486 | 1.00 | 1.00 | 1.00 | 1.00 | 1.00 | 0.10 | 1.00 | 1.00 | 1.00 | 1.00 |
| Mir546 | 1.00 | 1.00 | 1.00 | 1.00 | 1.00 | 1.00 | 1.00 | 1.00 | 1.00 | 1.00 |
| Mir6236 | 1.58 | 5.64 | 1.74 | 14.70 | 0.04 | 51.74 | 47.76 | 0.03 | 0.62 | 2.02 |
| Mir6244 | 1.00 | 1.00 | 1.00 | 1.00 | 1.00 | 1.00 | 1.00 | 1.00 | 1.00 | 1.00 |
| Mir6338 | 1.00 | 1.00 | 1.00 | 1.00 | 1.00 | 1.00 | 1.00 | 1.00 | 1.00 | 1.00 |
| Mir6340 | 1.00 | 1.00 | 53.26 | 1.00 | 1.00 | 24.22 | 1.00 | 1.00 | 1.00 | 33.96 |
| Mir6357 | 1.00 | 1.00 | 0.02 | 1.00 | 1.00 | 1.00 | 0.02 | 1.00 | 1.00 | 0.04 |
| Mir6363 | 1.00 | 1.00 | 1.00 | 1.00 | 13.54 | 1.00 | 1.00 | 0.53 | 1.00 | 1.00 |
| Mir6516 | 1.00 | 1.00 | 1.00 | 1.00 | 1.00 | 1.00 | 1.00 | 1.00 | 1.00 | 1.00 |
| Mir682 | 1.00 | 2549 | 1.00 | 1765 | 1.00 | 1.00 | 2870 | 1.00 | 1.00 | 1.00 |
| Mir6992 | 1.00 | 1.00 | 0.03 | 50.35 | 1.00 | 1.00 | 1.00 | 1.00 | 1.00 | 1.00 |
| Mir7-1 | 1.00 | 1.00 | 1.00 | 1.00 | 1.00 | 1.00 | 1.00 | 54.24 | 2.50 | 0.01 |
| Mir703 | 0.39 | 1.12 | 0.03 | 2.40 | 1.00 | 0.01 | 5.10 | 2.32 | 0.36 | 0.68 |
| Mir719 | 1.00 | 1.00 | 1.00 | 1.00 | 1.00 | 0.03 | 0.03 | 1.00 | 1.00 | 1.00 |
| Mir760 | 1.00 | 1.00 | 1.00 | 1.00 | 1.00 | 1.00 | 1.00 | 1.00 | 1.00 | 1.00 |
| Mir8091 | 1.00 | 1.00 | 1.00 | 1.00 | 1.00 | 1.00 | 1.00 | 1.00 | 0.22 | 6.89 |
| Mir8093 | 1.00 | 1.00 | 1.00 | 7.06 | 1.00 | 1.00 | 5.68 | 6.61 | 11.88 | 0.18 |

Fig. 37- 43

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Mir8094 | 1.00 | 0.08 | 40.20 | 1.00 | 91.50 | 26.75 | 1.30 | 1.00 | 0.36 | 31.21 | 0.83 | 33.06 |
| Mir8096 | 1.00 | 1.00 | 1.00 | 1.00 | 1.00 | 1.00 | 1.00 | 1.00 | 1.00 | 1.00 | 1.00 | 1.00 |
| Mir8097 | 1.00 | 1.00 | 1.00 | 1.00 | 1.00 | 1.00 | 1.00 | 1.00 | 1.00 | 1.00 | 1.00 | 1.00 |
| Mir8098 | 1.00 | 1.00 | 1.00 | 1.00 | 1.23 | 7.65 | 1.00 | 1.00 | 0.49 | 1.00 | 3.27 | 0.27 |
| Mir8099-1 | 1.00 | 1.00 | 0.07 | 0.10 | 1.00 | 13.66 | 1.00 | 1.00 | 12.95 | 1.00 | 0.10 | 1.00 |
| Mir8102 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 1.00 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 1.00 | 1.00 | 1.00 | 1.00 | 13.80 | 1.00 | 1.00 |
| Mir8112 | 1.00 | 1.00 | 1.00 | 1.00 | 0.42 | 1.00 | 1.15 | 0.07 | 1.00 | 0.11 | 0.06 | 6.89 |
| Mir8114 | 1.00 | 1.00 | 1.00 | 1.00 | 40.40 | 1.00 | 1.00 | 1.00 | 1.00 | 1.00 | 1.00 | 1.00 |
| Mir96 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 1.00 | 1.00 | 112 | 1.00 | 1.00 | 1.00 |
| Mt3 | 1.00 | 1.00 | 0.48 | 1.00 | 1.00 | 1.00 | 1.00 | 1.00 | 0.96 | 0.94 | 1.00 | 1.00 |
| Mttp | 1.00 | 1.00 | 1.03 | 1.01 | 0.95 | 1.20 | 0.96 | 0.81 | 1.00 | 0.97 | 0.94 | 0.90 |
| Muc13 | 0.71 | 0.68 | 1.00 | 1.00 | 1.00 | 1.00 | 1.00 | 1.00 | 1.00 | 1.00 | 1.00 | 1.00 |
| Muc15 | 1.00 | 1.00 | 1.00 | 1.00 | 1.00 | 1.00 | 1.00 | 1.00 | 1.00 | 1.00 | 1.00 | 1.00 |
| Muc5b | 1.00 | 1.00 | 1.00 | 1.00 | 1.00 | 1.00 | 1.00 | 1.00 | 1.39 | 1.00 | 1.00 | 1.00 |
| Mup1 | 16.60 | 1.00 | 1.00 | 1.00 | 1.00 | 1.00 | 1.00 | 1.00 | 1.00 | 1.00 | 1.00 | 1.00 |
| Mup10 | 12.70 | 1.00 | 1.01 | 1.42 | 1.00 | 1.00 | 1.00 | 1.00 | 1.00 | 1.00 | 1.00 | 1.00 |
| Mup12 | 11.73 | 1.00 | 1.00 | 1.00 | 1.00 | 1.00 | 1.00 | 1.00 | 1.00 | 1.00 | 1.00 | 1.00 |
| Mup13 | 9.99 | 1.00 | 1.00 | 1.00 | 1.00 | 1.00 | 1.00 | 1.00 | 1.00 | 1.00 | 1.00 | 1.00 |
| Mup14 | 5.81 | 1.00 | 1.00 | 1.00 | 1.00 | 1.00 | 1.00 | 1.00 | 1.00 | 1.00 | 1.00 | 1.00 |
| Mup15 | 15.72 | 1.00 | 1.68 | 1.92 | 0.87 | 0.48 | 1.00 | 1.00 | 1.00 | 1.00 | 1.00 | 1.00 |
| Mup2 | 21.56 | 1.00 | 2.98 | 1.12 | 2.78 | 1.74 | 1.00 | 1.00 | 1.00 | 1.00 | 1.00 | 1.00 |
| Mup3 | 15.66 | 1.00 | 1.00 | 1.00 | 1.00 | 1.00 | 1.00 | 1.00 | 1.00 | 1.00 | 1.00 | 1.00 |
| Mup8 | 11.73 | 1.00 | 1.00 | 1.00 | 1.00 | 1.00 | 1.00 | 1.00 | 1.00 | 1.00 | 1.00 | 1.00 |
| Mup9 | 25.72 | 1.00 | 2.40 | 1.72 | 1.51 | 0.66 | 1.00 | 1.00 | 1.00 | 1.00 | 1.00 | 1.00 |
| Ndufa3 | 0.48 | 0.69 | 1.05 | 1.04 | 0.88 | 1.02 | 0.83 | 0.71 | 0.77 | 0.95 | 1.30 | 0.86 |
| Npcd | 1.00 | 1.00 | 1.00 | 1.00 | 1.13 | 1.32 | 1.00 | 1.85 | 0.79 | 0.89 | 1.00 | 1.00 |
| Nr4a1 | 0.70 | 0.97 | 1.42 | 1.22 | 0.76 | 7.99 | 1.17 | 2.48 | 0.51 | 1.56 | 0.75 | 2.27 |
| Nxpe2 | 0.53 | 1.04 | 1.00 | 1.00 | 1.00 | 1.00 | 1.00 | 1.00 | 1.00 | 1.00 | 1.00 | 1.00 |
| OTTMUSG000000016609 | 1.00 | 1.00 | 1.00 | 1.00 | 1.00 | 1.00 | 1.00 | 1.00 | 1.00 | 1.00 | 1.00 | 1.00 |
| Oasl2 | 2.25 | 1.21 | 0.97 | 1.13 | 0.75 | 1.26 | 0.86 | 1.11 | 1.03 | 1.03 | 1.18 | 0.87 |
| Oaz1-ps | 0.50 | 0.00 | 1.00 | 1.00 | 1.00 | 1.00 | 2.96 | 1.00 | 0.14 | 1.00 | 0.06 | 1.00 |
| Ovch2 | 1.00 | 1.00 | 1.00 | 1.00 | 1.00 | 1.00 | 1.00 | 1.00 | 1.00 | 1.00 | 1.00 | 1.00 |
| Padi2 | 1.00 | 1.00 | 0.93 | 1.08 | 1.00 | 1.00 | 1.00 | 1.00 | 1.03 | 1.10 | 1.05 | 1.11 |
| Pax8 | 1.00 | 1.00 | 1.00 | 1.00 | 1.00 | 1.00 | 1.00 | 1.00 | 1.00 | 1.00 | 1.04 | 1.09 |
| Pck1 | 13.81 | 1.00 | 2.82 | 0.55 | 1.04 | 1.16 | 3.80 | 2.64 | 1.17 | 0.78 | 0.85 | 0.81 |
| Pdzk1 | 1.00 | 1.00 | 1.09 | 1.17 | 1.12 | 1.05 | 1.13 | 0.82 | 1.05 | 0.83 | 1.00 | 0.97 |
| Pdzk1ip1 | 1.03 | 0.47 | 1.00 | 1.00 | 1.00 | 1.00 | 1.00 | 1.00 | 1.01 | 1.10 | 1.10 | 0.97 |
| Phgr1 | 0.86 | 1.00 | 1.00 | 1.00 | 1.00 | 1.00 | 1.00 | 1.00 | 1.00 | 1.00 | 1.00 | 1.00 |
| Pira4 | 1.50 | 0.51 | 1.00 | 1.00 | 1.00 | 1.00 | 1.00 | 1.00 | 2.44 | 1.00 | 1.00 | 1.00 |
| Pla2g1b | 0.54 | 1.00 | 1.14 | 0.86 | 0.96 | 0.79 | 1.00 | 1.00 | 0.93 | 0.96 | 1.00 | 1.00 |
| Pnlip | 0.82 | 1.00 | 1.00 | 1.00 | 1.00 | 1.00 | 1.00 | 0.55 | 1.00 | 1.40 | 1.00 | 0.89 |
| Pnliprp1 | 1.00 | 1.00 | 1.00 | 1.00 | 1.00 | 1.00 | 1.00 | 1.00 | 1.00 | 1.00 | 1.00 | 1.00 |
| Pnliprp2 | 1.00 | 1.00 | 1.00 | 1.00 | 1.00 | 1.00 | 1.00 | 1.00 | 1.00 | 1.00 | 1.00 | 1.00 |
| Pou3f3 | 1.00 | 1.00 | 1.00 | 1.00 | 1.00 | 1.00 | 1.00 | 1.00 | 1.00 | 1.00 | 0.96 | 0.88 |
| Ppp1r12b | 1.00 | 1.00 | 0.65 | 0.97 | 1.24 | 0.75 | 1.66 | 1.34 | 1.73 | 1.24 | 1.00 | 1.00 |
| Prap1 | 1.00 | 1.00 | 1.00 | 1.00 | 1.00 | 1.00 | 1.00 | 1.00 | 1.00 | 1.00 | 1.00 | 1.00 |
| Prg4 | 10.19 | 3.45 | 0.43 | 0.85 | 0.92 | 0.73 | 0.80 | 0.72 | 1.68 | 0.86 | 1.00 | 1.00 |
| Prom2 | 1.00 | 1.00 | 1.00 | 1.00 | 1.00 | 1.00 | 1.00 | 1.00 | 0.95 | 1.12 | 1.10 | 1.15 |
| Prss2 | 0.61 | 2.97 | 1.00 | 1.00 | 1.00 | 1.00 | 1.00 | 0.76 | 1.00 | 2.04 | 1.00 | 1.07 |
| Prss8 | 1.00 | 1.00 | 1.00 | 1.00 | 1.00 | 1.00 | 1.00 | 1.00 | 1.02 | 0.84 | 0.99 | 0.84 |
| Ptgds | 1.00 | 1.00 | 1.00 | 1.00 | 1.00 | 1.00 | 0.89 | 1.01 | 1.00 | 1.00 | 1.00 | 1.00 |
| Rab11fip4 | 1.00 | 1.00 | 1.00 | 1.00 | 1.00 | 1.00 | 1.00 | 1.00 | 0.86 | 1.32 | 0.54 | 1.37 |
| Rab25 | 1.00 | 1.00 | 1.00 | 1.00 | 1.00 | 1.00 | 1.00 | 1.00 | 0.86 | 0.88 | 1.28 | 1.05 |
| Rbm11 | 1.00 | 1.00 | 1.00 | 1.00 | 1.00 | 1.00 | 1.00 | 1.00 | 1.00 | 1.00 | 1.00 | 1.32 |
| Rbp4 | 22.27 | 1.00 | 2.50 | 0.96 | 1.22 | 0.90 | 1.42 | 1.20 | 0.80 | 0.76 | 1.14 | 0.59 |
| Reg1 | 0.84 | 1.00 | 1.00 | 1.00 | 1.00 | 1.00 | 1.00 | 1.00 | 1.00 | 1.22 | 1.00 | 0.91 |
| Reg2 | 1.00 | 1.00 | 1.00 | 1.00 | 1.00 | 1.00 | 1.00 | 0.60 | 1.00 | 1.00 | 1.00 | 0.86 |

Fig. 37- 44

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Mir8094 | 35.43 | 26.62 | 1.38 | 2.81 | 2.95 | 1.93 | 0.69 | 0.14 | 1.00 | 1.00 | 0.32 | 2.85 |
| Mir8096 | 1.00 | 1.00 | 1.00 | 1.00 | 1.00 | 1.00 | 1.00 | 1.00 | 1.00 | 1.00 | 1.00 | 1.00 |
| Mir8097 | 1.00 | 1.00 | 1.00 | 1.00 | 1.00 | 1.00 | 1.00 | 1.00 | 1.00 | 1.00 | 1.00 | 1.00 |
| Mir8098 | 1.00 | 0.32 | 3.77 | 1.00 | 1.08 | 1.00 | 1.00 | 1.00 | 3.34 | 1.00 | 1.72 | 1.00 |
| Mir8099-1 | 8.99 | 1.00 | 1.00 | 1.00 | 1.00 | 1.00 | 1.00 | 1.00 | 1.00 | 1.39 | 0.12 | 0.03 |
| Mir8102 | 1.00 | 1.00 | 1.00 | 1.00 | 1.00 | 1.00 | 1.00 | 1.00 | 1.00 | 1.00 | 1.00 | 1.00 |
| Mir8103 | 1.00 | 1.00 | 1.00 | 260 | 1.00 | 1.00 | 1.00 | 1.00 | 1.00 | 1.00 | 1.00 | 1.00 |
| Mir8104 | 1.00 | 1.00 | 1.00 | 1.00 | 1.00 | 1.00 | 0.00 | 0.04 | 1.00 | 1.00 | 1.00 | 1.00 |
| Mir8112 | 7.26 | 1.00 | 0.78 | 0.10 | 1.00 | 7.19 | 5.01 | 0.06 | 4.98 | 8.34 | 1.00 | 0.75 |
| Mir8114 | 1.00 | 1.00 | 1.00 | 1.00 | 1.00 | 1.00 | 1.00 | 1.00 | 1.00 | 1.00 | 1.00 | 1.00 |
| Mir96 | 1.00 | 1.00 | 1.00 | 1.00 | 1.00 | 1.00 | 1.00 | 1.00 | 1.00 | 1.00 | 1.00 | 1.00 |
| Mirlet7d | 1.00 | 1.00 | 1.00 | 1.00 | 1.00 | 1.00 | 67.58 | 1.00 | 1.00 | 1.00 | 1.00 | 1.00 |
| Mt3 | 1.00 | 1.00 | 0.90 | 1.10 | 1.00 | 0.71 | 8.19 | 5.71 | 1.03 | 1.00 | 1.00 | 1.00 |
| Mttp | 1.00 | 0.93 | 0.91 | 1.25 | 5.94 | 3.52 | 1.26 | 0.94 | 1.06 | 1.04 | 1.00 | 1.00 |
| Muc13 | 1.00 | 1.00 | 1.07 | 1.04 | 24.47 | 10.08 | 1.00 | 1.00 | 1.00 | 1.00 | 0.90 | 1.00 |
| Muc15 | 1.00 | 1.00 | 1.00 | 1.00 | 0.82 | 0.94 | 65.12 | 26.22 | 0.93 | 1.31 | 1.00 | 1.00 |
| Muc5b | 1.00 | 1.00 | 1.00 | 1.00 | 1.00 | 1.00 | 13.48 | 1.00 | 1.00 | 1.00 | 1.00 | 1.00 |
| Mup1 | 0.95 | 1.17 | 1.00 | 1.00 | 0.29 | 0.97 | 1.00 | 8.42 | 1.00 | 1.00 | 1.00 | 1.00 |
| Mup10 | 0.94 | 1.18 | 1.00 | 1.00 | 0.51 | 1.28 | 1.00 | 6.65 | 1.00 | 1.00 | 1.00 | 1.00 |
| Mup12 | 0.95 | 1.24 | 1.00 | 1.00 | 0.19 | 0.86 | 1.00 | 7.13 | 1.00 | 1.00 | 1.00 | 1.00 |
| Mup13 | 0.92 | 1.18 | 1.00 | 1.00 | 0.52 | 1.57 | 1.00 | 5.71 | 1.00 | 1.00 | 1.00 | 1.00 |
| Mup14 | 1.83 | 1.46 | 1.00 | 1.00 | 0.76 | 1.00 | 1.00 | 4.74 | 1.00 | 1.00 | 1.00 | 1.00 |
| Mup15 | 0.99 | 1.23 | 1.00 | 1.00 | 0.28 | 0.95 | 1.09 | 12.83 | 1.00 | 0.51 | 1.00 | 1.00 |
| Mup2 | 0.86 | 1.13 | 1.00 | 0.83 | 0.43 | 1.27 | 1.92 | 8.76 | 0.94 | 1.19 | 1.00 | 1.00 |
| Mup3 | 1.00 | 1.26 | 1.00 | 1.00 | 0.21 | 0.87 | 1.00 | 7.35 | 1.00 | 1.00 | 1.00 | 1.00 |
| Mup8 | 0.93 | 1.15 | 1.00 | 1.00 | 0.33 | 1.07 | 1.00 | 5.84 | 1.00 | 1.00 | 1.00 | 1.00 |
| Mup9 | 1.03 | 1.22 | 1.00 | 0.65 | 0.29 | 1.05 | 2.20 | 5.31 | 1.00 | 0.77 | 1.00 | 1.00 |
| Ndufa3 | 0.73 | 0.82 | 0.83 | 0.74 | 1.13 | 1.10 | 1.27 | 1.68 | 2.81 | 0.98 | 1.01 | 0.85 |
| Npcd | 1.00 | 1.00 | 0.62 | 1.03 | 0.60 | 0.49 | 1.32 | 1.63 | 1.24 | 0.80 | 0.78 | 0.73 |
| Nr4a1 | 0.77 | 0.53 | 1.71 | 0.88 | 0.63 | 1.01 | 0.65 | 1.31 | 1.08 | 0.88 | 0.82 | 0.99 |
| Nxpe2 | 0.80 | 1.07 | 0.97 | 1.07 | 1.00 | 1.00 | 8.57 | 1.00 | 1.00 | 1.00 | 0.83 | 1.03 |
| OTTMUSG000000 16609 | 1.00 | 1.00 | 1.00 | 1.00 | 0.67 | 0.74 | 1.00 | 1.00 | 1.00 | 1.00 | 1.00 | 1.00 |
| Oasl2 | 0.83 | 0.91 | 0.88 | 0.73 | 1.09 | 1.21 | 0.68 | 0.97 | 0.75 | 1.01 | 1.14 | 0.97 |
| Oaz1-ps | 16.13 | 1.00 | 1.00 | 1.00 | 1.00 | 1.00 | 21.17 | 1.00 | 7.72 | 1.00 | 0.68 | 1.00 |
| Ovch2 | 1.00 | 1.00 | 1.00 | 1.00 | 1.00 | 1.00 | 1.98 | 14.78 | 1.00 | 1.00 | 1.00 | 1.00 |
| Padi2 | 1.00 | 1.00 | 0.91 | 1.01 | 0.85 | 0.99 | 7.23 | 1.89 | 0.84 | 1.19 | 0.95 | 1.12 |
| Pax8 | 1.00 | 1.00 | 0.82 | 1.02 | 1.00 | 1.00 | 6.39 | 8.33 | 1.00 | 1.00 | 1.00 | 1.00 |
| Pck1 | 0.98 | 0.85 | 0.96 | 0.82 | 0.71 | 0.89 | 0.79 | 0.79 | 0.66 | 1.07 | 2.37 | 0.68 |
| Pdzk1 | 0.86 | 0.96 | 1.17 | 0.78 | 1.29 | 0.91 | 8.61 | 6.45 | 1.18 | 0.99 | 1.16 | 0.94 |
| Pdzk1ip1 | 0.98 | 1.00 | 0.68 | 0.88 | 0.84 | 0.92 | 7.74 | 2.88 | 1.54 | 1.03 | 1.03 | 0.92 |
| Phgr1 | 1.00 | 1.00 | 0.75 | 0.89 | 1.30 | 1.16 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 1.00 | 1.00 | 1.00 | 1.00 |
| Pla2g1b | 0.66 | 1.32 | 1.74 | 6.23 | 0.84 | 1.03 | 1.02 | 0.86 | 1.88 | 1.04 | 35.55 | 0.13 |
| Pnlip | 1.00 | 5.70 | 1.94 | 65.25 | 3.19 | 63.64 | 1.00 | 1.00 | 1.00 | 1.00 | 155 | 0.03 |
| Pnliprp1 | 1.00 | 1.76 | 1.86 | 21.91 | 2.08 | 1.69 | 1.00 | 1.00 | 1.00 | 1.00 | 50.63 | 0.06 |
| Pnliprp2 | 1.00 | 1.00 | 2.88 | 5.51 | 1.14 | 0.98 | 1.00 | 1.00 | 1.00 | 1.00 | 12.63 | 0.22 |
| Pou3f3 | 1.00 | 1.00 | 0.92 | 1.44 | 1.00 | 1.00 | 5.02 | 7.86 | 0.93 | 1.00 | 1.00 | 1.00 |
| Ppp1r12b | 1.00 | 1.00 | 6.06 | 0.88 | 0.99 | 0.96 | 1.11 | 0.99 | 0.59 | 1.08 | 0.98 | 1.17 |
| Prap1 | 1.00 | 1.00 | 0.73 | 1.66 | 25.78 | 20.87 | 1.00 | 1.00 | 1.00 | 1.00 | 1.00 | 1.00 |
| Prg4 | 1.07 | 1.12 | 0.88 | 1.00 | 0.66 | 0.76 | 0.56 | 0.94 | 1.00 | 1.00 | 1.44 | 1.12 |
| Prom2 | 1.00 | 1.00 | 1.00 | 1.00 | 0.93 | 1.04 | 27.93 | 3.79 | 1.00 | 1.00 | 1.00 | 1.00 |
| Prss2 | 0.48 | 11.62 | 1.81 | 164 | 2.50 | 133 | 1.00 | 1.00 | 1.00 | 1.00 | 284 | 0.03 |
| Prss8 | 0.98 | 0.78 | 0.83 | 1.02 | 0.97 | 0.95 | 7.29 | 3.24 | 1.00 | 1.00 | 1.00 | 1.00 |
| Ptgds | 1.00 | 1.00 | 1.00 | 1.00 | 0.91 | 0.73 | 20.01 | 2.03 | 1.46 | 0.91 | 1.00 | 1.00 |
| Rab11fip4 | 1.37 | 0.48 | 3.68 | 0.74 | 1.04 | 1.09 | 5.68 | 1.93 | 0.74 | 1.13 | 0.88 | 1.05 |
| Rab25 | 1.00 | 1.00 | 0.81 | 0.97 | 1.06 | 1.01 | 8.41 | 4.16 | 1.00 | 1.00 | 1.00 | 1.00 |
| Rbm11 | 1.00 | 1.00 | 1.00 | 1.00 | 1.00 | 1.00 | 23.67 | 6.47 | 1.05 | 1.21 | 1.00 | 1.00 |
| Rbp4 | 0.91 | 0.95 | 0.60 | 0.92 | 0.57 | 1.09 | 0.86 | 1.00 | 1.95 | 1.12 | 1.01 | 0.67 |
| Reg1 | 1.00 | 3.94 | 1.65 | 58.45 | 2.86 | 24.71 | 1.00 | 1.00 | 1.00 | 1.00 | 89.89 | 0.03 |
| Reg2 | 1.00 | 4.18 | 1.30 | 62.25 | 1.81 | 44.46 | 1.00 | 1.00 | 1.00 | 1.00 | 88.44 | 0.03 |

Fig. 37- 45

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Mir8094 | 20.57 | 24.70 | 1.15 | 7.09 | 117 | 1.54 | 0.28 | 0.03 | 0.62 | 0.06 |
| Mir8096 | 1.00 | 1.00 | 1.00 | 1.00 | 1.00 | 1.00 | 1.00 | 1.00 | 9.78 | 1.00 |
| Mir8097 | 1.00 | 1.00 | 1.00 | 1.00 | 1.00 | 11.13 | 1.00 | 1.00 | 1.00 | 1.00 |
| Mir8098 | 1.00 | 1.00 | 9.16 | 0.13 | 1.00 | 1.00 | 1.00 | 1.00 | 1.00 | 1.00 |
| Mir8099-1 | 0.12 | 1.00 | 0.11 | 11.56 | 1.00 | 16.24 | 0.64 | 1.14 | 1.23 | 1.00 |
| Mir8102 | 1.00 | 1.00 | 1.00 | 1.00 | 1.00 | 1.00 | 5.22 | 1.00 | 1.00 | 1.00 |
| Mir8103 | 1.00 | 1.00 | 1.00 | 1.00 | 1.00 | 1.00 | 1.00 | 1.00 | 1.00 | 1.00 |
| Mir8104 | 350 | 1.00 | 108 | 1.00 | 1.00 | 1.00 | 1.00 | 1.00 | 1.00 | 1.00 |
| Mir8112 | 1.00 | 1.00 | 1.00 | 18.67 | 1.00 | 0.12 | 1.00 | 17.50 | 7.88 | 1.00 |
| Mir8114 | 1.00 | 1.00 | 1.00 | 1.00 | 1.00 | 1.00 | 1.00 | 1.00 | 1.00 | 1.00 |
| Mir96 | 1.00 | 1.00 | 1.00 | 1.00 | 1.00 | 1.00 | 63.61 | 1.00 | 1.00 | 1.00 |
| Mirlet7d | 1.00 | 1.00 | 128 | 1.00 | 1.00 | 1.00 | 1.00 | 1.00 | 1.00 | 1.00 |
| Mt3 | 1.00 | 1.00 | 0.90 | 0.64 | 0.96 | 0.98 | 0.60 | 0.54 | 1.00 | 1.00 |
| Mttp | 1.00 | 1.00 | 0.99 | 1.09 | 0.93 | 0.96 | 1.07 | 1.16 | 1.00 | 1.00 |
| Muc13 | 1.06 | 5.59 | 1.00 | 1.00 | 1.00 | 1.00 | 1.00 | 1.00 | 1.21 | 1.00 |
| Muc15 | 1.00 | 1.00 | 1.00 | 1.00 | 1.00 | 1.00 | 1.00 | 1.31 | 1.00 | 1.00 |
| Muc5b | 1.00 | 1.00 | 1.00 | 1.00 | 1.00 | 1.00 | 1.00 | 1.00 | 1.00 | 1.00 |
| Mup1 | 1.00 | 1.00 | 1.00 | 1.00 | 1.00 | 1.00 | 1.00 | 0.14 | 1.00 | 1.00 |
| Mup10 | 1.00 | 1.00 | 1.00 | 1.00 | 1.00 | 1.00 | 1.00 | 0.19 | 1.00 | 1.00 |
| Mup12 | 1.00 | 1.00 | 1.00 | 1.00 | 1.00 | 1.00 | 1.00 | 0.17 | 1.00 | 1.00 |
| Mup13 | 1.00 | 1.00 | 1.00 | 1.00 | 1.00 | 1.00 | 1.00 | 0.21 | 1.00 | 1.00 |
| Mup14 | 1.00 | 0.97 | 1.00 | 1.00 | 1.00 | 1.00 | 1.00 | 0.51 | 1.00 | 1.00 |
| Mup15 | 1.00 | 0.92 | 1.00 | 1.00 | 1.00 | 1.00 | 1.00 | 0.12 | 1.00 | 2.09 |
| Mup2 | 1.00 | 0.43 | 1.00 | 1.00 | 1.00 | 1.00 | 1.00 | 0.07 | 1.00 | 1.07 |
| Mup3 | 1.00 | 1.00 | 1.00 | 1.00 | 1.00 | 1.00 | 1.00 | 0.16 | 1.00 | 1.00 |
| Mup8 | 1.00 | 1.00 | 1.00 | 1.00 | 1.00 | 1.00 | 1.00 | 0.17 | 1.00 | 1.00 |
| Mup9 | 1.00 | 1.00 | 1.00 | 1.00 | 1.00 | 1.00 | 1.00 | 0.11 | 1.00 | 1.20 |
| Ndufa3 | 0.75 | 6.16 | 1.10 | 0.48 | 0.72 | 0.97 | 1.75 | 0.80 | 0.60 | 0.87 |
| Npcd | 1.00 | 1.00 | 5.92 | 0.57 | 0.62 | 0.96 | 1.29 | 0.96 | 1.00 | 1.00 |
| Nr4a1 | 0.89 | 1.00 | 1.29 | 1.57 | 1.47 | 1.59 | 1.31 | 1.02 | 0.86 | 1.10 |
| Nxpe2 | 1.00 | 1.00 | 1.00 | 1.00 | 1.00 | 1.00 | 1.00 | 1.00 | 0.80 | 0.84 |
| OTTMUSG000000016609 | 1.00 | 1.00 | 0.69 | 6.14 | 1.00 | 1.00 | 1.00 | 1.00 | 1.00 | 1.00 |
| Oasl2 | 1.00 | 1.00 | 1.48 | 0.85 | 1.53 | 3.09 | 0.84 | 8.60 | 1.44 | 1.04 |
| Oaz1-ps | 7.54 | 1.00 | 1.00 | 1.00 | 1.00 | 1.00 | 2.64 | 1.00 | 1.00 | 1.00 |
| Ovch2 | 1.00 | 1.00 | 1.00 | 1.00 | 1.00 | 1.00 | 1.00 | 1.00 | 1.00 | 1.00 |
| Padi2 | 1.07 | 1.22 | 1.13 | 1.25 | 1.11 | 1.21 | 1.12 | 0.93 | 1.11 | 1.12 |
| Pax8 | 1.00 | 1.00 | 1.00 | 1.00 | 1.00 | 1.00 | 1.00 | 1.00 | 0.83 | 0.83 |
| Pck1 | 0.78 | 1.48 | 1.00 | 1.00 | 1.00 | 1.00 | 1.07 | 0.94 | 1.00 | 0.47 |
| Pdzk1 | 1.00 | 1.00 | 0.99 | 1.73 | 1.02 | 0.97 | 1.11 | 1.20 | 1.01 | 1.00 |
| Pdzk1ip1 | 1.06 | 1.80 | 1.00 | 1.00 | 1.31 | 1.00 | 1.09 | 0.94 | 0.76 | 0.69 |
| Phgr1 | 2.31 | 6.22 | 1.00 | 1.00 | 1.00 | 1.00 | 1.00 | 1.00 | 1.00 | 1.00 |
| Pira4 | 1.00 | 1.00 | 1.00 | 1.00 | 1.00 | 1.00 | 1.00 | 1.00 | 20.07 | 1.61 |
| Pla2g1b | 0.82 | 1.35 | 1.22 | 1.00 | 1.00 | 1.00 | 0.89 | 1.00 | 0.37 | 0.86 |
| Pnlip | 0.96 | 1.07 | 1.56 | 1.14 | 1.00 | 1.29 | 1.23 | 1.20 | 1.00 | 1.00 |
| Pnliprp1 | 0.86 | 0.98 | 1.00 | 1.00 | 1.00 | 1.00 | 1.00 | 1.00 | 1.00 | 1.00 |
| Pnliprp2 | 0.90 | 0.97 | 1.00 | 1.00 | 1.00 | 1.00 | 1.00 | 1.00 | 1.00 | 1.00 |
| Pou3f3 | 1.00 | 1.00 | 0.97 | 1.06 | 1.02 | 0.98 | 1.01 | 1.23 | 1.00 | 1.00 |
| Ppp1r12b | 1.00 | 1.00 | 0.83 | 4.09 | 1.51 | 0.88 | 0.73 | 1.60 | 1.00 | 1.00 |
| Prap1 | 1.00 | 1.00 | 1.00 | 1.00 | 1.00 | 1.00 | 1.00 | 1.00 | 1.00 | 1.00 |
| Prg4 | 1.00 | 1.00 | 1.15 | 0.87 | 1.06 | 0.72 | 0.86 | 1.03 | 0.76 | 0.99 |
| Prom2 | 1.20 | 1.04 | 1.00 | 1.00 | 1.00 | 1.00 | 1.05 | 0.95 | 1.00 | 1.00 |
| Prss2 | 0.86 | 1.10 | 1.34 | 1.15 | 1.00 | 0.84 | 1.13 | 0.98 | 2.72 | 1.00 |
| Prss8 | 1.23 | 1.22 | 1.00 | 1.00 | 1.00 | 1.00 | 0.96 | 0.95 | 1.00 | 1.00 |
| Ptgds | 1.00 | 1.00 | 1.02 | 0.77 | 0.92 | 0.95 | 1.52 | 1.03 | 1.00 | 1.00 |
| Rab11fip4 | 1.29 | 0.59 | 0.85 | 2.61 | 1.34 | 0.90 | 0.90 | 1.15 | 2.50 | 1.45 |
| Rab25 | 0.98 | 1.08 | 1.00 | 1.00 | 1.00 | 1.00 | 1.08 | 0.91 | 1.00 | 1.00 |
| Rbm11 | 1.00 | 1.00 | 0.97 | 1.07 | 0.84 | 1.11 | 1.00 | 1.00 | 1.00 | 1.00 |
| Rbp4 | 0.72 | 1.69 | 1.24 | 0.91 | 0.71 | 0.72 | 1.28 | 0.70 | 1.00 | 1.18 |
| Reg1 | 0.93 | 1.22 | 1.00 | 1.00 | 1.00 | 1.00 | 1.00 | 1.00 | 1.00 | 1.00 |
| Reg2 | 0.80 | 1.20 | 1.00 | 1.01 | 1.00 | 1.00 | 1.20 | 1.24 | 1.04 | 1.00 |

Fig. 37- 46

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Reg3a | 1.00 | 1.00 | 1.00 | 1.00 | 1.00 | 1.00 | 1.00 | 1.00 | 1.00 | 1.00 | 1.00 | 1.00 |
| Reg3b | 1.00 | 1.00 | 1.00 | 1.00 | 1.00 | 1.02 | 1.00 | 1.00 | 1.00 | 1.00 | 1.00 | 1.17 |
| Reg3d | 1.00 | 1.00 | 1.00 | 1.00 | 1.00 | 1.00 | 1.00 | 1.00 | 1.00 | 1.00 | 1.00 | 1.00 |
| Reg3g | 1.00 | 1.00 | 1.00 | 1.00 | 1.00 | 1.00 | 3.10 | 1.65 | 1.06 | 0.91 | 1.00 | 1.00 |
| Rhcg | 1.00 | 1.00 | 1.00 | 1.00 | 1.00 | 1.00 | 1.00 | 1.00 | 1.00 | 1.00 | 1.06 | 1.13 |
| Rmrp | 1.00 | 1.00 | 1.00 | 1.52 | 1.00 | 1.00 | 1.00 | 1.00 | 1.00 | 1.00 | 1.00 | 1.00 |
| Rnase1 | 0.84 | 1.70 | 1.00 | 1.00 | 1.00 | 1.00 | 0.73 | 0.76 | 1.00 | 1.15 | 1.00 | 0.77 |
| Rnase10 | 1.00 | 1.00 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.00 | 1.00 | 1.00 | 1.00 |
| Rnase13 | 1.00 | 1.00 | 0.62 | 1.19 | 1.00 | 1.00 | 1.00 | 1.00 | 1.00 | 1.00 | 1.00 | 1.00 |
| Rnase4 | 6.07 | 1.74 | 1.03 | 1.02 | 0.93 | 0.84 | 0.93 | 1.01 | 0.99 | 0.85 | 1.08 | 0.87 |
| Rnase9 | 1.00 | 1.00 | 1.00 | 1.00 | 1.00 | 1.00 | 1.00 | 1.00 | 1.00 | 1.00 | 1.00 | 1.00 |
| Rnf186 | 1.00 | 1.00 | 1.00 | 1.00 | 1.00 | 1.00 | 1.00 | 1.00 | 1.13 | 0.90 | 1.19 | 0.93 |
| Rnu11 | 1.00 | 1.00 | 1.00 | 1.00 | 1.00 | 1.00 | 1.00 | 1.00 | 1.00 | 1.00 | 1.00 | 1.00 |
| Rps18 | 1.00 | 1.00 | 0.88 | 1.36 | 0.62 | 2.01 | 0.80 | 0.75 | 0.42 | 2.32 | 0.61 | 1.21 |
| Rtp4 | 1.00 | 0.65 | 0.72 | 0.92 | 0.95 | 0.96 | 0.69 | 1.07 | 0.99 | 1.06 | 1.43 | 0.96 |
| S100g | 1.00 | 1.00 | 1.00 | 1.00 | 1.00 | 1.00 | 1.00 | 1.00 | 0.91 | 0.79 | 1.14 | 0.95 |
| Saa3 | 8.87 | 3.64 | 1.00 | 1.00 | 1.00 | 1.00 | 0.80 | 1.04 | 1.19 | 1.07 | 1.00 | 1.00 |
| Scarna3b | 1.00 | 1.00 | 1.00 | 1.00 | 1.00 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scgb1a1 | 1.00 | 5.11 | 1.00 | 1.00 | 1.00 | 1.00 | 4.49 | 1.25 | 1.04 | 1.02 | 1.10 | 1.18 |
| Scube1 | 1.00 | 1.00 | 1.00 | 1.00 | 1.00 | 1.00 | 1.00 | 1.00 | 1.00 | 1.19 | 1.00 | 1.00 |
| Sdc3 | 6.41 | 2.84 | 1.14 | 0.88 | 1.15 | 1.00 | 1.07 | 1.06 | 1.07 | 1.05 | 0.88 | 1.00 |
| Serinc2 | 1.00 | 1.00 | 1.05 | 1.05 | 1.00 | 1.00 | 1.00 | 1.00 | 0.84 | 0.87 | 1.14 | 1.10 |
| Serpina1a | 28.06 | 1.00 | 1.09 | 0.66 | 0.95 | 0.65 | 0.83 | 1.21 | 0.95 | 0.72 | 1.11 | 0.79 |
| Serpina1b | 36.84 | 1.00 | 0.79 | 1.24 | 1.07 | 0.67 | 0.81 | 0.94 | 0.82 | 0.90 | 1.06 | 0.86 |
| Serpina1c | 44.11 | 1.00 | 1.54 | 0.89 | 1.04 | 1.04 | 0.62 | 1.09 | 0.76 | 0.80 | 1.20 | 0.76 |
| Serpina1d | 15.22 | 1.00 | 1.52 | 0.94 | 1.39 | 0.67 | 0.80 | 1.31 | 0.95 | 0.99 | 1.00 | 0.80 |
| Serpina1e | 8.13 | 1.00 | 1.00 | 1.00 | 1.42 | 0.93 | 1.00 | 0.99 | 0.76 | 0.72 | 1.26 | 0.77 |
| Serpina1f | 1.00 | 1.00 | 1.00 | 1.00 | 1.00 | 1.00 | 1.00 | 1.00 | 1.00 | 1.00 | 1.12 | 0.88 |
| Serpina3k | 53.31 | 1.00 | 1.39 | 0.94 | 2.18 | 0.71 | 1.00 | 1.00 | 1.00 | 1.00 | 1.00 | 1.00 |
| Serpina3n | 5.23 | 1.00 | 0.99 | 0.94 | 0.97 | 0.94 | 0.68 | 0.64 | 0.96 | 1.03 | 0.69 | 1.07 |
| Serpinb2 | 3.57 | 6.81 | 1.00 | 1.00 | 1.00 | 1.00 | 1.00 | 1.00 | 1.00 | 1.00 | 1.00 | 1.00 |
| Slc17a9 | 1.00 | 1.00 | 1.00 | 1.00 | 1.00 | 1.00 | 1.00 | 1.00 | 0.96 | 1.20 | 1.00 | 1.00 |
| Slc1a1 | 1.00 | 1.00 | 1.69 | 1.19 | 1.18 | 1.38 | 1.20 | 1.59 | 0.96 | 1.07 | 1.08 | 1.07 |
| Slc27a2 | 5.29 | 1.00 | 1.06 | 1.00 | 0.92 | 0.76 | 0.97 | 1.11 | 1.39 | 1.00 | 0.87 | 0.88 |
| Slc35f2 | 1.00 | 1.00 | 1.00 | 1.00 | 1.00 | 1.00 | 1.00 | 1.00 | 1.00 | 1.00 | 0.98 | 1.05 |
| Slc38a5 | 0.62 | 0.87 | 1.00 | 1.00 | 1.00 | 1.00 | 1.00 | 1.00 | 0.74 | 1.38 | 1.00 | 1.00 |
| Slc9a7 | 1.00 | 1.00 | 1.00 | 1.00 | 1.00 | 1.00 | 1.00 | 1.00 | 1.00 | 1.00 | 1.00 | 1.00 |
| Snora16a | 1.00 | 1.00 | 0.06 | 1.00 | 14.71 | 0.04 | 1.14 | 8.14 | 5.99 | 1.00 | 3.53 | 1.16 |
| Snora17 | 1.00 | 1.00 | 1.00 | 1.00 | 1.00 | 1.00 | 1.00 | 1.00 | 1.40 | 1.00 | 1.00 | 1.00 |
| Snora21 | 1.00 | 1.00 | 1.00 | 1.00 | 1.00 | 1.00 | 1.00 | 1.00 | 1.00 | 1.00 | 1.00 | 1.00 |
| Snora28 | 1.00 | 1.00 | 1.00 | 25.42 | 1.00 | 1.00 | 1.00 | 0.08 | 0.03 | 0.06 | 1.00 | 1.00 |
| Snora2b | 1.00 | 1.00 | 1.00 | 1.00 | 1.00 | 1.00 | 0.04 | 1.00 | 1.00 | 1.00 | 1.00 | 1.00 |
| Snora3 | 1.00 | 1.00 | 1.00 | 1.00 | 1.00 | 1.00 | 1.00 | 1.00 | 1.00 | 1.00 | 1.00 | 1.00 |
| Snora30 | 1.00 | 1.00 | 1.00 | 1.00 | 1.00 | 1.00 | 1.00 | 1.00 | 1.00 | 1.00 | 1.00 | 1.00 |
| Snora31 | 1.00 | 1.00 | 1.00 | 1.00 | 1.00 | 1.00 | 1.00 | 1.00 | 1.00 | 1.00 | 1.00 | 1.00 |
| Snora33 | 1.00 | 1.00 | 1.00 | 1.00 | 1.00 | 1.00 | 1.00 | 110 | 0.02 | 0.01 | 1.00 | 3.36 |
| Snora34 | 1.00 | 1.00 | 0.02 | 0.06 | 21.11 | 0.04 | 1.00 | 1.00 | 0.04 | 1.00 | 1.00 | 1.00 |
| Snora36b | 1.00 | 1.00 | 1.00 | 1.00 | 1.00 | 1.00 | 1.00 | 1.00 | 1.00 | 1.00 | 1.00 | 1.00 |
| Snora41 | 1.00 | 1.00 | 1.00 | 1.00 | 0.03 | 0.03 | 1.00 | 1.00 | 0.05 | 1.38 | 1.00 | 1.00 |
| Snora43 | 1.00 | 1.00 | 1.00 | 1.00 | 6.46 | 1.00 | 0.38 | 0.70 | 0.07 | 0.08 | 1.00 | 0.29 |
| Snora44 | 1.00 | 1.00 | 1.00 | 1.00 | 1.00 | 1.00 | 0.06 | 1.00 | 0.08 | 1.00 | 1.00 | 1.00 |
| Snora52 | 1.00 | 1.00 | 7.39 | 1.00 | 8.06 | 0.11 | 0.15 | 0.16 | 1.00 | 1.00 | 1.00 | 0.10 |
| Snora5c | 1.00 | 1.00 | 1.00 | 1.00 | 1.00 | 1.00 | 1.00 | 1.00 | 1.00 | 1.00 | 1.00 | 1.00 |
| Snora62 | 1.00 | 1.00 | 1.00 | 1.00 | 1.00 | 1.00 | 1.00 | 1.00 | 1.00 | 1.00 | 1.00 | 1.00 |
| Snora64 | 1.00 | 1.00 | 20.08 | 0.05 | 1.00 | 53.42 | 1.00 | 3.10 | 5.72 | 1.00 | 0.88 | 1.13 |
| Snora65 | 1.00 | 1.00 | 37.19 | 31.20 | 2.54 | 0.02 | 1.00 | 1.00 | 17.21 | 14.40 | 1.00 | 15.27 |
| Snora69 | 1.00 | 1.00 | 1.00 | 1.00 | 1.00 | 1.00 | 1.00 | 1.00 | 1.00 | 1.00 | 1.00 | 1.00 |
| Snora70 | 1.00 | 1.00 | 0.08 | 7.86 | 0.84 | 0.54 | 0.06 | 11.66 | 1.41 | 1.00 | 1.00 | 1.15 |

Fig. 37- 47

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Reg3a | 1.00 | 1.00 | 1.46 | 5.42 | 1.73 | 6.58 | 1.00 | 1.00 | 1.00 | 1.00 | 12.66 | 0.23 |
| Reg3b | 1.00 | 1.00 | 0.95 | 0.99 | 3.70 | 54.25 | 1.00 | 1.00 | 1.00 | 1.00 | 19.55 | 0.14 |
| Reg3d | 1.00 | 1.00 | 1.78 | 4.55 | 1.87 | 1.30 | 1.00 | 1.00 | 1.00 | 1.00 | 6.61 | 0.56 |
| Reg3g | 1.00 | 1.00 | 1.01 | 1.28 | 4.11 | 6.37 | 1.00 | 1.00 | 1.00 | 1.00 | 1.00 | 1.00 |
| Rhcg | 1.00 | 1.00 | 1.00 | 1.00 | 1.00 | 1.00 | 21.99 | 1.00 | 0.85 | 0.91 | 1.00 | 1.00 |
| Rmrp | 0.91 | 5.13 | 0.76 | 1.34 | 0.06 | 1.00 | 1.00 | 1.00 | 1.00 | 0.96 | 1.28 | 1.36 |
| Rnase1 | 0.94 | 5.19 | 1.69 | 103 | 2.30 | 1.72 | 3.18 | 2.64 | 1.00 | 1.00 | 197 | 0.03 |
| Rnase10 | 1.00 | 1.00 | 1.00 | 1.00 | 1.00 | 1.00 | 23.69 | 196 | 1.00 | 0.97 | 1.00 | 1.00 |
| Rnase12 | 1.00 | 1.00 | 1.00 | 1.00 | 1.00 | 1.00 | 56.44 | 12.51 | 1.00 | 1.00 | 0.87 | 1.22 |
| Rnase13 | 1.00 | 1.00 | 1.00 | 1.00 | 1.00 | 1.00 | 74.45 | 1.00 | 1.00 | 0.92 | 1.00 | 1.00 |
| Rnase4 | 0.84 | 0.99 | 0.77 | 1.13 | 1.13 | 0.99 | 0.77 | 0.86 | 0.75 | 1.02 | 1.04 | 0.81 |
| Rnase9 | 1.00 | 1.00 | 1.00 | 1.00 | 1.00 | 1.00 | 217 | 1.00 | 1.00 | 1.00 | 1.00 | 1.00 |
| Rnf186 | 1.19 | 0.64 | 0.92 | 1.08 | 2.19 | 0.98 | 5.51 | 5.04 | 1.00 | 1.00 | 0.87 | 1.00 |
| Rnu11 | 1.00 | 1.00 | 1.00 | 1.00 | 1.00 | 1.00 | 1.00 | 1.00 | 1.00 | 128 | 1.00 | 1.00 |
| Rps18 | 1.80 | 1.25 | 0.88 | 0.32 | 1.11 | 0.89 | 1.43 | 1.46 | 1.00 | 0.98 | 1.03 | 0.93 |
| Rtp4 | 0.71 | 1.11 | 0.81 | 0.85 | 1.24 | 2.05 | 0.74 | 0.93 | 1.00 | 1.00 | 0.94 | 0.76 |
| S100g | 1.00 | 1.00 | 0.72 | 1.86 | 9.54 | 3.36 | 2.15 | 1.00 | 1.00 | 1.00 | 1.00 | 1.00 |
| Saa3 | 0.69 | 0.96 | 1.03 | 0.65 | 0.15 | 1.52 | 0.33 | 1.78 | 1.00 | 1.00 | 1.67 | 2.25 |
| Scarna3b | 1.00 | 1.00 | 1.00 | 1.00 | 1.00 | 10.56 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 1.00 | 1.00 | 1.00 | 1.00 | 1.00 |
| Scgb1a1 | 0.52 | 1.00 | 0.55 | 1.00 | 0.85 | 1.18 | 1.00 | 1.00 | 1.00 | 1.00 | 0.72 | 0.97 |
| Scube1 | 1.00 | 1.00 | 1.24 | 0.89 | 1.03 | 1.12 | 5.32 | 2.06 | 1.00 | 1.00 | 1.13 | 1.11 |
| Sdc3 | 1.19 | 1.09 | 1.19 | 0.98 | 0.83 | 1.15 | 0.97 | 1.15 | 0.82 | 0.90 | 0.92 | 1.17 |
| Serinc2 | 0.89 | 1.23 | 0.94 | 1.05 | 1.16 | 1.08 | 3.67 | 7.72 | 1.28 | 0.83 | 1.05 | 0.98 |
| Serpina1a | 1.04 | 1.04 | 1.07 | 0.56 | 0.22 | 0.87 | 0.89 | 1.55 | 1.12 | 1.13 | 1.30 | 0.92 |
| Serpina1b | 1.03 | 1.06 | 0.83 | 0.55 | 0.28 | 0.78 | 0.73 | 1.28 | 0.77 | 1.03 | 1.09 | 1.01 |
| Serpina1c | 1.00 | 1.11 | 0.92 | 0.72 | 0.15 | 0.60 | 1.00 | 1.90 | 0.74 | 0.87 | 1.03 | 0.95 |
| Serpina1d | 1.05 | 1.04 | 1.00 | 0.62 | 0.24 | 1.00 | 1.00 | 1.75 | 0.76 | 1.00 | 1.13 | 0.85 |
| Serpina1e | 1.09 | 1.08 | 1.00 | 1.00 | 0.58 | 1.00 | 1.39 | 1.11 | 1.00 | 1.00 | 1.11 | 0.86 |
| Serpina1f | 1.00 | 1.00 | 1.00 | 1.00 | 1.00 | 1.00 | 18.72 | 1.00 | 1.00 | 1.00 | 1.00 | 1.00 |
| Serpina3k | 1.02 | 1.10 | 1.00 | 0.82 | 0.10 | 0.84 | 1.04 | 2.83 | 1.00 | 0.67 | 1.00 | 1.00 |
| Serpina3n | 1.01 | 1.09 | 0.93 | 0.85 | 0.67 | 0.96 | 0.73 | 1.14 | 0.96 | 1.01 | 1.11 | 0.83 |
| Serpinb2 | 1.00 | 1.00 | 1.00 | 1.00 | 0.82 | 1.05 | 1.00 | 1.19 | 1.00 | 1.00 | 0.88 | 1.05 |
| Slc17a9 | 0.56 | 1.11 | 0.84 | 1.00 | 1.23 | 1.10 | 4.11 | 5.93 | 1.17 | 0.95 | 0.98 | 1.44 |
| Slc1a1 | 1.00 | 1.00 | 0.83 | 1.17 | 1.00 | 1.00 | 1.16 | 5.46 | 1.00 | 1.00 | 1.00 | 1.00 |
| Slc27a2 | 1.07 | 0.92 | 0.85 | 1.00 | 0.65 | 0.96 | 6.21 | 4.46 | 1.00 | 1.00 | 0.77 | 0.69 |
| Slc35f2 | 1.00 | 1.00 | 0.80 | 1.44 | 1.48 | 1.07 | 5.21 | 3.16 | 0.84 | 1.02 | 1.09 | 0.84 |
| Slc38a5 | 1.00 | 1.00 | 1.00 | 1.00 | 0.91 | 0.87 | 143 | 5.16 | 1.47 | 0.76 | 0.93 | 1.16 |
| Slc9a7 | 1.00 | 1.00 | 1.00 | 1.00 | 1.00 | 1.00 | 1.00 | 1.00 | 1.00 | 1.00 | 1.00 | 1.00 |
| Snora16a | 1.00 | 1.00 | 34.66 | 0.06 | 0.65 | 0.97 | 3.62 | 2.79 | 1.00 | 8.13 | 1.23 | 22.47 |
| Snora17 | 1.00 | 1.00 | 1.00 | 1.00 | 8.56 | 0.48 | 1.00 | 1.00 | 1.00 | 1.00 | 0.15 | 0.11 |
| Snora21 | 1.00 | 1.00 | 1.00 | 1.00 | 1.00 | 1.00 | 1.00 | 0.10 | 1.00 | 1.00 | 6.66 | 8.35 |
| Snora28 | 1.00 | 1.00 | 15.45 | 1.00 | 1.00 | 1.00 | 1.00 | 1.00 | 1.00 | 1.00 | 1.00 | 1.00 |
| Snora2b | 1.00 | 1.00 | 1.00 | 1.00 | 1.00 | 1.00 | 1.00 | 1.00 | 1.00 | 1.00 | 1.00 | 1.00 |
| Snora3 | 1.00 | 10.63 | 1.00 | 1.00 | 0.98 | 0.07 | 0.70 | 1.00 | 1.00 | 1.00 | 1.00 | 0.05 |
| Snora30 | 1.00 | 1.00 | 1.00 | 1.00 | 1.00 | 1.00 | 33.37 | 1.00 | 1.00 | 1.00 | 1.00 | 1.00 |
| Snora31 | 1.00 | 1.00 | 1.00 | 1.00 | 1.00 | 0.04 | 36.43 | 44.61 | 1.00 | 1.00 | 1.00 | 1.00 |
| Snora33 | 1.00 | 1.00 | 1.00 | 1.00 | 1.00 | 0.01 | 1.00 | 1.00 | 52.81 | 1.00 | 55.73 | 0.01 |
| Snora34 | 1.00 | 1.00 | 1.00 | 0.04 | 1.00 | 15.92 | 1.00 | 13.09 | 1.00 | 1.00 | 1.00 | 32.05 |
| Snora36b | 1.00 | 1.00 | 1.00 | 1.00 | 1.00 | 1.00 | 1.00 | 20.17 | 1.00 | 1.00 | 1.00 | 24.81 |
| Snora41 | 1.00 | 0.03 | 1.00 | 0.03 | 0.99 | 0.04 | 1.00 | 0.02 | 18.81 | 36.05 | 1.00 | 0.03 |
| Snora43 | 0.18 | 3.93 | 6.13 | 2.17 | 1.00 | 0.10 | 10.66 | 1.40 | 1.00 | 14.29 | 0.10 | 0.15 |
| Snora44 | 1.00 | 1.00 | 20.44 | 1.00 | 1.00 | 1.00 | 1.00 | 1.00 | 1.00 | 1.00 | 1.00 | 1.00 |
| Snora52 | 1.00 | 0.11 | 1.58 | 0.11 | 1.00 | 0.08 | 1.44 | 0.70 | 1.00 | 1.00 | 0.82 | 1.00 |
| Snora5c | 1.00 | 1.00 | 1.00 | 1.00 | 1.00 | 1.00 | 1.00 | 1.00 | 1.00 | 1.00 | 134 | 1.00 |
| Snora62 | 1.00 | 1.00 | 1.00 | 1.00 | 1.00 | 1.00 | 5.81 | 1.00 | 1.00 | 1.00 | 1.00 | 1.00 |
| Snora64 | 1.00 | 0.04 | 1.00 | 1.00 | 0.02 | 0.02 | 1.38 | 0.02 | 1.09 | 1.00 | 0.81 | 34.70 |
| Snora65 | 1.00 | 1.00 | 0.02 | 1.00 | 0.02 | 0.96 | 10.82 | 26.17 | 1.00 | 1.00 | 0.81 | 1.00 |
| Snora69 | 1.00 | 9.29 | 1.00 | 0.06 | 1.00 | 0.08 | 1.00 | 1.00 | 1.00 | 1.00 | 0.09 | 0.06 |
| Snora70 | 0.11 | 12.39 | 0.04 | 0.04 | 1.47 | 2.90 | 0.36 | 1.04 | 1.00 | 1.00 | 2.45 | 0.45 |

Fig. 37-48

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Reg3a | 0.85 | 1.28 | 1.00 | 1.00 | 1.00 | 1.00 | 1.00 | 1.00 | 1.00 | 1.00 |
| Reg3b | 0.92 | 1.26 | 0.89 | 1.00 | 1.00 | 1.00 | 0.95 | 1.00 | 1.00 | 1.00 |
| Reg3d | 0.91 | 1.28 | 1.00 | 1.00 | 1.00 | 1.00 | 1.00 | 1.00 | 1.00 | 1.00 |
| Reg3g | 1.04 | 1.51 | 1.00 | 1.00 | 1.00 | 1.00 | 1.00 | 1.00 | 1.00 | 1.00 |
| Rhcg | 1.00 | 1.00 | 1.00 | 1.00 | 1.00 | 1.00 | 1.00 | 1.00 | 1.00 | 1.00 |
| Rmrp | 1.00 | 9.14 | 1.00 | 1.00 | 1.00 | 1.00 | 1.00 | 1.00 | 0.57 | 1.00 |
| Rnase1 | 0.85 | 1.14 | 1.80 | 1.17 | 1.31 | 1.14 | 1.08 | 1.01 | 1.01 | 1.00 |
| Rnase10 | 1.00 | 1.00 | 1.00 | 1.00 | 1.00 | 1.00 | 1.00 | 1.00 | 1.00 | 1.00 |
| Rnase12 | 1.00 | 1.00 | 1.00 | 1.00 | 1.00 | 1.00 | 1.00 | 1.00 | 1.01 | 1.52 |
| Rnase13 | 1.00 | 1.00 | 1.00 | 1.00 | 1.00 | 1.00 | 1.00 | 1.00 | 1.00 | 1.00 |
| Rnase4 | 0.93 | 1.09 | 0.92 | 0.72 | 1.11 | 1.23 | 1.05 | 1.00 | 0.81 | 1.09 |
| Rnase9 | 1.00 | 1.00 | 1.00 | 1.00 | 1.00 | 1.00 | 1.00 | 1.00 | 1.00 | 1.00 |
| Rnf186 | 0.96 | 1.24 | 1.00 | 1.00 | 1.00 | 1.00 | 1.00 | 1.00 | 1.00 | 1.00 |
| Rnu11 | 1.00 | 1.00 | 1.00 | 1.00 | 1.00 | 1.00 | 1.00 | 1.00 | 0.03 | 1.00 |
| Rps18 | 0.75 | 1.69 | 0.82 | 1.28 | 2.88 | 6.41 | 0.90 | 0.66 | 0.91 | 0.68 |
| Rtp4 | 1.00 | 1.00 | 1.25 | 0.78 | 0.88 | 2.00 | 1.14 | 5.50 | 1.16 | 1.01 |
| S100g | 1.00 | 1.00 | 1.00 | 1.00 | 1.00 | 1.00 | 1.00 | 1.00 | 1.00 | 1.00 |
| Saa3 | 0.38 | 1.00 | 1.00 | 1.00 | 1.57 | 8.73 | 0.26 | 1.81 | 1.49 | 1.55 |
| Scarna3b | 1.00 | 1.00 | 1.00 | 1.00 | 1.00 | 1.00 | 1.00 | 1.00 | 1.00 | 1.00 |
| Scarna8 | 1.00 | 1.00 | 1.00 | 1.00 | 1.00 | 1.00 | 1.00 | 39.27 | 1.00 | 0.06 |
| Scgb1a1 | 1.00 | 3.43 | 1.00 | 7.54 | 1.22 | 0.58 | 1.47 | 0.91 | 4.71 | 1.00 |
| Scube1 | 1.00 | 1.00 | 1.11 | 1.40 | 1.01 | 1.02 | 0.96 | 1.01 | 1.00 | 1.00 |
| Sdc3 | 1.00 | 1.00 | 0.96 | 1.20 | 1.01 | 1.04 | 1.00 | 1.26 | 1.17 | 0.90 |
| Serinc2 | 0.80 | 1.31 | 0.95 | 0.72 | 0.83 | 1.06 | 0.91 | 0.83 | 1.00 | 1.00 |
| Serpina1a | 1.00 | 1.00 | 1.00 | 1.00 | 1.04 | 1.00 | 0.61 | 0.41 | 1.00 | 1.00 |
| Serpina1b | 1.00 | 1.00 | 0.89 | 1.03 | 0.76 | 0.72 | 1.01 | 0.54 | 1.00 | 1.00 |
| Serpina1c | 1.00 | 1.00 | 0.86 | 0.69 | 1.20 | 1.13 | 0.45 | 0.23 | 1.00 | 1.37 |
| Serpina1d | 1.00 | 1.00 | 1.00 | 1.00 | 1.00 | 1.00 | 0.96 | 0.55 | 1.00 | 1.00 |
| Serpina1e | 1.00 | 0.96 | 1.00 | 1.00 | 1.00 | 1.00 | 0.90 | 0.95 | 1.00 | 1.00 |
| Serpina1f | 1.00 | 1.00 | 1.00 | 1.00 | 1.00 | 1.00 | 1.00 | 1.00 | 1.00 | 1.00 |
| Serpina3k | 1.00 | 0.51 | 1.00 | 1.00 | 1.00 | 1.00 | 1.00 | 0.13 | 1.00 | 1.02 |
| Serpina3n | 1.05 | 0.87 | 0.98 | 1.04 | 1.39 | 1.71 | 0.93 | 0.99 | 0.99 | 1.42 |
| Serpinb2 | 1.00 | 1.00 | 1.00 | 1.00 | 1.00 | 1.00 | 0.84 | 1.11 | 0.80 | 0.69 |
| Slc17a9 | 1.15 | 1.12 | 1.00 | 1.00 | 1.00 | 1.00 | 1.01 | 0.88 | 1.09 | 0.91 |
| Slc1a1 | 1.00 | 1.00 | 1.02 | 0.93 | 0.93 | 0.97 | 1.35 | 0.99 | 1.00 | 1.00 |
| Slc27a2 | 1.00 | 1.00 | 0.90 | 1.24 | 0.94 | 0.92 | 1.00 | 0.74 | 1.00 | 1.00 |
| Slc35f2 | 1.00 | 1.00 | 1.09 | 1.05 | 0.90 | 0.77 | 1.13 | 0.99 | 1.00 | 1.00 |
| Slc38a5 | 0.81 | 1.43 | 1.00 | 1.00 | 1.13 | 1.21 | 1.00 | 1.00 | 0.62 | 0.78 |
| Slc9a7 | 1.00 | 1.00 | 0.67 | 5.16 | 1.08 | 0.71 | 1.00 | 1.00 | 1.00 | 1.00 |
| Snora16a | 1.00 | 1.00 | 0.17 | 1.00 | 1.00 | 1.57 | 17.82 | 1.69 | 0.61 | 0.03 |
| Snora17 | 1.00 | 1.00 | 7.98 | 1.00 | 1.00 | 1.00 | 14.34 | 0.14 | 1.00 | 1.00 |
| Snora21 | 1.00 | 1.00 | 1.00 | 1.00 | 1.00 | 1.00 | 1.00 | 1.00 | 1.00 | 1.00 |
| Snora28 | 1.00 | 1.00 | 1.00 | 1.00 | 1.00 | 1.00 | 1.00 | 1.00 | 1.00 | 1.00 |
| Snora2b | 1.00 | 1.00 | 1.00 | 1.00 | 1.00 | 25.30 | 1.00 | 1.00 | 1.00 | 1.00 |
| Snora3 | 1.00 | 1.00 | 1.00 | 1.00 | 1.00 | 1.00 | 14.67 | 1.00 | 1.00 | 19.37 |
| Snora30 | 1.00 | 1.00 | 1.00 | 1.00 | 1.00 | 1.00 | 1.00 | 1.00 | 1.00 | 1.00 |
| Snora31 | 1.00 | 1.00 | 1.00 | 1.00 | 1.00 | 1.00 | 1.00 | 33.62 | 1.00 | 0.04 |
| Snora33 | 1.00 | 1.00 | 1.00 | 1.00 | 1.00 | 1.00 | 75.33 | 1.00 | 1.00 | 1.00 |
| Snora34 | 1.00 | 1.00 | 19.25 | 1.00 | 1.00 | 0.03 | 1.00 | 0.06 | 1.00 | 1.00 |
| Snora36b | 1.00 | 1.00 | 1.00 | 1.00 | 1.00 | 1.00 | 1.00 | 1.00 | 1.00 | 1.00 |
| Snora41 | 1.00 | 1.12 | 1.00 | 1.00 | 1.00 | 1.00 | 0.85 | 2.31 | 27.50 | 1.00 |
| Snora43 | 1.00 | 1.00 | 1.00 | 0.19 | 0.19 | 0.17 | 10.44 | 1.13 | 0.22 | 2.65 |
| Snora44 | 1.00 | 1.00 | 1.00 | 1.00 | 1.00 | 0.05 | 1.00 | 1.00 | 1.00 | 1.00 |
| Snora52 | 1.00 | 1.00 | 7.23 | 0.15 | 6.70 | 1.00 | 6.51 | 0.15 | 6.81 | 1.00 |
| Snora5c | 1.00 | 1.00 | 1.00 | 1.00 | 1.00 | 1.00 | 1.00 | 1.00 | 1.00 | 1.00 |
| Snora62 | 1.00 | 1.00 | 1.00 | 1.00 | 1.00 | 1.00 | 1.00 | 1.00 | 1.00 | 1.00 |
| Snora64 | 20.57 | 1.00 | 0.06 | 1.21 | 0.05 | 1.00 | 1.00 | 0.05 | 0.06 | 0.03 |
| Snora65 | 1.00 | 22.85 | 1.17 | 20.91 | 1.01 | 2.31 | 0.43 | 1.00 | 1.00 | 0.34 |
| Snora69 | 1.00 | 1.00 | 1.00 | 1.00 | 1.00 | 1.00 | 0.07 | 1.00 | 1.00 | 1.00 |
| Snora70 | 0.06 | 0.05 | 1.00 | 0.12 | 0.50 | 1.00 | 0.57 | 0.03 | 2.14 | 4.01 |

Fig. 37- 49

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Snora75 | 1.00 | 1.00 | 1.00 | 1.00 | 1.00 | 1.00 | 1.00 | 1.00 | 1.00 | 1.00 | 1.00 | 1.00 |
| Snora78 | 1.00 | 1.83 | 1.00 | 0.33 | 0.12 | 0.26 | 3.28 | 1.00 | 0.48 | 0.71 | 0.44 | 1.00 |
| Snora7a | 1.00 | 1.00 | 1.00 | 1.00 | 1.00 | 12.25 | 1.00 | 1.00 | 1.00 | 1.00 | 8.25 | 1.00 |
| Snora81 | 1.00 | 1.00 | 2.76 | 0.90 | 0.41 | 0.10 | 1.11 | 0.52 | 0.23 | 3.89 | 2.28 | 1.76 |
| Snord15a | 1.00 | 1.00 | 1.00 | 1.00 | 1.00 | 5.52 | 1.00 | 1.00 | 3.75 | 1.00 | 1.00 | 1.00 |
| Snord15b | 1.00 | 1.00 | 1.00 | 1.00 | 0.16 | 1.00 | 1.00 | 1.00 | 1.00 | 1.00 | 1.00 | 1.00 |
| Snord22 | 1.00 | 1.00 | 1.00 | 0.10 | 0.03 | 3.23 | 1.00 | 0.04 | 8.48 | 1.00 | 1.00 | 8.99 |
| Spag11a | 1.00 | 1.00 | 1.00 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 | 1.00 | 1.00 |
| Spin2c | 1.00 | 1.00 | 1.00 | 1.00 | 1.00 | 1.00 | 1.00 | 1.00 | 1.00 | 1.25 | 1.00 | 1.00 |
| Spink11 | 1.00 | 1.00 | 1.00 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 | 1.00 | 1.00 | 1.00 |
| Spink2 | 1.00 | 1.00 | 1.00 | 1.00 | 1.00 | 1.00 | 1.00 | 1.00 | 1.00 | 1.00 | 1.00 | 1.00 |
| Spink5 | 1.00 | 1.00 | 1.00 | 1.00 | 1.00 | 1.00 | 1.00 | 1.00 | 1.00 | 1.00 | 1.00 | 1.00 |
| Spink8 | 1.00 | 1.00 | 1.00 | 1.00 | 1.00 | 1.00 | 1.00 | 1.00 | 1.00 | 1.00 | 1.34 | 1.16 |
| Spint1 | 1.00 | 1.00 | 1.00 | 1.00 | 1.00 | 1.00 | 1.00 | 1.00 | 0.90 | 0.86 | 1.07 | 0.99 |
| Spock1 | 1.00 | 1.00 | 1.00 | 1.00 | 1.00 | 1.00 | 1.00 | 1.00 | 1.00 | 1.00 | 1.00 | 1.00 |
| Srd5a2 | 1.00 | 1.00 | 1.00 | 1.00 | 1.00 | 1.00 | 1.00 | 1.00 | 1.00 | 1.00 | 1.02 | 1.06 |
| St6gal1 | 1.00 | 1.00 | 1.07 | 0.92 | 0.97 | 1.11 | 0.93 | 1.21 | 0.98 | 1.08 | 1.00 | 1.06 |
| Susd4 | 1.00 | 1.00 | 1.00 | 1.00 | 1.00 | 1.00 | 1.00 | 1.00 | 1.26 | 1.15 | 0.73 | 1.53 |
| Sv2c | 1.00 | 1.00 | 1.00 | 1.00 | 1.00 | 1.00 | 1.00 | 1.00 | 1.00 | 1.00 | 1.00 | 1.00 |
| Sycn | 0.70 | 1.61 | 1.00 | 1.00 | 1.00 | 1.00 | 1.00 | 1.08 | 1.00 | 1.34 | 1.54 | 1.14 |
| Sytl4 | 0.77 | 0.63 | 1.00 | 1.00 | 0.86 | 1.04 | 1.11 | 0.99 | 0.94 | 0.93 | 1.07 | 1.15 |
| Tacstd2 | 1.14 | 1.00 | 1.00 | 1.00 | 1.00 | 1.00 | 1.00 | 1.00 | 1.03 | 1.02 | 1.02 | 0.98 |
| Tat | 5.21 | 1.00 | 1.00 | 1.00 | 1.00 | 1.00 | 1.00 | 1.00 | 1.00 | 1.00 | 1.00 | 1.00 |
| Tceal3 | 1.00 | 1.00 | 0.95 | 0.91 | 1.00 | 1.00 | 1.00 | 1.00 | 0.98 | 1.16 | 1.00 | 1.00 |
| Tcf7 | 1.00 | 1.00 | 1.00 | 1.00 | 1.00 | 1.00 | 1.00 | 1.00 | 1.30 | 0.83 | 1.00 | 1.00 |
| Teddm1 | 1.00 | 1.00 | 1.00 | 1.00 | 1.00 | 1.00 | 1.00 | 1.00 | 1.00 | 1.00 | 1.00 | 1.00 |
| Tff2 | 1.00 | 1.00 | 1.00 | 1.00 | 1.00 | 1.00 | 1.00 | 1.00 | 0.84 | 1.76 | 1.00 | 1.00 |
| Tff3 | 1.00 | 1.00 | 1.00 | 1.00 | 1.00 | 1.00 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 1.00 | 1.00 | 1.00 | 1.00 |
| Tgoln2 | 1.00 | 1.00 | 0.42 | 0.69 | 1.00 | 1.00 | 1.44 | 1.19 | 1.00 | 1.00 | 1.00 | 1.00 |
| Tgtp1 | 1.00 | 1.21 | 1.34 | 2.09 | 1.01 | 1.83 | 0.99 | 1.53 | 1.09 | 1.19 | 1.21 | 1.72 |
| Tgtp2 | 0.70 | 1.51 | 1.02 | 1.91 | 1.07 | 1.73 | 0.98 | 1.51 | 1.16 | 1.12 | 1.14 | 1.55 |
| Tm4sf20 | 1.00 | 1.00 | 1.00 | 1.00 | 1.00 | 1.00 | 1.00 | 1.00 | 1.00 | 1.00 | 1.00 | 1.00 |
| Tmem150c | 1.00 | 1.00 | 1.00 | 1.00 | 1.00 | 1.00 | 1.18 | 1.33 | 1.04 | 1.00 | 0.95 | 0.96 |
| Tmem178b | 1.00 | 1.00 | 1.00 | 1.00 | 1.00 | 1.00 | 1.00 | 1.00 | 1.00 | 1.00 | 1.00 | 1.00 |
| Tmem27 | 1.00 | 1.00 | 1.00 | 1.00 | 1.00 | 1.00 | 1.00 | 1.00 | 1.00 | 1.00 | 1.16 | 0.92 |
| Tox3 | 1.00 | 1.00 | 1.00 | 1.00 | 1.00 | 0.93 | 0.87 | 0.99 | 1.09 | 0.95 | 1.13 | 0.76 |
| Tpd52l1 | 1.00 | 1.00 | 1.18 | 0.91 | 0.86 | 1.09 | 0.94 | 0.87 | 1.00 | 1.45 | 1.10 | 0.90 |
| Trf | 7.89 | 1.67 | 1.56 | 1.05 | 0.96 | 0.94 | 1.07 | 1.17 | 0.95 | 1.03 | 1.09 | 1.13 |
| Trim56 | 1.00 | 1.00 | 0.43 | 0.97 | 1.19 | 1.06 | 1.92 | 1.08 | 1.40 | 1.21 | 0.29 | 1.00 |
| Try10 | 1.00 | 1.00 | 1.00 | 1.00 | 1.00 | 1.00 | 1.00 | 1.00 | 1.00 | 1.00 | 1.00 | 1.00 |
| Try4 | 0.58 | 2.35 | 1.00 | 1.00 | 1.00 | 1.00 | 1.00 | 1.01 | 1.00 | 1.29 | 1.00 | 1.25 |
| Try5 | 0.61 | 2.48 | 1.00 | 1.00 | 1.00 | 1.00 | 1.00 | 0.96 | 1.00 | 1.41 | 1.00 | 0.66 |
| Ttr | 12.53 | 1.00 | 1.00 | 1.00 | 1.00 | 1.00 | 1.00 | 1.00 | 1.00 | 1.00 | 1.27 | 0.89 |
| Ucp1 | 1.00 | 1.00 | 5.12 | 0.45 | 1.25 | 1.10 | 10.36 | 4.27 | 1.00 | 1.00 | 1.15 | 1.62 |
| Uhmk1 | 1.00 | 1.00 | 0.59 | 0.92 | 1.10 | 1.46 | 1.63 | 1.35 | 1.47 | 0.99 | 0.45 | 1.20 |
| Vasn | 1.00 | 1.00 | 1.03 | 1.15 | 0.89 | 0.89 | 1.11 | 1.03 | 0.99 | 0.96 | 0.71 | 1.11 |
| Vip | 1.00 | 1.00 | 1.00 | 1.00 | 1.00 | 1.00 | 1.00 | 1.00 | 1.00 | 1.00 | 1.00 | 1.00 |
| Vtn | 6.62 | 1.00 | 0.83 | 1.25 | 1.15 | 1.00 | 0.99 | 1.15 | 0.77 | 0.83 | 1.00 | 1.00 |
| Wfdc10 | 1.00 | 1.00 | 1.00 | 1.00 | 1.00 | 1.00 | 1.00 | 1.00 | 0.94 | 1.05 | 1.00 | 1.00 |
| Wfdc11 | 1.00 | 1.00 | 1.00 | 1.00 | 1.00 | 1.00 | 1.00 | 1.00 | 1.00 | 1.00 | 1.00 | 1.00 |
| Wfdc15b | 1.00 | 1.00 | 1.00 | 1.00 | 1.00 | 1.00 | 1.00 | 1.00 | 1.00 | 1.00 | 1.22 | 0.94 |
| Wfdc2 | 1.00 | 1.00 | 1.00 | 1.00 | 1.00 | 1.00 | 6.60 | 0.92 | 0.87 | 0.94 | 1.26 | 0.94 |
| Wfdc6a | 1.00 | 1.00 | 1.00 | 1.00 | 1.00 | 1.00 | 1.00 | 1.00 | 1.39 | 1.03 | 1.00 | 1.00 |
| Wfdc6b | 1.00 | 1.00 | 1.00 | 1.00 | 1.00 | 1.00 | 1.00 | 1.00 | 0.64 | 0.49 | 1.00 | 1.00 |
| Wfdc8 | 1.00 | 1.00 | 1.00 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 | 1.00 | 1.00 | 1.00 |
| Wwc1 | 1.00 | 1.00 | 1.00 | 1.00 | 1.00 | 1.00 | 1.00 | 1.00 | 0.98 | 1.00 | 0.80 | 1.02 |

Fig. 37- 50

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Snora75 | 1.00 | 1.00 | 1.00 | 1.00 | 1.00 | 0.03 | 1.00 | 1.00 | 1.00 | 1.00 | 14.93 | 1.00 |
| Snora78 | 0.46 | 1.00 | 0.42 | 2.51 | 3.88 | 5.52 | 1.00 | 1.41 | 6.25 | 0.18 | 0.38 | 7.97 |
| Snora7a | 1.00 | 1.00 | 0.04 | 1.00 | 1.00 | 7.96 | 1.00 | 1.00 | 1.00 | 1.00 | 1.00 | 15.81 |
| Snora81 | 0.46 | 1.13 | 2.41 | 1.61 | 0.86 | 0.87 | 0.96 | 0.89 | 2.89 | 0.46 | 1.00 | 8.93 |
| Snord15a | 1.00 | 1.00 | 4.45 | 1.34 | 0.22 | 1.00 | 1.00 | 1.00 | 1.00 | 1.00 | 0.29 | 1.00 |
| Snord15b | 1.00 | 1.00 | 0.21 | 0.17 | 0.07 | 1.95 | 1.00 | 1.00 | 1.00 | 1.00 | 0.27 | 0.75 |
| Snord22 | 0.91 | 1.00 | 0.51 | 0.02 | 0.49 | 4.83 | 0.71 | 7.70 | 7.14 | 1.00 | 1.09 | 0.52 |
| Spag11a | 1.00 | 1.00 | 1.00 | 1.00 | 1.00 | 1.00 | 72.00 | 11.84 | 1.00 | 1.00 | 1.00 | 1.00 |
| Spag11b | 1.00 | 1.00 | 1.00 | 1.00 | 1.00 | 1.00 | 797 | 482 | 1.00 | 1.00 | 1.00 | 1.00 |
| Spin2c | 1.00 | 1.00 | 1.00 | 1.12 | 0.73 | 0.84 | 7.83 | 2.50 | 1.56 | 0.84 | 1.00 | 1.00 |
| Spink11 | 1.00 | 1.00 | 1.00 | 1.00 | 1.00 | 1.00 | 178 | 1.00 | 1.00 | 1.00 | 1.00 | 1.00 |
| Spink12 | 1.00 | 1.00 | 1.00 | 1.00 | 1.00 | 1.60 | 49.02 | 1.00 | 1.00 | 1.00 | 1.00 | 1.00 |
| Spink2 | 1.00 | 1.00 | 1.00 | 1.00 | 1.00 | 1.00 | 194 | 1.00 | 1.22 | 1.08 | 1.00 | 1.00 |
| Spink5 | 1.00 | 1.00 | 1.00 | 1.00 | 0.87 | 0.95 | 22.31 | 1.00 | 1.00 | 1.00 | 1.00 | 1.00 |
| Spink8 | 1.00 | 1.00 | 1.00 | 1.00 | 1.00 | 1.00 | 324 | 6.18 | 1.98 | 2.07 | 1.00 | 1.00 |
| Spint1 | 1.00 | 1.00 | 0.87 | 0.89 | 1.05 | 0.97 | 6.36 | 3.46 | 1.17 | 0.97 | 1.00 | 1.00 |
| Spock1 | 1.00 | 1.00 | 1.09 | 1.00 | 1.00 | 1.00 | 5.73 | 1.00 | 1.00 | 1.00 | 1.00 | 1.00 |
| Srd5a2 | 1.00 | 1.00 | 1.00 | 1.00 | 1.00 | 1.00 | 12.03 | 4.78 | 1.00 | 1.00 | 1.00 | 1.00 |
| St6gal1 | 0.91 | 1.01 | 1.08 | 0.95 | 0.86 | 0.76 | 5.26 | 1.06 | 0.80 | 1.07 | 1.02 | 0.84 |
| Susd4 | 1.03 | 0.77 | 1.00 | 1.00 | 1.00 | 1.00 | 5.54 | 3.71 | 1.00 | 1.00 | 1.00 | 1.00 |
| Sv2c | 1.00 | 1.00 | 1.00 | 1.00 | 1.00 | 1.00 | 1.00 | 1.00 | 1.00 | 1.00 | 1.00 | 1.00 |
| Sycn | 0.40 | 5.74 | 0.79 | 1.16 | 2.79 | 4.25 | 1.00 | 1.00 | 1.00 | 1.00 | 231 | 0.04 |
| Sytl4 | 1.00 | 1.00 | 0.90 | 1.11 | 1.09 | 0.95 | 5.55 | 6.08 | 0.94 | 1.09 | 0.99 | 1.11 |
| Tacstd2 | 1.00 | 1.00 | 1.00 | 1.00 | 0.87 | 0.88 | 6.32 | 1.70 | 1.00 | 1.00 | 1.53 | 1.57 |
| Tat | 1.15 | 0.96 | 0.87 | 0.99 | 0.74 | 1.00 | 1.00 | 1.64 | 1.00 | 1.00 | 1.00 | 1.00 |
| Tceal3 | 1.00 | 1.00 | 0.87 | 0.99 | 0.59 | 1.06 | 4.27 | 5.04 | 1.18 | 1.15 | 1.08 | 1.24 |
| Tcf7 | 0.63 | 0.80 | 1.07 | 1.29 | 1.15 | 1.05 | 5.98 | 3.01 | 0.92 | 1.07 | 1.20 | 0.86 |
| Teddm1 | 1.00 | 1.00 | 1.00 | 1.00 | 1.00 | 1.00 | 20.83 | 240 | 1.00 | 1.00 | 1.00 | 1.00 |
| Tff2 | 1.00 | 1.00 | 2.51 | 2.84 | 1.20 | 1.26 | 1.00 | 1.00 | 1.00 | 1.00 | 8.45 | 0.38 |
| Tff3 | 1.04 | 1.31 | 0.76 | 1.01 | 4.48 | 1.79 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 30.75 | 0.03 | 1.00 | 1.00 |
| Tgoln2 | 1.71 | 0.20 | 5.29 | 1.00 | 0.39 | 5.97 | 1.00 | 1.00 | 0.26 | 1.43 | 1.00 | 1.00 |
| Tgtp1 | 0.80 | 1.30 | 1.21 | 1.21 | 1.41 | 1.56 | 0.78 | 1.28 | 1.00 | 1.00 | 1.14 | 1.24 |
| Tgtp2 | 1.12 | 1.22 | 1.23 | 1.13 | 1.59 | 1.64 | 0.82 | 1.36 | 1.00 | 1.00 | 1.08 | 1.27 |
| Tm4sf20 | 1.00 | 1.00 | 0.88 | 1.30 | 12.77 | 7.79 | 1.00 | 1.00 | 1.00 | 1.00 | 1.00 | 1.00 |
| Tmem150c | 1.00 | 1.00 | 1.00 | 1.00 | 1.00 | 1.00 | 9.49 | 23.90 | 1.32 | 1.08 | 1.00 | 1.09 |
| Tmem178b | 1.00 | 1.00 | 1.00 | 1.00 | 1.00 | 1.00 | 1.00 | 1.00 | 1.26 | 0.99 | 1.00 | 1.00 |
| Tmem27 | 1.00 | 1.00 | 1.00 | 1.00 | 0.71 | 0.92 | 5.02 | 1.14 | 1.00 | 1.00 | 1.00 | 1.00 |
| Tox3 | 1.00 | 1.00 | 0.91 | 1.17 | 1.08 | 1.04 | 6.35 | 1.00 | 1.00 | 1.00 | 1.00 | 1.00 |
| Tpd52l1 | 1.13 | 1.47 | 0.68 | 1.05 | 1.18 | 1.05 | 3.70 | 6.03 | 1.18 | 1.16 | 1.00 | 1.00 |
| Trf | 0.93 | 1.14 | 1.00 | 0.80 | 0.63 | 1.08 | 0.82 | 0.94 | 0.79 | 1.05 | 0.88 | 0.88 |
| Trim56 | 2.28 | 0.30 | 8.42 | 0.93 | 1.10 | 0.90 | 1.04 | 1.13 | 1.00 | 1.00 | 1.16 | 1.04 |
| Try10 | 1.00 | 1.00 | 1.37 | 1.58 | 1.88 | 1.02 | 1.00 | 1.00 | 1.00 | 1.00 | 5.78 | 0.78 |
| Try4 | 0.51 | 13.39 | 2.06 | 196 | 2.68 | 8.20 | 1.00 | 1.00 | 2.53 | 0.83 | 246 | 0.02 |
| Try5 | 0.81 | 10.31 | 1.78 | 155 | 2.58 | 16.79 | 1.00 | 1.00 | 1.28 | 0.75 | 188 | 0.02 |
| Ttr | 0.81 | 1.28 | 0.85 | 0.63 | 1.06 | 0.99 | 1.13 | 3.52 | 1.00 | 1.00 | 1.00 | 1.00 |
| Ucp1 | 1.00 | 1.00 | 1.00 | 1.00 | 1.00 | 1.00 | 1.00 | 1.00 | 1.00 | 1.00 | 1.00 | 1.00 |
| Uhmk1 | 2.67 | 0.24 | 8.28 | 0.91 | 1.18 | 1.14 | 1.06 | 0.97 | 0.45 | 1.07 | 0.88 | 1.16 |
| Vasn | 1.27 | 1.24 | 1.60 | 0.82 | 0.91 | 1.07 | 0.95 | 1.36 | 1.05 | 1.05 | 0.77 | 0.82 |
| Vip | 1.00 | 1.00 | 0.58 | 0.99 | 0.84 | 1.01 | 1.00 | 10.06 | 1.00 | 1.00 | 1.00 | 1.00 |
| Vtn | 0.91 | 1.28 | 1.02 | 0.94 | 0.90 | 1.31 | 0.87 | 0.93 | 1.00 | 1.00 | 1.00 | 1.00 |
| Wfdc10 | 1.00 | 1.00 | 1.00 | 1.00 | 1.10 | 1.00 | 247 | 44.36 | 1.46 | 0.99 | 1.00 | 1.00 |
| Wfdc11 | 1.00 | 1.00 | 1.00 | 1.00 | 1.00 | 1.00 | 5.08 | 1.00 | 1.00 | 1.00 | 1.00 | 1.00 |
| Wfdc15b | 1.00 | 1.00 | 1.00 | 1.00 | 1.34 | 1.85 | 13.19 | 5.58 | 1.00 | 1.00 | 1.00 | 1.00 |
| Wfdc2 | 1.11 | 0.91 | 0.80 | 0.80 | 1.16 | 1.00 | 1.54 | 1.12 | 1.00 | 1.00 | 1.00 | 1.00 |
| Wfdc6a | 1.00 | 1.00 | 1.00 | 1.00 | 1.00 | 1.00 | 7.46 | 1.76 | 1.19 | 0.89 | 1.00 | 1.00 |
| Wfdc6b | 1.00 | 1.00 | 1.00 | 1.00 | 1.00 | 1.00 | 15.27 | 1.00 | 1.48 | 1.31 | 1.00 | 1.00 |
| Wfdc8 | 1.00 | 1.00 | 1.00 | 1.00 | 1.00 | 1.00 | 13.55 | 1.00 | 1.00 | 1.00 | 1.00 | 1.00 |
| Wfdc9 | 1.00 | 1.00 | 1.00 | 1.00 | 1.00 | 1.00 | 20.61 | 1.00 | 1.12 | 1.00 | 1.00 | 1.00 |
| Wwc1 | 1.24 | 0.95 | 1.97 | 1.06 | 1.04 | 1.10 | 5.60 | 2.91 | 1.00 | 0.94 | 1.00 | 1.00 |

Fig. 37-51

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Snora75 | 1.00 | 1.00 | 1.00 | 1.00 | 1.00 | 1.00 | 1.00 | 1.00 | 1.00 | 1.00 |
| Snora78 | 1.00 | 1.00 | 3.07 | 1.00 | 0.17 | 1.00 | 0.15 | 3.27 | 1.00 | 0.18 |
| Snora7a | 1.00 | 11.48 | 1.00 | 0.06 | 8.67 | 1.00 | 1.00 | 1.00 | 8.75 | 1.00 |
| Snora81 | 3.17 | 3.39 | 0.35 | 1.07 | 0.49 | 0.80 | 0.85 | 0.44 | 1.89 | 1.84 |
| Snord15a | 1.00 | 1.00 | 1.00 | 1.00 | 1.00 | 1.00 | 1.00 | 1.00 | 0.15 | 1.00 |
| Snord15b | 5.01 | 1.00 | 1.00 | 1.00 | 0.23 | 1.00 | 0.85 | 1.12 | 1.00 | 1.32 |
| Snord22 | 1.00 | 27.01 | 1.00 | 0.03 | 10.30 | 0.03 | 2.13 | 22.95 | 0.61 | 2.68 |
| Spag11a | 1.00 | 1.00 | 1.00 | 1.00 | 1.00 | 1.00 | 1.00 | 1.00 | 1.00 | 1.00 |
| Spag11b | 1.00 | 1.00 | 1.00 | 1.00 | 1.00 | 1.00 | 1.00 | 1.00 | 1.00 | 1.00 |
| Spin2c | 1.00 | 1.00 | 0.87 | 0.64 | 0.92 | 1.23 | 1.11 | 0.94 | 1.00 | 1.00 |
| Spink11 | 1.00 | 1.00 | 1.00 | 1.00 | 1.00 | 1.00 | 1.00 | 1.00 | 1.00 | 1.00 |
| Spink12 | 1.00 | 1.00 | 1.00 | 1.00 | 1.00 | 1.00 | 1.00 | 1.00 | 1.00 | 1.00 |
| Spink2 | 1.00 | 1.00 | 1.00 | 1.00 | 1.00 | 1.00 | 1.00 | 1.00 | 0.77 | 0.78 |
| Spink5 | 1.00 | 1.00 | 1.00 | 1.00 | 1.00 | 1.00 | 0.99 | 1.00 | 1.00 | 1.00 |
| Spink8 | 1.00 | 1.00 | 0.63 | 0.64 | 0.77 | 0.73 | 1.00 | 1.00 | 1.00 | 1.00 |
| Spint1 | 0.90 | 1.02 | 1.00 | 1.00 | 0.86 | 1.19 | 1.08 | 0.96 | 1.00 | 1.00 |
| Spock1 | 1.00 | 1.00 | 0.96 | 1.30 | 0.91 | 0.99 | 1.00 | 1.00 | 1.00 | 1.00 |
| Srd5a2 | 1.00 | 1.00 | 1.00 | 1.00 | 1.00 | 1.00 | 1.00 | 1.00 | 1.00 | 1.00 |
| St6gal1 | 1.00 | 1.00 | 0.94 | 1.03 | 1.21 | 0.97 | 1.00 | 1.05 | 0.99 | 0.96 |
| Susd4 | 1.00 | 1.00 | 0.93 | 1.57 | 1.04 | 1.05 | 0.79 | 1.38 | 1.00 | 1.00 |
| Sv2c | 1.00 | 1.00 | 0.97 | 6.14 | 1.20 | 0.75 | 1.00 | 1.00 | 1.00 | 1.00 |
| Sycn | 0.95 | 1.03 | 1.52 | 1.00 | 1.00 | 1.32 | 1.15 | 1.55 | 1.12 | 1.00 |
| Sytl4 | 1.00 | 1.05 | 1.18 | 1.33 | 1.06 | 0.88 | 1.00 | 1.03 | 0.65 | 0.88 |
| Tacstd2 | 1.00 | 1.00 | 1.00 | 1.00 | 1.00 | 1.00 | 0.99 | 0.98 | 1.03 | 0.97 |
| Tat | 1.00 | 1.00 | 1.00 | 1.00 | 1.00 | 1.00 | 1.00 | 0.67 | 1.00 | 1.00 |
| Tceal3 | 1.00 | 1.00 | 1.01 | 0.67 | 0.88 | 0.97 | 0.61 | 0.90 | 0.84 | 0.65 |
| Tcf7 | 1.00 | 1.00 | 0.81 | 1.26 | 0.86 | 0.88 | 1.07 | 1.02 | 0.85 | 0.97 |
| Teddm1 | 1.00 | 1.00 | 1.00 | 1.00 | 1.00 | 1.00 | 1.00 | 1.00 | 1.00 | 1.00 |
| Tff2 | 1.00 | 1.23 | 1.00 | 1.00 | 1.00 | 1.00 | 1.00 | 1.00 | 1.00 | 1.00 |
| Tff3 | 1.77 | 8.31 | 1.00 | 1.00 | 1.00 | 1.00 | 1.00 | 1.00 | 1.00 | 1.00 |
| Tgif2lx2 | 1.00 | 1.00 | 1.00 | 1.00 | 1.00 | 1.00 | 1.00 | 1.00 | 1.00 | 1.00 |
| Tgoln2 | 1.00 | 0.85 | 1.00 | 1.69 | 1.00 | 1.00 | 1.00 | 1.00 | 3.87 | 1.00 |
| Tgtp1 | 1.00 | 1.04 | 1.00 | 1.00 | 1.00 | 1.06 | 1.00 | 12.95 | 0.92 | 1.05 |
| Tgtp2 | 1.00 | 1.11 | 1.00 | 1.00 | 1.00 | 1.11 | 1.00 | 7.77 | 0.87 | 1.12 |
| Tm4sf20 | 1.00 | 1.68 | 1.00 | 1.00 | 1.00 | 1.00 | 1.00 | 1.00 | 1.00 | 1.00 |
| Tmem150c | 1.00 | 1.00 | 1.00 | 1.18 | 1.05 | 0.96 | 1.00 | 1.04 | 1.00 | 1.00 |
| Tmem178b | 1.00 | 1.00 | 0.77 | 5.66 | 1.49 | 0.96 | 1.00 | 1.00 | 1.00 | 1.00 |
| Tmem27 | 1.14 | 1.61 | 1.00 | 1.00 | 1.00 | 1.00 | 1.00 | 1.00 | 1.00 | 1.00 |
| Tox3 | 1.00 | 1.00 | 0.90 | 1.05 | 0.97 | 1.04 | 1.00 | 1.00 | 1.00 | 1.00 |
| Tpd52l1 | 1.00 | 1.01 | 0.90 | 0.73 | 0.78 | 0.97 | 1.22 | 0.71 | 1.00 | 1.00 |
| Trf | 0.52 | 0.99 | 0.99 | 1.04 | 1.25 | 1.30 | 1.04 | 0.91 | 0.92 | 0.89 |
| Trim56 | 1.00 | 0.80 | 1.04 | 1.44 | 1.52 | 1.00 | 0.52 | 2.07 | 4.18 | 1.55 |
| Try10 | 0.96 | 1.17 | 1.00 | 1.00 | 1.00 | 1.00 | 1.00 | 1.00 | 1.00 | 1.00 |
| Try4 | 0.91 | 1.10 | 1.50 | 1.86 | 1.00 | 1.24 | 1.00 | 1.14 | 2.49 | 1.00 |
| Try5 | 0.89 | 1.07 | 1.86 | 0.86 | 1.00 | 0.95 | 1.13 | 1.47 | 2.48 | 1.00 |
| Ttr | 0.81 | 0.76 | 0.82 | 0.60 | 1.00 | 0.88 | 1.00 | 0.27 | 1.00 | 1.00 |
| Ucp1 | 1.00 | 1.00 | 1.00 | 1.00 | 1.00 | 1.00 | 1.00 | 1.00 | 1.00 | 1.00 |
| Uhmk1 | 1.00 | 1.00 | 0.76 | 5.67 | 1.33 | 0.78 | 0.66 | 1.66 | 4.65 | 2.15 |
| Vasn | 0.95 | 0.94 | 0.94 | 1.32 | 1.04 | 1.00 | 0.94 | 0.94 | 7.35 | 3.46 |
| Vip | 1.00 | 1.20 | 0.91 | 0.64 | 0.82 | 1.06 | 1.00 | 1.00 | 1.00 | 1.00 |
| Vtn | 0.79 | 1.14 | 1.02 | 0.95 | 0.94 | 0.96 | 1.07 | 0.85 | 1.00 | 1.00 |
| Wfdc10 | 1.00 | 1.00 | 1.00 | 1.00 | 1.00 | 1.00 | 1.00 | 1.00 | 1.00 | 1.00 |
| Wfdc11 | 1.00 | 1.00 | 1.00 | 1.00 | 1.00 | 1.00 | 1.00 | 1.00 | 1.00 | 1.00 |
| Wfdc15b | 1.00 | 1.06 | 1.00 | 1.00 | 1.00 | 1.00 | 1.00 | 1.00 | 1.00 | 1.00 |
| Wfdc2 | 1.00 | 1.59 | 1.00 | 1.00 | 0.94 | 1.00 | 1.17 | 0.80 | 1.00 | 1.00 |
| Wfdc6a | 1.00 | 1.00 | 1.00 | 1.00 | 1.00 | 1.00 | 1.00 | 1.00 | 1.00 | 1.00 |
| Wfdc6b | 1.00 | 1.00 | 1.00 | 1.00 | 1.00 | 1.00 | 1.00 | 1.00 | 1.00 | 1.00 |
| Wfdc8 | 1.00 | 1.00 | 1.00 | 1.00 | 1.00 | 1.00 | 1.00 | 1.00 | 1.00 | 1.00 |
| Wfdc9 | 1.00 | 1.00 | 1.00 | 1.00 | 1.00 | 1.00 | 1.00 | 1.00 | 1.00 | 1.00 |
| Wwc1 | 1.32 | 1.02 | 0.98 | 1.38 | 1.05 | 0.96 | 1.07 | 1.06 | 1.00 | 1.00 |

Fig. 37- 52

| Gene Name | Blood | | Skeletal muscle | | Brown fat | | Heart | | Lung | | Kidney | |
|---|---|---|---|---|---|---|---|---|---|---|---|---|
| | 3d | 7d | 3d | 7d | 3d | 7d | 3d | 7d | 3d | 7d | 3d | 7d |
| Xkrx | 1.00 | 1.00 | 1.00 | 1.00 | 0.76 | 1.88 | 1.00 | 1.00 | 1.00 | 1.00 | 0.69 | 1.00 |
| Zbed6 | 1.00 | 1.00 | 0.58 | 0.79 | 1.00 | 1.00 | 2.05 | 0.91 | 2.33 | 1.31 | 0.91 | 1.00 |
| Zbp1 | 1.00 | 1.00 | 1.00 | 1.00 | 1.00 | 1.00 | 1.00 | 1.81 | 1.12 | 2.64 | 1.00 | 1.00 |
| Zfp369 | 1.00 | 1.00 | 0.53 | 0.72 | 1.00 | 0.83 | 2.32 | 0.89 | 1.42 | 0.95 | 0.63 | 0.91 |
| Zfp648 | 1.00 | 1.00 | 1.00 | 1.00 | 1.00 | 1.00 | 1.00 | 1.00 | 1.00 | 1.00 | 1.00 | 1.00 |
| Zg16 | 0.81 | 1.00 | 1.00 | 1.00 | 1.00 | 1.28 | 1.00 | 0.72 | 1.00 | 1.30 | 1.00 | 0.89 |

Fig. 37- 53

| Gene Name | Liver | | Colon | | Stomach | | Adipose tissue | | Testis | | Spleen | |
|---|---|---|---|---|---|---|---|---|---|---|---|---|
| | 3d | 7d | 3d | 7d | 3d | 7d | 3d | 7d | 3d | 7d | 3d | 7d |
| Xkrx | 1.00 | 1.00 | 1.00 | 1.00 | 0.84 | 0.82 | 6.09 | 1.00 | 1.00 | 1.00 | 0.78 | 0.81 |
| Zbed6 | 3.25 | 0.19 | 13.22 | 1.01 | 1.02 | 1.10 | 1.00 | 1.00 | 0.32 | 1.22 | 0.87 | 1.50 |
| Zbp1 | 1.30 | 1.23 | 0.85 | 0.93 | 0.98 | 1.00 | 0.80 | 1.00 | 0.99 | 1.00 | 1.38 | 1.12 |
| Zfp369 | 2.07 | 0.37 | 5.51 | 0.79 | 0.81 | 1.02 | 0.87 | 1.00 | 1.00 | 1.00 | 0.82 | 1.66 |
| Zfp648 | 1.00 | 1.00 | 1.00 | 1.00 | 1.00 | 1.00 | 11.09 | 1.82 | 1.00 | 1.00 | 1.00 | 1.00 |
| Zg16 | 1.00 | 4.58 | 0.74 | 1.10 | 2.40 | 1.94 | 1.00 | 1.00 | 1.00 | 1.00 | 53.96 | 0.09 |

Fig. 37- 54

| Gene Name | Pancreas | | Left brain | | Right brain | | Ear (skin) | | Bone marrow | |
|---|---|---|---|---|---|---|---|---|---|---|
| | 3d | 7d | 3d | 7d | 3d | 7d | 3d | 7d | 3d | 7d |
| Xkrx | 1.00 | 1.00 | 0.75 | 1.12 | 0.82 | 1.11 | 1.01 | 1.02 | 0.71 | 0.85 |
| Zbed6 | 1.00 | 0.39 | 0.95 | 7.28 | 2.04 | 0.79 | 0.46 | 2.20 | 9.10 | 2.92 |
| Zbp1 | 1.00 | 1.00 | 1.00 | 1.00 | 1.00 | 1.00 | 1.00 | 6.33 | 1.15 | 1.44 |
| Zfp369 | 1.00 | 1.00 | 1.02 | 5.58 | 1.69 | 1.00 | 1.00 | 1.38 | 5.26 | 1.60 |
| Zfp648 | 1.00 | 1.00 | 1.00 | 1.00 | 1.00 | 1.00 | 1.39 | 1.17 | 1.00 | 1.00 |
| Zg16 | 0.80 | 1.13 | 1.96 | 0.59 | 1.00 | 0.84 | 0.67 | 0.95 | 0.92 | 0.51 |

Fig. 38 - 1

| Line No. | Group No. | | | | | Sub-Groups | Gene Name | Breast cancer |
|---|---|---|---|---|---|---|---|---|
| 1 | 3 | 4 | 5 | 6 | 7 | VII-2 | AGSK1 | 0.17 |
| 2 | 3 | 4 | 5 | 6 | 7 | VII-2 | CD70 | 0.16 |
| 3 | 3 | 4 | 5 | 6 | 7 | VII-2 | CRLF1 | 0.17 |
| 4 | 3 | 4 | 5 | 6 | 7 | VII-2 | PAMR1 | 0.18 |
| 5 | 3 | 4 | 5 | 6 | 7 | VII-2 | PRG4 | 0.13 |
| 6 | 3 | 4 | 5 | 6 | 7 | VII-1 | BHMT | 6.14 |
| 7 | 3 | 4 | 5 | 6 | 7 | VII-1 | CCL4L2 | 7.28 |
| 8 | 3 | 4 | 5 | 6 | 7 | VII-1 | CD163 | 5.39 |
| 9 | 3 | 4 | 5 | 6 | 7 | VII-1 | CSF3R | 5.15 |
| 10 | 3 | 4 | 5 | 6 | 7 | VII-1 | CXCL1 | 5.57 |
| 11 | 3 | 4 | 5 | 6 | 7 | VII-1 | ESR1 | 6.01 |
| 12 | 3 | 4 | 5 | 6 | 7 | VII-1 | FCGR3B | 7.18 |
| 13 | 3 | 4 | 5 | 6 | 7 | VII-1 | FGB | 5.45 |
| 14 | 3 | 4 | 5 | 6 | 7 | VII-1 | FGG | 6.00 |
| 15 | 3 | 4 | 5 | 6 | 7 | VII-1 | FGL1 | 6.00 |
| 16 | 3 | 4 | 5 | 6 | 7 | VII-1 | FPR1 | 7.27 |
| 17 | 3 | 4 | 5 | 6 | 7 | VII-1 | HIST1H2BN | 8.41 |
| 18 | 3 | 4 | 5 | 6 | 7 | VII-1 | HLA-DQA1 | 61.86 |
| 19 | 3 | 4 | 5 | 6 | 7 | VII-1 | IL7R | 5.77 |
| 20 | 3 | 4 | 5 | 6 | 7 | VII-1 | IL8 | 9.50 |
| 21 | 3 | 4 | 5 | 6 | 7 | VII-1 | LINC00260 | 5.98 |
| 22 | 3 | 4 | 5 | 6 | 7 | VII-1 | LOC100302650 | 7.46 |
| 23 | 3 | 4 | 5 | 6 | 7 | VII-1 | LOC286437 | 7.22 |
| 24 | 3 | 4 | 5 | 6 | 7 | VII-1 | LUST | 5.29 |
| 25 | 3 | 4 | 5 | 6 | 7 | VII-1 | MALAT1 | 6.53 |
| 26 | 3 | 4 | 5 | 6 | 7 | VII-1 | MIR1184-1 | 76.96 |
| 27 | 3 | 4 | 5 | 6 | 7 | VII-1 | MIR1247 | 7.23 |
| 28 | 3 | 4 | 5 | 6 | 7 | VII-1 | MIR1248 | 27.24 |
| 29 | 3 | 4 | 5 | 6 | 7 | VII-1 | MIR203 | 12.07 |
| 30 | 3 | 4 | 5 | 6 | 7 | VII-1 | MIR205 | 17.04 |
| 31 | 3 | 4 | 5 | 6 | 7 | VII-1 | MIR570 | 197.38 |
| 32 | 3 | 4 | 5 | 6 | 7 | VII-1 | NR4A3 | 5.28 |
| 33 | 3 | 4 | 5 | 6 | 7 | VII-1 | PTPLB | 5.41 |
| 34 | 3 | 4 | 5 | 6 | 7 | VII-1 | RPL21P44 | 6.00 |
| 35 | 3 | 4 | 5 | 6 | 7 | VII-1 | RPPH1 | 24.40 |
| 36 | 3 | 4 | 5 | 6 | 7 | VII-1 | RPS15AP10 | 7.72 |
| 37 | 3 | 4 | 5 | 6 | 7 | VII-1 | SCARNA4 | 15.90 |
| 38 | 3 | 4 | 5 | 6 | 7 | VII-1 | SIM2 | 7.59 |
| 39 | 3 | 4 | 5 | 6 | 7 | VII-1 | SNORA20 | 6.22 |
| 40 | 3 | 4 | 5 | 6 | 7 | VII-1 | SNORA31 | 25.48 |
| 41 | 3 | 4 | 5 | 6 | 7 | VII-1 | SNORA4 | 16.93 |
| 42 | 3 | 4 | 5 | 6 | 7 | VII-1 | SNORA77 | 8.98 |
| 43 | 3 | 4 | 5 | 6 | 7 | VII-1 | TNF | 6.21 |
| 44 | 3 | 4 | 5 | 6 | 7 | VII-1 | ZBTB20 | 6.65 |
| 45 | 3 | 4 | 5 | 6 | 7 | VII-1 | ZNF791 | 5.36 |
| 46 | 3 | 4 | 5 | 6 | | VI-2 | A4GALT | 0.44 |
| 47 | 3 | 4 | 5 | 6 | | VI-2 | ACHE | 0.41 |
| 48 | 3 | 4 | 5 | 6 | | VI-2 | ACTB | 0.50 |
| 49 | 3 | 4 | 5 | 6 | | VI-2 | ACTN4 | 0.46 |
| 50 | 3 | 4 | 5 | 6 | | VI-2 | ADA | 0.44 |
| 51 | 3 | 4 | 5 | 6 | | VI-2 | ADAMTS10 | 0.50 |
| 52 | 3 | 4 | 5 | 6 | | VI-2 | ADAMTS2 | 0.45 |
| 53 | 3 | 4 | 5 | 6 | | VI-2 | ADORA1 | 0.34 |
| 54 | 3 | 4 | 5 | 6 | | VI-2 | AES | 0.47 |
| 55 | 3 | 4 | 5 | 6 | | VI-2 | AGAP3 | 0.49 |
| 56 | 3 | 4 | 5 | 6 | | VI-2 | AGPAT2 | 0.41 |
| 57 | 3 | 4 | 5 | 6 | | VI-2 | ALDH16A1 | 0.47 |
| 58 | 3 | 4 | 5 | 6 | | VI-2 | ALKBH5 | 0.50 |
| 59 | 3 | 4 | 5 | 6 | | VI-2 | ANGPTL2 | 0.48 |
| 60 | 3 | 4 | 5 | 6 | | VI-2 | ANKRD13B | 0.47 |
| 61 | 3 | 4 | 5 | 6 | | VI-2 | ANKRD9 | 0.49 |
| 62 | 3 | 4 | 5 | 6 | | VI-2 | ANXA2 | 0.39 |
| 63 | 3 | 4 | 5 | 6 | | VI-2 | ANXA2P1 | 0.23 |
| 64 | 3 | 4 | 5 | 6 | | VI-2 | ANXA2P3 | 0.38 |
| 65 | 3 | 4 | 5 | 6 | | VI-2 | ANXA8 | 0.41 |
| 66 | 3 | 4 | 5 | 6 | | VI-2 | APLN | 0.26 |
| 67 | 3 | 4 | 5 | 6 | | VI-2 | AQP5 | 0.29 |
| 68 | 3 | 4 | 5 | 6 | | VI-2 | ARHGAP39 | 0.46 |
| 69 | 3 | 4 | 5 | 6 | | VI-2 | ARHGDIA | 0.39 |
| 70 | 3 | 4 | 5 | 6 | | VI-2 | ARL2 | 0.48 |
| 71 | 3 | 4 | 5 | 6 | | VI-2 | ARL8A | 0.47 |
| 72 | 3 | 4 | 5 | 6 | | VI-2 | ASF1B | 0.41 |
| 73 | 3 | 4 | 5 | 6 | | VI-2 | ASS1 | 0.49 |
| 74 | 3 | 4 | 5 | 6 | | VI-2 | ATP13A2 | 0.43 |
| 75 | 3 | 4 | 5 | 6 | | VI-2 | ATP1B2 | 0.48 |
| 76 | 3 | 4 | 5 | 6 | | VI-2 | ATP5L2 | 0.49 |
| 77 | 3 | 4 | 5 | 6 | | VI-2 | ATP6V1B1 | 0.43 |
| 78 | 3 | 4 | 5 | 6 | | VI-2 | ATP6V1F | 0.50 |
| 79 | 3 | 4 | 5 | 6 | | VI-2 | ATXN2L | 0.48 |
| 80 | 3 | 4 | 5 | 6 | | VI-2 | AUP1 | 0.49 |
| 81 | 3 | 4 | 5 | 6 | | VI-2 | BAD | 0.48 |
| 82 | 3 | 4 | 5 | 6 | | VI-2 | BCAN | 0.36 |
| 83 | 3 | 4 | 5 | 6 | | VI-2 | BCAP31 | 0.50 |
| 84 | 3 | 4 | 5 | 6 | | VI-2 | BCAR1 | 0.43 |
| 85 | 3 | 4 | 5 | 6 | | VI-2 | BDKRB2 | 0.41 |
| 86 | 3 | 4 | 5 | 6 | | VI-2 | BIRC5 | 0.35 |
| 87 | 3 | 4 | 5 | 6 | | VI-2 | BTBD2 | 0.46 |
| 88 | 3 | 4 | 5 | 6 | | VI-2 | C16orf13 | 0.49 |
| 89 | 3 | 4 | 5 | 6 | | VI-2 | C16orf74 | 0.25 |
| 90 | 3 | 4 | 5 | 6 | | VI-2 | C17orf58 | 0.43 |
| 91 | 3 | 4 | 5 | 6 | | VI-2 | C17orf61-PLSCR3 | 0.28 |
| 92 | 3 | 4 | 5 | 6 | | VI-2 | C19orf29-AS1 | 0.42 |
| 93 | 3 | 4 | 5 | 6 | | VI-2 | C19orf53 | 0.48 |
| 94 | 3 | 4 | 5 | 6 | | VI-2 | C1QTNF1 | 0.31 |
| 95 | 3 | 4 | 5 | 6 | | VI-2 | C1QTNF2 | 0.34 |
| 96 | 3 | 4 | 5 | 6 | | VI-2 | C1QTNF5 | 0.35 |
| 97 | 3 | 4 | 5 | 6 | | VI-2 | C20orf27 | 0.48 |
| 98 | 3 | 4 | 5 | 6 | | VI-2 | C2orf82 | 0.26 |
| 99 | 3 | 4 | 5 | 6 | | VI-2 | C6orf1 | 0.40 |
| 100 | 3 | 4 | 5 | 6 | | VI-2 | C6orf15 | 0.35 |
| 101 | 3 | 4 | 5 | 6 | | VI-2 | CACNB3 | 0.50 |
| 102 | 3 | 4 | 5 | 6 | | VI-2 | CAPNS1 | 0.44 |
| 103 | 3 | 4 | 5 | 6 | | VI-2 | CARM1 | 0.45 |
| 104 | 3 | 4 | 5 | 6 | | VI-2 | CASKIN2 | 0.48 |
| 105 | 3 | 4 | 5 | 6 | | VI-2 | CCBP2 | 0.34 |
| 106 | 3 | 4 | 5 | 6 | | VI-2 | CCDC101 | 0.46 |
| 107 | 3 | 4 | 5 | 6 | | VI-2 | CCDC102A | 0.47 |
| 108 | 3 | 4 | 5 | 6 | | VI-2 | CCDC163P | 0.25 |
| 109 | 3 | 4 | 5 | 6 | | VI-2 | CCDC42B | 0.40 |
| 110 | 3 | 4 | 5 | 6 | | VI-2 | CCDC64 | 0.44 |
| 111 | 3 | 4 | 5 | 6 | | VI-2 | CCL27 | 0.26 |
| 112 | 3 | 4 | 5 | 6 | | VI-2 | CCNB1 | 0.48 |
| 113 | 3 | 4 | 5 | 6 | | VI-2 | CCNB2 | 0.40 |
| 114 | 3 | 4 | 5 | 6 | | VI-2 | CCNO | 0.39 |
| 115 | 3 | 4 | 5 | 6 | | VI-2 | CD151 | 0.48 |
| 116 | 3 | 4 | 5 | 6 | | VI-2 | CD248 | 0.50 |
| 117 | 3 | 4 | 5 | 6 | | VI-2 | CD276 | 0.39 |
| 118 | 3 | 4 | 5 | 6 | | VI-2 | CD320 | 0.47 |
| 119 | 3 | 4 | 5 | 6 | | VI-2 | CD34 | 0.45 |
| 120 | 3 | 4 | 5 | 6 | | VI-2 | CDC20 | 0.43 |
| 121 | 3 | 4 | 5 | 6 | | VI-2 | CDCA5 | 0.50 |
| 122 | 3 | 4 | 5 | 6 | | VI-2 | CDCA8 | 0.46 |
| 123 | 3 | 4 | 5 | 6 | | VI-2 | CDK16 | 0.47 |
| 124 | 3 | 4 | 5 | 6 | | VI-2 | CDK2AP2 | 0.43 |
| 125 | 3 | 4 | 5 | 6 | | VI-2 | CDT1 | 0.35 |
| 126 | 3 | 4 | 5 | 6 | | VI-2 | CFL1 | 0.45 |
| 127 | 3 | 4 | 5 | 6 | | VI-2 | CHCHD4 | 0.48 |
| 128 | 3 | 4 | 5 | 6 | | VI-2 | CHRM1 | 0.42 |
| 129 | 3 | 4 | 5 | 6 | | VI-2 | CHST7 | 0.42 |
| 130 | 3 | 4 | 5 | 6 | | VI-2 | CIC | 0.48 |
| 131 | 3 | 4 | 5 | 6 | | VI-2 | CIDECP | 0.43 |
| 132 | 3 | 4 | 5 | 6 | | VI-2 | CISD3 | 0.49 |
| 133 | 3 | 4 | 5 | 6 | | VI-2 | CLEC3B | 0.44 |
| 134 | 3 | 4 | 5 | 6 | | VI-2 | CLIP3 | 0.48 |
| 135 | 3 | 4 | 5 | 6 | | VI-2 | COL18A1 | 0.46 |
| 136 | 3 | 4 | 5 | 6 | | VI-2 | COL5A1 | 0.45 |
| 137 | 3 | 4 | 5 | 6 | | VI-2 | COL5A3 | 0.43 |
| 138 | 3 | 4 | 5 | 6 | | VI-2 | COL6A1 | 0.49 |
| 139 | 3 | 4 | 5 | 6 | | VI-2 | CPSF1 | 0.35 |
| 140 | 3 | 4 | 5 | 6 | | VI-2 | CRIP1 | 0.23 |
| 141 | 3 | 4 | 5 | 6 | | VI-2 | CRTC2 | 0.45 |
| 142 | 3 | 4 | 5 | 6 | | VI-2 | CSPG4 | 0.48 |
| 143 | 3 | 4 | 5 | 6 | | VI-2 | CTU1 | 0.46 |
| 144 | 3 | 4 | 5 | 6 | | VI-2 | CTXN1 | 0.32 |
| 145 | 3 | 4 | 5 | 6 | | VI-2 | CX3CL1 | 0.49 |
| 146 | 3 | 4 | 5 | 6 | | VI-2 | CYB5R3 | 0.37 |
| 147 | 3 | 4 | 5 | 6 | | VI-2 | CYP21A1P | 0.26 |
| 148 | 3 | 4 | 5 | 6 | | VI-2 | CYP21A2 | 0.25 |
| 149 | 3 | 4 | 5 | 6 | | VI-2 | DBNDD2 | 0.45 |
| 150 | 3 | 4 | 5 | 6 | | VI-2 | DFNB31 | 0.42 |
| 151 | 3 | 4 | 5 | 6 | | VI-2 | DGCR6 | 0.29 |
| 152 | 3 | 4 | 5 | 6 | | VI-2 | DLK2 | 0.49 |
| 153 | 3 | 4 | 5 | 6 | | VI-2 | DOHH | 0.49 |
| 154 | 3 | 4 | 5 | 6 | | VI-2 | DPM2 | 0.47 |
| 155 | 3 | 4 | 5 | 6 | | VI-2 | DTX1 | 0.44 |
| 156 | 3 | 4 | 5 | 6 | | VI-2 | DUOX1 | 0.45 |
| 157 | 3 | 4 | 5 | 6 | | VI-2 | DYNLRB1 | 0.47 |
| 158 | 3 | 4 | 5 | 6 | | VI-2 | ECE1 | 0.48 |
| 159 | 3 | 4 | 5 | 6 | | VI-2 | EDN1 | 0.27 |
| 160 | 3 | 4 | 5 | 6 | | VI-2 | EEF1D | 0.49 |
| 161 | 3 | 4 | 5 | 6 | | VI-2 | EFNB3 | 0.47 |
| 162 | 3 | 4 | 5 | 6 | | VI-2 | EHD2 | 0.38 |
| 163 | 3 | 4 | 5 | 6 | | VI-2 | EHMT2 | 0.44 |
| 164 | 3 | 4 | 5 | 6 | | VI-2 | ELMO3 | 0.48 |
| 165 | 3 | 4 | 5 | 6 | | VI-2 | ELN | 0.27 |
| 166 | 3 | 4 | 5 | 6 | | VI-2 | EML3 | 0.48 |
| 167 | 3 | 4 | 5 | 6 | | VI-2 | EMP3 | 0.43 |
| 168 | 3 | 4 | 5 | 6 | | VI-2 | ENG | 0.38 |
| 169 | 3 | 4 | 5 | 6 | | VI-2 | EPCAM | 0.49 |
| 170 | 3 | 4 | 5 | 6 | | VI-2 | ERI3 | 0.47 |
| 171 | 3 | 4 | 5 | 6 | | VI-2 | EVPL | 0.48 |
| 172 | 3 | 4 | 5 | 6 | | VI-2 | EXOC3L2 | 0.45 |
| 173 | 3 | 4 | 5 | 6 | | VI-2 | F8A1 | 0.40 |
| 174 | 3 | 4 | 5 | 6 | | VI-2 | FAAH | 0.41 |
| 175 | 3 | 4 | 5 | 6 | | VI-2 | FAM127A | 0.48 |
| 176 | 3 | 4 | 5 | 6 | | VI-2 | FAM158A | 0.46 |
| 177 | 3 | 4 | 5 | 6 | | VI-2 | FAM180B | 0.49 |
| 178 | 3 | 4 | 5 | 6 | | VI-2 | FAM189B | 0.44 |
| 179 | 3 | 4 | 5 | 6 | | VI-2 | FAM195B | 0.49 |
| 180 | 3 | 4 | 5 | 6 | | VI-2 | FAM19A5 | 0.48 |
| 181 | 3 | 4 | 5 | 6 | | VI-2 | FAM203A | 0.47 |
| 182 | 3 | 4 | 5 | 6 | | VI-2 | FAM20C | 0.45 |
| 183 | 3 | 4 | 5 | 6 | | VI-2 | FAM211B | 0.46 |
| 184 | 3 | 4 | 5 | 6 | | VI-2 | FAM213B | 0.46 |
| 185 | 3 | 4 | 5 | 6 | | VI-2 | FAM27B | 0.48 |
| 186 | 3 | 4 | 5 | 6 | | VI-2 | FAM69C | 0.44 |
| 187 | 3 | 4 | 5 | 6 | | VI-2 | FAM89B | 0.46 |
| 188 | 3 | 4 | 5 | 6 | | VI-2 | FBXL19 | 0.44 |
| 189 | 3 | 4 | 5 | 6 | | VI-2 | FBXO2 | 0.41 |
| 190 | 3 | 4 | 5 | 6 | | VI-2 | FGFBP1 | 0.28 |

Fig. 38 - 2

| | | | | | | | | | | | | | | | |
|---|---|---|---|---|---|---|---|---|---|---|---|---|---|---|---|
| 191 | 3 | 4 | 5 | 6 | | VI-2 | FIZ1 | 0.46 | 287 | 3 | 4 | 5 | 6 | VI-2 | MLANA | 0.46 |
| 192 | 3 | 4 | 5 | 6 | | VI-2 | FJX1 | 0.38 | 288 | 3 | 4 | 5 | 6 | VI-2 | MLF2 | 0.48 |
| 193 | 3 | 4 | 5 | 6 | | VI-2 | FKBP1AP1 | 0.45 | 289 | 3 | 4 | 5 | 6 | VI-2 | MMP15 | 0.34 |
| 194 | 3 | 4 | 5 | 6 | | VI-2 | FLT3LG | 0.41 | 290 | 3 | 4 | 5 | 6 | VI-2 | MMP28 | 0.35 |
| 195 | 3 | 4 | 5 | 6 | | VI-2 | FOXP4 | 0.34 | 291 | 3 | 4 | 5 | 6 | VI-2 | MRPL24 | 0.47 |
| 196 | 3 | 4 | 5 | 6 | | VI-2 | FOXS1 | 0.31 | 292 | 3 | 4 | 5 | 6 | VI-2 | MRPL4 | 0.46 |
| 197 | 3 | 4 | 5 | 6 | | VI-2 | FUZ | 0.47 | 293 | 3 | 4 | 5 | 6 | VI-2 | MSN | 0.48 |
| 198 | 3 | 4 | 5 | 6 | | VI-2 | FXYD5 | 0.40 | 294 | 3 | 4 | 5 | 6 | VI-2 | MSX1 | 0.49 |
| 199 | 3 | 4 | 5 | 6 | | VI-2 | G6PC3 | 0.47 | 295 | 3 | 4 | 5 | 6 | VI-2 | MT1E | 0.37 |
| 200 | 3 | 4 | 5 | 6 | | VI-2 | GADD45GIP1 | 0.45 | 296 | 3 | 4 | 5 | 6 | VI-2 | MT1G | 0.40 |
| 201 | 3 | 4 | 5 | 6 | | VI-2 | GAL3ST4 | 0.45 | 297 | 3 | 4 | 5 | 6 | VI-2 | MT1H | 0.40 |
| 202 | 3 | 4 | 5 | 6 | | VI-2 | GALE | 0.44 | 298 | 3 | 4 | 5 | 6 | VI-2 | MT2A | 0.26 |
| 203 | 3 | 4 | 5 | 6 | | VI-2 | GAPDH | 0.39 | 299 | 3 | 4 | 5 | 6 | VI-2 | MUC7 | 0.36 |
| 204 | 3 | 4 | 5 | 6 | | VI-2 | GAS2L1 | 0.37 | 300 | 3 | 4 | 5 | 6 | VI-2 | MYADM | 0.45 |
| 205 | 3 | 4 | 5 | 6 | | VI-2 | GDF10 | 0.49 | 301 | 3 | 4 | 5 | 6 | VI-2 | MYBL2 | 0.34 |
| 206 | 3 | 4 | 5 | 6 | | VI-2 | GDPD5 | 0.50 | 302 | 3 | 4 | 5 | 6 | VI-2 | NACAD | 0.48 |
| 207 | 3 | 4 | 5 | 6 | | VI-2 | GFPT2 | 0.47 | 303 | 3 | 4 | 5 | 6 | VI-2 | NCKAP5L | 0.38 |
| 208 | 3 | 4 | 5 | 6 | | VI-2 | GGT1 | 0.50 | 304 | 3 | 4 | 5 | 6 | VI-2 | NDUFS7 | 0.49 |
| 209 | 3 | 4 | 5 | 6 | | VI-2 | GINS2 | 0.42 | 305 | 3 | 4 | 5 | 6 | VI-2 | NELF | 0.47 |
| 210 | 3 | 4 | 5 | 6 | | VI-2 | GIT1 | 0.43 | 306 | 3 | 4 | 5 | 6 | VI-2 | NFKBIL1 | 0.50 |
| 211 | 3 | 4 | 5 | 6 | | VI-2 | GJA4 | 0.30 | 307 | 3 | 4 | 5 | 6 | VI-2 | NGEF | 0.39 |
| 212 | 3 | 4 | 5 | 6 | | VI-2 | GJA5 | 0.47 | 308 | 3 | 4 | 5 | 6 | VI-2 | NGFR | 0.47 |
| 213 | 3 | 4 | 5 | 6 | | VI-2 | GLIS2 | 0.38 | 309 | 3 | 4 | 5 | 6 | VI-2 | NINJ2 | 0.43 |
| 214 | 3 | 4 | 5 | 6 | | VI-2 | GLTSCR1 | 0.39 | 310 | 3 | 4 | 5 | 6 | VI-2 | NKD2 | 0.39 |
| 215 | 3 | 4 | 5 | 6 | | VI-2 | GMPR | 0.35 | 311 | 3 | 4 | 5 | 6 | VI-2 | NNMT | 0.44 |
| 216 | 3 | 4 | 5 | 6 | | VI-2 | GPBAR1 | 0.40 | 312 | 3 | 4 | 5 | 6 | VI-2 | NOSIP | 0.50 |
| 217 | 3 | 4 | 5 | 6 | | VI-2 | GPI | 0.44 | 313 | 3 | 4 | 5 | 6 | VI-2 | NOVA2 | 0.44 |
| 218 | 3 | 4 | 5 | 6 | | VI-2 | GPR137 | 0.47 | 314 | 3 | 4 | 5 | 6 | VI-2 | NPRL3 | 0.43 |
| 219 | 3 | 4 | 5 | 6 | | VI-2 | GPR143 | 0.34 | 315 | 3 | 4 | 5 | 6 | VI-2 | NRM | 0.37 |
| 220 | 3 | 4 | 5 | 6 | | VI-2 | GPX4 | 0.42 | 316 | 3 | 4 | 5 | 6 | VI-2 | NT5DC2 | 0.41 |
| 221 | 3 | 4 | 5 | 6 | | VI-2 | GRAMD1A | 0.48 | 317 | 3 | 4 | 5 | 6 | VI-2 | NUBP2 | 0.48 |
| 222 | 3 | 4 | 5 | 6 | | VI-2 | GRK5 | 0.43 | 318 | 3 | 4 | 5 | 6 | VI-2 | NUDT1 | 0.45 |
| 223 | 3 | 4 | 5 | 6 | | VI-2 | GRM2 | 0.42 | 319 | 3 | 4 | 5 | 6 | VI-2 | NUTF2 | 0.27 |
| 224 | 3 | 4 | 5 | 6 | | VI-2 | GSTP1 | 0.49 | 320 | 3 | 4 | 5 | 6 | VI-2 | OCEL1 | 0.42 |
| 225 | 3 | 4 | 5 | 6 | | VI-2 | GSTT1 | 0.41 | 321 | 3 | 4 | 5 | 6 | VI-2 | OGFR | 0.47 |
| 226 | 3 | 4 | 5 | 6 | | VI-2 | GSTT2B | 0.47 | 322 | 3 | 4 | 5 | 6 | VI-2 | OLFM2 | 0.33 |
| 227 | 3 | 4 | 5 | 6 | | VI-2 | GTF2F1 | 0.50 | 323 | 3 | 4 | 5 | 6 | VI-2 | OTUB1 | 0.47 |
| 228 | 3 | 4 | 5 | 6 | | VI-2 | H1FX | 0.42 | 324 | 3 | 4 | 5 | 6 | VI-2 | PACS1 | 0.46 |
| 229 | 3 | 4 | 5 | 6 | | VI-2 | HCFC1R1 | 0.42 | 325 | 3 | 4 | 5 | 6 | VI-2 | PACSIN3 | 0.48 |
| 230 | 3 | 4 | 5 | 6 | | VI-2 | HDGF | 0.46 | 326 | 3 | 4 | 5 | 6 | VI-2 | PALM | 0.37 |
| 231 | 3 | 4 | 5 | 6 | | VI-2 | HEXIM2 | 0.39 | 327 | 3 | 4 | 5 | 6 | VI-2 | PAQR4 | 0.35 |
| 232 | 3 | 4 | 5 | 6 | | VI-2 | HEY1 | 0.46 | 328 | 3 | 4 | 5 | 6 | VI-2 | PARD6A | 0.49 |
| 233 | 3 | 4 | 5 | 6 | | VI-2 | HLA-C | 0.45 | 329 | 3 | 4 | 5 | 6 | VI-2 | PCSK1N | 0.28 |
| 234 | 3 | 4 | 5 | 6 | | VI-2 | HNRNPL | 0.35 | 330 | 3 | 4 | 5 | 6 | VI-2 | PDGFB | 0.44 |
| 235 | 3 | 4 | 5 | 6 | | VI-2 | HSD3B7 | 0.35 | 331 | 3 | 4 | 5 | 6 | VI-2 | PDLIM1 | 0.26 |
| 236 | 3 | 4 | 5 | 6 | | VI-2 | HSF1 | 0.49 | 332 | 3 | 4 | 5 | 6 | VI-2 | PDLIM4 | 0.35 |
| 237 | 3 | 4 | 5 | 6 | | VI-2 | ICAM2 | 0.40 | 333 | 3 | 4 | 5 | 6 | VI-2 | PELP1 | 0.46 |
| 238 | 3 | 4 | 5 | 6 | | VI-2 | IFI6 | 0.40 | 334 | 3 | 4 | 5 | 6 | VI-2 | PFN1 | 0.49 |
| 239 | 3 | 4 | 5 | 6 | | VI-2 | IGFBP2 | 0.49 | 335 | 3 | 4 | 5 | 6 | VI-2 | PHB | 0.46 |
| 240 | 3 | 4 | 5 | 6 | | VI-2 | IGFBP6 | 0.40 | 336 | 3 | 4 | 5 | 6 | VI-2 | PIGF | 0.44 |
| 241 | 3 | 4 | 5 | 6 | | VI-2 | IMPDH1 | 0.49 | 337 | 3 | 4 | 5 | 6 | VI-2 | PIP5K1C | 0.46 |
| 242 | 3 | 4 | 5 | 6 | | VI-2 | INF2 | 0.45 | 338 | 3 | 4 | 5 | 6 | VI-2 | PITPNM1 | 0.44 |
| 243 | 3 | 4 | 5 | 6 | | VI-2 | INHA | 0.45 | 339 | 3 | 4 | 5 | 6 | VI-2 | PLAT | 0.48 |
| 244 | 3 | 4 | 5 | 6 | | VI-2 | INPP5J | 0.49 | 340 | 3 | 4 | 5 | 6 | VI-2 | PLCB3 | 0.47 |
| 245 | 3 | 4 | 5 | 6 | | VI-2 | IPO4 | 0.49 | 341 | 3 | 4 | 5 | 6 | VI-2 | PLEC | 0.48 |
| 246 | 3 | 4 | 5 | 6 | | VI-2 | IRAK1 | 0.49 | 342 | 3 | 4 | 5 | 6 | VI-2 | PLEK2 | 0.46 |
| 247 | 3 | 4 | 5 | 6 | | VI-2 | ITGA11 | 0.43 | 343 | 3 | 4 | 5 | 6 | VI-2 | PLOD3 | 0.48 |
| 248 | 3 | 4 | 5 | 6 | | VI-2 | ITGA3 | 0.39 | 344 | 3 | 4 | 5 | 6 | VI-2 | PML | 0.48 |
| 249 | 3 | 4 | 5 | 6 | | VI-2 | ITGB4 | 0.35 | 345 | 3 | 4 | 5 | 6 | VI-2 | POMZP3 | 0.39 |
| 250 | 3 | 4 | 5 | 6 | | VI-2 | KANSL1-AS1 | 0.41 | 346 | 3 | 4 | 5 | 6 | VI-2 | PPAP2C | 0.40 |
| 251 | 3 | 4 | 5 | 6 | | VI-2 | KDELR1 | 0.48 | 347 | 3 | 4 | 5 | 6 | VI-2 | PPDPF | 0.33 |
| 252 | 3 | 4 | 5 | 6 | | VI-2 | KDM5B-AS1 | 0.48 | 348 | 3 | 4 | 5 | 6 | VI-2 | PPP1R14B | 0.47 |
| 253 | 3 | 4 | 5 | 6 | | VI-2 | KIFC1 | 0.40 | 349 | 3 | 4 | 5 | 6 | VI-2 | PPP1R16A | 0.45 |
| 254 | 3 | 4 | 5 | 6 | | VI-2 | KLC2 | 0.41 | 350 | 3 | 4 | 5 | 6 | VI-2 | PPP1R1B | 0.40 |
| 255 | 3 | 4 | 5 | 6 | | VI-2 | KRT14 | 0.30 | 351 | 3 | 4 | 5 | 6 | VI-2 | PQBP1 | 0.49 |
| 256 | 3 | 4 | 5 | 6 | | VI-2 | KRT31 | 0.50 | 352 | 3 | 4 | 5 | 6 | VI-2 | PRAF2 | 0.46 |
| 257 | 3 | 4 | 5 | 6 | | VI-2 | KRT5 | 0.29 | 353 | 3 | 4 | 5 | 6 | VI-2 | PRDX5 | 0.50 |
| 258 | 3 | 4 | 5 | 6 | | VI-2 | KRT6C | 0.39 | 354 | 3 | 4 | 5 | 6 | VI-2 | PRICKLE3 | 0.49 |
| 259 | 3 | 4 | 5 | 6 | | VI-2 | L1CAM | 0.41 | 355 | 3 | 4 | 5 | 6 | VI-2 | PRKACG | 0.34 |
| 260 | 3 | 4 | 5 | 6 | | VI-2 | LAMB2P1 | 0.44 | 356 | 3 | 4 | 5 | 6 | VI-2 | PRKAR1B | 0.40 |
| 261 | 3 | 4 | 5 | 6 | | VI-2 | LAMB3 | 0.40 | 357 | 3 | 4 | 5 | 6 | VI-2 | PRKD2 | 0.50 |
| 262 | 3 | 4 | 5 | 6 | | VI-2 | LAMC2 | 0.34 | 358 | 3 | 4 | 5 | 6 | VI-2 | PRMT1 | 0.46 |
| 263 | 3 | 4 | 5 | 6 | | VI-2 | LGALS2 | 0.38 | 359 | 3 | 4 | 5 | 6 | VI-2 | PRR12 | 0.46 |
| 264 | 3 | 4 | 5 | 6 | | VI-2 | LIMK1 | 0.49 | 360 | 3 | 4 | 5 | 6 | VI-2 | PRR7 | 0.26 |
| 265 | 3 | 4 | 5 | 6 | | VI-2 | LINC00116 | 0.50 | 361 | 3 | 4 | 5 | 6 | VI-2 | PRRX2 | 0.43 |
| 266 | 3 | 4 | 5 | 6 | | VI-2 | LMX1B | 0.44 | 362 | 3 | 4 | 5 | 6 | VI-2 | PSORS1C1 | 0.43 |
| 267 | 3 | 4 | 5 | 6 | | VI-2 | LOC113230 | 0.37 | 363 | 3 | 4 | 5 | 6 | VI-2 | PTMA | 0.47 |
| 268 | 3 | 4 | 5 | 6 | | VI-2 | LOC151534 | 0.49 | 364 | 3 | 4 | 5 | 6 | VI-2 | PTMS | 0.32 |
| 269 | 3 | 4 | 5 | 6 | | VI-2 | LOC152217 | 0.48 | 365 | 3 | 4 | 5 | 6 | VI-2 | PTOV1 | 0.47 |
| 270 | 3 | 4 | 5 | 6 | | VI-2 | LOC255130 | 0.33 | 366 | 3 | 4 | 5 | 6 | VI-2 | PTPN23 | 0.41 |
| 271 | 3 | 4 | 5 | 6 | | VI-2 | LOC283788 | 0.44 | 367 | 3 | 4 | 5 | 6 | VI-2 | PTRF | 0.45 |
| 272 | 3 | 4 | 5 | 6 | | VI-2 | LOC284889 | 0.42 | 368 | 3 | 4 | 5 | 6 | VI-2 | PTTG1 | 0.31 |
| 273 | 3 | 4 | 5 | 6 | | VI-2 | LOC644172 | 0.44 | 369 | 3 | 4 | 5 | 6 | VI-2 | PTTG3P | 0.49 |
| 274 | 3 | 4 | 5 | 6 | | VI-2 | LPCAT4 | 0.40 | 370 | 3 | 4 | 5 | 6 | VI-2 | PVRL2 | 0.49 |
| 275 | 3 | 4 | 5 | 6 | | VI-2 | LRRC23 | 0.49 | 371 | 3 | 4 | 5 | 6 | VI-2 | R3HDM4 | 0.45 |
| 276 | 3 | 4 | 5 | 6 | | VI-2 | LRRC26 | 0.35 | 372 | 3 | 4 | 5 | 6 | VI-2 | RAB11B | 0.46 |
| 277 | 3 | 4 | 5 | 6 | | VI-2 | LRRC45 | 0.50 | 373 | 3 | 4 | 5 | 6 | VI-2 | RAD23A | 0.45 |
| 278 | 3 | 4 | 5 | 6 | | VI-2 | LY6K | 0.49 | 374 | 3 | 4 | 5 | 6 | VI-2 | RALGDS | 0.46 |
| 279 | 3 | 4 | 5 | 6 | | VI-2 | LYPLA2 | 0.48 | 375 | 3 | 4 | 5 | 6 | VI-2 | RALY | 0.50 |
| 280 | 3 | 4 | 5 | 6 | | VI-2 | MAP3K10 | 0.45 | 376 | 3 | 4 | 5 | 6 | VI-2 | RAMP2 | 0.49 |
| 281 | 3 | 4 | 5 | 6 | | VI-2 | MAPK8IP1 | 0.36 | 377 | 3 | 4 | 5 | 6 | VI-2 | RARA | 0.40 |
| 282 | 3 | 4 | 5 | 6 | | VI-2 | MARCH9 | 0.46 | 378 | 3 | 4 | 5 | 6 | VI-2 | RAVER1 | 0.47 |
| 283 | 3 | 4 | 5 | 6 | | VI-2 | METTL1 | 0.44 | 379 | 3 | 4 | 5 | 6 | VI-2 | REM1 | 0.24 |
| 284 | 3 | 4 | 5 | 6 | | VI-2 | MFSD2A | 0.45 | 380 | 3 | 4 | 5 | 6 | VI-2 | REXO1 | 0.50 |
| 285 | 3 | 4 | 5 | 6 | | VI-2 | MIB2 | 0.45 | 381 | 3 | 4 | 5 | 6 | VI-2 | RGS14 | 0.46 |
| 286 | 3 | 4 | 5 | 6 | | VI-2 | MKL1 | 0.49 | 382 | 3 | 4 | 5 | 6 | VI-2 | RHCG | 0.49 |

Fig. 38 - 3

| | | | | | | | | | | | | | | | |
|---|---|---|---|---|---|---|---|---|---|---|---|---|---|---|---|
| 383 | 3 | 4 | 5 | 6 | | VI-2 | RHOB | 0.40 | 479 | 3 | 4 | 5 | 6 | VI-2 | WDR34 | 0.40 |
| 384 | 3 | 4 | 5 | 6 | | VI-2 | RIN1 | 0.41 | 480 | 3 | 4 | 5 | 6 | VI-2 | WNT10A | 0.34 |
| 385 | 3 | 4 | 5 | 6 | | VI-2 | RNASEH2A | 0.43 | 481 | 3 | 4 | 5 | 6 | VI-2 | WNT6 | 0.30 |
| 386 | 3 | 4 | 5 | 6 | | VI-2 | RNF126P1 | 0.41 | 482 | 3 | 4 | 5 | 6 | VI-2 | XRCC6BP1 | 0.41 |
| 387 | 3 | 4 | 5 | 6 | | VI-2 | RNF208 | 0.43 | 483 | 3 | 4 | 5 | 6 | VI-2 | YIF1B | 0.47 |
| 388 | 3 | 4 | 5 | 6 | | VI-2 | RPL12 | 0.45 | 484 | 3 | 4 | 5 | 6 | VI-2 | ZFPL1 | 0.49 |
| 389 | 3 | 4 | 5 | 6 | | VI-2 | RPP25 | 0.44 | 485 | 3 | 4 | 5 | 6 | VI-2 | ZNF205 | 0.41 |
| 390 | 3 | 4 | 5 | 6 | | VI-2 | RPS4X | 0.50 | 486 | 3 | 4 | 5 | 6 | VI-2 | ZNF358 | 0.47 |
| 391 | 3 | 4 | 5 | 6 | | VI-2 | RPUSD1 | 0.49 | 487 | 3 | 4 | 5 | 6 | VI-2 | ZNF362 | 0.49 |
| 392 | 3 | 4 | 5 | 6 | | VI-2 | RRP9 | 0.47 | 488 | 3 | 4 | 5 | 6 | VI-2 | ZNF414 | 0.49 |
| 393 | 3 | 4 | 5 | 6 | | VI-2 | RTEL1-TNFRSF6B | 0.49 | 489 | 3 | 4 | 5 | 6 | VI-2 | ZNF423 | 0.49 |
| 394 | 3 | 4 | 5 | 6 | | VI-2 | RUNDC3A | 0.47 | 490 | 3 | 4 | 5 | 6 | VI-2 | ZNF48 | 0.47 |
| 395 | 3 | 4 | 5 | 6 | | VI-2 | S100A11 | 0.39 | 491 | 3 | 4 | 5 | 6 | VI-2 | ZNF487P | 0.49 |
| 396 | 3 | 4 | 5 | 6 | | VI-2 | S100A2 | 0.27 | 492 | 3 | 4 | 5 | 6 | VI-2 | ZNF575 | 0.42 |
| 397 | 3 | 4 | 5 | 6 | | VI-2 | S100B | 0.50 | 493 | 3 | 4 | 5 | 6 | VI-2 | ZNF598 | 0.48 |
| 398 | 3 | 4 | 5 | 6 | | VI-2 | SARS2 | 0.49 | 494 | 3 | 4 | 5 | 6 | VI-2 | ZNF668 | 0.46 |
| 399 | 3 | 4 | 5 | 6 | | VI-2 | SCAMP4 | 0.49 | 495 | 3 | 4 | 5 | 6 | VI-2 | ZNF768 | 0.45 |
| 400 | 3 | 4 | 5 | 6 | | VI-2 | SCAND1 | 0.46 | 496 | 3 | 4 | 5 | 6 | VI-2 | ZNF775 | 0.46 |
| 401 | 3 | 4 | 5 | 6 | | VI-2 | SCLY | 0.46 | 497 | 3 | 4 | 5 | 6 | VI-2 | ZNF787 | 0.45 |
| 402 | 3 | 4 | 5 | 6 | | VI-2 | SEPW1 | 0.46 | 498 | 3 | 4 | 5 | 6 | VI-2 | ZWINT | 0.49 |
| 403 | 3 | 4 | 5 | 6 | | VI-2 | SERPINE1 | 0.41 | 499 | 3 | 4 | 5 | 6 | VI-1 | ABCA10 | 2.63 |
| 404 | 3 | 4 | 5 | 6 | | VI-2 | SETD1A | 0.47 | 500 | 3 | 4 | 5 | 6 | VI-1 | ABCA6 | 2.28 |
| 405 | 3 | 4 | 5 | 6 | | VI-2 | SF3A2 | 0.36 | 501 | 3 | 4 | 5 | 6 | VI-1 | ABCA8 | 2.29 |
| 406 | 3 | 4 | 5 | 6 | | VI-2 | SF3B4 | 0.45 | 502 | 3 | 4 | 5 | 6 | VI-1 | ACSS3 | 2.01 |
| 407 | 3 | 4 | 5 | 6 | | VI-2 | SFRP4 | 0.33 | 503 | 3 | 4 | 5 | 6 | VI-1 | ADAM10 | 2.27 |
| 408 | 3 | 4 | 5 | 6 | | VI-2 | SFTPD | 0.44 | 504 | 3 | 4 | 5 | 6 | VI-1 | ADAMTSL1 | 2.31 |
| 409 | 3 | 4 | 5 | 6 | | VI-2 | SH2D3A | 0.42 | 505 | 3 | 4 | 5 | 6 | VI-1 | ADH4 | 2.27 |
| 410 | 3 | 4 | 5 | 6 | | VI-2 | SIRT2 | 0.44 | 506 | 3 | 4 | 5 | 6 | VI-1 | ADRA1A | 3.02 |
| 411 | 3 | 4 | 5 | 6 | | VI-2 | SIRT6 | 0.42 | 507 | 3 | 4 | 5 | 6 | VI-1 | AKAP9 | 3.18 |
| 412 | 3 | 4 | 5 | 6 | | VI-2 | SLC13A2 | 0.34 | 508 | 3 | 4 | 5 | 6 | VI-1 | ALDOB | 2.80 |
| 413 | 3 | 4 | 5 | 6 | | VI-2 | SLC17A7 | 0.42 | 509 | 3 | 4 | 5 | 6 | VI-1 | ANKRD12 | 3.66 |
| 414 | 3 | 4 | 5 | 6 | | VI-2 | SLC25A19 | 0.44 | 510 | 3 | 4 | 5 | 6 | VI-1 | ANKRD18B | 2.53 |
| 415 | 3 | 4 | 5 | 6 | | VI-2 | SLC25A39 | 0.49 | 511 | 3 | 4 | 5 | 6 | VI-1 | ANKRD26 | 2.20 |
| 416 | 3 | 4 | 5 | 6 | | VI-2 | SLC27A3 | 0.45 | 512 | 3 | 4 | 5 | 6 | VI-1 | ANKRD36 | 2.03 |
| 417 | 3 | 4 | 5 | 6 | | VI-2 | SLC29A1 | 0.42 | 513 | 3 | 4 | 5 | 6 | VI-1 | ANKRD44 | 2.10 |
| 418 | 3 | 4 | 5 | 6 | | VI-2 | SLC9A1 | 0.46 | 514 | 3 | 4 | 5 | 6 | VI-1 | ARRDC4 | 2.04 |
| 419 | 3 | 4 | 5 | 6 | | VI-2 | SLC9A3 | 0.47 | 515 | 3 | 4 | 5 | 6 | VI-1 | ASIP | 2.11 |
| 420 | 3 | 4 | 5 | 6 | | VI-2 | SNAPC2 | 0.44 | 516 | 3 | 4 | 5 | 6 | VI-1 | ATE1 | 2.40 |
| 421 | 3 | 4 | 5 | 6 | | VI-2 | SNORA64 | 0.50 | 517 | 3 | 4 | 5 | 6 | VI-1 | ATF3 | 4.34 |
| 422 | 3 | 4 | 5 | 6 | | VI-2 | SNRPA | 0.48 | 518 | 3 | 4 | 5 | 6 | VI-1 | ATP12A | 2.97 |
| 423 | 3 | 4 | 5 | 6 | | VI-2 | SOLH | 0.47 | 519 | 3 | 4 | 5 | 6 | VI-1 | ATP8A1 | 2.24 |
| 424 | 3 | 4 | 5 | 6 | | VI-2 | SORBS3 | 0.44 | 520 | 3 | 4 | 5 | 6 | VI-1 | ATRX | 2.28 |
| 425 | 3 | 4 | 5 | 6 | | VI-2 | SOX10 | 0.35 | 521 | 3 | 4 | 5 | 6 | VI-1 | BCL2A1 | 3.52 |
| 426 | 3 | 4 | 5 | 6 | | VI-2 | SOX12 | 0.48 | 522 | 3 | 4 | 5 | 6 | VI-1 | BICC1 | 2.16 |
| 427 | 3 | 4 | 5 | 6 | | VI-2 | SOX15 | 0.36 | 523 | 3 | 4 | 5 | 6 | VI-1 | BOD1L | 3.06 |
| 428 | 3 | 4 | 5 | 6 | | VI-2 | SPDEF | 0.40 | 524 | 3 | 4 | 5 | 6 | VI-1 | BROX | 2.17 |
| 429 | 3 | 4 | 5 | 6 | | VI-2 | SRM | 0.49 | 525 | 3 | 4 | 5 | 6 | VI-1 | C14orf102 | 2.01 |
| 430 | 3 | 4 | 5 | 6 | | VI-2 | SSR4 | 0.50 | 526 | 3 | 4 | 5 | 6 | VI-1 | C14orf118 | 2.12 |
| 431 | 3 | 4 | 5 | 6 | | VI-2 | STAC2 | 0.30 | 527 | 3 | 4 | 5 | 6 | VI-1 | C14orf49 | 2.34 |
| 432 | 3 | 4 | 5 | 6 | | VI-2 | STC1 | 0.25 | 528 | 3 | 4 | 5 | 6 | VI-1 | C1QTNF7 | 2.07 |
| 433 | 3 | 4 | 5 | 6 | | VI-2 | STMN2 | 0.47 | 529 | 3 | 4 | 5 | 6 | VI-1 | C2orf49 | 2.07 |
| 434 | 3 | 4 | 5 | 6 | | VI-2 | SYNPO | 0.37 | 530 | 3 | 4 | 5 | 6 | VI-1 | C4orf34 | 2.04 |
| 435 | 3 | 4 | 5 | 6 | | VI-2 | TAF6 | 0.46 | 531 | 3 | 4 | 5 | 6 | VI-1 | C5AR1 | 2.59 |
| 436 | 3 | 4 | 5 | 6 | | VI-2 | TAGLN2 | 0.30 | 532 | 3 | 4 | 5 | 6 | VI-1 | C7orf58 | 2.16 |
| 437 | 3 | 4 | 5 | 6 | | VI-2 | TBX1 | 0.44 | 533 | 3 | 4 | 5 | 6 | VI-1 | C8orf4 | 2.08 |
| 438 | 3 | 4 | 5 | 6 | | VI-2 | TESK1 | 0.42 | 534 | 3 | 4 | 5 | 6 | VI-1 | C8orf84 | 2.43 |
| 439 | 3 | 4 | 5 | 6 | | VI-2 | TFAP4 | 0.43 | 535 | 3 | 4 | 5 | 6 | VI-1 | C9orf41 | 2.23 |
| 440 | 3 | 4 | 5 | 6 | | VI-2 | THRA | 0.40 | 536 | 3 | 4 | 5 | 6 | VI-1 | CBR3-AS1 | 2.45 |
| 441 | 3 | 4 | 5 | 6 | | VI-2 | TIAF1 | 0.47 | 537 | 3 | 4 | 5 | 6 | VI-1 | CCBE1 | 2.05 |
| 442 | 3 | 4 | 5 | 6 | | VI-2 | TIE1 | 0.48 | 538 | 3 | 4 | 5 | 6 | VI-1 | CCDC75 | 2.41 |
| 443 | 3 | 4 | 5 | 6 | | VI-2 | TK1 | 0.49 | 539 | 3 | 4 | 5 | 6 | VI-1 | CCL3L3 | 3.07 |
| 444 | 3 | 4 | 5 | 6 | | VI-2 | TMC4 | 0.46 | 540 | 3 | 4 | 5 | 6 | VI-1 | CCL4 | 4.54 |
| 445 | 3 | 4 | 5 | 6 | | VI-2 | TMCC2 | 0.43 | 541 | 3 | 4 | 5 | 6 | VI-1 | CCL8 | 4.77 |
| 446 | 3 | 4 | 5 | 6 | | VI-2 | TMEM139 | 0.47 | 542 | 3 | 4 | 5 | 6 | VI-1 | CCR4 | 4.88 |
| 447 | 3 | 4 | 5 | 6 | | VI-2 | TMEM161A | 0.48 | 543 | 3 | 4 | 5 | 6 | VI-1 | CD3G | 2.64 |
| 448 | 3 | 4 | 5 | 6 | | VI-2 | TMEM53 | 0.48 | 544 | 3 | 4 | 5 | 6 | VI-1 | CDNF | 2.56 |
| 449 | 3 | 4 | 5 | 6 | | VI-2 | TMUB1 | 0.45 | 545 | 3 | 4 | 5 | 6 | VI-1 | CH25H | 2.57 |
| 450 | 3 | 4 | 5 | 6 | | VI-2 | TNFRSF12A | 0.28 | 546 | 3 | 4 | 5 | 6 | VI-1 | CLCN4 | 2.12 |
| 451 | 3 | 4 | 5 | 6 | | VI-2 | TNFRSF1A | 0.49 | 547 | 3 | 4 | 5 | 6 | VI-1 | CLEC12A | 2.15 |
| 452 | 3 | 4 | 5 | 6 | | VI-2 | TNK1 | 0.45 | 548 | 3 | 4 | 5 | 6 | VI-1 | CLSTN2 | 2.28 |
| 453 | 3 | 4 | 5 | 6 | | VI-2 | TNNT1 | 0.40 | 549 | 3 | 4 | 5 | 6 | VI-1 | CNTN1 | 2.19 |
| 454 | 3 | 4 | 5 | 6 | | VI-2 | TNXA | 0.24 | 550 | 3 | 4 | 5 | 6 | VI-1 | COL8A1 | 2.14 |
| 455 | 3 | 4 | 5 | 6 | | VI-2 | TOMM40 | 0.43 | 551 | 3 | 4 | 5 | 6 | VI-1 | CORIN | 2.27 |
| 456 | 3 | 4 | 5 | 6 | | VI-2 | TONSL | 0.49 | 552 | 3 | 4 | 5 | 6 | VI-1 | CWF19L2 | 2.71 |
| 457 | 3 | 4 | 5 | 6 | | VI-2 | TP53I13 | 0.47 | 553 | 3 | 4 | 5 | 6 | VI-1 | CXCL3 | 2.25 |
| 458 | 3 | 4 | 5 | 6 | | VI-2 | TPGS1 | 0.50 | 554 | 3 | 4 | 5 | 6 | VI-1 | CXCR2 | 3.57 |
| 459 | 3 | 4 | 5 | 6 | | VI-2 | TPI1 | 0.47 | 555 | 3 | 4 | 5 | 6 | VI-1 | CYP4F2 | 3.24 |
| 460 | 3 | 4 | 5 | 6 | | VI-2 | TPPP | 0.36 | 556 | 3 | 4 | 5 | 6 | VI-1 | CYP4F3 | 2.74 |
| 461 | 3 | 4 | 5 | 6 | | VI-2 | TPX2 | 0.37 | 557 | 3 | 4 | 5 | 6 | VI-1 | DCP1A | 2.34 |
| 462 | 3 | 4 | 5 | 6 | | VI-2 | TRAF3IP2 | 0.49 | 558 | 3 | 4 | 5 | 6 | VI-1 | DCP2 | 2.24 |
| 463 | 3 | 4 | 5 | 6 | | VI-2 | TRAF7 | 0.47 | 559 | 3 | 4 | 5 | 6 | VI-1 | DEFB103B | 4.02 |
| 464 | 3 | 4 | 5 | 6 | | VI-2 | TRAPPC1 | 0.49 | 560 | 3 | 4 | 5 | 6 | VI-1 | DHRS2 | 3.08 |
| 465 | 3 | 4 | 5 | 6 | | VI-2 | TREX1 | 0.44 | 561 | 3 | 4 | 5 | 6 | VI-1 | DIO3 | 2.24 |
| 466 | 3 | 4 | 5 | 6 | | VI-2 | TRIM28 | 0.49 | 562 | 3 | 4 | 5 | 6 | VI-1 | DKFZP434I0714 | 2.07 |
| 467 | 3 | 4 | 5 | 6 | | VI-2 | TRPM4 | 0.47 | 563 | 3 | 4 | 5 | 6 | VI-1 | DNAJC27 | 2.18 |
| 468 | 3 | 4 | 5 | 6 | | VI-2 | TRPV4 | 0.40 | 564 | 3 | 4 | 5 | 6 | VI-1 | DPP8 | 2.30 |
| 469 | 3 | 4 | 5 | 6 | | VI-2 | TSTA3 | 0.43 | 565 | 3 | 4 | 5 | 6 | VI-1 | ENTPD5 | 2.16 |
| 470 | 3 | 4 | 5 | 6 | | VI-2 | TUBB4A | 0.26 | 566 | 3 | 4 | 5 | 6 | VI-1 | ERN1 | 2.43 |
| 471 | 3 | 4 | 5 | 6 | | VI-2 | TUBB6 | 0.45 | 567 | 3 | 4 | 5 | 6 | VI-1 | ESF1 | 2.92 |
| 472 | 3 | 4 | 5 | 6 | | VI-2 | TYR | 0.45 | 568 | 3 | 4 | 5 | 6 | VI-1 | EXOC6B | 2.50 |
| 473 | 3 | 4 | 5 | 6 | | VI-2 | UPK3BL | 0.46 | 569 | 3 | 4 | 5 | 6 | VI-1 | FAM126B | 2.86 |
| 474 | 3 | 4 | 5 | 6 | | VI-2 | URM1 | 0.48 | 570 | 3 | 4 | 5 | 6 | VI-1 | FAM217B | 2.92 |
| 475 | 3 | 4 | 5 | 6 | | VI-2 | VEGFB | 0.40 | 571 | 3 | 4 | 5 | 6 | VI-1 | FAM26E | 2.05 |
| 476 | 3 | 4 | 5 | 6 | | VI-2 | VEGFC | 0.50 | 572 | 3 | 4 | 5 | 6 | VI-1 | FAM46A | 2.35 |
| 477 | 3 | 4 | 5 | 6 | | VI-2 | WASH3P | 0.50 | 573 | 3 | 4 | 5 | 6 | VI-1 | FAM46C | 4.13 |
| 478 | 3 | 4 | 5 | 6 | | VI-2 | WASH5P | 0.35 | 574 | 3 | 4 | 5 | 6 | VI-1 | FAM73A | 2.45 |

Fig. 38 - 4

| | | | | | | | |
|---|---|---|---|---|---|---|---|
| 575 | 3 | 4 | 5 | 6 | VI-1 | FAT4 | 2.05 |
| 576 | 3 | 4 | 5 | 6 | VI-1 | FCGR2C | 2.36 |
| 577 | 3 | 4 | 5 | 6 | VI-1 | FCGR3A | 2.52 |
| 578 | 3 | 4 | 5 | 6 | VI-1 | FGFR1OP | 2.15 |
| 579 | 3 | 4 | 5 | 6 | VI-1 | FICD | 2.04 |
| 580 | 3 | 4 | 5 | 6 | VI-1 | FKBP5 | 2.22 |
| 581 | 3 | 4 | 5 | 6 | VI-1 | FUT11 | 2.04 |
| 582 | 3 | 4 | 5 | 6 | VI-1 | GCC2 | 2.37 |
| 583 | 3 | 4 | 5 | 6 | VI-1 | GFOD1 | 2.53 |
| 584 | 3 | 4 | 5 | 6 | VI-1 | GMCL1P1 | 2.06 |
| 585 | 3 | 4 | 5 | 6 | VI-1 | GNAL | 2.21 |
| 586 | 3 | 4 | 5 | 6 | VI-1 | GNMT | 4.79 |
| 587 | 3 | 4 | 5 | 6 | VI-1 | GPLD1 | 2.26 |
| 588 | 3 | 4 | 5 | 6 | VI-1 | GPR34 | 3.34 |
| 589 | 3 | 4 | 5 | 6 | VI-1 | HAO1 | 3.51 |
| 590 | 3 | 4 | 5 | 6 | VI-1 | HBA2 | 2.93 |
| 591 | 3 | 4 | 5 | 6 | VI-1 | HERC2P3 | 2.15 |
| 592 | 3 | 4 | 5 | 6 | VI-1 | HFE | 2.27 |
| 593 | 3 | 4 | 5 | 6 | VI-1 | HIATL2 | 2.18 |
| 594 | 3 | 4 | 5 | 6 | VI-1 | HIPK3 | 2.58 |
| 595 | 3 | 4 | 5 | 6 | VI-1 | HIST1H2AI | 2.36 |
| 596 | 3 | 4 | 5 | 6 | VI-1 | HIST1H2AL | 2.18 |
| 597 | 3 | 4 | 5 | 6 | VI-1 | HIST1H2AM | 2.20 |
| 598 | 3 | 4 | 5 | 6 | VI-1 | HIST1H4C | 2.90 |
| 599 | 3 | 4 | 5 | 6 | VI-1 | HIST1H4J | 2.61 |
| 600 | 3 | 4 | 5 | 6 | VI-1 | HIST1H4K | 2.46 |
| 601 | 3 | 4 | 5 | 6 | VI-1 | HLA-DRB6 | 4.55 |
| 602 | 3 | 4 | 5 | 6 | VI-1 | HLCS | 2.15 |
| 603 | 3 | 4 | 5 | 6 | VI-1 | HMBOX1 | 2.28 |
| 604 | 3 | 4 | 5 | 6 | VI-1 | HPR | 2.94 |
| 605 | 3 | 4 | 5 | 6 | VI-1 | HSP90AA6P | 2.96 |
| 606 | 3 | 4 | 5 | 6 | VI-1 | ID2-AS1 | 2.06 |
| 607 | 3 | 4 | 5 | 6 | VI-1 | IFI44L | 2.12 |
| 608 | 3 | 4 | 5 | 6 | VI-1 | IGF1 | 4.18 |
| 609 | 3 | 4 | 5 | 6 | VI-1 | INHBA | 2.15 |
| 610 | 3 | 4 | 5 | 6 | VI-1 | KBTBD11 | 2.62 |
| 611 | 3 | 4 | 5 | 6 | VI-1 | KBTBD7 | 2.74 |
| 612 | 3 | 4 | 5 | 6 | VI-1 | KCNH2 | 2.13 |
| 613 | 3 | 4 | 5 | 6 | VI-1 | KCNJ18 | 4.29 |
| 614 | 3 | 4 | 5 | 6 | VI-1 | KCNMA1 | 2.47 |
| 615 | 3 | 4 | 5 | 6 | VI-1 | KIAA0664L3 | 2.14 |
| 616 | 3 | 4 | 5 | 6 | VI-1 | KLHL8 | 2.01 |
| 617 | 3 | 4 | 5 | 6 | VI-1 | KLRAP1 | 2.41 |
| 618 | 3 | 4 | 5 | 6 | VI-1 | KRBA2 | 2.86 |
| 619 | 3 | 4 | 5 | 6 | VI-1 | KRTAP1-3 | 2.04 |
| 620 | 3 | 4 | 5 | 6 | VI-1 | KRTAP1-5 | 2.23 |
| 621 | 3 | 4 | 5 | 6 | VI-1 | KRTAP16-1 | 2.62 |
| 622 | 3 | 4 | 5 | 6 | VI-1 | KRTAP2-1 | 2.03 |
| 623 | 3 | 4 | 5 | 6 | VI-1 | KRTAP3-2 | 2.26 |
| 624 | 3 | 4 | 5 | 6 | VI-1 | KRTAP8-1 | 2.28 |
| 625 | 3 | 4 | 5 | 6 | VI-1 | KRTAP9-8 | 2.60 |
| 626 | 3 | 4 | 5 | 6 | VI-1 | KTN1 | 3.86 |
| 627 | 3 | 4 | 5 | 6 | VI-1 | LACC1 | 2.27 |
| 628 | 3 | 4 | 5 | 6 | VI-1 | LAIR1 | 2.12 |
| 629 | 3 | 4 | 5 | 6 | VI-1 | LAX1 | 2.06 |
| 630 | 3 | 4 | 5 | 6 | VI-1 | LGR5 | 2.19 |
| 631 | 3 | 4 | 5 | 6 | VI-1 | LINC00478 | 2.14 |
| 632 | 3 | 4 | 5 | 6 | VI-1 | LIPN | 3.56 |
| 633 | 3 | 4 | 5 | 6 | VI-1 | LOC100216546 | 3.74 |
| 634 | 3 | 4 | 5 | 6 | VI-1 | LOC100289230 | 2.35 |
| 635 | 3 | 4 | 5 | 6 | VI-1 | LOC100289511 | 2.32 |
| 636 | 3 | 4 | 5 | 6 | VI-1 | LOC100505815 | 3.68 |
| 637 | 3 | 4 | 5 | 6 | VI-1 | LOC158257 | 4.85 |
| 638 | 3 | 4 | 5 | 6 | VI-1 | LOC202181 | 4.07 |
| 639 | 3 | 4 | 5 | 6 | VI-1 | LOC619207 | 2.23 |
| 640 | 3 | 4 | 5 | 6 | VI-1 | LOC728640 | 3.42 |
| 641 | 3 | 4 | 5 | 6 | VI-1 | LOC728978 | 3.42 |
| 642 | 3 | 4 | 5 | 6 | VI-1 | LOC729739 | 2.08 |
| 643 | 3 | 4 | 5 | 6 | VI-1 | LPIN1 | 2.04 |
| 644 | 3 | 4 | 5 | 6 | VI-1 | LYSMD3 | 2.01 |
| 645 | 3 | 4 | 5 | 6 | VI-1 | LYVE1 | 2.51 |
| 646 | 3 | 4 | 5 | 6 | VI-1 | LZIC | 3.08 |
| 647 | 3 | 4 | 5 | 6 | VI-1 | MACROD2 | 2.13 |
| 648 | 3 | 4 | 5 | 6 | VI-1 | MAP1B | 2.10 |
| 649 | 3 | 4 | 5 | 6 | VI-1 | MASP2 | 4.12 |
| 650 | 3 | 4 | 5 | 6 | VI-1 | MC5R | 2.93 |
| 651 | 3 | 4 | 5 | 6 | VI-1 | MGAT4A | 2.31 |
| 652 | 3 | 4 | 5 | 6 | VI-1 | MIR17HG | 2.47 |
| 653 | 3 | 4 | 5 | 6 | VI-1 | MIR22HG | 2.23 |
| 654 | 3 | 4 | 5 | 6 | VI-1 | MIR320B2 | 4.80 |
| 655 | 3 | 4 | 5 | 6 | VI-1 | MPHOSPH8 | 2.16 |
| 656 | 3 | 4 | 5 | 6 | VI-1 | MRE11A | 2.15 |
| 657 | 3 | 4 | 5 | 6 | VI-1 | MRGPRX2 | 4.78 |
| 658 | 3 | 4 | 5 | 6 | VI-1 | MS4A4A | 2.80 |
| 659 | 3 | 4 | 5 | 6 | VI-1 | MS4A7 | 3.78 |
| 660 | 3 | 4 | 5 | 6 | VI-1 | MTRNR2L6 | 2.11 |
| 661 | 3 | 4 | 5 | 6 | VI-1 | MYOCD | 2.60 |
| 662 | 3 | 4 | 5 | 6 | VI-1 | NAIP | 2.73 |
| 663 | 3 | 4 | 5 | 6 | VI-1 | NBPF1 | 2.43 |
| 664 | 3 | 4 | 5 | 6 | VI-1 | NBPF9 | 2.10 |
| 665 | 3 | 4 | 5 | 6 | VI-1 | NEK6 | 2.92 |
| 666 | 3 | 4 | 5 | 6 | VI-1 | NELL2 | 3.47 |
| 667 | 3 | 4 | 5 | 6 | VI-1 | NEU3 | 2.28 |
| 668 | 3 | 4 | 5 | 6 | VI-1 | NID2 | 2.34 |
| 669 | 3 | 4 | 5 | 6 | VI-1 | NIPAL1 | 3.53 |
| 670 | 3 | 4 | 5 | 6 | VI-1 | NLRP10 | 2.68 |
| 671 | 3 | 4 | 5 | 6 | VI-1 | NPL | 2.65 |
| 672 | 3 | 4 | 5 | 6 | VI-1 | NR2C2 | 2.17 |
| 673 | 3 | 4 | 5 | 6 | VI-1 | OBFC2A | 2.49 |
| 674 | 3 | 4 | 5 | 6 | VI-1 | OGN | 2.42 |
| 675 | 3 | 4 | 5 | 6 | VI-1 | OLAH | 2.04 |
| 676 | 3 | 4 | 5 | 6 | VI-1 | P2RY13 | 3.62 |
| 677 | 3 | 4 | 5 | 6 | VI-1 | PARD6B | 2.01 |
| 678 | 3 | 4 | 5 | 6 | VI-1 | PCDH20 | 2.64 |
| 679 | 3 | 4 | 5 | 6 | VI-1 | PDE6A | 2.73 |
| 680 | 3 | 4 | 5 | 6 | VI-1 | PHF14 | 2.00 |
| 681 | 3 | 4 | 5 | 6 | VI-1 | PKD1L2 | 2.38 |
| 682 | 3 | 4 | 5 | 6 | VI-1 | PLG | 2.86 |
| 683 | 3 | 4 | 5 | 6 | VI-1 | POU2F2 | 2.47 |
| 684 | 3 | 4 | 5 | 6 | VI-1 | PPARA | 2.04 |
| 685 | 3 | 4 | 5 | 6 | VI-1 | PPIG | 3.16 |
| 686 | 3 | 4 | 5 | 6 | VI-1 | PPM1K | 3.34 |
| 687 | 3 | 4 | 5 | 6 | VI-1 | PRRC2C | 2.07 |
| 688 | 3 | 4 | 5 | 6 | VI-1 | PSG7 | 2.66 |
| 689 | 3 | 4 | 5 | 6 | VI-1 | PTGFR | 2.21 |
| 690 | 3 | 4 | 5 | 6 | VI-1 | PTGS2 | 4.76 |
| 691 | 3 | 4 | 5 | 6 | VI-1 | PTPRZ1 | 2.56 |
| 692 | 3 | 4 | 5 | 6 | VI-1 | PTX3 | 2.01 |
| 693 | 3 | 4 | 5 | 6 | VI-1 | RAPGEF6 | 2.01 |
| 694 | 3 | 4 | 5 | 6 | VI-1 | RBM41 | 2.65 |
| 695 | 3 | 4 | 5 | 6 | VI-1 | RGPD1 | 2.05 |
| 696 | 3 | 4 | 5 | 6 | VI-1 | ROR1 | 2.54 |
| 697 | 3 | 4 | 5 | 6 | VI-1 | RPL10L | 3.34 |
| 698 | 3 | 4 | 5 | 6 | VI-1 | RPL23AP64 | 4.68 |
| 699 | 3 | 4 | 5 | 6 | VI-1 | RPS10-NUDT3 | 2.37 |
| 700 | 3 | 4 | 5 | 6 | VI-1 | RUNX1T1 | 2.08 |
| 701 | 3 | 4 | 5 | 6 | VI-1 | SELL | 4.43 |
| 702 | 3 | 4 | 5 | 6 | VI-1 | SEPP1 | 2.16 |
| 703 | 3 | 4 | 5 | 6 | VI-1 | SEPSECS | 2.12 |
| 704 | 3 | 4 | 5 | 6 | VI-1 | SERPINC1 | 4.22 |
| 705 | 3 | 4 | 5 | 6 | VI-1 | SLA | 3.08 |
| 706 | 3 | 4 | 5 | 6 | VI-1 | SLC2A14 | 2.00 |
| 707 | 3 | 4 | 5 | 6 | VI-1 | SLC4A7 | 2.20 |
| 708 | 3 | 4 | 5 | 6 | VI-1 | SLC5A3 | 2.12 |
| 709 | 3 | 4 | 5 | 6 | VI-1 | SLIT2 | 3.29 |
| 710 | 3 | 4 | 5 | 6 | VI-1 | SMA4 | 4.32 |
| 711 | 3 | 4 | 5 | 6 | VI-1 | SNORA14B | 2.61 |
| 712 | 3 | 4 | 5 | 6 | VI-1 | SNORA16B | 2.81 |
| 713 | 3 | 4 | 5 | 6 | VI-1 | SNORA24 | 4.47 |
| 714 | 3 | 4 | 5 | 6 | VI-1 | SNORA29 | 3.22 |
| 715 | 3 | 4 | 5 | 6 | VI-1 | SNORA37 | 3.30 |
| 716 | 3 | 4 | 5 | 6 | VI-1 | SNORA38B | 2.92 |
| 717 | 3 | 4 | 5 | 6 | VI-1 | SNORA41 | 2.92 |
| 718 | 3 | 4 | 5 | 6 | VI-1 | SNORA47 | 2.37 |
| 719 | 3 | 4 | 5 | 6 | VI-1 | SNORA59A | 3.95 |
| 720 | 3 | 4 | 5 | 6 | VI-1 | SNORA59B | 2.80 |
| 721 | 3 | 4 | 5 | 6 | VI-1 | SNORA63 | 3.82 |
| 722 | 3 | 4 | 5 | 6 | VI-1 | SNORA65 | 2.53 |
| 723 | 3 | 4 | 5 | 6 | VI-1 | SNORA71C | 2.37 |
| 724 | 3 | 4 | 5 | 6 | VI-1 | SNORA72 | 4.29 |
| 725 | 3 | 4 | 5 | 6 | VI-1 | SNORA75 | 4.39 |
| 726 | 3 | 4 | 5 | 6 | VI-1 | SNORA9 | 2.81 |
| 727 | 3 | 4 | 5 | 6 | VI-1 | SNORD17 | 2.85 |
| 728 | 3 | 4 | 5 | 6 | VI-1 | SNORD97 | 2.10 |
| 729 | 3 | 4 | 5 | 6 | VI-1 | SOD2 | 4.01 |
| 730 | 3 | 4 | 5 | 6 | VI-1 | SON | 2.29 |
| 731 | 3 | 4 | 5 | 6 | VI-1 | SPDYE2 | 2.55 |
| 732 | 3 | 4 | 5 | 6 | VI-1 | SPIN3 | 2.05 |
| 733 | 3 | 4 | 5 | 6 | VI-1 | SPOCK1 | 2.22 |
| 734 | 3 | 4 | 5 | 6 | VI-1 | SPRR2F | 3.72 |
| 735 | 3 | 4 | 5 | 6 | VI-1 | SSPN | 2.11 |
| 736 | 3 | 4 | 5 | 6 | VI-1 | SWT1 | 2.70 |
| 737 | 3 | 4 | 5 | 6 | VI-1 | TAF1L | 3.26 |
| 738 | 3 | 4 | 5 | 6 | VI-1 | TAS2R5 | 2.02 |
| 739 | 3 | 4 | 5 | 6 | VI-1 | TBX18 | 2.69 |
| 740 | 3 | 4 | 5 | 6 | VI-1 | TCP11L2 | 2.14 |
| 741 | 3 | 4 | 5 | 6 | VI-1 | TEAD1 | 2.26 |
| 742 | 3 | 4 | 5 | 6 | VI-1 | THOC2 | 2.51 |
| 743 | 3 | 4 | 5 | 6 | VI-1 | THSD4 | 2.50 |
| 744 | 3 | 4 | 5 | 6 | VI-1 | TLR2 | 2.11 |
| 745 | 3 | 4 | 5 | 6 | VI-1 | TMEM170A | 2.08 |
| 746 | 3 | 4 | 5 | 6 | VI-1 | TMPRSS11F | 2.67 |
| 747 | 3 | 4 | 5 | 6 | VI-1 | TNFRSF10C | 2.50 |
| 748 | 3 | 4 | 5 | 6 | VI-1 | TRAF3IP3 | 2.18 |
| 749 | 3 | 4 | 5 | 6 | VI-1 | TREM1 | 2.44 |
| 750 | 3 | 4 | 5 | 6 | VI-1 | TRIM38 | 2.68 |
| 751 | 3 | 4 | 5 | 6 | VI-1 | TRIM52 | 2.28 |
| 752 | 3 | 4 | 5 | 6 | VI-1 | TRPV3 | 2.49 |
| 753 | 3 | 4 | 5 | 6 | VI-1 | TSSK4 | 2.35 |
| 754 | 3 | 4 | 5 | 6 | VI-1 | TSTD2 | 2.04 |
| 755 | 3 | 4 | 5 | 6 | VI-1 | TUB | 2.08 |
| 756 | 3 | 4 | 5 | 6 | VI-1 | UBXN7 | 2.78 |
| 757 | 3 | 4 | 5 | 6 | VI-1 | UOX | 3.60 |
| 758 | 3 | 4 | 5 | 6 | VI-1 | UPB1 | 2.75 |
| 759 | 3 | 4 | 5 | 6 | VI-1 | UPF3B | 2.19 |
| 760 | 3 | 4 | 5 | 6 | VI-1 | USP32P2 | 4.72 |
| 761 | 3 | 4 | 5 | 6 | VI-1 | VNN2 | 2.48 |
| 762 | 3 | 4 | 5 | 6 | VI-1 | ZBTB16 | 2.64 |
| 763 | 3 | 4 | 5 | 6 | VI-1 | ZBTB6 | 2.06 |
| 764 | 3 | 4 | 5 | 6 | VI-1 | ZDHHC21 | 2.32 |
| 765 | 3 | 4 | 5 | 6 | VI-1 | ZFHX3 | 2.01 |
| 766 | 3 | 4 | 5 | 6 | VI-1 | ZFP112 | 2.32 |

Fig. 38 - 5

| | | | | | | | |
|---|---|---|---|---|---|---|---|
| 767 | 3 | 4 | 5 | 6 | VI-1 | ZFP30 | 2.28 |
| 768 | 3 | 4 | 5 | 6 | VI-1 | ZKSCAN1 | 3.35 |
| 769 | 3 | 4 | 5 | 6 | VI-1 | ZNF107 | 2.52 |
| 770 | 3 | 4 | 5 | 6 | VI-1 | ZNF124 | 2.23 |
| 771 | 3 | 4 | 5 | 6 | VI-1 | ZNF136 | 2.09 |
| 772 | 3 | 4 | 5 | 6 | VI-1 | ZNF169 | 2.30 |
| 773 | 3 | 4 | 5 | 6 | VI-1 | ZNF189 | 2.01 |
| 774 | 3 | 4 | 5 | 6 | VI-1 | ZNF192 | 4.05 |
| 775 | 3 | 4 | 5 | 6 | VI-1 | ZNF20 | 2.10 |
| 776 | 3 | 4 | 5 | 6 | VI-1 | ZNF225 | 2.19 |
| 777 | 3 | 4 | 5 | 6 | VI-1 | ZNF234 | 2.85 |
| 778 | 3 | 4 | 5 | 6 | VI-1 | ZNF281 | 3.70 |
| 779 | 3 | 4 | 5 | 6 | VI-1 | ZNF292 | 2.04 |
| 780 | 3 | 4 | 5 | 6 | VI-1 | ZNF331 | 2.57 |
| 781 | 3 | 4 | 5 | 6 | VI-1 | ZNF347 | 2.37 |
| 782 | 3 | 4 | 5 | 6 | VI-1 | ZNF37A | 2.11 |
| 783 | 3 | 4 | 5 | 6 | VI-1 | ZNF397 | 2.70 |
| 784 | 3 | 4 | 5 | 6 | VI-1 | ZNF462 | 2.07 |
| 785 | 3 | 4 | 5 | 6 | VI-1 | ZNF506 | 2.81 |
| 786 | 3 | 4 | 5 | 6 | VI-1 | ZNF540 | 2.31 |
| 787 | 3 | 4 | 5 | 6 | VI-1 | ZNF550 | 2.84 |
| 788 | 3 | 4 | 5 | 6 | VI-1 | ZNF551 | 2.09 |
| 789 | 3 | 4 | 5 | 6 | VI-1 | ZNF611 | 2.11 |
| 790 | 3 | 4 | 5 | 6 | VI-1 | ZNF625 | 2.11 |
| 791 | 3 | 4 | 5 | 6 | VI-1 | ZNF658 | 2.12 |
| 792 | 3 | 4 | 5 | 6 | VI-1 | ZNF662 | 2.18 |
| 793 | 3 | 4 | 5 | 6 | VI-1 | ZNF714 | 2.13 |
| 794 | 3 | 4 | 5 | 6 | VI-1 | ZNF737 | 2.79 |
| 795 | 3 | 4 | 5 | 6 | VI-1 | ZNF761 | 2.34 |
| 796 | 3 | 4 | 5 | 6 | VI-1 | ZNF780B | 2.13 |
| 797 | 3 | 4 | 5 | 6 | VI-1 | ZNF793 | 2.88 |
| 798 | 3 | 4 | 5 | 6 | VI-1 | ZNF814 | 2.23 |
| 799 | 3 | 4 | 5 | 6 | VI-1 | ZNF844 | 2.88 |
| 800 | 3 | 4 | 5 | 6 | VI-1 | ZNF846 | 2.61 |
| 801 | 3 | 4 | 5 | 6 | VI-1 | ZNF91 | 3.01 |
| 802 | 3 | 4 | 5 | 6 | VI-1 | ZRANB2-AS1 | 2.31 |
| 803 | 3 | 4 | 5 | | V-2 | AAMP | 0.65 |
| 804 | 3 | 4 | 5 | | V-2 | AARS | 0.61 |
| 805 | 3 | 4 | 5 | | V-2 | AARSD1 | 0.65 |
| 806 | 3 | 4 | 5 | | V-2 | ABCB8 | 0.62 |
| 807 | 3 | 4 | 5 | | V-2 | ABCC3 | 0.60 |
| 808 | 3 | 4 | 5 | | V-2 | ABCD1 | 0.64 |
| 809 | 3 | 4 | 5 | | V-2 | ABCF3 | 0.59 |
| 810 | 3 | 4 | 5 | | V-2 | ABHD12 | 0.60 |
| 811 | 3 | 4 | 5 | | V-2 | ABHD14B | 0.64 |
| 812 | 3 | 4 | 5 | | V-2 | ABHD16B | 0.53 |
| 813 | 3 | 4 | 5 | | V-2 | ABHD4 | 0.66 |
| 814 | 3 | 4 | 5 | | V-2 | ABI3 | 0.66 |
| 815 | 3 | 4 | 5 | | V-2 | ABL1 | 0.58 |
| 816 | 3 | 4 | 5 | | V-2 | ABR | 0.66 |
| 817 | 3 | 4 | 5 | | V-2 | ABT1 | 0.66 |
| 818 | 3 | 4 | 5 | | V-2 | ABTB1 | 0.58 |
| 819 | 3 | 4 | 5 | | V-2 | ACAD5 | 0.51 |
| 820 | 3 | 4 | 5 | | V-2 | ACD | 0.53 |
| 821 | 3 | 4 | 5 | | V-2 | ACP2 | 0.56 |
| 822 | 3 | 4 | 5 | | V-2 | ACTR1B | 0.67 |
| 823 | 3 | 4 | 5 | | V-2 | ACVRL1 | 0.62 |
| 824 | 3 | 4 | 5 | | V-2 | ADAMTS14 | 0.51 |
| 825 | 3 | 4 | 5 | | V-2 | ADAMTS7 | 0.66 |
| 826 | 3 | 4 | 5 | | V-2 | ADAMTS8 | 0.63 |
| 827 | 3 | 4 | 5 | | V-2 | ADAT3 | 0.62 |
| 828 | 3 | 4 | 5 | | V-2 | ADCK3 | 0.61 |
| 829 | 3 | 4 | 5 | | V-2 | ADCK4 | 0.63 |
| 830 | 3 | 4 | 5 | | V-2 | ADPRHL2 | 0.60 |
| 831 | 3 | 4 | 5 | | V-2 | ADRA2A | 0.55 |
| 832 | 3 | 4 | 5 | | V-2 | ADRBK1 | 0.63 |
| 833 | 3 | 4 | 5 | | V-2 | ADRM1 | 0.54 |
| 834 | 3 | 4 | 5 | | V-2 | AFAP1L2 | 0.63 |
| 835 | 3 | 4 | 5 | | V-2 | AGRN | 0.56 |
| 836 | 3 | 4 | 5 | | V-2 | AHDC1 | 0.56 |
| 837 | 3 | 4 | 5 | | V-2 | AHSA1 | 0.59 |
| 838 | 3 | 4 | 5 | | V-2 | AIMP2 | 0.65 |
| 839 | 3 | 4 | 5 | | V-2 | AIP | 0.54 |
| 840 | 3 | 4 | 5 | | V-2 | AK1 | 0.59 |
| 841 | 3 | 4 | 5 | | V-2 | AKIP1 | 0.59 |
| 842 | 3 | 4 | 5 | | V-2 | AKR1C1 | 0.62 |
| 843 | 3 | 4 | 5 | | V-2 | AKT1 | 0.52 |
| 844 | 3 | 4 | 5 | | V-2 | AKT2 | 0.65 |
| 845 | 3 | 4 | 5 | | V-2 | ALDOC | 0.66 |
| 846 | 3 | 4 | 5 | | V-2 | ALG12 | 0.59 |
| 847 | 3 | 4 | 5 | | V-2 | ALKBH2 | 0.55 |
| 848 | 3 | 4 | 5 | | V-2 | ALKBH4 | 0.53 |
| 849 | 3 | 4 | 5 | | V-2 | ALYREF | 0.51 |
| 850 | 3 | 4 | 5 | | V-2 | AMIGO1 | 0.66 |
| 851 | 3 | 4 | 5 | | V-2 | ANAPC11 | 0.62 |
| 852 | 3 | 4 | 5 | | V-2 | ANAPC2 | 0.57 |
| 853 | 3 | 4 | 5 | | V-2 | ANGPTL4 | 0.61 |
| 854 | 3 | 4 | 5 | | V-2 | ANKRD13D | 0.62 |
| 855 | 3 | 4 | 5 | | V-2 | ANKRD19P | 0.62 |
| 856 | 3 | 4 | 5 | | V-2 | ANKRD54 | 0.53 |
| 857 | 3 | 4 | 5 | | V-2 | ANO8 | 0.65 |
| 858 | 3 | 4 | 5 | | V-2 | ANPEP | 0.62 |
| 859 | 3 | 4 | 5 | | V-2 | ANXA11 | 0.61 |
| 860 | 3 | 4 | 5 | | V-2 | ANXA2P2 | 0.51 |
| 861 | 3 | 4 | 5 | | V-2 | ANXA5 | 0.54 |
| 862 | 3 | 4 | 5 | | V-2 | AP1M1 | 0.56 |
| 863 | 3 | 4 | 5 | | V-2 | AP2A1 | 0.65 |
| 864 | 3 | 4 | 5 | | V-2 | AP3S1 | 0.67 |
| 865 | 3 | 4 | 5 | | V-2 | APCDD1 | 0.56 |
| 866 | 3 | 4 | 5 | | V-2 | APEH | 0.65 |
| 867 | 3 | 4 | 5 | | V-2 | APEX1 | 0.64 |
| 868 | 3 | 4 | 5 | | V-2 | APLNR | 0.55 |
| 869 | 3 | 4 | 5 | | V-2 | APOA1BP | 0.60 |
| 870 | 3 | 4 | 5 | | V-2 | APOBEC3B | 0.59 |
| 871 | 3 | 4 | 5 | | V-2 | APOBEC3D | 0.63 |
| 872 | 3 | 4 | 5 | | V-2 | APOL3 | 0.59 |
| 873 | 3 | 4 | 5 | | V-2 | ARAF | 0.60 |
| 874 | 3 | 4 | 5 | | V-2 | ARF5 | 0.55 |
| 875 | 3 | 4 | 5 | | V-2 | ARFIP2 | 0.65 |
| 876 | 3 | 4 | 5 | | V-2 | ARFRP1 | 0.56 |
| 877 | 3 | 4 | 5 | | V-2 | ARHGAP1 | 0.56 |
| 878 | 3 | 4 | 5 | | V-2 | ARHGAP10 | 0.65 |
| 879 | 3 | 4 | 5 | | V-2 | ARHGAP17 | 0.62 |
| 880 | 3 | 4 | 5 | | V-2 | ARHGAP8 | 0.64 |
| 881 | 3 | 4 | 5 | | V-2 | ARHGEF4 | 0.60 |
| 882 | 3 | 4 | 5 | | V-2 | ARL6IP4 | 0.51 |
| 883 | 3 | 4 | 5 | | V-2 | ARMC5 | 0.60 |
| 884 | 3 | 4 | 5 | | V-2 | ARMC7 | 0.55 |
| 885 | 3 | 4 | 5 | | V-2 | ARRDC1 | 0.54 |
| 886 | 3 | 4 | 5 | | V-2 | ASB6 | 0.66 |
| 887 | 3 | 4 | 5 | | V-2 | ASB9 | 0.66 |
| 888 | 3 | 4 | 5 | | V-2 | ASCC2 | 0.51 |
| 889 | 3 | 4 | 5 | | V-2 | ASGR1 | 0.56 |
| 890 | 3 | 4 | 5 | | V-2 | ASMTL-AS1 | 0.54 |
| 891 | 3 | 4 | 5 | | V-2 | ASPSCR1 | 0.56 |
| 892 | 3 | 4 | 5 | | V-2 | ATAD3A | 0.52 |
| 893 | 3 | 4 | 5 | | V-2 | ATG3 | 0.61 |
| 894 | 3 | 4 | 5 | | V-2 | ATG4B | 0.66 |
| 895 | 3 | 4 | 5 | | V-2 | ATN1 | 0.54 |
| 896 | 3 | 4 | 5 | | V-2 | ATP13A1 | 0.60 |
| 897 | 3 | 4 | 5 | | V-2 | ATP1A1OS | 0.65 |
| 898 | 3 | 4 | 5 | | V-2 | ATP5G2 | 0.60 |
| 899 | 3 | 4 | 5 | | V-2 | ATP5SL | 0.54 |
| 900 | 3 | 4 | 5 | | V-2 | ATP6V0E2 | 0.54 |
| 901 | 3 | 4 | 5 | | V-2 | ATRIP | 0.63 |
| 902 | 3 | 4 | 5 | | V-2 | ATXN7L2 | 0.63 |
| 903 | 3 | 4 | 5 | | V-2 | ATXN7L3 | 0.63 |
| 904 | 3 | 4 | 5 | | V-2 | AURKA | 0.55 |
| 905 | 3 | 4 | 5 | | V-2 | AURKAIP1 | 0.58 |
| 906 | 3 | 4 | 5 | | V-2 | AXL | 0.66 |
| 907 | 3 | 4 | 5 | | V-2 | AZI1 | 0.57 |
| 908 | 3 | 4 | 5 | | V-2 | B3GALT6 | 0.64 |
| 909 | 3 | 4 | 5 | | V-2 | B3GAT3 | 0.58 |
| 910 | 3 | 4 | 5 | | V-2 | B3GNT7 | 0.50 |
| 911 | 3 | 4 | 5 | | V-2 | B4GALT2 | 0.61 |
| 912 | 3 | 4 | 5 | | V-2 | B4GALT7 | 0.67 |
| 913 | 3 | 4 | 5 | | V-2 | B9D2 | 0.52 |
| 914 | 3 | 4 | 5 | | V-2 | BAHCC1 | 0.63 |
| 915 | 3 | 4 | 5 | | V-2 | BAIAP2 | 0.64 |
| 916 | 3 | 4 | 5 | | V-2 | BAIAP2L2 | 0.61 |
| 917 | 3 | 4 | 5 | | V-2 | BAIAP3 | 0.55 |
| 918 | 3 | 4 | 5 | | V-2 | BANF1 | 0.52 |
| 919 | 3 | 4 | 5 | | V-2 | BAP1 | 0.55 |
| 920 | 3 | 4 | 5 | | V-2 | BCL7B | 0.57 |
| 921 | 3 | 4 | 5 | | V-2 | BCL7C | 0.65 |
| 922 | 3 | 4 | 5 | | V-2 | BCRP3 | 0.61 |
| 923 | 3 | 4 | 5 | | V-2 | BEX2 | 0.51 |
| 924 | 3 | 4 | 5 | | V-2 | BGN | 0.59 |
| 925 | 3 | 4 | 5 | | V-2 | BOK | 0.55 |
| 926 | 3 | 4 | 5 | | V-2 | BOLA2 | 0.57 |
| 927 | 3 | 4 | 5 | | V-2 | BOP1 | 0.51 |
| 928 | 3 | 4 | 5 | | V-2 | BRF1 | 0.66 |
| 929 | 3 | 4 | 5 | | V-2 | BRF2 | 0.65 |
| 930 | 3 | 4 | 5 | | V-2 | BRI3 | 0.60 |
| 931 | 3 | 4 | 5 | | V-2 | BRMS1 | 0.50 |
| 932 | 3 | 4 | 5 | | V-2 | BST2 | 0.51 |
| 933 | 3 | 4 | 5 | | V-2 | BTBD6 | 0.60 |
| 934 | 3 | 4 | 5 | | V-2 | BYSL | 0.66 |
| 935 | 3 | 4 | 5 | | V-2 | C10orf2 | 0.58 |
| 936 | 3 | 4 | 5 | | V-2 | C10orf47 | 0.61 |
| 937 | 3 | 4 | 5 | | V-2 | C10orf54 | 0.53 |
| 938 | 3 | 4 | 5 | | V-2 | C10orf76 | 0.66 |
| 939 | 3 | 4 | 5 | | V-2 | C11orf24 | 0.54 |
| 940 | 3 | 4 | 5 | | V-2 | C11orf48 | 0.63 |
| 941 | 3 | 4 | 5 | | V-2 | C11orf51 | 0.57 |
| 942 | 3 | 4 | 5 | | V-2 | C11orf67 | 0.61 |
| 943 | 3 | 4 | 5 | | V-2 | C11orf83 | 0.60 |
| 944 | 3 | 4 | 5 | | V-2 | C12orf10 | 0.51 |
| 945 | 3 | 4 | 5 | | V-2 | C12orf43 | 0.67 |
| 946 | 3 | 4 | 5 | | V-2 | C12orf5 | 0.60 |
| 947 | 3 | 4 | 5 | | V-2 | C14orf166 | 0.64 |
| 948 | 3 | 4 | 5 | | V-2 | C15orf24 | 0.65 |
| 949 | 3 | 4 | 5 | | V-2 | C16orf42 | 0.50 |
| 950 | 3 | 4 | 5 | | V-2 | C16orf58 | 0.56 |
| 951 | 3 | 4 | 5 | | V-2 | C16orf80 | 0.63 |
| 952 | 3 | 4 | 5 | | V-2 | C16orf86 | 0.62 |
| 953 | 3 | 4 | 5 | | V-2 | C17orf101 | 0.67 |
| 954 | 3 | 4 | 5 | | V-2 | C17orf103 | 0.66 |
| 955 | 3 | 4 | 5 | | V-2 | C17orf49 | 0.57 |
| 956 | 3 | 4 | 5 | | V-2 | C17orf70 | 0.59 |
| 957 | 3 | 4 | 5 | | V-2 | C17orf76-AS1 | 0.57 |
| 958 | 3 | 4 | 5 | | V-2 | C17orf90 | 0.61 |

Fig. 38 - 6

| | | | | | | | | | | | | | | | |
|---|---|---|---|---|---|---|---|---|---|---|---|---|---|---|---|
| 959 | 3 | 4 | 5 | | V-2 | C19orf25 | 0.64 | 1055 | 3 | 4 | 5 | | V-2 | CKMT1B | 0.58 |
| 960 | 3 | 4 | 5 | | V-2 | C19orf29 | 0.55 | 1056 | 3 | 4 | 5 | | V-2 | CKS1B | 0.60 |
| 961 | 3 | 4 | 5 | | V-2 | C19orf43 | 0.53 | 1057 | 3 | 4 | 5 | | V-2 | CLCF1 | 0.52 |
| 962 | 3 | 4 | 5 | | V-2 | C19orf51 | 0.64 | 1058 | 3 | 4 | 5 | | V-2 | CLCN7 | 0.64 |
| 963 | 3 | 4 | 5 | | V-2 | C19orf70 | 0.50 | 1059 | 3 | 4 | 5 | | V-2 | CLDN11 | 0.57 |
| 964 | 3 | 4 | 5 | | V-2 | C19orf71 | 0.64 | 1060 | 3 | 4 | 5 | | V-2 | CLN3 | 0.61 |
| 965 | 3 | 4 | 5 | | V-2 | C19orf77 | 0.52 | 1061 | 3 | 4 | 5 | | V-2 | CLPTM1L | 0.62 |
| 966 | 3 | 4 | 5 | | V-2 | C1orf115 | 0.52 | 1062 | 3 | 4 | 5 | | V-2 | CLTA | 0.62 |
| 967 | 3 | 4 | 5 | | V-2 | C1orf216 | 0.65 | 1063 | 3 | 4 | 5 | | V-2 | CNN2 | 0.65 |
| 968 | 3 | 4 | 5 | | V-2 | C1orf86 | 0.55 | 1064 | 3 | 4 | 5 | | V-2 | CNNM1 | 0.62 |
| 969 | 3 | 4 | 5 | | V-2 | C1QTNF6 | 0.58 | 1065 | 3 | 4 | 5 | | V-2 | CNOT3 | 0.55 |
| 970 | 3 | 4 | 5 | | V-2 | C1QTNF9B-AS1 | 0.53 | 1066 | 3 | 4 | 5 | | V-2 | CNPPD1 | 0.56 |
| 971 | 3 | 4 | 5 | | V-2 | C20orf151 | 0.60 | 1067 | 3 | 4 | 5 | | V-2 | CNPY3 | 0.57 |
| 972 | 3 | 4 | 5 | | V-2 | C21orf119 | 0.66 | 1068 | 3 | 4 | 5 | | V-2 | CNTNAP3B | 0.57 |
| 973 | 3 | 4 | 5 | | V-2 | C21orf2 | 0.60 | 1069 | 3 | 4 | 5 | | V-2 | CNTROB | 0.59 |
| 974 | 3 | 4 | 5 | | V-2 | C21orf56 | 0.56 | 1070 | 3 | 4 | 5 | | V-2 | COASY | 0.63 |
| 975 | 3 | 4 | 5 | | V-2 | C21orf63 | 0.60 | 1071 | 3 | 4 | 5 | | V-2 | COBRA1 | 0.56 |
| 976 | 3 | 4 | 5 | | V-2 | C22orf13 | 0.62 | 1072 | 3 | 4 | 5 | | V-2 | COG4 | 0.63 |
| 977 | 3 | 4 | 5 | | V-2 | C2orf55 | 0.52 | 1073 | 3 | 4 | 5 | | V-2 | COL17A1 | 0.63 |
| 978 | 3 | 4 | 5 | | V-2 | C2orf81 | 0.58 | 1074 | 3 | 4 | 5 | | V-2 | COL4A2 | 0.51 |
| 979 | 3 | 4 | 5 | | V-2 | C3orf35 | 0.61 | 1075 | 3 | 4 | 5 | | V-2 | COL6A2 | 0.55 |
| 980 | 3 | 4 | 5 | | V-2 | C4orf42 | 0.62 | 1076 | 3 | 4 | 5 | | V-2 | COL9A3 | 0.61 |
| 981 | 3 | 4 | 5 | | V-2 | C5orf38 | 0.58 | 1077 | 3 | 4 | 5 | | V-2 | COPZ2 | 0.57 |
| 982 | 3 | 4 | 5 | | V-2 | C6orf108 | 0.57 | 1078 | 3 | 4 | 5 | | V-2 | COQ4 | 0.67 |
| 983 | 3 | 4 | 5 | | V-2 | C7orf11 | 0.59 | 1079 | 3 | 4 | 5 | | V-2 | COQ9 | 0.59 |
| 984 | 3 | 4 | 5 | | V-2 | C7orf26 | 0.66 | 1080 | 3 | 4 | 5 | | V-2 | CORO1B | 0.55 |
| 985 | 3 | 4 | 5 | | V-2 | C7orf44 | 0.65 | 1081 | 3 | 4 | 5 | | V-2 | CORO1C | 0.66 |
| 986 | 3 | 4 | 5 | | V-2 | C7orf49 | 0.65 | 1082 | 3 | 4 | 5 | | V-2 | CORO2B | 0.61 |
| 987 | 3 | 4 | 5 | | V-2 | C8orf82 | 0.60 | 1083 | 3 | 4 | 5 | | V-2 | COX4I1 | 0.62 |
| 988 | 3 | 4 | 5 | | V-2 | C9orf152 | 0.54 | 1084 | 3 | 4 | 5 | | V-2 | COX4NB | 0.61 |
| 989 | 3 | 4 | 5 | | V-2 | C9orf25 | 0.66 | 1085 | 3 | 4 | 5 | | V-2 | COX6A1 | 0.59 |
| 990 | 3 | 4 | 5 | | V-2 | C9orf37 | 0.52 | 1086 | 3 | 4 | 5 | | V-2 | CPNE2 | 0.54 |
| 991 | 3 | 4 | 5 | | V-2 | C9orf86 | 0.55 | 1087 | 3 | 4 | 5 | | V-2 | CPSF3L | 0.63 |
| 992 | 3 | 4 | 5 | | V-2 | C9orf89 | 0.53 | 1088 | 3 | 4 | 5 | | V-2 | CPT1A | 0.53 |
| 993 | 3 | 4 | 5 | | V-2 | C9orf9 | 0.53 | 1089 | 3 | 4 | 5 | | V-2 | CRABP2 | 0.66 |
| 994 | 3 | 4 | 5 | | V-2 | CA5BP1 | 0.51 | 1090 | 3 | 4 | 5 | | V-2 | CREB3 | 0.62 |
| 995 | 3 | 4 | 5 | | V-2 | CABIN1 | 0.60 | 1091 | 3 | 4 | 5 | | V-2 | CRELD2 | 0.52 |
| 996 | 3 | 4 | 5 | | V-2 | CABLES1 | 0.52 | 1092 | 3 | 4 | 5 | | V-2 | CRHR1 | 0.63 |
| 997 | 3 | 4 | 5 | | V-2 | CABLES2 | 0.64 | 1093 | 3 | 4 | 5 | | V-2 | CRTAC1 | 0.56 |
| 998 | 3 | 4 | 5 | | V-2 | CALHM2 | 0.55 | 1094 | 3 | 4 | 5 | | V-2 | CRTC1 | 0.65 |
| 999 | 3 | 4 | 5 | | V-2 | CAMKMT | 0.64 | 1095 | 3 | 4 | 5 | | V-2 | CSF1 | 0.57 |
| 1000 | 3 | 4 | 5 | | V-2 | CAMTA1 | 0.62 | 1096 | 3 | 4 | 5 | | V-2 | CSNK1G2 | 0.62 |
| 1001 | 3 | 4 | 5 | | V-2 | CAMTA2 | 0.52 | 1097 | 3 | 4 | 5 | | V-2 | CSNK2B | 0.66 |
| 1002 | 3 | 4 | 5 | | V-2 | CAPZB | 0.50 | 1098 | 3 | 4 | 5 | | V-2 | CTBP1 | 0.57 |
| 1003 | 3 | 4 | 5 | | V-2 | CARS2 | 0.50 | 1099 | 3 | 4 | 5 | | V-2 | CTDNEP1 | 0.54 |
| 1004 | 3 | 4 | 5 | | V-2 | CASP7 | 0.61 | 1100 | 3 | 4 | 5 | | V-2 | CTDSP1 | 0.55 |
| 1005 | 3 | 4 | 5 | | V-2 | CBX2 | 0.53 | 1101 | 3 | 4 | 5 | | V-2 | CTF1 | 0.54 |
| 1006 | 3 | 4 | 5 | | V-2 | CC2D1A | 0.57 | 1102 | 3 | 4 | 5 | | V-2 | CTHRC1 | 0.60 |
| 1007 | 3 | 4 | 5 | | V-2 | CCDC106 | 0.60 | 1103 | 3 | 4 | 5 | | V-2 | CTIF | 0.52 |
| 1008 | 3 | 4 | 5 | | V-2 | CCDC107 | 0.58 | 1104 | 3 | 4 | 5 | | V-2 | CTNNBL1 | 0.61 |
| 1009 | 3 | 4 | 5 | | V-2 | CCDC12 | 0.55 | 1105 | 3 | 4 | 5 | | V-2 | CUEDC1 | 0.57 |
| 1010 | 3 | 4 | 5 | | V-2 | CCDC167 | 0.63 | 1106 | 3 | 4 | 5 | | V-2 | CXCL14 | 0.60 |
| 1011 | 3 | 4 | 5 | | V-2 | CCDC23 | 0.65 | 1107 | 3 | 4 | 5 | | V-2 | CXXC1 | 0.57 |
| 1012 | 3 | 4 | 5 | | V-2 | CCDC48 | 0.62 | 1108 | 3 | 4 | 5 | | V-2 | CYB5D2 | 0.67 |
| 1013 | 3 | 4 | 5 | | V-2 | CCDC69 | 0.64 | 1109 | 3 | 4 | 5 | | V-2 | CYB5R1 | 0.59 |
| 1014 | 3 | 4 | 5 | | V-2 | CCDC71 | 0.55 | 1110 | 3 | 4 | 5 | | V-2 | CYHR1 | 0.67 |
| 1015 | 3 | 4 | 5 | | V-2 | CCDC8 | 0.62 | 1111 | 3 | 4 | 5 | | V-2 | CYP26B1 | 0.52 |
| 1016 | 3 | 4 | 5 | | V-2 | CCDC92 | 0.51 | 1112 | 3 | 4 | 5 | | V-2 | CYP4B1 | 0.60 |
| 1017 | 3 | 4 | 5 | | V-2 | CCHCR1 | 0.52 | 1113 | 3 | 4 | 5 | | V-2 | CYTH2 | 0.52 |
| 1018 | 3 | 4 | 5 | | V-2 | CD28P2 | 0.66 | 1114 | 3 | 4 | 5 | | V-2 | DAB2IP | 0.66 |
| 1019 | 3 | 4 | 5 | | V-2 | CD40 | 0.67 | 1115 | 3 | 4 | 5 | | V-2 | DACT1 | 0.63 |
| 1020 | 3 | 4 | 5 | | V-2 | CD63 | 0.63 | 1116 | 3 | 4 | 5 | | V-2 | DACT2 | 0.52 |
| 1021 | 3 | 4 | 5 | | V-2 | CD79B | 0.65 | 1117 | 3 | 4 | 5 | | V-2 | DAK | 0.55 |
| 1022 | 3 | 4 | 5 | | V-2 | CD81 | 0.61 | 1118 | 3 | 4 | 5 | | V-2 | DANCR | 0.66 |
| 1023 | 3 | 4 | 5 | | V-2 | CD9 | 0.57 | 1119 | 3 | 4 | 5 | | V-2 | DAP | 0.64 |
| 1024 | 3 | 4 | 5 | | V-2 | CD97 | 0.60 | 1120 | 3 | 4 | 5 | | V-2 | DAPK3 | 0.59 |
| 1025 | 3 | 4 | 5 | | V-2 | CD99 | 0.52 | 1121 | 3 | 4 | 5 | | V-2 | DAXX | 0.62 |
| 1026 | 3 | 4 | 5 | | V-2 | CDC123 | 0.59 | 1122 | 3 | 4 | 5 | | V-2 | DAZAP1 | 0.65 |
| 1027 | 3 | 4 | 5 | | V-2 | CDC26 | 0.67 | 1123 | 3 | 4 | 5 | | V-2 | DBNDD1 | 0.56 |
| 1028 | 3 | 4 | 5 | | V-2 | CDC37 | 0.57 | 1124 | 3 | 4 | 5 | | V-2 | DCAKD | 0.58 |
| 1029 | 3 | 4 | 5 | | V-2 | CDC42EP5 | 0.51 | 1125 | 3 | 4 | 5 | | V-2 | DCP1B | 0.57 |
| 1030 | 3 | 4 | 5 | | V-2 | CDCA7L | 0.58 | 1126 | 3 | 4 | 5 | | V-2 | DCPS | 0.59 |
| 1031 | 3 | 4 | 5 | | V-2 | CDH3 | 0.59 | 1127 | 3 | 4 | 5 | | V-2 | DCTN1 | 0.53 |
| 1032 | 3 | 4 | 5 | | V-2 | CDK4 | 0.67 | 1128 | 3 | 4 | 5 | | V-2 | DCXR | 0.58 |
| 1033 | 3 | 4 | 5 | | V-2 | CDK7 | 0.59 | 1129 | 3 | 4 | 5 | | V-2 | DDAH2 | 0.53 |
| 1034 | 3 | 4 | 5 | | V-2 | CDKN2AIPNL | 0.58 | 1130 | 3 | 4 | 5 | | V-2 | DDB2 | 0.63 |
| 1035 | 3 | 4 | 5 | | V-2 | CDKN2C | 0.63 | 1131 | 3 | 4 | 5 | | V-2 | DDOST | 0.65 |
| 1036 | 3 | 4 | 5 | | V-2 | CDKN3 | 0.53 | 1132 | 3 | 4 | 5 | | V-2 | DDR1 | 0.55 |
| 1037 | 3 | 4 | 5 | | V-2 | CEACAM19 | 0.51 | 1133 | 3 | 4 | 5 | | V-2 | DDX19A | 0.66 |
| 1038 | 3 | 4 | 5 | | V-2 | CECR5 | 0.59 | 1134 | 3 | 4 | 5 | | V-2 | DDX39A | 0.53 |
| 1039 | 3 | 4 | 5 | | V-2 | CENPL | 0.54 | 1135 | 3 | 4 | 5 | | V-2 | DDX41 | 0.62 |
| 1040 | 3 | 4 | 5 | | V-2 | CENPN | 0.60 | 1136 | 3 | 4 | 5 | | V-2 | DDX51 | 0.60 |
| 1041 | 3 | 4 | 5 | | V-2 | CEP55 | 0.55 | 1137 | 3 | 4 | 5 | | V-2 | DECR2 | 0.60 |
| 1042 | 3 | 4 | 5 | | V-2 | CERCAM | 0.67 | 1138 | 3 | 4 | 5 | | V-2 | DEDD | 0.65 |
| 1043 | 3 | 4 | 5 | | V-2 | CGREF1 | 0.59 | 1139 | 3 | 4 | 5 | | V-2 | DEDD2 | 0.56 |
| 1044 | 3 | 4 | 5 | | V-2 | CHAF1B | 0.64 | 1140 | 3 | 4 | 5 | | V-2 | DEF6 | 0.63 |
| 1045 | 3 | 4 | 5 | | V-2 | CHCHD5 | 0.56 | 1141 | 3 | 4 | 5 | | V-2 | DERA | 0.67 |
| 1046 | 3 | 4 | 5 | | V-2 | CHERP | 0.59 | 1142 | 3 | 4 | 5 | | V-2 | DEXI | 0.63 |
| 1047 | 3 | 4 | 5 | | V-2 | CHMP2A | 0.59 | 1143 | 3 | 4 | 5 | | V-2 | DGCR14 | 0.59 |
| 1048 | 3 | 4 | 5 | | V-2 | CHMP6 | 0.64 | 1144 | 3 | 4 | 5 | | V-2 | DGCR6L | 0.51 |
| 1049 | 3 | 4 | 5 | | V-2 | CHST12 | 0.62 | 1145 | 3 | 4 | 5 | | V-2 | DGKQ | 0.54 |
| 1050 | 3 | 4 | 5 | | V-2 | CHST14 | 0.58 | 1146 | 3 | 4 | 5 | | V-2 | DGKZ | 0.53 |
| 1051 | 3 | 4 | 5 | | V-2 | CIB2 | 0.54 | 1147 | 3 | 4 | 5 | | V-2 | DHRS13 | 0.51 |
| 1052 | 3 | 4 | 5 | | V-2 | CIDEB | 0.65 | 1148 | 3 | 4 | 5 | | V-2 | DHRS3 | 0.56 |
| 1053 | 3 | 4 | 5 | | V-2 | CINP | 0.57 | 1149 | 3 | 4 | 5 | | V-2 | DHRS4L2 | 0.58 |
| 1054 | 3 | 4 | 5 | | V-2 | CKB | 0.51 | 1150 | 3 | 4 | 5 | | V-2 | DHRSX | 0.64 |

Fig. 38 - 7

| | | | | | | | | | | | | | | | | | |
|---|---|---|---|---|---|---|---|---|---|---|---|---|---|---|---|---|---|
| 1151 | 3 | 4 | 5 | | | V-2 | DHX30 | 0.59 | 1246 | 3 | 4 | 5 | | | V-2 | FAM58A | 0.65 |
| 1152 | 3 | 4 | 5 | | | V-2 | DHX37 | 0.58 | 1247 | 3 | 4 | 5 | | | V-2 | FAM65A | 0.56 |
| 1153 | 3 | 4 | 5 | | | V-2 | DIRAS1 | 0.55 | 1248 | 3 | 4 | 5 | | | V-2 | FAM83B | 0.65 |
| 1154 | 3 | 4 | 5 | | | V-2 | DIS3L2 | 0.61 | 1249 | 3 | 4 | 5 | | | V-2 | FAM86A | 0.60 |
| 1155 | 3 | 4 | 5 | | | V-2 | DLX4 | 0.56 | 1250 | 3 | 4 | 5 | | | V-2 | FANCG | 0.65 |
| 1156 | 3 | 4 | 5 | | | V-2 | DMWD | 0.65 | 1251 | 3 | 4 | 5 | | | V-2 | FARS2 | 0.60 |
| 1157 | 3 | 4 | 5 | | | V-2 | DNAJC1 | 0.66 | 1252 | 3 | 4 | 5 | | | V-2 | FARSB | 0.59 |
| 1158 | 3 | 4 | 5 | | | V-2 | DNAJC14 | 0.66 | 1253 | 3 | 4 | 5 | | | V-2 | FASTK | 0.58 |
| 1159 | 3 | 4 | 5 | | | V-2 | DNAJC4 | 0.53 | 1254 | 3 | 4 | 5 | | | V-2 | FAU | 0.59 |
| 1160 | 3 | 4 | 5 | | | V-2 | DNAJC8 | 0.63 | 1255 | 3 | 4 | 5 | | | V-2 | FBL | 0.65 |
| 1161 | 3 | 4 | 5 | | | V-2 | DNM2 | 0.61 | 1256 | 3 | 4 | 5 | | | V-2 | FBN1 | 0.61 |
| 1162 | 3 | 4 | 5 | | | V-2 | DNTTIP1 | 0.52 | 1257 | 3 | 4 | 5 | | | V-2 | FBRS | 0.51 |
| 1163 | 3 | 4 | 5 | | | V-2 | DOC2B | 0.61 | 1258 | 3 | 4 | 5 | | | V-2 | FBRSL1 | 0.51 |
| 1164 | 3 | 4 | 5 | | | V-2 | DOK1 | 0.62 | 1259 | 3 | 4 | 5 | | | V-2 | FBXL16 | 0.55 |
| 1165 | 3 | 4 | 5 | | | V-2 | DOLK | 0.51 | 1260 | 3 | 4 | 5 | | | V-2 | FBXL8 | 0.58 |
| 1166 | 3 | 4 | 5 | | | V-2 | DPAGT1 | 0.64 | 1261 | 3 | 4 | 5 | | | V-2 | FBXO41 | 0.66 |
| 1167 | 3 | 4 | 5 | | | V-2 | DPEP2 | 0.61 | 1262 | 3 | 4 | 5 | | | V-2 | FBXO7 | 0.66 |
| 1168 | 3 | 4 | 5 | | | V-2 | DPF2 | 0.62 | 1263 | 3 | 4 | 5 | | | V-2 | FBXW4 | 0.61 |
| 1169 | 3 | 4 | 5 | | | V-2 | DPH2 | 0.63 | 1264 | 3 | 4 | 5 | | | V-2 | FBXW5 | 0.57 |
| 1170 | 3 | 4 | 5 | | | V-2 | DPM1 | 0.66 | 1265 | 3 | 4 | 5 | | | V-2 | FGD1 | 0.53 |
| 1171 | 3 | 4 | 5 | | | V-2 | DPP3 | 0.64 | 1266 | 3 | 4 | 5 | | | V-2 | FGD5 | 0.56 |
| 1172 | 3 | 4 | 5 | | | V-2 | DPP7 | 0.54 | 1267 | 3 | 4 | 5 | | | V-2 | FGF16 | 0.65 |
| 1173 | 3 | 4 | 5 | | | V-2 | DPY30 | 0.62 | 1268 | 3 | 4 | 5 | | | V-2 | FGFBP3 | 0.59 |
| 1174 | 3 | 4 | 5 | | | V-2 | DPYSL3 | 0.54 | 1269 | 3 | 4 | 5 | | | V-2 | FGFRL1 | 0.54 |
| 1175 | 3 | 4 | 5 | | | V-2 | DTNB | 0.58 | 1270 | 3 | 4 | 5 | | | V-2 | FHL3 | 0.50 |
| 1176 | 3 | 4 | 5 | | | V-2 | DTNBP1 | 0.63 | 1271 | 3 | 4 | 5 | | | V-2 | FHOD1 | 0.63 |
| 1177 | 3 | 4 | 5 | | | V-2 | DTX2P1-UPK3BP1-PMS2P11 | 0.61 | 1272 | 3 | 4 | 5 | | | V-2 | FIS1 | 0.60 |
| 1178 | 3 | 4 | 5 | | | V-2 | DTYMK | 0.55 | 1273 | 3 | 4 | 5 | | | V-2 | FKBP1A | 0.58 |
| 1179 | 3 | 4 | 5 | | | V-2 | DUS2L | 0.52 | 1274 | 3 | 4 | 5 | | | V-2 | FKBP2 | 0.50 |
| 1180 | 3 | 4 | 5 | | | V-2 | DUS3L | 0.52 | 1275 | 3 | 4 | 5 | | | V-2 | FKBPL | 0.64 |
| 1181 | 3 | 4 | 5 | | | V-2 | DUSP23 | 0.56 | 1276 | 3 | 4 | 5 | | | V-2 | FLAD1 | 0.58 |
| 1182 | 3 | 4 | 5 | | | V-2 | DVL1 | 0.52 | 1277 | 3 | 4 | 5 | | | V-2 | FLII | 0.58 |
| 1183 | 3 | 4 | 5 | | | V-2 | DVL2 | 0.62 | 1278 | 3 | 4 | 5 | | | V-2 | FLJ20021 | 0.51 |
| 1184 | 3 | 4 | 5 | | | V-2 | DVL3 | 0.63 | 1279 | 3 | 4 | 5 | | | V-2 | FLJ31485 | 0.66 |
| 1185 | 3 | 4 | 5 | | | V-2 | DYRK1B | 0.56 | 1280 | 3 | 4 | 5 | | | V-2 | FLJ44635 | 0.60 |
| 1186 | 3 | 4 | 5 | | | V-2 | E2F1 | 0.59 | 1281 | 3 | 4 | 5 | | | V-2 | FLJ46906 | 0.59 |
| 1187 | 3 | 4 | 5 | | | V-2 | E2F4 | 0.53 | 1282 | 3 | 4 | 5 | | | V-2 | FLYWCH2 | 0.51 |
| 1188 | 3 | 4 | 5 | | | V-2 | EDC4 | 0.56 | 1283 | 3 | 4 | 5 | | | V-2 | FMNL1 | 0.57 |
| 1189 | 3 | 4 | 5 | | | V-2 | EDF1 | 0.56 | 1284 | 3 | 4 | 5 | | | V-2 | FMOD | 0.62 |
| 1190 | 3 | 4 | 5 | | | V-2 | EEPD1 | 0.60 | 1285 | 3 | 4 | 5 | | | V-2 | FN3K | 0.65 |
| 1191 | 3 | 4 | 5 | | | V-2 | EFCAB4A | 0.56 | 1286 | 3 | 4 | 5 | | | V-2 | FNDC4 | 0.59 |
| 1192 | 3 | 4 | 5 | | | V-2 | EFHD2 | 0.59 | 1287 | 3 | 4 | 5 | | | V-2 | FOXF1 | 0.54 |
| 1193 | 3 | 4 | 5 | | | V-2 | EFS | 0.64 | 1288 | 3 | 4 | 5 | | | V-2 | FOXM1 | 0.53 |
| 1194 | 3 | 4 | 5 | | | V-2 | EFTUD2 | 0.59 | 1289 | 3 | 4 | 5 | | | V-2 | FPGS | 0.52 |
| 1195 | 3 | 4 | 5 | | | V-2 | EGFLAM | 0.56 | 1290 | 3 | 4 | 5 | | | V-2 | FRZB | 0.57 |
| 1196 | 3 | 4 | 5 | | | V-2 | EIF2AK1 | 0.59 | 1291 | 3 | 4 | 5 | | | V-2 | FSCN1 | 0.57 |
| 1197 | 3 | 4 | 5 | | | V-2 | EIF2D | 0.66 | 1292 | 3 | 4 | 5 | | | V-2 | FSTL3 | 0.59 |
| 1198 | 3 | 4 | 5 | | | V-2 | EIF3C | 0.55 | 1293 | 3 | 4 | 5 | | | V-2 | FTH1 | 0.52 |
| 1199 | 3 | 4 | 5 | | | V-2 | EIF3I | 0.64 | 1294 | 3 | 4 | 5 | | | V-2 | FTL | 0.64 |
| 1200 | 3 | 4 | 5 | | | V-2 | EIF4EBP3 | 0.61 | 1295 | 3 | 4 | 5 | | | V-2 | FTSJ1 | 0.67 |
| 1201 | 3 | 4 | 5 | | | V-2 | ELAC2 | 0.58 | 1296 | 3 | 4 | 5 | | | V-2 | FTSJD2 | 0.63 |
| 1202 | 3 | 4 | 5 | | | V-2 | ELF3 | 0.58 | 1297 | 3 | 4 | 5 | | | V-2 | FUK | 0.61 |
| 1203 | 3 | 4 | 5 | | | V-2 | ELF4 | 0.55 | 1298 | 3 | 4 | 5 | | | V-2 | FUNDC2 | 0.62 |
| 1204 | 3 | 4 | 5 | | | V-2 | ELMO1 | 0.65 | 1299 | 3 | 4 | 5 | | | V-2 | FUNDC2P2 | 0.53 |
| 1205 | 3 | 4 | 5 | | | V-2 | ELMO2 | 0.63 | 1300 | 3 | 4 | 5 | | | V-2 | FXR2 | 0.61 |
| 1206 | 3 | 4 | 5 | | | V-2 | ELOF1 | 0.52 | 1301 | 3 | 4 | 5 | | | V-2 | FYN | 0.64 |
| 1207 | 3 | 4 | 5 | | | V-2 | EMD | 0.62 | 1302 | 3 | 4 | 5 | | | V-2 | FZR1 | 0.66 |
| 1208 | 3 | 4 | 5 | | | V-2 | EML2 | 0.64 | 1303 | 3 | 4 | 5 | | | V-2 | GADD45G | 0.66 |
| 1209 | 3 | 4 | 5 | | | V-2 | ENO1 | 0.52 | 1304 | 3 | 4 | 5 | | | V-2 | GAK | 0.59 |
| 1210 | 3 | 4 | 5 | | | V-2 | ENTPD2 | 0.56 | 1305 | 3 | 4 | 5 | | | V-2 | GALNT2 | 0.61 |
| 1211 | 3 | 4 | 5 | | | V-2 | EPHB3 | 0.52 | 1306 | 3 | 4 | 5 | | | V-2 | GALNTL1 | 0.66 |
| 1212 | 3 | 4 | 5 | | | V-2 | EPHB4 | 0.53 | 1307 | 3 | 4 | 5 | | | V-2 | GAMT | 0.64 |
| 1213 | 3 | 4 | 5 | | | V-2 | EPHB6 | 0.58 | 1308 | 3 | 4 | 5 | | | V-2 | GANAB | 0.58 |
| 1214 | 3 | 4 | 5 | | | V-2 | EPHX1 | 0.60 | 1309 | 3 | 4 | 5 | | | V-2 | GAS1 | 0.60 |
| 1215 | 3 | 4 | 5 | | | V-2 | ERAL1 | 0.54 | 1310 | 3 | 4 | 5 | | | V-2 | GATAD2A | 0.57 |
| 1216 | 3 | 4 | 5 | | | V-2 | ERBB2 | 0.52 | 1311 | 3 | 4 | 5 | | | V-2 | GATSL3 | 0.65 |
| 1217 | 3 | 4 | 5 | | | V-2 | ERGIC3 | 0.60 | 1312 | 3 | 4 | 5 | | | V-2 | GBF1 | 0.66 |
| 1218 | 3 | 4 | 5 | | | V-2 | ESPN | 0.51 | 1313 | 3 | 4 | 5 | | | V-2 | GBP4 | 0.62 |
| 1219 | 3 | 4 | 5 | | | V-2 | ESRRA | 0.61 | 1314 | 3 | 4 | 5 | | | V-2 | GDI1 | 0.61 |
| 1220 | 3 | 4 | 5 | | | V-2 | ESYT1 | 0.61 | 1315 | 3 | 4 | 5 | | | V-2 | GEMIN6 | 0.59 |
| 1221 | 3 | 4 | 5 | | | V-2 | ETFB | 0.60 | 1316 | 3 | 4 | 5 | | | V-2 | GFER | 0.51 |
| 1222 | 3 | 4 | 5 | | | V-2 | EXOSC4 | 0.50 | 1317 | 3 | 4 | 5 | | | V-2 | GFRA3 | 0.55 |
| 1223 | 3 | 4 | 5 | | | V-2 | EXOSC6 | 0.64 | 1318 | 3 | 4 | 5 | | | V-2 | GGA3 | 0.60 |
| 1224 | 3 | 4 | 5 | | | V-2 | EXT1 | 0.52 | 1319 | 3 | 4 | 5 | | | V-2 | GGT5 | 0.62 |
| 1225 | 3 | 4 | 5 | | | V-2 | F10 | 0.54 | 1320 | 3 | 4 | 5 | | | V-2 | GGTLC2 | 0.56 |
| 1226 | 3 | 4 | 5 | | | V-2 | FADD | 0.64 | 1321 | 3 | 4 | 5 | | | V-2 | GIMAP5 | 0.67 |
| 1227 | 3 | 4 | 5 | | | V-2 | FAIM | 0.58 | 1322 | 3 | 4 | 5 | | | V-2 | GLB1 | 0.66 |
| 1228 | 3 | 4 | 5 | | | V-2 | FAM108A1 | 0.52 | 1323 | 3 | 4 | 5 | | | V-2 | GLIPR2 | 0.61 |
| 1229 | 3 | 4 | 5 | | | V-2 | FAM110B | 0.66 | 1324 | 3 | 4 | 5 | | | V-2 | GLS2 | 0.66 |
| 1230 | 3 | 4 | 5 | | | V-2 | FAM116B | 0.66 | 1325 | 3 | 4 | 5 | | | V-2 | GLT25D1 | 0.59 |
| 1231 | 3 | 4 | 5 | | | V-2 | FAM118B | 0.67 | 1326 | 3 | 4 | 5 | | | V-2 | GLTPD1 | 0.55 |
| 1232 | 3 | 4 | 5 | | | V-2 | FAM125A | 0.51 | 1327 | 3 | 4 | 5 | | | V-2 | GNAI2 | 0.55 |
| 1233 | 3 | 4 | 5 | | | V-2 | FAM125B | 0.65 | 1328 | 3 | 4 | 5 | | | V-2 | GNB1L | 0.64 |
| 1234 | 3 | 4 | 5 | | | V-2 | FAM127B | 0.62 | 1329 | 3 | 4 | 5 | | | V-2 | GNG10 | 0.55 |
| 1235 | 3 | 4 | 5 | | | V-2 | FAM127C | 0.57 | 1330 | 3 | 4 | 5 | | | V-2 | GNG5 | 0.57 |
| 1236 | 3 | 4 | 5 | | | V-2 | FAM160A2 | 0.67 | 1331 | 3 | 4 | 5 | | | V-2 | GORASP2 | 0.63 |
| 1237 | 3 | 4 | 5 | | | V-2 | FAM160B2 | 0.51 | 1332 | 3 | 4 | 5 | | | V-2 | GOT1 | 0.66 |
| 1238 | 3 | 4 | 5 | | | V-2 | FAM174B | 0.59 | 1333 | 3 | 4 | 5 | | | V-2 | GOT2 | 0.62 |
| 1239 | 3 | 4 | 5 | | | V-2 | FAM176A | 0.64 | 1334 | 3 | 4 | 5 | | | V-2 | GPAA1 | 0.62 |
| 1240 | 3 | 4 | 5 | | | V-2 | FAM176B | 0.62 | 1335 | 3 | 4 | 5 | | | V-2 | GPC1 | 0.61 |
| 1241 | 3 | 4 | 5 | | | V-2 | FAM181B | 0.64 | 1336 | 3 | 4 | 5 | | | V-2 | GPER | 0.53 |
| 1242 | 3 | 4 | 5 | | | V-2 | FAM195A | 0.66 | 1337 | 3 | 4 | 5 | | | V-2 | GPKOW | 0.60 |
| 1243 | 3 | 4 | 5 | | | V-2 | FAM212A | 0.56 | 1338 | 3 | 4 | 5 | | | V-2 | GPR108 | 0.51 |
| 1244 | 3 | 4 | 5 | | | V-2 | FAM3A | 0.54 | 1339 | 3 | 4 | 5 | | | V-2 | GPR153 | 0.56 |
| 1245 | 3 | 4 | 5 | | | V-2 | FAM50B | 0.60 | 1340 | 3 | 4 | 5 | | | V-2 | GPRC5B | 0.65 |
| | | | | | | | | | 1341 | 3 | 4 | 5 | | | V-2 | GPRC5C | 0.52 |

Fig. 38 - 8

| | | | | | | | | | | | | | | | | |
|---|---|---|---|---|---|---|---|---|---|---|---|---|---|---|---|---|
| 1342 | 3 | 4 | 5 | | V-2 | GPS1 | 0.57 | | 1438 | 3 | 4 | 5 | | V-2 | KIAA0284 | 0.51 |
| 1343 | 3 | 4 | 5 | | V-2 | GPSM1 | 0.66 | | 1439 | 3 | 4 | 5 | | V-2 | KIAA0930 | 0.62 |
| 1344 | 3 | 4 | 5 | | V-2 | GPX1 | 0.58 | | 1440 | 3 | 4 | 5 | | V-2 | KIAA1324 | 0.64 |
| 1345 | 3 | 4 | 5 | | V-2 | GRHPR | 0.59 | | 1441 | 3 | 4 | 5 | | V-2 | KIAA1522 | 0.57 |
| 1346 | 3 | 4 | 5 | | V-2 | GRINA | 0.61 | | 1442 | 3 | 4 | 5 | | V-2 | KIAA1967 | 0.66 |
| 1347 | 3 | 4 | 5 | | V-2 | GRWD1 | 0.52 | | 1443 | 3 | 4 | 5 | | V-2 | KIF17 | 0.67 |
| 1348 | 3 | 4 | 5 | | V-2 | GSN | 0.55 | | 1444 | 3 | 4 | 5 | | V-2 | KIF1C | 0.57 |
| 1349 | 3 | 4 | 5 | | V-2 | GSS | 0.64 | | 1445 | 3 | 4 | 5 | | V-2 | KIF22 | 0.57 |
| 1350 | 3 | 4 | 5 | | V-2 | GTF3C5 | 0.58 | | 1446 | 3 | 4 | 5 | | V-2 | KIF26A | 0.64 |
| 1351 | 3 | 4 | 5 | | V-2 | GTPBP6 | 0.57 | | 1447 | 3 | 4 | 5 | | V-2 | KLF2 | 0.59 |
| 1352 | 3 | 4 | 5 | | V-2 | GTSE1 | 0.67 | | 1448 | 3 | 4 | 5 | | V-2 | KLHL26 | 0.65 |
| 1353 | 3 | 4 | 5 | | V-2 | GUK1 | 0.57 | | 1449 | 3 | 4 | 5 | | V-2 | KLK1 | 0.60 |
| 1354 | 3 | 4 | 5 | | V-2 | GYPC | 0.65 | | 1450 | 3 | 4 | 5 | | V-2 | KPNA2 | 0.64 |
| 1355 | 3 | 4 | 5 | | V-2 | GYS1 | 0.55 | | 1451 | 3 | 4 | 5 | | V-2 | KRBA1 | 0.66 |
| 1356 | 3 | 4 | 5 | | V-2 | H2AFX | 0.54 | | 1452 | 3 | 4 | 5 | | V-2 | KRT19 | 0.51 |
| 1357 | 3 | 4 | 5 | | V-2 | HAGH | 0.63 | | 1453 | 3 | 4 | 5 | | V-2 | KRTCAP2 | 0.57 |
| 1358 | 3 | 4 | 5 | | V-2 | HAPLN3 | 0.55 | | 1454 | 3 | 4 | 5 | | V-2 | KRTCAP3 | 0.64 |
| 1359 | 3 | 4 | 5 | | V-2 | HAX1 | 0.62 | | 1455 | 3 | 4 | 5 | | V-2 | KXD1 | 0.61 |
| 1360 | 3 | 4 | 5 | | V-2 | HDAC3 | 0.61 | | 1456 | 3 | 4 | 5 | | V-2 | L3MBTL2 | 0.60 |
| 1361 | 3 | 4 | 5 | | V-2 | HDAC6 | 0.61 | | 1457 | 3 | 4 | 5 | | V-2 | LAG3 | 0.66 |
| 1362 | 3 | 4 | 5 | | V-2 | HDAC7 | 0.54 | | 1458 | 3 | 4 | 5 | | V-2 | LAMA3 | 0.59 |
| 1363 | 3 | 4 | 5 | | V-2 | HDGFRP2 | 0.59 | | 1459 | 3 | 4 | 5 | | V-2 | LAMB2 | 0.59 |
| 1364 | 3 | 4 | 5 | | V-2 | HEATR2 | 0.63 | | 1460 | 3 | 4 | 5 | | V-2 | LAMTOR2 | 0.56 |
| 1365 | 3 | 4 | 5 | | V-2 | HECTD3 | 0.59 | | 1461 | 3 | 4 | 5 | | V-2 | LAPTM4B | 0.64 |
| 1366 | 3 | 4 | 5 | | V-2 | HGS | 0.50 | | 1462 | 3 | 4 | 5 | | V-2 | LASP1 | 0.61 |
| 1367 | 3 | 4 | 5 | | V-2 | HGSNAT | 0.66 | | 1463 | 3 | 4 | 5 | | V-2 | LDHA | 0.56 |
| 1368 | 3 | 4 | 5 | | V-2 | HHLA3 | 0.61 | | 1464 | 3 | 4 | 5 | | V-2 | LENG1 | 0.56 |
| 1369 | 3 | 4 | 5 | | V-2 | HIGD2A | 0.52 | | 1465 | 3 | 4 | 5 | | V-2 | LEPREL4 | 0.50 |
| 1370 | 3 | 4 | 5 | | V-2 | HIP1R | 0.59 | | 1466 | 3 | 4 | 5 | | V-2 | LGALS1 | 0.53 |
| 1371 | 3 | 4 | 5 | | V-2 | HIVEP1 | 0.59 | | 1467 | 3 | 4 | 5 | | V-2 | LGALS3 | 0.59 |
| 1372 | 3 | 4 | 5 | | V-2 | HLA-B | 0.64 | | 1468 | 3 | 4 | 5 | | V-2 | LGALS7B | 0.55 |
| 1373 | 3 | 4 | 5 | | V-2 | HLA-E | 0.60 | | 1469 | 3 | 4 | 5 | | V-2 | LIG1 | 0.64 |
| 1374 | 3 | 4 | 5 | | V-2 | HM13 | 0.53 | | 1470 | 3 | 4 | 5 | | V-2 | LIN7B | 0.63 |
| 1375 | 3 | 4 | 5 | | V-2 | HMG20B | 0.53 | | 1471 | 3 | 4 | 5 | | V-2 | LINC00094 | 0.64 |
| 1376 | 3 | 4 | 5 | | V-2 | HOXA4 | 0.55 | | 1472 | 3 | 4 | 5 | | V-2 | LMCD1 | 0.53 |
| 1377 | 3 | 4 | 5 | | V-2 | HOXA7 | 0.60 | | 1473 | 3 | 4 | 5 | | V-2 | LMNB1 | 0.61 |
| 1378 | 3 | 4 | 5 | | V-2 | HOXB2 | 0.57 | | 1474 | 3 | 4 | 5 | | V-2 | LMTK3 | 0.61 |
| 1379 | 3 | 4 | 5 | | V-2 | HOXC9 | 0.52 | | 1475 | 3 | 4 | 5 | | V-2 | LOC100127888 | 0.60 |
| 1380 | 3 | 4 | 5 | | V-2 | HPCAL1 | 0.59 | | 1476 | 3 | 4 | 5 | | V-2 | LOC100128252 | 0.52 |
| 1381 | 3 | 4 | 5 | | V-2 | HPRT1 | 0.67 | | 1477 | 3 | 4 | 5 | | V-2 | LOC100132831 | 0.62 |
| 1382 | 3 | 4 | 5 | | V-2 | HPS1 | 0.60 | | 1478 | 3 | 4 | 5 | | V-2 | LOC100288123 | 0.63 |
| 1383 | 3 | 4 | 5 | | V-2 | HS3ST3A1 | 0.59 | | 1479 | 3 | 4 | 5 | | V-2 | LOC100499489 | 0.63 |
| 1384 | 3 | 4 | 5 | | V-2 | HSBP1 | 0.62 | | 1480 | 3 | 4 | 5 | | V-2 | LOC100505681 | 0.65 |
| 1385 | 3 | 4 | 5 | | V-2 | HSD11B2 | 0.51 | | 1481 | 3 | 4 | 5 | | V-2 | LOC148413 | 0.61 |
| 1386 | 3 | 4 | 5 | | V-2 | HTRA2 | 0.67 | | 1482 | 3 | 4 | 5 | | V-2 | LOC151009 | 0.56 |
| 1387 | 3 | 4 | 5 | | V-2 | HYAL2 | 0.59 | | 1483 | 3 | 4 | 5 | | V-2 | LOC339524 | 0.59 |
| 1388 | 3 | 4 | 5 | | V-2 | HYOU1 | 0.55 | | 1484 | 3 | 4 | 5 | | V-2 | LOC399744 | 0.67 |
| 1389 | 3 | 4 | 5 | | V-2 | ID3 | 0.63 | | 1485 | 3 | 4 | 5 | | V-2 | LOC493754 | 0.55 |
| 1390 | 3 | 4 | 5 | | V-2 | IDH3B | 0.59 | | 1486 | 3 | 4 | 5 | | V-2 | LOC550643 | 0.65 |
| 1391 | 3 | 4 | 5 | | V-2 | IDH3G | 0.52 | | 1487 | 3 | 4 | 5 | | V-2 | LOC613038 | 0.53 |
| 1392 | 3 | 4 | 5 | | V-2 | IFI27L1 | 0.50 | | 1488 | 3 | 4 | 5 | | V-2 | LOC645166 | 0.58 |
| 1393 | 3 | 4 | 5 | | V-2 | IFI35 | 0.66 | | 1489 | 3 | 4 | 5 | | V-2 | LOC728875 | 0.53 |
| 1394 | 3 | 4 | 5 | | V-2 | IFITM1 | 0.64 | | 1490 | 3 | 4 | 5 | | V-2 | LOC90784 | 0.60 |
| 1395 | 3 | 4 | 5 | | V-2 | IFITM10 | 0.61 | | 1491 | 3 | 4 | 5 | | V-2 | LONP1 | 0.63 |
| 1396 | 3 | 4 | 5 | | V-2 | IFITM3 | 0.50 | | 1492 | 3 | 4 | 5 | | V-2 | LOXL1 | 0.50 |
| 1397 | 3 | 4 | 5 | | V-2 | IFRD2 | 0.67 | | 1493 | 3 | 4 | 5 | | V-2 | LPHN1 | 0.61 |
| 1398 | 3 | 4 | 5 | | V-2 | IGF2 | 0.52 | | 1494 | 3 | 4 | 5 | | V-2 | LRP3 | 0.51 |
| 1399 | 3 | 4 | 5 | | V-2 | IGF2BP2 | 0.62 | | 1495 | 3 | 4 | 5 | | V-2 | LRP5 | 0.56 |
| 1400 | 3 | 4 | 5 | | V-2 | IGHMBP2 | 0.57 | | 1496 | 3 | 4 | 5 | | V-2 | LRRC42 | 0.67 |
| 1401 | 3 | 4 | 5 | | V-2 | IGSF8 | 0.54 | | 1497 | 3 | 4 | 5 | | V-2 | LRRC59 | 0.62 |
| 1402 | 3 | 4 | 5 | | V-2 | IKBKG | 0.58 | | 1498 | 3 | 4 | 5 | | V-2 | LRRN4CL | 0.59 |
| 1403 | 3 | 4 | 5 | | V-2 | IL17RC | 0.62 | | 1499 | 3 | 4 | 5 | | V-2 | LRSAM1 | 0.60 |
| 1404 | 3 | 4 | 5 | | V-2 | IL18BP | 0.63 | | 1500 | 3 | 4 | 5 | | V-2 | LSM1 | 0.62 |
| 1405 | 3 | 4 | 5 | | V-2 | IL2RG | 0.53 | | 1501 | 3 | 4 | 5 | | V-2 | LSM12 | 0.60 |
| 1406 | 3 | 4 | 5 | | V-2 | IL4R | 0.59 | | 1502 | 3 | 4 | 5 | | V-2 | LSM14B | 0.67 |
| 1407 | 3 | 4 | 5 | | V-2 | IMP3 | 0.61 | | 1503 | 3 | 4 | 5 | | V-2 | LSM4 | 0.59 |
| 1408 | 3 | 4 | 5 | | V-2 | IMP4 | 0.60 | | 1504 | 3 | 4 | 5 | | V-2 | LSS | 0.63 |
| 1409 | 3 | 4 | 5 | | V-2 | IMPA2 | 0.59 | | 1505 | 3 | 4 | 5 | | V-2 | LTBP4 | 0.66 |
| 1410 | 3 | 4 | 5 | | V-2 | INO80B | 0.63 | | 1506 | 3 | 4 | 5 | | V-2 | LTBR | 0.56 |
| 1411 | 3 | 4 | 5 | | V-2 | INPP5K | 0.62 | | 1507 | 3 | 4 | 5 | | V-2 | LURAP1 | 0.64 |
| 1412 | 3 | 4 | 5 | | V-2 | INTS9 | 0.58 | | 1508 | 3 | 4 | 5 | | V-2 | LYL1 | 0.60 |
| 1413 | 3 | 4 | 5 | | V-2 | IP6K1 | 0.64 | | 1509 | 3 | 4 | 5 | | V-2 | LYPD1 | 0.65 |
| 1414 | 3 | 4 | 5 | | V-2 | IQCE | 0.57 | | 1510 | 3 | 4 | 5 | | V-2 | LZTS2 | 0.59 |
| 1415 | 3 | 4 | 5 | | V-2 | IQSEC2 | 0.56 | | 1511 | 3 | 4 | 5 | | V-2 | MAF1 | 0.51 |
| 1416 | 3 | 4 | 5 | | V-2 | IRF2BPL | 0.58 | | 1512 | 3 | 4 | 5 | | V-2 | MAN1B1 | 0.65 |
| 1417 | 3 | 4 | 5 | | V-2 | IRF3 | 0.53 | | 1513 | 3 | 4 | 5 | | V-2 | MAP1S | 0.51 |
| 1418 | 3 | 4 | 5 | | V-2 | IRF5 | 0.64 | | 1514 | 3 | 4 | 5 | | V-2 | MAP2K7 | 0.52 |
| 1419 | 3 | 4 | 5 | | V-2 | IRF9 | 0.66 | | 1515 | 3 | 4 | 5 | | V-2 | MAP3K11 | 0.51 |
| 1420 | 3 | 4 | 5 | | V-2 | IRS1 | 0.63 | | 1516 | 3 | 4 | 5 | | V-2 | MAP3K14 | 0.67 |
| 1421 | 3 | 4 | 5 | | V-2 | IRX4 | 0.54 | | 1517 | 3 | 4 | 5 | | V-2 | MAP4 | 0.64 |
| 1422 | 3 | 4 | 5 | | V-2 | ISLR | 0.51 | | 1518 | 3 | 4 | 5 | | V-2 | MAPK3 | 0.64 |
| 1423 | 3 | 4 | 5 | | V-2 | ISM1 | 0.67 | | 1519 | 3 | 4 | 5 | | V-2 | MAPK7 | 0.61 |
| 1424 | 3 | 4 | 5 | | V-2 | ISY1 | 0.64 | | 1520 | 3 | 4 | 5 | | V-2 | MARCH2 | 0.61 |
| 1425 | 3 | 4 | 5 | | V-2 | ITIH5 | 0.50 | | 1521 | 3 | 4 | 5 | | V-2 | MARVELD1 | 0.55 |
| 1426 | 3 | 4 | 5 | | V-2 | ITPK1 | 0.50 | | 1522 | 3 | 4 | 5 | | V-2 | MARVELD3 | 0.63 |
| 1427 | 3 | 4 | 5 | | V-2 | ITPR2 | 0.65 | | 1523 | 3 | 4 | 5 | | V-2 | MB | 0.62 |
| 1428 | 3 | 4 | 5 | | V-2 | JMJD8 | 0.52 | | 1524 | 3 | 4 | 5 | | V-2 | MBD2 | 0.62 |
| 1429 | 3 | 4 | 5 | | V-2 | JOSD2 | 0.58 | | 1525 | 3 | 4 | 5 | | V-2 | MBD3 | 0.57 |
| 1430 | 3 | 4 | 5 | | V-2 | JUND | 0.62 | | 1526 | 3 | 4 | 5 | | V-2 | MC1R | 0.61 |
| 1431 | 3 | 4 | 5 | | V-2 | KAT8 | 0.65 | | 1527 | 3 | 4 | 5 | | V-2 | MCAT | 0.63 |
| 1432 | 3 | 4 | 5 | | V-2 | KCNAB2 | 0.51 | | 1528 | 3 | 4 | 5 | | V-2 | MCM2 | 0.62 |
| 1433 | 3 | 4 | 5 | | V-2 | KCNMB4 | 0.51 | | 1529 | 3 | 4 | 5 | | V-2 | MCM5 | 0.52 |
| 1434 | 3 | 4 | 5 | | V-2 | KCTD13 | 0.54 | | 1530 | 3 | 4 | 5 | | V-2 | MCM7 | 0.65 |
| 1435 | 3 | 4 | 5 | | V-2 | KDELR3 | 0.64 | | 1531 | 3 | 4 | 5 | | V-2 | MCRS1 | 0.62 |
| 1436 | 3 | 4 | 5 | | V-2 | KHSRP | 0.56 | | 1532 | 3 | 4 | 5 | | V-2 | MDFI | 0.50 |
| 1437 | 3 | 4 | 5 | | V-2 | KIAA0195 | 0.66 | | 1533 | 3 | 4 | 5 | | V-2 | MEA1 | 0.61 |

Fig. 38 - 9

| | | | | | | | | | | | | | | | | |
|---|---|---|---|---|---|---|---|---|---|---|---|---|---|---|---|---|
| 1534 | 3 | 4 | 5 | | | V-2 | MED11 | 0.65 | 1630 | 3 | 4 | 5 | | | V-2 | NDUFV1 | 0.63 |
| 1535 | 3 | 4 | 5 | | | V-2 | MED15 | 0.52 | 1631 | 3 | 4 | 5 | | | V-2 | NEK2 | 0.59 |
| 1536 | 3 | 4 | 5 | | | V-2 | MED24 | 0.52 | 1632 | 3 | 4 | 5 | | | V-2 | NENF | 0.62 |
| 1537 | 3 | 4 | 5 | | | V-2 | MED25 | 0.52 | 1633 | 3 | 4 | 5 | | | V-2 | NEURL1B | 0.58 |
| 1538 | 3 | 4 | 5 | | | V-2 | MED26 | 0.67 | 1634 | 3 | 4 | 5 | | | V-2 | NF2 | 0.57 |
| 1539 | 3 | 4 | 5 | | | V-2 | MED27 | 0.56 | 1635 | 3 | 4 | 5 | | | V-2 | NFATC1 | 0.54 |
| 1540 | 3 | 4 | 5 | | | V-2 | MEF2BNB | 0.62 | 1636 | 3 | 4 | 5 | | | V-2 | NFE2L1 | 0.58 |
| 1541 | 3 | 4 | 5 | | | V-2 | MEN1 | 0.52 | 1637 | 3 | 4 | 5 | | | V-2 | NFKB2 | 0.55 |
| 1542 | 3 | 4 | 5 | | | V-2 | MET | 0.62 | 1638 | 3 | 4 | 5 | | | V-2 | NFYC | 0.61 |
| 1543 | 3 | 4 | 5 | | | V-2 | METRN | 0.57 | 1639 | 3 | 4 | 5 | | | V-2 | NHP2 | 0.59 |
| 1544 | 3 | 4 | 5 | | | V-2 | MFGE8 | 0.58 | 1640 | 3 | 4 | 5 | | | V-2 | NHSL1 | 0.66 |
| 1545 | 3 | 4 | 5 | | | V-2 | MFSD10 | 0.65 | 1641 | 3 | 4 | 5 | | | V-2 | NIT1 | 0.66 |
| 1546 | 3 | 4 | 5 | | | V-2 | MFSD12 | 0.59 | 1642 | 3 | 4 | 5 | | | V-2 | NMB | 0.53 |
| 1547 | 3 | 4 | 5 | | | V-2 | MFSD7 | 0.61 | 1643 | 3 | 4 | 5 | | | V-2 | NMRAL1 | 0.64 |
| 1548 | 3 | 4 | 5 | | | V-2 | MGAT3 | 0.58 | 1644 | 3 | 4 | 5 | | | V-2 | NOB1 | 0.62 |
| 1549 | 3 | 4 | 5 | | | V-2 | MGRN1 | 0.59 | 1645 | 3 | 4 | 5 | | | V-2 | NOC2L | 0.50 |
| 1550 | 3 | 4 | 5 | | | V-2 | MICAL1 | 0.62 | 1646 | 3 | 4 | 5 | | | V-2 | NOL6 | 0.55 |
| 1551 | 3 | 4 | 5 | | | V-2 | MIEN1 | 0.53 | 1647 | 3 | 4 | 5 | | | V-2 | NONO | 0.65 |
| 1552 | 3 | 4 | 5 | | | V-2 | MIER2 | 0.55 | 1648 | 3 | 4 | 5 | | | V-2 | NOP16 | 0.62 |
| 1553 | 3 | 4 | 5 | | | V-2 | MIF4GD | 0.59 | 1649 | 3 | 4 | 5 | | | V-2 | NOV | 0.58 |
| 1554 | 3 | 4 | 5 | | | V-2 | MIIP | 0.64 | 1650 | 3 | 4 | 5 | | | V-2 | NPDC1 | 0.50 |
| 1555 | 3 | 4 | 5 | | | V-2 | MINK1 | 0.57 | 1651 | 3 | 4 | 5 | | | V-2 | NPHP4 | 0.61 |
| 1556 | 3 | 4 | 5 | | | V-2 | MKI67 | 0.56 | 1652 | 3 | 4 | 5 | | | V-2 | NPRL2 | 0.52 |
| 1557 | 3 | 4 | 5 | | | V-2 | MLLT1 | 0.66 | 1653 | 3 | 4 | 5 | | | V-2 | NPTXR | 0.53 |
| 1558 | 3 | 4 | 5 | | | V-2 | MMP11 | 0.60 | 1654 | 3 | 4 | 5 | | | V-2 | NR2F6 | 0.57 |
| 1559 | 3 | 4 | 5 | | | V-2 | MMP14 | 0.55 | 1655 | 3 | 4 | 5 | | | V-2 | NRBP1 | 0.56 |
| 1560 | 3 | 4 | 5 | | | V-2 | MOB3A | 0.63 | 1656 | 3 | 4 | 5 | | | V-2 | NRG2 | 0.51 |
| 1561 | 3 | 4 | 5 | | | V-2 | MOGS | 0.62 | 1657 | 3 | 4 | 5 | | | V-2 | NRSN2 | 0.54 |
| 1562 | 3 | 4 | 5 | | | V-2 | MORC2 | 0.62 | 1658 | 3 | 4 | 5 | | | V-2 | NSA2 | 0.67 |
| 1563 | 3 | 4 | 5 | | | V-2 | MORC2-AS1 | 0.66 | 1659 | 3 | 4 | 5 | | | V-2 | NT5C | 0.56 |
| 1564 | 3 | 4 | 5 | | | V-2 | MPDU1 | 0.62 | 1660 | 3 | 4 | 5 | | | V-2 | NTN1 | 0.61 |
| 1565 | 3 | 4 | 5 | | | V-2 | MPG | 0.51 | 1661 | 3 | 4 | 5 | | | V-2 | NTN4 | 0.67 |
| 1566 | 3 | 4 | 5 | | | V-2 | MRM1 | 0.66 | 1662 | 3 | 4 | 5 | | | V-2 | NUCB1 | 0.55 |
| 1567 | 3 | 4 | 5 | | | V-2 | MRP63 | 0.63 | 1663 | 3 | 4 | 5 | | | V-2 | NUDC | 0.59 |
| 1568 | 3 | 4 | 5 | | | V-2 | MRPL10 | 0.59 | 1664 | 3 | 4 | 5 | | | V-2 | NUDT11 | 0.62 |
| 1569 | 3 | 4 | 5 | | | V-2 | MRPL16 | 0.63 | 1665 | 3 | 4 | 5 | | | V-2 | NUDT22 | 0.60 |
| 1570 | 3 | 4 | 5 | | | V-2 | MRPL17 | 0.54 | 1666 | 3 | 4 | 5 | | | V-2 | NUMBL | 0.58 |
| 1571 | 3 | 4 | 5 | | | V-2 | MRPL18 | 0.67 | 1667 | 3 | 4 | 5 | | | V-2 | NUP188 | 0.59 |
| 1572 | 3 | 4 | 5 | | | V-2 | MRPL2 | 0.65 | 1668 | 3 | 4 | 5 | | | V-2 | NUP93 | 0.57 |
| 1573 | 3 | 4 | 5 | | | V-2 | MRPL23 | 0.57 | 1669 | 3 | 4 | 5 | | | V-2 | NXN | 0.63 |
| 1574 | 3 | 4 | 5 | | | V-2 | MRPL27 | 0.64 | 1670 | 3 | 4 | 5 | | | V-2 | OAF | 0.63 |
| 1575 | 3 | 4 | 5 | | | V-2 | MRPL28 | 0.53 | 1671 | 3 | 4 | 5 | | | V-2 | OAZ2 | 0.65 |
| 1576 | 3 | 4 | 5 | | | V-2 | MRPL34 | 0.55 | 1672 | 3 | 4 | 5 | | | V-2 | OBFC2B | 0.63 |
| 1577 | 3 | 4 | 5 | | | V-2 | MRPL38 | 0.56 | 1673 | 3 | 4 | 5 | | | V-2 | OGFRL1 | 0.64 |
| 1578 | 3 | 4 | 5 | | | V-2 | MRPL52 | 0.57 | 1674 | 3 | 4 | 5 | | | V-2 | OLA1 | 0.63 |
| 1579 | 3 | 4 | 5 | | | V-2 | MRPL53 | 0.54 | 1675 | 3 | 4 | 5 | | | V-2 | ORAI3 | 0.55 |
| 1580 | 3 | 4 | 5 | | | V-2 | MRPL54 | 0.66 | 1676 | 3 | 4 | 5 | | | V-2 | ORMDL3 | 0.66 |
| 1581 | 3 | 4 | 5 | | | V-2 | MRPL55 | 0.59 | 1677 | 3 | 4 | 5 | | | V-2 | OSBP2 | 0.59 |
| 1582 | 3 | 4 | 5 | | | V-2 | MRPL9 | 0.59 | 1678 | 3 | 4 | 5 | | | V-2 | OSBPL10 | 0.59 |
| 1583 | 3 | 4 | 5 | | | V-2 | MRPS18B | 0.65 | 1679 | 3 | 4 | 5 | | | V-2 | OSBPL5 | 0.53 |
| 1584 | 3 | 4 | 5 | | | V-2 | MRPS2 | 0.54 | 1680 | 3 | 4 | 5 | | | V-2 | OSR2 | 0.67 |
| 1585 | 3 | 4 | 5 | | | V-2 | MRPS24 | 0.62 | 1681 | 3 | 4 | 5 | | | V-2 | OTUD5 | 0.52 |
| 1586 | 3 | 4 | 5 | | | V-2 | MRPS26 | 0.62 | 1682 | 3 | 4 | 5 | | | V-2 | OTX1 | 0.67 |
| 1587 | 3 | 4 | 5 | | | V-2 | MRPS31 | 0.65 | 1683 | 3 | 4 | 5 | | | V-2 | OVCA2 | 0.52 |
| 1588 | 3 | 4 | 5 | | | V-2 | MRPS5 | 0.64 | 1684 | 3 | 4 | 5 | | | V-2 | P4HA2 | 0.55 |
| 1589 | 3 | 4 | 5 | | | V-2 | MRTO4 | 0.64 | 1685 | 3 | 4 | 5 | | | V-2 | PA2G4 | 0.56 |
| 1590 | 3 | 4 | 5 | | | V-2 | MSRA | 0.67 | 1686 | 3 | 4 | 5 | | | V-2 | PACS2 | 0.63 |
| 1591 | 3 | 4 | 5 | | | V-2 | MT1X | 0.57 | 1687 | 3 | 4 | 5 | | | V-2 | PADI2 | 0.51 |
| 1592 | 3 | 4 | 5 | | | V-2 | MTA2 | 0.57 | 1688 | 3 | 4 | 5 | | | V-2 | PAF1 | 0.59 |
| 1593 | 3 | 4 | 5 | | | V-2 | MTFMT | 0.65 | 1689 | 3 | 4 | 5 | | | V-2 | PAFAH1B3 | 0.55 |
| 1594 | 3 | 4 | 5 | | | V-2 | MTFP1 | 0.52 | 1690 | 3 | 4 | 5 | | | V-2 | PAK6 | 0.57 |
| 1595 | 3 | 4 | 5 | | | V-2 | MTSS1L | 0.62 | 1691 | 3 | 4 | 5 | | | V-2 | PALMD | 0.58 |
| 1596 | 3 | 4 | 5 | | | V-2 | MUC20 | 0.58 | 1692 | 3 | 4 | 5 | | | V-2 | PANK4 | 0.51 |
| 1597 | 3 | 4 | 5 | | | V-2 | MUSTN1 | 0.60 | 1693 | 3 | 4 | 5 | | | V-2 | PANX1 | 0.58 |
| 1598 | 3 | 4 | 5 | | | V-2 | MVP | 0.53 | 1694 | 3 | 4 | 5 | | | V-2 | PARL | 0.66 |
| 1599 | 3 | 4 | 5 | | | V-2 | MXRA8 | 0.52 | 1695 | 3 | 4 | 5 | | | V-2 | PARS2 | 0.60 |
| 1600 | 3 | 4 | 5 | | | V-2 | MYEOV | 0.58 | 1696 | 3 | 4 | 5 | | | V-2 | PARVB | 0.61 |
| 1601 | 3 | 4 | 5 | | | V-2 | MYH9 | 0.53 | 1697 | 3 | 4 | 5 | | | V-2 | PATZ1 | 0.61 |
| 1602 | 3 | 4 | 5 | | | V-2 | MYL12B | 0.64 | 1698 | 3 | 4 | 5 | | | V-2 | PBX2 | 0.66 |
| 1603 | 3 | 4 | 5 | | | V-2 | MYO1C | 0.56 | 1699 | 3 | 4 | 5 | | | V-2 | PCBD1 | 0.66 |
| 1604 | 3 | 4 | 5 | | | V-2 | MYPOP | 0.56 | 1700 | 3 | 4 | 5 | | | V-2 | PCBP1 | 0.64 |
| 1605 | 3 | 4 | 5 | | | V-2 | MZT2A | 0.66 | 1701 | 3 | 4 | 5 | | | V-2 | PCBP4 | 0.55 |
| 1606 | 3 | 4 | 5 | | | V-2 | MZT2B | 0.60 | 1702 | 3 | 4 | 5 | | | V-2 | PCDHGC3 | 0.56 |
| 1607 | 3 | 4 | 5 | | | V-2 | NAA10 | 0.51 | 1703 | 3 | 4 | 5 | | | V-2 | PCGF2 | 0.50 |
| 1608 | 3 | 4 | 5 | | | V-2 | NAA60 | 0.56 | 1704 | 3 | 4 | 5 | | | V-2 | PCIF1 | 0.59 |
| 1609 | 3 | 4 | 5 | | | V-2 | NAALADL1 | 0.58 | 1705 | 3 | 4 | 5 | | | V-2 | PCNA-AS1 | 0.63 |
| 1610 | 3 | 4 | 5 | | | V-2 | NAGPA | 0.61 | 1706 | 3 | 4 | 5 | | | V-2 | PCNXL3 | 0.60 |
| 1611 | 3 | 4 | 5 | | | V-2 | NANS | 0.60 | 1707 | 3 | 4 | 5 | | | V-2 | PCYT2 | 0.61 |
| 1612 | 3 | 4 | 5 | | | V-2 | NARF | 0.60 | 1708 | 3 | 4 | 5 | | | V-2 | PDAP1 | 0.53 |
| 1613 | 3 | 4 | 5 | | | V-2 | NCAPH2 | 0.56 | 1709 | 3 | 4 | 5 | | | V-2 | PDCD5 | 0.58 |
| 1614 | 3 | 4 | 5 | | | V-2 | NCK2 | 0.55 | 1710 | 3 | 4 | 5 | | | V-2 | PDE4A | 0.51 |
| 1615 | 3 | 4 | 5 | | | V-2 | NCOA5 | 0.63 | 1711 | 3 | 4 | 5 | | | V-2 | PDE6D | 0.57 |
| 1616 | 3 | 4 | 5 | | | V-2 | NCOR2 | 0.56 | 1712 | 3 | 4 | 5 | | | V-2 | PDE9A | 0.62 |
| 1617 | 3 | 4 | 5 | | | V-2 | NDNL2 | 0.66 | 1713 | 3 | 4 | 5 | | | V-2 | PDHA2 | 0.65 |
| 1618 | 3 | 4 | 5 | | | V-2 | NDOR1 | 0.51 | 1714 | 3 | 4 | 5 | | | V-2 | PDK2 | 0.57 |
| 1619 | 3 | 4 | 5 | | | V-2 | NDRG2 | 0.55 | 1715 | 3 | 4 | 5 | | | V-2 | PDK4 | 0.65 |
| 1620 | 3 | 4 | 5 | | | V-2 | NDUFA11 | 0.62 | 1716 | 3 | 4 | 5 | | | V-2 | PDXP | 0.64 |
| 1621 | 3 | 4 | 5 | | | V-2 | NDUFA13 | 0.52 | 1717 | 3 | 4 | 5 | | | V-2 | PDZD11 | 0.53 |
| 1622 | 3 | 4 | 5 | | | V-2 | NDUFA2 | 0.64 | 1718 | 3 | 4 | 5 | | | V-2 | PEF1 | 0.61 |
| 1623 | 3 | 4 | 5 | | | V-2 | NDUFA8 | 0.61 | 1719 | 3 | 4 | 5 | | | V-2 | PELI3 | 0.57 |
| 1624 | 3 | 4 | 5 | | | V-2 | NDUFB4 | 0.63 | 1720 | 3 | 4 | 5 | | | V-2 | PEMT | 0.53 |
| 1625 | 3 | 4 | 5 | | | V-2 | NDUFB7 | 0.52 | 1721 | 3 | 4 | 5 | | | V-2 | PER1 | 0.65 |
| 1626 | 3 | 4 | 5 | | | V-2 | NDUFB9 | 0.65 | 1722 | 3 | 4 | 5 | | | V-2 | PEX10 | 0.66 |
| 1627 | 3 | 4 | 5 | | | V-2 | NDUFS3 | 0.60 | 1723 | 3 | 4 | 5 | | | V-2 | PEX14 | 0.64 |
| 1628 | 3 | 4 | 5 | | | V-2 | NDUFS5 | 0.63 | 1724 | 3 | 4 | 5 | | | V-2 | PFDN1 | 0.65 |
| 1629 | 3 | 4 | 5 | | | V-2 | NDUFS8 | 0.52 | 1725 | 3 | 4 | 5 | | | V-2 | PFKL | 0.53 |

Fig. 38 - 10

| | | | | | | | | | | | | | | | | |
|---|---|---|---|---|---|---|---|---|---|---|---|---|---|---|---|---|
| 1726 | 3 | 4 | 5 | | | V-2 | PFKP | 0.59 | 1822 | 3 | 4 | 5 | | | V-2 | PTBP1 | 0.61 |
| 1727 | 3 | 4 | 5 | | | V-2 | PGAP3 | 0.60 | 1823 | 3 | 4 | 5 | | | V-2 | PTDSS2 | 0.54 |
| 1728 | 3 | 4 | 5 | | | V-2 | PGF | 0.50 | 1824 | 3 | 4 | 5 | | | V-2 | PTGES2 | 0.55 |
| 1729 | 3 | 4 | 5 | | | V-2 | PHC2 | 0.52 | 1825 | 3 | 4 | 5 | | | V-2 | PTK2B | 0.62 |
| 1730 | 3 | 4 | 5 | | | V-2 | PHF1 | 0.66 | 1826 | 3 | 4 | 5 | | | V-2 | PTK7 | 0.64 |
| 1731 | 3 | 4 | 5 | | | V-2 | PHF5A | 0.60 | 1827 | 3 | 4 | 5 | | | V-2 | PTP4A3 | 0.66 |
| 1732 | 3 | 4 | 5 | | | V-2 | PHLDB1 | 0.65 | 1828 | 3 | 4 | 5 | | | V-2 | PTPMT1 | 0.62 |
| 1733 | 3 | 4 | 5 | | | V-2 | PHLPP1 | 0.62 | 1829 | 3 | 4 | 5 | | | V-2 | PTPN18 | 0.64 |
| 1734 | 3 | 4 | 5 | | | V-2 | PHPT1 | 0.55 | 1830 | 3 | 4 | 5 | | | V-2 | PTPRU | 0.66 |
| 1735 | 3 | 4 | 5 | | | V-2 | PHRF1 | 0.64 | 1831 | 3 | 4 | 5 | | | V-2 | PTTG2 | 0.57 |
| 1736 | 3 | 4 | 5 | | | V-2 | PHYHIP | 0.66 | 1832 | 3 | 4 | 5 | | | V-2 | PXDC1 | 0.58 |
| 1737 | 3 | 4 | 5 | | | V-2 | PICK1 | 0.67 | 1833 | 3 | 4 | 5 | | | V-2 | PYCR1 | 0.64 |
| 1738 | 3 | 4 | 5 | | | V-2 | PIGO | 0.56 | 1834 | 3 | 4 | 5 | | | V-2 | PYGB | 0.60 |
| 1739 | 3 | 4 | 5 | | | V-2 | PIGU | 0.58 | 1835 | 3 | 4 | 5 | | | V-2 | PYGO2 | 0.64 |
| 1740 | 3 | 4 | 5 | | | V-2 | PIN1 | 0.57 | 1836 | 3 | 4 | 5 | | | V-2 | R3HCC1 | 0.59 |
| 1741 | 3 | 4 | 5 | | | V-2 | PITPNM3 | 0.64 | 1837 | 3 | 4 | 5 | | | V-2 | R3HDM2 | 0.65 |
| 1742 | 3 | 4 | 5 | | | V-2 | PKD1P1 | 0.67 | 1838 | 3 | 4 | 5 | | | V-2 | RAB11FIP3 | 0.65 |
| 1743 | 3 | 4 | 5 | | | V-2 | PKIG | 0.63 | 1839 | 3 | 4 | 5 | | | V-2 | RAB11FIP5 | 0.64 |
| 1744 | 3 | 4 | 5 | | | V-2 | PKMYT1 | 0.64 | 1840 | 3 | 4 | 5 | | | V-2 | RAB34 | 0.63 |
| 1745 | 3 | 4 | 5 | | | V-2 | PKN1 | 0.65 | 1841 | 3 | 4 | 5 | | | V-2 | RAB35 | 0.58 |
| 1746 | 3 | 4 | 5 | | | V-2 | PKNOX2 | 0.58 | 1842 | 3 | 4 | 5 | | | V-2 | RAB36 | 0.58 |
| 1747 | 3 | 4 | 5 | | | V-2 | PLA2G3 | 0.63 | 1843 | 3 | 4 | 5 | | | V-2 | RAB3IL1 | 0.50 |
| 1748 | 3 | 4 | 5 | | | V-2 | PLA2G4C | 0.61 | 1844 | 3 | 4 | 5 | | | V-2 | RAB40C | 0.53 |
| 1749 | 3 | 4 | 5 | | | V-2 | PLA2G4F | 0.66 | 1845 | 3 | 4 | 5 | | | V-2 | RAB43 | 0.59 |
| 1750 | 3 | 4 | 5 | | | V-2 | PLA2G6 | 0.61 | 1846 | 3 | 4 | 5 | | | V-2 | RAB4B | 0.64 |
| 1751 | 3 | 4 | 5 | | | V-2 | PLAC9 | 0.61 | 1847 | 3 | 4 | 5 | | | V-2 | RAB5C | 0.53 |
| 1752 | 3 | 4 | 5 | | | V-2 | PLCD3 | 0.63 | 1848 | 3 | 4 | 5 | | | V-2 | RAB8A | 0.63 |
| 1753 | 3 | 4 | 5 | | | V-2 | PLD2 | 0.66 | 1849 | 3 | 4 | 5 | | | V-2 | RABAC1 | 0.51 |
| 1754 | 3 | 4 | 5 | | | V-2 | PLEKHA4 | 0.53 | 1850 | 3 | 4 | 5 | | | V-2 | RABEP2 | 0.62 |
| 1755 | 3 | 4 | 5 | | | V-2 | PLEKHH3 | 0.53 | 1851 | 3 | 4 | 5 | | | V-2 | RABL2B | 0.67 |
| 1756 | 3 | 4 | 5 | | | V-2 | PLOD1 | 0.52 | 1852 | 3 | 4 | 5 | | | V-2 | RAD51B | 0.56 |
| 1757 | 3 | 4 | 5 | | | V-2 | PLTP | 0.55 | 1853 | 3 | 4 | 5 | | | V-2 | RADIL | 0.62 |
| 1758 | 3 | 4 | 5 | | | V-2 | PLXNB1 | 0.66 | 1854 | 3 | 4 | 5 | | | V-2 | RAI2 | 0.56 |
| 1759 | 3 | 4 | 5 | | | V-2 | PLXNB2 | 0.61 | 1855 | 3 | 4 | 5 | | | V-2 | RAMP3 | 0.55 |
| 1760 | 3 | 4 | 5 | | | V-2 | PMEPA1 | 0.65 | 1856 | 3 | 4 | 5 | | | V-2 | RAN | 0.67 |
| 1761 | 3 | 4 | 5 | | | V-2 | PMF1 | 0.54 | 1857 | 3 | 4 | 5 | | | V-2 | RANBP1 | 0.67 |
| 1762 | 3 | 4 | 5 | | | V-2 | PMP22 | 0.54 | 1858 | 3 | 4 | 5 | | | V-2 | RANBP3 | 0.50 |
| 1763 | 3 | 4 | 5 | | | V-2 | PNKD | 0.54 | 1859 | 3 | 4 | 5 | | | V-2 | RANGAP1 | 0.61 |
| 1764 | 3 | 4 | 5 | | | V-2 | PNKP | 0.55 | 1860 | 3 | 4 | 5 | | | V-2 | RAPGEF1 | 0.56 |
| 1765 | 3 | 4 | 5 | | | V-2 | PNPLA6 | 0.61 | 1861 | 3 | 4 | 5 | | | V-2 | RAPGEFL1 | 0.63 |
| 1766 | 3 | 4 | 5 | | | V-2 | POLD1 | 0.54 | 1862 | 3 | 4 | 5 | | | V-2 | RASD2 | 0.56 |
| 1767 | 3 | 4 | 5 | | | V-2 | POLD4 | 0.64 | 1863 | 3 | 4 | 5 | | | V-2 | RASSF7 | 0.58 |
| 1768 | 3 | 4 | 5 | | | V-2 | POLG | 0.66 | 1864 | 3 | 4 | 5 | | | V-2 | RBCK1 | 0.55 |
| 1769 | 3 | 4 | 5 | | | V-2 | POLR2E | 0.59 | 1865 | 3 | 4 | 5 | | | V-2 | RBFA | 0.62 |
| 1770 | 3 | 4 | 5 | | | V-2 | POLR2F | 0.58 | 1866 | 3 | 4 | 5 | | | V-2 | RBM10 | 0.59 |
| 1771 | 3 | 4 | 5 | | | V-2 | POLR2J | 0.64 | 1867 | 3 | 4 | 5 | | | V-2 | RBM38 | 0.62 |
| 1772 | 3 | 4 | 5 | | | V-2 | POLR2J3 | 0.57 | 1868 | 3 | 4 | 5 | | | V-2 | RCC1 | 0.56 |
| 1773 | 3 | 4 | 5 | | | V-2 | POLR2L | 0.56 | 1869 | 3 | 4 | 5 | | | V-2 | RCN3 | 0.56 |
| 1774 | 3 | 4 | 5 | | | V-2 | POLR3H | 0.58 | 1870 | 3 | 4 | 5 | | | V-2 | RCVRN | 0.51 |
| 1775 | 3 | 4 | 5 | | | V-2 | POLRMT | 0.61 | 1871 | 3 | 4 | 5 | | | V-2 | RDBP | 0.66 |
| 1776 | 3 | 4 | 5 | | | V-2 | POMGNT1 | 0.57 | 1872 | 3 | 4 | 5 | | | V-2 | REEP4 | 0.50 |
| 1777 | 3 | 4 | 5 | | | V-2 | POP7 | 0.51 | 1873 | 3 | 4 | 5 | | | V-2 | REM2 | 0.59 |
| 1778 | 3 | 4 | 5 | | | V-2 | POTEKP | 0.58 | 1874 | 3 | 4 | 5 | | | V-2 | REPIN1 | 0.66 |
| 1779 | 3 | 4 | 5 | | | V-2 | PPA1 | 0.57 | 1875 | 3 | 4 | 5 | | | V-2 | RFC2 | 0.64 |
| 1780 | 3 | 4 | 5 | | | V-2 | PPAN | 0.65 | 1876 | 3 | 4 | 5 | | | V-2 | RFC5 | 0.66 |
| 1781 | 3 | 4 | 5 | | | V-2 | PPFIA3 | 0.64 | 1877 | 3 | 4 | 5 | | | V-2 | RFNG | 0.56 |
| 1782 | 3 | 4 | 5 | | | V-2 | PPIA | 0.64 | 1878 | 3 | 4 | 5 | | | V-2 | RFTN1 | 0.65 |
| 1783 | 3 | 4 | 5 | | | V-2 | PPIB | 0.55 | 1879 | 3 | 4 | 5 | | | V-2 | RFXANK | 0.56 |
| 1784 | 3 | 4 | 5 | | | V-2 | PPIL1 | 0.64 | 1880 | 3 | 4 | 5 | | | V-2 | RGS12 | 0.67 |
| 1785 | 3 | 4 | 5 | | | V-2 | PPM1G | 0.55 | 1881 | 3 | 4 | 5 | | | V-2 | RHBDD2 | 0.52 |
| 1786 | 3 | 4 | 5 | | | V-2 | PPME1 | 0.53 | 1882 | 3 | 4 | 5 | | | V-2 | RHBDF2 | 0.57 |
| 1787 | 3 | 4 | 5 | | | V-2 | PPP1R11 | 0.58 | 1883 | 3 | 4 | 5 | | | V-2 | RHEB | 0.65 |
| 1788 | 3 | 4 | 5 | | | V-2 | PPP1R13B | 0.56 | 1884 | 3 | 4 | 5 | | | V-2 | RHOA | 0.66 |
| 1789 | 3 | 4 | 5 | | | V-2 | PPP1R37 | 0.56 | 1885 | 3 | 4 | 5 | | | V-2 | RHOBTB2 | 0.55 |
| 1790 | 3 | 4 | 5 | | | V-2 | PPP1R7 | 0.65 | 1886 | 3 | 4 | 5 | | | V-2 | RHOC | 0.52 |
| 1791 | 3 | 4 | 5 | | | V-2 | PPP2R5B | 0.54 | 1887 | 3 | 4 | 5 | | | V-2 | RIC8A | 0.64 |
| 1792 | 3 | 4 | 5 | | | V-2 | PPP2R5D | 0.57 | 1888 | 3 | 4 | 5 | | | V-2 | RILP | 0.63 |
| 1793 | 3 | 4 | 5 | | | V-2 | PPP4C | 0.57 | 1889 | 3 | 4 | 5 | | | V-2 | RIN3 | 0.54 |
| 1794 | 3 | 4 | 5 | | | V-2 | PPP5C | 0.63 | 1890 | 3 | 4 | 5 | | | V-2 | RING1 | 0.56 |
| 1795 | 3 | 4 | 5 | | | V-2 | PPP6R1 | 0.52 | 1891 | 3 | 4 | 5 | | | V-2 | RIPK3 | 0.63 |
| 1796 | 3 | 4 | 5 | | | V-2 | PPP6R2 | 0.60 | 1892 | 3 | 4 | 5 | | | V-2 | RMI2 | 0.52 |
| 1797 | 3 | 4 | 5 | | | V-2 | PQLC1 | 0.63 | 1893 | 3 | 4 | 5 | | | V-2 | RNASEK | 0.55 |
| 1798 | 3 | 4 | 5 | | | V-2 | PQLC2 | 0.63 | 1894 | 3 | 4 | 5 | | | V-2 | RNF123 | 0.66 |
| 1799 | 3 | 4 | 5 | | | V-2 | PRCC | 0.51 | 1895 | 3 | 4 | 5 | | | V-2 | RNF126 | 0.51 |
| 1800 | 3 | 4 | 5 | | | V-2 | PRDX6 | 0.65 | 1896 | 3 | 4 | 5 | | | V-2 | RNF220 | 0.53 |
| 1801 | 3 | 4 | 5 | | | V-2 | PRKACA | 0.50 | 1897 | 3 | 4 | 5 | | | V-2 | RNF25 | 0.63 |
| 1802 | 3 | 4 | 5 | | | V-2 | PRKAG1 | 0.67 | 1898 | 3 | 4 | 5 | | | V-2 | RNF31 | 0.67 |
| 1803 | 3 | 4 | 5 | | | V-2 | PRPF31 | 0.66 | 1899 | 3 | 4 | 5 | | | V-2 | RNF40 | 0.53 |
| 1804 | 3 | 4 | 5 | | | V-2 | PRR24 | 0.53 | 1900 | 3 | 4 | 5 | | | V-2 | RNF5P1 | 0.55 |
| 1805 | 3 | 4 | 5 | | | V-2 | PRR5 | 0.58 | 1901 | 3 | 4 | 5 | | | V-2 | RNH1 | 0.57 |
| 1806 | 3 | 4 | 5 | | | V-2 | PRRG2 | 0.61 | 1902 | 3 | 4 | 5 | | | V-2 | RNPEP | 0.66 |
| 1807 | 3 | 4 | 5 | | | V-2 | PRRT1 | 0.57 | 1903 | 3 | 4 | 5 | | | V-2 | RNPS1 | 0.57 |
| 1808 | 3 | 4 | 5 | | | V-2 | PRUNE | 0.62 | 1904 | 3 | 4 | 5 | | | V-2 | ROGDI | 0.61 |
| 1809 | 3 | 4 | 5 | | | V-2 | PSENEN | 0.66 | 1905 | 3 | 4 | 5 | | | V-2 | ROM1 | 0.63 |
| 1810 | 3 | 4 | 5 | | | V-2 | PSMB10 | 0.61 | 1906 | 3 | 4 | 5 | | | V-2 | RPA3 | 0.57 |
| 1811 | 3 | 4 | 5 | | | V-2 | PSMB7 | 0.56 | 1907 | 3 | 4 | 5 | | | V-2 | RPAP1 | 0.54 |
| 1812 | 3 | 4 | 5 | | | V-2 | PSMC3 | 0.64 | 1908 | 3 | 4 | 5 | | | V-2 | RPL10 | 0.60 |
| 1813 | 3 | 4 | 5 | | | V-2 | PSMC5 | 0.66 | 1909 | 3 | 4 | 5 | | | V-2 | RPL13AP20 | 0.62 |
| 1814 | 3 | 4 | 5 | | | V-2 | PSMD13 | 0.64 | 1910 | 3 | 4 | 5 | | | V-2 | RPL27A | 0.59 |
| 1815 | 3 | 4 | 5 | | | V-2 | PSMD4 | 0.63 | 1911 | 3 | 4 | 5 | | | V-2 | RPL28 | 0.63 |
| 1816 | 3 | 4 | 5 | | | V-2 | PSMD9 | 0.59 | 1912 | 3 | 4 | 5 | | | V-2 | RPL29 | 0.58 |
| 1817 | 3 | 4 | 5 | | | V-2 | PSME1 | 0.60 | 1913 | 3 | 4 | 5 | | | V-2 | RPL39L | 0.63 |
| 1818 | 3 | 4 | 5 | | | V-2 | PSMF1 | 0.61 | 1914 | 3 | 4 | 5 | | | V-2 | RPL4 | 0.66 |
| 1819 | 3 | 4 | 5 | | | V-2 | PSMG2 | 0.65 | 1915 | 3 | 4 | 5 | | | V-2 | RPL6 | 0.66 |
| 1820 | 3 | 4 | 5 | | | V-2 | PSMG3 | 0.60 | 1916 | 3 | 4 | 5 | | | V-2 | RPL7A | 0.65 |
| 1821 | 3 | 4 | 5 | | | V-2 | PSRC1 | 0.50 | 1917 | 3 | 4 | 5 | | | V-2 | RPL9 | 0.53 |

Fig. 38 - 11

| | | | | | | | | | | | | | | | |
|---|---|---|---|---|---|---|---|---|---|---|---|---|---|---|---|
| 1918 | 3 | 4 | 5 | | | V-2 | RPP21 | 0.53 | 2014 | 3 | 4 | 5 | | V-2 | SMARCB1 | 0.53 |
| 1919 | 3 | 4 | 5 | | | V-2 | RPP40 | 0.61 | 2015 | 3 | 4 | 5 | | V-2 | SMARCD1 | 0.58 |
| 1920 | 3 | 4 | 5 | | | V-2 | RPS13 | 0.59 | 2016 | 3 | 4 | 5 | | V-2 | SMO | 0.65 |
| 1921 | 3 | 4 | 5 | | | V-2 | RPS15 | 0.55 | 2017 | 3 | 4 | 5 | | V-2 | SMPD4 | 0.62 |
| 1922 | 3 | 4 | 5 | | | V-2 | RPS16 | 0.55 | 2018 | 3 | 4 | 5 | | V-2 | SMYD2 | 0.64 |
| 1923 | 3 | 4 | 5 | | | V-2 | RPS17 | 0.64 | 2019 | 3 | 4 | 5 | | V-2 | SMYD5 | 0.64 |
| 1924 | 3 | 4 | 5 | | | V-2 | RPS17L | 0.65 | 2020 | 3 | 4 | 5 | | V-2 | SNAPC4 | 0.53 |
| 1925 | 3 | 4 | 5 | | | V-2 | RPS19 | 0.67 | 2021 | 3 | 4 | 5 | | V-2 | SNAPC5 | 0.62 |
| 1926 | 3 | 4 | 5 | | | V-2 | RPS19BP1 | 0.66 | 2022 | 3 | 4 | 5 | | V-2 | SNF8 | 0.50 |
| 1927 | 3 | 4 | 5 | | | V-2 | RPS20 | 0.66 | 2023 | 3 | 4 | 5 | | V-2 | SNRPB | 0.61 |
| 1928 | 3 | 4 | 5 | | | V-2 | RPS6KA1 | 0.62 | 2024 | 3 | 4 | 5 | | V-2 | SNRPC | 0.66 |
| 1929 | 3 | 4 | 5 | | | V-2 | RPS6KA4 | 0.55 | 2025 | 3 | 4 | 5 | | V-2 | SNRPF | 0.58 |
| 1930 | 3 | 4 | 5 | | | V-2 | RPS6KB2 | 0.62 | 2026 | 3 | 4 | 5 | | V-2 | SNTA1 | 0.61 |
| 1931 | 3 | 4 | 5 | | | V-2 | RPS9 | 0.60 | 2027 | 3 | 4 | 5 | | V-2 | SNX15 | 0.56 |
| 1932 | 3 | 4 | 5 | | | V-2 | RPUSD3 | 0.54 | 2028 | 3 | 4 | 5 | | V-2 | SNX17 | 0.67 |
| 1933 | 3 | 4 | 5 | | | V-2 | RRAS | 0.50 | 2029 | 3 | 4 | 5 | | V-2 | SNX21 | 0.63 |
| 1934 | 3 | 4 | 5 | | | V-2 | RRBP1 | 0.61 | 2030 | 3 | 4 | 5 | | V-2 | SNX22 | 0.61 |
| 1935 | 3 | 4 | 5 | | | V-2 | RTN4 | 0.60 | 2031 | 3 | 4 | 5 | | V-2 | SOD3 | 0.56 |
| 1936 | 3 | 4 | 5 | | | V-2 | RTN4RL2 | 0.52 | 2032 | 3 | 4 | 5 | | V-2 | SOX13 | 0.60 |
| 1937 | 3 | 4 | 5 | | | V-2 | RUSC1 | 0.51 | 2033 | 3 | 4 | 5 | | V-2 | SOX8 | 0.57 |
| 1938 | 3 | 4 | 5 | | | V-2 | RUVBL2 | 0.51 | 2034 | 3 | 4 | 5 | | V-2 | SP2 | 0.60 |
| 1939 | 3 | 4 | 5 | | | V-2 | RXRB | 0.58 | 2035 | 3 | 4 | 5 | | V-2 | SPA17 | 0.54 |
| 1940 | 3 | 4 | 5 | | | V-2 | S100A3 | 0.66 | 2036 | 3 | 4 | 5 | | V-2 | SPARC | 0.58 |
| 1941 | 3 | 4 | 5 | | | V-2 | S100A4 | 0.62 | 2037 | 3 | 4 | 5 | | V-2 | SPNS1 | 0.59 |
| 1942 | 3 | 4 | 5 | | | V-2 | S100A6 | 0.64 | 2038 | 3 | 4 | 5 | | V-2 | SPON2 | 0.56 |
| 1943 | 3 | 4 | 5 | | | V-2 | S1PR2 | 0.59 | 2039 | 3 | 4 | 5 | | V-2 | SPRED2 | 0.58 |
| 1944 | 3 | 4 | 5 | | | V-2 | SAE1 | 0.57 | 2040 | 3 | 4 | 5 | | V-2 | SPRY2 | 0.67 |
| 1945 | 3 | 4 | 5 | | | V-2 | SALL2 | 0.61 | 2041 | 3 | 4 | 5 | | V-2 | SPRY4 | 0.51 |
| 1946 | 3 | 4 | 5 | | | V-2 | SBNO2 | 0.61 | 2042 | 3 | 4 | 5 | | V-2 | SPSB1 | 0.51 |
| 1947 | 3 | 4 | 5 | | | V-2 | SCARA3 | 0.66 | 2043 | 3 | 4 | 5 | | V-2 | SQSTM1 | 0.67 |
| 1948 | 3 | 4 | 5 | | | V-2 | SCARA5 | 0.57 | 2044 | 3 | 4 | 5 | | V-2 | SRA1 | 0.66 |
| 1949 | 3 | 4 | 5 | | | V-2 | SCARF2 | 0.66 | 2045 | 3 | 4 | 5 | | V-2 | SRC | 0.67 |
| 1950 | 3 | 4 | 5 | | | V-2 | SCN1B | 0.67 | 2046 | 3 | 4 | 5 | | V-2 | SRCAP | 0.62 |
| 1951 | 3 | 4 | 5 | | | V-2 | SCN4B | 0.59 | 2047 | 3 | 4 | 5 | | V-2 | SRPR | 0.56 |
| 1952 | 3 | 4 | 5 | | | V-2 | SCNM1 | 0.56 | 2048 | 3 | 4 | 5 | | V-2 | SRRM3 | 0.63 |
| 1953 | 3 | 4 | 5 | | | V-2 | SCO2 | 0.54 | 2049 | 3 | 4 | 5 | | V-2 | SRSF9 | 0.66 |
| 1954 | 3 | 4 | 5 | | | V-2 | SCRIB | 0.56 | 2050 | 3 | 4 | 5 | | V-2 | SSBP3 | 0.51 |
| 1955 | 3 | 4 | 5 | | | V-2 | SCYL1 | 0.56 | 2051 | 3 | 4 | 5 | | V-2 | SSC5D | 0.60 |
| 1956 | 3 | 4 | 5 | | | V-2 | SDC2 | 0.65 | 2052 | 3 | 4 | 5 | | V-2 | SSH3 | 0.53 |
| 1957 | 3 | 4 | 5 | | | V-2 | SDF4 | 0.63 | 2053 | 3 | 4 | 5 | | V-2 | SSSCA1 | 0.54 |
| 1958 | 3 | 4 | 5 | | | V-2 | SDHAF1 | 0.63 | 2054 | 3 | 4 | 5 | | V-2 | ST3GAL2 | 0.67 |
| 1959 | 3 | 4 | 5 | | | V-2 | SEC13 | 0.59 | 2055 | 3 | 4 | 5 | | V-2 | ST3GAL4 | 0.54 |
| 1960 | 3 | 4 | 5 | | | V-2 | SEC14L1 | 0.66 | 2056 | 3 | 4 | 5 | | V-2 | ST6GALNAC6 | 0.55 |
| 1961 | 3 | 4 | 5 | | | V-2 | SEC61B | 0.59 | 2057 | 3 | 4 | 5 | | V-2 | ST7 | 0.53 |
| 1962 | 3 | 4 | 5 | | | V-2 | SECTM1 | 0.54 | 2058 | 3 | 4 | 5 | | V-2 | ST7-AS1 | 0.54 |
| 1963 | 3 | 4 | 5 | | | V-2 | SEMA3F | 0.59 | 2059 | 3 | 4 | 5 | | V-2 | STARD3 | 0.62 |
| 1964 | 3 | 4 | 5 | | | V-2 | SEMA3G | 0.58 | 2060 | 3 | 4 | 5 | | V-2 | STEAP3 | 0.61 |
| 1965 | 3 | 4 | 5 | | | V-2 | SEMA4B | 0.63 | 2061 | 3 | 4 | 5 | | V-2 | STIP1 | 0.55 |
| 1966 | 3 | 4 | 5 | | | V-2 | SEMA5B | 0.56 | 2062 | 3 | 4 | 5 | | V-2 | STK11 | 0.58 |
| 1967 | 3 | 4 | 5 | | | V-2 | SEPN1 | 0.56 | 2063 | 3 | 4 | 5 | | V-2 | STK11IP | 0.57 |
| 1968 | 3 | 4 | 5 | | | V-2 | SEPT3 | 0.62 | 2064 | 3 | 4 | 5 | | V-2 | STK32B | 0.55 |
| 1969 | 3 | 4 | 5 | | | V-2 | SEPT9 | 0.57 | 2065 | 3 | 4 | 5 | | V-2 | STOML1 | 0.60 |
| 1970 | 3 | 4 | 5 | | | V-2 | SERPINH1 | 0.54 | 2066 | 3 | 4 | 5 | | V-2 | STRA13 | 0.57 |
| 1971 | 3 | 4 | 5 | | | V-2 | SF3B2 | 0.60 | 2067 | 3 | 4 | 5 | | V-2 | STRN4 | 0.53 |
| 1972 | 3 | 4 | 5 | | | V-2 | SFXN3 | 0.52 | 2068 | 3 | 4 | 5 | | V-2 | STX5 | 0.57 |
| 1973 | 3 | 4 | 5 | | | V-2 | SGSH | 0.60 | 2069 | 3 | 4 | 5 | | V-2 | STX8 | 0.66 |
| 1974 | 3 | 4 | 5 | | | V-2 | SGSM3 | 0.63 | 2070 | 3 | 4 | 5 | | V-2 | SUGP1 | 0.65 |
| 1975 | 3 | 4 | 5 | | | V-2 | SGTA | 0.54 | 2071 | 3 | 4 | 5 | | V-2 | SULF2 | 0.66 |
| 1976 | 3 | 4 | 5 | | | V-2 | SH2B2 | 0.56 | 2072 | 3 | 4 | 5 | | V-2 | SUMF2 | 0.62 |
| 1977 | 3 | 4 | 5 | | | V-2 | SH3BP4 | 0.56 | 2073 | 3 | 4 | 5 | | V-2 | SUPT4H1 | 0.59 |
| 1978 | 3 | 4 | 5 | | | V-2 | SHBGLB2 | 0.62 | 2074 | 3 | 4 | 5 | | V-2 | SUPT5H | 0.61 |
| 1979 | 3 | 4 | 5 | | | V-2 | SHARPIN | 0.53 | 2075 | 3 | 4 | 5 | | V-2 | SURF1 | 0.53 |
| 1980 | 3 | 4 | 5 | | | V-2 | SHISA3 | 0.66 | 2076 | 3 | 4 | 5 | | V-2 | SURF2 | 0.51 |
| 1981 | 3 | 4 | 5 | | | V-2 | SHISA5 | 0.59 | 2077 | 3 | 4 | 5 | | V-2 | SUV39H1 | 0.50 |
| 1982 | 3 | 4 | 5 | | | V-2 | SHKBP1 | 0.63 | 2078 | 3 | 4 | 5 | | V-2 | SYDE1 | 0.60 |
| 1983 | 3 | 4 | 5 | | | V-2 | SHQ1 | 0.65 | 2079 | 3 | 4 | 5 | | V-2 | SYMPK | 0.62 |
| 1984 | 3 | 4 | 5 | | | V-2 | SIGIRR | 0.65 | 2080 | 3 | 4 | 5 | | V-2 | SYT7 | 0.55 |
| 1985 | 3 | 4 | 5 | | | V-2 | SIGMAR1 | 0.54 | 2081 | 3 | 4 | 5 | | V-2 | SYTL1 | 0.63 |
| 1986 | 3 | 4 | 5 | | | V-2 | SIX5 | 0.57 | 2082 | 3 | 4 | 5 | | V-2 | SYVN1 | 0.53 |
| 1987 | 3 | 4 | 5 | | | V-2 | SKI | 0.63 | 2083 | 3 | 4 | 5 | | V-2 | TAB1 | 0.66 |
| 1988 | 3 | 4 | 5 | | | V-2 | SKIV2L | 0.60 | 2084 | 3 | 4 | 5 | | V-2 | TACC3 | 0.50 |
| 1989 | 3 | 4 | 5 | | | V-2 | SLC12A9 | 0.60 | 2085 | 3 | 4 | 5 | | V-2 | TAF12 | 0.61 |
| 1990 | 3 | 4 | 5 | | | V-2 | SLC16A5 | 0.66 | 2086 | 3 | 4 | 5 | | V-2 | TAF6L | 0.59 |
| 1991 | 3 | 4 | 5 | | | V-2 | SLC1A5 | 0.51 | 2087 | 3 | 4 | 5 | | V-2 | TAOK2 | 0.63 |
| 1992 | 3 | 4 | 5 | | | V-2 | SLC24A5 | 0.52 | 2088 | 3 | 4 | 5 | | V-2 | TARBP2 | 0.55 |
| 1993 | 3 | 4 | 5 | | | V-2 | SLC25A10 | 0.58 | 2089 | 3 | 4 | 5 | | V-2 | TAX1BP3 | 0.51 |
| 1994 | 3 | 4 | 5 | | | V-2 | SLC25A22 | 0.56 | 2090 | 3 | 4 | 5 | | V-2 | TBC1D10A | 0.53 |
| 1995 | 3 | 4 | 5 | | | V-2 | SLC25A34 | 0.67 | 2091 | 3 | 4 | 5 | | V-2 | TBC1D17 | 0.63 |
| 1996 | 3 | 4 | 5 | | | V-2 | SLC27A1 | 0.55 | 2092 | 3 | 4 | 5 | | V-2 | TBC1D22A | 0.66 |
| 1997 | 3 | 4 | 5 | | | V-2 | SLC2A4RG | 0.55 | 2093 | 3 | 4 | 5 | | V-2 | TBCB | 0.60 |
| 1998 | 3 | 4 | 5 | | | V-2 | SLC35B2 | 0.60 | 2094 | 3 | 4 | 5 | | V-2 | TBKBP1 | 0.63 |
| 1999 | 3 | 4 | 5 | | | V-2 | SLC35C2 | 0.63 | 2095 | 3 | 4 | 5 | | V-2 | TBL2 | 0.67 |
| 2000 | 3 | 4 | 5 | | | V-2 | SLC37A1 | 0.61 | 2096 | 3 | 4 | 5 | | V-2 | TBRG4 | 0.57 |
| 2001 | 3 | 4 | 5 | | | V-2 | SLC38A5 | 0.54 | 2097 | 3 | 4 | 5 | | V-2 | TBX2 | 0.59 |
| 2002 | 3 | 4 | 5 | | | V-2 | SLC39A1 | 0.51 | 2098 | 3 | 4 | 5 | | V-2 | TBX6 | 0.51 |
| 2003 | 3 | 4 | 5 | | | V-2 | SLC39A4 | 0.55 | 2099 | 3 | 4 | 5 | | V-2 | TBXA2R | 0.67 |
| 2004 | 3 | 4 | 5 | | | V-2 | SLC39A7 | 0.66 | 2100 | 3 | 4 | 5 | | V-2 | TCEA2 | 0.57 |
| 2005 | 3 | 4 | 5 | | | V-2 | SLC3A2 | 0.54 | 2101 | 3 | 4 | 5 | | V-2 | TCEB2 | 0.58 |
| 2006 | 3 | 4 | 5 | | | V-2 | SLC43A1 | 0.63 | 2102 | 3 | 4 | 5 | | V-2 | TCF19 | 0.60 |
| 2007 | 3 | 4 | 5 | | | V-2 | SLC44A2 | 0.58 | 2103 | 3 | 4 | 5 | | V-2 | TCF3 | 0.57 |
| 2008 | 3 | 4 | 5 | | | V-2 | SLC48A1 | 0.58 | 2104 | 3 | 4 | 5 | | V-2 | TCFL5 | 0.63 |
| 2009 | 3 | 4 | 5 | | | V-2 | SLC4A2 | 0.53 | 2105 | 3 | 4 | 5 | | V-2 | TCOF1 | 0.61 |
| 2010 | 3 | 4 | 5 | | | V-2 | SLC6A8 | 0.53 | 2106 | 3 | 4 | 5 | | V-2 | TCTN2 | 0.54 |
| 2011 | 3 | 4 | 5 | | | V-2 | SLC9A3R1 | 0.64 | 2107 | 3 | 4 | 5 | | V-2 | TEAD2 | 0.54 |
| 2012 | 3 | 4 | 5 | | | V-2 | SLX1B-SULT1A4 | 0.52 | 2108 | 3 | 4 | 5 | | V-2 | TEAD3 | 0.64 |
| 2013 | 3 | 4 | 5 | | | V-2 | SMAD7 | 0.55 | 2109 | 3 | 4 | 5 | | V-2 | TFAP2A | 0.65 |

Fig. 38 - 12

| | | | | | | | | | | | | | | | | |
|---|---|---|---|---|---|---|---|---|---|---|---|---|---|---|---|---|
| 2110 | 3 | 4 | 5 | | | V-2 | TFE3 | 0.56 | 2206 | 3 | 4 | 5 | | | V-2 | UBE2O | 0.62 |
| 2111 | 3 | 4 | 5 | | | V-2 | TFEB | 0.50 | 2207 | 3 | 4 | 5 | | | V-2 | UBE2V1 | 0.66 |
| 2112 | 3 | 4 | 5 | | | V-2 | TFIP11 | 0.66 | 2208 | 3 | 4 | 5 | | | V-2 | UBL4A | 0.64 |
| 2113 | 3 | 4 | 5 | | | V-2 | TGIF1 | 0.61 | 2209 | 3 | 4 | 5 | | | V-2 | UBOX5 | 0.61 |
| 2114 | 3 | 4 | 5 | | | V-2 | TGM3 | 0.57 | 2210 | 3 | 4 | 5 | | | V-2 | UBTF | 0.63 |
| 2115 | 3 | 4 | 5 | | | V-2 | TIMM17B | 0.51 | 2211 | 3 | 4 | 5 | | | V-2 | UBXN1 | 0.55 |
| 2116 | 3 | 4 | 5 | | | V-2 | TIMM44 | 0.63 | 2212 | 3 | 4 | 5 | | | V-2 | UBXN6 | 0.50 |
| 2117 | 3 | 4 | 5 | | | V-2 | TIMM8B | 0.63 | 2213 | 3 | 4 | 5 | | | V-2 | UFSP1 | 0.57 |
| 2118 | 3 | 4 | 5 | | | V-2 | TIMP1 | 0.59 | 2214 | 3 | 4 | 5 | | | V-2 | UNC119 | 0.65 |
| 2119 | 3 | 4 | 5 | | | V-2 | TIMP3 | 0.58 | 2215 | 3 | 4 | 5 | | | V-2 | UNC93B1 | 0.65 |
| 2120 | 3 | 4 | 5 | | | V-2 | TLE1 | 0.58 | 2216 | 3 | 4 | 5 | | | V-2 | UPRT | 0.64 |
| 2121 | 3 | 4 | 5 | | | V-2 | TM9SF4 | 0.61 | 2217 | 3 | 4 | 5 | | | V-2 | UQCR10 | 0.63 |
| 2122 | 3 | 4 | 5 | | | V-2 | TMED1 | 0.66 | 2218 | 3 | 4 | 5 | | | V-2 | UQCRC1 | 0.64 |
| 2123 | 3 | 4 | 5 | | | V-2 | TMEM11 | 0.54 | 2219 | 3 | 4 | 5 | | | V-2 | URGCP | 0.61 |
| 2124 | 3 | 4 | 5 | | | V-2 | TMEM133 | 0.65 | 2220 | 3 | 4 | 5 | | | V-2 | USE1 | 0.63 |
| 2125 | 3 | 4 | 5 | | | V-2 | TMEM134 | 0.51 | 2221 | 3 | 4 | 5 | | | V-2 | USF2 | 0.52 |
| 2126 | 3 | 4 | 5 | | | V-2 | TMEM141 | 0.62 | 2222 | 3 | 4 | 5 | | | V-2 | USP11 | 0.56 |
| 2127 | 3 | 4 | 5 | | | V-2 | TMEM160 | 0.51 | 2223 | 3 | 4 | 5 | | | V-2 | USP21 | 0.51 |
| 2128 | 3 | 4 | 5 | | | V-2 | TMEM173 | 0.57 | 2224 | 3 | 4 | 5 | | | V-2 | USP35 | 0.58 |
| 2129 | 3 | 4 | 5 | | | V-2 | TMEM179B | 0.50 | 2225 | 3 | 4 | 5 | | | V-2 | UTP14A | 0.63 |
| 2130 | 3 | 4 | 5 | | | V-2 | TMEM184B | 0.54 | 2226 | 3 | 4 | 5 | | | V-2 | VAC14 | 0.62 |
| 2131 | 3 | 4 | 5 | | | V-2 | TMEM205 | 0.60 | 2227 | 3 | 4 | 5 | | | V-2 | VASH1 | 0.66 |
| 2132 | 3 | 4 | 5 | | | V-2 | TMEM214 | 0.54 | 2228 | 3 | 4 | 5 | | | V-2 | VAT1 | 0.66 |
| 2133 | 3 | 4 | 5 | | | V-2 | TMEM222 | 0.62 | 2229 | 3 | 4 | 5 | | | V-2 | VAX2 | 0.57 |
| 2134 | 3 | 4 | 5 | | | V-2 | TMEM223 | 0.60 | 2230 | 3 | 4 | 5 | | | V-2 | VDAC1 | 0.66 |
| 2135 | 3 | 4 | 5 | | | V-2 | TMEM231 | 0.54 | 2231 | 3 | 4 | 5 | | | V-2 | VDAC2 | 0.61 |
| 2136 | 3 | 4 | 5 | | | V-2 | TMEM25 | 0.64 | 2232 | 3 | 4 | 5 | | | V-2 | VIM | 0.55 |
| 2137 | 3 | 4 | 5 | | | V-2 | TMEM39B | 0.60 | 2233 | 3 | 4 | 5 | | | V-2 | VIPR1 | 0.53 |
| 2138 | 3 | 4 | 5 | | | V-2 | TMEM43 | 0.57 | 2234 | 3 | 4 | 5 | | | V-2 | VPS18 | 0.64 |
| 2139 | 3 | 4 | 5 | | | V-2 | TMEM50A | 0.64 | 2235 | 3 | 4 | 5 | | | V-2 | VPS25 | 0.65 |
| 2140 | 3 | 4 | 5 | | | V-2 | TMEM51 | 0.58 | 2236 | 3 | 4 | 5 | | | V-2 | VPS28 | 0.54 |
| 2141 | 3 | 4 | 5 | | | V-2 | TMEM63B | 0.60 | 2237 | 3 | 4 | 5 | | | V-2 | VPS4A | 0.62 |
| 2142 | 3 | 4 | 5 | | | V-2 | TMEM79 | 0.62 | 2238 | 3 | 4 | 5 | | | V-2 | VPS52 | 0.64 |
| 2143 | 3 | 4 | 5 | | | V-2 | TMEM8A | 0.52 | 2239 | 3 | 4 | 5 | | | V-2 | VPS72 | 0.56 |
| 2144 | 3 | 4 | 5 | | | V-2 | TNFAIP8L1 | 0.61 | 2240 | 3 | 4 | 5 | | | V-2 | VSIG10L | 0.52 |
| 2145 | 3 | 4 | 5 | | | V-2 | TNFRSF18 | 0.50 | 2241 | 3 | 4 | 5 | | | V-2 | VSNL1 | 0.65 |
| 2146 | 3 | 4 | 5 | | | V-2 | TNFRSF8 | 0.58 | 2242 | 3 | 4 | 5 | | | V-2 | VWA1 | 0.62 |
| 2147 | 3 | 4 | 5 | | | V-2 | TNFSF12 | 0.60 | 2243 | 3 | 4 | 5 | | | V-2 | VWF | 0.51 |
| 2148 | 3 | 4 | 5 | | | V-2 | TNIP1 | 0.55 | 2244 | 3 | 4 | 5 | | | V-2 | WARS | 0.53 |
| 2149 | 3 | 4 | 5 | | | V-2 | TNIP2 | 0.61 | 2245 | 3 | 4 | 5 | | | V-2 | WBP2 | 0.57 |
| 2150 | 3 | 4 | 5 | | | V-2 | TNRC18 | 0.65 | 2246 | 3 | 4 | 5 | | | V-2 | WDR13 | 0.66 |
| 2151 | 3 | 4 | 5 | | | V-2 | TOR2A | 0.66 | 2247 | 3 | 4 | 5 | | | V-2 | WDR45 | 0.62 |
| 2152 | 3 | 4 | 5 | | | V-2 | TP53I11 | 0.66 | 2248 | 3 | 4 | 5 | | | V-2 | WDR46 | 0.62 |
| 2153 | 3 | 4 | 5 | | | V-2 | TP53TG1 | 0.59 | 2249 | 3 | 4 | 5 | | | V-2 | WDR74 | 0.58 |
| 2154 | 3 | 4 | 5 | | | V-2 | TP73 | 0.51 | 2250 | 3 | 4 | 5 | | | V-2 | WDR81 | 0.65 |
| 2155 | 3 | 4 | 5 | | | V-2 | TPM4 | 0.60 | 2251 | 3 | 4 | 5 | | | V-2 | WDR83 | 0.56 |
| 2156 | 3 | 4 | 5 | | | V-2 | TPRA1 | 0.51 | 2252 | 3 | 4 | 5 | | | V-2 | WFDC5 | 0.65 |
| 2157 | 3 | 4 | 5 | | | V-2 | TPRXL | 0.58 | 2253 | 3 | 4 | 5 | | | V-2 | WHSC2 | 0.61 |
| 2158 | 3 | 4 | 5 | | | V-2 | TPTEP1 | 0.66 | 2254 | 3 | 4 | 5 | | | V-2 | WIBG | 0.60 |
| 2159 | 3 | 4 | 5 | | | V-2 | TRADD | 0.59 | 2255 | 3 | 4 | 5 | | | V-2 | WIZ | 0.51 |
| 2160 | 3 | 4 | 5 | | | V-2 | TRAF2 | 0.63 | 2256 | 3 | 4 | 5 | | | V-2 | WNT4 | 0.53 |
| 2161 | 3 | 4 | 5 | | | V-2 | TRAF4 | 0.66 | 2257 | 3 | 4 | 5 | | | V-2 | WWP2 | 0.66 |
| 2162 | 3 | 4 | 5 | | | V-2 | TRAP1 | 0.59 | 2258 | 3 | 4 | 5 | | | V-2 | XAB2 | 0.60 |
| 2163 | 3 | 4 | 5 | | | V-2 | TRAPPC3 | 0.63 | 2259 | 3 | 4 | 5 | | | V-2 | XPNPEP2 | 0.54 |
| 2164 | 3 | 4 | 5 | | | V-2 | TRAPPC6A | 0.65 | 2260 | 3 | 4 | 5 | | | V-2 | XPO6 | 0.66 |
| 2165 | 3 | 4 | 5 | | | V-2 | TRIM16L | 0.63 | 2261 | 3 | 4 | 5 | | | V-2 | XRCC1 | 0.51 |
| 2166 | 3 | 4 | 5 | | | V-2 | TRIM21 | 0.65 | 2262 | 3 | 4 | 5 | | | V-2 | XXYLT1 | 0.56 |
| 2167 | 3 | 4 | 5 | | | V-2 | TRIM26 | 0.50 | 2263 | 3 | 4 | 5 | | | V-2 | XYLT2 | 0.55 |
| 2168 | 3 | 4 | 5 | | | V-2 | TRIM3 | 0.60 | 2264 | 3 | 4 | 5 | | | V-2 | YARS | 0.60 |
| 2169 | 3 | 4 | 5 | | | V-2 | TRIM41 | 0.59 | 2265 | 3 | 4 | 5 | | | V-2 | YBX1 | 0.54 |
| 2170 | 3 | 4 | 5 | | | V-2 | TRIM62 | 0.64 | 2266 | 3 | 4 | 5 | | | V-2 | YDJC | 0.60 |
| 2171 | 3 | 4 | 5 | | | V-2 | TRIM8 | 0.60 | 2267 | 3 | 4 | 5 | | | V-2 | YIF1A | 0.56 |
| 2172 | 3 | 4 | 5 | | | V-2 | TRIP6 | 0.59 | 2268 | 3 | 4 | 5 | | | V-2 | YIPF3 | 0.54 |
| 2173 | 3 | 4 | 5 | | | V-2 | TRMT112 | 0.60 | 2269 | 3 | 4 | 5 | | | V-2 | YPEL3 | 0.50 |
| 2174 | 3 | 4 | 5 | | | V-2 | TRMT2A | 0.66 | 2270 | 3 | 4 | 5 | | | V-2 | YPEL4 | 0.56 |
| 2175 | 3 | 4 | 5 | | | V-2 | TRMT61A | 0.59 | 2271 | 3 | 4 | 5 | | | V-2 | YWHAH | 0.59 |
| 2176 | 3 | 4 | 5 | | | V-2 | TRNP1 | 0.60 | 2272 | 3 | 4 | 5 | | | V-2 | YY1AP1 | 0.63 |
| 2177 | 3 | 4 | 5 | | | V-2 | TRUB2 | 0.59 | 2273 | 3 | 4 | 5 | | | V-2 | ZBTB12 | 0.53 |
| 2178 | 3 | 4 | 5 | | | V-2 | TSC2 | 0.64 | 2274 | 3 | 4 | 5 | | | V-2 | ZBTB45 | 0.51 |
| 2179 | 3 | 4 | 5 | | | V-2 | TSC22D3 | 0.51 | 2275 | 3 | 4 | 5 | | | V-2 | ZBTB47 | 0.58 |
| 2180 | 3 | 4 | 5 | | | V-2 | TSC22D4 | 0.55 | 2276 | 3 | 4 | 5 | | | V-2 | ZC3H18 | 0.50 |
| 2181 | 3 | 4 | 5 | | | V-2 | TSEN54 | 0.55 | 2277 | 3 | 4 | 5 | | | V-2 | ZC3H4 | 0.66 |
| 2182 | 3 | 4 | 5 | | | V-2 | TSFM | 0.66 | 2278 | 3 | 4 | 5 | | | V-2 | ZC3H7B | 0.62 |
| 2183 | 3 | 4 | 5 | | | V-2 | TSPAN9 | 0.58 | 2279 | 3 | 4 | 5 | | | V-2 | ZDHHC4 | 0.60 |
| 2184 | 3 | 4 | 5 | | | V-2 | TSPO | 0.57 | 2280 | 3 | 4 | 5 | | | V-2 | ZER1 | 0.58 |
| 2185 | 3 | 4 | 5 | | | V-2 | TSSC1 | 0.66 | 2281 | 3 | 4 | 5 | | | V-2 | ZFAND2B | 0.66 |
| 2186 | 3 | 4 | 5 | | | V-2 | TTC4 | 0.65 | 2282 | 3 | 4 | 5 | | | V-2 | ZFYVE1 | 0.61 |
| 2187 | 3 | 4 | 5 | | | V-2 | TTC7A | 0.51 | 2283 | 3 | 4 | 5 | | | V-2 | ZFYVE19 | 0.66 |
| 2188 | 3 | 4 | 5 | | | V-2 | TTLL5 | 0.59 | 2284 | 3 | 4 | 5 | | | V-2 | ZG16B | 0.59 |
| 2189 | 3 | 4 | 5 | | | V-2 | TTYH1 | 0.55 | 2285 | 3 | 4 | 5 | | | V-2 | ZGPAT | 0.51 |
| 2190 | 3 | 4 | 5 | | | V-2 | TUBA1B | 0.60 | 2286 | 3 | 4 | 5 | | | V-2 | ZMIZ2 | 0.56 |
| 2191 | 3 | 4 | 5 | | | V-2 | TUBG1 | 0.55 | 2287 | 3 | 4 | 5 | | | V-2 | ZMYND19 | 0.51 |
| 2192 | 3 | 4 | 5 | | | V-2 | TUBGCP2 | 0.67 | 2288 | 3 | 4 | 5 | | | V-2 | ZNF219 | 0.56 |
| 2193 | 3 | 4 | 5 | | | V-2 | TULP3 | 0.65 | 2289 | 3 | 4 | 5 | | | V-2 | ZNF319 | 0.56 |
| 2194 | 3 | 4 | 5 | | | V-2 | TUSC1 | 0.56 | 2290 | 3 | 4 | 5 | | | V-2 | ZNF384 | 0.63 |
| 2195 | 3 | 4 | 5 | | | V-2 | TUSC2 | 0.66 | 2291 | 3 | 4 | 5 | | | V-2 | ZNF408 | 0.54 |
| 2196 | 3 | 4 | 5 | | | V-2 | TXN | 0.64 | 2292 | 3 | 4 | 5 | | | V-2 | ZNF428 | 0.56 |
| 2197 | 3 | 4 | 5 | | | V-2 | TXNIP | 0.52 | 2293 | 3 | 4 | 5 | | | V-2 | ZNF444 | 0.50 |
| 2198 | 3 | 4 | 5 | | | V-2 | TYMP | 0.56 | 2294 | 3 | 4 | 5 | | | V-2 | ZNF446 | 0.57 |
| 2199 | 3 | 4 | 5 | | | V-2 | U2AF2 | 0.56 | 2295 | 3 | 4 | 5 | | | V-2 | ZNF467 | 0.57 |
| 2200 | 3 | 4 | 5 | | | V-2 | UAP1L1 | 0.65 | 2296 | 3 | 4 | 5 | | | V-2 | ZNF500 | 0.66 |
| 2201 | 3 | 4 | 5 | | | V-2 | UBA1 | 0.50 | 2297 | 3 | 4 | 5 | | | V-2 | ZNF503-AS2 | 0.55 |
| 2202 | 3 | 4 | 5 | | | V-2 | UBAP2L | 0.64 | 2298 | 3 | 4 | 5 | | | V-2 | ZNF511 | 0.59 |
| 2203 | 3 | 4 | 5 | | | V-2 | UBD | 0.56 | 2299 | 3 | 4 | 5 | | | V-2 | ZNF512B | 0.61 |
| 2204 | 3 | 4 | 5 | | | V-2 | UBE2J2 | 0.61 | 2300 | 3 | 4 | 5 | | | V-2 | ZNF574 | 0.54 |
| 2205 | 3 | 4 | 5 | | | V-2 | UBE2L3 | 0.64 | 2301 | 3 | 4 | 5 | | | V-2 | ZNF579 | 0.53 |

Fig. 38 - 13

| | | | | | | | | | | | | | | | |
|---|---|---|---|---|---|---|---|---|---|---|---|---|---|---|---|
| 2302 | 3 | 4 | 5 | | V-2 | ZNF580 | 0.54 | 2398 | 3 | 4 | 5 | | V-1 | CD46 | 1.72 |
| 2303 | 3 | 4 | 5 | | V-2 | ZNF629 | 0.61 | 2399 | 3 | 4 | 5 | | V-1 | CD99P1 | 1.64 |
| 2304 | 3 | 4 | 5 | | V-2 | ZNF646 | 0.67 | 2400 | 3 | 4 | 5 | | V-1 | CDC14A | 1.69 |
| 2305 | 3 | 4 | 5 | | V-2 | ZNF653 | 0.62 | 2401 | 3 | 4 | 5 | | V-1 | CDH11 | 1.62 |
| 2306 | 3 | 4 | 5 | | V-2 | ZNF687 | 0.59 | 2402 | 3 | 4 | 5 | | V-1 | CDH19 | 1.58 |
| 2307 | 3 | 4 | 5 | | V-2 | ZNF688 | 0.62 | 2403 | 3 | 4 | 5 | | V-1 | CENPC1 | 1.90 |
| 2308 | 3 | 4 | 5 | | V-2 | ZNF746 | 0.66 | 2404 | 3 | 4 | 5 | | V-1 | CEP41 | 1.64 |
| 2309 | 3 | 4 | 5 | | V-2 | ZNF821 | 0.63 | 2405 | 3 | 4 | 5 | | V-1 | CEP70 | 1.75 |
| 2310 | 3 | 4 | 5 | | V-2 | ZNF853 | 0.63 | 2406 | 3 | 4 | 5 | | V-1 | CFH | 1.50 |
| 2311 | 3 | 4 | 5 | | V-2 | ZNHIT1 | 0.56 | 2407 | 3 | 4 | 5 | | V-1 | CFLAR | 1.68 |
| 2312 | 3 | 4 | 5 | | V-2 | ZNHIT2 | 0.61 | 2408 | 3 | 4 | 5 | | V-1 | CHD6 | 1.79 |
| 2313 | 3 | 4 | 5 | | V-2 | ZYX | 0.56 | 2409 | 3 | 4 | 5 | | V-1 | CHD7 | 1.66 |
| 2314 | 3 | 4 | 5 | | V-1 | AAK1 | 1.63 | 2410 | 3 | 4 | 5 | | V-1 | CHD9 | 1.54 |
| 2315 | 3 | 4 | 5 | | V-1 | ABAT | 1.75 | 2411 | 3 | 4 | 5 | | V-1 | CHM | 1.55 |
| 2316 | 3 | 4 | 5 | | V-1 | ABCA1 | 1.59 | 2412 | 3 | 4 | 5 | | V-1 | CHST11 | 1.78 |
| 2317 | 3 | 4 | 5 | | V-1 | ACADSB | 1.55 | 2413 | 3 | 4 | 5 | | V-1 | CLCN5 | 1.53 |
| 2318 | 3 | 4 | 5 | | V-1 | ACER2 | 1.77 | 2414 | 3 | 4 | 5 | | V-1 | CLDN12 | 1.52 |
| 2319 | 3 | 4 | 5 | | V-1 | ADD3 | 1.79 | 2415 | 3 | 4 | 5 | | V-1 | CLEC2D | 1.53 |
| 2320 | 3 | 4 | 5 | | V-1 | ADNP | 1.73 | 2416 | 3 | 4 | 5 | | V-1 | CLIP4 | 1.56 |
| 2321 | 3 | 4 | 5 | | V-1 | ADRA1B | 1.60 | 2417 | 3 | 4 | 5 | | V-1 | CMPK2 | 1.53 |
| 2322 | 3 | 4 | 5 | | V-1 | AFF4 | 1.52 | 2418 | 3 | 4 | 5 | | V-1 | CMTM1 | 1.58 |
| 2323 | 3 | 4 | 5 | | V-1 | AGPAT4-IT1 | 1.51 | 2419 | 3 | 4 | 5 | | V-1 | CNKSR2 | 1.75 |
| 2324 | 3 | 4 | 5 | | V-1 | AGPAT5 | 1.68 | 2420 | 3 | 4 | 5 | | V-1 | COL14A1 | 1.66 |
| 2325 | 3 | 4 | 5 | | V-1 | AKAP10 | 1.68 | 2421 | 3 | 4 | 5 | | V-1 | COL28A1 | 1.52 |
| 2326 | 3 | 4 | 5 | | V-1 | AKAP11 | 1.51 | 2422 | 3 | 4 | 5 | | V-1 | COLEC12 | 1.76 |
| 2327 | 3 | 4 | 5 | | V-1 | AMDHD1 | 1.64 | 2423 | 3 | 4 | 5 | | V-1 | CPEB1 | 1.57 |
| 2328 | 3 | 4 | 5 | | V-1 | AMOT | 2.00 | 2424 | 3 | 4 | 5 | | V-1 | CPEB2 | 1.56 |
| 2329 | 3 | 4 | 5 | | V-1 | ANGPT1 | 1.78 | 2425 | 3 | 4 | 5 | | V-1 | CPM | 1.65 |
| 2330 | 3 | 4 | 5 | | V-1 | ANKDD1A | 1.59 | 2426 | 3 | 4 | 5 | | V-1 | CSGALNACT1 | 1.87 |
| 2331 | 3 | 4 | 5 | | V-1 | ANKHD1 | 1.62 | 2427 | 3 | 4 | 5 | | V-1 | CSGALNACT2 | 1.80 |
| 2332 | 3 | 4 | 5 | | V-1 | ANKIB1 | 1.67 | 2428 | 3 | 4 | 5 | | V-1 | CSNK1G1 | 1.51 |
| 2333 | 3 | 4 | 5 | | V-1 | ANKRD11 | 1.51 | 2429 | 3 | 4 | 5 | | V-1 | CTLA4 | 1.59 |
| 2334 | 3 | 4 | 5 | | V-1 | ANKRD36BP1 | 1.90 | 2430 | 3 | 4 | 5 | | V-1 | CUL5 | 1.51 |
| 2335 | 3 | 4 | 5 | | V-1 | ANKRD42 | 1.67 | 2431 | 3 | 4 | 5 | | V-1 | CUX2 | 1.54 |
| 2336 | 3 | 4 | 5 | | V-1 | AOX1 | 1.85 | 2432 | 3 | 4 | 5 | | V-1 | CXCR6 | 1.73 |
| 2337 | 3 | 4 | 5 | | V-1 | APOOL | 1.66 | 2433 | 3 | 4 | 5 | | V-1 | CXorf57 | 1.87 |
| 2338 | 3 | 4 | 5 | | V-1 | ARFGEF2 | 1.80 | 2434 | 3 | 4 | 5 | | V-1 | CYBRD1 | 1.79 |
| 2339 | 3 | 4 | 5 | | V-1 | ARG2 | 1.70 | 2435 | 3 | 4 | 5 | | V-1 | CYCS | 1.50 |
| 2340 | 3 | 4 | 5 | | V-1 | ARID3A | 1.68 | 2436 | 3 | 4 | 5 | | V-1 | CYP4V2 | 1.94 |
| 2341 | 3 | 4 | 5 | | V-1 | ARID4B | 1.89 | 2437 | 3 | 4 | 5 | | V-1 | CYR61 | 1.58 |
| 2342 | 3 | 4 | 5 | | V-1 | ARL10 | 1.78 | 2438 | 3 | 4 | 5 | | V-1 | DAAM1 | 1.85 |
| 2343 | 3 | 4 | 5 | | V-1 | ARL13B | 1.51 | 2439 | 3 | 4 | 5 | | V-1 | DAB2 | 1.95 |
| 2344 | 3 | 4 | 5 | | V-1 | ARSD | 1.55 | 2440 | 3 | 4 | 5 | | V-1 | DCAF10 | 1.58 |
| 2345 | 3 | 4 | 5 | | V-1 | ATAD2B | 1.84 | 2441 | 3 | 4 | 5 | | V-1 | DCD | 1.55 |
| 2346 | 3 | 4 | 5 | | V-1 | ATM | 1.98 | 2442 | 3 | 4 | 5 | | V-1 | DCLRE1C | 1.69 |
| 2347 | 3 | 4 | 5 | | V-1 | ATP11A | 1.76 | 2443 | 3 | 4 | 5 | | V-1 | DCUN1D1 | 1.57 |
| 2348 | 3 | 4 | 5 | | V-1 | ATP13A4 | 1.84 | 2444 | 3 | 4 | 5 | | V-1 | DCUN1D4 | 1.55 |
| 2349 | 3 | 4 | 5 | | V-1 | B3GALNT1 | 1.72 | 2445 | 3 | 4 | 5 | | V-1 | DDHD1 | 1.79 |
| 2350 | 3 | 4 | 5 | | V-1 | BACE1-AS | 1.53 | 2446 | 3 | 4 | 5 | | V-1 | DDIT4L | 1.84 |
| 2351 | 3 | 4 | 5 | | V-1 | BACH2 | 1.57 | 2447 | 3 | 4 | 5 | | V-1 | DDX46 | 1.64 |
| 2352 | 3 | 4 | 5 | | V-1 | BAZ1A | 1.54 | 2448 | 3 | 4 | 5 | | V-1 | DDX60 | 1.66 |
| 2353 | 3 | 4 | 5 | | V-1 | BAZ2B | 1.65 | 2449 | 3 | 4 | 5 | | V-1 | DEFA6 | 1.55 |
| 2354 | 3 | 4 | 5 | | V-1 | BB510 | 1.65 | 2450 | 3 | 4 | 5 | | V-1 | DET1 | 1.84 |
| 2355 | 3 | 4 | 5 | | V-1 | BCL2L11 | 1.65 | 2451 | 3 | 4 | 5 | | V-1 | DHX29 | 1.53 |
| 2356 | 3 | 4 | 5 | | V-1 | BHLHE41 | 1.80 | 2452 | 3 | 4 | 5 | | V-1 | DISC1 | 1.57 |
| 2357 | 3 | 4 | 5 | | V-1 | BIN2 | 1.80 | 2453 | 3 | 4 | 5 | | V-1 | DIXDC1 | 1.56 |
| 2358 | 3 | 4 | 5 | | V-1 | BIRC2 | 1.52 | 2454 | 3 | 4 | 5 | | V-1 | DNAJB14 | 1.82 |
| 2359 | 3 | 4 | 5 | | V-1 | BMS1P5 | 1.92 | 2455 | 3 | 4 | 5 | | V-1 | DNAJC18 | 1.74 |
| 2360 | 3 | 4 | 5 | | V-1 | BNC2 | 1.72 | 2456 | 3 | 4 | 5 | | V-1 | DNASE1 | 1.51 |
| 2361 | 3 | 4 | 5 | | V-1 | BTBD3 | 1.69 | 2457 | 3 | 4 | 5 | | V-1 | DOCK3 | 1.69 |
| 2362 | 3 | 4 | 5 | | V-1 | BTBD7 | 1.53 | 2458 | 3 | 4 | 5 | | V-1 | DOCK4 | 1.65 |
| 2363 | 3 | 4 | 5 | | V-1 | BTN2A3P | 1.57 | 2459 | 3 | 4 | 5 | | V-1 | DOCK5 | 1.95 |
| 2364 | 3 | 4 | 5 | | V-1 | C11orf54 | 1.60 | 2460 | 3 | 4 | 5 | | V-1 | DOCK8 | 1.66 |
| 2365 | 3 | 4 | 5 | | V-1 | C12orf35 | 2.00 | 2461 | 3 | 4 | 5 | | V-1 | DOPEY2 | 1.58 |
| 2366 | 3 | 4 | 5 | | V-1 | C14orf28 | 1.80 | 2462 | 3 | 4 | 5 | | V-1 | DPRXP4 | 1.81 |
| 2367 | 3 | 4 | 5 | | V-1 | C14orf37 | 1.56 | 2463 | 3 | 4 | 5 | | V-1 | DPYD | 1.87 |
| 2368 | 3 | 4 | 5 | | V-1 | C15orf52 | 1.68 | 2464 | 3 | 4 | 5 | | V-1 | DSTYK | 1.92 |
| 2369 | 3 | 4 | 5 | | V-1 | C17orf57 | 1.50 | 2465 | 3 | 4 | 5 | | V-1 | DYRK3 | 1.55 |
| 2370 | 3 | 4 | 5 | | V-1 | C17orf85 | 1.52 | 2466 | 3 | 4 | 5 | | V-1 | EBLN2 | 1.64 |
| 2371 | 3 | 4 | 5 | | V-1 | C1orf9 | 1.72 | 2467 | 3 | 4 | 5 | | V-1 | EDIL3 | 1.68 |
| 2372 | 3 | 4 | 5 | | V-1 | C20orf118 | 1.59 | 2468 | 3 | 4 | 5 | | V-1 | EFHA2 | 1.62 |
| 2373 | 3 | 4 | 5 | | V-1 | C20orf194 | 1.72 | 2469 | 3 | 4 | 5 | | V-1 | EHF | 1.66 |
| 2374 | 3 | 4 | 5 | | V-1 | C2CD2 | 1.61 | 2470 | 3 | 4 | 5 | | V-1 | EIF2AK2 | 1.76 |
| 2375 | 3 | 4 | 5 | | V-1 | C3 | 1.78 | 2471 | 3 | 4 | 5 | | V-1 | EIF4G3 | 1.85 |
| 2376 | 3 | 4 | 5 | | V-1 | C5orf46 | 1.91 | 2472 | 3 | 4 | 5 | | V-1 | EIF5 | 1.56 |
| 2377 | 3 | 4 | 5 | | V-1 | C5orf54 | 1.66 | 2473 | 3 | 4 | 5 | | V-1 | EIF5B | 1.78 |
| 2378 | 3 | 4 | 5 | | V-1 | C6orf120 | 1.64 | 2474 | 3 | 4 | 5 | | V-1 | ELK3 | 1.80 |
| 2379 | 3 | 4 | 5 | | V-1 | C6orf163 | 1.63 | 2475 | 3 | 4 | 5 | | V-1 | ELMOD2 | 1.56 |
| 2380 | 3 | 4 | 5 | | V-1 | C6orf62 | 1.61 | 2476 | 3 | 4 | 5 | | V-1 | EMR2 | 1.96 |
| 2381 | 3 | 4 | 5 | | V-1 | C7orf53 | 1.94 | 2477 | 3 | 4 | 5 | | V-1 | EMR4P | 1.69 |
| 2382 | 3 | 4 | 5 | | V-1 | C9orf5 | 1.51 | 2478 | 3 | 4 | 5 | | V-1 | EPG5 | 1.53 |
| 2383 | 3 | 4 | 5 | | V-1 | CA13 | 1.56 | 2479 | 3 | 4 | 5 | | V-1 | ERGIC2 | 1.56 |
| 2384 | 3 | 4 | 5 | | V-1 | CACNB4 | 1.82 | 2480 | 3 | 4 | 5 | | V-1 | ERI2 | 1.68 |
| 2385 | 3 | 4 | 5 | | V-1 | CAMK1D | 1.55 | 2481 | 3 | 4 | 5 | | V-1 | ESCO1 | 1.66 |
| 2386 | 3 | 4 | 5 | | V-1 | CASP8AP2 | 1.74 | 2482 | 3 | 4 | 5 | | V-1 | F13A1 | 1.69 |
| 2387 | 3 | 4 | 5 | | V-1 | CBL | 1.50 | 2483 | 3 | 4 | 5 | | V-1 | F2RL2 | 1.80 |
| 2388 | 3 | 4 | 5 | | V-1 | CCDC112 | 2.00 | 2484 | 3 | 4 | 5 | | V-1 | FAM115A | 1.74 |
| 2389 | 3 | 4 | 5 | | V-1 | CCDC134 | 1.54 | 2485 | 3 | 4 | 5 | | V-1 | FAM129A | 1.53 |
| 2390 | 3 | 4 | 5 | | V-1 | CCDC142 | 1.63 | 2486 | 3 | 4 | 5 | | V-1 | FAM133B | 1.62 |
| 2391 | 3 | 4 | 5 | | V-1 | CCDC152 | 1.72 | 2487 | 3 | 4 | 5 | | V-1 | FAM13A | 1.60 |
| 2392 | 3 | 4 | 5 | | V-1 | CCDC80 | 1.60 | 2488 | 3 | 4 | 5 | | V-1 | FAM13B | 1.51 |
| 2393 | 3 | 4 | 5 | | V-1 | CCDC88A | 1.82 | 2489 | 3 | 4 | 5 | | V-1 | FAM168A | 1.68 |
| 2394 | 3 | 4 | 5 | | V-1 | CCDC93 | 1.67 | 2490 | 3 | 4 | 5 | | V-1 | FAM175A | 1.52 |
| 2395 | 3 | 4 | 5 | | V-1 | CCNI | 1.57 | 2491 | 3 | 4 | 5 | | V-1 | FAM196B | 1.62 |
| 2396 | 3 | 4 | 5 | | V-1 | CCPG1 | 1.79 | 2492 | 3 | 4 | 5 | | V-1 | FAM208B | 1.80 |
| 2397 | 3 | 4 | 5 | | V-1 | CD163L1 | 1.60 | 2493 | 3 | 4 | 5 | | V-1 | FAM21A | 1.69 |

Fig. 38 - 14

| # | | | | | | | Gene | Value | # | | | | | | | Gene | Value |
|---|---|---|---|---|---|---|---|---|---|---|---|---|---|---|---|---|---|
| 2494 | 3 | 4 | 5 | | | V-1 | FAM25C | 1.83 | 2590 | 3 | 4 | 5 | | | V-1 | KRTAP4-7 | 1.92 |
| 2495 | 3 | 4 | 5 | | | V-1 | FAM49A | 1.66 | 2591 | 3 | 4 | 5 | | | V-1 | KRTAP4-9 | 1.95 |
| 2496 | 3 | 4 | 5 | | | V-1 | FAM63B | 1.92 | 2592 | 3 | 4 | 5 | | | V-1 | KRTAP5-2 | 1.81 |
| 2497 | 3 | 4 | 5 | | | V-1 | FASTKD1 | 1.56 | 2593 | 3 | 4 | 5 | | | V-1 | KRTAP5-3 | 1.63 |
| 2498 | 3 | 4 | 5 | | | V-1 | FFAR2 | 1.77 | 2594 | 3 | 4 | 5 | | | V-1 | KRTAP5-4 | 1.52 |
| 2499 | 3 | 4 | 5 | | | V-1 | FLJ42627 | 1.65 | 2595 | 3 | 4 | 5 | | | V-1 | KRTAP5-5 | 1.61 |
| 2500 | 3 | 4 | 5 | | | V-1 | FLJ42709 | 1.66 | 2596 | 3 | 4 | 5 | | | V-1 | KRTAP5-7 | 1.54 |
| 2501 | 3 | 4 | 5 | | | V-1 | FLVCR1 | 1.75 | 2597 | 3 | 4 | 5 | | | V-1 | KRTAP5-8 | 1.55 |
| 2502 | 3 | 4 | 5 | | | V-1 | FMO2 | 1.57 | 2598 | 3 | 4 | 5 | | | V-1 | KRTAP9-2 | 1.93 |
| 2503 | 3 | 4 | 5 | | | V-1 | FNDC3A | 1.58 | 2599 | 3 | 4 | 5 | | | V-1 | KRTAP9-3 | 1.88 |
| 2504 | 3 | 4 | 5 | | | V-1 | FOS | 1.56 | 2600 | 3 | 4 | 5 | | | V-1 | KRTAP9-4 | 1.91 |
| 2505 | 3 | 4 | 5 | | | V-1 | FPGT | 1.63 | 2601 | 3 | 4 | 5 | | | V-1 | LARP7 | 1.89 |
| 2506 | 3 | 4 | 5 | | | V-1 | FRMD4B | 1.61 | 2602 | 3 | 4 | 5 | | | V-1 | LCOR | 1.53 |
| 2507 | 3 | 4 | 5 | | | V-1 | FYCO1 | 1.84 | 2603 | 3 | 4 | 5 | | | V-1 | LCORL | 1.58 |
| 2508 | 3 | 4 | 5 | | | V-1 | GBP5 | 1.74 | 2604 | 3 | 4 | 5 | | | V-1 | LCP2 | 1.75 |
| 2509 | 3 | 4 | 5 | | | V-1 | GCA | 1.67 | 2605 | 3 | 4 | 5 | | | V-1 | LIFR | 1.80 |
| 2510 | 3 | 4 | 5 | | | V-1 | GCNT1 | 1.76 | 2606 | 3 | 4 | 5 | | | V-1 | LIG4 | 1.52 |
| 2511 | 3 | 4 | 5 | | | V-1 | GGTA1P | 1.53 | 2607 | 3 | 4 | 5 | | | V-1 | LIX1L | 1.70 |
| 2512 | 3 | 4 | 5 | | | V-1 | GK5 | 1.83 | 2608 | 3 | 4 | 5 | | | V-1 | LMLN | 1.87 |
| 2513 | 3 | 4 | 5 | | | V-1 | GLIPR1 | 1.65 | 2609 | 3 | 4 | 5 | | | V-1 | LMO7 | 1.50 |
| 2514 | 3 | 4 | 5 | | | V-1 | GLRB | 1.74 | 2610 | 3 | 4 | 5 | | | V-1 | LNX1 | 1.62 |
| 2515 | 3 | 4 | 5 | | | V-1 | GLT8D2 | 1.52 | 2611 | 3 | 4 | 5 | | | V-1 | LOC100129550 | 1.71 |
| 2516 | 3 | 4 | 5 | | | V-1 | GLYATL1 | 1.80 | 2612 | 3 | 4 | 5 | | | V-1 | LOC100129917 | 1.97 |
| 2517 | 3 | 4 | 5 | | | V-1 | GMF8 | 1.58 | 2613 | 3 | 4 | 5 | | | V-1 | LOC100132215 | 1.62 |
| 2518 | 3 | 4 | 5 | | | V-1 | GNG2 | 1.73 | 2614 | 3 | 4 | 5 | | | V-1 | LOC100132774 | 1.53 |
| 2519 | 3 | 4 | 5 | | | V-1 | GPR155 | 1.81 | 2615 | 3 | 4 | 5 | | | V-1 | LOC100190938 | 1.67 |
| 2520 | 3 | 4 | 5 | | | V-1 | GPR180 | 1.57 | 2616 | 3 | 4 | 5 | | | V-1 | LOC100272228 | 1.56 |
| 2521 | 3 | 4 | 5 | | | V-1 | GRAMD1C | 1.66 | 2617 | 3 | 4 | 5 | | | V-1 | LOC100287722 | 1.79 |
| 2522 | 3 | 4 | 5 | | | V-1 | GRPEL2 | 1.76 | 2618 | 3 | 4 | 5 | | | V-1 | LOC100288069 | 1.84 |
| 2523 | 3 | 4 | 5 | | | V-1 | GTF2A1 | 1.92 | 2619 | 3 | 4 | 5 | | | V-1 | LOC100288615 | 1.52 |
| 2524 | 3 | 4 | 5 | | | V-1 | GUSBP3 | 1.72 | 2620 | 3 | 4 | 5 | | | V-1 | LOC100505549 | 1.51 |
| 2525 | 3 | 4 | 5 | | | V-1 | GXYLT2 | 1.81 | 2621 | 3 | 4 | 5 | | | V-1 | LOC100506071 | 1.52 |
| 2526 | 3 | 4 | 5 | | | V-1 | GZF1 | 1.57 | 2622 | 3 | 4 | 5 | | | V-1 | LOC100506710 | 1.86 |
| 2527 | 3 | 4 | 5 | | | V-1 | GZMA | 1.86 | 2623 | 3 | 4 | 5 | | | V-1 | LOC100506990 | 1.68 |
| 2528 | 3 | 4 | 5 | | | V-1 | HCG11 | 1.59 | 2624 | 3 | 4 | 5 | | | V-1 | LOC100507117 | 1.65 |
| 2529 | 3 | 4 | 5 | | | V-1 | HCG27 | 1.81 | 2625 | 3 | 4 | 5 | | | V-1 | LOC100507387 | 1.79 |
| 2530 | 3 | 4 | 5 | | | V-1 | HEATR8 | 1.56 | 2626 | 3 | 4 | 5 | | | V-1 | LOC286367 | 1.79 |
| 2531 | 3 | 4 | 5 | | | V-1 | HERC6 | 1.58 | 2627 | 3 | 4 | 5 | | | V-1 | LOC386758 | 1.56 |
| 2532 | 3 | 4 | 5 | | | V-1 | HES1 | 1.92 | 2628 | 3 | 4 | 5 | | | V-1 | LOC400236 | 1.65 |
| 2533 | 3 | 4 | 5 | | | V-1 | HES5 | 1.84 | 2629 | 3 | 4 | 5 | | | V-1 | LOC440300 | 1.51 |
| 2534 | 3 | 4 | 5 | | | V-1 | HIBCH | 1.54 | 2630 | 3 | 4 | 5 | | | V-1 | LOC541473 | 1.79 |
| 2535 | 3 | 4 | 5 | | | V-1 | HIPK2 | 1.70 | 2631 | 3 | 4 | 5 | | | V-1 | LOC642852 | 1.78 |
| 2536 | 3 | 4 | 5 | | | V-1 | HIST2H2BF | 1.58 | 2632 | 3 | 4 | 5 | | | V-1 | LOC645513 | 1.50 |
| 2537 | 3 | 4 | 5 | | | V-1 | HLF | 2.00 | 2633 | 3 | 4 | 5 | | | V-1 | LOC647859 | 1.84 |
| 2538 | 3 | 4 | 5 | | | V-1 | HMGN5 | 1.93 | 2634 | 3 | 4 | 5 | | | V-1 | LOC652276 | 1.77 |
| 2539 | 3 | 4 | 5 | | | V-1 | HS3ST3B1 | 1.83 | 2635 | 3 | 4 | 5 | | | V-1 | LOC729603 | 1.56 |
| 2540 | 3 | 4 | 5 | | | V-1 | HSD17B2 | 1.90 | 2636 | 3 | 4 | 5 | | | V-1 | LPGAT1 | 1.54 |
| 2541 | 3 | 4 | 5 | | | V-1 | HSH2D | 1.56 | 2637 | 3 | 4 | 5 | | | V-1 | LPHN2 | 1.53 |
| 2542 | 3 | 4 | 5 | | | V-1 | HSP90AA1 | 1.59 | 2638 | 3 | 4 | 5 | | | V-1 | LPP | 1.78 |
| 2543 | 3 | 4 | 5 | | | V-1 | IBA57 | 1.50 | 2639 | 3 | 4 | 5 | | | V-1 | LRCH3 | 1.79 |
| 2544 | 3 | 4 | 5 | | | V-1 | IDI1 | 1.66 | 2640 | 3 | 4 | 5 | | | V-1 | LRRC49 | 1.58 |
| 2545 | 3 | 4 | 5 | | | V-1 | IL10 | 1.68 | 2641 | 3 | 4 | 5 | | | V-1 | LTC4S | 1.65 |
| 2546 | 3 | 4 | 5 | | | V-1 | IL6R | 1.72 | 2642 | 3 | 4 | 5 | | | V-1 | LUM | 1.56 |
| 2547 | 3 | 4 | 5 | | | V-1 | INPP4A | 1.59 | 2643 | 3 | 4 | 5 | | | V-1 | LYRM7 | 1.68 |
| 2548 | 3 | 4 | 5 | | | V-1 | INTU | 1.59 | 2644 | 3 | 4 | 5 | | | V-1 | LYST | 1.52 |
| 2549 | 3 | 4 | 5 | | | V-1 | INVS | 1.82 | 2645 | 3 | 4 | 5 | | | V-1 | MACC1 | 1.65 |
| 2550 | 3 | 4 | 5 | | | V-1 | ITGA9 | 1.54 | 2646 | 3 | 4 | 5 | | | V-1 | MAML2 | 1.71 |
| 2551 | 3 | 4 | 5 | | | V-1 | ITPR1 | 1.82 | 2647 | 3 | 4 | 5 | | | V-1 | MAN2A1 | 1.89 |
| 2552 | 3 | 4 | 5 | | | V-1 | ITSN2 | 1.51 | 2648 | 3 | 4 | 5 | | | V-1 | MAOA | 1.69 |
| 2553 | 3 | 4 | 5 | | | V-1 | JMJD1C | 1.50 | 2649 | 3 | 4 | 5 | | | V-1 | MAP3K8 | 1.69 |
| 2554 | 3 | 4 | 5 | | | V-1 | JRK | 1.85 | 2650 | 3 | 4 | 5 | | | V-1 | MARCH1 | 1.99 |
| 2555 | 3 | 4 | 5 | | | V-1 | JRKL | 1.53 | 2651 | 3 | 4 | 5 | | | V-1 | MAT2A | 1.63 |
| 2556 | 3 | 4 | 5 | | | V-1 | KAT6B | 1.55 | 2652 | 3 | 4 | 5 | | | V-1 | MATL2963 | 1.87 |
| 2557 | 3 | 4 | 5 | | | V-1 | KCND3 | 1.74 | 2653 | 3 | 4 | 5 | | | V-1 | MBD5 | 1.80 |
| 2558 | 3 | 4 | 5 | | | V-1 | KCNN2 | 1.87 | 2654 | 3 | 4 | 5 | | | V-1 | MDN1 | 1.53 |
| 2559 | 3 | 4 | 5 | | | V-1 | KCTD7 | 1.54 | 2655 | 3 | 4 | 5 | | | V-1 | MEIS2 | 1.55 |
| 2560 | 3 | 4 | 5 | | | V-1 | KDM6A | 1.64 | 2656 | 3 | 4 | 5 | | | V-1 | MFN1 | 1.50 |
| 2561 | 3 | 4 | 5 | | | V-1 | KIAA0564 | 1.74 | 2657 | 3 | 4 | 5 | | | V-1 | MIAT | 1.92 |
| 2562 | 3 | 4 | 5 | | | V-1 | KIAA0748 | 1.90 | 2658 | 3 | 4 | 5 | | | V-1 | MIR600HG | 1.73 |
| 2563 | 3 | 4 | 5 | | | V-1 | KIAA1147 | 1.99 | 2659 | 3 | 4 | 5 | | | V-1 | MIS12 | 1.51 |
| 2564 | 3 | 4 | 5 | | | V-1 | KIAA1161 | 1.51 | 2660 | 3 | 4 | 5 | | | V-1 | MLL | 1.75 |
| 2565 | 3 | 4 | 5 | | | V-1 | KIAA1244 | 1.60 | 2661 | 3 | 4 | 5 | | | V-1 | MLL3 | 1.86 |
| 2566 | 3 | 4 | 5 | | | V-1 | KIAA1432 | 1.59 | 2662 | 3 | 4 | 5 | | | V-1 | MNS1 | 1.63 |
| 2567 | 3 | 4 | 5 | | | V-1 | KIAA1468 | 1.87 | 2663 | 3 | 4 | 5 | | | V-1 | MOCOS | 1.56 |
| 2568 | 3 | 4 | 5 | | | V-1 | KIAA1586 | 1.58 | 2664 | 3 | 4 | 5 | | | V-1 | MON2 | 1.59 |
| 2569 | 3 | 4 | 5 | | | V-1 | KIAA1715 | 1.51 | 2665 | 3 | 4 | 5 | | | V-1 | MORC3 | 1.51 |
| 2570 | 3 | 4 | 5 | | | V-1 | KIAA1737 | 1.86 | 2666 | 3 | 4 | 5 | | | V-1 | MR1 | 1.71 |
| 2571 | 3 | 4 | 5 | | | V-1 | KIAA1826 | 1.73 | 2667 | 3 | 4 | 5 | | | V-1 | MRPS18C | 1.51 |
| 2572 | 3 | 4 | 5 | | | V-1 | KIAA1919 | 1.64 | 2668 | 3 | 4 | 5 | | | V-1 | MRPS25 | 1.68 |
| 2573 | 3 | 4 | 5 | | | V-1 | KIAA2018 | 1.57 | 2669 | 3 | 4 | 5 | | | V-1 | MRS2P2 | 1.76 |
| 2574 | 3 | 4 | 5 | | | V-1 | KIAA2026 | 1.93 | 2670 | 3 | 4 | 5 | | | V-1 | MSI2 | 1.60 |
| 2575 | 3 | 4 | 5 | | | V-1 | KIF1B | 1.57 | 2671 | 3 | 4 | 5 | | | V-1 | MTCP1 | 1.54 |
| 2576 | 3 | 4 | 5 | | | V-1 | KIF2A | 1.56 | 2672 | 3 | 4 | 5 | | | V-1 | MTMR10 | 1.73 |
| 2577 | 3 | 4 | 5 | | | V-1 | KIRREL | 1.70 | 2673 | 3 | 4 | 5 | | | V-1 | MTMR4 | 1.82 |
| 2578 | 3 | 4 | 5 | | | V-1 | KLHL2 | 1.69 | 2674 | 3 | 4 | 5 | | | V-1 | MTX3 | 1.81 |
| 2579 | 3 | 4 | 5 | | | V-1 | KLHL28 | 1.51 | 2675 | 3 | 4 | 5 | | | V-1 | MYSM1 | 1.86 |
| 2580 | 3 | 4 | 5 | | | V-1 | KLHL9 | 1.67 | 2676 | 3 | 4 | 5 | | | V-1 | N6AMT1 | 1.94 |
| 2581 | 3 | 4 | 5 | | | V-1 | KRR1 | 1.61 | 2677 | 3 | 4 | 5 | | | V-1 | NAALAD2 | 1.65 |
| 2582 | 3 | 4 | 5 | | | V-1 | KRTAP10-10 | 1.57 | 2678 | 3 | 4 | 5 | | | V-1 | NAMPT | 1.53 |
| 2583 | 3 | 4 | 5 | | | V-1 | KRTAP10-3 | 1.64 | 2679 | 3 | 4 | 5 | | | V-1 | NAP1L3 | 1.81 |
| 2584 | 3 | 4 | 5 | | | V-1 | KRTAP10-5 | 1.64 | 2680 | 3 | 4 | 5 | | | V-1 | NAP1L5 | 1.51 |
| 2585 | 3 | 4 | 5 | | | V-1 | KRTAP1-1 | 1.67 | 2681 | 3 | 4 | 5 | | | V-1 | NAV3 | 1.76 |
| 2586 | 3 | 4 | 5 | | | V-1 | KRTAP12-2 | 1.64 | 2682 | 3 | 4 | 5 | | | V-1 | NBPF11 | 1.65 |
| 2587 | 3 | 4 | 5 | | | V-1 | KRTAP17-1 | 1.61 | 2683 | 3 | 4 | 5 | | | V-1 | NBPF15 | 1.77 |
| 2588 | 3 | 4 | 5 | | | V-1 | KRTAP26-1 | 1.58 | 2684 | 3 | 4 | 5 | | | V-1 | NCF1 | 1.60 |
| 2589 | 3 | 4 | 5 | | | V-1 | KRTAP4-4 | 1.52 | 2685 | 3 | 4 | 5 | | | V-1 | NCOA2 | 1.96 |

Fig. 38 - 15

| | | | | | | | | |
|---|---|---|---|---|---|---|---|---|
| 2686 | 3 | 4 | 5 | | V-1 | NCOR1 | 1.63 |
| 2687 | 3 | 4 | 5 | | V-1 | NEAT1 | 1.94 |
| 2688 | 3 | 4 | 5 | | V-1 | NFATC2 | 1.57 |
| 2689 | 3 | 4 | 5 | | V-1 | NFKBID | 1.64 |
| 2690 | 3 | 4 | 5 | | V-1 | NHLH2 | 1.69 |
| 2691 | 3 | 4 | 5 | | V-1 | NHS | 1.77 |
| 2692 | 3 | 4 | 5 | | V-1 | NHSL2 | 1.65 |
| 2693 | 3 | 4 | 5 | | V-1 | NINL | 1.55 |
| 2694 | 3 | 4 | 5 | | V-1 | NLK | 1.69 |
| 2695 | 3 | 4 | 5 | | V-1 | NOL8 | 1.89 |
| 2696 | 3 | 4 | 5 | | V-1 | NPNT | 1.69 |
| 2697 | 3 | 4 | 5 | | V-1 | NPR2 | 1.64 |
| 2698 | 3 | 4 | 5 | | V-1 | NRP2 | 1.75 |
| 2699 | 3 | 4 | 5 | | V-1 | NRXN3 | 1.72 |
| 2700 | 3 | 4 | 5 | | V-1 | NUDT13 | 1.81 |
| 2701 | 3 | 4 | 5 | | V-1 | NUPL1 | 1.51 |
| 2702 | 3 | 4 | 5 | | V-1 | OR2A4 | 1.87 |
| 2703 | 3 | 4 | 5 | | V-1 | OR2A7 | 1.84 |
| 2704 | 3 | 4 | 5 | | V-1 | OSGEPL1 | 1.54 |
| 2705 | 3 | 4 | 5 | | V-1 | OSM | 1.84 |
| 2706 | 3 | 4 | 5 | | V-1 | PAFAH1B1 | 1.50 |
| 2707 | 3 | 4 | 5 | | V-1 | PAPD5 | 1.51 |
| 2708 | 3 | 4 | 5 | | V-1 | PAPOLB | 1.55 |
| 2709 | 3 | 4 | 5 | | V-1 | PARP8 | 1.89 |
| 2710 | 3 | 4 | 5 | | V-1 | PCDH18 | 1.74 |
| 2711 | 3 | 4 | 5 | | V-1 | PCDHGA6 | 1.65 |
| 2712 | 3 | 4 | 5 | | V-1 | PCMTD2 | 1.67 |
| 2713 | 3 | 4 | 5 | | V-1 | PCNX | 1.56 |
| 2714 | 3 | 4 | 5 | | V-1 | PDIK1L | 1.55 |
| 2715 | 3 | 4 | 5 | | V-1 | PDK1 | 1.67 |
| 2716 | 3 | 4 | 5 | | V-1 | PDP1 | 1.65 |
| 2717 | 3 | 4 | 5 | | V-1 | PDP2 | 1.86 |
| 2718 | 3 | 4 | 5 | | V-1 | PDZD2 | 1.77 |
| 2719 | 3 | 4 | 5 | | V-1 | PDZD8 | 1.62 |
| 2720 | 3 | 4 | 5 | | V-1 | PEAK1 | 1.51 |
| 2721 | 3 | 4 | 5 | | V-1 | PFKFB2 | 1.72 |
| 2722 | 3 | 4 | 5 | | V-1 | PHACTR1 | 1.84 |
| 2723 | 3 | 4 | 5 | | V-1 | PHC3 | 1.87 |
| 2724 | 3 | 4 | 5 | | V-1 | PHOSPHO1 | 1.55 |
| 2725 | 3 | 4 | 5 | | V-1 | PI15 | 1.57 |
| 2726 | 3 | 4 | 5 | | V-1 | PIAS2 | 1.69 |
| 2727 | 3 | 4 | 5 | | V-1 | PIGM | 1.93 |
| 2728 | 3 | 4 | 5 | | V-1 | PIK3AP1 | 2.00 |
| 2729 | 3 | 4 | 5 | | V-1 | PIK3R1 | 1.97 |
| 2730 | 3 | 4 | 5 | | V-1 | PIKFYVE | 1.92 |
| 2731 | 3 | 4 | 5 | | V-1 | PKP2 | 1.57 |
| 2732 | 3 | 4 | 5 | | V-1 | PLA2R1 | 1.58 |
| 2733 | 3 | 4 | 5 | | V-1 | PLEKHA2 | 1.68 |
| 2734 | 3 | 4 | 5 | | V-1 | PLEKHA5 | 1.54 |
| 2735 | 3 | 4 | 5 | | V-1 | PLEKHH2 | 1.66 |
| 2736 | 3 | 4 | 5 | | V-1 | PLGLB1 | 1.51 |
| 2737 | 3 | 4 | 5 | | V-1 | PLK1S1 | 1.58 |
| 2738 | 3 | 4 | 5 | | V-1 | PM20D2 | 1.73 |
| 2739 | 3 | 4 | 5 | | V-1 | PMS2 | 1.63 |
| 2740 | 3 | 4 | 5 | | V-1 | PNPLA8 | 1.60 |
| 2741 | 3 | 4 | 5 | | V-1 | POLG2 | 1.59 |
| 2742 | 3 | 4 | 5 | | V-1 | PON3 | 1.66 |
| 2743 | 3 | 4 | 5 | | V-1 | POU2F1 | 1.73 |
| 2744 | 3 | 4 | 5 | | V-1 | PPM1B | 1.55 |
| 2745 | 3 | 4 | 5 | | V-1 | PPP1R3B | 1.90 |
| 2746 | 3 | 4 | 5 | | V-1 | PRDM10 | 1.98 |
| 2747 | 3 | 4 | 5 | | V-1 | PRINS | 1.66 |
| 2748 | 3 | 4 | 5 | | V-1 | PRKACB | 1.64 |
| 2749 | 3 | 4 | 5 | | V-1 | PRKG1 | 1.97 |
| 2750 | 3 | 4 | 5 | | V-1 | PRKG2 | 1.56 |
| 2751 | 3 | 4 | 5 | | V-1 | PROM1 | 1.66 |
| 2752 | 3 | 4 | 5 | | V-1 | PRPF4B | 1.66 |
| 2753 | 3 | 4 | 5 | | V-1 | PRR14L | 1.82 |
| 2754 | 3 | 4 | 5 | | V-1 | PRRX1 | 1.62 |
| 2755 | 3 | 4 | 5 | | V-1 | PTAFR | 1.94 |
| 2756 | 3 | 4 | 5 | | V-1 | PTCD2 | 1.60 |
| 2757 | 3 | 4 | 5 | | V-1 | PTER | 1.54 |
| 2758 | 3 | 4 | 5 | | V-1 | PTGDS | 1.73 |
| 2759 | 3 | 4 | 5 | | V-1 | PTPDC1 | 1.65 |
| 2760 | 3 | 4 | 5 | | V-1 | PTPLAD2 | 1.92 |
| 2761 | 3 | 4 | 5 | | V-1 | PTPN12 | 1.67 |
| 2762 | 3 | 4 | 5 | | V-1 | PTPN14 | 1.82 |
| 2763 | 3 | 4 | 5 | | V-1 | PTPRE | 2.00 |
| 2764 | 3 | 4 | 5 | | V-1 | PURA | 1.83 |
| 2765 | 3 | 4 | 5 | | V-1 | PUS10 | 1.57 |
| 2766 | 3 | 4 | 5 | | V-1 | PWWP2A | 1.65 |
| 2767 | 3 | 4 | 5 | | V-1 | RAB3IP | 1.93 |
| 2768 | 3 | 4 | 5 | | V-1 | RAD50 | 1.63 |
| 2769 | 3 | 4 | 5 | | V-1 | RAP2A | 1.57 |
| 2770 | 3 | 4 | 5 | | V-1 | RAP2C | 1.50 |
| 2771 | 3 | 4 | 5 | | V-1 | RASSF6 | 1.94 |
| 2772 | 3 | 4 | 5 | | V-1 | RB1CC1 | 1.57 |
| 2773 | 3 | 4 | 5 | | V-1 | RBM18 | 1.63 |
| 2774 | 3 | 4 | 5 | | V-1 | RCSD1 | 1.54 |
| 2775 | 3 | 4 | 5 | | V-1 | RDH16 | 1.57 |
| 2776 | 3 | 4 | 5 | | V-1 | RDX | 1.57 |
| 2777 | 3 | 4 | 5 | | V-1 | REL | 1.85 |
| 2778 | 3 | 4 | 5 | | V-1 | RFESD | 1.54 |
| 2779 | 3 | 4 | 5 | | V-1 | RGPD4 | 1.78 |
| 2780 | 3 | 4 | 5 | | V-1 | RGS13 | 1.99 |
| 2781 | 3 | 4 | 5 | | V-1 | RGS16 | 1.81 |
| 2782 | 3 | 4 | 5 | | V-1 | RHD | 1.65 |
| 2783 | 3 | 4 | 5 | | V-1 | RHOBTB3 | 1.60 |
| 2784 | 3 | 4 | 5 | | V-1 | RHOU | 1.53 |
| 2785 | 3 | 4 | 5 | | V-1 | RMI1 | 2.00 |
| 2786 | 3 | 4 | 5 | | V-1 | RNASE1 | 1.71 |
| 2787 | 3 | 4 | 5 | | V-1 | RNASEH1 | 1.91 |
| 2788 | 3 | 4 | 5 | | V-1 | RNF170 | 1.84 |
| 2789 | 3 | 4 | 5 | | V-1 | RNF19A | 1.51 |
| 2790 | 3 | 4 | 5 | | V-1 | RNF212 | 1.61 |
| 2791 | 3 | 4 | 5 | | V-1 | RNF6 | 1.69 |
| 2792 | 3 | 4 | 5 | | V-1 | RNPC3 | 1.83 |
| 2793 | 3 | 4 | 5 | | V-1 | ROBO1 | 1.51 |
| 2794 | 3 | 4 | 5 | | V-1 | ROCK2 | 1.74 |
| 2795 | 3 | 4 | 5 | | V-1 | RPL36A | 1.84 |
| 2796 | 3 | 4 | 5 | | V-1 | RSBN1L | 1.89 |
| 2797 | 3 | 4 | 5 | | V-1 | SAMD9 | 1.56 |
| 2798 | 3 | 4 | 5 | | V-1 | SAMD9L | 1.95 |
| 2799 | 3 | 4 | 5 | | V-1 | SATB1 | 1.57 |
| 2800 | 3 | 4 | 5 | | V-1 | SCEL | 1.95 |
| 2801 | 3 | 4 | 5 | | V-1 | SCUBE3 | 1.60 |
| 2802 | 3 | 4 | 5 | | V-1 | SELRC1 | 1.51 |
| 2803 | 3 | 4 | 5 | | V-1 | SENP5 | 1.67 |
| 2804 | 3 | 4 | 5 | | V-1 | SEPT11 | 1.66 |
| 2805 | 3 | 4 | 5 | | V-1 | SERPINB9 | 1.66 |
| 2806 | 3 | 4 | 5 | | V-1 | SEZ6L | 1.52 |
| 2807 | 3 | 4 | 5 | | V-1 | SFMBT2 | 1.55 |
| 2808 | 3 | 4 | 5 | | V-1 | SGCD | 1.88 |
| 2809 | 3 | 4 | 5 | | V-1 | SHC3 | 1.71 |
| 2810 | 3 | 4 | 5 | | V-1 | SHCBP1 | 1.89 |
| 2811 | 3 | 4 | 5 | | V-1 | SIGLEC1 | 1.53 |
| 2812 | 3 | 4 | 5 | | V-1 | SIGLEC6 | 1.54 |
| 2813 | 3 | 4 | 5 | | V-1 | SIGLECP3 | 1.71 |
| 2814 | 3 | 4 | 5 | | V-1 | SLC30A7 | 1.60 |
| 2815 | 3 | 4 | 5 | | V-1 | SLC34A2 | 1.62 |
| 2816 | 3 | 4 | 5 | | V-1 | SLC35E3 | 1.54 |
| 2817 | 3 | 4 | 5 | | V-1 | SLC35F5 | 1.91 |
| 2818 | 3 | 4 | 5 | | V-1 | SLC3SG1 | 1.71 |
| 2819 | 3 | 4 | 5 | | V-1 | SLC38A3 | 1.55 |
| 2820 | 3 | 4 | 5 | | V-1 | SLC46A3 | 1.70 |
| 2821 | 3 | 4 | 5 | | V-1 | SLC6A1 | 1.87 |
| 2822 | 3 | 4 | 5 | | V-1 | SLC7A2 | 1.56 |
| 2823 | 3 | 4 | 5 | | V-1 | SLC8A1 | 1.81 |
| 2824 | 3 | 4 | 5 | | V-1 | SLC9A2 | 1.60 |
| 2825 | 3 | 4 | 5 | | V-1 | SLCO4C1 | 1.94 |
| 2826 | 3 | 4 | 5 | | V-1 | SLFN11 | 1.76 |
| 2827 | 3 | 4 | 5 | | V-1 | SLFN5 | 1.80 |
| 2828 | 3 | 4 | 5 | | V-1 | SLK | 1.51 |
| 2829 | 3 | 4 | 5 | | V-1 | SMA5 | 1.93 |
| 2830 | 3 | 4 | 5 | | V-1 | SMC3 | 1.55 |
| 2831 | 3 | 4 | 5 | | V-1 | SMG1 | 1.68 |
| 2832 | 3 | 4 | 5 | | V-1 | SNORA62 | 1.59 |
| 2833 | 3 | 4 | 5 | | V-1 | SNORD15B | 1.89 |
| 2834 | 3 | 4 | 5 | | V-1 | SNX13 | 1.70 |
| 2835 | 3 | 4 | 5 | | V-1 | SORL1 | 1.91 |
| 2836 | 3 | 4 | 5 | | V-1 | SPAG9 | 1.59 |
| 2837 | 3 | 4 | 5 | | V-1 | SPATA18 | 1.58 |
| 2838 | 3 | 4 | 5 | | V-1 | SPATA2S | 1.78 |
| 2839 | 3 | 4 | 5 | | V-1 | SPDYE6 | 1.70 |
| 2840 | 3 | 4 | 5 | | V-1 | SPIN1 | 1.68 |
| 2841 | 3 | 4 | 5 | | V-1 | SPIN4 | 1.69 |
| 2842 | 3 | 4 | 5 | | V-1 | SREK1IP1 | 1.63 |
| 2843 | 3 | 4 | 5 | | V-1 | SRGAP3 | 1.67 |
| 2844 | 3 | 4 | 5 | | V-1 | SSH2 | 1.98 |
| 2845 | 3 | 4 | 5 | | V-1 | STRN3 | 1.64 |
| 2846 | 3 | 4 | 5 | | V-1 | STX17 | 1.57 |
| 2847 | 3 | 4 | 5 | | V-1 | SUV39H2 | 1.50 |
| 2848 | 3 | 4 | 5 | | V-1 | SVIL | 1.78 |
| 2849 | 3 | 4 | 5 | | V-1 | SYNJ1 | 1.96 |
| 2850 | 3 | 4 | 5 | | V-1 | SYNPO2 | 1.57 |
| 2851 | 3 | 4 | 5 | | V-1 | SYPL2 | 1.72 |
| 2852 | 3 | 4 | 5 | | V-1 | TA83 | 1.77 |
| 2853 | 3 | 4 | 5 | | V-1 | TAL1 | 1.75 |
| 2854 | 3 | 4 | 5 | | V-1 | TBC1D24 | 1.59 |
| 2855 | 3 | 4 | 5 | | V-1 | TBXAS1 | 1.72 |
| 2856 | 3 | 4 | 5 | | V-1 | TCEAL2 | 1.66 |
| 2857 | 3 | 4 | 5 | | V-1 | TCEANC | 1.71 |
| 2858 | 3 | 4 | 5 | | V-1 | TCF12 | 1.62 |
| 2859 | 3 | 4 | 5 | | V-1 | TCF4 | 1.50 |
| 2860 | 3 | 4 | 5 | | V-1 | TCTEX1D4 | 1.55 |
| 2861 | 3 | 4 | 5 | | V-1 | TFDP2 | 1.53 |
| 2862 | 3 | 4 | 5 | | V-1 | TGFBR1 | 1.54 |
| 2863 | 3 | 4 | 5 | | V-1 | THAP6 | 1.62 |
| 2864 | 3 | 4 | 5 | | V-1 | THAP9 | 1.50 |
| 2865 | 3 | 4 | 5 | | V-1 | THUMPD1 | 1.63 |
| 2866 | 3 | 4 | 5 | | V-1 | TIMM8A | 1.50 |
| 2867 | 3 | 4 | 5 | | V-1 | TMED5 | 1.59 |
| 2868 | 3 | 4 | 5 | | V-1 | TMEM106A | 1.63 |
| 2869 | 3 | 4 | 5 | | V-1 | TMEM136 | 1.79 |
| 2870 | 3 | 4 | 5 | | V-1 | TMEM150C | 1.69 |
| 2871 | 3 | 4 | 5 | | V-1 | TMEM167B | 1.56 |
| 2872 | 3 | 4 | 5 | | V-1 | TMEM181 | 1.57 |
| 2873 | 3 | 4 | 5 | | V-1 | TMEM200A | 1.78 |
| 2874 | 3 | 4 | 5 | | V-1 | TMEM38B | 1.55 |
| 2875 | 3 | 4 | 5 | | V-1 | TMEM47 | 1.52 |
| 2876 | 3 | 4 | 5 | | V-1 | TMF1 | 1.50 |
| 2877 | 3 | 4 | 5 | | V-1 | TMTC2 | 1.79 |

Fig. 38 - 16

| | | | | | | | | | | | | | | | |
|---|---|---|---|---|---|---|---|---|---|---|---|---|---|---|---|
| 2878 | 3 | 4 | 5 | | V-1 | TNFRSF10D | 1.72 | 2974 | 3 | 4 | 5 | | V-1 | ZNF615 | 1.52 |
| 2879 | 3 | 4 | 5 | | V-1 | TNFRSF11A | 1.83 | 2975 | 3 | 4 | 5 | | V-1 | ZNF616 | 1.57 |
| 2880 | 3 | 4 | 5 | | V-1 | TNFSF8 | 1.92 | 2976 | 3 | 4 | 5 | | V-1 | ZNF618 | 1.61 |
| 2881 | 3 | 4 | 5 | | V-1 | TNRC6B | 1.83 | 2977 | 3 | 4 | 5 | | V-1 | ZNF641 | 1.57 |
| 2882 | 3 | 4 | 5 | | V-1 | TNRC6C | 1.95 | 2978 | 3 | 4 | 5 | | V-1 | ZNF70 | 1.82 |
| 2883 | 3 | 4 | 5 | | V-1 | TOP1P1 | 1.71 | 2979 | 3 | 4 | 5 | | V-1 | ZNF765 | 1.69 |
| 2884 | 3 | 4 | 5 | | V-1 | TOPORS | 1.63 | 2980 | 3 | 4 | 5 | | V-1 | ZNF773 | 1.68 |
| 2885 | 3 | 4 | 5 | | V-1 | TOX | 1.57 | 2981 | 3 | 4 | 5 | | V-1 | ZNF776 | 1.68 |
| 2886 | 3 | 4 | 5 | | V-1 | TP53BP1 | 1.80 | 2982 | 3 | 4 | 5 | | V-1 | ZNF778 | 1.84 |
| 2887 | 3 | 4 | 5 | | V-1 | TPK1 | 1.56 | 2983 | 3 | 4 | 5 | | V-1 | ZNF782 | 2.00 |
| 2888 | 3 | 4 | 5 | | V-1 | TPST1 | 1.55 | 2984 | 3 | 4 | 5 | | V-1 | ZNF788 | 1.61 |
| 2889 | 3 | 4 | 5 | | V-1 | TRAPPC6B | 1.54 | 2985 | 3 | 4 | 5 | | V-1 | ZNF79 | 1.63 |
| 2890 | 3 | 4 | 5 | | V-1 | TRIM22 | 1.86 | 2986 | 3 | 4 | 5 | | V-1 | ZNF8 | 1.79 |
| 2891 | 3 | 4 | 5 | | V-1 | TRIM23 | 1.92 | 2987 | 3 | 4 | 5 | | V-1 | ZNF800 | 1.58 |
| 2892 | 3 | 4 | 5 | | V-1 | TRIM33 | 1.79 | 2988 | 3 | 4 | 5 | | V-1 | ZNF808 | 1.97 |
| 2893 | 3 | 4 | 5 | | V-1 | TRIM78P | 1.86 | 2989 | 3 | 4 | 5 | | V-1 | ZNF816 | 1.90 |
| 2894 | 3 | 4 | 5 | | V-1 | TSHZ2 | 1.81 | 2990 | 3 | 4 | 5 | | V-1 | ZNF827 | 1.88 |
| 2895 | 3 | 4 | 5 | | V-1 | TUBD1 | 1.55 | 2991 | 3 | 4 | 5 | | V-1 | ZNF829 | 1.95 |
| 2896 | 3 | 4 | 5 | | V-1 | TWISTNB | 1.55 | 2992 | 3 | 4 | 5 | | V-1 | ZNF836 | 1.68 |
| 2897 | 3 | 4 | 5 | | V-1 | UACA | 1.65 | 2993 | 3 | 4 | 5 | | V-1 | ZNF845 | 1.51 |
| 2898 | 3 | 4 | 5 | | V-1 | UBE4A | 1.88 | 2994 | 3 | 4 | 5 | | V-1 | ZNF879 | 1.67 |
| 2899 | 3 | 4 | 5 | | V-1 | UGT2A1 | 1.91 | 2995 | 3 | 4 | 5 | | V-1 | ZNF93 | 1.83 |
| 2900 | 3 | 4 | 5 | | V-1 | USP46 | 1.81 | 2996 | 3 | 4 | 5 | | V-1 | ZSWIM3 | 1.56 |
| 2901 | 3 | 4 | 5 | | V-1 | USP51 | 1.59 | 2997 | 3 | 4 | 5 | | V-1 | ZZZ3 | 1.61 |
| 2902 | 3 | 4 | 5 | | V-1 | UTP23 | 1.74 | 2998 | 3 | 4 | | | IV-2 | A1BG | 0.93 |
| 2903 | 3 | 4 | 5 | | V-1 | VPS36 | 1.56 | 2999 | 3 | 4 | | | IV-2 | A2M | 0.76 |
| 2904 | 3 | 4 | 5 | | V-1 | VPS54 | 1.59 | 3000 | 3 | 4 | | | IV-2 | AAGAB | 0.94 |
| 2905 | 3 | 4 | 5 | | V-1 | WASF3 | 1.53 | 3001 | 3 | 4 | | | IV-2 | AARS2 | 0.96 |
| 2906 | 3 | 4 | 5 | | V-1 | WASL | 1.57 | 3002 | 3 | 4 | | | IV-2 | AATK | 0.68 |
| 2907 | 3 | 4 | 5 | | V-1 | WDFY2 | 1.60 | 3003 | 3 | 4 | | | IV-2 | ABCA2 | 0.67 |
| 2908 | 3 | 4 | 5 | | V-1 | WDFY3-AS2 | 1.85 | 3004 | 3 | 4 | | | IV-2 | ABCA7 | 0.72 |
| 2909 | 3 | 4 | 5 | | V-1 | WDR35 | 1.93 | 3005 | 3 | 4 | | | IV-2 | ABCB6 | 0.67 |
| 2910 | 3 | 4 | 5 | | V-1 | WDR72 | 1.73 | 3006 | 3 | 4 | | | IV-2 | ABCB7 | 0.93 |
| 2911 | 3 | 4 | 5 | | V-1 | WFDC1 | 1.59 | 3007 | 3 | 4 | | | IV-2 | ABCB9 | 0.82 |
| 2912 | 3 | 4 | 5 | | V-1 | WIPF1 | 1.58 | 3008 | 3 | 4 | | | IV-2 | ABCC1 | 0.83 |
| 2913 | 3 | 4 | 5 | | V-1 | WISP1 | 1.65 | 3009 | 3 | 4 | | | IV-2 | ABCC10 | 0.72 |
| 2914 | 3 | 4 | 5 | | V-1 | XIAP | 1.53 | 3010 | 3 | 4 | | | IV-2 | ABCC6 | 0.68 |
| 2915 | 3 | 4 | 5 | | V-1 | YPEL2 | 1.89 | 3011 | 3 | 4 | | | IV-2 | ABCE1 | 0.89 |
| 2916 | 3 | 4 | 5 | | V-1 | ZBTB3 | 1.60 | 3012 | 3 | 4 | | | IV-2 | ABCF2 | 0.69 |
| 2917 | 3 | 4 | 5 | | V-1 | ZBTB11 | 1.55 | 3013 | 3 | 4 | | | IV-2 | ABHD14A | 0.89 |
| 2918 | 3 | 4 | 5 | | V-1 | ZBTB26 | 1.54 | 3014 | 3 | 4 | | | IV-2 | ABHD15 | 0.69 |
| 2919 | 3 | 4 | 5 | | V-1 | ZBTB3 | 1.54 | 3015 | 3 | 4 | | | IV-2 | ABHD16A | 0.72 |
| 2920 | 3 | 4 | 5 | | V-1 | ZBTB34 | 1.96 | 3016 | 3 | 4 | | | IV-2 | ABHD2 | 0.91 |
| 2921 | 3 | 4 | 5 | | V-1 | ZC2HC1A | 1.56 | 3017 | 3 | 4 | | | IV-2 | ABTB2 | 0.78 |
| 2922 | 3 | 4 | 5 | | V-1 | ZC3H12C | 1.69 | 3018 | 3 | 4 | | | IV-2 | ACAA1 | 0.83 |
| 2923 | 3 | 4 | 5 | | V-1 | ZC3H12D | 1.65 | 3019 | 3 | 4 | | | IV-2 | ACAD10 | 0.84 |
| 2924 | 3 | 4 | 5 | | V-1 | ZC3H6 | 1.57 | 3020 | 3 | 4 | | | IV-2 | ACAD9 | 0.89 |
| 2925 | 3 | 4 | 5 | | V-1 | ZDHHC23 | 1.71 | 3021 | 3 | 4 | | | IV-2 | ACAT1 | 0.80 |
| 2926 | 3 | 4 | 5 | | V-1 | ZEB2 | 1.77 | 3022 | 3 | 4 | | | IV-2 | ACCN1 | 0.98 |
| 2927 | 3 | 4 | 5 | | V-1 | ZFP106 | 1.59 | 3023 | 3 | 4 | | | IV-2 | ACCN3 | 0.87 |
| 2928 | 3 | 4 | 5 | | V-1 | ZFP37 | 1.61 | 3024 | 3 | 4 | | | IV-2 | ACN9 | 0.83 |
| 2929 | 3 | 4 | 5 | | V-1 | ZFP62 | 1.86 | 3025 | 3 | 4 | | | IV-2 | ACOT11 | 0.90 |
| 2930 | 3 | 4 | 5 | | V-1 | ZFP82 | 1.70 | 3026 | 3 | 4 | | | IV-2 | ACOT8 | 0.77 |
| 2931 | 3 | 4 | 5 | | V-1 | ZFP90 | 1.69 | 3027 | 3 | 4 | | | IV-2 | ACP1 | 0.87 |
| 2932 | 3 | 4 | 5 | | V-1 | ZFYVE9 | 1.64 | 3028 | 3 | 4 | | | IV-2 | ACSS1 | 0.71 |
| 2933 | 3 | 4 | 5 | | V-1 | ZHX3 | 1.62 | 3029 | 3 | 4 | | | IV-2 | ACTC1 | 0.70 |
| 2934 | 3 | 4 | 5 | | V-1 | ZNF101 | 1.51 | 3030 | 3 | 4 | | | IV-2 | ACTL10 | 0.69 |
| 2935 | 3 | 4 | 5 | | V-1 | ZNF121 | 1.63 | 3031 | 3 | 4 | | | IV-2 | ACTL6A | 0.84 |
| 2936 | 3 | 4 | 5 | | V-1 | ZNF132 | 1.60 | 3032 | 3 | 4 | | | IV-2 | ACTN1 | 0.74 |
| 2937 | 3 | 4 | 5 | | V-1 | ZNF14 | 1.80 | 3033 | 3 | 4 | | | IV-2 | ACTR10 | 0.90 |
| 2938 | 3 | 4 | 5 | | V-1 | ZNF140 | 1.65 | 3034 | 3 | 4 | | | IV-2 | ACTR6 | 0.90 |
| 2939 | 3 | 4 | 5 | | V-1 | ZNF160 | 1.69 | 3035 | 3 | 4 | | | IV-2 | ACVR1 | 0.69 |
| 2940 | 3 | 4 | 5 | | V-1 | ZNF17 | 1.59 | 3036 | 3 | 4 | | | IV-2 | ACYP2 | 0.91 |
| 2941 | 3 | 4 | 5 | | V-1 | ZNF222 | 1.60 | 3037 | 3 | 4 | | | IV-2 | ADAM8 | 0.72 |
| 2942 | 3 | 4 | 5 | | V-1 | ZNF227 | 1.78 | 3038 | 3 | 4 | | | IV-2 | ADAMTS13 | 0.94 |
| 2943 | 3 | 4 | 5 | | V-1 | ZNF235 | 1.94 | 3039 | 3 | 4 | | | IV-2 | ADAMTSL4 | 0.70 |
| 2944 | 3 | 4 | 5 | | V-1 | ZNF250 | 1.59 | 3040 | 3 | 4 | | | IV-2 | ADARB1 | 0.95 |
| 2945 | 3 | 4 | 5 | | V-1 | ZNF267 | 1.97 | 3041 | 3 | 4 | | | IV-2 | ADC | 0.95 |
| 2946 | 3 | 4 | 5 | | V-1 | ZNF284 | 1.61 | 3042 | 3 | 4 | | | IV-2 | ADCY2 | 0.73 |
| 2947 | 3 | 4 | 5 | | V-1 | ZNF286A | 1.96 | 3043 | 3 | 4 | | | IV-2 | ADCY3 | 0.86 |
| 2948 | 3 | 4 | 5 | | V-1 | ZNF287 | 1.59 | 3044 | 3 | 4 | | | IV-2 | ADCY9 | 0.77 |
| 2949 | 3 | 4 | 5 | | V-1 | ZNF320 | 1.67 | 3045 | 3 | 4 | | | IV-2 | ADD1 | 0.72 |
| 2950 | 3 | 4 | 5 | | V-1 | ZNF334 | 1.55 | 3046 | 3 | 4 | | | IV-2 | ADI1 | 0.75 |
| 2951 | 3 | 4 | 5 | | V-1 | ZNF354A | 1.70 | 3047 | 3 | 4 | | | IV-2 | ADIPOR1 | 0.71 |
| 2952 | 3 | 4 | 5 | | V-1 | ZNF366 | 1.51 | 3048 | 3 | 4 | | | IV-2 | ADK | 0.99 |
| 2953 | 3 | 4 | 5 | | V-1 | ZNF383 | 1.90 | 3049 | 3 | 4 | | | IV-2 | ADORA2A | 0.96 |
| 2954 | 3 | 4 | 5 | | V-1 | ZNF385B | 1.50 | 3050 | 3 | 4 | | | IV-2 | ADORA2B | 0.70 |
| 2955 | 3 | 4 | 5 | | V-1 | ZNF404 | 1.96 | 3051 | 3 | 4 | | | IV-2 | ADPGK | 0.98 |
| 2956 | 3 | 4 | 5 | | V-1 | ZNF41 | 1.77 | 3052 | 3 | 4 | | | IV-2 | ADPRH | 0.84 |
| 2957 | 3 | 4 | 5 | | V-1 | ZNF418 | 1.85 | 3053 | 3 | 4 | | | IV-2 | ADRB1 | 0.98 |
| 2958 | 3 | 4 | 5 | | V-1 | ZNF420 | 1.91 | 3054 | 3 | 4 | | | IV-2 | ADSL | 0.94 |
| 2959 | 3 | 4 | 5 | | V-1 | ZNF43 | 1.54 | 3055 | 3 | 4 | | | IV-2 | ADSS | 0.78 |
| 2960 | 3 | 4 | 5 | | V-1 | ZNF436 | 1.77 | 3056 | 3 | 4 | | | IV-2 | AEBP1 | 0.85 |
| 2961 | 3 | 4 | 5 | | V-1 | ZNF440 | 1.88 | 3057 | 3 | 4 | | | IV-2 | AEBP2 | 0.98 |
| 2962 | 3 | 4 | 5 | | V-1 | ZNF470 | 1.53 | 3058 | 3 | 4 | | | IV-2 | AFG3L2 | 0.70 |
| 2963 | 3 | 4 | 5 | | V-1 | ZNF491 | 1.68 | 3059 | 3 | 4 | | | IV-2 | AGAP1 | 0.74 |
| 2964 | 3 | 4 | 5 | | V-1 | ZNF501 | 1.65 | 3060 | 3 | 4 | | | IV-2 | AGBL5 | 0.80 |
| 2965 | 3 | 4 | 5 | | V-1 | ZNF503-AS1 | 1.58 | 3061 | 3 | 4 | | | IV-2 | AGPAT6 | 0.73 |
| 2966 | 3 | 4 | 5 | | V-1 | ZNF507 | 1.56 | 3062 | 3 | 4 | | | IV-2 | AGPHD1 | 0.84 |
| 2967 | 3 | 4 | 5 | | V-1 | ZNF510 | 1.55 | 3063 | 3 | 4 | | | IV-2 | AGXT2L2 | 0.96 |
| 2968 | 3 | 4 | 5 | | V-1 | ZNF525 | 1.81 | 3064 | 3 | 4 | | | IV-2 | AHR | 0.81 |
| 2969 | 3 | 4 | 5 | | V-1 | ZNF527 | 1.61 | 3065 | 3 | 4 | | | IV-2 | AIDA | 0.84 |
| 2970 | 3 | 4 | 5 | | V-1 | ZNF532 | 1.97 | 3066 | 3 | 4 | | | IV-2 | AIF1L | 0.75 |
| 2971 | 3 | 4 | 5 | | V-1 | ZNF548 | 1.51 | 3067 | 3 | 4 | | | IV-2 | AIG1 | 0.79 |
| 2972 | 3 | 4 | 5 | | V-1 | ZNF557 | 1.77 | 3068 | 3 | 4 | | | IV-2 | AJAP1 | 0.95 |
| 2973 | 3 | 4 | 5 | | V-1 | ZNF567 | 1.65 | 3069 | 3 | 4 | | | IV-2 | AK2 | 0.97 |

Fig. 38 - 17

| | | | | | | | | | | | | | | |
|---|---|---|---|---|---|---|---|---|---|---|---|---|---|---|
| 3070 | 3 | 4 | | | IV-2 | AKAP1 | 0.92 | 3166 | 3 | 4 | | | IV-2 | ARMCX1 | 0.87 |
| 3071 | 3 | 4 | | | IV-2 | AKAP17A | 0.81 | 3167 | 3 | 4 | | | IV-2 | ARMCX6 | 0.87 |
| 3072 | 3 | 4 | | | IV-2 | AKAP6 | 0.95 | 3168 | 3 | 4 | | | IV-2 | ARNT2 | 0.86 |
| 3073 | 3 | 4 | | | IV-2 | AKD1 | 1.00 | 3169 | 3 | 4 | | | IV-2 | ARPC1A | 0.75 |
| 3074 | 3 | 4 | | | IV-2 | AKIRIN2 | 0.70 | 3170 | 3 | 4 | | | IV-2 | ARPC1B | 0.72 |
| 3075 | 3 | 4 | | | IV-2 | AKR1A1 | 0.95 | 3171 | 3 | 4 | | | IV-2 | ARPC2 | 0.73 |
| 3076 | 3 | 4 | | | IV-2 | AKR1B1 | 0.95 | 3172 | 3 | 4 | | | IV-2 | ARPC3 | 0.83 |
| 3077 | 3 | 4 | | | IV-2 | AKR1C2 | 0.75 | 3173 | 3 | 4 | | | IV-2 | ARPC5 | 0.94 |
| 3078 | 3 | 4 | | | IV-2 | AKR1C3 | 0.76 | 3174 | 3 | 4 | | | IV-2 | ARPP19 | 0.87 |
| 3079 | 3 | 4 | | | IV-2 | AKR1E2 | 0.88 | 3175 | 3 | 4 | | | IV-2 | ARRB2 | 0.81 |
| 3080 | 3 | 4 | | | IV-2 | ALAD | 0.75 | 3176 | 3 | 4 | | | IV-2 | ART4 | 0.94 |
| 3081 | 3 | 4 | | | IV-2 | ALAS1 | 0.92 | 3177 | 3 | 4 | | | IV-2 | ARV1 | 0.68 |
| 3082 | 3 | 4 | | | IV-2 | ALDH18A1 | 0.84 | 3178 | 3 | 4 | | | IV-2 | ASAP2 | 0.92 |
| 3083 | 3 | 4 | | | IV-2 | ALDH3A1 | 0.71 | 3179 | 3 | 4 | | | IV-2 | ASAP3 | 0.68 |
| 3084 | 3 | 4 | | | IV-2 | ALDH3B1 | 0.86 | 3180 | 3 | 4 | | | IV-2 | ASB14 | 0.99 |
| 3085 | 3 | 4 | | | IV-2 | ALDH4A1 | 0.85 | 3181 | 3 | 4 | | | IV-2 | ASCC1 | 0.92 |
| 3086 | 3 | 4 | | | IV-2 | ALDH7A1 | 0.96 | 3182 | 3 | 4 | | | IV-2 | ASH2L | 0.88 |
| 3087 | 3 | 4 | | | IV-2 | ALDH8A1 | 0.98 | 3183 | 3 | 4 | | | IV-2 | ASMTL | 0.76 |
| 3088 | 3 | 4 | | | IV-2 | ALG1 | 0.76 | 3184 | 3 | 4 | | | IV-2 | ASNSD1 | 0.91 |
| 3089 | 3 | 4 | | | IV-2 | ALG14 | 0.83 | 3185 | 3 | 4 | | | IV-2 | ASTN1 | 0.91 |
| 3090 | 3 | 4 | | | IV-2 | ALG2 | 0.91 | 3186 | 3 | 4 | | | IV-2 | ASUN | 0.90 |
| 3091 | 3 | 4 | | | IV-2 | ALKBH3 | 0.81 | 3187 | 3 | 4 | | | IV-2 | ATAD3C | 0.99 |
| 3092 | 3 | 4 | | | IV-2 | ALOX12 | 0.68 | 3188 | 3 | 4 | | | IV-2 | ATF5 | 0.72 |
| 3093 | 3 | 4 | | | IV-2 | ALOX5 | 0.79 | 3189 | 3 | 4 | | | IV-2 | ATF6B | 0.75 |
| 3094 | 3 | 4 | | | IV-2 | ALX1 | 0.78 | 3190 | 3 | 4 | | | IV-2 | ATG10 | 0.91 |
| 3095 | 3 | 4 | | | IV-2 | ALX3 | 0.99 | 3191 | 3 | 4 | | | IV-2 | ATG16L1 | 0.90 |
| 3096 | 3 | 4 | | | IV-2 | AMBRA1 | 0.76 | 3192 | 3 | 4 | | | IV-2 | ATG4A | 0.90 |
| 3097 | 3 | 4 | | | IV-2 | AMDHD2 | 0.82 | 3193 | 3 | 4 | | | IV-2 | ATG7 | 0.98 |
| 3098 | 3 | 4 | | | IV-2 | AMFR | 0.78 | 3194 | 3 | 4 | | | IV-2 | ATG9B | 0.75 |
| 3099 | 3 | 4 | | | IV-2 | AMH | 0.86 | 3195 | 3 | 4 | | | IV-2 | ATHL1 | 0.82 |
| 3100 | 3 | 4 | | | IV-2 | AMPD2 | 0.86 | 3196 | 3 | 4 | | | IV-2 | ATIC | 0.97 |
| 3101 | 3 | 4 | | | IV-2 | AMPD3 | 0.95 | 3197 | 3 | 4 | | | IV-2 | ATOX1 | 0.73 |
| 3102 | 3 | 4 | | | IV-2 | AMZ2 | 0.93 | 3198 | 3 | 4 | | | IV-2 | ATP13A5 | 0.87 |
| 3103 | 3 | 4 | | | IV-2 | ANAPC1 | 0.94 | 3199 | 3 | 4 | | | IV-2 | ATP1A1 | 0.69 |
| 3104 | 3 | 4 | | | IV-2 | ANAPC10 | 0.77 | 3200 | 3 | 4 | | | IV-2 | ATP1B1 | 0.76 |
| 3105 | 3 | 4 | | | IV-2 | ANAPC13 | 0.84 | 3201 | 3 | 4 | | | IV-2 | ATP1B3 | 0.68 |
| 3106 | 3 | 4 | | | IV-2 | ANAPC16 | 0.87 | 3202 | 3 | 4 | | | IV-2 | ATP2B1 | 0.97 |
| 3107 | 3 | 4 | | | IV-2 | ANAPC5 | 0.91 | 3203 | 3 | 4 | | | IV-2 | ATP2C2 | 0.97 |
| 3108 | 3 | 4 | | | IV-2 | ANGEL1 | 0.93 | 3204 | 3 | 4 | | | IV-2 | ATP5B | 0.86 |
| 3109 | 3 | 4 | | | IV-2 | ANGPTL1 | 0.95 | 3205 | 3 | 4 | | | IV-2 | ATP5C1 | 0.77 |
| 3110 | 3 | 4 | | | IV-2 | ANKLE1 | 0.87 | 3206 | 3 | 4 | | | IV-2 | ATP5E | 0.77 |
| 3111 | 3 | 4 | | | IV-2 | ANKLE2 | 0.82 | 3207 | 3 | 4 | | | IV-2 | ATP5EP2 | 0.76 |
| 3112 | 3 | 4 | | | IV-2 | ANKMY1 | 0.76 | 3208 | 3 | 4 | | | IV-2 | ATP5F1 | 0.87 |
| 3113 | 3 | 4 | | | IV-2 | ANKRD16 | 0.94 | 3209 | 3 | 4 | | | IV-2 | ATP5G1 | 0.83 |
| 3114 | 3 | 4 | | | IV-2 | ANKRD27 | 0.82 | 3210 | 3 | 4 | | | IV-2 | ATP5G3 | 0.99 |
| 3115 | 3 | 4 | | | IV-2 | ANKRD52 | 0.68 | 3211 | 3 | 4 | | | IV-2 | ATP5J | 0.87 |
| 3116 | 3 | 4 | | | IV-2 | ANKRD65 | 0.82 | 3212 | 3 | 4 | | | IV-2 | ATP5J2 | 0.97 |
| 3117 | 3 | 4 | | | IV-2 | ANKS6 | 0.85 | 3213 | 3 | 4 | | | IV-2 | ATP5L | 0.91 |
| 3118 | 3 | 4 | | | IV-2 | ANP32A | 0.72 | 3214 | 3 | 4 | | | IV-2 | ATP5O | 0.85 |
| 3119 | 3 | 4 | | | IV-2 | ANP32AP1 | 0.75 | 3215 | 3 | 4 | | | IV-2 | ATP6AP2 | 0.86 |
| 3120 | 3 | 4 | | | IV-2 | ANP32B | 0.77 | 3216 | 3 | 4 | | | IV-2 | ATP6V0E1 | 0.71 |
| 3121 | 3 | 4 | | | IV-2 | ANP32C | 0.80 | 3217 | 3 | 4 | | | IV-2 | ATP6V1E1 | 0.84 |
| 3122 | 3 | 4 | | | IV-2 | ANTXR1 | 0.98 | 3218 | 3 | 4 | | | IV-2 | ATP6V1E2 | 0.86 |
| 3123 | 3 | 4 | | | IV-2 | ANXA13 | 0.95 | 3219 | 3 | 4 | | | IV-2 | ATP6V1G1 | 0.83 |
| 3124 | 3 | 4 | | | IV-2 | ANXA4 | 0.84 | 3220 | 3 | 4 | | | IV-2 | ATP6V1G2 | 0.94 |
| 3125 | 3 | 4 | | | IV-2 | ANXA7 | 0.75 | 3221 | 3 | 4 | | | IV-2 | ATP6V1H | 0.99 |
| 3126 | 3 | 4 | | | IV-2 | AP1S2 | 0.98 | 3222 | 3 | 4 | | | IV-2 | ATP9B | 0.82 |
| 3127 | 3 | 4 | | | IV-2 | AP2A2 | 0.78 | 3223 | 3 | 4 | | | IV-2 | ATPAF1 | 0.79 |
| 3128 | 3 | 4 | | | IV-2 | AP2B1 | 0.75 | 3224 | 3 | 4 | | | IV-2 | ATPBD4 | 0.78 |
| 3129 | 3 | 4 | | | IV-2 | AP3D1 | 0.69 | 3225 | 3 | 4 | | | IV-2 | ATPIF1 | 0.86 |
| 3130 | 3 | 4 | | | IV-2 | APBA3 | 0.69 | 3226 | 3 | 4 | | | IV-2 | ATXN10 | 0.85 |
| 3131 | 3 | 4 | | | IV-2 | APBB1 | 0.67 | 3227 | 3 | 4 | | | IV-2 | AURKC | 0.84 |
| 3132 | 3 | 4 | | | IV-2 | API5 | 0.90 | 3228 | 3 | 4 | | | IV-2 | AUTS2 | 0.69 |
| 3133 | 3 | 4 | | | IV-2 | APIP | 0.87 | 3229 | 3 | 4 | | | IV-2 | B2M | 0.72 |
| 3134 | 3 | 4 | | | IV-2 | APLP2 | 0.79 | 3230 | 3 | 4 | | | IV-2 | B3GNT1 | 0.72 |
| 3135 | 3 | 4 | | | IV-2 | APOD | 0.99 | 3231 | 3 | 4 | | | IV-2 | B3GNT2 | 0.87 |
| 3136 | 3 | 4 | | | IV-2 | APOL1 | 0.73 | 3232 | 3 | 4 | | | IV-2 | B4GALNT4 | 0.81 |
| 3137 | 3 | 4 | | | IV-2 | APOL4 | 0.79 | 3233 | 3 | 4 | | | IV-2 | B4GALT3 | 0.73 |
| 3138 | 3 | 4 | | | IV-2 | APOPT1 | 0.75 | 3234 | 3 | 4 | | | IV-2 | B4GALT5 | 0.87 |
| 3139 | 3 | 4 | | | IV-2 | APP | 0.91 | 3235 | 3 | 4 | | | IV-2 | B4GALT6 | 0.94 |
| 3140 | 3 | 4 | | | IV-2 | AQP7P3 | 0.86 | 3236 | 3 | 4 | | | IV-2 | BAALC | 0.98 |
| 3141 | 3 | 4 | | | IV-2 | AQR | 0.75 | 3237 | 3 | 4 | | | IV-2 | BABAM1 | 0.73 |
| 3142 | 3 | 4 | | | IV-2 | ARAP1 | 0.89 | 3238 | 3 | 4 | | | IV-2 | BAG4 | 0.82 |
| 3143 | 3 | 4 | | | IV-2 | ARCN1 | 0.94 | 3239 | 3 | 4 | | | IV-2 | BAIAP2L1 | 0.73 |
| 3144 | 3 | 4 | | | IV-2 | ARF4 | 0.80 | 3240 | 3 | 4 | | | IV-2 | BANP | 0.73 |
| 3145 | 3 | 4 | | | IV-2 | ARFGAP2 | 0.71 | 3241 | 3 | 4 | | | IV-2 | BASP1P1 | 0.99 |
| 3146 | 3 | 4 | | | IV-2 | ARHGAP11A | 0.82 | 3242 | 3 | 4 | | | IV-2 | BATF2 | 0.95 |
| 3147 | 3 | 4 | | | IV-2 | ARHGAP31 | 0.82 | 3243 | 3 | 4 | | | IV-2 | BAX | 0.77 |
| 3148 | 3 | 4 | | | IV-2 | ARHGAP4 | 0.91 | 3244 | 3 | 4 | | | IV-2 | BBC3 | 0.69 |
| 3149 | 3 | 4 | | | IV-2 | ARHGAP44 | 0.89 | 3245 | 3 | 4 | | | IV-2 | BBIP1 | 0.73 |
| 3150 | 3 | 4 | | | IV-2 | ARHGDIB | 0.68 | 3246 | 3 | 4 | | | IV-2 | BBS1 | 0.74 |
| 3151 | 3 | 4 | | | IV-2 | ARHGEF1 | 0.75 | 3247 | 3 | 4 | | | IV-2 | BBS9 | 0.89 |
| 3152 | 3 | 4 | | | IV-2 | ARHGEF10L | 0.67 | 3248 | 3 | 4 | | | IV-2 | BCCIP | 0.93 |
| 3153 | 3 | 4 | | | IV-2 | ARHGEF11 | 0.70 | 3249 | 3 | 4 | | | IV-2 | BCDIN3D | 0.83 |
| 3154 | 3 | 4 | | | IV-2 | ARHGEF18 | 0.78 | 3250 | 3 | 4 | | | IV-2 | BCL11A | 0.86 |
| 3155 | 3 | 4 | | | IV-2 | ARHGEF2 | 0.73 | 3251 | 3 | 4 | | | IV-2 | BCL2L2 | 0.93 |
| 3156 | 3 | 4 | | | IV-2 | ARHGEF3 | 0.91 | 3252 | 3 | 4 | | | IV-2 | BCL6 | 0.88 |
| 3157 | 3 | 4 | | | IV-2 | ARHGEF40 | 0.73 | 3253 | 3 | 4 | | | IV-2 | BCR | 0.69 |
| 3158 | 3 | 4 | | | IV-2 | ARHGEF7 | 0.87 | 3254 | 3 | 4 | | | IV-2 | BCRP2 | 0.81 |
| 3159 | 3 | 4 | | | IV-2 | ARID3B | 0.75 | 3255 | 3 | 4 | | | IV-2 | BECN1 | 0.99 |
| 3160 | 3 | 4 | | | IV-2 | ARIH2 | 0.97 | 3256 | 3 | 4 | | | IV-2 | BEND7 | 0.96 |
| 3161 | 3 | 4 | | | IV-2 | ARL17B | 0.90 | 3257 | 3 | 4 | | | IV-2 | BET1L | 0.76 |
| 3162 | 3 | 4 | | | IV-2 | ARL2BP | 0.83 | 3258 | 3 | 4 | | | IV-2 | BEX4 | 0.84 |
| 3163 | 3 | 4 | | | IV-2 | ARL3 | 0.78 | 3259 | 3 | 4 | | | IV-2 | BFAR | 0.87 |
| 3164 | 3 | 4 | | | IV-2 | ARL6IP1 | 0.94 | 3260 | 3 | 4 | | | IV-2 | BHLHE40 | 0.84 |
| 3165 | 3 | 4 | | | IV-2 | ARL6IP5 | 0.78 | 3261 | 3 | 4 | | | IV-2 | BID | 0.94 |

Fig. 38 - 18

| | | | | | | | | | | | | | | |
|---|---|---|---|---|---|---|---|---|---|---|---|---|---|---|
| 3262 | 3 | 4 | | | IV-2 | BIN3 | 0.71 | 3358 | 3 | 4 | | | IV-2 | C1orf122 | 0.88 |
| 3263 | 3 | 4 | | | IV-2 | BLOC1S1 | 0.68 | 3359 | 3 | 4 | | | IV-2 | C1orf123 | 0.80 |
| 3264 | 3 | 4 | | | IV-2 | BLOC1S3 | 0.70 | 3360 | 3 | 4 | | | IV-2 | C1orf131 | 0.98 |
| 3265 | 3 | 4 | | | IV-2 | BLVRA | 0.93 | 3361 | 3 | 4 | | | IV-2 | C1orf198 | 0.68 |
| 3266 | 3 | 4 | | | IV-2 | BLVRB | 0.72 | 3362 | 3 | 4 | | | IV-2 | C1orf201 | 0.82 |
| 3267 | 3 | 4 | | | IV-2 | BMP8A | 0.96 | 3363 | 3 | 4 | | | IV-2 | C1orf212 | 0.71 |
| 3268 | 3 | 4 | | | IV-2 | BMX | 0.99 | 3364 | 3 | 4 | | | IV-2 | C1orf226 | 0.73 |
| 3269 | 3 | 4 | | | IV-2 | BNIP1 | 0.82 | 3365 | 3 | 4 | | | IV-2 | C1orf35 | 0.69 |
| 3270 | 3 | 4 | | | IV-2 | BNIP3 | 0.87 | 3366 | 3 | 4 | | | IV-2 | C1orf53 | 0.90 |
| 3271 | 3 | 4 | | | IV-2 | BNIPL | 0.98 | 3367 | 3 | 4 | | | IV-2 | C1orf56 | 0.75 |
| 3272 | 3 | 4 | | | IV-2 | BOC | 0.84 | 3368 | 3 | 4 | | | IV-2 | C1orf85 | 0.85 |
| 3273 | 3 | 4 | | | IV-2 | BOD1 | 0.74 | 3369 | 3 | 4 | | | IV-2 | C1QTNF4 | 0.76 |
| 3274 | 3 | 4 | | | IV-2 | BOD1P | 0.86 | 3370 | 3 | 4 | | | IV-2 | C1RL | 0.85 |
| 3275 | 3 | 4 | | | IV-2 | BOLA1 | 0.74 | 3371 | 3 | 4 | | | IV-2 | C2 | 0.79 |
| 3276 | 3 | 4 | | | IV-2 | BPGM | 0.75 | 3372 | 3 | 4 | | | IV-2 | C20orf111 | 0.87 |
| 3277 | 3 | 4 | | | IV-2 | BPHL | 0.73 | 3373 | 3 | 4 | | | IV-2 | C20orf20 | 0.77 |
| 3278 | 3 | 4 | | | IV-2 | BPNT1 | 0.74 | 3374 | 3 | 4 | | | IV-2 | C20orf96 | 0.74 |
| 3279 | 3 | 4 | | | IV-2 | BRD1 | 0.87 | 3375 | 3 | 4 | | | IV-2 | C21orf33 | 0.93 |
| 3280 | 3 | 4 | | | IV-2 | BRD2 | 0.84 | 3376 | 3 | 4 | | | IV-2 | C21orf59 | 0.82 |
| 3281 | 3 | 4 | | | IV-2 | BRD4 | 0.70 | 3377 | 3 | 4 | | | IV-2 | C21orf88 | 0.69 |
| 3282 | 3 | 4 | | | IV-2 | BRD7 | 0.79 | 3378 | 3 | 4 | | | IV-2 | C22orf25 | 0.77 |
| 3283 | 3 | 4 | | | IV-2 | BRE | 0.76 | 3379 | 3 | 4 | | | IV-2 | C22orf29 | 0.81 |
| 3284 | 3 | 4 | | | IV-2 | BREA2 | 0.89 | 3380 | 3 | 4 | | | IV-2 | C22orf32 | 0.87 |
| 3285 | 3 | 4 | | | IV-2 | BRIX1 | 0.87 | 3381 | 3 | 4 | | | IV-2 | C22orf39 | 0.86 |
| 3286 | 3 | 4 | | | IV-2 | BRK1 | 0.73 | 3382 | 3 | 4 | | | IV-2 | C2CD2L | 0.70 |
| 3287 | 3 | 4 | | | IV-2 | BRP44 | 0.79 | 3383 | 3 | 4 | | | IV-2 | C2orf29 | 0.94 |
| 3288 | 3 | 4 | | | IV-2 | BRP44L | 0.85 | 3384 | 3 | 4 | | | IV-2 | C2orf42 | 0.89 |
| 3289 | 3 | 4 | | | IV-2 | BRPF1 | 0.70 | 3385 | 3 | 4 | | | IV-2 | C3orf18 | 0.89 |
| 3290 | 3 | 4 | | | IV-2 | BSDC1 | 0.85 | 3386 | 3 | 4 | | | IV-2 | C3orf55 | 0.98 |
| 3291 | 3 | 4 | | | IV-2 | BTBD10 | 0.99 | 3387 | 3 | 4 | | | IV-2 | C3orf75 | 0.79 |
| 3292 | 3 | 4 | | | IV-2 | BTF3 | 0.81 | 3388 | 3 | 4 | | | IV-2 | C4orf27 | 0.73 |
| 3293 | 3 | 4 | | | IV-2 | BTF3L4 | 0.91 | 3389 | 3 | 4 | | | IV-2 | C4orf32 | 1.00 |
| 3294 | 3 | 4 | | | IV-2 | BTN3A3 | 0.85 | 3390 | 3 | 4 | | | IV-2 | C4orf33 | 0.94 |
| 3295 | 3 | 4 | | | IV-2 | BUB3 | 0.99 | 3391 | 3 | 4 | | | IV-2 | C4orf39 | 0.99 |
| 3296 | 3 | 4 | | | IV-2 | BUD13 | 0.72 | 3392 | 3 | 4 | | | IV-2 | C4orf43 | 0.91 |
| 3297 | 3 | 4 | | | IV-2 | BUD31 | 0.77 | 3393 | 3 | 4 | | | IV-2 | C4orf46 | 0.97 |
| 3298 | 3 | 4 | | | IV-2 | BZW2 | 0.73 | 3394 | 3 | 4 | | | IV-2 | C4orf47 | 0.82 |
| 3299 | 3 | 4 | | | IV-2 | C10orf11 | 0.89 | 3395 | 3 | 4 | | | IV-2 | C5orf15 | 0.80 |
| 3300 | 3 | 4 | | | IV-2 | C10orf114 | 0.84 | 3396 | 3 | 4 | | | IV-2 | C5orf20 | 0.82 |
| 3301 | 3 | 4 | | | IV-2 | C10orf25 | 0.91 | 3397 | 3 | 4 | | | IV-2 | C5orf25 | 0.86 |
| 3302 | 3 | 4 | | | IV-2 | C10orf35 | 0.81 | 3398 | 3 | 4 | | | IV-2 | C6orf115 | 0.73 |
| 3303 | 3 | 4 | | | IV-2 | C10orf55 | 0.90 | 3399 | 3 | 4 | | | IV-2 | C6orf130 | 0.98 |
| 3304 | 3 | 4 | | | IV-2 | C10orf58 | 0.81 | 3400 | 3 | 4 | | | IV-2 | C6orf136 | 0.68 |
| 3305 | 3 | 4 | | | IV-2 | C11orf1 | 0.76 | 3401 | 3 | 4 | | | IV-2 | C6orf192 | 0.84 |
| 3306 | 3 | 4 | | | IV-2 | C11orf31 | 0.74 | 3402 | 3 | 4 | | | IV-2 | C6orf203 | 0.94 |
| 3307 | 3 | 4 | | | IV-2 | C11orf35 | 0.73 | 3403 | 3 | 4 | | | IV-2 | C6orf48 | 0.74 |
| 3308 | 3 | 4 | | | IV-2 | C11orf52 | 0.70 | 3404 | 3 | 4 | | | IV-2 | C7orf13 | 0.69 |
| 3309 | 3 | 4 | | | IV-2 | C11orf63 | 0.78 | 3405 | 3 | 4 | | | IV-2 | C7orf25 | 0.80 |
| 3310 | 3 | 4 | | | IV-2 | C11orf80 | 0.73 | 3406 | 3 | 4 | | | IV-2 | C7orf42 | 0.88 |
| 3311 | 3 | 4 | | | IV-2 | C11orf9 | 0.96 | 3407 | 3 | 4 | | | IV-2 | C7orf50 | 0.73 |
| 3312 | 3 | 4 | | | IV-2 | C11orf93 | 0.83 | 3408 | 3 | 4 | | | IV-2 | C7orf55 | 0.91 |
| 3313 | 3 | 4 | | | IV-2 | C11orf95 | 0.85 | 3409 | 3 | 4 | | | IV-2 | C7orf61 | 0.99 |
| 3314 | 3 | 4 | | | IV-2 | C12orf32 | 0.76 | 3410 | 3 | 4 | | | IV-2 | C7orf73 | 0.75 |
| 3315 | 3 | 4 | | | IV-2 | C12orf47 | 0.94 | 3411 | 3 | 4 | | | IV-2 | C8orf33 | 0.81 |
| 3316 | 3 | 4 | | | IV-2 | C12orf57 | 0.67 | 3412 | 3 | 4 | | | IV-2 | C8orf42 | 0.98 |
| 3317 | 3 | 4 | | | IV-2 | C12orf68 | 1.00 | 3413 | 3 | 4 | | | IV-2 | C8orf47 | 0.99 |
| 3318 | 3 | 4 | | | IV-2 | C12orf75 | 0.97 | 3414 | 3 | 4 | | | IV-2 | C8orf76 | 0.93 |
| 3319 | 3 | 4 | | | IV-2 | C14orf109 | 0.94 | 3415 | 3 | 4 | | | IV-2 | C9orf114 | 0.69 |
| 3320 | 3 | 4 | | | IV-2 | C14orf119 | 0.75 | 3416 | 3 | 4 | | | IV-2 | C9orf123 | 0.81 |
| 3321 | 3 | 4 | | | IV-2 | C14orf133 | 0.74 | 3417 | 3 | 4 | | | IV-2 | C9orf24 | 0.99 |
| 3322 | 3 | 4 | | | IV-2 | C14orf142 | 0.75 | 3418 | 3 | 4 | | | IV-2 | C9orf30 | 0.78 |
| 3323 | 3 | 4 | | | IV-2 | C14orf159 | 0.70 | 3419 | 3 | 4 | | | IV-2 | C9orf46 | 0.79 |
| 3324 | 3 | 4 | | | IV-2 | C14orf167 | 0.95 | 3420 | 3 | 4 | | | IV-2 | C9orf64 | 0.77 |
| 3325 | 3 | 4 | | | IV-2 | C14orf176 | 0.81 | 3421 | 3 | 4 | | | IV-2 | C9orf78 | 0.94 |
| 3326 | 3 | 4 | | | IV-2 | C14orf2 | 0.87 | 3422 | 3 | 4 | | | IV-2 | C9orf82 | 0.93 |
| 3327 | 3 | 4 | | | IV-2 | C14orf43 | 0.87 | 3423 | 3 | 4 | | | IV-2 | C9orf85 | 0.72 |
| 3328 | 3 | 4 | | | IV-2 | C14orf79 | 0.84 | 3424 | 3 | 4 | | | IV-2 | C9orf95 | 0.79 |
| 3329 | 3 | 4 | | | IV-2 | C14orf93 | 0.68 | 3425 | 3 | 4 | | | IV-2 | CA11 | 0.69 |
| 3330 | 3 | 4 | | | IV-2 | C15orf23 | 0.89 | 3426 | 3 | 4 | | | IV-2 | CA12 | 0.73 |
| 3331 | 3 | 4 | | | IV-2 | C15orf44 | 0.70 | 3427 | 3 | 4 | | | IV-2 | CACNA2D2 | 0.92 |
| 3332 | 3 | 4 | | | IV-2 | C15orf57 | 0.72 | 3428 | 3 | 4 | | | IV-2 | CACYBP | 0.74 |
| 3333 | 3 | 4 | | | IV-2 | C15orf61 | 0.67 | 3429 | 3 | 4 | | | IV-2 | CAD | 0.94 |
| 3334 | 3 | 4 | | | IV-2 | C16orf46 | 0.95 | 3430 | 3 | 4 | | | IV-2 | CADM3 | 0.90 |
| 3335 | 3 | 4 | | | IV-2 | C16orf5 | 0.67 | 3431 | 3 | 4 | | | IV-2 | CALCOCO1 | 0.86 |
| 3336 | 3 | 4 | | | IV-2 | C16orf53 | 0.83 | 3432 | 3 | 4 | | | IV-2 | CALM1 | 0.82 |
| 3337 | 3 | 4 | | | IV-2 | C16orf55 | 0.73 | 3433 | 3 | 4 | | | IV-2 | CALM2 | 0.86 |
| 3338 | 3 | 4 | | | IV-2 | C16orf62 | 0.83 | 3434 | 3 | 4 | | | IV-2 | CALM3 | 0.73 |
| 3339 | 3 | 4 | | | IV-2 | C16orf70 | 0.96 | 3435 | 3 | 4 | | | IV-2 | CALR | 0.79 |
| 3340 | 3 | 4 | | | IV-2 | C16orf87 | 0.81 | 3436 | 3 | 4 | | | IV-2 | CALU | 0.93 |
| 3341 | 3 | 4 | | | IV-2 | C17orf107 | 0.84 | 3437 | 3 | 4 | | | IV-2 | CAMKK2 | 0.92 |
| 3342 | 3 | 4 | | | IV-2 | C17orf109 | 0.68 | 3438 | 3 | 4 | | | IV-2 | CAND2 | 0.70 |
| 3343 | 3 | 4 | | | IV-2 | C17orf51 | 0.92 | 3439 | 3 | 4 | | | IV-2 | CANX | 0.98 |
| 3344 | 3 | 4 | | | IV-2 | C17orf53 | 0.70 | 3440 | 3 | 4 | | | IV-2 | CAP1 | 0.90 |
| 3345 | 3 | 4 | | | IV-2 | C17orf62 | 0.72 | 3441 | 3 | 4 | | | IV-2 | CAPN5 | 0.86 |
| 3346 | 3 | 4 | | | IV-2 | C17orf63 | 0.69 | 3442 | 3 | 4 | | | IV-2 | CAPRIN1 | 0.92 |
| 3347 | 3 | 4 | | | IV-2 | C17orf67 | 0.95 | 3443 | 3 | 4 | | | IV-2 | CAPZA1 | 0.85 |
| 3348 | 3 | 4 | | | IV-2 | C17orf79 | 0.73 | 3444 | 3 | 4 | | | IV-2 | CAPZA2 | 0.85 |
| 3349 | 3 | 4 | | | IV-2 | C17orf81 | 0.71 | 3445 | 3 | 4 | | | IV-2 | CARD14 | 0.97 |
| 3350 | 3 | 4 | | | IV-2 | C18orf1 | 0.87 | 3446 | 3 | 4 | | | IV-2 | CARD9 | 0.92 |
| 3351 | 3 | 4 | | | IV-2 | C19orf44 | 0.71 | 3447 | 3 | 4 | | | IV-2 | CARHSP1 | 0.71 |
| 3352 | 3 | 4 | | | IV-2 | C19orf52 | 0.78 | 3448 | 3 | 4 | | | IV-2 | CARKD | 0.70 |
| 3353 | 3 | 4 | | | IV-2 | C19orf55 | 0.67 | 3449 | 3 | 4 | | | IV-2 | CARNS1 | 0.81 |
| 3354 | 3 | 4 | | | IV-2 | C19orf57 | 0.69 | 3450 | 3 | 4 | | | IV-2 | CARS | 0.78 |
| 3355 | 3 | 4 | | | IV-2 | C19orf60 | 0.71 | 3451 | 3 | 4 | | | IV-2 | CASC3 | 0.79 |
| 3356 | 3 | 4 | | | IV-2 | C19orf73 | 0.70 | 3452 | 3 | 4 | | | IV-2 | CASKIN1 | 0.99 |
| 3357 | 3 | 4 | | | IV-2 | C1GALT1C1 | 0.88 | 3453 | 3 | 4 | | | IV-2 | CASP2 | 0.83 |

Fig. 38 - 19

| | | | | | | | | | | | | | | |
|---|---|---|---|---|---|---|---|---|---|---|---|---|---|---|
| 3454 | 3 | 4 | | | IV-2 | CASP3 | 0.98 | 3550 | 3 | 4 | | | IV-2 | CERS2 | 0.71 |
| 3455 | 3 | 4 | | | IV-2 | CASP8 | 0.82 | 3551 | 3 | 4 | | | IV-2 | CERS5 | 0.79 |
| 3456 | 3 | 4 | | | IV-2 | CASP9 | 0.97 | 3552 | 3 | 4 | | | IV-2 | CERS6 | 0.99 |
| 3457 | 3 | 4 | | | IV-2 | CASQ1 | 0.90 | 3553 | 3 | 4 | | | IV-2 | CES2 | 0.74 |
| 3458 | 3 | 4 | | | IV-2 | CAST | 0.93 | 3554 | 3 | 4 | | | IV-2 | CETN2 | 0.78 |
| 3459 | 3 | 4 | | | IV-2 | CAV1 | 0.70 | 3555 | 3 | 4 | | | IV-2 | CETN3 | 0.86 |
| 3460 | 3 | 4 | | | IV-2 | CAV2 | 0.82 | 3556 | 3 | 4 | | | IV-2 | CFD | 0.90 |
| 3461 | 3 | 4 | | | IV-2 | CBFA2T3 | 0.88 | 3557 | 3 | 4 | | | IV-2 | CFDP1 | 0.94 |
| 3462 | 3 | 4 | | | IV-2 | CBLL1 | 0.95 | 3558 | 3 | 4 | | | IV-2 | CFHR1 | 0.82 |
| 3463 | 3 | 4 | | | IV-2 | CBR1 | 0.76 | 3559 | 3 | 4 | | | IV-2 | CHCHD1 | 0.88 |
| 3464 | 3 | 4 | | | IV-2 | CBS | 0.70 | 3560 | 3 | 4 | | | IV-2 | CHCHD10 | 0.73 |
| 3465 | 3 | 4 | | | IV-2 | CBWD2 | 0.89 | 3561 | 3 | 4 | | | IV-2 | CHCHD2 | 0.74 |
| 3466 | 3 | 4 | | | IV-2 | CBWD6 | 0.81 | 3562 | 3 | 4 | | | IV-2 | CHCHD3 | 0.69 |
| 3467 | 3 | 4 | | | IV-2 | CBX1 | 0.83 | 3563 | 3 | 4 | | | IV-2 | CHCHD8 | 0.69 |
| 3468 | 3 | 4 | | | IV-2 | CBX3 | 0.97 | 3564 | 3 | 4 | | | IV-2 | CHD3 | 0.80 |
| 3469 | 3 | 4 | | | IV-2 | CBX7 | 0.81 | 3565 | 3 | 4 | | | IV-2 | CHD4 | 0.95 |
| 3470 | 3 | 4 | | | IV-2 | CBX8 | 0.89 | 3566 | 3 | 4 | | | IV-2 | CHD8 | 0.83 |
| 3471 | 3 | 4 | | | IV-2 | CBY1 | 0.82 | 3567 | 3 | 4 | | | IV-2 | CHDH | 0.88 |
| 3472 | 3 | 4 | | | IV-2 | CC2D1B | 0.76 | 3568 | 3 | 4 | | | IV-2 | CHEK1 | 0.81 |
| 3473 | 3 | 4 | | | IV-2 | CCBL1 | 0.70 | 3569 | 3 | 4 | | | IV-2 | CHFR | 0.94 |
| 3474 | 3 | 4 | | | IV-2 | CCDC103 | 0.80 | 3570 | 3 | 4 | | | IV-2 | CHMP4A | 0.93 |
| 3475 | 3 | 4 | | | IV-2 | CCDC113 | 0.98 | 3571 | 3 | 4 | | | IV-2 | CHMP4B | 0.68 |
| 3476 | 3 | 4 | | | IV-2 | CCDC115 | 0.77 | 3572 | 3 | 4 | | | IV-2 | CHMP7 | 0.78 |
| 3477 | 3 | 4 | | | IV-2 | CCDC122 | 0.96 | 3573 | 3 | 4 | | | IV-2 | CHN1 | 0.81 |
| 3478 | 3 | 4 | | | IV-2 | CCDC126 | 0.80 | 3574 | 3 | 4 | | | IV-2 | CHN2 | 0.96 |
| 3479 | 3 | 4 | | | IV-2 | CCDC127 | 0.72 | 3575 | 3 | 4 | | | IV-2 | CHPF2 | 0.69 |
| 3480 | 3 | 4 | | | IV-2 | CCDC153 | 0.92 | 3576 | 3 | 4 | | | IV-2 | CHPT1 | 0.89 |
| 3481 | 3 | 4 | | | IV-2 | CCDC157 | 0.95 | 3577 | 3 | 4 | | | IV-2 | CHRNB1 | 0.75 |
| 3482 | 3 | 4 | | | IV-2 | CCDC165 | 0.70 | 3578 | 3 | 4 | | | IV-2 | CHST1 | 0.94 |
| 3483 | 3 | 4 | | | IV-2 | CCDC25 | 0.96 | 3579 | 3 | 4 | | | IV-2 | CHST10 | 0.74 |
| 3484 | 3 | 4 | | | IV-2 | CCDC28A | 0.89 | 3580 | 3 | 4 | | | IV-2 | CHST15 | 0.93 |
| 3485 | 3 | 4 | | | IV-2 | CCDC51 | 0.77 | 3581 | 3 | 4 | | | IV-2 | CHST3 | 0.67 |
| 3486 | 3 | 4 | | | IV-2 | CCDC56 | 0.71 | 3582 | 3 | 4 | | | IV-2 | CHSY1 | 0.85 |
| 3487 | 3 | 4 | | | IV-2 | CCDC59 | 0.89 | 3583 | 3 | 4 | | | IV-2 | CHTOP | 0.71 |
| 3488 | 3 | 4 | | | IV-2 | CCDC74A | 0.82 | 3584 | 3 | 4 | | | IV-2 | CIAPIN1 | 0.68 |
| 3489 | 3 | 4 | | | IV-2 | CCDC74B | 0.79 | 3585 | 3 | 4 | | | IV-2 | CIB1 | 0.68 |
| 3490 | 3 | 4 | | | IV-2 | CCDC85B | 0.67 | 3586 | 3 | 4 | | | IV-2 | CILP2 | 0.98 |
| 3491 | 3 | 4 | | | IV-2 | CCDC86 | 0.68 | 3587 | 3 | 4 | | | IV-2 | CIRBP | 0.87 |
| 3492 | 3 | 4 | | | IV-2 | CCDC88B | 0.85 | 3588 | 3 | 4 | | | IV-2 | CISD2 | 0.67 |
| 3493 | 3 | 4 | | | IV-2 | CCDC90B | 0.93 | 3589 | 3 | 4 | | | IV-2 | CITED2 | 0.67 |
| 3494 | 3 | 4 | | | IV-2 | CCNB1IP1 | 0.69 | 3590 | 3 | 4 | | | IV-2 | CKAP5 | 0.86 |
| 3495 | 3 | 4 | | | IV-2 | CCND3 | 0.71 | 3591 | 3 | 4 | | | IV-2 | CKLF-CMTM1 | 0.68 |
| 3496 | 3 | 4 | | | IV-2 | CCNH | 0.85 | 3592 | 3 | 4 | | | IV-2 | CKS2 | 0.73 |
| 3497 | 3 | 4 | | | IV-2 | CCNJL | 0.86 | 3593 | 3 | 4 | | | IV-2 | CLASP1 | 0.89 |
| 3498 | 3 | 4 | | | IV-2 | CCNK | 0.67 | 3594 | 3 | 4 | | | IV-2 | CLDN19 | 0.97 |
| 3499 | 3 | 4 | | | IV-2 | CCNY | 0.84 | 3595 | 3 | 4 | | | IV-2 | CLDND1 | 0.99 |
| 3500 | 3 | 4 | | | IV-2 | CCR10 | 0.75 | 3596 | 3 | 4 | | | IV-2 | CLEC12B | 0.69 |
| 3501 | 3 | 4 | | | IV-2 | CCT5 | 0.77 | 3597 | 3 | 4 | | | IV-2 | CLEC16A | 0.79 |
| 3502 | 3 | 4 | | | IV-2 | CCT6A | 0.76 | 3598 | 3 | 4 | | | IV-2 | CLEC18A | 0.97 |
| 3503 | 3 | 4 | | | IV-2 | CCT8 | 0.89 | 3599 | 3 | 4 | | | IV-2 | CLEC4GP1 | 0.69 |
| 3504 | 3 | 4 | | | IV-2 | CCZ1 | 0.83 | 3600 | 3 | 4 | | | IV-2 | CLEC9A | 1.00 |
| 3505 | 3 | 4 | | | IV-2 | CCZ1B | 0.84 | 3601 | 3 | 4 | | | IV-2 | CLIC2 | 0.86 |
| 3506 | 3 | 4 | | | IV-2 | CD109 | 0.99 | 3602 | 3 | 4 | | | IV-2 | CLIP1 | 0.90 |
| 3507 | 3 | 4 | | | IV-2 | CD160 | 0.90 | 3603 | 3 | 4 | | | IV-2 | CLNS1A | 0.79 |
| 3508 | 3 | 4 | | | IV-2 | CD164L2 | 0.83 | 3604 | 3 | 4 | | | IV-2 | CLP1 | 0.89 |
| 3509 | 3 | 4 | | | IV-2 | CD177 | 0.93 | 3605 | 3 | 4 | | | IV-2 | CLTCL1 | 0.96 |
| 3510 | 3 | 4 | | | IV-2 | CD3EAP | 0.71 | 3606 | 3 | 4 | | | IV-2 | CMC1 | 0.94 |
| 3511 | 3 | 4 | | | IV-2 | CD44 | 0.67 | 3607 | 3 | 4 | | | IV-2 | CMC2 | 0.79 |
| 3512 | 3 | 4 | | | IV-2 | CD58 | 0.75 | 3608 | 3 | 4 | | | IV-2 | CMKLR1 | 0.86 |
| 3513 | 3 | 4 | | | IV-2 | CD59 | 0.92 | 3609 | 3 | 4 | | | IV-2 | CMTM3 | 0.82 |
| 3514 | 3 | 4 | | | IV-2 | CD7 | 0.70 | 3610 | 3 | 4 | | | IV-2 | CMTM5 | 0.72 |
| 3515 | 3 | 4 | | | IV-2 | CD99L2 | 0.87 | 3611 | 3 | 4 | | | IV-2 | CNBP | 0.84 |
| 3516 | 3 | 4 | | | IV-2 | CDAN1 | 0.84 | 3612 | 3 | 4 | | | IV-2 | CNDP2 | 0.99 |
| 3517 | 3 | 4 | | | IV-2 | CDC27 | 0.99 | 3613 | 3 | 4 | | | IV-2 | CNEP1R1 | 0.96 |
| 3518 | 3 | 4 | | | IV-2 | CDC37L1 | 0.95 | 3614 | 3 | 4 | | | IV-2 | CNNM3 | 0.77 |
| 3519 | 3 | 4 | | | IV-2 | CDC42BPA | 0.97 | 3615 | 3 | 4 | | | IV-2 | CNNM4 | 0.99 |
| 3520 | 3 | 4 | | | IV-2 | CDC42BPB | 0.73 | 3616 | 3 | 4 | | | IV-2 | CNOT10 | 0.83 |
| 3521 | 3 | 4 | | | IV-2 | CDC42EP3 | 0.91 | 3617 | 3 | 4 | | | IV-2 | CNOT2 | 1.00 |
| 3522 | 3 | 4 | | | IV-2 | CDC45 | 0.93 | 3618 | 3 | 4 | | | IV-2 | CNPY4 | 0.67 |
| 3523 | 3 | 4 | | | IV-2 | CDC5L | 0.98 | 3619 | 3 | 4 | | | IV-2 | CNTF | 0.76 |
| 3524 | 3 | 4 | | | IV-2 | CDC6 | 0.97 | 3620 | 3 | 4 | | | IV-2 | CNTNAP1 | 0.77 |
| 3525 | 3 | 4 | | | IV-2 | CDH6 | 0.99 | 3621 | 3 | 4 | | | IV-2 | COG1 | 0.88 |
| 3526 | 3 | 4 | | | IV-2 | CDHR4 | 1.00 | 3622 | 3 | 4 | | | IV-2 | COG2 | 0.88 |
| 3527 | 3 | 4 | | | IV-2 | CDK11A | 0.79 | 3623 | 3 | 4 | | | IV-2 | COG7 | 0.72 |
| 3528 | 3 | 4 | | | IV-2 | CDK11B | 0.72 | 3624 | 3 | 4 | | | IV-2 | COL12A1 | 0.76 |
| 3529 | 3 | 4 | | | IV-2 | CDK13 | 0.90 | 3625 | 3 | 4 | | | IV-2 | COL5A2 | 0.87 |
| 3530 | 3 | 4 | | | IV-2 | CDK2 | 0.74 | 3626 | 3 | 4 | | | IV-2 | COL6A3 | 0.89 |
| 3531 | 3 | 4 | | | IV-2 | CDK5RAP1 | 0.75 | 3627 | 3 | 4 | | | IV-2 | COL8A2 | 0.89 |
| 3532 | 3 | 4 | | | IV-2 | CDK9 | 0.71 | 3628 | 3 | 4 | | | IV-2 | COL9A2 | 0.91 |
| 3533 | 3 | 4 | | | IV-2 | CDKAL1 | 0.93 | 3629 | 3 | 4 | | | IV-2 | COMMD3 | 0.82 |
| 3534 | 3 | 4 | | | IV-2 | CDKL3 | 0.97 | 3630 | 3 | 4 | | | IV-2 | COMMD5 | 0.73 |
| 3535 | 3 | 4 | | | IV-2 | CDKN1C | 0.80 | 3631 | 3 | 4 | | | IV-2 | COMMD9 | 0.72 |
| 3536 | 3 | 4 | | | IV-2 | CDKN2D | 0.77 | 3632 | 3 | 4 | | | IV-2 | COMTD1 | 0.69 |
| 3537 | 3 | 4 | | | IV-2 | CEACAM1 | 0.94 | 3633 | 3 | 4 | | | IV-2 | COPA | 0.83 |
| 3538 | 3 | 4 | | | IV-2 | CEACAM6 | 0.74 | 3634 | 3 | 4 | | | IV-2 | COPG1 | 0.69 |
| 3539 | 3 | 4 | | | IV-2 | CEBPD | 0.71 | 3635 | 3 | 4 | | | IV-2 | COPG2 | 0.88 |
| 3540 | 3 | 4 | | | IV-2 | CEBPG | 0.88 | 3636 | 3 | 4 | | | IV-2 | COPS2 | 0.98 |
| 3541 | 3 | 4 | | | IV-2 | CECR5-AS1 | 0.95 | 3637 | 3 | 4 | | | IV-2 | COPS4 | 0.88 |
| 3542 | 3 | 4 | | | IV-2 | CELSR1 | 0.92 | 3638 | 3 | 4 | | | IV-2 | COPS5 | 0.85 |
| 3543 | 3 | 4 | | | IV-2 | CEMP1 | 0.90 | 3639 | 3 | 4 | | | IV-2 | COPS6 | 0.69 |
| 3544 | 3 | 4 | | | IV-2 | CENPV | 0.92 | 3640 | 3 | 4 | | | IV-2 | COPS7A | 0.69 |
| 3545 | 3 | 4 | | | IV-2 | CEP104 | 0.87 | 3641 | 3 | 4 | | | IV-2 | COPS8 | 0.76 |
| 3546 | 3 | 4 | | | IV-2 | CEP19 | 0.74 | 3642 | 3 | 4 | | | IV-2 | COQ5 | 0.81 |
| 3547 | 3 | 4 | | | IV-2 | CEP250 | 0.78 | 3643 | 3 | 4 | | | IV-2 | COQ7 | 0.98 |
| 3548 | 3 | 4 | | | IV-2 | CEP85 | 0.91 | 3644 | 3 | 4 | | | IV-2 | CORO7 | 0.68 |
| 3549 | 3 | 4 | | | IV-2 | CEP89 | 0.92 | 3645 | 3 | 4 | | | IV-2 | COX11 | 0.91 |

Fig. 38 - 20

| | | | | | | | | | | | | | | | |
|---|---|---|---|---|---|---|---|---|---|---|---|---|---|---|---|
| 3646 | 3 | 4 | | | IV-2 | COX14 | 0.72 | 3742 | 3 | 4 | | | IV-2 | DES | 0.89 |
| 3647 | 3 | 4 | | | IV-2 | COX16 | 0.82 | 3743 | 3 | 4 | | | IV-2 | DGCR11 | 0.79 |
| 3648 | 3 | 4 | | | IV-2 | COX17 | 0.72 | 3744 | 3 | 4 | | | IV-2 | DGCR8 | 0.76 |
| 3649 | 3 | 4 | | | IV-2 | COX18 | 0.99 | 3745 | 3 | 4 | | | IV-2 | DGKD | 0.88 |
| 3650 | 3 | 4 | | | IV-2 | COX5B | 0.70 | 3746 | 3 | 4 | | | IV-2 | DGUOK | 0.68 |
| 3651 | 3 | 4 | | | IV-2 | COX6B1 | 0.68 | 3747 | 3 | 4 | | | IV-2 | DHDDS | 0.79 |
| 3652 | 3 | 4 | | | IV-2 | COX7A2 | 0.74 | 3748 | 3 | 4 | | | IV-2 | DHODH | 0.76 |
| 3653 | 3 | 4 | | | IV-2 | COX7A2L | 0.86 | 3749 | 3 | 4 | | | IV-2 | DHRS11 | 0.78 |
| 3654 | 3 | 4 | | | IV-2 | COX7C | 0.75 | 3750 | 3 | 4 | | | IV-2 | DHRS7 | 0.75 |
| 3655 | 3 | 4 | | | IV-2 | CPSF2 | 0.96 | 3751 | 3 | 4 | | | IV-2 | DHRS7B | 0.67 |
| 3656 | 3 | 4 | | | IV-2 | CPSF3 | 0.95 | 3752 | 3 | 4 | | | IV-2 | DHX16 | 0.81 |
| 3657 | 3 | 4 | | | IV-2 | CPSF7 | 0.73 | 3753 | 3 | 4 | | | IV-2 | DHX32 | 0.92 |
| 3658 | 3 | 4 | | | IV-2 | CPT1C | 0.70 | 3754 | 3 | 4 | | | IV-2 | DHX38 | 0.79 |
| 3659 | 3 | 4 | | | IV-2 | CPXM2 | 0.78 | 3755 | 3 | 4 | | | IV-2 | DHX9 | 0.78 |
| 3660 | 3 | 4 | | | IV-2 | CRAMP1L | 0.96 | 3756 | 3 | 4 | | | IV-2 | DIABLO | 0.77 |
| 3661 | 3 | 4 | | | IV-2 | CRCP | 0.83 | 3757 | 3 | 4 | | | IV-2 | DIDO1 | 0.83 |
| 3662 | 3 | 4 | | | IV-2 | CREB3L1 | 0.71 | 3758 | 3 | 4 | | | IV-2 | DIMT1 | 0.95 |
| 3663 | 3 | 4 | | | IV-2 | CREBBP | 0.83 | 3759 | 3 | 4 | | | IV-2 | DKC1 | 0.77 |
| 3664 | 3 | 4 | | | IV-2 | CRHR2 | 0.96 | 3760 | 3 | 4 | | | IV-2 | DKFZP586I1420 | 0.86 |
| 3665 | 3 | 4 | | | IV-2 | CRIP3 | 0.93 | 3761 | 3 | 4 | | | IV-2 | DLG3 | 0.95 |
| 3666 | 3 | 4 | | | IV-2 | CRISPLD2 | 0.99 | 3762 | 3 | 4 | | | IV-2 | DLG4 | 0.71 |
| 3667 | 3 | 4 | | | IV-2 | CRSP8P | 0.69 | 3763 | 3 | 4 | | | IV-2 | DLK1 | 0.91 |
| 3668 | 3 | 4 | | | IV-2 | CRTAP | 0.75 | 3764 | 3 | 4 | | | IV-2 | DLST | 0.69 |
| 3669 | 3 | 4 | | | IV-2 | CRTC3 | 0.75 | 3765 | 3 | 4 | | | IV-2 | DLX6 | 0.94 |
| 3670 | 3 | 4 | | | IV-2 | CRY1 | 0.70 | 3766 | 3 | 4 | | | IV-2 | DMD | 0.95 |
| 3671 | 3 | 4 | | | IV-2 | CRY2 | 0.70 | 3767 | 3 | 4 | | | IV-2 | DMRT3 | 0.88 |
| 3672 | 3 | 4 | | | IV-2 | CRYL1 | 0.79 | 3768 | 3 | 4 | | | IV-2 | DNAJA3 | 0.84 |
| 3673 | 3 | 4 | | | IV-2 | CRYZ | 0.83 | 3769 | 3 | 4 | | | IV-2 | DNAJA4 | 0.97 |
| 3674 | 3 | 4 | | | IV-2 | CRYZL1 | 0.95 | 3770 | 3 | 4 | | | IV-2 | DNAJB11 | 0.75 |
| 3675 | 3 | 4 | | | IV-2 | CSNK1D | 0.70 | 3771 | 3 | 4 | | | IV-2 | DNAJB12 | 0.72 |
| 3676 | 3 | 4 | | | IV-2 | CSNK1E | 0.68 | 3772 | 3 | 4 | | | IV-2 | DNAJB5 | 0.73 |
| 3677 | 3 | 4 | | | IV-2 | CSRP1 | 0.70 | 3773 | 3 | 4 | | | IV-2 | DNAJC11 | 0.80 |
| 3678 | 3 | 4 | | | IV-2 | CSRP2 | 0.95 | 3774 | 3 | 4 | | | IV-2 | DNAJC17 | 0.72 |
| 3679 | 3 | 4 | | | IV-2 | CSRP2BP | 0.73 | 3775 | 3 | 4 | | | IV-2 | DNAJC25 | 0.79 |
| 3680 | 3 | 4 | | | IV-2 | CSTF1 | 0.80 | 3776 | 3 | 4 | | | IV-2 | DNAJC9 | 0.75 |
| 3681 | 3 | 4 | | | IV-2 | CSTF2T | 0.97 | 3777 | 3 | 4 | | | IV-2 | DNAL4 | 0.70 |
| 3682 | 3 | 4 | | | IV-2 | CTAGE5 | 0.82 | 3778 | 3 | 4 | | | IV-2 | DNASE1L1 | 0.88 |
| 3683 | 3 | 4 | | | IV-2 | CTAGE7P | 0.78 | 3779 | 3 | 4 | | | IV-2 | DND1 | 0.86 |
| 3684 | 3 | 4 | | | IV-2 | CTBP2 | 0.83 | 3780 | 3 | 4 | | | IV-2 | DNMBP | 0.72 |
| 3685 | 3 | 4 | | | IV-2 | CTCF | 0.84 | 3781 | 3 | 4 | | | IV-2 | DNMT1 | 0.89 |
| 3686 | 3 | 4 | | | IV-2 | CTNNA1 | 0.80 | 3782 | 3 | 4 | | | IV-2 | DNPEP | 0.80 |
| 3687 | 3 | 4 | | | IV-2 | CTNNAL1 | 0.98 | 3783 | 3 | 4 | | | IV-2 | DOCK1 | 0.72 |
| 3688 | 3 | 4 | | | IV-2 | CTNS | 0.75 | 3784 | 3 | 4 | | | IV-2 | DOCK11 | 0.98 |
| 3689 | 3 | 4 | | | IV-2 | CTPS2 | 0.91 | 3785 | 3 | 4 | | | IV-2 | DOCK6 | 0.67 |
| 3690 | 3 | 4 | | | IV-2 | CTSH | 0.98 | 3786 | 3 | 4 | | | IV-2 | DOLPP1 | 0.70 |
| 3691 | 3 | 4 | | | IV-2 | CTSL1 | 0.82 | 3787 | 3 | 4 | | | IV-2 | DOT1L | 0.73 |
| 3692 | 3 | 4 | | | IV-2 | CTSZ | 0.69 | 3788 | 3 | 4 | | | IV-2 | DPH5 | 0.88 |
| 3693 | 3 | 4 | | | IV-2 | CTTN | 0.71 | 3789 | 3 | 4 | | | IV-2 | DPP4 | 0.79 |
| 3694 | 3 | 4 | | | IV-2 | CUL1 | 0.97 | 3790 | 3 | 4 | | | IV-2 | DRAM2 | 0.88 |
| 3695 | 3 | 4 | | | IV-2 | CWF19L1 | 0.76 | 3791 | 3 | 4 | | | IV-2 | DRG2 | 0.68 |
| 3696 | 3 | 4 | | | IV-2 | CWH43 | 0.87 | 3792 | 3 | 4 | | | IV-2 | DSCC1 | 0.86 |
| 3697 | 3 | 4 | | | IV-2 | CXorf26 | 0.86 | 3793 | 3 | 4 | | | IV-2 | DSCR3 | 0.98 |
| 3698 | 3 | 4 | | | IV-2 | CXorf56 | 0.73 | 3794 | 3 | 4 | | | IV-2 | DSN1 | 0.83 |
| 3699 | 3 | 4 | | | IV-2 | CXorf65 | 1.00 | 3795 | 3 | 4 | | | IV-2 | DSTN | 0.89 |
| 3700 | 3 | 4 | | | IV-2 | CXXC5 | 0.85 | 3796 | 3 | 4 | | | IV-2 | DTD1 | 0.72 |
| 3701 | 3 | 4 | | | IV-2 | CYB561 | 0.68 | 3797 | 3 | 4 | | | IV-2 | DUSP12 | 0.94 |
| 3702 | 3 | 4 | | | IV-2 | CYB561D2 | 0.82 | 3798 | 3 | 4 | | | IV-2 | DUSP22 | 0.77 |
| 3703 | 3 | 4 | | | IV-2 | CYB5B | 0.68 | 3799 | 3 | 4 | | | IV-2 | DUSP6 | 0.96 |
| 3704 | 3 | 4 | | | IV-2 | CYFIP1 | 0.81 | 3800 | 3 | 4 | | | IV-2 | DUSP8 | 0.68 |
| 3705 | 3 | 4 | | | IV-2 | CYP27A1 | 0.92 | 3801 | 3 | 4 | | | IV-2 | DUT | 0.80 |
| 3706 | 3 | 4 | | | IV-2 | CYP2E1 | 0.68 | 3802 | 3 | 4 | | | IV-2 | DYNC1I1 | 0.74 |
| 3707 | 3 | 4 | | | IV-2 | CYP3A4 | 0.91 | 3803 | 3 | 4 | | | IV-2 | DYNLL1 | 0.73 |
| 3708 | 3 | 4 | | | IV-2 | CYTH1 | 0.98 | 3804 | 3 | 4 | | | IV-2 | DYNLT1 | 0.83 |
| 3709 | 3 | 4 | | | IV-2 | CYTH3 | 0.88 | 3805 | 3 | 4 | | | IV-2 | DYRK2 | 0.76 |
| 3710 | 3 | 4 | | | IV-2 | DACH1 | 0.93 | 3806 | 3 | 4 | | | IV-2 | DYRK4 | 0.79 |
| 3711 | 3 | 4 | | | IV-2 | DACT3 | 0.83 | 3807 | 3 | 4 | | | IV-2 | E2F5 | 0.91 |
| 3712 | 3 | 4 | | | IV-2 | DAD1 | 0.71 | 3808 | 3 | 4 | | | IV-2 | EAPP | 0.83 |
| 3713 | 3 | 4 | | | IV-2 | DALRD3 | 0.68 | 3809 | 3 | 4 | | | IV-2 | EBAG9 | 0.82 |
| 3714 | 3 | 4 | | | IV-2 | DAP3 | 0.76 | 3810 | 3 | 4 | | | IV-2 | EBF2 | 0.76 |
| 3715 | 3 | 4 | | | IV-2 | DARS | 0.71 | 3811 | 3 | 4 | | | IV-2 | EBI3 | 0.91 |
| 3716 | 3 | 4 | | | IV-2 | DBF4 | 0.83 | 3812 | 3 | 4 | | | IV-2 | EBNA1BP2 | 0.85 |
| 3717 | 3 | 4 | | | IV-2 | DBI | 0.84 | 3813 | 3 | 4 | | | IV-2 | EBP | 0.82 |
| 3718 | 3 | 4 | | | IV-2 | DBP | 0.98 | 3814 | 3 | 4 | | | IV-2 | ECD | 0.96 |
| 3719 | 3 | 4 | | | IV-2 | DBR1 | 1.00 | 3815 | 3 | 4 | | | IV-2 | ECHS1 | 0.70 |
| 3720 | 3 | 4 | | | IV-2 | DCAF5 | 0.87 | 3816 | 3 | 4 | | | IV-2 | ECI1 | 0.71 |
| 3721 | 3 | 4 | | | IV-2 | DCAF6 | 0.90 | 3817 | 3 | 4 | | | IV-2 | ECI2 | 0.87 |
| 3722 | 3 | 4 | | | IV-2 | DCAF8 | 0.93 | 3818 | 3 | 4 | | | IV-2 | ECT2 | 0.75 |
| 3723 | 3 | 4 | | | IV-2 | DCHS1 | 0.74 | 3819 | 3 | 4 | | | IV-2 | EDC3 | 0.89 |
| 3724 | 3 | 4 | | | IV-2 | DCTD | 0.81 | 3820 | 3 | 4 | | | IV-2 | EDNRB | 0.91 |
| 3725 | 3 | 4 | | | IV-2 | DDT | 0.69 | 3821 | 3 | 4 | | | IV-2 | EEF1B2 | 0.68 |
| 3726 | 3 | 4 | | | IV-2 | DDTL | 0.97 | 3822 | 3 | 4 | | | IV-2 | EEF1E1 | 0.71 |
| 3727 | 3 | 4 | | | IV-2 | DDX1 | 0.87 | 3823 | 3 | 4 | | | IV-2 | EFEMP2 | 0.68 |
| 3728 | 3 | 4 | | | IV-2 | DDX10 | 0.73 | 3824 | 3 | 4 | | | IV-2 | EFHA1 | 0.91 |
| 3729 | 3 | 4 | | | IV-2 | DDX19B | 0.72 | 3825 | 3 | 4 | | | IV-2 | EFHC2 | 0.86 |
| 3730 | 3 | 4 | | | IV-2 | DDX20 | 0.95 | 3826 | 3 | 4 | | | IV-2 | EFNA4 | 0.77 |
| 3731 | 3 | 4 | | | IV-2 | DDX23 | 0.68 | 3827 | 3 | 4 | | | IV-2 | EFNA5 | 0.82 |
| 3732 | 3 | 4 | | | IV-2 | DDX24 | 0.87 | 3828 | 3 | 4 | | | IV-2 | EFR3B | 0.98 |
| 3733 | 3 | 4 | | | IV-2 | DDX27 | 0.99 | 3829 | 3 | 4 | | | IV-2 | EGFL6 | 0.93 |
| 3734 | 3 | 4 | | | IV-2 | DDX42 | 0.90 | 3830 | 3 | 4 | | | IV-2 | EGLN2 | 0.70 |
| 3735 | 3 | 4 | | | IV-2 | DDX47 | 0.96 | 3831 | 3 | 4 | | | IV-2 | EHBP1L1 | 0.72 |
| 3736 | 3 | 4 | | | IV-2 | DDX50 | 0.78 | 3832 | 3 | 4 | | | IV-2 | EHD4 | 0.78 |
| 3737 | 3 | 4 | | | IV-2 | DDX56 | 0.77 | 3833 | 3 | 4 | | | IV-2 | EHMT1 | 0.72 |
| 3738 | 3 | 4 | | | IV-2 | DECR1 | 0.99 | 3834 | 3 | 4 | | | IV-2 | EID1 | 0.83 |
| 3739 | 3 | 4 | | | IV-2 | DEF8 | 0.75 | 3835 | 3 | 4 | | | IV-2 | EID2 | 0.68 |
| 3740 | 3 | 4 | | | IV-2 | DENND4B | 0.72 | 3836 | 3 | 4 | | | IV-2 | EIF1B | 0.85 |
| 3741 | 3 | 4 | | | IV-2 | DEPDC1 | 0.92 | 3837 | 3 | 4 | | | IV-2 | EIF2B1 | 0.78 |

Fig. 38 - 21

| | | | | | | | | | | | | | | | |
|---|---|---|---|---|---|---|---|---|---|---|---|---|---|---|---|
| 3838 | 3 | 4 | | | IV-2 | EIF2B2 | 0.84 | 3934 | 3 | 4 | | | IV-2 | FAM211A | 0.74 |
| 3839 | 3 | 4 | | | IV-2 | EIF2B4 | 0.73 | 3935 | 3 | 4 | | | IV-2 | FAM214B | 0.73 |
| 3840 | 3 | 4 | | | IV-2 | EIF2B5 | 0.82 | 3936 | 3 | 4 | | | IV-2 | FAM218 | 0.89 |
| 3841 | 3 | 4 | | | IV-2 | EIF2S1 | 0.98 | 3937 | 3 | 4 | | | IV-2 | FAM32A | 0.85 |
| 3842 | 3 | 4 | | | IV-2 | EIF2S2 | 0.95 | 3938 | 3 | 4 | | | IV-2 | FAM35B | 0.99 |
| 3843 | 3 | 4 | | | IV-2 | EIF2S3 | 0.79 | 3939 | 3 | 4 | | | IV-2 | FAM3D | 0.83 |
| 3844 | 3 | 4 | | | IV-2 | EIF3E | 0.76 | 3940 | 3 | 4 | | | IV-2 | FAM40A | 0.69 |
| 3845 | 3 | 4 | | | IV-2 | EIF3H | 0.79 | 3941 | 3 | 4 | | | IV-2 | FAM49B | 0.88 |
| 3846 | 3 | 4 | | | IV-2 | EIF3M | 0.84 | 3942 | 3 | 4 | | | IV-2 | FAM53A | 0.96 |
| 3847 | 3 | 4 | | | IV-2 | EIF4A1 | 0.73 | 3943 | 3 | 4 | | | IV-2 | FAM58BP | 0.76 |
| 3848 | 3 | 4 | | | IV-2 | EIF4ENIF1 | 0.79 | 3944 | 3 | 4 | | | IV-2 | FAM59B | 0.74 |
| 3849 | 3 | 4 | | | IV-2 | ELAC1 | 0.89 | 3945 | 3 | 4 | | | IV-2 | FAM64A | 0.76 |
| 3850 | 3 | 4 | | | IV-2 | ELAVL1 | 0.90 | 3946 | 3 | 4 | | | IV-2 | FAM66C | 0.94 |
| 3851 | 3 | 4 | | | IV-2 | ELL | 0.77 | 3947 | 3 | 4 | | | IV-2 | FAM72A | 0.70 |
| 3852 | 3 | 4 | | | IV-2 | ELP3 | 0.73 | 3948 | 3 | 4 | | | IV-2 | FAM72B | 0.90 |
| 3853 | 3 | 4 | | | IV-2 | ELP4 | 0.76 | 3949 | 3 | 4 | | | IV-2 | FAM82A1 | 0.95 |
| 3854 | 3 | 4 | | | IV-2 | ELTD1 | 0.71 | 3950 | 3 | 4 | | | IV-2 | FAM82A2 | 0.80 |
| 3855 | 3 | 4 | | | IV-2 | EME2 | 0.84 | 3951 | 3 | 4 | | | IV-2 | FAM86C2P | 0.93 |
| 3856 | 3 | 4 | | | IV-2 | EMG1 | 0.73 | 3952 | 3 | 4 | | | IV-2 | FAM86EP | 0.73 |
| 3857 | 3 | 4 | | | IV-2 | EMID1 | 0.92 | 3953 | 3 | 4 | | | IV-2 | FAM86FP | 0.86 |
| 3858 | 3 | 4 | | | IV-2 | EMILIN2 | 0.84 | 3954 | 3 | 4 | | | IV-2 | FAM92A1 | 0.96 |
| 3859 | 3 | 4 | | | IV-2 | ENDOV | 0.83 | 3955 | 3 | 4 | | | IV-2 | FAM96A | 0.74 |
| 3860 | 3 | 4 | | | IV-2 | ENHO | 0.86 | 3956 | 3 | 4 | | | IV-2 | FAM96B | 0.76 |
| 3861 | 3 | 4 | | | IV-2 | ENO4 | 0.92 | 3957 | 3 | 4 | | | IV-2 | FAM98C | 0.70 |
| 3862 | 3 | 4 | | | IV-2 | ENOPH1 | 0.87 | 3958 | 3 | 4 | | | IV-2 | FANCA | 0.87 |
| 3863 | 3 | 4 | | | IV-2 | ENOX1 | 0.98 | 3959 | 3 | 4 | | | IV-2 | FANCD2 | 0.97 |
| 3864 | 3 | 4 | | | IV-2 | EN5A | 0.69 | 3960 | 3 | 4 | | | IV-2 | FANCF | 0.96 |
| 3865 | 3 | 4 | | | IV-2 | ENTPD1 | 0.95 | 3961 | 3 | 4 | | | IV-2 | FARP1 | 0.75 |
| 3866 | 3 | 4 | | | IV-2 | ENY2 | 0.93 | 3962 | 3 | 4 | | | IV-2 | FARP2 | 0.78 |
| 3867 | 3 | 4 | | | IV-2 | EPAS1 | 0.70 | 3963 | 3 | 4 | | | IV-2 | FAT1 | 0.71 |
| 3868 | 3 | 4 | | | IV-2 | EPB41L1 | 0.77 | 3964 | 3 | 4 | | | IV-2 | FBLN2 | 0.81 |
| 3869 | 3 | 4 | | | IV-2 | EPB41L3 | 0.91 | 3965 | 3 | 4 | | | IV-2 | FBLN5 | 0.85 |
| 3870 | 3 | 4 | | | IV-2 | EPB41L4A | 0.84 | 3966 | 3 | 4 | | | IV-2 | FBLN7 | 0.98 |
| 3871 | 3 | 4 | | | IV-2 | EPB41L4A-AS1 | 0.86 | 3967 | 3 | 4 | | | IV-2 | FBXL12 | 0.78 |
| 3872 | 3 | 4 | | | IV-2 | EPDR1 | 0.72 | 3968 | 3 | 4 | | | IV-2 | FBXL15 | 0.68 |
| 3873 | 3 | 4 | | | IV-2 | EPHA1 | 0.67 | 3969 | 3 | 4 | | | IV-2 | FBXL18 | 0.94 |
| 3874 | 3 | 4 | | | IV-2 | EPHX2 | 0.90 | 3970 | 3 | 4 | | | IV-2 | FBXL2 | 0.95 |
| 3875 | 3 | 4 | | | IV-2 | EPHX4 | 0.96 | 3971 | 3 | 4 | | | IV-2 | FBXL5 | 0.77 |
| 3876 | 3 | 4 | | | IV-2 | EPM2A | 0.97 | 3972 | 3 | 4 | | | IV-2 | FBXL7 | 0.71 |
| 3877 | 3 | 4 | | | IV-2 | EPN2 | 0.94 | 3973 | 3 | 4 | | | IV-2 | FBXO10 | 0.80 |
| 3878 | 3 | 4 | | | IV-2 | EPO | 0.89 | 3974 | 3 | 4 | | | IV-2 | FBXO17 | 0.77 |
| 3879 | 3 | 4 | | | IV-2 | EPS15L1 | 0.82 | 3975 | 3 | 4 | | | IV-2 | FBXO18 | 0.79 |
| 3880 | 3 | 4 | | | IV-2 | EPS8L1 | 0.80 | 3976 | 3 | 4 | | | IV-2 | FBXO22-AS1 | 0.95 |
| 3881 | 3 | 4 | | | IV-2 | ERAP2 | 0.70 | 3977 | 3 | 4 | | | IV-2 | FBXO25 | 0.71 |
| 3882 | 3 | 4 | | | IV-2 | ERBB3 | 0.99 | 3978 | 3 | 4 | | | IV-2 | FBXO32 | 0.90 |
| 3883 | 3 | 4 | | | IV-2 | ERCC2 | 0.85 | 3979 | 3 | 4 | | | IV-2 | FBXO36 | 0.89 |
| 3884 | 3 | 4 | | | IV-2 | ERCC3 | 0.91 | 3980 | 3 | 4 | | | IV-2 | FBXO4 | 0.92 |
| 3885 | 3 | 4 | | | IV-2 | ERGIC1 | 0.69 | 3981 | 3 | 4 | | | IV-2 | FBXO44 | 0.69 |
| 3886 | 3 | 4 | | | IV-2 | ERH | 0.75 | 3982 | 3 | 4 | | | IV-2 | FBXO5 | 0.93 |
| 3887 | 3 | 4 | | | IV-2 | ERI1 | 0.94 | 3983 | 3 | 4 | | | IV-2 | FBXO6 | 0.75 |
| 3888 | 3 | 4 | | | IV-2 | ERP44 | 0.92 | 3984 | 3 | 4 | | | IV-2 | FBXW8 | 0.90 |
| 3889 | 3 | 4 | | | IV-2 | ESD | 0.89 | 3985 | 3 | 4 | | | IV-2 | FCF1 | 0.88 |
| 3890 | 3 | 4 | | | IV-2 | ESPL1 | 0.71 | 3986 | 3 | 4 | | | IV-2 | FCGRT | 0.87 |
| 3891 | 3 | 4 | | | IV-2 | ESRP2 | 0.88 | 3987 | 3 | 4 | | | IV-2 | FCHSD1 | 0.77 |
| 3892 | 3 | 4 | | | IV-2 | ESYT2 | 0.78 | 3988 | 3 | 4 | | | IV-2 | FCRLA | 0.89 |
| 3893 | 3 | 4 | | | IV-2 | ETFA | 0.95 | 3989 | 3 | 4 | | | IV-2 | FDX1 | 0.74 |
| 3894 | 3 | 4 | | | IV-2 | ETV5 | 0.71 | 3990 | 3 | 4 | | | IV-2 | FDXACB1 | 0.98 |
| 3895 | 3 | 4 | | | IV-2 | EVC2 | 0.91 | 3991 | 3 | 4 | | | IV-2 | FERMT3 | 0.92 |
| 3896 | 3 | 4 | | | IV-2 | EVL | 0.88 | 3992 | 3 | 4 | | | IV-2 | FGFR1 | 0.68 |
| 3897 | 3 | 4 | | | IV-2 | EXD2 | 0.81 | 3993 | 3 | 4 | | | IV-2 | FHL2 | 0.74 |
| 3898 | 3 | 4 | | | IV-2 | EXOC2 | 0.82 | 3994 | 3 | 4 | | | IV-2 | FKBP10 | 0.75 |
| 3899 | 3 | 4 | | | IV-2 | EXOC7 | 0.72 | 3995 | 3 | 4 | | | IV-2 | FKBP15 | 0.78 |
| 3900 | 3 | 4 | | | IV-2 | EXOSC1 | 0.81 | 3996 | 3 | 4 | | | IV-2 | FKBP9 | 0.83 |
| 3901 | 3 | 4 | | | IV-2 | EXOSC10 | 0.87 | 3997 | 3 | 4 | | | IV-2 | FLI1 | 0.76 |
| 3902 | 3 | 4 | | | IV-2 | EXOSC2 | 0.80 | 3998 | 3 | 4 | | | IV-2 | FLJ10038 | 0.87 |
| 3903 | 3 | 4 | | | IV-2 | EXOSC7 | 0.75 | 3999 | 3 | 4 | | | IV-2 | FLJ10661 | 0.90 |
| 3904 | 3 | 4 | | | IV-2 | EXPH5 | 0.73 | 4000 | 3 | 4 | | | IV-2 | FLJ13197 | 0.98 |
| 3905 | 3 | 4 | | | IV-2 | EXT2 | 0.83 | 4001 | 3 | 4 | | | IV-2 | FLJ27352 | 0.73 |
| 3906 | 3 | 4 | | | IV-2 | EXTL2 | 0.91 | 4002 | 3 | 4 | | | IV-2 | FLJ27354 | 0.98 |
| 3907 | 3 | 4 | | | IV-2 | FAF1 | 0.86 | 4003 | 3 | 4 | | | IV-2 | FLJ30403 | 0.98 |
| 3908 | 3 | 4 | | | IV-2 | FAHD2A | 0.77 | 4004 | 3 | 4 | | | IV-2 | FLJ35390 | 0.72 |
| 3909 | 3 | 4 | | | IV-2 | FAIM2 | 0.94 | 4005 | 3 | 4 | | | IV-2 | FLJ39653 | 0.94 |
| 3910 | 3 | 4 | | | IV-2 | FAM101B | 0.88 | 4006 | 3 | 4 | | | IV-2 | FLJ41200 | 0.91 |
| 3911 | 3 | 4 | | | IV-2 | FAM103A1 | 0.86 | 4007 | 3 | 4 | | | IV-2 | FLJ43681 | 0.99 |
| 3912 | 3 | 4 | | | IV-2 | FAM104A | 0.89 | 4008 | 3 | 4 | | | IV-2 | FLNA | 0.83 |
| 3913 | 3 | 4 | | | IV-2 | FAM104B | 0.72 | 4009 | 3 | 4 | | | IV-2 | FLNB | 0.74 |
| 3914 | 3 | 4 | | | IV-2 | FAM107B | 0.70 | 4010 | 3 | 4 | | | IV-2 | FLRT1 | 0.84 |
| 3915 | 3 | 4 | | | IV-2 | FAM109B | 0.69 | 4011 | 3 | 4 | | | IV-2 | FNTA | 0.95 |
| 3916 | 3 | 4 | | | IV-2 | FAM114A1 | 0.87 | 4012 | 3 | 4 | | | IV-2 | FNTB | 0.83 |
| 3917 | 3 | 4 | | | IV-2 | FAM114A2 | 0.93 | 4013 | 3 | 4 | | | IV-2 | FOLR1 | 0.72 |
| 3918 | 3 | 4 | | | IV-2 | FAM116A | 0.97 | 4014 | 3 | 4 | | | IV-2 | FOPNL | 0.83 |
| 3919 | 3 | 4 | | | IV-2 | FAM120C | 0.84 | 4015 | 3 | 4 | | | IV-2 | FOXA1 | 0.88 |
| 3920 | 3 | 4 | | | IV-2 | FAM136A | 0.89 | 4016 | 3 | 4 | | | IV-2 | FOXD3 | 0.78 |
| 3921 | 3 | 4 | | | IV-2 | FAM162A | 0.82 | 4017 | 3 | 4 | | | IV-2 | FOXK2 | 0.68 |
| 3922 | 3 | 4 | | | IV-2 | FAM165B | 0.85 | 4018 | 3 | 4 | | | IV-2 | FOXO1 | 0.85 |
| 3923 | 3 | 4 | | | IV-2 | FAM166B | 0.88 | 4019 | 3 | 4 | | | IV-2 | FOXP1 | 0.90 |
| 3924 | 3 | 4 | | | IV-2 | FAM171A1 | 0.95 | 4020 | 3 | 4 | | | IV-2 | FOXP3 | 0.75 |
| 3925 | 3 | 4 | | | IV-2 | FAM171A2 | 0.95 | 4021 | 3 | 4 | | | IV-2 | FOXRED1 | 0.80 |
| 3926 | 3 | 4 | | | IV-2 | FAM173A | 0.71 | 4022 | 3 | 4 | | | IV-2 | FRG1 | 0.80 |
| 3927 | 3 | 4 | | | IV-2 | FAM178B | 0.99 | 4023 | 3 | 4 | | | IV-2 | FRMD4A | 0.74 |
| 3928 | 3 | 4 | | | IV-2 | FAM182A | 0.95 | 4024 | 3 | 4 | | | IV-2 | FR52 | 0.94 |
| 3929 | 3 | 4 | | | IV-2 | FAM188I | 0.85 | 4025 | 3 | 4 | | | IV-2 | FSTL1 | 0.81 |
| 3930 | 3 | 4 | | | IV-2 | FAM192A | 0.91 | 4026 | 3 | 4 | | | IV-2 | FTH1P3 | 0.90 |
| 3931 | 3 | 4 | | | IV-2 | FAM193A | 0.69 | 4027 | 3 | 4 | | | IV-2 | FTO | 0.75 |
| 3932 | 3 | 4 | | | IV-2 | FAM198A | 0.97 | 4028 | 3 | 4 | | | IV-2 | FTSJ2 | 0.77 |
| 3933 | 3 | 4 | | | IV-2 | FAM206A | 0.93 | 4029 | 3 | 4 | | | IV-2 | FTSJ3 | 0.76 |

Fig. 38 - 22

| | | | | | | | |
|---|---|---|---|---|---|---|---|
| 4030 | 3 | 4 | | IV-2 | F1X | 0.96 |
| 4031 | 3 | 4 | | IV-2 | FUBP1 | 0.79 |
| 4032 | 3 | 4 | | IV-2 | FUCA2 | 0.94 |
| 4033 | 3 | 4 | | IV-2 | FUT8 | 0.97 |
| 4034 | 3 | 4 | | IV-2 | FXYD7 | 0.70 |
| 4035 | 3 | 4 | | IV-2 | FZD1 | 0.77 |
| 4036 | 3 | 4 | | IV-2 | G3BP1 | 0.91 |
| 4037 | 3 | 4 | | IV-2 | GABARAPL1 | 0.86 |
| 4038 | 3 | 4 | | IV-2 | GABARAPL3 | 0.72 |
| 4039 | 3 | 4 | | IV-2 | GABPB1 | 0.95 |
| 4040 | 3 | 4 | | IV-2 | GADD45A | 0.76 |
| 4041 | 3 | 4 | | IV-2 | GALK2 | 0.98 |
| 4042 | 3 | 4 | | IV-2 | GALM | 0.97 |
| 4043 | 3 | 4 | | IV-2 | GALNTL2 | 0.90 |
| 4044 | 3 | 4 | | IV-2 | GAP43 | 0.91 |
| 4045 | 3 | 4 | | IV-2 | GAPDHS | 0.95 |
| 4046 | 3 | 4 | | IV-2 | GARS | 0.77 |
| 4047 | 3 | 4 | | IV-2 | GAS5 | 0.78 |
| 4048 | 3 | 4 | | IV-2 | GAS6 | 0.75 |
| 4049 | 3 | 4 | | IV-2 | GATA5 | 0.97 |
| 4050 | 3 | 4 | | IV-2 | GATAD2B | 0.82 |
| 4051 | 3 | 4 | | IV-2 | GATS | 0.69 |
| 4052 | 3 | 4 | | IV-2 | GATSL1 | 0.97 |
| 4053 | 3 | 4 | | IV-2 | GBAS | 0.86 |
| 4054 | 3 | 4 | | IV-2 | GBGT1 | 0.83 |
| 4055 | 3 | 4 | | IV-2 | GBP2 | 0.89 |
| 4056 | 3 | 4 | | IV-2 | GCH1 | 0.85 |
| 4057 | 3 | 4 | | IV-2 | GCHFR | 0.75 |
| 4058 | 3 | 4 | | IV-2 | GCN1L1 | 0.82 |
| 4059 | 3 | 4 | | IV-2 | GCSH | 0.87 |
| 4060 | 3 | 4 | | IV-2 | GDF11 | 0.79 |
| 4061 | 3 | 4 | | IV-2 | GDI2 | 0.73 |
| 4062 | 3 | 4 | | IV-2 | GDNF | 0.72 |
| 4063 | 3 | 4 | | IV-2 | GDPD3 | 0.81 |
| 4064 | 3 | 4 | | IV-2 | GEMIN5 | 0.98 |
| 4065 | 3 | 4 | | IV-2 | GEMIN7 | 0.80 |
| 4066 | 3 | 4 | | IV-2 | GEMIN8 | 0.99 |
| 4067 | 3 | 4 | | IV-2 | GFOD2 | 0.73 |
| 4068 | 3 | 4 | | IV-2 | GGA1 | 0.75 |
| 4069 | 3 | 4 | | IV-2 | GGPS1 | 0.97 |
| 4070 | 3 | 4 | | IV-2 | GHDC | 0.69 |
| 4071 | 3 | 4 | | IV-2 | GHITM | 0.97 |
| 4072 | 3 | 4 | | IV-2 | GIMAP1 | 0.75 |
| 4073 | 3 | 4 | | IV-2 | GINS1 | 0.98 |
| 4074 | 3 | 4 | | IV-2 | GINS3 | 0.67 |
| 4075 | 3 | 4 | | IV-2 | GIPC3 | 0.69 |
| 4076 | 3 | 4 | | IV-2 | GIPR | 0.71 |
| 4077 | 3 | 4 | | IV-2 | GIT2 | 0.95 |
| 4078 | 3 | 4 | | IV-2 | GJC1 | 0.73 |
| 4079 | 3 | 4 | | IV-2 | GJC3 | 0.93 |
| 4080 | 3 | 4 | | IV-2 | GLA | 0.81 |
| 4081 | 3 | 4 | | IV-2 | GLB1L2 | 0.89 |
| 4082 | 3 | 4 | | IV-2 | GLE1 | 0.86 |
| 4083 | 3 | 4 | | IV-2 | GLG1 | 0.89 |
| 4084 | 3 | 4 | | IV-2 | GLI3 | 0.99 |
| 4085 | 3 | 4 | | IV-2 | GLIS1 | 0.89 |
| 4086 | 3 | 4 | | IV-2 | GLOD4 | 0.68 |
| 4087 | 3 | 4 | | IV-2 | GLRX2 | 0.78 |
| 4088 | 3 | 4 | | IV-2 | GLRX5 | 0.69 |
| 4089 | 3 | 4 | | IV-2 | GLT8D1 | 0.86 |
| 4090 | 3 | 4 | | IV-2 | GLUD1 | 0.97 |
| 4091 | 3 | 4 | | IV-2 | GLUL | 0.98 |
| 4092 | 3 | 4 | | IV-2 | GLYCTK | 0.75 |
| 4093 | 3 | 4 | | IV-2 | GLYR1 | 0.79 |
| 4094 | 3 | 4 | | IV-2 | GMPPA | 0.68 |
| 4095 | 3 | 4 | | IV-2 | GMPR2 | 0.82 |
| 4096 | 3 | 4 | | IV-2 | GNA12 | 0.72 |
| 4097 | 3 | 4 | | IV-2 | GNB1 | 0.76 |
| 4098 | 3 | 4 | | IV-2 | GNL1 | 0.88 |
| 4099 | 3 | 4 | | IV-2 | GNL3 | 0.97 |
| 4100 | 3 | 4 | | IV-2 | GNPNAT1 | 0.87 |
| 4101 | 3 | 4 | | IV-2 | GNRHR2 | 0.73 |
| 4102 | 3 | 4 | | IV-2 | GOLGA1 | 1.00 |
| 4103 | 3 | 4 | | IV-2 | GOLGA2 | 0.73 |
| 4104 | 3 | 4 | | IV-2 | GOLGA7B | 0.76 |
| 4105 | 3 | 4 | | IV-2 | GOLPH3 | 0.80 |
| 4106 | 3 | 4 | | IV-2 | GOLPH3L | 0.99 |
| 4107 | 3 | 4 | | IV-2 | GPAT2 | 1.00 |
| 4108 | 3 | 4 | | IV-2 | GPBP1L1 | 0.91 |
| 4109 | 3 | 4 | | IV-2 | GPHN | 0.99 |
| 4110 | 3 | 4 | | IV-2 | GPN1 | 0.75 |
| 4111 | 3 | 4 | | IV-2 | GPR107 | 0.97 |
| 4112 | 3 | 4 | | IV-2 | GPR115 | 0.95 |
| 4113 | 3 | 4 | | IV-2 | GPR124 | 0.85 |
| 4114 | 3 | 4 | | IV-2 | GPR125 | 0.88 |
| 4115 | 3 | 4 | | IV-2 | GPR126 | 0.93 |
| 4116 | 3 | 4 | | IV-2 | GPR161 | 0.94 |
| 4117 | 3 | 4 | | IV-2 | GPR162 | 0.76 |
| 4118 | 3 | 4 | | IV-2 | GPR89A | 0.92 |
| 4119 | 3 | 4 | | IV-2 | GPX3 | 0.86 |
| 4120 | 3 | 4 | | IV-2 | GRAMD4 | 0.75 |
| 4121 | 3 | 4 | | IV-2 | GREB1 | 0.89 |
| 4122 | 3 | 4 | | IV-2 | GRHL2 | 0.85 |
| 4123 | 3 | 4 | | IV-2 | GRID1 | 0.69 |
| 4124 | 3 | 4 | | IV-2 | GRIN3B | 0.98 |
| 4125 | 3 | 4 | | IV-2 | GRIPAP1 | 0.86 |
| 4126 | 3 | 4 | | IV-2 | GRTP1 | 0.95 |
| 4127 | 3 | 4 | | IV-2 | GSG2 | 0.93 |
| 4128 | 3 | 4 | | IV-2 | GSR | 0.73 |
| 4129 | 3 | 4 | | IV-2 | GSTK1 | 0.69 |
| 4130 | 3 | 4 | | IV-2 | GSTM5 | 0.90 |
| 4131 | 3 | 4 | | IV-2 | GSTO1 | 0.77 |
| 4132 | 3 | 4 | | IV-2 | GTF2A2 | 0.80 |
| 4133 | 3 | 4 | | IV-2 | GTF2B | 0.84 |
| 4134 | 3 | 4 | | IV-2 | GTF2E2 | 0.83 |
| 4135 | 3 | 4 | | IV-2 | GTF2I | 0.94 |
| 4136 | 3 | 4 | | IV-2 | GTF3A | 0.71 |
| 4137 | 3 | 4 | | IV-2 | GTF3C2 | 0.90 |
| 4138 | 3 | 4 | | IV-2 | GTF3C6 | 0.86 |
| 4139 | 3 | 4 | | IV-2 | GTPBP4 | 0.96 |
| 4140 | 3 | 4 | | IV-2 | GTPBP5 | 0.83 |
| 4141 | 3 | 4 | | IV-2 | GUCY1A3 | 0.81 |
| 4142 | 3 | 4 | | IV-2 | GUCY1B3 | 0.81 |
| 4143 | 3 | 4 | | IV-2 | GUSB | 0.77 |
| 4144 | 3 | 4 | | IV-2 | GYG1 | 0.91 |
| 4145 | 3 | 4 | | IV-2 | GZMB | 0.91 |
| 4146 | 3 | 4 | | IV-2 | H1F0 | 0.76 |
| 4147 | 3 | 4 | | IV-2 | H2AFB3 | 0.87 |
| 4148 | 3 | 4 | | IV-2 | H2AFJ | 0.72 |
| 4149 | 3 | 4 | | IV-2 | H2AFV | 0.72 |
| 4150 | 3 | 4 | | IV-2 | H3F3AP4 | 0.83 |
| 4151 | 3 | 4 | | IV-2 | H3F3B | 0.73 |
| 4152 | 3 | 4 | | IV-2 | HAAO | 0.87 |
| 4153 | 3 | 4 | | IV-2 | HADH | 0.94 |
| 4154 | 3 | 4 | | IV-2 | HADHB | 0.97 |
| 4155 | 3 | 4 | | IV-2 | HAND2 | 0.84 |
| 4156 | 3 | 4 | | IV-2 | HARS | 0.68 |
| 4157 | 3 | 4 | | IV-2 | HAUS1 | 0.87 |
| 4158 | 3 | 4 | | IV-2 | HAUS4 | 0.70 |
| 4159 | 3 | 4 | | IV-2 | HBXIP | 0.75 |
| 4160 | 3 | 4 | | IV-2 | HCCS | 0.91 |
| 4161 | 3 | 4 | | IV-2 | HCG23 | 0.94 |
| 4162 | 3 | 4 | | IV-2 | HCG25 | 0.68 |
| 4163 | 3 | 4 | | IV-2 | HCK | 0.98 |
| 4164 | 3 | 4 | | IV-2 | HCN2 | 0.97 |
| 4165 | 3 | 4 | | IV-2 | HDAC1 | 0.89 |
| 4166 | 3 | 4 | | IV-2 | HDAC2 | 0.99 |
| 4167 | 3 | 4 | | IV-2 | HDAC5 | 0.78 |
| 4168 | 3 | 4 | | IV-2 | HDDC2 | 0.85 |
| 4169 | 3 | 4 | | IV-2 | HDLBP | 0.68 |
| 4170 | 3 | 4 | | IV-2 | HEATR6 | 0.87 |
| 4171 | 3 | 4 | | IV-2 | HEATR7A | 0.80 |
| 4172 | 3 | 4 | | IV-2 | HEBP1 | 0.74 |
| 4173 | 3 | 4 | | IV-2 | HEBP2 | 0.87 |
| 4174 | 3 | 4 | | IV-2 | HERPUD2 | 0.83 |
| 4175 | 3 | 4 | | IV-2 | HES2 | 0.88 |
| 4176 | 3 | 4 | | IV-2 | HEXA | 0.81 |
| 4177 | 3 | 4 | | IV-2 | HEXDC | 0.87 |
| 4178 | 3 | 4 | | IV-2 | HEXIM1 | 0.91 |
| 4179 | 3 | 4 | | IV-2 | HIAT1 | 0.89 |
| 4180 | 3 | 4 | | IV-2 | HINFP | 0.93 |
| 4181 | 3 | 4 | | IV-2 | HINT1 | 0.70 |
| 4182 | 3 | 4 | | IV-2 | HINT2 | 0.69 |
| 4183 | 3 | 4 | | IV-2 | HIRIP3 | 0.71 |
| 4184 | 3 | 4 | | IV-2 | HIST1H2AD | 0.89 |
| 4185 | 3 | 4 | | IV-2 | HIST1H2BI | 0.93 |
| 4186 | 3 | 4 | | IV-2 | HIST1H2BJ | 0.89 |
| 4187 | 3 | 4 | | IV-2 | HIST1H3G | 0.98 |
| 4188 | 3 | 4 | | IV-2 | HIVEP2 | 0.92 |
| 4189 | 3 | 4 | | IV-2 | HLA-A | 0.79 |
| 4190 | 3 | 4 | | IV-2 | HLA-DMA | 0.68 |
| 4191 | 3 | 4 | | IV-2 | HLA-F | 0.95 |
| 4192 | 3 | 4 | | IV-2 | HLX | 0.76 |
| 4193 | 3 | 4 | | IV-2 | HMCN1 | 0.88 |
| 4194 | 3 | 4 | | IV-2 | HMGB1 | 0.91 |
| 4195 | 3 | 4 | | IV-2 | HMGB2 | 0.76 |
| 4196 | 3 | 4 | | IV-2 | HMGCL | 0.84 |
| 4197 | 3 | 4 | | IV-2 | HMGN1 | 0.97 |
| 4198 | 3 | 4 | | IV-2 | HMGN2 | 0.83 |
| 4199 | 3 | 4 | | IV-2 | HMGN4 | 0.88 |
| 4200 | 3 | 4 | | IV-2 | HMGXB3 | 0.70 |
| 4201 | 3 | 4 | | IV-2 | HMGXB4 | 0.99 |
| 4202 | 3 | 4 | | IV-2 | HMHA1 | 0.92 |
| 4203 | 3 | 4 | | IV-2 | HN1L | 0.84 |
| 4204 | 3 | 4 | | IV-2 | HNMT | 0.98 |
| 4205 | 3 | 4 | | IV-2 | HNRNPA1 | 0.81 |
| 4206 | 3 | 4 | | IV-2 | HNRNPA1L2 | 0.74 |
| 4207 | 3 | 4 | | IV-2 | HNRNPAB | 0.75 |
| 4208 | 3 | 4 | | IV-2 | HNRNPC | 0.69 |
| 4209 | 3 | 4 | | IV-2 | HNRNPD | 0.80 |
| 4210 | 3 | 4 | | IV-2 | HNRNPK | 0.87 |
| 4211 | 3 | 4 | | IV-2 | HNRNPKP3 | 0.96 |
| 4212 | 3 | 4 | | IV-2 | HNRNPM | 0.73 |
| 4213 | 3 | 4 | | IV-2 | HNRNPR | 0.69 |
| 4214 | 3 | 4 | | IV-2 | HNRNPU | 0.94 |
| 4215 | 3 | 4 | | IV-2 | HNRNPUL2 | 0.76 |
| 4216 | 3 | 4 | | IV-2 | HOMER3 | 0.87 |
| 4217 | 3 | 4 | | IV-2 | HOXA-AS3 | 0.93 |
| 4218 | 3 | 4 | | IV-2 | HOXB4 | 0.81 |
| 4219 | 3 | 4 | | IV-2 | HOXC12 | 0.73 |
| 4220 | 3 | 4 | | IV-2 | HOXD-AS2 | 0.80 |
| 4221 | 3 | 4 | | IV-2 | HRSP12 | 0.87 |

Fig. 38 - 23

| | | | | | | | |
|---|---|---|---|---|---|---|---|
| 4222 | 3 | 4 | | | IV-2 | HSCB | 0.85 |
| 4223 | 3 | 4 | | | IV-2 | HSD17B10 | 0.70 |
| 4224 | 3 | 4 | | | IV-2 | HSD17B4 | 0.91 |
| 4225 | 3 | 4 | | | IV-2 | HSD17B7 | 0.94 |
| 4226 | 3 | 4 | | | IV-2 | HSDL2 | 0.96 |
| 4227 | 3 | 4 | | | IV-2 | HSP90AB1 | 0.70 |
| 4228 | 3 | 4 | | | IV-2 | HSPA1L | 0.84 |
| 4229 | 3 | 4 | | | IV-2 | HSPA2 | 0.84 |
| 4230 | 3 | 4 | | | IV-2 | HSPA5 | 0.93 |
| 4231 | 3 | 4 | | | IV-2 | HSPE1-MOB4 | 0.82 |
| 4232 | 3 | 4 | | | IV-2 | HTATIP2 | 0.70 |
| 4233 | 3 | 4 | | | IV-2 | HTATSF1 | 0.99 |
| 4234 | 3 | 4 | | | IV-2 | HTRA1 | 0.76 |
| 4235 | 3 | 4 | | | IV-2 | HTT | 0.80 |
| 4236 | 3 | 4 | | | IV-2 | HUNK | 0.72 |
| 4237 | 3 | 4 | | | IV-2 | HYAL3 | 0.71 |
| 4238 | 3 | 4 | | | IV-2 | IAH1 | 0.83 |
| 4239 | 3 | 4 | | | IV-2 | ID2B | 0.79 |
| 4240 | 3 | 4 | | | IV-2 | IDH3A | 0.84 |
| 4241 | 3 | 4 | | | IV-2 | IDI2 | 0.84 |
| 4242 | 3 | 4 | | | IV-2 | IER3IP1 | 0.73 |
| 4243 | 3 | 4 | | | IV-2 | IFIT5 | 0.93 |
| 4244 | 3 | 4 | | | IV-2 | IFNGR1 | 0.98 |
| 4245 | 3 | 4 | | | IV-2 | IFNGR2 | 0.69 |
| 4246 | 3 | 4 | | | IV-2 | IFT122 | 0.78 |
| 4247 | 3 | 4 | | | IV-2 | IFT140 | 0.77 |
| 4248 | 3 | 4 | | | IV-2 | IFT172 | 0.85 |
| 4249 | 3 | 4 | | | IV-2 | IFT46 | 0.72 |
| 4250 | 3 | 4 | | | IV-2 | IFT52 | 0.95 |
| 4251 | 3 | 4 | | | IV-2 | IFT57 | 0.98 |
| 4252 | 3 | 4 | | | IV-2 | IGFBP3 | 0.79 |
| 4253 | 3 | 4 | | | IV-2 | IGFBP4 | 0.69 |
| 4254 | 3 | 4 | | | IV-2 | IGFBP7 | 0.73 |
| 4255 | 3 | 4 | | | IV-2 | IGSF11 | 0.86 |
| 4256 | 3 | 4 | | | IV-2 | IGSF21 | 0.96 |
| 4257 | 3 | 4 | | | IV-2 | IK | 0.79 |
| 4258 | 3 | 4 | | | IV-2 | IL10RB | 0.90 |
| 4259 | 3 | 4 | | | IV-2 | IL11 | 0.85 |
| 4260 | 3 | 4 | | | IV-2 | IL17D | 0.75 |
| 4261 | 3 | 4 | | | IV-2 | IL17RA | 0.77 |
| 4262 | 3 | 4 | | | IV-2 | IL22RA1 | 0.75 |
| 4263 | 3 | 4 | | | IV-2 | IL27RA | 0.71 |
| 4264 | 3 | 4 | | | IV-2 | IL28RA | 0.85 |
| 4265 | 3 | 4 | | | IV-2 | IL3RA | 0.72 |
| 4266 | 3 | 4 | | | IV-2 | IL7 | 0.88 |
| 4267 | 3 | 4 | | | IV-2 | ILF2 | 0.87 |
| 4268 | 3 | 4 | | | IV-2 | ILK | 0.73 |
| 4269 | 3 | 4 | | | IV-2 | IMMT | 0.88 |
| 4270 | 3 | 4 | | | IV-2 | IMPAD1 | 0.89 |
| 4271 | 3 | 4 | | | IV-2 | INCENP | 0.91 |
| 4272 | 3 | 4 | | | IV-2 | ING1 | 0.79 |
| 4273 | 3 | 4 | | | IV-2 | ING2 | 0.68 |
| 4274 | 3 | 4 | | | IV-2 | ING4 | 0.90 |
| 4275 | 3 | 4 | | | IV-2 | INO80 | 0.79 |
| 4276 | 3 | 4 | | | IV-2 | INPP5A | 0.80 |
| 4277 | 3 | 4 | | | IV-2 | INPP5B | 0.80 |
| 4278 | 3 | 4 | | | IV-2 | INPP5D | 0.91 |
| 4279 | 3 | 4 | | | IV-2 | INTS10 | 0.84 |
| 4280 | 3 | 4 | | | IV-2 | INTS12 | 0.74 |
| 4281 | 3 | 4 | | | IV-2 | INTS4 | 0.85 |
| 4282 | 3 | 4 | | | IV-2 | INTS7 | 0.92 |
| 4283 | 3 | 4 | | | IV-2 | IP6K2 | 0.95 |
| 4284 | 3 | 4 | | | IV-2 | IPMK | 0.78 |
| 4285 | 3 | 4 | | | IV-2 | IPO5 | 0.99 |
| 4286 | 3 | 4 | | | IV-2 | IPO7 | 0.94 |
| 4287 | 3 | 4 | | | IV-2 | IPO9 | 0.94 |
| 4288 | 3 | 4 | | | IV-2 | IPPK | 0.80 |
| 4289 | 3 | 4 | | | IV-2 | IQGAP1 | 0.78 |
| 4290 | 3 | 4 | | | IV-2 | IQSEC1 | 0.97 |
| 4291 | 3 | 4 | | | IV-2 | IRAK2 | 0.95 |
| 4292 | 3 | 4 | | | IV-2 | IRAK4 | 0.97 |
| 4293 | 3 | 4 | | | IV-2 | IRF1 | 0.95 |
| 4294 | 3 | 4 | | | IV-2 | IRF2 | 0.77 |
| 4295 | 3 | 4 | | | IV-2 | ISCA1 | 0.82 |
| 4296 | 3 | 4 | | | IV-2 | ISCA2 | 0.73 |
| 4297 | 3 | 4 | | | IV-2 | IST1 | 0.84 |
| 4298 | 3 | 4 | | | IV-2 | ITFG2 | 0.92 |
| 4299 | 3 | 4 | | | IV-2 | ITGA10 | 0.94 |
| 4300 | 3 | 4 | | | IV-2 | ITGA6 | 0.84 |
| 4301 | 3 | 4 | | | IV-2 | ITGB7 | 0.68 |
| 4302 | 3 | 4 | | | IV-2 | ITM2A | 0.82 |
| 4303 | 3 | 4 | | | IV-2 | ITM2C | 0.70 |
| 4304 | 3 | 4 | | | IV-2 | ITPA | 0.69 |
| 4305 | 3 | 4 | | | IV-2 | ITPKB | 0.67 |
| 4306 | 3 | 4 | | | IV-2 | ITPRIPL1 | 0.85 |
| 4307 | 3 | 4 | | | IV-2 | JAK1 | 0.94 |
| 4308 | 3 | 4 | | | IV-2 | JAK3 | 0.81 |
| 4309 | 3 | 4 | | | IV-2 | JAM3 | 0.88 |
| 4310 | 3 | 4 | | | IV-2 | JARID2 | 0.96 |
| 4311 | 3 | 4 | | | IV-2 | JAZF1 | 0.72 |
| 4312 | 3 | 4 | | | IV-2 | JMJD4 | 0.82 |
| 4313 | 3 | 4 | | | IV-2 | JMJD6 | 0.91 |
| 4314 | 3 | 4 | | | IV-2 | JMJD7 | 0.93 |
| 4315 | 3 | 4 | | | IV-2 | JPH4 | 0.88 |
| 4316 | 3 | 4 | | | IV-2 | JTB | 0.70 |
| 4317 | 3 | 4 | | | IV-2 | KANSL1 | 0.84 |
| 4318 | 3 | 4 | | | IV-2 | KANSL2 | 0.97 |
| 4319 | 3 | 4 | | | IV-2 | KBTBD4 | 0.77 |
| 4320 | 3 | 4 | | | IV-2 | KCMF1 | 0.83 |
| 4321 | 3 | 4 | | | IV-2 | KCNC4 | 0.68 |
| 4322 | 3 | 4 | | | IV-2 | KCND1 | 0.75 |
| 4323 | 3 | 4 | | | IV-2 | KCNE1 | 1.00 |
| 4324 | 3 | 4 | | | IV-2 | KCNG1 | 0.97 |
| 4325 | 3 | 4 | | | IV-2 | KCNIP3 | 0.85 |
| 4326 | 3 | 4 | | | IV-2 | KCNJ11 | 1.00 |
| 4327 | 3 | 4 | | | IV-2 | KCNJ2-AS1 | 0.99 |
| 4328 | 3 | 4 | | | IV-2 | KCNS3 | 0.90 |
| 4329 | 3 | 4 | | | IV-2 | KCTD10 | 0.91 |
| 4330 | 3 | 4 | | | IV-2 | KCTD15 | 0.78 |
| 4331 | 3 | 4 | | | IV-2 | KCTD2 | 0.71 |
| 4332 | 3 | 4 | | | IV-2 | KCTD21 | 0.98 |
| 4333 | 3 | 4 | | | IV-2 | KCTD3 | 0.95 |
| 4334 | 3 | 4 | | | IV-2 | KDELC1 | 0.87 |
| 4335 | 3 | 4 | | | IV-2 | KDELR2 | 0.88 |
| 4336 | 3 | 4 | | | IV-2 | KDM1A | 0.75 |
| 4337 | 3 | 4 | | | IV-2 | KDM2A | 0.69 |
| 4338 | 3 | 4 | | | IV-2 | KDM2B | 0.80 |
| 4339 | 3 | 4 | | | IV-2 | KDM4A | 0.93 |
| 4340 | 3 | 4 | | | IV-2 | KDM4B | 0.70 |
| 4341 | 3 | 4 | | | IV-2 | KDM4C | 1.00 |
| 4342 | 3 | 4 | | | IV-2 | KDM4D | 0.86 |
| 4343 | 3 | 4 | | | IV-2 | KDM5C | 0.79 |
| 4344 | 3 | 4 | | | IV-2 | KDSR | 0.97 |
| 4345 | 3 | 4 | | | IV-2 | KHDRBS1 | 0.85 |
| 4346 | 3 | 4 | | | IV-2 | KHDRBS3 | 0.95 |
| 4347 | 3 | 4 | | | IV-2 | KIAA0040 | 0.73 |
| 4348 | 3 | 4 | | | IV-2 | KIAA0090 | 0.88 |
| 4349 | 3 | 4 | | | IV-2 | KIAA0319L | 0.81 |
| 4350 | 3 | 4 | | | IV-2 | KIAA0368 | 1.00 |
| 4351 | 3 | 4 | | | IV-2 | KIAA0664 | 0.67 |
| 4352 | 3 | 4 | | | IV-2 | KIAA0913 | 0.77 |
| 4353 | 3 | 4 | | | IV-2 | KIAA1191 | 0.80 |
| 4354 | 3 | 4 | | | IV-2 | KIAA1217 | 0.91 |
| 4355 | 3 | 4 | | | IV-2 | KIAA1614 | 0.88 |
| 4356 | 3 | 4 | | | IV-2 | KIAA1683 | 0.76 |
| 4357 | 3 | 4 | | | IV-2 | KIF13A | 0.95 |
| 4358 | 3 | 4 | | | IV-2 | KIF18B | 0.77 |
| 4359 | 3 | 4 | | | IV-2 | KIF9 | 0.87 |
| 4360 | 3 | 4 | | | IV-2 | KLB | 0.96 |
| 4361 | 3 | 4 | | | IV-2 | KLC1 | 0.95 |
| 4362 | 3 | 4 | | | IV-2 | KLC4 | 0.77 |
| 4363 | 3 | 4 | | | IV-2 | KLF14 | 0.99 |
| 4364 | 3 | 4 | | | IV-2 | KLF6 | 0.93 |
| 4365 | 3 | 4 | | | IV-2 | KLHDC2 | 0.98 |
| 4366 | 3 | 4 | | | IV-2 | KLHDC4 | 0.70 |
| 4367 | 3 | 4 | | | IV-2 | KLHL21 | 0.95 |
| 4368 | 3 | 4 | | | IV-2 | KLHL22 | 0.70 |
| 4369 | 3 | 4 | | | IV-2 | KPNA1 | 0.97 |
| 4370 | 3 | 4 | | | IV-2 | KRT19P2 | 0.75 |
| 4371 | 3 | 4 | | | IV-2 | KRT3 | 0.95 |
| 4372 | 3 | 4 | | | IV-2 | LAGE3 | 0.69 |
| 4373 | 3 | 4 | | | IV-2 | LAMP5 | 0.99 |
| 4374 | 3 | 4 | | | IV-2 | LANCL2 | 0.98 |
| 4375 | 3 | 4 | | | IV-2 | LAP3 | 0.86 |
| 4376 | 3 | 4 | | | IV-2 | LAPTM4A | 0.78 |
| 4377 | 3 | 4 | | | IV-2 | LARGE | 0.74 |
| 4378 | 3 | 4 | | | IV-2 | LARP1 | 0.99 |
| 4379 | 3 | 4 | | | IV-2 | LARP1B | 0.91 |
| 4380 | 3 | 4 | | | IV-2 | LARS2 | 0.72 |
| 4381 | 3 | 4 | | | IV-2 | LAS1L | 0.70 |
| 4382 | 3 | 4 | | | IV-2 | LAYN | 0.83 |
| 4383 | 3 | 4 | | | IV-2 | LBH | 0.74 |
| 4384 | 3 | 4 | | | IV-2 | LCMT1 | 0.87 |
| 4385 | 3 | 4 | | | IV-2 | LDOC1L | 0.81 |
| 4386 | 3 | 4 | | | IV-2 | LEMD2 | 0.67 |
| 4387 | 3 | 4 | | | IV-2 | LEMD3 | 0.93 |
| 4388 | 3 | 4 | | | IV-2 | LENG9 | 0.68 |
| 4389 | 3 | 4 | | | IV-2 | LEO1 | 0.88 |
| 4390 | 3 | 4 | | | IV-2 | LEPRE1 | 0.72 |
| 4391 | 3 | 4 | | | IV-2 | LEPREL1 | 0.77 |
| 4392 | 3 | 4 | | | IV-2 | LEPREL2 | 0.70 |
| 4393 | 3 | 4 | | | IV-2 | LEPROT | 0.97 |
| 4394 | 3 | 4 | | | IV-2 | LFNG | 0.79 |
| 4395 | 3 | 4 | | | IV-2 | LGALS4 | 0.78 |
| 4396 | 3 | 4 | | | IV-2 | LGR6 | 0.70 |
| 4397 | 3 | 4 | | | IV-2 | LHB | 0.95 |
| 4398 | 3 | 4 | | | IV-2 | LHFPL2 | 0.94 |
| 4399 | 3 | 4 | | | IV-2 | LIAS | 0.85 |
| 4400 | 3 | 4 | | | IV-2 | LIF | 0.78 |
| 4401 | 3 | 4 | | | IV-2 | LIME1 | 0.84 |
| 4402 | 3 | 4 | | | IV-2 | LIMS1 | 0.93 |
| 4403 | 3 | 4 | | | IV-2 | LINC00086 | 0.77 |
| 4404 | 3 | 4 | | | IV-2 | LINC00176 | 0.96 |
| 4405 | 3 | 4 | | | IV-2 | LINC00263 | 0.68 |
| 4406 | 3 | 4 | | | IV-2 | LINC00294 | 0.93 |
| 4407 | 3 | 4 | | | IV-2 | LINC00319 | 0.88 |
| 4408 | 3 | 4 | | | IV-2 | LINC00493 | 0.88 |
| 4409 | 3 | 4 | | | IV-2 | LINC00526 | 0.67 |
| 4410 | 3 | 4 | | | IV-2 | LINS | 0.75 |
| 4411 | 3 | 4 | | | IV-2 | LIPA | 0.98 |
| 4412 | 3 | 4 | | | IV-2 | LITAF | 0.98 |
| 4413 | 3 | 4 | | | IV-2 | LLGL2 | 0.80 |

Fig. 38 - 24

| | | | | | | | |
|---|---|---|---|---|---|---|---|
| 4414 | 3 | 4 | | | IV-2 | LLPH | 0.92 |
| 4415 | 3 | 4 | | | IV-2 | LMAN2L | 0.77 |
| 4416 | 3 | 4 | | | IV-2 | LMO2 | 0.76 |
| 4417 | 3 | 4 | | | IV-2 | LNPEP | 1.00 |
| 4418 | 3 | 4 | | | IV-2 | LOC100009676 | 0.82 |
| 4419 | 3 | 4 | | | IV-2 | LOC100093631 | 0.87 |
| 4420 | 3 | 4 | | | IV-2 | LOC100125556 | 0.98 |
| 4421 | 3 | 4 | | | IV-2 | LOC100128239 | 1.00 |
| 4422 | 3 | 4 | | | IV-2 | LOC100128361 | 0.98 |
| 4423 | 3 | 4 | | | IV-2 | LOC100128881 | 0.74 |
| 4424 | 3 | 4 | | | IV-2 | LOC100129046 | 0.96 |
| 4425 | 3 | 4 | | | IV-2 | LOC100129250 | 0.76 |
| 4426 | 3 | 4 | | | IV-2 | LOC100129361 | 0.82 |
| 4427 | 3 | 4 | | | IV-2 | LOC100129534 | 0.84 |
| 4428 | 3 | 4 | | | IV-2 | LOC100129722 | 0.90 |
| 4429 | 3 | 4 | | | IV-2 | LOC100130744 | 0.87 |
| 4430 | 3 | 4 | | | IV-2 | LOC100132707 | 0.93 |
| 4431 | 3 | 4 | | | IV-2 | LOC100133091 | 0.88 |
| 4432 | 3 | 4 | | | IV-2 | LOC100133669 | 0.70 |
| 4433 | 3 | 4 | | | IV-2 | LOC100287015 | 0.81 |
| 4434 | 3 | 4 | | | IV-2 | LOC100287042 | 0.82 |
| 4435 | 3 | 4 | | | IV-2 | LOC100287177 | 0.94 |
| 4436 | 3 | 4 | | | IV-2 | LOC100288198 | 0.83 |
| 4437 | 3 | 4 | | | IV-2 | LOC100288432 | 0.84 |
| 4438 | 3 | 4 | | | IV-2 | LOC100288637 | 0.99 |
| 4439 | 3 | 4 | | | IV-2 | LOC100288748 | 0.96 |
| 4440 | 3 | 4 | | | IV-2 | LOC100289255 | 0.72 |
| 4441 | 3 | 4 | | | IV-2 | LOC100289509 | 0.87 |
| 4442 | 3 | 4 | | | IV-2 | LOC100499466 | 0.88 |
| 4443 | 3 | 4 | | | IV-2 | LOC100505495 | 0.79 |
| 4444 | 3 | 4 | | | IV-2 | LOC100505624 | 0.85 |
| 4445 | 3 | 4 | | | IV-2 | LOC100505761 | 0.81 |
| 4446 | 3 | 4 | | | IV-2 | LOC100505806 | 0.73 |
| 4447 | 3 | 4 | | | IV-2 | LOC100505812 | 0.93 |
| 4448 | 3 | 4 | | | IV-2 | LOC100505876 | 0.72 |
| 4449 | 3 | 4 | | | IV-2 | LOC100505894 | 0.89 |
| 4450 | 3 | 4 | | | IV-2 | LOC100506068 | 0.81 |
| 4451 | 3 | 4 | | | IV-2 | LOC100506190 | 0.69 |
| 4452 | 3 | 4 | | | IV-2 | LOC100506207 | 0.98 |
| 4453 | 3 | 4 | | | IV-2 | LOC100506388 | 0.81 |
| 4454 | 3 | 4 | | | IV-2 | LOC100506668 | 0.78 |
| 4455 | 3 | 4 | | | IV-2 | LOC100506714 | 0.88 |
| 4456 | 3 | 4 | | | IV-2 | LOC100506930 | 0.84 |
| 4457 | 3 | 4 | | | IV-2 | LOC100506963 | 0.81 |
| 4458 | 3 | 4 | | | IV-2 | LOC100507373 | 0.79 |
| 4459 | 3 | 4 | | | IV-2 | LOC100507433 | 0.96 |
| 4460 | 3 | 4 | | | IV-2 | LOC100507567 | 0.69 |
| 4461 | 3 | 4 | | | IV-2 | LOC100859930 | 0.71 |
| 4462 | 3 | 4 | | | IV-2 | LOC115110 | 0.87 |
| 4463 | 3 | 4 | | | IV-2 | LOC143666 | 0.84 |
| 4464 | 3 | 4 | | | IV-2 | LOC154761 | 0.79 |
| 4465 | 3 | 4 | | | IV-2 | LOC220906 | 0.90 |
| 4466 | 3 | 4 | | | IV-2 | LOC254100 | 1.00 |
| 4467 | 3 | 4 | | | IV-2 | LOC283104 | 0.85 |
| 4468 | 3 | 4 | | | IV-2 | LOC283481 | 0.72 |
| 4469 | 3 | 4 | | | IV-2 | LOC284009 | 0.96 |
| 4470 | 3 | 4 | | | IV-2 | LOC284276 | 0.79 |
| 4471 | 3 | 4 | | | IV-2 | LOC284385 | 0.96 |
| 4472 | 3 | 4 | | | IV-2 | LOC284578 | 0.69 |
| 4473 | 3 | 4 | | | IV-2 | LOC285074 | 0.94 |
| 4474 | 3 | 4 | | | IV-2 | LOC285419 | 0.88 |
| 4475 | 3 | 4 | | | IV-2 | LOC340037 | 0.89 |
| 4476 | 3 | 4 | | | IV-2 | LOC375295 | 0.69 |
| 4477 | 3 | 4 | | | IV-2 | LOC387723 | 0.79 |
| 4478 | 3 | 4 | | | IV-2 | LOC388630 | 0.69 |
| 4479 | 3 | 4 | | | IV-2 | LOC389906 | 0.83 |
| 4480 | 3 | 4 | | | IV-2 | LOC400027 | 0.90 |
| 4481 | 3 | 4 | | | IV-2 | LOC400043 | 0.70 |
| 4482 | 3 | 4 | | | IV-2 | LOC400752 | 0.85 |
| 4483 | 3 | 4 | | | IV-2 | LOC401127 | 0.84 |
| 4484 | 3 | 4 | | | IV-2 | LOC401321 | 0.78 |
| 4485 | 3 | 4 | | | IV-2 | LOC439990 | 0.97 |
| 4486 | 3 | 4 | | | IV-2 | LOC440335 | 0.99 |
| 4487 | 3 | 4 | | | IV-2 | LOC644649 | 0.76 |
| 4488 | 3 | 4 | | | IV-2 | LOC644936 | 0.88 |
| 4489 | 3 | 4 | | | IV-2 | LOC645212 | 0.93 |
| 4490 | 3 | 4 | | | IV-2 | LOC646576 | 0.98 |
| 4491 | 3 | 4 | | | IV-2 | LOC646762 | 0.84 |
| 4492 | 3 | 4 | | | IV-2 | LOC648987 | 0.70 |
| 4493 | 3 | 4 | | | IV-2 | LOC653566 | 0.87 |
| 4494 | 3 | 4 | | | IV-2 | LOC728066 | 0.78 |
| 4495 | 3 | 4 | | | IV-2 | LOC728752 | 0.90 |
| 4496 | 3 | 4 | | | IV-2 | LOC728855 | 0.75 |
| 4497 | 3 | 4 | | | IV-2 | LOC729013 | 0.74 |
| 4498 | 3 | 4 | | | IV-2 | LOC729678 | 0.87 |
| 4499 | 3 | 4 | | | IV-2 | LOC729799 | 0.85 |
| 4500 | 3 | 4 | | | IV-2 | LOC80054 | 0.92 |
| 4501 | 3 | 4 | | | IV-2 | LOC84856 | 0.98 |
| 4502 | 3 | 4 | | | IV-2 | LOC92249 | 0.77 |
| 4503 | 3 | 4 | | | IV-2 | LOC93622 | 0.90 |
| 4504 | 3 | 4 | | | IV-2 | LOXL4 | 0.68 |
| 4505 | 3 | 4 | | | IV-2 | LPCAT1 | 0.74 |
| 4506 | 3 | 4 | | | IV-2 | LPCAT2 | 0.97 |
| 4507 | 3 | 4 | | | IV-2 | LPPR2 | 0.67 |
| 4508 | 3 | 4 | | | IV-2 | LRP2BP | 0.97 |
| 4509 | 3 | 4 | | | IV-2 | LRPAP1 | 0.71 |
| 4510 | 3 | 4 | | | IV-2 | LRR1 | 0.69 |
| 4511 | 3 | 4 | | | IV-2 | LRRC1 | 0.95 |
| 4512 | 3 | 4 | | | IV-2 | LRRC14 | 0.69 |
| 4513 | 3 | 4 | | | IV-2 | LRRC16B | 0.68 |
| 4514 | 3 | 4 | | | IV-2 | LRRC20 | 0.72 |
| 4515 | 3 | 4 | | | IV-2 | LRRC27 | 0.74 |
| 4516 | 3 | 4 | | | IV-2 | LRRC33 | 0.90 |
| 4517 | 3 | 4 | | | IV-2 | LRRC37B | 0.95 |
| 4518 | 3 | 4 | | | IV-2 | LRRC48 | 0.81 |
| 4519 | 3 | 4 | | | IV-2 | LRRC6 | 0.89 |
| 4520 | 3 | 4 | | | IV-2 | LRRC8C | 0.72 |
| 4521 | 3 | 4 | | | IV-2 | LRRC8D | 0.89 |
| 4522 | 3 | 4 | | | IV-2 | LRRFIP2 | 0.69 |
| 4523 | 3 | 4 | | | IV-2 | LRRN1 | 0.91 |
| 4524 | 3 | 4 | | | IV-2 | LRTOMT | 0.83 |
| 4525 | 3 | 4 | | | IV-2 | LSG1 | 0.91 |
| 4526 | 3 | 4 | | | IV-2 | LSM10 | 0.78 |
| 4527 | 3 | 4 | | | IV-2 | LSM14A | 0.85 |
| 4528 | 3 | 4 | | | IV-2 | LSMD1 | 0.70 |
| 4529 | 3 | 4 | | | IV-2 | LTB4R | 0.86 |
| 4530 | 3 | 4 | | | IV-2 | LTBP2 | 0.76 |
| 4531 | 3 | 4 | | | IV-2 | LTBP3 | 0.73 |
| 4532 | 3 | 4 | | | IV-2 | LURAP1L | 0.87 |
| 4533 | 3 | 4 | | | IV-2 | LXN | 0.71 |
| 4534 | 3 | 4 | | | IV-2 | LY6G6D | 0.99 |
| 4535 | 3 | 4 | | | IV-2 | LYRM1 | 0.88 |
| 4536 | 3 | 4 | | | IV-2 | LYRM4 | 0.68 |
| 4537 | 3 | 4 | | | IV-2 | LYSMD1 | 0.99 |
| 4538 | 3 | 4 | | | IV-2 | LYSMD4 | 1.00 |
| 4539 | 3 | 4 | | | IV-2 | MAD2L1BP | 0.89 |
| 4540 | 3 | 4 | | | IV-2 | MADD | 0.81 |
| 4541 | 3 | 4 | | | IV-2 | MAEA | 0.76 |
| 4542 | 3 | 4 | | | IV-2 | MAFF | 0.90 |
| 4543 | 3 | 4 | | | IV-2 | MAGED2 | 0.70 |
| 4544 | 3 | 4 | | | IV-2 | MAGED4B | 0.70 |
| 4545 | 3 | 4 | | | IV-2 | MAGEF1 | 0.82 |
| 4546 | 3 | 4 | | | IV-2 | MAGEH1 | 0.69 |
| 4547 | 3 | 4 | | | IV-2 | MALSU1 | 0.72 |
| 4548 | 3 | 4 | | | IV-2 | MAMLD1 | 0.68 |
| 4549 | 3 | 4 | | | IV-2 | MAMSTR | 0.90 |
| 4550 | 3 | 4 | | | IV-2 | MAN2B2 | 0.99 |
| 4551 | 3 | 4 | | | IV-2 | MANBAL | 0.77 |
| 4552 | 3 | 4 | | | IV-2 | MANF | 0.95 |
| 4553 | 3 | 4 | | | IV-2 | MAP1A | 0.80 |
| 4554 | 3 | 4 | | | IV-2 | MAP1LC3A | 0.75 |
| 4555 | 3 | 4 | | | IV-2 | MAP1LC3B | 0.95 |
| 4556 | 3 | 4 | | | IV-2 | MAP2K1 | 0.93 |
| 4557 | 3 | 4 | | | IV-2 | MAP3K12 | 0.84 |
| 4558 | 3 | 4 | | | IV-2 | MAP3K13 | 0.83 |
| 4559 | 3 | 4 | | | IV-2 | MAP3K3 | 0.68 |
| 4560 | 3 | 4 | | | IV-2 | MAP4K1 | 0.94 |
| 4561 | 3 | 4 | | | IV-2 | MAP4K2 | 0.70 |
| 4562 | 3 | 4 | | | IV-2 | MAPK1IP1L | 0.89 |
| 4563 | 3 | 4 | | | IV-2 | MAPK9 | 0.94 |
| 4564 | 3 | 4 | | | IV-2 | MAPKAP1 | 0.77 |
| 4565 | 3 | 4 | | | IV-2 | MAPKAPK5 | 0.83 |
| 4566 | 3 | 4 | | | IV-2 | MAPRE3 | 0.68 |
| 4567 | 3 | 4 | | | IV-2 | MAPT | 0.92 |
| 4568 | 3 | 4 | | | IV-2 | MARCH5 | 0.99 |
| 4569 | 3 | 4 | | | IV-2 | MARCKSL1 | 0.68 |
| 4570 | 3 | 4 | | | IV-2 | MARK3 | 0.84 |
| 4571 | 3 | 4 | | | IV-2 | MARS | 0.78 |
| 4572 | 3 | 4 | | | IV-2 | MASP1 | 0.68 |
| 4573 | 3 | 4 | | | IV-2 | MAT2B | 0.89 |
| 4574 | 3 | 4 | | | IV-2 | MATN2 | 0.96 |
| 4575 | 3 | 4 | | | IV-2 | MB21D2 | 0.75 |
| 4576 | 3 | 4 | | | IV-2 | MBD1 | 0.71 |
| 4577 | 3 | 4 | | | IV-2 | MBNL1 | 0.99 |
| 4578 | 3 | 4 | | | IV-2 | MBTPS1 | 0.87 |
| 4579 | 3 | 4 | | | IV-2 | MCCC2 | 0.97 |
| 4580 | 3 | 4 | | | IV-2 | MCEE | 0.89 |
| 4581 | 3 | 4 | | | IV-2 | MCHR1 | 0.93 |
| 4582 | 3 | 4 | | | IV-2 | MCM3 | 0.70 |
| 4583 | 3 | 4 | | | IV-2 | MCM3AP | 0.93 |
| 4584 | 3 | 4 | | | IV-2 | MCMBP | 0.98 |
| 4585 | 3 | 4 | | | IV-2 | MCOLN1 | 0.70 |
| 4586 | 3 | 4 | | | IV-2 | MCU | 0.69 |
| 4587 | 3 | 4 | | | IV-2 | MDC1 | 0.76 |
| 4588 | 3 | 4 | | | IV-2 | MDH1 | 0.81 |
| 4589 | 3 | 4 | | | IV-2 | ME2 | 0.89 |
| 4590 | 3 | 4 | | | IV-2 | MEAF6 | 0.73 |
| 4591 | 3 | 4 | | | IV-2 | MECP2 | 0.83 |
| 4592 | 3 | 4 | | | IV-2 | MECR | 0.93 |
| 4593 | 3 | 4 | | | IV-2 | MED12 | 0.73 |
| 4594 | 3 | 4 | | | IV-2 | MED18 | 0.74 |
| 4595 | 3 | 4 | | | IV-2 | MED21 | 0.95 |
| 4596 | 3 | 4 | | | IV-2 | MED22 | 0.74 |
| 4597 | 3 | 4 | | | IV-2 | MED29 | 0.82 |
| 4598 | 3 | 4 | | | IV-2 | MED4 | 0.83 |
| 4599 | 3 | 4 | | | IV-2 | MED6 | 0.97 |
| 4600 | 3 | 4 | | | IV-2 | MED8 | 0.92 |
| 4601 | 3 | 4 | | | IV-2 | MED9 | 0.80 |
| 4602 | 3 | 4 | | | IV-2 | MEF2D | 0.69 |
| 4603 | 3 | 4 | | | IV-2 | MEGF8 | 0.70 |
| 4604 | 3 | 4 | | | IV-2 | MEIS3P1 | 0.93 |
| 4605 | 3 | 4 | | | IV-2 | MELK | 1.00 |

Fig. 38 - 25

| | | | | | | | | | | | | | | |
|---|---|---|---|---|---|---|---|---|---|---|---|---|---|---|
| 4606 | 3 | 4 | | | IV-2 | MEOX2 | 0.69 | 4702 | 3 | 4 | | | IV-2 | MTMR11 | 0.69 |
| 4607 | 3 | 4 | | | IV-2 | MESDC1 | 0.70 | 4703 | 3 | 4 | | | IV-2 | MTMR14 | 0.71 |
| 4608 | 3 | 4 | | | IV-2 | MESDC2 | 0.96 | 4704 | 3 | 4 | | | IV-2 | MTRNR2L2 | 0.70 |
| 4609 | 3 | 4 | | | IV-2 | METTL19 | 0.89 | 4705 | 3 | 4 | | | IV-2 | MTUS1 | 0.83 |
| 4610 | 3 | 4 | | | IV-2 | METTL21A | 0.93 | 4706 | 3 | 4 | | | IV-2 | MTX1 | 0.68 |
| 4611 | 3 | 4 | | | IV-2 | METTL21B | 1.00 | 4707 | 3 | 4 | | | IV-2 | MTX2 | 1.00 |
| 4612 | 3 | 4 | | | IV-2 | MFAP4 | 0.85 | 4708 | 3 | 4 | | | IV-2 | MUM1 | 0.70 |
| 4613 | 3 | 4 | | | IV-2 | MFF | 0.79 | 4709 | 3 | 4 | | | IV-2 | MUTED | 0.99 |
| 4614 | 3 | 4 | | | IV-2 | MFN2 | 0.78 | 4710 | 3 | 4 | | | IV-2 | MXD4 | 0.70 |
| 4615 | 3 | 4 | | | IV-2 | MFNG | 0.74 | 4711 | 3 | 4 | | | IV-2 | MXRA7 | 0.70 |
| 4616 | 3 | 4 | | | IV-2 | MFSD3 | 0.73 | 4712 | 3 | 4 | | | IV-2 | MYCT1 | 0.87 |
| 4617 | 3 | 4 | | | IV-2 | MFSD4 | 0.97 | 4713 | 3 | 4 | | | IV-2 | MYEOV2 | 0.82 |
| 4618 | 3 | 4 | | | IV-2 | MGAT2 | 0.82 | 4714 | 3 | 4 | | | IV-2 | MYH10 | 0.94 |
| 4619 | 3 | 4 | | | IV-2 | MGAT4B | 0.69 | 4715 | 3 | 4 | | | IV-2 | MYL12A | 0.74 |
| 4620 | 3 | 4 | | | IV-2 | MGC16275 | 0.79 | 4716 | 3 | 4 | | | IV-2 | MYL3 | 0.80 |
| 4621 | 3 | 4 | | | IV-2 | MGC3771 | 0.91 | 4717 | 3 | 4 | | | IV-2 | MYL6B | 0.73 |
| 4622 | 3 | 4 | | | IV-2 | MGMT | 0.69 | 4718 | 3 | 4 | | | IV-2 | MYLIP | 1.00 |
| 4623 | 3 | 4 | | | IV-2 | MGST3 | 0.69 | 4719 | 3 | 4 | | | IV-2 | MYO10 | 0.91 |
| 4624 | 3 | 4 | | | IV-2 | MICAL3 | 0.85 | 4720 | 3 | 4 | | | IV-2 | MYO1D | 0.72 |
| 4625 | 3 | 4 | | | IV-2 | MICU1 | 0.71 | 4721 | 3 | 4 | | | IV-2 | MYO3A | 0.98 |
| 4626 | 3 | 4 | | | IV-2 | MID1 | 0.96 | 4722 | 3 | 4 | | | IV-2 | MYO7A | 0.84 |
| 4627 | 3 | 4 | | | IV-2 | MID1IP1 | 0.72 | 4723 | 3 | 4 | | | IV-2 | MYO9B | 0.70 |
| 4628 | 3 | 4 | | | IV-2 | MIER1 | 0.94 | 4724 | 3 | 4 | | | IV-2 | MYZAP | 0.76 |
| 4629 | 3 | 4 | | | IV-2 | MINOS1 | 0.80 | 4725 | 3 | 4 | | | IV-2 | N4BP2L1 | 0.93 |
| 4630 | 3 | 4 | | | IV-2 | MIPEP | 0.73 | 4726 | 3 | 4 | | | IV-2 | NAA20 | 0.83 |
| 4631 | 3 | 4 | | | IV-2 | MIR210HG | 0.93 | 4727 | 3 | 4 | | | IV-2 | NAAA | 0.83 |
| 4632 | 3 | 4 | | | IV-2 | MIR3648 | 0.97 | 4728 | 3 | 4 | | | IV-2 | NACA | 0.74 |
| 4633 | 3 | 4 | | | IV-2 | MIS18A | 0.89 | 4729 | 3 | 4 | | | IV-2 | NACA2 | 1.00 |
| 4634 | 3 | 4 | | | IV-2 | MKI67IP | 0.84 | 4730 | 3 | 4 | | | IV-2 | NACAP1 | 0.86 |
| 4635 | 3 | 4 | | | IV-2 | MKKS | 0.80 | 4731 | 3 | 4 | | | IV-2 | NADK | 0.77 |
| 4636 | 3 | 4 | | | IV-2 | MLH1 | 0.95 | 4732 | 3 | 4 | | | IV-2 | NADSYN1 | 0.97 |
| 4637 | 3 | 4 | | | IV-2 | MLL2 | 0.94 | 4733 | 3 | 4 | | | IV-2 | NAE1 | 0.89 |
| 4638 | 3 | 4 | | | IV-2 | MLLT3 | 0.92 | 4734 | 3 | 4 | | | IV-2 | NAF1 | 0.98 |
| 4639 | 3 | 4 | | | IV-2 | MLLT6 | 0.74 | 4735 | 3 | 4 | | | IV-2 | NAGK | 0.83 |
| 4640 | 3 | 4 | | | IV-2 | MLX | 0.71 | 4736 | 3 | 4 | | | IV-2 | NAGLU | 0.72 |
| 4641 | 3 | 4 | | | IV-2 | MMACHC | 0.76 | 4737 | 3 | 4 | | | IV-2 | NAGS | 0.98 |
| 4642 | 3 | 4 | | | IV-2 | MMADHC | 0.97 | 4738 | 3 | 4 | | | IV-2 | NANOS1 | 0.93 |
| 4643 | 3 | 4 | | | IV-2 | MMD | 0.97 | 4739 | 3 | 4 | | | IV-2 | NANP | 0.88 |
| 4644 | 3 | 4 | | | IV-2 | MMP2 | 0.77 | 4740 | 3 | 4 | | | IV-2 | NAP1L4 | 0.89 |
| 4645 | 3 | 4 | | | IV-2 | MMP24 | 0.73 | 4741 | 3 | 4 | | | IV-2 | NAPRT1 | 0.74 |
| 4646 | 3 | 4 | | | IV-2 | MNAT1 | 0.97 | 4742 | 3 | 4 | | | IV-2 | NARFL | 0.79 |
| 4647 | 3 | 4 | | | IV-2 | MNF1 | 0.96 | 4743 | 3 | 4 | | | IV-2 | NARS | 0.95 |
| 4648 | 3 | 4 | | | IV-2 | MOB2 | 0.75 | 4744 | 3 | 4 | | | IV-2 | NAT10 | 0.70 |
| 4649 | 3 | 4 | | | IV-2 | MOCS1 | 0.73 | 4745 | 3 | 4 | | | IV-2 | NAT14 | 0.72 |
| 4650 | 3 | 4 | | | IV-2 | MORF4L1 | 0.94 | 4746 | 3 | 4 | | | IV-2 | NBEAL2 | 0.75 |
| 4651 | 3 | 4 | | | IV-2 | MORF4L2 | 0.89 | 4747 | 3 | 4 | | | IV-2 | NBR1 | 0.94 |
| 4652 | 3 | 4 | | | IV-2 | MORN4 | 0.87 | 4748 | 3 | 4 | | | IV-2 | NCBP2 | 0.98 |
| 4653 | 3 | 4 | | | IV-2 | MOV10 | 0.68 | 4749 | 3 | 4 | | | IV-2 | NCKAP1 | 0.86 |
| 4654 | 3 | 4 | | | IV-2 | MPI | 0.77 | 4750 | 3 | 4 | | | IV-2 | NCL | 0.80 |
| 4655 | 3 | 4 | | | IV-2 | MPP1 | 0.91 | 4751 | 3 | 4 | | | IV-2 | NCSTN | 0.67 |
| 4656 | 3 | 4 | | | IV-2 | MPPE1 | 0.82 | 4752 | 3 | 4 | | | IV-2 | NDFIP1 | 0.88 |
| 4657 | 3 | 4 | | | IV-2 | MPPED2 | 0.93 | 4753 | 3 | 4 | | | IV-2 | NDN | 0.76 |
| 4658 | 3 | 4 | | | IV-2 | MPV17 | 0.73 | 4754 | 3 | 4 | | | IV-2 | NDNF | 0.77 |
| 4659 | 3 | 4 | | | IV-2 | MPV17L2 | 0.78 | 4755 | 3 | 4 | | | IV-2 | NDRG4 | 0.96 |
| 4660 | 3 | 4 | | | IV-2 | MPZL1 | 0.76 | 4756 | 3 | 4 | | | IV-2 | NDST2 | 0.97 |
| 4661 | 3 | 4 | | | IV-2 | MRAP | 0.88 | 4757 | 3 | 4 | | | IV-2 | NDUFA12 | 0.80 |
| 4662 | 3 | 4 | | | IV-2 | MRC2 | 0.77 | 4758 | 3 | 4 | | | IV-2 | NDUFA3 | 0.83 |
| 4663 | 3 | 4 | | | IV-2 | MRFAP1 | 0.72 | 4759 | 3 | 4 | | | IV-2 | NDUFA4 | 0.85 |
| 4664 | 3 | 4 | | | IV-2 | MRFAP1L1 | 0.77 | 4760 | 3 | 4 | | | IV-2 | NDUFA6 | 0.99 |
| 4665 | 3 | 4 | | | IV-2 | MRPL1 | 0.78 | 4761 | 3 | 4 | | | IV-2 | NDUFA7 | 0.67 |
| 4666 | 3 | 4 | | | IV-2 | MRPL11 | 0.69 | 4762 | 3 | 4 | | | IV-2 | NDUFA9 | 0.73 |
| 4667 | 3 | 4 | | | IV-2 | MRPL15 | 0.91 | 4763 | 3 | 4 | | | IV-2 | NDUFAB1 | 0.72 |
| 4668 | 3 | 4 | | | IV-2 | MRPL20 | 0.98 | 4764 | 3 | 4 | | | IV-2 | NDUFAF3 | 0.72 |
| 4669 | 3 | 4 | | | IV-2 | MRPL21 | 0.84 | 4765 | 3 | 4 | | | IV-2 | NDUFAF4 | 0.80 |
| 4670 | 3 | 4 | | | IV-2 | MRPL3 | 0.77 | 4766 | 3 | 4 | | | IV-2 | NDUFB10 | 0.69 |
| 4671 | 3 | 4 | | | IV-2 | MRPL32 | 0.85 | 4767 | 3 | 4 | | | IV-2 | NDUFB2 | 0.80 |
| 4672 | 3 | 4 | | | IV-2 | MRPL36 | 0.80 | 4768 | 3 | 4 | | | IV-2 | NDUFB5 | 0.87 |
| 4673 | 3 | 4 | | | IV-2 | MRPL39 | 0.71 | 4769 | 3 | 4 | | | IV-2 | NDUFB6 | 0.73 |
| 4674 | 3 | 4 | | | IV-2 | MRPL41 | 0.83 | 4770 | 3 | 4 | | | IV-2 | NDUFB8 | 0.75 |
| 4675 | 3 | 4 | | | IV-2 | MRPL42 | 0.86 | 4771 | 3 | 4 | | | IV-2 | NDUFC1 | 0.90 |
| 4676 | 3 | 4 | | | IV-2 | MRPL43 | 0.67 | 4772 | 3 | 4 | | | IV-2 | NDUFC2 | 0.99 |
| 4677 | 3 | 4 | | | IV-2 | MRPL44 | 0.68 | 4773 | 3 | 4 | | | IV-2 | NDUFS2 | 0.68 |
| 4678 | 3 | 4 | | | IV-2 | MRPL45P2 | 0.87 | 4774 | 3 | 4 | | | IV-2 | NDUFS4 | 1.00 |
| 4679 | 3 | 4 | | | IV-2 | MRPL46 | 0.71 | 4775 | 3 | 4 | | | IV-2 | NDUFS6 | 0.70 |
| 4680 | 3 | 4 | | | IV-2 | MRPL47 | 0.92 | 4776 | 3 | 4 | | | IV-2 | NDUFV2 | 0.69 |
| 4681 | 3 | 4 | | | IV-2 | MRPL48 | 0.73 | 4777 | 3 | 4 | | | IV-2 | NDUFV3 | 0.82 |
| 4682 | 3 | 4 | | | IV-2 | MRPL49 | 0.79 | 4778 | 3 | 4 | | | IV-2 | NECAB3 | 0.79 |
| 4683 | 3 | 4 | | | IV-2 | MRPL50 | 0.91 | 4779 | 3 | 4 | | | IV-2 | NEDD4L | 0.96 |
| 4684 | 3 | 4 | | | IV-2 | MRPL51 | 0.76 | 4780 | 3 | 4 | | | IV-2 | NEDD8 | 0.83 |
| 4685 | 3 | 4 | | | IV-2 | MRPS15 | 0.68 | 4781 | 3 | 4 | | | IV-2 | NEDD9 | 0.85 |
| 4686 | 3 | 4 | | | IV-2 | MRPS16 | 0.78 | 4782 | 3 | 4 | | | IV-2 | NEK8 | 0.85 |
| 4687 | 3 | 4 | | | IV-2 | MRPS17 | 0.84 | 4783 | 3 | 4 | | | IV-2 | NES | 0.76 |
| 4688 | 3 | 4 | | | IV-2 | MRPS22 | 0.86 | 4784 | 3 | 4 | | | IV-2 | NET1 | 0.80 |
| 4689 | 3 | 4 | | | IV-2 | MRPS35 | 0.87 | 4785 | 3 | 4 | | | IV-2 | NEU1 | 0.73 |
| 4690 | 3 | 4 | | | IV-2 | MRPS36 | 0.74 | 4786 | 3 | 4 | | | IV-2 | NEURL2 | 0.85 |
| 4691 | 3 | 4 | | | IV-2 | MRPS6 | 0.80 | 4787 | 3 | 4 | | | IV-2 | NFASC | 0.92 |
| 4692 | 3 | 4 | | | IV-2 | MRPS7 | 0.80 | 4788 | 3 | 4 | | | IV-2 | NFATC3 | 0.84 |
| 4693 | 3 | 4 | | | IV-2 | MRRF | 0.87 | 4789 | 3 | 4 | | | IV-2 | NFIC | 0.73 |
| 4694 | 3 | 4 | | | IV-2 | MSL3P1 | 0.84 | 4790 | 3 | 4 | | | IV-2 | NFKB1 | 0.80 |
| 4695 | 3 | 4 | | | IV-2 | MST1R | 0.68 | 4791 | 3 | 4 | | | IV-2 | NFYB | 0.97 |
| 4696 | 3 | 4 | | | IV-2 | MTA3 | 0.96 | 4792 | 3 | 4 | | | IV-2 | NGFRAP1 | 0.93 |
| 4697 | 3 | 4 | | | IV-2 | MTCH1 | 0.70 | 4793 | 3 | 4 | | | IV-2 | NGLY1 | 0.95 |
| 4698 | 3 | 4 | | | IV-2 | MTCP1NB | 0.79 | 4794 | 3 | 4 | | | IV-2 | NGRN | 0.68 |
| 4699 | 3 | 4 | | | IV-2 | MTG1 | 0.84 | 4795 | 3 | 4 | | | IV-2 | NIF3L1 | 0.77 |
| 4700 | 3 | 4 | | | IV-2 | MTHFSD | 0.86 | 4796 | 3 | 4 | | | IV-2 | NINJ1 | 0.74 |
| 4701 | 3 | 4 | | | IV-2 | MTM1 | 0.96 | 4797 | 3 | 4 | | | IV-2 | NIP7 | 0.93 |

Fig. 38 - 26

| | | | | | | | | | | | | | | |
|---|---|---|---|---|---|---|---|---|---|---|---|---|---|---|
| 4798 | 3 | 4 | | | IV-2 | NIPA2 | 0.94 | 4894 | 3 | 4 | | | IV-2 | PAICS | 0.69 |
| 4799 | 3 | 4 | | | IV-2 | NKAIN1 | 0.93 | 4895 | 3 | 4 | | | IV-2 | PAIP1 | 0.79 |
| 4800 | 3 | 4 | | | IV-2 | NKX3-1 | 0.88 | 4896 | 3 | 4 | | | IV-2 | PAK1IP1 | 0.83 |
| 4801 | 3 | 4 | | | IV-2 | NLGN3 | 0.87 | 4897 | 3 | 4 | | | IV-2 | PANX2 | 0.98 |
| 4802 | 3 | 4 | | | IV-2 | NLRC5 | 0.95 | 4898 | 3 | 4 | | | IV-2 | PAPLN | 0.90 |
| 4803 | 3 | 4 | | | IV-2 | NME2 | 0.69 | 4899 | 3 | 4 | | | IV-2 | PAQR7 | 0.96 |
| 4804 | 3 | 4 | | | IV-2 | NMI | 0.80 | 4900 | 3 | 4 | | | IV-2 | PARK7 | 0.81 |
| 4805 | 3 | 4 | | | IV-2 | NMT1 | 0.83 | 4901 | 3 | 4 | | | IV-2 | PARN | 0.68 |
| 4806 | 3 | 4 | | | IV-2 | NODAL | 0.95 | 4902 | 3 | 4 | | | IV-2 | PARP1 | 0.84 |
| 4807 | 3 | 4 | | | IV-2 | NOL10 | 0.96 | 4903 | 3 | 4 | | | IV-2 | PARP10 | 0.69 |
| 4808 | 3 | 4 | | | IV-2 | NOL11 | 0.96 | 4904 | 3 | 4 | | | IV-2 | PARP12 | 0.74 |
| 4809 | 3 | 4 | | | IV-2 | NOL7 | 0.77 | 4905 | 3 | 4 | | | IV-2 | PARP16 | 0.81 |
| 4810 | 3 | 4 | | | IV-2 | NOMO1 | 0.83 | 4906 | 3 | 4 | | | IV-2 | PARP6 | 0.70 |
| 4811 | 3 | 4 | | | IV-2 | NOMO2 | 0.75 | 4907 | 3 | 4 | | | IV-2 | PARVA | 0.96 |
| 4812 | 3 | 4 | | | IV-2 | NOMO3 | 0.73 | 4908 | 3 | 4 | | | IV-2 | PATL1 | 0.72 |
| 4813 | 3 | 4 | | | IV-2 | NOP10 | 0.69 | 4909 | 3 | 4 | | | IV-2 | PAXIP1 | 0.98 |
| 4814 | 3 | 4 | | | IV-2 | NOP14-AS1 | 0.84 | 4910 | 3 | 4 | | | IV-2 | PBX3 | 0.98 |
| 4815 | 3 | 4 | | | IV-2 | NOP56 | 0.73 | 4911 | 3 | 4 | | | IV-2 | PBXIP1 | 0.75 |
| 4816 | 3 | 4 | | | IV-2 | NOS3 | 0.82 | 4912 | 3 | 4 | | | IV-2 | PC | 0.91 |
| 4817 | 3 | 4 | | | IV-2 | NOTCH1 | 0.73 | 4913 | 3 | 4 | | | IV-2 | PCBP2 | 0.71 |
| 4818 | 3 | 4 | | | IV-2 | NPBWR1 | 0.97 | 4914 | 3 | 4 | | | IV-2 | PCDHB2 | 0.89 |
| 4819 | 3 | 4 | | | IV-2 | NPC2 | 0.97 | 4915 | 3 | 4 | | | IV-2 | PCGF1 | 0.89 |
| 4820 | 3 | 4 | | | IV-2 | NPEPPS | 0.91 | 4916 | 3 | 4 | | | IV-2 | PCGF5 | 0.86 |
| 4821 | 3 | 4 | | | IV-2 | NPHP1 | 0.98 | 4917 | 3 | 4 | | | IV-2 | PCX2 | 0.90 |
| 4822 | 3 | 4 | | | IV-2 | NPLOC4 | 0.71 | 4918 | 3 | 4 | | | IV-2 | PCMT1 | 0.80 |
| 4823 | 3 | 4 | | | IV-2 | NPM1 | 0.74 | 4919 | 3 | 4 | | | IV-2 | PCNA | 0.78 |
| 4824 | 3 | 4 | | | IV-2 | NPM3 | 0.71 | 4920 | 3 | 4 | | | IV-2 | PCNT | 0.99 |
| 4825 | 3 | 4 | | | IV-2 | NPR3 | 0.87 | 4921 | 3 | 4 | | | IV-2 | PCSK7 | 0.68 |
| 4826 | 3 | 4 | | | IV-2 | NPTN | 0.94 | 4922 | 3 | 4 | | | IV-2 | PDCD2 | 0.82 |
| 4827 | 3 | 4 | | | IV-2 | NPW | 0.92 | 4923 | 3 | 4 | | | IV-2 | PDCD6 | 0.81 |
| 4828 | 3 | 4 | | | IV-2 | NPY5R | 0.95 | 4924 | 3 | 4 | | | IV-2 | PDCD6IP | 0.92 |
| 4829 | 3 | 4 | | | IV-2 | NR2F2 | 0.71 | 4925 | 3 | 4 | | | IV-2 | PDCD7 | 0.95 |
| 4830 | 3 | 4 | | | IV-2 | NREP | 0.84 | 4926 | 3 | 4 | | | IV-2 | PDDC1 | 0.69 |
| 4831 | 3 | 4 | | | IV-2 | NRF1 | 0.80 | 4927 | 3 | 4 | | | IV-2 | PDE4D | 0.69 |
| 4832 | 3 | 4 | | | IV-2 | NRXN2 | 0.78 | 4928 | 3 | 4 | | | IV-2 | PDE6G | 0.93 |
| 4833 | 3 | 4 | | | IV-2 | NSL1 | 1.00 | 4929 | 3 | 4 | | | IV-2 | PDF | 0.81 |
| 4834 | 3 | 4 | | | IV-2 | NSMCE2 | 0.82 | 4930 | 3 | 4 | | | IV-2 | PDGFRB | 0.71 |
| 4835 | 3 | 4 | | | IV-2 | NSMCE4A | 0.81 | 4931 | 3 | 4 | | | IV-2 | PDHB | 0.87 |
| 4836 | 3 | 4 | | | IV-2 | NSUN2 | 0.89 | 4932 | 3 | 4 | | | IV-2 | PDIA3 | 0.82 |
| 4837 | 3 | 4 | | | IV-2 | NT5C3 | 0.89 | 4933 | 3 | 4 | | | IV-2 | PDIA4 | 0.67 |
| 4838 | 3 | 4 | | | IV-2 | NTHL1 | 0.74 | 4934 | 3 | 4 | | | IV-2 | PDLIM5 | 0.99 |
| 4839 | 3 | 4 | | | IV-2 | NTRK3 | 0.96 | 4935 | 3 | 4 | | | IV-2 | PDPN | 0.87 |
| 4840 | 3 | 4 | | | IV-2 | NUB1 | 0.87 | 4936 | 3 | 4 | | | IV-2 | PDRG1 | 0.94 |
| 4841 | 3 | 4 | | | IV-2 | NUDCD2 | 0.70 | 4937 | 3 | 4 | | | IV-2 | PDSS1 | 0.68 |
| 4842 | 3 | 4 | | | IV-2 | NUDT10 | 1.00 | 4938 | 3 | 4 | | | IV-2 | PDXDC1 | 0.84 |
| 4843 | 3 | 4 | | | IV-2 | NUDT15 | 0.73 | 4939 | 3 | 4 | | | IV-2 | PDXK | 0.94 |
| 4844 | 3 | 4 | | | IV-2 | NUDT16L1 | 0.67 | 4940 | 3 | 4 | | | IV-2 | PDZD4 | 0.74 |
| 4845 | 3 | 4 | | | IV-2 | NUDT16P1 | 0.97 | 4941 | 3 | 4 | | | IV-2 | PDZD7 | 0.80 |
| 4846 | 3 | 4 | | | IV-2 | NUDT2 | 0.89 | 4942 | 3 | 4 | | | IV-2 | PEA15 | 0.67 |
| 4847 | 3 | 4 | | | IV-2 | NUDT3 | 0.76 | 4943 | 3 | 4 | | | IV-2 | PEBP1 | 0.72 |
| 4848 | 3 | 4 | | | IV-2 | NUDT4 | 0.95 | 4944 | 3 | 4 | | | IV-2 | PELO | 0.69 |
| 4849 | 3 | 4 | | | IV-2 | NUDT5 | 0.89 | 4945 | 3 | 4 | | | IV-2 | PEPD | 0.76 |
| 4850 | 3 | 4 | | | IV-2 | NUDT6 | 0.81 | 4946 | 3 | 4 | | | IV-2 | PET112 | 0.95 |
| 4851 | 3 | 4 | | | IV-2 | NUDT9 | 0.82 | 4947 | 3 | 4 | | | IV-2 | PEX11B | 0.75 |
| 4852 | 3 | 4 | | | IV-2 | NUFIP1 | 0.76 | 4948 | 3 | 4 | | | IV-2 | PEX11G | 0.81 |
| 4853 | 3 | 4 | | | IV-2 | NUP160 | 0.82 | 4949 | 3 | 4 | | | IV-2 | PEX12 | 0.98 |
| 4854 | 3 | 4 | | | IV-2 | NUP214 | 0.77 | 4950 | 3 | 4 | | | IV-2 | PEX6 | 0.76 |
| 4855 | 3 | 4 | | | IV-2 | NUP35 | 0.97 | 4951 | 3 | 4 | | | IV-2 | PEX7 | 0.88 |
| 4856 | 3 | 4 | | | IV-2 | NUP54 | 0.92 | 4952 | 3 | 4 | | | IV-2 | PFAS | 0.67 |
| 4857 | 3 | 4 | | | IV-2 | NUP88 | 0.95 | 4953 | 3 | 4 | | | IV-2 | PFKM | 0.97 |
| 4858 | 3 | 4 | | | IV-2 | NUP98 | 0.88 | 4954 | 3 | 4 | | | IV-2 | PFN2 | 0.88 |
| 4859 | 3 | 4 | | | IV-2 | NUPR1 | 0.72 | 4955 | 3 | 4 | | | IV-2 | PGAP2 | 0.89 |
| 4860 | 3 | 4 | | | IV-2 | NVL | 0.92 | 4956 | 3 | 4 | | | IV-2 | PGK1 | 0.86 |
| 4861 | 3 | 4 | | | IV-2 | OASL | 0.93 | 4957 | 3 | 4 | | | IV-2 | PGM1 | 0.74 |
| 4862 | 3 | 4 | | | IV-2 | OAT | 0.79 | 4958 | 3 | 4 | | | IV-2 | PGM5P2 | 0.88 |
| 4863 | 3 | 4 | | | IV-2 | OBFC1 | 0.86 | 4959 | 3 | 4 | | | IV-2 | PGP | 0.70 |
| 4864 | 3 | 4 | | | IV-2 | OCA2 | 0.93 | 4960 | 3 | 4 | | | IV-2 | PGPEP1 | 0.90 |
| 4865 | 3 | 4 | | | IV-2 | OCIAD1 | 0.78 | 4961 | 3 | 4 | | | IV-2 | PHF10 | 0.89 |
| 4866 | 3 | 4 | | | IV-2 | ODF2 | 0.67 | 4962 | 3 | 4 | | | IV-2 | PHF12 | 0.72 |
| 4867 | 3 | 4 | | | IV-2 | OGFOD1 | 0.73 | 4963 | 3 | 4 | | | IV-2 | PHF13 | 0.78 |
| 4868 | 3 | 4 | | | IV-2 | OGFOD2 | 0.70 | 4964 | 3 | 4 | | | IV-2 | PHF17 | 0.80 |
| 4869 | 3 | 4 | | | IV-2 | OLFML2A | 0.74 | 4965 | 3 | 4 | | | IV-2 | PHF19 | 0.76 |
| 4870 | 3 | 4 | | | IV-2 | OLFML2B | 0.73 | 4966 | 3 | 4 | | | IV-2 | PHF2 | 0.76 |
| 4871 | 3 | 4 | | | IV-2 | OMA1 | 0.97 | 4967 | 3 | 4 | | | IV-2 | PHF21A | 0.82 |
| 4872 | 3 | 4 | | | IV-2 | OPN3 | 0.74 | 4968 | 3 | 4 | | | IV-2 | PHF23 | 0.75 |
| 4873 | 3 | 4 | | | IV-2 | OPRL1 | 0.99 | 4969 | 3 | 4 | | | IV-2 | PHF3 | 0.97 |
| 4874 | 3 | 4 | | | IV-2 | OPTN | 0.98 | 4970 | 3 | 4 | | | IV-2 | PHF8 | 0.88 |
| 4875 | 3 | 4 | | | IV-2 | ORS2N4 | 0.98 | 4971 | 3 | 4 | | | IV-2 | PHKG1 | 0.68 |
| 4876 | 3 | 4 | | | IV-2 | ORMDL2 | 0.86 | 4972 | 3 | 4 | | | IV-2 | PHLDA1 | 0.90 |
| 4877 | 3 | 4 | | | IV-2 | OSBPL2 | 0.97 | 4973 | 3 | 4 | | | IV-2 | PHLDA3 | 0.69 |
| 4878 | 3 | 4 | | | IV-2 | OSCP1 | 0.77 | 4974 | 3 | 4 | | | IV-2 | PHLDB3 | 0.68 |
| 4879 | 3 | 4 | | | IV-2 | OSMR | 0.99 | 4975 | 3 | 4 | | | IV-2 | PHYH | 0.74 |
| 4880 | 3 | 4 | | | IV-2 | OST4 | 0.85 | 4976 | 3 | 4 | | | IV-2 | PHYHIPL | 0.87 |
| 4881 | 3 | 4 | | | IV-2 | OSTC | 0.80 | 4977 | 3 | 4 | | | IV-2 | PI4K2A | 0.81 |
| 4882 | 3 | 4 | | | IV-2 | OTUD7B | 0.90 | 4978 | 3 | 4 | | | IV-2 | PI4KA | 0.80 |
| 4883 | 3 | 4 | | | IV-2 | OXA1L | 0.80 | 4979 | 3 | 4 | | | IV-2 | PI4KB | 0.69 |
| 4884 | 3 | 4 | | | IV-2 | OXSM | 0.74 | 4980 | 3 | 4 | | | IV-2 | PIAS3 | 0.79 |
| 4885 | 3 | 4 | | | IV-2 | OXSR1 | 0.87 | 4981 | 3 | 4 | | | IV-2 | PIEZO1 | 0.77 |
| 4886 | 3 | 4 | | | IV-2 | P2RX4 | 0.84 | 4982 | 3 | 4 | | | IV-2 | PIF1 | 0.93 |
| 4887 | 3 | 4 | | | IV-2 | P2RY11 | 0.72 | 4983 | 3 | 4 | | | IV-2 | PIGB | 0.90 |
| 4888 | 3 | 4 | | | IV-2 | P4HA1 | 0.79 | 4984 | 3 | 4 | | | IV-2 | PIGH | 0.99 |
| 4889 | 3 | 4 | | | IV-2 | P4HTM | 0.76 | 4985 | 3 | 4 | | | IV-2 | PIGO | 0.90 |
| 4890 | 3 | 4 | | | IV-2 | PAAF1 | 0.85 | 4986 | 3 | 4 | | | IV-2 | PIGY | 0.89 |
| 4891 | 3 | 4 | | | IV-2 | PACRG | 0.99 | 4987 | 3 | 4 | | | IV-2 | PIK3C8 | 0.92 |
| 4892 | 3 | 4 | | | IV-2 | PACSIN2 | 0.80 | 4988 | 3 | 4 | | | IV-2 | PIK3IP1 | 0.92 |
| 4893 | 3 | 4 | | | IV-2 | PAFAH1B2 | 0.94 | 4989 | 3 | 4 | | | IV-2 | PIK3R6 | 0.74 |

Fig. 38 - 27

| | | | | | | | | | | | | | | | |
|---|---|---|---|---|---|---|---|---|---|---|---|---|---|---|---|
| 4990 | 3 | 4 | | | IV-2 | PIP4K2A | 0.94 | 5086 | 3 | 4 | | | IV-2 | PRAM1 | 0.96 |
| 4991 | 3 | 4 | | | IV-2 | PIP4K2B | 0.99 | 5087 | 3 | 4 | | | IV-2 | PRC1 | 0.74 |
| 4992 | 3 | 4 | | | IV-2 | PIP4K2C | 0.68 | 5088 | 3 | 4 | | | IV-2 | PRCP | 0.99 |
| 4993 | 3 | 4 | | | IV-2 | PIP5K1A | 0.88 | 5089 | 3 | 4 | | | IV-2 | PRDX4 | 0.89 |
| 4994 | 3 | 4 | | | IV-2 | PIP5K1B | 0.98 | 5090 | 3 | 4 | | | IV-2 | PREB | 0.67 |
| 4995 | 3 | 4 | | | IV-2 | PIPSL | 0.77 | 5091 | 3 | 4 | | | IV-2 | PRELP | 0.86 |
| 4996 | 3 | 4 | | | IV-2 | PITHD1 | 0.78 | 5092 | 3 | 4 | | | IV-2 | PREP | 0.84 |
| 4997 | 3 | 4 | | | IV-2 | PITPNB | 0.91 | 5093 | 3 | 4 | | | IV-2 | PRIC285 | 0.88 |
| 4998 | 3 | 4 | | | IV-2 | PJA1 | 0.74 | 5094 | 3 | 4 | | | IV-2 | PRIM2 | 0.83 |
| 4999 | 3 | 4 | | | IV-2 | PKD1 | 0.84 | 5095 | 3 | 4 | | | IV-2 | PRIMA1 | 0.87 |
| 5000 | 3 | 4 | | | IV-2 | PKIA | 0.97 | 5096 | 3 | 4 | | | IV-2 | PRKAB1 | 0.76 |
| 5001 | 3 | 4 | | | IV-2 | PKP4 | 0.94 | 5097 | 3 | 4 | | | IV-2 | PRKAG2 | 0.93 |
| 5002 | 3 | 4 | | | IV-2 | PLA2G15 | 0.85 | 5098 | 3 | 4 | | | IV-2 | PRKCD | 0.70 |
| 5003 | 3 | 4 | | | IV-2 | PLA2G4A | 0.98 | 5099 | 3 | 4 | | | IV-2 | PRKCZ | 0.72 |
| 5004 | 3 | 4 | | | IV-2 | PLA2G4B | 0.76 | 5100 | 3 | 4 | | | IV-2 | PRKDC | 0.83 |
| 5005 | 3 | 4 | | | IV-2 | PLA2G5 | 0.68 | 5101 | 3 | 4 | | | IV-2 | PRKRA | 0.77 |
| 5006 | 3 | 4 | | | IV-2 | PLAA | 0.97 | 5102 | 3 | 4 | | | IV-2 | PRMT2 | 0.88 |
| 5007 | 3 | 4 | | | IV-2 | PLCD1 | 0.76 | 5103 | 3 | 4 | | | IV-2 | PRMT5 | 0.74 |
| 5008 | 3 | 4 | | | IV-2 | PLCG2 | 0.99 | 5104 | 3 | 4 | | | IV-2 | PRMT7 | 0.92 |
| 5009 | 3 | 4 | | | IV-2 | PLD4 | 0.97 | 5105 | 3 | 4 | | | IV-2 | PROCA1 | 0.76 |
| 5010 | 3 | 4 | | | IV-2 | PLEKHA3 | 0.93 | 5106 | 3 | 4 | | | IV-2 | PROCR | 0.93 |
| 5011 | 3 | 4 | | | IV-2 | PLEKHA6 | 0.92 | 5107 | 3 | 4 | | | IV-2 | PROSC | 0.94 |
| 5012 | 3 | 4 | | | IV-2 | PLEKHA7 | 0.98 | 5108 | 3 | 4 | | | IV-2 | PRPF18 | 0.99 |
| 5013 | 3 | 4 | | | IV-2 | PLEKHG1 | 0.91 | 5109 | 3 | 4 | | | IV-2 | PRPF4 | 0.79 |
| 5014 | 3 | 4 | | | IV-2 | PLEKHJ1 | 0.80 | 5110 | 3 | 4 | | | IV-2 | PRPS1 | 0.95 |
| 5015 | 3 | 4 | | | IV-2 | PLEKHM1 | 0.76 | 5111 | 3 | 4 | | | IV-2 | PRPS2 | 0.81 |
| 5016 | 3 | 4 | | | IV-2 | PLEKHN1 | 0.72 | 5112 | 3 | 4 | | | IV-2 | PRPSAP1 | 0.75 |
| 5017 | 3 | 4 | | | IV-2 | PLEKHO1 | 0.72 | 5113 | 3 | 4 | | | IV-2 | PRPSAP2 | 0.93 |
| 5018 | 3 | 4 | | | IV-2 | PLEKHO2 | 0.94 | 5114 | 3 | 4 | | | IV-2 | PRR11 | 0.71 |
| 5019 | 3 | 4 | | | IV-2 | PLP1 | 0.90 | 5115 | 3 | 4 | | | IV-2 | PRR13 | 0.87 |
| 5020 | 3 | 4 | | | IV-2 | PLRG1 | 0.99 | 5116 | 3 | 4 | | | IV-2 | PRSS12 | 0.80 |
| 5021 | 3 | 4 | | | IV-2 | PLS1 | 0.99 | 5117 | 3 | 4 | | | IV-2 | PRSS21 | 0.97 |
| 5022 | 3 | 4 | | | IV-2 | PLXNA1 | 0.80 | 5118 | 3 | 4 | | | IV-2 | PRSS36 | 0.76 |
| 5023 | 3 | 4 | | | IV-2 | PLXNA2 | 0.81 | 5119 | 3 | 4 | | | IV-2 | PSD4 | 0.72 |
| 5024 | 3 | 4 | | | IV-2 | PLXND1 | 0.80 | 5120 | 3 | 4 | | | IV-2 | PSG4 | 0.95 |
| 5025 | 3 | 4 | | | IV-2 | PMM1 | 0.71 | 5121 | 3 | 4 | | | IV-2 | PSIMCT-1 | 0.85 |
| 5026 | 3 | 4 | | | IV-2 | PMM2 | 0.70 | 5122 | 3 | 4 | | | IV-2 | PSMA1 | 0.92 |
| 5027 | 3 | 4 | | | IV-2 | PMPCA | 0.69 | 5123 | 3 | 4 | | | IV-2 | PSMA2 | 0.92 |
| 5028 | 3 | 4 | | | IV-2 | PMS2P1 | 0.97 | 5124 | 3 | 4 | | | IV-2 | PSMA6 | 0.80 |
| 5029 | 3 | 4 | | | IV-2 | PMS2P5 | 0.77 | 5125 | 3 | 4 | | | IV-2 | PSMA7 | 0.92 |
| 5030 | 3 | 4 | | | IV-2 | PNMA1 | 0.73 | 5126 | 3 | 4 | | | IV-2 | PSMB1 | 0.85 |
| 5031 | 3 | 4 | | | IV-2 | PNMAL2 | 0.71 | 5127 | 3 | 4 | | | IV-2 | PSMB3 | 0.84 |
| 5032 | 3 | 4 | | | IV-2 | PNO1 | 0.93 | 5128 | 3 | 4 | | | IV-2 | PSMB4 | 0.73 |
| 5033 | 3 | 4 | | | IV-2 | PNP | 0.95 | 5129 | 3 | 4 | | | IV-2 | PSMB9 | 0.67 |
| 5034 | 3 | 4 | | | IV-2 | PNPLA7 | 0.83 | 5130 | 3 | 4 | | | IV-2 | PSMC1 | 0.91 |
| 5035 | 3 | 4 | | | IV-2 | PNPO | 0.74 | 5131 | 3 | 4 | | | IV-2 | PSMC2 | 0.83 |
| 5036 | 3 | 4 | | | IV-2 | PODNL1 | 0.86 | 5132 | 3 | 4 | | | IV-2 | PSMD10 | 0.78 |
| 5037 | 3 | 4 | | | IV-2 | POGK | 0.91 | 5133 | 3 | 4 | | | IV-2 | PSMD14 | 0.94 |
| 5038 | 3 | 4 | | | IV-2 | POLA1 | 0.76 | 5134 | 3 | 4 | | | IV-2 | PSMD5 | 0.87 |
| 5039 | 3 | 4 | | | IV-2 | POLD3 | 0.88 | 5135 | 3 | 4 | | | IV-2 | PSMD6 | 0.99 |
| 5040 | 3 | 4 | | | IV-2 | POLE4 | 0.68 | 5136 | 3 | 4 | | | IV-2 | PSMD7 | 0.94 |
| 5041 | 3 | 4 | | | IV-2 | POLL | 0.73 | 5137 | 3 | 4 | | | IV-2 | PSMG1 | 0.83 |
| 5042 | 3 | 4 | | | IV-2 | POLR1E | 0.72 | 5138 | 3 | 4 | | | IV-2 | PSPC1 | 0.90 |
| 5043 | 3 | 4 | | | IV-2 | POLR2C | 0.72 | 5139 | 3 | 4 | | | IV-2 | PSPH | 0.95 |
| 5044 | 3 | 4 | | | IV-2 | POLR2G | 0.72 | 5140 | 3 | 4 | | | IV-2 | PTBP3 | 0.82 |
| 5045 | 3 | 4 | | | IV-2 | POLR2J4 | 0.88 | 5141 | 3 | 4 | | | IV-2 | PTCH2 | 0.82 |
| 5046 | 3 | 4 | | | IV-2 | POLR2K | 0.77 | 5142 | 3 | 4 | | | IV-2 | PTGES3 | 0.82 |
| 5047 | 3 | 4 | | | IV-2 | POLR3C | 0.91 | 5143 | 3 | 4 | | | IV-2 | PTGR1 | 0.88 |
| 5048 | 3 | 4 | | | IV-2 | POLR3D | 0.94 | 5144 | 3 | 4 | | | IV-2 | PTGR2 | 0.92 |
| 5049 | 3 | 4 | | | IV-2 | POLR3E | 0.78 | 5145 | 3 | 4 | | | IV-2 | PTP4A2 | 0.97 |
| 5050 | 3 | 4 | | | IV-2 | POLR3GL | 0.67 | 5146 | 3 | 4 | | | IV-2 | PTPLAD1 | 0.82 |
| 5051 | 3 | 4 | | | IV-2 | POLR3K | 0.86 | 5147 | 3 | 4 | | | IV-2 | PTPN1 | 0.85 |
| 5052 | 3 | 4 | | | IV-2 | POP4 | 0.69 | 5148 | 3 | 4 | | | IV-2 | PTPN6 | 0.68 |
| 5053 | 3 | 4 | | | IV-2 | POPDC2 | 0.93 | 5149 | 3 | 4 | | | IV-2 | PTPN9 | 0.74 |
| 5054 | 3 | 4 | | | IV-2 | PPA2 | 0.89 | 5150 | 3 | 4 | | | IV-2 | PTPRA | 0.83 |
| 5055 | 3 | 4 | | | IV-2 | PPAPDC1B | 0.90 | 5151 | 3 | 4 | | | IV-2 | PTPRN2 | 0.81 |
| 5056 | 3 | 4 | | | IV-2 | PPCS | 0.83 | 5152 | 3 | 4 | | | IV-2 | PTPRS | 0.71 |
| 5057 | 3 | 4 | | | IV-2 | PPFIA1 | 0.97 | 5153 | 3 | 4 | | | IV-2 | PTRH2 | 0.84 |
| 5058 | 3 | 4 | | | IV-2 | PPFIBP1 | 0.90 | 5154 | 3 | 4 | | | IV-2 | PTRHD1 | 0.67 |
| 5059 | 3 | 4 | | | IV-2 | PPHLN1 | 0.92 | 5155 | 3 | 4 | | | IV-2 | PUS1 | 0.70 |
| 5060 | 3 | 4 | | | IV-2 | PPIC | 0.82 | 5156 | 3 | 4 | | | IV-2 | PUS7 | 0.85 |
| 5061 | 3 | 4 | | | IV-2 | PPIP5K1 | 0.83 | 5157 | 3 | 4 | | | IV-2 | PUSL1 | 0.72 |
| 5062 | 3 | 4 | | | IV-2 | PPM1D | 0.89 | 5158 | 3 | 4 | | | IV-2 | PWP2 | 0.74 |
| 5063 | 3 | 4 | | | IV-2 | PPM1F | 0.85 | 5159 | 3 | 4 | | | IV-2 | PXDN | 0.98 |
| 5064 | 3 | 4 | | | IV-2 | PPM1M | 0.75 | 5160 | 3 | 4 | | | IV-2 | PXK | 0.89 |
| 5065 | 3 | 4 | | | IV-2 | PPM1N | 0.90 | 5161 | 3 | 4 | | | IV-2 | PYCR2 | 0.68 |
| 5066 | 3 | 4 | | | IV-2 | PPP1CC | 0.80 | 5162 | 3 | 4 | | | IV-2 | PYGM | 0.85 |
| 5067 | 3 | 4 | | | IV-2 | PPP1R10 | 0.90 | 5163 | 3 | 4 | | | IV-2 | QDPR | 0.81 |
| 5068 | 3 | 4 | | | IV-2 | PPP1R16B | 0.96 | 5164 | 3 | 4 | | | IV-2 | QPCTL | 0.70 |
| 5069 | 3 | 4 | | | IV-2 | PPP1R26 | 0.68 | 5165 | 3 | 4 | | | IV-2 | QRICH1 | 0.70 |
| 5070 | 3 | 4 | | | IV-2 | PPP1R32 | 0.93 | 5166 | 3 | 4 | | | IV-2 | QSOX2 | 0.98 |
| 5071 | 3 | 4 | | | IV-2 | PPP1R3F | 0.83 | 5167 | 3 | 4 | | | IV-2 | R3HDM1 | 0.94 |
| 5072 | 3 | 4 | | | IV-2 | PPP1R3G | 0.88 | 5168 | 3 | 4 | | | IV-2 | RAB12 | 1.00 |
| 5073 | 3 | 4 | | | IV-2 | PPP1R8 | 0.75 | 5169 | 3 | 4 | | | IV-2 | RAB13 | 0.71 |
| 5074 | 3 | 4 | | | IV-2 | PPP2CA | 0.87 | 5170 | 3 | 4 | | | IV-2 | RAB17 | 0.70 |
| 5075 | 3 | 4 | | | IV-2 | PPP2CB | 0.83 | 5171 | 3 | 4 | | | IV-2 | RAB20 | 0.77 |
| 5076 | 3 | 4 | | | IV-2 | PPP2R2A | 0.96 | 5172 | 3 | 4 | | | IV-2 | RAB21 | 0.96 |
| 5077 | 3 | 4 | | | IV-2 | PPP2R2B | 0.77 | 5173 | 3 | 4 | | | IV-2 | RAB22A | 0.97 |
| 5078 | 3 | 4 | | | IV-2 | PPP2R2D | 0.71 | 5174 | 3 | 4 | | | IV-2 | RAB24 | 0.79 |
| 5079 | 3 | 4 | | | IV-2 | PPP2R3A | 0.77 | 5175 | 3 | 4 | | | IV-2 | RAB28 | 0.91 |
| 5080 | 3 | 4 | | | IV-2 | PPP2R5A | 0.80 | 5176 | 3 | 4 | | | IV-2 | RAB2A | 0.81 |
| 5081 | 3 | 4 | | | IV-2 | PPP3CA | 0.93 | 5177 | 3 | 4 | | | IV-2 | RAB2B | 0.89 |
| 5082 | 3 | 4 | | | IV-2 | PPP3CC | 0.67 | 5178 | 3 | 4 | | | IV-2 | RAB3A | 0.78 |
| 5083 | 3 | 4 | | | IV-2 | PPP4R1 | 0.78 | 5179 | 3 | 4 | | | IV-2 | RAB40B | 0.80 |
| 5084 | 3 | 4 | | | IV-2 | PPP6C | 0.83 | 5180 | 3 | 4 | | | IV-2 | RAB6A | 0.89 |
| 5085 | 3 | 4 | | | IV-2 | PPT2 | 0.68 | 5181 | 3 | 4 | | | IV-2 | RAB6B | 0.93 |

Fig. 38 - 28

| | | | | | | | | | | | | | | |
|---|---|---|---|---|---|---|---|---|---|---|---|---|---|---|
| 5182 | 3 | 4 | | | | IV-2 | RAB7A | 0.67 | 5278 | 3 | 4 | | IV-2 | ROPN1 | 0.91 |
| 5183 | 3 | 4 | | | | IV-2 | RAB7L1 | 0.98 | 5279 | 3 | 4 | | IV-2 | RPA1 | 0.83 |
| 5184 | 3 | 4 | | | | IV-2 | RAB8GTA | 0.85 | 5280 | 3 | 4 | | IV-2 | RPA2 | 0.83 |
| 5185 | 3 | 4 | | | | IV-2 | RABL5 | 0.87 | 5281 | 3 | 4 | | IV-2 | RPAP2 | 0.94 |
| 5186 | 3 | 4 | | | | IV-2 | RAD51C | 1.00 | 5282 | 3 | 4 | | IV-2 | RPE | 0.91 |
| 5187 | 3 | 4 | | | | IV-2 | RAE1 | 0.80 | 5283 | 3 | 4 | | IV-2 | RPF1 | 0.77 |
| 5188 | 3 | 4 | | | | IV-2 | RAF1 | 0.77 | 5284 | 3 | 4 | | IV-2 | RPIA | 0.85 |
| 5189 | 3 | 4 | | | | IV-2 | RAI1 | 0.71 | 5285 | 3 | 4 | | IV-2 | RPL10A | 0.75 |
| 5190 | 3 | 4 | | | | IV-2 | RALA | 0.81 | 5286 | 3 | 4 | | IV-2 | RPL11 | 0.86 |
| 5191 | 3 | 4 | | | | IV-2 | RALB | 0.70 | 5287 | 3 | 4 | | IV-2 | RPL15 | 0.73 |
| 5192 | 3 | 4 | | | | IV-2 | RANBP10 | 0.80 | 5288 | 3 | 4 | | IV-2 | RPL17 | 0.83 |
| 5193 | 3 | 4 | | | | IV-2 | RAP1A | 0.99 | 5289 | 3 | 4 | | IV-2 | RPL17-C18ORF32 | 0.71 |
| 5194 | 3 | 4 | | | | IV-2 | RAP1B | 0.90 | 5290 | 3 | 4 | | IV-2 | RPL19 | 0.69 |
| 5195 | 3 | 4 | | | | IV-2 | RAP1GAP | 0.72 | 5291 | 3 | 4 | | IV-2 | RPL19P12 | 0.77 |
| 5196 | 3 | 4 | | | | IV-2 | RAP1GAP2 | 0.70 | 5292 | 3 | 4 | | IV-2 | RPL21P28 | 0.71 |
| 5197 | 3 | 4 | | | | IV-2 | RARRES3 | 0.79 | 5293 | 3 | 4 | | IV-2 | RPL22 | 0.85 |
| 5198 | 3 | 4 | | | | IV-2 | RARS | 0.88 | 5294 | 3 | 4 | | IV-2 | RPL23A | 0.82 |
| 5199 | 3 | 4 | | | | IV-2 | RASA3 | 0.76 | 5295 | 3 | 4 | | IV-2 | RPL23P8 | 0.87 |
| 5200 | 3 | 4 | | | | IV-2 | RASA4P | 0.69 | 5296 | 3 | 4 | | IV-2 | RPL24 | 0.75 |
| 5201 | 3 | 4 | | | | IV-2 | RASD1 | 0.77 | 5297 | 3 | 4 | | IV-2 | RPL26L1 | 0.77 |
| 5202 | 3 | 4 | | | | IV-2 | RASGEF1C | 0.93 | 5298 | 3 | 4 | | IV-2 | RPL27 | 0.72 |
| 5203 | 3 | 4 | | | | IV-2 | RASL10A | 0.68 | 5299 | 3 | 4 | | IV-2 | RPL29P2 | 0.83 |
| 5204 | 3 | 4 | | | | IV-2 | RASL11A | 0.90 | 5300 | 3 | 4 | | IV-2 | RPL30 | 0.78 |
| 5205 | 3 | 4 | | | | IV-2 | RASL12 | 0.96 | 5301 | 3 | 4 | | IV-2 | RPL32 | 0.69 |
| 5206 | 3 | 4 | | | | IV-2 | RASSF9 | 0.77 | 5302 | 3 | 4 | | IV-2 | RPL35A | 0.76 |
| 5207 | 3 | 4 | | | | IV-2 | RAX | 0.89 | 5303 | 3 | 4 | | IV-2 | RPL36 | 0.73 |
| 5208 | 3 | 4 | | | | IV-2 | RB1 | 0.96 | 5304 | 3 | 4 | | IV-2 | RPL36A-HNRNPH2 | 0.86 |
| 5209 | 3 | 4 | | | | IV-2 | RB8P7 | 0.91 | 5305 | 3 | 4 | | IV-2 | RPL37 | 0.74 |
| 5210 | 3 | 4 | | | | IV-2 | RBBP9 | 0.93 | 5306 | 3 | 4 | | IV-2 | RPL37A | 0.70 |
| 5211 | 3 | 4 | | | | IV-2 | RBM14-RBM4 | 0.81 | 5307 | 3 | 4 | | IV-2 | RPL41 | 0.87 |
| 5212 | 3 | 4 | | | | IV-2 | RBM17 | 0.91 | 5308 | 3 | 4 | | IV-2 | RPL5 | 0.90 |
| 5213 | 3 | 4 | | | | IV-2 | RBM19 | 0.96 | 5309 | 3 | 4 | | IV-2 | RPL7 | 0.85 |
| 5214 | 3 | 4 | | | | IV-2 | RBM22 | 0.74 | 5310 | 3 | 4 | | IV-2 | RPLP2 | 0.70 |
| 5215 | 3 | 4 | | | | IV-2 | RBM23 | 0.72 | 5311 | 3 | 4 | | IV-2 | RPN2 | 0.81 |
| 5216 | 3 | 4 | | | | IV-2 | RBM3 | 0.75 | 5312 | 3 | 4 | | IV-2 | RPP38 | 0.80 |
| 5217 | 3 | 4 | | | | IV-2 | RBM4 | 0.79 | 5313 | 3 | 4 | | IV-2 | RPRM | 0.92 |
| 5218 | 3 | 4 | | | | IV-2 | RBM4B | 0.81 | 5314 | 3 | 4 | | IV-2 | RPRML | 1.00 |
| 5219 | 3 | 4 | | | | IV-2 | RBMS2 | 0.83 | 5315 | 3 | 4 | | IV-2 | RPS11 | 0.68 |
| 5220 | 3 | 4 | | | | IV-2 | RBMX | 0.89 | 5316 | 3 | 4 | | IV-2 | RPS12 | 0.80 |
| 5221 | 3 | 4 | | | | IV-2 | RBMX2 | 0.92 | 5317 | 3 | 4 | | IV-2 | RPS23 | 0.99 |
| 5222 | 3 | 4 | | | | IV-2 | RBPMS2 | 0.73 | 5318 | 3 | 4 | | IV-2 | RPS27A | 0.92 |
| 5223 | 3 | 4 | | | | IV-2 | RCAN2 | 0.83 | 5319 | 3 | 4 | | IV-2 | RPS27L | 0.73 |
| 5224 | 3 | 4 | | | | IV-2 | RCCD1 | 0.77 | 5320 | 3 | 4 | | IV-2 | RPS29 | 0.89 |
| 5225 | 3 | 4 | | | | IV-2 | RCN2 | 0.88 | 5321 | 3 | 4 | | IV-2 | RPS2P32 | 0.90 |
| 5226 | 3 | 4 | | | | IV-2 | RDH14 | 0.78 | 5322 | 3 | 4 | | IV-2 | RPS3A | 0.88 |
| 5227 | 3 | 4 | | | | IV-2 | REEP2 | 0.81 | 5323 | 3 | 4 | | IV-2 | RPS6 | 0.74 |
| 5228 | 3 | 4 | | | | IV-2 | REEP5 | 0.96 | 5324 | 3 | 4 | | IV-2 | RPS7 | 0.68 |
| 5229 | 3 | 4 | | | | IV-2 | RELL1 | 0.96 | 5325 | 3 | 4 | | IV-2 | RPS8 | 0.70 |
| 5230 | 3 | 4 | | | | IV-2 | RELL2 | 0.89 | 5326 | 3 | 4 | | IV-2 | RPUSD4 | 0.71 |
| 5231 | 3 | 4 | | | | IV-2 | RELT | 0.68 | 5327 | 3 | 4 | | IV-2 | RRAGA | 0.72 |
| 5232 | 3 | 4 | | | | IV-2 | RENBP | 0.96 | 5328 | 3 | 4 | | IV-2 | RRAGD | 0.98 |
| 5233 | 3 | 4 | | | | IV-2 | REPS1 | 0.88 | 5329 | 3 | 4 | | IV-2 | RRN3P2 | 0.93 |
| 5234 | 3 | 4 | | | | IV-2 | RER1 | 0.77 | 5330 | 3 | 4 | | IV-2 | RRNAD1 | 0.67 |
| 5235 | 3 | 4 | | | | IV-2 | RERE | 0.78 | 5331 | 3 | 4 | | IV-2 | RRP36 | 0.73 |
| 5236 | 3 | 4 | | | | IV-2 | REXO1L2P | 0.93 | 5332 | 3 | 4 | | IV-2 | RRP8 | 0.92 |
| 5237 | 3 | 4 | | | | IV-2 | REXO2 | 0.84 | 5333 | 3 | 4 | | IV-2 | RSL1D1 | 0.89 |
| 5238 | 3 | 4 | | | | IV-2 | REXO4 | 0.76 | 5334 | 3 | 4 | | IV-2 | RSL24D1 | 0.83 |
| 5239 | 3 | 4 | | | | IV-2 | RFWD2 | 0.84 | 5335 | 3 | 4 | | IV-2 | RSPH3 | 0.68 |
| 5240 | 3 | 4 | | | | IV-2 | RFWD3 | 0.81 | 5336 | 3 | 4 | | IV-2 | RSU1 | 0.86 |
| 5241 | 3 | 4 | | | | IV-2 | RFXAP | 0.92 | 5337 | 3 | 4 | | IV-2 | RTCD1 | 0.78 |
| 5242 | 3 | 4 | | | | IV-2 | RGNEF | 0.67 | 5338 | 3 | 4 | | IV-2 | RUFY1 | 0.89 |
| 5243 | 3 | 4 | | | | IV-2 | RGS10 | 0.84 | 5339 | 3 | 4 | | IV-2 | RUNX3 | 0.75 |
| 5244 | 3 | 4 | | | | IV-2 | RGS19 | 0.81 | 5340 | 3 | 4 | | IV-2 | RUSC2 | 0.82 |
| 5245 | 3 | 4 | | | | IV-2 | RHBDD3 | 0.78 | 5341 | 3 | 4 | | IV-2 | RUVBL1 | 0.76 |
| 5246 | 3 | 4 | | | | IV-2 | RHEBL1 | 0.90 | 5342 | 3 | 4 | | IV-2 | RWDD1 | 0.90 |
| 5247 | 3 | 4 | | | | IV-2 | RILPL2 | 0.69 | 5343 | 3 | 4 | | IV-2 | RWDD2B | 0.71 |
| 5248 | 3 | 4 | | | | IV-2 | RINL | 0.70 | 5344 | 3 | 4 | | IV-2 | RWDD3 | 0.96 |
| 5249 | 3 | 4 | | | | IV-2 | RIPK4 | 0.67 | 5345 | 3 | 4 | | IV-2 | RWDD4 | 0.96 |
| 5250 | 3 | 4 | | | | IV-2 | RLF | 0.96 | 5346 | 3 | 4 | | IV-2 | RYR1 | 0.97 |
| 5251 | 3 | 4 | | | | IV-2 | RMND1 | 0.99 | 5347 | 3 | 4 | | IV-2 | SAAL1 | 0.98 |
| 5252 | 3 | 4 | | | | IV-2 | RN45S | 0.93 | 5348 | 3 | 4 | | IV-2 | SAFB | 0.78 |
| 5253 | 3 | 4 | | | | IV-2 | RNASE13 | 0.95 | 5349 | 3 | 4 | | IV-2 | SAFB2 | 0.86 |
| 5254 | 3 | 4 | | | | IV-2 | RNASEH2B | 0.86 | 5350 | 3 | 4 | | IV-2 | SAMM50 | 0.68 |
| 5255 | 3 | 4 | | | | IV-2 | RND2 | 0.83 | 5351 | 3 | 4 | | IV-2 | SAP18 | 0.76 |
| 5256 | 3 | 4 | | | | IV-2 | RNF113A | 0.71 | 5352 | 3 | 4 | | IV-2 | SARM1 | 0.84 |
| 5257 | 3 | 4 | | | | IV-2 | RNF114 | 0.83 | 5353 | 3 | 4 | | IV-2 | SART3 | 0.99 |
| 5258 | 3 | 4 | | | | IV-2 | RNF13 | 0.96 | 5354 | 3 | 4 | | IV-2 | SAYSD1 | 0.74 |
| 5259 | 3 | 4 | | | | IV-2 | RNF130 | 0.98 | 5355 | 3 | 4 | | IV-2 | SBDS | 0.86 |
| 5260 | 3 | 4 | | | | IV-2 | RNF135 | 0.84 | 5356 | 3 | 4 | | IV-2 | SBF1 | 0.68 |
| 5261 | 3 | 4 | | | | IV-2 | RNF145 | 0.86 | 5357 | 3 | 4 | | IV-2 | SCAF4 | 0.81 |
| 5262 | 3 | 4 | | | | IV-2 | RNF152 | 0.83 | 5358 | 3 | 4 | | IV-2 | SCAF8 | 0.91 |
| 5263 | 3 | 4 | | | | IV-2 | RNF166 | 0.84 | 5359 | 3 | 4 | | IV-2 | SCCPDH | 0.75 |
| 5264 | 3 | 4 | | | | IV-2 | RNF181 | 0.85 | 5360 | 3 | 4 | | IV-2 | SCD5 | 0.87 |
| 5265 | 3 | 4 | | | | IV-2 | RNF185 | 0.75 | 5361 | 3 | 4 | | IV-2 | SCHIP1 | 0.93 |
| 5266 | 3 | 4 | | | | IV-2 | RNF2 | 0.99 | 5362 | 3 | 4 | | IV-2 | SCMH1 | 0.78 |
| 5267 | 3 | 4 | | | | IV-2 | RNF214 | 0.87 | 5363 | 3 | 4 | | IV-2 | SCO1 | 0.84 |
| 5268 | 3 | 4 | | | | IV-2 | RNF216 | 0.89 | 5364 | 3 | 4 | | IV-2 | SCP2 | 0.97 |
| 5269 | 3 | 4 | | | | IV-2 | RNF216P1 | 0.86 | 5365 | 3 | 4 | | IV-2 | SDAD1 | 0.82 |
| 5270 | 3 | 4 | | | | IV-2 | RNF32 | 0.94 | 5366 | 3 | 4 | | IV-2 | SDC3 | 0.80 |
| 5271 | 3 | 4 | | | | IV-2 | RNF34 | 0.85 | 5367 | 3 | 4 | | IV-2 | SDCBP | 0.86 |
| 5272 | 3 | 4 | | | | IV-2 | RNF4 | 0.80 | 5368 | 3 | 4 | | IV-2 | SDCCAG3 | 0.73 |
| 5273 | 3 | 4 | | | | IV-2 | RNF41 | 0.88 | 5369 | 3 | 4 | | IV-2 | SDF2 | 0.77 |
| 5274 | 3 | 4 | | | | IV-2 | RNF43 | 0.75 | 5370 | 3 | 4 | | IV-2 | SDHA | 0.67 |
| 5275 | 3 | 4 | | | | IV-2 | RNF44 | 0.76 | 5371 | 3 | 4 | | IV-2 | SDHAP3 | 0.87 |
| 5276 | 3 | 4 | | | | IV-2 | RNF7 | 0.82 | 5372 | 3 | 4 | | IV-2 | SDHB | 0.87 |
| 5277 | 3 | 4 | | | | IV-2 | RNF8 | 0.78 | 5373 | 3 | 4 | | IV-2 | SDHD | 0.86 |

Fig. 38 - 29

| | | | | | | | | | | | | | | | |
|---|---|---|---|---|---|---|---|---|---|---|---|---|---|---|---|
| 5374 | 3 | 4 | | | IV-2 | SEC11A | 0.77 | 5470 | 3 | 4 | | | IV-2 | SLC37A4 | 0.68 |
| 5375 | 3 | 4 | | | IV-2 | SEC11C | 0.91 | 5471 | 3 | 4 | | | IV-2 | SLC38A10 | 0.88 |
| 5376 | 3 | 4 | | | IV-2 | SEC16A | 0.99 | 5472 | 3 | 4 | | | IV-2 | SLC38A7 | 0.82 |
| 5377 | 3 | 4 | | | IV-2 | SEC22A | 0.97 | 5473 | 3 | 4 | | | IV-2 | SLC38A9 | 0.97 |
| 5378 | 3 | 4 | | | IV-2 | SEC22C | 0.80 | 5474 | 3 | 4 | | | IV-2 | SLC39A8 | 0.90 |
| 5379 | 3 | 4 | | | IV-2 | SEC24C | 0.81 | 5475 | 3 | 4 | | | IV-2 | SLC41A3 | 0.90 |
| 5380 | 3 | 4 | | | IV-2 | SEC61A1 | 0.71 | 5476 | 3 | 4 | | | IV-2 | SLC44A4 | 0.91 |
| 5381 | 3 | 4 | | | IV-2 | SELM | 0.81 | 5477 | 3 | 4 | | | IV-2 | SLC45A1 | 0.77 |
| 5382 | 3 | 4 | | | IV-2 | SELS | 0.90 | 5478 | 3 | 4 | | | IV-2 | SLC46A1 | 0.99 |
| 5383 | 3 | 4 | | | IV-2 | SELT | 0.90 | 5479 | 3 | 4 | | | IV-2 | SLC4A11 | 0.78 |
| 5384 | 3 | 4 | | | IV-2 | SEMA3B | 0.80 | 5480 | 3 | 4 | | | IV-2 | SLC4A1AP | 0.98 |
| 5385 | 3 | 4 | | | IV-2 | SEMA4F | 0.84 | 5481 | 3 | 4 | | | IV-2 | SLC4A3 | 0.67 |
| 5386 | 3 | 4 | | | IV-2 | SEP15 | 0.83 | 5482 | 3 | 4 | | | IV-2 | SLC50A1 | 0.89 |
| 5387 | 3 | 4 | | | IV-2 | SEPHS1 | 0.81 | 5483 | 3 | 4 | | | IV-2 | SLC5A6 | 0.67 |
| 5388 | 3 | 4 | | | IV-2 | SEPHS2 | 0.95 | 5484 | 3 | 4 | | | IV-2 | SLC6A15 | 0.97 |
| 5389 | 3 | 4 | | | IV-2 | SEPT8 | 1.00 | 5485 | 3 | 4 | | | IV-2 | SLC6A6 | 0.97 |
| 5390 | 3 | 4 | | | IV-2 | SERF1B | 0.83 | 5486 | 3 | 4 | | | IV-2 | SLC7A6OS | 0.94 |
| 5391 | 3 | 4 | | | IV-2 | SERF2 | 0.76 | 5487 | 3 | 4 | | | IV-2 | SLC9A5 | 0.92 |
| 5392 | 3 | 4 | | | IV-2 | SERINC2 | 0.67 | 5488 | 3 | 4 | | | IV-2 | SLC9B2 | 0.92 |
| 5393 | 3 | 4 | | | IV-2 | SERPINA11 | 0.90 | 5489 | 3 | 4 | | | IV-2 | SLCO2A1 | 0.79 |
| 5394 | 3 | 4 | | | IV-2 | SERPINA5 | 0.76 | 5490 | 3 | 4 | | | IV-2 | SLCO4A1 | 0.78 |
| 5395 | 3 | 4 | | | IV-2 | SERPINB1 | 0.99 | 5491 | 3 | 4 | | | IV-2 | SLIT3 | 0.90 |
| 5396 | 3 | 4 | | | IV-2 | SERPINB6 | 0.73 | 5492 | 3 | 4 | | | IV-2 | SMAD3 | 0.87 |
| 5397 | 3 | 4 | | | IV-2 | SERPINF1 | 0.79 | 5493 | 3 | 4 | | | IV-2 | SMAD5-AS1 | 0.72 |
| 5398 | 3 | 4 | | | IV-2 | SERPINF2 | 0.79 | 5494 | 3 | 4 | | | IV-2 | SMAGP | 0.90 |
| 5399 | 3 | 4 | | | IV-2 | SERPING1 | 0.80 | 5495 | 3 | 4 | | | IV-2 | SMAP1 | 0.98 |
| 5400 | 3 | 4 | | | IV-2 | SESN1 | 1.00 | 5496 | 3 | 4 | | | IV-2 | SMARCAL1 | 0.95 |
| 5401 | 3 | 4 | | | IV-2 | SESN2 | 0.81 | 5497 | 3 | 4 | | | IV-2 | SMARCC2 | 0.68 |
| 5402 | 3 | 4 | | | IV-2 | SET | 0.78 | 5498 | 3 | 4 | | | IV-2 | SMARCD2 | 0.68 |
| 5403 | 3 | 4 | | | IV-2 | SETD1B | 0.83 | 5499 | 3 | 4 | | | IV-2 | SMARCE1 | 0.86 |
| 5404 | 3 | 4 | | | IV-2 | SETD3 | 0.94 | 5500 | 3 | 4 | | | IV-2 | SMC2 | 1.00 |
| 5405 | 3 | 4 | | | IV-2 | SETD8 | 0.70 | 5501 | 3 | 4 | | | IV-2 | SMCR7 | 0.71 |
| 5406 | 3 | 4 | | | IV-2 | SETDB1 | 0.91 | 5502 | 3 | 4 | | | IV-2 | SMG5 | 0.81 |
| 5407 | 3 | 4 | | | IV-2 | SF1 | 0.75 | 5503 | 3 | 4 | | | IV-2 | SMG6 | 0.84 |
| 5408 | 3 | 4 | | | IV-2 | SF3B14 | 0.82 | 5504 | 3 | 4 | | | IV-2 | SMG7 | 0.91 |
| 5409 | 3 | 4 | | | IV-2 | SFI1 | 0.74 | 5505 | 3 | 4 | | | IV-2 | SMG9 | 0.74 |
| 5410 | 3 | 4 | | | IV-2 | SFMBT1 | 1.00 | 5506 | 3 | 4 | | | IV-2 | SMTN | 0.70 |
| 5411 | 3 | 4 | | | IV-2 | SFPQ | 0.87 | 5507 | 3 | 4 | | | IV-2 | SMU1 | 0.76 |
| 5412 | 3 | 4 | | | IV-2 | SFT2D3 | 0.68 | 5508 | 3 | 4 | | | IV-2 | SMUG1 | 0.79 |
| 5413 | 3 | 4 | | | IV-2 | SFXN5 | 0.99 | 5509 | 3 | 4 | | | IV-2 | SMYD3 | 0.70 |
| 5414 | 3 | 4 | | | IV-2 | SGK3 | 0.81 | 5510 | 3 | 4 | | | IV-2 | SNAP23 | 0.97 |
| 5415 | 3 | 4 | | | IV-2 | SGPP1 | 0.83 | 5511 | 3 | 4 | | | IV-2 | SNAP47 | 0.70 |
| 5416 | 3 | 4 | | | IV-2 | SH2B1 | 0.68 | 5512 | 3 | 4 | | | IV-2 | SNAPIN | 0.81 |
| 5417 | 3 | 4 | | | IV-2 | SH3BP5 | 0.79 | 5513 | 3 | 4 | | | IV-2 | SNHG15 | 0.88 |
| 5418 | 3 | 4 | | | IV-2 | SH3D21 | 0.91 | 5514 | 3 | 4 | | | IV-2 | SNHG7 | 0.72 |
| 5419 | 3 | 4 | | | IV-2 | SH3GLB1 | 1.00 | 5515 | 3 | 4 | | | IV-2 | SNHG8 | 0.98 |
| 5420 | 3 | 4 | | | IV-2 | SH3PXD2B | 0.83 | 5516 | 3 | 4 | | | IV-2 | SNORA53 | 0.89 |
| 5421 | 3 | 4 | | | IV-2 | SH3TC1 | 0.79 | 5517 | 3 | 4 | | | IV-2 | SNORA74A | 0.95 |
| 5422 | 3 | 4 | | | IV-2 | SHC1 | 0.73 | 5518 | 3 | 4 | | | IV-2 | SNRNP200 | 0.97 |
| 5423 | 3 | 4 | | | IV-2 | SHFM1 | 0.91 | 5519 | 3 | 4 | | | IV-2 | SNRNP25 | 0.80 |
| 5424 | 3 | 4 | | | IV-2 | SHISA6 | 0.80 | 5520 | 3 | 4 | | | IV-2 | SNRNP27 | 0.75 |
| 5425 | 3 | 4 | | | IV-2 | SHMT1 | 0.71 | 5521 | 3 | 4 | | | IV-2 | SNRPB2 | 0.87 |
| 5426 | 3 | 4 | | | IV-2 | SHPK | 0.77 | 5522 | 3 | 4 | | | IV-2 | SNRPD1 | 0.92 |
| 5427 | 3 | 4 | | | IV-2 | SHROOM4 | 0.94 | 5523 | 3 | 4 | | | IV-2 | SNRPD3 | 0.84 |
| 5428 | 3 | 4 | | | IV-2 | SIAE | 0.94 | 5524 | 3 | 4 | | | IV-2 | SNRPE | 0.81 |
| 5429 | 3 | 4 | | | IV-2 | SIAH1 | 0.81 | 5525 | 3 | 4 | | | IV-2 | SNRPG | 0.90 |
| 5430 | 3 | 4 | | | IV-2 | SIK2 | 0.86 | 5526 | 3 | 4 | | | IV-2 | SNUPN | 0.75 |
| 5431 | 3 | 4 | | | IV-2 | SIK3 | 0.73 | 5527 | 3 | 4 | | | IV-2 | SNW1 | 0.72 |
| 5432 | 3 | 4 | | | IV-2 | SIL1 | 0.76 | 5528 | 3 | 4 | | | IV-2 | SNX11 | 0.84 |
| 5433 | 3 | 4 | | | IV-2 | SIN3A | 0.87 | 5529 | 3 | 4 | | | IV-2 | SNX2 | 0.92 |
| 5434 | 3 | 4 | | | IV-2 | SIRPA | 0.69 | 5530 | 3 | 4 | | | IV-2 | SNX25 | 0.98 |
| 5435 | 3 | 4 | | | IV-2 | SIRT3 | 0.75 | 5531 | 3 | 4 | | | IV-2 | SNX27 | 0.99 |
| 5436 | 3 | 4 | | | IV-2 | SIRT7 | 0.74 | 5532 | 3 | 4 | | | IV-2 | SNX29P2 | 0.99 |
| 5437 | 3 | 4 | | | IV-2 | SIVA1 | 0.69 | 5533 | 3 | 4 | | | IV-2 | SNX5 | 0.92 |
| 5438 | 3 | 4 | | | IV-2 | SIX2 | 0.97 | 5534 | 3 | 4 | | | IV-2 | SNX7 | 0.83 |
| 5439 | 3 | 4 | | | IV-2 | SKA2 | 0.96 | 5535 | 3 | 4 | | | IV-2 | SNX8 | 0.70 |
| 5440 | 3 | 4 | | | IV-2 | SKA3 | 0.91 | 5536 | 3 | 4 | | | IV-2 | SNX9 | 0.71 |
| 5441 | 3 | 4 | | | IV-2 | SKP1 | 0.92 | 5537 | 3 | 4 | | | IV-2 | SOCS1 | 0.97 |
| 5442 | 3 | 4 | | | IV-2 | SLAIN1 | 0.97 | 5538 | 3 | 4 | | | IV-2 | SOCS6 | 0.99 |
| 5443 | 3 | 4 | | | IV-2 | SLBP | 0.87 | 5539 | 3 | 4 | | | IV-2 | SOX2 | 0.84 |
| 5444 | 3 | 4 | | | IV-2 | SLC15A3 | 0.79 | 5540 | 3 | 4 | | | IV-2 | SP1 | 0.98 |
| 5445 | 3 | 4 | | | IV-2 | SLC15A4 | 0.73 | 5541 | 3 | 4 | | | IV-2 | SPAG16 | 0.90 |
| 5446 | 3 | 4 | | | IV-2 | SLC16A2 | 0.88 | 5542 | 3 | 4 | | | IV-2 | SPAG8 | 0.93 |
| 5447 | 3 | 4 | | | IV-2 | SLC1A1 | 0.72 | 5543 | 3 | 4 | | | IV-2 | SPATA7 | 0.76 |
| 5448 | 3 | 4 | | | IV-2 | SLC1A2 | 0.93 | 5544 | 3 | 4 | | | IV-2 | SPATS2 | 0.74 |
| 5449 | 3 | 4 | | | IV-2 | SLC1A7 | 0.99 | 5545 | 3 | 4 | | | IV-2 | SPCS1 | 0.95 |
| 5450 | 3 | 4 | | | IV-2 | SLC22A18 | 0.78 | 5546 | 3 | 4 | | | IV-2 | SPCS2 | 0.89 |
| 5451 | 3 | 4 | | | IV-2 | SLC22A23 | 0.71 | 5547 | 3 | 4 | | | IV-2 | SPDYA | 0.98 |
| 5452 | 3 | 4 | | | IV-2 | SLC24A6 | 0.73 | 5548 | 3 | 4 | | | IV-2 | SPECC1L | 0.79 |
| 5453 | 3 | 4 | | | IV-2 | SLC25A17 | 0.97 | 5549 | 3 | 4 | | | IV-2 | SPESP1 | 0.78 |
| 5454 | 3 | 4 | | | IV-2 | SLC25A20 | 0.79 | 5550 | 3 | 4 | | | IV-2 | SPG21 | 0.86 |
| 5455 | 3 | 4 | | | IV-2 | SLC25A26 | 0.97 | 5551 | 3 | 4 | | | IV-2 | SPHK1 | 0.73 |
| 5456 | 3 | 4 | | | IV-2 | SLC25A29 | 0.74 | 5552 | 3 | 4 | | | IV-2 | SPHK2 | 0.74 |
| 5457 | 3 | 4 | | | IV-2 | SLC25A3 | 0.95 | 5553 | 3 | 4 | | | IV-2 | SPINK1 | 0.94 |
| 5458 | 3 | 4 | | | IV-2 | SLC25A32 | 0.90 | 5554 | 3 | 4 | | | IV-2 | SPNS2 | 0.78 |
| 5459 | 3 | 4 | | | IV-2 | SLC25A33 | 0.91 | 5555 | 3 | 4 | | | IV-2 | SPOP | 0.91 |
| 5460 | 3 | 4 | | | IV-2 | SLC25A38 | 0.70 | 5556 | 3 | 4 | | | IV-2 | SPRY1 | 0.81 |
| 5461 | 3 | 4 | | | IV-2 | SLC25A42 | 0.80 | 5557 | 3 | 4 | | | IV-2 | SPRYD4 | 0.87 |
| 5462 | 3 | 4 | | | IV-2 | SLC25A44 | 0.92 | 5558 | 3 | 4 | | | IV-2 | SPRYD7 | 0.94 |
| 5463 | 3 | 4 | | | IV-2 | SLC26A1 | 0.72 | 5559 | 3 | 4 | | | IV-2 | SPTAN1 | 0.73 |
| 5464 | 3 | 4 | | | IV-2 | SLC26A11 | 0.78 | 5560 | 3 | 4 | | | IV-2 | SPTBN1 | 0.99 |
| 5465 | 3 | 4 | | | IV-2 | SLC29A2 | 0.79 | 5561 | 3 | 4 | | | IV-2 | SPTSSA | 0.91 |
| 5466 | 3 | 4 | | | IV-2 | SLC2A8 | 0.72 | 5562 | 3 | 4 | | | IV-2 | SRCIN1 | 0.91 |
| 5467 | 3 | 4 | | | IV-2 | SLC35A1 | 0.96 | 5563 | 3 | 4 | | | IV-2 | SRGAP2 | 0.88 |
| 5468 | 3 | 4 | | | IV-2 | SLC35D2 | 0.86 | 5564 | 3 | 4 | | | IV-2 | SRI | 0.87 |
| 5469 | 3 | 4 | | | IV-2 | SLC35F2 | 0.68 | 5565 | 3 | 4 | | | IV-2 | SRL | 0.92 |

Fig. 38 - 30

| | | | | | | | | | | | | | | |
|---|---|---|---|---|---|---|---|---|---|---|---|---|---|---|
| 5566 | 3 | 4 | | | IV-2 | SRP19 | 0.94 | 5662 | 3 | 4 | | | IV-2 | TCF25 | 0.79 |
| 5567 | 3 | 4 | | | IV-2 | SRP54 | 0.98 | 5663 | 3 | 4 | | | IV-2 | TCF7L2 | 0.87 |
| 5568 | 3 | 4 | | | IV-2 | SRP68 | 0.79 | 5664 | 3 | 4 | | | IV-2 | TCHP | 0.93 |
| 5569 | 3 | 4 | | | IV-2 | SRP9 | 0.95 | 5665 | 3 | 4 | | | IV-2 | TCN2 | 0.83 |
| 5570 | 3 | 4 | | | IV-2 | SRPK3 | 0.96 | 5666 | 3 | 4 | | | IV-2 | TCP1 | 0.86 |
| 5571 | 3 | 4 | | | IV-2 | SRPRB | 0.72 | 5667 | 3 | 4 | | | IV-2 | TCTA | 0.82 |
| 5572 | 3 | 4 | | | IV-2 | SRRD | 0.98 | 5668 | 3 | 4 | | | IV-2 | TCTEX1D1 | 0.95 |
| 5573 | 3 | 4 | | | IV-2 | SRRM1 | 0.96 | 5669 | 3 | 4 | | | IV-2 | TCTN1 | 0.91 |
| 5574 | 3 | 4 | | | IV-2 | SRRM2 | 0.87 | 5670 | 3 | 4 | | | IV-2 | TCTN3 | 0.82 |
| 5575 | 3 | 4 | | | IV-2 | SRSF3 | 0.90 | 5671 | 3 | 4 | | | IV-2 | TDP1 | 0.72 |
| 5576 | 3 | 4 | | | IV-2 | SRSF4 | 0.73 | 5672 | 3 | 4 | | | IV-2 | TDRD7 | 0.89 |
| 5577 | 3 | 4 | | | IV-2 | SRSF8 | 0.96 | 5673 | 3 | 4 | | | IV-2 | TEAD4 | 0.77 |
| 5578 | 3 | 4 | | | IV-2 | SSU72 | 0.92 | 5674 | 3 | 4 | | | IV-2 | TEC | 0.76 |
| 5579 | 3 | 4 | | | IV-2 | SSX2IP | 0.85 | 5675 | 3 | 4 | | | IV-2 | TECPR2 | 0.84 |
| 5580 | 3 | 4 | | | IV-2 | ST13 | 0.86 | 5676 | 3 | 4 | | | IV-2 | TERF2 | 0.86 |
| 5581 | 3 | 4 | | | IV-2 | ST13P4 | 0.80 | 5677 | 3 | 4 | | | IV-2 | TERF2IP | 0.80 |
| 5582 | 3 | 4 | | | IV-2 | ST20 | 0.94 | 5678 | 3 | 4 | | | IV-2 | TES | 0.72 |
| 5583 | 3 | 4 | | | IV-2 | ST3GAL3 | 0.75 | 5679 | 3 | 4 | | | IV-2 | TEX261 | 0.72 |
| 5584 | 3 | 4 | | | IV-2 | ST6GAL1 | 0.75 | 5680 | 3 | 4 | | | IV-2 | TFB2M | 0.78 |
| 5585 | 3 | 4 | | | IV-2 | ST6GALNAC3 | 0.93 | 5681 | 3 | 4 | | | IV-2 | TFDP1 | 0.81 |
| 5586 | 3 | 4 | | | IV-2 | ST6GALNAC5 | 1.00 | 5682 | 3 | 4 | | | IV-2 | TFG | 0.68 |
| 5587 | 3 | 4 | | | IV-2 | STAM | 1.00 | 5683 | 3 | 4 | | | IV-2 | TFR2 | 0.86 |
| 5588 | 3 | 4 | | | IV-2 | STAR | 0.87 | 5684 | 3 | 4 | | | IV-2 | TGFB3 | 0.79 |
| 5589 | 3 | 4 | | | IV-2 | STARD3NL | 0.91 | 5685 | 3 | 4 | | | IV-2 | TH1L | 0.73 |
| 5590 | 3 | 4 | | | IV-2 | STARD5 | 0.83 | 5686 | 3 | 4 | | | IV-2 | THADA | 0.86 |
| 5591 | 3 | 4 | | | IV-2 | STARD8 | 0.90 | 5687 | 3 | 4 | | | IV-2 | THEM4 | 0.79 |
| 5592 | 3 | 4 | | | IV-2 | STAT2 | 0.89 | 5688 | 3 | 4 | | | IV-2 | THOC7 | 0.85 |
| 5593 | 3 | 4 | | | IV-2 | STAT5A | 0.76 | 5689 | 3 | 4 | | | IV-2 | THRAP3 | 0.85 |
| 5594 | 3 | 4 | | | IV-2 | STAT5B | 0.88 | 5690 | 3 | 4 | | | IV-2 | THSD1 | 0.81 |
| 5595 | 3 | 4 | | | IV-2 | STAT6 | 0.67 | 5691 | 3 | 4 | | | IV-2 | THTPA | 0.85 |
| 5596 | 3 | 4 | | | IV-2 | STIM2 | 0.86 | 5692 | 3 | 4 | | | IV-2 | TIGD6 | 0.99 |
| 5597 | 3 | 4 | | | IV-2 | STK32C | 0.73 | 5693 | 3 | 4 | | | IV-2 | TIGD7 | 1.00 |
| 5598 | 3 | 4 | | | IV-2 | STK35 | 0.68 | 5694 | 3 | 4 | | | IV-2 | TIMELESS | 0.72 |
| 5599 | 3 | 4 | | | IV-2 | STMN3 | 0.79 | 5695 | 3 | 4 | | | IV-2 | TIMM10 | 0.79 |
| 5600 | 3 | 4 | | | IV-2 | STOM | 0.85 | 5696 | 3 | 4 | | | IV-2 | TIMM17A | 0.98 |
| 5601 | 3 | 4 | | | IV-2 | STOML2 | 0.76 | 5697 | 3 | 4 | | | IV-2 | TIMM21 | 0.91 |
| 5602 | 3 | 4 | | | IV-2 | STON1 | 0.86 | 5698 | 3 | 4 | | | IV-2 | TIMM22 | 0.68 |
| 5603 | 3 | 4 | | | IV-2 | STOX1 | 0.99 | 5699 | 3 | 4 | | | IV-2 | TIMM23 | 0.88 |
| 5604 | 3 | 4 | | | IV-2 | STT3A | 0.85 | 5700 | 3 | 4 | | | IV-2 | TIMM9 | 0.77 |
| 5605 | 3 | 4 | | | IV-2 | STX10 | 0.85 | 5701 | 3 | 4 | | | IV-2 | TIMMDC1 | 0.84 |
| 5606 | 3 | 4 | | | IV-2 | STX18 | 0.89 | 5702 | 3 | 4 | | | IV-2 | TIMP2 | 0.80 |
| 5607 | 3 | 4 | | | IV-2 | STX4 | 0.76 | 5703 | 3 | 4 | | | IV-2 | TK2 | 0.86 |
| 5608 | 3 | 4 | | | IV-2 | STXBP1 | 0.70 | 5704 | 3 | 4 | | | IV-2 | TLK1 | 0.95 |
| 5609 | 3 | 4 | | | IV-2 | STXBP3 | 0.92 | 5705 | 3 | 4 | | | IV-2 | TLK2 | 0.96 |
| 5610 | 3 | 4 | | | IV-2 | SUCLG1 | 0.87 | 5706 | 3 | 4 | | | IV-2 | TLN1 | 0.71 |
| 5611 | 3 | 4 | | | IV-2 | SULT1A1 | 0.92 | 5707 | 3 | 4 | | | IV-2 | TLR9 | 0.86 |
| 5612 | 3 | 4 | | | IV-2 | SUMO1 | 0.79 | 5708 | 3 | 4 | | | IV-2 | TM2D1 | 0.95 |
| 5613 | 3 | 4 | | | IV-2 | SUMO1P3 | 0.76 | 5709 | 3 | 4 | | | IV-2 | TM2D2 | 0.91 |
| 5614 | 3 | 4 | | | IV-2 | SUMO2 | 0.88 | 5710 | 3 | 4 | | | IV-2 | TM2D3 | 0.95 |
| 5615 | 3 | 4 | | | IV-2 | SUMO3 | 0.73 | 5711 | 3 | 4 | | | IV-2 | TM4SF1 | 0.76 |
| 5616 | 3 | 4 | | | IV-2 | SUOX | 0.85 | 5712 | 3 | 4 | | | IV-2 | TM7SF3 | 0.81 |
| 5617 | 3 | 4 | | | IV-2 | SUPT16H | 0.73 | 5713 | 3 | 4 | | | IV-2 | TM9SF3 | 0.98 |
| 5618 | 3 | 4 | | | IV-2 | SUPT6H | 0.77 | 5714 | 3 | 4 | | | IV-2 | TMBIM4 | 0.94 |
| 5619 | 3 | 4 | | | IV-2 | SURF6 | 0.78 | 5715 | 3 | 4 | | | IV-2 | TMCO1 | 0.75 |
| 5620 | 3 | 4 | | | IV-2 | SUSD3 | 0.87 | 5716 | 3 | 4 | | | IV-2 | TMCO6 | 0.75 |
| 5621 | 3 | 4 | | | IV-2 | SV2A | 0.99 | 5717 | 3 | 4 | | | IV-2 | TMED2 | 0.84 |
| 5622 | 3 | 4 | | | IV-2 | SWI5 | 0.79 | 5718 | 3 | 4 | | | IV-2 | TMED6 | 0.97 |
| 5623 | 3 | 4 | | | IV-2 | SYBU | 0.92 | 5719 | 3 | 4 | | | IV-2 | TMEM100 | 0.94 |
| 5624 | 3 | 4 | | | IV-2 | SYF2 | 0.87 | 5720 | 3 | 4 | | | IV-2 | TMEM106C | 0.72 |
| 5625 | 3 | 4 | | | IV-2 | SYN1 | 0.98 | 5721 | 3 | 4 | | | IV-2 | TMEM119 | 0.76 |
| 5626 | 3 | 4 | | | IV-2 | SYNC | 0.97 | 5722 | 3 | 4 | | | IV-2 | TMEM120A | 0.83 |
| 5627 | 3 | 4 | | | IV-2 | SYNCRIP | 0.99 | 5723 | 3 | 4 | | | IV-2 | TMEM120B | 0.79 |
| 5628 | 3 | 4 | | | IV-2 | SYNE2 | 0.69 | 5724 | 3 | 4 | | | IV-2 | TMEM125 | 0.84 |
| 5629 | 3 | 4 | | | IV-2 | SYNGAP1 | 0.68 | 5725 | 3 | 4 | | | IV-2 | TMEM128 | 0.92 |
| 5630 | 3 | 4 | | | IV-2 | SYP | 0.71 | 5726 | 3 | 4 | | | IV-2 | TMEM129 | 0.69 |
| 5631 | 3 | 4 | | | IV-2 | SYS1 | 0.80 | 5727 | 3 | 4 | | | IV-2 | TMEM131 | 0.87 |
| 5632 | 3 | 4 | | | IV-2 | TACO1 | 0.68 | 5728 | 3 | 4 | | | IV-2 | TMEM132A | 0.69 |
| 5633 | 3 | 4 | | | IV-2 | TACR2 | 0.82 | 5729 | 3 | 4 | | | IV-2 | TMEM132E | 0.91 |
| 5634 | 3 | 4 | | | IV-2 | TAF10 | 0.72 | 5730 | 3 | 4 | | | IV-2 | TMEM140 | 0.68 |
| 5635 | 3 | 4 | | | IV-2 | TAF15 | 0.68 | 5731 | 3 | 4 | | | IV-2 | TMEM14B | 0.72 |
| 5636 | 3 | 4 | | | IV-2 | TAF4 | 0.79 | 5732 | 3 | 4 | | | IV-2 | TMEM14C | 0.78 |
| 5637 | 3 | 4 | | | IV-2 | TAF5L | 0.89 | 5733 | 3 | 4 | | | IV-2 | TMEM171 | 0.94 |
| 5638 | 3 | 4 | | | IV-2 | TAF9 | 0.89 | 5734 | 3 | 4 | | | IV-2 | TMEM176A | 0.78 |
| 5639 | 3 | 4 | | | IV-2 | TAMM41 | 0.80 | 5735 | 3 | 4 | | | IV-2 | TMEM18 | 0.89 |
| 5640 | 3 | 4 | | | IV-2 | TANC2 | 0.91 | 5736 | 3 | 4 | | | IV-2 | TMEM184C | 0.95 |
| 5641 | 3 | 4 | | | IV-2 | TARS | 0.98 | 5737 | 3 | 4 | | | IV-2 | TMEM185A | 0.85 |
| 5642 | 3 | 4 | | | IV-2 | TARS2 | 0.80 | 5738 | 3 | 4 | | | IV-2 | TMEM185B | 0.95 |
| 5643 | 3 | 4 | | | IV-2 | TATDN1 | 0.67 | 5739 | 3 | 4 | | | IV-2 | TMEM186 | 0.83 |
| 5644 | 3 | 4 | | | IV-2 | TATDN3 | 0.95 | 5740 | 3 | 4 | | | IV-2 | TMEM199 | 0.95 |
| 5645 | 3 | 4 | | | IV-2 | TBC1D13 | 0.76 | 5741 | 3 | 4 | | | IV-2 | TMEM203 | 0.68 |
| 5646 | 3 | 4 | | | IV-2 | TBC1D15 | 0.97 | 5742 | 3 | 4 | | | IV-2 | TMEM204 | 0.68 |
| 5647 | 3 | 4 | | | IV-2 | TBC1D20 | 0.92 | 5743 | 3 | 4 | | | IV-2 | TMEM206 | 0.84 |
| 5648 | 3 | 4 | | | IV-2 | TBC1D7 | 0.82 | 5744 | 3 | 4 | | | IV-2 | TMEM208 | 0.78 |
| 5649 | 3 | 4 | | | IV-2 | TBC1D9B | 0.74 | 5745 | 3 | 4 | | | IV-2 | TMEM209 | 0.97 |
| 5650 | 3 | 4 | | | IV-2 | TBCD | 0.71 | 5746 | 3 | 4 | | | IV-2 | TMEM216 | 0.81 |
| 5651 | 3 | 4 | | | IV-2 | TBCK | 0.71 | 5747 | 3 | 4 | | | IV-2 | TMEM238 | 0.73 |
| 5652 | 3 | 4 | | | IV-2 | TBK1 | 0.99 | 5748 | 3 | 4 | | | IV-2 | TMEM242 | 0.82 |
| 5653 | 3 | 4 | | | IV-2 | TBL1X | 0.86 | 5749 | 3 | 4 | | | IV-2 | TMEM35 | 0.95 |
| 5654 | 3 | 4 | | | IV-2 | TBP | 0.95 | 5750 | 3 | 4 | | | IV-2 | TMEM42 | 0.80 |
| 5655 | 3 | 4 | | | IV-2 | TBPL1 | 0.82 | 5751 | 3 | 4 | | | IV-2 | TMEM5 | 0.98 |
| 5656 | 3 | 4 | | | IV-2 | TBX15 | 0.87 | 5752 | 3 | 4 | | | IV-2 | TMEM55B | 0.81 |
| 5657 | 3 | 4 | | | IV-2 | TBX3 | 0.94 | 5753 | 3 | 4 | | | IV-2 | TMEM59 | 0.74 |
| 5658 | 3 | 4 | | | IV-2 | TCEA3 | 0.82 | 5754 | 3 | 4 | | | IV-2 | TMEM65 | 0.82 |
| 5659 | 3 | 4 | | | IV-2 | TCEAL7 | 0.82 | 5755 | 3 | 4 | | | IV-2 | TMEM69 | 0.91 |
| 5660 | 3 | 4 | | | IV-2 | TCEAL8 | 0.76 | 5756 | 3 | 4 | | | IV-2 | TMEM70 | 0.86 |
| 5661 | 3 | 4 | | | IV-2 | TCEB1 | 0.85 | 5757 | 3 | 4 | | | IV-2 | TMEM80 | 0.96 |

Fig. 38 - 31

| | | | | | | | | | | | | | | |
|---|---|---|---|---|---|---|---|---|---|---|---|---|---|---|
| 5758 | 3 | 4 | | | IV-2 | TMEM81 | 0.73 | 5854 | 3 | 4 | | | IV-2 | TXNDC12 | 0.73 |
| 5759 | 3 | 4 | | | IV-2 | TMEM85 | 0.74 | 5855 | 3 | 4 | | | IV-2 | TXNDC15 | 0.77 |
| 5760 | 3 | 4 | | | IV-2 | TMEM87A | 0.97 | 5856 | 3 | 4 | | | IV-2 | TXNDC17 | 0.84 |
| 5761 | 3 | 4 | | | IV-2 | TMEM8B | 0.81 | 5857 | 3 | 4 | | | IV-2 | TXNDC5 | 0.81 |
| 5762 | 3 | 4 | | | IV-2 | TMEM9 | 0.71 | 5858 | 3 | 4 | | | IV-2 | TXNL4A | 0.73 |
| 5763 | 3 | 4 | | | IV-2 | TMEM98 | 0.92 | 5859 | 3 | 4 | | | IV-2 | TXNRD3 | 0.98 |
| 5764 | 3 | 4 | | | IV-2 | TMEM9B | 0.95 | 5860 | 3 | 4 | | | IV-2 | TYW1 | 0.90 |
| 5765 | 3 | 4 | | | IV-2 | TMIE | 0.97 | 5861 | 3 | 4 | | | IV-2 | UAP1 | 0.77 |
| 5766 | 3 | 4 | | | IV-2 | TMOD3 | 0.78 | 5862 | 3 | 4 | | | IV-2 | UBA2 | 0.82 |
| 5767 | 3 | 4 | | | IV-2 | TMPO | 0.89 | 5863 | 3 | 4 | | | IV-2 | UBA52 | 0.69 |
| 5768 | 3 | 4 | | | IV-2 | TMPRSS2 | 0.77 | 5864 | 3 | 4 | | | IV-2 | UBAC1 | 0.70 |
| 5769 | 3 | 4 | | | IV-2 | TMPRSS3 | 0.99 | 5865 | 3 | 4 | | | IV-2 | UBAP2 | 0.69 |
| 5770 | 3 | 4 | | | IV-2 | TMPRSS4 | 0.93 | 5866 | 3 | 4 | | | IV-2 | UBB | 0.73 |
| 5771 | 3 | 4 | | | IV-2 | TMPRSS6 | 0.82 | 5867 | 3 | 4 | | | IV-2 | UBC | 0.68 |
| 5772 | 3 | 4 | | | IV-2 | TMTC3 | 0.96 | 5868 | 3 | 4 | | | IV-2 | UBE2A | 0.98 |
| 5773 | 3 | 4 | | | IV-2 | TMUB2 | 0.72 | 5869 | 3 | 4 | | | IV-2 | UBE2B | 0.98 |
| 5774 | 3 | 4 | | | IV-2 | TMX2 | 0.76 | 5870 | 3 | 4 | | | IV-2 | UBE2D3 | 0.98 |
| 5775 | 3 | 4 | | | IV-2 | TNFRSF18 | 0.68 | 5871 | 3 | 4 | | | IV-2 | UBE2D4 | 0.99 |
| 5776 | 3 | 4 | | | IV-2 | TNFRSF4 | 0.98 | 5872 | 3 | 4 | | | IV-2 | UBE2E1 | 0.93 |
| 5777 | 3 | 4 | | | IV-2 | TNFSF10 | 0.84 | 5873 | 3 | 4 | | | IV-2 | UBE2E3 | 0.83 |
| 5778 | 3 | 4 | | | IV-2 | TNFSF13 | 0.91 | 5874 | 3 | 4 | | | IV-2 | UBE2G1 | 0.92 |
| 5779 | 3 | 4 | | | IV-2 | TNNT3 | 0.89 | 5875 | 3 | 4 | | | IV-2 | UBE2G2 | 0.84 |
| 5780 | 3 | 4 | | | IV-2 | TNPO2 | 0.87 | 5876 | 3 | 4 | | | IV-2 | UBE2I | 0.77 |
| 5781 | 3 | 4 | | | IV-2 | TNPO3 | 0.93 | 5877 | 3 | 4 | | | IV-2 | UBE2J1 | 0.97 |
| 5782 | 3 | 4 | | | IV-2 | TNS1 | 0.81 | 5878 | 3 | 4 | | | IV-2 | UBE2N | 0.86 |
| 5783 | 3 | 4 | | | IV-2 | TNS3 | 0.96 | 5879 | 3 | 4 | | | IV-2 | UBE2Q1 | 0.79 |
| 5784 | 3 | 4 | | | IV-2 | TOE1 | 0.92 | 5880 | 3 | 4 | | | IV-2 | UBE2Q2P2 | 0.81 |
| 5785 | 3 | 4 | | | IV-2 | TOM1L2 | 0.69 | 5881 | 3 | 4 | | | IV-2 | UBE2R2 | 0.77 |
| 5786 | 3 | 4 | | | IV-2 | TOMM34 | 0.69 | 5882 | 3 | 4 | | | IV-2 | UBE3B | 0.89 |
| 5787 | 3 | 4 | | | IV-2 | TOMM40L | 0.86 | 5883 | 3 | 4 | | | IV-2 | UBE3C | 0.90 |
| 5788 | 3 | 4 | | | IV-2 | TOMM5 | 0.76 | 5884 | 3 | 4 | | | IV-2 | UBN1 | 0.74 |
| 5789 | 3 | 4 | | | IV-2 | TOMM6 | 0.82 | 5885 | 3 | 4 | | | IV-2 | UBR4 | 0.90 |
| 5790 | 3 | 4 | | | IV-2 | TOMM7 | 0.81 | 5886 | 3 | 4 | | | IV-2 | UBR7 | 0.96 |
| 5791 | 3 | 4 | | | IV-2 | TOP2A | 0.75 | 5887 | 3 | 4 | | | IV-2 | UCK1 | 0.79 |
| 5792 | 3 | 4 | | | IV-2 | TOP3A | 0.84 | 5888 | 3 | 4 | | | IV-2 | UFC1 | 0.68 |
| 5793 | 3 | 4 | | | IV-2 | TOR1A | 0.74 | 5889 | 3 | 4 | | | IV-2 | UFD1L | 0.74 |
| 5794 | 3 | 4 | | | IV-2 | TOR1B | 0.90 | 5890 | 3 | 4 | | | IV-2 | UGP2 | 0.97 |
| 5795 | 3 | 4 | | | IV-2 | TOR3A | 0.75 | 5891 | 3 | 4 | | | IV-2 | UHRF1 | 0.68 |
| 5796 | 3 | 4 | | | IV-2 | TOX4 | 0.96 | 5892 | 3 | 4 | | | IV-2 | ULK1 | 0.71 |
| 5797 | 3 | 4 | | | IV-2 | TP53INP2 | 0.86 | 5893 | 3 | 4 | | | IV-2 | UMPS | 0.97 |
| 5798 | 3 | 4 | | | IV-2 | TPBG | 0.78 | 5894 | 3 | 4 | | | IV-2 | UNC13B | 0.94 |
| 5799 | 3 | 4 | | | IV-2 | TPCN1 | 0.74 | 5895 | 3 | 4 | | | IV-2 | UNC13D | 0.76 |
| 5800 | 3 | 4 | | | IV-2 | TPD52L1 | 0.72 | 5896 | 3 | 4 | | | IV-2 | UNK | 0.84 |
| 5801 | 3 | 4 | | | IV-2 | TPD52L2 | 0.70 | 5897 | 3 | 4 | | | IV-2 | UPF1 | 0.81 |
| 5802 | 3 | 4 | | | IV-2 | TPGS2 | 0.68 | 5898 | 3 | 4 | | | IV-2 | UQCR11 | 0.85 |
| 5803 | 3 | 4 | | | IV-2 | TPI1P3 | 0.94 | 5899 | 3 | 4 | | | IV-2 | UQCRB | 0.79 |
| 5804 | 3 | 4 | | | IV-2 | TPP1 | 0.76 | 5900 | 3 | 4 | | | IV-2 | UQCRBP1 | 0.83 |
| 5805 | 3 | 4 | | | IV-2 | TPT1 | 0.68 | 5901 | 3 | 4 | | | IV-2 | UQCRC2 | 0.95 |
| 5806 | 3 | 4 | | | IV-2 | TRA2B | 0.90 | 5902 | 3 | 4 | | | IV-2 | UQCRH | 0.72 |
| 5807 | 3 | 4 | | | IV-2 | TRAIP | 0.86 | 5903 | 3 | 4 | | | IV-2 | UQCRHL | 0.85 |
| 5808 | 3 | 4 | | | IV-2 | TRAK1 | 0.73 | 5904 | 3 | 4 | | | IV-2 | UQCRQ | 0.87 |
| 5809 | 3 | 4 | | | IV-2 | TRAM2 | 0.89 | 5905 | 3 | 4 | | | IV-2 | URI1 | 0.98 |
| 5810 | 3 | 4 | | | IV-2 | TRAPPC2P1 | 0.94 | 5906 | 3 | 4 | | | IV-2 | UROD | 0.68 |
| 5811 | 3 | 4 | | | IV-2 | TRAPPC4 | 0.98 | 5907 | 3 | 4 | | | IV-2 | USP10 | 0.90 |
| 5812 | 3 | 4 | | | IV-2 | TRERF1 | 0.99 | 5908 | 3 | 4 | | | IV-2 | USP19 | 0.78 |
| 5813 | 3 | 4 | | | IV-2 | TRIB2 | 0.99 | 5909 | 3 | 4 | | | IV-2 | USP20 | 0.73 |
| 5814 | 3 | 4 | | | IV-2 | TRIM11 | 0.81 | 5910 | 3 | 4 | | | IV-2 | USP27X | 0.80 |
| 5815 | 3 | 4 | | | IV-2 | TRIM27 | 0.86 | 5911 | 3 | 4 | | | IV-2 | USP36 | 0.92 |
| 5816 | 3 | 4 | | | IV-2 | TRIM32 | 0.93 | 5912 | 3 | 4 | | | IV-2 | USP39 | 0.70 |
| 5817 | 3 | 4 | | | IV-2 | TRIM37 | 0.97 | 5913 | 3 | 4 | | | IV-2 | USP4 | 0.83 |
| 5818 | 3 | 4 | | | IV-2 | TRIM39 | 0.87 | 5914 | 3 | 4 | | | IV-2 | USP54 | 0.79 |
| 5819 | 3 | 4 | | | IV-2 | TRIM68 | 0.97 | 5915 | 3 | 4 | | | IV-2 | USP7 | 0.85 |
| 5820 | 3 | 4 | | | IV-2 | TRIM7 | 0.75 | 5916 | 3 | 4 | | | IV-2 | UTP11L | 0.96 |
| 5821 | 3 | 4 | | | IV-2 | TRIOBP | 0.67 | 5917 | 3 | 4 | | | IV-2 | UTP20 | 0.93 |
| 5822 | 3 | 4 | | | IV-2 | TRIP13 | 0.78 | 5918 | 3 | 4 | | | IV-2 | UVRAG | 0.82 |
| 5823 | 3 | 4 | | | IV-2 | TRMT2B | 0.98 | 5919 | 3 | 4 | | | IV-2 | UXS1 | 0.68 |
| 5824 | 3 | 4 | | | IV-2 | TRMT61B | 0.81 | 5920 | 3 | 4 | | | IV-2 | UXT | 0.90 |
| 5825 | 3 | 4 | | | IV-2 | TRPC4AP | 0.73 | 5921 | 3 | 4 | | | IV-2 | VAMP3 | 0.86 |
| 5826 | 3 | 4 | | | IV-2 | TRPT1 | 0.80 | 5922 | 3 | 4 | | | IV-2 | VANGL2 | 0.95 |
| 5827 | 3 | 4 | | | IV-2 | TRRAP | 0.98 | 5923 | 3 | 4 | | | IV-2 | VAPA | 0.87 |
| 5828 | 3 | 4 | | | IV-2 | TSEN15 | 0.88 | 5924 | 3 | 4 | | | IV-2 | VBP1 | 0.91 |
| 5829 | 3 | 4 | | | IV-2 | TSG101 | 0.79 | 5925 | 3 | 4 | | | IV-2 | VCAN | 0.71 |
| 5830 | 3 | 4 | | | IV-2 | TSPAN12 | 0.75 | 5926 | 3 | 4 | | | IV-2 | VCL | 0.88 |
| 5831 | 3 | 4 | | | IV-2 | TSPAN18 | 0.92 | 5927 | 3 | 4 | | | IV-2 | VDAC3 | 0.80 |
| 5832 | 3 | 4 | | | IV-2 | TSPAN3 | 0.75 | 5928 | 3 | 4 | | | IV-2 | VEPH1 | 0.93 |
| 5833 | 3 | 4 | | | IV-2 | TSPAN31 | 0.93 | 5929 | 3 | 4 | | | IV-2 | VGLL4 | 0.75 |
| 5834 | 3 | 4 | | | IV-2 | TSR2 | 0.72 | 5930 | 3 | 4 | | | IV-2 | VHL | 0.93 |
| 5835 | 3 | 4 | | | IV-2 | TSSK6 | 0.84 | 5931 | 3 | 4 | | | IV-2 | VILL | 0.77 |
| 5836 | 3 | 4 | | | IV-2 | TSTD1 | 0.68 | 5932 | 3 | 4 | | | IV-2 | VMA21 | 0.87 |
| 5837 | 3 | 4 | | | IV-2 | TTC1 | 0.81 | 5933 | 3 | 4 | | | IV-2 | VMAC | 0.89 |
| 5838 | 3 | 4 | | | IV-2 | TTC19 | 0.86 | 5934 | 3 | 4 | | | IV-2 | VMO1 | 0.69 |
| 5839 | 3 | 4 | | | IV-2 | TTC21A | 0.92 | 5935 | 3 | 4 | | | IV-2 | VPS11 | 0.71 |
| 5840 | 3 | 4 | | | IV-2 | TTC31 | 0.85 | 5936 | 3 | 4 | | | IV-2 | VPS16 | 0.68 |
| 5841 | 3 | 4 | | | IV-2 | TTC32 | 0.97 | 5937 | 3 | 4 | | | IV-2 | VPS29 | 0.85 |
| 5842 | 3 | 4 | | | IV-2 | TTC7B | 0.80 | 5938 | 3 | 4 | | | IV-2 | VPS33B | 0.71 |
| 5843 | 3 | 4 | | | IV-2 | TTC9C | 0.99 | 5939 | 3 | 4 | | | IV-2 | VPS35 | 0.92 |
| 5844 | 3 | 4 | | | IV-2 | TTI1 | 0.91 | 5940 | 3 | 4 | | | IV-2 | VPS39 | 0.88 |
| 5845 | 3 | 4 | | | IV-2 | TTL | 0.95 | 5941 | 3 | 4 | | | IV-2 | VPS53 | 0.84 |
| 5846 | 3 | 4 | | | IV-2 | TTLL1 | 1.00 | 5942 | 3 | 4 | | | IV-2 | VRK1 | 0.85 |
| 5847 | 3 | 4 | | | IV-2 | TTYH2 | 0.85 | 5943 | 3 | 4 | | | IV-2 | VRK3 | 0.68 |
| 5848 | 3 | 4 | | | IV-2 | TUBA1A | 0.73 | 5944 | 3 | 4 | | | IV-2 | VSIG8 | 0.73 |
| 5849 | 3 | 4 | | | IV-2 | TUBB | 0.68 | 5945 | 3 | 4 | | | IV-2 | VTCN1 | 0.72 |
| 5850 | 3 | 4 | | | IV-2 | TUBB3 | 0.67 | 5946 | 3 | 4 | | | IV-2 | VTI1A | 0.86 |
| 5851 | 3 | 4 | | | IV-2 | TUFT1 | 0.69 | 5947 | 3 | 4 | | | IV-2 | VTI1B | 0.86 |
| 5852 | 3 | 4 | | | IV-2 | TWF1 | 0.99 | 5948 | 3 | 4 | | | IV-2 | VWA7 | 0.97 |
| 5853 | 3 | 4 | | | IV-2 | TXNDC11 | 0.73 | 5949 | 3 | 4 | | | IV-2 | WASF1 | 0.97 |

Fig. 38 - 32

| | | | | | | | |
|---|---|---|---|---|---|---|---|
| 5950 | 3 | 4 | | | IV-2 | WBP11 | 0.74 |
| 5951 | 3 | 4 | | | IV-2 | WBSCR16 | 0.80 |
| 5952 | 3 | 4 | | | IV-2 | WDR1 | 0.77 |
| 5953 | 3 | 4 | | | IV-2 | WDR20 | 0.90 |
| 5954 | 3 | 4 | | | IV-2 | WDR27 | 0.97 |
| 5955 | 3 | 4 | | | IV-2 | WDR43 | 0.87 |
| 5956 | 3 | 4 | | | IV-2 | WDR45L | 0.81 |
| 5957 | 3 | 4 | | | IV-2 | WDR5 | 0.70 |
| 5958 | 3 | 4 | | | IV-2 | WDR55 | 0.71 |
| 5959 | 3 | 4 | | | IV-2 | WDR76 | 0.88 |
| 5960 | 3 | 4 | | | IV-2 | WDR77 | 0.95 |
| 5961 | 3 | 4 | | | IV-2 | WDR83OS | 0.70 |
| 5962 | 3 | 4 | | | IV-2 | WDR86 | 0.94 |
| 5963 | 3 | 4 | | | IV-2 | WFS1 | 0.70 |
| 5964 | 3 | 4 | | | IV-2 | WHAMM | 0.86 |
| 5965 | 3 | 4 | | | IV-2 | WHSC1 | 0.92 |
| 5966 | 3 | 4 | | | IV-2 | WIPF3 | 0.72 |
| 5967 | 3 | 4 | | | IV-2 | WIPI2 | 0.81 |
| 5968 | 3 | 4 | | | IV-2 | WISP2 | 0.87 |
| 5969 | 3 | 4 | | | IV-2 | WNT3 | 0.80 |
| 5970 | 3 | 4 | | | IV-2 | WNT5B | 0.92 |
| 5971 | 3 | 4 | | | IV-2 | WRAP53 | 0.68 |
| 5972 | 3 | 4 | | | IV-2 | WRAP73 | 0.80 |
| 5973 | 3 | 4 | | | IV-2 | WRNIP1 | 0.71 |
| 5974 | 3 | 4 | | | IV-2 | WTAP | 0.93 |
| 5975 | 3 | 4 | | | IV-2 | WTIP | 0.67 |
| 5976 | 3 | 4 | | | IV-2 | WWP1 | 0.84 |
| 5977 | 3 | 4 | | | IV-2 | XKR8 | 0.74 |
| 5978 | 3 | 4 | | | IV-2 | XPC | 0.87 |
| 5979 | 3 | 4 | | | IV-2 | XPO5 | 0.89 |
| 5980 | 3 | 4 | | | IV-2 | XPO7 | 0.76 |
| 5981 | 3 | 4 | | | IV-2 | XPOT | 0.92 |
| 5982 | 3 | 4 | | | IV-2 | XRCC4 | 0.96 |
| 5983 | 3 | 4 | | | IV-2 | XRCC5 | 0.98 |
| 5984 | 3 | 4 | | | IV-2 | YARS2 | 0.97 |
| 5985 | 3 | 4 | | | IV-2 | YEATS2 | 0.94 |
| 5986 | 3 | 4 | | | IV-2 | YEATS4 | 0.87 |
| 5987 | 3 | 4 | | | IV-2 | YES1 | 0.92 |
| 5988 | 3 | 4 | | | IV-2 | YIPF1 | 0.69 |
| 5989 | 3 | 4 | | | IV-2 | YTHDF1 | 0.80 |
| 5990 | 3 | 4 | | | IV-2 | YWHAE | 0.68 |
| 5991 | 3 | 4 | | | IV-2 | YWHAG | 0.97 |
| 5992 | 3 | 4 | | | IV-2 | YWHAQ | 0.81 |
| 5993 | 3 | 4 | | | IV-2 | ZBTB2 | 0.97 |
| 5994 | 3 | 4 | | | IV-2 | ZBTB25 | 0.88 |
| 5995 | 3 | 4 | | | IV-2 | ZBTB4 | 0.69 |
| 5996 | 3 | 4 | | | IV-2 | ZBTB48 | 0.70 |
| 5997 | 3 | 4 | | | IV-2 | ZBTB49 | 0.79 |
| 5998 | 3 | 4 | | | IV-2 | ZC3H10 | 0.91 |
| 5999 | 3 | 4 | | | IV-2 | ZC3HC1 | 0.78 |
| 6000 | 3 | 4 | | | IV-2 | ZC4H2 | 0.78 |
| 6001 | 3 | 4 | | | IV-2 | ZCCHC17 | 0.77 |
| 6002 | 3 | 4 | | | IV-2 | ZCCHC24 | 0.75 |
| 6003 | 3 | 4 | | | IV-2 | ZCCHC3 | 0.90 |
| 6004 | 3 | 4 | | | IV-2 | ZCCHC8 | 0.96 |
| 6005 | 3 | 4 | | | IV-2 | ZCCHC9 | 0.96 |
| 6006 | 3 | 4 | | | IV-2 | ZCRB1 | 0.98 |
| 6007 | 3 | 4 | | | IV-2 | ZDHHC13 | 0.86 |
| 6008 | 3 | 4 | | | IV-2 | ZDHHC14 | 0.83 |
| 6009 | 3 | 4 | | | IV-2 | ZDHHC15 | 0.96 |
| 6010 | 3 | 4 | | | IV-2 | ZDHHC18 | 0.68 |
| 6011 | 3 | 4 | | | IV-2 | ZDHHC7 | 0.77 |
| 6012 | 3 | 4 | | | IV-2 | ZEB1-AS1 | 0.98 |
| 6013 | 3 | 4 | | | IV-2 | ZFAND1 | 0.88 |
| 6014 | 3 | 4 | | | IV-2 | ZFAND2A | 0.71 |
| 6015 | 3 | 4 | | | IV-2 | ZFAND3 | 0.70 |
| 6016 | 3 | 4 | | | IV-2 | ZFP36 | 0.94 |
| 6017 | 3 | 4 | | | IV-2 | ZFYVE27 | 0.74 |
| 6018 | 3 | 4 | | | IV-2 | ZFYVE28 | 0.73 |
| 6019 | 3 | 4 | | | IV-2 | ZHX2 | 0.82 |
| 6020 | 3 | 4 | | | IV-2 | ZMAT2 | 0.76 |
| 6021 | 3 | 4 | | | IV-2 | ZMAT5 | 0.74 |
| 6022 | 3 | 4 | | | IV-2 | ZMIZ1 | 0.82 |
| 6023 | 3 | 4 | | | IV-2 | ZMPSTE24 | 0.95 |
| 6024 | 3 | 4 | | | IV-2 | ZMYM3 | 0.76 |
| 6025 | 3 | 4 | | | IV-2 | ZMYND15 | 0.71 |
| 6026 | 3 | 4 | | | IV-2 | ZNF142 | 0.73 |
| 6027 | 3 | 4 | | | IV-2 | ZNF143 | 0.83 |
| 6028 | 3 | 4 | | | IV-2 | ZNF16 | 0.87 |
| 6029 | 3 | 4 | | | IV-2 | ZNF174 | 0.76 |
| 6030 | 3 | 4 | | | IV-2 | ZNF207 | 0.80 |
| 6031 | 3 | 4 | | | IV-2 | ZNF22 | 0.96 |
| 6032 | 3 | 4 | | | IV-2 | ZNF263 | 0.83 |
| 6033 | 3 | 4 | | | IV-2 | ZNF317 | 0.82 |
| 6034 | 3 | 4 | | | IV-2 | ZNF32 | 0.93 |
| 6035 | 3 | 4 | | | IV-2 | ZNF324B | 0.71 |
| 6036 | 3 | 4 | | | IV-2 | ZNF329 | 0.84 |
| 6037 | 3 | 4 | | | IV-2 | ZNF330 | 0.91 |
| 6038 | 3 | 4 | | | IV-2 | ZNF341 | 0.70 |
| 6039 | 3 | 4 | | | IV-2 | ZNF367 | 0.89 |
| 6040 | 3 | 4 | | | IV-2 | ZNF385C | 0.81 |
| 6041 | 3 | 4 | | | IV-2 | ZNF394 | 0.92 |
| 6042 | 3 | 4 | | | IV-2 | ZNF395 | 0.88 |
| 6043 | 3 | 4 | | | IV-2 | ZNF410 | 0.93 |
| 6044 | 3 | 4 | | | IV-2 | ZNF438 | 0.88 |
| 6045 | 3 | 4 | | | IV-2 | ZNF497 | 0.86 |
| 6046 | 3 | 4 | | | IV-2 | ZNF498 | 0.94 |
| 6047 | 3 | 4 | | | IV-2 | ZNF503 | 0.94 |
| 6048 | 3 | 4 | | | IV-2 | ZNF517 | 0.82 |
| 6049 | 3 | 4 | | | IV-2 | ZNF526 | 1.00 |
| 6050 | 3 | 4 | | | IV-2 | ZNF569 | 1.00 |
| 6051 | 3 | 4 | | | IV-2 | ZNF576 | 0.69 |
| 6052 | 3 | 4 | | | IV-2 | ZNF584 | 0.75 |
| 6053 | 3 | 4 | | | IV-2 | ZNF586 | 0.85 |
| 6054 | 3 | 4 | | | IV-2 | ZNF639 | 0.78 |
| 6055 | 3 | 4 | | | IV-2 | ZNF652 | 0.98 |
| 6056 | 3 | 4 | | | IV-2 | ZNF667 | 0.96 |
| 6057 | 3 | 4 | | | IV-2 | ZNF691 | 0.75 |
| 6058 | 3 | 4 | | | IV-2 | ZNF707 | 0.89 |
| 6059 | 3 | 4 | | | IV-2 | ZNF720 | 0.97 |
| 6060 | 3 | 4 | | | IV-2 | ZNF738 | 0.94 |
| 6061 | 3 | 4 | | | IV-2 | ZNF74 | 0.71 |
| 6062 | 3 | 4 | | | IV-2 | ZNF740 | 0.95 |
| 6063 | 3 | 4 | | | IV-2 | ZNF764 | 0.95 |
| 6064 | 3 | 4 | | | IV-2 | ZNF771 | 0.68 |
| 6065 | 3 | 4 | | | IV-2 | ZNF784 | 0.83 |
| 6066 | 3 | 4 | | | IV-2 | ZNF815 | 0.78 |
| 6067 | 3 | 4 | | | IV-2 | ZNF830 | 0.81 |
| 6068 | 3 | 4 | | | IV-2 | ZNF835 | 0.70 |
| 6069 | 3 | 4 | | | IV-2 | ZNFX1-AS1 | 0.71 |
| 6070 | 3 | 4 | | | IV-2 | ZNHIT6 | 0.94 |
| 6071 | 3 | 4 | | | IV-2 | ZSCAN2 | 0.77 |
| 6072 | 3 | 4 | | | IV-2 | ZSCAN22 | 0.97 |
| 6073 | 3 | 4 | | | IV-2 | ZXDC | 0.89 |
| 6074 | 3 | 4 | | | IV-2 | ZZEF1 | 0.87 |
| 6075 | 3 | 4 | | | IV-1 | A2LD1 | 1.16 |
| 6076 | 3 | 4 | | | IV-1 | AACSP1 | 1.09 |
| 6077 | 3 | 4 | | | IV-1 | AASDH | 1.35 |
| 6078 | 3 | 4 | | | IV-1 | ABCB10 | 1.35 |
| 6079 | 3 | 4 | | | IV-1 | ABCC5 | 1.22 |
| 6080 | 3 | 4 | | | IV-1 | ABHD3 | 1.32 |
| 6081 | 3 | 4 | | | IV-1 | ABI3BP | 1.03 |
| 6082 | 3 | 4 | | | IV-1 | ACAA2 | 1.05 |
| 6083 | 3 | 4 | | | IV-1 | ACACA | 1.15 |
| 6084 | 3 | 4 | | | IV-1 | ACAD8 | 1.24 |
| 6085 | 3 | 4 | | | IV-1 | ACAP2 | 1.38 |
| 6086 | 3 | 4 | | | IV-1 | ACBD3 | 1.04 |
| 6087 | 3 | 4 | | | IV-1 | ACLY | 1.02 |
| 6088 | 3 | 4 | | | IV-1 | ACO1 | 1.46 |
| 6089 | 3 | 4 | | | IV-1 | ACOT13 | 1.24 |
| 6090 | 3 | 4 | | | IV-1 | ACOT2 | 1.22 |
| 6091 | 3 | 4 | | | IV-1 | ACOX1 | 1.05 |
| 6092 | 3 | 4 | | | IV-1 | ACP5 | 1.23 |
| 6093 | 3 | 4 | | | IV-1 | ACRBP | 1.03 |
| 6094 | 3 | 4 | | | IV-1 | ACRC | 1.28 |
| 6095 | 3 | 4 | | | IV-1 | ACSL3 | 1.27 |
| 6096 | 3 | 4 | | | IV-1 | ACSL4 | 1.12 |
| 6097 | 3 | 4 | | | IV-1 | ACSL5 | 1.10 |
| 6098 | 3 | 4 | | | IV-1 | ACSM5 | 1.26 |
| 6099 | 3 | 4 | | | IV-1 | ACTA1 | 1.12 |
| 6100 | 3 | 4 | | | IV-1 | ACTG2 | 1.08 |
| 6101 | 3 | 4 | | | IV-1 | ACTR2 | 1.08 |
| 6102 | 3 | 4 | | | IV-1 | ACTR3 | 1.02 |
| 6103 | 3 | 4 | | | IV-1 | ACTR8 | 1.17 |
| 6104 | 3 | 4 | | | IV-1 | ACVR2B | 1.13 |
| 6105 | 3 | 4 | | | IV-1 | ADAL | 1.03 |
| 6106 | 3 | 4 | | | IV-1 | ADAM22 | 1.14 |
| 6107 | 3 | 4 | | | IV-1 | ADAM28 | 1.18 |
| 6108 | 3 | 4 | | | IV-1 | ADAM9 | 1.07 |
| 6109 | 3 | 4 | | | IV-1 | ADAMTS9-AS2 | 1.27 |
| 6110 | 3 | 4 | | | IV-1 | ADCY7 | 1.37 |
| 6111 | 3 | 4 | | | IV-1 | ADCYAP1 | 1.13 |
| 6112 | 3 | 4 | | | IV-1 | ADCYAP1R1 | 1.15 |
| 6113 | 3 | 4 | | | IV-1 | ADH1A | 1.03 |
| 6114 | 3 | 4 | | | IV-1 | ADH1C | 1.08 |
| 6115 | 3 | 4 | | | IV-1 | ADH5 | 1.09 |
| 6116 | 3 | 4 | | | IV-1 | ADIPOR2 | 1.02 |
| 6117 | 3 | 4 | | | IV-1 | ADNP2 | 1.25 |
| 6118 | 3 | 4 | | | IV-1 | ADORA3 | 1.45 |
| 6119 | 3 | 4 | | | IV-1 | AFAP1 | 1.04 |
| 6120 | 3 | 4 | | | IV-1 | AFF1 | 1.37 |
| 6121 | 3 | 4 | | | IV-1 | AFF3 | 1.09 |
| 6122 | 3 | 4 | | | IV-1 | AFTPH | 1.32 |
| 6123 | 3 | 4 | | | IV-1 | AGFG1 | 1.19 |
| 6124 | 3 | 4 | | | IV-1 | AGGF1 | 1.35 |
| 6125 | 3 | 4 | | | IV-1 | AGL | 1.19 |
| 6126 | 3 | 4 | | | IV-1 | AGPS | 1.07 |
| 6127 | 3 | 4 | | | IV-1 | AGR2 | 1.05 |
| 6128 | 3 | 4 | | | IV-1 | AGTPBP1 | 1.21 |
| 6129 | 3 | 4 | | | IV-1 | AHCTF1 | 1.17 |
| 6130 | 3 | 4 | | | IV-1 | AHCYL1 | 1.03 |
| 6131 | 3 | 4 | | | IV-1 | AHCYL2 | 1.07 |
| 6132 | 3 | 4 | | | IV-1 | AIMP1 | 1.08 |
| 6133 | 3 | 4 | | | IV-1 | AK3 | 1.04 |
| 6134 | 3 | 4 | | | IV-1 | AK7 | 1.09 |
| 6135 | 3 | 4 | | | IV-1 | AKAP13 | 1.02 |
| 6136 | 3 | 4 | | | IV-1 | AKIRIN1 | 1.05 |
| 6137 | 3 | 4 | | | IV-1 | AKNA | 1.10 |
| 6138 | 3 | 4 | | | IV-1 | ALCAM | 1.42 |
| 6139 | 3 | 4 | | | IV-1 | ALDH1L2 | 1.31 |
| 6140 | 3 | 4 | | | IV-1 | ALDH3A2 | 1.27 |
| 6141 | 3 | 4 | | | IV-1 | ALG10 | 1.12 |

Fig. 38 - 33

| | | | | | | | | | | | | | | | | |
|---|---|---|---|---|---|---|---|---|---|---|---|---|---|---|---|---|
| 6142 | 3 | 4 | | | IV-1 | ALG10B | 1.06 | 6238 | 3 | 4 | | | IV-1 | ASF1A | 1.18 |
| 6143 | 3 | 4 | | | IV-1 | ALG11 | 1.11 | 6239 | 3 | 4 | | | IV-1 | ASH1L | 1.41 |
| 6144 | 3 | 4 | | | IV-1 | ALG6 | 1.03 | 6240 | 3 | 4 | | | IV-1 | ASTE1 | 1.37 |
| 6145 | 3 | 4 | | | IV-1 | ALG9 | 1.18 | 6241 | 3 | 4 | | | IV-1 | ATAD1 | 1.17 |
| 6146 | 3 | 4 | | | IV-1 | ALKBH8 | 1.20 | 6242 | 3 | 4 | | | IV-1 | ATF2 | 1.35 |
| 6147 | 3 | 4 | | | IV-1 | ALMS1 | 1.20 | 6243 | 3 | 4 | | | IV-1 | ATF6 | 1.13 |
| 6148 | 3 | 4 | | | IV-1 | ALPK3 | 1.09 | 6244 | 3 | 4 | | | IV-1 | ATF7IP2 | 1.26 |
| 6149 | 3 | 4 | | | IV-1 | ALS2 | 1.11 | 6245 | 3 | 4 | | | IV-1 | ATG12 | 1.21 |
| 6150 | 3 | 4 | | | IV-1 | AMACR | 1.26 | 6246 | 3 | 4 | | | IV-1 | ATG14 | 1.20 |
| 6151 | 3 | 4 | | | IV-1 | AMIGO2 | 1.09 | 6247 | 3 | 4 | | | IV-1 | ATG2B | 1.24 |
| 6152 | 3 | 4 | | | IV-1 | AMMECR1L | 1.17 | 6248 | 3 | 4 | | | IV-1 | ATG4C | 1.07 |
| 6153 | 3 | 4 | | | IV-1 | AMN | 1.03 | 6249 | 3 | 4 | | | IV-1 | ATG5 | 1.08 |
| 6154 | 3 | 4 | | | IV-1 | AMN1 | 1.10 | 6250 | 3 | 4 | | | IV-1 | ATL2 | 1.06 |
| 6155 | 3 | 4 | | | IV-1 | AMY2A | 1.39 | 6251 | 3 | 4 | | | IV-1 | ATMIN | 1.08 |
| 6156 | 3 | 4 | | | IV-1 | ANGPT4 | 1.26 | 6252 | 3 | 4 | | | IV-1 | ATP11C | 1.22 |
| 6157 | 3 | 4 | | | IV-1 | ANKFY1 | 1.09 | 6253 | 3 | 4 | | | IV-1 | ATP13A3 | 1.42 |
| 6158 | 3 | 4 | | | IV-1 | ANKMY2 | 1.10 | 6254 | 3 | 4 | | | IV-1 | ATP2B4 | 1.17 |
| 6159 | 3 | 4 | | | IV-1 | ANKRA2 | 1.28 | 6255 | 3 | 4 | | | IV-1 | ATP2C1 | 1.02 |
| 6160 | 3 | 4 | | | IV-1 | ANKRD13A | 1.17 | 6256 | 3 | 4 | | | IV-1 | ATP5A1 | 1.09 |
| 6161 | 3 | 4 | | | IV-1 | ANKRD13C | 1.12 | 6257 | 3 | 4 | | | IV-1 | ATP6V0A2 | 1.13 |
| 6162 | 3 | 4 | | | IV-1 | ANKRD17 | 1.45 | 6258 | 3 | 4 | | | IV-1 | ATP6V1C1 | 1.37 |
| 6163 | 3 | 4 | | | IV-1 | ANKRD18A | 1.16 | 6259 | 3 | 4 | | | IV-1 | ATP7B | 1.37 |
| 6164 | 3 | 4 | | | IV-1 | ANKRD28 | 1.22 | 6260 | 3 | 4 | | | IV-1 | ATP8B4 | 1.07 |
| 6165 | 3 | 4 | | | IV-1 | ANKRD32 | 1.29 | 6261 | 3 | 4 | | | IV-1 | ATR | 1.03 |
| 6166 | 3 | 4 | | | IV-1 | ANKRD40 | 1.03 | 6262 | 3 | 4 | | | IV-1 | ATRN | 1.23 |
| 6167 | 3 | 4 | | | IV-1 | ANKRD46 | 1.43 | 6263 | 3 | 4 | | | IV-1 | ATXN1 | 1.25 |
| 6168 | 3 | 4 | | | IV-1 | ANKRD5 | 1.49 | 6264 | 3 | 4 | | | IV-1 | ATXN2 | 1.26 |
| 6169 | 3 | 4 | | | IV-1 | ANKRD50 | 1.08 | 6265 | 3 | 4 | | | IV-1 | ATXN3 | 1.20 |
| 6170 | 3 | 4 | | | IV-1 | ANKRD6 | 1.50 | 6266 | 3 | 4 | | | IV-1 | AUH | 1.20 |
| 6171 | 3 | 4 | | | IV-1 | ANKS1A | 1.04 | 6267 | 3 | 4 | | | IV-1 | AVL9 | 1.49 |
| 6172 | 3 | 4 | | | IV-1 | ANO6 | 1.03 | 6268 | 3 | 4 | | | IV-1 | AZI2 | 1.44 |
| 6173 | 3 | 4 | | | IV-1 | ANP32E | 1.10 | 6269 | 3 | 4 | | | IV-1 | AZIN1 | 1.05 |
| 6174 | 3 | 4 | | | IV-1 | ANTXR2 | 1.13 | 6270 | 3 | 4 | | | IV-1 | B3GALNT2 | 1.27 |
| 6175 | 3 | 4 | | | IV-1 | AOAH | 1.28 | 6271 | 3 | 4 | | | IV-1 | B3GALTL | 1.23 |
| 6176 | 3 | 4 | | | IV-1 | AP1AR | 1.31 | 6272 | 3 | 4 | | | IV-1 | B4GALT4 | 1.18 |
| 6177 | 3 | 4 | | | IV-1 | AP1G1 | 1.26 | 6273 | 3 | 4 | | | IV-1 | BACE1 | 1.01 |
| 6178 | 3 | 4 | | | IV-1 | AP1S3 | 1.19 | 6274 | 3 | 4 | | | IV-1 | BARD1 | 1.46 |
| 6179 | 3 | 4 | | | IV-1 | AP3B1 | 1.27 | 6275 | 3 | 4 | | | IV-1 | BAZ1B | 1.03 |
| 6180 | 3 | 4 | | | IV-1 | AP3M1 | 1.20 | 6276 | 3 | 4 | | | IV-1 | BAZ2A | 1.06 |
| 6181 | 3 | 4 | | | IV-1 | AP3M2 | 1.32 | 6277 | 3 | 4 | | | IV-1 | BB52 | 1.13 |
| 6182 | 3 | 4 | | | IV-1 | AP4E1 | 1.02 | 6278 | 3 | 4 | | | IV-1 | BBX | 1.50 |
| 6183 | 3 | 4 | | | IV-1 | AP4S1 | 1.24 | 6279 | 3 | 4 | | | IV-1 | BCAP29 | 1.08 |
| 6184 | 3 | 4 | | | IV-1 | APAF1 | 1.25 | 6280 | 3 | 4 | | | IV-1 | BCAS1 | 1.00 |
| 6185 | 3 | 4 | | | IV-1 | APBB1IP | 1.04 | 6281 | 3 | 4 | | | IV-1 | BCAS2 | 1.01 |
| 6186 | 3 | 4 | | | IV-1 | APC | 1.30 | 6282 | 3 | 4 | | | IV-1 | BCAS4 | 1.22 |
| 6187 | 3 | 4 | | | IV-1 | APLF | 1.18 | 6283 | 3 | 4 | | | IV-1 | BCAT1 | 1.28 |
| 6188 | 3 | 4 | | | IV-1 | APOA1 | 1.02 | 6284 | 3 | 4 | | | IV-1 | BCL2 | 1.20 |
| 6189 | 3 | 4 | | | IV-1 | APOBEC2 | 1.02 | 6285 | 3 | 4 | | | IV-1 | BCLAF1 | 1.08 |
| 6190 | 3 | 4 | | | IV-1 | APOBEC3A | 1.37 | 6286 | 3 | 4 | | | IV-1 | BDH1 | 1.08 |
| 6191 | 3 | 4 | | | IV-1 | APOL6 | 1.05 | 6287 | 3 | 4 | | | IV-1 | BDP1 | 1.48 |
| 6192 | 3 | 4 | | | IV-1 | APPBP2 | 1.04 | 6288 | 3 | 4 | | | IV-1 | BEST4 | 1.17 |
| 6193 | 3 | 4 | | | IV-1 | APPL2 | 1.02 | 6289 | 3 | 4 | | | IV-1 | BET1 | 1.16 |
| 6194 | 3 | 4 | | | IV-1 | APTX | 1.01 | 6290 | 3 | 4 | | | IV-1 | BEX5 | 1.05 |
| 6195 | 3 | 4 | | | IV-1 | ARFGEF1 | 1.29 | 6291 | 3 | 4 | | | IV-1 | BHLHA15 | 1.02 |
| 6196 | 3 | 4 | | | IV-1 | ARFIP1 | 1.37 | 6292 | 3 | 4 | | | IV-1 | BHLHB9 | 1.18 |
| 6197 | 3 | 4 | | | IV-1 | ARHGAP12 | 1.39 | 6293 | 3 | 4 | | | IV-1 | BICD1 | 1.02 |
| 6198 | 3 | 4 | | | IV-1 | ARHGAP15 | 1.50 | 6294 | 3 | 4 | | | IV-1 | BIRC6 | 1.47 |
| 6199 | 3 | 4 | | | IV-1 | ARHGAP18 | 1.06 | 6295 | 3 | 4 | | | IV-1 | BLOC1S2 | 1.05 |
| 6200 | 3 | 4 | | | IV-1 | ARHGAP19 | 1.36 | 6296 | 3 | 4 | | | IV-1 | BMP2K | 1.13 |
| 6201 | 3 | 4 | | | IV-1 | ARHGAP20 | 1.33 | 6297 | 3 | 4 | | | IV-1 | BMP8B | 1.27 |
| 6202 | 3 | 4 | | | IV-1 | ARHGAP24 | 1.12 | 6298 | 3 | 4 | | | IV-1 | BMPR2 | 1.16 |
| 6203 | 3 | 4 | | | IV-1 | ARHGAP25 | 1.13 | 6299 | 3 | 4 | | | IV-1 | BMS1 | 1.05 |
| 6204 | 3 | 4 | | | IV-1 | ARHGAP28 | 1.39 | 6300 | 3 | 4 | | | IV-1 | BMS1P4 | 1.37 |
| 6205 | 3 | 4 | | | IV-1 | ARHGAP29 | 1.14 | 6301 | 3 | 4 | | | IV-1 | BNIP2 | 1.14 |
| 6206 | 3 | 4 | | | IV-1 | ARHGAP32 | 1.04 | 6302 | 3 | 4 | | | IV-1 | BNIP3L | 1.38 |
| 6207 | 3 | 4 | | | IV-1 | ARHGAP5 | 1.14 | 6303 | 3 | 4 | | | IV-1 | BPTF | 1.34 |
| 6208 | 3 | 4 | | | IV-1 | ARHGAP9 | 1.02 | 6304 | 3 | 4 | | | IV-1 | BRAP | 1.05 |
| 6209 | 3 | 4 | | | IV-1 | ARHGEF26 | 1.45 | 6305 | 3 | 4 | | | IV-1 | BRCA1 | 1.08 |
| 6210 | 3 | 4 | | | IV-1 | ARHGEF6 | 1.43 | 6306 | 3 | 4 | | | IV-1 | BRCC3 | 1.16 |
| 6211 | 3 | 4 | | | IV-1 | ARHGEF9 | 1.05 | 6307 | 3 | 4 | | | IV-1 | BRMS1L | 1.19 |
| 6212 | 3 | 4 | | | IV-1 | ARID1A | 1.08 | 6308 | 3 | 4 | | | IV-1 | BRWD1 | 1.16 |
| 6213 | 3 | 4 | | | IV-1 | ARID1B | 1.31 | 6309 | 3 | 4 | | | IV-1 | BRWD3 | 1.48 |
| 6214 | 3 | 4 | | | IV-1 | ARID2 | 1.39 | 6310 | 3 | 4 | | | IV-1 | BST1 | 1.10 |
| 6215 | 3 | 4 | | | IV-1 | ARID5B | 1.17 | 6311 | 3 | 4 | | | IV-1 | BTBD1 | 1.03 |
| 6216 | 3 | 4 | | | IV-1 | ARIH1 | 1.19 | 6312 | 3 | 4 | | | IV-1 | BTBD16 | 1.08 |
| 6217 | 3 | 4 | | | IV-1 | ARL1 | 1.09 | 6313 | 3 | 4 | | | IV-1 | BTN2A2 | 1.09 |
| 6218 | 3 | 4 | | | IV-1 | ARL15 | 1.49 | 6314 | 3 | 4 | | | IV-1 | BTN3A1 | 1.15 |
| 6219 | 3 | 4 | | | IV-1 | ARL5B | 1.34 | 6315 | 3 | 4 | | | IV-1 | BVES | 1.26 |
| 6220 | 3 | 4 | | | IV-1 | ARL6 | 1.44 | 6316 | 3 | 4 | | | IV-1 | BZW1 | 1.06 |
| 6221 | 3 | 4 | | | IV-1 | ARL6IP6 | 1.01 | 6317 | 3 | 4 | | | IV-1 | C10orf140 | 1.17 |
| 6222 | 3 | 4 | | | IV-1 | ARMC1 | 1.08 | 6318 | 3 | 4 | | | IV-1 | C10orf32 | 1.08 |
| 6223 | 3 | 4 | | | IV-1 | ARMC12 | 1.05 | 6319 | 3 | 4 | | | IV-1 | C10orf46 | 1.40 |
| 6224 | 3 | 4 | | | IV-1 | ARMCX2 | 1.22 | 6320 | 3 | 4 | | | IV-1 | C10orf81 | 1.03 |
| 6225 | 3 | 4 | | | IV-1 | ARMCX5 | 1.07 | 6321 | 3 | 4 | | | IV-1 | C11orf21 | 1.37 |
| 6226 | 3 | 4 | | | IV-1 | ARNT | 1.10 | 6322 | 3 | 4 | | | IV-1 | C11orf46 | 1.47 |
| 6227 | 3 | 4 | | | IV-1 | ARPM1 | 1.06 | 6323 | 3 | 4 | | | IV-1 | C11orf57 | 1.30 |
| 6228 | 3 | 4 | | | IV-1 | ARRDC3 | 1.16 | 6324 | 3 | 4 | | | IV-1 | C11orf58 | 1.01 |
| 6229 | 3 | 4 | | | IV-1 | ARSB | 1.02 | 6325 | 3 | 4 | | | IV-1 | C11orf73 | 1.25 |
| 6230 | 3 | 4 | | | IV-1 | ARSK | 1.12 | 6326 | 3 | 4 | | | IV-1 | C12orf23 | 1.24 |
| 6231 | 3 | 4 | | | IV-1 | ASAH1 | 1.18 | 6327 | 3 | 4 | | | IV-1 | C12orf73 | 1.11 |
| 6232 | 3 | 4 | | | IV-1 | ASAP1 | 1.28 | 6328 | 3 | 4 | | | IV-1 | C12orf76 | 1.25 |
| 6233 | 3 | 4 | | | IV-1 | ASB1 | 1.36 | 6329 | 3 | 4 | | | IV-1 | C14orf132 | 1.49 |
| 6234 | 3 | 4 | | | IV-1 | ASB2 | 1.17 | 6330 | 3 | 4 | | | IV-1 | C14orf135 | 1.21 |
| 6235 | 3 | 4 | | | IV-1 | ASB7 | 1.09 | 6331 | 3 | 4 | | | IV-1 | C14orf45 | 1.20 |
| 6236 | 3 | 4 | | | IV-1 | ASB8 | 1.15 | 6332 | 3 | 4 | | | IV-1 | C14orf64 | 1.49 |
| 6237 | 3 | 4 | | | IV-1 | ASCC3 | 1.05 | 6333 | 3 | 4 | | | IV-1 | C15orf17 | 1.02 |

Fig. 38 - 34

| | | | | | | | | | | | | | | |
|---|---|---|---|---|---|---|---|---|---|---|---|---|---|---|
| 6334 | 3 | 4 | | | IV-1 | C15orf40 | 1.09 | 6430 | 3 | 4 | | | IV-1 | CATSPERG | 1.07 |
| 6335 | 3 | 4 | | | IV-1 | C15orf41 | 1.12 | 6431 | 3 | 4 | | | IV-1 | CBFA2T2 | 1.12 |
| 6336 | 3 | 4 | | | IV-1 | C15orf5 | 1.07 | 6432 | 3 | 4 | | | IV-1 | CBFB | 1.20 |
| 6337 | 3 | 4 | | | IV-1 | C15orf58 | 1.01 | 6433 | 3 | 4 | | | IV-1 | CBLN3 | 1.04 |
| 6338 | 3 | 4 | | | IV-1 | C16orf3 | 1.30 | 6434 | 3 | 4 | | | IV-1 | CBR4 | 1.27 |
| 6339 | 3 | 4 | | | IV-1 | C16orf52 | 1.49 | 6435 | 3 | 4 | | | IV-1 | CBWD3 | 1.06 |
| 6340 | 3 | 4 | | | IV-1 | C17orf108 | 1.16 | 6436 | 3 | 4 | | | IV-1 | CBX5 | 1.44 |
| 6341 | 3 | 4 | | | IV-1 | C17orf48 | 1.07 | 6437 | 3 | 4 | | | IV-1 | CC2D2A | 1.04 |
| 6342 | 3 | 4 | | | IV-1 | C17orf69 | 1.34 | 6438 | 3 | 4 | | | IV-1 | CCDC111 | 1.17 |
| 6343 | 3 | 4 | | | IV-1 | C17orf75 | 1.07 | 6439 | 3 | 4 | | | IV-1 | CCDC117 | 1.10 |
| 6344 | 3 | 4 | | | IV-1 | C17orf80 | 1.06 | 6440 | 3 | 4 | | | IV-1 | CCDC121 | 1.25 |
| 6345 | 3 | 4 | | | IV-1 | C18orf25 | 1.35 | 6441 | 3 | 4 | | | IV-1 | CCDC125 | 1.30 |
| 6346 | 3 | 4 | | | IV-1 | C19orf12 | 1.02 | 6442 | 3 | 4 | | | IV-1 | CCDC132 | 1.41 |
| 6347 | 3 | 4 | | | IV-1 | C19orf26 | 1.14 | 6443 | 3 | 4 | | | IV-1 | CCDC136 | 1.05 |
| 6348 | 3 | 4 | | | IV-1 | C19orf42 | 1.25 | 6444 | 3 | 4 | | | IV-1 | CCDC15 | 1.13 |
| 6349 | 3 | 4 | | | IV-1 | C19orf81 | 1.13 | 6445 | 3 | 4 | | | IV-1 | CCDC41 | 1.19 |
| 6350 | 3 | 4 | | | IV-1 | C1D | 1.08 | 6446 | 3 | 4 | | | IV-1 | CCDC43 | 1.11 |
| 6351 | 3 | 4 | | | IV-1 | C1orf109 | 1.28 | 6447 | 3 | 4 | | | IV-1 | CCDC68 | 1.03 |
| 6352 | 3 | 4 | | | IV-1 | C1orf130 | 1.14 | 6448 | 3 | 4 | | | IV-1 | CCDC71L | 1.29 |
| 6353 | 3 | 4 | | | IV-1 | C1orf150 | 1.31 | 6449 | 3 | 4 | | | IV-1 | CCDC88C | 1.14 |
| 6354 | 3 | 4 | | | IV-1 | C1orf158 | 1.15 | 6450 | 3 | 4 | | | IV-1 | CCDC89 | 1.46 |
| 6355 | 3 | 4 | | | IV-1 | C1orf162 | 1.33 | 6451 | 3 | 4 | | | IV-1 | CCDC91 | 1.14 |
| 6356 | 3 | 4 | | | IV-1 | C1orf21 | 1.03 | 6452 | 3 | 4 | | | IV-1 | CCL20 | 1.17 |
| 6357 | 3 | 4 | | | IV-1 | C1orf38 | 1.36 | 6453 | 3 | 4 | | | IV-1 | CCNC | 1.08 |
| 6358 | 3 | 4 | | | IV-1 | C1orf52 | 1.08 | 6454 | 3 | 4 | | | IV-1 | CCNG1 | 1.11 |
| 6359 | 3 | 4 | | | IV-1 | C1orf95 | 1.35 | 6455 | 3 | 4 | | | IV-1 | CCNG2 | 1.18 |
| 6360 | 3 | 4 | | | IV-1 | C1R | 1.03 | 6456 | 3 | 4 | | | IV-1 | CCNT1 | 1.34 |
| 6361 | 3 | 4 | | | IV-1 | C1S | 1.08 | 6457 | 3 | 4 | | | IV-1 | CCNYL1 | 1.19 |
| 6362 | 3 | 4 | | | IV-1 | C20orf166-AS1 | 1.08 | 6458 | 3 | 4 | | | IV-1 | CCP110 | 1.23 |
| 6363 | 3 | 4 | | | IV-1 | C20orf7 | 1.33 | 6459 | 3 | 4 | | | IV-1 | CCR8 | 1.43 |
| 6364 | 3 | 4 | | | IV-1 | C21orf15 | 1.15 | 6460 | 3 | 4 | | | IV-1 | CD14 | 1.47 |
| 6365 | 3 | 4 | | | IV-1 | C22orf46 | 1.24 | 6461 | 3 | 4 | | | IV-1 | CD164 | 1.01 |
| 6366 | 3 | 4 | | | IV-1 | C2CD3 | 1.37 | 6462 | 3 | 4 | | | IV-1 | CD200 | 1.36 |
| 6367 | 3 | 4 | | | IV-1 | C2orf15 | 1.25 | 6463 | 3 | 4 | | | IV-1 | CD247 | 1.45 |
| 6368 | 3 | 4 | | | IV-1 | C2orf44 | 1.45 | 6464 | 3 | 4 | | | IV-1 | CD274 | 1.23 |
| 6369 | 3 | 4 | | | IV-1 | C2orf63 | 1.21 | 6465 | 3 | 4 | | | IV-1 | CD28 | 1.24 |
| 6370 | 3 | 4 | | | IV-1 | C2orf68 | 1.10 | 6466 | 3 | 4 | | | IV-1 | CD300LB | 1.17 |
| 6371 | 3 | 4 | | | IV-1 | C2orf69 | 1.20 | 6467 | 3 | 4 | | | IV-1 | CD3D2 | 1.47 |
| 6372 | 3 | 4 | | | IV-1 | C3orf14 | 1.10 | 6468 | 3 | 4 | | | IV-1 | CD47 | 1.09 |
| 6373 | 3 | 4 | | | IV-1 | C3orf15 | 1.19 | 6469 | 3 | 4 | | | IV-1 | CDC14C | 1.09 |
| 6374 | 3 | 4 | | | IV-1 | C3orf17 | 1.07 | 6470 | 3 | 4 | | | IV-1 | CDC23 | 1.04 |
| 6375 | 3 | 4 | | | IV-1 | C3orf19 | 1.22 | 6471 | 3 | 4 | | | IV-1 | CDC40 | 1.36 |
| 6376 | 3 | 4 | | | IV-1 | C3orf23 | 1.06 | 6472 | 3 | 4 | | | IV-1 | CDC42SE1 | 1.17 |
| 6377 | 3 | 4 | | | IV-1 | C3orf70 | 1.13 | 6473 | 3 | 4 | | | IV-1 | CDC42SE2 | 1.04 |
| 6378 | 3 | 4 | | | IV-1 | C4orf3 | 1.05 | 6474 | 3 | 4 | | | IV-1 | CDC73 | 1.11 |
| 6379 | 3 | 4 | | | IV-1 | C5 | 1.14 | 6475 | 3 | 4 | | | IV-1 | CDH12 | 1.09 |
| 6380 | 3 | 4 | | | IV-1 | C5orf22 | 1.15 | 6476 | 3 | 4 | | | IV-1 | CDH2 | 1.05 |
| 6381 | 3 | 4 | | | IV-1 | C5orf24 | 1.42 | 6477 | 3 | 4 | | | IV-1 | CDK14 | 1.48 |
| 6382 | 3 | 4 | | | IV-1 | C5orf28 | 1.23 | 6478 | 3 | 4 | | | IV-1 | CDK5RAP2 | 1.15 |
| 6383 | 3 | 4 | | | IV-1 | C5orf30 | 1.28 | 6479 | 3 | 4 | | | IV-1 | CDK6 | 1.09 |
| 6384 | 3 | 4 | | | IV-1 | C5orf43 | 1.06 | 6480 | 3 | 4 | | | IV-1 | CDK8 | 1.26 |
| 6385 | 3 | 4 | | | IV-1 | C5orf44 | 1.45 | 6481 | 3 | 4 | | | IV-1 | CDKN1B | 1.12 |
| 6386 | 3 | 4 | | | IV-1 | C5orf45 | 1.12 | 6482 | 3 | 4 | | | IV-1 | CDKN2AIP | 1.14 |
| 6387 | 3 | 4 | | | IV-1 | C5orf51 | 1.50 | 6483 | 3 | 4 | | | IV-1 | CDS1 | 1.15 |
| 6388 | 3 | 4 | | | IV-1 | C5orf63 | 1.41 | 6484 | 3 | 4 | | | IV-1 | CDS2 | 1.07 |
| 6389 | 3 | 4 | | | IV-1 | C5orf65 | 1.01 | 6485 | 3 | 4 | | | IV-1 | CELF1 | 1.01 |
| 6390 | 3 | 4 | | | IV-1 | C6 | 1.06 | 6486 | 3 | 4 | | | IV-1 | CENPBD1 | 1.28 |
| 6391 | 3 | 4 | | | IV-1 | C6orf162 | 1.15 | 6487 | 3 | 4 | | | IV-1 | CENPJ | 1.23 |
| 6392 | 3 | 4 | | | IV-1 | C6orf211 | 1.35 | 6488 | 3 | 4 | | | IV-1 | CENPQ | 1.10 |
| 6393 | 3 | 4 | | | IV-1 | C6orf225 | 1.08 | 6489 | 3 | 4 | | | IV-1 | CEP120 | 1.33 |
| 6394 | 3 | 4 | | | IV-1 | C6orf57 | 1.23 | 6490 | 3 | 4 | | | IV-1 | CEP152 | 1.06 |
| 6395 | 3 | 4 | | | IV-1 | C6orf89 | 1.07 | 6491 | 3 | 4 | | | IV-1 | CEP170 | 1.48 |
| 6396 | 3 | 4 | | | IV-1 | C7orf23 | 1.26 | 6492 | 3 | 4 | | | IV-1 | CEP192 | 1.01 |
| 6397 | 3 | 4 | | | IV-1 | C7orf31 | 1.01 | 6493 | 3 | 4 | | | IV-1 | CEP350 | 1.34 |
| 6398 | 3 | 4 | | | IV-1 | C7orf41 | 1.19 | 6494 | 3 | 4 | | | IV-1 | CEP44 | 1.48 |
| 6399 | 3 | 4 | | | IV-1 | C8orf37 | 1.02 | 6495 | 3 | 4 | | | IV-1 | CEP57 | 1.26 |
| 6400 | 3 | 4 | | | IV-1 | C8orf38 | 1.32 | 6496 | 3 | 4 | | | IV-1 | CEP63 | 1.20 |
| 6401 | 3 | 4 | | | IV-1 | C8orf40 | 1.05 | 6497 | 3 | 4 | | | IV-1 | CEP68 | 1.18 |
| 6402 | 3 | 4 | | | IV-1 | C8orf56 | 1.33 | 6498 | 3 | 4 | | | IV-1 | CEP72 | 1.00 |
| 6403 | 3 | 4 | | | IV-1 | C8orf83 | 1.10 | 6499 | 3 | 4 | | | IV-1 | CEP76 | 1.26 |
| 6404 | 3 | 4 | | | IV-1 | C9orf106 | 1.16 | 6500 | 3 | 4 | | | IV-1 | CEP78 | 1.10 |
| 6405 | 3 | 4 | | | IV-1 | C9orf129 | 1.18 | 6501 | 3 | 4 | | | IV-1 | CEP8SL | 1.32 |
| 6406 | 3 | 4 | | | IV-1 | C9orf156 | 1.28 | 6502 | 3 | 4 | | | IV-1 | CEPT1 | 1.06 |
| 6407 | 3 | 4 | | | IV-1 | C9orf40 | 1.21 | 6503 | 3 | 4 | | | IV-1 | CES3 | 1.17 |
| 6408 | 3 | 4 | | | IV-1 | C9orf68 | 1.27 | 6504 | 3 | 4 | | | IV-1 | CGGBP1 | 1.43 |
| 6409 | 3 | 4 | | | IV-1 | C9orf71 | 1.40 | 6505 | 3 | 4 | | | IV-1 | CGNL1 | 1.25 |
| 6410 | 3 | 4 | | | IV-1 | C9orf91 | 1.05 | 6506 | 3 | 4 | | | IV-1 | CHAC1 | 1.49 |
| 6411 | 3 | 4 | | | IV-1 | CA5B | 1.22 | 6507 | 3 | 4 | | | IV-1 | CHAC2 | 1.18 |
| 6412 | 3 | 4 | | | IV-1 | CA8 | 1.47 | 6508 | 3 | 4 | | | IV-1 | CHAMP1 | 1.47 |
| 6413 | 3 | 4 | | | IV-1 | CACHD1 | 1.30 | 6509 | 3 | 4 | | | IV-1 | CHCHD7 | 1.08 |
| 6414 | 3 | 4 | | | IV-1 | CACNA1G | 1.17 | 6510 | 3 | 4 | | | IV-1 | CHD2 | 1.30 |
| 6415 | 3 | 4 | | | IV-1 | CADM1 | 1.28 | 6511 | 3 | 4 | | | IV-1 | CHIC1 | 1.26 |
| 6416 | 3 | 4 | | | IV-1 | CALCOCO2 | 1.01 | 6512 | 3 | 4 | | | IV-1 | CHML | 1.16 |
| 6417 | 3 | 4 | | | IV-1 | CALCRL | 1.49 | 6513 | 3 | 4 | | | IV-1 | CHMP2B | 1.06 |
| 6418 | 3 | 4 | | | IV-1 | CALML6 | 1.46 | 6514 | 3 | 4 | | | IV-1 | CHMP5 | 1.23 |
| 6419 | 3 | 4 | | | IV-1 | CAMK2D | 1.06 | 6515 | 3 | 4 | | | IV-1 | CHORDC1 | 1.03 |
| 6420 | 3 | 4 | | | IV-1 | CAMK2G | 1.14 | 6516 | 3 | 4 | | | IV-1 | CHRDL1 | 1.16 |
| 6421 | 3 | 4 | | | IV-1 | CAMSAP2 | 1.37 | 6517 | 3 | 4 | | | IV-1 | CHRNA10 | 1.16 |
| 6422 | 3 | 4 | | | IV-1 | CAPN7 | 1.20 | 6518 | 3 | 4 | | | IV-1 | CHUK | 1.01 |
| 6423 | 3 | 4 | | | IV-1 | CAPZA3 | 1.30 | 6519 | 3 | 4 | | | IV-1 | CHURC1 | 1.05 |
| 6424 | 3 | 4 | | | IV-1 | CARD6 | 1.20 | 6520 | 3 | 4 | | | IV-1 | CIAO1 | 1.13 |
| 6425 | 3 | 4 | | | IV-1 | CASC4 | 1.17 | 6521 | 3 | 4 | | | IV-1 | CIITA | 1.07 |
| 6426 | 3 | 4 | | | IV-1 | CASD1 | 1.23 | 6522 | 3 | 4 | | | IV-1 | CKAP2 | 1.06 |
| 6427 | 3 | 4 | | | IV-1 | CASP6 | 1.07 | 6523 | 3 | 4 | | | IV-1 | CKLF | 1.28 |
| 6428 | 3 | 4 | | | IV-1 | CAT | 1.01 | 6524 | 3 | 4 | | | IV-1 | CLASP2 | 1.26 |
| 6429 | 3 | 4 | | | IV-1 | CATSPER2P1 | 1.28 | 6525 | 3 | 4 | | | IV-1 | CLDN16 | 1.46 |

Fig. 38 - 35

| | | | | | | | | | | | | | | |
|---|---|---|---|---|---|---|---|---|---|---|---|---|---|---|
| 6526 | 3 | 4 | | | IV-1 | CLEC2B | 1.14 | 6622 | 3 | 4 | | | IV-1 | DCUN1D2 | 1.19 |
| 6527 | 3 | 4 | | | IV-1 | CLEC4A | 1.18 | 6623 | 3 | 4 | | | IV-1 | DCUN1D3 | 1.46 |
| 6528 | 3 | 4 | | | IV-1 | CLEC4F | 1.09 | 6624 | 3 | 4 | | | IV-1 | DDR2 | 1.43 |
| 6529 | 3 | 4 | | | IV-1 | CLEC7A | 1.35 | 6625 | 3 | 4 | | | IV-1 | DDX18 | 1.03 |
| 6530 | 3 | 4 | | | IV-1 | CLIC4 | 1.17 | 6626 | 3 | 4 | | | IV-1 | DDX5 | 1.22 |
| 6531 | 3 | 4 | | | IV-1 | CLIC5 | 1.04 | 6627 | 3 | 4 | | | IV-1 | DDX52 | 1.36 |
| 6532 | 3 | 4 | | | IV-1 | CLINT1 | 1.37 | 6628 | 3 | 4 | | | IV-1 | DDX58 | 1.14 |
| 6533 | 3 | 4 | | | IV-1 | CLN5 | 1.29 | 6629 | 3 | 4 | | | IV-1 | DDX59 | 1.08 |
| 6534 | 3 | 4 | | | IV-1 | CLOCK | 1.10 | 6630 | 3 | 4 | | | IV-1 | DDX6 | 1.19 |
| 6535 | 3 | 4 | | | IV-1 | CLTC | 1.12 | 6631 | 3 | 4 | | | IV-1 | DEFB1 | 1.27 |
| 6536 | 3 | 4 | | | IV-1 | CLUAP1 | 1.22 | 6632 | 3 | 4 | | | IV-1 | DEFB109P1 | 1.00 |
| 6537 | 3 | 4 | | | IV-1 | CMAS | 1.09 | 6633 | 3 | 4 | | | IV-1 | DEK | 1.12 |
| 6538 | 3 | 4 | | | IV-1 | CMBL | 1.26 | 6634 | 3 | 4 | | | IV-1 | DENND4A | 1.16 |
| 6539 | 3 | 4 | | | IV-1 | CMPK1 | 1.06 | 6635 | 3 | 4 | | | IV-1 | DENND4C | 1.23 |
| 6540 | 3 | 4 | | | IV-1 | CMTM4 | 1.31 | 6636 | 3 | 4 | | | IV-1 | DENND5A | 1.04 |
| 6541 | 3 | 4 | | | IV-1 | CMYA5 | 1.36 | 6637 | 3 | 4 | | | IV-1 | DENND5B | 1.01 |
| 6542 | 3 | 4 | | | IV-1 | CNOT1 | 1.38 | 6638 | 3 | 4 | | | IV-1 | DENR | 1.01 |
| 6543 | 3 | 4 | | | IV-1 | CNOT4 | 1.00 | 6639 | 3 | 4 | | | IV-1 | DEPDC5 | 1.20 |
| 6544 | 3 | 4 | | | IV-1 | CNOT6 | 1.06 | 6640 | 3 | 4 | | | IV-1 | DEPTOR | 1.28 |
| 6545 | 3 | 4 | | | IV-1 | CNOT6L | 1.15 | 6641 | 3 | 4 | | | IV-1 | DGKG | 1.00 |
| 6546 | 3 | 4 | | | IV-1 | CNOT7 | 1.11 | 6642 | 3 | 4 | | | IV-1 | DHFR | 1.35 |
| 6547 | 3 | 4 | | | IV-1 | CNOT8 | 1.03 | 6643 | 3 | 4 | | | IV-1 | DHH | 1.01 |
| 6548 | 3 | 4 | | | IV-1 | CNPY2 | 1.01 | 6644 | 3 | 4 | | | IV-1 | DHTKD1 | 1.40 |
| 6549 | 3 | 4 | | | IV-1 | COBLL1 | 1.35 | 6645 | 3 | 4 | | | IV-1 | DHX15 | 1.17 |
| 6550 | 3 | 4 | | | IV-1 | COG3 | 1.15 | 6646 | 3 | 4 | | | IV-1 | DHX33 | 1.25 |
| 6551 | 3 | 4 | | | IV-1 | COG5 | 1.03 | 6647 | 3 | 4 | | | IV-1 | DHX40 | 1.01 |
| 6552 | 3 | 4 | | | IV-1 | COIL | 1.17 | 6648 | 3 | 4 | | | IV-1 | DHX57 | 1.22 |
| 6553 | 3 | 4 | | | IV-1 | COL21A1 | 1.41 | 6649 | 3 | 4 | | | IV-1 | DIAPH2 | 1.20 |
| 6554 | 3 | 4 | | | IV-1 | COL4A3BP | 1.30 | 6650 | 3 | 4 | | | IV-1 | DICER1 | 1.26 |
| 6555 | 3 | 4 | | | IV-1 | COL6A6 | 1.26 | 6651 | 3 | 4 | | | IV-1 | DIEXF | 1.10 |
| 6556 | 3 | 4 | | | IV-1 | COMMD2 | 1.04 | 6652 | 3 | 4 | | | IV-1 | DIP2C | 1.43 |
| 6557 | 3 | 4 | | | IV-1 | COMMD8 | 1.00 | 6653 | 3 | 4 | | | IV-1 | DIS3 | 1.35 |
| 6558 | 3 | 4 | | | IV-1 | COPB1 | 1.30 | 6654 | 3 | 4 | | | IV-1 | DIS3L | 1.04 |
| 6559 | 3 | 4 | | | IV-1 | COPB2 | 1.10 | 6655 | 3 | 4 | | | IV-1 | DKK2 | 1.18 |
| 6560 | 3 | 4 | | | IV-1 | COQ10A | 1.06 | 6656 | 3 | 4 | | | IV-1 | DLAT | 1.02 |
| 6561 | 3 | 4 | | | IV-1 | COQ6 | 1.35 | 6657 | 3 | 4 | | | IV-1 | DLD | 1.37 |
| 6562 | 3 | 4 | | | IV-1 | COX19 | 1.17 | 6658 | 3 | 4 | | | IV-1 | DLG1 | 1.42 |
| 6563 | 3 | 4 | | | IV-1 | COX7B | 1.41 | 6659 | 3 | 4 | | | IV-1 | DLL1 | 1.21 |
| 6564 | 3 | 4 | | | IV-1 | CP | 1.44 | 6660 | 3 | 4 | | | IV-1 | DMBX1 | 1.09 |
| 6565 | 3 | 4 | | | IV-1 | CPD | 1.31 | 6661 | 3 | 4 | | | IV-1 | DMXL1 | 1.36 |
| 6566 | 3 | 4 | | | IV-1 | CPE | 1.12 | 6662 | 3 | 4 | | | IV-1 | DMXL2 | 1.46 |
| 6567 | 3 | 4 | | | IV-1 | CPEB3 | 1.23 | 6663 | 3 | 4 | | | IV-1 | DNAH17 | 1.08 |
| 6568 | 3 | 4 | | | IV-1 | CPOX | 1.08 | 6664 | 3 | 4 | | | IV-1 | DNAJA1 | 1.19 |
| 6569 | 3 | 4 | | | IV-1 | CPPED1 | 1.29 | 6665 | 3 | 4 | | | IV-1 | DNAJA2 | 1.16 |
| 6570 | 3 | 4 | | | IV-1 | CPQ | 1.04 | 6666 | 3 | 4 | | | IV-1 | DNAJB9 | 1.38 |
| 6571 | 3 | 4 | | | IV-1 | CPS1 | 1.44 | 6667 | 3 | 4 | | | IV-1 | DNAJC10 | 1.33 |
| 6572 | 3 | 4 | | | IV-1 | CPSF6 | 1.04 | 6668 | 3 | 4 | | | IV-1 | DNAJC15 | 1.22 |
| 6573 | 3 | 4 | | | IV-1 | CPT2 | 1.11 | 6669 | 3 | 4 | | | IV-1 | DNAJC16 | 1.46 |
| 6574 | 3 | 4 | | | IV-1 | CPXM1 | 1.30 | 6670 | 3 | 4 | | | IV-1 | DNAJC21 | 1.17 |
| 6575 | 3 | 4 | | | IV-1 | CREB1 | 1.08 | 6671 | 3 | 4 | | | IV-1 | DNAJC28 | 1.22 |
| 6576 | 3 | 4 | | | IV-1 | CREB3L2 | 1.21 | 6672 | 3 | 4 | | | IV-1 | DNAJC3 | 1.08 |
| 6577 | 3 | 4 | | | IV-1 | CREM | 1.43 | 6673 | 3 | 4 | | | IV-1 | DNAJC7 | 1.05 |
| 6578 | 3 | 4 | | | IV-1 | CRIM1 | 1.01 | 6674 | 3 | 4 | | | IV-1 | DNAL1 | 1.41 |
| 6579 | 3 | 4 | | | IV-1 | CRIPT | 1.05 | 6675 | 3 | 4 | | | IV-1 | DOCK10 | 1.45 |
| 6580 | 3 | 4 | | | IV-1 | CRISPLD1 | 1.06 | 6676 | 3 | 4 | | | IV-1 | DOCK7 | 1.23 |
| 6581 | 3 | 4 | | | IV-1 | CRK | 1.42 | 6677 | 3 | 4 | | | IV-1 | DOCK9 | 1.03 |
| 6582 | 3 | 4 | | | IV-1 | CRLF3 | 1.42 | 6678 | 3 | 4 | | | IV-1 | DOK7 | 1.12 |
| 6583 | 3 | 4 | | | IV-1 | CRNKL1 | 1.10 | 6679 | 3 | 4 | | | IV-1 | DONSON | 1.23 |
| 6584 | 3 | 4 | | | IV-1 | CSAG3 | 1.30 | 6680 | 3 | 4 | | | IV-1 | DOPEY1 | 1.30 |
| 6585 | 3 | 4 | | | IV-1 | CSDE1 | 1.12 | 6681 | 3 | 4 | | | IV-1 | DPH3 | 1.28 |
| 6586 | 3 | 4 | | | IV-1 | CSE1L | 1.03 | 6682 | 3 | 4 | | | IV-1 | DPP6 | 1.08 |
| 6587 | 3 | 4 | | | IV-1 | CSNK1G3 | 1.05 | 6683 | 3 | 4 | | | IV-1 | DPT | 1.45 |
| 6588 | 3 | 4 | | | IV-1 | CSTA | 1.22 | 6684 | 3 | 4 | | | IV-1 | DPY19L3 | 1.36 |
| 6589 | 3 | 4 | | | IV-1 | CTAGE1 | 1.01 | 6685 | 3 | 4 | | | IV-1 | DPY19L4 | 1.27 |
| 6590 | 3 | 4 | | | IV-1 | CTDSPL2 | 1.44 | 6686 | 3 | 4 | | | IV-1 | DRAM1 | 1.03 |
| 6591 | 3 | 4 | | | IV-1 | CTNNB1 | 1.34 | 6687 | 3 | 4 | | | IV-1 | DROSHA | 1.13 |
| 6592 | 3 | 4 | | | IV-1 | CTPS | 1.14 | 6688 | 3 | 4 | | | IV-1 | DSE | 1.49 |
| 6593 | 3 | 4 | | | IV-1 | CTR9 | 1.25 | 6689 | 3 | 4 | | | IV-1 | DSG2 | 1.16 |
| 6594 | 3 | 4 | | | IV-1 | CTSC | 1.41 | 6690 | 3 | 4 | | | IV-1 | DST | 1.35 |
| 6595 | 3 | 4 | | | IV-1 | CTSK | 1.30 | 6691 | 3 | 4 | | | IV-1 | DSTNP2 | 1.05 |
| 6596 | 3 | 4 | | | IV-1 | CTSO | 1.25 | 6692 | 3 | 4 | | | IV-1 | DTX3L | 1.06 |
| 6597 | 3 | 4 | | | IV-1 | CTTNBP2 | 1.39 | 6693 | 3 | 4 | | | IV-1 | DUS4L | 1.11 |
| 6598 | 3 | 4 | | | IV-1 | CUL2 | 1.07 | 6694 | 3 | 4 | | | IV-1 | DUSP15 | 1.27 |
| 6599 | 3 | 4 | | | IV-1 | CUL3 | 1.46 | 6695 | 3 | 4 | | | IV-1 | DUSP19 | 1.20 |
| 6600 | 3 | 4 | | | IV-1 | CUL4A | 1.11 | 6696 | 3 | 4 | | | IV-1 | DUSP3 | 1.04 |
| 6601 | 3 | 4 | | | IV-1 | CUL4B | 1.32 | 6697 | 3 | 4 | | | IV-1 | DUSP5P | 1.01 |
| 6602 | 3 | 4 | | | IV-1 | CUL9 | 1.05 | 6698 | 3 | 4 | | | IV-1 | DYNC1I2 | 1.21 |
| 6603 | 3 | 4 | | | IV-1 | CWC25 | 1.07 | 6699 | 3 | 4 | | | IV-1 | DYNC1LI2 | 1.47 |
| 6604 | 3 | 4 | | | IV-1 | CWC27 | 1.17 | 6700 | 3 | 4 | | | IV-1 | DYNLT3 | 1.11 |
| 6605 | 3 | 4 | | | IV-1 | CXADRP2 | 1.35 | 6701 | 3 | 4 | | | IV-1 | DYRK1A | 1.19 |
| 6606 | 3 | 4 | | | IV-1 | CXADRP3 | 1.14 | 6702 | 3 | 4 | | | IV-1 | DYX1C1 | 1.08 |
| 6607 | 3 | 4 | | | IV-1 | CXCL12 | 1.40 | 6703 | 3 | 4 | | | IV-1 | E2F3 | 1.43 |
| 6608 | 3 | 4 | | | IV-1 | CXorf38 | 1.01 | 6704 | 3 | 4 | | | IV-1 | E2F6 | 1.19 |
| 6609 | 3 | 4 | | | IV-1 | CYB5D1 | 1.05 | 6705 | 3 | 4 | | | IV-1 | EBF1 | 1.45 |
| 6610 | 3 | 4 | | | IV-1 | CYLD | 1.23 | 6706 | 3 | 4 | | | IV-1 | ECHDC1 | 1.33 |
| 6611 | 3 | 4 | | | IV-1 | CYP20A1 | 1.44 | 6707 | 3 | 4 | | | IV-1 | EDAR | 1.06 |
| 6612 | 3 | 4 | | | IV-1 | CYP2C9 | 1.24 | 6708 | 3 | 4 | | | IV-1 | EDEM3 | 1.24 |
| 6613 | 3 | 4 | | | IV-1 | CYP3A5 | 1.19 | 6709 | 3 | 4 | | | IV-1 | EDNRA | 1.35 |
| 6614 | 3 | 4 | | | IV-1 | CYS1 | 1.32 | 6710 | 3 | 4 | | | IV-1 | EEA1 | 1.08 |
| 6615 | 3 | 4 | | | IV-1 | DAPK1 | 1.49 | 6711 | 3 | 4 | | | IV-1 | EED | 1.27 |
| 6616 | 3 | 4 | | | IV-1 | DAPP1 | 1.05 | 6712 | 3 | 4 | | | IV-1 | EFCAB11 | 1.11 |
| 6617 | 3 | 4 | | | IV-1 | DCAF16 | 1.41 | 6713 | 3 | 4 | | | IV-1 | EFCAB4B | 1.36 |
| 6618 | 3 | 4 | | | IV-1 | DCBLD1 | 1.06 | 6714 | 3 | 4 | | | IV-1 | EFCAB7 | 1.21 |
| 6619 | 3 | 4 | | | IV-1 | DCBLD2 | 1.15 | 6715 | 3 | 4 | | | IV-1 | EFEMP1 | 1.07 |
| 6620 | 3 | 4 | | | IV-1 | DCN | 1.32 | 6716 | 3 | 4 | | | IV-1 | EFR3A | 1.03 |
| 6621 | 3 | 4 | | | IV-1 | DCTN4 | 1.31 | 6717 | 3 | 4 | | | IV-1 | EGLN1 | 1.00 |

Fig. 38 - 36

| | | | | | | | |
|---|---|---|---|---|---|---|---|
| 6718 | 3 | 4 | | | IV-1 | EHHADH | 1.21 |
| 6719 | 3 | 4 | | | IV-1 | EIF2A | 1.00 |
| 6720 | 3 | 4 | | | IV-1 | EIF2AK3 | 1.22 |
| 6721 | 3 | 4 | | | IV-1 | EIF2AK4 | 1.19 |
| 6722 | 3 | 4 | | | IV-1 | EIF2C4 | 1.48 |
| 6723 | 3 | 4 | | | IV-1 | EIF3J | 1.10 |
| 6724 | 3 | 4 | | | IV-1 | EIF4A2 | 1.09 |
| 6725 | 3 | 4 | | | IV-1 | EIF5A2 | 1.11 |
| 6726 | 3 | 4 | | | IV-1 | ELF2 | 1.14 |
| 6727 | 3 | 4 | | | IV-1 | ELFN2 | 1.09 |
| 6728 | 3 | 4 | | | IV-1 | ELK4 | 1.34 |
| 6729 | 3 | 4 | | | IV-1 | ELL3 | 1.10 |
| 6730 | 3 | 4 | | | IV-1 | ELP2 | 1.00 |
| 6731 | 3 | 4 | | | IV-1 | EMILIN1 | 1.37 |
| 6732 | 3 | 4 | | | IV-1 | EML1 | 1.27 |
| 6733 | 3 | 4 | | | IV-1 | EML4 | 1.38 |
| 6734 | 3 | 4 | | | IV-1 | EML6 | 1.13 |
| 6735 | 3 | 4 | | | IV-1 | ENAH | 1.06 |
| 6736 | 3 | 4 | | | IV-1 | ENC1 | 1.41 |
| 6737 | 3 | 4 | | | IV-1 | ENDOU | 1.06 |
| 6738 | 3 | 4 | | | IV-1 | ENOX2 | 1.18 |
| 6739 | 3 | 4 | | | IV-1 | ENTPD7 | 1.07 |
| 6740 | 3 | 4 | | | IV-1 | EP300 | 1.12 |
| 6741 | 3 | 4 | | | IV-1 | EP400 | 1.07 |
| 6742 | 3 | 4 | | | IV-1 | EPB41L5 | 1.20 |
| 6743 | 3 | 4 | | | IV-1 | EPC1 | 1.17 |
| 6744 | 3 | 4 | | | IV-1 | EPC2 | 1.38 |
| 6745 | 3 | 4 | | | IV-1 | EPHA3 | 1.15 |
| 6746 | 3 | 4 | | | IV-1 | EPS15 | 1.16 |
| 6747 | 3 | 4 | | | IV-1 | EPS8 | 1.08 |
| 6748 | 3 | 4 | | | IV-1 | ERCC4 | 1.24 |
| 6749 | 3 | 4 | | | IV-1 | ERCC8 | 1.19 |
| 6750 | 3 | 4 | | | IV-1 | ERICH1 | 1.09 |
| 6751 | 3 | 4 | | | IV-1 | ERLEC1 | 1.06 |
| 6752 | 3 | 4 | | | IV-1 | ERLIN2 | 1.12 |
| 6753 | 3 | 4 | | | IV-1 | ERVK13-1 | 1.27 |
| 6754 | 3 | 4 | | | IV-1 | ESRRG | 1.08 |
| 6755 | 3 | 4 | | | IV-1 | ETFDH | 1.23 |
| 6756 | 3 | 4 | | | IV-1 | ETS1 | 1.07 |
| 6757 | 3 | 4 | | | IV-1 | ETV6 | 1.07 |
| 6758 | 3 | 4 | | | IV-1 | EVC | 1.06 |
| 6759 | 3 | 4 | | | IV-1 | EVI5 | 1.20 |
| 6760 | 3 | 4 | | | IV-1 | EXOC1 | 1.11 |
| 6761 | 3 | 4 | | | IV-1 | EXOC5 | 1.26 |
| 6762 | 3 | 4 | | | IV-1 | EXOC6 | 1.24 |
| 6763 | 3 | 4 | | | IV-1 | EXOSC3 | 1.04 |
| 6764 | 3 | 4 | | | IV-1 | EYA3 | 1.26 |
| 6765 | 3 | 4 | | | IV-1 | EZH2 | 1.01 |
| 6766 | 3 | 4 | | | IV-1 | FAF2 | 1.10 |
| 6767 | 3 | 4 | | | IV-1 | FAM102B | 1.04 |
| 6768 | 3 | 4 | | | IV-1 | FAM105A | 1.25 |
| 6769 | 3 | 4 | | | IV-1 | FAM105B | 1.11 |
| 6770 | 3 | 4 | | | IV-1 | FAM115C | 1.21 |
| 6771 | 3 | 4 | | | IV-1 | FAM117B | 1.11 |
| 6772 | 3 | 4 | | | IV-1 | FAM120A | 1.09 |
| 6773 | 3 | 4 | | | IV-1 | FAM120AOS | 1.05 |
| 6774 | 3 | 4 | | | IV-1 | FAM122C | 1.34 |
| 6775 | 3 | 4 | | | IV-1 | FAM126A | 1.43 |
| 6776 | 3 | 4 | | | IV-1 | FAM13C | 1.47 |
| 6777 | 3 | 4 | | | IV-1 | FAM160B1 | 1.19 |
| 6778 | 3 | 4 | | | IV-1 | FAM161A | 1.33 |
| 6779 | 3 | 4 | | | IV-1 | FAM171B | 1.07 |
| 6780 | 3 | 4 | | | IV-1 | FAM172A | 1.17 |
| 6781 | 3 | 4 | | | IV-1 | FAM173B | 1.09 |
| 6782 | 3 | 4 | | | IV-1 | FAM175B | 1.12 |
| 6783 | 3 | 4 | | | IV-1 | FAM177A1 | 1.02 |
| 6784 | 3 | 4 | | | IV-1 | FAM182B | 1.13 |
| 6785 | 3 | 4 | | | IV-1 | FAM184B | 1.11 |
| 6786 | 3 | 4 | | | IV-1 | FAM190B | 1.09 |
| 6787 | 3 | 4 | | | IV-1 | FAM198B | 1.30 |
| 6788 | 3 | 4 | | | IV-1 | FAM199X | 1.31 |
| 6789 | 3 | 4 | | | IV-1 | FAM19A2 | 1.22 |
| 6790 | 3 | 4 | | | IV-1 | FAM200A | 1.32 |
| 6791 | 3 | 4 | | | IV-1 | FAM208A | 1.12 |
| 6792 | 3 | 4 | | | IV-1 | FAM209A | 1.27 |
| 6793 | 3 | 4 | | | IV-1 | FAM20B | 1.35 |
| 6794 | 3 | 4 | | | IV-1 | FAM210A | 1.07 |
| 6795 | 3 | 4 | | | IV-1 | FAM216A | 1.40 |
| 6796 | 3 | 4 | | | IV-1 | FAM21C | 1.19 |
| 6797 | 3 | 4 | | | IV-1 | FAM22D | 1.26 |
| 6798 | 3 | 4 | | | IV-1 | FAM22G | 1.44 |
| 6799 | 3 | 4 | | | IV-1 | FAM25A | 1.21 |
| 6800 | 3 | 4 | | | IV-1 | FAM41C | 1.09 |
| 6801 | 3 | 4 | | | IV-1 | FAM45B | 1.18 |
| 6802 | 3 | 4 | | | IV-1 | FAM55C | 1.21 |
| 6803 | 3 | 4 | | | IV-1 | FAM65C | 1.03 |
| 6804 | 3 | 4 | | | IV-1 | FAM71F2 | 1.30 |
| 6805 | 3 | 4 | | | IV-1 | FAM82B | 1.12 |
| 6806 | 3 | 4 | | | IV-1 | FAM84B | 1.30 |
| 6807 | 3 | 4 | | | IV-1 | FAM86B2 | 1.03 |
| 6808 | 3 | 4 | | | IV-1 | FAM89A | 1.07 |
| 6809 | 3 | 4 | | | IV-1 | FAM8A1 | 1.24 |
| 6810 | 3 | 4 | | | IV-1 | FAM91A1 | 1.05 |
| 6811 | 3 | 4 | | | IV-1 | FANCC | 1.14 |
| 6812 | 3 | 4 | | | IV-1 | FAS | 1.16 |
| 6813 | 3 | 4 | | | IV-1 | FASLG | 1.08 |
| 6814 | 3 | 4 | | | IV-1 | FASTKD2 | 1.47 |
| 6815 | 3 | 4 | | | IV-1 | FBLN1 | 1.37 |
| 6816 | 3 | 4 | | | IV-1 | FBXL19-AS1 | 1.13 |
| 6817 | 3 | 4 | | | IV-1 | FBXL22 | 1.08 |
| 6818 | 3 | 4 | | | IV-1 | FBXL3 | 1.23 |
| 6819 | 3 | 4 | | | IV-1 | FBXO11 | 1.08 |
| 6820 | 3 | 4 | | | IV-1 | FBXO21 | 1.19 |
| 6821 | 3 | 4 | | | IV-1 | FBXO22 | 1.30 |
| 6822 | 3 | 4 | | | IV-1 | FBXO3 | 1.25 |
| 6823 | 3 | 4 | | | IV-1 | FBXO38 | 1.32 |
| 6824 | 3 | 4 | | | IV-1 | FBXO9 | 1.33 |
| 6825 | 3 | 4 | | | IV-1 | FBXW11 | 1.15 |
| 6826 | 3 | 4 | | | IV-1 | FBXW2 | 1.21 |
| 6827 | 3 | 4 | | | IV-1 | FCAR | 1.23 |
| 6828 | 3 | 4 | | | IV-1 | FCHO2 | 1.48 |
| 6829 | 3 | 4 | | | IV-1 | FCHSD2 | 1.01 |
| 6830 | 3 | 4 | | | IV-1 | FECH | 1.05 |
| 6831 | 3 | 4 | | | IV-1 | FEM1C | 1.17 |
| 6832 | 3 | 4 | | | IV-1 | FETUB | 1.38 |
| 6833 | 3 | 4 | | | IV-1 | FGD4 | 1.28 |
| 6834 | 3 | 4 | | | IV-1 | FGD5-AS1 | 1.19 |
| 6835 | 3 | 4 | | | IV-1 | FGD6 | 1.28 |
| 6836 | 3 | 4 | | | IV-1 | FGF10 | 1.16 |
| 6837 | 3 | 4 | | | IV-1 | FGF7 | 1.07 |
| 6838 | 3 | 4 | | | IV-1 | FGFR1OP2 | 1.34 |
| 6839 | 3 | 4 | | | IV-1 | FGFR2 | 1.11 |
| 6840 | 3 | 4 | | | IV-1 | FGGY | 1.25 |
| 6841 | 3 | 4 | | | IV-1 | FH | 1.04 |
| 6842 | 3 | 4 | | | IV-1 | FHL5 | 1.17 |
| 6843 | 3 | 4 | | | IV-1 | FIBIN | 1.14 |
| 6844 | 3 | 4 | | | IV-1 | FIG4 | 1.03 |
| 6845 | 3 | 4 | | | IV-1 | FILIP1L | 1.44 |
| 6846 | 3 | 4 | | | IV-1 | FIP1L1 | 1.06 |
| 6847 | 3 | 4 | | | IV-1 | FLJ12334 | 1.07 |
| 6848 | 3 | 4 | | | IV-1 | FLJ14107 | 1.12 |
| 6849 | 3 | 4 | | | IV-1 | FLJ39639 | 1.19 |
| 6850 | 3 | 4 | | | IV-1 | FLJ39739 | 1.08 |
| 6851 | 3 | 4 | | | IV-1 | FLJ41484 | 1.31 |
| 6852 | 3 | 4 | | | IV-1 | FLJ45513 | 1.36 |
| 6853 | 3 | 4 | | | IV-1 | FLJ45983 | 1.39 |
| 6854 | 3 | 4 | | | IV-1 | FLNC | 1.10 |
| 6855 | 3 | 4 | | | IV-1 | FLT4 | 1.03 |
| 6856 | 3 | 4 | | | IV-1 | FMNL2 | 1.27 |
| 6857 | 3 | 4 | | | IV-1 | FMNL3 | 1.14 |
| 6858 | 3 | 4 | | | IV-1 | FMO3 | 1.02 |
| 6859 | 3 | 4 | | | IV-1 | FMR1 | 1.34 |
| 6860 | 3 | 4 | | | IV-1 | FN1 | 1.31 |
| 6861 | 3 | 4 | | | IV-1 | FN3KRP | 1.02 |
| 6862 | 3 | 4 | | | IV-1 | FNBP1 | 1.09 |
| 6863 | 3 | 4 | | | IV-1 | FNIP1 | 1.25 |
| 6864 | 3 | 4 | | | IV-1 | FOXJ3 | 1.13 |
| 6865 | 3 | 4 | | | IV-1 | FOXN2 | 1.18 |
| 6866 | 3 | 4 | | | IV-1 | FOXN3 | 1.04 |
| 6867 | 3 | 4 | | | IV-1 | FPS88 | 1.36 |
| 6868 | 3 | 4 | | | IV-1 | FPR2 | 1.38 |
| 6869 | 3 | 4 | | | IV-1 | FRA10AC1 | 1.35 |
| 6870 | 3 | 4 | | | IV-1 | FRAS1 | 1.05 |
| 6871 | 3 | 4 | | | IV-1 | FRG1B | 1.03 |
| 6872 | 3 | 4 | | | IV-1 | FRMD6-AS1 | 1.06 |
| 6873 | 3 | 4 | | | IV-1 | FRRS1 | 1.37 |
| 6874 | 3 | 4 | | | IV-1 | FRY | 1.08 |
| 6875 | 3 | 4 | | | IV-1 | FST | 1.45 |
| 6876 | 3 | 4 | | | IV-1 | FUBP3 | 1.05 |
| 6877 | 3 | 4 | | | IV-1 | FUCA1 | 1.17 |
| 6878 | 3 | 4 | | | IV-1 | FUNDC1 | 1.04 |
| 6879 | 3 | 4 | | | IV-1 | FUT1 | 1.12 |
| 6880 | 3 | 4 | | | IV-1 | FUT10 | 1.03 |
| 6881 | 3 | 4 | | | IV-1 | FUT4 | 1.34 |
| 6882 | 3 | 4 | | | IV-1 | FUT7 | 1.01 |
| 6883 | 3 | 4 | | | IV-1 | FXC1 | 1.15 |
| 6884 | 3 | 4 | | | IV-1 | FXR1 | 1.03 |
| 6885 | 3 | 4 | | | IV-1 | FZD3 | 1.30 |
| 6886 | 3 | 4 | | | IV-1 | FZD6 | 1.11 |
| 6887 | 3 | 4 | | | IV-1 | G2E3 | 1.32 |
| 6888 | 3 | 4 | | | IV-1 | GAB1 | 1.24 |
| 6889 | 3 | 4 | | | IV-1 | GAB3 | 1.29 |
| 6890 | 3 | 4 | | | IV-1 | GABARAPL2 | 1.18 |
| 6891 | 3 | 4 | | | IV-1 | GABPA | 1.27 |
| 6892 | 3 | 4 | | | IV-1 | GABRP | 1.24 |
| 6893 | 3 | 4 | | | IV-1 | GALNT11 | 1.05 |
| 6894 | 3 | 4 | | | IV-1 | GALNT4 | 1.34 |
| 6895 | 3 | 4 | | | IV-1 | GALNT7 | 1.25 |
| 6896 | 3 | 4 | | | IV-1 | GAPT | 1.45 |
| 6897 | 3 | 4 | | | IV-1 | GAPVD1 | 1.29 |
| 6898 | 3 | 4 | | | IV-1 | GART | 1.10 |
| 6899 | 3 | 4 | | | IV-1 | GAS2L3 | 1.07 |
| 6900 | 3 | 4 | | | IV-1 | GATA2 | 1.15 |
| 6901 | 3 | 4 | | | IV-1 | GATC | 1.25 |
| 6902 | 3 | 4 | | | IV-1 | GBE1 | 1.05 |
| 6903 | 3 | 4 | | | IV-1 | GBP1 | 1.48 |
| 6904 | 3 | 4 | | | IV-1 | GCFC2 | 1.17 |
| 6905 | 3 | 4 | | | IV-1 | GCLC | 1.16 |
| 6906 | 3 | 4 | | | IV-1 | GCNT4 | 1.49 |
| 6907 | 3 | 4 | | | IV-1 | GDPD1 | 1.36 |
| 6908 | 3 | 4 | | | IV-1 | GEMIN2 | 1.17 |
| 6909 | 3 | 4 | | | IV-1 | GFM1 | 1.41 |

Fig. 38 - 37

| | | | | | | | | | | | | | |
|---|---|---|---|---|---|---|---|---|---|---|---|---|---|
| 6910 | 3 | 4 | | | IV-1 | GFM2 | 1.24 | 7006 | 3 | 4 | | IV-1 | HEXB | 1.23 |
| 6911 | 3 | 4 | | | IV-1 | GFPT1 | 1.00 | 7007 | 3 | 4 | | IV-1 | HGD | 1.35 |
| 6912 | 3 | 4 | | | IV-1 | GGCX | 1.11 | 7008 | 3 | 4 | | IV-1 | HHAT | 1.12 |
| 6913 | 3 | 4 | | | IV-1 | GGH | 1.07 | 7009 | 3 | 4 | | IV-1 | HHIPL1 | 1.01 |
| 6914 | 3 | 4 | | | IV-1 | GGNBP2 | 1.33 | 7010 | 3 | 4 | | IV-1 | HIC2 | 1.03 |
| 6915 | 3 | 4 | | | IV-1 | GHRLOS | 1.29 | 7011 | 3 | 4 | | IV-1 | HIF1A | 1.37 |
| 6916 | 3 | 4 | | | IV-1 | GIGYF2 | 1.00 | 7012 | 3 | 4 | | IV-1 | HIGD1B | 1.41 |
| 6917 | 3 | 4 | | | IV-1 | GK3P | 1.02 | 7013 | 3 | 4 | | IV-1 | HILS1 | 1.01 |
| 6918 | 3 | 4 | | | IV-1 | GKAP1 | 1.01 | 7014 | 3 | 4 | | IV-1 | HIST1H1C | 1.00 |
| 6919 | 3 | 4 | | | IV-1 | GLB1L3 | 1.30 | 7015 | 3 | 4 | | IV-1 | HIST1H2AG | 1.12 |
| 6920 | 3 | 4 | | | IV-1 | GLCCI1 | 1.42 | 7016 | 3 | 4 | | IV-1 | HIST1H2BB | 1.14 |
| 6921 | 3 | 4 | | | IV-1 | GLDN | 1.11 | 7017 | 3 | 4 | | IV-1 | HIST1H2BH | 1.02 |
| 6922 | 3 | 4 | | | IV-1 | GLIS3 | 1.00 | 7018 | 3 | 4 | | IV-1 | HIST1H2BL | 1.21 |
| 6923 | 3 | 4 | | | IV-1 | GMNN | 1.46 | 7019 | 3 | 4 | | IV-1 | HIST1H2BO | 1.38 |
| 6924 | 3 | 4 | | | IV-1 | GNA13 | 1.20 | 7020 | 3 | 4 | | IV-1 | HIST1H3E | 1.19 |
| 6925 | 3 | 4 | | | IV-1 | GNA14 | 1.08 | 7021 | 3 | 4 | | IV-1 | HIST1H4B | 1.37 |
| 6926 | 3 | 4 | | | IV-1 | GNE | 1.14 | 7022 | 3 | 4 | | IV-1 | HIST1H4D | 1.36 |
| 6927 | 3 | 4 | | | IV-1 | GNL2 | 1.12 | 7023 | 3 | 4 | | IV-1 | HIST1H4H | 1.47 |
| 6928 | 3 | 4 | | | IV-1 | GNPAT | 1.37 | 7024 | 3 | 4 | | IV-1 | HIST1H4I | 1.27 |
| 6929 | 3 | 4 | | | IV-1 | GNPDA1 | 1.01 | 7025 | 3 | 4 | | IV-1 | HIST2H3C | 1.20 |
| 6930 | 3 | 4 | | | IV-1 | GNPDA2 | 1.10 | 7026 | 3 | 4 | | IV-1 | HK3 | 1.01 |
| 6931 | 3 | 4 | | | IV-1 | GNPTAB | 1.25 | 7027 | 3 | 4 | | IV-1 | HLTF | 1.37 |
| 6932 | 3 | 4 | | | IV-1 | GNS | 1.19 | 7028 | 3 | 4 | | IV-1 | HNRNPA2B1 | 1.16 |
| 6933 | 3 | 4 | | | IV-1 | GOLGA3 | 1.20 | 7029 | 3 | 4 | | IV-1 | HNRNPA3 | 1.23 |
| 6934 | 3 | 4 | | | IV-1 | GOLGB1 | 1.23 | 7030 | 3 | 4 | | IV-1 | HNRNPA3P1 | 1.10 |
| 6935 | 3 | 4 | | | IV-1 | GOLM1 | 1.03 | 7031 | 3 | 4 | | IV-1 | HNRNPH3 | 1.07 |
| 6936 | 3 | 4 | | | IV-1 | GOLT1B | 1.33 | 7032 | 3 | 4 | | IV-1 | HNRPLL | 1.20 |
| 6937 | 3 | 4 | | | IV-1 | GOPC | 1.47 | 7033 | 3 | 4 | | IV-1 | HOMER1 | 1.39 |
| 6938 | 3 | 4 | | | IV-1 | GOSR1 | 1.34 | 7034 | 3 | 4 | | IV-1 | HOOK3 | 1.38 |
| 6939 | 3 | 4 | | | IV-1 | GOSR2 | 1.04 | 7035 | 3 | 4 | | IV-1 | HPO7349 | 1.15 |
| 6940 | 3 | 4 | | | IV-1 | GP1BA | 1.19 | 7036 | 3 | 4 | | IV-1 | HP1BP3 | 1.12 |
| 6941 | 3 | 4 | | | IV-1 | GPATCH1 | 1.00 | 7037 | 3 | 4 | | IV-1 | HPGDS | 1.15 |
| 6942 | 3 | 4 | | | IV-1 | GPATCH4 | 1.05 | 7038 | 3 | 4 | | IV-1 | HPS3 | 1.10 |
| 6943 | 3 | 4 | | | IV-1 | GPATCH8 | 1.20 | 7039 | 3 | 4 | | IV-1 | HPS5 | 1.31 |
| 6944 | 3 | 4 | | | IV-1 | GPBP1 | 1.02 | 7040 | 3 | 4 | | IV-1 | HPX | 1.36 |
| 6945 | 3 | 4 | | | IV-1 | GPC4 | 1.17 | 7041 | 3 | 4 | | IV-1 | HS2ST1 | 1.08 |
| 6946 | 3 | 4 | | | IV-1 | GPC6 | 1.48 | 7042 | 3 | 4 | | IV-1 | HSD17B11 | 1.15 |
| 6947 | 3 | 4 | | | IV-1 | GPCPD1 | 1.31 | 7043 | 3 | 4 | | IV-1 | HSD17B14 | 1.09 |
| 6948 | 3 | 4 | | | IV-1 | GPD1L | 1.28 | 7044 | 3 | 4 | | IV-1 | HSDL1 | 1.37 |
| 6949 | 3 | 4 | | | IV-1 | GPD2 | 1.14 | 7045 | 3 | 4 | | IV-1 | HSP90AA4P | 1.12 |
| 6950 | 3 | 4 | | | IV-1 | GPM6A | 1.06 | 7046 | 3 | 4 | | IV-1 | HSP90AB4P | 1.06 |
| 6951 | 3 | 4 | | | IV-1 | GPR111 | 1.07 | 7047 | 3 | 4 | | IV-1 | HSP90B1 | 1.40 |
| 6952 | 3 | 4 | | | IV-1 | GPR132 | 1.30 | 7048 | 3 | 4 | | IV-1 | HSP90B3P | 1.37 |
| 6953 | 3 | 4 | | | IV-1 | GPR141 | 1.03 | 7049 | 3 | 4 | | IV-1 | HSPA12A | 1.28 |
| 6954 | 3 | 4 | | | IV-1 | GPR160 | 1.05 | 7050 | 3 | 4 | | IV-1 | HSPA13 | 1.30 |
| 6955 | 3 | 4 | | | IV-1 | GPR55 | 1.39 | 7051 | 3 | 4 | | IV-1 | HSPA14 | 1.08 |
| 6956 | 3 | 4 | | | IV-1 | GPR65 | 1.32 | 7052 | 3 | 4 | | IV-1 | HSPA4 | 1.40 |
| 6957 | 3 | 4 | | | IV-1 | GPR75 | 1.26 | 7053 | 3 | 4 | | IV-1 | HSPA9 | 1.00 |
| 6958 | 3 | 4 | | | IV-1 | GPR89B | 1.36 | 7054 | 3 | 4 | | IV-1 | HSPG2 | 1.03 |
| 6959 | 3 | 4 | | | IV-1 | GPR97 | 1.08 | 7055 | 3 | 4 | | IV-1 | HSPH1 | 1.37 |
| 6960 | 3 | 4 | | | IV-1 | GPRASP2 | 1.17 | 7056 | 3 | 4 | | IV-1 | HUS1 | 1.20 |
| 6961 | 3 | 4 | | | IV-1 | GPT2 | 1.44 | 7057 | 3 | 4 | | IV-1 | HVCN1 | 1.17 |
| 6962 | 3 | 4 | | | IV-1 | GPX8 | 1.02 | 7058 | 3 | 4 | | IV-1 | IBTK | 1.19 |
| 6963 | 3 | 4 | | | IV-1 | GRIA2 | 1.12 | 7059 | 3 | 4 | | IV-1 | ICA1L | 1.23 |
| 6964 | 3 | 4 | | | IV-1 | GRIA3 | 1.01 | 7060 | 3 | 4 | | IV-1 | ICAM1 | 1.23 |
| 6965 | 3 | 4 | | | IV-1 | GRIA4 | 1.27 | 7061 | 3 | 4 | | IV-1 | ICAM4 | 1.47 |
| 6966 | 3 | 4 | | | IV-1 | GRIK2 | 1.14 | 7062 | 3 | 4 | | IV-1 | ICK | 1.46 |
| 6967 | 3 | 4 | | | IV-1 | GRIN3A | 1.04 | 7063 | 3 | 4 | | IV-1 | ICOS | 1.21 |
| 6968 | 3 | 4 | | | IV-1 | GRIP1 | 1.24 | 7064 | 3 | 4 | | IV-1 | ID1 | 1.34 |
| 6969 | 3 | 4 | | | IV-1 | GSPT1 | 1.03 | 7065 | 3 | 4 | | IV-1 | IFI16 | 1.02 |
| 6970 | 3 | 4 | | | IV-1 | GSTA4 | 1.42 | 7066 | 3 | 4 | | IV-1 | IFIT1 | 1.41 |
| 6971 | 3 | 4 | | | IV-1 | GTDC1 | 1.07 | 7067 | 3 | 4 | | IV-1 | IFIT3 | 1.09 |
| 6972 | 3 | 4 | | | IV-1 | GTF2E1 | 1.01 | 7068 | 3 | 4 | | IV-1 | IFT74 | 1.11 |
| 6973 | 3 | 4 | | | IV-1 | GTF2F2 | 1.02 | 7069 | 3 | 4 | | IV-1 | IFT88 | 1.03 |
| 6974 | 3 | 4 | | | IV-1 | GTF2H1 | 1.23 | 7070 | 3 | 4 | | IV-1 | IGF1R | 1.32 |
| 6975 | 3 | 4 | | | IV-1 | GTF2H2B | 1.41 | 7071 | 3 | 4 | | IV-1 | IGFALS | 1.04 |
| 6976 | 3 | 4 | | | IV-1 | GTF2H2C | 1.29 | 7072 | 3 | 4 | | IV-1 | IGFBP5 | 1.23 |
| 6977 | 3 | 4 | | | IV-1 | GTF3C3 | 1.21 | 7073 | 3 | 4 | | IV-1 | IGIP | 1.29 |
| 6978 | 3 | 4 | | | IV-1 | GTPBP10 | 1.42 | 7074 | 3 | 4 | | IV-1 | IGSF9B | 1.16 |
| 6979 | 3 | 4 | | | IV-1 | GTPBP8 | 1.19 | 7075 | 3 | 4 | | IV-1 | IKZF3 | 1.03 |
| 6980 | 3 | 4 | | | IV-1 | GXYLT1 | 1.41 | 7076 | 3 | 4 | | IV-1 | IKZF4 | 1.14 |
| 6981 | 3 | 4 | | | IV-1 | GZMH | 1.25 | 7077 | 3 | 4 | | IV-1 | IKZF5 | 1.28 |
| 6982 | 3 | 4 | | | IV-1 | GZMM | 1.30 | 7078 | 3 | 4 | | IV-1 | IL12RB1 | 1.21 |
| 6983 | 3 | 4 | | | IV-1 | H2AFV | 1.13 | 7079 | 3 | 4 | | IV-1 | IL17RD | 1.41 |
| 6984 | 3 | 4 | | | IV-1 | H2AFZ | 1.46 | 7080 | 3 | 4 | | IV-1 | IL18RAP | 1.06 |
| 6985 | 3 | 4 | | | IV-1 | H2BFXP | 1.07 | 7081 | 3 | 4 | | IV-1 | IL1A | 1.25 |
| 6986 | 3 | 4 | | | IV-1 | HACL1 | 1.15 | 7082 | 3 | 4 | | IV-1 | IL1R1 | 1.24 |
| 6987 | 3 | 4 | | | IV-1 | HARBI1 | 1.41 | 7083 | 3 | 4 | | IV-1 | IL1RAP | 1.16 |
| 6988 | 3 | 4 | | | IV-1 | HAS2 | 1.12 | 7084 | 3 | 4 | | IV-1 | IL1RL1 | 1.24 |
| 6989 | 3 | 4 | | | IV-1 | HAS2-AS1 | 1.12 | 7085 | 3 | 4 | | IV-1 | IL2RA | 1.46 |
| 6990 | 3 | 4 | | | IV-1 | HBP1 | 1.04 | 7086 | 3 | 4 | | IV-1 | IL33 | 1.29 |
| 6991 | 3 | 4 | | | IV-1 | HBS1L | 1.30 | 7087 | 3 | 4 | | IV-1 | IL6ST | 1.23 |
| 6992 | 3 | 4 | | | IV-1 | HDHD1 | 1.01 | 7088 | 3 | 4 | | IV-1 | IMPA1 | 1.06 |
| 6993 | 3 | 4 | | | IV-1 | HDHD2 | 1.04 | 7089 | 3 | 4 | | IV-1 | IMPACT | 1.43 |
| 6994 | 3 | 4 | | | IV-1 | HEATR1 | 1.40 | 7090 | 3 | 4 | | IV-1 | INADL | 1.46 |
| 6995 | 3 | 4 | | | IV-1 | HECA | 1.13 | 7091 | 3 | 4 | | IV-1 | ING3 | 1.16 |
| 6996 | 3 | 4 | | | IV-1 | HECTD1 | 1.20 | 7092 | 3 | 4 | | IV-1 | INO80C | 1.03 |
| 6997 | 3 | 4 | | | IV-1 | HECW2 | 1.11 | 7093 | 3 | 4 | | IV-1 | INPP5F | 1.27 |
| 6998 | 3 | 4 | | | IV-1 | HEG1 | 1.25 | 7094 | 3 | 4 | | IV-1 | INTS2 | 1.25 |
| 6999 | 3 | 4 | | | IV-1 | HELQ | 1.28 | 7095 | 3 | 4 | | IV-1 | INTS8 | 1.18 |
| 7000 | 3 | 4 | | | IV-1 | HELZ | 1.40 | 7096 | 3 | 4 | | IV-1 | IPO11 | 1.03 |
| 7001 | 3 | 4 | | | IV-1 | HEPH | 1.50 | 7097 | 3 | 4 | | IV-1 | IQCD | 1.29 |
| 7002 | 3 | 4 | | | IV-1 | HERC1 | 1.25 | 7098 | 3 | 4 | | IV-1 | IQCG | 1.18 |
| 7003 | 3 | 4 | | | IV-1 | HERC2 | 1.05 | 7099 | 3 | 4 | | IV-1 | IQGAP2 | 1.50 |
| 7004 | 3 | 4 | | | IV-1 | HERC4 | 1.39 | 7100 | 3 | 4 | | IV-1 | IQSEC3 | 1.08 |
| 7005 | 3 | 4 | | | IV-1 | HESX1 | 1.01 | 7101 | 3 | 4 | | IV-1 | IRAK1BP1 | 1.13 |

Fig. 38 - 38

| | | | | | | | | | | | | | | | |
|---|---|---|---|---|---|---|---|---|---|---|---|---|---|---|---|
| 7102 | 3 | 4 | | | IV-1 | IREB2 | 1.30 | 7198 | 3 | 4 | | | IV-1 | KLHL20 | 1.43 |
| 7103 | 3 | 4 | | | IV-1 | IRGQ | 1.32 | 7199 | 3 | 4 | | | IV-1 | KLHL24 | 1.10 |
| 7104 | 3 | 4 | | | IV-1 | ITCH | 1.17 | 7200 | 3 | 4 | | | IV-1 | KLHL6 | 1.29 |
| 7105 | 3 | 4 | | | IV-1 | ITFG1 | 1.11 | 7201 | 3 | 4 | | | IV-1 | KLHL7 | 1.09 |
| 7106 | 3 | 4 | | | IV-1 | ITGA1 | 1.01 | 7202 | 3 | 4 | | | IV-1 | KNDC1 | 1.10 |
| 7107 | 3 | 4 | | | IV-1 | ITGA2 | 1.05 | 7203 | 3 | 4 | | | IV-1 | KPNA3 | 1.33 |
| 7108 | 3 | 4 | | | IV-1 | ITGA4 | 1.40 | 7204 | 3 | 4 | | | IV-1 | KPNA4 | 1.15 |
| 7109 | 3 | 4 | | | IV-1 | ITGA8 | 1.22 | 7205 | 3 | 4 | | | IV-1 | KPNB1 | 1.20 |
| 7110 | 3 | 4 | | | IV-1 | ITGAL | 1.35 | 7206 | 3 | 4 | | | IV-1 | KRCC1 | 1.22 |
| 7111 | 3 | 4 | | | IV-1 | ITGAV | 1.20 | 7207 | 3 | 4 | | | IV-1 | KRT26 | 1.08 |
| 7112 | 3 | 4 | | | IV-1 | ITGB3BP | 1.21 | 7208 | 3 | 4 | | | IV-1 | KRT33B | 1.03 |
| 7113 | 3 | 4 | | | IV-1 | ITGB8 | 1.08 | 7209 | 3 | 4 | | | IV-1 | KRT34 | 1.22 |
| 7114 | 3 | 4 | | | IV-1 | ITPR3 | 1.02 | 7210 | 3 | 4 | | | IV-1 | KRT81 | 1.31 |
| 7115 | 3 | 4 | | | IV-1 | ITPRIPL2 | 1.08 | 7211 | 3 | 4 | | | IV-1 | KRT82 | 1.12 |
| 7116 | 3 | 4 | | | IV-1 | ITSN1 | 1.11 | 7212 | 3 | 4 | | | IV-1 | KRT86 | 1.44 |
| 7117 | 3 | 4 | | | IV-1 | IVD | 1.32 | 7213 | 3 | 4 | | | IV-1 | KRTAP10-1 | 1.24 |
| 7118 | 3 | 4 | | | IV-1 | IVNS1ABP | 1.22 | 7214 | 3 | 4 | | | IV-1 | KRTAP10-12 | 1.13 |
| 7119 | 3 | 4 | | | IV-1 | IWS1 | 1.19 | 7215 | 3 | 4 | | | IV-1 | KRTAP10-2 | 1.19 |
| 7120 | 3 | 4 | | | IV-1 | JAG1 | 1.06 | 7216 | 3 | 4 | | | IV-1 | KRTAP10-7 | 1.28 |
| 7121 | 3 | 4 | | | IV-1 | JAK2 | 1.40 | 7217 | 3 | 4 | | | IV-1 | KRTAP10-8 | 1.03 |
| 7122 | 3 | 4 | | | IV-1 | JHDM1D | 1.26 | 7218 | 3 | 4 | | | IV-1 | KRTAP12-1 | 1.39 |
| 7123 | 3 | 4 | | | IV-1 | JKAMP | 1.00 | 7219 | 3 | 4 | | | IV-1 | KRTAP19-1 | 1.37 |
| 7124 | 3 | 4 | | | IV-1 | JPH2 | 1.10 | 7220 | 3 | 4 | | | IV-1 | KRTAP19-3 | 1.41 |
| 7125 | 3 | 4 | | | IV-1 | JPX | 1.41 | 7221 | 3 | 4 | | | IV-1 | KRTAP2-2 | 1.22 |
| 7126 | 3 | 4 | | | IV-1 | KAL1 | 1.03 | 7222 | 3 | 4 | | | IV-1 | KRTAP2-4 | 1.36 |
| 7127 | 3 | 4 | | | IV-1 | KALRN | 1.16 | 7223 | 3 | 4 | | | IV-1 | KRTAP24-1 | 1.04 |
| 7128 | 3 | 4 | | | IV-1 | KANK4 | 1.00 | 7224 | 3 | 4 | | | IV-1 | KRTAP4-1 | 1.44 |
| 7129 | 3 | 4 | | | IV-1 | KAT2B | 1.43 | 7225 | 3 | 4 | | | IV-1 | KRTAP4-11 | 1.12 |
| 7130 | 3 | 4 | | | IV-1 | KATNA1 | 1.04 | 7226 | 3 | 4 | | | IV-1 | KRTAP4-12 | 1.30 |
| 7131 | 3 | 4 | | | IV-1 | KATNAL1 | 1.30 | 7227 | 3 | 4 | | | IV-1 | KRTAP4-2 | 1.36 |
| 7132 | 3 | 4 | | | IV-1 | KBTBD2 | 1.25 | 7228 | 3 | 4 | | | IV-1 | KRTAP4-3 | 1.48 |
| 7133 | 3 | 4 | | | IV-1 | KBTBD3 | 1.20 | 7229 | 3 | 4 | | | IV-1 | KRTAP4-8 | 1.49 |
| 7134 | 3 | 4 | | | IV-1 | KBTBD6 | 1.43 | 7230 | 3 | 4 | | | IV-1 | KRTAP5-10 | 1.43 |
| 7135 | 3 | 4 | | | IV-1 | KCNA6 | 1.40 | 7231 | 3 | 4 | | | IV-1 | KRTAP5-11 | 1.19 |
| 7136 | 3 | 4 | | | IV-1 | KCNA81 | 1.22 | 7232 | 3 | 4 | | | IV-1 | KRTAP9-9 | 1.09 |
| 7137 | 3 | 4 | | | IV-1 | KCNIP1 | 1.03 | 7233 | 3 | 4 | | | IV-1 | KRTDAP | 1.00 |
| 7138 | 3 | 4 | | | IV-1 | KCNJ13 | 1.09 | 7234 | 3 | 4 | | | IV-1 | KTN1-AS1 | 1.04 |
| 7139 | 3 | 4 | | | IV-1 | KCNJ5 | 1.23 | 7235 | 3 | 4 | | | IV-1 | KY | 1.01 |
| 7140 | 3 | 4 | | | IV-1 | KCNMB3 | 1.25 | 7236 | 3 | 4 | | | IV-1 | L3MBTL3 | 1.31 |
| 7141 | 3 | 4 | | | IV-1 | KCNRG | 1.20 | 7237 | 3 | 4 | | | IV-1 | L3MBTL4 | 1.44 |
| 7142 | 3 | 4 | | | IV-1 | KCTD12 | 1.19 | 7238 | 3 | 4 | | | IV-1 | LAMA2 | 1.04 |
| 7143 | 3 | 4 | | | IV-1 | KCTD9 | 1.09 | 7239 | 3 | 4 | | | IV-1 | LAMA4 | 1.10 |
| 7144 | 3 | 4 | | | IV-1 | KDELC2 | 1.39 | 7240 | 3 | 4 | | | IV-1 | LAMC1 | 1.07 |
| 7145 | 3 | 4 | | | IV-1 | KDM1B | 1.04 | 7241 | 3 | 4 | | | IV-1 | LAMTOR3 | 1.04 |
| 7146 | 3 | 4 | | | IV-1 | KDM3A | 1.29 | 7242 | 3 | 4 | | | IV-1 | LARP4 | 1.49 |
| 7147 | 3 | 4 | | | IV-1 | KDM3B | 1.16 | 7243 | 3 | 4 | | | IV-1 | LARP4B | 1.20 |
| 7148 | 3 | 4 | | | IV-1 | KDM5A | 1.00 | 7244 | 3 | 4 | | | IV-1 | LATS2 | 1.34 |
| 7149 | 3 | 4 | | | IV-1 | KHNYN | 1.04 | 7245 | 3 | 4 | | | IV-1 | LBR | 1.31 |
| 7150 | 3 | 4 | | | IV-1 | KIAA0020 | 1.04 | 7246 | 3 | 4 | | | IV-1 | LCA5 | 1.02 |
| 7151 | 3 | 4 | | | IV-1 | KIAA0101 | 1.20 | 7247 | 3 | 4 | | | IV-1 | LCLAT1 | 1.39 |
| 7152 | 3 | 4 | | | IV-1 | KIAA0146 | 1.32 | 7248 | 3 | 4 | | | IV-1 | LCMT2 | 1.03 |
| 7153 | 3 | 4 | | | IV-1 | KIAA0182 | 1.04 | 7249 | 3 | 4 | | | IV-1 | LCNL1 | 1.48 |
| 7154 | 3 | 4 | | | IV-1 | KIAA0196 | 1.33 | 7250 | 3 | 4 | | | IV-1 | LEAP2 | 1.13 |
| 7155 | 3 | 4 | | | IV-1 | KIAA0226 | 1.04 | 7251 | 3 | 4 | | | IV-1 | LEF1 | 1.10 |
| 7156 | 3 | 4 | | | IV-1 | KIAA0226L | 1.25 | 7252 | 3 | 4 | | | IV-1 | LETMD1 | 1.11 |
| 7157 | 3 | 4 | | | IV-1 | KIAA0240 | 1.31 | 7253 | 3 | 4 | | | IV-1 | LGALS8 | 1.35 |
| 7158 | 3 | 4 | | | IV-1 | KIAA0317 | 1.02 | 7254 | 3 | 4 | | | IV-1 | LGI2 | 1.24 |
| 7159 | 3 | 4 | | | IV-1 | KIAA0355 | 1.10 | 7255 | 3 | 4 | | | IV-1 | LGMN | 1.22 |
| 7160 | 3 | 4 | | | IV-1 | KIAA0408 | 1.09 | 7256 | 3 | 4 | | | IV-1 | LGR4 | 1.04 |
| 7161 | 3 | 4 | | | IV-1 | KIAA0430 | 1.40 | 7257 | 3 | 4 | | | IV-1 | LILRA2 | 1.33 |
| 7162 | 3 | 4 | | | IV-1 | KIAA0494 | 1.28 | 7258 | 3 | 4 | | | IV-1 | LILRA4 | 1.11 |
| 7163 | 3 | 4 | | | IV-1 | KIAA0528 | 1.32 | 7259 | 3 | 4 | | | IV-1 | LILRB1 | 1.02 |
| 7164 | 3 | 4 | | | IV-1 | KIAA0586 | 1.21 | 7260 | 3 | 4 | | | IV-1 | LILRB4 | 1.35 |
| 7165 | 3 | 4 | | | IV-1 | KIAA0754 | 1.23 | 7261 | 3 | 4 | | | IV-1 | LILRB5 | 1.35 |
| 7166 | 3 | 4 | | | IV-1 | KIAA0889 | 1.03 | 7262 | 3 | 4 | | | IV-1 | LIMA1 | 1.05 |
| 7167 | 3 | 4 | | | IV-1 | KIAA0895 | 1.23 | 7263 | 3 | 4 | | | IV-1 | LIMD1 | 1.24 |
| 7168 | 3 | 4 | | | IV-1 | KIAA0947 | 1.40 | 7264 | 3 | 4 | | | IV-1 | LIMD2 | 1.07 |
| 7169 | 3 | 4 | | | IV-1 | KIAA1143 | 1.18 | 7265 | 3 | 4 | | | IV-1 | LIN52 | 1.25 |
| 7170 | 3 | 4 | | | IV-1 | KIAA1199 | 1.00 | 7266 | 3 | 4 | | | IV-1 | LIN54 | 1.19 |
| 7171 | 3 | 4 | | | IV-1 | KIAA1279 | 1.02 | 7267 | 3 | 4 | | | IV-1 | LIN7C | 1.19 |
| 7172 | 3 | 4 | | | IV-1 | KIAA1429 | 1.28 | 7268 | 3 | 4 | | | IV-1 | LIN9 | 1.03 |
| 7173 | 3 | 4 | | | IV-1 | KIAA1430 | 1.15 | 7269 | 3 | 4 | | | IV-1 | LINC00204A | 1.03 |
| 7174 | 3 | 4 | | | IV-1 | KIAA1462 | 1.19 | 7270 | 3 | 4 | | | IV-1 | LINC00310 | 1.05 |
| 7175 | 3 | 4 | | | IV-1 | KIAA1549 | 1.16 | 7271 | 3 | 4 | | | IV-1 | LINC00341 | 1.01 |
| 7176 | 3 | 4 | | | IV-1 | KIAA1598 | 1.10 | 7272 | 3 | 4 | | | IV-1 | LINC00426 | 1.13 |
| 7177 | 3 | 4 | | | IV-1 | KIAA1731 | 1.16 | 7273 | 3 | 4 | | | IV-1 | LINC00467 | 1.34 |
| 7178 | 3 | 4 | | | IV-1 | KIAA1755 | 1.04 | 7274 | 3 | 4 | | | IV-1 | LIPC | 1.14 |
| 7179 | 3 | 4 | | | IV-1 | KIAA1797 | 1.02 | 7275 | 3 | 4 | | | IV-1 | LIPG | 1.25 |
| 7180 | 3 | 4 | | | IV-1 | KIAA1908 | 1.09 | 7276 | 3 | 4 | | | IV-1 | LIPT1 | 1.17 |
| 7181 | 3 | 4 | | | IV-1 | KIDINS220 | 1.37 | 7277 | 3 | 4 | | | IV-1 | LIPT2 | 1.16 |
| 7182 | 3 | 4 | | | IV-1 | KIF16B | 1.02 | 7278 | 3 | 4 | | | IV-1 | LIX1 | 1.18 |
| 7183 | 3 | 4 | | | IV-1 | KIF20B | 1.36 | 7279 | 3 | 4 | | | IV-1 | LMAN1 | 1.43 |
| 7184 | 3 | 4 | | | IV-1 | KIF21A | 1.30 | 7280 | 3 | 4 | | | IV-1 | LMBR1 | 1.16 |
| 7185 | 3 | 4 | | | IV-1 | KIF21B | 1.22 | 7281 | 3 | 4 | | | IV-1 | LMBRD1 | 1.04 |
| 7186 | 3 | 4 | | | IV-1 | KIF3B | 1.08 | 7282 | 3 | 4 | | | IV-1 | LMTK2 | 1.33 |
| 7187 | 3 | 4 | | | IV-1 | KIT | 1.09 | 7283 | 3 | 4 | | | IV-1 | LNP1 | 1.01 |
| 7188 | 3 | 4 | | | IV-1 | KL | 1.03 | 7284 | 3 | 4 | | | IV-1 | LOC100128420 | 1.46 |
| 7189 | 3 | 4 | | | IV-1 | KLF11 | 1.11 | 7285 | 3 | 4 | | | IV-1 | LOC100129034 | 1.27 |
| 7190 | 3 | 4 | | | IV-1 | KLF8 | 1.38 | 7286 | 3 | 4 | | | IV-1 | LOC100129196 | 1.05 |
| 7191 | 3 | 4 | | | IV-1 | KLF9 | 1.03 | 7287 | 3 | 4 | | | IV-1 | LOC100129269 | 1.05 |
| 7192 | 3 | 4 | | | IV-1 | KLHDC10 | 1.35 | 7288 | 3 | 4 | | | IV-1 | LOC100129480 | 1.06 |
| 7193 | 3 | 4 | | | IV-1 | KLHDC5 | 1.36 | 7289 | 3 | 4 | | | IV-1 | LOC100129961 | 1.49 |
| 7194 | 3 | 4 | | | IV-1 | KLHDC9 | 1.46 | 7290 | 3 | 4 | | | IV-1 | LOC100130557 | 1.44 |
| 7195 | 3 | 4 | | | IV-1 | KLHL12 | 1.22 | 7291 | 3 | 4 | | | IV-1 | LOC100130581 | 1.40 |
| 7196 | 3 | 4 | | | IV-1 | KLHL15 | 1.27 | 7292 | 3 | 4 | | | IV-1 | LOC100130705 | 1.04 |
| 7197 | 3 | 4 | | | IV-1 | KLHL18 | 1.19 | 7293 | 3 | 4 | | | IV-1 | LOC100130890 | 1.05 |

Fig. 38 - 39

| | | | | | | | | | | | | | | | | |
|---|---|---|---|---|---|---|---|---|---|---|---|---|---|---|---|---|
| 7294 | 3 | 4 | | | | IV-1 | LOC100130950 | 1.04 | 7390 | 3 | 4 | | | | IV-1 | LRRC39 | 1.24 |
| 7295 | 3 | 4 | | | | IV-1 | LOC100131096 | 1.11 | 7391 | 3 | 4 | | | | IV-1 | LRRC4 | 1.45 |
| 7296 | 3 | 4 | | | | IV-1 | LOC100131726 | 1.20 | 7392 | 3 | 4 | | | | IV-1 | LRRC4C | 1.09 |
| 7297 | 3 | 4 | | | | IV-1 | LOC100132832 | 1.43 | 7393 | 3 | 4 | | | | IV-1 | LRRC57 | 1.07 |
| 7298 | 3 | 4 | | | | IV-1 | LOC100133286 | 1.03 | 7394 | 3 | 4 | | | | IV-1 | LRRK1 | 1.00 |
| 7299 | 3 | 4 | | | | IV-1 | LOC100134713 | 1.32 | 7395 | 3 | 4 | | | | IV-1 | LRRK2 | 1.20 |
| 7300 | 3 | 4 | | | | IV-1 | LOC100134868 | 1.16 | 7396 | 3 | 4 | | | | IV-1 | LRRN3 | 1.02 |
| 7301 | 3 | 4 | | | | IV-1 | LOC100192204 | 1.10 | 7397 | 3 | 4 | | | | IV-1 | LSM6 | 1.14 |
| 7302 | 3 | 4 | | | | IV-1 | LOC100240735 | 1.06 | 7398 | 3 | 4 | | | | IV-1 | LTN1 | 1.42 |
| 7303 | 3 | 4 | | | | IV-1 | LOC100286793 | 1.21 | 7399 | 3 | 4 | | | | IV-1 | LUC7L2 | 1.12 |
| 7304 | 3 | 4 | | | | IV-1 | LOC100287616 | 1.06 | 7400 | 3 | 4 | | | | IV-1 | LUZP1 | 1.24 |
| 7305 | 3 | 4 | | | | IV-1 | LOC100287765 | 1.09 | 7401 | 3 | 4 | | | | IV-1 | LY75 | 1.15 |
| 7306 | 3 | 4 | | | | IV-1 | LOC100289361 | 1.12 | 7402 | 3 | 4 | | | | IV-1 | LYAR | 1.09 |
| 7307 | 3 | 4 | | | | IV-1 | LOC100289561 | 1.14 | 7403 | 3 | 4 | | | | IV-1 | LYPLAL1 | 1.29 |
| 7308 | 3 | 4 | | | | IV-1 | LOC100335030 | 1.38 | 7404 | 3 | 4 | | | | IV-1 | LYRM2 | 1.31 |
| 7309 | 3 | 4 | | | | IV-1 | LOC100499405 | 1.02 | 7405 | 3 | 4 | | | | IV-1 | LYRM5 | 1.13 |
| 7310 | 3 | 4 | | | | IV-1 | LOC100505678 | 1.16 | 7406 | 3 | 4 | | | | IV-1 | LZTFL1 | 1.18 |
| 7311 | 3 | 4 | | | | IV-1 | LOC100505702 | 1.29 | 7407 | 3 | 4 | | | | IV-1 | MAB21L3 | 1.18 |
| 7312 | 3 | 4 | | | | IV-1 | LOC100505715 | 1.29 | 7408 | 3 | 4 | | | | IV-1 | MACF1 | 1.03 |
| 7313 | 3 | 4 | | | | IV-1 | LOC100505783 | 1.02 | 7409 | 3 | 4 | | | | IV-1 | MAFG | 1.04 |
| 7314 | 3 | 4 | | | | IV-1 | LOC100505933 | 1.18 | 7410 | 3 | 4 | | | | IV-1 | MAGI1 | 1.23 |
| 7315 | 3 | 4 | | | | IV-1 | LOC100506046 | 1.35 | 7411 | 3 | 4 | | | | IV-1 | MAGI3 | 1.44 |
| 7316 | 3 | 4 | | | | IV-1 | LOC100506334 | 1.05 | 7412 | 3 | 4 | | | | IV-1 | MAGIX | 1.08 |
| 7317 | 3 | 4 | | | | IV-1 | LOC100506451 | 1.13 | 7413 | 3 | 4 | | | | IV-1 | MAK16 | 1.18 |
| 7318 | 3 | 4 | | | | IV-1 | LOC100506548 | 1.10 | 7414 | 3 | 4 | | | | IV-1 | MALT1 | 1.48 |
| 7319 | 3 | 4 | | | | IV-1 | LOC100506599 | 1.19 | 7415 | 3 | 4 | | | | IV-1 | MAN1A1 | 1.18 |
| 7320 | 3 | 4 | | | | IV-1 | LOC100506730 | 1.08 | 7416 | 3 | 4 | | | | IV-1 | MAN1C1 | 1.10 |
| 7321 | 3 | 4 | | | | IV-1 | LOC100506776 | 1.07 | 7417 | 3 | 4 | | | | IV-1 | MANBA | 1.09 |
| 7322 | 3 | 4 | | | | IV-1 | LOC100506844 | 1.23 | 7418 | 3 | 4 | | | | IV-1 | MANEA | 1.40 |
| 7323 | 3 | 4 | | | | IV-1 | LOC100507062 | 1.27 | 7419 | 3 | 4 | | | | IV-1 | MAP1LC3B2 | 1.30 |
| 7324 | 3 | 4 | | | | IV-1 | LOC100507351 | 1.23 | 7420 | 3 | 4 | | | | IV-1 | MAP2 | 1.38 |
| 7325 | 3 | 4 | | | | IV-1 | LOC100507495 | 1.50 | 7421 | 3 | 4 | | | | IV-1 | MAP2K4 | 1.08 |
| 7326 | 3 | 4 | | | | IV-1 | LOC100507557 | 1.06 | 7422 | 3 | 4 | | | | IV-1 | MAP3K1 | 1.35 |
| 7327 | 3 | 4 | | | | IV-1 | LOC100508120 | 1.14 | 7423 | 3 | 4 | | | | IV-1 | MAP3K2 | 1.07 |
| 7328 | 3 | 4 | | | | IV-1 | LOC100616668 | 1.14 | 7424 | 3 | 4 | | | | IV-1 | MAP3K7 | 1.24 |
| 7329 | 3 | 4 | | | | IV-1 | LOC100652999 | 1.01 | 7425 | 3 | 4 | | | | IV-1 | MAP3K9 | 1.48 |
| 7330 | 3 | 4 | | | | IV-1 | LOC144481 | 1.00 | 7426 | 3 | 4 | | | | IV-1 | MAP4K3 | 1.08 |
| 7331 | 3 | 4 | | | | IV-1 | LOC147727 | 1.02 | 7427 | 3 | 4 | | | | IV-1 | MAP4K4 | 1.01 |
| 7332 | 3 | 4 | | | | IV-1 | LOC149837 | 1.02 | 7428 | 3 | 4 | | | | IV-1 | MAP4K5 | 1.01 |
| 7333 | 3 | 4 | | | | IV-1 | LOC153684 | 1.23 | 7429 | 3 | 4 | | | | IV-1 | MAPK1 | 1.28 |
| 7334 | 3 | 4 | | | | IV-1 | LOC157381 | 1.05 | 7430 | 3 | 4 | | | | IV-1 | MAPK14 | 1.14 |
| 7335 | 3 | 4 | | | | IV-1 | LOC158572 | 1.02 | 7431 | 3 | 4 | | | | IV-1 | MAPK8 | 1.24 |
| 7336 | 3 | 4 | | | | IV-1 | LOC254128 | 1.10 | 7432 | 3 | 4 | | | | IV-1 | MARCH6 | 1.44 |
| 7337 | 3 | 4 | | | | IV-1 | LOC255480 | 1.07 | 7433 | 3 | 4 | | | | IV-1 | MARCH7 | 1.33 |
| 7338 | 3 | 4 | | | | IV-1 | LOC256021 | 1.17 | 7434 | 3 | 4 | | | | IV-1 | MAS1L | 1.21 |
| 7339 | 3 | 4 | | | | IV-1 | LOC257396 | 1.06 | 7435 | 3 | 4 | | | | IV-1 | MATK | 1.45 |
| 7340 | 3 | 4 | | | | IV-1 | LOC283174 | 1.27 | 7436 | 3 | 4 | | | | IV-1 | MATR3 | 1.34 |
| 7341 | 3 | 4 | | | | IV-1 | LOC284837 | 1.25 | 7437 | 3 | 4 | | | | IV-1 | MAVS | 1.29 |
| 7342 | 3 | 4 | | | | IV-1 | LOC285033 | 1.18 | 7438 | 3 | 4 | | | | IV-1 | MB21D1 | 1.24 |
| 7343 | 3 | 4 | | | | IV-1 | LOC339290 | 1.04 | 7439 | 3 | 4 | | | | IV-1 | MBD4 | 1.12 |
| 7344 | 3 | 4 | | | | IV-1 | LOC339803 | 1.21 | 7440 | 3 | 4 | | | | IV-1 | MBIP | 1.00 |
| 7345 | 3 | 4 | | | | IV-1 | LOC340357 | 1.37 | 7441 | 3 | 4 | | | | IV-1 | MBLAC2 | 1.30 |
| 7346 | 3 | 4 | | | | IV-1 | LOC340544 | 1.15 | 7442 | 3 | 4 | | | | IV-1 | MBNL3 | 1.21 |
| 7347 | 3 | 4 | | | | IV-1 | LOC374443 | 1.32 | 7443 | 3 | 4 | | | | IV-1 | MBP | 1.02 |
| 7348 | 3 | 4 | | | | IV-1 | LOC390940 | 1.08 | 7444 | 3 | 4 | | | | IV-1 | MBTD1 | 1.40 |
| 7349 | 3 | 4 | | | | IV-1 | LOC391322 | 1.37 | 7445 | 3 | 4 | | | | IV-1 | MCART1 | 1.23 |
| 7350 | 3 | 4 | | | | IV-1 | LOC401588 | 1.17 | 7446 | 3 | 4 | | | | IV-1 | MCC | 1.13 |
| 7351 | 3 | 4 | | | | IV-1 | LOC440354 | 1.21 | 7447 | 3 | 4 | | | | IV-1 | MCCC1 | 1.33 |
| 7352 | 3 | 4 | | | | IV-1 | LOC440434 | 1.45 | 7448 | 3 | 4 | | | | IV-1 | MCFD2 | 1.34 |
| 7353 | 3 | 4 | | | | IV-1 | LOC440895 | 1.24 | 7449 | 3 | 4 | | | | IV-1 | MCM3AP-AS1 | 1.20 |
| 7354 | 3 | 4 | | | | IV-1 | LOC441454 | 1.13 | 7450 | 3 | 4 | | | | IV-1 | MCM6 | 1.14 |
| 7355 | 3 | 4 | | | | IV-1 | LOC550112 | 1.02 | 7451 | 3 | 4 | | | | IV-1 | MCM9 | 1.30 |
| 7356 | 3 | 4 | | | | IV-1 | LOC595101 | 1.45 | 7452 | 3 | 4 | | | | IV-1 | MCPH1 | 1.02 |
| 7357 | 3 | 4 | | | | IV-1 | LOC606724 | 1.02 | 7453 | 3 | 4 | | | | IV-1 | MDFIC | 1.37 |
| 7358 | 3 | 4 | | | | IV-1 | LOC642361 | 1.35 | 7454 | 3 | 4 | | | | IV-1 | MDM1 | 1.37 |
| 7359 | 3 | 4 | | | | IV-1 | LOC643387 | 1.43 | 7455 | 3 | 4 | | | | IV-1 | MDM2 | 1.32 |
| 7360 | 3 | 4 | | | | IV-1 | LOC646719 | 1.14 | 7456 | 3 | 4 | | | | IV-1 | MDM4 | 1.44 |
| 7361 | 3 | 4 | | | | IV-1 | LOC646851 | 1.08 | 7457 | 3 | 4 | | | | IV-1 | MDP1 | 1.06 |
| 7362 | 3 | 4 | | | | IV-1 | LOC653712 | 1.02 | 7458 | 3 | 4 | | | | IV-1 | MED13 | 1.32 |
| 7363 | 3 | 4 | | | | IV-1 | LOC727896 | 1.31 | 7459 | 3 | 4 | | | | IV-1 | MED13L | 1.36 |
| 7364 | 3 | 4 | | | | IV-1 | LOC728730 | 1.08 | 7460 | 3 | 4 | | | | IV-1 | MED14 | 1.07 |
| 7365 | 3 | 4 | | | | IV-1 | LOC728819 | 1.02 | 7461 | 3 | 4 | | | | IV-1 | MED17 | 1.06 |
| 7366 | 3 | 4 | | | | IV-1 | LOC729176 | 1.05 | 7462 | 3 | 4 | | | | IV-1 | MED7 | 1.13 |
| 7367 | 3 | 4 | | | | IV-1 | LOC729178 | 1.08 | 7463 | 3 | 4 | | | | IV-1 | MEF2A | 1.40 |
| 7368 | 3 | 4 | | | | IV-1 | LOC729683 | 1.02 | 7464 | 3 | 4 | | | | IV-1 | MEF2C | 1.18 |
| 7369 | 3 | 4 | | | | IV-1 | LOC730227 | 1.04 | 7465 | 3 | 4 | | | | IV-1 | MEFV | 1.37 |
| 7370 | 3 | 4 | | | | IV-1 | LOC730755 | 1.10 | 7466 | 3 | 4 | | | | IV-1 | METAP1 | 1.10 |
| 7371 | 3 | 4 | | | | IV-1 | LOC96610 | 1.42 | 7467 | 3 | 4 | | | | IV-1 | METAP2 | 1.05 |
| 7372 | 3 | 4 | | | | IV-1 | LOH12CR2 | 1.09 | 7468 | 3 | 4 | | | | IV-1 | METTL10 | 1.02 |
| 7373 | 3 | 4 | | | | IV-1 | LONRF1 | 1.27 | 7469 | 3 | 4 | | | | IV-1 | METTL12 | 1.03 |
| 7374 | 3 | 4 | | | | IV-1 | LONRF2 | 1.24 | 7470 | 3 | 4 | | | | IV-1 | METTL14 | 1.16 |
| 7375 | 3 | 4 | | | | IV-1 | LPAR1 | 1.35 | 7471 | 3 | 4 | | | | IV-1 | METTL15 | 1.19 |
| 7376 | 3 | 4 | | | | IV-1 | LPAR4 | 1.05 | 7472 | 3 | 4 | | | | IV-1 | METTL16 | 1.07 |
| 7377 | 3 | 4 | | | | IV-1 | LPAR6 | 1.46 | 7473 | 3 | 4 | | | | IV-1 | METTL21D | 1.03 |
| 7378 | 3 | 4 | | | | IV-1 | LPXN | 1.44 | 7474 | 3 | 4 | | | | IV-1 | METTL22 | 1.11 |
| 7379 | 3 | 4 | | | | IV-1 | LRCH1 | 1.01 | 7475 | 3 | 4 | | | | IV-1 | METTL24 | 1.16 |
| 7380 | 3 | 4 | | | | IV-1 | LRFN5 | 1.02 | 7476 | 3 | 4 | | | | IV-1 | METTL4 | 1.05 |
| 7381 | 3 | 4 | | | | IV-1 | LRIG3 | 1.18 | 7477 | 3 | 4 | | | | IV-1 | METTL7A | 1.11 |
| 7382 | 3 | 4 | | | | IV-1 | LRMP | 1.46 | 7478 | 3 | 4 | | | | IV-1 | METTL8 | 1.22 |
| 7383 | 3 | 4 | | | | IV-1 | LRP1 | 1.16 | 7479 | 3 | 4 | | | | IV-1 | MFAP1 | 1.08 |
| 7384 | 3 | 4 | | | | IV-1 | LRP12 | 1.33 | 7480 | 3 | 4 | | | | IV-1 | MFAP3 | 1.12 |
| 7385 | 3 | 4 | | | | IV-1 | LRP6 | 1.38 | 7481 | 3 | 4 | | | | IV-1 | MFSD1 | 1.04 |
| 7386 | 3 | 4 | | | | IV-1 | LRP8 | 1.12 | 7482 | 3 | 4 | | | | IV-1 | MFSD11 | 1.10 |
| 7387 | 3 | 4 | | | | IV-1 | LRPPRC | 1.11 | 7483 | 3 | 4 | | | | IV-1 | MFSD6 | 1.06 |
| 7388 | 3 | 4 | | | | IV-1 | LRRC2 | 1.37 | 7484 | 3 | 4 | | | | IV-1 | MGA | 1.25 |
| 7389 | 3 | 4 | | | | IV-1 | LRRC37BP1 | 1.11 | 7485 | 3 | 4 | | | | IV-1 | MGC21881 | 1.42 |

Fig. 38 - 40

| | | | | | | | | | | | | | | |
|---|---|---|---|---|---|---|---|---|---|---|---|---|---|---|
| 7486 | 3 | 4 | | | IV-1 | MGC27345 | 1.04 | 7582 | 3 | 4 | | | IV-1 | NBPF24 | 1.21 |
| 7487 | 3 | 4 | | | IV-1 | MGC39372 | 1.11 | 7583 | 3 | 4 | | | IV-1 | NBPF3 | 1.12 |
| 7488 | 3 | 4 | | | IV-1 | MGP | 1.04 | 7584 | 3 | 4 | | | IV-1 | NCAM1 | 1.21 |
| 7489 | 3 | 4 | | | IV-1 | MGST1 | 1.28 | 7585 | 3 | 4 | | | IV-1 | NCAPG2 | 1.23 |
| 7490 | 3 | 4 | | | IV-1 | MIB1 | 1.43 | 7586 | 3 | 4 | | | IV-1 | NCBP1 | 1.31 |
| 7491 | 3 | 4 | | | IV-1 | MIER3 | 1.49 | 7587 | 3 | 4 | | | IV-1 | NCF1B | 1.27 |
| 7492 | 3 | 4 | | | IV-1 | MINA | 1.11 | 7588 | 3 | 4 | | | IV-1 | NCF1C | 1.22 |
| 7493 | 3 | 4 | | | IV-1 | MIOS | 1.41 | 7589 | 3 | 4 | | | IV-1 | NCF4 | 1.04 |
| 7494 | 3 | 4 | | | IV-1 | MIR155HG | 1.14 | 7590 | 3 | 4 | | | IV-1 | NCOA1 | 1.38 |
| 7495 | 3 | 4 | | | IV-1 | MIS18BP1 | 1.06 | 7591 | 3 | 4 | | | IV-1 | NCOA3 | 1.28 |
| 7496 | 3 | 4 | | | IV-1 | MITF | 1.09 | 7592 | 3 | 4 | | | IV-1 | NDUFA10 | 1.07 |
| 7497 | 3 | 4 | | | IV-1 | MKL2 | 1.17 | 7593 | 3 | 4 | | | IV-1 | NECAB1 | 1.10 |
| 7498 | 3 | 4 | | | IV-1 | MKLN1 | 1.44 | 7594 | 3 | 4 | | | IV-1 | NECAP1 | 1.08 |
| 7499 | 3 | 4 | | | IV-1 | MKRN2 | 1.06 | 7595 | 3 | 4 | | | IV-1 | NEDD4 | 1.01 |
| 7500 | 3 | 4 | | | IV-1 | MKX | 1.04 | 7596 | 3 | 4 | | | IV-1 | NEFL | 1.38 |
| 7501 | 3 | 4 | | | IV-1 | MLL5 | 1.09 | 7597 | 3 | 4 | | | IV-1 | NEGR1 | 1.29 |
| 7502 | 3 | 4 | | | IV-1 | MLLT10 | 1.01 | 7598 | 3 | 4 | | | IV-1 | NEK1 | 1.15 |
| 7503 | 3 | 4 | | | IV-1 | MLLT4 | 1.29 | 7599 | 3 | 4 | | | IV-1 | NEK4 | 1.43 |
| 7504 | 3 | 4 | | | IV-1 | MLLT4-AS1 | 1.02 | 7600 | 3 | 4 | | | IV-1 | NEK7 | 1.42 |
| 7505 | 3 | 4 | | | IV-1 | MMAA | 1.24 | 7601 | 3 | 4 | | | IV-1 | NEK9 | 1.42 |
| 7506 | 3 | 4 | | | IV-1 | MMP23B | 1.01 | 7602 | 3 | 4 | | | IV-1 | NETO2 | 1.12 |
| 7507 | 3 | 4 | | | IV-1 | MMS22L | 1.06 | 7603 | 3 | 4 | | | IV-1 | NF1 | 1.11 |
| 7508 | 3 | 4 | | | IV-1 | MN1 | 1.42 | 7604 | 3 | 4 | | | IV-1 | NFATC2IP | 1.33 |
| 7509 | 3 | 4 | | | IV-1 | MOAP1 | 1.17 | 7605 | 3 | 4 | | | IV-1 | NFE2L2 | 1.12 |
| 7510 | 3 | 4 | | | IV-1 | MOB3B | 1.03 | 7606 | 3 | 4 | | | IV-1 | NFIA | 1.42 |
| 7511 | 3 | 4 | | | IV-1 | MOGAT1 | 1.13 | 7607 | 3 | 4 | | | IV-1 | NFIB | 1.40 |
| 7512 | 3 | 4 | | | IV-1 | MON1B | 1.36 | 7608 | 3 | 4 | | | IV-1 | NFX1 | 1.10 |
| 7513 | 3 | 4 | | | IV-1 | MORC4 | 1.01 | 7609 | 3 | 4 | | | IV-1 | NFYA | 1.14 |
| 7514 | 3 | 4 | | | IV-1 | MORN3 | 1.25 | 7610 | 3 | 4 | | | IV-1 | NHLRC2 | 1.11 |
| 7515 | 3 | 4 | | | IV-1 | MPHOSPH10 | 1.19 | 7611 | 3 | 4 | | | IV-1 | NID1 | 1.09 |
| 7516 | 3 | 4 | | | IV-1 | MPP2 | 1.24 | 7612 | 3 | 4 | | | IV-1 | NIN | 1.30 |
| 7517 | 3 | 4 | | | IV-1 | MPP5 | 1.35 | 7613 | 3 | 4 | | | IV-1 | NIPA1 | 1.03 |
| 7518 | 3 | 4 | | | IV-1 | MPP6 | 1.17 | 7614 | 3 | 4 | | | IV-1 | NIPBL | 1.10 |
| 7519 | 3 | 4 | | | IV-1 | MPRIP | 1.20 | 7615 | 3 | 4 | | | IV-1 | NKAP | 1.39 |
| 7520 | 3 | 4 | | | IV-1 | MRI1 | 1.12 | 7616 | 3 | 4 | | | IV-1 | NKIRAS1 | 1.06 |
| 7521 | 3 | 4 | | | IV-1 | MRPL19 | 1.10 | 7617 | 3 | 4 | | | IV-1 | NLGN4X | 1.24 |
| 7522 | 3 | 4 | | | IV-1 | MRPL30 | 1.01 | 7618 | 3 | 4 | | | IV-1 | NMD3 | 1.03 |
| 7523 | 3 | 4 | | | IV-1 | MRPL35 | 1.11 | 7619 | 3 | 4 | | | IV-1 | NME7 | 1.16 |
| 7524 | 3 | 4 | | | IV-1 | MRPS10 | 1.02 | 7620 | 3 | 4 | | | IV-1 | NMNAT1 | 1.17 |
| 7525 | 3 | 4 | | | IV-1 | MRPS14 | 1.23 | 7621 | 3 | 4 | | | IV-1 | NMNAT2 | 1.22 |
| 7526 | 3 | 4 | | | IV-1 | MRPS28 | 1.04 | 7622 | 3 | 4 | | | IV-1 | NMT2 | 1.13 |
| 7527 | 3 | 4 | | | IV-1 | MRS2 | 1.26 | 7623 | 3 | 4 | | | IV-1 | NMU | 1.03 |
| 7528 | 3 | 4 | | | IV-1 | MS4A14 | 1.01 | 7624 | 3 | 4 | | | IV-1 | NNT | 1.07 |
| 7529 | 3 | 4 | | | IV-1 | MSH2 | 1.19 | 7625 | 3 | 4 | | | IV-1 | NOM1 | 1.19 |
| 7530 | 3 | 4 | | | IV-1 | MSH3 | 1.46 | 7626 | 3 | 4 | | | IV-1 | NOP58 | 1.13 |
| 7531 | 3 | 4 | | | IV-1 | MSL1 | 1.07 | 7627 | 3 | 4 | | | IV-1 | NPAS1 | 1.08 |
| 7532 | 3 | 4 | | | IV-1 | MSL2 | 1.23 | 7628 | 3 | 4 | | | IV-1 | NPAT | 1.24 |
| 7533 | 3 | 4 | | | IV-1 | MSRB3 | 1.41 | 7629 | 3 | 4 | | | IV-1 | NPC1 | 1.34 |
| 7534 | 3 | 4 | | | IV-1 | MTAP | 1.15 | 7630 | 3 | 4 | | | IV-1 | NPFFR2 | 1.15 |
| 7535 | 3 | 4 | | | IV-1 | MTF2 | 1.49 | 7631 | 3 | 4 | | | IV-1 | NR3C1 | 1.13 |
| 7536 | 3 | 4 | | | IV-1 | MTHFD2L | 1.12 | 7632 | 3 | 4 | | | IV-1 | NR3C2 | 1.31 |
| 7537 | 3 | 4 | | | IV-1 | MTHFR | 1.07 | 7633 | 3 | 4 | | | IV-1 | NRD1 | 1.13 |
| 7538 | 3 | 4 | | | IV-1 | MTIF2 | 1.28 | 7634 | 3 | 4 | | | IV-1 | NRXN1 | 1.02 |
| 7539 | 3 | 4 | | | IV-1 | MTMR12 | 1.23 | 7635 | 3 | 4 | | | IV-1 | NSFP1 | 1.40 |
| 7540 | 3 | 4 | | | IV-1 | MTMR2 | 1.04 | 7636 | 3 | 4 | | | IV-1 | NSUN4 | 1.36 |
| 7541 | 3 | 4 | | | IV-1 | MTMR3 | 1.06 | 7637 | 3 | 4 | | | IV-1 | NSUN7 | 1.48 |
| 7542 | 3 | 4 | | | IV-1 | MTMR7 | 1.07 | 7638 | 3 | 4 | | | IV-1 | NT5C2 | 1.17 |
| 7543 | 3 | 4 | | | IV-1 | MTMR9 | 1.46 | 7639 | 3 | 4 | | | IV-1 | NT5DC1 | 1.04 |
| 7544 | 3 | 4 | | | IV-1 | MTO1 | 1.37 | 7640 | 3 | 4 | | | IV-1 | NT5DC3 | 1.41 |
| 7545 | 3 | 4 | | | IV-1 | MTOR | 1.14 | 7641 | 3 | 4 | | | IV-1 | NT5E | 1.40 |
| 7546 | 3 | 4 | | | IV-1 | MTPAP | 1.01 | 7642 | 3 | 4 | | | IV-1 | NTNG1 | 1.01 |
| 7547 | 3 | 4 | | | IV-1 | MTRF1L | 1.09 | 7643 | 3 | 4 | | | IV-1 | NTRK2 | 1.18 |
| 7548 | 3 | 4 | | | IV-1 | MTRNR2L10 | 1.44 | 7644 | 3 | 4 | | | IV-1 | NUBPL | 1.24 |
| 7549 | 3 | 4 | | | IV-1 | MTRR | 1.12 | 7645 | 3 | 4 | | | IV-1 | NUCB2 | 1.23 |
| 7550 | 3 | 4 | | | IV-1 | MTSS1 | 1.14 | 7646 | 3 | 4 | | | IV-1 | NUCKS1 | 1.35 |
| 7551 | 3 | 4 | | | IV-1 | MUDENG | 1.13 | 7647 | 3 | 4 | | | IV-1 | NUDCD1 | 1.01 |
| 7552 | 3 | 4 | | | IV-1 | MX2 | 1.03 | 7648 | 3 | 4 | | | IV-1 | NUDT21 | 1.44 |
| 7553 | 3 | 4 | | | IV-1 | MYBPC1 | 1.33 | 7649 | 3 | 4 | | | IV-1 | NUDT4P1 | 1.27 |
| 7554 | 3 | 4 | | | IV-1 | MYCBP2 | 1.47 | 7650 | 3 | 4 | | | IV-1 | NUDT7 | 1.03 |
| 7555 | 3 | 4 | | | IV-1 | MYH11 | 1.45 | 7651 | 3 | 4 | | | IV-1 | NUFIP2 | 1.29 |
| 7556 | 3 | 4 | | | IV-1 | MYLK-AS1 | 1.22 | 7652 | 3 | 4 | | | IV-1 | NUMB | 1.02 |
| 7557 | 3 | 4 | | | IV-1 | MYNN | 1.38 | 7653 | 3 | 4 | | | IV-1 | NUP133 | 1.22 |
| 7558 | 3 | 4 | | | IV-1 | MYO1F | 1.23 | 7654 | 3 | 4 | | | IV-1 | NUP153 | 1.29 |
| 7559 | 3 | 4 | | | IV-1 | MYO5A | 1.15 | 7655 | 3 | 4 | | | IV-1 | NUP205 | 1.04 |
| 7560 | 3 | 4 | | | IV-1 | MYO6 | 1.20 | 7656 | 3 | 4 | | | IV-1 | NUP210 | 1.04 |
| 7561 | 3 | 4 | | | IV-1 | MYO9A | 1.45 | 7657 | 3 | 4 | | | IV-1 | NUP43 | 1.00 |
| 7562 | 3 | 4 | | | IV-1 | MYOM1 | 1.12 | 7658 | 3 | 4 | | | IV-1 | NUP50 | 1.47 |
| 7563 | 3 | 4 | | | IV-1 | MZT1 | 1.05 | 7659 | 3 | 4 | | | IV-1 | O3FAR1 | 1.07 |
| 7564 | 3 | 4 | | | IV-1 | N4BP2 | 1.15 | 7660 | 3 | 4 | | | IV-1 | OAS1 | 1.02 |
| 7565 | 3 | 4 | | | IV-1 | NAA15 | 1.07 | 7661 | 3 | 4 | | | IV-1 | OCRL | 1.07 |
| 7566 | 3 | 4 | | | IV-1 | NAA25 | 1.42 | 7662 | 3 | 4 | | | IV-1 | ODZ3 | 1.06 |
| 7567 | 3 | 4 | | | IV-1 | NAA38 | 1.35 | 7663 | 3 | 4 | | | IV-1 | OGG1 | 1.17 |
| 7568 | 3 | 4 | | | IV-1 | NAALADL2 | 1.05 | 7664 | 3 | 4 | | | IV-1 | OIP5-AS1 | 1.42 |
| 7569 | 3 | 4 | | | IV-1 | NAB1 | 1.11 | 7665 | 3 | 4 | | | IV-1 | OLFML1 | 1.03 |
| 7570 | 3 | 4 | | | IV-1 | NACC2 | 1.31 | 7666 | 3 | 4 | | | IV-1 | OLFML3 | 1.15 |
| 7571 | 3 | 4 | | | IV-1 | NADKD1 | 1.02 | 7667 | 3 | 4 | | | IV-1 | OPA1 | 1.13 |
| 7572 | 3 | 4 | | | IV-1 | NAP1L1 | 1.15 | 7668 | 3 | 4 | | | IV-1 | OR2A20P | 1.26 |
| 7573 | 3 | 4 | | | IV-1 | NAP1L2 | 1.25 | 7669 | 3 | 4 | | | IV-1 | OR2A9P | 1.19 |
| 7574 | 3 | 4 | | | IV-1 | NAPEPLD | 1.35 | 7670 | 3 | 4 | | | IV-1 | OR7E12P | 1.07 |
| 7575 | 3 | 4 | | | IV-1 | NAPG | 1.30 | 7671 | 3 | 4 | | | IV-1 | OR7E91P | 1.13 |
| 7576 | 3 | 4 | | | IV-1 | NARG2 | 1.12 | 7672 | 3 | 4 | | | IV-1 | ORC2 | 1.19 |
| 7577 | 3 | 4 | | | IV-1 | NAT1 | 1.18 | 7673 | 3 | 4 | | | IV-1 | ORC4 | 1.21 |
| 7578 | 3 | 4 | | | IV-1 | NAV2 | 1.30 | 7674 | 3 | 4 | | | IV-1 | ORMDL1 | 1.27 |
| 7579 | 3 | 4 | | | IV-1 | NBN | 1.28 | 7675 | 3 | 4 | | | IV-1 | OSBPL1A | 1.01 |
| 7580 | 3 | 4 | | | IV-1 | NBPF14 | 1.24 | 7676 | 3 | 4 | | | IV-1 | OSBPL3 | 1.08 |
| 7581 | 3 | 4 | | | IV-1 | NBPF16 | 1.02 | 7677 | 3 | 4 | | | IV-1 | OSBPL8 | 1.08 |

Fig. 38 - 41

| | | | | | | | | | | | | | | |
|---|---|---|---|---|---|---|---|---|---|---|---|---|---|---|
| 7678 | 3 | 4 | | | IV-1 | OSTCP1 | 1.03 | 7774 | 3 | 4 | | | IV-1 | PGM2L1 | 1.04 |
| 7679 | 3 | 4 | | | IV-1 | OTC | 1.41 | 7775 | 3 | 4 | | | IV-1 | PGM5 | 1.09 |
| 7680 | 3 | 4 | | | IV-1 | OTUD4 | 1.15 | 7776 | 3 | 4 | | | IV-1 | PGRMC1 | 1.01 |
| 7681 | 3 | 4 | | | IV-1 | OTUD6B | 1.46 | 7777 | 3 | 4 | | | IV-1 | PHACTR2 | 1.42 |
| 7682 | 3 | 4 | | | IV-1 | OXCT1 | 1.04 | 7778 | 3 | 4 | | | IV-1 | PHAX | 1.09 |
| 7683 | 3 | 4 | | | IV-1 | OXNAD1 | 1.37 | 7779 | 3 | 4 | | | IV-1 | PHF16 | 1.39 |
| 7684 | 3 | 4 | | | IV-1 | OXR1 | 1.35 | 7780 | 3 | 4 | | | IV-1 | PHF20 | 1.33 |
| 7685 | 3 | 4 | | | IV-1 | P2RX7 | 1.21 | 7781 | 3 | 4 | | | IV-1 | PHF20L1 | 1.37 |
| 7686 | 3 | 4 | | | IV-1 | P2RY1 | 1.20 | 7782 | 3 | 4 | | | IV-1 | PHF6 | 1.10 |
| 7687 | 3 | 4 | | | IV-1 | P2RY12 | 1.41 | 7783 | 3 | 4 | | | IV-1 | PHKA1 | 1.08 |
| 7688 | 3 | 4 | | | IV-1 | P2RY4 | 1.37 | 7784 | 3 | 4 | | | IV-1 | PHKA2 | 1.04 |
| 7689 | 3 | 4 | | | IV-1 | PABPC5 | 1.04 | 7785 | 3 | 4 | | | IV-1 | PHKB | 1.23 |
| 7690 | 3 | 4 | | | IV-1 | PACRGL | 1.20 | 7786 | 3 | 4 | | | IV-1 | PHLDB2 | 1.27 |
| 7691 | 3 | 4 | | | IV-1 | PADI3 | 1.01 | 7787 | 3 | 4 | | | IV-1 | PHLPP2 | 1.43 |
| 7692 | 3 | 4 | | | IV-1 | PAFAH2 | 1.16 | 7788 | 3 | 4 | | | IV-1 | PHOSPHO2 | 1.36 |
| 7693 | 3 | 4 | | | IV-1 | PAIP2 | 1.02 | 7789 | 3 | 4 | | | IV-1 | PHTF2 | 1.43 |
| 7694 | 3 | 4 | | | IV-1 | PAK2 | 1.09 | 7790 | 3 | 4 | | | IV-1 | PI4K2B | 1.33 |
| 7695 | 3 | 4 | | | IV-1 | PALB2 | 1.08 | 7791 | 3 | 4 | | | IV-1 | PIAS1 | 1.44 |
| 7696 | 3 | 4 | | | IV-1 | PALLD | 1.02 | 7792 | 3 | 4 | | | IV-1 | PICALM | 1.02 |
| 7697 | 3 | 4 | | | IV-1 | PAM | 1.13 | 7793 | 3 | 4 | | | IV-1 | PID1 | 1.04 |
| 7698 | 3 | 4 | | | IV-1 | PAN3 | 1.34 | 7794 | 3 | 4 | | | IV-1 | PIEZO2 | 1.17 |
| 7699 | 3 | 4 | | | IV-1 | PAN3-AS1 | 1.17 | 7795 | 3 | 4 | | | IV-1 | PIGG | 1.45 |
| 7700 | 3 | 4 | | | IV-1 | PAPD4 | 1.23 | 7796 | 3 | 4 | | | IV-1 | PIGK | 1.13 |
| 7701 | 3 | 4 | | | IV-1 | PAPD7 | 1.29 | 7797 | 3 | 4 | | | IV-1 | PIGX | 1.05 |
| 7702 | 3 | 4 | | | IV-1 | PAPOLA | 1.04 | 7798 | 3 | 4 | | | IV-1 | PIK3C2A | 1.24 |
| 7703 | 3 | 4 | | | IV-1 | PAPOLG | 1.07 | 7799 | 3 | 4 | | | IV-1 | PIK3CA | 1.00 |
| 7704 | 3 | 4 | | | IV-1 | PAPPA | 1.15 | 7800 | 3 | 4 | | | IV-1 | PIK3R4 | 1.20 |
| 7705 | 3 | 4 | | | IV-1 | PAQR3 | 1.43 | 7801 | 3 | 4 | | | IV-1 | PIK3R5 | 1.14 |
| 7706 | 3 | 4 | | | IV-1 | PAQR9 | 1.18 | 7802 | 3 | 4 | | | IV-1 | PIM2 | 1.04 |
| 7707 | 3 | 4 | | | IV-1 | PARD3B | 1.37 | 7803 | 3 | 4 | | | IV-1 | PIP5K1P1 | 1.10 |
| 7708 | 3 | 4 | | | IV-1 | PARG | 1.14 | 7804 | 3 | 4 | | | IV-1 | PIR | 1.06 |
| 7709 | 3 | 4 | | | IV-1 | PARM1 | 1.11 | 7805 | 3 | 4 | | | IV-1 | PITRM1 | 1.07 |
| 7710 | 3 | 4 | | | IV-1 | PARP11 | 1.39 | 7806 | 3 | 4 | | | IV-1 | PITX2 | 1.36 |
| 7711 | 3 | 4 | | | IV-1 | PARP14 | 1.31 | 7807 | 3 | 4 | | | IV-1 | PJA2 | 1.45 |
| 7712 | 3 | 4 | | | IV-1 | PARP15 | 1.06 | 7808 | 3 | 4 | | | IV-1 | PKI55 | 1.06 |
| 7713 | 3 | 4 | | | IV-1 | PARP4 | 1.46 | 7809 | 3 | 4 | | | IV-1 | PKN2 | 1.43 |
| 7714 | 3 | 4 | | | IV-1 | PARP9 | 1.13 | 7810 | 3 | 4 | | | IV-1 | PKNOX1 | 1.11 |
| 7715 | 3 | 4 | | | IV-1 | PARPBP | 1.13 | 7811 | 3 | 4 | | | IV-1 | PLA2G12A | 1.46 |
| 7716 | 3 | 4 | | | IV-1 | PAR-SN | 1.10 | 7812 | 3 | 4 | | | IV-1 | PLA2G7 | 1.50 |
| 7717 | 3 | 4 | | | IV-1 | PAWR | 1.27 | 7813 | 3 | 4 | | | IV-1 | PLAC8L1 | 1.11 |
| 7718 | 3 | 4 | | | IV-1 | PAX1 | 1.35 | 7814 | 3 | 4 | | | IV-1 | PLAG1 | 1.06 |
| 7719 | 3 | 4 | | | IV-1 | PAX3 | 1.07 | 7815 | 3 | 4 | | | IV-1 | PLCB1 | 1.17 |
| 7720 | 3 | 4 | | | IV-1 | PBRM1 | 1.12 | 7816 | 3 | 4 | | | IV-1 | PLCL1 | 1.09 |
| 7721 | 3 | 4 | | | IV-1 | PBX1 | 1.27 | 7817 | 3 | 4 | | | IV-1 | PLD6 | 1.19 |
| 7722 | 3 | 4 | | | IV-1 | PCAT1 | 1.03 | 7818 | 3 | 4 | | | IV-1 | PLDN | 1.34 |
| 7723 | 3 | 4 | | | IV-1 | PCBD2 | 1.02 | 7819 | 3 | 4 | | | IV-1 | PLEKHA8 | 1.45 |
| 7724 | 3 | 4 | | | IV-1 | PCDH19 | 1.40 | 7820 | 3 | 4 | | | IV-1 | PLEKHA8P1 | 1.42 |
| 7725 | 3 | 4 | | | IV-1 | PCDH9 | 1.05 | 7821 | 3 | 4 | | | IV-1 | PLEKHH1 | 1.43 |
| 7726 | 3 | 4 | | | IV-1 | PCDHB10 | 1.24 | 7822 | 3 | 4 | | | IV-1 | PLEKHM1P | 1.14 |
| 7727 | 3 | 4 | | | IV-1 | PCDHB12 | 1.04 | 7823 | 3 | 4 | | | IV-1 | PLK4 | 1.07 |
| 7728 | 3 | 4 | | | IV-1 | PCDHB14 | 1.20 | 7824 | 3 | 4 | | | IV-1 | PLS3 | 1.01 |
| 7729 | 3 | 4 | | | IV-1 | PCDHB16 | 1.36 | 7825 | 3 | 4 | | | IV-1 | PLSCR4 | 1.12 |
| 7730 | 3 | 4 | | | IV-1 | PCDHB5 | 1.18 | 7826 | 3 | 4 | | | IV-1 | PLXDC2 | 1.16 |
| 7731 | 3 | 4 | | | IV-1 | PCDHGA3 | 1.19 | 7827 | 3 | 4 | | | IV-1 | PLXNC1 | 1.04 |
| 7732 | 3 | 4 | | | IV-1 | PCDHGA4 | 1.14 | 7828 | 3 | 4 | | | IV-1 | PMPCB | 1.07 |
| 7733 | 3 | 4 | | | IV-1 | PCDHGB2 | 1.48 | 7829 | 3 | 4 | | | IV-1 | PMS1 | 1.39 |
| 7734 | 3 | 4 | | | IV-1 | PCDHGB7 | 1.17 | 7830 | 3 | 4 | | | IV-1 | PMS2P3 | 1.15 |
| 7735 | 3 | 4 | | | IV-1 | PCF11 | 1.27 | 7831 | 3 | 4 | | | IV-1 | PNLDC1 | 1.47 |
| 7736 | 3 | 4 | | | IV-1 | PCM1 | 1.38 | 7832 | 3 | 4 | | | IV-1 | PNMA3 | 1.05 |
| 7737 | 3 | 4 | | | IV-1 | PCNP | 1.10 | 7833 | 3 | 4 | | | IV-1 | PNPT1 | 1.13 |
| 7738 | 3 | 4 | | | IV-1 | PCP2 | 1.21 | 7834 | 3 | 4 | | | IV-1 | PNRC2 | 1.22 |
| 7739 | 3 | 4 | | | IV-1 | PCSK5 | 1.00 | 7835 | 3 | 4 | | | IV-1 | POC1B | 1.37 |
| 7740 | 3 | 4 | | | IV-1 | PCSK6 | 1.34 | 7836 | 3 | 4 | | | IV-1 | PODN | 1.12 |
| 7741 | 3 | 4 | | | IV-1 | PCYOX1 | 1.43 | 7837 | 3 | 4 | | | IV-1 | PODXL | 1.02 |
| 7742 | 3 | 4 | | | IV-1 | PCYT1A | 1.42 | 7838 | 3 | 4 | | | IV-1 | POFUT1 | 1.01 |
| 7743 | 3 | 4 | | | IV-1 | PDCD10 | 1.38 | 7839 | 3 | 4 | | | IV-1 | POLH | 1.15 |
| 7744 | 3 | 4 | | | IV-1 | PDCD4 | 1.06 | 7840 | 3 | 4 | | | IV-1 | POLK | 1.43 |
| 7745 | 3 | 4 | | | IV-1 | PDCL | 1.05 | 7841 | 3 | 4 | | | IV-1 | POLR2B | 1.07 |
| 7746 | 3 | 4 | | | IV-1 | PDE3A | 1.30 | 7842 | 3 | 4 | | | IV-1 | POLR2M | 1.11 |
| 7747 | 3 | 4 | | | IV-1 | PDE4B | 1.13 | 7843 | 3 | 4 | | | IV-1 | POLR3G | 1.50 |
| 7748 | 3 | 4 | | | IV-1 | PDE4DIP | 1.09 | 7844 | 3 | 4 | | | IV-1 | POM121L9P | 1.39 |
| 7749 | 3 | 4 | | | IV-1 | PDE7A | 1.16 | 7845 | 3 | 4 | | | IV-1 | POMP | 1.24 |
| 7750 | 3 | 4 | | | IV-1 | PDE7B | 1.00 | 7846 | 3 | 4 | | | IV-1 | POP1 | 1.37 |
| 7751 | 3 | 4 | | | IV-1 | PDGFD | 1.48 | 7847 | 3 | 4 | | | IV-1 | POT1 | 1.47 |
| 7752 | 3 | 4 | | | IV-1 | PDGFRA | 1.26 | 7848 | 3 | 4 | | | IV-1 | POU5F1B | 1.01 |
| 7753 | 3 | 4 | | | IV-1 | PDHA1 | 1.02 | 7849 | 3 | 4 | | | IV-1 | PPAPDC1A | 1.15 |
| 7754 | 3 | 4 | | | IV-1 | PDHX | 1.09 | 7850 | 3 | 4 | | | IV-1 | PPAT | 1.07 |
| 7755 | 3 | 4 | | | IV-1 | PDSS A | 1.12 | 7851 | 3 | 4 | | | IV-1 | PPIAL4A | 1.12 |
| 7756 | 3 | 4 | | | IV-1 | PDS5B | 1.26 | 7852 | 3 | 4 | | | IV-1 | PPID | 1.13 |
| 7757 | 3 | 4 | | | IV-1 | PDSS2 | 1.23 | 7853 | 3 | 4 | | | IV-1 | PPIH | 1.22 |
| 7758 | 3 | 4 | | | IV-1 | PDZRN3 | 1.15 | 7854 | 3 | 4 | | | IV-1 | PPIP5K2 | 1.32 |
| 7759 | 3 | 4 | | | IV-1 | PDZRN4 | 1.26 | 7855 | 3 | 4 | | | IV-1 | PPM1A | 1.12 |
| 7760 | 3 | 4 | | | IV-1 | PEBP4 | 1.35 | 7856 | 3 | 4 | | | IV-1 | PPM1L | 1.19 |
| 7761 | 3 | 4 | | | IV-1 | PEG3 | 1.28 | 7857 | 3 | 4 | | | IV-1 | PPP1CB | 1.12 |
| 7762 | 3 | 4 | | | IV-1 | PELI1 | 1.07 | 7858 | 3 | 4 | | | IV-1 | PPP1R12A | 1.35 |
| 7763 | 3 | 4 | | | IV-1 | PELI2 | 1.38 | 7859 | 3 | 4 | | | IV-1 | PPP1R2 | 1.17 |
| 7764 | 3 | 4 | | | IV-1 | PER2 | 1.20 | 7860 | 3 | 4 | | | IV-1 | PPP1R21 | 1.24 |
| 7765 | 3 | 4 | | | IV-1 | PEX1 | 1.30 | 7861 | 3 | 4 | | | IV-1 | PPP1R3D | 1.25 |
| 7766 | 3 | 4 | | | IV-1 | PEX11A | 1.30 | 7862 | 3 | 4 | | | IV-1 | PPP2R5C | 1.13 |
| 7767 | 3 | 4 | | | IV-1 | PEX13 | 1.08 | 7863 | 3 | 4 | | | IV-1 | PPP2R5E | 1.48 |
| 7768 | 3 | 4 | | | IV-1 | PEX19 | 1.02 | 7864 | 3 | 4 | | | IV-1 | PPP3CB | 1.07 |
| 7769 | 3 | 4 | | | IV-1 | PEX2 | 1.01 | 7865 | 3 | 4 | | | IV-1 | PPP6R3 | 1.04 |
| 7770 | 3 | 4 | | | IV-1 | PEX3 | 1.37 | 7866 | 3 | 4 | | | IV-1 | PPPDE1 | 1.06 |
| 7771 | 3 | 4 | | | IV-1 | PFKFB4 | 1.16 | 7867 | 3 | 4 | | | IV-1 | PQLC3 | 1.05 |
| 7772 | 3 | 4 | | | IV-1 | PGBD4 | 1.20 | 7868 | 3 | 4 | | | IV-1 | PRDM11 | 1.01 |
| 7773 | 3 | 4 | | | IV-1 | PGGT1B | 1.22 | 7869 | 3 | 4 | | | IV-1 | PRDM15 | 1.01 |

Fig. 38 - 42

| | | | | | | | | | | | | | | |
|---|---|---|---|---|---|---|---|---|---|---|---|---|---|---|
| 7870 | 3 | 4 | | | IV-1 | PRDM16 | 1.33 | 7966 | 3 | 4 | | | IV-1 | RASGRP3 | 1.20 |
| 7871 | 3 | 4 | | | IV-1 | PRDM2 | 1.19 | 7967 | 3 | 4 | | | IV-1 | RASSF10 | 1.10 |
| 7872 | 3 | 4 | | | IV-1 | PRDM4 | 1.10 | 7968 | 3 | 4 | | | IV-1 | RASSF2 | 1.12 |
| 7873 | 3 | 4 | | | IV-1 | PRDM6 | 1.01 | 7969 | 3 | 4 | | | IV-1 | RASSF3 | 1.12 |
| 7874 | 3 | 4 | | | IV-1 | PRDM8 | 1.04 | 7970 | 3 | 4 | | | IV-1 | RAVER2 | 1.23 |
| 7875 | 3 | 4 | | | IV-1 | PRDX3 | 1.05 | 7971 | 3 | 4 | | | IV-1 | RBAK | 1.47 |
| 7876 | 3 | 4 | | | IV-1 | PRELID2 | 1.20 | 7972 | 3 | 4 | | | IV-1 | RBBP4 | 1.08 |
| 7877 | 3 | 4 | | | IV-1 | PREPL | 1.18 | 7973 | 3 | 4 | | | IV-1 | RBBP8 | 1.35 |
| 7878 | 3 | 4 | | | IV-1 | PREX1 | 1.08 | 7974 | 3 | 4 | | | IV-1 | RBFOX2 | 1.25 |
| 7879 | 3 | 4 | | | IV-1 | PRF1 | 1.17 | 7975 | 3 | 4 | | | IV-1 | RBL2 | 1.19 |
| 7880 | 3 | 4 | | | IV-1 | PRKAR1A | 1.18 | 7976 | 3 | 4 | | | IV-1 | RBM20 | 1.44 |
| 7881 | 3 | 4 | | | IV-1 | PRKCE | 1.31 | 7977 | 3 | 4 | | | IV-1 | RBM26 | 1.17 |
| 7882 | 3 | 4 | | | IV-1 | PRKCH | 1.12 | 7978 | 3 | 4 | | | IV-1 | RBM26-AS1 | 1.16 |
| 7883 | 3 | 4 | | | IV-1 | PRKCI | 1.22 | 7979 | 3 | 4 | | | IV-1 | RBM27 | 1.15 |
| 7884 | 3 | 4 | | | IV-1 | PRKCQ | 1.12 | 7980 | 3 | 4 | | | IV-1 | RBM28 | 1.02 |
| 7885 | 3 | 4 | | | IV-1 | PRKD3 | 1.17 | 7981 | 3 | 4 | | | IV-1 | RBM33 | 1.40 |
| 7886 | 3 | 4 | | | IV-1 | PRKRIR | 1.11 | 7982 | 3 | 4 | | | IV-1 | RBM43 | 1.30 |
| 7887 | 3 | 4 | | | IV-1 | PRLR | 1.32 | 7983 | 3 | 4 | | | IV-1 | RBM48 | 1.26 |
| 7888 | 3 | 4 | | | IV-1 | PRMT10 | 1.19 | 7984 | 3 | 4 | | | IV-1 | RBMS1 | 1.18 |
| 7889 | 3 | 4 | | | IV-1 | PRMT3 | 1.14 | 7985 | 3 | 4 | | | IV-1 | RBMS3 | 1.12 |
| 7890 | 3 | 4 | | | IV-1 | PRO0611 | 1.35 | 7986 | 3 | 4 | | | IV-1 | RBMXL1 | 1.06 |
| 7891 | 3 | 4 | | | IV-1 | PROK2 | 1.32 | 7987 | 3 | 4 | | | IV-1 | RC3H1 | 1.08 |
| 7892 | 3 | 4 | | | IV-1 | PROSER1 | 1.22 | 7988 | 3 | 4 | | | IV-1 | RC3H2 | 1.23 |
| 7893 | 3 | 4 | | | IV-1 | PRPF38A | 1.03 | 7989 | 3 | 4 | | | IV-1 | RCBTB1 | 1.30 |
| 7894 | 3 | 4 | | | IV-1 | PRPF40A | 1.11 | 7990 | 3 | 4 | | | IV-1 | RCHY1 | 1.32 |
| 7895 | 3 | 4 | | | IV-1 | PRPH2 | 1.08 | 7991 | 3 | 4 | | | IV-1 | RDH10 | 1.20 |
| 7896 | 3 | 4 | | | IV-1 | PRR5L | 1.32 | 7992 | 3 | 4 | | | IV-1 | RDH11 | 1.25 |
| 7897 | 3 | 4 | | | IV-1 | PRRC1 | 1.12 | 7993 | 3 | 4 | | | IV-1 | RDH13 | 1.35 |
| 7898 | 3 | 4 | | | IV-1 | PRRG1 | 1.07 | 7994 | 3 | 4 | | | IV-1 | REEP3 | 1.21 |
| 7899 | 3 | 4 | | | IV-1 | PRRG4 | 1.36 | 7995 | 3 | 4 | | | IV-1 | RELN | 1.08 |
| 7900 | 3 | 4 | | | IV-1 | PSD3 | 1.11 | 7996 | 3 | 4 | | | IV-1 | REPS2 | 1.03 |
| 7901 | 3 | 4 | | | IV-1 | PSIP1 | 1.46 | 7997 | 3 | 4 | | | IV-1 | RERGL | 1.39 |
| 7902 | 3 | 4 | | | IV-1 | PSMA3 | 1.04 | 7998 | 3 | 4 | | | IV-1 | REST | 1.12 |
| 7903 | 3 | 4 | | | IV-1 | PSMA4 | 1.03 | 7999 | 3 | 4 | | | IV-1 | RET | 1.11 |
| 7904 | 3 | 4 | | | IV-1 | PSMC6 | 1.43 | 8000 | 3 | 4 | | | IV-1 | REV3L | 1.33 |
| 7905 | 3 | 4 | | | IV-1 | PSMD1 | 1.38 | 8001 | 3 | 4 | | | IV-1 | RFC1 | 1.46 |
| 7906 | 3 | 4 | | | IV-1 | PSMD12 | 1.31 | 8002 | 3 | 4 | | | IV-1 | RFK | 1.30 |
| 7907 | 3 | 4 | | | IV-1 | PSME2 | 1.12 | 8003 | 3 | 4 | | | IV-1 | RFPL2 | 1.22 |
| 7908 | 3 | 4 | | | IV-1 | PSME4 | 1.07 | 8004 | 3 | 4 | | | IV-1 | RFTN2 | 1.27 |
| 7909 | 3 | 4 | | | IV-1 | PSORS1C3 | 1.38 | 8005 | 3 | 4 | | | IV-1 | RFX5 | 1.13 |
| 7910 | 3 | 4 | | | IV-1 | PSTPIP2 | 1.26 | 8006 | 3 | 4 | | | IV-1 | RFX7 | 1.40 |
| 7911 | 3 | 4 | | | IV-1 | PTCD1 | 1.30 | 8007 | 3 | 4 | | | IV-1 | RFX8 | 1.02 |
| 7912 | 3 | 4 | | | IV-1 | PTEN | 1.08 | 8008 | 3 | 4 | | | IV-1 | RGAG4 | 1.06 |
| 7913 | 3 | 4 | | | IV-1 | PTGDR2 | 1.12 | 8009 | 3 | 4 | | | IV-1 | RGL1 | 1.40 |
| 7914 | 3 | 4 | | | IV-1 | PTGER2 | 1.10 | 8010 | 3 | 4 | | | IV-1 | RGMB | 1.20 |
| 7915 | 3 | 4 | | | IV-1 | PTN | 1.45 | 8011 | 3 | 4 | | | IV-1 | RGPD3 | 1.14 |
| 7916 | 3 | 4 | | | IV-1 | PTPN11 | 1.24 | 8012 | 3 | 4 | | | IV-1 | RGS18 | 1.10 |
| 7917 | 3 | 4 | | | IV-1 | PTPN21 | 1.24 | 8013 | 3 | 4 | | | IV-1 | RGS9BP | 1.05 |
| 7918 | 3 | 4 | | | IV-1 | PTPN22 | 1.02 | 8014 | 3 | 4 | | | IV-1 | RHOT1 | 1.07 |
| 7919 | 3 | 4 | | | IV-1 | PTPN3 | 1.13 | 8015 | 3 | 4 | | | IV-1 | RIC8B | 1.08 |
| 7920 | 3 | 4 | | | IV-1 | PTPRD | 1.08 | 8016 | 3 | 4 | | | IV-1 | RICTOR | 1.25 |
| 7921 | 3 | 4 | | | IV-1 | PTPRG | 1.15 | 8017 | 3 | 4 | | | IV-1 | RIF1 | 1.23 |
| 7922 | 3 | 4 | | | IV-1 | PTPRJ | 1.44 | 8018 | 3 | 4 | | | IV-1 | RIN2 | 1.07 |
| 7923 | 3 | 4 | | | IV-1 | PTPRK | 1.06 | 8019 | 3 | 4 | | | IV-1 | RINT1 | 1.36 |
| 7924 | 3 | 4 | | | IV-1 | PUM1 | 1.04 | 8020 | 3 | 4 | | | IV-1 | RIOK1 | 1.12 |
| 7925 | 3 | 4 | | | IV-1 | PUM2 | 1.15 | 8021 | 3 | 4 | | | IV-1 | RIOK2 | 1.05 |
| 7926 | 3 | 4 | | | IV-1 | PUS7L | 1.13 | 8022 | 3 | 4 | | | IV-1 | RIOK3 | 1.30 |
| 7927 | 3 | 4 | | | IV-1 | PVRL3 | 1.22 | 8023 | 3 | 4 | | | IV-1 | RIPK1 | 1.14 |
| 7928 | 3 | 4 | | | IV-1 | PWP1 | 1.01 | 8024 | 3 | 4 | | | IV-1 | RIT1 | 1.25 |
| 7929 | 3 | 4 | | | IV-1 | QPRT | 1.22 | 8025 | 3 | 4 | | | IV-1 | RNASE2 | 1.41 |
| 7930 | 3 | 4 | | | IV-1 | QSER1 | 1.43 | 8026 | 3 | 4 | | | IV-1 | RNASE4 | 1.02 |
| 7931 | 3 | 4 | | | IV-1 | QTRTD1 | 1.19 | 8027 | 3 | 4 | | | IV-1 | RNASET2 | 1.20 |
| 7932 | 3 | 4 | | | IV-1 | RAB1A | 1.08 | 8028 | 3 | 4 | | | IV-1 | RNF103 | 1.40 |
| 7933 | 3 | 4 | | | IV-1 | RAB27A | 1.31 | 8029 | 3 | 4 | | | IV-1 | RNF11 | 1.09 |
| 7934 | 3 | 4 | | | IV-1 | RAB31 | 1.17 | 8030 | 3 | 4 | | | IV-1 | RNF115 | 1.27 |
| 7935 | 3 | 4 | | | IV-1 | RAB33B | 1.47 | 8031 | 3 | 4 | | | IV-1 | RNF138 | 1.06 |
| 7936 | 3 | 4 | | | IV-1 | RAB3B | 1.18 | 8032 | 3 | 4 | | | IV-1 | RNF138P1 | 1.17 |
| 7937 | 3 | 4 | | | IV-1 | RAB3GAP1 | 1.11 | 8033 | 3 | 4 | | | IV-1 | RNF14 | 1.11 |
| 7938 | 3 | 4 | | | IV-1 | RAB3GAP2 | 1.48 | 8034 | 3 | 4 | | | IV-1 | RNF141 | 1.14 |
| 7939 | 3 | 4 | | | IV-1 | RAB42 | 1.24 | 8035 | 3 | 4 | | | IV-1 | RNF144A | 1.02 |
| 7940 | 3 | 4 | | | IV-1 | RAB5A | 1.08 | 8036 | 3 | 4 | | | IV-1 | RNF146 | 1.16 |
| 7941 | 3 | 4 | | | IV-1 | RAB8B | 1.28 | 8037 | 3 | 4 | | | IV-1 | RNF149 | 1.08 |
| 7942 | 3 | 4 | | | IV-1 | RABEP1 | 1.37 | 8038 | 3 | 4 | | | IV-1 | RNF157 | 1.16 |
| 7943 | 3 | 4 | | | IV-1 | RABGAP1 | 1.02 | 8039 | 3 | 4 | | | IV-1 | RNF168 | 1.38 |
| 7944 | 3 | 4 | | | IV-1 | RABGAP1L | 1.29 | 8040 | 3 | 4 | | | IV-1 | RNF175 | 1.02 |
| 7945 | 3 | 4 | | | IV-1 | RABGEF1 | 1.23 | 8041 | 3 | 4 | | | IV-1 | RNF213 | 1.24 |
| 7946 | 3 | 4 | | | IV-1 | RABL3 | 1.29 | 8042 | 3 | 4 | | | IV-1 | RNF219 | 1.48 |
| 7947 | 3 | 4 | | | IV-1 | RAD1 | 1.36 | 8043 | 3 | 4 | | | IV-1 | RNF38 | 1.06 |
| 7948 | 3 | 4 | | | IV-1 | RAD18 | 1.03 | 8044 | 3 | 4 | | | IV-1 | RNFT1 | 1.17 |
| 7949 | 3 | 4 | | | IV-1 | RAD21 | 1.16 | 8045 | 3 | 4 | | | IV-1 | RNGTT | 1.05 |
| 7950 | 3 | 4 | | | IV-1 | RAD51AP1 | 1.01 | 8046 | 3 | 4 | | | IV-1 | RNMT | 1.04 |
| 7951 | 3 | 4 | | | IV-1 | RAD51D | 1.02 | 8047 | 3 | 4 | | | IV-1 | ROCK1 | 1.41 |
| 7952 | 3 | 4 | | | IV-1 | RALGAPA2 | 1.26 | 8048 | 3 | 4 | | | IV-1 | ROCK1P1 | 1.25 |
| 7953 | 3 | 4 | | | IV-1 | RALGAPB | 1.24 | 8049 | 3 | 4 | | | IV-1 | RP2 | 1.20 |
| 7954 | 3 | 4 | | | IV-1 | RALGPS1 | 1.47 | 8050 | 3 | 4 | | | IV-1 | RPAP3 | 1.23 |
| 7955 | 3 | 4 | | | IV-1 | RANBP2 | 1.34 | 8051 | 3 | 4 | | | IV-1 | RPGRIP1L | 1.08 |
| 7956 | 3 | 4 | | | IV-1 | RANBP6 | 1.10 | 8052 | 3 | 4 | | | IV-1 | RPL13AP6 | 1.05 |
| 7957 | 3 | 4 | | | IV-1 | RANBP9 | 1.02 | 8053 | 3 | 4 | | | IV-1 | RPL18 | 1.03 |
| 7958 | 3 | 4 | | | IV-1 | RAP1GDS1 | 1.00 | 8054 | 3 | 4 | | | IV-1 | RPL21 | 1.08 |
| 7959 | 3 | 4 | | | IV-1 | RAPGEF4 | 1.31 | 8055 | 3 | 4 | | | IV-1 | RPL22L1 | 1.07 |
| 7960 | 3 | 4 | | | IV-1 | RAPH1 | 1.18 | 8056 | 3 | 4 | | | IV-1 | RPL23AP7 | 1.39 |
| 7961 | 3 | 4 | | | IV-1 | RARB | 1.30 | 8057 | 3 | 4 | | | IV-1 | RPL32P3 | 1.43 |
| 7962 | 3 | 4 | | | IV-1 | RARS2 | 1.06 | 8058 | 3 | 4 | | | IV-1 | RPP14 | 1.46 |
| 7963 | 3 | 4 | | | IV-1 | RASA1 | 1.14 | 8059 | 3 | 4 | | | IV-1 | RPRD1A | 1.20 |
| 7964 | 3 | 4 | | | IV-1 | RASGEF1B | 1.29 | 8060 | 3 | 4 | | | IV-1 | RPRD1B | 1.09 |
| 7965 | 3 | 4 | | | IV-1 | RASGRF2 | 1.01 | 8061 | 3 | 4 | | | IV-1 | RPRD2 | 1.02 |

Fig. 38 - 43

| | | | | | | | | | | | | | | |
|---|---|---|---|---|---|---|---|---|---|---|---|---|---|---|
| 8062 | 3 | 4 | | | IV-1 | RPS15A | 1.09 | 8158 | 3 | 4 | | | IV-1 | SH3PXD2A | 1.18 |
| 8063 | 3 | 4 | | | IV-1 | RPS6KA3 | 1.17 | 8159 | 3 | 4 | | | IV-1 | SH3RF1 | 1.14 |
| 8064 | 3 | 4 | | | IV-1 | RPS6KA6 | 1.21 | 8160 | 3 | 4 | | | IV-1 | SH3YL1 | 1.10 |
| 8065 | 3 | 4 | | | IV-1 | RPS6KB1 | 1.27 | 8161 | 3 | 4 | | | IV-1 | SHC4 | 1.02 |
| 8066 | 3 | 4 | | | IV-1 | RPS6KC1 | 1.14 | 8162 | 3 | 4 | | | IV-1 | SHOC2 | 1.22 |
| 8067 | 3 | 4 | | | IV-1 | RRAGB | 1.09 | 8163 | 3 | 4 | | | IV-1 | SHOX2 | 1.46 |
| 8068 | 3 | 4 | | | IV-1 | RREB1 | 1.20 | 8164 | 3 | 4 | | | IV-1 | SHROOM3 | 1.33 |
| 8069 | 3 | 4 | | | IV-1 | RRM1 | 1.12 | 8165 | 3 | 4 | | | IV-1 | SIDT1 | 1.27 |
| 8070 | 3 | 4 | | | IV-1 | RRM2B | 1.02 | 8166 | 3 | 4 | | | IV-1 | SIGLEC8 | 1.31 |
| 8071 | 3 | 4 | | | IV-1 | RRN3 | 1.02 | 8167 | 3 | 4 | | | IV-1 | SIKE1 | 1.15 |
| 8072 | 3 | 4 | | | IV-1 | RRN3P3 | 1.16 | 8168 | 3 | 4 | | | IV-1 | SIPA1L2 | 1.18 |
| 8073 | 3 | 4 | | | IV-1 | RRP15 | 1.05 | 8169 | 3 | 4 | | | IV-1 | SIRPB2 | 1.08 |
| 8074 | 3 | 4 | | | IV-1 | RSAD2 | 1.41 | 8170 | 3 | 4 | | | IV-1 | SIRT1 | 1.37 |
| 8075 | 3 | 4 | | | IV-1 | RSBN1 | 1.13 | 8171 | 3 | 4 | | | IV-1 | SKIV2L2 | 1.30 |
| 8076 | 3 | 4 | | | IV-1 | RSC1A1 | 1.09 | 8172 | 3 | 4 | | | IV-1 | SKP2 | 1.13 |
| 8077 | 3 | 4 | | | IV-1 | RSRC1 | 1.28 | 8173 | 3 | 4 | | | IV-1 | SLAMF1 | 1.38 |
| 8078 | 3 | 4 | | | IV-1 | RTF1 | 1.17 | 8174 | 3 | 4 | | | IV-1 | SLC10A7 | 1.22 |
| 8079 | 3 | 4 | | | IV-1 | RUNDC1 | 1.00 | 8175 | 3 | 4 | | | IV-1 | SLC11A1 | 1.01 |
| 8080 | 3 | 4 | | | IV-1 | RUNX1 | 1.12 | 8176 | 3 | 4 | | | IV-1 | SLC11A2 | 1.27 |
| 8081 | 3 | 4 | | | IV-1 | RUSC1-AS1 | 1.14 | 8177 | 3 | 4 | | | IV-1 | SLC13A3 | 1.09 |
| 8082 | 3 | 4 | | | IV-1 | RYBP | 1.32 | 8178 | 3 | 4 | | | IV-1 | SLC16A1 | 1.20 |
| 8083 | 3 | 4 | | | IV-1 | S100A12 | 1.49 | 8179 | 3 | 4 | | | IV-1 | SLC16A8 | 1.06 |
| 8084 | 3 | 4 | | | IV-1 | S100PBP | 1.45 | 8180 | 3 | 4 | | | IV-1 | SLC22A15 | 1.50 |
| 8085 | 3 | 4 | | | IV-1 | SACM1L | 1.06 | 8181 | 3 | 4 | | | IV-1 | SLC22A18AS | 1.05 |
| 8086 | 3 | 4 | | | IV-1 | SACS | 1.44 | 8182 | 3 | 4 | | | IV-1 | SLC22A3 | 1.13 |
| 8087 | 3 | 4 | | | IV-1 | SAMHD1 | 1.41 | 8183 | 3 | 4 | | | IV-1 | SLC22A5 | 1.10 |
| 8088 | 3 | 4 | | | IV-1 | SAR1A | 1.08 | 8184 | 3 | 4 | | | IV-1 | SLC23A2 | 1.49 |
| 8089 | 3 | 4 | | | IV-1 | SAR1B | 1.34 | 8185 | 3 | 4 | | | IV-1 | SLC24A1 | 1.15 |
| 8090 | 3 | 4 | | | IV-1 | SASH1 | 1.46 | 8186 | 3 | 4 | | | IV-1 | SLC25A12 | 1.17 |
| 8091 | 3 | 4 | | | IV-1 | SAV1 | 1.08 | 8187 | 3 | 4 | | | IV-1 | SLC25A16 | 1.38 |
| 8092 | 3 | 4 | | | IV-1 | SBF2 | 1.20 | 8188 | 3 | 4 | | | IV-1 | SLC25A18 | 1.29 |
| 8093 | 3 | 4 | | | IV-1 | SBNO1 | 1.36 | 8189 | 3 | 4 | | | IV-1 | SLC25A24 | 1.17 |
| 8094 | 3 | 4 | | | IV-1 | SCAF11 | 1.33 | 8190 | 3 | 4 | | | IV-1 | SLC25A35 | 1.02 |
| 8095 | 3 | 4 | | | IV-1 | SCAI | 1.26 | 8191 | 3 | 4 | | | IV-1 | SLC25A46 | 1.33 |
| 8096 | 3 | 4 | | | IV-1 | SCAMP1 | 1.01 | 8192 | 3 | 4 | | | IV-1 | SLC26A4 | 1.24 |
| 8097 | 3 | 4 | | | IV-1 | SCARB2 | 1.05 | 8193 | 3 | 4 | | | IV-1 | SLC27A6 | 1.29 |
| 8098 | 3 | 4 | | | IV-1 | SCGB2A1 | 1.17 | 8194 | 3 | 4 | | | IV-1 | SLC28A3 | 1.36 |
| 8099 | 3 | 4 | | | IV-1 | SCLT1 | 1.10 | 8195 | 3 | 4 | | | IV-1 | SLC2A11 | 1.11 |
| 8100 | 3 | 4 | | | IV-1 | SCML2 | 1.03 | 8196 | 3 | 4 | | | IV-1 | SLC2A13 | 1.06 |
| 8101 | 3 | 4 | | | IV-1 | SCML4 | 1.21 | 8197 | 3 | 4 | | | IV-1 | SLC2A9 | 1.01 |
| 8102 | 3 | 4 | | | IV-1 | SCN9A | 1.33 | 8198 | 3 | 4 | | | IV-1 | SLC30A6 | 1.13 |
| 8103 | 3 | 4 | | | IV-1 | SCNN1G | 1.10 | 8199 | 3 | 4 | | | IV-1 | SLC30A9 | 1.06 |
| 8104 | 3 | 4 | | | IV-1 | SCOC | 1.01 | 8200 | 3 | 4 | | | IV-1 | SLC33A1 | 1.21 |
| 8105 | 3 | 4 | | | IV-1 | SCPEP1 | 1.12 | 8201 | 3 | 4 | | | IV-1 | SLC35A5 | 1.10 |
| 8106 | 3 | 4 | | | IV-1 | SCRN1 | 1.30 | 8202 | 3 | 4 | | | IV-1 | SLC35B1 | 1.04 |
| 8107 | 3 | 4 | | | IV-1 | SCRN3 | 1.40 | 8203 | 3 | 4 | | | IV-1 | SLC35B3 | 1.03 |
| 8108 | 3 | 4 | | | IV-1 | SCUBE1 | 1.11 | 8204 | 3 | 4 | | | IV-1 | SLC35B4 | 1.32 |
| 8109 | 3 | 4 | | | IV-1 | SCYL2 | 1.41 | 8205 | 3 | 4 | | | IV-1 | SLC35E2 | 1.38 |
| 8110 | 3 | 4 | | | IV-1 | SEC22B | 1.29 | 8206 | 3 | 4 | | | IV-1 | SLC35E2B | 1.37 |
| 8111 | 3 | 4 | | | IV-1 | SEC23A | 1.02 | 8207 | 3 | 4 | | | IV-1 | SLC35F1 | 1.07 |
| 8112 | 3 | 4 | | | IV-1 | SEC23IP | 1.30 | 8208 | 3 | 4 | | | IV-1 | SLC38A2 | 1.33 |
| 8113 | 3 | 4 | | | IV-1 | SEC24B | 1.35 | 8209 | 3 | 4 | | | IV-1 | SLC38A4 | 1.34 |
| 8114 | 3 | 4 | | | IV-1 | SEC24D | 1.20 | 8210 | 3 | 4 | | | IV-1 | SLC38A6 | 1.25 |
| 8115 | 3 | 4 | | | IV-1 | SEC31A | 1.02 | 8211 | 3 | 4 | | | IV-1 | SLC39A10 | 1.34 |
| 8116 | 3 | 4 | | | IV-1 | SEC62 | 1.36 | 8212 | 3 | 4 | | | IV-1 | SLC39A14 | 1.32 |
| 8117 | 3 | 4 | | | IV-1 | SEC63 | 1.07 | 8213 | 3 | 4 | | | IV-1 | SLC39A6 | 1.38 |
| 8118 | 3 | 4 | | | IV-1 | SECISBP2 | 1.36 | 8214 | 3 | 4 | | | IV-1 | SLC39A9 | 1.19 |
| 8119 | 3 | 4 | | | IV-1 | SECISBP2L | 1.35 | 8215 | 3 | 4 | | | IV-1 | SLC41A2 | 1.36 |
| 8120 | 3 | 4 | | | IV-1 | SEH1L | 1.06 | 8216 | 3 | 4 | | | IV-1 | SLC44A1 | 1.03 |
| 8121 | 3 | 4 | | | IV-1 | SEL1L | 1.30 | 8217 | 3 | 4 | | | IV-1 | SLC47A1 | 1.23 |
| 8122 | 3 | 4 | | | IV-1 | SELK | 1.14 | 8218 | 3 | 4 | | | IV-1 | SLC47A2 | 1.12 |
| 8123 | 3 | 4 | | | IV-1 | SEMA3C | 1.22 | 8219 | 3 | 4 | | | IV-1 | SLC4A5 | 1.50 |
| 8124 | 3 | 4 | | | IV-1 | SEMA3E | 1.35 | 8220 | 3 | 4 | | | IV-1 | SLC6A13 | 1.13 |
| 8125 | 3 | 4 | | | IV-1 | SEMA4D | 1.07 | 8221 | 3 | 4 | | | IV-1 | SLC7A5P1 | 1.42 |
| 8126 | 3 | 4 | | | IV-1 | SEMA4G | 1.10 | 8222 | 3 | 4 | | | IV-1 | SLC7A5P2 | 1.46 |
| 8127 | 3 | 4 | | | IV-1 | SEMA5A | 1.37 | 8223 | 3 | 4 | | | IV-1 | SLC7A7 | 1.06 |
| 8128 | 3 | 4 | | | IV-1 | SEMA6A | 1.19 | 8224 | 3 | 4 | | | IV-1 | SLC9A6 | 1.08 |
| 8129 | 3 | 4 | | | IV-1 | SEMA6D | 1.43 | 8225 | 3 | 4 | | | IV-1 | SLFN12 | 1.29 |
| 8130 | 3 | 4 | | | IV-1 | SENP1 | 1.10 | 8226 | 3 | 4 | | | IV-1 | SLITRK2 | 1.26 |
| 8131 | 3 | 4 | | | IV-1 | SENP2 | 1.23 | 8227 | 3 | 4 | | | IV-1 | SLITRK3 | 1.11 |
| 8132 | 3 | 4 | | | IV-1 | SENP8 | 1.22 | 8228 | 3 | 4 | | | IV-1 | SLITRK4 | 1.13 |
| 8133 | 3 | 4 | | | IV-1 | SEPT10 | 1.15 | 8229 | 3 | 4 | | | IV-1 | SLITRK5 | 1.35 |
| 8134 | 3 | 4 | | | IV-1 | SEPT2 | 1.06 | 8230 | 3 | 4 | | | IV-1 | SLMAP | 1.17 |
| 8135 | 3 | 4 | | | IV-1 | SEPT7 | 1.08 | 8231 | 3 | 4 | | | IV-1 | SLMO2 | 1.19 |
| 8136 | 3 | 4 | | | IV-1 | SERAC1 | 1.03 | 8232 | 3 | 4 | | | IV-1 | SLU7 | 1.33 |
| 8137 | 3 | 4 | | | IV-1 | SERINC1 | 1.10 | 8233 | 3 | 4 | | | IV-1 | SMAD2 | 1.01 |
| 8138 | 3 | 4 | | | IV-1 | SERPINA9 | 1.49 | 8234 | 3 | 4 | | | IV-1 | SMAD4 | 1.11 |
| 8139 | 3 | 4 | | | IV-1 | SERTAD2 | 1.33 | 8235 | 3 | 4 | | | IV-1 | SMAD5 | 1.27 |
| 8140 | 3 | 4 | | | IV-1 | SERTAD3 | 1.06 | 8236 | 3 | 4 | | | IV-1 | SMARCA2 | 1.21 |
| 8141 | 3 | 4 | | | IV-1 | SETD2 | 1.04 | 8237 | 3 | 4 | | | IV-1 | SMARCA5 | 1.19 |
| 8142 | 3 | 4 | | | IV-1 | SETD5 | 1.08 | 8238 | 3 | 4 | | | IV-1 | SMC5 | 1.03 |
| 8143 | 3 | 4 | | | IV-1 | SETD7 | 1.47 | 8239 | 3 | 4 | | | IV-1 | SMCHD1 | 1.30 |
| 8144 | 3 | 4 | | | IV-1 | SETDB2 | 1.33 | 8240 | 3 | 4 | | | IV-1 | SMCR7L | 1.06 |
| 8145 | 3 | 4 | | | IV-1 | SETMAR | 1.24 | 8241 | 3 | 4 | | | IV-1 | SMEK1 | 1.02 |
| 8146 | 3 | 4 | | | IV-1 | SETX | 1.08 | 8242 | 3 | 4 | | | IV-1 | SMEK2 | 1.18 |
| 8147 | 3 | 4 | | | IV-1 | SFRP1 | 1.08 | 8243 | 3 | 4 | | | IV-1 | SMNDC1 | 1.00 |
| 8148 | 3 | 4 | | | IV-1 | SFT2D2 | 1.11 | 8244 | 3 | 4 | | | IV-1 | SMPDL3B | 1.04 |
| 8149 | 3 | 4 | | | IV-1 | SGCB | 1.11 | 8245 | 3 | 4 | | | IV-1 | SMYD4 | 1.17 |
| 8150 | 3 | 4 | | | IV-1 | SGOL2 | 1.05 | 8246 | 3 | 4 | | | IV-1 | SNAI2 | 1.12 |
| 8151 | 3 | 4 | | | IV-1 | SGTB | 1.24 | 8247 | 3 | 4 | | | IV-1 | SNAI3 | 1.10 |
| 8152 | 3 | 4 | | | IV-1 | SH2B3 | 1.44 | 8248 | 3 | 4 | | | IV-1 | SNAPC1 | 1.07 |
| 8153 | 3 | 4 | | | IV-1 | SH2D1A | 1.00 | 8249 | 3 | 4 | | | IV-1 | SNED1 | 1.35 |
| 8154 | 3 | 4 | | | IV-1 | SH3BGRL | 1.01 | 8250 | 3 | 4 | | | IV-1 | SNHG4 | 1.42 |
| 8155 | 3 | 4 | | | IV-1 | SH3BP2 | 1.15 | 8251 | 3 | 4 | | | IV-1 | SNIP1 | 1.34 |
| 8156 | 3 | 4 | | | IV-1 | SH3D19 | 1.12 | 8252 | 3 | 4 | | | IV-1 | SNN | 1.16 |
| 8157 | 3 | 4 | | | IV-1 | SH3KBP1 | 1.18 | 8253 | 3 | 4 | | | IV-1 | SNORA67 | 1.11 |

Fig. 38 - 44

| | | | | | | | |
|---|---|---|---|---|---|---|---|
| 8254 | 3 | 4 | | | IV-1 | SNRNP48 | 1.19 |
| 8255 | 3 | 4 | | | IV-1 | SNTB2 | 1.48 |
| 8256 | 3 | 4 | | | IV-1 | SNX1 | 1.26 |
| 8257 | 3 | 4 | | | IV-1 | SNX14 | 1.37 |
| 8258 | 3 | 4 | | | IV-1 | SNX16 | 1.20 |
| 8259 | 3 | 4 | | | IV-1 | SNX18 | 1.11 |
| 8260 | 3 | 4 | | | IV-1 | SNX19 | 1.21 |
| 8261 | 3 | 4 | | | IV-1 | SNX24 | 1.11 |
| 8262 | 3 | 4 | | | IV-1 | SNX6 | 1.01 |
| 8263 | 3 | 4 | | | IV-1 | SOCS4 | 1.50 |
| 8264 | 3 | 4 | | | IV-1 | SOCS5 | 1.22 |
| 8265 | 3 | 4 | | | IV-1 | SORBS2 | 1.19 |
| 8266 | 3 | 4 | | | IV-1 | SORT1 | 1.18 |
| 8267 | 3 | 4 | | | IV-1 | SOS1 | 1.35 |
| 8268 | 3 | 4 | | | IV-1 | SOS2 | 1.01 |
| 8269 | 3 | 4 | | | IV-1 | SOWAHD | 1.18 |
| 8270 | 3 | 4 | | | IV-1 | SP140 | 1.14 |
| 8271 | 3 | 4 | | | IV-1 | SP3 | 1.29 |
| 8272 | 3 | 4 | | | IV-1 | SPAG5 | 1.00 |
| 8273 | 3 | 4 | | | IV-1 | SPARCL1 | 1.26 |
| 8274 | 3 | 4 | | | IV-1 | SPAST | 1.15 |
| 8275 | 3 | 4 | | | IV-1 | SPATA13 | 1.36 |
| 8276 | 3 | 4 | | | IV-1 | SPATA5 | 1.25 |
| 8277 | 3 | 4 | | | IV-1 | SPECC1 | 1.20 |
| 8278 | 3 | 4 | | | IV-1 | SPEF2 | 1.07 |
| 8279 | 3 | 4 | | | IV-1 | SPEN | 1.07 |
| 8280 | 3 | 4 | | | IV-1 | SPG11 | 1.36 |
| 8281 | 3 | 4 | | | IV-1 | SPG20 | 1.38 |
| 8282 | 3 | 4 | | | IV-1 | SPIRE1 | 1.37 |
| 8283 | 3 | 4 | | | IV-1 | SPOPL | 1.44 |
| 8284 | 3 | 4 | | | IV-1 | SPP1 | 1.38 |
| 8285 | 3 | 4 | | | IV-1 | SPPL2A | 1.14 |
| 8286 | 3 | 4 | | | IV-1 | SPRED1 | 1.19 |
| 8287 | 3 | 4 | | | IV-1 | SPTBN5 | 1.22 |
| 8288 | 3 | 4 | | | IV-1 | SPTLC1 | 1.03 |
| 8289 | 3 | 4 | | | IV-1 | SPTY2D1 | 1.37 |
| 8290 | 3 | 4 | | | IV-1 | SREBF1 | 1.14 |
| 8291 | 3 | 4 | | | IV-1 | SRPK2 | 1.11 |
| 8292 | 3 | 4 | | | IV-1 | SRR | 1.05 |
| 8293 | 3 | 4 | | | IV-1 | SRRM5 | 1.41 |
| 8294 | 3 | 4 | | | IV-1 | SRSF1 | 1.08 |
| 8295 | 3 | 4 | | | IV-1 | SRSF5 | 1.28 |
| 8296 | 3 | 4 | | | IV-1 | SRSF6 | 1.42 |
| 8297 | 3 | 4 | | | IV-1 | SRSF7 | 1.23 |
| 8298 | 3 | 4 | | | IV-1 | SS18 | 1.06 |
| 8299 | 3 | 4 | | | IV-1 | SSBP2 | 1.02 |
| 8300 | 3 | 4 | | | IV-1 | SSH1 | 1.35 |
| 8301 | 3 | 4 | | | IV-1 | SSR1 | 1.09 |
| 8302 | 3 | 4 | | | IV-1 | SSTR1 | 1.04 |
| 8303 | 3 | 4 | | | IV-1 | ST3GAL1 | 1.01 |
| 8304 | 3 | 4 | | | IV-1 | ST3GAL5 | 1.39 |
| 8305 | 3 | 4 | | | IV-1 | ST6GALNAC1 | 1.08 |
| 8306 | 3 | 4 | | | IV-1 | ST8SIA4 | 1.19 |
| 8307 | 3 | 4 | | | IV-1 | STAC | 1.02 |
| 8308 | 3 | 4 | | | IV-1 | STAG1 | 1.18 |
| 8309 | 3 | 4 | | | IV-1 | STAG2 | 1.06 |
| 8310 | 3 | 4 | | | IV-1 | STAG3L2 | 1.17 |
| 8311 | 3 | 4 | | | IV-1 | STAG3L3 | 1.33 |
| 8312 | 3 | 4 | | | IV-1 | STAM2 | 1.08 |
| 8313 | 3 | 4 | | | IV-1 | STAMBP | 1.16 |
| 8314 | 3 | 4 | | | IV-1 | STARD13 | 1.20 |
| 8315 | 3 | 4 | | | IV-1 | STIL | 1.07 |
| 8316 | 3 | 4 | | | IV-1 | STK10 | 1.04 |
| 8317 | 3 | 4 | | | IV-1 | STK17A | 1.11 |
| 8318 | 3 | 4 | | | IV-1 | STK19 | 1.07 |
| 8319 | 3 | 4 | | | IV-1 | STK3 | 1.10 |
| 8320 | 3 | 4 | | | IV-1 | STK38 | 1.03 |
| 8321 | 3 | 4 | | | IV-1 | STK38L | 1.49 |
| 8322 | 3 | 4 | | | IV-1 | STK4 | 1.46 |
| 8323 | 3 | 4 | | | IV-1 | STOX2 | 1.43 |
| 8324 | 3 | 4 | | | IV-1 | STRBP | 1.19 |
| 8325 | 3 | 4 | | | IV-1 | STRN | 1.03 |
| 8326 | 3 | 4 | | | IV-1 | STX12 | 1.01 |
| 8327 | 3 | 4 | | | IV-1 | STX3 | 1.23 |
| 8328 | 3 | 4 | | | IV-1 | STX7 | 1.33 |
| 8329 | 3 | 4 | | | IV-1 | STXBP5 | 1.27 |
| 8330 | 3 | 4 | | | IV-1 | STYX | 1.22 |
| 8331 | 3 | 4 | | | IV-1 | SUB1 | 1.11 |
| 8332 | 3 | 4 | | | IV-1 | SUCLA2 | 1.08 |
| 8333 | 3 | 4 | | | IV-1 | SUCNR1 | 1.06 |
| 8334 | 3 | 4 | | | IV-1 | SUDS3 | 1.14 |
| 8335 | 3 | 4 | | | IV-1 | SUGT1 | 1.00 |
| 8336 | 3 | 4 | | | IV-1 | SUGT1P1 | 1.00 |
| 8337 | 3 | 4 | | | IV-1 | SULT1C2 | 1.02 |
| 8338 | 3 | 4 | | | IV-1 | SULT1C4 | 1.44 |
| 8339 | 3 | 4 | | | IV-1 | SULT4A1 | 1.35 |
| 8340 | 3 | 4 | | | IV-1 | SUMO4 | 1.42 |
| 8341 | 3 | 4 | | | IV-1 | SUV420H1 | 1.27 |
| 8342 | 3 | 4 | | | IV-1 | SUZ12 | 1.17 |
| 8343 | 3 | 4 | | | IV-1 | SWAP70 | 1.39 |
| 8344 | 3 | 4 | | | IV-1 | SWSAP1 | 1.11 |
| 8345 | 3 | 4 | | | IV-1 | SYAP1 | 1.07 |
| 8346 | 3 | 4 | | | IV-1 | SYCE3 | 1.11 |
| 8347 | 3 | 4 | | | IV-1 | SYNJ2BP | 1.28 |
| 8348 | 3 | 4 | | | IV-1 | SYNRG | 1.28 |
| 8349 | 3 | 4 | | | IV-1 | SYT11 | 1.19 |
| 8350 | 3 | 4 | | | IV-1 | TADA2A | 1.04 |
| 8351 | 3 | 4 | | | IV-1 | TAF1 | 1.12 |
| 8352 | 3 | 4 | | | IV-1 | TAF11 | 1.02 |
| 8353 | 3 | 4 | | | IV-1 | TAF1D | 1.09 |
| 8354 | 3 | 4 | | | IV-1 | TAF2 | 1.13 |
| 8355 | 3 | 4 | | | IV-1 | TAF8 | 1.33 |
| 8356 | 3 | 4 | | | IV-1 | TAF9B | 1.06 |
| 8357 | 3 | 4 | | | IV-1 | TAGLN3 | 1.10 |
| 8358 | 3 | 4 | | | IV-1 | TANC1 | 1.18 |
| 8359 | 3 | 4 | | | IV-1 | TANK | 1.22 |
| 8360 | 3 | 4 | | | IV-1 | TAOK1 | 1.44 |
| 8361 | 3 | 4 | | | IV-1 | TAPT1 | 1.07 |
| 8362 | 3 | 4 | | | IV-1 | TARDBP | 1.00 |
| 8363 | 3 | 4 | | | IV-1 | TARP | 1.05 |
| 8364 | 3 | 4 | | | IV-1 | TAS2R4 | 1.03 |
| 8365 | 3 | 4 | | | IV-1 | TASP1 | 1.04 |
| 8366 | 3 | 4 | | | IV-1 | TAT | 1.05 |
| 8367 | 3 | 4 | | | IV-1 | TAX1BP1 | 1.12 |
| 8368 | 3 | 4 | | | IV-1 | TBC1D10C | 1.04 |
| 8369 | 3 | 4 | | | IV-1 | TBC1D12 | 1.26 |
| 8370 | 3 | 4 | | | IV-1 | TBC1D16 | 1.07 |
| 8371 | 3 | 4 | | | IV-1 | TBC1D23 | 1.19 |
| 8372 | 3 | 4 | | | IV-1 | TBC1D2B | 1.23 |
| 8373 | 3 | 4 | | | IV-1 | TBC1D5 | 1.26 |
| 8374 | 3 | 4 | | | IV-1 | TBC1D8B | 1.07 |
| 8375 | 3 | 4 | | | IV-1 | TBC1D9 | 1.19 |
| 8376 | 3 | 4 | | | IV-1 | TBCA | 1.17 |
| 8377 | 3 | 4 | | | IV-1 | TBCEL | 1.42 |
| 8378 | 3 | 4 | | | IV-1 | TBL1XR1 | 1.02 |
| 8379 | 3 | 4 | | | IV-1 | TBRG1 | 1.36 |
| 8380 | 3 | 4 | | | IV-1 | TC2N | 1.22 |
| 8381 | 3 | 4 | | | IV-1 | TCEA1 | 1.06 |
| 8382 | 3 | 4 | | | IV-1 | TCEAL5 | 1.14 |
| 8383 | 3 | 4 | | | IV-1 | TCTEX1D2 | 1.22 |
| 8384 | 3 | 4 | | | IV-1 | TDG | 1.33 |
| 8385 | 3 | 4 | | | IV-1 | TDP2 | 1.22 |
| 8386 | 3 | 4 | | | IV-1 | TDRD3 | 1.09 |
| 8387 | 3 | 4 | | | IV-1 | TDRKH | 1.43 |
| 8388 | 3 | 4 | | | IV-1 | TEP1 | 1.41 |
| 8389 | 3 | 4 | | | IV-1 | TERF1 | 1.09 |
| 8390 | 3 | 4 | | | IV-1 | TET2 | 1.17 |
| 8391 | 3 | 4 | | | IV-1 | TEX30 | 1.18 |
| 8392 | 3 | 4 | | | IV-1 | TFAM | 1.33 |
| 8393 | 3 | 4 | | | IV-1 | TFB1M | 1.18 |
| 8394 | 3 | 4 | | | IV-1 | TFCP2 | 1.01 |
| 8395 | 3 | 4 | | | IV-1 | TFCP2L1 | 1.21 |
| 8396 | 3 | 4 | | | IV-1 | TFPI | 1.34 |
| 8397 | 3 | 4 | | | IV-1 | TG | 1.07 |
| 8398 | 3 | 4 | | | IV-1 | TGFBR2 | 1.00 |
| 8399 | 3 | 4 | | | IV-1 | TGS1 | 1.22 |
| 8400 | 3 | 4 | | | IV-1 | THAP1 | 1.08 |
| 8401 | 3 | 4 | | | IV-1 | THAP2 | 1.07 |
| 8402 | 3 | 4 | | | IV-1 | THAP5 | 1.33 |
| 8403 | 3 | 4 | | | IV-1 | THAP7-AS1 | 1.12 |
| 8404 | 3 | 4 | | | IV-1 | THBS2 | 1.14 |
| 8405 | 3 | 4 | | | IV-1 | THUMPD3 | 1.09 |
| 8406 | 3 | 4 | | | IV-1 | TIAL1 | 1.02 |
| 8407 | 3 | 4 | | | IV-1 | TIFA | 1.04 |
| 8408 | 3 | 4 | | | IV-1 | TIGD1 | 1.07 |
| 8409 | 3 | 4 | | | IV-1 | TIGIT | 1.28 |
| 8410 | 3 | 4 | | | IV-1 | TIMD4 | 1.07 |
| 8411 | 3 | 4 | | | IV-1 | TIPRL | 1.14 |
| 8412 | 3 | 4 | | | IV-1 | TIRAP | 1.14 |
| 8413 | 3 | 4 | | | IV-1 | TJP1 | 1.11 |
| 8414 | 3 | 4 | | | IV-1 | TJP2 | 1.11 |
| 8415 | 3 | 4 | | | IV-1 | TLL1 | 1.38 |
| 8416 | 3 | 4 | | | IV-1 | TLR4 | 1.30 |
| 8417 | 3 | 4 | | | IV-1 | TLR6 | 1.13 |
| 8418 | 3 | 4 | | | IV-1 | TLR7 | 1.18 |
| 8419 | 3 | 4 | | | IV-1 | TLR8 | 1.24 |
| 8420 | 3 | 4 | | | IV-1 | TMC2 | 1.00 |
| 8421 | 3 | 4 | | | IV-1 | TMC5 | 1.03 |
| 8422 | 3 | 4 | | | IV-1 | TMC8 | 1.27 |
| 8423 | 3 | 4 | | | IV-1 | TMCC1 | 1.20 |
| 8424 | 3 | 4 | | | IV-1 | TMCO3 | 1.03 |
| 8425 | 3 | 4 | | | IV-1 | TMED10 | 1.04 |
| 8426 | 3 | 4 | | | IV-1 | TMED4 | 1.03 |
| 8427 | 3 | 4 | | | IV-1 | TMED7 | 1.26 |
| 8428 | 3 | 4 | | | IV-1 | TMEM116 | 1.27 |
| 8429 | 3 | 4 | | | IV-1 | TMEM123 | 1.39 |
| 8430 | 3 | 4 | | | IV-1 | TMEM132C | 1.30 |
| 8431 | 3 | 4 | | | IV-1 | TMEM135 | 1.14 |
| 8432 | 3 | 4 | | | IV-1 | TMEM144 | 1.20 |
| 8433 | 3 | 4 | | | IV-1 | TMEM14A | 1.13 |
| 8434 | 3 | 4 | | | IV-1 | TMEM161B | 1.14 |
| 8435 | 3 | 4 | | | IV-1 | TMEM165 | 1.00 |
| 8436 | 3 | 4 | | | IV-1 | TMEM167A | 1.35 |
| 8437 | 3 | 4 | | | IV-1 | TMEM168 | 1.50 |
| 8438 | 3 | 4 | | | IV-1 | TMEM17 | 1.01 |
| 8439 | 3 | 4 | | | IV-1 | TMEM170B | 1.22 |
| 8440 | 3 | 4 | | | IV-1 | TMEM176B | 1.13 |
| 8441 | 3 | 4 | | | IV-1 | TMEM2 | 1.34 |
| 8442 | 3 | 4 | | | IV-1 | TMEM217 | 1.14 |
| 8443 | 3 | 4 | | | IV-1 | TMEM218 | 1.12 |
| 8444 | 3 | 4 | | | IV-1 | TMEM27 | 1.16 |
| 8445 | 3 | 4 | | | IV-1 | TMEM30A | 1.18 |

Fig. 38 - 45

| | | | | | | | | | | | | | | |
|---|---|---|---|---|---|---|---|---|---|---|---|---|---|---|
| 8446 | 3 | 4 | | | IV-1 | TMEM33 | 1.03 | 8542 | 3 | 4 | | | IV-1 | UBA3 | 1.01 |
| 8447 | 3 | 4 | | | IV-1 | TMEM38A | 1.24 | 8543 | 3 | 4 | | | IV-1 | UBA5 | 1.18 |
| 8448 | 3 | 4 | | | IV-1 | TMEM39A | 1.12 | 8544 | 3 | 4 | | | IV-1 | UBA6 | 1.34 |
| 8449 | 3 | 4 | | | IV-1 | TMEM41B | 1.41 | 8545 | 3 | 4 | | | IV-1 | UBASH3A | 1.06 |
| 8450 | 3 | 4 | | | IV-1 | TMEM48 | 1.00 | 8546 | 3 | 4 | | | IV-1 | UBE2D1 | 1.01 |
| 8451 | 3 | 4 | | | IV-1 | TMEM50B | 1.01 | 8547 | 3 | 4 | | | IV-1 | UBE2H | 1.04 |
| 8452 | 3 | 4 | | | IV-1 | TMEM57 | 1.11 | 8548 | 3 | 4 | | | IV-1 | UBE2K | 1.05 |
| 8453 | 3 | 4 | | | IV-1 | TMEM64 | 1.43 | 8549 | 3 | 4 | | | IV-1 | UBE2Q2 | 1.21 |
| 8454 | 3 | 4 | | | IV-1 | TMEM68 | 1.07 | 8550 | 3 | 4 | | | IV-1 | UBE2V2 | 1.10 |
| 8455 | 3 | 4 | | | IV-1 | TMEM87B | 1.21 | 8551 | 3 | 4 | | | IV-1 | UBE3A | 1.36 |
| 8456 | 3 | 4 | | | IV-1 | TMEM88B | 1.11 | 8552 | 3 | 4 | | | IV-1 | UBLCP1 | 1.01 |
| 8457 | 3 | 4 | | | IV-1 | TMOD2 | 1.44 | 8553 | 3 | 4 | | | IV-1 | UBN2 | 1.37 |
| 8458 | 3 | 4 | | | IV-1 | TMTC1 | 1.15 | 8554 | 3 | 4 | | | IV-1 | UBP1 | 1.02 |
| 8459 | 3 | 4 | | | IV-1 | TMX3 | 1.42 | 8555 | 3 | 4 | | | IV-1 | UBQLN1 | 1.09 |
| 8460 | 3 | 4 | | | IV-1 | TNFAIP8 | 1.05 | 8556 | 3 | 4 | | | IV-1 | UBR1 | 1.20 |
| 8461 | 3 | 4 | | | IV-1 | TNFRSF10A | 1.04 | 8557 | 3 | 4 | | | IV-1 | UBR2 | 1.06 |
| 8462 | 3 | 4 | | | IV-1 | TNFRSF19 | 1.07 | 8558 | 3 | 4 | | | IV-1 | UBR3 | 1.31 |
| 8463 | 3 | 4 | | | IV-1 | TNFRSF21 | 1.10 | 8559 | 3 | 4 | | | IV-1 | UBR5 | 1.34 |
| 8464 | 3 | 4 | | | IV-1 | TNFSF9 | 1.25 | 8560 | 3 | 4 | | | IV-1 | UBTD2 | 1.05 |
| 8465 | 3 | 4 | | | IV-1 | TNIK | 1.05 | 8561 | 3 | 4 | | | IV-1 | UBXN10 | 1.49 |
| 8466 | 3 | 4 | | | IV-1 | TNKS | 1.44 | 8562 | 3 | 4 | | | IV-1 | UBXN2A | 1.03 |
| 8467 | 3 | 4 | | | IV-1 | TNKS2 | 1.17 | 8563 | 3 | 4 | | | IV-1 | UBXN4 | 1.37 |
| 8468 | 3 | 4 | | | IV-1 | TNMD | 1.03 | 8564 | 3 | 4 | | | IV-1 | UCHL5 | 1.18 |
| 8469 | 3 | 4 | | | IV-1 | TNNC1 | 1.36 | 8565 | 3 | 4 | | | IV-1 | UCKL1-AS1 | 1.39 |
| 8470 | 3 | 4 | | | IV-1 | TNNC2 | 1.04 | 8566 | 3 | 4 | | | IV-1 | UFL1 | 1.19 |
| 8471 | 3 | 4 | | | IV-1 | TNPO1 | 1.11 | 8567 | 3 | 4 | | | IV-1 | UFM1 | 1.16 |
| 8472 | 3 | 4 | | | IV-1 | TOMM70A | 1.04 | 8568 | 3 | 4 | | | IV-1 | UGGT1 | 1.18 |
| 8473 | 3 | 4 | | | IV-1 | TOP1 | 1.22 | 8569 | 3 | 4 | | | IV-1 | UGT8 | 1.13 |
| 8474 | 3 | 4 | | | IV-1 | TOP2B | 1.16 | 8570 | 3 | 4 | | | IV-1 | UHMK1 | 1.49 |
| 8475 | 3 | 4 | | | IV-1 | TOR1AIP1 | 1.35 | 8571 | 3 | 4 | | | IV-1 | UHRF1BP1L | 1.28 |
| 8476 | 3 | 4 | | | IV-1 | TOR1AIP2 | 1.16 | 8572 | 3 | 4 | | | IV-1 | ULK2 | 1.19 |
| 8477 | 3 | 4 | | | IV-1 | TOX3 | 1.18 | 8573 | 3 | 4 | | | IV-1 | ULK4 | 1.01 |
| 8478 | 3 | 4 | | | IV-1 | TP53BP2 | 1.18 | 8574 | 3 | 4 | | | IV-1 | UNC50 | 1.04 |
| 8479 | 3 | 4 | | | IV-1 | TP53INP1 | 1.43 | 8575 | 3 | 4 | | | IV-1 | UNKL | 1.06 |
| 8480 | 3 | 4 | | | IV-1 | TP73-AS1 | 1.19 | 8576 | 3 | 4 | | | IV-1 | UPK1A | 1.19 |
| 8481 | 3 | 4 | | | IV-1 | TPR | 1.19 | 8577 | 3 | 4 | | | IV-1 | UPK1B | 1.09 |
| 8482 | 3 | 4 | | | IV-1 | TRAF3IP1 | 1.03 | 8578 | 3 | 4 | | | IV-1 | URB1 | 1.47 |
| 8483 | 3 | 4 | | | IV-1 | TRAF6 | 1.01 | 8579 | 3 | 4 | | | IV-1 | UROS | 1.03 |
| 8484 | 3 | 4 | | | IV-1 | TRAM1L1 | 1.33 | 8580 | 3 | 4 | | | IV-1 | USO1 | 1.36 |
| 8485 | 3 | 4 | | | IV-1 | TRAPPC10 | 1.06 | 8581 | 3 | 4 | | | IV-1 | USP1 | 1.20 |
| 8486 | 3 | 4 | | | IV-1 | TRAPPC11 | 1.22 | 8582 | 3 | 4 | | | IV-1 | USP12 | 1.18 |
| 8487 | 3 | 4 | | | IV-1 | TRAPPC8 | 1.20 | 8583 | 3 | 4 | | | IV-1 | USP14 | 1.32 |
| 8488 | 3 | 4 | | | IV-1 | TRIM2 | 1.41 | 8584 | 3 | 4 | | | IV-1 | USP15 | 1.08 |
| 8489 | 3 | 4 | | | IV-1 | TRIM34 | 1.01 | 8585 | 3 | 4 | | | IV-1 | USP18 | 1.19 |
| 8490 | 3 | 4 | | | IV-1 | TRIM36 | 1.03 | 8586 | 3 | 4 | | | IV-1 | USP25 | 1.18 |
| 8491 | 3 | 4 | | | IV-1 | TRIM5 | 1.20 | 8587 | 3 | 4 | | | IV-1 | USP28 | 1.02 |
| 8492 | 3 | 4 | | | IV-1 | TRIM55 | 1.39 | 8588 | 3 | 4 | | | IV-1 | USP3 | 1.25 |
| 8493 | 3 | 4 | | | IV-1 | TRIM59 | 1.12 | 8589 | 3 | 4 | | | IV-1 | USP30 | 1.01 |
| 8494 | 3 | 4 | | | IV-1 | TRIM6 | 1.29 | 8590 | 3 | 4 | | | IV-1 | USP31 | 1.24 |
| 8495 | 3 | 4 | | | IV-1 | TRIM66 | 1.37 | 8591 | 3 | 4 | | | IV-1 | USP32 | 1.29 |
| 8496 | 3 | 4 | | | IV-1 | TRIM74 | 1.37 | 8592 | 3 | 4 | | | IV-1 | USP33 | 1.24 |
| 8497 | 3 | 4 | | | IV-1 | TRIM9 | 1.06 | 8593 | 3 | 4 | | | IV-1 | USP34 | 1.23 |
| 8498 | 3 | 4 | | | IV-1 | TRIO | 1.16 | 8594 | 3 | 4 | | | IV-1 | USP37 | 1.07 |
| 8499 | 3 | 4 | | | IV-1 | TRIP11 | 1.46 | 8595 | 3 | 4 | | | IV-1 | USP42 | 1.02 |
| 8500 | 3 | 4 | | | IV-1 | TRIP12 | 1.15 | 8596 | 3 | 4 | | | IV-1 | USP47 | 1.03 |
| 8501 | 3 | 4 | | | IV-1 | TRIP4 | 1.19 | 8597 | 3 | 4 | | | IV-1 | USP48 | 1.17 |
| 8502 | 3 | 4 | | | IV-1 | TRMT1L | 1.38 | 8598 | 3 | 4 | | | IV-1 | USP8 | 1.37 |
| 8503 | 3 | 4 | | | IV-1 | TRMT5 | 1.18 | 8599 | 3 | 4 | | | IV-1 | USP9X | 1.10 |
| 8504 | 3 | 4 | | | IV-1 | TRNT1 | 1.23 | 8600 | 3 | 4 | | | IV-1 | UST | 1.24 |
| 8505 | 3 | 4 | | | IV-1 | TROVE2 | 1.24 | 8601 | 3 | 4 | | | IV-1 | UTP15 | 1.46 |
| 8506 | 3 | 4 | | | IV-1 | TRPM2 | 1.01 | 8602 | 3 | 4 | | | IV-1 | UTRN | 1.04 |
| 8507 | 3 | 4 | | | IV-1 | TRPS1 | 1.47 | 8603 | 3 | 4 | | | IV-1 | VAMP7 | 1.03 |
| 8508 | 3 | 4 | | | IV-1 | TRUB1 | 1.00 | 8604 | 3 | 4 | | | IV-1 | VAPB | 1.29 |
| 8509 | 3 | 4 | | | IV-1 | TSC22D1-AS1 | 1.09 | 8605 | 3 | 4 | | | IV-1 | VASH2 | 1.19 |
| 8510 | 3 | 4 | | | IV-1 | TSC22D2 | 1.25 | 8606 | 3 | 4 | | | IV-1 | VAV1 | 1.23 |
| 8511 | 3 | 4 | | | IV-1 | TSEN2 | 1.37 | 8607 | 3 | 4 | | | IV-1 | VAV3 | 1.11 |
| 8512 | 3 | 4 | | | IV-1 | TSHZ1 | 1.05 | 8608 | 3 | 4 | | | IV-1 | VCPIP1 | 1.17 |
| 8513 | 3 | 4 | | | IV-1 | TSHZ3 | 1.25 | 8609 | 3 | 4 | | | IV-1 | VENTX | 1.03 |
| 8514 | 3 | 4 | | | IV-1 | TSLP | 1.03 | 8610 | 3 | 4 | | | IV-1 | VEZF1 | 1.05 |
| 8515 | 3 | 4 | | | IV-1 | TSNAX | 1.48 | 8611 | 3 | 4 | | | IV-1 | VEZT | 1.40 |
| 8516 | 3 | 4 | | | IV-1 | TSPAN6 | 1.30 | 8612 | 3 | 4 | | | IV-1 | VGLL2 | 1.12 |
| 8517 | 3 | 4 | | | IV-1 | TSPY26P | 1.02 | 8613 | 3 | 4 | | | IV-1 | VIT | 1.07 |
| 8518 | 3 | 4 | | | IV-1 | TSPYL2 | 1.08 | 8614 | 3 | 4 | | | IV-1 | VLDLR | 1.13 |
| 8519 | 3 | 4 | | | IV-1 | TSPYL4 | 1.17 | 8615 | 3 | 4 | | | IV-1 | VN1R1 | 1.47 |
| 8520 | 3 | 4 | | | IV-1 | TSPYL5 | 1.03 | 8616 | 3 | 4 | | | IV-1 | VNN1 | 1.08 |
| 8521 | 3 | 4 | | | IV-1 | TSR1 | 1.37 | 8617 | 3 | 4 | | | IV-1 | VPRBP | 1.35 |
| 8522 | 3 | 4 | | | IV-1 | TTC12 | 1.07 | 8618 | 3 | 4 | | | IV-1 | VPS13B | 1.24 |
| 8523 | 3 | 4 | | | IV-1 | TTC18 | 1.19 | 8619 | 3 | 4 | | | IV-1 | VPS13C | 1.49 |
| 8524 | 3 | 4 | | | IV-1 | TTC26 | 1.03 | 8620 | 3 | 4 | | | IV-1 | VPS26A | 1.07 |
| 8525 | 3 | 4 | | | IV-1 | TTC28 | 1.06 | 8621 | 3 | 4 | | | IV-1 | VPS37A | 1.14 |
| 8526 | 3 | 4 | | | IV-1 | TTC3 | 1.07 | 8622 | 3 | 4 | | | IV-1 | VPS41 | 1.48 |
| 8527 | 3 | 4 | | | IV-1 | TTC30B | 1.42 | 8623 | 3 | 4 | | | IV-1 | VPS4B | 1.16 |
| 8528 | 3 | 4 | | | IV-1 | TTC33 | 1.13 | 8624 | 3 | 4 | | | IV-1 | VSIG10 | 1.41 |
| 8529 | 3 | 4 | | | IV-1 | TTC37 | 1.16 | 8625 | 3 | 4 | | | IV-1 | VSTM4 | 1.36 |
| 8530 | 3 | 4 | | | IV-1 | TTC5 | 1.11 | 8626 | 3 | 4 | | | IV-1 | WAC | 1.08 |
| 8531 | 3 | 4 | | | IV-1 | TTC8 | 1.24 | 8627 | 3 | 4 | | | IV-1 | WAPAL | 1.05 |
| 8532 | 3 | 4 | | | IV-1 | TTF2 | 1.20 | 8628 | 3 | 4 | | | IV-1 | WDFY1 | 1.26 |
| 8533 | 3 | 4 | | | IV-1 | TTI2 | 1.09 | 8629 | 3 | 4 | | | IV-1 | WDFY3 | 1.33 |
| 8534 | 3 | 4 | | | IV-1 | TUBGCP5 | 1.23 | 8630 | 3 | 4 | | | IV-1 | WDPCP | 1.10 |
| 8535 | 3 | 4 | | | IV-1 | TUSC3 | 1.17 | 8631 | 3 | 4 | | | IV-1 | WDR11 | 1.36 |
| 8536 | 3 | 4 | | | IV-1 | TWSG1 | 1.07 | 8632 | 3 | 4 | | | IV-1 | WDR26 | 1.42 |
| 8537 | 3 | 4 | | | IV-1 | TXLNB | 1.31 | 8633 | 3 | 4 | | | IV-1 | WDR31 | 1.32 |
| 8538 | 3 | 4 | | | IV-1 | TXLNG | 1.31 | 8634 | 3 | 4 | | | IV-1 | WDR33 | 1.08 |
| 8539 | 3 | 4 | | | IV-1 | TXNDC9 | 1.13 | 8635 | 3 | 4 | | | IV-1 | WDR36 | 1.35 |
| 8540 | 3 | 4 | | | IV-1 | TXNRD1 | 1.11 | 8636 | 3 | 4 | | | IV-1 | WDR37 | 1.45 |
| 8541 | 3 | 4 | | | IV-1 | TYW3 | 1.37 | 8637 | 3 | 4 | | | IV-1 | WDR4 | 1.05 |

Fig. 38 - 46

| | | | | | | | | | | | | | | |
|---|---|---|---|---|---|---|---|---|---|---|---|---|---|---|
| 8638 | 3 | 4 | | | IV-1 | WDR41 | 1.11 | 8734 | 3 | 4 | | | IV-1 | ZNF24 | 1.27 |
| 8639 | 3 | 4 | | | IV-1 | WDR44 | 1.21 | 8735 | 3 | 4 | | | IV-1 | ZNF252 | 1.26 |
| 8640 | 3 | 4 | | | IV-1 | WDR47 | 1.05 | 8736 | 3 | 4 | | | IV-1 | ZNF256 | 1.18 |
| 8641 | 3 | 4 | | | IV-1 | WDR48 | 1.16 | 8737 | 3 | 4 | | | IV-1 | ZNF26 | 1.38 |
| 8642 | 3 | 4 | | | IV-1 | WDR53 | 1.08 | 8738 | 3 | 4 | | | IV-1 | ZNF260 | 1.32 |
| 8643 | 3 | 4 | | | IV-1 | WDR5B | 1.33 | 8739 | 3 | 4 | | | IV-1 | ZNF264 | 1.12 |
| 8644 | 3 | 4 | | | IV-1 | WDR61 | 1.06 | 8740 | 3 | 4 | | | IV-1 | ZNF271 | 1.37 |
| 8645 | 3 | 4 | | | IV-1 | WDR7 | 1.07 | 8741 | 3 | 4 | | | IV-1 | ZNF275 | 1.39 |
| 8646 | 3 | 4 | | | IV-1 | WDR73 | 1.18 | 8742 | 3 | 4 | | | IV-1 | ZNF277 | 1.28 |
| 8647 | 3 | 4 | | | IV-1 | WDR89 | 1.13 | 8743 | 3 | 4 | | | IV-1 | ZNF283 | 1.16 |
| 8648 | 3 | 4 | | | IV-1 | WDR92 | 1.11 | 8744 | 3 | 4 | | | IV-1 | ZNF285 | 1.33 |
| 8649 | 3 | 4 | | | IV-1 | WFDC2 | 1.41 | 8745 | 3 | 4 | | | IV-1 | ZNF304 | 1.22 |
| 8650 | 3 | 4 | | | IV-1 | WFIKKN2 | 1.11 | 8746 | 3 | 4 | | | IV-1 | ZNF311 | 1.06 |
| 8651 | 3 | 4 | | | IV-1 | WHAMMP2 | 1.18 | 8747 | 3 | 4 | | | IV-1 | ZNF318 | 1.24 |
| 8652 | 3 | 4 | | | IV-1 | WHSC1L1 | 1.06 | 8748 | 3 | 4 | | | IV-1 | ZNF322 | 1.46 |
| 8653 | 3 | 4 | | | IV-1 | WNT10B | 1.05 | 8749 | 3 | 4 | | | IV-1 | ZNF324 | 1.01 |
| 8654 | 3 | 4 | | | IV-1 | WRN | 1.23 | 8750 | 3 | 4 | | | IV-1 | ZNF343 | 1.10 |
| 8655 | 3 | 4 | | | IV-1 | WTH3DI | 1.09 | 8751 | 3 | 4 | | | IV-1 | ZNF346 | 1.06 |
| 8656 | 3 | 4 | | | IV-1 | WWC2 | 1.39 | 8752 | 3 | 4 | | | IV-1 | ZNF391 | 1.40 |
| 8657 | 3 | 4 | | | IV-1 | WWTR1 | 1.23 | 8753 | 3 | 4 | | | IV-1 | ZNF398 | 1.42 |
| 8658 | 3 | 4 | | | IV-1 | XG | 1.36 | 8754 | 3 | 4 | | | IV-1 | ZNF407 | 1.06 |
| 8659 | 3 | 4 | | | IV-1 | XGPY2 | 1.18 | 8755 | 3 | 4 | | | IV-1 | ZNF425 | 1.06 |
| 8660 | 3 | 4 | | | IV-1 | XPNPEP1 | 1.01 | 8756 | 3 | 4 | | | IV-1 | ZNF434 | 1.29 |
| 8661 | 3 | 4 | | | IV-1 | XPO1 | 1.37 | 8757 | 3 | 4 | | | IV-1 | ZNF44 | 1.31 |
| 8662 | 3 | 4 | | | IV-1 | XPO4 | 1.20 | 8758 | 3 | 4 | | | IV-1 | ZNF445 | 1.30 |
| 8663 | 3 | 4 | | | IV-1 | XPR1 | 1.05 | 8759 | 3 | 4 | | | IV-1 | ZNF469 | 1.20 |
| 8664 | 3 | 4 | | | IV-1 | XRCC2 | 1.03 | 8760 | 3 | 4 | | | IV-1 | ZNF484 | 1.14 |
| 8665 | 3 | 4 | | | IV-1 | XRN1 | 1.36 | 8761 | 3 | 4 | | | IV-1 | ZNF490 | 1.17 |
| 8666 | 3 | 4 | | | IV-1 | XYLB | 1.01 | 8762 | 3 | 4 | | | IV-1 | ZNF512 | 1.17 |
| 8667 | 3 | 4 | | | IV-1 | YAF2 | 1.13 | 8763 | 3 | 4 | | | IV-1 | ZNF516 | 1.35 |
| 8668 | 3 | 4 | | | IV-1 | YAP1 | 1.01 | 8764 | 3 | 4 | | | IV-1 | ZNF518B | 1.38 |
| 8669 | 3 | 4 | | | IV-1 | YIPF5 | 1.09 | 8765 | 3 | 4 | | | IV-1 | ZNF519 | 1.13 |
| 8670 | 3 | 4 | | | IV-1 | YIPF6 | 1.43 | 8766 | 3 | 4 | | | IV-1 | ZNF530 | 1.24 |
| 8671 | 3 | 4 | | | IV-1 | YME1L1 | 1.08 | 8767 | 3 | 4 | | | IV-1 | ZNF542 | 1.19 |
| 8672 | 3 | 4 | | | IV-1 | YPEL1 | 1.27 | 8768 | 3 | 4 | | | IV-1 | ZNF543 | 1.39 |
| 8673 | 3 | 4 | | | IV-1 | YTHDC1 | 1.05 | 8769 | 3 | 4 | | | IV-1 | ZNF544 | 1.35 |
| 8674 | 3 | 4 | | | IV-1 | YTHDF3 | 1.25 | 8770 | 3 | 4 | | | IV-1 | ZNF546 | 1.39 |
| 8675 | 3 | 4 | | | IV-1 | YY2 | 1.05 | 8771 | 3 | 4 | | | IV-1 | ZNF547 | 1.40 |
| 8676 | 3 | 4 | | | IV-1 | ZADH2 | 1.08 | 8772 | 3 | 4 | | | IV-1 | ZNF552 | 1.09 |
| 8677 | 3 | 4 | | | IV-1 | ZAK | 1.14 | 8773 | 3 | 4 | | | IV-1 | ZNF554 | 1.15 |
| 8678 | 3 | 4 | | | IV-1 | ZBP1 | 1.15 | 8774 | 3 | 4 | | | IV-1 | ZNF570 | 1.13 |
| 8679 | 3 | 4 | | | IV-1 | ZBT810 | 1.35 | 8775 | 3 | 4 | | | IV-1 | ZNF582 | 1.08 |
| 8680 | 3 | 4 | | | IV-1 | ZBTB33 | 1.06 | 8776 | 3 | 4 | | | IV-1 | ZNF583 | 1.43 |
| 8681 | 3 | 4 | | | IV-1 | ZBTB38 | 1.24 | 8777 | 3 | 4 | | | IV-1 | ZNF585A | 1.16 |
| 8682 | 3 | 4 | | | IV-1 | ZBTB41 | 1.16 | 8778 | 3 | 4 | | | IV-1 | ZNF585B | 1.31 |
| 8683 | 3 | 4 | | | IV-1 | ZBTB43 | 1.24 | 8779 | 3 | 4 | | | IV-1 | ZNF594 | 1.37 |
| 8684 | 3 | 4 | | | IV-1 | ZBTB44 | 1.31 | 8780 | 3 | 4 | | | IV-1 | ZNF597 | 1.08 |
| 8685 | 3 | 4 | | | IV-1 | ZBTB8A | 1.28 | 8781 | 3 | 4 | | | IV-1 | ZNF607 | 1.35 |
| 8686 | 3 | 4 | | | IV-1 | ZC3H11A | 1.21 | 8782 | 3 | 4 | | | IV-1 | ZNF608 | 1.33 |
| 8687 | 3 | 4 | | | IV-1 | ZC3H14 | 1.31 | 8783 | 3 | 4 | | | IV-1 | ZNF610 | 1.29 |
| 8688 | 3 | 4 | | | IV-1 | ZC3H15 | 1.02 | 8784 | 3 | 4 | | | IV-1 | ZNF623 | 1.23 |
| 8689 | 3 | 4 | | | IV-1 | ZC3HAV1 | 1.28 | 8785 | 3 | 4 | | | IV-1 | ZNF624 | 1.41 |
| 8690 | 3 | 4 | | | IV-1 | ZC3HAV1L | 1.46 | 8786 | 3 | 4 | | | IV-1 | ZNF627 | 1.38 |
| 8691 | 3 | 4 | | | IV-1 | ZCCHC10 | 1.16 | 8787 | 3 | 4 | | | IV-1 | ZNF644 | 1.27 |
| 8692 | 3 | 4 | | | IV-1 | ZCCHC11 | 1.14 | 8788 | 3 | 4 | | | IV-1 | ZNF654 | 1.43 |
| 8693 | 3 | 4 | | | IV-1 | ZCCHC14 | 1.01 | 8789 | 3 | 4 | | | IV-1 | ZNF655 | 1.03 |
| 8694 | 3 | 4 | | | IV-1 | ZCCHC2 | 1.05 | 8790 | 3 | 4 | | | IV-1 | ZNF664 | 1.32 |
| 8695 | 3 | 4 | | | IV-1 | ZCCHC6 | 1.33 | 8791 | 3 | 4 | | | IV-1 | ZNF670 | 1.14 |
| 8696 | 3 | 4 | | | IV-1 | ZCCHC7 | 1.18 | 8792 | 3 | 4 | | | IV-1 | ZNF681 | 1.32 |
| 8697 | 3 | 4 | | | IV-1 | ZD8F2 | 1.04 | 8793 | 3 | 4 | | | IV-1 | ZNF696 | 1.02 |
| 8698 | 3 | 4 | | | IV-1 | ZDHHC2 | 1.50 | 8794 | 3 | 4 | | | IV-1 | ZNF697 | 1.18 |
| 8699 | 3 | 4 | | | IV-1 | ZDHHC6 | 1.16 | 8795 | 3 | 4 | | | IV-1 | ZNF701 | 1.08 |
| 8700 | 3 | 4 | | | IV-1 | ZFAND4 | 1.01 | 8796 | 3 | 4 | | | IV-1 | ZNF702P | 1.04 |
| 8701 | 3 | 4 | | | IV-1 | ZFAND5 | 1.06 | 8797 | 3 | 4 | | | IV-1 | ZNF704 | 1.25 |
| 8702 | 3 | 4 | | | IV-1 | ZFAND6 | 1.09 | 8798 | 3 | 4 | | | IV-1 | ZNF709 | 1.03 |
| 8703 | 3 | 4 | | | IV-1 | ZFP1 | 1.05 | 8799 | 3 | 4 | | | IV-1 | ZNF713 | 1.23 |
| 8704 | 3 | 4 | | | IV-1 | ZFP161 | 1.27 | 8800 | 3 | 4 | | | IV-1 | ZNF749 | 1.04 |
| 8705 | 3 | 4 | | | IV-1 | ZFR | 1.10 | 8801 | 3 | 4 | | | IV-1 | ZNF766 | 1.18 |
| 8706 | 3 | 4 | | | IV-1 | ZFX | 1.22 | 8802 | 3 | 4 | | | IV-1 | ZNF77 | 1.14 |
| 8707 | 3 | 4 | | | IV-1 | ZFYVE16 | 1.47 | 8803 | 3 | 4 | | | IV-1 | ZNF783 | 1.04 |
| 8708 | 3 | 4 | | | IV-1 | ZFYVE20 | 1.37 | 8804 | 3 | 4 | | | IV-1 | ZNF785 | 1.05 |
| 8709 | 3 | 4 | | | IV-1 | ZFYVE26 | 1.42 | 8805 | 3 | 4 | | | IV-1 | ZNF786 | 1.04 |
| 8710 | 3 | 4 | | | IV-1 | ZKSCAN2 | 1.09 | 8806 | 3 | 4 | | | IV-1 | ZNF805 | 1.07 |
| 8711 | 3 | 4 | | | IV-1 | ZKSCAN3 | 1.46 | 8807 | 3 | 4 | | | IV-1 | ZNF813 | 1.01 |
| 8712 | 3 | 4 | | | IV-1 | ZKSCAN4 | 1.25 | 8808 | 3 | 4 | | | IV-1 | ZNF823 | 1.25 |
| 8713 | 3 | 4 | | | IV-1 | ZKSCAN5 | 1.29 | 8809 | 3 | 4 | | | IV-1 | ZNF833P | 1.05 |
| 8714 | 3 | 4 | | | IV-1 | ZMAT3 | 1.28 | 8810 | 3 | 4 | | | IV-1 | ZNF850 | 1.15 |
| 8715 | 3 | 4 | | | IV-1 | ZMYND11 | 1.12 | 8811 | 3 | 4 | | | IV-1 | ZNF860 | 1.20 |
| 8716 | 3 | 4 | | | IV-1 | ZMYND8 | 1.10 | 8812 | 3 | 4 | | | IV-1 | ZNF880 | 1.27 |
| 8717 | 3 | 4 | | | IV-1 | ZNF12 | 1.34 | 8813 | 3 | 4 | | | IV-1 | ZNF883 | 1.11 |
| 8718 | 3 | 4 | | | IV-1 | ZNF131 | 1.08 | 8814 | 3 | 4 | | | IV-1 | ZNFX1 | 1.04 |
| 8719 | 3 | 4 | | | IV-1 | ZNF135 | 1.38 | 8815 | 3 | 4 | | | IV-1 | ZNRD1 | 1.13 |
| 8720 | 3 | 4 | | | IV-1 | ZNF141 | 1.16 | 8816 | 3 | 4 | | | IV-1 | ZNRF3 | 1.11 |
| 8721 | 3 | 4 | | | IV-1 | ZNF146 | 1.23 | 8817 | 3 | 4 | | | IV-1 | ZP1 | 1.04 |
| 8722 | 3 | 4 | | | IV-1 | ZNF148 | 1.19 | 8818 | 3 | 4 | | | IV-1 | ZRANB1 | 1.29 |
| 8723 | 3 | 4 | | | IV-1 | ZNF155 | 1.18 | 8819 | 3 | 4 | | | IV-1 | ZSCAN20 | 1.28 |
| 8724 | 3 | 4 | | | IV-1 | ZNF165 | 1.46 | 8820 | 3 | 4 | | | IV-1 | ZW10 | 1.34 |
| 8725 | 3 | 4 | | | IV-1 | ZNF167 | 1.31 | 8821 | 3 | 4 | | | IV-1 | ZXDA | 1.37 |
| 8726 | 3 | 4 | | | IV-1 | ZNF180 | 1.45 | 8822 | 3 | 4 | | | IV-1 | ZYG11B | 1.43 |
| 8727 | 3 | 4 | | | IV-1 | ZNF193 | 1.03 | 8823 | 3 | | | | | 1/2-SBSRNA4 | 1.00 |
| 8728 | 3 | 4 | | | IV-1 | ZNF2 | 1.33 | 8824 | 3 | | | | | A1CF | 1.00 |
| 8729 | 3 | 4 | | | IV-1 | ZNF202 | 1.11 | 8825 | 3 | | | | | A2MP1 | 1.00 |
| 8730 | 3 | 4 | | | IV-1 | ZNF211 | 1.34 | 8826 | 3 | | | | | A4GNT | 1.00 |
| 8731 | 3 | 4 | | | IV-1 | ZNF217 | 1.31 | 8827 | 3 | | | | | AA06 | 1.00 |
| 8732 | 3 | 4 | | | IV-1 | ZNF229 | 1.11 | 8828 | 3 | | | | | AAA1 | 1.00 |
| 8733 | 3 | 4 | | | IV-1 | ZNF232 | 1.11 | 8829 | 3 | | | | | AADACL4 | 1.00 |

Fig. 38 - 47

| | | | | | | | | | | | | | |
|---|---|---|---|---|---|---|---|---|---|---|---|---|---|
| 8830 | 3 | | | | | AANAT | 1.00 | 8926 | 3 | | | AFP | 1.00 |
| 8831 | 3 | | | | | AATK-AS1 | 1.00 | 8927 | 3 | | | AGBL1 | 1.00 |
| 8832 | 3 | | | | | ABCA13 | 1.00 | 8928 | 3 | | | AGBL2 | 1.00 |
| 8833 | 3 | | | | | ABCA17P | 1.00 | 8929 | 3 | | | AGBL3 | 1.00 |
| 8834 | 3 | | | | | ABCA4 | 1.00 | 8930 | 3 | | | AGBL4 | 1.00 |
| 8835 | 3 | | | | | ABCB11 | 1.00 | 8931 | 3 | | | AGMAT | 1.00 |
| 8836 | 3 | | | | | ABCB4 | 1.00 | 8932 | 3 | | | AGMO | 1.00 |
| 8837 | 3 | | | | | ABCC11 | 1.00 | 8933 | 3 | | | AGR3 | 1.00 |
| 8838 | 3 | | | | | ABCC12 | 1.00 | 8934 | 3 | | | AGRP | 1.00 |
| 8839 | 3 | | | | | ABCC13 | 1.00 | 8935 | 3 | | | AGT | 1.00 |
| 8840 | 3 | | | | | ABCC2 | 1.00 | 8936 | 3 | | | AGTR2 | 1.00 |
| 8841 | 3 | | | | | ABCC6P1 | 1.00 | 8937 | 3 | | | AGXT | 1.00 |
| 8842 | 3 | | | | | ABCC6P2 | 1.00 | 8938 | 3 | | | AGXT2 | 1.00 |
| 8843 | 3 | | | | | ABCC8 | 1.00 | 8939 | 3 | | | AGXT2L1 | 1.00 |
| 8844 | 3 | | | | | ABCD2 | 1.00 | 8940 | 3 | | | AHSG | 1.00 |
| 8845 | 3 | | | | | ABCG2 | 1.00 | 8941 | 3 | | | AHSP | 1.00 |
| 8846 | 3 | | | | | ABCG4 | 1.00 | 8942 | 3 | | | AICDA | 1.00 |
| 8847 | 3 | | | | | ABCG5 | 1.00 | 8943 | 3 | | | AIFM3 | 1.00 |
| 8848 | 3 | | | | | ABCG8 | 1.00 | 8944 | 3 | | | AIM2 | 1.00 |
| 8849 | 3 | | | | | ABHD1 | 1.00 | 8945 | 3 | | | AIPL1 | 1.00 |
| 8850 | 3 | | | | | ABHD10 | 1.00 | 8946 | 3 | | | AIRE | 1.00 |
| 8851 | 3 | | | | | ABHD11-AS1 | 1.00 | 8947 | 3 | | | AK5 | 1.00 |
| 8852 | 3 | | | | | ABHD14A-ACY1 | 1.00 | 8948 | 3 | | | AK8 | 1.00 |
| 8853 | 3 | | | | | ABRA | 1.00 | 8949 | 3 | | | AKAP14 | 1.00 |
| 8854 | 3 | | | | | ACAN | 1.00 | 8950 | 3 | | | AKAP3 | 1.00 |
| 8855 | 3 | | | | | ACBD7 | 1.00 | 8951 | 3 | | | AKAP4 | 1.00 |
| 8856 | 3 | | | | | ACCN4 | 1.00 | 8952 | 3 | | | AKAP5 | 1.00 |
| 8857 | 3 | | | | | ACCN5 | 1.00 | 8953 | 3 | | | AKNAD1 | 1.00 |
| 8858 | 3 | | | | | ACCSL | 1.00 | 8954 | 3 | | | AKR1B10 | 1.00 |
| 8859 | 3 | | | | | ACE2 | 1.00 | 8955 | 3 | | | AKR1B15 | 1.00 |
| 8860 | 3 | | | | | ACMSD | 1.00 | 8956 | 3 | | | AKR1C4 | 1.00 |
| 8861 | 3 | | | | | ACOT12 | 1.00 | 8957 | 3 | | | AKR1CL1 | 1.00 |
| 8862 | 3 | | | | | ACOT6 | 1.00 | 8958 | 3 | | | AKR1D1 | 1.00 |
| 8863 | 3 | | | | | ACOXL | 1.00 | 8959 | 3 | | | ALAS2 | 1.00 |
| 8864 | 3 | | | | | ACPT | 1.00 | 8960 | 3 | | | ALB | 1.00 |
| 8865 | 3 | | | | | ACRV1 | 1.00 | 8961 | 3 | | | ALG1L | 1.00 |
| 8866 | 3 | | | | | ACSBG2 | 1.00 | 8962 | 3 | | | ALG1L2 | 1.00 |
| 8867 | 3 | | | | | ACSL6 | 1.00 | 8963 | 3 | | | ALK | 1.00 |
| 8868 | 3 | | | | | ACSM1 | 1.00 | 8964 | 3 | | | ALLC | 1.00 |
| 8869 | 3 | | | | | ACSM2A | 1.00 | 8965 | 3 | | | ALMS1P | 1.00 |
| 8870 | 3 | | | | | ACSM2B | 1.00 | 8966 | 3 | | | ALOX12P2 | 1.00 |
| 8871 | 3 | | | | | ACSM4 | 1.00 | 8967 | 3 | | | ALOX15P1 | 1.00 |
| 8872 | 3 | | | | | ACTBL2 | 1.00 | 8968 | 3 | | | ALPI | 1.00 |
| 8873 | 3 | | | | | ACTL6B | 1.00 | 8969 | 3 | | | ALPK2 | 1.00 |
| 8874 | 3 | | | | | ACTL7A | 1.00 | 8970 | 3 | | | ALPP | 1.00 |
| 8875 | 3 | | | | | ACTL7B | 1.00 | 8971 | 3 | | | ALPPL2 | 1.00 |
| 8876 | 3 | | | | | ACTL8 | 1.00 | 8972 | 3 | | | ALS2CR11 | 1.00 |
| 8877 | 3 | | | | | ACTL9 | 1.00 | 8973 | 3 | | | ALS2CR12 | 1.00 |
| 8878 | 3 | | | | | ACTN2 | 1.00 | 8974 | 3 | | | AMBN | 1.00 |
| 8879 | 3 | | | | | ACTN3 | 1.00 | 8975 | 3 | | | AMBP | 1.00 |
| 8880 | 3 | | | | | ACTR3BP2 | 1.00 | 8976 | 3 | | | AMELX | 1.00 |
| 8881 | 3 | | | | | ACTR3BP5 | 1.00 | 8977 | 3 | | | AMELY | 1.00 |
| 8882 | 3 | | | | | ACTR3C | 1.00 | 8978 | 3 | | | AMHR2 | 1.00 |
| 8883 | 3 | | | | | ACTRT1 | 1.00 | 8979 | 3 | | | AMPD1 | 1.00 |
| 8884 | 3 | | | | | ACTRT2 | 1.00 | 8980 | 3 | | | AMPH | 1.00 |
| 8885 | 3 | | | | | ACVR1C | 1.00 | 8981 | 3 | | | AMTN | 1.00 |
| 8886 | 3 | | | | | ACY3 | 1.00 | 8982 | 3 | | | AMY1B | 1.00 |
| 8887 | 3 | | | | | ADAD1 | 1.00 | 8983 | 3 | | | AMY1C | 1.00 |
| 8888 | 3 | | | | | ADAM12 | 1.00 | 8984 | 3 | | | AMZ1 | 1.00 |
| 8889 | 3 | | | | | ADAM18 | 1.00 | 8985 | 3 | | | ANGPTL3 | 1.00 |
| 8890 | 3 | | | | | ADAM2 | 1.00 | 8986 | 3 | | | ANGPTL6 | 1.00 |
| 8891 | 3 | | | | | ADAM20 | 1.00 | 8987 | 3 | | | ANK1 | 1.00 |
| 8892 | 3 | | | | | ADAM21 | 1.00 | 8988 | 3 | | | ANKAR | 1.00 |
| 8893 | 3 | | | | | ADAM21P1 | 1.00 | 8989 | 3 | | | ANKFN1 | 1.00 |
| 8894 | 3 | | | | | ADAM23 | 1.00 | 8990 | 3 | | | ANKRD1 | 1.00 |
| 8895 | 3 | | | | | ADAM29 | 1.00 | 8991 | 3 | | | ANKRD18DP | 1.00 |
| 8896 | 3 | | | | | ADAM30 | 1.00 | 8992 | 3 | | | ANKRD2 | 1.00 |
| 8897 | 3 | | | | | ADAM32 | 1.00 | 8993 | 3 | | | ANKRD20A1 | 1.00 |
| 8898 | 3 | | | | | ADAM3A | 1.00 | 8994 | 3 | | | ANKRD20A11P | 1.00 |
| 8899 | 3 | | | | | ADAM5P | 1.00 | 8995 | 3 | | | ANKRD20A2 | 1.00 |
| 8900 | 3 | | | | | ADAM6 | 1.00 | 8996 | 3 | | | ANKRD20A3 | 1.00 |
| 8901 | 3 | | | | | ADAM7 | 1.00 | 8997 | 3 | | | ANKRD20A4 | 1.00 |
| 8902 | 3 | | | | | ADAMDEC1 | 1.00 | 8998 | 3 | | | ANKRD20A5P | 1.00 |
| 8903 | 3 | | | | | ADAMTS12 | 1.00 | 8999 | 3 | | | ANKRD20A8P | 1.00 |
| 8904 | 3 | | | | | ADAMTS16 | 1.00 | 9000 | 3 | | | ANKRD20A9P | 1.00 |
| 8905 | 3 | | | | | ADAMTS18 | 1.00 | 9001 | 3 | | | ANKRD24 | 1.00 |
| 8906 | 3 | | | | | ADAMTS19 | 1.00 | 9002 | 3 | | | ANKRD26P1 | 1.00 |
| 8907 | 3 | | | | | ADAMTS20 | 1.00 | 9003 | 3 | | | ANKRD26P3 | 1.00 |
| 8908 | 3 | | | | | ADAMTS3 | 1.00 | 9004 | 3 | | | ANKRD30A | 1.00 |
| 8909 | 3 | | | | | ADAMTS6 | 1.00 | 9005 | 3 | | | ANKRD30B | 1.00 |
| 8910 | 3 | | | | | ADAMTSL2 | 1.00 | 9006 | 3 | | | ANKRD30BL | 1.00 |
| 8911 | 3 | | | | | ADARB2 | 1.00 | 9007 | 3 | | | ANKRD30BP2 | 1.00 |
| 8912 | 3 | | | | | ADARB2-AS1 | 1.00 | 9008 | 3 | | | ANKRD31 | 1.00 |
| 8913 | 3 | | | | | ADCY1 | 1.00 | 9009 | 3 | | | ANKRD33 | 1.00 |
| 8914 | 3 | | | | | ADCY10 | 1.00 | 9010 | 3 | | | ANKRD34A | 1.00 |
| 8915 | 3 | | | | | ADD2 | 1.00 | 9011 | 3 | | | ANKRD34B | 1.00 |
| 8916 | 3 | | | | | ADGB | 1.00 | 9012 | 3 | | | ANKRD34C | 1.00 |
| 8917 | 3 | | | | | ADH6 | 1.00 | 9013 | 3 | | | ANKRD36BP2 | 1.00 |
| 8918 | 3 | | | | | ADH7 | 1.00 | 9014 | 3 | | | ANKRD45 | 1.00 |
| 8919 | 3 | | | | | ADIG | 1.00 | 9015 | 3 | | | ANKRD55 | 1.00 |
| 8920 | 3 | | | | | ADM2 | 1.00 | 9016 | 3 | | | ANKRD62P1-PARP4P3 | 1.00 |
| 8921 | 3 | | | | | ADRA1D | 1.00 | 9017 | 3 | | | ANKRD63 | 1.00 |
| 8922 | 3 | | | | | ADRB3 | 1.00 | 9018 | 3 | | | ANKRD7 | 1.00 |
| 8923 | 3 | | | | | AFAP1-AS1 | 1.00 | 9019 | 3 | | | ANKS1B | 1.00 |
| 8924 | 3 | | | | | AFF2 | 1.00 | 9020 | 3 | | | ANKS4B | 1.00 |
| 8925 | 3 | | | | | AFM | 1.00 | | | | | | |

Fig. 38 - 48

| | | | | | | | | | | | | | | |
|---|---|---|---|---|---|---|---|---|---|---|---|---|---|---|
| 9021 | 3 | | | | | ANKUB1 | 1.00 | 9117 | 3 | | | | ATP1A3 | 1.00 |
| 9022 | 3 | | | | | ANO2 | 1.00 | 9118 | 3 | | | | ATP1A4 | 1.00 |
| 9023 | 3 | | | | | ANO3 | 1.00 | 9119 | 3 | | | | ATP1B4 | 1.00 |
| 9024 | 3 | | | | | ANO4 | 1.00 | 9120 | 3 | | | | ATP2A1 | 1.00 |
| 9025 | 3 | | | | | ANO5 | 1.00 | 9121 | 3 | | | | ATP2B2 | 1.00 |
| 9026 | 3 | | | | | ANO7 | 1.00 | 9122 | 3 | | | | ATP2B3 | 1.00 |
| 9027 | 3 | | | | | ANP32A-IT1 | 1.00 | 9123 | 3 | | | | ATP4A | 1.00 |
| 9028 | 3 | | | | | ANTXRL | 1.00 | 9124 | 3 | | | | ATP4B | 1.00 |
| 9029 | 3 | | | | | ANXA10 | 1.00 | 9125 | 3 | | | | ATP6V0CP3 | 1.00 |
| 9030 | 3 | | | | | AOX2P | 1.00 | 9126 | 3 | | | | ATP6V0D2 | 1.00 |
| 9031 | 3 | | | | | AP1B1P1 | 1.00 | 9127 | 3 | | | | ATP6V1G3 | 1.00 |
| 9032 | 3 | | | | | AP3B2 | 1.00 | 9128 | 3 | | | | ATP8A2 | 1.00 |
| 9033 | 3 | | | | | APC2 | 1.00 | 9129 | 3 | | | | ATP8B3 | 1.00 |
| 9034 | 3 | | | | | APCS | 1.00 | 9130 | 3 | | | | ATPAF1-AS1 | 1.00 |
| 9035 | 3 | | | | | APITD1-CORT | 1.00 | 9131 | 3 | | | | ATRNL1 | 1.00 |
| 9036 | 3 | | | | | APLP1 | 1.00 | 9132 | 3 | | | | ATXN3L | 1.00 |
| 9037 | 3 | | | | | APOA2 | 1.00 | 9133 | 3 | | | | ATXN8OS | 1.00 |
| 9038 | 3 | | | | | APOA4 | 1.00 | 9134 | 3 | | | | AVP | 1.00 |
| 9039 | 3 | | | | | APOA5 | 1.00 | 9135 | 3 | | | | AVPR1A | 1.00 |
| 9040 | 3 | | | | | APOB | 1.00 | 9136 | 3 | | | | AVPR1B | 1.00 |
| 9041 | 3 | | | | | APOBEC1 | 1.00 | 9137 | 3 | | | | AXDND1 | 1.00 |
| 9042 | 3 | | | | | APOBEC3H | 1.00 | 9138 | 3 | | | | AZU1 | 1.00 |
| 9043 | 3 | | | | | APOBEC4 | 1.00 | 9139 | 3 | | | | B3GALT1 | 1.00 |
| 9044 | 3 | | | | | APOC1P1 | 1.00 | 9140 | 3 | | | | B3GALT2 | 1.00 |
| 9045 | 3 | | | | | APOC3 | 1.00 | 9141 | 3 | | | | B3GALT5 | 1.00 |
| 9046 | 3 | | | | | APOC4 | 1.00 | 9142 | 3 | | | | B3GAT1 | 1.00 |
| 9047 | 3 | | | | | APOC4-APOC2 | 1.00 | 9143 | 3 | | | | B3GAT2 | 1.00 |
| 9048 | 3 | | | | | APOF | 1.00 | 9144 | 3 | | | | B3GNT6 | 1.00 |
| 9049 | 3 | | | | | APOH | 1.00 | 9145 | 3 | | | | B7H6 | 1.00 |
| 9050 | 3 | | | | | APOL5 | 1.00 | 9146 | 3 | | | | BAAT | 1.00 |
| 9051 | 3 | | | | | AQP10 | 1.00 | 9147 | 3 | | | | BAGE | 1.00 |
| 9052 | 3 | | | | | AQP11 | 1.00 | 9148 | 3 | | | | BAGE3 | 1.00 |
| 9053 | 3 | | | | | AQP12A | 1.00 | 9149 | 3 | | | | BAGE4 | 1.00 |
| 9054 | 3 | | | | | AQP12B | 1.00 | 9150 | 3 | | | | BAGE5 | 1.00 |
| 9055 | 3 | | | | | AQP2 | 1.00 | 9151 | 3 | | | | BAI2 | 1.00 |
| 9056 | 3 | | | | | AQP4 | 1.00 | 9152 | 3 | | | | BAI3 | 1.00 |
| 9057 | 3 | | | | | AQP6 | 1.00 | 9153 | 3 | | | | BANF2 | 1.00 |
| 9058 | 3 | | | | | AQP8 | 1.00 | 9154 | 3 | | | | BANK1 | 1.00 |
| 9059 | 3 | | | | | ARGFX | 1.00 | 9155 | 3 | | | | BARHL1 | 1.00 |
| 9060 | 3 | | | | | ARGFXP2 | 1.00 | 9156 | 3 | | | | BARHL2 | 1.00 |
| 9061 | 3 | | | | | ARHGAP11B | 1.00 | 9157 | 3 | | | | BARX1 | 1.00 |
| 9062 | 3 | | | | | ARHGAP19-SLIT1 | 1.00 | 9158 | 3 | | | | BCAR4 | 1.00 |
| 9063 | 3 | | | | | ARHGAP36 | 1.00 | 9159 | 3 | | | | BCL2L14 | 1.00 |
| 9064 | 3 | | | | | ARHGAP42 | 1.00 | 9160 | 3 | | | | BCL2L15 | 1.00 |
| 9065 | 3 | | | | | ARHGDIG | 1.00 | 9161 | 3 | | | | BCMO1 | 1.00 |
| 9066 | 3 | | | | | ARHGEF26-AS1 | 1.00 | 9162 | 3 | | | | BCO2 | 1.00 |
| 9067 | 3 | | | | | ARHGEF33 | 1.00 | 9163 | 3 | | | | BCORP1 | 1.00 |
| 9068 | 3 | | | | | ARHGEF38 | 1.00 | 9164 | 3 | | | | BCYRN1 | 1.00 |
| 9069 | 3 | | | | | ARID3C | 1.00 | 9165 | 3 | | | | BDAG1 | 1.00 |
| 9070 | 3 | | | | | ARL11 | 1.00 | 9166 | 3 | | | | BDNF | 1.00 |
| 9071 | 3 | | | | | ARL13A | 1.00 | 9167 | 3 | | | | BEND2 | 1.00 |
| 9072 | 3 | | | | | ARL14 | 1.00 | 9168 | 3 | | | | BEND3 | 1.00 |
| 9073 | 3 | | | | | ARL2-SNX15 | 1.00 | 9169 | 3 | | | | BEND4 | 1.00 |
| 9074 | 3 | | | | | ARL5C | 1.00 | 9170 | 3 | | | | BEND6 | 1.00 |
| 9075 | 3 | | | | | ARMC2 | 1.00 | 9171 | 3 | | | | BEST3 | 1.00 |
| 9076 | 3 | | | | | ARMC3 | 1.00 | 9172 | 3 | | | | BET3L | 1.00 |
| 9077 | 3 | | | | | ARMC4 | 1.00 | 9173 | 3 | | | | BEX1 | 1.00 |
| 9078 | 3 | | | | | ARMC9 | 1.00 | 9174 | 3 | | | | BFSP2 | 1.00 |
| 9079 | 3 | | | | | ARMS2 | 1.00 | 9175 | 3 | | | | BHLHA9 | 1.00 |
| 9080 | 3 | | | | | ARPP21 | 1.00 | 9176 | 3 | | | | BHLHE23 | 1.00 |
| 9081 | 3 | | | | | ARR3 | 1.00 | 9177 | 3 | | | | BIRC8 | 1.00 |
| 9082 | 3 | | | | | ARRDC5 | 1.00 | 9178 | 3 | | | | BIVM-ERCC5 | 1.00 |
| 9083 | 3 | | | | | ARSE | 1.00 | 9179 | 3 | | | | BK250D11 | 1.00 |
| 9084 | 3 | | | | | ARSH | 1.00 | 9180 | 3 | | | | BLID | 1.00 |
| 9085 | 3 | | | | | ART1 | 1.00 | 9181 | 3 | | | | BLK | 1.00 |
| 9086 | 3 | | | | | ART3 | 1.00 | 9182 | 3 | | | | BLM | 1.00 |
| 9087 | 3 | | | | | ART5 | 1.00 | 9183 | 3 | | | | BMP10 | 1.00 |
| 9088 | 3 | | | | | ARTN | 1.00 | 9184 | 3 | | | | BMP15 | 1.00 |
| 9089 | 3 | | | | | ARX | 1.00 | 9185 | 3 | | | | BMP3 | 1.00 |
| 9090 | 3 | | | | | ASAH2 | 1.00 | 9186 | 3 | | | | BMP5 | 1.00 |
| 9091 | 3 | | | | | ASAH2B | 1.00 | 9187 | 3 | | | | BMPER | 1.00 |
| 9092 | 3 | | | | | ASAP1-IT1 | 1.00 | 9188 | 3 | | | | BMPR1B | 1.00 |
| 9093 | 3 | | | | | ASB10 | 1.00 | 9189 | 3 | | | | BOK-AS1 | 1.00 |
| 9094 | 3 | | | | | ASB11 | 1.00 | 9190 | 3 | | | | BOLL | 1.00 |
| 9095 | 3 | | | | | ASB12 | 1.00 | 9191 | 3 | | | | BPESC1 | 1.00 |
| 9096 | 3 | | | | | ASB15 | 1.00 | 9192 | 3 | | | | BPI | 1.00 |
| 9097 | 3 | | | | | ASB17 | 1.00 | 9193 | 3 | | | | BPIFA1 | 1.00 |
| 9098 | 3 | | | | | ASB18 | 1.00 | 9194 | 3 | | | | BPIFA2 | 1.00 |
| 9099 | 3 | | | | | ASB4 | 1.00 | 9195 | 3 | | | | BPIFA3 | 1.00 |
| 9100 | 3 | | | | | ASB5 | 1.00 | 9196 | 3 | | | | BPIFA4P | 1.00 |
| 9101 | 3 | | | | | ASB9P1 | 1.00 | 9197 | 3 | | | | BPIFB1 | 1.00 |
| 9102 | 3 | | | | | ASCL1 | 1.00 | 9198 | 3 | | | | BPIFB2 | 1.00 |
| 9103 | 3 | | | | | ASCL3 | 1.00 | 9199 | 3 | | | | BPIFB3 | 1.00 |
| 9104 | 3 | | | | | ASCL4 | 1.00 | 9200 | 3 | | | | BPIFB4 | 1.00 |
| 9105 | 3 | | | | | ASMT | 1.00 | 9201 | 3 | | | | BPIFB6 | 1.00 |
| 9106 | 3 | | | | | ASPDH | 1.00 | 9202 | 3 | | | | BPY2 | 1.00 |
| 9107 | 3 | | | | | ASPG | 1.00 | 9203 | 3 | | | | BPY2B | 1.00 |
| 9108 | 3 | | | | | ASPHD1 | 1.00 | 9204 | 3 | | | | BRAF | 1.00 |
| 9109 | 3 | | | | | ASPM | 1.00 | 9205 | 3 | | | | BRCA2 | 1.00 |
| 9110 | 3 | | | | | ASTL | 1.00 | 9206 | 3 | | | | BRD7P3 | 1.00 |
| 9111 | 3 | | | | | ASXL3 | 1.00 | 9207 | 3 | | | | BRDT | 1.00 |
| 9112 | 3 | | | | | ASZ1 | 1.00 | 9208 | 3 | | | | BRIP1 | 1.00 |
| 9113 | 3 | | | | | ATAD5 | 1.00 | 9209 | 3 | | | | BRS3 | 1.00 |
| 9114 | 3 | | | | | ATCAY | 1.00 | 9210 | 3 | | | | BRSK1 | 1.00 |
| 9115 | 3 | | | | | ATOH1 | 1.00 | 9211 | 3 | | | | BRSK2 | 1.00 |
| 9116 | 3 | | | | | ATOH7 | 1.00 | 9212 | 3 | | | | BSN | 1.00 |

Fig. 38 - 49

| | | | | | | | | | | | | | | |
|---|---|---|---|---|---|---|---|---|---|---|---|---|---|---|
| 9213 | 3 | | | | | BSN-AS2 | 1.00 | 9309 | 3 | | | | C15orf55 | 1.00 |
| 9214 | 3 | | | | | BSND | 1.00 | 9310 | 3 | | | | C15orf56 | 1.00 |
| 9215 | 3 | | | | | BSPH1 | 1.00 | 9311 | 3 | | | | C15orf60 | 1.00 |
| 9216 | 3 | | | | | BSX | 1.00 | 9312 | 3 | | | | C16orf11 | 1.00 |
| 9217 | 3 | | | | | BTBD17 | 1.00 | 9313 | 3 | | | | C16orf59 | 1.00 |
| 9218 | 3 | | | | | BTBD18 | 1.00 | 9314 | 3 | | | | C16orf71 | 1.00 |
| 9219 | 3 | | | | | BTBD8 | 1.00 | 9315 | 3 | | | | C16orf73 | 1.00 |
| 9220 | 3 | | | | | BTF3P11 | 1.00 | 9316 | 3 | | | | C16orf78 | 1.00 |
| 9221 | 3 | | | | | BTG4 | 1.00 | 9317 | 3 | | | | C16orf82 | 1.00 |
| 9222 | 3 | | | | | BTLA | 1.00 | 9318 | 3 | | | | C16orf90 | 1.00 |
| 9223 | 3 | | | | | BTN1A1 | 1.00 | 9319 | 3 | | | | C16orf92 | 1.00 |
| 9224 | 3 | | | | | BTNL2 | 1.00 | 9320 | 3 | | | | C16orf93 | 1.00 |
| 9225 | 3 | | | | | BTNL3 | 1.00 | 9321 | 3 | | | | C16orf95 | 1.00 |
| 9226 | 3 | | | | | BTNL8 | 1.00 | 9322 | 3 | | | | C16orf96 | 1.00 |
| 9227 | 3 | | | | | BUB1 | 1.00 | 9323 | 3 | | | | C17orf102 | 1.00 |
| 9228 | 3 | | | | | BUB1B | 1.00 | 9324 | 3 | | | | C17orf104 | 1.00 |
| 9229 | 3 | | | | | BVES-AS1 | 1.00 | 9325 | 3 | | | | C17orf105 | 1.00 |
| 9230 | 3 | | | | | C10orf103 | 1.00 | 9326 | 3 | | | | C17orf110 | 1.00 |
| 9231 | 3 | | | | | C10orf107 | 1.00 | 9327 | 3 | | | | C17orf47 | 1.00 |
| 9232 | 3 | | | | | C10orf108 | 1.00 | 9328 | 3 | | | | C17orf50 | 1.00 |
| 9233 | 3 | | | | | C10orf111 | 1.00 | 9329 | 3 | | | | C17orf64 | 1.00 |
| 9234 | 3 | | | | | C10orf113 | 1.00 | 9330 | 3 | | | | C17orf66 | 1.00 |
| 9235 | 3 | | | | | C10orf12 | 1.00 | 9331 | 3 | | | | C17orf74 | 1.00 |
| 9236 | 3 | | | | | C10orf120 | 1.00 | 9332 | 3 | | | | C17orf77 | 1.00 |
| 9237 | 3 | | | | | C10orf122 | 1.00 | 9333 | 3 | | | | C17orf78 | 1.00 |
| 9238 | 3 | | | | | C10orf131 | 1.00 | 9334 | 3 | | | | C17orf82 | 1.00 |
| 9239 | 3 | | | | | C10orf136 | 1.00 | 9335 | 3 | | | | C17orf98 | 1.00 |
| 9240 | 3 | | | | | C10orf27 | 1.00 | 9336 | 3 | | | | C17orf99 | 1.00 |
| 9241 | 3 | | | | | C10orf32-AS3MT | 1.00 | 9337 | 3 | | | | C18orf26 | 1.00 |
| 9242 | 3 | | | | | C10orf40 | 1.00 | 9338 | 3 | | | | C18orf34 | 1.00 |
| 9243 | 3 | | | | | C10orf53 | 1.00 | 9339 | 3 | | | | C18orf42 | 1.00 |
| 9244 | 3 | | | | | C10orf62 | 1.00 | 9340 | 3 | | | | C18orf54 | 1.00 |
| 9245 | 3 | | | | | C10orf67 | 1.00 | 9341 | 3 | | | | C18orf56 | 1.00 |
| 9246 | 3 | | | | | C10orf68 | 1.00 | 9342 | 3 | | | | C18orf62 | 1.00 |
| 9247 | 3 | | | | | C10orf71 | 1.00 | 9343 | 3 | | | | C18orf63 | 1.00 |
| 9248 | 3 | | | | | C10orf82 | 1.00 | 9344 | 3 | | | | C19orf35 | 1.00 |
| 9249 | 3 | | | | | C10orf90 | 1.00 | 9345 | 3 | | | | C19orf45 | 1.00 |
| 9250 | 3 | | | | | C10orf96 | 1.00 | 9346 | 3 | | | | C19orf46 | 1.00 |
| 9251 | 3 | | | | | C11orf16 | 1.00 | 9347 | 3 | | | | C19orf59 | 1.00 |
| 9252 | 3 | | | | | C11orf34 | 1.00 | 9348 | 3 | | | | C19orf69 | 1.00 |
| 9253 | 3 | | | | | C11orf36 | 1.00 | 9349 | 3 | | | | C19orf75 | 1.00 |
| 9254 | 3 | | | | | C11orf40 | 1.00 | 9350 | 3 | | | | C19orf80 | 1.00 |
| 9255 | 3 | | | | | C11orf41 | 1.00 | 9351 | 3 | | | | C1orf100 | 1.00 |
| 9256 | 3 | | | | | C11orf42 | 1.00 | 9352 | 3 | | | | C1orf101 | 1.00 |
| 9257 | 3 | | | | | C11orf53 | 1.00 | 9353 | 3 | | | | C1orf105 | 1.00 |
| 9258 | 3 | | | | | C11orf65 | 1.00 | 9354 | 3 | | | | C1orf110 | 1.00 |
| 9259 | 3 | | | | | C11orf82 | 1.00 | 9355 | 3 | | | | C1orf111 | 1.00 |
| 9260 | 3 | | | | | C11orf85 | 1.00 | 9356 | 3 | | | | C1orf112 | 1.00 |
| 9261 | 3 | | | | | C11orf86 | 1.00 | 9357 | 3 | | | | C1orf114 | 1.00 |
| 9262 | 3 | | | | | C11orf87 | 1.00 | 9358 | 3 | | | | C1orf127 | 1.00 |
| 9263 | 3 | | | | | C11orf88 | 1.00 | 9359 | 3 | | | | C1orf129 | 1.00 |
| 9264 | 3 | | | | | C11orf91 | 1.00 | 9360 | 3 | | | | C1orf135 | 1.00 |
| 9265 | 3 | | | | | C11orf92 | 1.00 | 9361 | 3 | | | | C1orf140 | 1.00 |
| 9266 | 3 | | | | | C11orf94 | 1.00 | 9362 | 3 | | | | C1orf141 | 1.00 |
| 9267 | 3 | | | | | C12orf12 | 1.00 | 9363 | 3 | | | | C1orf146 | 1.00 |
| 9268 | 3 | | | | | C12orf33 | 1.00 | 9364 | 3 | | | | C1orf168 | 1.00 |
| 9269 | 3 | | | | | C12orf36 | 1.00 | 9365 | 3 | | | | C1orf173 | 1.00 |
| 9270 | 3 | | | | | C12orf37 | 1.00 | 9366 | 3 | | | | C1orf177 | 1.00 |
| 9271 | 3 | | | | | C12orf39 | 1.00 | 9367 | 3 | | | | C1orf180 | 1.00 |
| 9272 | 3 | | | | | C12orf40 | 1.00 | 9368 | 3 | | | | C1orf182 | 1.00 |
| 9273 | 3 | | | | | C12orf42 | 1.00 | 9369 | 3 | | | | C1orf185 | 1.00 |
| 9274 | 3 | | | | | C12orf50 | 1.00 | 9370 | 3 | | | | C1orf187 | 1.00 |
| 9275 | 3 | | | | | C12orf54 | 1.00 | 9371 | 3 | | | | C1orf189 | 1.00 |
| 9276 | 3 | | | | | C12orf56 | 1.00 | 9372 | 3 | | | | C1orf194 | 1.00 |
| 9277 | 3 | | | | | C12orf59 | 1.00 | 9373 | 3 | | | | C1orf200 | 1.00 |
| 9278 | 3 | | | | | C12orf60 | 1.00 | 9374 | 3 | | | | C1orf220 | 1.00 |
| 9279 | 3 | | | | | C12orf61 | 1.00 | 9375 | 3 | | | | C1orf227 | 1.00 |
| 9280 | 3 | | | | | C12orf69 | 1.00 | 9376 | 3 | | | | C1orf228 | 1.00 |
| 9281 | 3 | | | | | C12orf70 | 1.00 | 9377 | 3 | | | | C1orf229 | 1.00 |
| 9282 | 3 | | | | | C12orf71 | 1.00 | 9378 | 3 | | | | C1orf49 | 1.00 |
| 9283 | 3 | | | | | C12orf74 | 1.00 | 9379 | 3 | | | | C1orf61 | 1.00 |
| 9284 | 3 | | | | | C12orf77 | 1.00 | 9380 | 3 | | | | C1orf64 | 1.00 |
| 9285 | 3 | | | | | C13orf35 | 1.00 | 9381 | 3 | | | | C1orf65 | 1.00 |
| 9286 | 3 | | | | | C14orf105 | 1.00 | 9382 | 3 | | | | C1orf87 | 1.00 |
| 9287 | 3 | | | | | C14orf162 | 1.00 | 9383 | 3 | | | | C1orf94 | 1.00 |
| 9288 | 3 | | | | | C14orf165 | 1.00 | 9384 | 3 | | | | C1orf98 | 1.00 |
| 9289 | 3 | | | | | C14orf166B | 1.00 | 9385 | 3 | | | | C1QL1 | 1.00 |
| 9290 | 3 | | | | | C14orf177 | 1.00 | 9386 | 3 | | | | C1QL2 | 1.00 |
| 9291 | 3 | | | | | C14orf178 | 1.00 | 9387 | 3 | | | | C1QL3 | 1.00 |
| 9292 | 3 | | | | | C14orf182 | 1.00 | 9388 | 3 | | | | C1QL4 | 1.00 |
| 9293 | 3 | | | | | C14orf183 | 1.00 | 9389 | 3 | | | | C1QTNF3-AMACR | 1.00 |
| 9294 | 3 | | | | | C14orf23 | 1.00 | 9390 | 3 | | | | C1QTNF8 | 1.00 |
| 9295 | 3 | | | | | C14orf38 | 1.00 | 9391 | 3 | | | | C20orf123 | 1.00 |
| 9296 | 3 | | | | | C14orf39 | 1.00 | 9392 | 3 | | | | C20orf132 | 1.00 |
| 9297 | 3 | | | | | C14orf55 | 1.00 | 9393 | 3 | | | | C20orf141 | 1.00 |
| 9298 | 3 | | | | | C15orf2 | 1.00 | 9394 | 3 | | | | C20orf144 | 1.00 |
| 9299 | 3 | | | | | C15orf26 | 1.00 | 9395 | 3 | | | | C20orf152 | 1.00 |
| 9300 | 3 | | | | | C15orf32 | 1.00 | 9396 | 3 | | | | C20orf166 | 1.00 |
| 9301 | 3 | | | | | C15orf33 | 1.00 | 9397 | 3 | | | | C20orf173 | 1.00 |
| 9302 | 3 | | | | | C15orf34 | 1.00 | 9398 | 3 | | | | C20orf197 | 1.00 |
| 9303 | 3 | | | | | C15orf38-AP352 | 1.00 | 9399 | 3 | | | | C20orf201 | 1.00 |
| 9304 | 3 | | | | | C15orf42 | 1.00 | 9400 | 3 | | | | C20orf202 | 1.00 |
| 9305 | 3 | | | | | C15orf43 | 1.00 | 9401 | 3 | | | | C20orf203 | 1.00 |
| 9306 | 3 | | | | | C15orf50 | 1.00 | 9402 | 3 | | | | C20orf26 | 1.00 |
| 9307 | 3 | | | | | C15orf53 | 1.00 | 9403 | 3 | | | | C20orf79 | 1.00 |
| 9308 | 3 | | | | | C15orf54 | 1.00 | 9404 | 3 | | | | C20orf85 | 1.00 |

Fig. 38 - 50

| | | | | | | | | | | | |
|---|---|---|---|---|---|---|---|---|---|---|---|
| 9405 | 3 | | | | C20orf94 | 1.00 | 9501 | 3 | | C6orf99 | 1.00 |
| 9406 | 3 | | | | C21orf128 | 1.00 | 9502 | 3 | | C7orf10 | 1.00 |
| 9407 | 3 | | | | C21orf37 | 1.00 | 9503 | 3 | | C7orf33 | 1.00 |
| 9408 | 3 | | | | C21orf49 | 1.00 | 9504 | 3 | | C7orf34 | 1.00 |
| 9409 | 3 | | | | C21orf54 | 1.00 | 9505 | 3 | | C7orf45 | 1.00 |
| 9410 | 3 | | | | C21orf62 | 1.00 | 9506 | 3 | | C7orf57 | 1.00 |
| 9411 | 3 | | | | C21orf90 | 1.00 | 9507 | 3 | | C7orf62 | 1.00 |
| 9412 | 3 | | | | C21orf91-OT1 | 1.00 | 9508 | 3 | | C7orf65 | 1.00 |
| 9413 | 3 | | | | C22orf15 | 1.00 | 9509 | 3 | | C7orf66 | 1.00 |
| 9414 | 3 | | | | C22orf24 | 1.00 | 9510 | 3 | | C7orf69 | 1.00 |
| 9415 | 3 | | | | C22orf26 | 1.00 | 9511 | 3 | | C7orf71 | 1.00 |
| 9416 | 3 | | | | C22orf42 | 1.00 | 9512 | 3 | | C7orf72 | 1.00 |
| 9417 | 3 | | | | C22orf43 | 1.00 | 9513 | 3 | | C8A | 1.00 |
| 9418 | 3 | | | | C22orf45 | 1.00 | 9514 | 3 | | C8B | 1.00 |
| 9419 | 3 | | | | C2CD4A | 1.00 | 9515 | 3 | | C8G | 1.00 |
| 9420 | 3 | | | | C2orf16 | 1.00 | 9516 | 3 | | C8orf12 | 1.00 |
| 9421 | 3 | | | | C2orf27A | 1.00 | 9517 | 3 | | C8orf22 | 1.00 |
| 9422 | 3 | | | | C2orf27B | 1.00 | 9518 | 3 | | C8orf31 | 1.00 |
| 9423 | 3 | | | | C2orf48 | 1.00 | 9519 | 3 | | C8orf34 | 1.00 |
| 9424 | 3 | | | | C2orf50 | 1.00 | 9520 | 3 | | C8orf39 | 1.00 |
| 9425 | 3 | | | | C2orf51 | 1.00 | 9521 | 3 | | C8orf45 | 1.00 |
| 9426 | 3 | | | | C2orf53 | 1.00 | 9522 | 3 | | C8orf46 | 1.00 |
| 9427 | 3 | | | | C2orf57 | 1.00 | 9523 | 3 | | C8orf51 | 1.00 |
| 9428 | 3 | | | | C2orf61 | 1.00 | 9524 | 3 | | C8orf69 | 1.00 |
| 9429 | 3 | | | | C2orf62 | 1.00 | 9525 | 3 | | C8orf71 | 1.00 |
| 9430 | 3 | | | | C2orf65 | 1.00 | 9526 | 3 | | C8orf74 | 1.00 |
| 9431 | 3 | | | | C2orf66 | 1.00 | 9527 | 3 | | C8orf75 | 1.00 |
| 9432 | 3 | | | | C2orf70 | 1.00 | 9528 | 3 | | C8orf77 | 1.00 |
| 9433 | 3 | | | | C2orf71 | 1.00 | 9529 | 3 | | C8orf80 | 1.00 |
| 9434 | 3 | | | | C2orf73 | 1.00 | 9530 | 3 | | C8orf86 | 1.00 |
| 9435 | 3 | | | | C2orf77 | 1.00 | 9531 | 3 | | C8orf87 | 1.00 |
| 9436 | 3 | | | | C2orf78 | 1.00 | 9532 | 3 | | C8ORFK29 | 1.00 |
| 9437 | 3 | | | | C2orf80 | 1.00 | 9533 | 3 | | C9 | 1.00 |
| 9438 | 3 | | | | C2orf83 | 1.00 | 9534 | 3 | | C9orf102 | 1.00 |
| 9439 | 3 | | | | C2orf84 | 1.00 | 9535 | 3 | | C9orf11 | 1.00 |
| 9440 | 3 | | | | C2orf91 | 1.00 | 9536 | 3 | | C9orf117 | 1.00 |
| 9441 | 3 | | | | C3orf20 | 1.00 | 9537 | 3 | | C9orf128 | 1.00 |
| 9442 | 3 | | | | C3orf22 | 1.00 | 9538 | 3 | | C9orf131 | 1.00 |
| 9443 | 3 | | | | C3orf24 | 1.00 | 9539 | 3 | | C9orf135 | 1.00 |
| 9444 | 3 | | | | C3orf25 | 1.00 | 9540 | 3 | | C9orf139 | 1.00 |
| 9445 | 3 | | | | C3orf27 | 1.00 | 9541 | 3 | | C9orf146 | 1.00 |
| 9446 | 3 | | | | C3orf30 | 1.00 | 9542 | 3 | | C9orf153 | 1.00 |
| 9447 | 3 | | | | C3orf32 | 1.00 | 9543 | 3 | | C9orf163 | 1.00 |
| 9448 | 3 | | | | C3orf36 | 1.00 | 9544 | 3 | | C9orf170 | 1.00 |
| 9449 | 3 | | | | C3orf43 | 1.00 | 9545 | 3 | | C9orf171 | 1.00 |
| 9450 | 3 | | | | C3orf45 | 1.00 | 9546 | 3 | | C9orf174 | 1.00 |
| 9451 | 3 | | | | C3orf49 | 1.00 | 9547 | 3 | | C9orf29 | 1.00 |
| 9452 | 3 | | | | C3orf51 | 1.00 | 9548 | 3 | | C9orf30-TMEFF1 | 1.00 |
| 9453 | 3 | | | | C3orf65 | 1.00 | 9549 | 3 | | C9orf4 | 1.00 |
| 9454 | 3 | | | | C3orf67 | 1.00 | 9550 | 3 | | C9orf43 | 1.00 |
| 9455 | 3 | | | | C3orf72 | 1.00 | 9551 | 3 | | C9orf47 | 1.00 |
| 9456 | 3 | | | | C3orf77 | 1.00 | 9552 | 3 | | C9orf50 | 1.00 |
| 9457 | 3 | | | | C3orf79 | 1.00 | 9553 | 3 | | C9orf53 | 1.00 |
| 9458 | 3 | | | | C3orf80 | 1.00 | 9554 | 3 | | C9orf57 | 1.00 |
| 9459 | 3 | | | | C3P1 | 1.00 | 9555 | 3 | | C9orf66 | 1.00 |
| 9460 | 3 | | | | C4A | 1.00 | 9556 | 3 | | C9orf79 | 1.00 |
| 9461 | 3 | | | | C4B | 1.00 | 9557 | 3 | | C9orf84 | 1.00 |
| 9462 | 3 | | | | C4BPA | 1.00 | 9558 | 3 | | C9orf93 | 1.00 |
| 9463 | 3 | | | | C4BPB | 1.00 | 9559 | 3 | | C9orf96 | 1.00 |
| 9464 | 3 | | | | C4orf17 | 1.00 | 9560 | 3 | | CA1 | 1.00 |
| 9465 | 3 | | | | C4orf21 | 1.00 | 9561 | 3 | | CA10 | 1.00 |
| 9466 | 3 | | | | C4orf22 | 1.00 | 9562 | 3 | | CA14 | 1.00 |
| 9467 | 3 | | | | C4orf26 | 1.00 | 9563 | 3 | | CA5A | 1.00 |
| 9468 | 3 | | | | C4orf36 | 1.00 | 9564 | 3 | | CA7 | 1.00 |
| 9469 | 3 | | | | C4orf37 | 1.00 | 9565 | 3 | | CABP2 | 1.00 |
| 9470 | 3 | | | | C4orf38 | 1.00 | 9566 | 3 | | CABP5 | 1.00 |
| 9471 | 3 | | | | C4orf40 | 1.00 | 9567 | 3 | | CABP7 | 1.00 |
| 9472 | 3 | | | | C4orf44 | 1.00 | 9568 | 3 | | CABS1 | 1.00 |
| 9473 | 3 | | | | C4orf45 | 1.00 | 9569 | 3 | | CACNA1A | 1.00 |
| 9474 | 3 | | | | C4orf49 | 1.00 | 9570 | 3 | | CACNA1B | 1.00 |
| 9475 | 3 | | | | C4orf51 | 1.00 | 9571 | 3 | | CACNA1D | 1.00 |
| 9476 | 3 | | | | C4orf6 | 1.00 | 9572 | 3 | | CACNA1E | 1.00 |
| 9477 | 3 | | | | C5orf34 | 1.00 | 9573 | 3 | | CACNA1F | 1.00 |
| 9478 | 3 | | | | C5orf42 | 1.00 | 9574 | 3 | | CACNA1I | 1.00 |
| 9479 | 3 | | | | C5orf47 | 1.00 | 9575 | 3 | | CACNA1S | 1.00 |
| 9480 | 3 | | | | C5orf48 | 1.00 | 9576 | 3 | | CACNA2D1 | 1.00 |
| 9481 | 3 | | | | C5orf49 | 1.00 | 9577 | 3 | | CACNA2D3 | 1.00 |
| 9482 | 3 | | | | C5orf52 | 1.00 | 9578 | 3 | | CACNA2D4 | 1.00 |
| 9483 | 3 | | | | C5orf58 | 1.00 | 9579 | 3 | | CACNG1 | 1.00 |
| 9484 | 3 | | | | C5orf60 | 1.00 | 9580 | 3 | | CACNG2 | 1.00 |
| 9485 | 3 | | | | C5orf64 | 1.00 | 9581 | 3 | | CACNG3 | 1.00 |
| 9486 | 3 | | | | C6orf10 | 1.00 | 9582 | 3 | | CACNG5 | 1.00 |
| 9487 | 3 | | | | C6orf118 | 1.00 | 9583 | 3 | | CACNG6 | 1.00 |
| 9488 | 3 | | | | C6orf123 | 1.00 | 9584 | 3 | | CACNG7 | 1.00 |
| 9489 | 3 | | | | C6orf147 | 1.00 | 9585 | 3 | | CACNG8 | 1.00 |
| 9490 | 3 | | | | C6orf164 | 1.00 | 9586 | 3 | | CADM2 | 1.00 |
| 9491 | 3 | | | | C6orf165 | 1.00 | 9587 | 3 | | CADPS | 1.00 |
| 9492 | 3 | | | | C6orf174 | 1.00 | 9588 | 3 | | CAGE1 | 1.00 |
| 9493 | 3 | | | | C6orf195 | 1.00 | 9589 | 3 | | CALB1 | 1.00 |
| 9494 | 3 | | | | C6orf201 | 1.00 | 9590 | 3 | | CALCA | 1.00 |
| 9495 | 3 | | | | C6orf221 | 1.00 | 9591 | 3 | | CALCB | 1.00 |
| 9496 | 3 | | | | C6orf222 | 1.00 | 9592 | 3 | | CALCR | 1.00 |
| 9497 | 3 | | | | C6orf223 | 1.00 | 9593 | 3 | | CALHM1 | 1.00 |
| 9498 | 3 | | | | C6orf58 | 1.00 | 9594 | 3 | | CALHM3 | 1.00 |
| 9499 | 3 | | | | C6orf7 | 1.00 | 9595 | 3 | | CALN1 | 1.00 |
| 9500 | 3 | | | | C6orf97 | 1.00 | 9596 | 3 | | CALR3 | 1.00 |

Fig. 38 - 51

| | | | | | | | | | | | | | | | |
|---|---|---|---|---|---|---|---|---|---|---|---|---|---|---|---|
| 9597 | 3 | | | | | | CALY | 1.00 | 9693 | 3 | | | | CCNI2 | 1.00 |
| 9598 | 3 | | | | | | CAMK1G | 1.00 | 9694 | 3 | | | | CCR3 | 1.00 |
| 9599 | 3 | | | | | | CAMK2A | 1.00 | 9695 | 3 | | | | CCR9 | 1.00 |
| 9600 | 3 | | | | | | CAMK2N2 | 1.00 | 9696 | 3 | | | | CCT6B | 1.00 |
| 9601 | 3 | | | | | | CAMK4 | 1.00 | 9697 | 3 | | | | CCT8L2 | 1.00 |
| 9602 | 3 | | | | | | CAMKV | 1.00 | 9698 | 3 | | | | CD180 | 1.00 |
| 9603 | 3 | | | | | | CAMP | 1.00 | 9699 | 3 | | | | CD19 | 1.00 |
| 9604 | 3 | | | | | | CAPN13 | 1.00 | 9700 | 3 | | | | CD1D | 1.00 |
| 9605 | 3 | | | | | | CAPN14 | 1.00 | 9701 | 3 | | | | CD200R1L | 1.00 |
| 9606 | 3 | | | | | | CAPN8 | 1.00 | 9702 | 3 | | | | CD22 | 1.00 |
| 9607 | 3 | | | | | | CAPN9 | 1.00 | 9703 | 3 | | | | CD226 | 1.00 |
| 9608 | 3 | | | | | | CAPS2 | 1.00 | 9704 | 3 | | | | CD244 | 1.00 |
| 9609 | 3 | | | | | | CAPSL | 1.00 | 9705 | 3 | | | | CD300C | 1.00 |
| 9610 | 3 | | | | | | CARTPT | 1.00 | 9706 | 3 | | | | CD300LD | 1.00 |
| 9611 | 3 | | | | | | CASC1 | 1.00 | 9707 | 3 | | | | CD300LF | 1.00 |
| 9612 | 3 | | | | | | CASC2 | 1.00 | 9708 | 3 | | | | CD38 | 1.00 |
| 9613 | 3 | | | | | | CASC5 | 1.00 | 9709 | 3 | | | | CD5L | 1.00 |
| 9614 | 3 | | | | | | CASP12 | 1.00 | 9710 | 3 | | | | CD79A | 1.00 |
| 9615 | 3 | | | | | | CASP5 | 1.00 | 9711 | 3 | | | | CD80 | 1.00 |
| 9616 | 3 | | | | | | CASR | 1.00 | 9712 | 3 | | | | CDC20B | 1.00 |
| 9617 | 3 | | | | | | CATSPER1 | 1.00 | 9713 | 3 | | | | CDC25A | 1.00 |
| 9618 | 3 | | | | | | CATSPER3 | 1.00 | 9714 | 3 | | | | CDC25C | 1.00 |
| 9619 | 3 | | | | | | CATSPER4 | 1.00 | 9715 | 3 | | | | CDCA2 | 1.00 |
| 9620 | 3 | | | | | | CATSPERB | 1.00 | 9716 | 3 | | | | CDCP2 | 1.00 |
| 9621 | 3 | | | | | | CATSPERD | 1.00 | 9717 | 3 | | | | CDH10 | 1.00 |
| 9622 | 3 | | | | | | CAV3 | 1.00 | 9718 | 3 | | | | CDH15 | 1.00 |
| 9623 | 3 | | | | | | CBLN2 | 1.00 | 9719 | 3 | | | | CDH16 | 1.00 |
| 9624 | 3 | | | | | | CBLN4 | 1.00 | 9720 | 3 | | | | CDH17 | 1.00 |
| 9625 | 3 | | | | | | CBY3 | 1.00 | 9721 | 3 | | | | CDH18 | 1.00 |
| 9626 | 3 | | | | | | CC2D2B | 1.00 | 9722 | 3 | | | | CDH20 | 1.00 |
| 9627 | 3 | | | | | | CCDC105 | 1.00 | 9723 | 3 | | | | CDH26 | 1.00 |
| 9628 | 3 | | | | | | CCDC108 | 1.00 | 9724 | 3 | | | | CDH7 | 1.00 |
| 9629 | 3 | | | | | | CCDC11 | 1.00 | 9725 | 3 | | | | CDH8 | 1.00 |
| 9630 | 3 | | | | | | CCDC110 | 1.00 | 9726 | 3 | | | | CDH9 | 1.00 |
| 9631 | 3 | | | | | | CCDC116 | 1.00 | 9727 | 3 | | | | CDHR2 | 1.00 |
| 9632 | 3 | | | | | | CCDC13 | 1.00 | 9728 | 3 | | | | CDHR3 | 1.00 |
| 9633 | 3 | | | | | | CCDC135 | 1.00 | 9729 | 3 | | | | CDHR5 | 1.00 |
| 9634 | 3 | | | | | | CCDC138 | 1.00 | 9730 | 3 | | | | CDK15 | 1.00 |
| 9635 | 3 | | | | | | CCDC140 | 1.00 | 9731 | 3 | | | | CDK5R2 | 1.00 |
| 9636 | 3 | | | | | | CCDC141 | 1.00 | 9732 | 3 | | | | CDKL1 | 1.00 |
| 9637 | 3 | | | | | | CCDC144A | 1.00 | 9733 | 3 | | | | CDKL2 | 1.00 |
| 9638 | 3 | | | | | | CCDC144B | 1.00 | 9734 | 3 | | | | CDKL4 | 1.00 |
| 9639 | 3 | | | | | | CCDC144C | 1.00 | 9735 | 3 | | | | CDKL5 | 1.00 |
| 9640 | 3 | | | | | | CCDC144NL | 1.00 | 9736 | 3 | | | | CDKN2B-AS1 | 1.00 |
| 9641 | 3 | | | | | | CCDC147 | 1.00 | 9737 | 3 | | | | CDRT1 | 1.00 |
| 9642 | 3 | | | | | | CCDC148 | 1.00 | 9738 | 3 | | | | CDRT15 | 1.00 |
| 9643 | 3 | | | | | | CCDC150 | 1.00 | 9739 | 3 | | | | CDRT15L2 | 1.00 |
| 9644 | 3 | | | | | | CCDC151 | 1.00 | 9740 | 3 | | | | CDRT15P2 | 1.00 |
| 9645 | 3 | | | | | | CCDC154 | 1.00 | 9741 | 3 | | | | CDRT7 | 1.00 |
| 9646 | 3 | | | | | | CCDC155 | 1.00 | 9742 | 3 | | | | CDX1 | 1.00 |
| 9647 | 3 | | | | | | CCDC158 | 1.00 | 9743 | 3 | | | | CDX2 | 1.00 |
| 9648 | 3 | | | | | | CCDC160 | 1.00 | 9744 | 3 | | | | CDX4 | 1.00 |
| 9649 | 3 | | | | | | CCDC162P | 1.00 | 9745 | 3 | | | | CDY1 | 1.00 |
| 9650 | 3 | | | | | | CCDC164 | 1.00 | 9746 | 3 | | | | CDY1B | 1.00 |
| 9651 | 3 | | | | | | CCDC166 | 1.00 | 9747 | 3 | | | | CDY2A | 1.00 |
| 9652 | 3 | | | | | | CCDC168 | 1.00 | 9748 | 3 | | | | CDY2B | 1.00 |
| 9653 | 3 | | | | | | CCDC169 | 1.00 | 9749 | 3 | | | | CDYL2 | 1.00 |
| 9654 | 3 | | | | | | CCDC169-SOHLH2 | 1.00 | 9750 | 3 | | | | CEACAM16 | 1.00 |
| 9655 | 3 | | | | | | CCDC18 | 1.00 | 9751 | 3 | | | | CEACAM18 | 1.00 |
| 9656 | 3 | | | | | | CCDC19 | 1.00 | 9752 | 3 | | | | CEACAM20 | 1.00 |
| 9657 | 3 | | | | | | CCDC27 | 1.00 | 9753 | 3 | | | | CEACAM21 | 1.00 |
| 9658 | 3 | | | | | | CCDC30 | 1.00 | 9754 | 3 | | | | CEACAM22P | 1.00 |
| 9659 | 3 | | | | | | CCDC33 | 1.00 | 9755 | 3 | | | | CEACAM3 | 1.00 |
| 9660 | 3 | | | | | | CCDC36 | 1.00 | 9756 | 3 | | | | CEACAM4 | 1.00 |
| 9661 | 3 | | | | | | CCDC37 | 1.00 | 9757 | 3 | | | | CEACAM8 | 1.00 |
| 9662 | 3 | | | | | | CCDC38 | 1.00 | 9758 | 3 | | | | CEBPE | 1.00 |
| 9663 | 3 | | | | | | CCDC39 | 1.00 | 9759 | 3 | | | | CECR2 | 1.00 |
| 9664 | 3 | | | | | | CCDC42 | 1.00 | 9760 | 3 | | | | CECR3 | 1.00 |
| 9665 | 3 | | | | | | CCDC54 | 1.00 | 9761 | 3 | | | | CECR6 | 1.00 |
| 9666 | 3 | | | | | | CCDC60 | 1.00 | 9762 | 3 | | | | CELA1 | 1.00 |
| 9667 | 3 | | | | | | CCDC62 | 1.00 | 9763 | 3 | | | | CELA2A | 1.00 |
| 9668 | 3 | | | | | | CCDC63 | 1.00 | 9764 | 3 | | | | CELA2B | 1.00 |
| 9669 | 3 | | | | | | CCDC65 | 1.00 | 9765 | 3 | | | | CELA3A | 1.00 |
| 9670 | 3 | | | | | | CCDC67 | 1.00 | 9766 | 3 | | | | CELA3B | 1.00 |
| 9671 | 3 | | | | | | CCDC7 | 1.00 | 9767 | 3 | | | | CELF3 | 1.00 |
| 9672 | 3 | | | | | | CCDC70 | 1.00 | 9768 | 3 | | | | CELF4 | 1.00 |
| 9673 | 3 | | | | | | CCDC73 | 1.00 | 9769 | 3 | | | | CELF5 | 1.00 |
| 9674 | 3 | | | | | | CCDC78 | 1.00 | 9770 | 3 | | | | CELP | 1.00 |
| 9675 | 3 | | | | | | CCDC79 | 1.00 | 9771 | 3 | | | | CELSR3 | 1.00 |
| 9676 | 3 | | | | | | CCDC81 | 1.00 | 9772 | 3 | | | | CEND1 | 1.00 |
| 9677 | 3 | | | | | | CCDC83 | 1.00 | 9773 | 3 | | | | CENPE | 1.00 |
| 9678 | 3 | | | | | | CCDC87 | 1.00 | 9774 | 3 | | | | CENPI | 1.00 |
| 9679 | 3 | | | | | | CCIN | 1.00 | 9775 | 3 | | | | CENPVL1 | 1.00 |
| 9680 | 3 | | | | | | CCK | 1.00 | 9776 | 3 | | | | CEP128 | 1.00 |
| 9681 | 3 | | | | | | CCKAR | 1.00 | 9777 | 3 | | | | CEP170P1 | 1.00 |
| 9682 | 3 | | | | | | CCKBR | 1.00 | 9778 | 3 | | | | CEP290 | 1.00 |
| 9683 | 3 | | | | | | CCL1 | 1.00 | 9779 | 3 | | | | CEP97 | 1.00 |
| 9684 | 3 | | | | | | CCL11 | 1.00 | 9780 | 3 | | | | CER1 | 1.00 |
| 9685 | 3 | | | | | | CCL14-CCL15 | 1.00 | 9781 | 3 | | | | CERS1 | 1.00 |
| 9686 | 3 | | | | | | CCL15 | 1.00 | 9782 | 3 | | | | CES1P1 | 1.00 |
| 9687 | 3 | | | | | | CCL25 | 1.00 | 9783 | 3 | | | | CES1P2 | 1.00 |
| 9688 | 3 | | | | | | CCL3L1 | 1.00 | 9784 | 3 | | | | CES5A | 1.00 |
| 9689 | 3 | | | | | | CCL7 | 1.00 | 9785 | 3 | | | | CES5AP1 | 1.00 |
| 9690 | 3 | | | | | | CCNA1 | 1.00 | 9786 | 3 | | | | CETN1 | 1.00 |
| 9691 | 3 | | | | | | CCNB3 | 1.00 | 9787 | 3 | | | | CETN4P | 1.00 |
| 9692 | 3 | | | | | | CCNE2 | 1.00 | 9788 | 3 | | | | CETP | 1.00 |

Fig. 38 - 52

| | | | | | | | |
|---|---|---|---|---|---|---|---|
| 9789 | 3 | CFC1 | 1.00 | 9885 | 3 | CLVS2 | 1.00 |
| 9790 | 3 | CFC1B | 1.00 | 9886 | 3 | CLYBL | 1.00 |
| 9791 | 3 | CFHR2 | 1.00 | 9887 | 3 | CMTM2 | 1.00 |
| 9792 | 3 | CFHR3 | 1.00 | 9888 | 3 | CNBH6.4 | 1.00 |
| 9793 | 3 | CFHR4 | 1.00 | 9889 | 3 | CNBD1 | 1.00 |
| 9794 | 3 | CFHR5 | 1.00 | 9890 | 3 | CNDP1 | 1.00 |
| 9795 | 3 | CFL1P1 | 1.00 | 9891 | 3 | CNGA2 | 1.00 |
| 9796 | 3 | CFLAR-AS1 | 1.00 | 9892 | 3 | CNGA3 | 1.00 |
| 9797 | 3 | CGA | 1.00 | 9893 | 3 | CNGA4 | 1.00 |
| 9798 | 3 | CGB | 1.00 | 9894 | 3 | CNGB1 | 1.00 |
| 9799 | 3 | CGB1 | 1.00 | 9895 | 3 | CNGB3 | 1.00 |
| 9800 | 3 | CGB5 | 1.00 | 9896 | 3 | CNIH3 | 1.00 |
| 9801 | 3 | CGB8 | 1.00 | 9897 | 3 | CNPY1 | 1.00 |
| 9802 | 3 | CHAT | 1.00 | 9898 | 3 | CNR2 | 1.00 |
| 9803 | 3 | CHDS | 1.00 | 9899 | 3 | CNTD2 | 1.00 |
| 9804 | 3 | CHEK2P2 | 1.00 | 9900 | 3 | CNTN3 | 1.00 |
| 9805 | 3 | CHGB | 1.00 | 9901 | 3 | CNTN4 | 1.00 |
| 9806 | 3 | CHIA | 1.00 | 9902 | 3 | CNTN5 | 1.00 |
| 9807 | 3 | CHIT1 | 1.00 | 9903 | 3 | CNTN6 | 1.00 |
| 9808 | 3 | CHKB-CPT1B | 1.00 | 9904 | 3 | CNTNAP2 | 1.00 |
| 9809 | 3 | CHODL-AS1 | 1.00 | 9905 | 3 | CNTNAP4 | 1.00 |
| 9810 | 3 | CHRDL2 | 1.00 | 9906 | 3 | CNTNAP5 | 1.00 |
| 9811 | 3 | CHRFAM7A | 1.00 | 9907 | 3 | COL10A1 | 1.00 |
| 9812 | 3 | CHRM2 | 1.00 | 9908 | 3 | COL11A1 | 1.00 |
| 9813 | 3 | CHRM3 | 1.00 | 9909 | 3 | COL11A2 | 1.00 |
| 9814 | 3 | CHRM5 | 1.00 | 9910 | 3 | COL18A1-AS1 | 1.00 |
| 9815 | 3 | CHRNA1 | 1.00 | 9911 | 3 | COL19A1 | 1.00 |
| 9816 | 3 | CHRNA2 | 1.00 | 9912 | 3 | COL20A1 | 1.00 |
| 9817 | 3 | CHRNA3 | 1.00 | 9913 | 3 | COL22A1 | 1.00 |
| 9818 | 3 | CHRNA4 | 1.00 | 9914 | 3 | COL24A1 | 1.00 |
| 9819 | 3 | CHRNA5 | 1.00 | 9915 | 3 | COL25A1 | 1.00 |
| 9820 | 3 | CHRNA6 | 1.00 | 9916 | 3 | COL2A1 | 1.00 |
| 9821 | 3 | CHRNA7 | 1.00 | 9917 | 3 | COL4A3 | 1.00 |
| 9822 | 3 | CHRNA9 | 1.00 | 9918 | 3 | COL4A4 | 1.00 |
| 9823 | 3 | CHRNB2 | 1.00 | 9919 | 3 | COL6A4P1 | 1.00 |
| 9824 | 3 | CHRNB3 | 1.00 | 9920 | 3 | COL6A4P2 | 1.00 |
| 9825 | 3 | CHRNB4 | 1.00 | 9921 | 3 | COL9A1 | 1.00 |
| 9826 | 3 | CHRND | 1.00 | 9922 | 3 | COLEC10 | 1.00 |
| 9827 | 3 | CHRNG | 1.00 | 9923 | 3 | COLEC11 | 1.00 |
| 9828 | 3 | CHST13 | 1.00 | 9924 | 3 | CORO7-PAM16 | 1.00 |
| 9829 | 3 | CHST4 | 1.00 | 9925 | 3 | CORT | 1.00 |
| 9830 | 3 | CHST5 | 1.00 | 9926 | 3 | COX6A2 | 1.00 |
| 9831 | 3 | CHST6 | 1.00 | 9927 | 3 | COX7B2 | 1.00 |
| 9832 | 3 | CHST8 | 1.00 | 9928 | 3 | COX8C | 1.00 |
| 9833 | 3 | CHST9 | 1.00 | 9929 | 3 | CPA1 | 1.00 |
| 9834 | 3 | CHST9-AS1 | 1.00 | 9930 | 3 | CPA2 | 1.00 |
| 9835 | 3 | CHURC1-FNTB | 1.00 | 9931 | 3 | CPA5 | 1.00 |
| 9836 | 3 | CIB3 | 1.00 | 9932 | 3 | CPA6 | 1.00 |
| 9837 | 3 | CIB4 | 1.00 | 9933 | 3 | CPAMD8 | 1.00 |
| 9838 | 3 | CITED1 | 1.00 | 9934 | 3 | CPB1 | 1.00 |
| 9839 | 3 | CKAP2L | 1.00 | 9935 | 3 | CPB2 | 1.00 |
| 9840 | 3 | CKM | 1.00 | 9936 | 3 | CPLX2 | 1.00 |
| 9841 | 3 | CLC | 1.00 | 9937 | 3 | CPLX3 | 1.00 |
| 9842 | 3 | CLCA1 | 1.00 | 9938 | 3 | CPLX4 | 1.00 |
| 9843 | 3 | CLCA3P | 1.00 | 9939 | 3 | CPN1 | 1.00 |
| 9844 | 3 | CLCN1 | 1.00 | 9940 | 3 | CPN2 | 1.00 |
| 9845 | 3 | CLCNKA | 1.00 | 9941 | 3 | CPNE4 | 1.00 |
| 9846 | 3 | CLCNKB | 1.00 | 9942 | 3 | CPNE6 | 1.00 |
| 9847 | 3 | CLDN14 | 1.00 | 9943 | 3 | CPNE7 | 1.00 |
| 9848 | 3 | CLDN17 | 1.00 | 9944 | 3 | CPNE9 | 1.00 |
| 9849 | 3 | CLDN18 | 1.00 | 9945 | 3 | CPO | 1.00 |
| 9850 | 3 | CLDN2 | 1.00 | 9946 | 3 | CPS1-IT1 | 1.00 |
| 9851 | 3 | CLDN20 | 1.00 | 9947 | 3 | CPSF4L | 1.00 |
| 9852 | 3 | CLDN22 | 1.00 | 9948 | 3 | CPXCR1 | 1.00 |
| 9853 | 3 | CLDN24 | 1.00 | 9949 | 3 | CR1 | 1.00 |
| 9854 | 3 | CLDN25 | 1.00 | 9950 | 3 | CR1L | 1.00 |
| 9855 | 3 | CLDN6 | 1.00 | 9951 | 3 | CR2 | 1.00 |
| 9856 | 3 | CLDN9 | 1.00 | 9952 | 3 | CRB1 | 1.00 |
| 9857 | 3 | CLDND2 | 1.00 | 9953 | 3 | CREB3L3 | 1.00 |
| 9858 | 3 | CLEC17A | 1.00 | 9954 | 3 | CREG2 | 1.00 |
| 9859 | 3 | CLEC18B | 1.00 | 9955 | 3 | CRH | 1.00 |
| 9860 | 3 | CLEC18C | 1.00 | 9956 | 3 | CRHBP | 1.00 |
| 9861 | 3 | CLEC19A | 1.00 | 9957 | 3 | CRISP1 | 1.00 |
| 9862 | 3 | CLEC1B | 1.00 | 9958 | 3 | CRISP2 | 1.00 |
| 9863 | 3 | CLEC2L | 1.00 | 9959 | 3 | CRLF2 | 1.00 |
| 9864 | 3 | CLEC3A | 1.00 | 9960 | 3 | CRP | 1.00 |
| 9865 | 3 | CLEC4C | 1.00 | 9961 | 3 | CRTAM | 1.00 |
| 9866 | 3 | CLEC4D | 1.00 | 9962 | 3 | CRX | 1.00 |
| 9867 | 3 | CLEC4E | 1.00 | 9963 | 3 | CRYAA | 1.00 |
| 9868 | 3 | CLEC4M | 1.00 | 9964 | 3 | CRYBA1 | 1.00 |
| 9869 | 3 | CLEC6A | 1.00 | 9965 | 3 | CRYBA2 | 1.00 |
| 9870 | 3 | CLECL1 | 1.00 | 9966 | 3 | CRYBA4 | 1.00 |
| 9871 | 3 | CLGN | 1.00 | 9967 | 3 | CRYBB1 | 1.00 |
| 9872 | 3 | CLLU1 | 1.00 | 9968 | 3 | CRYBB2 | 1.00 |
| 9873 | 3 | CLLU1OS | 1.00 | 9969 | 3 | CRYBB3 | 1.00 |
| 9874 | 3 | CLNK | 1.00 | 9970 | 3 | CRYGA | 1.00 |
| 9875 | 3 | CLPS | 1.00 | 9971 | 3 | CRYGB | 1.00 |
| 9876 | 3 | CLPSL1 | 1.00 | 9972 | 3 | CRYGC | 1.00 |
| 9877 | 3 | CLPSL2 | 1.00 | 9973 | 3 | CRYGD | 1.00 |
| 9878 | 3 | CLRN1 | 1.00 | 9974 | 3 | CRYGN | 1.00 |
| 9879 | 3 | CLRN1-AS1 | 1.00 | 9975 | 3 | CRYM | 1.00 |
| 9880 | 3 | CLRN2 | 1.00 | 9976 | 3 | CRYM-AS1 | 1.00 |
| 9881 | 3 | CLRN3 | 1.00 | 9977 | 3 | CSAG1 | 1.00 |
| 9882 | 3 | CLSPN | 1.00 | 9978 | 3 | CSAG2 | 1.00 |
| 9883 | 3 | CLUL1 | 1.00 | 9979 | 3 | CSF2 | 1.00 |
| 9884 | 3 | CLVS1 | 1.00 | 9980 | 3 | CSH1 | 1.00 |

Fig. 38 - 53

| | | | | | | | | | | | | | | | | |
|---|---|---|---|---|---|---|---|---|---|---|---|---|---|---|---|---|
| 9981 | 3 | | | | | | CSH2 | 1.00 | 10077 | 3 | | | | | CYP1A2 | 1.00 |
| 9982 | 3 | | | | | | CSHL1 | 1.00 | 10078 | 3 | | | | | CYP1B1-AS1 | 1.00 |
| 9983 | 3 | | | | | | CSMD1 | 1.00 | 10079 | 3 | | | | | CYP24A1 | 1.00 |
| 9984 | 3 | | | | | | CSMD2 | 1.00 | 10080 | 3 | | | | | CYP26A1 | 1.00 |
| 9985 | 3 | | | | | | CSMD3 | 1.00 | 10081 | 3 | | | | | CYP26C1 | 1.00 |
| 9986 | 3 | | | | | | CSN1S1 | 1.00 | 10082 | 3 | | | | | CYP27B1 | 1.00 |
| 9987 | 3 | | | | | | CSN1S2AP | 1.00 | 10083 | 3 | | | | | CYP2A13 | 1.00 |
| 9988 | 3 | | | | | | CSN1S2BP | 1.00 | 10084 | 3 | | | | | CYP2A6 | 1.00 |
| 9989 | 3 | | | | | | CSN2 | 1.00 | 10085 | 3 | | | | | CYP2A7 | 1.00 |
| 9990 | 3 | | | | | | CSN3 | 1.00 | 10086 | 3 | | | | | CYP2B7P1 | 1.00 |
| 9991 | 3 | | | | | | CSNK1G2-AS1 | 1.00 | 10087 | 3 | | | | | CYP2C19 | 1.00 |
| 9992 | 3 | | | | | | CSPG4P1Y | 1.00 | 10088 | 3 | | | | | CYP2C8 | 1.00 |
| 9993 | 3 | | | | | | CSRNP3 | 1.00 | 10089 | 3 | | | | | CYP2F1 | 1.00 |
| 9994 | 3 | | | | | | CSRP3 | 1.00 | 10090 | 3 | | | | | CYP2G1P | 1.00 |
| 9995 | 3 | | | | | | CST1 | 1.00 | 10091 | 3 | | | | | CYP3A43 | 1.00 |
| 9996 | 3 | | | | | | CST11 | 1.00 | 10092 | 3 | | | | | CYP3A7 | 1.00 |
| 9997 | 3 | | | | | | CST2 | 1.00 | 10093 | 3 | | | | | CYP3A7-CYP3AP1 | 1.00 |
| 9998 | 3 | | | | | | CST4 | 1.00 | 10094 | 3 | | | | | CYP46A1 | 1.00 |
| 9999 | 3 | | | | | | CST5 | 1.00 | 10095 | 3 | | | | | CYP4A11 | 1.00 |
| 10000 | 3 | | | | | | CST8 | 1.00 | 10096 | 3 | | | | | CYP4A22 | 1.00 |
| 10001 | 3 | | | | | | CST9 | 1.00 | 10097 | 3 | | | | | CYP4F11 | 1.00 |
| 10002 | 3 | | | | | | CST9L | 1.00 | 10098 | 3 | | | | | CYP4F30P | 1.00 |
| 10003 | 3 | | | | | | CSTL1 | 1.00 | 10099 | 3 | | | | | CYP4F35P | 1.00 |
| 10004 | 3 | | | | | | CSTT | 1.00 | 10100 | 3 | | | | | CYP4Z1 | 1.00 |
| 10005 | 3 | | | | | | CT45A1 | 1.00 | 10101 | 3 | | | | | CYP4Z2P | 1.00 |
| 10006 | 3 | | | | | | CT45A2 | 1.00 | 10102 | 3 | | | | | CYP7A1 | 1.00 |
| 10007 | 3 | | | | | | CT45A3 | 1.00 | 10103 | 3 | | | | | CYP7B1 | 1.00 |
| 10008 | 3 | | | | | | CT45A4 | 1.00 | 10104 | 3 | | | | | CYP8B1 | 1.00 |
| 10009 | 3 | | | | | | CT45A5 | 1.00 | 10105 | 3 | | | | | CYSLTR2 | 1.00 |
| 10010 | 3 | | | | | | CT45A6 | 1.00 | 10106 | 3 | | | | | D21S2088E | 1.00 |
| 10011 | 3 | | | | | | CT47A1 | 1.00 | 10107 | 3 | | | | | DAB1 | 1.00 |
| 10012 | 3 | | | | | | CT47A10 | 1.00 | 10108 | 3 | | | | | DACH2 | 1.00 |
| 10013 | 3 | | | | | | CT47A11 | 1.00 | 10109 | 3 | | | | | DAND5 | 1.00 |
| 10014 | 3 | | | | | | CT47A4 | 1.00 | 10110 | 3 | | | | | DAO | 1.00 |
| 10015 | 3 | | | | | | CT47A5 | 1.00 | 10111 | 3 | | | | | DAOA | 1.00 |
| 10016 | 3 | | | | | | CT47A6 | 1.00 | 10112 | 3 | | | | | DAOA-AS1 | 1.00 |
| 10017 | 3 | | | | | | CT47A7 | 1.00 | 10113 | 3 | | | | | DAZ1 | 1.00 |
| 10018 | 3 | | | | | | CT47A8 | 1.00 | 10114 | 3 | | | | | DAZ2 | 1.00 |
| 10019 | 3 | | | | | | CT47B1 | 1.00 | 10115 | 3 | | | | | DAZ3 | 1.00 |
| 10020 | 3 | | | | | | CT62 | 1.00 | 10116 | 3 | | | | | DAZ4 | 1.00 |
| 10021 | 3 | | | | | | CTAG1A | 1.00 | 10117 | 3 | | | | | DAZL | 1.00 |
| 10022 | 3 | | | | | | CTAG1B | 1.00 | 10118 | 3 | | | | | DBC1 | 1.00 |
| 10023 | 3 | | | | | | CTAG2 | 1.00 | 10119 | 3 | | | | | DBH | 1.00 |
| 10024 | 3 | | | | | | CTAGE10P | 1.00 | 10120 | 3 | | | | | DBHLSP2 | 1.00 |
| 10025 | 3 | | | | | | CTAGE11P | 1.00 | 10121 | 3 | | | | | DBX1 | 1.00 |
| 10026 | 3 | | | | | | CTCFL | 1.00 | 10122 | 3 | | | | | DBX2 | 1.00 |
| 10027 | 3 | | | | | | CTH | 1.00 | 10123 | 3 | | | | | DCAF12L1 | 1.00 |
| 10028 | 3 | | | | | | CTNNA2 | 1.00 | 10124 | 3 | | | | | DCAF12L2 | 1.00 |
| 10029 | 3 | | | | | | CTNNA3 | 1.00 | 10125 | 3 | | | | | DCAF4L1 | 1.00 |
| 10030 | 3 | | | | | | CTRB1 | 1.00 | 10126 | 3 | | | | | DCAF4L2 | 1.00 |
| 10031 | 3 | | | | | | CTRB2 | 1.00 | 10127 | 3 | | | | | DCAF8L1 | 1.00 |
| 10032 | 3 | | | | | | CTRC | 1.00 | 10128 | 3 | | | | | DCAF8L2 | 1.00 |
| 10033 | 3 | | | | | | CTSE | 1.00 | 10129 | 3 | | | | | DCC | 1.00 |
| 10034 | 3 | | | | | | CTSL1P2 | 1.00 | 10130 | 3 | | | | | DCDC1 | 1.00 |
| 10035 | 3 | | | | | | CTSL1P8 | 1.00 | 10131 | 3 | | | | | DCDC2 | 1.00 |
| 10036 | 3 | | | | | | CTSL3 | 1.00 | 10132 | 3 | | | | | DCDC2B | 1.00 |
| 10037 | 3 | | | | | | CTXN2 | 1.00 | 10133 | 3 | | | | | DCDC5 | 1.00 |
| 10038 | 3 | | | | | | CTXN3 | 1.00 | 10134 | 3 | | | | | DCHS2 | 1.00 |
| 10039 | 3 | | | | | | CU8N | 1.00 | 10135 | 3 | | | | | DCLK3 | 1.00 |
| 10040 | 3 | | | | | | CUZD1 | 1.00 | 10136 | 3 | | | | | DCST1 | 1.00 |
| 10041 | 3 | | | | | | CXCL11 | 1.00 | 10137 | 3 | | | | | DCX | 1.00 |
| 10042 | 3 | | | | | | CXCL13 | 1.00 | 10138 | 3 | | | | | DDC | 1.00 |
| 10043 | 3 | | | | | | CXCL17 | 1.00 | 10139 | 3 | | | | | DDI1 | 1.00 |
| 10044 | 3 | | | | | | CXCL5 | 1.00 | 10140 | 3 | | | | | DDI2 | 1.00 |
| 10045 | 3 | | | | | | CXCL6 | 1.00 | 10141 | 3 | | | | | DDN | 1.00 |
| 10046 | 3 | | | | | | CXCR2P1 | 1.00 | 10142 | 3 | | | | | DDX11L1 | 1.00 |
| 10047 | 3 | | | | | | CXCR5 | 1.00 | 10143 | 3 | | | | | DDX11L10 | 1.00 |
| 10048 | 3 | | | | | | CXorf1 | 1.00 | 10144 | 3 | | | | | DDX11L9 | 1.00 |
| 10049 | 3 | | | | | | CXorf22 | 1.00 | 10145 | 3 | | | | | DDX2S | 1.00 |
| 10050 | 3 | | | | | | CXorf27 | 1.00 | 10146 | 3 | | | | | DDX3Y | 1.00 |
| 10051 | 3 | | | | | | CXorf28 | 1.00 | 10147 | 3 | | | | | DDX4 | 1.00 |
| 10052 | 3 | | | | | | CXorf30 | 1.00 | 10148 | 3 | | | | | DDX43 | 1.00 |
| 10053 | 3 | | | | | | CXorf31 | 1.00 | 10149 | 3 | | | | | DDX53 | 1.00 |
| 10054 | 3 | | | | | | CXorf41 | 1.00 | 10150 | 3 | | | | | DEC1 | 1.00 |
| 10055 | 3 | | | | | | CXorf48 | 1.00 | 10151 | 3 | | | | | DEFA1 | 1.00 |
| 10056 | 3 | | | | | | CXorf49B | 1.00 | 10152 | 3 | | | | | DEFA10P | 1.00 |
| 10057 | 3 | | | | | | CXorf51A | 1.00 | 10153 | 3 | | | | | DEFA1B | 1.00 |
| 10058 | 3 | | | | | | CXorf58 | 1.00 | 10154 | 3 | | | | | DEFA3 | 1.00 |
| 10059 | 3 | | | | | | CXorf59 | 1.00 | 10155 | 3 | | | | | DEFA4 | 1.00 |
| 10060 | 3 | | | | | | CXorf61 | 1.00 | 10156 | 3 | | | | | DEFA5 | 1.00 |
| 10061 | 3 | | | | | | CXorf64 | 1.00 | 10157 | 3 | | | | | DEFB103A | 1.00 |
| 10062 | 3 | | | | | | CXorf66 | 1.00 | 10158 | 3 | | | | | DEFB104B | 1.00 |
| 10063 | 3 | | | | | | CXorf68 | 1.00 | 10159 | 3 | | | | | DEFB105B | 1.00 |
| 10064 | 3 | | | | | | CXXC11 | 1.00 | 10160 | 3 | | | | | DEFB106B | 1.00 |
| 10065 | 3 | | | | | | CXXC1P1 | 1.00 | 10161 | 3 | | | | | DEFB107A | 1.00 |
| 10066 | 3 | | | | | | CXXC4 | 1.00 | 10162 | 3 | | | | | DEFB107B | 1.00 |
| 10067 | 3 | | | | | | CYCSP52 | 1.00 | 10163 | 3 | | | | | DEFB108B | 1.00 |
| 10068 | 3 | | | | | | CYLC1 | 1.00 | 10164 | 3 | | | | | DEFB109P1B | 1.00 |
| 10069 | 3 | | | | | | CYLC2 | 1.00 | 10165 | 3 | | | | | DEFB110 | 1.00 |
| 10070 | 3 | | | | | | CYMP | 1.00 | 10166 | 3 | | | | | DEFB112 | 1.00 |
| 10071 | 3 | | | | | | CYP11A1 | 1.00 | 10167 | 3 | | | | | DEFB113 | 1.00 |
| 10072 | 3 | | | | | | CYP11B1 | 1.00 | 10168 | 3 | | | | | DEFB114 | 1.00 |
| 10073 | 3 | | | | | | CYP11B2 | 1.00 | 10169 | 3 | | | | | DEFB115 | 1.00 |
| 10074 | 3 | | | | | | CYP17A1 | 1.00 | 10170 | 3 | | | | | DEFB116 | 1.00 |
| 10075 | 3 | | | | | | CYP19A1 | 1.00 | 10171 | 3 | | | | | DEFB118 | 1.00 |
| 10076 | 3 | | | | | | CYP1A1 | 1.00 | 10172 | 3 | | | | | DEFB119 | 1.00 |

Fig. 38 - 54

| | | | | | | | | | | | | | | | |
|---|---|---|---|---|---|---|---|---|---|---|---|---|---|---|---|
| 10173 | 3 | | | | | DEFB121 | 1.00 | 10269 | 3 | | | | | DNAJC27-AS1 | 1.00 |
| 10174 | 3 | | | | | DEFB122 | 1.00 | 10270 | 3 | | | | | DNAJC5B | 1.00 |
| 10175 | 3 | | | | | DEFB123 | 1.00 | 10271 | 3 | | | | | DNAJC5G | 1.00 |
| 10176 | 3 | | | | | DEFB125 | 1.00 | 10272 | 3 | | | | | DNAJC6 | 1.00 |
| 10177 | 3 | | | | | DEFB126 | 1.00 | 10273 | 3 | | | | | DNASE2B | 1.00 |
| 10178 | 3 | | | | | DEFB127 | 1.00 | 10274 | 3 | | | | | DNM1P35 | 1.00 |
| 10179 | 3 | | | | | DEFB128 | 1.00 | 10275 | 3 | | | | | DNM1P41 | 1.00 |
| 10180 | 3 | | | | | DEFB129 | 1.00 | 10276 | 3 | | | | | DNM1P46 | 1.00 |
| 10181 | 3 | | | | | DEFB130 | 1.00 | 10277 | 3 | | | | | DNM3 | 1.00 |
| 10182 | 3 | | | | | DEFB131 | 1.00 | 10278 | 3 | | | | | DNMBP-AS1 | 1.00 |
| 10183 | 3 | | | | | DEFB132 | 1.00 | 10279 | 3 | | | | | DNMT3L | 1.00 |
| 10184 | 3 | | | | | DEFB133 | 1.00 | 10280 | 3 | | | | | DNTT | 1.00 |
| 10185 | 3 | | | | | DEFB134 | 1.00 | 10281 | 3 | | | | | DOC2A | 1.00 |
| 10186 | 3 | | | | | DEFB135 | 1.00 | 10282 | 3 | | | | | DOC2GP | 1.00 |
| 10187 | 3 | | | | | DEFB136 | 1.00 | 10283 | 3 | | | | | DOK5 | 1.00 |
| 10188 | 3 | | | | | DEFB4A | 1.00 | 10284 | 3 | | | | | DOK6 | 1.00 |
| 10189 | 3 | | | | | DEFB4B | 1.00 | 10285 | 3 | | | | | DPCR1 | 1.00 |
| 10190 | 3 | | | | | DEFT1P | 1.00 | 10286 | 3 | | | | | DPEP1 | 1.00 |
| 10191 | 3 | | | | | DEPDC1B | 1.00 | 10287 | 3 | | | | | DPEP3 | 1.00 |
| 10192 | 3 | | | | | DEPDC4 | 1.00 | 10288 | 3 | | | | | DPF1 | 1.00 |
| 10193 | 3 | | | | | DERL3 | 1.00 | 10289 | 3 | | | | | DPF3 | 1.00 |
| 10194 | 3 | | | | | DGCR10 | 1.00 | 10290 | 3 | | | | | DPP10 | 1.00 |
| 10195 | 3 | | | | | DGCR9 | 1.00 | 10291 | 3 | | | | | DPPA2 | 1.00 |
| 10196 | 3 | | | | | DGKB | 1.00 | 10292 | 3 | | | | | DPPA3 | 1.00 |
| 10197 | 3 | | | | | DGKH | 1.00 | 10293 | 3 | | | | | DPPA4 | 1.00 |
| 10198 | 3 | | | | | DGKI | 1.00 | 10294 | 3 | | | | | DPPA5 | 1.00 |
| 10199 | 3 | | | | | DGKK | 1.00 | 10295 | 3 | | | | | DPRX | 1.00 |
| 10200 | 3 | | | | | DHDH | 1.00 | 10296 | 3 | | | | | DPY19L1P1 | 1.00 |
| 10201 | 3 | | | | | DHRS7C | 1.00 | 10297 | 3 | | | | | DPY19L2P1 | 1.00 |
| 10202 | 3 | | | | | DIAPH3 | 1.00 | 10298 | 3 | | | | | DPY19L2P2 | 1.00 |
| 10203 | 3 | | | | | DIO1 | 1.00 | 10299 | 3 | | | | | DPY19L2P3 | 1.00 |
| 10204 | 3 | | | | | DIRAS2 | 1.00 | 10300 | 3 | | | | | DPY19L2P4 | 1.00 |
| 10205 | 3 | | | | | DIRC1 | 1.00 | 10301 | 3 | | | | | DPYS | 1.00 |
| 10206 | 3 | | | | | DIRC3 | 1.00 | 10302 | 3 | | | | | DPYSL4 | 1.00 |
| 10207 | 3 | | | | | DISC2 | 1.00 | 10303 | 3 | | | | | DPYSL5 | 1.00 |
| 10208 | 3 | | | | | DISP2 | 1.00 | 10304 | 3 | | | | | DRD1 | 1.00 |
| 10209 | 3 | | | | | DKFZP434A062 | 1.00 | 10305 | 3 | | | | | DRD2 | 1.00 |
| 10210 | 3 | | | | | DKFZP434H168 | 1.00 | 10306 | 3 | | | | | DRD3 | 1.00 |
| 10211 | 3 | | | | | DKFZP434K028 | 1.00 | 10307 | 3 | | | | | DRD5 | 1.00 |
| 10212 | 3 | | | | | DKFZP434L187 | 1.00 | 10308 | 3 | | | | | DRGX | 1.00 |
| 10213 | 3 | | | | | DKFZp434L192 | 1.00 | 10309 | 3 | | | | | DRP2 | 1.00 |
| 10214 | 3 | | | | | DKFZp451B082 | 1.00 | 10310 | 3 | | | | | DSCAM | 1.00 |
| 10215 | 3 | | | | | DKFZP564C196 | 1.00 | 10311 | 3 | | | | | DSCAM-AS1 | 1.00 |
| 10216 | 3 | | | | | DKFZp566F0947 | 1.00 | 10312 | 3 | | | | | DSCAML1 | 1.00 |
| 10217 | 3 | | | | | DKFZp686D0853 | 1.00 | 10313 | 3 | | | | | DSCR10 | 1.00 |
| 10218 | 3 | | | | | DKFZp686K1684 | 1.00 | 10314 | 3 | | | | | DSCR4 | 1.00 |
| 10219 | 3 | | | | | DKFZp686O1327 | 1.00 | 10315 | 3 | | | | | DSCR6 | 1.00 |
| 10220 | 3 | | | | | DKFZp779M0652 | 1.00 | 10316 | 3 | | | | | DSCR8 | 1.00 |
| 10221 | 3 | | | | | DKK4 | 1.00 | 10317 | 3 | | | | | DSCR9 | 1.00 |
| 10222 | 3 | | | | | DKKL1 | 1.00 | 10318 | 3 | | | | | DSG4 | 1.00 |
| 10223 | 3 | | | | | DLEC1 | 1.00 | 10319 | 3 | | | | | DSPP | 1.00 |
| 10224 | 3 | | | | | DLEU2 | 1.00 | 10320 | 3 | | | | | DTHD1 | 1.00 |
| 10225 | 3 | | | | | DLEU2L | 1.00 | 10321 | 3 | | | | | DUPD1 | 1.00 |
| 10226 | 3 | | | | | DLEU7 | 1.00 | 10322 | 3 | | | | | DUSP13 | 1.00 |
| 10227 | 3 | | | | | DLGAP1 | 1.00 | 10323 | 3 | | | | | DUSP21 | 1.00 |
| 10228 | 3 | | | | | DLGAP2 | 1.00 | 10324 | 3 | | | | | DUSP26 | 1.00 |
| 10229 | 3 | | | | | DLGAP3 | 1.00 | 10325 | 3 | | | | | DUSP27 | 1.00 |
| 10230 | 3 | | | | | DLGAP5 | 1.00 | 10326 | 3 | | | | | DUSP9 | 1.00 |
| 10231 | 3 | | | | | DLL3 | 1.00 | 10327 | 3 | | | | | DUX2 | 1.00 |
| 10232 | 3 | | | | | DLX1 | 1.00 | 10328 | 3 | | | | | DUX4 | 1.00 |
| 10233 | 3 | | | | | DLX2 | 1.00 | 10329 | 3 | | | | | DUX4L2 | 1.00 |
| 10234 | 3 | | | | | DLX6-AS1 | 1.00 | 10330 | 3 | | | | | DUX4L3 | 1.00 |
| 10235 | 3 | | | | | DMBT1 | 1.00 | 10331 | 3 | | | | | DUX4L4 | 1.00 |
| 10236 | 3 | | | | | DMC1 | 1.00 | 10332 | 3 | | | | | DUX4L5 | 1.00 |
| 10237 | 3 | | | | | DMGDH | 1.00 | 10333 | 3 | | | | | DUX4L6 | 1.00 |
| 10238 | 3 | | | | | DMP1 | 1.00 | 10334 | 3 | | | | | DUXA | 1.00 |
| 10239 | 3 | | | | | DMRT1 | 1.00 | 10335 | 3 | | | | | DYDC1 | 1.00 |
| 10240 | 3 | | | | | DMRTA1 | 1.00 | 10336 | 3 | | | | | DYDC2 | 1.00 |
| 10241 | 3 | | | | | DMRTA2 | 1.00 | 10337 | 3 | | | | | DYNC2H1 | 1.00 |
| 10242 | 3 | | | | | DMRTB1 | 1.00 | 10338 | 3 | | | | | DYNLRB2 | 1.00 |
| 10243 | 3 | | | | | DMRTC1B | 1.00 | 10339 | 3 | | | | | DYTN | 1.00 |
| 10244 | 3 | | | | | DMRTC2 | 1.00 | 10340 | 3 | | | | | DYX1C1-CCPG1 | 1.00 |
| 10245 | 3 | | | | | DNA2 | 1.00 | 10341 | 3 | | | | | DZANK1-AS1 | 1.00 |
| 10246 | 3 | | | | | DNAAF1 | 1.00 | 10342 | 3 | | | | | E2F7 | 1.00 |
| 10247 | 3 | | | | | DNAH10 | 1.00 | 10343 | 3 | | | | | EBLN1 | 1.00 |
| 10248 | 3 | | | | | DNAH11 | 1.00 | 10344 | 3 | | | | | ECEL1 | 1.00 |
| 10249 | 3 | | | | | DNAH12 | 1.00 | 10345 | 3 | | | | | ECEL1P2 | 1.00 |
| 10250 | 3 | | | | | DNAH14 | 1.00 | 10346 | 3 | | | | | ECRP | 1.00 |
| 10251 | 3 | | | | | DNAH2 | 1.00 | 10347 | 3 | | | | | ECT2L | 1.00 |
| 10252 | 3 | | | | | DNAH3 | 1.00 | 10348 | 3 | | | | | EDDM3A | 1.00 |
| 10253 | 3 | | | | | DNAH5 | 1.00 | 10349 | 3 | | | | | EDDM3B | 1.00 |
| 10254 | 3 | | | | | DNAH6 | 1.00 | 10350 | 3 | | | | | EEF1DP3 | 1.00 |
| 10255 | 3 | | | | | DNAH7 | 1.00 | 10351 | 3 | | | | | EEF1E1-MUTED | 1.00 |
| 10256 | 3 | | | | | DNAH8 | 1.00 | 10352 | 3 | | | | | EFCAB10 | 1.00 |
| 10257 | 3 | | | | | DNAH9 | 1.00 | 10353 | 3 | | | | | EFCAB3 | 1.00 |
| 10258 | 3 | | | | | DNAI1 | 1.00 | 10354 | 3 | | | | | EFCAB5 | 1.00 |
| 10259 | 3 | | | | | DNAI2 | 1.00 | 10355 | 3 | | | | | EFCAB6 | 1.00 |
| 10260 | 3 | | | | | DNAJA1P5 | 1.00 | 10356 | 3 | | | | | EFCAB9 | 1.00 |
| 10261 | 3 | | | | | DNAJB13 | 1.00 | 10357 | 3 | | | | | EFHB | 1.00 |
| 10262 | 3 | | | | | DNAJB3 | 1.00 | 10358 | 3 | | | | | EFNA2 | 1.00 |
| 10263 | 3 | | | | | DNAJB7 | 1.00 | 10359 | 3 | | | | | EGF | 1.00 |
| 10264 | 3 | | | | | DNAJB8 | 1.00 | 10360 | 3 | | | | | EGFEM1P | 1.00 |
| 10265 | 3 | | | | | DNAJB8-AS1 | 1.00 | 10361 | 3 | | | | | EGFLAM-AS4 | 1.00 |
| 10266 | 3 | | | | | DNAJC12 | 1.00 | 10362 | 3 | | | | | EGOT | 1.00 |
| 10267 | 3 | | | | | DNAJC22 | 1.00 | 10363 | 3 | | | | | EGR4 | 1.00 |
| 10268 | 3 | | | | | DNAJC25-GNG10 | 1.00 | 10364 | 3 | | | | | EIF1AY | 1.00 |

Fig. 38 - 55

| | | | | | | | | | | | | | | |
|---|---|---|---|---|---|---|---|---|---|---|---|---|---|---|
| 10365 | 3 | | | | | EIF2C3 | 1.00 | 10461 | 3 | | | | FAM154A | 1.00 |
| 10366 | 3 | | | | | EIF3CL | 1.00 | 10462 | 3 | | | | FAM154B | 1.00 |
| 10367 | 3 | | | | | EIF4E1B | 1.00 | 10463 | 3 | | | | FAM155A | 1.00 |
| 10368 | 3 | | | | | ELAVL2 | 1.00 | 10464 | 3 | | | | FAM155B | 1.00 |
| 10369 | 3 | | | | | ELAVL3 | 1.00 | 10465 | 3 | | | | FAM157A | 1.00 |
| 10370 | 3 | | | | | ELAVL4 | 1.00 | 10466 | 3 | | | | FAM157B | 1.00 |
| 10371 | 3 | | | | | ELOVL2 | 1.00 | 10467 | 3 | | | | FAM159A | 1.00 |
| 10372 | 3 | | | | | ELSPBP1 | 1.00 | 10468 | 3 | | | | FAM159B | 1.00 |
| 10373 | 3 | | | | | EMBP1 | 1.00 | 10469 | 3 | | | | FAM163A | 1.00 |
| 10374 | 3 | | | | | EMID2 | 1.00 | 10470 | 3 | | | | FAM163B | 1.00 |
| 10375 | 3 | | | | | EML5 | 1.00 | 10471 | 3 | | | | FAM166A | 1.00 |
| 10376 | 3 | | | | | EMR1 | 1.00 | 10472 | 3 | | | | FAM169A | 1.00 |
| 10377 | 3 | | | | | EMR3 | 1.00 | 10473 | 3 | | | | FAM169B | 1.00 |
| 10378 | 3 | | | | | EMX1 | 1.00 | 10474 | 3 | | | | FAM170A | 1.00 |
| 10379 | 3 | | | | | EN2 | 1.00 | 10475 | 3 | | | | FAM170B | 1.00 |
| 10380 | 3 | | | | | ENAM | 1.00 | 10476 | 3 | | | | FAM172BP | 1.00 |
| 10381 | 3 | | | | | ENKUR | 1.00 | 10477 | 3 | | | | FAM177B | 1.00 |
| 10382 | 3 | | | | | ENO1-AS1 | 1.00 | 10478 | 3 | | | | FAM181A | 1.00 |
| 10383 | 3 | | | | | ENPP3 | 1.00 | 10479 | 3 | | | | FAM181A-AS1 | 1.00 |
| 10384 | 3 | | | | | ENPP6 | 1.00 | 10480 | 3 | | | | FAM183B | 1.00 |
| 10385 | 3 | | | | | ENPP7 | 1.00 | 10481 | 3 | | | | FAM184A | 1.00 |
| 10386 | 3 | | | | | ENTHD1 | 1.00 | 10482 | 3 | | | | FAM186A | 1.00 |
| 10387 | 3 | | | | | ENTPD3-AS1 | 1.00 | 10483 | 3 | | | | FAM186B | 1.00 |
| 10388 | 3 | | | | | ENTPD8 | 1.00 | 10484 | 3 | | | | FAM187B | 1.00 |
| 10389 | 3 | | | | | EOMES | 1.00 | 10485 | 3 | | | | FAM189A1 | 1.00 |
| 10390 | 3 | | | | | EPB42 | 1.00 | 10486 | 3 | | | | FAM188B-CDRT4 | 1.00 |
| 10391 | 3 | | | | | EPGN | 1.00 | 10487 | 3 | | | | FAM190A | 1.00 |
| 10392 | 3 | | | | | EPHA10 | 1.00 | 10488 | 3 | | | | FAM194A | 1.00 |
| 10393 | 3 | | | | | EPHA5 | 1.00 | 10489 | 3 | | | | FAM194B | 1.00 |
| 10394 | 3 | | | | | EPHA6 | 1.00 | 10490 | 3 | | | | FAM196A | 1.00 |
| 10395 | 3 | | | | | EPHA7 | 1.00 | 10491 | 3 | | | | FAM197Y2P | 1.00 |
| 10396 | 3 | | | | | EPHA8 | 1.00 | 10492 | 3 | | | | FAM197Y5 | 1.00 |
| 10397 | 3 | | | | | EPS8L3 | 1.00 | 10493 | 3 | | | | FAM19A1 | 1.00 |
| 10398 | 3 | | | | | EPX | 1.00 | 10494 | 3 | | | | FAM19A3 | 1.00 |
| 10399 | 3 | | | | | EPYC | 1.00 | 10495 | 3 | | | | FAM19A4 | 1.00 |
| 10400 | 3 | | | | | ERAS | 1.00 | 10496 | 3 | | | | FAM205A | 1.00 |
| 10401 | 3 | | | | | ERBB4 | 1.00 | 10497 | 3 | | | | FAM205B | 1.00 |
| 10402 | 3 | | | | | ERC2 | 1.00 | 10498 | 3 | | | | FAM215A | 1.00 |
| 10403 | 3 | | | | | ERCC6L | 1.00 | 10499 | 3 | | | | FAM216B | 1.00 |
| 10404 | 3 | | | | | ERMN | 1.00 | 10500 | 3 | | | | FAM217A | 1.00 |
| 10405 | 3 | | | | | ERN2 | 1.00 | 10501 | 3 | | | | FAM22F | 1.00 |
| 10406 | 3 | | | | | ERVFRD-1 | 1.00 | 10502 | 3 | | | | FAM24A | 1.00 |
| 10407 | 3 | | | | | ERVMER34-1 | 1.00 | 10503 | 3 | | | | FAM24B-CUZD1 | 1.00 |
| 10408 | 3 | | | | | ERVV-1 | 1.00 | 10504 | 3 | | | | FAM26D | 1.00 |
| 10409 | 3 | | | | | ERVV-2 | 1.00 | 10505 | 3 | | | | FAM27L | 1.00 |
| 10410 | 3 | | | | | ESCO2 | 1.00 | 10506 | 3 | | | | FAM3B | 1.00 |
| 10411 | 3 | | | | | ESM1 | 1.00 | 10507 | 3 | | | | FAM40B | 1.00 |
| 10412 | 3 | | | | | ESPNL | 1.00 | 10508 | 3 | | | | FAM41AY1 | 1.00 |
| 10413 | 3 | | | | | ESPNP | 1.00 | 10509 | 3 | | | | FAM41AY2 | 1.00 |
| 10414 | 3 | | | | | ESR2 | 1.00 | 10510 | 3 | | | | FAM43B | 1.00 |
| 10415 | 3 | | | | | ESRRB | 1.00 | 10511 | 3 | | | | FAM46D | 1.00 |
| 10416 | 3 | | | | | ESX1 | 1.00 | 10512 | 3 | | | | FAM47A | 1.00 |
| 10417 | 3 | | | | | ETV2 | 1.00 | 10513 | 3 | | | | FAM47B | 1.00 |
| 10418 | 3 | | | | | ETV3L | 1.00 | 10514 | 3 | | | | FAM47C | 1.00 |
| 10419 | 3 | | | | | EVX1 | 1.00 | 10515 | 3 | | | | FAM47E | 1.00 |
| 10420 | 3 | | | | | EVX2 | 1.00 | 10516 | 3 | | | | FAM47E-STBD1 | 1.00 |
| 10421 | 3 | | | | | EXD1 | 1.00 | 10517 | 3 | | | | FAM48B1 | 1.00 |
| 10422 | 3 | | | | | EXO1 | 1.00 | 10518 | 3 | | | | FAM48B2 | 1.00 |
| 10423 | 3 | | | | | EXOC3L1 | 1.00 | 10519 | 3 | | | | FAM55A | 1.00 |
| 10424 | 3 | | | | | EXOC3L4 | 1.00 | 10520 | 3 | | | | FAM55B | 1.00 |
| 10425 | 3 | | | | | EYA1 | 1.00 | 10521 | 3 | | | | FAM55D | 1.00 |
| 10426 | 3 | | | | | EYA4 | 1.00 | 10522 | 3 | | | | FAM57B | 1.00 |
| 10427 | 3 | | | | | EYS | 1.00 | 10523 | 3 | | | | FAM5B | 1.00 |
| 10428 | 3 | | | | | F11 | 1.00 | 10524 | 3 | | | | FAM5C | 1.00 |
| 10429 | 3 | | | | | F13B | 1.00 | 10525 | 3 | | | | FAM66A | 1.00 |
| 10430 | 3 | | | | | F2 | 1.00 | 10526 | 3 | | | | FAM66B | 1.00 |
| 10431 | 3 | | | | | F2RL3 | 1.00 | 10527 | 3 | | | | FAM66D | 1.00 |
| 10432 | 3 | | | | | F7 | 1.00 | 10528 | 3 | | | | FAM66E | 1.00 |
| 10433 | 3 | | | | | F8A2 | 1.00 | 10529 | 3 | | | | FAM71A | 1.00 |
| 10434 | 3 | | | | | F9 | 1.00 | 10530 | 3 | | | | FAM71B | 1.00 |
| 10435 | 3 | | | | | FABP1 | 1.00 | 10531 | 3 | | | | FAM71C | 1.00 |
| 10436 | 3 | | | | | FABP12 | 1.00 | 10532 | 3 | | | | FAM71D | 1.00 |
| 10437 | 3 | | | | | FABP2 | 1.00 | 10533 | 3 | | | | FAM71E2 | 1.00 |
| 10438 | 3 | | | | | FABP5P3 | 1.00 | 10534 | 3 | | | | FAM71F1 | 1.00 |
| 10439 | 3 | | | | | FABP6 | 1.00 | 10535 | 3 | | | | FAM74A1 | 1.00 |
| 10440 | 3 | | | | | FAM106A | 1.00 | 10536 | 3 | | | | FAM74A2 | 1.00 |
| 10441 | 3 | | | | | FAM106CP | 1.00 | 10537 | 3 | | | | FAM74A3 | 1.00 |
| 10442 | 3 | | | | | FAM123A | 1.00 | 10538 | 3 | | | | FAM74A4 | 1.00 |
| 10443 | 3 | | | | | FAM123C | 1.00 | 10539 | 3 | | | | FAM75A1 | 1.00 |
| 10444 | 3 | | | | | FAM129C | 1.00 | 10540 | 3 | | | | FAM75A2 | 1.00 |
| 10445 | 3 | | | | | FAM131B | 1.00 | 10541 | 3 | | | | FAM75A3 | 1.00 |
| 10446 | 3 | | | | | FAM131C | 1.00 | 10542 | 3 | | | | FAM75A4 | 1.00 |
| 10447 | 3 | | | | | FAM133A | 1.00 | 10543 | 3 | | | | FAM75A5 | 1.00 |
| 10448 | 3 | | | | | FAM135B | 1.00 | 10544 | 3 | | | | FAM75A6 | 1.00 |
| 10449 | 3 | | | | | FAM138A | 1.00 | 10545 | 3 | | | | FAM75A7 | 1.00 |
| 10450 | 3 | | | | | FAM138B | 1.00 | 10546 | 3 | | | | FAM75C1 | 1.00 |
| 10451 | 3 | | | | | FAM138C | 1.00 | 10547 | 3 | | | | FAM75C2 | 1.00 |
| 10452 | 3 | | | | | FAM138D | 1.00 | 10548 | 3 | | | | FAM75D1 | 1.00 |
| 10453 | 3 | | | | | FAM138E | 1.00 | 10549 | 3 | | | | FAM75D3 | 1.00 |
| 10454 | 3 | | | | | FAM138F | 1.00 | 10550 | 3 | | | | FAM75D4 | 1.00 |
| 10455 | 3 | | | | | FAM150A | 1.00 | 10551 | 3 | | | | FAM75D5 | 1.00 |
| 10456 | 3 | | | | | FAM151A | 1.00 | 10552 | 3 | | | | FAM81A | 1.00 |
| 10457 | 3 | | | | | FAM151B | 1.00 | 10553 | 3 | | | | FAM81B | 1.00 |
| 10458 | 3 | | | | | FAM153A | 1.00 | 10554 | 3 | | | | FAM90A1 | 1.00 |
| 10459 | 3 | | | | | FAM153B | 1.00 | 10555 | 3 | | | | FAM90A10 | 1.00 |
| 10460 | 3 | | | | | FAM153C | 1.00 | 10556 | 3 | | | | FAM90A10P | 1.00 |

Fig. 38 - 56

| | | | | | | | | | | | | | | | | | |
|---|---|---|---|---|---|---|---|---|---|---|---|---|---|---|---|---|---|
| 10557 | 3 | | | | | | FAM90A14 | 1.00 | 10653 | 3 | | | | | | FLJ22184 | 1.00 |
| 10558 | 3 | | | | | | FAM90A19 | 1.00 | 10654 | 3 | | | | | | FLJ22447 | 1.00 |
| 10559 | 3 | | | | | | FAM90A20 | 1.00 | 10655 | 3 | | | | | | FLJ22763 | 1.00 |
| 10560 | 3 | | | | | | FAM90A25P | 1.00 | 10656 | 3 | | | | | | FLJ23152 | 1.00 |
| 10561 | 3 | | | | | | FAM90A27P | 1.00 | 10657 | 3 | | | | | | FLJ25328 | 1.00 |
| 10562 | 3 | | | | | | FAM90A2P | 1.00 | 10658 | 3 | | | | | | FLJ25363 | 1.00 |
| 10563 | 3 | | | | | | FAM90A5 | 1.00 | 10659 | 3 | | | | | | FLJ25758 | 1.00 |
| 10564 | 3 | | | | | | FAM90A7 | 1.00 | 10660 | 3 | | | | | | FLJ26245 | 1.00 |
| 10565 | 3 | | | | | | FAM90A7P | 1.00 | 10661 | 3 | | | | | | FLJ26850 | 1.00 |
| 10566 | 3 | | | | | | FAM90A8 | 1.00 | 10662 | 3 | | | | | | FLJ30679 | 1.00 |
| 10567 | 3 | | | | | | FAM90A9 | 1.00 | 10663 | 3 | | | | | | FLJ30838 | 1.00 |
| 10568 | 3 | | | | | | FAM92A3 | 1.00 | 10664 | 3 | | | | | | FLJ31662 | 1.00 |
| 10569 | 3 | | | | | | FAM92B | 1.00 | 10665 | 3 | | | | | | FLJ31813 | 1.00 |
| 10570 | 3 | | | | | | FAM99A | 1.00 | 10666 | 3 | | | | | | FLJ32063 | 1.00 |
| 10571 | 3 | | | | | | FAM99B | 1.00 | 10667 | 3 | | | | | | FLJ33065 | 1.00 |
| 10572 | 3 | | | | | | FAM9A | 1.00 | 10668 | 3 | | | | | | FLJ33360 | 1.00 |
| 10573 | 3 | | | | | | FAM9B | 1.00 | 10669 | 3 | | | | | | FLJ33534 | 1.00 |
| 10574 | 3 | | | | | | FAM9C | 1.00 | 10670 | 3 | | | | | | FLJ33581 | 1.00 |
| 10575 | 3 | | | | | | FANCB | 1.00 | 10671 | 3 | | | | | | FLJ34208 | 1.00 |
| 10576 | 3 | | | | | | FANCM | 1.00 | 10672 | 3 | | | | | | FLJ34503 | 1.00 |
| 10577 | 3 | | | | | | FAS-AS1 | 1.00 | 10673 | 3 | | | | | | FLJ34690 | 1.00 |
| 10578 | 3 | | | | | | FAT3 | 1.00 | 10674 | 3 | | | | | | FLJ35024 | 1.00 |
| 10579 | 3 | | | | | | FATE1 | 1.00 | 10675 | 3 | | | | | | FLJ35282 | 1.00 |
| 10580 | 3 | | | | | | FAXC | 1.00 | 10676 | 3 | | | | | | FLJ35424 | 1.00 |
| 10581 | 3 | | | | | | FBN2 | 1.00 | 10677 | 3 | | | | | | FLJ35946 | 1.00 |
| 10582 | 3 | | | | | | FBN3 | 1.00 | 10678 | 3 | | | | | | FLJ36000 | 1.00 |
| 10583 | 3 | | | | | | FBP2 | 1.00 | 10679 | 3 | | | | | | FLJ36777 | 1.00 |
| 10584 | 3 | | | | | | FBXL13 | 1.00 | 10680 | 3 | | | | | | FLJ37035 | 1.00 |
| 10585 | 3 | | | | | | FBXL21 | 1.00 | 10681 | 3 | | | | | | FLJ37201 | 1.00 |
| 10586 | 3 | | | | | | FBXO15 | 1.00 | 10682 | 3 | | | | | | FLJ37505 | 1.00 |
| 10587 | 3 | | | | | | FBXO16 | 1.00 | 10683 | 3 | | | | | | FLJ38109 | 1.00 |
| 10588 | 3 | | | | | | FBXO24 | 1.00 | 10684 | 3 | | | | | | FLJ38576 | 1.00 |
| 10589 | 3 | | | | | | FBXO39 | 1.00 | 10685 | 3 | | | | | | FLJ39080 | 1.00 |
| 10590 | 3 | | | | | | FBXO40 | 1.00 | 10686 | 3 | | | | | | FLJ39534 | 1.00 |
| 10591 | 3 | | | | | | FBXO43 | 1.00 | 10687 | 3 | | | | | | FLJ40194 | 1.00 |
| 10592 | 3 | | | | | | FBXO47 | 1.00 | 10688 | 3 | | | | | | FLJ40288 | 1.00 |
| 10593 | 3 | | | | | | FBXO48 | 1.00 | 10689 | 3 | | | | | | FLJ40292 | 1.00 |
| 10594 | 3 | | | | | | FBXW10 | 1.00 | 10690 | 3 | | | | | | FLJ40434 | 1.00 |
| 10595 | 3 | | | | | | FBXW12 | 1.00 | 10691 | 3 | | | | | | FLJ41278 | 1.00 |
| 10596 | 3 | | | | | | FCAMR | 1.00 | 10692 | 3 | | | | | | FLJ41350 | 1.00 |
| 10597 | 3 | | | | | | FCGR1A | 1.00 | 10693 | 3 | | | | | | FLJ41649 | 1.00 |
| 10598 | 3 | | | | | | FCGR1B | 1.00 | 10694 | 3 | | | | | | FLJ41941 | 1.00 |
| 10599 | 3 | | | | | | FCGR1C | 1.00 | 10695 | 3 | | | | | | FLJ42102 | 1.00 |
| 10600 | 3 | | | | | | FCN2 | 1.00 | 10696 | 3 | | | | | | FLJ42280 | 1.00 |
| 10601 | 3 | | | | | | FCN3 | 1.00 | 10697 | 3 | | | | | | FLJ42289 | 1.00 |
| 10602 | 3 | | | | | | FCRL1 | 1.00 | 10698 | 3 | | | | | | FLJ42351 | 1.00 |
| 10603 | 3 | | | | | | FCRL2 | 1.00 | 10699 | 3 | | | | | | FLJ42969 | 1.00 |
| 10604 | 3 | | | | | | FCRL3 | 1.00 | 10700 | 3 | | | | | | FLJ43315 | 1.00 |
| 10605 | 3 | | | | | | FCRL4 | 1.00 | 10701 | 3 | | | | | | FLJ43390 | 1.00 |
| 10606 | 3 | | | | | | FCRL5 | 1.00 | 10702 | 3 | | | | | | FLJ43826 | 1.00 |
| 10607 | 3 | | | | | | FCRL6 | 1.00 | 10703 | 3 | | | | | | FLJ43860 | 1.00 |
| 10608 | 3 | | | | | | FCRL8 | 1.00 | 10704 | 3 | | | | | | FLJ43879 | 1.00 |
| 10609 | 3 | | | | | | FDCSP | 1.00 | 10705 | 3 | | | | | | FLJ44054 | 1.00 |
| 10610 | 3 | | | | | | FER | 1.00 | 10706 | 3 | | | | | | FLJ44511 | 1.00 |
| 10611 | 3 | | | | | | FER1L4 | 1.00 | 10707 | 3 | | | | | | FLJ45079 | 1.00 |
| 10612 | 3 | | | | | | FER1L5 | 1.00 | 10708 | 3 | | | | | | FLJ45974 | 1.00 |
| 10613 | 3 | | | | | | FER1L6 | 1.00 | 10709 | 3 | | | | | | FLJ46066 | 1.00 |
| 10614 | 3 | | | | | | FER1L6-AS1 | 1.00 | 10710 | 3 | | | | | | FLJ46257 | 1.00 |
| 10615 | 3 | | | | | | FERD3L | 1.00 | 10711 | 3 | | | | | | FLJ46284 | 1.00 |
| 10616 | 3 | | | | | | FEV | 1.00 | 10712 | 3 | | | | | | FLJ46300 | 1.00 |
| 10617 | 3 | | | | | | FEZF1 | 1.00 | 10713 | 3 | | | | | | FLJ46361 | 1.00 |
| 10618 | 3 | | | | | | FEZF2 | 1.00 | 10714 | 3 | | | | | | FLJ46446 | 1.00 |
| 10619 | 3 | | | | | | FFAR1 | 1.00 | 10715 | 3 | | | | | | FLT3 | 1.00 |
| 10620 | 3 | | | | | | FFAR3 | 1.00 | 10716 | 3 | | | | | | FMN2 | 1.00 |
| 10621 | 3 | | | | | | FGA | 1.00 | 10717 | 3 | | | | | | FMO6P | 1.00 |
| 10622 | 3 | | | | | | FGF12 | 1.00 | 10718 | 3 | | | | | | FMO9P | 1.00 |
| 10623 | 3 | | | | | | FGF14 | 1.00 | 10719 | 3 | | | | | | FMR1-AS1 | 1.00 |
| 10624 | 3 | | | | | | FGF14-IT1 | 1.00 | 10720 | 3 | | | | | | FMR1NB | 1.00 |
| 10625 | 3 | | | | | | FGF17 | 1.00 | 10721 | 3 | | | | | | FNDC7 | 1.00 |
| 10626 | 3 | | | | | | FGF19 | 1.00 | 10722 | 3 | | | | | | FNDC8 | 1.00 |
| 10627 | 3 | | | | | | FGF20 | 1.00 | 10723 | 3 | | | | | | FNDC9 | 1.00 |
| 10628 | 3 | | | | | | FGF21 | 1.00 | 10724 | 3 | | | | | | FOLH1 | 1.00 |
| 10629 | 3 | | | | | | FGF23 | 1.00 | 10725 | 3 | | | | | | FOLH1B | 1.00 |
| 10630 | 3 | | | | | | FGF3 | 1.00 | 10726 | 3 | | | | | | FOLR4 | 1.00 |
| 10631 | 3 | | | | | | FGF4 | 1.00 | 10727 | 3 | | | | | | FONG | 1.00 |
| 10632 | 3 | | | | | | FGF5 | 1.00 | 10728 | 3 | | | | | | FOXA2 | 1.00 |
| 10633 | 3 | | | | | | FGF6 | 1.00 | 10729 | 3 | | | | | | FOXA3 | 1.00 |
| 10634 | 3 | | | | | | FGF8 | 1.00 | 10730 | 3 | | | | | | FOXB1 | 1.00 |
| 10635 | 3 | | | | | | FGF9 | 1.00 | 10731 | 3 | | | | | | FOXB2 | 1.00 |
| 10636 | 3 | | | | | | FGFR4 | 1.00 | 10732 | 3 | | | | | | FOXD2 | 1.00 |
| 10637 | 3 | | | | | | FHAD1 | 1.00 | 10733 | 3 | | | | | | FOXD4 | 1.00 |
| 10638 | 3 | | | | | | FIBCD1 | 1.00 | 10734 | 3 | | | | | | FOXD4L1 | 1.00 |
| 10639 | 3 | | | | | | FIGLA | 1.00 | 10735 | 3 | | | | | | FOXD4L2 | 1.00 |
| 10640 | 3 | | | | | | FIGN | 1.00 | 10736 | 3 | | | | | | FOXD4L3 | 1.00 |
| 10641 | 3 | | | | | | FIGNL2 | 1.00 | 10737 | 3 | | | | | | FOXD4L5 | 1.00 |
| 10642 | 3 | | | | | | FILIP1 | 1.00 | 10738 | 3 | | | | | | FOXD4L6 | 1.00 |
| 10643 | 3 | | | | | | FKBP1A-SDCBP2 | 1.00 | 10739 | 3 | | | | | | FOXE3 | 1.00 |
| 10644 | 3 | | | | | | FKBP6 | 1.00 | 10740 | 3 | | | | | | FOXG1 | 1.00 |
| 10645 | 3 | | | | | | FKSG29 | 1.00 | 10741 | 3 | | | | | | FOXH1 | 1.00 |
| 10646 | 3 | | | | | | FLJ12825 | 1.00 | 10742 | 3 | | | | | | FOXI3 | 1.00 |
| 10647 | 3 | | | | | | FLJ13224 | 1.00 | 10743 | 3 | | | | | | FOXL1 | 1.00 |
| 10648 | 3 | | | | | | FLJ16171 | 1.00 | 10744 | 3 | | | | | | FOXL2 | 1.00 |
| 10649 | 3 | | | | | | FLJ16341 | 1.00 | 10745 | 3 | | | | | | FOXN4 | 1.00 |
| 10650 | 3 | | | | | | FLJ16779 | 1.00 | 10746 | 3 | | | | | | FOXR1 | 1.00 |
| 10651 | 3 | | | | | | FLJ20518 | 1.00 | 10747 | 3 | | | | | | FOXR2 | 1.00 |
| 10652 | 3 | | | | | | FLJ21408 | 1.00 | 10748 | 3 | | | | | | FPGT-TNNI3K | 1.00 |

Fig. 38 - 57

| | | | | | | | |
|---|---|---|---|---|---|---|---|
| 10749 | 3 | | FREM2 | 1.00 | 10845 | 3 | GATA1 | 1.00 |
| 10750 | 3 | | FREM3 | 1.00 | 10846 | 3 | GATA4 | 1.00 |
| 10751 | 3 | | FRG2 | 1.00 | 10847 | 3 | GATSL2 | 1.00 |
| 10752 | 3 | | FRG2B | 1.00 | 10848 | 3 | GBA3 | 1.00 |
| 10753 | 3 | | FRG2C | 1.00 | 10849 | 3 | GBP1PJ | 1.00 |
| 10754 | 3 | | FRK | 1.00 | 10850 | 3 | GBP6 | 1.00 |
| 10755 | 3 | | FRMD1 | 1.00 | 10851 | 3 | GBP7 | 1.00 |
| 10756 | 3 | | FRMD5 | 1.00 | 10852 | 3 | GBX1 | 1.00 |
| 10757 | 3 | | FRMD7 | 1.00 | 10853 | 3 | GBX2 | 1.00 |
| 10758 | 3 | | FRMPD2 | 1.00 | 10854 | 3 | GC | 1.00 |
| 10759 | 3 | | FRMPD2P1 | 1.00 | 10855 | 3 | GCFC1-AS1 | 1.00 |
| 10760 | 3 | | FRMPD4 | 1.00 | 10856 | 3 | GCG | 1.00 |
| 10761 | 3 | | FSBP | 1.00 | 10857 | 3 | GCGR | 1.00 |
| 10762 | 3 | | FSCB | 1.00 | 10858 | 3 | GCK | 1.00 |
| 10763 | 3 | | FSCN2 | 1.00 | 10859 | 3 | GCKR | 1.00 |
| 10764 | 3 | | FSCN3 | 1.00 | 10860 | 3 | GCM1 | 1.00 |
| 10765 | 3 | | FSD1 | 1.00 | 10861 | 3 | GCM2 | 1.00 |
| 10766 | 3 | | FSD1L | 1.00 | 10862 | 3 | GCNT3 | 1.00 |
| 10767 | 3 | | FSD2 | 1.00 | 10863 | 3 | GCNT7 | 1.00 |
| 10768 | 3 | | FSHB | 1.00 | 10864 | 3 | GCOM1 | 1.00 |
| 10769 | 3 | | FSHR | 1.00 | 10865 | 3 | GDA | 1.00 |
| 10770 | 3 | | FSIP1 | 1.00 | 10866 | 3 | GDAP1L1 | 1.00 |
| 10771 | 3 | | FSIP2 | 1.00 | 10867 | 3 | GDEP | 1.00 |
| 10772 | 3 | | FSTL5 | 1.00 | 10868 | 3 | GDF2 | 1.00 |
| 10773 | 3 | | FTCD | 1.00 | 10869 | 3 | GDF3 | 1.00 |
| 10774 | 3 | | FTHL17 | 1.00 | 10870 | 3 | GDF5 | 1.00 |
| 10775 | 3 | | FTLP10 | 1.00 | 10871 | 3 | GDF6 | 1.00 |
| 10776 | 3 | | FTMT | 1.00 | 10872 | 3 | GDF7 | 1.00 |
| 10777 | 3 | | FUT5 | 1.00 | 10873 | 3 | GDF9 | 1.00 |
| 10778 | 3 | | FUT6 | 1.00 | 10874 | 3 | GDPD4 | 1.00 |
| 10779 | 3 | | FUT9 | 1.00 | 10875 | 3 | GFAP | 1.00 |
| 10780 | 3 | | FXYD1 | 1.00 | 10876 | 3 | GFI1 | 1.00 |
| 10781 | 3 | | FXYD2 | 1.00 | 10877 | 3 | GFI1B | 1.00 |
| 10782 | 3 | | FXYD4 | 1.00 | 10878 | 3 | GFRA4 | 1.00 |
| 10783 | 3 | | FXYD6-FXYD2 | 1.00 | 10879 | 3 | GFRAL | 1.00 |
| 10784 | 3 | | FZD9 | 1.00 | 10880 | 3 | GGNBP1 | 1.00 |
| 10785 | 3 | | G6PC | 1.00 | 10881 | 3 | GGT3P | 1.00 |
| 10786 | 3 | | G6PC2 | 1.00 | 10882 | 3 | GGT8P | 1.00 |
| 10787 | 3 | | GAB4 | 1.00 | 10883 | 3 | GGTLC1 | 1.00 |
| 10788 | 3 | | GABBR2 | 1.00 | 10884 | 3 | GH1 | 1.00 |
| 10789 | 3 | | GABRA1 | 1.00 | 10885 | 3 | GH2 | 1.00 |
| 10790 | 3 | | GABRA2 | 1.00 | 10886 | 3 | GHRH | 1.00 |
| 10791 | 3 | | GABRA3 | 1.00 | 10887 | 3 | GHRHR | 1.00 |
| 10792 | 3 | | GABRA4 | 1.00 | 10888 | 3 | GHRL | 1.00 |
| 10793 | 3 | | GABRA5 | 1.00 | 10889 | 3 | GHSR | 1.00 |
| 10794 | 3 | | GABRA6 | 1.00 | 10890 | 3 | GIF | 1.00 |
| 10795 | 3 | | GABRB1 | 1.00 | 10891 | 3 | GIP | 1.00 |
| 10796 | 3 | | GABRB2 | 1.00 | 10892 | 3 | GJA10 | 1.00 |
| 10797 | 3 | | GABRB3 | 1.00 | 10893 | 3 | GJA3 | 1.00 |
| 10798 | 3 | | GABRD | 1.00 | 10894 | 3 | GJA8 | 1.00 |
| 10799 | 3 | | GABRG1 | 1.00 | 10895 | 3 | GJA9 | 1.00 |
| 10800 | 3 | | GABRG2 | 1.00 | 10896 | 3 | GJB7 | 1.00 |
| 10801 | 3 | | GABRG3 | 1.00 | 10897 | 3 | GJD2 | 1.00 |
| 10802 | 3 | | GABRQ | 1.00 | 10898 | 3 | GJD4 | 1.00 |
| 10803 | 3 | | GABRR1 | 1.00 | 10899 | 3 | GK2 | 1.00 |
| 10804 | 3 | | GABRR2 | 1.00 | 10900 | 3 | GKN1 | 1.00 |
| 10805 | 3 | | GABRR3 | 1.00 | 10901 | 3 | GKN2 | 1.00 |
| 10806 | 3 | | GAD1 | 1.00 | 10902 | 3 | GLIPR1L1 | 1.00 |
| 10807 | 3 | | GAD2 | 1.00 | 10903 | 3 | GLIPR1L2 | 1.00 |
| 10808 | 3 | | GADL1 | 1.00 | 10904 | 3 | GLIS3-AS1 | 1.00 |
| 10809 | 3 | | GAGE1 | 1.00 | 10905 | 3 | GLMN | 1.00 |
| 10810 | 3 | | GAGE10 | 1.00 | 10906 | 3 | GLOD5 | 1.00 |
| 10811 | 3 | | GAGE12B | 1.00 | 10907 | 3 | GLP1R | 1.00 |
| 10812 | 3 | | GAGE12C | 1.00 | 10908 | 3 | GLP2R | 1.00 |
| 10813 | 3 | | GAGE12D | 1.00 | 10909 | 3 | GLRA1 | 1.00 |
| 10814 | 3 | | GAGE12E | 1.00 | 10910 | 3 | GLRA2 | 1.00 |
| 10815 | 3 | | GAGE12F | 1.00 | 10911 | 3 | GLRA3 | 1.00 |
| 10816 | 3 | | GAGE12H | 1.00 | 10912 | 3 | GLRA4 | 1.00 |
| 10817 | 3 | | GAGE12I | 1.00 | 10913 | 3 | GLT25D2 | 1.00 |
| 10818 | 3 | | GAGE12J | 1.00 | 10914 | 3 | GLT6D1 | 1.00 |
| 10819 | 3 | | GAGE13 | 1.00 | 10915 | 3 | GLYATL3 | 1.00 |
| 10820 | 3 | | GAGE2A | 1.00 | 10916 | 3 | GLYCAM1 | 1.00 |
| 10821 | 3 | | GAGE2B | 1.00 | 10917 | 3 | GM140 | 1.00 |
| 10822 | 3 | | GAGE2C | 1.00 | 10918 | 3 | GML | 1.00 |
| 10823 | 3 | | GAGE2D | 1.00 | 10919 | 3 | GMNC | 1.00 |
| 10824 | 3 | | GAGE2E | 1.00 | 10920 | 3 | GNAS-AS1 | 1.00 |
| 10825 | 3 | | GAGE4 | 1.00 | 10921 | 3 | GNAT1 | 1.00 |
| 10826 | 3 | | GAGE5 | 1.00 | 10922 | 3 | GNAT2 | 1.00 |
| 10827 | 3 | | GAGE6 | 1.00 | 10923 | 3 | GNAT3 | 1.00 |
| 10828 | 3 | | GAGE7 | 1.00 | 10924 | 3 | GNG13 | 1.00 |
| 10829 | 3 | | GAGE8 | 1.00 | 10925 | 3 | GNG3 | 1.00 |
| 10830 | 3 | | GAL3ST2 | 1.00 | 10926 | 3 | GNG4 | 1.00 |
| 10831 | 3 | | GAL3ST3 | 1.00 | 10927 | 3 | GNG8 | 1.00 |
| 10832 | 3 | | GALNT13 | 1.00 | 10928 | 3 | GNGT1 | 1.00 |
| 10833 | 3 | | GALNT14 | 1.00 | 10929 | 3 | GNGT2 | 1.00 |
| 10834 | 3 | | GALNT5 | 1.00 | 10930 | 3 | GNN | 1.00 |
| 10835 | 3 | | GALNT8 | 1.00 | 10931 | 3 | GNRH2 | 1.00 |
| 10836 | 3 | | GALNT9 | 1.00 | 10932 | 3 | GNRHR | 1.00 |
| 10837 | 3 | | GALNTL5 | 1.00 | 10933 | 3 | GOLGA2P3Y | 1.00 |
| 10838 | 3 | | GALNTL6 | 1.00 | 10934 | 3 | GOLGA6A | 1.00 |
| 10839 | 3 | | GALP | 1.00 | 10935 | 3 | GOLGA6B | 1.00 |
| 10840 | 3 | | GALR1 | 1.00 | 10936 | 3 | GOLGA6C | 1.00 |
| 10841 | 3 | | GALR2 | 1.00 | 10937 | 3 | GOLGA6D | 1.00 |
| 10842 | 3 | | GALR3 | 1.00 | 10938 | 3 | GOLGA6L1 | 1.00 |
| 10843 | 3 | | GAS2 | 1.00 | 10939 | 3 | GOLGA6L6 | 1.00 |
| 10844 | 3 | | GAST | 1.00 | 10940 | 3 | GOLGA8C | 1.00 |

Fig. 38 - 58

| | | | | | | | |
|---|---|---|---|---|---|---|---|
| 10941 | 3 | | | | | GOLGA8DP | 1.00 |
| 10942 | 3 | | | | | GOLGA8E | 1.00 |
| 10943 | 3 | | | | | GOLGA8F | 1.00 |
| 10944 | 3 | | | | | GOLGA8G | 1.00 |
| 10945 | 3 | | | | | GOLGA8IP | 1.00 |
| 10946 | 3 | | | | | GOLT1A | 1.00 |
| 10947 | 3 | | | | | GOT1L1 | 1.00 |
| 10948 | 3 | | | | | GP2 | 1.00 |
| 10949 | 3 | | | | | GP5 | 1.00 |
| 10950 | 3 | | | | | GP9 | 1.00 |
| 10951 | 3 | | | | | GPA33 | 1.00 |
| 10952 | 3 | | | | | GPC5 | 1.00 |
| 10953 | 3 | | | | | GPCRLTM7 | 1.00 |
| 10954 | 3 | | | | | GPHA2 | 1.00 |
| 10955 | 3 | | | | | GPHB5 | 1.00 |
| 10956 | 3 | | | | | GPR101 | 1.00 |
| 10957 | 3 | | | | | GPR110 | 1.00 |
| 10958 | 3 | | | | | GPR112 | 1.00 |
| 10959 | 3 | | | | | GPR113 | 1.00 |
| 10960 | 3 | | | | | GPR114 | 1.00 |
| 10961 | 3 | | | | | GPR119 | 1.00 |
| 10962 | 3 | | | | | GPR123 | 1.00 |
| 10963 | 3 | | | | | GPR128 | 1.00 |
| 10964 | 3 | | | | | GPR135 | 1.00 |
| 10965 | 3 | | | | | GPR137C | 1.00 |
| 10966 | 3 | | | | | GPR139 | 1.00 |
| 10967 | 3 | | | | | GPR142 | 1.00 |
| 10968 | 3 | | | | | GPR144 | 1.00 |
| 10969 | 3 | | | | | GPR148 | 1.00 |
| 10970 | 3 | | | | | GPR149 | 1.00 |
| 10971 | 3 | | | | | GPR15 | 1.00 |
| 10972 | 3 | | | | | GPR150 | 1.00 |
| 10973 | 3 | | | | | GPR151 | 1.00 |
| 10974 | 3 | | | | | GPR152 | 1.00 |
| 10975 | 3 | | | | | GPR156 | 1.00 |
| 10976 | 3 | | | | | GPR158 | 1.00 |
| 10977 | 3 | | | | | GPR174 | 1.00 |
| 10978 | 3 | | | | | GPR179 | 1.00 |
| 10979 | 3 | | | | | GPR18 | 1.00 |
| 10980 | 3 | | | | | GPR182 | 1.00 |
| 10981 | 3 | | | | | GPR19 | 1.00 |
| 10982 | 3 | | | | | GPR21 | 1.00 |
| 10983 | 3 | | | | | GPR22 | 1.00 |
| 10984 | 3 | | | | | GPR25 | 1.00 |
| 10985 | 3 | | | | | GPR26 | 1.00 |
| 10986 | 3 | | | | | GPR31 | 1.00 |
| 10987 | 3 | | | | | GPR32 | 1.00 |
| 10988 | 3 | | | | | GPR33 | 1.00 |
| 10989 | 3 | | | | | GPR37L1 | 1.00 |
| 10990 | 3 | | | | | GPR39 | 1.00 |
| 10991 | 3 | | | | | GPR45 | 1.00 |
| 10992 | 3 | | | | | GPR50 | 1.00 |
| 10993 | 3 | | | | | GPR52 | 1.00 |
| 10994 | 3 | | | | | GPR6 | 1.00 |
| 10995 | 3 | | | | | GPR61 | 1.00 |
| 10996 | 3 | | | | | GPR62 | 1.00 |
| 10997 | 3 | | | | | GPR63 | 1.00 |
| 10998 | 3 | | | | | GPR64 | 1.00 |
| 10999 | 3 | | | | | GPR75-AS83 | 1.00 |
| 11000 | 3 | | | | | GPR78 | 1.00 |
| 11001 | 3 | | | | | GPR82 | 1.00 |
| 11002 | 3 | | | | | GPR83 | 1.00 |
| 11003 | 3 | | | | | GPR85 | 1.00 |
| 11004 | 3 | | | | | GPR88 | 1.00 |
| 11005 | 3 | | | | | GPR98 | 1.00 |
| 11006 | 3 | | | | | GPRC6A | 1.00 |
| 11007 | 3 | | | | | GPRIN3 | 1.00 |
| 11008 | 3 | | | | | GPX5 | 1.00 |
| 11009 | 3 | | | | | GPX6 | 1.00 |
| 11010 | 3 | | | | | GRAMD1B | 1.00 |
| 11011 | 3 | | | | | GRAPL | 1.00 |
| 11012 | 3 | | | | | GREB1L | 1.00 |
| 11013 | 3 | | | | | GRIA1 | 1.00 |
| 11014 | 3 | | | | | GRID2 | 1.00 |
| 11015 | 3 | | | | | GRID2IP | 1.00 |
| 11016 | 3 | | | | | GRIK1 | 1.00 |
| 11017 | 3 | | | | | GRIK1-AS1 | 1.00 |
| 11018 | 3 | | | | | GRIK1-AS2 | 1.00 |
| 11019 | 3 | | | | | GRIK4 | 1.00 |
| 11020 | 3 | | | | | GRIK5 | 1.00 |
| 11021 | 3 | | | | | GRIN1 | 1.00 |
| 11022 | 3 | | | | | GRIN2A | 1.00 |
| 11023 | 3 | | | | | GRIN2B | 1.00 |
| 11024 | 3 | | | | | GRIN2C | 1.00 |
| 11025 | 3 | | | | | GRIN2D | 1.00 |
| 11026 | 3 | | | | | GRK1 | 1.00 |
| 11027 | 3 | | | | | GRK4 | 1.00 |
| 11028 | 3 | | | | | GRK7 | 1.00 |
| 11029 | 3 | | | | | GRM1 | 1.00 |
| 11030 | 3 | | | | | GRM3 | 1.00 |
| 11031 | 3 | | | | | GRM4 | 1.00 |
| 11032 | 3 | | | | | GRM5 | 1.00 |
| 11033 | 3 | | | | | GRM6 | 1.00 |
| 11034 | 3 | | | | | GRM7 | 1.00 |
| 11035 | 3 | | | | | GRM8 | 1.00 |
| 11036 | 3 | | | | | GRP | 1.00 |
| 11037 | 3 | | | | | GRPR | 1.00 |
| 11038 | 3 | | | | | GRXCR1 | 1.00 |
| 11039 | 3 | | | | | GRXCR2 | 1.00 |
| 11040 | 3 | | | | | GSC2 | 1.00 |
| 11041 | 3 | | | | | GSG1 | 1.00 |
| 11042 | 3 | | | | | GSG1L | 1.00 |
| 11043 | 3 | | | | | GSTA1 | 1.00 |
| 11044 | 3 | | | | | GSTA2 | 1.00 |
| 11045 | 3 | | | | | GSTA5 | 1.00 |
| 11046 | 3 | | | | | GSTA7P | 1.00 |
| 11047 | 3 | | | | | GSTTP1 | 1.00 |
| 11048 | 3 | | | | | GSTTP2 | 1.00 |
| 11049 | 3 | | | | | GSX1 | 1.00 |
| 11050 | 3 | | | | | GSX2 | 1.00 |
| 11051 | 3 | | | | | GTF2A1L | 1.00 |
| 11052 | 3 | | | | | GTF2H2 | 1.00 |
| 11053 | 3 | | | | | GTF2H2D | 1.00 |
| 11054 | 3 | | | | | GTSF1 | 1.00 |
| 11055 | 3 | | | | | GTSF1L | 1.00 |
| 11056 | 3 | | | | | GUCA1A | 1.00 |
| 11057 | 3 | | | | | GUCA1C | 1.00 |
| 11058 | 3 | | | | | GUCA2A | 1.00 |
| 11059 | 3 | | | | | GUCA2B | 1.00 |
| 11060 | 3 | | | | | GUCY1A2 | 1.00 |
| 11061 | 3 | | | | | GUCY1B2 | 1.00 |
| 11062 | 3 | | | | | GUCY2C | 1.00 |
| 11063 | 3 | | | | | GUCY2D | 1.00 |
| 11064 | 3 | | | | | GUCY2E | 1.00 |
| 11065 | 3 | | | | | GUCY2F | 1.00 |
| 11066 | 3 | | | | | GUCY2GP | 1.00 |
| 11067 | 3 | | | | | GUSBP10 | 1.00 |
| 11068 | 3 | | | | | GUSBP2 | 1.00 |
| 11069 | 3 | | | | | GUSBP4 | 1.00 |
| 11070 | 3 | | | | | GVINP1 | 1.00 |
| 11071 | 3 | | | | | GYG2P1 | 1.00 |
| 11072 | 3 | | | | | GYPA | 1.00 |
| 11073 | 3 | | | | | GYPB | 1.00 |
| 11074 | 3 | | | | | GYPE | 1.00 |
| 11075 | 3 | | | | | GYS2 | 1.00 |
| 11076 | 3 | | | | | H1FNT | 1.00 |
| 11077 | 3 | | | | | H1FOO | 1.00 |
| 11078 | 3 | | | | | H2AFB1 | 1.00 |
| 11079 | 3 | | | | | H2AFB2 | 1.00 |
| 11080 | 3 | | | | | H2BFM | 1.00 |
| 11081 | 3 | | | | | H2BFWT | 1.00 |
| 11082 | 3 | | | | | HABP2 | 1.00 |
| 11083 | 3 | | | | | HAMP | 1.00 |
| 11084 | 3 | | | | | HAND1 | 1.00 |
| 11085 | 3 | | | | | HAP1 | 1.00 |
| 11086 | 3 | | | | | HAPLN1 | 1.00 |
| 11087 | 3 | | | | | HAPLN2 | 1.00 |
| 11088 | 3 | | | | | HAPLN4 | 1.00 |
| 11089 | 3 | | | | | HAR1A | 1.00 |
| 11090 | 3 | | | | | HAR1B | 1.00 |
| 11091 | 3 | | | | | HAVCR1 | 1.00 |
| 11092 | 3 | | | | | HBBP1 | 1.00 |
| 11093 | 3 | | | | | HBD | 1.00 |
| 11094 | 3 | | | | | HBE1 | 1.00 |
| 11095 | 3 | | | | | HBG1 | 1.00 |
| 11096 | 3 | | | | | HBG2 | 1.00 |
| 11097 | 3 | | | | | HBM | 1.00 |
| 11098 | 3 | | | | | HBQ1 | 1.00 |
| 11099 | 3 | | | | | HBZ | 1.00 |
| 11100 | 3 | | | | | HCAR1 | 1.00 |
| 11101 | 3 | | | | | HCG22 | 1.00 |
| 11102 | 3 | | | | | HCG4B | 1.00 |
| 11103 | 3 | | | | | HCG9 | 1.00 |
| 11104 | 3 | | | | | HCN1 | 1.00 |
| 11105 | 3 | | | | | HCN4 | 1.00 |
| 11106 | 3 | | | | | HCRT | 1.00 |
| 11107 | 3 | | | | | HCRTR1 | 1.00 |
| 11108 | 3 | | | | | HCRTR2 | 1.00 |
| 11109 | 3 | | | | | HDGFL1 | 1.00 |
| 11110 | 3 | | | | | HDX | 1.00 |
| 11111 | 3 | | | | | HEATR4 | 1.00 |
| 11112 | 3 | | | | | HEATR7B2 | 1.00 |
| 11113 | 3 | | | | | HEATR8-TTC4 | 1.00 |
| 11114 | 3 | | | | | HECW1 | 1.00 |
| 11115 | 3 | | | | | HELB | 1.00 |
| 11116 | 3 | | | | | HELLS | 1.00 |
| 11117 | 3 | | | | | HELT | 1.00 |
| 11118 | 3 | | | | | HEMGN | 1.00 |
| 11119 | 3 | | | | | HEPACAM | 1.00 |
| 11120 | 3 | | | | | HEPACAM2 | 1.00 |
| 11121 | 3 | | | | | HEPHL1 | 1.00 |
| 11122 | 3 | | | | | HERC2P4 | 1.00 |
| 11123 | 3 | | | | | HERC5 | 1.00 |
| 11124 | 3 | | | | | HES3 | 1.00 |
| 11125 | 3 | | | | | HES7 | 1.00 |
| 11126 | 3 | | | | | HFE2 | 1.00 |
| 11127 | 3 | | | | | HFM1 | 1.00 |
| 11128 | 3 | | | | | HGC6.3 | 1.00 |
| 11129 | 3 | | | | | HGF | 1.00 |
| 11130 | 3 | | | | | HGFAC | 1.00 |
| 11131 | 3 | | | | | HHIP | 1.00 |
| 11132 | 3 | | | | | HHIPL2 | 1.00 |

Fig. 38 - 59

| | | | | | | | |
|---|---|---|---|---|---|---|---|
| 11133 | 3 | | | | | HHLA1 | 1.00 |
| 11134 | 3 | | | | | HHLA2 | 1.00 |
| 11135 | 3 | | | | | HIGD1C | 1.00 |
| 11136 | 3 | | | | | HIGD2B | 1.00 |
| 11137 | 3 | | | | | HIPK4 | 1.00 |
| 11138 | 3 | | | | | HIST1H1A | 1.00 |
| 11139 | 3 | | | | | HIST1H1T | 1.00 |
| 11140 | 3 | | | | | HIST1H2AA | 1.00 |
| 11141 | 3 | | | | | HIST1H2AB | 1.00 |
| 11142 | 3 | | | | | HIST1H2AK | 1.00 |
| 11143 | 3 | | | | | HIST1H2APS1 | 1.00 |
| 11144 | 3 | | | | | HIST1H2BA | 1.00 |
| 11145 | 3 | | | | | HIST1H2BF | 1.00 |
| 11146 | 3 | | | | | HIST1H2BM | 1.00 |
| 11147 | 3 | | | | | HIST1H3A | 1.00 |
| 11148 | 3 | | | | | HIST1H3B | 1.00 |
| 11149 | 3 | | | | | HIST1H3C | 1.00 |
| 11150 | 3 | | | | | HIST1H3D | 1.00 |
| 11151 | 3 | | | | | HIST1H3F | 1.00 |
| 11152 | 3 | | | | | HIST1H3H | 1.00 |
| 11153 | 3 | | | | | HIST1H3I | 1.00 |
| 11154 | 3 | | | | | HIST1H3J | 1.00 |
| 11155 | 3 | | | | | HIST1H4A | 1.00 |
| 11156 | 3 | | | | | HIST1H4F | 1.00 |
| 11157 | 3 | | | | | HIST1H4G | 1.00 |
| 11158 | 3 | | | | | HIST1H4L | 1.00 |
| 11159 | 3 | | | | | HIST2H3D | 1.00 |
| 11160 | 3 | | | | | HIST3H3 | 1.00 |
| 11161 | 3 | | | | | HKDC1 | 1.00 |
| 11162 | 3 | | | | | HLA-DPB2 | 1.00 |
| 11163 | 3 | | | | | HLA-J | 1.00 |
| 11164 | 3 | | | | | HLA-L | 1.00 |
| 11165 | 3 | | | | | HMGA1P7 | 1.00 |
| 11166 | 3 | | | | | HMGA2 | 1.00 |
| 11167 | 3 | | | | | HMGB3P1 | 1.00 |
| 11168 | 3 | | | | | HMGB4 | 1.00 |
| 11169 | 3 | | | | | HMGCLL1 | 1.00 |
| 11170 | 3 | | | | | HMGN2P46 | 1.00 |
| 11171 | 3 | | | | | HMHB1 | 1.00 |
| 11172 | 3 | | | | | HMMR | 1.00 |
| 11173 | 3 | | | | | HMP19 | 1.00 |
| 11174 | 3 | | | | | HMSD | 1.00 |
| 11175 | 3 | | | | | HMX1 | 1.00 |
| 11176 | 3 | | | | | HMX2 | 1.00 |
| 11177 | 3 | | | | | HMX3 | 1.00 |
| 11178 | 3 | | | | | HNF1A | 1.00 |
| 11179 | 3 | | | | | HNF1A-AS1 | 1.00 |
| 11180 | 3 | | | | | HNF1B | 1.00 |
| 11181 | 3 | | | | | HNF4A | 1.00 |
| 11182 | 3 | | | | | HNF4G | 1.00 |
| 11183 | 3 | | | | | HNRNPA1P10 | 1.00 |
| 11184 | 3 | | | | | HNRNPCL1 | 1.00 |
| 11185 | 3 | | | | | HNRNPUL2-BSCL2 | 1.00 |
| 11186 | 3 | | | | | HORMAD1 | 1.00 |
| 11187 | 3 | | | | | HORMAD2 | 1.00 |
| 11188 | 3 | | | | | HOTTIP | 1.00 |
| 11189 | 3 | | | | | HOXA10-HOXA9 | 1.00 |
| 11190 | 3 | | | | | HOXA11 | 1.00 |
| 11191 | 3 | | | | | HOXA13 | 1.00 |
| 11192 | 3 | | | | | HOXA-AS5 | 1.00 |
| 11193 | 3 | | | | | HOXB1 | 1.00 |
| 11194 | 3 | | | | | HOXB13 | 1.00 |
| 11195 | 3 | | | | | HOXB9 | 1.00 |
| 11196 | 3 | | | | | HOXB-AS5 | 1.00 |
| 11197 | 3 | | | | | HOXD11 | 1.00 |
| 11198 | 3 | | | | | HOXD12 | 1.00 |
| 11199 | 3 | | | | | HOXD13 | 1.00 |
| 11200 | 3 | | | | | HP | 1.00 |
| 11201 | 3 | | | | | HPCA | 1.00 |
| 11202 | 3 | | | | | HPCAL4 | 1.00 |
| 11203 | 3 | | | | | HPD | 1.00 |
| 11204 | 3 | | | | | HPN | 1.00 |
| 11205 | 3 | | | | | HPVC1 | 1.00 |
| 11206 | 3 | | | | | HPYR1 | 1.00 |
| 11207 | 3 | | | | | HRASLS2 | 1.00 |
| 11208 | 3 | | | | | HRG | 1.00 |
| 11209 | 3 | | | | | HRH3 | 1.00 |
| 11210 | 3 | | | | | HRH4 | 1.00 |
| 11211 | 3 | | | | | HRK | 1.00 |
| 11212 | 3 | | | | | HRNR | 1.00 |
| 11213 | 3 | | | | | HS3ST5 | 1.00 |
| 11214 | 3 | | | | | HS6ST2 | 1.00 |
| 11215 | 3 | | | | | HS6ST3 | 1.00 |
| 11216 | 3 | | | | | HSD17B3 | 1.00 |
| 11217 | 3 | | | | | HSD3B2 | 1.00 |
| 11218 | 3 | | | | | HSD3BP4 | 1.00 |
| 11219 | 3 | | | | | HSF2BP | 1.00 |
| 11220 | 3 | | | | | HSF5 | 1.00 |
| 11221 | 3 | | | | | HSFX2 | 1.00 |
| 11222 | 3 | | | | | HSFY1 | 1.00 |
| 11223 | 3 | | | | | HSFY1P1 | 1.00 |
| 11224 | 3 | | | | | HSFY2 | 1.00 |
| 11225 | 3 | | | | | HSPB2-C11orf52 | 1.00 |
| 11226 | 3 | | | | | HSPB9 | 1.00 |
| 11227 | 3 | | | | | HSPC072 | 1.00 |
| 11228 | 3 | | | | | HTA | 1.00 |
| 11229 | 3 | | | | | HTN1 | 1.00 |
| 11230 | 3 | | | | | HTN3 | 1.00 |
| 11231 | 3 | | | | | HTR1A | 1.00 |
| 11232 | 3 | | | | | HTR1B | 1.00 |
| 11233 | 3 | | | | | HTR1D | 1.00 |
| 11234 | 3 | | | | | HTR1E | 1.00 |
| 11235 | 3 | | | | | HTR1F | 1.00 |
| 11236 | 3 | | | | | HTR2A | 1.00 |
| 11237 | 3 | | | | | HTR2B | 1.00 |
| 11238 | 3 | | | | | HTR2C | 1.00 |
| 11239 | 3 | | | | | HTR3A | 1.00 |
| 11240 | 3 | | | | | HTR3B | 1.00 |
| 11241 | 3 | | | | | HTR3C | 1.00 |
| 11242 | 3 | | | | | HTR3D | 1.00 |
| 11243 | 3 | | | | | HTR3E | 1.00 |
| 11244 | 3 | | | | | HTR4 | 1.00 |
| 11245 | 3 | | | | | HTR5A | 1.00 |
| 11246 | 3 | | | | | HTR6 | 1.00 |
| 11247 | 3 | | | | | HTR7 | 1.00 |
| 11248 | 3 | | | | | HTRA4 | 1.00 |
| 11249 | 3 | | | | | HTT-AS1 | 1.00 |
| 11250 | 3 | | | | | HULC | 1.00 |
| 11251 | 3 | | | | | HUS1B | 1.00 |
| 11252 | 3 | | | | | HYAL4 | 1.00 |
| 11253 | 3 | | | | | HYALP1 | 1.00 |
| 11254 | 3 | | | | | HYDIN | 1.00 |
| 11255 | 3 | | | | | HYMAI | 1.00 |
| 11256 | 3 | | | | | IAPP | 1.00 |
| 11257 | 3 | | | | | IBSP | 1.00 |
| 11258 | 3 | | | | | ICAM5 | 1.00 |
| 11259 | 3 | | | | | IDA5 | 1.00 |
| 11260 | 3 | | | | | IDO1 | 1.00 |
| 11261 | 3 | | | | | IDO2 | 1.00 |
| 11262 | 3 | | | | | IFIT1B | 1.00 |
| 11263 | 3 | | | | | IFITM5 | 1.00 |
| 11264 | 3 | | | | | IFLTD1 | 1.00 |
| 11265 | 3 | | | | | IFNA1 | 1.00 |
| 11266 | 3 | | | | | IFNA10 | 1.00 |
| 11267 | 3 | | | | | IFNA13 | 1.00 |
| 11268 | 3 | | | | | IFNA14 | 1.00 |
| 11269 | 3 | | | | | IFNA16 | 1.00 |
| 11270 | 3 | | | | | IFNA17 | 1.00 |
| 11271 | 3 | | | | | IFNA2 | 1.00 |
| 11272 | 3 | | | | | IFNA21 | 1.00 |
| 11273 | 3 | | | | | IFNA22P | 1.00 |
| 11274 | 3 | | | | | IFNA4 | 1.00 |
| 11275 | 3 | | | | | IFNA5 | 1.00 |
| 11276 | 3 | | | | | IFNA6 | 1.00 |
| 11277 | 3 | | | | | IFNA7 | 1.00 |
| 11278 | 3 | | | | | IFNA8 | 1.00 |
| 11279 | 3 | | | | | IFNB1 | 1.00 |
| 11280 | 3 | | | | | IFNE | 1.00 |
| 11281 | 3 | | | | | IFNG | 1.00 |
| 11282 | 3 | | | | | IFNK | 1.00 |
| 11283 | 3 | | | | | IFNW1 | 1.00 |
| 11284 | 3 | | | | | IGDCC3 | 1.00 |
| 11285 | 3 | | | | | IGF2-AS1 | 1.00 |
| 11286 | 3 | | | | | IGF2BP1 | 1.00 |
| 11287 | 3 | | | | | IGF2BP3 | 1.00 |
| 11288 | 3 | | | | | IGFBP1 | 1.00 |
| 11289 | 3 | | | | | IGFBPL1 | 1.00 |
| 11290 | 3 | | | | | IGFL1 | 1.00 |
| 11291 | 3 | | | | | IGFN1 | 1.00 |
| 11292 | 3 | | | | | IGLL1 | 1.00 |
| 11293 | 3 | | | | | IGSF11-AS1 | 1.00 |
| 11294 | 3 | | | | | IGSF22 | 1.00 |
| 11295 | 3 | | | | | IGSF23 | 1.00 |
| 11296 | 3 | | | | | IGSF5 | 1.00 |
| 11297 | 3 | | | | | IHH | 1.00 |
| 11298 | 3 | | | | | IL12A | 1.00 |
| 11299 | 3 | | | | | IL12B | 1.00 |
| 11300 | 3 | | | | | IL12RB2 | 1.00 |
| 11301 | 3 | | | | | IL13 | 1.00 |
| 11302 | 3 | | | | | IL13RA2 | 1.00 |
| 11303 | 3 | | | | | IL17A | 1.00 |
| 11304 | 3 | | | | | IL17C | 1.00 |
| 11305 | 3 | | | | | IL17F | 1.00 |
| 11306 | 3 | | | | | IL17REL | 1.00 |
| 11307 | 3 | | | | | IL19 | 1.00 |
| 11308 | 3 | | | | | IL1RAPL1 | 1.00 |
| 11309 | 3 | | | | | IL1RAPL2 | 1.00 |
| 11310 | 3 | | | | | IL2 | 1.00 |
| 11311 | 3 | | | | | IL20 | 1.00 |
| 11312 | 3 | | | | | IL21 | 1.00 |
| 11313 | 3 | | | | | IL21R | 1.00 |
| 11314 | 3 | | | | | IL22 | 1.00 |
| 11315 | 3 | | | | | IL22RA2 | 1.00 |
| 11316 | 3 | | | | | IL23A | 1.00 |
| 11317 | 3 | | | | | IL23R | 1.00 |
| 11318 | 3 | | | | | IL24 | 1.00 |
| 11319 | 3 | | | | | IL25 | 1.00 |
| 11320 | 3 | | | | | IL26 | 1.00 |
| 11321 | 3 | | | | | IL27 | 1.00 |
| 11322 | 3 | | | | | IL28A | 1.00 |
| 11323 | 3 | | | | | IL28B | 1.00 |
| 11324 | 3 | | | | | IL29 | 1.00 |

Fig. 38 - 60

| | | | | | | | | | | | | | | | | |
|---|---|---|---|---|---|---|---|---|---|---|---|---|---|---|---|---|
| 11325 | 3 | | | | | IL3 | 1.00 | | 11421 | 3 | | | | | KCND2 | 1.00 |
| 11326 | 3 | | | | | IL31 | 1.00 | | 11422 | 3 | | | | | KCNE1L | 1.00 |
| 11327 | 3 | | | | | IL31RA | 1.00 | | 11423 | 3 | | | | | KCNE2 | 1.00 |
| 11328 | 3 | | | | | IL36A | 1.00 | | 11424 | 3 | | | | | KCNF1 | 1.00 |
| 11329 | 3 | | | | | IL4 | 1.00 | | 11425 | 3 | | | | | KCNG2 | 1.00 |
| 11330 | 3 | | | | | IL5 | 1.00 | | 11426 | 3 | | | | | KCNG3 | 1.00 |
| 11331 | 3 | | | | | IL5RA | 1.00 | | 11427 | 3 | | | | | KCNG4 | 1.00 |
| 11332 | 3 | | | | | IL9 | 1.00 | | 11428 | 3 | | | | | KCNH1 | 1.00 |
| 11333 | 3 | | | | | IL9R | 1.00 | | 11429 | 3 | | | | | KCNH3 | 1.00 |
| 11334 | 3 | | | | | ILDR2 | 1.00 | | 11430 | 3 | | | | | KCNH4 | 1.00 |
| 11335 | 3 | | | | | IMPG1 | 1.00 | | 11431 | 3 | | | | | KCNH5 | 1.00 |
| 11336 | 3 | | | | | IMPG2 | 1.00 | | 11432 | 3 | | | | | KCNH6 | 1.00 |
| 11337 | 3 | | | | | INA | 1.00 | | 11433 | 3 | | | | | KCNH7 | 1.00 |
| 11338 | 3 | | | | | INGX | 1.00 | | 11434 | 3 | | | | | KCNH8 | 1.00 |
| 11339 | 3 | | | | | INHBC | 1.00 | | 11435 | 3 | | | | | KCNIP4 | 1.00 |
| 11340 | 3 | | | | | INHBE | 1.00 | | 11436 | 3 | | | | | KCNIP4-IT1 | 1.00 |
| 11341 | 3 | | | | | INMT-FAM188B | 1.00 | | 11437 | 3 | | | | | KCNJ10 | 1.00 |
| 11342 | 3 | | | | | INO80B-WBP1 | 1.00 | | 11438 | 3 | | | | | KCNJ16 | 1.00 |
| 11343 | 3 | | | | | INPP4B | 1.00 | | 11439 | 3 | | | | | KCNJ3 | 1.00 |
| 11344 | 3 | | | | | INS | 1.00 | | 11440 | 3 | | | | | KCNJ4 | 1.00 |
| 11345 | 3 | | | | | INSC | 1.00 | | 11441 | 3 | | | | | KCNJ6 | 1.00 |
| 11346 | 3 | | | | | INS-IGF2 | 1.00 | | 11442 | 3 | | | | | KCNJ9 | 1.00 |
| 11347 | 3 | | | | | INSL3 | 1.00 | | 11443 | 3 | | | | | KCNK10 | 1.00 |
| 11348 | 3 | | | | | INSL4 | 1.00 | | 11444 | 3 | | | | | KCNK12 | 1.00 |
| 11349 | 3 | | | | | INSL5 | 1.00 | | 11445 | 3 | | | | | KCNK13 | 1.00 |
| 11350 | 3 | | | | | INSL6 | 1.00 | | 11446 | 3 | | | | | KCNK16 | 1.00 |
| 11351 | 3 | | | | | INSM1 | 1.00 | | 11447 | 3 | | | | | KCNK17 | 1.00 |
| 11352 | 3 | | | | | INSM2 | 1.00 | | 11448 | 3 | | | | | KCNK18 | 1.00 |
| 11353 | 3 | | | | | INSRR | 1.00 | | 11449 | 3 | | | | | KCNK3 | 1.00 |
| 11354 | 3 | | | | | INTS4L1 | 1.00 | | 11450 | 3 | | | | | KCNK4 | 1.00 |
| 11355 | 3 | | | | | INTS4L2 | 1.00 | | 11451 | 3 | | | | | KCNK9 | 1.00 |
| 11356 | 3 | | | | | IP6K3 | 1.00 | | 11452 | 3 | | | | | KCNMB2 | 1.00 |
| 11357 | 3 | | | | | IPCEF1 | 1.00 | | 11453 | 3 | | | | | KCNN1 | 1.00 |
| 11358 | 3 | | | | | IQCA1 | 1.00 | | 11454 | 3 | | | | | KCNN3 | 1.00 |
| 11359 | 3 | | | | | IQCF1 | 1.00 | | 11455 | 3 | | | | | KCNQ1DN | 1.00 |
| 11360 | 3 | | | | | IQCF2 | 1.00 | | 11456 | 3 | | | | | KCNQ1OT1 | 1.00 |
| 11361 | 3 | | | | | IQCF3 | 1.00 | | 11457 | 3 | | | | | KCNQ2 | 1.00 |
| 11362 | 3 | | | | | IQCF4 | 1.00 | | 11458 | 3 | | | | | KCNQ3 | 1.00 |
| 11363 | 3 | | | | | IQCF5 | 1.00 | | 11459 | 3 | | | | | KCNQ5 | 1.00 |
| 11364 | 3 | | | | | IQCF6 | 1.00 | | 11460 | 3 | | | | | KCNS2 | 1.00 |
| 11365 | 3 | | | | | IQCH | 1.00 | | 11461 | 3 | | | | | KCNT1 | 1.00 |
| 11366 | 3 | | | | | IQCJ | 1.00 | | 11462 | 3 | | | | | KCNT2 | 1.00 |
| 11367 | 3 | | | | | IQUB | 1.00 | | 11463 | 3 | | | | | KCNU1 | 1.00 |
| 11368 | 3 | | | | | IRGC | 1.00 | | 11464 | 3 | | | | | KCNV1 | 1.00 |
| 11369 | 3 | | | | | IRGM | 1.00 | | 11465 | 3 | | | | | KCNV2 | 1.00 |
| 11370 | 3 | | | | | IRS4 | 1.00 | | 11466 | 3 | | | | | KCP | 1.00 |
| 11371 | 3 | | | | | ISL1 | 1.00 | | 11467 | 3 | | | | | KCTD14 | 1.00 |
| 11372 | 3 | | | | | ISL2 | 1.00 | | 11468 | 3 | | | | | KCTD16 | 1.00 |
| 11373 | 3 | | | | | ISM2 | 1.00 | | 11469 | 3 | | | | | KCTD19 | 1.00 |
| 11374 | 3 | | | | | ISPD | 1.00 | | 11470 | 3 | | | | | KCTD8 | 1.00 |
| 11375 | 3 | | | | | ISX | 1.00 | | 11471 | 3 | | | | | KDM4DL | 1.00 |
| 11376 | 3 | | | | | ISY1-RAB43 | 1.00 | | 11472 | 3 | | | | | KDM5D | 1.00 |
| 11377 | 3 | | | | | ITGA2B | 1.00 | | 11473 | 3 | | | | | KEL | 1.00 |
| 11378 | 3 | | | | | ITGAD | 1.00 | | 11474 | 3 | | | | | KERA | 1.00 |
| 11379 | 3 | | | | | ITGAE | 1.00 | | 11475 | 3 | | | | | KGFLP1 | 1.00 |
| 11380 | 3 | | | | | ITGB1BP2 | 1.00 | | 11476 | 3 | | | | | KHDC1 | 1.00 |
| 11381 | 3 | | | | | ITGB1BP3 | 1.00 | | 11477 | 3 | | | | | KHDC1L | 1.00 |
| 11382 | 3 | | | | | ITGB6 | 1.00 | | 11478 | 3 | | | | | KHDRBS2 | 1.00 |
| 11383 | 3 | | | | | ITIH1 | 1.00 | | 11479 | 3 | | | | | KIAA0087 | 1.00 |
| 11384 | 3 | | | | | ITIH2 | 1.00 | | 11480 | 3 | | | | | KIAA0125 | 1.00 |
| 11385 | 3 | | | | | ITIH3 | 1.00 | | 11481 | 3 | | | | | KIAA0319 | 1.00 |
| 11386 | 3 | | | | | ITIH6 | 1.00 | | 11482 | 3 | | | | | KIAA0825 | 1.00 |
| 11387 | 3 | | | | | ITLN1 | 1.00 | | 11483 | 3 | | | | | KIAA1024 | 1.00 |
| 11388 | 3 | | | | | ITLN2 | 1.00 | | 11484 | 3 | | | | | KIAA1107 | 1.00 |
| 11389 | 3 | | | | | ITPK1-AS1 | 1.00 | | 11485 | 3 | | | | | KIAA1210 | 1.00 |
| 11390 | 3 | | | | | ITPKA | 1.00 | | 11486 | 3 | | | | | KIAA1211 | 1.00 |
| 11391 | 3 | | | | | IYD | 1.00 | | 11487 | 3 | | | | | KIAA1239 | 1.00 |
| 11392 | 3 | | | | | IZUMO1 | 1.00 | | 11488 | 3 | | | | | KIAA1257 | 1.00 |
| 11393 | 3 | | | | | IZUMO2 | 1.00 | | 11489 | 3 | | | | | KIAA1383 | 1.00 |
| 11394 | 3 | | | | | JAKMIP1 | 1.00 | | 11490 | 3 | | | | | KIAA1524 | 1.00 |
| 11395 | 3 | | | | | JAKMIP2 | 1.00 | | 11491 | 3 | | | | | KIAA1656 | 1.00 |
| 11396 | 3 | | | | | JAKMIP3 | 1.00 | | 11492 | 3 | | | | | KIAA1751 | 1.00 |
| 11397 | 3 | | | | | JAZF1-AS1 | 1.00 | | 11493 | 3 | | | | | KIAA1804 | 1.00 |
| 11398 | 3 | | | | | JMJD7-PLA2G4B | 1.00 | | 11494 | 3 | | | | | KIAA1875 | 1.00 |
| 11399 | 3 | | | | | JPH1 | 1.00 | | 11495 | 3 | | | | | KIAA1958 | 1.00 |
| 11400 | 3 | | | | | JPH3 | 1.00 | | 11496 | 3 | | | | | KIAA1984 | 1.00 |
| 11401 | 3 | | | | | JSRP1 | 1.00 | | 11497 | 3 | | | | | KIAA2022 | 1.00 |
| 11402 | 3 | | | | | KAAG1 | 1.00 | | 11498 | 3 | | | | | KIF12 | 1.00 |
| 11403 | 3 | | | | | KATNAL2 | 1.00 | | 11499 | 3 | | | | | KIF14 | 1.00 |
| 11404 | 3 | | | | | KBTBD10 | 1.00 | | 11500 | 3 | | | | | KIF15 | 1.00 |
| 11405 | 3 | | | | | KBTBD12 | 1.00 | | 11501 | 3 | | | | | KIF18A | 1.00 |
| 11406 | 3 | | | | | KBTBD13 | 1.00 | | 11502 | 3 | | | | | KIF19 | 1.00 |
| 11407 | 3 | | | | | KBTBD5 | 1.00 | | 11503 | 3 | | | | | KIF24 | 1.00 |
| 11408 | 3 | | | | | KBTBD8 | 1.00 | | 11504 | 3 | | | | | KIF25 | 1.00 |
| 11409 | 3 | | | | | KC6 | 1.00 | | 11505 | 3 | | | | | KIF27 | 1.00 |
| 11410 | 3 | | | | | KCNA1 | 1.00 | | 11506 | 3 | | | | | KIF2B | 1.00 |
| 11411 | 3 | | | | | KCNA10 | 1.00 | | 11507 | 3 | | | | | KIF4A | 1.00 |
| 11412 | 3 | | | | | KCNA2 | 1.00 | | 11508 | 3 | | | | | KIF4B | 1.00 |
| 11413 | 3 | | | | | KCNA3 | 1.00 | | 11509 | 3 | | | | | KIF5A | 1.00 |
| 11414 | 3 | | | | | KCNA4 | 1.00 | | 11510 | 3 | | | | | KIF5C | 1.00 |
| 11415 | 3 | | | | | KCNA5 | 1.00 | | 11511 | 3 | | | | | KIF6 | 1.00 |
| 11416 | 3 | | | | | KCNA7 | 1.00 | | 11512 | 3 | | | | | KIR2DL1 | 1.00 |
| 11417 | 3 | | | | | KCNB1 | 1.00 | | 11513 | 3 | | | | | KIR2DL2 | 1.00 |
| 11418 | 3 | | | | | KCNB2 | 1.00 | | 11514 | 3 | | | | | KIR2DL3 | 1.00 |
| 11419 | 3 | | | | | KCNC1 | 1.00 | | 11515 | 3 | | | | | KIR2DL4 | 1.00 |
| 11420 | 3 | | | | | KCNC2 | 1.00 | | 11516 | 3 | | | | | KIR2DL5A | 1.00 |

Fig. 38 - 61

| | | | | | |
|---|---|---|---|---|---|
| 11517 | 3 | KIR2DL5B | 1.00 | 11613 | 3 | KRTAP22-2 | 1.00 |

| ID | Val | Gene | Score | ID | Val | Gene | Score |
|---|---|---|---|---|---|---|---|
| 11517 | 3 | KIR2DL5B | 1.00 | 11613 | 3 | KRTAP22-2 | 1.00 |
| 11518 | 3 | KIR2DS1 | 1.00 | 11614 | 3 | KRTAP23-1 | 1.00 |
| 11519 | 3 | KIR2DS2 | 1.00 | 11615 | 3 | KRTAP25-1 | 1.00 |
| 11520 | 3 | KIR2DS3 | 1.00 | 11616 | 3 | KRTAP27-1 | 1.00 |
| 11521 | 3 | KIR2DS4 | 1.00 | 11617 | 3 | KRTAP4-5 | 1.00 |
| 11522 | 3 | KIR2DS5 | 1.00 | 11618 | 3 | KRTAP5-1 | 1.00 |
| 11523 | 3 | KIR3DL1 | 1.00 | 11619 | 3 | KRTAP5-6 | 1.00 |
| 11524 | 3 | KIR3DL2 | 1.00 | 11620 | 3 | KRTAP5-9 | 1.00 |
| 11525 | 3 | KIR3DL3 | 1.00 | 11621 | 3 | KRTAP6-1 | 1.00 |
| 11526 | 3 | KIR3DS1 | 1.00 | 11622 | 3 | KRTAP6-2 | 1.00 |
| 11527 | 3 | KIR3DX1 | 1.00 | 11623 | 3 | KRTAP6-3 | 1.00 |
| 11528 | 3 | KIRREL2 | 1.00 | 11624 | 3 | KRTAP7-1 | 1.00 |
| 11529 | 3 | KIRREL3 | 1.00 | 11625 | 3 | KRTAP9-1 | 1.00 |
| 11530 | 3 | KIRREL3-AS3 | 1.00 | 11626 | 3 | KSR2 | 1.00 |
| 11531 | 3 | KISS1 | 1.00 | 11627 | 3 | KYNU | 1.00 |
| 11532 | 3 | KISS1R | 1.00 | 11628 | 3 | L1TD1 | 1.00 |
| 11533 | 3 | KLF1 | 1.00 | 11629 | 3 | LACE1 | 1.00 |
| 11534 | 3 | KLF17 | 1.00 | 11630 | 3 | LACRT | 1.00 |
| 11535 | 3 | KLHDC7A | 1.00 | 11631 | 3 | LAIR2 | 1.00 |
| 11536 | 3 | KLHDC7B | 1.00 | 11632 | 3 | LALBA | 1.00 |
| 11537 | 3 | KLHDC8A | 1.00 | 11633 | 3 | LAMA1 | 1.00 |
| 11538 | 3 | KLHL1 | 1.00 | 11634 | 3 | LANCL3 | 1.00 |
| 11539 | 3 | KLHL10 | 1.00 | 11635 | 3 | LBP | 1.00 |
| 11540 | 3 | KLHL11 | 1.00 | 11636 | 3 | LBX1 | 1.00 |
| 11541 | 3 | KLHL14 | 1.00 | 11637 | 3 | LBX2 | 1.00 |
| 11542 | 3 | KLHL31 | 1.00 | 11638 | 3 | LCA5L | 1.00 |
| 11543 | 3 | KLHL32 | 1.00 | 11639 | 3 | LCE3B | 1.00 |
| 11544 | 3 | KLHL33 | 1.00 | 11640 | 3 | LCE3C | 1.00 |
| 11545 | 3 | KLHL34 | 1.00 | 11641 | 3 | LCN1 | 1.00 |
| 11546 | 3 | KLHL35 | 1.00 | 11642 | 3 | LCN12 | 1.00 |
| 11547 | 3 | KLHL38 | 1.00 | 11643 | 3 | LCN15 | 1.00 |
| 11548 | 3 | KLHL4 | 1.00 | 11644 | 3 | LCN6 | 1.00 |
| 11549 | 3 | KLHL7-AS1 | 1.00 | 11645 | 3 | LCN8 | 1.00 |
| 11550 | 3 | KLK12 | 1.00 | 11646 | 3 | LCN9 | 1.00 |
| 11551 | 3 | KLK15 | 1.00 | 11647 | 3 | LCT | 1.00 |
| 11552 | 3 | KLK2 | 1.00 | 11648 | 3 | LCTL | 1.00 |
| 11553 | 3 | KLK3 | 1.00 | 11649 | 3 | LDHAL6A | 1.00 |
| 11554 | 3 | KLK4 | 1.00 | 11650 | 3 | LDHAL6B | 1.00 |
| 11555 | 3 | KLKB1 | 1.00 | 11651 | 3 | LDHC | 1.00 |
| 11556 | 3 | KLKP1 | 1.00 | 11652 | 3 | LDLRAD1 | 1.00 |
| 11557 | 3 | KLLN | 1.00 | 11653 | 3 | LECT1 | 1.00 |
| 11558 | 3 | KLRC1 | 1.00 | 11654 | 3 | LECT2 | 1.00 |
| 11559 | 3 | KLRC2 | 1.00 | 11655 | 3 | LEFTY1 | 1.00 |
| 11560 | 3 | KLRC3 | 1.00 | 11656 | 3 | LEFTY2 | 1.00 |
| 11561 | 3 | KLRC4 | 1.00 | 11657 | 3 | LEKR1 | 1.00 |
| 11562 | 3 | KLRC4-KLRK1 | 1.00 | 11658 | 3 | LELP1 | 1.00 |
| 11563 | 3 | KLRD1 | 1.00 | 11659 | 3 | LEMD1 | 1.00 |
| 11564 | 3 | KLRF1 | 1.00 | 11660 | 3 | LENEP | 1.00 |
| 11565 | 3 | KLRF2 | 1.00 | 11661 | 3 | LETM2 | 1.00 |
| 11566 | 3 | KLRG1 | 1.00 | 11662 | 3 | LEUTX | 1.00 |
| 11567 | 3 | KMO | 1.00 | 11663 | 3 | LGALS13 | 1.00 |
| 11568 | 3 | KNCN | 1.00 | 11664 | 3 | LGALS14 | 1.00 |
| 11569 | 3 | KNG1 | 1.00 | 11665 | 3 | LGALS16 | 1.00 |
| 11570 | 3 | KNTC1 | 1.00 | 11666 | 3 | LGALS17A | 1.00 |
| 11571 | 3 | KPNA5 | 1.00 | 11667 | 3 | LGALS8-AS1 | 1.00 |
| 11572 | 3 | KPNA7 | 1.00 | 11668 | 3 | LGALS9B | 1.00 |
| 11573 | 3 | KRT12 | 1.00 | 11669 | 3 | LGALS9C | 1.00 |
| 11574 | 3 | KRT13 | 1.00 | 11670 | 3 | LGI1 | 1.00 |
| 11575 | 3 | KRT18P55 | 1.00 | 11671 | 3 | LG5N | 1.00 |
| 11576 | 3 | KRT20 | 1.00 | 11672 | 3 | LHCGR | 1.00 |
| 11577 | 3 | KRT222 | 1.00 | 11673 | 3 | LHFPL1 | 1.00 |
| 11578 | 3 | KRT24 | 1.00 | 11674 | 3 | LHFPL3 | 1.00 |
| 11579 | 3 | KRT33A | 1.00 | 11675 | 3 | LHFPL4 | 1.00 |
| 11580 | 3 | KRT36 | 1.00 | 11676 | 3 | LHFPL5 | 1.00 |
| 11581 | 3 | KRT37 | 1.00 | 11677 | 3 | LHX1 | 1.00 |
| 11582 | 3 | KRT38 | 1.00 | 11678 | 3 | LHX3 | 1.00 |
| 11583 | 3 | KRT39 | 1.00 | 11679 | 3 | LHX4 | 1.00 |
| 11584 | 3 | KRT40 | 1.00 | 11680 | 3 | LHX5 | 1.00 |
| 11585 | 3 | KRT76 | 1.00 | 11681 | 3 | LHX8 | 1.00 |
| 11586 | 3 | KRT83 | 1.00 | 11682 | 3 | LHX9 | 1.00 |
| 11587 | 3 | KRT84 | 1.00 | 11683 | 3 | LILRA1 | 1.00 |
| 11588 | 3 | KRT8P41 | 1.00 | 11684 | 3 | LILRA3 | 1.00 |
| 11589 | 3 | KRTAP10-11 | 1.00 | 11685 | 3 | LILRA5 | 1.00 |
| 11590 | 3 | KRTAP10-4 | 1.00 | 11686 | 3 | LILRP2 | 1.00 |
| 11591 | 3 | KRTAP10-6 | 1.00 | 11687 | 3 | LIM2 | 1.00 |
| 11592 | 3 | KRTAP10-9 | 1.00 | 11688 | 3 | LIMS3-LOC440895 | 1.00 |
| 11593 | 3 | KRTAP12-3 | 1.00 | 11689 | 3 | LIN28A | 1.00 |
| 11594 | 3 | KRTAP12-4 | 1.00 | 11690 | 3 | LIN28B | 1.00 |
| 11595 | 3 | KRTAP13-1 | 1.00 | 11691 | 3 | LIN7A | 1.00 |
| 11596 | 3 | KRTAP13-2 | 1.00 | 11692 | 3 | LINC00028 | 1.00 |
| 11597 | 3 | KRTAP13-3 | 1.00 | 11693 | 3 | LINC00029 | 1.00 |
| 11598 | 3 | KRTAP13-4 | 1.00 | 11694 | 3 | LINC00032 | 1.00 |
| 11599 | 3 | KRTAP15-1 | 1.00 | 11695 | 3 | LINC00051 | 1.00 |
| 11600 | 3 | KRTAP19-2 | 1.00 | 11696 | 3 | LINC00052 | 1.00 |
| 11601 | 3 | KRTAP19-4 | 1.00 | 11697 | 3 | LINC00102 | 1.00 |
| 11602 | 3 | KRTAP19-5 | 1.00 | 11698 | 3 | LINC00111 | 1.00 |
| 11603 | 3 | KRTAP19-6 | 1.00 | 11699 | 3 | LINC00112 | 1.00 |
| 11604 | 3 | KRTAP19-7 | 1.00 | 11700 | 3 | LINC00113 | 1.00 |
| 11605 | 3 | KRTAP19-8 | 1.00 | 11701 | 3 | LINC00114 | 1.00 |
| 11606 | 3 | KRTAP20-1 | 1.00 | 11702 | 3 | LINC00158 | 1.00 |
| 11607 | 3 | KRTAP20-3 | 1.00 | 11703 | 3 | LINC00159 | 1.00 |
| 11608 | 3 | KRTAP20-4 | 1.00 | 11704 | 3 | LINC00160 | 1.00 |
| 11609 | 3 | KRTAP21-1 | 1.00 | 11705 | 3 | LINC00161 | 1.00 |
| 11610 | 3 | KRTAP21-2 | 1.00 | 11706 | 3 | LINC00163 | 1.00 |
| 11611 | 3 | KRTAP21-3 | 1.00 | 11707 | 3 | LINC00167 | 1.00 |
| 11612 | 3 | KRTAP22-1 | 1.00 | 11708 | 3 | LINC00184 | 1.00 |

Fig. 38 - 62

| | | | | | | | |
|---|---|---|---|---|---|---|---|
| 11709 | 3 | LINC00189 | 1.00 | 11805 | 3 | LIPI | 1.00 |
| 11710 | 3 | LINC00200 | 1.00 | 11806 | 3 | LIPJ | 1.00 |
| 11711 | 3 | LINC00202 | 1.00 | 11807 | 3 | LMAN1L | 1.00 |
| 11712 | 3 | LINC00207 | 1.00 | 11808 | 3 | LMBRD2 | 1.00 |
| 11713 | 3 | LINC00208 | 1.00 | 11809 | 3 | LMOD2 | 1.00 |
| 11714 | 3 | LINC00221 | 1.00 | 11810 | 3 | LMOD3 | 1.00 |
| 11715 | 3 | LINC00222 | 1.00 | 11811 | 3 | LMX1A | 1.00 |
| 11716 | 3 | LINC00226 | 1.00 | 11812 | 3 | LOC100093698 | 1.00 |
| 11717 | 3 | LINC00229 | 1.00 | 11813 | 3 | LOC100101266 | 1.00 |
| 11718 | 3 | LINC00230A | 1.00 | 11814 | 3 | LOC100124692 | 1.00 |
| 11719 | 3 | LINC00230B | 1.00 | 11815 | 3 | LOC100126784 | 1.00 |
| 11720 | 3 | LINC00235 | 1.00 | 11816 | 3 | LOC100128023 | 1.00 |
| 11721 | 3 | LINC00238 | 1.00 | 11817 | 3 | LOC100128054 | 1.00 |
| 11722 | 3 | LINC00239 | 1.00 | 11818 | 3 | LOC100128076 | 1.00 |
| 11723 | 3 | LINC00240 | 1.00 | 11819 | 3 | LOC100128098 | 1.00 |
| 11724 | 3 | LINC00242 | 1.00 | 11820 | 3 | LOC100128126 | 1.00 |
| 11725 | 3 | LINC00244 | 1.00 | 11821 | 3 | LOC100128176 | 1.00 |
| 11726 | 3 | LINC00246A | 1.00 | 11822 | 3 | LOC100128191 | 1.00 |
| 11727 | 3 | LINC00251 | 1.00 | 11823 | 3 | LOC100128264 | 1.00 |
| 11728 | 3 | LINC00254 | 1.00 | 11824 | 3 | LOC100128292 | 1.00 |
| 11729 | 3 | LINC00256A | 1.00 | 11825 | 3 | LOC100128496 | 1.00 |
| 11730 | 3 | LINC00256B | 1.00 | 11826 | 3 | LOC100128505 | 1.00 |
| 11731 | 3 | LINC00261 | 1.00 | 11827 | 3 | LOC100128511 | 1.00 |
| 11732 | 3 | LINC00264 | 1.00 | 11828 | 3 | LOC100128554 | 1.00 |
| 11733 | 3 | LINC00266-1 | 1.00 | 11829 | 3 | LOC100128568 | 1.00 |
| 11734 | 3 | LINC00271 | 1.00 | 11830 | 3 | LOC100128573 | 1.00 |
| 11735 | 3 | LINC00272 | 1.00 | 11831 | 3 | LOC100128590 | 1.00 |
| 11736 | 3 | LINC00273 | 1.00 | 11832 | 3 | LOC100128593 | 1.00 |
| 11737 | 3 | LINC00277 | 1.00 | 11833 | 3 | LOC100128640 | 1.00 |
| 11738 | 3 | LINC00281 | 1.00 | 11834 | 3 | LOC100128675 | 1.00 |
| 11739 | 3 | LINC00282 | 1.00 | 11835 | 3 | LOC100128682 | 1.00 |
| 11740 | 3 | LINC00284 | 1.00 | 11836 | 3 | LOC100128714 | 1.00 |
| 11741 | 3 | LINC00290 | 1.00 | 11837 | 3 | LOC100128750 | 1.00 |
| 11742 | 3 | LINC00293 | 1.00 | 11838 | 3 | LOC100128787 | 1.00 |
| 11743 | 3 | LINC00299 | 1.00 | 11839 | 3 | LOC100128788 | 1.00 |
| 11744 | 3 | LINC00301 | 1.00 | 11840 | 3 | LOC100128811 | 1.00 |
| 11745 | 3 | LINC00303 | 1.00 | 11841 | 3 | LOC100128946 | 1.00 |
| 11746 | 3 | LINC00304 | 1.00 | 11842 | 3 | LOC100128993 | 1.00 |
| 11747 | 3 | LINC00305 | 1.00 | 11843 | 3 | LOC100129027 | 1.00 |
| 11748 | 3 | LINC00307 | 1.00 | 11844 | 3 | LOC100129055 | 1.00 |
| 11749 | 3 | LINC00308 | 1.00 | 11845 | 3 | LOC100129083 | 1.00 |
| 11750 | 3 | LINC00309 | 1.00 | 11846 | 3 | LOC100129175 | 1.00 |
| 11751 | 3 | LINC00311 | 1.00 | 11847 | 3 | LOC100129213 | 1.00 |
| 11752 | 3 | LINC00313 | 1.00 | 11848 | 3 | LOC100129216 | 1.00 |
| 11753 | 3 | LINC00314 | 1.00 | 11849 | 3 | LOC100129316 | 1.00 |
| 11754 | 3 | LINC00315 | 1.00 | 11850 | 3 | LOC100129345 | 1.00 |
| 11755 | 3 | LINC00317 | 1.00 | 11851 | 3 | LOC100129407 | 1.00 |
| 11756 | 3 | LINC00320 | 1.00 | 11852 | 3 | LOC100129427 | 1.00 |
| 11757 | 3 | LINC00323 | 1.00 | 11853 | 3 | LOC100129515 | 1.00 |
| 11758 | 3 | LINC00326 | 1.00 | 11854 | 3 | LOC100129520 | 1.00 |
| 11759 | 3 | LINC00330 | 1.00 | 11855 | 3 | LOC100129617 | 1.00 |
| 11760 | 3 | LINC00336 | 1.00 | 11856 | 3 | LOC100129620 | 1.00 |
| 11761 | 3 | LINC00340 | 1.00 | 11857 | 3 | LOC100129636 | 1.00 |
| 11762 | 3 | LINC00346 | 1.00 | 11858 | 3 | LOC100129662 | 1.00 |
| 11763 | 3 | LINC00347 | 1.00 | 11859 | 3 | LOC100129716 | 1.00 |
| 11764 | 3 | LINC00410 | 1.00 | 11860 | 3 | LOC100129726 | 1.00 |
| 11765 | 3 | LINC00421 | 1.00 | 11861 | 3 | LOC100129845 | 1.00 |
| 11766 | 3 | LINC00442 | 1.00 | 11862 | 3 | LOC100129858 | 1.00 |
| 11767 | 3 | LINC00460 | 1.00 | 11863 | 3 | LOC100129924 | 1.00 |
| 11768 | 3 | LINC00461 | 1.00 | 11864 | 3 | LOC100129931 | 1.00 |
| 11769 | 3 | LINC00466 | 1.00 | 11865 | 3 | LOC100129935 | 1.00 |
| 11770 | 3 | LINC00469 | 1.00 | 11866 | 3 | LOC100130000 | 1.00 |
| 11771 | 3 | LINC00470 | 1.00 | 11867 | 3 | LOC100130155 | 1.00 |
| 11772 | 3 | LINC00471 | 1.00 | 11868 | 3 | LOC100130197 | 1.00 |
| 11773 | 3 | LINC00472 | 1.00 | 11869 | 3 | LOC100130231 | 1.00 |
| 11774 | 3 | LINC00473 | 1.00 | 11870 | 3 | LOC100130238 | 1.00 |
| 11775 | 3 | LINC00474 | 1.00 | 11871 | 3 | LOC100130264 | 1.00 |
| 11776 | 3 | LINC00475 | 1.00 | 11872 | 3 | LOC100130298 | 1.00 |
| 11777 | 3 | LINC00477 | 1.00 | 11873 | 3 | LOC100130301 | 1.00 |
| 11778 | 3 | LINC00482 | 1.00 | 11874 | 3 | LOC100130348 | 1.00 |
| 11779 | 3 | LINC00483 | 1.00 | 11875 | 3 | LOC100130357 | 1.00 |
| 11780 | 3 | LINC00485 | 1.00 | 11876 | 3 | LOC100130417 | 1.00 |
| 11781 | 3 | LINC00486 | 1.00 | 11877 | 3 | LOC100130451 | 1.00 |
| 11782 | 3 | LINC00487 | 1.00 | 11878 | 3 | LOC100130452 | 1.00 |
| 11783 | 3 | LINC00488 | 1.00 | 11879 | 3 | LOC100130480 | 1.00 |
| 11784 | 3 | LINC00494 | 1.00 | 11880 | 3 | LOC100130673 | 1.00 |
| 11785 | 3 | LINC00511 | 1.00 | 11881 | 3 | LOC100130700 | 1.00 |
| 11786 | 3 | LINC00514 | 1.00 | 11882 | 3 | LOC100130849 | 1.00 |
| 11787 | 3 | LINC00515 | 1.00 | 11883 | 3 | LOC100130872 | 1.00 |
| 11788 | 3 | LINC00518 | 1.00 | 11884 | 3 | LOC100130880 | 1.00 |
| 11789 | 3 | LINC00520 | 1.00 | 11885 | 3 | LOC100130894 | 1.00 |
| 11790 | 3 | LINC00521 | 1.00 | 11886 | 3 | LOC100130954 | 1.00 |
| 11791 | 3 | LINC00523 | 1.00 | 11887 | 3 | LOC100130964 | 1.00 |
| 11792 | 3 | LINC00525 | 1.00 | 11888 | 3 | LOC100130992 | 1.00 |
| 11793 | 3 | LINC00535 | 1.00 | 11889 | 3 | LOC100131047 | 1.00 |
| 11794 | 3 | LINC00536 | 1.00 | 11890 | 3 | LOC100131060 | 1.00 |
| 11795 | 3 | LINC00538 | 1.00 | 11891 | 3 | LOC100131138 | 1.00 |
| 11796 | 3 | LINC00547 | 1.00 | 11892 | 3 | LOC100131176 | 1.00 |
| 11797 | 3 | LINC00548 | 1.00 | 11893 | 3 | LOC100131208 | 1.00 |
| 11798 | 3 | LINC00550 | 1.00 | 11894 | 3 | LOC100131234 | 1.00 |
| 11799 | 3 | LINC00552 | 1.00 | 11895 | 3 | LOC100131257 | 1.00 |
| 11800 | 3 | LINC00574 | 1.00 | 11896 | 3 | LOC100131320 | 1.00 |
| 11801 | 3 | LINC00575 | 1.00 | 11897 | 3 | LOC100131347 | 1.00 |
| 11802 | 3 | LINGO3 | 1.00 | 11898 | 3 | LOC100131366 | 1.00 |
| 11803 | 3 | LINGO4 | 1.00 | 11899 | 3 | LOC100131496 | 1.00 |
| 11804 | 3 | LIPF | 1.00 | 11900 | 3 | LOC100131551 | 1.00 |

Fig. 38 - 63

| | | | | | | | | | | | | | | |
|---|---|---|---|---|---|---|---|---|---|---|---|---|---|---|
| 11901 | 3 | | | | | LOC100131628 | 1.00 | 11997 | 3 | | | | LOC100499183 | 1.00 |
| 11902 | 3 | | | | | LOC100131635 | 1.00 | 11998 | 3 | | | | LOC100499194 | 1.00 |
| 11903 | 3 | | | | | LOC100131655 | 1.00 | 11999 | 3 | | | | LOC100499227 | 1.00 |
| 11904 | 3 | | | | | LOC100131733 | 1.00 | 12000 | 3 | | | | LOC100499484 | 1.00 |
| 11905 | 3 | | | | | LOC100132077 | 1.00 | 12001 | 3 | | | | LOC100500773 | 1.00 |
| 11906 | 3 | | | | | LOC100132078 | 1.00 | 12002 | 3 | | | | LOC100500938 | 1.00 |
| 11907 | 3 | | | | | LOC100132146 | 1.00 | 12003 | 3 | | | | LOC100505474 | 1.00 |
| 11908 | 3 | | | | | LOC100132354 | 1.00 | 12004 | 3 | | | | LOC100505478 | 1.00 |
| 11909 | 3 | | | | | LOC100132396 | 1.00 | 12005 | 3 | | | | LOC100505536 | 1.00 |
| 11910 | 3 | | | | | LOC100132526 | 1.00 | 12006 | 3 | | | | LOC100505540 | 1.00 |
| 11911 | 3 | | | | | LOC100132735 | 1.00 | 12007 | 3 | | | | LOC100505545 | 1.00 |
| 11912 | 3 | | | | | LOC100132781 | 1.00 | 12008 | 3 | | | | LOC100505583 | 1.00 |
| 11913 | 3 | | | | | LOC100132987 | 1.00 | 12009 | 3 | | | | LOC100505619 | 1.00 |
| 11914 | 3 | | | | | LOC100133050 | 1.00 | 12010 | 3 | | | | LOC100505622 | 1.00 |
| 11915 | 3 | | | | | LOC100133123 | 1.00 | 12011 | 3 | | | | LOC100505658 | 1.00 |
| 11916 | 3 | | | | | LOC100133267 | 1.00 | 12012 | 3 | | | | LOC100505659 | 1.00 |
| 11917 | 3 | | | | | LOC100133308 | 1.00 | 12013 | 3 | | | | LOC100505676 | 1.00 |
| 11918 | 3 | | | | | LOC100133315 | 1.00 | 12014 | 3 | | | | LOC100505679 | 1.00 |
| 11919 | 3 | | | | | LOC100133461 | 1.00 | 12015 | 3 | | | | LOC100505695 | 1.00 |
| 11920 | 3 | | | | | LOC100133612 | 1.00 | 12016 | 3 | | | | LOC100505716 | 1.00 |
| 11921 | 3 | | | | | LOC100133920 | 1.00 | 12017 | 3 | | | | LOC100505718 | 1.00 |
| 11922 | 3 | | | | | LOC100133957 | 1.00 | 12018 | 3 | | | | LOC100505768 | 1.00 |
| 11923 | 3 | | | | | LOC100133985 | 1.00 | 12019 | 3 | | | | LOC100505776 | 1.00 |
| 11924 | 3 | | | | | LOC100134015 | 1.00 | 12020 | 3 | | | | LOC100505782 | 1.00 |
| 11925 | 3 | | | | | LOC100134259 | 1.00 | 12021 | 3 | | | | LOC100505795 | 1.00 |
| 11926 | 3 | | | | | LOC100134368 | 1.00 | 12022 | 3 | | | | LOC100505817 | 1.00 |
| 11927 | 3 | | | | | LOC100144595 | 1.00 | 12023 | 3 | | | | LOC100505826 | 1.00 |
| 11928 | 3 | | | | | LOC100144597 | 1.00 | 12024 | 3 | | | | LOC100505835 | 1.00 |
| 11929 | 3 | | | | | LOC100144602 | 1.00 | 12025 | 3 | | | | LOC100505841 | 1.00 |
| 11930 | 3 | | | | | LOC100144603 | 1.00 | 12026 | 3 | | | | LOC100505875 | 1.00 |
| 11931 | 3 | | | | | LOC100144604 | 1.00 | 12027 | 3 | | | | LOC100505912 | 1.00 |
| 11932 | 3 | | | | | LOC100169752 | 1.00 | 12028 | 3 | | | | LOC100505918 | 1.00 |
| 11933 | 3 | | | | | LOC100170939 | 1.00 | 12029 | 3 | | | | LOC100505964 | 1.00 |
| 11934 | 3 | | | | | LOC100188947 | 1.00 | 12030 | 3 | | | | LOC100505967 | 1.00 |
| 11935 | 3 | | | | | LOC100189589 | 1.00 | 12031 | 3 | | | | LOC100505978 | 1.00 |
| 11936 | 3 | | | | | LOC100190940 | 1.00 | 12032 | 3 | | | | LOC100505989 | 1.00 |
| 11937 | 3 | | | | | LOC100192378 | 1.00 | 12033 | 3 | | | | LOC100506012 | 1.00 |
| 11938 | 3 | | | | | LOC100192426 | 1.00 | 12034 | 3 | | | | LOC100506023 | 1.00 |
| 11939 | 3 | | | | | LOC100216001 | 1.00 | 12035 | 3 | | | | LOC100506025 | 1.00 |
| 11940 | 3 | | | | | LOC100216479 | 1.00 | 12036 | 3 | | | | LOC100506035 | 1.00 |
| 11941 | 3 | | | | | LOC100233209 | 1.00 | 12037 | 3 | | | | LOC100506050 | 1.00 |
| 11942 | 3 | | | | | LOC100240734 | 1.00 | 12038 | 3 | | | | LOC100506083 | 1.00 |
| 11943 | 3 | | | | | LOC100268168 | 1.00 | 12039 | 3 | | | | LOC100506085 | 1.00 |
| 11944 | 3 | | | | | LOC100270679 | 1.00 | 12040 | 3 | | | | LOC100506122 | 1.00 |
| 11945 | 3 | | | | | LOC100271702 | 1.00 | 12041 | 3 | | | | LOC100506134 | 1.00 |
| 11946 | 3 | | | | | LOC100271832 | 1.00 | 12042 | 3 | | | | LOC100506136 | 1.00 |
| 11947 | 3 | | | | | LOC100271836 | 1.00 | 12043 | 3 | | | | LOC100506172 | 1.00 |
| 11948 | 3 | | | | | LOC100272217 | 1.00 | 12044 | 3 | | | | LOC100506178 | 1.00 |
| 11949 | 3 | | | | | LOC100286844 | 1.00 | 12045 | 3 | | | | LOC100506195 | 1.00 |
| 11950 | 3 | | | | | LOC100286922 | 1.00 | 12046 | 3 | | | | LOC100506229 | 1.00 |
| 11951 | 3 | | | | | LOC100286938 | 1.00 | 12047 | 3 | | | | LOC100506241 | 1.00 |
| 11952 | 3 | | | | | LOC100286979 | 1.00 | 12048 | 3 | | | | LOC100506274 | 1.00 |
| 11953 | 3 | | | | | LOC100287010 | 1.00 | 12049 | 3 | | | | LOC100506321 | 1.00 |
| 11954 | 3 | | | | | LOC100287036 | 1.00 | 12050 | 3 | | | | LOC100506343 | 1.00 |
| 11955 | 3 | | | | | LOC100287216 | 1.00 | 12051 | 3 | | | | LOC100506368 | 1.00 |
| 11956 | 3 | | | | | LOC100287225 | 1.00 | 12052 | 3 | | | | LOC100506384 | 1.00 |
| 11957 | 3 | | | | | LOC100287314 | 1.00 | 12053 | 3 | | | | LOC100506385 | 1.00 |
| 11958 | 3 | | | | | LOC100287482 | 1.00 | 12054 | 3 | | | | LOC100506393 | 1.00 |
| 11959 | 3 | | | | | LOC100287559 | 1.00 | 12055 | 3 | | | | LOC100506409 | 1.00 |
| 11960 | 3 | | | | | LOC100287632 | 1.00 | 12056 | 3 | | | | LOC100506421 | 1.00 |
| 11961 | 3 | | | | | LOC100287718 | 1.00 | 12057 | 3 | | | | LOC100506422 | 1.00 |
| 11962 | 3 | | | | | LOC100287792 | 1.00 | 12058 | 3 | | | | LOC100506433 | 1.00 |
| 11963 | 3 | | | | | LOC100287814 | 1.00 | 12059 | 3 | | | | LOC100506462 | 1.00 |
| 11964 | 3 | | | | | LOC100287834 | 1.00 | 12060 | 3 | | | | LOC100506474 | 1.00 |
| 11965 | 3 | | | | | LOC100287846 | 1.00 | 12061 | 3 | | | | LOC100506497 | 1.00 |
| 11966 | 3 | | | | | LOC100287879 | 1.00 | 12062 | 3 | | | | LOC100506540 | 1.00 |
| 11967 | 3 | | | | | LOC100287944 | 1.00 | 12063 | 3 | | | | LOC100506585 | 1.00 |
| 11968 | 3 | | | | | LOC100288077 | 1.00 | 12064 | 3 | | | | LOC100506650 | 1.00 |
| 11969 | 3 | | | | | LOC100288079 | 1.00 | 12065 | 3 | | | | LOC100506655 | 1.00 |
| 11970 | 3 | | | | | LOC100288122 | 1.00 | 12066 | 3 | | | | LOC100506660 | 1.00 |
| 11971 | 3 | | | | | LOC100288181 | 1.00 | 12067 | 3 | | | | LOC100506688 | 1.00 |
| 11972 | 3 | | | | | LOC100288255 | 1.00 | 12068 | 3 | | | | LOC100506733 | 1.00 |
| 11973 | 3 | | | | | LOC100288346 | 1.00 | 12069 | 3 | | | | LOC100506757 | 1.00 |
| 11974 | 3 | | | | | LOC100288428 | 1.00 | 12070 | 3 | | | | LOC100506795 | 1.00 |
| 11975 | 3 | | | | | LOC100288524 | 1.00 | 12071 | 3 | | | | LOC100506801 | 1.00 |
| 11976 | 3 | | | | | LOC100288570 | 1.00 | 12072 | 3 | | | | LOC100506804 | 1.00 |
| 11977 | 3 | | | | | LOC100288814 | 1.00 | 12073 | 3 | | | | LOC100506810 | 1.00 |
| 11978 | 3 | | | | | LOC100288846 | 1.00 | 12074 | 3 | | | | LOC100506835 | 1.00 |
| 11979 | 3 | | | | | LOC100288974 | 1.00 | 12075 | 3 | | | | LOC100506888 | 1.00 |
| 11980 | 3 | | | | | LOC100289092 | 1.00 | 12076 | 3 | | | | LOC100506895 | 1.00 |
| 11981 | 3 | | | | | LOC100289178 | 1.00 | 12077 | 3 | | | | LOC100506994 | 1.00 |
| 11982 | 3 | | | | | LOC100289211 | 1.00 | 12078 | 3 | | | | LOC100507003 | 1.00 |
| 11983 | 3 | | | | | LOC100289495 | 1.00 | 12079 | 3 | | | | LOC100507032 | 1.00 |
| 11984 | 3 | | | | | LOC100289650 | 1.00 | 12080 | 3 | | | | LOC100507043 | 1.00 |
| 11985 | 3 | | | | | LOC100289656 | 1.00 | 12081 | 3 | | | | LOC100507050 | 1.00 |
| 11986 | 3 | | | | | LOC100289673 | 1.00 | 12082 | 3 | | | | LOC100507053 | 1.00 |
| 11987 | 3 | | | | | LOC100292680 | 1.00 | 12083 | 3 | | | | LOC100507055 | 1.00 |
| 11988 | 3 | | | | | LOC100293534 | 1.00 | 12084 | 3 | | | | LOC100507066 | 1.00 |
| 11989 | 3 | | | | | LOC100302401 | 1.00 | 12085 | 3 | | | | LOC100507086 | 1.00 |
| 11990 | 3 | | | | | LOC100302640 | 1.00 | 12086 | 3 | | | | LOC100507091 | 1.00 |
| 11991 | 3 | | | | | LOC100303749 | 1.00 | 12087 | 3 | | | | LOC100507096 | 1.00 |
| 11992 | 3 | | | | | LOC100306975 | 1.00 | 12088 | 3 | | | | LOC100507127 | 1.00 |
| 11993 | 3 | | | | | LOC100329135 | 1.00 | 12089 | 3 | | | | LOC100507140 | 1.00 |
| 11994 | 3 | | | | | LOC100379224 | 1.00 | 12090 | 3 | | | | LOC100507156 | 1.00 |
| 11995 | 3 | | | | | LOC100422737 | 1.00 | 12091 | 3 | | | | LOC100507173 | 1.00 |
| 11996 | 3 | | | | | LOC100498859 | 1.00 | 12092 | 3 | | | | LOC100507178 | 1.00 |

Fig. 38 - 64

| | | | | | | | | | | | | | |
|---|---|---|---|---|---|---|---|---|---|---|---|---|---|
| 12093 | 3 | | | | LOC100507194 | 1.00 | 12189 | 3 | | | | LOC153910 | 1.00 |
| 12094 | 3 | | | | LOC100507203 | 1.00 | 12190 | 3 | | | | LOC154092 | 1.00 |
| 12095 | 3 | | | | LOC100507205 | 1.00 | 12191 | 3 | | | | LOC154449 | 1.00 |
| 12096 | 3 | | | | LOC100507206 | 1.00 | 12192 | 3 | | | | LOC154822 | 1.00 |
| 12097 | 3 | | | | LOC100507218 | 1.00 | 12193 | 3 | | | | LOC154860 | 1.00 |
| 12098 | 3 | | | | LOC100507240 | 1.00 | 12194 | 3 | | | | LOC154872 | 1.00 |
| 12099 | 3 | | | | LOC100507244 | 1.00 | 12195 | 3 | | | | LOC157273 | 1.00 |
| 12100 | 3 | | | | LOC100507250 | 1.00 | 12196 | 3 | | | | LOC157627 | 1.00 |
| 12101 | 3 | | | | LOC100507266 | 1.00 | 12197 | 3 | | | | LOC158434 | 1.00 |
| 12102 | 3 | | | | LOC100507299 | 1.00 | 12198 | 3 | | | | LOC158435 | 1.00 |
| 12103 | 3 | | | | LOC100507300 | 1.00 | 12199 | 3 | | | | LOC158696 | 1.00 |
| 12104 | 3 | | | | LOC100507334 | 1.00 | 12200 | 3 | | | | LOC170425 | 1.00 |
| 12105 | 3 | | | | LOC100507341 | 1.00 | 12201 | 3 | | | | LOC1720 | 1.00 |
| 12106 | 3 | | | | LOC100507346 | 1.00 | 12202 | 3 | | | | LOC200261 | 1.00 |
| 12107 | 3 | | | | LOC100507362 | 1.00 | 12203 | 3 | | | | LOC200726 | 1.00 |
| 12108 | 3 | | | | LOC100507377 | 1.00 | 12204 | 3 | | | | LOC200772 | 1.00 |
| 12109 | 3 | | | | LOC100507389 | 1.00 | 12205 | 3 | | | | LOC201477 | 1.00 |
| 12110 | 3 | | | | LOC100507391 | 1.00 | 12206 | 3 | | | | LOC201617 | 1.00 |
| 12111 | 3 | | | | LOC100507404 | 1.00 | 12207 | 3 | | | | LOC201651 | 1.00 |
| 12112 | 3 | | | | LOC100507410 | 1.00 | 12208 | 3 | | | | LOC219731 | 1.00 |
| 12113 | 3 | | | | LOC100507421 | 1.00 | 12209 | 3 | | | | LOC221122 | 1.00 |
| 12114 | 3 | | | | LOC100507423 | 1.00 | 12210 | 3 | | | | LOC221442 | 1.00 |
| 12115 | 3 | | | | LOC100507443 | 1.00 | 12211 | 3 | | | | LOC253044 | 1.00 |
| 12116 | 3 | | | | LOC100507462 | 1.00 | 12212 | 3 | | | | LOC253573 | 1.00 |
| 12117 | 3 | | | | LOC100507466 | 1.00 | 12213 | 3 | | | | LOC253962 | 1.00 |
| 12118 | 3 | | | | LOC100507470 | 1.00 | 12214 | 3 | | | | LOC254099 | 1.00 |
| 12119 | 3 | | | | LOC100507472 | 1.00 | 12215 | 3 | | | | LOC254312 | 1.00 |
| 12120 | 3 | | | | LOC100507489 | 1.00 | 12216 | 3 | | | | LOC254559 | 1.00 |
| 12121 | 3 | | | | LOC100507537 | 1.00 | 12217 | 3 | | | | LOC254896 | 1.00 |
| 12122 | 3 | | | | LOC100507582 | 1.00 | 12218 | 3 | | | | LOC255025 | 1.00 |
| 12123 | 3 | | | | LOC100507584 | 1.00 | 12219 | 3 | | | | LOC255411 | 1.00 |
| 12124 | 3 | | | | LOC100507588 | 1.00 | 12220 | 3 | | | | LOC255654 | 1.00 |
| 12125 | 3 | | | | LOC100507589 | 1.00 | 12221 | 3 | | | | LOC256880 | 1.00 |
| 12126 | 3 | | | | LOC100507600 | 1.00 | 12222 | 3 | | | | LOC257358 | 1.00 |
| 12127 | 3 | | | | LOC100507605 | 1.00 | 12223 | 3 | | | | LOC282980 | 1.00 |
| 12128 | 3 | | | | LOC100507629 | 1.00 | 12224 | 3 | | | | LOC283033 | 1.00 |
| 12129 | 3 | | | | LOC100507634 | 1.00 | 12225 | 3 | | | | LOC283038 | 1.00 |
| 12130 | 3 | | | | LOC100507651 | 1.00 | 12226 | 3 | | | | LOC283089 | 1.00 |
| 12131 | 3 | | | | LOC100509575 | 1.00 | 12227 | 3 | | | | LOC283116 | 1.00 |
| 12132 | 3 | | | | LOC100509894 | 1.00 | 12228 | 3 | | | | LOC283177 | 1.00 |
| 12133 | 3 | | | | LOC100526771 | 1.00 | 12229 | 3 | | | | LOC283194 | 1.00 |
| 12134 | 3 | | | | LOC100616530 | 1.00 | 12230 | 3 | | | | LOC283214 | 1.00 |
| 12135 | 3 | | | | LOC100628307 | 1.00 | 12231 | 3 | | | | LOC283299 | 1.00 |
| 12136 | 3 | | | | LOC100631378 | 1.00 | 12232 | 3 | | | | LOC283332 | 1.00 |
| 12137 | 3 | | | | LOC100652730 | 1.00 | 12233 | 3 | | | | LOC283403 | 1.00 |
| 12138 | 3 | | | | LOC100652759 | 1.00 | 12234 | 3 | | | | LOC283440 | 1.00 |
| 12139 | 3 | | | | LOC100652770 | 1.00 | 12235 | 3 | | | | LOC283547 | 1.00 |
| 12140 | 3 | | | | LOC100652791 | 1.00 | 12236 | 3 | | | | LOC283585 | 1.00 |
| 12141 | 3 | | | | LOC100652846 | 1.00 | 12237 | 3 | | | | LOC283587 | 1.00 |
| 12142 | 3 | | | | LOC100652909 | 1.00 | 12238 | 3 | | | | LOC283683 | 1.00 |
| 12143 | 3 | | | | LOC100653515 | 1.00 | 12239 | 3 | | | | LOC283688 | 1.00 |
| 12144 | 3 | | | | LOC116437 | 1.00 | 12240 | 3 | | | | LOC283693 | 1.00 |
| 12145 | 3 | | | | LOC120824 | 1.00 | 12241 | 3 | | | | LOC283710 | 1.00 |
| 12146 | 3 | | | | LOC126536 | 1.00 | 12242 | 3 | | | | LOC283731 | 1.00 |
| 12147 | 3 | | | | LOC127841 | 1.00 | 12243 | 3 | | | | LOC283738 | 1.00 |
| 12148 | 3 | | | | LOC143188 | 1.00 | 12244 | 3 | | | | LOC283761 | 1.00 |
| 12149 | 3 | | | | LOC144486 | 1.00 | 12245 | 3 | | | | LOC283856 | 1.00 |
| 12150 | 3 | | | | LOC144742 | 1.00 | 12246 | 3 | | | | LOC283867 | 1.00 |
| 12151 | 3 | | | | LOC145216 | 1.00 | 12247 | 3 | | | | LOC283888 | 1.00 |
| 12152 | 3 | | | | LOC145474 | 1.00 | 12248 | 3 | | | | LOC283914 | 1.00 |
| 12153 | 3 | | | | LOC145663 | 1.00 | 12249 | 3 | | | | LOC284080 | 1.00 |
| 12154 | 3 | | | | LOC145820 | 1.00 | 12250 | 3 | | | | LOC284100 | 1.00 |
| 12155 | 3 | | | | LOC145837 | 1.00 | 12251 | 3 | | | | LOC284215 | 1.00 |
| 12156 | 3 | | | | LOC145845 | 1.00 | 12252 | 3 | | | | LOC284260 | 1.00 |
| 12157 | 3 | | | | LOC146336 | 1.00 | 12253 | 3 | | | | LOC284294 | 1.00 |
| 12158 | 3 | | | | LOC146481 | 1.00 | 12254 | 3 | | | | LOC284344 | 1.00 |
| 12159 | 3 | | | | LOC146513 | 1.00 | 12255 | 3 | | | | LOC284379 | 1.00 |
| 12160 | 3 | | | | LOC147093 | 1.00 | 12256 | 3 | | | | LOC284395 | 1.00 |
| 12161 | 3 | | | | LOC147646 | 1.00 | 12257 | 3 | | | | LOC284551 | 1.00 |
| 12162 | 3 | | | | LOC147670 | 1.00 | 12258 | 3 | | | | LOC284576 | 1.00 |
| 12163 | 3 | | | | LOC148145 | 1.00 | 12259 | 3 | | | | LOC284632 | 1.00 |
| 12164 | 3 | | | | LOC148696 | 1.00 | 12260 | 3 | | | | LOC284648 | 1.00 |
| 12165 | 3 | | | | LOC148709 | 1.00 | 12261 | 3 | | | | LOC284661 | 1.00 |
| 12166 | 3 | | | | LOC148824 | 1.00 | 12262 | 3 | | | | LOC284688 | 1.00 |
| 12167 | 3 | | | | LOC149086 | 1.00 | 12263 | 3 | | | | LOC284751 | 1.00 |
| 12168 | 3 | | | | LOC149373 | 1.00 | 12264 | 3 | | | | LOC284757 | 1.00 |
| 12169 | 3 | | | | LOC149773 | 1.00 | 12265 | 3 | | | | LOC284788 | 1.00 |
| 12170 | 3 | | | | LOC149950 | 1.00 | 12266 | 3 | | | | LOC284798 | 1.00 |
| 12171 | 3 | | | | LOC150185 | 1.00 | 12267 | 3 | | | | LOC284801 | 1.00 |
| 12172 | 3 | | | | LOC150197 | 1.00 | 12268 | 3 | | | | LOC284865 | 1.00 |
| 12173 | 3 | | | | LOC150381 | 1.00 | 12269 | 3 | | | | LOC284933 | 1.00 |
| 12174 | 3 | | | | LOC150527 | 1.00 | 12270 | 3 | | | | LOC284950 | 1.00 |
| 12175 | 3 | | | | LOC150568 | 1.00 | 12271 | 3 | | | | LOC284998 | 1.00 |
| 12176 | 3 | | | | LOC150622 | 1.00 | 12272 | 3 | | | | LOC285000 | 1.00 |
| 12177 | 3 | | | | LOC150935 | 1.00 | 12273 | 3 | | | | LOC285103 | 1.00 |
| 12178 | 3 | | | | LOC151171 | 1.00 | 12274 | 3 | | | | LOC285205 | 1.00 |
| 12179 | 3 | | | | LOC151174 | 1.00 | 12275 | 3 | | | | LOC285326 | 1.00 |
| 12180 | 3 | | | | LOC151300 | 1.00 | 12276 | 3 | | | | LOC285370 | 1.00 |
| 12181 | 3 | | | | LOC151475 | 1.00 | 12277 | 3 | | | | LOC285375 | 1.00 |
| 12182 | 3 | | | | LOC151484 | 1.00 | 12278 | 3 | | | | LOC285401 | 1.00 |
| 12183 | 3 | | | | LOC151658 | 1.00 | 12279 | 3 | | | | LOC285441 | 1.00 |
| 12184 | 3 | | | | LOC152024 | 1.00 | 12280 | 3 | | | | LOC285456 | 1.00 |
| 12185 | 3 | | | | LOC152225 | 1.00 | 12281 | 3 | | | | LOC285484 | 1.00 |
| 12186 | 3 | | | | LOC152578 | 1.00 | 12282 | 3 | | | | LOC285501 | 1.00 |
| 12187 | 3 | | | | LOC152742 | 1.00 | 12283 | 3 | | | | LOC285547 | 1.00 |
| 12188 | 3 | | | | LOC153469 | 1.00 | 12284 | 3 | | | | LOC285548 | 1.00 |

Fig. 38 - 65

| | | | | | | | | | | | | | | |
|---|---|---|---|---|---|---|---|---|---|---|---|---|---|---|
| 12285 | 3 | | | | | LOC285577 | 1.00 | 12381 | 3 | | | | LOC389791 | 1.00 |
| 12286 | 3 | | | | | LOC285593 | 1.00 | 12382 | 3 | | | | LOC390660 | 1.00 |
| 12287 | 3 | | | | | LOC285626 | 1.00 | 12383 | 3 | | | | LOC390705 | 1.00 |
| 12288 | 3 | | | | | LOC285627 | 1.00 | 12384 | 3 | | | | LOC390858 | 1.00 |
| 12289 | 3 | | | | | LOC285629 | 1.00 | 12385 | 3 | | | | LOC392196 | 1.00 |
| 12290 | 3 | | | | | LOC285692 | 1.00 | 12386 | 3 | | | | LOC392232 | 1.00 |
| 12291 | 3 | | | | | LOC285696 | 1.00 | 12387 | 3 | | | | LOC392364 | 1.00 |
| 12292 | 3 | | | | | LOC285740 | 1.00 | 12388 | 3 | | | | LOC399708 | 1.00 |
| 12293 | 3 | | | | | LOC285758 | 1.00 | 12389 | 3 | | | | LOC399715 | 1.00 |
| 12294 | 3 | | | | | LOC285762 | 1.00 | 12390 | 3 | | | | LOC399815 | 1.00 |
| 12295 | 3 | | | | | LOC285768 | 1.00 | 12391 | 3 | | | | LOC399829 | 1.00 |
| 12296 | 3 | | | | | LOC285796 | 1.00 | 12392 | 3 | | | | LOC399939 | 1.00 |
| 12297 | 3 | | | | | LOC285819 | 1.00 | 12393 | 3 | | | | LOC399940 | 1.00 |
| 12298 | 3 | | | | | LOC285847 | 1.00 | 12394 | 3 | | | | LOC400084 | 1.00 |
| 12299 | 3 | | | | | LOC285878 | 1.00 | 12395 | 3 | | | | LOC400238 | 1.00 |
| 12300 | 3 | | | | | LOC285889 | 1.00 | 12396 | 3 | | | | LOC400456 | 1.00 |
| 12301 | 3 | | | | | LOC285954 | 1.00 | 12397 | 3 | | | | LOC400548 | 1.00 |
| 12302 | 3 | | | | | LOC285965 | 1.00 | 12398 | 3 | | | | LOC400550 | 1.00 |
| 12303 | 3 | | | | | LOC285972 | 1.00 | 12399 | 3 | | | | LOC400558 | 1.00 |
| 12304 | 3 | | | | | LOC286002 | 1.00 | 12400 | 3 | | | | LOC400620 | 1.00 |
| 12305 | 3 | | | | | LOC286059 | 1.00 | 12401 | 3 | | | | LOC400643 | 1.00 |
| 12306 | 3 | | | | | LOC286083 | 1.00 | 12402 | 3 | | | | LOC400654 | 1.00 |
| 12307 | 3 | | | | | LOC286094 | 1.00 | 12403 | 3 | | | | LOC400655 | 1.00 |
| 12308 | 3 | | | | | LOC286114 | 1.00 | 12404 | 3 | | | | LOC400680 | 1.00 |
| 12309 | 3 | | | | | LOC286135 | 1.00 | 12405 | 3 | | | | LOC400684 | 1.00 |
| 12310 | 3 | | | | | LOC286177 | 1.00 | 12406 | 3 | | | | LOC400685 | 1.00 |
| 12311 | 3 | | | | | LOC286184 | 1.00 | 12407 | 3 | | | | LOC400794 | 1.00 |
| 12312 | 3 | | | | | LOC286186 | 1.00 | 12408 | 3 | | | | LOC400891 | 1.00 |
| 12313 | 3 | | | | | LOC286189 | 1.00 | 12409 | 3 | | | | LOC400940 | 1.00 |
| 12314 | 3 | | | | | LOC286190 | 1.00 | 12410 | 3 | | | | LOC400958 | 1.00 |
| 12315 | 3 | | | | | LOC286238 | 1.00 | 12411 | 3 | | | | LOC401134 | 1.00 |
| 12316 | 3 | | | | | LOC286297 | 1.00 | 12412 | 3 | | | | LOC401164 | 1.00 |
| 12317 | 3 | | | | | LOC286359 | 1.00 | 12413 | 3 | | | | LOC401177 | 1.00 |
| 12318 | 3 | | | | | LOC286370 | 1.00 | 12414 | 3 | | | | LOC401242 | 1.00 |
| 12319 | 3 | | | | | LOC286442 | 1.00 | 12415 | 3 | | | | LOC401324 | 1.00 |
| 12320 | 3 | | | | | LOC286467 | 1.00 | 12416 | 3 | | | | LOC401431 | 1.00 |
| 12321 | 3 | | | | | LOC338579 | 1.00 | 12417 | 3 | | | | LOC401463 | 1.00 |
| 12322 | 3 | | | | | LOC338588 | 1.00 | 12418 | 3 | | | | LOC401497 | 1.00 |
| 12323 | 3 | | | | | LOC338651 | 1.00 | 12419 | 3 | | | | LOC401557 | 1.00 |
| 12324 | 3 | | | | | LOC338739 | 1.00 | 12420 | 3 | | | | LOC401980 | 1.00 |
| 12325 | 3 | | | | | LOC338817 | 1.00 | 12421 | 3 | | | | LOC402160 | 1.00 |
| 12326 | 3 | | | | | LOC338963 | 1.00 | 12422 | 3 | | | | LOC402779 | 1.00 |
| 12327 | 3 | | | | | LOC339166 | 1.00 | 12423 | 3 | | | | LOC415056 | 1.00 |
| 12328 | 3 | | | | | LOC339240 | 1.00 | 12424 | 3 | | | | LOC439949 | 1.00 |
| 12329 | 3 | | | | | LOC339298 | 1.00 | 12425 | 3 | | | | LOC439950 | 1.00 |
| 12330 | 3 | | | | | LOC339442 | 1.00 | 12426 | 3 | | | | LOC440028 | 1.00 |
| 12331 | 3 | | | | | LOC339505 | 1.00 | 12427 | 3 | | | | LOC440040 | 1.00 |
| 12332 | 3 | | | | | LOC339529 | 1.00 | 12428 | 3 | | | | LOC440041 | 1.00 |
| 12333 | 3 | | | | | LOC339568 | 1.00 | 12429 | 3 | | | | LOC440117 | 1.00 |
| 12334 | 3 | | | | | LOC339593 | 1.00 | 12430 | 3 | | | | LOC440131 | 1.00 |
| 12335 | 3 | | | | | LOC339622 | 1.00 | 12431 | 3 | | | | LOC440173 | 1.00 |
| 12336 | 3 | | | | | LOC339666 | 1.00 | 12432 | 3 | | | | LOC440356 | 1.00 |
| 12337 | 3 | | | | | LOC339685 | 1.00 | 12433 | 3 | | | | LOC440461 | 1.00 |
| 12338 | 3 | | | | | LOC339788 | 1.00 | 12434 | 3 | | | | LOC440518 | 1.00 |
| 12339 | 3 | | | | | LOC339807 | 1.00 | 12435 | 3 | | | | LOC440563 | 1.00 |
| 12340 | 3 | | | | | LOC339822 | 1.00 | 12436 | 3 | | | | LOC440600 | 1.00 |
| 12341 | 3 | | | | | LOC339862 | 1.00 | 12437 | 3 | | | | LOC440700 | 1.00 |
| 12342 | 3 | | | | | LOC339874 | 1.00 | 12438 | 3 | | | | LOC440704 | 1.00 |
| 12343 | 3 | | | | | LOC339894 | 1.00 | 12439 | 3 | | | | LOC440896 | 1.00 |
| 12344 | 3 | | | | | LOC339926 | 1.00 | 12440 | 3 | | | | LOC440900 | 1.00 |
| 12345 | 3 | | | | | LOC339975 | 1.00 | 12441 | 3 | | | | LOC440905 | 1.00 |
| 12346 | 3 | | | | | LOC340017 | 1.00 | 12442 | 3 | | | | LOC440910 | 1.00 |
| 12347 | 3 | | | | | LOC340073 | 1.00 | 12443 | 3 | | | | LOC440925 | 1.00 |
| 12348 | 3 | | | | | LOC340074 | 1.00 | 12444 | 3 | | | | LOC440970 | 1.00 |
| 12349 | 3 | | | | | LOC340094 | 1.00 | 12445 | 3 | | | | LOC441009 | 1.00 |
| 12350 | 3 | | | | | LOC340107 | 1.00 | 12446 | 3 | | | | LOC441025 | 1.00 |
| 12351 | 3 | | | | | LOC340113 | 1.00 | 12447 | 3 | | | | LOC441177 | 1.00 |
| 12352 | 3 | | | | | LOC340508 | 1.00 | 12448 | 3 | | | | LOC441242 | 1.00 |
| 12353 | 3 | | | | | LOC340515 | 1.00 | 12449 | 3 | | | | LOC441495 | 1.00 |
| 12354 | 3 | | | | | LOC347411 | 1.00 | 12450 | 3 | | | | LOC441601 | 1.00 |
| 12355 | 3 | | | | | LOC348120 | 1.00 | 12451 | 3 | | | | LOC441666 | 1.00 |
| 12356 | 3 | | | | | LOC348761 | 1.00 | 12452 | 3 | | | | LOC442028 | 1.00 |
| 12357 | 3 | | | | | LOC349160 | 1.00 | 12453 | 3 | | | | LOC442132 | 1.00 |
| 12358 | 3 | | | | | LOC375010 | 1.00 | 12454 | 3 | | | | LOC442421 | 1.00 |
| 12359 | 3 | | | | | LOC375196 | 1.00 | 12455 | 3 | | | | LOC442459 | 1.00 |
| 12360 | 3 | | | | | LOC386597 | 1.00 | 12456 | 3 | | | | LOC442497 | 1.00 |
| 12361 | 3 | | | | | LOC387646 | 1.00 | 12457 | 3 | | | | LOC494141 | 1.00 |
| 12362 | 3 | | | | | LOC387895 | 1.00 | 12458 | 3 | | | | LOC494558 | 1.00 |
| 12363 | 3 | | | | | LOC388276 | 1.00 | 12459 | 3 | | | | LOC503519 | 1.00 |
| 12364 | 3 | | | | | LOC388387 | 1.00 | 12460 | 3 | | | | LOC550113 | 1.00 |
| 12365 | 3 | | | | | LOC388553 | 1.00 | 12461 | 3 | | | | LOC553103 | 1.00 |
| 12366 | 3 | | | | | LOC388588 | 1.00 | 12462 | 3 | | | | LOC554201 | 1.00 |
| 12367 | 3 | | | | | LOC388813 | 1.00 | 12463 | 3 | | | | LOC554223 | 1.00 |
| 12368 | 3 | | | | | LOC388906 | 1.00 | 12464 | 3 | | | | LOC574538 | 1.00 |
| 12369 | 3 | | | | | LOC388942 | 1.00 | 12465 | 3 | | | | LOC63930 | 1.00 |
| 12370 | 3 | | | | | LOC388946 | 1.00 | 12466 | 3 | | | | LOC641298 | 1.00 |
| 12371 | 3 | | | | | LOC388948 | 1.00 | 12467 | 3 | | | | LOC641364 | 1.00 |
| 12372 | 3 | | | | | LOC389023 | 1.00 | 12468 | 3 | | | | LOC641365 | 1.00 |
| 12373 | 3 | | | | | LOC389033 | 1.00 | 12469 | 3 | | | | LOC641367 | 1.00 |
| 12374 | 3 | | | | | LOC389043 | 1.00 | 12470 | 3 | | | | LOC641515 | 1.00 |
| 12375 | 3 | | | | | LOC389247 | 1.00 | 12471 | 3 | | | | LOC641518 | 1.00 |
| 12376 | 3 | | | | | LOC389332 | 1.00 | 12472 | 3 | | | | LOC641746 | 1.00 |
| 12377 | 3 | | | | | LOC389458 | 1.00 | 12473 | 3 | | | | LOC642236 | 1.00 |
| 12378 | 3 | | | | | LOC389634 | 1.00 | 12474 | 3 | | | | LOC642366 | 1.00 |
| 12379 | 3 | | | | | LOC389705 | 1.00 | 12475 | 3 | | | | LOC642426 | 1.00 |
| 12380 | 3 | | | | | LOC389765 | 1.00 | 12476 | 3 | | | | LOC642826 | 1.00 |

Fig. 38 - 66

| | | | | | | | | | | | | | | | | |
|---|---|---|---|---|---|---|---|---|---|---|---|---|---|---|---|---|
| 12477 | 3 | | | | | LOC642929 | 1.00 | 12573 | 3 | | | | | LOC729121 | 1.00 |
| 12478 | 3 | | | | | LOC643037 | 1.00 | 12574 | 3 | | | | | LOC729156 | 1.00 |
| 12479 | 3 | | | | | LOC643201 | 1.00 | 12575 | 3 | | | | | LOC729177 | 1.00 |
| 12480 | 3 | | | | | LOC643339 | 1.00 | 12576 | 3 | | | | | LOC729264 | 1.00 |
| 12481 | 3 | | | | | LOC643401 | 1.00 | 12577 | 3 | | | | | LOC729444 | 1.00 |
| 12482 | 3 | | | | | LOC643406 | 1.00 | 12578 | 3 | | | | | LOC729506 | 1.00 |
| 12483 | 3 | | | | | LOC643441 | 1.00 | 12579 | 3 | | | | | LOC729609 | 1.00 |
| 12484 | 3 | | | | | LOC643486 | 1.00 | 12580 | 3 | | | | | LOC729668 | 1.00 |
| 12485 | 3 | | | | | LOC643529 | 1.00 | 12581 | 3 | | | | | LOC729911 | 1.00 |
| 12486 | 3 | | | | | LOC643542 | 1.00 | 12582 | 3 | | | | | LOC729950 | 1.00 |
| 12487 | 3 | | | | | LOC643623 | 1.00 | 12583 | 3 | | | | | LOC729966 | 1.00 |
| 12488 | 3 | | | | | LOC643648 | 1.00 | 12584 | 3 | | | | | LOC729987 | 1.00 |
| 12489 | 3 | | | | | LOC643714 | 1.00 | 12585 | 3 | | | | | LOC730159 | 1.00 |
| 12490 | 3 | | | | | LOC643723 | 1.00 | 12586 | 3 | | | | | LOC730441 | 1.00 |
| 12491 | 3 | | | | | LOC643770 | 1.00 | 12587 | 3 | | | | | LOC730668 | 1.00 |
| 12492 | 3 | | | | | LOC643802 | 1.00 | 12588 | 3 | | | | | LOC730811 | 1.00 |
| 12493 | 3 | | | | | LOC643923 | 1.00 | 12589 | 3 | | | | | LOC731223 | 1.00 |
| 12494 | 3 | | | | | LOC643955 | 1.00 | 12590 | 3 | | | | | LOC731424 | 1.00 |
| 12495 | 3 | | | | | LOC644100 | 1.00 | 12591 | 3 | | | | | LOC731789 | 1.00 |
| 12496 | 3 | | | | | LOC644145 | 1.00 | 12592 | 3 | | | | | LOC732275 | 1.00 |
| 12497 | 3 | | | | | LOC644189 | 1.00 | 12593 | 3 | | | | | LOC81691 | 1.00 |
| 12498 | 3 | | | | | LOC644248 | 1.00 | 12594 | 3 | | | | | LOC84931 | 1.00 |
| 12499 | 3 | | | | | LOC644554 | 1.00 | 12595 | 3 | | | | | LOC84989 | 1.00 |
| 12500 | 3 | | | | | LOC644669 | 1.00 | 12596 | 3 | | | | | LOC90246 | 1.00 |
| 12501 | 3 | | | | | LOC644714 | 1.00 | 12597 | 3 | | | | | LOC90499 | 1.00 |
| 12502 | 3 | | | | | LOC644838 | 1.00 | 12598 | 3 | | | | | LOC91149 | 1.00 |
| 12503 | 3 | | | | | LOC644990 | 1.00 | 12599 | 3 | | | | | LOC91948 | 1.00 |
| 12504 | 3 | | | | | LOC645206 | 1.00 | 12600 | 3 | | | | | LOC93432 | 1.00 |
| 12505 | 3 | | | | | LOC645249 | 1.00 | 12601 | 3 | | | | | LONRF3 | 1.00 |
| 12506 | 3 | | | | | LOC645355 | 1.00 | 12602 | 3 | | | | | LOXHD1 | 1.00 |
| 12507 | 3 | | | | | LOC645431 | 1.00 | 12603 | 3 | | | | | LPA | 1.00 |
| 12508 | 3 | | | | | LOC645434 | 1.00 | 12604 | 3 | | | | | LPAL2 | 1.00 |
| 12509 | 3 | | | | | LOC645591 | 1.00 | 12605 | 3 | | | | | LPO | 1.00 |
| 12510 | 3 | | | | | LOC645752 | 1.00 | 12606 | 3 | | | | | LPPR1 | 1.00 |
| 12511 | 3 | | | | | LOC645949 | 1.00 | 12607 | 3 | | | | | LPPR3 | 1.00 |
| 12512 | 3 | | | | | LOC646168 | 1.00 | 12608 | 3 | | | | | LPPR5 | 1.00 |
| 12513 | 3 | | | | | LOC646268 | 1.00 | 12609 | 3 | | | | | LRAT | 1.00 |
| 12514 | 3 | | | | | LOC646278 | 1.00 | 12610 | 3 | | | | | LRCH2 | 1.00 |
| 12515 | 3 | | | | | LOC646324 | 1.00 | 12611 | 3 | | | | | LRFN2 | 1.00 |
| 12516 | 3 | | | | | LOC646329 | 1.00 | 12612 | 3 | | | | | LRGUK | 1.00 |
| 12517 | 3 | | | | | LOC646498 | 1.00 | 12613 | 3 | | | | | LRIT1 | 1.00 |
| 12518 | 3 | | | | | LOC646508 | 1.00 | 12614 | 3 | | | | | LRIT3 | 1.00 |
| 12519 | 3 | | | | | LOC646626 | 1.00 | 12615 | 3 | | | | | LRP1B | 1.00 |
| 12520 | 3 | | | | | LOC646627 | 1.00 | 12616 | 3 | | | | | LRP2 | 1.00 |
| 12521 | 3 | | | | | LOC646736 | 1.00 | 12617 | 3 | | | | | LRRC10 | 1.00 |
| 12522 | 3 | | | | | LOC646743 | 1.00 | 12618 | 3 | | | | | LRRC14B | 1.00 |
| 12523 | 3 | | | | | LOC646813 | 1.00 | 12619 | 3 | | | | | LRRC19 | 1.00 |
| 12524 | 3 | | | | | LOC646903 | 1.00 | 12620 | 3 | | | | | LRRC24 | 1.00 |
| 12525 | 3 | | | | | LOC646938 | 1.00 | 12621 | 3 | | | | | LRRC30 | 1.00 |
| 12526 | 3 | | | | | LOC646999 | 1.00 | 12622 | 3 | | | | | LRRC31 | 1.00 |
| 12527 | 3 | | | | | LOC647012 | 1.00 | 12623 | 3 | | | | | LRRC36 | 1.00 |
| 12528 | 3 | | | | | LOC647107 | 1.00 | 12624 | 3 | | | | | LRRC38 | 1.00 |
| 12529 | 3 | | | | | LOC647323 | 1.00 | 12625 | 3 | | | | | LRRC3B | 1.00 |
| 12530 | 3 | | | | | LOC647589 | 1.00 | 12626 | 3 | | | | | LRRC3C | 1.00 |
| 12531 | 3 | | | | | LOC647946 | 1.00 | 12627 | 3 | | | | | LRRC43 | 1.00 |
| 12532 | 3 | | | | | LOC648691 | 1.00 | 12628 | 3 | | | | | LRRC46 | 1.00 |
| 12533 | 3 | | | | | LOC648809 | 1.00 | 12629 | 3 | | | | | LRRC52 | 1.00 |
| 12534 | 3 | | | | | LOC649133 | 1.00 | 12630 | 3 | | | | | LRRC55 | 1.00 |
| 12535 | 3 | | | | | LOC649330 | 1.00 | 12631 | 3 | | | | | LRRC66 | 1.00 |
| 12536 | 3 | | | | | LOC650226 | 1.00 | 12632 | 3 | | | | | LRRC69 | 1.00 |
| 12537 | 3 | | | | | LOC650293 | 1.00 | 12633 | 3 | | | | | LRRC7 | 1.00 |
| 12538 | 3 | | | | | LOC650623 | 1.00 | 12634 | 3 | | | | | LRRC71 | 1.00 |
| 12539 | 3 | | | | | LOC653061 | 1.00 | 12635 | 3 | | | | | LRRC72 | 1.00 |
| 12540 | 3 | | | | | LOC653075 | 1.00 | 12636 | 3 | | | | | LRRC73 | 1.00 |
| 12541 | 3 | | | | | LOC653486 | 1.00 | 12637 | 3 | | | | | LRRD1 | 1.00 |
| 12542 | 3 | | | | | LOC653501 | 1.00 | 12638 | 3 | | | | | LRRIQ1 | 1.00 |
| 12543 | 3 | | | | | LOC653786 | 1.00 | 12639 | 3 | | | | | LRRIQ3 | 1.00 |
| 12544 | 3 | | | | | LOC723809 | 1.00 | 12640 | 3 | | | | | LRRIQ4 | 1.00 |
| 12545 | 3 | | | | | LOC727677 | 1.00 | 12641 | 3 | | | | | LRRN2 | 1.00 |
| 12546 | 3 | | | | | LOC727710 | 1.00 | 12642 | 3 | | | | | LRRN4 | 1.00 |
| 12547 | 3 | | | | | LOC727915 | 1.00 | 12643 | 3 | | | | | LRRTM2 | 1.00 |
| 12548 | 3 | | | | | LOC727924 | 1.00 | 12644 | 3 | | | | | LRRTM3 | 1.00 |
| 12549 | 3 | | | | | LOC727982 | 1.00 | 12645 | 3 | | | | | LRRTM4 | 1.00 |
| 12550 | 3 | | | | | LOC728012 | 1.00 | 12646 | 3 | | | | | LRTM1 | 1.00 |
| 12551 | 3 | | | | | LOC728040 | 1.00 | 12647 | 3 | | | | | LRTM2 | 1.00 |
| 12552 | 3 | | | | | LOC728084 | 1.00 | 12648 | 3 | | | | | LSAMP-AS3 | 1.00 |
| 12553 | 3 | | | | | LOC728175 | 1.00 | 12649 | 3 | | | | | LSM11 | 1.00 |
| 12554 | 3 | | | | | LOC728218 | 1.00 | 12650 | 3 | | | | | LTA | 1.00 |
| 12555 | 3 | | | | | LOC728228 | 1.00 | 12651 | 3 | | | | | LTK | 1.00 |
| 12556 | 3 | | | | | LOC728323 | 1.00 | 12652 | 3 | | | | | LUZP2 | 1.00 |
| 12557 | 3 | | | | | LOC728342 | 1.00 | 12653 | 3 | | | | | LUZP4 | 1.00 |
| 12558 | 3 | | | | | LOC728369 | 1.00 | 12654 | 3 | | | | | LY6G6E | 1.00 |
| 12559 | 3 | | | | | LOC728393 | 1.00 | 12655 | 3 | | | | | LY6G6F | 1.00 |
| 12560 | 3 | | | | | LOC728405 | 1.00 | 12656 | 3 | | | | | LY6H | 1.00 |
| 12561 | 3 | | | | | LOC728407 | 1.00 | 12657 | 3 | | | | | LY75-CD302 | 1.00 |
| 12562 | 3 | | | | | LOC728437 | 1.00 | 12658 | 3 | | | | | LY86-AS1 | 1.00 |
| 12563 | 3 | | | | | LOC728463 | 1.00 | 12659 | 3 | | | | | LYG2 | 1.00 |
| 12564 | 3 | | | | | LOC728558 | 1.00 | 12660 | 3 | | | | | LYPD4 | 1.00 |
| 12565 | 3 | | | | | LOC728606 | 1.00 | 12661 | 3 | | | | | LYPD6 | 1.00 |
| 12566 | 3 | | | | | LOC728716 | 1.00 | 12662 | 3 | | | | | LYZL1 | 1.00 |
| 12567 | 3 | | | | | LOC728723 | 1.00 | 12663 | 3 | | | | | LYZL2 | 1.00 |
| 12568 | 3 | | | | | LOC728724 | 1.00 | 12664 | 3 | | | | | LYZL4 | 1.00 |
| 12569 | 3 | | | | | LOC728989 | 1.00 | 12665 | 3 | | | | | LYZL6 | 1.00 |
| 12570 | 3 | | | | | LOC729041 | 1.00 | 12666 | 3 | | | | | M1 | 1.00 |
| 12571 | 3 | | | | | LOC729059 | 1.00 | 12667 | 3 | | | | | MAB21L2 | 1.00 |
| 12572 | 3 | | | | | LOC729080 | 1.00 | 12668 | 3 | | | | | MACROD2-AS1 | 1.00 |

Fig. 38 - 67

| | | | | | | | | | | | | | | | |
|---|---|---|---|---|---|---|---|---|---|---|---|---|---|---|---|
| 12669 | 3 | | | | | MADCAM1 | 1.00 | 12764 | 3 | | | | | MGC23270 | 1.00 |
| 12670 | 3 | | | | | MAEL | 1.00 | 12765 | 3 | | | | | MGC27382 | 1.00 |
| 12671 | 3 | | | | | MAFA | 1.00 | 12766 | 3 | | | | | MGC2889 | 1.00 |
| 12672 | 3 | | | | | MAG | 1.00 | 12767 | 3 | | | | | MGC34034 | 1.00 |
| 12673 | 3 | | | | | MAGEA1 | 1.00 | 12768 | 3 | | | | | MGC39584 | 1.00 |
| 12674 | 3 | | | | | MAGEA10 | 1.00 | 12769 | 3 | | | | | MGC4473 | 1.00 |
| 12675 | 3 | | | | | MAGEA10-MAGEAS | 1.00 | 12770 | 3 | | | | | MGC45800 | 1.00 |
| | | | | | | | | 12771 | 3 | | | | | MGC70870 | 1.00 |
| 12676 | 3 | | | | | MAGEA11 | 1.00 | 12772 | 3 | | | | | MIA2 | 1.00 |
| 12677 | 3 | | | | | MAGEA12 | 1.00 | 12773 | 3 | | | | | MIMT1 | 1.00 |
| 12678 | 3 | | | | | MAGEA2 | 1.00 | 12774 | 3 | | | | | MIOX | 1.00 |
| 12679 | 3 | | | | | MAGEA2B | 1.00 | 12775 | 3 | | | | | MIP | 1.00 |
| 12680 | 3 | | | | | MAGEA3 | 1.00 | 12776 | 3 | | | | | MIPOL1 | 1.00 |
| 12681 | 3 | | | | | MAGEA4 | 1.00 | 12777 | 3 | | | | | MIR100 | 1.00 |
| 12682 | 3 | | | | | MAGEA5 | 1.00 | 12778 | 3 | | | | | MIR101-1 | 1.00 |
| 12683 | 3 | | | | | MAGEA6 | 1.00 | 12779 | 3 | | | | | MIR101-2 | 1.00 |
| 12684 | 3 | | | | | MAGEA8 | 1.00 | 12780 | 3 | | | | | MIR103A1 | 1.00 |
| 12685 | 3 | | | | | MAGEA9 | 1.00 | 12781 | 3 | | | | | MIR103A2 | 1.00 |
| 12686 | 3 | | | | | MAGEA9B | 1.00 | 12782 | 3 | | | | | MIR103B1 | 1.00 |
| 12687 | 3 | | | | | MAGEB1 | 1.00 | 12783 | 3 | | | | | MIR103B2 | 1.00 |
| 12688 | 3 | | | | | MAGEB10 | 1.00 | 12784 | 3 | | | | | MIR105-1 | 1.00 |
| 12689 | 3 | | | | | MAGEB16 | 1.00 | 12785 | 3 | | | | | MIR105-2 | 1.00 |
| 12690 | 3 | | | | | MAGEB18 | 1.00 | 12786 | 3 | | | | | MIR106A | 1.00 |
| 12691 | 3 | | | | | MAGEB2 | 1.00 | 12787 | 3 | | | | | MIR106B | 1.00 |
| 12692 | 3 | | | | | MAGEB3 | 1.00 | 12788 | 3 | | | | | MIR107 | 1.00 |
| 12693 | 3 | | | | | MAGEB4 | 1.00 | 12789 | 3 | | | | | MIR10A | 1.00 |
| 12694 | 3 | | | | | MAGEB6 | 1.00 | 12790 | 3 | | | | | MIR10B | 1.00 |
| 12695 | 3 | | | | | MAGEC1 | 1.00 | 12791 | 3 | | | | | MIR1-1 | 1.00 |
| 12696 | 3 | | | | | MAGEC2 | 1.00 | 12792 | 3 | | | | | MIR1178 | 1.00 |
| 12697 | 3 | | | | | MAGEC3 | 1.00 | 12793 | 3 | | | | | MIR1179 | 1.00 |
| 12698 | 3 | | | | | MAGEE2 | 1.00 | 12794 | 3 | | | | | MIR1180 | 1.00 |
| 12699 | 3 | | | | | MAGEL2 | 1.00 | 12795 | 3 | | | | | MIR1181 | 1.00 |
| 12700 | 3 | | | | | MAK | 1.00 | 12796 | 3 | | | | | MIR1182 | 1.00 |
| 12701 | 3 | | | | | MANSC4 | 1.00 | 12797 | 3 | | | | | MIR1184-3 | 1.00 |
| 12702 | 3 | | | | | MAP2K6 | 1.00 | 12798 | 3 | | | | | MIR1185-1 | 1.00 |
| 12703 | 3 | | | | | MAP3K15 | 1.00 | 12799 | 3 | | | | | MIR1185-2 | 1.00 |
| 12704 | 3 | | | | | MAP7D2 | 1.00 | 12800 | 3 | | | | | MIR1193 | 1.00 |
| 12705 | 3 | | | | | MAP9 | 1.00 | 12801 | 3 | | | | | MIR1197 | 1.00 |
| 12706 | 3 | | | | | MAPK10 | 1.00 | 12802 | 3 | | | | | MIR1-2 | 1.00 |
| 12707 | 3 | | | | | MAPT-AS1 | 1.00 | 12803 | 3 | | | | | MIR1200 | 1.00 |
| 12708 | 3 | | | | | MAPT-IT1 | 1.00 | 12804 | 3 | | | | | MIR1203 | 1.00 |
| 12709 | 3 | | | | | MARCH10 | 1.00 | 12805 | 3 | | | | | MIR1204 | 1.00 |
| 12710 | 3 | | | | | MARCH11 | 1.00 | 12806 | 3 | | | | | MIR1205 | 1.00 |
| 12711 | 3 | | | | | MARCH4 | 1.00 | 12807 | 3 | | | | | MIR1206 | 1.00 |
| 12712 | 3 | | | | | MARK2P9 | 1.00 | 12808 | 3 | | | | | MIR1207 | 1.00 |
| 12713 | 3 | | | | | MAS1 | 1.00 | 12809 | 3 | | | | | MIR1208 | 1.00 |
| 12714 | 3 | | | | | MATN1 | 1.00 | 12810 | 3 | | | | | MIR122 | 1.00 |
| 12715 | 3 | | | | | MATN3 | 1.00 | 12811 | 3 | | | | | MIR1224 | 1.00 |
| 12716 | 3 | | | | | MBD3L1 | 1.00 | 12812 | 3 | | | | | MIR1225 | 1.00 |
| 12717 | 3 | | | | | MBD3L2 | 1.00 | 12813 | 3 | | | | | MIR1226 | 1.00 |
| 12718 | 3 | | | | | MBD3L3 | 1.00 | 12814 | 3 | | | | | MIR1227 | 1.00 |
| 12719 | 3 | | | | | MBD3L4 | 1.00 | 12815 | 3 | | | | | MIR1228 | 1.00 |
| 12720 | 3 | | | | | MBD3L5 | 1.00 | 12816 | 3 | | | | | MIR1229 | 1.00 |
| 12721 | 3 | | | | | MBL2 | 1.00 | 12817 | 3 | | | | | MIR1231 | 1.00 |
| 12722 | 3 | | | | | MBOAT4 | 1.00 | 12818 | 3 | | | | | MIR1233-1 | 1.00 |
| 12723 | 3 | | | | | MC2R | 1.00 | 12819 | 3 | | | | | MIR1233-2 | 1.00 |
| 12724 | 3 | | | | | MC3R | 1.00 | 12820 | 3 | | | | | MIR1234 | 1.00 |
| 12725 | 3 | | | | | MC4R | 1.00 | 12821 | 3 | | | | | MIR1236 | 1.00 |
| 12726 | 3 | | | | | MCART2 | 1.00 | 12822 | 3 | | | | | MIR1237 | 1.00 |
| 12727 | 3 | | | | | MCART3P | 1.00 | 12823 | 3 | | | | | MIR1238 | 1.00 |
| 12728 | 3 | | | | | MCART6 | 1.00 | 12824 | 3 | | | | | MIR124-1 | 1.00 |
| 12729 | 3 | | | | | MCCD1 | 1.00 | 12825 | 3 | | | | | MIR124-2 | 1.00 |
| 12730 | 3 | | | | | MCF2 | 1.00 | 12826 | 3 | | | | | MIR1243 | 1.00 |
| 12731 | 3 | | | | | MCF2L2 | 1.00 | 12827 | 3 | | | | | MIR124-3 | 1.00 |
| 12732 | 3 | | | | | MCHR2 | 1.00 | 12828 | 3 | | | | | MIR1244-1 | 1.00 |
| 12733 | 3 | | | | | MCM10 | 1.00 | 12829 | 3 | | | | | MIR1244-2 | 1.00 |
| 12734 | 3 | | | | | MDGA2 | 1.00 | 12830 | 3 | | | | | MIR1244-3 | 1.00 |
| 12735 | 3 | | | | | MDH1B | 1.00 | 12831 | 3 | | | | | MIR1245A | 1.00 |
| 12736 | 3 | | | | | MDS2 | 1.00 | 12832 | 3 | | | | | MIR1245B | 1.00 |
| 12737 | 3 | | | | | MED12L | 1.00 | 12833 | 3 | | | | | MIR1246 | 1.00 |
| 12738 | 3 | | | | | MEF2BNB-MEF2B | 1.00 | 12834 | 3 | | | | | MIR1249 | 1.00 |
| 12739 | 3 | | | | | MEG8 | 1.00 | 12835 | 3 | | | | | MIR1250 | 1.00 |
| 12740 | 3 | | | | | MEGF10 | 1.00 | 12836 | 3 | | | | | MIR1251 | 1.00 |
| 12741 | 3 | | | | | MEGF11 | 1.00 | 12837 | 3 | | | | | MIR1252 | 1.00 |
| 12742 | 3 | | | | | MEI1 | 1.00 | 12838 | 3 | | | | | MIR1253 | 1.00 |
| 12743 | 3 | | | | | MEIG1 | 1.00 | 12839 | 3 | | | | | MIR1256 | 1.00 |
| 12744 | 3 | | | | | MEP1A | 1.00 | 12840 | 3 | | | | | MIR1257 | 1.00 |
| 12745 | 3 | | | | | MEP1B | 1.00 | 12841 | 3 | | | | | MIR1258 | 1.00 |
| 12746 | 3 | | | | | MEPE | 1.00 | 12842 | 3 | | | | | MIR125A | 1.00 |
| 12747 | 3 | | | | | MESP2 | 1.00 | 12843 | 3 | | | | | MIR125B1 | 1.00 |
| 12748 | 3 | | | | | MESTIT1 | 1.00 | 12844 | 3 | | | | | MIR125B2 | 1.00 |
| 12749 | 3 | | | | | METTL11B | 1.00 | 12845 | 3 | | | | | MIR126 | 1.00 |
| 12750 | 3 | | | | | METTL21C | 1.00 | 12846 | 3 | | | | | MIR1260A | 1.00 |
| 12751 | 3 | | | | | METTL21CP1 | 1.00 | 12847 | 3 | | | | | MIR1260B | 1.00 |
| 12752 | 3 | | | | | MFSD2B | 1.00 | 12848 | 3 | | | | | MIR1262 | 1.00 |
| 12753 | 3 | | | | | MFSD6L | 1.00 | 12849 | 3 | | | | | MIR1264 | 1.00 |
| 12754 | 3 | | | | | MGAM | 1.00 | 12850 | 3 | | | | | MIR1265 | 1.00 |
| 12755 | 3 | | | | | MGAT4C | 1.00 | 12851 | 3 | | | | | MIR1266 | 1.00 |
| 12756 | 3 | | | | | MGAT5B | 1.00 | 12852 | 3 | | | | | MIR127 | 1.00 |
| 12757 | 3 | | | | | MGC12916 | 1.00 | 12853 | 3 | | | | | MIR1270-1 | 1.00 |
| 12758 | 3 | | | | | MGC14436 | 1.00 | 12854 | 3 | | | | | MIR1272 | 1.00 |
| 12759 | 3 | | | | | MGC15885 | 1.00 | 12855 | 3 | | | | | MIR1275 | 1.00 |
| 12760 | 3 | | | | | MGC16025 | 1.00 | 12856 | 3 | | | | | MIR1276 | 1.00 |
| 12761 | 3 | | | | | MGC16121 | 1.00 | 12857 | 3 | | | | | MIR1277 | 1.00 |
| 12762 | 3 | | | | | MGC16142 | 1.00 | 12858 | 3 | | | | | MIR1278 | 1.00 |
| 12763 | 3 | | | | | MGC16703 | 1.00 | 12859 | 3 | | | | | MIR1279 | 1.00 |

Fig. 38 - 68

| | | | | | | | | | | | | | | | | |
|---|---|---|---|---|---|---|---|---|---|---|---|---|---|---|---|---|
| 12860 | 3 | | | | | MIR1280 | 1.00 | 12956 | 3 | | | | | MIR1911 | 1.00 |
| 12861 | 3 | | | | | MIR1281 | 1.00 | 12957 | 3 | | | | | MIR1912 | 1.00 |
| 12862 | 3 | | | | | MIR128-1 | 1.00 | 12958 | 3 | | | | | MIR1913 | 1.00 |
| 12863 | 3 | | | | | MIR128-2 | 1.00 | 12959 | 3 | | | | | MIR1914 | 1.00 |
| 12864 | 3 | | | | | MIR1283-1 | 1.00 | 12960 | 3 | | | | | MIR1915 | 1.00 |
| 12865 | 3 | | | | | MIR1283-2 | 1.00 | 12961 | 3 | | | | | MIR192 | 1.00 |
| 12866 | 3 | | | | | MIR1284 | 1.00 | 12962 | 3 | | | | | MIR193A | 1.00 |
| 12867 | 3 | | | | | MIR1286 | 1.00 | 12963 | 3 | | | | | MIR193B | 1.00 |
| 12868 | 3 | | | | | MIR1287 | 1.00 | 12964 | 3 | | | | | MIR194-1 | 1.00 |
| 12869 | 3 | | | | | MIR1288 | 1.00 | 12965 | 3 | | | | | MIR194-2 | 1.00 |
| 12870 | 3 | | | | | MIR1289-2 | 1.00 | 12966 | 3 | | | | | MIR195 | 1.00 |
| 12871 | 3 | | | | | MIR1291 | 1.00 | 12967 | 3 | | | | | MIR196A1 | 1.00 |
| 12872 | 3 | | | | | MIR129-1 | 1.00 | 12968 | 3 | | | | | MIR196A2 | 1.00 |
| 12873 | 3 | | | | | MIR1292 | 1.00 | 12969 | 3 | | | | | MIR196B | 1.00 |
| 12874 | 3 | | | | | MIR129-2 | 1.00 | 12970 | 3 | | | | | MIR197 | 1.00 |
| 12875 | 3 | | | | | MIR1293 | 1.00 | 12971 | 3 | | | | | MIR1972-1 | 1.00 |
| 12876 | 3 | | | | | MIR1295A | 1.00 | 12972 | 3 | | | | | MIR1973 | 1.00 |
| 12877 | 3 | | | | | MIR1296 | 1.00 | 12973 | 3 | | | | | MIR1976 | 1.00 |
| 12878 | 3 | | | | | MIR1297 | 1.00 | 12974 | 3 | | | | | MIR198 | 1.00 |
| 12879 | 3 | | | | | MIR1298 | 1.00 | 12975 | 3 | | | | | MIR199A1 | 1.00 |
| 12880 | 3 | | | | | MIR1301 | 1.00 | 12976 | 3 | | | | | MIR199A2 | 1.00 |
| 12881 | 3 | | | | | MIR1304 | 1.00 | 12977 | 3 | | | | | MIR199B | 1.00 |
| 12882 | 3 | | | | | MIR1305 | 1.00 | 12978 | 3 | | | | | MIR19A | 1.00 |
| 12883 | 3 | | | | | MIR1306 | 1.00 | 12979 | 3 | | | | | MIR19B1 | 1.00 |
| 12884 | 3 | | | | | MIR130A | 1.00 | 12980 | 3 | | | | | MIR19B2 | 1.00 |
| 12885 | 3 | | | | | MIR130B | 1.00 | 12981 | 3 | | | | | MIR200A | 1.00 |
| 12886 | 3 | | | | | MIR132 | 1.00 | 12982 | 3 | | | | | MIR200B | 1.00 |
| 12887 | 3 | | | | | MIR1322 | 1.00 | 12983 | 3 | | | | | MIR200C | 1.00 |
| 12888 | 3 | | | | | MIR1323 | 1.00 | 12984 | 3 | | | | | MIR202 | 1.00 |
| 12889 | 3 | | | | | MIR1324 | 1.00 | 12985 | 3 | | | | | MIR204 | 1.00 |
| 12890 | 3 | | | | | MIR133A1 | 1.00 | 12986 | 3 | | | | | MIR2052 | 1.00 |
| 12891 | 3 | | | | | MIR133A2 | 1.00 | 12987 | 3 | | | | | MIR2053 | 1.00 |
| 12892 | 3 | | | | | MIR133B | 1.00 | 12988 | 3 | | | | | MIR2054 | 1.00 |
| 12893 | 3 | | | | | MIR134 | 1.00 | 12989 | 3 | | | | | MIR206 | 1.00 |
| 12894 | 3 | | | | | MIR1343 | 1.00 | 12990 | 3 | | | | | MIR208A | 1.00 |
| 12895 | 3 | | | | | MIR135A1 | 1.00 | 12991 | 3 | | | | | MIR208B | 1.00 |
| 12896 | 3 | | | | | MIR135A2 | 1.00 | 12992 | 3 | | | | | MIR20A | 1.00 |
| 12897 | 3 | | | | | MIR135B | 1.00 | 12993 | 3 | | | | | MIR20B | 1.00 |
| 12898 | 3 | | | | | MIR136 | 1.00 | 12994 | 3 | | | | | MIR21 | 1.00 |
| 12899 | 3 | | | | | MIR137 | 1.00 | 12995 | 3 | | | | | MIR211 | 1.00 |
| 12900 | 3 | | | | | MIR137HG | 1.00 | 12996 | 3 | | | | | MIR2110 | 1.00 |
| 12901 | 3 | | | | | MIR138-1 | 1.00 | 12997 | 3 | | | | | MIR2113 | 1.00 |
| 12902 | 3 | | | | | MIR138-2 | 1.00 | 12998 | 3 | | | | | MIR2114 | 1.00 |
| 12903 | 3 | | | | | MIR139 | 1.00 | 12999 | 3 | | | | | MIR2116 | 1.00 |
| 12904 | 3 | | | | | MIR140 | 1.00 | 13000 | 3 | | | | | MIR2117 | 1.00 |
| 12905 | 3 | | | | | MIR141 | 1.00 | 13001 | 3 | | | | | MIR212 | 1.00 |
| 12906 | 3 | | | | | MIR142 | 1.00 | 13002 | 3 | | | | | MIR214 | 1.00 |
| 12907 | 3 | | | | | MIR143 | 1.00 | 13003 | 3 | | | | | MIR215 | 1.00 |
| 12908 | 3 | | | | | MIR144 | 1.00 | 13004 | 3 | | | | | MIR216A | 1.00 |
| 12909 | 3 | | | | | MIR145 | 1.00 | 13005 | 3 | | | | | MIR216B | 1.00 |
| 12910 | 3 | | | | | MIR1468 | 1.00 | 13006 | 3 | | | | | MIR217 | 1.00 |
| 12911 | 3 | | | | | MIR1469 | 1.00 | 13007 | 3 | | | | | MIR218-1 | 1.00 |
| 12912 | 3 | | | | | MIR146A | 1.00 | 13008 | 3 | | | | | MIR218-2 | 1.00 |
| 12913 | 3 | | | | | MIR146B | 1.00 | 13009 | 3 | | | | | MIR219-1 | 1.00 |
| 12914 | 3 | | | | | MIR1470 | 1.00 | 13010 | 3 | | | | | MIR219-2 | 1.00 |
| 12915 | 3 | | | | | MIR1471 | 1.00 | 13011 | 3 | | | | | MIR22 | 1.00 |
| 12916 | 3 | | | | | MIR147A | 1.00 | 13012 | 3 | | | | | MIR221 | 1.00 |
| 12917 | 3 | | | | | MIR147B | 1.00 | 13013 | 3 | | | | | MIR222 | 1.00 |
| 12918 | 3 | | | | | MIR148A | 1.00 | 13014 | 3 | | | | | MIR223 | 1.00 |
| 12919 | 3 | | | | | MIR148B | 1.00 | 13015 | 3 | | | | | MIR2276 | 1.00 |
| 12920 | 3 | | | | | MIR149 | 1.00 | 13016 | 3 | | | | | MIR2277 | 1.00 |
| 12921 | 3 | | | | | MIR150 | 1.00 | 13017 | 3 | | | | | MIR2278 | 1.00 |
| 12922 | 3 | | | | | MIR152 | 1.00 | 13018 | 3 | | | | | MIR2355 | 1.00 |
| 12923 | 3 | | | | | MIR153-1 | 1.00 | 13019 | 3 | | | | | MIR2392 | 1.00 |
| 12924 | 3 | | | | | MIR153-2 | 1.00 | 13020 | 3 | | | | | MIR23A | 1.00 |
| 12925 | 3 | | | | | MIR1537 | 1.00 | 13021 | 3 | | | | | MIR23B | 1.00 |
| 12926 | 3 | | | | | MIR1538 | 1.00 | 13022 | 3 | | | | | MIR23C | 1.00 |
| 12927 | 3 | | | | | MIR1539 | 1.00 | 13023 | 3 | | | | | MIR24-1 | 1.00 |
| 12928 | 3 | | | | | MIR154 | 1.00 | 13024 | 3 | | | | | MIR24-2 | 1.00 |
| 12929 | 3 | | | | | MIR155 | 1.00 | 13025 | 3 | | | | | MIR2467 | 1.00 |
| 12930 | 3 | | | | | MIR15A | 1.00 | 13026 | 3 | | | | | MIR25 | 1.00 |
| 12931 | 3 | | | | | MIR15B | 1.00 | 13027 | 3 | | | | | MIR2681 | 1.00 |
| 12932 | 3 | | | | | MIR16-1 | 1.00 | 13028 | 3 | | | | | MIR2682 | 1.00 |
| 12933 | 3 | | | | | MIR16-2 | 1.00 | 13029 | 3 | | | | | MIR26A1 | 1.00 |
| 12934 | 3 | | | | | MIR17 | 1.00 | 13030 | 3 | | | | | MIR26A2 | 1.00 |
| 12935 | 3 | | | | | MIR181A1 | 1.00 | 13031 | 3 | | | | | MIR26B | 1.00 |
| 12936 | 3 | | | | | MIR181A2 | 1.00 | 13032 | 3 | | | | | MIR27A | 1.00 |
| 12937 | 3 | | | | | MIR181B1 | 1.00 | 13033 | 3 | | | | | MIR27B | 1.00 |
| 12938 | 3 | | | | | MIR181B2 | 1.00 | 13034 | 3 | | | | | MIR2861 | 1.00 |
| 12939 | 3 | | | | | MIR181C | 1.00 | 13035 | 3 | | | | | MIR2909 | 1.00 |
| 12940 | 3 | | | | | MIR182 | 1.00 | 13036 | 3 | | | | | MIR296 | 1.00 |
| 12941 | 3 | | | | | MIR1827 | 1.00 | 13037 | 3 | | | | | MIR2964A | 1.00 |
| 12942 | 3 | | | | | MIR183 | 1.00 | 13038 | 3 | | | | | MIR298 | 1.00 |
| 12943 | 3 | | | | | MIR184 | 1.00 | 13039 | 3 | | | | | MIR299 | 1.00 |
| 12944 | 3 | | | | | MIR185 | 1.00 | 13040 | 3 | | | | | MIR29A | 1.00 |
| 12945 | 3 | | | | | MIR186 | 1.00 | 13041 | 3 | | | | | MIR29B1 | 1.00 |
| 12946 | 3 | | | | | MIR187 | 1.00 | 13042 | 3 | | | | | MIR29B2 | 1.00 |
| 12947 | 3 | | | | | MIR188 | 1.00 | 13043 | 3 | | | | | MIR29C | 1.00 |
| 12948 | 3 | | | | | MIR18A | 1.00 | 13044 | 3 | | | | | MIR300 | 1.00 |
| 12949 | 3 | | | | | MIR18B | 1.00 | 13045 | 3 | | | | | MIR301A | 1.00 |
| 12950 | 3 | | | | | MIR1908 | 1.00 | 13046 | 3 | | | | | MIR301B | 1.00 |
| 12951 | 3 | | | | | MIR1909 | 1.00 | 13047 | 3 | | | | | MIR302A | 1.00 |
| 12952 | 3 | | | | | MIR190A | 1.00 | 13048 | 3 | | | | | MIR302B | 1.00 |
| 12953 | 3 | | | | | MIR190B | 1.00 | 13049 | 3 | | | | | MIR302C | 1.00 |
| 12954 | 3 | | | | | MIR191 | 1.00 | 13050 | 3 | | | | | MIR302D | 1.00 |
| 12955 | 3 | | | | | MIR1910 | 1.00 | 13051 | 3 | | | | | MIR302F | 1.00 |

Fig. 38 - 69

| | | | | | | | | | | | | | | |
|---|---|---|---|---|---|---|---|---|---|---|---|---|---|---|
| 13052 | 3 | | | | | MIR3064 | 1.00 | 13148 | 3 | | | | MIR320C1 | 1.00 |
| 13053 | 3 | | | | | MIR3065 | 1.00 | 13149 | 3 | | | | MIR320C2 | 1.00 |
| 13054 | 3 | | | | | MIR3074 | 1.00 | 13150 | 3 | | | | MIR320D1 | 1.00 |
| 13055 | 3 | | | | | MIR30A | 1.00 | 13151 | 3 | | | | MIR320D2 | 1.00 |
| 13056 | 3 | | | | | MIR30B | 1.00 | 13152 | 3 | | | | MIR320E | 1.00 |
| 13057 | 3 | | | | | MIR30C1 | 1.00 | 13153 | 3 | | | | MIR323A | 1.00 |
| 13058 | 3 | | | | | MIR30C2 | 1.00 | 13154 | 3 | | | | MIR323B | 1.00 |
| 13059 | 3 | | | | | MIR30D | 1.00 | 13155 | 3 | | | | MIR324 | 1.00 |
| 13060 | 3 | | | | | MIR30E | 1.00 | 13156 | 3 | | | | MIR326 | 1.00 |
| 13061 | 3 | | | | | MIR31 | 1.00 | 13157 | 3 | | | | MIR328 | 1.00 |
| 13062 | 3 | | | | | MIR3115 | 1.00 | 13158 | 3 | | | | MIR329-1 | 1.00 |
| 13063 | 3 | | | | | MIR3117 | 1.00 | 13159 | 3 | | | | MIR329-2 | 1.00 |
| 13064 | 3 | | | | | MIR3119-1 | 1.00 | 13160 | 3 | | | | MIR330 | 1.00 |
| 13065 | 3 | | | | | MIR3120 | 1.00 | 13161 | 3 | | | | MIR331 | 1.00 |
| 13066 | 3 | | | | | MIR3121 | 1.00 | 13162 | 3 | | | | MIR335 | 1.00 |
| 13067 | 3 | | | | | MIR3122 | 1.00 | 13163 | 3 | | | | MIR337 | 1.00 |
| 13068 | 3 | | | | | MIR3123 | 1.00 | 13164 | 3 | | | | MIR338 | 1.00 |
| 13069 | 3 | | | | | MIR3124 | 1.00 | 13165 | 3 | | | | MIR339 | 1.00 |
| 13070 | 3 | | | | | MIR3125 | 1.00 | 13166 | 3 | | | | MIR33A | 1.00 |
| 13071 | 3 | | | | | MIR3126 | 1.00 | 13167 | 3 | | | | MIR33B | 1.00 |
| 13072 | 3 | | | | | MIR3127 | 1.00 | 13168 | 3 | | | | MIR340 | 1.00 |
| 13073 | 3 | | | | | MIR3128 | 1.00 | 13169 | 3 | | | | MIR345 | 1.00 |
| 13074 | 3 | | | | | MIR3129 | 1.00 | 13170 | 3 | | | | MIR346 | 1.00 |
| 13075 | 3 | | | | | MIR3130-1 | 1.00 | 13171 | 3 | | | | MIR34A | 1.00 |
| 13076 | 3 | | | | | MIR3131 | 1.00 | 13172 | 3 | | | | MIR34B | 1.00 |
| 13077 | 3 | | | | | MIR3132 | 1.00 | 13173 | 3 | | | | MIR34C | 1.00 |
| 13078 | 3 | | | | | MIR3134 | 1.00 | 13174 | 3 | | | | MIR3529 | 1.00 |
| 13079 | 3 | | | | | MIR3136 | 1.00 | 13175 | 3 | | | | MIR3545 | 1.00 |
| 13080 | 3 | | | | | MIR3138 | 1.00 | 13176 | 3 | | | | MIR3591 | 1.00 |
| 13081 | 3 | | | | | MIR3140 | 1.00 | 13177 | 3 | | | | MIR3605 | 1.00 |
| 13082 | 3 | | | | | MIR3141 | 1.00 | 13178 | 3 | | | | MIR3606 | 1.00 |
| 13083 | 3 | | | | | MIR3142 | 1.00 | 13179 | 3 | | | | MIR3607 | 1.00 |
| 13084 | 3 | | | | | MIR3143 | 1.00 | 13180 | 3 | | | | MIR3609 | 1.00 |
| 13085 | 3 | | | | | MIR3145 | 1.00 | 13181 | 3 | | | | MIR3610 | 1.00 |
| 13086 | 3 | | | | | MIR3146 | 1.00 | 13182 | 3 | | | | MIR3612 | 1.00 |
| 13087 | 3 | | | | | MIR3147 | 1.00 | 13183 | 3 | | | | MIR3613 | 1.00 |
| 13088 | 3 | | | | | MIR3148 | 1.00 | 13184 | 3 | | | | MIR3614 | 1.00 |
| 13089 | 3 | | | | | MIR3150A | 1.00 | 13185 | 3 | | | | MIR3615 | 1.00 |
| 13090 | 3 | | | | | MIR3150B | 1.00 | 13186 | 3 | | | | MIR3616 | 1.00 |
| 13091 | 3 | | | | | MIR3151 | 1.00 | 13187 | 3 | | | | MIR3618 | 1.00 |
| 13092 | 3 | | | | | MIR3152 | 1.00 | 13188 | 3 | | | | MIR3619 | 1.00 |
| 13093 | 3 | | | | | MIR3153 | 1.00 | 13189 | 3 | | | | MIR362 | 1.00 |
| 13094 | 3 | | | | | MIR3154 | 1.00 | 13190 | 3 | | | | MIR3620 | 1.00 |
| 13095 | 3 | | | | | MIR3155A | 1.00 | 13191 | 3 | | | | MIR3621 | 1.00 |
| 13096 | 3 | | | | | MIR3155B | 1.00 | 13192 | 3 | | | | MIR3622A | 1.00 |
| 13097 | 3 | | | | | MIR3156-1 | 1.00 | 13193 | 3 | | | | MIR3622B | 1.00 |
| 13098 | 3 | | | | | MIR3156-2 | 1.00 | 13194 | 3 | | | | MIR363 | 1.00 |
| 13099 | 3 | | | | | MIR3156-3 | 1.00 | 13195 | 3 | | | | MIR3646 | 1.00 |
| 13100 | 3 | | | | | MIR3157 | 1.00 | 13196 | 3 | | | | MIR3649 | 1.00 |
| 13101 | 3 | | | | | MIR3158-2 | 1.00 | 13197 | 3 | | | | MIR3650 | 1.00 |
| 13102 | 3 | | | | | MIR3160-1 | 1.00 | 13198 | 3 | | | | MIR3651 | 1.00 |
| 13103 | 3 | | | | | MIR3160-2 | 1.00 | 13199 | 3 | | | | MIR3652 | 1.00 |
| 13104 | 3 | | | | | MIR3162 | 1.00 | 13200 | 3 | | | | MIR3653 | 1.00 |
| 13105 | 3 | | | | | MIR3165 | 1.00 | 13201 | 3 | | | | MIR3654 | 1.00 |
| 13106 | 3 | | | | | MIR3167 | 1.00 | 13202 | 3 | | | | MIR3655 | 1.00 |
| 13107 | 3 | | | | | MIR3169 | 1.00 | 13203 | 3 | | | | MIR3656 | 1.00 |
| 13108 | 3 | | | | | MIR3170 | 1.00 | 13204 | 3 | | | | MIR3658 | 1.00 |
| 13109 | 3 | | | | | MIR3173 | 1.00 | 13205 | 3 | | | | MIR3659 | 1.00 |
| 13110 | 3 | | | | | MIR3175 | 1.00 | 13206 | 3 | | | | MIR365A | 1.00 |
| 13111 | 3 | | | | | MIR3176 | 1.00 | 13207 | 3 | | | | MIR365B | 1.00 |
| 13112 | 3 | | | | | MIR3177 | 1.00 | 13208 | 3 | | | | MIR3660 | 1.00 |
| 13113 | 3 | | | | | MIR3178 | 1.00 | 13209 | 3 | | | | MIR3661 | 1.00 |
| 13114 | 3 | | | | | MIR3179-1 | 1.00 | 13210 | 3 | | | | MIR3662 | 1.00 |
| 13115 | 3 | | | | | MIR3179-3 | 1.00 | 13211 | 3 | | | | MIR3663 | 1.00 |
| 13116 | 3 | | | | | MIR3180-1 | 1.00 | 13212 | 3 | | | | MIR3664 | 1.00 |
| 13117 | 3 | | | | | MIR3180-2 | 1.00 | 13213 | 3 | | | | MIR3665 | 1.00 |
| 13118 | 3 | | | | | MIR3180-3 | 1.00 | 13214 | 3 | | | | MIR3666 | 1.00 |
| 13119 | 3 | | | | | MIR3180-4 | 1.00 | 13215 | 3 | | | | MIR3668 | 1.00 |
| 13120 | 3 | | | | | MIR3180-5 | 1.00 | 13216 | 3 | | | | MIR367 | 1.00 |
| 13121 | 3 | | | | | MIR3182 | 1.00 | 13217 | 3 | | | | MIR3671 | 1.00 |
| 13122 | 3 | | | | | MIR3183 | 1.00 | 13218 | 3 | | | | MIR3675 | 1.00 |
| 13123 | 3 | | | | | MIR3184 | 1.00 | 13219 | 3 | | | | MIR3676 | 1.00 |
| 13124 | 3 | | | | | MIR3185 | 1.00 | 13220 | 3 | | | | MIR3677 | 1.00 |
| 13125 | 3 | | | | | MIR3186 | 1.00 | 13221 | 3 | | | | MIR3678 | 1.00 |
| 13126 | 3 | | | | | MIR3187 | 1.00 | 13222 | 3 | | | | MIR3679 | 1.00 |
| 13127 | 3 | | | | | MIR3188 | 1.00 | 13223 | 3 | | | | MIR3680-1 | 1.00 |
| 13128 | 3 | | | | | MIR3189 | 1.00 | 13224 | 3 | | | | MIR3682 | 1.00 |
| 13129 | 3 | | | | | MIR3190 | 1.00 | 13225 | 3 | | | | MIR3684 | 1.00 |
| 13130 | 3 | | | | | MIR3191 | 1.00 | 13226 | 3 | | | | MIR3685 | 1.00 |
| 13131 | 3 | | | | | MIR3192 | 1.00 | 13227 | 3 | | | | MIR3687 | 1.00 |
| 13132 | 3 | | | | | MIR3193 | 1.00 | 13228 | 3 | | | | MIR3688-1 | 1.00 |
| 13133 | 3 | | | | | MIR3194 | 1.00 | 13229 | 3 | | | | MIR3688-2 | 1.00 |
| 13134 | 3 | | | | | MIR3196 | 1.00 | 13230 | 3 | | | | MIR3689A | 1.00 |
| 13135 | 3 | | | | | MIR3197 | 1.00 | 13231 | 3 | | | | MIR3689B | 1.00 |
| 13136 | 3 | | | | | MIR3198-1 | 1.00 | 13232 | 3 | | | | MIR3689C | 1.00 |
| 13137 | 3 | | | | | MIR3198-2 | 1.00 | 13233 | 3 | | | | MIR3689D1 | 1.00 |
| 13138 | 3 | | | | | MIR3199-1 | 1.00 | 13234 | 3 | | | | MIR3689D2 | 1.00 |
| 13139 | 3 | | | | | MIR3199-2 | 1.00 | 13235 | 3 | | | | MIR3689E | 1.00 |
| 13140 | 3 | | | | | MIR31HG | 1.00 | 13236 | 3 | | | | MIR3689F | 1.00 |
| 13141 | 3 | | | | | MIR32 | 1.00 | 13237 | 3 | | | | MIR369 | 1.00 |
| 13142 | 3 | | | | | MIR3200 | 1.00 | 13238 | 3 | | | | MIR3690 | 1.00 |
| 13143 | 3 | | | | | MIR3201 | 1.00 | 13239 | 3 | | | | MIR3691 | 1.00 |
| 13144 | 3 | | | | | MIR3202-1 | 1.00 | 13240 | 3 | | | | MIR3692 | 1.00 |
| 13145 | 3 | | | | | MIR3202-2 | 1.00 | 13241 | 3 | | | | MIR3714 | 1.00 |
| 13146 | 3 | | | | | MIR320A | 1.00 | 13242 | 3 | | | | MIR371A | 1.00 |
| 13147 | 3 | | | | | MIR320B1 | 1.00 | 13243 | 3 | | | | MIR371B | 1.00 |

Fig. 38 - 70

| | | | | | | | | | | | | | | |
|---|---|---|---|---|---|---|---|---|---|---|---|---|---|---|
| 13244 | 3 | | | | | MIR372 | 1.00 | 13340 | 3 | | | | MIR4279 | 1.00 |
| 13245 | 3 | | | | | MIR373 | 1.00 | 13341 | 3 | | | | MIR4280 | 1.00 |
| 13246 | 3 | | | | | MIR374A | 1.00 | 13342 | 3 | | | | MIR4281 | 1.00 |
| 13247 | 3 | | | | | MIR374B | 1.00 | 13343 | 3 | | | | MIR4282 | 1.00 |
| 13248 | 3 | | | | | MIR374C | 1.00 | 13344 | 3 | | | | MIR4283-1 | 1.00 |
| 13249 | 3 | | | | | MIR375 | 1.00 | 13345 | 3 | | | | MIR4283-2 | 1.00 |
| 13250 | 3 | | | | | MIR376A1 | 1.00 | 13346 | 3 | | | | MIR4284 | 1.00 |
| 13251 | 3 | | | | | MIR376A2 | 1.00 | 13347 | 3 | | | | MIR4285 | 1.00 |
| 13252 | 3 | | | | | MIR376B | 1.00 | 13348 | 3 | | | | MIR4287 | 1.00 |
| 13253 | 3 | | | | | MIR376C | 1.00 | 13349 | 3 | | | | MIR4288 | 1.00 |
| 13254 | 3 | | | | | MIR377 | 1.00 | 13350 | 3 | | | | MIR4289 | 1.00 |
| 13255 | 3 | | | | | MIR378C | 1.00 | 13351 | 3 | | | | MIR429 | 1.00 |
| 13256 | 3 | | | | | MIR378D1 | 1.00 | 13352 | 3 | | | | MIR4290 | 1.00 |
| 13257 | 3 | | | | | MIR378D2 | 1.00 | 13353 | 3 | | | | MIR4291 | 1.00 |
| 13258 | 3 | | | | | MIR378E | 1.00 | 13354 | 3 | | | | MIR4292 | 1.00 |
| 13259 | 3 | | | | | MIR378F | 1.00 | 13355 | 3 | | | | MIR4294 | 1.00 |
| 13260 | 3 | | | | | MIR379 | 1.00 | 13356 | 3 | | | | MIR4295 | 1.00 |
| 13261 | 3 | | | | | MIR380 | 1.00 | 13357 | 3 | | | | MIR4296 | 1.00 |
| 13262 | 3 | | | | | MIR381 | 1.00 | 13358 | 3 | | | | MIR4297 | 1.00 |
| 13263 | 3 | | | | | MIR382 | 1.00 | 13359 | 3 | | | | MIR4298 | 1.00 |
| 13264 | 3 | | | | | MIR383 | 1.00 | 13360 | 3 | | | | MIR4299 | 1.00 |
| 13265 | 3 | | | | | MIR384 | 1.00 | 13361 | 3 | | | | MIR4300 | 1.00 |
| 13266 | 3 | | | | | MIR3907 | 1.00 | 13362 | 3 | | | | MIR4301 | 1.00 |
| 13267 | 3 | | | | | MIR3908 | 1.00 | 13363 | 3 | | | | MIR4302 | 1.00 |
| 13268 | 3 | | | | | MIR3909 | 1.00 | 13364 | 3 | | | | MIR4303 | 1.00 |
| 13269 | 3 | | | | | MIR3910-1 | 1.00 | 13365 | 3 | | | | MIR4304 | 1.00 |
| 13270 | 3 | | | | | MIR3910-2 | 1.00 | 13366 | 3 | | | | MIR4305 | 1.00 |
| 13271 | 3 | | | | | MIR3911 | 1.00 | 13367 | 3 | | | | MIR4306 | 1.00 |
| 13272 | 3 | | | | | MIR3912 | 1.00 | 13368 | 3 | | | | MIR4307 | 1.00 |
| 13273 | 3 | | | | | MIR3913-1 | 1.00 | 13369 | 3 | | | | MIR4308 | 1.00 |
| 13274 | 3 | | | | | MIR3913-2 | 1.00 | 13370 | 3 | | | | MIR4309 | 1.00 |
| 13275 | 3 | | | | | MIR3914-1 | 1.00 | 13371 | 3 | | | | MIR431 | 1.00 |
| 13276 | 3 | | | | | MIR3914-2 | 1.00 | 13372 | 3 | | | | MIR4310 | 1.00 |
| 13277 | 3 | | | | | MIR3916 | 1.00 | 13373 | 3 | | | | MIR4311 | 1.00 |
| 13278 | 3 | | | | | MIR3917 | 1.00 | 13374 | 3 | | | | MIR4312 | 1.00 |
| 13279 | 3 | | | | | MIR3918 | 1.00 | 13375 | 3 | | | | MIR4313 | 1.00 |
| 13280 | 3 | | | | | MIR3919 | 1.00 | 13376 | 3 | | | | MIR4314 | 1.00 |
| 13281 | 3 | | | | | MIR3920 | 1.00 | 13377 | 3 | | | | MIR4315-2 | 1.00 |
| 13282 | 3 | | | | | MIR3921 | 1.00 | 13378 | 3 | | | | MIR4316 | 1.00 |
| 13283 | 3 | | | | | MIR3922 | 1.00 | 13379 | 3 | | | | MIR4317 | 1.00 |
| 13284 | 3 | | | | | MIR3924 | 1.00 | 13380 | 3 | | | | MIR4318 | 1.00 |
| 13285 | 3 | | | | | MIR3925 | 1.00 | 13381 | 3 | | | | MIR4319 | 1.00 |
| 13286 | 3 | | | | | MIR3926-1 | 1.00 | 13382 | 3 | | | | MIR432 | 1.00 |
| 13287 | 3 | | | | | MIR3926-2 | 1.00 | 13383 | 3 | | | | MIR4320 | 1.00 |
| 13288 | 3 | | | | | MIR3928 | 1.00 | 13384 | 3 | | | | MIR4321 | 1.00 |
| 13289 | 3 | | | | | MIR3935 | 1.00 | 13385 | 3 | | | | MIR4322 | 1.00 |
| 13290 | 3 | | | | | MIR3938 | 1.00 | 13386 | 3 | | | | MIR4323 | 1.00 |
| 13291 | 3 | | | | | MIR3939 | 1.00 | 13387 | 3 | | | | MIR4324 | 1.00 |
| 13292 | 3 | | | | | MIR3940 | 1.00 | 13388 | 3 | | | | MIR4325 | 1.00 |
| 13293 | 3 | | | | | MIR3941 | 1.00 | 13389 | 3 | | | | MIR4326 | 1.00 |
| 13294 | 3 | | | | | MIR3942 | 1.00 | 13390 | 3 | | | | MIR4327 | 1.00 |
| 13295 | 3 | | | | | MIR3943 | 1.00 | 13391 | 3 | | | | MIR4328 | 1.00 |
| 13296 | 3 | | | | | MIR3944 | 1.00 | 13392 | 3 | | | | MIR4329 | 1.00 |
| 13297 | 3 | | | | | MIR3945 | 1.00 | 13393 | 3 | | | | MIR433 | 1.00 |
| 13298 | 3 | | | | | MIR3960 | 1.00 | 13394 | 3 | | | | MIR4330 | 1.00 |
| 13299 | 3 | | | | | MIR3973 | 1.00 | 13395 | 3 | | | | MIR4417 | 1.00 |
| 13300 | 3 | | | | | MIR3974 | 1.00 | 13396 | 3 | | | | MIR4420 | 1.00 |
| 13301 | 3 | | | | | MIR3975 | 1.00 | 13397 | 3 | | | | MIR4422 | 1.00 |
| 13302 | 3 | | | | | MIR3976 | 1.00 | 13398 | 3 | | | | MIR4423 | 1.00 |
| 13303 | 3 | | | | | MIR3977 | 1.00 | 13399 | 3 | | | | MIR4424 | 1.00 |
| 13304 | 3 | | | | | MIR3978 | 1.00 | 13400 | 3 | | | | MIR4426 | 1.00 |
| 13305 | 3 | | | | | MIR409 | 1.00 | 13401 | 3 | | | | MIR4427 | 1.00 |
| 13306 | 3 | | | | | MIR410 | 1.00 | 13402 | 3 | | | | MIR4429 | 1.00 |
| 13307 | 3 | | | | | MIR411 | 1.00 | 13403 | 3 | | | | MIR4432 | 1.00 |
| 13308 | 3 | | | | | MIR412 | 1.00 | 13404 | 3 | | | | MIR4434 | 1.00 |
| 13309 | 3 | | | | | MIR421 | 1.00 | 13405 | 3 | | | | MIR4435-1 | 1.00 |
| 13310 | 3 | | | | | MIR423 | 1.00 | 13406 | 3 | | | | MIR4435-2 | 1.00 |
| 13311 | 3 | | | | | MIR424 | 1.00 | 13407 | 3 | | | | MIR4436A | 1.00 |
| 13312 | 3 | | | | | MIR425 | 1.00 | 13408 | 3 | | | | MIR4436B1 | 1.00 |
| 13313 | 3 | | | | | MIR4251 | 1.00 | 13409 | 3 | | | | MIR4437 | 1.00 |
| 13314 | 3 | | | | | MIR4252 | 1.00 | 13410 | 3 | | | | MIR4439 | 1.00 |
| 13315 | 3 | | | | | MIR4253 | 1.00 | 13411 | 3 | | | | MIR4440 | 1.00 |
| 13316 | 3 | | | | | MIR4254 | 1.00 | 13412 | 3 | | | | MIR4441 | 1.00 |
| 13317 | 3 | | | | | MIR4255 | 1.00 | 13413 | 3 | | | | MIR4442 | 1.00 |
| 13318 | 3 | | | | | MIR4256 | 1.00 | 13414 | 3 | | | | MIR4443 | 1.00 |
| 13319 | 3 | | | | | MIR4257 | 1.00 | 13415 | 3 | | | | MIR4444-1 | 1.00 |
| 13320 | 3 | | | | | MIR4258 | 1.00 | 13416 | 3 | | | | MIR4446 | 1.00 |
| 13321 | 3 | | | | | MIR4260 | 1.00 | 13417 | 3 | | | | MIR4449 | 1.00 |
| 13322 | 3 | | | | | MIR4261 | 1.00 | 13418 | 3 | | | | MIR4450 | 1.00 |
| 13323 | 3 | | | | | MIR4262 | 1.00 | 13419 | 3 | | | | MIR4451 | 1.00 |
| 13324 | 3 | | | | | MIR4263 | 1.00 | 13420 | 3 | | | | MIR4453 | 1.00 |
| 13325 | 3 | | | | | MIR4264 | 1.00 | 13421 | 3 | | | | MIR4454 | 1.00 |
| 13326 | 3 | | | | | MIR4265 | 1.00 | 13422 | 3 | | | | MIR4456 | 1.00 |
| 13327 | 3 | | | | | MIR4266 | 1.00 | 13423 | 3 | | | | MIR4457 | 1.00 |
| 13328 | 3 | | | | | MIR4267 | 1.00 | 13424 | 3 | | | | MIR4458 | 1.00 |
| 13329 | 3 | | | | | MIR4268 | 1.00 | 13425 | 3 | | | | MIR4460 | 1.00 |
| 13330 | 3 | | | | | MIR4269 | 1.00 | 13426 | 3 | | | | MIR4461 | 1.00 |
| 13331 | 3 | | | | | MIR4270 | 1.00 | 13427 | 3 | | | | MIR4462 | 1.00 |
| 13332 | 3 | | | | | MIR4271 | 1.00 | 13428 | 3 | | | | MIR4464 | 1.00 |
| 13333 | 3 | | | | | MIR4272 | 1.00 | 13429 | 3 | | | | MIR4465 | 1.00 |
| 13334 | 3 | | | | | MIR4273 | 1.00 | 13430 | 3 | | | | MIR4466 | 1.00 |
| 13335 | 3 | | | | | MIR4274 | 1.00 | 13431 | 3 | | | | MIR4467 | 1.00 |
| 13336 | 3 | | | | | MIR4275 | 1.00 | 13432 | 3 | | | | MIR4468 | 1.00 |
| 13337 | 3 | | | | | MIR4276 | 1.00 | 13433 | 3 | | | | MIR4469 | 1.00 |
| 13338 | 3 | | | | | MIR4277 | 1.00 | 13434 | 3 | | | | MIR4470 | 1.00 |
| 13339 | 3 | | | | | MIR4278 | 1.00 | 13435 | 3 | | | | MIR4471 | 1.00 |

Fig. 38 - 71

| | | | | | | | | | | | | | | |
|---|---|---|---|---|---|---|---|---|---|---|---|---|---|---|
| 13436 | 3 | | | | | MIR4472-1 | 1.00 | 13532 | 3 | | | | MIR4661 | 1.00 |
| 13437 | 3 | | | | | MIR4472-2 | 1.00 | 13533 | 3 | | | | MIR4663 | 1.00 |
| 13438 | 3 | | | | | MIR4473 | 1.00 | 13534 | 3 | | | | MIR4664 | 1.00 |
| 13439 | 3 | | | | | MIR4474 | 1.00 | 13535 | 3 | | | | MIR4665 | 1.00 |
| 13440 | 3 | | | | | MIR4475 | 1.00 | 13536 | 3 | | | | MIR4666A | 1.00 |
| 13441 | 3 | | | | | MIR4476 | 1.00 | 13537 | 3 | | | | MIR4667 | 1.00 |
| 13442 | 3 | | | | | MIR4478 | 1.00 | 13538 | 3 | | | | MIR4668 | 1.00 |
| 13443 | 3 | | | | | MIR4479 | 1.00 | 13539 | 3 | | | | MIR4669 | 1.00 |
| 13444 | 3 | | | | | MIR448 | 1.00 | 13540 | 3 | | | | MIR4670 | 1.00 |
| 13445 | 3 | | | | | MIR4480 | 1.00 | 13541 | 3 | | | | MIR4671 | 1.00 |
| 13446 | 3 | | | | | MIR4482-1 | 1.00 | 13542 | 3 | | | | MIR4672 | 1.00 |
| 13447 | 3 | | | | | MIR4483 | 1.00 | 13543 | 3 | | | | MIR4673 | 1.00 |
| 13448 | 3 | | | | | MIR4484 | 1.00 | 13544 | 3 | | | | MIR4674 | 1.00 |
| 13449 | 3 | | | | | MIR4485 | 1.00 | 13545 | 3 | | | | MIR4675 | 1.00 |
| 13450 | 3 | | | | | MIR4486 | 1.00 | 13546 | 3 | | | | MIR4676 | 1.00 |
| 13451 | 3 | | | | | MIR4488 | 1.00 | 13547 | 3 | | | | MIR4677 | 1.00 |
| 13452 | 3 | | | | | MIR4489 | 1.00 | 13548 | 3 | | | | MIR4678 | 1.00 |
| 13453 | 3 | | | | | MIR4490 | 1.00 | 13549 | 3 | | | | MIR4679-1 | 1.00 |
| 13454 | 3 | | | | | MIR4491 | 1.00 | 13550 | 3 | | | | MIR4679-2 | 1.00 |
| 13455 | 3 | | | | | MIR4492 | 1.00 | 13551 | 3 | | | | MIR4680 | 1.00 |
| 13456 | 3 | | | | | MIR4493 | 1.00 | 13552 | 3 | | | | MIR4681 | 1.00 |
| 13457 | 3 | | | | | MIR4497 | 1.00 | 13553 | 3 | | | | MIR4682 | 1.00 |
| 13458 | 3 | | | | | MIR4498 | 1.00 | 13554 | 3 | | | | MIR4683 | 1.00 |
| 13459 | 3 | | | | | MIR4499 | 1.00 | 13555 | 3 | | | | MIR4684 | 1.00 |
| 13460 | 3 | | | | | MIR449A | 1.00 | 13556 | 3 | | | | MIR4685 | 1.00 |
| 13461 | 3 | | | | | MIR449B | 1.00 | 13557 | 3 | | | | MIR4686 | 1.00 |
| 13462 | 3 | | | | | MIR449C | 1.00 | 13558 | 3 | | | | MIR4687 | 1.00 |
| 13463 | 3 | | | | | MIR4500 | 1.00 | 13559 | 3 | | | | MIR4688 | 1.00 |
| 13464 | 3 | | | | | MIR4500HG | 1.00 | 13560 | 3 | | | | MIR4689 | 1.00 |
| 13465 | 3 | | | | | MIR4503 | 1.00 | 13561 | 3 | | | | MIR4690 | 1.00 |
| 13466 | 3 | | | | | MIR4505 | 1.00 | 13562 | 3 | | | | MIR4691 | 1.00 |
| 13467 | 3 | | | | | MIR4508 | 1.00 | 13563 | 3 | | | | MIR4692 | 1.00 |
| 13468 | 3 | | | | | MIR4509-1 | 1.00 | 13564 | 3 | | | | MIR4693 | 1.00 |
| 13469 | 3 | | | | | MIR450A1 | 1.00 | 13565 | 3 | | | | MIR4694 | 1.00 |
| 13470 | 3 | | | | | MIR450A2 | 1.00 | 13566 | 3 | | | | MIR4695 | 1.00 |
| 13471 | 3 | | | | | MIR450B | 1.00 | 13567 | 3 | | | | MIR4696 | 1.00 |
| 13472 | 3 | | | | | MIR4510 | 1.00 | 13568 | 3 | | | | MIR4697 | 1.00 |
| 13473 | 3 | | | | | MIR4511 | 1.00 | 13569 | 3 | | | | MIR4698 | 1.00 |
| 13474 | 3 | | | | | MIR4513 | 1.00 | 13570 | 3 | | | | MIR4699 | 1.00 |
| 13475 | 3 | | | | | MIR4514 | 1.00 | 13571 | 3 | | | | MIR4700 | 1.00 |
| 13476 | 3 | | | | | MIR4515 | 1.00 | 13572 | 3 | | | | MIR4701 | 1.00 |
| 13477 | 3 | | | | | MIR4516 | 1.00 | 13573 | 3 | | | | MIR4703 | 1.00 |
| 13478 | 3 | | | | | MIR4517 | 1.00 | 13574 | 3 | | | | MIR4705 | 1.00 |
| 13479 | 3 | | | | | MIR4518 | 1.00 | 13575 | 3 | | | | MIR4706 | 1.00 |
| 13480 | 3 | | | | | MIR4519 | 1.00 | 13576 | 3 | | | | MIR4707 | 1.00 |
| 13481 | 3 | | | | | MIR451A | 1.00 | 13577 | 3 | | | | MIR4708 | 1.00 |
| 13482 | 3 | | | | | MIR451B | 1.00 | 13578 | 3 | | | | MIR4709 | 1.00 |
| 13483 | 3 | | | | | MIR452 | 1.00 | 13579 | 3 | | | | MIR4710 | 1.00 |
| 13484 | 3 | | | | | MIR4520A | 1.00 | 13580 | 3 | | | | MIR4711 | 1.00 |
| 13485 | 3 | | | | | MIR4520B | 1.00 | 13581 | 3 | | | | MIR4712 | 1.00 |
| 13486 | 3 | | | | | MIR4521 | 1.00 | 13582 | 3 | | | | MIR4713 | 1.00 |
| 13487 | 3 | | | | | MIR4522 | 1.00 | 13583 | 3 | | | | MIR4714 | 1.00 |
| 13488 | 3 | | | | | MIR4523 | 1.00 | 13584 | 3 | | | | MIR4715 | 1.00 |
| 13489 | 3 | | | | | MIR4524A | 1.00 | 13585 | 3 | | | | MIR4716 | 1.00 |
| 13490 | 3 | | | | | MIR4526 | 1.00 | 13586 | 3 | | | | MIR4717 | 1.00 |
| 13491 | 3 | | | | | MIR4529 | 1.00 | 13587 | 3 | | | | MIR4718 | 1.00 |
| 13492 | 3 | | | | | MIR4530 | 1.00 | 13588 | 3 | | | | MIR4719 | 1.00 |
| 13493 | 3 | | | | | MIR4531 | 1.00 | 13589 | 3 | | | | MIR4720 | 1.00 |
| 13494 | 3 | | | | | MIR4532 | 1.00 | 13590 | 3 | | | | MIR4721 | 1.00 |
| 13495 | 3 | | | | | MIR4533 | 1.00 | 13591 | 3 | | | | MIR4722 | 1.00 |
| 13496 | 3 | | | | | MIR4534 | 1.00 | 13592 | 3 | | | | MIR4723 | 1.00 |
| 13497 | 3 | | | | | MIR4535 | 1.00 | 13593 | 3 | | | | MIR4724 | 1.00 |
| 13498 | 3 | | | | | MIR4536-1 | 1.00 | 13594 | 3 | | | | MIR4725 | 1.00 |
| 13499 | 3 | | | | | MIR454 | 1.00 | 13595 | 3 | | | | MIR4726 | 1.00 |
| 13500 | 3 | | | | | MIR4540 | 1.00 | 13596 | 3 | | | | MIR4727 | 1.00 |
| 13501 | 3 | | | | | MIR455 | 1.00 | 13597 | 3 | | | | MIR4728 | 1.00 |
| 13502 | 3 | | | | | MIR4632 | 1.00 | 13598 | 3 | | | | MIR4729 | 1.00 |
| 13503 | 3 | | | | | MIR4633 | 1.00 | 13599 | 3 | | | | MIR4730 | 1.00 |
| 13504 | 3 | | | | | MIR4634 | 1.00 | 13600 | 3 | | | | MIR4731 | 1.00 |
| 13505 | 3 | | | | | MIR4635 | 1.00 | 13601 | 3 | | | | MIR4732 | 1.00 |
| 13506 | 3 | | | | | MIR4636 | 1.00 | 13602 | 3 | | | | MIR4733 | 1.00 |
| 13507 | 3 | | | | | MIR4637 | 1.00 | 13603 | 3 | | | | MIR4734 | 1.00 |
| 13508 | 3 | | | | | MIR4638 | 1.00 | 13604 | 3 | | | | MIR4735 | 1.00 |
| 13509 | 3 | | | | | MIR4639 | 1.00 | 13605 | 3 | | | | MIR4736 | 1.00 |
| 13510 | 3 | | | | | MIR4640 | 1.00 | 13606 | 3 | | | | MIR4737 | 1.00 |
| 13511 | 3 | | | | | MIR4641 | 1.00 | 13607 | 3 | | | | MIR4738 | 1.00 |
| 13512 | 3 | | | | | MIR4642 | 1.00 | 13608 | 3 | | | | MIR4739 | 1.00 |
| 13513 | 3 | | | | | MIR4643 | 1.00 | 13609 | 3 | | | | MIR4740 | 1.00 |
| 13514 | 3 | | | | | MIR4644 | 1.00 | 13610 | 3 | | | | MIR4741 | 1.00 |
| 13515 | 3 | | | | | MIR4645 | 1.00 | 13611 | 3 | | | | MIR4742 | 1.00 |
| 13516 | 3 | | | | | MIR4646 | 1.00 | 13612 | 3 | | | | MIR4743 | 1.00 |
| 13517 | 3 | | | | | MIR4647 | 1.00 | 13613 | 3 | | | | MIR4744 | 1.00 |
| 13518 | 3 | | | | | MIR4648 | 1.00 | 13614 | 3 | | | | MIR4745 | 1.00 |
| 13519 | 3 | | | | | MIR4649 | 1.00 | 13615 | 3 | | | | MIR4746 | 1.00 |
| 13520 | 3 | | | | | MIR4650-1 | 1.00 | 13616 | 3 | | | | MIR4747 | 1.00 |
| 13521 | 3 | | | | | MIR4651 | 1.00 | 13617 | 3 | | | | MIR4748 | 1.00 |
| 13522 | 3 | | | | | MIR4652 | 1.00 | 13618 | 3 | | | | MIR4749 | 1.00 |
| 13523 | 3 | | | | | MIR4653 | 1.00 | 13619 | 3 | | | | MIR4750 | 1.00 |
| 13524 | 3 | | | | | MIR4654 | 1.00 | 13620 | 3 | | | | MIR4751 | 1.00 |
| 13525 | 3 | | | | | MIR4655 | 1.00 | 13621 | 3 | | | | MIR4752 | 1.00 |
| 13526 | 3 | | | | | MIR4656 | 1.00 | 13622 | 3 | | | | MIR4753 | 1.00 |
| 13527 | 3 | | | | | MIR4657 | 1.00 | 13623 | 3 | | | | MIR4754 | 1.00 |
| 13528 | 3 | | | | | MIR4658 | 1.00 | 13624 | 3 | | | | MIR4755 | 1.00 |
| 13529 | 3 | | | | | MIR4659A | 1.00 | 13625 | 3 | | | | MIR4756 | 1.00 |
| 13530 | 3 | | | | | MIR4659B | 1.00 | 13626 | 3 | | | | MIR4757 | 1.00 |
| 13531 | 3 | | | | | MIR4660 | 1.00 | 13627 | 3 | | | | MIR4758 | 1.00 |

Fig. 38 - 72

| | | | | | | | | | | | | | | |
|---|---|---|---|---|---|---|---|---|---|---|---|---|---|---|
| 13628 | 3 | | | | | MIR4759 | 1.00 | 13724 | 3 | | | | MIR518B | 1.00 |
| 13629 | 3 | | | | | MIR4760 | 1.00 | 13725 | 3 | | | | MIR518C | 1.00 |
| 13630 | 3 | | | | | MIR4761 | 1.00 | 13726 | 3 | | | | MIR518D | 1.00 |
| 13631 | 3 | | | | | MIR4762 | 1.00 | 13727 | 3 | | | | MIR518E | 1.00 |
| 13632 | 3 | | | | | MIR4763 | 1.00 | 13728 | 3 | | | | MIR518F | 1.00 |
| 13633 | 3 | | | | | MIR4764 | 1.00 | 13729 | 3 | | | | MIR519A1 | 1.00 |
| 13634 | 3 | | | | | MIR4765 | 1.00 | 13730 | 3 | | | | MIR519A2 | 1.00 |
| 13635 | 3 | | | | | MIR4766 | 1.00 | 13731 | 3 | | | | MIR519B | 1.00 |
| 13636 | 3 | | | | | MIR4767 | 1.00 | 13732 | 3 | | | | MIR519C | 1.00 |
| 13637 | 3 | | | | | MIR4768 | 1.00 | 13733 | 3 | | | | MIR519D | 1.00 |
| 13638 | 3 | | | | | MIR4769 | 1.00 | 13734 | 3 | | | | MIR519E | 1.00 |
| 13639 | 3 | | | | | MIR4770 | 1.00 | 13735 | 3 | | | | MIR520A | 1.00 |
| 13640 | 3 | | | | | MIR4772 | 1.00 | 13736 | 3 | | | | MIR520B | 1.00 |
| 13641 | 3 | | | | | MIR4773-2 | 1.00 | 13737 | 3 | | | | MIR520C | 1.00 |
| 13642 | 3 | | | | | MIR4774 | 1.00 | 13738 | 3 | | | | MIR520D | 1.00 |
| 13643 | 3 | | | | | MIR4775 | 1.00 | 13739 | 3 | | | | MIR520E | 1.00 |
| 13644 | 3 | | | | | MIR4776-2 | 1.00 | 13740 | 3 | | | | MIR520F | 1.00 |
| 13645 | 3 | | | | | MIR4777 | 1.00 | 13741 | 3 | | | | MIR520G | 1.00 |
| 13646 | 3 | | | | | MIR4778 | 1.00 | 13742 | 3 | | | | MIR520H | 1.00 |
| 13647 | 3 | | | | | MIR4779 | 1.00 | 13743 | 3 | | | | MIR521-1 | 1.00 |
| 13648 | 3 | | | | | MIR4780 | 1.00 | 13744 | 3 | | | | MIR521-2 | 1.00 |
| 13649 | 3 | | | | | MIR4781 | 1.00 | 13745 | 3 | | | | MIR522 | 1.00 |
| 13650 | 3 | | | | | MIR4782 | 1.00 | 13746 | 3 | | | | MIR523 | 1.00 |
| 13651 | 3 | | | | | MIR4783 | 1.00 | 13747 | 3 | | | | MIR524 | 1.00 |
| 13652 | 3 | | | | | MIR4784 | 1.00 | 13748 | 3 | | | | MIR525 | 1.00 |
| 13653 | 3 | | | | | MIR4785 | 1.00 | 13749 | 3 | | | | MIR526A1 | 1.00 |
| 13654 | 3 | | | | | MIR4786 | 1.00 | 13750 | 3 | | | | MIR526A2 | 1.00 |
| 13655 | 3 | | | | | MIR4787 | 1.00 | 13751 | 3 | | | | MIR526B | 1.00 |
| 13656 | 3 | | | | | MIR4788 | 1.00 | 13752 | 3 | | | | MIR527 | 1.00 |
| 13657 | 3 | | | | | MIR4789 | 1.00 | 13753 | 3 | | | | MIR532 | 1.00 |
| 13658 | 3 | | | | | MIR4790 | 1.00 | 13754 | 3 | | | | MIR539 | 1.00 |
| 13659 | 3 | | | | | MIR4791 | 1.00 | 13755 | 3 | | | | MIR541 | 1.00 |
| 13660 | 3 | | | | | MIR4792 | 1.00 | 13756 | 3 | | | | MIR542 | 1.00 |
| 13661 | 3 | | | | | MIR4793 | 1.00 | 13757 | 3 | | | | MIR543 | 1.00 |
| 13662 | 3 | | | | | MIR4794 | 1.00 | 13758 | 3 | | | | MIR545 | 1.00 |
| 13663 | 3 | | | | | MIR4795 | 1.00 | 13759 | 3 | | | | MIR548A1 | 1.00 |
| 13664 | 3 | | | | | MIR4796 | 1.00 | 13760 | 3 | | | | MIR548A2 | 1.00 |
| 13665 | 3 | | | | | MIR4797 | 1.00 | 13761 | 3 | | | | MIR548A3 | 1.00 |
| 13666 | 3 | | | | | MIR4798 | 1.00 | 13762 | 3 | | | | MIR548AA1 | 1.00 |
| 13667 | 3 | | | | | MIR4799 | 1.00 | 13763 | 3 | | | | MIR548AA2 | 1.00 |
| 13668 | 3 | | | | | MIR4800 | 1.00 | 13764 | 3 | | | | MIR548AC | 1.00 |
| 13669 | 3 | | | | | MIR4801 | 1.00 | 13765 | 3 | | | | MIR548AD | 1.00 |
| 13670 | 3 | | | | | MIR4802 | 1.00 | 13766 | 3 | | | | MIR548AE2 | 1.00 |
| 13671 | 3 | | | | | MIR4803 | 1.00 | 13767 | 3 | | | | MIR548AI | 1.00 |
| 13672 | 3 | | | | | MIR4804 | 1.00 | 13768 | 3 | | | | MIR548AJ2 | 1.00 |
| 13673 | 3 | | | | | MIR483 | 1.00 | 13769 | 3 | | | | MIR548AL | 1.00 |
| 13674 | 3 | | | | | MIR484 | 1.00 | 13770 | 3 | | | | MIR548AN | 1.00 |
| 13675 | 3 | | | | | MIR485 | 1.00 | 13771 | 3 | | | | MIR548B | 1.00 |
| 13676 | 3 | | | | | MIR486 | 1.00 | 13772 | 3 | | | | MIR548C | 1.00 |
| 13677 | 3 | | | | | MIR487A | 1.00 | 13773 | 3 | | | | MIR548D2 | 1.00 |
| 13678 | 3 | | | | | MIR487B | 1.00 | 13774 | 3 | | | | MIR548F1 | 1.00 |
| 13679 | 3 | | | | | MIR488 | 1.00 | 13775 | 3 | | | | MIR548F2 | 1.00 |
| 13680 | 3 | | | | | MIR489 | 1.00 | 13776 | 3 | | | | MIR548F3 | 1.00 |
| 13681 | 3 | | | | | MIR490 | 1.00 | 13777 | 3 | | | | MIR548F4 | 1.00 |
| 13682 | 3 | | | | | MIR491 | 1.00 | 13778 | 3 | | | | MIR548F5 | 1.00 |
| 13683 | 3 | | | | | MIR493 | 1.00 | 13779 | 3 | | | | MIR548G | 1.00 |
| 13684 | 3 | | | | | MIR494 | 1.00 | 13780 | 3 | | | | MIR548H2 | 1.00 |
| 13685 | 3 | | | | | MIR495 | 1.00 | 13781 | 3 | | | | MIR548H3 | 1.00 |
| 13686 | 3 | | | | | MIR496 | 1.00 | 13782 | 3 | | | | MIR548H4 | 1.00 |
| 13687 | 3 | | | | | MIR497 | 1.00 | 13783 | 3 | | | | MIR548I1 | 1.00 |
| 13688 | 3 | | | | | MIR498 | 1.00 | 13784 | 3 | | | | MIR548I2 | 1.00 |
| 13689 | 3 | | | | | MIR499A | 1.00 | 13785 | 3 | | | | MIR548I3 | 1.00 |
| 13690 | 3 | | | | | MIR499B | 1.00 | 13786 | 3 | | | | MIR548I4 | 1.00 |
| 13691 | 3 | | | | | MIR500A | 1.00 | 13787 | 3 | | | | MIR548J | 1.00 |
| 13692 | 3 | | | | | MIR500B | 1.00 | 13788 | 3 | | | | MIR548K | 1.00 |
| 13693 | 3 | | | | | MIR501 | 1.00 | 13789 | 3 | | | | MIR548M | 1.00 |
| 13694 | 3 | | | | | MIR502 | 1.00 | 13790 | 3 | | | | MIR548N | 1.00 |
| 13695 | 3 | | | | | MIR503 | 1.00 | 13791 | 3 | | | | MIR548O2 | 1.00 |
| 13696 | 3 | | | | | MIR504 | 1.00 | 13792 | 3 | | | | MIR548Q | 1.00 |
| 13697 | 3 | | | | | MIR504Z | 1.00 | 13793 | 3 | | | | MIR548T | 1.00 |
| 13698 | 3 | | | | | MIR505 | 1.00 | 13794 | 3 | | | | MIR548W | 1.00 |
| 13699 | 3 | | | | | MIR506 | 1.00 | 13795 | 3 | | | | MIR548X | 1.00 |
| 13700 | 3 | | | | | MIR507 | 1.00 | 13796 | 3 | | | | MIR548Y | 1.00 |
| 13701 | 3 | | | | | MIR508 | 1.00 | 13797 | 3 | | | | MIR549 | 1.00 |
| 13702 | 3 | | | | | MIR509-1 | 1.00 | 13798 | 3 | | | | MIR550A3 | 1.00 |
| 13703 | 3 | | | | | MIR509-2 | 1.00 | 13799 | 3 | | | | MIR550B1 | 1.00 |
| 13704 | 3 | | | | | MIR509-3 | 1.00 | 13800 | 3 | | | | MIR550B2 | 1.00 |
| 13705 | 3 | | | | | MIR509S | 1.00 | 13801 | 3 | | | | MIR551A | 1.00 |
| 13706 | 3 | | | | | MIR510 | 1.00 | 13802 | 3 | | | | MIR551B | 1.00 |
| 13707 | 3 | | | | | MIR511-2 | 1.00 | 13803 | 3 | | | | MIR553 | 1.00 |
| 13708 | 3 | | | | | MIR512-1 | 1.00 | 13804 | 3 | | | | MIR554 | 1.00 |
| 13709 | 3 | | | | | MIR512-2 | 1.00 | 13805 | 3 | | | | MIR555 | 1.00 |
| 13710 | 3 | | | | | MIR514A1 | 1.00 | 13806 | 3 | | | | MIR556 | 1.00 |
| 13711 | 3 | | | | | MIR514A3 | 1.00 | 13807 | 3 | | | | MIR557 | 1.00 |
| 13712 | 3 | | | | | MIR514B | 1.00 | 13808 | 3 | | | | MIR558 | 1.00 |
| 13713 | 3 | | | | | MIR515-1 | 1.00 | 13809 | 3 | | | | MIR559 | 1.00 |
| 13714 | 3 | | | | | MIR515-2 | 1.00 | 13810 | 3 | | | | MIR561 | 1.00 |
| 13715 | 3 | | | | | MIR516A1 | 1.00 | 13811 | 3 | | | | MIR563 | 1.00 |
| 13716 | 3 | | | | | MIR516A2 | 1.00 | 13812 | 3 | | | | MIR564 | 1.00 |
| 13717 | 3 | | | | | MIR516B1 | 1.00 | 13813 | 3 | | | | MIR567 | 1.00 |
| 13718 | 3 | | | | | MIR516B2 | 1.00 | 13814 | 3 | | | | MIR568 | 1.00 |
| 13719 | 3 | | | | | MIR517A | 1.00 | 13815 | 3 | | | | MIR569 | 1.00 |
| 13720 | 3 | | | | | MIR517B | 1.00 | 13816 | 3 | | | | MIR572 | 1.00 |
| 13721 | 3 | | | | | MIR517C | 1.00 | 13817 | 3 | | | | MIR573 | 1.00 |
| 13722 | 3 | | | | | MIR518A1 | 1.00 | 13818 | 3 | | | | MIR574 | 1.00 |
| 13723 | 3 | | | | | MIR518A2 | 1.00 | 13819 | 3 | | | | MIR575 | 1.00 |

Fig. 38 - 73

| | | | | | | | | | | | | | | |
|---|---|---|---|---|---|---|---|---|---|---|---|---|---|---|
| 13820 | 3 | | | | | MIR577 | 1.00 | 13916 | 3 | | | | MIR769 | 1.00 |
| 13821 | 3 | | | | | MIR578 | 1.00 | 13917 | 3 | | | | MIR770 | 1.00 |
| 13822 | 3 | | | | | MIR580 | 1.00 | 13918 | 3 | | | | MIR802 | 1.00 |
| 13823 | 3 | | | | | MIR581 | 1.00 | 13919 | 3 | | | | MIR873 | 1.00 |
| 13824 | 3 | | | | | MIR583 | 1.00 | 13920 | 3 | | | | MIR874 | 1.00 |
| 13825 | 3 | | | | | MIR585 | 1.00 | 13921 | 3 | | | | MIR875 | 1.00 |
| 13826 | 3 | | | | | MIR586 | 1.00 | 13922 | 3 | | | | MIR876 | 1.00 |
| 13827 | 3 | | | | | MIR589 | 1.00 | 13923 | 3 | | | | MIR877 | 1.00 |
| 13828 | 3 | | | | | MIR590 | 1.00 | 13924 | 3 | | | | MIR885 | 1.00 |
| 13829 | 3 | | | | | MIR591 | 1.00 | 13925 | 3 | | | | MIR888 | 1.00 |
| 13830 | 3 | | | | | MIR592 | 1.00 | 13926 | 3 | | | | MIR889 | 1.00 |
| 13831 | 3 | | | | | MIR593 | 1.00 | 13927 | 3 | | | | MIR890 | 1.00 |
| 13832 | 3 | | | | | MIR595 | 1.00 | 13928 | 3 | | | | MIR891A | 1.00 |
| 13833 | 3 | | | | | MIR596 | 1.00 | 13929 | 3 | | | | MIR891B | 1.00 |
| 13834 | 3 | | | | | MIR597 | 1.00 | 13930 | 3 | | | | MIR892A | 1.00 |
| 13835 | 3 | | | | | MIR598 | 1.00 | 13931 | 3 | | | | MIR892B | 1.00 |
| 13836 | 3 | | | | | MIR599 | 1.00 | 13932 | 3 | | | | MIR9-1 | 1.00 |
| 13837 | 3 | | | | | MIR600 | 1.00 | 13933 | 3 | | | | MIR9-2 | 1.00 |
| 13838 | 3 | | | | | MIR601 | 1.00 | 13934 | 3 | | | | MIR920 | 1.00 |
| 13839 | 3 | | | | | MIR602 | 1.00 | 13935 | 3 | | | | MIR921 | 1.00 |
| 13840 | 3 | | | | | MIR603 | 1.00 | 13936 | 3 | | | | MIR922 | 1.00 |
| 13841 | 3 | | | | | MIR604 | 1.00 | 13937 | 3 | | | | MIR92A1 | 1.00 |
| 13842 | 3 | | | | | MIR605 | 1.00 | 13938 | 3 | | | | MIR92A2 | 1.00 |
| 13843 | 3 | | | | | MIR608 | 1.00 | 13939 | 3 | | | | MIR92B | 1.00 |
| 13844 | 3 | | | | | MIR609 | 1.00 | 13940 | 3 | | | | MIR93 | 1.00 |
| 13845 | 3 | | | | | MIR610 | 1.00 | 13941 | 3 | | | | MIR9-3 | 1.00 |
| 13846 | 3 | | | | | MIR611 | 1.00 | 13942 | 3 | | | | MIR933 | 1.00 |
| 13847 | 3 | | | | | MIR612 | 1.00 | 13943 | 3 | | | | MIR934 | 1.00 |
| 13848 | 3 | | | | | MIR613 | 1.00 | 13944 | 3 | | | | MIR935 | 1.00 |
| 13849 | 3 | | | | | MIR614 | 1.00 | 13945 | 3 | | | | MIR936 | 1.00 |
| 13850 | 3 | | | | | MIR615 | 1.00 | 13946 | 3 | | | | MIR937 | 1.00 |
| 13851 | 3 | | | | | MIR617 | 1.00 | 13947 | 3 | | | | MIR938 | 1.00 |
| 13852 | 3 | | | | | MIR618 | 1.00 | 13948 | 3 | | | | MIR939 | 1.00 |
| 13853 | 3 | | | | | MIR620 | 1.00 | 13949 | 3 | | | | MIR940 | 1.00 |
| 13854 | 3 | | | | | MIR621 | 1.00 | 13950 | 3 | | | | MIR941-1 | 1.00 |
| 13855 | 3 | | | | | MIR622 | 1.00 | 13951 | 3 | | | | MIR941-2 | 1.00 |
| 13856 | 3 | | | | | MIR623 | 1.00 | 13952 | 3 | | | | MIR941-3 | 1.00 |
| 13857 | 3 | | | | | MIR624 | 1.00 | 13953 | 3 | | | | MIR941-4 | 1.00 |
| 13858 | 3 | | | | | MIR626 | 1.00 | 13954 | 3 | | | | MIR942 | 1.00 |
| 13859 | 3 | | | | | MIR627 | 1.00 | 13955 | 3 | | | | MIR943 | 1.00 |
| 13860 | 3 | | | | | MIR628 | 1.00 | 13956 | 3 | | | | MIR944 | 1.00 |
| 13861 | 3 | | | | | MIR629 | 1.00 | 13957 | 3 | | | | MIR96 | 1.00 |
| 13862 | 3 | | | | | MIR630 | 1.00 | 13958 | 3 | | | | MIR98 | 1.00 |
| 13863 | 3 | | | | | MIR631 | 1.00 | 13959 | 3 | | | | MIR99A | 1.00 |
| 13864 | 3 | | | | | MIR632 | 1.00 | 13960 | 3 | | | | MIR99B | 1.00 |
| 13865 | 3 | | | | | MIR634 | 1.00 | 13961 | 3 | | | | MIRLET7A1 | 1.00 |
| 13866 | 3 | | | | | MIR635 | 1.00 | 13962 | 3 | | | | MIRLET7A2 | 1.00 |
| 13867 | 3 | | | | | MIR636 | 1.00 | 13963 | 3 | | | | MIRLET7A3 | 1.00 |
| 13868 | 3 | | | | | MIR637 | 1.00 | 13964 | 3 | | | | MIRLET7B | 1.00 |
| 13869 | 3 | | | | | MIR638 | 1.00 | 13965 | 3 | | | | MIRLET7C | 1.00 |
| 13870 | 3 | | | | | MIR639 | 1.00 | 13966 | 3 | | | | MIRLET7D | 1.00 |
| 13871 | 3 | | | | | MIR641 | 1.00 | 13967 | 3 | | | | MIRLET7E | 1.00 |
| 13872 | 3 | | | | | MIR642A | 1.00 | 13968 | 3 | | | | MIRLET7F1 | 1.00 |
| 13873 | 3 | | | | | MIR642B | 1.00 | 13969 | 3 | | | | MIRLET7F2 | 1.00 |
| 13874 | 3 | | | | | MIR643 | 1.00 | 13970 | 3 | | | | MIRLET7G | 1.00 |
| 13875 | 3 | | | | | MIR644A | 1.00 | 13971 | 3 | | | | MIRLET7I | 1.00 |
| 13876 | 3 | | | | | MIR645 | 1.00 | 13972 | 3 | | | | MIXL1 | 1.00 |
| 13877 | 3 | | | | | MIR647 | 1.00 | 13973 | 3 | | | | MKRN3 | 1.00 |
| 13878 | 3 | | | | | MIR648 | 1.00 | 13974 | 3 | | | | MKRN7P | 1.00 |
| 13879 | 3 | | | | | MIR650 | 1.00 | 13975 | 3 | | | | MLC1 | 1.00 |
| 13880 | 3 | | | | | MIR651 | 1.00 | 13976 | 3 | | | | MLK7-AS1 | 1.00 |
| 13881 | 3 | | | | | MIR653 | 1.00 | 13977 | 3 | | | | MLLT10P1 | 1.00 |
| 13882 | 3 | | | | | MIR654 | 1.00 | 13978 | 3 | | | | MLN | 1.00 |
| 13883 | 3 | | | | | MIR655 | 1.00 | 13979 | 3 | | | | MLNR | 1.00 |
| 13884 | 3 | | | | | MIR656 | 1.00 | 13980 | 3 | | | | MMD2 | 1.00 |
| 13885 | 3 | | | | | MIR657 | 1.00 | 13981 | 3 | | | | MMEL1 | 1.00 |
| 13886 | 3 | | | | | MIR658 | 1.00 | 13982 | 3 | | | | MMP1 | 1.00 |
| 13887 | 3 | | | | | MIR659 | 1.00 | 13983 | 3 | | | | MMP10 | 1.00 |
| 13888 | 3 | | | | | MIR660 | 1.00 | 13984 | 3 | | | | MMP12 | 1.00 |
| 13889 | 3 | | | | | MIR661 | 1.00 | 13985 | 3 | | | | MMP13 | 1.00 |
| 13890 | 3 | | | | | MIR662 | 1.00 | 13986 | 3 | | | | MMP16 | 1.00 |
| 13891 | 3 | | | | | MIR663A | 1.00 | 13987 | 3 | | | | MMP20 | 1.00 |
| 13892 | 3 | | | | | MIR663B | 1.00 | 13988 | 3 | | | | MMP21 | 1.00 |
| 13893 | 3 | | | | | MIR664 | 1.00 | 13989 | 3 | | | | MMP26 | 1.00 |
| 13894 | 3 | | | | | MIR665 | 1.00 | 13990 | 3 | | | | MMP3 | 1.00 |
| 13895 | 3 | | | | | MIR668 | 1.00 | 13991 | 3 | | | | MMP8 | 1.00 |
| 13896 | 3 | | | | | MIR670 | 1.00 | 13992 | 3 | | | | MND1 | 1.00 |
| 13897 | 3 | | | | | MIR671 | 1.00 | 13993 | 3 | | | | MNX1 | 1.00 |
| 13898 | 3 | | | | | MIR675 | 1.00 | 13994 | 3 | | | | MOB4 | 1.00 |
| 13899 | 3 | | | | | MIR676 | 1.00 | 13995 | 3 | | | | MOBP | 1.00 |
| 13900 | 3 | | | | | MIR708 | 1.00 | 13996 | 3 | | | | MOG | 1.00 |
| 13901 | 3 | | | | | MIR711 | 1.00 | 13997 | 3 | | | | MOGAT3 | 1.00 |
| 13902 | 3 | | | | | MIR718 | 1.00 | 13998 | 3 | | | | MORC1 | 1.00 |
| 13903 | 3 | | | | | MIR7-2 | 1.00 | 13999 | 3 | | | | MORN5 | 1.00 |
| 13904 | 3 | | | | | MIR7-3 | 1.00 | 14000 | 3 | | | | MOS | 1.00 |
| 13905 | 3 | | | | | MIR7-3HG | 1.00 | 14001 | 3 | | | | MOV10L1 | 1.00 |
| 13906 | 3 | | | | | MIR744 | 1.00 | 14002 | 3 | | | | MOXD2P | 1.00 |
| 13907 | 3 | | | | | MIR758 | 1.00 | 14003 | 3 | | | | MPHOSPH9 | 1.00 |
| 13908 | 3 | | | | | MIR759 | 1.00 | 14004 | 3 | | | | MPL | 1.00 |
| 13909 | 3 | | | | | MIR760 | 1.00 | 14005 | 3 | | | | MPO | 1.00 |
| 13910 | 3 | | | | | MIR761 | 1.00 | 14006 | 3 | | | | MPP4 | 1.00 |
| 13911 | 3 | | | | | MIR762 | 1.00 | 14007 | 3 | | | | MRGPRD | 1.00 |
| 13912 | 3 | | | | | MIR764 | 1.00 | 14008 | 3 | | | | MRGPRE | 1.00 |
| 13913 | 3 | | | | | MIR765 | 1.00 | 14009 | 3 | | | | MRGPRG | 1.00 |
| 13914 | 3 | | | | | MIR766 | 1.00 | 14010 | 3 | | | | MRGPRX1 | 1.00 |
| 13915 | 3 | | | | | MIR767 | 1.00 | 14011 | 3 | | | | MRGPRX3 | 1.00 |

Fig. 38 - 74

| | | | | | | | | | | | | | |
|---|---|---|---|---|---|---|---|---|---|---|---|---|---|
| 14012 | 3 | | | | | MRGPRX4 | 1.00 | 14108 | 3 | | | MYT1 | 1.00 |
| 14013 | 3 | | | | | MRO | 1.00 | 14109 | 3 | | | MYT1L | 1.00 |
| 14014 | 3 | | | | | MRVI1-AS1 | 1.00 | 14110 | 3 | | | MZB1 | 1.00 |
| 14015 | 3 | | | | | MS4A1 | 1.00 | 14111 | 3 | | | NAA11 | 1.00 |
| 14016 | 3 | | | | | MS4A10 | 1.00 | 14112 | 3 | | | NALCN | 1.00 |
| 14017 | 3 | | | | | MS4A12 | 1.00 | 14113 | 3 | | | NANOG | 1.00 |
| 14018 | 3 | | | | | MS4A13 | 1.00 | 14114 | 3 | | | NANOGNB | 1.00 |
| 14019 | 3 | | | | | MS4A15 | 1.00 | 14115 | 3 | | | NANOS2 | 1.00 |
| 14020 | 3 | | | | | MS4A3 | 1.00 | 14116 | 3 | | | NANOS3 | 1.00 |
| 14021 | 3 | | | | | MS4A5 | 1.00 | 14117 | 3 | | | NAP1L6 | 1.00 |
| 14022 | 3 | | | | | MS4A6E | 1.00 | 14118 | 3 | | | NAPSA | 1.00 |
| 14023 | 3 | | | | | MS4A8B | 1.00 | 14119 | 3 | | | NAT16 | 1.00 |
| 14024 | 3 | | | | | MSGN1 | 1.00 | 14120 | 3 | | | NAT2 | 1.00 |
| 14025 | 3 | | | | | MSH4 | 1.00 | 14121 | 3 | | | NAT8 | 1.00 |
| 14026 | 3 | | | | | MSH5 | 1.00 | 14122 | 3 | | | NAT8B | 1.00 |
| 14027 | 3 | | | | | MSI1 | 1.00 | 14123 | 3 | | | NAV2-AS4 | 1.00 |
| 14028 | 3 | | | | | MSLN | 1.00 | 14124 | 3 | | | NBEAL1 | 1.00 |
| 14029 | 3 | | | | | MSLNL | 1.00 | 14125 | 3 | | | NBEAP1 | 1.00 |
| 14030 | 3 | | | | | MSTN | 1.00 | 14126 | 3 | | | NBLA00301 | 1.00 |
| 14031 | 3 | | | | | MSX2P1 | 1.00 | 14127 | 3 | | | NBPF22P | 1.00 |
| 14032 | 3 | | | | | MT1B | 1.00 | 14128 | 3 | | | NBPF4 | 1.00 |
| 14033 | 3 | | | | | MT1DP | 1.00 | 14129 | 3 | | | NBPF6 | 1.00 |
| 14034 | 3 | | | | | MT1IP | 1.00 | 14130 | 3 | | | NBPF7 | 1.00 |
| 14035 | 3 | | | | | MT1JP | 1.00 | 14131 | 3 | | | NCAM2 | 1.00 |
| 14036 | 3 | | | | | MT3 | 1.00 | 14132 | 3 | | | NCAN | 1.00 |
| 14037 | 3 | | | | | MTBP | 1.00 | 14133 | 3 | | | NCAPG | 1.00 |
| 14038 | 3 | | | | | MTL5 | 1.00 | 14134 | 3 | | | NCAPH | 1.00 |
| 14039 | 3 | | | | | MTMR8 | 1.00 | 14135 | 3 | | | NCOR1P1 | 1.00 |
| 14040 | 3 | | | | | MTNR1A | 1.00 | 14136 | 3 | | | NCR1 | 1.00 |
| 14041 | 3 | | | | | MTNR1B | 1.00 | 14137 | 3 | | | NCR2 | 1.00 |
| 14042 | 3 | | | | | MTRNR2L1 | 1.00 | 14138 | 3 | | | NCRNA00185 | 1.00 |
| 14043 | 3 | | | | | MTRNR2L3 | 1.00 | 14139 | 3 | | | NCRUPAR | 1.00 |
| 14044 | 3 | | | | | MTRNR2L4 | 1.00 | 14140 | 3 | | | NDC80 | 1.00 |
| 14045 | 3 | | | | | MTRNR2L5 | 1.00 | 14141 | 3 | | | NDP | 1.00 |
| 14046 | 3 | | | | | MTRNR2L7 | 1.00 | 14142 | 3 | | | NDST3 | 1.00 |
| 14047 | 3 | | | | | MTRNR2L8 | 1.00 | 14143 | 3 | | | NDST4 | 1.00 |
| 14048 | 3 | | | | | MTTP | 1.00 | 14144 | 3 | | | NEB | 1.00 |
| 14049 | 3 | | | | | MTUS2 | 1.00 | 14145 | 3 | | | NECAB2 | 1.00 |
| 14050 | 3 | | | | | MTVR2 | 1.00 | 14146 | 3 | | | NEDD8-MDP1 | 1.00 |
| 14051 | 3 | | | | | MUC12 | 1.00 | 14147 | 3 | | | NEFH | 1.00 |
| 14052 | 3 | | | | | MUC13 | 1.00 | 14148 | 3 | | | NEFM | 1.00 |
| 14053 | 3 | | | | | MUC16 | 1.00 | 14149 | 3 | | | NEGR1-IT1 | 1.00 |
| 14054 | 3 | | | | | MUC17 | 1.00 | 14150 | 3 | | | NEIL3 | 1.00 |
| 14055 | 3 | | | | | MUC2 | 1.00 | 14151 | 3 | | | NEK10 | 1.00 |
| 14056 | 3 | | | | | MUC21 | 1.00 | 14152 | 3 | | | NEK5 | 1.00 |
| 14057 | 3 | | | | | MUC22 | 1.00 | 14153 | 3 | | | NELL1 | 1.00 |
| 14058 | 3 | | | | | MUC4 | 1.00 | 14154 | 3 | | | NETO1 | 1.00 |
| 14059 | 3 | | | | | MUC5B | 1.00 | 14155 | 3 | | | NEU4 | 1.00 |
| 14060 | 3 | | | | | MUM1L1 | 1.00 | 14156 | 3 | | | NEURL | 1.00 |
| 14061 | 3 | | | | | MURC | 1.00 | 14157 | 3 | | | NEURL3 | 1.00 |
| 14062 | 3 | | | | | MUSK | 1.00 | 14158 | 3 | | | NEUROD1 | 1.00 |
| 14063 | 3 | | | | | MYADM | 1.00 | 14159 | 3 | | | NEUROD2 | 1.00 |
| 14064 | 3 | | | | | MYADML2 | 1.00 | 14160 | 3 | | | NEUROD4 | 1.00 |
| 14065 | 3 | | | | | MYBL1 | 1.00 | 14161 | 3 | | | NEUROD6 | 1.00 |
| 14066 | 3 | | | | | MYBPC2 | 1.00 | 14162 | 3 | | | NEUROG1 | 1.00 |
| 14067 | 3 | | | | | MYBPC3 | 1.00 | 14163 | 3 | | | NEUROG2 | 1.00 |
| 14068 | 3 | | | | | MYBPH | 1.00 | 14164 | 3 | | | NEUROG3 | 1.00 |
| 14069 | 3 | | | | | MYBPHL | 1.00 | 14165 | 3 | | | NF1P2 | 1.00 |
| 14070 | 3 | | | | | MYCBPAP | 1.00 | 14166 | 3 | | | NGB | 1.00 |
| 14071 | 3 | | | | | MYCNOS | 1.00 | 14167 | 3 | | | NHLH1 | 1.00 |
| 14072 | 3 | | | | | MYF5 | 1.00 | 14168 | 3 | | | NIPSNAP3B | 1.00 |
| 14073 | 3 | | | | | MYF6 | 1.00 | 14169 | 3 | | | NKAIN2 | 1.00 |
| 14074 | 3 | | | | | MYH1 | 1.00 | 14170 | 3 | | | NKAIN3 | 1.00 |
| 14075 | 3 | | | | | MYH13 | 1.00 | 14171 | 3 | | | NKAIN4 | 1.00 |
| 14076 | 3 | | | | | MYH15 | 1.00 | 14172 | 3 | | | NKX1-2 | 1.00 |
| 14077 | 3 | | | | | MYH16 | 1.00 | 14173 | 3 | | | NKX2-1 | 1.00 |
| 14078 | 3 | | | | | MYH2 | 1.00 | 14174 | 3 | | | NKX2-2 | 1.00 |
| 14079 | 3 | | | | | MYH3 | 1.00 | 14175 | 3 | | | NKX2-3 | 1.00 |
| 14080 | 3 | | | | | MYH4 | 1.00 | 14176 | 3 | | | NKX2-4 | 1.00 |
| 14081 | 3 | | | | | MYH6 | 1.00 | 14177 | 3 | | | NKX2-5 | 1.00 |
| 14082 | 3 | | | | | MYH7 | 1.00 | 14178 | 3 | | | NKX2-6 | 1.00 |
| 14083 | 3 | | | | | MYH7B | 1.00 | 14179 | 3 | | | NKX2-8 | 1.00 |
| 14084 | 3 | | | | | MYH8 | 1.00 | 14180 | 3 | | | NKX3-2 | 1.00 |
| 14085 | 3 | | | | | MYL1 | 1.00 | 14181 | 3 | | | NKX6-1 | 1.00 |
| 14086 | 3 | | | | | MYL10 | 1.00 | 14182 | 3 | | | NKX6-2 | 1.00 |
| 14087 | 3 | | | | | MYL2 | 1.00 | 14183 | 3 | | | NKX6-3 | 1.00 |
| 14088 | 3 | | | | | MYL4 | 1.00 | 14184 | 3 | | | NLGN1 | 1.00 |
| 14089 | 3 | | | | | MYL7 | 1.00 | 14185 | 3 | | | NLGN4Y | 1.00 |
| 14090 | 3 | | | | | MYLK2 | 1.00 | 14186 | 3 | | | NLRC4 | 1.00 |
| 14091 | 3 | | | | | MYLK3 | 1.00 | 14187 | 3 | | | NLRP11 | 1.00 |
| 14092 | 3 | | | | | MYLK4 | 1.00 | 14188 | 3 | | | NLRP12 | 1.00 |
| 14093 | 3 | | | | | MYLPF | 1.00 | 14189 | 3 | | | NLRP13 | 1.00 |
| 14094 | 3 | | | | | MYO15A | 1.00 | 14190 | 3 | | | NLRP14 | 1.00 |
| 14095 | 3 | | | | | MYO16 | 1.00 | 14191 | 3 | | | NLRP4 | 1.00 |
| 14096 | 3 | | | | | MYO18B | 1.00 | 14192 | 3 | | | NLRP5 | 1.00 |
| 14097 | 3 | | | | | MYO1A | 1.00 | 14193 | 3 | | | NLRP6 | 1.00 |
| 14098 | 3 | | | | | MYO1H | 1.00 | 14194 | 3 | | | NLRP7 | 1.00 |
| 14099 | 3 | | | | | MYO3B | 1.00 | 14195 | 3 | | | NLRP8 | 1.00 |
| 14100 | 3 | | | | | MYO7B | 1.00 | 14196 | 3 | | | NLRP9 | 1.00 |
| 14101 | 3 | | | | | MYOD1 | 1.00 | 14197 | 3 | | | NMBR | 1.00 |
| 14102 | 3 | | | | | MYOG | 1.00 | 14198 | 3 | | | NME1-NME2 | 1.00 |
| 14103 | 3 | | | | | MYOT | 1.00 | 14199 | 3 | | | NME5 | 1.00 |
| 14104 | 3 | | | | | MYOZ1 | 1.00 | 14200 | 3 | | | NME9 | 1.00 |
| 14105 | 3 | | | | | MYOZ2 | 1.00 | 14201 | 3 | | | NMS | 1.00 |
| 14106 | 3 | | | | | MYOZ3 | 1.00 | 14202 | 3 | | | NMUR2 | 1.00 |
| 14107 | 3 | | | | | MYPN | 1.00 | 14203 | 3 | | | NOBOX | 1.00 |

Fig. 38 - 75

| | | | | | | | |
|---|---|---|---|---|---|---|---|
| 14204 | 3 | | NOG | 1.00 | 14300 | 3 | OPALIN | 1.00 |
| 14205 | 3 | | NOL4 | 1.00 | 14301 | 3 | OPCML | 1.00 |
| 14206 | 3 | | NOS1AP | 1.00 | 14302 | 3 | OPN1LW | 1.00 |
| 14207 | 3 | | NOS2 | 1.00 | 14303 | 3 | OPN1MW | 1.00 |
| 14208 | 3 | | NOTO | 1.00 | 14304 | 3 | OPN1MW2 | 1.00 |
| 14209 | 3 | | NOX1 | 1.00 | 14305 | 3 | OPN1SW | 1.00 |
| 14210 | 3 | | NOX3 | 1.00 | 14306 | 3 | OPN4 | 1.00 |
| 14211 | 3 | | NOX4 | 1.00 | 14307 | 3 | OPN5 | 1.00 |
| 14212 | 3 | | NOX5 | 1.00 | 14308 | 3 | OPRD1 | 1.00 |
| 14213 | 3 | | NOXO1 | 1.00 | 14309 | 3 | OPRK1 | 1.00 |
| 14214 | 3 | | NOXRED1 | 1.00 | 14310 | 3 | OPRM1 | 1.00 |
| 14215 | 3 | | NPAS3 | 1.00 | 14311 | 3 | OPTC | 1.00 |
| 14216 | 3 | | NPAS4 | 1.00 | 14312 | 3 | OR10A2 | 1.00 |
| 14217 | 3 | | NPBWR2 | 1.00 | 14313 | 3 | OR10A3 | 1.00 |
| 14218 | 3 | | NPC1L1 | 1.00 | 14314 | 3 | OR10A4 | 1.00 |
| 14219 | 3 | | NPFFR1 | 1.00 | 14315 | 3 | OR10A5 | 1.00 |
| 14220 | 3 | | NPHP3-AS1 | 1.00 | 14316 | 3 | OR10A6 | 1.00 |
| 14221 | 3 | | NPHS1 | 1.00 | 14317 | 3 | OR10A7 | 1.00 |
| 14222 | 3 | | NPHS2 | 1.00 | 14318 | 3 | OR10AD1 | 1.00 |
| 14223 | 3 | | NPM2 | 1.00 | 14319 | 3 | OR10AG1 | 1.00 |
| 14224 | 3 | | NPPA | 1.00 | 14320 | 3 | OR10C1 | 1.00 |
| 14225 | 3 | | NPPB | 1.00 | 14321 | 3 | OR10G2 | 1.00 |
| 14226 | 3 | | NPPC | 1.00 | 14322 | 3 | OR10G3 | 1.00 |
| 14227 | 3 | | NPS | 1.00 | 14323 | 3 | OR10G4 | 1.00 |
| 14228 | 3 | | NPSR1 | 1.00 | 14324 | 3 | OR10G7 | 1.00 |
| 14229 | 3 | | NPVF | 1.00 | 14325 | 3 | OR10G8 | 1.00 |
| 14230 | 3 | | NPY | 1.00 | 14326 | 3 | OR10G9 | 1.00 |
| 14231 | 3 | | NPY2R | 1.00 | 14327 | 3 | OR10H1 | 1.00 |
| 14232 | 3 | | NPY6R | 1.00 | 14328 | 3 | OR10H2 | 1.00 |
| 14233 | 3 | | NR0B1 | 1.00 | 14329 | 3 | OR10H3 | 1.00 |
| 14234 | 3 | | NR0B2 | 1.00 | 14330 | 3 | OR10H4 | 1.00 |
| 14235 | 3 | | NR1H4 | 1.00 | 14331 | 3 | OR10H5 | 1.00 |
| 14236 | 3 | | NR1I2 | 1.00 | 14332 | 3 | OR10J1 | 1.00 |
| 14237 | 3 | | NR1I3 | 1.00 | 14333 | 3 | OR10J3 | 1.00 |
| 14238 | 3 | | NR2E1 | 1.00 | 14334 | 3 | OR10J5 | 1.00 |
| 14239 | 3 | | NR2E3 | 1.00 | 14335 | 3 | OR10K1 | 1.00 |
| 14240 | 3 | | NR5A1 | 1.00 | 14336 | 3 | OR10K2 | 1.00 |
| 14241 | 3 | | NR6A1 | 1.00 | 14337 | 3 | OR10P1 | 1.00 |
| 14242 | 3 | | NRAP | 1.00 | 14338 | 3 | OR10Q1 | 1.00 |
| 14243 | 3 | | NRCAM | 1.00 | 14339 | 3 | OR10R2 | 1.00 |
| 14244 | 3 | | NRG3 | 1.00 | 14340 | 3 | OR10S1 | 1.00 |
| 14245 | 3 | | NRIP3 | 1.00 | 14341 | 3 | OR10T2 | 1.00 |
| 14246 | 3 | | NRK | 1.00 | 14342 | 3 | OR10V1 | 1.00 |
| 14247 | 3 | | NRL | 1.00 | 14343 | 3 | OR10V2P | 1.00 |
| 14248 | 3 | | NRON | 1.00 | 14344 | 3 | OR10W1 | 1.00 |
| 14249 | 3 | | NRSN1 | 1.00 | 14345 | 3 | OR10X1 | 1.00 |
| 14250 | 3 | | NT5C1A | 1.00 | 14346 | 3 | OR10Z1 | 1.00 |
| 14251 | 3 | | NT5C1B | 1.00 | 14347 | 3 | OR11A1 | 1.00 |
| 14252 | 3 | | NT5C1B-RDH14 | 1.00 | 14348 | 3 | OR11G2 | 1.00 |
| 14253 | 3 | | NTN3 | 1.00 | 14349 | 3 | OR11H1 | 1.00 |
| 14254 | 3 | | NTRK1 | 1.00 | 14350 | 3 | OR11H12 | 1.00 |
| 14255 | 3 | | NTS | 1.00 | 14351 | 3 | OR11H2 | 1.00 |
| 14256 | 3 | | NTSR1 | 1.00 | 14352 | 3 | OR11H4 | 1.00 |
| 14257 | 3 | | NTSR2 | 1.00 | 14353 | 3 | OR11H6 | 1.00 |
| 14258 | 3 | | NUDT9P1 | 1.00 | 14354 | 3 | OR11L1 | 1.00 |
| 14259 | 3 | | NUP155 | 1.00 | 14355 | 3 | OR12D2 | 1.00 |
| 14260 | 3 | | NUP210L | 1.00 | 14356 | 3 | OR12D3 | 1.00 |
| 14261 | 3 | | NUP210P1 | 1.00 | 14357 | 3 | OR13A1 | 1.00 |
| 14262 | 3 | | NUP62CL | 1.00 | 14358 | 3 | OR13C2 | 1.00 |
| 14263 | 3 | | NWD1 | 1.00 | 14359 | 3 | OR13C3 | 1.00 |
| 14264 | 3 | | NXF2 | 1.00 | 14360 | 3 | OR13C4 | 1.00 |
| 14265 | 3 | | NXF2B | 1.00 | 14361 | 3 | OR13C5 | 1.00 |
| 14266 | 3 | | NXF3 | 1.00 | 14362 | 3 | OR13C8 | 1.00 |
| 14267 | 3 | | NXF4 | 1.00 | 14363 | 3 | OR13C9 | 1.00 |
| 14268 | 3 | | NXF5 | 1.00 | 14364 | 3 | OR13D1 | 1.00 |
| 14269 | 3 | | NXNL1 | 1.00 | 14365 | 3 | OR13F1 | 1.00 |
| 14270 | 3 | | NXNL2 | 1.00 | 14366 | 3 | OR13G1 | 1.00 |
| 14271 | 3 | | NXPH1 | 1.00 | 14367 | 3 | OR13H1 | 1.00 |
| 14272 | 3 | | NXPH2 | 1.00 | 14368 | 3 | OR13J1 | 1.00 |
| 14273 | 3 | | NYAP2 | 1.00 | 14369 | 3 | OR14A16 | 1.00 |
| 14274 | 3 | | NYX | 1.00 | 14370 | 3 | OR14C36 | 1.00 |
| 14275 | 3 | | OC90 | 1.00 | 14371 | 3 | OR14I1 | 1.00 |
| 14276 | 3 | | OCLM | 1.00 | 14372 | 3 | OR14J1 | 1.00 |
| 14277 | 3 | | OCM | 1.00 | 14373 | 3 | OR1A1 | 1.00 |
| 14278 | 3 | | OCM2 | 1.00 | 14374 | 3 | OR1A2 | 1.00 |
| 14279 | 3 | | ODAM | 1.00 | 14375 | 3 | OR1B1 | 1.00 |
| 14280 | 3 | | ODF1 | 1.00 | 14376 | 3 | OR1C1 | 1.00 |
| 14281 | 3 | | ODF3 | 1.00 | 14377 | 3 | OR1D2 | 1.00 |
| 14282 | 3 | | ODF3L2 | 1.00 | 14378 | 3 | OR1D4 | 1.00 |
| 14283 | 3 | | ODF4 | 1.00 | 14379 | 3 | OR1D5 | 1.00 |
| 14284 | 3 | | ODZ1 | 1.00 | 14380 | 3 | OR1E1 | 1.00 |
| 14285 | 3 | | OGDHL | 1.00 | 14381 | 3 | OR1E2 | 1.00 |
| 14286 | 3 | | OIP5 | 1.00 | 14382 | 3 | OR1F1 | 1.00 |
| 14287 | 3 | | OIT3 | 1.00 | 14383 | 3 | OR1F2P | 1.00 |
| 14288 | 3 | | OLFM3 | 1.00 | 14384 | 3 | OR1G1 | 1.00 |
| 14289 | 3 | | OLFM4 | 1.00 | 14385 | 3 | OR1I1 | 1.00 |
| 14290 | 3 | | OLIG1 | 1.00 | 14386 | 3 | OR1J1 | 1.00 |
| 14291 | 3 | | OLIG2 | 1.00 | 14387 | 3 | OR1J2 | 1.00 |
| 14292 | 3 | | OLIG3 | 1.00 | 14388 | 3 | OR1J4 | 1.00 |
| 14293 | 3 | | OLR1 | 1.00 | 14389 | 3 | OR1K1 | 1.00 |
| 14294 | 3 | | OMG | 1.00 | 14390 | 3 | OR1L1 | 1.00 |
| 14295 | 3 | | OMP | 1.00 | 14391 | 3 | OR1L3 | 1.00 |
| 14296 | 3 | | ONECUT1 | 1.00 | 14392 | 3 | OR1L4 | 1.00 |
| 14297 | 3 | | ONECUT2 | 1.00 | 14393 | 3 | OR1L6 | 1.00 |
| 14298 | 3 | | ONECUT3 | 1.00 | 14394 | 3 | OR1L8 | 1.00 |
| 14299 | 3 | | OOEP | 1.00 | 14395 | 3 | OR1M1 | 1.00 |

Fig. 38 - 76

| | | | | | | | | | | | | |
|---|---|---|---|---|---|---|---|---|---|---|---|---|
| 14396 | 3 | | | | | OR1N1 | 1.00 | 14492 | 3 | | OR4F17 | 1.00 |
| 14397 | 3 | | | | | OR1N2 | 1.00 | 14493 | 3 | | OR4F21 | 1.00 |
| 14398 | 3 | | | | | OR1Q1 | 1.00 | 14494 | 3 | | OR4F29 | 1.00 |
| 14399 | 3 | | | | | OR1S1 | 1.00 | 14495 | 3 | | OR4F4 | 1.00 |
| 14400 | 3 | | | | | OR1S2 | 1.00 | 14496 | 3 | | OR4F5 | 1.00 |
| 14401 | 3 | | | | | OR2A1 | 1.00 | 14497 | 3 | | OR4F6 | 1.00 |
| 14402 | 3 | | | | | OR2A12 | 1.00 | 14498 | 3 | | OR4K1 | 1.00 |
| 14403 | 3 | | | | | OR2A14 | 1.00 | 14499 | 3 | | OR4K13 | 1.00 |
| 14404 | 3 | | | | | OR2A2 | 1.00 | 14500 | 3 | | OR4K14 | 1.00 |
| 14405 | 3 | | | | | OR2A25 | 1.00 | 14501 | 3 | | OR4K15 | 1.00 |
| 14406 | 3 | | | | | OR2A42 | 1.00 | 14502 | 3 | | OR4K17 | 1.00 |
| 14407 | 3 | | | | | OR2A5 | 1.00 | 14503 | 3 | | OR4K2 | 1.00 |
| 14408 | 3 | | | | | OR2AE1 | 1.00 | 14504 | 3 | | OR4K5 | 1.00 |
| 14409 | 3 | | | | | OR2AG1 | 1.00 | 14505 | 3 | | OR4L1 | 1.00 |
| 14410 | 3 | | | | | OR2AG2 | 1.00 | 14506 | 3 | | OR4M1 | 1.00 |
| 14411 | 3 | | | | | OR2AK2 | 1.00 | 14507 | 3 | | OR4M2 | 1.00 |
| 14412 | 3 | | | | | OR2AT4 | 1.00 | 14508 | 3 | | OR4N2 | 1.00 |
| 14413 | 3 | | | | | OR2B11 | 1.00 | 14509 | 3 | | OR4N3P | 1.00 |
| 14414 | 3 | | | | | OR2B2 | 1.00 | 14510 | 3 | | OR4N4 | 1.00 |
| 14415 | 3 | | | | | OR2B3 | 1.00 | 14511 | 3 | | OR4N5 | 1.00 |
| 14416 | 3 | | | | | OR2B6 | 1.00 | 14512 | 3 | | OR4P4 | 1.00 |
| 14417 | 3 | | | | | OR2C1 | 1.00 | 14513 | 3 | | OR4Q3 | 1.00 |
| 14418 | 3 | | | | | OR2C3 | 1.00 | 14514 | 3 | | OR4S1 | 1.00 |
| 14419 | 3 | | | | | OR2D2 | 1.00 | 14515 | 3 | | OR4S2 | 1.00 |
| 14420 | 3 | | | | | OR2D3 | 1.00 | 14516 | 3 | | OR4X1 | 1.00 |
| 14421 | 3 | | | | | OR2F1 | 1.00 | 14517 | 3 | | OR4X2 | 1.00 |
| 14422 | 3 | | | | | OR2F2 | 1.00 | 14518 | 3 | | OR51A2 | 1.00 |
| 14423 | 3 | | | | | OR2G2 | 1.00 | 14519 | 3 | | OR51A4 | 1.00 |
| 14424 | 3 | | | | | OR2G3 | 1.00 | 14520 | 3 | | OR51A7 | 1.00 |
| 14425 | 3 | | | | | OR2G6 | 1.00 | 14521 | 3 | | OR51B2 | 1.00 |
| 14426 | 3 | | | | | OR2H1 | 1.00 | 14522 | 3 | | OR51B4 | 1.00 |
| 14427 | 3 | | | | | OR2H2 | 1.00 | 14523 | 3 | | OR51B5 | 1.00 |
| 14428 | 3 | | | | | OR2J2 | 1.00 | 14524 | 3 | | OR51B6 | 1.00 |
| 14429 | 3 | | | | | OR2J3 | 1.00 | 14525 | 3 | | OR51D1 | 1.00 |
| 14430 | 3 | | | | | OR2K2 | 1.00 | 14526 | 3 | | OR51E1 | 1.00 |
| 14431 | 3 | | | | | OR2L13 | 1.00 | 14527 | 3 | | OR51E2 | 1.00 |
| 14432 | 3 | | | | | OR2L1P | 1.00 | 14528 | 3 | | OR51F1 | 1.00 |
| 14433 | 3 | | | | | OR2L2 | 1.00 | 14529 | 3 | | OR51F2 | 1.00 |
| 14434 | 3 | | | | | OR2L3 | 1.00 | 14530 | 3 | | OR51G1 | 1.00 |
| 14435 | 3 | | | | | OR2L8 | 1.00 | 14531 | 3 | | OR51G2 | 1.00 |
| 14436 | 3 | | | | | OR2M1P | 1.00 | 14532 | 3 | | OR51I1 | 1.00 |
| 14437 | 3 | | | | | OR2M2 | 1.00 | 14533 | 3 | | OR51I2 | 1.00 |
| 14438 | 3 | | | | | OR2M3 | 1.00 | 14534 | 3 | | OR51L1 | 1.00 |
| 14439 | 3 | | | | | OR2M4 | 1.00 | 14535 | 3 | | OR51M1 | 1.00 |
| 14440 | 3 | | | | | OR2M5 | 1.00 | 14536 | 3 | | OR51Q1 | 1.00 |
| 14441 | 3 | | | | | OR2M7 | 1.00 | 14537 | 3 | | OR51S1 | 1.00 |
| 14442 | 3 | | | | | OR2S2 | 1.00 | 14538 | 3 | | OR51T1 | 1.00 |
| 14443 | 3 | | | | | OR2T1 | 1.00 | 14539 | 3 | | OR51V1 | 1.00 |
| 14444 | 3 | | | | | OR2T10 | 1.00 | 14540 | 3 | | OR52A1 | 1.00 |
| 14445 | 3 | | | | | OR2T11 | 1.00 | 14541 | 3 | | OR52A5 | 1.00 |
| 14446 | 3 | | | | | OR2T12 | 1.00 | 14542 | 3 | | OR52B2 | 1.00 |
| 14447 | 3 | | | | | OR2T2 | 1.00 | 14543 | 3 | | OR52B4 | 1.00 |
| 14448 | 3 | | | | | OR2T27 | 1.00 | 14544 | 3 | | OR52B6 | 1.00 |
| 14449 | 3 | | | | | OR2T29 | 1.00 | 14545 | 3 | | OR52D1 | 1.00 |
| 14450 | 3 | | | | | OR2T3 | 1.00 | 14546 | 3 | | OR52E2 | 1.00 |
| 14451 | 3 | | | | | OR2T33 | 1.00 | 14547 | 3 | | OR52E4 | 1.00 |
| 14452 | 3 | | | | | OR2T34 | 1.00 | 14548 | 3 | | OR52E6 | 1.00 |
| 14453 | 3 | | | | | OR2T35 | 1.00 | 14549 | 3 | | OR52E8 | 1.00 |
| 14454 | 3 | | | | | OR2T4 | 1.00 | 14550 | 3 | | OR52H1 | 1.00 |
| 14455 | 3 | | | | | OR2T5 | 1.00 | 14551 | 3 | | OR52I1 | 1.00 |
| 14456 | 3 | | | | | OR2T6 | 1.00 | 14552 | 3 | | OR52I2 | 1.00 |
| 14457 | 3 | | | | | OR2T8 | 1.00 | 14553 | 3 | | OR52J3 | 1.00 |
| 14458 | 3 | | | | | OR2V2 | 1.00 | 14554 | 3 | | OR52K1 | 1.00 |
| 14459 | 3 | | | | | OR2W1 | 1.00 | 14555 | 3 | | OR52K2 | 1.00 |
| 14460 | 3 | | | | | OR2W3 | 1.00 | 14556 | 3 | | OR52L1 | 1.00 |
| 14461 | 3 | | | | | OR2W5 | 1.00 | 14557 | 3 | | OR52M1 | 1.00 |
| 14462 | 3 | | | | | OR2Y1 | 1.00 | 14558 | 3 | | OR52N1 | 1.00 |
| 14463 | 3 | | | | | OR2Z1 | 1.00 | 14559 | 3 | | OR52N2 | 1.00 |
| 14464 | 3 | | | | | OR3A1 | 1.00 | 14560 | 3 | | OR52N5 | 1.00 |
| 14465 | 3 | | | | | OR3A2 | 1.00 | 14561 | 3 | | OR52R1 | 1.00 |
| 14466 | 3 | | | | | OR3A3 | 1.00 | 14562 | 3 | | OR52W1 | 1.00 |
| 14467 | 3 | | | | | OR3A4P | 1.00 | 14563 | 3 | | OR56A1 | 1.00 |
| 14468 | 3 | | | | | OR4A15 | 1.00 | 14564 | 3 | | OR56A3 | 1.00 |
| 14469 | 3 | | | | | OR4A16 | 1.00 | 14565 | 3 | | OR56A4 | 1.00 |
| 14470 | 3 | | | | | OR4A47 | 1.00 | 14566 | 3 | | OR56A5 | 1.00 |
| 14471 | 3 | | | | | OR4A5 | 1.00 | 14567 | 3 | | OR56B1 | 1.00 |
| 14472 | 3 | | | | | OR4B1 | 1.00 | 14568 | 3 | | OR56B4 | 1.00 |
| 14473 | 3 | | | | | OR4C11 | 1.00 | 14569 | 3 | | OR5A1 | 1.00 |
| 14474 | 3 | | | | | OR4C12 | 1.00 | 14570 | 3 | | OR5A2 | 1.00 |
| 14475 | 3 | | | | | OR4C13 | 1.00 | 14571 | 3 | | OR5AC2 | 1.00 |
| 14476 | 3 | | | | | OR4C15 | 1.00 | 14572 | 3 | | OR5AK2 | 1.00 |
| 14477 | 3 | | | | | OR4C16 | 1.00 | 14573 | 3 | | OR5AK4P | 1.00 |
| 14478 | 3 | | | | | OR4C3 | 1.00 | 14574 | 3 | | OR5AN1 | 1.00 |
| 14479 | 3 | | | | | OR4C45 | 1.00 | 14575 | 3 | | OR5AP2 | 1.00 |
| 14480 | 3 | | | | | OR4C46 | 1.00 | 14576 | 3 | | OR5AR1 | 1.00 |
| 14481 | 3 | | | | | OR4C6 | 1.00 | 14577 | 3 | | OR5AS1 | 1.00 |
| 14482 | 3 | | | | | OR4D1 | 1.00 | 14578 | 3 | | OR5AU1 | 1.00 |
| 14483 | 3 | | | | | OR4D10 | 1.00 | 14579 | 3 | | OR5B12 | 1.00 |
| 14484 | 3 | | | | | OR4D11 | 1.00 | 14580 | 3 | | OR5B17 | 1.00 |
| 14485 | 3 | | | | | OR4D2 | 1.00 | 14581 | 3 | | OR5B2 | 1.00 |
| 14486 | 3 | | | | | OR4D5 | 1.00 | 14582 | 3 | | OR5B21 | 1.00 |
| 14487 | 3 | | | | | OR4D6 | 1.00 | 14583 | 3 | | OR5B3 | 1.00 |
| 14488 | 3 | | | | | OR4D9 | 1.00 | 14584 | 3 | | OR5C1 | 1.00 |
| 14489 | 3 | | | | | OR4E2 | 1.00 | 14585 | 3 | | OR5D13 | 1.00 |
| 14490 | 3 | | | | | OR4F15 | 1.00 | 14586 | 3 | | OR5D14 | 1.00 |
| 14491 | 3 | | | | | OR4F16 | 1.00 | 14587 | 3 | | OR5D16 | 1.00 |

Fig. 38 - 77

| | | | | | | | | |
|---|---|---|---|---|---|---|---|---|
| 14588 | 3 | | | | OR5D18 | 1.00 | | |
| 14589 | 3 | | | | OR5E1P | 1.00 | | |
| 14590 | 3 | | | | OR5F1 | 1.00 | | |
| 14591 | 3 | | | | OR5H1 | 1.00 | | |
| 14592 | 3 | | | | OR5H14 | 1.00 | | |
| 14593 | 3 | | | | OR5H15 | 1.00 | | |
| 14594 | 3 | | | | OR5H2 | 1.00 | | |
| 14595 | 3 | | | | OR5H6 | 1.00 | | |
| 14596 | 3 | | | | OR5I1 | 1.00 | | |
| 14597 | 3 | | | | OR5J2 | 1.00 | | |
| 14598 | 3 | | | | OR5K1 | 1.00 | | |
| 14599 | 3 | | | | OR5K2 | 1.00 | | |
| 14600 | 3 | | | | OR5K3 | 1.00 | | |
| 14601 | 3 | | | | OR5K4 | 1.00 | | |
| 14602 | 3 | | | | OR5L1 | 1.00 | | |
| 14603 | 3 | | | | OR5L2 | 1.00 | | |
| 14604 | 3 | | | | OR5M1 | 1.00 | | |
| 14605 | 3 | | | | OR5M10 | 1.00 | | |
| 14606 | 3 | | | | OR5M11 | 1.00 | | |
| 14607 | 3 | | | | OR5M3 | 1.00 | | |
| 14608 | 3 | | | | OR5M8 | 1.00 | | |
| 14609 | 3 | | | | OR5M9 | 1.00 | | |
| 14610 | 3 | | | | OR5P2 | 1.00 | | |
| 14611 | 3 | | | | OR5P3 | 1.00 | | |
| 14612 | 3 | | | | OR5R1 | 1.00 | | |
| 14613 | 3 | | | | OR5T1 | 1.00 | | |
| 14614 | 3 | | | | OR5T2 | 1.00 | | |
| 14615 | 3 | | | | OR5T3 | 1.00 | | |
| 14616 | 3 | | | | OR5V1 | 1.00 | | |
| 14617 | 3 | | | | OR5W2 | 1.00 | | |
| 14618 | 3 | | | | OR6A2 | 1.00 | | |
| 14619 | 3 | | | | OR6B1 | 1.00 | | |
| 14620 | 3 | | | | OR6B2 | 1.00 | | |
| 14621 | 3 | | | | OR6B3 | 1.00 | | |
| 14622 | 3 | | | | OR6C1 | 1.00 | | |
| 14623 | 3 | | | | OR6C2 | 1.00 | | |
| 14624 | 3 | | | | OR6C3 | 1.00 | | |
| 14625 | 3 | | | | OR6C4 | 1.00 | | |
| 14626 | 3 | | | | OR6C6 | 1.00 | | |
| 14627 | 3 | | | | OR6C65 | 1.00 | | |
| 14628 | 3 | | | | OR6C68 | 1.00 | | |
| 14629 | 3 | | | | OR6C70 | 1.00 | | |
| 14630 | 3 | | | | OR6C74 | 1.00 | | |
| 14631 | 3 | | | | OR6C75 | 1.00 | | |
| 14632 | 3 | | | | OR6C76 | 1.00 | | |
| 14633 | 3 | | | | OR6F1 | 1.00 | | |
| 14634 | 3 | | | | OR6K2 | 1.00 | | |
| 14635 | 3 | | | | OR6K3 | 1.00 | | |
| 14636 | 3 | | | | OR6K6 | 1.00 | | |
| 14637 | 3 | | | | OR6M1 | 1.00 | | |
| 14638 | 3 | | | | OR6N1 | 1.00 | | |
| 14639 | 3 | | | | OR6N2 | 1.00 | | |
| 14640 | 3 | | | | OR6P1 | 1.00 | | |
| 14641 | 3 | | | | OR6Q1 | 1.00 | | |
| 14642 | 3 | | | | OR6S1 | 1.00 | | |
| 14643 | 3 | | | | OR6T1 | 1.00 | | |
| 14644 | 3 | | | | OR6V1 | 1.00 | | |
| 14645 | 3 | | | | OR6W1P | 1.00 | | |
| 14646 | 3 | | | | OR6X1 | 1.00 | | |
| 14647 | 3 | | | | OR6Y1 | 1.00 | | |
| 14648 | 3 | | | | OR7A10 | 1.00 | | |
| 14649 | 3 | | | | OR7A17 | 1.00 | | |
| 14650 | 3 | | | | OR7A5 | 1.00 | | |
| 14651 | 3 | | | | OR7C1 | 1.00 | | |
| 14652 | 3 | | | | OR7C2 | 1.00 | | |
| 14653 | 3 | | | | OR7D2 | 1.00 | | |
| 14654 | 3 | | | | OR7D4 | 1.00 | | |
| 14655 | 3 | | | | OR7E156P | 1.00 | | |
| 14656 | 3 | | | | OR7E24 | 1.00 | | |
| 14657 | 3 | | | | OR7E2P | 1.00 | | |
| 14658 | 3 | | | | OR7E37P | 1.00 | | |
| 14659 | 3 | | | | OR7E5P | 1.00 | | |
| 14660 | 3 | | | | OR7G1 | 1.00 | | |
| 14661 | 3 | | | | OR7G2 | 1.00 | | |
| 14662 | 3 | | | | OR7G3 | 1.00 | | |
| 14663 | 3 | | | | OR8A1 | 1.00 | | |
| 14664 | 3 | | | | OR8B12 | 1.00 | | |
| 14665 | 3 | | | | OR8B2 | 1.00 | | |
| 14666 | 3 | | | | OR8B3 | 1.00 | | |
| 14667 | 3 | | | | OR8B4 | 1.00 | | |
| 14668 | 3 | | | | OR8B8 | 1.00 | | |
| 14669 | 3 | | | | OR8D1 | 1.00 | | |
| 14670 | 3 | | | | OR8D2 | 1.00 | | |
| 14671 | 3 | | | | OR8D4 | 1.00 | | |
| 14672 | 3 | | | | OR8G1 | 1.00 | | |
| 14673 | 3 | | | | OR8G2 | 1.00 | | |
| 14674 | 3 | | | | OR8G5 | 1.00 | | |
| 14675 | 3 | | | | OR8H1 | 1.00 | | |
| 14676 | 3 | | | | OR8H2 | 1.00 | | |
| 14677 | 3 | | | | OR8H3 | 1.00 | | |
| 14678 | 3 | | | | OR8I2 | 1.00 | | |
| 14679 | 3 | | | | OR8J1 | 1.00 | | |
| 14680 | 3 | | | | OR8J3 | 1.00 | | |
| 14681 | 3 | | | | OR8K1 | 1.00 | | |
| 14682 | 3 | | | | OR8K3 | 1.00 | | |
| 14683 | 3 | | | | OR8K5 | 1.00 | | |
| 14684 | 3 | | | | OR8S1 | 1.00 | | |
| 14685 | 3 | | | | OR8U1 | 1.00 | | |
| 14686 | 3 | | | | OR8U8 | 1.00 | | |
| 14687 | 3 | | | | OR9A2 | 1.00 | | |
| 14688 | 3 | | | | OR9A4 | 1.00 | | |
| 14689 | 3 | | | | OR9G4 | 1.00 | | |
| 14690 | 3 | | | | OR9G9 | 1.00 | | |
| 14691 | 3 | | | | OR9I1 | 1.00 | | |
| 14692 | 3 | | | | OR9K2 | 1.00 | | |
| 14693 | 3 | | | | OR9Q1 | 1.00 | | |
| 14694 | 3 | | | | OR9Q2 | 1.00 | | |
| 14695 | 3 | | | | ORC1 | 1.00 | | |
| 14696 | 3 | | | | ORM1 | 1.00 | | |
| 14697 | 3 | | | | ORM2 | 1.00 | | |
| 14698 | 3 | | | | OSTalpha | 1.00 | | |
| 14699 | 3 | | | | OSTBETA | 1.00 | | |
| 14700 | 3 | | | | OSTN | 1.00 | | |
| 14701 | 3 | | | | OTOA | 1.00 | | |
| 14702 | 3 | | | | OTOF | 1.00 | | |
| 14703 | 3 | | | | OTOGL | 1.00 | | |
| 14704 | 3 | | | | OTOL1 | 1.00 | | |
| 14705 | 3 | | | | OTOP2 | 1.00 | | |
| 14706 | 3 | | | | OTOP3 | 1.00 | | |
| 14707 | 3 | | | | OTOR | 1.00 | | |
| 14708 | 3 | | | | OTOS | 1.00 | | |
| 14709 | 3 | | | | OTP | 1.00 | | |
| 14710 | 3 | | | | OTUD6A | 1.00 | | |
| 14711 | 3 | | | | OTX2 | 1.00 | | |
| 14712 | 3 | | | | OTX2OS1 | 1.00 | | |
| 14713 | 3 | | | | OVCH1 | 1.00 | | |
| 14714 | 3 | | | | OVCH2 | 1.00 | | |
| 14715 | 3 | | | | OXCT2 | 1.00 | | |
| 14716 | 3 | | | | OXT | 1.00 | | |
| 14717 | 3 | | | | OXTR | 1.00 | | |
| 14718 | 3 | | | | P2RX3 | 1.00 | | |
| 14719 | 3 | | | | P2RX5 | 1.00 | | |
| 14720 | 3 | | | | P2RX5-TAX1BP3 | 1.00 | | |
| 14721 | 3 | | | | P2RX6 | 1.00 | | |
| 14722 | 3 | | | | P2RX6P | 1.00 | | |
| 14723 | 3 | | | | P4HA3 | 1.00 | | |
| 14724 | 3 | | | | PABPC1L2A | 1.00 | | |
| 14725 | 3 | | | | PABPC1L2B | 1.00 | | |
| 14726 | 3 | | | | PABPC1P2 | 1.00 | | |
| 14727 | 3 | | | | PABPC4L | 1.00 | | |
| 14728 | 3 | | | | PABPN1L | 1.00 | | |
| 14729 | 3 | | | | PACSIN1 | 1.00 | | |
| 14730 | 3 | | | | PADI4 | 1.00 | | |
| 14731 | 3 | | | | PADI6 | 1.00 | | |
| 14732 | 3 | | | | PAEP | 1.00 | | |
| 14733 | 3 | | | | PAGE1 | 1.00 | | |
| 14734 | 3 | | | | PAGE2 | 1.00 | | |
| 14735 | 3 | | | | PAGE2B | 1.00 | | |
| 14736 | 3 | | | | PAGE3 | 1.00 | | |
| 14737 | 3 | | | | PAGE4 | 1.00 | | |
| 14738 | 3 | | | | PAGE5 | 1.00 | | |
| 14739 | 3 | | | | PAH | 1.00 | | |
| 14740 | 3 | | | | PAK3 | 1.00 | | |
| 14741 | 3 | | | | PAK7 | 1.00 | | |
| 14742 | 3 | | | | PALM2 | 1.00 | | |
| 14743 | 3 | | | | PALM2-AKAP2 | 1.00 | | |
| 14744 | 3 | | | | PANX3 | 1.00 | | |
| 14745 | 3 | | | | PAPPA2 | 1.00 | | |
| 14746 | 3 | | | | PAR1 | 1.00 | | |
| 14747 | 3 | | | | PAR4 | 1.00 | | |
| 14748 | 3 | | | | PAR5 | 1.00 | | |
| 14749 | 3 | | | | PASD1 | 1.00 | | |
| 14750 | 3 | | | | PATE1 | 1.00 | | |
| 14751 | 3 | | | | PATE2 | 1.00 | | |
| 14752 | 3 | | | | PATE3 | 1.00 | | |
| 14753 | 3 | | | | PATE4 | 1.00 | | |
| 14754 | 3 | | | | PATL2 | 1.00 | | |
| 14755 | 3 | | | | PAX2 | 1.00 | | |
| 14756 | 3 | | | | PAX4 | 1.00 | | |
| 14757 | 3 | | | | PAX5 | 1.00 | | |
| 14758 | 3 | | | | PAX6 | 1.00 | | |
| 14759 | 3 | | | | PAX7 | 1.00 | | |
| 14760 | 3 | | | | PAX9 | 1.00 | | |
| 14761 | 3 | | | | PBK | 1.00 | | |
| 14762 | 3 | | | | PBOV1 | 1.00 | | |
| 14763 | 3 | | | | PCA3 | 1.00 | | |
| 14764 | 3 | | | | PCDH10 | 1.00 | | |
| 14765 | 3 | | | | PCDH11X | 1.00 | | |
| 14766 | 3 | | | | PCDH11Y | 1.00 | | |
| 14767 | 3 | | | | PCDH15 | 1.00 | | |
| 14768 | 3 | | | | PCDH17 | 1.00 | | |
| 14769 | 3 | | | | PCDH8 | 1.00 | | |
| 14770 | 3 | | | | PCDHA1 | 1.00 | | |
| 14771 | 3 | | | | PCDHA10 | 1.00 | | |
| 14772 | 3 | | | | PCDHA11 | 1.00 | | |
| 14773 | 3 | | | | PCDHA12 | 1.00 | | |
| 14774 | 3 | | | | PCDHA13 | 1.00 | | |
| 14775 | 3 | | | | PCDHA2 | 1.00 | | |
| 14776 | 3 | | | | PCDHA3 | 1.00 | | |
| 14777 | 3 | | | | PCDHA4 | 1.00 | | |
| 14778 | 3 | | | | PCDHA5 | 1.00 | | |
| 14779 | 3 | | | | PCDHA6 | 1.00 | | |

Fig. 38 - 78

| | | | | | | | | | | | | | | | | |
|---|---|---|---|---|---|---|---|---|---|---|---|---|---|---|---|---|
| 14780 | 3 | | | | | PCDHA7 | 1.00 | | 14875 | 3 | | | | | PLAC8 | 1.00 |
| 14781 | 3 | | | | | PCDHA8 | 1.00 | | 14876 | 3 | | | | | PLB1 | 1.00 |
| 14782 | 3 | | | | | PCDHA9 | 1.00 | | 14877 | 3 | | | | | PLCE1 | 1.00 |
| 14783 | 3 | | | | | PCDHAC1 | 1.00 | | 14878 | 3 | | | | | PLCH1 | 1.00 |
| 14784 | 3 | | | | | PCDHAC2 | 1.00 | | 14879 | 3 | | | | | PLCXD2 | 1.00 |
| 14785 | 3 | | | | | PCDHB1 | 1.00 | | 14880 | 3 | | | | | PLCXD3 | 1.00 |
| 14786 | 3 | | | | | PCDHB17 | 1.00 | | 14881 | 3 | | | | | PLCZ1 | 1.00 |
| 14787 | 3 | | | | | PCDHB18 | 1.00 | | 14882 | 3 | | | | | PLD5 | 1.00 |
| 14788 | 3 | | | | | PCDHB19P | 1.00 | | 14883 | 3 | | | | | PLEKHD1 | 1.00 |
| 14789 | 3 | | | | | PCDHB8 | 1.00 | | 14884 | 3 | | | | | PLEKHG4B | 1.00 |
| 14790 | 3 | | | | | PCDHGA1 | 1.00 | | 14885 | 3 | | | | | PLEKHG7 | 1.00 |
| 14791 | 3 | | | | | PCDHGA8 | 1.00 | | 14886 | 3 | | | | | PLGLA | 1.00 |
| 14792 | 3 | | | | | PCDHGB1 | 1.00 | | 14887 | 3 | | | | | PLGLB2 | 1.00 |
| 14793 | 3 | | | | | PCDHGB3 | 1.00 | | 14888 | 3 | | | | | PLK5 | 1.00 |
| 14794 | 3 | | | | | PCDHGB8P | 1.00 | | 14889 | 3 | | | | | PLSCR2 | 1.00 |
| 14795 | 3 | | | | | PCDHGC4 | 1.00 | | 14890 | 3 | | | | | PLSCR5 | 1.00 |
| 14796 | 3 | | | | | PCDHGC5 | 1.00 | | 14891 | 3 | | | | | PMCH | 1.00 |
| 14797 | 3 | | | | | PCDP1 | 1.00 | | 14892 | 3 | | | | | PMCHL1 | 1.00 |
| 14798 | 3 | | | | | PCGEM1 | 1.00 | | 14893 | 3 | | | | | PMCHL2 | 1.00 |
| 14799 | 3 | | | | | PCLO | 1.00 | | 14894 | 3 | | | | | PMFBP1 | 1.00 |
| 14800 | 3 | | | | | PCNAP1 | 1.00 | | 14895 | 3 | | | | | PNCK | 1.00 |
| 14801 | 3 | | | | | PCSK1 | 1.00 | | 14896 | 3 | | | | | PNLIP | 1.00 |
| 14802 | 3 | | | | | PCSK4 | 1.00 | | 14897 | 3 | | | | | PNLIPRP1 | 1.00 |
| 14803 | 3 | | | | | PCYT1B | 1.00 | | 14898 | 3 | | | | | PNLIPRP2 | 1.00 |
| 14804 | 3 | | | | | PDC | 1.00 | | 14899 | 3 | | | | | PNMA2 | 1.00 |
| 14805 | 3 | | | | | PDCD1 | 1.00 | | 14900 | 3 | | | | | PNMA5 | 1.00 |
| 14806 | 3 | | | | | PDCL2 | 1.00 | | 14901 | 3 | | | | | PNMA6A | 1.00 |
| 14807 | 3 | | | | | PDE10A | 1.00 | | 14902 | 3 | | | | | PNMA6C | 1.00 |
| 14808 | 3 | | | | | PDE11A | 1.00 | | 14903 | 3 | | | | | PNMA6D | 1.00 |
| 14809 | 3 | | | | | PDE1C | 1.00 | | 14904 | 3 | | | | | PNOC | 1.00 |
| 14810 | 3 | | | | | PDE3B | 1.00 | | 14905 | 3 | | | | | POLE2 | 1.00 |
| 14811 | 3 | | | | | PDE4C | 1.00 | | 14906 | 3 | | | | | POLN | 1.00 |
| 14812 | 3 | | | | | PDE6B | 1.00 | | 14907 | 3 | | | | | POLQ | 1.00 |
| 14813 | 3 | | | | | PDE6C | 1.00 | | 14908 | 3 | | | | | POM121L10P | 1.00 |
| 14814 | 3 | | | | | PDE6H | 1.00 | | 14909 | 3 | | | | | POM121L12 | 1.00 |
| 14815 | 3 | | | | | PDIA2 | 1.00 | | 14910 | 3 | | | | | POM121L1P | 1.00 |
| 14816 | 3 | | | | | PDILT | 1.00 | | 14911 | 3 | | | | | POM121L2 | 1.00 |
| 14817 | 3 | | | | | PDX1 | 1.00 | | 14912 | 3 | | | | | POM121L4P | 1.00 |
| 14818 | 3 | | | | | PDYN | 1.00 | | 14913 | 3 | | | | | POM121L8P | 1.00 |
| 14819 | 3 | | | | | PDZD3 | 1.00 | | 14914 | 3 | | | | | PON1 | 1.00 |
| 14820 | 3 | | | | | PDZD9 | 1.00 | | 14915 | 3 | | | | | POPDC3 | 1.00 |
| 14821 | 3 | | | | | PEG3-AS1 | 1.00 | | 14916 | 3 | | | | | POTEA | 1.00 |
| 14822 | 3 | | | | | PER4 | 1.00 | | 14917 | 3 | | | | | POTEB | 1.00 |
| 14823 | 3 | | | | | PEX5L | 1.00 | | 14918 | 3 | | | | | POTEC | 1.00 |
| 14824 | 3 | | | | | PF4 | 1.00 | | 14919 | 3 | | | | | POTED | 1.00 |
| 14825 | 3 | | | | | PF4V1 | 1.00 | | 14920 | 3 | | | | | POTEG | 1.00 |
| 14826 | 3 | | | | | PFKFB1 | 1.00 | | 14921 | 3 | | | | | POTEH | 1.00 |
| 14827 | 3 | | | | | PFN3 | 1.00 | | 14922 | 3 | | | | | POU1F1 | 1.00 |
| 14828 | 3 | | | | | PFN4 | 1.00 | | 14923 | 3 | | | | | POU2AF1 | 1.00 |
| 14829 | 3 | | | | | PGA3 | 1.00 | | 14924 | 3 | | | | | POU3F2 | 1.00 |
| 14830 | 3 | | | | | PGA4 | 1.00 | | 14925 | 3 | | | | | POU3F3 | 1.00 |
| 14831 | 3 | | | | | PGA5 | 1.00 | | 14926 | 3 | | | | | POU3F4 | 1.00 |
| 14832 | 3 | | | | | PGC | 1.00 | | 14927 | 3 | | | | | POU4F1 | 1.00 |
| 14833 | 3 | | | | | PGCP1 | 1.00 | | 14928 | 3 | | | | | POU4F2 | 1.00 |
| 14834 | 3 | | | | | PGK2 | 1.00 | | 14929 | 3 | | | | | POU4F3 | 1.00 |
| 14835 | 3 | | | | | PGLYRP1 | 1.00 | | 14930 | 3 | | | | | POU5F1P4 | 1.00 |
| 14836 | 3 | | | | | PGLYRP2 | 1.00 | | 14931 | 3 | | | | | POU5F2 | 1.00 |
| 14837 | 3 | | | | | PGPEP1L | 1.00 | | 14932 | 3 | | | | | POU6F2 | 1.00 |
| 14838 | 3 | | | | | PGR | 1.00 | | 14933 | 3 | | | | | PP12613 | 1.00 |
| 14839 | 3 | | | | | PHEX | 1.00 | | 14934 | 3 | | | | | PP14571 | 1.00 |
| 14840 | 3 | | | | | PHF21B | 1.00 | | 14935 | 3 | | | | | PP2D1 | 1.00 |
| 14841 | 3 | | | | | PHF2P1 | 1.00 | | 14936 | 3 | | | | | PPAN-P2RY11 | 1.00 |
| 14842 | 3 | | | | | PHGR1 | 1.00 | | 14937 | 3 | | | | | PPBP | 1.00 |
| 14843 | 3 | | | | | PHOSPHO2-KLHL23 | 1.00 | | 14938 | 3 | | | | | PPBPL2 | 1.00 |
| | | | | | | | | | 14939 | 3 | | | | | PPEF1 | 1.00 |
| 14844 | 3 | | | | | PHOX2A | 1.00 | | 14940 | 3 | | | | | PPEF2 | 1.00 |
| 14845 | 3 | | | | | PHOX2B | 1.00 | | 14941 | 3 | | | | | PPFIA2 | 1.00 |
| 14846 | 3 | | | | | PHTF1 | 1.00 | | 14942 | 3 | | | | | PPIAL4B | 1.00 |
| 14847 | 3 | | | | | PIH1D2 | 1.00 | | 14943 | 3 | | | | | PPIAL4C | 1.00 |
| 14848 | 3 | | | | | PIK3CG | 1.00 | | 14944 | 3 | | | | | PPIAL4D | 1.00 |
| 14849 | 3 | | | | | PIPOX | 1.00 | | 14945 | 3 | | | | | PPIAL4E | 1.00 |
| 14850 | 3 | | | | | PIR-FIGF | 1.00 | | 14946 | 3 | | | | | PPIAL4G | 1.00 |
| 14851 | 3 | | | | | PIRT | 1.00 | | 14947 | 3 | | | | | PPIL6 | 1.00 |
| 14852 | 3 | | | | | PISRT1 | 1.00 | | 14948 | 3 | | | | | PPM1E | 1.00 |
| 14853 | 3 | | | | | PITX3 | 1.00 | | 14949 | 3 | | | | | PPP1R14D | 1.00 |
| 14854 | 3 | | | | | PIWIL1 | 1.00 | | 14950 | 3 | | | | | PPP1R17 | 1.00 |
| 14855 | 3 | | | | | PIWIL2 | 1.00 | | 14951 | 3 | | | | | PPP1R1C | 1.00 |
| 14856 | 3 | | | | | PIWIL3 | 1.00 | | 14952 | 3 | | | | | PPP1R2P9 | 1.00 |
| 14857 | 3 | | | | | PIWIL4 | 1.00 | | 14953 | 3 | | | | | PPP1R36 | 1.00 |
| 14858 | 3 | | | | | PKD1L1 | 1.00 | | 14954 | 3 | | | | | PPP1R3A | 1.00 |
| 14859 | 3 | | | | | PKD1L3 | 1.00 | | 14955 | 3 | | | | | PPP1R42 | 1.00 |
| 14860 | 3 | | | | | PKD2L1 | 1.00 | | 14956 | 3 | | | | | PPP1R9A | 1.00 |
| 14861 | 3 | | | | | PKD2L2 | 1.00 | | 14957 | 3 | | | | | PPP3R2 | 1.00 |
| 14862 | 3 | | | | | PKDREJ | 1.00 | | 14958 | 3 | | | | | PPP4R1L | 1.00 |
| 14863 | 3 | | | | | PKHD1 | 1.00 | | 14959 | 3 | | | | | PPP4R4 | 1.00 |
| 14864 | 3 | | | | | PKHD1L1 | 1.00 | | 14960 | 3 | | | | | PPY | 1.00 |
| 14865 | 3 | | | | | PLA1A | 1.00 | | 14961 | 3 | | | | | PPY2 | 1.00 |
| 14866 | 3 | | | | | PLA2G10 | 1.00 | | 14962 | 3 | | | | | PRAC | 1.00 |
| 14867 | 3 | | | | | PLA2G12B | 1.00 | | 14963 | 3 | | | | | PRAME | 1.00 |
| 14868 | 3 | | | | | PLA2G1B | 1.00 | | 14964 | 3 | | | | | PRAMEF1 | 1.00 |
| 14869 | 3 | | | | | PLA2G2C | 1.00 | | 14965 | 3 | | | | | PRAMEF10 | 1.00 |
| 14870 | 3 | | | | | PLA2G2D | 1.00 | | 14966 | 3 | | | | | PRAMEF11 | 1.00 |
| 14871 | 3 | | | | | PLA2G2E | 1.00 | | 14967 | 3 | | | | | PRAMEF12 | 1.00 |
| 14872 | 3 | | | | | PLAC1 | 1.00 | | 14968 | 3 | | | | | PRAMEF13 | 1.00 |
| 14873 | 3 | | | | | PLAC1L | 1.00 | | 14969 | 3 | | | | | PRAMEF14 | 1.00 |
| 14874 | 3 | | | | | PLAC4 | 1.00 | | 14970 | 3 | | | | | PRAMEF15 | 1.00 |

Fig. 38 - 79

| | | | | | | | | | | | | | | | | |
|---|---|---|---|---|---|---|---|---|---|---|---|---|---|---|---|---|
| 14971 | 3 | | | | | | PRAMEF16 | 1.00 | 15067 | 3 | | | | | PSG2 | 1.00 |
| 14972 | 3 | | | | | | PRAMEF17 | 1.00 | 15068 | 3 | | | | | PSG3 | 1.00 |
| 14973 | 3 | | | | | | PRAMEF18 | 1.00 | 15069 | 3 | | | | | PSG5 | 1.00 |
| 14974 | 3 | | | | | | PRAMEF19 | 1.00 | 15070 | 3 | | | | | PSG6 | 1.00 |
| 14975 | 3 | | | | | | PRAMEF2 | 1.00 | 15071 | 3 | | | | | PSG8 | 1.00 |
| 14976 | 3 | | | | | | PRAMEF20 | 1.00 | 15072 | 3 | | | | | PSG9 | 1.00 |
| 14977 | 3 | | | | | | PRAMEF21 | 1.00 | 15073 | 3 | | | | | PSKH2 | 1.00 |
| 14978 | 3 | | | | | | PRAMEF22 | 1.00 | 15074 | 3 | | | | | PSMA8 | 1.00 |
| 14979 | 3 | | | | | | PRAMEF3 | 1.00 | 15075 | 3 | | | | | PSMB11 | 1.00 |
| 14980 | 3 | | | | | | PRAMEF4 | 1.00 | 15076 | 3 | | | | | PTCHD1 | 1.00 |
| 14981 | 3 | | | | | | PRAMEF5 | 1.00 | 15077 | 3 | | | | | PTCHD2 | 1.00 |
| 14982 | 3 | | | | | | PRAMEF6 | 1.00 | 15078 | 3 | | | | | PTCHD3 | 1.00 |
| 14983 | 3 | | | | | | PRAMEF7 | 1.00 | 15079 | 3 | | | | | PTCHD4 | 1.00 |
| 14984 | 3 | | | | | | PRAMEF8 | 1.00 | 15080 | 3 | | | | | PTCRA | 1.00 |
| 14985 | 3 | | | | | | PRAMEF9 | 1.00 | 15081 | 3 | | | | | PTF1A | 1.00 |
| 14986 | 3 | | | | | | PRAP1 | 1.00 | 15082 | 3 | | | | | PTGDR | 1.00 |
| 14987 | 3 | | | | | | PRB1 | 1.00 | 15083 | 3 | | | | | PTGER1 | 1.00 |
| 14988 | 3 | | | | | | PRB3 | 1.00 | 15084 | 3 | | | | | PTH | 1.00 |
| 14989 | 3 | | | | | | PRB4 | 1.00 | 15085 | 3 | | | | | PTH2 | 1.00 |
| 14990 | 3 | | | | | | PRCD | 1.00 | 15086 | 3 | | | | | PTH2R | 1.00 |
| 14991 | 3 | | | | | | PRDM12 | 1.00 | 15087 | 3 | | | | | PTPN4 | 1.00 |
| 14992 | 3 | | | | | | PRDM13 | 1.00 | 15088 | 3 | | | | | PTPN5 | 1.00 |
| 14993 | 3 | | | | | | PRDM14 | 1.00 | 15089 | 3 | | | | | PTPRH | 1.00 |
| 14994 | 3 | | | | | | PRDM5 | 1.00 | 15090 | 3 | | | | | PTPRN | 1.00 |
| 14995 | 3 | | | | | | PRDM7 | 1.00 | 15091 | 3 | | | | | PTPRO | 1.00 |
| 14996 | 3 | | | | | | PRDM9 | 1.00 | 15092 | 3 | | | | | PTPRQ | 1.00 |
| 14997 | 3 | | | | | | PREX2 | 1.00 | 15093 | 3 | | | | | PTPRR | 1.00 |
| 14998 | 3 | | | | | | PRG1 | 1.00 | 15094 | 3 | | | | | PTPRT | 1.00 |
| 14999 | 3 | | | | | | PRG3 | 1.00 | 15095 | 3 | | | | | PTPRVP | 1.00 |
| 15000 | 3 | | | | | | PRH1 | 1.00 | 15096 | 3 | | | | | PTX4 | 1.00 |
| 15001 | 3 | | | | | | PRH1-PRR4 | 1.00 | 15097 | 3 | | | | | PURG | 1.00 |
| 15002 | 3 | | | | | | PRH2 | 1.00 | 15098 | 3 | | | | | PVALB | 1.00 |
| 15003 | 3 | | | | | | PRHOXNB | 1.00 | 15099 | 3 | | | | | PVRL3-AS1 | 1.00 |
| 15004 | 3 | | | | | | PRKAA2 | 1.00 | 15100 | 3 | | | | | PWRN1 | 1.00 |
| 15005 | 3 | | | | | | PRKAG3 | 1.00 | 15101 | 3 | | | | | PWRN2 | 1.00 |
| 15006 | 3 | | | | | | PRKCG | 1.00 | 15102 | 3 | | | | | PXDNL | 1.00 |
| 15007 | 3 | | | | | | PRKY | 1.00 | 15103 | 3 | | | | | PXT1 | 1.00 |
| 15008 | 3 | | | | | | PRL | 1.00 | 15104 | 3 | | | | | PYDC2 | 1.00 |
| 15009 | 3 | | | | | | PRLH | 1.00 | 15105 | 3 | | | | | PYGO1 | 1.00 |
| 15010 | 3 | | | | | | PRLHR | 1.00 | 15106 | 3 | | | | | PYHIN1 | 1.00 |
| 15011 | 3 | | | | | | PRM1 | 1.00 | 15107 | 3 | | | | | PYY | 1.00 |
| 15012 | 3 | | | | | | PRM2 | 1.00 | 15108 | 3 | | | | | PYY2 | 1.00 |
| 15013 | 3 | | | | | | PRM3 | 1.00 | 15109 | 3 | | | | | PZP | 1.00 |
| 15014 | 3 | | | | | | PRMT8 | 1.00 | 15110 | 3 | | | | | QRFP | 1.00 |
| 15015 | 3 | | | | | | PRND | 1.00 | 15111 | 3 | | | | | QRFPR | 1.00 |
| 15016 | 3 | | | | | | PRNT | 1.00 | 15112 | 3 | | | | | QRICH2 | 1.00 |
| 15017 | 3 | | | | | | PRO1768 | 1.00 | 15113 | 3 | | | | | R3HDML | 1.00 |
| 15018 | 3 | | | | | | PROC | 1.00 | 15114 | 3 | | | | | RAB19 | 1.00 |
| 15019 | 3 | | | | | | PRODH2 | 1.00 | 15115 | 3 | | | | | RAB39A | 1.00 |
| 15020 | 3 | | | | | | PROK1 | 1.00 | 15116 | 3 | | | | | RAB39B | 1.00 |
| 15021 | 3 | | | | | | PROKR1 | 1.00 | 15117 | 3 | | | | | RAB3C | 1.00 |
| 15022 | 3 | | | | | | PROKR2 | 1.00 | 15118 | 3 | | | | | RAB40A | 1.00 |
| 15023 | 3 | | | | | | PROL1 | 1.00 | 15119 | 3 | | | | | RAB41 | 1.00 |
| 15024 | 3 | | | | | | PROP1 | 1.00 | 15120 | 3 | | | | | RAB4B-EGLN2 | 1.00 |
| 15025 | 3 | | | | | | PROX1 | 1.00 | 15121 | 3 | | | | | RAB9BP1 | 1.00 |
| 15026 | 3 | | | | | | PROX1-AS1 | 1.00 | 15122 | 3 | | | | | RAD21-AS1 | 1.00 |
| 15027 | 3 | | | | | | PROX2 | 1.00 | 15123 | 3 | | | | | RAD21L1 | 1.00 |
| 15028 | 3 | | | | | | PROZ | 1.00 | 15124 | 3 | | | | | RAD51AP2 | 1.00 |
| 15029 | 3 | | | | | | PRR15 | 1.00 | 15125 | 3 | | | | | RAD54B | 1.00 |
| 15030 | 3 | | | | | | PRR18 | 1.00 | 15126 | 3 | | | | | RAD54L | 1.00 |
| 15031 | 3 | | | | | | PRR19 | 1.00 | 15127 | 3 | | | | | RAD9B | 1.00 |
| 15032 | 3 | | | | | | PRR20B | 1.00 | 15128 | 3 | | | | | RAET1K | 1.00 |
| 15033 | 3 | | | | | | PRR20D | 1.00 | 15129 | 3 | | | | | RAG1 | 1.00 |
| 15034 | 3 | | | | | | PRR20E | 1.00 | 15130 | 3 | | | | | RAG2 | 1.00 |
| 15035 | 3 | | | | | | PRR21 | 1.00 | 15131 | 3 | | | | | RALYL | 1.00 |
| 15036 | 3 | | | | | | PRR23A | 1.00 | 15132 | 3 | | | | | RANBP17 | 1.00 |
| 15037 | 3 | | | | | | PRR23B | 1.00 | 15133 | 3 | | | | | RANBP3L | 1.00 |
| 15038 | 3 | | | | | | PRR23C | 1.00 | 15134 | 3 | | | | | RAPSN | 1.00 |
| 15039 | 3 | | | | | | PRR25 | 1.00 | 15135 | 3 | | | | | RASA2 | 1.00 |
| 15040 | 3 | | | | | | PRR5-ARHGAP8 | 1.00 | 15136 | 3 | | | | | RASEF | 1.00 |
| 15041 | 3 | | | | | | PRSS1 | 1.00 | 15137 | 3 | | | | | RASGRF1 | 1.00 |
| 15042 | 3 | | | | | | PRSS2 | 1.00 | 15138 | 3 | | | | | RASL10B | 1.00 |
| 15043 | 3 | | | | | | PRSS3OP | 1.00 | 15139 | 3 | | | | | RAX2 | 1.00 |
| 15044 | 3 | | | | | | PRSS33 | 1.00 | 15140 | 3 | | | | | RBAK-LOC389458 | 1.00 |
| 15045 | 3 | | | | | | PRSS35 | 1.00 | 15141 | 3 | | | | | RBFOX1 | 1.00 |
| 15046 | 3 | | | | | | PRSS37 | 1.00 | 15142 | 3 | | | | | RBFOX3 | 1.00 |
| 15047 | 3 | | | | | | PRSS38 | 1.00 | 15143 | 3 | | | | | RBKS | 1.00 |
| 15048 | 3 | | | | | | PRSS41 | 1.00 | 15144 | 3 | | | | | RBL1 | 1.00 |
| 15049 | 3 | | | | | | PRSS42 | 1.00 | 15145 | 3 | | | | | RBM11 | 1.00 |
| 15050 | 3 | | | | | | PRSS45 | 1.00 | 15146 | 3 | | | | | RBM44 | 1.00 |
| 15051 | 3 | | | | | | PRSS46 | 1.00 | 15147 | 3 | | | | | RBM46 | 1.00 |
| 15052 | 3 | | | | | | PRSS48 | 1.00 | 15148 | 3 | | | | | RBMXL2 | 1.00 |
| 15053 | 3 | | | | | | PRSS50 | 1.00 | 15149 | 3 | | | | | RBMXL3 | 1.00 |
| 15054 | 3 | | | | | | PRSS54 | 1.00 | 15150 | 3 | | | | | RBMY1A1 | 1.00 |
| 15055 | 3 | | | | | | PRSS55 | 1.00 | 15151 | 3 | | | | | RBMY1A3P | 1.00 |
| 15056 | 3 | | | | | | PRSS56 | 1.00 | 15152 | 3 | | | | | RBMY1B | 1.00 |
| 15057 | 3 | | | | | | PRSS57 | 1.00 | 15153 | 3 | | | | | RBMY1D | 1.00 |
| 15058 | 3 | | | | | | PRSS58 | 1.00 | 15154 | 3 | | | | | RBMY1E | 1.00 |
| 15059 | 3 | | | | | | PRTG | 1.00 | 15155 | 3 | | | | | RBMY1F | 1.00 |
| 15060 | 3 | | | | | | PRTN3 | 1.00 | 15156 | 3 | | | | | RBMY1J | 1.00 |
| 15061 | 3 | | | | | | PRY | 1.00 | 15157 | 3 | | | | | RBMY2EP | 1.00 |
| 15062 | 3 | | | | | | PSD | 1.00 | 15158 | 3 | | | | | RBMY2FP | 1.00 |
| 15063 | 3 | | | | | | PSD2 | 1.00 | 15159 | 3 | | | | | RBMY3AP | 1.00 |
| 15064 | 3 | | | | | | PSG1 | 1.00 | 15160 | 3 | | | | | RBP2 | 1.00 |
| 15065 | 3 | | | | | | PSG10P | 1.00 | 15161 | 3 | | | | | RBP3 | 1.00 |
| 15066 | 3 | | | | | | PSG11 | 1.00 | 15162 | 3 | | | | | RBPJL | 1.00 |

Fig. 38 - 80

| | | | | | | | |
|---|---|---|---|---|---|---|---|
| 15163 | 3 | | RCAN3AS | 1.00 | 15259 | 3 | RPA4 | 1.00 |
| 15164 | 3 | | RCOR2 | 1.00 | 15260 | 3 | RPE65 | 1.00 |
| 15165 | 3 | | RD3 | 1.00 | 15261 | 3 | RPGRIP1 | 1.00 |
| 15166 | 3 | | RDH8 | 1.00 | 15262 | 3 | RPH3A | 1.00 |
| 15167 | 3 | | RDM1 | 1.00 | 15263 | 3 | RPL13AP17 | 1.00 |
| 15168 | 3 | | REG1A | 1.00 | 15264 | 3 | RPL13AP3 | 1.00 |
| 15169 | 3 | | REG1B | 1.00 | 15265 | 3 | RPL13AP5 | 1.00 |
| 15170 | 3 | | REG1P | 1.00 | 15266 | 3 | RPL31P11 | 1.00 |
| 15171 | 3 | | REG3A | 1.00 | 15267 | 3 | RPL3L | 1.00 |
| 15172 | 3 | | REG3G | 1.00 | 15268 | 3 | RPLP0P2 | 1.00 |
| 15173 | 3 | | REG4 | 1.00 | 15269 | 3 | RPS16P5 | 1.00 |
| 15174 | 3 | | REN | 1.00 | 15270 | 3 | RPS21 | 1.00 |
| 15175 | 3 | | REREP3 | 1.00 | 15271 | 3 | RPS4Y1 | 1.00 |
| 15176 | 3 | | RESP18 | 1.00 | 15272 | 3 | RPS4Y2 | 1.00 |
| 15177 | 3 | | RETN | 1.00 | 15273 | 3 | RPS7P5 | 1.00 |
| 15178 | 3 | | RETNLB | 1.00 | 15274 | 3 | RPSAP52 | 1.00 |
| 15179 | 3 | | REXO1L1 | 1.00 | 15275 | 3 | RRH | 1.00 |
| 15180 | 3 | | RFPL1 | 1.00 | 15276 | 3 | RS1 | 1.00 |
| 15181 | 3 | | RFPL1-AS1 | 1.00 | 15277 | 3 | RSPH10B2 | 1.00 |
| 15182 | 3 | | RFPL3 | 1.00 | 15278 | 3 | RSPH4A | 1.00 |
| 15183 | 3 | | RFPL4A | 1.00 | 15279 | 3 | RSPH6A | 1.00 |
| 15184 | 3 | | RFPL4B | 1.00 | 15280 | 3 | RSPH9 | 1.00 |
| 15185 | 3 | | RFX3 | 1.00 | 15281 | 3 | RSPO2 | 1.00 |
| 15186 | 3 | | RFX4 | 1.00 | 15282 | 3 | RTBDN | 1.00 |
| 15187 | 3 | | RFX6 | 1.00 | 15283 | 3 | RTDR1 | 1.00 |
| 15188 | 3 | | RGAG1 | 1.00 | 15284 | 3 | RTKN2 | 1.00 |
| 15189 | 3 | | RGPD2 | 1.00 | 15285 | 3 | RTL1 | 1.00 |
| 15190 | 3 | | RGPD6 | 1.00 | 15286 | 3 | RTP1 | 1.00 |
| 15191 | 3 | | RGR | 1.00 | 15287 | 3 | RTP2 | 1.00 |
| 15192 | 3 | | RGS17 | 1.00 | 15288 | 3 | RTP3 | 1.00 |
| 15193 | 3 | | RGS20 | 1.00 | 15289 | 3 | RTTN | 1.00 |
| 15194 | 3 | | RGS21 | 1.00 | 15290 | 3 | RUFY4 | 1.00 |
| 15195 | 3 | | RGS22 | 1.00 | 15291 | 3 | RUNX1-IT1 | 1.00 |
| 15196 | 3 | | RGS4 | 1.00 | 15292 | 3 | RXFP1 | 1.00 |
| 15197 | 3 | | RGS7 | 1.00 | 15293 | 3 | RXFP2 | 1.00 |
| 15198 | 3 | | RGS7BP | 1.00 | 15294 | 3 | RXFP3 | 1.00 |
| 15199 | 3 | | RGS8 | 1.00 | 15295 | 3 | RXFP4 | 1.00 |
| 15200 | 3 | | RGS9 | 1.00 | 15296 | 3 | RYR2 | 1.00 |
| 15201 | 3 | | RGSL1 | 1.00 | 15297 | 3 | RYR3 | 1.00 |
| 15202 | 3 | | RHAG | 1.00 | 15298 | 3 | S100A5 | 1.00 |
| 15203 | 3 | | RHBDL3 | 1.00 | 15299 | 3 | S100A7A | 1.00 |
| 15204 | 3 | | RHCE | 1.00 | 15300 | 3 | S100A7L2 | 1.00 |
| 15205 | 3 | | RHO | 1.00 | 15301 | 3 | S100G | 1.00 |
| 15206 | 3 | | RHOXF2 | 1.00 | 15302 | 3 | S100Z | 1.00 |
| 15207 | 3 | | RHOXF2B | 1.00 | 15303 | 3 | SAA2-SAA4 | 1.00 |
| 15208 | 3 | | RIBC2 | 1.00 | 15304 | 3 | SAA3P | 1.00 |
| 15209 | 3 | | RIIAD1 | 1.00 | 15305 | 3 | SAA4 | 1.00 |
| 15210 | 3 | | RIMBP3 | 1.00 | 15306 | 3 | SAG | 1.00 |
| 15211 | 3 | | RIMBP3B | 1.00 | 15307 | 3 | SAGE1 | 1.00 |
| 15212 | 3 | | RIMBP3C | 1.00 | 15308 | 3 | SALL1 | 1.00 |
| 15213 | 3 | | RIMKLA | 1.00 | 15309 | 3 | SALL3 | 1.00 |
| 15214 | 3 | | RIMS1 | 1.00 | 15310 | 3 | SALL4 | 1.00 |
| 15215 | 3 | | RIMS2 | 1.00 | 15311 | 3 | SAMD11 | 1.00 |
| 15216 | 3 | | RIMS4 | 1.00 | 15312 | 3 | SAMD12 | 1.00 |
| 15217 | 3 | | RIPPLY1 | 1.00 | 15313 | 3 | SAMD12-AS1 | 1.00 |
| 15218 | 3 | | RIPPLY2 | 1.00 | 15314 | 3 | SAMD13 | 1.00 |
| 15219 | 3 | | RIT2 | 1.00 | 15315 | 3 | SAMD14 | 1.00 |
| 15220 | 3 | | RLBP1 | 1.00 | 15316 | 3 | SAMD15 | 1.00 |
| 15221 | 3 | | RLN1 | 1.00 | 15317 | 3 | SAMD3 | 1.00 |
| 15222 | 3 | | RLN2 | 1.00 | 15318 | 3 | SAMD7 | 1.00 |
| 15223 | 3 | | RLN3 | 1.00 | 15319 | 3 | SARDH | 1.00 |
| 15224 | 3 | | RLTPR | 1.00 | 15320 | 3 | SATL1 | 1.00 |
| 15225 | 3 | | RMST | 1.00 | 15321 | 3 | SBK2 | 1.00 |
| 15226 | 3 | | RNASE10 | 1.00 | 15322 | 3 | SCAND3 | 1.00 |
| 15227 | 3 | | RNASE11 | 1.00 | 15323 | 3 | SCARNA1 | 1.00 |
| 15228 | 3 | | RNASE12 | 1.00 | 15324 | 3 | SCARNA11 | 1.00 |
| 15229 | 3 | | RNASE3 | 1.00 | 15325 | 3 | SCARNA13 | 1.00 |
| 15230 | 3 | | RNASE8 | 1.00 | 15326 | 3 | SCARNA14 | 1.00 |
| 15231 | 3 | | RNASE9 | 1.00 | 15327 | 3 | SCARNA15 | 1.00 |
| 15232 | 3 | | RNF103-CHMP3 | 1.00 | 15328 | 3 | SCARNA18 | 1.00 |
| 15233 | 3 | | RNF113B | 1.00 | 15329 | 3 | SCARNA20 | 1.00 |
| 15234 | 3 | | RNF133 | 1.00 | 15330 | 3 | SCARNA21 | 1.00 |
| 15235 | 3 | | RNF148 | 1.00 | 15331 | 3 | SCARNA22 | 1.00 |
| 15236 | 3 | | RNF150 | 1.00 | 15332 | 3 | SCARNA23 | 1.00 |
| 15237 | 3 | | RNF151 | 1.00 | 15333 | 3 | SCARNA27 | 1.00 |
| 15238 | 3 | | RNF17 | 1.00 | 15334 | 3 | SCARNA3 | 1.00 |
| 15239 | 3 | | RNF182 | 1.00 | 15335 | 3 | SCARNA5 | 1.00 |
| 15240 | 3 | | RNF183 | 1.00 | 15336 | 3 | SCARNA6 | 1.00 |
| 15241 | 3 | | RNF186 | 1.00 | 15337 | 3 | SCARNA8 | 1.00 |
| 15242 | 3 | | RNF224 | 1.00 | 15338 | 3 | SCARNA9L | 1.00 |
| 15243 | 3 | | RNFT2 | 1.00 | 15339 | 3 | SCG2 | 1.00 |
| 15244 | 3 | | RNU4ATAC | 1.00 | 15340 | 3 | SCG3 | 1.00 |
| 15245 | 3 | | RNU5D-1 | 1.00 | 15341 | 3 | SCG5 | 1.00 |
| 15246 | 3 | | RNU5E-1 | 1.00 | 15342 | 3 | SCGB1A1 | 1.00 |
| 15247 | 3 | | RNU5F-1 | 1.00 | 15343 | 3 | SCGB1C1 | 1.00 |
| 15248 | 3 | | RNU6ATAC | 1.00 | 15344 | 3 | SCGB1D1 | 1.00 |
| 15249 | 3 | | RNU86 | 1.00 | 15345 | 3 | SCGB1D4 | 1.00 |
| 15250 | 3 | | RNY4 | 1.00 | 15346 | 3 | SCGB2B2 | 1.00 |
| 15251 | 3 | | RNY5 | 1.00 | 15347 | 3 | SCGB2B3P | 1.00 |
| 15252 | 3 | | ROPN1L | 1.00 | 15348 | 3 | SCGB3A2 | 1.00 |
| 15253 | 3 | | RORB | 1.00 | 15349 | 3 | SCGN | 1.00 |
| 15254 | 3 | | ROS1 | 1.00 | 15350 | 3 | SCIMP | 1.00 |
| 15255 | 3 | | RP1 | 1.00 | 15351 | 3 | SCN10A | 1.00 |
| 15256 | 3 | | RP11-165H21 | 1.00 | 15352 | 3 | SCN11A | 1.00 |
| 15257 | 3 | | RP1-177G6.2 | 1.00 | 15353 | 3 | SCN1A | 1.00 |
| 15258 | 3 | | RP1L1 | 1.00 | 15354 | 3 | SCN2A | 1.00 |

Fig. 38 - 81

| | | | | | | | | | | | | | | | |
|---|---|---|---|---|---|---|---|---|---|---|---|---|---|---|---|
| 15355 | 3 | | | | | SCN3A | 1.00 | 15451 | 3 | | | | | SLC14A2 | 1.00 |
| 15356 | 3 | | | | | SCN5A | 1.00 | 15452 | 3 | | | | | SLC15A2 | 1.00 |
| 15357 | 3 | | | | | SCN8A | 1.00 | 15453 | 3 | | | | | SLC15A5 | 1.00 |
| 15358 | 3 | | | | | SCRG1 | 1.00 | 15454 | 3 | | | | | SLC16A12 | 1.00 |
| 15359 | 3 | | | | | SCRT1 | 1.00 | 15455 | 3 | | | | | SLC16A7 | 1.00 |
| 15360 | 3 | | | | | SCRT2 | 1.00 | 15456 | 3 | | | | | SLC16A9 | 1.00 |
| 15361 | 3 | | | | | SCT | 1.00 | 15457 | 3 | | | | | SLC17A1 | 1.00 |
| 15362 | 3 | | | | | SCTR | 1.00 | 15458 | 3 | | | | | SLC17A2 | 1.00 |
| 15363 | 3 | | | | | SDC4P | 1.00 | 15459 | 3 | | | | | SLC17A3 | 1.00 |
| 15364 | 3 | | | | | SDS | 1.00 | 15460 | 3 | | | | | SLC17A4 | 1.00 |
| 15365 | 3 | | | | | SEBOX | 1.00 | 15461 | 3 | | | | | SLC17A6 | 1.00 |
| 15366 | 3 | | | | | SEC1 | 1.00 | 15462 | 3 | | | | | SLC17A8 | 1.00 |
| 15367 | 3 | | | | | SEC14L3 | 1.00 | 15463 | 3 | | | | | SLC18A1 | 1.00 |
| 15368 | 3 | | | | | SEL1L2 | 1.00 | 15464 | 3 | | | | | SLC18A3 | 1.00 |
| 15369 | 3 | | | | | SELV | 1.00 | 15465 | 3 | | | | | SLC22A1 | 1.00 |
| 15370 | 3 | | | | | SEMG1 | 1.00 | 15466 | 3 | | | | | SLC22A10 | 1.00 |
| 15371 | 3 | | | | | SEMG2 | 1.00 | 15467 | 3 | | | | | SLC22A11 | 1.00 |
| 15372 | 3 | | | | | SENP3-EIF4A1 | 1.00 | 15468 | 3 | | | | | SLC22A12 | 1.00 |
| 15373 | 3 | | | | | SEPT12 | 1.00 | 15469 | 3 | | | | | SLC22A13 | 1.00 |
| 15374 | 3 | | | | | SEPT14 | 1.00 | 15470 | 3 | | | | | SLC22A14 | 1.00 |
| 15375 | 3 | | | | | SEPT7L | 1.00 | 15471 | 3 | | | | | SLC22A16 | 1.00 |
| 15376 | 3 | | | | | SERF2-C15ORF63 | 1.00 | 15472 | 3 | | | | | SLC22A2 | 1.00 |
| 15377 | 3 | | | | | SERPINA10 | 1.00 | 15473 | 3 | | | | | SLC22A20 | 1.00 |
| 15378 | 3 | | | | | SERPINA13 | 1.00 | 15474 | 3 | | | | | SLC22A24 | 1.00 |
| 15379 | 3 | | | | | SERPINA4 | 1.00 | 15475 | 3 | | | | | SLC22A25 | 1.00 |
| 15380 | 3 | | | | | SERPINA6 | 1.00 | 15476 | 3 | | | | | SLC22A6 | 1.00 |
| 15381 | 3 | | | | | SERPINA7 | 1.00 | 15477 | 3 | | | | | SLC22A7 | 1.00 |
| 15382 | 3 | | | | | SERPINB10 | 1.00 | 15478 | 3 | | | | | SLC22A8 | 1.00 |
| 15383 | 3 | | | | | SERPINB11 | 1.00 | 15479 | 3 | | | | | SLC22A9 | 1.00 |
| 15384 | 3 | | | | | SERPIND1 | 1.00 | 15480 | 3 | | | | | SLC23A1 | 1.00 |
| 15385 | 3 | | | | | SERPINE3 | 1.00 | 15481 | 3 | | | | | SLC24A2 | 1.00 |
| 15386 | 3 | | | | | SERPINI2 | 1.00 | 15482 | 3 | | | | | SLC24A4 | 1.00 |
| 15387 | 3 | | | | | SERTM1 | 1.00 | 15483 | 3 | | | | | SLC25A2 | 1.00 |
| 15388 | 3 | | | | | SESN3 | 1.00 | 15484 | 3 | | | | | SLC25A21 | 1.00 |
| 15389 | 3 | | | | | SEZ6 | 1.00 | 15485 | 3 | | | | | SLC25A31 | 1.00 |
| 15390 | 3 | | | | | SFTA1P | 1.00 | 15486 | 3 | | | | | SLC25A41 | 1.00 |
| 15391 | 3 | | | | | SFTA2 | 1.00 | 15487 | 3 | | | | | SLC25A47 | 1.00 |
| 15392 | 3 | | | | | SFTA3 | 1.00 | 15488 | 3 | | | | | SLC26A3 | 1.00 |
| 15393 | 3 | | | | | SFTPA1 | 1.00 | 15489 | 3 | | | | | SLC26A5 | 1.00 |
| 15394 | 3 | | | | | SFTPA2 | 1.00 | 15490 | 3 | | | | | SLC26A7 | 1.00 |
| 15395 | 3 | | | | | SFTPB | 1.00 | 15491 | 3 | | | | | SLC26A8 | 1.00 |
| 15396 | 3 | | | | | SFTPC | 1.00 | 15492 | 3 | | | | | SLC27A5 | 1.00 |
| 15397 | 3 | | | | | SGCZ | 1.00 | 15493 | 3 | | | | | SLC28A1 | 1.00 |
| 15398 | 3 | | | | | SGIP1 | 1.00 | 15494 | 3 | | | | | SLC28A2 | 1.00 |
| 15399 | 3 | | | | | SGK110 | 1.00 | 15495 | 3 | | | | | SLC2A2 | 1.00 |
| 15400 | 3 | | | | | SGK196 | 1.00 | 15496 | 3 | | | | | SLC2A7 | 1.00 |
| 15401 | 3 | | | | | SGOL1 | 1.00 | 15497 | 3 | | | | | SLC30A10 | 1.00 |
| 15402 | 3 | | | | | SH2D1B | 1.00 | 15498 | 3 | | | | | SLC30A2 | 1.00 |
| 15403 | 3 | | | | | SH2D2A | 1.00 | 15499 | 3 | | | | | SLC30A3 | 1.00 |
| 15404 | 3 | | | | | SH2D4B | 1.00 | 15500 | 3 | | | | | SLC30A4 | 1.00 |
| 15405 | 3 | | | | | SH2D5 | 1.00 | 15501 | 3 | | | | | SLC30A8 | 1.00 |
| 15406 | 3 | | | | | SH2D6 | 1.00 | 15502 | 3 | | | | | SLC32A1 | 1.00 |
| 15407 | 3 | | | | | SH2D7 | 1.00 | 15503 | 3 | | | | | SLC34A1 | 1.00 |
| 15408 | 3 | | | | | SH3GL2 | 1.00 | 15504 | 3 | | | | | SLC34A3 | 1.00 |
| 15409 | 3 | | | | | SH3GL3 | 1.00 | 15505 | 3 | | | | | SLC35D3 | 1.00 |
| 15410 | 3 | | | | | SH3TC2 | 1.00 | 15506 | 3 | | | | | SLC35F3 | 1.00 |
| 15411 | 3 | | | | | SHANK1 | 1.00 | 15507 | 3 | | | | | SLC35F4 | 1.00 |
| 15412 | 3 | | | | | SH8G | 1.00 | 15508 | 3 | | | | | SLC35G3 | 1.00 |
| 15413 | 3 | | | | | SHCBP1L | 1.00 | 15509 | 3 | | | | | SLC35G5 | 1.00 |
| 15414 | 3 | | | | | SHD | 1.00 | 15510 | 3 | | | | | SLC35G6 | 1.00 |
| 15415 | 3 | | | | | SHH | 1.00 | 15511 | 3 | | | | | SLC36A2 | 1.00 |
| 15416 | 3 | | | | | SHISA7 | 1.00 | 15512 | 3 | | | | | SLC36A3 | 1.00 |
| 15417 | 3 | | | | | SHISA8 | 1.00 | 15513 | 3 | | | | | SLC38A11 | 1.00 |
| 15418 | 3 | | | | | SHISA9 | 1.00 | 15514 | 3 | | | | | SLC38A8 | 1.00 |
| 15419 | 3 | | | | | SHOX | 1.00 | 15515 | 3 | | | | | SLC39A12 | 1.00 |
| 15420 | 3 | | | | | SHPRH | 1.00 | 15516 | 3 | | | | | SLC39A5 | 1.00 |
| 15421 | 3 | | | | | SI | 1.00 | 15517 | 3 | | | | | SLC3A1 | 1.00 |
| 15422 | 3 | | | | | SIAH3 | 1.00 | 15518 | 3 | | | | | SLC45A2 | 1.00 |
| 15423 | 3 | | | | | SIGLEC11 | 1.00 | 15519 | 3 | | | | | SLC4A1 | 1.00 |
| 15424 | 3 | | | | | SIGLEC12 | 1.00 | 15520 | 3 | | | | | SLC4A10 | 1.00 |
| 15425 | 3 | | | | | SIGLEC14 | 1.00 | 15521 | 3 | | | | | SLC4A4 | 1.00 |
| 15426 | 3 | | | | | SIGLEC15 | 1.00 | 15522 | 3 | | | | | SLC4A8 | 1.00 |
| 15427 | 3 | | | | | SIGLEC16 | 1.00 | 15523 | 3 | | | | | SLC4A9 | 1.00 |
| 15428 | 3 | | | | | SIGLEC5 | 1.00 | 15524 | 3 | | | | | SLC5A11 | 1.00 |
| 15429 | 3 | | | | | SIGLEC7 | 1.00 | 15525 | 3 | | | | | SLC5A12 | 1.00 |
| 15430 | 3 | | | | | SIGLEC9 | 1.00 | 15526 | 3 | | | | | SLC5A2 | 1.00 |
| 15431 | 3 | | | | | SIM1 | 1.00 | 15527 | 3 | | | | | SLC5A4 | 1.00 |
| 15432 | 3 | | | | | SIRPD | 1.00 | 15528 | 3 | | | | | SLC5A5 | 1.00 |
| 15433 | 3 | | | | | SIX1 | 1.00 | 15529 | 3 | | | | | SLC5A7 | 1.00 |
| 15434 | 3 | | | | | SIX3 | 1.00 | 15530 | 3 | | | | | SLC5A8 | 1.00 |
| 15435 | 3 | | | | | SIX4 | 1.00 | 15531 | 3 | | | | | SLC6A10P | 1.00 |
| 15436 | 3 | | | | | SIX6 | 1.00 | 15532 | 3 | | | | | SLC6A12 | 1.00 |
| 15437 | 3 | | | | | SKA1 | 1.00 | 15533 | 3 | | | | | SLC6A18 | 1.00 |
| 15438 | 3 | | | | | SKINTL | 1.00 | 15534 | 3 | | | | | SLC6A19 | 1.00 |
| 15439 | 3 | | | | | SKOR1 | 1.00 | 15535 | 3 | | | | | SLC6A20 | 1.00 |
| 15440 | 3 | | | | | SLAMF9 | 1.00 | 15536 | 3 | | | | | SLC6A3 | 1.00 |
| 15441 | 3 | | | | | SLC10A1 | 1.00 | 15537 | 3 | | | | | SLC6A4 | 1.00 |
| 15442 | 3 | | | | | SLC10A2 | 1.00 | 15538 | 3 | | | | | SLC6A5 | 1.00 |
| 15443 | 3 | | | | | SLC10A4 | 1.00 | 15539 | 3 | | | | | SLC6A7 | 1.00 |
| 15444 | 3 | | | | | SLC10A5 | 1.00 | 15540 | 3 | | | | | SLC7A10 | 1.00 |
| 15445 | 3 | | | | | SLC12A1 | 1.00 | 15541 | 3 | | | | | SLC7A11 | 1.00 |
| 15446 | 3 | | | | | SLC12A3 | 1.00 | 15542 | 3 | | | | | SLC7A13 | 1.00 |
| 15447 | 3 | | | | | SLC12A5 | 1.00 | 15543 | 3 | | | | | SLC7A14 | 1.00 |
| 15448 | 3 | | | | | SLC13A1 | 1.00 | 15544 | 3 | | | | | SLC7A3 | 1.00 |
| 15449 | 3 | | | | | SLC13A4 | 1.00 | 15545 | 3 | | | | | SLC7A9 | 1.00 |
| 15450 | 3 | | | | | SLC13A5 | 1.00 | 15546 | 3 | | | | | SLC8A2 | 1.00 |

Fig. 38 - 82

| | | | | | | | | | | | | | | |
|---|---|---|---|---|---|---|---|---|---|---|---|---|---|---|
| 15547 | 3 | | | | | | SLC8A3 | 1.00 | 15643 | 3 | | | SNORA5A | 1.00 |
| 15548 | 3 | | | | | | SLC9A10 | 1.00 | 15644 | 3 | | | SNORA5B | 1.00 |
| 15549 | 3 | | | | | | SLC9A11 | 1.00 | 15645 | 3 | | | SNORA5C | 1.00 |
| 15550 | 3 | | | | | | SLC9A4 | 1.00 | 15646 | 3 | | | SNORA6 | 1.00 |
| 15551 | 3 | | | | | | SLC9A7 | 1.00 | 15647 | 3 | | | SNORA60 | 1.00 |
| 15552 | 3 | | | | | | SLC9A7P1 | 1.00 | 15648 | 3 | | | SNORA66 | 1.00 |
| 15553 | 3 | | | | | | SLC9B1 | 1.00 | 15649 | 3 | | | SNORA68 | 1.00 |
| 15554 | 3 | | | | | | SLCO1A2 | 1.00 | 15650 | 3 | | | SNORA69 | 1.00 |
| 15555 | 3 | | | | | | SLCO1B1 | 1.00 | 15651 | 3 | | | SNORA70B | 1.00 |
| 15556 | 3 | | | | | | SLCO1B3 | 1.00 | 15652 | 3 | | | SNORA70C | 1.00 |
| 15557 | 3 | | | | | | SLCO1B7 | 1.00 | 15653 | 3 | | | SNORA70D | 1.00 |
| 15558 | 3 | | | | | | SLCO1C1 | 1.00 | 15654 | 3 | | | SNORA70E | 1.00 |
| 15559 | 3 | | | | | | SLCO5A1 | 1.00 | 15655 | 3 | | | SNORA70F | 1.00 |
| 15560 | 3 | | | | | | SLCO6A1 | 1.00 | 15656 | 3 | | | SNORA70G | 1.00 |
| 15561 | 3 | | | | | | SLFN12L | 1.00 | 15657 | 3 | | | SNORA71B | 1.00 |
| 15562 | 3 | | | | | | SLFN14 | 1.00 | 15658 | 3 | | | SNORA71D | 1.00 |
| 15563 | 3 | | | | | | SLFNL1 | 1.00 | 15659 | 3 | | | SNORA74B | 1.00 |
| 15564 | 3 | | | | | | SLIT1 | 1.00 | 15660 | 3 | | | SNORA76 | 1.00 |
| 15565 | 3 | | | | | | SLIT2-IT1 | 1.00 | 15661 | 3 | | | SNORA78 | 1.00 |
| 15566 | 3 | | | | | | SLITRK1 | 1.00 | 15662 | 3 | | | SNORA79 | 1.00 |
| 15567 | 3 | | | | | | SLMO2-ATP5E | 1.00 | 15663 | 3 | | | SNORA7A | 1.00 |
| 15568 | 3 | | | | | | SMC1B | 1.00 | 15664 | 3 | | | SNORA7B | 1.00 |
| 15569 | 3 | | | | | | SMCP | 1.00 | 15665 | 3 | | | SNORA8 | 1.00 |
| 15570 | 3 | | | | | | SMCR5 | 1.00 | 15666 | 3 | | | SNORA80 | 1.00 |
| 15571 | 3 | | | | | | SMCR9 | 1.00 | 15667 | 3 | | | SNORA80B | 1.00 |
| 15572 | 3 | | | | | | SMEK3P | 1.00 | 15668 | 3 | | | SNORA84 | 1.00 |
| 15573 | 3 | | | | | | SMN1 | 1.00 | 15669 | 3 | | | SNORD100 | 1.00 |
| 15574 | 3 | | | | | | SMPX | 1.00 | 15670 | 3 | | | SNORD101 | 1.00 |
| 15575 | 3 | | | | | | SMR3A | 1.00 | 15671 | 3 | | | SNORD102 | 1.00 |
| 15576 | 3 | | | | | | SMR3B | 1.00 | 15672 | 3 | | | SNORD103A | 1.00 |
| 15577 | 3 | | | | | | SMTNL1 | 1.00 | 15673 | 3 | | | SNORD104 | 1.00 |
| 15578 | 3 | | | | | | SMYD1 | 1.00 | 15674 | 3 | | | SNORD105 | 1.00 |
| 15579 | 3 | | | | | | SNAP25 | 1.00 | 15675 | 3 | | | SNORD105B | 1.00 |
| 15580 | 3 | | | | | | SNAP91 | 1.00 | 15676 | 3 | | | SNORD107 | 1.00 |
| 15581 | 3 | | | | | | SNAR-A1 | 1.00 | 15677 | 3 | | | SNORD108 | 1.00 |
| 15582 | 3 | | | | | | SNAR-A11 | 1.00 | 15678 | 3 | | | SNORD109B | 1.00 |
| 15583 | 3 | | | | | | SNAR-A12 | 1.00 | 15679 | 3 | | | SNORD11 | 1.00 |
| 15584 | 3 | | | | | | SNAR-A13 | 1.00 | 15680 | 3 | | | SNORD110 | 1.00 |
| 15585 | 3 | | | | | | SNAR-A14 | 1.00 | 15681 | 3 | | | SNORD111 | 1.00 |
| 15586 | 3 | | | | | | SNAR-A2 | 1.00 | 15682 | 3 | | | SNORD111B | 1.00 |
| 15587 | 3 | | | | | | SNAR-A3 | 1.00 | 15683 | 3 | | | SNORD113-1 | 1.00 |
| 15588 | 3 | | | | | | SNAR-A6 | 1.00 | 15684 | 3 | | | SNORD113-2 | 1.00 |
| 15589 | 3 | | | | | | SNAR-A7 | 1.00 | 15685 | 3 | | | SNORD113-4 | 1.00 |
| 15590 | 3 | | | | | | SNAR-A8 | 1.00 | 15686 | 3 | | | SNORD113-5 | 1.00 |
| 15591 | 3 | | | | | | SNAR-B2 | 1.00 | 15687 | 3 | | | SNORD113-6 | 1.00 |
| 15592 | 3 | | | | | | SNAR-C2 | 1.00 | 15688 | 3 | | | SNORD113-7 | 1.00 |
| 15593 | 3 | | | | | | SNAR-C3 | 1.00 | 15689 | 3 | | | SNORD113-9 | 1.00 |
| 15594 | 3 | | | | | | SNAR-C4 | 1.00 | 15690 | 3 | | | SNORD114-1 | 1.00 |
| 15595 | 3 | | | | | | SNAR-C5 | 1.00 | 15691 | 3 | | | SNORD114-10 | 1.00 |
| 15596 | 3 | | | | | | SNAR-D | 1.00 | 15692 | 3 | | | SNORD114-11 | 1.00 |
| 15597 | 3 | | | | | | SNAR-E | 1.00 | 15693 | 3 | | | SNORD114-12 | 1.00 |
| 15598 | 3 | | | | | | SNAR-F | 1.00 | 15694 | 3 | | | SNORD114-13 | 1.00 |
| 15599 | 3 | | | | | | SNAR-G1 | 1.00 | 15695 | 3 | | | SNORD114-14 | 1.00 |
| 15600 | 3 | | | | | | SNAR-G2 | 1.00 | 15696 | 3 | | | SNORD114-15 | 1.00 |
| 15601 | 3 | | | | | | SNAR-H | 1.00 | 15697 | 3 | | | SNORD114-16 | 1.00 |
| 15602 | 3 | | | | | | SNAR-I | 1.00 | 15698 | 3 | | | SNORD114-17 | 1.00 |
| 15603 | 3 | | | | | | SNCB | 1.00 | 15699 | 3 | | | SNORD114-18 | 1.00 |
| 15604 | 3 | | | | | | SND1-IT1 | 1.00 | 15700 | 3 | | | SNORD114-19 | 1.00 |
| 15605 | 3 | | | | | | SNORA1 | 1.00 | 15701 | 3 | | | SNORD114-2 | 1.00 |
| 15606 | 3 | | | | | | SNORA10 | 1.00 | 15702 | 3 | | | SNORD114-20 | 1.00 |
| 15607 | 3 | | | | | | SNORA11B | 1.00 | 15703 | 3 | | | SNORD114-21 | 1.00 |
| 15608 | 3 | | | | | | SNORA11C | 1.00 | 15704 | 3 | | | SNORD114-22 | 1.00 |
| 15609 | 3 | | | | | | SNORA11D | 1.00 | 15705 | 3 | | | SNORD114-23 | 1.00 |
| 15610 | 3 | | | | | | SNORA11E | 1.00 | 15706 | 3 | | | SNORD114-24 | 1.00 |
| 15611 | 3 | | | | | | SNORA13 | 1.00 | 15707 | 3 | | | SNORD114-25 | 1.00 |
| 15612 | 3 | | | | | | SNORA14A | 1.00 | 15708 | 3 | | | SNORD114-26 | 1.00 |
| 15613 | 3 | | | | | | SNORA15 | 1.00 | 15709 | 3 | | | SNORD114-27 | 1.00 |
| 15614 | 3 | | | | | | SNORA16A | 1.00 | 15710 | 3 | | | SNORD114-28 | 1.00 |
| 15615 | 3 | | | | | | SNORA17 | 1.00 | 15711 | 3 | | | SNORD114-29 | 1.00 |
| 15616 | 3 | | | | | | SNORA18 | 1.00 | 15712 | 3 | | | SNORD114-3 | 1.00 |
| 15617 | 3 | | | | | | SNORA19 | 1.00 | 15713 | 3 | | | SNORD114-30 | 1.00 |
| 15618 | 3 | | | | | | SNORA23 | 1.00 | 15714 | 3 | | | SNORD114-31 | 1.00 |
| 15619 | 3 | | | | | | SNORA25 | 1.00 | 15715 | 3 | | | SNORD114-4 | 1.00 |
| 15620 | 3 | | | | | | SNORA26 | 1.00 | 15716 | 3 | | | SNORD114-5 | 1.00 |
| 15621 | 3 | | | | | | SNORA28 | 1.00 | 15717 | 3 | | | SNORD114-6 | 1.00 |
| 15622 | 3 | | | | | | SNORA2A | 1.00 | 15718 | 3 | | | SNORD114-7 | 1.00 |
| 15623 | 3 | | | | | | SNORA2B | 1.00 | 15719 | 3 | | | SNORD114-8 | 1.00 |
| 15624 | 3 | | | | | | SNORA30 | 1.00 | 15720 | 3 | | | SNORD114-9 | 1.00 |
| 15625 | 3 | | | | | | SNORA32 | 1.00 | 15721 | 3 | | | SNORD115-1 | 1.00 |
| 15626 | 3 | | | | | | SNORA33 | 1.00 | 15722 | 3 | | | SNORD115-10 | 1.00 |
| 15627 | 3 | | | | | | SNORA35 | 1.00 | 15723 | 3 | | | SNORD115-11 | 1.00 |
| 15628 | 3 | | | | | | SNORA36A | 1.00 | 15724 | 3 | | | SNORD115-12 | 1.00 |
| 15629 | 3 | | | | | | SNORA36B | 1.00 | 15725 | 3 | | | SNORD115-13 | 1.00 |
| 15630 | 3 | | | | | | SNORA36C | 1.00 | 15726 | 3 | | | SNORD115-14 | 1.00 |
| 15631 | 3 | | | | | | SNORA38 | 1.00 | 15727 | 3 | | | SNORD115-15 | 1.00 |
| 15632 | 3 | | | | | | SNORA39 | 1.00 | 15728 | 3 | | | SNORD115-16 | 1.00 |
| 15633 | 3 | | | | | | SNORA40 | 1.00 | 15729 | 3 | | | SNORD115-17 | 1.00 |
| 15634 | 3 | | | | | | SNORA42 | 1.00 | 15730 | 3 | | | SNORD115-18 | 1.00 |
| 15635 | 3 | | | | | | SNORA43 | 1.00 | 15731 | 3 | | | SNORD115-19 | 1.00 |
| 15636 | 3 | | | | | | SNORA46 | 1.00 | 15732 | 3 | | | SNORD115-2 | 1.00 |
| 15637 | 3 | | | | | | SNORA49 | 1.00 | 15733 | 3 | | | SNORD115-20 | 1.00 |
| 15638 | 3 | | | | | | SNORA50 | 1.00 | 15734 | 3 | | | SNORD115-21 | 1.00 |
| 15639 | 3 | | | | | | SNORA54 | 1.00 | 15735 | 3 | | | SNORD115-22 | 1.00 |
| 15640 | 3 | | | | | | SNORA55 | 1.00 | 15736 | 3 | | | SNORD115-23 | 1.00 |
| 15641 | 3 | | | | | | SNORA56 | 1.00 | 15737 | 3 | | | SNORD115-24 | 1.00 |
| 15642 | 3 | | | | | | SNORA58 | 1.00 | 15738 | 3 | | | SNORD115-25 | 1.00 |

Fig. 38 - 83

| | | | | | | | | | | | | | | | |
|---|---|---|---|---|---|---|---|---|---|---|---|---|---|---|---|
| 15739 | 3 | | | | | SNORD115-26 | 1.00 | 15835 | 3 | | | | | SNORD36A | 1.00 |
| 15740 | 3 | | | | | SNORD115-27 | 1.00 | 15836 | 3 | | | | | SNORD36B | 1.00 |
| 15741 | 3 | | | | | SNORD115-28 | 1.00 | 15837 | 3 | | | | | SNORD36C | 1.00 |
| 15742 | 3 | | | | | SNORD115-29 | 1.00 | 15838 | 3 | | | | | SNORD37 | 1.00 |
| 15743 | 3 | | | | | SNORD115-3 | 1.00 | 15839 | 3 | | | | | SNORD38A | 1.00 |
| 15744 | 3 | | | | | SNORD115-30 | 1.00 | 15840 | 3 | | | | | SNORD38B | 1.00 |
| 15745 | 3 | | | | | SNORD115-31 | 1.00 | 15841 | 3 | | | | | SNORD41 | 1.00 |
| 15746 | 3 | | | | | SNORD115-32 | 1.00 | 15842 | 3 | | | | | SNORD42A | 1.00 |
| 15747 | 3 | | | | | SNORD115-33 | 1.00 | 15843 | 3 | | | | | SNORD42B | 1.00 |
| 15748 | 3 | | | | | SNORD115-34 | 1.00 | 15844 | 3 | | | | | SNORD43 | 1.00 |
| 15749 | 3 | | | | | SNORD115-35 | 1.00 | 15845 | 3 | | | | | SNORD44 | 1.00 |
| 15750 | 3 | | | | | SNORD115-37 | 1.00 | 15846 | 3 | | | | | SNORD45A | 1.00 |
| 15751 | 3 | | | | | SNORD115-38 | 1.00 | 15847 | 3 | | | | | SNORD45B | 1.00 |
| 15752 | 3 | | | | | SNORD115-39 | 1.00 | 15848 | 3 | | | | | SNORD45C | 1.00 |
| 15753 | 3 | | | | | SNORD115-4 | 1.00 | 15849 | 3 | | | | | SNORD46 | 1.00 |
| 15754 | 3 | | | | | SNORD115-40 | 1.00 | 15850 | 3 | | | | | SNORD47 | 1.00 |
| 15755 | 3 | | | | | SNORD115-41 | 1.00 | 15851 | 3 | | | | | SNORD48 | 1.00 |
| 15756 | 3 | | | | | SNORD115-42 | 1.00 | 15852 | 3 | | | | | SNORD49A | 1.00 |
| 15757 | 3 | | | | | SNORD115-44 | 1.00 | 15853 | 3 | | | | | SNORD49B | 1.00 |
| 15758 | 3 | | | | | SNORD115-45 | 1.00 | 15854 | 3 | | | | | SNORD4A | 1.00 |
| 15759 | 3 | | | | | SNORD115-47 | 1.00 | 15855 | 3 | | | | | SNORD4B | 1.00 |
| 15760 | 3 | | | | | SNORD115-48 | 1.00 | 15856 | 3 | | | | | SNORD5 | 1.00 |
| 15761 | 3 | | | | | SNORD115-5 | 1.00 | 15857 | 3 | | | | | SNORD50A | 1.00 |
| 15762 | 3 | | | | | SNORD115-6 | 1.00 | 15858 | 3 | | | | | SNORD50B | 1.00 |
| 15763 | 3 | | | | | SNORD115-7 | 1.00 | 15859 | 3 | | | | | SNORD51 | 1.00 |
| 15764 | 3 | | | | | SNORD115-8 | 1.00 | 15860 | 3 | | | | | SNORD52 | 1.00 |
| 15765 | 3 | | | | | SNORD115-9 | 1.00 | 15861 | 3 | | | | | SNORD53 | 1.00 |
| 15766 | 3 | | | | | SNORD116-1 | 1.00 | 15862 | 3 | | | | | SNORD54 | 1.00 |
| 15767 | 3 | | | | | SNORD116-10 | 1.00 | 15863 | 3 | | | | | SNORD55 | 1.00 |
| 15768 | 3 | | | | | SNORD116-11 | 1.00 | 15864 | 3 | | | | | SNORD56 | 1.00 |
| 15769 | 3 | | | | | SNORD116-12 | 1.00 | 15865 | 3 | | | | | SNORD56B | 1.00 |
| 15770 | 3 | | | | | SNORD116-13 | 1.00 | 15866 | 3 | | | | | SNORD57 | 1.00 |
| 15771 | 3 | | | | | SNORD116-14 | 1.00 | 15867 | 3 | | | | | SNORD58A | 1.00 |
| 15772 | 3 | | | | | SNORD116-15 | 1.00 | 15868 | 3 | | | | | SNORD58B | 1.00 |
| 15773 | 3 | | | | | SNORD116-16 | 1.00 | 15869 | 3 | | | | | SNORD58C | 1.00 |
| 15774 | 3 | | | | | SNORD116-17 | 1.00 | 15870 | 3 | | | | | SNORD59A | 1.00 |
| 15775 | 3 | | | | | SNORD116-18 | 1.00 | 15871 | 3 | | | | | SNORD59B | 1.00 |
| 15776 | 3 | | | | | SNORD116-2 | 1.00 | 15872 | 3 | | | | | SNORD6 | 1.00 |
| 15777 | 3 | | | | | SNORD116-20 | 1.00 | 15873 | 3 | | | | | SNORD60 | 1.00 |
| 15778 | 3 | | | | | SNORD116-21 | 1.00 | 15874 | 3 | | | | | SNORD61 | 1.00 |
| 15779 | 3 | | | | | SNORD116-22 | 1.00 | 15875 | 3 | | | | | SNORD62A | 1.00 |
| 15780 | 3 | | | | | SNORD116-23 | 1.00 | 15876 | 3 | | | | | SNORD63 | 1.00 |
| 15781 | 3 | | | | | SNORD116-24 | 1.00 | 15877 | 3 | | | | | SNORD64 | 1.00 |
| 15782 | 3 | | | | | SNORD116-25 | 1.00 | 15878 | 3 | | | | | SNORD65 | 1.00 |
| 15783 | 3 | | | | | SNORD116-26 | 1.00 | 15879 | 3 | | | | | SNORD66 | 1.00 |
| 15784 | 3 | | | | | SNORD116-27 | 1.00 | 15880 | 3 | | | | | SNORD67 | 1.00 |
| 15785 | 3 | | | | | SNORD116-28 | 1.00 | 15881 | 3 | | | | | SNORD68 | 1.00 |
| 15786 | 3 | | | | | SNORD116-29 | 1.00 | 15882 | 3 | | | | | SNORD69 | 1.00 |
| 15787 | 3 | | | | | SNORD116-3 | 1.00 | 15883 | 3 | | | | | SNORD7 | 1.00 |
| 15788 | 3 | | | | | SNORD116-4 | 1.00 | 15884 | 3 | | | | | SNORD70 | 1.00 |
| 15789 | 3 | | | | | SNORD116-5 | 1.00 | 15885 | 3 | | | | | SNORD71 | 1.00 |
| 15790 | 3 | | | | | SNORD116-6 | 1.00 | 15886 | 3 | | | | | SNORD72 | 1.00 |
| 15791 | 3 | | | | | SNORD116-7 | 1.00 | 15887 | 3 | | | | | SNORD73A | 1.00 |
| 15792 | 3 | | | | | SNORD116-8 | 1.00 | 15888 | 3 | | | | | SNORD74 | 1.00 |
| 15793 | 3 | | | | | SNORD116-9 | 1.00 | 15889 | 3 | | | | | SNORD75 | 1.00 |
| 15794 | 3 | | | | | SNORD117 | 1.00 | 15890 | 3 | | | | | SNORD76 | 1.00 |
| 15795 | 3 | | | | | SNORD119 | 1.00 | 15891 | 3 | | | | | SNORD77 | 1.00 |
| 15796 | 3 | | | | | SNORD11B | 1.00 | 15892 | 3 | | | | | SNORD78 | 1.00 |
| 15797 | 3 | | | | | SNORD12 | 1.00 | 15893 | 3 | | | | | SNORD79 | 1.00 |
| 15798 | 3 | | | | | SNORD121A | 1.00 | 15894 | 3 | | | | | SNORD8 | 1.00 |
| 15799 | 3 | | | | | SNORD121B | 1.00 | 15895 | 3 | | | | | SNORD80 | 1.00 |
| 15800 | 3 | | | | | SNORD123 | 1.00 | 15896 | 3 | | | | | SNORD81 | 1.00 |
| 15801 | 3 | | | | | SNORD124 | 1.00 | 15897 | 3 | | | | | SNORD82 | 1.00 |
| 15802 | 3 | | | | | SNORD125 | 1.00 | 15898 | 3 | | | | | SNORD83A | 1.00 |
| 15803 | 3 | | | | | SNORD126 | 1.00 | 15899 | 3 | | | | | SNORD83B | 1.00 |
| 15804 | 3 | | | | | SNORD127 | 1.00 | 15900 | 3 | | | | | SNORD84 | 1.00 |
| 15805 | 3 | | | | | SNORD12B | 1.00 | 15901 | 3 | | | | | SNORD85 | 1.00 |
| 15806 | 3 | | | | | SNORD12C | 1.00 | 15902 | 3 | | | | | SNORD86 | 1.00 |
| 15807 | 3 | | | | | SNORD15A | 1.00 | 15903 | 3 | | | | | SNORD87 | 1.00 |
| 15808 | 3 | | | | | SNORD16 | 1.00 | 15904 | 3 | | | | | SNORD88A | 1.00 |
| 15809 | 3 | | | | | SNORD18A | 1.00 | 15905 | 3 | | | | | SNORD88B | 1.00 |
| 15810 | 3 | | | | | SNORD18B | 1.00 | 15906 | 3 | | | | | SNORD88C | 1.00 |
| 15811 | 3 | | | | | SNORD18C | 1.00 | 15907 | 3 | | | | | SNORD9 | 1.00 |
| 15812 | 3 | | | | | SNORD19 | 1.00 | 15908 | 3 | | | | | SNORD90 | 1.00 |
| 15813 | 3 | | | | | SNORD19B | 1.00 | 15909 | 3 | | | | | SNORD91A | 1.00 |
| 15814 | 3 | | | | | SNORD1A | 1.00 | 15910 | 3 | | | | | SNORD91B | 1.00 |
| 15815 | 3 | | | | | SNORD1B | 1.00 | 15911 | 3 | | | | | SNORD92 | 1.00 |
| 15816 | 3 | | | | | SNORD1C | 1.00 | 15912 | 3 | | | | | SNORD93 | 1.00 |
| 15817 | 3 | | | | | SNORD2 | 1.00 | 15913 | 3 | | | | | SNORD94 | 1.00 |
| 15818 | 3 | | | | | SNORD20 | 1.00 | 15914 | 3 | | | | | SNORD95 | 1.00 |
| 15819 | 3 | | | | | SNORD21 | 1.00 | 15915 | 3 | | | | | SNORD96A | 1.00 |
| 15820 | 3 | | | | | SNORD23 | 1.00 | 15916 | 3 | | | | | SNORD96B | 1.00 |
| 15821 | 3 | | | | | SNORD24 | 1.00 | 15917 | 3 | | | | | SNORD98 | 1.00 |
| 15822 | 3 | | | | | SNORD25 | 1.00 | 15918 | 3 | | | | | SNORD99 | 1.00 |
| 15823 | 3 | | | | | SNORD26 | 1.00 | 15919 | 3 | | | | | SNRPD2P2 | 1.00 |
| 15824 | 3 | | | | | SNORD27 | 1.00 | 15920 | 3 | | | | | SNTG1 | 1.00 |
| 15825 | 3 | | | | | SNORD28 | 1.00 | 15921 | 3 | | | | | SNTG2 | 1.00 |
| 15826 | 3 | | | | | SNORD29 | 1.00 | 15922 | 3 | | | | | SNTN | 1.00 |
| 15827 | 3 | | | | | SNORD30 | 1.00 | 15923 | 3 | | | | | SNURF | 1.00 |
| 15828 | 3 | | | | | SNORD31 | 1.00 | 15924 | 3 | | | | | SNX31 | 1.00 |
| 15829 | 3 | | | | | SNORD32A | 1.00 | 15925 | 3 | | | | | SNX32 | 1.00 |
| 15830 | 3 | | | | | SNORD32B | 1.00 | 15926 | 3 | | | | | SOAT2 | 1.00 |
| 15831 | 3 | | | | | SNORD33 | 1.00 | 15927 | 3 | | | | | SOHLH1 | 1.00 |
| 15832 | 3 | | | | | SNORD34 | 1.00 | 15928 | 3 | | | | | SOHLH2 | 1.00 |
| 15833 | 3 | | | | | SNORD35A | 1.00 | 15929 | 3 | | | | | SORCS3 | 1.00 |
| 15834 | 3 | | | | | SNORD35B | 1.00 | 15930 | 3 | | | | | SOST | 1.00 |

Fig. 38 - 84

| | | | | | | | | | | | | | | |
|---|---|---|---|---|---|---|---|---|---|---|---|---|---|---|
| 15931 | 3 | | | | | | SOWAHA | 1.00 | 16027 | 3 | | | | SSTR3 | 1.00 |
| 15932 | 3 | | | | | | SOX1 | 1.00 | 16028 | 3 | | | | SSTR4 | 1.00 |
| 15933 | 3 | | | | | | SOX11 | 1.00 | 16029 | 3 | | | | SSTR5 | 1.00 |
| 15934 | 3 | | | | | | SOX14 | 1.00 | 16030 | 3 | | | | SSX1 | 1.00 |
| 15935 | 3 | | | | | | SOX2-OT | 1.00 | 16031 | 3 | | | | SSX2 | 1.00 |
| 15936 | 3 | | | | | | SOX3 | 1.00 | 16032 | 3 | | | | SSX3 | 1.00 |
| 15937 | 3 | | | | | | SOX30 | 1.00 | 16033 | 3 | | | | SSX4 | 1.00 |
| 15938 | 3 | | | | | | SOX5 | 1.00 | 16034 | 3 | | | | SSX4B | 1.00 |
| 15939 | 3 | | | | | | SP7 | 1.00 | 16035 | 3 | | | | SSX5 | 1.00 |
| 15940 | 3 | | | | | | SPACA1 | 1.00 | 16036 | 3 | | | | SSX6 | 1.00 |
| 15941 | 3 | | | | | | SPACA3 | 1.00 | 16037 | 3 | | | | SSX7 | 1.00 |
| 15942 | 3 | | | | | | SPACA5 | 1.00 | 16038 | 3 | | | | SSX8 | 1.00 |
| 15943 | 3 | | | | | | SPACA5B | 1.00 | 16039 | 3 | | | | ST18 | 1.00 |
| 15944 | 3 | | | | | | SPACA7 | 1.00 | 16040 | 3 | | | | ST20-MTHFS | 1.00 |
| 15945 | 3 | | | | | | SPAG11A | 1.00 | 16041 | 3 | | | | ST6GAL2 | 1.00 |
| 15946 | 3 | | | | | | SPAG11B | 1.00 | 16042 | 3 | | | | ST7-AS2 | 1.00 |
| 15947 | 3 | | | | | | SPAG17 | 1.00 | 16043 | 3 | | | | ST7-OT3 | 1.00 |
| 15948 | 3 | | | | | | SPAG4 | 1.00 | 16044 | 3 | | | | ST7-OT4 | 1.00 |
| 15949 | 3 | | | | | | SPAG6 | 1.00 | 16045 | 3 | | | | ST8SIA2 | 1.00 |
| 15950 | 3 | | | | | | SPAM1 | 1.00 | 16046 | 3 | | | | ST8SIA3 | 1.00 |
| 15951 | 3 | | | | | | SPANXA1 | 1.00 | 16047 | 3 | | | | ST8SIA5 | 1.00 |
| 15952 | 3 | | | | | | SPANXA2 | 1.00 | 16048 | 3 | | | | ST8SIA6 | 1.00 |
| 15953 | 3 | | | | | | SPANXA2-OT1 | 1.00 | 16049 | 3 | | | | STAB2 | 1.00 |
| 15954 | 3 | | | | | | SPANXB2 | 1.00 | 16050 | 3 | | | | STAG3 | 1.00 |
| 15955 | 3 | | | | | | SPANXC | 1.00 | 16051 | 3 | | | | STAP1 | 1.00 |
| 15956 | 3 | | | | | | SPANXD | 1.00 | 16052 | 3 | | | | STARD4 | 1.00 |
| 15957 | 3 | | | | | | SPANXE | 1.00 | 16053 | 3 | | | | STARD6 | 1.00 |
| 15958 | 3 | | | | | | SPANXN1 | 1.00 | 16054 | 3 | | | | STAT4 | 1.00 |
| 15959 | 3 | | | | | | SPANXN2 | 1.00 | 16055 | 3 | | | | STATH | 1.00 |
| 15960 | 3 | | | | | | SPANXN3 | 1.00 | 16056 | 3 | | | | STEAP1B | 1.00 |
| 15961 | 3 | | | | | | SPANXN4 | 1.00 | 16057 | 3 | | | | STH | 1.00 |
| 15962 | 3 | | | | | | SPANXN5 | 1.00 | 16058 | 3 | | | | STK31 | 1.00 |
| 15963 | 3 | | | | | | SPATA12 | 1.00 | 16059 | 3 | | | | STK32A | 1.00 |
| 15964 | 3 | | | | | | SPATA16 | 1.00 | 16060 | 3 | | | | STK33 | 1.00 |
| 15965 | 3 | | | | | | SPATA17 | 1.00 | 16061 | 3 | | | | STL | 1.00 |
| 15966 | 3 | | | | | | SPATA19 | 1.00 | 16062 | 3 | | | | STMN4 | 1.00 |
| 15967 | 3 | | | | | | SPATA21 | 1.00 | 16063 | 3 | | | | STOML3 | 1.00 |
| 15968 | 3 | | | | | | SPATA22 | 1.00 | 16064 | 3 | | | | STON1-GTF2A1L | 1.00 |
| 15969 | 3 | | | | | | SPATA24 | 1.00 | 16065 | 3 | | | | STRA6 | 1.00 |
| 15970 | 3 | | | | | | SPATA3 | 1.00 | 16066 | 3 | | | | STRA8 | 1.00 |
| 15971 | 3 | | | | | | SPATA4 | 1.00 | 16067 | 3 | | | | STRC | 1.00 |
| 15972 | 3 | | | | | | SPATA8 | 1.00 | 16068 | 3 | | | | STX16-NPEPL1 | 1.00 |
| 15973 | 3 | | | | | | SPATA9 | 1.00 | 16069 | 3 | | | | STXBP4 | 1.00 |
| 15974 | 3 | | | | | | SPATC1 | 1.00 | 16070 | 3 | | | | STXBP5L | 1.00 |
| 15975 | 3 | | | | | | SPATS1 | 1.00 | 16071 | 3 | | | | STYK1 | 1.00 |
| 15976 | 3 | | | | | | SPC24 | 1.00 | 16072 | 3 | | | | SUGT1P3 | 1.00 |
| 15977 | 3 | | | | | | SPDYC | 1.00 | 16073 | 3 | | | | SULT1A2 | 1.00 |
| 15978 | 3 | | | | | | SPDYE1 | 1.00 | 16074 | 3 | | | | SULT1B1 | 1.00 |
| 15979 | 3 | | | | | | SPDYE3 | 1.00 | 16075 | 3 | | | | SULT1C2P1 | 1.00 |
| 15980 | 3 | | | | | | SPDYE4 | 1.00 | 16076 | 3 | | | | SULT1C3 | 1.00 |
| 15981 | 3 | | | | | | SPDYE5 | 1.00 | 16077 | 3 | | | | SULT2A1 | 1.00 |
| 15982 | 3 | | | | | | SPDYE7P | 1.00 | 16078 | 3 | | | | SULT6B1 | 1.00 |
| 15983 | 3 | | | | | | SPDYE8P | 1.00 | 16079 | 3 | | | | SUMO1P1 | 1.00 |
| 15984 | 3 | | | | | | SPEF1 | 1.00 | 16080 | 3 | | | | SUN3 | 1.00 |
| 15985 | 3 | | | | | | SPEM1 | 1.00 | 16081 | 3 | | | | SUN5 | 1.00 |
| 15986 | 3 | | | | | | SPERT | 1.00 | 16082 | 3 | | | | SV2C | 1.00 |
| 15987 | 3 | | | | | | SPG20OS | 1.00 | 16083 | 3 | | | | SVOP | 1.00 |
| 15988 | 3 | | | | | | SPHKAP | 1.00 | 16084 | 3 | | | | SVOPL | 1.00 |
| 15989 | 3 | | | | | | SPI8 | 1.00 | 16085 | 3 | | | | SYCE1 | 1.00 |
| 15990 | 3 | | | | | | SPIC | 1.00 | 16086 | 3 | | | | SYCE1L | 1.00 |
| 15991 | 3 | | | | | | SPINK13 | 1.00 | 16087 | 3 | | | | SYCE2 | 1.00 |
| 15992 | 3 | | | | | | SPINK14 | 1.00 | 16088 | 3 | | | | SYCN | 1.00 |
| 15993 | 3 | | | | | | SPINK2 | 1.00 | 16089 | 3 | | | | SYCP1 | 1.00 |
| 15994 | 3 | | | | | | SPINK4 | 1.00 | 16090 | 3 | | | | SYCP2 | 1.00 |
| 15995 | 3 | | | | | | SPINK6 | 1.00 | 16091 | 3 | | | | SYCP2L | 1.00 |
| 15996 | 3 | | | | | | SPINK8 | 1.00 | 16092 | 3 | | | | SYDE2 | 1.00 |
| 15997 | 3 | | | | | | SPINK9 | 1.00 | 16093 | 3 | | | | SYN3 | 1.00 |
| 15998 | 3 | | | | | | SPINLW1 | 1.00 | 16094 | 3 | | | | SYNDIG1 | 1.00 |
| 15999 | 3 | | | | | | SPINLW1-WFDC6 | 1.00 | 16095 | 3 | | | | SYNDIG1L | 1.00 |
| 16000 | 3 | | | | | | SPINT3 | 1.00 | 16096 | 3 | | | | SYNGR3 | 1.00 |
| 16001 | 3 | | | | | | SPINT4 | 1.00 | 16097 | 3 | | | | SYNGR4 | 1.00 |
| 16002 | 3 | | | | | | SPNS3 | 1.00 | 16098 | 3 | | | | SYNJ2BP-COX16 | 1.00 |
| 16003 | 3 | | | | | | SPO11 | 1.00 | 16099 | 3 | | | | SYNPO2L | 1.00 |
| 16004 | 3 | | | | | | SPOCD1 | 1.00 | 16100 | 3 | | | | SYNPR | 1.00 |
| 16005 | 3 | | | | | | SPOCK3 | 1.00 | 16101 | 3 | | | | SYS1-DBNDD2 | 1.00 |
| 16006 | 3 | | | | | | SPP2 | 1.00 | 16102 | 3 | | | | SYT1 | 1.00 |
| 16007 | 3 | | | | | | SPPL2C | 1.00 | 16103 | 3 | | | | SYT10 | 1.00 |
| 16008 | 3 | | | | | | SPRED3 | 1.00 | 16104 | 3 | | | | SYT13 | 1.00 |
| 16009 | 3 | | | | | | SPRNP1 | 1.00 | 16105 | 3 | | | | SYT14 | 1.00 |
| 16010 | 3 | | | | | | SPRR2C | 1.00 | 16106 | 3 | | | | SYT14L | 1.00 |
| 16011 | 3 | | | | | | SPRR3 | 1.00 | 16107 | 3 | | | | SYT16 | 1.00 |
| 16012 | 3 | | | | | | SPRY3 | 1.00 | 16108 | 3 | | | | SYT2 | 1.00 |
| 16013 | 3 | | | | | | SPRYD5 | 1.00 | 16109 | 3 | | | | SYT3 | 1.00 |
| 16014 | 3 | | | | | | SPTA1 | 1.00 | 16110 | 3 | | | | SYT4 | 1.00 |
| 16015 | 3 | | | | | | SPTBN4 | 1.00 | 16111 | 3 | | | | SYT5 | 1.00 |
| 16016 | 3 | | | | | | SPZ1 | 1.00 | 16112 | 3 | | | | SYT6 | 1.00 |
| 16017 | 3 | | | | | | SRCRB4D | 1.00 | 16113 | 3 | | | | SYT9 | 1.00 |
| 16018 | 3 | | | | | | SRD5A2 | 1.00 | 16114 | 3 | | | | SYTL5 | 1.00 |
| 16019 | 3 | | | | | | SRG7 | 1.00 | 16115 | 3 | | | | T | 1.00 |
| 16020 | 3 | | | | | | SRMS | 1.00 | 16116 | 3 | | | | TAAR1 | 1.00 |
| 16021 | 3 | | | | | | SRRM4 | 1.00 | 16117 | 3 | | | | TAAR2 | 1.00 |
| 16022 | 3 | | | | | | SRSF12 | 1.00 | 16118 | 3 | | | | TAAR3 | 1.00 |
| 16023 | 3 | | | | | | SRY | 1.00 | 16119 | 3 | | | | TAAR5 | 1.00 |
| 16024 | 3 | | | | | | SSPO | 1.00 | 16120 | 3 | | | | TAAR6 | 1.00 |
| 16025 | 3 | | | | | | SST | 1.00 | 16121 | 3 | | | | TAAR8 | 1.00 |
| 16026 | 3 | | | | | | SSTR2 | 1.00 | 16122 | 3 | | | | TAAR9 | 1.00 |

Fig. 38 - 85

| | | | | | | | |
|---|---|---|---|---|---|---|---|
| 16123 | 3 | | TAC1 | 1.00 | 16218 | 3 | TEX13A | 1.00 |
| 16124 | 3 | | TAC3 | 1.00 | 16219 | 3 | TEX13B | 1.00 |
| 16125 | 3 | | TAC4 | 1.00 | 16220 | 3 | TEX14 | 1.00 |
| 16126 | 3 | | TACR3 | 1.00 | 16221 | 3 | TEX15 | 1.00 |
| 16127 | 3 | | TAF1A | 1.00 | 16222 | 3 | TEX19 | 1.00 |
| 16128 | 3 | | TAF7L | 1.00 | 16223 | 3 | TEX21P | 1.00 |
| 16129 | 3 | | TAG | 1.00 | 16224 | 3 | TEX22 | 1.00 |
| 16130 | 3 | | tAKR | 1.00 | 16225 | 3 | TEX26 | 1.00 |
| 16131 | 3 | | TAL2 | 1.00 | 16226 | 3 | TEX26-AS1 | 1.00 |
| 16132 | 3 | | TARM1 | 1.00 | 16227 | 3 | TEX28 | 1.00 |
| 16133 | 3 | | TAS1R1 | 1.00 | 16228 | 3 | TEX29 | 1.00 |
| 16134 | 3 | | TAS1R2 | 1.00 | 16229 | 3 | TEX33 | 1.00 |
| 16135 | 3 | | TAS1R3 | 1.00 | 16230 | 3 | TEX34 | 1.00 |
| 16136 | 3 | | TAS2R1 | 1.00 | 16231 | 3 | TEX9 | 1.00 |
| 16137 | 3 | | TAS2R10 | 1.00 | 16232 | 3 | TFAMP1 | 1.00 |
| 16138 | 3 | | TAS2R13 | 1.00 | 16233 | 3 | TFAP2D | 1.00 |
| 16139 | 3 | | TAS2R16 | 1.00 | 16234 | 3 | TFDP3 | 1.00 |
| 16140 | 3 | | TAS2R19 | 1.00 | 16235 | 3 | TFEC | 1.00 |
| 16141 | 3 | | TAS2R3 | 1.00 | 16236 | 3 | TFF1 | 1.00 |
| 16142 | 3 | | TAS2R30 | 1.00 | 16237 | 3 | TFF2 | 1.00 |
| 16143 | 3 | | TAS2R31 | 1.00 | 16238 | 3 | TGIF2-C20ORF24 | 1.00 |
| 16144 | 3 | | TAS2R38 | 1.00 | 16239 | 3 | TGIF2LX | 1.00 |
| 16145 | 3 | | TAS2R39 | 1.00 | 16240 | 3 | TGIF2LY | 1.00 |
| 16146 | 3 | | TAS2R40 | 1.00 | 16241 | 3 | TGM4 | 1.00 |
| 16147 | 3 | | TAS2R41 | 1.00 | 16242 | 3 | TGM6 | 1.00 |
| 16148 | 3 | | TAS2R42 | 1.00 | 16243 | 3 | TGM7 | 1.00 |
| 16149 | 3 | | TAS2R43 | 1.00 | 16244 | 3 | TH | 1.00 |
| 16150 | 3 | | TAS2R46 | 1.00 | 16245 | 3 | THEG | 1.00 |
| 16151 | 3 | | TAS2R50 | 1.00 | 16246 | 3 | THEG5 | 1.00 |
| 16152 | 3 | | TAS2R60 | 1.00 | 16247 | 3 | THEGL | 1.00 |
| 16153 | 3 | | TAS2R7 | 1.00 | 16248 | 3 | THEMIS | 1.00 |
| 16154 | 3 | | TAS2R8 | 1.00 | 16249 | 3 | THPO | 1.00 |
| 16155 | 3 | | TAS2R9 | 1.00 | 16250 | 3 | THSD7A | 1.00 |
| 16156 | 3 | | TBC1D19 | 1.00 | 16251 | 3 | THSD7B | 1.00 |
| 16157 | 3 | | TBC1D21 | 1.00 | 16252 | 3 | TIAM2 | 1.00 |
| 16158 | 3 | | TBC1D26 | 1.00 | 16253 | 3 | TIGD3 | 1.00 |
| 16159 | 3 | | TBC1D28 | 1.00 | 16254 | 3 | TIGD4 | 1.00 |
| 16160 | 3 | | TBC1D29 | 1.00 | 16255 | 3 | TINAG | 1.00 |
| 16161 | 3 | | TBC1D3 | 1.00 | 16256 | 3 | TIPARP-AS1 | 1.00 |
| 16162 | 3 | | TBC1D30 | 1.00 | 16257 | 3 | TISP43 | 1.00 |
| 16163 | 3 | | TBC1D3P1-DHX40P1 | 1.00 | 16258 | 3 | TKTL1 | 1.00 |
| | | | | | 16259 | 3 | TKTL2 | 1.00 |
| 16164 | 3 | | TBC1D3P2 | 1.00 | 16260 | 3 | TLE6 | 1.00 |
| 16165 | 3 | | TBC1D3P5 | 1.00 | 16261 | 3 | TLL2 | 1.00 |
| 16166 | 3 | | TBL1Y | 1.00 | 16262 | 3 | TLR10 | 1.00 |
| 16167 | 3 | | TBPL2 | 1.00 | 16263 | 3 | TLR8-AS1 | 1.00 |
| 16168 | 3 | | TBR1 | 1.00 | 16264 | 3 | TLX1 | 1.00 |
| 16169 | 3 | | TBX10 | 1.00 | 16265 | 3 | TLX1NB | 1.00 |
| 16170 | 3 | | TBX20 | 1.00 | 16266 | 3 | TLX2 | 1.00 |
| 16171 | 3 | | TBX21 | 1.00 | 16267 | 3 | TLX3 | 1.00 |
| 16172 | 3 | | TBX22 | 1.00 | 16268 | 3 | TM4SF19 | 1.00 |
| 16173 | 3 | | TBX4 | 1.00 | 16269 | 3 | TM4SF19-TCTEX1D2 | 1.00 |
| 16174 | 3 | | TCAM1P | 1.00 | | | | |
| 16175 | 3 | | TCEB3B | 1.00 | 16270 | 3 | TM4SF20 | 1.00 |
| 16176 | 3 | | TCEB3C | 1.00 | 16271 | 3 | TM4SF4 | 1.00 |
| 16177 | 3 | | TCEB3CL | 1.00 | 16272 | 3 | TM4SF5 | 1.00 |
| 16178 | 3 | | TCERG1L | 1.00 | 16273 | 3 | TM6SF2 | 1.00 |
| 16179 | 3 | | TCF15 | 1.00 | 16274 | 3 | TM7SF4 | 1.00 |
| 16180 | 3 | | TCF21 | 1.00 | 16275 | 3 | TMC1 | 1.00 |
| 16181 | 3 | | TCF23 | 1.00 | 16276 | 3 | TMC3 | 1.00 |
| 16182 | 3 | | TCF24 | 1.00 | 16277 | 3 | TMC7 | 1.00 |
| 16183 | 3 | | TCHHL1 | 1.00 | 16278 | 3 | TMCO2 | 1.00 |
| 16184 | 3 | | TCL1A | 1.00 | 16279 | 3 | TMCO5A | 1.00 |
| 16185 | 3 | | TCL1B | 1.00 | 16280 | 3 | TMCO5B | 1.00 |
| 16186 | 3 | | TCL6 | 1.00 | 16281 | 3 | TMED11P | 1.00 |
| 16187 | 3 | | TCN1 | 1.00 | 16282 | 3 | TMED7-TICAM2 | 1.00 |
| 16188 | 3 | | TCP10 | 1.00 | 16283 | 3 | TMED8 | 1.00 |
| 16189 | 3 | | TCP10L | 1.00 | 16284 | 3 | TMEFF1 | 1.00 |
| 16190 | 3 | | TCP10L2 | 1.00 | 16285 | 3 | TMEFF2 | 1.00 |
| 16191 | 3 | | TCP11 | 1.00 | 16286 | 3 | TMEM105 | 1.00 |
| 16192 | 3 | | TCTE1 | 1.00 | 16287 | 3 | TMEM110-MUSTN1 | 1.00 |
| 16193 | 3 | | TCTE3 | 1.00 | | | | |
| 16194 | 3 | | TDGF1 | 1.00 | 16288 | 3 | TMEM114 | 1.00 |
| 16195 | 3 | | TDGF1P3 | 1.00 | 16289 | 3 | TMEM130 | 1.00 |
| 16196 | 3 | | TDH | 1.00 | 16290 | 3 | TMEM132D | 1.00 |
| 16197 | 3 | | TDO2 | 1.00 | 16291 | 3 | TMEM145 | 1.00 |
| 16198 | 3 | | TDRD1 | 1.00 | 16292 | 3 | TMEM14E | 1.00 |
| 16199 | 3 | | TDRD12 | 1.00 | 16293 | 3 | TMEM150B | 1.00 |
| 16200 | 3 | | TDRD5 | 1.00 | 16294 | 3 | TMEM151A | 1.00 |
| 16201 | 3 | | TDRD6 | 1.00 | 16295 | 3 | TMEM151B | 1.00 |
| 16202 | 3 | | TDRD9 | 1.00 | 16296 | 3 | TMEM155 | 1.00 |
| 16203 | 3 | | TDRG1 | 1.00 | 16297 | 3 | TMEM156 | 1.00 |
| 16204 | 3 | | TECRL | 1.00 | 16298 | 3 | TMEM163 | 1.00 |
| 16205 | 3 | | TECTA | 1.00 | 16299 | 3 | TMEM169 | 1.00 |
| 16206 | 3 | | TECTB | 1.00 | 16300 | 3 | TMEM174 | 1.00 |
| 16207 | 3 | | TEDDM1 | 1.00 | 16301 | 3 | TMEM179 | 1.00 |
| 16208 | 3 | | TEKT1 | 1.00 | 16302 | 3 | TMEM182 | 1.00 |
| 16209 | 3 | | TEKT2 | 1.00 | 16303 | 3 | TMEM189-UBE2V1 | 1.00 |
| 16210 | 3 | | TEKT4 | 1.00 | | | | |
| 16211 | 3 | | TEKT5 | 1.00 | 16304 | 3 | TMEM190 | 1.00 |
| 16212 | 3 | | TEPP | 1.00 | 16305 | 3 | TMEM191A | 1.00 |
| 16213 | 3 | | TERT | 1.00 | 16306 | 3 | TMEM191B | 1.00 |
| 16214 | 3 | | TET1 | 1.00 | 16307 | 3 | TMEM191C | 1.00 |
| 16215 | 3 | | TEX101 | 1.00 | 16308 | 3 | TMEM196 | 1.00 |
| 16216 | 3 | | TEX11 | 1.00 | 16309 | 3 | TMEM202 | 1.00 |
| 16217 | 3 | | TEX12 | 1.00 | 16310 | 3 | TMEM207 | 1.00 |

Fig. 38 - 86

| | | | | | | | | | | | | | | | |
|---|---|---|---|---|---|---|---|---|---|---|---|---|---|---|---|
| 16311 | 3 | | | | | | TMEM212 | 1.00 | 16407 | 3 | | | | TRIM49L1 | 1.00 |
| 16312 | 3 | | | | | | TMEM215 | 1.00 | 16408 | 3 | | | | TRIM49L2 | 1.00 |
| 16313 | 3 | | | | | | TMEM221 | 1.00 | 16409 | 3 | | | | TRIM50 | 1.00 |
| 16314 | 3 | | | | | | TMEM225 | 1.00 | 16410 | 3 | | | | TRIM53P | 1.00 |
| 16315 | 3 | | | | | | TMEM229A | 1.00 | 16411 | 3 | | | | TRIM54 | 1.00 |
| 16316 | 3 | | | | | | TMEM232 | 1.00 | 16412 | 3 | | | | TRIM58 | 1.00 |
| 16317 | 3 | | | | | | TMEM233 | 1.00 | 16413 | 3 | | | | TRIM60 | 1.00 |
| 16318 | 3 | | | | | | TMEM235 | 1.00 | 16414 | 3 | | | | TRIM61 | 1.00 |
| 16319 | 3 | | | | | | TMEM236 | 1.00 | 16415 | 3 | | | | TRIM63 | 1.00 |
| 16320 | 3 | | | | | | TMEM239 | 1.00 | 16416 | 3 | | | | TRIM64 | 1.00 |
| 16321 | 3 | | | | | | TMEM244 | 1.00 | 16417 | 3 | | | | TRIM64B | 1.00 |
| 16322 | 3 | | | | | | TMEM26 | 1.00 | 16418 | 3 | | | | TRIM64C | 1.00 |
| 16323 | 3 | | | | | | TMEM30C | 1.00 | 16419 | 3 | | | | TRIM67 | 1.00 |
| 16324 | 3 | | | | | | TMEM31 | 1.00 | 16420 | 3 | | | | TRIM69 | 1.00 |
| 16325 | 3 | | | | | | TMEM56-RWDD3 | 1.00 | 16421 | 3 | | | | TRIM6-TRIM34 | 1.00 |
| 16326 | 3 | | | | | | TMEM72 | 1.00 | 16422 | 3 | | | | TRIM71 | 1.00 |
| 16327 | 3 | | | | | | TMEM72-AS1 | 1.00 | 16423 | 3 | | | | TRIM72 | 1.00 |
| 16328 | 3 | | | | | | TMEM74 | 1.00 | 16424 | 3 | | | | TRIM77P | 1.00 |
| 16329 | 3 | | | | | | TMEM82 | 1.00 | 16425 | 3 | | | | TRIML1 | 1.00 |
| 16330 | 3 | | | | | | TMEM89 | 1.00 | 16426 | 3 | | | | TRIML2 | 1.00 |
| 16331 | 3 | | | | | | TMEM8C | 1.00 | 16427 | 3 | | | | TRPA1 | 1.00 |
| 16332 | 3 | | | | | | TMEM92 | 1.00 | 16428 | 3 | | | | TRPC2 | 1.00 |
| 16333 | 3 | | | | | | TMEM95 | 1.00 | 16429 | 3 | | | | TRPC3 | 1.00 |
| 16334 | 3 | | | | | | TMIGD1 | 1.00 | 16430 | 3 | | | | TRPC4 | 1.00 |
| 16335 | 3 | | | | | | TMIGD2 | 1.00 | 16431 | 3 | | | | TRPC5 | 1.00 |
| 16336 | 3 | | | | | | TMOD4 | 1.00 | 16432 | 3 | | | | TRPC7 | 1.00 |
| 16337 | 3 | | | | | | TMPPE | 1.00 | 16433 | 3 | | | | TRPM3 | 1.00 |
| 16338 | 3 | | | | | | TMPRSS11A | 1.00 | 16434 | 3 | | | | TRPM5 | 1.00 |
| 16339 | 3 | | | | | | TMPRSS11B | 1.00 | 16435 | 3 | | | | TRPM6 | 1.00 |
| 16340 | 3 | | | | | | TMPRSS11BNL | 1.00 | 16436 | 3 | | | | TRPM8 | 1.00 |
| 16341 | 3 | | | | | | TMPRSS11D | 1.00 | 16437 | 3 | | | | TRPV5 | 1.00 |
| 16342 | 3 | | | | | | TMPRSS11GP | 1.00 | 16438 | 3 | | | | TRY6 | 1.00 |
| 16343 | 3 | | | | | | TMPRSS12 | 1.00 | 16439 | 3 | | | | TSG1 | 1.00 |
| 16344 | 3 | | | | | | TMPRSS15 | 1.00 | 16440 | 3 | | | | TSGA10 | 1.00 |
| 16345 | 3 | | | | | | TMPRSS7 | 1.00 | 16441 | 3 | | | | TSGA10IP | 1.00 |
| 16346 | 3 | | | | | | TMPRSS9 | 1.00 | 16442 | 3 | | | | TSGA13 | 1.00 |
| 16347 | 3 | | | | | | TMSB15A | 1.00 | 16443 | 3 | | | | TSHB | 1.00 |
| 16348 | 3 | | | | | | TMSB15B | 1.00 | 16444 | 3 | | | | TSHR | 1.00 |
| 16349 | 3 | | | | | | TMSB4Y | 1.00 | 16445 | 3 | | | | TSIX | 1.00 |
| 16350 | 3 | | | | | | TNFAIP8L2-SCNM1 | 1.00 | 16446 | 3 | | | | TSNAX-DISC1 | 1.00 |
| 16351 | 3 | | | | | | TNFRSF13B | 1.00 | 16447 | 3 | | | | TSNAXIP1 | 1.00 |
| 16352 | 3 | | | | | | TNFRSF17 | 1.00 | 16448 | 3 | | | | TSPAN16 | 1.00 |
| 16353 | 3 | | | | | | TNFRSF9 | 1.00 | 16449 | 3 | | | | TSPAN19 | 1.00 |
| 16354 | 3 | | | | | | TNFSF11 | 1.00 | 16450 | 3 | | | | TSPAN32 | 1.00 |
| 16355 | 3 | | | | | | TNFSF12-TNFSF13 | 1.00 | 16451 | 3 | | | | TSPO2 | 1.00 |
| 16356 | 3 | | | | | | TNFSF15 | 1.00 | 16452 | 3 | | | | TSPY1 | 1.00 |
| 16357 | 3 | | | | | | TNFSF18 | 1.00 | 16453 | 3 | | | | TSPY2 | 1.00 |
| 16358 | 3 | | | | | | TNFSF4 | 1.00 | 16454 | 3 | | | | TSPY3 | 1.00 |
| 16359 | 3 | | | | | | TNIP3 | 1.00 | 16455 | 3 | | | | TSPY4 | 1.00 |
| 16360 | 3 | | | | | | TNNI1 | 1.00 | 16456 | 3 | | | | TSPY8 | 1.00 |
| 16361 | 3 | | | | | | TNNI3K | 1.00 | 16457 | 3 | | | | TSPYL6 | 1.00 |
| 16362 | 3 | | | | | | TNP1 | 1.00 | 16458 | 3 | | | | TSSK1B | 1.00 |
| 16363 | 3 | | | | | | TNP2 | 1.00 | 16459 | 3 | | | | TSSK2 | 1.00 |
| 16364 | 3 | | | | | | TNR | 1.00 | 16460 | 3 | | | | TTBK1 | 1.00 |
| 16365 | 3 | | | | | | TOB2P1 | 1.00 | 16461 | 3 | | | | TTBK2 | 1.00 |
| 16366 | 3 | | | | | | TOMM20L | 1.00 | 16462 | 3 | | | | TTC16 | 1.00 |
| 16367 | 3 | | | | | | TOP1P2 | 1.00 | 16463 | 3 | | | | TTC23L | 1.00 |
| 16368 | 3 | | | | | | TP53TG3 | 1.00 | 16464 | 3 | | | | TTC24 | 1.00 |
| 16369 | 3 | | | | | | TP53TG3B | 1.00 | 16465 | 3 | | | | TTC25 | 1.00 |
| 16370 | 3 | | | | | | TP53TG3C | 1.00 | 16466 | 3 | | | | TTC29 | 1.00 |
| 16371 | 3 | | | | | | TP53TG5 | 1.00 | 16467 | 3 | | | | TTC34 | 1.00 |
| 16372 | 3 | | | | | | TPD52L3 | 1.00 | 16468 | 3 | | | | TTC40 | 1.00 |
| 16373 | 3 | | | | | | TPH1 | 1.00 | 16469 | 3 | | | | TTC9B | 1.00 |
| 16374 | 3 | | | | | | TPH2 | 1.00 | 16470 | 3 | | | | TTK | 1.00 |
| 16375 | 3 | | | | | | TPI1P2 | 1.00 | 16471 | 3 | | | | TTLL10 | 1.00 |
| 16376 | 3 | | | | | | TPO | 1.00 | 16472 | 3 | | | | TTLL13 | 1.00 |
| 16377 | 3 | | | | | | TPPP2 | 1.00 | 16473 | 3 | | | | TTLL2 | 1.00 |
| 16378 | 3 | | | | | | TPRX1 | 1.00 | 16474 | 3 | | | | TTLL6 | 1.00 |
| 16379 | 3 | | | | | | TPTE | 1.00 | 16475 | 3 | | | | TTLL7 | 1.00 |
| 16380 | 3 | | | | | | TPTE2 | 1.00 | 16476 | 3 | | | | TTLL9 | 1.00 |
| 16381 | 3 | | | | | | TPTE2P1 | 1.00 | 16477 | 3 | | | | TTN | 1.00 |
| 16382 | 3 | | | | | | TPTE2P3 | 1.00 | 16478 | 3 | | | | TTPA | 1.00 |
| 16383 | 3 | | | | | | TPTE2P6 | 1.00 | 16479 | 3 | | | | TTR | 1.00 |
| 16384 | 3 | | | | | | TRDMT1 | 1.00 | 16480 | 3 | | | | TTTY1 | 1.00 |
| 16385 | 3 | | | | | | TRDN | 1.00 | 16481 | 3 | | | | TTTY10 | 1.00 |
| 16386 | 3 | | | | | | TREH | 1.00 | 16482 | 3 | | | | TTTY11 | 1.00 |
| 16387 | 3 | | | | | | TREM2 | 1.00 | 16483 | 3 | | | | TTTY12 | 1.00 |
| 16388 | 3 | | | | | | TREML1 | 1.00 | 16484 | 3 | | | | TTTY13 | 1.00 |
| 16389 | 3 | | | | | | TREML2 | 1.00 | 16485 | 3 | | | | TTTY14 | 1.00 |
| 16390 | 3 | | | | | | TREML2P1 | 1.00 | 16486 | 3 | | | | TTTY15 | 1.00 |
| 16391 | 3 | | | | | | TREML3 | 1.00 | 16487 | 3 | | | | TTTY16 | 1.00 |
| 16392 | 3 | | | | | | TREML4 | 1.00 | 16488 | 3 | | | | TTTY17A | 1.00 |
| 16393 | 3 | | | | | | TRH | 1.00 | 16489 | 3 | | | | TTTY18 | 1.00 |
| 16394 | 3 | | | | | | TRHDE | 1.00 | 16490 | 3 | | | | TTTY19 | 1.00 |
| 16395 | 3 | | | | | | TRHR | 1.00 | 16491 | 3 | | | | TTTY1B | 1.00 |
| 16396 | 3 | | | | | | TRIM10 | 1.00 | 16492 | 3 | | | | TTTY2 | 1.00 |
| 16397 | 3 | | | | | | TRIM15 | 1.00 | 16493 | 3 | | | | TTTY20 | 1.00 |
| 16398 | 3 | | | | | | TRIM31 | 1.00 | 16494 | 3 | | | | TTTY21 | 1.00 |
| 16399 | 3 | | | | | | TRIM39-RPP21 | 1.00 | 16495 | 3 | | | | TTTY21B | 1.00 |
| 16400 | 3 | | | | | | TRIM40 | 1.00 | 16496 | 3 | | | | TTTY22 | 1.00 |
| 16401 | 3 | | | | | | TRIM42 | 1.00 | 16497 | 3 | | | | TTTY23B | 1.00 |
| 16402 | 3 | | | | | | TRIM43 | 1.00 | 16498 | 3 | | | | TTTY3 | 1.00 |
| 16403 | 3 | | | | | | TRIM43B | 1.00 | 16499 | 3 | | | | TTTY3B | 1.00 |
| 16404 | 3 | | | | | | TRIM46 | 1.00 | 16500 | 3 | | | | TTTY4 | 1.00 |
| 16405 | 3 | | | | | | TRIM48 | 1.00 | 16501 | 3 | | | | TTTY4B | 1.00 |
| 16406 | 3 | | | | | | TRIM49 | 1.00 | 16502 | 3 | | | | TTTY5 | 1.00 |

Fig. 38 - 87

| | | | | | | | |
|---|---|---|---|---|---|---|---|
| 16503 | 3 | | TTTY6 | 1.00 | 16599 | 3 | VCX3B | 1.00 |
| 16504 | 3 | | TTTY6B | 1.00 | 16600 | 3 | VCY | 1.00 |
| 16505 | 3 | | TTTY7 | 1.00 | 16601 | 3 | VCY1B | 1.00 |
| 16506 | 3 | | TTTY7B | 1.00 | 16602 | 3 | VENTXP1 | 1.00 |
| 16507 | 3 | | TTTY8 | 1.00 | 16603 | 3 | VENTXP7 | 1.00 |
| 16508 | 3 | | TTTY8B | 1.00 | 16604 | 3 | VGF | 1.00 |
| 16509 | 3 | | TTTY9B | 1.00 | 16605 | 3 | VGLL1 | 1.00 |
| 16510 | 3 | | TUBA3C | 1.00 | 16606 | 3 | VHLL | 1.00 |
| 16511 | 3 | | TUBA3D | 1.00 | 16607 | 3 | VIL1 | 1.00 |
| 16512 | 3 | | TUBA3E | 1.00 | 16608 | 3 | VIP | 1.00 |
| 16513 | 3 | | TUBB1 | 1.00 | 16609 | 3 | VIPR2 | 1.00 |
| 16514 | 3 | | TUBB8 | 1.00 | 16610 | 3 | VN1R10P | 1.00 |
| 16515 | 3 | | TULP1 | 1.00 | 16611 | 3 | VN1R2 | 1.00 |
| 16516 | 3 | | TULP2 | 1.00 | 16612 | 3 | VN1R4 | 1.00 |
| 16517 | 3 | | TXK | 1.00 | 16613 | 3 | VN1R5 | 1.00 |
| 16518 | 3 | | TXLNG2P | 1.00 | 16614 | 3 | VNN3 | 1.00 |
| 16519 | 3 | | TXNDC2 | 1.00 | 16615 | 3 | VPREB1 | 1.00 |
| 16520 | 3 | | TXNDC3 | 1.00 | 16616 | 3 | VPREB3 | 1.00 |
| 16521 | 3 | | TXNDC8 | 1.00 | 16617 | 3 | VRTN | 1.00 |
| 16522 | 3 | | TXNRD3NB | 1.00 | 16618 | 3 | VSIG1 | 1.00 |
| 16523 | 3 | | U8AC2-AS1 | 1.00 | 16619 | 3 | VSTM1 | 1.00 |
| 16524 | 3 | | UBE2DNL | 1.00 | 16620 | 3 | VSTM2A | 1.00 |
| 16525 | 3 | | UBE2F-SCLY | 1.00 | 16621 | 3 | VSTM2B | 1.00 |
| 16526 | 3 | | UBE2Q2P1 | 1.00 | 16622 | 3 | VSTM5 | 1.00 |
| 16527 | 3 | | UBE2Q2P3 | 1.00 | 16623 | 3 | VSX1 | 1.00 |
| 16528 | 3 | | UBE2U | 1.00 | 16624 | 3 | VSX2 | 1.00 |
| 16529 | 3 | | UBL4B | 1.00 | 16625 | 3 | VTN | 1.00 |
| 16530 | 3 | | UBQLN3 | 1.00 | 16626 | 3 | VTRNA1-1 | 1.00 |
| 16531 | 3 | | UBTFL1 | 1.00 | 16627 | 3 | VTRNA1-2 | 1.00 |
| 16532 | 3 | | UCA1 | 1.00 | 16628 | 3 | VTRNA1-3 | 1.00 |
| 16533 | 3 | | UCMA | 1.00 | 16629 | 3 | VTRNA2-1 | 1.00 |
| 16534 | 3 | | UCN3 | 1.00 | 16630 | 3 | VWA3A | 1.00 |
| 16535 | 3 | | UCP1 | 1.00 | 16631 | 3 | VWA3B | 1.00 |
| 16536 | 3 | | UG0898H09 | 1.00 | 16632 | 3 | VWA5B1 | 1.00 |
| 16537 | 3 | | UGGT2 | 1.00 | 16633 | 3 | VWA5B2 | 1.00 |
| 16538 | 3 | | UGT1A1 | 1.00 | 16634 | 3 | VWC2L | 1.00 |
| 16539 | 3 | | UGT1A10 | 1.00 | 16635 | 3 | VWCE | 1.00 |
| 16540 | 3 | | UGT1A3 | 1.00 | 16636 | 3 | VWDE | 1.00 |
| 16541 | 3 | | UGT1A4 | 1.00 | 16637 | 3 | WBP2NL | 1.00 |
| 16542 | 3 | | UGT1A5 | 1.00 | 16638 | 3 | WBSCR28 | 1.00 |
| 16543 | 3 | | UGT1A7 | 1.00 | 16639 | 3 | WDHD1 | 1.00 |
| 16544 | 3 | | UGT1A8 | 1.00 | 16640 | 3 | WDR16 | 1.00 |
| 16545 | 3 | | UGT1A9 | 1.00 | 16641 | 3 | WDR17 | 1.00 |
| 16546 | 3 | | UGT2A2 | 1.00 | 16642 | 3 | WDR38 | 1.00 |
| 16547 | 3 | | UGT2A3 | 1.00 | 16643 | 3 | WDR49 | 1.00 |
| 16548 | 3 | | UGT2B10 | 1.00 | 16644 | 3 | WDR63 | 1.00 |
| 16549 | 3 | | UGT2B11 | 1.00 | 16645 | 3 | WDR64 | 1.00 |
| 16550 | 3 | | UGT2B15 | 1.00 | 16646 | 3 | WDR65 | 1.00 |
| 16551 | 3 | | UGT2B17 | 1.00 | 16647 | 3 | WDR66 | 1.00 |
| 16552 | 3 | | UGT2B28 | 1.00 | 16648 | 3 | WDR67 | 1.00 |
| 16553 | 3 | | UGT2B4 | 1.00 | 16649 | 3 | WDR69 | 1.00 |
| 16554 | 3 | | UGT2B7 | 1.00 | 16650 | 3 | WDR78 | 1.00 |
| 16555 | 3 | | UGT3A1 | 1.00 | 16651 | 3 | WDR87 | 1.00 |
| 16556 | 3 | | ULBP1 | 1.00 | 16652 | 3 | WDR88 | 1.00 |
| 16557 | 3 | | ULBP2 | 1.00 | 16653 | 3 | WDR93 | 1.00 |
| 16558 | 3 | | ULBP3 | 1.00 | 16654 | 3 | WDR96 | 1.00 |
| 16559 | 3 | | UMOD | 1.00 | 16655 | 3 | WEE2 | 1.00 |
| 16560 | 3 | | UMODL1 | 1.00 | 16656 | 3 | WFDC10A | 1.00 |
| 16561 | 3 | | UNC13A | 1.00 | 16657 | 3 | WFDC11 | 1.00 |
| 16562 | 3 | | UNC13C | 1.00 | 16658 | 3 | WFDC13 | 1.00 |
| 16563 | 3 | | UNC45B | 1.00 | 16659 | 3 | WFDC6 | 1.00 |
| 16564 | 3 | | UNC5A | 1.00 | 16660 | 3 | WFDC8 | 1.00 |
| 16565 | 3 | | UNC5C | 1.00 | 16661 | 3 | WFDC9 | 1.00 |
| 16566 | 3 | | UNC5D | 1.00 | 16662 | 3 | WNK3 | 1.00 |
| 16567 | 3 | | UNC79 | 1.00 | 16663 | 3 | WNT1 | 1.00 |
| 16568 | 3 | | UNC80 | 1.00 | 16664 | 3 | WNT8A | 1.00 |
| 16569 | 3 | | UNCX | 1.00 | 16665 | 3 | WNT8B | 1.00 |
| 16570 | 3 | | UNQ6494 | 1.00 | 16666 | 3 | WNT9B | 1.00 |
| 16571 | 3 | | UNQ6975 | 1.00 | 16667 | 3 | WT1 | 1.00 |
| 16572 | 3 | | UPK2 | 1.00 | 16668 | 3 | WT1-AS | 1.00 |
| 16573 | 3 | | UPK3A | 1.00 | 16669 | 3 | WWTR1-AS1 | 1.00 |
| 16574 | 3 | | UPP2 | 1.00 | 16670 | 3 | XAGE1A | 1.00 |
| 16575 | 3 | | URGCP-MRPS24 | 1.00 | 16671 | 3 | XAGE1C | 1.00 |
| 16576 | 3 | | UROC1 | 1.00 | 16672 | 3 | XAGE1E | 1.00 |
| 16577 | 3 | | USH1C | 1.00 | 16673 | 3 | XAGE2 | 1.00 |
| 16578 | 3 | | USH2A | 1.00 | 16674 | 3 | XAGE2B | 1.00 |
| 16579 | 3 | | USP17 | 1.00 | 16675 | 3 | XAGE3 | 1.00 |
| 16580 | 3 | | USP17L2 | 1.00 | 16676 | 3 | XAGE5 | 1.00 |
| 16581 | 3 | | USP17L6P | 1.00 | 16677 | 3 | XCL1 | 1.00 |
| 16582 | 3 | | USP26 | 1.00 | 16678 | 3 | XCL2 | 1.00 |
| 16583 | 3 | | USP29 | 1.00 | 16679 | 3 | XDH | 1.00 |
| 16584 | 3 | | USP44 | 1.00 | 16680 | 3 | XIRP1 | 1.00 |
| 16585 | 3 | | USP49 | 1.00 | 16681 | 3 | XIRP2 | 1.00 |
| 16586 | 3 | | USP50 | 1.00 | 16682 | 3 | XK | 1.00 |
| 16587 | 3 | | USP6 | 1.00 | 16683 | 3 | XKR3 | 1.00 |
| 16588 | 3 | | USP9Y | 1.00 | 16684 | 3 | XKR4 | 1.00 |
| 16589 | 3 | | UTF1 | 1.00 | 16685 | 3 | XKR5 | 1.00 |
| 16590 | 3 | | UTS2 | 1.00 | 16686 | 3 | XKR6 | 1.00 |
| 16591 | 3 | | UTS2D | 1.00 | 16687 | 3 | XKR7 | 1.00 |
| 16592 | 3 | | UTS2R | 1.00 | 16688 | 3 | XKR9 | 1.00 |
| 16593 | 3 | | UTY | 1.00 | 16689 | 3 | XKRY | 1.00 |
| 16594 | 3 | | VAT1L | 1.00 | 16690 | 3 | XKRY2 | 1.00 |
| 16595 | 3 | | VAX1 | 1.00 | 16691 | 3 | YIPF7 | 1.00 |
| 16596 | 3 | | VCX | 1.00 | 16692 | 3 | YSK4 | 1.00 |
| 16597 | 3 | | VCX2 | 1.00 | 16693 | 3 | ZACN | 1.00 |
| 16598 | 3 | | VCX3A | 1.00 | 16694 | 3 | ZAN | 1.00 |

Fig. 38 - 88

| | | | | | | | |
|---|---|---|---|---|---|---|---|
| 16695 | 3 | | | | | ZAR1 | 1.00 |
| 16696 | 3 | | | | | ZAR1L | 1.00 |
| 16697 | 3 | | | | | ZB8X | 1.00 |
| 16698 | 3 | | | | | ZBED6 | 1.00 |
| 16699 | 3 | | | | | ZBTB20-AS1 | 1.00 |
| 16700 | 3 | | | | | ZBTB32 | 1.00 |
| 16701 | 3 | | | | | ZBTB37 | 1.00 |
| 16702 | 3 | | | | | ZBTB8B | 1.00 |
| 16703 | 3 | | | | | ZC2HC1B | 1.00 |
| 16704 | 3 | | | | | ZC3H12B | 1.00 |
| 16705 | 3 | | | | | ZCCHC12 | 1.00 |
| 16706 | 3 | | | | | ZCCHC13 | 1.00 |
| 16707 | 3 | | | | | ZCCHC16 | 1.00 |
| 16708 | 3 | | | | | ZCCHC18 | 1.00 |
| 16709 | 3 | | | | | ZCCHC5 | 1.00 |
| 16710 | 3 | | | | | ZCWPW2 | 1.00 |
| 16711 | 3 | | | | | ZDHHC19 | 1.00 |
| 16712 | 3 | | | | | ZDHHC22 | 1.00 |
| 16713 | 3 | | | | | ZEB2-AS1 | 1.00 |
| 16714 | 3 | | | | | ZFAT-AS1 | 1.00 |
| 16715 | 3 | | | | | ZFHX2 | 1.00 |
| 16716 | 3 | | | | | ZFHX4 | 1.00 |
| 16717 | 3 | | | | | ZFP42 | 1.00 |
| 16718 | 3 | | | | | ZFP91-CNTF | 1.00 |
| 16719 | 3 | | | | | ZFP92 | 1.00 |
| 16720 | 3 | | | | | ZFR2 | 1.00 |
| 16721 | 3 | | | | | ZFY | 1.00 |
| 16722 | 3 | | | | | ZG16 | 1.00 |
| 16723 | 3 | | | | | ZIC1 | 1.00 |
| 16724 | 3 | | | | | ZIC2 | 1.00 |
| 16725 | 3 | | | | | ZIC3 | 1.00 |
| 16726 | 3 | | | | | ZIC4 | 1.00 |
| 16727 | 3 | | | | | ZIC5 | 1.00 |
| 16728 | 3 | | | | | ZIM2 | 1.00 |
| 16729 | 3 | | | | | ZIM3 | 1.00 |
| 16730 | 3 | | | | | ZMAT4 | 1.00 |
| 16731 | 3 | | | | | ZMYND10 | 1.00 |
| 16732 | 3 | | | | | ZMYND12 | 1.00 |
| 16733 | 3 | | | | | ZNF114 | 1.00 |
| 16734 | 3 | | | | | ZNF154 | 1.00 |
| 16735 | 3 | | | | | ZNF157 | 1.00 |
| 16736 | 3 | | | | | ZNF208 | 1.00 |
| 16737 | 3 | | | | | ZNF214 | 1.00 |
| 16738 | 3 | | | | | ZNF215 | 1.00 |
| 16739 | 3 | | | | | ZNF221 | 1.00 |
| 16740 | 3 | | | | | ZNF233 | 1.00 |
| 16741 | 3 | | | | | ZNF257 | 1.00 |
| 16742 | 3 | | | | | ZNF280A | 1.00 |
| 16743 | 3 | | | | | ZNF280B | 1.00 |
| 16744 | 3 | | | | | ZNF295-AS1 | 1.00 |
| 16745 | 3 | | | | | ZNF32-AS3 | 1.00 |
| 16746 | 3 | | | | | ZNF354C | 1.00 |
| 16747 | 3 | | | | | ZNF365 | 1.00 |
| 16748 | 3 | | | | | ZNF382 | 1.00 |
| 16749 | 3 | | | | | ZNF396 | 1.00 |
| 16750 | 3 | | | | | ZNF442 | 1.00 |
| 16751 | 3 | | | | | ZNF454 | 1.00 |
| 16752 | 3 | | | | | ZNF460 | 1.00 |
| 16753 | 3 | | | | | ZNF474 | 1.00 |
| 16754 | 3 | | | | | ZNF479 | 1.00 |
| 16755 | 3 | | | | | ZNF483 | 1.00 |
| 16756 | 3 | | | | | ZNF492 | 1.00 |
| 16757 | 3 | | | | | ZNF534 | 1.00 |
| 16758 | 3 | | | | | ZNF536 | 1.00 |
| 16759 | 3 | | | | | ZNF541 | 1.00 |
| 16760 | 3 | | | | | ZNF555 | 1.00 |
| 16761 | 3 | | | | | ZNF556 | 1.00 |
| 16762 | 3 | | | | | ZNF559-ZNF177 | 1.00 |
| 16763 | 3 | | | | | ZNF560 | 1.00 |
| 16764 | 3 | | | | | ZNF572 | 1.00 |
| 16765 | 3 | | | | | ZNF573 | 1.00 |
| 16766 | 3 | | | | | ZNF578 | 1.00 |
| 16767 | 3 | | | | | ZNF625-ZNF20 | 1.00 |
| 16768 | 3 | | | | | ZNF643 | 1.00 |
| 16769 | 3 | | | | | ZNF645 | 1.00 |
| 16770 | 3 | | | | | ZNF648 | 1.00 |
| 16771 | 3 | | | | | ZNF660 | 1.00 |
| 16772 | 3 | | | | | ZNF663 | 1.00 |
| 16773 | 3 | | | | | ZNF664-FAM101A | 1.00 |
| 16774 | 3 | | | | | ZNF665 | 1.00 |
| 16775 | 3 | | | | | ZNF670-ZNF695 | 1.00 |
| 16776 | 3 | | | | | ZNF676 | 1.00 |
| 16777 | 3 | | | | | ZNF677 | 1.00 |
| 16778 | 3 | | | | | ZNF678 | 1.00 |
| 16779 | 3 | | | | | ZNF679 | 1.00 |
| 16780 | 3 | | | | | ZNF695 | 1.00 |
| 16781 | 3 | | | | | ZNF699 | 1.00 |
| 16782 | 3 | | | | | ZNF705A | 1.00 |
| 16783 | 3 | | | | | ZNF705D | 1.00 |
| 16784 | 3 | | | | | ZNF705G | 1.00 |
| 16785 | 3 | | | | | ZNF716 | 1.00 |
| 16786 | 3 | | | | | ZNF717 | 1.00 |
| 16787 | 3 | | | | | ZNF718 | 1.00 |
| 16788 | 3 | | | | | ZNF724P | 1.00 |
| 16789 | 3 | | | | | ZNF726 | 1.00 |
| 16790 | 3 | | | | | ZNF727 | 1.00 |
| 16791 | 3 | | | | | ZNF729 | 1.00 |
| 16792 | 3 | | | | | ZNF732 | 1.00 |
| 16793 | 3 | | | | | ZNF735 | 1.00 |
| 16794 | 3 | | | | | ZNF736 | 1.00 |
| 16795 | 3 | | | | | ZNF781 | 1.00 |
| 16796 | 3 | | | | | ZNF80 | 1.00 |
| 16797 | 3 | | | | | ZNF804A | 1.00 |
| 16798 | 3 | | | | | ZNF804B | 1.00 |
| 16799 | 3 | | | | | ZNF81 | 1.00 |
| 16800 | 3 | | | | | ZNF812 | 1.00 |
| 16801 | 3 | | | | | ZNF816-ZNF321P | 1.00 |
| 16802 | 3 | | | | | ZNF826P | 1.00 |
| 16803 | 3 | | | | | ZNF831 | 1.00 |
| 16804 | 3 | | | | | ZNF843 | 1.00 |
| 16805 | 3 | | | | | ZNF847P | 1.00 |
| 16806 | 3 | | | | | ZNF876P | 1.00 |
| 16807 | 3 | | | | | ZNF878 | 1.00 |
| 16808 | 3 | | | | | ZNF890P | 1.00 |
| 16809 | 3 | | | | | ZNF90 | 1.00 |
| 16810 | 3 | | | | | ZNF98 | 1.00 |
| 16811 | 3 | | | | | ZNF99 | 1.00 |
| 16812 | 3 | | | | | ZNRD1-AS1 | 1.00 |
| 16813 | 3 | | | | | ZNRF2P1 | 1.00 |
| 16814 | 3 | | | | | ZNRF2P2 | 1.00 |
| 16815 | 3 | | | | | ZNRF4 | 1.00 |
| 16816 | 3 | | | | | ZP2 | 1.00 |
| 16817 | 3 | | | | | ZP4 | 1.00 |
| 16818 | 3 | | | | | ZPBP | 1.00 |
| 16819 | 3 | | | | | ZPBP2 | 1.00 |
| 16820 | 3 | | | | | ZPLD1 | 1.00 |
| 16821 | 3 | | | | | ZRANB2-AS2 | 1.00 |
| 16822 | 3 | | | | | ZRANB3 | 1.00 |
| 16823 | 3 | | | | | ZSCAN1 | 1.00 |
| 16824 | 3 | | | | | ZSCAN10 | 1.00 |
| 16825 | 3 | | | | | ZSCAN12P1 | 1.00 |
| 16826 | 3 | | | | | ZSCAN23 | 1.00 |
| 16827 | 3 | | | | | ZSCAN4 | 1.00 |
| 16828 | 3 | | | | | ZSCAN5B | 1.00 |
| 16829 | 3 | | | | | ZSWIM2 | 1.00 |
| 16830 | 3 | | | | | ZYG11A | 1.00 |

Fig. 39 - 1

| Line No. | Group No. | | | | | Sub-Groups | Gene Name | Lung cancer |
|---|---|---|---|---|---|---|---|---|
| 1 | 3 | 4 | 5 | 6 | 7 | VII-2 | AGSK1 | 0.15 |
| 2 | 3 | 4 | 5 | 6 | 7 | VII-2 | CD70 | 0.16 |
| 3 | 3 | 4 | 5 | 6 | 7 | VII-2 | CLDN11 | 0.19 |
| 4 | 3 | 4 | 5 | 6 | 7 | VII-2 | CRIP1 | 0.19 |
| 5 | 3 | 4 | 5 | 6 | 7 | VII-2 | CTXN1 | 0.18 |
| 6 | 3 | 4 | 5 | 6 | 7 | VII-2 | CYP2E1 | 0.15 |
| 7 | 3 | 4 | 5 | 6 | 7 | VII-2 | ELN | 0.19 |
| 8 | 3 | 4 | 5 | 6 | 7 | VII-2 | GALNTL1 | 0.20 |
| 9 | 3 | 4 | 5 | 6 | 7 | VII-2 | KRT6C | 0.15 |
| 10 | 3 | 4 | 5 | 6 | 7 | VII-2 | LOC255130 | 0.16 |
| 11 | 3 | 4 | 5 | 6 | 7 | VII-2 | LOC729799 | 0.19 |
| 12 | 3 | 4 | 5 | 6 | 7 | VII-2 | MASP1 | 0.16 |
| 13 | 3 | 4 | 5 | 6 | 7 | VII-2 | NTN1 | 0.19 |
| 14 | 3 | 4 | 5 | 6 | 7 | VII-2 | PCDHGB7 | 0.20 |
| 15 | 3 | 4 | 5 | 6 | 7 | VII-2 | PRG4 | 0.16 |
| 16 | 3 | 4 | 5 | 6 | 7 | VII-2 | RPL21 | 0.06 |
| 17 | 3 | 4 | 5 | 6 | 7 | VII-2 | RPL9 | 0.11 |
| 18 | 3 | 4 | 5 | 6 | 7 | VII-2 | TNXA | 0.19 |
| 19 | 3 | 4 | 5 | 6 | 7 | VII-2 | TPPP | 0.13 |
| 20 | 3 | 4 | 5 | 6 | 7 | VII-2 | WASH5P | 0.17 |
| 21 | 3 | 4 | 5 | 6 | 7 | VII-2 | ZNF423 | 0.20 |
| 22 | 3 | 4 | 5 | 6 | 7 | VII-1 | AKR1B10 | 7.70 |
| 23 | 3 | 4 | 5 | 6 | 7 | VII-1 | ANKRD12 | 5.03 |
| 24 | 3 | 4 | 5 | 6 | 7 | VII-1 | DCD | 11.06 |
| 25 | 3 | 4 | 5 | 6 | 7 | VII-1 | DDX3Y | 11.00 |
| 26 | 3 | 4 | 5 | 6 | 7 | VII-1 | EIF1AY | 8.88 |
| 27 | 3 | 4 | 5 | 6 | 7 | VII-1 | FCGR3B | 14.66 |
| 28 | 3 | 4 | 5 | 6 | 7 | VII-1 | FPR1 | 8.78 |
| 29 | 3 | 4 | 5 | 6 | 7 | VII-1 | HBA2 | 57.10 |
| 30 | 3 | 4 | 5 | 6 | 7 | VII-1 | HIST1H4B | 5.08 |
| 31 | 3 | 4 | 5 | 6 | 7 | VII-1 | HIST1H4C | 13.92 |
| 32 | 3 | 4 | 5 | 6 | 7 | VII-1 | HIST1H4J | 9.70 |
| 33 | 3 | 4 | 5 | 6 | 7 | VII-1 | HIST1H4K | 9.65 |
| 34 | 3 | 4 | 5 | 6 | 7 | VII-1 | HLA-DQA1 | 18.29 |
| 35 | 3 | 4 | 5 | 6 | 7 | VII-1 | INHBA | 9.40 |
| 36 | 3 | 4 | 5 | 6 | 7 | VII-1 | KCNJ18 | 5.51 |
| 37 | 3 | 4 | 5 | 6 | 7 | VII-1 | KDM5D | 7.88 |
| 38 | 3 | 4 | 5 | 6 | 7 | VII-1 | KTN1 | 7.03 |
| 39 | 3 | 4 | 5 | 6 | 7 | VII-1 | LINC00260 | 8.80 |
| 40 | 3 | 4 | 5 | 6 | 7 | VII-1 | LOC100216546 | 7.52 |
| 41 | 3 | 4 | 5 | 6 | 7 | VII-1 | LOC286437 | 12.22 |
| 42 | 3 | 4 | 5 | 6 | 7 | VII-1 | LOC728640 | 5.17 |
| 43 | 3 | 4 | 5 | 6 | 7 | VII-1 | MALAT1 | 13.95 |
| 44 | 3 | 4 | 5 | 6 | 7 | VII-1 | MIR1184-1 | 51.64 |
| 45 | 3 | 4 | 5 | 6 | 7 | VII-1 | MIR1247 | 6.09 |
| 46 | 3 | 4 | 5 | 6 | 7 | VII-1 | MIR3648 | 5.81 |
| 47 | 3 | 4 | 5 | 6 | 7 | VII-1 | NCRNA00185 | 6.42 |
| 48 | 3 | 4 | 5 | 6 | 7 | VII-1 | PRKY | 7.67 |
| 49 | 3 | 4 | 5 | 6 | 7 | VII-1 | RPL21P44 | 8.92 |
| 50 | 3 | 4 | 5 | 6 | 7 | VII-1 | RPPH1 | 104.50 |
| 51 | 3 | 4 | 5 | 6 | 7 | VII-1 | RPS15AP10 | 21.00 |
| 52 | 3 | 4 | 5 | 6 | 7 | VII-1 | RPS4Y1 | 135.38 |
| 53 | 3 | 4 | 5 | 6 | 7 | VII-1 | SCARNA4 | 16.91 |
| 54 | 3 | 4 | 5 | 6 | 7 | VII-1 | SCGB2A1 | 11.00 |
| 55 | 3 | 4 | 5 | 6 | 7 | VII-1 | SFTPA1 | 21.17 |
| 56 | 3 | 4 | 5 | 6 | 7 | VII-1 | SFTPA2 | 29.42 |
| 57 | 3 | 4 | 5 | 6 | 7 | VII-1 | SFTPB | 6.53 |
| 58 | 3 | 4 | 5 | 6 | 7 | VII-1 | SFTPC | 7.37 |
| 59 | 3 | 4 | 5 | 6 | 7 | VII-1 | SMA4 | 5.49 |
| 60 | 3 | 4 | 5 | 6 | 7 | VII-1 | SNORA31 | 16.08 |
| 61 | 3 | 4 | 5 | 6 | 7 | VII-1 | SNORA41 | 7.29 |
| 62 | 3 | 4 | 5 | 6 | 7 | VII-1 | SNORA42 | 6.65 |
| 63 | 3 | 4 | 5 | 6 | 7 | VII-1 | SNORA77 | 11.00 |
| 64 | 3 | 4 | 5 | 6 | 7 | VII-1 | SNORD94 | 5.83 |
| 65 | 3 | 4 | 5 | 6 | 7 | VII-1 | TXLNG2P | 7.48 |
| 66 | 3 | 4 | 5 | 6 | 7 | VII-1 | ZBTB20 | 11.00 |
| 67 | 3 | 4 | 5 | 6 | | VI-2 | A4GALT | 0.37 |
| 68 | 3 | 4 | 5 | 6 | | VI-2 | ABCA2 | 0.45 |
| 69 | 3 | 4 | 5 | 6 | | VI-2 | ABCA7 | 0.38 |
| 70 | 3 | 4 | 5 | 6 | | VI-2 | ABCB6 | 0.48 |
| 71 | 3 | 4 | 5 | 6 | | VI-2 | ABCC10 | 0.43 |
| 72 | 3 | 4 | 5 | 6 | | VI-2 | ABCC3 | 0.36 |
| 73 | 3 | 4 | 5 | 6 | | VI-2 | ABL1 | 0.36 |
| 74 | 3 | 4 | 5 | 6 | | VI-2 | ABR | 0.44 |
| 75 | 3 | 4 | 5 | 6 | | VI-2 | ACTA1 | 0.29 |
| 76 | 3 | 4 | 5 | 6 | | VI-2 | ACTB | 0.44 |
| 77 | 3 | 4 | 5 | 6 | | VI-2 | ACTC1 | 0.30 |
| 78 | 3 | 4 | 5 | 6 | | VI-2 | ACVRL1 | 0.44 |
| 79 | 3 | 4 | 5 | 6 | | VI-2 | ADAM8 | 0.41 |
| 80 | 3 | 4 | 5 | 6 | | VI-2 | ADAMTS10 | 0.34 |
| 81 | 3 | 4 | 5 | 6 | | VI-2 | ADAMTS2 | 0.28 |
| 82 | 3 | 4 | 5 | 6 | | VI-2 | ADAMTS8 | 0.44 |
| 83 | 3 | 4 | 5 | 6 | | VI-2 | ADAMTSL4 | 0.47 |
| 84 | 3 | 4 | 5 | 6 | | VI-2 | ADCY3 | 0.31 |
| 85 | 3 | 4 | 5 | 6 | | VI-2 | ADCY9 | 0.37 |
| 86 | 3 | 4 | 5 | 6 | | VI-2 | ADCYAP1R1 | 0.43 |
| 87 | 3 | 4 | 5 | 6 | | VI-2 | ADRA2A | 0.35 |
| 88 | 3 | 4 | 5 | 6 | | VI-2 | AEBP1 | 0.37 |
| 89 | 3 | 4 | 5 | 6 | | VI-2 | AGAP1 | 0.35 |
| 90 | 3 | 4 | 5 | 6 | | VI-2 | AGAP3 | 0.50 |
| 91 | 3 | 4 | 5 | 6 | | VI-2 | AGPAT6 | 0.48 |
| 92 | 3 | 4 | 5 | 6 | | VI-2 | AHDC1 | 0.35 |
| 93 | 3 | 4 | 5 | 6 | | VI-2 | AHR | 0.42 |
| 94 | 3 | 4 | 5 | 6 | | VI-2 | AKAP13 | 0.50 |
| 95 | 3 | 4 | 5 | 6 | | VI-2 | AKNA | 0.47 |
| 96 | 3 | 4 | 5 | 6 | | VI-2 | ALX3 | 0.48 |
| 97 | 3 | 4 | 5 | 6 | | VI-2 | AMIGO1 | 0.21 |
| 98 | 3 | 4 | 5 | 6 | | VI-2 | ANGPTL1 | 0.43 |
| 99 | 3 | 4 | 5 | 6 | | VI-2 | ANGPTL2 | 0.35 |
| 100 | 3 | 4 | 5 | 6 | | VI-2 | ANKMY1 | 0.32 |
| 101 | 3 | 4 | 5 | 6 | | VI-2 | ANKRD13B | 0.43 |
| 102 | 3 | 4 | 5 | 6 | | VI-2 | ANKRD52 | 0.46 |
| 103 | 3 | 4 | 5 | 6 | | VI-2 | ANP32C | 0.44 |
| 104 | 3 | 4 | 5 | 6 | | VI-2 | ANPEP | 0.29 |
| 105 | 3 | 4 | 5 | 6 | | VI-2 | ANTXR1 | 0.43 |
| 106 | 3 | 4 | 5 | 6 | | VI-2 | ANXA2 | 0.43 |
| 107 | 3 | 4 | 5 | 6 | | VI-2 | ANXA2P1 | 0.26 |
| 108 | 3 | 4 | 5 | 6 | | VI-2 | ANXA2P3 | 0.37 |
| 109 | 3 | 4 | 5 | 6 | | VI-2 | ANXA8 | 0.31 |
| 110 | 3 | 4 | 5 | 6 | | VI-2 | AP8B1 | 0.49 |
| 111 | 3 | 4 | 5 | 6 | | VI-2 | APCDD1 | 0.40 |
| 112 | 3 | 4 | 5 | 6 | | VI-2 | APLN | 0.26 |
| 113 | 3 | 4 | 5 | 6 | | VI-2 | APLNR | 0.43 |
| 114 | 3 | 4 | 5 | 6 | | VI-2 | APOBEC3D | 0.41 |
| 115 | 3 | 4 | 5 | 6 | | VI-2 | APOL4 | 0.32 |
| 116 | 3 | 4 | 5 | 6 | | VI-2 | ARHGAP17 | 0.49 |
| 117 | 3 | 4 | 5 | 6 | | VI-2 | ARHGAP31 | 0.39 |
| 118 | 3 | 4 | 5 | 6 | | VI-2 | ARHGAP4 | 0.44 |
| 119 | 3 | 4 | 5 | 6 | | VI-2 | ARHGAP9 | 0.45 |
| 120 | 3 | 4 | 5 | 6 | | VI-2 | ARHGDIA | 0.44 |
| 121 | 3 | 4 | 5 | 6 | | VI-2 | ARHGEF11 | 0.49 |
| 122 | 3 | 4 | 5 | 6 | | VI-2 | ARHGEF3 | 0.49 |
| 123 | 3 | 4 | 5 | 6 | | VI-2 | ARHGEF40 | 0.40 |
| 124 | 3 | 4 | 5 | 6 | | VI-2 | ARID3B | 0.41 |
| 125 | 3 | 4 | 5 | 6 | | VI-2 | ARL8A | 0.47 |
| 126 | 3 | 4 | 5 | 6 | | VI-2 | ARSB | 0.38 |
| 127 | 3 | 4 | 5 | 6 | | VI-2 | ATP1A1OS | 0.41 |
| 128 | 3 | 4 | 5 | 6 | | VI-2 | ATP1B2 | 0.49 |
| 129 | 3 | 4 | 5 | 6 | | VI-2 | ATRIP | 0.37 |
| 130 | 3 | 4 | 5 | 6 | | VI-2 | ATXN2L | 0.47 |
| 131 | 3 | 4 | 5 | 6 | | VI-2 | AXL | 0.46 |
| 132 | 3 | 4 | 5 | 6 | | VI-2 | AZI1 | 0.37 |
| 133 | 3 | 4 | 5 | 6 | | VI-2 | B3GNT7 | 0.36 |
| 134 | 3 | 4 | 5 | 6 | | VI-2 | BAHCC1 | 0.36 |
| 135 | 3 | 4 | 5 | 6 | | VI-2 | BCAN | 0.40 |
| 136 | 3 | 4 | 5 | 6 | | VI-2 | BCR | 0.49 |
| 137 | 3 | 4 | 5 | 6 | | VI-2 | BCRP3 | 0.43 |
| 138 | 3 | 4 | 5 | 6 | | VI-2 | BDKRB2 | 0.31 |
| 139 | 3 | 4 | 5 | 6 | | VI-2 | BGN | 0.42 |
| 140 | 3 | 4 | 5 | 6 | | VI-2 | BIRC5 | 0.42 |
| 141 | 3 | 4 | 5 | 6 | | VI-2 | BMP8A | 0.39 |
| 142 | 3 | 4 | 5 | 6 | | VI-2 | BOC | 0.41 |
| 143 | 3 | 4 | 5 | 6 | | VI-2 | BRPF1 | 0.40 |
| 144 | 3 | 4 | 5 | 6 | | VI-2 | C11orf21 | 0.37 |
| 145 | 3 | 4 | 5 | 6 | | VI-2 | C11orf24 | 0.43 |
| 146 | 3 | 4 | 5 | 6 | | VI-2 | C11orf63 | 0.42 |
| 147 | 3 | 4 | 5 | 6 | | VI-2 | C14orf43 | 0.35 |
| 148 | 3 | 4 | 5 | 6 | | VI-2 | C16orf55 | 0.42 |
| 149 | 3 | 4 | 5 | 6 | | VI-2 | C16orf74 | 0.32 |
| 150 | 3 | 4 | 5 | 6 | | VI-2 | C17orf51 | 0.46 |
| 151 | 3 | 4 | 5 | 6 | | VI-2 | C19orf29-AS1 | 0.38 |
| 152 | 3 | 4 | 5 | 6 | | VI-2 | C19orf44 | 0.44 |
| 153 | 3 | 4 | 5 | 6 | | VI-2 | C19orf55 | 0.46 |
| 154 | 3 | 4 | 5 | 6 | | VI-2 | C1orf198 | 0.48 |
| 155 | 3 | 4 | 5 | 6 | | VI-2 | C1orf226 | 0.46 |
| 156 | 3 | 4 | 5 | 6 | | VI-2 | C1QTNF2 | 0.26 |
| 157 | 3 | 4 | 5 | 6 | | VI-2 | C1QTNF5 | 0.40 |
| 158 | 3 | 4 | 5 | 6 | | VI-2 | C1R | 0.49 |
| 159 | 3 | 4 | 5 | 6 | | VI-2 | C2 | 0.30 |
| 160 | 3 | 4 | 5 | 6 | | VI-2 | C22orf29 | 0.48 |
| 161 | 3 | 4 | 5 | 6 | | VI-2 | C3 | 0.33 |
| 162 | 3 | 4 | 5 | 6 | | VI-2 | C3orf35 | 0.44 |
| 163 | 3 | 4 | 5 | 6 | | VI-2 | C5orf20 | 0.38 |
| 164 | 3 | 4 | 5 | 6 | | VI-2 | C6orf15 | 0.47 |
| 165 | 3 | 4 | 5 | 6 | | VI-2 | C9orf64 | 0.49 |
| 166 | 3 | 4 | 5 | 6 | | VI-2 | CA11 | 0.43 |
| 167 | 3 | 4 | 5 | 6 | | VI-2 | CA5B | 0.46 |
| 168 | 3 | 4 | 5 | 6 | | VI-2 | CABIN1 | 0.38 |
| 169 | 3 | 4 | 5 | 6 | | VI-2 | CABLES2 | 0.49 |
| 170 | 3 | 4 | 5 | 6 | | VI-2 | CACNB3 | 0.48 |
| 171 | 3 | 4 | 5 | 6 | | VI-2 | CAD | 0.46 |
| 172 | 3 | 4 | 5 | 6 | | VI-2 | CADM3 | 0.46 |
| 173 | 3 | 4 | 5 | 6 | | VI-2 | CALHM2 | 0.47 |
| 174 | 3 | 4 | 5 | 6 | | VI-2 | CAMTA2 | 0.49 |
| 175 | 3 | 4 | 5 | 6 | | VI-2 | CAND2 | 0.47 |
| 176 | 3 | 4 | 5 | 6 | | VI-2 | CAPN5 | 0.48 |
| 177 | 3 | 4 | 5 | 6 | | VI-2 | CBX2 | 0.33 |
| 178 | 3 | 4 | 5 | 6 | | VI-2 | CCBP2 | 0.21 |
| 179 | 3 | 4 | 5 | 6 | | VI-2 | CCDC101 | 0.38 |
| 180 | 3 | 4 | 5 | 6 | | VI-2 | CCDC102A | 0.34 |
| 181 | 3 | 4 | 5 | 6 | | VI-2 | CCDC163P | 0.25 |
| 182 | 3 | 4 | 5 | 6 | | VI-2 | CCDC165 | 0.36 |
| 183 | 3 | 4 | 5 | 6 | | VI-2 | CCDC48 | 0.41 |
| 184 | 3 | 4 | 5 | 6 | | VI-2 | CCDC64 | 0.35 |
| 185 | 3 | 4 | 5 | 6 | | VI-2 | CCDC88B | 0.35 |
| 186 | 3 | 4 | 5 | 6 | | VI-2 | CCDC92 | 0.48 |
| 187 | 3 | 4 | 5 | 6 | | VI-2 | CCL27 | 0.43 |
| 188 | 3 | 4 | 5 | 6 | | VI-2 | CCNB1 | 0.50 |
| 189 | 3 | 4 | 5 | 6 | | VI-2 | CCNB2 | 0.27 |
| 190 | 3 | 4 | 5 | 6 | | VI-2 | CD248 | 0.28 |

Fig. 39 - 2

| | | | | | | | |
|---|---|---|---|---|---|---|---|
| 191 | 3 | 4 | 5 | 6 | VI-2 | CD276 | 0.41 |
| 192 | 3 | 4 | 5 | 6 | VI-2 | CD34 | 0.36 |
| 193 | 3 | 4 | 5 | 6 | VI-2 | CD97 | 0.34 |
| 194 | 3 | 4 | 5 | 6 | VI-2 | CD99 | 0.47 |
| 195 | 3 | 4 | 5 | 6 | VI-2 | CDC20 | 0.46 |
| 196 | 3 | 4 | 5 | 6 | VI-2 | CDCA8 | 0.45 |
| 197 | 3 | 4 | 5 | 6 | VI-2 | CDK7 | 0.43 |
| 198 | 3 | 4 | 5 | 6 | VI-2 | CDKN3 | 0.50 |
| 199 | 3 | 4 | 5 | 6 | VI-2 | CENPL | 0.46 |
| 200 | 3 | 4 | 5 | 6 | VI-2 | CEP250 | 0.30 |
| 201 | 3 | 4 | 5 | 6 | VI-2 | CEP55 | 0.43 |
| 202 | 3 | 4 | 5 | 6 | VI-2 | CEP85 | 0.44 |
| 203 | 3 | 4 | 5 | 6 | VI-2 | CEP89 | 0.37 |
| 204 | 3 | 4 | 5 | 6 | VI-2 | CERCAM | 0.30 |
| 205 | 3 | 4 | 5 | 6 | VI-2 | CHD3 | 0.41 |
| 206 | 3 | 4 | 5 | 6 | VI-2 | CHPF2 | 0.46 |
| 207 | 3 | 4 | 5 | 6 | VI-2 | CHRDL1 | 0.50 |
| 208 | 3 | 4 | 5 | 6 | VI-2 | CHST10 | 0.43 |
| 209 | 3 | 4 | 5 | 6 | VI-2 | CHST11 | 0.47 |
| 210 | 3 | 4 | 5 | 6 | VI-2 | CHST3 | 0.34 |
| 211 | 3 | 4 | 5 | 6 | VI-2 | CHST7 | 0.49 |
| 212 | 3 | 4 | 5 | 6 | VI-2 | CIC | 0.37 |
| 213 | 3 | 4 | 5 | 6 | VI-2 | CIITA | 0.22 |
| 214 | 3 | 4 | 5 | 6 | VI-2 | CKB | 0.49 |
| 215 | 3 | 4 | 5 | 6 | VI-2 | CLCF1 | 0.44 |
| 216 | 3 | 4 | 5 | 6 | VI-2 | CLEC3B | 0.34 |
| 217 | 3 | 4 | 5 | 6 | VI-2 | CLEC7A | 0.34 |
| 218 | 3 | 4 | 5 | 6 | VI-2 | CLIC2 | 0.39 |
| 219 | 3 | 4 | 5 | 6 | VI-2 | CLIP3 | 0.38 |
| 220 | 3 | 4 | 5 | 6 | VI-2 | CNOT3 | 0.41 |
| 221 | 3 | 4 | 5 | 6 | VI-2 | CNPY4 | 0.48 |
| 222 | 3 | 4 | 5 | 6 | VI-2 | CNTNAP1 | 0.28 |
| 223 | 3 | 4 | 5 | 6 | VI-2 | CNTNAP3B | 0.37 |
| 224 | 3 | 4 | 5 | 6 | VI-2 | CNTROB | 0.39 |
| 225 | 3 | 4 | 5 | 6 | VI-2 | COG1 | 0.44 |
| 226 | 3 | 4 | 5 | 6 | VI-2 | COL14A1 | 0.38 |
| 227 | 3 | 4 | 5 | 6 | VI-2 | COL17A1 | 0.48 |
| 228 | 3 | 4 | 5 | 6 | VI-2 | COL18A1 | 0.38 |
| 229 | 3 | 4 | 5 | 6 | VI-2 | COL5A1 | 0.23 |
| 230 | 3 | 4 | 5 | 6 | VI-2 | COL5A2 | 0.48 |
| 231 | 3 | 4 | 5 | 6 | VI-2 | COL5A3 | 0.35 |
| 232 | 3 | 4 | 5 | 6 | VI-2 | COL6A1 | 0.31 |
| 233 | 3 | 4 | 5 | 6 | VI-2 | COL6A2 | 0.33 |
| 234 | 3 | 4 | 5 | 6 | VI-2 | COL6A3 | 0.30 |
| 235 | 3 | 4 | 5 | 6 | VI-2 | COL8A2 | 0.33 |
| 236 | 3 | 4 | 5 | 6 | VI-2 | COLEC12 | 0.36 |
| 237 | 3 | 4 | 5 | 6 | VI-2 | CORO1C | 0.47 |
| 238 | 3 | 4 | 5 | 6 | VI-2 | CORO2B | 0.42 |
| 239 | 3 | 4 | 5 | 6 | VI-2 | CP | 0.46 |
| 240 | 3 | 4 | 5 | 6 | VI-2 | CPQ | 0.46 |
| 241 | 3 | 4 | 5 | 6 | VI-2 | CPSF1 | 0.23 |
| 242 | 3 | 4 | 5 | 6 | VI-2 | CREB3L1 | 0.44 |
| 243 | 3 | 4 | 5 | 6 | VI-2 | CREBBP | 0.43 |
| 244 | 3 | 4 | 5 | 6 | VI-2 | CRLF1 | 0.36 |
| 245 | 3 | 4 | 5 | 6 | VI-2 | CRTAP | 0.49 |
| 246 | 3 | 4 | 5 | 6 | VI-2 | CRTC1 | 0.47 |
| 247 | 3 | 4 | 5 | 6 | VI-2 | CRTC2 | 0.46 |
| 248 | 3 | 4 | 5 | 6 | VI-2 | CRTC3 | 0.50 |
| 249 | 3 | 4 | 5 | 6 | VI-2 | CRY2 | 0.47 |
| 250 | 3 | 4 | 5 | 6 | VI-2 | CSF1 | 0.34 |
| 251 | 3 | 4 | 5 | 6 | VI-2 | CSPG4 | 0.28 |
| 252 | 3 | 4 | 5 | 6 | VI-2 | CTHRC1 | 0.50 |
| 253 | 3 | 4 | 5 | 6 | VI-2 | CTSK | 0.48 |
| 254 | 3 | 4 | 5 | 6 | VI-2 | CUEDC1 | 0.36 |
| 255 | 3 | 4 | 5 | 6 | VI-2 | CUL9 | 0.48 |
| 256 | 3 | 4 | 5 | 6 | VI-2 | CXCL14 | 0.36 |
| 257 | 3 | 4 | 5 | 6 | VI-2 | CYB5R3 | 0.43 |
| 258 | 3 | 4 | 5 | 6 | VI-2 | CYP21A1P | 0.32 |
| 259 | 3 | 4 | 5 | 6 | VI-2 | CYP21A2 | 0.36 |
| 260 | 3 | 4 | 5 | 6 | VI-2 | CYP26B1 | 0.31 |
| 261 | 3 | 4 | 5 | 6 | VI-2 | CYR61 | 0.34 |
| 262 | 3 | 4 | 5 | 6 | VI-2 | CYS1 | 0.39 |
| 263 | 3 | 4 | 5 | 6 | VI-2 | CYTH3 | 0.49 |
| 264 | 3 | 4 | 5 | 6 | VI-2 | DAB2IP | 0.49 |
| 265 | 3 | 4 | 5 | 6 | VI-2 | DACT1 | 0.36 |
| 266 | 3 | 4 | 5 | 6 | VI-2 | DCHS1 | 0.30 |
| 267 | 3 | 4 | 5 | 6 | VI-2 | DCTN1 | 0.41 |
| 268 | 3 | 4 | 5 | 6 | VI-2 | DDX51 | 0.47 |
| 269 | 3 | 4 | 5 | 6 | VI-2 | DEF6 | 0.46 |
| 270 | 3 | 4 | 5 | 6 | VI-2 | DENND4B | 0.45 |
| 271 | 3 | 4 | 5 | 6 | VI-2 | DFNB31 | 0.35 |
| 272 | 3 | 4 | 5 | 6 | VI-2 | DHX16 | 0.34 |
| 273 | 3 | 4 | 5 | 6 | VI-2 | DHX30 | 0.46 |
| 274 | 3 | 4 | 5 | 6 | VI-2 | DHX38 | 0.43 |
| 275 | 3 | 4 | 5 | 6 | VI-2 | DKK2 | 0.25 |
| 276 | 3 | 4 | 5 | 6 | VI-2 | DLX4 | 0.49 |
| 277 | 3 | 4 | 5 | 6 | VI-2 | DMWD | 0.39 |
| 278 | 3 | 4 | 5 | 6 | VI-2 | DNAJB5 | 0.43 |
| 279 | 3 | 4 | 5 | 6 | VI-2 | DND1 | 0.49 |
| 280 | 3 | 4 | 5 | 6 | VI-2 | DNMBP | 0.35 |
| 281 | 3 | 4 | 5 | 6 | VI-2 | DNMT1 | 0.44 |
| 282 | 3 | 4 | 5 | 6 | VI-2 | DOC2B | 0.36 |
| 283 | 3 | 4 | 5 | 6 | VI-2 | DOCK6 | 0.42 |
| 284 | 3 | 4 | 5 | 6 | VI-2 | DOT1L | 0.46 |
| 285 | 3 | 4 | 5 | 6 | VI-2 | DPEP2 | 0.42 |
| 286 | 3 | 4 | 5 | 6 | VI-2 | DPP4 | 0.35 |
| 287 | 3 | 4 | 5 | 6 | VI-2 | DPYSL3 | 0.29 |
| 288 | 3 | 4 | 5 | 6 | VI-2 | DTX2P1-UPK3BP1-PMS2P11 | 0.49 |
| 289 | 3 | 4 | 5 | 6 | VI-2 | DUOX1 | 0.48 |
| 290 | 3 | 4 | 5 | 6 | VI-2 | DVL3 | 0.43 |
| 291 | 3 | 4 | 5 | 6 | VI-2 | DYRK2 | 0.45 |
| 292 | 3 | 4 | 5 | 6 | VI-2 | ECE1 | 0.39 |
| 293 | 3 | 4 | 5 | 6 | VI-2 | EDC4 | 0.34 |
| 294 | 3 | 4 | 5 | 6 | VI-2 | EDN1 | 0.24 |
| 295 | 3 | 4 | 5 | 6 | VI-2 | EEPD1 | 0.49 |
| 296 | 3 | 4 | 5 | 6 | VI-2 | EFEMP2 | 0.40 |
| 297 | 3 | 4 | 5 | 6 | VI-2 | EFNB3 | 0.36 |
| 298 | 3 | 4 | 5 | 6 | VI-2 | EHBP1L1 | 0.24 |
| 299 | 3 | 4 | 5 | 6 | VI-2 | EHD2 | 0.41 |
| 300 | 3 | 4 | 5 | 6 | VI-2 | EHD4 | 0.49 |
| 301 | 3 | 4 | 5 | 6 | VI-2 | EHMT2 | 0.38 |
| 302 | 3 | 4 | 5 | 6 | VI-2 | EIF3C | 0.47 |
| 303 | 3 | 4 | 5 | 6 | VI-2 | EIF4ENIF1 | 0.50 |
| 304 | 3 | 4 | 5 | 6 | VI-2 | ELF4 | 0.28 |
| 305 | 3 | 4 | 5 | 6 | VI-2 | ELK3 | 0.22 |
| 306 | 3 | 4 | 5 | 6 | VI-2 | ELMO1 | 0.46 |
| 307 | 3 | 4 | 5 | 6 | VI-2 | EME2 | 0.36 |
| 308 | 3 | 4 | 5 | 6 | VI-2 | EMILIN2 | 0.35 |
| 309 | 3 | 4 | 5 | 6 | VI-2 | EML3 | 0.49 |
| 310 | 3 | 4 | 5 | 6 | VI-2 | EMP3 | 0.41 |
| 311 | 3 | 4 | 5 | 6 | VI-2 | ENG | 0.48 |
| 312 | 3 | 4 | 5 | 6 | VI-2 | EPC1 | 0.41 |
| 313 | 3 | 4 | 5 | 6 | VI-2 | EPHB6 | 0.43 |
| 314 | 3 | 4 | 5 | 6 | VI-2 | EVC | 0.22 |
| 315 | 3 | 4 | 5 | 6 | VI-2 | EVC2 | 0.39 |
| 316 | 3 | 4 | 5 | 6 | VI-2 | EVPL | 0.37 |
| 317 | 3 | 4 | 5 | 6 | VI-2 | EXOSC10 | 0.41 |
| 318 | 3 | 4 | 5 | 6 | VI-2 | EXOSC6 | 0.50 |
| 319 | 3 | 4 | 5 | 6 | VI-2 | EXPH5 | 0.39 |
| 320 | 3 | 4 | 5 | 6 | VI-2 | EXT1 | 0.34 |
| 321 | 3 | 4 | 5 | 6 | VI-2 | F10 | 0.27 |
| 322 | 3 | 4 | 5 | 6 | VI-2 | F13A1 | 0.34 |
| 323 | 3 | 4 | 5 | 6 | VI-2 | F2RL2 | 0.46 |
| 324 | 3 | 4 | 5 | 6 | VI-2 | FAM107B | 0.49 |
| 325 | 3 | 4 | 5 | 6 | VI-2 | FAM110B | 0.38 |
| 326 | 3 | 4 | 5 | 6 | VI-2 | FAM125B | 0.40 |
| 327 | 3 | 4 | 5 | 6 | VI-2 | FAM13C | 0.46 |
| 328 | 3 | 4 | 5 | 6 | VI-2 | FAM168A | 0.29 |
| 329 | 3 | 4 | 5 | 6 | VI-2 | FAM180B | 0.33 |
| 330 | 3 | 4 | 5 | 6 | VI-2 | FAM193A | 0.43 |
| 331 | 3 | 4 | 5 | 6 | VI-2 | FAM19A5 | 0.38 |
| 332 | 3 | 4 | 5 | 6 | VI-2 | FAM27B | 0.48 |
| 333 | 3 | 4 | 5 | 6 | VI-2 | FAM65A | 0.34 |
| 334 | 3 | 4 | 5 | 6 | VI-2 | FAM83B | 0.35 |
| 335 | 3 | 4 | 5 | 6 | VI-2 | FBLN2 | 0.36 |
| 336 | 3 | 4 | 5 | 6 | VI-2 | FBLN5 | 0.44 |
| 337 | 3 | 4 | 5 | 6 | VI-2 | FBLN7 | 0.47 |
| 338 | 3 | 4 | 5 | 6 | VI-2 | FBN1 | 0.30 |
| 339 | 3 | 4 | 5 | 6 | VI-2 | FBXL7 | 0.26 |
| 340 | 3 | 4 | 5 | 6 | VI-2 | FBXL8 | 0.49 |
| 341 | 3 | 4 | 5 | 6 | VI-2 | FBXO41 | 0.41 |
| 342 | 3 | 4 | 5 | 6 | VI-2 | FBXW8 | 0.47 |
| 343 | 3 | 4 | 5 | 6 | VI-2 | FCGR2C | 0.48 |
| 344 | 3 | 4 | 5 | 6 | VI-2 | FCHSD1 | 0.47 |
| 345 | 3 | 4 | 5 | 6 | VI-2 | FGD1 | 0.48 |
| 346 | 3 | 4 | 5 | 6 | VI-2 | FGD5 | 0.23 |
| 347 | 3 | 4 | 5 | 6 | VI-2 | FGFBP1 | 0.24 |
| 348 | 3 | 4 | 5 | 6 | VI-2 | FGFR1 | 0.41 |
| 349 | 3 | 4 | 5 | 6 | VI-2 | FHL3 | 0.41 |
| 350 | 3 | 4 | 5 | 6 | VI-2 | FIBIN | 0.49 |
| 351 | 3 | 4 | 5 | 6 | VI-2 | FKBP10 | 0.37 |
| 352 | 3 | 4 | 5 | 6 | VI-2 | FKBP9 | 0.44 |
| 353 | 3 | 4 | 5 | 6 | VI-2 | FLI1 | 0.40 |
| 354 | 3 | 4 | 5 | 6 | VI-2 | FLJI | 0.43 |
| 355 | 3 | 4 | 5 | 6 | VI-2 | FLNA | 0.25 |
| 356 | 3 | 4 | 5 | 6 | VI-2 | FLNC | 0.28 |
| 357 | 3 | 4 | 5 | 6 | VI-2 | FLT3LG | 0.24 |
| 358 | 3 | 4 | 5 | 6 | VI-2 | FLT4 | 0.36 |
| 359 | 3 | 4 | 5 | 6 | VI-2 | FMNL1 | 0.32 |
| 360 | 3 | 4 | 5 | 6 | VI-2 | FMNL3 | 0.49 |
| 361 | 3 | 4 | 5 | 6 | VI-2 | FMOD | 0.42 |
| 362 | 3 | 4 | 5 | 6 | VI-2 | FN1 | 0.38 |
| 363 | 3 | 4 | 5 | 6 | VI-2 | FOS | 0.36 |
| 364 | 3 | 4 | 5 | 6 | VI-2 | FOXM1 | 0.39 |
| 365 | 3 | 4 | 5 | 6 | VI-2 | FOXS1 | 0.28 |
| 366 | 3 | 4 | 5 | 6 | VI-2 | FSTL1 | 0.36 |
| 367 | 3 | 4 | 5 | 6 | VI-2 | FTO | 0.46 |
| 368 | 3 | 4 | 5 | 6 | VI-2 | FUT11 | 0.46 |
| 369 | 3 | 4 | 5 | 6 | VI-2 | FXYD5 | 0.35 |
| 370 | 3 | 4 | 5 | 6 | VI-2 | GALNT2 | 0.50 |
| 371 | 3 | 4 | 5 | 6 | VI-2 | GAS1 | 0.32 |
| 372 | 3 | 4 | 5 | 6 | VI-2 | GAS2L1 | 0.47 |
| 373 | 3 | 4 | 5 | 6 | VI-2 | GATA2 | 0.27 |
| 374 | 3 | 4 | 5 | 6 | VI-2 | GCNT1L1 | 0.49 |
| 375 | 3 | 4 | 5 | 6 | VI-2 | GDF10 | 0.29 |
| 376 | 3 | 4 | 5 | 6 | VI-2 | GDF11 | 0.41 |
| 377 | 3 | 4 | 5 | 6 | VI-2 | GIMAP5 | 0.43 |
| 378 | 3 | 4 | 5 | 6 | VI-2 | GIPR | 0.46 |
| 379 | 3 | 4 | 5 | 6 | VI-2 | GIT1 | 0.46 |
| 380 | 3 | 4 | 5 | 6 | VI-2 | GJA5 | 0.49 |
| 381 | 3 | 4 | 5 | 6 | VI-2 | GJC1 | 0.50 |

Fig. 39 - 3

| | | | | | | | | | | | | | | | | |
|---|---|---|---|---|---|---|---|---|---|---|---|---|---|---|---|---|
| 382 | 3 | 4 | 5 | 6 | | VI-2 | GLDN | 0.46 | | 478 | 3 | 4 | 5 | 6 | VI-2 | LAMA3 | 0.44 |
| 383 | 3 | 4 | 5 | 6 | | VI-2 | GLIPR2 | 0.49 | | 479 | 3 | 4 | 5 | 6 | VI-2 | LAMB2 | 0.35 |
| 384 | 3 | 4 | 5 | 6 | | VI-2 | GLIS2 | 0.30 | | 480 | 3 | 4 | 5 | 6 | VI-2 | LAMB2P1 | 0.48 |
| 385 | 3 | 4 | 5 | 6 | | VI-2 | GLT25D1 | 0.50 | | 481 | 3 | 4 | 5 | 6 | VI-2 | LAMB3 | 0.46 |
| 386 | 3 | 4 | 5 | 6 | | VI-2 | GLTSCR1 | 0.40 | | 482 | 3 | 4 | 5 | 6 | VI-2 | LAMC2 | 0.26 |
| 387 | 3 | 4 | 5 | 6 | | VI-2 | GNAI2 | 0.49 | | 483 | 3 | 4 | 5 | 6 | VI-2 | LDOC1L | 0.43 |
| 388 | 3 | 4 | 5 | 6 | | VI-2 | GP1BA | 0.21 | | 484 | 3 | 4 | 5 | 6 | VI-2 | LEPREL2 | 0.44 |
| 389 | 3 | 4 | 5 | 6 | | VI-2 | GPBAR1 | 0.47 | | 485 | 3 | 4 | 5 | 6 | VI-2 | LGALS2 | 0.32 |
| 390 | 3 | 4 | 5 | 6 | | VI-2 | GPR124 | 0.35 | | 486 | 3 | 4 | 5 | 6 | VI-2 | LIF | 0.28 |
| 391 | 3 | 4 | 5 | 6 | | VI-2 | GPR132 | 0.47 | | 487 | 3 | 4 | 5 | 6 | VI-2 | LILRB5 | 0.44 |
| 392 | 3 | 4 | 5 | 6 | | VI-2 | GPR153 | 0.49 | | 488 | 3 | 4 | 5 | 6 | VI-2 | LIX1L | 0.25 |
| 393 | 3 | 4 | 5 | 6 | | VI-2 | GPR162 | 0.45 | | 489 | 3 | 4 | 5 | 6 | VI-2 | LMX1B | 0.48 |
| 394 | 3 | 4 | 5 | 6 | | VI-2 | GPSM1 | 0.48 | | 490 | 3 | 4 | 5 | 6 | VI-2 | LOC100128881 | 0.48 |
| 395 | 3 | 4 | 5 | 6 | | VI-2 | GPX8 | 0.44 | | 491 | 3 | 4 | 5 | 6 | VI-2 | LOC100130744 | 0.44 |
| 396 | 3 | 4 | 5 | 6 | | VI-2 | GRID1 | 0.39 | | 492 | 3 | 4 | 5 | 6 | VI-2 | LOC100132831 | 0.48 |
| 397 | 3 | 4 | 5 | 6 | | VI-2 | GRK5 | 0.35 | | 493 | 3 | 4 | 5 | 6 | VI-2 | LOC100287042 | 0.43 |
| 398 | 3 | 4 | 5 | 6 | | VI-2 | GRM2 | 0.32 | | 494 | 3 | 4 | 5 | 6 | VI-2 | LOC100288123 | 0.41 |
| 399 | 3 | 4 | 5 | 6 | | VI-2 | GSTM5 | 0.40 | | 495 | 3 | 4 | 5 | 6 | VI-2 | LOC100506388 | 0.28 |
| 400 | 3 | 4 | 5 | 6 | | VI-2 | GSTT2B | 0.46 | | 496 | 3 | 4 | 5 | 6 | VI-2 | LOC255480 | 0.24 |
| 401 | 3 | 4 | 5 | 6 | | VI-2 | GTF2F1 | 0.49 | | 497 | 3 | 4 | 5 | 6 | VI-2 | LOC283788 | 0.43 |
| 402 | 3 | 4 | 5 | 6 | | VI-2 | H1FX | 0.47 | | 498 | 3 | 4 | 5 | 6 | VI-2 | LOC284276 | 0.42 |
| 403 | 3 | 4 | 5 | 6 | | VI-2 | HAND2 | 0.27 | | 499 | 3 | 4 | 5 | 6 | VI-2 | LOC389906 | 0.32 |
| 404 | 3 | 4 | 5 | 6 | | VI-2 | HAPLN3 | 0.47 | | 500 | 3 | 4 | 5 | 6 | VI-2 | LOC399744 | 0.48 |
| 405 | 3 | 4 | 5 | 6 | | VI-2 | HAS2 | 0.42 | | 501 | 3 | 4 | 5 | 6 | VI-2 | LOC400043 | 0.47 |
| 406 | 3 | 4 | 5 | 6 | | VI-2 | HCFC1R1 | 0.46 | | 502 | 3 | 4 | 5 | 6 | VI-2 | LOC645166 | 0.48 |
| 407 | 3 | 4 | 5 | 6 | | VI-2 | HDAC6 | 0.48 | | 503 | 3 | 4 | 5 | 6 | VI-2 | LOC646762 | 0.50 |
| 408 | 3 | 4 | 5 | 6 | | VI-2 | HDAC7 | 0.47 | | 504 | 3 | 4 | 5 | 6 | VI-2 | LOC728875 | 0.48 |
| 409 | 3 | 4 | 5 | 6 | | VI-2 | HDLBP | 0.47 | | 505 | 3 | 4 | 5 | 6 | VI-2 | LOC90784 | 0.23 |
| 410 | 3 | 4 | 5 | 6 | | VI-2 | HEATR6 | 0.45 | | 506 | 3 | 4 | 5 | 6 | VI-2 | LOXL1 | 0.25 |
| 411 | 3 | 4 | 5 | 6 | | VI-2 | HEXIM2 | 0.48 | | 507 | 3 | 4 | 5 | 6 | VI-2 | LPCAT4 | 0.40 |
| 412 | 3 | 4 | 5 | 6 | | VI-2 | HGSNAT | 0.48 | | 508 | 3 | 4 | 5 | 6 | VI-2 | LRP1 | 0.44 |
| 413 | 3 | 4 | 5 | 6 | | VI-2 | HIRIP3 | 0.45 | | 509 | 3 | 4 | 5 | 6 | VI-2 | LRP5 | 0.37 |
| 414 | 3 | 4 | 5 | 6 | | VI-2 | HIVEP1 | 0.26 | | 510 | 3 | 4 | 5 | 6 | VI-2 | LRRC23 | 0.40 |
| 415 | 3 | 4 | 5 | 6 | | VI-2 | HIVEP2 | 0.32 | | 511 | 3 | 4 | 5 | 6 | VI-2 | LRRC27 | 0.43 |
| 416 | 3 | 4 | 5 | 6 | | VI-2 | HLA-C | 0.42 | | 512 | 3 | 4 | 5 | 6 | VI-2 | LRRC33 | 0.35 |
| 417 | 3 | 4 | 5 | 6 | | VI-2 | HNRNPL | 0.40 | | 513 | 3 | 4 | 5 | 6 | VI-2 | LRRC45 | 0.49 |
| 418 | 3 | 4 | 5 | 6 | | VI-2 | HSD3B7 | 0.42 | | 514 | 3 | 4 | 5 | 6 | VI-2 | LRRC8C | 0.46 |
| 419 | 3 | 4 | 5 | 6 | | VI-2 | HSPG2 | 0.26 | | 515 | 3 | 4 | 5 | 6 | VI-2 | LRRK1 | 0.43 |
| 420 | 3 | 4 | 5 | 6 | | VI-2 | HTRA1 | 0.50 | | 516 | 3 | 4 | 5 | 6 | VI-2 | LRRN4CL | 0.37 |
| 421 | 3 | 4 | 5 | 6 | | VI-2 | HUNK | 0.27 | | 517 | 3 | 4 | 5 | 6 | VI-2 | LSS | 0.48 |
| 422 | 3 | 4 | 5 | 6 | | VI-2 | ICAM1 | 0.42 | | 518 | 3 | 4 | 5 | 6 | VI-2 | LTBP4 | 0.48 |
| 423 | 3 | 4 | 5 | 6 | | VI-2 | ID2B | 0.36 | | 519 | 3 | 4 | 5 | 6 | VI-2 | LURAP1 | 0.47 |
| 424 | 3 | 4 | 5 | 6 | | VI-2 | IFI6 | 0.31 | | 520 | 3 | 4 | 5 | 6 | VI-2 | LYL1 | 0.43 |
| 425 | 3 | 4 | 5 | 6 | | VI-2 | IFT122 | 0.44 | | 521 | 3 | 4 | 5 | 6 | VI-2 | MADD | 0.46 |
| 426 | 3 | 4 | 5 | 6 | | VI-2 | IGFBP3 | 0.43 | | 522 | 3 | 4 | 5 | 6 | VI-2 | MAN1A1 | 0.37 |
| 427 | 3 | 4 | 5 | 6 | | VI-2 | IGFBP4 | 0.48 | | 523 | 3 | 4 | 5 | 6 | VI-2 | MAP1A | 0.29 |
| 428 | 3 | 4 | 5 | 6 | | VI-2 | IGFBP5 | 0.35 | | 524 | 3 | 4 | 5 | 6 | VI-2 | MAP3K12 | 0.42 |
| 429 | 3 | 4 | 5 | 6 | | VI-2 | IGFBP6 | 0.47 | | 525 | 3 | 4 | 5 | 6 | VI-2 | MAP3K14 | 0.42 |
| 430 | 3 | 4 | 5 | 6 | | VI-2 | IGHMBP2 | 0.50 | | 526 | 3 | 4 | 5 | 6 | VI-2 | MAP4 | 0.44 |
| 431 | 3 | 4 | 5 | 6 | | VI-2 | IL17D | 0.36 | | 527 | 3 | 4 | 5 | 6 | VI-2 | MAPK8IP1 | 0.45 |
| 432 | 3 | 4 | 5 | 6 | | VI-2 | IL18BP | 0.44 | | 528 | 3 | 4 | 5 | 6 | VI-2 | MARVELD1 | 0.46 |
| 433 | 3 | 4 | 5 | 6 | | VI-2 | IL2RG | 0.25 | | 529 | 3 | 4 | 5 | 6 | VI-2 | MCM2 | 0.46 |
| 434 | 3 | 4 | 5 | 6 | | VI-2 | IL4R | 0.46 | | 530 | 3 | 4 | 5 | 6 | VI-2 | MDC1 | 0.28 |
| 435 | 3 | 4 | 5 | 6 | | VI-2 | INCENP | 0.33 | | 531 | 3 | 4 | 5 | 6 | VI-2 | MECP2 | 0.45 |
| 436 | 3 | 4 | 5 | 6 | | VI-2 | IQCE | 0.32 | | 532 | 3 | 4 | 5 | 6 | VI-2 | MED12 | 0.39 |
| 437 | 3 | 4 | 5 | 6 | | VI-2 | IRAK1 | 0.48 | | 533 | 3 | 4 | 5 | 6 | VI-2 | MED24 | 0.43 |
| 438 | 3 | 4 | 5 | 6 | | VI-2 | IRF2BPL | 0.47 | | 534 | 3 | 4 | 5 | 6 | VI-2 | MEF2D | 0.42 |
| 439 | 3 | 4 | 5 | 6 | | VI-2 | IRF3 | 0.43 | | 535 | 3 | 4 | 5 | 6 | VI-2 | MEGF8 | 0.49 |
| 440 | 3 | 4 | 5 | 6 | | VI-2 | IRF5 | 0.42 | | 536 | 3 | 4 | 5 | 6 | VI-2 | MFAP4 | 0.40 |
| 441 | 3 | 4 | 5 | 6 | | VI-2 | IRS1 | 0.29 | | 537 | 3 | 4 | 5 | 6 | VI-2 | MFGE8 | 0.46 |
| 442 | 3 | 4 | 5 | 6 | | VI-2 | ISLR | 0.32 | | 538 | 3 | 4 | 5 | 6 | VI-2 | MFSD2A | 0.37 |
| 443 | 3 | 4 | 5 | 6 | | VI-2 | ISM1 | 0.48 | | 539 | 3 | 4 | 5 | 6 | VI-2 | MIB2 | 0.49 |
| 444 | 3 | 4 | 5 | 6 | | VI-2 | ITGA11 | 0.20 | | 540 | 3 | 4 | 5 | 6 | VI-2 | MICAL1 | 0.36 |
| 445 | 3 | 4 | 5 | 6 | | VI-2 | ITGA3 | 0.36 | | 541 | 3 | 4 | 5 | 6 | VI-2 | MINK1 | 0.49 |
| 446 | 3 | 4 | 5 | 6 | | VI-2 | ITGAL | 0.41 | | 542 | 3 | 4 | 5 | 6 | VI-2 | MKI67 | 0.31 |
| 447 | 3 | 4 | 5 | 6 | | VI-2 | ITGB4 | 0.32 | | 543 | 3 | 4 | 5 | 6 | VI-2 | MKL1 | 0.48 |
| 448 | 3 | 4 | 5 | 6 | | VI-2 | ITGB7 | 0.47 | | 544 | 3 | 4 | 5 | 6 | VI-2 | MLL2 | 0.31 |
| 449 | 3 | 4 | 5 | 6 | | VI-2 | ITIH5 | 0.41 | | 545 | 3 | 4 | 5 | 6 | VI-2 | MLLT6 | 0.45 |
| 450 | 3 | 4 | 5 | 6 | | VI-2 | JAZF1 | 0.45 | | 546 | 3 | 4 | 5 | 6 | VI-2 | MMP11 | 0.39 |
| 451 | 3 | 4 | 5 | 6 | | VI-2 | JUND | 0.35 | | 547 | 3 | 4 | 5 | 6 | VI-2 | MMP14 | 0.44 |
| 452 | 3 | 4 | 5 | 6 | | VI-2 | KCNA6 | 0.44 | | 548 | 3 | 4 | 5 | 6 | VI-2 | MMP15 | 0.46 |
| 453 | 3 | 4 | 5 | 6 | | VI-2 | KCNAB2 | 0.37 | | 549 | 3 | 4 | 5 | 6 | VI-2 | MMP2 | 0.44 |
| 454 | 3 | 4 | 5 | 6 | | VI-2 | KCNMB4 | 0.50 | | 550 | 3 | 4 | 5 | 6 | VI-2 | MMP28 | 0.41 |
| 455 | 3 | 4 | 5 | 6 | | VI-2 | KDELC1 | 0.48 | | 551 | 3 | 4 | 5 | 6 | VI-2 | MN1 | 0.38 |
| 456 | 3 | 4 | 5 | 6 | | VI-2 | KDELR3 | 0.32 | | 552 | 3 | 4 | 5 | 6 | VI-2 | MOB3A | 0.49 |
| 457 | 3 | 4 | 5 | 6 | | VI-2 | KDM2A | 0.43 | | 553 | 3 | 4 | 5 | 6 | VI-2 | MORC2 | 0.46 |
| 458 | 3 | 4 | 5 | 6 | | VI-2 | KDM5C | 0.38 | | 554 | 3 | 4 | 5 | 6 | VI-2 | MOV10 | 0.46 |
| 459 | 3 | 4 | 5 | 6 | | VI-2 | KIAA0040 | 0.43 | | 555 | 3 | 4 | 5 | 6 | VI-2 | MRC2 | 0.28 |
| 460 | 3 | 4 | 5 | 6 | | VI-2 | KIAA0195 | 0.46 | | 556 | 3 | 4 | 5 | 6 | VI-2 | MSN | 0.35 |
| 461 | 3 | 4 | 5 | 6 | | VI-2 | KIAA0284 | 0.38 | | 557 | 3 | 4 | 5 | 6 | VI-2 | MST1R | 0.35 |
| 462 | 3 | 4 | 5 | 6 | | VI-2 | KIAA0889 | 0.30 | | 558 | 3 | 4 | 5 | 6 | VI-2 | MT2A | 0.37 |
| 463 | 3 | 4 | 5 | 6 | | VI-2 | KIAA0913 | 0.48 | | 559 | 3 | 4 | 5 | 6 | VI-2 | MTHFR | 0.45 |
| 464 | 3 | 4 | 5 | 6 | | VI-2 | KIAA1161 | 0.47 | | 560 | 3 | 4 | 5 | 6 | VI-2 | MYADM | 0.23 |
| 465 | 3 | 4 | 5 | 6 | | VI-2 | KIAA1614 | 0.38 | | 561 | 3 | 4 | 5 | 6 | VI-2 | MYBL2 | 0.33 |
| 466 | 3 | 4 | 5 | 6 | | VI-2 | KIAA1683 | 0.23 | | 562 | 3 | 4 | 5 | 6 | VI-2 | MYH9 | 0.37 |
| 467 | 3 | 4 | 5 | 6 | | VI-2 | KIF26A | 0.43 | | 563 | 3 | 4 | 5 | 6 | VI-2 | MYO9B | 0.36 |
| 468 | 3 | 4 | 5 | 6 | | VI-2 | KIFC1 | 0.34 | | 564 | 3 | 4 | 5 | 6 | VI-2 | NAA60 | 0.47 |
| 469 | 3 | 4 | 5 | 6 | | VI-2 | KIRREL | 0.27 | | 565 | 3 | 4 | 5 | 6 | VI-2 | NACAD | 0.29 |
| 470 | 3 | 4 | 5 | 6 | | VI-2 | KLF2 | 0.34 | | 566 | 3 | 4 | 5 | 6 | VI-2 | NBEAL2 | 0.35 |
| 471 | 3 | 4 | 5 | 6 | | VI-2 | KLF9 | 0.38 | | 567 | 3 | 4 | 5 | 6 | VI-2 | NCF4 | 0.44 |
| 472 | 3 | 4 | 5 | 6 | | VI-2 | KRT14 | 0.32 | | 568 | 3 | 4 | 5 | 6 | VI-2 | NCKAP5L | 0.36 |
| 473 | 3 | 4 | 5 | 6 | | VI-2 | KRT31 | 0.33 | | 569 | 3 | 4 | 5 | 6 | VI-2 | NCOA5 | 0.49 |
| 474 | 3 | 4 | 5 | 6 | | VI-2 | KRT5 | 0.28 | | 570 | 3 | 4 | 5 | 6 | VI-2 | NCOR2 | 0.39 |
| 475 | 3 | 4 | 5 | 6 | | VI-2 | KY | 0.40 | | 571 | 3 | 4 | 5 | 6 | VI-2 | NDST2 | 0.46 |
| 476 | 3 | 4 | 5 | 6 | | VI-2 | L1CAM | 0.44 | | 572 | 3 | 4 | 5 | 6 | VI-2 | NELF | 0.47 |
| 477 | 3 | 4 | 5 | 6 | | VI-2 | LAMA2 | 0.49 | | 573 | 3 | 4 | 5 | 6 | VI-2 | NEURL1B | 0.37 |

Fig. 39 - 4

| | | | | | | | | | | | | | | | |
|---|---|---|---|---|---|---|---|---|---|---|---|---|---|---|---|
| 574 | 3 | 4 | 5 | 6 | | VI-2 | NFASC | 0.41 | 670 | 3 | 4 | 5 | 6 | VI-2 | RAB11FIP3 | 0.48 |
| 575 | 3 | 4 | 5 | 6 | | VI-2 | NFATC1 | 0.34 | 671 | 3 | 4 | 5 | 6 | VI-2 | RAB11FIP5 | 0.43 |
| 576 | 3 | 4 | 5 | 6 | | VI-2 | NFE2L1 | 0.35 | 672 | 3 | 4 | 5 | 6 | VI-2 | RAB31 | 0.47 |
| 577 | 3 | 4 | 5 | 6 | | VI-2 | NFKB2 | 0.47 | 673 | 3 | 4 | 5 | 6 | VI-2 | RAB36 | 0.48 |
| 578 | 3 | 4 | 5 | 6 | | VI-2 | NGEF | 0.30 | 674 | 3 | 4 | 5 | 6 | VI-2 | RAB3IL1 | 0.35 |
| 579 | 3 | 4 | 5 | 6 | | VI-2 | NID1 | 0.50 | 675 | 3 | 4 | 5 | 6 | VI-2 | RAB43 | 0.47 |
| 580 | 3 | 4 | 5 | 6 | | VI-2 | NINJ2 | 0.43 | 676 | 3 | 4 | 5 | 6 | VI-2 | RAB4B | 0.42 |
| 581 | 3 | 4 | 5 | 6 | | VI-2 | NKD2 | 0.25 | 677 | 3 | 4 | 5 | 6 | VI-2 | RAD51D | 0.44 |
| 582 | 3 | 4 | 5 | 6 | | VI-2 | NLRC5 | 0.47 | 678 | 3 | 4 | 5 | 6 | VI-2 | RAI1 | 0.37 |
| 583 | 3 | 4 | 5 | 6 | | VI-2 | NOV | 0.41 | 679 | 3 | 4 | 5 | 6 | VI-2 | RAI2 | 0.49 |
| 584 | 3 | 4 | 5 | 6 | | VI-2 | NOVA2 | 0.32 | 680 | 3 | 4 | 5 | 6 | VI-2 | RALGDS | 0.31 |
| 585 | 3 | 4 | 5 | 6 | | VI-2 | NPHP4 | 0.40 | 681 | 3 | 4 | 5 | 6 | VI-2 | RANBP3 | 0.49 |
| 586 | 3 | 4 | 5 | 6 | | VI-2 | NPTXR | 0.42 | 682 | 3 | 4 | 5 | 6 | VI-2 | RAPGEF1 | 0.36 |
| 587 | 3 | 4 | 5 | 6 | | VI-2 | NRM | 0.39 | 683 | 3 | 4 | 5 | 6 | VI-2 | RARA | 0.31 |
| 588 | 3 | 4 | 5 | 6 | | VI-2 | NRSN2 | 0.47 | 684 | 3 | 4 | 5 | 6 | VI-2 | RASSF2 | 0.35 |
| 589 | 3 | 4 | 5 | 6 | | VI-2 | NUDT11 | 0.47 | 685 | 3 | 4 | 5 | 6 | VI-2 | RASSF9 | 0.39 |
| 590 | 3 | 4 | 5 | 6 | | VI-2 | NUMBL | 0.42 | 686 | 3 | 4 | 5 | 6 | VI-2 | RBMS2 | 0.48 |
| 591 | 3 | 4 | 5 | 6 | | VI-2 | NUP214 | 0.45 | 687 | 3 | 4 | 5 | 6 | VI-2 | RCN3 | 0.40 |
| 592 | 3 | 4 | 5 | 6 | | VI-2 | NUP93 | 0.40 | 688 | 3 | 4 | 5 | 6 | VI-2 | REEP2 | 0.46 |
| 593 | 3 | 4 | 5 | 6 | | VI-2 | NUTF2 | 0.40 | 689 | 3 | 4 | 5 | 6 | VI-2 | RELT | 0.31 |
| 594 | 3 | 4 | 5 | 6 | | VI-2 | OGFR | 0.48 | 690 | 3 | 4 | 5 | 6 | VI-2 | REM1 | 0.36 |
| 595 | 3 | 4 | 5 | 6 | | VI-2 | OLFM2 | 0.45 | 691 | 3 | 4 | 5 | 6 | VI-2 | RENBP | 0.41 |
| 596 | 3 | 4 | 5 | 6 | | VI-2 | OLFML1 | 0.33 | 692 | 3 | 4 | 5 | 6 | VI-2 | REXO1 | 0.42 |
| 597 | 3 | 4 | 5 | 6 | | VI-2 | OLFML2A | 0.37 | 693 | 3 | 4 | 5 | 6 | VI-2 | RFTN1 | 0.48 |
| 598 | 3 | 4 | 5 | 6 | | VI-2 | OLFML2B | 0.38 | 694 | 3 | 4 | 5 | 6 | VI-2 | RGAG4 | 0.43 |
| 599 | 3 | 4 | 5 | 6 | | VI-2 | OLFML3 | 0.39 | 695 | 3 | 4 | 5 | 6 | VI-2 | RGS14 | 0.36 |
| 600 | 3 | 4 | 5 | 6 | | VI-2 | OSBPL10 | 0.42 | 696 | 3 | 4 | 5 | 6 | VI-2 | RGS16 | 0.39 |
| 601 | 3 | 4 | 5 | 6 | | VI-2 | OSR2 | 0.25 | 697 | 3 | 4 | 5 | 6 | VI-2 | RHOB | 0.26 |
| 602 | 3 | 4 | 5 | 6 | | VI-2 | PACS1 | 0.42 | 698 | 3 | 4 | 5 | 6 | VI-2 | RHOBTB2 | 0.33 |
| 603 | 3 | 4 | 5 | 6 | | VI-2 | PALM | 0.44 | 699 | 3 | 4 | 5 | 6 | VI-2 | RIPK3 | 0.47 |
| 604 | 3 | 4 | 5 | 6 | | VI-2 | PAMR1 | 0.23 | 700 | 3 | 4 | 5 | 6 | VI-2 | RN45S | 0.47 |
| 605 | 3 | 4 | 5 | 6 | | VI-2 | PAPLN | 0.47 | 701 | 3 | 4 | 5 | 6 | VI-2 | RNF126P1 | 0.44 |
| 606 | 3 | 4 | 5 | 6 | | VI-2 | PAQR4 | 0.50 | 702 | 3 | 4 | 5 | 6 | VI-2 | RNF43 | 0.46 |
| 607 | 3 | 4 | 5 | 6 | | VI-2 | PARM1 | 0.48 | 703 | 3 | 4 | 5 | 6 | VI-2 | RPA3 | 0.40 |
| 608 | 3 | 4 | 5 | 6 | | VI-2 | PAX3 | 0.40 | 704 | 3 | 4 | 5 | 6 | VI-2 | RPAP1 | 0.49 |
| 609 | 3 | 4 | 5 | 6 | | VI-2 | PAXIP1 | 0.46 | 705 | 3 | 4 | 5 | 6 | VI-2 | RPL12 | 0.38 |
| 610 | 3 | 4 | 5 | 6 | | VI-2 | PCNA-AS1 | 0.46 | 706 | 3 | 4 | 5 | 6 | VI-2 | RPS4X | 0.42 |
| 611 | 3 | 4 | 5 | 6 | | VI-2 | PCNT | 0.38 | 707 | 3 | 4 | 5 | 6 | VI-2 | RRBP1 | 0.49 |
| 612 | 3 | 4 | 5 | 6 | | VI-2 | PCNXL3 | 0.45 | 708 | 3 | 4 | 5 | 6 | VI-2 | RRP9 | 0.46 |
| 613 | 3 | 4 | 5 | 6 | | VI-2 | PCSK1N | 0.34 | 709 | 3 | 4 | 5 | 6 | VI-2 | RTEL1-TNFRSF6B | 0.42 |
| 614 | 3 | 4 | 5 | 6 | | VI-2 | PDE4A | 0.32 | 710 | 3 | 4 | 5 | 6 | VI-2 | RUSC2 | 0.44 |
| 615 | 3 | 4 | 5 | 6 | | VI-2 | PDGFRA | 0.50 | 711 | 3 | 4 | 5 | 6 | VI-2 | S100A2 | 0.42 |
| 616 | 3 | 4 | 5 | 6 | | VI-2 | PDGFRB | 0.37 | 712 | 3 | 4 | 5 | 6 | VI-2 | S100A3 | 0.45 |
| 617 | 3 | 4 | 5 | 6 | | VI-2 | PDLIM1 | 0.36 | 713 | 3 | 4 | 5 | 6 | VI-2 | S1PR2 | 0.48 |
| 618 | 3 | 4 | 5 | 6 | | VI-2 | PEAK1 | 0.47 | 714 | 3 | 4 | 5 | 6 | VI-2 | SAFB | 0.49 |
| 619 | 3 | 4 | 5 | 6 | | VI-2 | PELP1 | 0.42 | 715 | 3 | 4 | 5 | 6 | VI-2 | SALL2 | 0.30 |
| 620 | 3 | 4 | 5 | 6 | | VI-2 | PER1 | 0.43 | 716 | 3 | 4 | 5 | 6 | VI-2 | SAMHD1 | 0.47 |
| 621 | 3 | 4 | 5 | 6 | | VI-2 | PHF12 | 0.48 | 717 | 3 | 4 | 5 | 6 | VI-2 | SARM1 | 0.35 |
| 622 | 3 | 4 | 5 | 6 | | VI-2 | PHF19 | 0.44 | 718 | 3 | 4 | 5 | 6 | VI-2 | SBF1 | 0.44 |
| 623 | 3 | 4 | 5 | 6 | | VI-2 | PHKG1 | 0.37 | 719 | 3 | 4 | 5 | 6 | VI-2 | SCARA3 | 0.44 |
| 624 | 3 | 4 | 5 | 6 | | VI-2 | PHRF1 | 0.43 | 720 | 3 | 4 | 5 | 6 | VI-2 | SCARA5 | 0.47 |
| 625 | 3 | 4 | 5 | 6 | | VI-2 | PIEZO1 | 0.36 | 721 | 3 | 4 | 5 | 6 | VI-2 | SCARF2 | 0.34 |
| 626 | 3 | 4 | 5 | 6 | | VI-2 | PIK3R5 | 0.42 | 722 | 3 | 4 | 5 | 6 | VI-2 | SCD5 | 0.49 |
| 627 | 3 | 4 | 5 | 6 | | VI-2 | PIK3R6 | 0.33 | 723 | 3 | 4 | 5 | 6 | VI-2 | SCN1B | 0.47 |
| 628 | 3 | 4 | 5 | 6 | | VI-2 | PIP5K1C | 0.46 | 724 | 3 | 4 | 5 | 6 | VI-2 | SCN4B | 0.32 |
| 629 | 3 | 4 | 5 | 6 | | VI-2 | PITPNM1 | 0.40 | 725 | 3 | 4 | 5 | 6 | VI-2 | SDC2 | 0.46 |
| 630 | 3 | 4 | 5 | 6 | | VI-2 | PITPNM3 | 0.31 | 726 | 3 | 4 | 5 | 6 | VI-2 | SDC3 | 0.49 |
| 631 | 3 | 4 | 5 | 6 | | VI-2 | PKD1 | 0.33 | 727 | 3 | 4 | 5 | 6 | VI-2 | SEC14L1 | 0.40 |
| 632 | 3 | 4 | 5 | 6 | | VI-2 | PKD1P1 | 0.29 | 728 | 3 | 4 | 5 | 6 | VI-2 | SECTM1 | 0.38 |
| 633 | 3 | 4 | 5 | 6 | | VI-2 | PLA2G4F | 0.48 | 729 | 3 | 4 | 5 | 6 | VI-2 | SEMA5B | 0.40 |
| 634 | 3 | 4 | 5 | 6 | | VI-2 | PLCB3 | 0.37 | 730 | 3 | 4 | 5 | 6 | VI-2 | SEPT9 | 0.49 |
| 635 | 3 | 4 | 5 | 6 | | VI-2 | PLEC | 0.22 | 731 | 3 | 4 | 5 | 6 | VI-2 | SERPINA5 | 0.39 |
| 636 | 3 | 4 | 5 | 6 | | VI-2 | PLEKHA4 | 0.29 | 732 | 3 | 4 | 5 | 6 | VI-2 | SERPINE1 | 0.25 |
| 637 | 3 | 4 | 5 | 6 | | VI-2 | PLEKHM1P | 0.27 | 733 | 3 | 4 | 5 | 6 | VI-2 | SERPINH1 | 0.43 |
| 638 | 3 | 4 | 5 | 6 | | VI-2 | PLEKHO1 | 0.49 | 734 | 3 | 4 | 5 | 6 | VI-2 | SETD1A | 0.32 |
| 639 | 3 | 4 | 5 | 6 | | VI-2 | PLOD3 | 0.46 | 735 | 3 | 4 | 5 | 6 | VI-2 | SETD1B | 0.45 |
| 640 | 3 | 4 | 5 | 6 | | VI-2 | PLTP | 0.21 | 736 | 3 | 4 | 5 | 6 | VI-2 | SF3A2 | 0.40 |
| 641 | 3 | 4 | 5 | 6 | | VI-2 | PLXNA2 | 0.48 | 737 | 3 | 4 | 5 | 6 | VI-2 | SF3B2 | 0.49 |
| 642 | 3 | 4 | 5 | 6 | | VI-2 | PLXNB1 | 0.42 | 738 | 3 | 4 | 5 | 6 | VI-2 | SFI1 | 0.45 |
| 643 | 3 | 4 | 5 | 6 | | VI-2 | PLXNB2 | 0.41 | 739 | 3 | 4 | 5 | 6 | VI-2 | SFRP4 | 0.20 |
| 644 | 3 | 4 | 5 | 6 | | VI-2 | PLXND1 | 0.38 | 740 | 3 | 4 | 5 | 6 | VI-2 | SFXN3 | 0.43 |
| 645 | 3 | 4 | 5 | 6 | | VI-2 | PML | 0.49 | 741 | 3 | 4 | 5 | 6 | VI-2 | SGPP1 | 0.47 |
| 646 | 3 | 4 | 5 | 6 | | VI-2 | PMP22 | 0.49 | 742 | 3 | 4 | 5 | 6 | VI-2 | SH3PXD2A | 0.44 |
| 647 | 3 | 4 | 5 | 6 | | VI-2 | POLG | 0.44 | 743 | 3 | 4 | 5 | 6 | VI-2 | SH3PXD2B | 0.34 |
| 648 | 3 | 4 | 5 | 6 | | VI-2 | POM ZP3 | 0.32 | 744 | 3 | 4 | 5 | 6 | VI-2 | SHROOM4 | 0.47 |
| 649 | 3 | 4 | 5 | 6 | | VI-2 | POPDC2 | 0.43 | 745 | 3 | 4 | 5 | 6 | VI-2 | SIGLEC1 | 0.31 |
| 650 | 3 | 4 | 5 | 6 | | VI-2 | POTEKP | 0.47 | 746 | 3 | 4 | 5 | 6 | VI-2 | SIK3 | 0.39 |
| 651 | 3 | 4 | 5 | 6 | | VI-2 | PPP1R16B | 0.42 | 747 | 3 | 4 | 5 | 6 | VI-2 | SKIV2L | 0.47 |
| 652 | 3 | 4 | 5 | 6 | | VI-2 | PPP6R1 | 0.47 | 748 | 3 | 4 | 5 | 6 | VI-2 | SLC16A2 | 0.46 |
| 653 | 3 | 4 | 5 | 6 | | VI-2 | PRAF2 | 0.42 | 749 | 3 | 4 | 5 | 6 | VI-2 | SLC16A5 | 0.50 |
| 654 | 3 | 4 | 5 | 6 | | VI-2 | PRELP | 0.48 | 750 | 3 | 4 | 5 | 6 | VI-2 | SLC17A7 | 0.36 |
| 655 | 3 | 4 | 5 | 6 | | VI-2 | PRIC285 | 0.36 | 751 | 3 | 4 | 5 | 6 | VI-2 | SLC22A23 | 0.47 |
| 656 | 3 | 4 | 5 | 6 | | VI-2 | PRKACG | 0.29 | 752 | 3 | 4 | 5 | 6 | VI-2 | SLC26A1 | 0.37 |
| 657 | 3 | 4 | 5 | 6 | | VI-2 | PRR12 | 0.30 | 753 | 3 | 4 | 5 | 6 | VI-2 | SLC29A1 | 0.44 |
| 658 | 3 | 4 | 5 | 6 | | VI-2 | PRR7 | 0.39 | 754 | 3 | 4 | 5 | 6 | VI-2 | SLC6A6 | 0.28 |
| 659 | 3 | 4 | 5 | 6 | | VI-2 | PRRX2 | 0.33 | 755 | 3 | 4 | 5 | 6 | VI-2 | SLC9A3 | 0.43 |
| 660 | 3 | 4 | 5 | 6 | | VI-2 | PSORS1C1 | 0.27 | 756 | 3 | 4 | 5 | 6 | VI-2 | SLIT3 | 0.25 |
| 661 | 3 | 4 | 5 | 6 | | VI-2 | PTCH2 | 0.29 | 757 | 3 | 4 | 5 | 6 | VI-2 | SMAD3 | 0.45 |
| 662 | 3 | 4 | 5 | 6 | | VI-2 | PTGDS | 0.50 | 758 | 3 | 4 | 5 | 6 | VI-2 | SMAD7 | 0.48 |
| 663 | 3 | 4 | 5 | 6 | | VI-2 | PTK2B | 0.45 | 759 | 3 | 4 | 5 | 6 | VI-2 | SMTN | 0.48 |
| 664 | 3 | 4 | 5 | 6 | | VI-2 | PTMS | 0.34 | 760 | 3 | 4 | 5 | 6 | VI-2 | SNAPC4 | 0.38 |
| 665 | 3 | 4 | 5 | 6 | | VI-2 | PTPN23 | 0.43 | 761 | 3 | 4 | 5 | 6 | VI-2 | SNED1 | 0.43 |
| 666 | 3 | 4 | 5 | 6 | | VI-2 | PTPN6 | 0.47 | 762 | 3 | 4 | 5 | 6 | VI-2 | SNRNP200 | 0.48 |
| 667 | 3 | 4 | 5 | 6 | | VI-2 | PTRF | 0.38 | 763 | 3 | 4 | 5 | 6 | VI-2 | SOX15 | 0.38 |
| 668 | 3 | 4 | 5 | 6 | | VI-2 | PTTG1 | 0.32 | 764 | 3 | 4 | 5 | 6 | VI-2 | SP2 | 0.50 |
| 669 | 3 | 4 | 5 | 6 | | VI-2 | QRICH1 | 0.44 | 765 | 3 | 4 | 5 | 6 | VI-2 | SPA17 | 0.49 |

Fig. 39 - 5

| # | | | | | | | |
|---|---|---|---|---|---|---|---|
| 766 | 3 | 4 | 5 | 6 | VI-2 | SPARC | 0.50 |
| 767 | 3 | 4 | 5 | 6 | VI-2 | SPEN | 0.38 |
| 768 | 3 | 4 | 5 | 6 | VI-2 | SPON2 | 0.46 |
| 769 | 3 | 4 | 5 | 6 | VI-2 | SPRED2 | 0.39 |
| 770 | 3 | 4 | 5 | 6 | VI-2 | SPRY1 | 0.41 |
| 771 | 3 | 4 | 5 | 6 | VI-2 | SPRY4 | 0.40 |
| 772 | 3 | 4 | 5 | 6 | VI-2 | SPSB1 | 0.46 |
| 773 | 3 | 4 | 5 | 6 | VI-2 | SPTAN1 | 0.45 |
| 774 | 3 | 4 | 5 | 6 | VI-2 | SRCAP | 0.27 |
| 775 | 3 | 4 | 5 | 6 | VI-2 | SRRM2 | 0.21 |
| 776 | 3 | 4 | 5 | 6 | VI-2 | SSCSD | 0.25 |
| 777 | 3 | 4 | 5 | 6 | VI-2 | SSH3 | 0.48 |
| 778 | 3 | 4 | 5 | 6 | VI-2 | STAG3L2 | 0.43 |
| 779 | 3 | 4 | 5 | 6 | VI-2 | STARD8 | 0.38 |
| 780 | 3 | 4 | 5 | 6 | VI-2 | STC1 | 0.28 |
| 781 | 3 | 4 | 5 | 6 | VI-2 | STEAP3 | 0.47 |
| 782 | 3 | 4 | 5 | 6 | VI-2 | STK32B | 0.33 |
| 783 | 3 | 4 | 5 | 6 | VI-2 | STK32C | 0.44 |
| 784 | 3 | 4 | 5 | 6 | VI-2 | STK35 | 0.41 |
| 785 | 3 | 4 | 5 | 6 | VI-2 | STMN2 | 0.37 |
| 786 | 3 | 4 | 5 | 6 | VI-2 | SUPT6H | 0.46 |
| 787 | 3 | 4 | 5 | 6 | VI-2 | SUV39H1 | 0.49 |
| 788 | 3 | 4 | 5 | 6 | VI-2 | SY8U | 0.46 |
| 789 | 3 | 4 | 5 | 6 | VI-2 | SYDE1 | 0.47 |
| 790 | 3 | 4 | 5 | 6 | VI-2 | SYMPK | 0.47 |
| 791 | 3 | 4 | 5 | 6 | VI-2 | SYNGAP1 | 0.36 |
| 792 | 3 | 4 | 5 | 6 | VI-2 | SYNPO | 0.38 |
| 793 | 3 | 4 | 5 | 6 | VI-2 | TACC3 | 0.37 |
| 794 | 3 | 4 | 5 | 6 | VI-2 | TACR2 | 0.29 |
| 795 | 3 | 4 | 5 | 6 | VI-2 | TADA2A | 0.40 |
| 796 | 3 | 4 | 5 | 6 | VI-2 | TAF6 | 0.47 |
| 797 | 3 | 4 | 5 | 6 | VI-2 | TAGLN2 | 0.35 |
| 798 | 3 | 4 | 5 | 6 | VI-2 | TAOK2 | 0.48 |
| 799 | 3 | 4 | 5 | 6 | VI-2 | TBC1D10C | 0.43 |
| 800 | 3 | 4 | 5 | 6 | VI-2 | TBC1D16 | 0.27 |
| 801 | 3 | 4 | 5 | 6 | VI-2 | TBX1 | 0.31 |
| 802 | 3 | 4 | 5 | 6 | VI-2 | TBX15 | 0.43 |
| 803 | 3 | 4 | 5 | 6 | VI-2 | TCOF1 | 0.50 |
| 804 | 3 | 4 | 5 | 6 | VI-2 | TCP11L2 | 0.50 |
| 805 | 3 | 4 | 5 | 6 | VI-2 | TFAP4 | 0.42 |
| 806 | 3 | 4 | 5 | 6 | VI-2 | TFEB | 0.49 |
| 807 | 3 | 4 | 5 | 6 | VI-2 | TFIP11 | 0.46 |
| 808 | 3 | 4 | 5 | 6 | VI-2 | TGFB3 | 0.42 |
| 809 | 3 | 4 | 5 | 6 | VI-2 | TGM3 | 0.39 |
| 810 | 3 | 4 | 5 | 6 | VI-2 | THRA | 0.30 |
| 811 | 3 | 4 | 5 | 6 | VI-2 | THSD1 | 0.46 |
| 812 | 3 | 4 | 5 | 6 | VI-2 | TIE1 | 0.35 |
| 813 | 3 | 4 | 5 | 6 | VI-2 | TIMP2 | 0.36 |
| 814 | 3 | 4 | 5 | 6 | VI-2 | TIMP3 | 0.47 |
| 815 | 3 | 4 | 5 | 6 | VI-2 | TLN1 | 0.38 |
| 816 | 3 | 4 | 5 | 6 | VI-2 | TMC8 | 0.48 |
| 817 | 3 | 4 | 5 | 6 | VI-2 | TMCC2 | 0.44 |
| 818 | 3 | 4 | 5 | 6 | VI-2 | TMEM119 | 0.35 |
| 819 | 3 | 4 | 5 | 6 | VI-2 | TMEM173 | 0.44 |
| 820 | 3 | 4 | 5 | 6 | VI-2 | TMEM231 | 0.42 |
| 821 | 3 | 4 | 5 | 6 | VI-2 | TMEM43 | 0.42 |
| 822 | 3 | 4 | 5 | 6 | VI-2 | TMOD3 | 0.46 |
| 823 | 3 | 4 | 5 | 6 | VI-2 | TNFRSF12A | 0.36 |
| 824 | 3 | 4 | 5 | 6 | VI-2 | TNFRSF1B | 0.43 |
| 825 | 3 | 4 | 5 | 6 | VI-2 | TNFSF12 | 0.47 |
| 826 | 3 | 4 | 5 | 6 | VI-2 | TNK1 | 0.49 |
| 827 | 3 | 4 | 5 | 6 | VI-2 | TNRC18 | 0.38 |
| 828 | 3 | 4 | 5 | 6 | VI-2 | TNS1 | 0.39 |
| 829 | 3 | 4 | 5 | 6 | VI-2 | TOM1L2 | 0.46 |
| 830 | 3 | 4 | 5 | 6 | VI-2 | TP73 | 0.45 |
| 831 | 3 | 4 | 5 | 6 | VI-2 | TPM4 | 0.48 |
| 832 | 3 | 4 | 5 | 6 | VI-2 | TPX2 | 0.43 |
| 833 | 3 | 4 | 5 | 6 | VI-2 | TRAM2 | 0.27 |
| 834 | 3 | 4 | 5 | 6 | VI-2 | TRERF1 | 0.39 |
| 835 | 3 | 4 | 5 | 6 | VI-2 | TRIM26 | 0.43 |
| 836 | 3 | 4 | 5 | 6 | VI-2 | TRIM3 | 0.48 |
| 837 | 3 | 4 | 5 | 6 | VI-2 | TRIO | 0.45 |
| 838 | 3 | 4 | 5 | 6 | VI-2 | TSC2 | 0.46 |
| 839 | 3 | 4 | 5 | 6 | VI-2 | TSC22D3 | 0.26 |
| 840 | 3 | 4 | 5 | 6 | VI-2 | TSHZ3 | 0.45 |
| 841 | 3 | 4 | 5 | 6 | VI-2 | TSPAN18 | 0.36 |
| 842 | 3 | 4 | 5 | 6 | VI-2 | TSPYL5 | 0.46 |
| 843 | 3 | 4 | 5 | 6 | VI-2 | TTC7A | 0.41 |
| 844 | 3 | 4 | 5 | 6 | VI-2 | TTLL5 | 0.42 |
| 845 | 3 | 4 | 5 | 6 | VI-2 | TUBB4A | 0.32 |
| 846 | 3 | 4 | 5 | 6 | VI-2 | TUBB6 | 0.50 |
| 847 | 3 | 4 | 5 | 6 | VI-2 | UBA1 | 0.45 |
| 848 | 3 | 4 | 5 | 6 | VI-2 | UBAP2L | 0.50 |
| 849 | 3 | 4 | 5 | 6 | VI-2 | UBD | 0.48 |
| 850 | 3 | 4 | 5 | 6 | VI-2 | UBE2O | 0.45 |
| 851 | 3 | 4 | 5 | 6 | VI-2 | UHRF1 | 0.48 |
| 852 | 3 | 4 | 5 | 6 | VI-2 | UNC13D | 0.46 |
| 853 | 3 | 4 | 5 | 6 | VI-2 | URGCP | 0.48 |
| 854 | 3 | 4 | 5 | 6 | VI-2 | USP21 | 0.49 |
| 855 | 3 | 4 | 5 | 6 | VI-2 | USP35 | 0.43 |
| 856 | 3 | 4 | 5 | 6 | VI-2 | USP36 | 0.44 |
| 857 | 3 | 4 | 5 | 6 | VI-2 | UST | 0.48 |
| 858 | 3 | 4 | 5 | 6 | VI-2 | VASH1 | 0.37 |
| 859 | 3 | 4 | 5 | 6 | VI-2 | VCAN | 0.40 |
| 860 | 3 | 4 | 5 | 6 | VI-2 | VEGFB | 0.47 |
| 861 | 3 | 4 | 5 | 6 | VI-2 | VEGFC | 0.40 |
| 862 | 3 | 4 | 5 | 6 | VI-2 | VENTX | 0.29 |
| 863 | 3 | 4 | 5 | 6 | VI-2 | VIM | 0.39 |
| 864 | 3 | 4 | 5 | 6 | VI-2 | VMAC | 0.30 |
| 865 | 3 | 4 | 5 | 6 | VI-2 | VPRBP | 0.39 |
| 866 | 3 | 4 | 5 | 6 | VI-2 | VSTM4 | 0.47 |
| 867 | 3 | 4 | 5 | 6 | VI-2 | VWF | 0.41 |
| 868 | 3 | 4 | 5 | 6 | VI-2 | WASH3P | 0.45 |
| 869 | 3 | 4 | 5 | 6 | VI-2 | WDR4 | 0.42 |
| 870 | 3 | 4 | 5 | 6 | VI-2 | WDR83 | 0.42 |
| 871 | 3 | 4 | 5 | 6 | VI-2 | WIPF1 | 0.44 |
| 872 | 3 | 4 | 5 | 6 | VI-2 | WISP2 | 0.41 |
| 873 | 3 | 4 | 5 | 6 | VI-2 | WNT10A | 0.30 |
| 874 | 3 | 4 | 5 | 6 | VI-2 | WNT3 | 0.32 |
| 875 | 3 | 4 | 5 | 6 | VI-2 | WNT4 | 0.42 |
| 876 | 3 | 4 | 5 | 6 | VI-2 | WNT6 | 0.48 |
| 877 | 3 | 4 | 5 | 6 | VI-2 | WTH3DI | 0.45 |
| 878 | 3 | 4 | 5 | 6 | VI-2 | XPC | 0.47 |
| 879 | 3 | 4 | 5 | 6 | VI-2 | XPNPEP2 | 0.43 |
| 880 | 3 | 4 | 5 | 6 | VI-2 | XPO6 | 0.42 |
| 881 | 3 | 4 | 5 | 6 | VI-2 | XRCC1 | 0.34 |
| 882 | 3 | 4 | 5 | 6 | VI-2 | YPEL4 | 0.33 |
| 883 | 3 | 4 | 5 | 6 | VI-2 | ZBTB12 | 0.46 |
| 884 | 3 | 4 | 5 | 6 | VI-2 | ZBTB25 | 0.48 |
| 885 | 3 | 4 | 5 | 6 | VI-2 | ZBTB4 | 0.42 |
| 886 | 3 | 4 | 5 | 6 | VI-2 | ZBTB47 | 0.35 |
| 887 | 3 | 4 | 5 | 6 | VI-2 | ZBTB48 | 0.48 |
| 888 | 3 | 4 | 5 | 6 | VI-2 | ZC3H18 | 0.47 |
| 889 | 3 | 4 | 5 | 6 | VI-2 | ZC3H4 | 0.45 |
| 890 | 3 | 4 | 5 | 6 | VI-2 | ZC3H7B | 0.47 |
| 891 | 3 | 4 | 5 | 6 | VI-2 | ZCCHC14 | 0.47 |
| 892 | 3 | 4 | 5 | 6 | VI-2 | ZCCHC24 | 0.48 |
| 893 | 3 | 4 | 5 | 6 | VI-2 | ZFP36 | 0.27 |
| 894 | 3 | 4 | 5 | 6 | VI-2 | ZHX2 | 0.35 |
| 895 | 3 | 4 | 5 | 6 | VI-2 | ZMIZ2 | 0.47 |
| 896 | 3 | 4 | 5 | 6 | VI-2 | ZNF142 | 0.30 |
| 897 | 3 | 4 | 5 | 6 | VI-2 | ZNF205 | 0.48 |
| 898 | 3 | 4 | 5 | 6 | VI-2 | ZNF317 | 0.47 |
| 899 | 3 | 4 | 5 | 6 | VI-2 | ZNF362 | 0.47 |
| 900 | 3 | 4 | 5 | 6 | VI-2 | ZNF438 | 0.48 |
| 901 | 3 | 4 | 5 | 6 | VI-2 | ZNF48 | 0.49 |
| 902 | 3 | 4 | 5 | 6 | VI-2 | ZNF487P | 0.41 |
| 903 | 3 | 4 | 5 | 6 | VI-2 | ZNF503-AS2 | 0.50 |
| 904 | 3 | 4 | 5 | 6 | VI-2 | ZNF512B | 0.44 |
| 905 | 3 | 4 | 5 | 6 | VI-2 | ZNF575 | 0.35 |
| 906 | 3 | 4 | 5 | 6 | VI-2 | ZNF608 | 0.44 |
| 907 | 3 | 4 | 5 | 6 | VI-2 | ZNF623 | 0.47 |
| 908 | 3 | 4 | 5 | 6 | VI-2 | ZNF629 | 0.39 |
| 909 | 3 | 4 | 5 | 6 | VI-2 | ZNF646 | 0.26 |
| 910 | 3 | 4 | 5 | 6 | VI-2 | ZNF668 | 0.48 |
| 911 | 3 | 4 | 5 | 6 | VI-2 | ZNF687 | 0.35 |
| 912 | 3 | 4 | 5 | 6 | VI-2 | ZNF768 | 0.47 |
| 913 | 3 | 4 | 5 | 6 | VI-2 | ZNF787 | 0.47 |
| 914 | 3 | 4 | 5 | 6 | VI-2 | ZNF853 | 0.43 |
| 915 | 3 | 4 | 5 | 6 | VI-2 | ZYX | 0.47 |
| 916 | 3 | 4 | 5 | 6 | VI-1 | ABCA8 | 2.06 |
| 917 | 3 | 4 | 5 | 6 | VI-1 | ACAD8 | 2.17 |
| 918 | 3 | 4 | 5 | 6 | VI-1 | ACO1 | 2.00 |
| 919 | 3 | 4 | 5 | 6 | VI-1 | AGR2 | 2.62 |
| 920 | 3 | 4 | 5 | 6 | VI-1 | AKAP9 | 3.76 |
| 921 | 3 | 4 | 5 | 6 | VI-1 | ALAS2 | 2.46 |
| 922 | 3 | 4 | 5 | 6 | VI-1 | ANKRD18B | 2.37 |
| 923 | 3 | 4 | 5 | 6 | VI-1 | ANKRD26 | 2.78 |
| 924 | 3 | 4 | 5 | 6 | VI-1 | ANKRD36 | 3.12 |
| 925 | 3 | 4 | 5 | 6 | VI-1 | APOBEC3A | 2.14 |
| 926 | 3 | 4 | 5 | 6 | VI-1 | AQP7P3 | 2.61 |
| 927 | 3 | 4 | 5 | 6 | VI-1 | ATP8A1 | 2.05 |
| 928 | 3 | 4 | 5 | 6 | VI-1 | ATRX | 3.36 |
| 929 | 3 | 4 | 5 | 6 | VI-1 | BCL2A1 | 2.34 |
| 930 | 3 | 4 | 5 | 6 | VI-1 | BHLHA15 | 3.01 |
| 931 | 3 | 4 | 5 | 6 | VI-1 | BOD1L | 3.58 |
| 932 | 3 | 4 | 5 | 6 | VI-1 | BPY2B | 2.01 |
| 933 | 3 | 4 | 5 | 6 | VI-1 | C2orf15 | 2.14 |
| 934 | 3 | 4 | 5 | 6 | VI-1 | C5orf46 | 2.26 |
| 935 | 3 | 4 | 5 | 6 | VI-1 | C5orf63 | 2.52 |
| 936 | 3 | 4 | 5 | 6 | VI-1 | C6orf163 | 2.96 |
| 937 | 3 | 4 | 5 | 6 | VI-1 | C7orf53 | 2.28 |
| 938 | 3 | 4 | 5 | 6 | VI-1 | CBR3-AS1 | 3.80 |
| 939 | 3 | 4 | 5 | 6 | VI-1 | CCDC142 | 2.75 |
| 940 | 3 | 4 | 5 | 6 | VI-1 | CCDC160 | 2.62 |
| 941 | 3 | 4 | 5 | 6 | VI-1 | CDH19 | 4.27 |
| 942 | 3 | 4 | 5 | 6 | VI-1 | CEACAM1 | 2.93 |
| 943 | 3 | 4 | 5 | 6 | VI-1 | CHD7 | 2.09 |
| 944 | 3 | 4 | 5 | 6 | VI-1 | COX7B | 2.08 |
| 945 | 3 | 4 | 5 | 6 | VI-1 | CSF3R | 4.05 |
| 946 | 3 | 4 | 5 | 6 | VI-1 | CSTA | 2.25 |
| 947 | 3 | 4 | 5 | 6 | VI-1 | CWF19L2 | 3.97 |
| 948 | 3 | 4 | 5 | 6 | VI-1 | CXCL1 | 3.26 |
| 949 | 3 | 4 | 5 | 6 | VI-1 | CXCR2 | 4.98 |
| 950 | 3 | 4 | 5 | 6 | VI-1 | CYP2C9 | 2.09 |
| 951 | 3 | 4 | 5 | 6 | VI-1 | CYP4F2 | 4.94 |
| 952 | 3 | 4 | 5 | 6 | VI-1 | DAAM1 | 2.00 |
| 953 | 3 | 4 | 5 | 6 | VI-1 | DCLRE1C | 2.12 |
| 954 | 3 | 4 | 5 | 6 | VI-1 | DCP1A | 2.56 |
| 955 | 3 | 4 | 5 | 6 | VI-1 | DEFB1 | 2.76 |
| 956 | 3 | 4 | 5 | 6 | VI-1 | DHRS2 | 3.49 |
| 957 | 3 | 4 | 5 | 6 | VI-1 | DNASE1 | 2.40 |

Fig. 39 - 6

| | | | | | | | | | | | | | | | | |
|---|---|---|---|---|---|---|---|---|---|---|---|---|---|---|---|---|
| 958 | 3 | 4 | 5 | 6 | | VI-1 | DPRXP4 | 2.76 | 1054 | 3 | 4 | 5 | 6 | | VI-1 | PDP2 | 2.04 |
| 959 | 3 | 4 | 5 | 6 | | VI-1 | EBLN2 | 3.00 | 1055 | 3 | 4 | 5 | 6 | | VI-1 | PHF14 | 2.34 |
| 960 | 3 | 4 | 5 | 6 | | VI-1 | EFCAB4A | 2.05 | 1056 | 3 | 4 | 5 | 6 | | VI-1 | PIGM | 2.46 |
| 961 | 3 | 4 | 5 | 6 | | VI-1 | EHF | 2.44 | 1057 | 3 | 4 | 5 | 6 | | VI-1 | PIP5K1B | 2.79 |
| 962 | 3 | 4 | 5 | 6 | | VI-1 | EIF5B | 2.23 | 1058 | 3 | 4 | 5 | 6 | | VI-1 | PLA2G7 | 2.46 |
| 963 | 3 | 4 | 5 | 6 | | VI-1 | ENC1 | 2.24 | 1059 | 3 | 4 | 5 | 6 | | VI-1 | PLA2R1 | 4.07 |
| 964 | 3 | 4 | 5 | 6 | | VI-1 | EPCAM | 2.12 | 1060 | 3 | 4 | 5 | 6 | | VI-1 | PON3 | 2.41 |
| 965 | 3 | 4 | 5 | 6 | | VI-1 | ERGIC2 | 2.28 | 1061 | 3 | 4 | 5 | 6 | | VI-1 | PPIG | 3.62 |
| 966 | 3 | 4 | 5 | 6 | | VI-1 | ESF1 | 4.48 | 1062 | 3 | 4 | 5 | 6 | | VI-1 | PPM1K | 2.93 |
| 967 | 3 | 4 | 5 | 6 | | VI-1 | FAM115A | 2.04 | 1063 | 3 | 4 | 5 | 6 | | VI-1 | PRINS | 2.91 |
| 968 | 3 | 4 | 5 | 6 | | VI-1 | FAM126B | 2.82 | 1064 | 3 | 4 | 5 | 6 | | VI-1 | PRRC2C | 2.21 |
| 969 | 3 | 4 | 5 | 6 | | VI-1 | FAM176A | 2.16 | 1065 | 3 | 4 | 5 | 6 | | VI-1 | PURA | 2.42 |
| 970 | 3 | 4 | 5 | 6 | | VI-1 | FAM217B | 2.43 | 1066 | 3 | 4 | 5 | 6 | | VI-1 | RAB17 | 2.07 |
| 971 | 3 | 4 | 5 | 6 | | VI-1 | FAM46A | 2.08 | 1067 | 3 | 4 | 5 | 6 | | VI-1 | RBM41 | 3.44 |
| 972 | 3 | 4 | 5 | 6 | | VI-1 | FAM46C | 2.56 | 1068 | 3 | 4 | 5 | 6 | | VI-1 | RERGL | 2.00 |
| 973 | 3 | 4 | 5 | 6 | | VI-1 | FAM63B | 2.54 | 1069 | 3 | 4 | 5 | 6 | | VI-1 | RHD | 2.80 |
| 974 | 3 | 4 | 5 | 6 | | VI-1 | FCGR3A | 4.04 | 1070 | 3 | 4 | 5 | 6 | | VI-1 | RNASE2 | 3.19 |
| 975 | 3 | 4 | 5 | 6 | | VI-1 | FETUB | 2.03 | 1071 | 3 | 4 | 5 | 6 | | VI-1 | RNF212 | 2.09 |
| 976 | 3 | 4 | 5 | 6 | | VI-1 | FFAR2 | 3.56 | 1072 | 3 | 4 | 5 | 6 | | VI-1 | ROPN1 | 2.22 |
| 977 | 3 | 4 | 5 | 6 | | VI-1 | FICD | 2.81 | 1073 | 3 | 4 | 5 | 6 | | VI-1 | RPL36A | 2.07 |
| 978 | 3 | 4 | 5 | 6 | | VI-1 | FLJ14107 | 2.01 | 1074 | 3 | 4 | 5 | 6 | | VI-1 | RSBN1L | 2.60 |
| 979 | 3 | 4 | 5 | 6 | | VI-1 | FLJ41200 | 2.53 | 1075 | 3 | 4 | 5 | 6 | | VI-1 | S100A12 | 4.94 |
| 980 | 3 | 4 | 5 | 6 | | VI-1 | FMO2 | 3.35 | 1076 | 3 | 4 | 5 | 6 | | VI-1 | SCGB3A2 | 2.12 |
| 981 | 3 | 4 | 5 | 6 | | VI-1 | FOXA1 | 2.33 | 1077 | 3 | 4 | 5 | 6 | | VI-1 | SELL | 4.25 |
| 982 | 3 | 4 | 5 | 6 | | VI-1 | FST | 2.44 | 1078 | 3 | 4 | 5 | 6 | | VI-1 | SLC25A18 | 2.70 |
| 983 | 3 | 4 | 5 | 6 | | VI-1 | GABRP | 2.07 | 1079 | 3 | 4 | 5 | 6 | | VI-1 | SLC26A7 | 2.39 |
| 984 | 3 | 4 | 5 | 6 | | VI-1 | GALNT7 | 3.32 | 1080 | 3 | 4 | 5 | 6 | | VI-1 | SLC35F5 | 2.34 |
| 985 | 3 | 4 | 5 | 6 | | VI-1 | GCC2 | 2.34 | 1081 | 3 | 4 | 5 | 6 | | VI-1 | SLC47A2 | 4.56 |
| 986 | 3 | 4 | 5 | 6 | | VI-1 | GFOD1 | 2.66 | 1082 | 3 | 4 | 5 | 6 | | VI-1 | SON | 2.37 |
| 987 | 3 | 4 | 5 | 6 | | VI-1 | GLRX2 | 2.25 | 1083 | 3 | 4 | 5 | 6 | | VI-1 | SORL1 | 2.48 |
| 988 | 3 | 4 | 5 | 6 | | VI-1 | GLYATL1 | 3.04 | 1084 | 3 | 4 | 5 | 6 | | VI-1 | SPDEF | 2.00 |
| 989 | 3 | 4 | 5 | 6 | | VI-1 | GPC6 | 2.09 | 1085 | 3 | 4 | 5 | 6 | | VI-1 | SPP1 | 4.51 |
| 990 | 3 | 4 | 5 | 6 | | VI-1 | GPR155 | 2.12 | 1086 | 3 | 4 | 5 | 6 | | VI-1 | STOX2 | 2.05 |
| 991 | 3 | 4 | 5 | 6 | | VI-1 | GPR160 | 2.23 | 1087 | 3 | 4 | 5 | 6 | | VI-1 | THOC2 | 3.17 |
| 992 | 3 | 4 | 5 | 6 | | VI-1 | GRIA2 | 2.12 | 1088 | 3 | 4 | 5 | 6 | | VI-1 | TMEM88B | 2.43 |
| 993 | 3 | 4 | 5 | 6 | | VI-1 | H2AFZ | 2.28 | 1089 | 3 | 4 | 5 | 6 | | VI-1 | TMPRSS2 | 2.79 |
| 994 | 3 | 4 | 5 | 6 | | VI-1 | HES1 | 3.21 | 1090 | 3 | 4 | 5 | 6 | | VI-1 | TMPRSS4 | 4.61 |
| 995 | 3 | 4 | 5 | 6 | | VI-1 | HI8CH | 2.49 | 1091 | 3 | 4 | 5 | 6 | | VI-1 | TNF | 2.43 |
| 996 | 3 | 4 | 5 | 6 | | VI-1 | HIST1H4D | 4.67 | 1092 | 3 | 4 | 5 | 6 | | VI-1 | TRIM38 | 2.33 |
| 997 | 3 | 4 | 5 | 6 | | VI-1 | HIST1H4H | 2.64 | 1093 | 3 | 4 | 5 | 6 | | VI-1 | TSH22 | 2.34 |
| 998 | 3 | 4 | 5 | 6 | | VI-1 | HLA-DRB6 | 3.48 | 1094 | 3 | 4 | 5 | 6 | | VI-1 | TSPAN6 | 2.34 |
| 999 | 3 | 4 | 5 | 6 | | VI-1 | HMBOX1 | 2.95 | 1095 | 3 | 4 | 5 | 6 | | VI-1 | TTTY14 | 3.73 |
| 1000 | 3 | 4 | 5 | 6 | | VI-1 | HSD17B2 | 4.57 | 1096 | 3 | 4 | 5 | 6 | | VI-1 | UBXN7 | 3.31 |
| 1001 | 3 | 4 | 5 | 6 | | VI-1 | HSP90AA1 | 2.10 | 1097 | 3 | 4 | 5 | 6 | | VI-1 | UGT2A1 | 2.65 |
| 1002 | 3 | 4 | 5 | 6 | | VI-1 | HSP90AA6P | 4.66 | 1098 | 3 | 4 | 5 | 6 | | VI-1 | UGT2B11 | 2.38 |
| 1003 | 3 | 4 | 5 | 6 | | VI-1 | IGF1 | 3.98 | 1099 | 3 | 4 | 5 | 6 | | VI-1 | UPK1A | 2.21 |
| 1004 | 3 | 4 | 5 | 6 | | VI-1 | IQGAP2 | 2.29 | 1100 | 3 | 4 | 5 | 6 | | VI-1 | USP9Y | 2.36 |
| 1005 | 3 | 4 | 5 | 6 | | VI-1 | KIAA1244 | 2.45 | 1101 | 3 | 4 | 5 | 6 | | VI-1 | VNN2 | 2.18 |
| 1006 | 3 | 4 | 5 | 6 | | VI-1 | KIAA1324 | 2.15 | 1102 | 3 | 4 | 5 | 6 | | VI-1 | WFDC2 | 2.03 |
| 1007 | 3 | 4 | 5 | 6 | | VI-1 | KIAA2026 | 2.27 | 1103 | 3 | 4 | 5 | 6 | | VI-1 | XGPY2 | 3.39 |
| 1008 | 3 | 4 | 5 | 6 | | VI-1 | KRT19 | 2.22 | 1104 | 3 | 4 | 5 | 6 | | VI-1 | ZFHX3 | 2.16 |
| 1009 | 3 | 4 | 5 | 6 | | VI-1 | LARP7 | 2.31 | 1105 | 3 | 4 | 5 | 6 | | VI-1 | ZFY | 2.42 |
| 1010 | 3 | 4 | 5 | 6 | | VI-1 | LOC100129269 | 3.03 | 1106 | 3 | 4 | 5 | 6 | | VI-1 | ZNF20 | 2.52 |
| 1011 | 3 | 4 | 5 | 6 | | VI-1 | LOC100192204 | 3.12 | 1107 | 3 | 4 | 5 | 6 | | VI-1 | ZNF281 | 3.27 |
| 1012 | 3 | 4 | 5 | 6 | | VI-1 | LOC100289230 | 2.88 | 1108 | 3 | 4 | 5 | 6 | | VI-1 | ZNF292 | 2.17 |
| 1013 | 3 | 4 | 5 | 6 | | VI-1 | LOC100292680 | 2.04 | 1109 | 3 | 4 | 5 | 6 | | VI-1 | ZNF43 | 2.00 |
| 1014 | 3 | 4 | 5 | 6 | | VI-1 | LOC100505649 | 2.11 | 1110 | 3 | 4 | 5 | 6 | | VI-1 | ZNF506 | 2.15 |
| 1015 | 3 | 4 | 5 | 6 | | VI-1 | LOC100507117 | 2.72 | 1111 | 3 | 4 | 5 | 6 | | VI-1 | ZNF540 | 2.57 |
| 1016 | 3 | 4 | 5 | 6 | | VI-1 | LOC202181 | 4.60 | 1112 | 3 | 4 | 5 | 6 | | VI-1 | ZNF547 | 2.06 |
| 1017 | 3 | 4 | 5 | 6 | | VI-1 | LOC286367 | 2.29 | 1113 | 3 | 4 | 5 | 6 | | VI-1 | ZNF714 | 2.53 |
| 1018 | 3 | 4 | 5 | 6 | | VI-1 | LOC391322 | 2.70 | 1114 | 3 | 4 | 5 | 6 | | VI-1 | ZNF737 | 2.16 |
| 1019 | 3 | 4 | 5 | 6 | | VI-1 | LOC440335 | 2.11 | 1115 | 3 | 4 | 5 | 6 | | VI-1 | ZNF791 | 4.92 |
| 1020 | 3 | 4 | 5 | 6 | | VI-1 | LOC440354 | 2.45 | 1116 | 3 | 4 | 5 | 6 | | VI-1 | ZNF793 | 2.57 |
| 1021 | 3 | 4 | 5 | 6 | | VI-1 | LOC440895 | 2.03 | 1117 | 3 | 4 | 5 | 6 | | VI-1 | ZNF814 | 2.34 |
| 1022 | 3 | 4 | 5 | 6 | | VI-1 | LOC728978 | 4.94 | 1118 | 3 | 4 | 5 | 6 | | VI-1 | ZNF91 | 4.03 |
| 1023 | 3 | 4 | 5 | 6 | | VI-1 | LOC729156 | 3.97 | 1119 | 3 | 4 | 5 | | | V-2 | A2M | 0.53 |
| 1024 | 3 | 4 | 5 | 6 | | VI-1 | LPIN1 | 3.19 | 1120 | 3 | 4 | 5 | | | V-2 | AARS | 0.59 |
| 1025 | 3 | 4 | 5 | 6 | | VI-1 | LRRC26 | 3.27 | 1121 | 3 | 4 | 5 | | | V-2 | ABCB8 | 0.52 |
| 1026 | 3 | 4 | 5 | 6 | | VI-1 | LTC4S | 2.27 | 1122 | 3 | 4 | 5 | | | V-2 | ABCC1 | 0.52 |
| 1027 | 3 | 4 | 5 | 6 | | VI-1 | LUST | 2.33 | 1123 | 3 | 4 | 5 | | | V-2 | ABCD1 | 0.58 |
| 1028 | 3 | 4 | 5 | 6 | | VI-1 | LZIC | 2.29 | 1124 | 3 | 4 | 5 | | | V-2 | ABCF2 | 0.64 |
| 1029 | 3 | 4 | 5 | 6 | | VI-1 | MAOA | 2.09 | 1125 | 3 | 4 | 5 | | | V-2 | ABHD2 | 0.66 |
| 1030 | 3 | 4 | 5 | 6 | | VI-1 | MAP1B | 2.16 | 1126 | 3 | 4 | 5 | | | V-2 | ABHD4 | 0.55 |
| 1031 | 3 | 4 | 5 | 6 | | VI-1 | MB | 2.40 | 1127 | 3 | 4 | 5 | | | V-2 | ABI3 | 0.65 |
| 1032 | 3 | 4 | 5 | 6 | | VI-1 | MGST1 | 2.90 | 1128 | 3 | 4 | 5 | | | V-2 | ABI3BP | 0.58 |
| 1033 | 3 | 4 | 5 | 6 | | VI-1 | MIR17HG | 2.91 | 1129 | 3 | 4 | 5 | | | V-2 | ABTB1 | 0.58 |
| 1034 | 3 | 4 | 5 | 6 | | VI-1 | MMD | 2.10 | 1130 | 3 | 4 | 5 | | | V-2 | ABTB2 | 0.57 |
| 1035 | 3 | 4 | 5 | 6 | | VI-1 | MPHOSPH8 | 2.85 | 1131 | 3 | 4 | 5 | | | V-2 | ACAD10 | 0.66 |
| 1036 | 3 | 4 | 5 | 6 | | VI-1 | MRAP | 3.22 | 1132 | 3 | 4 | 5 | | | V-2 | ACCN3 | 0.59 |
| 1037 | 3 | 4 | 5 | 6 | | VI-1 | MRS2P2 | 2.13 | 1133 | 3 | 4 | 5 | | | V-2 | ACD | 0.52 |
| 1038 | 3 | 4 | 5 | 6 | | VI-1 | MS4A7 | 2.36 | 1134 | 3 | 4 | 5 | | | V-2 | ACHE | 0.61 |
| 1039 | 3 | 4 | 5 | 6 | | VI-1 | MYBPC1 | 2.14 | 1135 | 3 | 4 | 5 | | | V-2 | ACTL10 | 0.65 |
| 1040 | 3 | 4 | 5 | 6 | | VI-1 | NAIP | 2.03 | 1136 | 3 | 4 | 5 | | | V-2 | ACTN4 | 0.52 |
| 1041 | 3 | 4 | 5 | 6 | | VI-1 | NCOR1 | 2.04 | 1137 | 3 | 4 | 5 | | | V-2 | ACVR1 | 0.57 |
| 1042 | 3 | 4 | 5 | 6 | | VI-1 | NEDD4L | 3.28 | 1138 | 3 | 4 | 5 | | | V-2 | ADAL | 0.63 |
| 1043 | 3 | 4 | 5 | 6 | | VI-1 | NEURL3 | 2.18 | 1139 | 3 | 4 | 5 | | | V-2 | ADAMTS14 | 0.50 |
| 1044 | 3 | 4 | 5 | 6 | | VI-1 | NFIB | 2.34 | 1140 | 3 | 4 | 5 | | | V-2 | ADAMTS7 | 0.51 |
| 1045 | 3 | 4 | 5 | 6 | | VI-1 | NPAS1 | 2.21 | 1141 | 3 | 4 | 5 | | | V-2 | ADAMTSL1 | 0.56 |
| 1046 | 3 | 4 | 5 | 6 | | VI-1 | NPL | 2.78 | 1142 | 3 | 4 | 5 | | | V-2 | ADARB1 | 0.60 |
| 1047 | 3 | 4 | 5 | 6 | | VI-1 | NPY5R | 2.30 | 1143 | 3 | 4 | 5 | | | V-2 | ADCK4 | 0.65 |
| 1048 | 3 | 4 | 5 | 6 | | VI-1 | NRXN3 | 2.52 | 1144 | 3 | 4 | 5 | | | V-2 | ADCY7 | 0.50 |
| 1049 | 3 | 4 | 5 | 6 | | VI-1 | NSUN7 | 2.14 | 1145 | 3 | 4 | 5 | | | V-2 | ADD1 | 0.54 |
| 1050 | 3 | 4 | 5 | 6 | | VI-1 | OLAH | 2.35 | 1146 | 3 | 4 | 5 | | | V-2 | ADORA2B | 0.64 |
| 1051 | 3 | 4 | 5 | 6 | | VI-1 | OSGEPL1 | 2.05 | 1147 | 3 | 4 | 5 | | | V-2 | ADPRH | 0.52 |
| 1052 | 3 | 4 | 5 | 6 | | VI-1 | PARD6B | 2.25 | 1148 | 3 | 4 | 5 | | | V-2 | ADRBK1 | 0.62 |
| 1053 | 3 | 4 | 5 | 6 | | VI-1 | PDE6A | 2.01 | 1149 | 3 | 4 | 5 | | | V-2 | AES | 0.57 |

Fig. 39 - 7

| | | | | | | | | | | | | | | | |
|---|---|---|---|---|---|---|---|---|---|---|---|---|---|---|---|
| 1150 | 3 | 4 | 5 | | | V-2 | AFAP1 | 0.54 | 1246 | 3 | 4 | 5 | | V-2 | BRD7 | 0.61 |
| 1151 | 3 | 4 | 5 | | | V-2 | AFAP1L2 | 0.54 | 1247 | 3 | 4 | 5 | | V-2 | BRF2 | 0.62 |
| 1152 | 3 | 4 | 5 | | | V-2 | AGRN | 0.58 | 1248 | 3 | 4 | 5 | | V-2 | BRMS1 | 0.63 |
| 1153 | 3 | 4 | 5 | | | V-2 | AHSA1 | 0.59 | 1249 | 3 | 4 | 5 | | V-2 | BST1 | 0.63 |
| 1154 | 3 | 4 | 5 | | | V-2 | AIMP2 | 0.66 | 1250 | 3 | 4 | 5 | | V-2 | BST2 | 0.51 |
| 1155 | 3 | 4 | 5 | | | V-2 | AIP | 0.53 | 1251 | 3 | 4 | 5 | | V-2 | BTBD2 | 0.53 |
| 1156 | 3 | 4 | 5 | | | V-2 | AKAP17A | 0.65 | 1252 | 3 | 4 | 5 | | V-2 | BTN2A2 | 0.64 |
| 1157 | 3 | 4 | 5 | | | V-2 | AKIP1 | 0.55 | 1253 | 3 | 4 | 5 | | V-2 | BTN3A1 | 0.66 |
| 1158 | 3 | 4 | 5 | | | V-2 | ALAD | 0.63 | 1254 | 3 | 4 | 5 | | V-2 | BTN3A3 | 0.65 |
| 1159 | 3 | 4 | 5 | | | V-2 | ALDH16A1 | 0.52 | 1255 | 3 | 4 | 5 | | V-2 | BUD13 | 0.62 |
| 1160 | 3 | 4 | 5 | | | V-2 | ALDH1L2 | 0.65 | 1256 | 3 | 4 | 5 | | V-2 | C10orf114 | 0.67 |
| 1161 | 3 | 4 | 5 | | | V-2 | ALDH3B1 | 0.65 | 1257 | 3 | 4 | 5 | | V-2 | C10orf54 | 0.57 |
| 1162 | 3 | 4 | 5 | | | V-2 | ALKBH2 | 0.55 | 1258 | 3 | 4 | 5 | | V-2 | C11orf93 | 0.65 |
| 1163 | 3 | 4 | 5 | | | V-2 | ALKBH4 | 0.57 | 1259 | 3 | 4 | 5 | | V-2 | C11orf95 | 0.66 |
| 1164 | 3 | 4 | 5 | | | V-2 | ALKBH5 | 0.51 | 1260 | 3 | 4 | 5 | | V-2 | C12orf10 | 0.60 |
| 1165 | 3 | 4 | 5 | | | V-2 | ALOX5 | 0.58 | 1261 | 3 | 4 | 5 | | V-2 | C12orf5 | 0.52 |
| 1166 | 3 | 4 | 5 | | | V-2 | ALYREF | 0.57 | 1262 | 3 | 4 | 5 | | V-2 | C14orf159 | 0.67 |
| 1167 | 3 | 4 | 5 | | | V-2 | AMBRA1 | 0.56 | 1263 | 3 | 4 | 5 | | V-2 | C14orf79 | 0.54 |
| 1168 | 3 | 4 | 5 | | | V-2 | AMPD2 | 0.64 | 1264 | 3 | 4 | 5 | | V-2 | C14orf93 | 0.52 |
| 1169 | 3 | 4 | 5 | | | V-2 | AMPD3 | 0.60 | 1265 | 3 | 4 | 5 | | V-2 | C16orf13 | 0.61 |
| 1170 | 3 | 4 | 5 | | | V-2 | ANAPC1 | 0.67 | 1266 | 3 | 4 | 5 | | V-2 | C16orf53 | 0.66 |
| 1171 | 3 | 4 | 5 | | | V-2 | ANAPC2 | 0.51 | 1267 | 3 | 4 | 5 | | V-2 | C16orf58 | 0.58 |
| 1172 | 3 | 4 | 5 | | | V-2 | ANGEL1 | 0.52 | 1268 | 3 | 4 | 5 | | V-2 | C16orf80 | 0.62 |
| 1173 | 3 | 4 | 5 | | | V-2 | ANKLE2 | 0.62 | 1269 | 3 | 4 | 5 | | V-2 | C17orf53 | 0.66 |
| 1174 | 3 | 4 | 5 | | | V-2 | ANKRD13D | 0.62 | 1270 | 3 | 4 | 5 | | V-2 | C17orf61-PLSCR3 | 0.52 |
| 1175 | 3 | 4 | 5 | | | V-2 | ANKS1A | 0.57 | 1271 | 3 | 4 | 5 | | V-2 | C17orf70 | 0.63 |
| 1176 | 3 | 4 | 5 | | | V-2 | ANKS6 | 0.55 | 1272 | 3 | 4 | 5 | | V-2 | C19orf29 | 0.53 |
| 1177 | 3 | 4 | 5 | | | V-2 | ANP32AP1 | 0.62 | 1273 | 3 | 4 | 5 | | V-2 | C19orf43 | 0.58 |
| 1178 | 3 | 4 | 5 | | | V-2 | ANXA11 | 0.59 | 1274 | 3 | 4 | 5 | | V-2 | C19orf51 | 0.64 |
| 1179 | 3 | 4 | 5 | | | V-2 | ANXA2P2 | 0.51 | 1275 | 3 | 4 | 5 | | V-2 | C19orf53 | 0.61 |
| 1180 | 3 | 4 | 5 | | | V-2 | ANXA5 | 0.62 | 1276 | 3 | 4 | 5 | | V-2 | C19orf57 | 0.54 |
| 1181 | 3 | 4 | 5 | | | V-2 | AP1M1 | 0.60 | 1277 | 3 | 4 | 5 | | V-2 | C19orf70 | 0.67 |
| 1182 | 3 | 4 | 5 | | | V-2 | AP2A1 | 0.61 | 1278 | 3 | 4 | 5 | | V-2 | C19orf71 | 0.56 |
| 1183 | 3 | 4 | 5 | | | V-2 | AP2A2 | 0.63 | 1279 | 3 | 4 | 5 | | V-2 | C19orf77 | 0.52 |
| 1184 | 3 | 4 | 5 | | | V-2 | AP2B1 | 0.56 | 1280 | 3 | 4 | 5 | | V-2 | C1orf201 | 0.66 |
| 1185 | 3 | 4 | 5 | | | V-2 | AP3D1 | 0.66 | 1281 | 3 | 4 | 5 | | V-2 | C1orf212 | 0.62 |
| 1186 | 3 | 4 | 5 | | | V-2 | AP4E1 | 0.65 | 1282 | 3 | 4 | 5 | | V-2 | C1orf216 | 0.55 |
| 1187 | 3 | 4 | 5 | | | V-2 | APOBEC3B | 0.59 | 1283 | 3 | 4 | 5 | | V-2 | C1orf86 | 0.64 |
| 1188 | 3 | 4 | 5 | | | V-2 | APOL1 | 0.62 | 1284 | 3 | 4 | 5 | | V-2 | C1orf95 | 0.53 |
| 1189 | 3 | 4 | 5 | | | V-2 | APOL3 | 0.52 | 1285 | 3 | 4 | 5 | | V-2 | C1QTNF1 | 0.50 |
| 1190 | 3 | 4 | 5 | | | V-2 | AQR | 0.66 | 1286 | 3 | 4 | 5 | | V-2 | C1QTNF6 | 0.52 |
| 1191 | 3 | 4 | 5 | | | V-2 | ARAF | 0.66 | 1287 | 3 | 4 | 5 | | V-2 | C1QTNF7 | 0.53 |
| 1192 | 3 | 4 | 5 | | | V-2 | ARAP1 | 0.67 | 1288 | 3 | 4 | 5 | | V-2 | C1S | 0.51 |
| 1193 | 3 | 4 | 5 | | | V-2 | ARHGAP1 | 0.61 | 1289 | 3 | 4 | 5 | | V-2 | C20orf118 | 0.51 |
| 1194 | 3 | 4 | 5 | | | V-2 | ARHGAP10 | 0.56 | 1290 | 3 | 4 | 5 | | V-2 | C20orf27 | 0.66 |
| 1195 | 3 | 4 | 5 | | | V-2 | ARHGAP11A | 0.60 | 1291 | 3 | 4 | 5 | | V-2 | C21orf2 | 0.51 |
| 1196 | 3 | 4 | 5 | | | V-2 | ARHGAP39 | 0.54 | 1292 | 3 | 4 | 5 | | V-2 | C22orf13 | 0.63 |
| 1197 | 3 | 4 | 5 | | | V-2 | ARHGDIB | 0.62 | 1293 | 3 | 4 | 5 | | V-2 | C22orf46 | 0.53 |
| 1198 | 3 | 4 | 5 | | | V-2 | ARHGEF1 | 0.60 | 1294 | 3 | 4 | 5 | | V-2 | C2CD2L | 0.66 |
| 1199 | 3 | 4 | 5 | | | V-2 | ARHGEF18 | 0.62 | 1295 | 3 | 4 | 5 | | V-2 | C2orf42 | 0.62 |
| 1200 | 3 | 4 | 5 | | | V-2 | ARHGEF2 | 0.62 | 1296 | 3 | 4 | 5 | | V-2 | C2orf55 | 0.58 |
| 1201 | 3 | 4 | 5 | | | V-2 | ARHGEF4 | 0.55 | 1297 | 3 | 4 | 5 | | V-2 | C3orf18 | 0.65 |
| 1202 | 3 | 4 | 5 | | | V-2 | ARHGEF7 | 0.61 | 1298 | 3 | 4 | 5 | | V-2 | C4orf42 | 0.58 |
| 1203 | 3 | 4 | 5 | | | V-2 | ARL2 | 0.59 | 1299 | 3 | 4 | 5 | | V-2 | C4orf46 | 0.60 |
| 1204 | 3 | 4 | 5 | | | V-2 | ARL3 | 0.55 | 1300 | 3 | 4 | 5 | | V-2 | C6orf1 | 0.53 |
| 1205 | 3 | 4 | 5 | | | V-2 | ARL6IP4 | 0.57 | 1301 | 3 | 4 | 5 | | V-2 | C6orf89 | 0.66 |
| 1206 | 3 | 4 | 5 | | | V-2 | ARMC5 | 0.60 | 1302 | 3 | 4 | 5 | | V-2 | C7orf26 | 0.65 |
| 1207 | 3 | 4 | 5 | | | V-2 | ARMC7 | 0.57 | 1303 | 3 | 4 | 5 | | V-2 | C7orf49 | 0.62 |
| 1208 | 3 | 4 | 5 | | | V-2 | ARMCX1 | 0.63 | 1304 | 3 | 4 | 5 | | V-2 | C8orf37 | 0.58 |
| 1209 | 3 | 4 | 5 | | | V-2 | ARNT | 0.67 | 1305 | 3 | 4 | 5 | | V-2 | C9orf114 | 0.63 |
| 1210 | 3 | 4 | 5 | | | V-2 | ARNT2 | 0.63 | 1306 | 3 | 4 | 5 | | V-2 | C9orf25 | 0.65 |
| 1211 | 3 | 4 | 5 | | | V-2 | ARRB2 | 0.65 | 1307 | 3 | 4 | 5 | | V-2 | C9orf37 | 0.66 |
| 1212 | 3 | 4 | 5 | | | V-2 | ASB6 | 0.62 | 1308 | 3 | 4 | 5 | | V-2 | C9orf86 | 0.62 |
| 1213 | 3 | 4 | 5 | | | V-2 | ASCC2 | 0.52 | 1309 | 3 | 4 | 5 | | V-2 | CA5BP1 | 0.51 |
| 1214 | 3 | 4 | 5 | | | V-2 | ASF1B | 0.57 | 1310 | 3 | 4 | 5 | | V-2 | CABLES1 | 0.51 |
| 1215 | 3 | 4 | 5 | | | V-2 | ASPSCR1 | 0.62 | 1311 | 3 | 4 | 5 | | V-2 | CALU | 0.63 |
| 1216 | 3 | 4 | 5 | | | V-2 | ATAD3A | 0.59 | 1312 | 3 | 4 | 5 | | V-2 | CAMK1D | 0.62 |
| 1217 | 3 | 4 | 5 | | | V-2 | ATHL1 | 0.51 | 1313 | 3 | 4 | 5 | | V-2 | CAMKK2 | 0.52 |
| 1218 | 3 | 4 | 5 | | | V-2 | ATN1 | 0.58 | 1314 | 3 | 4 | 5 | | V-2 | CAPNS1 | 0.59 |
| 1219 | 3 | 4 | 5 | | | V-2 | ATP13A1 | 0.50 | 1315 | 3 | 4 | 5 | | V-2 | CAPZB | 0.51 |
| 1220 | 3 | 4 | 5 | | | V-2 | ATP13A2 | 0.60 | 1316 | 3 | 4 | 5 | | V-2 | CARD6 | 0.66 |
| 1221 | 3 | 4 | 5 | | | V-2 | ATP5SL | 0.66 | 1317 | 3 | 4 | 5 | | V-2 | CARD9 | 0.60 |
| 1222 | 3 | 4 | 5 | | | V-2 | ATXN7L2 | 0.60 | 1318 | 3 | 4 | 5 | | V-2 | CARM1 | 0.54 |
| 1223 | 3 | 4 | 5 | | | V-2 | ATXN7L3 | 0.56 | 1319 | 3 | 4 | 5 | | V-2 | CARNS1 | 0.54 |
| 1224 | 3 | 4 | 5 | | | V-2 | AUP1 | 0.53 | 1320 | 3 | 4 | 5 | | V-2 | CARS | 0.66 |
| 1225 | 3 | 4 | 5 | | | V-2 | AURKA | 0.54 | 1321 | 3 | 4 | 5 | | V-2 | CARS2 | 0.58 |
| 1226 | 3 | 4 | 5 | | | V-2 | B3GAT3 | 0.66 | 1322 | 3 | 4 | 5 | | V-2 | CASC3 | 0.55 |
| 1227 | 3 | 4 | 5 | | | V-2 | B4GALT2 | 0.65 | 1323 | 3 | 4 | 5 | | V-2 | CASKIN2 | 0.63 |
| 1228 | 3 | 4 | 5 | | | V-2 | B4GALT5 | 0.57 | 1324 | 3 | 4 | 5 | | V-2 | CASP7 | 0.62 |
| 1229 | 3 | 4 | 5 | | | V-2 | B4GALT7 | 0.66 | 1325 | 3 | 4 | 5 | | V-2 | CASP8 | 0.57 |
| 1230 | 3 | 4 | 5 | | | V-2 | B9D2 | 0.56 | 1326 | 3 | 4 | 5 | | V-2 | CAV1 | 0.61 |
| 1231 | 3 | 4 | 5 | | | V-2 | BACE1 | 0.51 | 1327 | 3 | 4 | 5 | | V-2 | CBFA2T2 | 0.56 |
| 1232 | 3 | 4 | 5 | | | V-2 | BAD | 0.67 | 1328 | 3 | 4 | 5 | | V-2 | CBFA2T3 | 0.61 |
| 1233 | 3 | 4 | 5 | | | V-2 | BAIAP2 | 0.57 | 1329 | 3 | 4 | 5 | | V-2 | CBWD2 | 0.64 |
| 1234 | 3 | 4 | 5 | | | V-2 | BANP | 0.64 | 1330 | 3 | 4 | 5 | | V-2 | CBX7 | 0.63 |
| 1235 | 3 | 4 | 5 | | | V-2 | BAP1 | 0.52 | 1331 | 3 | 4 | 5 | | V-2 | CC2D1A | 0.64 |
| 1236 | 3 | 4 | 5 | | | V-2 | BAZ2A | 0.57 | 1332 | 3 | 4 | 5 | | V-2 | CC2D1B | 0.62 |
| 1237 | 3 | 4 | 5 | | | V-2 | BBS1 | 0.66 | 1333 | 3 | 4 | 5 | | V-2 | CCDC117 | 0.64 |
| 1238 | 3 | 4 | 5 | | | V-2 | BCAR1 | 0.54 | 1334 | 3 | 4 | 5 | | V-2 | CCDC127 | 0.57 |
| 1239 | 3 | 4 | 5 | | | V-2 | BCL7C | 0.56 | 1335 | 3 | 4 | 5 | | V-2 | CCDC167 | 0.56 |
| 1240 | 3 | 4 | 5 | | | V-2 | BET1L | 0.67 | 1336 | 3 | 4 | 5 | | V-2 | CCDC71 | 0.51 |
| 1241 | 3 | 4 | 5 | | | V-2 | BHLHE40 | 0.57 | 1337 | 3 | 4 | 5 | | V-2 | CCDC74A | 0.61 |
| 1242 | 3 | 4 | 5 | | | V-2 | BMS1 | 0.66 | 1338 | 3 | 4 | 5 | | V-2 | CCDC88C | 0.53 |
| 1243 | 3 | 4 | 5 | | | V-2 | BRD1 | 0.59 | 1339 | 3 | 4 | 5 | | V-2 | CCHCR1 | 0.52 |
| 1244 | 3 | 4 | 5 | | | V-2 | BRD2 | 0.54 | 1340 | 3 | 4 | 5 | | V-2 | CD109 | 0.64 |
| 1245 | 3 | 4 | 5 | | | V-2 | BRD4 | 0.65 | 1341 | 3 | 4 | 5 | | V-2 | CD247 | 0.59 |

Fig. 39 - 8

| | | | | | | | | | | | | | | | | |
|---|---|---|---|---|---|---|---|---|---|---|---|---|---|---|---|---|
| 1342 | 3 | 4 | 5 | | | V-2 | CD40 | 0.66 | 1438 | 3 | 4 | 5 | | | V-2 | DDB2 | 0.56 |
| 1343 | 3 | 4 | 5 | | | V-2 | CD58 | 0.57 | 1439 | 3 | 4 | 5 | | | V-2 | DDX10 | 0.57 |
| 1344 | 3 | 4 | 5 | | | V-2 | CD63 | 0.60 | 1440 | 3 | 4 | 5 | | | V-2 | DDX19B | 0.58 |
| 1345 | 3 | 4 | 5 | | | V-2 | CD7 | 0.58 | 1441 | 3 | 4 | 5 | | | V-2 | DDX23 | 0.54 |
| 1346 | 3 | 4 | 5 | | | V-2 | CD79B | 0.54 | 1442 | 3 | 4 | 5 | | | V-2 | DDX24 | 0.53 |
| 1347 | 3 | 4 | 5 | | | V-2 | CDAN1 | 0.60 | 1443 | 3 | 4 | 5 | | | V-2 | DDX41 | 0.66 |
| 1348 | 3 | 4 | 5 | | | V-2 | CDC26 | 0.53 | 1444 | 3 | 4 | 5 | | | V-2 | DDX50 | 0.65 |
| 1349 | 3 | 4 | 5 | | | V-2 | CDC37 | 0.55 | 1445 | 3 | 4 | 5 | | | V-2 | DEDD2 | 0.58 |
| 1350 | 3 | 4 | 5 | | | V-2 | CDC42BPB | 0.52 | 1446 | 3 | 4 | 5 | | | V-2 | DENND5A | 0.55 |
| 1351 | 3 | 4 | 5 | | | V-2 | CDC42EP3 | 0.62 | 1447 | 3 | 4 | 5 | | | V-2 | DES | 0.58 |
| 1352 | 3 | 4 | 5 | | | V-2 | CDC42EP5 | 0.65 | 1448 | 3 | 4 | 5 | | | V-2 | DGCR11 | 0.64 |
| 1353 | 3 | 4 | 5 | | | V-2 | CDCA7L | 0.52 | 1449 | 3 | 4 | 5 | | | V-2 | DGCR14 | 0.59 |
| 1354 | 3 | 4 | 5 | | | V-2 | CDH6 | 0.63 | 1450 | 3 | 4 | 5 | | | V-2 | DGCR6 | 0.67 |
| 1355 | 3 | 4 | 5 | | | V-2 | CDK11B | 0.59 | 1451 | 3 | 4 | 5 | | | V-2 | DGCR8 | 0.55 |
| 1356 | 3 | 4 | 5 | | | V-2 | CDK16 | 0.53 | 1452 | 3 | 4 | 5 | | | V-2 | DGKQ | 0.52 |
| 1357 | 3 | 4 | 5 | | | V-2 | CDK2AP2 | 0.55 | 1453 | 3 | 4 | 5 | | | V-2 | DHODH | 0.63 |
| 1358 | 3 | 4 | 5 | | | V-2 | CDK9 | 0.65 | 1454 | 3 | 4 | 5 | | | V-2 | DHRS7 | 0.59 |
| 1359 | 3 | 4 | 5 | | | V-2 | CDS2 | 0.65 | 1455 | 3 | 4 | 5 | | | V-2 | DHX37 | 0.51 |
| 1360 | 3 | 4 | 5 | | | V-2 | CDT1 | 0.65 | 1456 | 3 | 4 | 5 | | | V-2 | DHX9 | 0.62 |
| 1361 | 3 | 4 | 5 | | | V-2 | CEBPD | 0.59 | 1457 | 3 | 4 | 5 | | | V-2 | DIDO1 | 0.59 |
| 1362 | 3 | 4 | 5 | | | V-2 | CELSR1 | 0.62 | 1458 | 3 | 4 | 5 | | | V-2 | DIS3L2 | 0.62 |
| 1363 | 3 | 4 | 5 | | | V-2 | CEP104 | 0.58 | 1459 | 3 | 4 | 5 | | | V-2 | DLX2 | 0.67 |
| 1364 | 3 | 4 | 5 | | | V-2 | CEP72 | 0.61 | 1460 | 3 | 4 | 5 | | | V-2 | DLST | 0.58 |
| 1365 | 3 | 4 | 5 | | | V-2 | CFL1 | 0.51 | 1461 | 3 | 4 | 5 | | | V-2 | DNAJC11 | 0.61 |
| 1366 | 3 | 4 | 5 | | | V-2 | CGREF1 | 0.53 | 1462 | 3 | 4 | 5 | | | V-2 | DNAJC14 | 0.57 |
| 1367 | 3 | 4 | 5 | | | V-2 | CHAF1B | 0.52 | 1463 | 3 | 4 | 5 | | | V-2 | DNM2 | 0.55 |
| 1368 | 3 | 4 | 5 | | | V-2 | CHD4 | 0.61 | 1464 | 3 | 4 | 5 | | | V-2 | DNTTIP1 | 0.66 |
| 1369 | 3 | 4 | 5 | | | V-2 | CHD8 | 0.57 | 1465 | 3 | 4 | 5 | | | V-2 | DOCK1 | 0.63 |
| 1370 | 3 | 4 | 5 | | | V-2 | CHERP | 0.62 | 1466 | 3 | 4 | 5 | | | V-2 | DOCK8 | 0.67 |
| 1371 | 3 | 4 | 5 | | | V-2 | CHFR | 0.63 | 1467 | 3 | 4 | 5 | | | V-2 | DOK1 | 0.54 |
| 1372 | 3 | 4 | 5 | | | V-2 | CHN1 | 0.57 | 1468 | 3 | 4 | 5 | | | V-2 | DOLK | 0.64 |
| 1373 | 3 | 4 | 5 | | | V-2 | CHST12 | 0.63 | 1469 | 3 | 4 | 5 | | | V-2 | DPP7 | 0.59 |
| 1374 | 3 | 4 | 5 | | | V-2 | CHST14 | 0.53 | 1470 | 3 | 4 | 5 | | | V-2 | DRAM1 | 0.60 |
| 1375 | 3 | 4 | 5 | | | V-2 | CHST15 | 0.52 | 1471 | 3 | 4 | 5 | | | V-2 | DROSHA | 0.51 |
| 1376 | 3 | 4 | 5 | | | V-2 | CHSY1 | 0.53 | 1472 | 3 | 4 | 5 | | | V-2 | DSCR3 | 0.67 |
| 1377 | 3 | 4 | 5 | | | V-2 | CIDEB | 0.51 | 1473 | 3 | 4 | 5 | | | V-2 | DUS2L | 0.65 |
| 1378 | 3 | 4 | 5 | | | V-2 | CINP | 0.64 | 1474 | 3 | 4 | 5 | | | V-2 | DUS3L | 0.51 |
| 1379 | 3 | 4 | 5 | | | V-2 | CISD3 | 0.61 | 1475 | 3 | 4 | 5 | | | V-2 | DVL1 | 0.62 |
| 1380 | 3 | 4 | 5 | | | V-2 | CITED2 | 0.51 | 1476 | 3 | 4 | 5 | | | V-2 | DYNLRB1 | 0.61 |
| 1381 | 3 | 4 | 5 | | | V-2 | CKS2 | 0.62 | 1477 | 3 | 4 | 5 | | | V-2 | DYRK1B | 0.61 |
| 1382 | 3 | 4 | 5 | | | V-2 | CLASP1 | 0.65 | 1478 | 3 | 4 | 5 | | | V-2 | DYRK3 | 0.62 |
| 1383 | 3 | 4 | 5 | | | V-2 | CLCN7 | 0.65 | 1479 | 3 | 4 | 5 | | | V-2 | E2F4 | 0.55 |
| 1384 | 3 | 4 | 5 | | | V-2 | CLEC16A | 0.59 | 1480 | 3 | 4 | 5 | | | V-2 | ECT2 | 0.63 |
| 1385 | 3 | 4 | 5 | | | V-2 | CLEC4F | 0.66 | 1481 | 3 | 4 | 5 | | | V-2 | EDC3 | 0.60 |
| 1386 | 3 | 4 | 5 | | | V-2 | CLEC4GP1 | 0.58 | 1482 | 3 | 4 | 5 | | | V-2 | EDF1 | 0.65 |
| 1387 | 3 | 4 | 5 | | | V-2 | CMKLR1 | 0.58 | 1483 | 3 | 4 | 5 | | | V-2 | EDNRA | 0.59 |
| 1388 | 3 | 4 | 5 | | | V-2 | CMTM3 | 0.65 | 1484 | 3 | 4 | 5 | | | V-2 | EEF1D | 0.54 |
| 1389 | 3 | 4 | 5 | | | V-2 | CNN2 | 0.62 | 1485 | 3 | 4 | 5 | | | V-2 | EFHC2 | 0.61 |
| 1390 | 3 | 4 | 5 | | | V-2 | CNNM1 | 0.54 | 1486 | 3 | 4 | 5 | | | V-2 | EFHD2 | 0.63 |
| 1391 | 3 | 4 | 5 | | | V-2 | CNNM3 | 0.56 | 1487 | 3 | 4 | 5 | | | V-2 | EFTUD2 | 0.64 |
| 1392 | 3 | 4 | 5 | | | V-2 | CNNM4 | 0.55 | 1488 | 3 | 4 | 5 | | | V-2 | EGLN2 | 0.66 |
| 1393 | 3 | 4 | 5 | | | V-2 | CNOT10 | 0.64 | 1489 | 3 | 4 | 5 | | | V-2 | EHMT1 | 0.62 |
| 1394 | 3 | 4 | 5 | | | V-2 | CNPY3 | 0.60 | 1490 | 3 | 4 | 5 | | | V-2 | EIF2AK1 | 0.65 |
| 1395 | 3 | 4 | 5 | | | V-2 | COG4 | 0.58 | 1491 | 3 | 4 | 5 | | | V-2 | EIF2D | 0.61 |
| 1396 | 3 | 4 | 5 | | | V-2 | COG7 | 0.64 | 1492 | 3 | 4 | 5 | | | V-2 | ELAC2 | 0.56 |
| 1397 | 3 | 4 | 5 | | | V-2 | COL12A1 | 0.62 | 1493 | 3 | 4 | 5 | | | V-2 | ELMO2 | 0.65 |
| 1398 | 3 | 4 | 5 | | | V-2 | COL4A2 | 0.59 | 1494 | 3 | 4 | 5 | | | V-2 | ELMO3 | 0.55 |
| 1399 | 3 | 4 | 5 | | | V-2 | CORO1B | 0.53 | 1495 | 3 | 4 | 5 | | | V-2 | ELOF1 | 0.64 |
| 1400 | 3 | 4 | 5 | | | V-2 | CORO7 | 0.51 | 1496 | 3 | 4 | 5 | | | V-2 | ELP3 | 0.65 |
| 1401 | 3 | 4 | 5 | | | V-2 | CPNE2 | 0.54 | 1497 | 3 | 4 | 5 | | | V-2 | EMILIN1 | 0.61 |
| 1402 | 3 | 4 | 5 | | | V-2 | CPSF7 | 0.54 | 1498 | 3 | 4 | 5 | | | V-2 | ENHO | 0.57 |
| 1403 | 3 | 4 | 5 | | | V-2 | CPXM1 | 0.51 | 1499 | 3 | 4 | 5 | | | V-2 | ENTPD1 | 0.63 |
| 1404 | 3 | 4 | 5 | | | V-2 | CPXM2 | 0.58 | 1500 | 3 | 4 | 5 | | | V-2 | ENY2 | 0.61 |
| 1405 | 3 | 4 | 5 | | | V-2 | CRAMP1L | 0.50 | 1501 | 3 | 4 | 5 | | | V-2 | EP300 | 0.53 |
| 1406 | 3 | 4 | 5 | | | V-2 | CREB3 | 0.61 | 1502 | 3 | 4 | 5 | | | V-2 | EP400 | 0.66 |
| 1407 | 3 | 4 | 5 | | | V-2 | CREB3L2 | 0.55 | 1503 | 3 | 4 | 5 | | | V-2 | EPAS1 | 0.61 |
| 1408 | 3 | 4 | 5 | | | V-2 | CRHR1 | 0.63 | 1504 | 3 | 4 | 5 | | | V-2 | EPB41L3 | 0.57 |
| 1409 | 3 | 4 | 5 | | | V-2 | CRISPLD2 | 0.65 | 1505 | 3 | 4 | 5 | | | V-2 | EPHA1 | 0.66 |
| 1410 | 3 | 4 | 5 | | | V-2 | CRY1 | 0.50 | 1506 | 3 | 4 | 5 | | | V-2 | EPHB4 | 0.61 |
| 1411 | 3 | 4 | 5 | | | V-2 | CSNK1D | 0.60 | 1507 | 3 | 4 | 5 | | | V-2 | EPS15L1 | 0.63 |
| 1412 | 3 | 4 | 5 | | | V-2 | CSNK1E | 0.61 | 1508 | 3 | 4 | 5 | | | V-2 | ERBB2 | 0.64 |
| 1413 | 3 | 4 | 5 | | | V-2 | CSNK1G2 | 0.60 | 1509 | 3 | 4 | 5 | | | V-2 | ERCC3 | 0.63 |
| 1414 | 3 | 4 | 5 | | | V-2 | CSRP2BP | 0.56 | 1510 | 3 | 4 | 5 | | | V-2 | ERGIC1 | 0.66 |
| 1415 | 3 | 4 | 5 | | | V-2 | CTDSP1 | 0.58 | 1511 | 3 | 4 | 5 | | | V-2 | ERI3 | 0.51 |
| 1416 | 3 | 4 | 5 | | | V-2 | CTIF | 0.62 | 1512 | 3 | 4 | 5 | | | V-2 | ESPL1 | 0.56 |
| 1417 | 3 | 4 | 5 | | | V-2 | CTNNA1 | 0.65 | 1513 | 3 | 4 | 5 | | | V-2 | ESPN | 0.55 |
| 1418 | 3 | 4 | 5 | | | V-2 | CTNNAL1 | 0.66 | 1514 | 3 | 4 | 5 | | | V-2 | ESYT1 | 0.61 |
| 1419 | 3 | 4 | 5 | | | V-2 | CTNNBL1 | 0.61 | 1515 | 3 | 4 | 5 | | | V-2 | ESYT2 | 0.56 |
| 1420 | 3 | 4 | 5 | | | V-2 | CTSZ | 0.55 | 1516 | 3 | 4 | 5 | | | V-2 | ETS1 | 0.55 |
| 1421 | 3 | 4 | 5 | | | V-2 | CXCL12 | 0.56 | 1517 | 3 | 4 | 5 | | | V-2 | ETV5 | 0.67 |
| 1422 | 3 | 4 | 5 | | | V-2 | CXXC1 | 0.59 | 1518 | 3 | 4 | 5 | | | V-2 | EXOC7 | 0.58 |
| 1423 | 3 | 4 | 5 | | | V-2 | CXXC5 | 0.60 | 1519 | 3 | 4 | 5 | | | V-2 | EXOSC2 | 0.63 |
| 1424 | 3 | 4 | 5 | | | V-2 | CYTH2 | 0.51 | 1520 | 3 | 4 | 5 | | | V-2 | EXOSC4 | 0.64 |
| 1425 | 3 | 4 | 5 | | | V-2 | DAB2 | 0.52 | 1521 | 3 | 4 | 5 | | | V-2 | F8A1 | 0.55 |
| 1426 | 3 | 4 | 5 | | | V-2 | DACT2 | 0.51 | 1522 | 3 | 4 | 5 | | | V-2 | FAAH | 0.50 |
| 1427 | 3 | 4 | 5 | | | V-2 | DACT3 | 0.62 | 1523 | 3 | 4 | 5 | | | V-2 | FAM101B | 0.53 |
| 1428 | 3 | 4 | 5 | | | V-2 | DAK | 0.61 | 1524 | 3 | 4 | 5 | | | V-2 | FAM105A | 0.54 |
| 1429 | 3 | 4 | 5 | | | V-2 | DAP | 0.55 | 1525 | 3 | 4 | 5 | | | V-2 | FAM108A1 | 0.62 |
| 1430 | 3 | 4 | 5 | | | V-2 | DAPK3 | 0.54 | 1526 | 3 | 4 | 5 | | | V-2 | FAM109B | 0.60 |
| 1431 | 3 | 4 | 5 | | | V-2 | DAXX | 0.57 | 1527 | 3 | 4 | 5 | | | V-2 | FAM120C | 0.52 |
| 1432 | 3 | 4 | 5 | | | V-2 | DBNDD2 | 0.61 | 1528 | 3 | 4 | 5 | | | V-2 | FAM125A | 0.57 |
| 1433 | 3 | 4 | 5 | | | V-2 | DCAF5 | 0.53 | 1529 | 3 | 4 | 5 | | | V-2 | FAM127A | 0.58 |
| 1434 | 3 | 4 | 5 | | | V-2 | DCN | 0.51 | 1530 | 3 | 4 | 5 | | | V-2 | FAM158A | 0.57 |
| 1435 | 3 | 4 | 5 | | | V-2 | DCP1B | 0.58 | 1531 | 3 | 4 | 5 | | | V-2 | FAM160A2 | 0.50 |
| 1436 | 3 | 4 | 5 | | | V-2 | DCPS | 0.56 | 1532 | 3 | 4 | 5 | | | V-2 | FAM160B2 | 0.57 |
| 1437 | 3 | 4 | 5 | | | V-2 | DDAH2 | 0.52 | 1533 | 3 | 4 | 5 | | | V-2 | FAM176B | 0.56 |

Fig. 39 - 9

| | | | | | | | | | | | | | | | |
|---|---|---|---|---|---|---|---|---|---|---|---|---|---|---|---|
| 1534 | 3 | 4 | 5 | | V-2 | FAM198B | 0.57 | 1630 | 3 | 4 | 5 | | V-2 | GNL3 | 0.51 |
| 1535 | 3 | 4 | 5 | | V-2 | FAM195B | 0.59 | 1631 | 3 | 4 | 5 | | V-2 | GPATCH1 | 0.58 |
| 1536 | 3 | 4 | 5 | | V-2 | FAM198A | 0.51 | 1632 | 3 | 4 | 5 | | V-2 | GPATCH8 | 0.54 |
| 1537 | 3 | 4 | 5 | | V-2 | FAM203A | 0.61 | 1633 | 3 | 4 | 5 | | V-2 | GPC1 | 0.55 |
| 1538 | 3 | 4 | 5 | | V-2 | FAM20C | 0.50 | 1634 | 3 | 4 | 5 | | V-2 | GPER | 0.65 |
| 1539 | 3 | 4 | 5 | | V-2 | FAM211A | 0.60 | 1635 | 3 | 4 | 5 | | V-2 | GPI | 0.67 |
| 1540 | 3 | 4 | 5 | | V-2 | FAM212A | 0.58 | 1636 | 3 | 4 | 5 | | V-2 | GPKOW | 0.56 |
| 1541 | 3 | 4 | 5 | | V-2 | FAM213B | 0.55 | 1637 | 3 | 4 | 5 | | V-2 | GPR107 | 0.65 |
| 1542 | 3 | 4 | 5 | | V-2 | FAM40A | 0.55 | 1638 | 3 | 4 | 5 | | V-2 | GPR108 | 0.64 |
| 1543 | 3 | 4 | 5 | | V-2 | FAM50B | 0.62 | 1639 | 3 | 4 | 5 | | V-2 | GPR137 | 0.60 |
| 1544 | 3 | 4 | 5 | | V-2 | FAM69C | 0.61 | 1640 | 3 | 4 | 5 | | V-2 | GPR161 | 0.62 |
| 1545 | 3 | 4 | 5 | | V-2 | FAM86EP | 0.63 | 1641 | 3 | 4 | 5 | | V-2 | GPRC5B | 0.50 |
| 1546 | 3 | 4 | 5 | | V-2 | FAM89B | 0.58 | 1642 | 3 | 4 | 5 | | V-2 | GPRC5C | 0.60 |
| 1547 | 3 | 4 | 5 | | V-2 | FAM92A1 | 0.64 | 1643 | 3 | 4 | 5 | | V-2 | GRAMD1A | 0.52 |
| 1548 | 3 | 4 | 5 | | V-2 | FANCG | 0.65 | 1644 | 3 | 4 | 5 | | V-2 | GRAMD4 | 0.58 |
| 1549 | 3 | 4 | 5 | | V-2 | FARP1 | 0.58 | 1645 | 3 | 4 | 5 | | V-2 | GRHL2 | 0.65 |
| 1550 | 3 | 4 | 5 | | V-2 | FARS2 | 0.63 | 1646 | 3 | 4 | 5 | | V-2 | GRWD1 | 0.60 |
| 1551 | 3 | 4 | 5 | | V-2 | FAT1 | 0.60 | 1647 | 3 | 4 | 5 | | V-2 | GSN | 0.63 |
| 1552 | 3 | 4 | 5 | | V-2 | FAU | 0.65 | 1648 | 3 | 4 | 5 | | V-2 | GSTP1 | 0.67 |
| 1553 | 3 | 4 | 5 | | V-2 | FBRS | 0.60 | 1649 | 3 | 4 | 5 | | V-2 | GTF3C5 | 0.55 |
| 1554 | 3 | 4 | 5 | | V-2 | FBRSL1 | 0.54 | 1650 | 3 | 4 | 5 | | V-2 | GTPBP6 | 0.66 |
| 1555 | 3 | 4 | 5 | | V-2 | FBXL19 | 0.55 | 1651 | 3 | 4 | 5 | | V-2 | GTSE1 | 0.61 |
| 1556 | 3 | 4 | 5 | | V-2 | FBXO18 | 0.60 | 1652 | 3 | 4 | 5 | | V-2 | GUCY1A3 | 0.59 |
| 1557 | 3 | 4 | 5 | | V-2 | FCHSD2 | 0.59 | 1653 | 3 | 4 | 5 | | V-2 | GUCY1B3 | 0.63 |
| 1558 | 3 | 4 | 5 | | V-2 | FERMT3 | 0.55 | 1654 | 3 | 4 | 5 | | V-2 | GYPC | 0.62 |
| 1559 | 3 | 4 | 5 | | V-2 | FGF16 | 0.65 | 1655 | 3 | 4 | 5 | | V-2 | GYS1 | 0.65 |
| 1560 | 3 | 4 | 5 | | V-2 | FILIP1L | 0.64 | 1656 | 3 | 4 | 5 | | V-2 | H2AFX | 0.61 |
| 1561 | 3 | 4 | 5 | | V-2 | FIZ1 | 0.67 | 1657 | 3 | 4 | 5 | | V-2 | HCG25 | 0.54 |
| 1562 | 3 | 4 | 5 | | V-2 | FJX1 | 0.52 | 1658 | 3 | 4 | 5 | | V-2 | HCK | 0.57 |
| 1563 | 3 | 4 | 5 | | V-2 | FKBP15 | 0.64 | 1659 | 3 | 4 | 5 | | V-2 | HDAC3 | 0.63 |
| 1564 | 3 | 4 | 5 | | V-2 | FKBP1AP1 | 0.62 | 1660 | 3 | 4 | 5 | | V-2 | HDAC5 | 0.60 |
| 1565 | 3 | 4 | 5 | | V-2 | FKBP2 | 0.65 | 1661 | 3 | 4 | 5 | | V-2 | HDGF | 0.57 |
| 1566 | 3 | 4 | 5 | | V-2 | FLJ13197 | 0.51 | 1662 | 3 | 4 | 5 | | V-2 | HDGFRP2 | 0.58 |
| 1567 | 3 | 4 | 5 | | V-2 | FLJ20021 | 0.60 | 1663 | 3 | 4 | 5 | | V-2 | HEATR7A | 0.56 |
| 1568 | 3 | 4 | 5 | | V-2 | FLJ31485 | 0.56 | 1664 | 3 | 4 | 5 | | V-2 | HECTD3 | 0.66 |
| 1569 | 3 | 4 | 5 | | V-2 | FLJ35390 | 0.63 | 1665 | 3 | 4 | 5 | | V-2 | HEPH | 0.64 |
| 1570 | 3 | 4 | 5 | | V-2 | FLNB | 0.56 | 1666 | 3 | 4 | 5 | | V-2 | HERC2 | 0.63 |
| 1571 | 3 | 4 | 5 | | V-2 | FLRT1 | 0.67 | 1667 | 3 | 4 | 5 | | V-2 | HERPUD2 | 0.66 |
| 1572 | 3 | 4 | 5 | | V-2 | FLYWCH2 | 0.54 | 1668 | 3 | 4 | 5 | | V-2 | HEXIM1 | 0.65 |
| 1573 | 3 | 4 | 5 | | V-2 | FNBP1 | 0.51 | 1669 | 3 | 4 | 5 | | V-2 | HGS | 0.56 |
| 1574 | 3 | 4 | 5 | | V-2 | FOXF1 | 0.54 | 1670 | 3 | 4 | 5 | | V-2 | HIC2 | 0.52 |
| 1575 | 3 | 4 | 5 | | V-2 | FOXK2 | 0.57 | 1671 | 3 | 4 | 5 | | V-2 | HIP1R | 0.66 |
| 1576 | 3 | 4 | 5 | | V-2 | FOXO1 | 0.63 | 1672 | 3 | 4 | 5 | | V-2 | HLA-B | 0.63 |
| 1577 | 3 | 4 | 5 | | V-2 | FOXP4 | 0.53 | 1673 | 3 | 4 | 5 | | V-2 | HLA-DMA | 0.53 |
| 1578 | 3 | 4 | 5 | | V-2 | FPGS | 0.54 | 1674 | 3 | 4 | 5 | | V-2 | HLA-E | 0.50 |
| 1579 | 3 | 4 | 5 | | V-2 | FRG1B | 0.63 | 1675 | 3 | 4 | 5 | | V-2 | HLX | 0.54 |
| 1580 | 3 | 4 | 5 | | V-2 | FRMD4A | 0.50 | 1676 | 3 | 4 | 5 | | V-2 | HM13 | 0.65 |
| 1581 | 3 | 4 | 5 | | V-2 | FRS2 | 0.65 | 1677 | 3 | 4 | 5 | | V-2 | HMGXB3 | 0.56 |
| 1582 | 3 | 4 | 5 | | V-2 | FSCN1 | 0.55 | 1678 | 3 | 4 | 5 | | V-2 | HMHA1 | 0.60 |
| 1583 | 3 | 4 | 5 | | V-2 | FSTL3 | 0.60 | 1679 | 3 | 4 | 5 | | V-2 | HNRNPUL2 | 0.62 |
| 1584 | 3 | 4 | 5 | | V-2 | FTH1 | 0.51 | 1680 | 3 | 4 | 5 | | V-2 | HOMER3 | 0.58 |
| 1585 | 3 | 4 | 5 | | V-2 | FTSJD2 | 0.51 | 1681 | 3 | 4 | 5 | | V-2 | HOXA4 | 0.58 |
| 1586 | 3 | 4 | 5 | | V-2 | FUCA2 | 0.61 | 1682 | 3 | 4 | 5 | | V-2 | HOXC9 | 0.58 |
| 1587 | 3 | 4 | 5 | | V-2 | FUK | 0.56 | 1683 | 3 | 4 | 5 | | V-2 | HPGDS | 0.55 |
| 1588 | 3 | 4 | 5 | | V-2 | FUT8 | 0.56 | 1684 | 3 | 4 | 5 | | V-2 | HPS1 | 0.66 |
| 1589 | 3 | 4 | 5 | | V-2 | FUZ | 0.60 | 1685 | 3 | 4 | 5 | | V-2 | HPS3 | 0.65 |
| 1590 | 3 | 4 | 5 | | V-2 | FYN | 0.57 | 1686 | 3 | 4 | 5 | | V-2 | HS3ST3A1 | 0.50 |
| 1591 | 3 | 4 | 5 | | V-2 | FZR1 | 0.65 | 1687 | 3 | 4 | 5 | | V-2 | HSD17B14 | 0.58 |
| 1592 | 3 | 4 | 5 | | V-2 | G6PC3 | 0.61 | 1688 | 3 | 4 | 5 | | V-2 | HSF1 | 0.62 |
| 1593 | 3 | 4 | 5 | | V-2 | GAB3 | 0.63 | 1689 | 3 | 4 | 5 | | V-2 | HTT | 0.51 |
| 1594 | 3 | 4 | 5 | | V-2 | GADD45A | 0.61 | 1690 | 3 | 4 | 5 | | V-2 | HYOU1 | 0.52 |
| 1595 | 3 | 4 | 5 | | V-2 | GADD45GIP1 | 0.62 | 1691 | 3 | 4 | 5 | | V-2 | ID3 | 0.55 |
| 1596 | 3 | 4 | 5 | | V-2 | GAK | 0.55 | 1692 | 3 | 4 | 5 | | V-2 | IDH3G | 0.56 |
| 1597 | 3 | 4 | 5 | | V-2 | GAL3ST4 | 0.57 | 1693 | 3 | 4 | 5 | | V-2 | IFI35 | 0.58 |
| 1598 | 3 | 4 | 5 | | V-2 | GANAB | 0.61 | 1694 | 3 | 4 | 5 | | V-2 | IFIT1 | 0.61 |
| 1599 | 3 | 4 | 5 | | V-2 | GAPDH | 0.61 | 1695 | 3 | 4 | 5 | | V-2 | IFIT5 | 0.60 |
| 1600 | 3 | 4 | 5 | | V-2 | GATAD2A | 0.54 | 1696 | 3 | 4 | 5 | | V-2 | IFITM1 | 0.65 |
| 1601 | 3 | 4 | 5 | | V-2 | GATAD2B | 0.59 | 1697 | 3 | 4 | 5 | | V-2 | IFITM10 | 0.55 |
| 1602 | 3 | 4 | 5 | | V-2 | GATS | 0.52 | 1698 | 3 | 4 | 5 | | V-2 | IFITM3 | 0.55 |
| 1603 | 3 | 4 | 5 | | V-2 | GBF1 | 0.51 | 1699 | 3 | 4 | 5 | | V-2 | IFT140 | 0.52 |
| 1604 | 3 | 4 | 5 | | V-2 | GBGT1 | 0.66 | 1700 | 3 | 4 | 5 | | V-2 | IFT172 | 0.53 |
| 1605 | 3 | 4 | 5 | | V-2 | GBP2 | 0.66 | 1701 | 3 | 4 | 5 | | V-2 | IFT46 | 0.66 |
| 1606 | 3 | 4 | 5 | | V-2 | GBP4 | 0.59 | 1702 | 3 | 4 | 5 | | V-2 | IGFBP7 | 0.56 |
| 1607 | 3 | 4 | 5 | | V-2 | GDI1 | 0.63 | 1703 | 3 | 4 | 5 | | V-2 | IGSF8 | 0.60 |
| 1608 | 3 | 4 | 5 | | V-2 | GEMIN5 | 0.62 | 1704 | 3 | 4 | 5 | | V-2 | IK | 0.58 |
| 1609 | 3 | 4 | 5 | | V-2 | GFER | 0.59 | 1705 | 3 | 4 | 5 | | V-2 | IKBKG | 0.57 |
| 1610 | 3 | 4 | 5 | | V-2 | GGA3 | 0.56 | 1706 | 3 | 4 | 5 | | V-2 | IKZF5 | 0.59 |
| 1611 | 3 | 4 | 5 | | V-2 | GGT1 | 0.61 | 1707 | 3 | 4 | 5 | | V-2 | IL17RA | 0.53 |
| 1612 | 3 | 4 | 5 | | V-2 | GGT5 | 0.66 | 1708 | 3 | 4 | 5 | | V-2 | IL17RD | 0.56 |
| 1613 | 3 | 4 | 5 | | V-2 | GGTLC2 | 0.61 | 1709 | 3 | 4 | 5 | | V-2 | IL1RAP | 0.66 |
| 1614 | 3 | 4 | 5 | | V-2 | GHDC | 0.61 | 1710 | 3 | 4 | 5 | | V-2 | IL22RA1 | 0.63 |
| 1615 | 3 | 4 | 5 | | V-2 | GIGYF2 | 0.66 | 1711 | 3 | 4 | 5 | | V-2 | IL28RA | 0.59 |
| 1616 | 3 | 4 | 5 | | V-2 | GIMAP1 | 0.55 | 1712 | 3 | 4 | 5 | | V-2 | IL33 | 0.66 |
| 1617 | 3 | 4 | 5 | | V-2 | GINS2 | 0.50 | 1713 | 3 | 4 | 5 | | V-2 | IL7 | 0.59 |
| 1618 | 3 | 4 | 5 | | V-2 | GIPC3 | 0.51 | 1714 | 3 | 4 | 5 | | V-2 | ILK | 0.62 |
| 1619 | 3 | 4 | 5 | | V-2 | GIT2 | 0.61 | 1715 | 3 | 4 | 5 | | V-2 | IMP4 | 0.67 |
| 1620 | 3 | 4 | 5 | | V-2 | GJA4 | 0.61 | 1716 | 3 | 4 | 5 | | V-2 | IMPDH1 | 0.59 |
| 1621 | 3 | 4 | 5 | | V-2 | GLB1 | 0.53 | 1717 | 3 | 4 | 5 | | V-2 | INF2 | 0.53 |
| 1622 | 3 | 4 | 5 | | V-2 | GLG1 | 0.59 | 1718 | 3 | 4 | 5 | | V-2 | ING1 | 0.57 |
| 1623 | 3 | 4 | 5 | | V-2 | GLI3 | 0.51 | 1719 | 3 | 4 | 5 | | V-2 | INO80 | 0.59 |
| 1624 | 3 | 4 | 5 | | V-2 | GLIPR1 | 0.58 | 1720 | 3 | 4 | 5 | | V-2 | INO80B | 0.59 |
| 1625 | 3 | 4 | 5 | | V-2 | GLIS1 | 0.59 | 1721 | 3 | 4 | 5 | | V-2 | INPP5D | 0.51 |
| 1626 | 3 | 4 | 5 | | V-2 | GLS2 | 0.66 | 1722 | 3 | 4 | 5 | | V-2 | IP6K1 | 0.56 |
| 1627 | 3 | 4 | 5 | | V-2 | GLYCTK | 0.63 | 1723 | 3 | 4 | 5 | | V-2 | IPMK | 0.61 |
| 1628 | 3 | 4 | 5 | | V-2 | GNA12 | 0.54 | 1724 | 3 | 4 | 5 | | V-2 | IPO4 | 0.60 |
| 1629 | 3 | 4 | 5 | | V-2 | GNA14 | 0.62 | 1725 | 3 | 4 | 5 | | V-2 | IPO9 | 0.66 |

Fig. 39 - 10

| | | | | | | | | | | | | | | | | |
|---|---|---|---|---|---|---|---|---|---|---|---|---|---|---|---|---|
| 1726 | 3 | 4 | 5 | | | V-2 | IQSEC1 | 0.55 | 1822 | 3 | 4 | 5 | | | V-2 | LOC375295 | 0.65 |
| 1727 | 3 | 4 | 5 | | | V-2 | IQSEC2 | 0.66 | 1823 | 3 | 4 | 5 | | | V-2 | LOC388630 | 0.51 |
| 1728 | 3 | 4 | 5 | | | V-2 | IRF2 | 0.61 | 1824 | 3 | 4 | 5 | | | V-2 | LOC401127 | 0.58 |
| 1729 | 3 | 4 | 5 | | | V-2 | ISY1 | 0.54 | 1825 | 3 | 4 | 5 | | | V-2 | LOC440434 | 0.63 |
| 1730 | 3 | 4 | 5 | | | V-2 | ITM2C | 0.54 | 1826 | 3 | 4 | 5 | | | V-2 | LOC493754 | 0.57 |
| 1731 | 3 | 4 | 5 | | | V-2 | ITPK1 | 0.59 | 1827 | 3 | 4 | 5 | | | V-2 | LOC606724 | 0.58 |
| 1732 | 3 | 4 | 5 | | | V-2 | ITPKB | 0.62 | 1828 | 3 | 4 | 5 | | | V-2 | LOC643387 | 0.61 |
| 1733 | 3 | 4 | 5 | | | V-2 | ITPR3 | 0.59 | 1829 | 3 | 4 | 5 | | | V-2 | LOC644172 | 0.53 |
| 1734 | 3 | 4 | 5 | | | V-2 | ITPRIPL1 | 0.63 | 1830 | 3 | 4 | 5 | | | V-2 | LOC644936 | 0.67 |
| 1735 | 3 | 4 | 5 | | | V-2 | IWS1 | 0.64 | 1831 | 3 | 4 | 5 | | | V-2 | LOC648987 | 0.56 |
| 1736 | 3 | 4 | 5 | | | V-2 | JAM3 | 0.57 | 1832 | 3 | 4 | 5 | | | V-2 | LOXL4 | 0.66 |
| 1737 | 3 | 4 | 5 | | | V-2 | JARID2 | 0.60 | 1833 | 3 | 4 | 5 | | | V-2 | LPAR1 | 0.52 |
| 1738 | 3 | 4 | 5 | | | V-2 | JMJD6 | 0.60 | 1834 | 3 | 4 | 5 | | | V-2 | LPCAT1 | 0.67 |
| 1739 | 3 | 4 | 5 | | | V-2 | JMJD7 | 0.56 | 1835 | 3 | 4 | 5 | | | V-2 | LPHN1 | 0.62 |
| 1740 | 3 | 4 | 5 | | | V-2 | JPH2 | 0.63 | 1836 | 3 | 4 | 5 | | | V-2 | LPPR2 | 0.65 |
| 1741 | 3 | 4 | 5 | | | V-2 | KANSL1 | 0.57 | 1837 | 3 | 4 | 5 | | | V-2 | LRCH1 | 0.65 |
| 1742 | 3 | 4 | 5 | | | V-2 | KAT8 | 0.59 | 1838 | 3 | 4 | 5 | | | V-2 | LRP3 | 0.63 |
| 1743 | 3 | 4 | 5 | | | V-2 | KBTBD4 | 0.52 | 1839 | 3 | 4 | 5 | | | V-2 | LRRC14 | 0.57 |
| 1744 | 3 | 4 | 5 | | | V-2 | KCNC4 | 0.56 | 1840 | 3 | 4 | 5 | | | V-2 | LRRC16B | 0.55 |
| 1745 | 3 | 4 | 5 | | | V-2 | KCND1 | 0.65 | 1841 | 3 | 4 | 5 | | | V-2 | LRRC20 | 0.63 |
| 1746 | 3 | 4 | 5 | | | V-2 | KCNH2 | 0.59 | 1842 | 3 | 4 | 5 | | | V-2 | LRRC37B | 0.53 |
| 1747 | 3 | 4 | 5 | | | V-2 | KCNIP3 | 0.59 | 1843 | 3 | 4 | 5 | | | V-2 | LRRC42 | 0.64 |
| 1748 | 3 | 4 | 5 | | | V-2 | KCNS3 | 0.60 | 1844 | 3 | 4 | 5 | | | V-2 | LRRC48 | 0.61 |
| 1749 | 3 | 4 | 5 | | | V-2 | KCTD10 | 0.59 | 1845 | 3 | 4 | 5 | | | V-2 | LRRC59 | 0.67 |
| 1750 | 3 | 4 | 5 | | | V-2 | KCTD13 | 0.57 | 1846 | 3 | 4 | 5 | | | V-2 | LRRN1 | 0.55 |
| 1751 | 3 | 4 | 5 | | | V-2 | KDELR1 | 0.66 | 1847 | 3 | 4 | 5 | | | V-2 | LRSAM1 | 0.64 |
| 1752 | 3 | 4 | 5 | | | V-2 | KDM2B | 0.63 | 1848 | 3 | 4 | 5 | | | V-2 | LSM12 | 0.65 |
| 1753 | 3 | 4 | 5 | | | V-2 | KDM4A | 0.62 | 1849 | 3 | 4 | 5 | | | V-2 | LSM14B | 0.64 |
| 1754 | 3 | 4 | 5 | | | V-2 | KDM4B | 0.65 | 1850 | 3 | 4 | 5 | | | V-2 | LTBP2 | 0.52 |
| 1755 | 3 | 4 | 5 | | | V-2 | KDM5B-AS1 | 0.54 | 1851 | 3 | 4 | 5 | | | V-2 | LTBP3 | 0.62 |
| 1756 | 3 | 4 | 5 | | | V-2 | KHNYN | 0.57 | 1852 | 3 | 4 | 5 | | | V-2 | LUM | 0.52 |
| 1757 | 3 | 4 | 5 | | | V-2 | KIAA0226 | 0.61 | 1853 | 3 | 4 | 5 | | | V-2 | LUZP1 | 0.65 |
| 1758 | 3 | 4 | 5 | | | V-2 | KIAA0240 | 0.66 | 1854 | 3 | 4 | 5 | | | V-2 | LY6K | 0.60 |
| 1759 | 3 | 4 | 5 | | | V-2 | KIAA0355 | 0.58 | 1855 | 3 | 4 | 5 | | | V-2 | LYPD1 | 0.65 |
| 1760 | 3 | 4 | 5 | | | V-2 | KIAA0930 | 0.65 | 1856 | 3 | 4 | 5 | | | V-2 | LYPLA2 | 0.66 |
| 1761 | 3 | 4 | 5 | | | V-2 | KIAA1462 | 0.53 | 1857 | 3 | 4 | 5 | | | V-2 | LYVE1 | 0.56 |
| 1762 | 3 | 4 | 5 | | | V-2 | KIAA1967 | 0.65 | 1858 | 3 | 4 | 5 | | | V-2 | LZTS2 | 0.59 |
| 1763 | 3 | 4 | 5 | | | V-2 | KIF13A | 0.59 | 1859 | 3 | 4 | 5 | | | V-2 | MAF1 | 0.58 |
| 1764 | 3 | 4 | 5 | | | V-2 | KIF17 | 0.67 | 1860 | 3 | 4 | 5 | | | V-2 | MAFF | 0.59 |
| 1765 | 3 | 4 | 5 | | | V-2 | KIF1C | 0.53 | 1861 | 3 | 4 | 5 | | | V-2 | MAGED2 | 0.59 |
| 1766 | 3 | 4 | 5 | | | V-2 | KIF22 | 0.51 | 1862 | 3 | 4 | 5 | | | V-2 | MAGEH1 | 0.57 |
| 1767 | 3 | 4 | 5 | | | V-2 | KLC1 | 0.66 | 1863 | 3 | 4 | 5 | | | V-2 | MAML2 | 0.55 |
| 1768 | 3 | 4 | 5 | | | V-2 | KLC2 | 0.59 | 1864 | 3 | 4 | 5 | | | V-2 | MAMLD1 | 0.50 |
| 1769 | 3 | 4 | 5 | | | V-2 | KLHDC4 | 0.56 | 1865 | 3 | 4 | 5 | | | V-2 | MAN1B1 | 0.65 |
| 1770 | 3 | 4 | 5 | | | V-2 | KLHL22 | 0.66 | 1866 | 3 | 4 | 5 | | | V-2 | MAN1C1 | 0.61 |
| 1771 | 3 | 4 | 5 | | | V-2 | KLHL26 | 0.64 | 1867 | 3 | 4 | 5 | | | V-2 | MAN2B2 | 0.56 |
| 1772 | 3 | 4 | 5 | | | V-2 | KRBA1 | 0.62 | 1868 | 3 | 4 | 5 | | | V-2 | MAP1S | 0.53 |
| 1773 | 3 | 4 | 5 | | | V-2 | KXD1 | 0.65 | 1869 | 3 | 4 | 5 | | | V-2 | MAP2K7 | 0.59 |
| 1774 | 3 | 4 | 5 | | | V-2 | L3MBTL2 | 0.63 | 1870 | 3 | 4 | 5 | | | V-2 | MAP3K10 | 0.58 |
| 1775 | 3 | 4 | 5 | | | V-2 | LAG3 | 0.65 | 1871 | 3 | 4 | 5 | | | V-2 | MAP3K3 | 0.53 |
| 1776 | 3 | 4 | 5 | | | V-2 | LAMA4 | 0.65 | 1872 | 3 | 4 | 5 | | | V-2 | MAP4K2 | 0.61 |
| 1777 | 3 | 4 | 5 | | | V-2 | LAMC1 | 0.61 | 1873 | 3 | 4 | 5 | | | V-2 | MAPK7 | 0.61 |
| 1778 | 3 | 4 | 5 | | | V-2 | LARGE | 0.56 | 1874 | 3 | 4 | 5 | | | V-2 | MARCH9 | 0.54 |
| 1779 | 3 | 4 | 5 | | | V-2 | LAS1L | 0.60 | 1875 | 3 | 4 | 5 | | | V-2 | MARS | 0.63 |
| 1780 | 3 | 4 | 5 | | | V-2 | LASP1 | 0.57 | 1876 | 3 | 4 | 5 | | | V-2 | MB21D2 | 0.62 |
| 1781 | 3 | 4 | 5 | | | V-2 | LATS2 | 0.53 | 1877 | 3 | 4 | 5 | | | V-2 | MBD1 | 0.58 |
| 1782 | 3 | 4 | 5 | | | V-2 | LAYN | 0.54 | 1878 | 3 | 4 | 5 | | | V-2 | MBD2 | 0.61 |
| 1783 | 3 | 4 | 5 | | | V-2 | LBH | 0.62 | 1879 | 3 | 4 | 5 | | | V-2 | MBNL1 | 0.66 |
| 1784 | 3 | 4 | 5 | | | V-2 | LCP2 | 0.64 | 1880 | 3 | 4 | 5 | | | V-2 | MBTPS1 | 0.66 |
| 1785 | 3 | 4 | 5 | | | V-2 | LEMD3 | 0.65 | 1881 | 3 | 4 | 5 | | | V-2 | MCM3 | 0.63 |
| 1786 | 3 | 4 | 5 | | | V-2 | LENG1 | 0.53 | 1882 | 3 | 4 | 5 | | | V-2 | MCM3AP | 0.52 |
| 1787 | 3 | 4 | 5 | | | V-2 | LEO1 | 0.56 | 1883 | 3 | 4 | 5 | | | V-2 | MCM5 | 0.55 |
| 1788 | 3 | 4 | 5 | | | V-2 | LEPRE1 | 0.52 | 1884 | 3 | 4 | 5 | | | V-2 | MCM7 | 0.64 |
| 1789 | 3 | 4 | 5 | | | V-2 | LEPREL1 | 0.66 | 1885 | 3 | 4 | 5 | | | V-2 | MCPH1 | 0.66 |
| 1790 | 3 | 4 | 5 | | | V-2 | LEPREL4 | 0.54 | 1886 | 3 | 4 | 5 | | | V-2 | MCU | 0.52 |
| 1791 | 3 | 4 | 5 | | | V-2 | LGALS1 | 0.66 | 1887 | 3 | 4 | 5 | | | V-2 | MED11 | 0.64 |
| 1792 | 3 | 4 | 5 | | | V-2 | LHFPL2 | 0.67 | 1888 | 3 | 4 | 5 | | | V-2 | MED15 | 0.53 |
| 1793 | 3 | 4 | 5 | | | V-2 | LIG1 | 0.55 | 1889 | 3 | 4 | 5 | | | V-2 | MED22 | 0.63 |
| 1794 | 3 | 4 | 5 | | | V-2 | LIMD2 | 0.67 | 1890 | 3 | 4 | 5 | | | V-2 | MED25 | 0.51 |
| 1795 | 3 | 4 | 5 | | | V-2 | LIMK1 | 0.64 | 1891 | 3 | 4 | 5 | | | V-2 | MED27 | 0.63 |
| 1796 | 3 | 4 | 5 | | | V-2 | LINC00086 | 0.61 | 1892 | 3 | 4 | 5 | | | V-2 | MED29 | 0.64 |
| 1797 | 3 | 4 | 5 | | | V-2 | LINC00094 | 0.55 | 1893 | 3 | 4 | 5 | | | V-2 | MEN1 | 0.62 |
| 1798 | 3 | 4 | 5 | | | V-2 | LINC00204A | 0.56 | 1894 | 3 | 4 | 5 | | | V-2 | MEOX2 | 0.54 |
| 1799 | 3 | 4 | 5 | | | V-2 | LMCD1 | 0.57 | 1895 | 3 | 4 | 5 | | | V-2 | MESDC1 | 0.65 |
| 1800 | 3 | 4 | 5 | | | V-2 | LMNB1 | 0.61 | 1896 | 3 | 4 | 5 | | | V-2 | MET | 0.51 |
| 1801 | 3 | 4 | 5 | | | V-2 | LMO2 | 0.60 | 1897 | 3 | 4 | 5 | | | V-2 | MFNG | 0.56 |
| 1802 | 3 | 4 | 5 | | | V-2 | LMTK2 | 0.66 | 1898 | 3 | 4 | 5 | | | V-2 | MFSD12 | 0.61 |
| 1803 | 3 | 4 | 5 | | | V-2 | LOC100128252 | 0.62 | 1899 | 3 | 4 | 5 | | | V-2 | MGAT3 | 0.55 |
| 1804 | 3 | 4 | 5 | | | V-2 | LOC100128361 | 0.52 | 1900 | 3 | 4 | 5 | | | V-2 | MGC27345 | 0.66 |
| 1805 | 3 | 4 | 5 | | | V-2 | LOC100129034 | 0.60 | 1901 | 3 | 4 | 5 | | | V-2 | MGRN1 | 0.65 |
| 1806 | 3 | 4 | 5 | | | V-2 | LOC100129534 | 0.66 | 1902 | 3 | 4 | 5 | | | V-2 | MICAL3 | 0.50 |
| 1807 | 3 | 4 | 5 | | | V-2 | LOC100132707 | 0.52 | 1903 | 3 | 4 | 5 | | | V-2 | MIF4GD | 0.59 |
| 1808 | 3 | 4 | 5 | | | V-2 | LOC100133091 | 0.60 | 1904 | 3 | 4 | 5 | | | V-2 | MIPEP | 0.62 |
| 1809 | 3 | 4 | 5 | | | V-2 | LOC100133669 | 0.53 | 1905 | 3 | 4 | 5 | | | V-2 | MITF | 0.56 |
| 1810 | 3 | 4 | 5 | | | V-2 | LOC100288432 | 0.60 | 1906 | 3 | 4 | 5 | | | V-2 | MLLT1 | 0.57 |
| 1811 | 3 | 4 | 5 | | | V-2 | LOC100499466 | 0.60 | 1907 | 3 | 4 | 5 | | | V-2 | MMP23B | 0.52 |
| 1812 | 3 | 4 | 5 | | | V-2 | LOC100499489 | 0.64 | 1908 | 3 | 4 | 5 | | | V-2 | MO8B3 | 0.54 |
| 1813 | 3 | 4 | 5 | | | V-2 | LOC100505806 | 0.57 | 1909 | 3 | 4 | 5 | | | V-2 | MON1B | 0.56 |
| 1814 | 3 | 4 | 5 | | | V-2 | LOC100506668 | 0.54 | 1910 | 3 | 4 | 5 | | | V-2 | MORC2-AS1 | 0.59 |
| 1815 | 3 | 4 | 5 | | | V-2 | LOC100507373 | 0.64 | 1911 | 3 | 4 | 5 | | | V-2 | MORN3 | 0.66 |
| 1816 | 3 | 4 | 5 | | | V-2 | LOC113230 | 0.64 | 1912 | 3 | 4 | 5 | | | V-2 | MPG | 0.59 |
| 1817 | 3 | 4 | 5 | | | V-2 | LOC115110 | 0.53 | 1913 | 3 | 4 | 5 | | | V-2 | MPZL1 | 0.65 |
| 1818 | 3 | 4 | 5 | | | V-2 | LOC148413 | 0.66 | 1914 | 3 | 4 | 5 | | | V-2 | MRPL28 | 0.65 |
| 1819 | 3 | 4 | 5 | | | V-2 | LOC283174 | 0.62 | 1915 | 3 | 4 | 5 | | | V-2 | MRPL28 | 0.64 |
| 1820 | 3 | 4 | 5 | | | V-2 | LOC285033 | 0.55 | 1916 | 3 | 4 | 5 | | | V-2 | MRPL9 | 0.66 |
| 1821 | 3 | 4 | 5 | | | V-2 | LOC339524 | 0.65 | 1917 | 3 | 4 | 5 | | | V-2 | MT1E | 0.51 |

Fig. 39 - 11

| | | | | | | | | | | | | | | | |
|---|---|---|---|---|---|---|---|---|---|---|---|---|---|---|---|
| 1918 | 3 | 4 | 5 | | | V-2 | MT1G | 0.62 | 2014 | 3 | 4 | 5 | | V-2 | PARVA | 0.66 |
| 1919 | 3 | 4 | 5 | | | V-2 | MT1H | 0.63 | 2015 | 3 | 4 | 5 | | V-2 | PARVB | 0.62 |
| 1920 | 3 | 4 | 5 | | | V-2 | MTA2 | 0.58 | 2016 | 3 | 4 | 5 | | V-2 | PATL1 | 0.65 |
| 1921 | 3 | 4 | 5 | | | V-2 | MTMR11 | 0.50 | 2017 | 3 | 4 | 5 | | V-2 | PBX2 | 0.63 |
| 1922 | 3 | 4 | 5 | | | V-2 | MTMR3 | 0.52 | 2018 | 3 | 4 | 5 | | V-2 | PBXIP1 | 0.64 |
| 1923 | 3 | 4 | 5 | | | V-2 | MTSS1 | 0.63 | 2019 | 3 | 4 | 5 | | V-2 | PCBP4 | 0.61 |
| 1924 | 3 | 4 | 5 | | | V-2 | MTSS1L | 0.54 | 2020 | 3 | 4 | 5 | | V-2 | PCDHB10 | 0.52 |
| 1925 | 3 | 4 | 5 | | | V-2 | MTX1 | 0.57 | 2021 | 3 | 4 | 5 | | V-2 | PCDHB16 | 0.55 |
| 1926 | 3 | 4 | 5 | | | V-2 | MUM1 | 0.51 | 2022 | 3 | 4 | 5 | | V-2 | PCDHGB2 | 0.65 |
| 1927 | 3 | 4 | 5 | | | V-2 | MVP | 0.53 | 2023 | 3 | 4 | 5 | | V-2 | PCDHGC3 | 0.51 |
| 1928 | 3 | 4 | 5 | | | V-2 | MX2 | 0.51 | 2024 | 3 | 4 | 5 | | V-2 | PCGF2 | 0.60 |
| 1929 | 3 | 4 | 5 | | | V-2 | MXD4 | 0.64 | 2025 | 3 | 4 | 5 | | V-2 | PCIF1 | 0.61 |
| 1930 | 3 | 4 | 5 | | | V-2 | MXRA8 | 0.52 | 2026 | 3 | 4 | 5 | | V-2 | PCSK7 | 0.51 |
| 1931 | 3 | 4 | 5 | | | V-2 | MYCT1 | 0.58 | 2027 | 3 | 4 | 5 | | V-2 | PDAP1 | 0.60 |
| 1932 | 3 | 4 | 5 | | | V-2 | MYH10 | 0.61 | 2028 | 3 | 4 | 5 | | V-2 | PDE4D | 0.52 |
| 1933 | 3 | 4 | 5 | | | V-2 | MYH11 | 0.57 | 2029 | 3 | 4 | 5 | | V-2 | PDE4DIP | 0.65 |
| 1934 | 3 | 4 | 5 | | | V-2 | MYO1C | 0.64 | 2030 | 3 | 4 | 5 | | V-2 | PDGFB | 0.51 |
| 1935 | 3 | 4 | 5 | | | V-2 | MYPOP | 0.64 | 2031 | 3 | 4 | 5 | | V-2 | PDIA4 | 0.60 |
| 1936 | 3 | 4 | 5 | | | V-2 | NAA10 | 0.60 | 2032 | 3 | 4 | 5 | | V-2 | PDK2 | 0.64 |
| 1937 | 3 | 4 | 5 | | | V-2 | NAALADL1 | 0.60 | 2033 | 3 | 4 | 5 | | V-2 | PDLIM4 | 0.51 |
| 1938 | 3 | 4 | 5 | | | V-2 | NAB1 | 0.66 | 2034 | 3 | 4 | 5 | | V-2 | PDZD8 | 0.66 |
| 1939 | 3 | 4 | 5 | | | V-2 | NACC2 | 0.66 | 2035 | 3 | 4 | 5 | | V-2 | PDZRN3 | 0.61 |
| 1940 | 3 | 4 | 5 | | | V-2 | NAF1 | 0.66 | 2036 | 3 | 4 | 5 | | V-2 | PEA15 | 0.62 |
| 1941 | 3 | 4 | 5 | | | V-2 | NAGLU | 0.61 | 2037 | 3 | 4 | 5 | | V-2 | PELI3 | 0.53 |
| 1942 | 3 | 4 | 5 | | | V-2 | NAP1L3 | 0.60 | 2038 | 3 | 4 | 5 | | V-2 | PFAS | 0.50 |
| 1943 | 3 | 4 | 5 | | | V-2 | NARF | 0.63 | 2039 | 3 | 4 | 5 | | V-2 | PFKL | 0.59 |
| 1944 | 3 | 4 | 5 | | | V-2 | NAT14 | 0.58 | 2040 | 3 | 4 | 5 | | V-2 | PFKP | 0.53 |
| 1945 | 3 | 4 | 5 | | | V-2 | NCAPH2 | 0.61 | 2041 | 3 | 4 | 5 | | V-2 | PFN1 | 0.56 |
| 1946 | 3 | 4 | 5 | | | V-2 | NCK2 | 0.53 | 2042 | 3 | 4 | 5 | | V-2 | PGM5 | 0.50 |
| 1947 | 3 | 4 | 5 | | | V-2 | NCL | 0.54 | 2043 | 3 | 4 | 5 | | V-2 | PGPEP1 | 0.60 |
| 1948 | 3 | 4 | 5 | | | V-2 | NDNL2 | 0.60 | 2044 | 3 | 4 | 5 | | V-2 | PHC2 | 0.60 |
| 1949 | 3 | 4 | 5 | | | V-2 | NDOR1 | 0.58 | 2045 | 3 | 4 | 5 | | V-2 | PHF2 | 0.58 |
| 1950 | 3 | 4 | 5 | | | V-2 | NEDD9 | 0.56 | 2046 | 3 | 4 | 5 | | V-2 | PHF21A | 0.54 |
| 1951 | 3 | 4 | 5 | | | V-2 | NEK2 | 0.59 | 2047 | 3 | 4 | 5 | | V-2 | PHF3 | 0.59 |
| 1952 | 3 | 4 | 5 | | | V-2 | NES | 0.59 | 2048 | 3 | 4 | 5 | | V-2 | PHF8 | 0.56 |
| 1953 | 3 | 4 | 5 | | | V-2 | NEURL2 | 0.62 | 2049 | 3 | 4 | 5 | | V-2 | PHLDB1 | 0.50 |
| 1954 | 3 | 4 | 5 | | | V-2 | NF2 | 0.61 | 2050 | 3 | 4 | 5 | | V-2 | PI4K2A | 0.63 |
| 1955 | 3 | 4 | 5 | | | V-2 | NFKBIL1 | 0.64 | 2051 | 3 | 4 | 5 | | V-2 | PI4KA | 0.56 |
| 1956 | 3 | 4 | 5 | | | V-2 | NHSL1 | 0.52 | 2052 | 3 | 4 | 5 | | V-2 | PI4KB | 0.54 |
| 1957 | 3 | 4 | 5 | | | V-2 | NIT1 | 0.63 | 2053 | 3 | 4 | 5 | | V-2 | PID1 | 0.56 |
| 1958 | 3 | 4 | 5 | | | V-2 | NLGN3 | 0.54 | 2054 | 3 | 4 | 5 | | V-2 | PIGQ | 0.67 |
| 1959 | 3 | 4 | 5 | | | V-2 | NNMT | 0.57 | 2055 | 3 | 4 | 5 | | V-2 | PIGU | 0.66 |
| 1960 | 3 | 4 | 5 | | | V-2 | NOC2L | 0.57 | 2056 | 3 | 4 | 5 | | V-2 | PIK3CA | 0.65 |
| 1961 | 3 | 4 | 5 | | | V-2 | NOL6 | 0.50 | 2057 | 3 | 4 | 5 | | V-2 | PIP4K2B | 0.54 |
| 1962 | 3 | 4 | 5 | | | V-2 | NONO | 0.63 | 2058 | 3 | 4 | 5 | | V-2 | PIP5K1A | 0.67 |
| 1963 | 3 | 4 | 5 | | | V-2 | NOP16 | 0.66 | 2059 | 3 | 4 | 5 | | V-2 | PJA1 | 0.62 |
| 1964 | 3 | 4 | 5 | | | V-2 | NOSIP | 0.62 | 2060 | 3 | 4 | 5 | | V-2 | PKIG | 0.64 |
| 1965 | 3 | 4 | 5 | | | V-2 | NOTCH1 | 0.55 | 2061 | 3 | 4 | 5 | | V-2 | PKMYT1 | 0.57 |
| 1966 | 3 | 4 | 5 | | | V-2 | NPLOC4 | 0.66 | 2062 | 3 | 4 | 5 | | V-2 | PKN1 | 0.54 |
| 1967 | 3 | 4 | 5 | | | V-2 | NPRL2 | 0.52 | 2063 | 3 | 4 | 5 | | V-2 | PKNOX2 | 0.65 |
| 1968 | 3 | 4 | 5 | | | V-2 | NPRL3 | 0.62 | 2064 | 3 | 4 | 5 | | V-2 | PLA2G6 | 0.56 |
| 1969 | 3 | 4 | 5 | | | V-2 | NR3C1 | 0.66 | 2065 | 3 | 4 | 5 | | V-2 | PLAC9 | 0.52 |
| 1970 | 3 | 4 | 5 | | | V-2 | NR3C2 | 0.67 | 2066 | 3 | 4 | 5 | | V-2 | PLAT | 0.61 |
| 1971 | 3 | 4 | 5 | | | V-2 | NRBP1 | 0.60 | 2067 | 3 | 4 | 5 | | V-2 | PLCD3 | 0.58 |
| 1972 | 3 | 4 | 5 | | | V-2 | NREP | 0.56 | 2068 | 3 | 4 | 5 | | V-2 | PLD2 | 0.53 |
| 1973 | 3 | 4 | 5 | | | V-2 | NRF1 | 0.55 | 2069 | 3 | 4 | 5 | | V-2 | PLEK2 | 0.52 |
| 1974 | 3 | 4 | 5 | | | V-2 | NRP2 | 0.54 | 2070 | 3 | 4 | 5 | | V-2 | PLEKHA2 | 0.67 |
| 1975 | 3 | 4 | 5 | | | V-2 | NRXN2 | 0.57 | 2071 | 3 | 4 | 5 | | V-2 | PLEKHH3 | 0.55 |
| 1976 | 3 | 4 | 5 | | | V-2 | NT5DC2 | 0.65 | 2072 | 3 | 4 | 5 | | V-2 | PLEKHM1 | 0.56 |
| 1977 | 3 | 4 | 5 | | | V-2 | NT5E | 0.57 | 2073 | 3 | 4 | 5 | | V-2 | PLEKHN1 | 0.66 |
| 1978 | 3 | 4 | 5 | | | V-2 | NTRK2 | 0.62 | 2074 | 3 | 4 | 5 | | V-2 | PLEKHO2 | 0.57 |
| 1979 | 3 | 4 | 5 | | | V-2 | NUCB1 | 0.55 | 2075 | 3 | 4 | 5 | | V-2 | PLXNA1 | 0.50 |
| 1980 | 3 | 4 | 5 | | | V-2 | NUDC | 0.55 | 2076 | 3 | 4 | 5 | | V-2 | PMEPA1 | 0.65 |
| 1981 | 3 | 4 | 5 | | | V-2 | NUDT1 | 0.59 | 2077 | 3 | 4 | 5 | | V-2 | PNKP | 0.51 |
| 1982 | 3 | 4 | 5 | | | V-2 | NUDT5 | 0.66 | 2078 | 3 | 4 | 5 | | V-2 | PNMA1 | 0.61 |
| 1983 | 3 | 4 | 5 | | | V-2 | NUFIP1 | 0.67 | 2079 | 3 | 4 | 5 | | V-2 | PNMAL2 | 0.56 |
| 1984 | 3 | 4 | 5 | | | V-2 | NUP188 | 0.53 | 2080 | 3 | 4 | 5 | | V-2 | PNPLA6 | 0.56 |
| 1985 | 3 | 4 | 5 | | | V-2 | NUP98 | 0.61 | 2081 | 3 | 4 | 5 | | V-2 | PODN | 0.56 |
| 1986 | 3 | 4 | 5 | | | V-2 | OAF | 0.56 | 2082 | 3 | 4 | 5 | | V-2 | POFUT1 | 0.57 |
| 1987 | 3 | 4 | 5 | | | V-2 | OASL | 0.50 | 2083 | 3 | 4 | 5 | | V-2 | POLD1 | 0.58 |
| 1988 | 3 | 4 | 5 | | | V-2 | OAZ2 | 0.65 | 2084 | 3 | 4 | 5 | | V-2 | POLG2 | 0.64 |
| 1989 | 3 | 4 | 5 | | | V-2 | OBFC1 | 0.67 | 2085 | 3 | 4 | 5 | | V-2 | POLR2J3 | 0.55 |
| 1990 | 3 | 4 | 5 | | | V-2 | ODF2 | 0.56 | 2086 | 3 | 4 | 5 | | V-2 | POLR2J4 | 0.60 |
| 1991 | 3 | 4 | 5 | | | V-2 | OGFOD2 | 0.67 | 2087 | 3 | 4 | 5 | | V-2 | POLR3D | 0.64 |
| 1992 | 3 | 4 | 5 | | | V-2 | OGN | 0.58 | 2088 | 3 | 4 | 5 | | V-2 | POLR3H | 0.53 |
| 1993 | 3 | 4 | 5 | | | V-2 | ORAI3 | 0.62 | 2089 | 3 | 4 | 5 | | V-2 | POLRMT | 0.53 |
| 1994 | 3 | 4 | 5 | | | V-2 | OSBP2 | 0.52 | 2090 | 3 | 4 | 5 | | V-2 | POMGNT1 | 0.65 |
| 1995 | 3 | 4 | 5 | | | V-2 | OSBPL5 | 0.51 | 2091 | 3 | 4 | 5 | | V-2 | POP7 | 0.65 |
| 1996 | 3 | 4 | 5 | | | V-2 | OTUB1 | 0.64 | 2092 | 3 | 4 | 5 | | V-2 | PPAN | 0.53 |
| 1997 | 3 | 4 | 5 | | | V-2 | OTUD5 | 0.55 | 2093 | 3 | 4 | 5 | | V-2 | PPDPF | 0.51 |
| 1998 | 3 | 4 | 5 | | | V-2 | OTUD7B | 0.63 | 2094 | 3 | 4 | 5 | | V-2 | PPFIA3 | 0.63 |
| 1999 | 3 | 4 | 5 | | | V-2 | OVCA2 | 0.61 | 2095 | 3 | 4 | 5 | | V-2 | PPFIBP1 | 0.55 |
| 2000 | 3 | 4 | 5 | | | V-2 | OXSR1 | 0.62 | 2096 | 3 | 4 | 5 | | V-2 | PPIB | 0.66 |
| 2001 | 3 | 4 | 5 | | | V-2 | P4HA2 | 0.50 | 2097 | 3 | 4 | 5 | | V-2 | PPIP5K1 | 0.61 |
| 2002 | 3 | 4 | 5 | | | V-2 | PACS2 | 0.55 | 2098 | 3 | 4 | 5 | | V-2 | PPM1D | 0.63 |
| 2003 | 3 | 4 | 5 | | | V-2 | PACSIN3 | 0.61 | 2099 | 3 | 4 | 5 | | V-2 | PPM1F | 0.51 |
| 2004 | 3 | 4 | 5 | | | V-2 | PAF1 | 0.59 | 2100 | 3 | 4 | 5 | | V-2 | PPM1G | 0.56 |
| 2005 | 3 | 4 | 5 | | | V-2 | PAK6 | 0.50 | 2101 | 3 | 4 | 5 | | V-2 | PPM1M | 0.57 |
| 2006 | 3 | 4 | 5 | | | V-2 | PALLD | 0.64 | 2102 | 3 | 4 | 5 | | V-2 | PPP1R13B | 0.57 |
| 2007 | 3 | 4 | 5 | | | V-2 | PAM | 0.56 | 2103 | 3 | 4 | 5 | | V-2 | PPP1R16A | 0.60 |
| 2008 | 3 | 4 | 5 | | | V-2 | PANK4 | 0.65 | 2104 | 3 | 4 | 5 | | V-2 | PPP1R26 | 0.58 |
| 2009 | 3 | 4 | 5 | | | V-2 | PANX1 | 0.53 | 2105 | 3 | 4 | 5 | | V-2 | PPP1R3G | 0.59 |
| 2010 | 3 | 4 | 5 | | | V-2 | PARD6A | 0.64 | 2106 | 3 | 4 | 5 | | V-2 | PPP2R2B | 0.52 |
| 2011 | 3 | 4 | 5 | | | V-2 | PARP1 | 0.58 | 2107 | 3 | 4 | 5 | | V-2 | PPP2R2D | 0.54 |
| 2012 | 3 | 4 | 5 | | | V-2 | PARP12 | 0.61 | 2108 | 3 | 4 | 5 | | V-2 | PPP2R5B | 0.64 |
| 2013 | 3 | 4 | 5 | | | V-2 | PARP6 | 0.55 | 2109 | 3 | 4 | 5 | | V-2 | PPP2R5D | 0.57 |

Fig. 39 - 12

| | | | | | | | | | | | | | | | | | |
|---|---|---|---|---|---|---|---|---|---|---|---|---|---|---|---|---|---|
| 2110 | 3 | 4 | 5 | | | V-2 | PPP3CC | 0.65 | 2206 | 3 | 4 | 5 | | | V-2 | RING1 | 0.62 |
| 2111 | 3 | 4 | 5 | | | V-2 | PPP6R2 | 0.51 | 2207 | 3 | 4 | 5 | | | V-2 | RIPK4 | 0.59 |
| 2112 | 3 | 4 | 5 | | | V-2 | PPT2 | 0.52 | 2208 | 3 | 4 | 5 | | | V-2 | RLF | 0.60 |
| 2113 | 3 | 4 | 5 | | | V-2 | PQBP1 | 0.53 | 2209 | 3 | 4 | 5 | | | V-2 | RMI2 | 0.66 |
| 2114 | 3 | 4 | 5 | | | V-2 | PQLC2 | 0.61 | 2210 | 3 | 4 | 5 | | | V-2 | RNASE1 | 0.52 |
| 2115 | 3 | 4 | 5 | | | V-2 | PRCC | 0.59 | 2211 | 3 | 4 | 5 | | | V-2 | RNASEH2A | 0.62 |
| 2116 | 3 | 4 | 5 | | | V-2 | PRDM11 | 0.53 | 2212 | 3 | 4 | 5 | | | V-2 | RNF115 | 0.59 |
| 2117 | 3 | 4 | 5 | | | V-2 | PRDM15 | 0.58 | 2213 | 3 | 4 | 5 | | | V-2 | RNF144A | 0.65 |
| 2118 | 3 | 4 | 5 | | | V-2 | PRDX5 | 0.62 | 2214 | 3 | 4 | 5 | | | V-2 | RNF166 | 0.60 |
| 2119 | 3 | 4 | 5 | | | V-2 | PREX1 | 0.64 | 2215 | 3 | 4 | 5 | | | V-2 | RNF2 | 0.66 |
| 2120 | 3 | 4 | 5 | | | V-2 | PRICKLE3 | 0.55 | 2216 | 3 | 4 | 5 | | | V-2 | RNF213 | 0.66 |
| 2121 | 3 | 4 | 5 | | | V-2 | PRIMA1 | 0.66 | 2217 | 3 | 4 | 5 | | | V-2 | RNF214 | 0.55 |
| 2122 | 3 | 4 | 5 | | | V-2 | PRKACA | 0.51 | 2218 | 3 | 4 | 5 | | | V-2 | RNF216 | 0.61 |
| 2123 | 3 | 4 | 5 | | | V-2 | PRKAR1B | 0.52 | 2219 | 3 | 4 | 5 | | | V-2 | RNF220 | 0.55 |
| 2124 | 3 | 4 | 5 | | | V-2 | PRKD2 | 0.50 | 2220 | 3 | 4 | 5 | | | V-2 | RNF31 | 0.53 |
| 2125 | 3 | 4 | 5 | | | V-2 | PRMT1 | 0.59 | 2221 | 3 | 4 | 5 | | | V-2 | RNF4 | 0.66 |
| 2126 | 3 | 4 | 5 | | | V-2 | PRMT7 | 0.55 | 2222 | 3 | 4 | 5 | | | V-2 | RNF40 | 0.51 |
| 2127 | 3 | 4 | 5 | | | V-2 | PROCA1 | 0.65 | 2223 | 3 | 4 | 5 | | | V-2 | RNH1 | 0.60 |
| 2128 | 3 | 4 | 5 | | | V-2 | PRPF31 | 0.65 | 2224 | 3 | 4 | 5 | | | V-2 | RNMT | 0.66 |
| 2129 | 3 | 4 | 5 | | | V-2 | PRR11 | 0.57 | 2225 | 3 | 4 | 5 | | | V-2 | RNPS1 | 0.66 |
| 2130 | 3 | 4 | 5 | | | V-2 | PRR5 | 0.63 | 2226 | 3 | 4 | 5 | | | V-2 | RPP21 | 0.62 |
| 2131 | 3 | 4 | 5 | | | V-2 | PRRG1 | 0.54 | 2227 | 3 | 4 | 5 | | | V-2 | RPP25 | 0.63 |
| 2132 | 3 | 4 | 5 | | | V-2 | PRRT1 | 0.57 | 2228 | 3 | 4 | 5 | | | V-2 | RPS6KA4 | 0.66 |
| 2133 | 3 | 4 | 5 | | | V-2 | PRRX1 | 0.58 | 2229 | 3 | 4 | 5 | | | V-2 | RPUSD1 | 0.56 |
| 2134 | 3 | 4 | 5 | | | V-2 | PRSS12 | 0.51 | 2230 | 3 | 4 | 5 | | | V-2 | RPUSD4 | 0.67 |
| 2135 | 3 | 4 | 5 | | | V-2 | PRSS36 | 0.64 | 2231 | 3 | 4 | 5 | | | V-2 | RRAS | 0.66 |
| 2136 | 3 | 4 | 5 | | | V-2 | PSD4 | 0.56 | 2232 | 3 | 4 | 5 | | | V-2 | RSAD2 | 0.55 |
| 2137 | 3 | 4 | 5 | | | V-2 | PSMB10 | 0.63 | 2233 | 3 | 4 | 5 | | | V-2 | RSPH3 | 0.56 |
| 2138 | 3 | 4 | 5 | | | V-2 | PSMF1 | 0.56 | 2234 | 3 | 4 | 5 | | | V-2 | RSU1 | 0.62 |
| 2139 | 3 | 4 | 5 | | | V-2 | PSPC1 | 0.59 | 2235 | 3 | 4 | 5 | | | V-2 | RTN4RL2 | 0.55 |
| 2140 | 3 | 4 | 5 | | | V-2 | PTGDR2 | 0.59 | 2236 | 3 | 4 | 5 | | | V-2 | RUSC1 | 0.64 |
| 2141 | 3 | 4 | 5 | | | V-2 | PTGER2 | 0.52 | 2237 | 3 | 4 | 5 | | | V-2 | RUVBL2 | 0.62 |
| 2142 | 3 | 4 | 5 | | | V-2 | PTGFR | 0.63 | 2238 | 3 | 4 | 5 | | | V-2 | RXRB | 0.53 |
| 2143 | 3 | 4 | 5 | | | V-2 | PTK7 | 0.56 | 2239 | 3 | 4 | 5 | | | V-2 | S100A11 | 0.63 |
| 2144 | 3 | 4 | 5 | | | V-2 | PTMA | 0.54 | 2240 | 3 | 4 | 5 | | | V-2 | S100A4 | 0.51 |
| 2145 | 3 | 4 | 5 | | | V-2 | PTN | 0.53 | 2241 | 3 | 4 | 5 | | | V-2 | S100A6 | 0.65 |
| 2146 | 3 | 4 | 5 | | | V-2 | PTOV1 | 0.50 | 2242 | 3 | 4 | 5 | | | V-2 | SAE1 | 0.66 |
| 2147 | 3 | 4 | 5 | | | V-2 | PTPN1 | 0.66 | 2243 | 3 | 4 | 5 | | | V-2 | SAFB2 | 0.54 |
| 2148 | 3 | 4 | 5 | | | V-2 | PTPN18 | 0.65 | 2244 | 3 | 4 | 5 | | | V-2 | SARS2 | 0.54 |
| 2149 | 3 | 4 | 5 | | | V-2 | PTPN9 | 0.57 | 2245 | 3 | 4 | 5 | | | V-2 | SBNO2 | 0.61 |
| 2150 | 3 | 4 | 5 | | | V-2 | PTPRA | 0.57 | 2246 | 3 | 4 | 5 | | | V-2 | SCAF4 | 0.53 |
| 2151 | 3 | 4 | 5 | | | V-2 | PTPRS | 0.55 | 2247 | 3 | 4 | 5 | | | V-2 | SCAF8 | 0.54 |
| 2152 | 3 | 4 | 5 | | | V-2 | PTPRU | 0.52 | 2248 | 3 | 4 | 5 | | | V-2 | SCAND1 | 0.66 |
| 2153 | 3 | 4 | 5 | | | V-2 | PTTG3P | 0.63 | 2249 | 3 | 4 | 5 | | | V-2 | SCLY | 0.53 |
| 2154 | 3 | 4 | 5 | | | V-2 | PVRL2 | 0.63 | 2250 | 3 | 4 | 5 | | | V-2 | SCNM1 | 0.56 |
| 2155 | 3 | 4 | 5 | | | V-2 | PWP2 | 0.60 | 2251 | 3 | 4 | 5 | | | V-2 | SCYL1 | 0.60 |
| 2156 | 3 | 4 | 5 | | | V-2 | PXDC1 | 0.61 | 2252 | 3 | 4 | 5 | | | V-2 | SEC16A | 0.62 |
| 2157 | 3 | 4 | 5 | | | V-2 | PXK | 0.65 | 2253 | 3 | 4 | 5 | | | V-2 | SEC23A | 0.59 |
| 2158 | 3 | 4 | 5 | | | V-2 | PYGM | 0.55 | 2254 | 3 | 4 | 5 | | | V-2 | SEC24C | 0.65 |
| 2159 | 3 | 4 | 5 | | | V-2 | QPRT | 0.59 | 2255 | 3 | 4 | 5 | | | V-2 | SEC24D | 0.51 |
| 2160 | 3 | 4 | 5 | | | V-2 | QSOX2 | 0.65 | 2256 | 3 | 4 | 5 | | | V-2 | SEMA3B | 0.66 |
| 2161 | 3 | 4 | 5 | | | V-2 | R3HCC1 | 0.60 | 2257 | 3 | 4 | 5 | | | V-2 | SEMA3F | 0.55 |
| 2162 | 3 | 4 | 5 | | | V-2 | R3HDM2 | 0.60 | 2258 | 3 | 4 | 5 | | | V-2 | SEMA4D | 0.60 |
| 2163 | 3 | 4 | 5 | | | V-2 | R3HDM4 | 0.63 | 2259 | 3 | 4 | 5 | | | V-2 | SEMA4F | 0.65 |
| 2164 | 3 | 4 | 5 | | | V-2 | RAB11B | 0.64 | 2260 | 3 | 4 | 5 | | | V-2 | SEPN1 | 0.54 |
| 2165 | 3 | 4 | 5 | | | V-2 | RAB34 | 0.59 | 2261 | 3 | 4 | 5 | | | V-2 | SEPT3 | 0.62 |
| 2166 | 3 | 4 | 5 | | | V-2 | RAB35 | 0.61 | 2262 | 3 | 4 | 5 | | | V-2 | SEPT8 | 0.66 |
| 2167 | 3 | 4 | 5 | | | V-2 | RAB40C | 0.52 | 2263 | 3 | 4 | 5 | | | V-2 | SEPW1 | 0.61 |
| 2168 | 3 | 4 | 5 | | | V-2 | RAB5C | 0.58 | 2264 | 3 | 4 | 5 | | | V-2 | SERPINF1 | 0.55 |
| 2169 | 3 | 4 | 5 | | | V-2 | RABL2B | 0.62 | 2265 | 3 | 4 | 5 | | | V-2 | SERPING1 | 0.53 |
| 2170 | 3 | 4 | 5 | | | V-2 | RAD23A | 0.57 | 2266 | 3 | 4 | 5 | | | V-2 | SETD2 | 0.60 |
| 2171 | 3 | 4 | 5 | | | V-2 | RADIL | 0.62 | 2267 | 3 | 4 | 5 | | | V-2 | SETDB1 | 0.57 |
| 2172 | 3 | 4 | 5 | | | V-2 | RALB | 0.66 | 2268 | 3 | 4 | 5 | | | V-2 | SF3B4 | 0.54 |
| 2173 | 3 | 4 | 5 | | | V-2 | RALY | 0.58 | 2269 | 3 | 4 | 5 | | | V-2 | SFPQ | 0.64 |
| 2174 | 3 | 4 | 5 | | | V-2 | RANBP10 | 0.53 | 2270 | 3 | 4 | 5 | | | V-2 | SFTPD | 0.62 |
| 2175 | 3 | 4 | 5 | | | V-2 | RAP1GAP2 | 0.66 | 2271 | 3 | 4 | 5 | | | V-2 | SGCD | 0.61 |
| 2176 | 3 | 4 | 5 | | | V-2 | RAPGEFL1 | 0.65 | 2272 | 3 | 4 | 5 | | | V-2 | SGSH | 0.55 |
| 2177 | 3 | 4 | 5 | | | V-2 | RARRES3 | 0.63 | 2273 | 3 | 4 | 5 | | | V-2 | SGTA | 0.66 |
| 2178 | 3 | 4 | 5 | | | V-2 | RASA3 | 0.65 | 2274 | 3 | 4 | 5 | | | V-2 | SH2B2 | 0.58 |
| 2179 | 3 | 4 | 5 | | | V-2 | RASA4P | 0.50 | 2275 | 3 | 4 | 5 | | | V-2 | SH2B3 | 0.53 |
| 2180 | 3 | 4 | 5 | | | V-2 | RASL12 | 0.64 | 2276 | 3 | 4 | 5 | | | V-2 | SH2D3A | 0.52 |
| 2181 | 3 | 4 | 5 | | | V-2 | RAVER1 | 0.55 | 2277 | 3 | 4 | 5 | | | V-2 | SH3BP2 | 0.57 |
| 2182 | 3 | 4 | 5 | | | V-2 | RBCK1 | 0.66 | 2278 | 3 | 4 | 5 | | | V-2 | SH3BP4 | 0.59 |
| 2183 | 3 | 4 | 5 | | | V-2 | RBFOX2 | 0.52 | 2279 | 3 | 4 | 5 | | | V-2 | SH3TC1 | 0.52 |
| 2184 | 3 | 4 | 5 | | | V-2 | RBM10 | 0.57 | 2280 | 3 | 4 | 5 | | | V-2 | SHC1 | 0.63 |
| 2185 | 3 | 4 | 5 | | | V-2 | RBM19 | 0.61 | 2281 | 3 | 4 | 5 | | | V-2 | SHISA3 | 0.66 |
| 2186 | 3 | 4 | 5 | | | V-2 | RBM28 | 0.59 | 2282 | 3 | 4 | 5 | | | V-2 | SHISA5 | 0.64 |
| 2187 | 3 | 4 | 5 | | | V-2 | RCC1 | 0.61 | 2283 | 3 | 4 | 5 | | | V-2 | SHPK | 0.52 |
| 2188 | 3 | 4 | 5 | | | V-2 | RCSD1 | 0.55 | 2284 | 3 | 4 | 5 | | | V-2 | SHQ1 | 0.61 |
| 2189 | 3 | 4 | 5 | | | V-2 | RCVRN | 0.50 | 2285 | 3 | 4 | 5 | | | V-2 | SIGIRR | 0.58 |
| 2190 | 3 | 4 | 5 | | | V-2 | REEP4 | 0.55 | 2286 | 3 | 4 | 5 | | | V-2 | SIGMAR1 | 0.61 |
| 2191 | 3 | 4 | 5 | | | V-2 | REM2 | 0.59 | 2287 | 3 | 4 | 5 | | | V-2 | SIK2 | 0.57 |
| 2192 | 3 | 4 | 5 | | | V-2 | RERE | 0.60 | 2288 | 3 | 4 | 5 | | | V-2 | SIN3A | 0.51 |
| 2193 | 3 | 4 | 5 | | | V-2 | RFC5 | 0.55 | 2289 | 3 | 4 | 5 | | | V-2 | SIRPA | 0.57 |
| 2194 | 3 | 4 | 5 | | | V-2 | RFWD3 | 0.58 | 2290 | 3 | 4 | 5 | | | V-2 | SIRPB2 | 0.56 |
| 2195 | 3 | 4 | 5 | | | V-2 | RFXANK | 0.60 | 2291 | 3 | 4 | 5 | | | V-2 | SIRT2 | 0.57 |
| 2196 | 3 | 4 | 5 | | | V-2 | RGL1 | 0.59 | 2292 | 3 | 4 | 5 | | | V-2 | SIRT3 | 0.67 |
| 2197 | 3 | 4 | 5 | | | V-2 | RGNEF | 0.60 | 2293 | 3 | 4 | 5 | | | V-2 | SIRT6 | 0.60 |
| 2198 | 3 | 4 | 5 | | | V-2 | RGS10 | 0.66 | 2294 | 3 | 4 | 5 | | | V-2 | SIX5 | 0.61 |
| 2199 | 3 | 4 | 5 | | | V-2 | RGS12 | 0.56 | 2295 | 3 | 4 | 5 | | | V-2 | SKI | 0.54 |
| 2200 | 3 | 4 | 5 | | | V-2 | RHOC | 0.59 | 2296 | 3 | 4 | 5 | | | V-2 | SLC12A9 | 0.63 |
| 2201 | 3 | 4 | 5 | | | V-2 | RIC8A | 0.64 | 2297 | 3 | 4 | 5 | | | V-2 | SLC13A3 | 0.63 |
| 2202 | 3 | 4 | 5 | | | V-2 | RILP | 0.60 | 2298 | 3 | 4 | 5 | | | V-2 | SLC23A2 | 0.65 |
| 2203 | 3 | 4 | 5 | | | V-2 | RILPL2 | 0.61 | 2299 | 3 | 4 | 5 | | | V-2 | SLC25A38 | 0.65 |
| 2204 | 3 | 4 | 5 | | | V-2 | RIN1 | 0.54 | 2300 | 3 | 4 | 5 | | | V-2 | SLC26A11 | 0.64 |
| 2205 | 3 | 4 | 5 | | | V-2 | RIN3 | 0.50 | 2301 | 3 | 4 | 5 | | | V-2 | SLC27A3 | 0.52 |

Fig. 39 - 13

| | | | | | | | | | | | | | | |
|---|---|---|---|---|---|---|---|---|---|---|---|---|---|---|
| 2302 | 3 | 4 | 5 | | V-2 | SLC2A4RG | 0.60 | 2398 | 3 | 4 | 5 | | V-2 | TBCB | 0.65 |
| 2303 | 3 | 4 | 5 | | V-2 | SLC35E2B | 0.66 | 2399 | 3 | 4 | 5 | | V-2 | TBCD | 0.54 |
| 2304 | 3 | 4 | 5 | | V-2 | SLC35F2 | 0.61 | 2400 | 3 | 4 | 5 | | V-2 | TBL1X | 0.61 |
| 2305 | 3 | 4 | 5 | | V-2 | SLC38A5 | 0.64 | 2401 | 3 | 4 | 5 | | V-2 | TBRG4 | 0.61 |
| 2306 | 3 | 4 | 5 | | V-2 | SLC38A7 | 0.55 | 2402 | 3 | 4 | 5 | | V-2 | TBX6 | 0.52 |
| 2307 | 3 | 4 | 5 | | V-2 | SLC39A1 | 0.54 | 2403 | 3 | 4 | 5 | | V-2 | TCEA2 | 0.51 |
| 2308 | 3 | 4 | 5 | | V-2 | SLC39A4 | 0.59 | 2404 | 3 | 4 | 5 | | V-2 | TCF19 | 0.53 |
| 2309 | 3 | 4 | 5 | | V-2 | SLC3A2 | 0.66 | 2405 | 3 | 4 | 5 | | V-2 | TCF3 | 0.53 |
| 2310 | 3 | 4 | 5 | | V-2 | SLC46A1 | 0.64 | 2406 | 3 | 4 | 5 | | V-2 | TCN2 | 0.63 |
| 2311 | 3 | 4 | 5 | | V-2 | SLC4A2 | 0.54 | 2407 | 3 | 4 | 5 | | V-2 | TCTN2 | 0.51 |
| 2312 | 3 | 4 | 5 | | V-2 | SLC4A3 | 0.61 | 2408 | 3 | 4 | 5 | | V-2 | TDP1 | 0.54 |
| 2313 | 3 | 4 | 5 | | V-2 | SLC7A6OS | 0.60 | 2409 | 3 | 4 | 5 | | V-2 | TDRD7 | 0.58 |
| 2314 | 3 | 4 | 5 | | V-2 | SLC9A1 | 0.51 | 2410 | 3 | 4 | 5 | | V-2 | TEAD2 | 0.65 |
| 2315 | 3 | 4 | 5 | | V-2 | SLC9B2 | 0.64 | 2411 | 3 | 4 | 5 | | V-2 | TEAD4 | 0.67 |
| 2316 | 3 | 4 | 5 | | V-2 | SLCO4A1 | 0.67 | 2412 | 3 | 4 | 5 | | V-2 | TEC | 0.51 |
| 2317 | 3 | 4 | 5 | | V-2 | SLFN11 | 0.64 | 2413 | 3 | 4 | 5 | | V-2 | TECPR2 | 0.55 |
| 2318 | 3 | 4 | 5 | | V-2 | SLX1B-SULT1A4 | 0.54 | 2414 | 3 | 4 | 5 | | V-2 | TES | 0.57 |
| 2319 | 3 | 4 | 5 | | V-2 | SMARCAL1 | 0.56 | 2415 | 3 | 4 | 5 | | V-2 | TESK1 | 0.55 |
| 2320 | 3 | 4 | 5 | | V-2 | SMARCB1 | 0.52 | 2416 | 3 | 4 | 5 | | V-2 | TFE3 | 0.54 |
| 2321 | 3 | 4 | 5 | | V-2 | SMARCC2 | 0.63 | 2417 | 3 | 4 | 5 | | V-2 | TFPI | 0.66 |
| 2322 | 3 | 4 | 5 | | V-2 | SMARCD1 | 0.63 | 2418 | 3 | 4 | 5 | | V-2 | TGFBR2 | 0.66 |
| 2323 | 3 | 4 | 5 | | V-2 | SMG5 | 0.51 | 2419 | 3 | 4 | 5 | | V-2 | TGIF1 | 0.55 |
| 2324 | 3 | 4 | 5 | | V-2 | SMG6 | 0.54 | 2420 | 3 | 4 | 5 | | V-2 | THAP7-AS1 | 0.62 |
| 2325 | 3 | 4 | 5 | | V-2 | SMG7 | 0.64 | 2421 | 3 | 4 | 5 | | V-2 | THBS2 | 0.56 |
| 2326 | 3 | 4 | 5 | | V-2 | SMO | 0.57 | 2422 | 3 | 4 | 5 | | V-2 | THEM4 | 0.60 |
| 2327 | 3 | 4 | 5 | | V-2 | SMPD4 | 0.61 | 2423 | 3 | 4 | 5 | | V-2 | THRAP3 | 0.54 |
| 2328 | 3 | 4 | 5 | | V-2 | SMU1 | 0.65 | 2424 | 3 | 4 | 5 | | V-2 | THTPA | 0.63 |
| 2329 | 3 | 4 | 5 | | V-2 | SMYD3 | 0.61 | 2425 | 3 | 4 | 5 | | V-2 | TIMELESS | 0.52 |
| 2330 | 3 | 4 | 5 | | V-2 | SMYD5 | 0.66 | 2426 | 3 | 4 | 5 | | V-2 | TIMP1 | 0.54 |
| 2331 | 3 | 4 | 5 | | V-2 | SNAP47 | 0.66 | 2427 | 3 | 4 | 5 | | V-2 | TIRAP | 0.63 |
| 2332 | 3 | 4 | 5 | | V-2 | SNAPC2 | 0.63 | 2428 | 3 | 4 | 5 | | V-2 | TLE1 | 0.65 |
| 2333 | 3 | 4 | 5 | | V-2 | SNF8 | 0.61 | 2429 | 3 | 4 | 5 | | V-2 | TLR4 | 0.61 |
| 2334 | 3 | 4 | 5 | | V-2 | SNORA53 | 0.56 | 2430 | 3 | 4 | 5 | | V-2 | TM9SF4 | 0.59 |
| 2335 | 3 | 4 | 5 | | V-2 | SNRPA | 0.62 | 2431 | 3 | 4 | 5 | | V-2 | TMEM106A | 0.53 |
| 2336 | 3 | 4 | 5 | | V-2 | SNTA1 | 0.61 | 2432 | 3 | 4 | 5 | | V-2 | TMEM120B | 0.67 |
| 2337 | 3 | 4 | 5 | | V-2 | SNW1 | 0.63 | 2433 | 3 | 4 | 5 | | V-2 | TMEM140 | 0.66 |
| 2338 | 3 | 4 | 5 | | V-2 | SNX15 | 0.67 | 2434 | 3 | 4 | 5 | | V-2 | TMEM160 | 0.67 |
| 2339 | 3 | 4 | 5 | | V-2 | SNX21 | 0.57 | 2435 | 3 | 4 | 5 | | V-2 | TMEM179B | 0.64 |
| 2340 | 3 | 4 | 5 | | V-2 | SNX27 | 0.65 | 2436 | 3 | 4 | 5 | | V-2 | TMEM184B | 0.55 |
| 2341 | 3 | 4 | 5 | | V-2 | SNX8 | 0.64 | 2437 | 3 | 4 | 5 | | V-2 | TMEM214 | 0.64 |
| 2342 | 3 | 4 | 5 | | V-2 | SNX9 | 0.61 | 2438 | 3 | 4 | 5 | | V-2 | TMEM25 | 0.64 |
| 2343 | 3 | 4 | 5 | | V-2 | SOCS1 | 0.66 | 2439 | 3 | 4 | 5 | | V-2 | TMEM35 | 0.63 |
| 2344 | 3 | 4 | 5 | | V-2 | SOD3 | 0.53 | 2440 | 3 | 4 | 5 | | V-2 | TMEM39B | 0.55 |
| 2345 | 3 | 4 | 5 | | V-2 | SOLH | 0.51 | 2441 | 3 | 4 | 5 | | V-2 | TMEM51 | 0.66 |
| 2346 | 3 | 4 | 5 | | V-2 | SORBS3 | 0.52 | 2442 | 3 | 4 | 5 | | V-2 | TMEM63B | 0.60 |
| 2347 | 3 | 4 | 5 | | V-2 | SOX12 | 0.52 | 2443 | 3 | 4 | 5 | | V-2 | TMUB1 | 0.65 |
| 2348 | 3 | 4 | 5 | | V-2 | SPATA7 | 0.52 | 2444 | 3 | 4 | 5 | | V-2 | TNFAIP8L1 | 0.52 |
| 2349 | 3 | 4 | 5 | | V-2 | SPATS2 | 0.62 | 2445 | 3 | 4 | 5 | | V-2 | TNFRSF10A | 0.52 |
| 2350 | 3 | 4 | 5 | | V-2 | SPECC1 | 0.51 | 2446 | 3 | 4 | 5 | | V-2 | TNFRSF11A | 0.65 |
| 2351 | 3 | 4 | 5 | | V-2 | SPNS1 | 0.62 | 2447 | 3 | 4 | 5 | | V-2 | TNFRSF19 | 0.60 |
| 2352 | 3 | 4 | 5 | | V-2 | SPRY2 | 0.55 | 2448 | 3 | 4 | 5 | | V-2 | TNFRSF1A | 0.58 |
| 2353 | 3 | 4 | 5 | | V-2 | SRA1 | 0.62 | 2449 | 3 | 4 | 5 | | V-2 | TNFRSF1B | 0.56 |
| 2354 | 3 | 4 | 5 | | V-2 | SRC | 0.52 | 2450 | 3 | 4 | 5 | | V-2 | TNFRSF8 | 0.67 |
| 2355 | 3 | 4 | 5 | | V-2 | SRGAP2 | 0.51 | 2451 | 3 | 4 | 5 | | V-2 | TNFSF9 | 0.57 |
| 2356 | 3 | 4 | 5 | | V-2 | SRPR | 0.61 | 2452 | 3 | 4 | 5 | | V-2 | TNIP1 | 0.63 |
| 2357 | 3 | 4 | 5 | | V-2 | SRRM3 | 0.65 | 2453 | 3 | 4 | 5 | | V-2 | TNIP2 | 0.59 |
| 2358 | 3 | 4 | 5 | | V-2 | SRSF4 | 0.63 | 2454 | 3 | 4 | 5 | | V-2 | TNNC1 | 0.64 |
| 2359 | 3 | 4 | 5 | | V-2 | SSH1 | 0.55 | 2455 | 3 | 4 | 5 | | V-2 | TNNT1 | 0.52 |
| 2360 | 3 | 4 | 5 | | V-2 | SSSCA1 | 0.66 | 2456 | 3 | 4 | 5 | | V-2 | TNNT3 | 0.61 |
| 2361 | 3 | 4 | 5 | | V-2 | ST3GAL2 | 0.51 | 2457 | 3 | 4 | 5 | | V-2 | TNS3 | 0.53 |
| 2362 | 3 | 4 | 5 | | V-2 | ST6GAL1 | 0.54 | 2458 | 3 | 4 | 5 | | V-2 | TONSL | 0.50 |
| 2363 | 3 | 4 | 5 | | V-2 | ST6GALNAC6 | 0.60 | 2459 | 3 | 4 | 5 | | V-2 | TOP3A | 0.54 |
| 2364 | 3 | 4 | 5 | | V-2 | ST7 | 0.54 | 2460 | 3 | 4 | 5 | | V-2 | TOR3A | 0.64 |
| 2365 | 3 | 4 | 5 | | V-2 | STAG3L3 | 0.64 | 2461 | 3 | 4 | 5 | | V-2 | TP53BP1 | 0.60 |
| 2366 | 3 | 4 | 5 | | V-2 | STAR | 0.66 | 2462 | 3 | 4 | 5 | | V-2 | TP53BP2 | 0.65 |
| 2367 | 3 | 4 | 5 | | V-2 | STAT5B | 0.61 | 2463 | 3 | 4 | 5 | | V-2 | TP53I11 | 0.52 |
| 2368 | 3 | 4 | 5 | | V-2 | STAT6 | 0.60 | 2464 | 3 | 4 | 5 | | V-2 | TP53INP2 | 0.64 |
| 2369 | 3 | 4 | 5 | | V-2 | STIP1 | 0.59 | 2465 | 3 | 4 | 5 | | V-2 | TPCN1 | 0.64 |
| 2370 | 3 | 4 | 5 | | V-2 | STK10 | 0.56 | 2466 | 3 | 4 | 5 | | V-2 | TPGS2 | 0.61 |
| 2371 | 3 | 4 | 5 | | V-2 | STK11 | 0.65 | 2467 | 3 | 4 | 5 | | V-2 | TPP1 | 0.59 |
| 2372 | 3 | 4 | 5 | | V-2 | STK11IP | 0.51 | 2468 | 3 | 4 | 5 | | V-2 | TPRXL | 0.58 |
| 2373 | 3 | 4 | 5 | | V-2 | STMN3 | 0.53 | 2469 | 3 | 4 | 5 | | V-2 | TPTEP1 | 0.59 |
| 2374 | 3 | 4 | 5 | | V-2 | STON1 | 0.64 | 2470 | 3 | 4 | 5 | | V-2 | TRAF2 | 0.55 |
| 2375 | 3 | 4 | 5 | | V-2 | STRN4 | 0.59 | 2471 | 3 | 4 | 5 | | V-2 | TRAF3IP2 | 0.60 |
| 2376 | 3 | 4 | 5 | | V-2 | STXBP1 | 0.62 | 2472 | 3 | 4 | 5 | | V-2 | TRAF7 | 0.52 |
| 2377 | 3 | 4 | 5 | | V-2 | SULF2 | 0.56 | 2473 | 3 | 4 | 5 | | V-2 | TRAK1 | 0.54 |
| 2378 | 3 | 4 | 5 | | V-2 | SUPT5H | 0.55 | 2474 | 3 | 4 | 5 | | V-2 | TRAP1 | 0.53 |
| 2379 | 3 | 4 | 5 | | V-2 | SURF2 | 0.63 | 2475 | 3 | 4 | 5 | | V-2 | TRAPPC1 | 0.62 |
| 2380 | 3 | 4 | 5 | | V-2 | SUSD3 | 0.55 | 2476 | 3 | 4 | 5 | | V-2 | TREX1 | 0.60 |
| 2381 | 3 | 4 | 5 | | V-2 | SVIL | 0.62 | 2477 | 3 | 4 | 5 | | V-2 | TRIM21 | 0.60 |
| 2382 | 3 | 4 | 5 | | V-2 | SYNE2 | 0.59 | 2478 | 3 | 4 | 5 | | V-2 | TRIM28 | 0.61 |
| 2383 | 3 | 4 | 5 | | V-2 | SYNPO2 | 0.58 | 2479 | 3 | 4 | 5 | | V-2 | TRIM32 | 0.54 |
| 2384 | 3 | 4 | 5 | | V-2 | SYVN1 | 0.64 | 2480 | 3 | 4 | 5 | | V-2 | TRIM39 | 0.54 |
| 2385 | 3 | 4 | 5 | | V-2 | TAB1 | 0.62 | 2481 | 3 | 4 | 5 | | V-2 | TRIM41 | 0.67 |
| 2386 | 3 | 4 | 5 | | V-2 | TAF12 | 0.64 | 2482 | 3 | 4 | 5 | | V-2 | TRIM62 | 0.62 |
| 2387 | 3 | 4 | 5 | | V-2 | TAF15 | 0.54 | 2483 | 3 | 4 | 5 | | V-2 | TRIM68 | 0.67 |
| 2388 | 3 | 4 | 5 | | V-2 | TAF4 | 0.59 | 2484 | 3 | 4 | 5 | | V-2 | TRIM8 | 0.59 |
| 2389 | 3 | 4 | 5 | | V-2 | TAF5L | 0.64 | 2485 | 3 | 4 | 5 | | V-2 | TRIOBP | 0.65 |
| 2390 | 3 | 4 | 5 | | V-2 | TANC1 | 0.61 | 2486 | 3 | 4 | 5 | | V-2 | TRIP6 | 0.63 |
| 2391 | 3 | 4 | 5 | | V-2 | TANC2 | 0.51 | 2487 | 3 | 4 | 5 | | V-2 | TRMT2A | 0.62 |
| 2392 | 3 | 4 | 5 | | V-2 | TARS2 | 0.64 | 2488 | 3 | 4 | 5 | | V-2 | TRMT61A | 0.64 |
| 2393 | 3 | 4 | 5 | | V-2 | TAX1BP3 | 0.63 | 2489 | 3 | 4 | 5 | | V-2 | TRNP1 | 0.67 |
| 2394 | 3 | 4 | 5 | | V-2 | TBC1D10A | 0.66 | 2490 | 3 | 4 | 5 | | V-2 | TRPM4 | 0.59 |
| 2395 | 3 | 4 | 5 | | V-2 | TBC1D20 | 0.64 | 2491 | 3 | 4 | 5 | | V-2 | TRRAP | 0.62 |
| 2396 | 3 | 4 | 5 | | V-2 | TBC1D2B | 0.53 | 2492 | 3 | 4 | 5 | | V-2 | TSC22D2 | 0.59 |
| 2397 | 3 | 4 | 5 | | V-2 | TBC1D9B | 0.52 | 2493 | 3 | 4 | 5 | | V-2 | TSEN54 | 0.58 |

Fig. 39 - 14

| | | | | | | | | | | | | | | | | | |
|---|---|---|---|---|---|---|---|---|---|---|---|---|---|---|---|---|---|
| 2494 | 3 | 4 | 5 | | | V-2 | TSHZ1 | 0.57 | 2590 | 3 | 4 | 5 | | | V-2 | ZFYVE1 | 0.60 |
| 2495 | 3 | 4 | 5 | | | V-2 | TSPAN9 | 0.64 | 2591 | 3 | 4 | 5 | | | V-2 | ZFYVE28 | 0.55 |
| 2496 | 3 | 4 | 5 | | | V-2 | TSPYL2 | 0.58 | 2592 | 3 | 4 | 5 | | | V-2 | ZGPAT | 0.57 |
| 2497 | 3 | 4 | 5 | | | V-2 | TSPYL4 | 0.63 | 2593 | 3 | 4 | 5 | | | V-2 | ZMAT5 | 0.64 |
| 2498 | 3 | 4 | 5 | | | V-2 | TTC28 | 0.66 | 2594 | 3 | 4 | 5 | | | V-2 | ZMIZ1 | 0.55 |
| 2499 | 3 | 4 | 5 | | | V-2 | TTI1 | 0.57 | 2595 | 3 | 4 | 5 | | | V-2 | ZMYM3 | 0.60 |
| 2500 | 3 | 4 | 5 | | | V-2 | TTYH2 | 0.52 | 2596 | 3 | 4 | 5 | | | V-2 | ZMYND15 | 0.62 |
| 2501 | 3 | 4 | 5 | | | V-2 | TUBA1A | 0.51 | 2597 | 3 | 4 | 5 | | | V-2 | ZMYND19 | 0.63 |
| 2502 | 3 | 4 | 5 | | | V-2 | TUBA1B | 0.55 | 2598 | 3 | 4 | 5 | | | V-2 | ZNF16 | 0.64 |
| 2503 | 3 | 4 | 5 | | | V-2 | TUBB | 0.58 | 2599 | 3 | 4 | 5 | | | V-2 | ZNF174 | 0.64 |
| 2504 | 3 | 4 | 5 | | | V-2 | TUBB3 | 0.62 | 2600 | 3 | 4 | 5 | | | V-2 | ZNF318 | 0.52 |
| 2505 | 3 | 4 | 5 | | | V-2 | TUBGCP2 | 0.55 | 2601 | 3 | 4 | 5 | | | V-2 | ZNF319 | 0.51 |
| 2506 | 3 | 4 | 5 | | | V-2 | TUFT1 | 0.66 | 2602 | 3 | 4 | 5 | | | V-2 | ZNF324 | 0.50 |
| 2507 | 3 | 4 | 5 | | | V-2 | TULP3 | 0.51 | 2603 | 3 | 4 | 5 | | | V-2 | ZNF324B | 0.56 |
| 2508 | 3 | 4 | 5 | | | V-2 | TWSG1 | 0.63 | 2604 | 3 | 4 | 5 | | | V-2 | ZNF329 | 0.56 |
| 2509 | 3 | 4 | 5 | | | V-2 | U2AF2 | 0.59 | 2605 | 3 | 4 | 5 | | | V-2 | ZNF358 | 0.52 |
| 2510 | 3 | 4 | 5 | | | V-2 | UAP1L1 | 0.55 | 2606 | 3 | 4 | 5 | | | V-2 | ZNF367 | 0.56 |
| 2511 | 3 | 4 | 5 | | | V-2 | UBAP2 | 0.57 | 2607 | 3 | 4 | 5 | | | V-2 | ZNF384 | 0.53 |
| 2512 | 3 | 4 | 5 | | | V-2 | UBC | 0.57 | 2608 | 3 | 4 | 5 | | | V-2 | ZNF385B | 0.55 |
| 2513 | 3 | 4 | 5 | | | V-2 | UBN1 | 0.55 | 2609 | 3 | 4 | 5 | | | V-2 | ZNF407 | 0.63 |
| 2514 | 3 | 4 | 5 | | | V-2 | UBOX5 | 0.51 | 2610 | 3 | 4 | 5 | | | V-2 | ZNF445 | 0.54 |
| 2515 | 3 | 4 | 5 | | | V-2 | UBR4 | 0.65 | 2611 | 3 | 4 | 5 | | | V-2 | ZNF446 | 0.58 |
| 2516 | 3 | 4 | 5 | | | V-2 | UBTF | 0.55 | 2612 | 3 | 4 | 5 | | | V-2 | ZNF462 | 0.65 |
| 2517 | 3 | 4 | 5 | | | V-2 | UBXN1 | 0.56 | 2613 | 3 | 4 | 5 | | | V-2 | ZNF467 | 0.64 |
| 2518 | 3 | 4 | 5 | | | V-2 | UBXN6 | 0.60 | 2614 | 3 | 4 | 5 | | | V-2 | ZNF498 | 0.57 |
| 2519 | 3 | 4 | 5 | | | V-2 | UFSP1 | 0.65 | 2615 | 3 | 4 | 5 | | | V-2 | ZNF516 | 0.63 |
| 2520 | 3 | 4 | 5 | | | V-2 | UNK | 0.61 | 2616 | 3 | 4 | 5 | | | V-2 | ZNF550 | 0.59 |
| 2521 | 3 | 4 | 5 | | | V-2 | UPK3BL | 0.52 | 2617 | 3 | 4 | 5 | | | V-2 | ZNF574 | 0.57 |
| 2522 | 3 | 4 | 5 | | | V-2 | URM1 | 0.60 | 2618 | 3 | 4 | 5 | | | V-2 | ZNF586 | 0.60 |
| 2523 | 3 | 4 | 5 | | | V-2 | USF2 | 0.57 | 2619 | 3 | 4 | 5 | | | V-2 | ZNF597 | 0.60 |
| 2524 | 3 | 4 | 5 | | | V-2 | USP11 | 0.55 | 2620 | 3 | 4 | 5 | | | V-2 | ZNF598 | 0.54 |
| 2525 | 3 | 4 | 5 | | | V-2 | USP19 | 0.55 | 2621 | 3 | 4 | 5 | | | V-2 | ZNF667 | 0.53 |
| 2526 | 3 | 4 | 5 | | | V-2 | USP20 | 0.62 | 2622 | 3 | 4 | 5 | | | V-2 | ZNF70 | 0.57 |
| 2527 | 3 | 4 | 5 | | | V-2 | UTP14A | 0.62 | 2623 | 3 | 4 | 5 | | | V-2 | ZNF74 | 0.64 |
| 2528 | 3 | 4 | 5 | | | V-2 | UVRAG | 0.64 | 2624 | 3 | 4 | 5 | | | V-2 | ZNF740 | 0.66 |
| 2529 | 3 | 4 | 5 | | | V-2 | VAC14 | 0.58 | 2625 | 3 | 4 | 5 | | | V-2 | ZNF746 | 0.62 |
| 2530 | 3 | 4 | 5 | | | V-2 | VANGL2 | 0.62 | 2626 | 3 | 4 | 5 | | | V-2 | ZNF749 | 0.64 |
| 2531 | 3 | 4 | 5 | | | V-2 | VCL | 0.61 | 2627 | 3 | 4 | 5 | | | V-2 | ZNF783 | 0.54 |
| 2532 | 3 | 4 | 5 | | | V-2 | VILL | 0.62 | 2628 | 3 | 4 | 5 | | | V-2 | ZNF8 | 0.60 |
| 2533 | 3 | 4 | 5 | | | V-2 | VIPR1 | 0.58 | 2629 | 3 | 4 | 5 | | | V-2 | ZNF821 | 0.56 |
| 2534 | 3 | 4 | 5 | | | V-2 | VIT | 0.55 | 2630 | 3 | 4 | 5 | | | V-2 | ZNFX1 | 0.50 |
| 2535 | 3 | 4 | 5 | | | V-2 | VPS11 | 0.56 | 2631 | 3 | 4 | 5 | | | V-2 | ZNRF3 | 0.54 |
| 2536 | 3 | 4 | 5 | | | V-2 | VPS18 | 0.54 | 2632 | 3 | 4 | 5 | | | V-2 | ZZEF1 | 0.63 |
| 2537 | 3 | 4 | 5 | | | V-2 | VPS33B | 0.64 | 2633 | 3 | 4 | 5 | | | V-1 | 1/2-SBSRNA4 | 1.51 |
| 2538 | 3 | 4 | 5 | | | V-2 | VPS39 | 0.62 | 2634 | 3 | 4 | 5 | | | V-1 | ACAA2 | 1.88 |
| 2539 | 3 | 4 | 5 | | | V-2 | VPS72 | 0.56 | 2635 | 3 | 4 | 5 | | | V-1 | ACOT2 | 1.87 |
| 2540 | 3 | 4 | 5 | | | V-2 | VSIG8 | 0.51 | 2636 | 3 | 4 | 5 | | | V-1 | ACSL3 | 1.54 |
| 2541 | 3 | 4 | 5 | | | V-2 | VTI1A | 0.54 | 2637 | 3 | 4 | 5 | | | V-1 | ACYP2 | 1.52 |
| 2542 | 3 | 4 | 5 | | | V-2 | WASF1 | 0.51 | 2638 | 3 | 4 | 5 | | | V-1 | AGL | 1.55 |
| 2543 | 3 | 4 | 5 | | | V-2 | WASF3 | 0.66 | 2639 | 3 | 4 | 5 | | | V-1 | AGPAT4-IT1 | 1.80 |
| 2544 | 3 | 4 | 5 | | | V-2 | WBP11 | 0.66 | 2640 | 3 | 4 | 5 | | | V-1 | AGT | 1.52 |
| 2545 | 3 | 4 | 5 | | | V-2 | WDFY2 | 0.59 | 2641 | 3 | 4 | 5 | | | V-1 | ALAS1 | 1.64 |
| 2546 | 3 | 4 | 5 | | | V-2 | WDR1 | 0.66 | 2642 | 3 | 4 | 5 | | | V-1 | ALDH4A1 | 1.51 |
| 2547 | 3 | 4 | 5 | | | V-2 | WDR34 | 0.55 | 2643 | 3 | 4 | 5 | | | V-1 | ANGPTL4 | 1.84 |
| 2548 | 3 | 4 | 5 | | | V-2 | WDR43 | 0.67 | 2644 | 3 | 4 | 5 | | | V-1 | ANKRD46 | 1.58 |
| 2549 | 3 | 4 | 5 | | | V-2 | WDR45 | 0.62 | 2645 | 3 | 4 | 5 | | | V-1 | APOL6 | 1.55 |
| 2550 | 3 | 4 | 5 | | | V-2 | WDR46 | 0.59 | 2646 | 3 | 4 | 5 | | | V-1 | AQP5 | 1.82 |
| 2551 | 3 | 4 | 5 | | | V-2 | WDR47 | 0.64 | 2647 | 3 | 4 | 5 | | | V-1 | ARFGEF2 | 1.78 |
| 2552 | 3 | 4 | 5 | | | V-2 | WDR55 | 0.54 | 2648 | 3 | 4 | 5 | | | V-1 | ARHGAP8 | 1.72 |
| 2553 | 3 | 4 | 5 | | | V-2 | WDR81 | 0.58 | 2649 | 3 | 4 | 5 | | | V-1 | ARID4B | 1.95 |
| 2554 | 3 | 4 | 5 | | | V-2 | WFDC1 | 0.55 | 2650 | 3 | 4 | 5 | | | V-1 | ARRDC4 | 1.70 |
| 2555 | 3 | 4 | 5 | | | V-2 | WFDC5 | 0.62 | 2651 | 3 | 4 | 5 | | | V-1 | ASAH1 | 1.50 |
| 2556 | 3 | 4 | 5 | | | V-2 | WFS1 | 0.62 | 2652 | 3 | 4 | 5 | | | V-1 | ASIP | 1.97 |
| 2557 | 3 | 4 | 5 | | | V-2 | WHSC1 | 0.53 | 2653 | 3 | 4 | 5 | | | V-1 | ATP1B1 | 1.91 |
| 2558 | 3 | 4 | 5 | | | V-2 | WHSC1L1 | 0.67 | 2654 | 3 | 4 | 5 | | | V-1 | ATP5A1 | 1.58 |
| 2559 | 3 | 4 | 5 | | | V-2 | WHSC2 | 0.66 | 2655 | 3 | 4 | 5 | | | V-1 | ATP5G3 | 1.57 |
| 2560 | 3 | 4 | 5 | | | V-2 | WIPF3 | 0.59 | 2656 | 3 | 4 | 5 | | | V-1 | ATP5L | 1.51 |
| 2561 | 3 | 4 | 5 | | | V-2 | WIZ | 0.56 | 2657 | 3 | 4 | 5 | | | V-1 | AUH | 1.69 |
| 2562 | 3 | 4 | 5 | | | V-2 | WWTR1 | 0.63 | 2658 | 3 | 4 | 5 | | | V-1 | B3GALNT1 | 1.54 |
| 2563 | 3 | 4 | 5 | | | V-2 | XAB2 | 0.58 | 2659 | 3 | 4 | 5 | | | V-1 | BACE1-AS | 1.58 |
| 2564 | 3 | 4 | 5 | | | V-2 | XG | 0.52 | 2660 | 3 | 4 | 5 | | | V-1 | BAZ1A | 1.53 |
| 2565 | 3 | 4 | 5 | | | V-2 | XRCC6BP1 | 0.55 | 2661 | 3 | 4 | 5 | | | V-1 | BAZ2B | 1.85 |
| 2566 | 3 | 4 | 5 | | | V-2 | XXYLT1 | 0.51 | 2662 | 3 | 4 | 5 | | | V-1 | BCAS1 | 1.56 |
| 2567 | 3 | 4 | 5 | | | V-2 | XYLT2 | 0.55 | 2663 | 3 | 4 | 5 | | | V-1 | BDH1 | 1.55 |
| 2568 | 3 | 4 | 5 | | | V-2 | YARS | 0.65 | 2664 | 3 | 4 | 5 | | | V-1 | BET1 | 1.54 |
| 2569 | 3 | 4 | 5 | | | V-2 | YBX1 | 0.51 | 2665 | 3 | 4 | 5 | | | V-1 | BEX1 | 1.99 |
| 2570 | 3 | 4 | 5 | | | V-2 | YEATS2 | 0.60 | 2666 | 3 | 4 | 5 | | | V-1 | BEX5 | 1.73 |
| 2571 | 3 | 4 | 5 | | | V-2 | YEATS4 | 0.67 | 2667 | 3 | 4 | 5 | | | V-1 | BLOC1S2 | 1.53 |
| 2572 | 3 | 4 | 5 | | | V-2 | YIF1B | 0.63 | 2668 | 3 | 4 | 5 | | | V-1 | C10orf32 | 1.58 |
| 2573 | 3 | 4 | 5 | | | V-2 | YIPF3 | 0.66 | 2669 | 3 | 4 | 5 | | | V-1 | C10orf58 | 1.55 |
| 2574 | 3 | 4 | 5 | | | V-2 | YWHAH | 0.65 | 2670 | 3 | 4 | 5 | | | V-1 | C11orf73 | 1.63 |
| 2575 | 3 | 4 | 5 | | | V-2 | YY1AP1 | 0.53 | 2671 | 3 | 4 | 5 | | | V-1 | C14orf102 | 1.89 |
| 2576 | 3 | 4 | 5 | | | V-2 | ZBTB2 | 0.56 | 2672 | 3 | 4 | 5 | | | V-1 | C14orf2 | 1.55 |
| 2577 | 3 | 4 | 5 | | | V-2 | ZBTB45 | 0.66 | 2673 | 3 | 4 | 5 | | | V-1 | C14orf28 | 1.74 |
| 2578 | 3 | 4 | 5 | | | V-2 | ZBTB49 | 0.61 | 2674 | 3 | 4 | 5 | | | V-1 | C14orf64 | 1.58 |
| 2579 | 3 | 4 | 5 | | | V-2 | ZC3H12D | 0.56 | 2675 | 3 | 4 | 5 | | | V-1 | C17orf57 | 1.55 |
| 2580 | 3 | 4 | 5 | | | V-2 | ZC3HC1 | 0.62 | 2676 | 3 | 4 | 5 | | | V-1 | C1D | 1.54 |
| 2581 | 3 | 4 | 5 | | | V-2 | ZC4H2 | 0.62 | 2677 | 3 | 4 | 5 | | | V-1 | C1orf122 | 1.88 |
| 2582 | 3 | 4 | 5 | | | V-2 | ZDHHC14 | 0.56 | 2678 | 3 | 4 | 5 | | | V-1 | C1orf9 | 1.74 |
| 2583 | 3 | 4 | 5 | | | V-2 | ZDHHC18 | 0.65 | 2679 | 3 | 4 | 5 | | | V-1 | C21orf33 | 1.52 |
| 2584 | 3 | 4 | 5 | | | V-2 | ZDHHC7 | 0.59 | 2680 | 3 | 4 | 5 | | | V-1 | C2CD2 | 1.58 |
| 2585 | 3 | 4 | 5 | | | V-2 | ZER1 | 0.57 | 2681 | 3 | 4 | 5 | | | V-1 | C2orf63 | 1.92 |
| 2586 | 3 | 4 | 5 | | | V-2 | ZFAND3 | 0.66 | 2682 | 3 | 4 | 5 | | | V-1 | C3orf14 | 1.59 |
| 2587 | 3 | 4 | 5 | | | V-2 | ZFAND4 | 0.65 | 2683 | 3 | 4 | 5 | | | V-1 | C6orf120 | 1.50 |
| 2588 | 3 | 4 | 5 | | | V-2 | ZFP1 | 0.58 | 2684 | 3 | 4 | 5 | | | V-1 | C6orf62 | 1.77 |
| 2589 | 3 | 4 | 5 | | | V-2 | ZFX | 0.57 | 2685 | 3 | 4 | 5 | | | V-1 | C7orf55 | 1.75 |

Fig. 39 - 15

| | | | | | | | | | | | | | | | |
|---|---|---|---|---|---|---|---|---|---|---|---|---|---|---|---|
| 2686 | 3 | 4 | 5 | | V-1 | C8orf76 | 1.72 | 2782 | 3 | 4 | 5 | | V-1 | ID11 | 1.99 |
| 2687 | 3 | 4 | 5 | | V-1 | C9orf152 | 1.72 | 2783 | 3 | 4 | 5 | | V-1 | IL8 | 1.85 |
| 2688 | 3 | 4 | 5 | | V-1 | C9orf5 | 1.87 | 2784 | 3 | 4 | 5 | | V-1 | ITGB3BP | 1.75 |
| 2689 | 3 | 4 | 5 | | V-1 | CA13 | 1.58 | 2785 | 3 | 4 | 5 | | V-1 | ITPR1 | 1.76 |
| 2690 | 3 | 4 | 5 | | V-1 | CATSPER2P1 | 1.55 | 2786 | 3 | 4 | 5 | | V-1 | JRK | 1.83 |
| 2691 | 3 | 4 | 5 | | V-1 | CCDC112 | 1.51 | 2787 | 3 | 4 | 5 | | V-1 | KBTBD6 | 1.54 |
| 2692 | 3 | 4 | 5 | | V-1 | CCDC132 | 1.52 | 2788 | 3 | 4 | 5 | | V-1 | KBTBD7 | 1.58 |
| 2693 | 3 | 4 | 5 | | V-1 | CCDC88A | 1.52 | 2789 | 3 | 4 | 5 | | V-1 | KIAA1737 | 1.53 |
| 2694 | 3 | 4 | 5 | | V-1 | CD164 | 1.60 | 2790 | 3 | 4 | 5 | | V-1 | KIAA1826 | 1.69 |
| 2695 | 3 | 4 | 5 | | V-1 | CD46 | 1.60 | 2791 | 3 | 4 | 5 | | V-1 | KIF21A | 1.63 |
| 2696 | 3 | 4 | 5 | | V-1 | CD99P1 | 1.63 | 2792 | 3 | 4 | 5 | | V-1 | KLB | 1.82 |
| 2697 | 3 | 4 | 5 | | V-1 | CDNF | 1.64 | 2793 | 3 | 4 | 5 | | V-1 | KLHDC9 | 1.50 |
| 2698 | 3 | 4 | 5 | | V-1 | CECR5-AS1 | 1.67 | 2794 | 3 | 4 | 5 | | V-1 | KLHL2 | 1.72 |
| 2699 | 3 | 4 | 5 | | V-1 | CENPV | 1.71 | 2795 | 3 | 4 | 5 | | V-1 | KLHL8 | 1.79 |
| 2700 | 3 | 4 | 5 | | V-1 | CEP41 | 1.80 | 2796 | 3 | 4 | 5 | | V-1 | KRT19P2 | 1.84 |
| 2701 | 3 | 4 | 5 | | V-1 | CHCHD1 | 1.53 | 2797 | 3 | 4 | 5 | | V-1 | KRTDAP | 1.79 |
| 2702 | 3 | 4 | 5 | | V-1 | CHCHD10 | 1.64 | 2798 | 3 | 4 | 5 | | V-1 | LARP4 | 1.53 |
| 2703 | 3 | 4 | 5 | | V-1 | CHMP5 | 1.58 | 2799 | 3 | 4 | 5 | | V-1 | LETMD1 | 1.57 |
| 2704 | 3 | 4 | 5 | | V-1 | CMTM4 | 1.59 | 2800 | 3 | 4 | 5 | | V-1 | LIPN | 1.65 |
| 2705 | 3 | 4 | 5 | | V-1 | CNTN1 | 1.89 | 2801 | 3 | 4 | 5 | | V-1 | LIPT1 | 1.51 |
| 2706 | 3 | 4 | 5 | | V-1 | COL8A1 | 1.56 | 2802 | 3 | 4 | 5 | | V-1 | LIPT2 | 1.65 |
| 2707 | 3 | 4 | 5 | | V-1 | COX7A2 | 1.73 | 2803 | 3 | 4 | 5 | | V-1 | LOC100131726 | 1.59 |
| 2708 | 3 | 4 | 5 | | V-1 | CPM | 1.95 | 2804 | 3 | 4 | 5 | | V-1 | LOC100144604 | 1.63 |
| 2709 | 3 | 4 | 5 | | V-1 | CPT2 | 1.52 | 2805 | 3 | 4 | 5 | | V-1 | LOC100240735 | 1.62 |
| 2710 | 3 | 4 | 5 | | V-1 | CRISPLD1 | 1.89 | 2806 | 3 | 4 | 5 | | V-1 | LOC100289361 | 1.58 |
| 2711 | 3 | 4 | 5 | | V-1 | CSRP2 | 1.81 | 2807 | 3 | 4 | 5 | | V-1 | LOC100505815 | 1.82 |
| 2712 | 3 | 4 | 5 | | V-1 | CUX2 | 1.60 | 2808 | 3 | 4 | 5 | | V-1 | LOC100506599 | 1.64 |
| 2713 | 3 | 4 | 5 | | V-1 | CYCS | 1.62 | 2809 | 3 | 4 | 5 | | V-1 | LOC100506963 | 1.70 |
| 2714 | 3 | 4 | 5 | | V-1 | CYP20A1 | 1.72 | 2810 | 3 | 4 | 5 | | V-1 | LOC158257 | 1.91 |
| 2715 | 3 | 4 | 5 | | V-1 | CYP4F3 | 1.81 | 2811 | 3 | 4 | 5 | | V-1 | LOC284385 | 1.51 |
| 2716 | 3 | 4 | 5 | | V-1 | DAZ2 | 1.77 | 2812 | 3 | 4 | 5 | | V-1 | LOC643648 | 1.57 |
| 2717 | 3 | 4 | 5 | | V-1 | DAZ4 | 1.92 | 2813 | 3 | 4 | 5 | | V-1 | LOC644649 | 1.56 |
| 2718 | 3 | 4 | 5 | | V-1 | DCAF10 | 2.00 | 2814 | 3 | 4 | 5 | | V-1 | LOC652276 | 1.51 |
| 2719 | 3 | 4 | 5 | | V-1 | DCP2 | 1.72 | 2815 | 3 | 4 | 5 | | V-1 | LPP | 1.66 |
| 2720 | 3 | 4 | 5 | | V-1 | DDT | 1.62 | 2816 | 3 | 4 | 5 | | V-1 | LYRM5 | 1.50 |
| 2721 | 3 | 4 | 5 | | V-1 | DHRS11 | 1.57 | 2817 | 3 | 4 | 5 | | V-1 | LYRM7 | 1.62 |
| 2722 | 3 | 4 | 5 | | V-1 | DLD | 1.73 | 2818 | 3 | 4 | 5 | | V-1 | MACC1 | 1.57 |
| 2723 | 3 | 4 | 5 | | V-1 | DOPEY2 | 1.57 | 2819 | 3 | 4 | 5 | | V-1 | MFSD4 | 1.74 |
| 2724 | 3 | 4 | 5 | | V-1 | DPP8 | 1.94 | 2820 | 3 | 4 | 5 | | V-1 | MGAT4A | 1.98 |
| 2725 | 3 | 4 | 5 | | V-1 | DSG2 | 1.75 | 2821 | 3 | 4 | 5 | | V-1 | MSH3 | 1.66 |
| 2726 | 3 | 4 | 5 | | V-1 | DSTYK | 1.97 | 2822 | 3 | 4 | 5 | | V-1 | MYO9A | 1.91 |
| 2727 | 3 | 4 | 5 | | V-1 | EBF1 | 1.54 | 2823 | 3 | 4 | 5 | | V-1 | NCF1 | 1.85 |
| 2728 | 3 | 4 | 5 | | V-1 | ECHDC1 | 1.67 | 2824 | 3 | 4 | 5 | | V-1 | NELL2 | 1.64 |
| 2729 | 3 | 4 | 5 | | V-1 | EIF5 | 1.58 | 2825 | 3 | 4 | 5 | | V-1 | NFIA | 1.73 |
| 2730 | 3 | 4 | 5 | | V-1 | ERI2 | 1.71 | 2826 | 3 | 4 | 5 | | V-1 | NKAP | 1.51 |
| 2731 | 3 | 4 | 5 | | V-1 | ESRRG | 1.98 | 2827 | 3 | 4 | 5 | | V-1 | NTRK3 | 1.60 |
| 2732 | 3 | 4 | 5 | | V-1 | FAM133B | 1.80 | 2828 | 3 | 4 | 5 | | V-1 | OBFC2A | 1.74 |
| 2733 | 3 | 4 | 5 | | V-1 | FAM13A | 1.52 | 2829 | 3 | 4 | 5 | | V-1 | OR2A9P | 1.95 |
| 2734 | 3 | 4 | 5 | | V-1 | FAM195A | 1.59 | 2830 | 3 | 4 | 5 | | V-1 | P2RY13 | 1.66 |
| 2735 | 3 | 4 | 5 | | V-1 | FAM22G | 1.86 | 2831 | 3 | 4 | 5 | | V-1 | PADI2 | 1.55 |
| 2736 | 3 | 4 | 5 | | V-1 | FAM25C | 1.66 | 2832 | 3 | 4 | 5 | | V-1 | PAFAH2 | 1.54 |
| 2737 | 3 | 4 | 5 | | V-1 | FAM26E | 1.72 | 2833 | 3 | 4 | 5 | | V-1 | PAN3-AS1 | 1.61 |
| 2738 | 3 | 4 | 5 | | V-1 | FAM73A | 1.53 | 2834 | 3 | 4 | 5 | | V-1 | PAR-SN | 1.63 |
| 2739 | 3 | 4 | 5 | | V-1 | FAM89A | 1.66 | 2835 | 3 | 4 | 5 | | V-1 | PCAT1 | 1.91 |
| 2740 | 3 | 4 | 5 | | V-1 | FASTKD2 | 1.54 | 2836 | 3 | 4 | 5 | | V-1 | PCDH20 | 1.87 |
| 2741 | 3 | 4 | 5 | | V-1 | FBXO9 | 1.68 | 2837 | 3 | 4 | 5 | | V-1 | PCK2 | 1.68 |
| 2742 | 3 | 4 | 5 | | V-1 | FCN3 | 1.51 | 2838 | 3 | 4 | 5 | | V-1 | PDCD4 | 1.54 |
| 2743 | 3 | 4 | 5 | | V-1 | FKBP5 | 1.53 | 2839 | 3 | 4 | 5 | | V-1 | PDE9A | 1.97 |
| 2744 | 3 | 4 | 5 | | V-1 | FLJ39653 | 1.53 | 2840 | 3 | 4 | 5 | | V-1 | PEX11A | 1.99 |
| 2745 | 3 | 4 | 5 | | V-1 | FLVCR1 | 1.70 | 2841 | 3 | 4 | 5 | | V-1 | PFKFB2 | 1.60 |
| 2746 | 3 | 4 | 5 | | V-1 | FMNL2 | 1.63 | 2842 | 3 | 4 | 5 | | V-1 | PHKB | 1.51 |
| 2747 | 3 | 4 | 5 | | V-1 | FOLR1 | 1.71 | 2843 | 3 | 4 | 5 | | V-1 | PLCB1 | 1.81 |
| 2748 | 3 | 4 | 5 | | V-1 | FRMD6-AS1 | 1.51 | 2844 | 3 | 4 | 5 | | V-1 | PLEKHH1 | 1.72 |
| 2749 | 3 | 4 | 5 | | V-1 | FTH1P3 | 1.57 | 2845 | 3 | 4 | 5 | | V-1 | POLR3G | 1.56 |
| 2750 | 3 | 4 | 5 | | V-1 | FZD3 | 1.66 | 2846 | 3 | 4 | 5 | | V-1 | POMP | 1.68 |
| 2751 | 3 | 4 | 5 | | V-1 | GABARAPL2 | 1.71 | 2847 | 3 | 4 | 5 | | V-1 | POU2F1 | 1.67 |
| 2752 | 3 | 4 | 5 | | V-1 | GCA | 1.94 | 2848 | 3 | 4 | 5 | | V-1 | POU2F2 | 1.94 |
| 2753 | 3 | 4 | 5 | | V-1 | GCSH | 1.63 | 2849 | 3 | 4 | 5 | | V-1 | PPA2 | 1.63 |
| 2754 | 3 | 4 | 5 | | V-1 | GDPD1 | 1.53 | 2850 | 3 | 4 | 5 | | V-1 | PPBP | 1.55 |
| 2755 | 3 | 4 | 5 | | V-1 | GEMIN2 | 1.58 | 2851 | 3 | 4 | 5 | | V-1 | PPIH | 1.70 |
| 2756 | 3 | 4 | 5 | | V-1 | GJC3 | 1.61 | 2852 | 3 | 4 | 5 | | V-1 | PPP1R1B | 1.98 |
| 2757 | 3 | 4 | 5 | | V-1 | GK5 | 1.85 | 2853 | 3 | 4 | 5 | | V-1 | PRDX3 | 1.99 |
| 2758 | 3 | 4 | 5 | | V-1 | GLCCI1 | 1.58 | 2854 | 3 | 4 | 5 | | V-1 | PROM1 | 1.89 |
| 2759 | 3 | 4 | 5 | | V-1 | GNPAT | 1.56 | 2855 | 3 | 4 | 5 | | V-1 | PRRG4 | 1.69 |
| 2760 | 3 | 4 | 5 | | V-1 | GPR34 | 1.51 | 2856 | 3 | 4 | 5 | | V-1 | PTPN14 | 1.62 |
| 2761 | 3 | 4 | 5 | | V-1 | GPT2 | 1.56 | 2857 | 3 | 4 | 5 | | V-1 | PTPRZ1 | 1.89 |
| 2762 | 3 | 4 | 5 | | V-1 | GRAMD1C | 1.79 | 2858 | 3 | 4 | 5 | | V-1 | RAB3GAP2 | 1.57 |
| 2763 | 3 | 4 | 5 | | V-1 | GSTA4 | 1.96 | 2859 | 3 | 4 | 5 | | V-1 | RAB3IP | 1.61 |
| 2764 | 3 | 4 | 5 | | V-1 | H3F3AP4 | 1.50 | 2860 | 3 | 4 | 5 | | V-1 | RAD50 | 1.55 |
| 2765 | 3 | 4 | 5 | | V-1 | HADH | 1.53 | 2861 | 3 | 4 | 5 | | V-1 | RAP1GAP | 1.78 |
| 2766 | 3 | 4 | 5 | | V-1 | HADHB | 1.73 | 2862 | 3 | 4 | 5 | | V-1 | RARB | 1.56 |
| 2767 | 3 | 4 | 5 | | V-1 | HARBI1 | 1.54 | 2863 | 3 | 4 | 5 | | V-1 | RDH11 | 1.89 |
| 2768 | 3 | 4 | 5 | | V-1 | HBG2 | 1.64 | 2864 | 3 | 4 | 5 | | V-1 | RDH16 | 1.63 |
| 2769 | 3 | 4 | 5 | | V-1 | HFE | 1.77 | 2865 | 3 | 4 | 5 | | V-1 | RFC1 | 1.87 |
| 2770 | 3 | 4 | 5 | | V-1 | HIATL2 | 1.60 | 2866 | 3 | 4 | 5 | | V-1 | RGS20 | 1.69 |
| 2771 | 3 | 4 | 5 | | V-1 | HIST1H1C | 1.89 | 2867 | 3 | 4 | 5 | | V-1 | RMI1 | 1.52 |
| 2772 | 3 | 4 | 5 | | V-1 | HIST1H2BH | 1.66 | 2868 | 3 | 4 | 5 | | V-1 | RNF14 | 1.50 |
| 2773 | 3 | 4 | 5 | | V-1 | HIST1H2BJ | 1.57 | 2869 | 3 | 4 | 5 | | V-1 | RNF170 | 1.77 |
| 2774 | 3 | 4 | 5 | | V-1 | HIST1H2BO | 1.61 | 2870 | 3 | 4 | 5 | | V-1 | RPL18 | 1.75 |
| 2775 | 3 | 4 | 5 | | V-1 | HLCS | 1.62 | 2871 | 3 | 4 | 5 | | V-1 | RPL22L1 | 1.60 |
| 2776 | 3 | 4 | 5 | | V-1 | HMGN5 | 1.96 | 2872 | 3 | 4 | 5 | | V-1 | RPS15A | 1.72 |
| 2777 | 3 | 4 | 5 | | V-1 | HOOK3 | 1.63 | 2873 | 3 | 4 | 5 | | V-1 | RPS29 | 1.83 |
| 2778 | 3 | 4 | 5 | | V-1 | HOXC12 | 1.88 | 2874 | 3 | 4 | 5 | | V-1 | RRN3P3 | 1.57 |
| 2779 | 3 | 4 | 5 | | V-1 | HP07349 | 1.68 | 2875 | 3 | 4 | 5 | | V-1 | SCEL | 1.88 |
| 2780 | 3 | 4 | 5 | | V-1 | HSP90AA4P | 1.55 | 2876 | 3 | 4 | 5 | | V-1 | SCGB2B3P | 1.71 |
| 2781 | 3 | 4 | 5 | | V-1 | ID1 | 1.68 | 2877 | 3 | 4 | 5 | | V-1 | SCOC | 1.65 |

Fig. 39 - 16

| | | | | | | | | | | | | | | | |
|---|---|---|---|---|---|---|---|---|---|---|---|---|---|---|---|
| 2878 | 3 | 4 | 5 | | | V-1 | SCRG1 | 1.62 | 2974 | 3 | 4 | | | IV-2 | ABHD14A | 0.75 |
| 2879 | 3 | 4 | 5 | | | V-1 | SEC11C | 1.93 | 2975 | 3 | 4 | | | IV-2 | ABHD15 | 0.71 |
| 2880 | 3 | 4 | 5 | | | V-1 | SEC62 | 1.59 | 2976 | 3 | 4 | | | IV-2 | ABHD16A | 0.83 |
| 2881 | 3 | 4 | 5 | | | V-1 | SELK | 1.58 | 2977 | 3 | 4 | | | IV-2 | ABT1 | 0.71 |
| 2882 | 3 | 4 | 5 | | | V-1 | SEPSECS | 1.70 | 2978 | 3 | 4 | | | IV-2 | ACBD3 | 0.79 |
| 2883 | 3 | 4 | 5 | | | V-1 | SERAC1 | 1.63 | 2979 | 3 | 4 | | | IV-2 | ACCN1 | 0.98 |
| 2884 | 3 | 4 | 5 | | | V-1 | SFRP1 | 1.61 | 2980 | 3 | 4 | | | IV-2 | ACLY | 0.95 |
| 2885 | 3 | 4 | 5 | | | V-1 | SHC4 | 1.53 | 2981 | 3 | 4 | | | IV-2 | ACOT11 | 0.90 |
| 2886 | 3 | 4 | 5 | | | V-1 | SLC13A2 | 1.98 | 2982 | 3 | 4 | | | IV-2 | ACOT8 | 0.71 |
| 2887 | 3 | 4 | 5 | | | V-1 | SLC34A2 | 1.68 | 2983 | 3 | 4 | | | IV-2 | ACP2 | 0.74 |
| 2888 | 3 | 4 | 5 | | | V-1 | SLC35G1 | 1.56 | 2984 | 3 | 4 | | | IV-2 | ACRBP | 0.86 |
| 2889 | 3 | 4 | 5 | | | V-1 | SLC39A8 | 1.66 | 2985 | 3 | 4 | | | IV-2 | ACSS1 | 0.69 |
| 2890 | 3 | 4 | 5 | | | V-1 | SLC44A4 | 1.52 | 2986 | 3 | 4 | | | IV-2 | ACTG2 | 0.81 |
| 2891 | 3 | 4 | 5 | | | V-1 | SLC46A3 | 1.75 | 2987 | 3 | 4 | | | IV-2 | ACTL6A | 0.68 |
| 2892 | 3 | 4 | 5 | | | V-1 | SLC4A7 | 1.60 | 2988 | 3 | 4 | | | IV-2 | ACTN1 | 0.78 |
| 2893 | 3 | 4 | 5 | | | V-1 | SLC7A5P2 | 1.87 | 2989 | 3 | 4 | | | IV-2 | ACTR10 | 0.99 |
| 2894 | 3 | 4 | 5 | | | V-1 | SLCO4C1 | 1.84 | 2990 | 3 | 4 | | | IV-2 | ACTR1B | 0.84 |
| 2895 | 3 | 4 | 5 | | | V-1 | SNRPE | 1.51 | 2991 | 3 | 4 | | | IV-2 | ACTR2 | 0.93 |
| 2896 | 3 | 4 | 5 | | | V-1 | SNRPG | 1.51 | 2992 | 3 | 4 | | | IV-2 | ACTR3 | 0.96 |
| 2897 | 3 | 4 | 5 | | | V-1 | SOR8S2 | 1.82 | 2993 | 3 | 4 | | | IV-2 | ACTR8 | 0.78 |
| 2898 | 3 | 4 | 5 | | | V-1 | SOX2 | 1.59 | 2994 | 3 | 4 | | | IV-2 | ADA | 0.83 |
| 2899 | 3 | 4 | 5 | | | V-1 | SOX8 | 1.61 | 2995 | 3 | 4 | | | IV-2 | ADAM9 | 0.78 |
| 2900 | 3 | 4 | 5 | | | V-1 | SPESP1 | 1.60 | 2996 | 3 | 4 | | | IV-2 | ADAMTS9-AS2 | 0.90 |
| 2901 | 3 | 4 | 5 | | | V-1 | SREK1IP1 | 1.85 | 2997 | 3 | 4 | | | IV-2 | ADAT3 | 0.72 |
| 2902 | 3 | 4 | 5 | | | V-1 | SSPN | 1.69 | 2998 | 3 | 4 | | | IV-2 | ADC | 0.95 |
| 2903 | 3 | 4 | 5 | | | V-1 | ST20 | 1.55 | 2999 | 3 | 4 | | | IV-2 | ADCK3 | 0.81 |
| 2904 | 3 | 4 | 5 | | | V-1 | SWT1 | 1.98 | 3000 | 3 | 4 | | | IV-2 | ADCY2 | 0.68 |
| 2905 | 3 | 4 | 5 | | | V-1 | SYPL2 | 1.65 | 3001 | 3 | 4 | | | IV-2 | ADH5 | 0.96 |
| 2906 | 3 | 4 | 5 | | | V-1 | TBC1D24 | 1.54 | 3002 | 3 | 4 | | | IV-2 | ADI1 | 0.91 |
| 2907 | 3 | 4 | 5 | | | V-1 | TBCA | 1.78 | 3003 | 3 | 4 | | | IV-2 | ADIPOR1 | 0.92 |
| 2908 | 3 | 4 | 5 | | | V-1 | TDG | 1.88 | 3004 | 3 | 4 | | | IV-2 | ADIPOR2 | 0.94 |
| 2909 | 3 | 4 | 5 | | | V-1 | TEAD1 | 1.57 | 3005 | 3 | 4 | | | IV-2 | ADNP | 0.87 |
| 2910 | 3 | 4 | 5 | | | V-1 | TMEM116 | 1.69 | 3006 | 3 | 4 | | | IV-2 | ADNP2 | 0.70 |
| 2911 | 3 | 4 | 5 | | | V-1 | TMEM125 | 1.60 | 3007 | 3 | 4 | | | IV-2 | ADORA2A | 0.77 |
| 2912 | 3 | 4 | 5 | | | V-1 | TMEM136 | 1.75 | 3008 | 3 | 4 | | | IV-2 | ADPGK | 0.81 |
| 2913 | 3 | 4 | 5 | | | V-1 | TMEM144 | 1.82 | 3009 | 3 | 4 | | | IV-2 | ADPRHL2 | 0.73 |
| 2914 | 3 | 4 | 5 | | | V-1 | TMEM38B | 1.78 | 3010 | 3 | 4 | | | IV-2 | ADRA1B | 0.92 |
| 2915 | 3 | 4 | 5 | | | V-1 | TNMD | 1.72 | 3011 | 3 | 4 | | | IV-2 | ADRM1 | 0.73 |
| 2916 | 3 | 4 | 5 | | | V-1 | TNRC6C | 1.88 | 3012 | 3 | 4 | | | IV-2 | ADSL | 0.97 |
| 2917 | 3 | 4 | 5 | | | V-1 | TPD52L1 | 1.54 | 3013 | 3 | 4 | | | IV-2 | ADSS | 0.89 |
| 2918 | 3 | 4 | 5 | | | V-1 | TRIM2 | 1.92 | 3014 | 3 | 4 | | | IV-2 | AEBP2 | 0.94 |
| 2919 | 3 | 4 | 5 | | | V-1 | TRIM33 | 1.85 | 3015 | 3 | 4 | | | IV-2 | AFF1 | 0.82 |
| 2920 | 3 | 4 | 5 | | | V-1 | TRIM55 | 1.66 | 3016 | 3 | 4 | | | IV-2 | AFG3L2 | 0.76 |
| 2921 | 3 | 4 | 5 | | | V-1 | TRNT1 | 1.66 | 3017 | 3 | 4 | | | IV-2 | AGBL5 | 0.80 |
| 2922 | 3 | 4 | 5 | | | V-1 | TSLP | 1.52 | 3018 | 3 | 4 | | | IV-2 | AGPAT2 | 0.79 |
| 2923 | 3 | 4 | 5 | | | V-1 | TTYH1 | 1.94 | 3019 | 3 | 4 | | | IV-2 | AGPS | 0.90 |
| 2924 | 3 | 4 | 5 | | | V-1 | TUBD1 | 1.71 | 3020 | 3 | 4 | | | IV-2 | AGTPBP1 | 0.81 |
| 2925 | 3 | 4 | 5 | | | V-1 | TWISTNB | 1.58 | 3021 | 3 | 4 | | | IV-2 | AGXT2L2 | 0.87 |
| 2926 | 3 | 4 | 5 | | | V-1 | UBE2Q2P1 | 1.72 | 3022 | 3 | 4 | | | IV-2 | AHCTF1 | 0.82 |
| 2927 | 3 | 4 | 5 | | | V-1 | UBE3A | 1.59 | 3023 | 3 | 4 | | | IV-2 | AHCYL2 | 0.89 |
| 2928 | 3 | 4 | 5 | | | V-1 | UGT1A7 | 1.55 | 3024 | 3 | 4 | | | IV-2 | AIDA | 0.75 |
| 2929 | 3 | 4 | 5 | | | V-1 | UGT8 | 1.53 | 3025 | 3 | 4 | | | IV-2 | AJAP1 | 0.95 |
| 2930 | 3 | 4 | 5 | | | V-1 | UPF3B | 1.96 | 3026 | 3 | 4 | | | IV-2 | AK1 | 0.74 |
| 2931 | 3 | 4 | 5 | | | V-1 | UQCRQ | 1.71 | 3027 | 3 | 4 | | | IV-2 | AK2 | 0.83 |
| 2932 | 3 | 4 | 5 | | | V-1 | UROS | 1.70 | 3028 | 3 | 4 | | | IV-2 | AK7 | 0.92 |
| 2933 | 3 | 4 | 5 | | | V-1 | UTY | 1.66 | 3029 | 3 | 4 | | | IV-2 | AKAP1 | 0.82 |
| 2934 | 3 | 4 | 5 | | | V-1 | VN1R1 | 1.94 | 3030 | 3 | 4 | | | IV-2 | AKAP11 | 0.97 |
| 2935 | 3 | 4 | 5 | | | V-1 | VSIG10L | 1.63 | 3031 | 3 | 4 | | | IV-2 | AKAP6 | 0.95 |
| 2936 | 3 | 4 | 5 | | | V-1 | VTCN1 | 1.98 | 3032 | 3 | 4 | | | IV-2 | AKD1 | 0.78 |
| 2937 | 3 | 4 | 5 | | | V-1 | XIAP | 1.75 | 3033 | 3 | 4 | | | IV-2 | AKIRIN2 | 0.68 |
| 2938 | 3 | 4 | 5 | | | V-1 | ZDHHC21 | 1.77 | 3034 | 3 | 4 | | | IV-2 | AKR1B1 | 0.89 |
| 2939 | 3 | 4 | 5 | | | V-1 | ZDHHC23 | 1.50 | 3035 | 3 | 4 | | | IV-2 | AKR1E2 | 0.86 |
| 2940 | 3 | 4 | 5 | | | V-1 | ZFP30 | 1.82 | 3036 | 3 | 4 | | | IV-2 | AKT1 | 0.71 |
| 2941 | 3 | 4 | 5 | | | V-1 | ZG16B | 1.64 | 3037 | 3 | 4 | | | IV-2 | AKT2 | 0.68 |
| 2942 | 3 | 4 | 5 | | | V-1 | ZMAT3 | 1.64 | 3038 | 3 | 4 | | | IV-2 | ALDH18A1 | 0.86 |
| 2943 | 3 | 4 | 5 | | | V-1 | ZNF107 | 1.53 | 3039 | 3 | 4 | | | IV-2 | ALDH3A1 | 0.92 |
| 2944 | 3 | 4 | 5 | | | V-1 | ZNF14 | 1.95 | 3040 | 3 | 4 | | | IV-2 | ALDH3A2 | 0.92 |
| 2945 | 3 | 4 | 5 | | | V-1 | ZNF140 | 1.53 | 3041 | 3 | 4 | | | IV-2 | ALDH8A1 | 0.98 |
| 2946 | 3 | 4 | 5 | | | V-1 | ZNF234 | 1.63 | 3042 | 3 | 4 | | | IV-2 | ALG1 | 0.89 |
| 2947 | 3 | 4 | 5 | | | V-1 | ZNF267 | 1.57 | 3043 | 3 | 4 | | | IV-2 | ALG11 | 0.85 |
| 2948 | 3 | 4 | 5 | | | V-1 | ZNF271 | 1.69 | 3044 | 3 | 4 | | | IV-2 | ALG12 | 0.71 |
| 2949 | 3 | 4 | 5 | | | V-1 | ZNF277 | 1.81 | 3045 | 3 | 4 | | | IV-2 | ALG2 | 0.99 |
| 2950 | 3 | 4 | 5 | | | V-1 | ZNF320 | 1.54 | 3046 | 3 | 4 | | | IV-2 | ALG9 | 0.75 |
| 2951 | 3 | 4 | 5 | | | V-1 | ZNF37A | 1.54 | 3047 | 3 | 4 | | | IV-2 | ALKBH3 | 0.77 |
| 2952 | 3 | 4 | 5 | | | V-1 | ZNF404 | 1.73 | 3048 | 3 | 4 | | | IV-2 | ALKBH8 | 0.78 |
| 2953 | 3 | 4 | 5 | | | V-1 | ZNF573 | 1.52 | 3049 | 3 | 4 | | | IV-2 | ALOX12 | 0.81 |
| 2954 | 3 | 4 | 5 | | | V-1 | ZNF662 | 1.53 | 3050 | 3 | 4 | | | IV-2 | ALS2 | 0.80 |
| 2955 | 3 | 4 | 5 | | | V-1 | ZNF773 | 1.51 | 3051 | 3 | 4 | | | IV-2 | ALX1 | 0.78 |
| 2956 | 3 | 4 | 5 | | | V-1 | ZNF780B | 1.91 | 3052 | 3 | 4 | | | IV-2 | AMDHD2 | 0.98 |
| 2957 | 3 | 4 | 5 | | | V-1 | ZNF816 | 1.91 | 3053 | 3 | 4 | | | IV-2 | AMFR | 0.73 |
| 2958 | 3 | 4 | 5 | | | V-1 | ZNF879 | 1.93 | 3054 | 3 | 4 | | | IV-2 | AMH | 0.86 |
| 2959 | 3 | 4 | 5 | | | V-1 | ZNF93 | 1.62 | 3055 | 3 | 4 | | | IV-2 | AMMECR1L | 0.72 |
| 2960 | 3 | 4 | 5 | | | V-1 | ZNRD1 | 1.67 | 3056 | 3 | 4 | | | IV-2 | AMN | 0.98 |
| 2961 | 3 | 4 | 5 | | | V-1 | ZP1 | 1.58 | 3057 | 3 | 4 | | | IV-2 | AMOT | 0.96 |
| 2962 | 3 | 4 | | | | IV-2 | A1BG | 0.93 | 3058 | 3 | 4 | | | IV-2 | ANAPC10 | 0.89 |
| 2963 | 3 | 4 | | | | IV-2 | A2LD1 | 0.96 | 3059 | 3 | 4 | | | IV-2 | ANAPC5 | 0.75 |
| 2964 | 3 | 4 | | | | IV-2 | AAGAB | 0.96 | 3060 | 3 | 4 | | | IV-2 | ANGPT4 | 0.71 |
| 2965 | 3 | 4 | | | | IV-2 | AAMP | 0.85 | 3061 | 3 | 4 | | | IV-2 | ANKFY1 | 0.80 |
| 2966 | 3 | 4 | | | | IV-2 | AARS2 | 0.81 | 3062 | 3 | 4 | | | IV-2 | ANKLE1 | 0.87 |
| 2967 | 3 | 4 | | | | IV-2 | AARSD1 | 0.71 | 3063 | 3 | 4 | | | IV-2 | ANKRA2 | 0.96 |
| 2968 | 3 | 4 | | | | IV-2 | AATK | 0.92 | 3064 | 3 | 4 | | | IV-2 | ANKRD13A | 0.94 |
| 2969 | 3 | 4 | | | | IV-2 | ABCB7 | 0.78 | 3065 | 3 | 4 | | | IV-2 | ANKRD13C | 0.84 |
| 2970 | 3 | 4 | | | | IV-2 | ABCB9 | 0.87 | 3066 | 3 | 4 | | | IV-2 | ANKRD16 | 0.84 |
| 2971 | 3 | 4 | | | | IV-2 | ABCE1 | 0.96 | 3067 | 3 | 4 | | | IV-2 | ANKRD19P | 0.70 |
| 2972 | 3 | 4 | | | | IV-2 | ABCF3 | 0.67 | 3068 | 3 | 4 | | | IV-2 | ANKRD27 | 0.68 |
| 2973 | 3 | 4 | | | | IV-2 | ABHD12 | 0.75 | 3069 | 3 | 4 | | | IV-2 | ANKRD28 | 0.96 |

Fig. 39 - 17

| | | | | | | | | | | | | | | |
|---|---|---|---|---|---|---|---|---|---|---|---|---|---|---|
| 3070 | 3 | 4 | | | IV-2 | ANKRD40 | 0.76 | 3166 | 3 | 4 | | | IV-2 | ATF6B | 0.93 |
| 3071 | 3 | 4 | | | IV-2 | ANKRD50 | 0.71 | 3167 | 3 | 4 | | | IV-2 | ATG10 | 0.90 |
| 3072 | 3 | 4 | | | IV-2 | ANKRD54 | 0.78 | 3168 | 3 | 4 | | | IV-2 | ATG14 | 0.83 |
| 3073 | 3 | 4 | | | IV-2 | ANKRD65 | 0.67 | 3169 | 3 | 4 | | | IV-2 | ATG16L1 | 0.82 |
| 3074 | 3 | 4 | | | IV-2 | ANKRD9 | 0.71 | 3170 | 3 | 4 | | | IV-2 | ATG2B | 0.90 |
| 3075 | 3 | 4 | | | IV-2 | ANO6 | 0.76 | 3171 | 3 | 4 | | | IV-2 | ATG3 | 0.69 |
| 3076 | 3 | 4 | | | IV-2 | ANO8 | 0.69 | 3172 | 3 | 4 | | | IV-2 | ATG4A | 0.97 |
| 3077 | 3 | 4 | | | IV-2 | ANP32A | 0.72 | 3173 | 3 | 4 | | | IV-2 | ATG4B | 0.70 |
| 3078 | 3 | 4 | | | IV-2 | ANP32B | 0.84 | 3174 | 3 | 4 | | | IV-2 | ATG4C | 0.82 |
| 3079 | 3 | 4 | | | IV-2 | ANP32E | 0.91 | 3175 | 3 | 4 | | | IV-2 | ATG5 | 0.95 |
| 3080 | 3 | 4 | | | IV-2 | ANTXR2 | 0.71 | 3176 | 3 | 4 | | | IV-2 | ATG7 | 0.94 |
| 3081 | 3 | 4 | | | IV-2 | ANXA13 | 0.95 | 3177 | 3 | 4 | | | IV-2 | ATG9B | 0.76 |
| 3082 | 3 | 4 | | | IV-2 | ANXA4 | 1.00 | 3178 | 3 | 4 | | | IV-2 | ATIC | 0.81 |
| 3083 | 3 | 4 | | | IV-2 | ANXA7 | 0.81 | 3179 | 3 | 4 | | | IV-2 | ATMIN | 0.92 |
| 3084 | 3 | 4 | | | IV-2 | AOX1 | 0.90 | 3180 | 3 | 4 | | | IV-2 | ATOX1 | 0.92 |
| 3085 | 3 | 4 | | | IV-2 | AP1S2 | 0.81 | 3181 | 3 | 4 | | | IV-2 | ATP11A | 0.89 |
| 3086 | 3 | 4 | | | IV-2 | AP1S3 | 0.74 | 3182 | 3 | 4 | | | IV-2 | ATP11C | 0.92 |
| 3087 | 3 | 4 | | | IV-2 | AP3M1 | 0.97 | 3183 | 3 | 4 | | | IV-2 | ATP13A5 | 0.98 |
| 3088 | 3 | 4 | | | IV-2 | AP3S1 | 0.79 | 3184 | 3 | 4 | | | IV-2 | ATP1A1 | 0.96 |
| 3089 | 3 | 4 | | | IV-2 | APAF1 | 0.89 | 3185 | 3 | 4 | | | IV-2 | ATP1B3 | 0.78 |
| 3090 | 3 | 4 | | | IV-2 | APBA3 | 0.75 | 3186 | 3 | 4 | | | IV-2 | ATP2B1 | 0.67 |
| 3091 | 3 | 4 | | | IV-2 | APBB1IP | 0.85 | 3187 | 3 | 4 | | | IV-2 | ATP2B4 | 0.70 |
| 3092 | 3 | 4 | | | IV-2 | APC | 0.86 | 3188 | 3 | 4 | | | IV-2 | ATP2C2 | 0.89 |
| 3093 | 3 | 4 | | | IV-2 | APEH | 0.80 | 3189 | 3 | 4 | | | IV-2 | ATP5C1 | 0.98 |
| 3094 | 3 | 4 | | | IV-2 | APEX1 | 0.68 | 3190 | 3 | 4 | | | IV-2 | ATP5G2 | 0.95 |
| 3095 | 3 | 4 | | | IV-2 | API5 | 0.85 | 3191 | 3 | 4 | | | IV-2 | ATP5L2 | 0.68 |
| 3096 | 3 | 4 | | | IV-2 | APIP | 0.73 | 3192 | 3 | 4 | | | IV-2 | ATP6V0A2 | 0.76 |
| 3097 | 3 | 4 | | | IV-2 | APLF | 0.92 | 3193 | 3 | 4 | | | IV-2 | ATP6V0E2 | 0.88 |
| 3098 | 3 | 4 | | | IV-2 | APLP2 | 0.75 | 3194 | 3 | 4 | | | IV-2 | ATP6V1F | 0.73 |
| 3099 | 3 | 4 | | | IV-2 | APOA1BP | 0.73 | 3195 | 3 | 4 | | | IV-2 | ATP6V1G1 | 1.00 |
| 3100 | 3 | 4 | | | IV-2 | APOPT1 | 0.91 | 3196 | 3 | 4 | | | IV-2 | ATP6V1G2 | 0.94 |
| 3101 | 3 | 4 | | | IV-2 | APP | 0.89 | 3197 | 3 | 4 | | | IV-2 | ATP7B | 0.91 |
| 3102 | 3 | 4 | | | IV-2 | APPBP2 | 0.81 | 3198 | 3 | 4 | | | IV-2 | ATP9B | 0.86 |
| 3103 | 3 | 4 | | | IV-2 | APPL2 | 0.83 | 3199 | 3 | 4 | | | IV-2 | ATPBD4 | 0.85 |
| 3104 | 3 | 4 | | | IV-2 | ARCN1 | 0.70 | 3200 | 3 | 4 | | | IV-2 | ATRN | 0.73 |
| 3105 | 3 | 4 | | | IV-2 | ARF4 | 0.82 | 3201 | 3 | 4 | | | IV-2 | ATXN1 | 0.73 |
| 3106 | 3 | 4 | | | IV-2 | ARF5 | 0.75 | 3202 | 3 | 4 | | | IV-2 | ATXN10 | 0.96 |
| 3107 | 3 | 4 | | | IV-2 | ARFGAP2 | 0.78 | 3203 | 3 | 4 | | | IV-2 | ATXN3 | 0.97 |
| 3108 | 3 | 4 | | | IV-2 | ARFIP2 | 0.79 | 3204 | 3 | 4 | | | IV-2 | AURKAIP1 | 0.83 |
| 3109 | 3 | 4 | | | IV-2 | ARFRP1 | 0.88 | 3205 | 3 | 4 | | | IV-2 | AUTS2 | 0.69 |
| 3110 | 3 | 4 | | | IV-2 | ARHGAP12 | 0.96 | 3206 | 3 | 4 | | | IV-2 | AZIN1 | 0.96 |
| 3111 | 3 | 4 | | | IV-2 | ARHGAP18 | 0.86 | 3207 | 3 | 4 | | | IV-2 | B2M | 0.71 |
| 3112 | 3 | 4 | | | IV-2 | ARHGAP19 | 0.87 | 3208 | 3 | 4 | | | IV-2 | B3GALNT2 | 1.00 |
| 3113 | 3 | 4 | | | IV-2 | ARHGAP24 | 0.68 | 3209 | 3 | 4 | | | IV-2 | B3GALT6 | 0.79 |
| 3114 | 3 | 4 | | | IV-2 | ARHGAP25 | 0.75 | 3210 | 3 | 4 | | | IV-2 | B3GALTL | 0.91 |
| 3115 | 3 | 4 | | | IV-2 | ARHGAP28 | 0.87 | 3211 | 3 | 4 | | | IV-2 | B3GNT1 | 0.72 |
| 3116 | 3 | 4 | | | IV-2 | ARHGAP29 | 0.81 | 3212 | 3 | 4 | | | IV-2 | B3GNT2 | 0.98 |
| 3117 | 3 | 4 | | | IV-2 | ARHGAP32 | 0.78 | 3213 | 3 | 4 | | | IV-2 | B4GALNT4 | 0.81 |
| 3118 | 3 | 4 | | | IV-2 | ARHGAP44 | 0.79 | 3214 | 3 | 4 | | | IV-2 | B4GALT6 | 0.97 |
| 3119 | 3 | 4 | | | IV-2 | ARHGEF10L | 0.68 | 3215 | 3 | 4 | | | IV-2 | BAALC | 0.85 |
| 3120 | 3 | 4 | | | IV-2 | ARHGEF9 | 0.75 | 3216 | 3 | 4 | | | IV-2 | BABAM1 | 0.78 |
| 3121 | 3 | 4 | | | IV-2 | ARID1A | 0.80 | 3217 | 3 | 4 | | | IV-2 | BAG4 | 0.82 |
| 3122 | 3 | 4 | | | IV-2 | ARID1B | 0.83 | 3218 | 3 | 4 | | | IV-2 | BAIAP2L1 | 0.82 |
| 3123 | 3 | 4 | | | IV-2 | ARID3A | 0.82 | 3219 | 3 | 4 | | | IV-2 | BAIAP2L2 | 0.76 |
| 3124 | 3 | 4 | | | IV-2 | ARID5B | 0.69 | 3220 | 3 | 4 | | | IV-2 | BAIAP3 | 0.88 |
| 3125 | 3 | 4 | | | IV-2 | ARIH1 | 0.98 | 3221 | 3 | 4 | | | IV-2 | BANF1 | 0.72 |
| 3126 | 3 | 4 | | | IV-2 | ARIH2 | 0.89 | 3222 | 3 | 4 | | | IV-2 | BASP1P1 | 0.97 |
| 3127 | 3 | 4 | | | IV-2 | ARL13B | 0.84 | 3223 | 3 | 4 | | | IV-2 | BATF2 | 0.95 |
| 3128 | 3 | 4 | | | IV-2 | ARL17B | 0.90 | 3224 | 3 | 4 | | | IV-2 | BAX | 0.98 |
| 3129 | 3 | 4 | | | IV-2 | ARL2BP | 0.84 | 3225 | 3 | 4 | | | IV-2 | BAZ1B | 0.73 |
| 3130 | 3 | 4 | | | IV-2 | ARL6IP5 | 0.93 | 3226 | 3 | 4 | | | IV-2 | BBC3 | 0.78 |
| 3131 | 3 | 4 | | | IV-2 | ARL6IP6 | 0.77 | 3227 | 3 | 4 | | | IV-2 | BBIP1 | 0.76 |
| 3132 | 3 | 4 | | | IV-2 | ARMCX2 | 0.88 | 3228 | 3 | 4 | | | IV-2 | BBS2 | 0.73 |
| 3133 | 3 | 4 | | | IV-2 | ARMCX5 | 0.76 | 3229 | 3 | 4 | | | IV-2 | BBS9 | 0.70 |
| 3134 | 3 | 4 | | | IV-2 | ARMCX6 | 0.95 | 3230 | 3 | 4 | | | IV-2 | BCAP31 | 0.88 |
| 3135 | 3 | 4 | | | IV-2 | ARPC1B | 0.72 | 3231 | 3 | 4 | | | IV-2 | BCDIN3D | 0.93 |
| 3136 | 3 | 4 | | | IV-2 | ARPC2 | 0.88 | 3232 | 3 | 4 | | | IV-2 | BCL11A | 0.86 |
| 3137 | 3 | 4 | | | IV-2 | ARPC5 | 0.97 | 3233 | 3 | 4 | | | IV-2 | BCL2 | 0.86 |
| 3138 | 3 | 4 | | | IV-2 | ARPP19 | 0.93 | 3234 | 3 | 4 | | | IV-2 | BCL2L11 | 0.74 |
| 3139 | 3 | 4 | | | IV-2 | ARRDC1 | 0.80 | 3235 | 3 | 4 | | | IV-2 | BCL2L2 | 0.80 |
| 3140 | 3 | 4 | | | IV-2 | ARRDC3 | 0.77 | 3236 | 3 | 4 | | | IV-2 | BCL6 | 0.73 |
| 3141 | 3 | 4 | | | IV-2 | ARSK | 0.93 | 3237 | 3 | 4 | | | IV-2 | BCL7B | 0.72 |
| 3142 | 3 | 4 | | | IV-2 | ART4 | 0.94 | 3238 | 3 | 4 | | | IV-2 | BCLAF1 | 0.89 |
| 3143 | 3 | 4 | | | IV-2 | ARV1 | 0.95 | 3239 | 3 | 4 | | | IV-2 | BCRP2 | 0.81 |
| 3144 | 3 | 4 | | | IV-2 | ASAP1 | 0.81 | 3240 | 3 | 4 | | | IV-2 | BEST4 | 0.91 |
| 3145 | 3 | 4 | | | IV-2 | ASAP2 | 0.70 | 3241 | 3 | 4 | | | IV-2 | BEX2 | 0.83 |
| 3146 | 3 | 4 | | | IV-2 | ASAP3 | 0.85 | 3242 | 3 | 4 | | | IV-2 | BEX4 | 0.94 |
| 3147 | 3 | 4 | | | IV-2 | ASB1 | 0.67 | 3243 | 3 | 4 | | | IV-2 | BFAR | 0.87 |
| 3148 | 3 | 4 | | | IV-2 | ASB14 | 0.99 | 3244 | 3 | 4 | | | IV-2 | BHLHB9 | 0.75 |
| 3149 | 3 | 4 | | | IV-2 | ASB2 | 0.72 | 3245 | 3 | 4 | | | IV-2 | BICD1 | 0.94 |
| 3150 | 3 | 4 | | | IV-2 | ASB7 | 0.78 | 3246 | 3 | 4 | | | IV-2 | BID | 0.88 |
| 3151 | 3 | 4 | | | IV-2 | ASB9 | 0.71 | 3247 | 3 | 4 | | | IV-2 | BIN2 | 0.69 |
| 3152 | 3 | 4 | | | IV-2 | ASCC1 | 0.92 | 3248 | 3 | 4 | | | IV-2 | BIN3 | 0.68 |
| 3153 | 3 | 4 | | | IV-2 | ASGR1 | 0.81 | 3249 | 3 | 4 | | | IV-2 | BIRC2 | 0.93 |
| 3154 | 3 | 4 | | | IV-2 | ASH1L | 0.88 | 3250 | 3 | 4 | | | IV-2 | BLOC1S1 | 0.70 |
| 3155 | 3 | 4 | | | IV-2 | ASH2L | 0.82 | 3251 | 3 | 4 | | | IV-2 | BLOC1S3 | 0.97 |
| 3156 | 3 | 4 | | | IV-2 | ASMTL | 0.70 | 3252 | 3 | 4 | | | IV-2 | BLVRA | 0.78 |
| 3157 | 3 | 4 | | | IV-2 | ASNSD1 | 0.79 | 3253 | 3 | 4 | | | IV-2 | BLVRB | 0.89 |
| 3158 | 3 | 4 | | | IV-2 | ASS1 | 0.67 | 3254 | 3 | 4 | | | IV-2 | BMP2K | 0.71 |
| 3159 | 3 | 4 | | | IV-2 | ASTE1 | 0.98 | 3255 | 3 | 4 | | | IV-2 | BMP8B | 0.77 |
| 3160 | 3 | 4 | | | IV-2 | ASTN1 | 0.91 | 3256 | 3 | 4 | | | IV-2 | BMPR2 | 1.00 |
| 3161 | 3 | 4 | | | IV-2 | ASUN | 0.85 | 3257 | 3 | 4 | | | IV-2 | BMX | 0.99 |
| 3162 | 3 | 4 | | | IV-2 | ATAD3C | 0.99 | 3258 | 3 | 4 | | | IV-2 | BNC2 | 0.85 |
| 3163 | 3 | 4 | | | IV-2 | ATE1 | 0.98 | 3259 | 3 | 4 | | | IV-2 | BNIP2 | 1.00 |
| 3164 | 3 | 4 | | | IV-2 | ATF3 | 0.69 | 3260 | 3 | 4 | | | IV-2 | BNIPL | 0.94 |
| 3165 | 3 | 4 | | | IV-2 | ATF5 | 0.70 | 3261 | 3 | 4 | | | IV-2 | BOD1 | 0.85 |

Fig. 39 - 18

| | | | | | | | | | | | | | | | |
|---|---|---|---|---|---|---|---|---|---|---|---|---|---|---|---|
| 3262 | 3 | 4 | | | IV-2 | BOD1P | 0.86 | 3358 | 3 | 4 | | | IV-2 | C1QTNF98-AS1 | 0.73 |
| 3263 | 3 | 4 | | | IV-2 | BOK | 0.92 | 3359 | 3 | 4 | | | IV-2 | C1RL | 0.77 |
| 3264 | 3 | 4 | | | IV-2 | BOLA1 | 0.99 | 3360 | 3 | 4 | | | IV-2 | C20orf111 | 0.81 |
| 3265 | 3 | 4 | | | IV-2 | BOLA2 | 0.82 | 3361 | 3 | 4 | | | IV-2 | C20orf194 | 0.94 |
| 3266 | 3 | 4 | | | IV-2 | BOP1 | 0.68 | 3362 | 3 | 4 | | | IV-2 | C20orf20 | 0.93 |
| 3267 | 3 | 4 | | | IV-2 | BPGM | 0.88 | 3363 | 3 | 4 | | | IV-2 | C20orf96 | 0.73 |
| 3268 | 3 | 4 | | | IV-2 | BPHL | 0.82 | 3364 | 3 | 4 | | | IV-2 | C21orf119 | 0.89 |
| 3269 | 3 | 4 | | | IV-2 | BRAP | 0.93 | 3365 | 3 | 4 | | | IV-2 | C21orf56 | 0.69 |
| 3270 | 3 | 4 | | | IV-2 | BRCC3 | 0.97 | 3366 | 3 | 4 | | | IV-2 | C21orf59 | 0.87 |
| 3271 | 3 | 4 | | | IV-2 | BRE | 0.96 | 3367 | 3 | 4 | | | IV-2 | C21orf63 | 0.68 |
| 3272 | 3 | 4 | | | IV-2 | BREA2 | 0.89 | 3368 | 3 | 4 | | | IV-2 | C21orf88 | 0.69 |
| 3273 | 3 | 4 | | | IV-2 | BRF1 | 0.68 | 3369 | 3 | 4 | | | IV-2 | C22orf25 | 0.84 |
| 3274 | 3 | 4 | | | IV-2 | BRI3 | 0.90 | 3370 | 3 | 4 | | | IV-2 | C22orf39 | 0.83 |
| 3275 | 3 | 4 | | | IV-2 | BRIX1 | 0.83 | 3371 | 3 | 4 | | | IV-2 | C2CD3 | 0.93 |
| 3276 | 3 | 4 | | | IV-2 | BRK1 | 1.00 | 3372 | 3 | 4 | | | IV-2 | C2orf49 | 0.78 |
| 3277 | 3 | 4 | | | IV-2 | BRWD3 | 0.83 | 3373 | 3 | 4 | | | IV-2 | C2orf68 | 0.88 |
| 3278 | 3 | 4 | | | IV-2 | BSDC1 | 0.87 | 3374 | 3 | 4 | | | IV-2 | C2orf81 | 0.79 |
| 3279 | 3 | 4 | | | IV-2 | BTBD1 | 0.79 | 3375 | 3 | 4 | | | IV-2 | C3orf17 | 0.99 |
| 3280 | 3 | 4 | | | IV-2 | BTBD10 | 0.96 | 3376 | 3 | 4 | | | IV-2 | C3orf23 | 0.96 |
| 3281 | 3 | 4 | | | IV-2 | BTBD6 | 0.68 | 3377 | 3 | 4 | | | IV-2 | C3orf75 | 0.85 |
| 3282 | 3 | 4 | | | IV-2 | BTBD7 | 0.99 | 3378 | 3 | 4 | | | IV-2 | C4orf27 | 0.68 |
| 3283 | 3 | 4 | | | IV-2 | BTF3L4 | 0.89 | 3379 | 3 | 4 | | | IV-2 | C4orf32 | 0.92 |
| 3284 | 3 | 4 | | | IV-2 | BYSL | 0.69 | 3380 | 3 | 4 | | | IV-2 | C4orf33 | 0.80 |
| 3285 | 3 | 4 | | | IV-2 | BZW2 | 0.92 | 3381 | 3 | 4 | | | IV-2 | C4orf39 | 0.95 |
| 3286 | 3 | 4 | | | IV-2 | C10orf11 | 0.89 | 3382 | 3 | 4 | | | IV-2 | C4orf43 | 0.93 |
| 3287 | 3 | 4 | | | IV-2 | C10orf2 | 0.78 | 3383 | 3 | 4 | | | IV-2 | C4orf47 | 0.82 |
| 3288 | 3 | 4 | | | IV-2 | C10orf25 | 0.91 | 3384 | 3 | 4 | | | IV-2 | C5orf15 | 0.69 |
| 3289 | 3 | 4 | | | IV-2 | C10orf47 | 0.99 | 3385 | 3 | 4 | | | IV-2 | C5orf24 | 0.95 |
| 3290 | 3 | 4 | | | IV-2 | C10orf55 | 0.90 | 3386 | 3 | 4 | | | IV-2 | C5orf25 | 0.74 |
| 3291 | 3 | 4 | | | IV-2 | C10orf76 | 0.69 | 3387 | 3 | 4 | | | IV-2 | C5orf30 | 0.76 |
| 3292 | 3 | 4 | | | IV-2 | C11orf1 | 0.97 | 3388 | 3 | 4 | | | IV-2 | C5orf38 | 0.84 |
| 3293 | 3 | 4 | | | IV-2 | C11orf35 | 0.75 | 3389 | 3 | 4 | | | IV-2 | C5orf45 | 0.96 |
| 3294 | 3 | 4 | | | IV-2 | C11orf48 | 0.90 | 3390 | 3 | 4 | | | IV-2 | C5orf51 | 0.83 |
| 3295 | 3 | 4 | | | IV-2 | C11orf51 | 0.94 | 3391 | 3 | 4 | | | IV-2 | C5orf65 | 0.92 |
| 3296 | 3 | 4 | | | IV-2 | C11orf67 | 0.91 | 3392 | 3 | 4 | | | IV-2 | C6orf108 | 0.75 |
| 3297 | 3 | 4 | | | IV-2 | C11orf80 | 0.72 | 3393 | 3 | 4 | | | IV-2 | C6orf115 | 0.96 |
| 3298 | 3 | 4 | | | IV-2 | C11orf83 | 0.83 | 3394 | 3 | 4 | | | IV-2 | C6orf136 | 0.98 |
| 3299 | 3 | 4 | | | IV-2 | C11orf9 | 0.96 | 3395 | 3 | 4 | | | IV-2 | C6orf162 | 0.78 |
| 3300 | 3 | 4 | | | IV-2 | C12orf23 | 0.95 | 3396 | 3 | 4 | | | IV-2 | C6orf192 | 0.82 |
| 3301 | 3 | 4 | | | IV-2 | C12orf32 | 0.78 | 3397 | 3 | 4 | | | IV-2 | C6orf48 | 0.72 |
| 3302 | 3 | 4 | | | IV-2 | C12orf43 | 0.68 | 3398 | 3 | 4 | | | IV-2 | C7orf11 | 0.72 |
| 3303 | 3 | 4 | | | IV-2 | C12orf47 | 0.89 | 3399 | 3 | 4 | | | IV-2 | C7orf13 | 0.69 |
| 3304 | 3 | 4 | | | IV-2 | C12orf57 | 0.70 | 3400 | 3 | 4 | | | IV-2 | C7orf25 | 0.91 |
| 3305 | 3 | 4 | | | IV-2 | C12orf68 | 0.98 | 3401 | 3 | 4 | | | IV-2 | C7orf31 | 0.90 |
| 3306 | 3 | 4 | | | IV-2 | C12orf75 | 0.70 | 3402 | 3 | 4 | | | IV-2 | C7orf42 | 0.71 |
| 3307 | 3 | 4 | | | IV-2 | C14orf118 | 0.85 | 3403 | 3 | 4 | | | IV-2 | C7orf44 | 0.68 |
| 3308 | 3 | 4 | | | IV-2 | C14orf119 | 0.82 | 3404 | 3 | 4 | | | IV-2 | C7orf50 | 0.91 |
| 3309 | 3 | 4 | | | IV-2 | C14orf132 | 0.92 | 3405 | 3 | 4 | | | IV-2 | C7orf58 | 0.99 |
| 3310 | 3 | 4 | | | IV-2 | C14orf133 | 0.80 | 3406 | 3 | 4 | | | IV-2 | C7orf61 | 0.92 |
| 3311 | 3 | 4 | | | IV-2 | C14orf135 | 0.85 | 3407 | 3 | 4 | | | IV-2 | C8orf33 | 0.86 |
| 3312 | 3 | 4 | | | IV-2 | C14orf166 | 0.81 | 3408 | 3 | 4 | | | IV-2 | C8orf38 | 0.98 |
| 3313 | 3 | 4 | | | IV-2 | C14orf167 | 0.81 | 3409 | 3 | 4 | | | IV-2 | C8orf4 | 0.90 |
| 3314 | 3 | 4 | | | IV-2 | C14orf176 | 0.76 | 3410 | 3 | 4 | | | IV-2 | C8orf42 | 0.96 |
| 3315 | 3 | 4 | | | IV-2 | C14orf45 | 0.99 | 3411 | 3 | 4 | | | IV-2 | C8orf47 | 0.99 |
| 3316 | 3 | 4 | | | IV-2 | C14orf49 | 0.74 | 3412 | 3 | 4 | | | IV-2 | C8orf82 | 0.81 |
| 3317 | 3 | 4 | | | IV-2 | C15orf17 | 0.93 | 3413 | 3 | 4 | | | IV-2 | C8orf83 | 0.71 |
| 3318 | 3 | 4 | | | IV-2 | C15orf24 | 0.86 | 3414 | 3 | 4 | | | IV-2 | C9orf156 | 0.94 |
| 3319 | 3 | 4 | | | IV-2 | C15orf41 | 0.88 | 3415 | 3 | 4 | | | IV-2 | C9orf24 | 0.99 |
| 3320 | 3 | 4 | | | IV-2 | C15orf44 | 0.77 | 3416 | 3 | 4 | | | IV-2 | C9orf30 | 0.69 |
| 3321 | 3 | 4 | | | IV-2 | C15orf52 | 0.84 | 3417 | 3 | 4 | | | IV-2 | C9orf46 | 0.77 |
| 3322 | 3 | 4 | | | IV-2 | C15orf57 | 0.68 | 3418 | 3 | 4 | | | IV-2 | C9orf82 | 0.84 |
| 3323 | 3 | 4 | | | IV-2 | C15orf58 | 1.00 | 3419 | 3 | 4 | | | IV-2 | C9orf85 | 0.72 |
| 3324 | 3 | 4 | | | IV-2 | C15orf61 | 0.85 | 3420 | 3 | 4 | | | IV-2 | C9orf89 | 0.76 |
| 3325 | 3 | 4 | | | IV-2 | C16orf42 | 0.71 | 3421 | 3 | 4 | | | IV-2 | C9orf9 | 0.69 |
| 3326 | 3 | 4 | | | IV-2 | C16orf5 | 0.70 | 3422 | 3 | 4 | | | IV-2 | CA12 | 0.76 |
| 3327 | 3 | 4 | | | IV-2 | C16orf62 | 0.74 | 3423 | 3 | 4 | | | IV-2 | CACNA1G | 0.68 |
| 3328 | 3 | 4 | | | IV-2 | C16orf86 | 0.67 | 3424 | 3 | 4 | | | IV-2 | CACNA2D2 | 0.71 |
| 3329 | 3 | 4 | | | IV-2 | C16orf87 | 0.98 | 3425 | 3 | 4 | | | IV-2 | CACYBP | 0.87 |
| 3330 | 3 | 4 | | | IV-2 | C17orf101 | 0.68 | 3426 | 3 | 4 | | | IV-2 | CADM1 | 0.94 |
| 3331 | 3 | 4 | | | IV-2 | C17orf103 | 0.68 | 3427 | 3 | 4 | | | IV-2 | CALCOCO1 | 0.78 |
| 3332 | 3 | 4 | | | IV-2 | C17orf108 | 0.90 | 3428 | 3 | 4 | | | IV-2 | CALCOCO2 | 0.90 |
| 3333 | 3 | 4 | | | IV-2 | C17orf109 | 0.72 | 3429 | 3 | 4 | | | IV-2 | CALM1 | 0.71 |
| 3334 | 3 | 4 | | | IV-2 | C17orf49 | 0.71 | 3430 | 3 | 4 | | | IV-2 | CALM3 | 0.71 |
| 3335 | 3 | 4 | | | IV-2 | C17orf58 | 0.79 | 3431 | 3 | 4 | | | IV-2 | CALR | 0.97 |
| 3336 | 3 | 4 | | | IV-2 | C17orf62 | 0.74 | 3432 | 3 | 4 | | | IV-2 | CAMK2G | 0.97 |
| 3337 | 3 | 4 | | | IV-2 | C17orf63 | 0.69 | 3433 | 3 | 4 | | | IV-2 | CAMKMT | 0.85 |
| 3338 | 3 | 4 | | | IV-2 | C17orf67 | 0.95 | 3434 | 3 | 4 | | | IV-2 | CAMTA1 | 0.84 |
| 3339 | 3 | 4 | | | IV-2 | C17orf69 | 0.87 | 3435 | 3 | 4 | | | IV-2 | CANX | 0.99 |
| 3340 | 3 | 4 | | | IV-2 | C17orf75 | 0.84 | 3436 | 3 | 4 | | | IV-2 | CAP1 | 0.91 |
| 3341 | 3 | 4 | | | IV-2 | C17orf76-AS1 | 0.92 | 3437 | 3 | 4 | | | IV-2 | CAPRIN1 | 0.92 |
| 3342 | 3 | 4 | | | IV-2 | C17orf80 | 0.76 | 3438 | 3 | 4 | | | IV-2 | CAPZA2 | 0.95 |
| 3343 | 3 | 4 | | | IV-2 | C17orf81 | 0.77 | 3439 | 3 | 4 | | | IV-2 | CARD14 | 0.92 |
| 3344 | 3 | 4 | | | IV-2 | C17orf85 | 0.88 | 3440 | 3 | 4 | | | IV-2 | CARHSP1 | 0.69 |
| 3345 | 3 | 4 | | | IV-2 | C17orf90 | 0.69 | 3441 | 3 | 4 | | | IV-2 | CARKD | 0.88 |
| 3346 | 3 | 4 | | | IV-2 | C18orf1 | 0.88 | 3442 | 3 | 4 | | | IV-2 | CASC4 | 0.81 |
| 3347 | 3 | 4 | | | IV-2 | C19orf25 | 0.83 | 3443 | 3 | 4 | | | IV-2 | CASKIN1 | 0.99 |
| 3348 | 3 | 4 | | | IV-2 | C19orf52 | 0.91 | 3444 | 3 | 4 | | | IV-2 | CASP2 | 0.69 |
| 3349 | 3 | 4 | | | IV-2 | C19orf60 | 0.84 | 3445 | 3 | 4 | | | IV-2 | CASP3 | 0.76 |
| 3350 | 3 | 4 | | | IV-2 | C1GALT1C1 | 0.93 | 3446 | 3 | 4 | | | IV-2 | CASQ1 | 0.90 |
| 3351 | 3 | 4 | | | IV-2 | C1orf115 | 0.98 | 3447 | 3 | 4 | | | IV-2 | CAST | 0.97 |
| 3352 | 3 | 4 | | | IV-2 | C1orf123 | 0.90 | 3448 | 3 | 4 | | | IV-2 | CAV2 | 0.83 |
| 3353 | 3 | 4 | | | IV-2 | C1orf21 | 0.74 | 3449 | 3 | 4 | | | IV-2 | CBL | 0.67 |
| 3354 | 3 | 4 | | | IV-2 | C1orf35 | 0.90 | 3450 | 3 | 4 | | | IV-2 | CBLL1 | 0.72 |
| 3355 | 3 | 4 | | | IV-2 | C1orf53 | 0.90 | 3451 | 3 | 4 | | | IV-2 | CBLN3 | 0.71 |
| 3356 | 3 | 4 | | | IV-2 | C1orf56 | 0.82 | 3452 | 3 | 4 | | | IV-2 | CBR1 | 0.88 |
| 3357 | 3 | 4 | | | IV-2 | C1orf85 | 0.88 | 3453 | 3 | 4 | | | IV-2 | CBS | 0.68 |

Fig. 39 - 19

| | | | | | | | | | | | | | | | |
|---|---|---|---|---|---|---|---|---|---|---|---|---|---|---|---|
| 3454 | 3 | 4 | | | IV-2 | CBX1 | 0.76 | 3550 | 3 | 4 | | | IV-2 | CECR5 | 0.90 |
| 3455 | 3 | 4 | | | IV-2 | CBX5 | 0.83 | 3551 | 3 | 4 | | | IV-2 | CELF1 | 0.79 |
| 3456 | 3 | 4 | | | IV-2 | CBX8 | 0.77 | 3552 | 3 | 4 | | | IV-2 | CENPBD1 | 0.84 |
| 3457 | 3 | 4 | | | IV-2 | CBY1 | 0.84 | 3553 | 3 | 4 | | | IV-2 | CENPC1 | 0.78 |
| 3458 | 3 | 4 | | | IV-2 | CC2D2A | 0.87 | 3554 | 3 | 4 | | | IV-2 | CENPJ | 0.94 |
| 3459 | 3 | 4 | | | IV-2 | CCBE1 | 0.82 | 3555 | 3 | 4 | | | IV-2 | CENPN | 0.75 |
| 3460 | 3 | 4 | | | IV-2 | CC8L1 | 0.71 | 3556 | 3 | 4 | | | IV-2 | CEP120 | 0.97 |
| 3461 | 3 | 4 | | | IV-2 | CCDC103 | 0.92 | 3557 | 3 | 4 | | | IV-2 | CEP152 | 1.00 |
| 3462 | 3 | 4 | | | IV-2 | CCDC106 | 0.70 | 3558 | 3 | 4 | | | IV-2 | CEP170 | 0.91 |
| 3463 | 3 | 4 | | | IV-2 | CCDC107 | 0.73 | 3559 | 3 | 4 | | | IV-2 | CEP19 | 0.78 |
| 3464 | 3 | 4 | | | IV-2 | CCDC111 | 0.96 | 3560 | 3 | 4 | | | IV-2 | CEP192 | 1.00 |
| 3465 | 3 | 4 | | | IV-2 | CCDC113 | 0.70 | 3561 | 3 | 4 | | | IV-2 | CEP57 | 0.94 |
| 3466 | 3 | 4 | | | IV-2 | CCDC115 | 0.87 | 3562 | 3 | 4 | | | IV-2 | CEP63 | 0.99 |
| 3467 | 3 | 4 | | | IV-2 | CCDC12 | 0.71 | 3563 | 3 | 4 | | | IV-2 | CEP68 | 0.68 |
| 3468 | 3 | 4 | | | IV-2 | CCDC122 | 0.75 | 3564 | 3 | 4 | | | IV-2 | CEP78 | 0.87 |
| 3469 | 3 | 4 | | | IV-2 | CCDC126 | 0.74 | 3565 | 3 | 4 | | | IV-2 | CEP85L | 0.91 |
| 3470 | 3 | 4 | | | IV-2 | CCDC134 | 0.97 | 3566 | 3 | 4 | | | IV-2 | CERS2 | 0.82 |
| 3471 | 3 | 4 | | | IV-2 | CCDC152 | 0.87 | 3567 | 3 | 4 | | | IV-2 | CERS5 | 0.77 |
| 3472 | 3 | 4 | | | IV-2 | CCDC153 | 0.81 | 3568 | 3 | 4 | | | IV-2 | CERS6 | 1.00 |
| 3473 | 3 | 4 | | | IV-2 | CCDC157 | 0.95 | 3569 | 3 | 4 | | | IV-2 | CES2 | 0.86 |
| 3474 | 3 | 4 | | | IV-2 | CCDC23 | 0.70 | 3570 | 3 | 4 | | | IV-2 | CETN3 | 0.91 |
| 3475 | 3 | 4 | | | IV-2 | CCDC25 | 0.87 | 3571 | 3 | 4 | | | IV-2 | CFD | 0.81 |
| 3476 | 3 | 4 | | | IV-2 | CCDC41 | 0.89 | 3572 | 3 | 4 | | | IV-2 | CFH | 1.00 |
| 3477 | 3 | 4 | | | IV-2 | CCDC428 | 0.79 | 3573 | 3 | 4 | | | IV-2 | CGGBP1 | 0.93 |
| 3478 | 3 | 4 | | | IV-2 | CCDC51 | 0.88 | 3574 | 3 | 4 | | | IV-2 | CGNL1 | 0.89 |
| 3479 | 3 | 4 | | | IV-2 | CCDC59 | 0.93 | 3575 | 3 | 4 | | | IV-2 | CH25H | 0.76 |
| 3480 | 3 | 4 | | | IV-2 | CCDC69 | 0.72 | 3576 | 3 | 4 | | | IV-2 | CHAMP1 | 0.75 |
| 3481 | 3 | 4 | | | IV-2 | CCDC71L | 0.77 | 3577 | 3 | 4 | | | IV-2 | CHCHD3 | 0.94 |
| 3482 | 3 | 4 | | | IV-2 | CCDC8 | 0.96 | 3578 | 3 | 4 | | | IV-2 | CHCHD4 | 0.70 |
| 3483 | 3 | 4 | | | IV-2 | CCDC80 | 0.68 | 3579 | 3 | 4 | | | IV-2 | CHCHD5 | 0.75 |
| 3484 | 3 | 4 | | | IV-2 | CCDC85B | 0.77 | 3580 | 3 | 4 | | | IV-2 | CHCHD8 | 0.69 |
| 3485 | 3 | 4 | | | IV-2 | CCDC86 | 0.96 | 3581 | 3 | 4 | | | IV-2 | CHD2 | 0.79 |
| 3486 | 3 | 4 | | | IV-2 | CCDC93 | 0.89 | 3582 | 3 | 4 | | | IV-2 | CHEK1 | 0.78 |
| 3487 | 3 | 4 | | | IV-2 | CCL4 | 0.75 | 3583 | 3 | 4 | | | IV-2 | CHML | 0.95 |
| 3488 | 3 | 4 | | | IV-2 | CCL4L2 | 0.92 | 3584 | 3 | 4 | | | IV-2 | CHMP2A | 0.75 |
| 3489 | 3 | 4 | | | IV-2 | CCNB1IP1 | 0.68 | 3585 | 3 | 4 | | | IV-2 | CHMP4A | 0.95 |
| 3490 | 3 | 4 | | | IV-2 | CCND3 | 0.84 | 3586 | 3 | 4 | | | IV-2 | CHMP4B | 0.86 |
| 3491 | 3 | 4 | | | IV-2 | CCNG2 | 0.91 | 3587 | 3 | 4 | | | IV-2 | CHMP6 | 0.68 |
| 3492 | 3 | 4 | | | IV-2 | CCNH | 0.82 | 3588 | 3 | 4 | | | IV-2 | CHMP7 | 0.73 |
| 3493 | 3 | 4 | | | IV-2 | CCNJL | 0.86 | 3589 | 3 | 4 | | | IV-2 | CHN2 | 0.69 |
| 3494 | 3 | 4 | | | IV-2 | CCNK | 0.73 | 3590 | 3 | 4 | | | IV-2 | CHORDC1 | 0.96 |
| 3495 | 3 | 4 | | | IV-2 | CCNO | 0.96 | 3591 | 3 | 4 | | | IV-2 | CHPT1 | 0.89 |
| 3496 | 3 | 4 | | | IV-2 | CCNY | 0.74 | 3592 | 3 | 4 | | | IV-2 | CHRNB1 | 0.81 |
| 3497 | 3 | 4 | | | IV-2 | CCNYL1 | 0.90 | 3593 | 3 | 4 | | | IV-2 | CHTOP | 0.71 |
| 3498 | 3 | 4 | | | IV-2 | CCP110 | 0.89 | 3594 | 3 | 4 | | | IV-2 | CHURC1 | 0.71 |
| 3499 | 3 | 4 | | | IV-2 | CCR10 | 0.70 | 3595 | 3 | 4 | | | IV-2 | CIAO1 | 0.81 |
| 3500 | 3 | 4 | | | IV-2 | CCT5 | 0.87 | 3596 | 3 | 4 | | | IV-2 | CIAPIN1 | 0.88 |
| 3501 | 3 | 4 | | | IV-2 | CCT6A | 0.80 | 3597 | 3 | 4 | | | IV-2 | CIB1 | 0.88 |
| 3502 | 3 | 4 | | | IV-2 | CCZ1B | 0.95 | 3598 | 3 | 4 | | | IV-2 | CIDECP | 0.70 |
| 3503 | 3 | 4 | | | IV-2 | CD14 | 0.91 | 3599 | 3 | 4 | | | IV-2 | CILP2 | 0.98 |
| 3504 | 3 | 4 | | | IV-2 | CD151 | 0.76 | 3600 | 3 | 4 | | | IV-2 | CISD2 | 0.89 |
| 3505 | 3 | 4 | | | IV-2 | CD160 | 0.90 | 3601 | 3 | 4 | | | IV-2 | CKAP2 | 0.69 |
| 3506 | 3 | 4 | | | IV-2 | CD163 | 0.77 | 3602 | 3 | 4 | | | IV-2 | CKAP5 | 0.75 |
| 3507 | 3 | 4 | | | IV-2 | CD177 | 0.93 | 3603 | 3 | 4 | | | IV-2 | CKLF-CMTM1 | 0.68 |
| 3508 | 3 | 4 | | | IV-2 | CD2BP2 | 0.70 | 3604 | 3 | 4 | | | IV-2 | CKMT1B | 0.70 |
| 3509 | 3 | 4 | | | IV-2 | CD302 | 0.81 | 3605 | 3 | 4 | | | IV-2 | CKS1B | 0.96 |
| 3510 | 3 | 4 | | | IV-2 | CD320 | 0.92 | 3606 | 3 | 4 | | | IV-2 | CLCN5 | 0.81 |
| 3511 | 3 | 4 | | | IV-2 | CD3EAP | 0.90 | 3607 | 3 | 4 | | | IV-2 | CLDN19 | 0.97 |
| 3512 | 3 | 4 | | | IV-2 | CD3G | 0.92 | 3608 | 3 | 4 | | | IV-2 | CLEC12B | 0.90 |
| 3513 | 3 | 4 | | | IV-2 | CD44 | 0.73 | 3609 | 3 | 4 | | | IV-2 | CLEC18A | 0.97 |
| 3514 | 3 | 4 | | | IV-2 | CD47 | 0.71 | 3610 | 3 | 4 | | | IV-2 | CLEC2B | 0.88 |
| 3515 | 3 | 4 | | | IV-2 | CD81 | 0.71 | 3611 | 3 | 4 | | | IV-2 | CLEC4A | 0.82 |
| 3516 | 3 | 4 | | | IV-2 | CD9 | 0.68 | 3612 | 3 | 4 | | | IV-2 | CLEC9A | 0.99 |
| 3517 | 3 | 4 | | | IV-2 | CD99L2 | 0.69 | 3613 | 3 | 4 | | | IV-2 | CLIC4 | 0.82 |
| 3518 | 3 | 4 | | | IV-2 | CDC123 | 0.70 | 3614 | 3 | 4 | | | IV-2 | CLIC5 | 0.95 |
| 3519 | 3 | 4 | | | IV-2 | CDC23 | 0.96 | 3615 | 3 | 4 | | | IV-2 | CLINT1 | 1.00 |
| 3520 | 3 | 4 | | | IV-2 | CDC27 | 0.77 | 3616 | 3 | 4 | | | IV-2 | CLIP1 | 0.75 |
| 3521 | 3 | 4 | | | IV-2 | CDC37L1 | 0.93 | 3617 | 3 | 4 | | | IV-2 | CLN3 | 0.76 |
| 3522 | 3 | 4 | | | IV-2 | CDC42BPA | 0.70 | 3618 | 3 | 4 | | | IV-2 | CLP1 | 0.82 |
| 3523 | 3 | 4 | | | IV-2 | CDC42SE1 | 0.97 | 3619 | 3 | 4 | | | IV-2 | CLPTM1L | 0.80 |
| 3524 | 3 | 4 | | | IV-2 | CDC42SE2 | 0.71 | 3620 | 3 | 4 | | | IV-2 | CLSTN2 | 0.94 |
| 3525 | 3 | 4 | | | IV-2 | CDC45 | 0.93 | 3621 | 3 | 4 | | | IV-2 | CLTA | 0.76 |
| 3526 | 3 | 4 | | | IV-2 | CDC5L | 0.74 | 3622 | 3 | 4 | | | IV-2 | CLTCL1 | 0.92 |
| 3527 | 3 | 4 | | | IV-2 | CDC6 | 0.97 | 3623 | 3 | 4 | | | IV-2 | CLUAP1 | 0.93 |
| 3528 | 3 | 4 | | | IV-2 | CDC73 | 0.93 | 3624 | 3 | 4 | | | IV-2 | CMPK2 | 0.90 |
| 3529 | 3 | 4 | | | IV-2 | CDCA5 | 0.69 | 3625 | 3 | 4 | | | IV-2 | CMTM5 | 0.77 |
| 3530 | 3 | 4 | | | IV-2 | CDH11 | 0.68 | 3626 | 3 | 4 | | | IV-2 | CNBP | 0.87 |
| 3531 | 3 | 4 | | | IV-2 | CDH3 | 0.69 | 3627 | 3 | 4 | | | IV-2 | CNEP1R1 | 1.00 |
| 3532 | 3 | 4 | | | IV-2 | CDHR4 | 1.00 | 3628 | 3 | 4 | | | IV-2 | CNOT1 | 0.81 |
| 3533 | 3 | 4 | | | IV-2 | CDK11A | 0.86 | 3629 | 3 | 4 | | | IV-2 | CNOT4 | 0.72 |
| 3534 | 3 | 4 | | | IV-2 | CDK13 | 0.67 | 3630 | 3 | 4 | | | IV-2 | CNOT6 | 0.94 |
| 3535 | 3 | 4 | | | IV-2 | CDK14 | 0.81 | 3631 | 3 | 4 | | | IV-2 | CNOT6L | 0.95 |
| 3536 | 3 | 4 | | | IV-2 | CDK2 | 0.69 | 3632 | 3 | 4 | | | IV-2 | CNOT7 | 0.97 |
| 3537 | 3 | 4 | | | IV-2 | CDK4 | 0.77 | 3633 | 3 | 4 | | | IV-2 | CNPPD1 | 0.69 |
| 3538 | 3 | 4 | | | IV-2 | CDK5RAP1 | 0.72 | 3634 | 3 | 4 | | | IV-2 | CNTF | 0.76 |
| 3539 | 3 | 4 | | | IV-2 | CDK5RAP2 | 0.87 | 3635 | 3 | 4 | | | IV-2 | COASY | 0.74 |
| 3540 | 3 | 4 | | | IV-2 | CDK6 | 0.86 | 3636 | 3 | 4 | | | IV-2 | COBRA1 | 0.71 |
| 3541 | 3 | 4 | | | IV-2 | CDKAL1 | 0.79 | 3637 | 3 | 4 | | | IV-2 | COG2 | 0.81 |
| 3542 | 3 | 4 | | | IV-2 | CDKL3 | 0.97 | 3638 | 3 | 4 | | | IV-2 | COG3 | 1.00 |
| 3543 | 3 | 4 | | | IV-2 | CDKN1B | 0.96 | 3639 | 3 | 4 | | | IV-2 | COG5 | 0.92 |
| 3544 | 3 | 4 | | | IV-2 | CDKN2AIP | 0.83 | 3640 | 3 | 4 | | | IV-2 | COIL | 0.94 |
| 3545 | 3 | 4 | | | IV-2 | CDKN2AIPNL | 0.88 | 3641 | 3 | 4 | | | IV-2 | COL21A1 | 0.96 |
| 3546 | 3 | 4 | | | IV-2 | CDKN2C | 0.82 | 3642 | 3 | 4 | | | IV-2 | COL28A1 | 0.92 |
| 3547 | 3 | 4 | | | IV-2 | CDKN2D | 0.87 | 3643 | 3 | 4 | | | IV-2 | COL9A3 | 0.98 |
| 3548 | 3 | 4 | | | IV-2 | CEACAM19 | 0.71 | 3644 | 3 | 4 | | | IV-2 | COMMD2 | 0.84 |
| 3549 | 3 | 4 | | | IV-2 | CEBPG | 0.82 | 3645 | 3 | 4 | | | IV-2 | COMMD3 | 0.88 |

Fig. 39 - 20

| | | | | | | | | | | | | | | | |
|---|---|---|---|---|---|---|---|---|---|---|---|---|---|---|---|
| 3646 | 3 | 4 | | | IV-2 | COMMD5 | 0.86 | 3742 | 3 | 4 | | | IV-2 | DAPP1 | 0.84 |
| 3647 | 3 | 4 | | | IV-2 | COMMD8 | 0.87 | 3743 | 3 | 4 | | | IV-2 | DARS | 0.75 |
| 3648 | 3 | 4 | | | IV-2 | COMMD9 | 0.87 | 3744 | 3 | 4 | | | IV-2 | DAZAP1 | 0.80 |
| 3649 | 3 | 4 | | | IV-2 | COPA | 0.84 | 3745 | 3 | 4 | | | IV-2 | DBF4 | 0.74 |
| 3650 | 3 | 4 | | | IV-2 | COPB2 | 0.86 | 3746 | 3 | 4 | | | IV-2 | DBNDD1 | 0.83 |
| 3651 | 3 | 4 | | | IV-2 | COPG1 | 0.86 | 3747 | 3 | 4 | | | IV-2 | DBP | 0.81 |
| 3652 | 3 | 4 | | | IV-2 | COPS4 | 0.97 | 3748 | 3 | 4 | | | IV-2 | DBR1 | 0.97 |
| 3653 | 3 | 4 | | | IV-2 | COPS5 | 0.87 | 3749 | 3 | 4 | | | IV-2 | DCAF16 | 0.81 |
| 3654 | 3 | 4 | | | IV-2 | COPS6 | 0.79 | 3750 | 3 | 4 | | | IV-2 | DCAF6 | 0.88 |
| 3655 | 3 | 4 | | | IV-2 | COPS7A | 0.93 | 3751 | 3 | 4 | | | IV-2 | DCAF8 | 0.74 |
| 3656 | 3 | 4 | | | IV-2 | COPS8 | 0.91 | 3752 | 3 | 4 | | | IV-2 | DCAKD | 0.79 |
| 3657 | 3 | 4 | | | IV-2 | COPZ2 | 0.74 | 3753 | 3 | 4 | | | IV-2 | DCTD | 0.82 |
| 3658 | 3 | 4 | | | IV-2 | COQ4 | 0.88 | 3754 | 3 | 4 | | | IV-2 | DCUN1D2 | 0.83 |
| 3659 | 3 | 4 | | | IV-2 | COQ7 | 0.75 | 3755 | 3 | 4 | | | IV-2 | DCUN1D3 | 0.69 |
| 3660 | 3 | 4 | | | IV-2 | COQ9 | 0.93 | 3756 | 3 | 4 | | | IV-2 | DDOST | 0.77 |
| 3661 | 3 | 4 | | | IV-2 | COX11 | 0.86 | 3757 | 3 | 4 | | | IV-2 | DDR1 | 0.70 |
| 3662 | 3 | 4 | | | IV-2 | COX17 | 0.81 | 3758 | 3 | 4 | | | IV-2 | DDR2 | 0.99 |
| 3663 | 3 | 4 | | | IV-2 | COX19 | 1.00 | 3759 | 3 | 4 | | | IV-2 | DDX1 | 0.90 |
| 3664 | 3 | 4 | | | IV-2 | COX4I1 | 0.96 | 3760 | 3 | 4 | | | IV-2 | DDX19A | 0.68 |
| 3665 | 3 | 4 | | | IV-2 | COX4NB | 0.73 | 3761 | 3 | 4 | | | IV-2 | DDX20 | 0.85 |
| 3666 | 3 | 4 | | | IV-2 | CPEB1 | 0.89 | 3762 | 3 | 4 | | | IV-2 | DDX27 | 0.67 |
| 3667 | 3 | 4 | | | IV-2 | CPEB2 | 0.89 | 3763 | 3 | 4 | | | IV-2 | DDX39A | 0.69 |
| 3668 | 3 | 4 | | | IV-2 | CPOX | 0.98 | 3764 | 3 | 4 | | | IV-2 | DDX42 | 0.78 |
| 3669 | 3 | 4 | | | IV-2 | CPSF2 | 0.78 | 3765 | 3 | 4 | | | IV-2 | DDX47 | 0.99 |
| 3670 | 3 | 4 | | | IV-2 | CPSF3 | 0.84 | 3766 | 3 | 4 | | | IV-2 | DDX5 | 0.88 |
| 3671 | 3 | 4 | | | IV-2 | CPSF3L | 0.77 | 3767 | 3 | 4 | | | IV-2 | DDX56 | 0.68 |
| 3672 | 3 | 4 | | | IV-2 | CPSF6 | 0.87 | 3768 | 3 | 4 | | | IV-2 | DDX58 | 0.84 |
| 3673 | 3 | 4 | | | IV-2 | CPT1A | 0.95 | 3769 | 3 | 4 | | | IV-2 | DDX59 | 0.80 |
| 3674 | 3 | 4 | | | IV-2 | CPT1C | 0.67 | 3770 | 3 | 4 | | | IV-2 | DDX6 | 0.82 |
| 3675 | 3 | 4 | | | IV-2 | CRCP | 0.69 | 3771 | 3 | 4 | | | IV-2 | DEDD | 0.70 |
| 3676 | 3 | 4 | | | IV-2 | CREB1 | 0.75 | 3772 | 3 | 4 | | | IV-2 | DEF8 | 0.70 |
| 3677 | 3 | 4 | | | IV-2 | CRELD2 | 0.68 | 3773 | 3 | 4 | | | IV-2 | DEFA6 | 0.89 |
| 3678 | 3 | 4 | | | IV-2 | CRHR2 | 0.96 | 3774 | 3 | 4 | | | IV-2 | DEPDC1 | 0.92 |
| 3679 | 3 | 4 | | | IV-2 | CRIM1 | 0.89 | 3775 | 3 | 4 | | | IV-2 | DEPDC5 | 0.78 |
| 3680 | 3 | 4 | | | IV-2 | CRIP3 | 0.93 | 3776 | 3 | 4 | | | IV-2 | DERA | 0.85 |
| 3681 | 3 | 4 | | | IV-2 | CRLF3 | 0.84 | 3777 | 3 | 4 | | | IV-2 | DEXI | 0.68 |
| 3682 | 3 | 4 | | | IV-2 | CRNKL1 | 0.98 | 3778 | 3 | 4 | | | IV-2 | DGCR6L | 0.80 |
| 3683 | 3 | 4 | | | IV-2 | CRSP8P | 0.76 | 3779 | 3 | 4 | | | IV-2 | DGKD | 0.68 |
| 3684 | 3 | 4 | | | IV-2 | CRYL1 | 0.71 | 3780 | 3 | 4 | | | IV-2 | DGKZ | 0.74 |
| 3685 | 3 | 4 | | | IV-2 | CRYZ | 0.79 | 3781 | 3 | 4 | | | IV-2 | DGUOK | 0.75 |
| 3686 | 3 | 4 | | | IV-2 | CSAG3 | 0.98 | 3782 | 3 | 4 | | | IV-2 | DHDDS | 0.97 |
| 3687 | 3 | 4 | | | IV-2 | CSGALNACT1 | 0.90 | 3783 | 3 | 4 | | | IV-2 | DHRS13 | 0.75 |
| 3688 | 3 | 4 | | | IV-2 | CSGALNACT2 | 0.81 | 3784 | 3 | 4 | | | IV-2 | DHRS4L2 | 0.97 |
| 3689 | 3 | 4 | | | IV-2 | CSNK1G1 | 0.86 | 3785 | 3 | 4 | | | IV-2 | DHRSX | 0.87 |
| 3690 | 3 | 4 | | | IV-2 | CSNK1G3 | 0.79 | 3786 | 3 | 4 | | | IV-2 | DHX15 | 0.85 |
| 3691 | 3 | 4 | | | IV-2 | CSNK2B | 0.87 | 3787 | 3 | 4 | | | IV-2 | DHX32 | 0.92 |
| 3692 | 3 | 4 | | | IV-2 | CSRP1 | 0.78 | 3788 | 3 | 4 | | | IV-2 | DHX33 | 0.94 |
| 3693 | 3 | 4 | | | IV-2 | CSTF1 | 0.76 | 3789 | 3 | 4 | | | IV-2 | DHX40 | 0.96 |
| 3694 | 3 | 4 | | | IV-2 | CSTF2T | 0.86 | 3790 | 3 | 4 | | | IV-2 | DHX57 | 0.97 |
| 3695 | 3 | 4 | | | IV-2 | CTAGE5 | 0.78 | 3791 | 3 | 4 | | | IV-2 | DIABLO | 0.82 |
| 3696 | 3 | 4 | | | IV-2 | CTAGE7P | 0.73 | 3792 | 3 | 4 | | | IV-2 | DICER1 | 0.92 |
| 3697 | 3 | 4 | | | IV-2 | CTBP1 | 0.72 | 3793 | 3 | 4 | | | IV-2 | DIEXF | 0.74 |
| 3698 | 3 | 4 | | | IV-2 | CTBP2 | 0.89 | 3794 | 3 | 4 | | | IV-2 | DIP2C | 0.91 |
| 3699 | 3 | 4 | | | IV-2 | CTCF | 0.69 | 3795 | 3 | 4 | | | IV-2 | DIS3L | 0.70 |
| 3700 | 3 | 4 | | | IV-2 | CTDNEP1 | 0.80 | 3796 | 3 | 4 | | | IV-2 | DKC1 | 0.93 |
| 3701 | 3 | 4 | | | IV-2 | CTDSPL2 | 0.87 | 3797 | 3 | 4 | | | IV-2 | DKFZPS86I1420 | 0.98 |
| 3702 | 3 | 4 | | | IV-2 | CTLA4 | 0.99 | 3798 | 3 | 4 | | | IV-2 | DLG3 | 0.97 |
| 3703 | 3 | 4 | | | IV-2 | CTNS | 0.67 | 3799 | 3 | 4 | | | IV-2 | DLG4 | 0.78 |
| 3704 | 3 | 4 | | | IV-2 | CTPS2 | 0.77 | 3800 | 3 | 4 | | | IV-2 | DLK1 | 0.91 |
| 3705 | 3 | 4 | | | IV-2 | CTSC | 0.73 | 3801 | 3 | 4 | | | IV-2 | DLX6 | 0.86 |
| 3706 | 3 | 4 | | | IV-2 | CTSH | 0.80 | 3802 | 3 | 4 | | | IV-2 | DMD | 0.80 |
| 3707 | 3 | 4 | | | IV-2 | CTSL1 | 0.78 | 3803 | 3 | 4 | | | IV-2 | DMRT3 | 0.88 |
| 3708 | 3 | 4 | | | IV-2 | CTSO | 0.77 | 3804 | 3 | 4 | | | IV-2 | DNAH17 | 0.93 |
| 3709 | 3 | 4 | | | IV-2 | CTTN | 0.68 | 3805 | 3 | 4 | | | IV-2 | DNAJA1 | 0.96 |
| 3710 | 3 | 4 | | | IV-2 | CTTNBP2 | 0.95 | 3806 | 3 | 4 | | | IV-2 | DNAJA3 | 0.99 |
| 3711 | 3 | 4 | | | IV-2 | CTU1 | 0.80 | 3807 | 3 | 4 | | | IV-2 | DNAJA4 | 0.99 |
| 3712 | 3 | 4 | | | IV-2 | CUL1 | 0.84 | 3808 | 3 | 4 | | | IV-2 | DNAJB11 | 0.80 |
| 3713 | 3 | 4 | | | IV-2 | CUL2 | 0.95 | 3809 | 3 | 4 | | | IV-2 | DNAJB12 | 0.80 |
| 3714 | 3 | 4 | | | IV-2 | CUL4A | 0.95 | 3810 | 3 | 4 | | | IV-2 | DNAJC17 | 0.72 |
| 3715 | 3 | 4 | | | IV-2 | CWC25 | 0.91 | 3811 | 3 | 4 | | | IV-2 | DNAJC18 | 0.84 |
| 3716 | 3 | 4 | | | IV-2 | CWC27 | 0.99 | 3812 | 3 | 4 | | | IV-2 | DNAJC28 | 0.95 |
| 3717 | 3 | 4 | | | IV-2 | CWF19L1 | 0.81 | 3813 | 3 | 4 | | | IV-2 | DNAJC4 | 0.71 |
| 3718 | 3 | 4 | | | IV-2 | CWH43 | 0.96 | 3814 | 3 | 4 | | | IV-2 | DNAJC7 | 0.84 |
| 3719 | 3 | 4 | | | IV-2 | CX3CL1 | 0.69 | 3815 | 3 | 4 | | | IV-2 | DNAJC8 | 0.69 |
| 3720 | 3 | 4 | | | IV-2 | CXorf26 | 0.85 | 3816 | 3 | 4 | | | IV-2 | DNAJC9 | 0.73 |
| 3721 | 3 | 4 | | | IV-2 | CXorf38 | 0.69 | 3817 | 3 | 4 | | | IV-2 | DNAL1 | 0.89 |
| 3722 | 3 | 4 | | | IV-2 | CXorf56 | 0.92 | 3818 | 3 | 4 | | | IV-2 | DNAL4 | 0.78 |
| 3723 | 3 | 4 | | | IV-2 | CXorf65 | 0.85 | 3819 | 3 | 4 | | | IV-2 | DNASE1L1 | 0.80 |
| 3724 | 3 | 4 | | | IV-2 | CYB561 | 0.87 | 3820 | 3 | 4 | | | IV-2 | DNPEP | 0.73 |
| 3725 | 3 | 4 | | | IV-2 | CYB5B | 0.74 | 3821 | 3 | 4 | | | IV-2 | DOCK11 | 0.95 |
| 3726 | 3 | 4 | | | IV-2 | CYB5D1 | 0.75 | 3822 | 3 | 4 | | | IV-2 | DOCK7 | 0.97 |
| 3727 | 3 | 4 | | | IV-2 | CYB5D2 | 0.68 | 3823 | 3 | 4 | | | IV-2 | DOCK9 | 0.82 |
| 3728 | 3 | 4 | | | IV-2 | CYB5R1 | 0.70 | 3824 | 3 | 4 | | | IV-2 | DOHH | 0.68 |
| 3729 | 3 | 4 | | | IV-2 | CYBRD1 | 0.71 | 3825 | 3 | 4 | | | IV-2 | DOK7 | 0.97 |
| 3730 | 3 | 4 | | | IV-2 | CYFIP1 | 0.89 | 3826 | 3 | 4 | | | IV-2 | DOLPP1 | 0.91 |
| 3731 | 3 | 4 | | | IV-2 | CYHR1 | 0.87 | 3827 | 3 | 4 | | | IV-2 | DONSON | 0.95 |
| 3732 | 3 | 4 | | | IV-2 | CYLD | 0.86 | 3828 | 3 | 4 | | | IV-2 | DPAGT1 | 0.88 |
| 3733 | 3 | 4 | | | IV-2 | CYP3A4 | 0.90 | 3829 | 3 | 4 | | | IV-2 | DPF2 | 0.68 |
| 3734 | 3 | 4 | | | IV-2 | CYP3A5 | 0.98 | 3830 | 3 | 4 | | | IV-2 | DPH2 | 0.82 |
| 3735 | 3 | 4 | | | IV-2 | CYTH1 | 0.72 | 3831 | 3 | 4 | | | IV-2 | DPH3 | 0.97 |
| 3736 | 3 | 4 | | | IV-2 | DACH1 | 0.87 | 3832 | 3 | 4 | | | IV-2 | DPM1 | 0.73 |
| 3737 | 3 | 4 | | | IV-2 | DAD1 | 0.91 | 3833 | 3 | 4 | | | IV-2 | DPM2 | 0.91 |
| 3738 | 3 | 4 | | | IV-2 | DALRD3 | 0.90 | 3834 | 3 | 4 | | | IV-2 | DPP3 | 0.88 |
| 3739 | 3 | 4 | | | IV-2 | DANCR | 0.89 | 3835 | 3 | 4 | | | IV-2 | DPT | 0.82 |
| 3740 | 3 | 4 | | | IV-2 | DAP3 | 0.93 | 3836 | 3 | 4 | | | IV-2 | DPY19L3 | 0.94 |
| 3741 | 3 | 4 | | | IV-2 | DAPK1 | 0.71 | 3837 | 3 | 4 | | | IV-2 | DPY30 | 0.98 |

Fig. 39 - 21

| | | | | | | | | | | | | | | |
|---|---|---|---|---|---|---|---|---|---|---|---|---|---|---|
| 3838 | 3 | 4 | | | IV-2 | DRG2 | 0.69 | 3934 | 3 | 4 | | | IV-2 | EPS8 | 0.85 |
| 3839 | 3 | 4 | | | IV-2 | DSCC1 | 0.76 | 3935 | 3 | 4 | | | IV-2 | EPS8L1 | 0.98 |
| 3840 | 3 | 4 | | | IV-2 | DSE | 0.80 | 3936 | 3 | 4 | | | IV-2 | ERAL1 | 0.68 |
| 3841 | 3 | 4 | | | IV-2 | DSN1 | 1.00 | 3937 | 3 | 4 | | | IV-2 | ERAP2 | 0.68 |
| 3842 | 3 | 4 | | | IV-2 | DST | 0.96 | 3938 | 3 | 4 | | | IV-2 | ERCC2 | 0.72 |
| 3843 | 3 | 4 | | | IV-2 | DSTN | 0.94 | 3939 | 3 | 4 | | | IV-2 | ERGIC3 | 0.72 |
| 3844 | 3 | 4 | | | IV-2 | DTD1 | 0.80 | 3940 | 3 | 4 | | | IV-2 | ERI1 | 0.76 |
| 3845 | 3 | 4 | | | IV-2 | DTNB | 0.92 | 3941 | 3 | 4 | | | IV-2 | ERLIN2 | 0.90 |
| 3846 | 3 | 4 | | | IV-2 | DTNBP1 | 0.79 | 3942 | 3 | 4 | | | IV-2 | ERP44 | 0.82 |
| 3847 | 3 | 4 | | | IV-2 | DTX1 | 0.88 | 3943 | 3 | 4 | | | IV-2 | ERVK13-1 | 0.71 |
| 3848 | 3 | 4 | | | IV-2 | DTX3L | 0.75 | 3944 | 3 | 4 | | | IV-2 | ESRP2 | 0.85 |
| 3849 | 3 | 4 | | | IV-2 | DTYMK | 0.72 | 3945 | 3 | 4 | | | IV-2 | ESRRA | 0.98 |
| 3850 | 3 | 4 | | | IV-2 | DUSP12 | 0.86 | 3946 | 3 | 4 | | | IV-2 | EVI5 | 0.81 |
| 3851 | 3 | 4 | | | IV-2 | DUSP19 | 0.92 | 3947 | 3 | 4 | | | IV-2 | EVL | 0.95 |
| 3852 | 3 | 4 | | | IV-2 | DUSP23 | 0.77 | 3948 | 3 | 4 | | | IV-2 | EXD2 | 0.72 |
| 3853 | 3 | 4 | | | IV-2 | DUSP3 | 0.70 | 3949 | 3 | 4 | | | IV-2 | EXOC1 | 0.95 |
| 3854 | 3 | 4 | | | IV-2 | DUSP6 | 0.83 | 3950 | 3 | 4 | | | IV-2 | EXOC2 | 0.81 |
| 3855 | 3 | 4 | | | IV-2 | DUSP8 | 0.72 | 3951 | 3 | 4 | | | IV-2 | EXOC3L2 | 0.94 |
| 3856 | 3 | 4 | | | IV-2 | DUT | 0.95 | 3952 | 3 | 4 | | | IV-2 | EXOSC1 | 0.97 |
| 3857 | 3 | 4 | | | IV-2 | DVL2 | 0.69 | 3953 | 3 | 4 | | | IV-2 | EXOSC7 | 0.73 |
| 3858 | 3 | 4 | | | IV-2 | DYNC1LI2 | 0.96 | 3954 | 3 | 4 | | | IV-2 | EXT2 | 0.73 |
| 3859 | 3 | 4 | | | IV-2 | DYRK1A | 0.79 | 3955 | 3 | 4 | | | IV-2 | EXTL2 | 0.86 |
| 3860 | 3 | 4 | | | IV-2 | E2F1 | 0.82 | 3956 | 3 | 4 | | | IV-2 | EYA3 | 0.93 |
| 3861 | 3 | 4 | | | IV-2 | E2F5 | 0.87 | 3957 | 3 | 4 | | | IV-2 | EZH2 | 0.70 |
| 3862 | 3 | 4 | | | IV-2 | E2F6 | 0.95 | 3958 | 3 | 4 | | | IV-2 | FADD | 0.77 |
| 3863 | 3 | 4 | | | IV-2 | EAPP | 0.93 | 3959 | 3 | 4 | | | IV-2 | FAF1 | 0.93 |
| 3864 | 3 | 4 | | | IV-2 | EBAG9 | 0.92 | 3960 | 3 | 4 | | | IV-2 | FAF2 | 0.74 |
| 3865 | 3 | 4 | | | IV-2 | EBF2 | 0.82 | 3961 | 3 | 4 | | | IV-2 | FAHD2A | 0.82 |
| 3866 | 3 | 4 | | | IV-2 | EBI3 | 0.91 | 3962 | 3 | 4 | | | IV-2 | FAIM | 0.72 |
| 3867 | 3 | 4 | | | IV-2 | EBNA1BP2 | 1.00 | 3963 | 3 | 4 | | | IV-2 | FAIM2 | 0.94 |
| 3868 | 3 | 4 | | | IV-2 | ECD | 0.84 | 3964 | 3 | 4 | | | IV-2 | FAM102B | 0.72 |
| 3869 | 3 | 4 | | | IV-2 | EDAR | 0.90 | 3965 | 3 | 4 | | | IV-2 | FAM104A | 0.81 |
| 3870 | 3 | 4 | | | IV-2 | EDNRB | 0.89 | 3966 | 3 | 4 | | | IV-2 | FAM104B | 0.88 |
| 3871 | 3 | 4 | | | IV-2 | EEA1 | 0.82 | 3967 | 3 | 4 | | | IV-2 | FAM105B | 0.69 |
| 3872 | 3 | 4 | | | IV-2 | EED | 0.96 | 3968 | 3 | 4 | | | IV-2 | FAM114A1 | 0.82 |
| 3873 | 3 | 4 | | | IV-2 | EEF1B2 | 0.74 | 3969 | 3 | 4 | | | IV-2 | FAM114A2 | 0.83 |
| 3874 | 3 | 4 | | | IV-2 | EEF1E1 | 0.67 | 3970 | 3 | 4 | | | IV-2 | FAM116A | 0.80 |
| 3875 | 3 | 4 | | | IV-2 | EFCAB7 | 0.93 | 3971 | 3 | 4 | | | IV-2 | FAM116B | 0.93 |
| 3876 | 3 | 4 | | | IV-2 | EFEMP1 | 0.72 | 3972 | 3 | 4 | | | IV-2 | FAM117B | 0.91 |
| 3877 | 3 | 4 | | | IV-2 | EFHA1 | 0.85 | 3973 | 3 | 4 | | | IV-2 | FAM118B | 0.75 |
| 3878 | 3 | 4 | | | IV-2 | EFHA2 | 1.00 | 3974 | 3 | 4 | | | IV-2 | FAM120A | 0.88 |
| 3879 | 3 | 4 | | | IV-2 | EFNA4 | 0.98 | 3975 | 3 | 4 | | | IV-2 | FAM126A | 0.99 |
| 3880 | 3 | 4 | | | IV-2 | EFNA5 | 0.75 | 3976 | 3 | 4 | | | IV-2 | FAM127B | 0.83 |
| 3881 | 3 | 4 | | | IV-2 | EFR3A | 0.96 | 3977 | 3 | 4 | | | IV-2 | FAM127C | 0.67 |
| 3882 | 3 | 4 | | | IV-2 | EFS | 0.69 | 3978 | 3 | 4 | | | IV-2 | FAM129A | 0.99 |
| 3883 | 3 | 4 | | | IV-2 | EGFL6 | 0.79 | 3979 | 3 | 4 | | | IV-2 | FAM136A | 1.00 |
| 3884 | 3 | 4 | | | IV-2 | EGFLAM | 0.87 | 3980 | 3 | 4 | | | IV-2 | FAM160B1 | 0.95 |
| 3885 | 3 | 4 | | | IV-2 | EID1 | 0.73 | 3981 | 3 | 4 | | | IV-2 | FAM166B | 0.71 |
| 3886 | 3 | 4 | | | IV-2 | EID2 | 0.88 | 3982 | 3 | 4 | | | IV-2 | FAM171A1 | 0.73 |
| 3887 | 3 | 4 | | | IV-2 | EIF1B | 0.78 | 3983 | 3 | 4 | | | IV-2 | FAM171A2 | 0.95 |
| 3888 | 3 | 4 | | | IV-2 | EIF2AK3 | 0.87 | 3984 | 3 | 4 | | | IV-2 | FAM175A | 0.84 |
| 3889 | 3 | 4 | | | IV-2 | EIF2AK4 | 0.84 | 3985 | 3 | 4 | | | IV-2 | FAM177A1 | 0.93 |
| 3890 | 3 | 4 | | | IV-2 | EIF2B1 | 0.79 | 3986 | 3 | 4 | | | IV-2 | FAM178B | 0.88 |
| 3891 | 3 | 4 | | | IV-2 | EIF2B4 | 0.83 | 3987 | 3 | 4 | | | IV-2 | FAM181B | 0.82 |
| 3892 | 3 | 4 | | | IV-2 | EIF2B5 | 0.71 | 3988 | 3 | 4 | | | IV-2 | FAM182A | 0.93 |
| 3893 | 3 | 4 | | | IV-2 | EIF2C4 | 0.84 | 3989 | 3 | 4 | | | IV-2 | FAM182B | 0.88 |
| 3894 | 3 | 4 | | | IV-2 | EIF2S1 | 0.92 | 3990 | 3 | 4 | | | IV-2 | FAM188B1 | 0.98 |
| 3895 | 3 | 4 | | | IV-2 | EIF2S3 | 0.77 | 3991 | 3 | 4 | | | IV-2 | FAM190B | 0.90 |
| 3896 | 3 | 4 | | | IV-2 | EIF3E | 0.88 | 3992 | 3 | 4 | | | IV-2 | FAM192A | 0.79 |
| 3897 | 3 | 4 | | | IV-2 | EIF3H | 0.93 | 3993 | 3 | 4 | | | IV-2 | FAM198B | 0.77 |
| 3898 | 3 | 4 | | | IV-2 | EIF3I | 0.87 | 3994 | 3 | 4 | | | IV-2 | FAM206A | 0.98 |
| 3899 | 3 | 4 | | | IV-2 | EIF4A1 | 0.82 | 3995 | 3 | 4 | | | IV-2 | FAM208A | 0.84 |
| 3900 | 3 | 4 | | | IV-2 | EIF4G3 | 0.93 | 3996 | 3 | 4 | | | IV-2 | FAM208B | 0.96 |
| 3901 | 3 | 4 | | | IV-2 | EIF5A2 | 0.82 | 3997 | 3 | 4 | | | IV-2 | FAM209A | 0.89 |
| 3902 | 3 | 4 | | | IV-2 | ELAC1 | 0.91 | 3998 | 3 | 4 | | | IV-2 | FAM20B | 0.99 |
| 3903 | 3 | 4 | | | IV-2 | ELAVL1 | 0.90 | 3999 | 3 | 4 | | | IV-2 | FAM210A | 0.69 |
| 3904 | 3 | 4 | | | IV-2 | ELF2 | 0.80 | 4000 | 3 | 4 | | | IV-2 | FAM211B | 0.69 |
| 3905 | 3 | 4 | | | IV-2 | ELL | 0.75 | 4001 | 3 | 4 | | | IV-2 | FAM214B | 0.67 |
| 3906 | 3 | 4 | | | IV-2 | ELP4 | 0.76 | 4002 | 3 | 4 | | | IV-2 | FAM216A | 0.86 |
| 3907 | 3 | 4 | | | IV-2 | ELTD1 | 0.74 | 4003 | 3 | 4 | | | IV-2 | FAM21B | 0.83 |
| 3908 | 3 | 4 | | | IV-2 | EMD | 0.82 | 4004 | 3 | 4 | | | IV-2 | FAM21C | 0.72 |
| 3909 | 3 | 4 | | | IV-2 | EMG1 | 0.92 | 4005 | 3 | 4 | | | IV-2 | FAM32A | 0.96 |
| 3910 | 3 | 4 | | | IV-2 | EMID1 | 0.71 | 4006 | 3 | 4 | | | IV-2 | FAM35B | 0.95 |
| 3911 | 3 | 4 | | | IV-2 | EML1 | 0.84 | 4007 | 3 | 4 | | | IV-2 | FAM3A | 0.67 |
| 3912 | 3 | 4 | | | IV-2 | EML2 | 0.86 | 4008 | 3 | 4 | | | IV-2 | FAM49B | 0.80 |
| 3913 | 3 | 4 | | | IV-2 | EML4 | 0.96 | 4009 | 3 | 4 | | | IV-2 | FAM53A | 0.96 |
| 3914 | 3 | 4 | | | IV-2 | EMR2 | 0.91 | 4010 | 3 | 4 | | | IV-2 | FAM55C | 0.75 |
| 3915 | 3 | 4 | | | IV-2 | ENAH | 0.86 | 4011 | 3 | 4 | | | IV-2 | FAM58A | 0.81 |
| 3916 | 3 | 4 | | | IV-2 | ENDOU | 0.75 | 4012 | 3 | 4 | | | IV-2 | FAM58BP | 0.76 |
| 3917 | 3 | 4 | | | IV-2 | ENDOV | 0.79 | 4013 | 3 | 4 | | | IV-2 | FAM59B | 0.91 |
| 3918 | 3 | 4 | | | IV-2 | ENO1 | 0.84 | 4014 | 3 | 4 | | | IV-2 | FAM64A | 0.76 |
| 3919 | 3 | 4 | | | IV-2 | ENO4 | 0.92 | 4015 | 3 | 4 | | | IV-2 | FAM65C | 0.82 |
| 3920 | 3 | 4 | | | IV-2 | ENOPH1 | 0.98 | 4016 | 3 | 4 | | | IV-2 | FAM66C | 0.94 |
| 3921 | 3 | 4 | | | IV-2 | ENOX1 | 0.98 | 4017 | 3 | 4 | | | IV-2 | FAM72A | 0.80 |
| 3922 | 3 | 4 | | | IV-2 | ENOX2 | 0.96 | 4018 | 3 | 4 | | | IV-2 | FAM72B | 0.67 |
| 3923 | 3 | 4 | | | IV-2 | ENSA | 0.81 | 4019 | 3 | 4 | | | IV-2 | FAM82A1 | 0.91 |
| 3924 | 3 | 4 | | | IV-2 | EPB41L1 | 0.72 | 4020 | 3 | 4 | | | IV-2 | FAM82A2 | 0.95 |
| 3925 | 3 | 4 | | | IV-2 | EPB41L4A | 0.68 | 4021 | 3 | 4 | | | IV-2 | FAM86A | 0.82 |
| 3926 | 3 | 4 | | | IV-2 | EPB41L4A-AS1 | 0.99 | 4022 | 3 | 4 | | | IV-2 | FAM86C2P | 0.82 |
| 3927 | 3 | 4 | | | IV-2 | EPC2 | 0.82 | 4023 | 3 | 4 | | | IV-2 | FAM8A1 | 0.94 |
| 3928 | 3 | 4 | | | IV-2 | EPHB3 | 0.77 | 4024 | 3 | 4 | | | IV-2 | FAM91A1 | 0.79 |
| 3929 | 3 | 4 | | | IV-2 | EPHX1 | 0.79 | 4025 | 3 | 4 | | | IV-2 | FAM96B | 0.84 |
| 3930 | 3 | 4 | | | IV-2 | EPHX4 | 0.96 | 4026 | 3 | 4 | | | IV-2 | FAM98C | 0.83 |
| 3931 | 3 | 4 | | | IV-2 | EPM2A | 0.75 | 4027 | 3 | 4 | | | IV-2 | FANCA | 0.67 |
| 3932 | 3 | 4 | | | IV-2 | EPN2 | 0.72 | 4028 | 3 | 4 | | | IV-2 | FANCC | 0.73 |
| 3933 | 3 | 4 | | | IV-2 | EPO | 0.89 | 4029 | 3 | 4 | | | IV-2 | FANCD2 | 0.90 |

Fig. 39 - 22

| | | | | | | | | | | | | | | |
|---|---|---|---|---|---|---|---|---|---|---|---|---|---|---|
| 4030 | 3 | 4 | | | IV-2 | FARP2 | 0.75 | 4126 | 3 | 4 | | | IV-2 | GAS6 | 0.68 |
| 4031 | 3 | 4 | | | IV-2 | FARSB | 0.68 | 4127 | 3 | 4 | | | IV-2 | GATA5 | 0.97 |
| 4032 | 3 | 4 | | | IV-2 | FAS | 0.75 | 4128 | 3 | 4 | | | IV-2 | GATC | 0.94 |
| 4033 | 3 | 4 | | | IV-2 | FASTK | 0.74 | 4129 | 3 | 4 | | | IV-2 | GATSL1 | 0.97 |
| 4034 | 3 | 4 | | | IV-2 | FAT4 | 0.87 | 4130 | 3 | 4 | | | IV-2 | GBP1 | 0.76 |
| 4035 | 3 | 4 | | | IV-2 | FBL | 0.81 | 4131 | 3 | 4 | | | IV-2 | GCHFR | 0.96 |
| 4036 | 3 | 4 | | | IV-2 | FBLN1 | 0.69 | 4132 | 3 | 4 | | | IV-2 | GCNT1 | 0.80 |
| 4037 | 3 | 4 | | | IV-2 | FBXL12 | 0.68 | 4133 | 3 | 4 | | | IV-2 | GDI2 | 0.77 |
| 4038 | 3 | 4 | | | IV-2 | FBXL15 | 0.91 | 4134 | 3 | 4 | | | IV-2 | GDNF | 0.72 |
| 4039 | 3 | 4 | | | IV-2 | FBXL16 | 0.70 | 4135 | 3 | 4 | | | IV-2 | GDPD5 | 0.68 |
| 4040 | 3 | 4 | | | IV-2 | FBXL18 | 0.78 | 4136 | 3 | 4 | | | IV-2 | GEMIN6 | 0.68 |
| 4041 | 3 | 4 | | | IV-2 | FBXL2 | 0.79 | 4137 | 3 | 4 | | | IV-2 | GEMIN8 | 0.83 |
| 4042 | 3 | 4 | | | IV-2 | FBXL22 | 0.88 | 4138 | 3 | 4 | | | IV-2 | GFOD2 | 0.81 |
| 4043 | 3 | 4 | | | IV-2 | FBXL3 | 0.72 | 4139 | 3 | 4 | | | IV-2 | GFPT2 | 0.68 |
| 4044 | 3 | 4 | | | IV-2 | FBXL5 | 0.83 | 4140 | 3 | 4 | | | IV-2 | GGA1 | 0.72 |
| 4045 | 3 | 4 | | | IV-2 | FBXO10 | 0.71 | 4141 | 3 | 4 | | | IV-2 | GGCX | 0.70 |
| 4046 | 3 | 4 | | | IV-2 | FBXO11 | 0.87 | 4142 | 3 | 4 | | | IV-2 | GHRLOS | 0.98 |
| 4047 | 3 | 4 | | | IV-2 | FBXO17 | 0.72 | 4143 | 3 | 4 | | | IV-2 | GINS1 | 0.81 |
| 4048 | 3 | 4 | | | IV-2 | FBXO2 | 0.68 | 4144 | 3 | 4 | | | IV-2 | GINS3 | 0.69 |
| 4049 | 3 | 4 | | | IV-2 | FBXO25 | 0.87 | 4145 | 3 | 4 | | | IV-2 | GLA | 0.97 |
| 4050 | 3 | 4 | | | IV-2 | FBXO36 | 0.71 | 4146 | 3 | 4 | | | IV-2 | GLB1L2 | 0.89 |
| 4051 | 3 | 4 | | | IV-2 | FBXO38 | 0.96 | 4147 | 3 | 4 | | | IV-2 | GLE1 | 0.88 |
| 4052 | 3 | 4 | | | IV-2 | FBXO4 | 0.76 | 4148 | 3 | 4 | | | IV-2 | GLOD4 | 0.80 |
| 4053 | 3 | 4 | | | IV-2 | FBXO44 | 0.71 | 4149 | 3 | 4 | | | IV-2 | GLT8D1 | 0.76 |
| 4054 | 3 | 4 | | | IV-2 | FBXO5 | 0.87 | 4150 | 3 | 4 | | | IV-2 | GLT8D2 | 0.83 |
| 4055 | 3 | 4 | | | IV-2 | FBXO7 | 0.94 | 4151 | 3 | 4 | | | IV-2 | GLTPD1 | 0.95 |
| 4056 | 3 | 4 | | | IV-2 | FBXW11 | 0.82 | 4152 | 3 | 4 | | | IV-2 | GLUL | 0.70 |
| 4057 | 3 | 4 | | | IV-2 | FBXW4 | 0.74 | 4153 | 3 | 4 | | | IV-2 | GLYR1 | 0.69 |
| 4058 | 3 | 4 | | | IV-2 | FBXW5 | 0.68 | 4154 | 3 | 4 | | | IV-2 | GMCL1P1 | 0.89 |
| 4059 | 3 | 4 | | | IV-2 | FCF1 | 0.94 | 4155 | 3 | 4 | | | IV-2 | GMPPA | 0.90 |
| 4060 | 3 | 4 | | | IV-2 | FCGRT | 0.75 | 4156 | 3 | 4 | | | IV-2 | GMPR2 | 0.85 |
| 4061 | 3 | 4 | | | IV-2 | FCRLA | 0.89 | 4157 | 3 | 4 | | | IV-2 | GNA13 | 0.82 |
| 4062 | 3 | 4 | | | IV-2 | FECH | 0.84 | 4158 | 3 | 4 | | | IV-2 | GNB1 | 0.70 |
| 4063 | 3 | 4 | | | IV-2 | FEM1C | 0.88 | 4159 | 3 | 4 | | | IV-2 | GNB1L | 0.83 |
| 4064 | 3 | 4 | | | IV-2 | FGD5-AS1 | 0.88 | 4160 | 3 | 4 | | | IV-2 | GNG10 | 0.73 |
| 4065 | 3 | 4 | | | IV-2 | FGF7 | 0.90 | 4161 | 3 | 4 | | | IV-2 | GNG2 | 0.96 |
| 4066 | 3 | 4 | | | IV-2 | FGFBP3 | 0.93 | 4162 | 3 | 4 | | | IV-2 | GNG5 | 0.76 |
| 4067 | 3 | 4 | | | IV-2 | FGFR2 | 0.98 | 4163 | 3 | 4 | | | IV-2 | GNL2 | 0.79 |
| 4068 | 3 | 4 | | | IV-2 | FGFRL1 | 0.83 | 4164 | 3 | 4 | | | IV-2 | GNL3 | 0.89 |
| 4069 | 3 | 4 | | | IV-2 | FGGY | 0.83 | 4165 | 3 | 4 | | | IV-2 | GNPDA1 | 0.91 |
| 4070 | 3 | 4 | | | IV-2 | FHL2 | 0.99 | 4166 | 3 | 4 | | | IV-2 | GNPDA2 | 0.91 |
| 4071 | 3 | 4 | | | IV-2 | FHOD1 | 0.68 | 4167 | 3 | 4 | | | IV-2 | GNPNAT1 | 0.96 |
| 4072 | 3 | 4 | | | IV-2 | FIG4 | 0.78 | 4168 | 3 | 4 | | | IV-2 | GNRHR2 | 0.96 |
| 4073 | 3 | 4 | | | IV-2 | FIP1L1 | 0.75 | 4169 | 3 | 4 | | | IV-2 | GNS | 0.77 |
| 4074 | 3 | 4 | | | IV-2 | FIS1 | 0.82 | 4170 | 3 | 4 | | | IV-2 | GOLGA1 | 0.81 |
| 4075 | 3 | 4 | | | IV-2 | FKBP1A | 0.80 | 4171 | 3 | 4 | | | IV-2 | GOLGA2 | 0.70 |
| 4076 | 3 | 4 | | | IV-2 | FLAD1 | 0.73 | 4172 | 3 | 4 | | | IV-2 | GOLGA3 | 0.75 |
| 4077 | 3 | 4 | | | IV-2 | FLJ10661 | 0.68 | 4173 | 3 | 4 | | | IV-2 | GOLGA7B | 0.72 |
| 4078 | 3 | 4 | | | IV-2 | FLJ27354 | 0.98 | 4174 | 3 | 4 | | | IV-2 | GOLM1 | 0.94 |
| 4079 | 3 | 4 | | | IV-2 | FLJ39639 | 0.81 | 4175 | 3 | 4 | | | IV-2 | GOLPH3 | 0.73 |
| 4080 | 3 | 4 | | | IV-2 | FLJ42627 | 0.96 | 4176 | 3 | 4 | | | IV-2 | GOLPH3L | 0.96 |
| 4081 | 3 | 4 | | | IV-2 | FLJ43681 | 0.99 | 4177 | 3 | 4 | | | IV-2 | GORASP2 | 0.69 |
| 4082 | 3 | 4 | | | IV-2 | FLJ44635 | 0.84 | 4178 | 3 | 4 | | | IV-2 | GOSR1 | 0.79 |
| 4083 | 3 | 4 | | | IV-2 | FLJ45983 | 0.83 | 4179 | 3 | 4 | | | IV-2 | GOSR2 | 0.72 |
| 4084 | 3 | 4 | | | IV-2 | FLJ46906 | 0.98 | 4180 | 3 | 4 | | | IV-2 | GOT2 | 0.95 |
| 4085 | 3 | 4 | | | IV-2 | FN3KRP | 0.79 | 4181 | 3 | 4 | | | IV-2 | GPAA1 | 0.77 |
| 4086 | 3 | 4 | | | IV-2 | FNDC3A | 0.96 | 4182 | 3 | 4 | | | IV-2 | GPATCH4 | 0.84 |
| 4087 | 3 | 4 | | | IV-2 | FNIP1 | 0.77 | 4183 | 3 | 4 | | | IV-2 | GPBP1 | 0.91 |
| 4088 | 3 | 4 | | | IV-2 | FNTB | 0.93 | 4184 | 3 | 4 | | | IV-2 | GPBP1L1 | 0.77 |
| 4089 | 3 | 4 | | | IV-2 | FOPNL | 0.84 | 4185 | 3 | 4 | | | IV-2 | GPC4 | 0.93 |
| 4090 | 3 | 4 | | | IV-2 | FOXD3 | 0.89 | 4186 | 3 | 4 | | | IV-2 | GPHN | 0.83 |
| 4091 | 3 | 4 | | | IV-2 | FOXJ3 | 0.79 | 4187 | 3 | 4 | | | IV-2 | GPN1 | 0.83 |
| 4092 | 3 | 4 | | | IV-2 | FOXN2 | 0.77 | 4188 | 3 | 4 | | | IV-2 | GPR111 | 0.99 |
| 4093 | 3 | 4 | | | IV-2 | FOXN3 | 0.73 | 4189 | 3 | 4 | | | IV-2 | GPR115 | 0.72 |
| 4094 | 3 | 4 | | | IV-2 | FOXP1 | 0.93 | 4190 | 3 | 4 | | | IV-2 | GPR125 | 0.78 |
| 4095 | 3 | 4 | | | IV-2 | FOXP3 | 0.91 | 4191 | 3 | 4 | | | IV-2 | GPR126 | 0.89 |
| 4096 | 3 | 4 | | | IV-2 | FOXRED1 | 0.89 | 4192 | 3 | 4 | | | IV-2 | GPR143 | 0.70 |
| 4097 | 3 | 4 | | | IV-2 | FRG1 | 0.72 | 4193 | 3 | 4 | | | IV-2 | GPR55 | 0.97 |
| 4098 | 3 | 4 | | | IV-2 | FRY | 0.75 | 4194 | 3 | 4 | | | IV-2 | GPR89A | 0.94 |
| 4099 | 3 | 4 | | | IV-2 | FTL | 0.71 | 4195 | 3 | 4 | | | IV-2 | GPRASP2 | 0.86 |
| 4100 | 3 | 4 | | | IV-2 | FTSJ1 | 0.77 | 4196 | 3 | 4 | | | IV-2 | GPS1 | 0.74 |
| 4101 | 3 | 4 | | | IV-2 | FTSJ2 | 0.89 | 4197 | 3 | 4 | | | IV-2 | GPX1 | 0.68 |
| 4102 | 3 | 4 | | | IV-2 | FTSJ3 | 0.70 | 4198 | 3 | 4 | | | IV-2 | GPX4 | 0.73 |
| 4103 | 3 | 4 | | | IV-2 | FUBP1 | 0.67 | 4199 | 3 | 4 | | | IV-2 | GREB1 | 0.89 |
| 4104 | 3 | 4 | | | IV-2 | FUBP3 | 0.90 | 4200 | 3 | 4 | | | IV-2 | GRHPR | 0.81 |
| 4105 | 3 | 4 | | | IV-2 | FUNDC2 | 0.75 | 4201 | 3 | 4 | | | IV-2 | GRIN3B | 0.98 |
| 4106 | 3 | 4 | | | IV-2 | FUNDC2P2 | 0.68 | 4202 | 3 | 4 | | | IV-2 | GRINA | 0.81 |
| 4107 | 3 | 4 | | | IV-2 | FUT10 | 0.70 | 4203 | 3 | 4 | | | IV-2 | GRIP1 | 0.80 |
| 4108 | 3 | 4 | | | IV-2 | FUT4 | 0.93 | 4204 | 3 | 4 | | | IV-2 | GRIPAP1 | 0.82 |
| 4109 | 3 | 4 | | | IV-2 | FUT7 | 0.90 | 4205 | 3 | 4 | | | IV-2 | GRTP1 | 1.00 |
| 4110 | 3 | 4 | | | IV-2 | FXR2 | 0.72 | 4206 | 3 | 4 | | | IV-2 | GSG2 | 0.93 |
| 4111 | 3 | 4 | | | IV-2 | FXYD7 | 0.69 | 4207 | 3 | 4 | | | IV-2 | GSPT1 | 0.97 |
| 4112 | 3 | 4 | | | IV-2 | FYCO1 | 0.74 | 4208 | 3 | 4 | | | IV-2 | GSR | 0.84 |
| 4113 | 3 | 4 | | | IV-2 | FZD6 | 0.81 | 4209 | 3 | 4 | | | IV-2 | GSS | 0.68 |
| 4114 | 3 | 4 | | | IV-2 | G2E3 | 0.98 | 4210 | 3 | 4 | | | IV-2 | GSTK1 | 0.98 |
| 4115 | 3 | 4 | | | IV-2 | G3BP1 | 0.93 | 4211 | 3 | 4 | | | IV-2 | GSTO1 | 0.92 |
| 4116 | 3 | 4 | | | IV-2 | GABPB1 | 0.70 | 4212 | 3 | 4 | | | IV-2 | GSTT1 | 0.83 |
| 4117 | 3 | 4 | | | IV-2 | GADD45G | 0.77 | 4213 | 3 | 4 | | | IV-2 | GTDC1 | 0.76 |
| 4118 | 3 | 4 | | | IV-2 | GALM | 0.96 | 4214 | 3 | 4 | | | IV-2 | GTF2B | 0.78 |
| 4119 | 3 | 4 | | | IV-2 | GALNT11 | 0.79 | 4215 | 3 | 4 | | | IV-2 | GTF2E1 | 0.76 |
| 4120 | 3 | 4 | | | IV-2 | GAMT | 0.73 | 4216 | 3 | 4 | | | IV-2 | GTF2H2B | 0.81 |
| 4121 | 3 | 4 | | | IV-2 | GAP43 | 0.91 | 4217 | 3 | 4 | | | IV-2 | GTF3A | 0.87 |
| 4122 | 3 | 4 | | | IV-2 | GAPDHS | 0.95 | 4218 | 3 | 4 | | | IV-2 | GTF3C2 | 0.76 |
| 4123 | 3 | 4 | | | IV-2 | GAPT | 0.97 | 4219 | 3 | 4 | | | IV-2 | GTPBP4 | 1.00 |
| 4124 | 3 | 4 | | | IV-2 | GARS | 0.82 | 4220 | 3 | 4 | | | IV-2 | GTPBP5 | 0.81 |
| 4125 | 3 | 4 | | | IV-2 | GART | 0.91 | 4221 | 3 | 4 | | | IV-2 | GTPBP8 | 0.98 |

Fig. 39 - 23

| | | | | | | | | | | | | | | | |
|---|---|---|---|---|---|---|---|---|---|---|---|---|---|---|---|
| 4222 | 3 | 4 | | | IV-2 | GUK1 | 0.72 | 4318 | 3 | 4 | | | IV-2 | IBA57 | 0.72 |
| 4223 | 3 | 4 | | | IV-2 | GUSB | 0.67 | 4319 | 3 | 4 | | | IV-2 | ICA1L | 0.97 |
| 4224 | 3 | 4 | | | IV-2 | GXYLT2 | 0.82 | 4320 | 3 | 4 | | | IV-2 | ICAM2 | 0.68 |
| 4225 | 3 | 4 | | | IV-2 | GZMB | 0.91 | 4321 | 3 | 4 | | | IV-2 | IDH3B | 0.68 |
| 4226 | 3 | 4 | | | IV-2 | GZMH | 0.89 | 4322 | 3 | 4 | | | IV-2 | IDI2 | 0.68 |
| 4227 | 3 | 4 | | | IV-2 | H1F0 | 0.74 | 4323 | 3 | 4 | | | IV-2 | IDI2-AS1 | 0.82 |
| 4228 | 3 | 4 | | | IV-2 | H2AFB3 | 0.87 | 4324 | 3 | 4 | | | IV-2 | IFI16 | 0.73 |
| 4229 | 3 | 4 | | | IV-2 | H2AFV | 0.90 | 4325 | 3 | 4 | | | IV-2 | IFI27L1 | 0.71 |
| 4230 | 3 | 4 | | | IV-2 | H2AFY | 0.89 | 4326 | 3 | 4 | | | IV-2 | IFIT3 | 0.77 |
| 4231 | 3 | 4 | | | IV-2 | H3F3B | 0.82 | 4327 | 3 | 4 | | | IV-2 | IFNGR1 | 0.87 |
| 4232 | 3 | 4 | | | IV-2 | HAAO | 0.88 | 4328 | 3 | 4 | | | IV-2 | IFNGR2 | 0.93 |
| 4233 | 3 | 4 | | | IV-2 | HAGH | 0.97 | 4329 | 3 | 4 | | | IV-2 | IFRD2 | 0.99 |
| 4234 | 3 | 4 | | | IV-2 | HARS | 0.68 | 4330 | 3 | 4 | | | IV-2 | IFT52 | 0.90 |
| 4235 | 3 | 4 | | | IV-2 | HAUS1 | 0.76 | 4331 | 3 | 4 | | | IV-2 | IFT57 | 0.69 |
| 4236 | 3 | 4 | | | IV-2 | HAUS4 | 0.75 | 4332 | 3 | 4 | | | IV-2 | IGF1R | 0.74 |
| 4237 | 3 | 4 | | | IV-2 | HAX1 | 0.75 | 4333 | 3 | 4 | | | IV-2 | IGFALS | 0.90 |
| 4238 | 3 | 4 | | | IV-2 | HBP1 | 0.97 | 4334 | 3 | 4 | | | IV-2 | IGFBP2 | 0.76 |
| 4239 | 3 | 4 | | | IV-2 | HBS1L | 0.91 | 4335 | 3 | 4 | | | IV-2 | IGSF21 | 0.96 |
| 4240 | 3 | 4 | | | IV-2 | HCCS | 0.97 | 4336 | 3 | 4 | | | IV-2 | IKZF4 | 0.84 |
| 4241 | 3 | 4 | | | IV-2 | HCG23 | 0.94 | 4337 | 3 | 4 | | | IV-2 | IL11 | 0.85 |
| 4242 | 3 | 4 | | | IV-2 | HCG27 | 0.90 | 4338 | 3 | 4 | | | IV-2 | IL17RC | 0.89 |
| 4243 | 3 | 4 | | | IV-2 | HCN2 | 0.97 | 4339 | 3 | 4 | | | IV-2 | IL1R1 | 0.72 |
| 4244 | 3 | 4 | | | IV-2 | HDAC1 | 0.91 | 4340 | 3 | 4 | | | IV-2 | IL27RA | 0.70 |
| 4245 | 3 | 4 | | | IV-2 | HDAC2 | 0.84 | 4341 | 3 | 4 | | | IV-2 | IL6R | 0.75 |
| 4246 | 3 | 4 | | | IV-2 | HDHD1 | 0.90 | 4342 | 3 | 4 | | | IV-2 | IL6ST | 0.85 |
| 4247 | 3 | 4 | | | IV-2 | HEATR1 | 0.80 | 4343 | 3 | 4 | | | IV-2 | IL7R | 0.91 |
| 4248 | 3 | 4 | | | IV-2 | HEATR2 | 0.69 | 4344 | 3 | 4 | | | IV-2 | IMMT | 0.89 |
| 4249 | 3 | 4 | | | IV-2 | HEATR8 | 0.88 | 4345 | 3 | 4 | | | IV-2 | IMP3 | 0.81 |
| 4250 | 3 | 4 | | | IV-2 | HEBP1 | 0.88 | 4346 | 3 | 4 | | | IV-2 | IMPAD1 | 0.81 |
| 4251 | 3 | 4 | | | IV-2 | HECA | 0.82 | 4347 | 3 | 4 | | | IV-2 | ING2 | 0.87 |
| 4252 | 3 | 4 | | | IV-2 | HEG1 | 0.72 | 4348 | 3 | 4 | | | IV-2 | INHA | 0.72 |
| 4253 | 3 | 4 | | | IV-2 | HELQ | 0.84 | 4349 | 3 | 4 | | | IV-2 | INPP4A | 0.84 |
| 4254 | 3 | 4 | | | IV-2 | HERC1 | 0.80 | 4350 | 3 | 4 | | | IV-2 | INPP5A | 0.79 |
| 4255 | 3 | 4 | | | IV-2 | HES2 | 0.69 | 4351 | 3 | 4 | | | IV-2 | INPP5B | 0.71 |
| 4256 | 3 | 4 | | | IV-2 | HEXA | 0.70 | 4352 | 3 | 4 | | | IV-2 | INPP5J | 0.70 |
| 4257 | 3 | 4 | | | IV-2 | HEXB | 0.78 | 4353 | 3 | 4 | | | IV-2 | INPP5K | 0.71 |
| 4258 | 3 | 4 | | | IV-2 | HEXDC | 0.81 | 4354 | 3 | 4 | | | IV-2 | INTS10 | 0.89 |
| 4259 | 3 | 4 | | | IV-2 | HEY1 | 0.85 | 4355 | 3 | 4 | | | IV-2 | INTS12 | 0.74 |
| 4260 | 3 | 4 | | | IV-2 | HHAT | 0.91 | 4356 | 3 | 4 | | | IV-2 | INTS2 | 0.79 |
| 4261 | 3 | 4 | | | IV-2 | HHIPL1 | 0.91 | 4357 | 3 | 4 | | | IV-2 | INTS4 | 0.76 |
| 4262 | 3 | 4 | | | IV-2 | HHLA3 | 0.84 | 4358 | 3 | 4 | | | IV-2 | INTS7 | 0.83 |
| 4263 | 3 | 4 | | | IV-2 | HIAT1 | 0.87 | 4359 | 3 | 4 | | | IV-2 | INTS8 | 0.83 |
| 4264 | 3 | 4 | | | IV-2 | HIGD2A | 0.78 | 4360 | 3 | 4 | | | IV-2 | INTS9 | 0.70 |
| 4265 | 3 | 4 | | | IV-2 | HINFP | 0.74 | 4361 | 3 | 4 | | | IV-2 | INVS | 0.98 |
| 4266 | 3 | 4 | | | IV-2 | HIPK3 | 0.69 | 4362 | 3 | 4 | | | IV-2 | IPO5 | 0.94 |
| 4267 | 3 | 4 | | | IV-2 | HIST1H2AD | 0.89 | 4363 | 3 | 4 | | | IV-2 | IPO7 | 0.92 |
| 4268 | 3 | 4 | | | IV-2 | HIST1H2BI | 0.93 | 4364 | 3 | 4 | | | IV-2 | IPPK | 0.80 |
| 4269 | 3 | 4 | | | IV-2 | HIST1H3G | 0.98 | 4365 | 3 | 4 | | | IV-2 | IQCD | 1.00 |
| 4270 | 3 | 4 | | | IV-2 | HLA-A | 0.78 | 4366 | 3 | 4 | | | IV-2 | IQCG | 0.90 |
| 4271 | 3 | 4 | | | IV-2 | HLA-F | 0.76 | 4367 | 3 | 4 | | | IV-2 | IQGAP1 | 0.72 |
| 4272 | 3 | 4 | | | IV-2 | HLF | 0.95 | 4368 | 3 | 4 | | | IV-2 | IQSEC3 | 0.94 |
| 4273 | 3 | 4 | | | IV-2 | HMCN1 | 0.72 | 4369 | 3 | 4 | | | IV-2 | IRAK2 | 0.82 |
| 4274 | 3 | 4 | | | IV-2 | HMG20B | 0.71 | 4370 | 3 | 4 | | | IV-2 | IRAK4 | 0.94 |
| 4275 | 3 | 4 | | | IV-2 | HMGB1 | 0.83 | 4371 | 3 | 4 | | | IV-2 | IRF1 | 0.94 |
| 4276 | 3 | 4 | | | IV-2 | HMGB2 | 0.69 | 4372 | 3 | 4 | | | IV-2 | IRF9 | 0.77 |
| 4277 | 3 | 4 | | | IV-2 | HMGN2 | 1.00 | 4373 | 3 | 4 | | | IV-2 | IRGQ | 0.79 |
| 4278 | 3 | 4 | | | IV-2 | HMGN4 | 0.83 | 4374 | 3 | 4 | | | IV-2 | IRX4 | 0.76 |
| 4279 | 3 | 4 | | | IV-2 | HN1L | 0.85 | 4375 | 3 | 4 | | | IV-2 | ISCA1 | 0.96 |
| 4280 | 3 | 4 | | | IV-2 | HNRNPA1L2 | 0.69 | 4376 | 3 | 4 | | | IV-2 | IST1 | 0.88 |
| 4281 | 3 | 4 | | | IV-2 | HNRNPA2B1 | 0.97 | 4377 | 3 | 4 | | | IV-2 | ITCH | 0.92 |
| 4282 | 3 | 4 | | | IV-2 | HNRNPAB | 0.95 | 4378 | 3 | 4 | | | IV-2 | ITFG2 | 0.77 |
| 4283 | 3 | 4 | | | IV-2 | HNRNPC | 0.78 | 4379 | 3 | 4 | | | IV-2 | ITGA10 | 0.94 |
| 4284 | 3 | 4 | | | IV-2 | HNRNPD | 0.68 | 4380 | 3 | 4 | | | IV-2 | ITGA2 | 0.85 |
| 4285 | 3 | 4 | | | IV-2 | HNRNPK | 0.84 | 4381 | 3 | 4 | | | IV-2 | ITGA6 | 0.80 |
| 4286 | 3 | 4 | | | IV-2 | HNRNPKP3 | 0.76 | 4382 | 3 | 4 | | | IV-2 | ITM2A | 0.73 |
| 4287 | 3 | 4 | | | IV-2 | HNRNPM | 0.81 | 4383 | 3 | 4 | | | IV-2 | ITPA | 0.85 |
| 4288 | 3 | 4 | | | IV-2 | HNRNPR | 0.67 | 4384 | 3 | 4 | | | IV-2 | ITPR2 | 0.81 |
| 4289 | 3 | 4 | | | IV-2 | HNRNPU | 0.67 | 4385 | 3 | 4 | | | IV-2 | ITPRIPL2 | 0.86 |
| 4290 | 3 | 4 | | | IV-2 | HNRPLL | 0.74 | 4386 | 3 | 4 | | | IV-2 | ITSN1 | 0.89 |
| 4291 | 3 | 4 | | | IV-2 | HOXA-AS3 | 0.89 | 4387 | 3 | 4 | | | IV-2 | JAG1 | 0.73 |
| 4292 | 3 | 4 | | | IV-2 | HOXB2 | 0.96 | 4388 | 3 | 4 | | | IV-2 | JAK1 | 0.77 |
| 4293 | 3 | 4 | | | IV-2 | HOXB4 | 0.78 | 4389 | 3 | 4 | | | IV-2 | JAK2 | 0.96 |
| 4294 | 3 | 4 | | | IV-2 | HOXD-AS2 | 0.69 | 4390 | 3 | 4 | | | IV-2 | JAK3 | 0.70 |
| 4295 | 3 | 4 | | | IV-2 | HP1BP3 | 0.84 | 4391 | 3 | 4 | | | IV-2 | JHDM1D | 0.91 |
| 4296 | 3 | 4 | | | IV-2 | HPCAL1 | 0.83 | 4392 | 3 | 4 | | | IV-2 | JMJD8 | 0.68 |
| 4297 | 3 | 4 | | | IV-2 | HPRT1 | 0.84 | 4393 | 3 | 4 | | | IV-2 | JOSD2 | 0.96 |
| 4298 | 3 | 4 | | | IV-2 | HS2ST1 | 0.94 | 4394 | 3 | 4 | | | IV-2 | JPH4 | 0.88 |
| 4299 | 3 | 4 | | | IV-2 | HS3ST3B1 | 0.93 | 4395 | 3 | 4 | | | IV-2 | JPX | 0.74 |
| 4300 | 3 | 4 | | | IV-2 | HSBP1 | 0.76 | 4396 | 3 | 4 | | | IV-2 | JTB | 0.84 |
| 4301 | 3 | 4 | | | IV-2 | HSD11B2 | 0.69 | 4397 | 3 | 4 | | | IV-2 | KALRN | 0.98 |
| 4302 | 3 | 4 | | | IV-2 | HSD17B11 | 0.99 | 4398 | 3 | 4 | | | IV-2 | KANSL1-AS1 | 0.77 |
| 4303 | 3 | 4 | | | IV-2 | HSH2D | 0.87 | 4399 | 3 | 4 | | | IV-2 | KANSL2 | 0.98 |
| 4304 | 3 | 4 | | | IV-2 | HSP90AB1 | 0.77 | 4400 | 3 | 4 | | | IV-2 | KAT6B | 0.77 |
| 4305 | 3 | 4 | | | IV-2 | HSPA12A | 1.00 | 4401 | 3 | 4 | | | IV-2 | KATNA1 | 0.92 |
| 4306 | 3 | 4 | | | IV-2 | HSPA13 | 0.73 | 4402 | 3 | 4 | | | IV-2 | KATNAL1 | 0.69 |
| 4307 | 3 | 4 | | | IV-2 | HSPA1L | 0.81 | 4403 | 3 | 4 | | | IV-2 | KBTBD11 | 0.94 |
| 4308 | 3 | 4 | | | IV-2 | HSPA2 | 0.85 | 4404 | 3 | 4 | | | IV-2 | KBTBD2 | 0.88 |
| 4309 | 3 | 4 | | | IV-2 | HSPA4 | 0.95 | 4405 | 3 | 4 | | | IV-2 | KCMF1 | 0.85 |
| 4310 | 3 | 4 | | | IV-2 | HSPA5 | 0.82 | 4406 | 3 | 4 | | | IV-2 | KCNE1 | 1.00 |
| 4311 | 3 | 4 | | | IV-2 | HSPE1-MOB4 | 0.92 | 4407 | 3 | 4 | | | IV-2 | KCNG1 | 0.97 |
| 4312 | 3 | 4 | | | IV-2 | HTATIP2 | 0.92 | 4408 | 3 | 4 | | | IV-2 | KCNJ11 | 1.00 |
| 4313 | 3 | 4 | | | IV-2 | HTATSF1 | 0.75 | 4409 | 3 | 4 | | | IV-2 | KCNJ2-AS1 | 0.99 |
| 4314 | 3 | 4 | | | IV-2 | HTRA2 | 0.77 | 4410 | 3 | 4 | | | IV-2 | KCTD12 | 0.69 |
| 4315 | 3 | 4 | | | IV-2 | HYAL2 | 0.79 | 4411 | 3 | 4 | | | IV-2 | KCTD15 | 0.69 |
| 4316 | 3 | 4 | | | IV-2 | HYAL3 | 0.92 | 4412 | 3 | 4 | | | IV-2 | KCTD2 | 0.78 |
| 4317 | 3 | 4 | | | IV-2 | IAH1 | 0.73 | 4413 | 3 | 4 | | | IV-2 | KCTD21 | 0.76 |

Fig. 39 - 24

| | | | | | | | | | | | | | | |
|---|---|---|---|---|---|---|---|---|---|---|---|---|---|---|
| 4414 | 3 | 4 | | | IV-2 | KCTD3 | 0.84 | 4510 | 3 | 4 | | | IV-2 | LGALS3 | 0.71 |
| 4415 | 3 | 4 | | | IV-2 | KCTD7 | 0.78 | 4511 | 3 | 4 | | | IV-2 | LGALS4 | 0.76 |
| 4416 | 3 | 4 | | | IV-2 | KDELC2 | 0.76 | 4512 | 3 | 4 | | | IV-2 | LGALS7B | 0.83 |
| 4417 | 3 | 4 | | | IV-2 | KDELR2 | 0.85 | 4513 | 3 | 4 | | | IV-2 | LGMN | 0.76 |
| 4418 | 3 | 4 | | | IV-2 | KDM1A | 0.68 | 4514 | 3 | 4 | | | IV-2 | LGR4 | 0.89 |
| 4419 | 3 | 4 | | | IV-2 | KDM1B | 0.90 | 4515 | 3 | 4 | | | IV-2 | LGR5 | 0.90 |
| 4420 | 3 | 4 | | | IV-2 | KDM3B | 0.68 | 4516 | 3 | 4 | | | IV-2 | LGR6 | 0.68 |
| 4421 | 3 | 4 | | | IV-2 | KDM4C | 0.74 | 4517 | 3 | 4 | | | IV-2 | LHB | 0.95 |
| 4422 | 3 | 4 | | | IV-2 | KDM4D | 0.86 | 4518 | 3 | 4 | | | IV-2 | LIMA1 | 0.74 |
| 4423 | 3 | 4 | | | IV-2 | KDM5A | 0.94 | 4519 | 3 | 4 | | | IV-2 | LIMD1 | 0.93 |
| 4424 | 3 | 4 | | | IV-2 | KDM6A | 0.78 | 4520 | 3 | 4 | | | IV-2 | LIME1 | 0.68 |
| 4425 | 3 | 4 | | | IV-2 | KHDRBS1 | 0.77 | 4521 | 3 | 4 | | | IV-2 | LIMS1 | 0.70 |
| 4426 | 3 | 4 | | | IV-2 | KHDRBS3 | 0.82 | 4522 | 3 | 4 | | | IV-2 | LIN52 | 0.88 |
| 4427 | 3 | 4 | | | IV-2 | KHSRP | 0.67 | 4523 | 3 | 4 | | | IV-2 | LINC00116 | 0.83 |
| 4428 | 3 | 4 | | | IV-2 | KIAA0020 | 0.85 | 4524 | 3 | 4 | | | IV-2 | LINC00176 | 0.96 |
| 4429 | 3 | 4 | | | IV-2 | KIAA0090 | 0.69 | 4525 | 3 | 4 | | | IV-2 | LINC00263 | 0.89 |
| 4430 | 3 | 4 | | | IV-2 | KIAA0146 | 0.84 | 4526 | 3 | 4 | | | IV-2 | LINC00294 | 0.80 |
| 4431 | 3 | 4 | | | IV-2 | KIAA0182 | 0.78 | 4527 | 3 | 4 | | | IV-2 | LINC00319 | 0.84 |
| 4432 | 3 | 4 | | | IV-2 | KIAA0317 | 0.84 | 4528 | 3 | 4 | | | IV-2 | LINC00341 | 0.87 |
| 4433 | 3 | 4 | | | IV-2 | KIAA0319L | 0.82 | 4529 | 3 | 4 | | | IV-2 | LINC00526 | 0.82 |
| 4434 | 3 | 4 | | | IV-2 | KIAA0368 | 0.86 | 4530 | 3 | 4 | | | IV-2 | LIN5 | 0.69 |
| 4435 | 3 | 4 | | | IV-2 | KIAA0494 | 1.00 | 4531 | 3 | 4 | | | IV-2 | LIPC | 0.82 |
| 4436 | 3 | 4 | | | IV-2 | KIAA0586 | 0.77 | 4532 | 3 | 4 | | | IV-2 | LLGL2 | 0.82 |
| 4437 | 3 | 4 | | | IV-2 | KIAA0664 | 0.73 | 4533 | 3 | 4 | | | IV-2 | LMAN2L | 0.82 |
| 4438 | 3 | 4 | | | IV-2 | KIAA0748 | 0.92 | 4534 | 3 | 4 | | | IV-2 | LMLN | 0.81 |
| 4439 | 3 | 4 | | | IV-2 | KIAA0895 | 0.83 | 4535 | 3 | 4 | | | IV-2 | LNPEP | 1.00 |
| 4440 | 3 | 4 | | | IV-2 | KIAA0947 | 0.86 | 4536 | 3 | 4 | | | IV-2 | LNX1 | 0.93 |
| 4441 | 3 | 4 | | | IV-2 | KIAA1143 | 0.78 | 4537 | 3 | 4 | | | IV-2 | LOC100009676 | 0.73 |
| 4442 | 3 | 4 | | | IV-2 | KIAA1191 | 0.89 | 4538 | 3 | 4 | | | IV-2 | LOC100125556 | 0.90 |
| 4443 | 3 | 4 | | | IV-2 | KIAA1217 | 0.95 | 4539 | 3 | 4 | | | IV-2 | LOC100127888 | 0.87 |
| 4444 | 3 | 4 | | | IV-2 | KIAA1429 | 0.90 | 4540 | 3 | 4 | | | IV-2 | LOC100128239 | 0.96 |
| 4445 | 3 | 4 | | | IV-2 | KIAA1430 | 0.91 | 4541 | 3 | 4 | | | IV-2 | LOC100128420 | 0.92 |
| 4446 | 3 | 4 | | | IV-2 | KIAA1522 | 0.71 | 4542 | 3 | 4 | | | IV-2 | LOC100129046 | 0.96 |
| 4447 | 3 | 4 | | | IV-2 | KIAA1586 | 0.90 | 4543 | 3 | 4 | | | IV-2 | LOC100129196 | 0.89 |
| 4448 | 3 | 4 | | | IV-2 | KIAA1598 | 0.88 | 4544 | 3 | 4 | | | IV-2 | LOC100129550 | 0.88 |
| 4449 | 3 | 4 | | | IV-2 | KIAA1755 | 0.81 | 4545 | 3 | 4 | | | IV-2 | LOC100129722 | 0.90 |
| 4450 | 3 | 4 | | | IV-2 | KIAA1797 | 1.00 | 4546 | 3 | 4 | | | IV-2 | LOC100129917 | 0.87 |
| 4451 | 3 | 4 | | | IV-2 | KIAA1908 | 0.83 | 4547 | 3 | 4 | | | IV-2 | LOC100130581 | 0.75 |
| 4452 | 3 | 4 | | | IV-2 | KIAA1919 | 0.91 | 4548 | 3 | 4 | | | IV-2 | LOC100130705 | 0.86 |
| 4453 | 3 | 4 | | | IV-2 | KIDINS220 | 0.81 | 4549 | 3 | 4 | | | IV-2 | LOC100130950 | 0.91 |
| 4454 | 3 | 4 | | | IV-2 | KIF16B | 0.69 | 4550 | 3 | 4 | | | IV-2 | LOC100131096 | 0.88 |
| 4455 | 3 | 4 | | | IV-2 | KIF18B | 0.77 | 4551 | 3 | 4 | | | IV-2 | LOC100134713 | 0.96 |
| 4456 | 3 | 4 | | | IV-2 | KIF21B | 0.79 | 4552 | 3 | 4 | | | IV-2 | LOC100190938 | 0.80 |
| 4457 | 3 | 4 | | | IV-2 | KIF3B | 0.96 | 4553 | 3 | 4 | | | IV-2 | LOC100272228 | 0.75 |
| 4458 | 3 | 4 | | | IV-2 | KIF9 | 0.91 | 4554 | 3 | 4 | | | IV-2 | LOC100286793 | 0.97 |
| 4459 | 3 | 4 | | | IV-2 | KL | 0.95 | 4555 | 3 | 4 | | | IV-2 | LOC100287015 | 0.72 |
| 4460 | 3 | 4 | | | IV-2 | KLC4 | 0.74 | 4556 | 3 | 4 | | | IV-2 | LOC100287177 | 1.00 |
| 4461 | 3 | 4 | | | IV-2 | KLF11 | 0.68 | 4557 | 3 | 4 | | | IV-2 | LOC100287616 | 0.76 |
| 4462 | 3 | 4 | | | IV-2 | KLF14 | 0.99 | 4558 | 3 | 4 | | | IV-2 | LOC100287722 | 0.95 |
| 4463 | 3 | 4 | | | IV-2 | KLF6 | 0.73 | 4559 | 3 | 4 | | | IV-2 | LOC100288069 | 0.98 |
| 4464 | 3 | 4 | | | IV-2 | KLF8 | 0.88 | 4560 | 3 | 4 | | | IV-2 | LOC100288198 | 0.77 |
| 4465 | 3 | 4 | | | IV-2 | KLHL15 | 0.86 | 4561 | 3 | 4 | | | IV-2 | LOC100288637 | 0.92 |
| 4466 | 3 | 4 | | | IV-2 | KLHL18 | 0.70 | 4562 | 3 | 4 | | | IV-2 | LOC100289509 | 0.87 |
| 4467 | 3 | 4 | | | IV-2 | KLHL20 | 0.93 | 4563 | 3 | 4 | | | IV-2 | LOC100289511 | 0.81 |
| 4468 | 3 | 4 | | | IV-2 | KLHL21 | 0.73 | 4564 | 3 | 4 | | | IV-2 | LOC100335030 | 0.73 |
| 4469 | 3 | 4 | | | IV-2 | KLHL24 | 0.91 | 4565 | 3 | 4 | | | IV-2 | LOC100494405 | 0.88 |
| 4470 | 3 | 4 | | | IV-2 | KLHL7 | 0.88 | 4566 | 3 | 4 | | | IV-2 | LOC100505495 | 0.82 |
| 4471 | 3 | 4 | | | IV-2 | KPNA1 | 0.91 | 4567 | 3 | 4 | | | IV-2 | LOC100505624 | 0.74 |
| 4472 | 3 | 4 | | | IV-2 | KPNA2 | 0.72 | 4568 | 3 | 4 | | | IV-2 | LOC100505681 | 0.74 |
| 4473 | 3 | 4 | | | IV-2 | KPNA4 | 0.92 | 4569 | 3 | 4 | | | IV-2 | LOC100505812 | 0.89 |
| 4474 | 3 | 4 | | | IV-2 | KRT3 | 0.95 | 4570 | 3 | 4 | | | IV-2 | LOC100505876 | 0.86 |
| 4475 | 3 | 4 | | | IV-2 | KRT81 | 0.96 | 4571 | 3 | 4 | | | IV-2 | LOC100506068 | 0.81 |
| 4476 | 3 | 4 | | | IV-2 | KRT86 | 0.90 | 4572 | 3 | 4 | | | IV-2 | LOC100506190 | 0.89 |
| 4477 | 3 | 4 | | | IV-2 | KRTAP10-5 | 1.00 | 4573 | 3 | 4 | | | IV-2 | LOC100506207 | 0.98 |
| 4478 | 3 | 4 | | | IV-2 | KRTAP1-5 | 0.90 | 4574 | 3 | 4 | | | IV-2 | LOC100506334 | 0.96 |
| 4479 | 3 | 4 | | | IV-2 | KRTAP17-1 | 0.90 | 4575 | 3 | 4 | | | IV-2 | LOC100506548 | 0.82 |
| 4480 | 3 | 4 | | | IV-2 | KRTAP2-2 | 0.93 | 4576 | 3 | 4 | | | IV-2 | LOC100506730 | 0.97 |
| 4481 | 3 | 4 | | | IV-2 | KRTAP4-1 | 0.95 | 4577 | 3 | 4 | | | IV-2 | LOC100506930 | 0.90 |
| 4482 | 3 | 4 | | | IV-2 | KRTAP4-12 | 0.90 | 4578 | 3 | 4 | | | IV-2 | LOC100506990 | 0.77 |
| 4483 | 3 | 4 | | | IV-2 | KRTAP4-7 | 0.97 | 4579 | 3 | 4 | | | IV-2 | LOC100507351 | 0.90 |
| 4484 | 3 | 4 | | | IV-2 | KRTAP4-8 | 0.93 | 4580 | 3 | 4 | | | IV-2 | LOC100507433 | 0.96 |
| 4485 | 3 | 4 | | | IV-2 | KRTAP4-9 | 0.97 | 4581 | 3 | 4 | | | IV-2 | LOC100507567 | 0.89 |
| 4486 | 3 | 4 | | | IV-2 | KRTAP9-2 | 0.92 | 4582 | 3 | 4 | | | IV-2 | LOC100616668 | 0.91 |
| 4487 | 3 | 4 | | | IV-2 | KRTAP9-4 | 0.96 | 4583 | 3 | 4 | | | IV-2 | LOC100859930 | 0.84 |
| 4488 | 3 | 4 | | | IV-2 | KRTCAP2 | 0.70 | 4584 | 3 | 4 | | | IV-2 | LOC143666 | 0.71 |
| 4489 | 3 | 4 | | | IV-2 | KRTCAP3 | 0.87 | 4585 | 3 | 4 | | | IV-2 | LOC151534 | 0.68 |
| 4490 | 3 | 4 | | | IV-2 | KTN1-AS1 | 0.95 | 4586 | 3 | 4 | | | IV-2 | LOC152217 | 0.78 |
| 4491 | 3 | 4 | | | IV-2 | L3MBTL3 | 0.72 | 4587 | 3 | 4 | | | IV-2 | LOC154761 | 0.70 |
| 4492 | 3 | 4 | | | IV-2 | LAGE3 | 0.76 | 4588 | 3 | 4 | | | IV-2 | LOC254100 | 0.78 |
| 4493 | 3 | 4 | | | IV-2 | LAMTOR2 | 0.92 | 4589 | 3 | 4 | | | IV-2 | LOC254128 | 0.98 |
| 4494 | 3 | 4 | | | IV-2 | LANCL2 | 0.74 | 4590 | 3 | 4 | | | IV-2 | LOC283104 | 0.83 |
| 4495 | 3 | 4 | | | IV-2 | LAPTM4A | 0.98 | 4591 | 3 | 4 | | | IV-2 | LOC283481 | 0.87 |
| 4496 | 3 | 4 | | | IV-2 | LAPTM4B | 0.78 | 4592 | 3 | 4 | | | IV-2 | LOC284837 | 0.93 |
| 4497 | 3 | 4 | | | IV-2 | LARP1 | 0.82 | 4593 | 3 | 4 | | | IV-2 | LOC284889 | 0.67 |
| 4498 | 3 | 4 | | | IV-2 | LARP1B | 0.95 | 4594 | 3 | 4 | | | IV-2 | LOC285074 | 0.68 |
| 4499 | 3 | 4 | | | IV-2 | LARP4B | 0.93 | 4595 | 3 | 4 | | | IV-2 | LOC285419 | 0.88 |
| 4500 | 3 | 4 | | | IV-2 | LARS2 | 0.70 | 4596 | 3 | 4 | | | IV-2 | LOC339290 | 0.85 |
| 4501 | 3 | 4 | | | IV-2 | LCA5 | 0.71 | 4597 | 3 | 4 | | | IV-2 | LOC339803 | 0.76 |
| 4502 | 3 | 4 | | | IV-2 | LCMT2 | 0.76 | 4598 | 3 | 4 | | | IV-2 | LOC340037 | 0.89 |
| 4503 | 3 | 4 | | | IV-2 | LCORL | 0.97 | 4599 | 3 | 4 | | | IV-2 | LOC340544 | 0.95 |
| 4504 | 3 | 4 | | | IV-2 | LDHA | 0.99 | 4600 | 3 | 4 | | | IV-2 | LOC374443 | 0.93 |
| 4505 | 3 | 4 | | | IV-2 | LEF1 | 0.84 | 4601 | 3 | 4 | | | IV-2 | LOC387723 | 0.98 |
| 4506 | 3 | 4 | | | IV-2 | LEMD2 | 0.71 | 4602 | 3 | 4 | | | IV-2 | LOC400027 | 0.87 |
| 4507 | 3 | 4 | | | IV-2 | LENG9 | 0.90 | 4603 | 3 | 4 | | | IV-2 | LOC400752 | 0.68 |
| 4508 | 3 | 4 | | | IV-2 | LEPROT | 0.76 | 4604 | 3 | 4 | | | IV-2 | LOC401321 | 0.72 |
| 4509 | 3 | 4 | | | IV-2 | LFNG | 0.92 | 4605 | 3 | 4 | | | IV-2 | LOC439990 | 0.97 |

Fig. 39 - 25

| | | | | | | | | | | | | | | |
|---|---|---|---|---|---|---|---|---|---|---|---|---|---|---|
| 4606 | 3 | 4 | | | IV-2 | LOC440300 | 0.94 | 4702 | 3 | 4 | | | IV-2 | MBP | 0.72 |
| 4607 | 3 | 4 | | | IV-2 | LOC541473 | 0.82 | 4703 | 3 | 4 | | | IV-2 | MC1R | 0.69 |
| 4608 | 3 | 4 | | | IV-2 | LOC550112 | 0.86 | 4704 | 3 | 4 | | | IV-2 | MCART1 | 0.78 |
| 4609 | 3 | 4 | | | IV-2 | LOC550643 | 0.96 | 4705 | 3 | 4 | | | IV-2 | MCAT | 0.81 |
| 4610 | 3 | 4 | | | IV-2 | LOC595101 | 0.93 | 4706 | 3 | 4 | | | IV-2 | MCC | 0.81 |
| 4611 | 3 | 4 | | | IV-2 | LOC642852 | 0.75 | 4707 | 3 | 4 | | | IV-2 | MCEE | 0.97 |
| 4612 | 3 | 4 | | | IV-2 | LOC645212 | 0.97 | 4708 | 3 | 4 | | | IV-2 | MCFD2 | 0.91 |
| 4613 | 3 | 4 | | | IV-2 | LOC645513 | 0.95 | 4709 | 3 | 4 | | | IV-2 | MCHR1 | 0.93 |
| 4614 | 3 | 4 | | | IV-2 | LOC646576 | 0.98 | 4710 | 3 | 4 | | | IV-2 | MCM6 | 0.91 |
| 4615 | 3 | 4 | | | IV-2 | LOC646719 | 0.86 | 4711 | 3 | 4 | | | IV-2 | MCM9 | 0.87 |
| 4616 | 3 | 4 | | | IV-2 | LOC653566 | 0.98 | 4712 | 3 | 4 | | | IV-2 | MCMBP | 0.85 |
| 4617 | 3 | 4 | | | IV-2 | LOC728752 | 0.91 | 4713 | 3 | 4 | | | IV-2 | MCOLN1 | 0.74 |
| 4618 | 3 | 4 | | | IV-2 | LOC728855 | 0.78 | 4714 | 3 | 4 | | | IV-2 | MCRS1 | 0.72 |
| 4619 | 3 | 4 | | | IV-2 | LOC729013 | 0.76 | 4715 | 3 | 4 | | | IV-2 | MDFI | 0.96 |
| 4620 | 3 | 4 | | | IV-2 | LOC729176 | 0.74 | 4716 | 3 | 4 | | | IV-2 | MDFIC | 0.91 |
| 4621 | 3 | 4 | | | IV-2 | LOC84856 | 0.97 | 4717 | 3 | 4 | | | IV-2 | MDM1 | 0.81 |
| 4622 | 3 | 4 | | | IV-2 | LOC92249 | 0.93 | 4718 | 3 | 4 | | | IV-2 | MDM4 | 0.99 |
| 4623 | 3 | 4 | | | IV-2 | LONP1 | 0.75 | 4719 | 3 | 4 | | | IV-2 | MDN1 | 0.72 |
| 4624 | 3 | 4 | | | IV-2 | LONRF1 | 0.98 | 4720 | 3 | 4 | | | IV-2 | ME2 | 0.76 |
| 4625 | 3 | 4 | | | IV-2 | LPCAT2 | 0.88 | 4721 | 3 | 4 | | | IV-2 | MEA1 | 0.74 |
| 4626 | 3 | 4 | | | IV-2 | LPHN2 | 0.99 | 4722 | 3 | 4 | | | IV-2 | MEAF6 | 0.87 |
| 4627 | 3 | 4 | | | IV-2 | LRIG3 | 0.75 | 4723 | 3 | 4 | | | IV-2 | MED13L | 0.95 |
| 4628 | 3 | 4 | | | IV-2 | LRMP | 0.94 | 4724 | 3 | 4 | | | IV-2 | MED14 | 0.88 |
| 4629 | 3 | 4 | | | IV-2 | LRP12 | 0.91 | 4725 | 3 | 4 | | | IV-2 | MED17 | 0.90 |
| 4630 | 3 | 4 | | | IV-2 | LRP2BP | 0.97 | 4726 | 3 | 4 | | | IV-2 | MED18 | 1.00 |
| 4631 | 3 | 4 | | | IV-2 | LRPAP1 | 0.78 | 4727 | 3 | 4 | | | IV-2 | MED21 | 0.94 |
| 4632 | 3 | 4 | | | IV-2 | LRR1 | 0.72 | 4728 | 3 | 4 | | | IV-2 | MED26 | 0.68 |
| 4633 | 3 | 4 | | | IV-2 | LRRC1 | 0.92 | 4729 | 3 | 4 | | | IV-2 | MED4 | 0.85 |
| 4634 | 3 | 4 | | | IV-2 | LRRC37BP1 | 0.83 | 4730 | 3 | 4 | | | IV-2 | MED6 | 0.95 |
| 4635 | 3 | 4 | | | IV-2 | LRRC4 | 0.99 | 4731 | 3 | 4 | | | IV-2 | MED7 | 0.95 |
| 4636 | 3 | 4 | | | IV-2 | LRRC49 | 0.93 | 4732 | 3 | 4 | | | IV-2 | MEF2A | 0.82 |
| 4637 | 3 | 4 | | | IV-2 | LRRC57 | 0.80 | 4733 | 3 | 4 | | | IV-2 | MEF2BNB | 0.79 |
| 4638 | 3 | 4 | | | IV-2 | LRRC6 | 0.89 | 4734 | 3 | 4 | | | IV-2 | MEF2C | 0.72 |
| 4639 | 3 | 4 | | | IV-2 | LRRC8D | 0.87 | 4735 | 3 | 4 | | | IV-2 | MEIS3P1 | 0.67 |
| 4640 | 3 | 4 | | | IV-2 | LRRFIP2 | 0.70 | 4736 | 3 | 4 | | | IV-2 | MELK | 1.00 |
| 4641 | 3 | 4 | | | IV-2 | LRTOMT | 0.93 | 4737 | 3 | 4 | | | IV-2 | MESDC2 | 0.84 |
| 4642 | 3 | 4 | | | IV-2 | LSG1 | 0.76 | 4738 | 3 | 4 | | | IV-2 | METTL1 | 0.87 |
| 4643 | 3 | 4 | | | IV-2 | LSM1 | 0.81 | 4739 | 3 | 4 | | | IV-2 | METTL10 | 0.95 |
| 4644 | 3 | 4 | | | IV-2 | LSM10 | 0.88 | 4740 | 3 | 4 | | | IV-2 | METTL12 | 0.78 |
| 4645 | 3 | 4 | | | IV-2 | LSM14A | 0.70 | 4741 | 3 | 4 | | | IV-2 | METTL16 | 1.00 |
| 4646 | 3 | 4 | | | IV-2 | LSM4 | 0.95 | 4742 | 3 | 4 | | | IV-2 | METTL19 | 0.98 |
| 4647 | 3 | 4 | | | IV-2 | LTB4R | 0.81 | 4743 | 3 | 4 | | | IV-2 | METTL22 | 0.68 |
| 4648 | 3 | 4 | | | IV-2 | LTBR | 0.70 | 4744 | 3 | 4 | | | IV-2 | METTL4 | 0.79 |
| 4649 | 3 | 4 | | | IV-2 | LUC7L2 | 0.89 | 4745 | 3 | 4 | | | IV-2 | MFAP1 | 0.79 |
| 4650 | 3 | 4 | | | IV-2 | LURAP1L | 0.72 | 4746 | 3 | 4 | | | IV-2 | MFAP3 | 0.89 |
| 4651 | 3 | 4 | | | IV-2 | LXN | 0.79 | 4747 | 3 | 4 | | | IV-2 | MFF | 0.85 |
| 4652 | 3 | 4 | | | IV-2 | LY6G6D | 0.92 | 4748 | 3 | 4 | | | IV-2 | MFN2 | 0.67 |
| 4653 | 3 | 4 | | | IV-2 | LY75 | 0.95 | 4749 | 3 | 4 | | | IV-2 | MFSD10 | 0.76 |
| 4654 | 3 | 4 | | | IV-2 | LYRM4 | 0.90 | 4750 | 3 | 4 | | | IV-2 | MFSD6 | 0.77 |
| 4655 | 3 | 4 | | | IV-2 | LYSMD4 | 0.95 | 4751 | 3 | 4 | | | IV-2 | MFSD7 | 0.68 |
| 4656 | 3 | 4 | | | IV-2 | LZTFL1 | 0.96 | 4752 | 3 | 4 | | | IV-2 | MGA | 0.79 |
| 4657 | 3 | 4 | | | IV-2 | MACF1 | 0.72 | 4753 | 3 | 4 | | | IV-2 | MGAT2 | 0.71 |
| 4658 | 3 | 4 | | | IV-2 | MAD2L1BP | 0.91 | 4754 | 3 | 4 | | | IV-2 | MGAT4B | 0.74 |
| 4659 | 3 | 4 | | | IV-2 | MAEA | 0.95 | 4755 | 3 | 4 | | | IV-2 | MGC16275 | 0.73 |
| 4660 | 3 | 4 | | | IV-2 | MAGED4B | 0.77 | 4756 | 3 | 4 | | | IV-2 | MGC3771 | 0.91 |
| 4661 | 3 | 4 | | | IV-2 | MAGEF1 | 0.98 | 4757 | 3 | 4 | | | IV-2 | MGC39372 | 0.88 |
| 4662 | 3 | 4 | | | IV-2 | MAGI3 | 0.97 | 4758 | 3 | 4 | | | IV-2 | MGMT | 0.85 |
| 4663 | 3 | 4 | | | IV-2 | MALSU1 | 0.89 | 4759 | 3 | 4 | | | IV-2 | MGP | 0.99 |
| 4664 | 3 | 4 | | | IV-2 | MAMSTR | 0.90 | 4760 | 3 | 4 | | | IV-2 | MIAT | 0.93 |
| 4665 | 3 | 4 | | | IV-2 | MAN8A | 0.82 | 4761 | 3 | 4 | | | IV-2 | MICU1 | 0.83 |
| 4666 | 3 | 4 | | | IV-2 | MANBAL | 0.85 | 4762 | 3 | 4 | | | IV-2 | MID1 | 0.68 |
| 4667 | 3 | 4 | | | IV-2 | MAP2K1 | 0.92 | 4763 | 3 | 4 | | | IV-2 | MID1IP1 | 0.67 |
| 4668 | 3 | 4 | | | IV-2 | MAP3K1 | 0.90 | 4764 | 3 | 4 | | | IV-2 | MIEN1 | 0.90 |
| 4669 | 3 | 4 | | | IV-2 | MAP3K11 | 0.69 | 4765 | 3 | 4 | | | IV-2 | MIER1 | 0.87 |
| 4670 | 3 | 4 | | | IV-2 | MAP3K2 | 0.76 | 4766 | 3 | 4 | | | IV-2 | MIER2 | 0.72 |
| 4671 | 3 | 4 | | | IV-2 | MAP3K8 | 0.77 | 4767 | 3 | 4 | | | IV-2 | MIIP | 0.74 |
| 4672 | 3 | 4 | | | IV-2 | MAP4K1 | 0.94 | 4768 | 3 | 4 | | | IV-2 | MINA | 0.98 |
| 4673 | 3 | 4 | | | IV-2 | MAP4K3 | 0.99 | 4769 | 3 | 4 | | | IV-2 | MINOS1 | 0.83 |
| 4674 | 3 | 4 | | | IV-2 | MAP4K4 | 0.87 | 4770 | 3 | 4 | | | IV-2 | MIOS | 0.99 |
| 4675 | 3 | 4 | | | IV-2 | MAP4K5 | 0.95 | 4771 | 3 | 4 | | | IV-2 | MIR210HG | 0.91 |
| 4676 | 3 | 4 | | | IV-2 | MAPK1 | 0.94 | 4772 | 3 | 4 | | | IV-2 | MIS18BP1 | 0.75 |
| 4677 | 3 | 4 | | | IV-2 | MAPK14 | 0.82 | 4773 | 3 | 4 | | | IV-2 | MKI67IP | 0.82 |
| 4678 | 3 | 4 | | | IV-2 | MAPK1IP1L | 0.75 | 4774 | 3 | 4 | | | IV-2 | MKKS | 0.93 |
| 4679 | 3 | 4 | | | IV-2 | MAPK3 | 0.77 | 4775 | 3 | 4 | | | IV-2 | MKL2 | 0.80 |
| 4680 | 3 | 4 | | | IV-2 | MAPK9 | 0.88 | 4776 | 3 | 4 | | | IV-2 | MKRN2 | 0.89 |
| 4681 | 3 | 4 | | | IV-2 | MAPKAP1 | 0.84 | 4777 | 3 | 4 | | | IV-2 | MLANA | 0.68 |
| 4682 | 3 | 4 | | | IV-2 | MAPKAPK5 | 0.72 | 4778 | 3 | 4 | | | IV-2 | MLF2 | 0.69 |
| 4683 | 3 | 4 | | | IV-2 | MAPRE3 | 0.79 | 4779 | 3 | 4 | | | IV-2 | MLH1 | 0.71 |
| 4684 | 3 | 4 | | | IV-2 | MAPT | 0.86 | 4780 | 3 | 4 | | | IV-2 | MLL5 | 0.90 |
| 4685 | 3 | 4 | | | IV-2 | MARCH1 | 0.99 | 4781 | 3 | 4 | | | IV-2 | MLLT10 | 0.80 |
| 4686 | 3 | 4 | | | IV-2 | MARCH2 | 0.86 | 4782 | 3 | 4 | | | IV-2 | MLLT3 | 0.95 |
| 4687 | 3 | 4 | | | IV-2 | MARCH6 | 0.84 | 4783 | 3 | 4 | | | IV-2 | MLLT4-AS1 | 0.96 |
| 4688 | 3 | 4 | | | IV-2 | MARCH7 | 0.99 | 4784 | 3 | 4 | | | IV-2 | MLX | 0.81 |
| 4689 | 3 | 4 | | | IV-2 | MARCKSL1 | 0.97 | 4785 | 3 | 4 | | | IV-2 | MMACHC | 0.83 |
| 4690 | 3 | 4 | | | IV-2 | MARK3 | 0.69 | 4786 | 3 | 4 | | | IV-2 | MMP24 | 0.72 |
| 4691 | 3 | 4 | | | IV-2 | MAT2A | 0.85 | 4787 | 3 | 4 | | | IV-2 | MMS22L | 0.99 |
| 4692 | 3 | 4 | | | IV-2 | MAT2B | 0.99 | 4788 | 3 | 4 | | | IV-2 | MOB2 | 0.82 |
| 4693 | 3 | 4 | | | IV-2 | MATL2963 | 0.67 | 4789 | 3 | 4 | | | IV-2 | MOCS1 | 0.76 |
| 4694 | 3 | 4 | | | IV-2 | MATN2 | 0.74 | 4790 | 3 | 4 | | | IV-2 | MOGS | 0.71 |
| 4695 | 3 | 4 | | | IV-2 | MAVS | 0.84 | 4791 | 3 | 4 | | | IV-2 | MORC4 | 0.77 |
| 4696 | 3 | 4 | | | IV-2 | MB21D1 | 0.94 | 4792 | 3 | 4 | | | IV-2 | MORF4L2 | 0.75 |
| 4697 | 3 | 4 | | | IV-2 | MBD3 | 0.70 | 4793 | 3 | 4 | | | IV-2 | MPDU1 | 0.87 |
| 4698 | 3 | 4 | | | IV-2 | MBD4 | 0.90 | 4794 | 3 | 4 | | | IV-2 | MPP1 | 0.83 |
| 4699 | 3 | 4 | | | IV-2 | MBD5 | 0.93 | 4795 | 3 | 4 | | | IV-2 | MPPE1 | 0.79 |
| 4700 | 3 | 4 | | | IV-2 | MBLAC2 | 0.95 | 4796 | 3 | 4 | | | IV-2 | MPPED2 | 0.96 |
| 4701 | 3 | 4 | | | IV-2 | MBNL3 | 0.70 | 4797 | 3 | 4 | | | IV-2 | MPRIP | 0.67 |

Fig. 39 - 26

| | | | | | | | | | | | | | | | |
|---|---|---|---|---|---|---|---|---|---|---|---|---|---|---|---|
| 4798 | 3 | 4 | | | IV-2 | MPV17 | 0.87 | 4894 | 3 | 4 | | | IV-2 | NAGPA | 0.76 |
| 4799 | 3 | 4 | | | IV-2 | MPV17L2 | 0.99 | 4895 | 3 | 4 | | | IV-2 | NAGS | 0.98 |
| 4800 | 3 | 4 | | | IV-2 | MR1 | 0.91 | 4896 | 3 | 4 | | | IV-2 | NANOS1 | 0.87 |
| 4801 | 3 | 4 | | | IV-2 | MRE11A | 0.87 | 4897 | 3 | 4 | | | IV-2 | NANP | 0.73 |
| 4802 | 3 | 4 | | | IV-2 | MRFAP1 | 0.79 | 4898 | 3 | 4 | | | IV-2 | NANS | 0.94 |
| 4803 | 3 | 4 | | | IV-2 | MRFAP1L1 | 0.82 | 4899 | 3 | 4 | | | IV-2 | NAP1L2 | 0.94 |
| 4804 | 3 | 4 | | | IV-2 | MRM1 | 0.99 | 4900 | 3 | 4 | | | IV-2 | NAPRT1 | 0.85 |
| 4805 | 3 | 4 | | | IV-2 | MRP63 | 0.85 | 4901 | 3 | 4 | | | IV-2 | NARG2 | 0.97 |
| 4806 | 3 | 4 | | | IV-2 | MRPL1 | 0.79 | 4902 | 3 | 4 | | | IV-2 | NARS | 0.93 |
| 4807 | 3 | 4 | | | IV-2 | MRPL10 | 0.71 | 4903 | 3 | 4 | | | IV-2 | NAT1 | 0.89 |
| 4808 | 3 | 4 | | | IV-2 | MRPL11 | 0.88 | 4904 | 3 | 4 | | | IV-2 | NAT10 | 0.69 |
| 4809 | 3 | 4 | | | IV-2 | MRPL16 | 0.97 | 4905 | 3 | 4 | | | IV-2 | NAV2 | 0.99 |
| 4810 | 3 | 4 | | | IV-2 | MRPL17 | 0.71 | 4906 | 3 | 4 | | | IV-2 | NBPF1 | 0.69 |
| 4811 | 3 | 4 | | | IV-2 | MRPL18 | 0.73 | 4907 | 3 | 4 | | | IV-2 | NBPF14 | 0.82 |
| 4812 | 3 | 4 | | | IV-2 | MRPL23 | 0.79 | 4908 | 3 | 4 | | | IV-2 | NBPF16 | 0.79 |
| 4813 | 3 | 4 | | | IV-2 | MRPL24 | 0.82 | 4909 | 3 | 4 | | | IV-2 | NBPF24 | 0.82 |
| 4814 | 3 | 4 | | | IV-2 | MRPL3 | 0.93 | 4910 | 3 | 4 | | | IV-2 | NBR1 | 0.78 |
| 4815 | 3 | 4 | | | IV-2 | MRPL32 | 0.99 | 4911 | 3 | 4 | | | IV-2 | NCAM1 | 0.95 |
| 4816 | 3 | 4 | | | IV-2 | MRPL34 | 0.76 | 4912 | 3 | 4 | | | IV-2 | NCAPG2 | 0.89 |
| 4817 | 3 | 4 | | | IV-2 | MRPL35 | 0.97 | 4913 | 3 | 4 | | | IV-2 | NCBP2 | 0.96 |
| 4818 | 3 | 4 | | | IV-2 | MRPL38 | 0.81 | 4914 | 3 | 4 | | | IV-2 | NCKAP1 | 0.94 |
| 4819 | 3 | 4 | | | IV-2 | MRPL39 | 0.75 | 4915 | 3 | 4 | | | IV-2 | NCOA3 | 0.95 |
| 4820 | 3 | 4 | | | IV-2 | MRPL4 | 0.82 | 4916 | 3 | 4 | | | IV-2 | NCSTN | 0.73 |
| 4821 | 3 | 4 | | | IV-2 | MRPL42 | 0.79 | 4917 | 3 | 4 | | | IV-2 | NDN | 0.69 |
| 4822 | 3 | 4 | | | IV-2 | MRPL43 | 0.79 | 4918 | 3 | 4 | | | IV-2 | NDNF | 0.75 |
| 4823 | 3 | 4 | | | IV-2 | MRPL44 | 0.90 | 4919 | 3 | 4 | | | IV-2 | NDRG4 | 0.94 |
| 4824 | 3 | 4 | | | IV-2 | MRPL46 | 0.76 | 4920 | 3 | 4 | | | IV-2 | NDUFA11 | 0.89 |
| 4825 | 3 | 4 | | | IV-2 | MRPL49 | 0.92 | 4921 | 3 | 4 | | | IV-2 | NDUFA13 | 0.82 |
| 4826 | 3 | 4 | | | IV-2 | MRPL50 | 0.88 | 4922 | 3 | 4 | | | IV-2 | NDUFA2 | 0.93 |
| 4827 | 3 | 4 | | | IV-2 | MRPL52 | 0.89 | 4923 | 3 | 4 | | | IV-2 | NDUFA7 | 0.95 |
| 4828 | 3 | 4 | | | IV-2 | MRPL53 | 0.84 | 4924 | 3 | 4 | | | IV-2 | NDUFAF3 | 0.97 |
| 4829 | 3 | 4 | | | IV-2 | MRPL54 | 0.76 | 4925 | 3 | 4 | | | IV-2 | NDUFB10 | 0.85 |
| 4830 | 3 | 4 | | | IV-2 | MRPL55 | 0.75 | 4926 | 3 | 4 | | | IV-2 | NDUFB4 | 0.87 |
| 4831 | 3 | 4 | | | IV-2 | MRPS16 | 0.92 | 4927 | 3 | 4 | | | IV-2 | NDUFB7 | 0.78 |
| 4832 | 3 | 4 | | | IV-2 | MRPS18B | 0.94 | 4928 | 3 | 4 | | | IV-2 | NDUFB8 | 0.94 |
| 4833 | 3 | 4 | | | IV-2 | MRPS2 | 0.76 | 4929 | 3 | 4 | | | IV-2 | NDUFS3 | 0.87 |
| 4834 | 3 | 4 | | | IV-2 | MRPS22 | 0.92 | 4930 | 3 | 4 | | | IV-2 | NDUFS5 | 1.00 |
| 4835 | 3 | 4 | | | IV-2 | MRPS26 | 0.83 | 4931 | 3 | 4 | | | IV-2 | NDUFS7 | 0.82 |
| 4836 | 3 | 4 | | | IV-2 | MRPS31 | 0.87 | 4932 | 3 | 4 | | | IV-2 | NDUFS8 | 0.83 |
| 4837 | 3 | 4 | | | IV-2 | MRPS5 | 0.84 | 4933 | 3 | 4 | | | IV-2 | NDUFV1 | 0.77 |
| 4838 | 3 | 4 | | | IV-2 | MRPS6 | 0.95 | 4934 | 3 | 4 | | | IV-2 | NDUFV3 | 0.98 |
| 4839 | 3 | 4 | | | IV-2 | MRRF | 0.95 | 4935 | 3 | 4 | | | IV-2 | NEGR1 | 0.84 |
| 4840 | 3 | 4 | | | IV-2 | MRTO4 | 0.74 | 4936 | 3 | 4 | | | IV-2 | NEK4 | 0.81 |
| 4841 | 3 | 4 | | | IV-2 | MS4A14 | 0.95 | 4937 | 3 | 4 | | | IV-2 | NEK8 | 0.93 |
| 4842 | 3 | 4 | | | IV-2 | MS4A4A | 0.98 | 4938 | 3 | 4 | | | IV-2 | NEK9 | 0.80 |
| 4843 | 3 | 4 | | | IV-2 | MSH2 | 0.78 | 4939 | 3 | 4 | | | IV-2 | NENF | 0.68 |
| 4844 | 3 | 4 | | | IV-2 | MSI2 | 0.91 | 4940 | 3 | 4 | | | IV-2 | NET1 | 0.84 |
| 4845 | 3 | 4 | | | IV-2 | MSL1 | 0.85 | 4941 | 3 | 4 | | | IV-2 | NEU1 | 0.68 |
| 4846 | 3 | 4 | | | IV-2 | MSL2 | 0.73 | 4942 | 3 | 4 | | | IV-2 | NF1 | 0.87 |
| 4847 | 3 | 4 | | | IV-2 | MSL3P1 | 0.70 | 4943 | 3 | 4 | | | IV-2 | NFATC2 | 0.98 |
| 4848 | 3 | 4 | | | IV-2 | MSRA | 0.88 | 4944 | 3 | 4 | | | IV-2 | NFATC2IP | 0.88 |
| 4849 | 3 | 4 | | | IV-2 | MSRB3 | 0.72 | 4945 | 3 | 4 | | | IV-2 | NFATC3 | 0.76 |
| 4850 | 3 | 4 | | | IV-2 | MSX1 | 0.68 | 4946 | 3 | 4 | | | IV-2 | NFE2L2 | 0.84 |
| 4851 | 3 | 4 | | | IV-2 | MT1X | 0.97 | 4947 | 3 | 4 | | | IV-2 | NFIC | 0.76 |
| 4852 | 3 | 4 | | | IV-2 | MTAP | 0.99 | 4948 | 3 | 4 | | | IV-2 | NFKB1 | 0.80 |
| 4853 | 3 | 4 | | | IV-2 | MTCH1 | 0.78 | 4949 | 3 | 4 | | | IV-2 | NFKBID | 0.87 |
| 4854 | 3 | 4 | | | IV-2 | MTCP1NB | 0.89 | 4950 | 3 | 4 | | | IV-2 | NFX1 | 0.82 |
| 4855 | 3 | 4 | | | IV-2 | MTFMT | 0.76 | 4951 | 3 | 4 | | | IV-2 | NFYA | 0.69 |
| 4856 | 3 | 4 | | | IV-2 | MTG1 | 0.82 | 4952 | 3 | 4 | | | IV-2 | NFYB | 0.98 |
| 4857 | 3 | 4 | | | IV-2 | MTHFD2L | 0.95 | 4953 | 3 | 4 | | | IV-2 | NFYC | 0.82 |
| 4858 | 3 | 4 | | | IV-2 | MTHFSD | 0.97 | 4954 | 3 | 4 | | | IV-2 | NGFR | 0.85 |
| 4859 | 3 | 4 | | | IV-2 | MTIF2 | 0.85 | 4955 | 3 | 4 | | | IV-2 | NGRN | 0.71 |
| 4860 | 3 | 4 | | | IV-2 | MTM1 | 0.82 | 4956 | 3 | 4 | | | IV-2 | NHLH2 | 0.89 |
| 4861 | 3 | 4 | | | IV-2 | MTMR12 | 0.94 | 4957 | 3 | 4 | | | IV-2 | NHP2 | 0.72 |
| 4862 | 3 | 4 | | | IV-2 | MTMR14 | 0.68 | 4958 | 3 | 4 | | | IV-2 | NHS | 0.97 |
| 4863 | 3 | 4 | | | IV-2 | MTMR2 | 0.95 | 4959 | 3 | 4 | | | IV-2 | NID2 | 0.78 |
| 4864 | 3 | 4 | | | IV-2 | MTMR4 | 0.97 | 4960 | 3 | 4 | | | IV-2 | NIF3L1 | 0.87 |
| 4865 | 3 | 4 | | | IV-2 | MTO1 | 0.85 | 4961 | 3 | 4 | | | IV-2 | NIN | 0.97 |
| 4866 | 3 | 4 | | | IV-2 | MTOR | 0.95 | 4962 | 3 | 4 | | | IV-2 | NINJ1 | 0.97 |
| 4867 | 3 | 4 | | | IV-2 | MTPAP | 0.91 | 4963 | 3 | 4 | | | IV-2 | NINL | 0.74 |
| 4868 | 3 | 4 | | | IV-2 | MTRNR2L2 | 0.93 | 4964 | 3 | 4 | | | IV-2 | NIP7 | 0.97 |
| 4869 | 3 | 4 | | | IV-2 | MTUS1 | 0.91 | 4965 | 3 | 4 | | | IV-2 | NIPA1 | 0.83 |
| 4870 | 3 | 4 | | | IV-2 | MUC20 | 0.97 | 4966 | 3 | 4 | | | IV-2 | NIPBL | 0.93 |
| 4871 | 3 | 4 | | | IV-2 | MUSTN1 | 0.95 | 4967 | 3 | 4 | | | IV-2 | NKAIN1 | 0.93 |
| 4872 | 3 | 4 | | | IV-2 | MUTED | 0.82 | 4968 | 3 | 4 | | | IV-2 | NKX3-1 | 0.88 |
| 4873 | 3 | 4 | | | IV-2 | MXRA7 | 0.69 | 4969 | 3 | 4 | | | IV-2 | NM8 | 0.93 |
| 4874 | 3 | 4 | | | IV-2 | MYEOV | 0.80 | 4970 | 3 | 4 | | | IV-2 | NMI | 0.98 |
| 4875 | 3 | 4 | | | IV-2 | MYL12A | 0.83 | 4971 | 3 | 4 | | | IV-2 | NMNAT2 | 0.90 |
| 4876 | 3 | 4 | | | IV-2 | MYL12B | 0.85 | 4972 | 3 | 4 | | | IV-2 | NMRAL1 | 0.77 |
| 4877 | 3 | 4 | | | IV-2 | MYL3 | 0.80 | 4973 | 3 | 4 | | | IV-2 | NMT1 | 0.74 |
| 4878 | 3 | 4 | | | IV-2 | MYL6B | 0.75 | 4974 | 3 | 4 | | | IV-2 | NO81 | 0.74 |
| 4879 | 3 | 4 | | | IV-2 | MYLIP | 0.68 | 4975 | 3 | 4 | | | IV-2 | NODAL | 0.95 |
| 4880 | 3 | 4 | | | IV-2 | MYO10 | 0.75 | 4976 | 3 | 4 | | | IV-2 | NOL11 | 0.83 |
| 4881 | 3 | 4 | | | IV-2 | MYO1D | 0.68 | 4977 | 3 | 4 | | | IV-2 | NOL7 | 0.69 |
| 4882 | 3 | 4 | | | IV-2 | MYO1F | 0.70 | 4978 | 3 | 4 | | | IV-2 | NOM1 | 0.91 |
| 4883 | 3 | 4 | | | IV-2 | MYO3A | 0.98 | 4979 | 3 | 4 | | | IV-2 | NOMO1 | 0.80 |
| 4884 | 3 | 4 | | | IV-2 | MYO5A | 0.70 | 4980 | 3 | 4 | | | IV-2 | NOMO2 | 0.70 |
| 4885 | 3 | 4 | | | IV-2 | MYO7A | 0.82 | 4981 | 3 | 4 | | | IV-2 | NOMO3 | 0.79 |
| 4886 | 3 | 4 | | | IV-2 | MZT2A | 0.93 | 4982 | 3 | 4 | | | IV-2 | NOP14-AS1 | 0.73 |
| 4887 | 3 | 4 | | | IV-2 | MZT2B | 0.88 | 4983 | 3 | 4 | | | IV-2 | NOP56 | 0.70 |
| 4888 | 3 | 4 | | | IV-2 | N4BP2L1 | 0.85 | 4984 | 3 | 4 | | | IV-2 | NOP58 | 0.95 |
| 4889 | 3 | 4 | | | IV-2 | NAA15 | 0.98 | 4985 | 3 | 4 | | | IV-2 | NOS3 | 0.87 |
| 4890 | 3 | 4 | | | IV-2 | NAAA | 0.70 | 4986 | 3 | 4 | | | IV-2 | NPAT | 0.80 |
| 4891 | 3 | 4 | | | IV-2 | NAALAD2 | 0.95 | 4987 | 3 | 4 | | | IV-2 | NPBWR1 | 0.97 |
| 4892 | 3 | 4 | | | IV-2 | NACA | 0.89 | 4988 | 3 | 4 | | | IV-2 | NPDC1 | 0.76 |
| 4893 | 3 | 4 | | | IV-2 | NADK | 0.98 | 4989 | 3 | 4 | | | IV-2 | NPEPPS | 0.87 |

Fig. 39 - 27

| | | | | | | | | | | | | | | |
|---|---|---|---|---|---|---|---|---|---|---|---|---|---|---|
| 4990 | 3 | 4 | | | IV-2 | NPHP1 | 0.98 | 5086 | 3 | 4 | | | IV-2 | PARN | 0.71 |
| 4991 | 3 | 4 | | | IV-2 | NPM1 | 0.94 | 5087 | 3 | 4 | | | IV-2 | PARP10 | 0.67 |
| 4992 | 3 | 4 | | | IV-2 | NPM3 | 0.74 | 5088 | 3 | 4 | | | IV-2 | PARP11 | 0.87 |
| 4993 | 3 | 4 | | | IV-2 | NPNT | 0.97 | 5089 | 3 | 4 | | | IV-2 | PARP14 | 0.71 |
| 4994 | 3 | 4 | | | IV-2 | NPR2 | 0.71 | 5090 | 3 | 4 | | | IV-2 | PARP16 | 0.77 |
| 4995 | 3 | 4 | | | IV-2 | NPR3 | 0.88 | 5091 | 3 | 4 | | | IV-2 | PARP4 | 0.87 |
| 4996 | 3 | 4 | | | IV-2 | NPTN | 0.99 | 5092 | 3 | 4 | | | IV-2 | PARP9 | 0.74 |
| 4997 | 3 | 4 | | | IV-2 | NPW | 0.92 | 5093 | 3 | 4 | | | IV-2 | PARS2 | 0.77 |
| 4998 | 3 | 4 | | | IV-2 | NR2F2 | 0.67 | 5094 | 3 | 4 | | | IV-2 | PATZ1 | 0.70 |
| 4999 | 3 | 4 | | | IV-2 | NR2F6 | 0.92 | 5095 | 3 | 4 | | | IV-2 | PBRM1 | 0.95 |
| 5000 | 3 | 4 | | | IV-2 | NRD1 | 0.82 | 5096 | 3 | 4 | | | IV-2 | PBX1 | 0.88 |
| 5001 | 3 | 4 | | | IV-2 | NSA2 | 0.84 | 5097 | 3 | 4 | | | IV-2 | PCBD2 | 0.92 |
| 5002 | 3 | 4 | | | IV-2 | NSFP1 | 0.97 | 5098 | 3 | 4 | | | IV-2 | PCBP1 | 0.70 |
| 5003 | 3 | 4 | | | IV-2 | NSMCE2 | 0.87 | 5099 | 3 | 4 | | | IV-2 | PCBP2 | 0.82 |
| 5004 | 3 | 4 | | | IV-2 | NSMCE4A | 0.78 | 5100 | 3 | 4 | | | IV-2 | PCDH18 | 0.73 |
| 5005 | 3 | 4 | | | IV-2 | NSUN2 | 0.98 | 5101 | 3 | 4 | | | IV-2 | PCDHB14 | 0.83 |
| 5006 | 3 | 4 | | | IV-2 | NT5C | 0.71 | 5102 | 3 | 4 | | | IV-2 | PCDHB2 | 0.92 |
| 5007 | 3 | 4 | | | IV-2 | NT5C3 | 0.98 | 5103 | 3 | 4 | | | IV-2 | PCDHGA3 | 0.77 |
| 5008 | 3 | 4 | | | IV-2 | NT5DC3 | 0.75 | 5104 | 3 | 4 | | | IV-2 | PCDHGA4 | 0.90 |
| 5009 | 3 | 4 | | | IV-2 | NTHL1 | 0.74 | 5105 | 3 | 4 | | | IV-2 | PCDHGA6 | 0.79 |
| 5010 | 3 | 4 | | | IV-2 | NTN4 | 0.86 | 5106 | 3 | 4 | | | IV-2 | PCF11 | 0.86 |
| 5011 | 3 | 4 | | | IV-2 | NUB1 | 0.82 | 5107 | 3 | 4 | | | IV-2 | PCGF5 | 0.80 |
| 5012 | 3 | 4 | | | IV-2 | NUBP2 | 0.70 | 5108 | 3 | 4 | | | IV-2 | PCNA | 0.91 |
| 5013 | 3 | 4 | | | IV-2 | NUDCD1 | 0.91 | 5109 | 3 | 4 | | | IV-2 | PCNX | 0.90 |
| 5014 | 3 | 4 | | | IV-2 | NUDT10 | 0.84 | 5110 | 3 | 4 | | | IV-2 | PCYT1A | 0.68 |
| 5015 | 3 | 4 | | | IV-2 | NUDT15 | 0.90 | 5111 | 3 | 4 | | | IV-2 | PCYT2 | 0.83 |
| 5016 | 3 | 4 | | | IV-2 | NUDT16L1 | 0.98 | 5112 | 3 | 4 | | | IV-2 | PDCD5 | 0.69 |
| 5017 | 3 | 4 | | | IV-2 | NUDT16P1 | 0.97 | 5113 | 3 | 4 | | | IV-2 | PDCD6 | 0.97 |
| 5018 | 3 | 4 | | | IV-2 | NUDT22 | 0.80 | 5114 | 3 | 4 | | | IV-2 | PDCD6IP | 0.80 |
| 5019 | 3 | 4 | | | IV-2 | NUDT3 | 0.72 | 5115 | 3 | 4 | | | IV-2 | PDCL | 0.69 |
| 5020 | 3 | 4 | | | IV-2 | NUDT4 | 0.94 | 5116 | 3 | 4 | | | IV-2 | PDDC1 | 0.80 |
| 5021 | 3 | 4 | | | IV-2 | NUDT4P1 | 0.99 | 5117 | 3 | 4 | | | IV-2 | PDE6D | 0.67 |
| 5022 | 3 | 4 | | | IV-2 | NUDT6 | 0.75 | 5118 | 3 | 4 | | | IV-2 | PDE6G | 0.93 |
| 5023 | 3 | 4 | | | IV-2 | NUDT9 | 0.72 | 5119 | 3 | 4 | | | IV-2 | PDGFD | 0.85 |
| 5024 | 3 | 4 | | | IV-2 | NUFIP2 | 0.96 | 5120 | 3 | 4 | | | IV-2 | PDHA2 | 0.95 |
| 5025 | 3 | 4 | | | IV-2 | NUM8 | 0.72 | 5121 | 3 | 4 | | | IV-2 | PDIA3 | 0.92 |
| 5026 | 3 | 4 | | | IV-2 | NUP133 | 0.88 | 5122 | 3 | 4 | | | IV-2 | PDLIM5 | 0.99 |
| 5027 | 3 | 4 | | | IV-2 | NUP153 | 0.76 | 5123 | 3 | 4 | | | IV-2 | PDP1 | 0.90 |
| 5028 | 3 | 4 | | | IV-2 | NUP160 | 0.80 | 5124 | 3 | 4 | | | IV-2 | PDPN | 0.77 |
| 5029 | 3 | 4 | | | IV-2 | NUP205 | 0.78 | 5125 | 3 | 4 | | | IV-2 | PDS5B | 0.86 |
| 5030 | 3 | 4 | | | IV-2 | NUP210 | 0.84 | 5126 | 3 | 4 | | | IV-2 | PDSS1 | 0.76 |
| 5031 | 3 | 4 | | | IV-2 | NUP35 | 0.90 | 5127 | 3 | 4 | | | IV-2 | PDSS2 | 0.96 |
| 5032 | 3 | 4 | | | IV-2 | NUP43 | 0.89 | 5128 | 3 | 4 | | | IV-2 | PDXDC1 | 0.87 |
| 5033 | 3 | 4 | | | IV-2 | NUP54 | 0.91 | 5129 | 3 | 4 | | | IV-2 | PDXK | 0.83 |
| 5034 | 3 | 4 | | | IV-2 | NUP88 | 0.84 | 5130 | 3 | 4 | | | IV-2 | PDXP | 0.83 |
| 5035 | 3 | 4 | | | IV-2 | NUPR1 | 0.71 | 5131 | 3 | 4 | | | IV-2 | PDZD11 | 0.70 |
| 5036 | 3 | 4 | | | IV-2 | NVL | 0.84 | 5132 | 3 | 4 | | | IV-2 | PDZD4 | 0.68 |
| 5037 | 3 | 4 | | | IV-2 | NXN | 0.70 | 5133 | 3 | 4 | | | IV-2 | PDZD7 | 0.80 |
| 5038 | 3 | 4 | | | IV-2 | O3FAR1 | 0.95 | 5134 | 3 | 4 | | | IV-2 | PEF1 | 0.83 |
| 5039 | 3 | 4 | | | IV-2 | OAS1 | 0.95 | 5135 | 3 | 4 | | | IV-2 | PELI1 | 0.81 |
| 5040 | 3 | 4 | | | IV-2 | OAT | 0.78 | 5136 | 3 | 4 | | | IV-2 | PELI2 | 0.73 |
| 5041 | 3 | 4 | | | IV-2 | OBFC2B | 0.74 | 5137 | 3 | 4 | | | IV-2 | PELO | 0.78 |
| 5042 | 3 | 4 | | | IV-2 | OCEL1 | 0.88 | 5138 | 3 | 4 | | | IV-2 | PEPD | 0.79 |
| 5043 | 3 | 4 | | | IV-2 | OCRL | 0.83 | 5139 | 3 | 4 | | | IV-2 | PER2 | 0.71 |
| 5044 | 3 | 4 | | | IV-2 | OGFOD1 | 0.72 | 5140 | 3 | 4 | | | IV-2 | PEX1 | 0.90 |
| 5045 | 3 | 4 | | | IV-2 | OGFRL1 | 0.71 | 5141 | 3 | 4 | | | IV-2 | PEX10 | 0.88 |
| 5046 | 3 | 4 | | | IV-2 | OLA1 | 0.79 | 5142 | 3 | 4 | | | IV-2 | PEX11B | 0.97 |
| 5047 | 3 | 4 | | | IV-2 | OPN3 | 0.84 | 5143 | 3 | 4 | | | IV-2 | PEX12 | 0.75 |
| 5048 | 3 | 4 | | | IV-2 | OPRL1 | 0.99 | 5144 | 3 | 4 | | | IV-2 | PEX13 | 0.91 |
| 5049 | 3 | 4 | | | IV-2 | OPTN | 0.67 | 5145 | 3 | 4 | | | IV-2 | PEX14 | 0.67 |
| 5050 | 3 | 4 | | | IV-2 | OR2A20P | 0.98 | 5146 | 3 | 4 | | | IV-2 | PEX6 | 0.77 |
| 5051 | 3 | 4 | | | IV-2 | OR52N4 | 0.94 | 5147 | 3 | 4 | | | IV-2 | PFDN1 | 0.91 |
| 5052 | 3 | 4 | | | IV-2 | ORC2 | 0.72 | 5148 | 3 | 4 | | | IV-2 | PFKM | 0.72 |
| 5053 | 3 | 4 | | | IV-2 | ORMDL3 | 0.87 | 5149 | 3 | 4 | | | IV-2 | PGAP3 | 0.78 |
| 5054 | 3 | 4 | | | IV-2 | OSBPL2 | 0.99 | 5150 | 3 | 4 | | | IV-2 | PGF | 0.68 |
| 5055 | 3 | 4 | | | IV-2 | OSBPL3 | 0.77 | 5151 | 3 | 4 | | | IV-2 | PGGT1B | 0.98 |
| 5056 | 3 | 4 | | | IV-2 | OSBPL8 | 0.94 | 5152 | 3 | 4 | | | IV-2 | PGM5P2 | 0.86 |
| 5057 | 3 | 4 | | | IV-2 | OSMR | 0.75 | 5153 | 3 | 4 | | | IV-2 | PGP | 0.75 |
| 5058 | 3 | 4 | | | IV-2 | OTUD4 | 0.90 | 5154 | 3 | 4 | | | IV-2 | PHACTR1 | 0.84 |
| 5059 | 3 | 4 | | | IV-2 | OXA1L | 0.88 | 5155 | 3 | 4 | | | IV-2 | PHACTR2 | 0.82 |
| 5060 | 3 | 4 | | | IV-2 | OXSM | 1.00 | 5156 | 3 | 4 | | | IV-2 | PHB | 0.94 |
| 5061 | 3 | 4 | | | IV-2 | P2RX4 | 0.89 | 5157 | 3 | 4 | | | IV-2 | PHF1 | 0.72 |
| 5062 | 3 | 4 | | | IV-2 | P2RX7 | 0.76 | 5158 | 3 | 4 | | | IV-2 | PHF10 | 0.88 |
| 5063 | 3 | 4 | | | IV-2 | P2RY11 | 0.70 | 5159 | 3 | 4 | | | IV-2 | PHF13 | 0.76 |
| 5064 | 3 | 4 | | | IV-2 | P4HA1 | 0.75 | 5160 | 3 | 4 | | | IV-2 | PHF17 | 0.95 |
| 5065 | 3 | 4 | | | IV-2 | P4HTM | 0.77 | 5161 | 3 | 4 | | | IV-2 | PHF23 | 0.88 |
| 5066 | 3 | 4 | | | IV-2 | PA2G4 | 0.73 | 5162 | 3 | 4 | | | IV-2 | PHF5A | 0.72 |
| 5067 | 3 | 4 | | | IV-2 | PAAF1 | 0.90 | 5163 | 3 | 4 | | | IV-2 | PHF6 | 0.85 |
| 5068 | 3 | 4 | | | IV-2 | PACRG | 0.99 | 5164 | 3 | 4 | | | IV-2 | PHKA1 | 0.87 |
| 5069 | 3 | 4 | | | IV-2 | PACSIN2 | 0.81 | 5165 | 3 | 4 | | | IV-2 | PHKA2 | 0.91 |
| 5070 | 3 | 4 | | | IV-2 | PAFAH1B2 | 0.89 | 5166 | 3 | 4 | | | IV-2 | PHLDB3 | 0.69 |
| 5071 | 3 | 4 | | | IV-2 | PAFAH1B3 | 0.77 | 5167 | 3 | 4 | | | IV-2 | PHLPP1 | 0.74 |
| 5072 | 3 | 4 | | | IV-2 | PAICS | 0.70 | 5168 | 3 | 4 | | | IV-2 | PHPT1 | 0.78 |
| 5073 | 3 | 4 | | | IV-2 | PAIP1 | 0.80 | 5169 | 3 | 4 | | | IV-2 | PHTF2 | 0.78 |
| 5074 | 3 | 4 | | | IV-2 | PAK1IP1 | 0.98 | 5170 | 3 | 4 | | | IV-2 | PHYH | 0.95 |
| 5075 | 3 | 4 | | | IV-2 | PAK2 | 0.81 | 5171 | 3 | 4 | | | IV-2 | PHYHIP | 0.68 |
| 5076 | 3 | 4 | | | IV-2 | PALB2 | 0.69 | 5172 | 3 | 4 | | | IV-2 | PIAS1 | 0.75 |
| 5077 | 3 | 4 | | | IV-2 | PALMD | 0.76 | 5173 | 3 | 4 | | | IV-2 | PIAS3 | 0.67 |
| 5078 | 3 | 4 | | | IV-2 | PANX2 | 0.79 | 5174 | 3 | 4 | | | IV-2 | PICALM | 0.96 |
| 5079 | 3 | 4 | | | IV-2 | PAPD7 | 0.97 | 5175 | 3 | 4 | | | IV-2 | PICK1 | 0.79 |
| 5080 | 3 | 4 | | | IV-2 | PAPOLA | 0.98 | 5176 | 3 | 4 | | | IV-2 | PIF1 | 0.93 |
| 5081 | 3 | 4 | | | IV-2 | PAPOLB | 0.96 | 5177 | 3 | 4 | | | IV-2 | PIG8 | 0.78 |
| 5082 | 3 | 4 | | | IV-2 | PAPOLG | 0.75 | 5178 | 3 | 4 | | | IV-2 | PIGF | 0.95 |
| 5083 | 3 | 4 | | | IV-2 | PAQR7 | 0.94 | 5179 | 3 | 4 | | | IV-2 | PIGG | 1.00 |
| 5084 | 3 | 4 | | | IV-2 | PARD3B | 0.76 | 5180 | 3 | 4 | | | IV-2 | PIGO | 0.73 |
| 5085 | 3 | 4 | | | IV-2 | PARL | 0.87 | 5181 | 3 | 4 | | | IV-2 | PIK3C2A | 0.94 |

Fig. 39 - 28

| | | | | | | | | | | | | | | | |
|---|---|---|---|---|---|---|---|---|---|---|---|---|---|---|---|
| 5182 | 3 | 4 | | | IV-2 | PIK3IP1 | 0.71 | 5278 | 3 | 4 | | | IV-2 | PPP1R7 | 0.88 |
| 5183 | 3 | 4 | | | IV-2 | PIK3R4 | 0.81 | 5279 | 3 | 4 | | | IV-2 | PPP1R8 | 0.75 |
| 5184 | 3 | 4 | | | IV-2 | PIM2 | 0.75 | 5280 | 3 | 4 | | | IV-2 | PPP2CA | 0.94 |
| 5185 | 3 | 4 | | | IV-2 | PIN1 | 0.76 | 5281 | 3 | 4 | | | IV-2 | PPP2CB | 0.98 |
| 5186 | 3 | 4 | | | IV-2 | PIP4K2A | 0.67 | 5282 | 3 | 4 | | | IV-2 | PPP2R2A | 0.93 |
| 5187 | 3 | 4 | | | IV-2 | PIP4K2C | 0.78 | 5283 | 3 | 4 | | | IV-2 | PPP2R3A | 0.67 |
| 5188 | 3 | 4 | | | IV-2 | PIP5L | 0.72 | 5284 | 3 | 4 | | | IV-2 | PPP2R5C | 0.86 |
| 5189 | 3 | 4 | | | IV-2 | PITHD1 | 0.98 | 5285 | 3 | 4 | | | IV-2 | PPP3CB | 0.83 |
| 5190 | 3 | 4 | | | IV-2 | PITPNB | 0.74 | 5286 | 3 | 4 | | | IV-2 | PPP4C | 0.75 |
| 5191 | 3 | 4 | | | IV-2 | PITRM1 | 0.70 | 5287 | 3 | 4 | | | IV-2 | PPP4R1 | 0.69 |
| 5192 | 3 | 4 | | | IV-2 | PKI55 | 0.89 | 5288 | 3 | 4 | | | IV-2 | PPP5C | 0.80 |
| 5193 | 3 | 4 | | | IV-2 | PKIA | 0.74 | 5289 | 3 | 4 | | | IV-2 | PPP6C | 0.83 |
| 5194 | 3 | 4 | | | IV-2 | PKNOX1 | 0.78 | 5290 | 3 | 4 | | | IV-2 | PPP6R3 | 0.87 |
| 5195 | 3 | 4 | | | IV-2 | PKP4 | 0.77 | 5291 | 3 | 4 | | | IV-2 | PPPDE1 | 0.96 |
| 5196 | 3 | 4 | | | IV-2 | PLA2G15 | 0.76 | 5292 | 3 | 4 | | | IV-2 | PQLC1 | 0.90 |
| 5197 | 3 | 4 | | | IV-2 | PLA2G3 | 0.69 | 5293 | 3 | 4 | | | IV-2 | PQLC3 | 0.91 |
| 5198 | 3 | 4 | | | IV-2 | PLA2G4A | 0.75 | 5294 | 3 | 4 | | | IV-2 | PRAM1 | 0.69 |
| 5199 | 3 | 4 | | | IV-2 | PLA2G4B | 0.87 | 5295 | 3 | 4 | | | IV-2 | PRC1 | 0.67 |
| 5200 | 3 | 4 | | | IV-2 | PLA2G5 | 0.90 | 5296 | 3 | 4 | | | IV-2 | PRCP | 0.77 |
| 5201 | 3 | 4 | | | IV-2 | PLAA | 0.95 | 5297 | 3 | 4 | | | IV-2 | PRDM16 | 0.98 |
| 5202 | 3 | 4 | | | IV-2 | PLAC8L1 | 0.89 | 5298 | 3 | 4 | | | IV-2 | PRDM2 | 0.72 |
| 5203 | 3 | 4 | | | IV-2 | PLCD1 | 0.77 | 5299 | 3 | 4 | | | IV-2 | PRDM4 | 0.69 |
| 5204 | 3 | 4 | | | IV-2 | PLCG2 | 0.74 | 5300 | 3 | 4 | | | IV-2 | PRDM6 | 0.93 |
| 5205 | 3 | 4 | | | IV-2 | PLD4 | 0.92 | 5301 | 3 | 4 | | | IV-2 | PRDM8 | 0.74 |
| 5206 | 3 | 4 | | | IV-2 | PLD6 | 0.94 | 5302 | 3 | 4 | | | IV-2 | PRDX4 | 0.84 |
| 5207 | 3 | 4 | | | IV-2 | PLDN | 0.90 | 5303 | 3 | 4 | | | IV-2 | PRDX6 | 0.95 |
| 5208 | 3 | 4 | | | IV-2 | PLEKHA3 | 0.81 | 5304 | 3 | 4 | | | IV-2 | PREB | 0.95 |
| 5209 | 3 | 4 | | | IV-2 | PLEKHA6 | 0.69 | 5305 | 3 | 4 | | | IV-2 | PRF1 | 0.78 |
| 5210 | 3 | 4 | | | IV-2 | PLEKHA7 | 0.77 | 5306 | 3 | 4 | | | IV-2 | PRIM2 | 0.98 |
| 5211 | 3 | 4 | | | IV-2 | PLEKHG1 | 0.67 | 5307 | 3 | 4 | | | IV-2 | PRKAB1 | 0.86 |
| 5212 | 3 | 4 | | | IV-2 | PLEKHH2 | 0.70 | 5308 | 3 | 4 | | | IV-2 | PRKAG1 | 0.78 |
| 5213 | 3 | 4 | | | IV-2 | PLEKHJ1 | 0.99 | 5309 | 3 | 4 | | | IV-2 | PRKAR1A | 0.98 |
| 5214 | 3 | 4 | | | IV-2 | PLK1S1 | 0.97 | 5310 | 3 | 4 | | | IV-2 | PRKCD | 0.88 |
| 5215 | 3 | 4 | | | IV-2 | PLK4 | 0.89 | 5311 | 3 | 4 | | | IV-2 | PRKCE | 0.82 |
| 5216 | 3 | 4 | | | IV-2 | PLOD1 | 0.68 | 5312 | 3 | 4 | | | IV-2 | PRKCH | 0.88 |
| 5217 | 3 | 4 | | | IV-2 | PLP1 | 0.86 | 5313 | 3 | 4 | | | IV-2 | PRKCZ | 0.98 |
| 5218 | 3 | 4 | | | IV-2 | PLRG1 | 0.91 | 5314 | 3 | 4 | | | IV-2 | PRKD3 | 0.80 |
| 5219 | 3 | 4 | | | IV-2 | PLS3 | 0.91 | 5315 | 3 | 4 | | | IV-2 | PRKDC | 0.77 |
| 5220 | 3 | 4 | | | IV-2 | PLSCR4 | 0.71 | 5316 | 3 | 4 | | | IV-2 | PRKRIR | 0.79 |
| 5221 | 3 | 4 | | | IV-2 | PLXDC2 | 0.78 | 5317 | 3 | 4 | | | IV-2 | PRMT2 | 0.71 |
| 5222 | 3 | 4 | | | IV-2 | PLXNC1 | 0.76 | 5318 | 3 | 4 | | | IV-2 | PRMT5 | 0.67 |
| 5223 | 3 | 4 | | | IV-2 | PMF1 | 0.70 | 5319 | 3 | 4 | | | IV-2 | PROCR | 0.95 |
| 5224 | 3 | 4 | | | IV-2 | PMM2 | 0.77 | 5320 | 3 | 4 | | | IV-2 | PROSER1 | 0.89 |
| 5225 | 3 | 4 | | | IV-2 | PMPCA | 0.87 | 5321 | 3 | 4 | | | IV-2 | PRPF18 | 0.99 |
| 5226 | 3 | 4 | | | IV-2 | PMS1 | 0.98 | 5322 | 3 | 4 | | | IV-2 | PRPF38A | 0.80 |
| 5227 | 3 | 4 | | | IV-2 | PMS2 | 0.81 | 5323 | 3 | 4 | | | IV-2 | PRPF4 | 0.78 |
| 5228 | 3 | 4 | | | IV-2 | PMS2P1 | 0.89 | 5324 | 3 | 4 | | | IV-2 | PRPS1 | 0.78 |
| 5229 | 3 | 4 | | | IV-2 | PMS2P3 | 0.72 | 5325 | 3 | 4 | | | IV-2 | PRPS2 | 0.91 |
| 5230 | 3 | 4 | | | IV-2 | PMS2P5 | 0.85 | 5326 | 3 | 4 | | | IV-2 | PRR14L | 0.93 |
| 5231 | 3 | 4 | | | IV-2 | PNKD | 0.82 | 5327 | 3 | 4 | | | IV-2 | PRR24 | 0.90 |
| 5232 | 3 | 4 | | | IV-2 | PNP | 0.82 | 5328 | 3 | 4 | | | IV-2 | PRR5L | 0.68 |
| 5233 | 3 | 4 | | | IV-2 | PNPLA7 | 0.77 | 5329 | 3 | 4 | | | IV-2 | PRRC1 | 1.00 |
| 5234 | 3 | 4 | | | IV-2 | PNPO | 1.00 | 5330 | 3 | 4 | | | IV-2 | PRUNE | 0.94 |
| 5235 | 3 | 4 | | | IV-2 | PNRC2 | 0.95 | 5331 | 3 | 4 | | | IV-2 | PSD3 | 0.71 |
| 5236 | 3 | 4 | | | IV-2 | PODNL1 | 0.87 | 5332 | 3 | 4 | | | IV-2 | PSG4 | 0.95 |
| 5237 | 3 | 4 | | | IV-2 | PODXL | 0.76 | 5333 | 3 | 4 | | | IV-2 | PSIMCT-1 | 0.97 |
| 5238 | 3 | 4 | | | IV-2 | POGK | 0.74 | 5334 | 3 | 4 | | | IV-2 | PSMA3 | 0.96 |
| 5239 | 3 | 4 | | | IV-2 | POLA1 | 0.94 | 5335 | 3 | 4 | | | IV-2 | PSMA6 | 0.94 |
| 5240 | 3 | 4 | | | IV-2 | POLD3 | 0.68 | 5336 | 3 | 4 | | | IV-2 | PSMB4 | 0.98 |
| 5241 | 3 | 4 | | | IV-2 | POLD4 | 0.94 | 5337 | 3 | 4 | | | IV-2 | PSMB7 | 0.80 |
| 5242 | 3 | 4 | | | IV-2 | POLE4 | 0.83 | 5338 | 3 | 4 | | | IV-2 | PSMB9 | 0.83 |
| 5243 | 3 | 4 | | | IV-2 | POLK | 0.89 | 5339 | 3 | 4 | | | IV-2 | PSMC2 | 0.84 |
| 5244 | 3 | 4 | | | IV-2 | POLL | 0.76 | 5340 | 3 | 4 | | | IV-2 | PSMC3 | 0.75 |
| 5245 | 3 | 4 | | | IV-2 | POLR1E | 0.72 | 5341 | 3 | 4 | | | IV-2 | PSMC5 | 0.75 |
| 5246 | 3 | 4 | | | IV-2 | POLR2B | 0.78 | 5342 | 3 | 4 | | | IV-2 | PSMD10 | 0.97 |
| 5247 | 3 | 4 | | | IV-2 | POLR2C | 0.83 | 5343 | 3 | 4 | | | IV-2 | PSMD13 | 0.84 |
| 5248 | 3 | 4 | | | IV-2 | POLR2E | 0.73 | 5344 | 3 | 4 | | | IV-2 | PSMD4 | 0.78 |
| 5249 | 3 | 4 | | | IV-2 | POLR2F | 0.82 | 5345 | 3 | 4 | | | IV-2 | PSMD5 | 0.98 |
| 5250 | 3 | 4 | | | IV-2 | POLR2G | 0.79 | 5346 | 3 | 4 | | | IV-2 | PSMD9 | 0.80 |
| 5251 | 3 | 4 | | | IV-2 | POLR2J | 0.72 | 5347 | 3 | 4 | | | IV-2 | PSME1 | 0.73 |
| 5252 | 3 | 4 | | | IV-2 | POLR2K | 0.90 | 5348 | 3 | 4 | | | IV-2 | PSMG2 | 0.79 |
| 5253 | 3 | 4 | | | IV-2 | POLR2L | 0.72 | 5349 | 3 | 4 | | | IV-2 | PSMG3 | 0.84 |
| 5254 | 3 | 4 | | | IV-2 | POLR2M | 0.82 | 5350 | 3 | 4 | | | IV-2 | PSRC1 | 0.85 |
| 5255 | 3 | 4 | | | IV-2 | POLR3C | 0.86 | 5351 | 3 | 4 | | | IV-2 | PTBP1 | 0.75 |
| 5256 | 3 | 4 | | | IV-2 | POLR3E | 0.71 | 5352 | 3 | 4 | | | IV-2 | PTBP3 | 0.85 |
| 5257 | 3 | 4 | | | IV-2 | POLR3GL | 0.83 | 5353 | 3 | 4 | | | IV-2 | PTDSS2 | 0.76 |
| 5258 | 3 | 4 | | | IV-2 | POLR3K | 0.93 | 5354 | 3 | 4 | | | IV-2 | PTGES2 | 0.72 |
| 5259 | 3 | 4 | | | IV-2 | POP4 | 0.94 | 5355 | 3 | 4 | | | IV-2 | PTGS2 | 0.71 |
| 5260 | 3 | 4 | | | IV-2 | POT1 | 0.86 | 5356 | 3 | 4 | | | IV-2 | PTP4A2 | 0.87 |
| 5261 | 3 | 4 | | | IV-2 | POU5F1B | 0.87 | 5357 | 3 | 4 | | | IV-2 | PTP4A3 | 0.89 |
| 5262 | 3 | 4 | | | IV-2 | PPAP2C | 0.68 | 5358 | 3 | 4 | | | IV-2 | PTPLAD1 | 0.82 |
| 5263 | 3 | 4 | | | IV-2 | PPAT | 0.98 | 5359 | 3 | 4 | | | IV-2 | PTPLAD2 | 0.88 |
| 5264 | 3 | 4 | | | IV-2 | PPFIA1 | 0.74 | 5360 | 3 | 4 | | | IV-2 | PTPLB | 0.69 |
| 5265 | 3 | 4 | | | IV-2 | PPHLN1 | 0.85 | 5361 | 3 | 4 | | | IV-2 | PTPMT1 | 0.99 |
| 5266 | 3 | 4 | | | IV-2 | PPIA | 0.84 | 5362 | 3 | 4 | | | IV-2 | PTPN11 | 0.95 |
| 5267 | 3 | 4 | | | IV-2 | PPIC | 0.80 | 5363 | 3 | 4 | | | IV-2 | PTPN21 | 0.84 |
| 5268 | 3 | 4 | | | IV-2 | PPIL1 | 0.90 | 5364 | 3 | 4 | | | IV-2 | PTPN3 | 0.88 |
| 5269 | 3 | 4 | | | IV-2 | PPM1L | 0.90 | 5365 | 3 | 4 | | | IV-2 | PTPRE | 0.87 |
| 5270 | 3 | 4 | | | IV-2 | PPME1 | 0.71 | 5366 | 3 | 4 | | | IV-2 | PTPRK | 0.84 |
| 5271 | 3 | 4 | | | IV-2 | PPP1CC | 0.84 | 5367 | 3 | 4 | | | IV-2 | PTPRN2 | 0.87 |
| 5272 | 3 | 4 | | | IV-2 | PPP1R10 | 0.68 | 5368 | 3 | 4 | | | IV-2 | PTRHD1 | 0.84 |
| 5273 | 3 | 4 | | | IV-2 | PPP1R11 | 0.75 | 5369 | 3 | 4 | | | IV-2 | PTTG2 | 0.76 |
| 5274 | 3 | 4 | | | IV-2 | PPP1R14B | 0.73 | 5370 | 3 | 4 | | | IV-2 | PTX3 | 0.87 |
| 5275 | 3 | 4 | | | IV-2 | PPP1R32 | 0.93 | 5371 | 3 | 4 | | | IV-2 | PUM1 | 0.83 |
| 5276 | 3 | 4 | | | IV-2 | PPP1R37 | 0.77 | 5372 | 3 | 4 | | | IV-2 | PUS1 | 0.76 |
| 5277 | 3 | 4 | | | IV-2 | PPP1R3F | 0.70 | 5373 | 3 | 4 | | | IV-2 | PUS7 | 0.76 |

Fig. 39 - 29

| | | | | | | | | | | | | | | | |
|---|---|---|---|---|---|---|---|---|---|---|---|---|---|---|---|
| 5374 | 3 | 4 | | | IV-2 | PUSureated | 0.82 | 5470 | 3 | 4 | | | IV-2 | REV3L | 0.76 |
| 5375 | 3 | 4 | | | IV-2 | PVRL3 | 0.74 | 5471 | 3 | 4 | | | IV-2 | REXO1L2P | 0.93 |
| 5376 | 3 | 4 | | | IV-2 | PXDN | 0.87 | 5472 | 3 | 4 | | | IV-2 | REXO4 | 0.73 |
| 5377 | 3 | 4 | | | IV-2 | PYCR1 | 0.76 | 5473 | 3 | 4 | | | IV-2 | RFC2 | 0.77 |
| 5378 | 3 | 4 | | | IV-2 | PYCR2 | 0.82 | 5474 | 3 | 4 | | | IV-2 | RFNG | 0.76 |
| 5379 | 3 | 4 | | | IV-2 | PYGB | 0.85 | 5475 | 3 | 4 | | | IV-2 | RFTN2 | 0.78 |
| 5380 | 3 | 4 | | | IV-2 | PYGO2 | 0.68 | 5476 | 3 | 4 | | | IV-2 | RFX5 | 0.68 |
| 5381 | 3 | 4 | | | IV-2 | QPCTL | 0.68 | 5477 | 3 | 4 | | | IV-2 | RFX7 | 0.93 |
| 5382 | 3 | 4 | | | IV-2 | QTRTD1 | 0.98 | 5478 | 3 | 4 | | | IV-2 | RFX8 | 0.99 |
| 5383 | 3 | 4 | | | IV-2 | R3HDM1 | 0.85 | 5479 | 3 | 4 | | | IV-2 | RFXAP | 0.68 |
| 5384 | 3 | 4 | | | IV-2 | RAB13 | 0.81 | 5480 | 3 | 4 | | | IV-2 | RGMB | 0.73 |
| 5385 | 3 | 4 | | | IV-2 | RAB21 | 0.94 | 5481 | 3 | 4 | | | IV-2 | RGPD1 | 0.99 |
| 5386 | 3 | 4 | | | IV-2 | RAB22A | 0.90 | 5482 | 3 | 4 | | | IV-2 | RGS19 | 0.82 |
| 5387 | 3 | 4 | | | IV-2 | RAB24 | 0.94 | 5483 | 3 | 4 | | | IV-2 | RHBDD2 | 0.71 |
| 5388 | 3 | 4 | | | IV-2 | RAB28 | 0.83 | 5484 | 3 | 4 | | | IV-2 | RHBDF2 | 0.72 |
| 5389 | 3 | 4 | | | IV-2 | RAB33B | 0.83 | 5485 | 3 | 4 | | | IV-2 | RHEB | 0.80 |
| 5390 | 3 | 4 | | | IV-2 | RAB40B | 0.98 | 5486 | 3 | 4 | | | IV-2 | RHEBL1 | 0.75 |
| 5391 | 3 | 4 | | | IV-2 | RAB6A | 0.83 | 5487 | 3 | 4 | | | IV-2 | RHOA | 0.71 |
| 5392 | 3 | 4 | | | IV-2 | RAB6B | 0.77 | 5488 | 3 | 4 | | | IV-2 | RHOU | 0.79 |
| 5393 | 3 | 4 | | | IV-2 | RAB7A | 0.69 | 5489 | 3 | 4 | | | IV-2 | RIC8B | 0.77 |
| 5394 | 3 | 4 | | | IV-2 | RAB7L1 | 0.87 | 5490 | 3 | 4 | | | IV-2 | RICTOR | 0.89 |
| 5395 | 3 | 4 | | | IV-2 | RAB8A | 0.67 | 5491 | 3 | 4 | | | IV-2 | RIF1 | 0.77 |
| 5396 | 3 | 4 | | | IV-2 | RAB8B | 0.93 | 5492 | 3 | 4 | | | IV-2 | RIN2 | 0.76 |
| 5397 | 3 | 4 | | | IV-2 | RABAC1 | 0.68 | 5493 | 3 | 4 | | | IV-2 | RIOK1 | 0.95 |
| 5398 | 3 | 4 | | | IV-2 | RABEP2 | 0.69 | 5494 | 3 | 4 | | | IV-2 | RIOK2 | 0.87 |
| 5399 | 3 | 4 | | | IV-2 | RABGAP1 | 0.99 | 5495 | 3 | 4 | | | IV-2 | RIPK1 | 0.68 |
| 5400 | 3 | 4 | | | IV-2 | RABGAP1L | 0.89 | 5496 | 3 | 4 | | | IV-2 | RIT1 | 0.93 |
| 5401 | 3 | 4 | | | IV-2 | RABGEF1 | 0.79 | 5497 | 3 | 4 | | | IV-2 | RNASE13 | 0.95 |
| 5402 | 3 | 4 | | | IV-2 | RABL3 | 0.94 | 5498 | 3 | 4 | | | IV-2 | RNASEH1 | 0.73 |
| 5403 | 3 | 4 | | | IV-2 | RABL5 | 0.76 | 5499 | 3 | 4 | | | IV-2 | RNASEH2B | 0.70 |
| 5404 | 3 | 4 | | | IV-2 | RAD1 | 0.94 | 5500 | 3 | 4 | | | IV-2 | RNASEK | 0.78 |
| 5405 | 3 | 4 | | | IV-2 | RAD18 | 0.92 | 5501 | 3 | 4 | | | IV-2 | RNASET2 | 1.00 |
| 5406 | 3 | 4 | | | IV-2 | RAD51B | 0.91 | 5502 | 3 | 4 | | | IV-2 | RND2 | 0.77 |
| 5407 | 3 | 4 | | | IV-2 | RAD51C | 0.99 | 5503 | 3 | 4 | | | IV-2 | RNF11 | 0.98 |
| 5408 | 3 | 4 | | | IV-2 | RAE1 | 0.96 | 5504 | 3 | 4 | | | IV-2 | RNF113A | 0.78 |
| 5409 | 3 | 4 | | | IV-2 | RAF1 | 0.71 | 5505 | 3 | 4 | | | IV-2 | RNF114 | 0.81 |
| 5410 | 3 | 4 | | | IV-2 | RALA | 0.87 | 5506 | 3 | 4 | | | IV-2 | RNF123 | 0.70 |
| 5411 | 3 | 4 | | | IV-2 | RALGAPA2 | 0.85 | 5507 | 3 | 4 | | | IV-2 | RNF126 | 0.68 |
| 5412 | 3 | 4 | | | IV-2 | RALGAPB | 0.97 | 5508 | 3 | 4 | | | IV-2 | RNF13 | 0.96 |
| 5413 | 3 | 4 | | | IV-2 | RALGPS1 | 0.98 | 5509 | 3 | 4 | | | IV-2 | RNF130 | 0.86 |
| 5414 | 3 | 4 | | | IV-2 | RAMP2 | 0.70 | 5510 | 3 | 4 | | | IV-2 | RNF138 | 0.94 |
| 5415 | 3 | 4 | | | IV-2 | RAMP3 | 0.79 | 5511 | 3 | 4 | | | IV-2 | RNF141 | 0.90 |
| 5416 | 3 | 4 | | | IV-2 | RAN | 0.83 | 5512 | 3 | 4 | | | IV-2 | RNF145 | 0.71 |
| 5417 | 3 | 4 | | | IV-2 | RANBP1 | 0.77 | 5513 | 3 | 4 | | | IV-2 | RNF181 | 0.99 |
| 5418 | 3 | 4 | | | IV-2 | RANBP6 | 0.96 | 5514 | 3 | 4 | | | IV-2 | RNF185 | 0.75 |
| 5419 | 3 | 4 | | | IV-2 | RANBP9 | 0.82 | 5515 | 3 | 4 | | | IV-2 | RNF19A | 0.87 |
| 5420 | 3 | 4 | | | IV-2 | RANGAP1 | 0.73 | 5516 | 3 | 4 | | | IV-2 | RNF208 | 0.82 |
| 5421 | 3 | 4 | | | IV-2 | RAP1A | 0.93 | 5517 | 3 | 4 | | | IV-2 | RNF216P1 | 0.80 |
| 5422 | 3 | 4 | | | IV-2 | RAP1B | 0.91 | 5518 | 3 | 4 | | | IV-2 | RNF25 | 0.88 |
| 5423 | 3 | 4 | | | IV-2 | RAP1GDS1 | 0.95 | 5519 | 3 | 4 | | | IV-2 | RNF32 | 0.94 |
| 5424 | 3 | 4 | | | IV-2 | RAPH1 | 0.72 | 5520 | 3 | 4 | | | IV-2 | RNF34 | 0.82 |
| 5425 | 3 | 4 | | | IV-2 | RARS | 0.89 | 5521 | 3 | 4 | | | IV-2 | RNF38 | 0.79 |
| 5426 | 3 | 4 | | | IV-2 | RARS2 | 0.83 | 5522 | 3 | 4 | | | IV-2 | RNF41 | 0.79 |
| 5427 | 3 | 4 | | | IV-2 | RASA1 | 0.93 | 5523 | 3 | 4 | | | IV-2 | RNF44 | 0.76 |
| 5428 | 3 | 4 | | | IV-2 | RASD1 | 0.78 | 5524 | 3 | 4 | | | IV-2 | RNF5P1 | 0.71 |
| 5429 | 3 | 4 | | | IV-2 | RASD2 | 0.98 | 5525 | 3 | 4 | | | IV-2 | RNF8 | 0.87 |
| 5430 | 3 | 4 | | | IV-2 | RASGEF1B | 0.79 | 5526 | 3 | 4 | | | IV-2 | RNGTT | 0.84 |
| 5431 | 3 | 4 | | | IV-2 | RASGRF2 | 0.99 | 5527 | 3 | 4 | | | IV-2 | RNPEP | 0.81 |
| 5432 | 3 | 4 | | | IV-2 | RASL11A | 0.77 | 5528 | 3 | 4 | | | IV-2 | ROBO1 | 0.91 |
| 5433 | 3 | 4 | | | IV-2 | RASSF3 | 0.88 | 5529 | 3 | 4 | | | IV-2 | ROGDI | 0.93 |
| 5434 | 3 | 4 | | | IV-2 | RASSF7 | 0.74 | 5530 | 3 | 4 | | | IV-2 | ROM1 | 0.71 |
| 5435 | 3 | 4 | | | IV-2 | RAVER2 | 0.96 | 5531 | 3 | 4 | | | IV-2 | RP2 | 0.87 |
| 5436 | 3 | 4 | | | IV-2 | RAX | 0.89 | 5532 | 3 | 4 | | | IV-2 | RPA1 | 0.75 |
| 5437 | 3 | 4 | | | IV-2 | RBBP7 | 0.86 | 5533 | 3 | 4 | | | IV-2 | RPA2 | 0.86 |
| 5438 | 3 | 4 | | | IV-2 | RBBP9 | 0.80 | 5534 | 3 | 4 | | | IV-2 | RPAP2 | 0.90 |
| 5439 | 3 | 4 | | | IV-2 | RBFA | 0.69 | 5535 | 3 | 4 | | | IV-2 | RPAP3 | 0.83 |
| 5440 | 3 | 4 | | | IV-2 | RBL2 | 0.90 | 5536 | 3 | 4 | | | IV-2 | RPE | 0.99 |
| 5441 | 3 | 4 | | | IV-2 | RBM14-RBM4 | 0.69 | 5537 | 3 | 4 | | | IV-2 | RPF1 | 0.99 |
| 5442 | 3 | 4 | | | IV-2 | RBM17 | 0.92 | 5538 | 3 | 4 | | | IV-2 | RPL10 | 0.88 |
| 5443 | 3 | 4 | | | IV-2 | RBM22 | 0.80 | 5539 | 3 | 4 | | | IV-2 | RPL11 | 0.95 |
| 5444 | 3 | 4 | | | IV-2 | RBM23 | 0.77 | 5540 | 3 | 4 | | | IV-2 | RPL13AP20 | 0.79 |
| 5445 | 3 | 4 | | | IV-2 | RBM26 | 0.81 | 5541 | 3 | 4 | | | IV-2 | RPL15 | 0.95 |
| 5446 | 3 | 4 | | | IV-2 | RBM27 | 0.87 | 5542 | 3 | 4 | | | IV-2 | RPL17 | 0.93 |
| 5447 | 3 | 4 | | | IV-2 | RBM3 | 0.80 | 5543 | 3 | 4 | | | IV-2 | RPL17-C18ORF32 | 0.98 |
| 5448 | 3 | 4 | | | IV-2 | RBM33 | 0.76 | 5544 | 3 | 4 | | | IV-2 | RPL19 | 0.84 |
| 5449 | 3 | 4 | | | IV-2 | RBM38 | 0.69 | 5545 | 3 | 4 | | | IV-2 | RPL19P12 | 0.98 |
| 5450 | 3 | 4 | | | IV-2 | RBM4 | 0.87 | 5546 | 3 | 4 | | | IV-2 | RPL23AP7 | 0.89 |
| 5451 | 3 | 4 | | | IV-2 | RBM4B | 0.96 | 5547 | 3 | 4 | | | IV-2 | RPL24 | 0.95 |
| 5452 | 3 | 4 | | | IV-2 | RBM5 | 0.90 | 5548 | 3 | 4 | | | IV-2 | RPL26L1 | 0.99 |
| 5453 | 3 | 4 | | | IV-2 | RBMX | 0.77 | 5549 | 3 | 4 | | | IV-2 | RPL27 | 0.93 |
| 5454 | 3 | 4 | | | IV-2 | RBMXL1 | 0.79 | 5550 | 3 | 4 | | | IV-2 | RPL27A | 0.73 |
| 5455 | 3 | 4 | | | IV-2 | RC3H1 | 0.83 | 5551 | 3 | 4 | | | IV-2 | RPL28 | 0.73 |
| 5456 | 3 | 4 | | | IV-2 | RCBTB1 | 0.93 | 5552 | 3 | 4 | | | IV-2 | RPL29 | 0.68 |
| 5457 | 3 | 4 | | | IV-2 | RCCD1 | 0.93 | 5553 | 3 | 4 | | | IV-2 | RPL36A-HNRNPH2 | 0.76 |
| 5458 | 3 | 4 | | | IV-2 | RCN2 | 0.93 | 5554 | 3 | 4 | | | IV-2 | RPL37A | 0.90 |
| 5459 | 3 | 4 | | | IV-2 | RDBP | 0.73 | 5555 | 3 | 4 | | | IV-2 | RPL39L | 0.72 |
| 5460 | 3 | 4 | | | IV-2 | RDH13 | 0.84 | 5556 | 3 | 4 | | | IV-2 | RPL4 | 0.82 |
| 5461 | 3 | 4 | | | IV-2 | RDH14 | 0.78 | 5557 | 3 | 4 | | | IV-2 | RPL6 | 0.70 |
| 5462 | 3 | 4 | | | IV-2 | REEP3 | 0.99 | 5558 | 3 | 4 | | | IV-2 | RPL7A | 0.81 |
| 5463 | 3 | 4 | | | IV-2 | REL | 0.96 | 5559 | 3 | 4 | | | IV-2 | RPN2 | 0.94 |
| 5464 | 3 | 4 | | | IV-2 | RELL1 | 0.71 | 5560 | 3 | 4 | | | IV-2 | RPP38 | 0.90 |
| 5465 | 3 | 4 | | | IV-2 | RELL2 | 0.94 | 5561 | 3 | 4 | | | IV-2 | RPP40 | 0.86 |
| 5466 | 3 | 4 | | | IV-2 | REPIN1 | 0.84 | 5562 | 3 | 4 | | | IV-2 | RPRD1B | 0.80 |
| 5467 | 3 | 4 | | | IV-2 | REPS1 | 0.78 | 5563 | 3 | 4 | | | IV-2 | RPRD2 | 0.68 |
| 5468 | 3 | 4 | | | IV-2 | RER1 | 0.90 | 5564 | 3 | 4 | | | IV-2 | RPRM | 0.92 |
| 5469 | 3 | 4 | | | IV-2 | RET | 0.90 | 5565 | 3 | 4 | | | IV-2 | RPS11 | 0.85 |

Fig. 39 - 30

| | | | | | | | |
|---|---|---|---|---|---|---|---|
| 5566 | 3 | 4 | | | IV-2 | RPS13 | 0.85 |
| 5567 | 3 | 4 | | | IV-2 | RPS15 | 0.76 |
| 5568 | 3 | 4 | | | IV-2 | RPS16 | 0.86 |
| 5569 | 3 | 4 | | | IV-2 | RPS17 | 0.78 |
| 5570 | 3 | 4 | | | IV-2 | RPS17L | 0.76 |
| 5571 | 3 | 4 | | | IV-2 | RPS19 | 0.92 |
| 5572 | 3 | 4 | | | IV-2 | RPS20 | 0.85 |
| 5573 | 3 | 4 | | | IV-2 | RPS23 | 0.87 |
| 5574 | 3 | 4 | | | IV-2 | RPS6 | 0.88 |
| 5575 | 3 | 4 | | | IV-2 | RPS6KA1 | 0.70 |
| 5576 | 3 | 4 | | | IV-2 | RPS6KA3 | 0.71 |
| 5577 | 3 | 4 | | | IV-2 | RPS6KB1 | 0.99 |
| 5578 | 3 | 4 | | | IV-2 | RPS6KB2 | 0.70 |
| 5579 | 3 | 4 | | | IV-2 | RPS6KC1 | 0.68 |
| 5580 | 3 | 4 | | | IV-2 | RPS7 | 0.85 |
| 5581 | 3 | 4 | | | IV-2 | RPS8 | 0.96 |
| 5582 | 3 | 4 | | | IV-2 | RPS9 | 0.82 |
| 5583 | 3 | 4 | | | IV-2 | RPUSD3 | 0.80 |
| 5584 | 3 | 4 | | | IV-2 | RRAGA | 0.83 |
| 5585 | 3 | 4 | | | IV-2 | RRAGB | 0.97 |
| 5586 | 3 | 4 | | | IV-2 | RREB1 | 0.69 |
| 5587 | 3 | 4 | | | IV-2 | RRM2B | 0.85 |
| 5588 | 3 | 4 | | | IV-2 | RRN3 | 0.96 |
| 5589 | 3 | 4 | | | IV-2 | RRN3P2 | 0.88 |
| 5590 | 3 | 4 | | | IV-2 | RRNAD1 | 0.71 |
| 5591 | 3 | 4 | | | IV-2 | RRP15 | 0.94 |
| 5592 | 3 | 4 | | | IV-2 | RRP36 | 0.78 |
| 5593 | 3 | 4 | | | IV-2 | RRP8 | 0.73 |
| 5594 | 3 | 4 | | | IV-2 | RSBN1 | 0.91 |
| 5595 | 3 | 4 | | | IV-2 | RSC1A1 | 0.88 |
| 5596 | 3 | 4 | | | IV-2 | RSL1D1 | 0.83 |
| 5597 | 3 | 4 | | | IV-2 | RSRC1 | 0.88 |
| 5598 | 3 | 4 | | | IV-2 | RTCD1 | 0.77 |
| 5599 | 3 | 4 | | | IV-2 | RTN4 | 0.85 |
| 5600 | 3 | 4 | | | IV-2 | RUFY1 | 0.81 |
| 5601 | 3 | 4 | | | IV-2 | RUNDC3A | 0.76 |
| 5602 | 3 | 4 | | | IV-2 | RUNX1 | 0.99 |
| 5603 | 3 | 4 | | | IV-2 | RUNX1T1 | 0.71 |
| 5604 | 3 | 4 | | | IV-2 | RUNX3 | 0.86 |
| 5605 | 3 | 4 | | | IV-2 | RUSC1-AS1 | 0.75 |
| 5606 | 3 | 4 | | | IV-2 | RUVBL1 | 0.71 |
| 5607 | 3 | 4 | | | IV-2 | RWDD2B | 0.75 |
| 5608 | 3 | 4 | | | IV-2 | RYBP | 0.95 |
| 5609 | 3 | 4 | | | IV-2 | RYR1 | 0.97 |
| 5610 | 3 | 4 | | | IV-2 | S100PBP | 1.00 |
| 5611 | 3 | 4 | | | IV-2 | SAAL1 | 0.85 |
| 5612 | 3 | 4 | | | IV-2 | SACS | 0.96 |
| 5613 | 3 | 4 | | | IV-2 | SAMD9 | 0.91 |
| 5614 | 3 | 4 | | | IV-2 | SAMD9L | 0.68 |
| 5615 | 3 | 4 | | | IV-2 | SAMM50 | 0.90 |
| 5616 | 3 | 4 | | | IV-2 | SAP18 | 0.77 |
| 5617 | 3 | 4 | | | IV-2 | SAR1A | 0.96 |
| 5618 | 3 | 4 | | | IV-2 | SART3 | 0.72 |
| 5619 | 3 | 4 | | | IV-2 | SAV1 | 0.73 |
| 5620 | 3 | 4 | | | IV-2 | SAYSD1 | 0.92 |
| 5621 | 3 | 4 | | | IV-2 | SBDS | 0.84 |
| 5622 | 3 | 4 | | | IV-2 | SBF2 | 0.77 |
| 5623 | 3 | 4 | | | IV-2 | SCAF11 | 0.99 |
| 5624 | 3 | 4 | | | IV-2 | SCAMP1 | 0.97 |
| 5625 | 3 | 4 | | | IV-2 | SCAMP4 | 0.67 |
| 5626 | 3 | 4 | | | IV-2 | SCARB2 | 0.94 |
| 5627 | 3 | 4 | | | IV-2 | SCHIP1 | 0.93 |
| 5628 | 3 | 4 | | | IV-2 | SCMH1 | 0.80 |
| 5629 | 3 | 4 | | | IV-2 | SCNN1G | 0.74 |
| 5630 | 3 | 4 | | | IV-2 | SCO2 | 0.71 |
| 5631 | 3 | 4 | | | IV-2 | SCRIB | 0.67 |
| 5632 | 3 | 4 | | | IV-2 | SCRN1 | 0.73 |
| 5633 | 3 | 4 | | | IV-2 | SDAD1 | 0.74 |
| 5634 | 3 | 4 | | | IV-2 | SDCBP | 0.84 |
| 5635 | 3 | 4 | | | IV-2 | SDCCAG3 | 0.71 |
| 5636 | 3 | 4 | | | IV-2 | SDF2 | 0.99 |
| 5637 | 3 | 4 | | | IV-2 | SDF4 | 0.68 |
| 5638 | 3 | 4 | | | IV-2 | SDHA | 0.90 |
| 5639 | 3 | 4 | | | IV-2 | SDHAF1 | 0.74 |
| 5640 | 3 | 4 | | | IV-2 | SDHAP3 | 0.75 |
| 5641 | 3 | 4 | | | IV-2 | SEC11A | 0.98 |
| 5642 | 3 | 4 | | | IV-2 | SEC13 | 0.68 |
| 5643 | 3 | 4 | | | IV-2 | SEC22A | 0.90 |
| 5644 | 3 | 4 | | | IV-2 | SEC22C | 0.81 |
| 5645 | 3 | 4 | | | IV-2 | SEC23IP | 0.88 |
| 5646 | 3 | 4 | | | IV-2 | SEC31A | 0.77 |
| 5647 | 3 | 4 | | | IV-2 | SEC61A1 | 0.73 |
| 5648 | 3 | 4 | | | IV-2 | SEC63 | 0.96 |
| 5649 | 3 | 4 | | | IV-2 | SELM | 0.80 |
| 5650 | 3 | 4 | | | IV-2 | SELRC1 | 0.82 |
| 5651 | 3 | 4 | | | IV-2 | SEMA3C | 0.96 |
| 5652 | 3 | 4 | | | IV-2 | SEMA3G | 0.88 |
| 5653 | 3 | 4 | | | IV-2 | SEMA4B | 0.78 |
| 5654 | 3 | 4 | | | IV-2 | SEMA4G | 0.71 |
| 5655 | 3 | 4 | | | IV-2 | SEMA5A | 0.91 |
| 5656 | 3 | 4 | | | IV-2 | SEMA6A | 0.79 |
| 5657 | 3 | 4 | | | IV-2 | SEMA6D | 0.99 |
| 5658 | 3 | 4 | | | IV-2 | SENP1 | 0.84 |
| 5659 | 3 | 4 | | | IV-2 | SENP2 | 0.91 |
| 5660 | 3 | 4 | | | IV-2 | SEP15 | 0.95 |
| 5661 | 3 | 4 | | | IV-2 | SEPHS1 | 0.73 |
| 5662 | 3 | 4 | | | IV-2 | SEPT10 | 0.80 |
| 5663 | 3 | 4 | | | IV-2 | SERF1B | 0.97 |
| 5664 | 3 | 4 | | | IV-2 | SERF2 | 0.96 |
| 5665 | 3 | 4 | | | IV-2 | SERINC1 | 0.88 |
| 5666 | 3 | 4 | | | IV-2 | SERPINA11 | 0.90 |
| 5667 | 3 | 4 | | | IV-2 | SERPINB1 | 0.79 |
| 5668 | 3 | 4 | | | IV-2 | SERPINB6 | 0.89 |
| 5669 | 3 | 4 | | | IV-2 | SERPINB9 | 0.77 |
| 5670 | 3 | 4 | | | IV-2 | SERPINF2 | 0.69 |
| 5671 | 3 | 4 | | | IV-2 | SERTAD2 | 0.79 |
| 5672 | 3 | 4 | | | IV-2 | SERTAD3 | 0.92 |
| 5673 | 3 | 4 | | | IV-2 | SESN1 | 0.96 |
| 5674 | 3 | 4 | | | IV-2 | SESN2 | 0.86 |
| 5675 | 3 | 4 | | | IV-2 | SET | 0.92 |
| 5676 | 3 | 4 | | | IV-2 | SETD3 | 0.92 |
| 5677 | 3 | 4 | | | IV-2 | SETD5 | 0.89 |
| 5678 | 3 | 4 | | | IV-2 | SETD7 | 0.94 |
| 5679 | 3 | 4 | | | IV-2 | SETD8 | 0.77 |
| 5680 | 3 | 4 | | | IV-2 | SETX | 0.74 |
| 5681 | 3 | 4 | | | IV-2 | SEZ6L | 1.00 |
| 5682 | 3 | 4 | | | IV-2 | SF1 | 0.71 |
| 5683 | 3 | 4 | | | IV-2 | SFMBT1 | 0.89 |
| 5684 | 3 | 4 | | | IV-2 | SFT2D3 | 0.76 |
| 5685 | 3 | 4 | | | IV-2 | SFXN5 | 0.86 |
| 5686 | 3 | 4 | | | IV-2 | SGCB | 0.81 |
| 5687 | 3 | 4 | | | IV-2 | SGK3 | 0.77 |
| 5688 | 3 | 4 | | | IV-2 | SGSM3 | 0.71 |
| 5689 | 3 | 4 | | | IV-2 | SGTB | 0.91 |
| 5690 | 3 | 4 | | | IV-2 | SH2B1 | 0.70 |
| 5691 | 3 | 4 | | | IV-2 | SH3BGRL | 0.92 |
| 5692 | 3 | 4 | | | IV-2 | SH3BP5 | 0.75 |
| 5693 | 3 | 4 | | | IV-2 | SH3D19 | 0.69 |
| 5694 | 3 | 4 | | | IV-2 | SH3D21 | 0.73 |
| 5695 | 3 | 4 | | | IV-2 | SH3GLB1 | 0.92 |
| 5696 | 3 | 4 | | | IV-2 | SH3GLB2 | 0.71 |
| 5697 | 3 | 4 | | | IV-2 | SH3RF1 | 0.77 |
| 5698 | 3 | 4 | | | IV-2 | SHARPIN | 0.76 |
| 5699 | 3 | 4 | | | IV-2 | SHISA6 | 0.80 |
| 5700 | 3 | 4 | | | IV-2 | SHKBP1 | 0.74 |
| 5701 | 3 | 4 | | | IV-2 | SHMT1 | 0.98 |
| 5702 | 3 | 4 | | | IV-2 | SHOC2 | 0.85 |
| 5703 | 3 | 4 | | | IV-2 | SHOX2 | 0.71 |
| 5704 | 3 | 4 | | | IV-2 | SIAH1 | 0.74 |
| 5705 | 3 | 4 | | | IV-2 | SIGLECP3 | 0.97 |
| 5706 | 3 | 4 | | | IV-2 | SIKE1 | 0.98 |
| 5707 | 3 | 4 | | | IV-2 | SIL1 | 0.94 |
| 5708 | 3 | 4 | | | IV-2 | SIPA1L2 | 0.99 |
| 5709 | 3 | 4 | | | IV-2 | SIRT1 | 0.96 |
| 5710 | 3 | 4 | | | IV-2 | SIRT7 | 0.75 |
| 5711 | 3 | 4 | | | IV-2 | SIVA1 | 0.89 |
| 5712 | 3 | 4 | | | IV-2 | SIX2 | 0.97 |
| 5713 | 3 | 4 | | | IV-2 | SKA2 | 0.79 |
| 5714 | 3 | 4 | | | IV-2 | SKA3 | 0.91 |
| 5715 | 3 | 4 | | | IV-2 | SKP2 | 0.80 |
| 5716 | 3 | 4 | | | IV-2 | SLA | 0.96 |
| 5717 | 3 | 4 | | | IV-2 | SLAIN1 | 0.74 |
| 5718 | 3 | 4 | | | IV-2 | SLBP | 0.88 |
| 5719 | 3 | 4 | | | IV-2 | SLC10A7 | 0.93 |
| 5720 | 3 | 4 | | | IV-2 | SLC15A3 | 0.68 |
| 5721 | 3 | 4 | | | IV-2 | SLC15A4 | 0.77 |
| 5722 | 3 | 4 | | | IV-2 | SLC16A1 | 0.77 |
| 5723 | 3 | 4 | | | IV-2 | SLC1A1 | 0.91 |
| 5724 | 3 | 4 | | | IV-2 | SLC1A2 | 0.93 |
| 5725 | 3 | 4 | | | IV-2 | SLC1A7 | 0.93 |
| 5726 | 3 | 4 | | | IV-2 | SLC22A15 | 0.90 |
| 5727 | 3 | 4 | | | IV-2 | SLC22A3 | 0.95 |
| 5728 | 3 | 4 | | | IV-2 | SLC24A1 | 0.91 |
| 5729 | 3 | 4 | | | IV-2 | SLC24A5 | 0.74 |
| 5730 | 3 | 4 | | | IV-2 | SLC24A6 | 0.74 |
| 5731 | 3 | 4 | | | IV-2 | SLC25A10 | 0.94 |
| 5732 | 3 | 4 | | | IV-2 | SLC25A12 | 0.95 |
| 5733 | 3 | 4 | | | IV-2 | SLC25A19 | 0.76 |
| 5734 | 3 | 4 | | | IV-2 | SLC25A22 | 0.76 |
| 5735 | 3 | 4 | | | IV-2 | SLC25A24 | 0.78 |
| 5736 | 3 | 4 | | | IV-2 | SLC25A26 | 0.73 |
| 5737 | 3 | 4 | | | IV-2 | SLC25A32 | 0.69 |
| 5738 | 3 | 4 | | | IV-2 | SLC25A34 | 0.92 |
| 5739 | 3 | 4 | | | IV-2 | SLC25A39 | 0.74 |
| 5740 | 3 | 4 | | | IV-2 | SLC25A42 | 0.89 |
| 5741 | 3 | 4 | | | IV-2 | SLC25A44 | 0.71 |
| 5742 | 3 | 4 | | | IV-2 | SLC25A46 | 0.97 |
| 5743 | 3 | 4 | | | IV-2 | SLC27A1 | 0.69 |
| 5744 | 3 | 4 | | | IV-2 | SLC2A8 | 0.82 |
| 5745 | 3 | 4 | | | IV-2 | SLC30A6 | 0.88 |
| 5746 | 3 | 4 | | | IV-2 | SLC30A9 | 0.97 |
| 5747 | 3 | 4 | | | IV-2 | SLC33A1 | 0.82 |
| 5748 | 3 | 4 | | | IV-2 | SLC35A5 | 0.86 |
| 5749 | 3 | 4 | | | IV-2 | SLC35B2 | 0.84 |
| 5750 | 3 | 4 | | | IV-2 | SLC35B3 | 0.97 |
| 5751 | 3 | 4 | | | IV-2 | SLC35B4 | 0.82 |
| 5752 | 3 | 4 | | | IV-2 | SLC35C2 | 0.73 |
| 5753 | 3 | 4 | | | IV-2 | SLC35D2 | 0.76 |
| 5754 | 3 | 4 | | | IV-2 | SLC35E2 | 0.96 |
| 5755 | 3 | 4 | | | IV-2 | SLC37A1 | 0.68 |
| 5756 | 3 | 4 | | | IV-2 | SLC37A4 | 0.74 |
| 5757 | 3 | 4 | | | IV-2 | SLC38A10 | 0.67 |

Fig. 39 - 31

| | | | | | | | |
|---|---|---|---|---|---|---|---|
| 5758 | 3 | 4 | | | IV-2 | SLC38A2 | 0.90 |
| 5759 | 3 | 4 | | | IV-2 | SLC38A9 | 0.92 |
| 5760 | 3 | 4 | | | IV-2 | SLC39A10 | 0.92 |
| 5761 | 3 | 4 | | | IV-2 | SLC39A14 | 0.68 |
| 5762 | 3 | 4 | | | IV-2 | SLC39A7 | 0.68 |
| 5763 | 3 | 4 | | | IV-2 | SLC41A2 | 1.00 |
| 5764 | 3 | 4 | | | IV-2 | SLC41A3 | 0.77 |
| 5765 | 3 | 4 | | | IV-2 | SLC43A1 | 0.74 |
| 5766 | 3 | 4 | | | IV-2 | SLC44A1 | 0.88 |
| 5767 | 3 | 4 | | | IV-2 | SLC44A2 | 0.75 |
| 5768 | 3 | 4 | | | IV-2 | SLC45A1 | 0.73 |
| 5769 | 3 | 4 | | | IV-2 | SLC47A1 | 0.87 |
| 5770 | 3 | 4 | | | IV-2 | SLC48A1 | 0.72 |
| 5771 | 3 | 4 | | | IV-2 | SLC4A1AP | 0.70 |
| 5772 | 3 | 4 | | | IV-2 | SLC6A1 | 0.91 |
| 5773 | 3 | 4 | | | IV-2 | SLC6A15 | 0.97 |
| 5774 | 3 | 4 | | | IV-2 | SLC6A8 | 0.73 |
| 5775 | 3 | 4 | | | IV-2 | SLC7A2 | 0.77 |
| 5776 | 3 | 4 | | | IV-2 | SLC7A7 | 0.72 |
| 5777 | 3 | 4 | | | IV-2 | SLC8A1 | 0.80 |
| 5778 | 3 | 4 | | | IV-2 | SLC9A5 | 0.90 |
| 5779 | 3 | 4 | | | IV-2 | SLC9A6 | 0.81 |
| 5780 | 3 | 4 | | | IV-2 | SLCO2A1 | 0.77 |
| 5781 | 3 | 4 | | | IV-2 | SLFN5 | 0.70 |
| 5782 | 3 | 4 | | | IV-2 | SLIT2 | 0.69 |
| 5783 | 3 | 4 | | | IV-2 | SLITRK2 | 0.74 |
| 5784 | 3 | 4 | | | IV-2 | SLMAP | 0.93 |
| 5785 | 3 | 4 | | | IV-2 | SMAD2 | 0.88 |
| 5786 | 3 | 4 | | | IV-2 | SMAD4 | 0.81 |
| 5787 | 3 | 4 | | | IV-2 | SMAD5-AS1 | 0.83 |
| 5788 | 3 | 4 | | | IV-2 | SMARCA2 | 0.70 |
| 5789 | 3 | 4 | | | IV-2 | SMARCA5 | 0.88 |
| 5790 | 3 | 4 | | | IV-2 | SMARCD2 | 0.86 |
| 5791 | 3 | 4 | | | IV-2 | SMARCE1 | 0.85 |
| 5792 | 3 | 4 | | | IV-2 | SMC2 | 0.85 |
| 5793 | 3 | 4 | | | IV-2 | SMC5 | 0.71 |
| 5794 | 3 | 4 | | | IV-2 | SMCHD1 | 0.95 |
| 5795 | 3 | 4 | | | IV-2 | SMCR7 | 0.77 |
| 5796 | 3 | 4 | | | IV-2 | SMCR7L | 0.76 |
| 5797 | 3 | 4 | | | IV-2 | SMEK1 | 0.79 |
| 5798 | 3 | 4 | | | IV-2 | SMEK2 | 0.85 |
| 5799 | 3 | 4 | | | IV-2 | SMG9 | 0.92 |
| 5800 | 3 | 4 | | | IV-2 | SMNDC1 | 0.93 |
| 5801 | 3 | 4 | | | IV-2 | SMPDL3B | 0.99 |
| 5802 | 3 | 4 | | | IV-2 | SMYD2 | 0.93 |
| 5803 | 3 | 4 | | | IV-2 | SMYD4 | 0.78 |
| 5804 | 3 | 4 | | | IV-2 | SNAI2 | 0.82 |
| 5805 | 3 | 4 | | | IV-2 | SNAI3 | 0.86 |
| 5806 | 3 | 4 | | | IV-2 | SNAP23 | 0.74 |
| 5807 | 3 | 4 | | | IV-2 | SNAPC1 | 0.89 |
| 5808 | 3 | 4 | | | IV-2 | SNAPC5 | 0.75 |
| 5809 | 3 | 4 | | | IV-2 | SNAPIN | 0.99 |
| 5810 | 3 | 4 | | | IV-2 | SNIP1 | 0.83 |
| 5811 | 3 | 4 | | | IV-2 | SNORA74A | 0.95 |
| 5812 | 3 | 4 | | | IV-2 | SNRNP27 | 0.88 |
| 5813 | 3 | 4 | | | IV-2 | SNRNP48 | 0.99 |
| 5814 | 3 | 4 | | | IV-2 | SNRPB | 0.81 |
| 5815 | 3 | 4 | | | IV-2 | SNRPC | 0.85 |
| 5816 | 3 | 4 | | | IV-2 | SNRPD3 | 0.77 |
| 5817 | 3 | 4 | | | IV-2 | SNRPF | 0.82 |
| 5818 | 3 | 4 | | | IV-2 | SNUPN | 0.82 |
| 5819 | 3 | 4 | | | IV-2 | SNX1 | 0.79 |
| 5820 | 3 | 4 | | | IV-2 | SNX16 | 0.75 |
| 5821 | 3 | 4 | | | IV-2 | SNX17 | 0.87 |
| 5822 | 3 | 4 | | | IV-2 | SNX18 | 0.73 |
| 5823 | 3 | 4 | | | IV-2 | SNX19 | 0.86 |
| 5824 | 3 | 4 | | | IV-2 | SNX2 | 0.68 |
| 5825 | 3 | 4 | | | IV-2 | SNX22 | 0.68 |
| 5826 | 3 | 4 | | | IV-2 | SNX24 | 0.89 |
| 5827 | 3 | 4 | | | IV-2 | SNX29P2 | 0.99 |
| 5828 | 3 | 4 | | | IV-2 | SNX6 | 0.91 |
| 5829 | 3 | 4 | | | IV-2 | SNX7 | 0.68 |
| 5830 | 3 | 4 | | | IV-2 | SOCS5 | 0.76 |
| 5831 | 3 | 4 | | | IV-2 | SOCS6 | 0.85 |
| 5832 | 3 | 4 | | | IV-2 | SOD2 | 0.99 |
| 5833 | 3 | 4 | | | IV-2 | SOS1 | 0.90 |
| 5834 | 3 | 4 | | | IV-2 | SOS2 | 0.74 |
| 5835 | 3 | 4 | | | IV-2 | SOX13 | 0.78 |
| 5836 | 3 | 4 | | | IV-2 | SP1 | 0.68 |
| 5837 | 3 | 4 | | | IV-2 | SP3 | 0.75 |
| 5838 | 3 | 4 | | | IV-2 | SPAG5 | 0.76 |
| 5839 | 3 | 4 | | | IV-2 | SPAG8 | 0.86 |
| 5840 | 3 | 4 | | | IV-2 | SPARCL1 | 0.74 |
| 5841 | 3 | 4 | | | IV-2 | SPATA25 | 0.88 |
| 5842 | 3 | 4 | | | IV-2 | SPATA5 | 0.97 |
| 5843 | 3 | 4 | | | IV-2 | SPDYE2 | 0.95 |
| 5844 | 3 | 4 | | | IV-2 | SPDYE6 | 0.95 |
| 5845 | 3 | 4 | | | IV-2 | SPECC1L | 0.71 |
| 5846 | 3 | 4 | | | IV-2 | SPEF2 | 0.99 |
| 5847 | 3 | 4 | | | IV-2 | SPG20 | 0.82 |
| 5848 | 3 | 4 | | | IV-2 | SPHK1 | 0.85 |
| 5849 | 3 | 4 | | | IV-2 | SPHK2 | 0.74 |
| 5850 | 3 | 4 | | | IV-2 | SPINK1 | 0.94 |
| 5851 | 3 | 4 | | | IV-2 | SPNS2 | 0.92 |
| 5852 | 3 | 4 | | | IV-2 | SPOCK1 | 0.84 |
| 5853 | 3 | 4 | | | IV-2 | SPOP | 0.81 |
| 5854 | 3 | 4 | | | IV-2 | SPRED1 | 0.81 |
| 5855 | 3 | 4 | | | IV-2 | SPTBN1 | 0.67 |
| 5856 | 3 | 4 | | | IV-2 | SPTBN5 | 0.96 |
| 5857 | 3 | 4 | | | IV-2 | SPTY2D1 | 0.96 |
| 5858 | 3 | 4 | | | IV-2 | SQSTM1 | 0.78 |
| 5859 | 3 | 4 | | | IV-2 | SRGAP3 | 0.90 |
| 5860 | 3 | 4 | | | IV-2 | SRI | 0.87 |
| 5861 | 3 | 4 | | | IV-2 | SRL | 0.76 |
| 5862 | 3 | 4 | | | IV-2 | SRM | 0.77 |
| 5863 | 3 | 4 | | | IV-2 | SRP19 | 0.82 |
| 5864 | 3 | 4 | | | IV-2 | SRP68 | 0.95 |
| 5865 | 3 | 4 | | | IV-2 | SRPK3 | 0.96 |
| 5866 | 3 | 4 | | | IV-2 | SRPRB | 0.82 |
| 5867 | 3 | 4 | | | IV-2 | SRR | 0.80 |
| 5868 | 3 | 4 | | | IV-2 | SRRD | 0.85 |
| 5869 | 3 | 4 | | | IV-2 | SRRM1 | 0.82 |
| 5870 | 3 | 4 | | | IV-2 | SRSF1 | 0.92 |
| 5871 | 3 | 4 | | | IV-2 | SRSF3 | 0.83 |
| 5872 | 3 | 4 | | | IV-2 | SRSF9 | 0.82 |
| 5873 | 3 | 4 | | | IV-2 | SS18 | 0.96 |
| 5874 | 3 | 4 | | | IV-2 | SSBP2 | 0.87 |
| 5875 | 3 | 4 | | | IV-2 | SSBP3 | 0.68 |
| 5876 | 3 | 4 | | | IV-2 | SSH2 | 0.76 |
| 5877 | 3 | 4 | | | IV-2 | SSR1 | 0.90 |
| 5878 | 3 | 4 | | | IV-2 | SSR4 | 0.82 |
| 5879 | 3 | 4 | | | IV-2 | SSTR1 | 0.97 |
| 5880 | 3 | 4 | | | IV-2 | SSX2IP | 0.80 |
| 5881 | 3 | 4 | | | IV-2 | ST13 | 0.88 |
| 5882 | 3 | 4 | | | IV-2 | ST13P4 | 0.69 |
| 5883 | 3 | 4 | | | IV-2 | ST3GAL1 | 0.68 |
| 5884 | 3 | 4 | | | IV-2 | ST3GAL3 | 0.80 |
| 5885 | 3 | 4 | | | IV-2 | ST3GAL4 | 0.80 |
| 5886 | 3 | 4 | | | IV-2 | ST3GAL5 | 0.93 |
| 5887 | 3 | 4 | | | IV-2 | ST6GALNAC1 | 0.96 |
| 5888 | 3 | 4 | | | IV-2 | ST6GALNAC3 | 0.75 |
| 5889 | 3 | 4 | | | IV-2 | ST7-AS1 | 0.83 |
| 5890 | 3 | 4 | | | IV-2 | ST8SIA4 | 0.82 |
| 5891 | 3 | 4 | | | IV-2 | STAC | 0.69 |
| 5892 | 3 | 4 | | | IV-2 | STAG1 | 0.77 |
| 5893 | 3 | 4 | | | IV-2 | STAM | 0.79 |
| 5894 | 3 | 4 | | | IV-2 | STAM2 | 0.88 |
| 5895 | 3 | 4 | | | IV-2 | STAMBP | 1.00 |
| 5896 | 3 | 4 | | | IV-2 | STARD13 | 0.88 |
| 5897 | 3 | 4 | | | IV-2 | STARD3 | 0.71 |
| 5898 | 3 | 4 | | | IV-2 | STARD3NL | 0.82 |
| 5899 | 3 | 4 | | | IV-2 | STARD5 | 0.88 |
| 5900 | 3 | 4 | | | IV-2 | STAT2 | 0.67 |
| 5901 | 3 | 4 | | | IV-2 | STAT5A | 0.69 |
| 5902 | 3 | 4 | | | IV-2 | STIL | 0.98 |
| 5903 | 3 | 4 | | | IV-2 | STIM2 | 0.74 |
| 5904 | 3 | 4 | | | IV-2 | STK19 | 0.98 |
| 5905 | 3 | 4 | | | IV-2 | STK38 | 0.98 |
| 5906 | 3 | 4 | | | IV-2 | STK4 | 0.69 |
| 5907 | 3 | 4 | | | IV-2 | STOM | 0.72 |
| 5908 | 3 | 4 | | | IV-2 | STOML1 | 0.75 |
| 5909 | 3 | 4 | | | IV-2 | STOX1 | 0.99 |
| 5910 | 3 | 4 | | | IV-2 | STRA13 | 0.69 |
| 5911 | 3 | 4 | | | IV-2 | STRN | 0.98 |
| 5912 | 3 | 4 | | | IV-2 | STT3A | 0.88 |
| 5913 | 3 | 4 | | | IV-2 | STX10 | 0.80 |
| 5914 | 3 | 4 | | | IV-2 | STX18 | 0.95 |
| 5915 | 3 | 4 | | | IV-2 | STX3 | 0.90 |
| 5916 | 3 | 4 | | | IV-2 | STX4 | 0.74 |
| 5917 | 3 | 4 | | | IV-2 | STX5 | 0.72 |
| 5918 | 3 | 4 | | | IV-2 | STX7 | 0.98 |
| 5919 | 3 | 4 | | | IV-2 | STX8 | 0.69 |
| 5920 | 3 | 4 | | | IV-2 | STXBP3 | 0.88 |
| 5921 | 3 | 4 | | | IV-2 | STXBP5 | 0.99 |
| 5922 | 3 | 4 | | | IV-2 | STYX | 0.73 |
| 5923 | 3 | 4 | | | IV-2 | SUDS3 | 0.90 |
| 5924 | 3 | 4 | | | IV-2 | SUGP1 | 0.67 |
| 5925 | 3 | 4 | | | IV-2 | SUGT1 | 0.75 |
| 5926 | 3 | 4 | | | IV-2 | SUMF2 | 0.83 |
| 5927 | 3 | 4 | | | IV-2 | SUMO1P3 | 0.78 |
| 5928 | 3 | 4 | | | IV-2 | SUMO3 | 0.76 |
| 5929 | 3 | 4 | | | IV-2 | SUOX | 0.99 |
| 5930 | 3 | 4 | | | IV-2 | SUPT16H | 0.73 |
| 5931 | 3 | 4 | | | IV-2 | SUPT4H1 | 0.74 |
| 5932 | 3 | 4 | | | IV-2 | SURF1 | 0.75 |
| 5933 | 3 | 4 | | | IV-2 | SURF6 | 0.77 |
| 5934 | 3 | 4 | | | IV-2 | SV2A | 0.98 |
| 5935 | 3 | 4 | | | IV-2 | SWAP70 | 0.94 |
| 5936 | 3 | 4 | | | IV-2 | SWI5 | 0.87 |
| 5937 | 3 | 4 | | | IV-2 | SYAP1 | 0.75 |
| 5938 | 3 | 4 | | | IV-2 | SYCE3 | 1.00 |
| 5939 | 3 | 4 | | | IV-2 | SYF2 | 0.88 |
| 5940 | 3 | 4 | | | IV-2 | SYN1 | 0.98 |
| 5941 | 3 | 4 | | | IV-2 | SYNC | 0.76 |
| 5942 | 3 | 4 | | | IV-2 | SYNCRIP | 0.80 |
| 5943 | 3 | 4 | | | IV-2 | SYNRG | 0.88 |
| 5944 | 3 | 4 | | | IV-2 | SYP | 0.72 |
| 5945 | 3 | 4 | | | IV-2 | SYS1 | 0.86 |
| 5946 | 3 | 4 | | | IV-2 | SYT11 | 0.71 |
| 5947 | 3 | 4 | | | IV-2 | SYT7 | 0.92 |
| 5948 | 3 | 4 | | | IV-2 | SYTL1 | 0.91 |
| 5949 | 3 | 4 | | | IV-2 | TACO1 | 0.72 |

Fig. 39 - 32

| | | | | | | | | | | | | | | |
|---|---|---|---|---|---|---|---|---|---|---|---|---|---|---|
| 5950 | 3 | 4 | | | IV-2 | TAF1 | 0.83 | 6046 | 3 | 4 | | | IV-2 | TMED10 | 0.98 |
| 5951 | 3 | 4 | | | IV-2 | TAF10 | 0.82 | 6047 | 3 | 4 | | | IV-2 | TMED4 | 0.87 |
| 5952 | 3 | 4 | | | IV-2 | TAF1D | 0.97 | 6048 | 3 | 4 | | | IV-2 | TMED6 | 0.97 |
| 5953 | 3 | 4 | | | IV-2 | TAF1L | 0.90 | 6049 | 3 | 4 | | | IV-2 | TMEM106C | 0.78 |
| 5954 | 3 | 4 | | | IV-2 | TAF2 | 0.80 | 6050 | 3 | 4 | | | IV-2 | TMEM11 | 0.75 |
| 5955 | 3 | 4 | | | IV-2 | TAF6L | 0.87 | 6051 | 3 | 4 | | | IV-2 | TMEM129 | 0.79 |
| 5956 | 3 | 4 | | | IV-2 | TAF8 | 0.75 | 6052 | 3 | 4 | | | IV-2 | TMEM131 | 0.77 |
| 5957 | 3 | 4 | | | IV-2 | TAF9B | 0.87 | 6053 | 3 | 4 | | | IV-2 | TMEM132C | 0.75 |
| 5958 | 3 | 4 | | | IV-2 | TAL1 | 0.76 | 6054 | 3 | 4 | | | IV-2 | TMEM132E | 0.91 |
| 5959 | 3 | 4 | | | IV-2 | TAMM41 | 0.70 | 6055 | 3 | 4 | | | IV-2 | TMEM133 | 0.68 |
| 5960 | 3 | 4 | | | IV-2 | TANK | 0.97 | 6056 | 3 | 4 | | | IV-2 | TMEM134 | 0.76 |
| 5961 | 3 | 4 | | | IV-2 | TAPT1 | 0.93 | 6057 | 3 | 4 | | | IV-2 | TMEM141 | 0.79 |
| 5962 | 3 | 4 | | | IV-2 | TARBP2 | 0.74 | 6058 | 3 | 4 | | | IV-2 | TMEM150C | 0.82 |
| 5963 | 3 | 4 | | | IV-2 | TARDBP | 0.78 | 6059 | 3 | 4 | | | IV-2 | TMEM161A | 0.84 |
| 5964 | 3 | 4 | | | IV-2 | TATDN1 | 0.68 | 6060 | 3 | 4 | | | IV-2 | TMEM170A | 0.95 |
| 5965 | 3 | 4 | | | IV-2 | TBC1D12 | 0.97 | 6061 | 3 | 4 | | | IV-2 | TMEM171 | 0.94 |
| 5966 | 3 | 4 | | | IV-2 | TBC1D13 | 0.76 | 6062 | 3 | 4 | | | IV-2 | TMEM176A | 0.69 |
| 5967 | 3 | 4 | | | IV-2 | TBC1D15 | 0.77 | 6063 | 3 | 4 | | | IV-2 | TMEM176B | 0.75 |
| 5968 | 3 | 4 | | | IV-2 | TBC1D17 | 0.70 | 6064 | 3 | 4 | | | IV-2 | TMEM18 | 0.91 |
| 5969 | 3 | 4 | | | IV-2 | TBC1D22A | 0.73 | 6065 | 3 | 4 | | | IV-2 | TMEM184C | 0.81 |
| 5970 | 3 | 4 | | | IV-2 | TBC1D5 | 0.76 | 6066 | 3 | 4 | | | IV-2 | TMEM185A | 0.68 |
| 5971 | 3 | 4 | | | IV-2 | TBCEL | 0.72 | 6067 | 3 | 4 | | | IV-2 | TMEM185B | 0.69 |
| 5972 | 3 | 4 | | | IV-2 | TBCK | 0.78 | 6068 | 3 | 4 | | | IV-2 | TMEM199 | 0.81 |
| 5973 | 3 | 4 | | | IV-2 | TBK1 | 0.88 | 6069 | 3 | 4 | | | IV-2 | TMEM200A | 0.73 |
| 5974 | 3 | 4 | | | IV-2 | TBK8P1 | 0.76 | 6070 | 3 | 4 | | | IV-2 | TMEM203 | 0.90 |
| 5975 | 3 | 4 | | | IV-2 | TBL1XR1 | 0.95 | 6071 | 3 | 4 | | | IV-2 | TMEM204 | 0.80 |
| 5976 | 3 | 4 | | | IV-2 | TBL2 | 0.72 | 6072 | 3 | 4 | | | IV-2 | TMEM205 | 0.85 |
| 5977 | 3 | 4 | | | IV-2 | TBP | 0.80 | 6073 | 3 | 4 | | | IV-2 | TMEM206 | 0.84 |
| 5978 | 3 | 4 | | | IV-2 | TBRG1 | 0.88 | 6074 | 3 | 4 | | | IV-2 | TMEM209 | 0.80 |
| 5979 | 3 | 4 | | | IV-2 | TBX18 | 0.79 | 6075 | 3 | 4 | | | IV-2 | TMEM216 | 0.87 |
| 5980 | 3 | 4 | | | IV-2 | TBX2 | 0.68 | 6076 | 3 | 4 | | | IV-2 | TMEM217 | 0.96 |
| 5981 | 3 | 4 | | | IV-2 | TBX3 | 0.80 | 6077 | 3 | 4 | | | IV-2 | TMEM222 | 0.79 |
| 5982 | 3 | 4 | | | IV-2 | TBXA2R | 0.77 | 6078 | 3 | 4 | | | IV-2 | TMEM223 | 0.67 |
| 5983 | 3 | 4 | | | IV-2 | TCEA3 | 0.91 | 6079 | 3 | 4 | | | IV-2 | TMEM242 | 0.71 |
| 5984 | 3 | 4 | | | IV-2 | TCEAL2 | 0.77 | 6080 | 3 | 4 | | | IV-2 | TMEM39A | 0.72 |
| 5985 | 3 | 4 | | | IV-2 | TCEAL7 | 0.95 | 6081 | 3 | 4 | | | IV-2 | TMEM42 | 0.97 |
| 5986 | 3 | 4 | | | IV-2 | TCEAL8 | 0.84 | 6082 | 3 | 4 | | | IV-2 | TMEM48 | 0.94 |
| 5987 | 3 | 4 | | | IV-2 | TCEB1 | 1.00 | 6083 | 3 | 4 | | | IV-2 | TMEM5 | 0.78 |
| 5988 | 3 | 4 | | | IV-2 | TCEB2 | 0.82 | 6084 | 3 | 4 | | | IV-2 | TMEM50A | 0.82 |
| 5989 | 3 | 4 | | | IV-2 | TCF25 | 0.74 | 6085 | 3 | 4 | | | IV-2 | TMEM53 | 0.81 |
| 5990 | 3 | 4 | | | IV-2 | TCF7L2 | 0.77 | 6086 | 3 | 4 | | | IV-2 | TMEM55B | 0.79 |
| 5991 | 3 | 4 | | | IV-2 | TCFL5 | 0.68 | 6087 | 3 | 4 | | | IV-2 | TMEM57 | 0.91 |
| 5992 | 3 | 4 | | | IV-2 | TCHP | 0.68 | 6088 | 3 | 4 | | | IV-2 | TMEM65 | 0.80 |
| 5993 | 3 | 4 | | | IV-2 | TCP1 | 0.92 | 6089 | 3 | 4 | | | IV-2 | TMEM68 | 0.99 |
| 5994 | 3 | 4 | | | IV-2 | TCTEX1D1 | 0.95 | 6090 | 3 | 4 | | | IV-2 | TMEM69 | 0.97 |
| 5995 | 3 | 4 | | | IV-2 | TCTN1 | 0.81 | 6091 | 3 | 4 | | | IV-2 | TMEM79 | 0.84 |
| 5996 | 3 | 4 | | | IV-2 | TCTN3 | 0.85 | 6092 | 3 | 4 | | | IV-2 | TMEM80 | 0.92 |
| 5997 | 3 | 4 | | | IV-2 | TDRD3 | 0.78 | 6093 | 3 | 4 | | | IV-2 | TMEM85 | 0.90 |
| 5998 | 3 | 4 | | | IV-2 | TDRKH | 0.95 | 6094 | 3 | 4 | | | IV-2 | TMEM8A | 0.73 |
| 5999 | 3 | 4 | | | IV-2 | TEAD3 | 0.68 | 6095 | 3 | 4 | | | IV-2 | TMEM88 | 0.71 |
| 6000 | 3 | 4 | | | IV-2 | TEP1 | 0.98 | 6096 | 3 | 4 | | | IV-2 | TMEM9 | 0.83 |
| 6001 | 3 | 4 | | | IV-2 | TERF1 | 0.93 | 6097 | 3 | 4 | | | IV-2 | TMEM98 | 0.90 |
| 6002 | 3 | 4 | | | IV-2 | TERF2 | 0.90 | 6098 | 3 | 4 | | | IV-2 | TMIE | 0.94 |
| 6003 | 3 | 4 | | | IV-2 | TERF2IP | 0.77 | 6099 | 3 | 4 | | | IV-2 | TMPO | 0.69 |
| 6004 | 3 | 4 | | | IV-2 | TET2 | 0.84 | 6100 | 3 | 4 | | | IV-2 | TMPRSS6 | 0.70 |
| 6005 | 3 | 4 | | | IV-2 | TEX261 | 0.72 | 6101 | 3 | 4 | | | IV-2 | TMTC2 | 0.74 |
| 6006 | 3 | 4 | | | IV-2 | TFAM | 0.94 | 6102 | 3 | 4 | | | IV-2 | TMTC3 | 0.88 |
| 6007 | 3 | 4 | | | IV-2 | TFAP2A | 0.75 | 6103 | 3 | 4 | | | IV-2 | TMU82 | 0.72 |
| 6008 | 3 | 4 | | | IV-2 | TFB2M | 0.87 | 6104 | 3 | 4 | | | IV-2 | TNFAIP8 | 0.69 |
| 6009 | 3 | 4 | | | IV-2 | TFCP2 | 0.93 | 6105 | 3 | 4 | | | IV-2 | TNFRSF10D | 0.97 |
| 6010 | 3 | 4 | | | IV-2 | TFDP1 | 0.81 | 6106 | 3 | 4 | | | IV-2 | TNFRSF4 | 0.98 |
| 6011 | 3 | 4 | | | IV-2 | TFDP2 | 0.95 | 6107 | 3 | 4 | | | IV-2 | TNFSF10 | 0.94 |
| 6012 | 3 | 4 | | | IV-2 | TFG | 0.76 | 6108 | 3 | 4 | | | IV-2 | TNFSF13 | 0.95 |
| 6013 | 3 | 4 | | | IV-2 | TFR2 | 1.00 | 6109 | 3 | 4 | | | IV-2 | TNFSF8 | 0.86 |
| 6014 | 3 | 4 | | | IV-2 | TGFBR1 | 0.97 | 6110 | 3 | 4 | | | IV-2 | TNKS2 | 0.90 |
| 6015 | 3 | 4 | | | IV-2 | TGS1 | 0.69 | 6111 | 3 | 4 | | | IV-2 | TNPO1 | 0.95 |
| 6016 | 3 | 4 | | | IV-2 | TH1L | 0.92 | 6112 | 3 | 4 | | | IV-2 | TNPO2 | 0.73 |
| 6017 | 3 | 4 | | | IV-2 | THADA | 0.76 | 6113 | 3 | 4 | | | IV-2 | TNPO3 | 0.84 |
| 6018 | 3 | 4 | | | IV-2 | THAP1 | 0.85 | 6114 | 3 | 4 | | | IV-2 | TOMM34 | 0.69 |
| 6019 | 3 | 4 | | | IV-2 | THOC7 | 0.90 | 6115 | 3 | 4 | | | IV-2 | TOMM40 | 0.70 |
| 6020 | 3 | 4 | | | IV-2 | THUMPD3 | 0.92 | 6116 | 3 | 4 | | | IV-2 | TOMM40L | 0.88 |
| 6021 | 3 | 4 | | | IV-2 | TIAF1 | 0.75 | 6117 | 3 | 4 | | | IV-2 | TOP2A | 0.85 |
| 6022 | 3 | 4 | | | IV-2 | TIAL1 | 0.81 | 6118 | 3 | 4 | | | IV-2 | TOP2B | 0.95 |
| 6023 | 3 | 4 | | | IV-2 | TIGD1 | 0.96 | 6119 | 3 | 4 | | | IV-2 | TOPORS | 0.97 |
| 6024 | 3 | 4 | | | IV-2 | TIGD6 | 0.85 | 6120 | 3 | 4 | | | IV-2 | TOR1A | 0.69 |
| 6025 | 3 | 4 | | | IV-2 | TIGD7 | 0.79 | 6121 | 3 | 4 | | | IV-2 | TOR1AIP1 | 0.93 |
| 6026 | 3 | 4 | | | IV-2 | TIMM17B | 0.68 | 6122 | 3 | 4 | | | IV-2 | TOR1AIP2 | 0.99 |
| 6027 | 3 | 4 | | | IV-2 | TIMM22 | 0.70 | 6123 | 3 | 4 | | | IV-2 | TOR1B | 0.83 |
| 6028 | 3 | 4 | | | IV-2 | TIMM44 | 0.77 | 6124 | 3 | 4 | | | IV-2 | TOR2A | 0.86 |
| 6029 | 3 | 4 | | | IV-2 | TIPRL | 0.88 | 6125 | 3 | 4 | | | IV-2 | TOX | 0.90 |
| 6030 | 3 | 4 | | | IV-2 | TJP1 | 0.79 | 6126 | 3 | 4 | | | IV-2 | TOX4 | 0.74 |
| 6031 | 3 | 4 | | | IV-2 | TJP2 | 0.94 | 6127 | 3 | 4 | | | IV-2 | TP53I13 | 0.70 |
| 6032 | 3 | 4 | | | IV-2 | TK1 | 0.78 | 6128 | 3 | 4 | | | IV-2 | TP53INP1 | 0.89 |
| 6033 | 3 | 4 | | | IV-2 | TK2 | 0.77 | 6129 | 3 | 4 | | | IV-2 | TP53TG1 | 0.95 |
| 6034 | 3 | 4 | | | IV-2 | TLK1 | 0.94 | 6130 | 3 | 4 | | | IV-2 | TP73-AS1 | 0.70 |
| 6035 | 3 | 4 | | | IV-2 | TLK2 | 0.90 | 6131 | 3 | 4 | | | IV-2 | TPBG | 0.68 |
| 6036 | 3 | 4 | | | IV-2 | TLL1 | 1.00 | 6132 | 3 | 4 | | | IV-2 | TPD52L2 | 0.82 |
| 6037 | 3 | 4 | | | IV-2 | TLR9 | 0.86 | 6133 | 3 | 4 | | | IV-2 | TPGS1 | 0.70 |
| 6038 | 3 | 4 | | | IV-2 | TM2D1 | 0.84 | 6134 | 3 | 4 | | | IV-2 | TPI1 | 0.73 |
| 6039 | 3 | 4 | | | IV-2 | TM2D2 | 0.86 | 6135 | 3 | 4 | | | IV-2 | TPI1P3 | 0.94 |
| 6040 | 3 | 4 | | | IV-2 | TM4SF1 | 0.96 | 6136 | 3 | 4 | | | IV-2 | TPK1 | 0.87 |
| 6041 | 3 | 4 | | | IV-2 | TM7SF3 | 0.81 | 6137 | 3 | 4 | | | IV-2 | TPR | 0.68 |
| 6042 | 3 | 4 | | | IV-2 | TMCC1 | 0.83 | 6138 | 3 | 4 | | | IV-2 | TPRA1 | 0.71 |
| 6043 | 3 | 4 | | | IV-2 | TMCO3 | 0.88 | 6139 | 3 | 4 | | | IV-2 | TPST1 | 0.68 |
| 6044 | 3 | 4 | | | IV-2 | TMCO6 | 0.79 | 6140 | 3 | 4 | | | IV-2 | TPT1 | 0.83 |
| 6045 | 3 | 4 | | | IV-2 | TMED1 | 0.81 | 6141 | 3 | 4 | | | IV-2 | TRA2B | 0.95 |

Fig. 39 - 33

| | | | | | | | | | | | | | | | |
|---|---|---|---|---|---|---|---|---|---|---|---|---|---|---|---|
| 6142 | 3 | 4 | | | IV-2 | TRADD | 0.76 | 6238 | 3 | 4 | | | IV-2 | UBP1 | 0.79 |
| 6143 | 3 | 4 | | | IV-2 | TRAF3IP1 | 0.87 | 6239 | 3 | 4 | | | IV-2 | UBR2 | 0.81 |
| 6144 | 3 | 4 | | | IV-2 | TRAF6 | 0.89 | 6240 | 3 | 4 | | | IV-2 | UBR7 | 0.86 |
| 6145 | 3 | 4 | | | IV-2 | TRAIP | 0.80 | 6241 | 3 | 4 | | | IV-2 | UBTD2 | 0.79 |
| 6146 | 3 | 4 | | | IV-2 | TRAPPC10 | 0.68 | 6242 | 3 | 4 | | | IV-2 | UBXN10 | 0.73 |
| 6147 | 3 | 4 | | | IV-2 | TRAPPC3 | 0.88 | 6243 | 3 | 4 | | | IV-2 | UCK1 | 0.88 |
| 6148 | 3 | 4 | | | IV-2 | TRAPPC6A | 0.89 | 6244 | 3 | 4 | | | IV-2 | UCKL1-AS1 | 0.99 |
| 6149 | 3 | 4 | | | IV-2 | TRIB2 | 0.96 | 6245 | 3 | 4 | | | IV-2 | UFC1 | 0.87 |
| 6150 | 3 | 4 | | | IV-2 | TRIM11 | 0.82 | 6246 | 3 | 4 | | | IV-2 | UFD1L | 0.73 |
| 6151 | 3 | 4 | | | IV-2 | TRIM16L | 0.78 | 6247 | 3 | 4 | | | IV-2 | UFL1 | 0.94 |
| 6152 | 3 | 4 | | | IV-2 | TRIM22 | 0.99 | 6248 | 3 | 4 | | | IV-2 | UFM1 | 0.90 |
| 6153 | 3 | 4 | | | IV-2 | TRIM27 | 0.81 | 6249 | 3 | 4 | | | IV-2 | UGGT1 | 0.97 |
| 6154 | 3 | 4 | | | IV-2 | TRIM34 | 0.98 | 6250 | 3 | 4 | | | IV-2 | UHRF1BP1L | 0.90 |
| 6155 | 3 | 4 | | | IV-2 | TRIM37 | 0.71 | 6251 | 3 | 4 | | | IV-2 | ULK1 | 0.70 |
| 6156 | 3 | 4 | | | IV-2 | TRIM59 | 0.86 | 6252 | 3 | 4 | | | IV-2 | ULK2 | 1.00 |
| 6157 | 3 | 4 | | | IV-2 | TRIM6 | 0.95 | 6253 | 3 | 4 | | | IV-2 | UMPS | 0.83 |
| 6158 | 3 | 4 | | | IV-2 | TRIM66 | 0.83 | 6254 | 3 | 4 | | | IV-2 | UNC119 | 0.84 |
| 6159 | 3 | 4 | | | IV-2 | TRIM7 | 0.79 | 6255 | 3 | 4 | | | IV-2 | UNC13B | 0.78 |
| 6160 | 3 | 4 | | | IV-2 | TRIM74 | 1.00 | 6256 | 3 | 4 | | | IV-2 | UNC93B1 | 0.74 |
| 6161 | 3 | 4 | | | IV-2 | TRIP13 | 0.93 | 6257 | 3 | 4 | | | IV-2 | UNKL | 0.79 |
| 6162 | 3 | 4 | | | IV-2 | TRMT112 | 0.92 | 6258 | 3 | 4 | | | IV-2 | UPF1 | 0.69 |
| 6163 | 3 | 4 | | | IV-2 | TRMT2B | 0.81 | 6259 | 3 | 4 | | | IV-2 | UPRT | 0.72 |
| 6164 | 3 | 4 | | | IV-2 | TRMT61B | 0.86 | 6260 | 3 | 4 | | | IV-2 | UQCR10 | 0.86 |
| 6165 | 3 | 4 | | | IV-2 | TRPC4AP | 0.76 | 6261 | 3 | 4 | | | IV-2 | URB1 | 0.77 |
| 6166 | 3 | 4 | | | IV-2 | TRPV4 | 0.92 | 6262 | 3 | 4 | | | IV-2 | UROD | 0.75 |
| 6167 | 3 | 4 | | | IV-2 | TRUB1 | 0.82 | 6263 | 3 | 4 | | | IV-2 | USE1 | 0.69 |
| 6168 | 3 | 4 | | | IV-2 | TRUB2 | 0.83 | 6264 | 3 | 4 | | | IV-2 | USP1 | 0.97 |
| 6169 | 3 | 4 | | | IV-2 | TSC22D4 | 0.70 | 6265 | 3 | 4 | | | IV-2 | USP10 | 0.72 |
| 6170 | 3 | 4 | | | IV-2 | TSEN15 | 0.90 | 6266 | 3 | 4 | | | IV-2 | USP12 | 0.99 |
| 6171 | 3 | 4 | | | IV-2 | TSFM | 0.81 | 6267 | 3 | 4 | | | IV-2 | USP15 | 0.83 |
| 6172 | 3 | 4 | | | IV-2 | TSG101 | 0.84 | 6268 | 3 | 4 | | | IV-2 | USP25 | 0.89 |
| 6173 | 3 | 4 | | | IV-2 | TSPAN12 | 0.95 | 6269 | 3 | 4 | | | IV-2 | USP27X | 0.85 |
| 6174 | 3 | 4 | | | IV-2 | TSPAN3 | 0.90 | 6270 | 3 | 4 | | | IV-2 | USP28 | 0.89 |
| 6175 | 3 | 4 | | | IV-2 | TSPO | 0.94 | 6271 | 3 | 4 | | | IV-2 | USP30 | 0.88 |
| 6176 | 3 | 4 | | | IV-2 | TSR1 | 0.95 | 6272 | 3 | 4 | | | IV-2 | USP31 | 0.75 |
| 6177 | 3 | 4 | | | IV-2 | TSR2 | 0.72 | 6273 | 3 | 4 | | | IV-2 | USP32 | 0.78 |
| 6178 | 3 | 4 | | | IV-2 | TSSC1 | 0.98 | 6274 | 3 | 4 | | | IV-2 | USP37 | 0.78 |
| 6179 | 3 | 4 | | | IV-2 | TSSK4 | 0.71 | 6275 | 3 | 4 | | | IV-2 | USP39 | 0.73 |
| 6180 | 3 | 4 | | | IV-2 | TSTA3 | 0.79 | 6276 | 3 | 4 | | | IV-2 | USP4 | 0.71 |
| 6181 | 3 | 4 | | | IV-2 | TSTD2 | 0.74 | 6277 | 3 | 4 | | | IV-2 | USP42 | 0.93 |
| 6182 | 3 | 4 | | | IV-2 | TTC1 | 0.92 | 6278 | 3 | 4 | | | IV-2 | USP47 | 0.88 |
| 6183 | 3 | 4 | | | IV-2 | TTC12 | 0.95 | 6279 | 3 | 4 | | | IV-2 | USP48 | 0.86 |
| 6184 | 3 | 4 | | | IV-2 | TTC21A | 0.92 | 6280 | 3 | 4 | | | IV-2 | USP54 | 0.67 |
| 6185 | 3 | 4 | | | IV-2 | TTC30B | 0.79 | 6281 | 3 | 4 | | | IV-2 | USP7 | 0.87 |
| 6186 | 3 | 4 | | | IV-2 | TTC31 | 0.74 | 6282 | 3 | 4 | | | IV-2 | USP9X | 0.82 |
| 6187 | 3 | 4 | | | IV-2 | TTC32 | 0.71 | 6283 | 3 | 4 | | | IV-2 | UTP20 | 0.77 |
| 6188 | 3 | 4 | | | IV-2 | TTC33 | 0.88 | 6284 | 3 | 4 | | | IV-2 | UTRN | 0.82 |
| 6189 | 3 | 4 | | | IV-2 | TTC4 | 0.71 | 6285 | 3 | 4 | | | IV-2 | UXS1 | 0.76 |
| 6190 | 3 | 4 | | | IV-2 | TTC5 | 0.73 | 6286 | 3 | 4 | | | IV-2 | VAMP3 | 0.89 |
| 6191 | 3 | 4 | | | IV-2 | TTC7B | 0.87 | 6287 | 3 | 4 | | | IV-2 | VAMP7 | 0.99 |
| 6192 | 3 | 4 | | | IV-2 | TTC8 | 0.95 | 6288 | 3 | 4 | | | IV-2 | VAPA | 0.93 |
| 6193 | 3 | 4 | | | IV-2 | TTC9C | 0.79 | 6289 | 3 | 4 | | | IV-2 | VAT1 | 0.70 |
| 6194 | 3 | 4 | | | IV-2 | TTF2 | 0.68 | 6290 | 3 | 4 | | | IV-2 | VAV1 | 0.97 |
| 6195 | 3 | 4 | | | IV-2 | TTL | 0.76 | 6291 | 3 | 4 | | | IV-2 | VAV3 | 0.90 |
| 6196 | 3 | 4 | | | IV-2 | TTLL1 | 0.87 | 6292 | 3 | 4 | | | IV-2 | VAX2 | 0.78 |
| 6197 | 3 | 4 | | | IV-2 | TUB | 0.77 | 6293 | 3 | 4 | | | IV-2 | VCPIP1 | 0.80 |
| 6198 | 3 | 4 | | | IV-2 | TUBG1 | 0.76 | 6294 | 3 | 4 | | | IV-2 | VDAC2 | 0.93 |
| 6199 | 3 | 4 | | | IV-2 | TUBGCP5 | 0.84 | 6295 | 3 | 4 | | | IV-2 | VDAC3 | 0.94 |
| 6200 | 3 | 4 | | | IV-2 | TUSC1 | 0.67 | 6296 | 3 | 4 | | | IV-2 | VEPH1 | 0.93 |
| 6201 | 3 | 4 | | | IV-2 | TUSC2 | 0.76 | 6297 | 3 | 4 | | | IV-2 | VEZF1 | 0.77 |
| 6202 | 3 | 4 | | | IV-2 | TUSC3 | 0.70 | 6298 | 3 | 4 | | | IV-2 | VGLL4 | 0.70 |
| 6203 | 3 | 4 | | | IV-2 | TXLNG | 0.96 | 6299 | 3 | 4 | | | IV-2 | VHL | 0.82 |
| 6204 | 3 | 4 | | | IV-2 | TXNDC11 | 0.72 | 6300 | 3 | 4 | | | IV-2 | VMA21 | 0.91 |
| 6205 | 3 | 4 | | | IV-2 | TXNDC12 | 0.92 | 6301 | 3 | 4 | | | IV-2 | VMO1 | 0.75 |
| 6206 | 3 | 4 | | | IV-2 | TXNDC15 | 0.73 | 6302 | 3 | 4 | | | IV-2 | VPS13B | 0.73 |
| 6207 | 3 | 4 | | | IV-2 | TXNDC17 | 0.90 | 6303 | 3 | 4 | | | IV-2 | VPS13C | 0.99 |
| 6208 | 3 | 4 | | | IV-2 | TXNDC5 | 0.80 | 6304 | 3 | 4 | | | IV-2 | VPS16 | 0.72 |
| 6209 | 3 | 4 | | | IV-2 | TXNIP | 0.76 | 6305 | 3 | 4 | | | IV-2 | VPS25 | 0.91 |
| 6210 | 3 | 4 | | | IV-2 | TXNRD1 | 0.92 | 6306 | 3 | 4 | | | IV-2 | VPS28 | 0.84 |
| 6211 | 3 | 4 | | | IV-2 | TXNRD3 | 0.98 | 6307 | 3 | 4 | | | IV-2 | VPS29 | 0.90 |
| 6212 | 3 | 4 | | | IV-2 | TYMP | 0.85 | 6308 | 3 | 4 | | | IV-2 | VPS4A | 0.73 |
| 6213 | 3 | 4 | | | IV-2 | TYR | 0.84 | 6309 | 3 | 4 | | | IV-2 | VPS52 | 0.69 |
| 6214 | 3 | 4 | | | IV-2 | TYW1 | 0.95 | 6310 | 3 | 4 | | | IV-2 | VPS53 | 0.94 |
| 6215 | 3 | 4 | | | IV-2 | TYW3 | 0.87 | 6311 | 3 | 4 | | | IV-2 | VRK1 | 0.96 |
| 6216 | 3 | 4 | | | IV-2 | UBA2 | 0.95 | 6312 | 3 | 4 | | | IV-2 | VRK3 | 0.69 |
| 6217 | 3 | 4 | | | IV-2 | UBA52 | 0.85 | 6313 | 3 | 4 | | | IV-2 | VSNL1 | 0.71 |
| 6218 | 3 | 4 | | | IV-2 | UBAC1 | 0.85 | 6314 | 3 | 4 | | | IV-2 | VWA1 | 0.83 |
| 6219 | 3 | 4 | | | IV-2 | UBB | 0.73 | 6315 | 3 | 4 | | | IV-2 | VWA7 | 0.97 |
| 6220 | 3 | 4 | | | IV-2 | UBE2D1 | 0.87 | 6316 | 3 | 4 | | | IV-2 | WAC | 0.98 |
| 6221 | 3 | 4 | | | IV-2 | UBE2E3 | 0.98 | 6317 | 3 | 4 | | | IV-2 | WAPAL | 0.78 |
| 6222 | 3 | 4 | | | IV-2 | UBE2G1 | 0.91 | 6318 | 3 | 4 | | | IV-2 | WARS | 0.74 |
| 6223 | 3 | 4 | | | IV-2 | UBE2G2 | 0.74 | 6319 | 3 | 4 | | | IV-2 | WBP2 | 0.77 |
| 6224 | 3 | 4 | | | IV-2 | UBE2H | 0.80 | 6320 | 3 | 4 | | | IV-2 | WDFY1 | 0.71 |
| 6225 | 3 | 4 | | | IV-2 | UBE2I | 0.84 | 6321 | 3 | 4 | | | IV-2 | WDFY3 | 0.95 |
| 6226 | 3 | 4 | | | IV-2 | UBE2J1 | 0.78 | 6322 | 3 | 4 | | | IV-2 | WDR13 | 0.80 |
| 6227 | 3 | 4 | | | IV-2 | UBE2J2 | 0.78 | 6323 | 3 | 4 | | | IV-2 | WDR20 | 0.74 |
| 6228 | 3 | 4 | | | IV-2 | UBE2L3 | 0.74 | 6324 | 3 | 4 | | | IV-2 | WDR27 | 0.88 |
| 6229 | 3 | 4 | | | IV-2 | UBE2N | 0.95 | 6325 | 3 | 4 | | | IV-2 | WDR33 | 0.95 |
| 6230 | 3 | 4 | | | IV-2 | UBE2Q1 | 0.78 | 6326 | 3 | 4 | | | IV-2 | WDR37 | 0.83 |
| 6231 | 3 | 4 | | | IV-2 | UBE2Q2P2 | 0.81 | 6327 | 3 | 4 | | | IV-2 | WDR44 | 0.91 |
| 6232 | 3 | 4 | | | IV-2 | UBE2R2 | 0.81 | 6328 | 3 | 4 | | | IV-2 | WDR45L | 0.94 |
| 6233 | 3 | 4 | | | IV-2 | UBE2V1 | 0.88 | 6329 | 3 | 4 | | | IV-2 | WDR48 | 0.84 |
| 6234 | 3 | 4 | | | IV-2 | UBE3B | 0.76 | 6330 | 3 | 4 | | | IV-2 | WDR5 | 0.69 |
| 6235 | 3 | 4 | | | IV-2 | UBE3C | 0.82 | 6331 | 3 | 4 | | | IV-2 | WDR53 | 0.95 |
| 6236 | 3 | 4 | | | IV-2 | UBL4A | 0.81 | 6332 | 3 | 4 | | | IV-2 | WDR7 | 0.95 |
| 6237 | 3 | 4 | | | IV-2 | UBN2 | 0.95 | 6333 | 3 | 4 | | | IV-2 | WDR73 | 0.93 |

Fig. 39 - 34

| | | | | | | | | | | | | | | |
|---|---|---|---|---|---|---|---|---|---|---|---|---|---|---|
| 6334 | 3 | 4 | | | IV-2 | WDR74 | 0.69 | 6430 | 3 | 4 | | | IV-2 | ZNF330 | 0.80 |
| 6335 | 3 | 4 | | | IV-2 | WDR76 | 0.79 | 6431 | 3 | 4 | | | IV-2 | ZNF331 | 0.79 |
| 6336 | 3 | 4 | | | IV-2 | WDR89 | 0.75 | 6432 | 3 | 4 | | | IV-2 | ZNF341 | 0.76 |
| 6337 | 3 | 4 | | | IV-2 | WHAMM | 0.80 | 6433 | 3 | 4 | | | IV-2 | ZNF343 | 0.72 |
| 6338 | 3 | 4 | | | IV-2 | WIBG | 0.83 | 6434 | 3 | 4 | | | IV-2 | ZNF346 | 0.74 |
| 6339 | 3 | 4 | | | IV-2 | WIPI2 | 0.91 | 6435 | 3 | 4 | | | IV-2 | ZNF385C | 0.90 |
| 6340 | 3 | 4 | | | IV-2 | WNT10B | 0.86 | 6436 | 3 | 4 | | | IV-2 | ZNF394 | 0.78 |
| 6341 | 3 | 4 | | | IV-2 | WNT5B | 0.85 | 6437 | 3 | 4 | | | IV-2 | ZNF395 | 0.71 |
| 6342 | 3 | 4 | | | IV-2 | WRAP53 | 0.78 | 6438 | 3 | 4 | | | IV-2 | ZNF397 | 0.72 |
| 6343 | 3 | 4 | | | IV-2 | WRN | 0.95 | 6439 | 3 | 4 | | | IV-2 | ZNF408 | 0.70 |
| 6344 | 3 | 4 | | | IV-2 | WRNIP1 | 0.74 | 6440 | 3 | 4 | | | IV-2 | ZNF41 | 0.81 |
| 6345 | 3 | 4 | | | IV-2 | WTAP | 0.93 | 6441 | 3 | 4 | | | IV-2 | ZNF414 | 0.72 |
| 6346 | 3 | 4 | | | IV-2 | WTIP | 0.72 | 6442 | 3 | 4 | | | IV-2 | ZNF425 | 0.80 |
| 6347 | 3 | 4 | | | IV-2 | WWC2 | 0.96 | 6443 | 3 | 4 | | | IV-2 | ZNF428 | 0.68 |
| 6348 | 3 | 4 | | | IV-2 | WWP1 | 0.75 | 6444 | 3 | 4 | | | IV-2 | ZNF434 | 0.89 |
| 6349 | 3 | 4 | | | IV-2 | WWP2 | 0.81 | 6445 | 3 | 4 | | | IV-2 | ZNF436 | 0.90 |
| 6350 | 3 | 4 | | | IV-2 | XKR8 | 0.97 | 6446 | 3 | 4 | | | IV-2 | ZNF444 | 0.71 |
| 6351 | 3 | 4 | | | IV-2 | XPO4 | 0.88 | 6447 | 3 | 4 | | | IV-2 | ZNF469 | 0.87 |
| 6352 | 3 | 4 | | | IV-2 | XPO5 | 0.74 | 6448 | 3 | 4 | | | IV-2 | ZNF470 | 0.94 |
| 6353 | 3 | 4 | | | IV-2 | XPO7 | 0.73 | 6449 | 3 | 4 | | | IV-2 | ZNF490 | 0.78 |
| 6354 | 3 | 4 | | | IV-2 | XPOT | 0.70 | 6450 | 3 | 4 | | | IV-2 | ZNF497 | 0.81 |
| 6355 | 3 | 4 | | | IV-2 | XPR1 | 0.81 | 6451 | 3 | 4 | | | IV-2 | ZNF500 | 0.77 |
| 6356 | 3 | 4 | | | IV-2 | XRCC5 | 0.97 | 6452 | 3 | 4 | | | IV-2 | ZNF503 | 0.77 |
| 6357 | 3 | 4 | | | IV-2 | YAF2 | 0.96 | 6453 | 3 | 4 | | | IV-2 | ZNF510 | 0.89 |
| 6358 | 3 | 4 | | | IV-2 | YAP1 | 0.76 | 6454 | 3 | 4 | | | IV-2 | ZNF511 | 0.80 |
| 6359 | 3 | 4 | | | IV-2 | YDJC | 0.73 | 6455 | 3 | 4 | | | IV-2 | ZNF512 | 0.92 |
| 6360 | 3 | 4 | | | IV-2 | YES1 | 0.95 | 6456 | 3 | 4 | | | IV-2 | ZNF517 | 0.72 |
| 6361 | 3 | 4 | | | IV-2 | YIF1A | 0.75 | 6457 | 3 | 4 | | | IV-2 | ZNF526 | 0.85 |
| 6362 | 3 | 4 | | | IV-2 | YPEL1 | 0.78 | 6458 | 3 | 4 | | | IV-2 | ZNF530 | 0.86 |
| 6363 | 3 | 4 | | | IV-2 | YPEL2 | 0.82 | 6459 | 3 | 4 | | | IV-2 | ZNF532 | 0.73 |
| 6364 | 3 | 4 | | | IV-2 | YPEL3 | 0.75 | 6460 | 3 | 4 | | | IV-2 | ZNF542 | 0.94 |
| 6365 | 3 | 4 | | | IV-2 | YTHDC1 | 0.88 | 6461 | 3 | 4 | | | IV-2 | ZNF543 | 0.75 |
| 6366 | 3 | 4 | | | IV-2 | YTHDF1 | 0.71 | 6462 | 3 | 4 | | | IV-2 | ZNF548 | 0.94 |
| 6367 | 3 | 4 | | | IV-2 | YTHDF3 | 0.91 | 6463 | 3 | 4 | | | IV-2 | ZNF551 | 0.91 |
| 6368 | 3 | 4 | | | IV-2 | YWHAE | 0.86 | 6464 | 3 | 4 | | | IV-2 | ZNF554 | 0.78 |
| 6369 | 3 | 4 | | | IV-2 | YWHAG | 0.80 | 6465 | 3 | 4 | | | IV-2 | ZNF569 | 0.84 |
| 6370 | 3 | 4 | | | IV-2 | YWHAQ | 0.89 | 6466 | 3 | 4 | | | IV-2 | ZNF576 | 0.68 |
| 6371 | 3 | 4 | | | IV-2 | ZAK | 0.95 | 6467 | 3 | 4 | | | IV-2 | ZNF579 | 0.91 |
| 6372 | 3 | 4 | | | IV-2 | ZBTB1 | 0.98 | 6468 | 3 | 4 | | | IV-2 | ZNF580 | 0.72 |
| 6373 | 3 | 4 | | | IV-2 | ZBTB3 | 0.86 | 6469 | 3 | 4 | | | IV-2 | ZNF583 | 0.70 |
| 6374 | 3 | 4 | | | IV-2 | ZBTB38 | 0.68 | 6470 | 3 | 4 | | | IV-2 | ZNF584 | 0.85 |
| 6375 | 3 | 4 | | | IV-2 | ZBTB43 | 0.93 | 6471 | 3 | 4 | | | IV-2 | ZNF585B | 0.87 |
| 6376 | 3 | 4 | | | IV-2 | ZC3H10 | 0.77 | 6472 | 3 | 4 | | | IV-2 | ZNF616 | 0.94 |
| 6377 | 3 | 4 | | | IV-2 | ZC3H11A | 0.88 | 6473 | 3 | 4 | | | IV-2 | ZNF618 | 0.84 |
| 6378 | 3 | 4 | | | IV-2 | ZC3H12C | 0.96 | 6474 | 3 | 4 | | | IV-2 | ZNF624 | 0.80 |
| 6379 | 3 | 4 | | | IV-2 | ZC3H14 | 0.96 | 6475 | 3 | 4 | | | IV-2 | ZNF639 | 0.68 |
| 6380 | 3 | 4 | | | IV-2 | ZC3HAV1 | 0.96 | 6476 | 3 | 4 | | | IV-2 | ZNF641 | 0.72 |
| 6381 | 3 | 4 | | | IV-2 | ZCCHC11 | 0.71 | 6477 | 3 | 4 | | | IV-2 | ZNF652 | 0.98 |
| 6382 | 3 | 4 | | | IV-2 | ZCCHC17 | 0.94 | 6478 | 3 | 4 | | | IV-2 | ZNF653 | 0.75 |
| 6383 | 3 | 4 | | | IV-2 | ZCCHC3 | 0.72 | 6479 | 3 | 4 | | | IV-2 | ZNF655 | 0.97 |
| 6384 | 3 | 4 | | | IV-2 | ZCCHC8 | 0.76 | 6480 | 3 | 4 | | | IV-2 | ZNF664 | 0.96 |
| 6385 | 3 | 4 | | | IV-2 | ZCCHC9 | 0.97 | 6481 | 3 | 4 | | | IV-2 | ZNF688 | 0.72 |
| 6386 | 3 | 4 | | | IV-2 | ZDHHC13 | 0.99 | 6482 | 3 | 4 | | | IV-2 | ZNF691 | 0.89 |
| 6387 | 3 | 4 | | | IV-2 | ZDHHC15 | 0.96 | 6483 | 3 | 4 | | | IV-2 | ZNF696 | 0.81 |
| 6388 | 3 | 4 | | | IV-2 | ZDHHC4 | 0.93 | 6484 | 3 | 4 | | | IV-2 | ZNF701 | 0.68 |
| 6389 | 3 | 4 | | | IV-2 | ZDHHC6 | 0.95 | 6485 | 3 | 4 | | | IV-2 | ZNF704 | 0.84 |
| 6390 | 3 | 4 | | | IV-2 | ZEB2 | 0.73 | 6486 | 3 | 4 | | | IV-2 | ZNF707 | 0.78 |
| 6391 | 3 | 4 | | | IV-2 | ZFAND1 | 0.97 | 6487 | 3 | 4 | | | IV-2 | ZNF720 | 0.83 |
| 6392 | 3 | 4 | | | IV-2 | ZFAND2A | 0.73 | 6488 | 3 | 4 | | | IV-2 | ZNF738 | 0.94 |
| 6393 | 3 | 4 | | | IV-2 | ZFAND2B | 0.75 | 6489 | 3 | 4 | | | IV-2 | ZNF764 | 0.78 |
| 6394 | 3 | 4 | | | IV-2 | ZFAND5 | 0.90 | 6490 | 3 | 4 | | | IV-2 | ZNF766 | 0.95 |
| 6395 | 3 | 4 | | | IV-2 | ZFP1 | 0.80 | 6491 | 3 | 4 | | | IV-2 | ZNF77 | 0.77 |
| 6396 | 3 | 4 | | | IV-2 | ZFP161 | 0.79 | 6492 | 3 | 4 | | | IV-2 | ZNF771 | 0.68 |
| 6397 | 3 | 4 | | | IV-2 | ZFP37 | 0.90 | 6493 | 3 | 4 | | | IV-2 | ZNF775 | 0.73 |
| 6398 | 3 | 4 | | | IV-2 | ZFYVE19 | 0.79 | 6494 | 3 | 4 | | | IV-2 | ZNF776 | 0.96 |
| 6399 | 3 | 4 | | | IV-2 | ZFYVE20 | 0.83 | 6495 | 3 | 4 | | | IV-2 | ZNF785 | 0.77 |
| 6400 | 3 | 4 | | | IV-2 | ZFYVE26 | 0.75 | 6496 | 3 | 4 | | | IV-2 | ZNF786 | 0.88 |
| 6401 | 3 | 4 | | | IV-2 | ZFYVE27 | 0.77 | 6497 | 3 | 4 | | | IV-2 | ZNF800 | 0.90 |
| 6402 | 3 | 4 | | | IV-2 | ZFYVE9 | 0.87 | 6498 | 3 | 4 | | | IV-2 | ZNF805 | 0.86 |
| 6403 | 3 | 4 | | | IV-2 | ZHX3 | 0.71 | 6499 | 3 | 4 | | | IV-2 | ZNF808 | 0.94 |
| 6404 | 3 | 4 | | | IV-2 | ZKSCAN3 | 0.87 | 6500 | 3 | 4 | | | IV-2 | ZNF815 | 0.78 |
| 6405 | 3 | 4 | | | IV-2 | ZKSCAN5 | 0.89 | 6501 | 3 | 4 | | | IV-2 | ZNF830 | 0.72 |
| 6406 | 3 | 4 | | | IV-2 | ZMAT2 | 0.91 | 6502 | 3 | 4 | | | IV-2 | ZNF835 | 0.69 |
| 6407 | 3 | 4 | | | IV-2 | ZMPSTE24 | 0.93 | 6503 | 3 | 4 | | | IV-2 | ZNF836 | 0.75 |
| 6408 | 3 | 4 | | | IV-2 | ZMYND11 | 0.91 | 6504 | 3 | 4 | | | IV-2 | ZNF845 | 0.83 |
| 6409 | 3 | 4 | | | IV-2 | ZNF131 | 0.83 | 6505 | 3 | 4 | | | IV-2 | ZNFX1-AS1 | 0.99 |
| 6410 | 3 | 4 | | | IV-2 | ZNF135 | 0.77 | 6506 | 3 | 4 | | | IV-2 | ZNHIT1 | 0.71 |
| 6411 | 3 | 4 | | | IV-2 | ZNF143 | 0.72 | 6507 | 3 | 4 | | | IV-2 | ZNHIT2 | 0.89 |
| 6412 | 3 | 4 | | | IV-2 | ZNF146 | 0.96 | 6508 | 3 | 4 | | | IV-2 | ZNHIT6 | 0.84 |
| 6413 | 3 | 4 | | | IV-2 | ZNF160 | 0.92 | 6509 | 3 | 4 | | | IV-2 | ZRANB1 | 0.84 |
| 6414 | 3 | 4 | | | IV-2 | ZNF180 | 0.96 | 6510 | 3 | 4 | | | IV-2 | ZSCAN2 | 0.79 |
| 6415 | 3 | 4 | | | IV-2 | ZNF2 | 0.98 | 6511 | 3 | 4 | | | IV-2 | ZSCAN22 | 0.72 |
| 6416 | 3 | 4 | | | IV-2 | ZNF202 | 0.84 | 6512 | 3 | 4 | | | IV-2 | ZWINT | 0.74 |
| 6417 | 3 | 4 | | | IV-2 | ZNF207 | 0.79 | 6513 | 3 | 4 | | | IV-2 | ZXDA | 0.77 |
| 6418 | 3 | 4 | | | IV-2 | ZNF211 | 0.80 | 6514 | 3 | 4 | | | IV-2 | ZXDC | 0.79 |
| 6419 | 3 | 4 | | | IV-2 | ZNF217 | 0.73 | 6515 | 3 | 4 | | | IV-1 | AAK1 | 1.21 |
| 6420 | 3 | 4 | | | IV-2 | ZNF219 | 0.77 | 6516 | 3 | 4 | | | IV-1 | AASDH | 1.29 |
| 6421 | 3 | 4 | | | IV-2 | ZNF22 | 0.86 | 6517 | 3 | 4 | | | IV-1 | ABAT | 1.15 |
| 6422 | 3 | 4 | | | IV-2 | ZNF227 | 0.88 | 6518 | 3 | 4 | | | IV-1 | ABCA1 | 1.11 |
| 6423 | 3 | 4 | | | IV-2 | ZNF232 | 0.95 | 6519 | 3 | 4 | | | IV-1 | ABCA10 | 1.35 |
| 6424 | 3 | 4 | | | IV-2 | ZNF256 | 0.75 | 6520 | 3 | 4 | | | IV-1 | ABCA6 | 1.25 |
| 6425 | 3 | 4 | | | IV-2 | ZNF26 | 0.94 | 6521 | 3 | 4 | | | IV-1 | ABCB10 | 1.08 |
| 6426 | 3 | 4 | | | IV-2 | ZNF263 | 0.70 | 6522 | 3 | 4 | | | IV-1 | ABCC5 | 1.06 |
| 6427 | 3 | 4 | | | IV-2 | ZNF264 | 0.90 | 6523 | 3 | 4 | | | IV-1 | ABCC6 | 1.48 |
| 6428 | 3 | 4 | | | IV-2 | ZNF275 | 0.77 | 6524 | 3 | 4 | | | IV-1 | ABHD14B | 1.10 |
| 6429 | 3 | 4 | | | IV-2 | ZNF304 | 0.93 | 6525 | 3 | 4 | | | IV-1 | ABHD16B | 1.04 |

Fig. 39 - 35

| | | | | | | | | | | | | | | | |
|---|---|---|---|---|---|---|---|---|---|---|---|---|---|---|---|
| 6526 | 3 | 4 | | | IV-1 | ABHD3 | 1.30 | 6622 | 3 | 4 | | | IV-1 | ASCC3 | 1.10 |
| 6527 | 3 | 4 | | | IV-1 | ACAA1 | 1.39 | 6623 | 3 | 4 | | | IV-1 | ASF1A | 1.23 |
| 6528 | 3 | 4 | | | IV-1 | ACACA | 1.10 | 6624 | 3 | 4 | | | IV-1 | ASMTL-AS1 | 1.09 |
| 6529 | 3 | 4 | | | IV-1 | ACAD9 | 1.14 | 6625 | 3 | 4 | | | IV-1 | ATAD1 | 1.15 |
| 6530 | 3 | 4 | | | IV-1 | ACADS | 1.05 | 6626 | 3 | 4 | | | IV-1 | ATAD2B | 1.42 |
| 6531 | 3 | 4 | | | IV-1 | ACADSB | 1.18 | 6627 | 3 | 4 | | | IV-1 | ATF2 | 1.05 |
| 6532 | 3 | 4 | | | IV-1 | ACAP2 | 1.17 | 6628 | 3 | 4 | | | IV-1 | ATF6 | 1.05 |
| 6533 | 3 | 4 | | | IV-1 | ACAT1 | 1.18 | 6629 | 3 | 4 | | | IV-1 | ATF7IP2 | 1.09 |
| 6534 | 3 | 4 | | | IV-1 | ACN9 | 1.05 | 6630 | 3 | 4 | | | IV-1 | ATG12 | 1.15 |
| 6535 | 3 | 4 | | | IV-1 | ACOT13 | 1.37 | 6631 | 3 | 4 | | | IV-1 | ATL2 | 1.18 |
| 6536 | 3 | 4 | | | IV-1 | ACOX1 | 1.08 | 6632 | 3 | 4 | | | IV-1 | ATM | 1.25 |
| 6537 | 3 | 4 | | | IV-1 | ACP1 | 1.01 | 6633 | 3 | 4 | | | IV-1 | ATP12A | 1.25 |
| 6538 | 3 | 4 | | | IV-1 | ACP5 | 1.46 | 6634 | 3 | 4 | | | IV-1 | ATP13A3 | 1.38 |
| 6539 | 3 | 4 | | | IV-1 | ACRC | 1.05 | 6635 | 3 | 4 | | | IV-1 | ATP13A4 | 1.43 |
| 6540 | 3 | 4 | | | IV-1 | ACSL4 | 1.04 | 6636 | 3 | 4 | | | IV-1 | ATP2C1 | 1.01 |
| 6541 | 3 | 4 | | | IV-1 | ACSL5 | 1.30 | 6637 | 3 | 4 | | | IV-1 | ATP5B | 1.37 |
| 6542 | 3 | 4 | | | IV-1 | ACSM5 | 1.15 | 6638 | 3 | 4 | | | IV-1 | ATP5E | 1.34 |
| 6543 | 3 | 4 | | | IV-1 | ACSS3 | 1.31 | 6639 | 3 | 4 | | | IV-1 | ATP5EP2 | 1.17 |
| 6544 | 3 | 4 | | | IV-1 | ACTR6 | 1.44 | 6640 | 3 | 4 | | | IV-1 | ATP5F1 | 1.43 |
| 6545 | 3 | 4 | | | IV-1 | ADAM10 | 1.28 | 6641 | 3 | 4 | | | IV-1 | ATP5G1 | 1.12 |
| 6546 | 3 | 4 | | | IV-1 | ADAMTS13 | 1.08 | 6642 | 3 | 4 | | | IV-1 | ATP5J | 1.34 |
| 6547 | 3 | 4 | | | IV-1 | ADD3 | 1.28 | 6643 | 3 | 4 | | | IV-1 | ATP5J2 | 1.36 |
| 6548 | 3 | 4 | | | IV-1 | ADH1C | 1.06 | 6644 | 3 | 4 | | | IV-1 | ATP5O | 1.19 |
| 6549 | 3 | 4 | | | IV-1 | ADK | 1.06 | 6645 | 3 | 4 | | | IV-1 | ATP6AP2 | 1.02 |
| 6550 | 3 | 4 | | | IV-1 | ADORA1 | 1.22 | 6646 | 3 | 4 | | | IV-1 | ATP6V0E1 | 1.05 |
| 6551 | 3 | 4 | | | IV-1 | ADORA3 | 1.10 | 6647 | 3 | 4 | | | IV-1 | ATP6V1B1 | 1.42 |
| 6552 | 3 | 4 | | | IV-1 | ADRB1 | 1.27 | 6648 | 3 | 4 | | | IV-1 | ATP6V1C1 | 1.14 |
| 6553 | 3 | 4 | | | IV-1 | AFF4 | 1.06 | 6649 | 3 | 4 | | | IV-1 | ATP6V1E1 | 1.20 |
| 6554 | 3 | 4 | | | IV-1 | AFTPH | 1.26 | 6650 | 3 | 4 | | | IV-1 | ATP6V1E2 | 1.23 |
| 6555 | 3 | 4 | | | IV-1 | AGFG1 | 1.09 | 6651 | 3 | 4 | | | IV-1 | ATP6V1H | 1.22 |
| 6556 | 3 | 4 | | | IV-1 | AGGF1 | 1.13 | 6652 | 3 | 4 | | | IV-1 | ATPAF1 | 1.26 |
| 6557 | 3 | 4 | | | IV-1 | AGPAT5 | 1.36 | 6653 | 3 | 4 | | | IV-1 | ATPIF1 | 1.07 |
| 6558 | 3 | 4 | | | IV-1 | AGPHD1 | 1.08 | 6654 | 3 | 4 | | | IV-1 | ATXN2 | 1.28 |
| 6559 | 3 | 4 | | | IV-1 | AHCYL1 | 1.20 | 6655 | 3 | 4 | | | IV-1 | AURKC | 1.01 |
| 6560 | 3 | 4 | | | IV-1 | AHSP | 1.09 | 6656 | 3 | 4 | | | IV-1 | AZI2 | 1.47 |
| 6561 | 3 | 4 | | | IV-1 | AIF1L | 1.04 | 6657 | 3 | 4 | | | IV-1 | B4GALT3 | 1.02 |
| 6562 | 3 | 4 | | | IV-1 | AIG1 | 1.14 | 6658 | 3 | 4 | | | IV-1 | B4GALT4 | 1.03 |
| 6563 | 3 | 4 | | | IV-1 | AIMP1 | 1.05 | 6659 | 3 | 4 | | | IV-1 | BACH2 | 1.15 |
| 6564 | 3 | 4 | | | IV-1 | AK3 | 1.06 | 6660 | 3 | 4 | | | IV-1 | BBS10 | 1.21 |
| 6565 | 3 | 4 | | | IV-1 | AK5 | 1.12 | 6661 | 3 | 4 | | | IV-1 | BBX | 1.41 |
| 6566 | 3 | 4 | | | IV-1 | AKAP10 | 1.22 | 6662 | 3 | 4 | | | IV-1 | BCAP29 | 1.16 |
| 6567 | 3 | 4 | | | IV-1 | AKIRIN1 | 1.06 | 6663 | 3 | 4 | | | IV-1 | BCAS2 | 1.24 |
| 6568 | 3 | 4 | | | IV-1 | AKR1A1 | 1.12 | 6664 | 3 | 4 | | | IV-1 | BCAS4 | 1.05 |
| 6569 | 3 | 4 | | | IV-1 | AKR1C1 | 1.38 | 6665 | 3 | 4 | | | IV-1 | BCCIP | 1.20 |
| 6570 | 3 | 4 | | | IV-1 | AKR1C2 | 1.19 | 6666 | 3 | 4 | | | IV-1 | BCO2 | 1.10 |
| 6571 | 3 | 4 | | | IV-1 | AKR1C3 | 1.04 | 6667 | 3 | 4 | | | IV-1 | BDP1 | 1.30 |
| 6572 | 3 | 4 | | | IV-1 | ALCAM | 1.39 | 6668 | 3 | 4 | | | IV-1 | BECN1 | 1.02 |
| 6573 | 3 | 4 | | | IV-1 | ALDH7A1 | 1.16 | 6669 | 3 | 4 | | | IV-1 | BEND7 | 1.18 |
| 6574 | 3 | 4 | | | IV-1 | ALDOC | 1.31 | 6670 | 3 | 4 | | | IV-1 | BHLHE41 | 1.14 |
| 6575 | 3 | 4 | | | IV-1 | ALG14 | 1.24 | 6671 | 3 | 4 | | | IV-1 | BIRC6 | 1.20 |
| 6576 | 3 | 4 | | | IV-1 | ALG6 | 1.40 | 6672 | 3 | 4 | | | IV-1 | BMS1P5 | 1.28 |
| 6577 | 3 | 4 | | | IV-1 | AMACR | 1.14 | 6673 | 3 | 4 | | | IV-1 | BNIP1 | 1.02 |
| 6578 | 3 | 4 | | | IV-1 | AMIGO2 | 1.01 | 6674 | 3 | 4 | | | IV-1 | BNIP3 | 1.44 |
| 6579 | 3 | 4 | | | IV-1 | AMN1 | 1.15 | 6675 | 3 | 4 | | | IV-1 | BNIP3L | 1.48 |
| 6580 | 3 | 4 | | | IV-1 | AMZ2 | 1.03 | 6676 | 3 | 4 | | | IV-1 | BPNT1 | 1.13 |
| 6581 | 3 | 4 | | | IV-1 | ANAPC11 | 1.09 | 6677 | 3 | 4 | | | IV-1 | BPTF | 1.14 |
| 6582 | 3 | 4 | | | IV-1 | ANAPC13 | 1.14 | 6678 | 3 | 4 | | | IV-1 | BPY2 | 1.15 |
| 6583 | 3 | 4 | | | IV-1 | ANAPC16 | 1.18 | 6679 | 3 | 4 | | | IV-1 | BRCA1 | 1.13 |
| 6584 | 3 | 4 | | | IV-1 | ANGPT1 | 1.36 | 6680 | 3 | 4 | | | IV-1 | BRMS1L | 1.19 |
| 6585 | 3 | 4 | | | IV-1 | ANKDD1A | 1.03 | 6681 | 3 | 4 | | | IV-1 | BRP44 | 1.19 |
| 6586 | 3 | 4 | | | IV-1 | ANKHD1 | 1.47 | 6682 | 3 | 4 | | | IV-1 | BRP44L | 1.33 |
| 6587 | 3 | 4 | | | IV-1 | ANKIB1 | 1.23 | 6683 | 3 | 4 | | | IV-1 | BRWD1 | 1.33 |
| 6588 | 3 | 4 | | | IV-1 | ANKMY2 | 1.08 | 6684 | 3 | 4 | | | IV-1 | BTBD16 | 1.29 |
| 6589 | 3 | 4 | | | IV-1 | ANKRD11 | 1.26 | 6685 | 3 | 4 | | | IV-1 | BTBD3 | 1.19 |
| 6590 | 3 | 4 | | | IV-1 | ANKRD17 | 1.25 | 6686 | 3 | 4 | | | IV-1 | BTF3 | 1.07 |
| 6591 | 3 | 4 | | | IV-1 | ANKRD20A2 | 1.16 | 6687 | 3 | 4 | | | IV-1 | BUB3 | 1.12 |
| 6592 | 3 | 4 | | | IV-1 | ANKRD32 | 1.06 | 6688 | 3 | 4 | | | IV-1 | BUD31 | 1.03 |
| 6593 | 3 | 4 | | | IV-1 | ANKRD42 | 1.44 | 6689 | 3 | 4 | | | IV-1 | BVES | 1.07 |
| 6594 | 3 | 4 | | | IV-1 | ANKRD44 | 1.23 | 6690 | 3 | 4 | | | IV-1 | BZW1 | 1.32 |
| 6595 | 3 | 4 | | | IV-1 | ANKRD5 | 1.12 | 6691 | 3 | 4 | | | IV-1 | C10orf35 | 1.03 |
| 6596 | 3 | 4 | | | IV-1 | ANKRD6 | 1.23 | 6692 | 3 | 4 | | | IV-1 | C10orf46 | 1.19 |
| 6597 | 3 | 4 | | | IV-1 | AP1AR | 1.12 | 6693 | 3 | 4 | | | IV-1 | C10orf81 | 1.43 |
| 6598 | 3 | 4 | | | IV-1 | AP1G1 | 1.06 | 6694 | 3 | 4 | | | IV-1 | C10orf82 | 1.29 |
| 6599 | 3 | 4 | | | IV-1 | AP3B1 | 1.15 | 6695 | 3 | 4 | | | IV-1 | C11orf31 | 1.20 |
| 6600 | 3 | 4 | | | IV-1 | AP3M2 | 1.06 | 6696 | 3 | 4 | | | IV-1 | C11orf46 | 1.10 |
| 6601 | 3 | 4 | | | IV-1 | AP4S1 | 1.29 | 6697 | 3 | 4 | | | IV-1 | C11orf52 | 1.19 |
| 6602 | 3 | 4 | | | IV-1 | APOBEC2 | 1.16 | 6698 | 3 | 4 | | | IV-1 | C11orf54 | 1.48 |
| 6603 | 3 | 4 | | | IV-1 | APOD | 1.35 | 6699 | 3 | 4 | | | IV-1 | C11orf57 | 1.23 |
| 6604 | 3 | 4 | | | IV-1 | APOOL | 1.29 | 6700 | 3 | 4 | | | IV-1 | C11orf58 | 1.12 |
| 6605 | 3 | 4 | | | IV-1 | APTX | 1.10 | 6701 | 3 | 4 | | | IV-1 | C12orf35 | 1.03 |
| 6606 | 3 | 4 | | | IV-1 | ARFGEF1 | 1.13 | 6702 | 3 | 4 | | | IV-1 | C12orf73 | 1.36 |
| 6607 | 3 | 4 | | | IV-1 | ARFIP1 | 1.19 | 6703 | 3 | 4 | | | IV-1 | C12orf76 | 1.19 |
| 6608 | 3 | 4 | | | IV-1 | ARG2 | 1.33 | 6704 | 3 | 4 | | | IV-1 | C14orf109 | 1.40 |
| 6609 | 3 | 4 | | | IV-1 | ARHGAP15 | 1.15 | 6705 | 3 | 4 | | | IV-1 | C14orf142 | 1.09 |
| 6610 | 3 | 4 | | | IV-1 | ARHGAP5 | 1.08 | 6706 | 3 | 4 | | | IV-1 | C15orf23 | 1.03 |
| 6611 | 3 | 4 | | | IV-1 | ARHGEF26 | 1.29 | 6707 | 3 | 4 | | | IV-1 | C15orf40 | 1.04 |
| 6612 | 3 | 4 | | | IV-1 | ARHGEF6 | 1.20 | 6708 | 3 | 4 | | | IV-1 | C16orf46 | 1.02 |
| 6613 | 3 | 4 | | | IV-1 | ARID2 | 1.14 | 6709 | 3 | 4 | | | IV-1 | C16orf52 | 1.13 |
| 6614 | 3 | 4 | | | IV-1 | ARL1 | 1.11 | 6710 | 3 | 4 | | | IV-1 | C16orf70 | 1.09 |
| 6615 | 3 | 4 | | | IV-1 | ARL15 | 1.08 | 6711 | 3 | 4 | | | IV-1 | C16orf95 | 1.43 |
| 6616 | 3 | 4 | | | IV-1 | ARL6IP1 | 1.08 | 6712 | 3 | 4 | | | IV-1 | C17orf107 | 1.05 |
| 6617 | 3 | 4 | | | IV-1 | ARPC1A | 1.01 | 6713 | 3 | 4 | | | IV-1 | C17orf48 | 1.14 |
| 6618 | 3 | 4 | | | IV-1 | ARPC3 | 1.15 | 6714 | 3 | 4 | | | IV-1 | C17orf79 | 1.25 |
| 6619 | 3 | 4 | | | IV-1 | ARSD | 1.03 | 6715 | 3 | 4 | | | IV-1 | C18orf25 | 1.03 |
| 6620 | 3 | 4 | | | IV-1 | ART3 | 1.18 | 6716 | 3 | 4 | | | IV-1 | C19orf12 | 1.05 |
| 6621 | 3 | 4 | | | IV-1 | ASB8 | 1.28 | 6717 | 3 | 4 | | | IV-1 | C19orf26 | 1.38 |

Fig. 39 - 36

| | | | | | | | | | | | | | | | |
|---|---|---|---|---|---|---|---|---|---|---|---|---|---|---|---|
| 6718 | 3 | 4 | | | IV-1 | C19orf42 | 1.20 | 6814 | 3 | 4 | | | IV-1 | CEP350 | 1.14 |
| 6719 | 3 | 4 | | | IV-1 | C19orf46 | 1.38 | 6815 | 3 | 4 | | | IV-1 | CEP44 | 1.17 |
| 6720 | 3 | 4 | | | IV-1 | C19orf73 | 1.02 | 6816 | 3 | 4 | | | IV-1 | CEP70 | 1.26 |
| 6721 | 3 | 4 | | | IV-1 | C19orf81 | 1.05 | 6817 | 3 | 4 | | | IV-1 | CEP76 | 1.18 |
| 6722 | 3 | 4 | | | IV-1 | C1orf109 | 1.14 | 6818 | 3 | 4 | | | IV-1 | CEPT1 | 1.13 |
| 6723 | 3 | 4 | | | IV-1 | C1orf130 | 1.37 | 6819 | 3 | 4 | | | IV-1 | CETN2 | 1.01 |
| 6724 | 3 | 4 | | | IV-1 | C1orf131 | 1.13 | 6820 | 3 | 4 | | | IV-1 | CFDP1 | 1.08 |
| 6725 | 3 | 4 | | | IV-1 | C1orf162 | 1.04 | 6821 | 3 | 4 | | | IV-1 | CFHR1 | 1.05 |
| 6726 | 3 | 4 | | | IV-1 | C1orf38 | 1.27 | 6822 | 3 | 4 | | | IV-1 | CFLAR | 1.10 |
| 6727 | 3 | 4 | | | IV-1 | C1orf52 | 1.12 | 6823 | 3 | 4 | | | IV-1 | CHAC2 | 1.08 |
| 6728 | 3 | 4 | | | IV-1 | C1QTNF4 | 1.02 | 6824 | 3 | 4 | | | IV-1 | CHCHD2 | 1.11 |
| 6729 | 3 | 4 | | | IV-1 | C20orf151 | 1.02 | 6825 | 3 | 4 | | | IV-1 | CHCHD7 | 1.03 |
| 6730 | 3 | 4 | | | IV-1 | C20orf7 | 1.07 | 6826 | 3 | 4 | | | IV-1 | CHD6 | 1.00 |
| 6731 | 3 | 4 | | | IV-1 | C22orf32 | 1.33 | 6827 | 3 | 4 | | | IV-1 | CHD9 | 1.30 |
| 6732 | 3 | 4 | | | IV-1 | C2orf29 | 1.02 | 6828 | 3 | 4 | | | IV-1 | CHDH | 1.35 |
| 6733 | 3 | 4 | | | IV-1 | C2orf44 | 1.01 | 6829 | 3 | 4 | | | IV-1 | CHIC1 | 1.15 |
| 6734 | 3 | 4 | | | IV-1 | C2orf69 | 1.01 | 6830 | 3 | 4 | | | IV-1 | CHIT1 | 1.06 |
| 6735 | 3 | 4 | | | IV-1 | C2orf82 | 1.24 | 6831 | 3 | 4 | | | IV-1 | CHM | 1.05 |
| 6736 | 3 | 4 | | | IV-1 | C3orf19 | 1.02 | 6832 | 3 | 4 | | | IV-1 | CHMP2B | 1.14 |
| 6737 | 3 | 4 | | | IV-1 | C3orf55 | 1.45 | 6833 | 3 | 4 | | | IV-1 | CHRM1 | 1.33 |
| 6738 | 3 | 4 | | | IV-1 | C3orf70 | 1.13 | 6834 | 3 | 4 | | | IV-1 | CHRNA1 | 1.22 |
| 6739 | 3 | 4 | | | IV-1 | C3orf80 | 1.16 | 6835 | 3 | 4 | | | IV-1 | CHST1 | 1.10 |
| 6740 | 3 | 4 | | | IV-1 | C4orf3 | 1.14 | 6836 | 3 | 4 | | | IV-1 | CHUK | 1.03 |
| 6741 | 3 | 4 | | | IV-1 | C4orf34 | 1.32 | 6837 | 3 | 4 | | | IV-1 | CIB2 | 1.18 |
| 6742 | 3 | 4 | | | IV-1 | C5AR1 | 1.24 | 6838 | 3 | 4 | | | IV-1 | CIRBP | 1.05 |
| 6743 | 3 | 4 | | | IV-1 | C5orf22 | 1.21 | 6839 | 3 | 4 | | | IV-1 | CKLF | 1.28 |
| 6744 | 3 | 4 | | | IV-1 | C5orf28 | 1.23 | 6840 | 3 | 4 | | | IV-1 | CLASP2 | 1.09 |
| 6745 | 3 | 4 | | | IV-1 | C5orf43 | 1.13 | 6841 | 3 | 4 | | | IV-1 | CLCN4 | 1.03 |
| 6746 | 3 | 4 | | | IV-1 | C5orf42 | 1.24 | 6842 | 3 | 4 | | | IV-1 | CLCNKA | 1.07 |
| 6747 | 3 | 4 | | | IV-1 | C5orf54 | 1.45 | 6843 | 3 | 4 | | | IV-1 | CLDN12 | 1.29 |
| 6748 | 3 | 4 | | | IV-1 | C6 | 1.20 | 6844 | 3 | 4 | | | IV-1 | CLDN16 | 1.08 |
| 6749 | 3 | 4 | | | IV-1 | C6orf130 | 1.06 | 6845 | 3 | 4 | | | IV-1 | CLEC2D | 1.18 |
| 6750 | 3 | 4 | | | IV-1 | C6orf203 | 1.14 | 6846 | 3 | 4 | | | IV-1 | CLIP4 | 1.14 |
| 6751 | 3 | 4 | | | IV-1 | C6orf211 | 1.21 | 6847 | 3 | 4 | | | IV-1 | CLN5 | 1.30 |
| 6752 | 3 | 4 | | | IV-1 | C6orf225 | 1.09 | 6848 | 3 | 4 | | | IV-1 | CLNS1A | 1.01 |
| 6753 | 3 | 4 | | | IV-1 | C6orf57 | 1.49 | 6849 | 3 | 4 | | | IV-1 | CLTC | 1.15 |
| 6754 | 3 | 4 | | | IV-1 | C7orf23 | 1.12 | 6850 | 3 | 4 | | | IV-1 | CMAS | 1.27 |
| 6755 | 3 | 4 | | | IV-1 | C7orf41 | 1.21 | 6851 | 3 | 4 | | | IV-1 | CMBL | 1.19 |
| 6756 | 3 | 4 | | | IV-1 | C7orf73 | 1.13 | 6852 | 3 | 4 | | | IV-1 | CMC1 | 1.23 |
| 6757 | 3 | 4 | | | IV-1 | C8G | 1.06 | 6853 | 3 | 4 | | | IV-1 | CMC2 | 1.21 |
| 6758 | 3 | 4 | | | IV-1 | C8orf40 | 1.21 | 6854 | 3 | 4 | | | IV-1 | CMPK1 | 1.28 |
| 6759 | 3 | 4 | | | IV-1 | C8orf84 | 1.31 | 6855 | 3 | 4 | | | IV-1 | CNDP2 | 1.31 |
| 6760 | 3 | 4 | | | IV-1 | C9orf123 | 1.09 | 6856 | 3 | 4 | | | IV-1 | CNOT2 | 1.16 |
| 6761 | 3 | 4 | | | IV-1 | C9orf129 | 1.27 | 6857 | 3 | 4 | | | IV-1 | CNOT8 | 1.05 |
| 6762 | 3 | 4 | | | IV-1 | C9orf40 | 1.08 | 6858 | 3 | 4 | | | IV-1 | CNPY2 | 1.20 |
| 6763 | 3 | 4 | | | IV-1 | C9orf68 | 1.22 | 6859 | 3 | 4 | | | IV-1 | COBLL1 | 1.14 |
| 6764 | 3 | 4 | | | IV-1 | C9orf78 | 1.15 | 6860 | 3 | 4 | | | IV-1 | COL4A3BP | 1.27 |
| 6765 | 3 | 4 | | | IV-1 | C9orf91 | 1.18 | 6861 | 3 | 4 | | | IV-1 | COL9A2 | 1.24 |
| 6766 | 3 | 4 | | | IV-1 | C9orf95 | 1.03 | 6862 | 3 | 4 | | | IV-1 | COMTD1 | 1.39 |
| 6767 | 3 | 4 | | | IV-1 | CAB39 | 1.11 | 6863 | 3 | 4 | | | IV-1 | COPB1 | 1.02 |
| 6768 | 3 | 4 | | | IV-1 | CACHD1 | 1.02 | 6864 | 3 | 4 | | | IV-1 | COPG2 | 1.38 |
| 6769 | 3 | 4 | | | IV-1 | CACNB4 | 1.17 | 6865 | 3 | 4 | | | IV-1 | COPS2 | 1.02 |
| 6770 | 3 | 4 | | | IV-1 | CALCRL | 1.04 | 6866 | 3 | 4 | | | IV-1 | COQ10A | 1.06 |
| 6771 | 3 | 4 | | | IV-1 | CALM2 | 1.22 | 6867 | 3 | 4 | | | IV-1 | COQ5 | 1.13 |
| 6772 | 3 | 4 | | | IV-1 | CAMK2D | 1.16 | 6868 | 3 | 4 | | | IV-1 | COQ6 | 1.33 |
| 6773 | 3 | 4 | | | IV-1 | CAMSAP2 | 1.10 | 6869 | 3 | 4 | | | IV-1 | CORIN | 1.04 |
| 6774 | 3 | 4 | | | IV-1 | CAPN7 | 1.07 | 6870 | 3 | 4 | | | IV-1 | COX14 | 1.21 |
| 6775 | 3 | 4 | | | IV-1 | CAPZA1 | 1.01 | 6871 | 3 | 4 | | | IV-1 | COX16 | 1.34 |
| 6776 | 3 | 4 | | | IV-1 | CASD1 | 1.33 | 6872 | 3 | 4 | | | IV-1 | COX18 | 1.05 |
| 6777 | 3 | 4 | | | IV-1 | CASP6 | 1.18 | 6873 | 3 | 4 | | | IV-1 | COX5B | 1.17 |
| 6778 | 3 | 4 | | | IV-1 | CASP8AP2 | 1.09 | 6874 | 3 | 4 | | | IV-1 | COX6A1 | 1.08 |
| 6779 | 3 | 4 | | | IV-1 | CASP9 | 1.10 | 6875 | 3 | 4 | | | IV-1 | COX6B1 | 1.19 |
| 6780 | 3 | 4 | | | IV-1 | CAT | 1.33 | 6876 | 3 | 4 | | | IV-1 | COX7A2L | 1.12 |
| 6781 | 3 | 4 | | | IV-1 | CBFB | 1.15 | 6877 | 3 | 4 | | | IV-1 | COX7C | 1.29 |
| 6782 | 3 | 4 | | | IV-1 | CBR4 | 1.24 | 6878 | 3 | 4 | | | IV-1 | CPD | 1.31 |
| 6783 | 3 | 4 | | | IV-1 | CBWD3 | 1.23 | 6879 | 3 | 4 | | | IV-1 | CPE | 1.04 |
| 6784 | 3 | 4 | | | IV-1 | CBWD6 | 1.08 | 6880 | 3 | 4 | | | IV-1 | CPEB3 | 1.08 |
| 6785 | 3 | 4 | | | IV-1 | CBX3 | 1.14 | 6881 | 3 | 4 | | | IV-1 | CPPED1 | 1.09 |
| 6786 | 3 | 4 | | | IV-1 | CCDC121 | 1.02 | 6882 | 3 | 4 | | | IV-1 | CRABP2 | 1.01 |
| 6787 | 3 | 4 | | | IV-1 | CCDC125 | 1.16 | 6883 | 3 | 4 | | | IV-1 | CREM | 1.10 |
| 6788 | 3 | 4 | | | IV-1 | CCDC15 | 1.12 | 6884 | 3 | 4 | | | IV-1 | CRIPT | 1.11 |
| 6789 | 3 | 4 | | | IV-1 | CCDC28A | 1.15 | 6885 | 3 | 4 | | | IV-1 | CRK | 1.15 |
| 6790 | 3 | 4 | | | IV-1 | CCDC43 | 1.14 | 6886 | 3 | 4 | | | IV-1 | CRTAC1 | 1.13 |
| 6791 | 3 | 4 | | | IV-1 | CCDC56 | 1.03 | 6887 | 3 | 4 | | | IV-1 | CRYZL1 | 1.26 |
| 6792 | 3 | 4 | | | IV-1 | CCDC73 | 1.09 | 6888 | 3 | 4 | | | IV-1 | CSDE1 | 1.22 |
| 6793 | 3 | 4 | | | IV-1 | CCDC74B | 1.09 | 6889 | 3 | 4 | | | IV-1 | CSE1L | 1.06 |
| 6794 | 3 | 4 | | | IV-1 | CCDC908 | 1.10 | 6890 | 3 | 4 | | | IV-1 | CTF1 | 1.11 |
| 6795 | 3 | 4 | | | IV-1 | CCDC91 | 1.18 | 6891 | 3 | 4 | | | IV-1 | CTH | 1.41 |
| 6796 | 3 | 4 | | | IV-1 | CCL20 | 1.02 | 6892 | 3 | 4 | | | IV-1 | CTNNB1 | 1.10 |
| 6797 | 3 | 4 | | | IV-1 | CCNC | 1.44 | 6893 | 3 | 4 | | | IV-1 | CTPS | 1.34 |
| 6798 | 3 | 4 | | | IV-1 | CCNG1 | 1.25 | 6894 | 3 | 4 | | | IV-1 | CTR9 | 1.18 |
| 6799 | 3 | 4 | | | IV-1 | CCNJ | 1.06 | 6895 | 3 | 4 | | | IV-1 | CUL3 | 1.22 |
| 6800 | 3 | 4 | | | IV-1 | CCNT1 | 1.16 | 6896 | 3 | 4 | | | IV-1 | CUL4B | 1.07 |
| 6801 | 3 | 4 | | | IV-1 | CCPG1 | 1.36 | 6897 | 3 | 4 | | | IV-1 | CUL5 | 1.38 |
| 6802 | 3 | 4 | | | IV-1 | CCT8 | 1.04 | 6898 | 3 | 4 | | | IV-1 | CYB561D2 | 1.39 |
| 6803 | 3 | 4 | | | IV-1 | CCZ1 | 1.05 | 6899 | 3 | 4 | | | IV-1 | CYP27A1 | 1.00 |
| 6804 | 3 | 4 | | | IV-1 | CD164L2 | 1.25 | 6900 | 3 | 4 | | | IV-1 | CYP3A7 | 1.09 |
| 6805 | 3 | 4 | | | IV-1 | CD200 | 1.18 | 6901 | 3 | 4 | | | IV-1 | CYP4B1 | 1.44 |
| 6806 | 3 | 4 | | | IV-1 | CD59 | 1.17 | 6902 | 3 | 4 | | | IV-1 | CYP4V2 | 1.38 |
| 6807 | 3 | 4 | | | IV-1 | CDC14A | 1.17 | 6903 | 3 | 4 | | | IV-1 | DBI | 1.27 |
| 6808 | 3 | 4 | | | IV-1 | CDC40 | 1.05 | 6904 | 3 | 4 | | | IV-1 | DCBLD2 | 1.22 |
| 6809 | 3 | 4 | | | IV-1 | CDK8 | 1.10 | 6905 | 3 | 4 | | | IV-1 | DCTN4 | 1.10 |
| 6810 | 3 | 4 | | | IV-1 | CDKN1C | 1.42 | 6906 | 3 | 4 | | | IV-1 | DCUN1D1 | 1.06 |
| 6811 | 3 | 4 | | | IV-1 | CDS1 | 1.20 | 6907 | 3 | 4 | | | IV-1 | DCUN1D4 | 1.39 |
| 6812 | 3 | 4 | | | IV-1 | CEACAM6 | 1.38 | 6908 | 3 | 4 | | | IV-1 | DCXR | 1.16 |
| 6813 | 3 | 4 | | | IV-1 | CEMP1 | 1.09 | 6909 | 3 | 4 | | | IV-1 | DDHD1 | 1.34 |

Fig. 39 - 37

| | | | | | | | | | | | | | | | |
|---|---|---|---|---|---|---|---|---|---|---|---|---|---|---|---|
| 6910 | 3 | 4 | | | IV-1 | DDIT4L | 1.37 | 7006 | 3 | 4 | | | IV-1 | ETFA | 1.39 |
| 6911 | 3 | 4 | | | IV-1 | DDTL | 1.38 | 7007 | 3 | 4 | | | IV-1 | ETFB | 1.10 |
| 6912 | 3 | 4 | | | IV-1 | DDX18 | 1.08 | 7008 | 3 | 4 | | | IV-1 | ETFDH | 1.40 |
| 6913 | 3 | 4 | | | IV-1 | DDX46 | 1.44 | 7009 | 3 | 4 | | | IV-1 | ETV6 | 1.01 |
| 6914 | 3 | 4 | | | IV-1 | DDX52 | 1.17 | 7010 | 3 | 4 | | | IV-1 | EXOC5 | 1.16 |
| 6915 | 3 | 4 | | | IV-1 | DDX60 | 1.46 | 7011 | 3 | 4 | | | IV-1 | EXOC6 | 1.44 |
| 6916 | 3 | 4 | | | IV-1 | DECR1 | 1.19 | 7012 | 3 | 4 | | | IV-1 | EXOSC3 | 1.05 |
| 6917 | 3 | 4 | | | IV-1 | DECR2 | 1.14 | 7013 | 3 | 4 | | | IV-1 | FABP6 | 1.36 |
| 6918 | 3 | 4 | | | IV-1 | DEFB103B | 1.23 | 7014 | 3 | 4 | | | IV-1 | FAM103A1 | 1.13 |
| 6919 | 3 | 4 | | | IV-1 | DEK | 1.10 | 7015 | 3 | 4 | | | IV-1 | FAM115C | 1.11 |
| 6920 | 3 | 4 | | | IV-1 | DENND4C | 1.19 | 7016 | 3 | 4 | | | IV-1 | FAM120AOS | 1.05 |
| 6921 | 3 | 4 | | | IV-1 | DENR | 1.13 | 7017 | 3 | 4 | | | IV-1 | FAM122C | 1.30 |
| 6922 | 3 | 4 | | | IV-1 | DEPTOR | 1.38 | 7018 | 3 | 4 | | | IV-1 | FAM13B | 1.16 |
| 6923 | 3 | 4 | | | IV-1 | DET1 | 1.47 | 7019 | 3 | 4 | | | IV-1 | FAM161A | 1.02 |
| 6924 | 3 | 4 | | | IV-1 | DHFR | 1.18 | 7020 | 3 | 4 | | | IV-1 | FAM162A | 1.26 |
| 6925 | 3 | 4 | | | IV-1 | DHRS3 | 1.02 | 7021 | 3 | 4 | | | IV-1 | FAM165B | 1.25 |
| 6926 | 3 | 4 | | | IV-1 | DHRS7B | 1.03 | 7022 | 3 | 4 | | | IV-1 | FAM172A | 1.12 |
| 6927 | 3 | 4 | | | IV-1 | DHTKD1 | 1.38 | 7023 | 3 | 4 | | | IV-1 | FAM173A | 1.02 |
| 6928 | 3 | 4 | | | IV-1 | DHX29 | 1.21 | 7024 | 3 | 4 | | | IV-1 | FAM173B | 1.10 |
| 6929 | 3 | 4 | | | IV-1 | DIMT1 | 1.06 | 7025 | 3 | 4 | | | IV-1 | FAM174B | 1.19 |
| 6930 | 3 | 4 | | | IV-1 | DIO3 | 1.00 | 7026 | 3 | 4 | | | IV-1 | FAM175B | 1.12 |
| 6931 | 3 | 4 | | | IV-1 | DIRAS1 | 1.10 | 7027 | 3 | 4 | | | IV-1 | FAM184B | 1.05 |
| 6932 | 3 | 4 | | | IV-1 | DIS3 | 1.46 | 7028 | 3 | 4 | | | IV-1 | FAM199X | 1.29 |
| 6933 | 3 | 4 | | | IV-1 | DISC1 | 1.15 | 7029 | 3 | 4 | | | IV-1 | FAM200A | 1.11 |
| 6934 | 3 | 4 | | | IV-1 | DIXDC1 | 1.13 | 7030 | 3 | 4 | | | IV-1 | FAM25A | 1.05 |
| 6935 | 3 | 4 | | | IV-1 | DKFZP434I0714 | 1.46 | 7031 | 3 | 4 | | | IV-1 | FAM3D | 1.15 |
| 6936 | 3 | 4 | | | IV-1 | DLAT | 1.17 | 7032 | 3 | 4 | | | IV-1 | FAM45B | 1.47 |
| 6937 | 3 | 4 | | | IV-1 | DLG1 | 1.28 | 7033 | 3 | 4 | | | IV-1 | FAM49A | 1.06 |
| 6938 | 3 | 4 | | | IV-1 | DLL1 | 1.03 | 7034 | 3 | 4 | | | IV-1 | FAM81A | 1.33 |
| 6939 | 3 | 4 | | | IV-1 | DMXL1 | 1.05 | 7035 | 3 | 4 | | | IV-1 | FAM82B | 1.03 |
| 6940 | 3 | 4 | | | IV-1 | DMXL2 | 1.16 | 7036 | 3 | 4 | | | IV-1 | FAM84B | 1.15 |
| 6941 | 3 | 4 | | | IV-1 | DNAJA2 | 1.18 | 7037 | 3 | 4 | | | IV-1 | FAM86FP | 1.01 |
| 6942 | 3 | 4 | | | IV-1 | DNAJB14 | 1.42 | 7038 | 3 | 4 | | | IV-1 | FAM96A | 1.01 |
| 6943 | 3 | 4 | | | IV-1 | DNAJB9 | 1.20 | 7039 | 3 | 4 | | | IV-1 | FANCF | 1.07 |
| 6944 | 3 | 4 | | | IV-1 | DNAJC1 | 1.08 | 7040 | 3 | 4 | | | IV-1 | FASTKD1 | 1.47 |
| 6945 | 3 | 4 | | | IV-1 | DNAJC10 | 1.03 | 7041 | 3 | 4 | | | IV-1 | FBXO21 | 1.09 |
| 6946 | 3 | 4 | | | IV-1 | DNAJC15 | 1.17 | 7042 | 3 | 4 | | | IV-1 | FBXO22 | 1.15 |
| 6947 | 3 | 4 | | | IV-1 | DNAJC16 | 1.20 | 7043 | 3 | 4 | | | IV-1 | FBXO22-AS1 | 1.35 |
| 6948 | 3 | 4 | | | IV-1 | DNAJC21 | 1.14 | 7044 | 3 | 4 | | | IV-1 | FBXO3 | 1.16 |
| 6949 | 3 | 4 | | | IV-1 | DNAJC25 | 1.11 | 7045 | 3 | 4 | | | IV-1 | FBXO32 | 1.08 |
| 6950 | 3 | 4 | | | IV-1 | DNAJC27 | 1.21 | 7046 | 3 | 4 | | | IV-1 | FBXO6 | 1.12 |
| 6951 | 3 | 4 | | | IV-1 | DNAJC3 | 1.05 | 7047 | 3 | 4 | | | IV-1 | FBXW2 | 1.06 |
| 6952 | 3 | 4 | | | IV-1 | DOCK3 | 1.13 | 7048 | 3 | 4 | | | IV-1 | FCHO2 | 1.20 |
| 6953 | 3 | 4 | | | IV-1 | DOCK4 | 1.06 | 7049 | 3 | 4 | | | IV-1 | FDX1 | 1.29 |
| 6954 | 3 | 4 | | | IV-1 | DPH5 | 1.03 | 7050 | 3 | 4 | | | IV-1 | FDXACB1 | 1.12 |
| 6955 | 3 | 4 | | | IV-1 | DPP6 | 1.10 | 7051 | 3 | 4 | | | IV-1 | FGD4 | 1.10 |
| 6956 | 3 | 4 | | | IV-1 | DPY19L4 | 1.02 | 7052 | 3 | 4 | | | IV-1 | FGD6 | 1.12 |
| 6957 | 3 | 4 | | | IV-1 | DPYD | 1.26 | 7053 | 3 | 4 | | | IV-1 | FGFR1OP | 1.28 |
| 6958 | 3 | 4 | | | IV-1 | DRAM2 | 1.13 | 7054 | 3 | 4 | | | IV-1 | FGFR1OP2 | 1.14 |
| 6959 | 3 | 4 | | | IV-1 | DRD2 | 1.43 | 7055 | 3 | 4 | | | IV-1 | FGFR4 | 1.34 |
| 6960 | 3 | 4 | | | IV-1 | DSTNP2 | 1.16 | 7056 | 3 | 4 | | | IV-1 | FH | 1.49 |
| 6961 | 3 | 4 | | | IV-1 | DUS4L | 1.08 | 7057 | 3 | 4 | | | IV-1 | FKBPL | 1.05 |
| 6962 | 3 | 4 | | | IV-1 | DUSP22 | 1.11 | 7058 | 3 | 4 | | | IV-1 | FLJ10038 | 1.01 |
| 6963 | 3 | 4 | | | IV-1 | DYNC1I1 | 1.09 | 7059 | 3 | 4 | | | IV-1 | FLJ27352 | 1.12 |
| 6964 | 3 | 4 | | | IV-1 | DYNC1I2 | 1.39 | 7060 | 3 | 4 | | | IV-1 | FLJ30403 | 1.22 |
| 6965 | 3 | 4 | | | IV-1 | DYNLL1 | 1.02 | 7061 | 3 | 4 | | | IV-1 | FLJ39739 | 1.03 |
| 6966 | 3 | 4 | | | IV-1 | DYNLT1 | 1.34 | 7062 | 3 | 4 | | | IV-1 | FLJ45513 | 1.31 |
| 6967 | 3 | 4 | | | IV-1 | DYNLT3 | 1.04 | 7063 | 3 | 4 | | | IV-1 | FMO3 | 1.36 |
| 6968 | 3 | 4 | | | IV-1 | DYRK4 | 1.26 | 7064 | 3 | 4 | | | IV-1 | FMR1 | 1.28 |
| 6969 | 3 | 4 | | | IV-1 | E2F3 | 1.20 | 7065 | 3 | 4 | | | IV-1 | FN3K | 1.20 |
| 6970 | 3 | 4 | | | IV-1 | EBP | 1.38 | 7066 | 3 | 4 | | | IV-1 | FNDC4 | 1.09 |
| 6971 | 3 | 4 | | | IV-1 | ECHS1 | 1.23 | 7067 | 3 | 4 | | | IV-1 | FNTA | 1.10 |
| 6972 | 3 | 4 | | | IV-1 | ECI1 | 1.20 | 7068 | 3 | 4 | | | IV-1 | FP588 | 1.15 |
| 6973 | 3 | 4 | | | IV-1 | ECI2 | 1.17 | 7069 | 3 | 4 | | | IV-1 | FPGT | 1.33 |
| 6974 | 3 | 4 | | | IV-1 | EDEM3 | 1.03 | 7070 | 3 | 4 | | | IV-1 | FPR2 | 1.34 |
| 6975 | 3 | 4 | | | IV-1 | EFCAB11 | 1.18 | 7071 | 3 | 4 | | | IV-1 | FRA10AC1 | 1.36 |
| 6976 | 3 | 4 | | | IV-1 | EFR3B | 1.02 | 7072 | 3 | 4 | | | IV-1 | FRMD4B | 1.27 |
| 6977 | 3 | 4 | | | IV-1 | EGLN1 | 1.02 | 7073 | 3 | 4 | | | IV-1 | FRRS1 | 1.00 |
| 6978 | 3 | 4 | | | IV-1 | EHHADH | 1.24 | 7074 | 3 | 4 | | | IV-1 | FRZB | 1.15 |
| 6979 | 3 | 4 | | | IV-1 | EIF2A | 1.03 | 7075 | 3 | 4 | | | IV-1 | FTX | 1.20 |
| 6980 | 3 | 4 | | | IV-1 | EIF2AK2 | 1.18 | 7076 | 3 | 4 | | | IV-1 | FUCA1 | 1.13 |
| 6981 | 3 | 4 | | | IV-1 | EIF2B2 | 1.10 | 7077 | 3 | 4 | | | IV-1 | FUNDC1 | 1.06 |
| 6982 | 3 | 4 | | | IV-1 | EIF2S2 | 1.20 | 7078 | 3 | 4 | | | IV-1 | FUT1 | 1.01 |
| 6983 | 3 | 4 | | | IV-1 | EIF3J | 1.28 | 7079 | 3 | 4 | | | IV-1 | FXC1 | 1.02 |
| 6984 | 3 | 4 | | | IV-1 | EIF3M | 1.02 | 7080 | 3 | 4 | | | IV-1 | FXR1 | 1.06 |
| 6985 | 3 | 4 | | | IV-1 | EIF4A2 | 1.19 | 7081 | 3 | 4 | | | IV-1 | FZD1 | 1.21 |
| 6986 | 3 | 4 | | | IV-1 | EIF4EBP3 | 1.02 | 7082 | 3 | 4 | | | IV-1 | GAB1 | 1.14 |
| 6987 | 3 | 4 | | | IV-1 | ELF3 | 1.39 | 7083 | 3 | 4 | | | IV-1 | GABARAPL1 | 1.27 |
| 6988 | 3 | 4 | | | IV-1 | ELK4 | 1.06 | 7084 | 3 | 4 | | | IV-1 | GABPA | 1.11 |
| 6989 | 3 | 4 | | | IV-1 | ELL3 | 1.08 | 7085 | 3 | 4 | | | IV-1 | GALE | 1.04 |
| 6990 | 3 | 4 | | | IV-1 | ELMOD2 | 1.39 | 7086 | 3 | 4 | | | IV-1 | GALK2 | 1.11 |
| 6991 | 3 | 4 | | | IV-1 | ELP2 | 1.00 | 7087 | 3 | 4 | | | IV-1 | GALNTL2 | 1.16 |
| 6992 | 3 | 4 | | | IV-1 | ENTPD2 | 1.10 | 7088 | 3 | 4 | | | IV-1 | GAPVD1 | 1.03 |
| 6993 | 3 | 4 | | | IV-1 | EPB41L5 | 1.20 | 7089 | 3 | 4 | | | IV-1 | GAS2 | 1.16 |
| 6994 | 3 | 4 | | | IV-1 | EPDR1 | 1.11 | 7090 | 3 | 4 | | | IV-1 | GAS5 | 1.35 |
| 6995 | 3 | 4 | | | IV-1 | EPG5 | 1.20 | 7091 | 3 | 4 | | | IV-1 | GATSL3 | 1.00 |
| 6996 | 3 | 4 | | | IV-1 | EPHX2 | 1.16 | 7092 | 3 | 4 | | | IV-1 | GBAS | 1.14 |
| 6997 | 3 | 4 | | | IV-1 | EPS15 | 1.02 | 7093 | 3 | 4 | | | IV-1 | GBE1 | 1.00 |
| 6998 | 3 | 4 | | | IV-1 | ERBB3 | 1.34 | 7094 | 3 | 4 | | | IV-1 | GCFC2 | 1.25 |
| 6999 | 3 | 4 | | | IV-1 | ERCC4 | 1.00 | 7095 | 3 | 4 | | | IV-1 | GCH1 | 1.09 |
| 7000 | 3 | 4 | | | IV-1 | ERCC8 | 1.43 | 7096 | 3 | 4 | | | IV-1 | GCLC | 1.03 |
| 7001 | 3 | 4 | | | IV-1 | ERH | 1.09 | 7097 | 3 | 4 | | | IV-1 | GDPD3 | 1.13 |
| 7002 | 3 | 4 | | | IV-1 | ERICH1 | 1.11 | 7098 | 3 | 4 | | | IV-1 | GEMIN7 | 1.12 |
| 7003 | 3 | 4 | | | IV-1 | ERLEC1 | 1.21 | 7099 | 3 | 4 | | | IV-1 | GFM1 | 1.47 |
| 7004 | 3 | 4 | | | IV-1 | ESCO1 | 1.20 | 7100 | 3 | 4 | | | IV-1 | GFM2 | 1.35 |
| 7005 | 3 | 4 | | | IV-1 | ESD | 1.14 | 7101 | 3 | 4 | | | IV-1 | GFPT1 | 1.05 |

Fig. 39 - 38

| | | | | | | | | | | | | | | |
|---|---|---|---|---|---|---|---|---|---|---|---|---|---|---|
| 7102 | 3 | 4 | | | IV-1 | GFRA3 | 1.31 | 7198 | 3 | 4 | | | IV-1 | IBTK | 1.18 |
| 7103 | 3 | 4 | | | IV-1 | GGH | 1.29 | 7199 | 3 | 4 | | | IV-1 | ICK | 1.12 |
| 7104 | 3 | 4 | | | IV-1 | GGNBP2 | 1.14 | 7200 | 3 | 4 | | | IV-1 | IDH3A | 1.05 |
| 7105 | 3 | 4 | | | IV-1 | GGPS1 | 1.21 | 7201 | 3 | 4 | | | IV-1 | IER3IP1 | 1.07 |
| 7106 | 3 | 4 | | | IV-1 | GGTA1P | 1.23 | 7202 | 3 | 4 | | | IV-1 | IFI44L | 1.15 |
| 7107 | 3 | 4 | | | IV-1 | GHITM | 1.31 | 7203 | 3 | 4 | | | IV-1 | IFT74 | 1.18 |
| 7108 | 3 | 4 | | | IV-1 | GKAP1 | 1.04 | 7204 | 3 | 4 | | | IV-1 | IGF2 | 1.22 |
| 7109 | 3 | 4 | | | IV-1 | GLB1L3 | 1.37 | 7205 | 3 | 4 | | | IV-1 | IGF2BP2 | 1.06 |
| 7110 | 3 | 4 | | | IV-1 | GLRB | 1.34 | 7206 | 3 | 4 | | | IV-1 | IGIP | 1.04 |
| 7111 | 3 | 4 | | | IV-1 | GLRX5 | 1.10 | 7207 | 3 | 4 | | | IV-1 | IGSF11 | 1.01 |
| 7112 | 3 | 4 | | | IV-1 | GLUD1 | 1.01 | 7208 | 3 | 4 | | | IV-1 | IL10RB | 1.06 |
| 7113 | 3 | 4 | | | IV-1 | GMFB | 1.30 | 7209 | 3 | 4 | | | IV-1 | IL3RA | 1.04 |
| 7114 | 3 | 4 | | | IV-1 | GMNN | 1.49 | 7210 | 3 | 4 | | | IV-1 | ILF2 | 1.00 |
| 7115 | 3 | 4 | | | IV-1 | GMPR | 1.03 | 7211 | 3 | 4 | | | IV-1 | IMPA1 | 1.20 |
| 7116 | 3 | 4 | | | IV-1 | GNAL | 1.02 | 7212 | 3 | 4 | | | IV-1 | IMPA2 | 1.02 |
| 7117 | 3 | 4 | | | IV-1 | GNE | 1.24 | 7213 | 3 | 4 | | | IV-1 | IMPACT | 1.16 |
| 7118 | 3 | 4 | | | IV-1 | GNPTAB | 1.03 | 7214 | 3 | 4 | | | IV-1 | INADL | 1.40 |
| 7119 | 3 | 4 | | | IV-1 | GOLGB1 | 1.01 | 7215 | 3 | 4 | | | IV-1 | ING3 | 1.05 |
| 7120 | 3 | 4 | | | IV-1 | GOLT1B | 1.07 | 7216 | 3 | 4 | | | IV-1 | ING4 | 1.05 |
| 7121 | 3 | 4 | | | IV-1 | GOPC | 1.09 | 7217 | 3 | 4 | | | IV-1 | INO80C | 1.06 |
| 7122 | 3 | 4 | | | IV-1 | GOT1 | 1.19 | 7218 | 3 | 4 | | | IV-1 | INPP5F | 1.04 |
| 7123 | 3 | 4 | | | IV-1 | GPAT2 | 1.07 | 7219 | 3 | 4 | | | IV-1 | INTU | 1.17 |
| 7124 | 3 | 4 | | | IV-1 | GPCPD1 | 1.22 | 7220 | 3 | 4 | | | IV-1 | IPGK2 | 1.25 |
| 7125 | 3 | 4 | | | IV-1 | GPD1L | 1.05 | 7221 | 3 | 4 | | | IV-1 | IPO11 | 1.02 |
| 7126 | 3 | 4 | | | IV-1 | GPD2 | 1.38 | 7222 | 3 | 4 | | | IV-1 | IREB2 | 1.05 |
| 7127 | 3 | 4 | | | IV-1 | GPR180 | 1.01 | 7223 | 3 | 4 | | | IV-1 | ISCA2 | 1.01 |
| 7128 | 3 | 4 | | | IV-1 | GPR89B | 1.25 | 7224 | 3 | 4 | | | IV-1 | ITFG1 | 1.17 |
| 7129 | 3 | 4 | | | IV-1 | GPX3 | 1.40 | 7225 | 3 | 4 | | | IV-1 | ITGB8 | 1.40 |
| 7130 | 3 | 4 | | | IV-1 | GRPEL2 | 1.44 | 7226 | 3 | 4 | | | IV-1 | ITSN2 | 1.40 |
| 7131 | 3 | 4 | | | IV-1 | GTF2A2 | 1.00 | 7227 | 3 | 4 | | | IV-1 | IVD | 1.41 |
| 7132 | 3 | 4 | | | IV-1 | GTF2E2 | 1.11 | 7228 | 3 | 4 | | | IV-1 | IVNS1ABP | 1.07 |
| 7133 | 3 | 4 | | | IV-1 | GTF2F2 | 1.32 | 7229 | 3 | 4 | | | IV-1 | IKAMP | 1.17 |
| 7134 | 3 | 4 | | | IV-1 | GTF2H1 | 1.41 | 7230 | 3 | 4 | | | IV-1 | JMJD1C | 1.11 |
| 7135 | 3 | 4 | | | IV-1 | GTF2I | 1.05 | 7231 | 3 | 4 | | | IV-1 | JMJD4 | 1.06 |
| 7136 | 3 | 4 | | | IV-1 | GTF3C3 | 1.03 | 7232 | 3 | 4 | | | IV-1 | JRKL | 1.06 |
| 7137 | 3 | 4 | | | IV-1 | GTF3C6 | 1.26 | 7233 | 3 | 4 | | | IV-1 | KANK4 | 1.38 |
| 7138 | 3 | 4 | | | IV-1 | GTPBP10 | 1.04 | 7234 | 3 | 4 | | | IV-1 | KAT2B | 1.23 |
| 7139 | 3 | 4 | | | IV-1 | GUSBP3 | 1.36 | 7235 | 3 | 4 | | | IV-1 | KBTBD3 | 1.39 |
| 7140 | 3 | 4 | | | IV-1 | GUSBP4 | 1.14 | 7236 | 3 | 4 | | | IV-1 | KCNAB1 | 1.28 |
| 7141 | 3 | 4 | | | IV-1 | GXYLT1 | 1.01 | 7237 | 3 | 4 | | | IV-1 | KCNK12 | 1.05 |
| 7142 | 3 | 4 | | | IV-1 | GYG1 | 1.02 | 7238 | 3 | 4 | | | IV-1 | KCNMA1 | 1.11 |
| 7143 | 3 | 4 | | | IV-1 | GZF1 | 1.06 | 7239 | 3 | 4 | | | IV-1 | KCNMB3 | 1.31 |
| 7144 | 3 | 4 | | | IV-1 | GZMA | 1.36 | 7240 | 3 | 4 | | | IV-1 | KCNRG | 1.06 |
| 7145 | 3 | 4 | | | IV-1 | H2AFJ | 1.05 | 7241 | 3 | 4 | | | IV-1 | KCTD9 | 1.05 |
| 7146 | 3 | 4 | | | IV-1 | HACL1 | 1.31 | 7242 | 3 | 4 | | | IV-1 | KDM3A | 1.05 |
| 7147 | 3 | 4 | | | IV-1 | HBXIP | 1.06 | 7243 | 3 | 4 | | | IV-1 | KDSR | 1.08 |
| 7148 | 3 | 4 | | | IV-1 | HCG11 | 1.09 | 7244 | 3 | 4 | | | IV-1 | KIAA0196 | 1.01 |
| 7149 | 3 | 4 | | | IV-1 | HDDC2 | 1.16 | 7245 | 3 | 4 | | | IV-1 | KIAA0430 | 1.15 |
| 7150 | 3 | 4 | | | IV-1 | HDHD2 | 1.44 | 7246 | 3 | 4 | | | IV-1 | KIAA0528 | 1.17 |
| 7151 | 3 | 4 | | | IV-1 | HEBP2 | 1.35 | 7247 | 3 | 4 | | | IV-1 | KIAA0564 | 1.43 |
| 7152 | 3 | 4 | | | IV-1 | HECTD1 | 1.06 | 7248 | 3 | 4 | | | IV-1 | KIAA1147 | 1.08 |
| 7153 | 3 | 4 | | | IV-1 | HECW2 | 1.07 | 7249 | 3 | 4 | | | IV-1 | KIAA1279 | 1.13 |
| 7154 | 3 | 4 | | | IV-1 | HELT | 1.00 | 7250 | 3 | 4 | | | IV-1 | KIAA1432 | 1.18 |
| 7155 | 3 | 4 | | | IV-1 | HELZ | 1.03 | 7251 | 3 | 4 | | | IV-1 | KIAA1468 | 1.46 |
| 7156 | 3 | 4 | | | IV-1 | HERC4 | 1.11 | 7252 | 3 | 4 | | | IV-1 | KIAA1715 | 1.08 |
| 7157 | 3 | 4 | | | IV-1 | HERC6 | 1.18 | 7253 | 3 | 4 | | | IV-1 | KIAA2018 | 1.18 |
| 7158 | 3 | 4 | | | IV-1 | HES5 | 1.43 | 7254 | 3 | 4 | | | IV-1 | KIF1B | 1.21 |
| 7159 | 3 | 4 | | | IV-1 | HGD | 1.24 | 7255 | 3 | 4 | | | IV-1 | KIF20B | 1.21 |
| 7160 | 3 | 4 | | | IV-1 | HIF1A | 1.33 | 7256 | 3 | 4 | | | IV-1 | KIF2A | 1.12 |
| 7161 | 3 | 4 | | | IV-1 | HIGD1B | 1.22 | 7257 | 3 | 4 | | | IV-1 | KIT | 1.20 |
| 7162 | 3 | 4 | | | IV-1 | HINT1 | 1.22 | 7258 | 3 | 4 | | | IV-1 | KLHDC10 | 1.09 |
| 7163 | 3 | 4 | | | IV-1 | HINT2 | 1.08 | 7259 | 3 | 4 | | | IV-1 | KLHDC2 | 1.10 |
| 7164 | 3 | 4 | | | IV-1 | HIPK2 | 1.27 | 7260 | 3 | 4 | | | IV-1 | KLHDC5 | 1.06 |
| 7165 | 3 | 4 | | | IV-1 | HIST1H2AK | 1.05 | 7261 | 3 | 4 | | | IV-1 | KLHL12 | 1.02 |
| 7166 | 3 | 4 | | | IV-1 | HIST1H3A | 1.02 | 7262 | 3 | 4 | | | IV-1 | KLHL28 | 1.02 |
| 7167 | 3 | 4 | | | IV-1 | HIST1H3E | 1.04 | 7263 | 3 | 4 | | | IV-1 | KLHL9 | 1.07 |
| 7168 | 3 | 4 | | | IV-1 | HIST1H3H | 1.21 | 7264 | 3 | 4 | | | IV-1 | KLK1 | 1.03 |
| 7169 | 3 | 4 | | | IV-1 | HIST2H2BF | 1.08 | 7265 | 3 | 4 | | | IV-1 | KLRAP1 | 1.34 |
| 7170 | 3 | 4 | | | IV-1 | HIST2H3C | 1.27 | 7266 | 3 | 4 | | | IV-1 | KPNA3 | 1.11 |
| 7171 | 3 | 4 | | | IV-1 | HLTF | 1.13 | 7267 | 3 | 4 | | | IV-1 | KPNB1 | 1.03 |
| 7172 | 3 | 4 | | | IV-1 | HMGCL | 1.28 | 7268 | 3 | 4 | | | IV-1 | KRBA2 | 1.23 |
| 7173 | 3 | 4 | | | IV-1 | HMGN1 | 1.27 | 7269 | 3 | 4 | | | IV-1 | KRCC1 | 1.02 |
| 7174 | 3 | 4 | | | IV-1 | HMGXB4 | 1.08 | 7270 | 3 | 4 | | | IV-1 | KRR1 | 1.26 |
| 7175 | 3 | 4 | | | IV-1 | HNMT | 1.09 | 7271 | 3 | 4 | | | IV-1 | L3MBTL4 | 1.01 |
| 7176 | 3 | 4 | | | IV-1 | HNRNPA1 | 1.00 | 7272 | 3 | 4 | | | IV-1 | LACC1 | 1.42 |
| 7177 | 3 | 4 | | | IV-1 | HNRNPA3 | 1.08 | 7273 | 3 | 4 | | | IV-1 | LAIR1 | 1.38 |
| 7178 | 3 | 4 | | | IV-1 | HNRNPH3 | 1.04 | 7274 | 3 | 4 | | | IV-1 | LAMP5 | 1.06 |
| 7179 | 3 | 4 | | | IV-1 | HOMER1 | 1.34 | 7275 | 3 | 4 | | | IV-1 | LAMTOR3 | 1.27 |
| 7180 | 3 | 4 | | | IV-1 | HOXA7 | 1.00 | 7276 | 3 | 4 | | | IV-1 | LAP3 | 1.24 |
| 7181 | 3 | 4 | | | IV-1 | HP | 1.33 | 7277 | 3 | 4 | | | IV-1 | LBR | 1.07 |
| 7182 | 3 | 4 | | | IV-1 | HPS5 | 1.47 | 7278 | 3 | 4 | | | IV-1 | LCLAT1 | 1.09 |
| 7183 | 3 | 4 | | | IV-1 | HRSP12 | 1.06 | 7279 | 3 | 4 | | | IV-1 | LCMT1 | 1.31 |
| 7184 | 3 | 4 | | | IV-1 | HSCB | 1.03 | 7280 | 3 | 4 | | | IV-1 | LCOR | 1.08 |
| 7185 | 3 | 4 | | | IV-1 | HSD17B10 | 1.02 | 7281 | 3 | 4 | | | IV-1 | LGALS8 | 1.12 |
| 7186 | 3 | 4 | | | IV-1 | HSD17B4 | 1.07 | 7282 | 3 | 4 | | | IV-1 | LIAS | 1.02 |
| 7187 | 3 | 4 | | | IV-1 | HSD17B7 | 1.13 | 7283 | 3 | 4 | | | IV-1 | LIFR | 1.08 |
| 7188 | 3 | 4 | | | IV-1 | HSDL1 | 1.13 | 7284 | 3 | 4 | | | IV-1 | LIG4 | 1.08 |
| 7189 | 3 | 4 | | | IV-1 | HSDL2 | 1.32 | 7285 | 3 | 4 | | | IV-1 | LILRA2 | 1.15 |
| 7190 | 3 | 4 | | | IV-1 | HSP90AB4P | 1.31 | 7286 | 3 | 4 | | | IV-1 | LIN54 | 1.06 |
| 7191 | 3 | 4 | | | IV-1 | HSP90B1 | 1.21 | 7287 | 3 | 4 | | | IV-1 | LIN7B | 1.02 |
| 7192 | 3 | 4 | | | IV-1 | HSP90B3P | 1.24 | 7288 | 3 | 4 | | | IV-1 | LIN7C | 1.00 |
| 7193 | 3 | 4 | | | IV-1 | HSPA14 | 1.28 | 7289 | 3 | 4 | | | IV-1 | LIN9 | 1.13 |
| 7194 | 3 | 4 | | | IV-1 | HSPA9 | 1.16 | 7290 | 3 | 4 | | | IV-1 | LINC00310 | 1.08 |
| 7195 | 3 | 4 | | | IV-1 | HSPH1 | 1.05 | 7291 | 3 | 4 | | | IV-1 | LINC00467 | 1.01 |
| 7196 | 3 | 4 | | | IV-1 | HUS1 | 1.08 | 7292 | 3 | 4 | | | IV-1 | LINC00478 | 1.13 |
| 7197 | 3 | 4 | | | IV-1 | HVCN1 | 1.04 | 7293 | 3 | 4 | | | IV-1 | LINC00493 | 1.28 |

Fig. 39 - 39

| | | | | | | | |
|---|---|---|---|---|---|---|---|
| 7294 | 3 | 4 | | | IV-1 | LIPA | 1.09 |
| 7295 | 3 | 4 | | | IV-1 | LITAF | 1.23 |
| 7296 | 3 | 4 | | | IV-1 | LLPH | 1.12 |
| 7297 | 3 | 4 | | | IV-1 | LMAN1 | 1.28 |
| 7298 | 3 | 4 | | | IV-1 | LMBR1 | 1.04 |
| 7299 | 3 | 4 | | | IV-1 | LMBRD1 | 1.09 |
| 7300 | 3 | 4 | | | IV-1 | LMO7 | 1.34 |
| 7301 | 3 | 4 | | | IV-1 | LMTK3 | 1.05 |
| 7302 | 3 | 4 | | | IV-1 | LOC100093631 | 1.06 |
| 7303 | 3 | 4 | | | IV-1 | LOC100128511 | 1.43 |
| 7304 | 3 | 4 | | | IV-1 | LOC100128573 | 1.21 |
| 7305 | 3 | 4 | | | IV-1 | LOC100129250 | 1.27 |
| 7306 | 3 | 4 | | | IV-1 | LOC100129361 | 1.04 |
| 7307 | 3 | 4 | | | IV-1 | LOC100129480 | 1.03 |
| 7308 | 3 | 4 | | | IV-1 | LOC100132215 | 1.40 |
| 7309 | 3 | 4 | | | IV-1 | LOC100134259 | 1.09 |
| 7310 | 3 | 4 | | | IV-1 | LOC100144603 | 1.22 |
| 7311 | 3 | 4 | | | IV-1 | LOC100170939 | 1.23 |
| 7312 | 3 | 4 | | | IV-1 | LOC100288615 | 1.38 |
| 7313 | 3 | 4 | | | IV-1 | LOC100288748 | 1.17 |
| 7314 | 3 | 4 | | | IV-1 | LOC100289255 | 1.08 |
| 7315 | 3 | 4 | | | IV-1 | LOC100505695 | 1.12 |
| 7316 | 3 | 4 | | | IV-1 | LOC100505702 | 1.38 |
| 7317 | 3 | 4 | | | IV-1 | LOC100505761 | 1.12 |
| 7318 | 3 | 4 | | | IV-1 | LOC100505783 | 1.22 |
| 7319 | 3 | 4 | | | IV-1 | LOC100505894 | 1.00 |
| 7320 | 3 | 4 | | | IV-1 | LOC100506046 | 1.29 |
| 7321 | 3 | 4 | | | IV-1 | LOC100506710 | 1.15 |
| 7322 | 3 | 4 | | | IV-1 | LOC100506714 | 1.17 |
| 7323 | 3 | 4 | | | IV-1 | LOC100506844 | 1.11 |
| 7324 | 3 | 4 | | | IV-1 | LOC100507495 | 1.28 |
| 7325 | 3 | 4 | | | IV-1 | LOC100507557 | 1.03 |
| 7326 | 3 | 4 | | | IV-1 | LOC100508120 | 1.02 |
| 7327 | 3 | 4 | | | IV-1 | LOC100509894 | 1.48 |
| 7328 | 3 | 4 | | | IV-1 | LOC147727 | 1.33 |
| 7329 | 3 | 4 | | | IV-1 | LOC151009 | 1.03 |
| 7330 | 3 | 4 | | | IV-1 | LOC257396 | 1.19 |
| 7331 | 3 | 4 | | | IV-1 | LOC284009 | 1.44 |
| 7332 | 3 | 4 | | | IV-1 | LOC284578 | 1.10 |
| 7333 | 3 | 4 | | | IV-1 | LOC340357 | 1.01 |
| 7334 | 3 | 4 | | | IV-1 | LOC386758 | 1.13 |
| 7335 | 3 | 4 | | | IV-1 | LOC388588 | 1.31 |
| 7336 | 3 | 4 | | | IV-1 | LOC389033 | 1.04 |
| 7337 | 3 | 4 | | | IV-1 | LOC390940 | 1.04 |
| 7338 | 3 | 4 | | | IV-1 | LOC400236 | 1.31 |
| 7339 | 3 | 4 | | | IV-1 | LOC401588 | 1.16 |
| 7340 | 3 | 4 | | | IV-1 | LOC441454 | 1.14 |
| 7341 | 3 | 4 | | | IV-1 | LOC553103 | 1.08 |
| 7342 | 3 | 4 | | | IV-1 | LOC613038 | 1.22 |
| 7343 | 3 | 4 | | | IV-1 | LOC641746 | 1.29 |
| 7344 | 3 | 4 | | | IV-1 | LOC642361 | 1.08 |
| 7345 | 3 | 4 | | | IV-1 | LOC644990 | 1.05 |
| 7346 | 3 | 4 | | | IV-1 | LOC727896 | 1.08 |
| 7347 | 3 | 4 | | | IV-1 | LOC728066 | 1.18 |
| 7348 | 3 | 4 | | | IV-1 | LOC728606 | 1.49 |
| 7349 | 3 | 4 | | | IV-1 | LOC728730 | 1.04 |
| 7350 | 3 | 4 | | | IV-1 | LOC729178 | 1.11 |
| 7351 | 3 | 4 | | | IV-1 | LOC729678 | 1.24 |
| 7352 | 3 | 4 | | | IV-1 | LOC80054 | 1.14 |
| 7353 | 3 | 4 | | | IV-1 | LOC93622 | 1.12 |
| 7354 | 3 | 4 | | | IV-1 | LOC96610 | 1.05 |
| 7355 | 3 | 4 | | | IV-1 | LOH12CR2 | 1.06 |
| 7356 | 3 | 4 | | | IV-1 | LPAR6 | 1.11 |
| 7357 | 3 | 4 | | | IV-1 | LPGAT1 | 1.14 |
| 7358 | 3 | 4 | | | IV-1 | LPXN | 1.04 |
| 7359 | 3 | 4 | | | IV-1 | LRP6 | 1.04 |
| 7360 | 3 | 4 | | | IV-1 | LRPPRC | 1.05 |
| 7361 | 3 | 4 | | | IV-1 | LRRC2 | 1.00 |
| 7362 | 3 | 4 | | | IV-1 | LSM6 | 1.17 |
| 7363 | 3 | 4 | | | IV-1 | LSMD1 | 1.04 |
| 7364 | 3 | 4 | | | IV-1 | LTN1 | 1.20 |
| 7365 | 3 | 4 | | | IV-1 | LYAR | 1.34 |
| 7366 | 3 | 4 | | | IV-1 | LYPLAL1 | 1.34 |
| 7367 | 3 | 4 | | | IV-1 | LYRM1 | 1.09 |
| 7368 | 3 | 4 | | | IV-1 | LYRM2 | 1.30 |
| 7369 | 3 | 4 | | | IV-1 | LYSMD1 | 1.07 |
| 7370 | 3 | 4 | | | IV-1 | LYSMD3 | 1.08 |
| 7371 | 3 | 4 | | | IV-1 | LYST | 1.26 |
| 7372 | 3 | 4 | | | IV-1 | MACROD2 | 1.36 |
| 7373 | 3 | 4 | | | IV-1 | MAFG | 1.11 |
| 7374 | 3 | 4 | | | IV-1 | MAGEA11 | 1.11 |
| 7375 | 3 | 4 | | | IV-1 | MAGI1 | 1.15 |
| 7376 | 3 | 4 | | | IV-1 | MAGIX | 1.11 |
| 7377 | 3 | 4 | | | IV-1 | MAK16 | 1.02 |
| 7378 | 3 | 4 | | | IV-1 | MALT1 | 1.09 |
| 7379 | 3 | 4 | | | IV-1 | MANEA | 1.13 |
| 7380 | 3 | 4 | | | IV-1 | MANF | 1.17 |
| 7381 | 3 | 4 | | | IV-1 | MAP1LC3A | 1.22 |
| 7382 | 3 | 4 | | | IV-1 | MAP1LC3B | 1.07 |
| 7383 | 3 | 4 | | | IV-1 | MAP1LC3B2 | 1.08 |
| 7384 | 3 | 4 | | | IV-1 | MAP2 | 1.03 |
| 7385 | 3 | 4 | | | IV-1 | MAP2K4 | 1.04 |
| 7386 | 3 | 4 | | | IV-1 | MAP3K13 | 1.02 |
| 7387 | 3 | 4 | | | IV-1 | MAP3K7 | 1.05 |
| 7388 | 3 | 4 | | | IV-1 | MAPK10 | 1.25 |
| 7389 | 3 | 4 | | | IV-1 | MAPK8 | 1.20 |
| 7390 | 3 | 4 | | | IV-1 | MARCH5 | 1.00 |
| 7391 | 3 | 4 | | | IV-1 | MARVELD3 | 1.07 |
| 7392 | 3 | 4 | | | IV-1 | MASP2 | 1.05 |
| 7393 | 3 | 4 | | | IV-1 | MATK | 1.27 |
| 7394 | 3 | 4 | | | IV-1 | MATR3 | 1.24 |
| 7395 | 3 | 4 | | | IV-1 | MBIP | 1.09 |
| 7396 | 3 | 4 | | | IV-1 | MBTD1 | 1.11 |
| 7397 | 3 | 4 | | | IV-1 | MCCC1 | 1.49 |
| 7398 | 3 | 4 | | | IV-1 | MCCC2 | 1.11 |
| 7399 | 3 | 4 | | | IV-1 | MDH1 | 1.33 |
| 7400 | 3 | 4 | | | IV-1 | MDM2 | 1.20 |
| 7401 | 3 | 4 | | | IV-1 | MDP1 | 1.13 |
| 7402 | 3 | 4 | | | IV-1 | MECR | 1.09 |
| 7403 | 3 | 4 | | | IV-1 | MED13 | 1.21 |
| 7404 | 3 | 4 | | | IV-1 | MED8 | 1.11 |
| 7405 | 3 | 4 | | | IV-1 | MED9 | 1.19 |
| 7406 | 3 | 4 | | | IV-1 | MEIS2 | 1.02 |
| 7407 | 3 | 4 | | | IV-1 | METAP1 | 1.05 |
| 7408 | 3 | 4 | | | IV-1 | METAP2 | 1.38 |
| 7409 | 3 | 4 | | | IV-1 | METRN | 1.40 |
| 7410 | 3 | 4 | | | IV-1 | METTL14 | 1.03 |
| 7411 | 3 | 4 | | | IV-1 | METTL15 | 1.13 |
| 7412 | 3 | 4 | | | IV-1 | METTL21A | 1.13 |
| 7413 | 3 | 4 | | | IV-1 | METTL21B | 1.10 |
| 7414 | 3 | 4 | | | IV-1 | METTL21D | 1.25 |
| 7415 | 3 | 4 | | | IV-1 | METTL7A | 1.40 |
| 7416 | 3 | 4 | | | IV-1 | METTL8 | 1.13 |
| 7417 | 3 | 4 | | | IV-1 | MFN1 | 1.38 |
| 7418 | 3 | 4 | | | IV-1 | MFSD1 | 1.35 |
| 7419 | 3 | 4 | | | IV-1 | MFSD11 | 1.02 |
| 7420 | 3 | 4 | | | IV-1 | MFSD3 | 1.06 |
| 7421 | 3 | 4 | | | IV-1 | MGC21881 | 1.46 |
| 7422 | 3 | 4 | | | IV-1 | MGST3 | 1.06 |
| 7423 | 3 | 4 | | | IV-1 | MIB1 | 1.10 |
| 7424 | 3 | 4 | | | IV-1 | MIER3 | 1.23 |
| 7425 | 3 | 4 | | | IV-1 | MIR22HG | 1.27 |
| 7426 | 3 | 4 | | | IV-1 | MIR600HG | 1.13 |
| 7427 | 3 | 4 | | | IV-1 | MIS12 | 1.09 |
| 7428 | 3 | 4 | | | IV-1 | MIS18A | 1.10 |
| 7429 | 3 | 4 | | | IV-1 | MKLN1 | 1.30 |
| 7430 | 3 | 4 | | | IV-1 | MLL | 1.35 |
| 7431 | 3 | 4 | | | IV-1 | MLL3 | 1.22 |
| 7432 | 3 | 4 | | | IV-1 | MLLT4 | 1.26 |
| 7433 | 3 | 4 | | | IV-1 | MMAA | 1.18 |
| 7434 | 3 | 4 | | | IV-1 | MMADHC | 1.33 |
| 7435 | 3 | 4 | | | IV-1 | MNAT1 | 1.38 |
| 7436 | 3 | 4 | | | IV-1 | MNF1 | 1.07 |
| 7437 | 3 | 4 | | | IV-1 | MNS1 | 1.33 |
| 7438 | 3 | 4 | | | IV-1 | MOAP1 | 1.11 |
| 7439 | 3 | 4 | | | IV-1 | MOGAT1 | 1.15 |
| 7440 | 3 | 4 | | | IV-1 | MON2 | 1.16 |
| 7441 | 3 | 4 | | | IV-1 | MORC3 | 1.01 |
| 7442 | 3 | 4 | | | IV-1 | MORF4L1 | 1.06 |
| 7443 | 3 | 4 | | | IV-1 | MORN4 | 1.15 |
| 7444 | 3 | 4 | | | IV-1 | MPHOSPH10 | 1.04 |
| 7445 | 3 | 4 | | | IV-1 | MPI | 1.08 |
| 7446 | 3 | 4 | | | IV-1 | MPL | 1.24 |
| 7447 | 3 | 4 | | | IV-1 | MPP2 | 1.12 |
| 7448 | 3 | 4 | | | IV-1 | MPP5 | 1.30 |
| 7449 | 3 | 4 | | | IV-1 | MRI1 | 1.08 |
| 7450 | 3 | 4 | | | IV-1 | MRPL15 | 1.29 |
| 7451 | 3 | 4 | | | IV-1 | MRPL19 | 1.36 |
| 7452 | 3 | 4 | | | IV-1 | MRPL20 | 1.28 |
| 7453 | 3 | 4 | | | IV-1 | MRPL21 | 1.06 |
| 7454 | 3 | 4 | | | IV-1 | MRPL27 | 1.13 |
| 7455 | 3 | 4 | | | IV-1 | MRPL30 | 1.08 |
| 7456 | 3 | 4 | | | IV-1 | MRPL36 | 1.35 |
| 7457 | 3 | 4 | | | IV-1 | MRPL41 | 1.14 |
| 7458 | 3 | 4 | | | IV-1 | MRPL4SP2 | 1.21 |
| 7459 | 3 | 4 | | | IV-1 | MRPL47 | 1.21 |
| 7460 | 3 | 4 | | | IV-1 | MRPL48 | 1.24 |
| 7461 | 3 | 4 | | | IV-1 | MRPL51 | 1.06 |
| 7462 | 3 | 4 | | | IV-1 | MRPS10 | 1.25 |
| 7463 | 3 | 4 | | | IV-1 | MRPS14 | 1.11 |
| 7464 | 3 | 4 | | | IV-1 | MRPS15 | 1.06 |
| 7465 | 3 | 4 | | | IV-1 | MRPS17 | 1.04 |
| 7466 | 3 | 4 | | | IV-1 | MRPS18C | 1.48 |
| 7467 | 3 | 4 | | | IV-1 | MRPS24 | 1.00 |
| 7468 | 3 | 4 | | | IV-1 | MRPS25 | 1.32 |
| 7469 | 3 | 4 | | | IV-1 | MRPS28 | 1.20 |
| 7470 | 3 | 4 | | | IV-1 | MRPS35 | 1.23 |
| 7471 | 3 | 4 | | | IV-1 | MRPS36 | 1.10 |
| 7472 | 3 | 4 | | | IV-1 | MRPS7 | 1.03 |
| 7473 | 3 | 4 | | | IV-1 | MRS2 | 1.40 |
| 7474 | 3 | 4 | | | IV-1 | MTA3 | 1.13 |
| 7475 | 3 | 4 | | | IV-1 | MTCP1 | 1.33 |
| 7476 | 3 | 4 | | | IV-1 | MTF2 | 1.42 |
| 7477 | 3 | 4 | | | IV-1 | MTFP1 | 1.11 |
| 7478 | 3 | 4 | | | IV-1 | MTMR10 | 1.18 |
| 7479 | 3 | 4 | | | IV-1 | MTMR7 | 1.16 |
| 7480 | 3 | 4 | | | IV-1 | MTMR9 | 1.18 |
| 7481 | 3 | 4 | | | IV-1 | MTRF1L | 1.19 |
| 7482 | 3 | 4 | | | IV-1 | MTRNR2L1 | 1.09 |
| 7483 | 3 | 4 | | | IV-1 | MTRR | 1.21 |
| 7484 | 3 | 4 | | | IV-1 | MTX2 | 1.07 |
| 7485 | 3 | 4 | | | IV-1 | MTX3 | 1.46 |

Fig. 39 - 40

| | | | | | | | |
|---|---|---|---|---|---|---|---|
| 7486 | 3 | 4 | | | IV-1 | MUC7 | 1.14 |
| 7487 | 3 | 4 | | | IV-1 | MUDENG | 1.37 |
| 7488 | 3 | 4 | | | IV-1 | MYCBP2 | 1.48 |
| 7489 | 3 | 4 | | | IV-1 | MYEOV2 | 1.14 |
| 7490 | 3 | 4 | | | IV-1 | MYLK-AS1 | 1.43 |
| 7491 | 3 | 4 | | | IV-1 | MYNN | 1.11 |
| 7492 | 3 | 4 | | | IV-1 | MYO6 | 1.29 |
| 7493 | 3 | 4 | | | IV-1 | MYSM1 | 1.11 |
| 7494 | 3 | 4 | | | IV-1 | MYZAP | 1.03 |
| 7495 | 3 | 4 | | | IV-1 | MZT1 | 1.09 |
| 7496 | 3 | 4 | | | IV-1 | N6AMT1 | 1.25 |
| 7497 | 3 | 4 | | | IV-1 | NAA20 | 1.18 |
| 7498 | 3 | 4 | | | IV-1 | NAA25 | 1.11 |
| 7499 | 3 | 4 | | | IV-1 | NAA38 | 1.14 |
| 7500 | 3 | 4 | | | IV-1 | NACA2 | 1.29 |
| 7501 | 3 | 4 | | | IV-1 | NACAP1 | 1.01 |
| 7502 | 3 | 4 | | | IV-1 | NADKD1 | 1.18 |
| 7503 | 3 | 4 | | | IV-1 | NADSYN1 | 1.02 |
| 7504 | 3 | 4 | | | IV-1 | NAE1 | 1.30 |
| 7505 | 3 | 4 | | | IV-1 | NAGK | 1.04 |
| 7506 | 3 | 4 | | | IV-1 | NAMPT | 1.22 |
| 7507 | 3 | 4 | | | IV-1 | NAP1L1 | 1.25 |
| 7508 | 3 | 4 | | | IV-1 | NAP1L4 | 1.00 |
| 7509 | 3 | 4 | | | IV-1 | NAP1L5 | 1.04 |
| 7510 | 3 | 4 | | | IV-1 | NAPEPLD | 1.38 |
| 7511 | 3 | 4 | | | IV-1 | NAPG | 1.12 |
| 7512 | 3 | 4 | | | IV-1 | NAP5A | 1.13 |
| 7513 | 3 | 4 | | | IV-1 | NARFL | 1.24 |
| 7514 | 3 | 4 | | | IV-1 | NAV3 | 1.15 |
| 7515 | 3 | 4 | | | IV-1 | NBN | 1.11 |
| 7516 | 3 | 4 | | | IV-1 | NBPF15 | 1.37 |
| 7517 | 3 | 4 | | | IV-1 | NBPF3 | 1.09 |
| 7518 | 3 | 4 | | | IV-1 | NBPF9 | 1.26 |
| 7519 | 3 | 4 | | | IV-1 | NCBP1 | 1.26 |
| 7520 | 3 | 4 | | | IV-1 | NCF1B | 1.47 |
| 7521 | 3 | 4 | | | IV-1 | NCOA1 | 1.02 |
| 7522 | 3 | 4 | | | IV-1 | NDFIP1 | 1.03 |
| 7523 | 3 | 4 | | | IV-1 | NDP | 1.03 |
| 7524 | 3 | 4 | | | IV-1 | NDRG2 | 1.06 |
| 7525 | 3 | 4 | | | IV-1 | NDUFA10 | 1.09 |
| 7526 | 3 | 4 | | | IV-1 | NDUFA12 | 1.26 |
| 7527 | 3 | 4 | | | IV-1 | NDUFA3 | 1.29 |
| 7528 | 3 | 4 | | | IV-1 | NDUFA4 | 1.18 |
| 7529 | 3 | 4 | | | IV-1 | NDUFA6 | 1.46 |
| 7530 | 3 | 4 | | | IV-1 | NDUFA8 | 1.06 |
| 7531 | 3 | 4 | | | IV-1 | NDUFA9 | 1.08 |
| 7532 | 3 | 4 | | | IV-1 | NDUFAB1 | 1.12 |
| 7533 | 3 | 4 | | | IV-1 | NDUFAF4 | 1.34 |
| 7534 | 3 | 4 | | | IV-1 | NDUFB2 | 1.33 |
| 7535 | 3 | 4 | | | IV-1 | NDUFB5 | 1.37 |
| 7536 | 3 | 4 | | | IV-1 | NDUFB6 | 1.27 |
| 7537 | 3 | 4 | | | IV-1 | NDUFB9 | 1.00 |
| 7538 | 3 | 4 | | | IV-1 | NDUFC1 | 1.18 |
| 7539 | 3 | 4 | | | IV-1 | NDUFC2 | 1.26 |
| 7540 | 3 | 4 | | | IV-1 | NDUFS2 | 1.02 |
| 7541 | 3 | 4 | | | IV-1 | NDUFS4 | 1.13 |
| 7542 | 3 | 4 | | | IV-1 | NDUFS6 | 1.08 |
| 7543 | 3 | 4 | | | IV-1 | NDUFV2 | 1.01 |
| 7544 | 3 | 4 | | | IV-1 | NEAT1 | 1.22 |
| 7545 | 3 | 4 | | | IV-1 | NECAB1 | 1.10 |
| 7546 | 3 | 4 | | | IV-1 | NECAB3 | 1.33 |
| 7547 | 3 | 4 | | | IV-1 | NECAP1 | 1.05 |
| 7548 | 3 | 4 | | | IV-1 | NEDD4 | 1.17 |
| 7549 | 3 | 4 | | | IV-1 | NEDD8 | 1.09 |
| 7550 | 3 | 4 | | | IV-1 | NEK1 | 1.08 |
| 7551 | 3 | 4 | | | IV-1 | NEK6 | 1.05 |
| 7552 | 3 | 4 | | | IV-1 | NEK7 | 1.10 |
| 7553 | 3 | 4 | | | IV-1 | NELL1 | 1.23 |
| 7554 | 3 | 4 | | | IV-1 | NETO2 | 1.10 |
| 7555 | 3 | 4 | | | IV-1 | NGFRAP1 | 1.30 |
| 7556 | 3 | 4 | | | IV-1 | NGLY1 | 1.09 |
| 7557 | 3 | 4 | | | IV-1 | NIPA2 | 1.05 |
| 7558 | 3 | 4 | | | IV-1 | NKIRAS1 | 1.19 |
| 7559 | 3 | 4 | | | IV-1 | NLK | 1.35 |
| 7560 | 3 | 4 | | | IV-1 | NLRP10 | 1.16 |
| 7561 | 3 | 4 | | | IV-1 | NMD3 | 1.03 |
| 7562 | 3 | 4 | | | IV-1 | NME2 | 1.05 |
| 7563 | 3 | 4 | | | IV-1 | NME7 | 1.35 |
| 7564 | 3 | 4 | | | IV-1 | NMNAT1 | 1.03 |
| 7565 | 3 | 4 | | | IV-1 | NMT2 | 1.01 |
| 7566 | 3 | 4 | | | IV-1 | NMU | 1.26 |
| 7567 | 3 | 4 | | | IV-1 | NNT | 1.29 |
| 7568 | 3 | 4 | | | IV-1 | NOL10 | 1.02 |
| 7569 | 3 | 4 | | | IV-1 | NOL8 | 1.45 |
| 7570 | 3 | 4 | | | IV-1 | NOP10 | 1.20 |
| 7571 | 3 | 4 | | | IV-1 | NPC1 | 1.12 |
| 7572 | 3 | 4 | | | IV-1 | NPC2 | 1.08 |
| 7573 | 3 | 4 | | | IV-1 | NR2C2 | 1.17 |
| 7574 | 3 | 4 | | | IV-1 | NRG2 | 1.12 |
| 7575 | 3 | 4 | | | IV-1 | NRXN1 | 1.44 |
| 7576 | 3 | 4 | | | IV-1 | NSL1 | 1.05 |
| 7577 | 3 | 4 | | | IV-1 | NSUN4 | 1.28 |
| 7578 | 3 | 4 | | | IV-1 | NT5C2 | 1.04 |
| 7579 | 3 | 4 | | | IV-1 | NT5DC1 | 1.05 |
| 7580 | 3 | 4 | | | IV-1 | NUBPL | 1.22 |
| 7581 | 3 | 4 | | | IV-1 | NUCB2 | 1.44 |
| 7582 | 3 | 4 | | | IV-1 | NUCKS1 | 1.02 |
| 7583 | 3 | 4 | | | IV-1 | NUDCD2 | 1.06 |
| 7584 | 3 | 4 | | | IV-1 | NUDT13 | 1.19 |
| 7585 | 3 | 4 | | | IV-1 | NUDT2 | 1.17 |
| 7586 | 3 | 4 | | | IV-1 | NUDT21 | 1.05 |
| 7587 | 3 | 4 | | | IV-1 | NUDT7 | 1.15 |
| 7588 | 3 | 4 | | | IV-1 | NUP50 | 1.22 |
| 7589 | 3 | 4 | | | IV-1 | NUPL1 | 1.14 |
| 7590 | 3 | 4 | | | IV-1 | OCA2 | 1.01 |
| 7591 | 3 | 4 | | | IV-1 | OCIAD1 | 1.06 |
| 7592 | 3 | 4 | | | IV-1 | OGG1 | 1.33 |
| 7593 | 3 | 4 | | | IV-1 | OIP5-AS1 | 1.28 |
| 7594 | 3 | 4 | | | IV-1 | OMA1 | 1.36 |
| 7595 | 3 | 4 | | | IV-1 | OPA1 | 1.06 |
| 7596 | 3 | 4 | | | IV-1 | OR2A4 | 1.19 |
| 7597 | 3 | 4 | | | IV-1 | OR7E91P | 1.04 |
| 7598 | 3 | 4 | | | IV-1 | ORC4 | 1.05 |
| 7599 | 3 | 4 | | | IV-1 | ORMDL1 | 1.27 |
| 7600 | 3 | 4 | | | IV-1 | ORMDL2 | 1.05 |
| 7601 | 3 | 4 | | | IV-1 | OSBPL1A | 1.02 |
| 7602 | 3 | 4 | | | IV-1 | OSCP1 | 1.03 |
| 7603 | 3 | 4 | | | IV-1 | OST4 | 1.16 |
| 7604 | 3 | 4 | | | IV-1 | OSTC | 1.20 |
| 7605 | 3 | 4 | | | IV-1 | OSTCP1 | 1.41 |
| 7606 | 3 | 4 | | | IV-1 | OTUD6B | 1.11 |
| 7607 | 3 | 4 | | | IV-1 | OTX1 | 1.04 |
| 7608 | 3 | 4 | | | IV-1 | OXCT1 | 1.13 |
| 7609 | 3 | 4 | | | IV-1 | OXNAD1 | 1.03 |
| 7610 | 3 | 4 | | | IV-1 | OXR1 | 1.29 |
| 7611 | 3 | 4 | | | IV-1 | PACRGL | 1.05 |
| 7612 | 3 | 4 | | | IV-1 | PAFAH1B1 | 1.14 |
| 7613 | 3 | 4 | | | IV-1 | PAIP2 | 1.20 |
| 7614 | 3 | 4 | | | IV-1 | PAN3 | 1.07 |
| 7615 | 3 | 4 | | | IV-1 | PAPD4 | 1.09 |
| 7616 | 3 | 4 | | | IV-1 | PAPD5 | 1.00 |
| 7617 | 3 | 4 | | | IV-1 | PAQR3 | 1.13 |
| 7618 | 3 | 4 | | | IV-1 | PARG | 1.07 |
| 7619 | 3 | 4 | | | IV-1 | PARK7 | 1.11 |
| 7620 | 3 | 4 | | | IV-1 | PARP8 | 1.04 |
| 7621 | 3 | 4 | | | IV-1 | PAWR | 1.19 |
| 7622 | 3 | 4 | | | IV-1 | PAX6 | 1.01 |
| 7623 | 3 | 4 | | | IV-1 | PBX3 | 1.02 |
| 7624 | 3 | 4 | | | IV-1 | PC | 1.46 |
| 7625 | 3 | 4 | | | IV-1 | PCBD1 | 1.02 |
| 7626 | 3 | 4 | | | IV-1 | PCDH85 | 1.19 |
| 7627 | 3 | 4 | | | IV-1 | PCGF1 | 1.20 |
| 7628 | 3 | 4 | | | IV-1 | PCM1 | 1.19 |
| 7629 | 3 | 4 | | | IV-1 | PCMT1 | 1.09 |
| 7630 | 3 | 4 | | | IV-1 | PCMTD2 | 1.38 |
| 7631 | 3 | 4 | | | IV-1 | PCNP | 1.09 |
| 7632 | 3 | 4 | | | IV-1 | PCP2 | 1.04 |
| 7633 | 3 | 4 | | | IV-1 | PCSK6 | 1.10 |
| 7634 | 3 | 4 | | | IV-1 | PCYOX1 | 1.25 |
| 7635 | 3 | 4 | | | IV-1 | PDCD10 | 1.45 |
| 7636 | 3 | 4 | | | IV-1 | PDCD2 | 1.06 |
| 7637 | 3 | 4 | | | IV-1 | PDCD7 | 1.18 |
| 7638 | 3 | 4 | | | IV-1 | PDE3B | 1.37 |
| 7639 | 3 | 4 | | | IV-1 | PDE4B | 1.27 |
| 7640 | 3 | 4 | | | IV-1 | PDE7A | 1.16 |
| 7641 | 3 | 4 | | | IV-1 | PDF | 1.28 |
| 7642 | 3 | 4 | | | IV-1 | PDHA1 | 1.40 |
| 7643 | 3 | 4 | | | IV-1 | PDHB | 1.20 |
| 7644 | 3 | 4 | | | IV-1 | PDHX | 1.49 |
| 7645 | 3 | 4 | | | IV-1 | PDIK1L | 1.42 |
| 7646 | 3 | 4 | | | IV-1 | PDK1 | 1.20 |
| 7647 | 3 | 4 | | | IV-1 | PDK4 | 1.45 |
| 7648 | 3 | 4 | | | IV-1 | PDRG1 | 1.26 |
| 7649 | 3 | 4 | | | IV-1 | PDS5A | 1.02 |
| 7650 | 3 | 4 | | | IV-1 | PDZD2 | 1.23 |
| 7651 | 3 | 4 | | | IV-1 | PEBP1 | 1.10 |
| 7652 | 3 | 4 | | | IV-1 | PEBP4 | 1.30 |
| 7653 | 3 | 4 | | | IV-1 | PEMT | 1.15 |
| 7654 | 3 | 4 | | | IV-1 | PET112 | 1.24 |
| 7655 | 3 | 4 | | | IV-1 | PEX11G | 1.26 |
| 7656 | 3 | 4 | | | IV-1 | PEX19 | 1.22 |
| 7657 | 3 | 4 | | | IV-1 | PEX2 | 1.15 |
| 7658 | 3 | 4 | | | IV-1 | PEX3 | 1.49 |
| 7659 | 3 | 4 | | | IV-1 | PEX7 | 1.24 |
| 7660 | 3 | 4 | | | IV-1 | PFKFB4 | 1.27 |
| 7661 | 3 | 4 | | | IV-1 | PFN2 | 1.02 |
| 7662 | 3 | 4 | | | IV-1 | PGAP2 | 1.24 |
| 7663 | 3 | 4 | | | IV-1 | PGK1 | 1.03 |
| 7664 | 3 | 4 | | | IV-1 | PGM1 | 1.09 |
| 7665 | 3 | 4 | | | IV-1 | PGM2L1 | 1.36 |
| 7666 | 3 | 4 | | | IV-1 | PGRMC1 | 1.29 |
| 7667 | 3 | 4 | | | IV-1 | PHAX | 1.06 |
| 7668 | 3 | 4 | | | IV-1 | PHC3 | 1.08 |
| 7669 | 3 | 4 | | | IV-1 | PHF16 | 1.31 |
| 7670 | 3 | 4 | | | IV-1 | PHF20 | 1.14 |
| 7671 | 3 | 4 | | | IV-1 | PHF20L1 | 1.35 |
| 7672 | 3 | 4 | | | IV-1 | PHLDA1 | 1.29 |
| 7673 | 3 | 4 | | | IV-1 | PHLDA3 | 1.22 |
| 7674 | 3 | 4 | | | IV-1 | PHLDB2 | 1.16 |
| 7675 | 3 | 4 | | | IV-1 | PHOSPHO1 | 1.28 |
| 7676 | 3 | 4 | | | IV-1 | PHOSPHO2 | 1.38 |
| 7677 | 3 | 4 | | | IV-1 | PHYHIPL | 1.23 |

Fig. 39 - 41

| | | | | | | | | | | | | | | |
|---|---|---|---|---|---|---|---|---|---|---|---|---|---|---|
| 7678 | 3 | 4 | | | IV-1 | PI15 | 1.05 | 7774 | 3 | 4 | | | IV-1 | PTCD2 | 1.30 |
| 7679 | 3 | 4 | | | IV-1 | PI4K2B | 1.20 | 7775 | 3 | 4 | | | IV-1 | PTEN | 1.08 |
| 7680 | 3 | 4 | | | IV-1 | PIAS2 | 1.22 | 7776 | 3 | 4 | | | IV-1 | PTER | 1.34 |
| 7681 | 3 | 4 | | | IV-1 | PIGH | 1.34 | 7777 | 3 | 4 | | | IV-1 | PTGES3 | 1.04 |
| 7682 | 3 | 4 | | | IV-1 | PIGK | 1.29 | 7778 | 3 | 4 | | | IV-1 | PTGR1 | 1.18 |
| 7683 | 3 | 4 | | | IV-1 | PIGX | 1.41 | 7779 | 3 | 4 | | | IV-1 | PTGR2 | 1.27 |
| 7684 | 3 | 4 | | | IV-1 | PIGY | 1.13 | 7780 | 3 | 4 | | | IV-1 | PTPDC1 | 1.17 |
| 7685 | 3 | 4 | | | IV-1 | PIK3AP1 | 1.00 | 7781 | 3 | 4 | | | IV-1 | PTPN12 | 1.07 |
| 7686 | 3 | 4 | | | IV-1 | PIK3CB | 1.03 | 7782 | 3 | 4 | | | IV-1 | PTPRJ | 1.06 |
| 7687 | 3 | 4 | | | IV-1 | PIK3R1 | 1.14 | 7783 | 3 | 4 | | | IV-1 | PTRH2 | 1.09 |
| 7688 | 3 | 4 | | | IV-1 | PIKFYVE | 1.17 | 7784 | 3 | 4 | | | IV-1 | PUM2 | 1.01 |
| 7689 | 3 | 4 | | | IV-1 | PIR | 1.27 | 7785 | 3 | 4 | | | IV-1 | PUS10 | 1.33 |
| 7690 | 3 | 4 | | | IV-1 | PITX2 | 1.10 | 7786 | 3 | 4 | | | IV-1 | PWP1 | 1.07 |
| 7691 | 3 | 4 | | | IV-1 | PJA2 | 1.06 | 7787 | 3 | 4 | | | IV-1 | PWWP2A | 1.02 |
| 7692 | 3 | 4 | | | IV-1 | PKD1L2 | 1.29 | 7788 | 3 | 4 | | | IV-1 | QDPR | 1.25 |
| 7693 | 3 | 4 | | | IV-1 | PKN2 | 1.07 | 7789 | 3 | 4 | | | IV-1 | QSER1 | 1.18 |
| 7694 | 3 | 4 | | | IV-1 | PKP2 | 1.39 | 7790 | 3 | 4 | | | IV-1 | RAB12 | 1.14 |
| 7695 | 3 | 4 | | | IV-1 | PLA2G12A | 1.49 | 7791 | 3 | 4 | | | IV-1 | RAB1A | 1.19 |
| 7696 | 3 | 4 | | | IV-1 | PLA2G4C | 1.42 | 7792 | 3 | 4 | | | IV-1 | RAB20 | 1.10 |
| 7697 | 3 | 4 | | | IV-1 | PLAG1 | 1.29 | 7793 | 3 | 4 | | | IV-1 | RAB27A | 1.36 |
| 7698 | 3 | 4 | | | IV-1 | PLB1 | 1.36 | 7794 | 3 | 4 | | | IV-1 | RAB2A | 1.02 |
| 7699 | 3 | 4 | | | IV-1 | PLEKHA5 | 1.27 | 7795 | 3 | 4 | | | IV-1 | RAB3A | 1.01 |
| 7700 | 3 | 4 | | | IV-1 | PLEKHA8 | 1.11 | 7796 | 3 | 4 | | | IV-1 | RAB38 | 1.41 |
| 7701 | 3 | 4 | | | IV-1 | PLEKHA8P1 | 1.34 | 7797 | 3 | 4 | | | IV-1 | RAB5A | 1.07 |
| 7702 | 3 | 4 | | | IV-1 | PLGLB1 | 1.44 | 7798 | 3 | 4 | | | IV-1 | RABEP1 | 1.44 |
| 7703 | 3 | 4 | | | IV-1 | PLS1 | 1.17 | 7799 | 3 | 4 | | | IV-1 | RABGGTA | 1.03 |
| 7704 | 3 | 4 | | | IV-1 | PM20D2 | 1.27 | 7800 | 3 | 4 | | | IV-1 | RAD21 | 1.18 |
| 7705 | 3 | 4 | | | IV-1 | PMM1 | 1.15 | 7801 | 3 | 4 | | | IV-1 | RANBP2 | 1.08 |
| 7706 | 3 | 4 | | | IV-1 | PMPCB | 1.06 | 7802 | 3 | 4 | | | IV-1 | RAP2A | 1.01 |
| 7707 | 3 | 4 | | | IV-1 | PNLDC1 | 1.30 | 7803 | 3 | 4 | | | IV-1 | RAP2C | 1.24 |
| 7708 | 3 | 4 | | | IV-1 | PNO1 | 1.24 | 7804 | 3 | 4 | | | IV-1 | RAPGEF4 | 1.08 |
| 7709 | 3 | 4 | | | IV-1 | PNPLA8 | 1.41 | 7805 | 3 | 4 | | | IV-1 | RAPGEF6 | 1.32 |
| 7710 | 3 | 4 | | | IV-1 | PNPT1 | 1.00 | 7806 | 3 | 4 | | | IV-1 | RASGEF1C | 1.38 |
| 7711 | 3 | 4 | | | IV-1 | POC1B | 1.26 | 7807 | 3 | 4 | | | IV-1 | RASGRP3 | 1.27 |
| 7712 | 3 | 4 | | | IV-1 | POLH | 1.02 | 7808 | 3 | 4 | | | IV-1 | RASL10A | 1.03 |
| 7713 | 3 | 4 | | | IV-1 | POP1 | 1.17 | 7809 | 3 | 4 | | | IV-1 | RASL10B | 1.28 |
| 7714 | 3 | 4 | | | IV-1 | PPA1 | 1.17 | 7810 | 3 | 4 | | | IV-1 | RASSF10 | 1.02 |
| 7715 | 3 | 4 | | | IV-1 | PPAPDC1B | 1.03 | 7811 | 3 | 4 | | | IV-1 | RASSF6 | 1.06 |
| 7716 | 3 | 4 | | | IV-1 | PPARA | 1.11 | 7812 | 3 | 4 | | | IV-1 | RB1 | 1.03 |
| 7717 | 3 | 4 | | | IV-1 | PPCS | 1.07 | 7813 | 3 | 4 | | | IV-1 | RB1CC1 | 1.46 |
| 7718 | 3 | 4 | | | IV-1 | PPIAL4A | 1.39 | 7814 | 3 | 4 | | | IV-1 | RBAK | 1.24 |
| 7719 | 3 | 4 | | | IV-1 | PPID | 1.35 | 7815 | 3 | 4 | | | IV-1 | RBBP4 | 1.08 |
| 7720 | 3 | 4 | | | IV-1 | PPIP5K2 | 1.16 | 7816 | 3 | 4 | | | IV-1 | RBBP8 | 1.02 |
| 7721 | 3 | 4 | | | IV-1 | PPM1A | 1.02 | 7817 | 3 | 4 | | | IV-1 | RBKS | 1.04 |
| 7722 | 3 | 4 | | | IV-1 | PPM1B | 1.18 | 7818 | 3 | 4 | | | IV-1 | RBM18 | 1.17 |
| 7723 | 3 | 4 | | | IV-1 | PPM1N | 1.24 | 7819 | 3 | 4 | | | IV-1 | RBM43 | 1.14 |
| 7724 | 3 | 4 | | | IV-1 | PPP1CB | 1.35 | 7820 | 3 | 4 | | | IV-1 | RBM48 | 1.10 |
| 7725 | 3 | 4 | | | IV-1 | PPP1R12A | 1.24 | 7821 | 3 | 4 | | | IV-1 | RBMS1 | 1.21 |
| 7726 | 3 | 4 | | | IV-1 | PPP1R2 | 1.02 | 7822 | 3 | 4 | | | IV-1 | RBMX2 | 1.20 |
| 7727 | 3 | 4 | | | IV-1 | PPP1R21 | 1.04 | 7823 | 3 | 4 | | | IV-1 | RBPMS2 | 1.02 |
| 7728 | 3 | 4 | | | IV-1 | PPP1R3B | 1.15 | 7824 | 3 | 4 | | | IV-1 | RC3H2 | 1.33 |
| 7729 | 3 | 4 | | | IV-1 | PPP1R3D | 1.27 | 7825 | 3 | 4 | | | IV-1 | RCAN2 | 1.06 |
| 7730 | 3 | 4 | | | IV-1 | PPP2R5A | 1.29 | 7826 | 3 | 4 | | | IV-1 | RCHY1 | 1.16 |
| 7731 | 3 | 4 | | | IV-1 | PPP2R5E | 1.45 | 7827 | 3 | 4 | | | IV-1 | RDH10 | 1.40 |
| 7732 | 3 | 4 | | | IV-1 | PPP3CA | 1.14 | 7828 | 3 | 4 | | | IV-1 | RDX | 1.30 |
| 7733 | 3 | 4 | | | IV-1 | PRDM10 | 1.26 | 7829 | 3 | 4 | | | IV-1 | REEP5 | 1.03 |
| 7734 | 3 | 4 | | | IV-1 | PREP | 1.03 | 7830 | 3 | 4 | | | IV-1 | REST | 1.01 |
| 7735 | 3 | 4 | | | IV-1 | PREPL | 1.26 | 7831 | 3 | 4 | | | IV-1 | REXO2 | 1.18 |
| 7736 | 3 | 4 | | | IV-1 | PRKACB | 1.35 | 7832 | 3 | 4 | | | IV-1 | RFESD | 1.41 |
| 7737 | 3 | 4 | | | IV-1 | PRKAG2 | 1.08 | 7833 | 3 | 4 | | | IV-1 | RFK | 1.04 |
| 7738 | 3 | 4 | | | IV-1 | PRKCI | 1.07 | 7834 | 3 | 4 | | | IV-1 | RFWD2 | 1.10 |
| 7739 | 3 | 4 | | | IV-1 | PRKG1 | 1.25 | 7835 | 3 | 4 | | | IV-1 | RHBDD3 | 1.01 |
| 7740 | 3 | 4 | | | IV-1 | PRKRA | 1.10 | 7836 | 3 | 4 | | | IV-1 | RHCG | 1.01 |
| 7741 | 3 | 4 | | | IV-1 | PRLR | 1.04 | 7837 | 3 | 4 | | | IV-1 | RHOBTB3 | 1.44 |
| 7742 | 3 | 4 | | | IV-1 | PRMT10 | 1.05 | 7838 | 3 | 4 | | | IV-1 | RHOT1 | 1.04 |
| 7743 | 3 | 4 | | | IV-1 | PRMT3 | 1.19 | 7839 | 3 | 4 | | | IV-1 | RINL | 1.08 |
| 7744 | 3 | 4 | | | IV-1 | PRO0611 | 1.08 | 7840 | 3 | 4 | | | IV-1 | RINT1 | 1.16 |
| 7745 | 3 | 4 | | | IV-1 | PROSC | 1.12 | 7841 | 3 | 4 | | | IV-1 | RIOK3 | 1.08 |
| 7746 | 3 | 4 | | | IV-1 | PRPF40A | 1.04 | 7842 | 3 | 4 | | | IV-1 | RMND1 | 1.06 |
| 7747 | 3 | 4 | | | IV-1 | PRPF4B | 1.17 | 7843 | 3 | 4 | | | IV-1 | RNASE4 | 1.01 |
| 7748 | 3 | 4 | | | IV-1 | PRPSAP1 | 1.06 | 7844 | 3 | 4 | | | IV-1 | RNF103 | 1.10 |
| 7749 | 3 | 4 | | | IV-1 | PRPSAP2 | 1.20 | 7845 | 3 | 4 | | | IV-1 | RNF135 | 1.04 |
| 7750 | 3 | 4 | | | IV-1 | PRR13 | 1.03 | 7846 | 3 | 4 | | | IV-1 | RNF146 | 1.01 |
| 7751 | 3 | 4 | | | IV-1 | PRRG2 | 1.02 | 7847 | 3 | 4 | | | IV-1 | RNF149 | 1.10 |
| 7752 | 3 | 4 | | | IV-1 | PRSS21 | 1.33 | 7848 | 3 | 4 | | | IV-1 | RNF152 | 1.16 |
| 7753 | 3 | 4 | | | IV-1 | PSENEN | 1.04 | 7849 | 3 | 4 | | | IV-1 | RNF157 | 1.17 |
| 7754 | 3 | 4 | | | IV-1 | PSIP1 | 1.23 | 7850 | 3 | 4 | | | IV-1 | RNF168 | 1.19 |
| 7755 | 3 | 4 | | | IV-1 | PSMA1 | 1.17 | 7851 | 3 | 4 | | | IV-1 | RNF219 | 1.09 |
| 7756 | 3 | 4 | | | IV-1 | PSMA2 | 1.44 | 7852 | 3 | 4 | | | IV-1 | RNF6 | 1.18 |
| 7757 | 3 | 4 | | | IV-1 | PSMA4 | 1.14 | 7853 | 3 | 4 | | | IV-1 | RNF7 | 1.03 |
| 7758 | 3 | 4 | | | IV-1 | PSMA7 | 1.41 | 7854 | 3 | 4 | | | IV-1 | RNFT1 | 1.23 |
| 7759 | 3 | 4 | | | IV-1 | PSMB1 | 1.20 | 7855 | 3 | 4 | | | IV-1 | ROCK1 | 1.33 |
| 7760 | 3 | 4 | | | IV-1 | PSMB3 | 1.27 | 7856 | 3 | 4 | | | IV-1 | ROCK1P1 | 1.13 |
| 7761 | 3 | 4 | | | IV-1 | PSMC1 | 1.05 | 7857 | 3 | 4 | | | IV-1 | ROCK2 | 1.09 |
| 7762 | 3 | 4 | | | IV-1 | PSMC6 | 1.45 | 7858 | 3 | 4 | | | IV-1 | ROR1 | 1.46 |
| 7763 | 3 | 4 | | | IV-1 | PSMD1 | 1.32 | 7859 | 3 | 4 | | | IV-1 | RPIA | 1.11 |
| 7764 | 3 | 4 | | | IV-1 | PSMD12 | 1.03 | 7860 | 3 | 4 | | | IV-1 | RPL10A | 1.02 |
| 7765 | 3 | 4 | | | IV-1 | PSMD14 | 1.22 | 7861 | 3 | 4 | | | IV-1 | RPL13AP6 | 1.05 |
| 7766 | 3 | 4 | | | IV-1 | PSMD6 | 1.14 | 7862 | 3 | 4 | | | IV-1 | RPL21P28 | 1.30 |
| 7767 | 3 | 4 | | | IV-1 | PSMD7 | 1.06 | 7863 | 3 | 4 | | | IV-1 | RPL22 | 1.04 |
| 7768 | 3 | 4 | | | IV-1 | PSME2 | 1.14 | 7864 | 3 | 4 | | | IV-1 | RPL23A | 1.16 |
| 7769 | 3 | 4 | | | IV-1 | PSME4 | 1.16 | 7865 | 3 | 4 | | | IV-1 | RPL23P8 | 1.16 |
| 7770 | 3 | 4 | | | IV-1 | PSMG1 | 1.00 | 7866 | 3 | 4 | | | IV-1 | RPL29P2 | 1.18 |
| 7771 | 3 | 4 | | | IV-1 | PSPH | 1.05 | 7867 | 3 | 4 | | | IV-1 | RPL30 | 1.01 |
| 7772 | 3 | 4 | | | IV-1 | PSTPIP2 | 1.07 | 7868 | 3 | 4 | | | IV-1 | RPL32 | 1.01 |
| 7773 | 3 | 4 | | | IV-1 | PTAFR | 1.37 | 7869 | 3 | 4 | | | IV-1 | RPL32P3 | 1.31 |

Fig. 39 - 42

| | | | | | | | | | | | | | | | |
|---|---|---|---|---|---|---|---|---|---|---|---|---|---|---|---|
| 7870 | 3 | 4 | | | IV-1 | RPL35A | 1.10 | 7966 | 3 | 4 | | | IV-1 | SLC4A11 | 1.16 |
| 7871 | 3 | 4 | | | IV-1 | RPL36 | 1.02 | 7967 | 3 | 4 | | | IV-1 | SLC4A5 | 1.13 |
| 7872 | 3 | 4 | | | IV-1 | RPL37 | 1.01 | 7968 | 3 | 4 | | | IV-1 | SLC50A1 | 1.38 |
| 7873 | 3 | 4 | | | IV-1 | RPL41 | 1.46 | 7969 | 3 | 4 | | | IV-1 | SLC5A3 | 1.44 |
| 7874 | 3 | 4 | | | IV-1 | RPL5 | 1.13 | 7970 | 3 | 4 | | | IV-1 | SLC5A6 | 1.02 |
| 7875 | 3 | 4 | | | IV-1 | RPL7 | 1.06 | 7971 | 3 | 4 | | | IV-1 | SLC9A2 | 1.37 |
| 7876 | 3 | 4 | | | IV-1 | RPLP2 | 1.12 | 7972 | 3 | 4 | | | IV-1 | SLC9A3R1 | 1.04 |
| 7877 | 3 | 4 | | | IV-1 | RPP14 | 1.38 | 7973 | 3 | 4 | | | IV-1 | SLFN12 | 1.25 |
| 7878 | 3 | 4 | | | IV-1 | RPRD1A | 1.06 | 7974 | 3 | 4 | | | IV-1 | SLITRK4 | 1.33 |
| 7879 | 3 | 4 | | | IV-1 | RPRML | 1.08 | 7975 | 3 | 4 | | | IV-1 | SLK | 1.45 |
| 7880 | 3 | 4 | | | IV-1 | RPS10-NUDT3 | 1.29 | 7976 | 3 | 4 | | | IV-1 | SLMO2 | 1.10 |
| 7881 | 3 | 4 | | | IV-1 | RPS12 | 1.17 | 7977 | 3 | 4 | | | IV-1 | SLU7 | 1.22 |
| 7882 | 3 | 4 | | | IV-1 | RPS19BP1 | 1.02 | 7978 | 3 | 4 | | | IV-1 | SMAD5 | 1.04 |
| 7883 | 3 | 4 | | | IV-1 | RPS27A | 1.27 | 7979 | 3 | 4 | | | IV-1 | SMAGP | 1.28 |
| 7884 | 3 | 4 | | | IV-1 | RPS27L | 1.04 | 7980 | 3 | 4 | | | IV-1 | SMAP1 | 1.08 |
| 7885 | 3 | 4 | | | IV-1 | RPS2P32 | 1.32 | 7981 | 3 | 4 | | | IV-1 | SMC3 | 1.07 |
| 7886 | 3 | 4 | | | IV-1 | RPS3A | 1.41 | 7982 | 3 | 4 | | | IV-1 | SMG1 | 1.09 |
| 7887 | 3 | 4 | | | IV-1 | RPS6KA6 | 1.23 | 7983 | 3 | 4 | | | IV-1 | SMUG1 | 1.07 |
| 7888 | 3 | 4 | | | IV-1 | RRAGD | 1.24 | 7984 | 3 | 4 | | | IV-1 | SNHG15 | 1.02 |
| 7889 | 3 | 4 | | | IV-1 | RRM1 | 1.07 | 7985 | 3 | 4 | | | IV-1 | SNHG4 | 1.03 |
| 7890 | 3 | 4 | | | IV-1 | RSL24D1 | 1.10 | 7986 | 3 | 4 | | | IV-1 | SNHG7 | 1.13 |
| 7891 | 3 | 4 | | | IV-1 | RTF1 | 1.12 | 7987 | 3 | 4 | | | IV-1 | SNHG8 | 1.12 |
| 7892 | 3 | 4 | | | IV-1 | RUNDC1 | 1.14 | 7988 | 3 | 4 | | | IV-1 | SNN | 1.06 |
| 7893 | 3 | 4 | | | IV-1 | RWDD1 | 1.27 | 7989 | 3 | 4 | | | IV-1 | SNORA64 | 1.22 |
| 7894 | 3 | 4 | | | IV-1 | RWDD3 | 1.25 | 7990 | 3 | 4 | | | IV-1 | SNORA67 | 1.02 |
| 7895 | 3 | 4 | | | IV-1 | RWDD4 | 1.27 | 7991 | 3 | 4 | | | IV-1 | SNRNP25 | 1.32 |
| 7896 | 3 | 4 | | | IV-1 | S100B | 1.28 | 7992 | 3 | 4 | | | IV-1 | SNRPB2 | 1.22 |
| 7897 | 3 | 4 | | | IV-1 | SACM1L | 1.05 | 7993 | 3 | 4 | | | IV-1 | SNRPD1 | 1.02 |
| 7898 | 3 | 4 | | | IV-1 | SAR1B | 1.05 | 7994 | 3 | 4 | | | IV-1 | SNTB2 | 1.23 |
| 7899 | 3 | 4 | | | IV-1 | SASH1 | 1.12 | 7995 | 3 | 4 | | | IV-1 | SNX11 | 1.12 |
| 7900 | 3 | 4 | | | IV-1 | SATB1 | 1.13 | 7996 | 3 | 4 | | | IV-1 | SNX13 | 1.39 |
| 7901 | 3 | 4 | | | IV-1 | SBNO1 | 1.23 | 7997 | 3 | 4 | | | IV-1 | SNX14 | 1.03 |
| 7902 | 3 | 4 | | | IV-1 | SCAI | 1.22 | 7998 | 3 | 4 | | | IV-1 | SNX25 | 1.14 |
| 7903 | 3 | 4 | | | IV-1 | SCCPDH | 1.46 | 7999 | 3 | 4 | | | IV-1 | SNX5 | 1.15 |
| 7904 | 3 | 4 | | | IV-1 | SCO1 | 1.20 | 8000 | 3 | 4 | | | IV-1 | SOCS4 | 1.15 |
| 7905 | 3 | 4 | | | IV-1 | SCP2 | 1.39 | 8001 | 3 | 4 | | | IV-1 | SORT1 | 1.11 |
| 7906 | 3 | 4 | | | IV-1 | SCPEP1 | 1.09 | 8002 | 3 | 4 | | | IV-1 | SOWAHD | 1.29 |
| 7907 | 3 | 4 | | | IV-1 | SCRN3 | 1.06 | 8003 | 3 | 4 | | | IV-1 | SOX10 | 1.01 |
| 7908 | 3 | 4 | | | IV-1 | SCYL2 | 1.19 | 8004 | 3 | 4 | | | IV-1 | SPAG16 | 1.11 |
| 7909 | 3 | 4 | | | IV-1 | SDHB | 1.10 | 8005 | 3 | 4 | | | IV-1 | SPAG9 | 1.10 |
| 7910 | 3 | 4 | | | IV-1 | SDHD | 1.38 | 8006 | 3 | 4 | | | IV-1 | SPAST | 1.06 |
| 7911 | 3 | 4 | | | IV-1 | SEC22B | 1.22 | 8007 | 3 | 4 | | | IV-1 | SPATA13 | 1.08 |
| 7912 | 3 | 4 | | | IV-1 | SEC24B | 1.01 | 8008 | 3 | 4 | | | IV-1 | SPATA18 | 1.26 |
| 7913 | 3 | 4 | | | IV-1 | SEC61B | 1.05 | 8009 | 3 | 4 | | | IV-1 | SPCS1 | 1.42 |
| 7914 | 3 | 4 | | | IV-1 | SECISBP2 | 1.03 | 8010 | 3 | 4 | | | IV-1 | SPCS2 | 1.21 |
| 7915 | 3 | 4 | | | IV-1 | SECISBP2L | 1.25 | 8011 | 3 | 4 | | | IV-1 | SPDYA | 1.04 |
| 7916 | 3 | 4 | | | IV-1 | SEH1L | 1.02 | 8012 | 3 | 4 | | | IV-1 | SPG11 | 1.04 |
| 7917 | 3 | 4 | | | IV-1 | SEL1L | 1.05 | 8013 | 3 | 4 | | | IV-1 | SPG21 | 1.15 |
| 7918 | 3 | 4 | | | IV-1 | SELS | 1.25 | 8014 | 3 | 4 | | | IV-1 | SPIN1 | 1.12 |
| 7919 | 3 | 4 | | | IV-1 | SELT | 1.03 | 8015 | 3 | 4 | | | IV-1 | SPIN3 | 1.34 |
| 7920 | 3 | 4 | | | IV-1 | SENP5 | 1.05 | 8016 | 3 | 4 | | | IV-1 | SPIRE1 | 1.22 |
| 7921 | 3 | 4 | | | IV-1 | SENP8 | 1.38 | 8017 | 3 | 4 | | | IV-1 | SPOPL | 1.18 |
| 7922 | 3 | 4 | | | IV-1 | SEPHS2 | 1.28 | 8018 | 3 | 4 | | | IV-1 | SPPL2A | 1.24 |
| 7923 | 3 | 4 | | | IV-1 | SEPP1 | 1.35 | 8019 | 3 | 4 | | | IV-1 | SPRYD4 | 1.13 |
| 7924 | 3 | 4 | | | IV-1 | SEPT11 | 1.18 | 8020 | 3 | 4 | | | IV-1 | SPRYD7 | 1.03 |
| 7925 | 3 | 4 | | | IV-1 | SEPT2 | 1.02 | 8021 | 3 | 4 | | | IV-1 | SPTLC1 | 1.09 |
| 7926 | 3 | 4 | | | IV-1 | SEPT7 | 1.01 | 8022 | 3 | 4 | | | IV-1 | SPTSSA | 1.30 |
| 7927 | 3 | 4 | | | IV-1 | SERINC2 | 1.18 | 8023 | 3 | 4 | | | IV-1 | SRCIN1 | 1.13 |
| 7928 | 3 | 4 | | | IV-1 | SERPINA9 | 1.18 | 8024 | 3 | 4 | | | IV-1 | SREBF1 | 1.02 |
| 7929 | 3 | 4 | | | IV-1 | SETDB2 | 1.03 | 8025 | 3 | 4 | | | IV-1 | SRP54 | 1.10 |
| 7930 | 3 | 4 | | | IV-1 | SETMAR | 1.32 | 8026 | 3 | 4 | | | IV-1 | SRP9 | 1.31 |
| 7931 | 3 | 4 | | | IV-1 | SF3B14 | 1.17 | 8027 | 3 | 4 | | | IV-1 | SRPK2 | 1.05 |
| 7932 | 3 | 4 | | | IV-1 | SFMBT2 | 1.07 | 8028 | 3 | 4 | | | IV-1 | SRSF5 | 1.02 |
| 7933 | 3 | 4 | | | IV-1 | SFT2D2 | 1.00 | 8029 | 3 | 4 | | | IV-1 | SRSF6 | 1.17 |
| 7934 | 3 | 4 | | | IV-1 | SH3KBP1 | 1.05 | 8030 | 3 | 4 | | | IV-1 | SRSF7 | 1.08 |
| 7935 | 3 | 4 | | | IV-1 | SH3YL1 | 1.32 | 8031 | 3 | 4 | | | IV-1 | SRSF8 | 1.13 |
| 7936 | 3 | 4 | | | IV-1 | SHCBP1 | 1.50 | 8032 | 3 | 4 | | | IV-1 | SRY | 1.03 |
| 7937 | 3 | 4 | | | IV-1 | SHFM1 | 1.07 | 8033 | 3 | 4 | | | IV-1 | SSU72 | 1.16 |
| 7938 | 3 | 4 | | | IV-1 | SHROOM3 | 1.41 | 8034 | 3 | 4 | | | IV-1 | ST6GALNAC5 | 1.01 |
| 7939 | 3 | 4 | | | IV-1 | SIAE | 1.23 | 8035 | 3 | 4 | | | IV-1 | STAC2 | 1.45 |
| 7940 | 3 | 4 | | | IV-1 | SKIV2L2 | 1.14 | 8036 | 3 | 4 | | | IV-1 | STK17A | 1.11 |
| 7941 | 3 | 4 | | | IV-1 | SKP1 | 1.24 | 8037 | 3 | 4 | | | IV-1 | STK3 | 1.05 |
| 7942 | 3 | 4 | | | IV-1 | SLC11A2 | 1.24 | 8038 | 3 | 4 | | | IV-1 | STK38L | 1.23 |
| 7943 | 3 | 4 | | | IV-1 | SLC1A5 | 1.22 | 8039 | 3 | 4 | | | IV-1 | STOML2 | 1.14 |
| 7944 | 3 | 4 | | | IV-1 | SLC22A18 | 1.35 | 8040 | 3 | 4 | | | IV-1 | STRBP | 1.24 |
| 7945 | 3 | 4 | | | IV-1 | SLC22A5 | 1.04 | 8041 | 3 | 4 | | | IV-1 | STRN3 | 1.33 |
| 7946 | 3 | 4 | | | IV-1 | SLC23A1 | 1.10 | 8042 | 3 | 4 | | | IV-1 | STX12 | 1.06 |
| 7947 | 3 | 4 | | | IV-1 | SLC25A16 | 1.03 | 8043 | 3 | 4 | | | IV-1 | STX17 | 1.12 |
| 7948 | 3 | 4 | | | IV-1 | SLC25A17 | 1.27 | 8044 | 3 | 4 | | | IV-1 | SUB1 | 1.02 |
| 7949 | 3 | 4 | | | IV-1 | SLC25A20 | 1.39 | 8045 | 3 | 4 | | | IV-1 | SUCLA2 | 1.39 |
| 7950 | 3 | 4 | | | IV-1 | SLC25A29 | 1.02 | 8046 | 3 | 4 | | | IV-1 | SUCLG1 | 1.28 |
| 7951 | 3 | 4 | | | IV-1 | SLC25A3 | 1.30 | 8047 | 3 | 4 | | | IV-1 | SULT1A1 | 1.28 |
| 7952 | 3 | 4 | | | IV-1 | SLC25A33 | 1.43 | 8048 | 3 | 4 | | | IV-1 | SULT4A1 | 1.27 |
| 7953 | 3 | 4 | | | IV-1 | SLC25A35 | 1.38 | 8049 | 3 | 4 | | | IV-1 | SUMO1 | 1.04 |
| 7954 | 3 | 4 | | | IV-1 | SLC28A3 | 1.04 | 8050 | 3 | 4 | | | IV-1 | SUMO2 | 1.07 |
| 7955 | 3 | 4 | | | IV-1 | SLC29A2 | 1.23 | 8051 | 3 | 4 | | | IV-1 | SUV39H2 | 1.41 |
| 7956 | 3 | 4 | | | IV-1 | SLC2A11 | 1.02 | 8052 | 3 | 4 | | | IV-1 | SUV420H1 | 1.18 |
| 7957 | 3 | 4 | | | IV-1 | SLC2A9 | 1.05 | 8053 | 3 | 4 | | | IV-1 | SUZ12 | 1.05 |
| 7958 | 3 | 4 | | | IV-1 | SLC30A7 | 1.39 | 8054 | 3 | 4 | | | IV-1 | SWSAP1 | 1.28 |
| 7959 | 3 | 4 | | | IV-1 | SLC35A1 | 1.38 | 8055 | 3 | 4 | | | IV-1 | SYNJ1 | 1.20 |
| 7960 | 3 | 4 | | | IV-1 | SLC35B1 | 1.47 | 8056 | 3 | 4 | | | IV-1 | SYNJ2BP | 1.06 |
| 7961 | 3 | 4 | | | IV-1 | SLC35E3 | 1.35 | 8057 | 3 | 4 | | | IV-1 | TA83 | 1.13 |
| 7962 | 3 | 4 | | | IV-1 | SLC35F1 | 1.11 | 8058 | 3 | 4 | | | IV-1 | TAF11 | 1.13 |
| 7963 | 3 | 4 | | | IV-1 | SLC38A6 | 1.03 | 8059 | 3 | 4 | | | IV-1 | TAF9 | 1.10 |
| 7964 | 3 | 4 | | | IV-1 | SLC39A6 | 1.28 | 8060 | 3 | 4 | | | IV-1 | TAOK1 | 1.03 |
| 7965 | 3 | 4 | | | IV-1 | SLC39A9 | 1.27 | 8061 | 3 | 4 | | | IV-1 | TARS | 1.14 |

Fig. 39 - 43

| | | | | | | | | | | | | | | | |
|---|---|---|---|---|---|---|---|---|---|---|---|---|---|---|---|
| 8062 | 3 | 4 | | | IV-1 | TASP1 | 1.24 | 8158 | 3 | 4 | | | IV-1 | TOMM70A | 1.16 |
| 8063 | 3 | 4 | | | IV-1 | TATDN3 | 1.17 | 8159 | 3 | 4 | | | IV-1 | TOP1 | 1.23 |
| 8064 | 3 | 4 | | | IV-1 | TAX1BP1 | 1.14 | 8160 | 3 | 4 | | | IV-1 | TOP1P1 | 1.04 |
| 8065 | 3 | 4 | | | IV-1 | TBC1D23 | 1.14 | 8161 | 3 | 4 | | | IV-1 | TOX3 | 1.25 |
| 8066 | 3 | 4 | | | IV-1 | TBC1D7 | 1.44 | 8162 | 3 | 4 | | | IV-1 | TRAF4 | 1.12 |
| 8067 | 3 | 4 | | | IV-1 | TBC1D9 | 1.43 | 8163 | 3 | 4 | | | IV-1 | TRAM1L1 | 1.45 |
| 8068 | 3 | 4 | | | IV-1 | TBPL1 | 1.10 | 8164 | 3 | 4 | | | IV-1 | TRAPPC11 | 1.33 |
| 8069 | 3 | 4 | | | IV-1 | TC2N | 1.20 | 8165 | 3 | 4 | | | IV-1 | TRAPPC2P1 | 1.06 |
| 8070 | 3 | 4 | | | IV-1 | TCEA1 | 1.21 | 8166 | 3 | 4 | | | IV-1 | TRAPPC4 | 1.08 |
| 8071 | 3 | 4 | | | IV-1 | TCEANC | 1.26 | 8167 | 3 | 4 | | | IV-1 | TRAPPC6B | 1.20 |
| 8072 | 3 | 4 | | | IV-1 | TCF12 | 1.02 | 8168 | 3 | 4 | | | IV-1 | TRAPPC8 | 1.04 |
| 8073 | 3 | 4 | | | IV-1 | TCF15 | 1.25 | 8169 | 3 | 4 | | | IV-1 | TRIM23 | 1.19 |
| 8074 | 3 | 4 | | | IV-1 | TCF4 | 1.07 | 8170 | 3 | 4 | | | IV-1 | TRIM5 | 1.07 |
| 8075 | 3 | 4 | | | IV-1 | TCTA | 1.05 | 8171 | 3 | 4 | | | IV-1 | TRIM52 | 1.21 |
| 8076 | 3 | 4 | | | IV-1 | TCTEX1D2 | 1.28 | 8172 | 3 | 4 | | | IV-1 | TRIP11 | 1.04 |
| 8077 | 3 | 4 | | | IV-1 | TDP2 | 1.49 | 8173 | 3 | 4 | | | IV-1 | TRIP12 | 1.09 |
| 8078 | 3 | 4 | | | IV-1 | TEX101 | 1.33 | 8174 | 3 | 4 | | | IV-1 | TRIP4 | 1.30 |
| 8079 | 3 | 4 | | | IV-1 | TEX30 | 1.18 | 8175 | 3 | 4 | | | IV-1 | TRMT1L | 1.05 |
| 8080 | 3 | 4 | | | IV-1 | TFB1M | 1.03 | 8176 | 3 | 4 | | | IV-1 | TRMT5 | 1.09 |
| 8081 | 3 | 4 | | | IV-1 | TFCP2L1 | 1.09 | 8177 | 3 | 4 | | | IV-1 | TROVE2 | 1.01 |
| 8082 | 3 | 4 | | | IV-1 | THAP2 | 1.15 | 8178 | 3 | 4 | | | IV-1 | TRPS1 | 1.37 |
| 8083 | 3 | 4 | | | IV-1 | THAP5 | 1.03 | 8179 | 3 | 4 | | | IV-1 | TRPT1 | 1.21 |
| 8084 | 3 | 4 | | | IV-1 | THAP6 | 1.37 | 8180 | 3 | 4 | | | IV-1 | TSEN2 | 1.44 |
| 8085 | 3 | 4 | | | IV-1 | THAP9 | 1.20 | 8181 | 3 | 4 | | | IV-1 | TSNAX | 1.20 |
| 8086 | 3 | 4 | | | IV-1 | TH1SD4 | 1.14 | 8182 | 3 | 4 | | | IV-1 | TSPAN31 | 1.17 |
| 8087 | 3 | 4 | | | IV-1 | THUMPD1 | 1.45 | 8183 | 3 | 4 | | | IV-1 | TSSK6 | 1.14 |
| 8088 | 3 | 4 | | | IV-1 | TIFA | 1.21 | 8184 | 3 | 4 | | | IV-1 | TSTD1 | 1.25 |
| 8089 | 3 | 4 | | | IV-1 | TIMM10 | 1.15 | 8185 | 3 | 4 | | | IV-1 | TTC18 | 1.06 |
| 8090 | 3 | 4 | | | IV-1 | TIMM17A | 1.41 | 8186 | 3 | 4 | | | IV-1 | TTC19 | 1.09 |
| 8091 | 3 | 4 | | | IV-1 | TIMM21 | 1.05 | 8187 | 3 | 4 | | | IV-1 | TTC3 | 1.08 |
| 8092 | 3 | 4 | | | IV-1 | TIMM23 | 1.15 | 8188 | 3 | 4 | | | IV-1 | TTC37 | 1.04 |
| 8093 | 3 | 4 | | | IV-1 | TIMM8A | 1.44 | 8189 | 3 | 4 | | | IV-1 | TTI2 | 1.12 |
| 8094 | 3 | 4 | | | IV-1 | TIMM8B | 1.05 | 8190 | 3 | 4 | | | IV-1 | TTTY15 | 1.03 |
| 8095 | 3 | 4 | | | IV-1 | TIMM9 | 1.04 | 8191 | 3 | 4 | | | IV-1 | TWF1 | 1.04 |
| 8096 | 3 | 4 | | | IV-1 | TIMMDC1 | 1.02 | 8192 | 3 | 4 | | | IV-1 | TXN | 1.09 |
| 8097 | 3 | 4 | | | IV-1 | TLR2 | 1.34 | 8193 | 3 | 4 | | | IV-1 | TXNDC9 | 1.29 |
| 8098 | 3 | 4 | | | IV-1 | TM2D3 | 1.09 | 8194 | 3 | 4 | | | IV-1 | TXNL4A | 1.14 |
| 8099 | 3 | 4 | | | IV-1 | TM9SF3 | 1.07 | 8195 | 3 | 4 | | | IV-1 | UACA | 1.18 |
| 8100 | 3 | 4 | | | IV-1 | TM8IM4 | 1.11 | 8196 | 3 | 4 | | | IV-1 | UAP1 | 1.10 |
| 8101 | 3 | 4 | | | IV-1 | TMC4 | 1.37 | 8197 | 3 | 4 | | | IV-1 | UBA3 | 1.24 |
| 8102 | 3 | 4 | | | IV-1 | TMCO1 | 1.02 | 8198 | 3 | 4 | | | IV-1 | UBA5 | 1.00 |
| 8103 | 3 | 4 | | | IV-1 | TMED2 | 1.01 | 8199 | 3 | 4 | | | IV-1 | UBA6 | 1.37 |
| 8104 | 3 | 4 | | | IV-1 | TMED5 | 1.43 | 8200 | 3 | 4 | | | IV-1 | UBAC2-AS1 | 1.03 |
| 8105 | 3 | 4 | | | IV-1 | TMED7 | 1.03 | 8201 | 3 | 4 | | | IV-1 | UBE2A | 1.09 |
| 8106 | 3 | 4 | | | IV-1 | TMEM100 | 1.42 | 8202 | 3 | 4 | | | IV-1 | UBE2B | 1.19 |
| 8107 | 3 | 4 | | | IV-1 | TMEM120A | 1.11 | 8203 | 3 | 4 | | | IV-1 | UBE2D3 | 1.06 |
| 8108 | 3 | 4 | | | IV-1 | TMEM123 | 1.48 | 8204 | 3 | 4 | | | IV-1 | UBE2D4 | 1.05 |
| 8109 | 3 | 4 | | | IV-1 | TMEM128 | 1.02 | 8205 | 3 | 4 | | | IV-1 | UBE2E1 | 1.31 |
| 8110 | 3 | 4 | | | IV-1 | TMEM132A | 1.38 | 8206 | 3 | 4 | | | IV-1 | UBE2K | 1.02 |
| 8111 | 3 | 4 | | | IV-1 | TMEM135 | 1.15 | 8207 | 3 | 4 | | | IV-1 | UBE2Q2 | 1.16 |
| 8112 | 3 | 4 | | | IV-1 | TMEM139 | 1.10 | 8208 | 3 | 4 | | | IV-1 | UBE2V2 | 1.26 |
| 8113 | 3 | 4 | | | IV-1 | TMEM14A | 1.06 | 8209 | 3 | 4 | | | IV-1 | UBE4A | 1.47 |
| 8114 | 3 | 4 | | | IV-1 | TMEM148 | 1.08 | 8210 | 3 | 4 | | | IV-1 | UBLCP1 | 1.14 |
| 8115 | 3 | 4 | | | IV-1 | TMEM14C | 1.04 | 8211 | 3 | 4 | | | IV-1 | UBR1 | 1.08 |
| 8116 | 3 | 4 | | | IV-1 | TMEM161B | 1.29 | 8212 | 3 | 4 | | | IV-1 | UBR3 | 1.23 |
| 8117 | 3 | 4 | | | IV-1 | TMEM165 | 1.39 | 8213 | 3 | 4 | | | IV-1 | UBR5 | 1.13 |
| 8118 | 3 | 4 | | | IV-1 | TMEM167A | 1.17 | 8214 | 3 | 4 | | | IV-1 | UBXN2A | 1.05 |
| 8119 | 3 | 4 | | | IV-1 | TMEM167B | 1.34 | 8215 | 3 | 4 | | | IV-1 | UBXN4 | 1.20 |
| 8120 | 3 | 4 | | | IV-1 | TMEM168 | 1.33 | 8216 | 3 | 4 | | | IV-1 | UCHL5 | 1.06 |
| 8121 | 3 | 4 | | | IV-1 | TMEM17 | 1.45 | 8217 | 3 | 4 | | | IV-1 | UGP2 | 1.26 |
| 8122 | 3 | 4 | | | IV-1 | TMEM181 | 1.32 | 8218 | 3 | 4 | | | IV-1 | UHMK1 | 1.28 |
| 8123 | 3 | 4 | | | IV-1 | TMEM186 | 1.08 | 8219 | 3 | 4 | | | IV-1 | UNC50 | 1.27 |
| 8124 | 3 | 4 | | | IV-1 | TMEM2 | 1.10 | 8220 | 3 | 4 | | | IV-1 | UPB1 | 1.34 |
| 8125 | 3 | 4 | | | IV-1 | TMEM208 | 1.11 | 8221 | 3 | 4 | | | IV-1 | UQCR11 | 1.30 |
| 8126 | 3 | 4 | | | IV-1 | TMEM218 | 1.04 | 8222 | 3 | 4 | | | IV-1 | UQCRB | 1.07 |
| 8127 | 3 | 4 | | | IV-1 | TMEM238 | 1.29 | 8223 | 3 | 4 | | | IV-1 | UQCRBP1 | 1.04 |
| 8128 | 3 | 4 | | | IV-1 | TMEM30A | 1.03 | 8224 | 3 | 4 | | | IV-1 | UQCRC1 | 1.04 |
| 8129 | 3 | 4 | | | IV-1 | TMEM33 | 1.20 | 8225 | 3 | 4 | | | IV-1 | UQCRC2 | 1.37 |
| 8130 | 3 | 4 | | | IV-1 | TMEM38A | 1.02 | 8226 | 3 | 4 | | | IV-1 | UQCRH | 1.16 |
| 8131 | 3 | 4 | | | IV-1 | TMEM41B | 1.18 | 8227 | 3 | 4 | | | IV-1 | UQCRHL | 1.39 |
| 8132 | 3 | 4 | | | IV-1 | TMEM47 | 1.05 | 8228 | 3 | 4 | | | IV-1 | URI1 | 1.03 |
| 8133 | 3 | 4 | | | IV-1 | TMEM508 | 1.01 | 8229 | 3 | 4 | | | IV-1 | USO1 | 1.17 |
| 8134 | 3 | 4 | | | IV-1 | TMEM59 | 1.06 | 8230 | 3 | 4 | | | IV-1 | USP14 | 1.09 |
| 8135 | 3 | 4 | | | IV-1 | TMEM64 | 1.10 | 8231 | 3 | 4 | | | IV-1 | USP18 | 1.10 |
| 8136 | 3 | 4 | | | IV-1 | TMEM70 | 1.02 | 8232 | 3 | 4 | | | IV-1 | USP3 | 1.05 |
| 8137 | 3 | 4 | | | IV-1 | TMEM81 | 1.25 | 8233 | 3 | 4 | | | IV-1 | USP32P2 | 1.21 |
| 8138 | 3 | 4 | | | IV-1 | TMEM87A | 1.39 | 8234 | 3 | 4 | | | IV-1 | USP33 | 1.22 |
| 8139 | 3 | 4 | | | IV-1 | TMEM87B | 1.04 | 8235 | 3 | 4 | | | IV-1 | USP34 | 1.03 |
| 8140 | 3 | 4 | | | IV-1 | TMEM9B | 1.24 | 8236 | 3 | 4 | | | IV-1 | USP46 | 1.40 |
| 8141 | 3 | 4 | | | IV-1 | TMF1 | 1.10 | 8237 | 3 | 4 | | | IV-1 | USP8 | 1.33 |
| 8142 | 3 | 4 | | | IV-1 | TMOD2 | 1.03 | 8238 | 3 | 4 | | | IV-1 | UTP11L | 1.02 |
| 8143 | 3 | 4 | | | IV-1 | TMPRSS3 | 1.35 | 8239 | 3 | 4 | | | IV-1 | UTP15 | 1.02 |
| 8144 | 3 | 4 | | | IV-1 | TMSB15B | 1.00 | 8240 | 3 | 4 | | | IV-1 | UTP23 | 1.31 |
| 8145 | 3 | 4 | | | IV-1 | TMSB4Y | 1.48 | 8241 | 3 | 4 | | | IV-1 | UXT | 1.02 |
| 8146 | 3 | 4 | | | IV-1 | TMTC1 | 1.12 | 8242 | 3 | 4 | | | IV-1 | VAPB | 1.00 |
| 8147 | 3 | 4 | | | IV-1 | TMX2 | 1.05 | 8243 | 3 | 4 | | | IV-1 | VBP1 | 1.05 |
| 8148 | 3 | 4 | | | IV-1 | TMX3 | 1.21 | 8244 | 3 | 4 | | | IV-1 | VDAC1 | 1.06 |
| 8149 | 3 | 4 | | | IV-1 | TNFRSF10C | 1.29 | 8245 | 3 | 4 | | | IV-1 | VEZT | 1.08 |
| 8150 | 3 | 4 | | | IV-1 | TNFRSF21 | 1.02 | 8246 | 3 | 4 | | | IV-1 | VLDLR | 1.38 |
| 8151 | 3 | 4 | | | IV-1 | TNKS | 1.16 | 8247 | 3 | 4 | | | IV-1 | VPS26A | 1.13 |
| 8152 | 3 | 4 | | | IV-1 | TNNC2 | 1.33 | 8248 | 3 | 4 | | | IV-1 | VPS33S | 1.05 |
| 8153 | 3 | 4 | | | IV-1 | TNRC6B | 1.22 | 8249 | 3 | 4 | | | IV-1 | VPS36 | 1.22 |
| 8154 | 3 | 4 | | | IV-1 | TOE1 | 1.07 | 8250 | 3 | 4 | | | IV-1 | VPS37A | 1.06 |
| 8155 | 3 | 4 | | | IV-1 | TOMM5 | 1.19 | 8251 | 3 | 4 | | | IV-1 | VPS41 | 1.12 |
| 8156 | 3 | 4 | | | IV-1 | TOMM6 | 1.07 | 8252 | 3 | 4 | | | IV-1 | VPS4B | 1.01 |
| 8157 | 3 | 4 | | | IV-1 | TOMM7 | 1.40 | 8253 | 3 | 4 | | | IV-1 | VPS54 | 1.28 |

Fig. 39 - 44

| | | | | | | | | | | | | | | | |
|---|---|---|---|---|---|---|---|---|---|---|---|---|---|---|---|
| 8254 | 3 | 4 | | | IV-1 | VSIG10 | 1.21 | 8350 | 3 | 4 | | | IV-1 | ZNF507 | 1.02 |
| 8255 | 3 | 4 | | | IV-1 | VTI1B | 1.01 | 8351 | 3 | 4 | | | IV-1 | ZNF518B | 1.04 |
| 8256 | 3 | 4 | | | IV-1 | WASL | 1.21 | 8352 | 3 | 4 | | | IV-1 | ZNF525 | 1.21 |
| 8257 | 3 | 4 | | | IV-1 | WBSCR16 | 1.08 | 8353 | 3 | 4 | | | IV-1 | ZNF527 | 1.06 |
| 8258 | 3 | 4 | | | IV-1 | WDFY3-AS2 | 1.04 | 8354 | 3 | 4 | | | IV-1 | ZNF544 | 1.10 |
| 8259 | 3 | 4 | | | IV-1 | WDPCP | 1.19 | 8355 | 3 | 4 | | | IV-1 | ZNF552 | 1.21 |
| 8260 | 3 | 4 | | | IV-1 | WDR11 | 1.13 | 8356 | 3 | 4 | | | IV-1 | ZNF557 | 1.29 |
| 8261 | 3 | 4 | | | IV-1 | WDR26 | 1.19 | 8357 | 3 | 4 | | | IV-1 | ZNF567 | 1.09 |
| 8262 | 3 | 4 | | | IV-1 | WDR35 | 1.11 | 8358 | 3 | 4 | | | IV-1 | ZNF607 | 1.13 |
| 8263 | 3 | 4 | | | IV-1 | WDR36 | 1.22 | 8359 | 3 | 4 | | | IV-1 | ZNF610 | 1.30 |
| 8264 | 3 | 4 | | | IV-1 | WDR41 | 1.16 | 8360 | 3 | 4 | | | IV-1 | ZNF611 | 1.23 |
| 8265 | 3 | 4 | | | IV-1 | WDR58 | 1.29 | 8361 | 3 | 4 | | | IV-1 | ZNF615 | 1.08 |
| 8266 | 3 | 4 | | | IV-1 | WDR61 | 1.19 | 8362 | 3 | 4 | | | IV-1 | ZNF627 | 1.32 |
| 8267 | 3 | 4 | | | IV-1 | WDR72 | 1.34 | 8363 | 3 | 4 | | | IV-1 | ZNF644 | 1.13 |
| 8268 | 3 | 4 | | | IV-1 | WDR77 | 1.10 | 8364 | 3 | 4 | | | IV-1 | ZNF654 | 1.17 |
| 8269 | 3 | 4 | | | IV-1 | WDR83OS | 1.03 | 8365 | 3 | 4 | | | IV-1 | ZNF658 | 1.22 |
| 8270 | 3 | 4 | | | IV-1 | WDR86 | 1.12 | 8366 | 3 | 4 | | | IV-1 | ZNF665 | 1.18 |
| 8271 | 3 | 4 | | | IV-1 | WDR92 | 1.20 | 8367 | 3 | 4 | | | IV-1 | ZNF670 | 1.01 |
| 8272 | 3 | 4 | | | IV-1 | WRAP73 | 1.03 | 8368 | 3 | 4 | | | IV-1 | ZNF681 | 1.41 |
| 8273 | 3 | 4 | | | IV-1 | XAGE2B | 1.20 | 8369 | 3 | 4 | | | IV-1 | ZNF697 | 1.02 |
| 8274 | 3 | 4 | | | IV-1 | XPNPEP1 | 1.02 | 8370 | 3 | 4 | | | IV-1 | ZNF718 | 1.14 |
| 8275 | 3 | 4 | | | IV-1 | XPO1 | 1.27 | 8371 | 3 | 4 | | | IV-1 | ZNF761 | 1.21 |
| 8276 | 3 | 4 | | | IV-1 | XRCC4 | 1.08 | 8372 | 3 | 4 | | | IV-1 | ZNF765 | 1.40 |
| 8277 | 3 | 4 | | | IV-1 | XRN1 | 1.02 | 8373 | 3 | 4 | | | IV-1 | ZNF782 | 1.47 |
| 8278 | 3 | 4 | | | IV-1 | YARS2 | 1.03 | 8374 | 3 | 4 | | | IV-1 | ZNF784 | 1.02 |
| 8279 | 3 | 4 | | | IV-1 | YIPF1 | 1.12 | 8375 | 3 | 4 | | | IV-1 | ZNF788 | 1.27 |
| 8280 | 3 | 4 | | | IV-1 | YIPF5 | 1.10 | 8376 | 3 | 4 | | | IV-1 | ZNF79 | 1.13 |
| 8281 | 3 | 4 | | | IV-1 | YIPF6 | 1.16 | 8377 | 3 | 4 | | | IV-1 | ZNF823 | 1.20 |
| 8282 | 3 | 4 | | | IV-1 | YME1L1 | 1.03 | 8378 | 3 | 4 | | | IV-1 | ZNF827 | 1.25 |
| 8283 | 3 | 4 | | | IV-1 | ZADH2 | 1.07 | 8379 | 3 | 4 | | | IV-1 | ZNF829 | 1.04 |
| 8284 | 3 | 4 | | | IV-1 | ZBTB11 | 1.12 | 8380 | 3 | 4 | | | IV-1 | ZNF844 | 1.18 |
| 8285 | 3 | 4 | | | IV-1 | ZBTB16 | 1.02 | 8381 | 3 | 4 | | | IV-1 | ZNF846 | 1.43 |
| 8286 | 3 | 4 | | | IV-1 | ZBTB3 | 1.13 | 8382 | 3 | 4 | | | IV-1 | ZNF880 | 1.13 |
| 8287 | 3 | 4 | | | IV-1 | ZBTB34 | 1.46 | 8383 | 3 | 4 | | | IV-1 | ZRANB2-AS1 | 1.41 |
| 8288 | 3 | 4 | | | IV-1 | ZBTB41 | 1.03 | 8384 | 3 | 4 | | | IV-1 | ZSWIM3 | 1.09 |
| 8289 | 3 | 4 | | | IV-1 | ZBTB44 | 1.15 | 8385 | 3 | 4 | | | IV-1 | ZW10 | 1.17 |
| 8290 | 3 | 4 | | | IV-1 | ZBTB6 | 1.43 | 8386 | 3 | 4 | | | IV-1 | ZYG11B | 1.12 |
| 8291 | 3 | 4 | | | IV-1 | ZBTB8A | 1.11 | 8387 | 3 | 4 | | | IV-1 | ZZZ3 | 1.10 |
| 8292 | 3 | 4 | | | IV-1 | ZC2HC1A | 1.12 | 8388 | 3 | | | | | A1CF | 1.00 |
| 8293 | 3 | 4 | | | IV-1 | ZC3H15 | 1.28 | 8389 | 3 | | | | | A2MP1 | 1.00 |
| 8294 | 3 | 4 | | | IV-1 | ZC3H6 | 1.37 | 8390 | 3 | | | | | A4GNT | 1.00 |
| 8295 | 3 | 4 | | | IV-1 | ZCCHC10 | 1.08 | 8391 | 3 | | | | | AA06 | 1.00 |
| 8296 | 3 | 4 | | | IV-1 | ZCCHC2 | 1.11 | 8392 | 3 | | | | | AAA1 | 1.00 |
| 8297 | 3 | 4 | | | IV-1 | ZCCHC6 | 1.15 | 8393 | 3 | | | | | AACSP1 | 1.00 |
| 8298 | 3 | 4 | | | IV-1 | ZCCHC7 | 1.09 | 8394 | 3 | | | | | AADACL4 | 1.00 |
| 8299 | 3 | 4 | | | IV-1 | ZCR81 | 1.10 | 8395 | 3 | | | | | AANAT | 1.00 |
| 8300 | 3 | 4 | | | IV-1 | ZDHHC2 | 1.40 | 8396 | 3 | | | | | AATK-AS1 | 1.00 |
| 8301 | 3 | 4 | | | IV-1 | ZEB1-AS1 | 1.05 | 8397 | 3 | | | | | ABCA13 | 1.00 |
| 8302 | 3 | 4 | | | IV-1 | ZFAND6 | 1.32 | 8398 | 3 | | | | | ABCA17P | 1.00 |
| 8303 | 3 | 4 | | | IV-1 | ZFP106 | 1.26 | 8399 | 3 | | | | | ABCA4 | 1.00 |
| 8304 | 3 | 4 | | | IV-1 | ZFP112 | 1.08 | 8400 | 3 | | | | | ABCB11 | 1.00 |
| 8305 | 3 | 4 | | | IV-1 | ZFP62 | 1.14 | 8401 | 3 | | | | | ABC84 | 1.00 |
| 8306 | 3 | 4 | | | IV-1 | ZFP90 | 1.10 | 8402 | 3 | | | | | ABCC11 | 1.00 |
| 8307 | 3 | 4 | | | IV-1 | ZFR | 1.08 | 8403 | 3 | | | | | ABCC12 | 1.00 |
| 8308 | 3 | 4 | | | IV-1 | ZFYVE16 | 1.28 | 8404 | 3 | | | | | ABCC13 | 1.00 |
| 8309 | 3 | 4 | | | IV-1 | ZKSCAN1 | 1.26 | 8405 | 3 | | | | | ABCC2 | 1.00 |
| 8310 | 3 | 4 | | | IV-1 | ZKSCAN4 | 1.13 | 8406 | 3 | | | | | ABCC6P1 | 1.00 |
| 8311 | 3 | 4 | | | IV-1 | ZMYND8 | 1.21 | 8407 | 3 | | | | | ABCC6P2 | 1.00 |
| 8312 | 3 | 4 | | | IV-1 | ZNF101 | 1.37 | 8408 | 3 | | | | | ABCC8 | 1.00 |
| 8313 | 3 | 4 | | | IV-1 | ZNF12 | 1.09 | 8409 | 3 | | | | | ABCD2 | 1.00 |
| 8314 | 3 | 4 | | | IV-1 | ZNF124 | 1.45 | 8410 | 3 | | | | | ABCG2 | 1.00 |
| 8315 | 3 | 4 | | | IV-1 | ZNF132 | 1.03 | 8411 | 3 | | | | | ABCG4 | 1.00 |
| 8316 | 3 | 4 | | | IV-1 | ZNF136 | 1.34 | 8412 | 3 | | | | | ABCG5 | 1.00 |
| 8317 | 3 | 4 | | | IV-1 | ZNF141 | 1.07 | 8413 | 3 | | | | | ABCG8 | 1.00 |
| 8318 | 3 | 4 | | | IV-1 | ZNF148 | 1.14 | 8414 | 3 | | | | | ABHD1 | 1.00 |
| 8319 | 3 | 4 | | | IV-1 | ZNF155 | 1.16 | 8415 | 3 | | | | | ABHD10 | 1.00 |
| 8320 | 3 | 4 | | | IV-1 | ZNF165 | 1.40 | 8416 | 3 | | | | | ABHD11-AS1 | 1.00 |
| 8321 | 3 | 4 | | | IV-1 | ZNF17 | 1.20 | 8417 | 3 | | | | | ABHD14A-ACY1 | 1.00 |
| 8322 | 3 | 4 | | | IV-1 | ZNF189 | 1.49 | 8418 | 3 | | | | | ABRA | 1.00 |
| 8323 | 3 | 4 | | | IV-1 | ZNF193 | 1.03 | 8419 | 3 | | | | | ACAN | 1.00 |
| 8324 | 3 | 4 | | | IV-1 | ZNF222 | 1.27 | 8420 | 3 | | | | | ACBD7 | 1.00 |
| 8325 | 3 | 4 | | | IV-1 | ZNF225 | 1.30 | 8421 | 3 | | | | | ACCN4 | 1.00 |
| 8326 | 3 | 4 | | | IV-1 | ZNF235 | 1.14 | 8422 | 3 | | | | | ACCN5 | 1.00 |
| 8327 | 3 | 4 | | | IV-1 | ZNF24 | 1.05 | 8423 | 3 | | | | | ACCSL | 1.00 |
| 8328 | 3 | 4 | | | IV-1 | ZNF250 | 1.40 | 8424 | 3 | | | | | ACE2 | 1.00 |
| 8329 | 3 | 4 | | | IV-1 | ZNF252 | 1.17 | 8425 | 3 | | | | | ACER2 | 1.00 |
| 8330 | 3 | 4 | | | IV-1 | ZNF260 | 1.12 | 8426 | 3 | | | | | ACMSD | 1.00 |
| 8331 | 3 | 4 | | | IV-1 | ZNF283 | 1.11 | 8427 | 3 | | | | | ACOT12 | 1.00 |
| 8332 | 3 | 4 | | | IV-1 | ZNF285 | 1.33 | 8428 | 3 | | | | | ACOT6 | 1.00 |
| 8333 | 3 | 4 | | | IV-1 | ZNF286A | 1.38 | 8429 | 3 | | | | | ACOXL | 1.00 |
| 8334 | 3 | 4 | | | IV-1 | ZNF287 | 1.15 | 8430 | 3 | | | | | ACPT | 1.00 |
| 8335 | 3 | 4 | | | IV-1 | ZNF311 | 1.09 | 8431 | 3 | | | | | ACRV1 | 1.00 |
| 8336 | 3 | 4 | | | IV-1 | ZNF32 | 1.03 | 8432 | 3 | | | | | ACSBG2 | 1.00 |
| 8337 | 3 | 4 | | | IV-1 | ZNF322 | 1.09 | 8433 | 3 | | | | | ACSL6 | 1.00 |
| 8338 | 3 | 4 | | | IV-1 | ZNF334 | 1.13 | 8434 | 3 | | | | | ACSM1 | 1.00 |
| 8339 | 3 | 4 | | | IV-1 | ZNF347 | 1.37 | 8435 | 3 | | | | | ACSM2A | 1.00 |
| 8340 | 3 | 4 | | | IV-1 | ZNF354A | 1.49 | 8436 | 3 | | | | | ACSM2B | 1.00 |
| 8341 | 3 | 4 | | | IV-1 | ZNF383 | 1.09 | 8437 | 3 | | | | | ACSM4 | 1.00 |
| 8342 | 3 | 4 | | | IV-1 | ZNF398 | 1.12 | 8438 | 3 | | | | | ACTBL2 | 1.00 |
| 8343 | 3 | 4 | | | IV-1 | ZNF410 | 1.09 | 8439 | 3 | | | | | ACTL6B | 1.00 |
| 8344 | 3 | 4 | | | IV-1 | ZNF418 | 1.00 | 8440 | 3 | | | | | ACTL7A | 1.00 |
| 8345 | 3 | 4 | | | IV-1 | ZNF420 | 1.30 | 8441 | 3 | | | | | ACTL7B | 1.00 |
| 8346 | 3 | 4 | | | IV-1 | ZNF44 | 1.06 | 8442 | 3 | | | | | ACTL8 | 1.00 |
| 8347 | 3 | 4 | | | IV-1 | ZNF440 | 1.31 | 8443 | 3 | | | | | ACTL9 | 1.00 |
| 8348 | 3 | 4 | | | IV-1 | ZNF501 | 1.27 | 8444 | 3 | | | | | ACTN2 | 1.00 |
| 8349 | 3 | 4 | | | IV-1 | ZNF503-AS1 | 1.16 | 8445 | 3 | | | | | ACTN3 | 1.00 |

Fig. 39 - 45

| | | | | | | | | | | | | | | |
|---|---|---|---|---|---|---|---|---|---|---|---|---|---|---|
| 8446 | 3 | | | | | ACTR3BP2 | 1.00 | 8542 | 3 | | | | ALPK2 | 1.00 |
| 8447 | 3 | | | | | ACTR3BP5 | 1.00 | 8543 | 3 | | | | ALPK3 | 1.00 |
| 8448 | 3 | | | | | ACTR3C | 1.00 | 8544 | 3 | | | | ALPP | 1.00 |
| 8449 | 3 | | | | | ACTRT1 | 1.00 | 8545 | 3 | | | | ALPPL2 | 1.00 |
| 8450 | 3 | | | | | ACTRT2 | 1.00 | 8546 | 3 | | | | ALS2CR11 | 1.00 |
| 8451 | 3 | | | | | ACVR1C | 1.00 | 8547 | 3 | | | | ALS2CR12 | 1.00 |
| 8452 | 3 | | | | | ACVR2B | 1.00 | 8548 | 3 | | | | AMBN | 1.00 |
| 8453 | 3 | | | | | ACY3 | 1.00 | 8549 | 3 | | | | AMBP | 1.00 |
| 8454 | 3 | | | | | ADAD1 | 1.00 | 8550 | 3 | | | | AMDHD1 | 1.00 |
| 8455 | 3 | | | | | ADAM12 | 1.00 | 8551 | 3 | | | | AMELX | 1.00 |
| 8456 | 3 | | | | | ADAM18 | 1.00 | 8552 | 3 | | | | AMELY | 1.00 |
| 8457 | 3 | | | | | ADAM2 | 1.00 | 8553 | 3 | | | | AMHR2 | 1.00 |
| 8458 | 3 | | | | | ADAM20 | 1.00 | 8554 | 3 | | | | AMPD1 | 1.00 |
| 8459 | 3 | | | | | ADAM21 | 1.00 | 8555 | 3 | | | | AMPH | 1.00 |
| 8460 | 3 | | | | | ADAM21P1 | 1.00 | 8556 | 3 | | | | AMTN | 1.00 |
| 8461 | 3 | | | | | ADAM22 | 1.00 | 8557 | 3 | | | | AMY1B | 1.00 |
| 8462 | 3 | | | | | ADAM23 | 1.00 | 8558 | 3 | | | | AMY1C | 1.00 |
| 8463 | 3 | | | | | ADAM28 | 1.00 | 8559 | 3 | | | | AMY2A | 1.00 |
| 8464 | 3 | | | | | ADAM29 | 1.00 | 8560 | 3 | | | | AMZ1 | 1.00 |
| 8465 | 3 | | | | | ADAM30 | 1.00 | 8561 | 3 | | | | ANGPTL3 | 1.00 |
| 8466 | 3 | | | | | ADAM32 | 1.00 | 8562 | 3 | | | | ANGPTL6 | 1.00 |
| 8467 | 3 | | | | | ADAM3A | 1.00 | 8563 | 3 | | | | ANK1 | 1.00 |
| 8468 | 3 | | | | | ADAM5P | 1.00 | 8564 | 3 | | | | ANKAR | 1.00 |
| 8469 | 3 | | | | | ADAM6 | 1.00 | 8565 | 3 | | | | ANKFN1 | 1.00 |
| 8470 | 3 | | | | | ADAM7 | 1.00 | 8566 | 3 | | | | ANKRD1 | 1.00 |
| 8471 | 3 | | | | | ADAMDEC1 | 1.00 | 8567 | 3 | | | | ANKRD18A | 1.00 |
| 8472 | 3 | | | | | ADAMTS12 | 1.00 | 8568 | 3 | | | | ANKRD18DP | 1.00 |
| 8473 | 3 | | | | | ADAMTS16 | 1.00 | 8569 | 3 | | | | ANKRD2 | 1.00 |
| 8474 | 3 | | | | | ADAMTS18 | 1.00 | 8570 | 3 | | | | ANKRD20A1 | 1.00 |
| 8475 | 3 | | | | | ADAMTS19 | 1.00 | 8571 | 3 | | | | ANKRD20A11P | 1.00 |
| 8476 | 3 | | | | | ADAMTS20 | 1.00 | 8572 | 3 | | | | ANKRD20A3 | 1.00 |
| 8477 | 3 | | | | | ADAMTS3 | 1.00 | 8573 | 3 | | | | ANKRD20A4 | 1.00 |
| 8478 | 3 | | | | | ADAMTS6 | 1.00 | 8574 | 3 | | | | ANKRD20A5P | 1.00 |
| 8479 | 3 | | | | | ADAMTSL2 | 1.00 | 8575 | 3 | | | | ANKRD20A8P | 1.00 |
| 8480 | 3 | | | | | ADARB2 | 1.00 | 8576 | 3 | | | | ANKRD20A9P | 1.00 |
| 8481 | 3 | | | | | ADARB2-AS1 | 1.00 | 8577 | 3 | | | | ANKRD24 | 1.00 |
| 8482 | 3 | | | | | ADCY1 | 1.00 | 8578 | 3 | | | | ANKRD26P1 | 1.00 |
| 8483 | 3 | | | | | ADCY10 | 1.00 | 8579 | 3 | | | | ANKRD26P3 | 1.00 |
| 8484 | 3 | | | | | ADCYAP1 | 1.00 | 8580 | 3 | | | | ANKRD30A | 1.00 |
| 8485 | 3 | | | | | ADD2 | 1.00 | 8581 | 3 | | | | ANKRD30B | 1.00 |
| 8486 | 3 | | | | | ADGB | 1.00 | 8582 | 3 | | | | ANKRD30BL | 1.00 |
| 8487 | 3 | | | | | ADH1A | 1.00 | 8583 | 3 | | | | ANKRD30BP2 | 1.00 |
| 8488 | 3 | | | | | ADH4 | 1.00 | 8584 | 3 | | | | ANKRD31 | 1.00 |
| 8489 | 3 | | | | | ADH6 | 1.00 | 8585 | 3 | | | | ANKRD33 | 1.00 |
| 8490 | 3 | | | | | ADH7 | 1.00 | 8586 | 3 | | | | ANKRD34A | 1.00 |
| 8491 | 3 | | | | | ADIG | 1.00 | 8587 | 3 | | | | ANKRD34B | 1.00 |
| 8492 | 3 | | | | | ADM2 | 1.00 | 8588 | 3 | | | | ANKRD34C | 1.00 |
| 8493 | 3 | | | | | ADRA1A | 1.00 | 8589 | 3 | | | | ANKRD36BP1 | 1.00 |
| 8494 | 3 | | | | | ADRA1D | 1.00 | 8590 | 3 | | | | ANKRD36BP2 | 1.00 |
| 8495 | 3 | | | | | ADRB3 | 1.00 | 8591 | 3 | | | | ANKRD45 | 1.00 |
| 8496 | 3 | | | | | AFAP1-AS1 | 1.00 | 8592 | 3 | | | | ANKRD55 | 1.00 |
| 8497 | 3 | | | | | AFF2 | 1.00 | 8593 | 3 | | | | ANKRD62P1-PARP4P3 | 1.00 |
| 8498 | 3 | | | | | AFF3 | 1.00 | 8594 | 3 | | | | ANKRD63 | 1.00 |
| 8499 | 3 | | | | | AFM | 1.00 | 8595 | 3 | | | | ANKRD7 | 1.00 |
| 8500 | 3 | | | | | AFP | 1.00 | 8596 | 3 | | | | ANKS1B | 1.00 |
| 8501 | 3 | | | | | AGBL1 | 1.00 | 8597 | 3 | | | | ANKS4B | 1.00 |
| 8502 | 3 | | | | | AGBL2 | 1.00 | 8598 | 3 | | | | ANKUB1 | 1.00 |
| 8503 | 3 | | | | | AGBL3 | 1.00 | 8599 | 3 | | | | ANO2 | 1.00 |
| 8504 | 3 | | | | | AGBL4 | 1.00 | 8600 | 3 | | | | ANO3 | 1.00 |
| 8505 | 3 | | | | | AGMAT | 1.00 | 8601 | 3 | | | | ANO4 | 1.00 |
| 8506 | 3 | | | | | AGMO | 1.00 | 8602 | 3 | | | | ANO5 | 1.00 |
| 8507 | 3 | | | | | AGR3 | 1.00 | 8603 | 3 | | | | ANO7 | 1.00 |
| 8508 | 3 | | | | | AGRP | 1.00 | 8604 | 3 | | | | ANP32A-IT1 | 1.00 |
| 8509 | 3 | | | | | AGTR2 | 1.00 | 8605 | 3 | | | | ANTXRL | 1.00 |
| 8510 | 3 | | | | | AGXT | 1.00 | 8606 | 3 | | | | ANXA10 | 1.00 |
| 8511 | 3 | | | | | AGXT2 | 1.00 | 8607 | 3 | | | | AOAH | 1.00 |
| 8512 | 3 | | | | | AGXT2L1 | 1.00 | 8608 | 3 | | | | AOX2P | 1.00 |
| 8513 | 3 | | | | | AHSG | 1.00 | 8609 | 3 | | | | AP1B1P1 | 1.00 |
| 8514 | 3 | | | | | AICDA | 1.00 | 8610 | 3 | | | | AP3B2 | 1.00 |
| 8515 | 3 | | | | | AIFM3 | 1.00 | 8611 | 3 | | | | APC2 | 1.00 |
| 8516 | 3 | | | | | AIM2 | 1.00 | 8612 | 3 | | | | APCS | 1.00 |
| 8517 | 3 | | | | | AIPL1 | 1.00 | 8613 | 3 | | | | APITD1-CORT | 1.00 |
| 8518 | 3 | | | | | AIRE | 1.00 | 8614 | 3 | | | | APLP1 | 1.00 |
| 8519 | 3 | | | | | AK8 | 1.00 | 8615 | 3 | | | | APOA1 | 1.00 |
| 8520 | 3 | | | | | AKAP14 | 1.00 | 8616 | 3 | | | | APOA2 | 1.00 |
| 8521 | 3 | | | | | AKAP3 | 1.00 | 8617 | 3 | | | | APOA4 | 1.00 |
| 8522 | 3 | | | | | AKAP4 | 1.00 | 8618 | 3 | | | | APOA5 | 1.00 |
| 8523 | 3 | | | | | AKAP5 | 1.00 | 8619 | 3 | | | | APOB | 1.00 |
| 8524 | 3 | | | | | AKNAD1 | 1.00 | 8620 | 3 | | | | APOBEC1 | 1.00 |
| 8525 | 3 | | | | | AKR1B15 | 1.00 | 8621 | 3 | | | | APOBEC3H | 1.00 |
| 8526 | 3 | | | | | AKR1C4 | 1.00 | 8622 | 3 | | | | APOBEC4 | 1.00 |
| 8527 | 3 | | | | | AKR1CL1 | 1.00 | 8623 | 3 | | | | APOC1P1 | 1.00 |
| 8528 | 3 | | | | | AKR1D1 | 1.00 | 8624 | 3 | | | | APOC3 | 1.00 |
| 8529 | 3 | | | | | ALB | 1.00 | 8625 | 3 | | | | APOC4 | 1.00 |
| 8530 | 3 | | | | | ALDOB | 1.00 | 8626 | 3 | | | | APOC4-APOC2 | 1.00 |
| 8531 | 3 | | | | | ALG10 | 1.00 | 8627 | 3 | | | | APOF | 1.00 |
| 8532 | 3 | | | | | ALG10B | 1.00 | 8628 | 3 | | | | APOH | 1.00 |
| 8533 | 3 | | | | | ALG1L | 1.00 | 8629 | 3 | | | | APOL5 | 1.00 |
| 8534 | 3 | | | | | ALG1L2 | 1.00 | 8630 | 3 | | | | AQP10 | 1.00 |
| 8535 | 3 | | | | | ALK | 1.00 | 8631 | 3 | | | | AQP11 | 1.00 |
| 8536 | 3 | | | | | ALLC | 1.00 | 8632 | 3 | | | | AQP12A | 1.00 |
| 8537 | 3 | | | | | ALMS1 | 1.00 | 8633 | 3 | | | | AQP12B | 1.00 |
| 8538 | 3 | | | | | ALMS1P | 1.00 | 8634 | 3 | | | | AQP2 | 1.00 |
| 8539 | 3 | | | | | ALOX12P2 | 1.00 | 8635 | 3 | | | | AQP4 | 1.00 |
| 8540 | 3 | | | | | ALOX15P1 | 1.00 | 8636 | 3 | | | | AQP6 | 1.00 |
| 8541 | 3 | | | | | ALPI | 1.00 | | | | | | | |

Fig. 39 - 46

| | | | | | | | | | | | | | |
|---|---|---|---|---|---|---|---|---|---|---|---|---|---|
| 8637 | 3 | | | | | AQP8 | 1.00 | 8733 | 3 | | | B7H6 | 1.00 |
| 8638 | 3 | | | | | ARGFX | 1.00 | 8734 | 3 | | | BAAT | 1.00 |
| 8639 | 3 | | | | | ARGFXP2 | 1.00 | 8735 | 3 | | | BAGE | 1.00 |
| 8640 | 3 | | | | | ARHGAP11B | 1.00 | 8736 | 3 | | | BAGE3 | 1.00 |
| 8641 | 3 | | | | | ARHGAP19-SLIT1 | 1.00 | 8737 | 3 | | | BAGE4 | 1.00 |
| 8642 | 3 | | | | | ARHGAP20 | 1.00 | 8738 | 3 | | | BAGE5 | 1.00 |
| 8643 | 3 | | | | | ARHGAP36 | 1.00 | 8739 | 3 | | | BAI2 | 1.00 |
| 8644 | 3 | | | | | ARHGAP42 | 1.00 | 8740 | 3 | | | BAI3 | 1.00 |
| 8645 | 3 | | | | | ARHGDIG | 1.00 | 8741 | 3 | | | BANF2 | 1.00 |
| 8646 | 3 | | | | | ARHGEF26-AS1 | 1.00 | 8742 | 3 | | | BANK1 | 1.00 |
| 8647 | 3 | | | | | ARHGEF33 | 1.00 | 8743 | 3 | | | BARD1 | 1.00 |
| 8648 | 3 | | | | | ARHGEF38 | 1.00 | 8744 | 3 | | | BARHL1 | 1.00 |
| 8649 | 3 | | | | | ARID3C | 1.00 | 8745 | 3 | | | BARHL2 | 1.00 |
| 8650 | 3 | | | | | ARL10 | 1.00 | 8746 | 3 | | | BARX1 | 1.00 |
| 8651 | 3 | | | | | ARL11 | 1.00 | 8747 | 3 | | | BCAR4 | 1.00 |
| 8652 | 3 | | | | | ARL13A | 1.00 | 8748 | 3 | | | BCAT1 | 1.00 |
| 8653 | 3 | | | | | ARL14 | 1.00 | 8749 | 3 | | | BCL2L14 | 1.00 |
| 8654 | 3 | | | | | ARL2-SNX15 | 1.00 | 8750 | 3 | | | BCL2L15 | 1.00 |
| 8655 | 3 | | | | | ARL5B | 1.00 | 8751 | 3 | | | BCMO1 | 1.00 |
| 8656 | 3 | | | | | ARL5C | 1.00 | 8752 | 3 | | | BCORP1 | 1.00 |
| 8657 | 3 | | | | | ARL6 | 1.00 | 8753 | 3 | | | BCYRN1 | 1.00 |
| 8658 | 3 | | | | | ARMC1 | 1.00 | 8754 | 3 | | | BDAG1 | 1.00 |
| 8659 | 3 | | | | | ARMC12 | 1.00 | 8755 | 3 | | | BDNF | 1.00 |
| 8660 | 3 | | | | | ARMC2 | 1.00 | 8756 | 3 | | | BEND2 | 1.00 |
| 8661 | 3 | | | | | ARMC3 | 1.00 | 8757 | 3 | | | BEND3 | 1.00 |
| 8662 | 3 | | | | | ARMC4 | 1.00 | 8758 | 3 | | | BEND4 | 1.00 |
| 8663 | 3 | | | | | ARMC9 | 1.00 | 8759 | 3 | | | BEND6 | 1.00 |
| 8664 | 3 | | | | | ARMS2 | 1.00 | 8760 | 3 | | | BEST3 | 1.00 |
| 8665 | 3 | | | | | ARPM1 | 1.00 | 8761 | 3 | | | BET3L | 1.00 |
| 8666 | 3 | | | | | ARPP21 | 1.00 | 8762 | 3 | | | BFSP2 | 1.00 |
| 8667 | 3 | | | | | ARR3 | 1.00 | 8763 | 3 | | | BHLHA9 | 1.00 |
| 8668 | 3 | | | | | ARRDC5 | 1.00 | 8764 | 3 | | | BHLHE23 | 1.00 |
| 8669 | 3 | | | | | ARSE | 1.00 | 8765 | 3 | | | BHMT | 1.00 |
| 8670 | 3 | | | | | ARSH | 1.00 | 8766 | 3 | | | BICC1 | 1.00 |
| 8671 | 3 | | | | | ART1 | 1.00 | 8767 | 3 | | | BIRC8 | 1.00 |
| 8672 | 3 | | | | | ART5 | 1.00 | 8768 | 3 | | | BIVM-ERCC5 | 1.00 |
| 8673 | 3 | | | | | ARTN | 1.00 | 8769 | 3 | | | BK250D11 | 1.00 |
| 8674 | 3 | | | | | ARX | 1.00 | 8770 | 3 | | | BLID | 1.00 |
| 8675 | 3 | | | | | ASAH2 | 1.00 | 8771 | 3 | | | BLK | 1.00 |
| 8676 | 3 | | | | | ASAH2B | 1.00 | 8772 | 3 | | | BLM | 1.00 |
| 8677 | 3 | | | | | ASAP1-IT1 | 1.00 | 8773 | 3 | | | BMP10 | 1.00 |
| 8678 | 3 | | | | | ASB10 | 1.00 | 8774 | 3 | | | BMP15 | 1.00 |
| 8679 | 3 | | | | | ASB11 | 1.00 | 8775 | 3 | | | BMP3 | 1.00 |
| 8680 | 3 | | | | | ASB12 | 1.00 | 8776 | 3 | | | BMP5 | 1.00 |
| 8681 | 3 | | | | | ASB15 | 1.00 | 8777 | 3 | | | BMPER | 1.00 |
| 8682 | 3 | | | | | ASB17 | 1.00 | 8778 | 3 | | | BMPR1B | 1.00 |
| 8683 | 3 | | | | | ASB18 | 1.00 | 8779 | 3 | | | BMS1P4 | 1.00 |
| 8684 | 3 | | | | | ASB4 | 1.00 | 8780 | 3 | | | BOK-AS1 | 1.00 |
| 8685 | 3 | | | | | ASB5 | 1.00 | 8781 | 3 | | | BOLL | 1.00 |
| 8686 | 3 | | | | | ASB9P1 | 1.00 | 8782 | 3 | | | BPESC1 | 1.00 |
| 8687 | 3 | | | | | ASCL1 | 1.00 | 8783 | 3 | | | BPI | 1.00 |
| 8688 | 3 | | | | | ASCL3 | 1.00 | 8784 | 3 | | | BPIFA1 | 1.00 |
| 8689 | 3 | | | | | ASCL4 | 1.00 | 8785 | 3 | | | BPIFA2 | 1.00 |
| 8690 | 3 | | | | | ASMT | 1.00 | 8786 | 3 | | | BPIFA3 | 1.00 |
| 8691 | 3 | | | | | ASPDH | 1.00 | 8787 | 3 | | | BPIFA4P | 1.00 |
| 8692 | 3 | | | | | ASPG | 1.00 | 8788 | 3 | | | BPIFB1 | 1.00 |
| 8693 | 3 | | | | | ASPHD1 | 1.00 | 8789 | 3 | | | BPIFB2 | 1.00 |
| 8694 | 3 | | | | | ASPM | 1.00 | 8790 | 3 | | | BPIFB3 | 1.00 |
| 8695 | 3 | | | | | ASTL | 1.00 | 8791 | 3 | | | BPIFB4 | 1.00 |
| 8696 | 3 | | | | | ASXL3 | 1.00 | 8792 | 3 | | | BPIFB6 | 1.00 |
| 8697 | 3 | | | | | ASZ1 | 1.00 | 8793 | 3 | | | BRAF | 1.00 |
| 8698 | 3 | | | | | ATAD5 | 1.00 | 8794 | 3 | | | BRCA2 | 1.00 |
| 8699 | 3 | | | | | ATCAY | 1.00 | 8795 | 3 | | | BRD7P3 | 1.00 |
| 8700 | 3 | | | | | ATOH1 | 1.00 | 8796 | 3 | | | BRDT | 1.00 |
| 8701 | 3 | | | | | ATOH7 | 1.00 | 8797 | 3 | | | BRIP1 | 1.00 |
| 8702 | 3 | | | | | ATP1A3 | 1.00 | 8798 | 3 | | | BROX | 1.00 |
| 8703 | 3 | | | | | ATP1A4 | 1.00 | 8799 | 3 | | | BRS3 | 1.00 |
| 8704 | 3 | | | | | ATP1B4 | 1.00 | 8800 | 3 | | | BRSK1 | 1.00 |
| 8705 | 3 | | | | | ATP2A1 | 1.00 | 8801 | 3 | | | BRSK2 | 1.00 |
| 8706 | 3 | | | | | ATP2B2 | 1.00 | 8802 | 3 | | | BSN | 1.00 |
| 8707 | 3 | | | | | ATP2B3 | 1.00 | 8803 | 3 | | | BSN-AS2 | 1.00 |
| 8708 | 3 | | | | | ATP4A | 1.00 | 8804 | 3 | | | BSND | 1.00 |
| 8709 | 3 | | | | | ATP4B | 1.00 | 8805 | 3 | | | BSPH1 | 1.00 |
| 8710 | 3 | | | | | ATP6V0CP3 | 1.00 | 8806 | 3 | | | BSX | 1.00 |
| 8711 | 3 | | | | | ATP6V0D2 | 1.00 | 8807 | 3 | | | BTBD17 | 1.00 |
| 8712 | 3 | | | | | ATP6V1G3 | 1.00 | 8808 | 3 | | | BTBD18 | 1.00 |
| 8713 | 3 | | | | | ATP8A2 | 1.00 | 8809 | 3 | | | BTBD8 | 1.00 |
| 8714 | 3 | | | | | ATP8B3 | 1.00 | 8810 | 3 | | | BTF3P11 | 1.00 |
| 8715 | 3 | | | | | ATP8B4 | 1.00 | 8811 | 3 | | | BTG4 | 1.00 |
| 8716 | 3 | | | | | ATPAF1-AS1 | 1.00 | 8812 | 3 | | | BTLA | 1.00 |
| 8717 | 3 | | | | | ATR | 1.00 | 8813 | 3 | | | BTN1A1 | 1.00 |
| 8718 | 3 | | | | | ATRNL1 | 1.00 | 8814 | 3 | | | BTN2A3P | 1.00 |
| 8719 | 3 | | | | | ATXN3L | 1.00 | 8815 | 3 | | | BTNL2 | 1.00 |
| 8720 | 3 | | | | | ATXN8OS | 1.00 | 8816 | 3 | | | BTNL3 | 1.00 |
| 8721 | 3 | | | | | AVL9 | 1.00 | 8817 | 3 | | | BTNL8 | 1.00 |
| 8722 | 3 | | | | | AVP | 1.00 | 8818 | 3 | | | BUB1 | 1.00 |
| 8723 | 3 | | | | | AVPR1A | 1.00 | 8819 | 3 | | | BUB1B | 1.00 |
| 8724 | 3 | | | | | AVPR1B | 1.00 | 8820 | 3 | | | BVES-AS1 | 1.00 |
| 8725 | 3 | | | | | AXDND1 | 1.00 | 8821 | 3 | | | C10orf103 | 1.00 |
| 8726 | 3 | | | | | AZU1 | 1.00 | 8822 | 3 | | | C10orf107 | 1.00 |
| 8727 | 3 | | | | | B3GALT1 | 1.00 | 8823 | 3 | | | C10orf108 | 1.00 |
| 8728 | 3 | | | | | B3GALT2 | 1.00 | 8824 | 3 | | | C10orf111 | 1.00 |
| 8729 | 3 | | | | | B3GALT5 | 1.00 | 8825 | 3 | | | C10orf113 | 1.00 |
| 8730 | 3 | | | | | B3GAT1 | 1.00 | 8826 | 3 | | | C10orf12 | 1.00 |
| 8731 | 3 | | | | | B3GAT2 | 1.00 | 8827 | 3 | | | C10orf120 | 1.00 |
| 8732 | 3 | | | | | B3GNT6 | 1.00 | 8828 | 3 | | | C10orf122 | 1.00 |

Fig. 39 - 47

| | | | | | | | | | | | | | | | | |
|---|---|---|---|---|---|---|---|---|---|---|---|---|---|---|---|---|
| 8829 | 3 | | | | | C10orf131 | 1.00 | 8925 | 3 | | | | | C17orf77 | 1.00 |
| 8830 | 3 | | | | | C10orf136 | 1.00 | 8926 | 3 | | | | | C17orf78 | 1.00 |
| 8831 | 3 | | | | | C10orf140 | 1.00 | 8927 | 3 | | | | | C17orf82 | 1.00 |
| 8832 | 3 | | | | | C10orf27 | 1.00 | 8928 | 3 | | | | | C17orf98 | 1.00 |
| 8833 | 3 | | | | | C10orf32-AS3MT | 1.00 | 8929 | 3 | | | | | C17orf99 | 1.00 |
| 8834 | 3 | | | | | C10orf40 | 1.00 | 8930 | 3 | | | | | C18orf26 | 1.00 |
| 8835 | 3 | | | | | C10orf53 | 1.00 | 8931 | 3 | | | | | C18orf34 | 1.00 |
| 8836 | 3 | | | | | C10orf62 | 1.00 | 8932 | 3 | | | | | C18orf42 | 1.00 |
| 8837 | 3 | | | | | C10orf67 | 1.00 | 8933 | 3 | | | | | C18orf54 | 1.00 |
| 8838 | 3 | | | | | C10orf68 | 1.00 | 8934 | 3 | | | | | C18orf56 | 1.00 |
| 8839 | 3 | | | | | C10orf71 | 1.00 | 8935 | 3 | | | | | C18orf62 | 1.00 |
| 8840 | 3 | | | | | C10orf90 | 1.00 | 8936 | 3 | | | | | C18orf63 | 1.00 |
| 8841 | 3 | | | | | C10orf96 | 1.00 | 8937 | 3 | | | | | C19orf35 | 1.00 |
| 8842 | 3 | | | | | C11orf16 | 1.00 | 8938 | 3 | | | | | C19orf45 | 1.00 |
| 8843 | 3 | | | | | C11orf34 | 1.00 | 8939 | 3 | | | | | C19orf59 | 1.00 |
| 8844 | 3 | | | | | C11orf36 | 1.00 | 8940 | 3 | | | | | C19orf69 | 1.00 |
| 8845 | 3 | | | | | C11orf40 | 1.00 | 8941 | 3 | | | | | C19orf75 | 1.00 |
| 8846 | 3 | | | | | C11orf41 | 1.00 | 8942 | 3 | | | | | C19orf80 | 1.00 |
| 8847 | 3 | | | | | C11orf42 | 1.00 | 8943 | 3 | | | | | C1orf100 | 1.00 |
| 8848 | 3 | | | | | C11orf53 | 1.00 | 8944 | 3 | | | | | C1orf101 | 1.00 |
| 8849 | 3 | | | | | C11orf65 | 1.00 | 8945 | 3 | | | | | C1orf105 | 1.00 |
| 8850 | 3 | | | | | C11orf82 | 1.00 | 8946 | 3 | | | | | C1orf110 | 1.00 |
| 8851 | 3 | | | | | C11orf85 | 1.00 | 8947 | 3 | | | | | C1orf111 | 1.00 |
| 8852 | 3 | | | | | C11orf86 | 1.00 | 8948 | 3 | | | | | C1orf112 | 1.00 |
| 8853 | 3 | | | | | C11orf87 | 1.00 | 8949 | 3 | | | | | C1orf114 | 1.00 |
| 8854 | 3 | | | | | C11orf88 | 1.00 | 8950 | 3 | | | | | C1orf127 | 1.00 |
| 8855 | 3 | | | | | C11orf91 | 1.00 | 8951 | 3 | | | | | C1orf129 | 1.00 |
| 8856 | 3 | | | | | C11orf92 | 1.00 | 8952 | 3 | | | | | C1orf135 | 1.00 |
| 8857 | 3 | | | | | C11orf94 | 1.00 | 8953 | 3 | | | | | C1orf140 | 1.00 |
| 8858 | 3 | | | | | C12orf12 | 1.00 | 8954 | 3 | | | | | C1orf141 | 1.00 |
| 8859 | 3 | | | | | C12orf33 | 1.00 | 8955 | 3 | | | | | C1orf146 | 1.00 |
| 8860 | 3 | | | | | C12orf36 | 1.00 | 8956 | 3 | | | | | C1orf150 | 1.00 |
| 8861 | 3 | | | | | C12orf37 | 1.00 | 8957 | 3 | | | | | C1orf158 | 1.00 |
| 8862 | 3 | | | | | C12orf39 | 1.00 | 8958 | 3 | | | | | C1orf168 | 1.00 |
| 8863 | 3 | | | | | C12orf40 | 1.00 | 8959 | 3 | | | | | C1orf173 | 1.00 |
| 8864 | 3 | | | | | C12orf42 | 1.00 | 8960 | 3 | | | | | C1orf177 | 1.00 |
| 8865 | 3 | | | | | C12orf50 | 1.00 | 8961 | 3 | | | | | C1orf180 | 1.00 |
| 8866 | 3 | | | | | C12orf54 | 1.00 | 8962 | 3 | | | | | C1orf182 | 1.00 |
| 8867 | 3 | | | | | C12orf56 | 1.00 | 8963 | 3 | | | | | C1orf185 | 1.00 |
| 8868 | 3 | | | | | C12orf59 | 1.00 | 8964 | 3 | | | | | C1orf187 | 1.00 |
| 8869 | 3 | | | | | C12orf60 | 1.00 | 8965 | 3 | | | | | C1orf189 | 1.00 |
| 8870 | 3 | | | | | C12orf61 | 1.00 | 8966 | 3 | | | | | C1orf194 | 1.00 |
| 8871 | 3 | | | | | C12orf69 | 1.00 | 8967 | 3 | | | | | C1orf200 | 1.00 |
| 8872 | 3 | | | | | C12orf70 | 1.00 | 8968 | 3 | | | | | C1orf220 | 1.00 |
| 8873 | 3 | | | | | C12orf71 | 1.00 | 8969 | 3 | | | | | C1orf227 | 1.00 |
| 8874 | 3 | | | | | C12orf74 | 1.00 | 8970 | 3 | | | | | C1orf228 | 1.00 |
| 8875 | 3 | | | | | C12orf77 | 1.00 | 8971 | 3 | | | | | C1orf229 | 1.00 |
| 8876 | 3 | | | | | C13orf35 | 1.00 | 8972 | 3 | | | | | C1orf49 | 1.00 |
| 8877 | 3 | | | | | C14orf105 | 1.00 | 8973 | 3 | | | | | C1orf61 | 1.00 |
| 8878 | 3 | | | | | C14orf162 | 1.00 | 8974 | 3 | | | | | C1orf64 | 1.00 |
| 8879 | 3 | | | | | C14orf165 | 1.00 | 8975 | 3 | | | | | C1orf65 | 1.00 |
| 8880 | 3 | | | | | C14orf166B | 1.00 | 8976 | 3 | | | | | C1orf87 | 1.00 |
| 8881 | 3 | | | | | C14orf177 | 1.00 | 8977 | 3 | | | | | C1orf94 | 1.00 |
| 8882 | 3 | | | | | C14orf178 | 1.00 | 8978 | 3 | | | | | C1orf98 | 1.00 |
| 8883 | 3 | | | | | C14orf182 | 1.00 | 8979 | 3 | | | | | C1QL1 | 1.00 |
| 8884 | 3 | | | | | C14orf183 | 1.00 | 8980 | 3 | | | | | C1QL2 | 1.00 |
| 8885 | 3 | | | | | C14orf23 | 1.00 | 8981 | 3 | | | | | C1QL3 | 1.00 |
| 8886 | 3 | | | | | C14orf37 | 1.00 | 8982 | 3 | | | | | C1QL4 | 1.00 |
| 8887 | 3 | | | | | C14orf38 | 1.00 | 8983 | 3 | | | | | C1QTNF3-AMACR | 1.00 |
| 8888 | 3 | | | | | C14orf39 | 1.00 | 8984 | 3 | | | | | C1QTNF8 | 1.00 |
| 8889 | 3 | | | | | C14orf55 | 1.00 | 8985 | 3 | | | | | C20orf123 | 1.00 |
| 8890 | 3 | | | | | C15orf2 | 1.00 | 8986 | 3 | | | | | C20orf132 | 1.00 |
| 8891 | 3 | | | | | C15orf26 | 1.00 | 8987 | 3 | | | | | C20orf141 | 1.00 |
| 8892 | 3 | | | | | C15orf32 | 1.00 | 8988 | 3 | | | | | C20orf144 | 1.00 |
| 8893 | 3 | | | | | C15orf33 | 1.00 | 8989 | 3 | | | | | C20orf152 | 1.00 |
| 8894 | 3 | | | | | C15orf34 | 1.00 | 8990 | 3 | | | | | C20orf166 | 1.00 |
| 8895 | 3 | | | | | C15orf38-AP3S2 | 1.00 | 8991 | 3 | | | | | C20orf166-AS1 | 1.00 |
| 8896 | 3 | | | | | C15orf42 | 1.00 | 8992 | 3 | | | | | C20orf173 | 1.00 |
| 8897 | 3 | | | | | C15orf43 | 1.00 | 8993 | 3 | | | | | C20orf197 | 1.00 |
| 8898 | 3 | | | | | C15orf5 | 1.00 | 8994 | 3 | | | | | C20orf201 | 1.00 |
| 8899 | 3 | | | | | C15orf50 | 1.00 | 8995 | 3 | | | | | C20orf202 | 1.00 |
| 8900 | 3 | | | | | C15orf53 | 1.00 | 8996 | 3 | | | | | C20orf203 | 1.00 |
| 8901 | 3 | | | | | C15orf54 | 1.00 | 8997 | 3 | | | | | C20orf26 | 1.00 |
| 8902 | 3 | | | | | C15orf55 | 1.00 | 8998 | 3 | | | | | C20orf79 | 1.00 |
| 8903 | 3 | | | | | C15orf56 | 1.00 | 8999 | 3 | | | | | C20orf85 | 1.00 |
| 8904 | 3 | | | | | C15orf60 | 1.00 | 9000 | 3 | | | | | C20orf94 | 1.00 |
| 8905 | 3 | | | | | C16orf11 | 1.00 | 9001 | 3 | | | | | C21orf128 | 1.00 |
| 8906 | 3 | | | | | C16orf3 | 1.00 | 9002 | 3 | | | | | C21orf15 | 1.00 |
| 8907 | 3 | | | | | C16orf59 | 1.00 | 9003 | 3 | | | | | C21orf37 | 1.00 |
| 8908 | 3 | | | | | C16orf71 | 1.00 | 9004 | 3 | | | | | C21orf49 | 1.00 |
| 8909 | 3 | | | | | C16orf73 | 1.00 | 9005 | 3 | | | | | C21orf54 | 1.00 |
| 8910 | 3 | | | | | C16orf78 | 1.00 | 9006 | 3 | | | | | C21orf62 | 1.00 |
| 8911 | 3 | | | | | C16orf82 | 1.00 | 9007 | 3 | | | | | C21orf90 | 1.00 |
| 8912 | 3 | | | | | C16orf90 | 1.00 | 9008 | 3 | | | | | C21orf91-OT1 | 1.00 |
| 8913 | 3 | | | | | C16orf92 | 1.00 | 9009 | 3 | | | | | C22orf15 | 1.00 |
| 8914 | 3 | | | | | C16orf93 | 1.00 | 9010 | 3 | | | | | C22orf24 | 1.00 |
| 8915 | 3 | | | | | C16orf96 | 1.00 | 9011 | 3 | | | | | C22orf26 | 1.00 |
| 8916 | 3 | | | | | C17orf102 | 1.00 | 9012 | 3 | | | | | C22orf42 | 1.00 |
| 8917 | 3 | | | | | C17orf104 | 1.00 | 9013 | 3 | | | | | C22orf43 | 1.00 |
| 8918 | 3 | | | | | C17orf105 | 1.00 | 9014 | 3 | | | | | C22orf45 | 1.00 |
| 8919 | 3 | | | | | C17orf110 | 1.00 | 9015 | 3 | | | | | C2CD4A | 1.00 |
| 8920 | 3 | | | | | C17orf47 | 1.00 | 9016 | 3 | | | | | C2orf16 | 1.00 |
| 8921 | 3 | | | | | C17orf50 | 1.00 | 9017 | 3 | | | | | C2orf27A | 1.00 |
| 8922 | 3 | | | | | C17orf64 | 1.00 | 9018 | 3 | | | | | C2orf27B | 1.00 |
| 8923 | 3 | | | | | C17orf66 | 1.00 | 9019 | 3 | | | | | C2orf48 | 1.00 |
| 8924 | 3 | | | | | C17orf74 | 1.00 | 9020 | 3 | | | | | C2orf50 | 1.00 |

Fig. 39 - 48

| | | | | | | | | | | | | | | |
|---|---|---|---|---|---|---|---|---|---|---|---|---|---|---|
| 9021 | 3 | | | | | C2orf51 | 1.00 | 9117 | 3 | | | | C8orf45 | 1.00 |
| 9022 | 3 | | | | | C2orf53 | 1.00 | 9118 | 3 | | | | C8orf46 | 1.00 |
| 9023 | 3 | | | | | C2orf57 | 1.00 | 9119 | 3 | | | | C8orf51 | 1.00 |
| 9024 | 3 | | | | | C2orf61 | 1.00 | 9120 | 3 | | | | C8orf56 | 1.00 |
| 9025 | 3 | | | | | C2orf62 | 1.00 | 9121 | 3 | | | | C8orf69 | 1.00 |
| 9026 | 3 | | | | | C2orf65 | 1.00 | 9122 | 3 | | | | C8orf71 | 1.00 |
| 9027 | 3 | | | | | C2orf66 | 1.00 | 9123 | 3 | | | | C8orf74 | 1.00 |
| 9028 | 3 | | | | | C2orf70 | 1.00 | 9124 | 3 | | | | C8orf75 | 1.00 |
| 9029 | 3 | | | | | C2orf71 | 1.00 | 9125 | 3 | | | | C8orf77 | 1.00 |
| 9030 | 3 | | | | | C2orf73 | 1.00 | 9126 | 3 | | | | C8orf80 | 1.00 |
| 9031 | 3 | | | | | C2orf77 | 1.00 | 9127 | 3 | | | | C8orf86 | 1.00 |
| 9032 | 3 | | | | | C2orf78 | 1.00 | 9128 | 3 | | | | C8orf87 | 1.00 |
| 9033 | 3 | | | | | C2orf80 | 1.00 | 9129 | 3 | | | | C8ORFK29 | 1.00 |
| 9034 | 3 | | | | | C2orf83 | 1.00 | 9130 | 3 | | | | C9 | 1.00 |
| 9035 | 3 | | | | | C2orf84 | 1.00 | 9131 | 3 | | | | C9orf102 | 1.00 |
| 9036 | 3 | | | | | C2orf91 | 1.00 | 9132 | 3 | | | | C9orf106 | 1.00 |
| 9037 | 3 | | | | | C3orf15 | 1.00 | 9133 | 3 | | | | C9orf11 | 1.00 |
| 9038 | 3 | | | | | C3orf20 | 1.00 | 9134 | 3 | | | | C9orf117 | 1.00 |
| 9039 | 3 | | | | | C3orf22 | 1.00 | 9135 | 3 | | | | C9orf128 | 1.00 |
| 9040 | 3 | | | | | C3orf24 | 1.00 | 9136 | 3 | | | | C9orf131 | 1.00 |
| 9041 | 3 | | | | | C3orf25 | 1.00 | 9137 | 3 | | | | C9orf135 | 1.00 |
| 9042 | 3 | | | | | C3orf27 | 1.00 | 9138 | 3 | | | | C9orf139 | 1.00 |
| 9043 | 3 | | | | | C3orf30 | 1.00 | 9139 | 3 | | | | C9orf146 | 1.00 |
| 9044 | 3 | | | | | C3orf32 | 1.00 | 9140 | 3 | | | | C9orf153 | 1.00 |
| 9045 | 3 | | | | | C3orf36 | 1.00 | 9141 | 3 | | | | C9orf163 | 1.00 |
| 9046 | 3 | | | | | C3orf43 | 1.00 | 9142 | 3 | | | | C9orf170 | 1.00 |
| 9047 | 3 | | | | | C3orf45 | 1.00 | 9143 | 3 | | | | C9orf171 | 1.00 |
| 9048 | 3 | | | | | C3orf49 | 1.00 | 9144 | 3 | | | | C9orf174 | 1.00 |
| 9049 | 3 | | | | | C3orf51 | 1.00 | 9145 | 3 | | | | C9orf29 | 1.00 |
| 9050 | 3 | | | | | C3orf65 | 1.00 | 9146 | 3 | | | | C9orf30-TMEFF1 | 1.00 |
| 9051 | 3 | | | | | C3orf67 | 1.00 | 9147 | 3 | | | | C9orf4 | 1.00 |
| 9052 | 3 | | | | | C3orf72 | 1.00 | 9148 | 3 | | | | C9orf41 | 1.00 |
| 9053 | 3 | | | | | C3orf77 | 1.00 | 9149 | 3 | | | | C9orf43 | 1.00 |
| 9054 | 3 | | | | | C3orf79 | 1.00 | 9150 | 3 | | | | C9orf47 | 1.00 |
| 9055 | 3 | | | | | C3P1 | 1.00 | 9151 | 3 | | | | C9orf50 | 1.00 |
| 9056 | 3 | | | | | C4A | 1.00 | 9152 | 3 | | | | C9orf53 | 1.00 |
| 9057 | 3 | | | | | C4B | 1.00 | 9153 | 3 | | | | C9orf57 | 1.00 |
| 9058 | 3 | | | | | C4BPA | 1.00 | 9154 | 3 | | | | C9orf66 | 1.00 |
| 9059 | 3 | | | | | C4BPB | 1.00 | 9155 | 3 | | | | C9orf71 | 1.00 |
| 9060 | 3 | | | | | C4orf17 | 1.00 | 9156 | 3 | | | | C9orf79 | 1.00 |
| 9061 | 3 | | | | | C4orf21 | 1.00 | 9157 | 3 | | | | C9orf84 | 1.00 |
| 9062 | 3 | | | | | C4orf22 | 1.00 | 9158 | 3 | | | | C9orf93 | 1.00 |
| 9063 | 3 | | | | | C4orf26 | 1.00 | 9159 | 3 | | | | C9orf96 | 1.00 |
| 9064 | 3 | | | | | C4orf36 | 1.00 | 9160 | 3 | | | | CA1 | 1.00 |
| 9065 | 3 | | | | | C4orf37 | 1.00 | 9161 | 3 | | | | CA10 | 1.00 |
| 9066 | 3 | | | | | C4orf38 | 1.00 | 9162 | 3 | | | | CA14 | 1.00 |
| 9067 | 3 | | | | | C4orf40 | 1.00 | 9163 | 3 | | | | CA5A | 1.00 |
| 9068 | 3 | | | | | C4orf44 | 1.00 | 9164 | 3 | | | | CA7 | 1.00 |
| 9069 | 3 | | | | | C4orf45 | 1.00 | 9165 | 3 | | | | CABP2 | 1.00 |
| 9070 | 3 | | | | | C4orf49 | 1.00 | 9166 | 3 | | | | CABP5 | 1.00 |
| 9071 | 3 | | | | | C4orf51 | 1.00 | 9167 | 3 | | | | CABP7 | 1.00 |
| 9072 | 3 | | | | | C4orf6 | 1.00 | 9168 | 3 | | | | CABS1 | 1.00 |
| 9073 | 3 | | | | | C5 | 1.00 | 9169 | 3 | | | | CACNA1A | 1.00 |
| 9074 | 3 | | | | | C5orf34 | 1.00 | 9170 | 3 | | | | CACNA1B | 1.00 |
| 9075 | 3 | | | | | C5orf42 | 1.00 | 9171 | 3 | | | | CACNA1D | 1.00 |
| 9076 | 3 | | | | | C5orf47 | 1.00 | 9172 | 3 | | | | CACNA1E | 1.00 |
| 9077 | 3 | | | | | C5orf48 | 1.00 | 9173 | 3 | | | | CACNA1F | 1.00 |
| 9078 | 3 | | | | | C5orf49 | 1.00 | 9174 | 3 | | | | CACNA1I | 1.00 |
| 9079 | 3 | | | | | C5orf52 | 1.00 | 9175 | 3 | | | | CACNA1S | 1.00 |
| 9080 | 3 | | | | | C5orf58 | 1.00 | 9176 | 3 | | | | CACNA2D1 | 1.00 |
| 9081 | 3 | | | | | C5orf60 | 1.00 | 9177 | 3 | | | | CACNA2D3 | 1.00 |
| 9082 | 3 | | | | | C5orf64 | 1.00 | 9178 | 3 | | | | CACNA2D4 | 1.00 |
| 9083 | 3 | | | | | C6orf10 | 1.00 | 9179 | 3 | | | | CACNG1 | 1.00 |
| 9084 | 3 | | | | | C6orf118 | 1.00 | 9180 | 3 | | | | CACNG2 | 1.00 |
| 9085 | 3 | | | | | C6orf123 | 1.00 | 9181 | 3 | | | | CACNG3 | 1.00 |
| 9086 | 3 | | | | | C6orf147 | 1.00 | 9182 | 3 | | | | CACNG5 | 1.00 |
| 9087 | 3 | | | | | C6orf164 | 1.00 | 9183 | 3 | | | | CACNG6 | 1.00 |
| 9088 | 3 | | | | | C6orf165 | 1.00 | 9184 | 3 | | | | CACNG7 | 1.00 |
| 9089 | 3 | | | | | C6orf174 | 1.00 | 9185 | 3 | | | | CACNG8 | 1.00 |
| 9090 | 3 | | | | | C6orf195 | 1.00 | 9186 | 3 | | | | CADM2 | 1.00 |
| 9091 | 3 | | | | | C6orf201 | 1.00 | 9187 | 3 | | | | CADPS | 1.00 |
| 9092 | 3 | | | | | C6orf221 | 1.00 | 9188 | 3 | | | | CAGE1 | 1.00 |
| 9093 | 3 | | | | | C6orf222 | 1.00 | 9189 | 3 | | | | CALB1 | 1.00 |
| 9094 | 3 | | | | | C6orf223 | 1.00 | 9190 | 3 | | | | CALCA | 1.00 |
| 9095 | 3 | | | | | C6orf58 | 1.00 | 9191 | 3 | | | | CALCB | 1.00 |
| 9096 | 3 | | | | | C6orf7 | 1.00 | 9192 | 3 | | | | CALCR | 1.00 |
| 9097 | 3 | | | | | C6orf97 | 1.00 | 9193 | 3 | | | | CALHM1 | 1.00 |
| 9098 | 3 | | | | | C6orf99 | 1.00 | 9194 | 3 | | | | CALHM3 | 1.00 |
| 9099 | 3 | | | | | C7orf10 | 1.00 | 9195 | 3 | | | | CALML6 | 1.00 |
| 9100 | 3 | | | | | C7orf33 | 1.00 | 9196 | 3 | | | | CALN1 | 1.00 |
| 9101 | 3 | | | | | C7orf34 | 1.00 | 9197 | 3 | | | | CALR3 | 1.00 |
| 9102 | 3 | | | | | C7orf45 | 1.00 | 9198 | 3 | | | | CALY | 1.00 |
| 9103 | 3 | | | | | C7orf57 | 1.00 | 9199 | 3 | | | | CAMK1G | 1.00 |
| 9104 | 3 | | | | | C7orf62 | 1.00 | 9200 | 3 | | | | CAMK2A | 1.00 |
| 9105 | 3 | | | | | C7orf65 | 1.00 | 9201 | 3 | | | | CAMK2N2 | 1.00 |
| 9106 | 3 | | | | | C7orf66 | 1.00 | 9202 | 3 | | | | CAMK4 | 1.00 |
| 9107 | 3 | | | | | C7orf69 | 1.00 | 9203 | 3 | | | | CAMKV | 1.00 |
| 9108 | 3 | | | | | C7orf71 | 1.00 | 9204 | 3 | | | | CAMP | 1.00 |
| 9109 | 3 | | | | | C7orf72 | 1.00 | 9205 | 3 | | | | CAPN13 | 1.00 |
| 9110 | 3 | | | | | C8A | 1.00 | 9206 | 3 | | | | CAPN14 | 1.00 |
| 9111 | 3 | | | | | C8B | 1.00 | 9207 | 3 | | | | CAPN8 | 1.00 |
| 9112 | 3 | | | | | C8orf12 | 1.00 | 9208 | 3 | | | | CAPN9 | 1.00 |
| 9113 | 3 | | | | | C8orf22 | 1.00 | 9209 | 3 | | | | CAPS2 | 1.00 |
| 9114 | 3 | | | | | C8orf31 | 1.00 | 9210 | 3 | | | | CAPSL | 1.00 |
| 9115 | 3 | | | | | C8orf34 | 1.00 | 9211 | 3 | | | | CAPZA3 | 1.00 |
| 9116 | 3 | | | | | C8orf39 | 1.00 | 9212 | 3 | | | | CARTPT | 1.00 |

Fig. 39 - 49

| | | | | | | | |
|---|---|---|---|---|---|---|---|
| 9213 | 3 | | | CASC1 | 1.00 | | |
| 9214 | 3 | | | CASC2 | 1.00 | | |
| 9215 | 3 | | | CASC5 | 1.00 | | |
| 9216 | 3 | | | CASP12 | 1.00 | | |
| 9217 | 3 | | | CASP5 | 1.00 | | |
| 9218 | 3 | | | CASR | 1.00 | | |
| 9219 | 3 | | | CATSPER1 | 1.00 | | |
| 9220 | 3 | | | CATSPER3 | 1.00 | | |
| 9221 | 3 | | | CATSPER4 | 1.00 | | |
| 9222 | 3 | | | CATSPERB | 1.00 | | |
| 9223 | 3 | | | CATSPERD | 1.00 | | |
| 9224 | 3 | | | CATSPERG | 1.00 | | |
| 9225 | 3 | | | CAV3 | 1.00 | | |
| 9226 | 3 | | | CBLN2 | 1.00 | | |
| 9227 | 3 | | | CBLN4 | 1.00 | | |
| 9228 | 3 | | | CBY3 | 1.00 | | |
| 9229 | 3 | | | CC2D2B | 1.00 | | |
| 9230 | 3 | | | CCDC105 | 1.00 | | |
| 9231 | 3 | | | CCDC108 | 1.00 | | |
| 9232 | 3 | | | CCDC11 | 1.00 | | |
| 9233 | 3 | | | CCDC110 | 1.00 | | |
| 9234 | 3 | | | CCDC116 | 1.00 | | |
| 9235 | 3 | | | CCDC13 | 1.00 | | |
| 9236 | 3 | | | CCDC135 | 1.00 | | |
| 9237 | 3 | | | CCDC136 | 1.00 | | |
| 9238 | 3 | | | CCDC138 | 1.00 | | |
| 9239 | 3 | | | CCDC140 | 1.00 | | |
| 9240 | 3 | | | CCDC141 | 1.00 | | |
| 9241 | 3 | | | CCDC144A | 1.00 | | |
| 9242 | 3 | | | CCDC144B | 1.00 | | |
| 9243 | 3 | | | CCDC144C | 1.00 | | |
| 9244 | 3 | | | CCDC144NL | 1.00 | | |
| 9245 | 3 | | | CCDC147 | 1.00 | | |
| 9246 | 3 | | | CCDC148 | 1.00 | | |
| 9247 | 3 | | | CCDC150 | 1.00 | | |
| 9248 | 3 | | | CCDC151 | 1.00 | | |
| 9249 | 3 | | | CCDC154 | 1.00 | | |
| 9250 | 3 | | | CCDC155 | 1.00 | | |
| 9251 | 3 | | | CCDC158 | 1.00 | | |
| 9252 | 3 | | | CCDC162P | 1.00 | | |
| 9253 | 3 | | | CCDC164 | 1.00 | | |
| 9254 | 3 | | | CCDC166 | 1.00 | | |
| 9255 | 3 | | | CCDC168 | 1.00 | | |
| 9256 | 3 | | | CCDC169 | 1.00 | | |
| 9257 | 3 | | | CCDC169-SOHLH2 | 1.00 | | |
| 9258 | 3 | | | CCDC18 | 1.00 | | |
| 9259 | 3 | | | CCDC19 | 1.00 | | |
| 9260 | 3 | | | CCDC27 | 1.00 | | |
| 9261 | 3 | | | CCDC30 | 1.00 | | |
| 9262 | 3 | | | CCDC33 | 1.00 | | |
| 9263 | 3 | | | CCDC36 | 1.00 | | |
| 9264 | 3 | | | CCDC37 | 1.00 | | |
| 9265 | 3 | | | CCDC38 | 1.00 | | |
| 9266 | 3 | | | CCDC39 | 1.00 | | |
| 9267 | 3 | | | CCDC42 | 1.00 | | |
| 9268 | 3 | | | CCDC54 | 1.00 | | |
| 9269 | 3 | | | CCDC60 | 1.00 | | |
| 9270 | 3 | | | CCDC62 | 1.00 | | |
| 9271 | 3 | | | CCDC63 | 1.00 | | |
| 9272 | 3 | | | CCDC65 | 1.00 | | |
| 9273 | 3 | | | CCDC67 | 1.00 | | |
| 9274 | 3 | | | CCDC68 | 1.00 | | |
| 9275 | 3 | | | CCDC7 | 1.00 | | |
| 9276 | 3 | | | CCDC70 | 1.00 | | |
| 9277 | 3 | | | CCDC75 | 1.00 | | |
| 9278 | 3 | | | CCDC78 | 1.00 | | |
| 9279 | 3 | | | CCDC79 | 1.00 | | |
| 9280 | 3 | | | CCDC81 | 1.00 | | |
| 9281 | 3 | | | CCDC83 | 1.00 | | |
| 9282 | 3 | | | CCDC87 | 1.00 | | |
| 9283 | 3 | | | CCDC89 | 1.00 | | |
| 9284 | 3 | | | CCIN | 1.00 | | |
| 9285 | 3 | | | CCK | 1.00 | | |
| 9286 | 3 | | | CCKAR | 1.00 | | |
| 9287 | 3 | | | CCKBR | 1.00 | | |
| 9288 | 3 | | | CCL1 | 1.00 | | |
| 9289 | 3 | | | CCL11 | 1.00 | | |
| 9290 | 3 | | | CCL14-CCL15 | 1.00 | | |
| 9291 | 3 | | | CCL15 | 1.00 | | |
| 9292 | 3 | | | CCL25 | 1.00 | | |
| 9293 | 3 | | | CCL3L1 | 1.00 | | |
| 9294 | 3 | | | CCL3L3 | 1.00 | | |
| 9295 | 3 | | | CCL7 | 1.00 | | |
| 9296 | 3 | | | CCL8 | 1.00 | | |
| 9297 | 3 | | | CCNA1 | 1.00 | | |
| 9298 | 3 | | | CCNB3 | 1.00 | | |
| 9299 | 3 | | | CCNE2 | 1.00 | | |
| 9300 | 3 | | | CCNI2 | 1.00 | | |
| 9301 | 3 | | | CCR3 | 1.00 | | |
| 9302 | 3 | | | CCR4 | 1.00 | | |
| 9303 | 3 | | | CCR8 | 1.00 | | |
| 9304 | 3 | | | CCR9 | 1.00 | | |
| 9305 | 3 | | | CCT6B | 1.00 | | |
| 9306 | 3 | | | CCT8L2 | 1.00 | | |
| 9307 | 3 | | | CD163L1 | 1.00 | | |
| 9308 | 3 | | | CD180 | 1.00 | | |
| 9309 | 3 | | | CD19 | 1.00 | | |
| 9310 | 3 | | | CD1D | 1.00 | | |
| 9311 | 3 | | | CD200R1L | 1.00 | | |
| 9312 | 3 | | | CD22 | 1.00 | | |
| 9313 | 3 | | | CD226 | 1.00 | | |
| 9314 | 3 | | | CD244 | 1.00 | | |
| 9315 | 3 | | | CD274 | 1.00 | | |
| 9316 | 3 | | | CD28 | 1.00 | | |
| 9317 | 3 | | | CD300C | 1.00 | | |
| 9318 | 3 | | | CD300LB | 1.00 | | |
| 9319 | 3 | | | CD300LD | 1.00 | | |
| 9320 | 3 | | | CD300LF | 1.00 | | |
| 9321 | 3 | | | CD38 | 1.00 | | |
| 9322 | 3 | | | CD5L | 1.00 | | |
| 9323 | 3 | | | CD79A | 1.00 | | |
| 9324 | 3 | | | CD80 | 1.00 | | |
| 9325 | 3 | | | CDC14C | 1.00 | | |
| 9326 | 3 | | | CDC20B | 1.00 | | |
| 9327 | 3 | | | CDC25A | 1.00 | | |
| 9328 | 3 | | | CDC25C | 1.00 | | |
| 9329 | 3 | | | CDCA2 | 1.00 | | |
| 9330 | 3 | | | CDCP2 | 1.00 | | |
| 9331 | 3 | | | CDH10 | 1.00 | | |
| 9332 | 3 | | | CDH12 | 1.00 | | |
| 9333 | 3 | | | CDH15 | 1.00 | | |
| 9334 | 3 | | | CDH16 | 1.00 | | |
| 9335 | 3 | | | CDH17 | 1.00 | | |
| 9336 | 3 | | | CDH18 | 1.00 | | |
| 9337 | 3 | | | CDH2 | 1.00 | | |
| 9338 | 3 | | | CDH20 | 1.00 | | |
| 9339 | 3 | | | CDH26 | 1.00 | | |
| 9340 | 3 | | | CDH7 | 1.00 | | |
| 9341 | 3 | | | CDH8 | 1.00 | | |
| 9342 | 3 | | | CDH9 | 1.00 | | |
| 9343 | 3 | | | CDHR2 | 1.00 | | |
| 9344 | 3 | | | CDHR3 | 1.00 | | |
| 9345 | 3 | | | CDHR5 | 1.00 | | |
| 9346 | 3 | | | CDK15 | 1.00 | | |
| 9347 | 3 | | | CDK5R2 | 1.00 | | |
| 9348 | 3 | | | CDKL1 | 1.00 | | |
| 9349 | 3 | | | CDKL2 | 1.00 | | |
| 9350 | 3 | | | CDKL4 | 1.00 | | |
| 9351 | 3 | | | CDKL5 | 1.00 | | |
| 9352 | 3 | | | CDKN2B-AS1 | 1.00 | | |
| 9353 | 3 | | | CDRT1 | 1.00 | | |
| 9354 | 3 | | | CDRT15 | 1.00 | | |
| 9355 | 3 | | | CDRT15L2 | 1.00 | | |
| 9356 | 3 | | | CDRT15P2 | 1.00 | | |
| 9357 | 3 | | | CDRT7 | 1.00 | | |
| 9358 | 3 | | | CDX1 | 1.00 | | |
| 9359 | 3 | | | CDX2 | 1.00 | | |
| 9360 | 3 | | | CDX4 | 1.00 | | |
| 9361 | 3 | | | CDY1 | 1.00 | | |
| 9362 | 3 | | | CDY1B | 1.00 | | |
| 9363 | 3 | | | CDY2A | 1.00 | | |
| 9364 | 3 | | | CDY2B | 1.00 | | |
| 9365 | 3 | | | CDYL2 | 1.00 | | |
| 9366 | 3 | | | CEACAM16 | 1.00 | | |
| 9367 | 3 | | | CEACAM18 | 1.00 | | |
| 9368 | 3 | | | CEACAM20 | 1.00 | | |
| 9369 | 3 | | | CEACAM21 | 1.00 | | |
| 9370 | 3 | | | CEACAM22P | 1.00 | | |
| 9371 | 3 | | | CEACAM3 | 1.00 | | |
| 9372 | 3 | | | CEACAM4 | 1.00 | | |
| 9373 | 3 | | | CEACAM8 | 1.00 | | |
| 9374 | 3 | | | CEBPE | 1.00 | | |
| 9375 | 3 | | | CECR2 | 1.00 | | |
| 9376 | 3 | | | CECR3 | 1.00 | | |
| 9377 | 3 | | | CECR6 | 1.00 | | |
| 9378 | 3 | | | CELA1 | 1.00 | | |
| 9379 | 3 | | | CELA2A | 1.00 | | |
| 9380 | 3 | | | CELA2B | 1.00 | | |
| 9381 | 3 | | | CELA3A | 1.00 | | |
| 9382 | 3 | | | CELA3B | 1.00 | | |
| 9383 | 3 | | | CELF3 | 1.00 | | |
| 9384 | 3 | | | CELF4 | 1.00 | | |
| 9385 | 3 | | | CELF5 | 1.00 | | |
| 9386 | 3 | | | CELP | 1.00 | | |
| 9387 | 3 | | | CELSR3 | 1.00 | | |
| 9388 | 3 | | | CEND1 | 1.00 | | |
| 9389 | 3 | | | CENPE | 1.00 | | |
| 9390 | 3 | | | CENPI | 1.00 | | |
| 9391 | 3 | | | CENPQ | 1.00 | | |
| 9392 | 3 | | | CENPVL1 | 1.00 | | |
| 9393 | 3 | | | CEP128 | 1.00 | | |
| 9394 | 3 | | | CEP170P1 | 1.00 | | |
| 9395 | 3 | | | CEP290 | 1.00 | | |
| 9396 | 3 | | | CEP97 | 1.00 | | |
| 9397 | 3 | | | CER1 | 1.00 | | |
| 9398 | 3 | | | CERS1 | 1.00 | | |
| 9399 | 3 | | | CES1P1 | 1.00 | | |
| 9400 | 3 | | | CES1P2 | 1.00 | | |
| 9401 | 3 | | | CES3 | 1.00 | | |
| 9402 | 3 | | | CES5A | 1.00 | | |
| 9403 | 3 | | | CES5AP1 | 1.00 | | |
| 9404 | 3 | | | CETN1 | 1.00 | | |

Fig. 39 - 50

| | | | | | | | |
|---|---|---|---|---|---|---|---|
| 9405 | 3 | | | | | CETN4P | 1.00 |
| 9406 | 3 | | | | | CETP | 1.00 |
| 9407 | 3 | | | | | CFC1 | 1.00 |
| 9408 | 3 | | | | | CFC1B | 1.00 |
| 9409 | 3 | | | | | CFHR2 | 1.00 |
| 9410 | 3 | | | | | CFHR3 | 1.00 |
| 9411 | 3 | | | | | CFHR4 | 1.00 |
| 9412 | 3 | | | | | CFHR5 | 1.00 |
| 9413 | 3 | | | | | CFL1P1 | 1.00 |
| 9414 | 3 | | | | | CFLAR-AS1 | 1.00 |
| 9415 | 3 | | | | | CGA | 1.00 |
| 9416 | 3 | | | | | CGB | 1.00 |
| 9417 | 3 | | | | | CGB1 | 1.00 |
| 9418 | 3 | | | | | CGB5 | 1.00 |
| 9419 | 3 | | | | | CGB8 | 1.00 |
| 9420 | 3 | | | | | CHAC1 | 1.00 |
| 9421 | 3 | | | | | CHAT | 1.00 |
| 9422 | 3 | | | | | CHD5 | 1.00 |
| 9423 | 3 | | | | | CHEK2P2 | 1.00 |
| 9424 | 3 | | | | | CHGB | 1.00 |
| 9425 | 3 | | | | | CHIA | 1.00 |
| 9426 | 3 | | | | | CHKB-CPT1B | 1.00 |
| 9427 | 3 | | | | | CHODL-AS1 | 1.00 |
| 9428 | 3 | | | | | CHRDL2 | 1.00 |
| 9429 | 3 | | | | | CHRFAM7A | 1.00 |
| 9430 | 3 | | | | | CHRM2 | 1.00 |
| 9431 | 3 | | | | | CHRM3 | 1.00 |
| 9432 | 3 | | | | | CHRM5 | 1.00 |
| 9433 | 3 | | | | | CHRNA10 | 1.00 |
| 9434 | 3 | | | | | CHRNA2 | 1.00 |
| 9435 | 3 | | | | | CHRNA3 | 1.00 |
| 9436 | 3 | | | | | CHRNA4 | 1.00 |
| 9437 | 3 | | | | | CHRNA5 | 1.00 |
| 9438 | 3 | | | | | CHRNA6 | 1.00 |
| 9439 | 3 | | | | | CHRNA7 | 1.00 |
| 9440 | 3 | | | | | CHRNA9 | 1.00 |
| 9441 | 3 | | | | | CHRNB2 | 1.00 |
| 9442 | 3 | | | | | CHRNB3 | 1.00 |
| 9443 | 3 | | | | | CHRNB4 | 1.00 |
| 9444 | 3 | | | | | CHRND | 1.00 |
| 9445 | 3 | | | | | CHRNG | 1.00 |
| 9446 | 3 | | | | | CHST13 | 1.00 |
| 9447 | 3 | | | | | CHST4 | 1.00 |
| 9448 | 3 | | | | | CHST5 | 1.00 |
| 9449 | 3 | | | | | CHST6 | 1.00 |
| 9450 | 3 | | | | | CHST8 | 1.00 |
| 9451 | 3 | | | | | CHST9 | 1.00 |
| 9452 | 3 | | | | | CHST9-AS1 | 1.00 |
| 9453 | 3 | | | | | CHURC1-FNTB | 1.00 |
| 9454 | 3 | | | | | CIB3 | 1.00 |
| 9455 | 3 | | | | | CIB4 | 1.00 |
| 9456 | 3 | | | | | CITED1 | 1.00 |
| 9457 | 3 | | | | | CKAP2L | 1.00 |
| 9458 | 3 | | | | | CKM | 1.00 |
| 9459 | 3 | | | | | CLC | 1.00 |
| 9460 | 3 | | | | | CLCA1 | 1.00 |
| 9461 | 3 | | | | | CLCA3P | 1.00 |
| 9462 | 3 | | | | | CLCN1 | 1.00 |
| 9463 | 3 | | | | | CLCNKB | 1.00 |
| 9464 | 3 | | | | | CLDN14 | 1.00 |
| 9465 | 3 | | | | | CLDN17 | 1.00 |
| 9466 | 3 | | | | | CLDN18 | 1.00 |
| 9467 | 3 | | | | | CLDN2 | 1.00 |
| 9468 | 3 | | | | | CLDN20 | 1.00 |
| 9469 | 3 | | | | | CLDN22 | 1.00 |
| 9470 | 3 | | | | | CLDN24 | 1.00 |
| 9471 | 3 | | | | | CLDN25 | 1.00 |
| 9472 | 3 | | | | | CLDN6 | 1.00 |
| 9473 | 3 | | | | | CLDN9 | 1.00 |
| 9474 | 3 | | | | | CLDND1 | 1.00 |
| 9475 | 3 | | | | | CLDND2 | 1.00 |
| 9476 | 3 | | | | | CLEC12A | 1.00 |
| 9477 | 3 | | | | | CLEC17A | 1.00 |
| 9478 | 3 | | | | | CLEC18B | 1.00 |
| 9479 | 3 | | | | | CLEC18C | 1.00 |
| 9480 | 3 | | | | | CLEC19A | 1.00 |
| 9481 | 3 | | | | | CLEC1B | 1.00 |
| 9482 | 3 | | | | | CLEC2L | 1.00 |
| 9483 | 3 | | | | | CLEC3A | 1.00 |
| 9484 | 3 | | | | | CLEC4C | 1.00 |
| 9485 | 3 | | | | | CLEC4D | 1.00 |
| 9486 | 3 | | | | | CLEC4E | 1.00 |
| 9487 | 3 | | | | | CLEC4M | 1.00 |
| 9488 | 3 | | | | | CLEC6A | 1.00 |
| 9489 | 3 | | | | | CLECL1 | 1.00 |
| 9490 | 3 | | | | | CLGN | 1.00 |
| 9491 | 3 | | | | | CLLU1 | 1.00 |
| 9492 | 3 | | | | | CLLU1OS | 1.00 |
| 9493 | 3 | | | | | CLNK | 1.00 |
| 9494 | 3 | | | | | CLOCK | 1.00 |
| 9495 | 3 | | | | | CLPS | 1.00 |
| 9496 | 3 | | | | | CLPSL1 | 1.00 |
| 9497 | 3 | | | | | CLPSL2 | 1.00 |
| 9498 | 3 | | | | | CLRN1 | 1.00 |
| 9499 | 3 | | | | | CLRN1-AS1 | 1.00 |
| 9500 | 3 | | | | | CLRN2 | 1.00 |
| 9501 | 3 | | | | | CLRN3 | 1.00 |
| 9502 | 3 | | | | | CLSPN | 1.00 |
| 9503 | 3 | | | | | CLUL1 | 1.00 |
| 9504 | 3 | | | | | CLVS1 | 1.00 |
| 9505 | 3 | | | | | CLVS2 | 1.00 |
| 9506 | 3 | | | | | CLYBL | 1.00 |
| 9507 | 3 | | | | | CMTM1 | 1.00 |
| 9508 | 3 | | | | | CMTM2 | 1.00 |
| 9509 | 3 | | | | | CMYA5 | 1.00 |
| 9510 | 3 | | | | | CNBH6.4 | 1.00 |
| 9511 | 3 | | | | | CNBD1 | 1.00 |
| 9512 | 3 | | | | | CNDP1 | 1.00 |
| 9513 | 3 | | | | | CNGA2 | 1.00 |
| 9514 | 3 | | | | | CNGA3 | 1.00 |
| 9515 | 3 | | | | | CNGA4 | 1.00 |
| 9516 | 3 | | | | | CNGB1 | 1.00 |
| 9517 | 3 | | | | | CNGB3 | 1.00 |
| 9518 | 3 | | | | | CNIH3 | 1.00 |
| 9519 | 3 | | | | | CNKSR2 | 1.00 |
| 9520 | 3 | | | | | CNPY1 | 1.00 |
| 9521 | 3 | | | | | CNR2 | 1.00 |
| 9522 | 3 | | | | | CNTD2 | 1.00 |
| 9523 | 3 | | | | | CNTN3 | 1.00 |
| 9524 | 3 | | | | | CNTN4 | 1.00 |
| 9525 | 3 | | | | | CNTN5 | 1.00 |
| 9526 | 3 | | | | | CNTN6 | 1.00 |
| 9527 | 3 | | | | | CNTNAP2 | 1.00 |
| 9528 | 3 | | | | | CNTNAP4 | 1.00 |
| 9529 | 3 | | | | | CNTNAP5 | 1.00 |
| 9530 | 3 | | | | | COL10A1 | 1.00 |
| 9531 | 3 | | | | | COL11A1 | 1.00 |
| 9532 | 3 | | | | | COL11A2 | 1.00 |
| 9533 | 3 | | | | | COL18A1-AS1 | 1.00 |
| 9534 | 3 | | | | | COL19A1 | 1.00 |
| 9535 | 3 | | | | | COL20A1 | 1.00 |
| 9536 | 3 | | | | | COL22A1 | 1.00 |
| 9537 | 3 | | | | | COL24A1 | 1.00 |
| 9538 | 3 | | | | | COL25A1 | 1.00 |
| 9539 | 3 | | | | | COL2A1 | 1.00 |
| 9540 | 3 | | | | | COL4A3 | 1.00 |
| 9541 | 3 | | | | | COL4A4 | 1.00 |
| 9542 | 3 | | | | | COL6A4P1 | 1.00 |
| 9543 | 3 | | | | | COL6A4P2 | 1.00 |
| 9544 | 3 | | | | | COL6A6 | 1.00 |
| 9545 | 3 | | | | | COL9A1 | 1.00 |
| 9546 | 3 | | | | | COLEC10 | 1.00 |
| 9547 | 3 | | | | | COLEC11 | 1.00 |
| 9548 | 3 | | | | | CORO7-PAM16 | 1.00 |
| 9549 | 3 | | | | | CORT | 1.00 |
| 9550 | 3 | | | | | COX6A2 | 1.00 |
| 9551 | 3 | | | | | COX7B2 | 1.00 |
| 9552 | 3 | | | | | COX8C | 1.00 |
| 9553 | 3 | | | | | CPA1 | 1.00 |
| 9554 | 3 | | | | | CPA2 | 1.00 |
| 9555 | 3 | | | | | CPA5 | 1.00 |
| 9556 | 3 | | | | | CPA6 | 1.00 |
| 9557 | 3 | | | | | CPAMD8 | 1.00 |
| 9558 | 3 | | | | | CPB1 | 1.00 |
| 9559 | 3 | | | | | CPB2 | 1.00 |
| 9560 | 3 | | | | | CPLX2 | 1.00 |
| 9561 | 3 | | | | | CPLX3 | 1.00 |
| 9562 | 3 | | | | | CPLX4 | 1.00 |
| 9563 | 3 | | | | | CPN1 | 1.00 |
| 9564 | 3 | | | | | CPN2 | 1.00 |
| 9565 | 3 | | | | | CPNE4 | 1.00 |
| 9566 | 3 | | | | | CPNE6 | 1.00 |
| 9567 | 3 | | | | | CPNE7 | 1.00 |
| 9568 | 3 | | | | | CPNE9 | 1.00 |
| 9569 | 3 | | | | | CPO | 1.00 |
| 9570 | 3 | | | | | CPS1 | 1.00 |
| 9571 | 3 | | | | | CPS1-IT1 | 1.00 |
| 9572 | 3 | | | | | CPSF4L | 1.00 |
| 9573 | 3 | | | | | CPXCR1 | 1.00 |
| 9574 | 3 | | | | | CR1 | 1.00 |
| 9575 | 3 | | | | | CR1L | 1.00 |
| 9576 | 3 | | | | | CR2 | 1.00 |
| 9577 | 3 | | | | | CRB1 | 1.00 |
| 9578 | 3 | | | | | CREB3L3 | 1.00 |
| 9579 | 3 | | | | | CREG2 | 1.00 |
| 9580 | 3 | | | | | CRH | 1.00 |
| 9581 | 3 | | | | | CRHBP | 1.00 |
| 9582 | 3 | | | | | CRISP1 | 1.00 |
| 9583 | 3 | | | | | CRISP2 | 1.00 |
| 9584 | 3 | | | | | CRLF2 | 1.00 |
| 9585 | 3 | | | | | CRP | 1.00 |
| 9586 | 3 | | | | | CRTAM | 1.00 |
| 9587 | 3 | | | | | CRX | 1.00 |
| 9588 | 3 | | | | | CRYAA | 1.00 |
| 9589 | 3 | | | | | CRYBA1 | 1.00 |
| 9590 | 3 | | | | | CRYBA2 | 1.00 |
| 9591 | 3 | | | | | CRYBA4 | 1.00 |
| 9592 | 3 | | | | | CRYBB1 | 1.00 |
| 9593 | 3 | | | | | CRYBB2 | 1.00 |
| 9594 | 3 | | | | | CRYBB3 | 1.00 |
| 9595 | 3 | | | | | CRYGA | 1.00 |
| 9596 | 3 | | | | | CRYGB | 1.00 |

Fig. 39 - 51

| | | | | | | | | | | | | | | | |
|---|---|---|---|---|---|---|---|---|---|---|---|---|---|---|---|
| 9597 | 3 | | | | | | CRYGC | 1.00 | 9693 | 3 | | | | CXorf68 | 1.00 |
| 9598 | 3 | | | | | | CRYGD | 1.00 | 9694 | 3 | | | | CXXC11 | 1.00 |
| 9599 | 3 | | | | | | CRYGN | 1.00 | 9695 | 3 | | | | CXXC1P1 | 1.00 |
| 9600 | 3 | | | | | | CRYM | 1.00 | 9696 | 3 | | | | CXXC4 | 1.00 |
| 9601 | 3 | | | | | | CRYM-AS1 | 1.00 | 9697 | 3 | | | | CYCSP52 | 1.00 |
| 9602 | 3 | | | | | | CSAG1 | 1.00 | 9698 | 3 | | | | CYLC1 | 1.00 |
| 9603 | 3 | | | | | | CSAG2 | 1.00 | 9699 | 3 | | | | CYLC2 | 1.00 |
| 9604 | 3 | | | | | | CSF2 | 1.00 | 9700 | 3 | | | | CYMP | 1.00 |
| 9605 | 3 | | | | | | CSH1 | 1.00 | 9701 | 3 | | | | CYP11A1 | 1.00 |
| 9606 | 3 | | | | | | CSH2 | 1.00 | 9702 | 3 | | | | CYP11B1 | 1.00 |
| 9607 | 3 | | | | | | CSHL1 | 1.00 | 9703 | 3 | | | | CYP11B2 | 1.00 |
| 9608 | 3 | | | | | | CSMD1 | 1.00 | 9704 | 3 | | | | CYP17A1 | 1.00 |
| 9609 | 3 | | | | | | CSMD2 | 1.00 | 9705 | 3 | | | | CYP19A1 | 1.00 |
| 9610 | 3 | | | | | | CSMD3 | 1.00 | 9706 | 3 | | | | CYP1A1 | 1.00 |
| 9611 | 3 | | | | | | CSN1S1 | 1.00 | 9707 | 3 | | | | CYP1A2 | 1.00 |
| 9612 | 3 | | | | | | CSN1S2AP | 1.00 | 9708 | 3 | | | | CYP1B1-AS1 | 1.00 |
| 9613 | 3 | | | | | | CSN1S2BP | 1.00 | 9709 | 3 | | | | CYP24A1 | 1.00 |
| 9614 | 3 | | | | | | CSN2 | 1.00 | 9710 | 3 | | | | CYP26A1 | 1.00 |
| 9615 | 3 | | | | | | CSN3 | 1.00 | 9711 | 3 | | | | CYP26C1 | 1.00 |
| 9616 | 3 | | | | | | CSNK1G2-AS1 | 1.00 | 9712 | 3 | | | | CYP27B1 | 1.00 |
| 9617 | 3 | | | | | | CSPG4P1Y | 1.00 | 9713 | 3 | | | | CYP2A13 | 1.00 |
| 9618 | 3 | | | | | | CSRNP3 | 1.00 | 9714 | 3 | | | | CYP2A6 | 1.00 |
| 9619 | 3 | | | | | | CSRP3 | 1.00 | 9715 | 3 | | | | CYP2A7 | 1.00 |
| 9620 | 3 | | | | | | CST1 | 1.00 | 9716 | 3 | | | | CYP2B7P1 | 1.00 |
| 9621 | 3 | | | | | | CST11 | 1.00 | 9717 | 3 | | | | CYP2C19 | 1.00 |
| 9622 | 3 | | | | | | CST2 | 1.00 | 9718 | 3 | | | | CYP2C8 | 1.00 |
| 9623 | 3 | | | | | | CST4 | 1.00 | 9719 | 3 | | | | CYP2F1 | 1.00 |
| 9624 | 3 | | | | | | CST5 | 1.00 | 9720 | 3 | | | | CYP2G1P | 1.00 |
| 9625 | 3 | | | | | | CST8 | 1.00 | 9721 | 3 | | | | CYP3A43 | 1.00 |
| 9626 | 3 | | | | | | CST9 | 1.00 | 9722 | 3 | | | | CYP3A7-CYP3AP1 | 1.00 |
| 9627 | 3 | | | | | | CST9L | 1.00 | 9723 | 3 | | | | CYP46A1 | 1.00 |
| 9628 | 3 | | | | | | CSTL1 | 1.00 | 9724 | 3 | | | | CYP4A11 | 1.00 |
| 9629 | 3 | | | | | | CSTT | 1.00 | 9725 | 3 | | | | CYP4A22 | 1.00 |
| 9630 | 3 | | | | | | CT45A1 | 1.00 | 9726 | 3 | | | | CYP4F11 | 1.00 |
| 9631 | 3 | | | | | | CT45A2 | 1.00 | 9727 | 3 | | | | CYP4F30P | 1.00 |
| 9632 | 3 | | | | | | CT45A3 | 1.00 | 9728 | 3 | | | | CYP4F35P | 1.00 |
| 9633 | 3 | | | | | | CT45A4 | 1.00 | 9729 | 3 | | | | CYP4Z1 | 1.00 |
| 9634 | 3 | | | | | | CT45A5 | 1.00 | 9730 | 3 | | | | CYP4Z2P | 1.00 |
| 9635 | 3 | | | | | | CT45A6 | 1.00 | 9731 | 3 | | | | CYP7A1 | 1.00 |
| 9636 | 3 | | | | | | CT47A1 | 1.00 | 9732 | 3 | | | | CYP7B1 | 1.00 |
| 9637 | 3 | | | | | | CT47A10 | 1.00 | 9733 | 3 | | | | CYP8B1 | 1.00 |
| 9638 | 3 | | | | | | CT47A11 | 1.00 | 9734 | 3 | | | | CYSLTR2 | 1.00 |
| 9639 | 3 | | | | | | CT47A4 | 1.00 | 9735 | 3 | | | | D21S2088E | 1.00 |
| 9640 | 3 | | | | | | CT47A5 | 1.00 | 9736 | 3 | | | | DAB1 | 1.00 |
| 9641 | 3 | | | | | | CT47A6 | 1.00 | 9737 | 3 | | | | DACH2 | 1.00 |
| 9642 | 3 | | | | | | CT47A7 | 1.00 | 9738 | 3 | | | | DAND5 | 1.00 |
| 9643 | 3 | | | | | | CT47A8 | 1.00 | 9739 | 3 | | | | DAO | 1.00 |
| 9644 | 3 | | | | | | CT47B1 | 1.00 | 9740 | 3 | | | | DAOA | 1.00 |
| 9645 | 3 | | | | | | CT62 | 1.00 | 9741 | 3 | | | | DAOA-AS1 | 1.00 |
| 9646 | 3 | | | | | | CTAG1A | 1.00 | 9742 | 3 | | | | DAZ1 | 1.00 |
| 9647 | 3 | | | | | | CTAG1B | 1.00 | 9743 | 3 | | | | DAZ3 | 1.00 |
| 9648 | 3 | | | | | | CTAG2 | 1.00 | 9744 | 3 | | | | DAZL | 1.00 |
| 9649 | 3 | | | | | | CTAGE1 | 1.00 | 9745 | 3 | | | | DBC1 | 1.00 |
| 9650 | 3 | | | | | | CTAGE10P | 1.00 | 9746 | 3 | | | | DBH | 1.00 |
| 9651 | 3 | | | | | | CTAGE11P | 1.00 | 9747 | 3 | | | | DBILSP2 | 1.00 |
| 9652 | 3 | | | | | | CTCFL | 1.00 | 9748 | 3 | | | | DBX1 | 1.00 |
| 9653 | 3 | | | | | | CTNNA2 | 1.00 | 9749 | 3 | | | | DBX2 | 1.00 |
| 9654 | 3 | | | | | | CTNNA3 | 1.00 | 9750 | 3 | | | | DCAF12L1 | 1.00 |
| 9655 | 3 | | | | | | CTRB1 | 1.00 | 9751 | 3 | | | | DCAF12L2 | 1.00 |
| 9656 | 3 | | | | | | CTRB2 | 1.00 | 9752 | 3 | | | | DCAF4L1 | 1.00 |
| 9657 | 3 | | | | | | CTRC | 1.00 | 9753 | 3 | | | | DCAF4L2 | 1.00 |
| 9658 | 3 | | | | | | CTSE | 1.00 | 9754 | 3 | | | | DCAF8L1 | 1.00 |
| 9659 | 3 | | | | | | CTSL1P2 | 1.00 | 9755 | 3 | | | | DCAF8L2 | 1.00 |
| 9660 | 3 | | | | | | CTSL1P8 | 1.00 | 9756 | 3 | | | | DCBLD1 | 1.00 |
| 9661 | 3 | | | | | | CTSL3 | 1.00 | 9757 | 3 | | | | DCC | 1.00 |
| 9662 | 3 | | | | | | CTXN2 | 1.00 | 9758 | 3 | | | | DCDC1 | 1.00 |
| 9663 | 3 | | | | | | CTXN3 | 1.00 | 9759 | 3 | | | | DCDC2 | 1.00 |
| 9664 | 3 | | | | | | CUBN | 1.00 | 9760 | 3 | | | | DCDC2B | 1.00 |
| 9665 | 3 | | | | | | CUZD1 | 1.00 | 9761 | 3 | | | | DCDC5 | 1.00 |
| 9666 | 3 | | | | | | CXADRP2 | 1.00 | 9762 | 3 | | | | DCHS2 | 1.00 |
| 9667 | 3 | | | | | | CXADRP3 | 1.00 | 9763 | 3 | | | | DCLK3 | 1.00 |
| 9668 | 3 | | | | | | CXCL11 | 1.00 | 9764 | 3 | | | | DCST1 | 1.00 |
| 9669 | 3 | | | | | | CXCL13 | 1.00 | 9765 | 3 | | | | DCX | 1.00 |
| 9670 | 3 | | | | | | CXCL17 | 1.00 | 9766 | 3 | | | | DDC | 1.00 |
| 9671 | 3 | | | | | | CXCL3 | 1.00 | 9767 | 3 | | | | DDI1 | 1.00 |
| 9672 | 3 | | | | | | CXCL5 | 1.00 | 9768 | 3 | | | | DDI2 | 1.00 |
| 9673 | 3 | | | | | | CXCL6 | 1.00 | 9769 | 3 | | | | DDN | 1.00 |
| 9674 | 3 | | | | | | CXCR2P1 | 1.00 | 9770 | 3 | | | | DDX11L1 | 1.00 |
| 9675 | 3 | | | | | | CXCR5 | 1.00 | 9771 | 3 | | | | DDX11L10 | 1.00 |
| 9676 | 3 | | | | | | CXCR6 | 1.00 | 9772 | 3 | | | | DDX11L9 | 1.00 |
| 9677 | 3 | | | | | | CXorf1 | 1.00 | 9773 | 3 | | | | DDX25 | 1.00 |
| 9678 | 3 | | | | | | CXorf22 | 1.00 | 9774 | 3 | | | | DDX4 | 1.00 |
| 9679 | 3 | | | | | | CXorf27 | 1.00 | 9775 | 3 | | | | DDX43 | 1.00 |
| 9680 | 3 | | | | | | CXorf28 | 1.00 | 9776 | 3 | | | | DDX53 | 1.00 |
| 9681 | 3 | | | | | | CXorf30 | 1.00 | 9777 | 3 | | | | DEC1 | 1.00 |
| 9682 | 3 | | | | | | CXorf31 | 1.00 | 9778 | 3 | | | | DEFA1 | 1.00 |
| 9683 | 3 | | | | | | CXorf41 | 1.00 | 9779 | 3 | | | | DEFA10P | 1.00 |
| 9684 | 3 | | | | | | CXorf48 | 1.00 | 9780 | 3 | | | | DEFA1B | 1.00 |
| 9685 | 3 | | | | | | CXorf49B | 1.00 | 9781 | 3 | | | | DEFA3 | 1.00 |
| 9686 | 3 | | | | | | CXorf51A | 1.00 | 9782 | 3 | | | | DEFA4 | 1.00 |
| 9687 | 3 | | | | | | CXorf57 | 1.00 | 9783 | 3 | | | | DEFA5 | 1.00 |
| 9688 | 3 | | | | | | CXorf58 | 1.00 | 9784 | 3 | | | | DEFB103A | 1.00 |
| 9689 | 3 | | | | | | CXorf59 | 1.00 | 9785 | 3 | | | | DEFB104B | 1.00 |
| 9690 | 3 | | | | | | CXorf61 | 1.00 | 9786 | 3 | | | | DEFB105B | 1.00 |
| 9691 | 3 | | | | | | CXorf64 | 1.00 | 9787 | 3 | | | | DEFB106B | 1.00 |
| 9692 | 3 | | | | | | CXorf66 | 1.00 | 9788 | 3 | | | | DEFB107A | 1.00 |

Fig. 39 - 52

| | | | | | | | | | | | | | | |
|---|---|---|---|---|---|---|---|---|---|---|---|---|---|---|
| 9789 | 3 | | | | | DEFB107B | 1.00 | 9885 | 3 | | | | DNAH2 | 1.00 |
| 9790 | 3 | | | | | DEFB108B | 1.00 | 9886 | 3 | | | | DNAH3 | 1.00 |
| 9791 | 3 | | | | | DEFB109P1 | 1.00 | 9887 | 3 | | | | DNAH5 | 1.00 |
| 9792 | 3 | | | | | DEFB109P1B | 1.00 | 9888 | 3 | | | | DNAH6 | 1.00 |
| 9793 | 3 | | | | | DEFB110 | 1.00 | 9889 | 3 | | | | DNAH7 | 1.00 |
| 9794 | 3 | | | | | DEFB112 | 1.00 | 9890 | 3 | | | | DNAH8 | 1.00 |
| 9795 | 3 | | | | | DEFB113 | 1.00 | 9891 | 3 | | | | DNAH9 | 1.00 |
| 9796 | 3 | | | | | DEFB114 | 1.00 | 9892 | 3 | | | | DNAI1 | 1.00 |
| 9797 | 3 | | | | | DEFB115 | 1.00 | 9893 | 3 | | | | DNAI2 | 1.00 |
| 9798 | 3 | | | | | DEFB116 | 1.00 | 9894 | 3 | | | | DNAJA1P5 | 1.00 |
| 9799 | 3 | | | | | DEFB118 | 1.00 | 9895 | 3 | | | | DNAJB13 | 1.00 |
| 9800 | 3 | | | | | DEFB119 | 1.00 | 9896 | 3 | | | | DNAJB3 | 1.00 |
| 9801 | 3 | | | | | DEFB121 | 1.00 | 9897 | 3 | | | | DNAJB7 | 1.00 |
| 9802 | 3 | | | | | DEFB122 | 1.00 | 9898 | 3 | | | | DNAJB8 | 1.00 |
| 9803 | 3 | | | | | DEFB123 | 1.00 | 9899 | 3 | | | | DNAJB8-AS1 | 1.00 |
| 9804 | 3 | | | | | DEFB125 | 1.00 | 9900 | 3 | | | | DNAJC12 | 1.00 |
| 9805 | 3 | | | | | DEFB126 | 1.00 | 9901 | 3 | | | | DNAJC22 | 1.00 |
| 9806 | 3 | | | | | DEFB127 | 1.00 | 9902 | 3 | | | | DNAJC25-GNG10 | 1.00 |
| 9807 | 3 | | | | | DEFB128 | 1.00 | 9903 | 3 | | | | DNAJC27-AS1 | 1.00 |
| 9808 | 3 | | | | | DEFB129 | 1.00 | 9904 | 3 | | | | DNAJC5B | 1.00 |
| 9809 | 3 | | | | | DEFB130 | 1.00 | 9905 | 3 | | | | DNAJC5G | 1.00 |
| 9810 | 3 | | | | | DEFB131 | 1.00 | 9906 | 3 | | | | DNAJC6 | 1.00 |
| 9811 | 3 | | | | | DEFB132 | 1.00 | 9907 | 3 | | | | DNASE2B | 1.00 |
| 9812 | 3 | | | | | DEFB133 | 1.00 | 9908 | 3 | | | | DNM1P35 | 1.00 |
| 9813 | 3 | | | | | DEFB134 | 1.00 | 9909 | 3 | | | | DNM1P41 | 1.00 |
| 9814 | 3 | | | | | DEFB135 | 1.00 | 9910 | 3 | | | | DNM1P46 | 1.00 |
| 9815 | 3 | | | | | DEFB136 | 1.00 | 9911 | 3 | | | | DNM3 | 1.00 |
| 9816 | 3 | | | | | DEFB4A | 1.00 | 9912 | 3 | | | | DNMBP-AS1 | 1.00 |
| 9817 | 3 | | | | | DEFB4B | 1.00 | 9913 | 3 | | | | DNMT3L | 1.00 |
| 9818 | 3 | | | | | DEFT1P | 1.00 | 9914 | 3 | | | | DNTT | 1.00 |
| 9819 | 3 | | | | | DENND4A | 1.00 | 9915 | 3 | | | | DOC2A | 1.00 |
| 9820 | 3 | | | | | DENND5B | 1.00 | 9916 | 3 | | | | DOC2GP | 1.00 |
| 9821 | 3 | | | | | DEPDC1B | 1.00 | 9917 | 3 | | | | DOCK10 | 1.00 |
| 9822 | 3 | | | | | DEPDC4 | 1.00 | 9918 | 3 | | | | DOCK5 | 1.00 |
| 9823 | 3 | | | | | DERL3 | 1.00 | 9919 | 3 | | | | DOK5 | 1.00 |
| 9824 | 3 | | | | | DGCR10 | 1.00 | 9920 | 3 | | | | DOK6 | 1.00 |
| 9825 | 3 | | | | | DGCR9 | 1.00 | 9921 | 3 | | | | DOPEY1 | 1.00 |
| 9826 | 3 | | | | | DGKB | 1.00 | 9922 | 3 | | | | DPCR1 | 1.00 |
| 9827 | 3 | | | | | DGKG | 1.00 | 9923 | 3 | | | | DPEP1 | 1.00 |
| 9828 | 3 | | | | | DGKH | 1.00 | 9924 | 3 | | | | DPEP3 | 1.00 |
| 9829 | 3 | | | | | DGKI | 1.00 | 9925 | 3 | | | | DPF1 | 1.00 |
| 9830 | 3 | | | | | DGKK | 1.00 | 9926 | 3 | | | | DPF3 | 1.00 |
| 9831 | 3 | | | | | DHDH | 1.00 | 9927 | 3 | | | | DPP10 | 1.00 |
| 9832 | 3 | | | | | DHH | 1.00 | 9928 | 3 | | | | DPPA2 | 1.00 |
| 9833 | 3 | | | | | DHRS7C | 1.00 | 9929 | 3 | | | | DPPA3 | 1.00 |
| 9834 | 3 | | | | | DIAPH2 | 1.00 | 9930 | 3 | | | | DPPA4 | 1.00 |
| 9835 | 3 | | | | | DIAPH3 | 1.00 | 9931 | 3 | | | | DPPA5 | 1.00 |
| 9836 | 3 | | | | | DIO1 | 1.00 | 9932 | 3 | | | | DPRX | 1.00 |
| 9837 | 3 | | | | | DIRAS2 | 1.00 | 9933 | 3 | | | | DPY19L1P1 | 1.00 |
| 9838 | 3 | | | | | DIRC1 | 1.00 | 9934 | 3 | | | | DPY19L2P1 | 1.00 |
| 9839 | 3 | | | | | DIRC3 | 1.00 | 9935 | 3 | | | | DPY19L2P2 | 1.00 |
| 9840 | 3 | | | | | DISC2 | 1.00 | 9936 | 3 | | | | DPY19L2P3 | 1.00 |
| 9841 | 3 | | | | | DISP2 | 1.00 | 9937 | 3 | | | | DPY19L2P4 | 1.00 |
| 9842 | 3 | | | | | DKFZP434A062 | 1.00 | 9938 | 3 | | | | DPYS | 1.00 |
| 9843 | 3 | | | | | DKFZP434H168 | 1.00 | 9939 | 3 | | | | DPYSL4 | 1.00 |
| 9844 | 3 | | | | | DKFZP434K028 | 1.00 | 9940 | 3 | | | | DPYSL5 | 1.00 |
| 9845 | 3 | | | | | DKFZP434L187 | 1.00 | 9941 | 3 | | | | DRD1 | 1.00 |
| 9846 | 3 | | | | | DKFZp434L192 | 1.00 | 9942 | 3 | | | | DRD3 | 1.00 |
| 9847 | 3 | | | | | DKFZp451B082 | 1.00 | 9943 | 3 | | | | DRD5 | 1.00 |
| 9848 | 3 | | | | | DKFZP564C196 | 1.00 | 9944 | 3 | | | | DRGX | 1.00 |
| 9849 | 3 | | | | | DKFZp566F0947 | 1.00 | 9945 | 3 | | | | DRP2 | 1.00 |
| 9850 | 3 | | | | | DKFZp686D0853 | 1.00 | 9946 | 3 | | | | DSCAM | 1.00 |
| 9851 | 3 | | | | | DKFZp686K1684 | 1.00 | 9947 | 3 | | | | DSCAM-AS1 | 1.00 |
| 9852 | 3 | | | | | DKFZp686O1327 | 1.00 | 9948 | 3 | | | | DSCAML1 | 1.00 |
| 9853 | 3 | | | | | DKFZp779M0652 | 1.00 | 9949 | 3 | | | | DSCR10 | 1.00 |
| 9854 | 3 | | | | | DKK4 | 1.00 | 9950 | 3 | | | | DSCR4 | 1.00 |
| 9855 | 3 | | | | | DKKL1 | 1.00 | 9951 | 3 | | | | DSCR6 | 1.00 |
| 9856 | 3 | | | | | DLEC1 | 1.00 | 9952 | 3 | | | | DSCR8 | 1.00 |
| 9857 | 3 | | | | | DLEU2 | 1.00 | 9953 | 3 | | | | DSCR9 | 1.00 |
| 9858 | 3 | | | | | DLEU2L | 1.00 | 9954 | 3 | | | | DSG4 | 1.00 |
| 9859 | 3 | | | | | DLEU7 | 1.00 | 9955 | 3 | | | | DSPP | 1.00 |
| 9860 | 3 | | | | | DLGAP1 | 1.00 | 9956 | 3 | | | | DTHD1 | 1.00 |
| 9861 | 3 | | | | | DLGAP2 | 1.00 | 9957 | 3 | | | | DUPD1 | 1.00 |
| 9862 | 3 | | | | | DLGAP3 | 1.00 | 9958 | 3 | | | | DUSP13 | 1.00 |
| 9863 | 3 | | | | | DLGAP5 | 1.00 | 9959 | 3 | | | | DUSP15 | 1.00 |
| 9864 | 3 | | | | | DLL3 | 1.00 | 9960 | 3 | | | | DUSP21 | 1.00 |
| 9865 | 3 | | | | | DLX1 | 1.00 | 9961 | 3 | | | | DUSP26 | 1.00 |
| 9866 | 3 | | | | | DLX2 | 1.00 | 9962 | 3 | | | | DUSP27 | 1.00 |
| 9867 | 3 | | | | | DLX6-AS1 | 1.00 | 9963 | 3 | | | | DUSP5P | 1.00 |
| 9868 | 3 | | | | | DMBT1 | 1.00 | 9964 | 3 | | | | DUSP9 | 1.00 |
| 9869 | 3 | | | | | DMBX1 | 1.00 | 9965 | 3 | | | | DUX2 | 1.00 |
| 9870 | 3 | | | | | DMC1 | 1.00 | 9966 | 3 | | | | DUX4 | 1.00 |
| 9871 | 3 | | | | | DMGDH | 1.00 | 9967 | 3 | | | | DUX4L2 | 1.00 |
| 9872 | 3 | | | | | DMP1 | 1.00 | 9968 | 3 | | | | DUX4L3 | 1.00 |
| 9873 | 3 | | | | | DMRT1 | 1.00 | 9969 | 3 | | | | DUX4L4 | 1.00 |
| 9874 | 3 | | | | | DMRTA1 | 1.00 | 9970 | 3 | | | | DUX4L5 | 1.00 |
| 9875 | 3 | | | | | DMRTA2 | 1.00 | 9971 | 3 | | | | DUX4L6 | 1.00 |
| 9876 | 3 | | | | | DMRTB1 | 1.00 | 9972 | 3 | | | | DUXA | 1.00 |
| 9877 | 3 | | | | | DMRTC1B | 1.00 | 9973 | 3 | | | | DYDC1 | 1.00 |
| 9878 | 3 | | | | | DMRTC2 | 1.00 | 9974 | 3 | | | | DYDC2 | 1.00 |
| 9879 | 3 | | | | | DNA2 | 1.00 | 9975 | 3 | | | | DYNC2H1 | 1.00 |
| 9880 | 3 | | | | | DNAAF1 | 1.00 | 9976 | 3 | | | | DYNLRB2 | 1.00 |
| 9881 | 3 | | | | | DNAH10 | 1.00 | 9977 | 3 | | | | DYTN | 1.00 |
| 9882 | 3 | | | | | DNAH11 | 1.00 | 9978 | 3 | | | | DYX1C1 | 1.00 |
| 9883 | 3 | | | | | DNAH12 | 1.00 | 9979 | 3 | | | | DYX1C1-CCPG1 | 1.00 |
| 9884 | 3 | | | | | DNAH14 | 1.00 | 9980 | 3 | | | | DZANK1-AS1 | 1.00 |

Fig. 39 - 53

| | | | | | | | | | | | | | | |
|---|---|---|---|---|---|---|---|---|---|---|---|---|---|---|
| 9981 | 3 | | | | E2F7 | 1.00 | 10077 | 3 | | | | F11 | 1.00 |
| 9982 | 3 | | | | EBLN1 | 1.00 | 10078 | 3 | | | | F13B | 1.00 |
| 9983 | 3 | | | | ECEL1 | 1.00 | 10079 | 3 | | | | F2 | 1.00 |
| 9984 | 3 | | | | ECEL1P2 | 1.00 | 10080 | 3 | | | | F2RL3 | 1.00 |
| 9985 | 3 | | | | ECRP | 1.00 | 10081 | 3 | | | | F7 | 1.00 |
| 9986 | 3 | | | | ECT2L | 1.00 | 10082 | 3 | | | | F8A2 | 1.00 |
| 9987 | 3 | | | | EDDM3A | 1.00 | 10083 | 3 | | | | F9 | 1.00 |
| 9988 | 3 | | | | EDDM3B | 1.00 | 10084 | 3 | | | | FABP1 | 1.00 |
| 9989 | 3 | | | | EDIL3 | 1.00 | 10085 | 3 | | | | FABP12 | 1.00 |
| 9990 | 3 | | | | EEF1DP3 | 1.00 | 10086 | 3 | | | | FABP2 | 1.00 |
| 9991 | 3 | | | | EEF1E1-MUTED | 1.00 | 10087 | 3 | | | | FABP5P3 | 1.00 |
| 9992 | 3 | | | | EFCAB10 | 1.00 | 10088 | 3 | | | | FAM106A | 1.00 |
| 9993 | 3 | | | | EFCAB3 | 1.00 | 10089 | 3 | | | | FAM106CP | 1.00 |
| 9994 | 3 | | | | EFCAB4B | 1.00 | 10090 | 3 | | | | FAM123A | 1.00 |
| 9995 | 3 | | | | EFCAB5 | 1.00 | 10091 | 3 | | | | FAM123C | 1.00 |
| 9996 | 3 | | | | EFCAB6 | 1.00 | 10092 | 3 | | | | FAM129C | 1.00 |
| 9997 | 3 | | | | EFCAB9 | 1.00 | 10093 | 3 | | | | FAM131B | 1.00 |
| 9998 | 3 | | | | EFHB | 1.00 | 10094 | 3 | | | | FAM131C | 1.00 |
| 9999 | 3 | | | | EFNA2 | 1.00 | 10095 | 3 | | | | FAM133A | 1.00 |
| 10000 | 3 | | | | EGF | 1.00 | 10096 | 3 | | | | FAM135B | 1.00 |
| 10001 | 3 | | | | EGFEM1P | 1.00 | 10097 | 3 | | | | FAM138A | 1.00 |
| 10002 | 3 | | | | EGFLAM-AS4 | 1.00 | 10098 | 3 | | | | FAM138B | 1.00 |
| 10003 | 3 | | | | EGOT | 1.00 | 10099 | 3 | | | | FAM138C | 1.00 |
| 10004 | 3 | | | | EGR4 | 1.00 | 10100 | 3 | | | | FAM138D | 1.00 |
| 10005 | 3 | | | | EIF2C3 | 1.00 | 10101 | 3 | | | | FAM138E | 1.00 |
| 10006 | 3 | | | | EIF3CL | 1.00 | 10102 | 3 | | | | FAM138F | 1.00 |
| 10007 | 3 | | | | EIF4E1B | 1.00 | 10103 | 3 | | | | FAM150A | 1.00 |
| 10008 | 3 | | | | ELAVL2 | 1.00 | 10104 | 3 | | | | FAM151A | 1.00 |
| 10009 | 3 | | | | ELAVL3 | 1.00 | 10105 | 3 | | | | FAM151B | 1.00 |
| 10010 | 3 | | | | ELAVL4 | 1.00 | 10106 | 3 | | | | FAM153A | 1.00 |
| 10011 | 3 | | | | ELFN2 | 1.00 | 10107 | 3 | | | | FAM153B | 1.00 |
| 10012 | 3 | | | | ELOVL2 | 1.00 | 10108 | 3 | | | | FAM153C | 1.00 |
| 10013 | 3 | | | | ELSPBP1 | 1.00 | 10109 | 3 | | | | FAM154A | 1.00 |
| 10014 | 3 | | | | EMBP1 | 1.00 | 10110 | 3 | | | | FAM154B | 1.00 |
| 10015 | 3 | | | | EMID2 | 1.00 | 10111 | 3 | | | | FAM155A | 1.00 |
| 10016 | 3 | | | | EML5 | 1.00 | 10112 | 3 | | | | FAM155B | 1.00 |
| 10017 | 3 | | | | EML6 | 1.00 | 10113 | 3 | | | | FAM157A | 1.00 |
| 10018 | 3 | | | | EMR1 | 1.00 | 10114 | 3 | | | | FAM157B | 1.00 |
| 10019 | 3 | | | | EMR3 | 1.00 | 10115 | 3 | | | | FAM159A | 1.00 |
| 10020 | 3 | | | | EMR4P | 1.00 | 10116 | 3 | | | | FAM159B | 1.00 |
| 10021 | 3 | | | | EMX1 | 1.00 | 10117 | 3 | | | | FAM163A | 1.00 |
| 10022 | 3 | | | | EN2 | 1.00 | 10118 | 3 | | | | FAM163B | 1.00 |
| 10023 | 3 | | | | ENAM | 1.00 | 10119 | 3 | | | | FAM166A | 1.00 |
| 10024 | 3 | | | | ENKUR | 1.00 | 10120 | 3 | | | | FAM169A | 1.00 |
| 10025 | 3 | | | | ENO1-AS1 | 1.00 | 10121 | 3 | | | | FAM169B | 1.00 |
| 10026 | 3 | | | | ENPP3 | 1.00 | 10122 | 3 | | | | FAM170A | 1.00 |
| 10027 | 3 | | | | ENPP6 | 1.00 | 10123 | 3 | | | | FAM170B | 1.00 |
| 10028 | 3 | | | | ENPP7 | 1.00 | 10124 | 3 | | | | FAM171B | 1.00 |
| 10029 | 3 | | | | ENTHD1 | 1.00 | 10125 | 3 | | | | FAM172BP | 1.00 |
| 10030 | 3 | | | | ENTPD3-AS1 | 1.00 | 10126 | 3 | | | | FAM177B | 1.00 |
| 10031 | 3 | | | | ENTPD5 | 1.00 | 10127 | 3 | | | | FAM181A | 1.00 |
| 10032 | 3 | | | | ENTPD7 | 1.00 | 10128 | 3 | | | | FAM181A-AS1 | 1.00 |
| 10033 | 3 | | | | ENTPD8 | 1.00 | 10129 | 3 | | | | FAM183B | 1.00 |
| 10034 | 3 | | | | EOMES | 1.00 | 10130 | 3 | | | | FAM184A | 1.00 |
| 10035 | 3 | | | | EPB42 | 1.00 | 10131 | 3 | | | | FAM186A | 1.00 |
| 10036 | 3 | | | | EPGN | 1.00 | 10132 | 3 | | | | FAM186B | 1.00 |
| 10037 | 3 | | | | EPHA10 | 1.00 | 10133 | 3 | | | | FAM187B | 1.00 |
| 10038 | 3 | | | | EPHA3 | 1.00 | 10134 | 3 | | | | FAM189A1 | 1.00 |
| 10039 | 3 | | | | EPHA5 | 1.00 | 10135 | 3 | | | | FAM18B2-CDRT4 | 1.00 |
| 10040 | 3 | | | | EPHA6 | 1.00 | 10136 | 3 | | | | FAM190A | 1.00 |
| 10041 | 3 | | | | EPHA7 | 1.00 | 10137 | 3 | | | | FAM194A | 1.00 |
| 10042 | 3 | | | | EPHA8 | 1.00 | 10138 | 3 | | | | FAM194B | 1.00 |
| 10043 | 3 | | | | EPS8L3 | 1.00 | 10139 | 3 | | | | FAM196A | 1.00 |
| 10044 | 3 | | | | EPX | 1.00 | 10140 | 3 | | | | FAM196B | 1.00 |
| 10045 | 3 | | | | EPYC | 1.00 | 10141 | 3 | | | | FAM197Y2P | 1.00 |
| 10046 | 3 | | | | ERAS | 1.00 | 10142 | 3 | | | | FAM197Y5 | 1.00 |
| 10047 | 3 | | | | ERBB4 | 1.00 | 10143 | 3 | | | | FAM19A1 | 1.00 |
| 10048 | 3 | | | | ERC2 | 1.00 | 10144 | 3 | | | | FAM19A2 | 1.00 |
| 10049 | 3 | | | | ERCC6L | 1.00 | 10145 | 3 | | | | FAM19A3 | 1.00 |
| 10050 | 3 | | | | ERMN | 1.00 | 10146 | 3 | | | | FAM19A4 | 1.00 |
| 10051 | 3 | | | | ERN1 | 1.00 | 10147 | 3 | | | | FAM205A | 1.00 |
| 10052 | 3 | | | | ERN2 | 1.00 | 10148 | 3 | | | | FAM205B | 1.00 |
| 10053 | 3 | | | | ERVFRD-1 | 1.00 | 10149 | 3 | | | | FAM215A | 1.00 |
| 10054 | 3 | | | | ERVMER34-1 | 1.00 | 10150 | 3 | | | | FAM216B | 1.00 |
| 10055 | 3 | | | | ERVV-1 | 1.00 | 10151 | 3 | | | | FAM217A | 1.00 |
| 10056 | 3 | | | | ERVV-2 | 1.00 | 10152 | 3 | | | | FAM21A | 1.00 |
| 10057 | 3 | | | | ESCO2 | 1.00 | 10153 | 3 | | | | FAM22D | 1.00 |
| 10058 | 3 | | | | ESM1 | 1.00 | 10154 | 3 | | | | FAM22F | 1.00 |
| 10059 | 3 | | | | ESPNL | 1.00 | 10155 | 3 | | | | FAM24A | 1.00 |
| 10060 | 3 | | | | ESPNP | 1.00 | 10156 | 3 | | | | FAM24B-CUZD1 | 1.00 |
| 10061 | 3 | | | | ESR1 | 1.00 | 10157 | 3 | | | | FAM26D | 1.00 |
| 10062 | 3 | | | | ESR2 | 1.00 | 10158 | 3 | | | | FAM27L | 1.00 |
| 10063 | 3 | | | | ESRRB | 1.00 | 10159 | 3 | | | | FAM3B | 1.00 |
| 10064 | 3 | | | | ESX1 | 1.00 | 10160 | 3 | | | | FAM40B | 1.00 |
| 10065 | 3 | | | | ETV2 | 1.00 | 10161 | 3 | | | | FAM41AY1 | 1.00 |
| 10066 | 3 | | | | ETV3L | 1.00 | 10162 | 3 | | | | FAM41AY2 | 1.00 |
| 10067 | 3 | | | | EVX1 | 1.00 | 10163 | 3 | | | | FAM41C | 1.00 |
| 10068 | 3 | | | | EVX2 | 1.00 | 10164 | 3 | | | | FAM43B | 1.00 |
| 10069 | 3 | | | | EXD1 | 1.00 | 10165 | 3 | | | | FAM46D | 1.00 |
| 10070 | 3 | | | | EXO1 | 1.00 | 10166 | 3 | | | | FAM47A | 1.00 |
| 10071 | 3 | | | | EXOC3L1 | 1.00 | 10167 | 3 | | | | FAM47B | 1.00 |
| 10072 | 3 | | | | EXOC3L4 | 1.00 | 10168 | 3 | | | | FAM47C | 1.00 |
| 10073 | 3 | | | | EXOC6B | 1.00 | 10169 | 3 | | | | FAM47E | 1.00 |
| 10074 | 3 | | | | EYA1 | 1.00 | 10170 | 3 | | | | FAM47E-STBD1 | 1.00 |
| 10075 | 3 | | | | EYA4 | 1.00 | 10171 | 3 | | | | FAM48B1 | 1.00 |
| 10076 | 3 | | | | EYS | 1.00 | 10172 | 3 | | | | FAM48B2 | 1.00 |

Fig. 39 - 54

| | | | | | | | | | | | | | | | | | | |
|---|---|---|---|---|---|---|---|---|---|---|---|---|---|---|---|---|---|---|
| 10173 | 3 | | | | | | FAM55A | 1.00 | | 10269 | 3 | | | | | | FER1L5 | 1.00 |
| 10174 | 3 | | | | | | FAM55B | 1.00 | | 10270 | 3 | | | | | | FER1L6 | 1.00 |
| 10175 | 3 | | | | | | FAM55D | 1.00 | | 10271 | 3 | | | | | | FER1L6-AS1 | 1.00 |
| 10176 | 3 | | | | | | FAM57B | 1.00 | | 10272 | 3 | | | | | | FERD3L | 1.00 |
| 10177 | 3 | | | | | | FAM5B | 1.00 | | 10273 | 3 | | | | | | FEV | 1.00 |
| 10178 | 3 | | | | | | FAM5C | 1.00 | | 10274 | 3 | | | | | | FEZF1 | 1.00 |
| 10179 | 3 | | | | | | FAM66A | 1.00 | | 10275 | 3 | | | | | | FEZF2 | 1.00 |
| 10180 | 3 | | | | | | FAM66B | 1.00 | | 10276 | 3 | | | | | | FFAR1 | 1.00 |
| 10181 | 3 | | | | | | FAM66D | 1.00 | | 10277 | 3 | | | | | | FFAR3 | 1.00 |
| 10182 | 3 | | | | | | FAM66E | 1.00 | | 10278 | 3 | | | | | | FGA | 1.00 |
| 10183 | 3 | | | | | | FAM71A | 1.00 | | 10279 | 3 | | | | | | FGB | 1.00 |
| 10184 | 3 | | | | | | FAM71B | 1.00 | | 10280 | 3 | | | | | | FGF10 | 1.00 |
| 10185 | 3 | | | | | | FAM71C | 1.00 | | 10281 | 3 | | | | | | FGF12 | 1.00 |
| 10186 | 3 | | | | | | FAM71D | 1.00 | | 10282 | 3 | | | | | | FGF14 | 1.00 |
| 10187 | 3 | | | | | | FAM71E2 | 1.00 | | 10283 | 3 | | | | | | FGF14-IT1 | 1.00 |
| 10188 | 3 | | | | | | FAM71F1 | 1.00 | | 10284 | 3 | | | | | | FGF17 | 1.00 |
| 10189 | 3 | | | | | | FAM71F2 | 1.00 | | 10285 | 3 | | | | | | FGF19 | 1.00 |
| 10190 | 3 | | | | | | FAM74A1 | 1.00 | | 10286 | 3 | | | | | | FGF20 | 1.00 |
| 10191 | 3 | | | | | | FAM74A2 | 1.00 | | 10287 | 3 | | | | | | FGF21 | 1.00 |
| 10192 | 3 | | | | | | FAM74A3 | 1.00 | | 10288 | 3 | | | | | | FGF23 | 1.00 |
| 10193 | 3 | | | | | | FAM74A4 | 1.00 | | 10289 | 3 | | | | | | FGF3 | 1.00 |
| 10194 | 3 | | | | | | FAM75A1 | 1.00 | | 10290 | 3 | | | | | | FGF4 | 1.00 |
| 10195 | 3 | | | | | | FAM75A2 | 1.00 | | 10291 | 3 | | | | | | FGF5 | 1.00 |
| 10196 | 3 | | | | | | FAM75A3 | 1.00 | | 10292 | 3 | | | | | | FGF6 | 1.00 |
| 10197 | 3 | | | | | | FAM75A4 | 1.00 | | 10293 | 3 | | | | | | FGF8 | 1.00 |
| 10198 | 3 | | | | | | FAM75A5 | 1.00 | | 10294 | 3 | | | | | | FGF9 | 1.00 |
| 10199 | 3 | | | | | | FAM75A6 | 1.00 | | 10295 | 3 | | | | | | FGG | 1.00 |
| 10200 | 3 | | | | | | FAM75A7 | 1.00 | | 10296 | 3 | | | | | | FGL1 | 1.00 |
| 10201 | 3 | | | | | | FAM75C1 | 1.00 | | 10297 | 3 | | | | | | FHAD1 | 1.00 |
| 10202 | 3 | | | | | | FAM75C2 | 1.00 | | 10298 | 3 | | | | | | FHL5 | 1.00 |
| 10203 | 3 | | | | | | FAM75D1 | 1.00 | | 10299 | 3 | | | | | | FIBCD1 | 1.00 |
| 10204 | 3 | | | | | | FAM75D3 | 1.00 | | 10300 | 3 | | | | | | FIGLA | 1.00 |
| 10205 | 3 | | | | | | FAM75D4 | 1.00 | | 10301 | 3 | | | | | | FIGN | 1.00 |
| 10206 | 3 | | | | | | FAM75D5 | 1.00 | | 10302 | 3 | | | | | | FIGNL2 | 1.00 |
| 10207 | 3 | | | | | | FAM81B | 1.00 | | 10303 | 3 | | | | | | FILIP1 | 1.00 |
| 10208 | 3 | | | | | | FAM86B2 | 1.00 | | 10304 | 3 | | | | | | FKBP1A-SDCBP2 | 1.00 |
| 10209 | 3 | | | | | | FAM90A1 | 1.00 | | 10305 | 3 | | | | | | FKBP6 | 1.00 |
| 10210 | 3 | | | | | | FAM90A10 | 1.00 | | 10306 | 3 | | | | | | FKSG29 | 1.00 |
| 10211 | 3 | | | | | | FAM90A10P | 1.00 | | 10307 | 3 | | | | | | FLJ12334 | 1.00 |
| 10212 | 3 | | | | | | FAM90A14 | 1.00 | | 10308 | 3 | | | | | | FLJ12825 | 1.00 |
| 10213 | 3 | | | | | | FAM90A19 | 1.00 | | 10309 | 3 | | | | | | FLJ13224 | 1.00 |
| 10214 | 3 | | | | | | FAM90A20 | 1.00 | | 10310 | 3 | | | | | | FLJ16171 | 1.00 |
| 10215 | 3 | | | | | | FAM90A25P | 1.00 | | 10311 | 3 | | | | | | FLJ16341 | 1.00 |
| 10216 | 3 | | | | | | FAM90A27P | 1.00 | | 10312 | 3 | | | | | | FLJ16779 | 1.00 |
| 10217 | 3 | | | | | | FAM90A2P | 1.00 | | 10313 | 3 | | | | | | FLJ20518 | 1.00 |
| 10218 | 3 | | | | | | FAM90A5 | 1.00 | | 10314 | 3 | | | | | | FLJ21408 | 1.00 |
| 10219 | 3 | | | | | | FAM90A7 | 1.00 | | 10315 | 3 | | | | | | FLJ22184 | 1.00 |
| 10220 | 3 | | | | | | FAM90A7P | 1.00 | | 10316 | 3 | | | | | | FLJ22447 | 1.00 |
| 10221 | 3 | | | | | | FAM90A8 | 1.00 | | 10317 | 3 | | | | | | FLJ22763 | 1.00 |
| 10222 | 3 | | | | | | FAM90A9 | 1.00 | | 10318 | 3 | | | | | | FLJ23152 | 1.00 |
| 10223 | 3 | | | | | | FAM92A3 | 1.00 | | 10319 | 3 | | | | | | FLJ25328 | 1.00 |
| 10224 | 3 | | | | | | FAM92B | 1.00 | | 10320 | 3 | | | | | | FLJ25363 | 1.00 |
| 10225 | 3 | | | | | | FAM99A | 1.00 | | 10321 | 3 | | | | | | FLJ25758 | 1.00 |
| 10226 | 3 | | | | | | FAM99B | 1.00 | | 10322 | 3 | | | | | | FLJ26245 | 1.00 |
| 10227 | 3 | | | | | | FAM9A | 1.00 | | 10323 | 3 | | | | | | FLJ26850 | 1.00 |
| 10228 | 3 | | | | | | FAM9B | 1.00 | | 10324 | 3 | | | | | | FLJ30679 | 1.00 |
| 10229 | 3 | | | | | | FAM9C | 1.00 | | 10325 | 3 | | | | | | FLJ30838 | 1.00 |
| 10230 | 3 | | | | | | FANCB | 1.00 | | 10326 | 3 | | | | | | FLJ31662 | 1.00 |
| 10231 | 3 | | | | | | FANCM | 1.00 | | 10327 | 3 | | | | | | FLJ31813 | 1.00 |
| 10232 | 3 | | | | | | FAS-AS1 | 1.00 | | 10328 | 3 | | | | | | FLJ32063 | 1.00 |
| 10233 | 3 | | | | | | FASLG | 1.00 | | 10329 | 3 | | | | | | FLJ33065 | 1.00 |
| 10234 | 3 | | | | | | FAT3 | 1.00 | | 10330 | 3 | | | | | | FLJ33360 | 1.00 |
| 10235 | 3 | | | | | | FATE1 | 1.00 | | 10331 | 3 | | | | | | FLJ33534 | 1.00 |
| 10236 | 3 | | | | | | FAXC | 1.00 | | 10332 | 3 | | | | | | FLJ33581 | 1.00 |
| 10237 | 3 | | | | | | FBN2 | 1.00 | | 10333 | 3 | | | | | | FLJ34208 | 1.00 |
| 10238 | 3 | | | | | | FBN3 | 1.00 | | 10334 | 3 | | | | | | FLJ34503 | 1.00 |
| 10239 | 3 | | | | | | FBP2 | 1.00 | | 10335 | 3 | | | | | | FLJ34690 | 1.00 |
| 10240 | 3 | | | | | | FBXL13 | 1.00 | | 10336 | 3 | | | | | | FLJ35024 | 1.00 |
| 10241 | 3 | | | | | | FBXL19-AS1 | 1.00 | | 10337 | 3 | | | | | | FLJ35282 | 1.00 |
| 10242 | 3 | | | | | | FBXL21 | 1.00 | | 10338 | 3 | | | | | | FLJ35424 | 1.00 |
| 10243 | 3 | | | | | | FBXO15 | 1.00 | | 10339 | 3 | | | | | | FLJ35946 | 1.00 |
| 10244 | 3 | | | | | | FBXO16 | 1.00 | | 10340 | 3 | | | | | | FLJ36000 | 1.00 |
| 10245 | 3 | | | | | | FBXO24 | 1.00 | | 10341 | 3 | | | | | | FLJ36777 | 1.00 |
| 10246 | 3 | | | | | | FBXO39 | 1.00 | | 10342 | 3 | | | | | | FLJ37035 | 1.00 |
| 10247 | 3 | | | | | | FBXO40 | 1.00 | | 10343 | 3 | | | | | | FLJ37201 | 1.00 |
| 10248 | 3 | | | | | | FBXO43 | 1.00 | | 10344 | 3 | | | | | | FLJ37505 | 1.00 |
| 10249 | 3 | | | | | | FBXO47 | 1.00 | | 10345 | 3 | | | | | | FLJ38109 | 1.00 |
| 10250 | 3 | | | | | | FBXO48 | 1.00 | | 10346 | 3 | | | | | | FLJ38576 | 1.00 |
| 10251 | 3 | | | | | | FBXW10 | 1.00 | | 10347 | 3 | | | | | | FLJ39080 | 1.00 |
| 10252 | 3 | | | | | | FBXW12 | 1.00 | | 10348 | 3 | | | | | | FLJ39534 | 1.00 |
| 10253 | 3 | | | | | | FCAMR | 1.00 | | 10349 | 3 | | | | | | FLJ40194 | 1.00 |
| 10254 | 3 | | | | | | FCAR | 1.00 | | 10350 | 3 | | | | | | FLJ40288 | 1.00 |
| 10255 | 3 | | | | | | FCGR1A | 1.00 | | 10351 | 3 | | | | | | FLJ40292 | 1.00 |
| 10256 | 3 | | | | | | FCGR1B | 1.00 | | 10352 | 3 | | | | | | FLJ40434 | 1.00 |
| 10257 | 3 | | | | | | FCGR1C | 1.00 | | 10353 | 3 | | | | | | FLJ41278 | 1.00 |
| 10258 | 3 | | | | | | FCN2 | 1.00 | | 10354 | 3 | | | | | | FLJ41350 | 1.00 |
| 10259 | 3 | | | | | | FCRL1 | 1.00 | | 10355 | 3 | | | | | | FLJ41484 | 1.00 |
| 10260 | 3 | | | | | | FCRL2 | 1.00 | | 10356 | 3 | | | | | | FLJ41649 | 1.00 |
| 10261 | 3 | | | | | | FCRL3 | 1.00 | | 10357 | 3 | | | | | | FLJ41941 | 1.00 |
| 10262 | 3 | | | | | | FCRL4 | 1.00 | | 10358 | 3 | | | | | | FLJ42102 | 1.00 |
| 10263 | 3 | | | | | | FCRL5 | 1.00 | | 10359 | 3 | | | | | | FLJ42280 | 1.00 |
| 10264 | 3 | | | | | | FCRL6 | 1.00 | | 10360 | 3 | | | | | | FLJ42289 | 1.00 |
| 10265 | 3 | | | | | | FCRLB | 1.00 | | 10361 | 3 | | | | | | FLJ42351 | 1.00 |
| 10266 | 3 | | | | | | FDCSP | 1.00 | | 10362 | 3 | | | | | | FLJ42709 | 1.00 |
| 10267 | 3 | | | | | | FER | 1.00 | | 10363 | 3 | | | | | | FLJ42969 | 1.00 |
| 10268 | 3 | | | | | | FER1L4 | 1.00 | | 10364 | 3 | | | | | | FLJ43315 | 1.00 |

Fig. 39 - 55

| | | | | | | | | | | | | | | |
|---|---|---|---|---|---|---|---|---|---|---|---|---|---|---|
| 10365 | 3 | | | | | FLJ43390 | 1.00 | 10461 | 3 | | | | GABRB1 | 1.00 |
| 10366 | 3 | | | | | FLJ43826 | 1.00 | 10462 | 3 | | | | GABRB2 | 1.00 |
| 10367 | 3 | | | | | FLJ43860 | 1.00 | 10463 | 3 | | | | GABRB3 | 1.00 |
| 10368 | 3 | | | | | FLJ43879 | 1.00 | 10464 | 3 | | | | GABRD | 1.00 |
| 10369 | 3 | | | | | FLJ44054 | 1.00 | 10465 | 3 | | | | GABRG1 | 1.00 |
| 10370 | 3 | | | | | FLJ44511 | 1.00 | 10466 | 3 | | | | GABRG2 | 1.00 |
| 10371 | 3 | | | | | FLJ45079 | 1.00 | 10467 | 3 | | | | GABRG3 | 1.00 |
| 10372 | 3 | | | | | FLJ45974 | 1.00 | 10468 | 3 | | | | GABRQ | 1.00 |
| 10373 | 3 | | | | | FLJ46066 | 1.00 | 10469 | 3 | | | | GABRR1 | 1.00 |
| 10374 | 3 | | | | | FLJ46257 | 1.00 | 10470 | 3 | | | | GABRR2 | 1.00 |
| 10375 | 3 | | | | | FLJ46284 | 1.00 | 10471 | 3 | | | | GABRR3 | 1.00 |
| 10376 | 3 | | | | | FLJ46300 | 1.00 | 10472 | 3 | | | | GAD1 | 1.00 |
| 10377 | 3 | | | | | FLJ46361 | 1.00 | 10473 | 3 | | | | GAD2 | 1.00 |
| 10378 | 3 | | | | | FLJ46446 | 1.00 | 10474 | 3 | | | | GADL1 | 1.00 |
| 10379 | 3 | | | | | FLT3 | 1.00 | 10475 | 3 | | | | GAGE1 | 1.00 |
| 10380 | 3 | | | | | FMN2 | 1.00 | 10476 | 3 | | | | GAGE10 | 1.00 |
| 10381 | 3 | | | | | FMO6P | 1.00 | 10477 | 3 | | | | GAGE12B | 1.00 |
| 10382 | 3 | | | | | FMO9P | 1.00 | 10478 | 3 | | | | GAGE12C | 1.00 |
| 10383 | 3 | | | | | FMR1-AS1 | 1.00 | 10479 | 3 | | | | GAGE12D | 1.00 |
| 10384 | 3 | | | | | FMR1NB | 1.00 | 10480 | 3 | | | | GAGE12E | 1.00 |
| 10385 | 3 | | | | | FNDC7 | 1.00 | 10481 | 3 | | | | GAGE12F | 1.00 |
| 10386 | 3 | | | | | FNDC8 | 1.00 | 10482 | 3 | | | | GAGE12H | 1.00 |
| 10387 | 3 | | | | | FNDC9 | 1.00 | 10483 | 3 | | | | GAGE12I | 1.00 |
| 10388 | 3 | | | | | FOLH1 | 1.00 | 10484 | 3 | | | | GAGE12J | 1.00 |
| 10389 | 3 | | | | | FOLH1B | 1.00 | 10485 | 3 | | | | GAGE13 | 1.00 |
| 10390 | 3 | | | | | FOLR4 | 1.00 | 10486 | 3 | | | | GAGE2A | 1.00 |
| 10391 | 3 | | | | | FONG | 1.00 | 10487 | 3 | | | | GAGE2B | 1.00 |
| 10392 | 3 | | | | | FOXA2 | 1.00 | 10488 | 3 | | | | GAGE2C | 1.00 |
| 10393 | 3 | | | | | FOXA3 | 1.00 | 10489 | 3 | | | | GAGE2D | 1.00 |
| 10394 | 3 | | | | | FOXB1 | 1.00 | 10490 | 3 | | | | GAGE2E | 1.00 |
| 10395 | 3 | | | | | FOXB2 | 1.00 | 10491 | 3 | | | | GAGE4 | 1.00 |
| 10396 | 3 | | | | | FOXD2 | 1.00 | 10492 | 3 | | | | GAGE5 | 1.00 |
| 10397 | 3 | | | | | FOXD4 | 1.00 | 10493 | 3 | | | | GAGE6 | 1.00 |
| 10398 | 3 | | | | | FOXD4L1 | 1.00 | 10494 | 3 | | | | GAGE7 | 1.00 |
| 10399 | 3 | | | | | FOXD4L2 | 1.00 | 10495 | 3 | | | | GAGE8 | 1.00 |
| 10400 | 3 | | | | | FOXD4L3 | 1.00 | 10496 | 3 | | | | GAL3ST2 | 1.00 |
| 10401 | 3 | | | | | FOXD4L5 | 1.00 | 10497 | 3 | | | | GAL3ST3 | 1.00 |
| 10402 | 3 | | | | | FOXD4L6 | 1.00 | 10498 | 3 | | | | GALNT13 | 1.00 |
| 10403 | 3 | | | | | FOXE3 | 1.00 | 10499 | 3 | | | | GALNT14 | 1.00 |
| 10404 | 3 | | | | | FOXG1 | 1.00 | 10500 | 3 | | | | GALNT4 | 1.00 |
| 10405 | 3 | | | | | FOXH1 | 1.00 | 10501 | 3 | | | | GALNT5 | 1.00 |
| 10406 | 3 | | | | | FOXI3 | 1.00 | 10502 | 3 | | | | GALNT8 | 1.00 |
| 10407 | 3 | | | | | FOXL1 | 1.00 | 10503 | 3 | | | | GALNT9 | 1.00 |
| 10408 | 3 | | | | | FOXL2 | 1.00 | 10504 | 3 | | | | GALNTL5 | 1.00 |
| 10409 | 3 | | | | | FOXN4 | 1.00 | 10505 | 3 | | | | GALNTL6 | 1.00 |
| 10410 | 3 | | | | | FOXR1 | 1.00 | 10506 | 3 | | | | GALP | 1.00 |
| 10411 | 3 | | | | | FOXR2 | 1.00 | 10507 | 3 | | | | GALR1 | 1.00 |
| 10412 | 3 | | | | | FPGT-TNNI3K | 1.00 | 10508 | 3 | | | | GALR2 | 1.00 |
| 10413 | 3 | | | | | FRAS1 | 1.00 | 10509 | 3 | | | | GALR3 | 1.00 |
| 10414 | 3 | | | | | FREM2 | 1.00 | 10510 | 3 | | | | GAS2L3 | 1.00 |
| 10415 | 3 | | | | | FREM3 | 1.00 | 10511 | 3 | | | | GAST | 1.00 |
| 10416 | 3 | | | | | FRG2 | 1.00 | 10512 | 3 | | | | GATA1 | 1.00 |
| 10417 | 3 | | | | | FRG2B | 1.00 | 10513 | 3 | | | | GATA4 | 1.00 |
| 10418 | 3 | | | | | FRG2C | 1.00 | 10514 | 3 | | | | GATSL2 | 1.00 |
| 10419 | 3 | | | | | FRK | 1.00 | 10515 | 3 | | | | GBA3 | 1.00 |
| 10420 | 3 | | | | | FRMD1 | 1.00 | 10516 | 3 | | | | GBP1P1 | 1.00 |
| 10421 | 3 | | | | | FRMD5 | 1.00 | 10517 | 3 | | | | GBP5 | 1.00 |
| 10422 | 3 | | | | | FRMD7 | 1.00 | 10518 | 3 | | | | GBP6 | 1.00 |
| 10423 | 3 | | | | | FRMPD2 | 1.00 | 10519 | 3 | | | | GBP7 | 1.00 |
| 10424 | 3 | | | | | FRMPD2P1 | 1.00 | 10520 | 3 | | | | GBX1 | 1.00 |
| 10425 | 3 | | | | | FRMPD4 | 1.00 | 10521 | 3 | | | | GBX2 | 1.00 |
| 10426 | 3 | | | | | FSBP | 1.00 | 10522 | 3 | | | | GC | 1.00 |
| 10427 | 3 | | | | | FSCB | 1.00 | 10523 | 3 | | | | GCFC1-AS1 | 1.00 |
| 10428 | 3 | | | | | FSCN2 | 1.00 | 10524 | 3 | | | | GCG | 1.00 |
| 10429 | 3 | | | | | FSCN3 | 1.00 | 10525 | 3 | | | | GCGR | 1.00 |
| 10430 | 3 | | | | | FSD1 | 1.00 | 10526 | 3 | | | | GCK | 1.00 |
| 10431 | 3 | | | | | FSD1L | 1.00 | 10527 | 3 | | | | GCKR | 1.00 |
| 10432 | 3 | | | | | FSD2 | 1.00 | 10528 | 3 | | | | GCM1 | 1.00 |
| 10433 | 3 | | | | | FSHB | 1.00 | 10529 | 3 | | | | GCM2 | 1.00 |
| 10434 | 3 | | | | | FSHR | 1.00 | 10530 | 3 | | | | GCNT3 | 1.00 |
| 10435 | 3 | | | | | FSIP1 | 1.00 | 10531 | 3 | | | | GCNT4 | 1.00 |
| 10436 | 3 | | | | | FSIP2 | 1.00 | 10532 | 3 | | | | GCNT7 | 1.00 |
| 10437 | 3 | | | | | FSTL5 | 1.00 | 10533 | 3 | | | | GCOM1 | 1.00 |
| 10438 | 3 | | | | | FTCD | 1.00 | 10534 | 3 | | | | GDA | 1.00 |
| 10439 | 3 | | | | | FTHL17 | 1.00 | 10535 | 3 | | | | GDAP1L1 | 1.00 |
| 10440 | 3 | | | | | FTLP10 | 1.00 | 10536 | 3 | | | | GDEP | 1.00 |
| 10441 | 3 | | | | | FTMT | 1.00 | 10537 | 3 | | | | GDF2 | 1.00 |
| 10442 | 3 | | | | | FUT5 | 1.00 | 10538 | 3 | | | | GDF3 | 1.00 |
| 10443 | 3 | | | | | FUT6 | 1.00 | 10539 | 3 | | | | GDF5 | 1.00 |
| 10444 | 3 | | | | | FUT9 | 1.00 | 10540 | 3 | | | | GDF6 | 1.00 |
| 10445 | 3 | | | | | FXYD1 | 1.00 | 10541 | 3 | | | | GDF7 | 1.00 |
| 10446 | 3 | | | | | FXYD2 | 1.00 | 10542 | 3 | | | | GDF9 | 1.00 |
| 10447 | 3 | | | | | FXYD4 | 1.00 | 10543 | 3 | | | | GDPD4 | 1.00 |
| 10448 | 3 | | | | | FXYD6-FXYD2 | 1.00 | 10544 | 3 | | | | GFAP | 1.00 |
| 10449 | 3 | | | | | FZD9 | 1.00 | 10545 | 3 | | | | GFI1 | 1.00 |
| 10450 | 3 | | | | | G6PC | 1.00 | 10546 | 3 | | | | GFI1B | 1.00 |
| 10451 | 3 | | | | | G6PC2 | 1.00 | 10547 | 3 | | | | GFRA4 | 1.00 |
| 10452 | 3 | | | | | GAB4 | 1.00 | 10548 | 3 | | | | GFRAL | 1.00 |
| 10453 | 3 | | | | | GABARAPL3 | 1.00 | 10549 | 3 | | | | GGNBP1 | 1.00 |
| 10454 | 3 | | | | | GABBR2 | 1.00 | 10550 | 3 | | | | GGT3P | 1.00 |
| 10455 | 3 | | | | | GABRA1 | 1.00 | 10551 | 3 | | | | GGT8P | 1.00 |
| 10456 | 3 | | | | | GABRA2 | 1.00 | 10552 | 3 | | | | GGTLC1 | 1.00 |
| 10457 | 3 | | | | | GABRA3 | 1.00 | 10553 | 3 | | | | GH1 | 1.00 |
| 10458 | 3 | | | | | GABRA4 | 1.00 | 10554 | 3 | | | | GH2 | 1.00 |
| 10459 | 3 | | | | | GABRA5 | 1.00 | 10555 | 3 | | | | GHRH | 1.00 |
| 10460 | 3 | | | | | GABRA6 | 1.00 | 10556 | 3 | | | | GHRHR | 1.00 |

Fig. 39 - 56

| | | | | | | | | | | | | | | |
|---|---|---|---|---|---|---|---|---|---|---|---|---|---|---|
| 10557 | 3 | | | | | GHRL | 1.00 | 10653 | 3 | | | | GPR179 | 1.00 |
| 10558 | 3 | | | | | GHSR | 1.00 | 10654 | 3 | | | | GPR18 | 1.00 |
| 10559 | 3 | | | | | GIF | 1.00 | 10655 | 3 | | | | GPR182 | 1.00 |
| 10560 | 3 | | | | | GIP | 1.00 | 10656 | 3 | | | | GPR19 | 1.00 |
| 10561 | 3 | | | | | GJA10 | 1.00 | 10657 | 3 | | | | GPR21 | 1.00 |
| 10562 | 3 | | | | | GJA3 | 1.00 | 10658 | 3 | | | | GPR22 | 1.00 |
| 10563 | 3 | | | | | GJA8 | 1.00 | 10659 | 3 | | | | GPR25 | 1.00 |
| 10564 | 3 | | | | | GJA9 | 1.00 | 10660 | 3 | | | | GPR26 | 1.00 |
| 10565 | 3 | | | | | GJB7 | 1.00 | 10661 | 3 | | | | GPR31 | 1.00 |
| 10566 | 3 | | | | | GJD2 | 1.00 | 10662 | 3 | | | | GPR32 | 1.00 |
| 10567 | 3 | | | | | GJD4 | 1.00 | 10663 | 3 | | | | GPR33 | 1.00 |
| 10568 | 3 | | | | | GK2 | 1.00 | 10664 | 3 | | | | GPR37L1 | 1.00 |
| 10569 | 3 | | | | | GK3P | 1.00 | 10665 | 3 | | | | GPR39 | 1.00 |
| 10570 | 3 | | | | | GKN1 | 1.00 | 10666 | 3 | | | | GPR45 | 1.00 |
| 10571 | 3 | | | | | GKN2 | 1.00 | 10667 | 3 | | | | GPR50 | 1.00 |
| 10572 | 3 | | | | | GLIPR1L1 | 1.00 | 10668 | 3 | | | | GPR52 | 1.00 |
| 10573 | 3 | | | | | GLIPR1L2 | 1.00 | 10669 | 3 | | | | GPR6 | 1.00 |
| 10574 | 3 | | | | | GLIS3 | 1.00 | 10670 | 3 | | | | GPR61 | 1.00 |
| 10575 | 3 | | | | | GLIS3-AS1 | 1.00 | 10671 | 3 | | | | GPR62 | 1.00 |
| 10576 | 3 | | | | | GLMN | 1.00 | 10672 | 3 | | | | GPR63 | 1.00 |
| 10577 | 3 | | | | | GLOD5 | 1.00 | 10673 | 3 | | | | GPR64 | 1.00 |
| 10578 | 3 | | | | | GLP1R | 1.00 | 10674 | 3 | | | | GPR65 | 1.00 |
| 10579 | 3 | | | | | GLP2R | 1.00 | 10675 | 3 | | | | GPR75 | 1.00 |
| 10580 | 3 | | | | | GLRA1 | 1.00 | 10676 | 3 | | | | GPR75-ASB3 | 1.00 |
| 10581 | 3 | | | | | GLRA2 | 1.00 | 10677 | 3 | | | | GPR78 | 1.00 |
| 10582 | 3 | | | | | GLRA3 | 1.00 | 10678 | 3 | | | | GPR82 | 1.00 |
| 10583 | 3 | | | | | GLRA4 | 1.00 | 10679 | 3 | | | | GPR83 | 1.00 |
| 10584 | 3 | | | | | GLT25D2 | 1.00 | 10680 | 3 | | | | GPR85 | 1.00 |
| 10585 | 3 | | | | | GLT6D1 | 1.00 | 10681 | 3 | | | | GPR88 | 1.00 |
| 10586 | 3 | | | | | GLYATL3 | 1.00 | 10682 | 3 | | | | GPR97 | 1.00 |
| 10587 | 3 | | | | | GLYCAM1 | 1.00 | 10683 | 3 | | | | GPR98 | 1.00 |
| 10588 | 3 | | | | | GM140 | 1.00 | 10684 | 3 | | | | GPRC6A | 1.00 |
| 10589 | 3 | | | | | GML | 1.00 | 10685 | 3 | | | | GPRIN3 | 1.00 |
| 10590 | 3 | | | | | GMNC | 1.00 | 10686 | 3 | | | | GPX5 | 1.00 |
| 10591 | 3 | | | | | GNAS-AS1 | 1.00 | 10687 | 3 | | | | GPX6 | 1.00 |
| 10592 | 3 | | | | | GNAT1 | 1.00 | 10688 | 3 | | | | GRAMD1B | 1.00 |
| 10593 | 3 | | | | | GNAT2 | 1.00 | 10689 | 3 | | | | GRAPL | 1.00 |
| 10594 | 3 | | | | | GNAT3 | 1.00 | 10690 | 3 | | | | GREB3L | 1.00 |
| 10595 | 3 | | | | | GNG13 | 1.00 | 10691 | 3 | | | | GRIA1 | 1.00 |
| 10596 | 3 | | | | | GNG3 | 1.00 | 10692 | 3 | | | | GRIA3 | 1.00 |
| 10597 | 3 | | | | | GNG4 | 1.00 | 10693 | 3 | | | | GRIA4 | 1.00 |
| 10598 | 3 | | | | | GNG8 | 1.00 | 10694 | 3 | | | | GRID2 | 1.00 |
| 10599 | 3 | | | | | GNGT1 | 1.00 | 10695 | 3 | | | | GRID2IP | 1.00 |
| 10600 | 3 | | | | | GNGT2 | 1.00 | 10696 | 3 | | | | GRIK1 | 1.00 |
| 10601 | 3 | | | | | GNMT | 1.00 | 10697 | 3 | | | | GRIK1-AS1 | 1.00 |
| 10602 | 3 | | | | | GNN | 1.00 | 10698 | 3 | | | | GRIK1-AS2 | 1.00 |
| 10603 | 3 | | | | | GNRH2 | 1.00 | 10699 | 3 | | | | GRIK2 | 1.00 |
| 10604 | 3 | | | | | GNRHR | 1.00 | 10700 | 3 | | | | GRIK4 | 1.00 |
| 10605 | 3 | | | | | GOLGA2P3Y | 1.00 | 10701 | 3 | | | | GRIK5 | 1.00 |
| 10606 | 3 | | | | | GOLGA6A | 1.00 | 10702 | 3 | | | | GRIN1 | 1.00 |
| 10607 | 3 | | | | | GOLGA6B | 1.00 | 10703 | 3 | | | | GRIN2A | 1.00 |
| 10608 | 3 | | | | | GOLGA6C | 1.00 | 10704 | 3 | | | | GRIN2B | 1.00 |
| 10609 | 3 | | | | | GOLGA6D | 1.00 | 10705 | 3 | | | | GRIN2C | 1.00 |
| 10610 | 3 | | | | | GOLGA6L1 | 1.00 | 10706 | 3 | | | | GRIN2D | 1.00 |
| 10611 | 3 | | | | | GOLGA6L6 | 1.00 | 10707 | 3 | | | | GRIN3A | 1.00 |
| 10612 | 3 | | | | | GOLGA8C | 1.00 | 10708 | 3 | | | | GRK1 | 1.00 |
| 10613 | 3 | | | | | GOLGA8DP | 1.00 | 10709 | 3 | | | | GRK4 | 1.00 |
| 10614 | 3 | | | | | GOLGA8E | 1.00 | 10710 | 3 | | | | GRK7 | 1.00 |
| 10615 | 3 | | | | | GOLGA8F | 1.00 | 10711 | 3 | | | | GRM1 | 1.00 |
| 10616 | 3 | | | | | GOLGA8G | 1.00 | 10712 | 3 | | | | GRM3 | 1.00 |
| 10617 | 3 | | | | | GOLGA8IP | 1.00 | 10713 | 3 | | | | GRM4 | 1.00 |
| 10618 | 3 | | | | | GOLT1A | 1.00 | 10714 | 3 | | | | GRM5 | 1.00 |
| 10619 | 3 | | | | | GOT1L1 | 1.00 | 10715 | 3 | | | | GRM6 | 1.00 |
| 10620 | 3 | | | | | GP2 | 1.00 | 10716 | 3 | | | | GRM7 | 1.00 |
| 10621 | 3 | | | | | GP5 | 1.00 | 10717 | 3 | | | | GRM8 | 1.00 |
| 10622 | 3 | | | | | GP9 | 1.00 | 10718 | 3 | | | | GRP | 1.00 |
| 10623 | 3 | | | | | GPA33 | 1.00 | 10719 | 3 | | | | GRPR | 1.00 |
| 10624 | 3 | | | | | GPC5 | 1.00 | 10720 | 3 | | | | GRXCR1 | 1.00 |
| 10625 | 3 | | | | | GPCRLTM7 | 1.00 | 10721 | 3 | | | | GRXCR2 | 1.00 |
| 10626 | 3 | | | | | GPHA2 | 1.00 | 10722 | 3 | | | | GSC2 | 1.00 |
| 10627 | 3 | | | | | GPHBS | 1.00 | 10723 | 3 | | | | GSG1 | 1.00 |
| 10628 | 3 | | | | | GPLD1 | 1.00 | 10724 | 3 | | | | GSG1L | 1.00 |
| 10629 | 3 | | | | | GPM6A | 1.00 | 10725 | 3 | | | | GSTA1 | 1.00 |
| 10630 | 3 | | | | | GPR101 | 1.00 | 10726 | 3 | | | | GSTA2 | 1.00 |
| 10631 | 3 | | | | | GPR110 | 1.00 | 10727 | 3 | | | | GSTA5 | 1.00 |
| 10632 | 3 | | | | | GPR112 | 1.00 | 10728 | 3 | | | | GSTA7P | 1.00 |
| 10633 | 3 | | | | | GPR113 | 1.00 | 10729 | 3 | | | | GSTTP1 | 1.00 |
| 10634 | 3 | | | | | GPR114 | 1.00 | 10730 | 3 | | | | GSTTP2 | 1.00 |
| 10635 | 3 | | | | | GPR119 | 1.00 | 10731 | 3 | | | | GSX1 | 1.00 |
| 10636 | 3 | | | | | GPR123 | 1.00 | 10732 | 3 | | | | GSX2 | 1.00 |
| 10637 | 3 | | | | | GPR128 | 1.00 | 10733 | 3 | | | | GTF2A1 | 1.00 |
| 10638 | 3 | | | | | GPR135 | 1.00 | 10734 | 3 | | | | GTF2A1L | 1.00 |
| 10639 | 3 | | | | | GPR137C | 1.00 | 10735 | 3 | | | | GTF2H2 | 1.00 |
| 10640 | 3 | | | | | GPR139 | 1.00 | 10736 | 3 | | | | GTF2H2C | 1.00 |
| 10641 | 3 | | | | | GPR141 | 1.00 | 10737 | 3 | | | | GTF2H2D | 1.00 |
| 10642 | 3 | | | | | GPR142 | 1.00 | 10738 | 3 | | | | GTSF1 | 1.00 |
| 10643 | 3 | | | | | GPR144 | 1.00 | 10739 | 3 | | | | GTSF1L | 1.00 |
| 10644 | 3 | | | | | GPR148 | 1.00 | 10740 | 3 | | | | GUCA1A | 1.00 |
| 10645 | 3 | | | | | GPR149 | 1.00 | 10741 | 3 | | | | GUCA1C | 1.00 |
| 10646 | 3 | | | | | GPR15 | 1.00 | 10742 | 3 | | | | GUCA2A | 1.00 |
| 10647 | 3 | | | | | GPR150 | 1.00 | 10743 | 3 | | | | GUCA2B | 1.00 |
| 10648 | 3 | | | | | GPR151 | 1.00 | 10744 | 3 | | | | GUCY1A2 | 1.00 |
| 10649 | 3 | | | | | GPR152 | 1.00 | 10745 | 3 | | | | GUCY1B2 | 1.00 |
| 10650 | 3 | | | | | GPR156 | 1.00 | 10746 | 3 | | | | GUCY2C | 1.00 |
| 10651 | 3 | | | | | GPR158 | 1.00 | 10747 | 3 | | | | GUCY2D | 1.00 |
| 10652 | 3 | | | | | GPR174 | 1.00 | 10748 | 3 | | | | GUCY2E | 1.00 |

Fig. 39 - 57

| | | | | | | | | | | | | | | | | | | |
|---|---|---|---|---|---|---|---|---|---|---|---|---|---|---|---|---|---|---|
| 10749 | 3 | | | | | | GUCY2F | 1.00 | | 10845 | 3 | | | | | | HIST1H3I | 1.00 |
| 10750 | 3 | | | | | | GUCY2GP | 1.00 | | 10846 | 3 | | | | | | HIST1H3J | 1.00 |
| 10751 | 3 | | | | | | GUSBP10 | 1.00 | | 10847 | 3 | | | | | | HIST1H4A | 1.00 |
| 10752 | 3 | | | | | | GUSBP2 | 1.00 | | 10848 | 3 | | | | | | HIST1H4F | 1.00 |
| 10753 | 3 | | | | | | GVINP1 | 1.00 | | 10849 | 3 | | | | | | HIST1H4G | 1.00 |
| 10754 | 3 | | | | | | GYG2P1 | 1.00 | | 10850 | 3 | | | | | | HIST1H4I | 1.00 |
| 10755 | 3 | | | | | | GYPA | 1.00 | | 10851 | 3 | | | | | | HIST1H4L | 1.00 |
| 10756 | 3 | | | | | | GYPB | 1.00 | | 10852 | 3 | | | | | | HIST2H3D | 1.00 |
| 10757 | 3 | | | | | | GYPE | 1.00 | | 10853 | 3 | | | | | | HIST3H3 | 1.00 |
| 10758 | 3 | | | | | | GYS2 | 1.00 | | 10854 | 3 | | | | | | HK3 | 1.00 |
| 10759 | 3 | | | | | | GZMM | 1.00 | | 10855 | 3 | | | | | | HKDC1 | 1.00 |
| 10760 | 3 | | | | | | H1FNT | 1.00 | | 10856 | 3 | | | | | | HLA-DPB2 | 1.00 |
| 10761 | 3 | | | | | | H1FOO | 1.00 | | 10857 | 3 | | | | | | HLA-J | 1.00 |
| 10762 | 3 | | | | | | H2AFB1 | 1.00 | | 10858 | 3 | | | | | | HLA-L | 1.00 |
| 10763 | 3 | | | | | | H2AFB2 | 1.00 | | 10859 | 3 | | | | | | HMGA1P7 | 1.00 |
| 10764 | 3 | | | | | | H2BFM | 1.00 | | 10860 | 3 | | | | | | HMGA2 | 1.00 |
| 10765 | 3 | | | | | | H2BFWT | 1.00 | | 10861 | 3 | | | | | | HMGB3P1 | 1.00 |
| 10766 | 3 | | | | | | H2BFXP | 1.00 | | 10862 | 3 | | | | | | HMGB4 | 1.00 |
| 10767 | 3 | | | | | | HABP2 | 1.00 | | 10863 | 3 | | | | | | HMGCLL1 | 1.00 |
| 10768 | 3 | | | | | | HAMP | 1.00 | | 10864 | 3 | | | | | | HMGN2P46 | 1.00 |
| 10769 | 3 | | | | | | HAND1 | 1.00 | | 10865 | 3 | | | | | | HMHB1 | 1.00 |
| 10770 | 3 | | | | | | HAO1 | 1.00 | | 10866 | 3 | | | | | | HMMR | 1.00 |
| 10771 | 3 | | | | | | HAP1 | 1.00 | | 10867 | 3 | | | | | | HMP19 | 1.00 |
| 10772 | 3 | | | | | | HAPLN1 | 1.00 | | 10868 | 3 | | | | | | HMSD | 1.00 |
| 10773 | 3 | | | | | | HAPLN2 | 1.00 | | 10869 | 3 | | | | | | HMX1 | 1.00 |
| 10774 | 3 | | | | | | HAPLN4 | 1.00 | | 10870 | 3 | | | | | | HMX2 | 1.00 |
| 10775 | 3 | | | | | | HAR1A | 1.00 | | 10871 | 3 | | | | | | HMX3 | 1.00 |
| 10776 | 3 | | | | | | HAR1B | 1.00 | | 10872 | 3 | | | | | | HNF1A | 1.00 |
| 10777 | 3 | | | | | | HAS2-AS1 | 1.00 | | 10873 | 3 | | | | | | HNF1A-AS1 | 1.00 |
| 10778 | 3 | | | | | | HAVCR1 | 1.00 | | 10874 | 3 | | | | | | HNF1B | 1.00 |
| 10779 | 3 | | | | | | HBBP1 | 1.00 | | 10875 | 3 | | | | | | HNF4A | 1.00 |
| 10780 | 3 | | | | | | HBD | 1.00 | | 10876 | 3 | | | | | | HNF4G | 1.00 |
| 10781 | 3 | | | | | | HBE1 | 1.00 | | 10877 | 3 | | | | | | HNRNPA1P10 | 1.00 |
| 10782 | 3 | | | | | | HBG1 | 1.00 | | 10878 | 3 | | | | | | HNRNPA3P1 | 1.00 |
| 10783 | 3 | | | | | | HBM | 1.00 | | 10879 | 3 | | | | | | HNRNPCL1 | 1.00 |
| 10784 | 3 | | | | | | HBQ1 | 1.00 | | 10880 | 3 | | | | | | HNRNPUL2-BSCL2 | 1.00 |
| 10785 | 3 | | | | | | HBZ | 1.00 | | 10881 | 3 | | | | | | HORMAD1 | 1.00 |
| 10786 | 3 | | | | | | HCAR1 | 1.00 | | 10882 | 3 | | | | | | HORMAD2 | 1.00 |
| 10787 | 3 | | | | | | HCG22 | 1.00 | | 10883 | 3 | | | | | | HOTTIP | 1.00 |
| 10788 | 3 | | | | | | HCG4B | 1.00 | | 10884 | 3 | | | | | | HOXA10-HOXA9 | 1.00 |
| 10789 | 3 | | | | | | HCG9 | 1.00 | | 10885 | 3 | | | | | | HOXA11 | 1.00 |
| 10790 | 3 | | | | | | HCN1 | 1.00 | | 10886 | 3 | | | | | | HOXA13 | 1.00 |
| 10791 | 3 | | | | | | HCN4 | 1.00 | | 10887 | 3 | | | | | | HOXA-AS5 | 1.00 |
| 10792 | 3 | | | | | | HCRT | 1.00 | | 10888 | 3 | | | | | | HOXB1 | 1.00 |
| 10793 | 3 | | | | | | HCRTR1 | 1.00 | | 10889 | 3 | | | | | | HOXB13 | 1.00 |
| 10794 | 3 | | | | | | HCRTR2 | 1.00 | | 10890 | 3 | | | | | | HOXB9 | 1.00 |
| 10795 | 3 | | | | | | HDGFL1 | 1.00 | | 10891 | 3 | | | | | | HOXB-AS5 | 1.00 |
| 10796 | 3 | | | | | | HDX | 1.00 | | 10892 | 3 | | | | | | HOXD11 | 1.00 |
| 10797 | 3 | | | | | | HEATR4 | 1.00 | | 10893 | 3 | | | | | | HOXD12 | 1.00 |
| 10798 | 3 | | | | | | HEATR7B2 | 1.00 | | 10894 | 3 | | | | | | HOXD13 | 1.00 |
| 10799 | 3 | | | | | | HEATR8-TTC4 | 1.00 | | 10895 | 3 | | | | | | HPCA | 1.00 |
| 10800 | 3 | | | | | | HECW1 | 1.00 | | 10896 | 3 | | | | | | HPCAL4 | 1.00 |
| 10801 | 3 | | | | | | HELB | 1.00 | | 10897 | 3 | | | | | | HPD | 1.00 |
| 10802 | 3 | | | | | | HELLS | 1.00 | | 10898 | 3 | | | | | | HPN | 1.00 |
| 10803 | 3 | | | | | | HEMGN | 1.00 | | 10899 | 3 | | | | | | HPR | 1.00 |
| 10804 | 3 | | | | | | HEPACAM | 1.00 | | 10900 | 3 | | | | | | HPVC1 | 1.00 |
| 10805 | 3 | | | | | | HEPACAM2 | 1.00 | | 10901 | 3 | | | | | | HPX | 1.00 |
| 10806 | 3 | | | | | | HEPHL1 | 1.00 | | 10902 | 3 | | | | | | HPYR1 | 1.00 |
| 10807 | 3 | | | | | | HERC2P3 | 1.00 | | 10903 | 3 | | | | | | HRASLS2 | 1.00 |
| 10808 | 3 | | | | | | HERC2P4 | 1.00 | | 10904 | 3 | | | | | | HRG | 1.00 |
| 10809 | 3 | | | | | | HERC5 | 1.00 | | 10905 | 3 | | | | | | HRH3 | 1.00 |
| 10810 | 3 | | | | | | HES3 | 1.00 | | 10906 | 3 | | | | | | HRH4 | 1.00 |
| 10811 | 3 | | | | | | HES7 | 1.00 | | 10907 | 3 | | | | | | HRK | 1.00 |
| 10812 | 3 | | | | | | HESX1 | 1.00 | | 10908 | 3 | | | | | | HRNR | 1.00 |
| 10813 | 3 | | | | | | HFE2 | 1.00 | | 10909 | 3 | | | | | | HS3ST5 | 1.00 |
| 10814 | 3 | | | | | | HFM1 | 1.00 | | 10910 | 3 | | | | | | HS6ST2 | 1.00 |
| 10815 | 3 | | | | | | HGC6.3 | 1.00 | | 10911 | 3 | | | | | | HS6ST3 | 1.00 |
| 10816 | 3 | | | | | | HGF | 1.00 | | 10912 | 3 | | | | | | HSD17B3 | 1.00 |
| 10817 | 3 | | | | | | HGFAC | 1.00 | | 10913 | 3 | | | | | | HSD3B2 | 1.00 |
| 10818 | 3 | | | | | | HHIP | 1.00 | | 10914 | 3 | | | | | | HSD3BP4 | 1.00 |
| 10819 | 3 | | | | | | HHIPL2 | 1.00 | | 10915 | 3 | | | | | | HSF2BP | 1.00 |
| 10820 | 3 | | | | | | HHLA1 | 1.00 | | 10916 | 3 | | | | | | HSF5 | 1.00 |
| 10821 | 3 | | | | | | HHLA2 | 1.00 | | 10917 | 3 | | | | | | HSFX2 | 1.00 |
| 10822 | 3 | | | | | | HIGD1C | 1.00 | | 10918 | 3 | | | | | | HSFY1 | 1.00 |
| 10823 | 3 | | | | | | HIGD2B | 1.00 | | 10919 | 3 | | | | | | HSFY1P1 | 1.00 |
| 10824 | 3 | | | | | | HILS1 | 1.00 | | 10920 | 3 | | | | | | HSFY2 | 1.00 |
| 10825 | 3 | | | | | | HIPK4 | 1.00 | | 10921 | 3 | | | | | | HSPB2-C11orfS2 | 1.00 |
| 10826 | 3 | | | | | | HIST1H1A | 1.00 | | 10922 | 3 | | | | | | HSPB9 | 1.00 |
| 10827 | 3 | | | | | | HIST1H1T | 1.00 | | 10923 | 3 | | | | | | HSPC072 | 1.00 |
| 10828 | 3 | | | | | | HIST1H2AA | 1.00 | | 10924 | 3 | | | | | | HTA | 1.00 |
| 10829 | 3 | | | | | | HIST1H2AB | 1.00 | | 10925 | 3 | | | | | | HTN1 | 1.00 |
| 10830 | 3 | | | | | | HIST1H2AG | 1.00 | | 10926 | 3 | | | | | | HTN3 | 1.00 |
| 10831 | 3 | | | | | | HIST1H2AJ | 1.00 | | 10927 | 3 | | | | | | HTR1A | 1.00 |
| 10832 | 3 | | | | | | HIST1H2AL | 1.00 | | 10928 | 3 | | | | | | HTR1B | 1.00 |
| 10833 | 3 | | | | | | HIST1H2AM | 1.00 | | 10929 | 3 | | | | | | HTR1D | 1.00 |
| 10834 | 3 | | | | | | HIST1H2APS1 | 1.00 | | 10930 | 3 | | | | | | HTR1E | 1.00 |
| 10835 | 3 | | | | | | HIST1H2BA | 1.00 | | 10931 | 3 | | | | | | HTR1F | 1.00 |
| 10836 | 3 | | | | | | HIST1H2BB | 1.00 | | 10932 | 3 | | | | | | HTR2A | 1.00 |
| 10837 | 3 | | | | | | HIST1H2BF | 1.00 | | 10933 | 3 | | | | | | HTR2B | 1.00 |
| 10838 | 3 | | | | | | HIST1H2BL | 1.00 | | 10934 | 3 | | | | | | HTR2C | 1.00 |
| 10839 | 3 | | | | | | HIST1H2BM | 1.00 | | 10935 | 3 | | | | | | HTR3A | 1.00 |
| 10840 | 3 | | | | | | HIST1H2BN | 1.00 | | 10936 | 3 | | | | | | HTR3B | 1.00 |
| 10841 | 3 | | | | | | HIST1H3B | 1.00 | | 10937 | 3 | | | | | | HTR3C | 1.00 |
| 10842 | 3 | | | | | | HIST1H3C | 1.00 | | 10938 | 3 | | | | | | HTR3D | 1.00 |
| 10843 | 3 | | | | | | HIST1H3D | 1.00 | | 10939 | 3 | | | | | | HTR3E | 1.00 |
| 10844 | 3 | | | | | | HIST1H3F | 1.00 | | 10940 | 3 | | | | | | HTR4 | 1.00 |

Fig. 39 - 58

| | | | | | | | | | | | | | | | |
|---|---|---|---|---|---|---|---|---|---|---|---|---|---|---|---|
| 10941 | 3 | | | | | HTR5A | 1.00 | 11037 | 3 | | | | | IL5 | 1.00 |
| 10942 | 3 | | | | | HTR6 | 1.00 | 11038 | 3 | | | | | IL5RA | 1.00 |
| 10943 | 3 | | | | | HTR7 | 1.00 | 11039 | 3 | | | | | IL9 | 1.00 |
| 10944 | 3 | | | | | HTRA4 | 1.00 | 11040 | 3 | | | | | IL9R | 1.00 |
| 10945 | 3 | | | | | HTT-AS1 | 1.00 | 11041 | 3 | | | | | ILDR2 | 1.00 |
| 10946 | 3 | | | | | HULC | 1.00 | 11042 | 3 | | | | | IMPG1 | 1.00 |
| 10947 | 3 | | | | | HUS1B | 1.00 | 11043 | 3 | | | | | IMPG2 | 1.00 |
| 10948 | 3 | | | | | HYAL4 | 1.00 | 11044 | 3 | | | | | INA | 1.00 |
| 10949 | 3 | | | | | HYALP1 | 1.00 | 11045 | 3 | | | | | INGX | 1.00 |
| 10950 | 3 | | | | | HYDIN | 1.00 | 11046 | 3 | | | | | INHBC | 1.00 |
| 10951 | 3 | | | | | HYMAI | 1.00 | 11047 | 3 | | | | | INHBE | 1.00 |
| 10952 | 3 | | | | | IAPP | 1.00 | 11048 | 3 | | | | | INMT-FAM188B | 1.00 |
| 10953 | 3 | | | | | IBSP | 1.00 | 11049 | 3 | | | | | INO80B-WBP1 | 1.00 |
| 10954 | 3 | | | | | ICAM4 | 1.00 | 11050 | 3 | | | | | INPP4B | 1.00 |
| 10955 | 3 | | | | | ICAM5 | 1.00 | 11051 | 3 | | | | | INS | 1.00 |
| 10956 | 3 | | | | | ICOS | 1.00 | 11052 | 3 | | | | | INSC | 1.00 |
| 10957 | 3 | | | | | IDAS | 1.00 | 11053 | 3 | | | | | INS-IGF2 | 1.00 |
| 10958 | 3 | | | | | IDO1 | 1.00 | 11054 | 3 | | | | | INSL3 | 1.00 |
| 10959 | 3 | | | | | IDO2 | 1.00 | 11055 | 3 | | | | | INSL4 | 1.00 |
| 10960 | 3 | | | | | IFIT1B | 1.00 | 11056 | 3 | | | | | INSL5 | 1.00 |
| 10961 | 3 | | | | | IFITM5 | 1.00 | 11057 | 3 | | | | | INSL6 | 1.00 |
| 10962 | 3 | | | | | IFLTD1 | 1.00 | 11058 | 3 | | | | | INSM1 | 1.00 |
| 10963 | 3 | | | | | IFNA1 | 1.00 | 11059 | 3 | | | | | INSM2 | 1.00 |
| 10964 | 3 | | | | | IFNA10 | 1.00 | 11060 | 3 | | | | | INSRR | 1.00 |
| 10965 | 3 | | | | | IFNA13 | 1.00 | 11061 | 3 | | | | | INTS4L1 | 1.00 |
| 10966 | 3 | | | | | IFNA14 | 1.00 | 11062 | 3 | | | | | INTS4L2 | 1.00 |
| 10967 | 3 | | | | | IFNA16 | 1.00 | 11063 | 3 | | | | | IP6K3 | 1.00 |
| 10968 | 3 | | | | | IFNA17 | 1.00 | 11064 | 3 | | | | | IPCEF1 | 1.00 |
| 10969 | 3 | | | | | IFNA2 | 1.00 | 11065 | 3 | | | | | IQCA1 | 1.00 |
| 10970 | 3 | | | | | IFNA21 | 1.00 | 11066 | 3 | | | | | IQCF1 | 1.00 |
| 10971 | 3 | | | | | IFNA22P | 1.00 | 11067 | 3 | | | | | IQCF2 | 1.00 |
| 10972 | 3 | | | | | IFNA4 | 1.00 | 11068 | 3 | | | | | IQCF3 | 1.00 |
| 10973 | 3 | | | | | IFNA5 | 1.00 | 11069 | 3 | | | | | IQCF4 | 1.00 |
| 10974 | 3 | | | | | IFNA6 | 1.00 | 11070 | 3 | | | | | IQCF5 | 1.00 |
| 10975 | 3 | | | | | IFNA7 | 1.00 | 11071 | 3 | | | | | IQCF6 | 1.00 |
| 10976 | 3 | | | | | IFNA8 | 1.00 | 11072 | 3 | | | | | IQCH | 1.00 |
| 10977 | 3 | | | | | IFNB1 | 1.00 | 11073 | 3 | | | | | IQCJ | 1.00 |
| 10978 | 3 | | | | | IFNE | 1.00 | 11074 | 3 | | | | | IQUB | 1.00 |
| 10979 | 3 | | | | | IFNG | 1.00 | 11075 | 3 | | | | | IRAK1BP1 | 1.00 |
| 10980 | 3 | | | | | IFNK | 1.00 | 11076 | 3 | | | | | IRGC | 1.00 |
| 10981 | 3 | | | | | IFNW1 | 1.00 | 11077 | 3 | | | | | IRGM | 1.00 |
| 10982 | 3 | | | | | IFT88 | 1.00 | 11078 | 3 | | | | | IRS4 | 1.00 |
| 10983 | 3 | | | | | IGDCC3 | 1.00 | 11079 | 3 | | | | | ISL1 | 1.00 |
| 10984 | 3 | | | | | IGF2-AS1 | 1.00 | 11080 | 3 | | | | | ISL2 | 1.00 |
| 10985 | 3 | | | | | IGF2BP1 | 1.00 | 11081 | 3 | | | | | ISM2 | 1.00 |
| 10986 | 3 | | | | | IGF2BP3 | 1.00 | 11082 | 3 | | | | | ISPD | 1.00 |
| 10987 | 3 | | | | | IGFBP1 | 1.00 | 11083 | 3 | | | | | ISX | 1.00 |
| 10988 | 3 | | | | | IGFBPL1 | 1.00 | 11084 | 3 | | | | | ISY1-RAB43 | 1.00 |
| 10989 | 3 | | | | | IGFL1 | 1.00 | 11085 | 3 | | | | | ITGA1 | 1.00 |
| 10990 | 3 | | | | | IGFN1 | 1.00 | 11086 | 3 | | | | | ITGA2B | 1.00 |
| 10991 | 3 | | | | | IGLL1 | 1.00 | 11087 | 3 | | | | | ITGA4 | 1.00 |
| 10992 | 3 | | | | | IGSF11-AS1 | 1.00 | 11088 | 3 | | | | | ITGA8 | 1.00 |
| 10993 | 3 | | | | | IGSF22 | 1.00 | 11089 | 3 | | | | | ITGA9 | 1.00 |
| 10994 | 3 | | | | | IGSF23 | 1.00 | 11090 | 3 | | | | | ITGAD | 1.00 |
| 10995 | 3 | | | | | IGSF5 | 1.00 | 11091 | 3 | | | | | ITGAE | 1.00 |
| 10996 | 3 | | | | | IGSF9B | 1.00 | 11092 | 3 | | | | | ITGAV | 1.00 |
| 10997 | 3 | | | | | IHH | 1.00 | 11093 | 3 | | | | | ITGB1BP2 | 1.00 |
| 10998 | 3 | | | | | IKZF3 | 1.00 | 11094 | 3 | | | | | ITGB1BP3 | 1.00 |
| 10999 | 3 | | | | | IL10 | 1.00 | 11095 | 3 | | | | | ITGB6 | 1.00 |
| 11000 | 3 | | | | | IL12A | 1.00 | 11096 | 3 | | | | | ITIH1 | 1.00 |
| 11001 | 3 | | | | | IL12B | 1.00 | 11097 | 3 | | | | | ITIH2 | 1.00 |
| 11002 | 3 | | | | | IL12RB1 | 1.00 | 11098 | 3 | | | | | ITIH3 | 1.00 |
| 11003 | 3 | | | | | IL12RB2 | 1.00 | 11099 | 3 | | | | | ITIH6 | 1.00 |
| 11004 | 3 | | | | | IL13 | 1.00 | 11100 | 3 | | | | | ITLN1 | 1.00 |
| 11005 | 3 | | | | | IL13RA2 | 1.00 | 11101 | 3 | | | | | ITLN2 | 1.00 |
| 11006 | 3 | | | | | IL17A | 1.00 | 11102 | 3 | | | | | ITPK1-AS1 | 1.00 |
| 11007 | 3 | | | | | IL17C | 1.00 | 11103 | 3 | | | | | ITPKA | 1.00 |
| 11008 | 3 | | | | | IL17F | 1.00 | 11104 | 3 | | | | | IYD | 1.00 |
| 11009 | 3 | | | | | IL17REL | 1.00 | 11105 | 3 | | | | | IZUMO1 | 1.00 |
| 11010 | 3 | | | | | IL18RAP | 1.00 | 11106 | 3 | | | | | IZUMO2 | 1.00 |
| 11011 | 3 | | | | | IL19 | 1.00 | 11107 | 3 | | | | | JAKMIP1 | 1.00 |
| 11012 | 3 | | | | | IL1A | 1.00 | 11108 | 3 | | | | | JAKMIP2 | 1.00 |
| 11013 | 3 | | | | | IL1RAPL1 | 1.00 | 11109 | 3 | | | | | JAKMIP3 | 1.00 |
| 11014 | 3 | | | | | IL1RAPL2 | 1.00 | 11110 | 3 | | | | | JAZF1-AS1 | 1.00 |
| 11015 | 3 | | | | | IL1RL1 | 1.00 | 11111 | 3 | | | | | JMJD7-PLA2G4B | 1.00 |
| 11016 | 3 | | | | | IL2 | 1.00 | 11112 | 3 | | | | | JPH1 | 1.00 |
| 11017 | 3 | | | | | IL20 | 1.00 | 11113 | 3 | | | | | JPH3 | 1.00 |
| 11018 | 3 | | | | | IL21 | 1.00 | 11114 | 3 | | | | | JSRP1 | 1.00 |
| 11019 | 3 | | | | | IL21R | 1.00 | 11115 | 3 | | | | | KAAG1 | 1.00 |
| 11020 | 3 | | | | | IL22 | 1.00 | 11116 | 3 | | | | | KAL1 | 1.00 |
| 11021 | 3 | | | | | IL22RA2 | 1.00 | 11117 | 3 | | | | | KATNAL2 | 1.00 |
| 11022 | 3 | | | | | IL23A | 1.00 | 11118 | 3 | | | | | KBTBD10 | 1.00 |
| 11023 | 3 | | | | | IL23R | 1.00 | 11119 | 3 | | | | | KBTBD12 | 1.00 |
| 11024 | 3 | | | | | IL24 | 1.00 | 11120 | 3 | | | | | KBTBD13 | 1.00 |
| 11025 | 3 | | | | | IL25 | 1.00 | 11121 | 3 | | | | | KBTBD5 | 1.00 |
| 11026 | 3 | | | | | IL26 | 1.00 | 11122 | 3 | | | | | KBTBD8 | 1.00 |
| 11027 | 3 | | | | | IL27 | 1.00 | 11123 | 3 | | | | | KC6 | 1.00 |
| 11028 | 3 | | | | | IL28A | 1.00 | 11124 | 3 | | | | | KCNA1 | 1.00 |
| 11029 | 3 | | | | | IL28B | 1.00 | 11125 | 3 | | | | | KCNA10 | 1.00 |
| 11030 | 3 | | | | | IL29 | 1.00 | 11126 | 3 | | | | | KCNA2 | 1.00 |
| 11031 | 3 | | | | | IL2RA | 1.00 | 11127 | 3 | | | | | KCNA3 | 1.00 |
| 11032 | 3 | | | | | IL3 | 1.00 | 11128 | 3 | | | | | KCNA4 | 1.00 |
| 11033 | 3 | | | | | IL31 | 1.00 | 11129 | 3 | | | | | KCNA5 | 1.00 |
| 11034 | 3 | | | | | IL31RA | 1.00 | 11130 | 3 | | | | | KCNA7 | 1.00 |
| 11035 | 3 | | | | | IL36A | 1.00 | 11131 | 3 | | | | | KCNB1 | 1.00 |
| 11036 | 3 | | | | | IL4 | 1.00 | 11132 | 3 | | | | | KCNB2 | 1.00 |

Fig. 39 - 59

| | | | | | | | | | | | | | | |
|---|---|---|---|---|---|---|---|---|---|---|---|---|---|---|
| 11133 | 3 | | | | | KCNC1 | 1.00 | 11229 | 3 | | | | KIF25 | 1.00 |
| 11134 | 3 | | | | | KCNC2 | 1.00 | 11230 | 3 | | | | KIF27 | 1.00 |
| 11135 | 3 | | | | | KCND2 | 1.00 | 11231 | 3 | | | | KIF28 | 1.00 |
| 11136 | 3 | | | | | KCND3 | 1.00 | 11232 | 3 | | | | KIF4A | 1.00 |
| 11137 | 3 | | | | | KCNE1L | 1.00 | 11233 | 3 | | | | KIF4B | 1.00 |
| 11138 | 3 | | | | | KCNE2 | 1.00 | 11234 | 3 | | | | KIF5A | 1.00 |
| 11139 | 3 | | | | | KCNF1 | 1.00 | 11235 | 3 | | | | KIF5C | 1.00 |
| 11140 | 3 | | | | | KCNG2 | 1.00 | 11236 | 3 | | | | KIF6 | 1.00 |
| 11141 | 3 | | | | | KCNG3 | 1.00 | 11237 | 3 | | | | KIR2DL1 | 1.00 |
| 11142 | 3 | | | | | KCNG4 | 1.00 | 11238 | 3 | | | | KIR2DL2 | 1.00 |
| 11143 | 3 | | | | | KCNH1 | 1.00 | 11239 | 3 | | | | KIR2DL3 | 1.00 |
| 11144 | 3 | | | | | KCNH3 | 1.00 | 11240 | 3 | | | | KIR2DL4 | 1.00 |
| 11145 | 3 | | | | | KCNH4 | 1.00 | 11241 | 3 | | | | KIR2DL5A | 1.00 |
| 11146 | 3 | | | | | KCNH5 | 1.00 | 11242 | 3 | | | | KIR2DL5B | 1.00 |
| 11147 | 3 | | | | | KCNH6 | 1.00 | 11243 | 3 | | | | KIR2DS1 | 1.00 |
| 11148 | 3 | | | | | KCNH7 | 1.00 | 11244 | 3 | | | | KIR2DS2 | 1.00 |
| 11149 | 3 | | | | | KCNH8 | 1.00 | 11245 | 3 | | | | KIR2DS3 | 1.00 |
| 11150 | 3 | | | | | KCNIP1 | 1.00 | 11246 | 3 | | | | KIR2DS4 | 1.00 |
| 11151 | 3 | | | | | KCNIP4 | 1.00 | 11247 | 3 | | | | KIR2DS5 | 1.00 |
| 11152 | 3 | | | | | KCNIP4-IT1 | 1.00 | 11248 | 3 | | | | KIR3DL1 | 1.00 |
| 11153 | 3 | | | | | KCNJ10 | 1.00 | 11249 | 3 | | | | KIR3DL2 | 1.00 |
| 11154 | 3 | | | | | KCNJ13 | 1.00 | 11250 | 3 | | | | KIR3DL3 | 1.00 |
| 11155 | 3 | | | | | KCNJ16 | 1.00 | 11251 | 3 | | | | KIR3DS1 | 1.00 |
| 11156 | 3 | | | | | KCNJ3 | 1.00 | 11252 | 3 | | | | KIR3DX1 | 1.00 |
| 11157 | 3 | | | | | KCNJ4 | 1.00 | 11253 | 3 | | | | KIRREL2 | 1.00 |
| 11158 | 3 | | | | | KCNJ5 | 1.00 | 11254 | 3 | | | | KIRREL3 | 1.00 |
| 11159 | 3 | | | | | KCNJ6 | 1.00 | 11255 | 3 | | | | KIRREL3-AS3 | 1.00 |
| 11160 | 3 | | | | | KCNJ9 | 1.00 | 11256 | 3 | | | | KISS1 | 1.00 |
| 11161 | 3 | | | | | KCNK10 | 1.00 | 11257 | 3 | | | | KISS1R | 1.00 |
| 11162 | 3 | | | | | KCNK13 | 1.00 | 11258 | 3 | | | | KLF1 | 1.00 |
| 11163 | 3 | | | | | KCNK16 | 1.00 | 11259 | 3 | | | | KLF17 | 1.00 |
| 11164 | 3 | | | | | KCNK17 | 1.00 | 11260 | 3 | | | | KLHDC7A | 1.00 |
| 11165 | 3 | | | | | KCNK18 | 1.00 | 11261 | 3 | | | | KLHDC7B | 1.00 |
| 11166 | 3 | | | | | KCNK3 | 1.00 | 11262 | 3 | | | | KLHDC8A | 1.00 |
| 11167 | 3 | | | | | KCNK4 | 1.00 | 11263 | 3 | | | | KLHL1 | 1.00 |
| 11168 | 3 | | | | | KCNK9 | 1.00 | 11264 | 3 | | | | KLHL10 | 1.00 |
| 11169 | 3 | | | | | KCNMB2 | 1.00 | 11265 | 3 | | | | KLHL11 | 1.00 |
| 11170 | 3 | | | | | KCNN1 | 1.00 | 11266 | 3 | | | | KLHL14 | 1.00 |
| 11171 | 3 | | | | | KCNN2 | 1.00 | 11267 | 3 | | | | KLHL31 | 1.00 |
| 11172 | 3 | | | | | KCNN3 | 1.00 | 11268 | 3 | | | | KLHL32 | 1.00 |
| 11173 | 3 | | | | | KCNQ1DN | 1.00 | 11269 | 3 | | | | KLHL33 | 1.00 |
| 11174 | 3 | | | | | KCNQ1OT1 | 1.00 | 11270 | 3 | | | | KLHL34 | 1.00 |
| 11175 | 3 | | | | | KCNQ2 | 1.00 | 11271 | 3 | | | | KLHL35 | 1.00 |
| 11176 | 3 | | | | | KCNQ3 | 1.00 | 11272 | 3 | | | | KLHL38 | 1.00 |
| 11177 | 3 | | | | | KCNQ5 | 1.00 | 11273 | 3 | | | | KLHL4 | 1.00 |
| 11178 | 3 | | | | | KCNS2 | 1.00 | 11274 | 3 | | | | KLHL6 | 1.00 |
| 11179 | 3 | | | | | KCNT1 | 1.00 | 11275 | 3 | | | | KLHL7-AS1 | 1.00 |
| 11180 | 3 | | | | | KCNT2 | 1.00 | 11276 | 3 | | | | KLK12 | 1.00 |
| 11181 | 3 | | | | | KCNU1 | 1.00 | 11277 | 3 | | | | KLK15 | 1.00 |
| 11182 | 3 | | | | | KCNV1 | 1.00 | 11278 | 3 | | | | KLK2 | 1.00 |
| 11183 | 3 | | | | | KCNV2 | 1.00 | 11279 | 3 | | | | KLK3 | 1.00 |
| 11184 | 3 | | | | | KCP | 1.00 | 11280 | 3 | | | | KLK4 | 1.00 |
| 11185 | 3 | | | | | KCTD14 | 1.00 | 11281 | 3 | | | | KLKB1 | 1.00 |
| 11186 | 3 | | | | | KCTD16 | 1.00 | 11282 | 3 | | | | KLKP1 | 1.00 |
| 11187 | 3 | | | | | KCTD19 | 1.00 | 11283 | 3 | | | | KLLN | 1.00 |
| 11188 | 3 | | | | | KCTD8 | 1.00 | 11284 | 3 | | | | KLRC1 | 1.00 |
| 11189 | 3 | | | | | KDM4DL | 1.00 | 11285 | 3 | | | | KLRC2 | 1.00 |
| 11190 | 3 | | | | | KEL | 1.00 | 11286 | 3 | | | | KLRC3 | 1.00 |
| 11191 | 3 | | | | | KERA | 1.00 | 11287 | 3 | | | | KLRC4 | 1.00 |
| 11192 | 3 | | | | | KGFLP1 | 1.00 | 11288 | 3 | | | | KLRC4-KLRK1 | 1.00 |
| 11193 | 3 | | | | | KHDC1 | 1.00 | 11289 | 3 | | | | KLRD1 | 1.00 |
| 11194 | 3 | | | | | KHDC1L | 1.00 | 11290 | 3 | | | | KLRF1 | 1.00 |
| 11195 | 3 | | | | | KHDRBS2 | 1.00 | 11291 | 3 | | | | KLRF2 | 1.00 |
| 11196 | 3 | | | | | KIAA0087 | 1.00 | 11292 | 3 | | | | KLRG1 | 1.00 |
| 11197 | 3 | | | | | KIAA0101 | 1.00 | 11293 | 3 | | | | KMO | 1.00 |
| 11198 | 3 | | | | | KIAA0125 | 1.00 | 11294 | 3 | | | | KNCN | 1.00 |
| 11199 | 3 | | | | | KIAA0226L | 1.00 | 11295 | 3 | | | | KNDC1 | 1.00 |
| 11200 | 3 | | | | | KIAA0319 | 1.00 | 11296 | 3 | | | | KNG1 | 1.00 |
| 11201 | 3 | | | | | KIAA0408 | 1.00 | 11297 | 3 | | | | KNTC1 | 1.00 |
| 11202 | 3 | | | | | KIAA0664L3 | 1.00 | 11298 | 3 | | | | KPNA5 | 1.00 |
| 11203 | 3 | | | | | KIAA0754 | 1.00 | 11299 | 3 | | | | KPNA7 | 1.00 |
| 11204 | 3 | | | | | KIAA0825 | 1.00 | 11300 | 3 | | | | KRT12 | 1.00 |
| 11205 | 3 | | | | | KIAA1024 | 1.00 | 11301 | 3 | | | | KRT13 | 1.00 |
| 11206 | 3 | | | | | KIAA1107 | 1.00 | 11302 | 3 | | | | KRT18P55 | 1.00 |
| 11207 | 3 | | | | | KIAA1199 | 1.00 | 11303 | 3 | | | | KRT20 | 1.00 |
| 11208 | 3 | | | | | KIAA1210 | 1.00 | 11304 | 3 | | | | KRT222 | 1.00 |
| 11209 | 3 | | | | | KIAA1211 | 1.00 | 11305 | 3 | | | | KRT24 | 1.00 |
| 11210 | 3 | | | | | KIAA1239 | 1.00 | 11306 | 3 | | | | KRT26 | 1.00 |
| 11211 | 3 | | | | | KIAA1257 | 1.00 | 11307 | 3 | | | | KRT33A | 1.00 |
| 11212 | 3 | | | | | KIAA1383 | 1.00 | 11308 | 3 | | | | KRT33B | 1.00 |
| 11213 | 3 | | | | | KIAA1524 | 1.00 | 11309 | 3 | | | | KRT34 | 1.00 |
| 11214 | 3 | | | | | KIAA1549 | 1.00 | 11310 | 3 | | | | KRT36 | 1.00 |
| 11215 | 3 | | | | | KIAA1656 | 1.00 | 11311 | 3 | | | | KRT37 | 1.00 |
| 11216 | 3 | | | | | KIAA1731 | 1.00 | 11312 | 3 | | | | KRT38 | 1.00 |
| 11217 | 3 | | | | | KIAA1751 | 1.00 | 11313 | 3 | | | | KRT39 | 1.00 |
| 11218 | 3 | | | | | KIAA1804 | 1.00 | 11314 | 3 | | | | KRT40 | 1.00 |
| 11219 | 3 | | | | | KIAA1875 | 1.00 | 11315 | 3 | | | | KRT76 | 1.00 |
| 11220 | 3 | | | | | KIAA1958 | 1.00 | 11316 | 3 | | | | KRT82 | 1.00 |
| 11221 | 3 | | | | | KIAA1984 | 1.00 | 11317 | 3 | | | | KRT83 | 1.00 |
| 11222 | 3 | | | | | KIAA2022 | 1.00 | 11318 | 3 | | | | KRT84 | 1.00 |
| 11223 | 3 | | | | | KIF12 | 1.00 | 11319 | 3 | | | | KRT8P41 | 1.00 |
| 11224 | 3 | | | | | KIF14 | 1.00 | 11320 | 3 | | | | KRTAP10-1 | 1.00 |
| 11225 | 3 | | | | | KIF15 | 1.00 | 11321 | 3 | | | | KRTAP10-10 | 1.00 |
| 11226 | 3 | | | | | KIF18A | 1.00 | 11322 | 3 | | | | KRTAP10-11 | 1.00 |
| 11227 | 3 | | | | | KIF19 | 1.00 | 11323 | 3 | | | | KRTAP10-12 | 1.00 |
| 11228 | 3 | | | | | KIF24 | 1.00 | 11324 | 3 | | | | KRTAP10-2 | 1.00 |

Fig. 39 - 60

| | | | | | | | | | | | | | |
|---|---|---|---|---|---|---|---|---|---|---|---|---|---|
| 11325 | 3 | | | | | KRTAP10-3 | 1.00 | 11421 | 3 | | | LEAP2 | 1.00 |
| 11326 | 3 | | | | | KRTAP10-4 | 1.00 | 11422 | 3 | | | LECT1 | 1.00 |
| 11327 | 3 | | | | | KRTAP10-6 | 1.00 | 11423 | 3 | | | LECT2 | 1.00 |
| 11328 | 3 | | | | | KRTAP10-7 | 1.00 | 11424 | 3 | | | LEFTY1 | 1.00 |
| 11329 | 3 | | | | | KRTAP10-8 | 1.00 | 11425 | 3 | | | LEFTY2 | 1.00 |
| 11330 | 3 | | | | | KRTAP10-9 | 1.00 | 11426 | 3 | | | LEKR1 | 1.00 |
| 11331 | 3 | | | | | KRTAP1-1 | 1.00 | 11427 | 3 | | | LELP1 | 1.00 |
| 11332 | 3 | | | | | KRTAP12-1 | 1.00 | 11428 | 3 | | | LEMD1 | 1.00 |
| 11333 | 3 | | | | | KRTAP12-2 | 1.00 | 11429 | 3 | | | LENEP | 1.00 |
| 11334 | 3 | | | | | KRTAP12-3 | 1.00 | 11430 | 3 | | | LETM2 | 1.00 |
| 11335 | 3 | | | | | KRTAP12-4 | 1.00 | 11431 | 3 | | | LEUTX | 1.00 |
| 11336 | 3 | | | | | KRTAP1-3 | 1.00 | 11432 | 3 | | | LGALS13 | 1.00 |
| 11337 | 3 | | | | | KRTAP13-1 | 1.00 | 11433 | 3 | | | LGALS14 | 1.00 |
| 11338 | 3 | | | | | KRTAP13-2 | 1.00 | 11434 | 3 | | | LGALS16 | 1.00 |
| 11339 | 3 | | | | | KRTAP13-3 | 1.00 | 11435 | 3 | | | LGALS17A | 1.00 |
| 11340 | 3 | | | | | KRTAP13-4 | 1.00 | 11436 | 3 | | | LGALS8-AS1 | 1.00 |
| 11341 | 3 | | | | | KRTAP15-1 | 1.00 | 11437 | 3 | | | LGALS9B | 1.00 |
| 11342 | 3 | | | | | KRTAP16-1 | 1.00 | 11438 | 3 | | | LGALS9C | 1.00 |
| 11343 | 3 | | | | | KRTAP19-1 | 1.00 | 11439 | 3 | | | LGI1 | 1.00 |
| 11344 | 3 | | | | | KRTAP19-2 | 1.00 | 11440 | 3 | | | LGI2 | 1.00 |
| 11345 | 3 | | | | | KRTAP19-3 | 1.00 | 11441 | 3 | | | LGSN | 1.00 |
| 11346 | 3 | | | | | KRTAP19-4 | 1.00 | 11442 | 3 | | | LHCGR | 1.00 |
| 11347 | 3 | | | | | KRTAP19-5 | 1.00 | 11443 | 3 | | | LHFPL1 | 1.00 |
| 11348 | 3 | | | | | KRTAP19-6 | 1.00 | 11444 | 3 | | | LHFPL3 | 1.00 |
| 11349 | 3 | | | | | KRTAP19-7 | 1.00 | 11445 | 3 | | | LHFPL4 | 1.00 |
| 11350 | 3 | | | | | KRTAP19-8 | 1.00 | 11446 | 3 | | | LHFPL5 | 1.00 |
| 11351 | 3 | | | | | KRTAP20-1 | 1.00 | 11447 | 3 | | | LHX1 | 1.00 |
| 11352 | 3 | | | | | KRTAP20-3 | 1.00 | 11448 | 3 | | | LHX3 | 1.00 |
| 11353 | 3 | | | | | KRTAP20-4 | 1.00 | 11449 | 3 | | | LHX4 | 1.00 |
| 11354 | 3 | | | | | KRTAP2-1 | 1.00 | 11450 | 3 | | | LHX5 | 1.00 |
| 11355 | 3 | | | | | KRTAP21-1 | 1.00 | 11451 | 3 | | | LHX8 | 1.00 |
| 11356 | 3 | | | | | KRTAP21-2 | 1.00 | 11452 | 3 | | | LHX9 | 1.00 |
| 11357 | 3 | | | | | KRTAP21-3 | 1.00 | 11453 | 3 | | | LILRA1 | 1.00 |
| 11358 | 3 | | | | | KRTAP22-1 | 1.00 | 11454 | 3 | | | LILRA3 | 1.00 |
| 11359 | 3 | | | | | KRTAP22-2 | 1.00 | 11455 | 3 | | | LILRA4 | 1.00 |
| 11360 | 3 | | | | | KRTAP23-1 | 1.00 | 11456 | 3 | | | LILRA5 | 1.00 |
| 11361 | 3 | | | | | KRTAP2-4 | 1.00 | 11457 | 3 | | | LILRB1 | 1.00 |
| 11362 | 3 | | | | | KRTAP24-1 | 1.00 | 11458 | 3 | | | LILRB4 | 1.00 |
| 11363 | 3 | | | | | KRTAP25-1 | 1.00 | 11459 | 3 | | | LILRP2 | 1.00 |
| 11364 | 3 | | | | | KRTAP26-1 | 1.00 | 11460 | 3 | | | LIM2 | 1.00 |
| 11365 | 3 | | | | | KRTAP27-1 | 1.00 | 11461 | 3 | | | LIMS3-LOC440895 | 1.00 |
| 11366 | 3 | | | | | KRTAP3-2 | 1.00 | 11462 | 3 | | | LIN28A | 1.00 |
| 11367 | 3 | | | | | KRTAP4-11 | 1.00 | 11463 | 3 | | | LIN28B | 1.00 |
| 11368 | 3 | | | | | KRTAP4-2 | 1.00 | 11464 | 3 | | | LIN7A | 1.00 |
| 11369 | 3 | | | | | KRTAP4-3 | 1.00 | 11465 | 3 | | | LINC00028 | 1.00 |
| 11370 | 3 | | | | | KRTAP4-4 | 1.00 | 11466 | 3 | | | LINC00029 | 1.00 |
| 11371 | 3 | | | | | KRTAP4-5 | 1.00 | 11467 | 3 | | | LINC00032 | 1.00 |
| 11372 | 3 | | | | | KRTAP5-1 | 1.00 | 11468 | 3 | | | LINC00051 | 1.00 |
| 11373 | 3 | | | | | KRTAP5-10 | 1.00 | 11469 | 3 | | | LINC00052 | 1.00 |
| 11374 | 3 | | | | | KRTAP5-11 | 1.00 | 11470 | 3 | | | LINC00102 | 1.00 |
| 11375 | 3 | | | | | KRTAP5-2 | 1.00 | 11471 | 3 | | | LINC00111 | 1.00 |
| 11376 | 3 | | | | | KRTAP5-3 | 1.00 | 11472 | 3 | | | LINC00112 | 1.00 |
| 11377 | 3 | | | | | KRTAP5-4 | 1.00 | 11473 | 3 | | | LINC00113 | 1.00 |
| 11378 | 3 | | | | | KRTAP5-5 | 1.00 | 11474 | 3 | | | LINC00114 | 1.00 |
| 11379 | 3 | | | | | KRTAP5-6 | 1.00 | 11475 | 3 | | | LINC00158 | 1.00 |
| 11380 | 3 | | | | | KRTAP5-7 | 1.00 | 11476 | 3 | | | LINC00159 | 1.00 |
| 11381 | 3 | | | | | KRTAP5-8 | 1.00 | 11477 | 3 | | | LINC00160 | 1.00 |
| 11382 | 3 | | | | | KRTAP5-9 | 1.00 | 11478 | 3 | | | LINC00161 | 1.00 |
| 11383 | 3 | | | | | KRTAP6-1 | 1.00 | 11479 | 3 | | | LINC00163 | 1.00 |
| 11384 | 3 | | | | | KRTAP6-2 | 1.00 | 11480 | 3 | | | LINC00167 | 1.00 |
| 11385 | 3 | | | | | KRTAP6-3 | 1.00 | 11481 | 3 | | | LINC00184 | 1.00 |
| 11386 | 3 | | | | | KRTAP7-1 | 1.00 | 11482 | 3 | | | LINC00189 | 1.00 |
| 11387 | 3 | | | | | KRTAP8-1 | 1.00 | 11483 | 3 | | | LINC00200 | 1.00 |
| 11388 | 3 | | | | | KRTAP9-1 | 1.00 | 11484 | 3 | | | LINC00202 | 1.00 |
| 11389 | 3 | | | | | KRTAP9-3 | 1.00 | 11485 | 3 | | | LINC00207 | 1.00 |
| 11390 | 3 | | | | | KRTAP9-8 | 1.00 | 11486 | 3 | | | LINC00208 | 1.00 |
| 11391 | 3 | | | | | KRTAP9-9 | 1.00 | 11487 | 3 | | | LINC00221 | 1.00 |
| 11392 | 3 | | | | | KSR2 | 1.00 | 11488 | 3 | | | LINC00222 | 1.00 |
| 11393 | 3 | | | | | KYNU | 1.00 | 11489 | 3 | | | LINC00226 | 1.00 |
| 11394 | 3 | | | | | L1TD1 | 1.00 | 11490 | 3 | | | LINC00229 | 1.00 |
| 11395 | 3 | | | | | LACE1 | 1.00 | 11491 | 3 | | | LINC00230A | 1.00 |
| 11396 | 3 | | | | | LACRT | 1.00 | 11492 | 3 | | | LINC00230B | 1.00 |
| 11397 | 3 | | | | | LAIR2 | 1.00 | 11493 | 3 | | | LINC00235 | 1.00 |
| 11398 | 3 | | | | | LALBA | 1.00 | 11494 | 3 | | | LINC00238 | 1.00 |
| 11399 | 3 | | | | | LAMA1 | 1.00 | 11495 | 3 | | | LINC00239 | 1.00 |
| 11400 | 3 | | | | | LANCL3 | 1.00 | 11496 | 3 | | | LINC00240 | 1.00 |
| 11401 | 3 | | | | | LAX1 | 1.00 | 11497 | 3 | | | LINC00242 | 1.00 |
| 11402 | 3 | | | | | LBP | 1.00 | 11498 | 3 | | | LINC00244 | 1.00 |
| 11403 | 3 | | | | | LBX1 | 1.00 | 11499 | 3 | | | LINC00246A | 1.00 |
| 11404 | 3 | | | | | LBX2 | 1.00 | 11500 | 3 | | | LINC00251 | 1.00 |
| 11405 | 3 | | | | | LCA5L | 1.00 | 11501 | 3 | | | LINC00254 | 1.00 |
| 11406 | 3 | | | | | LCE3B | 1.00 | 11502 | 3 | | | LINC00256A | 1.00 |
| 11407 | 3 | | | | | LCE3C | 1.00 | 11503 | 3 | | | LINC00256B | 1.00 |
| 11408 | 3 | | | | | LCN1 | 1.00 | 11504 | 3 | | | LINC00261 | 1.00 |
| 11409 | 3 | | | | | LCN12 | 1.00 | 11505 | 3 | | | LINC00264 | 1.00 |
| 11410 | 3 | | | | | LCN15 | 1.00 | 11506 | 3 | | | LINC00266-1 | 1.00 |
| 11411 | 3 | | | | | LCN6 | 1.00 | 11507 | 3 | | | LINC00271 | 1.00 |
| 11412 | 3 | | | | | LCN8 | 1.00 | 11508 | 3 | | | LINC00272 | 1.00 |
| 11413 | 3 | | | | | LCN9 | 1.00 | 11509 | 3 | | | LINC00273 | 1.00 |
| 11414 | 3 | | | | | LCNL1 | 1.00 | 11510 | 3 | | | LINC00277 | 1.00 |
| 11415 | 3 | | | | | LCT | 1.00 | 11511 | 3 | | | LINC00281 | 1.00 |
| 11416 | 3 | | | | | LCTL | 1.00 | 11512 | 3 | | | LINC00282 | 1.00 |
| 11417 | 3 | | | | | LDHAL6A | 1.00 | 11513 | 3 | | | LINC00284 | 1.00 |
| 11418 | 3 | | | | | LDHAL6B | 1.00 | 11514 | 3 | | | LINC00290 | 1.00 |
| 11419 | 3 | | | | | LDHC | 1.00 | 11515 | 3 | | | LINC00293 | 1.00 |
| 11420 | 3 | | | | | LDLRAD1 | 1.00 | 11516 | 3 | | | LINC00299 | 1.00 |

Fig. 39 - 61

| | | | | | | | | | | | | | |
|---|---|---|---|---|---|---|---|---|---|---|---|---|---|
| 11517 | 3 | | | | LINC00301 | 1.00 | 11613 | 3 | | | | LOC100128787 | 1.00 |
| 11518 | 3 | | | | LINC00303 | 1.00 | 11614 | 3 | | | | LOC100128788 | 1.00 |
| 11519 | 3 | | | | LINC00304 | 1.00 | 11615 | 3 | | | | LOC100128811 | 1.00 |
| 11520 | 3 | | | | LINC00305 | 1.00 | 11616 | 3 | | | | LOC100128946 | 1.00 |
| 11521 | 3 | | | | LINC00307 | 1.00 | 11617 | 3 | | | | LOC100128993 | 1.00 |
| 11522 | 3 | | | | LINC00308 | 1.00 | 11618 | 3 | | | | LOC100129027 | 1.00 |
| 11523 | 3 | | | | LINC00309 | 1.00 | 11619 | 3 | | | | LOC100129055 | 1.00 |
| 11524 | 3 | | | | LINC00311 | 1.00 | 11620 | 3 | | | | LOC100129083 | 1.00 |
| 11525 | 3 | | | | LINC00313 | 1.00 | 11621 | 3 | | | | LOC100129175 | 1.00 |
| 11526 | 3 | | | | LINC00314 | 1.00 | 11622 | 3 | | | | LOC100129213 | 1.00 |
| 11527 | 3 | | | | LINC00315 | 1.00 | 11623 | 3 | | | | LOC100129216 | 1.00 |
| 11528 | 3 | | | | LINC00317 | 1.00 | 11624 | 3 | | | | LOC100129316 | 1.00 |
| 11529 | 3 | | | | LINC00320 | 1.00 | 11625 | 3 | | | | LOC100129345 | 1.00 |
| 11530 | 3 | | | | LINC00323 | 1.00 | 11626 | 3 | | | | LOC100129407 | 1.00 |
| 11531 | 3 | | | | LINC00326 | 1.00 | 11627 | 3 | | | | LOC100129427 | 1.00 |
| 11532 | 3 | | | | LINC00330 | 1.00 | 11628 | 3 | | | | LOC100129515 | 1.00 |
| 11533 | 3 | | | | LINC00336 | 1.00 | 11629 | 3 | | | | LOC100129520 | 1.00 |
| 11534 | 3 | | | | LINC00340 | 1.00 | 11630 | 3 | | | | LOC100129617 | 1.00 |
| 11535 | 3 | | | | LINC00346 | 1.00 | 11631 | 3 | | | | LOC100129620 | 1.00 |
| 11536 | 3 | | | | LINC00347 | 1.00 | 11632 | 3 | | | | LOC100129636 | 1.00 |
| 11537 | 3 | | | | LINC00410 | 1.00 | 11633 | 3 | | | | LOC100129662 | 1.00 |
| 11538 | 3 | | | | LINC00421 | 1.00 | 11634 | 3 | | | | LOC100129718 | 1.00 |
| 11539 | 3 | | | | LINC00426 | 1.00 | 11635 | 3 | | | | LOC100129726 | 1.00 |
| 11540 | 3 | | | | LINC00442 | 1.00 | 11636 | 3 | | | | LOC100129845 | 1.00 |
| 11541 | 3 | | | | LINC00460 | 1.00 | 11637 | 3 | | | | LOC100129858 | 1.00 |
| 11542 | 3 | | | | LINC00461 | 1.00 | 11638 | 3 | | | | LOC100129924 | 1.00 |
| 11543 | 3 | | | | LINC00466 | 1.00 | 11639 | 3 | | | | LOC100129931 | 1.00 |
| 11544 | 3 | | | | LINC00469 | 1.00 | 11640 | 3 | | | | LOC100129935 | 1.00 |
| 11545 | 3 | | | | LINC00470 | 1.00 | 11641 | 3 | | | | LOC100129961 | 1.00 |
| 11546 | 3 | | | | LINC00471 | 1.00 | 11642 | 3 | | | | LOC100130000 | 1.00 |
| 11547 | 3 | | | | LINC00472 | 1.00 | 11643 | 3 | | | | LOC100130155 | 1.00 |
| 11548 | 3 | | | | LINC00473 | 1.00 | 11644 | 3 | | | | LOC100130197 | 1.00 |
| 11549 | 3 | | | | LINC00474 | 1.00 | 11645 | 3 | | | | LOC100130231 | 1.00 |
| 11550 | 3 | | | | LINC00475 | 1.00 | 11646 | 3 | | | | LOC100130238 | 1.00 |
| 11551 | 3 | | | | LINC00477 | 1.00 | 11647 | 3 | | | | LOC100130264 | 1.00 |
| 11552 | 3 | | | | LINC00482 | 1.00 | 11648 | 3 | | | | LOC100130298 | 1.00 |
| 11553 | 3 | | | | LINC00483 | 1.00 | 11649 | 3 | | | | LOC100130301 | 1.00 |
| 11554 | 3 | | | | LINC00485 | 1.00 | 11650 | 3 | | | | LOC100130348 | 1.00 |
| 11555 | 3 | | | | LINC00486 | 1.00 | 11651 | 3 | | | | LOC100130357 | 1.00 |
| 11556 | 3 | | | | LINC00487 | 1.00 | 11652 | 3 | | | | LOC100130417 | 1.00 |
| 11557 | 3 | | | | LINC00488 | 1.00 | 11653 | 3 | | | | LOC100130451 | 1.00 |
| 11558 | 3 | | | | LINC00494 | 1.00 | 11654 | 3 | | | | LOC100130452 | 1.00 |
| 11559 | 3 | | | | LINC00511 | 1.00 | 11655 | 3 | | | | LOC100130480 | 1.00 |
| 11560 | 3 | | | | LINC00514 | 1.00 | 11656 | 3 | | | | LOC100130557 | 1.00 |
| 11561 | 3 | | | | LINC00515 | 1.00 | 11657 | 3 | | | | LOC100130673 | 1.00 |
| 11562 | 3 | | | | LINC00518 | 1.00 | 11658 | 3 | | | | LOC100130700 | 1.00 |
| 11563 | 3 | | | | LINC00520 | 1.00 | 11659 | 3 | | | | LOC100130849 | 1.00 |
| 11564 | 3 | | | | LINC00521 | 1.00 | 11660 | 3 | | | | LOC100130872 | 1.00 |
| 11565 | 3 | | | | LINC00523 | 1.00 | 11661 | 3 | | | | LOC100130880 | 1.00 |
| 11566 | 3 | | | | LINC00525 | 1.00 | 11662 | 3 | | | | LOC100130890 | 1.00 |
| 11567 | 3 | | | | LINC00535 | 1.00 | 11663 | 3 | | | | LOC100130894 | 1.00 |
| 11568 | 3 | | | | LINC00536 | 1.00 | 11664 | 3 | | | | LOC100130954 | 1.00 |
| 11569 | 3 | | | | LINC00538 | 1.00 | 11665 | 3 | | | | LOC100130964 | 1.00 |
| 11570 | 3 | | | | LINC00547 | 1.00 | 11666 | 3 | | | | LOC100130992 | 1.00 |
| 11571 | 3 | | | | LINC00548 | 1.00 | 11667 | 3 | | | | LOC100131047 | 1.00 |
| 11572 | 3 | | | | LINC00550 | 1.00 | 11668 | 3 | | | | LOC100131060 | 1.00 |
| 11573 | 3 | | | | LINC00552 | 1.00 | 11669 | 3 | | | | LOC100131138 | 1.00 |
| 11574 | 3 | | | | LINC00574 | 1.00 | 11670 | 3 | | | | LOC100131176 | 1.00 |
| 11575 | 3 | | | | LINC00575 | 1.00 | 11671 | 3 | | | | LOC100131208 | 1.00 |
| 11576 | 3 | | | | LINGO3 | 1.00 | 11672 | 3 | | | | LOC100131234 | 1.00 |
| 11577 | 3 | | | | LINGO4 | 1.00 | 11673 | 3 | | | | LOC100131257 | 1.00 |
| 11578 | 3 | | | | LIPF | 1.00 | 11674 | 3 | | | | LOC100131320 | 1.00 |
| 11579 | 3 | | | | LIPG | 1.00 | 11675 | 3 | | | | LOC100131347 | 1.00 |
| 11580 | 3 | | | | LIPI | 1.00 | 11676 | 3 | | | | LOC100131366 | 1.00 |
| 11581 | 3 | | | | LIPJ | 1.00 | 11677 | 3 | | | | LOC100131496 | 1.00 |
| 11582 | 3 | | | | LIX1 | 1.00 | 11678 | 3 | | | | LOC100131551 | 1.00 |
| 11583 | 3 | | | | LMAN1L | 1.00 | 11679 | 3 | | | | LOC100131626 | 1.00 |
| 11584 | 3 | | | | LMBRD2 | 1.00 | 11680 | 3 | | | | LOC100131635 | 1.00 |
| 11585 | 3 | | | | LMOD2 | 1.00 | 11681 | 3 | | | | LOC100131655 | 1.00 |
| 11586 | 3 | | | | LMOD3 | 1.00 | 11682 | 3 | | | | LOC100131733 | 1.00 |
| 11587 | 3 | | | | LMX1A | 1.00 | 11683 | 3 | | | | LOC100132077 | 1.00 |
| 11588 | 3 | | | | LNP1 | 1.00 | 11684 | 3 | | | | LOC100132078 | 1.00 |
| 11589 | 3 | | | | LOC100093698 | 1.00 | 11685 | 3 | | | | LOC100132146 | 1.00 |
| 11590 | 3 | | | | LOC100101266 | 1.00 | 11686 | 3 | | | | LOC100132354 | 1.00 |
| 11591 | 3 | | | | LOC100124692 | 1.00 | 11687 | 3 | | | | LOC100132396 | 1.00 |
| 11592 | 3 | | | | LOC100126784 | 1.00 | 11688 | 3 | | | | LOC100132526 | 1.00 |
| 11593 | 3 | | | | LOC100128023 | 1.00 | 11689 | 3 | | | | LOC100132735 | 1.00 |
| 11594 | 3 | | | | LOC100128054 | 1.00 | 11690 | 3 | | | | LOC100132774 | 1.00 |
| 11595 | 3 | | | | LOC100128076 | 1.00 | 11691 | 3 | | | | LOC100132781 | 1.00 |
| 11596 | 3 | | | | LOC100128098 | 1.00 | 11692 | 3 | | | | LOC100132832 | 1.00 |
| 11597 | 3 | | | | LOC100128126 | 1.00 | 11693 | 3 | | | | LOC100132987 | 1.00 |
| 11598 | 3 | | | | LOC100128176 | 1.00 | 11694 | 3 | | | | LOC100133050 | 1.00 |
| 11599 | 3 | | | | LOC100128191 | 1.00 | 11695 | 3 | | | | LOC100133123 | 1.00 |
| 11600 | 3 | | | | LOC100128264 | 1.00 | 11696 | 3 | | | | LOC100133267 | 1.00 |
| 11601 | 3 | | | | LOC100128292 | 1.00 | 11697 | 3 | | | | LOC100133286 | 1.00 |
| 11602 | 3 | | | | LOC100128496 | 1.00 | 11698 | 3 | | | | LOC100133308 | 1.00 |
| 11603 | 3 | | | | LOC100128505 | 1.00 | 11699 | 3 | | | | LOC100133315 | 1.00 |
| 11604 | 3 | | | | LOC100128554 | 1.00 | 11700 | 3 | | | | LOC100133461 | 1.00 |
| 11605 | 3 | | | | LOC100128568 | 1.00 | 11701 | 3 | | | | LOC100133612 | 1.00 |
| 11606 | 3 | | | | LOC100128590 | 1.00 | 11702 | 3 | | | | LOC100133920 | 1.00 |
| 11607 | 3 | | | | LOC100128593 | 1.00 | 11703 | 3 | | | | LOC100133957 | 1.00 |
| 11608 | 3 | | | | LOC100128640 | 1.00 | 11704 | 3 | | | | LOC100133985 | 1.00 |
| 11609 | 3 | | | | LOC100128675 | 1.00 | 11705 | 3 | | | | LOC100134015 | 1.00 |
| 11610 | 3 | | | | LOC100128682 | 1.00 | 11706 | 3 | | | | LOC100134368 | 1.00 |
| 11611 | 3 | | | | LOC100128714 | 1.00 | 11707 | 3 | | | | LOC100134868 | 1.00 |
| 11612 | 3 | | | | LOC100128750 | 1.00 | 11708 | 3 | | | | LOC100144595 | 1.00 |

Fig. 39 - 62

| | | | | | | | | | | | | | | |
|---|---|---|---|---|---|---|---|---|---|---|---|---|---|---|
| 11709 | 3 | | | | | LOC100144597 | 1.00 | 11805 | 3 | | | | LOC100505835 | 1.00 |
| 11710 | 3 | | | | | LOC100144602 | 1.00 | 11806 | 3 | | | | LOC100505841 | 1.00 |
| 11711 | 3 | | | | | LOC100169752 | 1.00 | 11807 | 3 | | | | LOC100505875 | 1.00 |
| 11712 | 3 | | | | | LOC100188947 | 1.00 | 11808 | 3 | | | | LOC100505912 | 1.00 |
| 11713 | 3 | | | | | LOC100189589 | 1.00 | 11809 | 3 | | | | LOC100505918 | 1.00 |
| 11714 | 3 | | | | | LOC100190940 | 1.00 | 11810 | 3 | | | | LOC100505933 | 1.00 |
| 11715 | 3 | | | | | LOC100192378 | 1.00 | 11811 | 3 | | | | LOC100505964 | 1.00 |
| 11716 | 3 | | | | | LOC100192426 | 1.00 | 11812 | 3 | | | | LOC100505967 | 1.00 |
| 11717 | 3 | | | | | LOC100216001 | 1.00 | 11813 | 3 | | | | LOC100505978 | 1.00 |
| 11718 | 3 | | | | | LOC100216479 | 1.00 | 11814 | 3 | | | | LOC100505989 | 1.00 |
| 11719 | 3 | | | | | LOC100233209 | 1.00 | 11815 | 3 | | | | LOC100506012 | 1.00 |
| 11720 | 3 | | | | | LOC100240734 | 1.00 | 11816 | 3 | | | | LOC100506023 | 1.00 |
| 11721 | 3 | | | | | LOC100268168 | 1.00 | 11817 | 3 | | | | LOC100506025 | 1.00 |
| 11722 | 3 | | | | | LOC100270679 | 1.00 | 11818 | 3 | | | | LOC100506035 | 1.00 |
| 11723 | 3 | | | | | LOC100271702 | 1.00 | 11819 | 3 | | | | LOC100506050 | 1.00 |
| 11724 | 3 | | | | | LOC100271832 | 1.00 | 11820 | 3 | | | | LOC100506071 | 1.00 |
| 11725 | 3 | | | | | LOC100271836 | 1.00 | 11821 | 3 | | | | LOC100506083 | 1.00 |
| 11726 | 3 | | | | | LOC100272217 | 1.00 | 11822 | 3 | | | | LOC100506085 | 1.00 |
| 11727 | 3 | | | | | LOC100286844 | 1.00 | 11823 | 3 | | | | LOC100506122 | 1.00 |
| 11728 | 3 | | | | | LOC100286922 | 1.00 | 11824 | 3 | | | | LOC100506134 | 1.00 |
| 11729 | 3 | | | | | LOC100286938 | 1.00 | 11825 | 3 | | | | LOC100506136 | 1.00 |
| 11730 | 3 | | | | | LOC100286979 | 1.00 | 11826 | 3 | | | | LOC100506172 | 1.00 |
| 11731 | 3 | | | | | LOC100287010 | 1.00 | 11827 | 3 | | | | LOC100506178 | 1.00 |
| 11732 | 3 | | | | | LOC100287036 | 1.00 | 11828 | 3 | | | | LOC100506195 | 1.00 |
| 11733 | 3 | | | | | LOC100287216 | 1.00 | 11829 | 3 | | | | LOC100506229 | 1.00 |
| 11734 | 3 | | | | | LOC100287225 | 1.00 | 11830 | 3 | | | | LOC100506241 | 1.00 |
| 11735 | 3 | | | | | LOC100287314 | 1.00 | 11831 | 3 | | | | LOC100506274 | 1.00 |
| 11736 | 3 | | | | | LOC100287482 | 1.00 | 11832 | 3 | | | | LOC100506321 | 1.00 |
| 11737 | 3 | | | | | LOC100287559 | 1.00 | 11833 | 3 | | | | LOC100506343 | 1.00 |
| 11738 | 3 | | | | | LOC100287632 | 1.00 | 11834 | 3 | | | | LOC100506368 | 1.00 |
| 11739 | 3 | | | | | LOC100287718 | 1.00 | 11835 | 3 | | | | LOC100506384 | 1.00 |
| 11740 | 3 | | | | | LOC100287765 | 1.00 | 11836 | 3 | | | | LOC100506385 | 1.00 |
| 11741 | 3 | | | | | LOC100287792 | 1.00 | 11837 | 3 | | | | LOC100506393 | 1.00 |
| 11742 | 3 | | | | | LOC100287814 | 1.00 | 11838 | 3 | | | | LOC100506409 | 1.00 |
| 11743 | 3 | | | | | LOC100287834 | 1.00 | 11839 | 3 | | | | LOC100506421 | 1.00 |
| 11744 | 3 | | | | | LOC100287846 | 1.00 | 11840 | 3 | | | | LOC100506422 | 1.00 |
| 11745 | 3 | | | | | LOC100287879 | 1.00 | 11841 | 3 | | | | LOC100506433 | 1.00 |
| 11746 | 3 | | | | | LOC100287944 | 1.00 | 11842 | 3 | | | | LOC100506451 | 1.00 |
| 11747 | 3 | | | | | LOC100288077 | 1.00 | 11843 | 3 | | | | LOC100506462 | 1.00 |
| 11748 | 3 | | | | | LOC100288079 | 1.00 | 11844 | 3 | | | | LOC100506474 | 1.00 |
| 11749 | 3 | | | | | LOC100288122 | 1.00 | 11845 | 3 | | | | LOC100506497 | 1.00 |
| 11750 | 3 | | | | | LOC100288181 | 1.00 | 11846 | 3 | | | | LOC100506540 | 1.00 |
| 11751 | 3 | | | | | LOC100288255 | 1.00 | 11847 | 3 | | | | LOC100506585 | 1.00 |
| 11752 | 3 | | | | | LOC100288346 | 1.00 | 11848 | 3 | | | | LOC100506650 | 1.00 |
| 11753 | 3 | | | | | LOC100288428 | 1.00 | 11849 | 3 | | | | LOC100506655 | 1.00 |
| 11754 | 3 | | | | | LOC100288524 | 1.00 | 11850 | 3 | | | | LOC100506660 | 1.00 |
| 11755 | 3 | | | | | LOC100288570 | 1.00 | 11851 | 3 | | | | LOC100506688 | 1.00 |
| 11756 | 3 | | | | | LOC100288814 | 1.00 | 11852 | 3 | | | | LOC100506733 | 1.00 |
| 11757 | 3 | | | | | LOC100288846 | 1.00 | 11853 | 3 | | | | LOC100506757 | 1.00 |
| 11758 | 3 | | | | | LOC100288974 | 1.00 | 11854 | 3 | | | | LOC100506776 | 1.00 |
| 11759 | 3 | | | | | LOC100289092 | 1.00 | 11855 | 3 | | | | LOC100506795 | 1.00 |
| 11760 | 3 | | | | | LOC100289178 | 1.00 | 11856 | 3 | | | | LOC100506801 | 1.00 |
| 11761 | 3 | | | | | LOC100289211 | 1.00 | 11857 | 3 | | | | LOC100506804 | 1.00 |
| 11762 | 3 | | | | | LOC100289495 | 1.00 | 11858 | 3 | | | | LOC100506810 | 1.00 |
| 11763 | 3 | | | | | LOC100289561 | 1.00 | 11859 | 3 | | | | LOC100506835 | 1.00 |
| 11764 | 3 | | | | | LOC100289650 | 1.00 | 11860 | 3 | | | | LOC100506888 | 1.00 |
| 11765 | 3 | | | | | LOC100289656 | 1.00 | 11861 | 3 | | | | LOC100506895 | 1.00 |
| 11766 | 3 | | | | | LOC100289673 | 1.00 | 11862 | 3 | | | | LOC100506994 | 1.00 |
| 11767 | 3 | | | | | LOC100293534 | 1.00 | 11863 | 3 | | | | LOC100507003 | 1.00 |
| 11768 | 3 | | | | | LOC100302401 | 1.00 | 11864 | 3 | | | | LOC100507032 | 1.00 |
| 11769 | 3 | | | | | LOC100302640 | 1.00 | 11865 | 3 | | | | LOC100507043 | 1.00 |
| 11770 | 3 | | | | | LOC100302650 | 1.00 | 11866 | 3 | | | | LOC100507050 | 1.00 |
| 11771 | 3 | | | | | LOC100303749 | 1.00 | 11867 | 3 | | | | LOC100507053 | 1.00 |
| 11772 | 3 | | | | | LOC100306975 | 1.00 | 11868 | 3 | | | | LOC100507055 | 1.00 |
| 11773 | 3 | | | | | LOC100329135 | 1.00 | 11869 | 3 | | | | LOC100507062 | 1.00 |
| 11774 | 3 | | | | | LOC100379224 | 1.00 | 11870 | 3 | | | | LOC100507066 | 1.00 |
| 11775 | 3 | | | | | LOC100422737 | 1.00 | 11871 | 3 | | | | LOC100507086 | 1.00 |
| 11776 | 3 | | | | | LOC100498859 | 1.00 | 11872 | 3 | | | | LOC100507091 | 1.00 |
| 11777 | 3 | | | | | LOC100499183 | 1.00 | 11873 | 3 | | | | LOC100507096 | 1.00 |
| 11778 | 3 | | | | | LOC100499194 | 1.00 | 11874 | 3 | | | | LOC100507127 | 1.00 |
| 11779 | 3 | | | | | LOC100499227 | 1.00 | 11875 | 3 | | | | LOC100507140 | 1.00 |
| 11780 | 3 | | | | | LOC100499484 | 1.00 | 11876 | 3 | | | | LOC100507156 | 1.00 |
| 11781 | 3 | | | | | LOC100500773 | 1.00 | 11877 | 3 | | | | LOC100507173 | 1.00 |
| 11782 | 3 | | | | | LOC100500938 | 1.00 | 11878 | 3 | | | | LOC100507178 | 1.00 |
| 11783 | 3 | | | | | LOC100505474 | 1.00 | 11879 | 3 | | | | LOC100507194 | 1.00 |
| 11784 | 3 | | | | | LOC100505478 | 1.00 | 11880 | 3 | | | | LOC100507203 | 1.00 |
| 11785 | 3 | | | | | LOC100505536 | 1.00 | 11881 | 3 | | | | LOC100507205 | 1.00 |
| 11786 | 3 | | | | | LOC100505540 | 1.00 | 11882 | 3 | | | | LOC100507206 | 1.00 |
| 11787 | 3 | | | | | LOC100505545 | 1.00 | 11883 | 3 | | | | LOC100507218 | 1.00 |
| 11788 | 3 | | | | | LOC100505583 | 1.00 | 11884 | 3 | | | | LOC100507240 | 1.00 |
| 11789 | 3 | | | | | LOC100505619 | 1.00 | 11885 | 3 | | | | LOC100507244 | 1.00 |
| 11790 | 3 | | | | | LOC100505622 | 1.00 | 11886 | 3 | | | | LOC100507250 | 1.00 |
| 11791 | 3 | | | | | LOC100505658 | 1.00 | 11887 | 3 | | | | LOC100507266 | 1.00 |
| 11792 | 3 | | | | | LOC100505659 | 1.00 | 11888 | 3 | | | | LOC100507299 | 1.00 |
| 11793 | 3 | | | | | LOC100505676 | 1.00 | 11889 | 3 | | | | LOC100507300 | 1.00 |
| 11794 | 3 | | | | | LOC100505678 | 1.00 | 11890 | 3 | | | | LOC100507334 | 1.00 |
| 11795 | 3 | | | | | LOC100505679 | 1.00 | 11891 | 3 | | | | LOC100507341 | 1.00 |
| 11796 | 3 | | | | | LOC100505715 | 1.00 | 11892 | 3 | | | | LOC100507346 | 1.00 |
| 11797 | 3 | | | | | LOC100505716 | 1.00 | 11893 | 3 | | | | LOC100507362 | 1.00 |
| 11798 | 3 | | | | | LOC100505718 | 1.00 | 11894 | 3 | | | | LOC100507377 | 1.00 |
| 11799 | 3 | | | | | LOC100505768 | 1.00 | 11895 | 3 | | | | LOC100507387 | 1.00 |
| 11800 | 3 | | | | | LOC100505776 | 1.00 | 11896 | 3 | | | | LOC100507389 | 1.00 |
| 11801 | 3 | | | | | LOC100505782 | 1.00 | 11897 | 3 | | | | LOC100507391 | 1.00 |
| 11802 | 3 | | | | | LOC100505795 | 1.00 | 11898 | 3 | | | | LOC100507404 | 1.00 |
| 11803 | 3 | | | | | LOC100505817 | 1.00 | 11899 | 3 | | | | LOC100507410 | 1.00 |
| 11804 | 3 | | | | | LOC100505826 | 1.00 | 11900 | 3 | | | | LOC100507421 | 1.00 |

Fig. 39 - 63

| | | | | | | | | | | | | | | |
|---|---|---|---|---|---|---|---|---|---|---|---|---|---|---|
| 11901 | 3 | | | | | LOC100507423 | 1.00 | 11997 | 3 | | | | LOC201477 | 1.00 |
| 11902 | 3 | | | | | LOC100507443 | 1.00 | 11998 | 3 | | | | LOC201617 | 1.00 |
| 11903 | 3 | | | | | LOC100507462 | 1.00 | 11999 | 3 | | | | LOC201651 | 1.00 |
| 11904 | 3 | | | | | LOC100507466 | 1.00 | 12000 | 3 | | | | LOC219731 | 1.00 |
| 11905 | 3 | | | | | LOC100507470 | 1.00 | 12001 | 3 | | | | LOC220906 | 1.00 |
| 11906 | 3 | | | | | LOC100507472 | 1.00 | 12002 | 3 | | | | LOC221122 | 1.00 |
| 11907 | 3 | | | | | LOC100507489 | 1.00 | 12003 | 3 | | | | LOC221442 | 1.00 |
| 11908 | 3 | | | | | LOC100507537 | 1.00 | 12004 | 3 | | | | LOC253044 | 1.00 |
| 11909 | 3 | | | | | LOC100507582 | 1.00 | 12005 | 3 | | | | LOC253573 | 1.00 |
| 11910 | 3 | | | | | LOC100507584 | 1.00 | 12006 | 3 | | | | LOC253962 | 1.00 |
| 11911 | 3 | | | | | LOC100507588 | 1.00 | 12007 | 3 | | | | LOC254099 | 1.00 |
| 11912 | 3 | | | | | LOC100507589 | 1.00 | 12008 | 3 | | | | LOC254312 | 1.00 |
| 11913 | 3 | | | | | LOC100507600 | 1.00 | 12009 | 3 | | | | LOC254559 | 1.00 |
| 11914 | 3 | | | | | LOC100507605 | 1.00 | 12010 | 3 | | | | LOC254896 | 1.00 |
| 11915 | 3 | | | | | LOC100507629 | 1.00 | 12011 | 3 | | | | LOC255025 | 1.00 |
| 11916 | 3 | | | | | LOC100507634 | 1.00 | 12012 | 3 | | | | LOC255411 | 1.00 |
| 11917 | 3 | | | | | LOC100507651 | 1.00 | 12013 | 3 | | | | LOC255654 | 1.00 |
| 11918 | 3 | | | | | LOC100509575 | 1.00 | 12014 | 3 | | | | LOC256021 | 1.00 |
| 11919 | 3 | | | | | LOC100526771 | 1.00 | 12015 | 3 | | | | LOC256880 | 1.00 |
| 11920 | 3 | | | | | LOC100616530 | 1.00 | 12016 | 3 | | | | LOC257358 | 1.00 |
| 11921 | 3 | | | | | LOC100628307 | 1.00 | 12017 | 3 | | | | LOC282980 | 1.00 |
| 11922 | 3 | | | | | LOC100631378 | 1.00 | 12018 | 3 | | | | LOC283033 | 1.00 |
| 11923 | 3 | | | | | LOC100652730 | 1.00 | 12019 | 3 | | | | LOC283038 | 1.00 |
| 11924 | 3 | | | | | LOC100652759 | 1.00 | 12020 | 3 | | | | LOC283089 | 1.00 |
| 11925 | 3 | | | | | LOC100652770 | 1.00 | 12021 | 3 | | | | LOC283116 | 1.00 |
| 11926 | 3 | | | | | LOC100652791 | 1.00 | 12022 | 3 | | | | LOC283177 | 1.00 |
| 11927 | 3 | | | | | LOC100652846 | 1.00 | 12023 | 3 | | | | LOC283194 | 1.00 |
| 11928 | 3 | | | | | LOC100652909 | 1.00 | 12024 | 3 | | | | LOC283214 | 1.00 |
| 11929 | 3 | | | | | LOC100652999 | 1.00 | 12025 | 3 | | | | LOC283299 | 1.00 |
| 11930 | 3 | | | | | LOC100653515 | 1.00 | 12026 | 3 | | | | LOC283332 | 1.00 |
| 11931 | 3 | | | | | LOC116437 | 1.00 | 12027 | 3 | | | | LOC283403 | 1.00 |
| 11932 | 3 | | | | | LOC120824 | 1.00 | 12028 | 3 | | | | LOC283440 | 1.00 |
| 11933 | 3 | | | | | LOC126536 | 1.00 | 12029 | 3 | | | | LOC283547 | 1.00 |
| 11934 | 3 | | | | | LOC127841 | 1.00 | 12030 | 3 | | | | LOC283585 | 1.00 |
| 11935 | 3 | | | | | LOC143188 | 1.00 | 12031 | 3 | | | | LOC283587 | 1.00 |
| 11936 | 3 | | | | | LOC144481 | 1.00 | 12032 | 3 | | | | LOC283683 | 1.00 |
| 11937 | 3 | | | | | LOC144486 | 1.00 | 12033 | 3 | | | | LOC283688 | 1.00 |
| 11938 | 3 | | | | | LOC144742 | 1.00 | 12034 | 3 | | | | LOC283693 | 1.00 |
| 11939 | 3 | | | | | LOC145216 | 1.00 | 12035 | 3 | | | | LOC283710 | 1.00 |
| 11940 | 3 | | | | | LOC145474 | 1.00 | 12036 | 3 | | | | LOC283731 | 1.00 |
| 11941 | 3 | | | | | LOC145663 | 1.00 | 12037 | 3 | | | | LOC283738 | 1.00 |
| 11942 | 3 | | | | | LOC145820 | 1.00 | 12038 | 3 | | | | LOC283761 | 1.00 |
| 11943 | 3 | | | | | LOC145837 | 1.00 | 12039 | 3 | | | | LOC283856 | 1.00 |
| 11944 | 3 | | | | | LOC145845 | 1.00 | 12040 | 3 | | | | LOC283867 | 1.00 |
| 11945 | 3 | | | | | LOC146336 | 1.00 | 12041 | 3 | | | | LOC283888 | 1.00 |
| 11946 | 3 | | | | | LOC146481 | 1.00 | 12042 | 3 | | | | LOC283914 | 1.00 |
| 11947 | 3 | | | | | LOC146513 | 1.00 | 12043 | 3 | | | | LOC284080 | 1.00 |
| 11948 | 3 | | | | | LOC147093 | 1.00 | 12044 | 3 | | | | LOC284100 | 1.00 |
| 11949 | 3 | | | | | LOC147646 | 1.00 | 12045 | 3 | | | | LOC284215 | 1.00 |
| 11950 | 3 | | | | | LOC147670 | 1.00 | 12046 | 3 | | | | LOC284260 | 1.00 |
| 11951 | 3 | | | | | LOC148145 | 1.00 | 12047 | 3 | | | | LOC284294 | 1.00 |
| 11952 | 3 | | | | | LOC148696 | 1.00 | 12048 | 3 | | | | LOC284344 | 1.00 |
| 11953 | 3 | | | | | LOC148709 | 1.00 | 12049 | 3 | | | | LOC284379 | 1.00 |
| 11954 | 3 | | | | | LOC148824 | 1.00 | 12050 | 3 | | | | LOC284395 | 1.00 |
| 11955 | 3 | | | | | LOC149086 | 1.00 | 12051 | 3 | | | | LOC284551 | 1.00 |
| 11956 | 3 | | | | | LOC149373 | 1.00 | 12052 | 3 | | | | LOC284576 | 1.00 |
| 11957 | 3 | | | | | LOC149773 | 1.00 | 12053 | 3 | | | | LOC284632 | 1.00 |
| 11958 | 3 | | | | | LOC149837 | 1.00 | 12054 | 3 | | | | LOC284648 | 1.00 |
| 11959 | 3 | | | | | LOC149950 | 1.00 | 12055 | 3 | | | | LOC284661 | 1.00 |
| 11960 | 3 | | | | | LOC150185 | 1.00 | 12056 | 3 | | | | LOC284688 | 1.00 |
| 11961 | 3 | | | | | LOC150197 | 1.00 | 12057 | 3 | | | | LOC284751 | 1.00 |
| 11962 | 3 | | | | | LOC150381 | 1.00 | 12058 | 3 | | | | LOC284757 | 1.00 |
| 11963 | 3 | | | | | LOC150527 | 1.00 | 12059 | 3 | | | | LOC284788 | 1.00 |
| 11964 | 3 | | | | | LOC150568 | 1.00 | 12060 | 3 | | | | LOC284798 | 1.00 |
| 11965 | 3 | | | | | LOC150622 | 1.00 | 12061 | 3 | | | | LOC284801 | 1.00 |
| 11966 | 3 | | | | | LOC150935 | 1.00 | 12062 | 3 | | | | LOC284865 | 1.00 |
| 11967 | 3 | | | | | LOC151171 | 1.00 | 12063 | 3 | | | | LOC284933 | 1.00 |
| 11968 | 3 | | | | | LOC151174 | 1.00 | 12064 | 3 | | | | LOC284950 | 1.00 |
| 11969 | 3 | | | | | LOC151300 | 1.00 | 12065 | 3 | | | | LOC284998 | 1.00 |
| 11970 | 3 | | | | | LOC151475 | 1.00 | 12066 | 3 | | | | LOC285000 | 1.00 |
| 11971 | 3 | | | | | LOC151484 | 1.00 | 12067 | 3 | | | | LOC285103 | 1.00 |
| 11972 | 3 | | | | | LOC151658 | 1.00 | 12068 | 3 | | | | LOC285205 | 1.00 |
| 11973 | 3 | | | | | LOC152024 | 1.00 | 12069 | 3 | | | | LOC285326 | 1.00 |
| 11974 | 3 | | | | | LOC152225 | 1.00 | 12070 | 3 | | | | LOC285370 | 1.00 |
| 11975 | 3 | | | | | LOC152578 | 1.00 | 12071 | 3 | | | | LOC285375 | 1.00 |
| 11976 | 3 | | | | | LOC152742 | 1.00 | 12072 | 3 | | | | LOC285401 | 1.00 |
| 11977 | 3 | | | | | LOC153469 | 1.00 | 12073 | 3 | | | | LOC285441 | 1.00 |
| 11978 | 3 | | | | | LOC153684 | 1.00 | 12074 | 3 | | | | LOC285456 | 1.00 |
| 11979 | 3 | | | | | LOC153910 | 1.00 | 12075 | 3 | | | | LOC285484 | 1.00 |
| 11980 | 3 | | | | | LOC154092 | 1.00 | 12076 | 3 | | | | LOC285501 | 1.00 |
| 11981 | 3 | | | | | LOC154449 | 1.00 | 12077 | 3 | | | | LOC285547 | 1.00 |
| 11982 | 3 | | | | | LOC154822 | 1.00 | 12078 | 3 | | | | LOC285548 | 1.00 |
| 11983 | 3 | | | | | LOC154860 | 1.00 | 12079 | 3 | | | | LOC285577 | 1.00 |
| 11984 | 3 | | | | | LOC154872 | 1.00 | 12080 | 3 | | | | LOC285593 | 1.00 |
| 11985 | 3 | | | | | LOC157273 | 1.00 | 12081 | 3 | | | | LOC285626 | 1.00 |
| 11986 | 3 | | | | | LOC157381 | 1.00 | 12082 | 3 | | | | LOC285627 | 1.00 |
| 11987 | 3 | | | | | LOC157627 | 1.00 | 12083 | 3 | | | | LOC285629 | 1.00 |
| 11988 | 3 | | | | | LOC158434 | 1.00 | 12084 | 3 | | | | LOC285692 | 1.00 |
| 11989 | 3 | | | | | LOC158435 | 1.00 | 12085 | 3 | | | | LOC285696 | 1.00 |
| 11990 | 3 | | | | | LOC158572 | 1.00 | 12086 | 3 | | | | LOC285740 | 1.00 |
| 11991 | 3 | | | | | LOC158696 | 1.00 | 12087 | 3 | | | | LOC285758 | 1.00 |
| 11992 | 3 | | | | | LOC170425 | 1.00 | 12088 | 3 | | | | LOC285762 | 1.00 |
| 11993 | 3 | | | | | LOC1720 | 1.00 | 12089 | 3 | | | | LOC285768 | 1.00 |
| 11994 | 3 | | | | | LOC200261 | 1.00 | 12090 | 3 | | | | LOC285796 | 1.00 |
| 11995 | 3 | | | | | LOC200726 | 1.00 | 12091 | 3 | | | | LOC285819 | 1.00 |
| 11996 | 3 | | | | | LOC200772 | 1.00 | 12092 | 3 | | | | LOC285847 | 1.00 |

Fig. 39 - 64

| | | | | | | | | | | | | | | | |
|---|---|---|---|---|---|---|---|---|---|---|---|---|---|---|---|
| 12093 | 3 | | | | | LOC285878 | 1.00 | 12189 | 3 | | | | | LOC400548 | 1.00 |
| 12094 | 3 | | | | | LOC285889 | 1.00 | 12190 | 3 | | | | | LOC400550 | 1.00 |
| 12095 | 3 | | | | | LOC285954 | 1.00 | 12191 | 3 | | | | | LOC400558 | 1.00 |
| 12096 | 3 | | | | | LOC285965 | 1.00 | 12192 | 3 | | | | | LOC400620 | 1.00 |
| 12097 | 3 | | | | | LOC285972 | 1.00 | 12193 | 3 | | | | | LOC400643 | 1.00 |
| 12098 | 3 | | | | | LOC286002 | 1.00 | 12194 | 3 | | | | | LOC400654 | 1.00 |
| 12099 | 3 | | | | | LOC286059 | 1.00 | 12195 | 3 | | | | | LOC400655 | 1.00 |
| 12100 | 3 | | | | | LOC286083 | 1.00 | 12196 | 3 | | | | | LOC400680 | 1.00 |
| 12101 | 3 | | | | | LOC286094 | 1.00 | 12197 | 3 | | | | | LOC400684 | 1.00 |
| 12102 | 3 | | | | | LOC286114 | 1.00 | 12198 | 3 | | | | | LOC400685 | 1.00 |
| 12103 | 3 | | | | | LOC286135 | 1.00 | 12199 | 3 | | | | | LOC400794 | 1.00 |
| 12104 | 3 | | | | | LOC286177 | 1.00 | 12200 | 3 | | | | | LOC400891 | 1.00 |
| 12105 | 3 | | | | | LOC286184 | 1.00 | 12201 | 3 | | | | | LOC400940 | 1.00 |
| 12106 | 3 | | | | | LOC286186 | 1.00 | 12202 | 3 | | | | | LOC400958 | 1.00 |
| 12107 | 3 | | | | | LOC286189 | 1.00 | 12203 | 3 | | | | | LOC401134 | 1.00 |
| 12108 | 3 | | | | | LOC286190 | 1.00 | 12204 | 3 | | | | | LOC401164 | 1.00 |
| 12109 | 3 | | | | | LOC286238 | 1.00 | 12205 | 3 | | | | | LOC401177 | 1.00 |
| 12110 | 3 | | | | | LOC286297 | 1.00 | 12206 | 3 | | | | | LOC401242 | 1.00 |
| 12111 | 3 | | | | | LOC286359 | 1.00 | 12207 | 3 | | | | | LOC401324 | 1.00 |
| 12112 | 3 | | | | | LOC286370 | 1.00 | 12208 | 3 | | | | | LOC401431 | 1.00 |
| 12113 | 3 | | | | | LOC286442 | 1.00 | 12209 | 3 | | | | | LOC401463 | 1.00 |
| 12114 | 3 | | | | | LOC286467 | 1.00 | 12210 | 3 | | | | | LOC401497 | 1.00 |
| 12115 | 3 | | | | | LOC338579 | 1.00 | 12211 | 3 | | | | | LOC401557 | 1.00 |
| 12116 | 3 | | | | | LOC338588 | 1.00 | 12212 | 3 | | | | | LOC401980 | 1.00 |
| 12117 | 3 | | | | | LOC338651 | 1.00 | 12213 | 3 | | | | | LOC402160 | 1.00 |
| 12118 | 3 | | | | | LOC338739 | 1.00 | 12214 | 3 | | | | | LOC402779 | 1.00 |
| 12119 | 3 | | | | | LOC338817 | 1.00 | 12215 | 3 | | | | | LOC415056 | 1.00 |
| 12120 | 3 | | | | | LOC338963 | 1.00 | 12216 | 3 | | | | | LOC439949 | 1.00 |
| 12121 | 3 | | | | | LOC339166 | 1.00 | 12217 | 3 | | | | | LOC439950 | 1.00 |
| 12122 | 3 | | | | | LOC339240 | 1.00 | 12218 | 3 | | | | | LOC440028 | 1.00 |
| 12123 | 3 | | | | | LOC339298 | 1.00 | 12219 | 3 | | | | | LOC440040 | 1.00 |
| 12124 | 3 | | | | | LOC339442 | 1.00 | 12220 | 3 | | | | | LOC440041 | 1.00 |
| 12125 | 3 | | | | | LOC339505 | 1.00 | 12221 | 3 | | | | | LOC440117 | 1.00 |
| 12126 | 3 | | | | | LOC339529 | 1.00 | 12222 | 3 | | | | | LOC440131 | 1.00 |
| 12127 | 3 | | | | | LOC339568 | 1.00 | 12223 | 3 | | | | | LOC440173 | 1.00 |
| 12128 | 3 | | | | | LOC339593 | 1.00 | 12224 | 3 | | | | | LOC440356 | 1.00 |
| 12129 | 3 | | | | | LOC339622 | 1.00 | 12225 | 3 | | | | | LOC440461 | 1.00 |
| 12130 | 3 | | | | | LOC339666 | 1.00 | 12226 | 3 | | | | | LOC440518 | 1.00 |
| 12131 | 3 | | | | | LOC339685 | 1.00 | 12227 | 3 | | | | | LOC440563 | 1.00 |
| 12132 | 3 | | | | | LOC339788 | 1.00 | 12228 | 3 | | | | | LOC440600 | 1.00 |
| 12133 | 3 | | | | | LOC339807 | 1.00 | 12229 | 3 | | | | | LOC440700 | 1.00 |
| 12134 | 3 | | | | | LOC339822 | 1.00 | 12230 | 3 | | | | | LOC440704 | 1.00 |
| 12135 | 3 | | | | | LOC339862 | 1.00 | 12231 | 3 | | | | | LOC440896 | 1.00 |
| 12136 | 3 | | | | | LOC339874 | 1.00 | 12232 | 3 | | | | | LOC440900 | 1.00 |
| 12137 | 3 | | | | | LOC339894 | 1.00 | 12233 | 3 | | | | | LOC440905 | 1.00 |
| 12138 | 3 | | | | | LOC339926 | 1.00 | 12234 | 3 | | | | | LOC440910 | 1.00 |
| 12139 | 3 | | | | | LOC339975 | 1.00 | 12235 | 3 | | | | | LOC440925 | 1.00 |
| 12140 | 3 | | | | | LOC340017 | 1.00 | 12236 | 3 | | | | | LOC440970 | 1.00 |
| 12141 | 3 | | | | | LOC340073 | 1.00 | 12237 | 3 | | | | | LOC441009 | 1.00 |
| 12142 | 3 | | | | | LOC340074 | 1.00 | 12238 | 3 | | | | | LOC441025 | 1.00 |
| 12143 | 3 | | | | | LOC340094 | 1.00 | 12239 | 3 | | | | | LOC441177 | 1.00 |
| 12144 | 3 | | | | | LOC340107 | 1.00 | 12240 | 3 | | | | | LOC441242 | 1.00 |
| 12145 | 3 | | | | | LOC340113 | 1.00 | 12241 | 3 | | | | | LOC441495 | 1.00 |
| 12146 | 3 | | | | | LOC340508 | 1.00 | 12242 | 3 | | | | | LOC441601 | 1.00 |
| 12147 | 3 | | | | | LOC340515 | 1.00 | 12243 | 3 | | | | | LOC441666 | 1.00 |
| 12148 | 3 | | | | | LOC347411 | 1.00 | 12244 | 3 | | | | | LOC442028 | 1.00 |
| 12149 | 3 | | | | | LOC348120 | 1.00 | 12245 | 3 | | | | | LOC442132 | 1.00 |
| 12150 | 3 | | | | | LOC348761 | 1.00 | 12246 | 3 | | | | | LOC442421 | 1.00 |
| 12151 | 3 | | | | | LOC349160 | 1.00 | 12247 | 3 | | | | | LOC442459 | 1.00 |
| 12152 | 3 | | | | | LOC375010 | 1.00 | 12248 | 3 | | | | | LOC442497 | 1.00 |
| 12153 | 3 | | | | | LOC375196 | 1.00 | 12249 | 3 | | | | | LOC494141 | 1.00 |
| 12154 | 3 | | | | | LOC386597 | 1.00 | 12250 | 3 | | | | | LOC494558 | 1.00 |
| 12155 | 3 | | | | | LOC387646 | 1.00 | 12251 | 3 | | | | | LOC503519 | 1.00 |
| 12156 | 3 | | | | | LOC387895 | 1.00 | 12252 | 3 | | | | | LOC550113 | 1.00 |
| 12157 | 3 | | | | | LOC388276 | 1.00 | 12253 | 3 | | | | | LOC554201 | 1.00 |
| 12158 | 3 | | | | | LOC388387 | 1.00 | 12254 | 3 | | | | | LOC554223 | 1.00 |
| 12159 | 3 | | | | | LOC388553 | 1.00 | 12255 | 3 | | | | | LOC574538 | 1.00 |
| 12160 | 3 | | | | | LOC388813 | 1.00 | 12256 | 3 | | | | | LOC619207 | 1.00 |
| 12161 | 3 | | | | | LOC388906 | 1.00 | 12257 | 3 | | | | | LOC63930 | 1.00 |
| 12162 | 3 | | | | | LOC388942 | 1.00 | 12258 | 3 | | | | | LOC641298 | 1.00 |
| 12163 | 3 | | | | | LOC388946 | 1.00 | 12259 | 3 | | | | | LOC641364 | 1.00 |
| 12164 | 3 | | | | | LOC388948 | 1.00 | 12260 | 3 | | | | | LOC641365 | 1.00 |
| 12165 | 3 | | | | | LOC389023 | 1.00 | 12261 | 3 | | | | | LOC641367 | 1.00 |
| 12166 | 3 | | | | | LOC389043 | 1.00 | 12262 | 3 | | | | | LOC641515 | 1.00 |
| 12167 | 3 | | | | | LOC389247 | 1.00 | 12263 | 3 | | | | | LOC641518 | 1.00 |
| 12168 | 3 | | | | | LOC389332 | 1.00 | 12264 | 3 | | | | | LOC642236 | 1.00 |
| 12169 | 3 | | | | | LOC389458 | 1.00 | 12265 | 3 | | | | | LOC642366 | 1.00 |
| 12170 | 3 | | | | | LOC389634 | 1.00 | 12266 | 3 | | | | | LOC642426 | 1.00 |
| 12171 | 3 | | | | | LOC389705 | 1.00 | 12267 | 3 | | | | | LOC642826 | 1.00 |
| 12172 | 3 | | | | | LOC389765 | 1.00 | 12268 | 3 | | | | | LOC642929 | 1.00 |
| 12173 | 3 | | | | | LOC389791 | 1.00 | 12269 | 3 | | | | | LOC643037 | 1.00 |
| 12174 | 3 | | | | | LOC390660 | 1.00 | 12270 | 3 | | | | | LOC643201 | 1.00 |
| 12175 | 3 | | | | | LOC390705 | 1.00 | 12271 | 3 | | | | | LOC643339 | 1.00 |
| 12176 | 3 | | | | | LOC390858 | 1.00 | 12272 | 3 | | | | | LOC643401 | 1.00 |
| 12177 | 3 | | | | | LOC392196 | 1.00 | 12273 | 3 | | | | | LOC643406 | 1.00 |
| 12178 | 3 | | | | | LOC392232 | 1.00 | 12274 | 3 | | | | | LOC643441 | 1.00 |
| 12179 | 3 | | | | | LOC392364 | 1.00 | 12275 | 3 | | | | | LOC643486 | 1.00 |
| 12180 | 3 | | | | | LOC399708 | 1.00 | 12276 | 3 | | | | | LOC643529 | 1.00 |
| 12181 | 3 | | | | | LOC399715 | 1.00 | 12277 | 3 | | | | | LOC643542 | 1.00 |
| 12182 | 3 | | | | | LOC399815 | 1.00 | 12278 | 3 | | | | | LOC643623 | 1.00 |
| 12183 | 3 | | | | | LOC399829 | 1.00 | 12279 | 3 | | | | | LOC643714 | 1.00 |
| 12184 | 3 | | | | | LOC399939 | 1.00 | 12280 | 3 | | | | | LOC643723 | 1.00 |
| 12185 | 3 | | | | | LOC399940 | 1.00 | 12281 | 3 | | | | | LOC643770 | 1.00 |
| 12186 | 3 | | | | | LOC400084 | 1.00 | 12282 | 3 | | | | | LOC643802 | 1.00 |
| 12187 | 3 | | | | | LOC400238 | 1.00 | 12283 | 3 | | | | | LOC643923 | 1.00 |
| 12188 | 3 | | | | | LOC400456 | 1.00 | 12284 | 3 | | | | | LOC643955 | 1.00 |

Fig. 39 - 65

| | | | | | | | | | | | | | | | |
|---|---|---|---|---|---|---|---|---|---|---|---|---|---|---|---|
| 12285 | 3 | | | | | | LOC644100 | 1.00 | 12381 | 3 | | | | LOC730441 | 1.00 |
| 12286 | 3 | | | | | | LOC644145 | 1.00 | 12382 | 3 | | | | LOC730668 | 1.00 |
| 12287 | 3 | | | | | | LOC644189 | 1.00 | 12383 | 3 | | | | LOC730755 | 1.00 |
| 12288 | 3 | | | | | | LOC644248 | 1.00 | 12384 | 3 | | | | LOC730811 | 1.00 |
| 12289 | 3 | | | | | | LOC644554 | 1.00 | 12385 | 3 | | | | LOC731223 | 1.00 |
| 12290 | 3 | | | | | | LOC644669 | 1.00 | 12386 | 3 | | | | LOC731424 | 1.00 |
| 12291 | 3 | | | | | | LOC644714 | 1.00 | 12387 | 3 | | | | LOC731789 | 1.00 |
| 12292 | 3 | | | | | | LOC644838 | 1.00 | 12388 | 3 | | | | LOC732275 | 1.00 |
| 12293 | 3 | | | | | | LOC645206 | 1.00 | 12389 | 3 | | | | LOC81691 | 1.00 |
| 12294 | 3 | | | | | | LOC645249 | 1.00 | 12390 | 3 | | | | LOC84931 | 1.00 |
| 12295 | 3 | | | | | | LOC645355 | 1.00 | 12391 | 3 | | | | LOC84989 | 1.00 |
| 12296 | 3 | | | | | | LOC645431 | 1.00 | 12392 | 3 | | | | LOC90246 | 1.00 |
| 12297 | 3 | | | | | | LOC645434 | 1.00 | 12393 | 3 | | | | LOC90499 | 1.00 |
| 12298 | 3 | | | | | | LOC645591 | 1.00 | 12394 | 3 | | | | LOC91149 | 1.00 |
| 12299 | 3 | | | | | | LOC645752 | 1.00 | 12395 | 3 | | | | LOC91948 | 1.00 |
| 12300 | 3 | | | | | | LOC645949 | 1.00 | 12396 | 3 | | | | LOC93432 | 1.00 |
| 12301 | 3 | | | | | | LOC646168 | 1.00 | 12397 | 3 | | | | LONRF2 | 1.00 |
| 12302 | 3 | | | | | | LOC646268 | 1.00 | 12398 | 3 | | | | LONRF3 | 1.00 |
| 12303 | 3 | | | | | | LOC646278 | 1.00 | 12399 | 3 | | | | LOXHD1 | 1.00 |
| 12304 | 3 | | | | | | LOC646324 | 1.00 | 12400 | 3 | | | | LPA | 1.00 |
| 12305 | 3 | | | | | | LOC646329 | 1.00 | 12401 | 3 | | | | LPAL2 | 1.00 |
| 12306 | 3 | | | | | | LOC646498 | 1.00 | 12402 | 3 | | | | LPAR4 | 1.00 |
| 12307 | 3 | | | | | | LOC646508 | 1.00 | 12403 | 3 | | | | LPO | 1.00 |
| 12308 | 3 | | | | | | LOC646626 | 1.00 | 12404 | 3 | | | | LPPR1 | 1.00 |
| 12309 | 3 | | | | | | LOC646627 | 1.00 | 12405 | 3 | | | | LPPR3 | 1.00 |
| 12310 | 3 | | | | | | LOC646736 | 1.00 | 12406 | 3 | | | | LPPR5 | 1.00 |
| 12311 | 3 | | | | | | LOC646743 | 1.00 | 12407 | 3 | | | | LRAT | 1.00 |
| 12312 | 3 | | | | | | LOC646813 | 1.00 | 12408 | 3 | | | | LRCH2 | 1.00 |
| 12313 | 3 | | | | | | LOC646851 | 1.00 | 12409 | 3 | | | | LRCH3 | 1.00 |
| 12314 | 3 | | | | | | LOC646903 | 1.00 | 12410 | 3 | | | | LRFN2 | 1.00 |
| 12315 | 3 | | | | | | LOC646938 | 1.00 | 12411 | 3 | | | | LRFN5 | 1.00 |
| 12316 | 3 | | | | | | LOC646999 | 1.00 | 12412 | 3 | | | | LRGUK | 1.00 |
| 12317 | 3 | | | | | | LOC647012 | 1.00 | 12413 | 3 | | | | LRIT1 | 1.00 |
| 12318 | 3 | | | | | | LOC647107 | 1.00 | 12414 | 3 | | | | LRIT3 | 1.00 |
| 12319 | 3 | | | | | | LOC647323 | 1.00 | 12415 | 3 | | | | LRP1B | 1.00 |
| 12320 | 3 | | | | | | LOC647589 | 1.00 | 12416 | 3 | | | | LRP2 | 1.00 |
| 12321 | 3 | | | | | | LOC647859 | 1.00 | 12417 | 3 | | | | LRP8 | 1.00 |
| 12322 | 3 | | | | | | LOC647946 | 1.00 | 12418 | 3 | | | | LRRC10 | 1.00 |
| 12323 | 3 | | | | | | LOC648691 | 1.00 | 12419 | 3 | | | | LRRC14B | 1.00 |
| 12324 | 3 | | | | | | LOC648809 | 1.00 | 12420 | 3 | | | | LRRC19 | 1.00 |
| 12325 | 3 | | | | | | LOC649133 | 1.00 | 12421 | 3 | | | | LRRC24 | 1.00 |
| 12326 | 3 | | | | | | LOC649330 | 1.00 | 12422 | 3 | | | | LRRC30 | 1.00 |
| 12327 | 3 | | | | | | LOC650226 | 1.00 | 12423 | 3 | | | | LRRC31 | 1.00 |
| 12328 | 3 | | | | | | LOC650293 | 1.00 | 12424 | 3 | | | | LRRC36 | 1.00 |
| 12329 | 3 | | | | | | LOC650623 | 1.00 | 12425 | 3 | | | | LRRC38 | 1.00 |
| 12330 | 3 | | | | | | LOC653061 | 1.00 | 12426 | 3 | | | | LRRC39 | 1.00 |
| 12331 | 3 | | | | | | LOC653075 | 1.00 | 12427 | 3 | | | | LRRC3B | 1.00 |
| 12332 | 3 | | | | | | LOC653486 | 1.00 | 12428 | 3 | | | | LRRC3C | 1.00 |
| 12333 | 3 | | | | | | LOC653501 | 1.00 | 12429 | 3 | | | | LRRC43 | 1.00 |
| 12334 | 3 | | | | | | LOC653712 | 1.00 | 12430 | 3 | | | | LRRC46 | 1.00 |
| 12335 | 3 | | | | | | LOC653786 | 1.00 | 12431 | 3 | | | | LRRC4C | 1.00 |
| 12336 | 3 | | | | | | LOC723809 | 1.00 | 12432 | 3 | | | | LRRC52 | 1.00 |
| 12337 | 3 | | | | | | LOC727677 | 1.00 | 12433 | 3 | | | | LRRC55 | 1.00 |
| 12338 | 3 | | | | | | LOC727710 | 1.00 | 12434 | 3 | | | | LRRC66 | 1.00 |
| 12339 | 3 | | | | | | LOC727915 | 1.00 | 12435 | 3 | | | | LRRC69 | 1.00 |
| 12340 | 3 | | | | | | LOC727924 | 1.00 | 12436 | 3 | | | | LRRC7 | 1.00 |
| 12341 | 3 | | | | | | LOC727982 | 1.00 | 12437 | 3 | | | | LRRC71 | 1.00 |
| 12342 | 3 | | | | | | LOC728012 | 1.00 | 12438 | 3 | | | | LRRC72 | 1.00 |
| 12343 | 3 | | | | | | LOC728040 | 1.00 | 12439 | 3 | | | | LRRC73 | 1.00 |
| 12344 | 3 | | | | | | LOC728084 | 1.00 | 12440 | 3 | | | | LRRD1 | 1.00 |
| 12345 | 3 | | | | | | LOC728175 | 1.00 | 12441 | 3 | | | | LRRIQ1 | 1.00 |
| 12346 | 3 | | | | | | LOC728218 | 1.00 | 12442 | 3 | | | | LRRIQ3 | 1.00 |
| 12347 | 3 | | | | | | LOC728228 | 1.00 | 12443 | 3 | | | | LRRIQ4 | 1.00 |
| 12348 | 3 | | | | | | LOC728323 | 1.00 | 12444 | 3 | | | | LRRK2 | 1.00 |
| 12349 | 3 | | | | | | LOC728342 | 1.00 | 12445 | 3 | | | | LRRN2 | 1.00 |
| 12350 | 3 | | | | | | LOC728369 | 1.00 | 12446 | 3 | | | | LRRN3 | 1.00 |
| 12351 | 3 | | | | | | LOC728393 | 1.00 | 12447 | 3 | | | | LRRN4 | 1.00 |
| 12352 | 3 | | | | | | LOC728405 | 1.00 | 12448 | 3 | | | | LRRTM2 | 1.00 |
| 12353 | 3 | | | | | | LOC728407 | 1.00 | 12449 | 3 | | | | LRRTM3 | 1.00 |
| 12354 | 3 | | | | | | LOC728437 | 1.00 | 12450 | 3 | | | | LRRTM4 | 1.00 |
| 12355 | 3 | | | | | | LOC728463 | 1.00 | 12451 | 3 | | | | LRTM1 | 1.00 |
| 12356 | 3 | | | | | | LOC728558 | 1.00 | 12452 | 3 | | | | LRTM2 | 1.00 |
| 12357 | 3 | | | | | | LOC728716 | 1.00 | 12453 | 3 | | | | LSAMP-AS3 | 1.00 |
| 12358 | 3 | | | | | | LOC728723 | 1.00 | 12454 | 3 | | | | LSM11 | 1.00 |
| 12359 | 3 | | | | | | LOC728724 | 1.00 | 12455 | 3 | | | | LTA | 1.00 |
| 12360 | 3 | | | | | | LOC728819 | 1.00 | 12456 | 3 | | | | LTK | 1.00 |
| 12361 | 3 | | | | | | LOC728989 | 1.00 | 12457 | 3 | | | | LUZP2 | 1.00 |
| 12362 | 3 | | | | | | LOC729041 | 1.00 | 12458 | 3 | | | | LUZP4 | 1.00 |
| 12363 | 3 | | | | | | LOC729059 | 1.00 | 12459 | 3 | | | | LY6G6E | 1.00 |
| 12364 | 3 | | | | | | LOC729080 | 1.00 | 12460 | 3 | | | | LY6G6F | 1.00 |
| 12365 | 3 | | | | | | LOC729121 | 1.00 | 12461 | 3 | | | | LY6H | 1.00 |
| 12366 | 3 | | | | | | LOC729177 | 1.00 | 12462 | 3 | | | | LY75-CD302 | 1.00 |
| 12367 | 3 | | | | | | LOC729264 | 1.00 | 12463 | 3 | | | | LY86-AS1 | 1.00 |
| 12368 | 3 | | | | | | LOC729444 | 1.00 | 12464 | 3 | | | | LYG2 | 1.00 |
| 12369 | 3 | | | | | | LOC729506 | 1.00 | 12465 | 3 | | | | LYPD4 | 1.00 |
| 12370 | 3 | | | | | | LOC729603 | 1.00 | 12466 | 3 | | | | LYPD6 | 1.00 |
| 12371 | 3 | | | | | | LOC729609 | 1.00 | 12467 | 3 | | | | LYZL1 | 1.00 |
| 12372 | 3 | | | | | | LOC729668 | 1.00 | 12468 | 3 | | | | LYZL2 | 1.00 |
| 12373 | 3 | | | | | | LOC729683 | 1.00 | 12469 | 3 | | | | LYZL4 | 1.00 |
| 12374 | 3 | | | | | | LOC729739 | 1.00 | 12470 | 3 | | | | LYZL6 | 1.00 |
| 12375 | 3 | | | | | | LOC729911 | 1.00 | 12471 | 3 | | | | M1 | 1.00 |
| 12376 | 3 | | | | | | LOC729950 | 1.00 | 12472 | 3 | | | | MAB21L2 | 1.00 |
| 12377 | 3 | | | | | | LOC729966 | 1.00 | 12473 | 3 | | | | MAB21L3 | 1.00 |
| 12378 | 3 | | | | | | LOC729987 | 1.00 | 12474 | 3 | | | | MACROD2-AS1 | 1.00 |
| 12379 | 3 | | | | | | LOC730159 | 1.00 | 12475 | 3 | | | | MADCAM1 | 1.00 |
| 12380 | 3 | | | | | | LOC730227 | 1.00 | 12476 | 3 | | | | MAEL | 1.00 |

Fig. 39 - 66

| | | | | | | | | | | | | | | | | |
|---|---|---|---|---|---|---|---|---|---|---|---|---|---|---|---|---|
| 12477 | 3 | | | | | MAFA | 1.00 | | 12572 | 3 | | | | | MGC16121 | 1.00 |
| 12478 | 3 | | | | | MAG | 1.00 | | 12573 | 3 | | | | | MGC16142 | 1.00 |
| 12479 | 3 | | | | | MAGEA1 | 1.00 | | 12574 | 3 | | | | | MGC16703 | 1.00 |
| 12480 | 3 | | | | | MAGEA10 | 1.00 | | 12575 | 3 | | | | | MGC23270 | 1.00 |
| 12481 | 3 | | | | | MAGEA10-MAGEA5 | 1.00 | | 12576 | 3 | | | | | MGC27382 | 1.00 |
| | | | | | | | | | 12577 | 3 | | | | | MGC2889 | 1.00 |
| 12482 | 3 | | | | | MAGEA12 | 1.00 | | 12578 | 3 | | | | | MGC34034 | 1.00 |
| 12483 | 3 | | | | | MAGEA2 | 1.00 | | 12579 | 3 | | | | | MGC39584 | 1.00 |
| 12484 | 3 | | | | | MAGEA2B | 1.00 | | 12580 | 3 | | | | | MGC4473 | 1.00 |
| 12485 | 3 | | | | | MAGEA3 | 1.00 | | 12581 | 3 | | | | | MGC45800 | 1.00 |
| 12486 | 3 | | | | | MAGEA4 | 1.00 | | 12582 | 3 | | | | | MGC70870 | 1.00 |
| 12487 | 3 | | | | | MAGEA5 | 1.00 | | 12583 | 3 | | | | | MIA2 | 1.00 |
| 12488 | 3 | | | | | MAGEA6 | 1.00 | | 12584 | 3 | | | | | MIMT1 | 1.00 |
| 12489 | 3 | | | | | MAGEA8 | 1.00 | | 12585 | 3 | | | | | MIOX | 1.00 |
| 12490 | 3 | | | | | MAGEA9 | 1.00 | | 12586 | 3 | | | | | MIP | 1.00 |
| 12491 | 3 | | | | | MAGEA9B | 1.00 | | 12587 | 3 | | | | | MIPOL1 | 1.00 |
| 12492 | 3 | | | | | MAGEB1 | 1.00 | | 12588 | 3 | | | | | MIR100 | 1.00 |
| 12493 | 3 | | | | | MAGEB10 | 1.00 | | 12589 | 3 | | | | | MIR101-1 | 1.00 |
| 12494 | 3 | | | | | MAGEB16 | 1.00 | | 12590 | 3 | | | | | MIR101-2 | 1.00 |
| 12495 | 3 | | | | | MAGEB18 | 1.00 | | 12591 | 3 | | | | | MIR103A1 | 1.00 |
| 12496 | 3 | | | | | MAGEB2 | 1.00 | | 12592 | 3 | | | | | MIR103A2 | 1.00 |
| 12497 | 3 | | | | | MAGEB3 | 1.00 | | 12593 | 3 | | | | | MIR103B1 | 1.00 |
| 12498 | 3 | | | | | MAGEB4 | 1.00 | | 12594 | 3 | | | | | MIR103B2 | 1.00 |
| 12499 | 3 | | | | | MAGEB6 | 1.00 | | 12595 | 3 | | | | | MIR105-1 | 1.00 |
| 12500 | 3 | | | | | MAGEC1 | 1.00 | | 12596 | 3 | | | | | MIR105-2 | 1.00 |
| 12501 | 3 | | | | | MAGEC2 | 1.00 | | 12597 | 3 | | | | | MIR106A | 1.00 |
| 12502 | 3 | | | | | MAGEC3 | 1.00 | | 12598 | 3 | | | | | MIR106B | 1.00 |
| 12503 | 3 | | | | | MAGEE2 | 1.00 | | 12599 | 3 | | | | | MIR107 | 1.00 |
| 12504 | 3 | | | | | MAGEL2 | 1.00 | | 12600 | 3 | | | | | MIR10A | 1.00 |
| 12505 | 3 | | | | | MAK | 1.00 | | 12601 | 3 | | | | | MIR10B | 1.00 |
| 12506 | 3 | | | | | MAN2A1 | 1.00 | | 12602 | 3 | | | | | MIR1-1 | 1.00 |
| 12507 | 3 | | | | | MANSC4 | 1.00 | | 12603 | 3 | | | | | MIR1178 | 1.00 |
| 12508 | 3 | | | | | MAP2K6 | 1.00 | | 12604 | 3 | | | | | MIR1179 | 1.00 |
| 12509 | 3 | | | | | MAP3K15 | 1.00 | | 12605 | 3 | | | | | MIR1180 | 1.00 |
| 12510 | 3 | | | | | MAP3K9 | 1.00 | | 12606 | 3 | | | | | MIR1181 | 1.00 |
| 12511 | 3 | | | | | MAP7D2 | 1.00 | | 12607 | 3 | | | | | MIR1182 | 1.00 |
| 12512 | 3 | | | | | MAP9 | 1.00 | | 12608 | 3 | | | | | MIR1184-3 | 1.00 |
| 12513 | 3 | | | | | MAPT-AS1 | 1.00 | | 12609 | 3 | | | | | MIR1185-1 | 1.00 |
| 12514 | 3 | | | | | MAPT-IT1 | 1.00 | | 12610 | 3 | | | | | MIR1185-2 | 1.00 |
| 12515 | 3 | | | | | MARCH10 | 1.00 | | 12611 | 3 | | | | | MIR1193 | 1.00 |
| 12516 | 3 | | | | | MARCH11 | 1.00 | | 12612 | 3 | | | | | MIR1197 | 1.00 |
| 12517 | 3 | | | | | MARCH4 | 1.00 | | 12613 | 3 | | | | | MIR1-2 | 1.00 |
| 12518 | 3 | | | | | MARK2P9 | 1.00 | | 12614 | 3 | | | | | MIR1200 | 1.00 |
| 12519 | 3 | | | | | MAS1 | 1.00 | | 12615 | 3 | | | | | MIR1203 | 1.00 |
| 12520 | 3 | | | | | MAS1L | 1.00 | | 12616 | 3 | | | | | MIR1204 | 1.00 |
| 12521 | 3 | | | | | MATN1 | 1.00 | | 12617 | 3 | | | | | MIR1205 | 1.00 |
| 12522 | 3 | | | | | MATN3 | 1.00 | | 12618 | 3 | | | | | MIR1206 | 1.00 |
| 12523 | 3 | | | | | MBD3L1 | 1.00 | | 12619 | 3 | | | | | MIR1207 | 1.00 |
| 12524 | 3 | | | | | MBD3L2 | 1.00 | | 12620 | 3 | | | | | MIR1208 | 1.00 |
| 12525 | 3 | | | | | MBD3L3 | 1.00 | | 12621 | 3 | | | | | MIR122 | 1.00 |
| 12526 | 3 | | | | | MBD3L4 | 1.00 | | 12622 | 3 | | | | | MIR1224 | 1.00 |
| 12527 | 3 | | | | | MBD3L5 | 1.00 | | 12623 | 3 | | | | | MIR1225 | 1.00 |
| 12528 | 3 | | | | | MBL2 | 1.00 | | 12624 | 3 | | | | | MIR1226 | 1.00 |
| 12529 | 3 | | | | | MBOAT4 | 1.00 | | 12625 | 3 | | | | | MIR1227 | 1.00 |
| 12530 | 3 | | | | | MC2R | 1.00 | | 12626 | 3 | | | | | MIR1228 | 1.00 |
| 12531 | 3 | | | | | MC3R | 1.00 | | 12627 | 3 | | | | | MIR1229 | 1.00 |
| 12532 | 3 | | | | | MC4R | 1.00 | | 12628 | 3 | | | | | MIR1231 | 1.00 |
| 12533 | 3 | | | | | MC5R | 1.00 | | 12629 | 3 | | | | | MIR1233-1 | 1.00 |
| 12534 | 3 | | | | | MCART2 | 1.00 | | 12630 | 3 | | | | | MIR1233-2 | 1.00 |
| 12535 | 3 | | | | | MCART3P | 1.00 | | 12631 | 3 | | | | | MIR1234 | 1.00 |
| 12536 | 3 | | | | | MCART6 | 1.00 | | 12632 | 3 | | | | | MIR1236 | 1.00 |
| 12537 | 3 | | | | | MCCD1 | 1.00 | | 12633 | 3 | | | | | MIR1237 | 1.00 |
| 12538 | 3 | | | | | MCF2 | 1.00 | | 12634 | 3 | | | | | MIR1238 | 1.00 |
| 12539 | 3 | | | | | MCF2L2 | 1.00 | | 12635 | 3 | | | | | MIR124-1 | 1.00 |
| 12540 | 3 | | | | | MCHR2 | 1.00 | | 12636 | 3 | | | | | MIR124-2 | 1.00 |
| 12541 | 3 | | | | | MCM10 | 1.00 | | 12637 | 3 | | | | | MIR1243 | 1.00 |
| 12542 | 3 | | | | | MCM3AP-AS1 | 1.00 | | 12638 | 3 | | | | | MIR124-3 | 1.00 |
| 12543 | 3 | | | | | MDGA2 | 1.00 | | 12639 | 3 | | | | | MIR1244-1 | 1.00 |
| 12544 | 3 | | | | | MDH1B | 1.00 | | 12640 | 3 | | | | | MIR1244-2 | 1.00 |
| 12545 | 3 | | | | | MDS2 | 1.00 | | 12641 | 3 | | | | | MIR1244-3 | 1.00 |
| 12546 | 3 | | | | | MED12L | 1.00 | | 12642 | 3 | | | | | MIR1245A | 1.00 |
| 12547 | 3 | | | | | MEF2BNB-MEF2B | 1.00 | | 12643 | 3 | | | | | MIR1245B | 1.00 |
| 12548 | 3 | | | | | MEFV | 1.00 | | 12644 | 3 | | | | | MIR1246 | 1.00 |
| 12549 | 3 | | | | | MEG8 | 1.00 | | 12645 | 3 | | | | | MIR1248 | 1.00 |
| 12550 | 3 | | | | | MEGF10 | 1.00 | | 12646 | 3 | | | | | MIR1249 | 1.00 |
| 12551 | 3 | | | | | MEGF11 | 1.00 | | 12647 | 3 | | | | | MIR1250 | 1.00 |
| 12552 | 3 | | | | | MEI1 | 1.00 | | 12648 | 3 | | | | | MIR1251 | 1.00 |
| 12553 | 3 | | | | | MEIG1 | 1.00 | | 12649 | 3 | | | | | MIR1252 | 1.00 |
| 12554 | 3 | | | | | MEP1A | 1.00 | | 12650 | 3 | | | | | MIR1253 | 1.00 |
| 12555 | 3 | | | | | MEP1B | 1.00 | | 12651 | 3 | | | | | MIR1256 | 1.00 |
| 12556 | 3 | | | | | MEPE | 1.00 | | 12652 | 3 | | | | | MIR1257 | 1.00 |
| 12557 | 3 | | | | | MESP2 | 1.00 | | 12653 | 3 | | | | | MIR1258 | 1.00 |
| 12558 | 3 | | | | | MESTIT1 | 1.00 | | 12654 | 3 | | | | | MIR125A | 1.00 |
| 12559 | 3 | | | | | METTL11B | 1.00 | | 12655 | 3 | | | | | MIR125B1 | 1.00 |
| 12560 | 3 | | | | | METTL21C | 1.00 | | 12656 | 3 | | | | | MIR125B2 | 1.00 |
| 12561 | 3 | | | | | METTL21CP1 | 1.00 | | 12657 | 3 | | | | | MIR126 | 1.00 |
| 12562 | 3 | | | | | METTL24 | 1.00 | | 12658 | 3 | | | | | MIR1260A | 1.00 |
| 12563 | 3 | | | | | MFSD2B | 1.00 | | 12659 | 3 | | | | | MIR1260B | 1.00 |
| 12564 | 3 | | | | | MFSD6L | 1.00 | | 12660 | 3 | | | | | MIR1262 | 1.00 |
| 12565 | 3 | | | | | MGAM | 1.00 | | 12661 | 3 | | | | | MIR1264 | 1.00 |
| 12566 | 3 | | | | | MGAT4C | 1.00 | | 12662 | 3 | | | | | MIR1265 | 1.00 |
| 12567 | 3 | | | | | MGAT5B | 1.00 | | 12663 | 3 | | | | | MIR1266 | 1.00 |
| 12568 | 3 | | | | | MGC12916 | 1.00 | | 12664 | 3 | | | | | MIR127 | 1.00 |
| 12569 | 3 | | | | | MGC14436 | 1.00 | | 12665 | 3 | | | | | MIR1270-1 | 1.00 |
| 12570 | 3 | | | | | MGC15885 | 1.00 | | 12666 | 3 | | | | | MIR1272 | 1.00 |
| 12571 | 3 | | | | | MGC16025 | 1.00 | | 12667 | 3 | | | | | MIR1275 | 1.00 |

Fig. 39 - 67

| | | | | | | | | | | | | | | | | |
|---|---|---|---|---|---|---|---|---|---|---|---|---|---|---|---|---|
| 12668 | 3 | | | | | MIR1276 | 1.00 | | 12764 | 3 | | | | | MIR1909 | 1.00 |
| 12669 | 3 | | | | | MIR1277 | 1.00 | | 12765 | 3 | | | | | MIR190A | 1.00 |
| 12670 | 3 | | | | | MIR1278 | 1.00 | | 12766 | 3 | | | | | MIR190B | 1.00 |
| 12671 | 3 | | | | | MIR1279 | 1.00 | | 12767 | 3 | | | | | MIR191 | 1.00 |
| 12672 | 3 | | | | | MIR1280 | 1.00 | | 12768 | 3 | | | | | MIR1910 | 1.00 |
| 12673 | 3 | | | | | MIR1281 | 1.00 | | 12769 | 3 | | | | | MIR1911 | 1.00 |
| 12674 | 3 | | | | | MIR128-1 | 1.00 | | 12770 | 3 | | | | | MIR1912 | 1.00 |
| 12675 | 3 | | | | | MIR128-2 | 1.00 | | 12771 | 3 | | | | | MIR1913 | 1.00 |
| 12676 | 3 | | | | | MIR1283-1 | 1.00 | | 12772 | 3 | | | | | MIR1914 | 1.00 |
| 12677 | 3 | | | | | MIR1283-2 | 1.00 | | 12773 | 3 | | | | | MIR1915 | 1.00 |
| 12678 | 3 | | | | | MIR1284 | 1.00 | | 12774 | 3 | | | | | MIR192 | 1.00 |
| 12679 | 3 | | | | | MIR1286 | 1.00 | | 12775 | 3 | | | | | MIR193A | 1.00 |
| 12680 | 3 | | | | | MIR1287 | 1.00 | | 12776 | 3 | | | | | MIR193B | 1.00 |
| 12681 | 3 | | | | | MIR1288 | 1.00 | | 12777 | 3 | | | | | MIR194-1 | 1.00 |
| 12682 | 3 | | | | | MIR1289-2 | 1.00 | | 12778 | 3 | | | | | MIR194-2 | 1.00 |
| 12683 | 3 | | | | | MIR1291 | 1.00 | | 12779 | 3 | | | | | MIR195 | 1.00 |
| 12684 | 3 | | | | | MIR129-1 | 1.00 | | 12780 | 3 | | | | | MIR196A1 | 1.00 |
| 12685 | 3 | | | | | MIR1292 | 1.00 | | 12781 | 3 | | | | | MIR196A2 | 1.00 |
| 12686 | 3 | | | | | MIR129-2 | 1.00 | | 12782 | 3 | | | | | MIR196B | 1.00 |
| 12687 | 3 | | | | | MIR1293 | 1.00 | | 12783 | 3 | | | | | MIR197 | 1.00 |
| 12688 | 3 | | | | | MIR1295A | 1.00 | | 12784 | 3 | | | | | MIR1972-1 | 1.00 |
| 12689 | 3 | | | | | MIR1296 | 1.00 | | 12785 | 3 | | | | | MIR1973 | 1.00 |
| 12690 | 3 | | | | | MIR1297 | 1.00 | | 12786 | 3 | | | | | MIR1976 | 1.00 |
| 12691 | 3 | | | | | MIR1298 | 1.00 | | 12787 | 3 | | | | | MIR198 | 1.00 |
| 12692 | 3 | | | | | MIR1301 | 1.00 | | 12788 | 3 | | | | | MIR199A1 | 1.00 |
| 12693 | 3 | | | | | MIR1304 | 1.00 | | 12789 | 3 | | | | | MIR199A2 | 1.00 |
| 12694 | 3 | | | | | MIR1305 | 1.00 | | 12790 | 3 | | | | | MIR199B | 1.00 |
| 12695 | 3 | | | | | MIR1306 | 1.00 | | 12791 | 3 | | | | | MIR19A | 1.00 |
| 12696 | 3 | | | | | MIR130A | 1.00 | | 12792 | 3 | | | | | MIR19B1 | 1.00 |
| 12697 | 3 | | | | | MIR130B | 1.00 | | 12793 | 3 | | | | | MIR19B2 | 1.00 |
| 12698 | 3 | | | | | MIR132 | 1.00 | | 12794 | 3 | | | | | MIR200A | 1.00 |
| 12699 | 3 | | | | | MIR1322 | 1.00 | | 12795 | 3 | | | | | MIR200B | 1.00 |
| 12700 | 3 | | | | | MIR1323 | 1.00 | | 12796 | 3 | | | | | MIR200C | 1.00 |
| 12701 | 3 | | | | | MIR1324 | 1.00 | | 12797 | 3 | | | | | MIR202 | 1.00 |
| 12702 | 3 | | | | | MIR133A1 | 1.00 | | 12798 | 3 | | | | | MIR203 | 1.00 |
| 12703 | 3 | | | | | MIR133A2 | 1.00 | | 12799 | 3 | | | | | MIR204 | 1.00 |
| 12704 | 3 | | | | | MIR133B | 1.00 | | 12800 | 3 | | | | | MIR205 | 1.00 |
| 12705 | 3 | | | | | MIR134 | 1.00 | | 12801 | 3 | | | | | MIR2052 | 1.00 |
| 12706 | 3 | | | | | MIR1343 | 1.00 | | 12802 | 3 | | | | | MIR2053 | 1.00 |
| 12707 | 3 | | | | | MIR135A1 | 1.00 | | 12803 | 3 | | | | | MIR2054 | 1.00 |
| 12708 | 3 | | | | | MIR135A2 | 1.00 | | 12804 | 3 | | | | | MIR206 | 1.00 |
| 12709 | 3 | | | | | MIR135B | 1.00 | | 12805 | 3 | | | | | MIR208A | 1.00 |
| 12710 | 3 | | | | | MIR136 | 1.00 | | 12806 | 3 | | | | | MIR208B | 1.00 |
| 12711 | 3 | | | | | MIR137 | 1.00 | | 12807 | 3 | | | | | MIR20A | 1.00 |
| 12712 | 3 | | | | | MIR137HG | 1.00 | | 12808 | 3 | | | | | MIR20B | 1.00 |
| 12713 | 3 | | | | | MIR138-1 | 1.00 | | 12809 | 3 | | | | | MIR21 | 1.00 |
| 12714 | 3 | | | | | MIR138-2 | 1.00 | | 12810 | 3 | | | | | MIR211 | 1.00 |
| 12715 | 3 | | | | | MIR139 | 1.00 | | 12811 | 3 | | | | | MIR2110 | 1.00 |
| 12716 | 3 | | | | | MIR140 | 1.00 | | 12812 | 3 | | | | | MIR2113 | 1.00 |
| 12717 | 3 | | | | | MIR141 | 1.00 | | 12813 | 3 | | | | | MIR2114 | 1.00 |
| 12718 | 3 | | | | | MIR142 | 1.00 | | 12814 | 3 | | | | | MIR2116 | 1.00 |
| 12719 | 3 | | | | | MIR143 | 1.00 | | 12815 | 3 | | | | | MIR2117 | 1.00 |
| 12720 | 3 | | | | | MIR144 | 1.00 | | 12816 | 3 | | | | | MIR212 | 1.00 |
| 12721 | 3 | | | | | MIR145 | 1.00 | | 12817 | 3 | | | | | MIR214 | 1.00 |
| 12722 | 3 | | | | | MIR1468 | 1.00 | | 12818 | 3 | | | | | MIR215 | 1.00 |
| 12723 | 3 | | | | | MIR1469 | 1.00 | | 12819 | 3 | | | | | MIR216A | 1.00 |
| 12724 | 3 | | | | | MIR146A | 1.00 | | 12820 | 3 | | | | | MIR216B | 1.00 |
| 12725 | 3 | | | | | MIR146B | 1.00 | | 12821 | 3 | | | | | MIR217 | 1.00 |
| 12726 | 3 | | | | | MIR1470 | 1.00 | | 12822 | 3 | | | | | MIR218-1 | 1.00 |
| 12727 | 3 | | | | | MIR1471 | 1.00 | | 12823 | 3 | | | | | MIR218-2 | 1.00 |
| 12728 | 3 | | | | | MIR147A | 1.00 | | 12824 | 3 | | | | | MIR219-1 | 1.00 |
| 12729 | 3 | | | | | MIR147B | 1.00 | | 12825 | 3 | | | | | MIR219-2 | 1.00 |
| 12730 | 3 | | | | | MIR148A | 1.00 | | 12826 | 3 | | | | | MIR22 | 1.00 |
| 12731 | 3 | | | | | MIR148B | 1.00 | | 12827 | 3 | | | | | MIR221 | 1.00 |
| 12732 | 3 | | | | | MIR149 | 1.00 | | 12828 | 3 | | | | | MIR222 | 1.00 |
| 12733 | 3 | | | | | MIR150 | 1.00 | | 12829 | 3 | | | | | MIR223 | 1.00 |
| 12734 | 3 | | | | | MIR152 | 1.00 | | 12830 | 3 | | | | | MIR2276 | 1.00 |
| 12735 | 3 | | | | | MIR153-1 | 1.00 | | 12831 | 3 | | | | | MIR2277 | 1.00 |
| 12736 | 3 | | | | | MIR153-2 | 1.00 | | 12832 | 3 | | | | | MIR2278 | 1.00 |
| 12737 | 3 | | | | | MIR1537 | 1.00 | | 12833 | 3 | | | | | MIR2355 | 1.00 |
| 12738 | 3 | | | | | MIR1538 | 1.00 | | 12834 | 3 | | | | | MIR2392 | 1.00 |
| 12739 | 3 | | | | | MIR1539 | 1.00 | | 12835 | 3 | | | | | MIR23A | 1.00 |
| 12740 | 3 | | | | | MIR154 | 1.00 | | 12836 | 3 | | | | | MIR23B | 1.00 |
| 12741 | 3 | | | | | MIR155 | 1.00 | | 12837 | 3 | | | | | MIR23C | 1.00 |
| 12742 | 3 | | | | | MIR155HG | 1.00 | | 12838 | 3 | | | | | MIR24-1 | 1.00 |
| 12743 | 3 | | | | | MIR15A | 1.00 | | 12839 | 3 | | | | | MIR24-2 | 1.00 |
| 12744 | 3 | | | | | MIR15B | 1.00 | | 12840 | 3 | | | | | MIR2467 | 1.00 |
| 12745 | 3 | | | | | MIR16-1 | 1.00 | | 12841 | 3 | | | | | MIR25 | 1.00 |
| 12746 | 3 | | | | | MIR16-2 | 1.00 | | 12842 | 3 | | | | | MIR2681 | 1.00 |
| 12747 | 3 | | | | | MIR17 | 1.00 | | 12843 | 3 | | | | | MIR2682 | 1.00 |
| 12748 | 3 | | | | | MIR181A1 | 1.00 | | 12844 | 3 | | | | | MIR26A1 | 1.00 |
| 12749 | 3 | | | | | MIR181A2 | 1.00 | | 12845 | 3 | | | | | MIR26A2 | 1.00 |
| 12750 | 3 | | | | | MIR181B1 | 1.00 | | 12846 | 3 | | | | | MIR26B | 1.00 |
| 12751 | 3 | | | | | MIR181B2 | 1.00 | | 12847 | 3 | | | | | MIR27A | 1.00 |
| 12752 | 3 | | | | | MIR181C | 1.00 | | 12848 | 3 | | | | | MIR27B | 1.00 |
| 12753 | 3 | | | | | MIR182 | 1.00 | | 12849 | 3 | | | | | MIR2861 | 1.00 |
| 12754 | 3 | | | | | MIR1827 | 1.00 | | 12850 | 3 | | | | | MIR2909 | 1.00 |
| 12755 | 3 | | | | | MIR183 | 1.00 | | 12851 | 3 | | | | | MIR296 | 1.00 |
| 12756 | 3 | | | | | MIR184 | 1.00 | | 12852 | 3 | | | | | MIR2964A | 1.00 |
| 12757 | 3 | | | | | MIR185 | 1.00 | | 12853 | 3 | | | | | MIR298 | 1.00 |
| 12758 | 3 | | | | | MIR186 | 1.00 | | 12854 | 3 | | | | | MIR299 | 1.00 |
| 12759 | 3 | | | | | MIR187 | 1.00 | | 12855 | 3 | | | | | MIR29A | 1.00 |
| 12760 | 3 | | | | | MIR188 | 1.00 | | 12856 | 3 | | | | | MIR29B1 | 1.00 |
| 12761 | 3 | | | | | MIR18A | 1.00 | | 12857 | 3 | | | | | MIR29B2 | 1.00 |
| 12762 | 3 | | | | | MIR18B | 1.00 | | 12858 | 3 | | | | | MIR29C | 1.00 |
| 12763 | 3 | | | | | MIR1908 | 1.00 | | 12859 | 3 | | | | | MIR300 | 1.00 |

Fig. 39 - 68

| | | | | | | | | | | | | | | | |
|---|---|---|---|---|---|---|---|---|---|---|---|---|---|---|---|
| 12860 | 3 | | | | | MIR301A | 1.00 | 12956 | 3 | | | | | MIR32 | 1.00 |
| 12861 | 3 | | | | | MIR301B | 1.00 | 12957 | 3 | | | | | MIR3200 | 1.00 |
| 12862 | 3 | | | | | MIR302A | 1.00 | 12958 | 3 | | | | | MIR3201 | 1.00 |
| 12863 | 3 | | | | | MIR302B | 1.00 | 12959 | 3 | | | | | MIR3202-1 | 1.00 |
| 12864 | 3 | | | | | MIR302C | 1.00 | 12960 | 3 | | | | | MIR3202-2 | 1.00 |
| 12865 | 3 | | | | | MIR302D | 1.00 | 12961 | 3 | | | | | MIR320A | 1.00 |
| 12866 | 3 | | | | | MIR302F | 1.00 | 12962 | 3 | | | | | MIR320B1 | 1.00 |
| 12867 | 3 | | | | | MIR3064 | 1.00 | 12963 | 3 | | | | | MIR320B2 | 1.00 |
| 12868 | 3 | | | | | MIR3065 | 1.00 | 12964 | 3 | | | | | MIR320C1 | 1.00 |
| 12869 | 3 | | | | | MIR3074 | 1.00 | 12965 | 3 | | | | | MIR320C2 | 1.00 |
| 12870 | 3 | | | | | MIR30A | 1.00 | 12966 | 3 | | | | | MIR320D1 | 1.00 |
| 12871 | 3 | | | | | MIR30B | 1.00 | 12967 | 3 | | | | | MIR320D2 | 1.00 |
| 12872 | 3 | | | | | MIR30C1 | 1.00 | 12968 | 3 | | | | | MIR320E | 1.00 |
| 12873 | 3 | | | | | MIR30C2 | 1.00 | 12969 | 3 | | | | | MIR323A | 1.00 |
| 12874 | 3 | | | | | MIR30D | 1.00 | 12970 | 3 | | | | | MIR323B | 1.00 |
| 12875 | 3 | | | | | MIR30E | 1.00 | 12971 | 3 | | | | | MIR324 | 1.00 |
| 12876 | 3 | | | | | MIR31 | 1.00 | 12972 | 3 | | | | | MIR326 | 1.00 |
| 12877 | 3 | | | | | MIR3115 | 1.00 | 12973 | 3 | | | | | MIR328 | 1.00 |
| 12878 | 3 | | | | | MIR3117 | 1.00 | 12974 | 3 | | | | | MIR329-1 | 1.00 |
| 12879 | 3 | | | | | MIR3119-1 | 1.00 | 12975 | 3 | | | | | MIR329-2 | 1.00 |
| 12880 | 3 | | | | | MIR3120 | 1.00 | 12976 | 3 | | | | | MIR330 | 1.00 |
| 12881 | 3 | | | | | MIR3121 | 1.00 | 12977 | 3 | | | | | MIR331 | 1.00 |
| 12882 | 3 | | | | | MIR3122 | 1.00 | 12978 | 3 | | | | | MIR335 | 1.00 |
| 12883 | 3 | | | | | MIR3123 | 1.00 | 12979 | 3 | | | | | MIR337 | 1.00 |
| 12884 | 3 | | | | | MIR3124 | 1.00 | 12980 | 3 | | | | | MIR338 | 1.00 |
| 12885 | 3 | | | | | MIR3125 | 1.00 | 12981 | 3 | | | | | MIR339 | 1.00 |
| 12886 | 3 | | | | | MIR3126 | 1.00 | 12982 | 3 | | | | | MIR33A | 1.00 |
| 12887 | 3 | | | | | MIR3127 | 1.00 | 12983 | 3 | | | | | MIR33B | 1.00 |
| 12888 | 3 | | | | | MIR3128 | 1.00 | 12984 | 3 | | | | | MIR340 | 1.00 |
| 12889 | 3 | | | | | MIR3129 | 1.00 | 12985 | 3 | | | | | MIR345 | 1.00 |
| 12890 | 3 | | | | | MIR3130-1 | 1.00 | 12986 | 3 | | | | | MIR346 | 1.00 |
| 12891 | 3 | | | | | MIR3131 | 1.00 | 12987 | 3 | | | | | MIR34A | 1.00 |
| 12892 | 3 | | | | | MIR3132 | 1.00 | 12988 | 3 | | | | | MIR34B | 1.00 |
| 12893 | 3 | | | | | MIR3134 | 1.00 | 12989 | 3 | | | | | MIR34C | 1.00 |
| 12894 | 3 | | | | | MIR3136 | 1.00 | 12990 | 3 | | | | | MIR3529 | 1.00 |
| 12895 | 3 | | | | | MIR3138 | 1.00 | 12991 | 3 | | | | | MIR3545 | 1.00 |
| 12896 | 3 | | | | | MIR3140 | 1.00 | 12992 | 3 | | | | | MIR3591 | 1.00 |
| 12897 | 3 | | | | | MIR3141 | 1.00 | 12993 | 3 | | | | | MIR3605 | 1.00 |
| 12898 | 3 | | | | | MIR3142 | 1.00 | 12994 | 3 | | | | | MIR3606 | 1.00 |
| 12899 | 3 | | | | | MIR3143 | 1.00 | 12995 | 3 | | | | | MIR3607 | 1.00 |
| 12900 | 3 | | | | | MIR3145 | 1.00 | 12996 | 3 | | | | | MIR3609 | 1.00 |
| 12901 | 3 | | | | | MIR3146 | 1.00 | 12997 | 3 | | | | | MIR3610 | 1.00 |
| 12902 | 3 | | | | | MIR3147 | 1.00 | 12998 | 3 | | | | | MIR3612 | 1.00 |
| 12903 | 3 | | | | | MIR3148 | 1.00 | 12999 | 3 | | | | | MIR3613 | 1.00 |
| 12904 | 3 | | | | | MIR3150A | 1.00 | 13000 | 3 | | | | | MIR3614 | 1.00 |
| 12905 | 3 | | | | | MIR3150B | 1.00 | 13001 | 3 | | | | | MIR3615 | 1.00 |
| 12906 | 3 | | | | | MIR3151 | 1.00 | 13002 | 3 | | | | | MIR3616 | 1.00 |
| 12907 | 3 | | | | | MIR3152 | 1.00 | 13003 | 3 | | | | | MIR3618 | 1.00 |
| 12908 | 3 | | | | | MIR3153 | 1.00 | 13004 | 3 | | | | | MIR3619 | 1.00 |
| 12909 | 3 | | | | | MIR3154 | 1.00 | 13005 | 3 | | | | | MIR362 | 1.00 |
| 12910 | 3 | | | | | MIR3155A | 1.00 | 13006 | 3 | | | | | MIR3620 | 1.00 |
| 12911 | 3 | | | | | MIR3155B | 1.00 | 13007 | 3 | | | | | MIR3621 | 1.00 |
| 12912 | 3 | | | | | MIR3156-1 | 1.00 | 13008 | 3 | | | | | MIR3622A | 1.00 |
| 12913 | 3 | | | | | MIR3156-2 | 1.00 | 13009 | 3 | | | | | MIR3622B | 1.00 |
| 12914 | 3 | | | | | MIR3156-3 | 1.00 | 13010 | 3 | | | | | MIR363 | 1.00 |
| 12915 | 3 | | | | | MIR3157 | 1.00 | 13011 | 3 | | | | | MIR3646 | 1.00 |
| 12916 | 3 | | | | | MIR3158-2 | 1.00 | 13012 | 3 | | | | | MIR3649 | 1.00 |
| 12917 | 3 | | | | | MIR3160-1 | 1.00 | 13013 | 3 | | | | | MIR3650 | 1.00 |
| 12918 | 3 | | | | | MIR3160-2 | 1.00 | 13014 | 3 | | | | | MIR3651 | 1.00 |
| 12919 | 3 | | | | | MIR3162 | 1.00 | 13015 | 3 | | | | | MIR3652 | 1.00 |
| 12920 | 3 | | | | | MIR3165 | 1.00 | 13016 | 3 | | | | | MIR3653 | 1.00 |
| 12921 | 3 | | | | | MIR3167 | 1.00 | 13017 | 3 | | | | | MIR3654 | 1.00 |
| 12922 | 3 | | | | | MIR3169 | 1.00 | 13018 | 3 | | | | | MIR3655 | 1.00 |
| 12923 | 3 | | | | | MIR3170 | 1.00 | 13019 | 3 | | | | | MIR3656 | 1.00 |
| 12924 | 3 | | | | | MIR3173 | 1.00 | 13020 | 3 | | | | | MIR3658 | 1.00 |
| 12925 | 3 | | | | | MIR3175 | 1.00 | 13021 | 3 | | | | | MIR3659 | 1.00 |
| 12926 | 3 | | | | | MIR3176 | 1.00 | 13022 | 3 | | | | | MIR365A | 1.00 |
| 12927 | 3 | | | | | MIR3177 | 1.00 | 13023 | 3 | | | | | MIR365B | 1.00 |
| 12928 | 3 | | | | | MIR3178 | 1.00 | 13024 | 3 | | | | | MIR3660 | 1.00 |
| 12929 | 3 | | | | | MIR3179-1 | 1.00 | 13025 | 3 | | | | | MIR3661 | 1.00 |
| 12930 | 3 | | | | | MIR3179-3 | 1.00 | 13026 | 3 | | | | | MIR3662 | 1.00 |
| 12931 | 3 | | | | | MIR3180-1 | 1.00 | 13027 | 3 | | | | | MIR3663 | 1.00 |
| 12932 | 3 | | | | | MIR3180-2 | 1.00 | 13028 | 3 | | | | | MIR3664 | 1.00 |
| 12933 | 3 | | | | | MIR3180-3 | 1.00 | 13029 | 3 | | | | | MIR3665 | 1.00 |
| 12934 | 3 | | | | | MIR3180-4 | 1.00 | 13030 | 3 | | | | | MIR3666 | 1.00 |
| 12935 | 3 | | | | | MIR3180-5 | 1.00 | 13031 | 3 | | | | | MIR3668 | 1.00 |
| 12936 | 3 | | | | | MIR3182 | 1.00 | 13032 | 3 | | | | | MIR367 | 1.00 |
| 12937 | 3 | | | | | MIR3183 | 1.00 | 13033 | 3 | | | | | MIR3671 | 1.00 |
| 12938 | 3 | | | | | MIR3184 | 1.00 | 13034 | 3 | | | | | MIR3675 | 1.00 |
| 12939 | 3 | | | | | MIR3185 | 1.00 | 13035 | 3 | | | | | MIR3676 | 1.00 |
| 12940 | 3 | | | | | MIR3186 | 1.00 | 13036 | 3 | | | | | MIR3677 | 1.00 |
| 12941 | 3 | | | | | MIR3187 | 1.00 | 13037 | 3 | | | | | MIR3678 | 1.00 |
| 12942 | 3 | | | | | MIR3188 | 1.00 | 13038 | 3 | | | | | MIR3679 | 1.00 |
| 12943 | 3 | | | | | MIR3189 | 1.00 | 13039 | 3 | | | | | MIR3680-1 | 1.00 |
| 12944 | 3 | | | | | MIR3190 | 1.00 | 13040 | 3 | | | | | MIR3682 | 1.00 |
| 12945 | 3 | | | | | MIR3191 | 1.00 | 13041 | 3 | | | | | MIR3684 | 1.00 |
| 12946 | 3 | | | | | MIR3192 | 1.00 | 13042 | 3 | | | | | MIR3685 | 1.00 |
| 12947 | 3 | | | | | MIR3193 | 1.00 | 13043 | 3 | | | | | MIR3687 | 1.00 |
| 12948 | 3 | | | | | MIR3194 | 1.00 | 13044 | 3 | | | | | MIR3688-1 | 1.00 |
| 12949 | 3 | | | | | MIR3196 | 1.00 | 13045 | 3 | | | | | MIR3688-2 | 1.00 |
| 12950 | 3 | | | | | MIR3197 | 1.00 | 13046 | 3 | | | | | MIR3689A | 1.00 |
| 12951 | 3 | | | | | MIR3198-1 | 1.00 | 13047 | 3 | | | | | MIR3689B | 1.00 |
| 12952 | 3 | | | | | MIR3198-2 | 1.00 | 13048 | 3 | | | | | MIR3689C | 1.00 |
| 12953 | 3 | | | | | MIR3199-1 | 1.00 | 13049 | 3 | | | | | MIR3689D1 | 1.00 |
| 12954 | 3 | | | | | MIR3199-2 | 1.00 | 13050 | 3 | | | | | MIR3689D2 | 1.00 |
| 12955 | 3 | | | | | MIR31HG | 1.00 | 13051 | 3 | | | | | MIR3689E | 1.00 |

Fig. 39 - 69

| | | | | | | | | | | | | | |
|---|---|---|---|---|---|---|---|---|---|---|---|---|---|
| 13052 | 3 | | | | | MIR3689F | 1.00 | 13148 | 3 | | | MIR4271 | 1.00 |
| 13053 | 3 | | | | | MIR369 | 1.00 | 13149 | 3 | | | MIR4272 | 1.00 |
| 13054 | 3 | | | | | MIR3690 | 1.00 | 13150 | 3 | | | MIR4273 | 1.00 |
| 13055 | 3 | | | | | MIR3691 | 1.00 | 13151 | 3 | | | MIR4274 | 1.00 |
| 13056 | 3 | | | | | MIR3692 | 1.00 | 13152 | 3 | | | MIR4275 | 1.00 |
| 13057 | 3 | | | | | MIR3714 | 1.00 | 13153 | 3 | | | MIR4276 | 1.00 |
| 13058 | 3 | | | | | MIR371A | 1.00 | 13154 | 3 | | | MIR4277 | 1.00 |
| 13059 | 3 | | | | | MIR371B | 1.00 | 13155 | 3 | | | MIR4278 | 1.00 |
| 13060 | 3 | | | | | MIR372 | 1.00 | 13156 | 3 | | | MIR4279 | 1.00 |
| 13061 | 3 | | | | | MIR373 | 1.00 | 13157 | 3 | | | MIR4280 | 1.00 |
| 13062 | 3 | | | | | MIR374A | 1.00 | 13158 | 3 | | | MIR4281 | 1.00 |
| 13063 | 3 | | | | | MIR374B | 1.00 | 13159 | 3 | | | MIR4282 | 1.00 |
| 13064 | 3 | | | | | MIR374C | 1.00 | 13160 | 3 | | | MIR4283-1 | 1.00 |
| 13065 | 3 | | | | | MIR375 | 1.00 | 13161 | 3 | | | MIR4283-2 | 1.00 |
| 13066 | 3 | | | | | MIR376A1 | 1.00 | 13162 | 3 | | | MIR4284 | 1.00 |
| 13067 | 3 | | | | | MIR376A2 | 1.00 | 13163 | 3 | | | MIR4285 | 1.00 |
| 13068 | 3 | | | | | MIR376B | 1.00 | 13164 | 3 | | | MIR4287 | 1.00 |
| 13069 | 3 | | | | | MIR376C | 1.00 | 13165 | 3 | | | MIR4288 | 1.00 |
| 13070 | 3 | | | | | MIR377 | 1.00 | 13166 | 3 | | | MIR4289 | 1.00 |
| 13071 | 3 | | | | | MIR378C | 1.00 | 13167 | 3 | | | MIR429 | 1.00 |
| 13072 | 3 | | | | | MIR378D1 | 1.00 | 13168 | 3 | | | MIR4290 | 1.00 |
| 13073 | 3 | | | | | MIR378D2 | 1.00 | 13169 | 3 | | | MIR4291 | 1.00 |
| 13074 | 3 | | | | | MIR378E | 1.00 | 13170 | 3 | | | MIR4292 | 1.00 |
| 13075 | 3 | | | | | MIR378F | 1.00 | 13171 | 3 | | | MIR4294 | 1.00 |
| 13076 | 3 | | | | | MIR379 | 1.00 | 13172 | 3 | | | MIR4295 | 1.00 |
| 13077 | 3 | | | | | MIR380 | 1.00 | 13173 | 3 | | | MIR4296 | 1.00 |
| 13078 | 3 | | | | | MIR381 | 1.00 | 13174 | 3 | | | MIR4297 | 1.00 |
| 13079 | 3 | | | | | MIR382 | 1.00 | 13175 | 3 | | | MIR4298 | 1.00 |
| 13080 | 3 | | | | | MIR383 | 1.00 | 13176 | 3 | | | MIR4299 | 1.00 |
| 13081 | 3 | | | | | MIR384 | 1.00 | 13177 | 3 | | | MIR4300 | 1.00 |
| 13082 | 3 | | | | | MIR3907 | 1.00 | 13178 | 3 | | | MIR4301 | 1.00 |
| 13083 | 3 | | | | | MIR3908 | 1.00 | 13179 | 3 | | | MIR4302 | 1.00 |
| 13084 | 3 | | | | | MIR3909 | 1.00 | 13180 | 3 | | | MIR4303 | 1.00 |
| 13085 | 3 | | | | | MIR3910-1 | 1.00 | 13181 | 3 | | | MIR4304 | 1.00 |
| 13086 | 3 | | | | | MIR3910-2 | 1.00 | 13182 | 3 | | | MIR4305 | 1.00 |
| 13087 | 3 | | | | | MIR3911 | 1.00 | 13183 | 3 | | | MIR4306 | 1.00 |
| 13088 | 3 | | | | | MIR3912 | 1.00 | 13184 | 3 | | | MIR4307 | 1.00 |
| 13089 | 3 | | | | | MIR3913-1 | 1.00 | 13185 | 3 | | | MIR4308 | 1.00 |
| 13090 | 3 | | | | | MIR3913-2 | 1.00 | 13186 | 3 | | | MIR4309 | 1.00 |
| 13091 | 3 | | | | | MIR3914-1 | 1.00 | 13187 | 3 | | | MIR431 | 1.00 |
| 13092 | 3 | | | | | MIR3914-2 | 1.00 | 13188 | 3 | | | MIR4310 | 1.00 |
| 13093 | 3 | | | | | MIR3916 | 1.00 | 13189 | 3 | | | MIR4311 | 1.00 |
| 13094 | 3 | | | | | MIR3917 | 1.00 | 13190 | 3 | | | MIR4312 | 1.00 |
| 13095 | 3 | | | | | MIR3918 | 1.00 | 13191 | 3 | | | MIR4313 | 1.00 |
| 13096 | 3 | | | | | MIR3919 | 1.00 | 13192 | 3 | | | MIR4314 | 1.00 |
| 13097 | 3 | | | | | MIR3920 | 1.00 | 13193 | 3 | | | MIR4315-2 | 1.00 |
| 13098 | 3 | | | | | MIR3921 | 1.00 | 13194 | 3 | | | MIR4316 | 1.00 |
| 13099 | 3 | | | | | MIR3922 | 1.00 | 13195 | 3 | | | MIR4317 | 1.00 |
| 13100 | 3 | | | | | MIR3924 | 1.00 | 13196 | 3 | | | MIR4318 | 1.00 |
| 13101 | 3 | | | | | MIR3925 | 1.00 | 13197 | 3 | | | MIR4319 | 1.00 |
| 13102 | 3 | | | | | MIR3926-1 | 1.00 | 13198 | 3 | | | MIR432 | 1.00 |
| 13103 | 3 | | | | | MIR3926-2 | 1.00 | 13199 | 3 | | | MIR4320 | 1.00 |
| 13104 | 3 | | | | | MIR3928 | 1.00 | 13200 | 3 | | | MIR4321 | 1.00 |
| 13105 | 3 | | | | | MIR3935 | 1.00 | 13201 | 3 | | | MIR4322 | 1.00 |
| 13106 | 3 | | | | | MIR3938 | 1.00 | 13202 | 3 | | | MIR4323 | 1.00 |
| 13107 | 3 | | | | | MIR3939 | 1.00 | 13203 | 3 | | | MIR4324 | 1.00 |
| 13108 | 3 | | | | | MIR3940 | 1.00 | 13204 | 3 | | | MIR4325 | 1.00 |
| 13109 | 3 | | | | | MIR3941 | 1.00 | 13205 | 3 | | | MIR4326 | 1.00 |
| 13110 | 3 | | | | | MIR3942 | 1.00 | 13206 | 3 | | | MIR4327 | 1.00 |
| 13111 | 3 | | | | | MIR3943 | 1.00 | 13207 | 3 | | | MIR4328 | 1.00 |
| 13112 | 3 | | | | | MIR3944 | 1.00 | 13208 | 3 | | | MIR4329 | 1.00 |
| 13113 | 3 | | | | | MIR3945 | 1.00 | 13209 | 3 | | | MIR433 | 1.00 |
| 13114 | 3 | | | | | MIR3960 | 1.00 | 13210 | 3 | | | MIR4330 | 1.00 |
| 13115 | 3 | | | | | MIR3973 | 1.00 | 13211 | 3 | | | MIR4417 | 1.00 |
| 13116 | 3 | | | | | MIR3974 | 1.00 | 13212 | 3 | | | MIR4420 | 1.00 |
| 13117 | 3 | | | | | MIR3975 | 1.00 | 13213 | 3 | | | MIR4422 | 1.00 |
| 13118 | 3 | | | | | MIR3976 | 1.00 | 13214 | 3 | | | MIR4423 | 1.00 |
| 13119 | 3 | | | | | MIR3977 | 1.00 | 13215 | 3 | | | MIR4424 | 1.00 |
| 13120 | 3 | | | | | MIR3978 | 1.00 | 13216 | 3 | | | MIR4426 | 1.00 |
| 13121 | 3 | | | | | MIR409 | 1.00 | 13217 | 3 | | | MIR4427 | 1.00 |
| 13122 | 3 | | | | | MIR410 | 1.00 | 13218 | 3 | | | MIR4429 | 1.00 |
| 13123 | 3 | | | | | MIR411 | 1.00 | 13219 | 3 | | | MIR4432 | 1.00 |
| 13124 | 3 | | | | | MIR412 | 1.00 | 13220 | 3 | | | MIR4434 | 1.00 |
| 13125 | 3 | | | | | MIR421 | 1.00 | 13221 | 3 | | | MIR4435-1 | 1.00 |
| 13126 | 3 | | | | | MIR423 | 1.00 | 13222 | 3 | | | MIR4435-2 | 1.00 |
| 13127 | 3 | | | | | MIR424 | 1.00 | 13223 | 3 | | | MIR4436A | 1.00 |
| 13128 | 3 | | | | | MIR425 | 1.00 | 13224 | 3 | | | MIR4436B1 | 1.00 |
| 13129 | 3 | | | | | MIR4251 | 1.00 | 13225 | 3 | | | MIR4437 | 1.00 |
| 13130 | 3 | | | | | MIR4252 | 1.00 | 13226 | 3 | | | MIR4439 | 1.00 |
| 13131 | 3 | | | | | MIR4253 | 1.00 | 13227 | 3 | | | MIR4440 | 1.00 |
| 13132 | 3 | | | | | MIR4254 | 1.00 | 13228 | 3 | | | MIR4441 | 1.00 |
| 13133 | 3 | | | | | MIR4255 | 1.00 | 13229 | 3 | | | MIR4442 | 1.00 |
| 13134 | 3 | | | | | MIR4256 | 1.00 | 13230 | 3 | | | MIR4443 | 1.00 |
| 13135 | 3 | | | | | MIR4257 | 1.00 | 13231 | 3 | | | MIR4444-1 | 1.00 |
| 13136 | 3 | | | | | MIR4258 | 1.00 | 13232 | 3 | | | MIR4446 | 1.00 |
| 13137 | 3 | | | | | MIR4260 | 1.00 | 13233 | 3 | | | MIR4449 | 1.00 |
| 13138 | 3 | | | | | MIR4261 | 1.00 | 13234 | 3 | | | MIR4450 | 1.00 |
| 13139 | 3 | | | | | MIR4262 | 1.00 | 13235 | 3 | | | MIR4451 | 1.00 |
| 13140 | 3 | | | | | MIR4263 | 1.00 | 13236 | 3 | | | MIR4453 | 1.00 |
| 13141 | 3 | | | | | MIR4264 | 1.00 | 13237 | 3 | | | MIR4454 | 1.00 |
| 13142 | 3 | | | | | MIR4265 | 1.00 | 13238 | 3 | | | MIR4456 | 1.00 |
| 13143 | 3 | | | | | MIR4266 | 1.00 | 13239 | 3 | | | MIR4457 | 1.00 |
| 13144 | 3 | | | | | MIR4267 | 1.00 | 13240 | 3 | | | MIR4458 | 1.00 |
| 13145 | 3 | | | | | MIR4268 | 1.00 | 13241 | 3 | | | MIR4460 | 1.00 |
| 13146 | 3 | | | | | MIR4269 | 1.00 | 13242 | 3 | | | MIR4461 | 1.00 |
| 13147 | 3 | | | | | MIR4270 | 1.00 | 13243 | 3 | | | MIR4462 | 1.00 |

Fig. 39 - 70

| | | | | | | | | | | | | | | |
|---|---|---|---|---|---|---|---|---|---|---|---|---|---|---|
| 13244 | 3 | | | | | MIR4464 | 1.00 | 13340 | 3 | | | | MIR4654 | 1.00 |
| 13245 | 3 | | | | | MIR4465 | 1.00 | 13341 | 3 | | | | MIR4655 | 1.00 |
| 13246 | 3 | | | | | MIR4466 | 1.00 | 13342 | 3 | | | | MIR4656 | 1.00 |
| 13247 | 3 | | | | | MIR4467 | 1.00 | 13343 | 3 | | | | MIR4657 | 1.00 |
| 13248 | 3 | | | | | MIR4468 | 1.00 | 13344 | 3 | | | | MIR4658 | 1.00 |
| 13249 | 3 | | | | | MIR4469 | 1.00 | 13345 | 3 | | | | MIR4659A | 1.00 |
| 13250 | 3 | | | | | MIR4470 | 1.00 | 13346 | 3 | | | | MIR4659B | 1.00 |
| 13251 | 3 | | | | | MIR4471 | 1.00 | 13347 | 3 | | | | MIR4660 | 1.00 |
| 13252 | 3 | | | | | MIR4472-1 | 1.00 | 13348 | 3 | | | | MIR4661 | 1.00 |
| 13253 | 3 | | | | | MIR4472-2 | 1.00 | 13349 | 3 | | | | MIR4663 | 1.00 |
| 13254 | 3 | | | | | MIR4473 | 1.00 | 13350 | 3 | | | | MIR4664 | 1.00 |
| 13255 | 3 | | | | | MIR4474 | 1.00 | 13351 | 3 | | | | MIR4665 | 1.00 |
| 13256 | 3 | | | | | MIR4475 | 1.00 | 13352 | 3 | | | | MIR4666A | 1.00 |
| 13257 | 3 | | | | | MIR4476 | 1.00 | 13353 | 3 | | | | MIR4667 | 1.00 |
| 13258 | 3 | | | | | MIR4478 | 1.00 | 13354 | 3 | | | | MIR4668 | 1.00 |
| 13259 | 3 | | | | | MIR4479 | 1.00 | 13355 | 3 | | | | MIR4669 | 1.00 |
| 13260 | 3 | | | | | MIR448 | 1.00 | 13356 | 3 | | | | MIR4670 | 1.00 |
| 13261 | 3 | | | | | MIR4480 | 1.00 | 13357 | 3 | | | | MIR4671 | 1.00 |
| 13262 | 3 | | | | | MIR4482-1 | 1.00 | 13358 | 3 | | | | MIR4672 | 1.00 |
| 13263 | 3 | | | | | MIR4483 | 1.00 | 13359 | 3 | | | | MIR4673 | 1.00 |
| 13264 | 3 | | | | | MIR4484 | 1.00 | 13360 | 3 | | | | MIR4674 | 1.00 |
| 13265 | 3 | | | | | MIR4485 | 1.00 | 13361 | 3 | | | | MIR4675 | 1.00 |
| 13266 | 3 | | | | | MIR4486 | 1.00 | 13362 | 3 | | | | MIR4676 | 1.00 |
| 13267 | 3 | | | | | MIR4488 | 1.00 | 13363 | 3 | | | | MIR4677 | 1.00 |
| 13268 | 3 | | | | | MIR4489 | 1.00 | 13364 | 3 | | | | MIR4678 | 1.00 |
| 13269 | 3 | | | | | MIR4490 | 1.00 | 13365 | 3 | | | | MIR4679-1 | 1.00 |
| 13270 | 3 | | | | | MIR4491 | 1.00 | 13366 | 3 | | | | MIR4679-2 | 1.00 |
| 13271 | 3 | | | | | MIR4492 | 1.00 | 13367 | 3 | | | | MIR4680 | 1.00 |
| 13272 | 3 | | | | | MIR4493 | 1.00 | 13368 | 3 | | | | MIR4681 | 1.00 |
| 13273 | 3 | | | | | MIR4497 | 1.00 | 13369 | 3 | | | | MIR4682 | 1.00 |
| 13274 | 3 | | | | | MIR4498 | 1.00 | 13370 | 3 | | | | MIR4683 | 1.00 |
| 13275 | 3 | | | | | MIR4499 | 1.00 | 13371 | 3 | | | | MIR4684 | 1.00 |
| 13276 | 3 | | | | | MIR449A | 1.00 | 13372 | 3 | | | | MIR4685 | 1.00 |
| 13277 | 3 | | | | | MIR449B | 1.00 | 13373 | 3 | | | | MIR4686 | 1.00 |
| 13278 | 3 | | | | | MIR449C | 1.00 | 13374 | 3 | | | | MIR4687 | 1.00 |
| 13279 | 3 | | | | | MIR4500 | 1.00 | 13375 | 3 | | | | MIR4688 | 1.00 |
| 13280 | 3 | | | | | MIR4500HG | 1.00 | 13376 | 3 | | | | MIR4689 | 1.00 |
| 13281 | 3 | | | | | MIR4503 | 1.00 | 13377 | 3 | | | | MIR4690 | 1.00 |
| 13282 | 3 | | | | | MIR4505 | 1.00 | 13378 | 3 | | | | MIR4691 | 1.00 |
| 13283 | 3 | | | | | MIR4508 | 1.00 | 13379 | 3 | | | | MIR4692 | 1.00 |
| 13284 | 3 | | | | | MIR4509-1 | 1.00 | 13380 | 3 | | | | MIR4693 | 1.00 |
| 13285 | 3 | | | | | MIR450A1 | 1.00 | 13381 | 3 | | | | MIR4694 | 1.00 |
| 13286 | 3 | | | | | MIR450A2 | 1.00 | 13382 | 3 | | | | MIR4695 | 1.00 |
| 13287 | 3 | | | | | MIR450B | 1.00 | 13383 | 3 | | | | MIR4696 | 1.00 |
| 13288 | 3 | | | | | MIR4510 | 1.00 | 13384 | 3 | | | | MIR4697 | 1.00 |
| 13289 | 3 | | | | | MIR4511 | 1.00 | 13385 | 3 | | | | MIR4698 | 1.00 |
| 13290 | 3 | | | | | MIR4513 | 1.00 | 13386 | 3 | | | | MIR4699 | 1.00 |
| 13291 | 3 | | | | | MIR4514 | 1.00 | 13387 | 3 | | | | MIR4700 | 1.00 |
| 13292 | 3 | | | | | MIR4515 | 1.00 | 13388 | 3 | | | | MIR4701 | 1.00 |
| 13293 | 3 | | | | | MIR4516 | 1.00 | 13389 | 3 | | | | MIR4703 | 1.00 |
| 13294 | 3 | | | | | MIR4517 | 1.00 | 13390 | 3 | | | | MIR4705 | 1.00 |
| 13295 | 3 | | | | | MIR4518 | 1.00 | 13391 | 3 | | | | MIR4706 | 1.00 |
| 13296 | 3 | | | | | MIR4519 | 1.00 | 13392 | 3 | | | | MIR4707 | 1.00 |
| 13297 | 3 | | | | | MIR451A | 1.00 | 13393 | 3 | | | | MIR4708 | 1.00 |
| 13298 | 3 | | | | | MIR451B | 1.00 | 13394 | 3 | | | | MIR4709 | 1.00 |
| 13299 | 3 | | | | | MIR452 | 1.00 | 13395 | 3 | | | | MIR4710 | 1.00 |
| 13300 | 3 | | | | | MIR4520A | 1.00 | 13396 | 3 | | | | MIR4711 | 1.00 |
| 13301 | 3 | | | | | MIR4520B | 1.00 | 13397 | 3 | | | | MIR4712 | 1.00 |
| 13302 | 3 | | | | | MIR4521 | 1.00 | 13398 | 3 | | | | MIR4713 | 1.00 |
| 13303 | 3 | | | | | MIR4522 | 1.00 | 13399 | 3 | | | | MIR4714 | 1.00 |
| 13304 | 3 | | | | | MIR4523 | 1.00 | 13400 | 3 | | | | MIR4715 | 1.00 |
| 13305 | 3 | | | | | MIR4524A | 1.00 | 13401 | 3 | | | | MIR4716 | 1.00 |
| 13306 | 3 | | | | | MIR4526 | 1.00 | 13402 | 3 | | | | MIR4717 | 1.00 |
| 13307 | 3 | | | | | MIR4529 | 1.00 | 13403 | 3 | | | | MIR4718 | 1.00 |
| 13308 | 3 | | | | | MIR4530 | 1.00 | 13404 | 3 | | | | MIR4719 | 1.00 |
| 13309 | 3 | | | | | MIR4531 | 1.00 | 13405 | 3 | | | | MIR4720 | 1.00 |
| 13310 | 3 | | | | | MIR4532 | 1.00 | 13406 | 3 | | | | MIR4721 | 1.00 |
| 13311 | 3 | | | | | MIR4533 | 1.00 | 13407 | 3 | | | | MIR4722 | 1.00 |
| 13312 | 3 | | | | | MIR4534 | 1.00 | 13408 | 3 | | | | MIR4723 | 1.00 |
| 13313 | 3 | | | | | MIR4535 | 1.00 | 13409 | 3 | | | | MIR4724 | 1.00 |
| 13314 | 3 | | | | | MIR4536-1 | 1.00 | 13410 | 3 | | | | MIR4725 | 1.00 |
| 13315 | 3 | | | | | MIR454 | 1.00 | 13411 | 3 | | | | MIR4726 | 1.00 |
| 13316 | 3 | | | | | MIR4540 | 1.00 | 13412 | 3 | | | | MIR4727 | 1.00 |
| 13317 | 3 | | | | | MIR455 | 1.00 | 13413 | 3 | | | | MIR4728 | 1.00 |
| 13318 | 3 | | | | | MIR4632 | 1.00 | 13414 | 3 | | | | MIR4729 | 1.00 |
| 13319 | 3 | | | | | MIR4633 | 1.00 | 13415 | 3 | | | | MIR4730 | 1.00 |
| 13320 | 3 | | | | | MIR4634 | 1.00 | 13416 | 3 | | | | MIR4731 | 1.00 |
| 13321 | 3 | | | | | MIR4635 | 1.00 | 13417 | 3 | | | | MIR4732 | 1.00 |
| 13322 | 3 | | | | | MIR4636 | 1.00 | 13418 | 3 | | | | MIR4733 | 1.00 |
| 13323 | 3 | | | | | MIR4637 | 1.00 | 13419 | 3 | | | | MIR4734 | 1.00 |
| 13324 | 3 | | | | | MIR4638 | 1.00 | 13420 | 3 | | | | MIR4735 | 1.00 |
| 13325 | 3 | | | | | MIR4639 | 1.00 | 13421 | 3 | | | | MIR4736 | 1.00 |
| 13326 | 3 | | | | | MIR4640 | 1.00 | 13422 | 3 | | | | MIR4737 | 1.00 |
| 13327 | 3 | | | | | MIR4641 | 1.00 | 13423 | 3 | | | | MIR4738 | 1.00 |
| 13328 | 3 | | | | | MIR4642 | 1.00 | 13424 | 3 | | | | MIR4739 | 1.00 |
| 13329 | 3 | | | | | MIR4643 | 1.00 | 13425 | 3 | | | | MIR4740 | 1.00 |
| 13330 | 3 | | | | | MIR4644 | 1.00 | 13426 | 3 | | | | MIR4741 | 1.00 |
| 13331 | 3 | | | | | MIR4645 | 1.00 | 13427 | 3 | | | | MIR4742 | 1.00 |
| 13332 | 3 | | | | | MIR4646 | 1.00 | 13428 | 3 | | | | MIR4743 | 1.00 |
| 13333 | 3 | | | | | MIR4647 | 1.00 | 13429 | 3 | | | | MIR4744 | 1.00 |
| 13334 | 3 | | | | | MIR4648 | 1.00 | 13430 | 3 | | | | MIR4745 | 1.00 |
| 13335 | 3 | | | | | MIR4649 | 1.00 | 13431 | 3 | | | | MIR4746 | 1.00 |
| 13336 | 3 | | | | | MIR4650-1 | 1.00 | 13432 | 3 | | | | MIR4747 | 1.00 |
| 13337 | 3 | | | | | MIR4651 | 1.00 | 13433 | 3 | | | | MIR4748 | 1.00 |
| 13338 | 3 | | | | | MIR4652 | 1.00 | 13434 | 3 | | | | MIR4749 | 1.00 |
| 13339 | 3 | | | | | MIR4653 | 1.00 | 13435 | 3 | | | | MIR4750 | 1.00 |

Fig. 39 - 71

| | | | | | | | | | | | | | | |
|---|---|---|---|---|---|---|---|---|---|---|---|---|---|---|
| 13436 | 3 | | | | | | MIR4751 | 1.00 | 13532 | 3 | | | MIR516A2 | 1.00 |
| 13437 | 3 | | | | | | MIR4752 | 1.00 | 13533 | 3 | | | MIR516B1 | 1.00 |
| 13438 | 3 | | | | | | MIR4753 | 1.00 | 13534 | 3 | | | MIR516B2 | 1.00 |
| 13439 | 3 | | | | | | MIR4754 | 1.00 | 13535 | 3 | | | MIR517A | 1.00 |
| 13440 | 3 | | | | | | MIR4755 | 1.00 | 13536 | 3 | | | MIR517B | 1.00 |
| 13441 | 3 | | | | | | MIR4756 | 1.00 | 13537 | 3 | | | MIR517C | 1.00 |
| 13442 | 3 | | | | | | MIR4757 | 1.00 | 13538 | 3 | | | MIR518A1 | 1.00 |
| 13443 | 3 | | | | | | MIR4758 | 1.00 | 13539 | 3 | | | MIR518A2 | 1.00 |
| 13444 | 3 | | | | | | MIR4759 | 1.00 | 13540 | 3 | | | MIR518B | 1.00 |
| 13445 | 3 | | | | | | MIR4760 | 1.00 | 13541 | 3 | | | MIR518C | 1.00 |
| 13446 | 3 | | | | | | MIR4761 | 1.00 | 13542 | 3 | | | MIR518D | 1.00 |
| 13447 | 3 | | | | | | MIR4762 | 1.00 | 13543 | 3 | | | MIR518E | 1.00 |
| 13448 | 3 | | | | | | MIR4763 | 1.00 | 13544 | 3 | | | MIR518F | 1.00 |
| 13449 | 3 | | | | | | MIR4764 | 1.00 | 13545 | 3 | | | MIR519A1 | 1.00 |
| 13450 | 3 | | | | | | MIR4765 | 1.00 | 13546 | 3 | | | MIR519A2 | 1.00 |
| 13451 | 3 | | | | | | MIR4766 | 1.00 | 13547 | 3 | | | MIR519B | 1.00 |
| 13452 | 3 | | | | | | MIR4767 | 1.00 | 13548 | 3 | | | MIR519C | 1.00 |
| 13453 | 3 | | | | | | MIR4768 | 1.00 | 13549 | 3 | | | MIR519D | 1.00 |
| 13454 | 3 | | | | | | MIR4769 | 1.00 | 13550 | 3 | | | MIR519E | 1.00 |
| 13455 | 3 | | | | | | MIR4770 | 1.00 | 13551 | 3 | | | MIR520A | 1.00 |
| 13456 | 3 | | | | | | MIR4772 | 1.00 | 13552 | 3 | | | MIR520B | 1.00 |
| 13457 | 3 | | | | | | MIR4773-2 | 1.00 | 13553 | 3 | | | MIR520C | 1.00 |
| 13458 | 3 | | | | | | MIR4774 | 1.00 | 13554 | 3 | | | MIR520D | 1.00 |
| 13459 | 3 | | | | | | MIR4775 | 1.00 | 13555 | 3 | | | MIR520E | 1.00 |
| 13460 | 3 | | | | | | MIR4776-2 | 1.00 | 13556 | 3 | | | MIR520F | 1.00 |
| 13461 | 3 | | | | | | MIR4777 | 1.00 | 13557 | 3 | | | MIR520G | 1.00 |
| 13462 | 3 | | | | | | MIR4778 | 1.00 | 13558 | 3 | | | MIR520H | 1.00 |
| 13463 | 3 | | | | | | MIR4779 | 1.00 | 13559 | 3 | | | MIR521-1 | 1.00 |
| 13464 | 3 | | | | | | MIR4780 | 1.00 | 13560 | 3 | | | MIR521-2 | 1.00 |
| 13465 | 3 | | | | | | MIR4781 | 1.00 | 13561 | 3 | | | MIR522 | 1.00 |
| 13466 | 3 | | | | | | MIR4782 | 1.00 | 13562 | 3 | | | MIR523 | 1.00 |
| 13467 | 3 | | | | | | MIR4783 | 1.00 | 13563 | 3 | | | MIR524 | 1.00 |
| 13468 | 3 | | | | | | MIR4784 | 1.00 | 13564 | 3 | | | MIR525 | 1.00 |
| 13469 | 3 | | | | | | MIR4785 | 1.00 | 13565 | 3 | | | MIR526A1 | 1.00 |
| 13470 | 3 | | | | | | MIR4786 | 1.00 | 13566 | 3 | | | MIR526A2 | 1.00 |
| 13471 | 3 | | | | | | MIR4787 | 1.00 | 13567 | 3 | | | MIR526B | 1.00 |
| 13472 | 3 | | | | | | MIR4788 | 1.00 | 13568 | 3 | | | MIR527 | 1.00 |
| 13473 | 3 | | | | | | MIR4789 | 1.00 | 13569 | 3 | | | MIR532 | 1.00 |
| 13474 | 3 | | | | | | MIR4790 | 1.00 | 13570 | 3 | | | MIR539 | 1.00 |
| 13475 | 3 | | | | | | MIR4791 | 1.00 | 13571 | 3 | | | MIR541 | 1.00 |
| 13476 | 3 | | | | | | MIR4792 | 1.00 | 13572 | 3 | | | MIR542 | 1.00 |
| 13477 | 3 | | | | | | MIR4793 | 1.00 | 13573 | 3 | | | MIR543 | 1.00 |
| 13478 | 3 | | | | | | MIR4794 | 1.00 | 13574 | 3 | | | MIR545 | 1.00 |
| 13479 | 3 | | | | | | MIR4795 | 1.00 | 13575 | 3 | | | MIR548A1 | 1.00 |
| 13480 | 3 | | | | | | MIR4796 | 1.00 | 13576 | 3 | | | MIR548A2 | 1.00 |
| 13481 | 3 | | | | | | MIR4797 | 1.00 | 13577 | 3 | | | MIR548A3 | 1.00 |
| 13482 | 3 | | | | | | MIR4798 | 1.00 | 13578 | 3 | | | MIR548AA1 | 1.00 |
| 13483 | 3 | | | | | | MIR4799 | 1.00 | 13579 | 3 | | | MIR548AA2 | 1.00 |
| 13484 | 3 | | | | | | MIR4800 | 1.00 | 13580 | 3 | | | MIR548AC | 1.00 |
| 13485 | 3 | | | | | | MIR4801 | 1.00 | 13581 | 3 | | | MIR548AD | 1.00 |
| 13486 | 3 | | | | | | MIR4802 | 1.00 | 13582 | 3 | | | MIR548AE2 | 1.00 |
| 13487 | 3 | | | | | | MIR4803 | 1.00 | 13583 | 3 | | | MIR548AI | 1.00 |
| 13488 | 3 | | | | | | MIR4804 | 1.00 | 13584 | 3 | | | MIR548AJ2 | 1.00 |
| 13489 | 3 | | | | | | MIR483 | 1.00 | 13585 | 3 | | | MIR548AL | 1.00 |
| 13490 | 3 | | | | | | MIR484 | 1.00 | 13586 | 3 | | | MIR548AN | 1.00 |
| 13491 | 3 | | | | | | MIR485 | 1.00 | 13587 | 3 | | | MIR548B | 1.00 |
| 13492 | 3 | | | | | | MIR486 | 1.00 | 13588 | 3 | | | MIR548C | 1.00 |
| 13493 | 3 | | | | | | MIR487A | 1.00 | 13589 | 3 | | | MIR548D2 | 1.00 |
| 13494 | 3 | | | | | | MIR487B | 1.00 | 13590 | 3 | | | MIR548F1 | 1.00 |
| 13495 | 3 | | | | | | MIR488 | 1.00 | 13591 | 3 | | | MIR548F2 | 1.00 |
| 13496 | 3 | | | | | | MIR489 | 1.00 | 13592 | 3 | | | MIR548F3 | 1.00 |
| 13497 | 3 | | | | | | MIR490 | 1.00 | 13593 | 3 | | | MIR548F4 | 1.00 |
| 13498 | 3 | | | | | | MIR491 | 1.00 | 13594 | 3 | | | MIR548F5 | 1.00 |
| 13499 | 3 | | | | | | MIR493 | 1.00 | 13595 | 3 | | | MIR548G | 1.00 |
| 13500 | 3 | | | | | | MIR494 | 1.00 | 13596 | 3 | | | MIR548H2 | 1.00 |
| 13501 | 3 | | | | | | MIR495 | 1.00 | 13597 | 3 | | | MIR548H3 | 1.00 |
| 13502 | 3 | | | | | | MIR496 | 1.00 | 13598 | 3 | | | MIR548H4 | 1.00 |
| 13503 | 3 | | | | | | MIR497 | 1.00 | 13599 | 3 | | | MIR548I1 | 1.00 |
| 13504 | 3 | | | | | | MIR498 | 1.00 | 13600 | 3 | | | MIR548I2 | 1.00 |
| 13505 | 3 | | | | | | MIR499A | 1.00 | 13601 | 3 | | | MIR548I3 | 1.00 |
| 13506 | 3 | | | | | | MIR499B | 1.00 | 13602 | 3 | | | MIR548I4 | 1.00 |
| 13507 | 3 | | | | | | MIR500A | 1.00 | 13603 | 3 | | | MIR548J | 1.00 |
| 13508 | 3 | | | | | | MIR500B | 1.00 | 13604 | 3 | | | MIR548K | 1.00 |
| 13509 | 3 | | | | | | MIR501 | 1.00 | 13605 | 3 | | | MIR548M | 1.00 |
| 13510 | 3 | | | | | | MIR502 | 1.00 | 13606 | 3 | | | MIR548N | 1.00 |
| 13511 | 3 | | | | | | MIR503 | 1.00 | 13607 | 3 | | | MIR548O2 | 1.00 |
| 13512 | 3 | | | | | | MIR504 | 1.00 | 13608 | 3 | | | MIR548Q | 1.00 |
| 13513 | 3 | | | | | | MIR5047 | 1.00 | 13609 | 3 | | | MIR548T | 1.00 |
| 13514 | 3 | | | | | | MIR505 | 1.00 | 13610 | 3 | | | MIR548W | 1.00 |
| 13515 | 3 | | | | | | MIR506 | 1.00 | 13611 | 3 | | | MIR548X | 1.00 |
| 13516 | 3 | | | | | | MIR507 | 1.00 | 13612 | 3 | | | MIR548Y | 1.00 |
| 13517 | 3 | | | | | | MIR508 | 1.00 | 13613 | 3 | | | MIR549 | 1.00 |
| 13518 | 3 | | | | | | MIR509-1 | 1.00 | 13614 | 3 | | | MIR550A3 | 1.00 |
| 13519 | 3 | | | | | | MIR509-2 | 1.00 | 13615 | 3 | | | MIR550B1 | 1.00 |
| 13520 | 3 | | | | | | MIR509-3 | 1.00 | 13616 | 3 | | | MIR550B2 | 1.00 |
| 13521 | 3 | | | | | | MIR509S | 1.00 | 13617 | 3 | | | MIR551A | 1.00 |
| 13522 | 3 | | | | | | MIR510 | 1.00 | 13618 | 3 | | | MIR551B | 1.00 |
| 13523 | 3 | | | | | | MIR511-2 | 1.00 | 13619 | 3 | | | MIR553 | 1.00 |
| 13524 | 3 | | | | | | MIR512-1 | 1.00 | 13620 | 3 | | | MIR554 | 1.00 |
| 13525 | 3 | | | | | | MIR512-2 | 1.00 | 13621 | 3 | | | MIR555 | 1.00 |
| 13526 | 3 | | | | | | MIR514A1 | 1.00 | 13622 | 3 | | | MIR556 | 1.00 |
| 13527 | 3 | | | | | | MIR514A3 | 1.00 | 13623 | 3 | | | MIR557 | 1.00 |
| 13528 | 3 | | | | | | MIR514B | 1.00 | 13624 | 3 | | | MIR558 | 1.00 |
| 13529 | 3 | | | | | | MIR515-1 | 1.00 | 13625 | 3 | | | MIR559 | 1.00 |
| 13530 | 3 | | | | | | MIR515-2 | 1.00 | 13626 | 3 | | | MIR561 | 1.00 |
| 13531 | 3 | | | | | | MIR516A1 | 1.00 | 13627 | 3 | | | MIR563 | 1.00 |

Fig. 39 - 72

| | | | | | | | | | | | | | | | |
|---|---|---|---|---|---|---|---|---|---|---|---|---|---|---|---|
| 13628 | 3 | | | | | MIR564 | 1.00 | 13724 | 3 | | | | | MIR758 | 1.00 |
| 13629 | 3 | | | | | MIR567 | 1.00 | 13725 | 3 | | | | | MIR759 | 1.00 |
| 13630 | 3 | | | | | MIR568 | 1.00 | 13726 | 3 | | | | | MIR760 | 1.00 |
| 13631 | 3 | | | | | MIR569 | 1.00 | 13727 | 3 | | | | | MIR761 | 1.00 |
| 13632 | 3 | | | | | MIR570 | 1.00 | 13728 | 3 | | | | | MIR762 | 1.00 |
| 13633 | 3 | | | | | MIR572 | 1.00 | 13729 | 3 | | | | | MIR764 | 1.00 |
| 13634 | 3 | | | | | MIR573 | 1.00 | 13730 | 3 | | | | | MIR765 | 1.00 |
| 13635 | 3 | | | | | MIR574 | 1.00 | 13731 | 3 | | | | | MIR766 | 1.00 |
| 13636 | 3 | | | | | MIR575 | 1.00 | 13732 | 3 | | | | | MIR767 | 1.00 |
| 13637 | 3 | | | | | MIR577 | 1.00 | 13733 | 3 | | | | | MIR769 | 1.00 |
| 13638 | 3 | | | | | MIR578 | 1.00 | 13734 | 3 | | | | | MIR770 | 1.00 |
| 13639 | 3 | | | | | MIR580 | 1.00 | 13735 | 3 | | | | | MIR802 | 1.00 |
| 13640 | 3 | | | | | MIR581 | 1.00 | 13736 | 3 | | | | | MIR873 | 1.00 |
| 13641 | 3 | | | | | MIR583 | 1.00 | 13737 | 3 | | | | | MIR874 | 1.00 |
| 13642 | 3 | | | | | MIR585 | 1.00 | 13738 | 3 | | | | | MIR875 | 1.00 |
| 13643 | 3 | | | | | MIR586 | 1.00 | 13739 | 3 | | | | | MIR876 | 1.00 |
| 13644 | 3 | | | | | MIR589 | 1.00 | 13740 | 3 | | | | | MIR877 | 1.00 |
| 13645 | 3 | | | | | MIR590 | 1.00 | 13741 | 3 | | | | | MIR885 | 1.00 |
| 13646 | 3 | | | | | MIR591 | 1.00 | 13742 | 3 | | | | | MIR888 | 1.00 |
| 13647 | 3 | | | | | MIR592 | 1.00 | 13743 | 3 | | | | | MIR889 | 1.00 |
| 13648 | 3 | | | | | MIR593 | 1.00 | 13744 | 3 | | | | | MIR890 | 1.00 |
| 13649 | 3 | | | | | MIR595 | 1.00 | 13745 | 3 | | | | | MIR891A | 1.00 |
| 13650 | 3 | | | | | MIR596 | 1.00 | 13746 | 3 | | | | | MIR891B | 1.00 |
| 13651 | 3 | | | | | MIR597 | 1.00 | 13747 | 3 | | | | | MIR892A | 1.00 |
| 13652 | 3 | | | | | MIR598 | 1.00 | 13748 | 3 | | | | | MIR892B | 1.00 |
| 13653 | 3 | | | | | MIR599 | 1.00 | 13749 | 3 | | | | | MIR9-1 | 1.00 |
| 13654 | 3 | | | | | MIR600 | 1.00 | 13750 | 3 | | | | | MIR9-2 | 1.00 |
| 13655 | 3 | | | | | MIR601 | 1.00 | 13751 | 3 | | | | | MIR920 | 1.00 |
| 13656 | 3 | | | | | MIR602 | 1.00 | 13752 | 3 | | | | | MIR921 | 1.00 |
| 13657 | 3 | | | | | MIR603 | 1.00 | 13753 | 3 | | | | | MIR922 | 1.00 |
| 13658 | 3 | | | | | MIR604 | 1.00 | 13754 | 3 | | | | | MIR92A1 | 1.00 |
| 13659 | 3 | | | | | MIR605 | 1.00 | 13755 | 3 | | | | | MIR92A2 | 1.00 |
| 13660 | 3 | | | | | MIR608 | 1.00 | 13756 | 3 | | | | | MIR92B | 1.00 |
| 13661 | 3 | | | | | MIR609 | 1.00 | 13757 | 3 | | | | | MIR93 | 1.00 |
| 13662 | 3 | | | | | MIR610 | 1.00 | 13758 | 3 | | | | | MIR9-3 | 1.00 |
| 13663 | 3 | | | | | MIR611 | 1.00 | 13759 | 3 | | | | | MIR933 | 1.00 |
| 13664 | 3 | | | | | MIR612 | 1.00 | 13760 | 3 | | | | | MIR934 | 1.00 |
| 13665 | 3 | | | | | MIR613 | 1.00 | 13761 | 3 | | | | | MIR935 | 1.00 |
| 13666 | 3 | | | | | MIR614 | 1.00 | 13762 | 3 | | | | | MIR936 | 1.00 |
| 13667 | 3 | | | | | MIR615 | 1.00 | 13763 | 3 | | | | | MIR937 | 1.00 |
| 13668 | 3 | | | | | MIR617 | 1.00 | 13764 | 3 | | | | | MIR938 | 1.00 |
| 13669 | 3 | | | | | MIR618 | 1.00 | 13765 | 3 | | | | | MIR939 | 1.00 |
| 13670 | 3 | | | | | MIR620 | 1.00 | 13766 | 3 | | | | | MIR940 | 1.00 |
| 13671 | 3 | | | | | MIR621 | 1.00 | 13767 | 3 | | | | | MIR941-1 | 1.00 |
| 13672 | 3 | | | | | MIR622 | 1.00 | 13768 | 3 | | | | | MIR941-2 | 1.00 |
| 13673 | 3 | | | | | MIR623 | 1.00 | 13769 | 3 | | | | | MIR941-3 | 1.00 |
| 13674 | 3 | | | | | MIR624 | 1.00 | 13770 | 3 | | | | | MIR941-4 | 1.00 |
| 13675 | 3 | | | | | MIR626 | 1.00 | 13771 | 3 | | | | | MIR942 | 1.00 |
| 13676 | 3 | | | | | MIR627 | 1.00 | 13772 | 3 | | | | | MIR943 | 1.00 |
| 13677 | 3 | | | | | MIR628 | 1.00 | 13773 | 3 | | | | | MIR944 | 1.00 |
| 13678 | 3 | | | | | MIR629 | 1.00 | 13774 | 3 | | | | | MIR96 | 1.00 |
| 13679 | 3 | | | | | MIR630 | 1.00 | 13775 | 3 | | | | | MIR98 | 1.00 |
| 13680 | 3 | | | | | MIR631 | 1.00 | 13776 | 3 | | | | | MIR99A | 1.00 |
| 13681 | 3 | | | | | MIR632 | 1.00 | 13777 | 3 | | | | | MIR99B | 1.00 |
| 13682 | 3 | | | | | MIR634 | 1.00 | 13778 | 3 | | | | | MIRLET7A1 | 1.00 |
| 13683 | 3 | | | | | MIR635 | 1.00 | 13779 | 3 | | | | | MIRLET7A2 | 1.00 |
| 13684 | 3 | | | | | MIR636 | 1.00 | 13780 | 3 | | | | | MIRLET7A3 | 1.00 |
| 13685 | 3 | | | | | MIR637 | 1.00 | 13781 | 3 | | | | | MIRLET7B | 1.00 |
| 13686 | 3 | | | | | MIR638 | 1.00 | 13782 | 3 | | | | | MIRLET7C | 1.00 |
| 13687 | 3 | | | | | MIR639 | 1.00 | 13783 | 3 | | | | | MIRLET7D | 1.00 |
| 13688 | 3 | | | | | MIR641 | 1.00 | 13784 | 3 | | | | | MIRLET7E | 1.00 |
| 13689 | 3 | | | | | MIR642A | 1.00 | 13785 | 3 | | | | | MIRLET7F1 | 1.00 |
| 13690 | 3 | | | | | MIR642B | 1.00 | 13786 | 3 | | | | | MIRLET7F2 | 1.00 |
| 13691 | 3 | | | | | MIR643 | 1.00 | 13787 | 3 | | | | | MIRLET7G | 1.00 |
| 13692 | 3 | | | | | MIR644A | 1.00 | 13788 | 3 | | | | | MIRLET7I | 1.00 |
| 13693 | 3 | | | | | MIR645 | 1.00 | 13789 | 3 | | | | | MIXL1 | 1.00 |
| 13694 | 3 | | | | | MIR647 | 1.00 | 13790 | 3 | | | | | MKRN3 | 1.00 |
| 13695 | 3 | | | | | MIR648 | 1.00 | 13791 | 3 | | | | | MKRN7P | 1.00 |
| 13696 | 3 | | | | | MIR650 | 1.00 | 13792 | 3 | | | | | MKX | 1.00 |
| 13697 | 3 | | | | | MIR651 | 1.00 | 13793 | 3 | | | | | MLC1 | 1.00 |
| 13698 | 3 | | | | | MIR653 | 1.00 | 13794 | 3 | | | | | MLK7-AS1 | 1.00 |
| 13699 | 3 | | | | | MIR654 | 1.00 | 13795 | 3 | | | | | MLLT10P1 | 1.00 |
| 13700 | 3 | | | | | MIR655 | 1.00 | 13796 | 3 | | | | | MLN | 1.00 |
| 13701 | 3 | | | | | MIR656 | 1.00 | 13797 | 3 | | | | | MLNR | 1.00 |
| 13702 | 3 | | | | | MIR657 | 1.00 | 13798 | 3 | | | | | MMD2 | 1.00 |
| 13703 | 3 | | | | | MIR658 | 1.00 | 13799 | 3 | | | | | MMEL1 | 1.00 |
| 13704 | 3 | | | | | MIR659 | 1.00 | 13800 | 3 | | | | | MMP1 | 1.00 |
| 13705 | 3 | | | | | MIR660 | 1.00 | 13801 | 3 | | | | | MMP10 | 1.00 |
| 13706 | 3 | | | | | MIR661 | 1.00 | 13802 | 3 | | | | | MMP12 | 1.00 |
| 13707 | 3 | | | | | MIR662 | 1.00 | 13803 | 3 | | | | | MMP13 | 1.00 |
| 13708 | 3 | | | | | MIR663A | 1.00 | 13804 | 3 | | | | | MMP16 | 1.00 |
| 13709 | 3 | | | | | MIR663B | 1.00 | 13805 | 3 | | | | | MMP20 | 1.00 |
| 13710 | 3 | | | | | MIR664 | 1.00 | 13806 | 3 | | | | | MMP21 | 1.00 |
| 13711 | 3 | | | | | MIR665 | 1.00 | 13807 | 3 | | | | | MMP26 | 1.00 |
| 13712 | 3 | | | | | MIR668 | 1.00 | 13808 | 3 | | | | | MMP3 | 1.00 |
| 13713 | 3 | | | | | MIR670 | 1.00 | 13809 | 3 | | | | | MMP8 | 1.00 |
| 13714 | 3 | | | | | MIR671 | 1.00 | 13810 | 3 | | | | | MND1 | 1.00 |
| 13715 | 3 | | | | | MIR675 | 1.00 | 13811 | 3 | | | | | MNX1 | 1.00 |
| 13716 | 3 | | | | | MIR676 | 1.00 | 13812 | 3 | | | | | MOB4 | 1.00 |
| 13717 | 3 | | | | | MIR708 | 1.00 | 13813 | 3 | | | | | MOBP | 1.00 |
| 13718 | 3 | | | | | MIR711 | 1.00 | 13814 | 3 | | | | | MOCOS | 1.00 |
| 13719 | 3 | | | | | MIR718 | 1.00 | 13815 | 3 | | | | | MOG | 1.00 |
| 13720 | 3 | | | | | MIR7-2 | 1.00 | 13816 | 3 | | | | | MOGAT3 | 1.00 |
| 13721 | 3 | | | | | MIR7-3 | 1.00 | 13817 | 3 | | | | | MORC1 | 1.00 |
| 13722 | 3 | | | | | MIR7-3HG | 1.00 | 13818 | 3 | | | | | MORN5 | 1.00 |
| 13723 | 3 | | | | | MIR744 | 1.00 | 13819 | 3 | | | | | MOS | 1.00 |

Fig. 39 - 73

| | | | | | | | | | | | | | | |
|---|---|---|---|---|---|---|---|---|---|---|---|---|---|---|
| 13820 | 3 | | | | | MOV10L1 | 1.00 | 13916 | 3 | | | | MYO16 | 1.00 |
| 13821 | 3 | | | | | MOXD2P | 1.00 | 13917 | 3 | | | | MYO18B | 1.00 |
| 13822 | 3 | | | | | MPHOSPH9 | 1.00 | 13918 | 3 | | | | MYO1A | 1.00 |
| 13823 | 3 | | | | | MPO | 1.00 | 13919 | 3 | | | | MYO1H | 1.00 |
| 13824 | 3 | | | | | MPP4 | 1.00 | 13920 | 3 | | | | MYO3B | 1.00 |
| 13825 | 3 | | | | | MPP6 | 1.00 | 13921 | 3 | | | | MYO7B | 1.00 |
| 13826 | 3 | | | | | MRGPRD | 1.00 | 13922 | 3 | | | | MYOCD | 1.00 |
| 13827 | 3 | | | | | MRGPRE | 1.00 | 13923 | 3 | | | | MYOD1 | 1.00 |
| 13828 | 3 | | | | | MRGPRG | 1.00 | 13924 | 3 | | | | MYOG | 1.00 |
| 13829 | 3 | | | | | MRGPRX1 | 1.00 | 13925 | 3 | | | | MYOM1 | 1.00 |
| 13830 | 3 | | | | | MRGPRX2 | 1.00 | 13926 | 3 | | | | MYOT | 1.00 |
| 13831 | 3 | | | | | MRGPRX3 | 1.00 | 13927 | 3 | | | | MYOZ1 | 1.00 |
| 13832 | 3 | | | | | MRGPRX4 | 1.00 | 13928 | 3 | | | | MYOZ2 | 1.00 |
| 13833 | 3 | | | | | MRO | 1.00 | 13929 | 3 | | | | MYOZ3 | 1.00 |
| 13834 | 3 | | | | | MRVI1-AS1 | 1.00 | 13930 | 3 | | | | MYPN | 1.00 |
| 13835 | 3 | | | | | MS4A1 | 1.00 | 13931 | 3 | | | | MYT1 | 1.00 |
| 13836 | 3 | | | | | MS4A10 | 1.00 | 13932 | 3 | | | | MYT1L | 1.00 |
| 13837 | 3 | | | | | MS4A12 | 1.00 | 13933 | 3 | | | | MZB1 | 1.00 |
| 13838 | 3 | | | | | MS4A13 | 1.00 | 13934 | 3 | | | | N4BP2 | 1.00 |
| 13839 | 3 | | | | | MS4A15 | 1.00 | 13935 | 3 | | | | NAA11 | 1.00 |
| 13840 | 3 | | | | | MS4A3 | 1.00 | 13936 | 3 | | | | NAALADL2 | 1.00 |
| 13841 | 3 | | | | | MS4A5 | 1.00 | 13937 | 3 | | | | NALCN | 1.00 |
| 13842 | 3 | | | | | MS4A6E | 1.00 | 13938 | 3 | | | | NANOG | 1.00 |
| 13843 | 3 | | | | | MS4A8B | 1.00 | 13939 | 3 | | | | NANOGNB | 1.00 |
| 13844 | 3 | | | | | MSGN1 | 1.00 | 13940 | 3 | | | | NANOS2 | 1.00 |
| 13845 | 3 | | | | | MSH4 | 1.00 | 13941 | 3 | | | | NANOS3 | 1.00 |
| 13846 | 3 | | | | | MSH5 | 1.00 | 13942 | 3 | | | | NAP1L6 | 1.00 |
| 13847 | 3 | | | | | MSI1 | 1.00 | 13943 | 3 | | | | NAT16 | 1.00 |
| 13848 | 3 | | | | | MSLN | 1.00 | 13944 | 3 | | | | NAT2 | 1.00 |
| 13849 | 3 | | | | | MSLNL | 1.00 | 13945 | 3 | | | | NAT8 | 1.00 |
| 13850 | 3 | | | | | MSTN | 1.00 | 13946 | 3 | | | | NAT8B | 1.00 |
| 13851 | 3 | | | | | MSX2P1 | 1.00 | 13947 | 3 | | | | NAV2-AS4 | 1.00 |
| 13852 | 3 | | | | | MT1B | 1.00 | 13948 | 3 | | | | NBEAL1 | 1.00 |
| 13853 | 3 | | | | | MT1DP | 1.00 | 13949 | 3 | | | | NBEAP1 | 1.00 |
| 13854 | 3 | | | | | MT1IP | 1.00 | 13950 | 3 | | | | NBLA00301 | 1.00 |
| 13855 | 3 | | | | | MT1JP | 1.00 | 13951 | 3 | | | | NBPF11 | 1.00 |
| 13856 | 3 | | | | | MT3 | 1.00 | 13952 | 3 | | | | NBPF22P | 1.00 |
| 13857 | 3 | | | | | MTBP | 1.00 | 13953 | 3 | | | | NBPF4 | 1.00 |
| 13858 | 3 | | | | | MTL5 | 1.00 | 13954 | 3 | | | | NBPF6 | 1.00 |
| 13859 | 3 | | | | | MTMR8 | 1.00 | 13955 | 3 | | | | NBPF7 | 1.00 |
| 13860 | 3 | | | | | MTNR1A | 1.00 | 13956 | 3 | | | | NCAM2 | 1.00 |
| 13861 | 3 | | | | | MTNR1B | 1.00 | 13957 | 3 | | | | NCAN | 1.00 |
| 13862 | 3 | | | | | MTRNR2L10 | 1.00 | 13958 | 3 | | | | NCAPG | 1.00 |
| 13863 | 3 | | | | | MTRNR2L3 | 1.00 | 13959 | 3 | | | | NCAPH | 1.00 |
| 13864 | 3 | | | | | MTRNR2L4 | 1.00 | 13960 | 3 | | | | NCF1C | 1.00 |
| 13865 | 3 | | | | | MTRNR2L5 | 1.00 | 13961 | 3 | | | | NCOA2 | 1.00 |
| 13866 | 3 | | | | | MTRNR2L6 | 1.00 | 13962 | 3 | | | | NCOR1P1 | 1.00 |
| 13867 | 3 | | | | | MTRNR2L7 | 1.00 | 13963 | 3 | | | | NCR1 | 1.00 |
| 13868 | 3 | | | | | MTRNR2L8 | 1.00 | 13964 | 3 | | | | NCR2 | 1.00 |
| 13869 | 3 | | | | | MTTP | 1.00 | 13965 | 3 | | | | NCRUPAR | 1.00 |
| 13870 | 3 | | | | | MTUS2 | 1.00 | 13966 | 3 | | | | NDC80 | 1.00 |
| 13871 | 3 | | | | | MTVR2 | 1.00 | 13967 | 3 | | | | NDST3 | 1.00 |
| 13872 | 3 | | | | | MUC12 | 1.00 | 13968 | 3 | | | | NDST4 | 1.00 |
| 13873 | 3 | | | | | MUC13 | 1.00 | 13969 | 3 | | | | NEB | 1.00 |
| 13874 | 3 | | | | | MUC16 | 1.00 | 13970 | 3 | | | | NECAB2 | 1.00 |
| 13875 | 3 | | | | | MUC17 | 1.00 | 13971 | 3 | | | | NEDD8-MDP1 | 1.00 |
| 13876 | 3 | | | | | MUC2 | 1.00 | 13972 | 3 | | | | NEFH | 1.00 |
| 13877 | 3 | | | | | MUC21 | 1.00 | 13973 | 3 | | | | NEFL | 1.00 |
| 13878 | 3 | | | | | MUC22 | 1.00 | 13974 | 3 | | | | NEFM | 1.00 |
| 13879 | 3 | | | | | MUC4 | 1.00 | 13975 | 3 | | | | NEGR1-IT1 | 1.00 |
| 13880 | 3 | | | | | MUC5B | 1.00 | 13976 | 3 | | | | NEIL3 | 1.00 |
| 13881 | 3 | | | | | MUM1L1 | 1.00 | 13977 | 3 | | | | NEK10 | 1.00 |
| 13882 | 3 | | | | | MURC | 1.00 | 13978 | 3 | | | | NEK5 | 1.00 |
| 13883 | 3 | | | | | MUSK | 1.00 | 13979 | 3 | | | | NETO1 | 1.00 |
| 13884 | 3 | | | | | MYADML | 1.00 | 13980 | 3 | | | | NEU3 | 1.00 |
| 13885 | 3 | | | | | MYADML2 | 1.00 | 13981 | 3 | | | | NEU4 | 1.00 |
| 13886 | 3 | | | | | MYBL1 | 1.00 | 13982 | 3 | | | | NEURL | 1.00 |
| 13887 | 3 | | | | | MYBPC2 | 1.00 | 13983 | 3 | | | | NEUROD1 | 1.00 |
| 13888 | 3 | | | | | MYBPC3 | 1.00 | 13984 | 3 | | | | NEUROD2 | 1.00 |
| 13889 | 3 | | | | | MYBPH | 1.00 | 13985 | 3 | | | | NEUROD4 | 1.00 |
| 13890 | 3 | | | | | MYBPHL | 1.00 | 13986 | 3 | | | | NEUROD6 | 1.00 |
| 13891 | 3 | | | | | MYCBPAP | 1.00 | 13987 | 3 | | | | NEUROG1 | 1.00 |
| 13892 | 3 | | | | | MYCNOS | 1.00 | 13988 | 3 | | | | NEUROG2 | 1.00 |
| 13893 | 3 | | | | | MYF5 | 1.00 | 13989 | 3 | | | | NEUROG3 | 1.00 |
| 13894 | 3 | | | | | MYF6 | 1.00 | 13990 | 3 | | | | NF1P2 | 1.00 |
| 13895 | 3 | | | | | MYH1 | 1.00 | 13991 | 3 | | | | NGB | 1.00 |
| 13896 | 3 | | | | | MYH13 | 1.00 | 13992 | 3 | | | | NHLH1 | 1.00 |
| 13897 | 3 | | | | | MYH15 | 1.00 | 13993 | 3 | | | | NHLRC2 | 1.00 |
| 13898 | 3 | | | | | MYH16 | 1.00 | 13994 | 3 | | | | NHSL2 | 1.00 |
| 13899 | 3 | | | | | MYH2 | 1.00 | 13995 | 3 | | | | NIPAL1 | 1.00 |
| 13900 | 3 | | | | | MYH3 | 1.00 | 13996 | 3 | | | | NIPSNAP3B | 1.00 |
| 13901 | 3 | | | | | MYH4 | 1.00 | 13997 | 3 | | | | NKAIN2 | 1.00 |
| 13902 | 3 | | | | | MYH6 | 1.00 | 13998 | 3 | | | | NKAIN3 | 1.00 |
| 13903 | 3 | | | | | MYH7 | 1.00 | 13999 | 3 | | | | NKAIN4 | 1.00 |
| 13904 | 3 | | | | | MYH7B | 1.00 | 14000 | 3 | | | | NKX1-2 | 1.00 |
| 13905 | 3 | | | | | MYH8 | 1.00 | 14001 | 3 | | | | NKX2-1 | 1.00 |
| 13906 | 3 | | | | | MYL1 | 1.00 | 14002 | 3 | | | | NKX2-2 | 1.00 |
| 13907 | 3 | | | | | MYL10 | 1.00 | 14003 | 3 | | | | NKX2-3 | 1.00 |
| 13908 | 3 | | | | | MYL2 | 1.00 | 14004 | 3 | | | | NKX2-4 | 1.00 |
| 13909 | 3 | | | | | MYL4 | 1.00 | 14005 | 3 | | | | NKX2-5 | 1.00 |
| 13910 | 3 | | | | | MYL7 | 1.00 | 14006 | 3 | | | | NKX2-6 | 1.00 |
| 13911 | 3 | | | | | MYLK2 | 1.00 | 14007 | 3 | | | | NKX2-8 | 1.00 |
| 13912 | 3 | | | | | MYLK3 | 1.00 | 14008 | 3 | | | | NKX3-2 | 1.00 |
| 13913 | 3 | | | | | MYLK4 | 1.00 | 14009 | 3 | | | | NKX6-1 | 1.00 |
| 13914 | 3 | | | | | MYLPF | 1.00 | 14010 | 3 | | | | NKX6-2 | 1.00 |
| 13915 | 3 | | | | | MYO15A | 1.00 | 14011 | 3 | | | | NKX6-3 | 1.00 |

Fig. 39 - 74

| | | | | | | | | | | | | | |
|---|---|---|---|---|---|---|---|---|---|---|---|---|---|
| 14012 | 3 | | | | | NLGN1 | 1.00 | 14108 | 3 | | | OCLN | 1.00 |
| 14013 | 3 | | | | | NLGN4X | 1.00 | 14109 | 3 | | | OCM | 1.00 |
| 14014 | 3 | | | | | NLGN4Y | 1.00 | 14110 | 3 | | | OCM2 | 1.00 |
| 14015 | 3 | | | | | NLRC4 | 1.00 | 14111 | 3 | | | ODAM | 1.00 |
| 14016 | 3 | | | | | NLRP11 | 1.00 | 14112 | 3 | | | ODF1 | 1.00 |
| 14017 | 3 | | | | | NLRP12 | 1.00 | 14113 | 3 | | | ODF3 | 1.00 |
| 14018 | 3 | | | | | NLRP13 | 1.00 | 14114 | 3 | | | ODF3L2 | 1.00 |
| 14019 | 3 | | | | | NLRP14 | 1.00 | 14115 | 3 | | | ODF4 | 1.00 |
| 14020 | 3 | | | | | NLRP4 | 1.00 | 14116 | 3 | | | ODZ1 | 1.00 |
| 14021 | 3 | | | | | NLRP5 | 1.00 | 14117 | 3 | | | ODZ3 | 1.00 |
| 14022 | 3 | | | | | NLRP6 | 1.00 | 14118 | 3 | | | OGDHL | 1.00 |
| 14023 | 3 | | | | | NLRP7 | 1.00 | 14119 | 3 | | | OIP5 | 1.00 |
| 14024 | 3 | | | | | NLRP8 | 1.00 | 14120 | 3 | | | OIT3 | 1.00 |
| 14025 | 3 | | | | | NLRP9 | 1.00 | 14121 | 3 | | | OLFM3 | 1.00 |
| 14026 | 3 | | | | | NMBR | 1.00 | 14122 | 3 | | | OLFM4 | 1.00 |
| 14027 | 3 | | | | | NME1-NME2 | 1.00 | 14123 | 3 | | | OLIG1 | 1.00 |
| 14028 | 3 | | | | | NME5 | 1.00 | 14124 | 3 | | | OLIG2 | 1.00 |
| 14029 | 3 | | | | | NME9 | 1.00 | 14125 | 3 | | | OLIG3 | 1.00 |
| 14030 | 3 | | | | | NMS | 1.00 | 14126 | 3 | | | OLR1 | 1.00 |
| 14031 | 3 | | | | | NMUR2 | 1.00 | 14127 | 3 | | | OMG | 1.00 |
| 14032 | 3 | | | | | NOBOX | 1.00 | 14128 | 3 | | | OMP | 1.00 |
| 14033 | 3 | | | | | NOG | 1.00 | 14129 | 3 | | | ONECUT1 | 1.00 |
| 14034 | 3 | | | | | NOL4 | 1.00 | 14130 | 3 | | | ONECUT2 | 1.00 |
| 14035 | 3 | | | | | NOS1AP | 1.00 | 14131 | 3 | | | ONECUT3 | 1.00 |
| 14036 | 3 | | | | | NOS2 | 1.00 | 14132 | 3 | | | OOEP | 1.00 |
| 14037 | 3 | | | | | NOTO | 1.00 | 14133 | 3 | | | OPALIN | 1.00 |
| 14038 | 3 | | | | | NOX1 | 1.00 | 14134 | 3 | | | OPCML | 1.00 |
| 14039 | 3 | | | | | NOX3 | 1.00 | 14135 | 3 | | | OPN1LW | 1.00 |
| 14040 | 3 | | | | | NOX4 | 1.00 | 14136 | 3 | | | OPN1MW | 1.00 |
| 14041 | 3 | | | | | NOX5 | 1.00 | 14137 | 3 | | | OPN1MW2 | 1.00 |
| 14042 | 3 | | | | | NOXO1 | 1.00 | 14138 | 3 | | | OPN1SW | 1.00 |
| 14043 | 3 | | | | | NOXRED1 | 1.00 | 14139 | 3 | | | OPN4 | 1.00 |
| 14044 | 3 | | | | | NPAS3 | 1.00 | 14140 | 3 | | | OPN5 | 1.00 |
| 14045 | 3 | | | | | NPAS4 | 1.00 | 14141 | 3 | | | OPRD1 | 1.00 |
| 14046 | 3 | | | | | NPBWR2 | 1.00 | 14142 | 3 | | | OPRK1 | 1.00 |
| 14047 | 3 | | | | | NPC1L1 | 1.00 | 14143 | 3 | | | OPRM1 | 1.00 |
| 14048 | 3 | | | | | NPFFR1 | 1.00 | 14144 | 3 | | | OPTC | 1.00 |
| 14049 | 3 | | | | | NPFFR2 | 1.00 | 14145 | 3 | | | OR10A2 | 1.00 |
| 14050 | 3 | | | | | NPHP3-AS1 | 1.00 | 14146 | 3 | | | OR10A3 | 1.00 |
| 14051 | 3 | | | | | NPHS1 | 1.00 | 14147 | 3 | | | OR10A4 | 1.00 |
| 14052 | 3 | | | | | NPHS2 | 1.00 | 14148 | 3 | | | OR10A5 | 1.00 |
| 14053 | 3 | | | | | NPM2 | 1.00 | 14149 | 3 | | | OR10A6 | 1.00 |
| 14054 | 3 | | | | | NPPA | 1.00 | 14150 | 3 | | | OR10A7 | 1.00 |
| 14055 | 3 | | | | | NPPB | 1.00 | 14151 | 3 | | | OR10AD1 | 1.00 |
| 14056 | 3 | | | | | NPPC | 1.00 | 14152 | 3 | | | OR10AG1 | 1.00 |
| 14057 | 3 | | | | | NPS | 1.00 | 14153 | 3 | | | OR10C1 | 1.00 |
| 14058 | 3 | | | | | NPSR1 | 1.00 | 14154 | 3 | | | OR10G2 | 1.00 |
| 14059 | 3 | | | | | NPVF | 1.00 | 14155 | 3 | | | OR10G3 | 1.00 |
| 14060 | 3 | | | | | NPY | 1.00 | 14156 | 3 | | | OR10G4 | 1.00 |
| 14061 | 3 | | | | | NPY2R | 1.00 | 14157 | 3 | | | OR10G7 | 1.00 |
| 14062 | 3 | | | | | NPY6R | 1.00 | 14158 | 3 | | | OR10G8 | 1.00 |
| 14063 | 3 | | | | | NR0B1 | 1.00 | 14159 | 3 | | | OR10G9 | 1.00 |
| 14064 | 3 | | | | | NR0B2 | 1.00 | 14160 | 3 | | | OR10H1 | 1.00 |
| 14065 | 3 | | | | | NR1H4 | 1.00 | 14161 | 3 | | | OR10H2 | 1.00 |
| 14066 | 3 | | | | | NR1I2 | 1.00 | 14162 | 3 | | | OR10H3 | 1.00 |
| 14067 | 3 | | | | | NR1I3 | 1.00 | 14163 | 3 | | | OR10H4 | 1.00 |
| 14068 | 3 | | | | | NR2E1 | 1.00 | 14164 | 3 | | | OR10H5 | 1.00 |
| 14069 | 3 | | | | | NR2E3 | 1.00 | 14165 | 3 | | | OR10J1 | 1.00 |
| 14070 | 3 | | | | | NR4A3 | 1.00 | 14166 | 3 | | | OR10J3 | 1.00 |
| 14071 | 3 | | | | | NR5A1 | 1.00 | 14167 | 3 | | | OR10J5 | 1.00 |
| 14072 | 3 | | | | | NR6A1 | 1.00 | 14168 | 3 | | | OR10K1 | 1.00 |
| 14073 | 3 | | | | | NRAP | 1.00 | 14169 | 3 | | | OR10K2 | 1.00 |
| 14074 | 3 | | | | | NRCAM | 1.00 | 14170 | 3 | | | OR10P1 | 1.00 |
| 14075 | 3 | | | | | NRG3 | 1.00 | 14171 | 3 | | | OR10Q1 | 1.00 |
| 14076 | 3 | | | | | NRIP3 | 1.00 | 14172 | 3 | | | OR10R2 | 1.00 |
| 14077 | 3 | | | | | NRK | 1.00 | 14173 | 3 | | | OR10S1 | 1.00 |
| 14078 | 3 | | | | | NRL | 1.00 | 14174 | 3 | | | OR10T2 | 1.00 |
| 14079 | 3 | | | | | NRON | 1.00 | 14175 | 3 | | | OR10V1 | 1.00 |
| 14080 | 3 | | | | | NRSN1 | 1.00 | 14176 | 3 | | | OR10V2P | 1.00 |
| 14081 | 3 | | | | | NT5C1A | 1.00 | 14177 | 3 | | | OR10W1 | 1.00 |
| 14082 | 3 | | | | | NT5C1B | 1.00 | 14178 | 3 | | | OR10X1 | 1.00 |
| 14083 | 3 | | | | | NT5C1B-RDH14 | 1.00 | 14179 | 3 | | | OR10Z1 | 1.00 |
| 14084 | 3 | | | | | NTN3 | 1.00 | 14180 | 3 | | | OR11A1 | 1.00 |
| 14085 | 3 | | | | | NTNG1 | 1.00 | 14181 | 3 | | | OR11G2 | 1.00 |
| 14086 | 3 | | | | | NTRK1 | 1.00 | 14182 | 3 | | | OR11H1 | 1.00 |
| 14087 | 3 | | | | | NTS | 1.00 | 14183 | 3 | | | OR11H12 | 1.00 |
| 14088 | 3 | | | | | NTSR1 | 1.00 | 14184 | 3 | | | OR11H2 | 1.00 |
| 14089 | 3 | | | | | NTSR2 | 1.00 | 14185 | 3 | | | OR11H4 | 1.00 |
| 14090 | 3 | | | | | NUDT9P1 | 1.00 | 14186 | 3 | | | OR11H6 | 1.00 |
| 14091 | 3 | | | | | NUP155 | 1.00 | 14187 | 3 | | | OR11L1 | 1.00 |
| 14092 | 3 | | | | | NUP210L | 1.00 | 14188 | 3 | | | OR12D2 | 1.00 |
| 14093 | 3 | | | | | NUP210P1 | 1.00 | 14189 | 3 | | | OR12D3 | 1.00 |
| 14094 | 3 | | | | | NUP62CL | 1.00 | 14190 | 3 | | | OR13A1 | 1.00 |
| 14095 | 3 | | | | | NWD1 | 1.00 | 14191 | 3 | | | OR13C2 | 1.00 |
| 14096 | 3 | | | | | NXF2 | 1.00 | 14192 | 3 | | | OR13C3 | 1.00 |
| 14097 | 3 | | | | | NXF2B | 1.00 | 14193 | 3 | | | OR13C4 | 1.00 |
| 14098 | 3 | | | | | NXF3 | 1.00 | 14194 | 3 | | | OR13C5 | 1.00 |
| 14099 | 3 | | | | | NXF4 | 1.00 | 14195 | 3 | | | OR13C8 | 1.00 |
| 14100 | 3 | | | | | NXF5 | 1.00 | 14196 | 3 | | | OR13C9 | 1.00 |
| 14101 | 3 | | | | | NXNL1 | 1.00 | 14197 | 3 | | | OR13D1 | 1.00 |
| 14102 | 3 | | | | | NXNL2 | 1.00 | 14198 | 3 | | | OR13F1 | 1.00 |
| 14103 | 3 | | | | | NXPH1 | 1.00 | 14199 | 3 | | | OR13G1 | 1.00 |
| 14104 | 3 | | | | | NXPH2 | 1.00 | 14200 | 3 | | | OR13H1 | 1.00 |
| 14105 | 3 | | | | | NYAP2 | 1.00 | 14201 | 3 | | | OR13J1 | 1.00 |
| 14106 | 3 | | | | | NYX | 1.00 | 14202 | 3 | | | OR14A16 | 1.00 |
| 14107 | 3 | | | | | OC90 | 1.00 | 14203 | 3 | | | OR14C36 | 1.00 |

Fig. 39 - 75

| | | | | | | | | | | | | | | |
|---|---|---|---|---|---|---|---|---|---|---|---|---|---|---|
| 14204 | 3 | | | | | OR14I1 | 1.00 | 14300 | 3 | | | | OR3A3 | 1.00 |
| 14205 | 3 | | | | | OR14I1 | 1.00 | 14301 | 3 | | | | OR3A4P | 1.00 |
| 14206 | 3 | | | | | OR1A1 | 1.00 | 14302 | 3 | | | | OR4A15 | 1.00 |
| 14207 | 3 | | | | | OR1A2 | 1.00 | 14303 | 3 | | | | OR4A16 | 1.00 |
| 14208 | 3 | | | | | OR1B1 | 1.00 | 14304 | 3 | | | | OR4A47 | 1.00 |
| 14209 | 3 | | | | | OR1C1 | 1.00 | 14305 | 3 | | | | OR4A5 | 1.00 |
| 14210 | 3 | | | | | OR1D2 | 1.00 | 14306 | 3 | | | | OR4B1 | 1.00 |
| 14211 | 3 | | | | | OR1D4 | 1.00 | 14307 | 3 | | | | OR4C11 | 1.00 |
| 14212 | 3 | | | | | OR1D5 | 1.00 | 14308 | 3 | | | | OR4C12 | 1.00 |
| 14213 | 3 | | | | | OR1E1 | 1.00 | 14309 | 3 | | | | OR4C13 | 1.00 |
| 14214 | 3 | | | | | OR1E2 | 1.00 | 14310 | 3 | | | | OR4C15 | 1.00 |
| 14215 | 3 | | | | | OR1F1 | 1.00 | 14311 | 3 | | | | OR4C16 | 1.00 |
| 14216 | 3 | | | | | OR1F2P | 1.00 | 14312 | 3 | | | | OR4C3 | 1.00 |
| 14217 | 3 | | | | | OR1G1 | 1.00 | 14313 | 3 | | | | OR4C45 | 1.00 |
| 14218 | 3 | | | | | OR1I1 | 1.00 | 14314 | 3 | | | | OR4C46 | 1.00 |
| 14219 | 3 | | | | | OR1J1 | 1.00 | 14315 | 3 | | | | OR4C6 | 1.00 |
| 14220 | 3 | | | | | OR1J2 | 1.00 | 14316 | 3 | | | | OR4D1 | 1.00 |
| 14221 | 3 | | | | | OR1J4 | 1.00 | 14317 | 3 | | | | OR4D10 | 1.00 |
| 14222 | 3 | | | | | OR1K1 | 1.00 | 14318 | 3 | | | | OR4D11 | 1.00 |
| 14223 | 3 | | | | | OR1L1 | 1.00 | 14319 | 3 | | | | OR4D2 | 1.00 |
| 14224 | 3 | | | | | OR1L3 | 1.00 | 14320 | 3 | | | | OR4D5 | 1.00 |
| 14225 | 3 | | | | | OR1L4 | 1.00 | 14321 | 3 | | | | OR4D6 | 1.00 |
| 14226 | 3 | | | | | OR1L6 | 1.00 | 14322 | 3 | | | | OR4D9 | 1.00 |
| 14227 | 3 | | | | | OR1L8 | 1.00 | 14323 | 3 | | | | OR4E2 | 1.00 |
| 14228 | 3 | | | | | OR1M1 | 1.00 | 14324 | 3 | | | | OR4F15 | 1.00 |
| 14229 | 3 | | | | | OR1N1 | 1.00 | 14325 | 3 | | | | OR4F16 | 1.00 |
| 14230 | 3 | | | | | OR1N2 | 1.00 | 14326 | 3 | | | | OR4F17 | 1.00 |
| 14231 | 3 | | | | | OR1Q1 | 1.00 | 14327 | 3 | | | | OR4F21 | 1.00 |
| 14232 | 3 | | | | | OR1S1 | 1.00 | 14328 | 3 | | | | OR4F29 | 1.00 |
| 14233 | 3 | | | | | OR1S2 | 1.00 | 14329 | 3 | | | | OR4F4 | 1.00 |
| 14234 | 3 | | | | | OR2A1 | 1.00 | 14330 | 3 | | | | OR4F5 | 1.00 |
| 14235 | 3 | | | | | OR2A12 | 1.00 | 14331 | 3 | | | | OR4F6 | 1.00 |
| 14236 | 3 | | | | | OR2A14 | 1.00 | 14332 | 3 | | | | OR4K1 | 1.00 |
| 14237 | 3 | | | | | OR2A2 | 1.00 | 14333 | 3 | | | | OR4K13 | 1.00 |
| 14238 | 3 | | | | | OR2A25 | 1.00 | 14334 | 3 | | | | OR4K14 | 1.00 |
| 14239 | 3 | | | | | OR2A42 | 1.00 | 14335 | 3 | | | | OR4K15 | 1.00 |
| 14240 | 3 | | | | | OR2A5 | 1.00 | 14336 | 3 | | | | OR4K17 | 1.00 |
| 14241 | 3 | | | | | OR2A7 | 1.00 | 14337 | 3 | | | | OR4K2 | 1.00 |
| 14242 | 3 | | | | | OR2AE1 | 1.00 | 14338 | 3 | | | | OR4K5 | 1.00 |
| 14243 | 3 | | | | | OR2AG1 | 1.00 | 14339 | 3 | | | | OR4L1 | 1.00 |
| 14244 | 3 | | | | | OR2AG2 | 1.00 | 14340 | 3 | | | | OR4M1 | 1.00 |
| 14245 | 3 | | | | | OR2AK2 | 1.00 | 14341 | 3 | | | | OR4M2 | 1.00 |
| 14246 | 3 | | | | | OR2AT4 | 1.00 | 14342 | 3 | | | | OR4N2 | 1.00 |
| 14247 | 3 | | | | | OR2B11 | 1.00 | 14343 | 3 | | | | OR4N3P | 1.00 |
| 14248 | 3 | | | | | OR2B2 | 1.00 | 14344 | 3 | | | | OR4N4 | 1.00 |
| 14249 | 3 | | | | | OR2B3 | 1.00 | 14345 | 3 | | | | OR4N5 | 1.00 |
| 14250 | 3 | | | | | OR2B6 | 1.00 | 14346 | 3 | | | | OR4P4 | 1.00 |
| 14251 | 3 | | | | | OR2C1 | 1.00 | 14347 | 3 | | | | OR4Q3 | 1.00 |
| 14252 | 3 | | | | | OR2C3 | 1.00 | 14348 | 3 | | | | OR4S1 | 1.00 |
| 14253 | 3 | | | | | OR2D2 | 1.00 | 14349 | 3 | | | | OR4S2 | 1.00 |
| 14254 | 3 | | | | | OR2D3 | 1.00 | 14350 | 3 | | | | OR4X1 | 1.00 |
| 14255 | 3 | | | | | OR2F1 | 1.00 | 14351 | 3 | | | | OR4X2 | 1.00 |
| 14256 | 3 | | | | | OR2F2 | 1.00 | 14352 | 3 | | | | OR51A2 | 1.00 |
| 14257 | 3 | | | | | OR2G2 | 1.00 | 14353 | 3 | | | | OR51A4 | 1.00 |
| 14258 | 3 | | | | | OR2G3 | 1.00 | 14354 | 3 | | | | OR51A7 | 1.00 |
| 14259 | 3 | | | | | OR2G6 | 1.00 | 14355 | 3 | | | | OR51B2 | 1.00 |
| 14260 | 3 | | | | | OR2H1 | 1.00 | 14356 | 3 | | | | OR51B4 | 1.00 |
| 14261 | 3 | | | | | OR2H2 | 1.00 | 14357 | 3 | | | | OR51B5 | 1.00 |
| 14262 | 3 | | | | | OR2J2 | 1.00 | 14358 | 3 | | | | OR51B6 | 1.00 |
| 14263 | 3 | | | | | OR2J3 | 1.00 | 14359 | 3 | | | | OR51D1 | 1.00 |
| 14264 | 3 | | | | | OR2K2 | 1.00 | 14360 | 3 | | | | OR51E1 | 1.00 |
| 14265 | 3 | | | | | OR2L13 | 1.00 | 14361 | 3 | | | | OR51E2 | 1.00 |
| 14266 | 3 | | | | | OR2L1P | 1.00 | 14362 | 3 | | | | OR51F1 | 1.00 |
| 14267 | 3 | | | | | OR2L2 | 1.00 | 14363 | 3 | | | | OR51F2 | 1.00 |
| 14268 | 3 | | | | | OR2L3 | 1.00 | 14364 | 3 | | | | OR51G1 | 1.00 |
| 14269 | 3 | | | | | OR2L8 | 1.00 | 14365 | 3 | | | | OR51G2 | 1.00 |
| 14270 | 3 | | | | | OR2M1P | 1.00 | 14366 | 3 | | | | OR51I1 | 1.00 |
| 14271 | 3 | | | | | OR2M2 | 1.00 | 14367 | 3 | | | | OR51I2 | 1.00 |
| 14272 | 3 | | | | | OR2M3 | 1.00 | 14368 | 3 | | | | OR51L1 | 1.00 |
| 14273 | 3 | | | | | OR2M4 | 1.00 | 14369 | 3 | | | | OR51M1 | 1.00 |
| 14274 | 3 | | | | | OR2M5 | 1.00 | 14370 | 3 | | | | OR51Q1 | 1.00 |
| 14275 | 3 | | | | | OR2M7 | 1.00 | 14371 | 3 | | | | OR51S1 | 1.00 |
| 14276 | 3 | | | | | OR2S2 | 1.00 | 14372 | 3 | | | | OR51T1 | 1.00 |
| 14277 | 3 | | | | | OR2T1 | 1.00 | 14373 | 3 | | | | OR51V1 | 1.00 |
| 14278 | 3 | | | | | OR2T10 | 1.00 | 14374 | 3 | | | | OR52A1 | 1.00 |
| 14279 | 3 | | | | | OR2T11 | 1.00 | 14375 | 3 | | | | OR52A5 | 1.00 |
| 14280 | 3 | | | | | OR2T12 | 1.00 | 14376 | 3 | | | | OR52B2 | 1.00 |
| 14281 | 3 | | | | | OR2T2 | 1.00 | 14377 | 3 | | | | OR52B4 | 1.00 |
| 14282 | 3 | | | | | OR2T27 | 1.00 | 14378 | 3 | | | | OR52B6 | 1.00 |
| 14283 | 3 | | | | | OR2T29 | 1.00 | 14379 | 3 | | | | OR52D1 | 1.00 |
| 14284 | 3 | | | | | OR2T3 | 1.00 | 14380 | 3 | | | | OR52E2 | 1.00 |
| 14285 | 3 | | | | | OR2T33 | 1.00 | 14381 | 3 | | | | OR52E4 | 1.00 |
| 14286 | 3 | | | | | OR2T34 | 1.00 | 14382 | 3 | | | | OR52E6 | 1.00 |
| 14287 | 3 | | | | | OR2T35 | 1.00 | 14383 | 3 | | | | OR52E8 | 1.00 |
| 14288 | 3 | | | | | OR2T4 | 1.00 | 14384 | 3 | | | | OR52H1 | 1.00 |
| 14289 | 3 | | | | | OR2T5 | 1.00 | 14385 | 3 | | | | OR52I1 | 1.00 |
| 14290 | 3 | | | | | OR2T6 | 1.00 | 14386 | 3 | | | | OR52I2 | 1.00 |
| 14291 | 3 | | | | | OR2T8 | 1.00 | 14387 | 3 | | | | OR52J3 | 1.00 |
| 14292 | 3 | | | | | OR2V2 | 1.00 | 14388 | 3 | | | | OR52K1 | 1.00 |
| 14293 | 3 | | | | | OR2W1 | 1.00 | 14389 | 3 | | | | OR52K2 | 1.00 |
| 14294 | 3 | | | | | OR2W3 | 1.00 | 14390 | 3 | | | | OR52L1 | 1.00 |
| 14295 | 3 | | | | | OR2W5 | 1.00 | 14391 | 3 | | | | OR52M1 | 1.00 |
| 14296 | 3 | | | | | OR2Y1 | 1.00 | 14392 | 3 | | | | OR52N1 | 1.00 |
| 14297 | 3 | | | | | OR2Z1 | 1.00 | 14393 | 3 | | | | OR52N2 | 1.00 |
| 14298 | 3 | | | | | OR3A1 | 1.00 | 14394 | 3 | | | | OR52N5 | 1.00 |
| 14299 | 3 | | | | | OR3A2 | 1.00 | 14395 | 3 | | | | OR52R1 | 1.00 |

Fig. 39 - 76

| | | | | | | | |
|---|---|---|---|---|---|---|---|
| 14396 | 3 | OR52W1 | 1.00 | 14492 | 3 | OR7E2P | 1.00 |
| 14397 | 3 | OR56A1 | 1.00 | 14493 | 3 | OR7E37P | 1.00 |
| 14398 | 3 | OR56A3 | 1.00 | 14494 | 3 | OR7E5P | 1.00 |
| 14399 | 3 | OR56A4 | 1.00 | 14495 | 3 | OR7G1 | 1.00 |
| 14400 | 3 | OR56A5 | 1.00 | 14496 | 3 | OR7G2 | 1.00 |
| 14401 | 3 | OR56B1 | 1.00 | 14497 | 3 | OR7G3 | 1.00 |
| 14402 | 3 | OR56B4 | 1.00 | 14498 | 3 | OR8A1 | 1.00 |
| 14403 | 3 | OR5A1 | 1.00 | 14499 | 3 | OR8B12 | 1.00 |
| 14404 | 3 | OR5A2 | 1.00 | 14500 | 3 | OR8B2 | 1.00 |
| 14405 | 3 | OR5AC2 | 1.00 | 14501 | 3 | OR8B3 | 1.00 |
| 14406 | 3 | OR5AK2 | 1.00 | 14502 | 3 | OR8B4 | 1.00 |
| 14407 | 3 | OR5AK4P | 1.00 | 14503 | 3 | OR8B8 | 1.00 |
| 14408 | 3 | OR5AN1 | 1.00 | 14504 | 3 | OR8D1 | 1.00 |
| 14409 | 3 | OR5AP2 | 1.00 | 14505 | 3 | OR8D2 | 1.00 |
| 14410 | 3 | OR5AR1 | 1.00 | 14506 | 3 | OR8D4 | 1.00 |
| 14411 | 3 | OR5AS1 | 1.00 | 14507 | 3 | OR8G1 | 1.00 |
| 14412 | 3 | OR5AU1 | 1.00 | 14508 | 3 | OR8G2 | 1.00 |
| 14413 | 3 | OR5B12 | 1.00 | 14509 | 3 | OR8G5 | 1.00 |
| 14414 | 3 | OR5B17 | 1.00 | 14510 | 3 | OR8H1 | 1.00 |
| 14415 | 3 | OR5B2 | 1.00 | 14511 | 3 | OR8H2 | 1.00 |
| 14416 | 3 | OR5B21 | 1.00 | 14512 | 3 | OR8H3 | 1.00 |
| 14417 | 3 | OR5B3 | 1.00 | 14513 | 3 | OR8I2 | 1.00 |
| 14418 | 3 | OR5C1 | 1.00 | 14514 | 3 | OR8J1 | 1.00 |
| 14419 | 3 | OR5D13 | 1.00 | 14515 | 3 | OR8J3 | 1.00 |
| 14420 | 3 | OR5D14 | 1.00 | 14516 | 3 | OR8K1 | 1.00 |
| 14421 | 3 | OR5D16 | 1.00 | 14517 | 3 | OR8K3 | 1.00 |
| 14422 | 3 | OR5D18 | 1.00 | 14518 | 3 | OR8K5 | 1.00 |
| 14423 | 3 | OR5E1P | 1.00 | 14519 | 3 | OR8S1 | 1.00 |
| 14424 | 3 | OR5F1 | 1.00 | 14520 | 3 | OR8U1 | 1.00 |
| 14425 | 3 | OR5H1 | 1.00 | 14521 | 3 | OR8U8 | 1.00 |
| 14426 | 3 | OR5H14 | 1.00 | 14522 | 3 | OR9A2 | 1.00 |
| 14427 | 3 | OR5H15 | 1.00 | 14523 | 3 | OR9A4 | 1.00 |
| 14428 | 3 | OR5H2 | 1.00 | 14524 | 3 | OR9G4 | 1.00 |
| 14429 | 3 | OR5H6 | 1.00 | 14525 | 3 | OR9G9 | 1.00 |
| 14430 | 3 | OR5I1 | 1.00 | 14526 | 3 | OR9I1 | 1.00 |
| 14431 | 3 | OR5J2 | 1.00 | 14527 | 3 | OR9K2 | 1.00 |
| 14432 | 3 | OR5K1 | 1.00 | 14528 | 3 | OR9Q1 | 1.00 |
| 14433 | 3 | OR5K2 | 1.00 | 14529 | 3 | OR9Q2 | 1.00 |
| 14434 | 3 | OR5K3 | 1.00 | 14530 | 3 | ORC1 | 1.00 |
| 14435 | 3 | OR5K4 | 1.00 | 14531 | 3 | ORM1 | 1.00 |
| 14436 | 3 | OR5L1 | 1.00 | 14532 | 3 | ORM2 | 1.00 |
| 14437 | 3 | OR5L2 | 1.00 | 14533 | 3 | OSM | 1.00 |
| 14438 | 3 | OR5M1 | 1.00 | 14534 | 3 | OSTalpha | 1.00 |
| 14439 | 3 | OR5M10 | 1.00 | 14535 | 3 | OSTBETA | 1.00 |
| 14440 | 3 | OR5M11 | 1.00 | 14536 | 3 | OSTN | 1.00 |
| 14441 | 3 | OR5M3 | 1.00 | 14537 | 3 | OTC | 1.00 |
| 14442 | 3 | OR5M8 | 1.00 | 14538 | 3 | OTOA | 1.00 |
| 14443 | 3 | OR5M9 | 1.00 | 14539 | 3 | OTOF | 1.00 |
| 14444 | 3 | OR5P2 | 1.00 | 14540 | 3 | OTOGL | 1.00 |
| 14445 | 3 | OR5P3 | 1.00 | 14541 | 3 | OTOL1 | 1.00 |
| 14446 | 3 | OR5R1 | 1.00 | 14542 | 3 | OTOP2 | 1.00 |
| 14447 | 3 | OR5T1 | 1.00 | 14543 | 3 | OTOP3 | 1.00 |
| 14448 | 3 | OR5T2 | 1.00 | 14544 | 3 | OTOR | 1.00 |
| 14449 | 3 | OR5T3 | 1.00 | 14545 | 3 | OTOS | 1.00 |
| 14450 | 3 | OR5V1 | 1.00 | 14546 | 3 | OTP | 1.00 |
| 14451 | 3 | OR5W2 | 1.00 | 14547 | 3 | OTUD6A | 1.00 |
| 14452 | 3 | OR6A2 | 1.00 | 14548 | 3 | OTX2 | 1.00 |
| 14453 | 3 | OR6B1 | 1.00 | 14549 | 3 | OTX2OS1 | 1.00 |
| 14454 | 3 | OR6B2 | 1.00 | 14550 | 3 | OVCH1 | 1.00 |
| 14455 | 3 | OR6B3 | 1.00 | 14551 | 3 | OVCH2 | 1.00 |
| 14456 | 3 | OR6C1 | 1.00 | 14552 | 3 | OXCT2 | 1.00 |
| 14457 | 3 | OR6C2 | 1.00 | 14553 | 3 | OXT | 1.00 |
| 14458 | 3 | OR6C3 | 1.00 | 14554 | 3 | OXTR | 1.00 |
| 14459 | 3 | OR6C4 | 1.00 | 14555 | 3 | P2RX3 | 1.00 |
| 14460 | 3 | OR6C6 | 1.00 | 14556 | 3 | P2RX5 | 1.00 |
| 14461 | 3 | OR6C65 | 1.00 | 14557 | 3 | P2RX5-TAX1BP3 | 1.00 |
| 14462 | 3 | OR6C68 | 1.00 | 14558 | 3 | P2RX6 | 1.00 |
| 14463 | 3 | OR6C70 | 1.00 | 14559 | 3 | P2RX6P | 1.00 |
| 14464 | 3 | OR6C74 | 1.00 | 14560 | 3 | P2RY1 | 1.00 |
| 14465 | 3 | OR6C75 | 1.00 | 14561 | 3 | P2RY12 | 1.00 |
| 14466 | 3 | OR6C76 | 1.00 | 14562 | 3 | P2RY4 | 1.00 |
| 14467 | 3 | OR6F1 | 1.00 | 14563 | 3 | P4HA3 | 1.00 |
| 14468 | 3 | OR6K2 | 1.00 | 14564 | 3 | PABPC1L2A | 1.00 |
| 14469 | 3 | OR6K3 | 1.00 | 14565 | 3 | PABPC1L2B | 1.00 |
| 14470 | 3 | OR6K6 | 1.00 | 14566 | 3 | PABPC1P2 | 1.00 |
| 14471 | 3 | OR6M1 | 1.00 | 14567 | 3 | PABPC4L | 1.00 |
| 14472 | 3 | OR6N1 | 1.00 | 14568 | 3 | PABPC5 | 1.00 |
| 14473 | 3 | OR6N2 | 1.00 | 14569 | 3 | PABPN1L | 1.00 |
| 14474 | 3 | OR6P1 | 1.00 | 14570 | 3 | PACSIN1 | 1.00 |
| 14475 | 3 | OR6Q1 | 1.00 | 14571 | 3 | PADI3 | 1.00 |
| 14476 | 3 | OR6S1 | 1.00 | 14572 | 3 | PADI4 | 1.00 |
| 14477 | 3 | OR6T1 | 1.00 | 14573 | 3 | PADI6 | 1.00 |
| 14478 | 3 | OR6V1 | 1.00 | 14574 | 3 | PAEP | 1.00 |
| 14479 | 3 | OR6W1P | 1.00 | 14575 | 3 | PAGE1 | 1.00 |
| 14480 | 3 | OR6X1 | 1.00 | 14576 | 3 | PAGE2 | 1.00 |
| 14481 | 3 | OR6Y1 | 1.00 | 14577 | 3 | PAGE2B | 1.00 |
| 14482 | 3 | OR7A10 | 1.00 | 14578 | 3 | PAGE3 | 1.00 |
| 14483 | 3 | OR7A17 | 1.00 | 14579 | 3 | PAGE4 | 1.00 |
| 14484 | 3 | OR7A5 | 1.00 | 14580 | 3 | PAGE5 | 1.00 |
| 14485 | 3 | OR7C1 | 1.00 | 14581 | 3 | PAH | 1.00 |
| 14486 | 3 | OR7C2 | 1.00 | 14582 | 3 | PAK3 | 1.00 |
| 14487 | 3 | OR7D2 | 1.00 | 14583 | 3 | PAK7 | 1.00 |
| 14488 | 3 | OR7D4 | 1.00 | 14584 | 3 | PALM2 | 1.00 |
| 14489 | 3 | OR7E12P | 1.00 | 14585 | 3 | PALM2-AKAP2 | 1.00 |
| 14490 | 3 | OR7E156P | 1.00 | 14586 | 3 | PANX3 | 1.00 |
| 14491 | 3 | OR7E24 | 1.00 | 14587 | 3 | PAPPA | 1.00 |

Fig. 39 - 77

| | | | | |
|---|---|---|---|---|
| 14588 | 3 | PAPPA2 | 1.00 | |
| 14589 | 3 | PAQR9 | 1.00 | |
| 14590 | 3 | PAR1 | 1.00 | |
| 14591 | 3 | PAR4 | 1.00 | |
| 14592 | 3 | PAR5 | 1.00 | |
| 14593 | 3 | PARP15 | 1.00 | |
| 14594 | 3 | PARPBP | 1.00 | |
| 14595 | 3 | PASD1 | 1.00 | |
| 14596 | 3 | PATE1 | 1.00 | |
| 14597 | 3 | PATE2 | 1.00 | |
| 14598 | 3 | PATE3 | 1.00 | |
| 14599 | 3 | PATE4 | 1.00 | |
| 14600 | 3 | PATL2 | 1.00 | |
| 14601 | 3 | PAX1 | 1.00 | |
| 14602 | 3 | PAX2 | 1.00 | |
| 14603 | 3 | PAX4 | 1.00 | |
| 14604 | 3 | PAX5 | 1.00 | |
| 14605 | 3 | PAX7 | 1.00 | |
| 14606 | 3 | PAX9 | 1.00 | |
| 14607 | 3 | PBK | 1.00 | |
| 14608 | 3 | PBOV1 | 1.00 | |
| 14609 | 3 | PCA3 | 1.00 | |
| 14610 | 3 | PCDH10 | 1.00 | |
| 14611 | 3 | PCDH11X | 1.00 | |
| 14612 | 3 | PCDH11Y | 1.00 | |
| 14613 | 3 | PCDH15 | 1.00 | |
| 14614 | 3 | PCDH17 | 1.00 | |
| 14615 | 3 | PCDH19 | 1.00 | |
| 14616 | 3 | PCDH8 | 1.00 | |
| 14617 | 3 | PCDH9 | 1.00 | |
| 14618 | 3 | PCDHA1 | 1.00 | |
| 14619 | 3 | PCDHA10 | 1.00 | |
| 14620 | 3 | PCDHA11 | 1.00 | |
| 14621 | 3 | PCDHA12 | 1.00 | |
| 14622 | 3 | PCDHA13 | 1.00 | |
| 14623 | 3 | PCDHA2 | 1.00 | |
| 14624 | 3 | PCDHA3 | 1.00 | |
| 14625 | 3 | PCDHA4 | 1.00 | |
| 14626 | 3 | PCDHA5 | 1.00 | |
| 14627 | 3 | PCDHA6 | 1.00 | |
| 14628 | 3 | PCDHA7 | 1.00 | |
| 14629 | 3 | PCDHA8 | 1.00 | |
| 14630 | 3 | PCDHA9 | 1.00 | |
| 14631 | 3 | PCDHAC1 | 1.00 | |
| 14632 | 3 | PCDHAC2 | 1.00 | |
| 14633 | 3 | PCDHB1 | 1.00 | |
| 14634 | 3 | PCDHB12 | 1.00 | |
| 14635 | 3 | PCDHB17 | 1.00 | |
| 14636 | 3 | PCDHB18 | 1.00 | |
| 14637 | 3 | PCDHB19P | 1.00 | |
| 14638 | 3 | PCDHB8 | 1.00 | |
| 14639 | 3 | PCDHGA1 | 1.00 | |
| 14640 | 3 | PCDHGA8 | 1.00 | |
| 14641 | 3 | PCDHGB1 | 1.00 | |
| 14642 | 3 | PCDHGB3 | 1.00 | |
| 14643 | 3 | PCDHGB8P | 1.00 | |
| 14644 | 3 | PCDHGC4 | 1.00 | |
| 14645 | 3 | PCDHGC5 | 1.00 | |
| 14646 | 3 | PCDP1 | 1.00 | |
| 14647 | 3 | PCGEM1 | 1.00 | |
| 14648 | 3 | PCLO | 1.00 | |
| 14649 | 3 | PCNAP1 | 1.00 | |
| 14650 | 3 | PCSK1 | 1.00 | |
| 14651 | 3 | PCSK4 | 1.00 | |
| 14652 | 3 | PCSK5 | 1.00 | |
| 14653 | 3 | PCYT1B | 1.00 | |
| 14654 | 3 | PDC | 1.00 | |
| 14655 | 3 | PDCD1 | 1.00 | |
| 14656 | 3 | PDCL2 | 1.00 | |
| 14657 | 3 | PDE10A | 1.00 | |
| 14658 | 3 | PDE11A | 1.00 | |
| 14659 | 3 | PDE1C | 1.00 | |
| 14660 | 3 | PDE3A | 1.00 | |
| 14661 | 3 | PDE4C | 1.00 | |
| 14662 | 3 | PDE6B | 1.00 | |
| 14663 | 3 | PDE6C | 1.00 | |
| 14664 | 3 | PDE6H | 1.00 | |
| 14665 | 3 | PDE7B | 1.00 | |
| 14666 | 3 | PDIA2 | 1.00 | |
| 14667 | 3 | PDILT | 1.00 | |
| 14668 | 3 | PDX1 | 1.00 | |
| 14669 | 3 | PDYN | 1.00 | |
| 14670 | 3 | PDZD3 | 1.00 | |
| 14671 | 3 | PDZD9 | 1.00 | |
| 14672 | 3 | PDZRN4 | 1.00 | |
| 14673 | 3 | PEG3 | 1.00 | |
| 14674 | 3 | PEG3-AS1 | 1.00 | |
| 14675 | 3 | PER4 | 1.00 | |
| 14676 | 3 | PEX5L | 1.00 | |
| 14677 | 3 | PF4 | 1.00 | |
| 14678 | 3 | PF4V1 | 1.00 | |
| 14679 | 3 | PFKFB1 | 1.00 | |
| 14680 | 3 | PFN3 | 1.00 | |
| 14681 | 3 | PFN4 | 1.00 | |
| 14682 | 3 | PGA3 | 1.00 | |
| 14683 | 3 | PGA4 | 1.00 | |
| 14684 | 3 | PGA5 | 1.00 | |
| 14685 | 3 | PGBD4 | 1.00 | |
| 14686 | 3 | PGC | 1.00 | |
| 14687 | 3 | PGCP1 | 1.00 | |
| 14688 | 3 | PGK2 | 1.00 | |
| 14689 | 3 | PGLYRP1 | 1.00 | |
| 14690 | 3 | PGLYRP2 | 1.00 | |
| 14691 | 3 | PGPEP1L | 1.00 | |
| 14692 | 3 | PGR | 1.00 | |
| 14693 | 3 | PHEX | 1.00 | |
| 14694 | 3 | PHF21B | 1.00 | |
| 14695 | 3 | PHF2P1 | 1.00 | |
| 14696 | 3 | PHGR1 | 1.00 | |
| 14697 | 3 | PHLPP2 | 1.00 | |
| 14698 | 3 | PHOSPHO2-KLHL23 | 1.00 | |
| 14699 | 3 | PHOX2A | 1.00 | |
| 14700 | 3 | PHOX2B | 1.00 | |
| 14701 | 3 | PHTF1 | 1.00 | |
| 14702 | 3 | PIEZO2 | 1.00 | |
| 14703 | 3 | PIH1D2 | 1.00 | |
| 14704 | 3 | PIK3CG | 1.00 | |
| 14705 | 3 | PIP5K1P1 | 1.00 | |
| 14706 | 3 | PIPOX | 1.00 | |
| 14707 | 3 | PIR-FIGF | 1.00 | |
| 14708 | 3 | PIRT | 1.00 | |
| 14709 | 3 | PISRT1 | 1.00 | |
| 14710 | 3 | PITX3 | 1.00 | |
| 14711 | 3 | PIWIL1 | 1.00 | |
| 14712 | 3 | PIWIL2 | 1.00 | |
| 14713 | 3 | PIWIL3 | 1.00 | |
| 14714 | 3 | PIWIL4 | 1.00 | |
| 14715 | 3 | PKD1L1 | 1.00 | |
| 14716 | 3 | PKD1L3 | 1.00 | |
| 14717 | 3 | PKD2L1 | 1.00 | |
| 14718 | 3 | PKD2L2 | 1.00 | |
| 14719 | 3 | PKDREJ | 1.00 | |
| 14720 | 3 | PKHD1 | 1.00 | |
| 14721 | 3 | PKHD1L1 | 1.00 | |
| 14722 | 3 | PLA1A | 1.00 | |
| 14723 | 3 | PLA2G10 | 1.00 | |
| 14724 | 3 | PLA2G12B | 1.00 | |
| 14725 | 3 | PLA2G1B | 1.00 | |
| 14726 | 3 | PLA2G2C | 1.00 | |
| 14727 | 3 | PLA2G2D | 1.00 | |
| 14728 | 3 | PLA2G2E | 1.00 | |
| 14729 | 3 | PLAC1 | 1.00 | |
| 14730 | 3 | PLAC1L | 1.00 | |
| 14731 | 3 | PLAC4 | 1.00 | |
| 14732 | 3 | PLAC8 | 1.00 | |
| 14733 | 3 | PLCE1 | 1.00 | |
| 14734 | 3 | PLCH1 | 1.00 | |
| 14735 | 3 | PLCL1 | 1.00 | |
| 14736 | 3 | PLCXD2 | 1.00 | |
| 14737 | 3 | PLCXD3 | 1.00 | |
| 14738 | 3 | PLCZ1 | 1.00 | |
| 14739 | 3 | PLD5 | 1.00 | |
| 14740 | 3 | PLEKHD1 | 1.00 | |
| 14741 | 3 | PLEKHG4B | 1.00 | |
| 14742 | 3 | PLEKHG7 | 1.00 | |
| 14743 | 3 | PLG | 1.00 | |
| 14744 | 3 | PLGLA | 1.00 | |
| 14745 | 3 | PLGLB2 | 1.00 | |
| 14746 | 3 | PLK5 | 1.00 | |
| 14747 | 3 | PLSCR2 | 1.00 | |
| 14748 | 3 | PLSCR5 | 1.00 | |
| 14749 | 3 | PMCH | 1.00 | |
| 14750 | 3 | PMCHL1 | 1.00 | |
| 14751 | 3 | PMCHL2 | 1.00 | |
| 14752 | 3 | PMFBP1 | 1.00 | |
| 14753 | 3 | PNCK | 1.00 | |
| 14754 | 3 | PNLIP | 1.00 | |
| 14755 | 3 | PNLIPRP1 | 1.00 | |
| 14756 | 3 | PNLIPRP2 | 1.00 | |
| 14757 | 3 | PNMA2 | 1.00 | |
| 14758 | 3 | PNMA3 | 1.00 | |
| 14759 | 3 | PNMA5 | 1.00 | |
| 14760 | 3 | PNMA6A | 1.00 | |
| 14761 | 3 | PNMA6C | 1.00 | |
| 14762 | 3 | PNMA6D | 1.00 | |
| 14763 | 3 | PNOC | 1.00 | |
| 14764 | 3 | POLE2 | 1.00 | |
| 14765 | 3 | POLN | 1.00 | |
| 14766 | 3 | POLQ | 1.00 | |
| 14767 | 3 | POM121L10P | 1.00 | |
| 14768 | 3 | POM121L12 | 1.00 | |
| 14769 | 3 | POM121L1P | 1.00 | |
| 14770 | 3 | POM121L2 | 1.00 | |
| 14771 | 3 | POM121L4P | 1.00 | |
| 14772 | 3 | POM121L8P | 1.00 | |
| 14773 | 3 | POM121L9P | 1.00 | |
| 14774 | 3 | PON1 | 1.00 | |
| 14775 | 3 | POPDC3 | 1.00 | |
| 14776 | 3 | POTEA | 1.00 | |
| 14777 | 3 | POTEB | 1.00 | |
| 14778 | 3 | POTEC | 1.00 | |

Fig. 39 - 78

| | | | | | | | | |
|---|---|---|---|---|---|---|---|---|
| 14779 | 3 | | | | POTED | 1.00 |
| 14780 | 3 | | | | POTEG | 1.00 |
| 14781 | 3 | | | | POTEH | 1.00 |
| 14782 | 3 | | | | POU1F1 | 1.00 |
| 14783 | 3 | | | | POU2AF1 | 1.00 |
| 14784 | 3 | | | | POU3F2 | 1.00 |
| 14785 | 3 | | | | POU3F3 | 1.00 |
| 14786 | 3 | | | | POU3F4 | 1.00 |
| 14787 | 3 | | | | POU4F1 | 1.00 |
| 14788 | 3 | | | | POU4F2 | 1.00 |
| 14789 | 3 | | | | POU4F3 | 1.00 |
| 14790 | 3 | | | | POU5F1P4 | 1.00 |
| 14791 | 3 | | | | POU5F2 | 1.00 |
| 14792 | 3 | | | | POU6F2 | 1.00 |
| 14793 | 3 | | | | PP12613 | 1.00 |
| 14794 | 3 | | | | PP14571 | 1.00 |
| 14795 | 3 | | | | PP2D1 | 1.00 |
| 14796 | 3 | | | | PPAN-P2RY11 | 1.00 |
| 14797 | 3 | | | | PPAPDC1A | 1.00 |
| 14798 | 3 | | | | PPBPL2 | 1.00 |
| 14799 | 3 | | | | PPEF1 | 1.00 |
| 14800 | 3 | | | | PPEF2 | 1.00 |
| 14801 | 3 | | | | PPFIA2 | 1.00 |
| 14802 | 3 | | | | PPIAL4B | 1.00 |
| 14803 | 3 | | | | PPIAL4C | 1.00 |
| 14804 | 3 | | | | PPIAL4D | 1.00 |
| 14805 | 3 | | | | PPIAL4E | 1.00 |
| 14806 | 3 | | | | PPIAL4G | 1.00 |
| 14807 | 3 | | | | PPIL6 | 1.00 |
| 14808 | 3 | | | | PPM1E | 1.00 |
| 14809 | 3 | | | | PPP1R14D | 1.00 |
| 14810 | 3 | | | | PPP1R17 | 1.00 |
| 14811 | 3 | | | | PPP1R1C | 1.00 |
| 14812 | 3 | | | | PPP1R2P9 | 1.00 |
| 14813 | 3 | | | | PPP1R36 | 1.00 |
| 14814 | 3 | | | | PPP1R3A | 1.00 |
| 14815 | 3 | | | | PPP1R42 | 1.00 |
| 14816 | 3 | | | | PPP1R9A | 1.00 |
| 14817 | 3 | | | | PPP3R2 | 1.00 |
| 14818 | 3 | | | | PPP4R1L | 1.00 |
| 14819 | 3 | | | | PPP4R4 | 1.00 |
| 14820 | 3 | | | | PPY | 1.00 |
| 14821 | 3 | | | | PPY2 | 1.00 |
| 14822 | 3 | | | | PRAC | 1.00 |
| 14823 | 3 | | | | PRAME | 1.00 |
| 14824 | 3 | | | | PRAMEF1 | 1.00 |
| 14825 | 3 | | | | PRAMEF10 | 1.00 |
| 14826 | 3 | | | | PRAMEF11 | 1.00 |
| 14827 | 3 | | | | PRAMEF12 | 1.00 |
| 14828 | 3 | | | | PRAMEF13 | 1.00 |
| 14829 | 3 | | | | PRAMEF14 | 1.00 |
| 14830 | 3 | | | | PRAMEF15 | 1.00 |
| 14831 | 3 | | | | PRAMEF16 | 1.00 |
| 14832 | 3 | | | | PRAMEF17 | 1.00 |
| 14833 | 3 | | | | PRAMEF18 | 1.00 |
| 14834 | 3 | | | | PRAMEF19 | 1.00 |
| 14835 | 3 | | | | PRAMEF2 | 1.00 |
| 14836 | 3 | | | | PRAMEF20 | 1.00 |
| 14837 | 3 | | | | PRAMEF21 | 1.00 |
| 14838 | 3 | | | | PRAMEF22 | 1.00 |
| 14839 | 3 | | | | PRAMEF3 | 1.00 |
| 14840 | 3 | | | | PRAMEF4 | 1.00 |
| 14841 | 3 | | | | PRAMEF5 | 1.00 |
| 14842 | 3 | | | | PRAMEF6 | 1.00 |
| 14843 | 3 | | | | PRAMEF7 | 1.00 |
| 14844 | 3 | | | | PRAMEF8 | 1.00 |
| 14845 | 3 | | | | PRAMEF9 | 1.00 |
| 14846 | 3 | | | | PRAP1 | 1.00 |
| 14847 | 3 | | | | PRB1 | 1.00 |
| 14848 | 3 | | | | PRB3 | 1.00 |
| 14849 | 3 | | | | PRB4 | 1.00 |
| 14850 | 3 | | | | PRCD | 1.00 |
| 14851 | 3 | | | | PRDM12 | 1.00 |
| 14852 | 3 | | | | PRDM13 | 1.00 |
| 14853 | 3 | | | | PRDM14 | 1.00 |
| 14854 | 3 | | | | PRDM5 | 1.00 |
| 14855 | 3 | | | | PRDM7 | 1.00 |
| 14856 | 3 | | | | PRDM9 | 1.00 |
| 14857 | 3 | | | | PRELID2 | 1.00 |
| 14858 | 3 | | | | PREX2 | 1.00 |
| 14859 | 3 | | | | PRG1 | 1.00 |
| 14860 | 3 | | | | PRG3 | 1.00 |
| 14861 | 3 | | | | PRH1 | 1.00 |
| 14862 | 3 | | | | PRH1-PRR4 | 1.00 |
| 14863 | 3 | | | | PRH2 | 1.00 |
| 14864 | 3 | | | | PRHOXNB | 1.00 |
| 14865 | 3 | | | | PRKAA2 | 1.00 |
| 14866 | 3 | | | | PRKAG3 | 1.00 |
| 14867 | 3 | | | | PRKCG | 1.00 |
| 14868 | 3 | | | | PRKCQ | 1.00 |
| 14869 | 3 | | | | PRKG2 | 1.00 |
| 14870 | 3 | | | | PRL | 1.00 |
| 14871 | 3 | | | | PRLH | 1.00 |
| 14872 | 3 | | | | PRLHR | 1.00 |
| 14873 | 3 | | | | PRM1 | 1.00 |
| 14874 | 3 | | | | PRM2 | 1.00 |
| 14875 | 3 | | | | PRM3 | 1.00 |
| 14876 | 3 | | | | PRMT8 | 1.00 |
| 14877 | 3 | | | | PRND | 1.00 |
| 14878 | 3 | | | | PRNT | 1.00 |
| 14879 | 3 | | | | PRO1768 | 1.00 |
| 14880 | 3 | | | | PROC | 1.00 |
| 14881 | 3 | | | | PRODH2 | 1.00 |
| 14882 | 3 | | | | PROK1 | 1.00 |
| 14883 | 3 | | | | PROK2 | 1.00 |
| 14884 | 3 | | | | PROKR1 | 1.00 |
| 14885 | 3 | | | | PROKR2 | 1.00 |
| 14886 | 3 | | | | PROL1 | 1.00 |
| 14887 | 3 | | | | PROP1 | 1.00 |
| 14888 | 3 | | | | PROX1 | 1.00 |
| 14889 | 3 | | | | PROX1-AS1 | 1.00 |
| 14890 | 3 | | | | PROX2 | 1.00 |
| 14891 | 3 | | | | PROZ | 1.00 |
| 14892 | 3 | | | | PRPH2 | 1.00 |
| 14893 | 3 | | | | PRR15 | 1.00 |
| 14894 | 3 | | | | PRR18 | 1.00 |
| 14895 | 3 | | | | PRR19 | 1.00 |
| 14896 | 3 | | | | PRR20B | 1.00 |
| 14897 | 3 | | | | PRR20D | 1.00 |
| 14898 | 3 | | | | PRR20E | 1.00 |
| 14899 | 3 | | | | PRR21 | 1.00 |
| 14900 | 3 | | | | PRR23A | 1.00 |
| 14901 | 3 | | | | PRR23B | 1.00 |
| 14902 | 3 | | | | PRR23C | 1.00 |
| 14903 | 3 | | | | PRR25 | 1.00 |
| 14904 | 3 | | | | PRR5-ARHGAP8 | 1.00 |
| 14905 | 3 | | | | PRSS1 | 1.00 |
| 14906 | 3 | | | | PRSS2 | 1.00 |
| 14907 | 3 | | | | PRSS30P | 1.00 |
| 14908 | 3 | | | | PRSS33 | 1.00 |
| 14909 | 3 | | | | PRSS35 | 1.00 |
| 14910 | 3 | | | | PRSS37 | 1.00 |
| 14911 | 3 | | | | PRSS38 | 1.00 |
| 14912 | 3 | | | | PRSS41 | 1.00 |
| 14913 | 3 | | | | PRSS42 | 1.00 |
| 14914 | 3 | | | | PRSS45 | 1.00 |
| 14915 | 3 | | | | PRSS46 | 1.00 |
| 14916 | 3 | | | | PRSS48 | 1.00 |
| 14917 | 3 | | | | PRSS50 | 1.00 |
| 14918 | 3 | | | | PRSS54 | 1.00 |
| 14919 | 3 | | | | PRSS55 | 1.00 |
| 14920 | 3 | | | | PRSS56 | 1.00 |
| 14921 | 3 | | | | PRSS57 | 1.00 |
| 14922 | 3 | | | | PRSS58 | 1.00 |
| 14923 | 3 | | | | PRTG | 1.00 |
| 14924 | 3 | | | | PRTN3 | 1.00 |
| 14925 | 3 | | | | PRY | 1.00 |
| 14926 | 3 | | | | PSD | 1.00 |
| 14927 | 3 | | | | PSD2 | 1.00 |
| 14928 | 3 | | | | PSG1 | 1.00 |
| 14929 | 3 | | | | PSG10P | 1.00 |
| 14930 | 3 | | | | PSG11 | 1.00 |
| 14931 | 3 | | | | PSG2 | 1.00 |
| 14932 | 3 | | | | PSG3 | 1.00 |
| 14933 | 3 | | | | PSG5 | 1.00 |
| 14934 | 3 | | | | PSG6 | 1.00 |
| 14935 | 3 | | | | PSG7 | 1.00 |
| 14936 | 3 | | | | PSG8 | 1.00 |
| 14937 | 3 | | | | PSG9 | 1.00 |
| 14938 | 3 | | | | PSKH2 | 1.00 |
| 14939 | 3 | | | | PSMA8 | 1.00 |
| 14940 | 3 | | | | PSMB11 | 1.00 |
| 14941 | 3 | | | | PSORS1C3 | 1.00 |
| 14942 | 3 | | | | PTCD1 | 1.00 |
| 14943 | 3 | | | | PTCHD1 | 1.00 |
| 14944 | 3 | | | | PTCHD2 | 1.00 |
| 14945 | 3 | | | | PTCHD3 | 1.00 |
| 14946 | 3 | | | | PTCHD4 | 1.00 |
| 14947 | 3 | | | | PTCRA | 1.00 |
| 14948 | 3 | | | | PTF1A | 1.00 |
| 14949 | 3 | | | | PTGDR | 1.00 |
| 14950 | 3 | | | | PTGER1 | 1.00 |
| 14951 | 3 | | | | PTH | 1.00 |
| 14952 | 3 | | | | PTH2 | 1.00 |
| 14953 | 3 | | | | PTH2R | 1.00 |
| 14954 | 3 | | | | PTPN22 | 1.00 |
| 14955 | 3 | | | | PTPN4 | 1.00 |
| 14956 | 3 | | | | PTPN5 | 1.00 |
| 14957 | 3 | | | | PTPRD | 1.00 |
| 14958 | 3 | | | | PTPRG | 1.00 |
| 14959 | 3 | | | | PTPRH | 1.00 |
| 14960 | 3 | | | | PTPRN | 1.00 |
| 14961 | 3 | | | | PTPRO | 1.00 |
| 14962 | 3 | | | | PTPRQ | 1.00 |
| 14963 | 3 | | | | PTPRR | 1.00 |
| 14964 | 3 | | | | PTPRT | 1.00 |
| 14965 | 3 | | | | PTPRVP | 1.00 |
| 14966 | 3 | | | | PTX4 | 1.00 |
| 14967 | 3 | | | | PURG | 1.00 |
| 14968 | 3 | | | | PUS7L | 1.00 |
| 14969 | 3 | | | | PVALB | 1.00 |
| 14970 | 3 | | | | PVRL3-AS1 | 1.00 |

Fig. 39 - 79

| | | | | | | | | | | | | | | |
|---|---|---|---|---|---|---|---|---|---|---|---|---|---|---|
| 14971 | 3 | | | | | | PWRN1 | 1.00 | 15067 | 3 | | | RGPD2 | 1.00 |
| 14972 | 3 | | | | | | PWRN2 | 1.00 | 15068 | 3 | | | RGPD3 | 1.00 |
| 14973 | 3 | | | | | | PXDNL | 1.00 | 15069 | 3 | | | RGPD4 | 1.00 |
| 14974 | 3 | | | | | | PXT1 | 1.00 | 15070 | 3 | | | RGPD6 | 1.00 |
| 14975 | 3 | | | | | | PYDC2 | 1.00 | 15071 | 3 | | | RGR | 1.00 |
| 14976 | 3 | | | | | | PYGO1 | 1.00 | 15072 | 3 | | | RGS13 | 1.00 |
| 14977 | 3 | | | | | | PYHIN1 | 1.00 | 15073 | 3 | | | RGS17 | 1.00 |
| 14978 | 3 | | | | | | PYY | 1.00 | 15074 | 3 | | | RGS18 | 1.00 |
| 14979 | 3 | | | | | | PYY2 | 1.00 | 15075 | 3 | | | RGS21 | 1.00 |
| 14980 | 3 | | | | | | PZP | 1.00 | 15076 | 3 | | | RGS22 | 1.00 |
| 14981 | 3 | | | | | | QRFP | 1.00 | 15077 | 3 | | | RGS4 | 1.00 |
| 14982 | 3 | | | | | | QRFPR | 1.00 | 15078 | 3 | | | RGS7 | 1.00 |
| 14983 | 3 | | | | | | QRICH2 | 1.00 | 15079 | 3 | | | RGS7BP | 1.00 |
| 14984 | 3 | | | | | | R3HDML | 1.00 | 15080 | 3 | | | RGS8 | 1.00 |
| 14985 | 3 | | | | | | RAB19 | 1.00 | 15081 | 3 | | | RGS9 | 1.00 |
| 14986 | 3 | | | | | | RAB2B | 1.00 | 15082 | 3 | | | RGS9BP | 1.00 |
| 14987 | 3 | | | | | | RAB39A | 1.00 | 15083 | 3 | | | RGSL1 | 1.00 |
| 14988 | 3 | | | | | | RAB39B | 1.00 | 15084 | 3 | | | RHAG | 1.00 |
| 14989 | 3 | | | | | | RAB3C | 1.00 | 15085 | 3 | | | RHBDL3 | 1.00 |
| 14990 | 3 | | | | | | RAB3GAP1 | 1.00 | 15086 | 3 | | | RHCE | 1.00 |
| 14991 | 3 | | | | | | RAB40A | 1.00 | 15087 | 3 | | | RHO | 1.00 |
| 14992 | 3 | | | | | | RAB41 | 1.00 | 15088 | 3 | | | RHOXF2 | 1.00 |
| 14993 | 3 | | | | | | RAB42 | 1.00 | 15089 | 3 | | | RHOXF2B | 1.00 |
| 14994 | 3 | | | | | | RAB4B-EGLN2 | 1.00 | 15090 | 3 | | | RIBC2 | 1.00 |
| 14995 | 3 | | | | | | RAB9BP1 | 1.00 | 15091 | 3 | | | RIIAD1 | 1.00 |
| 14996 | 3 | | | | | | RAD21-AS1 | 1.00 | 15092 | 3 | | | RIMBP3 | 1.00 |
| 14997 | 3 | | | | | | RAD21L1 | 1.00 | 15093 | 3 | | | RIMBP3B | 1.00 |
| 14998 | 3 | | | | | | RAD51AP1 | 1.00 | 15094 | 3 | | | RIMBP3C | 1.00 |
| 14999 | 3 | | | | | | RAD51AP2 | 1.00 | 15095 | 3 | | | RIMKLA | 1.00 |
| 15000 | 3 | | | | | | RAD54B | 1.00 | 15096 | 3 | | | RIMS1 | 1.00 |
| 15001 | 3 | | | | | | RAD54L | 1.00 | 15097 | 3 | | | RIMS2 | 1.00 |
| 15002 | 3 | | | | | | RAD9B | 1.00 | 15098 | 3 | | | RIMS4 | 1.00 |
| 15003 | 3 | | | | | | RAET1K | 1.00 | 15099 | 3 | | | RIPPLY1 | 1.00 |
| 15004 | 3 | | | | | | RAG1 | 1.00 | 15100 | 3 | | | RIPPLY2 | 1.00 |
| 15005 | 3 | | | | | | RAG2 | 1.00 | 15101 | 3 | | | RIT2 | 1.00 |
| 15006 | 3 | | | | | | RALYL | 1.00 | 15102 | 3 | | | RLBP1 | 1.00 |
| 15007 | 3 | | | | | | RANBP17 | 1.00 | 15103 | 3 | | | RLN1 | 1.00 |
| 15008 | 3 | | | | | | RANBP3L | 1.00 | 15104 | 3 | | | RLN2 | 1.00 |
| 15009 | 3 | | | | | | RAPSN | 1.00 | 15105 | 3 | | | RLN3 | 1.00 |
| 15010 | 3 | | | | | | RASA2 | 1.00 | 15106 | 3 | | | RLTPR | 1.00 |
| 15011 | 3 | | | | | | RASEF | 1.00 | 15107 | 3 | | | RMST | 1.00 |
| 15012 | 3 | | | | | | RASGRF1 | 1.00 | 15108 | 3 | | | RNASE10 | 1.00 |
| 15013 | 3 | | | | | | RAX2 | 1.00 | 15109 | 3 | | | RNASE11 | 1.00 |
| 15014 | 3 | | | | | | RBAK-LOC389458 | 1.00 | 15110 | 3 | | | RNASE12 | 1.00 |
| 15015 | 3 | | | | | | RBFOX1 | 1.00 | 15111 | 3 | | | RNASE3 | 1.00 |
| 15016 | 3 | | | | | | RBFOX3 | 1.00 | 15112 | 3 | | | RNASE8 | 1.00 |
| 15017 | 3 | | | | | | RBL1 | 1.00 | 15113 | 3 | | | RNASE9 | 1.00 |
| 15018 | 3 | | | | | | RBM11 | 1.00 | 15114 | 3 | | | RNF103-CHMP3 | 1.00 |
| 15019 | 3 | | | | | | RBM20 | 1.00 | 15115 | 3 | | | RNF113B | 1.00 |
| 15020 | 3 | | | | | | RBM26-AS1 | 1.00 | 15116 | 3 | | | RNF133 | 1.00 |
| 15021 | 3 | | | | | | RBM44 | 1.00 | 15117 | 3 | | | RNF138P1 | 1.00 |
| 15022 | 3 | | | | | | RBM46 | 1.00 | 15118 | 3 | | | RNF148 | 1.00 |
| 15023 | 3 | | | | | | RBMXL2 | 1.00 | 15119 | 3 | | | RNF150 | 1.00 |
| 15024 | 3 | | | | | | RBMXL3 | 1.00 | 15120 | 3 | | | RNF151 | 1.00 |
| 15025 | 3 | | | | | | RBMY1A1 | 1.00 | 15121 | 3 | | | RNF17 | 1.00 |
| 15026 | 3 | | | | | | RBMY1A3P | 1.00 | 15122 | 3 | | | RNF175 | 1.00 |
| 15027 | 3 | | | | | | RBMY1B | 1.00 | 15123 | 3 | | | RNF182 | 1.00 |
| 15028 | 3 | | | | | | RBMY1D | 1.00 | 15124 | 3 | | | RNF183 | 1.00 |
| 15029 | 3 | | | | | | RBMY1E | 1.00 | 15125 | 3 | | | RNF186 | 1.00 |
| 15030 | 3 | | | | | | RBMY1F | 1.00 | 15126 | 3 | | | RNF224 | 1.00 |
| 15031 | 3 | | | | | | RBMY1J | 1.00 | 15127 | 3 | | | RNFT2 | 1.00 |
| 15032 | 3 | | | | | | RBMY2EP | 1.00 | 15128 | 3 | | | RNPC3 | 1.00 |
| 15033 | 3 | | | | | | RBMY2FP | 1.00 | 15129 | 3 | | | RNU4ATAC | 1.00 |
| 15034 | 3 | | | | | | RBMY3AP | 1.00 | 15130 | 3 | | | RNU5D-1 | 1.00 |
| 15035 | 3 | | | | | | RBP2 | 1.00 | 15131 | 3 | | | RNU5E-1 | 1.00 |
| 15036 | 3 | | | | | | RBP3 | 1.00 | 15132 | 3 | | | RNU5F-1 | 1.00 |
| 15037 | 3 | | | | | | RBPJL | 1.00 | 15133 | 3 | | | RNU6ATAC | 1.00 |
| 15038 | 3 | | | | | | RCAN3AS | 1.00 | 15134 | 3 | | | RNU86 | 1.00 |
| 15039 | 3 | | | | | | RCOR2 | 1.00 | 15135 | 3 | | | RNY4 | 1.00 |
| 15040 | 3 | | | | | | RD3 | 1.00 | 15136 | 3 | | | RNY5 | 1.00 |
| 15041 | 3 | | | | | | RDH8 | 1.00 | 15137 | 3 | | | ROPN1L | 1.00 |
| 15042 | 3 | | | | | | RDM1 | 1.00 | 15138 | 3 | | | RORB | 1.00 |
| 15043 | 3 | | | | | | REG1A | 1.00 | 15139 | 3 | | | ROS1 | 1.00 |
| 15044 | 3 | | | | | | REG1B | 1.00 | 15140 | 3 | | | RP1 | 1.00 |
| 15045 | 3 | | | | | | REG1P | 1.00 | 15141 | 3 | | | RP11-165H21 | 1.00 |
| 15046 | 3 | | | | | | REG3A | 1.00 | 15142 | 3 | | | RP1-177G6.2 | 1.00 |
| 15047 | 3 | | | | | | REG3G | 1.00 | 15143 | 3 | | | RP1L1 | 1.00 |
| 15048 | 3 | | | | | | REG4 | 1.00 | 15144 | 3 | | | RPA4 | 1.00 |
| 15049 | 3 | | | | | | RELN | 1.00 | 15145 | 3 | | | RPE65 | 1.00 |
| 15050 | 3 | | | | | | REN | 1.00 | 15146 | 3 | | | RPGRIP1 | 1.00 |
| 15051 | 3 | | | | | | REPS2 | 1.00 | 15147 | 3 | | | RPGRIP1L | 1.00 |
| 15052 | 3 | | | | | | REREP3 | 1.00 | 15148 | 3 | | | RPH3A | 1.00 |
| 15053 | 3 | | | | | | RESP18 | 1.00 | 15149 | 3 | | | RPL10L | 1.00 |
| 15054 | 3 | | | | | | RETN | 1.00 | 15150 | 3 | | | RPL13AP17 | 1.00 |
| 15055 | 3 | | | | | | RETNLB | 1.00 | 15151 | 3 | | | RPL13AP3 | 1.00 |
| 15056 | 3 | | | | | | REXO1L1 | 1.00 | 15152 | 3 | | | RPL13AP5 | 1.00 |
| 15057 | 3 | | | | | | RFPL1 | 1.00 | 15153 | 3 | | | RPL23AP64 | 1.00 |
| 15058 | 3 | | | | | | RFPL1-AS1 | 1.00 | 15154 | 3 | | | RPL31P11 | 1.00 |
| 15059 | 3 | | | | | | RFPL2 | 1.00 | 15155 | 3 | | | RPL3L | 1.00 |
| 15060 | 3 | | | | | | RFPL3 | 1.00 | 15156 | 3 | | | RPLP0P2 | 1.00 |
| 15061 | 3 | | | | | | RFPL4A | 1.00 | 15157 | 3 | | | RPS16P5 | 1.00 |
| 15062 | 3 | | | | | | RFPL4B | 1.00 | 15158 | 3 | | | RPS21 | 1.00 |
| 15063 | 3 | | | | | | RFX3 | 1.00 | 15159 | 3 | | | RPS4Y2 | 1.00 |
| 15064 | 3 | | | | | | RFX4 | 1.00 | 15160 | 3 | | | RPS7P5 | 1.00 |
| 15065 | 3 | | | | | | RFX6 | 1.00 | 15161 | 3 | | | RPSAP52 | 1.00 |
| 15066 | 3 | | | | | | RGAG1 | 1.00 | 15162 | 3 | | | RRH | 1.00 |

Fig. 39 - 80

| | | | | | | | | | | | | | |
|---|---|---|---|---|---|---|---|---|---|---|---|---|---|
| 15163 | 3 | | | | | RS1 | 1.00 | 15259 | 3 | | | SELV | 1.00 |
| 15164 | 3 | | | | | RSPH10B2 | 1.00 | 15260 | 3 | | | SEMA3E | 1.00 |
| 15165 | 3 | | | | | RSPH4A | 1.00 | 15261 | 3 | | | SEMG1 | 1.00 |
| 15166 | 3 | | | | | RSPH6A | 1.00 | 15262 | 3 | | | SEMG2 | 1.00 |
| 15167 | 3 | | | | | RSPH9 | 1.00 | 15263 | 3 | | | SENP3-EIF4A1 | 1.00 |
| 15168 | 3 | | | | | RSPO2 | 1.00 | 15264 | 3 | | | SEPT12 | 1.00 |
| 15169 | 3 | | | | | RTBDN | 1.00 | 15265 | 3 | | | SEPT14 | 1.00 |
| 15170 | 3 | | | | | RTDR1 | 1.00 | 15266 | 3 | | | SEPT7L | 1.00 |
| 15171 | 3 | | | | | RTKN2 | 1.00 | 15267 | 3 | | | SERF2-C15ORF63 | 1.00 |
| 15172 | 3 | | | | | RTL1 | 1.00 | 15268 | 3 | | | SERPINA10 | 1.00 |
| 15173 | 3 | | | | | RTP1 | 1.00 | 15269 | 3 | | | SERPINA13 | 1.00 |
| 15174 | 3 | | | | | RTP2 | 1.00 | 15270 | 3 | | | SERPINA4 | 1.00 |
| 15175 | 3 | | | | | RTP3 | 1.00 | 15271 | 3 | | | SERPINA6 | 1.00 |
| 15176 | 3 | | | | | RTTN | 1.00 | 15272 | 3 | | | SERPINA7 | 1.00 |
| 15177 | 3 | | | | | RUFY4 | 1.00 | 15273 | 3 | | | SERPINB10 | 1.00 |
| 15178 | 3 | | | | | RUNX1-IT1 | 1.00 | 15274 | 3 | | | SERPINB11 | 1.00 |
| 15179 | 3 | | | | | RXFP1 | 1.00 | 15275 | 3 | | | SERPINC1 | 1.00 |
| 15180 | 3 | | | | | RXFP2 | 1.00 | 15276 | 3 | | | SERPIND1 | 1.00 |
| 15181 | 3 | | | | | RXFP3 | 1.00 | 15277 | 3 | | | SERPINE3 | 1.00 |
| 15182 | 3 | | | | | RXFP4 | 1.00 | 15278 | 3 | | | SERPINI2 | 1.00 |
| 15183 | 3 | | | | | RYR2 | 1.00 | 15279 | 3 | | | SERTM1 | 1.00 |
| 15184 | 3 | | | | | RYR3 | 1.00 | 15280 | 3 | | | SESN3 | 1.00 |
| 15185 | 3 | | | | | S100A5 | 1.00 | 15281 | 3 | | | SEZ6 | 1.00 |
| 15186 | 3 | | | | | S100A7A | 1.00 | 15282 | 3 | | | SFTA1P | 1.00 |
| 15187 | 3 | | | | | S100A7L2 | 1.00 | 15283 | 3 | | | SFTA2 | 1.00 |
| 15188 | 3 | | | | | S100G | 1.00 | 15284 | 3 | | | SFTA3 | 1.00 |
| 15189 | 3 | | | | | S100Z | 1.00 | 15285 | 3 | | | SGCZ | 1.00 |
| 15190 | 3 | | | | | SAA2-SAA4 | 1.00 | 15286 | 3 | | | SGIP1 | 1.00 |
| 15191 | 3 | | | | | SAA3P | 1.00 | 15287 | 3 | | | SGK110 | 1.00 |
| 15192 | 3 | | | | | SAA4 | 1.00 | 15288 | 3 | | | SGK196 | 1.00 |
| 15193 | 3 | | | | | SAG | 1.00 | 15289 | 3 | | | SGOL1 | 1.00 |
| 15194 | 3 | | | | | SAGE1 | 1.00 | 15290 | 3 | | | SGOL2 | 1.00 |
| 15195 | 3 | | | | | SALL1 | 1.00 | 15291 | 3 | | | SH2D1A | 1.00 |
| 15196 | 3 | | | | | SALL3 | 1.00 | 15292 | 3 | | | SH2D1B | 1.00 |
| 15197 | 3 | | | | | SALL4 | 1.00 | 15293 | 3 | | | SH2D2A | 1.00 |
| 15198 | 3 | | | | | SAMD11 | 1.00 | 15294 | 3 | | | SH2D4B | 1.00 |
| 15199 | 3 | | | | | SAMD12 | 1.00 | 15295 | 3 | | | SH2D5 | 1.00 |
| 15200 | 3 | | | | | SAMD12-AS1 | 1.00 | 15296 | 3 | | | SH2D6 | 1.00 |
| 15201 | 3 | | | | | SAMD13 | 1.00 | 15297 | 3 | | | SH2D7 | 1.00 |
| 15202 | 3 | | | | | SAMD14 | 1.00 | 15298 | 3 | | | SH3GL2 | 1.00 |
| 15203 | 3 | | | | | SAMD15 | 1.00 | 15299 | 3 | | | SH3GL3 | 1.00 |
| 15204 | 3 | | | | | SAMD3 | 1.00 | 15300 | 3 | | | SH3TC2 | 1.00 |
| 15205 | 3 | | | | | SAMD7 | 1.00 | 15301 | 3 | | | SHANK1 | 1.00 |
| 15206 | 3 | | | | | SARDH | 1.00 | 15302 | 3 | | | SHBG | 1.00 |
| 15207 | 3 | | | | | SATL1 | 1.00 | 15303 | 3 | | | SHC3 | 1.00 |
| 15208 | 3 | | | | | SBK2 | 1.00 | 15304 | 3 | | | SHCBP1L | 1.00 |
| 15209 | 3 | | | | | SCAND3 | 1.00 | 15305 | 3 | | | SHD | 1.00 |
| 15210 | 3 | | | | | SCARNA1 | 1.00 | 15306 | 3 | | | SHH | 1.00 |
| 15211 | 3 | | | | | SCARNA11 | 1.00 | 15307 | 3 | | | SHISA7 | 1.00 |
| 15212 | 3 | | | | | SCARNA13 | 1.00 | 15308 | 3 | | | SHISA8 | 1.00 |
| 15213 | 3 | | | | | SCARNA14 | 1.00 | 15309 | 3 | | | SHISA9 | 1.00 |
| 15214 | 3 | | | | | SCARNA15 | 1.00 | 15310 | 3 | | | SHOX | 1.00 |
| 15215 | 3 | | | | | SCARNA18 | 1.00 | 15311 | 3 | | | SHPRH | 1.00 |
| 15216 | 3 | | | | | SCARNA20 | 1.00 | 15312 | 3 | | | SI | 1.00 |
| 15217 | 3 | | | | | SCARNA21 | 1.00 | 15313 | 3 | | | SIAH3 | 1.00 |
| 15218 | 3 | | | | | SCARNA22 | 1.00 | 15314 | 3 | | | SIDT1 | 1.00 |
| 15219 | 3 | | | | | SCARNA23 | 1.00 | 15315 | 3 | | | SIGLEC11 | 1.00 |
| 15220 | 3 | | | | | SCARNA27 | 1.00 | 15316 | 3 | | | SIGLEC12 | 1.00 |
| 15221 | 3 | | | | | SCARNA3 | 1.00 | 15317 | 3 | | | SIGLEC14 | 1.00 |
| 15222 | 3 | | | | | SCARNA5 | 1.00 | 15318 | 3 | | | SIGLEC15 | 1.00 |
| 15223 | 3 | | | | | SCARNA6 | 1.00 | 15319 | 3 | | | SIGLEC16 | 1.00 |
| 15224 | 3 | | | | | SCARNA8 | 1.00 | 15320 | 3 | | | SIGLEC5 | 1.00 |
| 15225 | 3 | | | | | SCARNA9L | 1.00 | 15321 | 3 | | | SIGLEC6 | 1.00 |
| 15226 | 3 | | | | | SCG2 | 1.00 | 15322 | 3 | | | SIGLEC7 | 1.00 |
| 15227 | 3 | | | | | SCG3 | 1.00 | 15323 | 3 | | | SIGLEC8 | 1.00 |
| 15228 | 3 | | | | | SCG5 | 1.00 | 15324 | 3 | | | SIGLEC9 | 1.00 |
| 15229 | 3 | | | | | SCGB1A1 | 1.00 | 15325 | 3 | | | SIM1 | 1.00 |
| 15230 | 3 | | | | | SCGB1C1 | 1.00 | 15326 | 3 | | | SIM2 | 1.00 |
| 15231 | 3 | | | | | SCGB1D1 | 1.00 | 15327 | 3 | | | SIRPD | 1.00 |
| 15232 | 3 | | | | | SCGB1D4 | 1.00 | 15328 | 3 | | | SIX1 | 1.00 |
| 15233 | 3 | | | | | SCGB2B2 | 1.00 | 15329 | 3 | | | SIX3 | 1.00 |
| 15234 | 3 | | | | | SCGN | 1.00 | 15330 | 3 | | | SIX4 | 1.00 |
| 15235 | 3 | | | | | SCIMP | 1.00 | 15331 | 3 | | | SIX6 | 1.00 |
| 15236 | 3 | | | | | SCLT1 | 1.00 | 15332 | 3 | | | SKA1 | 1.00 |
| 15237 | 3 | | | | | SCML2 | 1.00 | 15333 | 3 | | | SKINTL | 1.00 |
| 15238 | 3 | | | | | SCML4 | 1.00 | 15334 | 3 | | | SKOR1 | 1.00 |
| 15239 | 3 | | | | | SCN10A | 1.00 | 15335 | 3 | | | SLAMF1 | 1.00 |
| 15240 | 3 | | | | | SCN11A | 1.00 | 15336 | 3 | | | SLAMF9 | 1.00 |
| 15241 | 3 | | | | | SCN1A | 1.00 | 15337 | 3 | | | SLC10A1 | 1.00 |
| 15242 | 3 | | | | | SCN2A | 1.00 | 15338 | 3 | | | SLC10A2 | 1.00 |
| 15243 | 3 | | | | | SCN3A | 1.00 | 15339 | 3 | | | SLC10A4 | 1.00 |
| 15244 | 3 | | | | | SCN5A | 1.00 | 15340 | 3 | | | SLC10A5 | 1.00 |
| 15245 | 3 | | | | | SCN8A | 1.00 | 15341 | 3 | | | SLC11A1 | 1.00 |
| 15246 | 3 | | | | | SCN9A | 1.00 | 15342 | 3 | | | SLC12A1 | 1.00 |
| 15247 | 3 | | | | | SCRT1 | 1.00 | 15343 | 3 | | | SLC12A3 | 1.00 |
| 15248 | 3 | | | | | SCRT2 | 1.00 | 15344 | 3 | | | SLC12A5 | 1.00 |
| 15249 | 3 | | | | | SCT | 1.00 | 15345 | 3 | | | SLC13A1 | 1.00 |
| 15250 | 3 | | | | | SCTR | 1.00 | 15346 | 3 | | | SLC13A4 | 1.00 |
| 15251 | 3 | | | | | SCUBE1 | 1.00 | 15347 | 3 | | | SLC13A5 | 1.00 |
| 15252 | 3 | | | | | SCUBE3 | 1.00 | 15348 | 3 | | | SLC14A2 | 1.00 |
| 15253 | 3 | | | | | SDC4P | 1.00 | 15349 | 3 | | | SLC15A2 | 1.00 |
| 15254 | 3 | | | | | SDS | 1.00 | 15350 | 3 | | | SLC15A5 | 1.00 |
| 15255 | 3 | | | | | SEBOX | 1.00 | 15351 | 3 | | | SLC16A12 | 1.00 |
| 15256 | 3 | | | | | SEC1 | 1.00 | 15352 | 3 | | | SLC16A7 | 1.00 |
| 15257 | 3 | | | | | SEC14L3 | 1.00 | 15353 | 3 | | | SLC16A8 | 1.00 |
| 15258 | 3 | | | | | SEL1L2 | 1.00 | 15354 | 3 | | | SLC16A9 | 1.00 |

Fig. 39 - 81

| | | | | | | | | | | | | | | | |
|---|---|---|---|---|---|---|---|---|---|---|---|---|---|---|---|
| 15355 | 3 | | | | | SLC17A1 | 1.00 | 15451 | 3 | | | | | SLC8A2 | 1.00 |
| 15356 | 3 | | | | | SLC17A2 | 1.00 | 15452 | 3 | | | | | SLC8A3 | 1.00 |
| 15357 | 3 | | | | | SLC17A3 | 1.00 | 15453 | 3 | | | | | SLC9A10 | 1.00 |
| 15358 | 3 | | | | | SLC17A4 | 1.00 | 15454 | 3 | | | | | SLC9A11 | 1.00 |
| 15359 | 3 | | | | | SLC17A6 | 1.00 | 15455 | 3 | | | | | SLC9A4 | 1.00 |
| 15360 | 3 | | | | | SLC17A8 | 1.00 | 15456 | 3 | | | | | SLC9A7 | 1.00 |
| 15361 | 3 | | | | | SLC18A1 | 1.00 | 15457 | 3 | | | | | SLC9A7P1 | 1.00 |
| 15362 | 3 | | | | | SLC18A3 | 1.00 | 15458 | 3 | | | | | SLC9B1 | 1.00 |
| 15363 | 3 | | | | | SLC22A1 | 1.00 | 15459 | 3 | | | | | SLCO1A2 | 1.00 |
| 15364 | 3 | | | | | SLC22A10 | 1.00 | 15460 | 3 | | | | | SLCO1B1 | 1.00 |
| 15365 | 3 | | | | | SLC22A11 | 1.00 | 15461 | 3 | | | | | SLCO1B3 | 1.00 |
| 15366 | 3 | | | | | SLC22A12 | 1.00 | 15462 | 3 | | | | | SLCO1B7 | 1.00 |
| 15367 | 3 | | | | | SLC22A13 | 1.00 | 15463 | 3 | | | | | SLCO1C1 | 1.00 |
| 15368 | 3 | | | | | SLC22A14 | 1.00 | 15464 | 3 | | | | | SLCO5A1 | 1.00 |
| 15369 | 3 | | | | | SLC22A16 | 1.00 | 15465 | 3 | | | | | SLCO6A1 | 1.00 |
| 15370 | 3 | | | | | SLC22A18AS | 1.00 | 15466 | 3 | | | | | SLFN12L | 1.00 |
| 15371 | 3 | | | | | SLC22A2 | 1.00 | 15467 | 3 | | | | | SLFN14 | 1.00 |
| 15372 | 3 | | | | | SLC22A20 | 1.00 | 15468 | 3 | | | | | SLFNL1 | 1.00 |
| 15373 | 3 | | | | | SLC22A24 | 1.00 | 15469 | 3 | | | | | SLIT1 | 1.00 |
| 15374 | 3 | | | | | SLC22A25 | 1.00 | 15470 | 3 | | | | | SLIT2-IT1 | 1.00 |
| 15375 | 3 | | | | | SLC22A6 | 1.00 | 15471 | 3 | | | | | SLITRK1 | 1.00 |
| 15376 | 3 | | | | | SLC22A7 | 1.00 | 15472 | 3 | | | | | SLITRK3 | 1.00 |
| 15377 | 3 | | | | | SLC22A8 | 1.00 | 15473 | 3 | | | | | SLITRK5 | 1.00 |
| 15378 | 3 | | | | | SLC22A9 | 1.00 | 15474 | 3 | | | | | SLMO2-ATP5E | 1.00 |
| 15379 | 3 | | | | | SLC24A2 | 1.00 | 15475 | 3 | | | | | SMA5 | 1.00 |
| 15380 | 3 | | | | | SLC24A4 | 1.00 | 15476 | 3 | | | | | SMC1B | 1.00 |
| 15381 | 3 | | | | | SLC25A2 | 1.00 | 15477 | 3 | | | | | SMCP | 1.00 |
| 15382 | 3 | | | | | SLC25A21 | 1.00 | 15478 | 3 | | | | | SMCR5 | 1.00 |
| 15383 | 3 | | | | | SLC25A31 | 1.00 | 15479 | 3 | | | | | SMCR9 | 1.00 |
| 15384 | 3 | | | | | SLC25A41 | 1.00 | 15480 | 3 | | | | | SMEK3P | 1.00 |
| 15385 | 3 | | | | | SLC25A47 | 1.00 | 15481 | 3 | | | | | SMN1 | 1.00 |
| 15386 | 3 | | | | | SLC26A3 | 1.00 | 15482 | 3 | | | | | SMPX | 1.00 |
| 15387 | 3 | | | | | SLC26A4 | 1.00 | 15483 | 3 | | | | | SMR3A | 1.00 |
| 15388 | 3 | | | | | SLC26A5 | 1.00 | 15484 | 3 | | | | | SMR3B | 1.00 |
| 15389 | 3 | | | | | SLC26A8 | 1.00 | 15485 | 3 | | | | | SMTNL1 | 1.00 |
| 15390 | 3 | | | | | SLC27A5 | 1.00 | 15486 | 3 | | | | | SMYD1 | 1.00 |
| 15391 | 3 | | | | | SLC27A6 | 1.00 | 15487 | 3 | | | | | SNAP25 | 1.00 |
| 15392 | 3 | | | | | SLC28A1 | 1.00 | 15488 | 3 | | | | | SNAP91 | 1.00 |
| 15393 | 3 | | | | | SLC28A2 | 1.00 | 15489 | 3 | | | | | SNAR-A1 | 1.00 |
| 15394 | 3 | | | | | SLC2A13 | 1.00 | 15490 | 3 | | | | | SNAR-A11 | 1.00 |
| 15395 | 3 | | | | | SLC2A14 | 1.00 | 15491 | 3 | | | | | SNAR-A12 | 1.00 |
| 15396 | 3 | | | | | SLC2A2 | 1.00 | 15492 | 3 | | | | | SNAR-A13 | 1.00 |
| 15397 | 3 | | | | | SLC2A7 | 1.00 | 15493 | 3 | | | | | SNAR-A14 | 1.00 |
| 15398 | 3 | | | | | SLC30A10 | 1.00 | 15494 | 3 | | | | | SNAR-A2 | 1.00 |
| 15399 | 3 | | | | | SLC30A2 | 1.00 | 15495 | 3 | | | | | SNAR-A3 | 1.00 |
| 15400 | 3 | | | | | SLC30A3 | 1.00 | 15496 | 3 | | | | | SNAR-A6 | 1.00 |
| 15401 | 3 | | | | | SLC30A4 | 1.00 | 15497 | 3 | | | | | SNAR-A7 | 1.00 |
| 15402 | 3 | | | | | SLC30A8 | 1.00 | 15498 | 3 | | | | | SNAR-A8 | 1.00 |
| 15403 | 3 | | | | | SLC32A1 | 1.00 | 15499 | 3 | | | | | SNAR-B2 | 1.00 |
| 15404 | 3 | | | | | SLC34A1 | 1.00 | 15500 | 3 | | | | | SNAR-C2 | 1.00 |
| 15405 | 3 | | | | | SLC34A3 | 1.00 | 15501 | 3 | | | | | SNAR-C3 | 1.00 |
| 15406 | 3 | | | | | SLC35D3 | 1.00 | 15502 | 3 | | | | | SNAR-C4 | 1.00 |
| 15407 | 3 | | | | | SLC35F3 | 1.00 | 15503 | 3 | | | | | SNAR-C5 | 1.00 |
| 15408 | 3 | | | | | SLC35F4 | 1.00 | 15504 | 3 | | | | | SNAR-D | 1.00 |
| 15409 | 3 | | | | | SLC35G3 | 1.00 | 15505 | 3 | | | | | SNAR-E | 1.00 |
| 15410 | 3 | | | | | SLC35G5 | 1.00 | 15506 | 3 | | | | | SNAR-F | 1.00 |
| 15411 | 3 | | | | | SLC35G6 | 1.00 | 15507 | 3 | | | | | SNAR-G1 | 1.00 |
| 15412 | 3 | | | | | SLC36A2 | 1.00 | 15508 | 3 | | | | | SNAR-G2 | 1.00 |
| 15413 | 3 | | | | | SLC36A3 | 1.00 | 15509 | 3 | | | | | SNAR-H | 1.00 |
| 15414 | 3 | | | | | SLC38A11 | 1.00 | 15510 | 3 | | | | | SNAR-I | 1.00 |
| 15415 | 3 | | | | | SLC38A3 | 1.00 | 15511 | 3 | | | | | SNCB | 1.00 |
| 15416 | 3 | | | | | SLC38A4 | 1.00 | 15512 | 3 | | | | | SND1-IT1 | 1.00 |
| 15417 | 3 | | | | | SLC38A8 | 1.00 | 15513 | 3 | | | | | SNORA1 | 1.00 |
| 15418 | 3 | | | | | SLC39A12 | 1.00 | 15514 | 3 | | | | | SNORA10 | 1.00 |
| 15419 | 3 | | | | | SLC39A5 | 1.00 | 15515 | 3 | | | | | SNORA11B | 1.00 |
| 15420 | 3 | | | | | SLC3A1 | 1.00 | 15516 | 3 | | | | | SNORA11C | 1.00 |
| 15421 | 3 | | | | | SLC45A2 | 1.00 | 15517 | 3 | | | | | SNORA11D | 1.00 |
| 15422 | 3 | | | | | SLC4A1 | 1.00 | 15518 | 3 | | | | | SNORA11E | 1.00 |
| 15423 | 3 | | | | | SLC4A10 | 1.00 | 15519 | 3 | | | | | SNORA13 | 1.00 |
| 15424 | 3 | | | | | SLC4A4 | 1.00 | 15520 | 3 | | | | | SNORA14A | 1.00 |
| 15425 | 3 | | | | | SLC4A8 | 1.00 | 15521 | 3 | | | | | SNORA14B | 1.00 |
| 15426 | 3 | | | | | SLC4A9 | 1.00 | 15522 | 3 | | | | | SNORA15 | 1.00 |
| 15427 | 3 | | | | | SLC5A11 | 1.00 | 15523 | 3 | | | | | SNORA16A | 1.00 |
| 15428 | 3 | | | | | SLC5A12 | 1.00 | 15524 | 3 | | | | | SNORA16B | 1.00 |
| 15429 | 3 | | | | | SLC5A2 | 1.00 | 15525 | 3 | | | | | SNORA17 | 1.00 |
| 15430 | 3 | | | | | SLC5A4 | 1.00 | 15526 | 3 | | | | | SNORA18 | 1.00 |
| 15431 | 3 | | | | | SLC5A5 | 1.00 | 15527 | 3 | | | | | SNORA19 | 1.00 |
| 15432 | 3 | | | | | SLC5A7 | 1.00 | 15528 | 3 | | | | | SNORA20 | 1.00 |
| 15433 | 3 | | | | | SLC5A8 | 1.00 | 15529 | 3 | | | | | SNORA23 | 1.00 |
| 15434 | 3 | | | | | SLC6A10P | 1.00 | 15530 | 3 | | | | | SNORA24 | 1.00 |
| 15435 | 3 | | | | | SLC6A12 | 1.00 | 15531 | 3 | | | | | SNORA25 | 1.00 |
| 15436 | 3 | | | | | SLC6A13 | 1.00 | 15532 | 3 | | | | | SNORA26 | 1.00 |
| 15437 | 3 | | | | | SLC6A18 | 1.00 | 15533 | 3 | | | | | SNORA28 | 1.00 |
| 15438 | 3 | | | | | SLC6A19 | 1.00 | 15534 | 3 | | | | | SNORA29 | 1.00 |
| 15439 | 3 | | | | | SLC6A20 | 1.00 | 15535 | 3 | | | | | SNORA2A | 1.00 |
| 15440 | 3 | | | | | SLC6A3 | 1.00 | 15536 | 3 | | | | | SNORA2B | 1.00 |
| 15441 | 3 | | | | | SLC6A4 | 1.00 | 15537 | 3 | | | | | SNORA30 | 1.00 |
| 15442 | 3 | | | | | SLC6A5 | 1.00 | 15538 | 3 | | | | | SNORA32 | 1.00 |
| 15443 | 3 | | | | | SLC6A7 | 1.00 | 15539 | 3 | | | | | SNORA33 | 1.00 |
| 15444 | 3 | | | | | SLC7A10 | 1.00 | 15540 | 3 | | | | | SNORA35 | 1.00 |
| 15445 | 3 | | | | | SLC7A11 | 1.00 | 15541 | 3 | | | | | SNORA36A | 1.00 |
| 15446 | 3 | | | | | SLC7A13 | 1.00 | 15542 | 3 | | | | | SNORA36B | 1.00 |
| 15447 | 3 | | | | | SLC7A14 | 1.00 | 15543 | 3 | | | | | SNORA36C | 1.00 |
| 15448 | 3 | | | | | SLC7A3 | 1.00 | 15544 | 3 | | | | | SNORA37 | 1.00 |
| 15449 | 3 | | | | | SLC7A5P1 | 1.00 | 15545 | 3 | | | | | SNORA38 | 1.00 |
| 15450 | 3 | | | | | SLC7A9 | 1.00 | 15546 | 3 | | | | | SNORA38B | 1.00 |

Fig. 39 - 82

| | | | | | | | | | | | | | | |
|---|---|---|---|---|---|---|---|---|---|---|---|---|---|---|
| 15547 | 3 | | | | | SNORA39 | 1.00 | 15643 | 3 | | | | SNORD114-7 | 1.00 |
| 15548 | 3 | | | | | SNORA4 | 1.00 | 15644 | 3 | | | | SNORD114-8 | 1.00 |
| 15549 | 3 | | | | | SNORA40 | 1.00 | 15645 | 3 | | | | SNORD114-9 | 1.00 |
| 15550 | 3 | | | | | SNORA43 | 1.00 | 15646 | 3 | | | | SNORD115-1 | 1.00 |
| 15551 | 3 | | | | | SNORA46 | 1.00 | 15647 | 3 | | | | SNORD115-10 | 1.00 |
| 15552 | 3 | | | | | SNORA47 | 1.00 | 15648 | 3 | | | | SNORD115-11 | 1.00 |
| 15553 | 3 | | | | | SNORA49 | 1.00 | 15649 | 3 | | | | SNORD115-12 | 1.00 |
| 15554 | 3 | | | | | SNORA50 | 1.00 | 15650 | 3 | | | | SNORD115-13 | 1.00 |
| 15555 | 3 | | | | | SNORA54 | 1.00 | 15651 | 3 | | | | SNORD115-14 | 1.00 |
| 15556 | 3 | | | | | SNORA55 | 1.00 | 15652 | 3 | | | | SNORD115-15 | 1.00 |
| 15557 | 3 | | | | | SNORA56 | 1.00 | 15653 | 3 | | | | SNORD115-16 | 1.00 |
| 15558 | 3 | | | | | SNORA58 | 1.00 | 15654 | 3 | | | | SNORD115-17 | 1.00 |
| 15559 | 3 | | | | | SNORA59A | 1.00 | 15655 | 3 | | | | SNORD115-18 | 1.00 |
| 15560 | 3 | | | | | SNORA59B | 1.00 | 15656 | 3 | | | | SNORD115-19 | 1.00 |
| 15561 | 3 | | | | | SNORA5A | 1.00 | 15657 | 3 | | | | SNORD115-2 | 1.00 |
| 15562 | 3 | | | | | SNORA5B | 1.00 | 15658 | 3 | | | | SNORD115-20 | 1.00 |
| 15563 | 3 | | | | | SNORA5C | 1.00 | 15659 | 3 | | | | SNORD115-21 | 1.00 |
| 15564 | 3 | | | | | SNORA6 | 1.00 | 15660 | 3 | | | | SNORD115-22 | 1.00 |
| 15565 | 3 | | | | | SNORA60 | 1.00 | 15661 | 3 | | | | SNORD115-23 | 1.00 |
| 15566 | 3 | | | | | SNORA62 | 1.00 | 15662 | 3 | | | | SNORD115-24 | 1.00 |
| 15567 | 3 | | | | | SNORA63 | 1.00 | 15663 | 3 | | | | SNORD115-25 | 1.00 |
| 15568 | 3 | | | | | SNORA65 | 1.00 | 15664 | 3 | | | | SNORD115-26 | 1.00 |
| 15569 | 3 | | | | | SNORA66 | 1.00 | 15665 | 3 | | | | SNORD115-27 | 1.00 |
| 15570 | 3 | | | | | SNORA68 | 1.00 | 15666 | 3 | | | | SNORD115-28 | 1.00 |
| 15571 | 3 | | | | | SNORA69 | 1.00 | 15667 | 3 | | | | SNORD115-29 | 1.00 |
| 15572 | 3 | | | | | SNORA70B | 1.00 | 15668 | 3 | | | | SNORD115-3 | 1.00 |
| 15573 | 3 | | | | | SNORA70C | 1.00 | 15669 | 3 | | | | SNORD115-30 | 1.00 |
| 15574 | 3 | | | | | SNORA70D | 1.00 | 15670 | 3 | | | | SNORD115-31 | 1.00 |
| 15575 | 3 | | | | | SNORA70E | 1.00 | 15671 | 3 | | | | SNORD115-32 | 1.00 |
| 15576 | 3 | | | | | SNORA70F | 1.00 | 15672 | 3 | | | | SNORD115-33 | 1.00 |
| 15577 | 3 | | | | | SNORA70G | 1.00 | 15673 | 3 | | | | SNORD115-34 | 1.00 |
| 15578 | 3 | | | | | SNORA71B | 1.00 | 15674 | 3 | | | | SNORD115-35 | 1.00 |
| 15579 | 3 | | | | | SNORA71C | 1.00 | 15675 | 3 | | | | SNORD115-37 | 1.00 |
| 15580 | 3 | | | | | SNORA71D | 1.00 | 15676 | 3 | | | | SNORD115-38 | 1.00 |
| 15581 | 3 | | | | | SNORA72 | 1.00 | 15677 | 3 | | | | SNORD115-39 | 1.00 |
| 15582 | 3 | | | | | SNORA74B | 1.00 | 15678 | 3 | | | | SNORD115-4 | 1.00 |
| 15583 | 3 | | | | | SNORA75 | 1.00 | 15679 | 3 | | | | SNORD115-40 | 1.00 |
| 15584 | 3 | | | | | SNORA76 | 1.00 | 15680 | 3 | | | | SNORD115-41 | 1.00 |
| 15585 | 3 | | | | | SNORA78 | 1.00 | 15681 | 3 | | | | SNORD115-42 | 1.00 |
| 15586 | 3 | | | | | SNORA79 | 1.00 | 15682 | 3 | | | | SNORD115-44 | 1.00 |
| 15587 | 3 | | | | | SNORA7A | 1.00 | 15683 | 3 | | | | SNORD115-45 | 1.00 |
| 15588 | 3 | | | | | SNORA7B | 1.00 | 15684 | 3 | | | | SNORD115-47 | 1.00 |
| 15589 | 3 | | | | | SNORA8 | 1.00 | 15685 | 3 | | | | SNORD115-48 | 1.00 |
| 15590 | 3 | | | | | SNORA80 | 1.00 | 15686 | 3 | | | | SNORD115-5 | 1.00 |
| 15591 | 3 | | | | | SNORA80B | 1.00 | 15687 | 3 | | | | SNORD115-6 | 1.00 |
| 15592 | 3 | | | | | SNORA84 | 1.00 | 15688 | 3 | | | | SNORD115-7 | 1.00 |
| 15593 | 3 | | | | | SNORA9 | 1.00 | 15689 | 3 | | | | SNORD115-8 | 1.00 |
| 15594 | 3 | | | | | SNORD100 | 1.00 | 15690 | 3 | | | | SNORD115-9 | 1.00 |
| 15595 | 3 | | | | | SNORD101 | 1.00 | 15691 | 3 | | | | SNORD116-1 | 1.00 |
| 15596 | 3 | | | | | SNORD102 | 1.00 | 15692 | 3 | | | | SNORD116-10 | 1.00 |
| 15597 | 3 | | | | | SNORD103A | 1.00 | 15693 | 3 | | | | SNORD116-11 | 1.00 |
| 15598 | 3 | | | | | SNORD104 | 1.00 | 15694 | 3 | | | | SNORD116-12 | 1.00 |
| 15599 | 3 | | | | | SNORD105 | 1.00 | 15695 | 3 | | | | SNORD116-13 | 1.00 |
| 15600 | 3 | | | | | SNORD105B | 1.00 | 15696 | 3 | | | | SNORD116-14 | 1.00 |
| 15601 | 3 | | | | | SNORD107 | 1.00 | 15697 | 3 | | | | SNORD116-15 | 1.00 |
| 15602 | 3 | | | | | SNORD108 | 1.00 | 15698 | 3 | | | | SNORD116-16 | 1.00 |
| 15603 | 3 | | | | | SNORD109B | 1.00 | 15699 | 3 | | | | SNORD116-17 | 1.00 |
| 15604 | 3 | | | | | SNORD11 | 1.00 | 15700 | 3 | | | | SNORD116-18 | 1.00 |
| 15605 | 3 | | | | | SNORD110 | 1.00 | 15701 | 3 | | | | SNORD116-2 | 1.00 |
| 15606 | 3 | | | | | SNORD111 | 1.00 | 15702 | 3 | | | | SNORD116-20 | 1.00 |
| 15607 | 3 | | | | | SNORD111B | 1.00 | 15703 | 3 | | | | SNORD116-21 | 1.00 |
| 15608 | 3 | | | | | SNORD113-1 | 1.00 | 15704 | 3 | | | | SNORD116-22 | 1.00 |
| 15609 | 3 | | | | | SNORD113-2 | 1.00 | 15705 | 3 | | | | SNORD116-23 | 1.00 |
| 15610 | 3 | | | | | SNORD113-4 | 1.00 | 15706 | 3 | | | | SNORD116-24 | 1.00 |
| 15611 | 3 | | | | | SNORD113-5 | 1.00 | 15707 | 3 | | | | SNORD116-25 | 1.00 |
| 15612 | 3 | | | | | SNORD113-6 | 1.00 | 15708 | 3 | | | | SNORD116-26 | 1.00 |
| 15613 | 3 | | | | | SNORD113-7 | 1.00 | 15709 | 3 | | | | SNORD116-27 | 1.00 |
| 15614 | 3 | | | | | SNORD113-9 | 1.00 | 15710 | 3 | | | | SNORD116-28 | 1.00 |
| 15615 | 3 | | | | | SNORD114-1 | 1.00 | 15711 | 3 | | | | SNORD116-29 | 1.00 |
| 15616 | 3 | | | | | SNORD114-10 | 1.00 | 15712 | 3 | | | | SNORD116-3 | 1.00 |
| 15617 | 3 | | | | | SNORD114-11 | 1.00 | 15713 | 3 | | | | SNORD116-4 | 1.00 |
| 15618 | 3 | | | | | SNORD114-12 | 1.00 | 15714 | 3 | | | | SNORD116-5 | 1.00 |
| 15619 | 3 | | | | | SNORD114-13 | 1.00 | 15715 | 3 | | | | SNORD116-6 | 1.00 |
| 15620 | 3 | | | | | SNORD114-14 | 1.00 | 15716 | 3 | | | | SNORD116-7 | 1.00 |
| 15621 | 3 | | | | | SNORD114-15 | 1.00 | 15717 | 3 | | | | SNORD116-8 | 1.00 |
| 15622 | 3 | | | | | SNORD114-16 | 1.00 | 15718 | 3 | | | | SNORD116-9 | 1.00 |
| 15623 | 3 | | | | | SNORD114-17 | 1.00 | 15719 | 3 | | | | SNORD117 | 1.00 |
| 15624 | 3 | | | | | SNORD114-18 | 1.00 | 15720 | 3 | | | | SNORD119 | 1.00 |
| 15625 | 3 | | | | | SNORD114-19 | 1.00 | 15721 | 3 | | | | SNORD11B | 1.00 |
| 15626 | 3 | | | | | SNORD114-2 | 1.00 | 15722 | 3 | | | | SNORD12 | 1.00 |
| 15627 | 3 | | | | | SNORD114-20 | 1.00 | 15723 | 3 | | | | SNORD121A | 1.00 |
| 15628 | 3 | | | | | SNORD114-21 | 1.00 | 15724 | 3 | | | | SNORD121B | 1.00 |
| 15629 | 3 | | | | | SNORD114-22 | 1.00 | 15725 | 3 | | | | SNORD123 | 1.00 |
| 15630 | 3 | | | | | SNORD114-23 | 1.00 | 15726 | 3 | | | | SNORD124 | 1.00 |
| 15631 | 3 | | | | | SNORD114-24 | 1.00 | 15727 | 3 | | | | SNORD125 | 1.00 |
| 15632 | 3 | | | | | SNORD114-25 | 1.00 | 15728 | 3 | | | | SNORD126 | 1.00 |
| 15633 | 3 | | | | | SNORD114-26 | 1.00 | 15729 | 3 | | | | SNORD127 | 1.00 |
| 15634 | 3 | | | | | SNORD114-27 | 1.00 | 15730 | 3 | | | | SNORD12B | 1.00 |
| 15635 | 3 | | | | | SNORD114-28 | 1.00 | 15731 | 3 | | | | SNORD12C | 1.00 |
| 15636 | 3 | | | | | SNORD114-29 | 1.00 | 15732 | 3 | | | | SNORD15A | 1.00 |
| 15637 | 3 | | | | | SNORD114-3 | 1.00 | 15733 | 3 | | | | SNORD15B | 1.00 |
| 15638 | 3 | | | | | SNORD114-30 | 1.00 | 15734 | 3 | | | | SNORD16 | 1.00 |
| 15639 | 3 | | | | | SNORD114-31 | 1.00 | 15735 | 3 | | | | SNORD17 | 1.00 |
| 15640 | 3 | | | | | SNORD114-4 | 1.00 | 15736 | 3 | | | | SNORD18A | 1.00 |
| 15641 | 3 | | | | | SNORD114-5 | 1.00 | 15737 | 3 | | | | SNORD18B | 1.00 |
| 15642 | 3 | | | | | SNORD114-6 | 1.00 | 15738 | 3 | | | | SNORD18C | 1.00 |

Fig. 39 - 83

| | | | | | | | | | | | | | | | | |
|---|---|---|---|---|---|---|---|---|---|---|---|---|---|---|---|---|
| 15739 | 3 | | | | | SNORD19 | 1.00 | 15835 | 3 | | | | | SNORD90 | 1.00 |
| 15740 | 3 | | | | | SNORD19B | 1.00 | 15836 | 3 | | | | | SNORD91A | 1.00 |
| 15741 | 3 | | | | | SNORD1A | 1.00 | 15837 | 3 | | | | | SNORD91B | 1.00 |
| 15742 | 3 | | | | | SNORD1B | 1.00 | 15838 | 3 | | | | | SNORD92 | 1.00 |
| 15743 | 3 | | | | | SNORD1C | 1.00 | 15839 | 3 | | | | | SNORD93 | 1.00 |
| 15744 | 3 | | | | | SNORD2 | 1.00 | 15840 | 3 | | | | | SNORD95 | 1.00 |
| 15745 | 3 | | | | | SNORD20 | 1.00 | 15841 | 3 | | | | | SNORD96A | 1.00 |
| 15746 | 3 | | | | | SNORD21 | 1.00 | 15842 | 3 | | | | | SNORD96B | 1.00 |
| 15747 | 3 | | | | | SNORD23 | 1.00 | 15843 | 3 | | | | | SNORD97 | 1.00 |
| 15748 | 3 | | | | | SNORD24 | 1.00 | 15844 | 3 | | | | | SNORD98 | 1.00 |
| 15749 | 3 | | | | | SNORD25 | 1.00 | 15845 | 3 | | | | | SNORD99 | 1.00 |
| 15750 | 3 | | | | | SNORD26 | 1.00 | 15846 | 3 | | | | | SNRPD2P2 | 1.00 |
| 15751 | 3 | | | | | SNORD27 | 1.00 | 15847 | 3 | | | | | SNTG1 | 1.00 |
| 15752 | 3 | | | | | SNORD28 | 1.00 | 15848 | 3 | | | | | SNTG2 | 1.00 |
| 15753 | 3 | | | | | SNORD29 | 1.00 | 15849 | 3 | | | | | SNTN | 1.00 |
| 15754 | 3 | | | | | SNORD30 | 1.00 | 15850 | 3 | | | | | SNURF | 1.00 |
| 15755 | 3 | | | | | SNORD31 | 1.00 | 15851 | 3 | | | | | SNX31 | 1.00 |
| 15756 | 3 | | | | | SNORD32A | 1.00 | 15852 | 3 | | | | | SNX32 | 1.00 |
| 15757 | 3 | | | | | SNORD32B | 1.00 | 15853 | 3 | | | | | SOAT2 | 1.00 |
| 15758 | 3 | | | | | SNORD33 | 1.00 | 15854 | 3 | | | | | SOHLH1 | 1.00 |
| 15759 | 3 | | | | | SNORD34 | 1.00 | 15855 | 3 | | | | | SOHLH2 | 1.00 |
| 15760 | 3 | | | | | SNORD35A | 1.00 | 15856 | 3 | | | | | SORCS3 | 1.00 |
| 15761 | 3 | | | | | SNORD35B | 1.00 | 15857 | 3 | | | | | SOST | 1.00 |
| 15762 | 3 | | | | | SNORD36A | 1.00 | 15858 | 3 | | | | | SOWAHA | 1.00 |
| 15763 | 3 | | | | | SNORD36B | 1.00 | 15859 | 3 | | | | | SOX1 | 1.00 |
| 15764 | 3 | | | | | SNORD36C | 1.00 | 15860 | 3 | | | | | SOX11 | 1.00 |
| 15765 | 3 | | | | | SNORD37 | 1.00 | 15861 | 3 | | | | | SOX14 | 1.00 |
| 15766 | 3 | | | | | SNORD38A | 1.00 | 15862 | 3 | | | | | SOX2-OT | 1.00 |
| 15767 | 3 | | | | | SNORD38B | 1.00 | 15863 | 3 | | | | | SOX3 | 1.00 |
| 15768 | 3 | | | | | SNORD41 | 1.00 | 15864 | 3 | | | | | SOX30 | 1.00 |
| 15769 | 3 | | | | | SNORD42A | 1.00 | 15865 | 3 | | | | | SOX5 | 1.00 |
| 15770 | 3 | | | | | SNORD42B | 1.00 | 15866 | 3 | | | | | SP140 | 1.00 |
| 15771 | 3 | | | | | SNORD43 | 1.00 | 15867 | 3 | | | | | SP7 | 1.00 |
| 15772 | 3 | | | | | SNORD44 | 1.00 | 15868 | 3 | | | | | SPACA1 | 1.00 |
| 15773 | 3 | | | | | SNORD45A | 1.00 | 15869 | 3 | | | | | SPACA3 | 1.00 |
| 15774 | 3 | | | | | SNORD45B | 1.00 | 15870 | 3 | | | | | SPACA5 | 1.00 |
| 15775 | 3 | | | | | SNORD45C | 1.00 | 15871 | 3 | | | | | SPACA5B | 1.00 |
| 15776 | 3 | | | | | SNORD46 | 1.00 | 15872 | 3 | | | | | SPACA7 | 1.00 |
| 15777 | 3 | | | | | SNORD47 | 1.00 | 15873 | 3 | | | | | SPAG11A | 1.00 |
| 15778 | 3 | | | | | SNORD48 | 1.00 | 15874 | 3 | | | | | SPAG11B | 1.00 |
| 15779 | 3 | | | | | SNORD49A | 1.00 | 15875 | 3 | | | | | SPAG17 | 1.00 |
| 15780 | 3 | | | | | SNORD49B | 1.00 | 15876 | 3 | | | | | SPAG4 | 1.00 |
| 15781 | 3 | | | | | SNORD4A | 1.00 | 15877 | 3 | | | | | SPAG6 | 1.00 |
| 15782 | 3 | | | | | SNORD4B | 1.00 | 15878 | 3 | | | | | SPAM1 | 1.00 |
| 15783 | 3 | | | | | SNORD5 | 1.00 | 15879 | 3 | | | | | SPANXA1 | 1.00 |
| 15784 | 3 | | | | | SNORD50A | 1.00 | 15880 | 3 | | | | | SPANXA2 | 1.00 |
| 15785 | 3 | | | | | SNORD50B | 1.00 | 15881 | 3 | | | | | SPANXA2-OT1 | 1.00 |
| 15786 | 3 | | | | | SNORD51 | 1.00 | 15882 | 3 | | | | | SPANXB2 | 1.00 |
| 15787 | 3 | | | | | SNORD52 | 1.00 | 15883 | 3 | | | | | SPANXC | 1.00 |
| 15788 | 3 | | | | | SNORD53 | 1.00 | 15884 | 3 | | | | | SPANXD | 1.00 |
| 15789 | 3 | | | | | SNORD54 | 1.00 | 15885 | 3 | | | | | SPANXE | 1.00 |
| 15790 | 3 | | | | | SNORD55 | 1.00 | 15886 | 3 | | | | | SPANXN1 | 1.00 |
| 15791 | 3 | | | | | SNORD56 | 1.00 | 15887 | 3 | | | | | SPANXN2 | 1.00 |
| 15792 | 3 | | | | | SNORD56B | 1.00 | 15888 | 3 | | | | | SPANXN3 | 1.00 |
| 15793 | 3 | | | | | SNORD57 | 1.00 | 15889 | 3 | | | | | SPANXN4 | 1.00 |
| 15794 | 3 | | | | | SNORD58A | 1.00 | 15890 | 3 | | | | | SPANXN5 | 1.00 |
| 15795 | 3 | | | | | SNORD58B | 1.00 | 15891 | 3 | | | | | SPATA12 | 1.00 |
| 15796 | 3 | | | | | SNORD58C | 1.00 | 15892 | 3 | | | | | SPATA16 | 1.00 |
| 15797 | 3 | | | | | SNORD59A | 1.00 | 15893 | 3 | | | | | SPATA17 | 1.00 |
| 15798 | 3 | | | | | SNORD59B | 1.00 | 15894 | 3 | | | | | SPATA19 | 1.00 |
| 15799 | 3 | | | | | SNORD6 | 1.00 | 15895 | 3 | | | | | SPATA21 | 1.00 |
| 15800 | 3 | | | | | SNORD60 | 1.00 | 15896 | 3 | | | | | SPATA22 | 1.00 |
| 15801 | 3 | | | | | SNORD61 | 1.00 | 15897 | 3 | | | | | SPATA24 | 1.00 |
| 15802 | 3 | | | | | SNORD62A | 1.00 | 15898 | 3 | | | | | SPATA3 | 1.00 |
| 15803 | 3 | | | | | SNORD63 | 1.00 | 15899 | 3 | | | | | SPATA4 | 1.00 |
| 15804 | 3 | | | | | SNORD64 | 1.00 | 15900 | 3 | | | | | SPATA8 | 1.00 |
| 15805 | 3 | | | | | SNORD65 | 1.00 | 15901 | 3 | | | | | SPATA9 | 1.00 |
| 15806 | 3 | | | | | SNORD66 | 1.00 | 15902 | 3 | | | | | SPATC1 | 1.00 |
| 15807 | 3 | | | | | SNORD67 | 1.00 | 15903 | 3 | | | | | SPATS1 | 1.00 |
| 15808 | 3 | | | | | SNORD68 | 1.00 | 15904 | 3 | | | | | SPC24 | 1.00 |
| 15809 | 3 | | | | | SNORD69 | 1.00 | 15905 | 3 | | | | | SPDYC | 1.00 |
| 15810 | 3 | | | | | SNORD7 | 1.00 | 15906 | 3 | | | | | SPDYE1 | 1.00 |
| 15811 | 3 | | | | | SNORD70 | 1.00 | 15907 | 3 | | | | | SPDYE3 | 1.00 |
| 15812 | 3 | | | | | SNORD71 | 1.00 | 15908 | 3 | | | | | SPDYE4 | 1.00 |
| 15813 | 3 | | | | | SNORD72 | 1.00 | 15909 | 3 | | | | | SPDYE5 | 1.00 |
| 15814 | 3 | | | | | SNORD73A | 1.00 | 15910 | 3 | | | | | SPDYE7P | 1.00 |
| 15815 | 3 | | | | | SNORD74 | 1.00 | 15911 | 3 | | | | | SPDYE8P | 1.00 |
| 15816 | 3 | | | | | SNORD75 | 1.00 | 15912 | 3 | | | | | SPEF1 | 1.00 |
| 15817 | 3 | | | | | SNORD76 | 1.00 | 15913 | 3 | | | | | SPEM1 | 1.00 |
| 15818 | 3 | | | | | SNORD77 | 1.00 | 15914 | 3 | | | | | SPERT | 1.00 |
| 15819 | 3 | | | | | SNORD78 | 1.00 | 15915 | 3 | | | | | SPG20OS | 1.00 |
| 15820 | 3 | | | | | SNORD79 | 1.00 | 15916 | 3 | | | | | SPHKAP | 1.00 |
| 15821 | 3 | | | | | SNORD8 | 1.00 | 15917 | 3 | | | | | SPIB | 1.00 |
| 15822 | 3 | | | | | SNORD80 | 1.00 | 15918 | 3 | | | | | SPIC | 1.00 |
| 15823 | 3 | | | | | SNORD81 | 1.00 | 15919 | 3 | | | | | SPIN4 | 1.00 |
| 15824 | 3 | | | | | SNORD82 | 1.00 | 15920 | 3 | | | | | SPINK13 | 1.00 |
| 15825 | 3 | | | | | SNORD83A | 1.00 | 15921 | 3 | | | | | SPINK14 | 1.00 |
| 15826 | 3 | | | | | SNORD83B | 1.00 | 15922 | 3 | | | | | SPINK2 | 1.00 |
| 15827 | 3 | | | | | SNORD84 | 1.00 | 15923 | 3 | | | | | SPINK4 | 1.00 |
| 15828 | 3 | | | | | SNORD85 | 1.00 | 15924 | 3 | | | | | SPINK6 | 1.00 |
| 15829 | 3 | | | | | SNORD86 | 1.00 | 15925 | 3 | | | | | SPINK8 | 1.00 |
| 15830 | 3 | | | | | SNORD87 | 1.00 | 15926 | 3 | | | | | SPINK9 | 1.00 |
| 15831 | 3 | | | | | SNORD88A | 1.00 | 15927 | 3 | | | | | SPINLW1 | 1.00 |
| 15832 | 3 | | | | | SNORD88B | 1.00 | 15928 | 3 | | | | | SPINLW1-WFDC6 | 1.00 |
| 15833 | 3 | | | | | SNORD88C | 1.00 | 15929 | 3 | | | | | SPINT3 | 1.00 |
| 15834 | 3 | | | | | SNORD9 | 1.00 | 15930 | 3 | | | | | SPINT4 | 1.00 |

Fig. 39 - 84

| | | | | | | | | | | | | | | | |
|---|---|---|---|---|---|---|---|---|---|---|---|---|---|---|---|
| 15931 | 3 | | | | | | SPNS3 | 1.00 | 16027 | 3 | | | | SYCP2L | 1.00 |
| 15932 | 3 | | | | | | SPO11 | 1.00 | 16028 | 3 | | | | SYDE2 | 1.00 |
| 15933 | 3 | | | | | | SPOCD1 | 1.00 | 16029 | 3 | | | | SYN3 | 1.00 |
| 15934 | 3 | | | | | | SPOCK3 | 1.00 | 16030 | 3 | | | | SYNDIG1 | 1.00 |
| 15935 | 3 | | | | | | SPP2 | 1.00 | 16031 | 3 | | | | SYNDIG1L | 1.00 |
| 15936 | 3 | | | | | | SPPL2C | 1.00 | 16032 | 3 | | | | SYNGR3 | 1.00 |
| 15937 | 3 | | | | | | SPRED3 | 1.00 | 16033 | 3 | | | | SYNGR4 | 1.00 |
| 15938 | 3 | | | | | | SPRNP1 | 1.00 | 16034 | 3 | | | | SYNJ2BP-COX16 | 1.00 |
| 15939 | 3 | | | | | | SPRR2C | 1.00 | 16035 | 3 | | | | SYNPO2L | 1.00 |
| 15940 | 3 | | | | | | SPRR2F | 1.00 | 16036 | 3 | | | | SYNPR | 1.00 |
| 15941 | 3 | | | | | | SPRR3 | 1.00 | 16037 | 3 | | | | SYS1-DBNDD2 | 1.00 |
| 15942 | 3 | | | | | | SPRY3 | 1.00 | 16038 | 3 | | | | SYT1 | 1.00 |
| 15943 | 3 | | | | | | SPRYD5 | 1.00 | 16039 | 3 | | | | SYT10 | 1.00 |
| 15944 | 3 | | | | | | SPTA1 | 1.00 | 16040 | 3 | | | | SYT13 | 1.00 |
| 15945 | 3 | | | | | | SPTBN4 | 1.00 | 16041 | 3 | | | | SYT14 | 1.00 |
| 15946 | 3 | | | | | | SPZ1 | 1.00 | 16042 | 3 | | | | SYT14L | 1.00 |
| 15947 | 3 | | | | | | SRCRB4D | 1.00 | 16043 | 3 | | | | SYT16 | 1.00 |
| 15948 | 3 | | | | | | SRD5A2 | 1.00 | 16044 | 3 | | | | SYT2 | 1.00 |
| 15949 | 3 | | | | | | SRG7 | 1.00 | 16045 | 3 | | | | SYT3 | 1.00 |
| 15950 | 3 | | | | | | SRMS | 1.00 | 16046 | 3 | | | | SYT4 | 1.00 |
| 15951 | 3 | | | | | | SRRM4 | 1.00 | 16047 | 3 | | | | SYT5 | 1.00 |
| 15952 | 3 | | | | | | SRRM5 | 1.00 | 16048 | 3 | | | | SYT6 | 1.00 |
| 15953 | 3 | | | | | | SRSF12 | 1.00 | 16049 | 3 | | | | SYT9 | 1.00 |
| 15954 | 3 | | | | | | SSPO | 1.00 | 16050 | 3 | | | | SYTL5 | 1.00 |
| 15955 | 3 | | | | | | SST | 1.00 | 16051 | 3 | | | | T | 1.00 |
| 15956 | 3 | | | | | | SSTR2 | 1.00 | 16052 | 3 | | | | TAAR1 | 1.00 |
| 15957 | 3 | | | | | | SSTR3 | 1.00 | 16053 | 3 | | | | TAAR2 | 1.00 |
| 15958 | 3 | | | | | | SSTR4 | 1.00 | 16054 | 3 | | | | TAAR3 | 1.00 |
| 15959 | 3 | | | | | | SSTR5 | 1.00 | 16055 | 3 | | | | TAAR5 | 1.00 |
| 15960 | 3 | | | | | | SSX1 | 1.00 | 16056 | 3 | | | | TAAR6 | 1.00 |
| 15961 | 3 | | | | | | SSX2 | 1.00 | 16057 | 3 | | | | TAAR8 | 1.00 |
| 15962 | 3 | | | | | | SSX3 | 1.00 | 16058 | 3 | | | | TAAR9 | 1.00 |
| 15963 | 3 | | | | | | SSX4 | 1.00 | 16059 | 3 | | | | TAC1 | 1.00 |
| 15964 | 3 | | | | | | SSX4B | 1.00 | 16060 | 3 | | | | TAC3 | 1.00 |
| 15965 | 3 | | | | | | SSX5 | 1.00 | 16061 | 3 | | | | TAC4 | 1.00 |
| 15966 | 3 | | | | | | SSX6 | 1.00 | 16062 | 3 | | | | TACR3 | 1.00 |
| 15967 | 3 | | | | | | SSX7 | 1.00 | 16063 | 3 | | | | TAF1A | 1.00 |
| 15968 | 3 | | | | | | SSX8 | 1.00 | 16064 | 3 | | | | TAF7L | 1.00 |
| 15969 | 3 | | | | | | ST18 | 1.00 | 16065 | 3 | | | | TAG | 1.00 |
| 15970 | 3 | | | | | | ST20-MTHFS | 1.00 | 16066 | 3 | | | | TAGLN3 | 1.00 |
| 15971 | 3 | | | | | | ST6GAL2 | 1.00 | 16067 | 3 | | | | tAKR | 1.00 |
| 15972 | 3 | | | | | | ST7-AS2 | 1.00 | 16068 | 3 | | | | TAL2 | 1.00 |
| 15973 | 3 | | | | | | ST7-OT3 | 1.00 | 16069 | 3 | | | | TARM1 | 1.00 |
| 15974 | 3 | | | | | | ST7-OT4 | 1.00 | 16070 | 3 | | | | TARP | 1.00 |
| 15975 | 3 | | | | | | ST8SIA2 | 1.00 | 16071 | 3 | | | | TAS1R1 | 1.00 |
| 15976 | 3 | | | | | | ST8SIA3 | 1.00 | 16072 | 3 | | | | TAS1R2 | 1.00 |
| 15977 | 3 | | | | | | ST8SIA5 | 1.00 | 16073 | 3 | | | | TAS1R3 | 1.00 |
| 15978 | 3 | | | | | | ST8SIA6 | 1.00 | 16074 | 3 | | | | TAS2R1 | 1.00 |
| 15979 | 3 | | | | | | STAB2 | 1.00 | 16075 | 3 | | | | TAS2R10 | 1.00 |
| 15980 | 3 | | | | | | STAG2 | 1.00 | 16076 | 3 | | | | TAS2R13 | 1.00 |
| 15981 | 3 | | | | | | STAG3 | 1.00 | 16077 | 3 | | | | TAS2R16 | 1.00 |
| 15982 | 3 | | | | | | STAP1 | 1.00 | 16078 | 3 | | | | TAS2R19 | 1.00 |
| 15983 | 3 | | | | | | STARD4 | 1.00 | 16079 | 3 | | | | TAS2R3 | 1.00 |
| 15984 | 3 | | | | | | STARD6 | 1.00 | 16080 | 3 | | | | TAS2R30 | 1.00 |
| 15985 | 3 | | | | | | STAT4 | 1.00 | 16081 | 3 | | | | TAS2R31 | 1.00 |
| 15986 | 3 | | | | | | STATH | 1.00 | 16082 | 3 | | | | TAS2R38 | 1.00 |
| 15987 | 3 | | | | | | STEAP1B | 1.00 | 16083 | 3 | | | | TAS2R39 | 1.00 |
| 15988 | 3 | | | | | | STH | 1.00 | 16084 | 3 | | | | TAS2R4 | 1.00 |
| 15989 | 3 | | | | | | STK31 | 1.00 | 16085 | 3 | | | | TAS2R40 | 1.00 |
| 15990 | 3 | | | | | | STK32A | 1.00 | 16086 | 3 | | | | TAS2R41 | 1.00 |
| 15991 | 3 | | | | | | STK33 | 1.00 | 16087 | 3 | | | | TAS2R42 | 1.00 |
| 15992 | 3 | | | | | | STL | 1.00 | 16088 | 3 | | | | TAS2R43 | 1.00 |
| 15993 | 3 | | | | | | STMN4 | 1.00 | 16089 | 3 | | | | TAS2R46 | 1.00 |
| 15994 | 3 | | | | | | STOML3 | 1.00 | 16090 | 3 | | | | TAS2R5 | 1.00 |
| 15995 | 3 | | | | | | STON1-GTF2A1L | 1.00 | 16091 | 3 | | | | TAS2R50 | 1.00 |
| 15996 | 3 | | | | | | STRA6 | 1.00 | 16092 | 3 | | | | TAS2R60 | 1.00 |
| 15997 | 3 | | | | | | STRA8 | 1.00 | 16093 | 3 | | | | TAS2R7 | 1.00 |
| 15998 | 3 | | | | | | STRC | 1.00 | 16094 | 3 | | | | TAS2R8 | 1.00 |
| 15999 | 3 | | | | | | STX16-NPEPL1 | 1.00 | 16095 | 3 | | | | TAS2R9 | 1.00 |
| 16000 | 3 | | | | | | STXBP4 | 1.00 | 16096 | 3 | | | | TAT | 1.00 |
| 16001 | 3 | | | | | | STXBP5L | 1.00 | 16097 | 3 | | | | TBC1D19 | 1.00 |
| 16002 | 3 | | | | | | STYK1 | 1.00 | 16098 | 3 | | | | TBC1D21 | 1.00 |
| 16003 | 3 | | | | | | SUCNR1 | 1.00 | 16099 | 3 | | | | TBC1D26 | 1.00 |
| 16004 | 3 | | | | | | SUGT1P1 | 1.00 | 16100 | 3 | | | | TBC1D28 | 1.00 |
| 16005 | 3 | | | | | | SUGT1P3 | 1.00 | 16101 | 3 | | | | TBC1D29 | 1.00 |
| 16006 | 3 | | | | | | SULT1A2 | 1.00 | 16102 | 3 | | | | TBC1D3 | 1.00 |
| 16007 | 3 | | | | | | SULT1B1 | 1.00 | 16103 | 3 | | | | TBC1D30 | 1.00 |
| 16008 | 3 | | | | | | SULT1C2 | 1.00 | 16104 | 3 | | | | TBC1D3P1-DHX40P1 | 1.00 |
| 16009 | 3 | | | | | | SULT1C2P1 | 1.00 | 16105 | 3 | | | | TBC1D3P2 | 1.00 |
| 16010 | 3 | | | | | | SULT1C3 | 1.00 | 16106 | 3 | | | | TBC1D3P5 | 1.00 |
| 16011 | 3 | | | | | | SULT1C4 | 1.00 | 16107 | 3 | | | | TBC1D8B | 1.00 |
| 16012 | 3 | | | | | | SULT2A1 | 1.00 | 16108 | 3 | | | | TBL1Y | 1.00 |
| 16013 | 3 | | | | | | SULT6B1 | 1.00 | 16109 | 3 | | | | TBPL2 | 1.00 |
| 16014 | 3 | | | | | | SUMO1P1 | 1.00 | 16110 | 3 | | | | TBR1 | 1.00 |
| 16015 | 3 | | | | | | SUMO4 | 1.00 | 16111 | 3 | | | | TBX10 | 1.00 |
| 16016 | 3 | | | | | | SUN3 | 1.00 | 16112 | 3 | | | | TBX20 | 1.00 |
| 16017 | 3 | | | | | | SUN5 | 1.00 | 16113 | 3 | | | | TBX21 | 1.00 |
| 16018 | 3 | | | | | | SV2C | 1.00 | 16114 | 3 | | | | TBX22 | 1.00 |
| 16019 | 3 | | | | | | SVOP | 1.00 | 16115 | 3 | | | | TBX4 | 1.00 |
| 16020 | 3 | | | | | | SVOPL | 1.00 | 16116 | 3 | | | | TBXA51 | 1.00 |
| 16021 | 3 | | | | | | SYCE1 | 1.00 | 16117 | 3 | | | | TCAM1P | 1.00 |
| 16022 | 3 | | | | | | SYCE1L | 1.00 | 16118 | 3 | | | | TCEAL5 | 1.00 |
| 16023 | 3 | | | | | | SYCE2 | 1.00 | 16119 | 3 | | | | TCEB3B | 1.00 |
| 16024 | 3 | | | | | | SYCN | 1.00 | 16120 | 3 | | | | TCEB3C | 1.00 |
| 16025 | 3 | | | | | | SYCP1 | 1.00 | 16121 | 3 | | | | TCEB3CL | 1.00 |
| 16026 | 3 | | | | | | SYCP2 | 1.00 | | | | | | | |

Fig. 39 - 85

| | | | | | | | | | | | | | | |
|---|---|---|---|---|---|---|---|---|---|---|---|---|---|---|
| 16122 | 3 | | | | | TCERG1L | 1.00 | 16218 | 3 | | | | TM4SF19-TCTEX1D2 | 1.00 |
| 16123 | 3 | | | | | TCF21 | 1.00 | 16219 | 3 | | | | TM4SF20 | 1.00 |
| 16124 | 3 | | | | | TCF23 | 1.00 | 16220 | 3 | | | | TM4SF4 | 1.00 |
| 16125 | 3 | | | | | TCF24 | 1.00 | 16221 | 3 | | | | TM4SF5 | 1.00 |
| 16126 | 3 | | | | | TCHHL1 | 1.00 | 16222 | 3 | | | | TM6SF2 | 1.00 |
| 16127 | 3 | | | | | TCL1A | 1.00 | 16223 | 3 | | | | TM7SF4 | 1.00 |
| 16128 | 3 | | | | | TCL1B | 1.00 | 16224 | 3 | | | | TMC1 | 1.00 |
| 16129 | 3 | | | | | TCL6 | 1.00 | 16225 | 3 | | | | TMC2 | 1.00 |
| 16130 | 3 | | | | | TCN1 | 1.00 | 16226 | 3 | | | | TMC3 | 1.00 |
| 16131 | 3 | | | | | TCP10 | 1.00 | 16227 | 3 | | | | TMC5 | 1.00 |
| 16132 | 3 | | | | | TCP10L | 1.00 | 16228 | 3 | | | | TMC7 | 1.00 |
| 16133 | 3 | | | | | TCP10L2 | 1.00 | 16229 | 3 | | | | TMCO2 | 1.00 |
| 16134 | 3 | | | | | TCP11 | 1.00 | 16230 | 3 | | | | TMCO5A | 1.00 |
| 16135 | 3 | | | | | TCTE1 | 1.00 | 16231 | 3 | | | | TMCO5B | 1.00 |
| 16136 | 3 | | | | | TCTE3 | 1.00 | 16232 | 3 | | | | TMED11P | 1.00 |
| 16137 | 3 | | | | | TCTEX1D4 | 1.00 | 16233 | 3 | | | | TMED7-TICAM2 | 1.00 |
| 16138 | 3 | | | | | TDGF1 | 1.00 | 16234 | 3 | | | | TMED8 | 1.00 |
| 16139 | 3 | | | | | TDGF1P3 | 1.00 | 16235 | 3 | | | | TMEFF1 | 1.00 |
| 16140 | 3 | | | | | TDH | 1.00 | 16236 | 3 | | | | TMEFF2 | 1.00 |
| 16141 | 3 | | | | | TDO2 | 1.00 | 16237 | 3 | | | | TMEM105 | 1.00 |
| 16142 | 3 | | | | | TDRD1 | 1.00 | 16238 | 3 | | | | TMEM110-MUSTN1 | 1.00 |
| 16143 | 3 | | | | | TDRD12 | 1.00 | 16239 | 3 | | | | TMEM114 | 1.00 |
| 16144 | 3 | | | | | TDRD5 | 1.00 | 16240 | 3 | | | | TMEM130 | 1.00 |
| 16145 | 3 | | | | | TDRD6 | 1.00 | 16241 | 3 | | | | TMEM132D | 1.00 |
| 16146 | 3 | | | | | TDRD9 | 1.00 | 16242 | 3 | | | | TMEM145 | 1.00 |
| 16147 | 3 | | | | | TDRG1 | 1.00 | 16243 | 3 | | | | TMEM14E | 1.00 |
| 16148 | 3 | | | | | TECRL | 1.00 | 16244 | 3 | | | | TMEM150B | 1.00 |
| 16149 | 3 | | | | | TECTA | 1.00 | 16245 | 3 | | | | TMEM151A | 1.00 |
| 16150 | 3 | | | | | TECTB | 1.00 | 16246 | 3 | | | | TMEM151B | 1.00 |
| 16151 | 3 | | | | | TEDDM1 | 1.00 | 16247 | 3 | | | | TMEM155 | 1.00 |
| 16152 | 3 | | | | | TEKT1 | 1.00 | 16248 | 3 | | | | TMEM156 | 1.00 |
| 16153 | 3 | | | | | TEKT2 | 1.00 | 16249 | 3 | | | | TMEM163 | 1.00 |
| 16154 | 3 | | | | | TEKT4 | 1.00 | 16250 | 3 | | | | TMEM169 | 1.00 |
| 16155 | 3 | | | | | TEKT5 | 1.00 | 16251 | 3 | | | | TMEM170B | 1.00 |
| 16156 | 3 | | | | | TEPP | 1.00 | 16252 | 3 | | | | TMEM174 | 1.00 |
| 16157 | 3 | | | | | TERT | 1.00 | 16253 | 3 | | | | TMEM179 | 1.00 |
| 16158 | 3 | | | | | TET1 | 1.00 | 16254 | 3 | | | | TMEM182 | 1.00 |
| 16159 | 3 | | | | | TEX11 | 1.00 | 16255 | 3 | | | | TMEM189-UBE2V1 | 1.00 |
| 16160 | 3 | | | | | TEX12 | 1.00 | 16256 | 3 | | | | TMEM190 | 1.00 |
| 16161 | 3 | | | | | TEX13A | 1.00 | 16257 | 3 | | | | TMEM191A | 1.00 |
| 16162 | 3 | | | | | TEX13B | 1.00 | 16258 | 3 | | | | TMEM191B | 1.00 |
| 16163 | 3 | | | | | TEX14 | 1.00 | 16259 | 3 | | | | TMEM191C | 1.00 |
| 16164 | 3 | | | | | TEX15 | 1.00 | 16260 | 3 | | | | TMEM196 | 1.00 |
| 16165 | 3 | | | | | TEX19 | 1.00 | 16261 | 3 | | | | TMEM202 | 1.00 |
| 16166 | 3 | | | | | TEX21P | 1.00 | 16262 | 3 | | | | TMEM207 | 1.00 |
| 16167 | 3 | | | | | TEX22 | 1.00 | 16263 | 3 | | | | TMEM212 | 1.00 |
| 16168 | 3 | | | | | TEX26 | 1.00 | 16264 | 3 | | | | TMEM215 | 1.00 |
| 16169 | 3 | | | | | TEX26-AS1 | 1.00 | 16265 | 3 | | | | TMEM221 | 1.00 |
| 16170 | 3 | | | | | TEX28 | 1.00 | 16266 | 3 | | | | TMEM225 | 1.00 |
| 16171 | 3 | | | | | TEX29 | 1.00 | 16267 | 3 | | | | TMEM229A | 1.00 |
| 16172 | 3 | | | | | TEX33 | 1.00 | 16268 | 3 | | | | TMEM232 | 1.00 |
| 16173 | 3 | | | | | TEX34 | 1.00 | 16269 | 3 | | | | TMEM233 | 1.00 |
| 16174 | 3 | | | | | TEX9 | 1.00 | 16270 | 3 | | | | TMEM235 | 1.00 |
| 16175 | 3 | | | | | TFAMP1 | 1.00 | 16271 | 3 | | | | TMEM236 | 1.00 |
| 16176 | 3 | | | | | TFAP2D | 1.00 | 16272 | 3 | | | | TMEM239 | 1.00 |
| 16177 | 3 | | | | | TFDP3 | 1.00 | 16273 | 3 | | | | TMEM244 | 1.00 |
| 16178 | 3 | | | | | TFEC | 1.00 | 16274 | 3 | | | | TMEM26 | 1.00 |
| 16179 | 3 | | | | | TFF1 | 1.00 | 16275 | 3 | | | | TMEM27 | 1.00 |
| 16180 | 3 | | | | | TFF2 | 1.00 | 16276 | 3 | | | | TMEM30C | 1.00 |
| 16181 | 3 | | | | | TG | 1.00 | 16277 | 3 | | | | TMEM31 | 1.00 |
| 16182 | 3 | | | | | TGIF2-C20ORF24 | 1.00 | 16278 | 3 | | | | TMEM56-RWDD3 | 1.00 |
| 16183 | 3 | | | | | TGIF2LX | 1.00 | 16279 | 3 | | | | TMEM72 | 1.00 |
| 16184 | 3 | | | | | TGIF2LY | 1.00 | 16280 | 3 | | | | TMEM72-AS1 | 1.00 |
| 16185 | 3 | | | | | TGM4 | 1.00 | 16281 | 3 | | | | TMEM74 | 1.00 |
| 16186 | 3 | | | | | TGM6 | 1.00 | 16282 | 3 | | | | TMEM82 | 1.00 |
| 16187 | 3 | | | | | TGM7 | 1.00 | 16283 | 3 | | | | TMEM89 | 1.00 |
| 16188 | 3 | | | | | TH | 1.00 | 16284 | 3 | | | | TMEM8C | 1.00 |
| 16189 | 3 | | | | | THEG | 1.00 | 16285 | 3 | | | | TMEM92 | 1.00 |
| 16190 | 3 | | | | | THEG5 | 1.00 | 16286 | 3 | | | | TMEM95 | 1.00 |
| 16191 | 3 | | | | | THEGL | 1.00 | 16287 | 3 | | | | TMIGD1 | 1.00 |
| 16192 | 3 | | | | | THEMIS | 1.00 | 16288 | 3 | | | | TMIGD2 | 1.00 |
| 16193 | 3 | | | | | THPO | 1.00 | 16289 | 3 | | | | TMOD4 | 1.00 |
| 16194 | 3 | | | | | THSD7A | 1.00 | 16290 | 3 | | | | TMPPE | 1.00 |
| 16195 | 3 | | | | | THSD7B | 1.00 | 16291 | 3 | | | | TMPRSS11A | 1.00 |
| 16196 | 3 | | | | | TIAM2 | 1.00 | 16292 | 3 | | | | TMPRSS11B | 1.00 |
| 16197 | 3 | | | | | TIGD3 | 1.00 | 16293 | 3 | | | | TMPRSS11BNL | 1.00 |
| 16198 | 3 | | | | | TIGD4 | 1.00 | 16294 | 3 | | | | TMPRSS11D | 1.00 |
| 16199 | 3 | | | | | TIGIT | 1.00 | 16295 | 3 | | | | TMPRSS11F | 1.00 |
| 16200 | 3 | | | | | TIMD4 | 1.00 | 16296 | 3 | | | | TMPRSS11GP | 1.00 |
| 16201 | 3 | | | | | TINAG | 1.00 | 16297 | 3 | | | | TMPRSS12 | 1.00 |
| 16202 | 3 | | | | | TIPARP-AS1 | 1.00 | 16298 | 3 | | | | TMPRSS15 | 1.00 |
| 16203 | 3 | | | | | TISP43 | 1.00 | 16299 | 3 | | | | TMPRSS7 | 1.00 |
| 16204 | 3 | | | | | TKTL1 | 1.00 | 16300 | 3 | | | | TMPRSS9 | 1.00 |
| 16205 | 3 | | | | | TKTL2 | 1.00 | 16301 | 3 | | | | TMSB15A | 1.00 |
| 16206 | 3 | | | | | TLE6 | 1.00 | 16302 | 3 | | | | TNFAIP8L2-SCNM1 | 1.00 |
| 16207 | 3 | | | | | TLL2 | 1.00 | 16303 | 3 | | | | TNFRSF13B | 1.00 |
| 16208 | 3 | | | | | TLR10 | 1.00 | 16304 | 3 | | | | TNFRSF17 | 1.00 |
| 16209 | 3 | | | | | TLR6 | 1.00 | 16305 | 3 | | | | TNFSF9 | 1.00 |
| 16210 | 3 | | | | | TLR7 | 1.00 | 16306 | 3 | | | | TNFSF11 | 1.00 |
| 16211 | 3 | | | | | TLR8 | 1.00 | 16307 | 3 | | | | TNFSF12-TNFSF13 | 1.00 |
| 16212 | 3 | | | | | TLR8-AS1 | 1.00 | 16308 | 3 | | | | TNFSF15 | 1.00 |
| 16213 | 3 | | | | | TLX1 | 1.00 | 16309 | 3 | | | | TNFSF18 | 1.00 |
| 16214 | 3 | | | | | TLX1NB | 1.00 | 16310 | 3 | | | | TNFSF4 | 1.00 |
| 16215 | 3 | | | | | TLX2 | 1.00 | | | | | | | |
| 16216 | 3 | | | | | TLX3 | 1.00 | | | | | | | |
| 16217 | 3 | | | | | TM4SF19 | 1.00 | | | | | | | |

Fig. 39 - 86

| | | | | | | | | | | | | | | | |
|---|---|---|---|---|---|---|---|---|---|---|---|---|---|---|---|
| 16311 | 3 | | | | | | TNIK | 1.00 | 16407 | 3 | | | | TSNAX-DISC1 | 1.00 |
| 16312 | 3 | | | | | | TNIP3 | 1.00 | 16408 | 3 | | | | TSNAXIP1 | 1.00 |
| 16313 | 3 | | | | | | TNNI1 | 1.00 | 16409 | 3 | | | | TSPAN16 | 1.00 |
| 16314 | 3 | | | | | | TNNI3K | 1.00 | 16410 | 3 | | | | TSPAN19 | 1.00 |
| 16315 | 3 | | | | | | TNP1 | 1.00 | 16411 | 3 | | | | TSPAN32 | 1.00 |
| 16316 | 3 | | | | | | TNP2 | 1.00 | 16412 | 3 | | | | TSPO2 | 1.00 |
| 16317 | 3 | | | | | | TNR | 1.00 | 16413 | 3 | | | | TSPY1 | 1.00 |
| 16318 | 3 | | | | | | TOB2P1 | 1.00 | 16414 | 3 | | | | TSPY2 | 1.00 |
| 16319 | 3 | | | | | | TOMM20L | 1.00 | 16415 | 3 | | | | TSPY26P | 1.00 |
| 16320 | 3 | | | | | | TOP1P2 | 1.00 | 16416 | 3 | | | | TSPY3 | 1.00 |
| 16321 | 3 | | | | | | TP53TG3 | 1.00 | 16417 | 3 | | | | TSPY4 | 1.00 |
| 16322 | 3 | | | | | | TP53TG3B | 1.00 | 16418 | 3 | | | | TSPY8 | 1.00 |
| 16323 | 3 | | | | | | TP53TG3C | 1.00 | 16419 | 3 | | | | TSPYL6 | 1.00 |
| 16324 | 3 | | | | | | TP53TG5 | 1.00 | 16420 | 3 | | | | TSSK1B | 1.00 |
| 16325 | 3 | | | | | | TPD52L3 | 1.00 | 16421 | 3 | | | | TSSK2 | 1.00 |
| 16326 | 3 | | | | | | TPH1 | 1.00 | 16422 | 3 | | | | TTBK1 | 1.00 |
| 16327 | 3 | | | | | | TPH2 | 1.00 | 16423 | 3 | | | | TTBK2 | 1.00 |
| 16328 | 3 | | | | | | TPI1P2 | 1.00 | 16424 | 3 | | | | TTC16 | 1.00 |
| 16329 | 3 | | | | | | TPO | 1.00 | 16425 | 3 | | | | TTC23L | 1.00 |
| 16330 | 3 | | | | | | TPPP2 | 1.00 | 16426 | 3 | | | | TTC24 | 1.00 |
| 16331 | 3 | | | | | | TPRX1 | 1.00 | 16427 | 3 | | | | TTC25 | 1.00 |
| 16332 | 3 | | | | | | TPTE | 1.00 | 16428 | 3 | | | | TTC26 | 1.00 |
| 16333 | 3 | | | | | | TPTE2 | 1.00 | 16429 | 3 | | | | TTC29 | 1.00 |
| 16334 | 3 | | | | | | TPTE2P1 | 1.00 | 16430 | 3 | | | | TTC34 | 1.00 |
| 16335 | 3 | | | | | | TPTE2P3 | 1.00 | 16431 | 3 | | | | TTC40 | 1.00 |
| 16336 | 3 | | | | | | TPTE2P6 | 1.00 | 16432 | 3 | | | | TTC9B | 1.00 |
| 16337 | 3 | | | | | | TRAF3IP3 | 1.00 | 16433 | 3 | | | | TTK | 1.00 |
| 16338 | 3 | | | | | | TRDMT1 | 1.00 | 16434 | 3 | | | | TTLL10 | 1.00 |
| 16339 | 3 | | | | | | TRDN | 1.00 | 16435 | 3 | | | | TTLL13 | 1.00 |
| 16340 | 3 | | | | | | TREH | 1.00 | 16436 | 3 | | | | TTLL2 | 1.00 |
| 16341 | 3 | | | | | | TREM1 | 1.00 | 16437 | 3 | | | | TTLL6 | 1.00 |
| 16342 | 3 | | | | | | TREM2 | 1.00 | 16438 | 3 | | | | TTLL7 | 1.00 |
| 16343 | 3 | | | | | | TREML1 | 1.00 | 16439 | 3 | | | | TTLL9 | 1.00 |
| 16344 | 3 | | | | | | TREML2 | 1.00 | 16440 | 3 | | | | TTN | 1.00 |
| 16345 | 3 | | | | | | TREML2P1 | 1.00 | 16441 | 3 | | | | TTPA | 1.00 |
| 16346 | 3 | | | | | | TREML3 | 1.00 | 16442 | 3 | | | | TTR | 1.00 |
| 16347 | 3 | | | | | | TREML4 | 1.00 | 16443 | 3 | | | | TTTY1 | 1.00 |
| 16348 | 3 | | | | | | TRH | 1.00 | 16444 | 3 | | | | TTTY10 | 1.00 |
| 16349 | 3 | | | | | | TRHDE | 1.00 | 16445 | 3 | | | | TTTY11 | 1.00 |
| 16350 | 3 | | | | | | TRHR | 1.00 | 16446 | 3 | | | | TTTY12 | 1.00 |
| 16351 | 3 | | | | | | TRIM10 | 1.00 | 16447 | 3 | | | | TTTY13 | 1.00 |
| 16352 | 3 | | | | | | TRIM15 | 1.00 | 16448 | 3 | | | | TTTY16 | 1.00 |
| 16353 | 3 | | | | | | TRIM31 | 1.00 | 16449 | 3 | | | | TTTY17A | 1.00 |
| 16354 | 3 | | | | | | TRIM36 | 1.00 | 16450 | 3 | | | | TTTY18 | 1.00 |
| 16355 | 3 | | | | | | TRIM39-RPP21 | 1.00 | 16451 | 3 | | | | TTTY19 | 1.00 |
| 16356 | 3 | | | | | | TRIM40 | 1.00 | 16452 | 3 | | | | TTTY1B | 1.00 |
| 16357 | 3 | | | | | | TRIM42 | 1.00 | 16453 | 3 | | | | TTTY2 | 1.00 |
| 16358 | 3 | | | | | | TRIM43 | 1.00 | 16454 | 3 | | | | TTTY20 | 1.00 |
| 16359 | 3 | | | | | | TRIM43B | 1.00 | 16455 | 3 | | | | TTTY21 | 1.00 |
| 16360 | 3 | | | | | | TRIM46 | 1.00 | 16456 | 3 | | | | TTTY21B | 1.00 |
| 16361 | 3 | | | | | | TRIM48 | 1.00 | 16457 | 3 | | | | TTTY22 | 1.00 |
| 16362 | 3 | | | | | | TRIM49 | 1.00 | 16458 | 3 | | | | TTTY23B | 1.00 |
| 16363 | 3 | | | | | | TRIM49L1 | 1.00 | 16459 | 3 | | | | TTTY3 | 1.00 |
| 16364 | 3 | | | | | | TRIM49L2 | 1.00 | 16460 | 3 | | | | TTTY3B | 1.00 |
| 16365 | 3 | | | | | | TRIM50 | 1.00 | 16461 | 3 | | | | TTTY4 | 1.00 |
| 16366 | 3 | | | | | | TRIM53P | 1.00 | 16462 | 3 | | | | TTTY4B | 1.00 |
| 16367 | 3 | | | | | | TRIM54 | 1.00 | 16463 | 3 | | | | TTTY5 | 1.00 |
| 16368 | 3 | | | | | | TRIM58 | 1.00 | 16464 | 3 | | | | TTTY6 | 1.00 |
| 16369 | 3 | | | | | | TRIM60 | 1.00 | 16465 | 3 | | | | TTTY6B | 1.00 |
| 16370 | 3 | | | | | | TRIM61 | 1.00 | 16466 | 3 | | | | TTTY7 | 1.00 |
| 16371 | 3 | | | | | | TRIM63 | 1.00 | 16467 | 3 | | | | TTTY7B | 1.00 |
| 16372 | 3 | | | | | | TRIM64 | 1.00 | 16468 | 3 | | | | TTTY8 | 1.00 |
| 16373 | 3 | | | | | | TRIM64B | 1.00 | 16469 | 3 | | | | TTTY8B | 1.00 |
| 16374 | 3 | | | | | | TRIM64C | 1.00 | 16470 | 3 | | | | TTTY9B | 1.00 |
| 16375 | 3 | | | | | | TRIM67 | 1.00 | 16471 | 3 | | | | TUBA3C | 1.00 |
| 16376 | 3 | | | | | | TRIM69 | 1.00 | 16472 | 3 | | | | TUBA3D | 1.00 |
| 16377 | 3 | | | | | | TRIM6-TRIM34 | 1.00 | 16473 | 3 | | | | TUBA3E | 1.00 |
| 16378 | 3 | | | | | | TRIM71 | 1.00 | 16474 | 3 | | | | TUBB1 | 1.00 |
| 16379 | 3 | | | | | | TRIM72 | 1.00 | 16475 | 3 | | | | TUBB8 | 1.00 |
| 16380 | 3 | | | | | | TRIM77P | 1.00 | 16476 | 3 | | | | TULP1 | 1.00 |
| 16381 | 3 | | | | | | TRIM78P | 1.00 | 16477 | 3 | | | | TULP2 | 1.00 |
| 16382 | 3 | | | | | | TRIM9 | 1.00 | 16478 | 3 | | | | TXK | 1.00 |
| 16383 | 3 | | | | | | TRIML1 | 1.00 | 16479 | 3 | | | | TXLNB | 1.00 |
| 16384 | 3 | | | | | | TRIML2 | 1.00 | 16480 | 3 | | | | TXNDC2 | 1.00 |
| 16385 | 3 | | | | | | TRPA1 | 1.00 | 16481 | 3 | | | | TXNDC3 | 1.00 |
| 16386 | 3 | | | | | | TRPC2 | 1.00 | 16482 | 3 | | | | TXNDC8 | 1.00 |
| 16387 | 3 | | | | | | TRPC3 | 1.00 | 16483 | 3 | | | | TXNRD3NB | 1.00 |
| 16388 | 3 | | | | | | TRPC4 | 1.00 | 16484 | 3 | | | | UBASH3A | 1.00 |
| 16389 | 3 | | | | | | TRPC5 | 1.00 | 16485 | 3 | | | | UBE2DNL | 1.00 |
| 16390 | 3 | | | | | | TRPC7 | 1.00 | 16486 | 3 | | | | UBE2F-SCLY | 1.00 |
| 16391 | 3 | | | | | | TRPM2 | 1.00 | 16487 | 3 | | | | UBE2Q2P3 | 1.00 |
| 16392 | 3 | | | | | | TRPM3 | 1.00 | 16488 | 3 | | | | UBE2U | 1.00 |
| 16393 | 3 | | | | | | TRPM5 | 1.00 | 16489 | 3 | | | | UBL4B | 1.00 |
| 16394 | 3 | | | | | | TRPM6 | 1.00 | 16490 | 3 | | | | UBQLN3 | 1.00 |
| 16395 | 3 | | | | | | TRPM8 | 1.00 | 16491 | 3 | | | | UBQLNL | 1.00 |
| 16396 | 3 | | | | | | TRPV3 | 1.00 | 16492 | 3 | | | | UBTFL1 | 1.00 |
| 16397 | 3 | | | | | | TRPV5 | 1.00 | 16493 | 3 | | | | UCA1 | 1.00 |
| 16398 | 3 | | | | | | TRY6 | 1.00 | 16494 | 3 | | | | UCMA | 1.00 |
| 16399 | 3 | | | | | | TSC22D1-AS1 | 1.00 | 16495 | 3 | | | | UCN3 | 1.00 |
| 16400 | 3 | | | | | | TSG1 | 1.00 | 16496 | 3 | | | | UCP1 | 1.00 |
| 16401 | 3 | | | | | | TSGA10 | 1.00 | 16497 | 3 | | | | UG0898H09 | 1.00 |
| 16402 | 3 | | | | | | TSGA10IP | 1.00 | 16498 | 3 | | | | UGGT2 | 1.00 |
| 16403 | 3 | | | | | | TSGA13 | 1.00 | 16499 | 3 | | | | UGT1A1 | 1.00 |
| 16404 | 3 | | | | | | TSHB | 1.00 | 16500 | 3 | | | | UGT1A10 | 1.00 |
| 16405 | 3 | | | | | | TSHR | 1.00 | 16501 | 3 | | | | UGT1A3 | 1.00 |
| 16406 | 3 | | | | | | TSIX | 1.00 | 16502 | 3 | | | | UGT1A4 | 1.00 |

Fig. 39 - 87

| | | | | | | | | | | | | | | | | | |
|---|---|---|---|---|---|---|---|---|---|---|---|---|---|---|---|---|---|
| 16503 | 3 | | | | | | UGT1A5 | 1.00 | 16599 | 3 | | | | | | VWCE | 1.00 |
| 16504 | 3 | | | | | | UGT1A8 | 1.00 | 16600 | 3 | | | | | | VWDE | 1.00 |
| 16505 | 3 | | | | | | UGT1A9 | 1.00 | 16601 | 3 | | | | | | WBP2NL | 1.00 |
| 16506 | 3 | | | | | | UGT2A2 | 1.00 | 16602 | 3 | | | | | | WBSCR28 | 1.00 |
| 16507 | 3 | | | | | | UGT2A3 | 1.00 | 16603 | 3 | | | | | | WDHD1 | 1.00 |
| 16508 | 3 | | | | | | UGT2B10 | 1.00 | 16604 | 3 | | | | | | WDR16 | 1.00 |
| 16509 | 3 | | | | | | UGT2B15 | 1.00 | 16605 | 3 | | | | | | WDR17 | 1.00 |
| 16510 | 3 | | | | | | UGT2B17 | 1.00 | 16606 | 3 | | | | | | WDR31 | 1.00 |
| 16511 | 3 | | | | | | UGT2B28 | 1.00 | 16607 | 3 | | | | | | WDR38 | 1.00 |
| 16512 | 3 | | | | | | UGT2B4 | 1.00 | 16608 | 3 | | | | | | WDR49 | 1.00 |
| 16513 | 3 | | | | | | UGT2B7 | 1.00 | 16609 | 3 | | | | | | WDR63 | 1.00 |
| 16514 | 3 | | | | | | UGT3A1 | 1.00 | 16610 | 3 | | | | | | WDR64 | 1.00 |
| 16515 | 3 | | | | | | ULBP1 | 1.00 | 16611 | 3 | | | | | | WDR65 | 1.00 |
| 16516 | 3 | | | | | | ULBP2 | 1.00 | 16612 | 3 | | | | | | WDR66 | 1.00 |
| 16517 | 3 | | | | | | ULBP3 | 1.00 | 16613 | 3 | | | | | | WDR67 | 1.00 |
| 16518 | 3 | | | | | | ULK4 | 1.00 | 16614 | 3 | | | | | | WDR69 | 1.00 |
| 16519 | 3 | | | | | | UMOD | 1.00 | 16615 | 3 | | | | | | WDR78 | 1.00 |
| 16520 | 3 | | | | | | UMODL1 | 1.00 | 16616 | 3 | | | | | | WDR87 | 1.00 |
| 16521 | 3 | | | | | | UNC13A | 1.00 | 16617 | 3 | | | | | | WDR88 | 1.00 |
| 16522 | 3 | | | | | | UNC13C | 1.00 | 16618 | 3 | | | | | | WDR93 | 1.00 |
| 16523 | 3 | | | | | | UNC45B | 1.00 | 16619 | 3 | | | | | | WDR96 | 1.00 |
| 16524 | 3 | | | | | | UNC5A | 1.00 | 16620 | 3 | | | | | | WEE2 | 1.00 |
| 16525 | 3 | | | | | | UNC5C | 1.00 | 16621 | 3 | | | | | | WFDC10A | 1.00 |
| 16526 | 3 | | | | | | UNC5D | 1.00 | 16622 | 3 | | | | | | WFDC11 | 1.00 |
| 16527 | 3 | | | | | | UNC79 | 1.00 | 16623 | 3 | | | | | | WFDC13 | 1.00 |
| 16528 | 3 | | | | | | UNC80 | 1.00 | 16624 | 3 | | | | | | WFDC6 | 1.00 |
| 16529 | 3 | | | | | | UNCX | 1.00 | 16625 | 3 | | | | | | WFDC8 | 1.00 |
| 16530 | 3 | | | | | | UNQ6494 | 1.00 | 16626 | 3 | | | | | | WFDC9 | 1.00 |
| 16531 | 3 | | | | | | UNQ6975 | 1.00 | 16627 | 3 | | | | | | WFIKKN2 | 1.00 |
| 16532 | 3 | | | | | | UOX | 1.00 | 16628 | 3 | | | | | | WHAMMP2 | 1.00 |
| 16533 | 3 | | | | | | UPK1B | 1.00 | 16629 | 3 | | | | | | WISP1 | 1.00 |
| 16534 | 3 | | | | | | UPK2 | 1.00 | 16630 | 3 | | | | | | WNK3 | 1.00 |
| 16535 | 3 | | | | | | UPK3A | 1.00 | 16631 | 3 | | | | | | WNT1 | 1.00 |
| 16536 | 3 | | | | | | UPP2 | 1.00 | 16632 | 3 | | | | | | WNT8A | 1.00 |
| 16537 | 3 | | | | | | URGCP-MRPS24 | 1.00 | 16633 | 3 | | | | | | WNT8B | 1.00 |
| 16538 | 3 | | | | | | UROC1 | 1.00 | 16634 | 3 | | | | | | WNT9B | 1.00 |
| 16539 | 3 | | | | | | USH1C | 1.00 | 16635 | 3 | | | | | | WT1 | 1.00 |
| 16540 | 3 | | | | | | USH2A | 1.00 | 16636 | 3 | | | | | | WT1-AS | 1.00 |
| 16541 | 3 | | | | | | USP17 | 1.00 | 16637 | 3 | | | | | | WWTR1-AS1 | 1.00 |
| 16542 | 3 | | | | | | USP17L2 | 1.00 | 16638 | 3 | | | | | | XAGE3A | 1.00 |
| 16543 | 3 | | | | | | USP17L6P | 1.00 | 16639 | 3 | | | | | | XAGE1C | 1.00 |
| 16544 | 3 | | | | | | USP26 | 1.00 | 16640 | 3 | | | | | | XAGE1E | 1.00 |
| 16545 | 3 | | | | | | USP29 | 1.00 | 16641 | 3 | | | | | | XAGE2 | 1.00 |
| 16546 | 3 | | | | | | USP44 | 1.00 | 16642 | 3 | | | | | | XAGE3 | 1.00 |
| 16547 | 3 | | | | | | USP49 | 1.00 | 16643 | 3 | | | | | | XAGE5 | 1.00 |
| 16548 | 3 | | | | | | USP50 | 1.00 | 16644 | 3 | | | | | | XCL1 | 1.00 |
| 16549 | 3 | | | | | | USP51 | 1.00 | 16645 | 3 | | | | | | XCL2 | 1.00 |
| 16550 | 3 | | | | | | USP6 | 1.00 | 16646 | 3 | | | | | | XDH | 1.00 |
| 16551 | 3 | | | | | | UTF1 | 1.00 | 16647 | 3 | | | | | | XIRP1 | 1.00 |
| 16552 | 3 | | | | | | UTS2 | 1.00 | 16648 | 3 | | | | | | XIRP2 | 1.00 |
| 16553 | 3 | | | | | | UTS2D | 1.00 | 16649 | 3 | | | | | | XK | 1.00 |
| 16554 | 3 | | | | | | UTS2R | 1.00 | 16650 | 3 | | | | | | XKR3 | 1.00 |
| 16555 | 3 | | | | | | VASH2 | 1.00 | 16651 | 3 | | | | | | XKR4 | 1.00 |
| 16556 | 3 | | | | | | VAT1L | 1.00 | 16652 | 3 | | | | | | XKR5 | 1.00 |
| 16557 | 3 | | | | | | VAX1 | 1.00 | 16653 | 3 | | | | | | XKR6 | 1.00 |
| 16558 | 3 | | | | | | VCX | 1.00 | 16654 | 3 | | | | | | XKR7 | 1.00 |
| 16559 | 3 | | | | | | VCX2 | 1.00 | 16655 | 3 | | | | | | XKR9 | 1.00 |
| 16560 | 3 | | | | | | VCX3A | 1.00 | 16656 | 3 | | | | | | XKRY | 1.00 |
| 16561 | 3 | | | | | | VCX3B | 1.00 | 16657 | 3 | | | | | | XKRY2 | 1.00 |
| 16562 | 3 | | | | | | VCY | 1.00 | 16658 | 3 | | | | | | XRCC2 | 1.00 |
| 16563 | 3 | | | | | | VCY1B | 1.00 | 16659 | 3 | | | | | | XYLB | 1.00 |
| 16564 | 3 | | | | | | VENTXP1 | 1.00 | 16660 | 3 | | | | | | YIPF7 | 1.00 |
| 16565 | 3 | | | | | | VENTXP7 | 1.00 | 16661 | 3 | | | | | | YSK4 | 1.00 |
| 16566 | 3 | | | | | | VGF | 1.00 | 16662 | 3 | | | | | | YY2 | 1.00 |
| 16567 | 3 | | | | | | VGLL1 | 1.00 | 16663 | 3 | | | | | | ZACN | 1.00 |
| 16568 | 3 | | | | | | VGLL2 | 1.00 | 16664 | 3 | | | | | | ZAN | 1.00 |
| 16569 | 3 | | | | | | VHLL | 1.00 | 16665 | 3 | | | | | | ZAR1 | 1.00 |
| 16570 | 3 | | | | | | VIL1 | 1.00 | 16666 | 3 | | | | | | ZAR1L | 1.00 |
| 16571 | 3 | | | | | | VIP | 1.00 | 16667 | 3 | | | | | | ZBBX | 1.00 |
| 16572 | 3 | | | | | | VIPR2 | 1.00 | 16668 | 3 | | | | | | ZBED6 | 1.00 |
| 16573 | 3 | | | | | | VN1R10P | 1.00 | 16669 | 3 | | | | | | ZBP1 | 1.00 |
| 16574 | 3 | | | | | | VN1R2 | 1.00 | 16670 | 3 | | | | | | ZBTB10 | 1.00 |
| 16575 | 3 | | | | | | VN1R4 | 1.00 | 16671 | 3 | | | | | | ZBTB20-AS1 | 1.00 |
| 16576 | 3 | | | | | | VN1R5 | 1.00 | 16672 | 3 | | | | | | ZBTB26 | 1.00 |
| 16577 | 3 | | | | | | VNN1 | 1.00 | 16673 | 3 | | | | | | ZBTB32 | 1.00 |
| 16578 | 3 | | | | | | VNN3 | 1.00 | 16674 | 3 | | | | | | ZBTB37 | 1.00 |
| 16579 | 3 | | | | | | VPREB1 | 1.00 | 16675 | 3 | | | | | | ZBTB8B | 1.00 |
| 16580 | 3 | | | | | | VPREB3 | 1.00 | 16676 | 3 | | | | | | ZC2HC1B | 1.00 |
| 16581 | 3 | | | | | | VRTN | 1.00 | 16677 | 3 | | | | | | ZC3H12B | 1.00 |
| 16582 | 3 | | | | | | VSIG1 | 1.00 | 16678 | 3 | | | | | | ZC3HAV1L | 1.00 |
| 16583 | 3 | | | | | | VSTM1 | 1.00 | 16679 | 3 | | | | | | ZCCHC12 | 1.00 |
| 16584 | 3 | | | | | | VSTM2A | 1.00 | 16680 | 3 | | | | | | ZCCHC13 | 1.00 |
| 16585 | 3 | | | | | | VSTM2B | 1.00 | 16681 | 3 | | | | | | ZCCHC16 | 1.00 |
| 16586 | 3 | | | | | | VSTM5 | 1.00 | 16682 | 3 | | | | | | ZCCHC18 | 1.00 |
| 16587 | 3 | | | | | | VSX1 | 1.00 | 16683 | 3 | | | | | | ZCCHC5 | 1.00 |
| 16588 | 3 | | | | | | VSX2 | 1.00 | 16684 | 3 | | | | | | ZCWPW2 | 1.00 |
| 16589 | 3 | | | | | | VTN | 1.00 | 16685 | 3 | | | | | | ZDBF2 | 1.00 |
| 16590 | 3 | | | | | | VTRNA1-1 | 1.00 | 16686 | 3 | | | | | | ZDHHC19 | 1.00 |
| 16591 | 3 | | | | | | VTRNA1-2 | 1.00 | 16687 | 3 | | | | | | ZDHHC22 | 1.00 |
| 16592 | 3 | | | | | | VTRNA1-3 | 1.00 | 16688 | 3 | | | | | | ZEB2-AS1 | 1.00 |
| 16593 | 3 | | | | | | VTRNA2-1 | 1.00 | 16689 | 3 | | | | | | ZFAT-AS1 | 1.00 |
| 16594 | 3 | | | | | | VWA3A | 1.00 | 16690 | 3 | | | | | | ZFHX2 | 1.00 |
| 16595 | 3 | | | | | | VWA3B | 1.00 | 16691 | 3 | | | | | | ZFHX4 | 1.00 |
| 16596 | 3 | | | | | | VWA5B1 | 1.00 | 16692 | 3 | | | | | | ZFP42 | 1.00 |
| 16597 | 3 | | | | | | VWA5B2 | 1.00 | 16693 | 3 | | | | | | ZFP82 | 1.00 |
| 16598 | 3 | | | | | | VWC2L | 1.00 | 16694 | 3 | | | | | | ZFP91-CNTF | 1.00 |

Fig. 39 - 88

| | | | | | | | |
|---|---|---|---|---|---|---|---|
| 16695 | 3 | | | | ZFP92 | 1.00 |
| 16696 | 3 | | | | ZFR2 | 1.00 |
| 16697 | 3 | | | | ZG16 | 1.00 |
| 16698 | 3 | | | | ZIC1 | 1.00 |
| 16699 | 3 | | | | ZIC2 | 1.00 |
| 16700 | 3 | | | | ZIC3 | 1.00 |
| 16701 | 3 | | | | ZIC4 | 1.00 |
| 16702 | 3 | | | | ZIC5 | 1.00 |
| 16703 | 3 | | | | ZIM2 | 1.00 |
| 16704 | 3 | | | | ZIM3 | 1.00 |
| 16705 | 3 | | | | ZKSCAN2 | 1.00 |
| 16706 | 3 | | | | ZMAT4 | 1.00 |
| 16707 | 3 | | | | ZMYND10 | 1.00 |
| 16708 | 3 | | | | ZMYND12 | 1.00 |
| 16709 | 3 | | | | ZNF114 | 1.00 |
| 16710 | 3 | | | | ZNF121 | 1.00 |
| 16711 | 3 | | | | ZNF154 | 1.00 |
| 16712 | 3 | | | | ZNF157 | 1.00 |
| 16713 | 3 | | | | ZNF167 | 1.00 |
| 16714 | 3 | | | | ZNF169 | 1.00 |
| 16715 | 3 | | | | ZNF192 | 1.00 |
| 16716 | 3 | | | | ZNF208 | 1.00 |
| 16717 | 3 | | | | ZNF214 | 1.00 |
| 16718 | 3 | | | | ZNF215 | 1.00 |
| 16719 | 3 | | | | ZNF221 | 1.00 |
| 16720 | 3 | | | | ZNF229 | 1.00 |
| 16721 | 3 | | | | ZNF233 | 1.00 |
| 16722 | 3 | | | | ZNF257 | 1.00 |
| 16723 | 3 | | | | ZNF280A | 1.00 |
| 16724 | 3 | | | | ZNF280B | 1.00 |
| 16725 | 3 | | | | ZNF284 | 1.00 |
| 16726 | 3 | | | | ZNF295-AS1 | 1.00 |
| 16727 | 3 | | | | ZNF32-AS3 | 1.00 |
| 16728 | 3 | | | | ZNF354C | 1.00 |
| 16729 | 3 | | | | ZNF365 | 1.00 |
| 16730 | 3 | | | | ZNF366 | 1.00 |
| 16731 | 3 | | | | ZNF382 | 1.00 |
| 16732 | 3 | | | | ZNF391 | 1.00 |
| 16733 | 3 | | | | ZNF396 | 1.00 |
| 16734 | 3 | | | | ZNF442 | 1.00 |
| 16735 | 3 | | | | ZNF454 | 1.00 |
| 16736 | 3 | | | | ZNF460 | 1.00 |
| 16737 | 3 | | | | ZNF474 | 1.00 |
| 16738 | 3 | | | | ZNF479 | 1.00 |
| 16739 | 3 | | | | ZNF483 | 1.00 |
| 16740 | 3 | | | | ZNF484 | 1.00 |
| 16741 | 3 | | | | ZNF491 | 1.00 |
| 16742 | 3 | | | | ZNF492 | 1.00 |
| 16743 | 3 | | | | ZNF519 | 1.00 |
| 16744 | 3 | | | | ZNF534 | 1.00 |
| 16745 | 3 | | | | ZNF536 | 1.00 |
| 16746 | 3 | | | | ZNF541 | 1.00 |
| 16747 | 3 | | | | ZNF546 | 1.00 |
| 16748 | 3 | | | | ZNF555 | 1.00 |
| 16749 | 3 | | | | ZNF556 | 1.00 |
| 16750 | 3 | | | | ZNF559-ZNF177 | 1.00 |
| 16751 | 3 | | | | ZNF560 | 1.00 |
| 16752 | 3 | | | | ZNF570 | 1.00 |
| 16753 | 3 | | | | ZNF572 | 1.00 |
| 16754 | 3 | | | | ZNF578 | 1.00 |
| 16755 | 3 | | | | ZNF582 | 1.00 |
| 16756 | 3 | | | | ZNF585A | 1.00 |
| 16757 | 3 | | | | ZNF594 | 1.00 |
| 16758 | 3 | | | | ZNF625 | 1.00 |
| 16759 | 3 | | | | ZNF625-ZNF20 | 1.00 |
| 16760 | 3 | | | | ZNF643 | 1.00 |
| 16761 | 3 | | | | ZNF645 | 1.00 |
| 16762 | 3 | | | | ZNF648 | 1.00 |
| 16763 | 3 | | | | ZNF660 | 1.00 |
| 16764 | 3 | | | | ZNF663 | 1.00 |
| 16765 | 3 | | | | ZNF664-FAM101A | 1.00 |
| 16766 | 3 | | | | ZNF670-ZNF695 | 1.00 |
| 16767 | 3 | | | | ZNF676 | 1.00 |
| 16768 | 3 | | | | ZNF677 | 1.00 |
| 16769 | 3 | | | | ZNF678 | 1.00 |
| 16770 | 3 | | | | ZNF679 | 1.00 |
| 16771 | 3 | | | | ZNF695 | 1.00 |
| 16772 | 3 | | | | ZNF699 | 1.00 |
| 16773 | 3 | | | | ZNF702P | 1.00 |
| 16774 | 3 | | | | ZNF705A | 1.00 |
| 16775 | 3 | | | | ZNF705D | 1.00 |
| 16776 | 3 | | | | ZNF705G | 1.00 |
| 16777 | 3 | | | | ZNF709 | 1.00 |
| 16778 | 3 | | | | ZNF713 | 1.00 |
| 16779 | 3 | | | | ZNF716 | 1.00 |
| 16780 | 3 | | | | ZNF717 | 1.00 |
| 16781 | 3 | | | | ZNF724P | 1.00 |
| 16782 | 3 | | | | ZNF726 | 1.00 |
| 16783 | 3 | | | | ZNF727 | 1.00 |
| 16784 | 3 | | | | ZNF729 | 1.00 |
| 16785 | 3 | | | | ZNF732 | 1.00 |
| 16786 | 3 | | | | ZNF735 | 1.00 |
| 16787 | 3 | | | | ZNF736 | 1.00 |
| 16788 | 3 | | | | ZNF778 | 1.00 |
| 16789 | 3 | | | | ZNF781 | 1.00 |
| 16790 | 3 | | | | ZNF80 | 1.00 |
| 16791 | 3 | | | | ZNF804A | 1.00 |
| 16792 | 3 | | | | ZNF804B | 1.00 |
| 16793 | 3 | | | | ZNF81 | 1.00 |
| 16794 | 3 | | | | ZNF812 | 1.00 |
| 16795 | 3 | | | | ZNF813 | 1.00 |
| 16796 | 3 | | | | ZNF816-ZNF321P | 1.00 |
| 16797 | 3 | | | | ZNF826P | 1.00 |
| 16798 | 3 | | | | ZNF831 | 1.00 |
| 16799 | 3 | | | | ZNF833P | 1.00 |
| 16800 | 3 | | | | ZNF843 | 1.00 |
| 16801 | 3 | | | | ZNF847P | 1.00 |
| 16802 | 3 | | | | ZNF850 | 1.00 |
| 16803 | 3 | | | | ZNF860 | 1.00 |
| 16804 | 3 | | | | ZNF876P | 1.00 |
| 16805 | 3 | | | | ZNF878 | 1.00 |
| 16806 | 3 | | | | ZNF883 | 1.00 |
| 16807 | 3 | | | | ZNF890P | 1.00 |
| 16808 | 3 | | | | ZNF90 | 1.00 |
| 16809 | 3 | | | | ZNF98 | 1.00 |
| 16810 | 3 | | | | ZNF99 | 1.00 |
| 16811 | 3 | | | | ZNRD1-AS1 | 1.00 |
| 16812 | 3 | | | | ZNRF2P1 | 1.00 |
| 16813 | 3 | | | | ZNRF2P2 | 1.00 |
| 16814 | 3 | | | | ZNRF4 | 1.00 |
| 16815 | 3 | | | | ZP2 | 1.00 |
| 16816 | 3 | | | | ZP4 | 1.00 |
| 16817 | 3 | | | | ZPBP | 1.00 |
| 16818 | 3 | | | | ZPBP2 | 1.00 |
| 16819 | 3 | | | | ZPLD1 | 1.00 |
| 16820 | 3 | | | | ZRANB2-AS2 | 1.00 |
| 16821 | 3 | | | | ZRANB3 | 1.00 |
| 16822 | 3 | | | | ZSCAN1 | 1.00 |
| 16823 | 3 | | | | ZSCAN10 | 1.00 |
| 16824 | 3 | | | | ZSCAN12P1 | 1.00 |
| 16825 | 3 | | | | ZSCAN20 | 1.00 |
| 16826 | 3 | | | | ZSCAN23 | 1.00 |
| 16827 | 3 | | | | ZSCAN4 | 1.00 |
| 16828 | 3 | | | | ZSCAN5B | 1.00 |
| 16829 | 3 | | | | ZSWIM2 | 1.00 |
| 16830 | 3 | | | | ZYG11A | 1.00 |

Fig. 40 - 1

| Line No. | Group No. | | | | | Sub-Groups | Gene Name | Breast cancer |
|---|---|---|---|---|---|---|---|---|
| 1 | 3 | 4 | 5 | 6 | 7 | VII-2 | CD88 | 0.19 |
| 2 | 3 | 4 | 5 | 6 | 7 | VII-2 | FAM45A | 0.12 |
| 3 | 3 | 4 | 5 | 6 | 7 | VII-2 | HP | 0.16 |
| 4 | 3 | 4 | 5 | 6 | 7 | VII-1 | ABHD3 | 5.05 |
| 5 | 3 | 4 | 5 | 6 | 7 | VII-1 | ADCK1 | 5.54 |
| 6 | 3 | 4 | 5 | 6 | 7 | VII-1 | AGRN | 8.11 |
| 7 | 3 | 4 | 5 | 6 | 7 | VII-1 | AKAP9 | 5.65 |
| 8 | 3 | 4 | 5 | 6 | 7 | VII-1 | ALS2CL | 5.29 |
| 9 | 3 | 4 | 5 | 6 | 7 | VII-1 | AMT | 8.17 |
| 10 | 3 | 4 | 5 | 6 | 7 | VII-1 | AMY2B | 9.78 |
| 11 | 3 | 4 | 5 | 6 | 7 | VII-1 | ANO9 | 6.65 |
| 12 | 3 | 4 | 5 | 6 | 7 | VII-1 | ASMTL-AS1 | 5.44 |
| 13 | 3 | 4 | 5 | 6 | 7 | VII-1 | ATF3 | 11.44 |
| 14 | 3 | 4 | 5 | 6 | 7 | VII-1 | AVIL | 8.50 |
| 15 | 3 | 4 | 5 | 6 | 7 | VII-1 | C2 | 5.30 |
| 16 | 3 | 4 | 5 | 6 | 7 | VII-1 | C20orf118 | 7.25 |
| 17 | 3 | 4 | 5 | 6 | 7 | VII-1 | CAPN3 | 6.27 |
| 18 | 3 | 4 | 5 | 6 | 7 | VII-1 | CCL2 | 6.48 |
| 19 | 3 | 4 | 5 | 6 | 7 | VII-1 | CHMP5 | 5.67 |
| 20 | 3 | 4 | 5 | 6 | 7 | VII-1 | CRIPAK | 5.41 |
| 21 | 3 | 4 | 5 | 6 | 7 | VII-1 | DDX60 | 13.68 |
| 22 | 3 | 4 | 5 | 6 | 7 | VII-1 | DHX58 | 9.85 |
| 23 | 3 | 4 | 5 | 6 | 7 | VII-1 | DMXL2 | 6.56 |
| 24 | 3 | 4 | 5 | 6 | 7 | VII-1 | DOCK4 | 6.30 |
| 25 | 3 | 4 | 5 | 6 | 7 | VII-1 | ENGASE | 6.85 |
| 26 | 3 | 4 | 5 | 6 | 7 | VII-1 | FAM111A | 6.24 |
| 27 | 3 | 4 | 5 | 6 | 7 | VII-1 | FAM156B | 5.77 |
| 28 | 3 | 4 | 5 | 6 | 7 | VII-1 | FTSJD2 | 5.36 |
| 29 | 3 | 4 | 5 | 6 | 7 | VII-1 | GBP1P1 | 6.92 |
| 30 | 3 | 4 | 5 | 6 | 7 | VII-1 | GBP4 | 5.84 |
| 31 | 3 | 4 | 5 | 6 | 7 | VII-1 | GLI1 | 5.99 |
| 32 | 3 | 4 | 5 | 6 | 7 | VII-1 | HERC2 | 5.29 |
| 33 | 3 | 4 | 5 | 6 | 7 | VII-1 | HERC2P2 | 10.07 |
| 34 | 3 | 4 | 5 | 6 | 7 | VII-1 | HERC6 | 9.07 |
| 35 | 3 | 4 | 5 | 6 | 7 | VII-1 | HES4 | 7.44 |
| 36 | 3 | 4 | 5 | 6 | 7 | VII-1 | HIST2H2BF | 5.45 |
| 37 | 3 | 4 | 5 | 6 | 7 | VII-1 | HNRNPH2 | 19.16 |
| 38 | 3 | 4 | 5 | 6 | 7 | VII-1 | HSP90AA6P | 5.03 |
| 39 | 3 | 4 | 5 | 6 | 7 | VII-1 | HSPA7 | 8.51 |
| 40 | 3 | 4 | 5 | 6 | 7 | VII-1 | IFI44 | 41.70 |
| 41 | 3 | 4 | 5 | 6 | 7 | VII-1 | IFIH1 | 8.26 |
| 42 | 3 | 4 | 5 | 6 | 7 | VII-1 | IFIT5 | 6.95 |
| 43 | 3 | 4 | 5 | 6 | 7 | VII-1 | IRF7 | 9.47 |
| 44 | 3 | 4 | 5 | 6 | 7 | VII-1 | KCND1 | 5.06 |
| 45 | 3 | 4 | 5 | 6 | 7 | VII-1 | KIAA0895L | 11.00 |
| 46 | 3 | 4 | 5 | 6 | 7 | VII-1 | KIAA1683 | 7.73 |
| 47 | 3 | 4 | 5 | 6 | 7 | VII-1 | KRT72 | 11.44 |
| 48 | 3 | 4 | 5 | 6 | 7 | VII-1 | LAMP3 | 7.99 |
| 49 | 3 | 4 | 5 | 6 | 7 | VII-1 | LINC00189 | 6.86 |
| 50 | 3 | 4 | 5 | 6 | 7 | VII-1 | LOC100131564 | 9.87 |
| 51 | 3 | 4 | 5 | 6 | 7 | VII-1 | LOC100216546 | 6.24 |
| 52 | 3 | 4 | 5 | 6 | 7 | VII-1 | LOC100294362 | 5.34 |
| 53 | 3 | 4 | 5 | 6 | 7 | VII-1 | LOC100630923 | 5.26 |
| 54 | 3 | 4 | 5 | 6 | 7 | VII-1 | LOC158257 | 6.10 |
| 55 | 3 | 4 | 5 | 6 | 7 | VII-1 | LOC200772 | 5.28 |
| 56 | 3 | 4 | 5 | 6 | 7 | VII-1 | LOC283663 | 6.38 |
| 57 | 3 | 4 | 5 | 6 | 7 | VII-1 | LOC391322 | 5.03 |
| 58 | 3 | 4 | 5 | 6 | 7 | VII-1 | LRWD1 | 8.17 |
| 59 | 3 | 4 | 5 | 6 | 7 | VII-1 | LUC7L3 | 5.74 |
| 60 | 3 | 4 | 5 | 6 | 7 | VII-1 | LY6E | 14.14 |
| 61 | 3 | 4 | 5 | 6 | 7 | VII-1 | MAGI2-AS3 | 6.77 |
| 62 | 3 | 4 | 5 | 6 | 7 | VII-1 | MIR1184-3 | 135.00 |
| 63 | 3 | 4 | 5 | 6 | 7 | VII-1 | MIR3665 | 57.75 |
| 64 | 3 | 4 | 5 | 6 | 7 | VII-1 | MIR4313 | 139.39 |
| 65 | 3 | 4 | 5 | 6 | 7 | VII-1 | MIR573 | 226.95 |
| 66 | 3 | 4 | 5 | 6 | 7 | VII-1 | MOV10 | 9.56 |
| 67 | 3 | 4 | 5 | 6 | 7 | VII-1 | MT2A | 6.16 |
| 68 | 3 | 4 | 5 | 6 | 7 | VII-1 | MUSTN1 | 7.16 |
| 69 | 3 | 4 | 5 | 6 | 7 | VII-1 | MYOF | 6.38 |
| 70 | 3 | 4 | 5 | 6 | 7 | VII-1 | NCAPH2 | 11.27 |
| 71 | 3 | 4 | 5 | 6 | 7 | VII-1 | NEXN | 12.08 |
| 72 | 3 | 4 | 5 | 6 | 7 | VII-1 | NKTR | 5.22 |
| 73 | 3 | 4 | 5 | 6 | 7 | VII-1 | NXF1 | 5.19 |
| 74 | 3 | 4 | 5 | 6 | 7 | VII-1 | OAS1 | 25.97 |
| 75 | 3 | 4 | 5 | 6 | 7 | VII-1 | OAS2 | 16.11 |
| 76 | 3 | 4 | 5 | 6 | 7 | VII-1 | OAS3 | 33.06 |
| 77 | 3 | 4 | 5 | 6 | 7 | VII-1 | OASL | 14.62 |
| 78 | 3 | 4 | 5 | 6 | 7 | VII-1 | OTOF | 11.69 |
| 79 | 3 | 4 | 5 | 6 | 7 | VII-1 | PAN2 | 5.02 |
| 80 | 3 | 4 | 5 | 6 | 7 | VII-1 | PAQR6 | 8.28 |
| 81 | 3 | 4 | 5 | 6 | 7 | VII-1 | PARP10 | 6.73 |
| 82 | 3 | 4 | 5 | 6 | 7 | VII-1 | PARP12 | 11.09 |
| 83 | 3 | 4 | 5 | 6 | 7 | VII-1 | PARP14 | 10.20 |
| 84 | 3 | 4 | 5 | 6 | 7 | VII-1 | PARP9 | 7.01 |
| 85 | 3 | 4 | 5 | 6 | 7 | VII-1 | PCGF3 | 5.22 |
| 86 | 3 | 4 | 5 | 6 | 7 | VII-1 | PLGLB1 | 5.69 |
| 87 | 3 | 4 | 5 | 6 | 7 | VII-1 | PLSCR1 | 6.75 |
| 88 | 3 | 4 | 5 | 6 | 7 | VII-1 | PNISR | 5.28 |
| 89 | 3 | 4 | 5 | 6 | 7 | VII-1 | PPP1R3E | 7.21 |
| 90 | 3 | 4 | 5 | 6 | 7 | VII-1 | PRIC285 | 6.76 |
| 91 | 3 | 4 | 5 | 6 | 7 | VII-1 | PRRG4 | 5.94 |
| 92 | 3 | 4 | 5 | 6 | 7 | VII-1 | PSME2 | 5.05 |
| 93 | 3 | 4 | 5 | 6 | 7 | VII-1 | REC8 | 7.88 |
| 94 | 3 | 4 | 5 | 6 | 7 | VII-1 | RGPD1 | 5.63 |
| 95 | 3 | 4 | 5 | 6 | 7 | VII-1 | RGPD2 | 5.73 |
| 96 | 3 | 4 | 5 | 6 | 7 | VII-1 | RNF213 | 8.65 |
| 97 | 3 | 4 | 5 | 6 | 7 | VII-1 | RTP4 | 8.73 |
| 98 | 3 | 4 | 5 | 6 | 7 | VII-1 | RUFY4 | 5.48 |
| 99 | 3 | 4 | 5 | 6 | 7 | VII-1 | SAMD4A | 6.62 |
| 100 | 3 | 4 | 5 | 6 | 7 | VII-1 | SAMD9 | 5.66 |
| 101 | 3 | 4 | 5 | 6 | 7 | VII-1 | SAMD9L | 11.19 |
| 102 | 3 | 4 | 5 | 6 | 7 | VII-1 | SCARNA4 | 18.67 |
| 103 | 3 | 4 | 5 | 6 | 7 | VII-1 | SCO2 | 14.07 |
| 104 | 3 | 4 | 5 | 6 | 7 | VII-1 | SEC31B | 6.15 |
| 105 | 3 | 4 | 5 | 6 | 7 | VII-1 | SESTD1 | 6.50 |
| 106 | 3 | 4 | 5 | 6 | 7 | VII-1 | SIGLEC1 | 71.83 |
| 107 | 3 | 4 | 5 | 6 | 7 | VII-1 | SMTNL1 | 58.71 |
| 108 | 3 | 4 | 5 | 6 | 7 | VII-1 | SNORA11D | 11.00 |
| 109 | 3 | 4 | 5 | 6 | 7 | VII-1 | SNORA11E | 11.00 |
| 110 | 3 | 4 | 5 | 6 | 7 | VII-1 | SNORA37 | 9.33 |
| 111 | 3 | 4 | 5 | 6 | 7 | VII-1 | SNORA40 | 21.00 |
| 112 | 3 | 4 | 5 | 6 | 7 | VII-1 | SNORA42 | 7.39 |
| 113 | 3 | 4 | 5 | 6 | 7 | VII-1 | SNORA44 | 16.17 |
| 114 | 3 | 4 | 5 | 6 | 7 | VII-1 | SNORA55 | 6.51 |
| 115 | 3 | 4 | 5 | 6 | 7 | VII-1 | SNORA5A | 7.39 |
| 116 | 3 | 4 | 5 | 6 | 7 | VII-1 | SP140 | 5.23 |
| 117 | 3 | 4 | 5 | 6 | 7 | VII-1 | SPATS2L | 9.66 |
| 118 | 3 | 4 | 5 | 6 | 7 | VII-1 | STAB1 | 5.38 |
| 119 | 3 | 4 | 5 | 6 | 7 | VII-1 | STAT1 | 6.58 |
| 120 | 3 | 4 | 5 | 6 | 7 | VII-1 | STAT2 | 12.95 |
| 121 | 3 | 4 | 5 | 6 | 7 | VII-1 | STX16 | 5.16 |
| 122 | 3 | 4 | 5 | 6 | 7 | VII-1 | SUMO1P1 | 5.79 |
| 123 | 3 | 4 | 5 | 6 | 7 | VII-1 | TAP2 | 6.64 |
| 124 | 3 | 4 | 5 | 6 | 7 | VII-1 | TBC1D3H | 5.17 |
| 125 | 3 | 4 | 5 | 6 | 7 | VII-1 | TCN2 | 5.41 |
| 126 | 3 | 4 | 5 | 6 | 7 | VII-1 | THBS3 | 5.39 |
| 127 | 3 | 4 | 5 | 6 | 7 | VII-1 | TRIM22 | 7.83 |
| 128 | 3 | 4 | 5 | 6 | 7 | VII-1 | TRIM5 | 5.11 |
| 129 | 3 | 4 | 5 | 6 | 7 | VII-1 | TRIM56 | 5.61 |
| 130 | 3 | 4 | 5 | 6 | 7 | VII-1 | TRIM78P | 8.68 |
| 131 | 3 | 4 | 5 | 6 | 7 | VII-1 | TTC14 | 5.42 |
| 132 | 3 | 4 | 5 | 6 | 7 | VII-1 | UBA7 | 5.07 |
| 133 | 3 | 4 | 5 | 6 | 7 | VII-1 | USP18 | 11.00 |
| 134 | 3 | 4 | 5 | 6 | 7 | VII-1 | VEGFA | 5.90 |
| 135 | 3 | 4 | 5 | 6 | 7 | VII-1 | WDR60 | 5.16 |
| 136 | 3 | 4 | 5 | 6 | 7 | VII-1 | ZBP1 | 9.88 |
| 137 | 3 | 4 | 5 | 6 | 7 | VII-1 | ZC3H6 | 5.16 |
| 138 | 3 | 4 | 5 | 6 | 7 | VII-1 | ZCCHC2 | 9.18 |
| 139 | 3 | 4 | 5 | 6 | 7 | VII-1 | ZNF117 | 6.23 |
| 140 | 3 | 4 | 5 | 6 | 7 | VII-1 | ZNF514 | 5.66 |
| 141 | 3 | 4 | 5 | 6 | | VI-2 | C12orf57 | 0.42 |
| 142 | 3 | 4 | 5 | 6 | | VI-2 | CCDC167 | 0.25 |
| 143 | 3 | 4 | 5 | 6 | | VI-2 | CD8A | 0.23 |
| 144 | 3 | 4 | 5 | 6 | | VI-2 | COX20 | 0.43 |
| 145 | 3 | 4 | 5 | 6 | | VI-2 | DUSP2 | 0.46 |
| 146 | 3 | 4 | 5 | 6 | | VI-2 | EEF1B2 | 0.32 |
| 147 | 3 | 4 | 5 | 6 | | VI-2 | FB | 0.36 |
| 148 | 3 | 4 | 5 | 6 | | VI-2 | FCRL6 | 0.27 |
| 149 | 3 | 4 | 5 | 6 | | VI-2 | FUNDC2 | 0.45 |
| 150 | 3 | 4 | 5 | 6 | | VI-2 | GNG10 | 0.44 |
| 151 | 3 | 4 | 5 | 6 | | VI-2 | ID2B | 0.35 |
| 152 | 3 | 4 | 5 | 6 | | VI-2 | KLRB1 | 0.25 |
| 153 | 3 | 4 | 5 | 6 | | VI-2 | KLRD1 | 0.38 |
| 154 | 3 | 4 | 5 | 6 | | VI-2 | NCALD | 0.38 |
| 155 | 3 | 4 | 5 | 6 | | VI-2 | NDUFAF2 | 0.49 |
| 156 | 3 | 4 | 5 | 6 | | VI-2 | PPDPF | 0.34 |
| 157 | 3 | 4 | 5 | 6 | | VI-2 | PPP2R2B | 0.30 |
| 158 | 3 | 4 | 5 | 6 | | VI-2 | PRSS23 | 0.34 |
| 159 | 3 | 4 | 5 | 6 | | VI-2 | PTCH1 | 0.36 |
| 160 | 3 | 4 | 5 | 6 | | VI-2 | RPL12 | 0.45 |
| 161 | 3 | 4 | 5 | 6 | | VI-2 | RPL21P28 | 0.37 |
| 162 | 3 | 4 | 5 | 6 | | VI-2 | RPL27 | 0.50 |
| 163 | 3 | 4 | 5 | 6 | | VI-2 | RPS10 | 0.39 |
| 164 | 3 | 4 | 5 | 6 | | VI-2 | RPS14 | 0.41 |
| 165 | 3 | 4 | 5 | 6 | | VI-2 | RPS3 | 0.40 |
| 166 | 3 | 4 | 5 | 6 | | VI-2 | RPS6 | 0.48 |
| 167 | 3 | 4 | 5 | 6 | | VI-2 | RPS7 | 0.46 |
| 168 | 3 | 4 | 5 | 6 | | VI-2 | RPSAP9 | 0.46 |
| 169 | 3 | 4 | 5 | 6 | | VI-2 | S1PR5 | 0.43 |
| 170 | 3 | 4 | 5 | 6 | | VI-2 | SIGLEC14 | 0.22 |
| 171 | 3 | 4 | 5 | 6 | | VI-1 | A1BG-AS1 | 2.57 |
| 172 | 3 | 4 | 5 | 6 | | VI-1 | AAAS | 2.44 |
| 173 | 3 | 4 | 5 | 6 | | VI-1 | AAK1 | 2.37 |
| 174 | 3 | 4 | 5 | 6 | | VI-1 | AARS | 2.22 |
| 175 | 3 | 4 | 5 | 6 | | VI-1 | AARS2 | 2.43 |
| 176 | 3 | 4 | 5 | 6 | | VI-1 | AASDH | 2.18 |
| 177 | 3 | 4 | 5 | 6 | | VI-1 | ABAT | 2.04 |
| 178 | 3 | 4 | 5 | 6 | | VI-1 | ABCB8 | 2.82 |
| 179 | 3 | 4 | 5 | 6 | | VI-1 | ABCC1 | 2.51 |
| 180 | 3 | 4 | 5 | 6 | | VI-1 | ABCC10 | 2.51 |
| 181 | 3 | 4 | 5 | 6 | | VI-1 | ABCC5 | 3.69 |
| 182 | 3 | 4 | 5 | 6 | | VI-1 | ABCD1 | 3.17 |
| 183 | 3 | 4 | 5 | 6 | | VI-1 | ABCD4 | 2.54 |
| 184 | 3 | 4 | 5 | 6 | | VI-1 | ABCF3 | 2.16 |
| 185 | 3 | 4 | 5 | 6 | | VI-1 | ABCG1 | 3.12 |
| 186 | 3 | 4 | 5 | 6 | | VI-1 | ABHD16A | 2.52 |
| 187 | 3 | 4 | 5 | 6 | | VI-1 | ABHD16B | 2.17 |
| 188 | 3 | 4 | 5 | 6 | | VI-1 | ABR | 2.02 |
| 189 | 3 | 4 | 5 | 6 | | VI-1 | ACAD10 | 2.71 |
| 190 | 3 | 4 | 5 | 6 | | VI-1 | ACAD11 | 2.24 |

Fig. 40 - 2

| | | | | | | | |
|---|---|---|---|---|---|---|---|
| 191 | 3 | 4 | 5 | 6 | VI-1 | ACAD8 | 2.92 |
| 192 | 3 | 4 | 5 | 6 | VI-1 | ACAD9 | 2.03 |
| 193 | 3 | 4 | 5 | 6 | VI-1 | ACADVL | 2.98 |
| 194 | 3 | 4 | 5 | 6 | VI-1 | ACAP1 | 2.07 |
| 195 | 3 | 4 | 5 | 6 | VI-1 | ACAP2 | 2.22 |
| 196 | 3 | 4 | 5 | 6 | VI-1 | ACAP3 | 3.23 |
| 197 | 3 | 4 | 5 | 6 | VI-1 | ACBD4 | 3.06 |
| 198 | 3 | 4 | 5 | 6 | VI-1 | ACCS | 2.18 |
| 199 | 3 | 4 | 5 | 6 | VI-1 | ACIN1 | 2.77 |
| 200 | 3 | 4 | 5 | 6 | VI-1 | ACO1 | 4.66 |
| 201 | 3 | 4 | 5 | 6 | VI-1 | ACOT9 | 4.33 |
| 202 | 3 | 4 | 5 | 6 | VI-1 | ACOX1 | 2.25 |
| 203 | 3 | 4 | 5 | 6 | VI-1 | ACOX3 | 2.14 |
| 204 | 3 | 4 | 5 | 6 | VI-1 | ACP2 | 2.14 |
| 205 | 3 | 4 | 5 | 6 | VI-1 | ACP5 | 2.09 |
| 206 | 3 | 4 | 5 | 6 | VI-1 | ACRC | 2.22 |
| 207 | 3 | 4 | 5 | 6 | VI-1 | ACSF2 | 2.50 |
| 208 | 3 | 4 | 5 | 6 | VI-1 | ACSF3 | 2.32 |
| 209 | 3 | 4 | 5 | 6 | VI-1 | ACSS1 | 2.07 |
| 210 | 3 | 4 | 5 | 6 | VI-1 | ACSS2 | 2.65 |
| 211 | 3 | 4 | 5 | 6 | VI-1 | ACTR5 | 2.53 |
| 212 | 3 | 4 | 5 | 6 | VI-1 | ACVR1 | 2.20 |
| 213 | 3 | 4 | 5 | 6 | VI-1 | ACVR2A | 2.55 |
| 214 | 3 | 4 | 5 | 6 | VI-1 | ACVR2B | 2.07 |
| 215 | 3 | 4 | 5 | 6 | VI-1 | ADAM1 | 4.53 |
| 216 | 3 | 4 | 5 | 6 | VI-1 | ADAM17 | 2.57 |
| 217 | 3 | 4 | 5 | 6 | VI-1 | ADAM28 | 2.84 |
| 218 | 3 | 4 | 5 | 6 | VI-1 | ADAM8 | 2.01 |
| 219 | 3 | 4 | 5 | 6 | VI-1 | ADAM9 | 2.31 |
| 220 | 3 | 4 | 5 | 6 | VI-1 | ADAR | 3.53 |
| 221 | 3 | 4 | 5 | 6 | VI-1 | ADCK4 | 2.14 |
| 222 | 3 | 4 | 5 | 6 | VI-1 | ADCK5 | 2.34 |
| 223 | 3 | 4 | 5 | 6 | VI-1 | ADCY3 | 2.01 |
| 224 | 3 | 4 | 5 | 6 | VI-1 | ADCY4 | 2.65 |
| 225 | 3 | 4 | 5 | 6 | VI-1 | ADCY7 | 3.82 |
| 226 | 3 | 4 | 5 | 6 | VI-1 | ADD2 | 2.20 |
| 227 | 3 | 4 | 5 | 6 | VI-1 | ADHFE1 | 2.50 |
| 228 | 3 | 4 | 5 | 6 | VI-1 | ADPGK | 2.10 |
| 229 | 3 | 4 | 5 | 6 | VI-1 | ADPRH | 2.24 |
| 230 | 3 | 4 | 5 | 6 | VI-1 | AEBP1 | 2.48 |
| 231 | 3 | 4 | 5 | 6 | VI-1 | AFF1 | 3.52 |
| 232 | 3 | 4 | 5 | 6 | VI-1 | AFF4 | 2.21 |
| 233 | 3 | 4 | 5 | 6 | VI-1 | AFG3L1P | 3.37 |
| 234 | 3 | 4 | 5 | 6 | VI-1 | AFTPH | 2.05 |
| 235 | 3 | 4 | 5 | 6 | VI-1 | AGAP5 | 4.18 |
| 236 | 3 | 4 | 5 | 6 | VI-1 | AGAP9 | 2.04 |
| 237 | 3 | 4 | 5 | 6 | VI-1 | AGL | 2.53 |
| 238 | 3 | 4 | 5 | 6 | VI-1 | AGPAT3 | 2.40 |
| 239 | 3 | 4 | 5 | 6 | VI-1 | AGPAT4 | 2.58 |
| 240 | 3 | 4 | 5 | 6 | VI-1 | AGXT2L2 | 3.08 |
| 241 | 3 | 4 | 5 | 6 | VI-1 | AHCYL2 | 2.62 |
| 242 | 3 | 4 | 5 | 6 | VI-1 | AKAP12 | 3.30 |
| 243 | 3 | 4 | 5 | 6 | VI-1 | AKAP13 | 2.33 |
| 244 | 3 | 4 | 5 | 6 | VI-1 | AKAP17A | 3.26 |
| 245 | 3 | 4 | 5 | 6 | VI-1 | AKAP8L | 2.35 |
| 246 | 3 | 4 | 5 | 6 | VI-1 | AKIRIN2 | 2.02 |
| 247 | 3 | 4 | 5 | 6 | VI-1 | AKR1A1 | 2.26 |
| 248 | 3 | 4 | 5 | 6 | VI-1 | ALDH3A2 | 2.03 |
| 249 | 3 | 4 | 5 | 6 | VI-1 | ALG13 | 3.15 |
| 250 | 3 | 4 | 5 | 6 | VI-1 | ALG6 | 2.76 |
| 251 | 3 | 4 | 5 | 6 | VI-1 | ALG8 | 3.01 |
| 252 | 3 | 4 | 5 | 6 | VI-1 | ALKBH4 | 3.20 |
| 253 | 3 | 4 | 5 | 6 | VI-1 | ALKBH6 | 2.58 |
| 254 | 3 | 4 | 5 | 6 | VI-1 | ALOX5 | 2.13 |
| 255 | 3 | 4 | 5 | 6 | VI-1 | ALS2CR8 | 2.59 |
| 256 | 3 | 4 | 5 | 6 | VI-1 | AMACR | 2.09 |
| 257 | 3 | 4 | 5 | 6 | VI-1 | AMBRA1 | 2.11 |
| 258 | 3 | 4 | 5 | 6 | VI-1 | AMDHD2 | 2.29 |
| 259 | 3 | 4 | 5 | 6 | VI-1 | AMIGO2 | 2.68 |
| 260 | 3 | 4 | 5 | 6 | VI-1 | AMIGO3 | 2.49 |
| 261 | 3 | 4 | 5 | 6 | VI-1 | AMN1 | 3.06 |
| 262 | 3 | 4 | 5 | 6 | VI-1 | ANAPC2 | 2.52 |
| 263 | 3 | 4 | 5 | 6 | VI-1 | ANAPC4 | 2.93 |
| 264 | 3 | 4 | 5 | 6 | VI-1 | ANAPC7 | 2.09 |
| 265 | 3 | 4 | 5 | 6 | VI-1 | ANKDD1A | 3.43 |
| 266 | 3 | 4 | 5 | 6 | VI-1 | ANKFY1 | 3.84 |
| 267 | 3 | 4 | 5 | 6 | VI-1 | ANKHD1 | 3.36 |
| 268 | 3 | 4 | 5 | 6 | VI-1 | ANKIB1 | 2.07 |
| 269 | 3 | 4 | 5 | 6 | VI-1 | ANKRA2 | 2.06 |
| 270 | 3 | 4 | 5 | 6 | VI-1 | ANKRD10 | 2.39 |
| 271 | 3 | 4 | 5 | 6 | VI-1 | ANKRD11 | 2.39 |
| 272 | 3 | 4 | 5 | 6 | VI-1 | ANKRD12 | 4.49 |
| 273 | 3 | 4 | 5 | 6 | VI-1 | ANKRD13A | 2.58 |
| 274 | 3 | 4 | 5 | 6 | VI-1 | ANKRD13D | 2.62 |
| 275 | 3 | 4 | 5 | 6 | VI-1 | ANKRD17 | 2.28 |
| 276 | 3 | 4 | 5 | 6 | VI-1 | ANKRD26 | 2.86 |
| 277 | 3 | 4 | 5 | 6 | VI-1 | ANKRD28 | 2.82 |
| 278 | 3 | 4 | 5 | 6 | VI-1 | ANKRD32 | 3.27 |
| 279 | 3 | 4 | 5 | 6 | VI-1 | ANKRD34B | 2.35 |
| 280 | 3 | 4 | 5 | 6 | VI-1 | ANKRD44 | 2.75 |
| 281 | 3 | 4 | 5 | 6 | VI-1 | ANKRD49 | 2.01 |
| 282 | 3 | 4 | 5 | 6 | VI-1 | ANKRD5 | 2.00 |
| 283 | 3 | 4 | 5 | 6 | VI-1 | ANKRD52 | 2.29 |
| 284 | 3 | 4 | 5 | 6 | VI-1 | ANKS1A | 2.78 |
| 285 | 3 | 4 | 5 | 6 | VI-1 | ANKZF1 | 2.91 |
| 286 | 3 | 4 | 5 | 6 | VI-1 | ANO6 | 2.26 |
| 287 | 3 | 4 | 5 | 6 | VI-1 | ANO8 | 3.31 |
| 288 | 3 | 4 | 5 | 6 | VI-1 | ANTXR2 | 2.11 |
| 289 | 3 | 4 | 5 | 6 | VI-1 | ANXA5 | 2.25 |
| 290 | 3 | 4 | 5 | 6 | VI-1 | AP1AR | 2.22 |
| 291 | 3 | 4 | 5 | 6 | VI-1 | AP1G1 | 2.16 |
| 292 | 3 | 4 | 5 | 6 | VI-1 | AP1G2 | 4.83 |
| 293 | 3 | 4 | 5 | 6 | VI-1 | AP2A2 | 2.07 |
| 294 | 3 | 4 | 5 | 6 | VI-1 | AP3B1 | 2.16 |
| 295 | 3 | 4 | 5 | 6 | VI-1 | AP3M2 | 2.73 |
| 296 | 3 | 4 | 5 | 6 | VI-1 | AP4B1 | 2.78 |
| 297 | 3 | 4 | 5 | 6 | VI-1 | AP4E1 | 2.05 |
| 298 | 3 | 4 | 5 | 6 | VI-1 | AP5B1 | 2.84 |
| 299 | 3 | 4 | 5 | 6 | VI-1 | APAF1 | 2.63 |
| 300 | 3 | 4 | 5 | 6 | VI-1 | APBB1IP | 2.32 |
| 301 | 3 | 4 | 5 | 6 | VI-1 | APC | 2.23 |
| 302 | 3 | 4 | 5 | 6 | VI-1 | APH1B | 2.38 |
| 303 | 3 | 4 | 5 | 6 | VI-1 | APLP2 | 2.16 |
| 304 | 3 | 4 | 5 | 6 | VI-1 | APOBEC3D | 2.07 |
| 305 | 3 | 4 | 5 | 6 | VI-1 | APOBEC3F | 2.54 |
| 306 | 3 | 4 | 5 | 6 | VI-1 | APOBR | 3.34 |
| 307 | 3 | 4 | 5 | 6 | VI-1 | APOL1 | 4.61 |
| 308 | 3 | 4 | 5 | 6 | VI-1 | APOL2 | 4.48 |
| 309 | 3 | 4 | 5 | 6 | VI-1 | APOL3 | 2.21 |
| 310 | 3 | 4 | 5 | 6 | VI-1 | APOL4 | 4.29 |
| 311 | 3 | 4 | 5 | 6 | VI-1 | APOL6 | 4.62 |
| 312 | 3 | 4 | 5 | 6 | VI-1 | APPBP2 | 2.26 |
| 313 | 3 | 4 | 5 | 6 | VI-1 | ARAP1 | 3.06 |
| 314 | 3 | 4 | 5 | 6 | VI-1 | ARFGAP1 | 2.01 |
| 315 | 3 | 4 | 5 | 6 | VI-1 | ARFGEF2 | 2.37 |
| 316 | 3 | 4 | 5 | 6 | VI-1 | ARFIP1 | 2.50 |
| 317 | 3 | 4 | 5 | 6 | VI-1 | ARGLU1 | 3.18 |
| 318 | 3 | 4 | 5 | 6 | VI-1 | ARHGAP17 | 3.00 |
| 319 | 3 | 4 | 5 | 6 | VI-1 | ARHGAP22 | 2.14 |
| 320 | 3 | 4 | 5 | 6 | VI-1 | ARHGAP26 | 2.36 |
| 321 | 3 | 4 | 5 | 6 | VI-1 | ARHGAP27 | 2.79 |
| 322 | 3 | 4 | 5 | 6 | VI-1 | ARHGAP4 | 2.63 |
| 323 | 3 | 4 | 5 | 6 | VI-1 | ARHGAP9 | 2.31 |
| 324 | 3 | 4 | 5 | 6 | VI-1 | ARHGEF1 | 3.39 |
| 325 | 3 | 4 | 5 | 6 | VI-1 | ARHGEF11 | 3.46 |
| 326 | 3 | 4 | 5 | 6 | VI-1 | ARHGEF40 | 2.20 |
| 327 | 3 | 4 | 5 | 6 | VI-1 | ARHGEF7 | 2.68 |
| 328 | 3 | 4 | 5 | 6 | VI-1 | ARID1A | 2.42 |
| 329 | 3 | 4 | 5 | 6 | VI-1 | ARID4A | 2.84 |
| 330 | 3 | 4 | 5 | 6 | VI-1 | ARID4B | 2.94 |
| 331 | 3 | 4 | 5 | 6 | VI-1 | ARMC5 | 2.14 |
| 332 | 3 | 4 | 5 | 6 | VI-1 | ARMCX2 | 2.22 |
| 333 | 3 | 4 | 5 | 6 | VI-1 | ARMCX3 | 2.65 |
| 334 | 3 | 4 | 5 | 6 | VI-1 | ARNTL | 2.09 |
| 335 | 3 | 4 | 5 | 6 | VI-1 | ARSA | 3.77 |
| 336 | 3 | 4 | 5 | 6 | VI-1 | ARSB | 2.28 |
| 337 | 3 | 4 | 5 | 6 | VI-1 | ASAH1 | 2.40 |
| 338 | 3 | 4 | 5 | 6 | VI-1 | ASAP1 | 2.42 |
| 339 | 3 | 4 | 5 | 6 | VI-1 | ASAP2 | 3.16 |
| 340 | 3 | 4 | 5 | 6 | VI-1 | ASB16 | 3.83 |
| 341 | 3 | 4 | 5 | 6 | VI-1 | ASB3 | 2.63 |
| 342 | 3 | 4 | 5 | 6 | VI-1 | ASCC3 | 2.56 |
| 343 | 3 | 4 | 5 | 6 | VI-1 | ASL | 2.13 |
| 344 | 3 | 4 | 5 | 6 | VI-1 | ASNS | 3.78 |
| 345 | 3 | 4 | 5 | 6 | VI-1 | ASPHD2 | 2.36 |
| 346 | 3 | 4 | 5 | 6 | VI-1 | ASXL1 | 2.06 |
| 347 | 3 | 4 | 5 | 6 | VI-1 | ATAD2B | 2.52 |
| 348 | 3 | 4 | 5 | 6 | VI-1 | ATAD3B | 3.54 |
| 349 | 3 | 4 | 5 | 6 | VI-1 | ATF6B | 2.02 |
| 350 | 3 | 4 | 5 | 6 | VI-1 | ATF7 | 2.62 |
| 351 | 3 | 4 | 5 | 6 | VI-1 | ATF7IP | 2.54 |
| 352 | 3 | 4 | 5 | 6 | VI-1 | ATF7IP2 | 2.13 |
| 353 | 3 | 4 | 5 | 6 | VI-1 | ATG2A | 2.70 |
| 354 | 3 | 4 | 5 | 6 | VI-1 | ATG2B | 2.82 |
| 355 | 3 | 4 | 5 | 6 | VI-1 | ATG7 | 2.36 |
| 356 | 3 | 4 | 5 | 6 | VI-1 | ATL2 | 2.08 |
| 357 | 3 | 4 | 5 | 6 | VI-1 | ATM | 2.93 |
| 358 | 3 | 4 | 5 | 6 | VI-1 | ATN1 | 2.05 |
| 359 | 3 | 4 | 5 | 6 | VI-1 | ATP10D | 3.03 |
| 360 | 3 | 4 | 5 | 6 | VI-1 | ATP11A | 2.22 |
| 361 | 3 | 4 | 5 | 6 | VI-1 | ATP11C | 2.82 |
| 362 | 3 | 4 | 5 | 6 | VI-1 | ATP13A1 | 3.14 |
| 363 | 3 | 4 | 5 | 6 | VI-1 | ATP1A1 | 2.28 |
| 364 | 3 | 4 | 5 | 6 | VI-1 | ATP1B3 | 2.05 |
| 365 | 3 | 4 | 5 | 6 | VI-1 | ATP2A2 | 2.63 |
| 366 | 3 | 4 | 5 | 6 | VI-1 | ATP2B1 | 2.65 |
| 367 | 3 | 4 | 5 | 6 | VI-1 | ATP2C1 | 2.61 |
| 368 | 3 | 4 | 5 | 6 | VI-1 | ATP5J2-PTCD1 | 2.35 |
| 369 | 3 | 4 | 5 | 6 | VI-1 | ATP6V0A1 | 3.10 |
| 370 | 3 | 4 | 5 | 6 | VI-1 | ATP6V1B2 | 2.18 |
| 371 | 3 | 4 | 5 | 6 | VI-1 | ATP6V1C2 | 2.50 |
| 372 | 3 | 4 | 5 | 6 | VI-1 | ATP6V1D | 2.44 |
| 373 | 3 | 4 | 5 | 6 | VI-1 | ATP6V1G2-DDX39B | 2.23 |
| 374 | 3 | 4 | 5 | 6 | VI-1 | ATP7A | 2.26 |
| 375 | 3 | 4 | 5 | 6 | VI-1 | ATP8A1 | 3.10 |
| 376 | 3 | 4 | 5 | 6 | VI-1 | ATR | 2.76 |
| 377 | 3 | 4 | 5 | 6 | VI-1 | ATRX | 3.52 |
| 378 | 3 | 4 | 5 | 6 | VI-1 | ATXN2 | 3.03 |
| 379 | 3 | 4 | 5 | 6 | VI-1 | ATXN2L | 2.65 |
| 380 | 3 | 4 | 5 | 6 | VI-1 | ATXN7 | 3.21 |
| 381 | 3 | 4 | 5 | 6 | VI-1 | ATXN7L1 | 2.37 |

Fig. 40 - 3

| | | | | | | | | | | | | | | | |
|---|---|---|---|---|---|---|---|---|---|---|---|---|---|---|---|
| 382 | 3 | 4 | 5 | 6 | | VI-1 | ATXN7L2 | 2.09 | 478 | 3 | 4 | 5 | 6 | VI-1 | C2CD2L | 3.06 |
| 383 | 3 | 4 | 5 | 6 | | VI-1 | AZI1 | 2.31 | 479 | 3 | 4 | 5 | 6 | VI-1 | C2CD3 | 2.63 |
| 384 | 3 | 4 | 5 | 6 | | VI-1 | B3GNTL1 | 3.34 | 480 | 3 | 4 | 5 | 6 | VI-1 | C2orf29 | 2.31 |
| 385 | 3 | 4 | 5 | 6 | | VI-1 | BACE1-AS | 2.69 | 481 | 3 | 4 | 5 | 6 | VI-1 | C2orf56 | 2.07 |
| 386 | 3 | 4 | 5 | 6 | | VI-1 | BACH1 | 2.35 | 482 | 3 | 4 | 5 | 6 | VI-1 | C2orf89 | 2.11 |
| 387 | 3 | 4 | 5 | 6 | | VI-1 | BAIAP2 | 2.53 | 483 | 3 | 4 | 5 | 6 | VI-1 | C3orf62 | 3.51 |
| 388 | 3 | 4 | 5 | 6 | | VI-1 | BAX | 2.65 | 484 | 3 | 4 | 5 | 6 | VI-1 | C4orf32 | 2.69 |
| 389 | 3 | 4 | 5 | 6 | | VI-1 | BAZ1A | 3.55 | 485 | 3 | 4 | 5 | 6 | VI-1 | C4orf33 | 3.39 |
| 390 | 3 | 4 | 5 | 6 | | VI-1 | BAZ2A | 2.58 | 486 | 3 | 4 | 5 | 6 | VI-1 | C5orf41 | 2.72 |
| 391 | 3 | 4 | 5 | 6 | | VI-1 | BAZ2B | 3.07 | 487 | 3 | 4 | 5 | 6 | VI-1 | C5orf51 | 2.08 |
| 392 | 3 | 4 | 5 | 6 | | VI-1 | BBX | 2.48 | 488 | 3 | 4 | 5 | 6 | VI-1 | C5orf63 | 2.17 |
| 393 | 3 | 4 | 5 | 6 | | VI-1 | BCL2L2-PABPN1 | 3.10 | 489 | 3 | 4 | 5 | 6 | VI-1 | C6orf211 | 2.02 |
| 394 | 3 | 4 | 5 | 6 | | VI-1 | BCL9 | 2.13 | 490 | 3 | 4 | 5 | 6 | VI-1 | C6orf62 | 2.79 |
| 395 | 3 | 4 | 5 | 6 | | VI-1 | BCS1L | 2.89 | 491 | 3 | 4 | 5 | 6 | VI-1 | C6orf97 | 2.72 |
| 396 | 3 | 4 | 5 | 6 | | VI-1 | BDP1 | 2.03 | 492 | 3 | 4 | 5 | 6 | VI-1 | C7orf34 | 3.70 |
| 397 | 3 | 4 | 5 | 6 | | VI-1 | BIN3 | 2.30 | 493 | 3 | 4 | 5 | 6 | VI-1 | C7orf61 | 2.57 |
| 398 | 3 | 4 | 5 | 6 | | VI-1 | BIRC2 | 2.23 | 494 | 3 | 4 | 5 | 6 | VI-1 | C8orf44 | 3.37 |
| 399 | 3 | 4 | 5 | 6 | | VI-1 | BIRC6 | 2.80 | 495 | 3 | 4 | 5 | 6 | VI-1 | C8orf58 | 4.15 |
| 400 | 3 | 4 | 5 | 6 | | VI-1 | BLOC1S1-RDH5 | 3.81 | 496 | 3 | 4 | 5 | 6 | VI-1 | C8orf73 | 2.64 |
| 401 | 3 | 4 | 5 | 6 | | VI-1 | BLZF1 | 2.30 | 497 | 3 | 4 | 5 | 6 | VI-1 | C9orf114 | 2.27 |
| 402 | 3 | 4 | 5 | 6 | | VI-1 | BMPR2 | 2.12 | 498 | 3 | 4 | 5 | 6 | VI-1 | C9orf25 | 2.26 |
| 403 | 3 | 4 | 5 | 6 | | VI-1 | BNIP3 | 2.89 | 499 | 3 | 4 | 5 | 6 | VI-1 | C9orf37 | 2.37 |
| 404 | 3 | 4 | 5 | 6 | | VI-1 | BOD1L | 3.85 | 500 | 3 | 4 | 5 | 6 | VI-1 | C9orf66 | 2.50 |
| 405 | 3 | 4 | 5 | 6 | | VI-1 | BOP1 | 2.43 | 501 | 3 | 4 | 5 | 6 | VI-1 | C9orf72 | 2.95 |
| 406 | 3 | 4 | 5 | 6 | | VI-1 | BPTF | 2.46 | 502 | 3 | 4 | 5 | 6 | VI-1 | C9orf78 | 2.69 |
| 407 | 3 | 4 | 5 | 6 | | VI-1 | BRAT1 | 2.20 | 503 | 3 | 4 | 5 | 6 | VI-1 | C9orf91 | 4.54 |
| 408 | 3 | 4 | 5 | 6 | | VI-1 | BRCA1 | 4.11 | 504 | 3 | 4 | 5 | 6 | VI-1 | CACNA1I | 3.90 |
| 409 | 3 | 4 | 5 | 6 | | VI-1 | BRD4 | 2.09 | 505 | 3 | 4 | 5 | 6 | VI-1 | CACNB1 | 2.15 |
| 410 | 3 | 4 | 5 | 6 | | VI-1 | BROX | 2.09 | 506 | 3 | 4 | 5 | 6 | VI-1 | CACNB4 | 2.59 |
| 411 | 3 | 4 | 5 | 6 | | VI-1 | BST2 | 4.09 | 507 | 3 | 4 | 5 | 6 | VI-1 | CAD | 3.11 |
| 412 | 3 | 4 | 5 | 6 | | VI-1 | BTAF1 | 4.15 | 508 | 3 | 4 | 5 | 6 | VI-1 | CADM4 | 4.24 |
| 413 | 3 | 4 | 5 | 6 | | VI-1 | BTK | 2.36 | 509 | 3 | 4 | 5 | 6 | VI-1 | CAHM | 2.89 |
| 414 | 3 | 4 | 5 | 6 | | VI-1 | BTN2A1 | 2.97 | 510 | 3 | 4 | 5 | 6 | VI-1 | CALCOCO1 | 2.36 |
| 415 | 3 | 4 | 5 | 6 | | VI-1 | BTN2A2 | 4.14 | 511 | 3 | 4 | 5 | 6 | VI-1 | CALCOCO2 | 2.52 |
| 416 | 3 | 4 | 5 | 6 | | VI-1 | BTN2A3P | 2.26 | 512 | 3 | 4 | 5 | 6 | VI-1 | CALML4 | 2.87 |
| 417 | 3 | 4 | 5 | 6 | | VI-1 | BTN3A1 | 4.72 | 513 | 3 | 4 | 5 | 6 | VI-1 | CAMK2G | 2.05 |
| 418 | 3 | 4 | 5 | 6 | | VI-1 | BTN3A2 | 2.86 | 514 | 3 | 4 | 5 | 6 | VI-1 | CAPN10 | 2.96 |
| 419 | 3 | 4 | 5 | 6 | | VI-1 | BTN3A3 | 3.36 | 515 | 3 | 4 | 5 | 6 | VI-1 | CAPN2 | 2.35 |
| 420 | 3 | 4 | 5 | 6 | | VI-1 | C10orf137 | 2.79 | 516 | 3 | 4 | 5 | 6 | VI-1 | CARD16 | 2.19 |
| 421 | 3 | 4 | 5 | 6 | | VI-1 | C10orf47 | 2.49 | 517 | 3 | 4 | 5 | 6 | VI-1 | CARD6 | 2.24 |
| 422 | 3 | 4 | 5 | 6 | | VI-1 | C11orf30 | 2.43 | 518 | 3 | 4 | 5 | 6 | VI-1 | CARD8 | 3.42 |
| 423 | 3 | 4 | 5 | 6 | | VI-1 | C11orf61 | 2.99 | 519 | 3 | 4 | 5 | 6 | VI-1 | CARKD | 2.24 |
| 424 | 3 | 4 | 5 | 6 | | VI-1 | C11orf82 | 2.50 | 520 | 3 | 4 | 5 | 6 | VI-1 | CARS | 2.05 |
| 425 | 3 | 4 | 5 | 6 | | VI-1 | C12orf35 | 2.02 | 521 | 3 | 4 | 5 | 6 | VI-1 | CASP1 | 2.74 |
| 426 | 3 | 4 | 5 | 6 | | VI-1 | C12orf4 | 2.49 | 522 | 3 | 4 | 5 | 6 | VI-1 | CASP10 | 3.36 |
| 427 | 3 | 4 | 5 | 6 | | VI-1 | C12orf5 | 2.40 | 523 | 3 | 4 | 5 | 6 | VI-1 | CASP7 | 2.05 |
| 428 | 3 | 4 | 5 | 6 | | VI-1 | C12orf51 | 2.82 | 524 | 3 | 4 | 5 | 6 | VI-1 | CASP8 | 2.07 |
| 429 | 3 | 4 | 5 | 6 | | VI-1 | C12orf76 | 2.44 | 525 | 3 | 4 | 5 | 6 | VI-1 | CASP8AP2 | 2.15 |
| 430 | 3 | 4 | 5 | 6 | | VI-1 | C14orf101 | 2.52 | 526 | 3 | 4 | 5 | 6 | VI-1 | CASZ1 | 2.17 |
| 431 | 3 | 4 | 5 | 6 | | VI-1 | C14orf102 | 2.63 | 527 | 3 | 4 | 5 | 6 | VI-1 | CBFA2T2 | 2.17 |
| 432 | 3 | 4 | 5 | 6 | | VI-1 | C14orf149 | 3.87 | 528 | 3 | 4 | 5 | 6 | VI-1 | CBFA2T3 | 2.06 |
| 433 | 3 | 4 | 5 | 6 | | VI-1 | C14orf159 | 3.61 | 529 | 3 | 4 | 5 | 6 | VI-1 | CBL | 2.55 |
| 434 | 3 | 4 | 5 | 6 | | VI-1 | C14orf21 | 2.51 | 530 | 3 | 4 | 5 | 6 | VI-1 | CBLN3 | 3.47 |
| 435 | 3 | 4 | 5 | 6 | | VI-1 | C14orf28 | 2.13 | 531 | 3 | 4 | 5 | 6 | VI-1 | CC2D1A | 2.27 |
| 436 | 3 | 4 | 5 | 6 | | VI-1 | C14orf80 | 3.19 | 532 | 3 | 4 | 5 | 6 | VI-1 | CC2D1B | 2.29 |
| 437 | 3 | 4 | 5 | 6 | | VI-1 | C15orf17 | 2.44 | 533 | 3 | 4 | 5 | 6 | VI-1 | CCAR1 | 3.96 |
| 438 | 3 | 4 | 5 | 6 | | VI-1 | C15orf39 | 2.31 | 534 | 3 | 4 | 5 | 6 | VI-1 | CCBL1 | 2.46 |
| 439 | 3 | 4 | 5 | 6 | | VI-1 | C15orf62 | 2.55 | 535 | 3 | 4 | 5 | 6 | VI-1 | CCDC130 | 2.75 |
| 440 | 3 | 4 | 5 | 6 | | VI-1 | C15orf63 | 2.06 | 536 | 3 | 4 | 5 | 6 | VI-1 | CCDC14 | 4.07 |
| 441 | 3 | 4 | 5 | 6 | | VI-1 | C16orf48 | 3.10 | 537 | 3 | 4 | 5 | 6 | VI-1 | CCDC142 | 3.43 |
| 442 | 3 | 4 | 5 | 6 | | VI-1 | C16orf52 | 3.44 | 538 | 3 | 4 | 5 | 6 | VI-1 | CCDC149 | 2.50 |
| 443 | 3 | 4 | 5 | 6 | | VI-1 | C16orf70 | 2.69 | 539 | 3 | 4 | 5 | 6 | VI-1 | CCDC17 | 4.55 |
| 444 | 3 | 4 | 5 | 6 | | VI-1 | C16orf86 | 2.11 | 540 | 3 | 4 | 5 | 6 | VI-1 | CCDC18 | 2.15 |
| 445 | 3 | 4 | 5 | 6 | | VI-1 | C16orf88 | 2.05 | 541 | 3 | 4 | 5 | 6 | VI-1 | CCDC22 | 2.17 |
| 446 | 3 | 4 | 5 | 6 | | VI-1 | C17orf65 | 3.35 | 542 | 3 | 4 | 5 | 6 | VI-1 | CCDC61 | 2.09 |
| 447 | 3 | 4 | 5 | 6 | | VI-1 | C17orf70 | 2.07 | 543 | 3 | 4 | 5 | 6 | VI-1 | CCDC76 | 2.76 |
| 448 | 3 | 4 | 5 | 6 | | VI-1 | C17orf72 | 2.26 | 544 | 3 | 4 | 5 | 6 | VI-1 | CCDC77 | 2.24 |
| 449 | 3 | 4 | 5 | 6 | | VI-1 | C17orf85 | 2.04 | 545 | 3 | 4 | 5 | 6 | VI-1 | CCDC88B | 2.83 |
| 450 | 3 | 4 | 5 | 6 | | VI-1 | C18orf25 | 3.28 | 546 | 3 | 4 | 5 | 6 | VI-1 | CCDC88C | 2.09 |
| 451 | 3 | 4 | 5 | 6 | | VI-1 | C18orf8 | 2.13 | 547 | 3 | 4 | 5 | 6 | VI-1 | CCDC93 | 2.73 |
| 452 | 3 | 4 | 5 | 6 | | VI-1 | C19orf44 | 2.04 | 548 | 3 | 4 | 5 | 6 | VI-1 | CCDC97 | 2.04 |
| 453 | 3 | 4 | 5 | 6 | | VI-1 | C19orf54 | 3.02 | 549 | 3 | 4 | 5 | 6 | VI-1 | CCHCR1 | 2.71 |
| 454 | 3 | 4 | 5 | 6 | | VI-1 | C19orf55 | 2.22 | 550 | 3 | 4 | 5 | 6 | VI-1 | CCNA2 | 2.42 |
| 455 | 3 | 4 | 5 | 6 | | VI-1 | C19orf6 | 3.30 | 551 | 3 | 4 | 5 | 6 | VI-1 | CCND2 | 2.01 |
| 456 | 3 | 4 | 5 | 6 | | VI-1 | C19orf66 | 4.32 | 552 | 3 | 4 | 5 | 6 | VI-1 | CCNJ | 2.39 |
| 457 | 3 | 4 | 5 | 6 | | VI-1 | C1GALT1 | 2.69 | 553 | 3 | 4 | 5 | 6 | VI-1 | CCNK | 2.28 |
| 458 | 3 | 4 | 5 | 6 | | VI-1 | C1QA | 2.16 | 554 | 3 | 4 | 5 | 6 | VI-1 | CCNL1 | 3.95 |
| 459 | 3 | 4 | 5 | 6 | | VI-1 | C1QTNF6 | 2.98 | 555 | 3 | 4 | 5 | 6 | VI-1 | CCNT2 | 2.19 |
| 460 | 3 | 4 | 5 | 6 | | VI-1 | C1R | 2.10 | 556 | 3 | 4 | 5 | 6 | VI-1 | CCR1 | 3.66 |
| 461 | 3 | 4 | 5 | 6 | | VI-1 | C1orf115 | 2.49 | 557 | 3 | 4 | 5 | 6 | VI-1 | CCR10 | 2.31 |
| 462 | 3 | 4 | 5 | 6 | | VI-1 | C1orf150 | 2.88 | 558 | 3 | 4 | 5 | 6 | VI-1 | CCR9 | 2.62 |
| 463 | 3 | 4 | 5 | 6 | | VI-1 | C1orf159 | 2.20 | 559 | 3 | 4 | 5 | 6 | VI-1 | CCRL2 | 2.82 |
| 464 | 3 | 4 | 5 | 6 | | VI-1 | C1orf162 | 2.55 | 560 | 3 | 4 | 5 | 6 | VI-1 | CCRN4L | 2.36 |
| 465 | 3 | 4 | 5 | 6 | | VI-1 | C1orf186 | 2.00 | 561 | 3 | 4 | 5 | 6 | VI-1 | CCT6P1 | 3.59 |
| 466 | 3 | 4 | 5 | 6 | | VI-1 | C1orf201 | 3.64 | 562 | 3 | 4 | 5 | 6 | VI-1 | CCT8 | 2.05 |
| 467 | 3 | 4 | 5 | 6 | | VI-1 | C1orf220 | 2.24 | 563 | 3 | 4 | 5 | 6 | VI-1 | CD2AP | 2.28 |
| 468 | 3 | 4 | 5 | 6 | | VI-1 | C1orf27 | 2.49 | 564 | 3 | 4 | 5 | 6 | VI-1 | CD300LF | 2.61 |
| 469 | 3 | 4 | 5 | 6 | | VI-1 | C1orf56 | 2.06 | 565 | 3 | 4 | 5 | 6 | VI-1 | CD37 | 2.03 |
| 470 | 3 | 4 | 5 | 6 | | VI-1 | C1orf9 | 2.20 | 566 | 3 | 4 | 5 | 6 | VI-1 | CD38 | 3.58 |
| 471 | 3 | 4 | 5 | 6 | | VI-1 | C1orf96 | 2.69 | 567 | 3 | 4 | 5 | 6 | VI-1 | CD46 | 3.04 |
| 472 | 3 | 4 | 5 | 6 | | VI-1 | C20orf112 | 2.45 | 568 | 3 | 4 | 5 | 6 | VI-1 | CD53 | 2.28 |
| 473 | 3 | 4 | 5 | 6 | | VI-1 | C20orf194 | 2.72 | 569 | 3 | 4 | 5 | 6 | VI-1 | CD83 | 3.25 |
| 474 | 3 | 4 | 5 | 6 | | VI-1 | C21orf15 | 2.89 | 570 | 3 | 4 | 5 | 6 | VI-1 | CD97 | 2.83 |
| 475 | 3 | 4 | 5 | 6 | | VI-1 | C21orf58 | 2.35 | 571 | 3 | 4 | 5 | 6 | VI-1 | CDAN1 | 2.78 |
| 476 | 3 | 4 | 5 | 6 | | VI-1 | C22orf23 | 4.06 | 572 | 3 | 4 | 5 | 6 | VI-1 | CDC16 | 2.51 |
| 477 | 3 | 4 | 5 | 6 | | VI-1 | C2CD2 | 2.92 | 573 | 3 | 4 | 5 | 6 | VI-1 | CDC42EP2 | 2.04 |

Fig. 40 - 4

| | | | | | | | | | | | | | | | |
|---|---|---|---|---|---|---|---|---|---|---|---|---|---|---|---|
| 574 | 3 | 4 | 5 | 6 | | VI-1 | CDC42EP4 | 2.01 | 670 | 3 | 4 | 5 | 6 | VI-1 | COPA | 2.39 |
| 575 | 3 | 4 | 5 | 6 | | VI-1 | CDC7 | 2.62 | 671 | 3 | 4 | 5 | 6 | VI-1 | COPG1 | 2.55 |
| 576 | 3 | 4 | 5 | 6 | | VI-1 | CDH23 | 4.85 | 672 | 3 | 4 | 5 | 6 | VI-1 | COQ10A | 2.79 |
| 577 | 3 | 4 | 5 | 6 | | VI-1 | CDK11A | 3.47 | 673 | 3 | 4 | 5 | 6 | VI-1 | COQ6 | 2.01 |
| 578 | 3 | 4 | 5 | 6 | | VI-1 | CDK11B | 2.53 | 674 | 3 | 4 | 5 | 6 | VI-1 | CORO1B | 2.15 |
| 579 | 3 | 4 | 5 | 6 | | VI-1 | CDK14 | 2.17 | 675 | 3 | 4 | 5 | 6 | VI-1 | CORO2A | 2.22 |
| 580 | 3 | 4 | 5 | 6 | | VI-1 | CDK16 | 2.22 | 676 | 3 | 4 | 5 | 6 | VI-1 | CORO7 | 2.17 |
| 581 | 3 | 4 | 5 | 6 | | VI-1 | CDK17 | 2.83 | 677 | 3 | 4 | 5 | 6 | VI-1 | COX19 | 2.18 |
| 582 | 3 | 4 | 5 | 6 | | VI-1 | CDK19 | 2.09 | 678 | 3 | 4 | 5 | 6 | VI-1 | CPEB2 | 3.76 |
| 583 | 3 | 4 | 5 | 6 | | VI-1 | CDK2 | 2.23 | 679 | 3 | 4 | 5 | 6 | VI-1 | CPEB3 | 3.23 |
| 584 | 3 | 4 | 5 | 6 | | VI-1 | CDK3 | 3.22 | 680 | 3 | 4 | 5 | 6 | VI-1 | CPOX | 2.54 |
| 585 | 3 | 4 | 5 | 6 | | VI-1 | CDK5RAP1 | 2.01 | 681 | 3 | 4 | 5 | 6 | VI-1 | CPSF1 | 2.30 |
| 586 | 3 | 4 | 5 | 6 | | VI-1 | CDK5RAP2 | 2.24 | 682 | 3 | 4 | 5 | 6 | VI-1 | CPSF3L | 2.05 |
| 587 | 3 | 4 | 5 | 6 | | VI-1 | CECR6 | 4.35 | 683 | 3 | 4 | 5 | 6 | VI-1 | CPSF6 | 3.15 |
| 588 | 3 | 4 | 5 | 6 | | VI-1 | CELF1 | 3.05 | 684 | 3 | 4 | 5 | 6 | VI-1 | CPSF7 | 2.38 |
| 589 | 3 | 4 | 5 | 6 | | VI-1 | CELF2 | 2.91 | 685 | 3 | 4 | 5 | 6 | VI-1 | CPT2 | 2.14 |
| 590 | 3 | 4 | 5 | 6 | | VI-1 | CELF6 | 2.68 | 686 | 3 | 4 | 5 | 6 | VI-1 | CRAMP1L | 2.42 |
| 591 | 3 | 4 | 5 | 6 | | VI-1 | CEMP1 | 3.15 | 687 | 3 | 4 | 5 | 6 | VI-1 | CREB1 | 2.15 |
| 592 | 3 | 4 | 5 | 6 | | VI-1 | CEP135 | 2.90 | 688 | 3 | 4 | 5 | 6 | VI-1 | CREB8P | 2.10 |
| 593 | 3 | 4 | 5 | 6 | | VI-1 | CEP152 | 2.49 | 689 | 3 | 4 | 5 | 6 | VI-1 | CREBZF | 3.62 |
| 594 | 3 | 4 | 5 | 6 | | VI-1 | CEP164 | 2.89 | 690 | 3 | 4 | 5 | 6 | VI-1 | CRELD1 | 2.30 |
| 595 | 3 | 4 | 5 | 6 | | VI-1 | CEP170 | 2.04 | 691 | 3 | 4 | 5 | 6 | VI-1 | CROCC | 4.09 |
| 596 | 3 | 4 | 5 | 6 | | VI-1 | CEP192 | 2.16 | 692 | 3 | 4 | 5 | 6 | VI-1 | CROCCP3 | 2.74 |
| 597 | 3 | 4 | 5 | 6 | | VI-1 | CEP350 | 2.28 | 693 | 3 | 4 | 5 | 6 | VI-1 | CROT | 2.04 |
| 598 | 3 | 4 | 5 | 6 | | VI-1 | CEP44 | 2.75 | 694 | 3 | 4 | 5 | 6 | VI-1 | CRTC1 | 2.43 |
| 599 | 3 | 4 | 5 | 6 | | VI-1 | CEP63 | 2.76 | 695 | 3 | 4 | 5 | 6 | VI-1 | CRYZL1 | 2.43 |
| 600 | 3 | 4 | 5 | 6 | | VI-1 | CEP85 | 2.21 | 696 | 3 | 4 | 5 | 6 | VI-1 | CSF1R | 2.35 |
| 601 | 3 | 4 | 5 | 6 | | VI-1 | CEP95 | 2.34 | 697 | 3 | 4 | 5 | 6 | VI-1 | CSF2RB | 2.20 |
| 602 | 3 | 4 | 5 | 6 | | VI-1 | CEP97 | 2.02 | 698 | 3 | 4 | 5 | 6 | VI-1 | CSF3R | 2.36 |
| 603 | 3 | 4 | 5 | 6 | | VI-1 | CERK1 | 2.37 | 699 | 3 | 4 | 5 | 6 | VI-1 | CSPP1 | 3.53 |
| 604 | 3 | 4 | 5 | 6 | | VI-1 | CERS6 | 2.02 | 700 | 3 | 4 | 5 | 6 | VI-1 | CSTF3 | 2.68 |
| 605 | 3 | 4 | 5 | 6 | | VI-1 | CES4A | 2.86 | 701 | 3 | 4 | 5 | 6 | VI-1 | CTAGE10P | 2.27 |
| 606 | 3 | 4 | 5 | 6 | | VI-1 | CFL2 | 2.04 | 702 | 3 | 4 | 5 | 6 | VI-1 | CT8S | 2.18 |
| 607 | 3 | 4 | 5 | 6 | | VI-1 | CFLAR | 2.03 | 703 | 3 | 4 | 5 | 6 | VI-1 | CTC1 | 2.38 |
| 608 | 3 | 4 | 5 | 6 | | VI-1 | CG030 | 4.90 | 704 | 3 | 4 | 5 | 6 | VI-1 | CTIF | 2.06 |
| 609 | 3 | 4 | 5 | 6 | | VI-1 | CGGBP1 | 2.23 | 705 | 3 | 4 | 5 | 6 | VI-1 | CTLA4 | 2.52 |
| 610 | 3 | 4 | 5 | 6 | | VI-1 | CHAD | 2.05 | 706 | 3 | 4 | 5 | 6 | VI-1 | CTNNA1 | 2.64 |
| 611 | 3 | 4 | 5 | 6 | | VI-1 | CHAF1A | 2.03 | 707 | 3 | 4 | 5 | 6 | VI-1 | CTNNB1 | 3.01 |
| 612 | 3 | 4 | 5 | 6 | | VI-1 | CHD1 | 2.88 | 708 | 3 | 4 | 5 | 6 | VI-1 | CTNS | 2.13 |
| 613 | 3 | 4 | 5 | 6 | | VI-1 | CHD2 | 3.00 | 709 | 3 | 4 | 5 | 6 | VI-1 | CTPS | 2.11 |
| 614 | 3 | 4 | 5 | 6 | | VI-1 | CHD3 | 2.23 | 710 | 3 | 4 | 5 | 6 | VI-1 | CTSK | 2.80 |
| 615 | 3 | 4 | 5 | 6 | | VI-1 | CHD4 | 2.39 | 711 | 3 | 4 | 5 | 6 | VI-1 | CTSL1 | 4.81 |
| 616 | 3 | 4 | 5 | 6 | | VI-1 | CHD6 | 2.12 | 712 | 3 | 4 | 5 | 6 | VI-1 | CTSZ | 2.29 |
| 617 | 3 | 4 | 5 | 6 | | VI-1 | CHD7 | 2.87 | 713 | 3 | 4 | 5 | 6 | VI-1 | CUL1 | 3.06 |
| 618 | 3 | 4 | 5 | 6 | | VI-1 | CHD8 | 2.17 | 714 | 3 | 4 | 5 | 6 | VI-1 | CUL7 | 2.73 |
| 619 | 3 | 4 | 5 | 6 | | VI-1 | CHERP | 2.14 | 715 | 3 | 4 | 5 | 6 | VI-1 | CUL9 | 3.21 |
| 620 | 3 | 4 | 5 | 6 | | VI-1 | CHFR | 2.05 | 716 | 3 | 4 | 5 | 6 | VI-1 | CWC25 | 3.11 |
| 621 | 3 | 4 | 5 | 6 | | VI-1 | CHORDC1 | 2.30 | 717 | 3 | 4 | 5 | 6 | VI-1 | CWF19L2 | 2.88 |
| 622 | 3 | 4 | 5 | 6 | | VI-1 | CHPF2 | 2.13 | 718 | 3 | 4 | 5 | 6 | VI-1 | CXCL16 | 2.18 |
| 623 | 3 | 4 | 5 | 6 | | VI-1 | CHRNA10 | 2.36 | 719 | 3 | 4 | 5 | 6 | VI-1 | CXXC1 | 2.28 |
| 624 | 3 | 4 | 5 | 6 | | VI-1 | CHST15 | 2.27 | 720 | 3 | 4 | 5 | 6 | VI-1 | CXorf21 | 2.76 |
| 625 | 3 | 4 | 5 | 6 | | VI-1 | CHTF18 | 2.05 | 721 | 3 | 4 | 5 | 6 | VI-1 | CXorf23 | 3.56 |
| 626 | 3 | 4 | 5 | 6 | | VI-1 | CIR1 | 2.88 | 722 | 3 | 4 | 5 | 6 | VI-1 | CXorf65 | 3.76 |
| 627 | 3 | 4 | 5 | 6 | | VI-1 | CIRBP | 2.71 | 723 | 3 | 4 | 5 | 6 | VI-1 | CYB561 | 2.57 |
| 628 | 3 | 4 | 5 | 6 | | VI-1 | CIRBP-AS1 | 2.09 | 724 | 3 | 4 | 5 | 6 | VI-1 | CYP1B1-AS1 | 2.22 |
| 629 | 3 | 4 | 5 | 6 | | VI-1 | CLASP1 | 2.21 | 725 | 3 | 4 | 5 | 6 | VI-1 | CYP2D7P1 | 2.52 |
| 630 | 3 | 4 | 5 | 6 | | VI-1 | CLASP2 | 2.14 | 726 | 3 | 4 | 5 | 6 | VI-1 | CYP4F2 | 2.91 |
| 631 | 3 | 4 | 5 | 6 | | VI-1 | CLASRP | 2.58 | 727 | 3 | 4 | 5 | 6 | VI-1 | CYTH1 | 2.54 |
| 632 | 3 | 4 | 5 | 6 | | VI-1 | CLCC1 | 2.13 | 728 | 3 | 4 | 5 | 6 | VI-1 | D2HGDH | 4.69 |
| 633 | 3 | 4 | 5 | 6 | | VI-1 | CLCN5 | 2.57 | 729 | 3 | 4 | 5 | 6 | VI-1 | DAAM1 | 2.15 |
| 634 | 3 | 4 | 5 | 6 | | VI-1 | CLCN6 | 3.94 | 730 | 3 | 4 | 5 | 6 | VI-1 | DAB2 | 3.51 |
| 635 | 3 | 4 | 5 | 6 | | VI-1 | CLCN7 | 4.13 | 731 | 3 | 4 | 5 | 6 | VI-1 | DACT1 | 2.65 |
| 636 | 3 | 4 | 5 | 6 | | VI-1 | CLDN15 | 3.71 | 732 | 3 | 4 | 5 | 6 | VI-1 | DAGLB | 2.57 |
| 637 | 3 | 4 | 5 | 6 | | VI-1 | CLDN23 | 2.61 | 733 | 3 | 4 | 5 | 6 | VI-1 | DAPP1 | 3.26 |
| 638 | 3 | 4 | 5 | 6 | | VI-1 | CLDN7 | 2.63 | 734 | 3 | 4 | 5 | 6 | VI-1 | DAZAP1 | 2.35 |
| 639 | 3 | 4 | 5 | 6 | | VI-1 | CLEC16A | 2.09 | 735 | 3 | 4 | 5 | 6 | VI-1 | DBF4B | 4.37 |
| 640 | 3 | 4 | 5 | 6 | | VI-1 | CLEC18A | 2.29 | 736 | 3 | 4 | 5 | 6 | VI-1 | DBN1 | 3.27 |
| 641 | 3 | 4 | 5 | 6 | | VI-1 | CLEC1A | 3.66 | 737 | 3 | 4 | 5 | 6 | VI-1 | DCAF10 | 2.40 |
| 642 | 3 | 4 | 5 | 6 | | VI-1 | CLEC2B | 2.41 | 738 | 3 | 4 | 5 | 6 | VI-1 | DCAF11 | 2.14 |
| 643 | 3 | 4 | 5 | 6 | | VI-1 | CLEC4A | 2.04 | 739 | 3 | 4 | 5 | 6 | VI-1 | DCAF15 | 2.29 |
| 644 | 3 | 4 | 5 | 6 | | VI-1 | CLEC7A | 3.80 | 740 | 3 | 4 | 5 | 6 | VI-1 | DCHS1 | 3.04 |
| 645 | 3 | 4 | 5 | 6 | | VI-1 | CLIC4 | 2.39 | 741 | 3 | 4 | 5 | 6 | VI-1 | DCLRE1C | 2.35 |
| 646 | 3 | 4 | 5 | 6 | | VI-1 | CLIP4 | 3.22 | 742 | 3 | 4 | 5 | 6 | VI-1 | DCP1A | 2.24 |
| 647 | 3 | 4 | 5 | 6 | | VI-1 | CLK2 | 2.88 | 743 | 3 | 4 | 5 | 6 | VI-1 | DCP2 | 2.37 |
| 648 | 3 | 4 | 5 | 6 | | VI-1 | CLK2P | 2.67 | 744 | 3 | 4 | 5 | 6 | VI-1 | DCUN1D3 | 2.39 |
| 649 | 3 | 4 | 5 | 6 | | VI-1 | CLN3 | 2.63 | 745 | 3 | 4 | 5 | 6 | VI-1 | DDAH2 | 2.08 |
| 650 | 3 | 4 | 5 | 6 | | VI-1 | CLN8 | 2.49 | 746 | 3 | 4 | 5 | 6 | VI-1 | DDB2 | 3.08 |
| 651 | 3 | 4 | 5 | 6 | | VI-1 | CLSTN1 | 2.07 | 747 | 3 | 4 | 5 | 6 | VI-1 | DDHD1 | 3.31 |
| 652 | 3 | 4 | 5 | 6 | | VI-1 | CLTC | 2.64 | 748 | 3 | 4 | 5 | 6 | VI-1 | DDIT3 | 2.64 |
| 653 | 3 | 4 | 5 | 6 | | VI-1 | CMC2 | 2.02 | 749 | 3 | 4 | 5 | 6 | VI-1 | DDR1 | 2.07 |
| 654 | 3 | 4 | 5 | 6 | | VI-1 | CMIP | 2.52 | 750 | 3 | 4 | 5 | 6 | VI-1 | DDX12P | 2.52 |
| 655 | 3 | 4 | 5 | 6 | | VI-1 | CMTM4 | 2.06 | 751 | 3 | 4 | 5 | 6 | VI-1 | DDX17 | 3.48 |
| 656 | 3 | 4 | 5 | 6 | | VI-1 | CNDP2 | 2.54 | 752 | 3 | 4 | 5 | 6 | VI-1 | DDX26B | 4.82 |
| 657 | 3 | 4 | 5 | 6 | | VI-1 | CNOT1 | 2.06 | 753 | 3 | 4 | 5 | 6 | VI-1 | DDX27 | 2.06 |
| 658 | 3 | 4 | 5 | 6 | | VI-1 | CNP | 2.52 | 754 | 3 | 4 | 5 | 6 | VI-1 | DDX31 | 2.26 |
| 659 | 3 | 4 | 5 | 6 | | VI-1 | CNST | 2.41 | 755 | 3 | 4 | 5 | 6 | VI-1 | DDX39A | 2.27 |
| 660 | 3 | 4 | 5 | 6 | | VI-1 | CNTD1 | 4.39 | 756 | 3 | 4 | 5 | 6 | VI-1 | DDX39B | 3.41 |
| 661 | 3 | 4 | 5 | 6 | | VI-1 | CNTRL | 3.07 | 757 | 3 | 4 | 5 | 6 | VI-1 | DDX3X | 2.26 |
| 662 | 3 | 4 | 5 | 6 | | VI-1 | CNTROB | 2.16 | 758 | 3 | 4 | 5 | 6 | VI-1 | DDX5 | 3.05 |
| 663 | 3 | 4 | 5 | 6 | | VI-1 | COG1 | 2.41 | 759 | 3 | 4 | 5 | 6 | VI-1 | DDX51 | 2.46 |
| 664 | 3 | 4 | 5 | 6 | | VI-1 | COG3 | 2.57 | 760 | 3 | 4 | 5 | 6 | VI-1 | DDX52 | 2.10 |
| 665 | 3 | 4 | 5 | 6 | | VI-1 | COG4 | 2.74 | 761 | 3 | 4 | 5 | 6 | VI-1 | DDX55 | 2.97 |
| 666 | 3 | 4 | 5 | 6 | | VI-1 | COG7 | 2.23 | 762 | 3 | 4 | 5 | 6 | VI-1 | DDX56 | 3.21 |
| 667 | 3 | 4 | 5 | 6 | | VI-1 | COL4A3BP | 2.20 | 763 | 3 | 4 | 5 | 6 | VI-1 | DECR1 | 2.88 |
| 668 | 3 | 4 | 5 | 6 | | VI-1 | COL8A2 | 2.03 | 764 | 3 | 4 | 5 | 6 | VI-1 | DEK | 2.23 |
| 669 | 3 | 4 | 5 | 6 | | VI-1 | COMMD3 | 2.16 | 765 | 3 | 4 | 5 | 6 | VI-1 | DENND1A | 3.40 |

Fig. 40 - 5

| | | | | | | | |
|---|---|---|---|---|---|---|---|
| 766 | 3 | 4 | 5 | 6 | VI-1 | DENND1C | 2.09 |
| 767 | 3 | 4 | 5 | 6 | VI-1 | DENND4B | 3.32 |
| 768 | 3 | 4 | 5 | 6 | VI-1 | DENND4C | 2.21 |
| 769 | 3 | 4 | 5 | 6 | VI-1 | DENND5A | 2.15 |
| 770 | 3 | 4 | 5 | 6 | VI-1 | DERL3 | 2.42 |
| 771 | 3 | 4 | 5 | 6 | VI-1 | DET1 | 2.02 |
| 772 | 3 | 4 | 5 | 6 | VI-1 | DFFB | 2.11 |
| 773 | 3 | 4 | 5 | 6 | VI-1 | DGAT1 | 2.40 |
| 774 | 3 | 4 | 5 | 6 | VI-1 | DGCR8 | 2.26 |
| 775 | 3 | 4 | 5 | 6 | VI-1 | DGKA | 3.13 |
| 776 | 3 | 4 | 5 | 6 | VI-1 | DGKD | 2.17 |
| 777 | 3 | 4 | 5 | 6 | VI-1 | DGKE | 2.16 |
| 778 | 3 | 4 | 5 | 6 | VI-1 | DGKQ | 2.30 |
| 779 | 3 | 4 | 5 | 6 | VI-1 | DHFR | 2.18 |
| 780 | 3 | 4 | 5 | 6 | VI-1 | DHFRL1 | 2.01 |
| 781 | 3 | 4 | 5 | 6 | VI-1 | DHPS | 2.17 |
| 782 | 3 | 4 | 5 | 6 | VI-1 | DHRS1 | 3.45 |
| 783 | 3 | 4 | 5 | 6 | VI-1 | DHTKD1 | 2.00 |
| 784 | 3 | 4 | 5 | 6 | VI-1 | DHX16 | 2.07 |
| 785 | 3 | 4 | 5 | 6 | VI-1 | DHX29 | 2.10 |
| 786 | 3 | 4 | 5 | 6 | VI-1 | DHX33 | 2.19 |
| 787 | 3 | 4 | 5 | 6 | VI-1 | DHX34 | 3.41 |
| 788 | 3 | 4 | 5 | 6 | VI-1 | DHX36 | 2.19 |
| 789 | 3 | 4 | 5 | 6 | VI-1 | DHX37 | 2.38 |
| 790 | 3 | 4 | 5 | 6 | VI-1 | DHX38 | 2.43 |
| 791 | 3 | 4 | 5 | 6 | VI-1 | DICER1 | 3.37 |
| 792 | 3 | 4 | 5 | 6 | VI-1 | DICER1-AS1 | 2.43 |
| 793 | 3 | 4 | 5 | 6 | VI-1 | DIDO1 | 2.27 |
| 794 | 3 | 4 | 5 | 6 | VI-1 | DIP2A | 3.13 |
| 795 | 3 | 4 | 5 | 6 | VI-1 | DIP2B | 2.62 |
| 796 | 3 | 4 | 5 | 6 | VI-1 | DIS3L2 | 2.13 |
| 797 | 3 | 4 | 5 | 6 | VI-1 | DISC1 | 2.47 |
| 798 | 3 | 4 | 5 | 6 | VI-1 | DKFZP434I0714 | 3.49 |
| 799 | 3 | 4 | 5 | 6 | VI-1 | DKFZP586I1420 | 2.02 |
| 800 | 3 | 4 | 5 | 6 | VI-1 | DLEU2 | 3.09 |
| 801 | 3 | 4 | 5 | 6 | VI-1 | DLEU2L | 2.01 |
| 802 | 3 | 4 | 5 | 6 | VI-1 | DLG1 | 2.14 |
| 803 | 3 | 4 | 5 | 6 | VI-1 | DMTF1 | 3.15 |
| 804 | 3 | 4 | 5 | 6 | VI-1 | DMWD | 2.03 |
| 805 | 3 | 4 | 5 | 6 | VI-1 | DNAH1 | 3.90 |
| 806 | 3 | 4 | 5 | 6 | VI-1 | DNAJA1 | 2.01 |
| 807 | 3 | 4 | 5 | 6 | VI-1 | DNAJC11 | 2.35 |
| 808 | 3 | 4 | 5 | 6 | VI-1 | DNAJC13 | 3.09 |
| 809 | 3 | 4 | 5 | 6 | VI-1 | DNAJC2 | 3.83 |
| 810 | 3 | 4 | 5 | 6 | VI-1 | DNAJC7 | 2.06 |
| 811 | 3 | 4 | 5 | 6 | VI-1 | DNASE1 | 3.59 |
| 812 | 3 | 4 | 5 | 6 | VI-1 | DNHD1 | 3.06 |
| 813 | 3 | 4 | 5 | 6 | VI-1 | DNM3 | 2.69 |
| 814 | 3 | 4 | 5 | 6 | VI-1 | DNMBP | 2.15 |
| 815 | 3 | 4 | 5 | 6 | VI-1 | DNMT3A | 2.06 |
| 816 | 3 | 4 | 5 | 6 | VI-1 | DNPEP | 2.37 |
| 817 | 3 | 4 | 5 | 6 | VI-1 | DOCK11 | 2.01 |
| 818 | 3 | 4 | 5 | 6 | VI-1 | DOCK2 | 2.36 |
| 819 | 3 | 4 | 5 | 6 | VI-1 | DOCK5 | 2.99 |
| 820 | 3 | 4 | 5 | 6 | VI-1 | DOCK8 | 2.75 |
| 821 | 3 | 4 | 5 | 6 | VI-1 | DONSON | 2.58 |
| 822 | 3 | 4 | 5 | 6 | VI-1 | DOT1L | 2.94 |
| 823 | 3 | 4 | 5 | 6 | VI-1 | DPAGT1 | 2.04 |
| 824 | 3 | 4 | 5 | 6 | VI-1 | DPY19L3 | 2.08 |
| 825 | 3 | 4 | 5 | 6 | VI-1 | DSN1 | 2.32 |
| 826 | 3 | 4 | 5 | 6 | VI-1 | DSTYK | 2.17 |
| 827 | 3 | 4 | 5 | 6 | VI-1 | DTNB | 2.09 |
| 828 | 3 | 4 | 5 | 6 | VI-1 | DTWD1 | 2.14 |
| 829 | 3 | 4 | 5 | 6 | VI-1 | DTX2P1-UPK3BP1-PMS2P11 | 2.75 |
| 830 | 3 | 4 | 5 | 6 | VI-1 | DTX3 | 2.20 |
| 831 | 3 | 4 | 5 | 6 | VI-1 | DTX3L | 4.34 |
| 832 | 3 | 4 | 5 | 6 | VI-1 | DUSP18 | 3.94 |
| 833 | 3 | 4 | 5 | 6 | VI-1 | DUSP3 | 2.23 |
| 834 | 3 | 4 | 5 | 6 | VI-1 | DUSP6 | 2.81 |
| 835 | 3 | 4 | 5 | 6 | VI-1 | DVL2 | 2.19 |
| 836 | 3 | 4 | 5 | 6 | VI-1 | DVL3 | 2.31 |
| 837 | 3 | 4 | 5 | 6 | VI-1 | DYNC1H1 | 3.37 |
| 838 | 3 | 4 | 5 | 6 | VI-1 | DYNC1LI1 | 2.09 |
| 839 | 3 | 4 | 5 | 6 | VI-1 | DYNC1LI2 | 2.81 |
| 840 | 3 | 4 | 5 | 6 | VI-1 | DYRK1A | 2.01 |
| 841 | 3 | 4 | 5 | 6 | VI-1 | E2F1 | 2.51 |
| 842 | 3 | 4 | 5 | 6 | VI-1 | EAF2 | 2.02 |
| 843 | 3 | 4 | 5 | 6 | VI-1 | EBLN2 | 2.20 |
| 844 | 3 | 4 | 5 | 6 | VI-1 | ECE1 | 2.81 |
| 845 | 3 | 4 | 5 | 6 | VI-1 | EDC4 | 2.53 |
| 846 | 3 | 4 | 5 | 6 | VI-1 | EDEM3 | 2.54 |
| 847 | 3 | 4 | 5 | 6 | VI-1 | EFCAB2 | 2.19 |
| 848 | 3 | 4 | 5 | 6 | VI-1 | EFEMP2 | 2.68 |
| 849 | 3 | 4 | 5 | 6 | VI-1 | EFHC1 | 2.36 |
| 850 | 3 | 4 | 5 | 6 | VI-1 | EFR3A | 2.27 |
| 851 | 3 | 4 | 5 | 6 | VI-1 | EGFL7 | 2.40 |
| 852 | 3 | 4 | 5 | 6 | VI-1 | EGLN3 | 2.29 |
| 853 | 3 | 4 | 5 | 6 | VI-1 | EGR2 | 2.05 |
| 854 | 3 | 4 | 5 | 6 | VI-1 | EID2B | 2.42 |
| 855 | 3 | 4 | 5 | 6 | VI-1 | EIF2B4 | 2.47 |
| 856 | 3 | 4 | 5 | 6 | VI-1 | EIF2B5 | 2.37 |
| 857 | 3 | 4 | 5 | 6 | VI-1 | EIF2C3 | 2.18 |
| 858 | 3 | 4 | 5 | 6 | VI-1 | EIF4G1 | 2.19 |
| 859 | 3 | 4 | 5 | 6 | VI-1 | EIF4G3 | 3.56 |
| 860 | 3 | 4 | 5 | 6 | VI-1 | EIF5B | 2.76 |
| 861 | 3 | 4 | 5 | 6 | VI-1 | ELF1 | 2.20 |
| 862 | 3 | 4 | 5 | 6 | VI-1 | ELF2 | 2.02 |
| 863 | 3 | 4 | 5 | 6 | VI-1 | ELF4 | 2.14 |
| 864 | 3 | 4 | 5 | 6 | VI-1 | ELL | 2.16 |
| 865 | 3 | 4 | 5 | 6 | VI-1 | ELMOD3 | 3.25 |
| 866 | 3 | 4 | 5 | 6 | VI-1 | ELP2 | 2.11 |
| 867 | 3 | 4 | 5 | 6 | VI-1 | EML2 | 2.89 |
| 868 | 3 | 4 | 5 | 6 | VI-1 | EML3 | 2.21 |
| 869 | 3 | 4 | 5 | 6 | VI-1 | EML4 | 2.16 |
| 870 | 3 | 4 | 5 | 6 | VI-1 | EMP3 | 2.09 |
| 871 | 3 | 4 | 5 | 6 | VI-1 | EMR2 | 2.18 |
| 872 | 3 | 4 | 5 | 6 | VI-1 | ENO2 | 3.00 |
| 873 | 3 | 4 | 5 | 6 | VI-1 | ENTPD1 | 2.21 |
| 874 | 3 | 4 | 5 | 6 | VI-1 | ENTPD4 | 2.90 |
| 875 | 3 | 4 | 5 | 6 | VI-1 | ENTPD6 | 2.37 |
| 876 | 3 | 4 | 5 | 6 | VI-1 | EP300 | 2.55 |
| 877 | 3 | 4 | 5 | 6 | VI-1 | EP400 | 2.82 |
| 878 | 3 | 4 | 5 | 6 | VI-1 | EPG5 | 3.35 |
| 879 | 3 | 4 | 5 | 6 | VI-1 | EPHB1 | 2.68 |
| 880 | 3 | 4 | 5 | 6 | VI-1 | EPHB2 | 3.83 |
| 881 | 3 | 4 | 5 | 6 | VI-1 | EPHB6 | 2.47 |
| 882 | 3 | 4 | 5 | 6 | VI-1 | EPM2AIP1 | 4.30 |
| 883 | 3 | 4 | 5 | 6 | VI-1 | EPPK1 | 2.39 |
| 884 | 3 | 4 | 5 | 6 | VI-1 | EPS15 | 2.08 |
| 885 | 3 | 4 | 5 | 6 | VI-1 | EPT1 | 2.80 |
| 886 | 3 | 4 | 5 | 6 | VI-1 | ERBB2IP | 2.11 |
| 887 | 3 | 4 | 5 | 6 | VI-1 | ERCC5 | 2.05 |
| 888 | 3 | 4 | 5 | 6 | VI-1 | ERI2 | 2.60 |
| 889 | 3 | 4 | 5 | 6 | VI-1 | ERICH1 | 3.24 |
| 890 | 3 | 4 | 5 | 6 | VI-1 | ERMN | 3.84 |
| 891 | 3 | 4 | 5 | 6 | VI-1 | ERO1LB | 2.45 |
| 892 | 3 | 4 | 5 | 6 | VI-1 | ERP44 | 2.17 |
| 893 | 3 | 4 | 5 | 6 | VI-1 | ERVK13-1 | 2.76 |
| 894 | 3 | 4 | 5 | 6 | VI-1 | ESF1 | 2.89 |
| 895 | 3 | 4 | 5 | 6 | VI-1 | ETV6 | 2.74 |
| 896 | 3 | 4 | 5 | 6 | VI-1 | EVL | 2.11 |
| 897 | 3 | 4 | 5 | 6 | VI-1 | EWSR1 | 2.04 |
| 898 | 3 | 4 | 5 | 6 | VI-1 | EXOC1 | 2.61 |
| 899 | 3 | 4 | 5 | 6 | VI-1 | EXOC3 | 2.15 |
| 900 | 3 | 4 | 5 | 6 | VI-1 | EXOC3L1 | 2.28 |
| 901 | 3 | 4 | 5 | 6 | VI-1 | EXOC8 | 2.58 |
| 902 | 3 | 4 | 5 | 6 | VI-1 | EXOG | 2.24 |
| 903 | 3 | 4 | 5 | 6 | VI-1 | EXOSC10 | 2.21 |
| 904 | 3 | 4 | 5 | 6 | VI-1 | EXOSC8 | 2.12 |
| 905 | 3 | 4 | 5 | 6 | VI-1 | EXOSC9 | 2.21 |
| 906 | 3 | 4 | 5 | 6 | VI-1 | EYA3 | 2.35 |
| 907 | 3 | 4 | 5 | 6 | VI-1 | EZH1 | 3.03 |
| 908 | 3 | 4 | 5 | 6 | VI-1 | F11R | 2.32 |
| 909 | 3 | 4 | 5 | 6 | VI-1 | F5 | 2.38 |
| 910 | 3 | 4 | 5 | 6 | VI-1 | FADS3 | 2.58 |
| 911 | 3 | 4 | 5 | 6 | VI-1 | FAM110A | 2.06 |
| 912 | 3 | 4 | 5 | 6 | VI-1 | FAM113A | 3.58 |
| 913 | 3 | 4 | 5 | 6 | VI-1 | FAM117B | 2.20 |
| 914 | 3 | 4 | 5 | 6 | VI-1 | FAM118A | 2.80 |
| 915 | 3 | 4 | 5 | 6 | VI-1 | FAM120A | 2.55 |
| 916 | 3 | 4 | 5 | 6 | VI-1 | FAM120C | 2.23 |
| 917 | 3 | 4 | 5 | 6 | VI-1 | FAM122B | 3.55 |
| 918 | 3 | 4 | 5 | 6 | VI-1 | FAM122C | 4.24 |
| 919 | 3 | 4 | 5 | 6 | VI-1 | FAM126B | 2.53 |
| 920 | 3 | 4 | 5 | 6 | VI-1 | FAM134B | 2.83 |
| 921 | 3 | 4 | 5 | 6 | VI-1 | FAM135A | 2.52 |
| 922 | 3 | 4 | 5 | 6 | VI-1 | FAM13A | 3.88 |
| 923 | 3 | 4 | 5 | 6 | VI-1 | FAM149B1 | 2.25 |
| 924 | 3 | 4 | 5 | 6 | VI-1 | FAM158A | 3.03 |
| 925 | 3 | 4 | 5 | 6 | VI-1 | FAM160A2 | 2.23 |
| 926 | 3 | 4 | 5 | 6 | VI-1 | FAM160B1 | 2.17 |
| 927 | 3 | 4 | 5 | 6 | VI-1 | FAM160B2 | 3.44 |
| 928 | 3 | 4 | 5 | 6 | VI-1 | FAM168A | 2.75 |
| 929 | 3 | 4 | 5 | 6 | VI-1 | FAM178A | 2.48 |
| 930 | 3 | 4 | 5 | 6 | VI-1 | FAM184B | 2.14 |
| 931 | 3 | 4 | 5 | 6 | VI-1 | FAM188A | 2.50 |
| 932 | 3 | 4 | 5 | 6 | VI-1 | FAM189B | 2.11 |
| 933 | 3 | 4 | 5 | 6 | VI-1 | FAM188B | 3.19 |
| 934 | 3 | 4 | 5 | 6 | VI-1 | FAM192A | 2.45 |
| 935 | 3 | 4 | 5 | 6 | VI-1 | FAM208B | 2.64 |
| 936 | 3 | 4 | 5 | 6 | VI-1 | FAM209A | 3.91 |
| 937 | 3 | 4 | 5 | 6 | VI-1 | FAM209B | 3.29 |
| 938 | 3 | 4 | 5 | 6 | VI-1 | FAM214A | 2.43 |
| 939 | 3 | 4 | 5 | 6 | VI-1 | FAM21B | 2.32 |
| 940 | 3 | 4 | 5 | 6 | VI-1 | FAM21C | 3.37 |
| 941 | 3 | 4 | 5 | 6 | VI-1 | FAM40A | 2.37 |
| 942 | 3 | 4 | 5 | 6 | VI-1 | FAM45B | 2.25 |
| 943 | 3 | 4 | 5 | 6 | VI-1 | FAM46A | 4.55 |
| 944 | 3 | 4 | 5 | 6 | VI-1 | FAM48A | 2.43 |
| 945 | 3 | 4 | 5 | 6 | VI-1 | FAM63B | 2.07 |
| 946 | 3 | 4 | 5 | 6 | VI-1 | FAM65A | 2.42 |
| 947 | 3 | 4 | 5 | 6 | VI-1 | FAM69A | 2.00 |
| 948 | 3 | 4 | 5 | 6 | VI-1 | FAM73B | 2.27 |
| 949 | 3 | 4 | 5 | 6 | VI-1 | FAM76B | 3.09 |
| 950 | 3 | 4 | 5 | 6 | VI-1 | FAM8A1 | 3.86 |
| 951 | 3 | 4 | 5 | 6 | VI-1 | FAM91A1 | 3.01 |
| 952 | 3 | 4 | 5 | 6 | VI-1 | FAN1 | 2.46 |
| 953 | 3 | 4 | 5 | 6 | VI-1 | FANCA | 4.69 |
| 954 | 3 | 4 | 5 | 6 | VI-1 | FANCD2 | 2.32 |
| 955 | 3 | 4 | 5 | 6 | VI-1 | FANCL | 2.36 |
| 956 | 3 | 4 | 5 | 6 | VI-1 | FAR1 | 2.26 |

Fig. 40 - 6

| | | | | | | | | | | | | | | | |
|---|---|---|---|---|---|---|---|---|---|---|---|---|---|---|---|
| 957 | 3 | 4 | 5 | 6 | | VI-1 | FAR2 | 3.74 | 1053 | 3 | 4 | 5 | 6 | VI-1 | GANC | 2.26 |
| 958 | 3 | 4 | 5 | 6 | | VI-1 | FASTK | 2.20 | 1054 | 3 | 4 | 5 | 6 | VI-1 | GATAD1 | 2.56 |
| 959 | 3 | 4 | 5 | 6 | | VI-1 | FASTKD1 | 2.26 | 1055 | 3 | 4 | 5 | 6 | VI-1 | GATSL3 | 2.09 |
| 960 | 3 | 4 | 5 | 6 | | VI-1 | FBRSL1 | 2.19 | 1056 | 3 | 4 | 5 | 6 | VI-1 | GBA | 2.31 |
| 961 | 3 | 4 | 5 | 6 | | VI-1 | FBXL19 | 2.09 | 1057 | 3 | 4 | 5 | 6 | VI-1 | GBAP1 | 2.51 |
| 962 | 3 | 4 | 5 | 6 | | VI-1 | FBXL20 | 2.23 | 1058 | 3 | 4 | 5 | 6 | VI-1 | GBF1 | 2.73 |
| 963 | 3 | 4 | 5 | 6 | | VI-1 | FBXL6 | 2.85 | 1059 | 3 | 4 | 5 | 6 | VI-1 | GBP2 | 3.52 |
| 964 | 3 | 4 | 5 | 6 | | VI-1 | FBXL8 | 3.16 | 1060 | 3 | 4 | 5 | 6 | VI-1 | GBP6 | 4.71 |
| 965 | 3 | 4 | 5 | 6 | | VI-1 | FBXO11 | 2.74 | 1061 | 3 | 4 | 5 | 6 | VI-1 | GCC1 | 2.11 |
| 966 | 3 | 4 | 5 | 6 | | VI-1 | FBXO18 | 2.01 | 1062 | 3 | 4 | 5 | 6 | VI-1 | GCC2 | 2.84 |
| 967 | 3 | 4 | 5 | 6 | | VI-1 | FBXO22 | 2.38 | 1063 | 3 | 4 | 5 | 6 | VI-1 | GCFC1 | 2.78 |
| 968 | 3 | 4 | 5 | 6 | | VI-1 | FBXO22-AS1 | 2.30 | 1064 | 3 | 4 | 5 | 6 | VI-1 | GCFC1-AS1 | 2.35 |
| 969 | 3 | 4 | 5 | 6 | | VI-1 | FBXO41 | 2.20 | 1065 | 3 | 4 | 5 | 6 | VI-1 | GCH1 | 3.63 |
| 970 | 3 | 4 | 5 | 6 | | VI-1 | FBXO42 | 2.05 | 1066 | 3 | 4 | 5 | 6 | VI-1 | GCN1L1 | 2.80 |
| 971 | 3 | 4 | 5 | 6 | | VI-1 | FBXO44 | 3.52 | 1067 | 3 | 4 | 5 | 6 | VI-1 | GDAP2 | 2.08 |
| 972 | 3 | 4 | 5 | 6 | | VI-1 | FBXO6 | 3.09 | 1068 | 3 | 4 | 5 | 6 | VI-1 | GDI1 | 2.22 |
| 973 | 3 | 4 | 5 | 6 | | VI-1 | FBXW7 | 2.24 | 1069 | 3 | 4 | 5 | 6 | VI-1 | GEMIN5 | 2.19 |
| 974 | 3 | 4 | 5 | 6 | | VI-1 | FBXW8 | 2.70 | 1070 | 3 | 4 | 5 | 6 | VI-1 | GEMIN7 | 3.01 |
| 975 | 3 | 4 | 5 | 6 | | VI-1 | FCGR1A | 4.60 | 1071 | 3 | 4 | 5 | 6 | VI-1 | GEN1 | 2.53 |
| 976 | 3 | 4 | 5 | 6 | | VI-1 | FCGR1B | 4.81 | 1072 | 3 | 4 | 5 | 6 | VI-1 | GFM1 | 2.01 |
| 977 | 3 | 4 | 5 | 6 | | VI-1 | FCGR1C | 4.66 | 1073 | 3 | 4 | 5 | 6 | VI-1 | GFPT1 | 2.06 |
| 978 | 3 | 4 | 5 | 6 | | VI-1 | FCGR2C | 3.14 | 1074 | 3 | 4 | 5 | 6 | VI-1 | GGA1 | 2.76 |
| 979 | 3 | 4 | 5 | 6 | | VI-1 | FCGR3A | 2.40 | 1075 | 3 | 4 | 5 | 6 | VI-1 | GGA2 | 2.23 |
| 980 | 3 | 4 | 5 | 6 | | VI-1 | FCHSD1 | 3.71 | 1076 | 3 | 4 | 5 | 6 | VI-1 | GGA3 | 2.58 |
| 981 | 3 | 4 | 5 | 6 | | VI-1 | FDX1L | 2.12 | 1077 | 3 | 4 | 5 | 6 | VI-1 | GGCX | 3.30 |
| 982 | 3 | 4 | 5 | 6 | | VI-1 | FDXR | 3.01 | 1078 | 3 | 4 | 5 | 6 | VI-1 | GGT7 | 4.04 |
| 983 | 3 | 4 | 5 | 6 | | VI-1 | FES | 2.14 | 1079 | 3 | 4 | 5 | 6 | VI-1 | GHRLOS | 2.52 |
| 984 | 3 | 4 | 5 | 6 | | VI-1 | FGD3 | 2.54 | 1080 | 3 | 4 | 5 | 6 | VI-1 | GIGYF1 | 3.02 |
| 985 | 3 | 4 | 5 | 6 | | VI-1 | FGD4 | 2.39 | 1081 | 3 | 4 | 5 | 6 | VI-1 | GIMAP8 | 2.57 |
| 986 | 3 | 4 | 5 | 6 | | VI-1 | FGFRL1 | 2.32 | 1082 | 3 | 4 | 5 | 6 | VI-1 | GIT2 | 2.24 |
| 987 | 3 | 4 | 5 | 6 | | VI-1 | FGL2 | 2.91 | 1083 | 3 | 4 | 5 | 6 | VI-1 | GJA9-MYCBP | 2.26 |
| 988 | 3 | 4 | 5 | 6 | | VI-1 | FHDC1 | 2.18 | 1084 | 3 | 4 | 5 | 6 | VI-1 | GK | 2.65 |
| 989 | 3 | 4 | 5 | 6 | | VI-1 | FHIT | 2.55 | 1085 | 3 | 4 | 5 | 6 | VI-1 | GLB1L | 2.25 |
| 990 | 3 | 4 | 5 | 6 | | VI-1 | FHOD1 | 2.58 | 1086 | 3 | 4 | 5 | 6 | VI-1 | GLI4 | 2.13 |
| 991 | 3 | 4 | 5 | 6 | | VI-1 | FIG4 | 2.25 | 1087 | 3 | 4 | 5 | 6 | VI-1 | GLRX2 | 2.38 |
| 992 | 3 | 4 | 5 | 6 | | VI-1 | FIGNL1 | 2.08 | 1088 | 3 | 4 | 5 | 6 | VI-1 | GLS | 2.74 |
| 993 | 3 | 4 | 5 | 6 | | VI-1 | FITM1 | 2.97 | 1089 | 3 | 4 | 5 | 6 | VI-1 | GLT25D1 | 2.23 |
| 994 | 3 | 4 | 5 | 6 | | VI-1 | FKBP11 | 2.05 | 1090 | 3 | 4 | 5 | 6 | VI-1 | GLTSCR1 | 2.18 |
| 995 | 3 | 4 | 5 | 6 | | VI-1 | FKBP15 | 3.35 | 1091 | 3 | 4 | 5 | 6 | VI-1 | GLYCTK | 2.14 |
| 996 | 3 | 4 | 5 | 6 | | VI-1 | FKBP3 | 2.15 | 1092 | 3 | 4 | 5 | 6 | VI-1 | GMIP | 2.27 |
| 997 | 3 | 4 | 5 | 6 | | VI-1 | FKBPL | 2.25 | 1093 | 3 | 4 | 5 | 6 | VI-1 | GMPPB | 2.15 |
| 998 | 3 | 4 | 5 | 6 | | VI-1 | FKRP | 2.01 | 1094 | 3 | 4 | 5 | 6 | VI-1 | GNB4 | 2.24 |
| 999 | 3 | 4 | 5 | 6 | | VI-1 | FLCN | 3.24 | 1095 | 3 | 4 | 5 | 6 | VI-1 | GNL3L | 2.03 |
| 1000 | 3 | 4 | 5 | 6 | | VI-1 | FLII | 2.10 | 1096 | 3 | 4 | 5 | 6 | VI-1 | GNS | 2.67 |
| 1001 | 3 | 4 | 5 | 6 | | VI-1 | FLJ10038 | 2.09 | 1097 | 3 | 4 | 5 | 6 | VI-1 | GOLGA1 | 3.44 |
| 1002 | 3 | 4 | 5 | 6 | | VI-1 | FLJ12334 | 3.42 | 1098 | 3 | 4 | 5 | 6 | VI-1 | GOLGA2 | 3.00 |
| 1003 | 3 | 4 | 5 | 6 | | VI-1 | FLJ31306 | 2.98 | 1099 | 3 | 4 | 5 | 6 | VI-1 | GOLGA2P5 | 4.27 |
| 1004 | 3 | 4 | 5 | 6 | | VI-1 | FLJ39639 | 2.59 | 1100 | 3 | 4 | 5 | 6 | VI-1 | GOLGA3 | 2.40 |
| 1005 | 3 | 4 | 5 | 6 | | VI-1 | FLJ41484 | 4.09 | 1101 | 3 | 4 | 5 | 6 | VI-1 | GOLGA6L9 | 2.42 |
| 1006 | 3 | 4 | 5 | 6 | | VI-1 | FLJ42627 | 3.03 | 1102 | 3 | 4 | 5 | 6 | VI-1 | GOLGA7B | 2.30 |
| 1007 | 3 | 4 | 5 | 6 | | VI-1 | FLJ45340 | 4.23 | 1103 | 3 | 4 | 5 | 6 | VI-1 | GOLGB1 | 3.07 |
| 1008 | 3 | 4 | 5 | 6 | | VI-1 | FLJ45513 | 2.32 | 1104 | 3 | 4 | 5 | 6 | VI-1 | GOLPH3L | 2.04 |
| 1009 | 3 | 4 | 5 | 6 | | VI-1 | FLNA | 2.06 | 1105 | 3 | 4 | 5 | 6 | VI-1 | GOPC | 2.18 |
| 1010 | 3 | 4 | 5 | 6 | | VI-1 | FLVCR1 | 2.83 | 1106 | 3 | 4 | 5 | 6 | VI-1 | GORAB | 2.14 |
| 1011 | 3 | 4 | 5 | 6 | | VI-1 | FLYWCH1 | 3.23 | 1107 | 3 | 4 | 5 | 6 | VI-1 | GORASP1 | 2.52 |
| 1012 | 3 | 4 | 5 | 6 | | VI-1 | FMN1 | 3.35 | 1108 | 3 | 4 | 5 | 6 | VI-1 | GPBAR1 | 2.27 |
| 1013 | 3 | 4 | 5 | 6 | | VI-1 | FMNL1 | 2.42 | 1109 | 3 | 4 | 5 | 6 | VI-1 | GPBP1 | 2.07 |
| 1014 | 3 | 4 | 5 | 6 | | VI-1 | FMNL2 | 3.37 | 1110 | 3 | 4 | 5 | 6 | VI-1 | GPCPD1 | 2.84 |
| 1015 | 3 | 4 | 5 | 6 | | VI-1 | FMR1 | 3.55 | 1111 | 3 | 4 | 5 | 6 | VI-1 | GPD2 | 3.05 |
| 1016 | 3 | 4 | 5 | 6 | | VI-1 | FNBP4 | 3.15 | 1112 | 3 | 4 | 5 | 6 | VI-1 | GPR107 | 2.29 |
| 1017 | 3 | 4 | 5 | 6 | | VI-1 | FNDC3A | 2.53 | 1113 | 3 | 4 | 5 | 6 | VI-1 | GPR155 | 3.73 |
| 1018 | 3 | 4 | 5 | 6 | | VI-1 | FNDC3B | 2.16 | 1114 | 3 | 4 | 5 | 6 | VI-1 | GPR172A | 2.02 |
| 1019 | 3 | 4 | 5 | 6 | | VI-1 | FNIP1 | 2.42 | 1115 | 3 | 4 | 5 | 6 | VI-1 | GPR89C | 2.25 |
| 1020 | 3 | 4 | 5 | 6 | | VI-1 | FNIP2 | 2.43 | 1116 | 3 | 4 | 5 | 6 | VI-1 | GRAMD1B | 4.04 |
| 1021 | 3 | 4 | 5 | 6 | | VI-1 | FNTB | 3.68 | 1117 | 3 | 4 | 5 | 6 | VI-1 | GRAMD4 | 2.74 |
| 1022 | 3 | 4 | 5 | 6 | | VI-1 | FOS | 2.18 | 1118 | 3 | 4 | 5 | 6 | VI-1 | GRHL1 | 2.54 |
| 1023 | 3 | 4 | 5 | 6 | | VI-1 | FOXJ2 | 2.07 | 1119 | 3 | 4 | 5 | 6 | VI-1 | GRIPAP1 | 4.15 |
| 1024 | 3 | 4 | 5 | 6 | | VI-1 | FOXJ3 | 2.01 | 1120 | 3 | 4 | 5 | 6 | VI-1 | GSDMD | 2.79 |
| 1025 | 3 | 4 | 5 | 6 | | VI-1 | FOXM1 | 2.33 | 1121 | 3 | 4 | 5 | 6 | VI-1 | GTF2H4 | 2.32 |
| 1026 | 3 | 4 | 5 | 6 | | VI-1 | FOXP1 | 2.57 | 1122 | 3 | 4 | 5 | 6 | VI-1 | GTF2IRD2 | 2.28 |
| 1027 | 3 | 4 | 5 | 6 | | VI-1 | FRA10AC1 | 2.26 | 1123 | 3 | 4 | 5 | 6 | VI-1 | GTF2IRD2B | 2.29 |
| 1028 | 3 | 4 | 5 | 6 | | VI-1 | FRAT1 | 2.03 | 1124 | 3 | 4 | 5 | 6 | VI-1 | GTF3C1 | 2.32 |
| 1029 | 3 | 4 | 5 | 6 | | VI-1 | FRMD4B | 3.10 | 1125 | 3 | 4 | 5 | 6 | VI-1 | GTF3C3 | 2.00 |
| 1030 | 3 | 4 | 5 | 6 | | VI-1 | FRY | 3.34 | 1126 | 3 | 4 | 5 | 6 | VI-1 | GTPBP1 | 2.88 |
| 1031 | 3 | 4 | 5 | 6 | | VI-1 | FRYL | 2.35 | 1127 | 3 | 4 | 5 | 6 | VI-1 | GTPBP2 | 3.03 |
| 1032 | 3 | 4 | 5 | 6 | | VI-1 | FSTL3 | 2.12 | 1128 | 3 | 4 | 5 | 6 | VI-1 | GTPBP3 | 2.38 |
| 1033 | 3 | 4 | 5 | 6 | | VI-1 | FUBP3 | 2.03 | 1129 | 3 | 4 | 5 | 6 | VI-1 | GUCA1B | 2.14 |
| 1034 | 3 | 4 | 5 | 6 | | VI-1 | FUK | 2.49 | 1130 | 3 | 4 | 5 | 6 | VI-1 | GUF1 | 2.30 |
| 1035 | 3 | 4 | 5 | 6 | | VI-1 | FUNDC1 | 2.31 | 1131 | 3 | 4 | 5 | 6 | VI-1 | GUSB | 2.06 |
| 1036 | 3 | 4 | 5 | 6 | | VI-1 | FUT10 | 2.10 | 1132 | 3 | 4 | 5 | 6 | VI-1 | H2AFZ | 2.44 |
| 1037 | 3 | 4 | 5 | 6 | | VI-1 | FUT4 | 2.03 | 1133 | 3 | 4 | 5 | 6 | VI-1 | HADHB | 2.76 |
| 1038 | 3 | 4 | 5 | 6 | | VI-1 | FXR2 | 2.05 | 1134 | 3 | 4 | 5 | 6 | VI-1 | HAL | 3.01 |
| 1039 | 3 | 4 | 5 | 6 | | VI-1 | FYB | 2.90 | 1135 | 3 | 4 | 5 | 6 | VI-1 | HAPLN3 | 2.86 |
| 1040 | 3 | 4 | 5 | 6 | | VI-1 | FZR1 | 2.12 | 1136 | 3 | 4 | 5 | 6 | VI-1 | HARBI1 | 2.87 |
| 1041 | 3 | 4 | 5 | 6 | | VI-1 | GAB1 | 2.68 | 1137 | 3 | 4 | 5 | 6 | VI-1 | HARS | 2.13 |
| 1042 | 3 | 4 | 5 | 6 | | VI-1 | GAB2 | 2.10 | 1138 | 3 | 4 | 5 | 6 | VI-1 | HARS2 | 2.49 |
| 1043 | 3 | 4 | 5 | 6 | | VI-1 | GAB3 | 2.00 | 1139 | 3 | 4 | 5 | 6 | VI-1 | HAUS5 | 3.01 |
| 1044 | 3 | 4 | 5 | 6 | | VI-1 | GADD45B | 2.38 | 1140 | 3 | 4 | 5 | 6 | VI-1 | HCFC1 | 2.39 |
| 1045 | 3 | 4 | 5 | 6 | | VI-1 | GAK | 2.47 | 1141 | 3 | 4 | 5 | 6 | VI-1 | HCG26 | 3.81 |
| 1046 | 3 | 4 | 5 | 6 | | VI-1 | GALC | 2.35 | 1142 | 3 | 4 | 5 | 6 | VI-1 | HDAC10 | 3.07 |
| 1047 | 3 | 4 | 5 | 6 | | VI-1 | GALM | 2.76 | 1143 | 3 | 4 | 5 | 6 | VI-1 | HDAC6 | 3.22 |
| 1048 | 3 | 4 | 5 | 6 | | VI-1 | GALNS | 2.72 | 1144 | 3 | 4 | 5 | 6 | VI-1 | HDAC7 | 2.08 |
| 1049 | 3 | 4 | 5 | 6 | | VI-1 | GALNT3 | 2.74 | 1145 | 3 | 4 | 5 | 6 | VI-1 | HEATR1 | 2.54 |
| 1050 | 3 | 4 | 5 | 6 | | VI-1 | GALNT4 | 2.16 | 1146 | 3 | 4 | 5 | 6 | VI-1 | HEATR5B | 3.11 |
| 1051 | 3 | 4 | 5 | 6 | | VI-1 | GALNT7 | 2.33 | 1147 | 3 | 4 | 5 | 6 | VI-1 | HEATR6 | 2.23 |
| 1052 | 3 | 4 | 5 | 6 | | VI-1 | GALT | 2.97 | 1148 | 3 | 4 | 5 | 6 | VI-1 | HEATR7A | 2.83 |

Fig. 40 - 7

| | | | | | | | | | | | | | | | |
|---|---|---|---|---|---|---|---|---|---|---|---|---|---|---|---|
| 1149 | 3 | 4 | 5 | 6 | | VI-1 | HEBP1 | 2.53 | 1245 | 3 | 4 | 5 | 6 | VI-1 | ING3 | 2.19 |
| 1150 | 3 | 4 | 5 | 6 | | VI-1 | HECA | 2.45 | 1246 | 3 | 4 | 5 | 6 | VI-1 | ING4 | 2.29 |
| 1151 | 3 | 4 | 5 | 6 | | VI-1 | HECTD1 | 2.22 | 1247 | 3 | 4 | 5 | 6 | VI-1 | ING5 | 2.27 |
| 1152 | 3 | 4 | 5 | 6 | | VI-1 | HECTD3 | 2.13 | 1248 | 3 | 4 | 5 | 6 | VI-1 | INO80B | 2.11 |
| 1153 | 3 | 4 | 5 | 6 | | VI-1 | HELZ | 2.09 | 1249 | 3 | 4 | 5 | 6 | VI-1 | INO80D | 2.32 |
| 1154 | 3 | 4 | 5 | 6 | | VI-1 | HEMK1 | 4.63 | 1250 | 3 | 4 | 5 | 6 | VI-1 | INO80E | 2.02 |
| 1155 | 3 | 4 | 5 | 6 | | VI-1 | HERC1 | 2.25 | 1251 | 3 | 4 | 5 | 6 | VI-1 | INPP4A | 2.68 |
| 1156 | 3 | 4 | 5 | 6 | | VI-1 | HERC2P3 | 3.13 | 1252 | 3 | 4 | 5 | 6 | VI-1 | INPP5D | 2.65 |
| 1157 | 3 | 4 | 5 | 6 | | VI-1 | HERC2P7 | 3.14 | 1253 | 3 | 4 | 5 | 6 | VI-1 | INPP5E | 2.47 |
| 1158 | 3 | 4 | 5 | 6 | | VI-1 | HERC3 | 2.85 | 1254 | 3 | 4 | 5 | 6 | VI-1 | INPP5F | 3.00 |
| 1159 | 3 | 4 | 5 | 6 | | VI-1 | HERC4 | 2.60 | 1255 | 3 | 4 | 5 | 6 | VI-1 | INPPL1 | 2.73 |
| 1160 | 3 | 4 | 5 | 6 | | VI-1 | HERPUD2 | 2.02 | 1256 | 3 | 4 | 5 | 6 | VI-1 | INTS1 | 2.34 |
| 1161 | 3 | 4 | 5 | 6 | | VI-1 | HEXIM1 | 2.35 | 1257 | 3 | 4 | 5 | 6 | VI-1 | INTS2 | 2.08 |
| 1162 | 3 | 4 | 5 | 6 | | VI-1 | HEXIM2 | 2.84 | 1258 | 3 | 4 | 5 | 6 | VI-1 | INTS3 | 3.63 |
| 1163 | 3 | 4 | 5 | 6 | | VI-1 | HGF | 2.68 | 1259 | 3 | 4 | 5 | 6 | VI-1 | INTS4 | 2.82 |
| 1164 | 3 | 4 | 5 | 6 | | VI-1 | HGS | 3.04 | 1260 | 3 | 4 | 5 | 6 | VI-1 | INTS8 | 2.42 |
| 1165 | 3 | 4 | 5 | 6 | | VI-1 | HHEX | 2.70 | 1261 | 3 | 4 | 5 | 6 | VI-1 | INVS | 2.13 |
| 1166 | 3 | 4 | 5 | 6 | | VI-1 | HINT3 | 2.59 | 1262 | 3 | 4 | 5 | 6 | VI-1 | IP6K2 | 2.14 |
| 1167 | 3 | 4 | 5 | 6 | | VI-1 | HIP1R | 2.24 | 1263 | 3 | 4 | 5 | 6 | VI-1 | IPO4 | 2.58 |
| 1168 | 3 | 4 | 5 | 6 | | VI-1 | HIST1H1T | 2.12 | 1264 | 3 | 4 | 5 | 6 | VI-1 | IPO8 | 2.33 |
| 1169 | 3 | 4 | 5 | 6 | | VI-1 | HIST1H2BE | 2.18 | 1265 | 3 | 4 | 5 | 6 | VI-1 | IPO9 | 2.33 |
| 1170 | 3 | 4 | 5 | 6 | | VI-1 | HIST1H2BG | 3.55 | 1266 | 3 | 4 | 5 | 6 | VI-1 | IPPK | 2.16 |
| 1171 | 3 | 4 | 5 | 6 | | VI-1 | HIST1H2BN | 2.41 | 1267 | 3 | 4 | 5 | 6 | VI-1 | IQCE | 2.21 |
| 1172 | 3 | 4 | 5 | 6 | | VI-1 | HIST1H3E | 2.42 | 1268 | 3 | 4 | 5 | 6 | VI-1 | IQSEC1 | 2.49 |
| 1173 | 3 | 4 | 5 | 6 | | VI-1 | HIST1H3H | 2.09 | 1269 | 3 | 4 | 5 | 6 | VI-1 | IREB2 | 2.06 |
| 1174 | 3 | 4 | 5 | 6 | | VI-1 | HIST2H2BA | 2.33 | 1270 | 3 | 4 | 5 | 6 | VI-1 | IRF1 | 2.48 |
| 1175 | 3 | 4 | 5 | 6 | | VI-1 | HIST2H2BE | 2.52 | 1271 | 3 | 4 | 5 | 6 | VI-1 | IRF2 | 2.12 |
| 1176 | 3 | 4 | 5 | 6 | | VI-1 | HIVEP1 | 2.99 | 1272 | 3 | 4 | 5 | 6 | VI-1 | IRF2BP2 | 2.35 |
| 1177 | 3 | 4 | 5 | 6 | | VI-1 | HK2 | 2.31 | 1273 | 3 | 4 | 5 | 6 | VI-1 | IRF5 | 3.91 |
| 1178 | 3 | 4 | 5 | 6 | | VI-1 | HK3 | 3.85 | 1274 | 3 | 4 | 5 | 6 | VI-1 | IRF9 | 4.14 |
| 1179 | 3 | 4 | 5 | 6 | | VI-1 | HKDC1 | 2.92 | 1275 | 3 | 4 | 5 | 6 | VI-1 | IRGQ | 2.41 |
| 1180 | 3 | 4 | 5 | 6 | | VI-1 | HLA-A | 2.20 | 1276 | 3 | 4 | 5 | 6 | VI-1 | ISG20 | 2.29 |
| 1181 | 3 | 4 | 5 | 6 | | VI-1 | HLA-DMA | 2.09 | 1277 | 3 | 4 | 5 | 6 | VI-1 | ISM1 | 2.59 |
| 1182 | 3 | 4 | 5 | 6 | | VI-1 | HLA-F | 2.34 | 1278 | 3 | 4 | 5 | 6 | VI-1 | IST1 | 2.19 |
| 1183 | 3 | 4 | 5 | 6 | | VI-1 | HLA-G | 2.02 | 1279 | 3 | 4 | 5 | 6 | VI-1 | ISYNA1 | 3.96 |
| 1184 | 3 | 4 | 5 | 6 | | VI-1 | HMBOX1 | 2.28 | 1280 | 3 | 4 | 5 | 6 | VI-1 | ITFG1 | 2.44 |
| 1185 | 3 | 4 | 5 | 6 | | VI-1 | HMGCR | 2.15 | 1281 | 3 | 4 | 5 | 6 | VI-1 | ITGA4 | 2.37 |
| 1186 | 3 | 4 | 5 | 6 | | VI-1 | HMGCS1 | 2.05 | 1282 | 3 | 4 | 5 | 6 | VI-1 | ITGA5 | 2.46 |
| 1187 | 3 | 4 | 5 | 6 | | VI-1 | HMGN3 | 2.49 | 1283 | 3 | 4 | 5 | 6 | VI-1 | ITGAL | 2.20 |
| 1188 | 3 | 4 | 5 | 6 | | VI-1 | HMGN5 | 2.98 | 1284 | 3 | 4 | 5 | 6 | VI-1 | ITGAM | 2.45 |
| 1189 | 3 | 4 | 5 | 6 | | VI-1 | HMHA1 | 2.49 | 1285 | 3 | 4 | 5 | 6 | VI-1 | ITGAV | 2.21 |
| 1190 | 3 | 4 | 5 | 6 | | VI-1 | HMOX1 | 2.05 | 1286 | 3 | 4 | 5 | 6 | VI-1 | ITIH4 | 3.62 |
| 1191 | 3 | 4 | 5 | 6 | | VI-1 | HNRNPA2B1 | 2.62 | 1287 | 3 | 4 | 5 | 6 | VI-1 | ITPA | 2.44 |
| 1192 | 3 | 4 | 5 | 6 | | VI-1 | HNRNPA3 | 2.83 | 1288 | 3 | 4 | 5 | 6 | VI-1 | ITPK1 | 2.09 |
| 1193 | 3 | 4 | 5 | 6 | | VI-1 | HNRNPD | 2.13 | 1289 | 3 | 4 | 5 | 6 | VI-1 | ITPR2 | 2.92 |
| 1194 | 3 | 4 | 5 | 6 | | VI-1 | HNRNPH1 | 2.46 | 1290 | 3 | 4 | 5 | 6 | VI-1 | ITPR3 | 2.99 |
| 1195 | 3 | 4 | 5 | 6 | | VI-1 | HNRNPH3 | 3.22 | 1291 | 3 | 4 | 5 | 6 | VI-1 | ITPRIP | 2.15 |
| 1196 | 3 | 4 | 5 | 6 | | VI-1 | HNRNPM | 2.44 | 1292 | 3 | 4 | 5 | 6 | VI-1 | ITSN1 | 2.30 |
| 1197 | 3 | 4 | 5 | 6 | | VI-1 | HNRNPU | 2.10 | 1293 | 3 | 4 | 5 | 6 | VI-1 | ITSN2 | 2.41 |
| 1198 | 3 | 4 | 5 | 6 | | VI-1 | HOMER3 | 2.48 | 1294 | 3 | 4 | 5 | 6 | VI-1 | IZUMO4 | 2.24 |
| 1199 | 3 | 4 | 5 | 6 | | VI-1 | HOOK3 | 2.23 | 1295 | 3 | 4 | 5 | 6 | VI-1 | JAK1 | 2.07 |
| 1200 | 3 | 4 | 5 | 6 | | VI-1 | HOXB3 | 3.28 | 1296 | 3 | 4 | 5 | 6 | VI-1 | JAK2 | 3.21 |
| 1201 | 3 | 4 | 5 | 6 | | VI-1 | HP1BP3 | 2.44 | 1297 | 3 | 4 | 5 | 6 | VI-1 | JAK3 | 2.20 |
| 1202 | 3 | 4 | 5 | 6 | | VI-1 | HPS3 | 2.12 | 1298 | 3 | 4 | 5 | 6 | VI-1 | JARID2 | 2.51 |
| 1203 | 3 | 4 | 5 | 6 | | VI-1 | HPS4 | 2.05 | 1299 | 3 | 4 | 5 | 6 | VI-1 | JHDM1D | 2.33 |
| 1204 | 3 | 4 | 5 | 6 | | VI-1 | HPS5 | 2.29 | 1300 | 3 | 4 | 5 | 6 | VI-1 | JKAMP | 2.24 |
| 1205 | 3 | 4 | 5 | 6 | | VI-1 | HSD17B7P2 | 2.96 | 1301 | 3 | 4 | 5 | 6 | VI-1 | JMJD1C | 2.32 |
| 1206 | 3 | 4 | 5 | 6 | | VI-1 | HSDL1 | 2.25 | 1302 | 3 | 4 | 5 | 6 | VI-1 | JMJD7 | 3.22 |
| 1207 | 3 | 4 | 5 | 6 | | VI-1 | HSFX1 | 2.33 | 1303 | 3 | 4 | 5 | 6 | VI-1 | JRK | 2.59 |
| 1208 | 3 | 4 | 5 | 6 | | VI-1 | HSH2D | 3.61 | 1304 | 3 | 4 | 5 | 6 | VI-1 | JRKL | 2.85 |
| 1209 | 3 | 4 | 5 | 6 | | VI-1 | HSP90AA1 | 2.28 | 1305 | 3 | 4 | 5 | 6 | VI-1 | JUN | 2.20 |
| 1210 | 3 | 4 | 5 | 6 | | VI-1 | HSP90AA4P | 2.47 | 1306 | 3 | 4 | 5 | 6 | VI-1 | KANSL1L | 2.51 |
| 1211 | 3 | 4 | 5 | 6 | | VI-1 | HSP90B1 | 2.47 | 1307 | 3 | 4 | 5 | 6 | VI-1 | KAT2A | 4.53 |
| 1212 | 3 | 4 | 5 | 6 | | VI-1 | HSP90B3P | 2.66 | 1308 | 3 | 4 | 5 | 6 | VI-1 | KBTBD2 | 2.04 |
| 1213 | 3 | 4 | 5 | 6 | | VI-1 | HSPBAP1 | 2.30 | 1309 | 3 | 4 | 5 | 6 | VI-1 | KCNC3 | 2.17 |
| 1214 | 3 | 4 | 5 | 6 | | VI-1 | HSPH1 | 3.04 | 1310 | 3 | 4 | 5 | 6 | VI-1 | KCNG1 | 2.74 |
| 1215 | 3 | 4 | 5 | 6 | | VI-1 | HTT | 2.34 | 1311 | 3 | 4 | 5 | 6 | VI-1 | KCNIP2 | 2.32 |
| 1216 | 3 | 4 | 5 | 6 | | VI-1 | HUWE1 | 2.35 | 1312 | 3 | 4 | 5 | 6 | VI-1 | KCNK6 | 2.14 |
| 1217 | 3 | 4 | 5 | 6 | | VI-1 | IDE | 2.18 | 1313 | 3 | 4 | 5 | 6 | VI-1 | KCTD13 | 2.05 |
| 1218 | 3 | 4 | 5 | 6 | | VI-1 | IDH1 | 2.18 | 1314 | 3 | 4 | 5 | 6 | VI-1 | KCTD15 | 2.21 |
| 1219 | 3 | 4 | 5 | 6 | | VI-1 | IER2 | 2.30 | 1315 | 3 | 4 | 5 | 6 | VI-1 | KCTD7 | 2.34 |
| 1220 | 3 | 4 | 5 | 6 | | VI-1 | IFFO1 | 3.52 | 1316 | 3 | 4 | 5 | 6 | VI-1 | KDM1B | 2.60 |
| 1221 | 3 | 4 | 5 | 6 | | VI-1 | IFI16 | 3.89 | 1317 | 3 | 4 | 5 | 6 | VI-1 | KDM2A | 2.21 |
| 1222 | 3 | 4 | 5 | 6 | | VI-1 | IFI30 | 2.40 | 1318 | 3 | 4 | 5 | 6 | VI-1 | KDM2B | 2.28 |
| 1223 | 3 | 4 | 5 | 6 | | VI-1 | IFI35 | 4.68 | 1319 | 3 | 4 | 5 | 6 | VI-1 | KDM3B | 2.27 |
| 1224 | 3 | 4 | 5 | 6 | | VI-1 | IFRD1 | 2.41 | 1320 | 3 | 4 | 5 | 6 | VI-1 | KDM4C | 2.19 |
| 1225 | 3 | 4 | 5 | 6 | | VI-1 | IFT27 | 2.38 | 1321 | 3 | 4 | 5 | 6 | VI-1 | KDM5B | 2.29 |
| 1226 | 3 | 4 | 5 | 6 | | VI-1 | IFT80 | 4.40 | 1322 | 3 | 4 | 5 | 6 | VI-1 | KDM5C | 2.58 |
| 1227 | 3 | 4 | 5 | 6 | | VI-1 | IGF2BP3 | 4.53 | 1323 | 3 | 4 | 5 | 6 | VI-1 | KDM6A | 2.36 |
| 1228 | 3 | 4 | 5 | 6 | | VI-1 | IGF2R | 2.42 | 1324 | 3 | 4 | 5 | 6 | VI-1 | KHSRP | 2.02 |
| 1229 | 3 | 4 | 5 | 6 | | VI-1 | IGHMBP2 | 2.72 | 1325 | 3 | 4 | 5 | 6 | VI-1 | KIAA0141 | 2.26 |
| 1230 | 3 | 4 | 5 | 6 | | VI-1 | IGIP | 3.03 | 1326 | 3 | 4 | 5 | 6 | VI-1 | KIAA0146 | 3.45 |
| 1231 | 3 | 4 | 5 | 6 | | VI-1 | IGSF8 | 2.02 | 1327 | 3 | 4 | 5 | 6 | VI-1 | KIAA0182 | 3.34 |
| 1232 | 3 | 4 | 5 | 6 | | VI-1 | IKBKAP | 2.27 | 1328 | 3 | 4 | 5 | 6 | VI-1 | KIAA0195 | 2.31 |
| 1233 | 3 | 4 | 5 | 6 | | VI-1 | IKBKB | 2.64 | 1329 | 3 | 4 | 5 | 6 | VI-1 | KIAA0196 | 2.07 |
| 1234 | 3 | 4 | 5 | 6 | | VI-1 | IKBKG | 2.01 | 1330 | 3 | 4 | 5 | 6 | VI-1 | KIAA0226 | 4.14 |
| 1235 | 3 | 4 | 5 | 6 | | VI-1 | IL12RB1 | 2.10 | 1331 | 3 | 4 | 5 | 6 | VI-1 | KIAA0319L | 3.93 |
| 1236 | 3 | 4 | 5 | 6 | | VI-1 | IL15 | 3.66 | 1332 | 3 | 4 | 5 | 6 | VI-1 | KIAA0355 | 2.10 |
| 1237 | 3 | 4 | 5 | 6 | | VI-1 | IL15RA | 2.47 | 1333 | 3 | 4 | 5 | 6 | VI-1 | KIAA0368 | 2.32 |
| 1238 | 3 | 4 | 5 | 6 | | VI-1 | IL17RA | 2.14 | 1334 | 3 | 4 | 5 | 6 | VI-1 | KIAA0415 | 3.07 |
| 1239 | 3 | 4 | 5 | 6 | | VI-1 | IL1R1 | 2.43 | 1335 | 3 | 4 | 5 | 6 | VI-1 | KIAA0528 | 2.56 |
| 1240 | 3 | 4 | 5 | 6 | | VI-1 | IL4I1 | 2.02 | 1336 | 3 | 4 | 5 | 6 | VI-1 | KIAA0556 | 3.61 |
| 1241 | 3 | 4 | 5 | 6 | | VI-1 | ILF3 | 2.44 | 1337 | 3 | 4 | 5 | 6 | VI-1 | KIAA0586 | 2.07 |
| 1242 | 3 | 4 | 5 | 6 | | VI-1 | ILKAP | 2.26 | 1338 | 3 | 4 | 5 | 6 | VI-1 | KIAA0664 | 2.23 |
| 1243 | 3 | 4 | 5 | 6 | | VI-1 | INADL | 2.02 | 1339 | 3 | 4 | 5 | 6 | VI-1 | KIAA0664L3 | 3.63 |
| 1244 | 3 | 4 | 5 | 6 | | VI-1 | INCENP | 2.25 | 1340 | 3 | 4 | 5 | 6 | VI-1 | KIAA0753 | 2.16 |

Fig. 40 - 8

| | | | | | | | | | | | | | | | |
|---|---|---|---|---|---|---|---|---|---|---|---|---|---|---|---|
| 1341 | 3 | 4 | 5 | 6 | | VI-1 | KIAA0907 | 3.23 | 1437 | 3 | 4 | 5 | 6 | VI-1 | LOC100130744 | 2.44 |
| 1342 | 3 | 4 | 5 | 6 | | VI-1 | KIAA0913 | 2.95 | 1438 | 3 | 4 | 5 | 6 | VI-1 | LOC100130855 | 2.93 |
| 1343 | 3 | 4 | 5 | 6 | | VI-1 | KIAA0922 | 2.19 | 1439 | 3 | 4 | 5 | 6 | VI-1 | LOC100130950 | 2.29 |
| 1344 | 3 | 4 | 5 | 6 | | VI-1 | KIAA1009 | 3.32 | 1440 | 3 | 4 | 5 | 6 | VI-1 | LOC100131096 | 3.16 |
| 1345 | 3 | 4 | 5 | 6 | | VI-1 | KIAA1033 | 2.64 | 1441 | 3 | 4 | 5 | 6 | VI-1 | LOC100131733 | 2.00 |
| 1346 | 3 | 4 | 5 | 6 | | VI-1 | KIAA1109 | 4.28 | 1442 | 3 | 4 | 5 | 6 | VI-1 | LOC100132352 | 2.50 |
| 1347 | 3 | 4 | 5 | 6 | | VI-1 | KIAA1432 | 2.41 | 1443 | 3 | 4 | 5 | 6 | VI-1 | LOC100133991 | 3.84 |
| 1348 | 3 | 4 | 5 | 6 | | VI-1 | KIAA1467 | 2.10 | 1444 | 3 | 4 | 5 | 6 | VI-1 | LOC100170939 | 2.19 |
| 1349 | 3 | 4 | 5 | 6 | | VI-1 | KIAA1468 | 3.23 | 1445 | 3 | 4 | 5 | 6 | VI-1 | LOC100233209 | 3.03 |
| 1350 | 3 | 4 | 5 | 6 | | VI-1 | KIAA1522 | 2.23 | 1446 | 3 | 4 | 5 | 6 | VI-1 | LOC100270804 | 3.79 |
| 1351 | 3 | 4 | 5 | 6 | | VI-1 | KIAA1731 | 2.97 | 1447 | 3 | 4 | 5 | 6 | VI-1 | LOC100272228 | 2.76 |
| 1352 | 3 | 4 | 5 | 6 | | VI-1 | KIAA1841 | 2.35 | 1448 | 3 | 4 | 5 | 6 | VI-1 | LOC100287722 | 4.36 |
| 1353 | 3 | 4 | 5 | 6 | | VI-1 | KIAA1919 | 2.82 | 1449 | 3 | 4 | 5 | 6 | VI-1 | LOC100288123 | 2.99 |
| 1354 | 3 | 4 | 5 | 6 | | VI-1 | KIAA1958 | 2.74 | 1450 | 3 | 4 | 5 | 6 | VI-1 | LOC100288432 | 2.41 |
| 1355 | 3 | 4 | 5 | 6 | | VI-1 | KIAA2026 | 2.50 | 1451 | 3 | 4 | 5 | 6 | VI-1 | LOC100288615 | 4.37 |
| 1356 | 3 | 4 | 5 | 6 | | VI-1 | KIDINS220 | 2.44 | 1452 | 3 | 4 | 5 | 6 | VI-1 | LOC100329109 | 2.53 |
| 1357 | 3 | 4 | 5 | 6 | | VI-1 | KIF1B | 2.32 | 1453 | 3 | 4 | 5 | 6 | VI-1 | LOC100499177 | 2.12 |
| 1358 | 3 | 4 | 5 | 6 | | VI-1 | KIF20B | 2.55 | 1454 | 3 | 4 | 5 | 6 | VI-1 | LOC100499466 | 2.01 |
| 1359 | 3 | 4 | 5 | 6 | | VI-1 | KIF5B | 2.24 | 1455 | 3 | 4 | 5 | 6 | VI-1 | LOC100505549 | 2.40 |
| 1360 | 3 | 4 | 5 | 6 | | VI-1 | KIN | 2.55 | 1456 | 3 | 4 | 5 | 6 | VI-1 | LOC100505648 | 4.82 |
| 1361 | 3 | 4 | 5 | 6 | | VI-1 | KLC4 | 2.08 | 1457 | 3 | 4 | 5 | 6 | VI-1 | LOC100505761 | 2.10 |
| 1362 | 3 | 4 | 5 | 6 | | VI-1 | KLF6 | 2.41 | 1458 | 3 | 4 | 5 | 6 | VI-1 | LOC100505854 | 2.36 |
| 1363 | 3 | 4 | 5 | 6 | | VI-1 | KLHDC10 | 2.09 | 1459 | 3 | 4 | 5 | 6 | VI-1 | LOC100505875 | 2.74 |
| 1364 | 3 | 4 | 5 | 6 | | VI-1 | KLHL17 | 3.05 | 1460 | 3 | 4 | 5 | 6 | VI-1 | LOC100506033 | 4.70 |
| 1365 | 3 | 4 | 5 | 6 | | VI-1 | KLHL3 | 2.23 | 1461 | 3 | 4 | 5 | 6 | VI-1 | LOC100506124 | 2.20 |
| 1366 | 3 | 4 | 5 | 6 | | VI-1 | KLHL5 | 2.22 | 1462 | 3 | 4 | 5 | 6 | VI-1 | LOC100506233 | 2.56 |
| 1367 | 3 | 4 | 5 | 6 | | VI-1 | KLHL6 | 2.81 | 1463 | 3 | 4 | 5 | 6 | VI-1 | LOC100506343 | 2.82 |
| 1368 | 3 | 4 | 5 | 6 | | VI-1 | KLHL9 | 2.40 | 1464 | 3 | 4 | 5 | 6 | VI-1 | LOC100506469 | 4.68 |
| 1369 | 3 | 4 | 5 | 6 | | VI-1 | KPNA6 | 2.05 | 1465 | 3 | 4 | 5 | 6 | VI-1 | LOC100506710 | 2.32 |
| 1370 | 3 | 4 | 5 | 6 | | VI-1 | KPNB1 | 2.42 | 1466 | 3 | 4 | 5 | 6 | VI-1 | LOC100506801 | 2.05 |
| 1371 | 3 | 4 | 5 | 6 | | VI-1 | KPTN | 4.67 | 1467 | 3 | 4 | 5 | 6 | VI-1 | LOC100506866 | 2.56 |
| 1372 | 3 | 4 | 5 | 6 | | VI-1 | KRI1 | 2.27 | 1468 | 3 | 4 | 5 | 6 | VI-1 | LOC100507373 | 2.19 |
| 1373 | 3 | 4 | 5 | 6 | | VI-1 | KRT73 | 4.42 | 1469 | 3 | 4 | 5 | 6 | VI-1 | LOC100507387 | 3.26 |
| 1374 | 3 | 4 | 5 | 6 | | VI-1 | KTN1 | 2.02 | 1470 | 3 | 4 | 5 | 6 | VI-1 | LOC100507424 | 3.52 |
| 1375 | 3 | 4 | 5 | 6 | | VI-1 | KYNU | 2.85 | 1471 | 3 | 4 | 5 | 6 | VI-1 | LOC100507463 | 2.01 |
| 1376 | 3 | 4 | 5 | 6 | | VI-1 | L3MBTL3 | 2.37 | 1472 | 3 | 4 | 5 | 6 | VI-1 | LOC100507495 | 2.16 |
| 1377 | 3 | 4 | 5 | 6 | | VI-1 | LACC1 | 2.47 | 1473 | 3 | 4 | 5 | 6 | VI-1 | LOC100527964 | 3.82 |
| 1378 | 3 | 4 | 5 | 6 | | VI-1 | LACTB | 2.21 | 1474 | 3 | 4 | 5 | 6 | VI-1 | LOC100652768 | 4.37 |
| 1379 | 3 | 4 | 5 | 6 | | VI-1 | LAMP1 | 2.21 | 1475 | 3 | 4 | 5 | 6 | VI-1 | LOC147727 | 2.34 |
| 1380 | 3 | 4 | 5 | 6 | | VI-1 | LAMP2 | 2.31 | 1476 | 3 | 4 | 5 | 6 | VI-1 | LOC150776 | 2.49 |
| 1381 | 3 | 4 | 5 | 6 | | VI-1 | LARP1B | 2.21 | 1477 | 3 | 4 | 5 | 6 | VI-1 | LOC153684 | 3.74 |
| 1382 | 3 | 4 | 5 | 6 | | VI-1 | LARP4 | 2.14 | 1478 | 3 | 4 | 5 | 6 | VI-1 | LOC155060 | 2.78 |
| 1383 | 3 | 4 | 5 | 6 | | VI-1 | LARP4B | 2.07 | 1479 | 3 | 4 | 5 | 6 | VI-1 | LOC202181 | 4.64 |
| 1384 | 3 | 4 | 5 | 6 | | VI-1 | LARP7 | 2.73 | 1480 | 3 | 4 | 5 | 6 | VI-1 | LOC202781 | 3.14 |
| 1385 | 3 | 4 | 5 | 6 | | VI-1 | LARS | 2.04 | 1481 | 3 | 4 | 5 | 6 | VI-1 | LOC221442 | 2.50 |
| 1386 | 3 | 4 | 5 | 6 | | VI-1 | LATS2 | 2.58 | 1482 | 3 | 4 | 5 | 6 | VI-1 | LOC254100 | 2.50 |
| 1387 | 3 | 4 | 5 | 6 | | VI-1 | LBR | 2.10 | 1483 | 3 | 4 | 5 | 6 | VI-1 | LOC255512 | 2.14 |
| 1388 | 3 | 4 | 5 | 6 | | VI-1 | LCOR | 2.54 | 1484 | 3 | 4 | 5 | 6 | VI-1 | LOC283089 | 2.47 |
| 1389 | 3 | 4 | 5 | 6 | | VI-1 | LCORL | 2.08 | 1485 | 3 | 4 | 5 | 6 | VI-1 | LOC283174 | 3.69 |
| 1390 | 3 | 4 | 5 | 6 | | VI-1 | LCP2 | 2.43 | 1486 | 3 | 4 | 5 | 6 | VI-1 | LOC283710 | 2.41 |
| 1391 | 3 | 4 | 5 | 6 | | VI-1 | LDLRAP1 | 2.23 | 1487 | 3 | 4 | 5 | 6 | VI-1 | LOC284408 | 2.03 |
| 1392 | 3 | 4 | 5 | 6 | | VI-1 | LEPRE1 | 2.74 | 1488 | 3 | 4 | 5 | 6 | VI-1 | LOC285033 | 2.41 |
| 1393 | 3 | 4 | 5 | 6 | | VI-1 | LEPROT | 2.01 | 1489 | 3 | 4 | 5 | 6 | VI-1 | LOC285540 | 3.14 |
| 1394 | 3 | 4 | 5 | 6 | | VI-1 | LETM2 | 2.51 | 1490 | 3 | 4 | 5 | 6 | VI-1 | LOC285965 | 2.27 |
| 1395 | 3 | 4 | 5 | 6 | | VI-1 | LETMD1 | 2.46 | 1491 | 3 | 4 | 5 | 6 | VI-1 | LOC286437 | 4.00 |
| 1396 | 3 | 4 | 5 | 6 | | VI-1 | LGALS8 | 2.59 | 1492 | 3 | 4 | 5 | 6 | VI-1 | LOC338758 | 3.32 |
| 1397 | 3 | 4 | 5 | 6 | | VI-1 | LGALS9 | 3.14 | 1493 | 3 | 4 | 5 | 6 | VI-1 | LOC399753 | 2.20 |
| 1398 | 3 | 4 | 5 | 6 | | VI-1 | LGALSL | 2.69 | 1494 | 3 | 4 | 5 | 6 | VI-1 | LOC399940 | 3.70 |
| 1399 | 3 | 4 | 5 | 6 | | VI-1 | LIG1 | 3.38 | 1495 | 3 | 4 | 5 | 6 | VI-1 | LOC400236 | 2.01 |
| 1400 | 3 | 4 | 5 | 6 | | VI-1 | LIG4 | 2.19 | 1496 | 3 | 4 | 5 | 6 | VI-1 | LOC400657 | 2.06 |
| 1401 | 3 | 4 | 5 | 6 | | VI-1 | LILRA6 | 2.10 | 1497 | 3 | 4 | 5 | 6 | VI-1 | LOC401010 | 2.11 |
| 1402 | 3 | 4 | 5 | 6 | | VI-1 | LILRB1 | 2.29 | 1498 | 3 | 4 | 5 | 6 | VI-1 | LOC401588 | 3.57 |
| 1403 | 3 | 4 | 5 | 6 | | VI-1 | LILRB2 | 3.01 | 1499 | 3 | 4 | 5 | 6 | VI-1 | LOC439994 | 2.40 |
| 1404 | 3 | 4 | 5 | 6 | | VI-1 | LILRB3 | 3.19 | 1500 | 3 | 4 | 5 | 6 | VI-1 | LOC440354 | 2.52 |
| 1405 | 3 | 4 | 5 | 6 | | VI-1 | LIMD1 | 2.29 | 1501 | 3 | 4 | 5 | 6 | VI-1 | LOC440434 | 3.05 |
| 1406 | 3 | 4 | 5 | 6 | | VI-1 | LIMS1 | 2.10 | 1502 | 3 | 4 | 5 | 6 | VI-1 | LOC595101 | 2.20 |
| 1407 | 3 | 4 | 5 | 6 | | VI-1 | LINC00115 | 2.14 | 1503 | 3 | 4 | 5 | 6 | VI-1 | LOC613038 | 3.01 |
| 1408 | 3 | 4 | 5 | 6 | | VI-1 | LINC00260 | 2.02 | 1504 | 3 | 4 | 5 | 6 | VI-1 | LOC641298 | 2.30 |
| 1409 | 3 | 4 | 5 | 6 | | VI-1 | LINC00265 | 4.01 | 1505 | 3 | 4 | 5 | 6 | VI-1 | LOC641518 | 2.78 |
| 1410 | 3 | 4 | 5 | 6 | | VI-1 | LINC00294 | 2.72 | 1506 | 3 | 4 | 5 | 6 | VI-1 | LOC642361 | 3.58 |
| 1411 | 3 | 4 | 5 | 6 | | VI-1 | LINC00338 | 2.98 | 1507 | 3 | 4 | 5 | 6 | VI-1 | LOC642846 | 2.81 |
| 1412 | 3 | 4 | 5 | 6 | | VI-1 | LINC00341 | 2.32 | 1508 | 3 | 4 | 5 | 6 | VI-1 | LOC642852 | 2.80 |
| 1413 | 3 | 4 | 5 | 6 | | VI-1 | LINC00476 | 2.18 | 1509 | 3 | 4 | 5 | 6 | VI-1 | LOC643387 | 2.27 |
| 1414 | 3 | 4 | 5 | 6 | | VI-1 | LINC00482 | 2.38 | 1510 | 3 | 4 | 5 | 6 | VI-1 | LOC643837 | 2.07 |
| 1415 | 3 | 4 | 5 | 6 | | VI-1 | LINC00487 | 4.50 | 1511 | 3 | 4 | 5 | 6 | VI-1 | LOC644656 | 3.59 |
| 1416 | 3 | 4 | 5 | 6 | | VI-1 | LMAN1 | 2.12 | 1512 | 3 | 4 | 5 | 6 | VI-1 | LOC646329 | 2.30 |
| 1417 | 3 | 4 | 5 | 6 | | VI-1 | LMBR1L | 2.77 | 1513 | 3 | 4 | 5 | 6 | VI-1 | LOC646719 | 2.91 |
| 1418 | 3 | 4 | 5 | 6 | | VI-1 | LMBRD1 | 2.07 | 1514 | 3 | 4 | 5 | 6 | VI-1 | LOC648987 | 2.12 |
| 1419 | 3 | 4 | 5 | 6 | | VI-1 | LMF1 | 4.06 | 1515 | 3 | 4 | 5 | 6 | VI-1 | LOC729513 | 2.65 |
| 1420 | 3 | 4 | 5 | 6 | | VI-1 | LMF2 | 3.22 | 1516 | 3 | 4 | 5 | 6 | VI-1 | LOC80054 | 2.46 |
| 1421 | 3 | 4 | 5 | 6 | | VI-1 | LMNB1 | 2.44 | 1517 | 3 | 4 | 5 | 6 | VI-1 | LOC90834 | 2.99 |
| 1422 | 3 | 4 | 5 | 6 | | VI-1 | LMO2 | 3.69 | 1518 | 3 | 4 | 5 | 6 | VI-1 | LONP1 | 2.48 |
| 1423 | 3 | 4 | 5 | 6 | | VI-1 | LMO4 | 2.08 | 1519 | 3 | 4 | 5 | 6 | VI-1 | LONP2 | 2.00 |
| 1424 | 3 | 4 | 5 | 6 | | VI-1 | LMO7 | 2.12 | 1520 | 3 | 4 | 5 | 6 | VI-1 | LONRF1 | 2.42 |
| 1425 | 3 | 4 | 5 | 6 | | VI-1 | LOC100124692 | 2.36 | 1521 | 3 | 4 | 5 | 6 | VI-1 | LONRF3 | 2.25 |
| 1426 | 3 | 4 | 5 | 6 | | VI-1 | LOC100128071 | 4.60 | 1522 | 3 | 4 | 5 | 6 | VI-1 | LOXHD1 | 2.40 |
| 1427 | 3 | 4 | 5 | 6 | | VI-1 | LOC100128398 | 3.02 | 1523 | 3 | 4 | 5 | 6 | VI-1 | LOXL3 | 3.23 |
| 1428 | 3 | 4 | 5 | 6 | | VI-1 | LOC100128682 | 2.05 | 1524 | 3 | 4 | 5 | 6 | VI-1 | LPHN1 | 2.77 |
| 1429 | 3 | 4 | 5 | 6 | | VI-1 | LOC100128881 | 4.99 | 1525 | 3 | 4 | 5 | 6 | VI-1 | LPP | 3.76 |
| 1430 | 3 | 4 | 5 | 6 | | VI-1 | LOC100129387 | 3.50 | 1526 | 3 | 4 | 5 | 6 | VI-1 | LPXN | 2.04 |
| 1431 | 3 | 4 | 5 | 6 | | VI-1 | LOC100129556 | 2.39 | 1527 | 3 | 4 | 5 | 6 | VI-1 | LRCH3 | 2.03 |
| 1432 | 3 | 4 | 5 | 6 | | VI-1 | LOC100129726 | 3.84 | 1528 | 3 | 4 | 5 | 6 | VI-1 | LRIG2 | 2.05 |
| 1433 | 3 | 4 | 5 | 6 | | VI-1 | LOC100129917 | 3.89 | 1529 | 3 | 4 | 5 | 6 | VI-1 | LRMP | 2.04 |
| 1434 | 3 | 4 | 5 | 6 | | VI-1 | LOC100130357 | 2.38 | 1530 | 3 | 4 | 5 | 6 | VI-1 | LRP12 | 2.18 |
| 1435 | 3 | 4 | 5 | 6 | | VI-1 | LOC100130557 | 2.13 | 1531 | 3 | 4 | 5 | 6 | VI-1 | LRRC14 | 2.26 |
| 1436 | 3 | 4 | 5 | 6 | | VI-1 | LOC100130581 | 2.04 | 1532 | 3 | 4 | 5 | 6 | VI-1 | LRRC27 | 2.84 |

Fig. 40 - 9

| | | | | | | | | | | | | | | | | |
|---|---|---|---|---|---|---|---|---|---|---|---|---|---|---|---|---|
| 1533 | 3 | 4 | 5 | 6 | | VI-1 | LRRC33 | 2.63 | 1629 | 3 | 4 | 5 | 6 | | VI-1 | MGC27345 | 2.25 |
| 1534 | 3 | 4 | 5 | 6 | | VI-1 | LRRC37A4 | 3.01 | 1630 | 3 | 4 | 5 | 6 | | VI-1 | MGEA5 | 3.64 |
| 1535 | 3 | 4 | 5 | 6 | | VI-1 | LRRC37B | 2.53 | 1631 | 3 | 4 | 5 | 6 | | VI-1 | MIA3 | 2.85 |
| 1536 | 3 | 4 | 5 | 6 | | VI-1 | LRRC45 | 3.04 | 1632 | 3 | 4 | 5 | 6 | | VI-1 | MIB1 | 2.16 |
| 1537 | 3 | 4 | 5 | 6 | | VI-1 | LRRC6 | 4.41 | 1633 | 3 | 4 | 5 | 6 | | VI-1 | MIB2 | 2.82 |
| 1538 | 3 | 4 | 5 | 6 | | VI-1 | LRRC8C | 2.06 | 1634 | 3 | 4 | 5 | 6 | | VI-1 | MICAL3 | 2.80 |
| 1539 | 3 | 4 | 5 | 6 | | VI-1 | LRRC8D | 2.04 | 1635 | 3 | 4 | 5 | 6 | | VI-1 | MICALL1 | 2.50 |
| 1540 | 3 | 4 | 5 | 6 | | VI-1 | LRRCC1 | 2.02 | 1636 | 3 | 4 | 5 | 6 | | VI-1 | MIER2 | 2.27 |
| 1541 | 3 | 4 | 5 | 6 | | VI-1 | LRRFIP1 | 2.03 | 1637 | 3 | 4 | 5 | 6 | | VI-1 | MIIP | 2.09 |
| 1542 | 3 | 4 | 5 | 6 | | VI-1 | LRRFIP2 | 2.18 | 1638 | 3 | 4 | 5 | 6 | | VI-1 | MIS18BP1 | 2.42 |
| 1543 | 3 | 4 | 5 | 6 | | VI-1 | LRRK1 | 2.48 | 1639 | 3 | 4 | 5 | 6 | | VI-1 | MITF | 2.57 |
| 1544 | 3 | 4 | 5 | 6 | | VI-1 | LRRK2 | 3.11 | 1640 | 3 | 4 | 5 | 6 | | VI-1 | MKI67 | 2.83 |
| 1545 | 3 | 4 | 5 | 6 | | VI-1 | LRRN2 | 4.63 | 1641 | 3 | 4 | 5 | 6 | | VI-1 | MKL1 | 2.20 |
| 1546 | 3 | 4 | 5 | 6 | | VI-1 | LRSAM1 | 2.67 | 1642 | 3 | 4 | 5 | 6 | | VI-1 | MKLN1 | 2.72 |
| 1547 | 3 | 4 | 5 | 6 | | VI-1 | LTB4R2 | 2.51 | 1643 | 3 | 4 | 5 | 6 | | VI-1 | MLKL | 3.20 |
| 1548 | 3 | 4 | 5 | 6 | | VI-1 | LTBR | 2.14 | 1644 | 3 | 4 | 5 | 6 | | VI-1 | MLL2 | 2.28 |
| 1549 | 3 | 4 | 5 | 6 | | VI-1 | LTN1 | 2.41 | 1645 | 3 | 4 | 5 | 6 | | VI-1 | MLL3 | 2.61 |
| 1550 | 3 | 4 | 5 | 6 | | VI-1 | LY6G5C | 2.28 | 1646 | 3 | 4 | 5 | 6 | | VI-1 | MLL4 | 2.01 |
| 1551 | 3 | 4 | 5 | 6 | | VI-1 | LYSMD2 | 2.55 | 1647 | 3 | 4 | 5 | 6 | | VI-1 | MLL5 | 2.42 |
| 1552 | 3 | 4 | 5 | 6 | | VI-1 | LYSMD4 | 2.18 | 1648 | 3 | 4 | 5 | 6 | | VI-1 | MLXIP | 2.16 |
| 1553 | 3 | 4 | 5 | 6 | | VI-1 | LYST | 2.50 | 1649 | 3 | 4 | 5 | 6 | | VI-1 | MMS19 | 2.50 |
| 1554 | 3 | 4 | 5 | 6 | | VI-1 | LZIC | 2.18 | 1650 | 3 | 4 | 5 | 6 | | VI-1 | MOB1B | 2.49 |
| 1555 | 3 | 4 | 5 | 6 | | VI-1 | LZTR1 | 2.97 | 1651 | 3 | 4 | 5 | 6 | | VI-1 | MOB3B | 2.05 |
| 1556 | 3 | 4 | 5 | 6 | | VI-1 | LZTS2 | 2.09 | 1652 | 3 | 4 | 5 | 6 | | VI-1 | MOB4 | 3.38 |
| 1557 | 3 | 4 | 5 | 6 | | VI-1 | MACF1 | 2.67 | 1653 | 3 | 4 | 5 | 6 | | VI-1 | MOGS | 2.55 |
| 1558 | 3 | 4 | 5 | 6 | | VI-1 | MAD2L1BP | 2.17 | 1654 | 3 | 4 | 5 | 6 | | VI-1 | MON2 | 3.24 |
| 1559 | 3 | 4 | 5 | 6 | | VI-1 | MAF | 2.16 | 1655 | 3 | 4 | 5 | 6 | | VI-1 | MORC3 | 2.49 |
| 1560 | 3 | 4 | 5 | 6 | | VI-1 | MAFG | 2.74 | 1656 | 3 | 4 | 5 | 6 | | VI-1 | MOSPD2 | 2.17 |
| 1561 | 3 | 4 | 5 | 6 | | VI-1 | MAFK | 2.10 | 1657 | 3 | 4 | 5 | 6 | | VI-1 | MPHOSPH8 | 3.79 |
| 1562 | 3 | 4 | 5 | 6 | | VI-1 | MALT1 | 2.13 | 1658 | 3 | 4 | 5 | 6 | | VI-1 | MPRIP | 2.16 |
| 1563 | 3 | 4 | 5 | 6 | | VI-1 | MAN1A1 | 2.17 | 1659 | 3 | 4 | 5 | 6 | | VI-1 | MR1 | 2.51 |
| 1564 | 3 | 4 | 5 | 6 | | VI-1 | MAN1A2 | 2.63 | 1660 | 3 | 4 | 5 | 6 | | VI-1 | MRE11A | 2.84 |
| 1565 | 3 | 4 | 5 | 6 | | VI-1 | MAN2C1 | 3.06 | 1661 | 3 | 4 | 5 | 6 | | VI-1 | MRI1 | 3.53 |
| 1566 | 3 | 4 | 5 | 6 | | VI-1 | MANBA | 2.89 | 1662 | 3 | 4 | 5 | 6 | | VI-1 | MRPL42P5 | 2.29 |
| 1567 | 3 | 4 | 5 | 6 | | VI-1 | MAP3K1 | 2.48 | 1663 | 3 | 4 | 5 | 6 | | VI-1 | MRPL44 | 2.11 |
| 1568 | 3 | 4 | 5 | 6 | | VI-1 | MAP3K10 | 2.30 | 1664 | 3 | 4 | 5 | 6 | | VI-1 | MRPS18C | 2.26 |
| 1569 | 3 | 4 | 5 | 6 | | VI-1 | MAP3K12 | 2.69 | 1665 | 3 | 4 | 5 | 6 | | VI-1 | MRPS25 | 3.35 |
| 1570 | 3 | 4 | 5 | 6 | | VI-1 | MAP3K5 | 2.61 | 1666 | 3 | 4 | 5 | 6 | | VI-1 | MRRF | 2.02 |
| 1571 | 3 | 4 | 5 | 6 | | VI-1 | MAP4 | 2.27 | 1667 | 3 | 4 | 5 | 6 | | VI-1 | MSL3 | 2.30 |
| 1572 | 3 | 4 | 5 | 6 | | VI-1 | MAP4K2 | 2.20 | 1668 | 3 | 4 | 5 | 6 | | VI-1 | MST4 | 2.15 |
| 1573 | 3 | 4 | 5 | 6 | | VI-1 | MAP4K3 | 2.26 | 1669 | 3 | 4 | 5 | 6 | | VI-1 | MSTO1 | 3.02 |
| 1574 | 3 | 4 | 5 | 6 | | VI-1 | MAP4K5 | 2.44 | 1670 | 3 | 4 | 5 | 6 | | VI-1 | MSTO2P | 2.95 |
| 1575 | 3 | 4 | 5 | 6 | | VI-1 | MAPKBP1 | 2.20 | 1671 | 3 | 4 | 5 | 6 | | VI-1 | MTA1 | 2.67 |
| 1576 | 3 | 4 | 5 | 6 | | VI-1 | MAPRE1 | 2.04 | 1672 | 3 | 4 | 5 | 6 | | VI-1 | MTAP | 2.05 |
| 1577 | 3 | 4 | 5 | 6 | | VI-1 | MAPRE3 | 2.14 | 1673 | 3 | 4 | 5 | 6 | | VI-1 | MTF1 | 2.61 |
| 1578 | 3 | 4 | 5 | 6 | | VI-1 | 42435 | 2.07 | 1674 | 3 | 4 | 5 | 6 | | VI-1 | MTF2 | 2.24 |
| 1579 | 3 | 4 | 5 | 6 | | VI-1 | MARCKS | 2.07 | 1675 | 3 | 4 | 5 | 6 | | VI-1 | MTG1 | 3.25 |
| 1580 | 3 | 4 | 5 | 6 | | VI-1 | MARS | 3.08 | 1676 | 3 | 4 | 5 | 6 | | VI-1 | MTHFR | 2.85 |
| 1581 | 3 | 4 | 5 | 6 | | VI-1 | MAST4 | 2.27 | 1677 | 3 | 4 | 5 | 6 | | VI-1 | MTL5 | 2.32 |
| 1582 | 3 | 4 | 5 | 6 | | VI-1 | MAT2A | 2.19 | 1678 | 3 | 4 | 5 | 6 | | VI-1 | MTMR4 | 2.38 |
| 1583 | 3 | 4 | 5 | 6 | | VI-1 | MATL2963 | 2.78 | 1679 | 3 | 4 | 5 | 6 | | VI-1 | MTMR9 | 2.15 |
| 1584 | 3 | 4 | 5 | 6 | | VI-1 | MAU2 | 2.08 | 1680 | 3 | 4 | 5 | 6 | | VI-1 | MTOR | 2.54 |
| 1585 | 3 | 4 | 5 | 6 | | VI-1 | MAVS | 2.14 | 1681 | 3 | 4 | 5 | 6 | | VI-1 | MTPAP | 2.46 |
| 1586 | 3 | 4 | 5 | 6 | | VI-1 | MBD1 | 2.30 | 1682 | 3 | 4 | 5 | 6 | | VI-1 | MTRF1 | 3.90 |
| 1587 | 3 | 4 | 5 | 6 | | VI-1 | MBOAT1 | 2.95 | 1683 | 3 | 4 | 5 | 6 | | VI-1 | MTU51 | 2.97 |
| 1588 | 3 | 4 | 5 | 6 | | VI-1 | MBTD1 | 2.33 | 1684 | 3 | 4 | 5 | 6 | | VI-1 | MTX1 | 2.46 |
| 1589 | 3 | 4 | 5 | 6 | | VI-1 | MC1R | 2.25 | 1685 | 3 | 4 | 5 | 6 | | VI-1 | MTX3 | 2.25 |
| 1590 | 3 | 4 | 5 | 6 | | VI-1 | MCC | 2.45 | 1686 | 3 | 4 | 5 | 6 | | VI-1 | MUM1 | 2.84 |
| 1591 | 3 | 4 | 5 | 6 | | VI-1 | MCL1 | 2.35 | 1687 | 3 | 4 | 5 | 6 | | VI-1 | MUTED-TXNDC5 | 3.55 |
| 1592 | 3 | 4 | 5 | 6 | | VI-1 | MCM3AP | 2.47 | 1688 | 3 | 4 | 5 | 6 | | VI-1 | MVP | 2.60 |
| 1593 | 3 | 4 | 5 | 6 | | VI-1 | MCM7 | 2.38 | 1689 | 3 | 4 | 5 | 6 | | VI-1 | MX2 | 4.71 |
| 1594 | 3 | 4 | 5 | 6 | | VI-1 | MCM8 | 2.88 | 1690 | 3 | 4 | 5 | 6 | | VI-1 | MYADM | 2.66 |
| 1595 | 3 | 4 | 5 | 6 | | VI-1 | MCM9 | 2.10 | 1691 | 3 | 4 | 5 | 6 | | VI-1 | MYBPC3 | 3.24 |
| 1596 | 3 | 4 | 5 | 6 | | VI-1 | MCTS1 | 3.66 | 1692 | 3 | 4 | 5 | 6 | | VI-1 | MYCBP2 | 3.23 |
| 1597 | 3 | 4 | 5 | 6 | | VI-1 | MDC1 | 2.19 | 1693 | 3 | 4 | 5 | 6 | | VI-1 | MYCT1 | 3.03 |
| 1598 | 3 | 4 | 5 | 6 | | VI-1 | MDK | 3.68 | 1694 | 3 | 4 | 5 | 6 | | VI-1 | MYLIP | 2.27 |
| 1599 | 3 | 4 | 5 | 6 | | VI-1 | MDM1 | 2.23 | 1695 | 3 | 4 | 5 | 6 | | VI-1 | MYO18A | 2.85 |
| 1600 | 3 | 4 | 5 | 6 | | VI-1 | MDM4 | 3.17 | 1696 | 3 | 4 | 5 | 6 | | VI-1 | MYO19 | 2.99 |
| 1601 | 3 | 4 | 5 | 6 | | VI-1 | MDN1 | 3.20 | 1697 | 3 | 4 | 5 | 6 | | VI-1 | MYO1F | 2.12 |
| 1602 | 3 | 4 | 5 | 6 | | VI-1 | MDS2 | 3.58 | 1698 | 3 | 4 | 5 | 6 | | VI-1 | MYO5A | 2.08 |
| 1603 | 3 | 4 | 5 | 6 | | VI-1 | MED12 | 2.65 | 1699 | 3 | 4 | 5 | 6 | | VI-1 | MYO9B | 2.18 |
| 1604 | 3 | 4 | 5 | 6 | | VI-1 | MED13 | 2.49 | 1700 | 3 | 4 | 5 | 6 | | VI-1 | MYSM1 | 3.08 |
| 1605 | 3 | 4 | 5 | 6 | | VI-1 | MED13L | 2.41 | 1701 | 3 | 4 | 5 | 6 | | VI-1 | MZF1 | 3.72 |
| 1606 | 3 | 4 | 5 | 6 | | VI-1 | MED14 | 2.08 | 1702 | 3 | 4 | 5 | 6 | | VI-1 | N4BP2L1 | 2.42 |
| 1607 | 3 | 4 | 5 | 6 | | VI-1 | MED15 | 2.40 | 1703 | 3 | 4 | 5 | 6 | | VI-1 | N4BP2L2 | 2.97 |
| 1608 | 3 | 4 | 5 | 6 | | VI-1 | MED17 | 2.05 | 1704 | 3 | 4 | 5 | 6 | | VI-1 | N6AMT1 | 2.51 |
| 1609 | 3 | 4 | 5 | 6 | | VI-1 | MED23 | 2.65 | 1705 | 3 | 4 | 5 | 6 | | VI-1 | NAA16 | 2.43 |
| 1610 | 3 | 4 | 5 | 6 | | VI-1 | MED24 | 2.06 | 1706 | 3 | 4 | 5 | 6 | | VI-1 | NAA25 | 2.41 |
| 1611 | 3 | 4 | 5 | 6 | | VI-1 | MEF2A | 2.65 | 1707 | 3 | 4 | 5 | 6 | | VI-1 | NAA38 | 2.16 |
| 1612 | 3 | 4 | 5 | 6 | | VI-1 | MEFV | 2.72 | 1708 | 3 | 4 | 5 | 6 | | VI-1 | NACC2 | 2.46 |
| 1613 | 3 | 4 | 5 | 6 | | VI-1 | MEGF6 | 4.57 | 1709 | 3 | 4 | 5 | 6 | | VI-1 | NADK | 3.46 |
| 1614 | 3 | 4 | 5 | 6 | | VI-1 | MEGF8 | 2.12 | 1710 | 3 | 4 | 5 | 6 | | VI-1 | NADSYN1 | 2.56 |
| 1615 | 3 | 4 | 5 | 6 | | VI-1 | MEPCE | 2.13 | 1711 | 3 | 4 | 5 | 6 | | VI-1 | NAIP | 2.69 |
| 1616 | 3 | 4 | 5 | 6 | | VI-1 | METTL14 | 2.06 | 1712 | 3 | 4 | 5 | 6 | | VI-1 | NAP1L3 | 2.35 |
| 1617 | 3 | 4 | 5 | 6 | | VI-1 | METTL21D | 3.21 | 1713 | 3 | 4 | 5 | 6 | | VI-1 | NAPA | 2.42 |
| 1618 | 3 | 4 | 5 | 6 | | VI-1 | METTL3 | 2.78 | 1714 | 3 | 4 | 5 | 6 | | VI-1 | NAPB | 3.80 |
| 1619 | 3 | 4 | 5 | 6 | | VI-1 | METTL4 | 2.82 | 1715 | 3 | 4 | 5 | 6 | | VI-1 | NARFL | 2.33 |
| 1620 | 3 | 4 | 5 | 6 | | VI-1 | MFGE8 | 2.34 | 1716 | 3 | 4 | 5 | 6 | | VI-1 | NARS | 2.10 |
| 1621 | 3 | 4 | 5 | 6 | | VI-1 | MFN1 | 2.43 | 1717 | 3 | 4 | 5 | 6 | | VI-1 | NAT1 | 2.05 |
| 1622 | 3 | 4 | 5 | 6 | | VI-1 | MFSD1 | 2.19 | 1718 | 3 | 4 | 5 | 6 | | VI-1 | NAT9 | 2.57 |
| 1623 | 3 | 4 | 5 | 6 | | VI-1 | MFSD11 | 2.22 | 1719 | 3 | 4 | 5 | 6 | | VI-1 | NBAS | 2.10 |
| 1624 | 3 | 4 | 5 | 6 | | VI-1 | MFSD12 | 2.52 | 1720 | 3 | 4 | 5 | 6 | | VI-1 | NBN | 2.36 |
| 1625 | 3 | 4 | 5 | 6 | | VI-1 | MFSD3 | 2.57 | 1721 | 3 | 4 | 5 | 6 | | VI-1 | NBPF10 | 4.64 |
| 1626 | 3 | 4 | 5 | 6 | | VI-1 | MFSD6L | 2.06 | 1722 | 3 | 4 | 5 | 6 | | VI-1 | NBPF11 | 2.27 |
| 1627 | 3 | 4 | 5 | 6 | | VI-1 | MFSD8 | 3.42 | 1723 | 3 | 4 | 5 | 6 | | VI-1 | NBPF16 | 4.39 |
| 1628 | 3 | 4 | 5 | 6 | | VI-1 | MGA | 2.06 | 1724 | 3 | 4 | 5 | 6 | | VI-1 | NBPF24 | 3.89 |

Fig. 40 - 10

| | | | | | | | | | | | | | | | | |
|---|---|---|---|---|---|---|---|---|---|---|---|---|---|---|---|---|
| 1725 | 3 | 4 | 5 | 6 | | VI-1 | NBR1 | 2.08 | 1821 | 3 | 4 | 5 | 6 | | VI-1 | NUP133 | 2.08 |
| 1726 | 3 | 4 | 5 | 6 | | VI-1 | NCAPD2 | 2.15 | 1822 | 3 | 4 | 5 | 6 | | VI-1 | NUP160 | 2.05 |
| 1727 | 3 | 4 | 5 | 6 | | VI-1 | NCBP1 | 2.33 | 1823 | 3 | 4 | 5 | 6 | | VI-1 | NUP188 | 2.23 |
| 1728 | 3 | 4 | 5 | 6 | | VI-1 | NCDN | 2.37 | 1824 | 3 | 4 | 5 | 6 | | VI-1 | NUP205 | 2.65 |
| 1729 | 3 | 4 | 5 | 6 | | VI-1 | NCF2 | 2.16 | 1825 | 3 | 4 | 5 | 6 | | VI-1 | NUP210 | 2.45 |
| 1730 | 3 | 4 | 5 | 6 | | VI-1 | NCF4 | 2.23 | 1826 | 3 | 4 | 5 | 6 | | VI-1 | NUP43 | 2.41 |
| 1731 | 3 | 4 | 5 | 6 | | VI-1 | NCKAP1L | 2.14 | 1827 | 3 | 4 | 5 | 6 | | VI-1 | NUP62 | 2.09 |
| 1732 | 3 | 4 | 5 | 6 | | VI-1 | NCKAP5L | 2.25 | 1828 | 3 | 4 | 5 | 6 | | VI-1 | NUP85 | 2.73 |
| 1733 | 3 | 4 | 5 | 6 | | VI-1 | NCKIPSD | 2.08 | 1829 | 3 | 4 | 5 | 6 | | VI-1 | NUSAP1 | 2.72 |
| 1734 | 3 | 4 | 5 | 6 | | VI-1 | NCLN | 2.10 | 1830 | 3 | 4 | 5 | 6 | | VI-1 | OBFC2A | 3.95 |
| 1735 | 3 | 4 | 5 | 6 | | VI-1 | NCOA1 | 2.09 | 1831 | 3 | 4 | 5 | 6 | | VI-1 | OBSCN | 3.42 |
| 1736 | 3 | 4 | 5 | 6 | | VI-1 | NCOA3 | 2.96 | 1832 | 3 | 4 | 5 | 6 | | VI-1 | OCLM | 2.59 |
| 1737 | 3 | 4 | 5 | 6 | | VI-1 | NCOA6 | 2.00 | 1833 | 3 | 4 | 5 | 6 | | VI-1 | OCRL | 2.49 |
| 1738 | 3 | 4 | 5 | 6 | | VI-1 | NCOA7 | 2.92 | 1834 | 3 | 4 | 5 | 6 | | VI-1 | ODF2 | 2.57 |
| 1739 | 3 | 4 | 5 | 6 | | VI-1 | NCOR1 | 2.44 | 1835 | 3 | 4 | 5 | 6 | | VI-1 | ODF2L | 2.66 |
| 1740 | 3 | 4 | 5 | 6 | | VI-1 | NCOR2 | 2.41 | 1836 | 3 | 4 | 5 | 6 | | VI-1 | OFD1 | 2.67 |
| 1741 | 3 | 4 | 5 | 6 | | VI-1 | NCSTN | 2.39 | 1837 | 3 | 4 | 5 | 6 | | VI-1 | OGFOD2 | 2.88 |
| 1742 | 3 | 4 | 5 | 6 | | VI-1 | NDC80 | 2.50 | 1838 | 3 | 4 | 5 | 6 | | VI-1 | OGT | 4.85 |
| 1743 | 3 | 4 | 5 | 6 | | VI-1 | NDOR1 | 2.78 | 1839 | 3 | 4 | 5 | 6 | | VI-1 | OPRL1 | 2.69 |
| 1744 | 3 | 4 | 5 | 6 | | VI-1 | NDUFAF1 | 2.01 | 1840 | 3 | 4 | 5 | 6 | | VI-1 | OR2B6 | 2.11 |
| 1745 | 3 | 4 | 5 | 6 | | VI-1 | NDUFC2-KCTD14 | 2.52 | 1841 | 3 | 4 | 5 | 6 | | VI-1 | ORAI2 | 2.20 |
| 1746 | 3 | 4 | 5 | 6 | | VI-1 | NECAB3 | 2.11 | 1842 | 3 | 4 | 5 | 6 | | VI-1 | ORAOV1 | 2.03 |
| 1747 | 3 | 4 | 5 | 6 | | VI-1 | NECAP1 | 2.38 | 1843 | 3 | 4 | 5 | 6 | | VI-1 | ORC2 | 2.75 |
| 1748 | 3 | 4 | 5 | 6 | | VI-1 | NEDD9 | 2.18 | 1844 | 3 | 4 | 5 | 6 | | VI-1 | ORC3 | 2.34 |
| 1749 | 3 | 4 | 5 | 6 | | VI-1 | NEK8 | 3.04 | 1845 | 3 | 4 | 5 | 6 | | VI-1 | ORMDL1 | 2.50 |
| 1750 | 3 | 4 | 5 | 6 | | VI-1 | NEK9 | 2.41 | 1846 | 3 | 4 | 5 | 6 | | VI-1 | OS9 | 2.18 |
| 1751 | 3 | 4 | 5 | 6 | | VI-1 | NELF | 2.09 | 1847 | 3 | 4 | 5 | 6 | | VI-1 | OSBP | 2.00 |
| 1752 | 3 | 4 | 5 | 6 | | VI-1 | NEMF | 3.88 | 1848 | 3 | 4 | 5 | 6 | | VI-1 | OSBPL2 | 2.22 |
| 1753 | 3 | 4 | 5 | 6 | | VI-1 | NETO2 | 2.34 | 1849 | 3 | 4 | 5 | 6 | | VI-1 | OSBPL3 | 2.02 |
| 1754 | 3 | 4 | 5 | 6 | | VI-1 | NEU3 | 2.11 | 1850 | 3 | 4 | 5 | 6 | | VI-1 | OSCAR | 2.81 |
| 1755 | 3 | 4 | 5 | 6 | | VI-1 | NEURL4 | 2.55 | 1851 | 3 | 4 | 5 | 6 | | VI-1 | OSGEPL1 | 2.40 |
| 1756 | 3 | 4 | 5 | 6 | | VI-1 | NF1 | 2.18 | 1852 | 3 | 4 | 5 | 6 | | VI-1 | OSGIN2 | 2.15 |
| 1757 | 3 | 4 | 5 | 6 | | VI-1 | NFAT5 | 3.35 | 1853 | 3 | 4 | 5 | 6 | | VI-1 | OTUD1 | 2.67 |
| 1758 | 3 | 4 | 5 | 6 | | VI-1 | NFATC2IP | 3.12 | 1854 | 3 | 4 | 5 | 6 | | VI-1 | OTUD3 | 3.33 |
| 1759 | 3 | 4 | 5 | 6 | | VI-1 | NFKB1 | 2.01 | 1855 | 3 | 4 | 5 | 6 | | VI-1 | OTUD4 | 2.15 |
| 1760 | 3 | 4 | 5 | 6 | | VI-1 | NFKB2 | 2.31 | 1856 | 3 | 4 | 5 | 6 | | VI-1 | OTUD5 | 2.51 |
| 1761 | 3 | 4 | 5 | 6 | | VI-1 | NFKBIE | 2.09 | 1857 | 3 | 4 | 5 | 6 | | VI-1 | P2RY1 | 2.08 |
| 1762 | 3 | 4 | 5 | 6 | | VI-1 | NFRKB | 3.22 | 1858 | 3 | 4 | 5 | 6 | | VI-1 | P2RY12 | 3.19 |
| 1763 | 3 | 4 | 5 | 6 | | VI-1 | NFS1 | 2.29 | 1859 | 3 | 4 | 5 | 6 | | VI-1 | P2RY13 | 2.24 |
| 1764 | 3 | 4 | 5 | 6 | | VI-1 | NHLRC3 | 2.59 | 1860 | 3 | 4 | 5 | 6 | | VI-1 | P2RY6 | 3.09 |
| 1765 | 3 | 4 | 5 | 6 | | VI-1 | NHSL2 | 2.03 | 1861 | 3 | 4 | 5 | 6 | | VI-1 | P4HTM | 2.11 |
| 1766 | 3 | 4 | 5 | 6 | | VI-1 | NICN1 | 4.17 | 1862 | 3 | 4 | 5 | 6 | | VI-1 | PABPC1L | 4.68 |
| 1767 | 3 | 4 | 5 | 6 | | VI-1 | NIN | 2.24 | 1863 | 3 | 4 | 5 | 6 | | VI-1 | PABPN1 | 2.15 |
| 1768 | 3 | 4 | 5 | 6 | | VI-1 | NIPBL | 2.43 | 1864 | 3 | 4 | 5 | 6 | | VI-1 | PAFAH1B1 | 2.02 |
| 1769 | 3 | 4 | 5 | 6 | | VI-1 | NISCH | 3.04 | 1865 | 3 | 4 | 5 | 6 | | VI-1 | PAN3 | 3.17 |
| 1770 | 3 | 4 | 5 | 6 | | VI-1 | NIT1 | 2.66 | 1866 | 3 | 4 | 5 | 6 | | VI-1 | PAN3-AS1 | 3.39 |
| 1771 | 3 | 4 | 5 | 6 | | VI-1 | NKRF | 2.07 | 1867 | 3 | 4 | 5 | 6 | | VI-1 | PANK2 | 3.29 |
| 1772 | 3 | 4 | 5 | 6 | | VI-1 | NLRC4 | 2.32 | 1868 | 3 | 4 | 5 | 6 | | VI-1 | PANX1 | 2.10 |
| 1773 | 3 | 4 | 5 | 6 | | VI-1 | NLRC5 | 4.13 | 1869 | 3 | 4 | 5 | 6 | | VI-1 | PAOX | 2.72 |
| 1774 | 3 | 4 | 5 | 6 | | VI-1 | NLRP1 | 4.43 | 1870 | 3 | 4 | 5 | 6 | | VI-1 | PAPD5 | 2.25 |
| 1775 | 3 | 4 | 5 | 6 | | VI-1 | NLRP3 | 2.85 | 1871 | 3 | 4 | 5 | 6 | | VI-1 | PAPD7 | 3.14 |
| 1776 | 3 | 4 | 5 | 6 | | VI-1 | NMI | 3.84 | 1872 | 3 | 4 | 5 | 6 | | VI-1 | PAPOLA | 2.07 |
| 1777 | 3 | 4 | 5 | 6 | | VI-1 | NMT1 | 2.01 | 1873 | 3 | 4 | 5 | 6 | | VI-1 | PAPOLG | 2.44 |
| 1778 | 3 | 4 | 5 | 6 | | VI-1 | NOC2L | 2.04 | 1874 | 3 | 4 | 5 | 6 | | VI-1 | PAPSS2 | 2.90 |
| 1779 | 3 | 4 | 5 | 6 | | VI-1 | NOD1 | 3.88 | 1875 | 3 | 4 | 5 | 6 | | VI-1 | PARM1 | 2.44 |
| 1780 | 3 | 4 | 5 | 6 | | VI-1 | NOL3 | 2.58 | 1876 | 3 | 4 | 5 | 6 | | VI-1 | PARN | 2.08 |
| 1781 | 3 | 4 | 5 | 6 | | VI-1 | NOL8 | 2.76 | 1877 | 3 | 4 | 5 | 6 | | VI-1 | PARP11 | 2.14 |
| 1782 | 3 | 4 | 5 | 6 | | VI-1 | NOL9 | 2.43 | 1878 | 3 | 4 | 5 | 6 | | VI-1 | PARP3 | 3.01 |
| 1783 | 3 | 4 | 5 | 6 | | VI-1 | NOM1 | 2.55 | 1879 | 3 | 4 | 5 | 6 | | VI-1 | PARP4 | 2.26 |
| 1784 | 3 | 4 | 5 | 6 | | VI-1 | NOMO1 | 2.08 | 1880 | 3 | 4 | 5 | 6 | | VI-1 | PARP6 | 2.31 |
| 1785 | 3 | 4 | 5 | 6 | | VI-1 | NOMO2 | 2.01 | 1881 | 3 | 4 | 5 | 6 | | VI-1 | PARP8 | 2.19 |
| 1786 | 3 | 4 | 5 | 6 | | VI-1 | NOP2 | 2.31 | 1882 | 3 | 4 | 5 | 6 | | VI-1 | PARVG | 3.13 |
| 1787 | 3 | 4 | 5 | 6 | | VI-1 | NOP56 | 2.10 | 1883 | 3 | 4 | 5 | 6 | | VI-1 | PATL1 | 3.56 |
| 1788 | 3 | 4 | 5 | 6 | | VI-1 | NOTCH2 | 3.36 | 1884 | 3 | 4 | 5 | 6 | | VI-1 | PBLD | 2.20 |
| 1789 | 3 | 4 | 5 | 6 | | VI-1 | NOTCH2NL | 2.19 | 1885 | 3 | 4 | 5 | 6 | | VI-1 | PBRM1 | 2.00 |
| 1790 | 3 | 4 | 5 | 6 | | VI-1 | NPC2 | 2.51 | 1886 | 3 | 4 | 5 | 6 | | VI-1 | PBX2 | 2.24 |
| 1791 | 3 | 4 | 5 | 6 | | VI-1 | NPEPL1 | 4.38 | 1887 | 3 | 4 | 5 | 6 | | VI-1 | PBX3 | 2.11 |
| 1792 | 3 | 4 | 5 | 6 | | VI-1 | NPEPPS | 2.25 | 1888 | 3 | 4 | 5 | 6 | | VI-1 | PBX4 | 2.30 |
| 1793 | 3 | 4 | 5 | 6 | | VI-1 | NPFF | 3.05 | 1889 | 3 | 4 | 5 | 6 | | VI-1 | PCF11 | 2.73 |
| 1794 | 3 | 4 | 5 | 6 | | VI-1 | NPHP3 | 3.68 | 1890 | 3 | 4 | 5 | 6 | | VI-1 | PCK2 | 2.57 |
| 1795 | 3 | 4 | 5 | 6 | | VI-1 | NPPA-AS1 | 3.15 | 1891 | 3 | 4 | 5 | 6 | | VI-1 | PCM1 | 2.02 |
| 1796 | 3 | 4 | 5 | 6 | | VI-1 | NPTN | 2.00 | 1892 | 3 | 4 | 5 | 6 | | VI-1 | PCMT1 | 2.03 |
| 1797 | 3 | 4 | 5 | 6 | | VI-1 | NR2C1 | 3.29 | 1893 | 3 | 4 | 5 | 6 | | VI-1 | PCMTD2 | 2.45 |
| 1798 | 3 | 4 | 5 | 6 | | VI-1 | NR2C2 | 2.22 | 1894 | 3 | 4 | 5 | 6 | | VI-1 | PCNXL3 | 2.20 |
| 1799 | 3 | 4 | 5 | 6 | | VI-1 | NRBP2 | 3.46 | 1895 | 3 | 4 | 5 | 6 | | VI-1 | PCP2 | 3.46 |
| 1800 | 3 | 4 | 5 | 6 | | VI-1 | NRD1 | 2.14 | 1896 | 3 | 4 | 5 | 6 | | VI-1 | PDCD11 | 2.32 |
| 1801 | 3 | 4 | 5 | 6 | | VI-1 | NRIP1 | 2.04 | 1897 | 3 | 4 | 5 | 6 | | VI-1 | PDCD6IP | 2.94 |
| 1802 | 3 | 4 | 5 | 6 | | VI-1 | NRIP2 | 2.84 | 1898 | 3 | 4 | 5 | 6 | | VI-1 | PDCD7 | 2.09 |
| 1803 | 3 | 4 | 5 | 6 | | VI-1 | NRN1L | 2.22 | 1899 | 3 | 4 | 5 | 6 | | VI-1 | PDCL3 | 2.05 |
| 1804 | 3 | 4 | 5 | 6 | | VI-1 | NSMAF | 2.06 | 1900 | 3 | 4 | 5 | 6 | | VI-1 | PDDC1 | 2.25 |
| 1805 | 3 | 4 | 5 | 6 | | VI-1 | NSRP1 | 2.13 | 1901 | 3 | 4 | 5 | 6 | | VI-1 | PDE1B | 4.54 |
| 1806 | 3 | 4 | 5 | 6 | | VI-1 | NSUN2 | 2.08 | 1902 | 3 | 4 | 5 | 6 | | VI-1 | PDE3B | 2.20 |
| 1807 | 3 | 4 | 5 | 6 | | VI-1 | NSUN5 | 2.46 | 1903 | 3 | 4 | 5 | 6 | | VI-1 | PDE4B | 2.05 |
| 1808 | 3 | 4 | 5 | 6 | | VI-1 | NSUN6 | 2.67 | 1904 | 3 | 4 | 5 | 6 | | VI-1 | PDE4DIP | 2.77 |
| 1809 | 3 | 4 | 5 | 6 | | VI-1 | NT5C2 | 2.89 | 1905 | 3 | 4 | 5 | 6 | | VI-1 | PDE7A | 2.31 |
| 1810 | 3 | 4 | 5 | 6 | | VI-1 | NT5C3 | 4.86 | 1906 | 3 | 4 | 5 | 6 | | VI-1 | PDE8A | 3.19 |
| 1811 | 3 | 4 | 5 | 6 | | VI-1 | NTHL1 | 2.18 | 1907 | 3 | 4 | 5 | 6 | | VI-1 | PDGFA | 2.04 |
| 1812 | 3 | 4 | 5 | 6 | | VI-1 | NTSR1 | 2.95 | 1908 | 3 | 4 | 5 | 6 | | VI-1 | PDHX | 2.12 |
| 1813 | 3 | 4 | 5 | 6 | | VI-1 | NUB1 | 4.00 | 1909 | 3 | 4 | 5 | 6 | | VI-1 | PDLIM5 | 2.25 |
| 1814 | 3 | 4 | 5 | 6 | | VI-1 | NUDT13 | 2.01 | 1910 | 3 | 4 | 5 | 6 | | VI-1 | PDSS1 | 2.08 |
| 1815 | 3 | 4 | 5 | 6 | | VI-1 | NUDT18 | 2.37 | 1911 | 3 | 4 | 5 | 6 | | VI-1 | PDXDC1 | 2.18 |
| 1816 | 3 | 4 | 5 | 6 | | VI-1 | NUDT7 | 3.17 | 1912 | 3 | 4 | 5 | 6 | | VI-1 | PDXDC2P | 3.75 |
| 1817 | 3 | 4 | 5 | 6 | | VI-1 | NUDT9 | 2.31 | 1913 | 3 | 4 | 5 | 6 | | VI-1 | PELI2 | 2.23 |
| 1818 | 3 | 4 | 5 | 6 | | VI-1 | NUFIP2 | 2.16 | 1914 | 3 | 4 | 5 | 6 | | VI-1 | PEX16 | 2.10 |
| 1819 | 3 | 4 | 5 | 6 | | VI-1 | NUMA1 | 2.34 | 1915 | 3 | 4 | 5 | 6 | | VI-1 | PEX5 | 2.03 |
| 1820 | 3 | 4 | 5 | 6 | | VI-1 | NUMBL | 2.63 | 1916 | 3 | 4 | 5 | 6 | | VI-1 | PFKP | 2.19 |

Fig. 40 - 11

| | | | | | | | | | | | | | | | |
|---|---|---|---|---|---|---|---|---|---|---|---|---|---|---|---|
| 1917 | 3 | 4 | 5 | 6 | | VI-1 | PFN1P2 | 2.36 | 2013 | 3 | 4 | 5 | 6 | VI-1 | POLRMT | 2.14 |
| 1918 | 3 | 4 | 5 | 6 | | VI-1 | PGAP2 | 2.06 | 2014 | 3 | 4 | 5 | 6 | VI-1 | POMT1 | 2.11 |
| 1919 | 3 | 4 | 5 | 6 | | VI-1 | PGBD2 | 2.13 | 2015 | 3 | 4 | 5 | 6 | VI-1 | POU2F1 | 2.74 |
| 1920 | 3 | 4 | 5 | 6 | | VI-1 | PGBD3 | 2.05 | 2016 | 3 | 4 | 5 | 6 | VI-1 | POU6F1 | 2.94 |
| 1921 | 3 | 4 | 5 | 6 | | VI-1 | PGGT1B | 2.19 | 2017 | 3 | 4 | 5 | 6 | VI-1 | PPAPDC2 | 2.24 |
| 1922 | 3 | 4 | 5 | 6 | | VI-1 | PGM3 | 2.79 | 2018 | 3 | 4 | 5 | 6 | VI-1 | PPARD | 2.08 |
| 1923 | 3 | 4 | 5 | 6 | | VI-1 | PGS1 | 2.06 | 2019 | 3 | 4 | 5 | 6 | VI-1 | PPARGC1B | 3.09 |
| 1924 | 3 | 4 | 5 | 6 | | VI-1 | PHACTR4 | 2.24 | 2020 | 3 | 4 | 5 | 6 | VI-1 | PPCDC | 2.45 |
| 1925 | 3 | 4 | 5 | 6 | | VI-1 | PHC1 | 3.70 | 2021 | 3 | 4 | 5 | 6 | VI-1 | PPFIA1 | 2.15 |
| 1926 | 3 | 4 | 5 | 6 | | VI-1 | PHC3 | 2.50 | 2022 | 3 | 4 | 5 | 6 | VI-1 | PPFIBP2 | 2.59 |
| 1927 | 3 | 4 | 5 | 6 | | VI-1 | PHF10 | 2.10 | 2023 | 3 | 4 | 5 | 6 | VI-1 | PPIEL | 2.35 |
| 1928 | 3 | 4 | 5 | 6 | | VI-1 | PHF11 | 3.60 | 2024 | 3 | 4 | 5 | 6 | VI-1 | PPIL2 | 2.41 |
| 1929 | 3 | 4 | 5 | 6 | | VI-1 | PHF20L1 | 2.81 | 2025 | 3 | 4 | 5 | 6 | VI-1 | PPL | 3.65 |
| 1930 | 3 | 4 | 5 | 6 | | VI-1 | PHF21A | 2.28 | 2026 | 3 | 4 | 5 | 6 | VI-1 | PPM1K | 2.29 |
| 1931 | 3 | 4 | 5 | 6 | | VI-1 | PHF3 | 2.23 | 2027 | 3 | 4 | 5 | 6 | VI-1 | PPP1R12A | 2.51 |
| 1932 | 3 | 4 | 5 | 6 | | VI-1 | PHF6 | 2.17 | 2028 | 3 | 4 | 5 | 6 | VI-1 | PPP1R12B | 3.38 |
| 1933 | 3 | 4 | 5 | 6 | | VI-1 | PHIP | 4.48 | 2029 | 3 | 4 | 5 | 6 | VI-1 | PPP1R12C | 2.19 |
| 1934 | 3 | 4 | 5 | 6 | | VI-1 | PHKA2 | 2.96 | 2030 | 3 | 4 | 5 | 6 | VI-1 | PPP1R16A | 2.92 |
| 1935 | 3 | 4 | 5 | 6 | | VI-1 | PHKB | 2.60 | 2031 | 3 | 4 | 5 | 6 | VI-1 | PPP1R21 | 2.60 |
| 1936 | 3 | 4 | 5 | 6 | | VI-1 | PHKG2 | 2.41 | 2032 | 3 | 4 | 5 | 6 | VI-1 | PPP1R26 | 2.39 |
| 1937 | 3 | 4 | 5 | 6 | | VI-1 | PHLDB3 | 2.23 | 2033 | 3 | 4 | 5 | 6 | VI-1 | PPP1R37 | 2.18 |
| 1938 | 3 | 4 | 5 | 6 | | VI-1 | PHTF1 | 2.62 | 2034 | 3 | 4 | 5 | 6 | VI-1 | PPP1R3D | 2.04 |
| 1939 | 3 | 4 | 5 | 6 | | VI-1 | PI4K2B | 2.38 | 2035 | 3 | 4 | 5 | 6 | VI-1 | PPP2R1B | 2.40 |
| 1940 | 3 | 4 | 5 | 6 | | VI-1 | PI4KA | 2.66 | 2036 | 3 | 4 | 5 | 6 | VI-1 | PPP4R1L | 2.82 |
| 1941 | 3 | 4 | 5 | 6 | | VI-1 | PI4KAP2 | 3.32 | 2037 | 3 | 4 | 5 | 6 | VI-1 | PPP6R2 | 2.19 |
| 1942 | 3 | 4 | 5 | 6 | | VI-1 | PIAS3 | 2.02 | 2038 | 3 | 4 | 5 | 6 | VI-1 | PPP6R3 | 2.12 |
| 1943 | 3 | 4 | 5 | 6 | | VI-1 | PICALM | 2.36 | 2039 | 3 | 4 | 5 | 6 | VI-1 | PPTC7 | 2.19 |
| 1944 | 3 | 4 | 5 | 6 | | VI-1 | PICK1 | 2.96 | 2040 | 3 | 4 | 5 | 6 | VI-1 | PPWD1 | 2.60 |
| 1945 | 3 | 4 | 5 | 6 | | VI-1 | PIDD | 3.37 | 2041 | 3 | 4 | 5 | 6 | VI-1 | PRAM1 | 2.40 |
| 1946 | 3 | 4 | 5 | 6 | | VI-1 | PIEZO1 | 3.07 | 2042 | 3 | 4 | 5 | 6 | VI-1 | PRDM1 | 2.03 |
| 1947 | 3 | 4 | 5 | 6 | | VI-1 | PIGA | 2.01 | 2043 | 3 | 4 | 5 | 6 | VI-1 | PRDM10 | 2.53 |
| 1948 | 3 | 4 | 5 | 6 | | VI-1 | PIGB | 2.49 | 2044 | 3 | 4 | 5 | 6 | VI-1 | PRDM15 | 3.04 |
| 1949 | 3 | 4 | 5 | 6 | | VI-1 | PIGG | 4.28 | 2045 | 3 | 4 | 5 | 6 | VI-1 | PREPL | 2.10 |
| 1950 | 3 | 4 | 5 | 6 | | VI-1 | PIGH | 2.03 | 2046 | 3 | 4 | 5 | 6 | VI-1 | PRICKLE1 | 2.59 |
| 1951 | 3 | 4 | 5 | 6 | | VI-1 | PIGM | 2.84 | 2047 | 3 | 4 | 5 | 6 | VI-1 | PRICKLE4 | 2.38 |
| 1952 | 3 | 4 | 5 | 6 | | VI-1 | PIGV | 2.19 | 2048 | 3 | 4 | 5 | 6 | VI-1 | PRIM2 | 2.05 |
| 1953 | 3 | 4 | 5 | 6 | | VI-1 | PIK3AP1 | 2.68 | 2049 | 3 | 4 | 5 | 6 | VI-1 | PRKAB2 | 2.56 |
| 1954 | 3 | 4 | 5 | 6 | | VI-1 | PIK3C2A | 2.27 | 2050 | 3 | 4 | 5 | 6 | VI-1 | PRKAG2 | 2.34 |
| 1955 | 3 | 4 | 5 | 6 | | VI-1 | PIK3C3 | 2.10 | 2051 | 3 | 4 | 5 | 6 | VI-1 | PRKCD | 2.11 |
| 1956 | 3 | 4 | 5 | 6 | | VI-1 | PIK3CB | 2.18 | 2052 | 3 | 4 | 5 | 6 | VI-1 | PRKD2 | 3.40 |
| 1957 | 3 | 4 | 5 | 6 | | VI-1 | PIK3R4 | 2.25 | 2053 | 3 | 4 | 5 | 6 | VI-1 | PRKDC | 2.12 |
| 1958 | 3 | 4 | 5 | 6 | | VI-1 | PIKFYVE | 2.56 | 2054 | 3 | 4 | 5 | 6 | VI-1 | PROCA1 | 4.01 |
| 1959 | 3 | 4 | 5 | 6 | | VI-1 | PION | 3.01 | 2055 | 3 | 4 | 5 | 6 | VI-1 | PROSER1 | 2.14 |
| 1960 | 3 | 4 | 5 | 6 | | VI-1 | PIP4K2C | 2.36 | 2056 | 3 | 4 | 5 | 6 | VI-1 | PRPF3 | 2.98 |
| 1961 | 3 | 4 | 5 | 6 | | VI-1 | PISD | 2.57 | 2057 | 3 | 4 | 5 | 6 | VI-1 | PRPF38B | 2.14 |
| 1962 | 3 | 4 | 5 | 6 | | VI-1 | PITRM1 | 2.18 | 2058 | 3 | 4 | 5 | 6 | VI-1 | PRPF39 | 3.83 |
| 1963 | 3 | 4 | 5 | 6 | | VI-1 | PKD1 | 2.76 | 2059 | 3 | 4 | 5 | 6 | VI-1 | PRPF40A | 2.23 |
| 1964 | 3 | 4 | 5 | 6 | | VI-1 | PKD1P1 | 2.41 | 2060 | 3 | 4 | 5 | 6 | VI-1 | PRPF4B | 3.27 |
| 1965 | 3 | 4 | 5 | 6 | | VI-1 | PKD2 | 2.80 | 2061 | 3 | 4 | 5 | 6 | VI-1 | PRPF8 | 2.30 |
| 1966 | 3 | 4 | 5 | 6 | | VI-1 | PKI55 | 2.04 | 2062 | 3 | 4 | 5 | 6 | VI-1 | PRR14L | 2.32 |
| 1967 | 3 | 4 | 5 | 6 | | VI-1 | PKN2 | 3.90 | 2063 | 3 | 4 | 5 | 6 | VI-1 | PRR24 | 2.05 |
| 1968 | 3 | 4 | 5 | 6 | | VI-1 | PLA2G4A | 2.83 | 2064 | 3 | 4 | 5 | 6 | VI-1 | PRRC2C | 3.21 |
| 1969 | 3 | 4 | 5 | 6 | | VI-1 | PLAC8 | 2.00 | 2065 | 3 | 4 | 5 | 6 | VI-1 | PSAP | 2.29 |
| 1970 | 3 | 4 | 5 | 6 | | VI-1 | PLAGL2 | 2.08 | 2066 | 3 | 4 | 5 | 6 | VI-1 | PSEN2 | 2.44 |
| 1971 | 3 | 4 | 5 | 6 | | VI-1 | PLAUR | 2.61 | 2067 | 3 | 4 | 5 | 6 | VI-1 | PSIP1 | 2.05 |
| 1972 | 3 | 4 | 5 | 6 | | VI-1 | PLCB3 | 2.65 | 2068 | 3 | 4 | 5 | 6 | VI-1 | PSMA1 | 2.24 |
| 1973 | 3 | 4 | 5 | 6 | | VI-1 | PLCG1 | 2.19 | 2069 | 3 | 4 | 5 | 6 | VI-1 | PSMB10 | 2.59 |
| 1974 | 3 | 4 | 5 | 6 | | VI-1 | PLCG2 | 2.08 | 2070 | 3 | 4 | 5 | 6 | VI-1 | PSMB9 | 2.22 |
| 1975 | 3 | 4 | 5 | 6 | | VI-1 | PLCXD1 | 2.90 | 2071 | 3 | 4 | 5 | 6 | VI-1 | PSMD1 | 2.07 |
| 1976 | 3 | 4 | 5 | 6 | | VI-1 | PLD1 | 2.11 | 2072 | 3 | 4 | 5 | 6 | VI-1 | PSME1 | 2.05 |
| 1977 | 3 | 4 | 5 | 6 | | VI-1 | PLD6 | 2.36 | 2073 | 3 | 4 | 5 | 6 | VI-1 | PSME4 | 2.00 |
| 1978 | 3 | 4 | 5 | 6 | | VI-1 | PLEC | 3.35 | 2074 | 3 | 4 | 5 | 6 | VI-1 | PSTPIP2 | 3.18 |
| 1979 | 3 | 4 | 5 | 6 | | VI-1 | PLEKHA8P1 | 2.90 | 2075 | 3 | 4 | 5 | 6 | VI-1 | PTAR1 | 2.79 |
| 1980 | 3 | 4 | 5 | 6 | | VI-1 | PLEKHG2 | 3.30 | 2076 | 3 | 4 | 5 | 6 | VI-1 | PTBP1 | 2.05 |
| 1981 | 3 | 4 | 5 | 6 | | VI-1 | PLEKHG3 | 2.15 | 2077 | 3 | 4 | 5 | 6 | VI-1 | PTBP2 | 2.95 |
| 1982 | 3 | 4 | 5 | 6 | | VI-1 | PLEKHM1 | 2.05 | 2078 | 3 | 4 | 5 | 6 | VI-1 | PTCD3 | 2.90 |
| 1983 | 3 | 4 | 5 | 6 | | VI-1 | PLEKHO1 | 2.03 | 2079 | 3 | 4 | 5 | 6 | VI-1 | PTGDS | 3.04 |
| 1984 | 3 | 4 | 5 | 6 | | VI-1 | PLK1 | 2.02 | 2080 | 3 | 4 | 5 | 6 | VI-1 | PTK2B | 2.52 |
| 1985 | 3 | 4 | 5 | 6 | | VI-1 | PLOD1 | 2.05 | 2081 | 3 | 4 | 5 | 6 | VI-1 | PTOV1 | 2.29 |
| 1986 | 3 | 4 | 5 | 6 | | VI-1 | PLOD3 | 2.21 | 2082 | 3 | 4 | 5 | 6 | VI-1 | PTPLAD2 | 2.14 |
| 1987 | 3 | 4 | 5 | 6 | | VI-1 | PLXDC1 | 2.08 | 2083 | 3 | 4 | 5 | 6 | VI-1 | PTPN12 | 2.27 |
| 1988 | 3 | 4 | 5 | 6 | | VI-1 | PLXDC2 | 2.12 | 2084 | 3 | 4 | 5 | 6 | VI-1 | PTPN23 | 2.51 |
| 1989 | 3 | 4 | 5 | 6 | | VI-1 | PLXNA3 | 3.51 | 2085 | 3 | 4 | 5 | 6 | VI-1 | PTPRC | 2.25 |
| 1990 | 3 | 4 | 5 | 6 | | VI-1 | PM20D2 | 2.20 | 2086 | 3 | 4 | 5 | 6 | VI-1 | PTPRE | 3.12 |
| 1991 | 3 | 4 | 5 | 6 | | VI-1 | PMAIP1 | 3.57 | 2087 | 3 | 4 | 5 | 6 | VI-1 | PUM1 | 2.50 |
| 1992 | 3 | 4 | 5 | 6 | | VI-1 | PML | 4.98 | 2088 | 3 | 4 | 5 | 6 | VI-1 | PURB | 2.33 |
| 1993 | 3 | 4 | 5 | 6 | | VI-1 | PMS1 | 2.59 | 2089 | 3 | 4 | 5 | 6 | VI-1 | PUS1 | 2.18 |
| 1994 | 3 | 4 | 5 | 6 | | VI-1 | PMS2P3 | 3.05 | 2090 | 3 | 4 | 5 | 6 | VI-1 | PUS10 | 2.95 |
| 1995 | 3 | 4 | 5 | 6 | | VI-1 | PNKP | 2.84 | 2091 | 3 | 4 | 5 | 6 | VI-1 | PWWP2B | 2.10 |
| 1996 | 3 | 4 | 5 | 6 | | VI-1 | PNN | 3.84 | 2092 | 3 | 4 | 5 | 6 | VI-1 | PYGM | 3.98 |
| 1997 | 3 | 4 | 5 | 6 | | VI-1 | PNPT1 | 3.28 | 2093 | 3 | 4 | 5 | 6 | VI-1 | PYGO2 | 2.07 |
| 1998 | 3 | 4 | 5 | 6 | | VI-1 | POFUT2 | 3.42 | 2094 | 3 | 4 | 5 | 6 | VI-1 | QKI | 2.13 |
| 1999 | 3 | 4 | 5 | 6 | | VI-1 | POGZ | 3.46 | 2095 | 3 | 4 | 5 | 6 | VI-1 | QSOX2 | 3.28 |
| 2000 | 3 | 4 | 5 | 6 | | VI-1 | POLA2 | 2.56 | 2096 | 3 | 4 | 5 | 6 | VI-1 | QTRT1 | 3.13 |
| 2001 | 3 | 4 | 5 | 6 | | VI-1 | POLB | 2.15 | 2097 | 3 | 4 | 5 | 6 | VI-1 | QTRTD1 | 2.33 |
| 2002 | 3 | 4 | 5 | 6 | | VI-1 | POLD1 | 2.10 | 2098 | 3 | 4 | 5 | 6 | VI-1 | RAB11FIP1 | 2.61 |
| 2003 | 3 | 4 | 5 | 6 | | VI-1 | POLE | 3.63 | 2099 | 3 | 4 | 5 | 6 | VI-1 | RAB12 | 3.35 |
| 2004 | 3 | 4 | 5 | 6 | | VI-1 | POLG2 | 2.16 | 2100 | 3 | 4 | 5 | 6 | VI-1 | RAB14 | 2.26 |
| 2005 | 3 | 4 | 5 | 6 | | VI-1 | POLH | 2.75 | 2101 | 3 | 4 | 5 | 6 | VI-1 | RAB24 | 4.29 |
| 2006 | 3 | 4 | 5 | 6 | | VI-1 | POLI | 3.27 | 2102 | 3 | 4 | 5 | 6 | VI-1 | RAB37 | 2.08 |
| 2007 | 3 | 4 | 5 | 6 | | VI-1 | POLK | 2.04 | 2103 | 3 | 4 | 5 | 6 | VI-1 | RAB3GAP1 | 2.29 |
| 2008 | 3 | 4 | 5 | 6 | | VI-1 | POLM | 2.24 | 2104 | 3 | 4 | 5 | 6 | VI-1 | RAB3GAP2 | 2.12 |
| 2009 | 3 | 4 | 5 | 6 | | VI-1 | POLR2A | 2.93 | 2105 | 3 | 4 | 5 | 6 | VI-1 | RAB3IP | 3.30 |
| 2010 | 3 | 4 | 5 | 6 | | VI-1 | POLR2H | 2.45 | 2106 | 3 | 4 | 5 | 6 | VI-1 | RAB8A | 2.10 |
| 2011 | 3 | 4 | 5 | 6 | | VI-1 | POLR2J4 | 2.38 | 2107 | 3 | 4 | 5 | 6 | VI-1 | RABEP2 | 2.40 |
| 2012 | 3 | 4 | 5 | 6 | | VI-1 | POLR3A | 2.06 | 2108 | 3 | 4 | 5 | 6 | VI-1 | RABGAP1 | 2.33 |

Fig. 40 - 12

| | | | | | | | | | | | | | | | |
|---|---|---|---|---|---|---|---|---|---|---|---|---|---|---|---|
| 2109 | 3 | 4 | 5 | 6 | | VI-1 | RABGAP1L | 2.49 | 2205 | 3 | 4 | 5 | 6 | VI-1 | RNFT1 | 2.13 |
| 2110 | 3 | 4 | 5 | 6 | | VI-1 | RABGGTA | 2.73 | 2206 | 3 | 4 | 5 | 6 | VI-1 | RNPC3 | 4.48 |
| 2111 | 3 | 4 | 5 | 6 | | VI-1 | RABGGTB | 2.00 | 2207 | 3 | 4 | 5 | 6 | VI-1 | ROCK1 | 2.15 |
| 2112 | 3 | 4 | 5 | 6 | | VI-1 | RAC1 | 2.18 | 2208 | 3 | 4 | 5 | 6 | VI-1 | ROCK1P1 | 2.40 |
| 2113 | 3 | 4 | 5 | 6 | | VI-1 | RAD52 | 4.00 | 2209 | 3 | 4 | 5 | 6 | VI-1 | ROCK2 | 2.50 |
| 2114 | 3 | 4 | 5 | 6 | | VI-1 | RAD9A | 2.89 | 2210 | 3 | 4 | 5 | 6 | VI-1 | RPAIN | 2.35 |
| 2115 | 3 | 4 | 5 | 6 | | VI-1 | RAF1 | 2.44 | 2211 | 3 | 4 | 5 | 6 | VI-1 | RPAP3 | 2.32 |
| 2116 | 3 | 4 | 5 | 6 | | VI-1 | RALGAPA1 | 2.15 | 2212 | 3 | 4 | 5 | 6 | VI-1 | RPL18 | 2.00 |
| 2117 | 3 | 4 | 5 | 6 | | VI-1 | RALGAPA2 | 2.06 | 2213 | 3 | 4 | 5 | 6 | VI-1 | RPL21P44 | 4.95 |
| 2118 | 3 | 4 | 5 | 6 | | VI-1 | RALGAPB | 2.18 | 2214 | 3 | 4 | 5 | 6 | VI-1 | RPL32P3 | 4.61 |
| 2119 | 3 | 4 | 5 | 6 | | VI-1 | RALGPS1 | 2.34 | 2215 | 3 | 4 | 5 | 6 | VI-1 | RPL36A | 2.17 |
| 2120 | 3 | 4 | 5 | 6 | | VI-1 | RANBP6 | 2.40 | 2216 | 3 | 4 | 5 | 6 | VI-1 | RPP30 | 2.07 |
| 2121 | 3 | 4 | 5 | 6 | | VI-1 | RANGAP1 | 2.29 | 2217 | 3 | 4 | 5 | 6 | VI-1 | RPS15AP10 | 3.93 |
| 2122 | 3 | 4 | 5 | 6 | | VI-1 | RAP1GAP2 | 2.03 | 2218 | 3 | 4 | 5 | 6 | VI-1 | RPS6KC1 | 2.07 |
| 2123 | 3 | 4 | 5 | 6 | | VI-1 | RAP2C | 2.01 | 2219 | 3 | 4 | 5 | 6 | VI-1 | RRAGC | 2.05 |
| 2124 | 3 | 4 | 5 | 6 | | VI-1 | RASA1 | 2.60 | 2220 | 3 | 4 | 5 | 6 | VI-1 | RRBP1 | 2.72 |
| 2125 | 3 | 4 | 5 | 6 | | VI-1 | RASA4P | 2.63 | 2221 | 3 | 4 | 5 | 6 | VI-1 | RREB1 | 2.46 |
| 2126 | 3 | 4 | 5 | 6 | | VI-1 | RASAL3 | 2.14 | 2222 | 3 | 4 | 5 | 6 | VI-1 | RRM2 | 2.59 |
| 2127 | 3 | 4 | 5 | 6 | | VI-1 | RASGEF1B | 3.14 | 2223 | 3 | 4 | 5 | 6 | VI-1 | RRM28 | 2.42 |
| 2128 | 3 | 4 | 5 | 6 | | VI-1 | RASGRP2 | 2.51 | 2224 | 3 | 4 | 5 | 6 | VI-1 | RRN3P1 | 2.72 |
| 2129 | 3 | 4 | 5 | 6 | | VI-1 | RB1 | 2.16 | 2225 | 3 | 4 | 5 | 6 | VI-1 | RRN3P2 | 2.44 |
| 2130 | 3 | 4 | 5 | 6 | | VI-1 | RBAK | 2.06 | 2226 | 3 | 4 | 5 | 6 | VI-1 | RRN3P3 | 2.95 |
| 2131 | 3 | 4 | 5 | 6 | | VI-1 | RBBP6 | 2.97 | 2227 | 3 | 4 | 5 | 6 | VI-1 | RRNAD1 | 2.18 |
| 2132 | 3 | 4 | 5 | 6 | | VI-1 | RBCK1 | 2.92 | 2228 | 3 | 4 | 5 | 6 | VI-1 | RSAD1 | 2.18 |
| 2133 | 3 | 4 | 5 | 6 | | VI-1 | RBM10 | 2.43 | 2229 | 3 | 4 | 5 | 6 | VI-1 | RSBN1L | 2.47 |
| 2134 | 3 | 4 | 5 | 6 | | VI-1 | RBM11 | 2.20 | 2230 | 3 | 4 | 5 | 6 | VI-1 | RSF1 | 2.89 |
| 2135 | 3 | 4 | 5 | 6 | | VI-1 | RBM14 | 2.42 | 2231 | 3 | 4 | 5 | 6 | VI-1 | RSPH3 | 2.55 |
| 2136 | 3 | 4 | 5 | 6 | | VI-1 | RBM14-RBM4 | 2.14 | 2232 | 3 | 4 | 5 | 6 | VI-1 | RUFY2 | 3.09 |
| 2137 | 3 | 4 | 5 | 6 | | VI-1 | RBM19 | 2.54 | 2233 | 3 | 4 | 5 | 6 | VI-1 | RUFY3 | 4.21 |
| 2138 | 3 | 4 | 5 | 6 | | VI-1 | RBM23 | 2.24 | 2234 | 3 | 4 | 5 | 6 | VI-1 | RUNDC1 | 2.37 |
| 2139 | 3 | 4 | 5 | 6 | | VI-1 | RBM25 | 3.91 | 2235 | 3 | 4 | 5 | 6 | VI-1 | RUNX2 | 2.02 |
| 2140 | 3 | 4 | 5 | 6 | | VI-1 | RBM26 | 2.20 | 2236 | 3 | 4 | 5 | 6 | VI-1 | RWDD3 | 2.04 |
| 2141 | 3 | 4 | 5 | 6 | | VI-1 | RBM28 | 2.25 | 2237 | 3 | 4 | 5 | 6 | VI-1 | S100PBP | 2.13 |
| 2142 | 3 | 4 | 5 | 6 | | VI-1 | RBM39 | 2.86 | 2238 | 3 | 4 | 5 | 6 | VI-1 | SACS | 2.15 |
| 2143 | 3 | 4 | 5 | 6 | | VI-1 | RBM41 | 2.63 | 2239 | 3 | 4 | 5 | 6 | VI-1 | SAFB | 2.30 |
| 2144 | 3 | 4 | 5 | 6 | | VI-1 | RBM43 | 2.43 | 2240 | 3 | 4 | 5 | 6 | VI-1 | SAFB2 | 2.52 |
| 2145 | 3 | 4 | 5 | 6 | | VI-1 | RBM5 | 2.83 | 2241 | 3 | 4 | 5 | 6 | VI-1 | SAMD1 | 2.16 |
| 2146 | 3 | 4 | 5 | 6 | | VI-1 | RBM6 | 4.18 | 2242 | 3 | 4 | 5 | 6 | VI-1 | SAMD4B | 2.09 |
| 2147 | 3 | 4 | 5 | 6 | | VI-1 | RBMS1 | 2.42 | 2243 | 3 | 4 | 5 | 6 | VI-1 | SAMD8 | 2.54 |
| 2148 | 3 | 4 | 5 | 6 | | VI-1 | RBP5 | 2.31 | 2244 | 3 | 4 | 5 | 6 | VI-1 | SAMHD1 | 2.32 |
| 2149 | 3 | 4 | 5 | 6 | | VI-1 | RC3H1 | 2.39 | 2245 | 3 | 4 | 5 | 6 | VI-1 | SAP30L | 2.09 |
| 2150 | 3 | 4 | 5 | 6 | | VI-1 | RCBTB1 | 2.45 | 2246 | 3 | 4 | 5 | 6 | VI-1 | SARM1 | 2.15 |
| 2151 | 3 | 4 | 5 | 6 | | VI-1 | RCBTB2 | 2.66 | 2247 | 3 | 4 | 5 | 6 | VI-1 | SART1 | 2.02 |
| 2152 | 3 | 4 | 5 | 6 | | VI-1 | RCC2 | 2.06 | 2248 | 3 | 4 | 5 | 6 | VI-1 | SART3 | 2.06 |
| 2153 | 3 | 4 | 5 | 6 | | VI-1 | RCCD1 | 2.11 | 2249 | 3 | 4 | 5 | 6 | VI-1 | SASH1 | 2.05 |
| 2154 | 3 | 4 | 5 | 6 | | VI-1 | RCE1 | 2.19 | 2250 | 3 | 4 | 5 | 6 | VI-1 | SASS6 | 2.28 |
| 2155 | 3 | 4 | 5 | 6 | | VI-1 | RCOR1 | 2.09 | 2251 | 3 | 4 | 5 | 6 | VI-1 | SAT1 | 3.36 |
| 2156 | 3 | 4 | 5 | 6 | | VI-1 | RCOR3 | 2.15 | 2252 | 3 | 4 | 5 | 6 | VI-1 | SAV1 | 2.13 |
| 2157 | 3 | 4 | 5 | 6 | | VI-1 | RDH11 | 2.31 | 2253 | 3 | 4 | 5 | 6 | VI-1 | SBF2 | 2.28 |
| 2158 | 3 | 4 | 5 | 6 | | VI-1 | RDH13 | 2.72 | 2254 | 3 | 4 | 5 | 6 | VI-1 | SBNO1 | 2.02 |
| 2159 | 3 | 4 | 5 | 6 | | VI-1 | RDH5 | 3.95 | 2255 | 3 | 4 | 5 | 6 | VI-1 | SCAF11 | 2.29 |
| 2160 | 3 | 4 | 5 | 6 | | VI-1 | RECQL | 2.15 | 2256 | 3 | 4 | 5 | 6 | VI-1 | SCAF4 | 2.10 |
| 2161 | 3 | 4 | 5 | 6 | | VI-1 | RECQL5 | 2.86 | 2257 | 3 | 4 | 5 | 6 | VI-1 | SCAMP1 | 2.23 |
| 2162 | 3 | 4 | 5 | 6 | | VI-1 | REEP4 | 2.12 | 2258 | 3 | 4 | 5 | 6 | VI-1 | SCAND2 | 2.35 |
| 2163 | 3 | 4 | 5 | 6 | | VI-1 | RELA | 2.03 | 2259 | 3 | 4 | 5 | 6 | VI-1 | SCAPER | 3.47 |
| 2164 | 3 | 4 | 5 | 6 | | VI-1 | RELT | 2.28 | 2260 | 3 | 4 | 5 | 6 | VI-1 | SCARB2 | 3.08 |
| 2165 | 3 | 4 | 5 | 6 | | VI-1 | RENBP | 2.66 | 2261 | 3 | 4 | 5 | 6 | VI-1 | SCARF1 | 2.88 |
| 2166 | 3 | 4 | 5 | 6 | | VI-1 | RERE | 2.70 | 2262 | 3 | 4 | 5 | 6 | VI-1 | SCARNA10 | 3.06 |
| 2167 | 3 | 4 | 5 | 6 | | VI-1 | RETSAT | 2.23 | 2263 | 3 | 4 | 5 | 6 | VI-1 | SCARNA16 | 3.25 |
| 2168 | 3 | 4 | 5 | 6 | | VI-1 | REV1 | 2.30 | 2264 | 3 | 4 | 5 | 6 | VI-1 | SCLT1 | 2.80 |
| 2169 | 3 | 4 | 5 | 6 | | VI-1 | REV3L | 2.26 | 2265 | 3 | 4 | 5 | 6 | VI-1 | SCLY | 2.08 |
| 2170 | 3 | 4 | 5 | 6 | | VI-1 | RFC4 | 2.12 | 2266 | 3 | 4 | 5 | 6 | VI-1 | SCML1 | 3.77 |
| 2171 | 3 | 4 | 5 | 6 | | VI-1 | RFX1 | 2.59 | 2267 | 3 | 4 | 5 | 6 | VI-1 | SCRIB | 2.57 |
| 2172 | 3 | 4 | 5 | 6 | | VI-1 | RFX5 | 2.10 | 2268 | 3 | 4 | 5 | 6 | VI-1 | SCRN2 | 2.28 |
| 2173 | 3 | 4 | 5 | 6 | | VI-1 | RFXAP | 2.09 | 2269 | 3 | 4 | 5 | 6 | VI-1 | SDCBP | 2.11 |
| 2174 | 3 | 4 | 5 | 6 | | VI-1 | RG9MTD3 | 3.15 | 2270 | 3 | 4 | 5 | 6 | VI-1 | SDCCAG3 | 2.18 |
| 2175 | 3 | 4 | 5 | 6 | | VI-1 | RGAG4 | 4.09 | 2271 | 3 | 4 | 5 | 6 | VI-1 | SDHAP2 | 2.71 |
| 2176 | 3 | 4 | 5 | 6 | | VI-1 | RGPD3 | 2.17 | 2272 | 3 | 4 | 5 | 6 | VI-1 | SDR39U1 | 3.02 |
| 2177 | 3 | 4 | 5 | 6 | | VI-1 | RGPD4 | 3.71 | 2273 | 3 | 4 | 5 | 6 | VI-1 | SEC16A | 2.10 |
| 2178 | 3 | 4 | 5 | 6 | | VI-1 | RGS12 | 3.08 | 2274 | 3 | 4 | 5 | 6 | VI-1 | SEC24C | 2.11 |
| 2179 | 3 | 4 | 5 | 6 | | VI-1 | RHBDF2 | 3.96 | 2275 | 3 | 4 | 5 | 6 | VI-1 | SEC24D | 2.12 |
| 2180 | 3 | 4 | 5 | 6 | | VI-1 | RHD | 2.10 | 2276 | 3 | 4 | 5 | 6 | VI-1 | SEC31A | 2.25 |
| 2181 | 3 | 4 | 5 | 6 | | VI-1 | RHOT1 | 2.05 | 2277 | 3 | 4 | 5 | 6 | VI-1 | SEC62 | 2.04 |
| 2182 | 3 | 4 | 5 | 6 | | VI-1 | RHOT2 | 2.87 | 2278 | 3 | 4 | 5 | 6 | VI-1 | SECISBP2 | 2.71 |
| 2183 | 3 | 4 | 5 | 6 | | VI-1 | RHPN1 | 3.25 | 2279 | 3 | 4 | 5 | 6 | VI-1 | SECTM1 | 2.11 |
| 2184 | 3 | 4 | 5 | 6 | | VI-1 | RICTOR | 3.18 | 2280 | 3 | 4 | 5 | 6 | VI-1 | SEL1L | 2.10 |
| 2185 | 3 | 4 | 5 | 6 | | VI-1 | RIMKLB | 3.21 | 2281 | 3 | 4 | 5 | 6 | VI-1 | SELO | 3.02 |
| 2186 | 3 | 4 | 5 | 6 | | VI-1 | RIOK3 | 2.16 | 2282 | 3 | 4 | 5 | 6 | VI-1 | SEMA3C | 2.51 |
| 2187 | 3 | 4 | 5 | 6 | | VI-1 | RIPK1 | 2.16 | 2283 | 3 | 4 | 5 | 6 | VI-1 | SEMA4B | 2.23 |
| 2188 | 3 | 4 | 5 | 6 | | VI-1 | RIPK2 | 2.00 | 2284 | 3 | 4 | 5 | 6 | VI-1 | SEMA4D | 2.77 |
| 2189 | 3 | 4 | 5 | 6 | | VI-1 | RIPK3 | 3.52 | 2285 | 3 | 4 | 5 | 6 | VI-1 | SENP6 | 2.30 |
| 2190 | 3 | 4 | 5 | 6 | | VI-1 | RLTPR | 2.84 | 2286 | 3 | 4 | 5 | 6 | VI-1 | SENP7 | 2.53 |
| 2191 | 3 | 4 | 5 | 6 | | VI-1 | RMI2 | 2.29 | 2287 | 3 | 4 | 5 | 6 | VI-1 | SEPSECS | 2.32 |
| 2192 | 3 | 4 | 5 | 6 | | VI-1 | RNASE6 | 2.23 | 2288 | 3 | 4 | 5 | 6 | VI-1 | 42617 | 4.56 |
| 2193 | 3 | 4 | 5 | 6 | | VI-1 | RNASEH2C | 2.65 | 2289 | 3 | 4 | 5 | 6 | VI-1 | 42619 | 2.06 |
| 2194 | 3 | 4 | 5 | 6 | | VI-1 | RNASEL | 2.53 | 2290 | 3 | 4 | 5 | 6 | VI-1 | SEPT7P2 | 2.17 |
| 2195 | 3 | 4 | 5 | 6 | | VI-1 | RNF114 | 2.21 | 2291 | 3 | 4 | 5 | 6 | VI-1 | SERAC1 | 2.03 |
| 2196 | 3 | 4 | 5 | 6 | | VI-1 | RNF13 | 2.06 | 2292 | 3 | 4 | 5 | 6 | VI-1 | SETD1B | 2.09 |
| 2197 | 3 | 4 | 5 | 6 | | VI-1 | RNF135 | 2.26 | 2293 | 3 | 4 | 5 | 6 | VI-1 | SETD2 | 2.28 |
| 2198 | 3 | 4 | 5 | 6 | | VI-1 | RNF145 | 2.02 | 2294 | 3 | 4 | 5 | 6 | VI-1 | SETD4 | 3.08 |
| 2199 | 3 | 4 | 5 | 6 | | VI-1 | RNF149 | 2.54 | 2295 | 3 | 4 | 5 | 6 | VI-1 | SETD5 | 2.36 |
| 2200 | 3 | 4 | 5 | 6 | | VI-1 | RNF166 | 2.16 | 2296 | 3 | 4 | 5 | 6 | VI-1 | SETD6 | 2.86 |
| 2201 | 3 | 4 | 5 | 6 | | VI-1 | RNF169 | 2.35 | 2297 | 3 | 4 | 5 | 6 | VI-1 | SETDB1 | 2.49 |
| 2202 | 3 | 4 | 5 | 6 | | VI-1 | RNF19A | 2.38 | 2298 | 3 | 4 | 5 | 6 | VI-1 | SETDB2 | 2.44 |
| 2203 | 3 | 4 | 5 | 6 | | VI-1 | RNF31 | 2.74 | 2299 | 3 | 4 | 5 | 6 | VI-1 | SETX | 2.69 |
| 2204 | 3 | 4 | 5 | 6 | | VI-1 | RNF38 | 2.02 | 2300 | 3 | 4 | 5 | 6 | VI-1 | SF1 | 2.27 |

Fig. 40 - 13

| | | | | | | | | | | | | | | |
|---|---|---|---|---|---|---|---|---|---|---|---|---|---|---|
| 2301 | 3 | 4 | 5 | 6 | | VI-1 | SF3B1 | 3.39 | 2397 | 3 | 4 | 5 | 6 | | VI-1 | SMG9 | 2.36 |
| 2302 | 3 | 4 | 5 | 6 | | VI-1 | SF1 | 2.83 | 2398 | 3 | 4 | 5 | 6 | | VI-1 | SMPD4 | 2.01 |
| 2303 | 3 | 4 | 5 | 6 | | VI-1 | SFMBT2 | 2.45 | 2399 | 3 | 4 | 5 | 6 | | VI-1 | SMURF1 | 2.03 |
| 2304 | 3 | 4 | 5 | 6 | | VI-1 | SFPQ | 2.21 | 2400 | 3 | 4 | 5 | 6 | | VI-1 | SNAPC3 | 3.31 |
| 2305 | 3 | 4 | 5 | 6 | | VI-1 | SFSWAP | 2.21 | 2401 | 3 | 4 | 5 | 6 | | VI-1 | SNAPC4 | 2.73 |
| 2306 | 3 | 4 | 5 | 6 | | VI-1 | SFXN4 | 2.29 | 2402 | 3 | 4 | 5 | 6 | | VI-1 | SNHG1 | 2.06 |
| 2307 | 3 | 4 | 5 | 6 | | VI-1 | SGK3 | 2.06 | 2403 | 3 | 4 | 5 | 6 | | VI-1 | SNHG11 | 2.59 |
| 2308 | 3 | 4 | 5 | 6 | | VI-1 | SGK494 | 3.82 | 2404 | 3 | 4 | 5 | 6 | | VI-1 | SNHG7 | 3.00 |
| 2309 | 3 | 4 | 5 | 6 | | VI-1 | SGOL2 | 2.02 | 2405 | 3 | 4 | 5 | 6 | | VI-1 | SNORA6 | 4.24 |
| 2310 | 3 | 4 | 5 | 6 | | VI-1 | SGSH | 2.18 | 2406 | 3 | 4 | 5 | 6 | | VI-1 | SNRNP200 | 2.20 |
| 2311 | 3 | 4 | 5 | 6 | | VI-1 | SGSM2 | 3.19 | 2407 | 3 | 4 | 5 | 6 | | VI-1 | SNRNP35 | 2.08 |
| 2312 | 3 | 4 | 5 | 6 | | VI-1 | SGSM3 | 2.66 | 2408 | 3 | 4 | 5 | 6 | | VI-1 | SNX19 | 2.01 |
| 2313 | 3 | 4 | 5 | 6 | | VI-1 | SH2B1 | 3.75 | 2409 | 3 | 4 | 5 | 6 | | VI-1 | SNX21 | 2.67 |
| 2314 | 3 | 4 | 5 | 6 | | VI-1 | SH2B3 | 2.25 | 2410 | 3 | 4 | 5 | 6 | | VI-1 | SNX27 | 2.82 |
| 2315 | 3 | 4 | 5 | 6 | | VI-1 | SH2D3C | 2.54 | 2411 | 3 | 4 | 5 | 6 | | VI-1 | SOLH | 2.11 |
| 2316 | 3 | 4 | 5 | 6 | | VI-1 | SH3BP2 | 2.72 | 2412 | 3 | 4 | 5 | 6 | | VI-1 | SON | 2.90 |
| 2317 | 3 | 4 | 5 | 6 | | VI-1 | SHISA5 | 3.03 | 2413 | 3 | 4 | 5 | 6 | | VI-1 | SORL1 | 2.11 |
| 2318 | 3 | 4 | 5 | 6 | | VI-1 | SHPRH | 2.06 | 2414 | 3 | 4 | 5 | 6 | | VI-1 | SOS1 | 2.70 |
| 2319 | 3 | 4 | 5 | 6 | | VI-1 | SIGLEC12 | 2.87 | 2415 | 3 | 4 | 5 | 6 | | VI-1 | SP1 | 2.24 |
| 2320 | 3 | 4 | 5 | 6 | | VI-1 | SIGLEC16 | 4.19 | 2416 | 3 | 4 | 5 | 6 | | VI-1 | SP100 | 3.57 |
| 2321 | 3 | 4 | 5 | 6 | | VI-1 | SIGLEC9 | 2.01 | 2417 | 3 | 4 | 5 | 6 | | VI-1 | SP110 | 3.47 |
| 2322 | 3 | 4 | 5 | 6 | | VI-1 | SIK3 | 2.72 | 2418 | 3 | 4 | 5 | 6 | | VI-1 | SP140L | 3.48 |
| 2323 | 3 | 4 | 5 | 6 | | VI-1 | SIN3B | 2.63 | 2419 | 3 | 4 | 5 | 6 | | VI-1 | SPAG5-AS1 | 2.37 |
| 2324 | 3 | 4 | 5 | 6 | | VI-1 | SIPA1L1 | 3.05 | 2420 | 3 | 4 | 5 | 6 | | VI-1 | SPAG9 | 2.60 |
| 2325 | 3 | 4 | 5 | 6 | | VI-1 | SIRT1 | 2.24 | 2421 | 3 | 4 | 5 | 6 | | VI-1 | SPATA5L1 | 3.03 |
| 2326 | 3 | 4 | 5 | 6 | | VI-1 | SIRT7 | 2.67 | 2422 | 3 | 4 | 5 | 6 | | VI-1 | SPDYE2 | 4.95 |
| 2327 | 3 | 4 | 5 | 6 | | VI-1 | SKIL | 2.81 | 2423 | 3 | 4 | 5 | 6 | | VI-1 | SPDYE6 | 2.97 |
| 2328 | 3 | 4 | 5 | 6 | | VI-1 | SKIV2L | 2.81 | 2424 | 3 | 4 | 5 | 6 | | VI-1 | SPECC1 | 2.89 |
| 2329 | 3 | 4 | 5 | 6 | | VI-1 | SKP2 | 2.22 | 2425 | 3 | 4 | 5 | 6 | | VI-1 | SPEN | 2.29 |
| 2330 | 3 | 4 | 5 | 6 | | VI-1 | SLC11A2 | 2.10 | 2426 | 3 | 4 | 5 | 6 | | VI-1 | SPG11 | 3.31 |
| 2331 | 3 | 4 | 5 | 6 | | VI-1 | SLC12A4 | 2.68 | 2427 | 3 | 4 | 5 | 6 | | VI-1 | SPG7 | 2.74 |
| 2332 | 3 | 4 | 5 | 6 | | VI-1 | SLC12A6 | 2.32 | 2428 | 3 | 4 | 5 | 6 | | VI-1 | SPHK1 | 2.35 |
| 2333 | 3 | 4 | 5 | 6 | | VI-1 | SLC12A9 | 2.58 | 2429 | 3 | 4 | 5 | 6 | | VI-1 | SPNS1 | 2.08 |
| 2334 | 3 | 4 | 5 | 6 | | VI-1 | SLC15A2 | 3.56 | 2430 | 3 | 4 | 5 | 6 | | VI-1 | SPOCD1 | 2.32 |
| 2335 | 3 | 4 | 5 | 6 | | VI-1 | SLC15A4 | 2.31 | 2431 | 3 | 4 | 5 | 6 | | VI-1 | SPOPL | 2.42 |
| 2336 | 3 | 4 | 5 | 6 | | VI-1 | SLC16A13 | 2.42 | 2432 | 3 | 4 | 5 | 6 | | VI-1 | SPPL2A | 2.08 |
| 2337 | 3 | 4 | 5 | 6 | | VI-1 | SLC16A3 | 2.06 | 2433 | 3 | 4 | 5 | 6 | | VI-1 | SPPL2B | 3.22 |
| 2338 | 3 | 4 | 5 | 6 | | VI-1 | SLC16A5 | 2.61 | 2434 | 3 | 4 | 5 | 6 | | VI-1 | SPPL3 | 2.39 |
| 2339 | 3 | 4 | 5 | 6 | | VI-1 | SLC16A6 | 3.51 | 2435 | 3 | 4 | 5 | 6 | | VI-1 | SPRED2 | 2.04 |
| 2340 | 3 | 4 | 5 | 6 | | VI-1 | SLC17A5 | 2.57 | 2436 | 3 | 4 | 5 | 6 | | VI-1 | SPRN | 2.52 |
| 2341 | 3 | 4 | 5 | 6 | | VI-1 | SLC17A9 | 4.53 | 2437 | 3 | 4 | 5 | 6 | | VI-1 | SPSB1 | 2.23 |
| 2342 | 3 | 4 | 5 | 6 | | VI-1 | SLC20A1 | 2.58 | 2438 | 3 | 4 | 5 | 6 | | VI-1 | SPTLC1 | 2.10 |
| 2343 | 3 | 4 | 5 | 6 | | VI-1 | SLC22A15 | 3.45 | 2439 | 3 | 4 | 5 | 6 | | VI-1 | SPTLC2 | 2.25 |
| 2344 | 3 | 4 | 5 | 6 | | VI-1 | SLC22A17 | 3.07 | 2440 | 3 | 4 | 5 | 6 | | VI-1 | SQRDL | 2.37 |
| 2345 | 3 | 4 | 5 | 6 | | VI-1 | SLC22A4 | 4.49 | 2441 | 3 | 4 | 5 | 6 | | VI-1 | SR8D1 | 3.25 |
| 2346 | 3 | 4 | 5 | 6 | | VI-1 | SLC22A5 | 2.24 | 2442 | 3 | 4 | 5 | 6 | | VI-1 | SRC | 3.46 |
| 2347 | 3 | 4 | 5 | 6 | | VI-1 | SLC23A2 | 2.81 | 2443 | 3 | 4 | 5 | 6 | | VI-1 | SREBF1 | 2.01 |
| 2348 | 3 | 4 | 5 | 6 | | VI-1 | SLC24A1 | 2.16 | 2444 | 3 | 4 | 5 | 6 | | VI-1 | SREK1 | 2.69 |
| 2349 | 3 | 4 | 5 | 6 | | VI-1 | SLC25A13 | 2.64 | 2445 | 3 | 4 | 5 | 6 | | VI-1 | SRGAP2 | 4.09 |
| 2350 | 3 | 4 | 5 | 6 | | VI-1 | SLC25A22 | 2.43 | 2446 | 3 | 4 | 5 | 6 | | VI-1 | SRGAP2P2 | 3.04 |
| 2351 | 3 | 4 | 5 | 6 | | VI-1 | SLC25A25 | 2.35 | 2447 | 3 | 4 | 5 | 6 | | VI-1 | SRRM1 | 2.07 |
| 2352 | 3 | 4 | 5 | 6 | | VI-1 | SLC25A28 | 3.10 | 2448 | 3 | 4 | 5 | 6 | | VI-1 | SRRM2 | 4.67 |
| 2353 | 3 | 4 | 5 | 6 | | VI-1 | SLC25A30 | 2.44 | 2449 | 3 | 4 | 5 | 6 | | VI-1 | SRRT | 2.20 |
| 2354 | 3 | 4 | 5 | 6 | | VI-1 | SLC25A34 | 2.66 | 2450 | 3 | 4 | 5 | 6 | | VI-1 | SRSF1 | 2.05 |
| 2355 | 3 | 4 | 5 | 6 | | VI-1 | SLC25A45 | 2.41 | 2451 | 3 | 4 | 5 | 6 | | VI-1 | SRSF11 | 3.22 |
| 2356 | 3 | 4 | 5 | 6 | | VI-1 | SLC26A1 | 2.39 | 2452 | 3 | 4 | 5 | 6 | | VI-1 | SRSF5 | 3.67 |
| 2357 | 3 | 4 | 5 | 6 | | VI-1 | SLC26A6 | 3.79 | 2453 | 3 | 4 | 5 | 6 | | VI-1 | SRSF6 | 2.84 |
| 2358 | 3 | 4 | 5 | 6 | | VI-1 | SLC27A3 | 3.40 | 2454 | 3 | 4 | 5 | 6 | | VI-1 | SRSF7 | 2.54 |
| 2359 | 3 | 4 | 5 | 6 | | VI-1 | SLC2A11 | 2.73 | 2455 | 3 | 4 | 5 | 6 | | VI-1 | SS18 | 2.11 |
| 2360 | 3 | 4 | 5 | 6 | | VI-1 | SLC30A1 | 2.09 | 2456 | 3 | 4 | 5 | 6 | | VI-1 | SS18L1 | 4.77 |
| 2361 | 3 | 4 | 5 | 6 | | VI-1 | SLC30A7 | 2.90 | 2457 | 3 | 4 | 5 | 6 | | VI-1 | SSBP2 | 2.11 |
| 2362 | 3 | 4 | 5 | 6 | | VI-1 | SLC35B1 | 2.32 | 2458 | 3 | 4 | 5 | 6 | | VI-1 | SSX2IP | 2.20 |
| 2363 | 3 | 4 | 5 | 6 | | VI-1 | SLC35B3 | 2.72 | 2459 | 3 | 4 | 5 | 6 | | VI-1 | ST3GAL5 | 2.88 |
| 2364 | 3 | 4 | 5 | 6 | | VI-1 | SLC35E2B | 2.73 | 2460 | 3 | 4 | 5 | 6 | | VI-1 | ST7L | 2.33 |
| 2365 | 3 | 4 | 5 | 6 | | VI-1 | SLC35F5 | 2.36 | 2461 | 3 | 4 | 5 | 6 | | VI-1 | STAG3L1 | 4.27 |
| 2366 | 3 | 4 | 5 | 6 | | VI-1 | SLC37A1 | 2.43 | 2462 | 3 | 4 | 5 | 6 | | VI-1 | STAG3L2 | 3.61 |
| 2367 | 3 | 4 | 5 | 6 | | VI-1 | SLC38A10 | 2.60 | 2463 | 3 | 4 | 5 | 6 | | VI-1 | STAG3L3 | 4.09 |
| 2368 | 3 | 4 | 5 | 6 | | VI-1 | SLC38A2 | 2.49 | 2464 | 3 | 4 | 5 | 6 | | VI-1 | STAG3L4 | 2.17 |
| 2369 | 3 | 4 | 5 | 6 | | VI-1 | SLC38A9 | 2.38 | 2465 | 3 | 4 | 5 | 6 | | VI-1 | STAM2 | 2.10 |
| 2370 | 3 | 4 | 5 | 6 | | VI-1 | SLC3A2 | 2.87 | 2466 | 3 | 4 | 5 | 6 | | VI-1 | STAMBP | 2.09 |
| 2371 | 3 | 4 | 5 | 6 | | VI-1 | SLC44A1 | 2.04 | 2467 | 3 | 4 | 5 | 6 | | VI-1 | STARD3 | 2.18 |
| 2372 | 3 | 4 | 5 | 6 | | VI-1 | SLC4A2 | 2.58 | 2468 | 3 | 4 | 5 | 6 | | VI-1 | STARD4 | 2.04 |
| 2373 | 3 | 4 | 5 | 6 | | VI-1 | SLC4A5 | 2.04 | 2469 | 3 | 4 | 5 | 6 | | VI-1 | STARD8 | 3.40 |
| 2374 | 3 | 4 | 5 | 6 | | VI-1 | SLC5A3 | 2.63 | 2470 | 3 | 4 | 5 | 6 | | VI-1 | STAT3 | 2.45 |
| 2375 | 3 | 4 | 5 | 6 | | VI-1 | SLC5A6 | 2.11 | 2471 | 3 | 4 | 5 | 6 | | VI-1 | STAT5A | 2.03 |
| 2376 | 3 | 4 | 5 | 6 | | VI-1 | SLC6A6 | 2.43 | 2472 | 3 | 4 | 5 | 6 | | VI-1 | STAT6 | 2.55 |
| 2377 | 3 | 4 | 5 | 6 | | VI-1 | SLC7A6 | 2.88 | 2473 | 3 | 4 | 5 | 6 | | VI-1 | STIM2 | 2.14 |
| 2378 | 3 | 4 | 5 | 6 | | VI-1 | SLC9A1 | 2.20 | 2474 | 3 | 4 | 5 | 6 | | VI-1 | STK11IP | 2.60 |
| 2379 | 3 | 4 | 5 | 6 | | VI-1 | SLC9A8 | 3.36 | 2475 | 3 | 4 | 5 | 6 | | VI-1 | STK19 | 3.06 |
| 2380 | 3 | 4 | 5 | 6 | | VI-1 | SLC9A9 | 2.19 | 2476 | 3 | 4 | 5 | 6 | | VI-1 | STK24 | 2.00 |
| 2381 | 3 | 4 | 5 | 6 | | VI-1 | SLCO3A1 | 2.01 | 2477 | 3 | 4 | 5 | 6 | | VI-1 | STK3 | 2.13 |
| 2382 | 3 | 4 | 5 | 6 | | VI-1 | SLFN11 | 4.43 | 2478 | 3 | 4 | 5 | 6 | | VI-1 | STK36 | 2.84 |
| 2383 | 3 | 4 | 5 | 6 | | VI-1 | SLFN12 | 3.53 | 2479 | 3 | 4 | 5 | 6 | | VI-1 | STK38 | 2.28 |
| 2384 | 3 | 4 | 5 | 6 | | VI-1 | SLITRK4 | 2.27 | 2480 | 3 | 4 | 5 | 6 | | VI-1 | STK38L | 2.08 |
| 2385 | 3 | 4 | 5 | 6 | | VI-1 | SLTM | 2.23 | 2481 | 3 | 4 | 5 | 6 | | VI-1 | STRADA | 2.05 |
| 2386 | 3 | 4 | 5 | 6 | | VI-1 | SLX4 | 2.78 | 2482 | 3 | 4 | 5 | 6 | | VI-1 | STRN3 | 2.02 |
| 2387 | 3 | 4 | 5 | 6 | | VI-1 | SMA4 | 3.87 | 2483 | 3 | 4 | 5 | 6 | | VI-1 | STS | 2.24 |
| 2388 | 3 | 4 | 5 | 6 | | VI-1 | SMA5 | 2.54 | 2484 | 3 | 4 | 5 | 6 | | VI-1 | STT3A | 2.12 |
| 2389 | 3 | 4 | 5 | 6 | | VI-1 | SMAD1 | 3.09 | 2485 | 3 | 4 | 5 | 6 | | VI-1 | STX11 | 2.52 |
| 2390 | 3 | 4 | 5 | 6 | | VI-1 | SMARCAD1 | 2.01 | 2486 | 3 | 4 | 5 | 6 | | VI-1 | STX16-NPEPL1 | 2.44 |
| 2391 | 3 | 4 | 5 | 6 | | VI-1 | SMARCC2 | 2.32 | 2487 | 3 | 4 | 5 | 6 | | VI-1 | STX17 | 2.97 |
| 2392 | 3 | 4 | 5 | 6 | | VI-1 | SMC4 | 3.31 | 2488 | 3 | 4 | 5 | 6 | | VI-1 | STX2 | 4.05 |
| 2393 | 3 | 4 | 5 | 6 | | VI-1 | SMC6 | 2.25 | 2489 | 3 | 4 | 5 | 6 | | VI-1 | STX4 | 2.13 |
| 2394 | 3 | 4 | 5 | 6 | | VI-1 | SMCHD1 | 3.96 | 2490 | 3 | 4 | 5 | 6 | | VI-1 | STX7 | 3.32 |
| 2395 | 3 | 4 | 5 | 6 | | VI-1 | SMG1 | 3.49 | 2491 | 3 | 4 | 5 | 6 | | VI-1 | STXBP3 | 2.66 |
| 2396 | 3 | 4 | 5 | 6 | | VI-1 | SMG5 | 2.83 | 2492 | 3 | 4 | 5 | 6 | | VI-1 | STXBP5 | 2.05 |

Fig. 40 - 14

| | | | | | | | |
|---|---|---|---|---|---|---|---|
| 2493 | 3 | 4 | 5 | 6 | VI-1 | SUDS3 | 2.14 |
| 2494 | 3 | 4 | 5 | 6 | VI-1 | SUGP2 | 4.31 |
| 2495 | 3 | 4 | 5 | 6 | VI-1 | SULF2 | 2.35 |
| 2496 | 3 | 4 | 5 | 6 | VI-1 | SUMO4 | 2.13 |
| 2497 | 3 | 4 | 5 | 6 | VI-1 | SUN1 | 3.00 |
| 2498 | 3 | 4 | 5 | 6 | VI-1 | SUOX | 2.20 |
| 2499 | 3 | 4 | 5 | 6 | VI-1 | SUPT5H | 2.31 |
| 2500 | 3 | 4 | 5 | 6 | VI-1 | SUPT6H | 2.13 |
| 2501 | 3 | 4 | 5 | 6 | VI-1 | SUPT7L | 2.39 |
| 2502 | 3 | 4 | 5 | 6 | VI-1 | SURF6 | 2.14 |
| 2503 | 3 | 4 | 5 | 6 | VI-1 | SUV39H2 | 2.23 |
| 2504 | 3 | 4 | 5 | 6 | VI-1 | SVIL | 2.26 |
| 2505 | 3 | 4 | 5 | 6 | VI-1 | SYMPK | 2.28 |
| 2506 | 3 | 4 | 5 | 6 | VI-1 | SYNE2 | 3.02 |
| 2507 | 3 | 4 | 5 | 6 | VI-1 | SYNJ1 | 2.57 |
| 2508 | 3 | 4 | 5 | 6 | VI-1 | SYNRG | 2.04 |
| 2509 | 3 | 4 | 5 | 6 | VI-1 | SYTL1 | 2.13 |
| 2510 | 3 | 4 | 5 | 6 | VI-1 | SYVN1 | 2.22 |
| 2511 | 3 | 4 | 5 | 6 | VI-1 | SZT2 | 3.32 |
| 2512 | 3 | 4 | 5 | 6 | VI-1 | TA83 | 2.45 |
| 2513 | 3 | 4 | 5 | 6 | VI-1 | TACC1 | 2.70 |
| 2514 | 3 | 4 | 5 | 6 | VI-1 | TAF1 | 2.27 |
| 2515 | 3 | 4 | 5 | 6 | VI-1 | TAF1B | 2.20 |
| 2516 | 3 | 4 | 5 | 6 | VI-1 | TAF1C | 3.99 |
| 2517 | 3 | 4 | 5 | 6 | VI-1 | TAF3 | 2.24 |
| 2518 | 3 | 4 | 5 | 6 | VI-1 | TAF5 | 2.00 |
| 2519 | 3 | 4 | 5 | 6 | VI-1 | TAF6L | 2.43 |
| 2520 | 3 | 4 | 5 | 6 | VI-1 | TAGAP | 2.21 |
| 2521 | 3 | 4 | 5 | 6 | VI-1 | TAGLN | 4.08 |
| 2522 | 3 | 4 | 5 | 6 | VI-1 | TAMM41 | 2.31 |
| 2523 | 3 | 4 | 5 | 6 | VI-1 | TAOK1 | 2.01 |
| 2524 | 3 | 4 | 5 | 6 | VI-1 | TAOK2 | 2.36 |
| 2525 | 3 | 4 | 5 | 6 | VI-1 | TAP1 | 3.46 |
| 2526 | 3 | 4 | 5 | 6 | VI-1 | TAPBP | 2.06 |
| 2527 | 3 | 4 | 5 | 6 | VI-1 | TAPBPL | 2.16 |
| 2528 | 3 | 4 | 5 | 6 | VI-1 | TARBP1 | 3.08 |
| 2529 | 3 | 4 | 5 | 6 | VI-1 | TARDBP | 2.55 |
| 2530 | 3 | 4 | 5 | 6 | VI-1 | TAZ | 2.47 |
| 2531 | 3 | 4 | 5 | 6 | VI-1 | TBC1D1 | 2.06 |
| 2532 | 3 | 4 | 5 | 6 | VI-1 | TBC1D2 | 3.17 |
| 2533 | 3 | 4 | 5 | 6 | VI-1 | TBC1D24 | 2.26 |
| 2534 | 3 | 4 | 5 | 6 | VI-1 | TBC1D2B | 2.07 |
| 2535 | 3 | 4 | 5 | 6 | VI-1 | TBC1D3G | 2.76 |
| 2536 | 3 | 4 | 5 | 6 | VI-1 | TBC1D5 | 2.02 |
| 2537 | 3 | 4 | 5 | 6 | VI-1 | TBC1D7 | 2.14 |
| 2538 | 3 | 4 | 5 | 6 | VI-1 | TBC1D9B | 2.26 |
| 2539 | 3 | 4 | 5 | 6 | VI-1 | TBCD | 2.86 |
| 2540 | 3 | 4 | 5 | 6 | VI-1 | TBCK | 2.12 |
| 2541 | 3 | 4 | 5 | 6 | VI-1 | TBK1 | 2.29 |
| 2542 | 3 | 4 | 5 | 6 | VI-1 | TBRG1 | 2.25 |
| 2543 | 3 | 4 | 5 | 6 | VI-1 | TBX19 | 2.65 |
| 2544 | 3 | 4 | 5 | 6 | VI-1 | TBXA2R | 2.01 |
| 2545 | 3 | 4 | 5 | 6 | VI-1 | TCAP | 2.34 |
| 2546 | 3 | 4 | 5 | 6 | VI-1 | TCEA3 | 2.28 |
| 2547 | 3 | 4 | 5 | 6 | VI-1 | TCERG1 | 2.25 |
| 2548 | 3 | 4 | 5 | 6 | VI-1 | TCF7L1 | 2.02 |
| 2549 | 3 | 4 | 5 | 6 | VI-1 | TCF7L2 | 2.61 |
| 2550 | 3 | 4 | 5 | 6 | VI-1 | TCHP | 2.47 |
| 2551 | 3 | 4 | 5 | 6 | VI-1 | TCP11L1 | 2.15 |
| 2552 | 3 | 4 | 5 | 6 | VI-1 | TDG | 2.26 |
| 2553 | 3 | 4 | 5 | 6 | VI-1 | TDRD7 | 3.39 |
| 2554 | 3 | 4 | 5 | 6 | VI-1 | TECPR1 | 2.30 |
| 2555 | 3 | 4 | 5 | 6 | VI-1 | TEN1-CDK3 | 4.10 |
| 2556 | 3 | 4 | 5 | 6 | VI-1 | TEP1 | 4.64 |
| 2557 | 3 | 4 | 5 | 6 | VI-1 | TET3 | 2.18 |
| 2558 | 3 | 4 | 5 | 6 | VI-1 | TFB1M | 2.63 |
| 2559 | 3 | 4 | 5 | 6 | VI-1 | TFRC | 2.28 |
| 2560 | 3 | 4 | 5 | 6 | VI-1 | TH1L | 2.00 |
| 2561 | 3 | 4 | 5 | 6 | VI-1 | THADA | 2.70 |
| 2562 | 3 | 4 | 5 | 6 | VI-1 | THOC1 | 2.67 |
| 2563 | 3 | 4 | 5 | 6 | VI-1 | THOC2 | 3.04 |
| 2564 | 3 | 4 | 5 | 6 | VI-1 | TIA1 | 4.30 |
| 2565 | 3 | 4 | 5 | 6 | VI-1 | TIAF1 | 3.43 |
| 2566 | 3 | 4 | 5 | 6 | VI-1 | TIAL1 | 2.08 |
| 2567 | 3 | 4 | 5 | 6 | VI-1 | TICAM2 | 2.90 |
| 2568 | 3 | 4 | 5 | 6 | VI-1 | TIFA | 2.27 |
| 2569 | 3 | 4 | 5 | 6 | VI-1 | TIGD7 | 2.33 |
| 2570 | 3 | 4 | 5 | 6 | VI-1 | TIMELESS | 2.82 |
| 2571 | 3 | 4 | 5 | 6 | VI-1 | TJAP1 | 2.14 |
| 2572 | 3 | 4 | 5 | 6 | VI-1 | TJP2 | 2.81 |
| 2573 | 3 | 4 | 5 | 6 | VI-1 | TLE4 | 2.58 |
| 2574 | 3 | 4 | 5 | 6 | VI-1 | TLN1 | 2.50 |
| 2575 | 3 | 4 | 5 | 6 | VI-1 | TLR10 | 2.48 |
| 2576 | 3 | 4 | 5 | 6 | VI-1 | TLR5 | 2.04 |
| 2577 | 3 | 4 | 5 | 6 | VI-1 | TLR6 | 2.24 |
| 2578 | 3 | 4 | 5 | 6 | VI-1 | TLR9 | 3.21 |
| 2579 | 3 | 4 | 5 | 6 | VI-1 | TM2D3 | 2.08 |
| 2580 | 3 | 4 | 5 | 6 | VI-1 | TM9SF1 | 2.05 |
| 2581 | 3 | 4 | 5 | 6 | VI-1 | TM9SF2 | 2.08 |
| 2582 | 3 | 4 | 5 | 6 | VI-1 | TM9SF4 | 2.12 |
| 2583 | 3 | 4 | 5 | 6 | VI-1 | TMC6 | 2.07 |
| 2584 | 3 | 4 | 5 | 6 | VI-1 | TMC8 | 2.80 |
| 2585 | 3 | 4 | 5 | 6 | VI-1 | TMCO6 | 2.04 |
| 2586 | 3 | 4 | 5 | 6 | VI-1 | TMEM110 | 2.37 |
| 2587 | 3 | 4 | 5 | 6 | VI-1 | TMEM123 | 3.20 |
| 2588 | 3 | 4 | 5 | 6 | VI-1 | TMEM131 | 2.84 |
| 2589 | 3 | 4 | 5 | 6 | VI-1 | TMEM143 | 3.27 |
| 2590 | 3 | 4 | 5 | 6 | VI-1 | TMEM144 | 2.97 |
| 2591 | 3 | 4 | 5 | 6 | VI-1 | TMEM161B | 2.33 |
| 2592 | 3 | 4 | 5 | 6 | VI-1 | TMEM168 | 2.22 |
| 2593 | 3 | 4 | 5 | 6 | VI-1 | TMEM173 | 2.04 |
| 2594 | 3 | 4 | 5 | 6 | VI-1 | TMEM180 | 2.67 |
| 2595 | 3 | 4 | 5 | 6 | VI-1 | TMEM181 | 2.68 |
| 2596 | 3 | 4 | 5 | 6 | VI-1 | TMEM194A | 2.47 |
| 2597 | 3 | 4 | 5 | 6 | VI-1 | TMEM198B | 3.34 |
| 2598 | 3 | 4 | 5 | 6 | VI-1 | TMEM201 | 2.36 |
| 2599 | 3 | 4 | 5 | 6 | VI-1 | TMEM220 | 2.30 |
| 2600 | 3 | 4 | 5 | 6 | VI-1 | TMEM234 | 2.28 |
| 2601 | 3 | 4 | 5 | 6 | VI-1 | TMEM43 | 2.14 |
| 2602 | 3 | 4 | 5 | 6 | VI-1 | TMEM45B | 2.14 |
| 2603 | 3 | 4 | 5 | 6 | VI-1 | TMEM55A | 2.17 |
| 2604 | 3 | 4 | 5 | 6 | VI-1 | TMEM60 | 3.13 |
| 2605 | 3 | 4 | 5 | 6 | VI-1 | TMEM62 | 2.60 |
| 2606 | 3 | 4 | 5 | 6 | VI-1 | TMEM63A | 3.44 |
| 2607 | 3 | 4 | 5 | 6 | VI-1 | TMEM65 | 2.26 |
| 2608 | 3 | 4 | 5 | 6 | VI-1 | TMEM79 | 3.72 |
| 2609 | 3 | 4 | 5 | 6 | VI-1 | TMEM80 | 2.79 |
| 2610 | 3 | 4 | 5 | 6 | VI-1 | TMEM81 | 2.89 |
| 2611 | 3 | 4 | 5 | 6 | VI-1 | TMEM87A | 2.13 |
| 2612 | 3 | 4 | 5 | 6 | VI-1 | TMEM87B | 2.07 |
| 2613 | 3 | 4 | 5 | 6 | VI-1 | TMF1 | 2.12 |
| 2614 | 3 | 4 | 5 | 6 | VI-1 | TMOD2 | 3.89 |
| 2615 | 3 | 4 | 5 | 6 | VI-1 | TMPPE | 2.24 |
| 2616 | 3 | 4 | 5 | 6 | VI-1 | TMTC1 | 2.10 |
| 2617 | 3 | 4 | 5 | 6 | VI-1 | TMTC2 | 2.25 |
| 2618 | 3 | 4 | 5 | 6 | VI-1 | TMUB2 | 2.72 |
| 2619 | 3 | 4 | 5 | 6 | VI-1 | TMX2 | 2.03 |
| 2620 | 3 | 4 | 5 | 6 | VI-1 | TMX3 | 2.41 |
| 2621 | 3 | 4 | 5 | 6 | VI-1 | TNFRSF10B | 3.43 |
| 2622 | 3 | 4 | 5 | 6 | VI-1 | TNFRSF10D | 3.79 |
| 2623 | 3 | 4 | 5 | 6 | VI-1 | TNFRSF14 | 2.32 |
| 2624 | 3 | 4 | 5 | 6 | VI-1 | TNFRSF1B | 2.04 |
| 2625 | 3 | 4 | 5 | 6 | VI-1 | TNFSF10 | 3.42 |
| 2626 | 3 | 4 | 5 | 6 | VI-1 | TNFSF13B | 3.82 |
| 2627 | 3 | 4 | 5 | 6 | VI-1 | TNK1 | 2.16 |
| 2628 | 3 | 4 | 5 | 6 | VI-1 | TNKS | 2.42 |
| 2629 | 3 | 4 | 5 | 6 | VI-1 | TNKS2 | 2.03 |
| 2630 | 3 | 4 | 5 | 6 | VI-1 | TNPO2 | 2.30 |
| 2631 | 3 | 4 | 5 | 6 | VI-1 | TNRC18 | 2.34 |
| 2632 | 3 | 4 | 5 | 6 | VI-1 | TNRC6A | 2.24 |
| 2633 | 3 | 4 | 5 | 6 | VI-1 | TNRC6B | 2.72 |
| 2634 | 3 | 4 | 5 | 6 | VI-1 | TOM1L2 | 2.02 |
| 2635 | 3 | 4 | 5 | 6 | VI-1 | TOP1 | 2.38 |
| 2636 | 3 | 4 | 5 | 6 | VI-1 | TOP1P1 | 2.29 |
| 2637 | 3 | 4 | 5 | 6 | VI-1 | TOP3A | 2.01 |
| 2638 | 3 | 4 | 5 | 6 | VI-1 | TOP3B | 3.45 |
| 2639 | 3 | 4 | 5 | 6 | VI-1 | TOPBP1 | 2.20 |
| 2640 | 3 | 4 | 5 | 6 | VI-1 | TOR1A | 2.21 |
| 2641 | 3 | 4 | 5 | 6 | VI-1 | TOR1AIP2 | 2.10 |
| 2642 | 3 | 4 | 5 | 6 | VI-1 | TOR1B | 4.56 |
| 2643 | 3 | 4 | 5 | 6 | VI-1 | TP53BP1 | 3.09 |
| 2644 | 3 | 4 | 5 | 6 | VI-1 | TP53I13 | 2.22 |
| 2645 | 3 | 4 | 5 | 6 | VI-1 | TP53INP1 | 2.20 |
| 2646 | 3 | 4 | 5 | 6 | VI-1 | TP73-AS1 | 3.05 |
| 2647 | 3 | 4 | 5 | 6 | VI-1 | TPCN1 | 2.96 |
| 2648 | 3 | 4 | 5 | 6 | VI-1 | TPCN2 | 2.45 |
| 2649 | 3 | 4 | 5 | 6 | VI-1 | TPP1 | 3.20 |
| 2650 | 3 | 4 | 5 | 6 | VI-1 | TPP2 | 2.50 |
| 2651 | 3 | 4 | 5 | 6 | VI-1 | TPR | 2.25 |
| 2652 | 3 | 4 | 5 | 6 | VI-1 | TPT1-AS1 | 2.41 |
| 2653 | 3 | 4 | 5 | 6 | VI-1 | TRA2A | 2.28 |
| 2654 | 3 | 4 | 5 | 6 | VI-1 | TRABD | 2.15 |
| 2655 | 3 | 4 | 5 | 6 | VI-1 | TRAF3IP2-AS1 | 2.71 |
| 2656 | 3 | 4 | 5 | 6 | VI-1 | TRAF5 | 2.13 |
| 2657 | 3 | 4 | 5 | 6 | VI-1 | TRAF6 | 2.00 |
| 2658 | 3 | 4 | 5 | 6 | VI-1 | TRAFD1 | 3.16 |
| 2659 | 3 | 4 | 5 | 6 | VI-1 | TRAK1 | 2.16 |
| 2660 | 3 | 4 | 5 | 6 | VI-1 | TRAM2 | 2.78 |
| 2661 | 3 | 4 | 5 | 6 | VI-1 | TRANK1 | 4.66 |
| 2662 | 3 | 4 | 5 | 6 | VI-1 | TRAPPC11 | 2.37 |
| 2663 | 3 | 4 | 5 | 6 | VI-1 | TREML4 | 3.19 |
| 2664 | 3 | 4 | 5 | 6 | VI-1 | TREX1 | 3.03 |
| 2665 | 3 | 4 | 5 | 6 | VI-1 | TRIB1 | 2.55 |
| 2666 | 3 | 4 | 5 | 6 | VI-1 | TRIB2 | 3.49 |
| 2667 | 3 | 4 | 5 | 6 | VI-1 | TRIM14 | 3.00 |
| 2668 | 3 | 4 | 5 | 6 | VI-1 | TRIM21 | 2.45 |
| 2669 | 3 | 4 | 5 | 6 | VI-1 | TRIM25 | 3.44 |
| 2670 | 3 | 4 | 5 | 6 | VI-1 | TRIM26 | 2.06 |
| 2671 | 3 | 4 | 5 | 6 | VI-1 | TRIM3 | 2.42 |
| 2672 | 3 | 4 | 5 | 6 | VI-1 | TRIM33 | 2.87 |
| 2673 | 3 | 4 | 5 | 6 | VI-1 | TRIM34 | 2.60 |
| 2674 | 3 | 4 | 5 | 6 | VI-1 | TRIM38 | 4.06 |
| 2675 | 3 | 4 | 5 | 6 | VI-1 | TRIM41 | 2.47 |
| 2676 | 3 | 4 | 5 | 6 | VI-1 | TRIM44 | 2.23 |
| 2677 | 3 | 4 | 5 | 6 | VI-1 | TRIM52 | 2.02 |
| 2678 | 3 | 4 | 5 | 6 | VI-1 | TRIM6 | 4.02 |
| 2679 | 3 | 4 | 5 | 6 | VI-1 | TRIP6 | 2.31 |
| 2680 | 3 | 4 | 5 | 6 | VI-1 | TRMT1 | 2.47 |
| 2681 | 3 | 4 | 5 | 6 | VI-1 | TRMT1L | 2.62 |
| 2682 | 3 | 4 | 5 | 6 | VI-1 | TRMT2A | 2.32 |
| 2683 | 3 | 4 | 5 | 6 | VI-1 | TRMT5 | 2.14 |
| 2684 | 3 | 4 | 5 | 6 | VI-1 | TRMU | 3.07 |

Fig. 40 - 15

| | | | | | | | | | | | | | | | |
|---|---|---|---|---|---|---|---|---|---|---|---|---|---|---|---|
| 2685 | 3 | 4 | 5 | 6 | | VI-1 | TRNT1 | 2.44 | 2781 | 3 | 4 | 5 | 6 | VI-1 | VIPR1 | 2.45 |
| 2686 | 3 | 4 | 5 | 6 | | VI-1 | TRPC4AP | 2.75 | 2782 | 3 | 4 | 5 | 6 | VI-1 | VMAC | 2.14 |
| 2687 | 3 | 4 | 5 | 6 | | VI-1 | TRPV1 | 2.13 | 2783 | 3 | 4 | 5 | 6 | VI-1 | VMO1 | 2.43 |
| 2688 | 3 | 4 | 5 | 6 | | VI-1 | TRRAP | 2.90 | 2784 | 3 | 4 | 5 | 6 | VI-1 | VPS11 | 2.07 |
| 2689 | 3 | 4 | 5 | 6 | | VI-1 | TSC1 | 2.57 | 2785 | 3 | 4 | 5 | 6 | VI-1 | VPS13A | 2.16 |
| 2690 | 3 | 4 | 5 | 6 | | VI-1 | TSC2 | 2.40 | 2786 | 3 | 4 | 5 | 6 | VI-1 | VPS13B | 2.96 |
| 2691 | 3 | 4 | 5 | 6 | | VI-1 | TSHZ2 | 3.31 | 2787 | 3 | 4 | 5 | 6 | VI-1 | VPS13C | 4.20 |
| 2692 | 3 | 4 | 5 | 6 | | VI-1 | TSPAN32 | 3.38 | 2788 | 3 | 4 | 5 | 6 | VI-1 | VPS13D | 2.49 |
| 2693 | 3 | 4 | 5 | 6 | | VI-1 | TSPYL2 | 3.35 | 2789 | 3 | 4 | 5 | 6 | VI-1 | VPS16 | 3.03 |
| 2694 | 3 | 4 | 5 | 6 | | VI-1 | TSSK4 | 2.32 | 2790 | 3 | 4 | 5 | 6 | VI-1 | VPS39 | 2.53 |
| 2695 | 3 | 4 | 5 | 6 | | VI-1 | TTC13 | 2.96 | 2791 | 3 | 4 | 5 | 6 | VI-1 | VPS41 | 2.41 |
| 2696 | 3 | 4 | 5 | 6 | | VI-1 | TTC17 | 2.18 | 2792 | 3 | 4 | 5 | 6 | VI-1 | VPS45 | 2.82 |
| 2697 | 3 | 4 | 5 | 6 | | VI-1 | TTC21B | 2.71 | 2793 | 3 | 4 | 5 | 6 | VI-1 | VPS52 | 2.54 |
| 2698 | 3 | 4 | 5 | 6 | | VI-1 | TTC31 | 2.63 | 2794 | 3 | 4 | 5 | 6 | VI-1 | VPS53 | 3.89 |
| 2699 | 3 | 4 | 5 | 6 | | VI-1 | TTF1 | 2.87 | 2795 | 3 | 4 | 5 | 6 | VI-1 | VPS54 | 2.19 |
| 2700 | 3 | 4 | 5 | 6 | | VI-1 | TTF2 | 2.59 | 2796 | 3 | 4 | 5 | 6 | VI-1 | VPS8 | 2.35 |
| 2701 | 3 | 4 | 5 | 6 | | VI-1 | TTYH2 | 2.07 | 2797 | 3 | 4 | 5 | 6 | VI-1 | VRK2 | 2.79 |
| 2702 | 3 | 4 | 5 | 6 | | VI-1 | TTYH3 | 2.66 | 2798 | 3 | 4 | 5 | 6 | VI-1 | VTI1A | 2.01 |
| 2703 | 3 | 4 | 5 | 6 | | VI-1 | TUBE1 | 2.18 | 2799 | 3 | 4 | 5 | 6 | VI-1 | WASH7P | 2.30 |
| 2704 | 3 | 4 | 5 | 6 | | VI-1 | TUBG2 | 2.37 | 2800 | 3 | 4 | 5 | 6 | VI-1 | WASL | 2.10 |
| 2705 | 3 | 4 | 5 | 6 | | VI-1 | TUBGCP4 | 3.09 | 2801 | 3 | 4 | 5 | 6 | VI-1 | WBP4 | 2.10 |
| 2706 | 3 | 4 | 5 | 6 | | VI-1 | TUBGCP6 | 3.98 | 2802 | 3 | 4 | 5 | 6 | VI-1 | WDFY1 | 3.05 |
| 2707 | 3 | 4 | 5 | 6 | | VI-1 | TUFT1 | 2.88 | 2803 | 3 | 4 | 5 | 6 | VI-1 | WDFY2 | 2.49 |
| 2708 | 3 | 4 | 5 | 6 | | VI-1 | TUG1 | 3.47 | 2804 | 3 | 4 | 5 | 6 | VI-1 | WDFY3 | 2.72 |
| 2709 | 3 | 4 | 5 | 6 | | VI-1 | TUT1 | 2.05 | 2805 | 3 | 4 | 5 | 6 | VI-1 | WDFY4 | 2.27 |
| 2710 | 3 | 4 | 5 | 6 | | VI-1 | TXLNB | 2.49 | 2806 | 3 | 4 | 5 | 6 | VI-1 | WDR11 | 2.29 |
| 2711 | 3 | 4 | 5 | 6 | | VI-1 | TYK2 | 2.67 | 2807 | 3 | 4 | 5 | 6 | VI-1 | WDR26 | 2.31 |
| 2712 | 3 | 4 | 5 | 6 | | VI-1 | TYSND1 | 2.06 | 2808 | 3 | 4 | 5 | 6 | VI-1 | WDR33 | 2.73 |
| 2713 | 3 | 4 | 5 | 6 | | VI-1 | TYW5 | 2.26 | 2809 | 3 | 4 | 5 | 6 | VI-1 | WDR34 | 2.00 |
| 2714 | 3 | 4 | 5 | 6 | | VI-1 | U2SURP | 2.41 | 2810 | 3 | 4 | 5 | 6 | VI-1 | WDR37 | 2.11 |
| 2715 | 3 | 4 | 5 | 6 | | VI-1 | UBA1 | 2.14 | 2811 | 3 | 4 | 5 | 6 | VI-1 | WDR44 | 2.24 |
| 2716 | 3 | 4 | 5 | 6 | | VI-1 | UBA3 | 2.57 | 2812 | 3 | 4 | 5 | 6 | VI-1 | WDR5 | 2.03 |
| 2717 | 3 | 4 | 5 | 6 | | VI-1 | UBA6 | 3.04 | 2813 | 3 | 4 | 5 | 6 | VI-1 | WDR59 | 2.46 |
| 2718 | 3 | 4 | 5 | 6 | | VI-1 | UBAP2 | 2.71 | 2814 | 3 | 4 | 5 | 6 | VI-1 | WDR5B | 2.74 |
| 2719 | 3 | 4 | 5 | 6 | | VI-1 | UBE2L6 | 4.51 | 2815 | 3 | 4 | 5 | 6 | VI-1 | WDR6 | 2.73 |
| 2720 | 3 | 4 | 5 | 6 | | VI-1 | UBE3B | 2.51 | 2816 | 3 | 4 | 5 | 6 | VI-1 | WDR7 | 2.13 |
| 2721 | 3 | 4 | 5 | 6 | | VI-1 | UBE4A | 3.03 | 2817 | 3 | 4 | 5 | 6 | VI-1 | WDR73 | 2.49 |
| 2722 | 3 | 4 | 5 | 6 | | VI-1 | UBN1 | 2.25 | 2818 | 3 | 4 | 5 | 6 | VI-1 | WDR75 | 2.26 |
| 2723 | 3 | 4 | 5 | 6 | | VI-1 | UBN2 | 2.67 | 2819 | 3 | 4 | 5 | 6 | VI-1 | WDR77 | 2.14 |
| 2724 | 3 | 4 | 5 | 6 | | VI-1 | UBP1 | 2.37 | 2820 | 3 | 4 | 5 | 6 | VI-1 | WDR81 | 2.67 |
| 2725 | 3 | 4 | 5 | 6 | | VI-1 | UBQLN2 | 2.40 | 2821 | 3 | 4 | 5 | 6 | VI-1 | WDR85 | 2.95 |
| 2726 | 3 | 4 | 5 | 6 | | VI-1 | UBQLNL | 2.21 | 2822 | 3 | 4 | 5 | 6 | VI-1 | WDR91 | 2.65 |
| 2727 | 3 | 4 | 5 | 6 | | VI-1 | UBR1 | 2.67 | 2823 | 3 | 4 | 5 | 6 | VI-1 | WDSUB1 | 2.06 |
| 2728 | 3 | 4 | 5 | 6 | | VI-1 | UBR2 | 2.87 | 2824 | 3 | 4 | 5 | 6 | VI-1 | WDYHV1 | 2.47 |
| 2729 | 3 | 4 | 5 | 6 | | VI-1 | UBR3 | 2.01 | 2825 | 3 | 4 | 5 | 6 | VI-1 | WHAMM | 2.12 |
| 2730 | 3 | 4 | 5 | 6 | | VI-1 | UBR4 | 2.98 | 2826 | 3 | 4 | 5 | 6 | VI-1 | WHSC1 | 2.15 |
| 2731 | 3 | 4 | 5 | 6 | | VI-1 | UBR5 | 2.68 | 2827 | 3 | 4 | 5 | 6 | VI-1 | WHSC2 | 2.06 |
| 2732 | 3 | 4 | 5 | 6 | | VI-1 | UBXN4 | 2.30 | 2828 | 3 | 4 | 5 | 6 | VI-1 | WIPF1 | 2.02 |
| 2733 | 3 | 4 | 5 | 6 | | VI-1 | UCHL3 | 2.12 | 2829 | 3 | 4 | 5 | 6 | VI-1 | WIPF2 | 2.30 |
| 2734 | 3 | 4 | 5 | 6 | | VI-1 | UCKL1 | 2.17 | 2830 | 3 | 4 | 5 | 6 | VI-1 | WIZ | 2.24 |
| 2735 | 3 | 4 | 5 | 6 | | VI-1 | UCN | 2.31 | 2831 | 3 | 4 | 5 | 6 | VI-1 | WNT10A | 2.52 |
| 2736 | 3 | 4 | 5 | 6 | | VI-1 | UCP3 | 2.67 | 2832 | 3 | 4 | 5 | 6 | VI-1 | WNT5B | 2.19 |
| 2737 | 3 | 4 | 5 | 6 | | VI-1 | UGGT1 | 2.10 | 2833 | 3 | 4 | 5 | 6 | VI-1 | WRAP73 | 2.22 |
| 2738 | 3 | 4 | 5 | 6 | | VI-1 | UGT2B11 | 2.04 | 2834 | 3 | 4 | 5 | 6 | VI-1 | WSB1 | 3.67 |
| 2739 | 3 | 4 | 5 | 6 | | VI-1 | UHRF1 | 2.06 | 2835 | 3 | 4 | 5 | 6 | VI-1 | WWC3 | 2.11 |
| 2740 | 3 | 4 | 5 | 6 | | VI-1 | UHRF2 | 2.78 | 2836 | 3 | 4 | 5 | 6 | VI-1 | WWP1 | 2.25 |
| 2741 | 3 | 4 | 5 | 6 | | VI-1 | ULK1 | 2.05 | 2837 | 3 | 4 | 5 | 6 | VI-1 | WWP2 | 2.04 |
| 2742 | 3 | 4 | 5 | 6 | | VI-1 | ULK3 | 2.18 | 2838 | 3 | 4 | 5 | 6 | VI-1 | XAB2 | 2.14 |
| 2743 | 3 | 4 | 5 | 6 | | VI-1 | UNC13D | 2.50 | 2839 | 3 | 4 | 5 | 6 | VI-1 | XIAP | 2.53 |
| 2744 | 3 | 4 | 5 | 6 | | VI-1 | UNC45A | 2.19 | 2840 | 3 | 4 | 5 | 6 | VI-1 | XPC | 2.62 |
| 2745 | 3 | 4 | 5 | 6 | | VI-1 | UNC93B1 | 4.44 | 2841 | 3 | 4 | 5 | 6 | VI-1 | XPNPEP1 | 2.79 |
| 2746 | 3 | 4 | 5 | 6 | | VI-1 | UNKL | 4.06 | 2842 | 3 | 4 | 5 | 6 | VI-1 | XPO1 | 3.06 |
| 2747 | 3 | 4 | 5 | 6 | | VI-1 | UPF1 | 2.34 | 2843 | 3 | 4 | 5 | 6 | VI-1 | XPO4 | 2.30 |
| 2748 | 3 | 4 | 5 | 6 | | VI-1 | UPF2 | 2.60 | 2844 | 3 | 4 | 5 | 6 | VI-1 | XRN1 | 3.57 |
| 2749 | 3 | 4 | 5 | 6 | | VI-1 | UPF3A | 2.15 | 2845 | 3 | 4 | 5 | 6 | VI-1 | YBEY | 2.62 |
| 2750 | 3 | 4 | 5 | 6 | | VI-1 | UPF3B | 2.69 | 2846 | 3 | 4 | 5 | 6 | VI-1 | YEATS2 | 2.74 |
| 2751 | 3 | 4 | 5 | 6 | | VI-1 | URB1 | 2.41 | 2847 | 3 | 4 | 5 | 6 | VI-1 | YIPF4 | 2.70 |
| 2752 | 3 | 4 | 5 | 6 | | VI-1 | USF1 | 2.47 | 2848 | 3 | 4 | 5 | 6 | VI-1 | YJEFN3 | 2.60 |
| 2753 | 3 | 4 | 5 | 6 | | VI-1 | USP11 | 2.07 | 2849 | 3 | 4 | 5 | 6 | VI-1 | YTHDC1 | 2.10 |
| 2754 | 3 | 4 | 5 | 6 | | VI-1 | USP19 | 3.00 | 2850 | 3 | 4 | 5 | 6 | VI-1 | YTHDC2 | 2.98 |
| 2755 | 3 | 4 | 5 | 6 | | VI-1 | USP24 | 2.40 | 2851 | 3 | 4 | 5 | 6 | VI-1 | YWHAB | 2.00 |
| 2756 | 3 | 4 | 5 | 6 | | VI-1 | USP25 | 2.65 | 2852 | 3 | 4 | 5 | 6 | VI-1 | ZBED5 | 2.81 |
| 2757 | 3 | 4 | 5 | 6 | | VI-1 | USP3 | 2.32 | 2853 | 3 | 4 | 5 | 6 | VI-1 | ZBED6 | 2.09 |
| 2758 | 3 | 4 | 5 | 6 | | VI-1 | USP32 | 2.14 | 2854 | 3 | 4 | 5 | 6 | VI-1 | ZBTB20 | 2.43 |
| 2759 | 3 | 4 | 5 | 6 | | VI-1 | USP32P2 | 3.52 | 2855 | 3 | 4 | 5 | 6 | VI-1 | ZBTB26 | 2.95 |
| 2760 | 3 | 4 | 5 | 6 | | VI-1 | USP33 | 2.49 | 2856 | 3 | 4 | 5 | 6 | VI-1 | ZBTB32 | 2.42 |
| 2761 | 3 | 4 | 5 | 6 | | VI-1 | USP34 | 2.28 | 2857 | 3 | 4 | 5 | 6 | VI-1 | ZBTB34 | 2.20 |
| 2762 | 3 | 4 | 5 | 6 | | VI-1 | USP35 | 2.72 | 2858 | 3 | 4 | 5 | 6 | VI-1 | ZBTB40 | 3.21 |
| 2763 | 3 | 4 | 5 | 6 | | VI-1 | USP36 | 2.03 | 2859 | 3 | 4 | 5 | 6 | VI-1 | ZBTB43 | 2.02 |
| 2764 | 3 | 4 | 5 | 6 | | VI-1 | USP4 | 2.51 | 2860 | 3 | 4 | 5 | 6 | VI-1 | ZBTB46 | 2.06 |
| 2765 | 3 | 4 | 5 | 6 | | VI-1 | USP40 | 2.09 | 2861 | 3 | 4 | 5 | 6 | VI-1 | ZC3H11A | 2.83 |
| 2766 | 3 | 4 | 5 | 6 | | VI-1 | USP42 | 2.58 | 2862 | 3 | 4 | 5 | 6 | VI-1 | ZC3H12D | 2.59 |
| 2767 | 3 | 4 | 5 | 6 | | VI-1 | USP6NL | 2.04 | 2863 | 3 | 4 | 5 | 6 | VI-1 | ZC3H13 | 2.60 |
| 2768 | 3 | 4 | 5 | 6 | | VI-1 | USP7 | 2.11 | 2864 | 3 | 4 | 5 | 6 | VI-1 | ZC3H14 | 2.06 |
| 2769 | 3 | 4 | 5 | 6 | | VI-1 | USP8 | 2.28 | 2865 | 3 | 4 | 5 | 6 | VI-1 | ZC3H7A | 2.45 |
| 2770 | 3 | 4 | 5 | 6 | | VI-1 | USP9X | 2.09 | 2866 | 3 | 4 | 5 | 6 | VI-1 | ZC3HAV1 | 2.88 |
| 2771 | 3 | 4 | 5 | 6 | | VI-1 | USPL1 | 2.66 | 2867 | 3 | 4 | 5 | 6 | VI-1 | ZCCHC11 | 2.08 |
| 2772 | 3 | 4 | 5 | 6 | | VI-1 | UTP6 | 2.22 | 2868 | 3 | 4 | 5 | 6 | VI-1 | ZCCHC14 | 2.14 |
| 2773 | 3 | 4 | 5 | 6 | | VI-1 | UTRN | 3.01 | 2869 | 3 | 4 | 5 | 6 | VI-1 | ZCCHC6 | 2.48 |
| 2774 | 3 | 4 | 5 | 6 | | VI-1 | UVRAG | 2.17 | 2870 | 3 | 4 | 5 | 6 | VI-1 | ZCCHC8 | 2.15 |
| 2775 | 3 | 4 | 5 | 6 | | VI-1 | VAMP5 | 2.28 | 2871 | 3 | 4 | 5 | 6 | VI-1 | ZCWPW1 | 2.16 |
| 2776 | 3 | 4 | 5 | 6 | | VI-1 | VAV1 | 2.16 | 2872 | 3 | 4 | 5 | 6 | VI-1 | ZDHHC13 | 3.01 |
| 2777 | 3 | 4 | 5 | 6 | | VI-1 | VCL | 2.37 | 2873 | 3 | 4 | 5 | 6 | VI-1 | ZDHHC17 | 3.22 |
| 2778 | 3 | 4 | 5 | 6 | | VI-1 | VCPIP1 | 2.38 | 2874 | 3 | 4 | 5 | 6 | VI-1 | ZDHHC21 | 2.53 |
| 2779 | 3 | 4 | 5 | 6 | | VI-1 | VDR | 2.39 | 2875 | 3 | 4 | 5 | 6 | VI-1 | ZDHHC6 | 2.07 |
| 2780 | 3 | 4 | 5 | 6 | | VI-1 | VILL | 2.38 | 2876 | 3 | 4 | 5 | 6 | VI-1 | ZDHHC8 | 2.62 |

Fig. 40 - 16

| | | | | | | | | | | | | | | | |
|---|---|---|---|---|---|---|---|---|---|---|---|---|---|---|---|
| 2877 | 3 | 4 | 5 | 6 | | VI-1 | ZEB1-AS1 | 2.37 | 2973 | 3 | 4 | 5 | 6 | VI-1 | ZNF76 | 2.24 |
| 2878 | 3 | 4 | 5 | 6 | | VI-1 | ZEB2 | 2.45 | 2974 | 3 | 4 | 5 | 6 | VI-1 | ZNF763 | 2.28 |
| 2879 | 3 | 4 | 5 | 6 | | VI-1 | ZFAND4 | 2.03 | 2975 | 3 | 4 | 5 | 6 | VI-1 | ZNF780A | 2.21 |
| 2880 | 3 | 4 | 5 | 6 | | VI-1 | ZFAND5 | 2.56 | 2976 | 3 | 4 | 5 | 6 | VI-1 | ZNF780B | 2.88 |
| 2881 | 3 | 4 | 5 | 6 | | VI-1 | ZFC3H1 | 3.97 | 2977 | 3 | 4 | 5 | 6 | VI-1 | ZNF782 | 2.52 |
| 2882 | 3 | 4 | 5 | 6 | | VI-1 | ZFP106 | 2.11 | 2978 | 3 | 4 | 5 | 6 | VI-1 | ZNF783 | 2.45 |
| 2883 | 3 | 4 | 5 | 6 | | VI-1 | ZFP3 | 2.09 | 2979 | 3 | 4 | 5 | 6 | VI-1 | ZNF785 | 2.77 |
| 2884 | 3 | 4 | 5 | 6 | | VI-1 | ZFP62 | 2.37 | 2980 | 3 | 4 | 5 | 6 | VI-1 | ZNF81 | 2.79 |
| 2885 | 3 | 4 | 5 | 6 | | VI-1 | ZFYVE16 | 2.67 | 2981 | 3 | 4 | 5 | 6 | VI-1 | ZNF814 | 2.85 |
| 2886 | 3 | 4 | 5 | 6 | | VI-1 | ZFYVE19 | 2.06 | 2982 | 3 | 4 | 5 | 6 | VI-1 | ZNF83 | 2.78 |
| 2887 | 3 | 4 | 5 | 6 | | VI-1 | ZFYVE20 | 2.03 | 2983 | 3 | 4 | 5 | 6 | VI-1 | ZNF836 | 2.14 |
| 2888 | 3 | 4 | 5 | 6 | | VI-1 | ZFYVE26 | 3.63 | 2984 | 3 | 4 | 5 | 6 | VI-1 | ZNF839 | 2.43 |
| 2889 | 3 | 4 | 5 | 6 | | VI-1 | ZFYVE27 | 2.82 | 2985 | 3 | 4 | 5 | 6 | VI-1 | ZNF841 | 2.87 |
| 2890 | 3 | 4 | 5 | 6 | | VI-1 | ZKSCAN1 | 2.11 | 2986 | 3 | 4 | 5 | 6 | VI-1 | ZNF862 | 2.79 |
| 2891 | 3 | 4 | 5 | 6 | | VI-1 | ZKSCAN3 | 2.12 | 2987 | 3 | 4 | 5 | 6 | VI-1 | ZNF91 | 2.13 |
| 2892 | 3 | 4 | 5 | 6 | | VI-1 | ZMAT1 | 4.98 | 2988 | 3 | 4 | 5 | 6 | VI-1 | ZNFX1 | 3.05 |
| 2893 | 3 | 4 | 5 | 6 | | VI-1 | ZMIZ1 | 2.31 | 2989 | 3 | 4 | 5 | 6 | VI-1 | ZRANB2 | 3.42 |
| 2894 | 3 | 4 | 5 | 6 | | VI-1 | ZMIZ2 | 3.18 | 2990 | 3 | 4 | 5 | 6 | VI-1 | ZRANB2-AS1 | 2.94 |
| 2895 | 3 | 4 | 5 | 6 | | VI-1 | ZMYM1 | 2.10 | 2991 | 3 | 4 | 5 | 6 | VI-1 | ZSCAN16 | 2.14 |
| 2896 | 3 | 4 | 5 | 6 | | VI-1 | ZMYM2 | 2.13 | 2992 | 3 | 4 | 5 | 6 | VI-1 | ZSCAN18 | 2.35 |
| 2897 | 3 | 4 | 5 | 6 | | VI-1 | ZMYM3 | 3.12 | 2993 | 3 | 4 | 5 | 6 | VI-1 | ZSCAN22 | 2.05 |
| 2898 | 3 | 4 | 5 | 6 | | VI-1 | ZMYM5 | 2.08 | 2994 | 3 | 4 | 5 | 6 | VI-1 | ZSCAN29 | 2.06 |
| 2899 | 3 | 4 | 5 | 6 | | VI-1 | ZMYM6 | 2.42 | 2995 | 3 | 4 | 5 | 6 | VI-1 | ZSCAN30 | 3.76 |
| 2900 | 3 | 4 | 5 | 6 | | VI-1 | ZMYND8 | 2.85 | 2996 | 3 | 4 | 5 | 6 | VI-1 | ZSWIM4 | 2.30 |
| 2901 | 3 | 4 | 5 | 6 | | VI-1 | ZNF10 | 2.08 | 2997 | 3 | 4 | 5 | 6 | VI-1 | ZSWIM6 | 2.50 |
| 2902 | 3 | 4 | 5 | 6 | | VI-1 | ZNF12 | 2.01 | 2998 | 3 | 4 | 5 | 6 | VI-1 | ZXDC | 2.25 |
| 2903 | 3 | 4 | 5 | 6 | | VI-1 | ZNF137P | 2.82 | 2999 | 3 | 4 | 5 | 6 | VI-1 | ZZEF1 | 2.38 |
| 2904 | 3 | 4 | 5 | 6 | | VI-1 | ZNF169 | 2.67 | 3000 | 3 | 4 | 5 | | V-2 | ALKBH7 | 0.64 |
| 2905 | 3 | 4 | 5 | 6 | | VI-1 | ZNF18 | 2.59 | 3001 | 3 | 4 | 5 | | V-2 | ATP5I | 0.62 |
| 2906 | 3 | 4 | 5 | 6 | | VI-1 | ZNF182 | 2.61 | 3002 | 3 | 4 | 5 | | V-2 | ATP5J2 | 0.62 |
| 2907 | 3 | 4 | 5 | 6 | | VI-1 | ZNF192 | 2.02 | 3003 | 3 | 4 | 5 | | V-2 | ATP5L2 | 0.57 |
| 2908 | 3 | 4 | 5 | 6 | | VI-1 | ZNF20 | 2.17 | 3004 | 3 | 4 | 5 | | V-2 | BNIP1 | 0.62 |
| 2909 | 3 | 4 | 5 | 6 | | VI-1 | ZNF200 | 3.16 | 3005 | 3 | 4 | 5 | | V-2 | C9orf172 | 0.62 |
| 2910 | 3 | 4 | 5 | 6 | | VI-1 | ZNF202 | 2.34 | 3006 | 3 | 4 | 5 | | V-2 | CCDC65 | 0.62 |
| 2911 | 3 | 4 | 5 | 6 | | VI-1 | ZNF224 | 2.88 | 3007 | 3 | 4 | 5 | | V-2 | CD3D | 0.51 |
| 2912 | 3 | 4 | 5 | 6 | | VI-1 | ZNF226 | 2.53 | 3008 | 3 | 4 | 5 | | V-2 | CD48 | 0.66 |
| 2913 | 3 | 4 | 5 | 6 | | VI-1 | ZNF230 | 2.63 | 3009 | 3 | 4 | 5 | | V-2 | CHCHD5 | 0.62 |
| 2914 | 3 | 4 | 5 | 6 | | VI-1 | ZNF234 | 2.42 | 3010 | 3 | 4 | 5 | | V-2 | CRTAM | 0.58 |
| 2915 | 3 | 4 | 5 | 6 | | VI-1 | ZNF238 | 2.16 | 3011 | 3 | 4 | 5 | | V-2 | DLG3 | 0.66 |
| 2916 | 3 | 4 | 5 | 6 | | VI-1 | ZNF248 | 3.34 | 3012 | 3 | 4 | 5 | | V-2 | EEF1A1 | 0.52 |
| 2917 | 3 | 4 | 5 | 6 | | VI-1 | ZNF251 | 2.20 | 3013 | 3 | 4 | 5 | | V-2 | EEF1G | 0.58 |
| 2918 | 3 | 4 | 5 | 6 | | VI-1 | ZNF266 | 2.44 | 3014 | 3 | 4 | 5 | | V-2 | ENPP4 | 0.61 |
| 2919 | 3 | 4 | 5 | 6 | | VI-1 | ZNF267 | 2.07 | 3015 | 3 | 4 | 5 | | V-2 | FLJ44635 | 0.56 |
| 2920 | 3 | 4 | 5 | 6 | | VI-1 | ZNF271 | 2.18 | 3016 | 3 | 4 | 5 | | V-2 | FTH1P3 | 0.64 |
| 2921 | 3 | 4 | 5 | 6 | | VI-1 | ZNF275 | 2.06 | 3017 | 3 | 4 | 5 | | V-2 | GNB1L | 0.65 |
| 2922 | 3 | 4 | 5 | 6 | | VI-1 | ZNF276 | 2.41 | 3018 | 3 | 4 | 5 | | V-2 | GPR56 | 0.62 |
| 2923 | 3 | 4 | 5 | 6 | | VI-1 | ZNF282 | 2.03 | 3019 | 3 | 4 | 5 | | V-2 | GPX7 | 0.61 |
| 2924 | 3 | 4 | 5 | 6 | | VI-1 | ZNF318 | 2.27 | 3020 | 3 | 4 | 5 | | V-2 | GZMM | 0.59 |
| 2925 | 3 | 4 | 5 | 6 | | VI-1 | ZNF321P | 2.46 | 3021 | 3 | 4 | 5 | | V-2 | ID2 | 0.53 |
| 2926 | 3 | 4 | 5 | 6 | | VI-1 | ZNF326 | 2.48 | 3022 | 3 | 4 | 5 | | V-2 | ITPRIPL1 | 0.60 |
| 2927 | 3 | 4 | 5 | 6 | | VI-1 | ZNF333 | 3.16 | 3023 | 3 | 4 | 5 | | V-2 | LOC100287482 | 0.59 |
| 2928 | 3 | 4 | 5 | 6 | | VI-1 | ZNF335 | 2.55 | 3024 | 3 | 4 | 5 | | V-2 | LOC100506776 | 0.64 |
| 2929 | 3 | 4 | 5 | 6 | | VI-1 | ZNF337 | 2.73 | 3025 | 3 | 4 | 5 | | V-2 | LOC284889 | 0.65 |
| 2930 | 3 | 4 | 5 | 6 | | VI-1 | ZNF341 | 2.53 | 3026 | 3 | 4 | 5 | | V-2 | MIF | 0.56 |
| 2931 | 3 | 4 | 5 | 6 | | VI-1 | ZNF345 | 2.85 | 3027 | 3 | 4 | 5 | | V-2 | NQO2 | 0.57 |
| 2932 | 3 | 4 | 5 | 6 | | VI-1 | ZNF354B | 3.03 | 3028 | 3 | 4 | 5 | | V-2 | PDCD1 | 0.50 |
| 2933 | 3 | 4 | 5 | 6 | | VI-1 | ZNF367 | 2.67 | 3029 | 3 | 4 | 5 | | V-2 | PDZD8 | 0.67 |
| 2934 | 3 | 4 | 5 | 6 | | VI-1 | ZNF37A | 2.01 | 3030 | 3 | 4 | 5 | | V-2 | PLEK2 | 0.57 |
| 2935 | 3 | 4 | 5 | 6 | | VI-1 | ZNF37BP | 4.32 | 3031 | 3 | 4 | 5 | | V-2 | PLEKHF1 | 0.51 |
| 2936 | 3 | 4 | 5 | 6 | | VI-1 | ZNF397 | 2.54 | 3032 | 3 | 4 | 5 | | V-2 | PROX2 | 0.62 |
| 2937 | 3 | 4 | 5 | 6 | | VI-1 | ZNF417 | 2.18 | 3033 | 3 | 4 | 5 | | V-2 | PRF1 | 0.66 |
| 2938 | 3 | 4 | 5 | 6 | | VI-1 | ZNF429 | 2.86 | 3034 | 3 | 4 | 5 | | V-2 | PTPN4 | 0.58 |
| 2939 | 3 | 4 | 5 | 6 | | VI-1 | ZNF431 | 2.00 | 3035 | 3 | 4 | 5 | | V-2 | PTRHD1 | 0.59 |
| 2940 | 3 | 4 | 5 | 6 | | VI-1 | ZNF438 | 2.60 | 3036 | 3 | 4 | 5 | | V-2 | RPA3 | 0.55 |
| 2941 | 3 | 4 | 5 | 6 | | VI-1 | ZNF439 | 2.51 | 3037 | 3 | 4 | 5 | | V-2 | RPL13 | 0.57 |
| 2942 | 3 | 4 | 5 | 6 | | VI-1 | ZNF44 | 2.34 | 3038 | 3 | 4 | 5 | | V-2 | RPL13AP20 | 0.63 |
| 2943 | 3 | 4 | 5 | 6 | | VI-1 | ZNF440 | 2.16 | 3039 | 3 | 4 | 5 | | V-2 | RPL17 | 0.54 |
| 2944 | 3 | 4 | 5 | 6 | | VI-1 | ZNF451 | 2.03 | 3040 | 3 | 4 | 5 | | V-2 | RPL18A | 0.66 |
| 2945 | 3 | 4 | 5 | 6 | | VI-1 | ZNF493 | 3.09 | 3041 | 3 | 4 | 5 | | V-2 | RPL27A | 0.57 |
| 2946 | 3 | 4 | 5 | 6 | | VI-1 | ZNF496 | 3.39 | 3042 | 3 | 4 | 5 | | V-2 | RPL29 | 0.65 |
| 2947 | 3 | 4 | 5 | 6 | | VI-1 | ZNF512 | 2.28 | 3043 | 3 | 4 | 5 | | V-2 | RPL3 | 0.56 |
| 2948 | 3 | 4 | 5 | 6 | | VI-1 | ZNF513 | 2.59 | 3044 | 3 | 4 | 5 | | V-2 | RPL35 | 0.58 |
| 2949 | 3 | 4 | 5 | 6 | | VI-1 | ZNF518A | 2.32 | 3045 | 3 | 4 | 5 | | V-2 | RPL38 | 0.64 |
| 2950 | 3 | 4 | 5 | 6 | | VI-1 | ZNF529 | 2.35 | 3046 | 3 | 4 | 5 | | V-2 | RPL39 | 0.57 |
| 2951 | 3 | 4 | 5 | 6 | | VI-1 | ZNF532 | 2.44 | 3047 | 3 | 4 | 5 | | V-2 | RPL6 | 0.53 |
| 2952 | 3 | 4 | 5 | 6 | | VI-1 | ZNF540 | 2.98 | 3048 | 3 | 4 | 5 | | V-2 | RPL8 | 0.66 |
| 2953 | 3 | 4 | 5 | 6 | | VI-1 | ZNF548 | 2.54 | 3049 | 3 | 4 | 5 | | V-2 | RPLP0 | 0.54 |
| 2954 | 3 | 4 | 5 | 6 | | VI-1 | ZNF558 | 3.27 | 3050 | 3 | 4 | 5 | | V-2 | RPLP1 | 0.54 |
| 2955 | 3 | 4 | 5 | 6 | | VI-1 | ZNF580 | 2.17 | 3051 | 3 | 4 | 5 | | V-2 | RPS17 | 0.52 |
| 2956 | 3 | 4 | 5 | 6 | | VI-1 | ZNF587 | 2.76 | 3052 | 3 | 4 | 5 | | V-2 | RPS17L | 0.52 |
| 2957 | 3 | 4 | 5 | 6 | | VI-1 | ZNF587B | 2.10 | 3053 | 3 | 4 | 5 | | V-2 | RPS20 | 0.67 |
| 2958 | 3 | 4 | 5 | 6 | | VI-1 | ZNF589 | 2.54 | 3054 | 3 | 4 | 5 | | V-2 | RPS25 | 0.63 |
| 2959 | 3 | 4 | 5 | 6 | | VI-1 | ZNF592 | 2.03 | 3055 | 3 | 4 | 5 | | V-2 | RPS27 | 0.64 |
| 2960 | 3 | 4 | 5 | 6 | | VI-1 | ZNF594 | 3.39 | 3056 | 3 | 4 | 5 | | V-2 | RPS4X | 0.52 |
| 2961 | 3 | 4 | 5 | 6 | | VI-1 | ZNF605 | 2.74 | 3057 | 3 | 4 | 5 | | V-2 | RPS5 | 0.62 |
| 2962 | 3 | 4 | 5 | 6 | | VI-1 | ZNF611 | 2.23 | 3058 | 3 | 4 | 5 | | V-2 | RPS8 | 0.64 |
| 2963 | 3 | 4 | 5 | 6 | | VI-1 | ZNF616 | 2.18 | 3059 | 3 | 4 | 5 | | V-2 | RPSA | 0.50 |
| 2964 | 3 | 4 | 5 | 6 | | VI-1 | ZNF638 | 2.70 | 3060 | 3 | 4 | 5 | | V-2 | RPSAP58 | 0.56 |
| 2965 | 3 | 4 | 5 | 6 | | VI-1 | ZNF646 | 2.27 | 3061 | 3 | 4 | 5 | | V-2 | SIT1 | 0.65 |
| 2966 | 3 | 4 | 5 | 6 | | VI-1 | ZNF652 | 2.05 | 3062 | 3 | 4 | 5 | | V-2 | SKAP1 | 0.61 |
| 2967 | 3 | 4 | 5 | 6 | | VI-1 | ZNF654 | 2.01 | 3063 | 3 | 4 | 5 | | V-2 | SLC25A5-AS1 | 0.53 |
| 2968 | 3 | 4 | 5 | 6 | | VI-1 | ZNF69 | 2.21 | 3064 | 3 | 4 | 5 | | V-2 | SNRPD2 | 0.59 |
| 2969 | 3 | 4 | 5 | 6 | | VI-1 | ZNF700 | 3.42 | 3065 | 3 | 4 | 5 | | V-2 | SPRY2 | 0.65 |
| 2970 | 3 | 4 | 5 | 6 | | VI-1 | ZNF707 | 2.41 | 3066 | 3 | 4 | 5 | | V-2 | TBX21 | 0.56 |
| 2971 | 3 | 4 | 5 | 6 | | VI-1 | ZNF75A | 2.05 | 3067 | 3 | 4 | 5 | | V-2 | TPT1 | 0.51 |
| 2972 | 3 | 4 | 5 | 6 | | VI-1 | ZNF75D | 2.05 | 3068 | 3 | 4 | 5 | | V-2 | TSTA3 | 0.65 |

Fig. 40 - 17

| | | | | | | | | | | | | | | |
|---|---|---|---|---|---|---|---|---|---|---|---|---|---|---|
| 3069 | 3 | 4 | 5 | | | V-2 | YBX1 | 0.57 | 3165 | 3 | 4 | 5 | | | V-1 | ALG10B | 1.65 |
| 3070 | 3 | 4 | 5 | | | V-2 | YEATS4 | 0.65 | 3166 | 3 | 4 | 5 | | | V-1 | ALG12 | 1.63 |
| 3071 | 3 | 4 | 5 | | | V-2 | ZNF853 | 0.64 | 3167 | 3 | 4 | 5 | | | V-1 | AMD1 | 1.81 |
| 3072 | 3 | 4 | 5 | | | V-1 | AACS | 1.90 | 3168 | 3 | 4 | 5 | | | V-1 | AMICA1 | 1.79 |
| 3073 | 3 | 4 | 5 | | | V-1 | AAMP | 1.98 | 3169 | 3 | 4 | 5 | | | V-1 | AMMECR1 | 1.98 |
| 3074 | 3 | 4 | 5 | | | V-1 | AASDHPPT | 1.73 | 3170 | 3 | 4 | 5 | | | V-1 | AMMECR1L | 1.94 |
| 3075 | 3 | 4 | 5 | | | V-1 | AATF | 1.62 | 3171 | 3 | 4 | 5 | | | V-1 | AMY1A | 1.57 |
| 3076 | 3 | 4 | 5 | | | V-1 | AATK | 1.67 | 3172 | 3 | 4 | 5 | | | V-1 | AMZ2P1 | 1.90 |
| 3077 | 3 | 4 | 5 | | | V-1 | ABCA11P | 1.53 | 3173 | 3 | 4 | 5 | | | V-1 | ANAPC1 | 1.88 |
| 3078 | 3 | 4 | 5 | | | V-1 | ABCB10 | 1.86 | 3174 | 3 | 4 | 5 | | | V-1 | ANAPC5 | 1.92 |
| 3079 | 3 | 4 | 5 | | | V-1 | ABCB7 | 1.52 | 3175 | 3 | 4 | 5 | | | V-1 | ANGEL1 | 1.63 |
| 3080 | 3 | 4 | 5 | | | V-1 | ABCC6P2 | 1.51 | 3176 | 3 | 4 | 5 | | | V-1 | ANGEL2 | 1.80 |
| 3081 | 3 | 4 | 5 | | | V-1 | ABCF1 | 1.77 | 3177 | 3 | 4 | 5 | | | V-1 | ANK3 | 1.68 |
| 3082 | 3 | 4 | 5 | | | V-1 | ABHD10 | 1.53 | 3178 | 3 | 4 | 5 | | | V-1 | ANKLE2 | 1.91 |
| 3083 | 3 | 4 | 5 | | | V-1 | ABHD15 | 1.81 | 3179 | 3 | 4 | 5 | | | V-1 | ANKMY1 | 1.54 |
| 3084 | 3 | 4 | 5 | | | V-1 | ABHD2 | 1.68 | 3180 | 3 | 4 | 5 | | | V-1 | ANKMY2 | 1.85 |
| 3085 | 3 | 4 | 5 | | | V-1 | ABHD5 | 1.68 | 3181 | 3 | 4 | 5 | | | V-1 | ANKRD27 | 1.65 |
| 3086 | 3 | 4 | 5 | | | V-1 | ABHD8 | 1.57 | 3182 | 3 | 4 | 5 | | | V-1 | ANKRD33B | 1.72 |
| 3087 | 3 | 4 | 5 | | | V-1 | ABI1 | 1.91 | 3183 | 3 | 4 | 5 | | | V-1 | ANKRD36BP1 | 1.66 |
| 3088 | 3 | 4 | 5 | | | V-1 | ABI3 | 1.62 | 3184 | 3 | 4 | 5 | | | V-1 | ANKRD40 | 1.67 |
| 3089 | 3 | 4 | 5 | | | V-1 | ABL2 | 1.77 | 3185 | 3 | 4 | 5 | | | V-1 | ANKRD42 | 1.53 |
| 3090 | 3 | 4 | 5 | | | V-1 | ABTB2 | 1.80 | 3186 | 3 | 4 | 5 | | | V-1 | ANKRD54 | 1.56 |
| 3091 | 3 | 4 | 5 | | | V-1 | ACAA1 | 1.79 | 3187 | 3 | 4 | 5 | | | V-1 | ANKS3 | 1.82 |
| 3092 | 3 | 4 | 5 | | | V-1 | ACACB | 1.61 | 3188 | 3 | 4 | 5 | | | V-1 | ANO10 | 1.52 |
| 3093 | 3 | 4 | 5 | | | V-1 | ACAD5 | 1.69 | 3189 | 3 | 4 | 5 | | | V-1 | ANP32D | 1.51 |
| 3094 | 3 | 4 | 5 | | | V-1 | ACAT2 | 1.61 | 3190 | 3 | 4 | 5 | | | V-1 | ANPEP | 1.98 |
| 3095 | 3 | 4 | 5 | | | V-1 | ACBD3 | 1.69 | 3191 | 3 | 4 | 5 | | | V-1 | AOAH | 1.53 |
| 3096 | 3 | 4 | 5 | | | V-1 | ACBD5 | 1.65 | 3192 | 3 | 4 | 5 | | | V-1 | AP1B1 | 1.94 |
| 3097 | 3 | 4 | 5 | | | V-1 | ACD | 1.58 | 3193 | 3 | 4 | 5 | | | V-1 | AP1M1 | 1.68 |
| 3098 | 3 | 4 | 5 | | | V-1 | ACER2 | 1.78 | 3194 | 3 | 4 | 5 | | | V-1 | AP2A1 | 1.84 |
| 3099 | 3 | 4 | 5 | | | V-1 | ACLY | 1.95 | 3195 | 3 | 4 | 5 | | | V-1 | AP2B1 | 1.88 |
| 3100 | 3 | 4 | 5 | | | V-1 | ACO2 | 1.80 | 3196 | 3 | 4 | 5 | | | V-1 | AP3D1 | 1.95 |
| 3101 | 3 | 4 | 5 | | | V-1 | ACOT13 | 1.84 | 3197 | 3 | 4 | 5 | | | V-1 | AP3M1 | 1.71 |
| 3102 | 3 | 4 | 5 | | | V-1 | ACOT7 | 1.52 | 3198 | 3 | 4 | 5 | | | V-1 | AP4M1 | 1.68 |
| 3103 | 3 | 4 | 5 | | | V-1 | ACPL2 | 1.55 | 3199 | 3 | 4 | 5 | | | V-1 | AP5A3 | 1.59 |
| 3104 | 3 | 4 | 5 | | | V-1 | ACRBP | 1.89 | 3200 | 3 | 4 | 5 | | | V-1 | APEH | 1.62 |
| 3105 | 3 | 4 | 5 | | | V-1 | ACSL3 | 1.71 | 3201 | 3 | 4 | 5 | | | V-1 | APEX2 | 1.62 |
| 3106 | 3 | 4 | 5 | | | V-1 | ACSL4 | 1.92 | 3202 | 3 | 4 | 5 | | | V-1 | API5 | 1.52 |
| 3107 | 3 | 4 | 5 | | | V-1 | ACSL5 | 1.90 | 3203 | 3 | 4 | 5 | | | V-1 | APPL1 | 1.60 |
| 3108 | 3 | 4 | 5 | | | V-1 | ACTL6A | 1.54 | 3204 | 3 | 4 | 5 | | | V-1 | APPL2 | 1.72 |
| 3109 | 3 | 4 | 5 | | | V-1 | ACTN1 | 1.94 | 3205 | 3 | 4 | 5 | | | V-1 | APTX | 1.52 |
| 3110 | 3 | 4 | 5 | | | V-1 | ACTN4 | 1.69 | 3206 | 3 | 4 | 5 | | | V-1 | AQP9 | 1.56 |
| 3111 | 3 | 4 | 5 | | | V-1 | ACTR1A | 1.60 | 3207 | 3 | 4 | 5 | | | V-1 | AQR | 1.99 |
| 3112 | 3 | 4 | 5 | | | V-1 | ACTR1B | 1.56 | 3208 | 3 | 4 | 5 | | | V-1 | ARAF | 1.68 |
| 3113 | 3 | 4 | 5 | | | V-1 | ACTR2 | 1.65 | 3209 | 3 | 4 | 5 | | | V-1 | ARAP2 | 1.89 |
| 3114 | 3 | 4 | 5 | | | V-1 | ACVR1B | 1.57 | 3210 | 3 | 4 | 5 | | | V-1 | ARCN1 | 1.58 |
| 3115 | 3 | 4 | 5 | | | V-1 | ACYP1 | 1.53 | 3211 | 3 | 4 | 5 | | | V-1 | ARFGAP2 | 1.71 |
| 3116 | 3 | 4 | 5 | | | V-1 | ACYP2 | 1.89 | 3212 | 3 | 4 | 5 | | | V-1 | ARFGEF1 | 1.77 |
| 3117 | 3 | 4 | 5 | | | V-1 | ADAM10 | 1.94 | 3213 | 3 | 4 | 5 | | | V-1 | ARFRP1 | 1.93 |
| 3118 | 3 | 4 | 5 | | | V-1 | ADAMTSL5 | 1.84 | 3214 | 3 | 4 | 5 | | | V-1 | ARG2 | 1.70 |
| 3119 | 3 | 4 | 5 | | | V-1 | ADARB1 | 1.93 | 3215 | 3 | 4 | 5 | | | V-1 | ARHGAP1 | 1.61 |
| 3120 | 3 | 4 | 5 | | | V-1 | ADAT1 | 1.70 | 3216 | 3 | 4 | 5 | | | V-1 | ARHGAP11A | 1.68 |
| 3121 | 3 | 4 | 5 | | | V-1 | ADAT2 | 1.86 | 3217 | 3 | 4 | 5 | | | V-1 | ARHGAP18 | 1.85 |
| 3122 | 3 | 4 | 5 | | | V-1 | ADAT3 | 1.52 | 3218 | 3 | 4 | 5 | | | V-1 | ARHGAP19 | 1.96 |
| 3123 | 3 | 4 | 5 | | | V-1 | ADCK3 | 1.57 | 3219 | 3 | 4 | 5 | | | V-1 | ARHGAP25 | 1.67 |
| 3124 | 3 | 4 | 5 | | | V-1 | ADCY9 | 1.72 | 3220 | 3 | 4 | 5 | | | V-1 | ARHGAP30 | 1.99 |
| 3125 | 3 | 4 | 5 | | | V-1 | ADNP | 1.96 | 3221 | 3 | 4 | 5 | | | V-1 | ARHGAP33 | 1.78 |
| 3126 | 3 | 4 | 5 | | | V-1 | ADO | 1.83 | 3222 | 3 | 4 | 5 | | | V-1 | ARHGEF18 | 2.00 |
| 3127 | 3 | 4 | 5 | | | V-1 | ADPRHL2 | 1.66 | 3223 | 3 | 4 | 5 | | | V-1 | ARHGEF19 | 1.59 |
| 3128 | 3 | 4 | 5 | | | V-1 | ADRBK1 | 1.95 | 3224 | 3 | 4 | 5 | | | V-1 | ARHGEF2 | 1.96 |
| 3129 | 3 | 4 | 5 | | | V-1 | ADRM1 | 1.58 | 3225 | 3 | 4 | 5 | | | V-1 | ARHGEF6 | 1.85 |
| 3130 | 3 | 4 | 5 | | | V-1 | ADSL | 1.63 | 3226 | 3 | 4 | 5 | | | V-1 | ARID1B | 1.89 |
| 3131 | 3 | 4 | 5 | | | V-1 | ADSS | 1.61 | 3227 | 3 | 4 | 5 | | | V-1 | ARID2 | 1.72 |
| 3132 | 3 | 4 | 5 | | | V-1 | AEBP2 | 1.53 | 3228 | 3 | 4 | 5 | | | V-1 | ARID3A | 1.91 |
| 3133 | 3 | 4 | 5 | | | V-1 | AEN | 1.93 | 3229 | 3 | 4 | 5 | | | V-1 | ARID3B | 1.54 |
| 3134 | 3 | 4 | 5 | | | V-1 | AFAP1L2 | 1.60 | 3230 | 3 | 4 | 5 | | | V-1 | ARID5B | 1.67 |
| 3135 | 3 | 4 | 5 | | | V-1 | AFG3L2 | 1.57 | 3231 | 3 | 4 | 5 | | | V-1 | ARIH1 | 1.83 |
| 3136 | 3 | 4 | 5 | | | V-1 | AFMID | 1.65 | 3232 | 3 | 4 | 5 | | | V-1 | ARIH2 | 1.73 |
| 3137 | 3 | 4 | 5 | | | V-1 | AGAP2 | 1.58 | 3233 | 3 | 4 | 5 | | | V-1 | ARL11 | 1.70 |
| 3138 | 3 | 4 | 5 | | | V-1 | AGFG1 | 1.62 | 3234 | 3 | 4 | 5 | | | V-1 | ARL13B | 1.69 |
| 3139 | 3 | 4 | 5 | | | V-1 | AGGF1 | 1.56 | 3235 | 3 | 4 | 5 | | | V-1 | ARL15 | 1.58 |
| 3140 | 3 | 4 | 5 | | | V-1 | AGK | 1.99 | 3236 | 3 | 4 | 5 | | | V-1 | ARL5B | 1.79 |
| 3141 | 3 | 4 | 5 | | | V-1 | AGPAT5 | 1.79 | 3237 | 3 | 4 | 5 | | | V-1 | ARL6IP6 | 1.54 |
| 3142 | 3 | 4 | 5 | | | V-1 | AGPAT6 | 1.90 | 3238 | 3 | 4 | 5 | | | V-1 | ARL8B | 1.97 |
| 3143 | 3 | 4 | 5 | | | V-1 | AGPAT9 | 1.83 | 3239 | 3 | 4 | 5 | | | V-1 | ARMC6 | 1.77 |
| 3144 | 3 | 4 | 5 | | | V-1 | AGPS | 1.96 | 3240 | 3 | 4 | 5 | | | V-1 | ARMC7 | 1.56 |
| 3145 | 3 | 4 | 5 | | | V-1 | AHCTF1 | 1.81 | 3241 | 3 | 4 | 5 | | | V-1 | ARMC8 | 1.92 |
| 3146 | 3 | 4 | 5 | | | V-1 | AHCYL1 | 1.93 | 3242 | 3 | 4 | 5 | | | V-1 | ARMCX1 | 1.57 |
| 3147 | 3 | 4 | 5 | | | V-1 | AIFM1 | 1.78 | 3243 | 3 | 4 | 5 | | | V-1 | ARMCX5 | 1.51 |
| 3148 | 3 | 4 | 5 | | | V-1 | AIFM2 | 1.96 | 3244 | 3 | 4 | 5 | | | V-1 | ARNT | 1.98 |
| 3149 | 3 | 4 | 5 | | | V-1 | AIFM3 | 1.61 | 3245 | 3 | 4 | 5 | | | V-1 | ARPC1A | 1.76 |
| 3150 | 3 | 4 | 5 | | | V-1 | AIM1 | 1.91 | 3246 | 3 | 4 | 5 | | | V-1 | ARRB2 | 1.68 |
| 3151 | 3 | 4 | 5 | | | V-1 | AIMP1 | 1.71 | 3247 | 3 | 4 | 5 | | | V-1 | ARRDC1 | 1.60 |
| 3152 | 3 | 4 | 5 | | | V-1 | AK2 | 1.50 | 3248 | 3 | 4 | 5 | | | V-1 | ARRDC2 | 1.97 |
| 3153 | 3 | 4 | 5 | | | V-1 | AKAP1 | 1.89 | 3249 | 3 | 4 | 5 | | | V-1 | ARSG | 1.88 |
| 3154 | 3 | 4 | 5 | | | V-1 | AKAP10 | 1.71 | 3250 | 3 | 4 | 5 | | | V-1 | ASB1 | 1.66 |
| 3155 | 3 | 4 | 5 | | | V-1 | AKAP11 | 1.79 | 3251 | 3 | 4 | 5 | | | V-1 | ASB6 | 1.58 |
| 3156 | 3 | 4 | 5 | | | V-1 | AKAP8 | 1.95 | 3252 | 3 | 4 | 5 | | | V-1 | ASB8 | 1.66 |
| 3157 | 3 | 4 | 5 | | | V-1 | AKIRIN1 | 1.65 | 3253 | 3 | 4 | 5 | | | V-1 | ASH1L | 1.95 |
| 3158 | 3 | 4 | 5 | | | V-1 | AKNA | 1.54 | 3254 | 3 | 4 | 5 | | | V-1 | ASH2L | 1.55 |
| 3159 | 3 | 4 | 5 | | | V-1 | AKT2 | 1.55 | 3255 | 3 | 4 | 5 | | | V-1 | ASPH | 1.66 |
| 3160 | 3 | 4 | 5 | | | V-1 | AKTIP | 1.60 | 3256 | 3 | 4 | 5 | | | V-1 | ASTE1 | 1.69 |
| 3161 | 3 | 4 | 5 | | | V-1 | ALAD | 1.54 | 3257 | 3 | 4 | 5 | | | V-1 | ATAT1 | 1.80 |
| 3162 | 3 | 4 | 5 | | | V-1 | ALAS1 | 1.85 | 3258 | 3 | 4 | 5 | | | V-1 | ATF2 | 1.65 |
| 3163 | 3 | 4 | 5 | | | V-1 | ALG1 | 1.71 | 3259 | 3 | 4 | 5 | | | V-1 | ATF6 | 1.75 |
| 3164 | 3 | 4 | 5 | | | V-1 | ALG10 | 1.88 | 3260 | 3 | 4 | 5 | | | V-1 | ATG12 | 1.88 |

Fig. 40 - 18

| | | | | | | | | | | | | | | | |
|---|---|---|---|---|---|---|---|---|---|---|---|---|---|---|---|
| 3261 | 3 | 4 | 5 | | | V-1 | ATG13 | 1.50 | 3357 | 3 | 4 | 5 | | V-1 | BYSL | 1.63 |
| 3262 | 3 | 4 | 5 | | | V-1 | ATG14 | 1.63 | 3358 | 3 | 4 | 5 | | V-1 | C10orf116 | 1.91 |
| 3263 | 3 | 4 | 5 | | | V-1 | ATG16L1 | 1.71 | 3359 | 3 | 4 | 5 | | V-1 | C10orf118 | 1.67 |
| 3264 | 3 | 4 | 5 | | | V-1 | ATG4B | 1.94 | 3360 | 3 | 4 | 5 | | V-1 | C10orf28 | 1.61 |
| 3265 | 3 | 4 | 5 | | | V-1 | ATG4C | 1.65 | 3361 | 3 | 4 | 5 | | V-1 | C10orf46 | 1.59 |
| 3266 | 3 | 4 | 5 | | | V-1 | ATG4D | 1.81 | 3362 | 3 | 4 | 5 | | V-1 | C10orf58 | 1.71 |
| 3267 | 3 | 4 | 5 | | | V-1 | ATG9A | 1.90 | 3363 | 3 | 4 | 5 | | V-1 | C10orf76 | 1.99 |
| 3268 | 3 | 4 | 5 | | | V-1 | ATP10A | 1.90 | 3364 | 3 | 4 | 5 | | V-1 | C10orf88 | 1.55 |
| 3269 | 3 | 4 | 5 | | | V-1 | ATP13A2 | 1.66 | 3365 | 3 | 4 | 5 | | V-1 | C11orf10 | 1.54 |
| 3270 | 3 | 4 | 5 | | | V-1 | ATP13A3 | 1.89 | 3366 | 3 | 4 | 5 | | V-1 | C11orf35 | 1.67 |
| 3271 | 3 | 4 | 5 | | | V-1 | ATP5B | 1.62 | 3367 | 3 | 4 | 5 | | V-1 | C11orf48 | 1.69 |
| 3272 | 3 | 4 | 5 | | | V-1 | ATP5H | 1.57 | 3368 | 3 | 4 | 5 | | V-1 | C11orf63 | 1.99 |
| 3273 | 3 | 4 | 5 | | | V-1 | ATP5S | 1.83 | 3369 | 3 | 4 | 5 | | V-1 | C11orf68 | 1.69 |
| 3274 | 3 | 4 | 5 | | | V-1 | ATP6AP1 | 1.97 | 3370 | 3 | 4 | 5 | | V-1 | C11orf73 | 1.57 |
| 3275 | 3 | 4 | 5 | | | V-1 | ATP6AP2 | 1.83 | 3371 | 3 | 4 | 5 | | V-1 | C11orf75 | 1.75 |
| 3276 | 3 | 4 | 5 | | | V-1 | ATP6V0E1 | 1.68 | 3372 | 3 | 4 | 5 | | V-1 | C11orf95 | 1.81 |
| 3277 | 3 | 4 | 5 | | | V-1 | ATP6V1A | 1.82 | 3373 | 3 | 4 | 5 | | V-1 | C12orf47 | 1.88 |
| 3278 | 3 | 4 | 5 | | | V-1 | ATP6V1C1 | 1.80 | 3374 | 3 | 4 | 5 | | V-1 | C12orf73 | 1.63 |
| 3279 | 3 | 4 | 5 | | | V-1 | ATP6V1E1 | 1.85 | 3375 | 3 | 4 | 5 | | V-1 | C14orf118 | 1.77 |
| 3280 | 3 | 4 | 5 | | | V-1 | ATP6V1E2 | 1.59 | 3376 | 3 | 4 | 5 | | V-1 | C14orf135 | 1.82 |
| 3281 | 3 | 4 | 5 | | | V-1 | ATP6V1H | 1.74 | 3377 | 3 | 4 | 5 | | V-1 | C14orf182 | 1.58 |
| 3282 | 3 | 4 | 5 | | | V-1 | ATP8B2 | 1.57 | 3378 | 3 | 4 | 5 | | V-1 | C14orf43 | 1.80 |
| 3283 | 3 | 4 | 5 | | | V-1 | ATPBD4 | 1.52 | 3379 | 3 | 4 | 5 | | V-1 | C14orf93 | 1.96 |
| 3284 | 3 | 4 | 5 | | | V-1 | ATRIP | 1.78 | 3380 | 3 | 4 | 5 | | V-1 | C15orf40 | 1.63 |
| 3285 | 3 | 4 | 5 | | | V-1 | ATXN3 | 1.76 | 3381 | 3 | 4 | 5 | | V-1 | C15orf41 | 1.85 |
| 3286 | 3 | 4 | 5 | | | V-1 | AUP1 | 1.96 | 3382 | 3 | 4 | 5 | | V-1 | C15orf52 | 1.98 |
| 3287 | 3 | 4 | 5 | | | V-1 | AURKA | 1.60 | 3383 | 3 | 4 | 5 | | V-1 | C15orf58 | 1.66 |
| 3288 | 3 | 4 | 5 | | | V-1 | AURKAPS1 | 1.91 | 3384 | 3 | 4 | 5 | | V-1 | C16orf45 | 1.80 |
| 3289 | 3 | 4 | 5 | | | V-1 | AVL9 | 1.65 | 3385 | 3 | 4 | 5 | | V-1 | C16orf5 | 1.79 |
| 3290 | 3 | 4 | 5 | | | V-1 | AVPI1 | 1.65 | 3386 | 3 | 4 | 5 | | V-1 | C16orf58 | 1.70 |
| 3291 | 3 | 4 | 5 | | | V-1 | AZI2 | 2.00 | 3387 | 3 | 4 | 5 | | V-1 | C16orf62 | 1.87 |
| 3292 | 3 | 4 | 5 | | | V-1 | B3GALT6 | 1.57 | 3388 | 3 | 4 | 5 | | V-1 | C16orf79 | 1.84 |
| 3293 | 3 | 4 | 5 | | | V-1 | B3GAT3 | 1.70 | 3389 | 3 | 4 | 5 | | V-1 | C16orf93 | 1.76 |
| 3294 | 3 | 4 | 5 | | | V-1 | B3GNT2 | 1.53 | 3390 | 3 | 4 | 5 | | V-1 | C17orf48 | 1.73 |
| 3295 | 3 | 4 | 5 | | | V-1 | B3GNT5 | 1.61 | 3391 | 3 | 4 | 5 | | V-1 | C17orf62 | 1.89 |
| 3296 | 3 | 4 | 5 | | | V-1 | B3GNT9 | 1.62 | 3392 | 3 | 4 | 5 | | V-1 | C17orf80 | 1.63 |
| 3297 | 3 | 4 | 5 | | | V-1 | B4GALT5 | 1.60 | 3393 | 3 | 4 | 5 | | V-1 | C17orf90 | 1.65 |
| 3298 | 3 | 4 | 5 | | | V-1 | BAHD1 | 1.83 | 3394 | 3 | 4 | 5 | | V-1 | C18orf21 | 1.78 |
| 3299 | 3 | 4 | 5 | | | V-1 | BAMBI | 1.71 | 3395 | 3 | 4 | 5 | | V-1 | C18orf32 | 1.92 |
| 3300 | 3 | 4 | 5 | | | V-1 | BANP | 1.93 | 3396 | 3 | 4 | 5 | | V-1 | C19orf29 | 1.72 |
| 3301 | 3 | 4 | 5 | | | V-1 | BBC3 | 1.79 | 3397 | 3 | 4 | 5 | | V-1 | C19orf42 | 1.64 |
| 3302 | 3 | 4 | 5 | | | V-1 | BBIP1 | 1.71 | 3398 | 3 | 4 | 5 | | V-1 | C19orf52 | 1.96 |
| 3303 | 3 | 4 | 5 | | | V-1 | BBS1 | 1.92 | 3399 | 3 | 4 | 5 | | V-1 | C19orf60 | 1.60 |
| 3304 | 3 | 4 | 5 | | | V-1 | BBS10 | 1.78 | 3400 | 3 | 4 | 5 | | V-1 | C1GALT1C1 | 1.84 |
| 3305 | 3 | 4 | 5 | | | V-1 | BBS2 | 1.93 | 3401 | 3 | 4 | 5 | | V-1 | C1QC | 1.71 |
| 3306 | 3 | 4 | 5 | | | V-1 | BBS4 | 1.77 | 3402 | 3 | 4 | 5 | | V-1 | C1RL | 1.93 |
| 3307 | 3 | 4 | 5 | | | V-1 | BBS7 | 1.65 | 3403 | 3 | 4 | 5 | | V-1 | C1orf109 | 1.86 |
| 3308 | 3 | 4 | 5 | | | V-1 | BCAS2 | 1.61 | 3404 | 3 | 4 | 5 | | V-1 | C1orf122 | 1.91 |
| 3309 | 3 | 4 | 5 | | | V-1 | BCAS3 | 1.73 | 3405 | 3 | 4 | 5 | | V-1 | C1orf124 | 1.82 |
| 3310 | 3 | 4 | 5 | | | V-1 | BCCIP | 1.78 | 3406 | 3 | 4 | 5 | | V-1 | C1orf131 | 1.85 |
| 3311 | 3 | 4 | 5 | | | V-1 | BCKDHB | 1.55 | 3407 | 3 | 4 | 5 | | V-1 | C1orf200 | 1.65 |
| 3312 | 3 | 4 | 5 | | | V-1 | BCKDK | 1.65 | 3408 | 3 | 4 | 5 | | V-1 | C1orf213 | 1.65 |
| 3313 | 3 | 4 | 5 | | | V-1 | BCL10 | 1.85 | 3409 | 3 | 4 | 5 | | V-1 | C1orf31 | 1.84 |
| 3314 | 3 | 4 | 5 | | | V-1 | BCLAF1 | 1.86 | 3410 | 3 | 4 | 5 | | V-1 | C1orf35 | 1.72 |
| 3315 | 3 | 4 | 5 | | | V-1 | BCR | 1.50 | 3411 | 3 | 4 | 5 | | V-1 | C1orf38 | 1.78 |
| 3316 | 3 | 4 | 5 | | | V-1 | BCRP3 | 1.97 | 3412 | 3 | 4 | 5 | | V-1 | C1orf52 | 1.88 |
| 3317 | 3 | 4 | 5 | | | V-1 | BECN1 | 1.74 | 3413 | 3 | 4 | 5 | | V-1 | C20orf111 | 1.59 |
| 3318 | 3 | 4 | 5 | | | V-1 | BHLHA15 | 1.65 | 3414 | 3 | 4 | 5 | | V-1 | C20orf197 | 1.95 |
| 3319 | 3 | 4 | 5 | | | V-1 | BICD2 | 1.92 | 3415 | 3 | 4 | 5 | | V-1 | C20orf29 | 1.50 |
| 3320 | 3 | 4 | 5 | | | V-1 | BIN2 | 1.62 | 3416 | 3 | 4 | 5 | | V-1 | C20orf72 | 1.95 |
| 3321 | 3 | 4 | 5 | | | V-1 | BIRC3 | 1.84 | 3417 | 3 | 4 | 5 | | V-1 | C20orf94 | 1.54 |
| 3322 | 3 | 4 | 5 | | | V-1 | BIVM | 1.92 | 3418 | 3 | 4 | 5 | | V-1 | C21orf2 | 1.98 |
| 3323 | 3 | 4 | 5 | | | V-1 | BLM | 1.56 | 3419 | 3 | 4 | 5 | | V-1 | C21orf59 | 1.91 |
| 3324 | 3 | 4 | 5 | | | V-1 | BLOC1S2 | 1.75 | 3420 | 3 | 4 | 5 | | V-1 | C22orf28 | 1.76 |
| 3325 | 3 | 4 | 5 | | | V-1 | BLOC1S3 | 1.59 | 3421 | 3 | 4 | 5 | | V-1 | C22orf29 | 1.77 |
| 3326 | 3 | 4 | 5 | | | V-1 | BMF | 1.63 | 3422 | 3 | 4 | 5 | | V-1 | C2orf18 | 1.78 |
| 3327 | 3 | 4 | 5 | | | V-1 | BMP2K | 1.54 | 3423 | 3 | 4 | 5 | | V-1 | C2orf42 | 1.83 |
| 3328 | 3 | 4 | 5 | | | V-1 | BMP8A | 1.77 | 3424 | 3 | 4 | 5 | | V-1 | C2orf49 | 1.51 |
| 3329 | 3 | 4 | 5 | | | V-1 | BMP8B | 1.87 | 3425 | 3 | 4 | 5 | | V-1 | C2orf68 | 1.93 |
| 3330 | 3 | 4 | 5 | | | V-1 | BNIP2 | 1.78 | 3426 | 3 | 4 | 5 | | V-1 | C2orf69 | 1.67 |
| 3331 | 3 | 4 | 5 | | | V-1 | BNIP3L | 1.93 | 3427 | 3 | 4 | 5 | | V-1 | C3orf14 | 1.61 |
| 3332 | 3 | 4 | 5 | | | V-1 | BORA | 1.92 | 3428 | 3 | 4 | 5 | | V-1 | C3orf17 | 1.58 |
| 3333 | 3 | 4 | 5 | | | V-1 | BRAP | 1.89 | 3429 | 3 | 4 | 5 | | V-1 | C3orf19 | 1.65 |
| 3334 | 3 | 4 | 5 | | | V-1 | BRD1 | 1.88 | 3430 | 3 | 4 | 5 | | V-1 | C3orf23 | 1.80 |
| 3335 | 3 | 4 | 5 | | | V-1 | BRD2 | 1.62 | 3431 | 3 | 4 | 5 | | V-1 | C3orf37 | 1.62 |
| 3336 | 3 | 4 | 5 | | | V-1 | BRD3 | 1.96 | 3432 | 3 | 4 | 5 | | V-1 | C3orf38 | 1.68 |
| 3337 | 3 | 4 | 5 | | | V-1 | BRD7 | 1.63 | 3433 | 3 | 4 | 5 | | V-1 | C3orf58 | 1.80 |
| 3338 | 3 | 4 | 5 | | | V-1 | BRD8 | 1.54 | 3434 | 3 | 4 | 5 | | V-1 | C3orf64 | 1.74 |
| 3339 | 3 | 4 | 5 | | | V-1 | BRD9 | 1.91 | 3435 | 3 | 4 | 5 | | V-1 | C3orf71 | 1.57 |
| 3340 | 3 | 4 | 5 | | | V-1 | BRE | 1.99 | 3436 | 3 | 4 | 5 | | V-1 | C4orf29 | 1.86 |
| 3341 | 3 | 4 | 5 | | | V-1 | BRF1 | 1.62 | 3437 | 3 | 4 | 5 | | V-1 | C4orf34 | 1.63 |
| 3342 | 3 | 4 | 5 | | | V-1 | BRI3 | 1.85 | 3438 | 3 | 4 | 5 | | V-1 | C4orf43 | 1.64 |
| 3343 | 3 | 4 | 5 | | | V-1 | BRMS1 | 1.56 | 3439 | 3 | 4 | 5 | | V-1 | C5AR1 | 1.61 |
| 3344 | 3 | 4 | 5 | | | V-1 | BRP44L | 1.63 | 3440 | 3 | 4 | 5 | | V-1 | C5orf15 | 1.92 |
| 3345 | 3 | 4 | 5 | | | V-1 | BRPF1 | 1.54 | 3441 | 3 | 4 | 5 | | V-1 | C5orf22 | 1.77 |
| 3346 | 3 | 4 | 5 | | | V-1 | BRWD1 | 1.84 | 3442 | 3 | 4 | 5 | | V-1 | C5orf24 | 1.83 |
| 3347 | 3 | 4 | 5 | | | V-1 | BRWD3 | 1.85 | 3443 | 3 | 4 | 5 | | V-1 | C5orf28 | 1.71 |
| 3348 | 3 | 4 | 5 | | | V-1 | BSCL2 | 1.53 | 3444 | 3 | 4 | 5 | | V-1 | C5orf39 | 1.59 |
| 3349 | 3 | 4 | 5 | | | V-1 | BSDC1 | 1.75 | 3445 | 3 | 4 | 5 | | V-1 | C5orf43 | 1.67 |
| 3350 | 3 | 4 | 5 | | | V-1 | BTBD19 | 1.97 | 3446 | 3 | 4 | 5 | | V-1 | C5orf44 | 1.54 |
| 3351 | 3 | 4 | 5 | | | V-1 | BTBD2 | 1.75 | 3447 | 3 | 4 | 5 | | V-1 | C6orf106 | 1.77 |
| 3352 | 3 | 4 | 5 | | | V-1 | BTBD7 | 1.60 | 3448 | 3 | 4 | 5 | | V-1 | C6orf120 | 1.76 |
| 3353 | 3 | 4 | 5 | | | V-1 | BTBD9 | 1.80 | 3449 | 3 | 4 | 5 | | V-1 | C6orf192 | 1.89 |
| 3354 | 3 | 4 | 5 | | | V-1 | BTD | 1.61 | 3450 | 3 | 4 | 5 | | V-1 | C6orf203 | 1.60 |
| 3355 | 3 | 4 | 5 | | | V-1 | BTRC | 1.69 | 3451 | 3 | 4 | 5 | | V-1 | C6orf226 | 1.85 |
| 3356 | 3 | 4 | 5 | | | V-1 | BUB3 | 1.61 | 3452 | 3 | 4 | 5 | | V-1 | C6orf228 | 1.52 |

Fig. 40 - 19

| | | | | | | | | | | | | | | | |
|---|---|---|---|---|---|---|---|---|---|---|---|---|---|---|---|
| 3453 | 3 | 4 | 5 | | | V-1 | C6orf47 | 1.80 | 3549 | 3 | 4 | 5 | | V-1 | CDC23 | 1.54 |
| 3454 | 3 | 4 | 5 | | | V-1 | C6orf89 | 1.53 | 3550 | 3 | 4 | 5 | | V-1 | CDC25B | 1.86 |
| 3455 | 3 | 4 | 5 | | | V-1 | C7orf23 | 1.65 | 3551 | 3 | 4 | 5 | | V-1 | CDC27 | 1.84 |
| 3456 | 3 | 4 | 5 | | | V-1 | C7orf25 | 1.75 | 3552 | 3 | 4 | 5 | | V-1 | CDC40 | 1.88 |
| 3457 | 3 | 4 | 5 | | | V-1 | C7orf26 | 1.62 | 3553 | 3 | 4 | 5 | | V-1 | CDC42SE1 | 1.98 |
| 3458 | 3 | 4 | 5 | | | V-1 | C7orf31 | 1.89 | 3554 | 3 | 4 | 5 | | V-1 | CDC73 | 1.85 |
| 3459 | 3 | 4 | 5 | | | V-1 | C7orf49 | 1.96 | 3555 | 3 | 4 | 5 | | V-1 | CDK12 | 1.51 |
| 3460 | 3 | 4 | 5 | | | V-1 | C8orf39 | 1.64 | 3556 | 3 | 4 | 5 | | V-1 | CDK13 | 1.93 |
| 3461 | 3 | 4 | 5 | | | V-1 | C8orf82 | 1.94 | 3557 | 3 | 4 | 5 | | V-1 | CDK18 | 1.63 |
| 3462 | 3 | 4 | 5 | | | V-1 | C8orf83 | 1.67 | 3558 | 3 | 4 | 5 | | V-1 | CDK20 | 1.77 |
| 3463 | 3 | 4 | 5 | | | V-1 | C9orf129 | 1.58 | 3559 | 3 | 4 | 5 | | V-1 | CDK8 | 1.59 |
| 3464 | 3 | 4 | 5 | | | V-1 | C9orf142 | 1.91 | 3560 | 3 | 4 | 5 | | V-1 | CDK9 | 1.61 |
| 3465 | 3 | 4 | 5 | | | V-1 | C9orf167 | 1.78 | 3561 | 3 | 4 | 5 | | V-1 | CDKAL1 | 1.69 |
| 3466 | 3 | 4 | 5 | | | V-1 | C9orf46 | 1.71 | 3562 | 3 | 4 | 5 | | V-1 | CDRT4 | 1.88 |
| 3467 | 3 | 4 | 5 | | | V-1 | C9orf5 | 1.68 | 3563 | 3 | 4 | 5 | | V-1 | CDS2 | 1.83 |
| 3468 | 3 | 4 | 5 | | | V-1 | C9orf80 | 1.63 | 3564 | 3 | 4 | 5 | | V-1 | CDV3 | 1.69 |
| 3469 | 3 | 4 | 5 | | | V-1 | C9orf95 | 1.70 | 3565 | 3 | 4 | 5 | | V-1 | CDYL | 1.62 |
| 3470 | 3 | 4 | 5 | | | V-1 | CA11 | 1.54 | 3566 | 3 | 4 | 5 | | V-1 | CEBPG | 1.60 |
| 3471 | 3 | 4 | 5 | | | V-1 | CA13 | 1.71 | 3567 | 3 | 4 | 5 | | V-1 | CEBPZ | 1.68 |
| 3472 | 3 | 4 | 5 | | | V-1 | CA5BP1 | 1.62 | 3568 | 3 | 4 | 5 | | V-1 | CECR5 | 1.67 |
| 3473 | 3 | 4 | 5 | | | V-1 | CABLES2 | 1.54 | 3569 | 3 | 4 | 5 | | V-1 | CENPO | 1.75 |
| 3474 | 3 | 4 | 5 | | | V-1 | CACNA2D4 | 1.74 | 3570 | 3 | 4 | 5 | | V-1 | CENPW | 1.73 |
| 3475 | 3 | 4 | 5 | | | V-1 | CAMK2D | 1.95 | 3571 | 3 | 4 | 5 | | V-1 | CEP104 | 1.86 |
| 3476 | 3 | 4 | 5 | | | V-1 | CAMKK2 | 1.56 | 3572 | 3 | 4 | 5 | | V-1 | CEP120 | 1.81 |
| 3477 | 3 | 4 | 5 | | | V-1 | CAMSAP2 | 1.65 | 3573 | 3 | 4 | 5 | | V-1 | CEP170P1 | 1.52 |
| 3478 | 3 | 4 | 5 | | | V-1 | CAMTA2 | 1.84 | 3574 | 3 | 4 | 5 | | V-1 | CEP250 | 1.63 |
| 3479 | 3 | 4 | 5 | | | V-1 | CAND1 | 1.81 | 3575 | 3 | 4 | 5 | | V-1 | CEP290 | 1.64 |
| 3480 | 3 | 4 | 5 | | | V-1 | CANX | 1.52 | 3576 | 3 | 4 | 5 | | V-1 | CEP57 | 1.54 |
| 3481 | 3 | 4 | 5 | | | V-1 | CAP1 | 1.58 | 3577 | 3 | 4 | 5 | | V-1 | CEP85L | 1.92 |
| 3482 | 3 | 4 | 5 | | | V-1 | CAPN7 | 1.99 | 3578 | 3 | 4 | 5 | | V-1 | CEP89 | 1.75 |
| 3483 | 3 | 4 | 5 | | | V-1 | CAPRIN1 | 1.89 | 3579 | 3 | 4 | 5 | | V-1 | CEPT1 | 1.98 |
| 3484 | 3 | 4 | 5 | | | V-1 | CAPZA1 | 1.61 | 3580 | 3 | 4 | 5 | | V-1 | CERS2 | 1.71 |
| 3485 | 3 | 4 | 5 | | | V-1 | CAPZA2 | 1.55 | 3581 | 3 | 4 | 5 | | V-1 | CERS5 | 1.99 |
| 3486 | 3 | 4 | 5 | | | V-1 | CARD11 | 1.52 | 3582 | 3 | 4 | 5 | | V-1 | CFDP1 | 1.53 |
| 3487 | 3 | 4 | 5 | | | V-1 | CARNS1 | 1.95 | 3583 | 3 | 4 | 5 | | V-1 | CFLAR-AS1 | 1.95 |
| 3488 | 3 | 4 | 5 | | | V-1 | CARS2 | 2.00 | 3584 | 3 | 4 | 5 | | V-1 | CFP | 1.95 |
| 3489 | 3 | 4 | 5 | | | V-1 | CASD1 | 1.59 | 3585 | 3 | 4 | 5 | | V-1 | CHAMP1 | 1.91 |
| 3490 | 3 | 4 | 5 | | | V-1 | CA5K | 1.64 | 3586 | 3 | 4 | 5 | | V-1 | CHCHD1 | 1.68 |
| 3491 | 3 | 4 | 5 | | | V-1 | CASP2 | 1.61 | 3587 | 3 | 4 | 5 | | V-1 | CHCHD10 | 1.57 |
| 3492 | 3 | 4 | 5 | | | V-1 | CASP3 | 1.54 | 3588 | 3 | 4 | 5 | | V-1 | CHCHD7 | 1.60 |
| 3493 | 3 | 4 | 5 | | | V-1 | CASP6 | 1.58 | 3589 | 3 | 4 | 5 | | V-1 | CHD1L | 1.69 |
| 3494 | 3 | 4 | 5 | | | V-1 | CASP9 | 1.73 | 3590 | 3 | 4 | 5 | | V-1 | CHD9 | 1.69 |
| 3495 | 3 | 4 | 5 | | | V-1 | CAV2 | 1.92 | 3591 | 3 | 4 | 5 | | V-1 | CHID1 | 1.54 |
| 3496 | 3 | 4 | 5 | | | V-1 | CBFB | 1.70 | 3592 | 3 | 4 | 5 | | V-1 | CHMP1B | 2.00 |
| 3497 | 3 | 4 | 5 | | | V-1 | CBLL1 | 1.58 | 3593 | 3 | 4 | 5 | | V-1 | CHMP2B | 1.73 |
| 3498 | 3 | 4 | 5 | | | V-1 | CBR1 | 1.94 | 3594 | 3 | 4 | 5 | | V-1 | CHMP7 | 1.90 |
| 3499 | 3 | 4 | 5 | | | V-1 | CBR4 | 1.73 | 3595 | 3 | 4 | 5 | | V-1 | CHRNB1 | 1.68 |
| 3500 | 3 | 4 | 5 | | | V-1 | CBX3 | 1.58 | 3596 | 3 | 4 | 5 | | V-1 | CHST14 | 1.58 |
| 3501 | 3 | 4 | 5 | | | V-1 | CBX3P2 | 1.69 | 3597 | 3 | 4 | 5 | | V-1 | CHSY1 | 1.58 |
| 3502 | 3 | 4 | 5 | | | V-1 | CBX7 | 1.67 | 3598 | 3 | 4 | 5 | | V-1 | CHTOP | 1.66 |
| 3503 | 3 | 4 | 5 | | | V-1 | CCBL2 | 1.56 | 3599 | 3 | 4 | 5 | | V-1 | CHUK | 1.84 |
| 3504 | 3 | 4 | 5 | | | V-1 | CCDC101 | 1.56 | 3600 | 3 | 4 | 5 | | V-1 | CHURC1-FNTB | 1.73 |
| 3505 | 3 | 4 | 5 | | | V-1 | CCDC111 | 1.55 | 3601 | 3 | 4 | 5 | | V-1 | CIRH1A | 1.70 |
| 3506 | 3 | 4 | 5 | | | V-1 | CCDC112 | 1.78 | 3602 | 3 | 4 | 5 | | V-1 | CISH | 1.68 |
| 3507 | 3 | 4 | 5 | | | V-1 | CCDC120 | 1.89 | 3603 | 3 | 4 | 5 | | V-1 | CITED2 | 1.51 |
| 3508 | 3 | 4 | 5 | | | V-1 | CCDC132 | 1.94 | 3604 | 3 | 4 | 5 | | V-1 | CKAP4 | 1.55 |
| 3509 | 3 | 4 | 5 | | | V-1 | CCDC137 | 1.78 | 3605 | 3 | 4 | 5 | | V-1 | CLCN3 | 1.82 |
| 3510 | 3 | 4 | 5 | | | V-1 | CCDC28A | 1.60 | 3606 | 3 | 4 | 5 | | V-1 | CLEC2D | 1.80 |
| 3511 | 3 | 4 | 5 | | | V-1 | CCDC39 | 1.97 | 3607 | 3 | 4 | 5 | | V-1 | CLINT1 | 1.54 |
| 3512 | 3 | 4 | 5 | | | V-1 | CCDC428 | 1.73 | 3608 | 3 | 4 | 5 | | V-1 | CLIP2 | 1.91 |
| 3513 | 3 | 4 | 5 | | | V-1 | CCDC43 | 1.60 | 3609 | 3 | 4 | 5 | | V-1 | CLK3 | 1.82 |
| 3514 | 3 | 4 | 5 | | | V-1 | CCDC47 | 1.62 | 3610 | 3 | 4 | 5 | | V-1 | CLN5 | 1.99 |
| 3515 | 3 | 4 | 5 | | | V-1 | CCDC6 | 1.86 | 3611 | 3 | 4 | 5 | | V-1 | CLOCK | 1.75 |
| 3516 | 3 | 4 | 5 | | | V-1 | CCDC82 | 1.72 | 3612 | 3 | 4 | 5 | | V-1 | CLPTM1 | 1.60 |
| 3517 | 3 | 4 | 5 | | | V-1 | CCDC9 | 1.83 | 3613 | 3 | 4 | 5 | | V-1 | CLPTM1L | 1.63 |
| 3518 | 3 | 4 | 5 | | | V-1 | CCDC90B | 1.55 | 3614 | 3 | 4 | 5 | | V-1 | CLSTN3 | 1.98 |
| 3519 | 3 | 4 | 5 | | | V-1 | CCDC91 | 1.50 | 3615 | 3 | 4 | 5 | | V-1 | CMAS | 1.57 |
| 3520 | 3 | 4 | 5 | | | V-1 | CCDC99 | 1.81 | 3616 | 3 | 4 | 5 | | V-1 | CMKLR1 | 1.67 |
| 3521 | 3 | 4 | 5 | | | V-1 | CCM2 | 1.60 | 3617 | 3 | 4 | 5 | | V-1 | CMTM3 | 1.92 |
| 3522 | 3 | 4 | 5 | | | V-1 | CCNDBP1 | 1.56 | 3618 | 3 | 4 | 5 | | V-1 | CMTM6 | 1.54 |
| 3523 | 3 | 4 | 5 | | | V-1 | CCNF | 1.81 | 3619 | 3 | 4 | 5 | | V-1 | CMTM7 | 1.62 |
| 3524 | 3 | 4 | 5 | | | V-1 | CCNG1 | 1.56 | 3620 | 3 | 4 | 5 | | V-1 | CNBP | 1.61 |
| 3525 | 3 | 4 | 5 | | | V-1 | CCNG2 | 1.58 | 3621 | 3 | 4 | 5 | | V-1 | CNEP1R1 | 1.83 |
| 3526 | 3 | 4 | 5 | | | V-1 | CCNT1 | 1.90 | 3622 | 3 | 4 | 5 | | V-1 | CNIH4 | 1.70 |
| 3527 | 3 | 4 | 5 | | | V-1 | CCNYL1 | 1.73 | 3623 | 3 | 4 | 5 | | V-1 | CNNM3 | 1.57 |
| 3528 | 3 | 4 | 5 | | | V-1 | CCP110 | 1.99 | 3624 | 3 | 4 | 5 | | V-1 | CNNM4 | 1.86 |
| 3529 | 3 | 4 | 5 | | | V-1 | CCT2 | 1.51 | 3625 | 3 | 4 | 5 | | V-1 | CNO | 1.55 |
| 3530 | 3 | 4 | 5 | | | V-1 | CCT5 | 1.63 | 3626 | 3 | 4 | 5 | | V-1 | CNOT10 | 1.59 |
| 3531 | 3 | 4 | 5 | | | V-1 | CCT6A | 1.52 | 3627 | 3 | 4 | 5 | | V-1 | CNOT2 | 2.00 |
| 3532 | 3 | 4 | 5 | | | V-1 | CCZ1 | 1.77 | 3628 | 3 | 4 | 5 | | V-1 | CNOT3 | 1.99 |
| 3533 | 3 | 4 | 5 | | | V-1 | CD14 | 1.92 | 3629 | 3 | 4 | 5 | | V-1 | CNOT4 | 1.89 |
| 3534 | 3 | 4 | 5 | | | V-1 | CD164 | 1.81 | 3630 | 3 | 4 | 5 | | V-1 | CNOT6 | 1.59 |
| 3535 | 3 | 4 | 5 | | | V-1 | CD1A | 1.58 | 3631 | 3 | 4 | 5 | | V-1 | CNOT6L | 1.55 |
| 3536 | 3 | 4 | 5 | | | V-1 | CD1D | 1.99 | 3632 | 3 | 4 | 5 | | V-1 | CNOT8 | 1.89 |
| 3537 | 3 | 4 | 5 | | | V-1 | CD200R1 | 1.74 | 3633 | 3 | 4 | 5 | | V-1 | CNPY4 | 1.81 |
| 3538 | 3 | 4 | 5 | | | V-1 | CD209 | 1.64 | 3634 | 3 | 4 | 5 | | V-1 | CNTLN | 1.87 |
| 3539 | 3 | 4 | 5 | | | V-1 | CD300A | 1.98 | 3635 | 3 | 4 | 5 | | V-1 | COA5 | 1.99 |
| 3540 | 3 | 4 | 5 | | | V-1 | CD300C | 1.75 | 3636 | 3 | 4 | 5 | | V-1 | COASY | 1.89 |
| 3541 | 3 | 4 | 5 | | | V-1 | CD300LB | 1.91 | 3637 | 3 | 4 | 5 | | V-1 | COG2 | 1.56 |
| 3542 | 3 | 4 | 5 | | | V-1 | CD58 | 1.87 | 3638 | 3 | 4 | 5 | | V-1 | COG5 | 1.65 |
| 3543 | 3 | 4 | 5 | | | V-1 | CD6 | 1.57 | 3639 | 3 | 4 | 5 | | V-1 | COG6 | 1.68 |
| 3544 | 3 | 4 | 5 | | | V-1 | CD84 | 1.55 | 3640 | 3 | 4 | 5 | | V-1 | COG8 | 1.71 |
| 3545 | 3 | 4 | 5 | | | V-1 | CD86 | 1.98 | 3641 | 3 | 4 | 5 | | V-1 | COMMD10 | 1.55 |
| 3546 | 3 | 4 | 5 | | | V-1 | CD93 | 1.78 | 3642 | 3 | 4 | 5 | | V-1 | COMMD4 | 1.59 |
| 3547 | 3 | 4 | 5 | | | V-1 | CD99P1 | 1.75 | 3643 | 3 | 4 | 5 | | V-1 | COMTD1 | 1.98 |
| 3548 | 3 | 4 | 5 | | | V-1 | CDADC1 | 1.75 | 3644 | 3 | 4 | 5 | | V-1 | COPB1 | 1.72 |

Fig. 40 - 20

| | | | | | | | |
|---|---|---|---|---|---|---|---|
| 3645 | 3 | 4 | 5 | V-1 | COPB2 | 1.93 |
| 3646 | 3 | 4 | 5 | V-1 | COPS6 | 1.61 |
| 3647 | 3 | 4 | 5 | V-1 | COPS7A | 1.51 |
| 3648 | 3 | 4 | 5 | V-1 | COPS7B | 2.00 |
| 3649 | 3 | 4 | 5 | V-1 | COQ2 | 1.60 |
| 3650 | 3 | 4 | 5 | V-1 | COQ5 | 1.59 |
| 3651 | 3 | 4 | 5 | V-1 | CORO1A | 1.65 |
| 3652 | 3 | 4 | 5 | V-1 | CORO1C | 1.66 |
| 3653 | 3 | 4 | 5 | V-1 | COX15 | 1.67 |
| 3654 | 3 | 4 | 5 | V-1 | COX18 | 1.62 |
| 3655 | 3 | 4 | 5 | V-1 | CPEB4 | 1.62 |
| 3656 | 3 | 4 | 5 | V-1 | CPNE1 | 1.71 |
| 3657 | 3 | 4 | 5 | V-1 | CPPED1 | 1.85 |
| 3658 | 3 | 4 | 5 | V-1 | CPSF2 | 1.66 |
| 3659 | 3 | 4 | 5 | V-1 | CPSF3 | 1.71 |
| 3660 | 3 | 4 | 5 | V-1 | CPSF4 | 1.83 |
| 3661 | 3 | 4 | 5 | V-1 | CR1 | 1.72 |
| 3662 | 3 | 4 | 5 | V-1 | CR8N | 1.53 |
| 3663 | 3 | 4 | 5 | V-1 | CREB3L4 | 1.62 |
| 3664 | 3 | 4 | 5 | V-1 | CREG1 | 1.51 |
| 3665 | 3 | 4 | 5 | V-1 | CREM | 1.64 |
| 3666 | 3 | 4 | 5 | V-1 | CRK | 1.51 |
| 3667 | 3 | 4 | 5 | V-1 | CRKL | 1.52 |
| 3668 | 3 | 4 | 5 | V-1 | CRLS1 | 1.63 |
| 3669 | 3 | 4 | 5 | V-1 | CRNKL1 | 1.70 |
| 3670 | 3 | 4 | 5 | V-1 | CRTC2 | 1.58 |
| 3671 | 3 | 4 | 5 | V-1 | CRTC3 | 1.88 |
| 3672 | 3 | 4 | 5 | V-1 | CRY2 | 1.73 |
| 3673 | 3 | 4 | 5 | V-1 | CRYGS | 1.98 |
| 3674 | 3 | 4 | 5 | V-1 | CS | 1.57 |
| 3675 | 3 | 4 | 5 | V-1 | CSE1L | 1.94 |
| 3676 | 3 | 4 | 5 | V-1 | CSGALNACT2 | 1.90 |
| 3677 | 3 | 4 | 5 | V-1 | CSK | 1.92 |
| 3678 | 3 | 4 | 5 | V-1 | CSNK1A1 | 1.62 |
| 3679 | 3 | 4 | 5 | V-1 | CSNK1D | 1.57 |
| 3680 | 3 | 4 | 5 | V-1 | CSNK1E | 1.64 |
| 3681 | 3 | 4 | 5 | V-1 | CSNK1G1 | 1.84 |
| 3682 | 3 | 4 | 5 | V-1 | CSNK1G2 | 1.64 |
| 3683 | 3 | 4 | 5 | V-1 | CSRNP1 | 1.72 |
| 3684 | 3 | 4 | 5 | V-1 | CSRNP2 | 1.99 |
| 3685 | 3 | 4 | 5 | V-1 | CSTA | 1.79 |
| 3686 | 3 | 4 | 5 | V-1 | CSTF2T | 1.63 |
| 3687 | 3 | 4 | 5 | V-1 | CTAGE1 | 1.57 |
| 3688 | 3 | 4 | 5 | V-1 | CTAGE11P | 1.54 |
| 3689 | 3 | 4 | 5 | V-1 | CTAGE5 | 1.76 |
| 3690 | 3 | 4 | 5 | V-1 | CTAGE7P | 1.83 |
| 3691 | 3 | 4 | 5 | V-1 | CTBP2 | 1.68 |
| 3692 | 3 | 4 | 5 | V-1 | CTCF | 1.69 |
| 3693 | 3 | 4 | 5 | V-1 | CTDSP2 | 1.65 |
| 3694 | 3 | 4 | 5 | V-1 | CTNNBL1 | 1.72 |
| 3695 | 3 | 4 | 5 | V-1 | CTR9 | 1.94 |
| 3696 | 3 | 4 | 5 | V-1 | CTSA | 1.83 |
| 3697 | 3 | 4 | 5 | V-1 | CTSB | 1.54 |
| 3698 | 3 | 4 | 5 | V-1 | CTSD | 1.66 |
| 3699 | 3 | 4 | 5 | V-1 | CTSF | 1.61 |
| 3700 | 3 | 4 | 5 | V-1 | CTSS | 1.80 |
| 3701 | 3 | 4 | 5 | V-1 | CTTN | 1.87 |
| 3702 | 3 | 4 | 5 | V-1 | CTTNBP2NL | 1.66 |
| 3703 | 3 | 4 | 5 | V-1 | CTU1 | 1.79 |
| 3704 | 3 | 4 | 5 | V-1 | CUEDC1 | 1.95 |
| 3705 | 3 | 4 | 5 | V-1 | CUL2 | 1.55 |
| 3706 | 3 | 4 | 5 | V-1 | CUL3 | 1.88 |
| 3707 | 3 | 4 | 5 | V-1 | CUL4A | 1.91 |
| 3708 | 3 | 4 | 5 | V-1 | CUL4B | 1.74 |
| 3709 | 3 | 4 | 5 | V-1 | CUL5 | 1.72 |
| 3710 | 3 | 4 | 5 | V-1 | CUTC | 1.80 |
| 3711 | 3 | 4 | 5 | V-1 | CUX1 | 1.50 |
| 3712 | 3 | 4 | 5 | V-1 | CWC22 | 1.67 |
| 3713 | 3 | 4 | 5 | V-1 | CXCR1 | 1.82 |
| 3714 | 3 | 4 | 5 | V-1 | CXCR2 | 1.82 |
| 3715 | 3 | 4 | 5 | V-1 | CXorf38 | 1.73 |
| 3716 | 3 | 4 | 5 | V-1 | CYB561D1 | 1.68 |
| 3717 | 3 | 4 | 5 | V-1 | CYB561D2 | 1.66 |
| 3718 | 3 | 4 | 5 | V-1 | CYB5D1 | 1.84 |
| 3719 | 3 | 4 | 5 | V-1 | CYB5R4 | 1.53 |
| 3720 | 3 | 4 | 5 | V-1 | CYBASC3 | 1.60 |
| 3721 | 3 | 4 | 5 | V-1 | CYHR1 | 1.61 |
| 3722 | 3 | 4 | 5 | V-1 | CYLD | 1.94 |
| 3723 | 3 | 4 | 5 | V-1 | CYP20A1 | 2.00 |
| 3724 | 3 | 4 | 5 | V-1 | CYP2U1 | 1.82 |
| 3725 | 3 | 4 | 5 | V-1 | CYP4F22 | 1.78 |
| 3726 | 3 | 4 | 5 | V-1 | CYTH4 | 1.69 |
| 3727 | 3 | 4 | 5 | V-1 | CYTIP | 1.74 |
| 3728 | 3 | 4 | 5 | V-1 | DAG1 | 1.74 |
| 3729 | 3 | 4 | 5 | V-1 | DAGLA | 1.85 |
| 3730 | 3 | 4 | 5 | V-1 | DALRD3 | 1.74 |
| 3731 | 3 | 4 | 5 | V-1 | DAPK3 | 1.98 |
| 3732 | 3 | 4 | 5 | V-1 | DBNDD2 | 1.77 |
| 3733 | 3 | 4 | 5 | V-1 | DBNL | 1.58 |
| 3734 | 3 | 4 | 5 | V-1 | DBR1 | 1.66 |
| 3735 | 3 | 4 | 5 | V-1 | DBT | 1.76 |
| 3736 | 3 | 4 | 5 | V-1 | DCAF16 | 1.83 |
| 3737 | 3 | 4 | 5 | V-1 | DCAF17 | 1.70 |
| 3738 | 3 | 4 | 5 | V-1 | DCAF5 | 1.93 |
| 3739 | 3 | 4 | 5 | V-1 | DCAF7 | 1.89 |
| 3740 | 3 | 4 | 5 | V-1 | DCAF8 | 1.94 |
| 3741 | 3 | 4 | 5 | V-1 | DCAKD | 1.58 |
| 3742 | 3 | 4 | 5 | V-1 | DCLRE1A | 1.52 |
| 3743 | 3 | 4 | 5 | V-1 | DCPS | 1.77 |
| 3744 | 3 | 4 | 5 | V-1 | DCTN1 | 1.62 |
| 3745 | 3 | 4 | 5 | V-1 | DCTN4 | 1.93 |
| 3746 | 3 | 4 | 5 | V-1 | DCTN5 | 1.79 |
| 3747 | 3 | 4 | 5 | V-1 | DCUN1D4 | 1.80 |
| 3748 | 3 | 4 | 5 | V-1 | DDA1 | 1.58 |
| 3749 | 3 | 4 | 5 | V-1 | DDB1 | 1.74 |
| 3750 | 3 | 4 | 5 | V-1 | DDHD2 | 1.78 |
| 3751 | 3 | 4 | 5 | V-1 | DDX1 | 1.72 |
| 3752 | 3 | 4 | 5 | V-1 | DDX18 | 1.90 |
| 3753 | 3 | 4 | 5 | V-1 | DDX19A | 1.71 |
| 3754 | 3 | 4 | 5 | V-1 | DDX20 | 1.54 |
| 3755 | 3 | 4 | 5 | V-1 | DDX21 | 1.64 |
| 3756 | 3 | 4 | 5 | V-1 | DDX23 | 1.70 |
| 3757 | 3 | 4 | 5 | V-1 | DDX24 | 1.70 |
| 3758 | 3 | 4 | 5 | V-1 | DDX41 | 1.53 |
| 3759 | 3 | 4 | 5 | V-1 | DDX42 | 1.98 |
| 3760 | 3 | 4 | 5 | V-1 | DDX46 | 1.79 |
| 3761 | 3 | 4 | 5 | V-1 | DDX47 | 1.72 |
| 3762 | 3 | 4 | 5 | V-1 | DDX59 | 1.50 |
| 3763 | 3 | 4 | 5 | V-1 | DEAF1 | 1.80 |
| 3764 | 3 | 4 | 5 | V-1 | DEDD | 1.64 |
| 3765 | 3 | 4 | 5 | V-1 | DEF6 | 1.87 |
| 3766 | 3 | 4 | 5 | V-1 | DENND1B | 1.81 |
| 3767 | 3 | 4 | 5 | V-1 | DENND4A | 1.70 |
| 3768 | 3 | 4 | 5 | V-1 | DENND5B | 1.94 |
| 3769 | 3 | 4 | 5 | V-1 | DEPDC5 | 1.95 |
| 3770 | 3 | 4 | 5 | V-1 | DERA | 1.83 |
| 3771 | 3 | 4 | 5 | V-1 | DERL2 | 1.51 |
| 3772 | 3 | 4 | 5 | V-1 | DEXI | 1.69 |
| 3773 | 3 | 4 | 5 | V-1 | DGCR14 | 1.88 |
| 3774 | 3 | 4 | 5 | V-1 | DGCR2 | 1.87 |
| 3775 | 3 | 4 | 5 | V-1 | DGKZ | 1.83 |
| 3776 | 3 | 4 | 5 | V-1 | DGUOK | 1.51 |
| 3777 | 3 | 4 | 5 | V-1 | DHDDS | 1.77 |
| 3778 | 3 | 4 | 5 | V-1 | DHODH | 1.67 |
| 3779 | 3 | 4 | 5 | V-1 | DHRS11 | 1.51 |
| 3780 | 3 | 4 | 5 | V-1 | DHRS7B | 1.65 |
| 3781 | 3 | 4 | 5 | V-1 | DHX15 | 1.85 |
| 3782 | 3 | 4 | 5 | V-1 | DHX30 | 1.86 |
| 3783 | 3 | 4 | 5 | V-1 | DHX32 | 1.85 |
| 3784 | 3 | 4 | 5 | V-1 | DHX40 | 1.62 |
| 3785 | 3 | 4 | 5 | V-1 | DHX8 | 1.97 |
| 3786 | 3 | 4 | 5 | V-1 | DHX9 | 1.89 |
| 3787 | 3 | 4 | 5 | V-1 | DIAPH1 | 1.91 |
| 3788 | 3 | 4 | 5 | V-1 | DIAPH2 | 1.75 |
| 3789 | 3 | 4 | 5 | V-1 | DIEXF | 1.92 |
| 3790 | 3 | 4 | 5 | V-1 | DIRC2 | 1.86 |
| 3791 | 3 | 4 | 5 | V-1 | DIS3 | 1.81 |
| 3792 | 3 | 4 | 5 | V-1 | DKC1 | 1.86 |
| 3793 | 3 | 4 | 5 | V-1 | DLAT | 1.73 |
| 3794 | 3 | 4 | 5 | V-1 | DLD | 1.94 |
| 3795 | 3 | 4 | 5 | V-1 | DLG4 | 1.76 |
| 3796 | 3 | 4 | 5 | V-1 | DLGAP4 | 1.83 |
| 3797 | 3 | 4 | 5 | V-1 | DLST | 1.77 |
| 3798 | 3 | 4 | 5 | V-1 | DMAP1 | 2.00 |
| 3799 | 3 | 4 | 5 | V-1 | DNAJB11 | 1.65 |
| 3800 | 3 | 4 | 5 | V-1 | DNAJB12 | 1.51 |
| 3801 | 3 | 4 | 5 | V-1 | DNAJB14 | 1.66 |
| 3802 | 3 | 4 | 5 | V-1 | DNAJB4 | 1.98 |
| 3803 | 3 | 4 | 5 | V-1 | DNAJB6 | 1.63 |
| 3804 | 3 | 4 | 5 | V-1 | DNAJC1 | 1.62 |
| 3805 | 3 | 4 | 5 | V-1 | DNAJC10 | 1.91 |
| 3806 | 3 | 4 | 5 | V-1 | DNAJC15 | 1.50 |
| 3807 | 3 | 4 | 5 | V-1 | DNAJC16 | 1.96 |
| 3808 | 3 | 4 | 5 | V-1 | DNAJC19 | 1.61 |
| 3809 | 3 | 4 | 5 | V-1 | DNAJC27 | 1.63 |
| 3810 | 3 | 4 | 5 | V-1 | DNAJC5 | 1.69 |
| 3811 | 3 | 4 | 5 | V-1 | DND1 | 1.97 |
| 3812 | 3 | 4 | 5 | V-1 | DNM1L | 1.93 |
| 3813 | 3 | 4 | 5 | V-1 | DNM2 | 1.69 |
| 3814 | 3 | 4 | 5 | V-1 | DOHH | 1.79 |
| 3815 | 3 | 4 | 5 | V-1 | DOK3 | 1.60 |
| 3816 | 3 | 4 | 5 | V-1 | DOPEY2 | 1.79 |
| 3817 | 3 | 4 | 5 | V-1 | DPF2 | 1.85 |
| 3818 | 3 | 4 | 5 | V-1 | DPH2 | 1.81 |
| 3819 | 3 | 4 | 5 | V-1 | DPP7 | 1.80 |
| 3820 | 3 | 4 | 5 | V-1 | DPP8 | 1.94 |
| 3821 | 3 | 4 | 5 | V-1 | DPP9 | 1.95 |
| 3822 | 3 | 4 | 5 | V-1 | DRAP1 | 1.82 |
| 3823 | 3 | 4 | 5 | V-1 | DRG2 | 1.92 |
| 3824 | 3 | 4 | 5 | V-1 | DSCR3 | 1.55 |
| 3825 | 3 | 4 | 5 | V-1 | DSE | 1.81 |
| 3826 | 3 | 4 | 5 | V-1 | DTNBP1 | 1.57 |
| 3827 | 3 | 4 | 5 | V-1 | DTWD2 | 1.62 |
| 3828 | 3 | 4 | 5 | V-1 | DTX2 | 1.50 |
| 3829 | 3 | 4 | 5 | V-1 | DUS4L | 1.55 |
| 3830 | 3 | 4 | 5 | V-1 | DUSP10 | 1.52 |
| 3831 | 3 | 4 | 5 | V-1 | DUSP22 | 1.80 |
| 3832 | 3 | 4 | 5 | V-1 | DUSP28 | 1.79 |
| 3833 | 3 | 4 | 5 | V-1 | DUSP7 | 1.85 |
| 3834 | 3 | 4 | 5 | V-1 | DUT | 1.87 |
| 3835 | 3 | 4 | 5 | V-1 | DVL1 | 1.90 |
| 3836 | 3 | 4 | 5 | V-1 | DYNC1I2 | 1.93 |

Fig. 40 - 21

| | | | | | | | | | | | | | | | |
|---|---|---|---|---|---|---|---|---|---|---|---|---|---|---|---|
| 3837 | 3 | 4 | 5 | | | V-1 | DYNLL2 | 1.66 | 3933 | 3 | 4 | 5 | | V-1 | FAM120AOS | 1.61 |
| 3838 | 3 | 4 | 5 | | | V-1 | DZIP3 | 1.54 | 3934 | 3 | 4 | 5 | | V-1 | FAM120B | 1.88 |
| 3839 | 3 | 4 | 5 | | | V-1 | E2F3 | 1.71 | 3935 | 3 | 4 | 5 | | V-1 | FAM122A | 1.56 |
| 3840 | 3 | 4 | 5 | | | V-1 | E2F6 | 1.71 | 3936 | 3 | 4 | 5 | | V-1 | FAM123B | 1.85 |
| 3841 | 3 | 4 | 5 | | | V-1 | E4F1 | 1.86 | 3937 | 3 | 4 | 5 | | V-1 | FAM126A | 1.99 |
| 3842 | 3 | 4 | 5 | | | V-1 | EAF1 | 1.67 | 3938 | 3 | 4 | 5 | | V-1 | FAM127A | 1.56 |
| 3843 | 3 | 4 | 5 | | | V-1 | EBF1 | 1.59 | 3939 | 3 | 4 | 5 | | V-1 | FAM127B | 1.77 |
| 3844 | 3 | 4 | 5 | | | V-1 | ECD | 1.62 | 3940 | 3 | 4 | 5 | | V-1 | FAM131A | 1.52 |
| 3845 | 3 | 4 | 5 | | | V-1 | ECHS1 | 1.57 | 3941 | 3 | 4 | 5 | | V-1 | FAM136A | 1.72 |
| 3846 | 3 | 4 | 5 | | | V-1 | ECT2 | 1.68 | 3942 | 3 | 4 | 5 | | V-1 | FAM13B | 1.85 |
| 3847 | 3 | 4 | 5 | | | V-1 | EDARADD | 1.63 | 3943 | 3 | 4 | 5 | | V-1 | FAM151B | 1.92 |
| 3848 | 3 | 4 | 5 | | | V-1 | EDC3 | 1.57 | 3944 | 3 | 4 | 5 | | V-1 | FAM161B | 1.53 |
| 3849 | 3 | 4 | 5 | | | V-1 | EDEM1 | 1.95 | 3945 | 3 | 4 | 5 | | V-1 | FAM173A | 1.63 |
| 3850 | 3 | 4 | 5 | | | V-1 | EDEM2 | 1.75 | 3946 | 3 | 4 | 5 | | V-1 | FAM174A | 1.95 |
| 3851 | 3 | 4 | 5 | | | V-1 | EEA1 | 1.71 | 3947 | 3 | 4 | 5 | | V-1 | FAM175B | 1.67 |
| 3852 | 3 | 4 | 5 | | | V-1 | EED | 1.56 | 3948 | 3 | 4 | 5 | | V-1 | FAM177B | 1.79 |
| 3853 | 3 | 4 | 5 | | | V-1 | EEF1E1-MUTED | 1.77 | 3949 | 3 | 4 | 5 | | V-1 | FAM179B | 1.75 |
| 3854 | 3 | 4 | 5 | | | V-1 | EEF2K | 1.96 | 3950 | 3 | 4 | 5 | | V-1 | FAM188I | 1.87 |
| 3855 | 3 | 4 | 5 | | | V-1 | EEPD1 | 1.64 | 3951 | 3 | 4 | 5 | | V-1 | FAM193A | 1.88 |
| 3856 | 3 | 4 | 5 | | | V-1 | EFCAB4A | 1.85 | 3952 | 3 | 4 | 5 | | V-1 | FAM199X | 1.99 |
| 3857 | 3 | 4 | 5 | | | V-1 | EFHA1 | 1.70 | 3953 | 3 | 4 | 5 | | V-1 | FAM206A | 1.56 |
| 3858 | 3 | 4 | 5 | | | V-1 | EFNB1 | 1.97 | 3954 | 3 | 4 | 5 | | V-1 | FAM208A | 1.79 |
| 3859 | 3 | 4 | 5 | | | V-1 | EFTUD1 | 1.73 | 3955 | 3 | 4 | 5 | | V-1 | FAM213A | 1.73 |
| 3860 | 3 | 4 | 5 | | | V-1 | EFTUD2 | 1.75 | 3956 | 3 | 4 | 5 | | V-1 | FAM49A | 1.80 |
| 3861 | 3 | 4 | 5 | | | V-1 | EGLN1 | 1.66 | 3957 | 3 | 4 | 5 | | V-1 | FAM49B | 1.64 |
| 3862 | 3 | 4 | 5 | | | V-1 | EHBP1 | 1.79 | 3958 | 3 | 4 | 5 | | V-1 | FAM50A | 1.52 |
| 3863 | 3 | 4 | 5 | | | V-1 | EHD4 | 1.69 | 3959 | 3 | 4 | 5 | | V-1 | FAM54B | 1.71 |
| 3864 | 3 | 4 | 5 | | | V-1 | EHMT1 | 1.71 | 3960 | 3 | 4 | 5 | | V-1 | FAM63A | 1.91 |
| 3865 | 3 | 4 | 5 | | | V-1 | EHMT2 | 1.79 | 3961 | 3 | 4 | 5 | | V-1 | FAM65B | 1.90 |
| 3866 | 3 | 4 | 5 | | | V-1 | EI24 | 1.54 | 3962 | 3 | 4 | 5 | | V-1 | FAM73A | 1.54 |
| 3867 | 3 | 4 | 5 | | | V-1 | EID2 | 1.77 | 3963 | 3 | 4 | 5 | | V-1 | FAM76A | 1.74 |
| 3868 | 3 | 4 | 5 | | | V-1 | EIF2A | 1.54 | 3964 | 3 | 4 | 5 | | V-1 | FAM78A | 1.82 |
| 3869 | 3 | 4 | 5 | | | V-1 | EIF2AK3 | 1.75 | 3965 | 3 | 4 | 5 | | V-1 | FAM81B | 1.82 |
| 3870 | 3 | 4 | 5 | | | V-1 | EIF2B3 | 1.82 | 3966 | 3 | 4 | 5 | | V-1 | FAM82B | 1.60 |
| 3871 | 3 | 4 | 5 | | | V-1 | EIF2C1 | 1.86 | 3967 | 3 | 4 | 5 | | V-1 | FAM98A | 1.89 |
| 3872 | 3 | 4 | 5 | | | V-1 | EIF2C4 | 1.73 | 3968 | 3 | 4 | 5 | | V-1 | FANCE | 1.62 |
| 3873 | 3 | 4 | 5 | | | V-1 | EIF3A | 1.71 | 3969 | 3 | 4 | 5 | | V-1 | FANCF | 1.62 |
| 3874 | 3 | 4 | 5 | | | V-1 | EIF3B | 1.65 | 3970 | 3 | 4 | 5 | | V-1 | FANCG | 1.96 |
| 3875 | 3 | 4 | 5 | | | V-1 | EIF3J | 1.68 | 3971 | 3 | 4 | 5 | | V-1 | FARSA | 1.73 |
| 3876 | 3 | 4 | 5 | | | V-1 | EIF4A2 | 1.70 | 3972 | 3 | 4 | 5 | | V-1 | FASTKD3 | 1.75 |
| 3877 | 3 | 4 | 5 | | | V-1 | EIF4G2 | 1.59 | 3973 | 3 | 4 | 5 | | V-1 | FASTKD5 | 1.58 |
| 3878 | 3 | 4 | 5 | | | V-1 | EIF4H | 1.62 | 3974 | 3 | 4 | 5 | | V-1 | FBF1 | 1.60 |
| 3879 | 3 | 4 | 5 | | | V-1 | EIF5 | 1.87 | 3975 | 3 | 4 | 5 | | V-1 | FBLN7 | 1.77 |
| 3880 | 3 | 4 | 5 | | | V-1 | ELAVL1 | 1.62 | 3976 | 3 | 4 | 5 | | V-1 | FBN2 | 1.83 |
| 3881 | 3 | 4 | 5 | | | V-1 | ELL2 | 1.84 | 3977 | 3 | 4 | 5 | | V-1 | FBP1 | 1.93 |
| 3882 | 3 | 4 | 5 | | | V-1 | ELL3 | 1.88 | 3978 | 3 | 4 | 5 | | V-1 | FBRS | 1.91 |
| 3883 | 3 | 4 | 5 | | | V-1 | ELMO1 | 1.63 | 3979 | 3 | 4 | 5 | | V-1 | FBXL15 | 1.86 |
| 3884 | 3 | 4 | 5 | | | V-1 | ELMO2 | 1.78 | 3980 | 3 | 4 | 5 | | V-1 | FBXL18 | 1.79 |
| 3885 | 3 | 4 | 5 | | | V-1 | ELMO3 | 1.50 | 3981 | 3 | 4 | 5 | | V-1 | FBXL4 | 1.52 |
| 3886 | 3 | 4 | 5 | | | V-1 | ELMOD2 | 1.54 | 3982 | 3 | 4 | 5 | | V-1 | FBXL5 | 1.98 |
| 3887 | 3 | 4 | 5 | | | V-1 | ELOVL5 | 1.61 | 3983 | 3 | 4 | 5 | | V-1 | FBXO21 | 1.78 |
| 3888 | 3 | 4 | 5 | | | V-1 | EMD | 1.59 | 3984 | 3 | 4 | 5 | | V-1 | FBXO28 | 1.79 |
| 3889 | 3 | 4 | 5 | | | V-1 | EME2 | 1.60 | 3985 | 3 | 4 | 5 | | V-1 | FBXO30 | 1.90 |
| 3890 | 3 | 4 | 5 | | | V-1 | ENDOV | 1.61 | 3986 | 3 | 4 | 5 | | V-1 | FBXO33 | 1.71 |
| 3891 | 3 | 4 | 5 | | | V-1 | ENO1 | 1.65 | 3987 | 3 | 4 | 5 | | V-1 | FBXO34 | 1.59 |
| 3892 | 3 | 4 | 5 | | | V-1 | EP400NL | 1.58 | 3988 | 3 | 4 | 5 | | V-1 | FBXO38 | 1.87 |
| 3893 | 3 | 4 | 5 | | | V-1 | EPB41L5 | 1.81 | 3989 | 3 | 4 | 5 | | V-1 | FBXO45 | 1.50 |
| 3894 | 3 | 4 | 5 | | | V-1 | EPC2 | 1.71 | 3990 | 3 | 4 | 5 | | V-1 | FBXO46 | 1.77 |
| 3895 | 3 | 4 | 5 | | | V-1 | EPN1 | 1.59 | 3991 | 3 | 4 | 5 | | V-1 | FBXO48 | 1.66 |
| 3896 | 3 | 4 | 5 | | | V-1 | EPS15L1 | 1.85 | 3992 | 3 | 4 | 5 | | V-1 | FBXO8 | 1.86 |
| 3897 | 3 | 4 | 5 | | | V-1 | ERCC1 | 1.76 | 3993 | 3 | 4 | 5 | | V-1 | FBXW11 | 1.66 |
| 3898 | 3 | 4 | 5 | | | V-1 | ERCC3 | 1.81 | 3994 | 3 | 4 | 5 | | V-1 | FBXW4 | 1.62 |
| 3899 | 3 | 4 | 5 | | | V-1 | ERCC6 | 1.85 | 3995 | 3 | 4 | 5 | | V-1 | FBXW4P1 | 1.53 |
| 3900 | 3 | 4 | 5 | | | V-1 | ERGIC2 | 1.82 | 3996 | 3 | 4 | 5 | | V-1 | FCER1G | 1.67 |
| 3901 | 3 | 4 | 5 | | | V-1 | ERI1 | 1.88 | 3997 | 3 | 4 | 5 | | V-1 | FCGR2A | 1.53 |
| 3902 | 3 | 4 | 5 | | | V-1 | ERLIN2 | 1.77 | 3998 | 3 | 4 | 5 | | V-1 | FCGR2B | 1.80 |
| 3903 | 3 | 4 | 5 | | | V-1 | ETAA1 | 1.67 | 3999 | 3 | 4 | 5 | | V-1 | FCGRT | 1.81 |
| 3904 | 3 | 4 | 5 | | | V-1 | ETF1 | 1.59 | 4000 | 3 | 4 | 5 | | V-1 | FCHO1 | 1.95 |
| 3905 | 3 | 4 | 5 | | | V-1 | ETFB | 1.50 | 4001 | 3 | 4 | 5 | | V-1 | FCHSD2 | 1.90 |
| 3906 | 3 | 4 | 5 | | | V-1 | ETFDH | 1.58 | 4002 | 3 | 4 | 5 | | V-1 | FCN1 | 1.91 |
| 3907 | 3 | 4 | 5 | | | V-1 | ETHE1 | 1.52 | 4003 | 3 | 4 | 5 | | V-1 | FDXACB1 | 1.60 |
| 3908 | 3 | 4 | 5 | | | V-1 | ETNK1 | 1.77 | 4004 | 3 | 4 | 5 | | V-1 | FERMT3 | 1.60 |
| 3909 | 3 | 4 | 5 | | | V-1 | EVI2B | 1.93 | 4005 | 3 | 4 | 5 | | V-1 | FEZ2 | 1.67 |
| 3910 | 3 | 4 | 5 | | | V-1 | EVI5 | 1.66 | 4006 | 3 | 4 | 5 | | V-1 | FGD5-AS1 | 1.52 |
| 3911 | 3 | 4 | 5 | | | V-1 | EXD2 | 1.63 | 4007 | 3 | 4 | 5 | | V-1 | FGFBP3 | 1.59 |
| 3912 | 3 | 4 | 5 | | | V-1 | EXOC2 | 1.90 | 4008 | 3 | 4 | 5 | | V-1 | FGFR1OP | 1.95 |
| 3913 | 3 | 4 | 5 | | | V-1 | EXOC4 | 1.62 | 4009 | 3 | 4 | 5 | | V-1 | FGFR1OP2 | 1.66 |
| 3914 | 3 | 4 | 5 | | | V-1 | EXOC7 | 1.95 | 4010 | 3 | 4 | 5 | | V-1 | FGR | 1.91 |
| 3915 | 3 | 4 | 5 | | | V-1 | EXOSC1 | 1.73 | 4011 | 3 | 4 | 5 | | V-1 | FHL2 | 1.95 |
| 3916 | 3 | 4 | 5 | | | V-1 | EXOSC7 | 1.68 | 4012 | 3 | 4 | 5 | | V-1 | FIBP | 1.55 |
| 3917 | 3 | 4 | 5 | | | V-1 | EXT1 | 1.94 | 4013 | 3 | 4 | 5 | | V-1 | FICD | 1.75 |
| 3918 | 3 | 4 | 5 | | | V-1 | EXT2 | 1.76 | 4014 | 3 | 4 | 5 | | V-1 | FIP1L1 | 1.56 |
| 3919 | 3 | 4 | 5 | | | V-1 | EZH2 | 1.92 | 4015 | 3 | 4 | 5 | | V-1 | FIZ1 | 1.56 |
| 3920 | 3 | 4 | 5 | | | V-1 | EZR | 1.90 | 4016 | 3 | 4 | 5 | | V-1 | FKBP4 | 1.93 |
| 3921 | 3 | 4 | 5 | | | V-1 | F13A1 | 1.51 | 4017 | 3 | 4 | 5 | | V-1 | FKTN | 1.86 |
| 3922 | 3 | 4 | 5 | | | V-1 | F2RL1 | 1.66 | 4018 | 3 | 4 | 5 | | V-1 | FLAD1 | 1.63 |
| 3923 | 3 | 4 | 5 | | | V-1 | FAAH | 1.99 | 4019 | 3 | 4 | 5 | | V-1 | FLI1 | 1.53 |
| 3924 | 3 | 4 | 5 | | | V-1 | FAF1 | 1.57 | 4020 | 3 | 4 | 5 | | V-1 | FLJ35390 | 1.57 |
| 3925 | 3 | 4 | 5 | | | V-1 | FAF2 | 1.59 | 4021 | 3 | 4 | 5 | | V-1 | FLJ46906 | 1.79 |
| 3926 | 3 | 4 | 5 | | | V-1 | FAHD1 | 1.65 | 4022 | 3 | 4 | 5 | | V-1 | FMNL3 | 1.96 |
| 3927 | 3 | 4 | 5 | | | V-1 | FAM102B | 1.84 | 4023 | 3 | 4 | 5 | | V-1 | FNBP1L | 1.65 |
| 3928 | 3 | 4 | 5 | | | V-1 | FAM103A1 | 1.60 | 4024 | 3 | 4 | 5 | | V-1 | FNTA | 1.73 |
| 3929 | 3 | 4 | 5 | | | V-1 | FAM105B | 1.94 | 4025 | 3 | 4 | 5 | | V-1 | FOSL2 | 1.78 |
| 3930 | 3 | 4 | 5 | | | V-1 | FAM108C1 | 1.94 | 4026 | 3 | 4 | 5 | | V-1 | FOXN2 | 1.58 |
| 3931 | 3 | 4 | 5 | | | V-1 | FAM115C | 2.00 | 4027 | 3 | 4 | 5 | | V-1 | FOXN3 | 1.70 |
| 3932 | 3 | 4 | 5 | | | V-1 | FAM116B | 1.63 | 4028 | 3 | 4 | 5 | | V-1 | FOXO3 | 1.77 |

Fig. 40 - 22

| | | | | | | | | | | | | | | | |
|---|---|---|---|---|---|---|---|---|---|---|---|---|---|---|---|
| 4029 | 3 | 4 | 5 | | | V-1 | FOXO3B | 1.53 | 4125 | 3 | 4 | 5 | | V-1 | GPBP1L1 | 1.64 |
| 4030 | 3 | 4 | 5 | | | V-1 | FOXRED1 | 1.89 | 4126 | 3 | 4 | 5 | | V-1 | GPC2 | 1.87 |
| 4031 | 3 | 4 | 5 | | | V-1 | FPGT | 1.98 | 4127 | 3 | 4 | 5 | | V-1 | GPN2 | 1.78 |
| 4032 | 3 | 4 | 5 | | | V-1 | FPR1 | 1.58 | 4128 | 3 | 4 | 5 | | V-1 | GPR108 | 1.81 |
| 4033 | 3 | 4 | 5 | | | V-1 | FPR2 | 1.55 | 4129 | 3 | 4 | 5 | | V-1 | GPR137 | 1.88 |
| 4034 | 3 | 4 | 5 | | | V-1 | FRAT2 | 1.97 | 4130 | 3 | 4 | 5 | | V-1 | GPR137B | 1.58 |
| 4035 | 3 | 4 | 5 | | | V-1 | FRMD8 | 1.67 | 4131 | 3 | 4 | 5 | | V-1 | GPR141 | 1.52 |
| 4036 | 3 | 4 | 5 | | | V-1 | FTO | 1.66 | 4132 | 3 | 4 | 5 | | V-1 | GPR171 | 1.68 |
| 4037 | 3 | 4 | 5 | | | V-1 | FTSJ1 | 1.69 | 4133 | 3 | 4 | 5 | | V-1 | GPR180 | 1.87 |
| 4038 | 3 | 4 | 5 | | | V-1 | FTSJ3 | 1.85 | 4134 | 3 | 4 | 5 | | V-1 | GPR65 | 1.79 |
| 4039 | 3 | 4 | 5 | | | V-1 | FUBP1 | 1.92 | 4135 | 3 | 4 | 5 | | V-1 | GPR75 | 1.57 |
| 4040 | 3 | 4 | 5 | | | V-1 | FUS | 1.94 | 4136 | 3 | 4 | 5 | | V-1 | GPR77 | 1.78 |
| 4041 | 3 | 4 | 5 | | | V-1 | FUZ | 1.77 | 4137 | 3 | 4 | 5 | | V-1 | GPS1 | 1.50 |
| 4042 | 3 | 4 | 5 | | | V-1 | FXR1 | 1.88 | 4138 | 3 | 4 | 5 | | V-1 | GPSM1 | 1.80 |
| 4043 | 3 | 4 | 5 | | | V-1 | FYCO1 | 1.68 | 4139 | 3 | 4 | 5 | | V-1 | GRAMD1C | 1.74 |
| 4044 | 3 | 4 | 5 | | | V-1 | G3BP1 | 1.58 | 4140 | 3 | 4 | 5 | | V-1 | GRASP | 1.70 |
| 4045 | 3 | 4 | 5 | | | V-1 | GAA | 1.91 | 4141 | 3 | 4 | 5 | | V-1 | GRB2 | 1.53 |
| 4046 | 3 | 4 | 5 | | | V-1 | GABARAPL1 | 1.92 | 4142 | 3 | 4 | 5 | | V-1 | GRSF1 | 1.79 |
| 4047 | 3 | 4 | 5 | | | V-1 | GABPA | 1.64 | 4143 | 3 | 4 | 5 | | V-1 | GSK3B | 1.62 |
| 4048 | 3 | 4 | 5 | | | V-1 | GABPB1 | 1.80 | 4144 | 3 | 4 | 5 | | V-1 | GSS | 1.61 |
| 4049 | 3 | 4 | 5 | | | V-1 | GALK1 | 1.57 | 4145 | 3 | 4 | 5 | | V-1 | GSTK1 | 1.92 |
| 4050 | 3 | 4 | 5 | | | V-1 | GALK2 | 1.91 | 4146 | 3 | 4 | 5 | | V-1 | GSTO1 | 1.61 |
| 4051 | 3 | 4 | 5 | | | V-1 | GALNT10 | 1.56 | 4147 | 3 | 4 | 5 | | V-1 | GTF2F1 | 1.61 |
| 4052 | 3 | 4 | 5 | | | V-1 | GALNT12 | 1.69 | 4148 | 3 | 4 | 5 | | V-1 | GTF2F2 | 1.61 |
| 4053 | 3 | 4 | 5 | | | V-1 | GALNT2 | 1.50 | 4149 | 3 | 4 | 5 | | V-1 | GTF2H1 | 1.85 |
| 4054 | 3 | 4 | 5 | | | V-1 | GALNT6 | 1.53 | 4150 | 3 | 4 | 5 | | V-1 | GTF2H2B | 1.58 |
| 4055 | 3 | 4 | 5 | | | V-1 | GAMT | 1.77 | 4151 | 3 | 4 | 5 | | V-1 | GTF2I | 1.75 |
| 4056 | 3 | 4 | 5 | | | V-1 | GANAB | 1.98 | 4152 | 3 | 4 | 5 | | V-1 | GTF3C2 | 1.61 |
| 4057 | 3 | 4 | 5 | | | V-1 | GAPVD1 | 1.92 | 4153 | 3 | 4 | 5 | | V-1 | GTF3C5 | 1.66 |
| 4058 | 3 | 4 | 5 | | | V-1 | GAR1 | 1.57 | 4154 | 3 | 4 | 5 | | V-1 | GTF3C6 | 1.59 |
| 4059 | 3 | 4 | 5 | | | V-1 | GARS | 1.56 | 4155 | 3 | 4 | 5 | | V-1 | GTPBP4 | 1.71 |
| 4060 | 3 | 4 | 5 | | | V-1 | GART | 1.81 | 4156 | 3 | 4 | 5 | | V-1 | GTPBP5 | 1.85 |
| 4061 | 3 | 4 | 5 | | | V-1 | GAS8 | 1.77 | 4157 | 3 | 4 | 5 | | V-1 | GUSBP3 | 1.66 |
| 4062 | 3 | 4 | 5 | | | V-1 | GATAD2A | 1.52 | 4158 | 3 | 4 | 5 | | V-1 | GXYLT1 | 1.67 |
| 4063 | 3 | 4 | 5 | | | V-1 | GATAD2B | 1.99 | 4159 | 3 | 4 | 5 | | V-1 | GYS1 | 1.76 |
| 4064 | 3 | 4 | 5 | | | V-1 | GATS | 1.96 | 4160 | 3 | 4 | 5 | | V-1 | GZF1 | 1.71 |
| 4065 | 3 | 4 | 5 | | | V-1 | GBA2 | 1.92 | 4161 | 3 | 4 | 5 | | V-1 | H2AFJ | 1.81 |
| 4066 | 3 | 4 | 5 | | | V-1 | GBE1 | 1.57 | 4162 | 3 | 4 | 5 | | V-1 | H2AFY | 1.78 |
| 4067 | 3 | 4 | 5 | | | V-1 | GCA | 1.53 | 4163 | 3 | 4 | 5 | | V-1 | H3F3AP4 | 1.61 |
| 4068 | 3 | 4 | 5 | | | V-1 | GCDH | 2.00 | 4164 | 3 | 4 | 5 | | V-1 | H3F3B | 1.73 |
| 4069 | 3 | 4 | 5 | | | V-1 | GCET2 | 1.64 | 4165 | 3 | 4 | 5 | | V-1 | HACE1 | 1.72 |
| 4070 | 3 | 4 | 5 | | | V-1 | GCFC2 | 1.69 | 4166 | 3 | 4 | 5 | | V-1 | HACL1 | 1.52 |
| 4071 | 3 | 4 | 5 | | | V-1 | GCLC | 1.58 | 4167 | 3 | 4 | 5 | | V-1 | HAUS3 | 1.59 |
| 4072 | 3 | 4 | 5 | | | V-1 | GCM1 | 1.56 | 4168 | 3 | 4 | 5 | | V-1 | HAUS6 | 1.72 |
| 4073 | 3 | 4 | 5 | | | V-1 | GCNT1 | 1.79 | 4169 | 3 | 4 | 5 | | V-1 | HAUS7 | 1.75 |
| 4074 | 3 | 4 | 5 | | | V-1 | GDAP1 | 1.76 | 4170 | 3 | 4 | 5 | | V-1 | HAUS8 | 1.56 |
| 4075 | 3 | 4 | 5 | | | V-1 | GEMIN8 | 1.97 | 4171 | 3 | 4 | 5 | | V-1 | HBEGF | 1.61 |
| 4076 | 3 | 4 | 5 | | | V-1 | GET4 | 1.64 | 4172 | 3 | 4 | 5 | | V-1 | HBP1 | 1.91 |
| 4077 | 3 | 4 | 5 | | | V-1 | GFM2 | 1.88 | 4173 | 3 | 4 | 5 | | V-1 | HCAR2 | 1.86 |
| 4078 | 3 | 4 | 5 | | | V-1 | GGCT | 1.54 | 4174 | 3 | 4 | 5 | | V-1 | HCAR3 | 1.55 |
| 4079 | 3 | 4 | 5 | | | V-1 | GGNBP2 | 1.82 | 4175 | 3 | 4 | 5 | | V-1 | HCFC2 | 1.69 |
| 4080 | 3 | 4 | 5 | | | V-1 | GGPS1 | 1.62 | 4176 | 3 | 4 | 5 | | V-1 | HCG11 | 1.79 |
| 4081 | 3 | 4 | 5 | | | V-1 | GHDC | 2.00 | 4177 | 3 | 4 | 5 | | V-1 | HCG18 | 1.82 |
| 4082 | 3 | 4 | 5 | | | V-1 | GIGYF2 | 1.92 | 4178 | 3 | 4 | 5 | | V-1 | HCLS1 | 1.82 |
| 4083 | 3 | 4 | 5 | | | V-1 | GIMAP1 | 1.67 | 4179 | 3 | 4 | 5 | | V-1 | HCP5 | 1.75 |
| 4084 | 3 | 4 | 5 | | | V-1 | GIMAP2 | 1.77 | 4180 | 3 | 4 | 5 | | V-1 | HDAC1 | 1.93 |
| 4085 | 3 | 4 | 5 | | | V-1 | GIMAP4 | 1.93 | 4181 | 3 | 4 | 5 | | V-1 | HDAC2 | 1.56 |
| 4086 | 3 | 4 | 5 | | | V-1 | GK3P | 1.87 | 4182 | 3 | 4 | 5 | | V-1 | HDAC4 | 1.73 |
| 4087 | 3 | 4 | 5 | | | V-1 | GK5 | 1.68 | 4183 | 3 | 4 | 5 | | V-1 | HDAC5 | 1.83 |
| 4088 | 3 | 4 | 5 | | | V-1 | GKAP1 | 1.77 | 4184 | 3 | 4 | 5 | | V-1 | HDAC8 | 1.59 |
| 4089 | 3 | 4 | 5 | | | V-1 | GLA | 1.61 | 4185 | 3 | 4 | 5 | | V-1 | HDLBP | 1.69 |
| 4090 | 3 | 4 | 5 | | | V-1 | GLB1 | 1.50 | 4186 | 3 | 4 | 5 | | V-1 | HEATR5A | 1.92 |
| 4091 | 3 | 4 | 5 | | | V-1 | GLCCI1 | 1.78 | 4187 | 3 | 4 | 5 | | V-1 | HELQ | 1.67 |
| 4092 | 3 | 4 | 5 | | | V-1 | GLCE | 1.66 | 4188 | 3 | 4 | 5 | | V-1 | HERPUD1 | 1.70 |
| 4093 | 3 | 4 | 5 | | | V-1 | GLE1 | 1.90 | 4189 | 3 | 4 | 5 | | V-1 | HEXA | 1.77 |
| 4094 | 3 | 4 | 5 | | | V-1 | GLG1 | 1.99 | 4190 | 3 | 4 | 5 | | V-1 | HEXB | 1.59 |
| 4095 | 3 | 4 | 5 | | | V-1 | GLIPR1 | 1.58 | 4191 | 3 | 4 | 5 | | V-1 | HGD | 1.91 |
| 4096 | 3 | 4 | 5 | | | V-1 | GLUD1 | 1.61 | 4192 | 3 | 4 | 5 | | V-1 | HGSNAT | 1.66 |
| 4097 | 3 | 4 | 5 | | | V-1 | GLUL | 1.77 | 4193 | 3 | 4 | 5 | | V-1 | HIAT1 | 1.71 |
| 4098 | 3 | 4 | 5 | | | V-1 | GLYR1 | 1.69 | 4194 | 3 | 4 | 5 | | V-1 | HIATL1 | 1.66 |
| 4099 | 3 | 4 | 5 | | | V-1 | GMEB1 | 1.86 | 4195 | 3 | 4 | 5 | | V-1 | HIBCH | 1.72 |
| 4100 | 3 | 4 | 5 | | | V-1 | GMEB2 | 1.81 | 4196 | 3 | 4 | 5 | | V-1 | HIF1A | 1.83 |
| 4101 | 3 | 4 | 5 | | | V-1 | GMFB | 1.80 | 4197 | 3 | 4 | 5 | | V-1 | HIF1AN | 1.77 |
| 4102 | 3 | 4 | 5 | | | V-1 | GMPR2 | 1.56 | 4198 | 3 | 4 | 5 | | V-1 | HINFP | 1.60 |
| 4103 | 3 | 4 | 5 | | | V-1 | GNA13 | 1.91 | 4199 | 3 | 4 | 5 | | V-1 | HIPK1 | 1.89 |
| 4104 | 3 | 4 | 5 | | | V-1 | GNA15 | 1.58 | 4200 | 3 | 4 | 5 | | V-1 | HIPK2 | 1.61 |
| 4105 | 3 | 4 | 5 | | | V-1 | GNAI3 | 1.92 | 4201 | 3 | 4 | 5 | | V-1 | HIRA | 1.80 |
| 4106 | 3 | 4 | 5 | | | V-1 | GNB1 | 1.61 | 4202 | 3 | 4 | 5 | | V-1 | HIRIP3 | 1.80 |
| 4107 | 3 | 4 | 5 | | | V-1 | GNE | 1.75 | 4203 | 3 | 4 | 5 | | V-1 | HIST1H2BC | 1.76 |
| 4108 | 3 | 4 | 5 | | | V-1 | GNG5 | 1.50 | 4204 | 3 | 4 | 5 | | V-1 | HIST1H2BH | 1.92 |
| 4109 | 3 | 4 | 5 | | | V-1 | GNL2 | 1.85 | 4205 | 3 | 4 | 5 | | V-1 | HIST1H2BJ | 1.76 |
| 4110 | 3 | 4 | 5 | | | V-1 | GNL3 | 1.60 | 4206 | 3 | 4 | 5 | | V-1 | HIST2H2AA3 | 1.65 |
| 4111 | 3 | 4 | 5 | | | V-1 | GNMT | 1.98 | 4207 | 3 | 4 | 5 | | V-1 | HIST2H2AC | 1.89 |
| 4112 | 3 | 4 | 5 | | | V-1 | GNPAT | 1.73 | 4208 | 3 | 4 | 5 | | V-1 | HIST2H3C | 1.73 |
| 4113 | 3 | 4 | 5 | | | V-1 | GNPDA1 | 1.88 | 4209 | 3 | 4 | 5 | | V-1 | HIST4H4 | 1.78 |
| 4114 | 3 | 4 | 5 | | | V-1 | GOLGA4 | 1.83 | 4210 | 3 | 4 | 5 | | V-1 | HIVEP2 | 1.72 |
| 4115 | 3 | 4 | 5 | | | V-1 | GOLGA5 | 1.65 | 4211 | 3 | 4 | 5 | | V-1 | HK1 | 1.98 |
| 4116 | 3 | 4 | 5 | | | V-1 | GOLT1B | 1.54 | 4212 | 3 | 4 | 5 | | V-1 | HKR1 | 1.80 |
| 4117 | 3 | 4 | 5 | | | V-1 | GON4L | 2.00 | 4213 | 3 | 4 | 5 | | V-1 | HLA-B | 1.88 |
| 4118 | 3 | 4 | 5 | | | V-1 | GOSR1 | 1.85 | 4214 | 3 | 4 | 5 | | V-1 | HLA-C | 1.68 |
| 4119 | 3 | 4 | 5 | | | V-1 | GOSR2 | 1.68 | 4215 | 3 | 4 | 5 | | V-1 | HLA-DMB | 1.69 |
| 4120 | 3 | 4 | 5 | | | V-1 | GOT2 | 1.72 | 4216 | 3 | 4 | 5 | | V-1 | HLA-E | 1.71 |
| 4121 | 3 | 4 | 5 | | | V-1 | GPAM | 1.63 | 4217 | 3 | 4 | 5 | | V-1 | HLTF | 1.62 |
| 4122 | 3 | 4 | 5 | | | V-1 | GPATCH1 | 1.85 | 4218 | 3 | 4 | 5 | | V-1 | HM13 | 1.59 |
| 4123 | 3 | 4 | 5 | | | V-1 | GPATCH3 | 1.83 | 4219 | 3 | 4 | 5 | | V-1 | HMG20A | 1.50 |
| 4124 | 3 | 4 | 5 | | | V-1 | GPATCH8 | 1.56 | 4220 | 3 | 4 | 5 | | V-1 | HMGN1 | 1.85 |

Fig. 40 - 23

| | | | | | | | | | | | | | | | |
|---|---|---|---|---|---|---|---|---|---|---|---|---|---|---|---|
| 4221 | 3 | 4 | 5 | | | V-1 | HMGN4 | 1.56 | 4317 | 3 | 4 | 5 | | V-1 | JPX | 1.61 |
| 4222 | 3 | 4 | 5 | | | V-1 | HNRNPA0 | 1.52 | 4318 | 3 | 4 | 5 | | V-1 | KANSL1 | 1.88 |
| 4223 | 3 | 4 | 5 | | | V-1 | HNRNPA8 | 1.73 | 4319 | 3 | 4 | 5 | | V-1 | KANSL3 | 1.91 |
| 4224 | 3 | 4 | 5 | | | V-1 | HNRNPK | 1.84 | 4320 | 3 | 4 | 5 | | V-1 | KAT2B | 1.66 |
| 4225 | 3 | 4 | 5 | | | V-1 | HNRNPKP3 | 1.96 | 4321 | 3 | 4 | 5 | | V-1 | KAT6A | 1.67 |
| 4226 | 3 | 4 | 5 | | | V-1 | HNRNPR | 1.73 | 4322 | 3 | 4 | 5 | | V-1 | KAT7 | 1.59 |
| 4227 | 3 | 4 | 5 | | | V-1 | HNRNPUL2 | 1.97 | 4323 | 3 | 4 | 5 | | V-1 | KATNB1 | 1.71 |
| 4228 | 3 | 4 | 5 | | | V-1 | HNRPDL | 2.00 | 4324 | 3 | 4 | 5 | | V-1 | KCNMB3 | 1.68 |
| 4229 | 3 | 4 | 5 | | | V-1 | HNRPLL | 1.64 | 4325 | 3 | 4 | 5 | | V-1 | KCNQ1 | 1.51 |
| 4230 | 3 | 4 | 5 | | | V-1 | HOOK1 | 1.68 | 4326 | 3 | 4 | 5 | | V-1 | KCTD11 | 1.91 |
| 4231 | 3 | 4 | 5 | | | V-1 | HOOK2 | 1.84 | 4327 | 3 | 4 | 5 | | V-1 | KCTD17 | 1.87 |
| 4232 | 3 | 4 | 5 | | | V-1 | HOXA1 | 1.51 | 4328 | 3 | 4 | 5 | | V-1 | KCTD18 | 1.65 |
| 4233 | 3 | 4 | 5 | | | V-1 | HRAS | 1.81 | 4329 | 3 | 4 | 5 | | V-1 | KCTD21 | 1.62 |
| 4234 | 3 | 4 | 5 | | | V-1 | HS1BP3 | 1.77 | 4330 | 3 | 4 | 5 | | V-1 | KCTD3 | 1.66 |
| 4235 | 3 | 4 | 5 | | | V-1 | HS2ST1 | 1.51 | 4331 | 3 | 4 | 5 | | V-1 | KCTD6 | 1.78 |
| 4236 | 3 | 4 | 5 | | | V-1 | HSD17B1 | 1.74 | 4332 | 3 | 4 | 5 | | V-1 | KCTD9 | 1.98 |
| 4237 | 3 | 4 | 5 | | | V-1 | HSD17B11 | 1.86 | 4333 | 3 | 4 | 5 | | V-1 | KDELR1 | 1.69 |
| 4238 | 3 | 4 | 5 | | | V-1 | HSD17B12 | 1.81 | 4334 | 3 | 4 | 5 | | V-1 | KDELR2 | 1.65 |
| 4239 | 3 | 4 | 5 | | | V-1 | HSD17B13 | 1.77 | 4335 | 3 | 4 | 5 | | V-1 | KDM1A | 1.76 |
| 4240 | 3 | 4 | 5 | | | V-1 | HSD17B7 | 1.76 | 4336 | 3 | 4 | 5 | | V-1 | KDM3A | 1.92 |
| 4241 | 3 | 4 | 5 | | | V-1 | HSF1 | 1.55 | 4337 | 3 | 4 | 5 | | V-1 | KDM4A | 1.71 |
| 4242 | 3 | 4 | 5 | | | V-1 | HSF2 | 1.56 | 4338 | 3 | 4 | 5 | | V-1 | KDM5A | 1.96 |
| 4243 | 3 | 4 | 5 | | | V-1 | HSP90AB1 | 1.89 | 4339 | 3 | 4 | 5 | | V-1 | KDSR | 1.65 |
| 4244 | 3 | 4 | 5 | | | V-1 | HSP90AB3P | 1.71 | 4340 | 3 | 4 | 5 | | V-1 | KHNYN | 1.73 |
| 4245 | 3 | 4 | 5 | | | V-1 | HSPA1A | 1.72 | 4341 | 3 | 4 | 5 | | V-1 | KIAA0020 | 1.73 |
| 4246 | 3 | 4 | 5 | | | V-1 | HSPA1B | 1.87 | 4342 | 3 | 4 | 5 | | V-1 | KIAA0040 | 1.72 |
| 4247 | 3 | 4 | 5 | | | V-1 | HSPA5 | 1.71 | 4343 | 3 | 4 | 5 | | V-1 | KIAA0100 | 1.55 |
| 4248 | 3 | 4 | 5 | | | V-1 | HSPA9 | 1.82 | 4344 | 3 | 4 | 5 | | V-1 | KIAA0226L | 1.91 |
| 4249 | 3 | 4 | 5 | | | V-1 | HSPD1 | 1.88 | 4345 | 3 | 4 | 5 | | V-1 | KIAA0232 | 1.62 |
| 4250 | 3 | 4 | 5 | | | V-1 | HTATIP2 | 1.60 | 4346 | 3 | 4 | 5 | | V-1 | KIAA0240 | 1.72 |
| 4251 | 3 | 4 | 5 | | | V-1 | HUS1 | 1.80 | 4347 | 3 | 4 | 5 | | V-1 | KIAA0247 | 1.86 |
| 4252 | 3 | 4 | 5 | | | V-1 | HVCN1 | 1.57 | 4348 | 3 | 4 | 5 | | V-1 | KIAA0319 | 1.66 |
| 4253 | 3 | 4 | 5 | | | V-1 | IARS | 1.82 | 4349 | 3 | 4 | 5 | | V-1 | KIAA0494 | 1.55 |
| 4254 | 3 | 4 | 5 | | | V-1 | IBA57 | 1.98 | 4350 | 3 | 4 | 5 | | V-1 | KIAA0513 | 1.89 |
| 4255 | 3 | 4 | 5 | | | V-1 | IBTK | 1.66 | 4351 | 3 | 4 | 5 | | V-1 | KIAA1147 | 1.85 |
| 4256 | 3 | 4 | 5 | | | V-1 | ICAM1 | 1.77 | 4352 | 3 | 4 | 5 | | V-1 | KIAA1279 | 1.79 |
| 4257 | 3 | 4 | 5 | | | V-1 | ICAM2 | 1.80 | 4353 | 3 | 4 | 5 | | V-1 | KIAA1407 | 1.57 |
| 4258 | 3 | 4 | 5 | | | V-1 | IDH2 | 1.61 | 4354 | 3 | 4 | 5 | | V-1 | KIAA1429 | 1.58 |
| 4259 | 3 | 4 | 5 | | | V-1 | IDH3A | 1.93 | 4355 | 3 | 4 | 5 | | V-1 | KIAA1586 | 1.65 |
| 4260 | 3 | 4 | 5 | | | V-1 | IDH3G | 1.52 | 4356 | 3 | 4 | 5 | | V-1 | KIAA1609 | 1.95 |
| 4261 | 3 | 4 | 5 | | | V-1 | IDI2-AS1 | 1.76 | 4357 | 3 | 4 | 5 | | V-1 | KIAA1797 | 1.66 |
| 4262 | 3 | 4 | 5 | | | V-1 | IER5 | 1.95 | 4358 | 3 | 4 | 5 | | V-1 | KIAA1826 | 1.50 |
| 4263 | 3 | 4 | 5 | | | V-1 | IFNAR1 | 1.62 | 4359 | 3 | 4 | 5 | | V-1 | KIAA1908 | 1.81 |
| 4264 | 3 | 4 | 5 | | | V-1 | IFNAR2 | 1.64 | 4360 | 3 | 4 | 5 | | V-1 | KIAA1967 | 1.96 |
| 4265 | 3 | 4 | 5 | | | V-1 | IFNGR2 | 1.86 | 4361 | 3 | 4 | 5 | | V-1 | KIAA2013 | 1.65 |
| 4266 | 3 | 4 | 5 | | | V-1 | IFT43 | 1.90 | 4362 | 3 | 4 | 5 | | V-1 | KIAA2018 | 1.57 |
| 4267 | 3 | 4 | 5 | | | V-1 | IKBIP | 1.56 | 4363 | 3 | 4 | 5 | | V-1 | KIF13A | 1.75 |
| 4268 | 3 | 4 | 5 | | | V-1 | IKBKE | 1.80 | 4364 | 3 | 4 | 5 | | V-1 | KIF1C | 1.71 |
| 4269 | 3 | 4 | 5 | | | V-1 | IKZF1 | 1.54 | 4365 | 3 | 4 | 5 | | V-1 | KIF21B | 1.62 |
| 4270 | 3 | 4 | 5 | | | V-1 | IKZF4 | 1.62 | 4366 | 3 | 4 | 5 | | V-1 | KIF22 | 1.70 |
| 4271 | 3 | 4 | 5 | | | V-1 | IL10RA | 1.51 | 4367 | 3 | 4 | 5 | | V-1 | KIF3B | 1.82 |
| 4272 | 3 | 4 | 5 | | | V-1 | IL10RB | 1.72 | 4368 | 3 | 4 | 5 | | V-1 | KIFC3 | 1.69 |
| 4273 | 3 | 4 | 5 | | | V-1 | IL17RC | 1.73 | 4369 | 3 | 4 | 5 | | V-1 | KIR2DL1 | 1.63 |
| 4274 | 3 | 4 | 5 | | | V-1 | IL18BP | 1.80 | 4370 | 3 | 4 | 5 | | V-1 | KLC1 | 1.92 |
| 4275 | 3 | 4 | 5 | | | V-1 | IL27RA | 1.83 | 4371 | 3 | 4 | 5 | | V-1 | KLF10 | 1.85 |
| 4276 | 3 | 4 | 5 | | | V-1 | IL2RG | 1.52 | 4372 | 3 | 4 | 5 | | V-1 | KLF16 | 1.65 |
| 4277 | 3 | 4 | 5 | | | V-1 | IL6R | 1.69 | 4373 | 3 | 4 | 5 | | V-1 | KLF2 | 1.62 |
| 4278 | 3 | 4 | 5 | | | V-1 | IL6ST | 1.93 | 4374 | 3 | 4 | 5 | | V-1 | KLF3 | 1.82 |
| 4279 | 3 | 4 | 5 | | | V-1 | ILK | 1.66 | 4375 | 3 | 4 | 5 | | V-1 | KLF7 | 1.65 |
| 4280 | 3 | 4 | 5 | | | V-1 | IMMT | 1.75 | 4376 | 3 | 4 | 5 | | V-1 | KLF8 | 1.78 |
| 4281 | 3 | 4 | 5 | | | V-1 | IMPA1 | 1.75 | 4377 | 3 | 4 | 5 | | V-1 | KLHDC1 | 1.69 |
| 4282 | 3 | 4 | 5 | | | V-1 | INO80 | 1.70 | 4378 | 3 | 4 | 5 | | V-1 | KLHDC2 | 1.65 |
| 4283 | 3 | 4 | 5 | | | V-1 | INPP1 | 1.78 | 4379 | 3 | 4 | 5 | | V-1 | KLHDC4 | 1.76 |
| 4284 | 3 | 4 | 5 | | | V-1 | INSIG2 | 1.99 | 4380 | 3 | 4 | 5 | | V-1 | KLHDC5 | 1.89 |
| 4285 | 3 | 4 | 5 | | | V-1 | INTS12 | 1.51 | 4381 | 3 | 4 | 5 | | V-1 | KLHL12 | 1.79 |
| 4286 | 3 | 4 | 5 | | | V-1 | INTS6 | 1.89 | 4382 | 3 | 4 | 5 | | V-1 | KLHL15 | 1.65 |
| 4287 | 3 | 4 | 5 | | | V-1 | INTS7 | 1.76 | 4383 | 3 | 4 | 5 | | V-1 | KLHL18 | 1.99 |
| 4288 | 3 | 4 | 5 | | | V-1 | INTS9 | 1.66 | 4384 | 3 | 4 | 5 | | V-1 | KLHL20 | 1.78 |
| 4289 | 3 | 4 | 5 | | | V-1 | IP6K1 | 1.55 | 4385 | 3 | 4 | 5 | | V-1 | KLHL21 | 1.90 |
| 4290 | 3 | 4 | 5 | | | V-1 | IPCEF1 | 1.74 | 4386 | 3 | 4 | 5 | | V-1 | KLHL24 | 1.82 |
| 4291 | 3 | 4 | 5 | | | V-1 | IPMK | 1.74 | 4387 | 3 | 4 | 5 | | V-1 | KLHL25 | 1.77 |
| 4292 | 3 | 4 | 5 | | | V-1 | IPO13 | 1.72 | 4388 | 3 | 4 | 5 | | V-1 | KLHL26 | 1.97 |
| 4293 | 3 | 4 | 5 | | | V-1 | IPP | 1.60 | 4389 | 3 | 4 | 5 | | V-1 | KLHL28 | 1.86 |
| 4294 | 3 | 4 | 5 | | | V-1 | IPW | 1.78 | 4390 | 3 | 4 | 5 | | V-1 | KPNA1 | 1.66 |
| 4295 | 3 | 4 | 5 | | | V-1 | IQCG | 1.65 | 4391 | 3 | 4 | 5 | | V-1 | KPNA2 | 1.92 |
| 4296 | 3 | 4 | 5 | | | V-1 | IQGAP1 | 1.81 | 4392 | 3 | 4 | 5 | | V-1 | KPNA3 | 1.63 |
| 4297 | 3 | 4 | 5 | | | V-1 | IQGAP2 | 1.67 | 4393 | 3 | 4 | 5 | | V-1 | KPNA4 | 1.54 |
| 4298 | 3 | 4 | 5 | | | V-1 | IRAK1 | 1.53 | 4394 | 3 | 4 | 5 | | V-1 | KPNA5 | 1.56 |
| 4299 | 3 | 4 | 5 | | | V-1 | IRAK2 | 1.99 | 4395 | 3 | 4 | 5 | | V-1 | KRAS | 1.56 |
| 4300 | 3 | 4 | 5 | | | V-1 | IRAK4 | 1.97 | 4396 | 3 | 4 | 5 | | V-1 | KRBA1 | 1.93 |
| 4301 | 3 | 4 | 5 | | | V-1 | IRF3 | 1.92 | 4397 | 3 | 4 | 5 | | V-1 | KRIT1 | 1.80 |
| 4302 | 3 | 4 | 5 | | | V-1 | IRS1 | 1.88 | 4398 | 3 | 4 | 5 | | V-1 | KRR1 | 1.53 |
| 4303 | 3 | 4 | 5 | | | V-1 | ITCH | 1.86 | 4399 | 3 | 4 | 5 | | V-1 | KTI12 | 1.81 |
| 4304 | 3 | 4 | 5 | | | V-1 | ITFG2 | 1.65 | 4400 | 3 | 4 | 5 | | V-1 | KY | 1.55 |
| 4305 | 3 | 4 | 5 | | | V-1 | ITFG3 | 1.71 | 4401 | 3 | 4 | 5 | | V-1 | L3MBTL2 | 1.80 |
| 4306 | 3 | 4 | 5 | | | V-1 | ITGA6 | 1.50 | 4402 | 3 | 4 | 5 | | V-1 | LAGE3 | 1.89 |
| 4307 | 3 | 4 | 5 | | | V-1 | ITGB7 | 1.93 | 4403 | 3 | 4 | 5 | | V-1 | LAMB2P1 | 1.62 |
| 4308 | 3 | 4 | 5 | | | V-1 | ITM2B | 1.76 | 4404 | 3 | 4 | 5 | | V-1 | LAMC1 | 1.64 |
| 4309 | 3 | 4 | 5 | | | V-1 | ITPKB | 1.84 | 4405 | 3 | 4 | 5 | | V-1 | LAMP5 | 1.54 |
| 4310 | 3 | 4 | 5 | | | V-1 | IVD | 1.70 | 4406 | 3 | 4 | 5 | | V-1 | LAMTOR3 | 1.54 |
| 4311 | 3 | 4 | 5 | | | V-1 | IVNS1ABP | 1.75 | 4407 | 3 | 4 | 5 | | V-1 | LANCL3 | 1.73 |
| 4312 | 3 | 4 | 5 | | | V-1 | IWS1 | 1.73 | 4408 | 3 | 4 | 5 | | V-1 | LAPTM4A | 1.79 |
| 4313 | 3 | 4 | 5 | | | V-1 | JAG1 | 1.69 | 4409 | 3 | 4 | 5 | | V-1 | LAPTM4B | 1.96 |
| 4314 | 3 | 4 | 5 | | | V-1 | JMJD5 | 1.80 | 4410 | 3 | 4 | 5 | | V-1 | LAS1L | 1.88 |
| 4315 | 3 | 4 | 5 | | | V-1 | JMJD6 | 1.78 | 4411 | 3 | 4 | 5 | | V-1 | LASP1 | 1.75 |
| 4316 | 3 | 4 | 5 | | | V-1 | JMY | 1.93 | 4412 | 3 | 4 | 5 | | V-1 | LAT2 | 1.97 |

Fig. 40 - 24

| | | | | | | | |
|---|---|---|---|---|---|---|---|
| 4413 | 3 | 4 | 5 | | V-1 | LATS1 | 1.59 |
| 4414 | 3 | 4 | 5 | | V-1 | LCMT1 | 1.53 |
| 4415 | 3 | 4 | 5 | | V-1 | LCP1 | 1.59 |
| 4416 | 3 | 4 | 5 | | V-1 | LDB1 | 1.56 |
| 4417 | 3 | 4 | 5 | | V-1 | LEMD2 | 1.84 |
| 4418 | 3 | 4 | 5 | | V-1 | LEMD3 | 1.52 |
| 4419 | 3 | 4 | 5 | | V-1 | LEO1 | 1.72 |
| 4420 | 3 | 4 | 5 | | V-1 | LEPROTL1 | 1.51 |
| 4421 | 3 | 4 | 5 | | V-1 | LETM1 | 1.94 |
| 4422 | 3 | 4 | 5 | | V-1 | LFNG | 1.72 |
| 4423 | 3 | 4 | 5 | | V-1 | LGALS9B | 1.61 |
| 4424 | 3 | 4 | 5 | | V-1 | LIG3 | 1.85 |
| 4425 | 3 | 4 | 5 | | V-1 | LILRA2 | 1.62 |
| 4426 | 3 | 4 | 5 | | V-1 | LIMD2 | 1.54 |
| 4427 | 3 | 4 | 5 | | V-1 | LIMK1 | 1.99 |
| 4428 | 3 | 4 | 5 | | V-1 | LIMK2 | 1.81 |
| 4429 | 3 | 4 | 5 | | V-1 | LIMS2 | 1.59 |
| 4430 | 3 | 4 | 5 | | V-1 | LIMS3L | 1.72 |
| 4431 | 3 | 4 | 5 | | V-1 | LIN37 | 1.55 |
| 4432 | 3 | 4 | 5 | | V-1 | LIN7C | 1.55 |
| 4433 | 3 | 4 | 5 | | V-1 | LINC00256A | 1.66 |
| 4434 | 3 | 4 | 5 | | V-1 | LINS | 1.90 |
| 4435 | 3 | 4 | 5 | | V-1 | LIPA | 1.55 |
| 4436 | 3 | 4 | 5 | | V-1 | LIPT1 | 1.83 |
| 4437 | 3 | 4 | 5 | | V-1 | LITAF | 1.52 |
| 4438 | 3 | 4 | 5 | | V-1 | LMBR1 | 1.64 |
| 4439 | 3 | 4 | 5 | | V-1 | LMBRD2 | 1.83 |
| 4440 | 3 | 4 | 5 | | V-1 | LMNB2 | 1.52 |
| 4441 | 3 | 4 | 5 | | V-1 | LMTK2 | 1.96 |
| 4442 | 3 | 4 | 5 | | V-1 | LOC100093631 | 1.85 |
| 4443 | 3 | 4 | 5 | | V-1 | LOC100128822 | 1.65 |
| 4444 | 3 | 4 | 5 | | V-1 | LOC100130093 | 1.57 |
| 4445 | 3 | 4 | 5 | | V-1 | LOC100131094 | 1.69 |
| 4446 | 3 | 4 | 5 | | V-1 | LOC100131434 | 1.51 |
| 4447 | 3 | 4 | 5 | | V-1 | LOC100132077 | 1.65 |
| 4448 | 3 | 4 | 5 | | V-1 | LOC100133669 | 1.80 |
| 4449 | 3 | 4 | 5 | | V-1 | LOC100287042 | 1.63 |
| 4450 | 3 | 4 | 5 | | V-1 | LOC100289511 | 1.72 |
| 4451 | 3 | 4 | 5 | | V-1 | LOC100506068 | 1.74 |
| 4452 | 3 | 4 | 5 | | V-1 | LOC100506472 | 1.63 |
| 4453 | 3 | 4 | 5 | | V-1 | LOC100506963 | 1.93 |
| 4454 | 3 | 4 | 5 | | V-1 | LOC100507034 | 1.91 |
| 4455 | 3 | 4 | 5 | | V-1 | LOC100507392 | 1.81 |
| 4456 | 3 | 4 | 5 | | V-1 | LOC100507412 | 1.80 |
| 4457 | 3 | 4 | 5 | | V-1 | LOC100507632 | 1.82 |
| 4458 | 3 | 4 | 5 | | V-1 | LOC100859930 | 1.78 |
| 4459 | 3 | 4 | 5 | | V-1 | LOC148189 | 1.79 |
| 4460 | 3 | 4 | 5 | | V-1 | LOC148413 | 1.70 |
| 4461 | 3 | 4 | 5 | | V-1 | LOC256021 | 1.71 |
| 4462 | 3 | 4 | 5 | | V-1 | LOC282997 | 1.85 |
| 4463 | 3 | 4 | 5 | | V-1 | LOC284440 | 1.72 |
| 4464 | 3 | 4 | 5 | | V-1 | LOC285359 | 1.63 |
| 4465 | 3 | 4 | 5 | | V-1 | LOC286059 | 1.52 |
| 4466 | 3 | 4 | 5 | | V-1 | LOC339290 | 1.92 |
| 4467 | 3 | 4 | 5 | | V-1 | LOC340037 | 1.58 |
| 4468 | 3 | 4 | 5 | | V-1 | LOC388387 | 1.61 |
| 4469 | 3 | 4 | 5 | | V-1 | LOC389765 | 1.83 |
| 4470 | 3 | 4 | 5 | | V-1 | LOC399744 | 1.53 |
| 4471 | 3 | 4 | 5 | | V-1 | LOC400027 | 1.98 |
| 4472 | 3 | 4 | 5 | | V-1 | LOC400927 | 1.67 |
| 4473 | 3 | 4 | 5 | | V-1 | LOC439949 | 1.85 |
| 4474 | 3 | 4 | 5 | | V-1 | LOC541473 | 1.65 |
| 4475 | 3 | 4 | 5 | | V-1 | LOC606724 | 1.94 |
| 4476 | 3 | 4 | 5 | | V-1 | LOC644936 | 1.59 |
| 4477 | 3 | 4 | 5 | | V-1 | LOC645212 | 1.54 |
| 4478 | 3 | 4 | 5 | | V-1 | LOC645513 | 1.70 |
| 4479 | 3 | 4 | 5 | | V-1 | LOC645676 | 1.92 |
| 4480 | 3 | 4 | 5 | | V-1 | LOC646214 | 1.52 |
| 4481 | 3 | 4 | 5 | | V-1 | LOC647979 | 1.74 |
| 4482 | 3 | 4 | 5 | | V-1 | LOC727896 | 1.80 |
| 4483 | 3 | 4 | 5 | | V-1 | LOC728084 | 1.85 |
| 4484 | 3 | 4 | 5 | | V-1 | LOC728855 | 1.94 |
| 4485 | 3 | 4 | 5 | | V-1 | LOC728875 | 1.91 |
| 4486 | 3 | 4 | 5 | | V-1 | LOC728178 | 1.83 |
| 4487 | 3 | 4 | 5 | | V-1 | LOC729852 | 1.61 |
| 4488 | 3 | 4 | 5 | | V-1 | LOC92249 | 1.90 |
| 4489 | 3 | 4 | 5 | | V-1 | LPCAT3 | 1.79 |
| 4490 | 3 | 4 | 5 | | V-1 | LPCAT4 | 1.55 |
| 4491 | 3 | 4 | 5 | | V-1 | LPGAT1 | 1.75 |
| 4492 | 3 | 4 | 5 | | V-1 | LPIN1 | 1.88 |
| 4493 | 3 | 4 | 5 | | V-1 | LRCH1 | 1.81 |
| 4494 | 3 | 4 | 5 | | V-1 | LRIF1 | 1.59 |
| 4495 | 3 | 4 | 5 | | V-1 | LRRC23 | 1.65 |
| 4496 | 3 | 4 | 5 | | V-1 | LRRC25 | 1.90 |
| 4497 | 3 | 4 | 5 | | V-1 | LRRC28 | 1.52 |
| 4498 | 3 | 4 | 5 | | V-1 | LRRC29 | 1.51 |
| 4499 | 3 | 4 | 5 | | V-1 | LRRC41 | 1.70 |
| 4500 | 3 | 4 | 5 | | V-1 | LRRC47 | 1.83 |
| 4501 | 3 | 4 | 5 | | V-1 | LRRC58 | 1.84 |
| 4502 | 3 | 4 | 5 | | V-1 | LRRC59 | 1.94 |
| 4503 | 3 | 4 | 5 | | V-1 | LRRC70 | 1.54 |
| 4504 | 3 | 4 | 5 | | V-1 | LRRC8B | 1.65 |
| 4505 | 3 | 4 | 5 | | V-1 | LRTOMT | 1.67 |
| 4506 | 3 | 4 | 5 | | V-1 | LSG1 | 1.55 |
| 4507 | 3 | 4 | 5 | | V-1 | LSM11 | 1.51 |
| 4508 | 3 | 4 | 5 | | V-1 | LSM14B | 1.83 |
| 4509 | 3 | 4 | 5 | | V-1 | LSS | 1.54 |
| 4510 | 3 | 4 | 5 | | V-1 | LTBP4 | 1.95 |
| 4511 | 3 | 4 | 5 | | V-1 | LTV1 | 1.51 |
| 4512 | 3 | 4 | 5 | | V-1 | LUC7L2 | 1.71 |
| 4513 | 3 | 4 | 5 | | V-1 | LXN | 1.60 |
| 4514 | 3 | 4 | 5 | | V-1 | LVAR | 1.59 |
| 4515 | 3 | 4 | 5 | | V-1 | LYG1 | 1.72 |
| 4516 | 3 | 4 | 5 | | V-1 | LYN | 1.93 |
| 4517 | 3 | 4 | 5 | | V-1 | LYPD3 | 1.59 |
| 4518 | 3 | 4 | 5 | | V-1 | LYPLAL1 | 1.89 |
| 4519 | 3 | 4 | 5 | | V-1 | LYRM5 | 1.79 |
| 4520 | 3 | 4 | 5 | | V-1 | LZTFL1 | 1.50 |
| 4521 | 3 | 4 | 5 | | V-1 | M6PR | 1.54 |
| 4522 | 3 | 4 | 5 | | V-1 | MAD1L1 | 1.57 |
| 4523 | 3 | 4 | 5 | | V-1 | MAEA | 1.70 |
| 4524 | 3 | 4 | 5 | | V-1 | MAML1 | 1.88 |
| 4525 | 3 | 4 | 5 | | V-1 | MAN2A2 | 1.88 |
| 4526 | 3 | 4 | 5 | | V-1 | MAN2B2 | 1.54 |
| 4527 | 3 | 4 | 5 | | V-1 | MANBAL | 1.90 |
| 4528 | 3 | 4 | 5 | | V-1 | MANEA | 1.53 |
| 4529 | 3 | 4 | 5 | | V-1 | MAP1A | 1.87 |
| 4530 | 3 | 4 | 5 | | V-1 | MAP1S | 1.58 |
| 4531 | 3 | 4 | 5 | | V-1 | MAP2K1 | 1.97 |
| 4532 | 3 | 4 | 5 | | V-1 | MAP2K4 | 1.70 |
| 4533 | 3 | 4 | 5 | | V-1 | MAP2K6 | 1.79 |
| 4534 | 3 | 4 | 5 | | V-1 | MAP3K11 | 1.93 |
| 4535 | 3 | 4 | 5 | | V-1 | MAP3K14 | 1.55 |
| 4536 | 3 | 4 | 5 | | V-1 | MAP3K2 | 1.83 |
| 4537 | 3 | 4 | 5 | | V-1 | MAP3K3 | 1.58 |
| 4538 | 3 | 4 | 5 | | V-1 | MAP3K4 | 1.63 |
| 4539 | 3 | 4 | 5 | | V-1 | MAP3K8 | 1.75 |
| 4540 | 3 | 4 | 5 | | V-1 | MAP4K4 | 1.93 |
| 4541 | 3 | 4 | 5 | | V-1 | MAP7D3 | 1.86 |
| 4542 | 3 | 4 | 5 | | V-1 | MAPK1 | 1.55 |
| 4543 | 3 | 4 | 5 | | V-1 | MAPK13 | 1.65 |
| 4544 | 3 | 4 | 5 | | V-1 | MAPK1IP1L | 1.89 |
| 4545 | 3 | 4 | 5 | | V-1 | MAPK7 | 1.85 |
| 4546 | 3 | 4 | 5 | | V-1 | MAPK9 | 1.53 |
| 4547 | 3 | 4 | 5 | | V-1 | MAPKAP1 | 1.56 |
| 4548 | 3 | 4 | 5 | | V-1 | MAPRE2 | 1.79 |
| 4549 | 3 | 4 | 5 | | V-1 | 42432 | 1.63 |
| 4550 | 3 | 4 | 5 | | V-1 | 42434 | 1.82 |
| 4551 | 3 | 4 | 5 | | V-1 | 42436 | 1.75 |
| 4552 | 3 | 4 | 5 | | V-1 | MARK2 | 1.93 |
| 4553 | 3 | 4 | 5 | | V-1 | MARK4 | 1.84 |
| 4554 | 3 | 4 | 5 | | V-1 | MAST2 | 1.69 |
| 4555 | 3 | 4 | 5 | | V-1 | MAT2B | 1.54 |
| 4556 | 3 | 4 | 5 | | V-1 | MAX | 1.79 |
| 4557 | 3 | 4 | 5 | | V-1 | MB21D1 | 1.94 |
| 4558 | 3 | 4 | 5 | | V-1 | MBD2 | 1.66 |
| 4559 | 3 | 4 | 5 | | V-1 | MBD3 | 1.75 |
| 4560 | 3 | 4 | 5 | | V-1 | MBD4 | 1.97 |
| 4561 | 3 | 4 | 5 | | V-1 | MBD5 | 1.82 |
| 4562 | 3 | 4 | 5 | | V-1 | MBIP | 1.66 |
| 4563 | 3 | 4 | 5 | | V-1 | MBNL1 | 1.75 |
| 4564 | 3 | 4 | 5 | | V-1 | MBOAT4 | 1.75 |
| 4565 | 3 | 4 | 5 | | V-1 | MBOAT7 | 2.00 |
| 4566 | 3 | 4 | 5 | | V-1 | MBTPS1 | 1.86 |
| 4567 | 3 | 4 | 5 | | V-1 | MBTPS2 | 1.54 |
| 4568 | 3 | 4 | 5 | | V-1 | MCCC2 | 1.83 |
| 4569 | 3 | 4 | 5 | | V-1 | MCMBP | 1.89 |
| 4570 | 3 | 4 | 5 | | V-1 | MCPH1 | 1.71 |
| 4571 | 3 | 4 | 5 | | V-1 | MCRS1 | 1.63 |
| 4572 | 3 | 4 | 5 | | V-1 | MCTP1 | 1.83 |
| 4573 | 3 | 4 | 5 | | V-1 | MCTP2 | 1.69 |
| 4574 | 3 | 4 | 5 | | V-1 | MCU | 1.78 |
| 4575 | 3 | 4 | 5 | | V-1 | MDGA1 | 1.85 |
| 4576 | 3 | 4 | 5 | | V-1 | ME2 | 1.82 |
| 4577 | 3 | 4 | 5 | | V-1 | MED1 | 1.65 |
| 4578 | 3 | 4 | 5 | | V-1 | MED16 | 1.61 |
| 4579 | 3 | 4 | 5 | | V-1 | MED22 | 1.73 |
| 4580 | 3 | 4 | 5 | | V-1 | MED27 | 1.51 |
| 4581 | 3 | 4 | 5 | | V-1 | MED28 | 1.65 |
| 4582 | 3 | 4 | 5 | | V-1 | MED7 | 1.54 |
| 4583 | 3 | 4 | 5 | | V-1 | MED8 | 1.70 |
| 4584 | 3 | 4 | 5 | | V-1 | MEF2D | 1.99 |
| 4585 | 3 | 4 | 5 | | V-1 | MEMO1 | 1.50 |
| 4586 | 3 | 4 | 5 | | V-1 | MEN1 | 1.79 |
| 4587 | 3 | 4 | 5 | | V-1 | MERTK | 1.71 |
| 4588 | 3 | 4 | 5 | | V-1 | MESDC1 | 1.54 |
| 4589 | 3 | 4 | 5 | | V-1 | METAP1 | 1.62 |
| 4590 | 3 | 4 | 5 | | V-1 | METAP2 | 1.64 |
| 4591 | 3 | 4 | 5 | | V-1 | METTL13 | 1.67 |
| 4592 | 3 | 4 | 5 | | V-1 | METTL16 | 1.67 |
| 4593 | 3 | 4 | 5 | | V-1 | METTL18 | 1.53 |
| 4594 | 3 | 4 | 5 | | V-1 | METTL19 | 1.97 |
| 4595 | 3 | 4 | 5 | | V-1 | METTL20 | 1.52 |
| 4596 | 3 | 4 | 5 | | V-1 | METTL21A | 1.84 |
| 4597 | 3 | 4 | 5 | | V-1 | METTL21B | 1.66 |
| 4598 | 3 | 4 | 5 | | V-1 | METTL22 | 1.81 |
| 4599 | 3 | 4 | 5 | | V-1 | METTL8 | 1.63 |
| 4600 | 3 | 4 | 5 | | V-1 | MFAP1 | 1.76 |
| 4601 | 3 | 4 | 5 | | V-1 | MFAP3 | 1.90 |
| 4602 | 3 | 4 | 5 | | V-1 | MFSD10 | 1.93 |
| 4603 | 3 | 4 | 5 | | V-1 | MFSD2A | 1.83 |
| 4604 | 3 | 4 | 5 | | V-1 | MFSD5 | 1.57 |

Fig. 40 - 25

| | | | | | | | | | | | | | | | | | |
|---|---|---|---|---|---|---|---|---|---|---|---|---|---|---|---|---|---|
| 4605 | 3 | 4 | 5 | | V-1 | MFSD6 | 1.63 | | 4701 | 3 | 4 | 5 | | V-1 | MYD88 | 1.86 |
| 4606 | 3 | 4 | 5 | | V-1 | MGAM | 1.94 | | 4702 | 3 | 4 | 5 | | V-1 | MYH9 | 1.97 |
| 4607 | 3 | 4 | 5 | | V-1 | MGAT1 | 1.71 | | 4703 | 3 | 4 | 5 | | V-1 | MYL12A | 1.55 |
| 4608 | 3 | 4 | 5 | | V-1 | MGAT4A | 1.63 | | 4704 | 3 | 4 | 5 | | V-1 | MYO1G | 1.82 |
| 4609 | 3 | 4 | 5 | | V-1 | MGAT4B | 1.74 | | 4705 | 3 | 4 | 5 | | V-1 | MYOM1 | 1.54 |
| 4610 | 3 | 4 | 5 | | V-1 | MGC12982 | 1.85 | | 4706 | 3 | 4 | 5 | | V-1 | MYPOP | 1.75 |
| 4611 | 3 | 4 | 5 | | V-1 | MGC16142 | 1.61 | | 4707 | 3 | 4 | 5 | | V-1 | N4BP1 | 1.55 |
| 4612 | 3 | 4 | 5 | | V-1 | MGC23284 | 1.94 | | 4708 | 3 | 4 | 5 | | V-1 | NAA15 | 1.61 |
| 4613 | 3 | 4 | 5 | | V-1 | MGC39372 | 1.95 | | 4709 | 3 | 4 | 5 | | V-1 | NAA30 | 1.51 |
| 4614 | 3 | 4 | 5 | | V-1 | MGRN1 | 1.97 | | 4710 | 3 | 4 | 5 | | V-1 | NAA35 | 1.56 |
| 4615 | 3 | 4 | 5 | | V-1 | MGST2 | 1.69 | | 4711 | 3 | 4 | 5 | | V-1 | NAA40 | 1.73 |
| 4616 | 3 | 4 | 5 | | V-1 | MICU1 | 1.86 | | 4712 | 3 | 4 | 5 | | V-1 | NAB1 | 1.88 |
| 4617 | 3 | 4 | 5 | | V-1 | MID1IP1 | 1.91 | | 4713 | 3 | 4 | 5 | | V-1 | NAB2 | 1.65 |
| 4618 | 3 | 4 | 5 | | V-1 | MIER1 | 1.64 | | 4714 | 3 | 4 | 5 | | V-1 | NADKD1 | 1.73 |
| 4619 | 3 | 4 | 5 | | V-1 | MIER3 | 1.63 | | 4715 | 3 | 4 | 5 | | V-1 | NAE1 | 1.53 |
| 4620 | 3 | 4 | 5 | | V-1 | MINA | 1.96 | | 4716 | 3 | 4 | 5 | | V-1 | NAGLU | 1.71 |
| 4621 | 3 | 4 | 5 | | V-1 | MINK1 | 1.91 | | 4717 | 3 | 4 | 5 | | V-1 | NAGPA | 1.77 |
| 4622 | 3 | 4 | 5 | | V-1 | MIOS | 1.60 | | 4718 | 3 | 4 | 5 | | V-1 | NAIF1 | 1.83 |
| 4623 | 3 | 4 | 5 | | V-1 | MIR155HG | 1.98 | | 4719 | 3 | 4 | 5 | | V-1 | NANOS1 | 1.66 |
| 4624 | 3 | 4 | 5 | | V-1 | MIR17HG | 1.68 | | 4720 | 3 | 4 | 5 | | V-1 | NAP1L1 | 1.67 |
| 4625 | 3 | 4 | 5 | | V-1 | MIRLET7BHG | 1.91 | | 4721 | 3 | 4 | 5 | | V-1 | NAP1L4 | 1.50 |
| 4626 | 3 | 4 | 5 | | V-1 | MITD1 | 1.98 | | 4722 | 3 | 4 | 5 | | V-1 | NAPEPLD | 1.89 |
| 4627 | 3 | 4 | 5 | | V-1 | MKI67IP | 1.54 | | 4723 | 3 | 4 | 5 | | V-1 | NAPG | 1.99 |
| 4628 | 3 | 4 | 5 | | V-1 | MKL2 | 1.78 | | 4724 | 3 | 4 | 5 | | V-1 | NASP | 1.80 |
| 4629 | 3 | 4 | 5 | | V-1 | MKRN2 | 1.73 | | 4725 | 3 | 4 | 5 | | V-1 | NAT10 | 1.88 |
| 4630 | 3 | 4 | 5 | | V-1 | MKS1 | 1.81 | | 4726 | 3 | 4 | 5 | | V-1 | NAT14 | 1.54 |
| 4631 | 3 | 4 | 5 | | V-1 | MLLT10 | 1.80 | | 4727 | 3 | 4 | 5 | | V-1 | NCAPD3 | 1.79 |
| 4632 | 3 | 4 | 5 | | V-1 | MLLT6 | 1.81 | | 4728 | 3 | 4 | 5 | | V-1 | NCBP2 | 1.58 |
| 4633 | 3 | 4 | 5 | | V-1 | MLYCD | 1.58 | | 4729 | 3 | 4 | 5 | | V-1 | NCOA2 | 1.86 |
| 4634 | 3 | 4 | 5 | | V-1 | MMAA | 1.73 | | 4730 | 3 | 4 | 5 | | V-1 | NCOA4 | 1.61 |
| 4635 | 3 | 4 | 5 | | V-1 | MMACHC | 1.73 | | 4731 | 3 | 4 | 5 | | V-1 | NCOA5 | 1.71 |
| 4636 | 3 | 4 | 5 | | V-1 | MMADHC | 1.78 | | 4732 | 3 | 4 | 5 | | V-1 | NDRG1 | 1.94 |
| 4637 | 3 | 4 | 5 | | V-1 | MME | 1.85 | | 4733 | 3 | 4 | 5 | | V-1 | NDRG3 | 1.63 |
| 4638 | 3 | 4 | 5 | | V-1 | MNDA | 1.97 | | 4734 | 3 | 4 | 5 | | V-1 | NDST2 | 1.70 |
| 4639 | 3 | 4 | 5 | | V-1 | MNF1 | 1.66 | | 4735 | 3 | 4 | 5 | | V-1 | NDUFA10 | 1.85 |
| 4640 | 3 | 4 | 5 | | V-1 | MNT | 1.68 | | 4736 | 3 | 4 | 5 | | V-1 | NDUFA12 | 1.61 |
| 4641 | 3 | 4 | 5 | | V-1 | MOB1A | 1.68 | | 4737 | 3 | 4 | 5 | | V-1 | NDUFA3 | 1.73 |
| 4642 | 3 | 4 | 5 | | V-1 | MOB3C | 1.78 | | 4738 | 3 | 4 | 5 | | V-1 | NDUFA9 | 1.94 |
| 4643 | 3 | 4 | 5 | | V-1 | MON1B | 1.51 | | 4739 | 3 | 4 | 5 | | V-1 | NDUFAF3 | 1.84 |
| 4644 | 3 | 4 | 5 | | V-1 | MORC2 | 1.77 | | 4740 | 3 | 4 | 5 | | V-1 | NDUFB1 | 1.87 |
| 4645 | 3 | 4 | 5 | | V-1 | MORF4L1 | 1.69 | | 4741 | 3 | 4 | 5 | | V-1 | NDUFS1 | 1.56 |
| 4646 | 3 | 4 | 5 | | V-1 | MORF4L2 | 1.77 | | 4742 | 3 | 4 | 5 | | V-1 | NDUFS2 | 1.92 |
| 4647 | 3 | 4 | 5 | | V-1 | MOSPD1 | 1.51 | | 4743 | 3 | 4 | 5 | | V-1 | NDUFV1 | 1.62 |
| 4648 | 3 | 4 | 5 | | V-1 | MPHOSPH6 | 1.78 | | 4744 | 3 | 4 | 5 | | V-1 | NDUFV3 | 1.66 |
| 4649 | 3 | 4 | 5 | | V-1 | MPHOSPH9 | 1.51 | | 4745 | 3 | 4 | 5 | | V-1 | NEDD1 | 1.83 |
| 4650 | 3 | 4 | 5 | | V-1 | MPND | 1.50 | | 4746 | 3 | 4 | 5 | | V-1 | NEDD4 | 1.62 |
| 4651 | 3 | 4 | 5 | | V-1 | MPP5 | 1.60 | | 4747 | 3 | 4 | 5 | | V-1 | NEIL1 | 1.73 |
| 4652 | 3 | 4 | 5 | | V-1 | MPP7 | 1.60 | | 4748 | 3 | 4 | 5 | | V-1 | NEK1 | 1.55 |
| 4653 | 3 | 4 | 5 | | V-1 | MPPE1 | 1.91 | | 4749 | 3 | 4 | 5 | | V-1 | NEK6 | 1.75 |
| 4654 | 3 | 4 | 5 | | V-1 | MRM1 | 1.61 | | 4750 | 3 | 4 | 5 | | V-1 | NET1 | 1.60 |
| 4655 | 3 | 4 | 5 | | V-1 | MRPL1 | 1.62 | | 4751 | 3 | 4 | 5 | | V-1 | NEU1 | 1.80 |
| 4656 | 3 | 4 | 5 | | V-1 | MRPL13 | 1.86 | | 4752 | 3 | 4 | 5 | | V-1 | NFAM1 | 1.88 |
| 4657 | 3 | 4 | 5 | | V-1 | MRPL18 | 1.94 | | 4753 | 3 | 4 | 5 | | V-1 | NFATC3 | 1.57 |
| 4658 | 3 | 4 | 5 | | V-1 | MRPL35 | 1.62 | | 4754 | 3 | 4 | 5 | | V-1 | NFE2L1 | 1.88 |
| 4659 | 3 | 4 | 5 | | V-1 | MRPL38 | 1.81 | | 4755 | 3 | 4 | 5 | | V-1 | NFE2L2 | 1.89 |
| 4660 | 3 | 4 | 5 | | V-1 | MRPL42 | 1.61 | | 4756 | 3 | 4 | 5 | | V-1 | NFIA | 1.51 |
| 4661 | 3 | 4 | 5 | | V-1 | MRPS14 | 1.79 | | 4757 | 3 | 4 | 5 | | V-1 | NFIC | 1.57 |
| 4662 | 3 | 4 | 5 | | V-1 | MRPS18B | 1.56 | | 4758 | 3 | 4 | 5 | | V-1 | NFIL3 | 1.80 |
| 4663 | 3 | 4 | 5 | | V-1 | MRPS21 | 1.62 | | 4759 | 3 | 4 | 5 | | V-1 | NFKBIB | 1.56 |
| 4664 | 3 | 4 | 5 | | V-1 | MRPS31 | 1.87 | | 4760 | 3 | 4 | 5 | | V-1 | NFX1 | 1.68 |
| 4665 | 3 | 4 | 5 | | V-1 | MRPS5 | 1.97 | | 4761 | 3 | 4 | 5 | | V-1 | NFYA | 1.94 |
| 4666 | 3 | 4 | 5 | | V-1 | MRPS9 | 1.70 | | 4762 | 3 | 4 | 5 | | V-1 | NFYC | 1.91 |
| 4667 | 3 | 4 | 5 | | V-1 | MRS2 | 1.53 | | 4763 | 3 | 4 | 5 | | V-1 | NGFRAP1 | 1.93 |
| 4668 | 3 | 4 | 5 | | V-1 | MRS2P2 | 1.69 | | 4764 | 3 | 4 | 5 | | V-1 | NGLY1 | 1.71 |
| 4669 | 3 | 4 | 5 | | V-1 | MSH6 | 1.87 | | 4765 | 3 | 4 | 5 | | V-1 | NHLRC2 | 1.94 |
| 4670 | 3 | 4 | 5 | | V-1 | MSL2 | 1.90 | | 4766 | 3 | 4 | 5 | | V-1 | NIPA2 | 1.71 |
| 4671 | 3 | 4 | 5 | | V-1 | MSL3P1 | 1.55 | | 4767 | 3 | 4 | 5 | | V-1 | NKAP | 1.61 |
| 4672 | 3 | 4 | 5 | | V-1 | MSS51 | 1.73 | | 4768 | 3 | 4 | 5 | | V-1 | NKIRAS2 | 1.73 |
| 4673 | 3 | 4 | 5 | | V-1 | MTA2 | 1.60 | | 4769 | 3 | 4 | 5 | | V-1 | NLK | 1.97 |
| 4674 | 3 | 4 | 5 | | V-1 | MTA3 | 1.56 | | 4770 | 3 | 4 | 5 | | V-1 | NME3 | 1.59 |
| 4675 | 3 | 4 | 5 | | V-1 | MTCH1 | 1.81 | | 4771 | 3 | 4 | 5 | | V-1 | NME7 | 1.63 |
| 4676 | 3 | 4 | 5 | | V-1 | MTDH | 1.79 | | 4772 | 3 | 4 | 5 | | V-1 | NMNAT1 | 1.53 |
| 4677 | 3 | 4 | 5 | | V-1 | MTERF | 1.77 | | 4773 | 3 | 4 | 5 | | V-1 | NMNAT3 | 1.65 |
| 4678 | 3 | 4 | 5 | | V-1 | MTERFD1 | 1.82 | | 4774 | 3 | 4 | 5 | | V-1 | NMRAL1 | 1.63 |
| 4679 | 3 | 4 | 5 | | V-1 | MTERFD2 | 1.50 | | 4775 | 3 | 4 | 5 | | V-1 | NNAT | 1.96 |
| 4680 | 3 | 4 | 5 | | V-1 | MTERFD3 | 1.59 | | 4776 | 3 | 4 | 5 | | V-1 | NNT | 1.96 |
| 4681 | 3 | 4 | 5 | | V-1 | MTFR1 | 1.54 | | 4777 | 3 | 4 | 5 | | V-1 | NOC3L | 1.51 |
| 4682 | 3 | 4 | 5 | | V-1 | MTHFD2 | 1.60 | | 4778 | 3 | 4 | 5 | | V-1 | NOC4L | 2.00 |
| 4683 | 3 | 4 | 5 | | V-1 | MTHFSD | 1.98 | | 4779 | 3 | 4 | 5 | | V-1 | NOL6 | 1.79 |
| 4684 | 3 | 4 | 5 | | V-1 | MTM1 | 1.72 | | 4780 | 3 | 4 | 5 | | V-1 | NOLC1 | 1.77 |
| 4685 | 3 | 4 | 5 | | V-1 | MTMR1 | 1.65 | | 4781 | 3 | 4 | 5 | | V-1 | NOMO3 | 1.91 |
| 4686 | 3 | 4 | 5 | | V-1 | MTMR10 | 1.90 | | 4782 | 3 | 4 | 5 | | V-1 | NOP10 | 1.52 |
| 4687 | 3 | 4 | 5 | | V-1 | MTMR14 | 1.51 | | 4783 | 3 | 4 | 5 | | V-1 | NOP14 | 1.53 |
| 4688 | 3 | 4 | 5 | | V-1 | MTMR3 | 1.94 | | 4784 | 3 | 4 | 5 | | V-1 | NOP58 | 1.87 |
| 4689 | 3 | 4 | 5 | | V-1 | MTMR6 | 1.75 | | 4785 | 3 | 4 | 5 | | V-1 | NPC1 | 1.81 |
| 4690 | 3 | 4 | 5 | | V-1 | MTO1 | 1.71 | | 4786 | 3 | 4 | 5 | | V-1 | NPHP4 | 1.80 |
| 4691 | 3 | 4 | 5 | | V-1 | MTPN | 1.80 | | 4787 | 3 | 4 | 5 | | V-1 | NPL | 1.93 |
| 4692 | 3 | 4 | 5 | | V-1 | MTRF1L | 1.64 | | 4788 | 3 | 4 | 5 | | V-1 | NPLOC4 | 1.71 |
| 4693 | 3 | 4 | 5 | | V-1 | MTRR | 1.98 | | 4789 | 3 | 4 | 5 | | V-1 | NR1H2 | 1.56 |
| 4694 | 3 | 4 | 5 | | V-1 | MTSS1 | 1.66 | | 4790 | 3 | 4 | 5 | | V-1 | NR3C1 | 1.61 |
| 4695 | 3 | 4 | 5 | | V-1 | MTX2 | 1.56 | | 4791 | 3 | 4 | 5 | | V-1 | NRADDP | 1.59 |
| 4696 | 3 | 4 | 5 | | V-1 | MUDENG | 1.69 | | 4792 | 3 | 4 | 5 | | V-1 | NRF1 | 1.61 |
| 4697 | 3 | 4 | 5 | | V-1 | MUS81 | 1.85 | | 4793 | 3 | 4 | 5 | | V-1 | NRP1 | 1.93 |
| 4698 | 3 | 4 | 5 | | V-1 | MUT | 1.71 | | 4794 | 3 | 4 | 5 | | V-1 | NSD1 | 1.76 |
| 4699 | 3 | 4 | 5 | | V-1 | MVD | 1.82 | | 4795 | 3 | 4 | 5 | | V-1 | NSF | 1.88 |
| 4700 | 3 | 4 | 5 | | V-1 | MXRA8 | 1.85 | | 4796 | 3 | 4 | 5 | | V-1 | NSMCE4A | 1.56 |

Fig. 40 - 26

| | | | | | | | | | | | | | | | | |
|---|---|---|---|---|---|---|---|---|---|---|---|---|---|---|---|---|
| 4797 | 3 | 4 | 5 | | | V-1 | NSUN3 | 1.69 | 4893 | 3 | 4 | 5 | | | V-1 | PGRMC2 | 1.78 |
| 4798 | 3 | 4 | 5 | | | V-1 | NT5C | 1.66 | 4894 | 3 | 4 | 5 | | | V-1 | PHF12 | 1.66 |
| 4799 | 3 | 4 | 5 | | | V-1 | NT5DC3 | 1.51 | 4895 | 3 | 4 | 5 | | | V-1 | PHF13 | 1.65 |
| 4800 | 3 | 4 | 5 | | | V-1 | NUDC | 1.69 | 4896 | 3 | 4 | 5 | | | V-1 | PHF15 | 1.55 |
| 4801 | 3 | 4 | 5 | | | V-1 | NUDCD3 | 1.53 | 4897 | 3 | 4 | 5 | | | V-1 | PHF17 | 1.78 |
| 4802 | 3 | 4 | 5 | | | V-1 | NUDT19 | 1.66 | 4898 | 3 | 4 | 5 | | | V-1 | PHF19 | 1.65 |
| 4803 | 3 | 4 | 5 | | | V-1 | NUDT22 | 1.67 | 4899 | 3 | 4 | 5 | | | V-1 | PHF2 | 1.92 |
| 4804 | 3 | 4 | 5 | | | V-1 | NUDT4P1 | 1.53 | 4900 | 3 | 4 | 5 | | | V-1 | PHF20 | 1.79 |
| 4805 | 3 | 4 | 5 | | | V-1 | NUMB | 1.68 | 4901 | 3 | 4 | 5 | | | V-1 | PHF8 | 1.98 |
| 4806 | 3 | 4 | 5 | | | V-1 | NUP153 | 1.72 | 4902 | 3 | 4 | 5 | | | V-1 | PHLPP2 | 1.51 |
| 4807 | 3 | 4 | 5 | | | V-1 | NUP155 | 1.67 | 4903 | 3 | 4 | 5 | | | V-1 | PHRF1 | 1.89 |
| 4808 | 3 | 4 | 5 | | | V-1 | NUP37 | 1.75 | 4904 | 3 | 4 | 5 | | | V-1 | PHTF2 | 1.87 |
| 4809 | 3 | 4 | 5 | | | V-1 | NUP54 | 1.50 | 4905 | 3 | 4 | 5 | | | V-1 | PI16 | 1.55 |
| 4810 | 3 | 4 | 5 | | | V-1 | NUP93 | 1.87 | 4906 | 3 | 4 | 5 | | | V-1 | PI4KB | 1.75 |
| 4811 | 3 | 4 | 5 | | | V-1 | NUP98 | 1.97 | 4907 | 3 | 4 | 5 | | | V-1 | PIAS2 | 1.72 |
| 4812 | 3 | 4 | 5 | | | V-1 | NUPL1 | 1.83 | 4908 | 3 | 4 | 5 | | | V-1 | PIAS4 | 1.77 |
| 4813 | 3 | 4 | 5 | | | V-1 | NUPL2 | 1.82 | 4909 | 3 | 4 | 5 | | | V-1 | PIBF1 | 1.74 |
| 4814 | 3 | 4 | 5 | | | V-1 | OGDH | 1.78 | 4910 | 3 | 4 | 5 | | | V-1 | PIGN | 1.69 |
| 4815 | 3 | 4 | 5 | | | V-1 | OGFOD1 | 1.88 | 4911 | 3 | 4 | 5 | | | V-1 | PIGO | 1.76 |
| 4816 | 3 | 4 | 5 | | | V-1 | OGFR | 1.97 | 4912 | 3 | 4 | 5 | | | V-1 | PIGQ | 1.85 |
| 4817 | 3 | 4 | 5 | | | V-1 | OGFRL1 | 1.51 | 4913 | 3 | 4 | 5 | | | V-1 | PIGS | 1.64 |
| 4818 | 3 | 4 | 5 | | | V-1 | OGG1 | 1.90 | 4914 | 3 | 4 | 5 | | | V-1 | PIGX | 1.51 |
| 4819 | 3 | 4 | 5 | | | V-1 | OLFM2 | 1.53 | 4915 | 3 | 4 | 5 | | | V-1 | PIH1D1 | 1.71 |
| 4820 | 3 | 4 | 5 | | | V-1 | OMA1 | 1.85 | 4916 | 3 | 4 | 5 | | | V-1 | PIK3CA | 1.65 |
| 4821 | 3 | 4 | 5 | | | V-1 | OMG | 1.78 | 4917 | 3 | 4 | 5 | | | V-1 | PIK3CD | 1.92 |
| 4822 | 3 | 4 | 5 | | | V-1 | OPA1 | 1.92 | 4918 | 3 | 4 | 5 | | | V-1 | PIK3R5 | 1.97 |
| 4823 | 3 | 4 | 5 | | | V-1 | OPA3 | 1.51 | 4919 | 3 | 4 | 5 | | | V-1 | PIP4K2B | 1.82 |
| 4824 | 3 | 4 | 5 | | | V-1 | OR52K1 | 1.55 | 4920 | 3 | 4 | 5 | | | V-1 | PIP5K1A | 1.72 |
| 4825 | 3 | 4 | 5 | | | V-1 | ORAI3 | 1.76 | 4921 | 3 | 4 | 5 | | | V-1 | PIP5K1C | 1.89 |
| 4826 | 3 | 4 | 5 | | | V-1 | ORC4 | 1.95 | 4922 | 3 | 4 | 5 | | | V-1 | PITPNB | 1.62 |
| 4827 | 3 | 4 | 5 | | | V-1 | OSBPL11 | 1.96 | 4923 | 3 | 4 | 5 | | | V-1 | PJA2 | 1.91 |
| 4828 | 3 | 4 | 5 | | | V-1 | OSBPL1A | 1.51 | 4924 | 3 | 4 | 5 | | | V-1 | PKM2 | 1.72 |
| 4829 | 3 | 4 | 5 | | | V-1 | OSBPL9 | 1.88 | 4925 | 3 | 4 | 5 | | | V-1 | PKN1 | 1.83 |
| 4830 | 3 | 4 | 5 | | | V-1 | OSTM1 | 1.76 | 4926 | 3 | 4 | 5 | | | V-1 | PKP4 | 1.66 |
| 4831 | 3 | 4 | 5 | | | V-1 | OTUD6B | 1.53 | 4927 | 3 | 4 | 5 | | | V-1 | PLA2G12A | 1.71 |
| 4832 | 3 | 4 | 5 | | | V-1 | OXA1L | 1.76 | 4928 | 3 | 4 | 5 | | | V-1 | PLAA | 1.98 |
| 4833 | 3 | 4 | 5 | | | V-1 | OXR1 | 1.65 | 4929 | 3 | 4 | 5 | | | V-1 | PLCB1 | 1.74 |
| 4834 | 3 | 4 | 5 | | | V-1 | OXSR1 | 1.67 | 4930 | 3 | 4 | 5 | | | V-1 | PLCH2 | 1.77 |
| 4835 | 3 | 4 | 5 | | | V-1 | P2RY11 | 1.54 | 4931 | 3 | 4 | 5 | | | V-1 | PLDN | 1.63 |
| 4836 | 3 | 4 | 5 | | | V-1 | P4HA1 | 1.93 | 4932 | 3 | 4 | 5 | | | V-1 | PLEK | 1.75 |
| 4837 | 3 | 4 | 5 | | | V-1 | PACRGL | 1.84 | 4933 | 3 | 4 | 5 | | | V-1 | PLEKHA2 | 1.65 |
| 4838 | 3 | 4 | 5 | | | V-1 | PACS2 | 1.97 | 4934 | 3 | 4 | 5 | | | V-1 | PLEKHA8 | 1.93 |
| 4839 | 3 | 4 | 5 | | | V-1 | PACSIN2 | 1.75 | 4935 | 3 | 4 | 5 | | | V-1 | PLEKHF2 | 1.96 |
| 4840 | 3 | 4 | 5 | | | V-1 | PAF1 | 1.61 | 4936 | 3 | 4 | 5 | | | V-1 | PLEKHG4 | 1.88 |
| 4841 | 3 | 4 | 5 | | | V-1 | PAG1 | 1.69 | 4937 | 3 | 4 | 5 | | | V-1 | PLEKHJ1 | 1.93 |
| 4842 | 3 | 4 | 5 | | | V-1 | PAICS | 1.67 | 4938 | 3 | 4 | 5 | | | V-1 | PLEKHM2 | 1.99 |
| 4843 | 3 | 4 | 5 | | | V-1 | PAIP2B | 1.63 | 4939 | 3 | 4 | 5 | | | V-1 | PLEKHM3 | 1.66 |
| 4844 | 3 | 4 | 5 | | | V-1 | PAK2 | 1.94 | 4940 | 3 | 4 | 5 | | | V-1 | PLEKHO2 | 1.80 |
| 4845 | 3 | 4 | 5 | | | V-1 | PAK4 | 1.72 | 4941 | 3 | 4 | 5 | | | V-1 | PLIN3 | 1.88 |
| 4846 | 3 | 4 | 5 | | | V-1 | PANK4 | 1.58 | 4942 | 3 | 4 | 5 | | | V-1 | PLK1S1 | 1.95 |
| 4847 | 3 | 4 | 5 | | | V-1 | PAPD4 | 1.90 | 4943 | 3 | 4 | 5 | | | V-1 | PLRG1 | 1.86 |
| 4848 | 3 | 4 | 5 | | | V-1 | PAQR3 | 1.64 | 4944 | 3 | 4 | 5 | | | V-1 | PLXNA1 | 1.59 |
| 4849 | 3 | 4 | 5 | | | V-1 | PARD3 | 1.66 | 4945 | 3 | 4 | 5 | | | V-1 | PLXNC1 | 1.57 |
| 4850 | 3 | 4 | 5 | | | V-1 | PARG | 1.58 | 4946 | 3 | 4 | 5 | | | V-1 | PMPCA | 1.98 |
| 4851 | 3 | 4 | 5 | | | V-1 | PBXIP1 | 1.92 | 4947 | 3 | 4 | 5 | | | V-1 | PMS2 | 1.56 |
| 4852 | 3 | 4 | 5 | | | V-1 | PCBP2 | 1.53 | 4948 | 3 | 4 | 5 | | | V-1 | PMS2CL | 1.80 |
| 4853 | 3 | 4 | 5 | | | V-1 | PCDH12 | 1.77 | 4949 | 3 | 4 | 5 | | | V-1 | PMS2P4 | 1.56 |
| 4854 | 3 | 4 | 5 | | | V-1 | PCID2 | 1.60 | 4950 | 3 | 4 | 5 | | | V-1 | PNMA1 | 1.68 |
| 4855 | 3 | 4 | 5 | | | V-1 | PCIF1 | 1.50 | 4951 | 3 | 4 | 5 | | | V-1 | PNMA3 | 1.82 |
| 4856 | 3 | 4 | 5 | | | V-1 | PCNA | 1.96 | 4952 | 3 | 4 | 5 | | | V-1 | PNPLA6 | 1.97 |
| 4857 | 3 | 4 | 5 | | | V-1 | PCNT | 2.00 | 4953 | 3 | 4 | 5 | | | V-1 | PNPO | 1.72 |
| 4858 | 3 | 4 | 5 | | | V-1 | PCNX | 1.79 | 4954 | 3 | 4 | 5 | | | V-1 | PNRC1 | 1.72 |
| 4859 | 3 | 4 | 5 | | | V-1 | PCNXL2 | 1.70 | 4955 | 3 | 4 | 5 | | | V-1 | PNRC2 | 1.55 |
| 4860 | 3 | 4 | 5 | | | V-1 | PCSK5 | 1.81 | 4956 | 3 | 4 | 5 | | | V-1 | POFUT1 | 1.57 |
| 4861 | 3 | 4 | 5 | | | V-1 | PCSK7 | 1.96 | 4957 | 3 | 4 | 5 | | | V-1 | POGK | 1.87 |
| 4862 | 3 | 4 | 5 | | | V-1 | PCYOX1L | 2.00 | 4958 | 3 | 4 | 5 | | | V-1 | POGLUT1 | 1.61 |
| 4863 | 3 | 4 | 5 | | | V-1 | PDCD10 | 1.57 | 4959 | 3 | 4 | 5 | | | V-1 | POLA1 | 1.65 |
| 4864 | 3 | 4 | 5 | | | V-1 | PDCD1LG2 | 1.83 | 4960 | 3 | 4 | 5 | | | V-1 | POLD3 | 1.91 |
| 4865 | 3 | 4 | 5 | | | V-1 | PDCD4 | 1.73 | 4961 | 3 | 4 | 5 | | | V-1 | POLD4 | 1.74 |
| 4866 | 3 | 4 | 5 | | | V-1 | PDCD6 | 1.62 | 4962 | 3 | 4 | 5 | | | V-1 | POLDIP3 | 1.97 |
| 4867 | 3 | 4 | 5 | | | V-1 | PDE12 | 1.58 | 4963 | 3 | 4 | 5 | | | V-1 | POLG | 1.94 |
| 4868 | 3 | 4 | 5 | | | V-1 | PDE4A | 1.64 | 4964 | 3 | 4 | 5 | | | V-1 | POLR1B | 1.91 |
| 4869 | 3 | 4 | 5 | | | V-1 | PDE6B | 1.74 | 4965 | 3 | 4 | 5 | | | V-1 | POLR1C | 1.60 |
| 4870 | 3 | 4 | 5 | | | V-1 | PDE6D | 1.52 | 4966 | 3 | 4 | 5 | | | V-1 | POLR2B | 1.52 |
| 4871 | 3 | 4 | 5 | | | V-1 | PDHA1 | 1.78 | 4967 | 3 | 4 | 5 | | | V-1 | POLR2E | 1.66 |
| 4872 | 3 | 4 | 5 | | | V-1 | PDIA3 | 1.87 | 4968 | 3 | 4 | 5 | | | V-1 | POLR2J2 | 1.88 |
| 4873 | 3 | 4 | 5 | | | V-1 | PDIA3P | 1.54 | 4969 | 3 | 4 | 5 | | | V-1 | POLR3B | 1.53 |
| 4874 | 3 | 4 | 5 | | | V-1 | PDIA4 | 1.79 | 4970 | 3 | 4 | 5 | | | V-1 | POLR3E | 1.80 |
| 4875 | 3 | 4 | 5 | | | V-1 | PDK3 | 1.57 | 4971 | 3 | 4 | 5 | | | V-1 | POM121 | 1.77 |
| 4876 | 3 | 4 | 5 | | | V-1 | PDLIM2 | 1.94 | 4972 | 3 | 4 | 5 | | | V-1 | POM121C | 1.84 |
| 4877 | 3 | 4 | 5 | | | V-1 | PDP1 | 1.88 | 4973 | 3 | 4 | 5 | | | V-1 | POMP | 1.95 |
| 4878 | 3 | 4 | 5 | | | V-1 | PDPK1 | 1.81 | 4974 | 3 | 4 | 5 | | | V-1 | POMT2 | 1.53 |
| 4879 | 3 | 4 | 5 | | | V-1 | PDS5A | 1.78 | 4975 | 3 | 4 | 5 | | | V-1 | POP5 | 1.54 |
| 4880 | 3 | 4 | 5 | | | V-1 | PDS5B | 1.82 | 4976 | 3 | 4 | 5 | | | V-1 | POR | 1.62 |
| 4881 | 3 | 4 | 5 | | | V-1 | PDSS2 | 1.53 | 4977 | 3 | 4 | 5 | | | V-1 | PP7080 | 1.98 |
| 4882 | 3 | 4 | 5 | | | V-1 | PDXK | 1.64 | 4978 | 3 | 4 | 5 | | | V-1 | PPAT | 1.62 |
| 4883 | 3 | 4 | 5 | | | V-1 | PELP1 | 1.87 | 4979 | 3 | 4 | 5 | | | V-1 | PPHLN1 | 1.61 |
| 4884 | 3 | 4 | 5 | | | V-1 | PER2 | 1.85 | 4980 | 3 | 4 | 5 | | | V-1 | PPIF | 1.65 |
| 4885 | 3 | 4 | 5 | | | V-1 | PES1 | 1.53 | 4981 | 3 | 4 | 5 | | | V-1 | PPIG | 1.56 |
| 4886 | 3 | 4 | 5 | | | V-1 | PEX1 | 1.97 | 4982 | 3 | 4 | 5 | | | V-1 | PPIL3 | 1.63 |
| 4887 | 3 | 4 | 5 | | | V-1 | PEX12 | 1.61 | 4983 | 3 | 4 | 5 | | | V-1 | PPIP5K1 | 1.97 |
| 4888 | 3 | 4 | 5 | | | V-1 | PEX26 | 1.66 | 4984 | 3 | 4 | 5 | | | V-1 | PPIP5K2 | 1.91 |
| 4889 | 3 | 4 | 5 | | | V-1 | PFKL | 1.93 | 4985 | 3 | 4 | 5 | | | V-1 | PPM1D | 1.92 |
| 4890 | 3 | 4 | 5 | | | V-1 | PFKM | 1.98 | 4986 | 3 | 4 | 5 | | | V-1 | PPME1 | 1.57 |
| 4891 | 3 | 4 | 5 | | | V-1 | PGBD4 | 1.91 | 4987 | 3 | 4 | 5 | | | V-1 | PPP1R10 | 1.97 |
| 4892 | 3 | 4 | 5 | | | V-1 | PGM2L1 | 1.86 | 4988 | 3 | 4 | 5 | | | V-1 | PPP1R11 | 1.67 |

Fig. 40 - 27

| | | | | | | | | | | | | | | | |
|---|---|---|---|---|---|---|---|---|---|---|---|---|---|---|---|
| 4989 | 3 | 4 | 5 | | V-1 | PPP1R15B | 1.82 | 5085 | 3 | 4 | 5 | | V-1 | PTGES2 | 1.57 |
| 4990 | 3 | 4 | 5 | | V-1 | PPP1R35 | 1.89 | 5086 | 3 | 4 | 5 | | V-1 | PTGES3 | 1.61 |
| 4991 | 3 | 4 | 5 | | V-1 | PPP1R3F | 1.74 | 5087 | 3 | 4 | 5 | | V-1 | PTK2 | 1.83 |
| 4992 | 3 | 4 | 5 | | V-1 | PPP1R9B | 1.60 | 5088 | 3 | 4 | 5 | | V-1 | PTP4A1 | 1.58 |
| 4993 | 3 | 4 | 5 | | V-1 | PPP2CB | 1.86 | 5089 | 3 | 4 | 5 | | V-1 | PTPN1 | 1.79 |
| 4994 | 3 | 4 | 5 | | V-1 | PPP2R2A | 1.97 | 5090 | 3 | 4 | 5 | | V-1 | PTPN11 | 1.67 |
| 4995 | 3 | 4 | 5 | | V-1 | PPP2R2D | 1.67 | 5091 | 3 | 4 | 5 | | V-1 | PTPN2 | 1.54 |
| 4996 | 3 | 4 | 5 | | V-1 | PPP2R3B | 1.62 | 5092 | 3 | 4 | 5 | | V-1 | PTPN22 | 1.58 |
| 4997 | 3 | 4 | 5 | | V-1 | PPP2R3C | 1.81 | 5093 | 3 | 4 | 5 | | V-1 | PTPN6 | 1.82 |
| 4998 | 3 | 4 | 5 | | V-1 | PPP2R4 | 1.62 | 5094 | 3 | 4 | 5 | | V-1 | PTPRJ | 1.51 |
| 4999 | 3 | 4 | 5 | | V-1 | PPP2R5A | 1.95 | 5095 | 3 | 4 | 5 | | V-1 | PTS | 1.54 |
| 5000 | 3 | 4 | 5 | | V-1 | PPP2R5C | 1.60 | 5096 | 3 | 4 | 5 | | V-1 | PTX3 | 1.58 |
| 5001 | 3 | 4 | 5 | | V-1 | PPP2R5E | 1.73 | 5097 | 3 | 4 | 5 | | V-1 | PUM2 | 1.82 |
| 5002 | 3 | 4 | 5 | | V-1 | PPP3CA | 1.56 | 5098 | 3 | 4 | 5 | | V-1 | PURA | 1.86 |
| 5003 | 3 | 4 | 5 | | V-1 | PPP3CB | 1.66 | 5099 | 3 | 4 | 5 | | V-1 | PUS3 | 1.53 |
| 5004 | 3 | 4 | 5 | | V-1 | PPP3R1 | 1.66 | 5100 | 3 | 4 | 5 | | V-1 | PUS7L | 1.80 |
| 5005 | 3 | 4 | 5 | | V-1 | PPP4R1 | 1.85 | 5101 | 3 | 4 | 5 | | V-1 | PUSL1 | 1.69 |
| 5006 | 3 | 4 | 5 | | V-1 | PPP6R1 | 1.53 | 5102 | 3 | 4 | 5 | | V-1 | PWP2 | 1.76 |
| 5007 | 3 | 4 | 5 | | V-1 | PPPDE2 | 1.69 | 5103 | 3 | 4 | 5 | | V-1 | PWWP2A | 1.81 |
| 5008 | 3 | 4 | 5 | | V-1 | PPRC1 | 1.74 | 5104 | 3 | 4 | 5 | | V-1 | PXDC1 | 1.73 |
| 5009 | 3 | 4 | 5 | | V-1 | PPT2 | 1.58 | 5105 | 3 | 4 | 5 | | V-1 | PXMP4 | 1.51 |
| 5010 | 3 | 4 | 5 | | V-1 | PQLC2 | 1.93 | 5106 | 3 | 4 | 5 | | V-1 | PXN | 1.64 |
| 5011 | 3 | 4 | 5 | | V-1 | PQLC3 | 1.51 | 5107 | 3 | 4 | 5 | | V-1 | PYCR2 | 1.58 |
| 5012 | 3 | 4 | 5 | | V-1 | PRAF2 | 1.51 | 5108 | 3 | 4 | 5 | | V-1 | PYROXD1 | 1.82 |
| 5013 | 3 | 4 | 5 | | V-1 | PRCP | 1.96 | 5109 | 3 | 4 | 5 | | V-1 | PYROXD2 | 1.69 |
| 5014 | 3 | 4 | 5 | | V-1 | PRDM2 | 1.79 | 5110 | 3 | 4 | 5 | | V-1 | QPCTL | 1.64 |
| 5015 | 3 | 4 | 5 | | V-1 | PRDM4 | 1.51 | 5111 | 3 | 4 | 5 | | V-1 | QRICH1 | 1.85 |
| 5016 | 3 | 4 | 5 | | V-1 | PRDX1 | 1.70 | 5112 | 3 | 4 | 5 | | V-1 | QSOX1 | 1.74 |
| 5017 | 3 | 4 | 5 | | V-1 | PRDX3 | 1.83 | 5113 | 3 | 4 | 5 | | V-1 | R3HDM2 | 1.69 |
| 5018 | 3 | 4 | 5 | | V-1 | PREB | 1.67 | 5114 | 3 | 4 | 5 | | V-1 | RAB10 | 1.61 |
| 5019 | 3 | 4 | 5 | | V-1 | PREP | 1.67 | 5115 | 3 | 4 | 5 | | V-1 | RAB11A | 1.73 |
| 5020 | 3 | 4 | 5 | | V-1 | PREX1 | 1.63 | 5116 | 3 | 4 | 5 | | V-1 | RAB11FIP2 | 1.96 |
| 5021 | 3 | 4 | 5 | | V-1 | PRICKLE3 | 1.57 | 5117 | 3 | 4 | 5 | | V-1 | RAB11FIP3 | 1.94 |
| 5022 | 3 | 4 | 5 | | V-1 | PRKAA1 | 1.56 | 5118 | 3 | 4 | 5 | | V-1 | RAB11FIP4 | 1.57 |
| 5023 | 3 | 4 | 5 | | V-1 | PRKAB1 | 1.92 | 5119 | 3 | 4 | 5 | | V-1 | RAB15 | 1.66 |
| 5024 | 3 | 4 | 5 | | V-1 | PRKAR1A | 1.79 | 5120 | 3 | 4 | 5 | | V-1 | RAB1A | 1.93 |
| 5025 | 3 | 4 | 5 | | V-1 | PRKCB | 1.82 | 5121 | 3 | 4 | 5 | | V-1 | RAB21 | 1.58 |
| 5026 | 3 | 4 | 5 | | V-1 | PRKCI | 1.59 | 5122 | 3 | 4 | 5 | | V-1 | RAB28 | 1.68 |
| 5027 | 3 | 4 | 5 | | V-1 | PRKD3 | 1.63 | 5123 | 3 | 4 | 5 | | V-1 | RAB2A | 1.56 |
| 5028 | 3 | 4 | 5 | | V-1 | PRKRA | 1.59 | 5124 | 3 | 4 | 5 | | V-1 | RAB2B | 1.68 |
| 5029 | 3 | 4 | 5 | | V-1 | PRKX | 1.83 | 5125 | 3 | 4 | 5 | | V-1 | RAB31 | 1.98 |
| 5030 | 3 | 4 | 5 | | V-1 | PRMT10 | 1.61 | 5126 | 3 | 4 | 5 | | V-1 | RAB33B | 1.75 |
| 5031 | 3 | 4 | 5 | | V-1 | PRMT2 | 1.60 | 5127 | 3 | 4 | 5 | | V-1 | RAB3D | 1.64 |
| 5032 | 3 | 4 | 5 | | V-1 | PRMT5 | 1.57 | 5128 | 3 | 4 | 5 | | V-1 | RAB5A | 1.68 |
| 5033 | 3 | 4 | 5 | | V-1 | PRORSD1P | 1.78 | 5129 | 3 | 4 | 5 | | V-1 | RAB8B | 1.86 |
| 5034 | 3 | 4 | 5 | | V-1 | PROSC | 1.81 | 5130 | 3 | 4 | 5 | | V-1 | RABEP1 | 1.73 |
| 5035 | 3 | 4 | 5 | | V-1 | PRPF18 | 1.99 | 5131 | 3 | 4 | 5 | | V-1 | RABL2A | 1.98 |
| 5036 | 3 | 4 | 5 | | V-1 | PRPF19 | 1.61 | 5132 | 3 | 4 | 5 | | V-1 | RABL2B | 1.73 |
| 5037 | 3 | 4 | 5 | | V-1 | PRPF31 | 1.66 | 5133 | 3 | 4 | 5 | | V-1 | RACGAP1 | 1.98 |
| 5038 | 3 | 4 | 5 | | V-1 | PRPF3SA | 1.69 | 5134 | 3 | 4 | 5 | | V-1 | RAD17 | 1.57 |
| 5039 | 3 | 4 | 5 | | V-1 | PRPF4 | 1.61 | 5135 | 3 | 4 | 5 | | V-1 | RAD18 | 1.67 |
| 5040 | 3 | 4 | 5 | | V-1 | PRPF6 | 1.77 | 5136 | 3 | 4 | 5 | | V-1 | RAD21 | 1.85 |
| 5041 | 3 | 4 | 5 | | V-1 | PRPSAP1 | 1.73 | 5137 | 3 | 4 | 5 | | V-1 | RAD50 | 1.96 |
| 5042 | 3 | 4 | 5 | | V-1 | PRPSAP2 | 1.61 | 5138 | 3 | 4 | 5 | | V-1 | RAD51C | 1.55 |
| 5043 | 3 | 4 | 5 | | V-1 | PRR11 | 1.96 | 5139 | 3 | 4 | 5 | | V-1 | RAD51D | 1.69 |
| 5044 | 3 | 4 | 5 | | V-1 | PRR12 | 1.86 | 5140 | 3 | 4 | 5 | | V-1 | RAD54L2 | 1.53 |
| 5045 | 3 | 4 | 5 | | V-1 | PRR13 | 1.72 | 5141 | 3 | 4 | 5 | | V-1 | RAI1 | 1.98 |
| 5046 | 3 | 4 | 5 | | V-1 | PRR14 | 1.89 | 5142 | 3 | 4 | 5 | | V-1 | RALA | 1.51 |
| 5047 | 3 | 4 | 5 | | V-1 | PRR3 | 1.67 | 5143 | 3 | 4 | 5 | | V-1 | RALBP1 | 1.86 |
| 5048 | 3 | 4 | 5 | | V-1 | PRRC1 | 1.83 | 5144 | 3 | 4 | 5 | | V-1 | RANBP2 | 1.95 |
| 5049 | 3 | 4 | 5 | | V-1 | PRRC2A | 1.57 | 5145 | 3 | 4 | 5 | | V-1 | RANBP3 | 1.56 |
| 5050 | 3 | 4 | 5 | | V-1 | PRRT1 | 1.51 | 5146 | 3 | 4 | 5 | | V-1 | RANBP9 | 1.96 |
| 5051 | 3 | 4 | 5 | | V-1 | PRRT2 | 1.93 | 5147 | 3 | 4 | 5 | | V-1 | RAPGEF2 | 1.88 |
| 5052 | 3 | 4 | 5 | | V-1 | PRRT3 | 1.65 | 5148 | 3 | 4 | 5 | | V-1 | RAPGEF6 | 1.67 |
| 5053 | 3 | 4 | 5 | | V-1 | PRSS53 | 1.90 | 5149 | 3 | 4 | 5 | | V-1 | RAPH1 | 1.68 |
| 5054 | 3 | 4 | 5 | | V-1 | PRUNE | 1.72 | 5150 | 3 | 4 | 5 | | V-1 | RARA | 1.80 |
| 5055 | 3 | 4 | 5 | | V-1 | PRX | 1.63 | 5151 | 3 | 4 | 5 | | V-1 | RARG | 1.85 |
| 5056 | 3 | 4 | 5 | | V-1 | PSAT1 | 1.91 | 5152 | 3 | 4 | 5 | | V-1 | RASA3 | 1.71 |
| 5057 | 3 | 4 | 5 | | V-1 | PSD4 | 1.83 | 5153 | 3 | 4 | 5 | | V-1 | RASGRP4 | 1.85 |
| 5058 | 3 | 4 | 5 | | V-1 | PSEN1 | 1.87 | 5154 | 3 | 4 | 5 | | V-1 | RASSF1 | 1.70 |
| 5059 | 3 | 4 | 5 | | V-1 | PSENEN | 1.85 | 5155 | 3 | 4 | 5 | | V-1 | RASSF5 | 1.58 |
| 5060 | 3 | 4 | 5 | | V-1 | PSIMCT-1 | 1.59 | 5156 | 3 | 4 | 5 | | V-1 | RAVER1 | 1.79 |
| 5061 | 3 | 4 | 5 | | V-1 | PSMA3 | 1.71 | 5157 | 3 | 4 | 5 | | V-1 | RB1CC1 | 1.67 |
| 5062 | 3 | 4 | 5 | | V-1 | PSMA4 | 1.79 | 5158 | 3 | 4 | 5 | | V-1 | RBBP4 | 1.71 |
| 5063 | 3 | 4 | 5 | | V-1 | PSMA7 | 1.52 | 5159 | 3 | 4 | 5 | | V-1 | RBBP5 | 1.65 |
| 5064 | 3 | 4 | 5 | | V-1 | PSMB6 | 1.71 | 5160 | 3 | 4 | 5 | | V-1 | RBBP7 | 1.55 |
| 5065 | 3 | 4 | 5 | | V-1 | PSMB8 | 1.85 | 5161 | 3 | 4 | 5 | | V-1 | RBBP8 | 1.98 |
| 5066 | 3 | 4 | 5 | | V-1 | PSMC1 | 1.55 | 5162 | 3 | 4 | 5 | | V-1 | RBL2 | 1.78 |
| 5067 | 3 | 4 | 5 | | V-1 | PSMC2 | 1.52 | 5163 | 3 | 4 | 5 | | V-1 | RBM12 | 1.54 |
| 5068 | 3 | 4 | 5 | | V-1 | PSMC5 | 1.57 | 5164 | 3 | 4 | 5 | | V-1 | RBM17 | 1.83 |
| 5069 | 3 | 4 | 5 | | V-1 | PSMC6 | 1.87 | 5165 | 3 | 4 | 5 | | V-1 | RBM22 | 1.91 |
| 5070 | 3 | 4 | 5 | | V-1 | PSMD12 | 1.67 | 5166 | 3 | 4 | 5 | | V-1 | RBM27 | 1.60 |
| 5071 | 3 | 4 | 5 | | V-1 | PSMD13 | 1.55 | 5167 | 3 | 4 | 5 | | V-1 | RBM34 | 1.56 |
| 5072 | 3 | 4 | 5 | | V-1 | PSMD2 | 1.69 | 5168 | 3 | 4 | 5 | | V-1 | RBM45 | 1.78 |
| 5073 | 3 | 4 | 5 | | V-1 | PSMD3 | 1.53 | 5169 | 3 | 4 | 5 | | V-1 | RBM47 | 1.74 |
| 5074 | 3 | 4 | 5 | | V-1 | PSMD6 | 1.79 | 5170 | 3 | 4 | 5 | | V-1 | RBM4B | 1.69 |
| 5075 | 3 | 4 | 5 | | V-1 | PSMG2 | 1.62 | 5171 | 3 | 4 | 5 | | V-1 | RBM7 | 1.54 |
| 5076 | 3 | 4 | 5 | | V-1 | PSPC1 | 1.89 | 5172 | 3 | 4 | 5 | | V-1 | RBMX2 | 1.63 |
| 5077 | 3 | 4 | 5 | | V-1 | PSRC1 | 1.52 | 5173 | 3 | 4 | 5 | | V-1 | RBPJ | 1.77 |
| 5078 | 3 | 4 | 5 | | V-1 | PSTPIP1 | 1.88 | 5174 | 3 | 4 | 5 | | V-1 | RBX1 | 1.72 |
| 5079 | 3 | 4 | 5 | | V-1 | PTAFR | 1.77 | 5175 | 3 | 4 | 5 | | V-1 | RCC1 | 1.54 |
| 5080 | 3 | 4 | 5 | | V-1 | PTCD2 | 1.58 | 5176 | 3 | 4 | 5 | | V-1 | RCN1 | 1.66 |
| 5081 | 3 | 4 | 5 | | V-1 | PTDSS1 | 1.54 | 5177 | 3 | 4 | 5 | | V-1 | RCSD1 | 1.51 |
| 5082 | 3 | 4 | 5 | | V-1 | PTDSS2 | 1.59 | 5178 | 3 | 4 | 5 | | V-1 | RDH10 | 1.87 |
| 5083 | 3 | 4 | 5 | | V-1 | PTEN | 1.75 | 5179 | 3 | 4 | 5 | | V-1 | RDX | 1.74 |
| 5084 | 3 | 4 | 5 | | V-1 | PTGER4 | 1.88 | 5180 | 3 | 4 | 5 | | V-1 | RECK | 1.59 |

Fig. 40 - 28

| | | | | | | | | | | | | | | | | |
|---|---|---|---|---|---|---|---|---|---|---|---|---|---|---|---|---|
| 5181 | 3 | 4 | 5 | | | V-1 | REEP3 | 1.64 | 5277 | 3 | 4 | 5 | | | V-1 | SAP30BP | 1.93 |
| 5182 | 3 | 4 | 5 | | | V-1 | REL | 1.69 | 5278 | 3 | 4 | 5 | | | V-1 | SAR1A | 1.52 |
| 5183 | 3 | 4 | 5 | | | V-1 | REPS1 | 1.85 | 5279 | 3 | 4 | 5 | | | V-1 | SAR1B | 1.72 |
| 5184 | 3 | 4 | 5 | | | V-1 | RER1 | 1.77 | 5280 | 3 | 4 | 5 | | | V-1 | SASH3 | 1.53 |
| 5185 | 3 | 4 | 5 | | | V-1 | REST | 1.54 | 5281 | 3 | 4 | 5 | | | V-1 | SAT2 | 1.73 |
| 5186 | 3 | 4 | 5 | | | V-1 | REXO1 | 1.69 | 5282 | 3 | 4 | 5 | | | V-1 | SATB1 | 1.98 |
| 5187 | 3 | 4 | 5 | | | V-1 | RFC5 | 1.88 | 5283 | 3 | 4 | 5 | | | V-1 | SBF1 | 1.78 |
| 5188 | 3 | 4 | 5 | | | V-1 | RFNG | 1.55 | 5284 | 3 | 4 | 5 | | | V-1 | SC5DL | 1.54 |
| 5189 | 3 | 4 | 5 | | | V-1 | RFT1 | 1.84 | 5285 | 3 | 4 | 5 | | | V-1 | SCAF1 | 1.85 |
| 5190 | 3 | 4 | 5 | | | V-1 | RFWD3 | 1.89 | 5286 | 3 | 4 | 5 | | | V-1 | SCAF8 | 1.78 |
| 5191 | 3 | 4 | 5 | | | V-1 | RFX3 | 1.83 | 5287 | 3 | 4 | 5 | | | V-1 | SCAI | 1.88 |
| 5192 | 3 | 4 | 5 | | | V-1 | RGP1 | 1.52 | 5288 | 3 | 4 | 5 | | | V-1 | SCAMP3 | 1.93 |
| 5193 | 3 | 4 | 5 | | | V-1 | RGS10 | 1.50 | 5289 | 3 | 4 | 5 | | | V-1 | SCAP | 1.64 |
| 5194 | 3 | 4 | 5 | | | V-1 | RGS14 | 1.67 | 5290 | 3 | 4 | 5 | | | V-1 | SCCPDH | 1.56 |
| 5195 | 3 | 4 | 5 | | | V-1 | RGS2 | 1.71 | 5291 | 3 | 4 | 5 | | | V-1 | SCFD1 | 1.69 |
| 5196 | 3 | 4 | 5 | | | V-1 | RHBDD1 | 1.90 | 5292 | 3 | 4 | 5 | | | V-1 | SCG81C1 | 1.63 |
| 5197 | 3 | 4 | 5 | | | V-1 | RHBDD2 | 1.54 | 5293 | 3 | 4 | 5 | | | V-1 | SCMH1 | 1.80 |
| 5198 | 3 | 4 | 5 | | | V-1 | RHBDD3 | 1.91 | 5294 | 3 | 4 | 5 | | | V-1 | SCML4 | 1.83 |
| 5199 | 3 | 4 | 5 | | | V-1 | RHOH | 1.54 | 5295 | 3 | 4 | 5 | | | V-1 | SCO1 | 1.76 |
| 5200 | 3 | 4 | 5 | | | V-1 | RHOQ | 1.52 | 5296 | 3 | 4 | 5 | | | V-1 | SCRN3 | 1.79 |
| 5201 | 3 | 4 | 5 | | | V-1 | RIC3 | 1.89 | 5297 | 3 | 4 | 5 | | | V-1 | SCYL2 | 1.95 |
| 5202 | 3 | 4 | 5 | | | V-1 | RIC8B | 1.71 | 5298 | 3 | 4 | 5 | | | V-1 | SCYL3 | 1.65 |
| 5203 | 3 | 4 | 5 | | | V-1 | RIF1 | 1.98 | 5299 | 3 | 4 | 5 | | | V-1 | SDAD1 | 1.60 |
| 5204 | 3 | 4 | 5 | | | V-1 | RIN3 | 1.53 | 5300 | 3 | 4 | 5 | | | V-1 | SDC3 | 1.75 |
| 5205 | 3 | 4 | 5 | | | V-1 | RING1 | 1.74 | 5301 | 3 | 4 | 5 | | | V-1 | SDCCAG8 | 1.65 |
| 5206 | 3 | 4 | 5 | | | V-1 | RINL | 1.63 | 5302 | 3 | 4 | 5 | | | V-1 | SDF2 | 1.56 |
| 5207 | 3 | 4 | 5 | | | V-1 | RINT1 | 1.90 | 5303 | 3 | 4 | 5 | | | V-1 | SDHA | 1.78 |
| 5208 | 3 | 4 | 5 | | | V-1 | RIOK1 | 1.51 | 5304 | 3 | 4 | 5 | | | V-1 | SDHC | 1.51 |
| 5209 | 3 | 4 | 5 | | | V-1 | RIT1 | 1.66 | 5305 | 3 | 4 | 5 | | | V-1 | SDPR | 1.84 |
| 5210 | 3 | 4 | 5 | | | V-1 | RMI1 | 1.98 | 5306 | 3 | 4 | 5 | | | V-1 | SDSL | 1.88 |
| 5211 | 3 | 4 | 5 | | | V-1 | RMND5A | 1.61 | 5307 | 3 | 4 | 5 | | | V-1 | SEC11A | 1.50 |
| 5212 | 3 | 4 | 5 | | | V-1 | RMND5B | 1.63 | 5308 | 3 | 4 | 5 | | | V-1 | SEC14L1 | 1.80 |
| 5213 | 3 | 4 | 5 | | | V-1 | RNASEH1 | 1.71 | 5309 | 3 | 4 | 5 | | | V-1 | SEC22A | 1.57 |
| 5214 | 3 | 4 | 5 | | | V-1 | RNF103 | 1.89 | 5310 | 3 | 4 | 5 | | | V-1 | SEC22B | 1.86 |
| 5215 | 3 | 4 | 5 | | | V-1 | RNF111 | 1.74 | 5311 | 3 | 4 | 5 | | | V-1 | SEC22C | 1.51 |
| 5216 | 3 | 4 | 5 | | | V-1 | RNF121 | 1.85 | 5312 | 3 | 4 | 5 | | | V-1 | SEC23A | 1.55 |
| 5217 | 3 | 4 | 5 | | | V-1 | RNF138 | 1.65 | 5313 | 3 | 4 | 5 | | | V-1 | SEC23B | 1.65 |
| 5218 | 3 | 4 | 5 | | | V-1 | RNF138P1 | 1.67 | 5314 | 3 | 4 | 5 | | | V-1 | SEC23IP | 1.86 |
| 5219 | 3 | 4 | 5 | | | V-1 | RNF141 | 1.59 | 5315 | 3 | 4 | 5 | | | V-1 | SEC24A | 1.73 |
| 5220 | 3 | 4 | 5 | | | V-1 | RNF146 | 1.66 | 5316 | 3 | 4 | 5 | | | V-1 | SEC24B | 1.63 |
| 5221 | 3 | 4 | 5 | | | V-1 | RNF168 | 1.78 | 5317 | 3 | 4 | 5 | | | V-1 | SEC61A1 | 1.97 |
| 5222 | 3 | 4 | 5 | | | V-1 | RNF170 | 1.96 | 5318 | 3 | 4 | 5 | | | V-1 | SEC63 | 1.64 |
| 5223 | 3 | 4 | 5 | | | V-1 | RNF181 | 1.76 | 5319 | 3 | 4 | 5 | | | V-1 | SEH1L | 1.56 |
| 5224 | 3 | 4 | 5 | | | V-1 | RNF185 | 1.96 | 5320 | 3 | 4 | 5 | | | V-1 | SEMA4A | 1.92 |
| 5225 | 3 | 4 | 5 | | | V-1 | RNF19B | 1.77 | 5321 | 3 | 4 | 5 | | | V-1 | SENP2 | 1.98 |
| 5226 | 3 | 4 | 5 | | | V-1 | RNF20 | 1.85 | 5322 | 3 | 4 | 5 | | | V-1 | SENP3 | 1.87 |
| 5227 | 3 | 4 | 5 | | | V-1 | RNF214 | 1.86 | 5323 | 3 | 4 | 5 | | | V-1 | SENP5 | 1.87 |
| 5228 | 3 | 4 | 5 | | | V-1 | RNF215 | 1.83 | 5324 | 3 | 4 | 5 | | | V-1 | SEPHS2 | 1.65 |
| 5229 | 3 | 4 | 5 | | | V-1 | RNF216 | 1.82 | 5325 | 3 | 4 | 5 | | | V-1 | SEPN1 | 1.89 |
| 5230 | 3 | 4 | 5 | | | V-1 | RNF216P1 | 1.55 | 5326 | 3 | 4 | 5 | | | V-1 | 42614 | 1.52 |
| 5231 | 3 | 4 | 5 | | | V-1 | RNF34 | 1.59 | 5327 | 3 | 4 | 5 | | | V-1 | 42623 | 1.53 |
| 5232 | 3 | 4 | 5 | | | V-1 | RNF40 | 1.98 | 5328 | 3 | 4 | 5 | | | V-1 | 42615 | 1.55 |
| 5233 | 3 | 4 | 5 | | | V-1 | RNF44 | 1.64 | 5329 | 3 | 4 | 5 | | | V-1 | 42620 | 1.62 |
| 5234 | 3 | 4 | 5 | | | V-1 | RNF6 | 1.64 | 5330 | 3 | 4 | 5 | | | V-1 | SERINC1 | 1.93 |
| 5235 | 3 | 4 | 5 | | | V-1 | RNGTT | 1.65 | 5331 | 3 | 4 | 5 | | | V-1 | SERINC3 | 1.90 |
| 5236 | 3 | 4 | 5 | | | V-1 | RNMT | 1.67 | 5332 | 3 | 4 | 5 | | | V-1 | SERINC5 | 1.83 |
| 5237 | 3 | 4 | 5 | | | V-1 | RNPEP | 1.83 | 5333 | 3 | 4 | 5 | | | V-1 | SERPINA1 | 1.83 |
| 5238 | 3 | 4 | 5 | | | V-1 | RP2 | 1.72 | 5334 | 3 | 4 | 5 | | | V-1 | SERPINB8 | 1.66 |
| 5239 | 3 | 4 | 5 | | | V-1 | RP9 | 1.51 | 5335 | 3 | 4 | 5 | | | V-1 | SERPINE2 | 1.65 |
| 5240 | 3 | 4 | 5 | | | V-1 | RPL13P5 | 1.79 | 5336 | 3 | 4 | 5 | | | V-1 | SERTAD1 | 1.55 |
| 5241 | 3 | 4 | 5 | | | V-1 | RPL22L1 | 1.66 | 5337 | 3 | 4 | 5 | | | V-1 | SERTAD2 | 1.69 |
| 5242 | 3 | 4 | 5 | | | V-1 | RPL23AP53 | 1.59 | 5338 | 3 | 4 | 5 | | | V-1 | SERTAD3 | 1.54 |
| 5243 | 3 | 4 | 5 | | | V-1 | RPN2 | 1.76 | 5339 | 3 | 4 | 5 | | | V-1 | SETD1A | 1.98 |
| 5244 | 3 | 4 | 5 | | | V-1 | RPP25 | 1.72 | 5340 | 3 | 4 | 5 | | | V-1 | SETD8 | 1.68 |
| 5245 | 3 | 4 | 5 | | | V-1 | RPRD1B | 1.51 | 5341 | 3 | 4 | 5 | | | V-1 | SF3A1 | 1.84 |
| 5246 | 3 | 4 | 5 | | | V-1 | RPRD2 | 1.92 | 5342 | 3 | 4 | 5 | | | V-1 | SF3B2 | 1.71 |
| 5247 | 3 | 4 | 5 | | | V-1 | RPS6KA3 | 1.65 | 5343 | 3 | 4 | 5 | | | V-1 | SF3B3 | 1.99 |
| 5248 | 3 | 4 | 5 | | | V-1 | RPS6KA5 | 1.74 | 5344 | 3 | 4 | 5 | | | V-1 | SF3B4 | 1.57 |
| 5249 | 3 | 4 | 5 | | | V-1 | RPS6KB1 | 1.59 | 5345 | 3 | 4 | 5 | | | V-1 | SFT2D3 | 1.72 |
| 5250 | 3 | 4 | 5 | | | V-1 | RQCD1 | 1.64 | 5346 | 3 | 4 | 5 | | | V-1 | SFXN3 | 1.60 |
| 5251 | 3 | 4 | 5 | | | V-1 | RRAGA | 1.60 | 5347 | 3 | 4 | 5 | | | V-1 | SFXN5 | 1.85 |
| 5252 | 3 | 4 | 5 | | | V-1 | RRAGB | 1.95 | 5348 | 3 | 4 | 5 | | | V-1 | SGMS1 | 1.54 |
| 5253 | 3 | 4 | 5 | | | V-1 | RRAGD | 1.53 | 5349 | 3 | 4 | 5 | | | V-1 | SGOL1 | 1.93 |
| 5254 | 3 | 4 | 5 | | | V-1 | RRAS | 1.77 | 5350 | 3 | 4 | 5 | | | V-1 | SGPP1 | 1.74 |
| 5255 | 3 | 4 | 5 | | | V-1 | RRM1 | 1.61 | 5351 | 3 | 4 | 5 | | | V-1 | SGTB | 1.53 |
| 5256 | 3 | 4 | 5 | | | V-1 | RRN3 | 1.94 | 5352 | 3 | 4 | 5 | | | V-1 | SH2B2 | 2.00 |
| 5257 | 3 | 4 | 5 | | | V-1 | RRP15 | 1.71 | 5353 | 3 | 4 | 5 | | | V-1 | SH2D3A | 1.71 |
| 5258 | 3 | 4 | 5 | | | V-1 | RRP8 | 1.68 | 5354 | 3 | 4 | 5 | | | V-1 | SH3BP1 | 1.54 |
| 5259 | 3 | 4 | 5 | | | V-1 | RSRC2 | 1.98 | 5355 | 3 | 4 | 5 | | | V-1 | SH3GL1P1 | 1.79 |
| 5260 | 3 | 4 | 5 | | | V-1 | RTCD1 | 1.53 | 5356 | 3 | 4 | 5 | | | V-1 | SH3GLB1 | 1.50 |
| 5261 | 3 | 4 | 5 | | | V-1 | RTEL1 | 1.50 | 5357 | 3 | 4 | 5 | | | V-1 | SH3KBP1 | 1.60 |
| 5262 | 3 | 4 | 5 | | | V-1 | RTF1 | 1.92 | 5358 | 3 | 4 | 5 | | | V-1 | SH3YL1 | 1.98 |
| 5263 | 3 | 4 | 5 | | | V-1 | RTN4 | 1.79 | 5359 | 3 | 4 | 5 | | | V-1 | SHC1 | 1.66 |
| 5264 | 3 | 4 | 5 | | | V-1 | RUFY1 | 1.95 | 5360 | 3 | 4 | 5 | | | V-1 | SHOC2 | 1.56 |
| 5265 | 3 | 4 | 5 | | | V-1 | RUNX1 | 1.91 | 5361 | 3 | 4 | 5 | | | V-1 | SIGIRR | 1.73 |
| 5266 | 3 | 4 | 5 | | | V-1 | RUSC1 | 1.90 | 5362 | 3 | 4 | 5 | | | V-1 | SIGLEC7 | 1.59 |
| 5267 | 3 | 4 | 5 | | | V-1 | RWDD2A | 1.63 | 5363 | 3 | 4 | 5 | | | V-1 | SIK2 | 1.95 |
| 5268 | 3 | 4 | 5 | | | V-1 | RWDD4 | 1.63 | 5364 | 3 | 4 | 5 | | | V-1 | SIPA1 | 1.66 |
| 5269 | 3 | 4 | 5 | | | V-1 | RXRA | 1.51 | 5365 | 3 | 4 | 5 | | | V-1 | SIRT3 | 1.85 |
| 5270 | 3 | 4 | 5 | | | V-1 | RXRB | 1.90 | 5366 | 3 | 4 | 5 | | | V-1 | SIRT5 | 1.97 |
| 5271 | 3 | 4 | 5 | | | V-1 | S100A13 | 1.91 | 5367 | 3 | 4 | 5 | | | V-1 | SKAP2 | 1.73 |
| 5272 | 3 | 4 | 5 | | | V-1 | S1PR2 | 1.90 | 5368 | 3 | 4 | 5 | | | V-1 | SKI | 1.71 |
| 5273 | 3 | 4 | 5 | | | V-1 | SAAL1 | 1.76 | 5369 | 3 | 4 | 5 | | | V-1 | SKIV2L2 | 1.74 |
| 5274 | 3 | 4 | 5 | | | V-1 | SAC3D1 | 1.86 | 5370 | 3 | 4 | 5 | | | V-1 | SLAIN2 | 1.51 |
| 5275 | 3 | 4 | 5 | | | V-1 | SACM1L | 1.79 | 5371 | 3 | 4 | 5 | | | V-1 | SLBP | 1.52 |
| 5276 | 3 | 4 | 5 | | | V-1 | SAP130 | 1.69 | 5372 | 3 | 4 | 5 | | | V-1 | SLC10A7 | 1.88 |

Fig. 40 - 29

| | | | | | | | | | | | | | | | |
|---|---|---|---|---|---|---|---|---|---|---|---|---|---|---|---|
| 5373 | 3 | 4 | 5 | | | V-1 | SLC12A2 | 1.60 | 5469 | 3 | 4 | 5 | | V-1 | SNX20 | 1.97 |
| 5374 | 3 | 4 | 5 | | | V-1 | SLC15A3 | 1.73 | 5470 | 3 | 4 | 5 | | V-1 | SNX22 | 1.98 |
| 5375 | 3 | 4 | 5 | | | V-1 | SLC19A1 | 1.99 | 5471 | 3 | 4 | 5 | | V-1 | SNX24 | 1.75 |
| 5376 | 3 | 4 | 5 | | | V-1 | SLC19A2 | 1.93 | 5472 | 3 | 4 | 5 | | V-1 | SNX25 | 1.71 |
| 5377 | 3 | 4 | 5 | | | V-1 | SLC1A5 | 1.82 | 5473 | 3 | 4 | 5 | | V-1 | SNX30 | 1.78 |
| 5378 | 3 | 4 | 5 | | | V-1 | SLC22A1 | 1.89 | 5474 | 3 | 4 | 5 | | V-1 | SNX5 | 1.87 |
| 5379 | 3 | 4 | 5 | | | V-1 | SLC22A16 | 1.85 | 5475 | 3 | 4 | 5 | | V-1 | SNX6 | 1.84 |
| 5380 | 3 | 4 | 5 | | | V-1 | SLC24A6 | 1.93 | 5476 | 3 | 4 | 5 | | V-1 | SNX9 | 1.72 |
| 5381 | 3 | 4 | 5 | | | V-1 | SLC25A11 | 1.50 | 5477 | 3 | 4 | 5 | | V-1 | SOAT1 | 1.92 |
| 5382 | 3 | 4 | 5 | | | V-1 | SLC25A16 | 1.83 | 5478 | 3 | 4 | 5 | | V-1 | SOCS4 | 1.96 |
| 5383 | 3 | 4 | 5 | | | V-1 | SLC25A17 | 1.73 | 5479 | 3 | 4 | 5 | | V-1 | SOCS6 | 1.81 |
| 5384 | 3 | 4 | 5 | | | V-1 | SLC25A19 | 1.70 | 5480 | 3 | 4 | 5 | | V-1 | SOCS7 | 1.79 |
| 5385 | 3 | 4 | 5 | | | V-1 | SLC25A23 | 1.70 | 5481 | 3 | 4 | 5 | | V-1 | SOD2 | 1.56 |
| 5386 | 3 | 4 | 5 | | | V-1 | SLC25A24 | 1.62 | 5482 | 3 | 4 | 5 | | V-1 | SOS2 | 1.76 |
| 5387 | 3 | 4 | 5 | | | V-1 | SLC25A35 | 1.70 | 5483 | 3 | 4 | 5 | | V-1 | SOWAHC | 1.82 |
| 5388 | 3 | 4 | 5 | | | V-1 | SLC25A36 | 1.58 | 5484 | 3 | 4 | 5 | | V-1 | SOWAHD | 1.95 |
| 5389 | 3 | 4 | 5 | | | V-1 | SLC25A46 | 1.57 | 5485 | 3 | 4 | 5 | | V-1 | SOX12 | 1.57 |
| 5390 | 3 | 4 | 5 | | | V-1 | SLC26A2 | 1.62 | 5486 | 3 | 4 | 5 | | V-1 | SP2 | 1.84 |
| 5391 | 3 | 4 | 5 | | | V-1 | SLC27A4 | 1.67 | 5487 | 3 | 4 | 5 | | V-1 | SP3 | 1.93 |
| 5392 | 3 | 4 | 5 | | | V-1 | SLC29A2 | 1.91 | 5488 | 3 | 4 | 5 | | V-1 | SPAST | 1.86 |
| 5393 | 3 | 4 | 5 | | | V-1 | SLC2A3 | 1.62 | 5489 | 3 | 4 | 5 | | V-1 | SPATA13 | 1.96 |
| 5394 | 3 | 4 | 5 | | | V-1 | SLC31A1 | 1.84 | 5490 | 3 | 4 | 5 | | V-1 | SPATA2 | 1.66 |
| 5395 | 3 | 4 | 5 | | | V-1 | SLC35A1 | 1.90 | 5491 | 3 | 4 | 5 | | V-1 | SPATA5 | 1.54 |
| 5396 | 3 | 4 | 5 | | | V-1 | SLC35A3 | 1.54 | 5492 | 3 | 4 | 5 | | V-1 | SPATA6 | 1.82 |
| 5397 | 3 | 4 | 5 | | | V-1 | SLC35A4 | 1.55 | 5493 | 3 | 4 | 5 | | V-1 | SPATS2 | 1.57 |
| 5398 | 3 | 4 | 5 | | | V-1 | SLC35A5 | 1.81 | 5494 | 3 | 4 | 5 | | V-1 | SPCS2 | 1.77 |
| 5399 | 3 | 4 | 5 | | | V-1 | SLC35C1 | 1.91 | 5495 | 3 | 4 | 5 | | V-1 | SPG20 | 1.91 |
| 5400 | 3 | 4 | 5 | | | V-1 | SLC35C2 | 1.88 | 5496 | 3 | 4 | 5 | | V-1 | SPICE1 | 1.99 |
| 5401 | 3 | 4 | 5 | | | V-1 | SLC35D1 | 1.54 | 5497 | 3 | 4 | 5 | | V-1 | SPIN1 | 1.60 |
| 5402 | 3 | 4 | 5 | | | V-1 | SLC35E1 | 1.51 | 5498 | 3 | 4 | 5 | | V-1 | SPIN2B | 1.92 |
| 5403 | 3 | 4 | 5 | | | V-1 | SLC35E4 | 1.58 | 5499 | 3 | 4 | 5 | | V-1 | SPOP | 1.94 |
| 5404 | 3 | 4 | 5 | | | V-1 | SLC36A4 | 1.93 | 5500 | 3 | 4 | 5 | | V-1 | SPRED1 | 1.94 |
| 5405 | 3 | 4 | 5 | | | V-1 | SLC37A3 | 1.92 | 5501 | 3 | 4 | 5 | | V-1 | SPTSSA | 1.72 |
| 5406 | 3 | 4 | 5 | | | V-1 | SLC37A4 | 1.81 | 5502 | 3 | 4 | 5 | | V-1 | SQSTM1 | 1.86 |
| 5407 | 3 | 4 | 5 | | | V-1 | SLC39A10 | 1.98 | 5503 | 3 | 4 | 5 | | V-1 | SRCAP | 1.97 |
| 5408 | 3 | 4 | 5 | | | V-1 | SLC39A13 | 1.60 | 5504 | 3 | 4 | 5 | | V-1 | SRD5A1P1 | 1.91 |
| 5409 | 3 | 4 | 5 | | | V-1 | SLC39A6 | 1.68 | 5505 | 3 | 4 | 5 | | V-1 | SREBF2 | 1.55 |
| 5410 | 3 | 4 | 5 | | | V-1 | SLC39A7 | 1.81 | 5506 | 3 | 4 | 5 | | V-1 | SREK1IP1 | 1.51 |
| 5411 | 3 | 4 | 5 | | | V-1 | SLC43A2 | 1.77 | 5507 | 3 | 4 | 5 | | V-1 | SRP19 | 1.91 |
| 5412 | 3 | 4 | 5 | | | V-1 | SLC44A2 | 1.91 | 5508 | 3 | 4 | 5 | | V-1 | SRP54 | 1.74 |
| 5413 | 3 | 4 | 5 | | | V-1 | SLC45A4 | 1.52 | 5509 | 3 | 4 | 5 | | V-1 | SRP68 | 1.88 |
| 5414 | 3 | 4 | 5 | | | V-1 | SLC46A1 | 1.97 | 5510 | 3 | 4 | 5 | | V-1 | SRPK2 | 1.77 |
| 5415 | 3 | 4 | 5 | | | V-1 | SLC46A3 | 1.94 | 5511 | 3 | 4 | 5 | | V-1 | SRSF10 | 1.96 |
| 5416 | 3 | 4 | 5 | | | V-1 | SLC4A1AP | 1.64 | 5512 | 3 | 4 | 5 | | V-1 | SRSF2 | 1.97 |
| 5417 | 3 | 4 | 5 | | | V-1 | SLC4A7 | 1.70 | 5513 | 3 | 4 | 5 | | V-1 | SRSF4 | 1.91 |
| 5418 | 3 | 4 | 5 | | | V-1 | SLC50A1 | 1.58 | 5514 | 3 | 4 | 5 | | V-1 | SRSF8 | 1.61 |
| 5419 | 3 | 4 | 5 | | | V-1 | SLC7A5P2 | 1.52 | 5515 | 3 | 4 | 5 | | V-1 | SS18L2 | 1.77 |
| 5420 | 3 | 4 | 5 | | | V-1 | SLC9A6 | 1.53 | 5516 | 3 | 4 | 5 | | V-1 | SSB | 1.70 |
| 5421 | 3 | 4 | 5 | | | V-1 | SLFN13 | 1.98 | 5517 | 3 | 4 | 5 | | V-1 | SSBP3 | 1.81 |
| 5422 | 3 | 4 | 5 | | | V-1 | SLK | 1.90 | 5518 | 3 | 4 | 5 | | V-1 | SSBP4 | 1.70 |
| 5423 | 3 | 4 | 5 | | | V-1 | SLMAP | 1.74 | 5519 | 3 | 4 | 5 | | V-1 | SSFA2 | 1.96 |
| 5424 | 3 | 4 | 5 | | | V-1 | SLU7 | 1.99 | 5520 | 3 | 4 | 5 | | V-1 | SSR1 | 1.77 |
| 5425 | 3 | 4 | 5 | | | V-1 | SMAD2 | 1.67 | 5521 | 3 | 4 | 5 | | V-1 | ST8SIA4 | 1.84 |
| 5426 | 3 | 4 | 5 | | | V-1 | SMAD3 | 1.84 | 5522 | 3 | 4 | 5 | | V-1 | STAG1 | 1.82 |
| 5427 | 3 | 4 | 5 | | | V-1 | SMAD4 | 1.77 | 5523 | 3 | 4 | 5 | | V-1 | STAG2 | 1.95 |
| 5428 | 3 | 4 | 5 | | | V-1 | SMAP1 | 1.78 | 5524 | 3 | 4 | 5 | | V-1 | STAM | 1.77 |
| 5429 | 3 | 4 | 5 | | | V-1 | SMARCA2 | 1.71 | 5525 | 3 | 4 | 5 | | V-1 | STAT4 | 1.56 |
| 5430 | 3 | 4 | 5 | | | V-1 | SMARCA4 | 1.94 | 5526 | 3 | 4 | 5 | | V-1 | STAT5B | 1.70 |
| 5431 | 3 | 4 | 5 | | | V-1 | SMARCA5 | 1.67 | 5527 | 3 | 4 | 5 | | V-1 | STAU1 | 1.78 |
| 5432 | 3 | 4 | 5 | | | V-1 | SMARCAL1 | 1.72 | 5528 | 3 | 4 | 5 | | V-1 | STAU2 | 1.52 |
| 5433 | 3 | 4 | 5 | | | V-1 | SMARCC1 | 1.69 | 5529 | 3 | 4 | 5 | | V-1 | STEAP3 | 1.89 |
| 5434 | 3 | 4 | 5 | | | V-1 | SMARCD1 | 1.68 | 5530 | 3 | 4 | 5 | | V-1 | STEAP4 | 1.81 |
| 5435 | 3 | 4 | 5 | | | V-1 | SMARCD2 | 1.93 | 5531 | 3 | 4 | 5 | | V-1 | STIM1 | 1.74 |
| 5436 | 3 | 4 | 5 | | | V-1 | SMC3 | 1.93 | 5532 | 3 | 4 | 5 | | V-1 | STIP1 | 1.66 |
| 5437 | 3 | 4 | 5 | | | V-1 | SMC5 | 1.77 | 5533 | 3 | 4 | 5 | | V-1 | STK10 | 1.70 |
| 5438 | 3 | 4 | 5 | | | V-1 | SMCR7 | 1.68 | 5534 | 3 | 4 | 5 | | V-1 | STK25 | 1.88 |
| 5439 | 3 | 4 | 5 | | | V-1 | SMCR8 | 1.85 | 5535 | 3 | 4 | 5 | | V-1 | STK35 | 1.83 |
| 5440 | 3 | 4 | 5 | | | V-1 | SMEK1 | 1.95 | 5536 | 3 | 4 | 5 | | V-1 | STK4 | 1.57 |
| 5441 | 3 | 4 | 5 | | | V-1 | SMG6 | 1.77 | 5537 | 3 | 4 | 5 | | V-1 | STRN | 1.77 |
| 5442 | 3 | 4 | 5 | | | V-1 | SMG7 | 1.70 | 5538 | 3 | 4 | 5 | | V-1 | STRN4 | 1.66 |
| 5443 | 3 | 4 | 5 | | | V-1 | SMG8 | 1.75 | 5539 | 3 | 4 | 5 | | V-1 | STX12 | 1.88 |
| 5444 | 3 | 4 | 5 | | | V-1 | SMN2 | 1.94 | 5540 | 3 | 4 | 5 | | V-1 | STX1A | 1.93 |
| 5445 | 3 | 4 | 5 | | | V-1 | SMNDC1 | 1.76 | 5541 | 3 | 4 | 5 | | V-1 | STX6 | 1.92 |
| 5446 | 3 | 4 | 5 | | | V-1 | SMPD1 | 1.79 | 5542 | 3 | 4 | 5 | | V-1 | STXBP2 | 1.64 |
| 5447 | 3 | 4 | 5 | | | V-1 | SMPD2 | 1.71 | 5543 | 3 | 4 | 5 | | V-1 | STYXL1 | 1.79 |
| 5448 | 3 | 4 | 5 | | | V-1 | SMPDL3B | 1.57 | 5544 | 3 | 4 | 5 | | V-1 | SUCLA2 | 1.75 |
| 5449 | 3 | 4 | 5 | | | V-1 | SMS | 1.67 | 5545 | 3 | 4 | 5 | | V-1 | SUFU | 1.97 |
| 5450 | 3 | 4 | 5 | | | V-1 | SMU1 | 1.89 | 5546 | 3 | 4 | 5 | | V-1 | SUGP1 | 1.89 |
| 5451 | 3 | 4 | 5 | | | V-1 | SMYD4 | 1.57 | 5547 | 3 | 4 | 5 | | V-1 | SULT1B1 | 1.50 |
| 5452 | 3 | 4 | 5 | | | V-1 | SNAP29 | 1.50 | 5548 | 3 | 4 | 5 | | V-1 | SUMO2 | 1.52 |
| 5453 | 3 | 4 | 5 | | | V-1 | SND1-IT1 | 1.62 | 5549 | 3 | 4 | 5 | | V-1 | SUN2 | 1.78 |
| 5454 | 3 | 4 | 5 | | | V-1 | SNIP1 | 1.92 | 5550 | 3 | 4 | 5 | | V-1 | SUPT16H | 1.84 |
| 5455 | 3 | 4 | 5 | | | V-1 | SNRK | 1.87 | 5551 | 3 | 4 | 5 | | V-1 | SUPT3H | 1.52 |
| 5456 | 3 | 4 | 5 | | | V-1 | SNRNP48 | 1.75 | 5552 | 3 | 4 | 5 | | V-1 | SUV420H1 | 1.73 |
| 5457 | 3 | 4 | 5 | | | V-1 | SNRPA1 | 1.75 | 5553 | 3 | 4 | 5 | | V-1 | SUV420H2 | 1.69 |
| 5458 | 3 | 4 | 5 | | | V-1 | SNRPD1 | 1.55 | 5554 | 3 | 4 | 5 | | V-1 | SUZ12 | 1.75 |
| 5459 | 3 | 4 | 5 | | | V-1 | SNTB1 | 1.74 | 5555 | 3 | 4 | 5 | | V-1 | SWT1 | 2.00 |
| 5460 | 3 | 4 | 5 | | | V-1 | SNTB2 | 1.98 | 5556 | 3 | 4 | 5 | | V-1 | SYF2 | 1.51 |
| 5461 | 3 | 4 | 5 | | | V-1 | SNW1 | 1.84 | 5557 | 3 | 4 | 5 | | V-1 | SYK | 1.66 |
| 5462 | 3 | 4 | 5 | | | V-1 | SNX1 | 2.00 | 5558 | 3 | 4 | 5 | | V-1 | SYNCRIP | 1.93 |
| 5463 | 3 | 4 | 5 | | | V-1 | SNX10 | 1.96 | 5559 | 3 | 4 | 5 | | V-1 | SYNJ2 | 1.96 |
| 5464 | 3 | 4 | 5 | | | V-1 | SNX11 | 1.56 | 5560 | 3 | 4 | 5 | | V-1 | SYNJ2BP | 1.80 |
| 5465 | 3 | 4 | 5 | | | V-1 | SNX13 | 1.83 | 5561 | 3 | 4 | 5 | | V-1 | SYPL1 | 1.90 |
| 5466 | 3 | 4 | 5 | | | V-1 | SNX14 | 1.88 | 5562 | 3 | 4 | 5 | | V-1 | SYTL4 | 1.72 |
| 5467 | 3 | 4 | 5 | | | V-1 | SNX16 | 1.53 | 5563 | 3 | 4 | 5 | | V-1 | TAB2 | 1.61 |
| 5468 | 3 | 4 | 5 | | | V-1 | SNX2 | 1.61 | 5564 | 3 | 4 | 5 | | V-1 | TACC3 | 1.66 |

Fig. 40 - 30

| | | | | | | | | | | | | | |
|---|---|---|---|---|---|---|---|---|---|---|---|---|---|
| 5565 | 3 | 4 | 5 | | V-1 | TADA1 | 1.79 | 5661 | 3 | 4 | 5 | V-1 | TMEM127 | 1.68 |
| 5566 | 3 | 4 | 5 | | V-1 | TAF11 | 1.90 | 5662 | 3 | 4 | 5 | V-1 | TMEM129 | 1.51 |
| 5567 | 3 | 4 | 5 | | V-1 | TAF1D | 1.84 | 5663 | 3 | 4 | 5 | V-1 | TMEM135 | 1.76 |
| 5568 | 3 | 4 | 5 | | V-1 | TAF1L | 1.74 | 5664 | 3 | 4 | 5 | V-1 | TMEM138 | 1.68 |
| 5569 | 3 | 4 | 5 | | V-1 | TAF2 | 1.88 | 5665 | 3 | 4 | 5 | V-1 | TMEM150A | 1.79 |
| 5570 | 3 | 4 | 5 | | V-1 | TAF4 | 1.97 | 5666 | 3 | 4 | 5 | V-1 | TMEM154 | 1.76 |
| 5571 | 3 | 4 | 5 | | V-1 | TAF7 | 1.78 | 5667 | 3 | 4 | 5 | V-1 | TMEM156 | 1.75 |
| 5572 | 3 | 4 | 5 | | V-1 | TANK | 1.63 | 5668 | 3 | 4 | 5 | V-1 | TMEM159 | 1.76 |
| 5573 | 3 | 4 | 5 | | V-1 | TAOK3 | 1.76 | 5669 | 3 | 4 | 5 | V-1 | TMEM161A | 1.96 |
| 5574 | 3 | 4 | 5 | | V-1 | TAPT1 | 1.68 | 5670 | 3 | 4 | 5 | V-1 | TMEM167A | 1.70 |
| 5575 | 3 | 4 | 5 | | V-1 | TARBP2 | 1.67 | 5671 | 3 | 4 | 5 | V-1 | TMEM167B | 1.85 |
| 5576 | 3 | 4 | 5 | | V-1 | TARS | 1.64 | 5672 | 3 | 4 | 5 | V-1 | TMEM169 | 1.96 |
| 5577 | 3 | 4 | 5 | | V-1 | TARS2 | 1.83 | 5673 | 3 | 4 | 5 | V-1 | TMEM175 | 1.93 |
| 5578 | 3 | 4 | 5 | | V-1 | TATDN3 | 1.72 | 5674 | 3 | 4 | 5 | V-1 | TMEM184B | 1.75 |
| 5579 | 3 | 4 | 5 | | V-1 | TAX1BP1 | 1.51 | 5675 | 3 | 4 | 5 | V-1 | TMEM185A | 1.78 |
| 5580 | 3 | 4 | 5 | | V-1 | TBC1D10C | 1.76 | 5676 | 3 | 4 | 5 | V-1 | TMEM186 | 1.85 |
| 5581 | 3 | 4 | 5 | | V-1 | TBC1D13 | 1.55 | 5677 | 3 | 4 | 5 | V-1 | TMEM19 | 1.50 |
| 5582 | 3 | 4 | 5 | | V-1 | TBC1D15 | 1.53 | 5678 | 3 | 4 | 5 | V-1 | TMEM192 | 1.60 |
| 5583 | 3 | 4 | 5 | | V-1 | TBC1D17 | 1.67 | 5679 | 3 | 4 | 5 | V-1 | TMEM194B | 1.92 |
| 5584 | 3 | 4 | 5 | | V-1 | TBC1D20 | 1.87 | 5680 | 3 | 4 | 5 | V-1 | TMEM199 | 1.71 |
| 5585 | 3 | 4 | 5 | | V-1 | TBC1D23 | 1.96 | 5681 | 3 | 4 | 5 | V-1 | TMEM2 | 1.59 |
| 5586 | 3 | 4 | 5 | | V-1 | TBCC | 1.86 | 5682 | 3 | 4 | 5 | V-1 | TMEM209 | 1.73 |
| 5587 | 3 | 4 | 5 | | V-1 | TBCEL | 1.66 | 5683 | 3 | 4 | 5 | V-1 | TMEM214 | 1.94 |
| 5588 | 3 | 4 | 5 | | V-1 | TBL2 | 1.62 | 5684 | 3 | 4 | 5 | V-1 | TMEM30A | 1.90 |
| 5589 | 3 | 4 | 5 | | V-1 | TBL3 | 1.82 | 5685 | 3 | 4 | 5 | V-1 | TMEM33 | 1.90 |
| 5590 | 3 | 4 | 5 | | V-1 | TBPL1 | 1.54 | 5686 | 3 | 4 | 5 | V-1 | TMEM39A | 1.61 |
| 5591 | 3 | 4 | 5 | | V-1 | TBRG4 | 1.76 | 5687 | 3 | 4 | 5 | V-1 | TMEM39B | 1.82 |
| 5592 | 3 | 4 | 5 | | V-1 | TCEAL1 | 1.55 | 5688 | 3 | 4 | 5 | V-1 | TMEM40 | 1.71 |
| 5593 | 3 | 4 | 5 | | V-1 | TCEB3 | 1.56 | 5689 | 3 | 4 | 5 | V-1 | TMEM42 | 1.93 |
| 5594 | 3 | 4 | 5 | | V-1 | TCF20 | 1.70 | 5690 | 3 | 4 | 5 | V-1 | TMEM48 | 1.55 |
| 5595 | 3 | 4 | 5 | | V-1 | TCF25 | 1.86 | 5691 | 3 | 4 | 5 | V-1 | TMEM53 | 1.69 |
| 5596 | 3 | 4 | 5 | | V-1 | TCF3 | 1.83 | 5692 | 3 | 4 | 5 | V-1 | TMEM55B | 1.89 |
| 5597 | 3 | 4 | 5 | | V-1 | TCP11L2 | 1.81 | 5693 | 3 | 4 | 5 | V-1 | TMEM57 | 1.65 |
| 5598 | 3 | 4 | 5 | | V-1 | TCTN1 | 1.68 | 5694 | 3 | 4 | 5 | V-1 | TMEM66 | 1.75 |
| 5599 | 3 | 4 | 5 | | V-1 | TDP2 | 1.50 | 5695 | 3 | 4 | 5 | V-1 | TMEM68 | 1.79 |
| 5600 | 3 | 4 | 5 | | V-1 | TDRKH | 1.55 | 5696 | 3 | 4 | 5 | V-1 | TMEM69 | 1.89 |
| 5601 | 3 | 4 | 5 | | V-1 | TECPR2 | 1.58 | 5697 | 3 | 4 | 5 | V-1 | TMEM71 | 1.74 |
| 5602 | 3 | 4 | 5 | | V-1 | TERF2 | 1.66 | 5698 | 3 | 4 | 5 | V-1 | TMEM86A | 1.60 |
| 5603 | 3 | 4 | 5 | | V-1 | TESK1 | 1.77 | 5699 | 3 | 4 | 5 | V-1 | TMEM91 | 1.91 |
| 5604 | 3 | 4 | 5 | | V-1 | TESK2 | 1.60 | 5700 | 3 | 4 | 5 | V-1 | TMLHE | 1.84 |
| 5605 | 3 | 4 | 5 | | V-1 | TET2 | 1.94 | 5701 | 3 | 4 | 5 | V-1 | TMOD3 | 1.78 |
| 5606 | 3 | 4 | 5 | | V-1 | TEX10 | 1.90 | 5702 | 3 | 4 | 5 | V-1 | TMPO | 1.51 |
| 5607 | 3 | 4 | 5 | | V-1 | TEX261 | 1.72 | 5703 | 3 | 4 | 5 | V-1 | TMTC3 | 1.81 |
| 5608 | 3 | 4 | 5 | | V-1 | TFAM | 1.57 | 5704 | 3 | 4 | 5 | V-1 | TMX1 | 1.70 |
| 5609 | 3 | 4 | 5 | | V-1 | TFAP2E | 1.80 | 5705 | 3 | 4 | 5 | V-1 | TNFAIP1 | 1.83 |
| 5610 | 3 | 4 | 5 | | V-1 | TFCP2 | 1.88 | 5706 | 3 | 4 | 5 | V-1 | TNFAIP3 | 1.92 |
| 5611 | 3 | 4 | 5 | | V-1 | TFE3 | 1.90 | 5707 | 3 | 4 | 5 | V-1 | TNFAIP8L1 | 1.59 |
| 5612 | 3 | 4 | 5 | | V-1 | TFEB | 1.52 | 5708 | 3 | 4 | 5 | V-1 | TNFRSF10A | 1.61 |
| 5613 | 3 | 4 | 5 | | V-1 | TFG | 1.97 | 5709 | 3 | 4 | 5 | V-1 | TNFRSF1A | 1.52 |
| 5614 | 3 | 4 | 5 | | V-1 | TFIP11 | 1.90 | 5710 | 3 | 4 | 5 | V-1 | TNFRSF6B | 1.74 |
| 5615 | 3 | 4 | 5 | | V-1 | TFPT | 1.50 | 5711 | 3 | 4 | 5 | V-1 | TNFSF14 | 1.92 |
| 5616 | 3 | 4 | 5 | | V-1 | TGDS | 1.55 | 5712 | 3 | 4 | 5 | V-1 | TNKS1BP1 | 1.87 |
| 5617 | 3 | 4 | 5 | | V-1 | TGFB1I1 | 1.72 | 5713 | 3 | 4 | 5 | V-1 | TNPO1 | 1.77 |
| 5618 | 3 | 4 | 5 | | V-1 | TGFBR1 | 1.88 | 5714 | 3 | 4 | 5 | V-1 | TNPO3 | 1.74 |
| 5619 | 3 | 4 | 5 | | V-1 | TGFBR2 | 1.71 | 5715 | 3 | 4 | 5 | V-1 | TOE1 | 1.59 |
| 5620 | 3 | 4 | 5 | | V-1 | TGIF2 | 1.59 | 5716 | 3 | 4 | 5 | V-1 | TOLLIP | 1.54 |
| 5621 | 3 | 4 | 5 | | V-1 | TGOLN2 | 1.94 | 5717 | 3 | 4 | 5 | V-1 | TOM1 | 1.60 |
| 5622 | 3 | 4 | 5 | | V-1 | THAP2 | 1.80 | 5718 | 3 | 4 | 5 | V-1 | TOP2A | 1.56 |
| 5623 | 3 | 4 | 5 | | V-1 | THAP9 | 1.65 | 5719 | 3 | 4 | 5 | V-1 | TOP2B | 1.92 |
| 5624 | 3 | 4 | 5 | | V-1 | THEM4 | 1.59 | 5720 | 3 | 4 | 5 | V-1 | TOR1AIP1 | 1.59 |
| 5625 | 3 | 4 | 5 | | V-1 | THG1L | 1.79 | 5721 | 3 | 4 | 5 | V-1 | TOR3A | 1.60 |
| 5626 | 3 | 4 | 5 | | V-1 | THOP1 | 1.70 | 5722 | 3 | 4 | 5 | V-1 | TOX4 | 1.62 |
| 5627 | 3 | 4 | 5 | | V-1 | THRAP3 | 1.70 | 5723 | 3 | 4 | 5 | V-1 | TP53BP2 | 1.55 |
| 5628 | 3 | 4 | 5 | | V-1 | THSD1P1 | 1.91 | 5724 | 3 | 4 | 5 | V-1 | TPD52L2 | 1.73 |
| 5629 | 3 | 4 | 5 | | V-1 | THTPA | 1.51 | 5725 | 3 | 4 | 5 | V-1 | TPK1 | 1.92 |
| 5630 | 3 | 4 | 5 | | V-1 | THUMPD1 | 1.71 | 5726 | 3 | 4 | 5 | V-1 | TPPP3 | 1.59 |
| 5631 | 3 | 4 | 5 | | V-1 | THUMPD2 | 1.97 | 5727 | 3 | 4 | 5 | V-1 | TPRG1L | 1.69 |
| 5632 | 3 | 4 | 5 | | V-1 | THUMPD3 | 1.66 | 5728 | 3 | 4 | 5 | V-1 | TRA2B | 1.78 |
| 5633 | 3 | 4 | 5 | | V-1 | THYN1 | 1.65 | 5729 | 3 | 4 | 5 | V-1 | TRADD | 1.56 |
| 5634 | 3 | 4 | 5 | | V-1 | TICAM1 | 1.90 | 5730 | 3 | 4 | 5 | V-1 | TRAF2 | 1.63 |
| 5635 | 3 | 4 | 5 | | V-1 | TIGD3 | 1.63 | 5731 | 3 | 4 | 5 | V-1 | TRAF3 | 1.77 |
| 5636 | 3 | 4 | 5 | | V-1 | TIMM44 | 1.66 | 5732 | 3 | 4 | 5 | V-1 | TRAF3IP2 | 1.94 |
| 5637 | 3 | 4 | 5 | | V-1 | TIMM8A | 1.68 | 5733 | 3 | 4 | 5 | V-1 | TRAF3IP3 | 1.85 |
| 5638 | 3 | 4 | 5 | | V-1 | TIMP2 | 1.61 | 5734 | 3 | 4 | 5 | V-1 | TRAF4 | 1.78 |
| 5639 | 3 | 4 | 5 | | V-1 | TIPARP | 1.83 | 5735 | 3 | 4 | 5 | V-1 | TRAP1 | 1.84 |
| 5640 | 3 | 4 | 5 | | V-1 | TIRAP | 1.66 | 5736 | 3 | 4 | 5 | V-1 | TRAPPC10 | 1.63 |
| 5641 | 3 | 4 | 5 | | V-1 | TK1 | 1.85 | 5737 | 3 | 4 | 5 | V-1 | TRAPPC12 | 1.60 |
| 5642 | 3 | 4 | 5 | | V-1 | TLE2 | 1.84 | 5738 | 3 | 4 | 5 | V-1 | TRAPPC6B | 1.96 |
| 5643 | 3 | 4 | 5 | | V-1 | TLE3 | 1.54 | 5739 | 3 | 4 | 5 | V-1 | TRAPPC8 | 1.88 |
| 5644 | 3 | 4 | 5 | | V-1 | TLK1 | 1.68 | 5740 | 3 | 4 | 5 | V-1 | TRAPPC9 | 1.91 |
| 5645 | 3 | 4 | 5 | | V-1 | TLK2 | 1.99 | 5741 | 3 | 4 | 5 | V-1 | TRDMT1 | 1.60 |
| 5646 | 3 | 4 | 5 | | V-1 | TLR1 | 1.86 | 5742 | 3 | 4 | 5 | V-1 | TREM1 | 1.72 |
| 5647 | 3 | 4 | 5 | | V-1 | TLR8 | 2.00 | 5743 | 3 | 4 | 5 | V-1 | TREX2 | 1.71 |
| 5648 | 3 | 4 | 5 | | V-1 | TM9SF3 | 1.59 | 5744 | 3 | 4 | 5 | V-1 | TRIM11 | 1.91 |
| 5649 | 3 | 4 | 5 | | V-1 | TMC4 | 1.96 | 5745 | 3 | 4 | 5 | V-1 | TRIM13 | 1.73 |
| 5650 | 3 | 4 | 5 | | V-1 | TMCC3 | 1.60 | 5746 | 3 | 4 | 5 | V-1 | TRIM23 | 1.60 |
| 5651 | 3 | 4 | 5 | | V-1 | TMCO4 | 1.77 | 5747 | 3 | 4 | 5 | V-1 | TRIM24 | 1.76 |
| 5652 | 3 | 4 | 5 | | V-1 | TMCO7 | 1.50 | 5748 | 3 | 4 | 5 | V-1 | TRIM27 | 1.73 |
| 5653 | 3 | 4 | 5 | | V-1 | TMED4 | 1.62 | 5749 | 3 | 4 | 5 | V-1 | TRIM28 | 1.90 |
| 5654 | 3 | 4 | 5 | | V-1 | TMED5 | 1.68 | 5750 | 3 | 4 | 5 | V-1 | TRIM35 | 1.76 |
| 5655 | 3 | 4 | 5 | | V-1 | TMED7 | 1.55 | 5751 | 3 | 4 | 5 | V-1 | TRIM37 | 1.71 |
| 5656 | 3 | 4 | 5 | | V-1 | TMEM104 | 1.97 | 5752 | 3 | 4 | 5 | V-1 | TRIM39 | 1.56 |
| 5657 | 3 | 4 | 5 | | V-1 | TMEM115 | 1.62 | 5753 | 3 | 4 | 5 | V-1 | TRIM62 | 1.89 |
| 5658 | 3 | 4 | 5 | | V-1 | TMEM120B | 1.52 | 5754 | 3 | 4 | 5 | V-1 | TRIM65 | 1.69 |
| 5659 | 3 | 4 | 5 | | V-1 | TMEM126A | 1.66 | 5755 | 3 | 4 | 5 | V-1 | TRIM68 | 1.68 |
| 5660 | 3 | 4 | 5 | | V-1 | TMEM126B | 1.79 | 5756 | 3 | 4 | 5 | V-1 | TRIM69 | 1.77 |

Fig. 40 - 31

| | | | | | | | | | | | | | | |
|---|---|---|---|---|---|---|---|---|---|---|---|---|---|---|
| 5757 | 3 | 4 | 5 | | V-1 | TRIM8 | 1.85 | 5853 | 3 | 4 | 5 | V-1 | URB2 | 1.82 |
| 5758 | 3 | 4 | 5 | | V-1 | TRIOBP | 1.65 | 5854 | 3 | 4 | 5 | V-1 | URGCP | 1.63 |
| 5759 | 3 | 4 | 5 | | V-1 | TRIP11 | 1.97 | 5855 | 3 | 4 | 5 | V-1 | USO1 | 1.97 |
| 5760 | 3 | 4 | 5 | | V-1 | TRIP12 | 1.60 | 5856 | 3 | 4 | 5 | V-1 | USP1 | 1.63 |
| 5761 | 3 | 4 | 5 | | V-1 | TRIP4 | 1.65 | 5857 | 3 | 4 | 5 | V-1 | USP14 | 1.57 |
| 5762 | 3 | 4 | 5 | | V-1 | TRIT1 | 1.91 | 5858 | 3 | 4 | 5 | V-1 | USP16 | 1.99 |
| 5763 | 3 | 4 | 5 | | V-1 | TRMT11 | 1.51 | 5859 | 3 | 4 | 5 | V-1 | USP20 | 1.91 |
| 5764 | 3 | 4 | 5 | | V-1 | TRMT2B | 1.89 | 5860 | 3 | 4 | 5 | V-1 | USP21 | 1.90 |
| 5765 | 3 | 4 | 5 | | V-1 | TRMT6 | 1.75 | 5861 | 3 | 4 | 5 | V-1 | USP22 | 1.95 |
| 5766 | 3 | 4 | 5 | | V-1 | TRMT61A | 1.59 | 5862 | 3 | 4 | 5 | V-1 | USP27X | 1.94 |
| 5767 | 3 | 4 | 5 | | V-1 | TRMT61B | 1.82 | 5863 | 3 | 4 | 5 | V-1 | USP31 | 1.60 |
| 5768 | 3 | 4 | 5 | | V-1 | TRNAU1AP | 1.68 | 5864 | 3 | 4 | 5 | V-1 | USP37 | 1.72 |
| 5769 | 3 | 4 | 5 | | V-1 | TROVE2 | 1.67 | 5865 | 3 | 4 | 5 | V-1 | USP39 | 1.67 |
| 5770 | 3 | 4 | 5 | | V-1 | TRPM7 | 1.71 | 5866 | 3 | 4 | 5 | V-1 | USP45 | 1.56 |
| 5771 | 3 | 4 | 5 | | V-1 | TRPT1 | 1.88 | 5867 | 3 | 4 | 5 | V-1 | USP47 | 1.86 |
| 5772 | 3 | 4 | 5 | | V-1 | TRPV2 | 1.78 | 5868 | 3 | 4 | 5 | V-1 | USP48 | 1.92 |
| 5773 | 3 | 4 | 5 | | V-1 | TSC22D2 | 1.85 | 5869 | 3 | 4 | 5 | V-1 | USP5 | 1.56 |
| 5774 | 3 | 4 | 5 | | V-1 | TSEN2 | 1.97 | 5870 | 3 | 4 | 5 | V-1 | USP54 | 1.63 |
| 5775 | 3 | 4 | 5 | | V-1 | TSEN34 | 1.61 | 5871 | 3 | 4 | 5 | V-1 | UTP14C | 1.59 |
| 5776 | 3 | 4 | 5 | | V-1 | TSPAN17 | 1.72 | 5872 | 3 | 4 | 5 | V-1 | UTP15 | 1.91 |
| 5777 | 3 | 4 | 5 | | V-1 | TSPAN3 | 1.53 | 5873 | 3 | 4 | 5 | V-1 | UTP18 | 1.54 |
| 5778 | 3 | 4 | 5 | | V-1 | TSPYL1 | 1.54 | 5874 | 3 | 4 | 5 | V-1 | UTP20 | 1.63 |
| 5779 | 3 | 4 | 5 | | V-1 | TSPYL4 | 1.87 | 5875 | 3 | 4 | 5 | V-1 | UTP3 | 1.86 |
| 5780 | 3 | 4 | 5 | | V-1 | TSR1 | 1.91 | 5876 | 3 | 4 | 5 | V-1 | UXS1 | 1.64 |
| 5781 | 3 | 4 | 5 | | V-1 | TST | 1.52 | 5877 | 3 | 4 | 5 | V-1 | VAC14 | 1.93 |
| 5782 | 3 | 4 | 5 | | V-1 | TSTD2 | 1.81 | 5878 | 3 | 4 | 5 | V-1 | VAMP2 | 1.94 |
| 5783 | 3 | 4 | 5 | | V-1 | TTC21A | 1.87 | 5879 | 3 | 4 | 5 | V-1 | VAMP3 | 1.64 |
| 5784 | 3 | 4 | 5 | | V-1 | TTC3 | 1.64 | 5880 | 3 | 4 | 5 | V-1 | VAMP4 | 2.00 |
| 5785 | 3 | 4 | 5 | | V-1 | TTC32 | 1.57 | 5881 | 3 | 4 | 5 | V-1 | VAV3 | 1.88 |
| 5786 | 3 | 4 | 5 | | V-1 | TTC35 | 1.61 | 5882 | 3 | 4 | 5 | V-1 | VCP | 1.68 |
| 5787 | 3 | 4 | 5 | | V-1 | TTC37 | 1.74 | 5883 | 3 | 4 | 5 | V-1 | VDAC1 | 1.75 |
| 5788 | 3 | 4 | 5 | | V-1 | TTC39B | 1.80 | 5884 | 3 | 4 | 5 | V-1 | VDAC2 | 1.60 |
| 5789 | 3 | 4 | 5 | | V-1 | TTC39C | 1.71 | 5885 | 3 | 4 | 5 | V-1 | VDAC3 | 1.50 |
| 5790 | 3 | 4 | 5 | | V-1 | TTI1 | 1.80 | 5886 | 3 | 4 | 5 | V-1 | VENTXP7 | 1.69 |
| 5791 | 3 | 4 | 5 | | V-1 | TTL | 1.90 | 5887 | 3 | 4 | 5 | V-1 | VEZF1 | 1.88 |
| 5792 | 3 | 4 | 5 | | V-1 | TTLL1 | 1.59 | 5888 | 3 | 4 | 5 | V-1 | VIM | 1.76 |
| 5793 | 3 | 4 | 5 | | V-1 | TTLL12 | 1.72 | 5889 | 3 | 4 | 5 | V-1 | VNN2 | 1.76 |
| 5794 | 3 | 4 | 5 | | V-1 | TTLL5 | 1.91 | 5890 | 3 | 4 | 5 | V-1 | VPS18 | 1.61 |
| 5795 | 3 | 4 | 5 | | V-1 | TTPAL | 1.61 | 5891 | 3 | 4 | 5 | V-1 | VPS26A | 1.93 |
| 5796 | 3 | 4 | 5 | | V-1 | TUBD1 | 1.94 | 5892 | 3 | 4 | 5 | V-1 | VPS33B | 1.85 |
| 5797 | 3 | 4 | 5 | | V-1 | TUBGCP2 | 1.50 | 5893 | 3 | 4 | 5 | V-1 | VPS35 | 1.73 |
| 5798 | 3 | 4 | 5 | | V-1 | TUBGCP3 | 1.83 | 5894 | 3 | 4 | 5 | V-1 | VPS36 | 1.78 |
| 5799 | 3 | 4 | 5 | | V-1 | TUBGCP5 | 1.65 | 5895 | 3 | 4 | 5 | V-1 | VPS37C | 1.50 |
| 5800 | 3 | 4 | 5 | | V-1 | TWF1 | 1.61 | 5896 | 3 | 4 | 5 | V-1 | VPS4B | 1.52 |
| 5801 | 3 | 4 | 5 | | V-1 | TXK | 1.50 | 5897 | 3 | 4 | 5 | V-1 | VTA1 | 1.93 |
| 5802 | 3 | 4 | 5 | | V-1 | TXLNA | 2.00 | 5898 | 3 | 4 | 5 | V-1 | VWA5A | 1.94 |
| 5803 | 3 | 4 | 5 | | V-1 | TXNDC11 | 1.64 | 5899 | 3 | 4 | 5 | V-1 | WAC | 1.81 |
| 5804 | 3 | 4 | 5 | | V-1 | TXNDC16 | 1.93 | 5900 | 3 | 4 | 5 | V-1 | WAPAL | 1.58 |
| 5805 | 3 | 4 | 5 | | V-1 | TXNIP | 1.94 | 5901 | 3 | 4 | 5 | V-1 | WAS | 1.92 |
| 5806 | 3 | 4 | 5 | | V-1 | TXNL4B | 1.77 | 5902 | 3 | 4 | 5 | V-1 | WASF2 | 1.54 |
| 5807 | 3 | 4 | 5 | | V-1 | TYW1 | 1.52 | 5903 | 3 | 4 | 5 | V-1 | WASH3P | 1.70 |
| 5808 | 3 | 4 | 5 | | V-1 | U2AF1L4 | 1.80 | 5904 | 3 | 4 | 5 | V-1 | WBP11 | 1.55 |
| 5809 | 3 | 4 | 5 | | V-1 | U2AF2 | 1.80 | 5905 | 3 | 4 | 5 | V-1 | WBP2 | 1.62 |
| 5810 | 3 | 4 | 5 | | V-1 | UAP1 | 1.53 | 5906 | 3 | 4 | 5 | V-1 | WBP5 | 1.76 |
| 5811 | 3 | 4 | 5 | | V-1 | UBA5 | 1.76 | 5907 | 3 | 4 | 5 | V-1 | WDR18 | 1.64 |
| 5812 | 3 | 4 | 5 | | V-1 | UBAC1 | 1.75 | 5908 | 3 | 4 | 5 | V-1 | WDR24 | 1.97 |
| 5813 | 3 | 4 | 5 | | V-1 | UBAP2L | 1.73 | 5909 | 3 | 4 | 5 | V-1 | WDR25 | 1.69 |
| 5814 | 3 | 4 | 5 | | V-1 | UBASH3B | 1.73 | 5910 | 3 | 4 | 5 | V-1 | WDR3 | 1.64 |
| 5815 | 3 | 4 | 5 | | V-1 | UBC | 1.63 | 5911 | 3 | 4 | 5 | V-1 | WDR36 | 1.76 |
| 5816 | 3 | 4 | 5 | | V-1 | UBE2A | 1.63 | 5912 | 3 | 4 | 5 | V-1 | WDR4 | 1.92 |
| 5817 | 3 | 4 | 5 | | V-1 | UBE2B | 1.69 | 5913 | 3 | 4 | 5 | V-1 | WDR45L | 1.79 |
| 5818 | 3 | 4 | 5 | | V-1 | UBE2C | 1.72 | 5914 | 3 | 4 | 5 | V-1 | WDR46 | 1.71 |
| 5819 | 3 | 4 | 5 | | V-1 | UBE2D3 | 1.55 | 5915 | 3 | 4 | 5 | V-1 | WDR47 | 1.97 |
| 5820 | 3 | 4 | 5 | | V-1 | UBE2G2 | 1.80 | 5916 | 3 | 4 | 5 | V-1 | WDR48 | 1.95 |
| 5821 | 3 | 4 | 5 | | V-1 | UBE2H | 1.76 | 5917 | 3 | 4 | 5 | V-1 | WDR52 | 1.60 |
| 5822 | 3 | 4 | 5 | | V-1 | UBE2J1 | 1.99 | 5918 | 3 | 4 | 5 | V-1 | WDR55 | 1.77 |
| 5823 | 3 | 4 | 5 | | V-1 | UBE2J2 | 1.54 | 5919 | 3 | 4 | 5 | V-1 | WDR74 | 1.58 |
| 5824 | 3 | 4 | 5 | | V-1 | UBE2K | 1.93 | 5920 | 3 | 4 | 5 | V-1 | WDR92 | 1.66 |
| 5825 | 3 | 4 | 5 | | V-1 | UBE2Q1 | 1.53 | 5921 | 3 | 4 | 5 | V-1 | WHAMMP3 | 1.85 |
| 5826 | 3 | 4 | 5 | | V-1 | UBE2S | 1.72 | 5922 | 3 | 4 | 5 | V-1 | WIPI1 | 1.81 |
| 5827 | 3 | 4 | 5 | | V-1 | UBE2W | 1.81 | 5923 | 3 | 4 | 5 | V-1 | WIPI2 | 1.93 |
| 5828 | 3 | 4 | 5 | | V-1 | UBE2Z | 1.57 | 5924 | 3 | 4 | 5 | V-1 | WNK1 | 1.53 |
| 5829 | 3 | 4 | 5 | | V-1 | UBE3A | 1.86 | 5925 | 3 | 4 | 5 | V-1 | WNT10B | 1.63 |
| 5830 | 3 | 4 | 5 | | V-1 | UBE3C | 1.67 | 5926 | 3 | 4 | 5 | V-1 | WRNIP1 | 1.52 |
| 5831 | 3 | 4 | 5 | | V-1 | UBE4B | 1.91 | 5927 | 3 | 4 | 5 | V-1 | XKR8 | 1.96 |
| 5832 | 3 | 4 | 5 | | V-1 | UBFD1 | 1.81 | 5928 | 3 | 4 | 5 | V-1 | XPA | 1.51 |
| 5833 | 3 | 4 | 5 | | V-1 | UBLCP1 | 1.69 | 5929 | 3 | 4 | 5 | V-1 | XPO6 | 1.51 |
| 5834 | 3 | 4 | 5 | | V-1 | UBOX5 | 1.56 | 5930 | 3 | 4 | 5 | V-1 | XPO7 | 1.68 |
| 5835 | 3 | 4 | 5 | | V-1 | UBQLN1 | 1.99 | 5931 | 3 | 4 | 5 | V-1 | XPOT | 1.51 |
| 5836 | 3 | 4 | 5 | | V-1 | UBR7 | 1.58 | 5932 | 3 | 4 | 5 | V-1 | XPR1 | 1.86 |
| 5837 | 3 | 4 | 5 | | V-1 | UBTD2 | 1.66 | 5933 | 3 | 4 | 5 | V-1 | XRCC1 | 1.77 |
| 5838 | 3 | 4 | 5 | | V-1 | UBXN2B | 1.87 | 5934 | 3 | 4 | 5 | V-1 | XRCC4 | 1.52 |
| 5839 | 3 | 4 | 5 | | V-1 | UBXN7 | 1.61 | 5935 | 3 | 4 | 5 | V-1 | XRCC5 | 1.93 |
| 5840 | 3 | 4 | 5 | | V-1 | UCKL1-AS1 | 1.71 | 5936 | 3 | 4 | 5 | V-1 | XXYLT1 | 1.67 |
| 5841 | 3 | 4 | 5 | | V-1 | UEVLD | 1.66 | 5937 | 3 | 4 | 5 | V-1 | XYLT1 | 1.58 |
| 5842 | 3 | 4 | 5 | | V-1 | UFL1 | 1.67 | 5938 | 3 | 4 | 5 | V-1 | XYLT2 | 1.62 |
| 5843 | 3 | 4 | 5 | | V-1 | UFM1 | 1.80 | 5939 | 3 | 4 | 5 | V-1 | YARS2 | 1.66 |
| 5844 | 3 | 4 | 5 | | V-1 | UHRF1BP1L | 1.68 | 5940 | 3 | 4 | 5 | V-1 | YIPF5 | 1.69 |
| 5845 | 3 | 4 | 5 | | V-1 | UIMC1 | 1.72 | 5941 | 3 | 4 | 5 | V-1 | YIPF6 | 1.98 |
| 5846 | 3 | 4 | 5 | | V-1 | ULK2 | 1.78 | 5942 | 3 | 4 | 5 | V-1 | YKT6 | 1.51 |
| 5847 | 3 | 4 | 5 | | V-1 | UNC50 | 1.97 | 5943 | 3 | 4 | 5 | V-1 | YLPM1 | 1.98 |
| 5848 | 3 | 4 | 5 | | V-1 | UNC5CL | 1.95 | 5944 | 3 | 4 | 5 | V-1 | YME1L1 | 1.55 |
| 5849 | 3 | 4 | 5 | | V-1 | UNK | 1.87 | 5945 | 3 | 4 | 5 | V-1 | YPEL5 | 1.58 |
| 5850 | 3 | 4 | 5 | | V-1 | UQCC | 1.75 | 5946 | 3 | 4 | 5 | V-1 | YTHDF1 | 1.62 |
| 5851 | 3 | 4 | 5 | | V-1 | UQCRC1 | 1.71 | 5947 | 3 | 4 | 5 | V-1 | YTHDF2 | 1.82 |
| 5852 | 3 | 4 | 5 | | V-1 | UQCRQ | 1.61 | 5948 | 3 | 4 | 5 | V-1 | YWHAG | 1.85 |

Fig. 40 - 32

| | | | | | | | | | | | | | | |
|---|---|---|---|---|---|---|---|---|---|---|---|---|---|---|
| 5949 | 3 | 4 | 5 | | | V-1 | YWHAH | 1.79 | 6045 | 3 | 4 | 5 | | V-1 | ZNF296 | 1.78 |
| 5950 | 3 | 4 | 5 | | | V-1 | YWHAZ | 1.64 | 6046 | 3 | 4 | 5 | | V-1 | ZNF302 | 1.96 |
| 5951 | 3 | 4 | 5 | | | V-1 | ZADH2 | 1.85 | 6047 | 3 | 4 | 5 | | V-1 | ZNF317 | 1.65 |
| 5952 | 3 | 4 | 5 | | | V-1 | ZAP70 | 1.82 | 6048 | 3 | 4 | 5 | | V-1 | ZNF322 | 1.52 |
| 5953 | 3 | 4 | 5 | | | V-1 | ZBTB1 | 1.82 | 6049 | 3 | 4 | 5 | | V-1 | ZNF324 | 1.54 |
| 5954 | 3 | 4 | 5 | | | V-1 | ZBTB11 | 1.67 | 6050 | 3 | 4 | 5 | | V-1 | ZNF330 | 1.84 |
| 5955 | 3 | 4 | 5 | | | V-1 | ZBTB17 | 1.87 | 6051 | 3 | 4 | 5 | | V-1 | ZNF331 | 1.69 |
| 5956 | 3 | 4 | 5 | | | V-1 | ZBTB2 | 1.52 | 6052 | 3 | 4 | 5 | | V-1 | ZNF33A | 1.90 |
| 5957 | 3 | 4 | 5 | | | V-1 | ZBTB25 | 1.88 | 6053 | 3 | 4 | 5 | | V-1 | ZNF338 | 1.64 |
| 5958 | 3 | 4 | 5 | | | V-1 | ZBTB3 | 1.57 | 6054 | 3 | 4 | 5 | | V-1 | ZNF343 | 1.79 |
| 5959 | 3 | 4 | 5 | | | V-1 | ZBTB33 | 1.61 | 6055 | 3 | 4 | 5 | | V-1 | ZNF346 | 1.51 |
| 5960 | 3 | 4 | 5 | | | V-1 | ZBTB37 | 1.52 | 6056 | 3 | 4 | 5 | | V-1 | ZNF350 | 1.95 |
| 5961 | 3 | 4 | 5 | | | V-1 | ZBTB45 | 1.53 | 6057 | 3 | 4 | 5 | | V-1 | ZNF366 | 1.74 |
| 5962 | 3 | 4 | 5 | | | V-1 | ZBTB47 | 1.83 | 6058 | 3 | 4 | 5 | | V-1 | ZNF382 | 1.75 |
| 5963 | 3 | 4 | 5 | | | V-1 | ZBTB48 | 1.88 | 6059 | 3 | 4 | 5 | | V-1 | ZNF384 | 1.96 |
| 5964 | 3 | 4 | 5 | | | V-1 | ZBTB49 | 1.58 | 6060 | 3 | 4 | 5 | | V-1 | ZNF385D | 1.66 |
| 5965 | 3 | 4 | 5 | | | V-1 | ZBTB7A | 1.87 | 6061 | 3 | 4 | 5 | | V-1 | ZNF395 | 1.51 |
| 5966 | 3 | 4 | 5 | | | V-1 | ZBTB7B | 1.52 | 6062 | 3 | 4 | 5 | | V-1 | ZNF398 | 1.67 |
| 5967 | 3 | 4 | 5 | | | V-1 | ZC2HC1A | 1.62 | 6063 | 3 | 4 | 5 | | V-1 | ZNF407 | 1.66 |
| 5968 | 3 | 4 | 5 | | | V-1 | ZC3H15 | 1.60 | 6064 | 3 | 4 | 5 | | V-1 | ZNF408 | 1.78 |
| 5969 | 3 | 4 | 5 | | | V-1 | ZC3H18 | 1.83 | 6065 | 3 | 4 | 5 | | V-1 | ZNF418 | 1.54 |
| 5970 | 3 | 4 | 5 | | | V-1 | ZC3H3 | 1.65 | 6066 | 3 | 4 | 5 | | V-1 | ZNF419 | 1.96 |
| 5971 | 3 | 4 | 5 | | | V-1 | ZC3H4 | 1.81 | 6067 | 3 | 4 | 5 | | V-1 | ZNF43 | 1.57 |
| 5972 | 3 | 4 | 5 | | | V-1 | ZC3H7B | 1.78 | 6068 | 3 | 4 | 5 | | V-1 | ZNF430 | 1.65 |
| 5973 | 3 | 4 | 5 | | | V-1 | ZC3H8 | 1.54 | 6069 | 3 | 4 | 5 | | V-1 | ZNF434 | 1.51 |
| 5974 | 3 | 4 | 5 | | | V-1 | ZDHHC14 | 1.52 | 6070 | 3 | 4 | 5 | | V-1 | ZNF436 | 1.79 |
| 5975 | 3 | 4 | 5 | | | V-1 | ZDHHC16 | 1.54 | 6071 | 3 | 4 | 5 | | V-1 | ZNF441 | 1.75 |
| 5976 | 3 | 4 | 5 | | | V-1 | ZDHHC18 | 1.82 | 6072 | 3 | 4 | 5 | | V-1 | ZNF443 | 1.63 |
| 5977 | 3 | 4 | 5 | | | V-1 | ZDHHC23 | 1.81 | 6073 | 3 | 4 | 5 | | V-1 | ZNF444 | 1.68 |
| 5978 | 3 | 4 | 5 | | | V-1 | ZDHHC5 | 1.75 | 6074 | 3 | 4 | 5 | | V-1 | ZNF445 | 1.79 |
| 5979 | 3 | 4 | 5 | | | V-1 | ZDHHC7 | 1.88 | 6075 | 3 | 4 | 5 | | V-1 | ZNF446 | 1.71 |
| 5980 | 3 | 4 | 5 | | | V-1 | ZEB1 | 1.55 | 6076 | 3 | 4 | 5 | | V-1 | ZNF449 | 1.56 |
| 5981 | 3 | 4 | 5 | | | V-1 | ZFAND2A | 1.59 | 6077 | 3 | 4 | 5 | | V-1 | ZNF484 | 1.59 |
| 5982 | 3 | 4 | 5 | | | V-1 | ZFAND3 | 1.55 | 6078 | 3 | 4 | 5 | | V-1 | ZNF487P | 1.57 |
| 5983 | 3 | 4 | 5 | | | V-1 | ZFP14 | 1.59 | 6079 | 3 | 4 | 5 | | V-1 | ZNF498 | 1.69 |
| 5984 | 3 | 4 | 5 | | | V-1 | ZFP36 | 1.84 | 6080 | 3 | 4 | 5 | | V-1 | ZNF500 | 1.53 |
| 5985 | 3 | 4 | 5 | | | V-1 | ZFP36L1 | 1.87 | 6081 | 3 | 4 | 5 | | V-1 | ZNF506 | 1.90 |
| 5986 | 3 | 4 | 5 | | | V-1 | ZFP36L2 | 1.77 | 6082 | 3 | 4 | 5 | | V-1 | ZNF516 | 1.89 |
| 5987 | 3 | 4 | 5 | | | V-1 | ZFP41 | 1.97 | 6083 | 3 | 4 | 5 | | V-1 | ZNF517 | 1.62 |
| 5988 | 3 | 4 | 5 | | | V-1 | ZFP91 | 1.64 | 6084 | 3 | 4 | 5 | | V-1 | ZNF518B | 1.90 |
| 5989 | 3 | 4 | 5 | | | V-1 | ZFPL1 | 1.73 | 6085 | 3 | 4 | 5 | | V-1 | ZNF526 | 1.50 |
| 5990 | 3 | 4 | 5 | | | V-1 | ZFX | 1.87 | 6086 | 3 | 4 | 5 | | V-1 | ZNF543 | 1.71 |
| 5991 | 3 | 4 | 5 | | | V-1 | ZFYVE1 | 1.79 | 6087 | 3 | 4 | 5 | | V-1 | ZNF546 | 1.81 |
| 5992 | 3 | 4 | 5 | | | V-1 | ZGPAT | 1.99 | 6088 | 3 | 4 | 5 | | V-1 | ZNF549 | 1.59 |
| 5993 | 3 | 4 | 5 | | | V-1 | ZHX1 | 1.62 | 6089 | 3 | 4 | 5 | | V-1 | ZNF554 | 1.83 |
| 5994 | 3 | 4 | 5 | | | V-1 | ZHX2 | 1.94 | 6090 | 3 | 4 | 5 | | V-1 | ZNF561 | 1.70 |
| 5995 | 3 | 4 | 5 | | | V-1 | ZIK1 | 1.51 | 6091 | 3 | 4 | 5 | | V-1 | ZNF563 | 1.70 |
| 5996 | 3 | 4 | 5 | | | V-1 | ZKSCAN4 | 1.93 | 6092 | 3 | 4 | 5 | | V-1 | ZNF564 | 1.94 |
| 5997 | 3 | 4 | 5 | | | V-1 | ZKSCAN5 | 1.69 | 6093 | 3 | 4 | 5 | | V-1 | ZNF575 | 1.71 |
| 5998 | 3 | 4 | 5 | | | V-1 | ZMAT3 | 1.82 | 6094 | 3 | 4 | 5 | | V-1 | ZNF577 | 1.97 |
| 5999 | 3 | 4 | 5 | | | V-1 | ZMPSTE24 | 1.62 | 6095 | 3 | 4 | 5 | | V-1 | ZNF579 | 1.91 |
| 6000 | 3 | 4 | 5 | | | V-1 | ZMYM4 | 1.82 | 6096 | 3 | 4 | 5 | | V-1 | ZNF582 | 1.53 |
| 6001 | 3 | 4 | 5 | | | V-1 | ZMYND19 | 1.66 | 6097 | 3 | 4 | 5 | | V-1 | ZNF585A | 1.75 |
| 6002 | 3 | 4 | 5 | | | V-1 | ZNF107 | 1.55 | 6098 | 3 | 4 | 5 | | V-1 | ZNF585B | 1.62 |
| 6003 | 3 | 4 | 5 | | | V-1 | ZNF121 | 1.68 | 6099 | 3 | 4 | 5 | | V-1 | ZNF586 | 1.51 |
| 6004 | 3 | 4 | 5 | | | V-1 | ZNF124 | 1.53 | 6100 | 3 | 4 | 5 | | V-1 | ZNF598 | 1.87 |
| 6005 | 3 | 4 | 5 | | | V-1 | ZNF133 | 1.82 | 6101 | 3 | 4 | 5 | | V-1 | ZNF600 | 1.59 |
| 6006 | 3 | 4 | 5 | | | V-1 | ZNF136 | 1.57 | 6102 | 3 | 4 | 5 | | V-1 | ZNF606 | 1.76 |
| 6007 | 3 | 4 | 5 | | | V-1 | ZNF140 | 1.71 | 6103 | 3 | 4 | 5 | | V-1 | ZNF609 | 1.76 |
| 6008 | 3 | 4 | 5 | | | V-1 | ZNF142 | 1.94 | 6104 | 3 | 4 | 5 | | V-1 | ZNF615 | 1.57 |
| 6009 | 3 | 4 | 5 | | | V-1 | ZNF143 | 1.65 | 6105 | 3 | 4 | 5 | | V-1 | ZNF619 | 1.58 |
| 6010 | 3 | 4 | 5 | | | V-1 | ZNF146 | 1.70 | 6106 | 3 | 4 | 5 | | V-1 | ZNF620 | 1.77 |
| 6011 | 3 | 4 | 5 | | | V-1 | ZNF148 | 1.62 | 6107 | 3 | 4 | 5 | | V-1 | ZNF621 | 1.81 |
| 6012 | 3 | 4 | 5 | | | V-1 | ZNF160 | 1.74 | 6108 | 3 | 4 | 5 | | V-1 | ZNF623 | 1.84 |
| 6013 | 3 | 4 | 5 | | | V-1 | ZNF167 | 1.53 | 6109 | 3 | 4 | 5 | | V-1 | ZNF624 | 1.69 |
| 6014 | 3 | 4 | 5 | | | V-1 | ZNF175 | 2.00 | 6110 | 3 | 4 | 5 | | V-1 | ZNF630 | 1.89 |
| 6015 | 3 | 4 | 5 | | | V-1 | ZNF187 | 1.68 | 6111 | 3 | 4 | 5 | | V-1 | ZNF642 | 1.75 |
| 6016 | 3 | 4 | 5 | | | V-1 | ZNF189 | 1.88 | 6112 | 3 | 4 | 5 | | V-1 | ZNF644 | 1.52 |
| 6017 | 3 | 4 | 5 | | | V-1 | ZNF193 | 1.67 | 6113 | 3 | 4 | 5 | | V-1 | ZNF655 | 1.98 |
| 6018 | 3 | 4 | 5 | | | V-1 | ZNF195 | 1.69 | 6114 | 3 | 4 | 5 | | V-1 | ZNF658 | 1.63 |
| 6019 | 3 | 4 | 5 | | | V-1 | ZNF197 | 1.85 | 6115 | 3 | 4 | 5 | | V-1 | ZNF664 | 1.76 |
| 6020 | 3 | 4 | 5 | | | V-1 | ZNF2 | 1.52 | 6116 | 3 | 4 | 5 | | V-1 | ZNF669 | 1.57 |
| 6021 | 3 | 4 | 5 | | | V-1 | ZNF207 | 1.54 | 6117 | 3 | 4 | 5 | | V-1 | ZNF671 | 1.57 |
| 6022 | 3 | 4 | 5 | | | V-1 | ZNF211 | 1.93 | 6118 | 3 | 4 | 5 | | V-1 | ZNF672 | 1.55 |
| 6023 | 3 | 4 | 5 | | | V-1 | ZNF212 | 1.73 | 6119 | 3 | 4 | 5 | | V-1 | ZNF673 | 1.77 |
| 6024 | 3 | 4 | 5 | | | V-1 | ZNF213 | 1.77 | 6120 | 3 | 4 | 5 | | V-1 | ZNF674 | 1.72 |
| 6025 | 3 | 4 | 5 | | | V-1 | ZNF217 | 1.68 | 6121 | 3 | 4 | 5 | | V-1 | ZNF678 | 1.78 |
| 6026 | 3 | 4 | 5 | | | V-1 | ZNF219 | 1.58 | 6122 | 3 | 4 | 5 | | V-1 | ZNF681 | 1.69 |
| 6027 | 3 | 4 | 5 | | | V-1 | ZNF223 | 1.84 | 6123 | 3 | 4 | 5 | | V-1 | ZNF682 | 1.70 |
| 6028 | 3 | 4 | 5 | | | V-1 | ZNF225 | 1.70 | 6124 | 3 | 4 | 5 | | V-1 | ZNF687 | 1.78 |
| 6029 | 3 | 4 | 5 | | | V-1 | ZNF232 | 1.70 | 6125 | 3 | 4 | 5 | | V-1 | ZNF697 | 1.99 |
| 6030 | 3 | 4 | 5 | | | V-1 | ZNF235 | 1.51 | 6126 | 3 | 4 | 5 | | V-1 | ZNF7 | 1.65 |
| 6031 | 3 | 4 | 5 | | | V-1 | ZNF236 | 1.88 | 6127 | 3 | 4 | 5 | | V-1 | ZNF70 | 1.75 |
| 6032 | 3 | 4 | 5 | | | V-1 | ZNF24 | 1.95 | 6128 | 3 | 4 | 5 | | V-1 | ZNF701 | 1.60 |
| 6033 | 3 | 4 | 5 | | | V-1 | ZNF25 | 1.54 | 6129 | 3 | 4 | 5 | | V-1 | ZNF702P | 1.64 |
| 6034 | 3 | 4 | 5 | | | V-1 | ZNF259 | 1.56 | 6130 | 3 | 4 | 5 | | V-1 | ZNF710 | 1.78 |
| 6035 | 3 | 4 | 5 | | | V-1 | ZNF263 | 1.62 | 6131 | 3 | 4 | 5 | | V-1 | ZNF714 | 1.93 |
| 6036 | 3 | 4 | 5 | | | V-1 | ZNF264 | 2.00 | 6132 | 3 | 4 | 5 | | V-1 | ZNF720 | 1.65 |
| 6037 | 3 | 4 | 5 | | | V-1 | ZNF274 | 1.54 | 6133 | 3 | 4 | 5 | | V-1 | ZNF721 | 1.85 |
| 6038 | 3 | 4 | 5 | | | V-1 | ZNF28 | 1.55 | 6134 | 3 | 4 | 5 | | V-1 | ZNF738 | 1.75 |
| 6039 | 3 | 4 | 5 | | | V-1 | ZNF280D | 1.69 | 6135 | 3 | 4 | 5 | | V-1 | ZNF746 | 1.57 |
| 6040 | 3 | 4 | 5 | | | V-1 | ZNF281 | 1.94 | 6136 | 3 | 4 | 5 | | V-1 | ZNF761 | 1.82 |
| 6041 | 3 | 4 | 5 | | | V-1 | ZNF283 | 1.54 | 6137 | 3 | 4 | 5 | | V-1 | ZNF764 | 1.62 |
| 6042 | 3 | 4 | 5 | | | V-1 | ZNF284 | 1.60 | 6138 | 3 | 4 | 5 | | V-1 | ZNF766 | 1.93 |
| 6043 | 3 | 4 | 5 | | | V-1 | ZNF292 | 1.80 | 6139 | 3 | 4 | 5 | | V-1 | ZNF768 | 1.69 |
| 6044 | 3 | 4 | 5 | | | V-1 | ZNF295 | 1.84 | 6140 | 3 | 4 | 5 | | V-1 | ZNF770 | 1.98 |

Fig. 40 - 33

| | | | | | | | | | | | | | | |
|---|---|---|---|---|---|---|---|---|---|---|---|---|---|---|
| 6141 | 3 | 4 | 5 | | V-1 | ZNF772 | 1.61 | 6237 | 3 | 4 | | | IV-2 | C19orf70 | 0.83 |
| 6142 | 3 | 4 | 5 | | V-1 | ZNF773 | 1.67 | 6238 | 3 | 4 | | | IV-2 | C1D | 0.96 |
| 6143 | 3 | 4 | 5 | | V-1 | ZNF776 | 1.85 | 6239 | 3 | 4 | | | IV-2 | C1QBP | 0.78 |
| 6144 | 3 | 4 | 5 | | V-1 | ZNF778 | 1.84 | 6240 | 3 | 4 | | | IV-2 | C1QL3 | 0.97 |
| 6145 | 3 | 4 | 5 | | V-1 | ZNF784 | 1.95 | 6241 | 3 | 4 | | | IV-2 | C1orf151-NBL1 | 0.88 |
| 6146 | 3 | 4 | 5 | | V-1 | ZNF79 | 1.64 | 6242 | 3 | 4 | | | IV-2 | C1orf86 | 0.89 |
| 6147 | 3 | 4 | 5 | | V-1 | ZNF791 | 1.50 | 6243 | 3 | 4 | | | IV-2 | C20orf196 | 0.86 |
| 6148 | 3 | 4 | 5 | | V-1 | ZNF8 | 1.61 | 6244 | 3 | 4 | | | IV-2 | C20orf3 | 0.84 |
| 6149 | 3 | 4 | 5 | | V-1 | ZNF805 | 1.89 | 6245 | 3 | 4 | | | IV-2 | C21orf119 | 0.91 |
| 6150 | 3 | 4 | 5 | | V-1 | ZNF808 | 1.61 | 6246 | 3 | 4 | | | IV-2 | C22orf13 | 0.90 |
| 6151 | 3 | 4 | 5 | | V-1 | ZNF815 | 1.61 | 6247 | 3 | 4 | | | IV-2 | C2orf28 | 0.96 |
| 6152 | 3 | 4 | 5 | | V-1 | ZNF816 | 1.56 | 6248 | 3 | 4 | | | IV-2 | C2orf81 | 0.88 |
| 6153 | 3 | 4 | 5 | | V-1 | ZNF830 | 1.70 | 6249 | 3 | 4 | | | IV-2 | C3orf18 | 0.88 |
| 6154 | 3 | 4 | 5 | | V-1 | ZNF84 | 1.85 | 6250 | 3 | 4 | | | IV-2 | C5orf20 | 0.91 |
| 6155 | 3 | 4 | 5 | | V-1 | ZNF846 | 1.83 | 6251 | 3 | 4 | | | IV-2 | C6orf1 | 0.83 |
| 6156 | 3 | 4 | 5 | | V-1 | ZNF879 | 1.99 | 6252 | 3 | 4 | | | IV-2 | C6orf108 | 0.92 |
| 6157 | 3 | 4 | 5 | | V-1 | ZNF93 | 1.52 | 6253 | 3 | 4 | | | IV-2 | C8orf40 | 0.82 |
| 6158 | 3 | 4 | 5 | | V-1 | ZNRF1 | 1.57 | 6254 | 3 | 4 | | | IV-2 | C9orf16 | 0.77 |
| 6159 | 3 | 4 | 5 | | V-1 | ZRANB1 | 1.55 | 6255 | 3 | 4 | | | IV-2 | C9orf21 | 0.94 |
| 6160 | 3 | 4 | 5 | | V-1 | ZRSR2 | 1.94 | 6256 | 3 | 4 | | | IV-2 | CAPZB | 0.86 |
| 6161 | 3 | 4 | 5 | | V-1 | ZSWIM1 | 1.85 | 6257 | 3 | 4 | | | IV-2 | CAT | 0.95 |
| 6162 | 3 | 4 | 5 | | V-1 | ZSWIM3 | 1.68 | 6258 | 3 | 4 | | | IV-2 | CBLB | 0.99 |
| 6163 | 3 | 4 | 5 | | V-1 | ZSWIM7 | 1.81 | 6259 | 3 | 4 | | | IV-2 | CCDC102A | 0.79 |
| 6164 | 3 | 4 | 5 | | V-1 | ZW10 | 1.82 | 6260 | 3 | 4 | | | IV-2 | CCDC122 | 0.99 |
| 6165 | 3 | 4 | 5 | | V-1 | ZWILCH | 1.55 | 6261 | 3 | 4 | | | IV-2 | CCDC124 | 0.87 |
| 6166 | 3 | 4 | 5 | | V-1 | ZYG11B | 1.83 | 6262 | 3 | 4 | | | IV-2 | CCDC125 | 0.98 |
| 6167 | 3 | 4 | 5 | | IV-2 | A2LD1 | 0.79 | 6263 | 3 | 4 | | | IV-2 | CCDC163P | 0.85 |
| 6168 | 3 | 4 | | | IV-2 | ABCC4 | 0.88 | 6264 | 3 | 4 | | | IV-2 | CCDC23 | 0.68 |
| 6169 | 3 | 4 | | | IV-2 | ABHD14A | 0.74 | 6265 | 3 | 4 | | | IV-2 | CCDC28B | 0.85 |
| 6170 | 3 | 4 | | | IV-2 | ABT1 | 0.97 | 6266 | 3 | 4 | | | IV-2 | CCDC51 | 0.96 |
| 6171 | 3 | 4 | | | IV-2 | ACOT4 | 0.93 | 6267 | 3 | 4 | | | IV-2 | CCDC8 | 0.70 |
| 6172 | 3 | 4 | | | IV-2 | ADAL | 0.98 | 6268 | 3 | 4 | | | IV-2 | CCDC75 | 0.73 |
| 6173 | 3 | 4 | | | IV-2 | ADARB2 | 0.93 | 6269 | 3 | 4 | | | IV-2 | CCL23 | 0.97 |
| 6174 | 3 | 4 | | | IV-2 | ADORA2A | 0.94 | 6270 | 3 | 4 | | | IV-2 | CCL28 | 0.72 |
| 6175 | 3 | 4 | | | IV-2 | AES | 0.71 | 6271 | 3 | 4 | | | IV-2 | CCND3 | 0.99 |
| 6176 | 3 | 4 | | | IV-2 | AFAP1 | 0.82 | 6272 | 3 | 4 | | | IV-2 | CCT7 | 0.89 |
| 6177 | 3 | 4 | | | IV-2 | AGBL5 | 0.98 | 6273 | 3 | 4 | | | IV-2 | CD2 | 0.70 |
| 6178 | 3 | 4 | | | IV-2 | AHCY | 0.96 | 6274 | 3 | 4 | | | IV-2 | CD226 | 0.95 |
| 6179 | 3 | 4 | | | IV-2 | AKAP5 | 0.97 | 6275 | 3 | 4 | | | IV-2 | CD24 | 0.92 |
| 6180 | 3 | 4 | | | IV-2 | AKT1S1 | 0.89 | 6276 | 3 | 4 | | | IV-2 | CD247 | 0.92 |
| 6181 | 3 | 4 | | | IV-2 | ALDH1B1 | 0.78 | 6277 | 3 | 4 | | | IV-2 | CD52 | 0.73 |
| 6182 | 3 | 4 | | | IV-2 | ALKBH2 | 0.96 | 6278 | 3 | 4 | | | IV-2 | CD7 | 0.86 |
| 6183 | 3 | 4 | | | IV-2 | ANKRD19P | 0.82 | 6279 | 3 | 4 | | | IV-2 | CD82 | 0.79 |
| 6184 | 3 | 4 | | | IV-2 | AP3S2 | 0.87 | 6280 | 3 | 4 | | | IV-2 | CD99 | 0.86 |
| 6185 | 3 | 4 | | | IV-2 | AP4S1 | 0.96 | 6281 | 3 | 4 | | | IV-2 | CDA | 0.83 |
| 6186 | 3 | 4 | | | IV-2 | APEX1 | 0.93 | 6282 | 3 | 4 | | | IV-2 | CDC123 | 0.92 |
| 6187 | 3 | 4 | | | IV-2 | APITD1-CORT | 0.87 | 6283 | 3 | 4 | | | IV-2 | CDCA4 | 0.94 |
| 6188 | 3 | 4 | | | IV-2 | APOA1BP | 0.86 | 6284 | 3 | 4 | | | IV-2 | CDK2AP2 | 0.88 |
| 6189 | 3 | 4 | | | IV-2 | APOO | 0.96 | 6285 | 3 | 4 | | | IV-2 | CDK5R1 | 0.90 |
| 6190 | 3 | 4 | | | IV-2 | APRT | 1.00 | 6286 | 3 | 4 | | | IV-2 | CDKN2A | 0.96 |
| 6191 | 3 | 4 | | | IV-2 | AREG | 0.91 | 6287 | 3 | 4 | | | IV-2 | CDKN2AIPNL | 0.94 |
| 6192 | 3 | 4 | | | IV-2 | ARF5 | 0.90 | 6288 | 3 | 4 | | | IV-2 | CDKN2C | 0.93 |
| 6193 | 3 | 4 | | | IV-2 | ARHGAP10 | 0.77 | 6289 | 3 | 4 | | | IV-2 | CENPH | 0.94 |
| 6194 | 3 | 4 | | | IV-2 | ARHGDIB | 0.95 | 6290 | 3 | 4 | | | IV-2 | CENPL | 0.68 |
| 6195 | 3 | 4 | | | IV-2 | ARPC5L | 0.96 | 6291 | 3 | 4 | | | IV-2 | CETN2 | 0.90 |
| 6196 | 3 | 4 | | | IV-2 | ASNA1 | 0.94 | 6292 | 3 | 4 | | | IV-2 | CFH | 0.93 |
| 6197 | 3 | 4 | | | IV-2 | ASNSD1 | 0.93 | 6293 | 3 | 4 | | | IV-2 | CFL1 | 0.99 |
| 6198 | 3 | 4 | | | IV-2 | ATL3 | 0.96 | 6294 | 3 | 4 | | | IV-2 | CHMP6 | 0.99 |
| 6199 | 3 | 4 | | | IV-2 | ATP5EP2 | 0.92 | 6295 | 3 | 4 | | | IV-2 | CHRNE | 0.94 |
| 6200 | 3 | 4 | | | IV-2 | ATP5O | 0.99 | 6296 | 3 | 4 | | | IV-2 | CHST10 | 0.97 |
| 6201 | 3 | 4 | | | IV-2 | ATP6V1F | 0.86 | 6297 | 3 | 4 | | | IV-2 | CHST12 | 0.99 |
| 6202 | 3 | 4 | | | IV-2 | B3GALT2 | 0.95 | 6298 | 3 | 4 | | | IV-2 | CINP | 0.87 |
| 6203 | 3 | 4 | | | IV-2 | B4GALNT3 | 0.98 | 6299 | 3 | 4 | | | IV-2 | CISD3 | 0.85 |
| 6204 | 3 | 4 | | | IV-2 | B4GALT2 | 0.96 | 6300 | 3 | 4 | | | IV-2 | CLEC4G | 0.98 |
| 6205 | 3 | 4 | | | IV-2 | B4GALT6 | 0.93 | 6301 | 3 | 4 | | | IV-2 | CLIC5 | 0.88 |
| 6206 | 3 | 4 | | | IV-2 | BAD | 0.97 | 6302 | 3 | 4 | | | IV-2 | CNR2 | 0.95 |
| 6207 | 3 | 4 | | | IV-2 | BATF | 0.92 | 6303 | 3 | 4 | | | IV-2 | CNTNAP2 | 0.96 |
| 6208 | 3 | 4 | | | IV-2 | BCL7B | 0.99 | 6304 | 3 | 4 | | | IV-2 | COCH | 0.97 |
| 6209 | 3 | 4 | | | IV-2 | BCL7C | 0.91 | 6305 | 3 | 4 | | | IV-2 | COMMD1 | 0.81 |
| 6210 | 3 | 4 | | | IV-2 | BDH2 | 0.88 | 6306 | 3 | 4 | | | IV-2 | COMMD3-BMI1 | 0.98 |
| 6211 | 3 | 4 | | | IV-2 | BEX2 | 0.91 | 6307 | 3 | 4 | | | IV-2 | COPE | 1.00 |
| 6212 | 3 | 4 | | | IV-2 | BICD1 | 0.96 | 6308 | 3 | 4 | | | IV-2 | COPZ1 | 0.96 |
| 6213 | 3 | 4 | | | IV-2 | BIK | 0.92 | 6309 | 3 | 4 | | | IV-2 | COX4I1 | 0.76 |
| 6214 | 3 | 4 | | | IV-2 | BMP2 | 1.00 | 6310 | 3 | 4 | | | IV-2 | COX5A | 0.98 |
| 6215 | 3 | 4 | | | IV-2 | BPHL | 0.71 | 6311 | 3 | 4 | | | IV-2 | COX6B1 | 0.98 |
| 6216 | 3 | 4 | | | IV-2 | BRI3BP | 0.74 | 6312 | 3 | 4 | | | IV-2 | CRISP3 | 0.79 |
| 6217 | 3 | 4 | | | IV-2 | BRP44 | 0.88 | 6313 | 3 | 4 | | | IV-2 | CRSP8P | 0.97 |
| 6218 | 3 | 4 | | | IV-2 | BTF3 | 0.99 | 6314 | 3 | 4 | | | IV-2 | CTAGE15P | 0.97 |
| 6219 | 3 | 4 | | | IV-2 | BTF3P11 | 0.94 | 6315 | 3 | 4 | | | IV-2 | CTNNAL1 | 0.97 |
| 6220 | 3 | 4 | | | IV-2 | C10orf11 | 0.90 | 6316 | 3 | 4 | | | IV-2 | CTNNBIP1 | 0.94 |
| 6221 | 3 | 4 | | | IV-2 | C11orf2 | 0.99 | 6317 | 3 | 4 | | | IV-2 | CTSE | 0.90 |
| 6222 | 3 | 4 | | | IV-2 | C11orf74 | 0.72 | 6318 | 3 | 4 | | | IV-2 | CTU2 | 0.89 |
| 6223 | 3 | 4 | | | IV-2 | C12orf10 | 0.89 | 6319 | 3 | 4 | | | IV-2 | CXXC5 | 0.98 |
| 6224 | 3 | 4 | | | IV-2 | C12orf29 | 0.78 | 6320 | 3 | 4 | | | IV-2 | CYBRD1 | 0.89 |
| 6225 | 3 | 4 | | | IV-2 | C12orf32 | 0.95 | 6321 | 3 | 4 | | | IV-2 | CYTH3 | 0.90 |
| 6226 | 3 | 4 | | | IV-2 | C12orf42 | 1.00 | 6322 | 3 | 4 | | | IV-2 | DBI | 0.87 |
| 6227 | 3 | 4 | | | IV-2 | C12orf43 | 0.77 | 6323 | 3 | 4 | | | IV-2 | DCK | 0.98 |
| 6228 | 3 | 4 | | | IV-2 | C14orf132 | 0.98 | 6324 | 3 | 4 | | | IV-2 | DDX11L9 | 0.97 |
| 6229 | 3 | 4 | | | IV-2 | C14orf167 | 0.89 | 6325 | 3 | 4 | | | IV-2 | DEFB109P1 | 0.94 |
| 6230 | 3 | 4 | | | IV-2 | C15orf50 | 1.00 | 6326 | 3 | 4 | | | IV-2 | DES | 0.95 |
| 6231 | 3 | 4 | | | IV-2 | C16orf91 | 0.71 | 6327 | 3 | 4 | | | IV-2 | DGAT2 | 0.93 |
| 6232 | 3 | 4 | | | IV-2 | C17orf58 | 0.78 | 6328 | 3 | 4 | | | IV-2 | DGCR6 | 0.92 |
| 6233 | 3 | 4 | | | IV-2 | C18orf1 | 0.98 | 6329 | 3 | 4 | | | IV-2 | DGCR6L | 0.91 |
| 6234 | 3 | 4 | | | IV-2 | C19orf43 | 0.88 | 6330 | 3 | 4 | | | IV-2 | DHRS3 | 0.85 |
| 6235 | 3 | 4 | | | IV-2 | C19orf53 | 0.68 | 6331 | 3 | 4 | | | IV-2 | DHRS7 | 0.92 |
| 6236 | 3 | 4 | | | IV-2 | C19orf63 | 0.95 | 6332 | 3 | 4 | | | IV-2 | DIABLO | 0.95 |

Fig. 40 - 34

| | | | | | | | | | | | | | | | |
|---|---|---|---|---|---|---|---|---|---|---|---|---|---|---|---|
| 6333 | 3 | 4 | | | IV-2 | DLG5 | 1.00 | 6429 | 3 | 4 | | | IV-2 | GSR | 0.98 |
| 6334 | 3 | 4 | | | IV-2 | DMKN | 1.00 | 6430 | 3 | 4 | | | IV-2 | GTDC1 | 0.97 |
| 6335 | 3 | 4 | | | IV-2 | DNAAF2 | 0.96 | 6431 | 3 | 4 | | | IV-2 | GTF2A2 | 0.93 |
| 6336 | 3 | 4 | | | IV-2 | DNAJB9 | 0.81 | 6432 | 3 | 4 | | | IV-2 | GTF3A | 0.80 |
| 6337 | 3 | 4 | | | IV-2 | DNAJC18 | 0.98 | 6433 | 3 | 4 | | | IV-2 | GTSF1 | 0.92 |
| 6338 | 3 | 4 | | | IV-2 | DNAJC9 | 0.83 | 6434 | 3 | 4 | | | IV-2 | H2AFB2 | 0.93 |
| 6339 | 3 | 4 | | | IV-2 | DPH3P1 | 0.91 | 6435 | 3 | 4 | | | IV-2 | HENMT1 | 0.99 |
| 6340 | 3 | 4 | | | IV-2 | DPH5 | 0.75 | 6436 | 3 | 4 | | | IV-2 | HES6 | 0.89 |
| 6341 | 3 | 4 | | | IV-2 | DPY19L1 | 0.95 | 6437 | 3 | 4 | | | IV-2 | HIGD1A | 0.97 |
| 6342 | 3 | 4 | | | IV-2 | DPY30 | 0.86 | 6438 | 3 | 4 | | | IV-2 | HINT1 | 0.74 |
| 6343 | 3 | 4 | | | IV-2 | DSTN | 0.92 | 6439 | 3 | 4 | | | IV-2 | HLA-DPB2 | 1.00 |
| 6344 | 3 | 4 | | | IV-2 | DTD1 | 0.98 | 6440 | 3 | 4 | | | IV-2 | HMOX2 | 0.96 |
| 6345 | 3 | 4 | | | IV-2 | DUSP14 | 0.78 | 6441 | 3 | 4 | | | IV-2 | HN1 | 0.91 |
| 6346 | 3 | 4 | | | IV-2 | DUSP19 | 0.99 | 6442 | 3 | 4 | | | IV-2 | HNRNPUL2-BSCL2 | 0.95 |
| 6347 | 3 | 4 | | | IV-2 | DUSP23 | 0.85 | 6443 | 3 | 4 | | | IV-2 | HOXA10 | 1.00 |
| 6348 | 3 | 4 | | | IV-2 | DYRK3 | 0.99 | 6444 | 3 | 4 | | | IV-2 | HOXA9 | 0.99 |
| 6349 | 3 | 4 | | | IV-2 | EBP | 0.81 | 6445 | 3 | 4 | | | IV-2 | HRASLS5 | 0.94 |
| 6350 | 3 | 4 | | | IV-2 | ECI2 | 0.91 | 6446 | 3 | 4 | | | IV-2 | HS3ST3A1 | 0.87 |
| 6351 | 3 | 4 | | | IV-2 | EDF1 | 0.96 | 6447 | 3 | 4 | | | IV-2 | HS3ST3B1 | 0.93 |
| 6352 | 3 | 4 | | | IV-2 | EEF1D | 0.80 | 6448 | 3 | 4 | | | IV-2 | HSC8 | 0.93 |
| 6353 | 3 | 4 | | | IV-2 | EEF2 | 0.90 | 6449 | 3 | 4 | | | IV-2 | HSD17B8 | 0.90 |
| 6354 | 3 | 4 | | | IV-2 | EFCAB4B | 0.97 | 6450 | 3 | 4 | | | IV-2 | HSPB11 | 0.81 |
| 6355 | 3 | 4 | | | IV-2 | EFNA1 | 0.92 | 6451 | 3 | 4 | | | IV-2 | HSPE1-MOB4 | 0.88 |
| 6356 | 3 | 4 | | | IV-2 | EFNA3 | 0.97 | 6452 | 3 | 4 | | | IV-2 | ICA1L | 0.87 |
| 6357 | 3 | 4 | | | IV-2 | EIF2D | 0.90 | 6453 | 3 | 4 | | | IV-2 | IFT46 | 0.87 |
| 6358 | 3 | 4 | | | IV-2 | EIF3F | 0.77 | 6454 | 3 | 4 | | | IV-2 | IL28RA | 0.80 |
| 6359 | 3 | 4 | | | IV-2 | EIF3IP1 | 0.85 | 6455 | 3 | 4 | | | IV-2 | IL7R | 0.81 |
| 6360 | 3 | 4 | | | IV-2 | EIF3K | 0.78 | 6456 | 3 | 4 | | | IV-2 | INO80B-WBP1 | 0.90 |
| 6361 | 3 | 4 | | | IV-2 | EIF3L | 0.70 | 6457 | 3 | 4 | | | IV-2 | ISCA1 | 0.80 |
| 6362 | 3 | 4 | | | IV-2 | EIF4B | 0.83 | 6458 | 3 | 4 | | | IV-2 | ISOC1 | 0.87 |
| 6363 | 3 | 4 | | | IV-2 | EIF5A | 0.71 | 6459 | 3 | 4 | | | IV-2 | ITLN1 | 0.89 |
| 6364 | 3 | 4 | | | IV-2 | EIF5A2 | 0.84 | 6460 | 3 | 4 | | | IV-2 | ITM2A | 1.00 |
| 6365 | 3 | 4 | | | IV-2 | ELANE | 0.86 | 6461 | 3 | 4 | | | IV-2 | JAKMIP2 | 0.88 |
| 6366 | 3 | 4 | | | IV-2 | ELK2AP | 0.91 | 6462 | 3 | 4 | | | IV-2 | KATNAL1 | 1.00 |
| 6367 | 3 | 4 | | | IV-2 | ENTPD5 | 0.97 | 6463 | 3 | 4 | | | IV-2 | KBTBD3 | 0.92 |
| 6368 | 3 | 4 | | | IV-2 | ENY2 | 0.92 | 6464 | 3 | 4 | | | IV-2 | KBTBD6 | 0.99 |
| 6369 | 3 | 4 | | | IV-2 | EPS8L2 | 0.78 | 6465 | 3 | 4 | | | IV-2 | KEL | 0.99 |
| 6370 | 3 | 4 | | | IV-2 | ERF | 0.77 | 6466 | 3 | 4 | | | IV-2 | KIAA1143 | 0.89 |
| 6371 | 3 | 4 | | | IV-2 | ERN1 | 0.77 | 6467 | 3 | 4 | | | IV-2 | KIAA1671 | 0.93 |
| 6372 | 3 | 4 | | | IV-2 | EXOSC4 | 0.99 | 6468 | 3 | 4 | | | IV-2 | KIF21A | 0.96 |
| 6373 | 3 | 4 | | | IV-2 | FAIM | 0.90 | 6469 | 3 | 4 | | | IV-2 | KLHDC3 | 0.96 |
| 6374 | 3 | 4 | | | IV-2 | FAM108A1 | 0.80 | 6470 | 3 | 4 | | | IV-2 | KRT10 | 0.76 |
| 6375 | 3 | 4 | | | IV-2 | FAM111B | 0.99 | 6471 | 3 | 4 | | | IV-2 | KRT18 | 0.99 |
| 6376 | 3 | 4 | | | IV-2 | FAM124B | 0.98 | 6472 | 3 | 4 | | | IV-2 | LAMTOR1 | 0.85 |
| 6377 | 3 | 4 | | | IV-2 | FAM125B | 0.93 | 6473 | 3 | 4 | | | IV-2 | LBH | 0.93 |
| 6378 | 3 | 4 | | | IV-2 | FAM129A | 0.90 | 6474 | 3 | 4 | | | IV-2 | LDHD | 0.91 |
| 6379 | 3 | 4 | | | IV-2 | FAM162A | 0.68 | 6475 | 3 | 4 | | | IV-2 | LEPREL4 | 0.94 |
| 6380 | 3 | 4 | | | IV-2 | FAM169A | 0.84 | 6476 | 3 | 4 | | | IV-2 | LGR6 | 0.70 |
| 6381 | 3 | 4 | | | IV-2 | FAM195A | 0.70 | 6477 | 3 | 4 | | | IV-2 | LHPP | 0.94 |
| 6382 | 3 | 4 | | | IV-2 | FAM195B | 0.88 | 6478 | 3 | 4 | | | IV-2 | LIM2 | 0.99 |
| 6383 | 3 | 4 | | | IV-2 | FAM207A | 0.75 | 6479 | 3 | 4 | | | IV-2 | LIME1 | 0.91 |
| 6384 | 3 | 4 | | | IV-2 | FAM278 | 0.91 | 6480 | 3 | 4 | | | IV-2 | LIN7B | 0.93 |
| 6385 | 3 | 4 | | | IV-2 | FAM35B | 0.97 | 6481 | 3 | 4 | | | IV-2 | LINC00092 | 0.97 |
| 6386 | 3 | 4 | | | IV-2 | FAM58A | 0.90 | 6482 | 3 | 4 | | | IV-2 | LINC00116 | 0.78 |
| 6387 | 3 | 4 | | | IV-2 | FAM58BP | 0.84 | 6483 | 3 | 4 | | | IV-2 | LINC00239 | 1.00 |
| 6388 | 3 | 4 | | | IV-2 | FAM89B | 0.75 | 6484 | 3 | 4 | | | IV-2 | LINC00467 | 0.97 |
| 6389 | 3 | 4 | | | IV-2 | FARS2 | 0.85 | 6485 | 3 | 4 | | | IV-2 | LINGO2 | 0.98 |
| 6390 | 3 | 4 | | | IV-2 | FAU | 0.71 | 6486 | 3 | 4 | | | IV-2 | LIPC | 0.93 |
| 6391 | 3 | 4 | | | IV-2 | FBL | 0.95 | 6487 | 3 | 4 | | | IV-2 | LIPT2 | 0.88 |
| 6392 | 3 | 4 | | | IV-2 | FBLN2 | 0.98 | 6488 | 3 | 4 | | | IV-2 | LIX1L | 0.81 |
| 6393 | 3 | 4 | | | IV-2 | FBXL13 | 0.99 | 6489 | 3 | 4 | | | IV-2 | LOC100287616 | 0.85 |
| 6394 | 3 | 4 | | | IV-2 | FBXO32 | 0.79 | 6490 | 3 | 4 | | | IV-2 | LOC100505681 | 0.99 |
| 6395 | 3 | 4 | | | IV-2 | FDPSL2A | 0.98 | 6491 | 3 | 4 | | | IV-2 | LOC100505687 | 0.91 |
| 6396 | 3 | 4 | | | IV-2 | FEM1B | 0.95 | 6492 | 3 | 4 | | | IV-2 | LOC100505702 | 0.91 |
| 6397 | 3 | 4 | | | IV-2 | FKBP2 | 1.00 | 6493 | 3 | 4 | | | IV-2 | LOC100506668 | 0.93 |
| 6398 | 3 | 4 | | | IV-2 | FLJ27352 | 0.97 | 6494 | 3 | 4 | | | IV-2 | LOC100506930 | 1.00 |
| 6399 | 3 | 4 | | | IV-2 | FLJ39653 | 0.83 | 6495 | 3 | 4 | | | IV-2 | LOC100507218 | 0.99 |
| 6400 | 3 | 4 | | | IV-2 | FLYWCH2 | 0.79 | 6496 | 3 | 4 | | | IV-2 | LOC100507246 | 0.98 |
| 6401 | 3 | 4 | | | IV-2 | FUT11 | 0.83 | 6497 | 3 | 4 | | | IV-2 | LOC254559 | 0.85 |
| 6402 | 3 | 4 | | | IV-2 | FXYD2 | 0.99 | 6498 | 3 | 4 | | | IV-2 | LOC283104 | 0.96 |
| 6403 | 3 | 4 | | | IV-2 | FXYD7 | 0.84 | 6499 | 3 | 4 | | | IV-2 | LOC387723 | 0.96 |
| 6404 | 3 | 4 | | | IV-2 | FZD6 | 0.97 | 6500 | 3 | 4 | | | IV-2 | LOC390940 | 0.94 |
| 6405 | 3 | 4 | | | IV-2 | GADD45GIP1 | 0.80 | 6501 | 3 | 4 | | | IV-2 | LOC400685 | 0.95 |
| 6406 | 3 | 4 | | | IV-2 | GAPDH | 0.89 | 6502 | 3 | 4 | | | IV-2 | LOC493754 | 0.95 |
| 6407 | 3 | 4 | | | IV-2 | GATM | 0.96 | 6503 | 3 | 4 | | | IV-2 | LOC550643 | 0.85 |
| 6408 | 3 | 4 | | | IV-2 | GCHFR | 0.89 | 6504 | 3 | 4 | | | IV-2 | LOC644714 | 0.96 |
| 6409 | 3 | 4 | | | IV-2 | GFI1 | 0.72 | 6505 | 3 | 4 | | | IV-2 | LOC654342 | 0.97 |
| 6410 | 3 | 4 | | | IV-2 | GFOD1 | 0.68 | 6506 | 3 | 4 | | | IV-2 | LOC729862 | 0.95 |
| 6411 | 3 | 4 | | | IV-2 | GINS3 | 0.76 | 6507 | 3 | 4 | | | IV-2 | LRRC61 | 0.86 |
| 6412 | 3 | 4 | | | IV-2 | GIPC1 | 0.80 | 6508 | 3 | 4 | | | IV-2 | LSM1 | 0.92 |
| 6413 | 3 | 4 | | | IV-2 | GLIS2 | 0.91 | 6509 | 3 | 4 | | | IV-2 | LSM2 | 0.90 |
| 6414 | 3 | 4 | | | IV-2 | GLO1 | 0.90 | 6510 | 3 | 4 | | | IV-2 | LSM7 | 0.94 |
| 6415 | 3 | 4 | | | IV-2 | GLTSCR2 | 0.92 | 6511 | 3 | 4 | | | IV-2 | LTBP2 | 0.97 |
| 6416 | 3 | 4 | | | IV-2 | GNAO1 | 0.96 | 6512 | 3 | 4 | | | IV-2 | LYPD2 | 0.75 |
| 6417 | 3 | 4 | | | IV-2 | GNB2L1 | 0.69 | 6513 | 3 | 4 | | | IV-2 | LYRM4 | 0.78 |
| 6418 | 3 | 4 | | | IV-2 | GNG8 | 0.90 | 6514 | 3 | 4 | | | IV-2 | MADCAM1 | 0.92 |
| 6419 | 3 | 4 | | | IV-2 | GNGT2 | 0.97 | 6515 | 3 | 4 | | | IV-2 | MAF1 | 0.85 |
| 6420 | 3 | 4 | | | IV-2 | GNPDA2 | 0.85 | 6516 | 3 | 4 | | | IV-2 | MANEAL | 0.96 |
| 6421 | 3 | 4 | | | IV-2 | GPR133 | 0.99 | 6517 | 3 | 4 | | | IV-2 | MBLAC2 | 0.95 |
| 6422 | 3 | 4 | | | IV-2 | GPR153 | 0.98 | 6518 | 3 | 4 | | | IV-2 | MCART2 | 0.97 |
| 6423 | 3 | 4 | | | IV-2 | GPR157 | 0.80 | 6519 | 3 | 4 | | | IV-2 | MDP1 | 0.73 |
| 6424 | 3 | 4 | | | IV-2 | GPR27 | 0.79 | 6520 | 3 | 4 | | | IV-2 | MEA1 | 0.84 |
| 6425 | 3 | 4 | | | IV-2 | GPR82 | 0.90 | 6521 | 3 | 4 | | | IV-2 | METTL1 | 0.92 |
| 6426 | 3 | 4 | | | IV-2 | GPSM3 | 0.98 | 6522 | 3 | 4 | | | IV-2 | MFNG | 0.97 |
| 6427 | 3 | 4 | | | IV-2 | GPX4 | 0.74 | 6523 | 3 | 4 | | | IV-2 | MFSD2B | 0.97 |
| 6428 | 3 | 4 | | | IV-2 | GRHPR | 0.97 | 6524 | 3 | 4 | | | IV-2 | MGC12916 | 0.95 |

Fig. 40 - 35

| | | | | | | | |
|---|---|---|---|---|---|---|---|
| 6525 | 3 | 4 | | | IV-2 | MIR3648 | 0.99 |
| 6526 | 3 | 4 | | | IV-2 | MNAT1 | 0.75 |
| 6527 | 3 | 4 | | | IV-2 | MORN3 | 0.91 |
| 6528 | 3 | 4 | | | IV-2 | MPST | 1.00 |
| 6529 | 3 | 4 | | | IV-2 | MREG | 0.89 |
| 6530 | 3 | 4 | | | IV-2 | MRPL11 | 0.94 |
| 6531 | 3 | 4 | | | IV-2 | MRPL21 | 0.82 |
| 6532 | 3 | 4 | | | IV-2 | MRPL22 | 0.95 |
| 6533 | 3 | 4 | | | IV-2 | MRPL24 | 0.89 |
| 6534 | 3 | 4 | | | IV-2 | MRPL34 | 0.84 |
| 6535 | 3 | 4 | | | IV-2 | MRPL36 | 0.76 |
| 6536 | 3 | 4 | | | IV-2 | MRPL39 | 0.95 |
| 6537 | 3 | 4 | | | IV-2 | MRPL40 | 0.91 |
| 6538 | 3 | 4 | | | IV-2 | MRPL43 | 0.97 |
| 6539 | 3 | 4 | | | IV-2 | MRPL45 | 0.91 |
| 6540 | 3 | 4 | | | IV-2 | MRPL48 | 0.88 |
| 6541 | 3 | 4 | | | IV-2 | MRPL49 | 0.85 |
| 6542 | 3 | 4 | | | IV-2 | MRPL53 | 0.94 |
| 6543 | 3 | 4 | | | IV-2 | MRPL54 | 0.83 |
| 6544 | 3 | 4 | | | IV-2 | MRPS15 | 0.82 |
| 6545 | 3 | 4 | | | IV-2 | MRPS18A | 0.97 |
| 6546 | 3 | 4 | | | IV-2 | MRPS23 | 0.97 |
| 6547 | 3 | 4 | | | IV-2 | MRPS26 | 0.92 |
| 6548 | 3 | 4 | | | IV-2 | MRPS27 | 0.94 |
| 6549 | 3 | 4 | | | IV-2 | MSMO1 | 0.85 |
| 6550 | 3 | 4 | | | IV-2 | MSRB3 | 0.91 |
| 6551 | 3 | 4 | | | IV-2 | MTCP1NB | 0.95 |
| 6552 | 3 | 4 | | | IV-2 | MTFP1 | 0.72 |
| 6553 | 3 | 4 | | | IV-2 | MTHFS | 0.97 |
| 6554 | 3 | 4 | | | IV-2 | MTRNR2L1 | 0.98 |
| 6555 | 3 | 4 | | | IV-2 | MYEOV | 0.81 |
| 6556 | 3 | 4 | | | IV-2 | MZT2B | 0.78 |
| 6557 | 3 | 4 | | | IV-2 | NCR1 | 0.84 |
| 6558 | 3 | 4 | | | IV-2 | NDN | 0.97 |
| 6559 | 3 | 4 | | | IV-2 | NDUFA1 | 0.69 |
| 6560 | 3 | 4 | | | IV-2 | NDUFA11 | 0.86 |
| 6561 | 3 | 4 | | | IV-2 | NDUFA13 | 0.93 |
| 6562 | 3 | 4 | | | IV-2 | NDUFA4 | 0.71 |
| 6563 | 3 | 4 | | | IV-2 | NDUFA7 | 0.89 |
| 6564 | 3 | 4 | | | IV-2 | NDUFB10 | 0.99 |
| 6565 | 3 | 4 | | | IV-2 | NDUFB11 | 0.85 |
| 6566 | 3 | 4 | | | IV-2 | NDUFB2 | 0.89 |
| 6567 | 3 | 4 | | | IV-2 | NDUFB4 | 0.98 |
| 6568 | 3 | 4 | | | IV-2 | NDUFB6 | 0.96 |
| 6569 | 3 | 4 | | | IV-2 | NDUFB7 | 0.79 |
| 6570 | 3 | 4 | | | IV-2 | NDUFB8 | 0.87 |
| 6571 | 3 | 4 | | | IV-2 | NDUFC2 | 0.79 |
| 6572 | 3 | 4 | | | IV-2 | NDUFS5 | 0.84 |
| 6573 | 3 | 4 | | | IV-2 | NHP2 | 0.92 |
| 6574 | 3 | 4 | | | IV-2 | NIPA1 | 0.92 |
| 6575 | 3 | 4 | | | IV-2 | NIPSNAP1 | 0.81 |
| 6576 | 3 | 4 | | | IV-2 | NMB | 0.98 |
| 6577 | 3 | 4 | | | IV-2 | NOL7 | 0.96 |
| 6578 | 3 | 4 | | | IV-2 | NPBWR1 | 0.99 |
| 6579 | 3 | 4 | | | IV-2 | NPM1 | 0.91 |
| 6580 | 3 | 4 | | | IV-2 | NR6A1 | 0.95 |
| 6581 | 3 | 4 | | | IV-2 | NRL | 0.99 |
| 6582 | 3 | 4 | | | IV-2 | NRSN2 | 0.97 |
| 6583 | 3 | 4 | | | IV-2 | NSA2 | 0.79 |
| 6584 | 3 | 4 | | | IV-2 | NT5DC1 | 1.00 |
| 6585 | 3 | 4 | | | IV-2 | NUDT14 | 0.97 |
| 6586 | 3 | 4 | | | IV-2 | NUDT3 | 0.86 |
| 6587 | 3 | 4 | | | IV-2 | NUDT4 | 0.88 |
| 6588 | 3 | 4 | | | IV-2 | NUTF2 | 0.80 |
| 6589 | 3 | 4 | | | IV-2 | NXPH4 | 1.00 |
| 6590 | 3 | 4 | | | IV-2 | NXT1 | 0.70 |
| 6591 | 3 | 4 | | | IV-2 | OAZ1 | 0.99 |
| 6592 | 3 | 4 | | | IV-2 | OAZ3 | 0.91 |
| 6593 | 3 | 4 | | | IV-2 | OBFC1 | 0.97 |
| 6594 | 3 | 4 | | | IV-2 | OCIAD2 | 0.72 |
| 6595 | 3 | 4 | | | IV-2 | OCM | 0.93 |
| 6596 | 3 | 4 | | | IV-2 | OLA1 | 0.97 |
| 6597 | 3 | 4 | | | IV-2 | ORAI1 | 0.94 |
| 6598 | 3 | 4 | | | IV-2 | PAAF1 | 1.00 |
| 6599 | 3 | 4 | | | IV-2 | PACSIN1 | 0.91 |
| 6600 | 3 | 4 | | | IV-2 | PARD6A | 0.88 |
| 6601 | 3 | 4 | | | IV-2 | PARS2 | 0.93 |
| 6602 | 3 | 4 | | | IV-2 | PCBD1 | 0.82 |
| 6603 | 3 | 4 | | | IV-2 | PCDH1 | 0.95 |
| 6604 | 3 | 4 | | | IV-2 | PCDH9 | 0.98 |
| 6605 | 3 | 4 | | | IV-2 | PEA15 | 0.95 |
| 6606 | 3 | 4 | | | IV-2 | PERP | 0.97 |
| 6607 | 3 | 4 | | | IV-2 | PEX2 | 0.92 |
| 6608 | 3 | 4 | | | IV-2 | PEX7 | 0.98 |
| 6609 | 3 | 4 | | | IV-2 | PFDN4 | 0.71 |
| 6610 | 3 | 4 | | | IV-2 | PFN1 | 0.90 |
| 6611 | 3 | 4 | | | IV-2 | PGAM1 | 0.99 |
| 6612 | 3 | 4 | | | IV-2 | PGAM4 | 0.86 |
| 6613 | 3 | 4 | | | IV-2 | PHB | 0.88 |
| 6614 | 3 | 4 | | | IV-2 | PHB2 | 0.88 |
| 6615 | 3 | 4 | | | IV-2 | PHF5A | 0.75 |
| 6616 | 3 | 4 | | | IV-2 | PHLDB2 | 0.88 |
| 6617 | 3 | 4 | | | IV-2 | PHOSPHO2 | 0.99 |
| 6618 | 3 | 4 | | | IV-2 | PIGF | 0.95 |
| 6619 | 3 | 4 | | | IV-2 | PIGY | 0.93 |
| 6620 | 3 | 4 | | | IV-2 | PIK3R3 | 0.93 |
| 6621 | 3 | 4 | | | IV-2 | PIN1P1 | 0.86 |
| 6622 | 3 | 4 | | | IV-2 | PINX1 | 0.89 |
| 6623 | 3 | 4 | | | IV-2 | PITPNC1 | 0.96 |
| 6624 | 3 | 4 | | | IV-2 | PLCXD2 | 0.89 |
| 6625 | 3 | 4 | | | IV-2 | PMS2P1 | 0.80 |
| 6626 | 3 | 4 | | | IV-2 | POLE3 | 1.00 |
| 6627 | 3 | 4 | | | IV-2 | POLR2C | 0.87 |
| 6628 | 3 | 4 | | | IV-2 | POLR2G | 0.96 |
| 6629 | 3 | 4 | | | IV-2 | POLR2K | 0.82 |
| 6630 | 3 | 4 | | | IV-2 | POLR2L | 0.70 |
| 6631 | 3 | 4 | | | IV-2 | POP7 | 0.89 |
| 6632 | 3 | 4 | | | IV-2 | PPA2 | 0.90 |
| 6633 | 3 | 4 | | | IV-2 | PPIA | 0.90 |
| 6634 | 3 | 4 | | | IV-2 | PPIL1 | 1.00 |
| 6635 | 3 | 4 | | | IV-2 | PPP1R15B | 0.92 |
| 6636 | 3 | 4 | | | IV-2 | PRADC1 | 0.68 |
| 6637 | 3 | 4 | | | IV-2 | PRKACB | 0.76 |
| 6638 | 3 | 4 | | | IV-2 | PRKACG | 0.77 |
| 6639 | 3 | 4 | | | IV-2 | PRKAR1B | 0.94 |
| 6640 | 3 | 4 | | | IV-2 | PRKCH | 0.92 |
| 6641 | 3 | 4 | | | IV-2 | PRKRIR | 0.95 |
| 6642 | 3 | 4 | | | IV-2 | PROCR | 0.82 |
| 6643 | 3 | 4 | | | IV-2 | PRR5L | 0.93 |
| 6644 | 3 | 4 | | | IV-2 | PSMD9 | 0.96 |
| 6645 | 3 | 4 | | | IV-2 | PSMG1 | 0.95 |
| 6646 | 3 | 4 | | | IV-2 | PTCD1 | 0.97 |
| 6647 | 3 | 4 | | | IV-2 | PTMA | 0.99 |
| 6648 | 3 | 4 | | | IV-2 | PTPLB | 0.98 |
| 6649 | 3 | 4 | | | IV-2 | PTPRCAP | 0.70 |
| 6650 | 3 | 4 | | | IV-2 | PTRH1 | 0.98 |
| 6651 | 3 | 4 | | | IV-2 | PTTG3P | 0.96 |
| 6652 | 3 | 4 | | | IV-2 | PVRL1 | 0.72 |
| 6653 | 3 | 4 | | | IV-2 | RAB33A | 0.70 |
| 6654 | 3 | 4 | | | IV-2 | RAB39B | 0.83 |
| 6655 | 3 | 4 | | | IV-2 | RAB6B | 0.85 |
| 6656 | 3 | 4 | | | IV-2 | RABAC1 | 0.93 |
| 6657 | 3 | 4 | | | IV-2 | RBBP9 | 0.93 |
| 6658 | 3 | 4 | | | IV-2 | RCN2 | 0.70 |
| 6659 | 3 | 4 | | | IV-2 | RGPD8 | 0.93 |
| 6660 | 3 | 4 | | | IV-2 | RHOF | 0.91 |
| 6661 | 3 | 4 | | | IV-2 | RHOU | 0.99 |
| 6662 | 3 | 4 | | | IV-2 | RNASEK-C17ORF49 | 0.92 |
| 6663 | 3 | 4 | | | IV-2 | RNF103-CHMP3 | 0.97 |
| 6664 | 3 | 4 | | | IV-2 | RNF11 | 0.97 |
| 6665 | 3 | 4 | | | IV-2 | RNF5P1 | 0.98 |
| 6666 | 3 | 4 | | | IV-2 | RPH3AL | 0.75 |
| 6667 | 3 | 4 | | | IV-2 | RPL10 | 0.87 |
| 6668 | 3 | 4 | | | IV-2 | RPL10A | 0.71 |
| 6669 | 3 | 4 | | | IV-2 | RPL11 | 0.73 |
| 6670 | 3 | 4 | | | IV-2 | RPL13A | 0.71 |
| 6671 | 3 | 4 | | | IV-2 | RPL13AP6 | 0.91 |
| 6672 | 3 | 4 | | | IV-2 | RPL14 | 0.75 |
| 6673 | 3 | 4 | | | IV-2 | RPL15 | 0.70 |
| 6674 | 3 | 4 | | | IV-2 | RPL19 | 0.87 |
| 6675 | 3 | 4 | | | IV-2 | RPL23A | 0.93 |
| 6676 | 3 | 4 | | | IV-2 | RPL23P8 | 0.94 |
| 6677 | 3 | 4 | | | IV-2 | RPL24 | 0.69 |
| 6678 | 3 | 4 | | | IV-2 | RPL26 | 0.84 |
| 6679 | 3 | 4 | | | IV-2 | RPL30 | 0.78 |
| 6680 | 3 | 4 | | | IV-2 | RPL35A | 0.68 |
| 6681 | 3 | 4 | | | IV-2 | RPL36 | 0.86 |
| 6682 | 3 | 4 | | | IV-2 | RPL36A-HNRNPH2 | 0.81 |
| 6683 | 3 | 4 | | | IV-2 | RPL36AL | 0.75 |
| 6684 | 3 | 4 | | | IV-2 | RPL37 | 0.97 |
| 6685 | 3 | 4 | | | IV-2 | RPL37A | 0.73 |
| 6686 | 3 | 4 | | | IV-2 | RPL4 | 0.78 |
| 6687 | 3 | 4 | | | IV-2 | RPL41 | 0.82 |
| 6688 | 3 | 4 | | | IV-2 | RPL5 | 0.72 |
| 6689 | 3 | 4 | | | IV-2 | RPL7 | 0.74 |
| 6690 | 3 | 4 | | | IV-2 | RPL7A | 0.70 |
| 6691 | 3 | 4 | | | IV-2 | RPP21 | 0.71 |
| 6692 | 3 | 4 | | | IV-2 | RPS11 | 0.73 |
| 6693 | 3 | 4 | | | IV-2 | RPS12 | 0.89 |
| 6694 | 3 | 4 | | | IV-2 | RPS13 | 0.77 |
| 6695 | 3 | 4 | | | IV-2 | RPS15 | 0.78 |
| 6696 | 3 | 4 | | | IV-2 | RPS15A | 0.79 |
| 6697 | 3 | 4 | | | IV-2 | RPS16 | 0.72 |
| 6698 | 3 | 4 | | | IV-2 | RPS18 | 0.92 |
| 6699 | 3 | 4 | | | IV-2 | RPS19 | 0.83 |
| 6700 | 3 | 4 | | | IV-2 | RPS19BP1 | 0.99 |
| 6701 | 3 | 4 | | | IV-2 | RPS2 | 0.69 |
| 6702 | 3 | 4 | | | IV-2 | RPS23 | 0.96 |
| 6703 | 3 | 4 | | | IV-2 | RPS24 | 0.88 |
| 6704 | 3 | 4 | | | IV-2 | RPS27A | 0.97 |
| 6705 | 3 | 4 | | | IV-2 | RPS29 | 0.71 |
| 6706 | 3 | 4 | | | IV-2 | RPS9 | 0.83 |
| 6707 | 3 | 4 | | | IV-2 | RSC1A1 | 0.98 |
| 6708 | 3 | 4 | | | IV-2 | RSL1D1 | 0.91 |
| 6709 | 3 | 4 | | | IV-2 | RSL24D1 | 0.87 |
| 6710 | 3 | 4 | | | IV-2 | RWDD1 | 0.84 |
| 6711 | 3 | 4 | | | IV-2 | S1PR4 | 0.98 |
| 6712 | 3 | 4 | | | IV-2 | SAMD3 | 0.68 |
| 6713 | 3 | 4 | | | IV-2 | SCARNA2 | 0.94 |
| 6714 | 3 | 4 | | | IV-2 | SCT | 0.96 |
| 6715 | 3 | 4 | | | IV-2 | SELT | 0.82 |

Fig. 40 - 36

| | | | | | | | | | | | | | | | |
|---|---|---|---|---|---|---|---|---|---|---|---|---|---|---|---|
| 6716 | 3 | 4 | | | IV-2 | SEMG1 | 0.97 | 6812 | 3 | 4 | | | IV-2 | TSPAN7 | 0.93 |
| 6717 | 3 | 4 | | | IV-2 | SEPW1 | 0.79 | 6813 | 3 | 4 | | | IV-2 | TSPO | 0.83 |
| 6718 | 3 | 4 | | | IV-2 | SERF2 | 0.82 | 6814 | 3 | 4 | | | IV-2 | TSPYL5 | 0.91 |
| 6719 | 3 | 4 | | | IV-2 | SERPINF2 | 0.90 | 6815 | 3 | 4 | | | IV-2 | TSTD1 | 0.84 |
| 6720 | 3 | 4 | | | IV-2 | SESN3 | 0.68 | 6816 | 3 | 4 | | | IV-2 | TTC38 | 0.92 |
| 6721 | 3 | 4 | | | IV-2 | SETD9 | 0.94 | 6817 | 3 | 4 | | | IV-2 | UBE2M | 0.95 |
| 6722 | 3 | 4 | | | IV-2 | SF3B5 | 0.97 | 6818 | 3 | 4 | | | IV-2 | UBE2MP1 | 0.99 |
| 6723 | 3 | 4 | | | IV-2 | SGCB | 0.98 | 6819 | 3 | 4 | | | IV-2 | UBE2NL | 0.80 |
| 6724 | 3 | 4 | | | IV-2 | SGPP2 | 0.92 | 6820 | 3 | 4 | | | IV-2 | UBE2Q2 | 0.89 |
| 6725 | 3 | 4 | | | IV-2 | SH3BGRL3 | 0.89 | 6821 | 3 | 4 | | | IV-2 | UBL4A | 0.97 |
| 6726 | 3 | 4 | | | IV-2 | SH3BP4 | 0.98 | 6822 | 3 | 4 | | | IV-2 | UBTD1 | 0.82 |
| 6727 | 3 | 4 | | | IV-2 | SH3BP5 | 0.99 | 6823 | 3 | 4 | | | IV-2 | UFC1 | 0.87 |
| 6728 | 3 | 4 | | | IV-2 | SHFM1 | 0.87 | 6824 | 3 | 4 | | | IV-2 | UGCG | 0.95 |
| 6729 | 3 | 4 | | | IV-2 | SIVA1 | 0.86 | 6825 | 3 | 4 | | | IV-2 | UPB1 | 0.96 |
| 6730 | 3 | 4 | | | IV-2 | SLAMF6 | 0.85 | 6826 | 3 | 4 | | | IV-2 | UQCR10 | 0.82 |
| 6731 | 3 | 4 | | | IV-2 | SLAMF7 | 0.93 | 6827 | 3 | 4 | | | IV-2 | UQCR11 | 0.98 |
| 6732 | 3 | 4 | | | IV-2 | SLC20A2 | 0.97 | 6828 | 3 | 4 | | | IV-2 | UQCRB | 0.81 |
| 6733 | 3 | 4 | | | IV-2 | SLC25A33 | 0.96 | 6829 | 3 | 4 | | | IV-2 | UQCRBP1 | 0.73 |
| 6734 | 3 | 4 | | | IV-2 | SLC25A6 | 0.85 | 6830 | 3 | 4 | | | IV-2 | UQCRH | 0.77 |
| 6735 | 3 | 4 | | | IV-2 | SLC2A1 | 0.76 | 6831 | 3 | 4 | | | IV-2 | USE1 | 0.90 |
| 6736 | 3 | 4 | | | IV-2 | SLC2A8 | 0.78 | 6832 | 3 | 4 | | | IV-2 | UST | 0.82 |
| 6737 | 3 | 4 | | | IV-2 | SLC30A4 | 0.94 | 6833 | 3 | 4 | | | IV-2 | UTS2 | 1.00 |
| 6738 | 3 | 4 | | | IV-2 | SLC39A4 | 0.82 | 6834 | 3 | 4 | | | IV-2 | UXT | 0.78 |
| 6739 | 3 | 4 | | | IV-2 | SLC6A9 | 0.92 | 6835 | 3 | 4 | | | IV-2 | VANGL1 | 0.96 |
| 6740 | 3 | 4 | | | IV-2 | SLC7A5 | 0.97 | 6836 | 3 | 4 | | | IV-2 | VEPH1 | 0.99 |
| 6741 | 3 | 4 | | | IV-2 | SLC9A3R2 | 1.00 | 6837 | 3 | 4 | | | IV-2 | VHLL | 0.92 |
| 6742 | 3 | 4 | | | IV-2 | SMAGP | 0.80 | 6838 | 3 | 4 | | | IV-2 | VTI1B | 0.92 |
| 6743 | 3 | 4 | | | IV-2 | SMYD3 | 0.84 | 6839 | 3 | 4 | | | IV-2 | WASF1 | 0.96 |
| 6744 | 3 | 4 | | | IV-2 | SNRPN | 0.78 | 6840 | 3 | 4 | | | IV-2 | WIBG | 0.82 |
| 6745 | 3 | 4 | | | IV-2 | SNTA1 | 0.90 | 6841 | 3 | 4 | | | IV-2 | WTH3DI | 0.90 |
| 6746 | 3 | 4 | | | IV-2 | SNURF | 0.94 | 6842 | 3 | 4 | | | IV-2 | XCR1 | 0.98 |
| 6747 | 3 | 4 | | | IV-2 | SPDYC | 0.99 | 6843 | 3 | 4 | | | IV-2 | YES1 | 0.89 |
| 6748 | 3 | 4 | | | IV-2 | SPIN4 | 0.96 | 6844 | 3 | 4 | | | IV-2 | ZBTB38 | 0.88 |
| 6749 | 3 | 4 | | | IV-2 | SPIRE1 | 0.97 | 6845 | 3 | 4 | | | IV-2 | ZCCHC17 | 0.95 |
| 6750 | 3 | 4 | | | IV-2 | SPNS2 | 0.90 | 6846 | 3 | 4 | | | IV-2 | ZFAND1 | 0.83 |
| 6751 | 3 | 4 | | | IV-2 | SPTA1 | 0.99 | 6847 | 3 | 4 | | | IV-2 | ZFP30 | 0.99 |
| 6752 | 3 | 4 | | | IV-2 | SRP14 | 0.84 | 6848 | 3 | 4 | | | IV-2 | ZFP37 | 0.94 |
| 6753 | 3 | 4 | | | IV-2 | SSNA1 | 1.00 | 6849 | 3 | 4 | | | IV-2 | ZFP57 | 0.94 |
| 6754 | 3 | 4 | | | IV-2 | SSR2 | 0.90 | 6850 | 3 | 4 | | | IV-2 | ZFPM1 | 0.98 |
| 6755 | 3 | 4 | | | IV-2 | SSR4 | 0.89 | 6851 | 3 | 4 | | | IV-2 | ZNF134 | 0.97 |
| 6756 | 3 | 4 | | | IV-2 | ST13P4 | 0.95 | 6852 | 3 | 4 | | | IV-2 | ZNF205 | 1.00 |
| 6757 | 3 | 4 | | | IV-2 | ST3GAL4 | 0.96 | 6853 | 3 | 4 | | | IV-2 | ZNF32 | 0.75 |
| 6758 | 3 | 4 | | | IV-2 | ST6GALNAC1 | 0.98 | 6854 | 3 | 4 | | | IV-2 | ZNF329 | 1.00 |
| 6759 | 3 | 4 | | | IV-2 | ST8SIA6 | 0.93 | 6855 | 3 | 4 | | | IV-2 | ZNF35 | 0.88 |
| 6760 | 3 | 4 | | | IV-2 | STBD1 | 0.85 | 6856 | 3 | 4 | | | IV-2 | ZNF428 | 0.95 |
| 6761 | 3 | 4 | | | IV-2 | STX8 | 0.83 | 6857 | 3 | 4 | | | IV-2 | ZNF48 | 1.00 |
| 6762 | 3 | 4 | | | IV-2 | SUMO3 | 0.99 | 6858 | 3 | 4 | | | IV-2 | ZNF501 | 0.91 |
| 6763 | 3 | 4 | | | IV-2 | SYNC | 0.94 | 6859 | 3 | 4 | | | IV-2 | ZNF576 | 1.00 |
| 6764 | 3 | 4 | | | IV-2 | SYT11 | 0.93 | 6860 | 3 | 4 | | | IV-2 | ZNF584 | 0.82 |
| 6765 | 3 | 4 | | | IV-2 | TAS2R40 | 0.68 | 6861 | 3 | 4 | | | IV-2 | ZNF595 | 0.84 |
| 6766 | 3 | 4 | | | IV-2 | TBC1D12 | 0.99 | 6862 | 3 | 4 | | | IV-2 | ZNF608 | 0.99 |
| 6767 | 3 | 4 | | | IV-2 | TBC1D14 | 0.99 | 6863 | 3 | 4 | | | IV-2 | ZNF614 | 0.93 |
| 6768 | 3 | 4 | | | IV-2 | TC2N | 0.83 | 6864 | 3 | 4 | | | IV-2 | ZNF643 | 0.96 |
| 6769 | 3 | 4 | | | IV-2 | TCEAL3 | 0.95 | 6865 | 3 | 4 | | | IV-2 | ZNF649 | 0.98 |
| 6770 | 3 | 4 | | | IV-2 | TCEB2 | 0.78 | 6866 | 3 | 4 | | | IV-2 | ZNF658B | 0.96 |
| 6771 | 3 | 4 | | | IV-2 | TCTEX1D2 | 0.92 | 6867 | 3 | 4 | | | IV-2 | ZNF675 | 0.84 |
| 6772 | 3 | 4 | | | IV-2 | TEN1 | 0.91 | 6868 | 3 | 4 | | | IV-2 | ZNF709 | 0.95 |
| 6773 | 3 | 4 | | | IV-2 | TEX264 | 0.92 | 6869 | 3 | 4 | | | IV-2 | ZNF71 | 0.75 |
| 6774 | 3 | 4 | | | IV-2 | THAP7-AS1 | 0.83 | 6870 | 3 | 4 | | | IV-2 | ZNF718 | 0.82 |
| 6775 | 3 | 4 | | | IV-2 | THEM5 | 0.88 | 6871 | 3 | 4 | | | IV-2 | ZNF724P | 0.97 |
| 6776 | 3 | 4 | | | IV-2 | THEM6 | 0.74 | 6872 | 3 | 4 | | | IV-2 | ZNF827 | 0.98 |
| 6777 | 3 | 4 | | | IV-2 | THRA | 0.97 | 6873 | 3 | 4 | | | IV-2 | ZNF837 | 0.96 |
| 6778 | 3 | 4 | | | IV-2 | TIFAB | 0.86 | 6874 | 3 | 4 | | | IV-2 | ZNF883 | 0.96 |
| 6779 | 3 | 4 | | | IV-2 | TIGD6 | 0.96 | 6875 | 3 | 4 | | | IV-2 | ZP3 | 0.93 |
| 6780 | 3 | 4 | | | IV-2 | TIMM17B | 0.94 | 6876 | 3 | 4 | | | IV-1 | 1/2-SBSRNA4 | 1.22 |
| 6781 | 3 | 4 | | | IV-2 | TIMM8B | 0.77 | 6877 | 3 | 4 | | | IV-1 | AAGAB | 1.44 |
| 6782 | 3 | 4 | | | IV-2 | TKTL1 | 0.85 | 6878 | 3 | 4 | | | IV-1 | AANAT | 1.27 |
| 6783 | 3 | 4 | | | IV-2 | TMCO3 | 0.87 | 6879 | 3 | 4 | | | IV-1 | AARSD1 | 1.15 |
| 6784 | 3 | 4 | | | IV-2 | TMED3 | 0.79 | 6880 | 3 | 4 | | | IV-1 | AASS | 1.42 |
| 6785 | 3 | 4 | | | IV-2 | TMEM109 | 0.99 | 6881 | 3 | 4 | | | IV-1 | ABCA5 | 1.22 |
| 6786 | 3 | 4 | | | IV-2 | TMEM141 | 0.83 | 6882 | 3 | 4 | | | IV-1 | ABCD2 | 1.11 |
| 6787 | 3 | 4 | | | IV-2 | TMEM148 | 0.95 | 6883 | 3 | 4 | | | IV-1 | ABCD3 | 1.49 |
| 6788 | 3 | 4 | | | IV-2 | TMEM216 | 0.84 | 6884 | 3 | 4 | | | IV-1 | ABCE1 | 1.44 |
| 6789 | 3 | 4 | | | IV-2 | TMEM38B | 0.98 | 6885 | 3 | 4 | | | IV-1 | ABCF2 | 1.43 |
| 6790 | 3 | 4 | | | IV-2 | TMEM63C | 0.92 | 6886 | 3 | 4 | | | IV-1 | ABHD12 | 1.47 |
| 6791 | 3 | 4 | | | IV-2 | TMEM64 | 0.99 | 6887 | 3 | 4 | | | IV-1 | ABHD13 | 1.30 |
| 6792 | 3 | 4 | | | IV-2 | TMEM9 | 0.76 | 6888 | 3 | 4 | | | IV-1 | ABHD14B | 1.06 |
| 6793 | 3 | 4 | | | IV-2 | TMEM97 | 0.90 | 6889 | 3 | 4 | | | IV-1 | ABHD4 | 1.36 |
| 6794 | 3 | 4 | | | IV-2 | TMIE | 0.94 | 6890 | 3 | 4 | | | IV-1 | ABHD6 | 1.24 |
| 6795 | 3 | 4 | | | IV-2 | TMUB1 | 0.81 | 6891 | 3 | 4 | | | IV-1 | ACAA2 | 1.06 |
| 6796 | 3 | 4 | | | IV-2 | TNFRSF21 | 0.90 | 6892 | 3 | 4 | | | IV-1 | ACACA | 1.41 |
| 6797 | 3 | 4 | | | IV-2 | TNFSF12 | 0.69 | 6893 | 3 | 4 | | | IV-1 | ACADM | 1.38 |
| 6798 | 3 | 4 | | | IV-2 | TNNC2 | 0.99 | 6894 | 3 | 4 | | | IV-1 | ACADSB | 1.28 |
| 6799 | 3 | 4 | | | IV-2 | TNXA | 0.98 | 6895 | 3 | 4 | | | IV-1 | ACAT1 | 1.17 |
| 6800 | 3 | 4 | | | IV-2 | TNXB | 0.95 | 6896 | 3 | 4 | | | IV-1 | ACBD6 | 1.09 |
| 6801 | 3 | 4 | | | IV-2 | TOMM22 | 0.82 | 6897 | 3 | 4 | | | IV-1 | ACCN2 | 1.02 |
| 6802 | 3 | 4 | | | IV-2 | TOMM6 | 0.89 | 6898 | 3 | 4 | | | IV-1 | ACN9 | 1.05 |
| 6803 | 3 | 4 | | | IV-2 | TOMM7 | 0.88 | 6899 | 3 | 4 | | | IV-1 | ACOT1 | 1.05 |
| 6804 | 3 | 4 | | | IV-2 | TOX | 0.72 | 6900 | 3 | 4 | | | IV-1 | ACOT7 | 1.24 |
| 6805 | 3 | 4 | | | IV-2 | TP53TG1 | 0.73 | 6901 | 3 | 4 | | | IV-1 | ACOT8 | 1.40 |
| 6806 | 3 | 4 | | | IV-2 | TPGS1 | 0.95 | 6902 | 3 | 4 | | | IV-1 | ACP1 | 1.24 |
| 6807 | 3 | 4 | | | IV-2 | TPTEP1 | 0.73 | 6903 | 3 | 4 | | | IV-1 | ACP6 | 1.48 |
| 6808 | 3 | 4 | | | IV-2 | TRAPPC1 | 0.95 | 6904 | 3 | 4 | | | IV-1 | ACPP | 1.12 |
| 6809 | 3 | 4 | | | IV-2 | TRAPPC6A | 0.91 | 6905 | 3 | 4 | | | IV-1 | ACSM3 | 1.23 |
| 6810 | 3 | 4 | | | IV-2 | TRAT1 | 0.92 | 6906 | 3 | 4 | | | IV-1 | ACTB | 1.14 |
| 6811 | 3 | 4 | | | IV-2 | TRIB3 | 0.95 | 6907 | 3 | 4 | | | IV-1 | ACTG1 | 1.34 |

Fig. 40 - 37

| | | | | | | | | | | | | | | |
|---|---|---|---|---|---|---|---|---|---|---|---|---|---|---|
| 6908 | 3 | 4 | | | IV-1 | ACTL10 | 1.32 | 7004 | 3 | 4 | | | IV-1 | ARF3 | 1.47 |
| 6909 | 3 | 4 | | | IV-1 | ACTR10 | 1.46 | 7005 | 3 | 4 | | | IV-1 | ARF4 | 1.22 |
| 6910 | 3 | 4 | | | IV-1 | ACTR3 | 1.40 | 7006 | 3 | 4 | | | IV-1 | ARF6 | 1.41 |
| 6911 | 3 | 4 | | | IV-1 | ACTR3B | 1.42 | 7007 | 3 | 4 | | | IV-1 | ARFGAP3 | 1.38 |
| 6912 | 3 | 4 | | | IV-1 | ACTR6 | 1.35 | 7008 | 3 | 4 | | | IV-1 | ARFIP2 | 1.50 |
| 6913 | 3 | 4 | | | IV-1 | ACTR8 | 1.48 | 7009 | 3 | 4 | | | IV-1 | ARGFXP2 | 1.29 |
| 6914 | 3 | 4 | | | IV-1 | ACVRL1 | 1.34 | 7010 | 3 | 4 | | | IV-1 | ARHGAP11B | 1.49 |
| 6915 | 3 | 4 | | | IV-1 | ACY1 | 1.10 | 7011 | 3 | 4 | | | IV-1 | ARHGAP12 | 1.49 |
| 6916 | 3 | 4 | | | IV-1 | ADA | 1.34 | 7012 | 3 | 4 | | | IV-1 | ARHGAP15 | 1.14 |
| 6917 | 3 | 4 | | | IV-1 | ADAM19 | 1.13 | 7013 | 3 | 4 | | | IV-1 | ARHGAP35 | 1.18 |
| 6918 | 3 | 4 | | | IV-1 | ADAMTS10 | 1.07 | 7014 | 3 | 4 | | | IV-1 | ARHGAP5-AS1 | 1.00 |
| 6919 | 3 | 4 | | | IV-1 | ADAP1 | 1.14 | 7015 | 3 | 4 | | | IV-1 | ARHGDIA | 1.20 |
| 6920 | 3 | 4 | | | IV-1 | ADCK2 | 1.29 | 7016 | 3 | 4 | | | IV-1 | ARHGEF3 | 1.38 |
| 6921 | 3 | 4 | | | IV-1 | ADD1 | 1.42 | 7017 | 3 | 4 | | | IV-1 | ARHGEF35 | 1.20 |
| 6922 | 3 | 4 | | | IV-1 | ADD3 | 1.49 | 7018 | 3 | 4 | | | IV-1 | ARHGEF5 | 1.07 |
| 6923 | 3 | 4 | | | IV-1 | ADH5 | 1.11 | 7019 | 3 | 4 | | | IV-1 | ARHGEF9 | 1.01 |
| 6924 | 3 | 4 | | | IV-1 | ADI1 | 1.12 | 7020 | 3 | 4 | | | IV-1 | ARID5A | 1.31 |
| 6925 | 3 | 4 | | | IV-1 | ADIPOR2 | 1.39 | 7021 | 3 | 4 | | | IV-1 | ARL1 | 1.29 |
| 6926 | 3 | 4 | | | IV-1 | ADK | 1.17 | 7022 | 3 | 4 | | | IV-1 | ARL10 | 1.16 |
| 6927 | 3 | 4 | | | IV-1 | ADM2 | 1.14 | 7023 | 3 | 4 | | | IV-1 | ARL17B | 1.44 |
| 6928 | 3 | 4 | | | IV-1 | ADNP2 | 1.36 | 7024 | 3 | 4 | | | IV-1 | ARL2 | 1.21 |
| 6929 | 3 | 4 | | | IV-1 | AGAP3 | 1.03 | 7025 | 3 | 4 | | | IV-1 | ARL2BP | 1.41 |
| 6930 | 3 | 4 | | | IV-1 | AGFG2 | 1.28 | 7026 | 3 | 4 | | | IV-1 | ARL3 | 1.03 |
| 6931 | 3 | 4 | | | IV-1 | AGPAT1 | 1.29 | 7027 | 3 | 4 | | | IV-1 | ARL4C | 1.13 |
| 6932 | 3 | 4 | | | IV-1 | AGPAT2 | 1.21 | 7028 | 3 | 4 | | | IV-1 | ARL4D | 1.19 |
| 6933 | 3 | 4 | | | IV-1 | AGTPBP1 | 1.31 | 7029 | 3 | 4 | | | IV-1 | ARL5A | 1.15 |
| 6934 | 3 | 4 | | | IV-1 | AGTRAP | 1.44 | 7030 | 3 | 4 | | | IV-1 | ARL6IP1 | 1.38 |
| 6935 | 3 | 4 | | | IV-1 | AHSA1 | 1.33 | 7031 | 3 | 4 | | | IV-1 | ARL6IP4 | 1.01 |
| 6936 | 3 | 4 | | | IV-1 | AIDA | 1.44 | 7032 | 3 | 4 | | | IV-1 | ARL6IP5 | 1.16 |
| 6937 | 3 | 4 | | | IV-1 | AIF1 | 1.33 | 7033 | 3 | 4 | | | IV-1 | ARL8A | 1.38 |
| 6938 | 3 | 4 | | | IV-1 | AIG1 | 1.11 | 7034 | 3 | 4 | | | IV-1 | ARMC1 | 1.12 |
| 6939 | 3 | 4 | | | IV-1 | AIMP2 | 1.20 | 7035 | 3 | 4 | | | IV-1 | ARMC10 | 1.50 |
| 6940 | 3 | 4 | | | IV-1 | AIP | 1.06 | 7036 | 3 | 4 | | | IV-1 | ARMC2 | 1.45 |
| 6941 | 3 | 4 | | | IV-1 | AK3 | 1.38 | 7037 | 3 | 4 | | | IV-1 | ARMCX4 | 1.47 |
| 6942 | 3 | 4 | | | IV-1 | AKD1 | 1.50 | 7038 | 3 | 4 | | | IV-1 | ARMCX6 | 1.43 |
| 6943 | 3 | 4 | | | IV-1 | AKIP1 | 1.44 | 7039 | 3 | 4 | | | IV-1 | ARPC1B | 1.45 |
| 6944 | 3 | 4 | | | IV-1 | AKR1B1 | 1.19 | 7040 | 3 | 4 | | | IV-1 | ARPC2 | 1.27 |
| 6945 | 3 | 4 | | | IV-1 | AKR7A2 | 1.26 | 7041 | 3 | 4 | | | IV-1 | ARPC3 | 1.16 |
| 6946 | 3 | 4 | | | IV-1 | AKR7A2P1 | 1.13 | 7042 | 3 | 4 | | | IV-1 | ARPC4 | 1.13 |
| 6947 | 3 | 4 | | | IV-1 | AKT1 | 1.28 | 7043 | 3 | 4 | | | IV-1 | ARPC5 | 1.39 |
| 6948 | 3 | 4 | | | IV-1 | AKT3 | 1.47 | 7044 | 3 | 4 | | | IV-1 | ARPP19 | 1.22 |
| 6949 | 3 | 4 | | | IV-1 | ALDH4A1 | 1.29 | 7045 | 3 | 4 | | | IV-1 | ARRB1 | 1.06 |
| 6950 | 3 | 4 | | | IV-1 | ALDH9A1 | 1.24 | 7046 | 3 | 4 | | | IV-1 | ARSK | 1.10 |
| 6951 | 3 | 4 | | | IV-1 | ALDOA | 1.20 | 7047 | 3 | 4 | | | IV-1 | ASB7 | 1.41 |
| 6952 | 3 | 4 | | | IV-1 | ALDOC | 1.14 | 7048 | 3 | 4 | | | IV-1 | ASB9P1 | 1.38 |
| 6953 | 3 | 4 | | | IV-1 | ALG11 | 1.49 | 7049 | 3 | 4 | | | IV-1 | ASCC1 | 1.30 |
| 6954 | 3 | 4 | | | IV-1 | ALG2 | 1.49 | 7050 | 3 | 4 | | | IV-1 | ASF1A | 1.20 |
| 6955 | 3 | 4 | | | IV-1 | ALG9 | 1.45 | 7051 | 3 | 4 | | | IV-1 | ASMTL | 1.27 |
| 6956 | 3 | 4 | | | IV-1 | ALKBH1 | 1.42 | 7052 | 3 | 4 | | | IV-1 | ASUN | 1.44 |
| 6957 | 3 | 4 | | | IV-1 | ALKBH3 | 1.19 | 7053 | 3 | 4 | | | IV-1 | ASXL2 | 1.45 |
| 6958 | 3 | 4 | | | IV-1 | ALKBH5 | 1.12 | 7054 | 3 | 4 | | | IV-1 | ATAD1 | 1.33 |
| 6959 | 3 | 4 | | | IV-1 | ALKBH8 | 1.32 | 7055 | 3 | 4 | | | IV-1 | ATAD5 | 1.12 |
| 6960 | 3 | 4 | | | IV-1 | ALS2 | 1.16 | 7056 | 3 | 4 | | | IV-1 | ATE1 | 1.36 |
| 6961 | 3 | 4 | | | IV-1 | ALX3 | 1.25 | 7057 | 3 | 4 | | | IV-1 | ATF1 | 1.02 |
| 6962 | 3 | 4 | | | IV-1 | ALYREF | 1.44 | 7058 | 3 | 4 | | | IV-1 | ATF4 | 1.31 |
| 6963 | 3 | 4 | | | IV-1 | AMFR | 1.24 | 7059 | 3 | 4 | | | IV-1 | ATG3 | 1.32 |
| 6964 | 3 | 4 | | | IV-1 | AMOT | 1.05 | 7060 | 3 | 4 | | | IV-1 | ATG4A | 1.47 |
| 6965 | 3 | 4 | | | IV-1 | AMPD3 | 1.50 | 7061 | 3 | 4 | | | IV-1 | ATG5 | 1.50 |
| 6966 | 3 | 4 | | | IV-1 | AMY2A | 1.12 | 7062 | 3 | 4 | | | IV-1 | ATIC | 1.38 |
| 6967 | 3 | 4 | | | IV-1 | AMZ2 | 1.09 | 7063 | 3 | 4 | | | IV-1 | ATMIN | 1.22 |
| 6968 | 3 | 4 | | | IV-1 | ANAPC10 | 1.33 | 7064 | 3 | 4 | | | IV-1 | ATP11B | 1.49 |
| 6969 | 3 | 4 | | | IV-1 | ANAPC13 | 1.49 | 7065 | 3 | 4 | | | IV-1 | ATP2A3 | 1.35 |
| 6970 | 3 | 4 | | | IV-1 | ANAPC16 | 1.14 | 7066 | 3 | 4 | | | IV-1 | ATP2B4 | 1.33 |
| 6971 | 3 | 4 | | | IV-1 | ANGPT1 | 1.00 | 7067 | 3 | 4 | | | IV-1 | ATP5A1 | 1.39 |
| 6972 | 3 | 4 | | | IV-1 | ANKH | 1.37 | 7068 | 3 | 4 | | | IV-1 | ATP5C1 | 1.28 |
| 6973 | 3 | 4 | | | IV-1 | ANKHD1-EIF4EBP3 | 1.27 | 7069 | 3 | 4 | | | IV-1 | ATP5D | 1.03 |
| 6974 | 3 | 4 | | | IV-1 | ANKLE1 | 1.35 | 7070 | 3 | 4 | | | IV-1 | ATP5F1 | 1.03 |
| 6975 | 3 | 4 | | | IV-1 | ANKRD13C | 1.23 | 7071 | 3 | 4 | | | IV-1 | ATP5G1 | 1.15 |
| 6976 | 3 | 4 | | | IV-1 | ANKRD23 | 1.27 | 7072 | 3 | 4 | | | IV-1 | ATP5G2 | 1.17 |
| 6977 | 3 | 4 | | | IV-1 | ANKRD34A | 1.15 | 7073 | 3 | 4 | | | IV-1 | ATP5G3 | 1.48 |
| 6978 | 3 | 4 | | | IV-1 | ANKRD36 | 1.48 | 7074 | 3 | 4 | | | IV-1 | ATP5J | 1.26 |
| 6979 | 3 | 4 | | | IV-1 | ANKRD36B | 1.22 | 7075 | 3 | 4 | | | IV-1 | ATP5L | 1.13 |
| 6980 | 3 | 4 | | | IV-1 | ANKRD39 | 1.01 | 7076 | 3 | 4 | | | IV-1 | ATP5SL | 1.29 |
| 6981 | 3 | 4 | | | IV-1 | ANKRD46 | 1.31 | 7077 | 3 | 4 | | | IV-1 | ATP6V0A2 | 1.46 |
| 6982 | 3 | 4 | | | IV-1 | ANKRD6 | 1.40 | 7078 | 3 | 4 | | | IV-1 | ATP6V0C | 1.11 |
| 6983 | 3 | 4 | | | IV-1 | ANKS6 | 1.27 | 7079 | 3 | 4 | | | IV-1 | ATP6V0D1 | 1.36 |
| 6984 | 3 | 4 | | | IV-1 | ANP32A | 1.20 | 7080 | 3 | 4 | | | IV-1 | ATP6V0E2 | 1.03 |
| 6985 | 3 | 4 | | | IV-1 | ANP32A-IT1 | 1.01 | 7081 | 3 | 4 | | | IV-1 | ATP6V1G1 | 1.28 |
| 6986 | 3 | 4 | | | IV-1 | ANP32AP1 | 1.21 | 7082 | 3 | 4 | | | IV-1 | ATP6V1G2 | 1.39 |
| 6987 | 3 | 4 | | | IV-1 | ANP32B | 1.42 | 7083 | 3 | 4 | | | IV-1 | ATP8B5P | 1.23 |
| 6988 | 3 | 4 | | | IV-1 | ANP32C | 1.26 | 7084 | 3 | 4 | | | IV-1 | ATP9B | 1.41 |
| 6989 | 3 | 4 | | | IV-1 | ANP32E | 1.18 | 7085 | 3 | 4 | | | IV-1 | ATPAF1 | 1.17 |
| 6990 | 3 | 4 | | | IV-1 | ANXA11 | 1.36 | 7086 | 3 | 4 | | | IV-1 | ATPAF2 | 1.26 |
| 6991 | 3 | 4 | | | IV-1 | ANXA6 | 1.32 | 7087 | 3 | 4 | | | IV-1 | ATPIF1 | 1.33 |
| 6992 | 3 | 4 | | | IV-1 | ANXA7 | 1.41 | 7088 | 3 | 4 | | | IV-1 | ATXN1 | 1.34 |
| 6993 | 3 | 4 | | | IV-1 | AP1M2 | 1.18 | 7089 | 3 | 4 | | | IV-1 | ATXN10 | 1.40 |
| 6994 | 3 | 4 | | | IV-1 | AP1S1 | 1.11 | 7090 | 3 | 4 | | | IV-1 | ATXN1L | 1.45 |
| 6995 | 3 | 4 | | | IV-1 | AP2M1 | 1.18 | 7091 | 3 | 4 | | | IV-1 | ATXN7L3 | 1.48 |
| 6996 | 3 | 4 | | | IV-1 | AP2S1 | 1.32 | 7092 | 3 | 4 | | | IV-1 | ATXN7L3B | 1.44 |
| 6997 | 3 | 4 | | | IV-1 | AP3S1 | 1.36 | 7093 | 3 | 4 | | | IV-1 | AUH | 1.27 |
| 6998 | 3 | 4 | | | IV-1 | APH1A | 1.39 | 7094 | 3 | 4 | | | IV-1 | AURKAIP1 | 1.42 |
| 6999 | 3 | 4 | | | IV-1 | APIP | 1.25 | 7095 | 3 | 4 | | | IV-1 | AVEN | 1.41 |
| 7000 | 3 | 4 | | | IV-1 | APOBEC3C | 1.37 | 7096 | 3 | 4 | | | IV-1 | AXIN1 | 1.35 |
| 7001 | 3 | 4 | | | IV-1 | APOBEC3G | 1.29 | 7097 | 3 | 4 | | | IV-1 | AZIN1 | 1.05 |
| 7002 | 3 | 4 | | | IV-1 | APOPT1 | 1.13 | 7098 | 3 | 4 | | | IV-1 | AZU1 | 1.20 |
| 7003 | 3 | 4 | | | IV-1 | ARF1 | 1.35 | 7099 | 3 | 4 | | | IV-1 | B2M | 1.40 |

Fig. 40 - 38

| | | | | | | | | | | | | | | |
|---|---|---|---|---|---|---|---|---|---|---|---|---|---|---|
| 7100 | 3 | 4 | | | IV-1 | B3GALT4 | 1.42 | 7196 | 3 | 4 | | | IV-1 | C14orf169 | 1.27 |
| 7101 | 3 | 4 | | | IV-1 | B3GALTL | 1.42 | 7197 | 3 | 4 | | | IV-1 | C14orf2 | 1.20 |
| 7102 | 3 | 4 | | | IV-1 | B3GNT1 | 1.15 | 7198 | 3 | 4 | | | IV-1 | C14orf49 | 1.29 |
| 7103 | 3 | 4 | | | IV-1 | B4GALT1 | 1.49 | 7199 | 3 | 4 | | | IV-1 | C15orf23 | 1.13 |
| 7104 | 3 | 4 | | | IV-1 | B4GALT3 | 1.14 | 7200 | 3 | 4 | | | IV-1 | C15orf24 | 1.24 |
| 7105 | 3 | 4 | | | IV-1 | B4GALT7 | 1.29 | 7201 | 3 | 4 | | | IV-1 | C15orf34 | 1.22 |
| 7106 | 3 | 4 | | | IV-1 | BABAM1 | 1.07 | 7202 | 3 | 4 | | | IV-1 | C15orf44 | 1.11 |
| 7107 | 3 | 4 | | | IV-1 | BACE2 | 1.13 | 7203 | 3 | 4 | | | IV-1 | C15orf57 | 1.46 |
| 7108 | 3 | 4 | | | IV-1 | BAG2 | 1.02 | 7204 | 3 | 4 | | | IV-1 | C15orf61 | 1.38 |
| 7109 | 3 | 4 | | | IV-1 | BAG4 | 1.19 | 7205 | 3 | 4 | | | IV-1 | C16orf13 | 1.12 |
| 7110 | 3 | 4 | | | IV-1 | BAG5 | 1.46 | 7206 | 3 | 4 | | | IV-1 | C16orf42 | 1.32 |
| 7111 | 3 | 4 | | | IV-1 | BAHCC1 | 1.05 | 7207 | 3 | 4 | | | IV-1 | C16orf53 | 1.13 |
| 7112 | 3 | 4 | | | IV-1 | BAK1 | 1.50 | 7208 | 3 | 4 | | | IV-1 | C16orf54 | 1.33 |
| 7113 | 3 | 4 | | | IV-1 | BANF1 | 1.03 | 7209 | 3 | 4 | | | IV-1 | C16orf55 | 1.33 |
| 7114 | 3 | 4 | | | IV-1 | BAP1 | 1.32 | 7210 | 3 | 4 | | | IV-1 | C16orf57 | 1.10 |
| 7115 | 3 | 4 | | | IV-1 | BARD1 | 1.39 | 7211 | 3 | 4 | | | IV-1 | C16orf72 | 1.46 |
| 7116 | 3 | 4 | | | IV-1 | BBS12 | 1.30 | 7212 | 3 | 4 | | | IV-1 | C16orf80 | 1.11 |
| 7117 | 3 | 4 | | | IV-1 | BBS9 | 1.23 | 7213 | 3 | 4 | | | IV-1 | C16orf87 | 1.31 |
| 7118 | 3 | 4 | | | IV-1 | BCAP29 | 1.34 | 7214 | 3 | 4 | | | IV-1 | C17orf101 | 1.03 |
| 7119 | 3 | 4 | | | IV-1 | BCAP31 | 1.08 | 7215 | 3 | 4 | | | IV-1 | C17orf103 | 1.30 |
| 7120 | 3 | 4 | | | IV-1 | BCAT2 | 1.39 | 7216 | 3 | 4 | | | IV-1 | C17orf39 | 1.07 |
| 7121 | 3 | 4 | | | IV-1 | BCDIN3D | 1.20 | 7217 | 3 | 4 | | | IV-1 | C17orf49 | 1.01 |
| 7122 | 3 | 4 | | | IV-1 | BCKDHA | 1.25 | 7218 | 3 | 4 | | | IV-1 | C17orf51 | 1.27 |
| 7123 | 3 | 4 | | | IV-1 | BCL2 | 1.46 | 7219 | 3 | 4 | | | IV-1 | C17orf57 | 1.46 |
| 7124 | 3 | 4 | | | IV-1 | BCL2L11 | 1.32 | 7220 | 3 | 4 | | | IV-1 | C17orf59 | 1.11 |
| 7125 | 3 | 4 | | | IV-1 | BCL2L13 | 1.47 | 7221 | 3 | 4 | | | IV-1 | C17orf63 | 1.44 |
| 7126 | 3 | 4 | | | IV-1 | BCORL1 | 1.34 | 7222 | 3 | 4 | | | IV-1 | C17orf67 | 1.27 |
| 7127 | 3 | 4 | | | IV-1 | BDH1 | 1.48 | 7223 | 3 | 4 | | | IV-1 | C17orf75 | 1.12 |
| 7128 | 3 | 4 | | | IV-1 | BEAN1 | 1.04 | 7224 | 3 | 4 | | | IV-1 | C17orf81 | 1.21 |
| 7129 | 3 | 4 | | | IV-1 | BET1 | 1.49 | 7225 | 3 | 4 | | | IV-1 | C17orf89 | 1.21 |
| 7130 | 3 | 4 | | | IV-1 | BET1L | 1.20 | 7226 | 3 | 4 | | | IV-1 | C18orf54 | 1.28 |
| 7131 | 3 | 4 | | | IV-1 | BEX4 | 1.20 | 7227 | 3 | 4 | | | IV-1 | C19orf10 | 1.08 |
| 7132 | 3 | 4 | | | IV-1 | BEX5 | 1.00 | 7228 | 3 | 4 | | | IV-1 | C19orf12 | 1.38 |
| 7133 | 3 | 4 | | | IV-1 | BFAR | 1.30 | 7229 | 3 | 4 | | | IV-1 | C19orf24 | 1.08 |
| 7134 | 3 | 4 | | | IV-1 | BHLHE40 | 1.07 | 7230 | 3 | 4 | | | IV-1 | C19orf25 | 1.26 |
| 7135 | 3 | 4 | | | IV-1 | BHLHE41 | 1.29 | 7231 | 3 | 4 | | | IV-1 | C19orf29-AS1 | 1.49 |
| 7136 | 3 | 4 | | | IV-1 | BID | 1.43 | 7232 | 3 | 4 | | | IV-1 | C19orf38 | 1.32 |
| 7137 | 3 | 4 | | | IV-1 | BIN1 | 1.16 | 7233 | 3 | 4 | | | IV-1 | C19orf40 | 1.39 |
| 7138 | 3 | 4 | | | IV-1 | BLCAP | 1.41 | 7234 | 3 | 4 | | | IV-1 | C19orf47 | 1.06 |
| 7139 | 3 | 4 | | | IV-1 | BLMH | 1.34 | 7235 | 3 | 4 | | | IV-1 | C19orf48 | 1.09 |
| 7140 | 3 | 4 | | | IV-1 | BMS1P4 | 1.42 | 7236 | 3 | 4 | | | IV-1 | C19orf59 | 1.35 |
| 7141 | 3 | 4 | | | IV-1 | BNIPL | 1.33 | 7237 | 3 | 4 | | | IV-1 | C19orf73 | 1.29 |
| 7142 | 3 | 4 | | | IV-1 | BOD1 | 1.23 | 7238 | 3 | 4 | | | IV-1 | C1QTNF3 | 1.24 |
| 7143 | 3 | 4 | | | IV-1 | BOLA1 | 1.22 | 7239 | 3 | 4 | | | IV-1 | C1orf116 | 1.04 |
| 7144 | 3 | 4 | | | IV-1 | BOLA2 | 1.23 | 7240 | 3 | 4 | | | IV-1 | C1orf123 | 1.38 |
| 7145 | 3 | 4 | | | IV-1 | BOLA3 | 1.07 | 7241 | 3 | 4 | | | IV-1 | C1orf144 | 1.07 |
| 7146 | 3 | 4 | | | IV-1 | BPNT1 | 1.40 | 7242 | 3 | 4 | | | IV-1 | C1orf172 | 1.05 |
| 7147 | 3 | 4 | | | IV-1 | BRAF | 1.33 | 7243 | 3 | 4 | | | IV-1 | C1orf174 | 1.09 |
| 7148 | 3 | 4 | | | IV-1 | BRCC3 | 1.29 | 7244 | 3 | 4 | | | IV-1 | C1orf204 | 1.27 |
| 7149 | 3 | 4 | | | IV-1 | BRF2 | 1.42 | 7245 | 3 | 4 | | | IV-1 | C1orf212 | 1.07 |
| 7150 | 3 | 4 | | | IV-1 | BRIX1 | 1.27 | 7246 | 3 | 4 | | | IV-1 | C1orf216 | 1.38 |
| 7151 | 3 | 4 | | | IV-1 | BRK1 | 1.01 | 7247 | 3 | 4 | | | IV-1 | C1orf43 | 1.34 |
| 7152 | 3 | 4 | | | IV-1 | BRMS1L | 1.18 | 7248 | 3 | 4 | | | IV-1 | C1orf50 | 1.40 |
| 7153 | 3 | 4 | | | IV-1 | BRPF3 | 1.35 | 7249 | 3 | 4 | | | IV-1 | C1orf55 | 1.46 |
| 7154 | 3 | 4 | | | IV-1 | BSG | 1.21 | 7250 | 3 | 4 | | | IV-1 | C1orf74 | 1.23 |
| 7155 | 3 | 4 | | | IV-1 | BTBD1 | 1.40 | 7251 | 3 | 4 | | | IV-1 | C20orf11 | 1.30 |
| 7156 | 3 | 4 | | | IV-1 | BTBD10 | 1.42 | 7252 | 3 | 4 | | | IV-1 | C20orf20 | 1.07 |
| 7157 | 3 | 4 | | | IV-1 | BTBD6 | 1.15 | 7253 | 3 | 4 | | | IV-1 | C20orf30 | 1.17 |
| 7158 | 3 | 4 | | | IV-1 | BTF3L4 | 1.06 | 7254 | 3 | 4 | | | IV-1 | C20orf4 | 1.49 |
| 7159 | 3 | 4 | | | IV-1 | BTG1 | 1.44 | 7255 | 3 | 4 | | | IV-1 | C20orf43 | 1.40 |
| 7160 | 3 | 4 | | | IV-1 | BTG2 | 1.40 | 7256 | 3 | 4 | | | IV-1 | C20orf96 | 1.30 |
| 7161 | 3 | 4 | | | IV-1 | BUD13 | 1.35 | 7257 | 3 | 4 | | | IV-1 | C21orf33 | 1.27 |
| 7162 | 3 | 4 | | | IV-1 | BUD31 | 1.22 | 7258 | 3 | 4 | | | IV-1 | C21orf49 | 1.31 |
| 7163 | 3 | 4 | | | IV-1 | BZW1 | 1.39 | 7259 | 3 | 4 | | | IV-1 | C21orf63 | 1.34 |
| 7164 | 3 | 4 | | | IV-1 | BZW2 | 1.32 | 7260 | 3 | 4 | | | IV-1 | C21orf91 | 1.36 |
| 7165 | 3 | 4 | | | IV-1 | C10orf12 | 1.23 | 7261 | 3 | 4 | | | IV-1 | C22orf39 | 1.16 |
| 7166 | 3 | 4 | | | IV-1 | C10orf26 | 1.08 | 7262 | 3 | 4 | | | IV-1 | C22orf40 | 1.07 |
| 7167 | 3 | 4 | | | IV-1 | C10orf32 | 1.42 | 7263 | 3 | 4 | | | IV-1 | C2orf43 | 1.17 |
| 7168 | 3 | 4 | | | IV-1 | C10orf54 | 1.50 | 7264 | 3 | 4 | | | IV-1 | C2orf44 | 1.30 |
| 7169 | 3 | 4 | | | IV-1 | C10orf95 | 1.01 | 7265 | 3 | 4 | | | IV-1 | C2orf47 | 1.49 |
| 7170 | 3 | 4 | | | IV-1 | C11orf24 | 1.42 | 7266 | 3 | 4 | | | IV-1 | C2orf55 | 1.34 |
| 7171 | 3 | 4 | | | IV-1 | C11orf31 | 1.09 | 7267 | 3 | 4 | | | IV-1 | C2orf74 | 1.39 |
| 7172 | 3 | 4 | | | IV-1 | C11orf46 | 1.01 | 7268 | 3 | 4 | | | IV-1 | C2orf88 | 1.46 |
| 7173 | 3 | 4 | | | IV-1 | C11orf49 | 1.43 | 7269 | 3 | 4 | | | IV-1 | C3orf25 | 1.13 |
| 7174 | 3 | 4 | | | IV-1 | C11orf54 | 1.43 | 7270 | 3 | 4 | | | IV-1 | C3orf26 | 1.25 |
| 7175 | 3 | 4 | | | IV-1 | C11orf57 | 1.09 | 7271 | 3 | 4 | | | IV-1 | C3orf39 | 1.06 |
| 7176 | 3 | 4 | | | IV-1 | C11orf58 | 1.43 | 7272 | 3 | 4 | | | IV-1 | C3orf75 | 1.03 |
| 7177 | 3 | 4 | | | IV-1 | C11orf71 | 1.41 | 7273 | 3 | 4 | | | IV-1 | C4orf27 | 1.09 |
| 7178 | 3 | 4 | | | IV-1 | C11orf83 | 1.26 | 7274 | 3 | 4 | | | IV-1 | C4orf3 | 1.39 |
| 7179 | 3 | 4 | | | IV-1 | C11orf84 | 1.22 | 7275 | 3 | 4 | | | IV-1 | C4orf46 | 1.31 |
| 7180 | 3 | 4 | | | IV-1 | C12orf23 | 1.18 | 7276 | 3 | 4 | | | IV-1 | C4orf52 | 1.11 |
| 7181 | 3 | 4 | | | IV-1 | C12orf26 | 1.25 | 7277 | 3 | 4 | | | IV-1 | C5 | 1.18 |
| 7182 | 3 | 4 | | | IV-1 | C12orf44 | 1.09 | 7278 | 3 | 4 | | | IV-1 | C5orf55 | 1.03 |
| 7183 | 3 | 4 | | | IV-1 | C12orf45 | 1.19 | 7279 | 3 | 4 | | | IV-1 | C5orf62 | 1.20 |
| 7184 | 3 | 4 | | | IV-1 | C12orf49 | 1.19 | 7280 | 3 | 4 | | | IV-1 | C6orf115 | 1.29 |
| 7185 | 3 | 4 | | | IV-1 | C12orf52 | 1.06 | 7281 | 3 | 4 | | | IV-1 | C6orf130 | 1.38 |
| 7186 | 3 | 4 | | | IV-1 | C12orf65 | 1.15 | 7282 | 3 | 4 | | | IV-1 | C6orf48 | 1.27 |
| 7187 | 3 | 4 | | | IV-1 | C12orf66 | 1.30 | 7283 | 3 | 4 | | | IV-1 | C6orf70 | 1.37 |
| 7188 | 3 | 4 | | | IV-1 | C14orf1 | 1.12 | 7284 | 3 | 4 | | | IV-1 | C6orf72 | 1.33 |
| 7189 | 3 | 4 | | | IV-1 | C14orf109 | 1.33 | 7285 | 3 | 4 | | | IV-1 | C7orf11 | 1.14 |
| 7190 | 3 | 4 | | | IV-1 | C14orf119 | 1.33 | 7286 | 3 | 4 | | | IV-1 | C7orf13 | 1.13 |
| 7191 | 3 | 4 | | | IV-1 | C14orf126 | 1.07 | 7287 | 3 | 4 | | | IV-1 | C7orf29 | 1.12 |
| 7192 | 3 | 4 | | | IV-1 | C14orf129 | 1.08 | 7288 | 3 | 4 | | | IV-1 | C7orf41 | 1.44 |
| 7193 | 3 | 4 | | | IV-1 | C14orf133 | 1.40 | 7289 | 3 | 4 | | | IV-1 | C7orf42 | 1.48 |
| 7194 | 3 | 4 | | | IV-1 | C14orf142 | 1.00 | 7290 | 3 | 4 | | | IV-1 | C7orf44 | 1.28 |
| 7195 | 3 | 4 | | | IV-1 | C14orf166 | 1.11 | 7291 | 3 | 4 | | | IV-1 | C7orf46 | 1.26 |

Fig. 40 - 39

| | | | | | | | | | | | | | | | |
|---|---|---|---|---|---|---|---|---|---|---|---|---|---|---|---|
| 7292 | 3 | 4 | | | IV-1 | C7orf50 | 1.16 | 7388 | 3 | 4 | | | IV-1 | CCT4 | 1.04 |
| 7293 | 3 | 4 | | | IV-1 | C7orf60 | 1.23 | 7389 | 3 | 4 | | | IV-1 | CD1C | 1.10 |
| 7294 | 3 | 4 | | | IV-1 | C7orf70 | 1.22 | 7390 | 3 | 4 | | | IV-1 | CD28P2 | 1.45 |
| 7295 | 3 | 4 | | | IV-1 | C7orf73 | 1.08 | 7391 | 3 | 4 | | | IV-1 | CD302 | 1.14 |
| 7296 | 3 | 4 | | | IV-1 | C8orf33 | 1.09 | 7392 | 3 | 4 | | | IV-1 | CD3EAP | 1.16 |
| 7297 | 3 | 4 | | | IV-1 | C8orf37 | 1.22 | 7393 | 3 | 4 | | | IV-1 | CD44 | 1.43 |
| 7298 | 3 | 4 | | | IV-1 | C8orf44-SGK3 | 1.04 | 7394 | 3 | 4 | | | IV-1 | CD47 | 1.49 |
| 7299 | 3 | 4 | | | IV-1 | C8orf55 | 1.27 | 7395 | 3 | 4 | | | IV-1 | CD55 | 1.41 |
| 7300 | 3 | 4 | | | IV-1 | C9orf100 | 1.42 | 7396 | 3 | 4 | | | IV-1 | CD59 | 1.42 |
| 7301 | 3 | 4 | | | IV-1 | C9orf102 | 1.07 | 7397 | 3 | 4 | | | IV-1 | CD63 | 1.31 |
| 7302 | 3 | 4 | | | IV-1 | C9orf103 | 1.22 | 7398 | 3 | 4 | | | IV-1 | CD81 | 1.25 |
| 7303 | 3 | 4 | | | IV-1 | C9orf123 | 1.08 | 7399 | 3 | 4 | | | IV-1 | CD99L2 | 1.16 |
| 7304 | 3 | 4 | | | IV-1 | C9orf156 | 1.23 | 7400 | 3 | 4 | | | IV-1 | CDC14A | 1.50 |
| 7305 | 3 | 4 | | | IV-1 | C9orf23 | 1.18 | 7401 | 3 | 4 | | | IV-1 | CDC14C | 1.01 |
| 7306 | 3 | 4 | | | IV-1 | C9orf3 | 1.33 | 7402 | 3 | 4 | | | IV-1 | CDC20 | 1.04 |
| 7307 | 3 | 4 | | | IV-1 | C9orf41 | 1.22 | 7403 | 3 | 4 | | | IV-1 | CDC26 | 1.40 |
| 7308 | 3 | 4 | | | IV-1 | C9orf64 | 1.49 | 7404 | 3 | 4 | | | IV-1 | CDC37 | 1.48 |
| 7309 | 3 | 4 | | | IV-1 | C9orf69 | 1.33 | 7405 | 3 | 4 | | | IV-1 | CDC37L1 | 1.03 |
| 7310 | 3 | 4 | | | IV-1 | C9orf7 | 1.27 | 7406 | 3 | 4 | | | IV-1 | CDC42 | 1.12 |
| 7311 | 3 | 4 | | | IV-1 | C9orf82 | 1.33 | 7407 | 3 | 4 | | | IV-1 | CDC42EP3 | 1.38 |
| 7312 | 3 | 4 | | | IV-1 | C9orf85 | 1.31 | 7408 | 3 | 4 | | | IV-1 | CDC42SE2 | 1.14 |
| 7313 | 3 | 4 | | | IV-1 | C9orf86 | 1.41 | 7409 | 3 | 4 | | | IV-1 | CDC5L | 1.50 |
| 7314 | 3 | 4 | | | IV-1 | C9orf89 | 1.17 | 7410 | 3 | 4 | | | IV-1 | CDCA7 | 1.38 |
| 7315 | 3 | 4 | | | IV-1 | CA4 | 1.41 | 7411 | 3 | 4 | | | IV-1 | CDIPT | 1.44 |
| 7316 | 3 | 4 | | | IV-1 | CA5B | 1.43 | 7412 | 3 | 4 | | | IV-1 | CDK2AP1 | 1.47 |
| 7317 | 3 | 4 | | | IV-1 | CAB39 | 1.29 | 7413 | 3 | 4 | | | IV-1 | CDK4 | 1.35 |
| 7318 | 3 | 4 | | | IV-1 | CAB39L | 1.26 | 7414 | 3 | 4 | | | IV-1 | CDK5 | 1.40 |
| 7319 | 3 | 4 | | | IV-1 | CABIN1 | 1.41 | 7415 | 3 | 4 | | | IV-1 | CDK7 | 1.35 |
| 7320 | 3 | 4 | | | IV-1 | CACNA1A | 1.12 | 7416 | 3 | 4 | | | IV-1 | CDKL1 | 1.33 |
| 7321 | 3 | 4 | | | IV-1 | CACYBP | 1.29 | 7417 | 3 | 4 | | | IV-1 | CDKL5 | 1.31 |
| 7322 | 3 | 4 | | | IV-1 | CALD1 | 1.05 | 7418 | 3 | 4 | | | IV-1 | CDKN1B | 1.42 |
| 7323 | 3 | 4 | | | IV-1 | CALHM2 | 1.36 | 7419 | 3 | 4 | | | IV-1 | CDKN2AIP | 1.15 |
| 7324 | 3 | 4 | | | IV-1 | CALM1 | 1.18 | 7420 | 3 | 4 | | | IV-1 | CDR2 | 1.29 |
| 7325 | 3 | 4 | | | IV-1 | CALM2 | 1.46 | 7421 | 3 | 4 | | | IV-1 | CDRT15P1 | 1.28 |
| 7326 | 3 | 4 | | | IV-1 | CALM3 | 1.18 | 7422 | 3 | 4 | | | IV-1 | CEACAM19 | 1.19 |
| 7327 | 3 | 4 | | | IV-1 | CALR | 1.39 | 7423 | 3 | 4 | | | IV-1 | CEBPA | 1.34 |
| 7328 | 3 | 4 | | | IV-1 | CALU | 1.44 | 7424 | 3 | 4 | | | IV-1 | CENPB | 1.27 |
| 7329 | 3 | 4 | | | IV-1 | CAMK1D | 1.25 | 7425 | 3 | 4 | | | IV-1 | CENPF | 1.00 |
| 7330 | 3 | 4 | | | IV-1 | CAMKMT | 1.16 | 7426 | 3 | 4 | | | IV-1 | CENPJ | 1.24 |
| 7331 | 3 | 4 | | | IV-1 | CAMLG | 1.22 | 7427 | 3 | 4 | | | IV-1 | CENPM | 1.09 |
| 7332 | 3 | 4 | | | IV-1 | CAMTA1 | 1.18 | 7428 | 3 | 4 | | | IV-1 | CENPN | 1.36 |
| 7333 | 3 | 4 | | | IV-1 | CANT1 | 1.31 | 7429 | 3 | 4 | | | IV-1 | CEP57L1 | 1.24 |
| 7334 | 3 | 4 | | | IV-1 | CAPN1 | 1.43 | 7430 | 3 | 4 | | | IV-1 | CEP78 | 1.11 |
| 7335 | 3 | 4 | | | IV-1 | CAPNS1 | 1.32 | 7431 | 3 | 4 | | | IV-1 | CERK | 1.22 |
| 7336 | 3 | 4 | | | IV-1 | CARD14 | 1.06 | 7432 | 3 | 4 | | | IV-1 | CES2 | 1.45 |
| 7337 | 3 | 4 | | | IV-1 | CARHSP1 | 1.14 | 7433 | 3 | 4 | | | IV-1 | CETN3 | 1.05 |
| 7338 | 3 | 4 | | | IV-1 | CASC4 | 1.18 | 7434 | 3 | 4 | | | IV-1 | CETP | 1.01 |
| 7339 | 3 | 4 | | | IV-1 | CASP4 | 1.47 | 7435 | 3 | 4 | | | IV-1 | CGRRF1 | 1.48 |
| 7340 | 3 | 4 | | | IV-1 | CASS4 | 1.12 | 7436 | 3 | 4 | | | IV-1 | CHAC2 | 1.43 |
| 7341 | 3 | 4 | | | IV-1 | CAV1 | 1.09 | 7437 | 3 | 4 | | | IV-1 | CHCHD2 | 1.36 |
| 7342 | 3 | 4 | | | IV-1 | CBR3-AS1 | 1.49 | 7438 | 3 | 4 | | | IV-1 | CHCHD3 | 1.19 |
| 7343 | 3 | 4 | | | IV-1 | CBX1 | 1.34 | 7439 | 3 | 4 | | | IV-1 | CHCHD4 | 1.01 |
| 7344 | 3 | 4 | | | IV-1 | CBX4 | 1.49 | 7440 | 3 | 4 | | | IV-1 | CHCHD8 | 1.29 |
| 7345 | 3 | 4 | | | IV-1 | CBX6 | 1.39 | 7441 | 3 | 4 | | | IV-1 | CHEK1 | 1.05 |
| 7346 | 3 | 4 | | | IV-1 | CBX8 | 1.07 | 7442 | 3 | 4 | | | IV-1 | CHEK2 | 1.26 |
| 7347 | 3 | 4 | | | IV-1 | CBY1 | 1.42 | 7443 | 3 | 4 | | | IV-1 | CHIC2 | 1.34 |
| 7348 | 3 | 4 | | | IV-1 | CCDC104 | 1.06 | 7444 | 3 | 4 | | | IV-1 | CHM | 1.33 |
| 7349 | 3 | 4 | | | IV-1 | CCDC107 | 1.03 | 7445 | 3 | 4 | | | IV-1 | CHMP1A | 1.33 |
| 7350 | 3 | 4 | | | IV-1 | CCDC108B | 1.29 | 7446 | 3 | 4 | | | IV-1 | CHMP2A | 1.33 |
| 7351 | 3 | 4 | | | IV-1 | CCDC115 | 1.24 | 7447 | 3 | 4 | | | IV-1 | CHMP3 | 1.46 |
| 7352 | 3 | 4 | | | IV-1 | CCDC117 | 1.32 | 7448 | 3 | 4 | | | IV-1 | CHMP4A | 1.34 |
| 7353 | 3 | 4 | | | IV-1 | CCDC12 | 1.40 | 7449 | 3 | 4 | | | IV-1 | CHMP4B | 1.28 |
| 7354 | 3 | 4 | | | IV-1 | CCDC121 | 1.50 | 7450 | 3 | 4 | | | IV-1 | CHN1 | 1.06 |
| 7355 | 3 | 4 | | | IV-1 | CCDC126 | 1.12 | 7451 | 3 | 4 | | | IV-1 | CHP | 1.27 |
| 7356 | 3 | 4 | | | IV-1 | CCDC127 | 1.12 | 7452 | 3 | 4 | | | IV-1 | CHPF | 1.45 |
| 7357 | 3 | 4 | | | IV-1 | CCDC134 | 1.05 | 7453 | 3 | 4 | | | IV-1 | CHRAC1 | 1.23 |
| 7358 | 3 | 4 | | | IV-1 | CCDC147 | 1.21 | 7454 | 3 | 4 | | | IV-1 | CHST11 | 1.30 |
| 7359 | 3 | 4 | | | IV-1 | CCDC152 | 1.10 | 7455 | 3 | 4 | | | IV-1 | CHTF8 | 1.47 |
| 7360 | 3 | 4 | | | IV-1 | CCDC153 | 1.27 | 7456 | 3 | 4 | | | IV-1 | CHURC1 | 1.36 |
| 7361 | 3 | 4 | | | IV-1 | CCDC24 | 1.10 | 7457 | 3 | 4 | | | IV-1 | CIAO1 | 1.50 |
| 7362 | 3 | 4 | | | IV-1 | CCDC25 | 1.15 | 7458 | 3 | 4 | | | IV-1 | CIAPIN1 | 1.28 |
| 7363 | 3 | 4 | | | IV-1 | CCDC34 | 1.39 | 7459 | 3 | 4 | | | IV-1 | CIB1 | 1.26 |
| 7364 | 3 | 4 | | | IV-1 | CCDC53 | 1.33 | 7460 | 3 | 4 | | | IV-1 | CIC | 1.40 |
| 7365 | 3 | 4 | | | IV-1 | CCDC56 | 1.23 | 7461 | 3 | 4 | | | IV-1 | CIDEB | 1.38 |
| 7366 | 3 | 4 | | | IV-1 | CCDC57 | 1.25 | 7462 | 3 | 4 | | | IV-1 | CIDECP | 1.38 |
| 7367 | 3 | 4 | | | IV-1 | CCDC59 | 1.16 | 7463 | 3 | 4 | | | IV-1 | CISD1 | 1.03 |
| 7368 | 3 | 4 | | | IV-1 | CCDC69 | 1.16 | 7464 | 3 | 4 | | | IV-1 | CISD2 | 1.44 |
| 7369 | 3 | 4 | | | IV-1 | CCDC71 | 1.33 | 7465 | 3 | 4 | | | IV-1 | CIZ1 | 1.26 |
| 7370 | 3 | 4 | | | IV-1 | CCDC71L | 1.46 | 7466 | 3 | 4 | | | IV-1 | CKAP2 | 1.36 |
| 7371 | 3 | 4 | | | IV-1 | CCDC85B | 1.05 | 7467 | 3 | 4 | | | IV-1 | CKS1B | 1.02 |
| 7372 | 3 | 4 | | | IV-1 | CCDC85C | 1.08 | 7468 | 3 | 4 | | | IV-1 | CLCF1 | 1.10 |
| 7373 | 3 | 4 | | | IV-1 | CCDC90A | 1.18 | 7469 | 3 | 4 | | | IV-1 | CLDND1 | 1.09 |
| 7374 | 3 | 4 | | | IV-1 | CCDC92 | 1.12 | 7470 | 3 | 4 | | | IV-1 | CLIC1 | 1.14 |
| 7375 | 3 | 4 | | | IV-1 | CCDC94 | 1.08 | 7471 | 3 | 4 | | | IV-1 | CLIC2 | 1.36 |
| 7376 | 3 | 4 | | | IV-1 | CCDC96 | 1.47 | 7472 | 3 | 4 | | | IV-1 | CLIP1 | 1.42 |
| 7377 | 3 | 4 | | | IV-1 | CCNB1IP1 | 1.12 | 7473 | 3 | 4 | | | IV-1 | CLNS1A | 1.11 |
| 7378 | 3 | 4 | | | IV-1 | CCNC | 1.12 | 7474 | 3 | 4 | | | IV-1 | CLP1 | 1.38 |
| 7379 | 3 | 4 | | | IV-1 | CCND1 | 1.04 | 7475 | 3 | 4 | | | IV-1 | CLPP | 1.02 |
| 7380 | 3 | 4 | | | IV-1 | CCNE1 | 1.18 | 7476 | 3 | 4 | | | IV-1 | CLPX | 1.36 |
| 7381 | 3 | 4 | | | IV-1 | CCNH | 1.24 | 7477 | 3 | 4 | | | IV-1 | CLTA | 1.41 |
| 7382 | 3 | 4 | | | IV-1 | CCNI | 1.08 | 7478 | 3 | 4 | | | IV-1 | CLTB | 1.17 |
| 7383 | 3 | 4 | | | IV-1 | CCNY | 1.12 | 7479 | 3 | 4 | | | IV-1 | CLTCL1 | 1.40 |
| 7384 | 3 | 4 | | | IV-1 | CCPG1 | 1.50 | 7480 | 3 | 4 | | | IV-1 | CLUAP1 | 1.22 |
| 7385 | 3 | 4 | | | IV-1 | CCR8 | 1.26 | 7481 | 3 | 4 | | | IV-1 | CMPK1 | 1.18 |
| 7386 | 3 | 4 | | | IV-1 | CCS | 1.49 | 7482 | 3 | 4 | | | IV-1 | CNFN | 1.21 |
| 7387 | 3 | 4 | | | IV-1 | CCT3 | 1.47 | 7483 | 3 | 4 | | | IV-1 | CNIH | 1.26 |

Fig. 40 - 40

| | | | | | | | | | | | | | | |
|---|---|---|---|---|---|---|---|---|---|---|---|---|---|---|
| 7484 | 3 | 4 | | | IV-1 | CNKSR2 | 1.21 | 7580 | 3 | 4 | | | IV-1 | CYP2D6 | 1.12 |
| 7485 | 3 | 4 | | | IV-1 | CNN2 | 1.22 | 7581 | 3 | 4 | | | IV-1 | CYP51A1 | 1.38 |
| 7486 | 3 | 4 | | | IV-1 | CNN3 | 1.20 | 7582 | 3 | 4 | | | IV-1 | DAD1 | 1.34 |
| 7487 | 3 | 4 | | | IV-1 | CNOT7 | 1.48 | 7583 | 3 | 4 | | | IV-1 | DANCR | 1.03 |
| 7488 | 3 | 4 | | | IV-1 | CNPY2 | 1.16 | 7584 | 3 | 4 | | | IV-1 | DAP | 1.25 |
| 7489 | 3 | 4 | | | IV-1 | CNPY3 | 1.30 | 7585 | 3 | 4 | | | IV-1 | DAP3 | 1.33 |
| 7490 | 3 | 4 | | | IV-1 | CNTNAP1 | 1.15 | 7586 | 3 | 4 | | | IV-1 | DARS | 1.18 |
| 7491 | 3 | 4 | | | IV-1 | CNTNAP3B | 1.30 | 7587 | 3 | 4 | | | IV-1 | DARS2 | 1.40 |
| 7492 | 3 | 4 | | | IV-1 | COBRA1 | 1.41 | 7588 | 3 | 4 | | | IV-1 | DAXX | 1.38 |
| 7493 | 3 | 4 | | | IV-1 | COIL | 1.35 | 7589 | 3 | 4 | | | IV-1 | DAZAP2 | 1.42 |
| 7494 | 3 | 4 | | | IV-1 | COL19A1 | 1.22 | 7590 | 3 | 4 | | | IV-1 | DBF4 | 1.10 |
| 7495 | 3 | 4 | | | IV-1 | COL6A1 | 1.03 | 7591 | 3 | 4 | | | IV-1 | DBH | 1.24 |
| 7496 | 3 | 4 | | | IV-1 | COMMD2 | 1.05 | 7592 | 3 | 4 | | | IV-1 | DBP | 1.28 |
| 7497 | 3 | 4 | | | IV-1 | COMMD5 | 1.37 | 7593 | 3 | 4 | | | IV-1 | DCAF13 | 1.01 |
| 7498 | 3 | 4 | | | IV-1 | COMMD7 | 1.01 | 7594 | 3 | 4 | | | IV-1 | DCAF4L1 | 1.04 |
| 7499 | 3 | 4 | | | IV-1 | COMMD8 | 1.18 | 7595 | 3 | 4 | | | IV-1 | DCBLD2 | 1.27 |
| 7500 | 3 | 4 | | | IV-1 | COMMD9 | 1.27 | 7596 | 3 | 4 | | | IV-1 | DCLRE1B | 1.28 |
| 7501 | 3 | 4 | | | IV-1 | COPS2 | 1.30 | 7597 | 3 | 4 | | | IV-1 | DCP1B | 1.03 |
| 7502 | 3 | 4 | | | IV-1 | COPS3 | 1.04 | 7598 | 3 | 4 | | | IV-1 | DCTD | 1.28 |
| 7503 | 3 | 4 | | | IV-1 | COPS4 | 1.21 | 7599 | 3 | 4 | | | IV-1 | DCTN2 | 1.45 |
| 7504 | 3 | 4 | | | IV-1 | COPS5 | 1.40 | 7600 | 3 | 4 | | | IV-1 | DCTN3 | 1.05 |
| 7505 | 3 | 4 | | | IV-1 | COPS8 | 1.03 | 7601 | 3 | 4 | | | IV-1 | DCTN6 | 1.12 |
| 7506 | 3 | 4 | | | IV-1 | COQ10B | 1.39 | 7602 | 3 | 4 | | | IV-1 | DCTPP1 | 1.04 |
| 7507 | 3 | 4 | | | IV-1 | COQ3 | 1.34 | 7603 | 3 | 4 | | | IV-1 | DCUN1D1 | 1.34 |
| 7508 | 3 | 4 | | | IV-1 | COQ4 | 1.46 | 7604 | 3 | 4 | | | IV-1 | DCUN1D2 | 1.50 |
| 7509 | 3 | 4 | | | IV-1 | COQ7 | 1.39 | 7605 | 3 | 4 | | | IV-1 | DCXR | 1.24 |
| 7510 | 3 | 4 | | | IV-1 | COQ9 | 1.39 | 7606 | 3 | 4 | | | IV-1 | DDI2 | 1.09 |
| 7511 | 3 | 4 | | | IV-1 | CORO2B | 1.06 | 7607 | 3 | 4 | | | IV-1 | DDO | 1.39 |
| 7512 | 3 | 4 | | | IV-1 | COTL1 | 1.16 | 7608 | 3 | 4 | | | IV-1 | DDOST | 1.49 |
| 7513 | 3 | 4 | | | IV-1 | COX10 | 1.27 | 7609 | 3 | 4 | | | IV-1 | DDRGK1 | 1.42 |
| 7514 | 3 | 4 | | | IV-1 | COX11 | 1.05 | 7610 | 3 | 4 | | | IV-1 | DDT | 1.10 |
| 7515 | 3 | 4 | | | IV-1 | COX14 | 1.08 | 7611 | 3 | 4 | | | IV-1 | DDTL | 1.43 |
| 7516 | 3 | 4 | | | IV-1 | COX16 | 1.09 | 7612 | 3 | 4 | | | IV-1 | DDX10 | 1.43 |
| 7517 | 3 | 4 | | | IV-1 | COX17 | 1.08 | 7613 | 3 | 4 | | | IV-1 | DDX19B | 1.32 |
| 7518 | 3 | 4 | | | IV-1 | COX4NB | 1.32 | 7614 | 3 | 4 | | | IV-1 | DDX28 | 1.24 |
| 7519 | 3 | 4 | | | IV-1 | COX5B | 1.15 | 7615 | 3 | 4 | | | IV-1 | DDX49 | 1.23 |
| 7520 | 3 | 4 | | | IV-1 | COX6A1 | 1.08 | 7616 | 3 | 4 | | | IV-1 | DDX50 | 1.01 |
| 7521 | 3 | 4 | | | IV-1 | COX6C | 1.21 | 7617 | 3 | 4 | | | IV-1 | DDX6 | 1.27 |
| 7522 | 3 | 4 | | | IV-1 | COX7A2L | 1.34 | 7618 | 3 | 4 | | | IV-1 | DECR2 | 1.14 |
| 7523 | 3 | 4 | | | IV-1 | COX7C | 1.15 | 7619 | 3 | 4 | | | IV-1 | DEDD2 | 1.47 |
| 7524 | 3 | 4 | | | IV-1 | COX8A | 1.22 | 7620 | 3 | 4 | | | IV-1 | DEGS1 | 1.47 |
| 7525 | 3 | 4 | | | IV-1 | CPD | 1.38 | 7621 | 3 | 4 | | | IV-1 | DENND2D | 1.47 |
| 7526 | 3 | 4 | | | IV-1 | CPNE2 | 1.11 | 7622 | 3 | 4 | | | IV-1 | DENR | 1.44 |
| 7527 | 3 | 4 | | | IV-1 | CPNE3 | 1.46 | 7623 | 3 | 4 | | | IV-1 | DERL1 | 1.28 |
| 7528 | 3 | 4 | | | IV-1 | CPQ | 1.40 | 7624 | 3 | 4 | | | IV-1 | DFFA | 1.26 |
| 7529 | 3 | 4 | | | IV-1 | CRABP2 | 1.34 | 7625 | 3 | 4 | | | IV-1 | DGKG | 1.49 |
| 7530 | 3 | 4 | | | IV-1 | CRCP | 1.08 | 7626 | 3 | 4 | | | IV-1 | DHCR7 | 1.10 |
| 7531 | 3 | 4 | | | IV-1 | CREB3 | 1.35 | 7627 | 3 | 4 | | | IV-1 | DHRS13 | 1.04 |
| 7532 | 3 | 4 | | | IV-1 | CREBL2 | 1.36 | 7628 | 3 | 4 | | | IV-1 | DHRS4L2 | 1.49 |
| 7533 | 3 | 4 | | | IV-1 | CRELD2 | 1.25 | 7629 | 3 | 4 | | | IV-1 | DHRSX | 1.22 |
| 7534 | 3 | 4 | | | IV-1 | CRIM1 | 1.22 | 7630 | 3 | 4 | | | IV-1 | DIMT1 | 1.38 |
| 7535 | 3 | 4 | | | IV-1 | CRIPT | 1.10 | 7631 | 3 | 4 | | | IV-1 | DIS3L | 1.49 |
| 7536 | 3 | 4 | | | IV-1 | CRLF3 | 1.45 | 7632 | 3 | 4 | | | IV-1 | DISP1 | 1.47 |
| 7537 | 3 | 4 | | | IV-1 | CRTAP | 1.12 | 7633 | 3 | 4 | | | IV-1 | DLEU1 | 1.07 |
| 7538 | 3 | 4 | | | IV-1 | CRY1 | 1.36 | 7634 | 3 | 4 | | | IV-1 | DLL1 | 1.26 |
| 7539 | 3 | 4 | | | IV-1 | CRYL1 | 1.17 | 7635 | 3 | 4 | | | IV-1 | DNAJA2 | 1.31 |
| 7540 | 3 | 4 | | | IV-1 | CSDE1 | 1.47 | 7636 | 3 | 4 | | | IV-1 | DNAJA3 | 1.40 |
| 7541 | 3 | 4 | | | IV-1 | CSNK1A1L | 1.26 | 7637 | 3 | 4 | | | IV-1 | DNAJB1 | 1.24 |
| 7542 | 3 | 4 | | | IV-1 | CSNK1A1P1 | 1.40 | 7638 | 3 | 4 | | | IV-1 | DNAJC14 | 1.38 |
| 7543 | 3 | 4 | | | IV-1 | CSNK1G3 | 1.37 | 7639 | 3 | 4 | | | IV-1 | DNAJC17 | 1.28 |
| 7544 | 3 | 4 | | | IV-1 | CSNK2A1 | 1.29 | 7640 | 3 | 4 | | | IV-1 | DNAJC21 | 1.41 |
| 7545 | 3 | 4 | | | IV-1 | CSNK2A1P | 1.18 | 7641 | 3 | 4 | | | IV-1 | DNAJC24 | 1.24 |
| 7546 | 3 | 4 | | | IV-1 | CSNK2A2 | 1.49 | 7642 | 3 | 4 | | | IV-1 | DNAJC25 | 1.48 |
| 7547 | 3 | 4 | | | IV-1 | CSNK2B | 1.41 | 7643 | 3 | 4 | | | IV-1 | DNAJC3 | 1.49 |
| 7548 | 3 | 4 | | | IV-1 | CSRP1 | 1.33 | 7644 | 3 | 4 | | | IV-1 | DNAJC4 | 1.15 |
| 7549 | 3 | 4 | | | IV-1 | CSTB | 1.10 | 7645 | 3 | 4 | | | IV-1 | DNAJC8 | 1.03 |
| 7550 | 3 | 4 | | | IV-1 | CSTF1 | 1.29 | 7646 | 3 | 4 | | | IV-1 | DNAL1 | 1.05 |
| 7551 | 3 | 4 | | | IV-1 | CSTF2 | 1.15 | 7647 | 3 | 4 | | | IV-1 | DNAL4 | 1.37 |
| 7552 | 3 | 4 | | | IV-1 | CTAGE4 | 1.39 | 7648 | 3 | 4 | | | IV-1 | DNASE1L2 | 1.16 |
| 7553 | 3 | 4 | | | IV-1 | CTBP1 | 1.41 | 7649 | 3 | 4 | | | IV-1 | DNTTIP1 | 1.33 |
| 7554 | 3 | 4 | | | IV-1 | CTDNEP1 | 1.44 | 7650 | 3 | 4 | | | IV-1 | DNTTIP2 | 1.22 |
| 7555 | 3 | 4 | | | IV-1 | CTDP1 | 1.49 | 7651 | 3 | 4 | | | IV-1 | DOK1 | 1.50 |
| 7556 | 3 | 4 | | | IV-1 | CTDSP1 | 1.31 | 7652 | 3 | 4 | | | IV-1 | DOK2 | 1.13 |
| 7557 | 3 | 4 | | | IV-1 | CTDSPL2 | 1.45 | 7653 | 3 | 4 | | | IV-1 | DOLK | 1.34 |
| 7558 | 3 | 4 | | | IV-1 | CTPS2 | 1.17 | 7654 | 3 | 4 | | | IV-1 | DOLPP1 | 1.34 |
| 7559 | 3 | 4 | | | IV-1 | CTSC | 1.37 | 7655 | 3 | 4 | | | IV-1 | DPH1 | 1.38 |
| 7560 | 3 | 4 | | | IV-1 | CUEDC2 | 1.30 | 7656 | 3 | 4 | | | IV-1 | DPH3 | 1.15 |
| 7561 | 3 | 4 | | | IV-1 | CUTA | 1.02 | 7657 | 3 | 4 | | | IV-1 | DPM1 | 1.47 |
| 7562 | 3 | 4 | | | IV-1 | CWC15 | 1.32 | 7658 | 3 | 4 | | | IV-1 | DPY19L4 | 1.34 |
| 7563 | 3 | 4 | | | IV-1 | CWC27 | 1.42 | 7659 | 3 | 4 | | | IV-1 | DR1 | 1.38 |
| 7564 | 3 | 4 | | | IV-1 | CWF19L1 | 1.20 | 7660 | 3 | 4 | | | IV-1 | DRAM2 | 1.43 |
| 7565 | 3 | 4 | | | IV-1 | CXCR7 | 1.32 | 7661 | 3 | 4 | | | IV-1 | DRG1 | 1.09 |
| 7566 | 3 | 4 | | | IV-1 | CXorf26 | 1.22 | 7662 | 3 | 4 | | | IV-1 | DSP | 1.21 |
| 7567 | 3 | 4 | | | IV-1 | CXorf40A | 1.42 | 7663 | 3 | 4 | | | IV-1 | DSTNP2 | 1.45 |
| 7568 | 3 | 4 | | | IV-1 | CXorf40B | 1.41 | 7664 | 3 | 4 | | | IV-1 | DTYMK | 1.40 |
| 7569 | 3 | 4 | | | IV-1 | CXorf56 | 1.33 | 7665 | 3 | 4 | | | IV-1 | DUS1L | 1.44 |
| 7570 | 3 | 4 | | | IV-1 | CXorf57 | 1.37 | 7666 | 3 | 4 | | | IV-1 | DUS2L | 1.49 |
| 7571 | 3 | 4 | | | IV-1 | CYB5B | 1.24 | 7667 | 3 | 4 | | | IV-1 | DUS3L | 1.33 |
| 7572 | 3 | 4 | | | IV-1 | CYB5D2 | 1.07 | 7668 | 3 | 4 | | | IV-1 | DUSP11 | 1.31 |
| 7573 | 3 | 4 | | | IV-1 | CYB5R1 | 1.42 | 7669 | 3 | 4 | | | IV-1 | DUSP12 | 1.33 |
| 7574 | 3 | 4 | | | IV-1 | CYB5R3 | 1.09 | 7670 | 3 | 4 | | | IV-1 | DUSP16 | 1.22 |
| 7575 | 3 | 4 | | | IV-1 | CYB5RL | 1.46 | 7671 | 3 | 4 | | | IV-1 | DUSP8 | 1.45 |
| 7576 | 3 | 4 | | | IV-1 | CYC1 | 1.27 | 7672 | 3 | 4 | | | IV-1 | DYM | 1.15 |
| 7577 | 3 | 4 | | | IV-1 | CYCS | 1.26 | 7673 | 3 | 4 | | | IV-1 | DYNLL1 | 1.41 |
| 7578 | 3 | 4 | | | IV-1 | CYFIP2 | 1.37 | 7674 | 3 | 4 | | | IV-1 | DYNLRB1 | 1.23 |
| 7579 | 3 | 4 | | | IV-1 | CYP21A1P | 1.04 | 7675 | 3 | 4 | | | IV-1 | DYNLT3 | 1.32 |

Fig. 40 - 41

| | | | | | | | | | | | | | |
|---|---|---|---|---|---|---|---|---|---|---|---|---|---|
| 7676 | 3 | 4 | | | IV-1 | DYRK1B | 1.21 | 7772 | 3 | 4 | | IV-1 | EXOSC5 | 1.19 |
| 7677 | 3 | 4 | | | IV-1 | DYRK4 | 1.05 | 7773 | 3 | 4 | | IV-1 | EXOSC6 | 1.43 |
| 7678 | 3 | 4 | | | IV-1 | E2F4 | 1.17 | 7774 | 3 | 4 | | IV-1 | EXTL2 | 1.28 |
| 7679 | 3 | 4 | | | IV-1 | EAPP | 1.37 | 7775 | 3 | 4 | | IV-1 | EXTL3 | 1.44 |
| 7680 | 3 | 4 | | | IV-1 | EARS2 | 1.49 | 7776 | 3 | 4 | | IV-1 | F12 | 1.03 |
| 7681 | 3 | 4 | | | IV-1 | EBAG9 | 1.10 | 7777 | 3 | 4 | | IV-1 | F2R | 1.13 |
| 7682 | 3 | 4 | | | IV-1 | EBNA1BP2 | 1.40 | 7778 | 3 | 4 | | IV-1 | F8A1 | 1.43 |
| 7683 | 3 | 4 | | | IV-1 | EBPL | 1.09 | 7779 | 3 | 4 | | IV-1 | FADD | 1.13 |
| 7684 | 3 | 4 | | | IV-1 | ECH1 | 1.28 | 7780 | 3 | 4 | | IV-1 | FAHD2A | 1.14 |
| 7685 | 3 | 4 | | | IV-1 | ECHDC1 | 1.50 | 7781 | 3 | 4 | | IV-1 | FAHD2B | 1.20 |
| 7686 | 3 | 4 | | | IV-1 | ECI1 | 1.06 | 7782 | 3 | 4 | | IV-1 | FAM100A | 1.40 |
| 7687 | 3 | 4 | | | IV-1 | EDA2R | 1.06 | 7783 | 3 | 4 | | IV-1 | FAM100B | 1.44 |
| 7688 | 3 | 4 | | | IV-1 | EEF1E1 | 1.01 | 7784 | 3 | 4 | | IV-1 | FAM104A | 1.10 |
| 7689 | 3 | 4 | | | IV-1 | EFHC2 | 1.30 | 7785 | 3 | 4 | | IV-1 | FAM104B | 1.01 |
| 7690 | 3 | 4 | | | IV-1 | EFHD1 | 1.15 | 7786 | 3 | 4 | | IV-1 | FAM105A | 1.37 |
| 7691 | 3 | 4 | | | IV-1 | EFHD2 | 1.26 | 7787 | 3 | 4 | | IV-1 | FAM107B | 1.43 |
| 7692 | 3 | 4 | | | IV-1 | EFNA4 | 1.31 | 7788 | 3 | 4 | | IV-1 | FAM108B1 | 1.33 |
| 7693 | 3 | 4 | | | IV-1 | EGF | 1.46 | 7789 | 3 | 4 | | IV-1 | FAM114A1 | 1.34 |
| 7694 | 3 | 4 | | | IV-1 | EGFL6 | 1.06 | 7790 | 3 | 4 | | IV-1 | FAM114A2 | 1.33 |
| 7695 | 3 | 4 | | | IV-1 | EGLN2 | 1.04 | 7791 | 3 | 4 | | IV-1 | FAM116A | 1.37 |
| 7696 | 3 | 4 | | | IV-1 | EGR3 | 1.40 | 7792 | 3 | 4 | | IV-1 | FAM133B | 1.04 |
| 7697 | 3 | 4 | | | IV-1 | EHD1 | 1.23 | 7793 | 3 | 4 | | IV-1 | FAM134A | 1.39 |
| 7698 | 3 | 4 | | | IV-1 | EID1 | 1.22 | 7794 | 3 | 4 | | IV-1 | FAM134C | 1.24 |
| 7699 | 3 | 4 | | | IV-1 | EIF1 | 1.26 | 7795 | 3 | 4 | | IV-1 | FAM153B | 1.01 |
| 7700 | 3 | 4 | | | IV-1 | EIF1AD | 1.44 | 7796 | 3 | 4 | | IV-1 | FAM153C | 1.47 |
| 7701 | 3 | 4 | | | IV-1 | EIF1AX | 1.23 | 7797 | 3 | 4 | | IV-1 | FAM168B | 1.35 |
| 7702 | 3 | 4 | | | IV-1 | EIF1B | 1.35 | 7798 | 3 | 4 | | IV-1 | FAM172A | 1.15 |
| 7703 | 3 | 4 | | | IV-1 | EIF2B1 | 1.46 | 7799 | 3 | 4 | | IV-1 | FAM173B | 1.10 |
| 7704 | 3 | 4 | | | IV-1 | EIF2B2 | 1.39 | 7800 | 3 | 4 | | IV-1 | FAM174B | 1.22 |
| 7705 | 3 | 4 | | | IV-1 | EIF2S1 | 1.32 | 7801 | 3 | 4 | | IV-1 | FAM175A | 1.19 |
| 7706 | 3 | 4 | | | IV-1 | EIF2S2 | 1.27 | 7802 | 3 | 4 | | IV-1 | FAM176B | 1.24 |
| 7707 | 3 | 4 | | | IV-1 | EIF2S3 | 1.33 | 7803 | 3 | 4 | | IV-1 | FAM177A1 | 1.30 |
| 7708 | 3 | 4 | | | IV-1 | EIF3C | 1.41 | 7804 | 3 | 4 | | IV-1 | FAM185A | 1.48 |
| 7709 | 3 | 4 | | | IV-1 | EIF3D | 1.01 | 7805 | 3 | 4 | | IV-1 | FAM190B | 1.31 |
| 7710 | 3 | 4 | | | IV-1 | EIF3E | 1.04 | 7806 | 3 | 4 | | IV-1 | FAM19A2 | 1.33 |
| 7711 | 3 | 4 | | | IV-1 | EIF3G | 1.01 | 7807 | 3 | 4 | | IV-1 | FAM200A | 1.34 |
| 7712 | 3 | 4 | | | IV-1 | EIF3H | 1.03 | 7808 | 3 | 4 | | IV-1 | FAM203A | 1.17 |
| 7713 | 3 | 4 | | | IV-1 | EIF3I | 1.06 | 7809 | 3 | 4 | | IV-1 | FAM204A | 1.22 |
| 7714 | 3 | 4 | | | IV-1 | EIF3M | 1.26 | 7810 | 3 | 4 | | IV-1 | FAM208 | 1.28 |
| 7715 | 3 | 4 | | | IV-1 | EIF4A1 | 1.31 | 7811 | 3 | 4 | | IV-1 | FAM210A | 1.40 |
| 7716 | 3 | 4 | | | IV-1 | EIF4A3 | 1.25 | 7812 | 3 | 4 | | IV-1 | FAM212A | 1.34 |
| 7717 | 3 | 4 | | | IV-1 | EIF4E | 1.07 | 7813 | 3 | 4 | | IV-1 | FAM213B | 1.31 |
| 7718 | 3 | 4 | | | IV-1 | EIF4E2 | 1.11 | 7814 | 3 | 4 | | IV-1 | FAM217B | 1.14 |
| 7719 | 3 | 4 | | | IV-1 | EIF4E3 | 1.36 | 7815 | 3 | 4 | | IV-1 | FAM22A | 1.37 |
| 7720 | 3 | 4 | | | IV-1 | EIF4EBP2 | 1.11 | 7816 | 3 | 4 | | IV-1 | FAM22D | 1.41 |
| 7721 | 3 | 4 | | | IV-1 | EIF4ENIF1 | 1.48 | 7817 | 3 | 4 | | IV-1 | FAM27A | 1.01 |
| 7722 | 3 | 4 | | | IV-1 | EIF5AL1 | 1.08 | 7818 | 3 | 4 | | IV-1 | FAM32A | 1.33 |
| 7723 | 3 | 4 | | | IV-1 | EIF6 | 1.34 | 7819 | 3 | 4 | | IV-1 | FAM35A | 1.21 |
| 7724 | 3 | 4 | | | IV-1 | ELAC1 | 1.11 | 7820 | 3 | 4 | | IV-1 | FAM35B2 | 1.09 |
| 7725 | 3 | 4 | | | IV-1 | ELK1 | 1.29 | 7821 | 3 | 4 | | IV-1 | FAM3A | 1.43 |
| 7726 | 3 | 4 | | | IV-1 | ELK3 | 1.21 | 7822 | 3 | 4 | | IV-1 | FAM43A | 1.28 |
| 7727 | 3 | 4 | | | IV-1 | ELOF1 | 1.21 | 7823 | 3 | 4 | | IV-1 | FAM53B | 1.50 |
| 7728 | 3 | 4 | | | IV-1 | ELOVL1 | 1.41 | 7824 | 3 | 4 | | IV-1 | FAM53C | 1.21 |
| 7729 | 3 | 4 | | | IV-1 | ELP3 | 1.21 | 7825 | 3 | 4 | | IV-1 | FAM55C | 1.30 |
| 7730 | 3 | 4 | | | IV-1 | ELP4 | 1.25 | 7826 | 3 | 4 | | IV-1 | FAM60A | 1.00 |
| 7731 | 3 | 4 | | | IV-1 | EM8 | 1.15 | 7827 | 3 | 4 | | IV-1 | FAM65C | 1.20 |
| 7732 | 3 | 4 | | | IV-1 | EMBP1 | 1.18 | 7828 | 3 | 4 | | IV-1 | FAM71E1 | 1.42 |
| 7733 | 3 | 4 | | | IV-1 | EMG1 | 1.07 | 7829 | 3 | 4 | | IV-1 | FAM72A | 1.45 |
| 7734 | 3 | 4 | | | IV-1 | EMR3 | 1.12 | 7830 | 3 | 4 | | IV-1 | FAM72B | 1.02 |
| 7735 | 3 | 4 | | | IV-1 | ENO3 | 1.26 | 7831 | 3 | 4 | | IV-1 | FAM72D | 1.11 |
| 7736 | 3 | 4 | | | IV-1 | ENOPH1 | 1.21 | 7832 | 3 | 4 | | IV-1 | FAM82A1 | 1.38 |
| 7737 | 3 | 4 | | | IV-1 | ENOSF1 | 1.30 | 7833 | 3 | 4 | | IV-1 | FAM82A2 | 1.33 |
| 7738 | 3 | 4 | | | IV-1 | ENOX2 | 1.49 | 7834 | 3 | 4 | | IV-1 | FAM83D | 1.29 |
| 7739 | 3 | 4 | | | IV-1 | ENSA | 1.08 | 7835 | 3 | 4 | | IV-1 | FAM83G | 1.35 |
| 7740 | 3 | 4 | | | IV-1 | ENTPD7 | 1.40 | 7836 | 3 | 4 | | IV-1 | FAM83H | 1.47 |
| 7741 | 3 | 4 | | | IV-1 | EPB41 | 1.21 | 7837 | 3 | 4 | | IV-1 | FAM86A | 1.32 |
| 7742 | 3 | 4 | | | IV-1 | EPB41L4A | 1.24 | 7838 | 3 | 4 | | IV-1 | FAM96A | 1.18 |
| 7743 | 3 | 4 | | | IV-1 | EPB41L4A-AS1 | 1.07 | 7839 | 3 | 4 | | IV-1 | FAM96B | 1.40 |
| 7744 | 3 | 4 | | | IV-1 | EPC1 | 1.49 | 7840 | 3 | 4 | | IV-1 | FAM98C | 1.43 |
| 7745 | 3 | 4 | | | IV-1 | EPM2A | 1.11 | 7841 | 3 | 4 | | IV-1 | FANCI | 1.17 |
| 7746 | 3 | 4 | | | IV-1 | EPRS | 1.46 | 7842 | 3 | 4 | | IV-1 | FANCM | 1.09 |
| 7747 | 3 | 4 | | | IV-1 | EPS8 | 1.03 | 7843 | 3 | 4 | | IV-1 | FARP2 | 1.39 |
| 7748 | 3 | 4 | | | IV-1 | ERAL1 | 1.15 | 7844 | 3 | 4 | | IV-1 | FASTKD2 | 1.37 |
| 7749 | 3 | 4 | | | IV-1 | ERCC8 | 1.32 | 7845 | 3 | 4 | | IV-1 | FBXL12 | 1.49 |
| 7750 | 3 | 4 | | | IV-1 | ERGIC1 | 1.41 | 7846 | 3 | 4 | | IV-1 | FBXL14 | 1.42 |
| 7751 | 3 | 4 | | | IV-1 | ERGIC3 | 1.11 | 7847 | 3 | 4 | | IV-1 | FBXL17 | 1.37 |
| 7752 | 3 | 4 | | | IV-1 | ERH | 1.31 | 7848 | 3 | 4 | | IV-1 | FBXL19-AS1 | 1.15 |
| 7753 | 3 | 4 | | | IV-1 | ERI3 | 1.10 | 7849 | 3 | 4 | | IV-1 | FBXL3 | 1.34 |
| 7754 | 3 | 4 | | | IV-1 | ERLEC1 | 1.14 | 7850 | 3 | 4 | | IV-1 | FBXO10 | 1.31 |
| 7755 | 3 | 4 | | | IV-1 | ERMAP | 1.50 | 7851 | 3 | 4 | | IV-1 | FBXO25 | 1.34 |
| 7756 | 3 | 4 | | | IV-1 | ERO1L | 1.31 | 7852 | 3 | 4 | | IV-1 | FBXO3 | 1.48 |
| 7757 | 3 | 4 | | | IV-1 | ERP29 | 1.21 | 7853 | 3 | 4 | | IV-1 | FBXO31 | 1.19 |
| 7758 | 3 | 4 | | | IV-1 | ESCO1 | 1.42 | 7854 | 3 | 4 | | IV-1 | FBXO39 | 1.15 |
| 7759 | 3 | 4 | | | IV-1 | ESR2 | 1.14 | 7855 | 3 | 4 | | IV-1 | FBXO5 | 1.25 |
| 7760 | 3 | 4 | | | IV-1 | ESRRA | 1.38 | 7856 | 3 | 4 | | IV-1 | FBXW2 | 1.41 |
| 7761 | 3 | 4 | | | IV-1 | ESYT1 | 1.31 | 7857 | 3 | 4 | | IV-1 | FBXW5 | 1.19 |
| 7762 | 3 | 4 | | | IV-1 | ESYT2 | 1.35 | 7858 | 3 | 4 | | IV-1 | FBXW9 | 1.24 |
| 7763 | 3 | 4 | | | IV-1 | ETFA | 1.34 | 7859 | 3 | 4 | | IV-1 | FCAR | 1.44 |
| 7764 | 3 | 4 | | | IV-1 | ETS2 | 1.40 | 7860 | 3 | 4 | | IV-1 | FCF1 | 1.43 |
| 7765 | 3 | 4 | | | IV-1 | ETV3 | 1.09 | 7861 | 3 | 4 | | IV-1 | FCRLB | 1.12 |
| 7766 | 3 | 4 | | | IV-1 | EVI2A | 1.35 | 7862 | 3 | 4 | | IV-1 | FDFT1 | 1.38 |
| 7767 | 3 | 4 | | | IV-1 | EVI5L | 1.34 | 7863 | 3 | 4 | | IV-1 | FDPS | 1.34 |
| 7768 | 3 | 4 | | | IV-1 | EXOC5 | 1.39 | 7864 | 3 | 4 | | IV-1 | FDX1 | 1.24 |
| 7769 | 3 | 4 | | | IV-1 | EXOC6 | 1.43 | 7865 | 3 | 4 | | IV-1 | FEM1A | 1.20 |
| 7770 | 3 | 4 | | | IV-1 | EXOSC2 | 1.34 | 7866 | 3 | 4 | | IV-1 | FEM1C | 1.34 |
| 7771 | 3 | 4 | | | IV-1 | EXOSC3 | 1.50 | 7867 | 3 | 4 | | IV-1 | FEN1 | 1.38 |

Fig. 40 - 42

| | | | | | | | | | | | | | | | |
|---|---|---|---|---|---|---|---|---|---|---|---|---|---|---|---|
| 7868 | 3 | 4 | | | IV-1 | FGF13 | 1.15 | 7964 | 3 | 4 | | | IV-1 | GPANK1 | 1.22 |
| 7869 | 3 | 4 | | | IV-1 | FGFR1 | 1.18 | 7965 | 3 | 4 | | | IV-1 | GPATCH2 | 1.25 |
| 7870 | 3 | 4 | | | IV-1 | FITM2 | 1.48 | 7966 | 3 | 4 | | | IV-1 | GPATCH4 | 1.34 |
| 7871 | 3 | 4 | | | IV-1 | FKBP14 | 1.44 | 7967 | 3 | 4 | | | IV-1 | GPC4 | 1.06 |
| 7872 | 3 | 4 | | | IV-1 | FKBP1A | 1.41 | 7968 | 3 | 4 | | | IV-1 | GPD1L | 1.41 |
| 7873 | 3 | 4 | | | IV-1 | FKBP1AP1 | 1.27 | 7969 | 3 | 4 | | | IV-1 | GPI | 1.32 |
| 7874 | 3 | 4 | | | IV-1 | FLJ27354 | 1.43 | 7970 | 3 | 4 | | | IV-1 | GPKOW | 1.22 |
| 7875 | 3 | 4 | | | IV-1 | FLJ31813 | 1.08 | 7971 | 3 | 4 | | | IV-1 | GPM6B | 1.32 |
| 7876 | 3 | 4 | | | IV-1 | FLJ33065 | 1.04 | 7972 | 3 | 4 | | | IV-1 | GPN1 | 1.29 |
| 7877 | 3 | 4 | | | IV-1 | FLJ33630 | 1.41 | 7973 | 3 | 4 | | | IV-1 | GPR132 | 1.43 |
| 7878 | 3 | 4 | | | IV-1 | FLJ38109 | 1.30 | 7974 | 3 | 4 | | | IV-1 | GPR160 | 1.31 |
| 7879 | 3 | 4 | | | IV-1 | FLOT2 | 1.25 | 7975 | 3 | 4 | | | IV-1 | GPR183 | 1.42 |
| 7880 | 3 | 4 | | | IV-1 | FLT3 | 1.29 | 7976 | 3 | 4 | | | IV-1 | GPR55 | 1.26 |
| 7881 | 3 | 4 | | | IV-1 | FLT3LG | 1.45 | 7977 | 3 | 4 | | | IV-1 | GPR68 | 1.00 |
| 7882 | 3 | 4 | | | IV-1 | FMO4 | 1.37 | 7978 | 3 | 4 | | | IV-1 | GPR84 | 1.31 |
| 7883 | 3 | 4 | | | IV-1 | FN8P1 | 1.47 | 7979 | 3 | 4 | | | IV-1 | GPR89A | 1.30 |
| 7884 | 3 | 4 | | | IV-1 | FOPNL | 1.22 | 7980 | 3 | 4 | | | IV-1 | GPRC5D | 1.28 |
| 7885 | 3 | 4 | | | IV-1 | FOXK2 | 1.45 | 7981 | 3 | 4 | | | IV-1 | GPS2 | 1.22 |
| 7886 | 3 | 4 | | | IV-1 | FPGS | 1.13 | 7982 | 3 | 4 | | | IV-1 | GPT2 | 1.11 |
| 7887 | 3 | 4 | | | IV-1 | FRG1 | 1.13 | 7983 | 3 | 4 | | | IV-1 | GRAMD1A | 1.40 |
| 7888 | 3 | 4 | | | IV-1 | FRMD8P1 | 1.42 | 7984 | 3 | 4 | | | IV-1 | GRAMD3 | 1.16 |
| 7889 | 3 | 4 | | | IV-1 | FRS2 | 1.39 | 7985 | 3 | 4 | | | IV-1 | GRAP2 | 1.16 |
| 7890 | 3 | 4 | | | IV-1 | FRS3 | 1.43 | 7986 | 3 | 4 | | | IV-1 | GRIN3A | 1.09 |
| 7891 | 3 | 4 | | | IV-1 | FTH1 | 1.18 | 7987 | 3 | 4 | | | IV-1 | GRINA | 1.09 |
| 7892 | 3 | 4 | | | IV-1 | FTSJ2 | 1.44 | 7988 | 3 | 4 | | | IV-1 | GRK5 | 1.49 |
| 7893 | 3 | 4 | | | IV-1 | FTSJD1 | 1.30 | 7989 | 3 | 4 | | | IV-1 | GRK6 | 1.22 |
| 7894 | 3 | 4 | | | IV-1 | FTX | 1.03 | 7990 | 3 | 4 | | | IV-1 | GRPEL1 | 1.13 |
| 7895 | 3 | 4 | | | IV-1 | FUT8 | 1.39 | 7991 | 3 | 4 | | | IV-1 | GRPEL2 | 1.37 |
| 7896 | 3 | 4 | | | IV-1 | FXC1 | 1.20 | 7992 | 3 | 4 | | | IV-1 | GRWD1 | 1.10 |
| 7897 | 3 | 4 | | | IV-1 | FXYD5 | 1.23 | 7993 | 3 | 4 | | | IV-1 | GSK3A | 1.33 |
| 7898 | 3 | 4 | | | IV-1 | FYN | 1.37 | 7994 | 3 | 4 | | | IV-1 | GSTCD | 1.04 |
| 7899 | 3 | 4 | | | IV-1 | FYTTD1 | 1.49 | 7995 | 3 | 4 | | | IV-1 | GTF2A1 | 1.04 |
| 7900 | 3 | 4 | | | IV-1 | G2E3 | 1.48 | 7996 | 3 | 4 | | | IV-1 | GTF2B | 1.33 |
| 7901 | 3 | 4 | | | IV-1 | G3BP2 | 1.45 | 7997 | 3 | 4 | | | IV-1 | GTF2E1 | 1.30 |
| 7902 | 3 | 4 | | | IV-1 | G6PD | 1.37 | 7998 | 3 | 4 | | | IV-1 | GTF2E2 | 1.32 |
| 7903 | 3 | 4 | | | IV-1 | GABARAP | 1.30 | 7999 | 3 | 4 | | | IV-1 | GTF2H2D | 1.00 |
| 7904 | 3 | 4 | | | IV-1 | GABARAPL2 | 1.35 | 8000 | 3 | 4 | | | IV-1 | GTF2H3 | 1.17 |
| 7905 | 3 | 4 | | | IV-1 | GABPB2 | 1.42 | 8001 | 3 | 4 | | | IV-1 | GTF2H5 | 1.29 |
| 7906 | 3 | 4 | | | IV-1 | GADD45A | 1.05 | 8002 | 3 | 4 | | | IV-1 | GTF2IRD2P1 | 1.29 |
| 7907 | 3 | 4 | | | IV-1 | GALE | 1.38 | 8003 | 3 | 4 | | | IV-1 | GTF3C4 | 1.38 |
| 7908 | 3 | 4 | | | IV-1 | GALNT1 | 1.23 | 8004 | 3 | 4 | | | IV-1 | GTPBP10 | 1.31 |
| 7909 | 3 | 4 | | | IV-1 | GALNT11 | 1.34 | 8005 | 3 | 4 | | | IV-1 | GTPBP6 | 1.44 |
| 7910 | 3 | 4 | | | IV-1 | GATC | 1.32 | 8006 | 3 | 4 | | | IV-1 | GTPBP8 | 1.47 |
| 7911 | 3 | 4 | | | IV-1 | GATSL2 | 1.18 | 8007 | 3 | 4 | | | IV-1 | GUSBP1 | 1.17 |
| 7912 | 3 | 4 | | | IV-1 | GBAS | 1.04 | 8008 | 3 | 4 | | | IV-1 | GUSBP5 | 1.01 |
| 7913 | 3 | 4 | | | IV-1 | GBGT1 | 1.23 | 8009 | 3 | 4 | | | IV-1 | GYG1 | 1.02 |
| 7914 | 3 | 4 | | | IV-1 | GCLM | 1.43 | 8010 | 3 | 4 | | | IV-1 | H19 | 1.31 |
| 7915 | 3 | 4 | | | IV-1 | GCNT2 | 1.48 | 8011 | 3 | 4 | | | IV-1 | H1FX | 1.49 |
| 7916 | 3 | 4 | | | IV-1 | GCNT4 | 1.02 | 8012 | 3 | 4 | | | IV-1 | H2AFV | 1.05 |
| 7917 | 3 | 4 | | | IV-1 | GDE1 | 1.36 | 8013 | 3 | 4 | | | IV-1 | H2AFX | 1.09 |
| 7918 | 3 | 4 | | | IV-1 | GDF11 | 1.09 | 8014 | 3 | 4 | | | IV-1 | H2AFY2 | 1.19 |
| 7919 | 3 | 4 | | | IV-1 | GDI2 | 1.30 | 8015 | 3 | 4 | | | IV-1 | H3F3C | 1.22 |
| 7920 | 3 | 4 | | | IV-1 | GDPD1 | 1.02 | 8016 | 3 | 4 | | | IV-1 | HA8P4 | 1.43 |
| 7921 | 3 | 4 | | | IV-1 | GEMIN4 | 1.48 | 8017 | 3 | 4 | | | IV-1 | HADH | 1.40 |
| 7922 | 3 | 4 | | | IV-1 | GEMIN6 | 1.04 | 8018 | 3 | 4 | | | IV-1 | HADHA | 1.16 |
| 7923 | 3 | 4 | | | IV-1 | GEMIN8P4 | 1.46 | 8019 | 3 | 4 | | | IV-1 | HAGHL | 1.07 |
| 7924 | 3 | 4 | | | IV-1 | GFER | 1.26 | 8020 | 3 | 4 | | | IV-1 | HAT1 | 1.31 |
| 7925 | 3 | 4 | | | IV-1 | GGTA1P | 1.39 | 8021 | 3 | 4 | | | IV-1 | HAUS1 | 1.12 |
| 7926 | 3 | 4 | | | IV-1 | GHITM | 1.19 | 8022 | 3 | 4 | | | IV-1 | HAUS2 | 1.20 |
| 7927 | 3 | 4 | | | IV-1 | GIMAP5 | 1.28 | 8023 | 3 | 4 | | | IV-1 | HAUS4 | 1.05 |
| 7928 | 3 | 4 | | | IV-1 | GIMAP6 | 1.16 | 8024 | 3 | 4 | | | IV-1 | HAX1 | 1.10 |
| 7929 | 3 | 4 | | | IV-1 | GIMAP7 | 1.11 | 8025 | 3 | 4 | | | IV-1 | HBS1L | 1.36 |
| 7930 | 3 | 4 | | | IV-1 | GIN1 | 1.27 | 8026 | 3 | 4 | | | IV-1 | HBXIP | 1.31 |
| 7931 | 3 | 4 | | | IV-1 | GIPC3 | 1.32 | 8027 | 3 | 4 | | | IV-1 | HCCS | 1.28 |
| 7932 | 3 | 4 | | | IV-1 | GIT1 | 1.45 | 8028 | 3 | 4 | | | IV-1 | HCFC1R1 | 1.39 |
| 7933 | 3 | 4 | | | IV-1 | GLIPR2 | 1.33 | 8029 | 3 | 4 | | | IV-1 | HCK | 1.19 |
| 7934 | 3 | 4 | | | IV-1 | GLOD4 | 1.31 | 8030 | 3 | 4 | | | IV-1 | HCST | 1.17 |
| 7935 | 3 | 4 | | | IV-1 | GLRX3 | 1.07 | 8031 | 3 | 4 | | | IV-1 | HDAC11 | 1.35 |
| 7936 | 3 | 4 | | | IV-1 | GLT1D1 | 1.41 | 8032 | 3 | 4 | | | IV-1 | HDAC3 | 1.40 |
| 7937 | 3 | 4 | | | IV-1 | GLT8D1 | 1.48 | 8033 | 3 | 4 | | | IV-1 | HDDC2 | 1.24 |
| 7938 | 3 | 4 | | | IV-1 | GLTP | 1.20 | 8034 | 3 | 4 | | | IV-1 | HDDC3 | 1.10 |
| 7939 | 3 | 4 | | | IV-1 | GLTPD1 | 1.12 | 8035 | 3 | 4 | | | IV-1 | HDGF | 1.10 |
| 7940 | 3 | 4 | | | IV-1 | GLUD2 | 1.31 | 8036 | 3 | 4 | | | IV-1 | HDGFRP2 | 1.47 |
| 7941 | 3 | 4 | | | IV-1 | GMCL1 | 1.03 | 8037 | 3 | 4 | | | IV-1 | HDHD1 | 1.43 |
| 7942 | 3 | 4 | | | IV-1 | GMCL1P1 | 1.04 | 8038 | 3 | 4 | | | IV-1 | HDHD2 | 1.30 |
| 7943 | 3 | 4 | | | IV-1 | GMFG | 1.38 | 8039 | 3 | 4 | | | IV-1 | HEATR2 | 1.45 |
| 7944 | 3 | 4 | | | IV-1 | GMNN | 1.24 | 8040 | 3 | 4 | | | IV-1 | HEATR3 | 1.39 |
| 7945 | 3 | 4 | | | IV-1 | GMPS | 1.37 | 8041 | 3 | 4 | | | IV-1 | HEBP2 | 1.14 |
| 7946 | 3 | 4 | | | IV-1 | GNA11 | 1.38 | 8042 | 3 | 4 | | | IV-1 | HHAT | 1.28 |
| 7947 | 3 | 4 | | | IV-1 | GNAI2 | 1.26 | 8043 | 3 | 4 | | | IV-1 | HHLA3 | 1.17 |
| 7948 | 3 | 4 | | | IV-1 | GNAL | 1.25 | 8044 | 3 | 4 | | | IV-1 | HIBADH | 1.19 |
| 7949 | 3 | 4 | | | IV-1 | GNAQ | 1.24 | 8045 | 3 | 4 | | | IV-1 | HIGD2A | 1.32 |
| 7950 | 3 | 4 | | | IV-1 | GNB2 | 1.36 | 8046 | 3 | 4 | | | IV-1 | HILPDA | 1.14 |
| 7951 | 3 | 4 | | | IV-1 | GNB5 | 1.50 | 8047 | 3 | 4 | | | IV-1 | HINT2 | 1.22 |
| 7952 | 3 | 4 | | | IV-1 | GNG11 | 1.35 | 8048 | 3 | 4 | | | IV-1 | HIPK3 | 1.27 |
| 7953 | 3 | 4 | | | IV-1 | GNG2 | 1.13 | 8049 | 3 | 4 | | | IV-1 | HIST1H2AC | 1.39 |
| 7954 | 3 | 4 | | | IV-1 | GNL1 | 1.41 | 8050 | 3 | 4 | | | IV-1 | HIST1H2AJ | 1.06 |
| 7955 | 3 | 4 | | | IV-1 | GNPNAT1 | 1.46 | 8051 | 3 | 4 | | | IV-1 | HIST1H2BK | 1.39 |
| 7956 | 3 | 4 | | | IV-1 | GNPTAB | 1.24 | 8052 | 3 | 4 | | | IV-1 | HIST1H2BL | 1.02 |
| 7957 | 3 | 4 | | | IV-1 | GNPTG | 1.43 | 8053 | 3 | 4 | | | IV-1 | HIST1H3J | 1.41 |
| 7958 | 3 | 4 | | | IV-1 | GNRHR2 | 1.36 | 8054 | 3 | 4 | | | IV-1 | HIST1H4I | 1.04 |
| 7959 | 3 | 4 | | | IV-1 | GOLGA7 | 1.03 | 8055 | 3 | 4 | | | IV-1 | HIST2H3D | 1.01 |
| 7960 | 3 | 4 | | | IV-1 | GOLPH3 | 1.45 | 8056 | 3 | 4 | | | IV-1 | HIST3H2BB | 1.03 |
| 7961 | 3 | 4 | | | IV-1 | GORASP2 | 1.33 | 8057 | 3 | 4 | | | IV-1 | HIVEP3 | 1.06 |
| 7962 | 3 | 4 | | | IV-1 | GOT1 | 1.35 | 8058 | 3 | 4 | | | IV-1 | HLA-DPB1 | 1.45 |
| 7963 | 3 | 4 | | | IV-1 | GPAA1 | 1.48 | 8059 | 3 | 4 | | | IV-1 | HLA-DQB2 | 1.25 |

Fig. 40 - 43

| | | | | | | | | | | | | | | |
|---|---|---|---|---|---|---|---|---|---|---|---|---|---|---|
| 8060 | 3 | 4 | | | IV-1 | HLA-DRA | 1.38 | 8156 | 3 | 4 | | | IV-1 | IQCC | 1.37 |
| 8061 | 3 | 4 | | | IV-1 | HLA-J | 1.13 | 8157 | 3 | 4 | | | IV-1 | IRF2BP1 | 1.45 |
| 8062 | 3 | 4 | | | IV-1 | HLCS | 1.03 | 8158 | 3 | 4 | | | IV-1 | IRF2BPL | 1.16 |
| 8063 | 3 | 4 | | | IV-1 | HMG20B | 1.48 | 8159 | 3 | 4 | | | IV-1 | ISCA2 | 1.36 |
| 8064 | 3 | 4 | | | IV-1 | HMGA1 | 1.12 | 8160 | 3 | 4 | | | IV-1 | ISCU | 1.32 |
| 8065 | 3 | 4 | | | IV-1 | HMGB1 | 1.13 | 8161 | 3 | 4 | | | IV-1 | ISG20L2 | 1.43 |
| 8066 | 3 | 4 | | | IV-1 | HMGCL | 1.40 | 8162 | 3 | 4 | | | IV-1 | ISOC2 | 1.46 |
| 8067 | 3 | 4 | | | IV-1 | HMGN2 | 1.36 | 8163 | 3 | 4 | | | IV-1 | ISY1 | 1.50 |
| 8068 | 3 | 4 | | | IV-1 | HMGXB3 | 1.44 | 8164 | 3 | 4 | | | IV-1 | ITGB1 | 1.19 |
| 8069 | 3 | 4 | | | IV-1 | HMGXB4 | 1.18 | 8165 | 3 | 4 | | | IV-1 | ITGB1BP1 | 1.16 |
| 8070 | 3 | 4 | | | IV-1 | HN1L | 1.40 | 8166 | 3 | 4 | | | IV-1 | ITGB2 | 1.45 |
| 8071 | 3 | 4 | | | IV-1 | HNRNPA1 | 1.14 | 8167 | 3 | 4 | | | IV-1 | ITK | 1.15 |
| 8072 | 3 | 4 | | | IV-1 | HNRNPA1L2 | 1.06 | 8168 | 3 | 4 | | | IV-1 | ITM2C | 1.41 |
| 8073 | 3 | 4 | | | IV-1 | HNRNPC | 1.28 | 8169 | 3 | 4 | | | IV-1 | JAGN1 | 1.44 |
| 8074 | 3 | 4 | | | IV-1 | HNRNPF | 1.25 | 8170 | 3 | 4 | | | IV-1 | JAZF1 | 1.15 |
| 8075 | 3 | 4 | | | IV-1 | HNRNPL | 1.03 | 8171 | 3 | 4 | | | IV-1 | JMJD4 | 1.15 |
| 8076 | 3 | 4 | | | IV-1 | HNRNPUL1 | 1.32 | 8172 | 3 | 4 | | | IV-1 | JMJD8 | 1.27 |
| 8077 | 3 | 4 | | | IV-1 | HOMEZ | 1.36 | 8173 | 3 | 4 | | | IV-1 | JOSD1 | 1.18 |
| 8078 | 3 | 4 | | | IV-1 | HORMAD1 | 1.05 | 8174 | 3 | 4 | | | IV-1 | JOSD2 | 1.31 |
| 8079 | 3 | 4 | | | IV-1 | HOXB4 | 1.15 | 8175 | 3 | 4 | | | IV-1 | JTB | 1.31 |
| 8080 | 3 | 4 | | | IV-1 | HPCAL1 | 1.21 | 8176 | 3 | 4 | | | IV-1 | JUNB | 1.49 |
| 8081 | 3 | 4 | | | IV-1 | HPRT1 | 1.18 | 8177 | 3 | 4 | | | IV-1 | JUND | 1.48 |
| 8082 | 3 | 4 | | | IV-1 | HPS6 | 1.41 | 8178 | 3 | 4 | | | IV-1 | KANSL2 | 1.36 |
| 8083 | 3 | 4 | | | IV-1 | HRASLS | 1.05 | 8179 | 3 | 4 | | | IV-1 | KARS | 1.43 |
| 8084 | 3 | 4 | | | IV-1 | HRASLS2 | 1.03 | 8180 | 3 | 4 | | | IV-1 | KAT5 | 1.24 |
| 8085 | 3 | 4 | | | IV-1 | HRH2 | 1.02 | 8181 | 3 | 4 | | | IV-1 | KAT8 | 1.39 |
| 8086 | 3 | 4 | | | IV-1 | HRSP12 | 1.09 | 8182 | 3 | 4 | | | IV-1 | KATNA1 | 1.34 |
| 8087 | 3 | 4 | | | IV-1 | HS6ST1 | 1.12 | 8183 | 3 | 4 | | | IV-1 | KBTBD4 | 1.28 |
| 8088 | 3 | 4 | | | IV-1 | HSBP1 | 1.11 | 8184 | 3 | 4 | | | IV-1 | KBTBD7 | 1.49 |
| 8089 | 3 | 4 | | | IV-1 | HSD17B10 | 1.16 | 8185 | 3 | 4 | | | IV-1 | KBTBD8 | 1.28 |
| 8090 | 3 | 4 | | | IV-1 | HSD3B7 | 1.45 | 8186 | 3 | 4 | | | IV-1 | KCMF1 | 1.33 |
| 8091 | 3 | 4 | | | IV-1 | HSDL2 | 1.01 | 8187 | 3 | 4 | | | IV-1 | KCNAB2 | 1.24 |
| 8092 | 3 | 4 | | | IV-1 | HSF4 | 1.39 | 8188 | 3 | 4 | | | IV-1 | KCNAB3 | 1.45 |
| 8093 | 3 | 4 | | | IV-1 | HSP90AB2P | 1.13 | 8189 | 3 | 4 | | | IV-1 | KCNC4 | 1.16 |
| 8094 | 3 | 4 | | | IV-1 | HSPA13 | 1.18 | 8190 | 3 | 4 | | | IV-1 | KCNE3 | 1.31 |
| 8095 | 3 | 4 | | | IV-1 | HSPA14 | 1.34 | 8191 | 3 | 4 | | | IV-1 | KCNRG | 1.39 |
| 8096 | 3 | 4 | | | IV-1 | HSPA1L | 1.34 | 8192 | 3 | 4 | | | IV-1 | KCTD10 | 1.13 |
| 8097 | 3 | 4 | | | IV-1 | HSPA8 | 1.28 | 8193 | 3 | 4 | | | IV-1 | KCTD2 | 1.39 |
| 8098 | 3 | 4 | | | IV-1 | HSPBP1 | 1.01 | 8194 | 3 | 4 | | | IV-1 | KCTD20 | 1.15 |
| 8099 | 3 | 4 | | | IV-1 | HTATSF1 | 1.42 | 8195 | 3 | 4 | | | IV-1 | KCTD5 | 1.50 |
| 8100 | 3 | 4 | | | IV-1 | HYAL1 | 1.47 | 8196 | 3 | 4 | | | IV-1 | KDELC2 | 1.10 |
| 8101 | 3 | 4 | | | IV-1 | HYAL2 | 1.10 | 8197 | 3 | 4 | | | IV-1 | KDM4B | 1.47 |
| 8102 | 3 | 4 | | | IV-1 | HYLS1 | 1.23 | 8198 | 3 | 4 | | | IV-1 | KEAP1 | 1.14 |
| 8103 | 3 | 4 | | | IV-1 | HYOU1 | 1.47 | 8199 | 3 | 4 | | | IV-1 | KHDRBS1 | 1.48 |
| 8104 | 3 | 4 | | | IV-1 | IAH1 | 1.04 | 8200 | 3 | 4 | | | IV-1 | KHK | 1.29 |
| 8105 | 3 | 4 | | | IV-1 | IARS2 | 1.49 | 8201 | 3 | 4 | | | IV-1 | KIAA0317 | 1.34 |
| 8106 | 3 | 4 | | | IV-1 | ICA1 | 1.33 | 8202 | 3 | 4 | | | IV-1 | KIAA0391 | 1.05 |
| 8107 | 3 | 4 | | | IV-1 | ICAM3 | 1.30 | 8203 | 3 | 4 | | | IV-1 | KIAA0825 | 1.10 |
| 8108 | 3 | 4 | | | IV-1 | ICK | 1.47 | 8204 | 3 | 4 | | | IV-1 | KIAA0947 | 1.49 |
| 8109 | 3 | 4 | | | IV-1 | ICMT | 1.31 | 8205 | 3 | 4 | | | IV-1 | KIAA1107 | 1.03 |
| 8110 | 3 | 4 | | | IV-1 | ICT1 | 1.25 | 8206 | 3 | 4 | | | IV-1 | KIAA1191 | 1.29 |
| 8111 | 3 | 4 | | | IV-1 | IDH3B | 1.48 | 8207 | 3 | 4 | | | IV-1 | KIAA1328 | 1.20 |
| 8112 | 3 | 4 | | | IV-1 | IDI2 | 1.50 | 8208 | 3 | 4 | | | IV-1 | KIAA1383 | 1.32 |
| 8113 | 3 | 4 | | | IV-1 | IDS | 1.41 | 8209 | 3 | 4 | | | IV-1 | KIAA1430 | 1.14 |
| 8114 | 3 | 4 | | | IV-1 | IER3IP1 | 1.31 | 8210 | 3 | 4 | | | IV-1 | KIAA1704 | 1.19 |
| 8115 | 3 | 4 | | | IV-1 | IER5L | 1.50 | 8211 | 3 | 4 | | | IV-1 | KIAA1715 | 1.06 |
| 8116 | 3 | 4 | | | IV-1 | IFI27L1 | 1.27 | 8212 | 3 | 4 | | | IV-1 | KIAA1737 | 1.48 |
| 8117 | 3 | 4 | | | IV-1 | IFI27L2 | 1.26 | 8213 | 3 | 4 | | | IV-1 | KIF23 | 1.04 |
| 8118 | 3 | 4 | | | IV-1 | IFRD2 | 1.24 | 8214 | 3 | 4 | | | IV-1 | KIF2A | 1.43 |
| 8119 | 3 | 4 | | | IV-1 | IFT122 | 1.48 | 8215 | 3 | 4 | | | IV-1 | KIF3A | 1.42 |
| 8120 | 3 | 4 | | | IV-1 | IFT20 | 1.37 | 8216 | 3 | 4 | | | IV-1 | KIF5C | 1.17 |
| 8121 | 3 | 4 | | | IV-1 | IFT52 | 1.29 | 8217 | 3 | 4 | | | IV-1 | KIFAP3 | 1.46 |
| 8122 | 3 | 4 | | | IV-1 | IFT57 | 1.47 | 8218 | 3 | 4 | | | IV-1 | KIR2DL4 | 1.48 |
| 8123 | 3 | 4 | | | IV-1 | IGBP1 | 1.23 | 8219 | 3 | 4 | | | IV-1 | KLF13 | 1.41 |
| 8124 | 3 | 4 | | | IV-1 | IGBP1P1 | 1.07 | 8220 | 3 | 4 | | | IV-1 | KLHL22 | 1.41 |
| 8125 | 3 | 4 | | | IV-1 | IGFLR1 | 1.28 | 8221 | 3 | 4 | | | IV-1 | KLHL36 | 1.47 |
| 8126 | 3 | 4 | | | IV-1 | IGSF6 | 1.40 | 8222 | 3 | 4 | | | IV-1 | KLHL7 | 1.27 |
| 8127 | 3 | 4 | | | IV-1 | IK | 1.49 | 8223 | 3 | 4 | | | IV-1 | KLRAP1 | 1.39 |
| 8128 | 3 | 4 | | | IV-1 | IKZF5 | 1.22 | 8224 | 3 | 4 | | | IV-1 | KRCC1 | 1.17 |
| 8129 | 3 | 4 | | | IV-1 | IL16 | 1.40 | 8225 | 3 | 4 | | | IV-1 | KRTAP5-1 | 1.06 |
| 8130 | 3 | 4 | | | IV-1 | IL27 | 1.36 | 8226 | 3 | 4 | | | IV-1 | KRTCAP2 | 1.29 |
| 8131 | 3 | 4 | | | IV-1 | IL2RA | 1.43 | 8227 | 3 | 4 | | | IV-1 | KXD1 | 1.17 |
| 8132 | 3 | 4 | | | IV-1 | IL32 | 1.03 | 8228 | 3 | 4 | | | IV-1 | LACTB2 | 1.34 |
| 8133 | 3 | 4 | | | IV-1 | IL4R | 1.34 | 8229 | 3 | 4 | | | IV-1 | LAMTOR2 | 1.18 |
| 8134 | 3 | 4 | | | IV-1 | IL7 | 1.35 | 8230 | 3 | 4 | | | IV-1 | LANCL1 | 1.46 |
| 8135 | 3 | 4 | | | IV-1 | IL9R | 1.04 | 8231 | 3 | 4 | | | IV-1 | LANCL2 | 1.44 |
| 8136 | 3 | 4 | | | IV-1 | ILF2 | 1.27 | 8232 | 3 | 4 | | | IV-1 | LAPTM5 | 1.49 |
| 8137 | 3 | 4 | | | IV-1 | ILVBL | 1.41 | 8233 | 3 | 4 | | | IV-1 | LARGE | 1.28 |
| 8138 | 3 | 4 | | | IV-1 | IMMP2L | 1.11 | 8234 | 3 | 4 | | | IV-1 | LARS2 | 1.23 |
| 8139 | 3 | 4 | | | IV-1 | IMP3 | 1.29 | 8235 | 3 | 4 | | | IV-1 | LAT | 1.31 |
| 8140 | 3 | 4 | | | IV-1 | IMP4 | 1.38 | 8236 | 3 | 4 | | | IV-1 | LCK | 1.07 |
| 8141 | 3 | 4 | | | IV-1 | IMPACT | 1.16 | 8237 | 3 | 4 | | | IV-1 | LDHA | 1.45 |
| 8142 | 3 | 4 | | | IV-1 | IMPAD1 | 1.33 | 8238 | 3 | 4 | | | IV-1 | LDHB | 1.27 |
| 8143 | 3 | 4 | | | IV-1 | IMPDH1 | 1.09 | 8239 | 3 | 4 | | | IV-1 | LDOC1L | 1.18 |
| 8144 | 3 | 4 | | | IV-1 | IMPDH2 | 1.41 | 8240 | 3 | 4 | | | IV-1 | LENG1 | 1.12 |
| 8145 | 3 | 4 | | | IV-1 | INCA1 | 1.22 | 8241 | 3 | 4 | | | IV-1 | LGMN | 1.50 |
| 8146 | 3 | 4 | | | IV-1 | ING1 | 1.20 | 8242 | 3 | 4 | | | IV-1 | LHX4 | 1.14 |
| 8147 | 3 | 4 | | | IV-1 | ING2 | 1.26 | 8243 | 3 | 4 | | | IV-1 | LILRA1 | 1.40 |
| 8148 | 3 | 4 | | | IV-1 | INPP5B | 1.47 | 8244 | 3 | 4 | | | IV-1 | LIMA1 | 1.03 |
| 8149 | 3 | 4 | | | IV-1 | INPP5K | 1.26 | 8245 | 3 | 4 | | | IV-1 | LIN52 | 1.09 |
| 8150 | 3 | 4 | | | IV-1 | INSIG1 | 1.26 | 8246 | 3 | 4 | | | IV-1 | LIN54 | 1.43 |
| 8151 | 3 | 4 | | | IV-1 | INTS10 | 1.33 | 8247 | 3 | 4 | | | IV-1 | LINC00085 | 1.29 |
| 8152 | 3 | 4 | | | IV-1 | INTS5 | 1.46 | 8248 | 3 | 4 | | | IV-1 | LINC00094 | 1.21 |
| 8153 | 3 | 4 | | | IV-1 | IPO11 | 1.09 | 8249 | 3 | 4 | | | IV-1 | LINC00246A | 1.49 |
| 8154 | 3 | 4 | | | IV-1 | IPO5 | 1.37 | 8250 | 3 | 4 | | | IV-1 | LINC00256B | 1.09 |
| 8155 | 3 | 4 | | | IV-1 | IPO7 | 1.39 | 8251 | 3 | 4 | | | IV-1 | LINC00263 | 1.39 |

Fig. 40 - 44

| | | | | | | | | | | | | | | | |
|---|---|---|---|---|---|---|---|---|---|---|---|---|---|---|---|
| 8252 | 3 | 4 | | | IV-1 | LINC00324 | 1.21 | 8348 | 3 | 4 | | | IV-1 | LOC494127 | 1.22 |
| 8253 | 3 | 4 | | | IV-1 | LINC00493 | 1.49 | 8349 | 3 | 4 | | | IV-1 | LOC541471 | 1.05 |
| 8254 | 3 | 4 | | | IV-1 | LINC00526 | 1.40 | 8350 | 3 | 4 | | | IV-1 | LOC643723 | 1.18 |
| 8255 | 3 | 4 | | | IV-1 | LLGL1 | 1.42 | 8351 | 3 | 4 | | | IV-1 | LOC646278 | 1.32 |
| 8256 | 3 | 4 | | | IV-1 | LLPH | 1.39 | 8352 | 3 | 4 | | | IV-1 | LOC649395 | 1.02 |
| 8257 | 3 | 4 | | | IV-1 | LMAN2 | 1.36 | 8353 | 3 | 4 | | | IV-1 | LOC650623 | 1.12 |
| 8258 | 3 | 4 | | | IV-1 | LMAN2L | 1.50 | 8354 | 3 | 4 | | | IV-1 | LOC653075 | 1.02 |
| 8259 | 3 | 4 | | | IV-1 | LMLN | 1.44 | 8355 | 3 | 4 | | | IV-1 | LOC653513 | 1.37 |
| 8260 | 3 | 4 | | | IV-1 | LMTK3 | 1.09 | 8356 | 3 | 4 | | | IV-1 | LOC653566 | 1.38 |
| 8261 | 3 | 4 | | | IV-1 | LNX2 | 1.33 | 8357 | 3 | 4 | | | IV-1 | LOC727849 | 1.39 |
| 8262 | 3 | 4 | | | IV-1 | LOC100009676 | 1.04 | 8358 | 3 | 4 | | | IV-1 | LOC728024 | 1.12 |
| 8263 | 3 | 4 | | | IV-1 | LOC100128191 | 1.50 | 8359 | 3 | 4 | | | IV-1 | LOC728175 | 1.27 |
| 8264 | 3 | 4 | | | IV-1 | LOC100128288 | 1.49 | 8360 | 3 | 4 | | | IV-1 | LOC728323 | 1.16 |
| 8265 | 3 | 4 | | | IV-1 | LOC100128573 | 1.44 | 8361 | 3 | 4 | | | IV-1 | LOC728377 | 1.04 |
| 8266 | 3 | 4 | | | IV-1 | LOC100129138 | 1.08 | 8362 | 3 | 4 | | | IV-1 | LOC728431 | 1.43 |
| 8267 | 3 | 4 | | | IV-1 | LOC100129196 | 1.43 | 8363 | 3 | 4 | | | IV-1 | LOC728613 | 1.34 |
| 8268 | 3 | 4 | | | IV-1 | LOC100129361 | 1.21 | 8364 | 3 | 4 | | | IV-1 | LOC728739 | 1.04 |
| 8269 | 3 | 4 | | | IV-1 | LOC100129534 | 1.24 | 8365 | 3 | 4 | | | IV-1 | LOC728752 | 1.26 |
| 8270 | 3 | 4 | | | IV-1 | LOC100129617 | 1.32 | 8366 | 3 | 4 | | | IV-1 | LOC728758 | 1.05 |
| 8271 | 3 | 4 | | | IV-1 | LOC100129931 | 1.18 | 8367 | 3 | 4 | | | IV-1 | LOC729020 | 1.27 |
| 8272 | 3 | 4 | | | IV-1 | LOC100129961 | 1.31 | 8368 | 3 | 4 | | | IV-1 | LOC729234 | 1.38 |
| 8273 | 3 | 4 | | | IV-1 | LOC100130331 | 1.30 | 8369 | 3 | 4 | | | IV-1 | LOC729678 | 1.48 |
| 8274 | 3 | 4 | | | IV-1 | LOC100130992 | 1.19 | 8370 | 3 | 4 | | | IV-1 | LOC729683 | 1.33 |
| 8275 | 3 | 4 | | | IV-1 | LOC100131193 | 1.05 | 8371 | 3 | 4 | | | IV-1 | LOC729799 | 1.38 |
| 8276 | 3 | 4 | | | IV-1 | LOC100131655 | 1.48 | 8372 | 3 | 4 | | | IV-1 | LOC93622 | 1.18 |
| 8277 | 3 | 4 | | | IV-1 | LOC100132163 | 1.29 | 8373 | 3 | 4 | | | IV-1 | LOH12CR1 | 1.26 |
| 8278 | 3 | 4 | | | IV-1 | LOC100132273 | 1.42 | 8374 | 3 | 4 | | | IV-1 | LPAR5 | 1.06 |
| 8279 | 3 | 4 | | | IV-1 | LOC100132707 | 1.40 | 8375 | 3 | 4 | | | IV-1 | LPCAT1 | 1.39 |
| 8280 | 3 | 4 | | | IV-1 | LOC100132724 | 1.05 | 8376 | 3 | 4 | | | IV-1 | LPP-AS2 | 1.32 |
| 8281 | 3 | 4 | | | IV-1 | LOC100132831 | 1.01 | 8377 | 3 | 4 | | | IV-1 | LRP10 | 1.50 |
| 8282 | 3 | 4 | | | IV-1 | LOC100132832 | 1.38 | 8378 | 3 | 4 | | | IV-1 | LRP8 | 1.20 |
| 8283 | 3 | 4 | | | IV-1 | LOC100133091 | 1.40 | 8379 | 3 | 4 | | | IV-1 | LRPAP1 | 1.41 |
| 8284 | 3 | 4 | | | IV-1 | LOC100144603 | 1.12 | 8380 | 3 | 4 | | | IV-1 | LRR1 | 1.13 |
| 8285 | 3 | 4 | | | IV-1 | LOC100286844 | 1.31 | 8381 | 3 | 4 | | | IV-1 | LRRC16A | 1.38 |
| 8286 | 3 | 4 | | | IV-1 | LOC100288637 | 1.34 | 8382 | 3 | 4 | | | IV-1 | LRRC20 | 1.05 |
| 8287 | 3 | 4 | | | IV-1 | LOC100288842 | 1.06 | 8383 | 3 | 4 | | | IV-1 | LRRC3 | 1.25 |
| 8288 | 3 | 4 | | | IV-1 | LOC100288846 | 1.45 | 8384 | 3 | 4 | | | IV-1 | LRRC37A3 | 1.36 |
| 8289 | 3 | 4 | | | IV-1 | LOC100294145 | 1.35 | 8385 | 3 | 4 | | | IV-1 | LRRC37BP1 | 1.49 |
| 8290 | 3 | 4 | | | IV-1 | LOC100335030 | 1.23 | 8386 | 3 | 4 | | | IV-1 | LRRC40 | 1.26 |
| 8291 | 3 | 4 | | | IV-1 | LOC100379224 | 1.48 | 8387 | 3 | 4 | | | IV-1 | LRRC42 | 1.25 |
| 8292 | 3 | 4 | | | IV-1 | LOC100499405 | 1.00 | 8388 | 3 | 4 | | | IV-1 | LRRC57 | 1.39 |
| 8293 | 3 | 4 | | | IV-1 | LOC100499489 | 1.13 | 8389 | 3 | 4 | | | IV-1 | LRRC8A | 1.23 |
| 8294 | 3 | 4 | | | IV-1 | LOC100505483 | 1.31 | 8390 | 3 | 4 | | | IV-1 | LSM10 | 1.11 |
| 8295 | 3 | 4 | | | IV-1 | LOC100505576 | 1.23 | 8391 | 3 | 4 | | | IV-1 | LSM12 | 1.31 |
| 8296 | 3 | 4 | | | IV-1 | LOC100505622 | 1.47 | 8392 | 3 | 4 | | | IV-1 | LSM14A | 1.41 |
| 8297 | 3 | 4 | | | IV-1 | LOC100505715 | 1.11 | 8393 | 3 | 4 | | | IV-1 | LSM3 | 1.47 |
| 8298 | 3 | 4 | | | IV-1 | LOC100505812 | 1.41 | 8394 | 3 | 4 | | | IV-1 | LSM4 | 1.31 |
| 8299 | 3 | 4 | | | IV-1 | LOC100505876 | 1.13 | 8395 | 3 | 4 | | | IV-1 | LSM5 | 1.37 |
| 8300 | 3 | 4 | | | IV-1 | LOC100506046 | 1.10 | 8396 | 3 | 4 | | | IV-1 | LSM6 | 1.07 |
| 8301 | 3 | 4 | | | IV-1 | LOC100506190 | 1.24 | 8397 | 3 | 4 | | | IV-1 | LSP1 | 1.33 |
| 8302 | 3 | 4 | | | IV-1 | LOC100506321 | 1.05 | 8398 | 3 | 4 | | | IV-1 | LSR | 1.36 |
| 8303 | 3 | 4 | | | IV-1 | LOC100506548 | 1.38 | 8399 | 3 | 4 | | | IV-1 | LTB | 1.29 |
| 8304 | 3 | 4 | | | IV-1 | LOC100506585 | 1.38 | 8400 | 3 | 4 | | | IV-1 | LTK | 1.08 |
| 8305 | 3 | 4 | | | IV-1 | LOC100506649 | 1.13 | 8401 | 3 | 4 | | | IV-1 | LY9 | 1.14 |
| 8306 | 3 | 4 | | | IV-1 | LOC100506686 | 1.02 | 8402 | 3 | 4 | | | IV-1 | LYPLA1 | 1.01 |
| 8307 | 3 | 4 | | | IV-1 | LOC100506714 | 1.13 | 8403 | 3 | 4 | | | IV-1 | LYPLA2 | 1.25 |
| 8308 | 3 | 4 | | | IV-1 | LOC100506730 | 1.13 | 8404 | 3 | 4 | | | IV-1 | LYRM1 | 1.38 |
| 8309 | 3 | 4 | | | IV-1 | LOC100506779 | 1.38 | 8405 | 3 | 4 | | | IV-1 | LYRM2 | 1.21 |
| 8310 | 3 | 4 | | | IV-1 | LOC100507117 | 1.36 | 8406 | 3 | 4 | | | IV-1 | LYRM7 | 1.41 |
| 8311 | 3 | 4 | | | IV-1 | LOC100507501 | 1.36 | 8407 | 3 | 4 | | | IV-1 | LYSMD3 | 1.34 |
| 8312 | 3 | 4 | | | IV-1 | LOC100507557 | 1.24 | 8408 | 3 | 4 | | | IV-1 | LYVE1 | 1.27 |
| 8313 | 3 | 4 | | | IV-1 | LOC100507634 | 1.31 | 8409 | 3 | 4 | | | IV-1 | MAD2L1 | 1.13 |
| 8314 | 3 | 4 | | | IV-1 | LOC100508120 | 1.26 | 8410 | 3 | 4 | | | IV-1 | MAD2L2 | 1.01 |
| 8315 | 3 | 4 | | | IV-1 | LOC100630918 | 1.49 | 8411 | 3 | 4 | | | IV-1 | MAGED2 | 1.39 |
| 8316 | 3 | 4 | | | IV-1 | LOC100652846 | 1.16 | 8412 | 3 | 4 | | | IV-1 | MAGEH1 | 1.21 |
| 8317 | 3 | 4 | | | IV-1 | LOC139201 | 1.24 | 8413 | 3 | 4 | | | IV-1 | MAGOH | 1.19 |
| 8318 | 3 | 4 | | | IV-1 | LOC145783 | 1.03 | 8414 | 3 | 4 | | | IV-1 | MAGOHB | 1.44 |
| 8319 | 3 | 4 | | | IV-1 | LOC149837 | 1.33 | 8415 | 3 | 4 | | | IV-1 | MAGT1 | 1.07 |
| 8320 | 3 | 4 | | | IV-1 | LOC152217 | 1.31 | 8416 | 3 | 4 | | | IV-1 | MAK16 | 1.16 |
| 8321 | 3 | 4 | | | IV-1 | LOC220906 | 1.27 | 8417 | 3 | 4 | | | IV-1 | MAL | 1.35 |
| 8322 | 3 | 4 | | | IV-1 | LOC254128 | 1.47 | 8418 | 3 | 4 | | | IV-1 | MALSU1 | 1.01 |
| 8323 | 3 | 4 | | | IV-1 | LOC283194 | 1.38 | 8419 | 3 | 4 | | | IV-1 | MAMDC4 | 1.03 |
| 8324 | 3 | 4 | | | IV-1 | LOC283692 | 1.05 | 8420 | 3 | 4 | | | IV-1 | MAML3 | 1.47 |
| 8325 | 3 | 4 | | | IV-1 | LOC284023 | 1.20 | 8421 | 3 | 4 | | | IV-1 | MAN1B1 | 1.30 |
| 8326 | 3 | 4 | | | IV-1 | LOC284757 | 1.17 | 8422 | 3 | 4 | | | IV-1 | MANF | 1.29 |
| 8327 | 3 | 4 | | | IV-1 | LOC285819 | 1.02 | 8423 | 3 | 4 | | | IV-1 | MAP1LC3B | 1.43 |
| 8328 | 3 | 4 | | | IV-1 | LOC286367 | 1.18 | 8424 | 3 | 4 | | | IV-1 | MAP1LC3B2 | 1.27 |
| 8329 | 3 | 4 | | | IV-1 | LOC339803 | 1.49 | 8425 | 3 | 4 | | | IV-1 | MAP2K2 | 1.27 |
| 8330 | 3 | 4 | | | IV-1 | LOC339874 | 1.07 | 8426 | 3 | 4 | | | IV-1 | MAP2K3 | 1.48 |
| 8331 | 3 | 4 | | | IV-1 | LOC340544 | 1.33 | 8427 | 3 | 4 | | | IV-1 | MAP2K5 | 1.32 |
| 8332 | 3 | 4 | | | IV-1 | LOC341056 | 1.29 | 8428 | 3 | 4 | | | IV-1 | MAP2K7 | 1.33 |
| 8333 | 3 | 4 | | | IV-1 | LOC344967 | 1.28 | 8429 | 3 | 4 | | | IV-1 | MAP3K13 | 1.31 |
| 8334 | 3 | 4 | | | IV-1 | LOC374443 | 1.33 | 8430 | 3 | 4 | | | IV-1 | MAP3K6 | 1.30 |
| 8335 | 3 | 4 | | | IV-1 | LOC375190 | 1.28 | 8431 | 3 | 4 | | | IV-1 | MAP3K7 | 1.47 |
| 8336 | 3 | 4 | | | IV-1 | LOC386758 | 1.46 | 8432 | 3 | 4 | | | IV-1 | MAP4K1 | 1.01 |
| 8337 | 3 | 4 | | | IV-1 | LOC387646 | 1.16 | 8433 | 3 | 4 | | | IV-1 | MAP7D1 | 1.41 |
| 8338 | 3 | 4 | | | IV-1 | LOC387647 | 1.49 | 8434 | 3 | 4 | | | IV-1 | MAP9 | 1.23 |
| 8339 | 3 | 4 | | | IV-1 | LOC388499 | 1.08 | 8435 | 3 | 4 | | | IV-1 | MAPK11 | 1.05 |
| 8340 | 3 | 4 | | | IV-1 | LOC389834 | 1.41 | 8436 | 3 | 4 | | | IV-1 | MAPK14 | 1.39 |
| 8341 | 3 | 4 | | | IV-1 | LOC400604 | 1.10 | 8437 | 3 | 4 | | | IV-1 | MAPK3 | 1.37 |
| 8342 | 3 | 4 | | | IV-1 | LOC401127 | 1.22 | 8438 | 3 | 4 | | | IV-1 | MAPK6 | 1.41 |
| 8343 | 3 | 4 | | | IV-1 | LOC401397 | 1.36 | 8439 | 3 | 4 | | | IV-1 | MAPKAPK2 | 1.20 |
| 8344 | 3 | 4 | | | IV-1 | LOC401431 | 1.04 | 8440 | 3 | 4 | | | IV-1 | MAPKAPK3 | 1.36 |
| 8345 | 3 | 4 | | | IV-1 | LOC407835 | 1.29 | 8441 | 3 | 4 | | | IV-1 | MAPKAPK5 | 1.21 |
| 8346 | 3 | 4 | | | IV-1 | LOC440288 | 1.35 | 8442 | 3 | 4 | | | IV-1 | 42438 | 1.48 |
| 8347 | 3 | 4 | | | IV-1 | LOC440894 | 1.37 | 8443 | 3 | 4 | | | IV-1 | MARCKSL1 | 1.24 |

Fig. 40 - 45

| | | | | | | | | | | | | | | | |
|---|---|---|---|---|---|---|---|---|---|---|---|---|---|---|---|
| 8444 | 3 | 4 | | | IV-1 | MARK3 | 1.43 | 8540 | 3 | 4 | | | IV-1 | MPO | 1.21 |
| 8445 | 3 | 4 | | | IV-1 | MARS2 | 1.31 | 8541 | 3 | 4 | | | IV-1 | MPV17 | 1.39 |
| 8446 | 3 | 4 | | | IV-1 | MATR3 | 1.41 | 8542 | 3 | 4 | | | IV-1 | MPV17L2 | 1.39 |
| 8447 | 3 | 4 | | | IV-1 | MAZ | 1.23 | 8543 | 3 | 4 | | | IV-1 | MPZL3 | 1.08 |
| 8448 | 3 | 4 | | | IV-1 | MB21D2 | 1.32 | 8544 | 3 | 4 | | | IV-1 | MRFAP1 | 1.34 |
| 8449 | 3 | 4 | | | IV-1 | MBLAC1 | 1.01 | 8545 | 3 | 4 | | | IV-1 | MRFAP1L1 | 1.15 |
| 8450 | 3 | 4 | | | IV-1 | MBNL2 | 1.14 | 8546 | 3 | 4 | | | IV-1 | MRP63 | 1.07 |
| 8451 | 3 | 4 | | | IV-1 | MBNL3 | 1.07 | 8547 | 3 | 4 | | | IV-1 | MRPL10 | 1.06 |
| 8452 | 3 | 4 | | | IV-1 | MBP | 1.44 | 8548 | 3 | 4 | | | IV-1 | MRPL12 | 1.06 |
| 8453 | 3 | 4 | | | IV-1 | MCART1 | 1.27 | 8549 | 3 | 4 | | | IV-1 | MRPL14 | 1.00 |
| 8454 | 3 | 4 | | | IV-1 | MCAT | 1.40 | 8550 | 3 | 4 | | | IV-1 | MRPL15 | 1.15 |
| 8455 | 3 | 4 | | | IV-1 | MCCC1 | 1.28 | 8551 | 3 | 4 | | | IV-1 | MRPL16 | 1.43 |
| 8456 | 3 | 4 | | | IV-1 | MCF2L | 1.15 | 8552 | 3 | 4 | | | IV-1 | MRPL17 | 1.22 |
| 8457 | 3 | 4 | | | IV-1 | MCF2L-AS1 | 1.13 | 8553 | 3 | 4 | | | IV-1 | MRPL2 | 1.41 |
| 8458 | 3 | 4 | | | IV-1 | MCFD2 | 1.44 | 8554 | 3 | 4 | | | IV-1 | MRPL20 | 1.34 |
| 8459 | 3 | 4 | | | IV-1 | MCM3AP-AS1 | 1.45 | 8555 | 3 | 4 | | | IV-1 | MRPL23 | 1.27 |
| 8460 | 3 | 4 | | | IV-1 | MCM5 | 1.47 | 8556 | 3 | 4 | | | IV-1 | MRPL28 | 1.26 |
| 8461 | 3 | 4 | | | IV-1 | MCOLN2 | 1.25 | 8557 | 3 | 4 | | | IV-1 | MRPL3 | 1.06 |
| 8462 | 3 | 4 | | | IV-1 | MDFIC | 1.27 | 8558 | 3 | 4 | | | IV-1 | MRPL30 | 1.06 |
| 8463 | 3 | 4 | | | IV-1 | MDH1 | 1.37 | 8559 | 3 | 4 | | | IV-1 | MRPL32 | 1.21 |
| 8464 | 3 | 4 | | | IV-1 | MDH2 | 1.40 | 8560 | 3 | 4 | | | IV-1 | MRPL37 | 1.29 |
| 8465 | 3 | 4 | | | IV-1 | MEAF6 | 1.18 | 8561 | 3 | 4 | | | IV-1 | MRPL46 | 1.13 |
| 8466 | 3 | 4 | | | IV-1 | MECP2 | 1.38 | 8562 | 3 | 4 | | | IV-1 | MRPL47 | 1.24 |
| 8467 | 3 | 4 | | | IV-1 | MECR | 1.09 | 8563 | 3 | 4 | | | IV-1 | MRPL50 | 1.07 |
| 8468 | 3 | 4 | | | IV-1 | MED10 | 1.46 | 8564 | 3 | 4 | | | IV-1 | MRPL51 | 1.14 |
| 8469 | 3 | 4 | | | IV-1 | MED11 | 1.25 | 8565 | 3 | 4 | | | IV-1 | MRPL52 | 1.41 |
| 8470 | 3 | 4 | | | IV-1 | MED18 | 1.00 | 8566 | 3 | 4 | | | IV-1 | MRPL55 | 1.19 |
| 8471 | 3 | 4 | | | IV-1 | MED19 | 1.43 | 8567 | 3 | 4 | | | IV-1 | MRPL9 | 1.25 |
| 8472 | 3 | 4 | | | IV-1 | MED20 | 1.23 | 8568 | 3 | 4 | | | IV-1 | MRPS10 | 1.34 |
| 8473 | 3 | 4 | | | IV-1 | MED21 | 1.46 | 8569 | 3 | 4 | | | IV-1 | MRPS11 | 1.19 |
| 8474 | 3 | 4 | | | IV-1 | MED26 | 1.43 | 8570 | 3 | 4 | | | IV-1 | MRPS12 | 1.13 |
| 8475 | 3 | 4 | | | IV-1 | MED29 | 1.17 | 8571 | 3 | 4 | | | IV-1 | MRPS16 | 1.18 |
| 8476 | 3 | 4 | | | IV-1 | MED30 | 1.21 | 8572 | 3 | 4 | | | IV-1 | MRPS17 | 1.23 |
| 8477 | 3 | 4 | | | IV-1 | MED31 | 1.03 | 8573 | 3 | 4 | | | IV-1 | MRPS2 | 1.34 |
| 8478 | 3 | 4 | | | IV-1 | MED4 | 1.45 | 8574 | 3 | 4 | | | IV-1 | MRPS22 | 1.45 |
| 8479 | 3 | 4 | | | IV-1 | MED6 | 1.49 | 8575 | 3 | 4 | | | IV-1 | MRPS24 | 1.16 |
| 8480 | 3 | 4 | | | IV-1 | MED9 | 1.19 | 8576 | 3 | 4 | | | IV-1 | MRPS30 | 1.42 |
| 8481 | 3 | 4 | | | IV-1 | MEF2BNB | 1.16 | 8577 | 3 | 4 | | | IV-1 | MRPS33 | 1.33 |
| 8482 | 3 | 4 | | | IV-1 | MEGF9 | 1.39 | 8578 | 3 | 4 | | | IV-1 | MRPS34 | 1.14 |
| 8483 | 3 | 4 | | | IV-1 | MESDC2 | 1.39 | 8579 | 3 | 4 | | | IV-1 | MRPS35 | 1.36 |
| 8484 | 3 | 4 | | | IV-1 | METAP1D | 1.20 | 8580 | 3 | 4 | | | IV-1 | MRPS36 | 1.07 |
| 8485 | 3 | 4 | | | IV-1 | METRN | 1.24 | 8581 | 3 | 4 | | | IV-1 | MRPS6 | 1.35 |
| 8486 | 3 | 4 | | | IV-1 | METRNL | 1.11 | 8582 | 3 | 4 | | | IV-1 | MRPS7 | 1.17 |
| 8487 | 3 | 4 | | | IV-1 | METTL10 | 1.36 | 8583 | 3 | 4 | | | IV-1 | MRTO4 | 1.06 |
| 8488 | 3 | 4 | | | IV-1 | METTL11A | 1.48 | 8584 | 3 | 4 | | | IV-1 | MSH5-SAPCD1 | 1.19 |
| 8489 | 3 | 4 | | | IV-1 | METTL12 | 1.15 | 8585 | 3 | 4 | | | IV-1 | MSI2 | 1.48 |
| 8490 | 3 | 4 | | | IV-1 | METTL15 | 1.41 | 8586 | 3 | 4 | | | IV-1 | MSN | 1.29 |
| 8491 | 3 | 4 | | | IV-1 | METTL23 | 1.40 | 8587 | 3 | 4 | | | IV-1 | MSRA | 1.42 |
| 8492 | 3 | 4 | | | IV-1 | METTL2A | 1.07 | 8588 | 3 | 4 | | | IV-1 | MT1X | 1.24 |
| 8493 | 3 | 4 | | | IV-1 | METTL28 | 1.30 | 8589 | 3 | 4 | | | IV-1 | MTCH2 | 1.30 |
| 8494 | 3 | 4 | | | IV-1 | METTL5 | 1.04 | 8590 | 3 | 4 | | | IV-1 | MTCP1 | 1.27 |
| 8495 | 3 | 4 | | | IV-1 | METTL6 | 1.40 | 8591 | 3 | 4 | | | IV-1 | MTFMT | 1.42 |
| 8496 | 3 | 4 | | | IV-1 | METTL9 | 1.11 | 8592 | 3 | 4 | | | IV-1 | MTHFD2L | 1.30 |
| 8497 | 3 | 4 | | | IV-1 | MEX3C | 1.08 | 8593 | 3 | 4 | | | IV-1 | MTIF2 | 1.28 |
| 8498 | 3 | 4 | | | IV-1 | MEX3D | 1.25 | 8594 | 3 | 4 | | | IV-1 | MTIF3 | 1.34 |
| 8499 | 3 | 4 | | | IV-1 | MFF | 1.27 | 8595 | 3 | 4 | | | IV-1 | MTMR12 | 1.50 |
| 8500 | 3 | 4 | | | IV-1 | MGAT2 | 1.30 | 8596 | 3 | 4 | | | IV-1 | MTMR2 | 1.18 |
| 8501 | 3 | 4 | | | IV-1 | MGAT5 | 1.33 | 8597 | 3 | 4 | | | IV-1 | MUL1 | 1.20 |
| 8502 | 3 | 4 | | | IV-1 | MGC21881 | 1.27 | 8598 | 3 | 4 | | | IV-1 | MUTED | 1.14 |
| 8503 | 3 | 4 | | | IV-1 | MGC2752 | 1.21 | 8599 | 3 | 4 | | | IV-1 | MUTYH | 1.41 |
| 8504 | 3 | 4 | | | IV-1 | MGC72080 | 1.47 | 8600 | 3 | 4 | | | IV-1 | MXD4 | 1.10 |
| 8505 | 3 | 4 | | | IV-1 | MGMT | 1.19 | 8601 | 3 | 4 | | | IV-1 | MYCBP | 1.25 |
| 8506 | 3 | 4 | | | IV-1 | MGST3 | 1.05 | 8602 | 3 | 4 | | | IV-1 | MYEOV2 | 1.21 |
| 8507 | 3 | 4 | | | IV-1 | MID2 | 1.44 | 8603 | 3 | 4 | | | IV-1 | MYH11 | 1.00 |
| 8508 | 3 | 4 | | | IV-1 | MIDN | 1.39 | 8604 | 3 | 4 | | | IV-1 | MYH3 | 1.20 |
| 8509 | 3 | 4 | | | IV-1 | MIF4GD | 1.09 | 8605 | 3 | 4 | | | IV-1 | MYL12B | 1.07 |
| 8510 | 3 | 4 | | | IV-1 | MINOS1 | 1.24 | 8606 | 3 | 4 | | | IV-1 | MYNN | 1.38 |
| 8511 | 3 | 4 | | | IV-1 | MINPP1 | 1.27 | 8607 | 3 | 4 | | | IV-1 | MYO1D | 1.39 |
| 8512 | 3 | 4 | | | IV-1 | MIS12 | 1.40 | 8608 | 3 | 4 | | | IV-1 | MZT1 | 1.22 |
| 8513 | 3 | 4 | | | IV-1 | MIS18A | 1.18 | 8609 | 3 | 4 | | | IV-1 | MZT2A | 1.03 |
| 8514 | 3 | 4 | | | IV-1 | MKKS | 1.49 | 8610 | 3 | 4 | | | IV-1 | N4BP2 | 1.38 |
| 8515 | 3 | 4 | | | IV-1 | MKNK2 | 1.11 | 8611 | 3 | 4 | | | IV-1 | NAA10 | 1.39 |
| 8516 | 3 | 4 | | | IV-1 | MLEC | 1.24 | 8612 | 3 | 4 | | | IV-1 | NAA20 | 1.36 |
| 8517 | 3 | 4 | | | IV-1 | MLF2 | 1.06 | 8613 | 3 | 4 | | | IV-1 | NAA50 | 1.17 |
| 8518 | 3 | 4 | | | IV-1 | MLH1 | 1.42 | 8614 | 3 | 4 | | | IV-1 | NAA60 | 1.34 |
| 8519 | 3 | 4 | | | IV-1 | MLH3 | 1.23 | 8615 | 3 | 4 | | | IV-1 | NAALADL1 | 1.21 |
| 8520 | 3 | 4 | | | IV-1 | MLLT1 | 1.46 | 8616 | 3 | 4 | | | IV-1 | NACA | 1.13 |
| 8521 | 3 | 4 | | | IV-1 | MLLT11 | 1.46 | 8617 | 3 | 4 | | | IV-1 | NACA2 | 1.35 |
| 8522 | 3 | 4 | | | IV-1 | MLLT3 | 1.17 | 8618 | 3 | 4 | | | IV-1 | NACAP1 | 1.08 |
| 8523 | 3 | 4 | | | IV-1 | MLST8 | 1.26 | 8619 | 3 | 4 | | | IV-1 | NACC1 | 1.22 |
| 8524 | 3 | 4 | | | IV-1 | MLX | 1.30 | 8620 | 3 | 4 | | | IV-1 | NAGS | 1.45 |
| 8525 | 3 | 4 | | | IV-1 | MMGT1 | 1.49 | 8621 | 3 | 4 | | | IV-1 | NAMPT | 1.33 |
| 8526 | 3 | 4 | | | IV-1 | MMP24 | 1.18 | 8622 | 3 | 4 | | | IV-1 | NANP | 1.22 |
| 8527 | 3 | 4 | | | IV-1 | MMS22L | 1.25 | 8623 | 3 | 4 | | | IV-1 | NANS | 1.34 |
| 8528 | 3 | 4 | | | IV-1 | MOAP1 | 1.22 | 8624 | 3 | 4 | | | IV-1 | NAP1L5 | 1.34 |
| 8529 | 3 | 4 | | | IV-1 | MOB2 | 1.46 | 8625 | 3 | 4 | | | IV-1 | NAPSA | 1.28 |
| 8530 | 3 | 4 | | | IV-1 | MOB3A | 1.50 | 8626 | 3 | 4 | | | IV-1 | NARF | 1.04 |
| 8531 | 3 | 4 | | | IV-1 | MOCS2 | 1.20 | 8627 | 3 | 4 | | | IV-1 | NARG2 | 1.33 |
| 8532 | 3 | 4 | | | IV-1 | MOCS3 | 1.39 | 8628 | 3 | 4 | | | IV-1 | NARS2 | 1.34 |
| 8533 | 3 | 4 | | | IV-1 | MON1A | 1.44 | 8629 | 3 | 4 | | | IV-1 | NAT6 | 1.33 |
| 8534 | 3 | 4 | | | IV-1 | MORC4 | 1.28 | 8630 | 3 | 4 | | | IV-1 | NAV1 | 1.04 |
| 8535 | 3 | 4 | | | IV-1 | MORN2 | 1.06 | 8631 | 3 | 4 | | | IV-1 | NCK1 | 1.12 |
| 8536 | 3 | 4 | | | IV-1 | MPDU1 | 1.36 | 8632 | 3 | 4 | | | IV-1 | NCK2 | 1.07 |
| 8537 | 3 | 4 | | | IV-1 | MPG | 1.06 | 8633 | 3 | 4 | | | IV-1 | NDE1 | 1.49 |
| 8538 | 3 | 4 | | | IV-1 | MPHOSPH10 | 1.30 | 8634 | 3 | 4 | | | IV-1 | NDEL1 | 1.40 |
| 8539 | 3 | 4 | | | IV-1 | MPL | 1.44 | 8635 | 3 | 4 | | | IV-1 | NDFIP1 | 1.31 |

Fig. 40 - 46

| | | | | | | | | | | | | | | |
|---|---|---|---|---|---|---|---|---|---|---|---|---|---|---|
| 8636 | 3 | 4 | | | IV-1 | NDNL2 | 1.17 | 8732 | 3 | 4 | | | IV-1 | OBFC2B | 1.17 |
| 8637 | 3 | 4 | | | IV-1 | NDST1 | 1.39 | 8733 | 3 | 4 | | | IV-1 | OCEL1 | 1.47 |
| 8638 | 3 | 4 | | | IV-1 | NDUFA5 | 1.19 | 8734 | 3 | 4 | | | IV-1 | OCIAD1 | 1.43 |
| 8639 | 3 | 4 | | | IV-1 | NDUFA6 | 1.36 | 8735 | 3 | 4 | | | IV-1 | OIP5-AS1 | 1.11 |
| 8640 | 3 | 4 | | | IV-1 | NDUFA8 | 1.05 | 8736 | 3 | 4 | | | IV-1 | OPLAH | 1.25 |
| 8641 | 3 | 4 | | | IV-1 | NDUFB3 | 1.36 | 8737 | 3 | 4 | | | IV-1 | OR10G2 | 1.07 |
| 8642 | 3 | 4 | | | IV-1 | NDUFB5 | 1.09 | 8738 | 3 | 4 | | | IV-1 | OR10V2P | 1.11 |
| 8643 | 3 | 4 | | | IV-1 | NDUFB9 | 1.00 | 8739 | 3 | 4 | | | IV-1 | ORC5 | 1.26 |
| 8644 | 3 | 4 | | | IV-1 | NDUFC1 | 1.39 | 8740 | 3 | 4 | | | IV-1 | ORMDL2 | 1.38 |
| 8645 | 3 | 4 | | | IV-1 | NDUFS3 | 1.05 | 8741 | 3 | 4 | | | IV-1 | ORMDL3 | 1.23 |
| 8646 | 3 | 4 | | | IV-1 | NDUFS4 | 1.12 | 8742 | 3 | 4 | | | IV-1 | OSBPL8 | 1.01 |
| 8647 | 3 | 4 | | | IV-1 | NDUFS6 | 1.45 | 8743 | 3 | 4 | | | IV-1 | OST4 | 1.08 |
| 8648 | 3 | 4 | | | IV-1 | NDUFS7 | 1.25 | 8744 | 3 | 4 | | | IV-1 | OSTC | 1.06 |
| 8649 | 3 | 4 | | | IV-1 | NDUFS8 | 1.04 | 8745 | 3 | 4 | | | IV-1 | OSTCP1 | 1.44 |
| 8650 | 3 | 4 | | | IV-1 | NDUFV2 | 1.08 | 8746 | 3 | 4 | | | IV-1 | OSTF1 | 1.41 |
| 8651 | 3 | 4 | | | IV-1 | NECAP2 | 1.34 | 8747 | 3 | 4 | | | IV-1 | OTUB1 | 1.42 |
| 8652 | 3 | 4 | | | IV-1 | NEDD8 | 1.11 | 8748 | 3 | 4 | | | IV-1 | OTUD7B | 1.23 |
| 8653 | 3 | 4 | | | IV-1 | NEDD8-MDP1 | 1.27 | 8749 | 3 | 4 | | | IV-1 | OTX1 | 1.46 |
| 8654 | 3 | 4 | | | IV-1 | NEFH | 1.35 | 8750 | 3 | 4 | | | IV-1 | OVCA2 | 1.13 |
| 8655 | 3 | 4 | | | IV-1 | NEK3 | 1.49 | 8751 | 3 | 4 | | | IV-1 | OXSM | 1.36 |
| 8656 | 3 | 4 | | | IV-1 | NEK7 | 1.45 | 8752 | 3 | 4 | | | IV-1 | P2RY8 | 1.12 |
| 8657 | 3 | 4 | | | IV-1 | NENF | 1.13 | 8753 | 3 | 4 | | | IV-1 | P4HB | 1.28 |
| 8658 | 3 | 4 | | | IV-1 | NF2 | 1.42 | 8754 | 3 | 4 | | | IV-1 | PA2G4 | 1.30 |
| 8659 | 3 | 4 | | | IV-1 | NFKBIL1 | 1.35 | 8755 | 3 | 4 | | | IV-1 | PA2G4P4 | 1.20 |
| 8660 | 3 | 4 | | | IV-1 | NFU1 | 1.23 | 8756 | 3 | 4 | | | IV-1 | PABPC1 | 1.20 |
| 8661 | 3 | 4 | | | IV-1 | NFYB | 1.41 | 8757 | 3 | 4 | | | IV-1 | PABPC3 | 1.31 |
| 8662 | 3 | 4 | | | IV-1 | NGDN | 1.05 | 8758 | 3 | 4 | | | IV-1 | PACS1 | 1.23 |
| 8663 | 3 | 4 | | | IV-1 | NGRN | 1.28 | 8759 | 3 | 4 | | | IV-1 | PAFAH1B2 | 1.29 |
| 8664 | 3 | 4 | | | IV-1 | NHEJ1 | 1.49 | 8760 | 3 | 4 | | | IV-1 | PAFAH1B3 | 1.06 |
| 8665 | 3 | 4 | | | IV-1 | NHLRC1 | 1.09 | 8761 | 3 | 4 | | | IV-1 | PAFAH2 | 1.04 |
| 8666 | 3 | 4 | | | IV-1 | NHLRC4 | 1.24 | 8762 | 3 | 4 | | | IV-1 | PAIP1 | 1.14 |
| 8667 | 3 | 4 | | | IV-1 | NHP2L1 | 1.02 | 8763 | 3 | 4 | | | IV-1 | PAIP2 | 1.25 |
| 8668 | 3 | 4 | | | IV-1 | NHSL1 | 1.30 | 8764 | 3 | 4 | | | IV-1 | PAK1IP1 | 1.19 |
| 8669 | 3 | 4 | | | IV-1 | NIF3L1 | 1.41 | 8765 | 3 | 4 | | | IV-1 | PALB2 | 1.18 |
| 8670 | 3 | 4 | | | IV-1 | NIP7 | 1.09 | 8766 | 3 | 4 | | | IV-1 | PALLD | 1.38 |
| 8671 | 3 | 4 | | | IV-1 | NIPAL2 | 1.43 | 8767 | 3 | 4 | | | IV-1 | PANK3 | 1.15 |
| 8672 | 3 | 4 | | | IV-1 | NIT2 | 1.41 | 8768 | 3 | 4 | | | IV-1 | PAPOLB | 1.45 |
| 8673 | 3 | 4 | | | IV-1 | NLGN2 | 1.14 | 8769 | 3 | 4 | | | IV-1 | PAPSS1 | 1.36 |
| 8674 | 3 | 4 | | | IV-1 | NLRC3 | 1.40 | 8770 | 3 | 4 | | | IV-1 | PAR-SN | 1.36 |
| 8675 | 3 | 4 | | | IV-1 | NLRX1 | 1.19 | 8771 | 3 | 4 | | | IV-1 | PAR5 | 1.08 |
| 8676 | 3 | 4 | | | IV-1 | NMD3 | 1.13 | 8772 | 3 | 4 | | | IV-1 | PARK7 | 1.16 |
| 8677 | 3 | 4 | | | IV-1 | NME1 | 1.05 | 8773 | 3 | 4 | | | IV-1 | PARL | 1.16 |
| 8678 | 3 | 4 | | | IV-1 | NME2 | 1.12 | 8774 | 3 | 4 | | | IV-1 | PARP16 | 1.00 |
| 8679 | 3 | 4 | | | IV-1 | NME6 | 1.14 | 8775 | 3 | 4 | | | IV-1 | PARP2 | 1.16 |
| 8680 | 3 | 4 | | | IV-1 | NMT2 | 1.50 | 8776 | 3 | 4 | | | IV-1 | PARVB | 1.13 |
| 8681 | 3 | 4 | | | IV-1 | NOA1 | 1.23 | 8777 | 3 | 4 | | | IV-1 | PATZ1 | 1.50 |
| 8682 | 3 | 4 | | | IV-1 | NOB1 | 1.18 | 8778 | 3 | 4 | | | IV-1 | PAXIP1 | 1.31 |
| 8683 | 3 | 4 | | | IV-1 | NOL10 | 1.45 | 8779 | 3 | 4 | | | IV-1 | PCBD2 | 1.45 |
| 8684 | 3 | 4 | | | IV-1 | NOL11 | 1.43 | 8780 | 3 | 4 | | | IV-1 | PCBP1 | 1.45 |
| 8685 | 3 | 4 | | | IV-1 | NONO | 1.39 | 8781 | 3 | 4 | | | IV-1 | PCBP4 | 1.01 |
| 8686 | 3 | 4 | | | IV-1 | NOP14-AS1 | 1.28 | 8782 | 3 | 4 | | | IV-1 | PCGF6 | 1.38 |
| 8687 | 3 | 4 | | | IV-1 | NOP16 | 1.22 | 8783 | 3 | 4 | | | IV-1 | PCMTD1 | 1.45 |
| 8688 | 3 | 4 | | | IV-1 | NOSIP | 1.04 | 8784 | 3 | 4 | | | IV-1 | PCNP | 1.45 |
| 8689 | 3 | 4 | | | IV-1 | NOXA1 | 1.32 | 8785 | 3 | 4 | | | IV-1 | PCP4L1 | 1.13 |
| 8690 | 3 | 4 | | | IV-1 | NPHP3-ACAD11 | 1.40 | 8786 | 3 | 4 | | | IV-1 | PCTP | 1.23 |
| 8691 | 3 | 4 | | | IV-1 | NPM3 | 1.03 | 8787 | 3 | 4 | | | IV-1 | PCYOX1 | 1.34 |
| 8692 | 3 | 4 | | | IV-1 | NPPA | 1.30 | 8788 | 3 | 4 | | | IV-1 | PCYT1A | 1.33 |
| 8693 | 3 | 4 | | | IV-1 | NPRL2 | 1.25 | 8789 | 3 | 4 | | | IV-1 | PCYT1B | 1.39 |
| 8694 | 3 | 4 | | | IV-1 | NR1D2 | 1.14 | 8790 | 3 | 4 | | | IV-1 | PCYT2 | 1.12 |
| 8695 | 3 | 4 | | | IV-1 | NR1H3 | 1.10 | 8791 | 3 | 4 | | | IV-1 | PDAP1 | 1.36 |
| 8696 | 3 | 4 | | | IV-1 | NR2C2AP | 1.47 | 8792 | 3 | 4 | | | IV-1 | PDCD2 | 1.18 |
| 8697 | 3 | 4 | | | IV-1 | NR4A2 | 1.06 | 8793 | 3 | 4 | | | IV-1 | PDCD2L | 1.18 |
| 8698 | 3 | 4 | | | IV-1 | NRAS | 1.42 | 8794 | 3 | 4 | | | IV-1 | PDCL | 1.29 |
| 8699 | 3 | 4 | | | IV-1 | NRBF2 | 1.39 | 8795 | 3 | 4 | | | IV-1 | PDE9A | 1.03 |
| 8700 | 3 | 4 | | | IV-1 | NRBP1 | 1.39 | 8796 | 3 | 4 | | | IV-1 | PDHA2 | 1.49 |
| 8701 | 3 | 4 | | | IV-1 | NRG4 | 1.04 | 8797 | 3 | 4 | | | IV-1 | PDHB | 1.42 |
| 8702 | 3 | 4 | | | IV-1 | NRN1 | 1.35 | 8798 | 3 | 4 | | | IV-1 | PDIA6 | 1.49 |
| 8703 | 3 | 4 | | | IV-1 | NSDHL | 1.32 | 8799 | 3 | 4 | | | IV-1 | PDIK1L | 1.34 |
| 8704 | 3 | 4 | | | IV-1 | NSFP1 | 1.14 | 8800 | 3 | 4 | | | IV-1 | PDK1 | 1.45 |
| 8705 | 3 | 4 | | | IV-1 | NSL1 | 1.47 | 8801 | 3 | 4 | | | IV-1 | PDK2 | 1.13 |
| 8706 | 3 | 4 | | | IV-1 | NSMCE1 | 1.28 | 8802 | 3 | 4 | | | IV-1 | PDLIM1 | 1.27 |
| 8707 | 3 | 4 | | | IV-1 | NSUN4 | 1.45 | 8803 | 3 | 4 | | | IV-1 | PDP2 | 1.45 |
| 8708 | 3 | 4 | | | IV-1 | NT5DC2 | 1.35 | 8804 | 3 | 4 | | | IV-1 | PDRG1 | 1.05 |
| 8709 | 3 | 4 | | | IV-1 | NTAN1 | 1.20 | 8805 | 3 | 4 | | | IV-1 | PDXP | 1.08 |
| 8710 | 3 | 4 | | | IV-1 | NUAK2 | 1.46 | 8806 | 3 | 4 | | | IV-1 | PDZD11 | 1.01 |
| 8711 | 3 | 4 | | | IV-1 | NUBP1 | 1.47 | 8807 | 3 | 4 | | | IV-1 | PEBP1 | 1.12 |
| 8712 | 3 | 4 | | | IV-1 | NUBP2 | 1.21 | 8808 | 3 | 4 | | | IV-1 | PECAM1 | 1.46 |
| 8713 | 3 | 4 | | | IV-1 | NUBPL | 1.36 | 8809 | 3 | 4 | | | IV-1 | PECR | 1.14 |
| 8714 | 3 | 4 | | | IV-1 | NUCB1 | 1.25 | 8810 | 3 | 4 | | | IV-1 | PEF1 | 1.44 |
| 8715 | 3 | 4 | | | IV-1 | NUCB2 | 1.39 | 8811 | 3 | 4 | | | IV-1 | PELO | 1.38 |
| 8716 | 3 | 4 | | | IV-1 | NUDCD1 | 1.12 | 8812 | 3 | 4 | | | IV-1 | PEMT | 1.48 |
| 8717 | 3 | 4 | | | IV-1 | NUDCD2 | 1.11 | 8813 | 3 | 4 | | | IV-1 | PEPD | 1.24 |
| 8718 | 3 | 4 | | | IV-1 | NUDT1 | 1.03 | 8814 | 3 | 4 | | | IV-1 | PET112 | 1.39 |
| 8719 | 3 | 4 | | | IV-1 | NUDT15 | 1.12 | 8815 | 3 | 4 | | | IV-1 | PET117 | 1.42 |
| 8720 | 3 | 4 | | | IV-1 | NUDT16L1 | 1.35 | 8816 | 3 | 4 | | | IV-1 | PEX10 | 1.31 |
| 8721 | 3 | 4 | | | IV-1 | NUDT17 | 1.09 | 8817 | 3 | 4 | | | IV-1 | PEX11A | 1.39 |
| 8722 | 3 | 4 | | | IV-1 | NUDT21 | 1.25 | 8818 | 3 | 4 | | | IV-1 | PEX11B | 1.49 |
| 8723 | 3 | 4 | | | IV-1 | NUDT5 | 1.15 | 8819 | 3 | 4 | | | IV-1 | PEX13 | 1.47 |
| 8724 | 3 | 4 | | | IV-1 | NUDT6 | 1.19 | 8820 | 3 | 4 | | | IV-1 | PEX14 | 1.40 |
| 8725 | 3 | 4 | | | IV-1 | NUFIP1 | 1.23 | 8821 | 3 | 4 | | | IV-1 | PEX19 | 1.27 |
| 8726 | 3 | 4 | | | IV-1 | NUP214 | 1.33 | 8822 | 3 | 4 | | | IV-1 | PEX3 | 1.25 |
| 8727 | 3 | 4 | | | IV-1 | NUP50 | 1.29 | 8823 | 3 | 4 | | | IV-1 | PFDN1 | 1.11 |
| 8728 | 3 | 4 | | | IV-1 | NUS1 | 1.49 | 8824 | 3 | 4 | | | IV-1 | PFDN2 | 1.42 |
| 8729 | 3 | 4 | | | IV-1 | NVL | 1.44 | 8825 | 3 | 4 | | | IV-1 | PFDN6 | 1.23 |
| 8730 | 3 | 4 | | | IV-1 | NXT2 | 1.08 | 8826 | 3 | 4 | | | IV-1 | PGAM5 | 1.03 |
| 8731 | 3 | 4 | | | IV-1 | OAT | 1.08 | 8827 | 3 | 4 | | | IV-1 | PGAP1 | 1.12 |

Fig. 40 - 47

| | | | | | | | | | | | | | | | | |
|---|---|---|---|---|---|---|---|---|---|---|---|---|---|---|---|---|
| 8828 | 3 | 4 | | | IV-1 | PGAP3 | 1.14 | 8924 | 3 | 4 | | | IV-1 | PPC5 | 1.17 |
| 8829 | 3 | 4 | | | IV-1 | PGD | 1.24 | 8925 | 3 | 4 | | | IV-1 | PPIAL4A | 1.35 |
| 8830 | 3 | 4 | | | IV-1 | PGK1 | 1.26 | 8926 | 3 | 4 | | | IV-1 | PPIAL4D | 1.32 |
| 8831 | 3 | 4 | | | IV-1 | PGLS | 1.27 | 8927 | 3 | 4 | | | IV-1 | PPI8 | 1.10 |
| 8832 | 3 | 4 | | | IV-1 | PGM1 | 1.08 | 8928 | 3 | 4 | | | IV-1 | PPID | 1.40 |
| 8833 | 3 | 4 | | | IV-1 | PGPEP1 | 1.50 | 8929 | 3 | 4 | | | IV-1 | PPIE | 1.12 |
| 8834 | 3 | 4 | | | IV-1 | PGRMC1 | 1.48 | 8930 | 3 | 4 | | | IV-1 | PPIL4 | 1.39 |
| 8835 | 3 | 4 | | | IV-1 | PHACTR1 | 1.36 | 8931 | 3 | 4 | | | IV-1 | PPM1B | 1.38 |
| 8836 | 3 | 4 | | | IV-1 | PHAX | 1.30 | 8932 | 3 | 4 | | | IV-1 | PPM1G | 1.47 |
| 8837 | 3 | 4 | | | IV-1 | PHF23 | 1.44 | 8933 | 3 | 4 | | | IV-1 | PPM1H | 1.40 |
| 8838 | 3 | 4 | | | IV-1 | PHLDA1 | 1.03 | 8934 | 3 | 4 | | | IV-1 | PPM1M | 1.10 |
| 8839 | 3 | 4 | | | IV-1 | PHPT1 | 1.30 | 8935 | 3 | 4 | | | IV-1 | PPM1N | 1.39 |
| 8840 | 3 | 4 | | | IV-1 | PHYH | 1.14 | 8936 | 3 | 4 | | | IV-1 | PPP1CA | 1.10 |
| 8841 | 3 | 4 | | | IV-1 | PI4K2A | 1.19 | 8937 | 3 | 4 | | | IV-1 | PPP1CB | 1.48 |
| 8842 | 3 | 4 | | | IV-1 | PIAS1 | 1.39 | 8938 | 3 | 4 | | | IV-1 | PPP1CC | 1.42 |
| 8843 | 3 | 4 | | | IV-1 | PIGC | 1.43 | 8939 | 3 | 4 | | | IV-1 | PPP1R13B | 1.43 |
| 8844 | 3 | 4 | | | IV-1 | PIGK | 1.31 | 8940 | 3 | 4 | | | IV-1 | PPP1R14B | 1.05 |
| 8845 | 3 | 4 | | | IV-1 | PIGP | 1.48 | 8941 | 3 | 4 | | | IV-1 | PPP1R15A | 1.37 |
| 8846 | 3 | 4 | | | IV-1 | PIGT | 1.22 | 8942 | 3 | 4 | | | IV-1 | PPP1R18 | 1.47 |
| 8847 | 3 | 4 | | | IV-1 | PIGU | 1.16 | 8943 | 3 | 4 | | | IV-1 | PPP1R2 | 1.27 |
| 8848 | 3 | 4 | | | IV-1 | PIK3CG | 1.32 | 8944 | 3 | 4 | | | IV-1 | PPP1R2P3 | 1.06 |
| 8849 | 3 | 4 | | | IV-1 | PIK3IP1 | 1.28 | 8945 | 3 | 4 | | | IV-1 | PPP1R7 | 1.49 |
| 8850 | 3 | 4 | | | IV-1 | PIK3R1 | 1.32 | 8946 | 3 | 4 | | | IV-1 | PPP1R8 | 1.07 |
| 8851 | 3 | 4 | | | IV-1 | PIK3R2 | 1.28 | 8947 | 3 | 4 | | | IV-1 | PPP2CA | 1.39 |
| 8852 | 3 | 4 | | | IV-1 | PILRA | 1.43 | 8948 | 3 | 4 | | | IV-1 | PPP2R1A | 1.44 |
| 8853 | 3 | 4 | | | IV-1 | PIN1 | 1.08 | 8949 | 3 | 4 | | | IV-1 | PPP2R5D | 1.40 |
| 8854 | 3 | 4 | | | IV-1 | PIN4 | 1.15 | 8950 | 3 | 4 | | | IV-1 | PPP3CC | 1.08 |
| 8855 | 3 | 4 | | | IV-1 | PIP4K2A | 1.18 | 8951 | 3 | 4 | | | IV-1 | PPP4C | 1.30 |
| 8856 | 3 | 4 | | | IV-1 | PIPSK1B | 1.27 | 8952 | 3 | 4 | | | IV-1 | PPP4R2 | 1.30 |
| 8857 | 3 | 4 | | | IV-1 | PIPSL | 1.19 | 8953 | 3 | 4 | | | IV-1 | PPP5C | 1.20 |
| 8858 | 3 | 4 | | | IV-1 | PITHD1 | 1.20 | 8954 | 3 | 4 | | | IV-1 | PPP6C | 1.36 |
| 8859 | 3 | 4 | | | IV-1 | PITPNA | 1.32 | 8955 | 3 | 4 | | | IV-1 | PPPDE1 | 1.42 |
| 8860 | 3 | 4 | | | IV-1 | PITPNM1 | 1.48 | 8956 | 3 | 4 | | | IV-1 | PQBP1 | 1.12 |
| 8861 | 3 | 4 | | | IV-1 | PJA1 | 1.32 | 8957 | 3 | 4 | | | IV-1 | PRC1 | 1.46 |
| 8862 | 3 | 4 | | | IV-1 | PKNOX1 | 1.37 | 8958 | 3 | 4 | | | IV-1 | PRCC | 1.36 |
| 8863 | 3 | 4 | | | IV-1 | PLA2G4C | 1.29 | 8959 | 3 | 4 | | | IV-1 | PRDM5 | 1.47 |
| 8864 | 3 | 4 | | | IV-1 | PLB1 | 1.30 | 8960 | 3 | 4 | | | IV-1 | PRDX4 | 1.14 |
| 8865 | 3 | 4 | | | IV-1 | PLBD1 | 1.04 | 8961 | 3 | 4 | | | IV-1 | PRDX6 | 1.03 |
| 8866 | 3 | 4 | | | IV-1 | PLCD1 | 1.15 | 8962 | 3 | 4 | | | IV-1 | PRELID1 | 1.06 |
| 8867 | 3 | 4 | | | IV-1 | PLCD3 | 1.12 | 8963 | 3 | 4 | | | IV-1 | PRIM1 | 1.49 |
| 8868 | 3 | 4 | | | IV-1 | PLCL1 | 1.03 | 8964 | 3 | 4 | | | IV-1 | PRKACA | 1.34 |
| 8869 | 3 | 4 | | | IV-1 | PLCL2 | 1.45 | 8965 | 3 | 4 | | | IV-1 | PRKAG1 | 1.34 |
| 8870 | 3 | 4 | | | IV-1 | PLD3 | 1.49 | 8966 | 3 | 4 | | | IV-1 | PRKAR2A | 1.02 |
| 8871 | 3 | 4 | | | IV-1 | PLEKHA1 | 1.24 | 8967 | 3 | 4 | | | IV-1 | PRKCQ | 1.47 |
| 8872 | 3 | 4 | | | IV-1 | PLEKHA3 | 1.31 | 8968 | 3 | 4 | | | IV-1 | PRKCSH | 1.31 |
| 8873 | 3 | 4 | | | IV-1 | PLEKHB2 | 1.47 | 8969 | 3 | 4 | | | IV-1 | PRKRIP1 | 1.29 |
| 8874 | 3 | 4 | | | IV-1 | PLGLA | 1.10 | 8970 | 3 | 4 | | | IV-1 | PRMT1 | 1.06 |
| 8875 | 3 | 4 | | | IV-1 | PLIN2 | 1.35 | 8971 | 3 | 4 | | | IV-1 | PRMT6 | 1.48 |
| 8876 | 3 | 4 | | | IV-1 | PLK3 | 1.42 | 8972 | 3 | 4 | | | IV-1 | PRNP | 1.17 |
| 8877 | 3 | 4 | | | IV-1 | PLLP | 1.24 | 8973 | 3 | 4 | | | IV-1 | PROX2 | 1.16 |
| 8878 | 3 | 4 | | | IV-1 | PLP2 | 1.07 | 8974 | 3 | 4 | | | IV-1 | PRPS1 | 1.30 |
| 8879 | 3 | 4 | | | IV-1 | PLXNA2 | 1.01 | 8975 | 3 | 4 | | | IV-1 | PRR16 | 1.12 |
| 8880 | 3 | 4 | | | IV-1 | PMF1 | 1.08 | 8976 | 3 | 4 | | | IV-1 | PRR7 | 1.07 |
| 8881 | 3 | 4 | | | IV-1 | PMM1 | 1.19 | 8977 | 3 | 4 | | | IV-1 | PSKH1 | 1.17 |
| 8882 | 3 | 4 | | | IV-1 | PMM2 | 1.40 | 8978 | 3 | 4 | | | IV-1 | PSMA2 | 1.39 |
| 8883 | 3 | 4 | | | IV-1 | PMPCB | 1.37 | 8979 | 3 | 4 | | | IV-1 | PSMA5 | 1.48 |
| 8884 | 3 | 4 | | | IV-1 | PMS2P5 | 1.04 | 8980 | 3 | 4 | | | IV-1 | PSMA6 | 1.21 |
| 8885 | 3 | 4 | | | IV-1 | PMVK | 1.05 | 8981 | 3 | 4 | | | IV-1 | PSMB1 | 1.40 |
| 8886 | 3 | 4 | | | IV-1 | PNKD | 1.18 | 8982 | 3 | 4 | | | IV-1 | PSMB2 | 1.36 |
| 8887 | 3 | 4 | | | IV-1 | PNO1 | 1.18 | 8983 | 3 | 4 | | | IV-1 | PSMB3 | 1.48 |
| 8888 | 3 | 4 | | | IV-1 | PNP | 1.43 | 8984 | 3 | 4 | | | IV-1 | PSMB4 | 1.21 |
| 8889 | 3 | 4 | | | IV-1 | PNPLA2 | 1.39 | 8985 | 3 | 4 | | | IV-1 | PSMB5 | 1.39 |
| 8890 | 3 | 4 | | | IV-1 | PNPLA4 | 1.12 | 8986 | 3 | 4 | | | IV-1 | PSMB7 | 1.16 |
| 8891 | 3 | 4 | | | IV-1 | PNPLA8 | 1.41 | 8987 | 3 | 4 | | | IV-1 | PSMC3 | 1.34 |
| 8892 | 3 | 4 | | | IV-1 | POC1B | 1.11 | 8988 | 3 | 4 | | | IV-1 | PSMC4 | 1.26 |
| 8893 | 3 | 4 | | | IV-1 | POC5 | 1.37 | 8989 | 3 | 4 | | | IV-1 | PSMD10 | 1.16 |
| 8894 | 3 | 4 | | | IV-1 | PODXL2 | 1.01 | 8990 | 3 | 4 | | | IV-1 | PSMD11 | 1.31 |
| 8895 | 3 | 4 | | | IV-1 | POLD2 | 1.21 | 8991 | 3 | 4 | | | IV-1 | PSMD14 | 1.28 |
| 8896 | 3 | 4 | | | IV-1 | POLDIP2 | 1.45 | 8992 | 3 | 4 | | | IV-1 | PSMD4 | 1.30 |
| 8897 | 3 | 4 | | | IV-1 | POLR1E | 1.12 | 8993 | 3 | 4 | | | IV-1 | PSMD5 | 1.38 |
| 8898 | 3 | 4 | | | IV-1 | POLR2D | 1.19 | 8994 | 3 | 4 | | | IV-1 | PSMD7 | 1.31 |
| 8899 | 3 | 4 | | | IV-1 | POLR2F | 1.12 | 8995 | 3 | 4 | | | IV-1 | PSMD8 | 1.10 |
| 8900 | 3 | 4 | | | IV-1 | POLR2J | 1.18 | 8996 | 3 | 4 | | | IV-1 | PSME3 | 1.45 |
| 8901 | 3 | 4 | | | IV-1 | POLR2M | 1.06 | 8997 | 3 | 4 | | | IV-1 | PSMF1 | 1.10 |
| 8902 | 3 | 4 | | | IV-1 | POLR3C | 1.47 | 8998 | 3 | 4 | | | IV-1 | PSMG3 | 1.20 |
| 8903 | 3 | 4 | | | IV-1 | POLR3D | 1.33 | 8999 | 3 | 4 | | | IV-1 | PSMG4 | 1.41 |
| 8904 | 3 | 4 | | | IV-1 | POLR3F | 1.50 | 9000 | 3 | 4 | | | IV-1 | PSPH | 1.19 |
| 8905 | 3 | 4 | | | IV-1 | POLR3G | 1.42 | 9001 | 3 | 4 | | | IV-1 | PTBP3 | 1.38 |
| 8906 | 3 | 4 | | | IV-1 | POLR3GL | 1.43 | 9002 | 3 | 4 | | | IV-1 | PTENP1 | 1.44 |
| 8907 | 3 | 4 | | | IV-1 | POLR3H | 1.28 | 9003 | 3 | 4 | | | IV-1 | PTER | 1.44 |
| 8908 | 3 | 4 | | | IV-1 | POLR3K | 1.07 | 9004 | 3 | 4 | | | IV-1 | PTGER2 | 1.02 |
| 8909 | 3 | 4 | | | IV-1 | POMGNT1 | 1.49 | 9005 | 3 | 4 | | | IV-1 | PTGES | 1.48 |
| 8910 | 3 | 4 | | | IV-1 | POP1 | 1.41 | 9006 | 3 | 4 | | | IV-1 | PTGFRN | 1.10 |
| 8911 | 3 | 4 | | | IV-1 | POP4 | 1.30 | 9007 | 3 | 4 | | | IV-1 | PTGR2 | 1.28 |
| 8912 | 3 | 4 | | | IV-1 | POPDC2 | 1.37 | 9008 | 3 | 4 | | | IV-1 | PTK6 | 1.24 |
| 8913 | 3 | 4 | | | IV-1 | PORCN | 1.24 | 9009 | 3 | 4 | | | IV-1 | PTP4A2 | 1.16 |
| 8914 | 3 | 4 | | | IV-1 | POT1 | 1.41 | 9010 | 3 | 4 | | | IV-1 | PTP4A3 | 1.18 |
| 8915 | 3 | 4 | | | IV-1 | POTEE | 1.03 | 9011 | 3 | 4 | | | IV-1 | PTPLAD1 | 1.42 |
| 8916 | 3 | 4 | | | IV-1 | POTEF | 1.24 | 9012 | 3 | 4 | | | IV-1 | PTPMT1 | 1.17 |
| 8917 | 3 | 4 | | | IV-1 | POTEKP | 1.05 | 9013 | 3 | 4 | | | IV-1 | PTPN18 | 1.43 |
| 8918 | 3 | 4 | | | IV-1 | POTEM | 1.05 | 9014 | 3 | 4 | | | IV-1 | PTPN7 | 1.05 |
| 8919 | 3 | 4 | | | IV-1 | POU5F1 | 1.18 | 9015 | 3 | 4 | | | IV-1 | PTPN9 | 1.38 |
| 8920 | 3 | 4 | | | IV-1 | POU5F1B | 1.05 | 9016 | 3 | 4 | | | IV-1 | PTPRA | 1.30 |
| 8921 | 3 | 4 | | | IV-1 | PPA1 | 1.05 | 9017 | 3 | 4 | | | IV-1 | PTPRK | 1.17 |
| 8922 | 3 | 4 | | | IV-1 | PPAN | 1.47 | 9018 | 3 | 4 | | | IV-1 | PTPRS | 1.05 |
| 8923 | 3 | 4 | | | IV-1 | PPARA | 1.34 | 9019 | 3 | 4 | | | IV-1 | PTTG1IP | 1.42 |

Fig. 40 - 48

| | | | | | | | | | | | | | | | |
|---|---|---|---|---|---|---|---|---|---|---|---|---|---|---|---|
| 9020 | 3 | 4 | | | IV-1 | PUF60 | 1.35 | 9116 | 3 | 4 | | | IV-1 | RGL1 | 1.29 |
| 9021 | 3 | 4 | | | IV-1 | PUS7 | 1.42 | 9117 | 3 | 4 | | | IV-1 | RGS18 | 1.43 |
| 9022 | 3 | 4 | | | IV-1 | PVRIG | 1.24 | 9118 | 3 | 4 | | | IV-1 | RGS19 | 1.49 |
| 9023 | 3 | 4 | | | IV-1 | PWP1 | 1.26 | 9119 | 3 | 4 | | | IV-1 | RGS3 | 1.31 |
| 9024 | 3 | 4 | | | IV-1 | PXK | 1.27 | 9120 | 3 | 4 | | | IV-1 | RHEB | 1.08 |
| 9025 | 3 | 4 | | | IV-1 | PXMP2 | 1.01 | 9121 | 3 | 4 | | | IV-1 | RHEBL1 | 1.10 |
| 9026 | 3 | 4 | | | IV-1 | PYCRL | 1.03 | 9122 | 3 | 4 | | | IV-1 | RHOA | 1.48 |
| 9027 | 3 | 4 | | | IV-1 | PYGL | 1.11 | 9123 | 3 | 4 | | | IV-1 | RHOG | 1.18 |
| 9028 | 3 | 4 | | | IV-1 | PYHIN1 | 1.25 | 9124 | 3 | 4 | | | IV-1 | RIC8A | 1.41 |
| 9029 | 3 | 4 | | | IV-1 | ProSAPiP1 | 1.31 | 9125 | 3 | 4 | | | IV-1 | RILPL2 | 1.37 |
| 9030 | 3 | 4 | | | IV-1 | QARS | 1.08 | 9126 | 3 | 4 | | | IV-1 | RIMBP3 | 1.37 |
| 9031 | 3 | 4 | | | IV-1 | QPRT | 1.02 | 9127 | 3 | 4 | | | IV-1 | RIMBP3B | 1.33 |
| 9032 | 3 | 4 | | | IV-1 | R3HCC1 | 1.09 | 9128 | 3 | 4 | | | IV-1 | RIMS3 | 1.04 |
| 9033 | 3 | 4 | | | IV-1 | RAB11B | 1.16 | 9129 | 3 | 4 | | | IV-1 | RIOK2 | 1.03 |
| 9034 | 3 | 4 | | | IV-1 | RAB11FIP5 | 1.06 | 9130 | 3 | 4 | | | IV-1 | RLF | 1.50 |
| 9035 | 3 | 4 | | | IV-1 | RAB1B | 1.36 | 9131 | 3 | 4 | | | IV-1 | RLIM | 1.39 |
| 9036 | 3 | 4 | | | IV-1 | RAB1B | 1.05 | 9132 | 3 | 4 | | | IV-1 | RLN2 | 1.25 |
| 9037 | 3 | 4 | | | IV-1 | RAB20 | 1.06 | 9133 | 3 | 4 | | | IV-1 | RMND1 | 1.47 |
| 9038 | 3 | 4 | | | IV-1 | RAB22A | 1.48 | 9134 | 3 | 4 | | | IV-1 | RNASEH2A | 1.32 |
| 9039 | 3 | 4 | | | IV-1 | RAB27A | 1.33 | 9135 | 3 | 4 | | | IV-1 | RNASEH2B | 1.41 |
| 9040 | 3 | 4 | | | IV-1 | RAB32 | 1.41 | 9136 | 3 | 4 | | | IV-1 | RNASEK | 1.47 |
| 9041 | 3 | 4 | | | IV-1 | RAB35 | 1.37 | 9137 | 3 | 4 | | | IV-1 | RNF113A | 1.27 |
| 9042 | 3 | 4 | | | IV-1 | RAB36 | 1.10 | 9138 | 3 | 4 | | | IV-1 | RNF115 | 1.20 |
| 9043 | 3 | 4 | | | IV-1 | RAB3A | 1.04 | 9139 | 3 | 4 | | | IV-1 | RNF125 | 1.24 |
| 9044 | 3 | 4 | | | IV-1 | RAB40B | 1.30 | 9140 | 3 | 4 | | | IV-1 | RNF126 | 1.37 |
| 9045 | 3 | 4 | | | IV-1 | RAB40C | 1.32 | 9141 | 3 | 4 | | | IV-1 | RNF126P1 | 1.00 |
| 9046 | 3 | 4 | | | IV-1 | RAB43 | 1.44 | 9142 | 3 | 4 | | | IV-1 | RNF130 | 1.38 |
| 9047 | 3 | 4 | | | IV-1 | RAB4A | 1.45 | 9143 | 3 | 4 | | | IV-1 | RNF139 | 1.26 |
| 9048 | 3 | 4 | | | IV-1 | RAB4B | 1.33 | 9144 | 3 | 4 | | | IV-1 | RNF14 | 1.24 |
| 9049 | 3 | 4 | | | IV-1 | RAB5B | 1.20 | 9145 | 3 | 4 | | | IV-1 | RNF144A | 1.36 |
| 9050 | 3 | 4 | | | IV-1 | RAB5C | 1.14 | 9146 | 3 | 4 | | | IV-1 | RNF144B | 1.22 |
| 9051 | 3 | 4 | | | IV-1 | RAB6A | 1.22 | 9147 | 3 | 4 | | | IV-1 | RNF167 | 1.22 |
| 9052 | 3 | 4 | | | IV-1 | RAB6C | 1.10 | 9148 | 3 | 4 | | | IV-1 | RNF187 | 1.14 |
| 9053 | 3 | 4 | | | IV-1 | RAB7A | 1.26 | 9149 | 3 | 4 | | | IV-1 | RNF2 | 1.14 |
| 9054 | 3 | 4 | | | IV-1 | RAB7L1 | 1.11 | 9150 | 3 | 4 | | | IV-1 | RNF219 | 1.16 |
| 9055 | 3 | 4 | | | IV-1 | RAB9A | 1.37 | 9151 | 3 | 4 | | | IV-1 | RNF220 | 1.33 |
| 9056 | 3 | 4 | | | IV-1 | RABEPK | 1.19 | 9152 | 3 | 4 | | | IV-1 | RNF25 | 1.46 |
| 9057 | 3 | 4 | | | IV-1 | RABGEF1 | 1.42 | 9153 | 3 | 4 | | | IV-1 | RNF26 | 1.33 |
| 9058 | 3 | 4 | | | IV-1 | RABIF | 1.20 | 9154 | 3 | 4 | | | IV-1 | RNF32 | 1.23 |
| 9059 | 3 | 4 | | | IV-1 | RABL3 | 1.18 | 9155 | 3 | 4 | | | IV-1 | RNF4 | 1.39 |
| 9060 | 3 | 4 | | | IV-1 | RAC2 | 1.40 | 9156 | 3 | 4 | | | IV-1 | RNF41 | 1.43 |
| 9061 | 3 | 4 | | | IV-1 | RACGAP1P | 1.40 | 9157 | 3 | 4 | | | IV-1 | RNF7 | 1.26 |
| 9062 | 3 | 4 | | | IV-1 | RAD1 | 1.15 | 9158 | 3 | 4 | | | IV-1 | RNF8 | 1.46 |
| 9063 | 3 | 4 | | | IV-1 | RAD23A | 1.24 | 9159 | 3 | 4 | | | IV-1 | RNMTL1 | 1.29 |
| 9064 | 3 | 4 | | | IV-1 | RAD23B | 1.46 | 9160 | 3 | 4 | | | IV-1 | RNPEPL1 | 1.13 |
| 9065 | 3 | 4 | | | IV-1 | RAD51B | 1.08 | 9161 | 3 | 4 | | | IV-1 | RNPS1 | 1.31 |
| 9066 | 3 | 4 | | | IV-1 | RAE1 | 1.19 | 9162 | 3 | 4 | | | IV-1 | ROGDI | 1.26 |
| 9067 | 3 | 4 | | | IV-1 | RALGDS | 1.33 | 9163 | 3 | 4 | | | IV-1 | RPA1 | 1.23 |
| 9068 | 3 | 4 | | | IV-1 | RALY | 1.28 | 9164 | 3 | 4 | | | IV-1 | RPA2 | 1.17 |
| 9069 | 3 | 4 | | | IV-1 | RAN | 1.17 | 9165 | 3 | 4 | | | IV-1 | RPAP2 | 1.35 |
| 9070 | 3 | 4 | | | IV-1 | RANBP1 | 1.08 | 9166 | 3 | 4 | | | IV-1 | RPE | 1.42 |
| 9071 | 3 | 4 | | | IV-1 | RANGRF | 1.27 | 9167 | 3 | 4 | | | IV-1 | RPF1 | 1.18 |
| 9072 | 3 | 4 | | | IV-1 | RAP1A | 1.44 | 9168 | 3 | 4 | | | IV-1 | RPIA | 1.35 |
| 9073 | 3 | 4 | | | IV-1 | RAP1B | 1.25 | 9169 | 3 | 4 | | | IV-1 | RPL17-C18ORF32 | 1.04 |
| 9074 | 3 | 4 | | | IV-1 | RAP1GDS1 | 1.49 | 9170 | 3 | 4 | | | IV-1 | RPL19P12 | 1.08 |
| 9075 | 3 | 4 | | | IV-1 | RAP2A | 1.02 | 9171 | 3 | 4 | | | IV-1 | RPL22 | 1.24 |
| 9076 | 3 | 4 | | | IV-1 | RAP2B | 1.48 | 9172 | 3 | 4 | | | IV-1 | RPL23 | 1.41 |
| 9077 | 3 | 4 | | | IV-1 | RAPGEF1 | 1.16 | 9173 | 3 | 4 | | | IV-1 | RPL26L1 | 1.28 |
| 9078 | 3 | 4 | | | IV-1 | RARRES3 | 1.41 | 9174 | 3 | 4 | | | IV-1 | RPL28 | 1.27 |
| 9079 | 3 | 4 | | | IV-1 | RARS | 1.30 | 9175 | 3 | 4 | | | IV-1 | RPL29P2 | 1.47 |
| 9080 | 3 | 4 | | | IV-1 | RARS2 | 1.43 | 9176 | 3 | 4 | | | IV-1 | RPL32 | 1.03 |
| 9081 | 3 | 4 | | | IV-1 | RASA2 | 1.35 | 9177 | 3 | 4 | | | IV-1 | RPL34 | 1.30 |
| 9082 | 3 | 4 | | | IV-1 | RASSF2 | 1.19 | 9178 | 3 | 4 | | | IV-1 | RPL7L1 | 1.39 |
| 9083 | 3 | 4 | | | IV-1 | RASSF3 | 1.48 | 9179 | 3 | 4 | | | IV-1 | RPLP2 | 1.27 |
| 9084 | 3 | 4 | | | IV-1 | RAVER2 | 1.00 | 9180 | 3 | 4 | | | IV-1 | RPN1 | 1.29 |
| 9085 | 3 | 4 | | | IV-1 | RBFA | 1.23 | 9181 | 3 | 4 | | | IV-1 | RPP14 | 1.43 |
| 9086 | 3 | 4 | | | IV-1 | RBL1 | 1.31 | 9182 | 3 | 4 | | | IV-1 | RPP38 | 1.23 |
| 9087 | 3 | 4 | | | IV-1 | RBM15 | 1.32 | 9183 | 3 | 4 | | | IV-1 | RPP40 | 1.43 |
| 9088 | 3 | 4 | | | IV-1 | RBM15B | 1.22 | 9184 | 3 | 4 | | | IV-1 | RPRD1A | 1.42 |
| 9089 | 3 | 4 | | | IV-1 | RBM18 | 1.44 | 9185 | 3 | 4 | | | IV-1 | RPS10P7 | 1.28 |
| 9090 | 3 | 4 | | | IV-1 | RBM4 | 1.40 | 9186 | 3 | 4 | | | IV-1 | RPS27L | 1.34 |
| 9091 | 3 | 4 | | | IV-1 | RBM42 | 1.29 | 9187 | 3 | 4 | | | IV-1 | RPS2P32 | 1.06 |
| 9092 | 3 | 4 | | | IV-1 | RBM48 | 1.33 | 9188 | 3 | 4 | | | IV-1 | RPS6KA1 | 1.45 |
| 9093 | 3 | 4 | | | IV-1 | RBM8A | 1.15 | 9189 | 3 | 4 | | | IV-1 | RPS6KA2 | 1.12 |
| 9094 | 3 | 4 | | | IV-1 | RBMX | 1.44 | 9190 | 3 | 4 | | | IV-1 | RPS6KB2 | 1.46 |
| 9095 | 3 | 4 | | | IV-1 | RBMXL1 | 1.27 | 9191 | 3 | 4 | | | IV-1 | RPUSD1 | 1.25 |
| 9096 | 3 | 4 | | | IV-1 | RBPMS | 1.02 | 9192 | 3 | 4 | | | IV-1 | RPUSD2 | 1.26 |
| 9097 | 3 | 4 | | | IV-1 | RC3H2 | 1.45 | 9193 | 3 | 4 | | | IV-1 | RPUSD3 | 1.26 |
| 9098 | 3 | 4 | | | IV-1 | RCHY1 | 1.45 | 9194 | 3 | 4 | | | IV-1 | RPUSD4 | 1.32 |
| 9099 | 3 | 4 | | | IV-1 | RCL1 | 1.47 | 9195 | 3 | 4 | | | IV-1 | RRAS2 | 1.19 |
| 9100 | 3 | 4 | | | IV-1 | RDBP | 1.08 | 9196 | 3 | 4 | | | IV-1 | RRP1 | 1.43 |
| 9101 | 3 | 4 | | | IV-1 | RDH14 | 1.37 | 9197 | 3 | 4 | | | IV-1 | RRP36 | 1.21 |
| 9102 | 3 | 4 | | | IV-1 | REEP5 | 1.30 | 9198 | 3 | 4 | | | IV-1 | RRP7A | 1.18 |
| 9103 | 3 | 4 | | | IV-1 | RELB | 1.38 | 9199 | 3 | 4 | | | IV-1 | RRP9 | 1.12 |
| 9104 | 3 | 4 | | | IV-1 | REPIN1 | 1.44 | 9200 | 3 | 4 | | | IV-1 | RSBN1 | 1.36 |
| 9105 | 3 | 4 | | | IV-1 | REXO2 | 1.20 | 9201 | 3 | 4 | | | IV-1 | RSG1 | 1.24 |
| 9106 | 3 | 4 | | | IV-1 | REXO4 | 1.40 | 9202 | 3 | 4 | | | IV-1 | RSPH9 | 1.03 |
| 9107 | 3 | 4 | | | IV-1 | RFC2 | 1.25 | 9203 | 3 | 4 | | | IV-1 | RSPRY1 | 1.26 |
| 9108 | 3 | 4 | | | IV-1 | RFC3 | 1.27 | 9204 | 3 | 4 | | | IV-1 | RSRC1 | 1.24 |
| 9109 | 3 | 4 | | | IV-1 | RFFL | 1.16 | 9205 | 3 | 4 | | | IV-1 | RSU1 | 1.20 |
| 9110 | 3 | 4 | | | IV-1 | RFK | 1.19 | 9206 | 3 | 4 | | | IV-1 | RTN3 | 1.44 |
| 9111 | 3 | 4 | | | IV-1 | RFPL2 | 1.02 | 9207 | 3 | 4 | | | IV-1 | RTN4IP1 | 1.19 |
| 9112 | 3 | 4 | | | IV-1 | RFTN1 | 1.25 | 9208 | 3 | 4 | | | IV-1 | RUNX3 | 1.09 |
| 9113 | 3 | 4 | | | IV-1 | RFWD2 | 1.45 | 9209 | 3 | 4 | | | IV-1 | RUSC1-AS1 | 1.01 |
| 9114 | 3 | 4 | | | IV-1 | RG9MTD1 | 1.22 | 9210 | 3 | 4 | | | IV-1 | RUVBL1 | 1.07 |
| 9115 | 3 | 4 | | | IV-1 | RG9MTD2 | 1.36 | 9211 | 3 | 4 | | | IV-1 | RUVBL2 | 1.03 |

Fig. 40 - 49

| | | | | | | | |
|---|---|---|---|---|---|---|---|
| 9212 | 3 | 4 | | IV-1 | RYBP | 1.43 |
| 9213 | 3 | 4 | | IV-1 | RYK | 1.46 |
| 9214 | 3 | 4 | | IV-1 | S100A11 | 1.05 |
| 9215 | 3 | 4 | | IV-1 | S1PR1 | 1.01 |
| 9216 | 3 | 4 | | IV-1 | SAE1 | 1.09 |
| 9217 | 3 | 4 | | IV-1 | SALL2 | 1.13 |
| 9218 | 3 | 4 | | IV-1 | SAMD10 | 1.29 |
| 9219 | 3 | 4 | | IV-1 | SAMM50 | 1.39 |
| 9220 | 3 | 4 | | IV-1 | SAP18 | 1.36 |
| 9221 | 3 | 4 | | IV-1 | SAPCD1 | 1.16 |
| 9222 | 3 | 4 | | IV-1 | SARDH | 1.01 |
| 9223 | 3 | 4 | | IV-1 | SARS | 1.37 |
| 9224 | 3 | 4 | | IV-1 | SARS2 | 1.27 |
| 9225 | 3 | 4 | | IV-1 | SAYSD1 | 1.41 |
| 9226 | 3 | 4 | | IV-1 | SBDS | 1.37 |
| 9227 | 3 | 4 | | IV-1 | SBDSP1 | 1.23 |
| 9228 | 3 | 4 | | IV-1 | SBF1P1 | 1.49 |
| 9229 | 3 | 4 | | IV-1 | SCAMP2 | 1.45 |
| 9230 | 3 | 4 | | IV-1 | SCAMP4 | 1.26 |
| 9231 | 3 | 4 | | IV-1 | SCAND1 | 1.13 |
| 9232 | 3 | 4 | | IV-1 | SCFD2 | 1.23 |
| 9233 | 3 | 4 | | IV-1 | SCGB3A2 | 1.05 |
| 9234 | 3 | 4 | | IV-1 | SCNM1 | 1.31 |
| 9235 | 3 | 4 | | IV-1 | SCOC | 1.40 |
| 9236 | 3 | 4 | | IV-1 | SCP2 | 1.18 |
| 9237 | 3 | 4 | | IV-1 | SCYL1 | 1.37 |
| 9238 | 3 | 4 | | IV-1 | SDCBP2 | 1.06 |
| 9239 | 3 | 4 | | IV-1 | SDF2L1 | 1.38 |
| 9240 | 3 | 4 | | IV-1 | SDF4 | 1.48 |
| 9241 | 3 | 4 | | IV-1 | SDHAF1 | 1.06 |
| 9242 | 3 | 4 | | IV-1 | SDHAF2 | 1.09 |
| 9243 | 3 | 4 | | IV-1 | SDHD | 1.20 |
| 9244 | 3 | 4 | | IV-1 | SDR42E1 | 1.10 |
| 9245 | 3 | 4 | | IV-1 | SEC11C | 1.10 |
| 9246 | 3 | 4 | | IV-1 | SEC13 | 1.32 |
| 9247 | 3 | 4 | | IV-1 | SEC14L5 | 1.05 |
| 9248 | 3 | 4 | | IV-1 | SEC61B | 1.40 |
| 9249 | 3 | 4 | | IV-1 | SEC58P2L | 1.43 |
| 9250 | 3 | 4 | | IV-1 | SELM | 1.20 |
| 9251 | 3 | 4 | | IV-1 | SELPLG | 1.37 |
| 9252 | 3 | 4 | | IV-1 | SELRC1 | 1.39 |
| 9253 | 3 | 4 | | IV-1 | SELS | 1.39 |
| 9254 | 3 | 4 | | IV-1 | SEMA3B | 1.25 |
| 9255 | 3 | 4 | | IV-1 | SEMA4C | 1.30 |
| 9256 | 3 | 4 | | IV-1 | SEMA4F | 1.20 |
| 9257 | 3 | 4 | | IV-1 | SEMA4G | 1.22 |
| 9258 | 3 | 4 | | IV-1 | SENP1 | 1.38 |
| 9259 | 3 | 4 | | IV-1 | 42628 | 1.01 |
| 9260 | 3 | 4 | | IV-1 | SEPHS1 | 1.44 |
| 9261 | 3 | 4 | | IV-1 | 42624 | 1.09 |
| 9262 | 3 | 4 | | IV-1 | 42621 | 1.26 |
| 9263 | 3 | 4 | | IV-1 | 42622 | 1.27 |
| 9264 | 3 | 4 | | IV-1 | SER8P1 | 1.40 |
| 9265 | 3 | 4 | | IV-1 | SERF1B | 1.29 |
| 9266 | 3 | 4 | | IV-1 | SERGEF | 1.13 |
| 9267 | 3 | 4 | | IV-1 | SERINC4 | 1.03 |
| 9268 | 3 | 4 | | IV-1 | SERP1 | 1.10 |
| 9269 | 3 | 4 | | IV-1 | SERPINB1 | 1.27 |
| 9270 | 3 | 4 | | IV-1 | SERPINB6 | 1.12 |
| 9271 | 3 | 4 | | IV-1 | SERPINB9 | 1.41 |
| 9272 | 3 | 4 | | IV-1 | SERPINE1 | 1.27 |
| 9273 | 3 | 4 | | IV-1 | SERPINH1 | 1.40 |
| 9274 | 3 | 4 | | IV-1 | SESN2 | 1.36 |
| 9275 | 3 | 4 | | IV-1 | SET | 1.47 |
| 9276 | 3 | 4 | | IV-1 | SETD3 | 1.33 |
| 9277 | 3 | 4 | | IV-1 | SETMAR | 1.44 |
| 9278 | 3 | 4 | | IV-1 | SF3A2 | 1.27 |
| 9279 | 3 | 4 | | IV-1 | SF3A3 | 1.44 |
| 9280 | 3 | 4 | | IV-1 | SF3B14 | 1.41 |
| 9281 | 3 | 4 | | IV-1 | SFMBT1 | 1.46 |
| 9282 | 3 | 4 | | IV-1 | SFR1 | 1.45 |
| 9283 | 3 | 4 | | IV-1 | SFXN1 | 1.13 |
| 9284 | 3 | 4 | | IV-1 | SFXN2 | 1.50 |
| 9285 | 3 | 4 | | IV-1 | SGK1 | 1.46 |
| 9286 | 3 | 4 | | IV-1 | SGPL1 | 1.32 |
| 9287 | 3 | 4 | | IV-1 | SGTA | 1.15 |
| 9288 | 3 | 4 | | IV-1 | SH3BGRL | 1.35 |
| 9289 | 3 | 4 | | IV-1 | SH3BP5L | 1.43 |
| 9290 | 3 | 4 | | IV-1 | SH3D21 | 1.30 |
| 9291 | 3 | 4 | | IV-1 | SH3GL1 | 1.26 |
| 9292 | 3 | 4 | | IV-1 | SH3GL1P2 | 1.25 |
| 9293 | 3 | 4 | | IV-1 | SH3RF1 | 1.27 |
| 9294 | 3 | 4 | | IV-1 | SHKBP1 | 1.47 |
| 9295 | 3 | 4 | | IV-1 | SHMT2 | 1.16 |
| 9296 | 3 | 4 | | IV-1 | SHPK | 1.36 |
| 9297 | 3 | 4 | | IV-1 | SHQ1 | 1.41 |
| 9298 | 3 | 4 | | IV-1 | SIAH1 | 1.50 |
| 9299 | 3 | 4 | | IV-1 | SIGLEC5 | 1.30 |
| 9300 | 3 | 4 | | IV-1 | SIGMAR1 | 1.12 |
| 9301 | 3 | 4 | | IV-1 | SIKE1 | 1.49 |
| 9302 | 3 | 4 | | IV-1 | SIN3A | 1.36 |
| 9303 | 3 | 4 | | IV-1 | SIPA1L2 | 1.44 |
| 9304 | 3 | 4 | | IV-1 | SIRPA | 1.23 |
| 9305 | 3 | 4 | | IV-1 | SIRT2 | 1.34 |
| 9306 | 3 | 4 | | IV-1 | SIRT4 | 1.00 |
| 9307 | 3 | 4 | | IV-1 | SIRT6 | 1.35 |
| 9308 | 3 | 4 | | IV-1 | SKA2 | 1.40 |
| 9309 | 3 | 4 | | IV-1 | SKP1 | 1.11 |
| 9310 | 3 | 4 | | IV-1 | SKP1P2 | 1.05 |
| 9311 | 3 | 4 | | IV-1 | SLA | 1.43 |
| 9312 | 3 | 4 | | IV-1 | SLAIN1 | 1.10 |
| 9313 | 3 | 4 | | IV-1 | SLAMF1 | 1.23 |
| 9314 | 3 | 4 | | IV-1 | SLC10A3 | 1.14 |
| 9315 | 3 | 4 | | IV-1 | SLC16A1 | 1.47 |
| 9316 | 3 | 4 | | IV-1 | SLC16A7 | 1.21 |
| 9317 | 3 | 4 | | IV-1 | SLC18A2 | 1.15 |
| 9318 | 3 | 4 | | IV-1 | SLC23A3 | 1.16 |
| 9319 | 3 | 4 | | IV-1 | SLC25A1 | 1.19 |
| 9320 | 3 | 4 | | IV-1 | SLC25A12 | 1.45 |
| 9321 | 3 | 4 | | IV-1 | SLC25A15 | 1.09 |
| 9322 | 3 | 4 | | IV-1 | SLC25A26 | 1.03 |
| 9323 | 3 | 4 | | IV-1 | SLC25A3 | 1.45 |
| 9324 | 3 | 4 | | IV-1 | SLC25A32 | 1.44 |
| 9325 | 3 | 4 | | IV-1 | SLC25A38 | 1.25 |
| 9326 | 3 | 4 | | IV-1 | SLC25A4 | 1.11 |
| 9327 | 3 | 4 | | IV-1 | SLC25A40 | 1.46 |
| 9328 | 3 | 4 | | IV-1 | SLC25A42 | 1.34 |
| 9329 | 3 | 4 | | IV-1 | SLC25A43 | 1.35 |
| 9330 | 3 | 4 | | IV-1 | SLC25A44 | 1.26 |
| 9331 | 3 | 4 | | IV-1 | SLC25A5 | 1.21 |
| 9332 | 3 | 4 | | IV-1 | SLC2A13 | 1.05 |
| 9333 | 3 | 4 | | IV-1 | SLC2A4RG | 1.09 |
| 9334 | 3 | 4 | | IV-1 | SLC2A5 | 1.34 |
| 9335 | 3 | 4 | | IV-1 | SLC30A5 | 1.27 |
| 9336 | 3 | 4 | | IV-1 | SLC30A6 | 1.29 |
| 9337 | 3 | 4 | | IV-1 | SLC30A9 | 1.25 |
| 9338 | 3 | 4 | | IV-1 | SLC33A1 | 1.42 |
| 9339 | 3 | 4 | | IV-1 | SLC35A2 | 1.35 |
| 9340 | 3 | 4 | | IV-1 | SLC35B2 | 1.35 |
| 9341 | 3 | 4 | | IV-1 | SLC35B4 | 1.34 |
| 9342 | 3 | 4 | | IV-1 | SLC35D2 | 1.35 |
| 9343 | 3 | 4 | | IV-1 | SLC35E3 | 1.45 |
| 9344 | 3 | 4 | | IV-1 | SLC35F2 | 1.38 |
| 9345 | 3 | 4 | | IV-1 | SLC38A1 | 1.35 |
| 9346 | 3 | 4 | | IV-1 | SLC38A6 | 1.18 |
| 9347 | 3 | 4 | | IV-1 | SLC39A1 | 1.23 |
| 9348 | 3 | 4 | | IV-1 | SLC39A11 | 1.28 |
| 9349 | 3 | 4 | | IV-1 | SLC39A14 | 1.21 |
| 9350 | 3 | 4 | | IV-1 | SLC39A3 | 1.48 |
| 9351 | 3 | 4 | | IV-1 | SLC39A8 | 1.19 |
| 9352 | 3 | 4 | | IV-1 | SLC39A9 | 1.33 |
| 9353 | 3 | 4 | | IV-1 | SLC40A1 | 1.24 |
| 9354 | 3 | 4 | | IV-1 | SLC41A1 | 1.34 |
| 9355 | 3 | 4 | | IV-1 | SLC43A1 | 1.38 |
| 9356 | 3 | 4 | | IV-1 | SLC48A1 | 1.13 |
| 9357 | 3 | 4 | | IV-1 | SLC6A16 | 1.44 |
| 9358 | 3 | 4 | | IV-1 | SLC7A1 | 1.40 |
| 9359 | 3 | 4 | | IV-1 | SLC7A6OS | 1.28 |
| 9360 | 3 | 4 | | IV-1 | SLC9A3R1 | 1.32 |
| 9361 | 3 | 4 | | IV-1 | SLC9B2 | 1.28 |
| 9362 | 3 | 4 | | IV-1 | SLMO2 | 1.21 |
| 9363 | 3 | 4 | | IV-1 | SMAD5 | 1.12 |
| 9364 | 3 | 4 | | IV-1 | SMAD7 | 1.24 |
| 9365 | 3 | 4 | | IV-1 | SMARCB1 | 1.32 |
| 9366 | 3 | 4 | | IV-1 | SMARCE1 | 1.07 |
| 9367 | 3 | 4 | | IV-1 | SMCR7L | 1.43 |
| 9368 | 3 | 4 | | IV-1 | SMEK2 | 1.38 |
| 9369 | 3 | 4 | | IV-1 | SMURF2 | 1.48 |
| 9370 | 3 | 4 | | IV-1 | SMYD2 | 1.27 |
| 9371 | 3 | 4 | | IV-1 | SMYD5 | 1.16 |
| 9372 | 3 | 4 | | IV-1 | SNAI1 | 1.02 |
| 9373 | 3 | 4 | | IV-1 | SNAI3 | 1.18 |
| 9374 | 3 | 4 | | IV-1 | SNAP23 | 1.49 |
| 9375 | 3 | 4 | | IV-1 | SNAP47 | 1.43 |
| 9376 | 3 | 4 | | IV-1 | SNAPC1 | 1.13 |
| 9377 | 3 | 4 | | IV-1 | SNAPC2 | 1.20 |
| 9378 | 3 | 4 | | IV-1 | SNAPC5 | 1.39 |
| 9379 | 3 | 4 | | IV-1 | SNAPIN | 1.20 |
| 9380 | 3 | 4 | | IV-1 | SND1 | 1.44 |
| 9381 | 3 | 4 | | IV-1 | SNF8 | 1.16 |
| 9382 | 3 | 4 | | IV-1 | SNHG15 | 1.43 |
| 9383 | 3 | 4 | | IV-1 | SNHG4 | 1.26 |
| 9384 | 3 | 4 | | IV-1 | SNHG6 | 1.28 |
| 9385 | 3 | 4 | | IV-1 | SNHG8 | 1.20 |
| 9386 | 3 | 4 | | IV-1 | SNN | 1.36 |
| 9387 | 3 | 4 | | IV-1 | SNRNP27 | 1.27 |
| 9388 | 3 | 4 | | IV-1 | SNRNP40 | 1.34 |
| 9389 | 3 | 4 | | IV-1 | SNRPA | 1.47 |
| 9390 | 3 | 4 | | IV-1 | SNRPB | 1.17 |
| 9391 | 3 | 4 | | IV-1 | SNRPB2 | 1.43 |
| 9392 | 3 | 4 | | IV-1 | SNRPC | 1.21 |
| 9393 | 3 | 4 | | IV-1 | SNRPD3 | 1.10 |
| 9394 | 3 | 4 | | IV-1 | SNRPE | 1.09 |
| 9395 | 3 | 4 | | IV-1 | SNRPF | 1.11 |
| 9396 | 3 | 4 | | IV-1 | SNRPG | 1.21 |
| 9397 | 3 | 4 | | IV-1 | SNUPN | 1.38 |
| 9398 | 3 | 4 | | IV-1 | SNX12 | 1.36 |
| 9399 | 3 | 4 | | IV-1 | SNX15 | 1.41 |
| 9400 | 3 | 4 | | IV-1 | SNX17 | 1.34 |
| 9401 | 3 | 4 | | IV-1 | SNX18 | 1.23 |
| 9402 | 3 | 4 | | IV-1 | SNX3 | 1.11 |
| 9403 | 3 | 4 | | IV-1 | SNX4 | 1.41 |

Fig. 40 - 50

| | | | | | | | | | | | | | | | |
|---|---|---|---|---|---|---|---|---|---|---|---|---|---|---|---|
| 9404 | 3 | 4 | | | IV-1 | SOCS5 | 1.30 | 9500 | 3 | 4 | | | IV-1 | TAC4 | 1.49 |
| 9405 | 3 | 4 | | | IV-1 | SOD1 | 1.07 | 9501 | 3 | 4 | | | IV-1 | TACO1 | 1.13 |
| 9406 | 3 | 4 | | | IV-1 | SORBS3 | 1.44 | 9502 | 3 | 4 | | | IV-1 | TADA2A | 1.19 |
| 9407 | 3 | 4 | | | IV-1 | SORD | 1.19 | 9503 | 3 | 4 | | | IV-1 | TADA2B | 1.33 |
| 9408 | 3 | 4 | | | IV-1 | SOX8 | 1.13 | 9504 | 3 | 4 | | | IV-1 | TADA3 | 1.18 |
| 9409 | 3 | 4 | | | IV-1 | SP4 | 1.13 | 9505 | 3 | 4 | | | IV-1 | TAF10 | 1.20 |
| 9410 | 3 | 4 | | | IV-1 | SPAG7 | 1.30 | 9506 | 3 | 4 | | | IV-1 | TAF12 | 1.21 |
| 9411 | 3 | 4 | | | IV-1 | SPCS1 | 1.49 | 9507 | 3 | 4 | | | IV-1 | TAF13 | 1.48 |
| 9412 | 3 | 4 | | | IV-1 | SPCS3 | 1.15 | 9508 | 3 | 4 | | | IV-1 | TAF1A | 1.47 |
| 9413 | 3 | 4 | | | IV-1 | SPDYE1 | 1.39 | 9509 | 3 | 4 | | | IV-1 | TAF5L | 1.29 |
| 9414 | 3 | 4 | | | IV-1 | SPDYE5 | 1.11 | 9510 | 3 | 4 | | | IV-1 | TAF6 | 1.44 |
| 9415 | 3 | 4 | | | IV-1 | SPECC1L | 1.44 | 9511 | 3 | 4 | | | IV-1 | TAF9 | 1.30 |
| 9416 | 3 | 4 | | | IV-1 | SPEG | 1.33 | 9512 | 3 | 4 | | | IV-1 | TAF9B | 1.22 |
| 9417 | 3 | 4 | | | IV-1 | SPG21 | 1.49 | 9513 | 3 | 4 | | | IV-1 | TAGLN2 | 1.32 |
| 9418 | 3 | 4 | | | IV-1 | SPHAR | 1.35 | 9514 | 3 | 4 | | | IV-1 | TALDO1 | 1.08 |
| 9419 | 3 | 4 | | | IV-1 | SPI1 | 1.40 | 9515 | 3 | 4 | | | IV-1 | TANC2 | 1.24 |
| 9420 | 3 | 4 | | | IV-1 | SPIN2A | 1.03 | 9516 | 3 | 4 | | | IV-1 | TAS2R14 | 1.23 |
| 9421 | 3 | 4 | | | IV-1 | SPINT2 | 1.03 | 9517 | 3 | 4 | | | IV-1 | TAS2R4 | 1.12 |
| 9422 | 3 | 4 | | | IV-1 | SPN | 1.26 | 9518 | 3 | 4 | | | IV-1 | TAS2R5 | 1.37 |
| 9423 | 3 | 4 | | | IV-1 | SPRY1 | 1.14 | 9519 | 3 | 4 | | | IV-1 | TASP1 | 1.42 |
| 9424 | 3 | 4 | | | IV-1 | SPRYD3 | 1.08 | 9520 | 3 | 4 | | | IV-1 | TATDN1 | 1.00 |
| 9425 | 3 | 4 | | | IV-1 | SPRYD7 | 1.20 | 9521 | 3 | 4 | | | IV-1 | TATDN2 | 1.50 |
| 9426 | 3 | 4 | | | IV-1 | SPSB2 | 1.27 | 9522 | 3 | 4 | | | IV-1 | TAX1BP3 | 1.48 |
| 9427 | 3 | 4 | | | IV-1 | SPTY2D1 | 1.50 | 9523 | 3 | 4 | | | IV-1 | TBC1D10A | 1.31 |
| 9428 | 3 | 4 | | | IV-1 | SQLE | 1.42 | 9524 | 3 | 4 | | | IV-1 | TBC1D10B | 1.38 |
| 9429 | 3 | 4 | | | IV-1 | SRA1 | 1.14 | 9525 | 3 | 4 | | | IV-1 | TBC1D22A | 1.39 |
| 9430 | 3 | 4 | | | IV-1 | SRF | 1.14 | 9526 | 3 | 4 | | | IV-1 | TBCA | 1.18 |
| 9431 | 3 | 4 | | | IV-1 | SRFBP1 | 1.24 | 9527 | 3 | 4 | | | IV-1 | TBCB | 1.02 |
| 9432 | 3 | 4 | | | IV-1 | SRGN | 1.23 | 9528 | 3 | 4 | | | IV-1 | TBCCD1 | 1.12 |
| 9433 | 3 | 4 | | | IV-1 | SRI | 1.01 | 9529 | 3 | 4 | | | IV-1 | TBCE | 1.14 |
| 9434 | 3 | 4 | | | IV-1 | SRM | 1.20 | 9530 | 3 | 4 | | | IV-1 | TBL1X | 1.04 |
| 9435 | 3 | 4 | | | IV-1 | SRP72 | 1.31 | 9531 | 3 | 4 | | | IV-1 | TBL1XR1 | 1.35 |
| 9436 | 3 | 4 | | | IV-1 | SRP9 | 1.15 | 9532 | 3 | 4 | | | IV-1 | TBP | 1.37 |
| 9437 | 3 | 4 | | | IV-1 | SRPK1 | 1.30 | 9533 | 3 | 4 | | | IV-1 | TBXAS1 | 1.43 |
| 9438 | 3 | 4 | | | IV-1 | SRPR | 1.41 | 9534 | 3 | 4 | | | IV-1 | TCEA1 | 1.40 |
| 9439 | 3 | 4 | | | IV-1 | SRPRB | 1.01 | 9535 | 3 | 4 | | | IV-1 | TCEA2 | 1.27 |
| 9440 | 3 | 4 | | | IV-1 | SRRD | 1.13 | 9536 | 3 | 4 | | | IV-1 | TCEAL4 | 1.19 |
| 9441 | 3 | 4 | | | IV-1 | SRSF3 | 1.46 | 9537 | 3 | 4 | | | IV-1 | TCEAL8 | 1.11 |
| 9442 | 3 | 4 | | | IV-1 | SRSF9 | 1.28 | 9538 | 3 | 4 | | | IV-1 | TCEANC | 1.14 |
| 9443 | 3 | 4 | | | IV-1 | SSBP1 | 1.11 | 9539 | 3 | 4 | | | IV-1 | TCEANC2 | 1.47 |
| 9444 | 3 | 4 | | | IV-1 | SSH1 | 1.27 | 9540 | 3 | 4 | | | IV-1 | TCEB1 | 1.13 |
| 9445 | 3 | 4 | | | IV-1 | SSH2 | 1.42 | 9541 | 3 | 4 | | | IV-1 | TCFL5 | 1.14 |
| 9446 | 3 | 4 | | | IV-1 | SSPN | 1.17 | 9542 | 3 | 4 | | | IV-1 | TCP1 | 1.47 |
| 9447 | 3 | 4 | | | IV-1 | SSR3 | 1.25 | 9543 | 3 | 4 | | | IV-1 | TCTA | 1.38 |
| 9448 | 3 | 4 | | | IV-1 | SSRP1 | 1.31 | 9544 | 3 | 4 | | | IV-1 | TCTEX1D4 | 1.22 |
| 9449 | 3 | 4 | | | IV-1 | SSSCA1 | 1.36 | 9545 | 3 | 4 | | | IV-1 | TCTN2 | 1.06 |
| 9450 | 3 | 4 | | | IV-1 | ST13 | 1.26 | 9546 | 3 | 4 | | | IV-1 | TCTN3 | 1.46 |
| 9451 | 3 | 4 | | | IV-1 | ST3GAL2 | 1.12 | 9547 | 3 | 4 | | | IV-1 | TDP1 | 1.45 |
| 9452 | 3 | 4 | | | IV-1 | ST3GAL3 | 1.12 | 9548 | 3 | 4 | | | IV-1 | TDRD3 | 1.21 |
| 9453 | 3 | 4 | | | IV-1 | ST6GAL1 | 1.17 | 9549 | 3 | 4 | | | IV-1 | TEAD2 | 1.47 |
| 9454 | 3 | 4 | | | IV-1 | ST6GALNAC3 | 1.45 | 9550 | 3 | 4 | | | IV-1 | TEC | 1.21 |
| 9455 | 3 | 4 | | | IV-1 | STAMBPL1 | 1.41 | 9551 | 3 | 4 | | | IV-1 | TECR | 1.49 |
| 9456 | 3 | 4 | | | IV-1 | STARD7 | 1.21 | 9552 | 3 | 4 | | | IV-1 | TERF1 | 1.32 |
| 9457 | 3 | 4 | | | IV-1 | STK11 | 1.35 | 9553 | 3 | 4 | | | IV-1 | TERF2IP | 1.37 |
| 9458 | 3 | 4 | | | IV-1 | STK16 | 1.03 | 9554 | 3 | 4 | | | IV-1 | TES | 1.24 |
| 9459 | 3 | 4 | | | IV-1 | STK17A | 1.27 | 9555 | 3 | 4 | | | IV-1 | TEX2 | 1.16 |
| 9460 | 3 | 4 | | | IV-1 | STK17B | 1.25 | 9556 | 3 | 4 | | | IV-1 | TEX30 | 1.39 |
| 9461 | 3 | 4 | | | IV-1 | STK39 | 1.06 | 9557 | 3 | 4 | | | IV-1 | TEX34 | 1.47 |
| 9462 | 3 | 4 | | | IV-1 | STK40 | 1.49 | 9558 | 3 | 4 | | | IV-1 | TFAMP1 | 1.11 |
| 9463 | 3 | 4 | | | IV-1 | STMN1 | 1.23 | 9559 | 3 | 4 | | | IV-1 | TFAP4 | 1.36 |
| 9464 | 3 | 4 | | | IV-1 | STOM | 1.11 | 9560 | 3 | 4 | | | IV-1 | TFB2M | 1.08 |
| 9465 | 3 | 4 | | | IV-1 | STOML1 | 1.46 | 9561 | 3 | 4 | | | IV-1 | TFDP1 | 1.49 |
| 9466 | 3 | 4 | | | IV-1 | STOML2 | 1.43 | 9562 | 3 | 4 | | | IV-1 | TFR2 | 1.03 |
| 9467 | 3 | 4 | | | IV-1 | STON1 | 1.12 | 9563 | 3 | 4 | | | IV-1 | TGFB1 | 1.35 |
| 9468 | 3 | 4 | | | IV-1 | STRAP | 1.18 | 9564 | 3 | 4 | | | IV-1 | TGFB3 | 1.42 |
| 9469 | 3 | 4 | | | IV-1 | STT3B | 1.47 | 9565 | 3 | 4 | | | IV-1 | TGFBRAP1 | 1.48 |
| 9470 | 3 | 4 | | | IV-1 | STUB1 | 1.17 | 9566 | 3 | 4 | | | IV-1 | TGIF1 | 1.44 |
| 9471 | 3 | 4 | | | IV-1 | STX18 | 1.46 | 9567 | 3 | 4 | | | IV-1 | THAP1 | 1.21 |
| 9472 | 3 | 4 | | | IV-1 | STX5 | 1.18 | 9568 | 3 | 4 | | | IV-1 | THAP11 | 1.19 |
| 9473 | 3 | 4 | | | IV-1 | STYX | 1.11 | 9569 | 3 | 4 | | | IV-1 | THAP3 | 1.43 |
| 9474 | 3 | 4 | | | IV-1 | SUB1 | 1.20 | 9570 | 3 | 4 | | | IV-1 | THAP4 | 1.06 |
| 9475 | 3 | 4 | | | IV-1 | SUCLG1 | 1.27 | 9571 | 3 | 4 | | | IV-1 | THAP5 | 1.10 |
| 9476 | 3 | 4 | | | IV-1 | SUCLG2 | 1.24 | 9572 | 3 | 4 | | | IV-1 | THAP6 | 1.43 |
| 9477 | 3 | 4 | | | IV-1 | SUCNR1 | 1.11 | 9573 | 3 | 4 | | | IV-1 | THAP7 | 1.15 |
| 9478 | 3 | 4 | | | IV-1 | SUGT1 | 1.35 | 9574 | 3 | 4 | | | IV-1 | THAP8 | 1.37 |
| 9479 | 3 | 4 | | | IV-1 | SUMF1 | 1.14 | 9575 | 3 | 4 | | | IV-1 | THBD | 1.20 |
| 9480 | 3 | 4 | | | IV-1 | SUMF2 | 1.13 | 9576 | 3 | 4 | | | IV-1 | THOC5 | 1.18 |
| 9481 | 3 | 4 | | | IV-1 | SUMO1 | 1.24 | 9577 | 3 | 4 | | | IV-1 | THOC7 | 1.15 |
| 9482 | 3 | 4 | | | IV-1 | SUMO1P3 | 1.00 | 9578 | 3 | 4 | | | IV-1 | TIGD2 | 1.41 |
| 9483 | 3 | 4 | | | IV-1 | SUPT4H1 | 1.11 | 9579 | 3 | 4 | | | IV-1 | TIGD5 | 1.49 |
| 9484 | 3 | 4 | | | IV-1 | SUPV3L1 | 1.48 | 9580 | 3 | 4 | | | IV-1 | TIMM13 | 1.03 |
| 9485 | 3 | 4 | | | IV-1 | SURF1 | 1.09 | 9581 | 3 | 4 | | | IV-1 | TIMM17A | 1.45 |
| 9486 | 3 | 4 | | | IV-1 | SURF2 | 1.22 | 9582 | 3 | 4 | | | IV-1 | TIMM21 | 1.21 |
| 9487 | 3 | 4 | | | IV-1 | SURF4 | 1.12 | 9583 | 3 | 4 | | | IV-1 | TIMM22 | 1.01 |
| 9488 | 3 | 4 | | | IV-1 | SUSD3 | 1.36 | 9584 | 3 | 4 | | | IV-1 | TIMM23 | 1.49 |
| 9489 | 3 | 4 | | | IV-1 | SUSD4 | 1.43 | 9585 | 3 | 4 | | | IV-1 | TIMM50 | 1.29 |
| 9490 | 3 | 4 | | | IV-1 | SUV39H1 | 1.26 | 9586 | 3 | 4 | | | IV-1 | TIMM9 | 1.14 |
| 9491 | 3 | 4 | | | IV-1 | SUZ12P | 1.19 | 9587 | 3 | 4 | | | IV-1 | TIMMDC1 | 1.22 |
| 9492 | 3 | 4 | | | IV-1 | SVIP | 1.45 | 9588 | 3 | 4 | | | IV-1 | TINF2 | 1.02 |
| 9493 | 3 | 4 | | | IV-1 | SW15 | 1.23 | 9589 | 3 | 4 | | | IV-1 | TIPIN | 1.27 |
| 9494 | 3 | 4 | | | IV-1 | SYAP1 | 1.39 | 9590 | 3 | 4 | | | IV-1 | TIPRL | 1.42 |
| 9495 | 3 | 4 | | | IV-1 | SYNE1 | 1.39 | 9591 | 3 | 4 | | | IV-1 | TJP3 | 1.20 |
| 9496 | 3 | 4 | | | IV-1 | SYNGR2 | 1.16 | 9592 | 3 | 4 | | | IV-1 | TKT | 1.20 |
| 9497 | 3 | 4 | | | IV-1 | SYS1 | 1.13 | 9593 | 3 | 4 | | | IV-1 | TM2D1 | 1.27 |
| 9498 | 3 | 4 | | | IV-1 | SYTL3 | 1.38 | 9594 | 3 | 4 | | | IV-1 | TM2D2 | 1.36 |
| 9499 | 3 | 4 | | | IV-1 | TA81 | 1.48 | 9595 | 3 | 4 | | | IV-1 | TM7SF3 | 1.47 |

Fig. 40 - 51

| | | | | | | | | | | | | | | | | |
|---|---|---|---|---|---|---|---|---|---|---|---|---|---|---|---|---|
| 9596 | 3 | 4 | | | IV-1 | TM8IM1 | 1.44 | 9692 | 3 | 4 | | | IV-1 | TRAPPC2 | 1.25 |
| 9597 | 3 | 4 | | | IV-1 | TMBIM4 | 1.45 | 9693 | 3 | 4 | | | IV-1 | TRAPPC2L | 1.35 |
| 9598 | 3 | 4 | | | IV-1 | TM8IM6 | 1.27 | 9694 | 3 | 4 | | | IV-1 | TRAPPC2P1 | 1.32 |
| 9599 | 3 | 4 | | | IV-1 | TMCC1 | 1.32 | 9695 | 3 | 4 | | | IV-1 | TRAPPC3 | 1.35 |
| 9600 | 3 | 4 | | | IV-1 | TMCO1 | 1.29 | 9696 | 3 | 4 | | | IV-1 | TRAPPC4 | 1.22 |
| 9601 | 3 | 4 | | | IV-1 | TMED1 | 1.23 | 9697 | 3 | 4 | | | IV-1 | TRAPPC5 | 1.27 |
| 9602 | 3 | 4 | | | IV-1 | TMED10 | 1.08 | 9698 | 3 | 4 | | | IV-1 | TRERF1 | 1.49 |
| 9603 | 3 | 4 | | | IV-1 | TMED10P1 | 1.02 | 9699 | 3 | 4 | | | IV-1 | TRIAP1 | 1.35 |
| 9604 | 3 | 4 | | | IV-1 | TMED11P | 1.21 | 9700 | 3 | 4 | | | IV-1 | TRIM16 | 1.43 |
| 9605 | 3 | 4 | | | IV-1 | TMED2 | 1.15 | 9701 | 3 | 4 | | | IV-1 | TRIM16L | 1.43 |
| 9606 | 3 | 4 | | | IV-1 | TMED8 | 1.08 | 9702 | 3 | 4 | | | IV-1 | TRIM17 | 1.14 |
| 9607 | 3 | 4 | | | IV-1 | TMED9 | 1.02 | 9703 | 3 | 4 | | | IV-1 | TRIM32 | 1.04 |
| 9608 | 3 | 4 | | | IV-1 | TMEM101 | 1.07 | 9704 | 3 | 4 | | | IV-1 | TRIM4 | 1.42 |
| 9609 | 3 | 4 | | | IV-1 | TMEM102 | 1.45 | 9705 | 3 | 4 | | | IV-1 | TRIM40 | 1.15 |
| 9610 | 3 | 4 | | | IV-1 | TMEM106B | 1.44 | 9706 | 3 | 4 | | | IV-1 | TRIM46 | 1.19 |
| 9611 | 3 | 4 | | | IV-1 | TMEM107 | 1.26 | 9707 | 3 | 4 | | | IV-1 | TRIM59 | 1.11 |
| 9612 | 3 | 4 | | | IV-1 | TMEM11 | 1.10 | 9708 | 3 | 4 | | | IV-1 | TRIM74 | 1.07 |
| 9613 | 3 | 4 | | | IV-1 | TMEM128 | 1.30 | 9709 | 3 | 4 | | | IV-1 | TRIP10 | 1.34 |
| 9614 | 3 | 4 | | | IV-1 | TMEM134 | 1.25 | 9710 | 3 | 4 | | | IV-1 | TRMT112 | 1.21 |
| 9615 | 3 | 4 | | | IV-1 | TMEM147 | 1.04 | 9711 | 3 | 4 | | | IV-1 | TRUB1 | 1.07 |
| 9616 | 3 | 4 | | | IV-1 | TMEM14A | 1.40 | 9712 | 3 | 4 | | | IV-1 | TRUB2 | 1.26 |
| 9617 | 3 | 4 | | | IV-1 | TMEM14C | 1.10 | 9713 | 3 | 4 | | | IV-1 | TSC22D4 | 1.41 |
| 9618 | 3 | 4 | | | IV-1 | TMEM158 | 1.03 | 9714 | 3 | 4 | | | IV-1 | TSEN15 | 1.01 |
| 9619 | 3 | 4 | | | IV-1 | TMEM160 | 1.26 | 9715 | 3 | 4 | | | IV-1 | TSEN54 | 1.06 |
| 9620 | 3 | 4 | | | IV-1 | TMEM165 | 1.46 | 9716 | 3 | 4 | | | IV-1 | TSFM | 1.32 |
| 9621 | 3 | 4 | | | IV-1 | TMEM170A | 1.43 | 9717 | 3 | 4 | | | IV-1 | TSG101 | 1.43 |
| 9622 | 3 | 4 | | | IV-1 | TMEM179B | 1.31 | 9718 | 3 | 4 | | | IV-1 | TSHZ1 | 1.05 |
| 9623 | 3 | 4 | | | IV-1 | TMEM18 | 1.19 | 9719 | 3 | 4 | | | IV-1 | TSHZ3 | 1.12 |
| 9624 | 3 | 4 | | | IV-1 | TMEM184C | 1.24 | 9720 | 3 | 4 | | | IV-1 | TSN | 1.32 |
| 9625 | 3 | 4 | | | IV-1 | TMEM185B | 1.22 | 9721 | 3 | 4 | | | IV-1 | TSNARE1 | 1.25 |
| 9626 | 3 | 4 | | | IV-1 | TMEM187 | 1.48 | 9722 | 3 | 4 | | | IV-1 | TSNAX | 1.42 |
| 9627 | 3 | 4 | | | IV-1 | TMEM189 | 1.15 | 9723 | 3 | 4 | | | IV-1 | TSPAN14 | 1.36 |
| 9628 | 3 | 4 | | | IV-1 | TMEM203 | 1.05 | 9724 | 3 | 4 | | | IV-1 | TSPAN16 | 1.09 |
| 9629 | 3 | 4 | | | IV-1 | TMEM206 | 1.42 | 9725 | 3 | 4 | | | IV-1 | TSPAN31 | 1.38 |
| 9630 | 3 | 4 | | | IV-1 | TMEM218 | 1.49 | 9726 | 3 | 4 | | | IV-1 | TSR2 | 1.11 |
| 9631 | 3 | 4 | | | IV-1 | TMEM219 | 1.26 | 9727 | 3 | 4 | | | IV-1 | TSSC1 | 1.18 |
| 9632 | 3 | 4 | | | IV-1 | TMEM222 | 1.32 | 9728 | 3 | 4 | | | IV-1 | TSSC4 | 1.15 |
| 9633 | 3 | 4 | | | IV-1 | TMEM223 | 1.08 | 9729 | 3 | 4 | | | IV-1 | TTC1 | 1.25 |
| 9634 | 3 | 4 | | | IV-1 | TMEM229B | 1.22 | 9730 | 3 | 4 | | | IV-1 | TTC19 | 1.46 |
| 9635 | 3 | 4 | | | IV-1 | TMEM238 | 1.00 | 9731 | 3 | 4 | | | IV-1 | TTC26 | 1.13 |
| 9636 | 3 | 4 | | | IV-1 | TMEM241 | 1.21 | 9732 | 3 | 4 | | | IV-1 | TTC33 | 1.32 |
| 9637 | 3 | 4 | | | IV-1 | TMEM242 | 1.09 | 9733 | 3 | 4 | | | IV-1 | TTC3P1 | 1.45 |
| 9638 | 3 | 4 | | | IV-1 | TMEM30B | 1.00 | 9734 | 3 | 4 | | | IV-1 | TTC4 | 1.16 |
| 9639 | 3 | 4 | | | IV-1 | TMEM41A | 1.34 | 9735 | 3 | 4 | | | IV-1 | TTC5 | 1.06 |
| 9640 | 3 | 4 | | | IV-1 | TMEM41B | 1.45 | 9736 | 3 | 4 | | | IV-1 | TTC9 | 1.08 |
| 9641 | 3 | 4 | | | IV-1 | TMEM5 | 1.46 | 9737 | 3 | 4 | | | IV-1 | TTC9C | 1.42 |
| 9642 | 3 | 4 | | | IV-1 | TMEM50A | 1.27 | 9738 | 3 | 4 | | | IV-1 | TTI2 | 1.41 |
| 9643 | 3 | 4 | | | IV-1 | TMEM50B | 1.24 | 9739 | 3 | 4 | | | IV-1 | TTLL11 | 1.35 |
| 9644 | 3 | 4 | | | IV-1 | TMEM59 | 1.39 | 9740 | 3 | 4 | | | IV-1 | TTLL4 | 1.22 |
| 9645 | 3 | 4 | | | IV-1 | TMEM70 | 1.09 | 9741 | 3 | 4 | | | IV-1 | TTN | 1.23 |
| 9646 | 3 | 4 | | | IV-1 | TMEM85 | 1.13 | 9742 | 3 | 4 | | | IV-1 | TUBA1A | 1.18 |
| 9647 | 3 | 4 | | | IV-1 | TMEM8A | 1.31 | 9743 | 3 | 4 | | | IV-1 | TUBA1B | 1.22 |
| 9648 | 3 | 4 | | | IV-1 | TMEM8B | 1.49 | 9744 | 3 | 4 | | | IV-1 | TUBA1C | 1.27 |
| 9649 | 3 | 4 | | | IV-1 | TMEM93 | 1.33 | 9745 | 3 | 4 | | | IV-1 | TUBA4A | 1.00 |
| 9650 | 3 | 4 | | | IV-1 | TMEM99 | 1.10 | 9746 | 3 | 4 | | | IV-1 | TUBB | 1.37 |
| 9651 | 3 | 4 | | | IV-1 | TMEM98 | 1.46 | 9747 | 3 | 4 | | | IV-1 | TUBB4B | 1.05 |
| 9652 | 3 | 4 | | | IV-1 | TMIGD2 | 1.29 | 9748 | 3 | 4 | | | IV-1 | TUBG1 | 1.36 |
| 9653 | 3 | 4 | | | IV-1 | TMPRSS13 | 1.08 | 9749 | 3 | 4 | | | IV-1 | TUFM | 1.15 |
| 9654 | 3 | 4 | | | IV-1 | TMSB10 | 1.29 | 9750 | 3 | 4 | | | IV-1 | TULP3 | 1.49 |
| 9655 | 3 | 4 | | | IV-1 | TMSB4X | 1.20 | 9751 | 3 | 4 | | | IV-1 | TUSC2 | 1.05 |
| 9656 | 3 | 4 | | | IV-1 | TMTC4 | 1.29 | 9752 | 3 | 4 | | | IV-1 | TWF2 | 1.24 |
| 9657 | 3 | 4 | | | IV-1 | TMX4 | 1.14 | 9753 | 3 | 4 | | | IV-1 | TWISTNB | 1.01 |
| 9658 | 3 | 4 | | | IV-1 | TNFAIP8 | 1.41 | 9754 | 3 | 4 | | | IV-1 | TWSG1 | 1.25 |
| 9659 | 3 | 4 | | | IV-1 | TNFAIP8L2 | 1.26 | 9755 | 3 | 4 | | | IV-1 | TXN2 | 1.04 |
| 9660 | 3 | 4 | | | IV-1 | TNFRSF4 | 1.35 | 9756 | 3 | 4 | | | IV-1 | TXNDC12 | 1.35 |
| 9661 | 3 | 4 | | | IV-1 | TNFRSF8 | 1.29 | 9757 | 3 | 4 | | | IV-1 | TXNDC15 | 1.07 |
| 9662 | 3 | 4 | | | IV-1 | TNFRSF9 | 1.24 | 9758 | 3 | 4 | | | IV-1 | TXNDC17 | 1.36 |
| 9663 | 3 | 4 | | | IV-1 | TNFSF15 | 1.43 | 9759 | 3 | 4 | | | IV-1 | TXNDC3 | 1.36 |
| 9664 | 3 | 4 | | | IV-1 | TNIP2 | 1.37 | 9760 | 3 | 4 | | | IV-1 | TXNDC9 | 1.02 |
| 9665 | 3 | 4 | | | IV-1 | TNNI2 | 1.45 | 9761 | 3 | 4 | | | IV-1 | TXNL1 | 1.28 |
| 9666 | 3 | 4 | | | IV-1 | TNNT3 | 1.40 | 9762 | 3 | 4 | | | IV-1 | TXNL4A | 1.21 |
| 9667 | 3 | 4 | | | IV-1 | TOB1 | 1.04 | 9763 | 3 | 4 | | | IV-1 | TXNRD1 | 1.47 |
| 9668 | 3 | 4 | | | IV-1 | TOB2 | 1.35 | 9764 | 3 | 4 | | | IV-1 | TYMS | 1.16 |
| 9669 | 3 | 4 | | | IV-1 | TOMM20 | 1.21 | 9765 | 3 | 4 | | | IV-1 | TYROBP | 1.13 |
| 9670 | 3 | 4 | | | IV-1 | TOMM34 | 1.33 | 9766 | 3 | 4 | | | IV-1 | TYW1B | 1.07 |
| 9671 | 3 | 4 | | | IV-1 | TOMM40 | 1.45 | 9767 | 3 | 4 | | | IV-1 | TYW3 | 1.30 |
| 9672 | 3 | 4 | | | IV-1 | TOMM40L | 1.14 | 9768 | 3 | 4 | | | IV-1 | U2AF1 | 1.43 |
| 9673 | 3 | 4 | | | IV-1 | TOMM5 | 1.04 | 9769 | 3 | 4 | | | IV-1 | UACA | 1.39 |
| 9674 | 3 | 4 | | | IV-1 | TOMM70A | 1.36 | 9770 | 3 | 4 | | | IV-1 | UBA2 | 1.39 |
| 9675 | 3 | 4 | | | IV-1 | TOPORS | 1.47 | 9771 | 3 | 4 | | | IV-1 | UBAC2 | 1.34 |
| 9676 | 3 | 4 | | | IV-1 | TOR2A | 1.07 | 9772 | 3 | 4 | | | IV-1 | UBAP1 | 1.06 |
| 9677 | 3 | 4 | | | IV-1 | TP53I11 | 1.04 | 9773 | 3 | 4 | | | IV-1 | UBE2D2 | 1.16 |
| 9678 | 3 | 4 | | | IV-1 | TP53RK | 1.02 | 9774 | 3 | 4 | | | IV-1 | UBE2D4 | 1.18 |
| 9679 | 3 | 4 | | | IV-1 | TPD52 | 1.48 | 9775 | 3 | 4 | | | IV-1 | UBE2E1 | 1.45 |
| 9680 | 3 | 4 | | | IV-1 | TPI1 | 1.12 | 9776 | 3 | 4 | | | IV-1 | UBE2E3 | 1.35 |
| 9681 | 3 | 4 | | | IV-1 | TPM1 | 1.04 | 9777 | 3 | 4 | | | IV-1 | UBE2F | 1.43 |
| 9682 | 3 | 4 | | | IV-1 | TPM3 | 1.24 | 9778 | 3 | 4 | | | IV-1 | UBE2G1 | 1.43 |
| 9683 | 3 | 4 | | | IV-1 | TPM4 | 1.12 | 9779 | 3 | 4 | | | IV-1 | UBE2I | 1.32 |
| 9684 | 3 | 4 | | | IV-1 | TPMT | 1.28 | 9780 | 3 | 4 | | | IV-1 | UBE2L3 | 1.32 |
| 9685 | 3 | 4 | | | IV-1 | TPPP | 1.32 | 9781 | 3 | 4 | | | IV-1 | UBE2N | 1.10 |
| 9686 | 3 | 4 | | | IV-1 | TPRA1 | 1.46 | 9782 | 3 | 4 | | | IV-1 | UBE2R2 | 1.44 |
| 9687 | 3 | 4 | | | IV-1 | TPRKB | 1.35 | 9783 | 3 | 4 | | | IV-1 | UBE2V1 | 1.19 |
| 9688 | 3 | 4 | | | IV-1 | TPST2 | 1.17 | 9784 | 3 | 4 | | | IV-1 | UBE2V2 | 1.29 |
| 9689 | 3 | 4 | | | IV-1 | TRAF7 | 1.42 | 9785 | 3 | 4 | | | IV-1 | UBIAD1 | 1.26 |
| 9690 | 3 | 4 | | | IV-1 | TRAK2 | 1.28 | 9786 | 3 | 4 | | | IV-1 | UBL3 | 1.37 |
| 9691 | 3 | 4 | | | IV-1 | TRAM1 | 1.20 | 9787 | 3 | 4 | | | IV-1 | UBL7 | 1.07 |

Fig. 40 - 52

| | | | | | | | | | | | | | | |
|---|---|---|---|---|---|---|---|---|---|---|---|---|---|---|
| 9788 | 3 | 4 | | | IV-1 | UBQLN4 | 1.46 | 9884 | 3 | 4 | | | IV-1 | WSB2 | 1.31 |
| 9789 | 3 | 4 | | | IV-1 | U8TF | 1.47 | 9885 | 3 | 4 | | | IV-1 | WTAP | 1.49 |
| 9790 | 3 | 4 | | | IV-1 | UBXN1 | 1.36 | 9886 | 3 | 4 | | | IV-1 | WWC2 | 1.10 |
| 9791 | 3 | 4 | | | IV-1 | UBXN2A | 1.32 | 9887 | 3 | 4 | | | IV-1 | WWOX | 1.32 |
| 9792 | 3 | 4 | | | IV-1 | UBXN8 | 1.12 | 9888 | 3 | 4 | | | IV-1 | XBP1 | 1.12 |
| 9793 | 3 | 4 | | | IV-1 | UCHL5 | 1.43 | 9889 | 3 | 4 | | | IV-1 | XPNPEP3 | 1.47 |
| 9794 | 3 | 4 | | | IV-1 | UCK1 | 1.40 | 9890 | 3 | 4 | | | IV-1 | XRCC6 | 1.23 |
| 9795 | 3 | 4 | | | IV-1 | UCP2 | 1.41 | 9891 | 3 | 4 | | | IV-1 | XRN2 | 1.28 |
| 9796 | 3 | 4 | | | IV-1 | UFD1L | 1.03 | 9892 | 3 | 4 | | | IV-1 | YAE1D1 | 1.49 |
| 9797 | 3 | 4 | | | IV-1 | UFSP1 | 1.47 | 9893 | 3 | 4 | | | IV-1 | YAF2 | 1.31 |
| 9798 | 3 | 4 | | | IV-1 | UFSP2 | 1.49 | 9894 | 3 | 4 | | | IV-1 | YDJC | 1.37 |
| 9799 | 3 | 4 | | | IV-1 | UGDH | 1.36 | 9895 | 3 | 4 | | | IV-1 | YIF1A | 1.18 |
| 9800 | 3 | 4 | | | IV-1 | UGP2 | 1.28 | 9896 | 3 | 4 | | | IV-1 | YIF1B | 1.10 |
| 9801 | 3 | 4 | | | IV-1 | UHMK1 | 1.23 | 9897 | 3 | 4 | | | IV-1 | YIPF1 | 1.46 |
| 9802 | 3 | 4 | | | IV-1 | UMPS | 1.10 | 9898 | 3 | 4 | | | IV-1 | YIPF2 | 1.29 |
| 9803 | 3 | 4 | | | IV-1 | UNC119 | 1.29 | 9899 | 3 | 4 | | | IV-1 | YIPF3 | 1.47 |
| 9804 | 3 | 4 | | | IV-1 | UNC119B | 1.16 | 9900 | 3 | 4 | | | IV-1 | YPEL1 | 1.10 |
| 9805 | 3 | 4 | | | IV-1 | UNG | 1.02 | 9901 | 3 | 4 | | | IV-1 | YPEL2 | 1.30 |
| 9806 | 3 | 4 | | | IV-1 | UPRT | 1.27 | 9902 | 3 | 4 | | | IV-1 | YRDC | 1.42 |
| 9807 | 3 | 4 | | | IV-1 | UQCRC2 | 1.28 | 9903 | 3 | 4 | | | IV-1 | YTHDF3 | 1.48 |
| 9808 | 3 | 4 | | | IV-1 | UQCRFS1 | 1.06 | 9904 | 3 | 4 | | | IV-1 | YWHAE | 1.18 |
| 9809 | 3 | 4 | | | IV-1 | UQCRHL | 1.06 | 9905 | 3 | 4 | | | IV-1 | YWHAQ | 1.20 |
| 9810 | 3 | 4 | | | IV-1 | URI1 | 1.36 | 9906 | 3 | 4 | | | IV-1 | YY1 | 1.38 |
| 9811 | 3 | 4 | | | IV-1 | URM1 | 1.02 | 9907 | 3 | 4 | | | IV-1 | ZAK | 1.17 |
| 9812 | 3 | 4 | | | IV-1 | UROD | 1.16 | 9908 | 3 | 4 | | | IV-1 | ZBED1 | 1.14 |
| 9813 | 3 | 4 | | | IV-1 | UROS | 1.38 | 9909 | 3 | 4 | | | IV-1 | ZBED3 | 1.29 |
| 9814 | 3 | 4 | | | IV-1 | USF2 | 1.32 | 9910 | 3 | 4 | | | IV-1 | ZBED4 | 1.25 |
| 9815 | 3 | 4 | | | IV-1 | USP12 | 1.41 | 9911 | 3 | 4 | | | IV-1 | ZBTB12 | 1.01 |
| 9816 | 3 | 4 | | | IV-1 | USP28 | 1.11 | 9912 | 3 | 4 | | | IV-1 | ZBTB22 | 1.10 |
| 9817 | 3 | 4 | | | IV-1 | USP30 | 1.47 | 9913 | 3 | 4 | | | IV-1 | ZBTB4 | 1.39 |
| 9818 | 3 | 4 | | | IV-1 | USP32P1 | 1.18 | 9914 | 3 | 4 | | | IV-1 | ZBTB41 | 1.25 |
| 9819 | 3 | 4 | | | IV-1 | USP38 | 1.37 | 9915 | 3 | 4 | | | IV-1 | ZBTB42 | 1.19 |
| 9820 | 3 | 4 | | | IV-1 | USP44 | 1.06 | 9916 | 3 | 4 | | | IV-1 | ZBTB44 | 1.41 |
| 9821 | 3 | 4 | | | IV-1 | USP46 | 1.24 | 9917 | 3 | 4 | | | IV-1 | ZBT85 | 1.44 |
| 9822 | 3 | 4 | | | IV-1 | USP49 | 1.24 | 9918 | 3 | 4 | | | IV-1 | ZBTB6 | 1.25 |
| 9823 | 3 | 4 | | | IV-1 | USP6 | 1.15 | 9919 | 3 | 4 | | | IV-1 | ZBTB9 | 1.40 |
| 9824 | 3 | 4 | | | IV-1 | UTP11L | 1.49 | 9920 | 3 | 4 | | | IV-1 | ZC3H10 | 1.47 |
| 9825 | 3 | 4 | | | IV-1 | UTP14A | 1.28 | 9921 | 3 | 4 | | | IV-1 | ZC3H12C | 1.03 |
| 9826 | 3 | 4 | | | IV-1 | UTP23 | 1.40 | 9922 | 3 | 4 | | | IV-1 | ZC3HAV1L | 1.41 |
| 9827 | 3 | 4 | | | IV-1 | VAMP7 | 1.49 | 9923 | 3 | 4 | | | IV-1 | ZC3HC1 | 1.41 |
| 9828 | 3 | 4 | | | IV-1 | VAMP8 | 1.13 | 9924 | 3 | 4 | | | IV-1 | ZC4H2 | 1.42 |
| 9829 | 3 | 4 | | | IV-1 | VAPA | 1.08 | 9925 | 3 | 4 | | | IV-1 | ZCCHC10 | 1.27 |
| 9830 | 3 | 4 | | | IV-1 | VAPB | 1.49 | 9926 | 3 | 4 | | | IV-1 | ZCCHC18 | 1.37 |
| 9831 | 3 | 4 | | | IV-1 | VARS2 | 1.10 | 9927 | 3 | 4 | | | IV-1 | ZCCHC3 | 1.41 |
| 9832 | 3 | 4 | | | IV-1 | VASP | 1.47 | 9928 | 3 | 4 | | | IV-1 | ZCCHC4 | 1.45 |
| 9833 | 3 | 4 | | | IV-1 | VAT1 | 1.49 | 9929 | 3 | 4 | | | IV-1 | ZCCHC7 | 1.49 |
| 9834 | 3 | 4 | | | IV-1 | VBP1 | 1.43 | 9930 | 3 | 4 | | | IV-1 | ZCCHC9 | 1.17 |
| 9835 | 3 | 4 | | | IV-1 | VEGFB | 1.14 | 9931 | 3 | 4 | | | IV-1 | ZCRB1 | 1.17 |
| 9836 | 3 | 4 | | | IV-1 | VEZT | 1.30 | 9932 | 3 | 4 | | | IV-1 | ZDBF2 | 1.37 |
| 9837 | 3 | 4 | | | IV-1 | VGLL4 | 1.47 | 9933 | 3 | 4 | | | IV-1 | ZDHHC12 | 1.35 |
| 9838 | 3 | 4 | | | IV-1 | VHL | 1.36 | 9934 | 3 | 4 | | | IV-1 | ZDHHC2 | 1.20 |
| 9839 | 3 | 4 | | | IV-1 | VKORC1 | 1.10 | 9935 | 3 | 4 | | | IV-1 | ZDHHC20 | 1.39 |
| 9840 | 3 | 4 | | | IV-1 | VKORC1L1 | 1.19 | 9936 | 3 | 4 | | | IV-1 | ZDHHC24 | 1.09 |
| 9841 | 3 | 4 | | | IV-1 | VMA21 | 1.23 | 9937 | 3 | 4 | | | IV-1 | ZDHHC3 | 1.27 |
| 9842 | 3 | 4 | | | IV-1 | VMP1 | 1.41 | 9938 | 3 | 4 | | | IV-1 | ZDHHC4 | 1.15 |
| 9843 | 3 | 4 | | | IV-1 | VOPP1 | 1.14 | 9939 | 3 | 4 | | | IV-1 | ZDHHC9 | 1.10 |
| 9844 | 3 | 4 | | | IV-1 | VPS25 | 1.24 | 9940 | 3 | 4 | | | IV-1 | ZFAND2B | 1.36 |
| 9845 | 3 | 4 | | | IV-1 | VPS26B | 1.38 | 9941 | 3 | 4 | | | IV-1 | ZFAND6 | 1.49 |
| 9846 | 3 | 4 | | | IV-1 | VPS28 | 1.21 | 9942 | 3 | 4 | | | IV-1 | ZFAT | 1.38 |
| 9847 | 3 | 4 | | | IV-1 | VPS29 | 1.19 | 9943 | 3 | 4 | | | IV-1 | ZFP161 | 1.38 |
| 9848 | 3 | 4 | | | IV-1 | VPS33A | 1.35 | 9944 | 3 | 4 | | | IV-1 | ZFP28 | 1.21 |
| 9849 | 3 | 4 | | | IV-1 | VPS37A | 1.34 | 9945 | 3 | 4 | | | IV-1 | ZFR | 1.46 |
| 9850 | 3 | 4 | | | IV-1 | VPS37B | 1.45 | 9946 | 3 | 4 | | | IV-1 | ZFYVE21 | 1.35 |
| 9851 | 3 | 4 | | | IV-1 | VPS4A | 1.45 | 9947 | 3 | 4 | | | IV-1 | ZFYVE28 | 1.33 |
| 9852 | 3 | 4 | | | IV-1 | VPS72 | 1.14 | 9948 | 3 | 4 | | | IV-1 | ZGLP1 | 1.02 |
| 9853 | 3 | 4 | | | IV-1 | VRK1 | 1.43 | 9949 | 3 | 4 | | | IV-1 | ZHX3 | 1.47 |
| 9854 | 3 | 4 | | | IV-1 | VRK3 | 1.43 | 9950 | 3 | 4 | | | IV-1 | ZKSCAN2 | 1.26 |
| 9855 | 3 | 4 | | | IV-1 | VSIG10 | 1.27 | 9951 | 3 | 4 | | | IV-1 | ZMAT2 | 1.35 |
| 9856 | 3 | 4 | | | IV-1 | VSIG2 | 1.14 | 9952 | 3 | 4 | | | IV-1 | ZMAT5 | 1.19 |
| 9857 | 3 | 4 | | | IV-1 | VWF | 1.00 | 9953 | 3 | 4 | | | IV-1 | ZMYM6NB | 1.24 |
| 9858 | 3 | 4 | | | IV-1 | WARS2 | 1.47 | 9954 | 3 | 4 | | | IV-1 | ZMYND11 | 1.21 |
| 9859 | 3 | 4 | | | IV-1 | WBP1 | 1.14 | 9955 | 3 | 4 | | | IV-1 | ZMYND15 | 1.28 |
| 9860 | 3 | 4 | | | IV-1 | WBP11P1 | 1.34 | 9956 | 3 | 4 | | | IV-1 | ZNF101 | 1.48 |
| 9861 | 3 | 4 | | | IV-1 | WBSCR16 | 1.25 | 9957 | 3 | 4 | | | IV-1 | ZNF131 | 1.44 |
| 9862 | 3 | 4 | | | IV-1 | WBSCR22 | 1.29 | 9958 | 3 | 4 | | | IV-1 | ZNF138 | 1.50 |
| 9863 | 3 | 4 | | | IV-1 | WDR1 | 1.48 | 9959 | 3 | 4 | | | IV-1 | ZNF14 | 1.12 |
| 9864 | 3 | 4 | | | IV-1 | WDR12 | 1.10 | 9960 | 3 | 4 | | | IV-1 | ZNF141 | 1.50 |
| 9865 | 3 | 4 | | | IV-1 | WDR20 | 1.47 | 9961 | 3 | 4 | | | IV-1 | ZNF16 | 1.22 |
| 9866 | 3 | 4 | | | IV-1 | WDR35 | 1.35 | 9962 | 3 | 4 | | | IV-1 | ZNF17 | 1.21 |
| 9867 | 3 | 4 | | | IV-1 | WDR43 | 1.12 | 9963 | 3 | 4 | | | IV-1 | ZNF174 | 1.15 |
| 9868 | 3 | 4 | | | IV-1 | WDR45 | 1.25 | 9964 | 3 | 4 | | | IV-1 | ZNF180 | 1.49 |
| 9869 | 3 | 4 | | | IV-1 | WDR53 | 1.41 | 9965 | 3 | 4 | | | IV-1 | ZNF181 | 1.48 |
| 9870 | 3 | 4 | | | IV-1 | WDR61 | 1.33 | 9966 | 3 | 4 | | | IV-1 | ZNF184 | 1.24 |
| 9871 | 3 | 4 | | | IV-1 | WDR70 | 1.44 | 9967 | 3 | 4 | | | IV-1 | ZNF185 | 1.24 |
| 9872 | 3 | 4 | | | IV-1 | WDR76 | 1.43 | 9968 | 3 | 4 | | | IV-1 | ZNF19 | 1.22 |
| 9873 | 3 | 4 | | | IV-1 | WDR82 | 1.32 | 9969 | 3 | 4 | | | IV-1 | ZNF208 | 1.38 |
| 9874 | 3 | 4 | | | IV-1 | WDR83 | 1.42 | 9970 | 3 | 4 | | | IV-1 | ZNF22 | 1.09 |
| 9875 | 3 | 4 | | | IV-1 | WDR83OS | 1.38 | 9971 | 3 | 4 | | | IV-1 | ZNF222 | 1.34 |
| 9876 | 3 | 4 | | | IV-1 | WDR89 | 1.38 | 9972 | 3 | 4 | | | IV-1 | ZNF227 | 1.44 |
| 9877 | 3 | 4 | | | IV-1 | WDTC1 | 1.33 | 9973 | 3 | 4 | | | IV-1 | ZNF250 | 1.37 |
| 9878 | 3 | 4 | | | IV-1 | WEE1 | 1.20 | 9974 | 3 | 4 | | | IV-1 | ZNF252 | 1.44 |
| 9879 | 3 | 4 | | | IV-1 | WFS1 | 1.45 | 9975 | 3 | 4 | | | IV-1 | ZNF253 | 1.12 |
| 9880 | 3 | 4 | | | IV-1 | WHSC1L1 | 1.43 | 9976 | 3 | 4 | | | IV-1 | ZNF254 | 1.40 |
| 9881 | 3 | 4 | | | IV-1 | WRAP53 | 1.16 | 9977 | 3 | 4 | | | IV-1 | ZNF257 | 1.01 |
| 9882 | 3 | 4 | | | IV-1 | WRB | 1.16 | 9978 | 3 | 4 | | | IV-1 | ZNF26 | 1.47 |
| 9883 | 3 | 4 | | | IV-1 | WRN | 1.24 | 9979 | 3 | 4 | | | IV-1 | ZNF260 | 1.15 |

Fig. 40 - 53

| | | | | | | | | | | | | | | |
|---|---|---|---|---|---|---|---|---|---|---|---|---|---|---|
| 9980 | 3 | 4 | | | IV-1 | ZNF268 | 1.29 | 10076 | 3 | 4 | | | IV-1 | ZNF792 | 1.11 |
| 9981 | 3 | 4 | | | IV-1 | ZNF273 | 1.27 | 10077 | 3 | 4 | | | IV-1 | ZNF793 | 1.28 |
| 9982 | 3 | 4 | | | IV-1 | ZNF277 | 1.21 | 10078 | 3 | 4 | | | IV-1 | ZNF799 | 1.49 |
| 9983 | 3 | 4 | | | IV-1 | ZNF280C | 1.36 | 10079 | 3 | 4 | | | IV-1 | ZNF80 | 1.02 |
| 9984 | 3 | 4 | | | IV-1 | ZNF285 | 1.25 | 10080 | 3 | 4 | | | IV-1 | ZNF800 | 1.46 |
| 9985 | 3 | 4 | | | IV-1 | ZNF286A | 1.43 | 10081 | 3 | 4 | | | IV-1 | ZNF821 | 1.26 |
| 9986 | 3 | 4 | | | IV-1 | ZNF286B | 1.22 | 10082 | 3 | 4 | | | IV-1 | ZNF823 | 1.02 |
| 9987 | 3 | 4 | | | IV-1 | ZNF287 | 1.08 | 10083 | 3 | 4 | | | IV-1 | ZNF829 | 1.33 |
| 9988 | 3 | 4 | | | IV-1 | ZNF3 | 1.41 | 10084 | 3 | 4 | | | IV-1 | ZNF835 | 1.48 |
| 9989 | 3 | 4 | | | IV-1 | ZNF30 | 1.41 | 10085 | 3 | 4 | | | IV-1 | ZNF845 | 1.20 |
| 9990 | 3 | 4 | | | IV-1 | ZNF300 | 1.42 | 10086 | 3 | 4 | | | IV-1 | ZNF85 | 1.23 |
| 9991 | 3 | 4 | | | IV-1 | ZNF319 | 1.14 | 10087 | 3 | 4 | | | IV-1 | ZNF850 | 1.09 |
| 9992 | 3 | 4 | | | IV-1 | ZNF324B | 1.31 | 10088 | 3 | 4 | | | IV-1 | ZNF865 | 1.36 |
| 9993 | 3 | 4 | | | IV-1 | ZNF34 | 1.37 | 10089 | 3 | 4 | | | IV-1 | ZNF890P | 1.31 |
| 9994 | 3 | 4 | | | IV-1 | ZNF358 | 1.19 | 10090 | 3 | 4 | | | IV-1 | ZNF92 | 1.49 |
| 9995 | 3 | 4 | | | IV-1 | ZNF362 | 1.08 | 10091 | 3 | 4 | | | IV-1 | ZNFX1-AS1 | 1.34 |
| 9996 | 3 | 4 | | | IV-1 | ZNF383 | 1.15 | 10092 | 3 | 4 | | | IV-1 | ZNHIT1 | 1.14 |
| 9997 | 3 | 4 | | | IV-1 | ZNF394 | 1.26 | 10093 | 3 | 4 | | | IV-1 | ZNHIT2 | 1.14 |
| 9998 | 3 | 4 | | | IV-1 | ZNF404 | 1.34 | 10094 | 3 | 4 | | | IV-1 | ZNHIT3 | 1.04 |
| 9999 | 3 | 4 | | | IV-1 | ZNF41 | 1.49 | 10095 | 3 | 4 | | | IV-1 | ZNRD1 | 1.48 |
| 10000 | 3 | 4 | | | IV-1 | ZNF410 | 1.17 | 10096 | 3 | 4 | | | IV-1 | ZNRF2 | 1.35 |
| 10001 | 3 | 4 | | | IV-1 | ZNF414 | 1.33 | 10097 | 3 | 4 | | | IV-1 | ZSCAN12 | 1.18 |
| 10002 | 3 | 4 | | | IV-1 | ZNF415 | 1.22 | 10098 | 3 | 4 | | | IV-1 | ZSCAN2 | 1.22 |
| 10003 | 3 | 4 | | | IV-1 | ZNF416 | 1.05 | 10099 | 3 | 4 | | | IV-1 | ZSCAN21 | 1.22 |
| 10004 | 3 | 4 | | | IV-1 | ZNF420 | 1.33 | 10100 | 3 | 4 | | | IV-1 | ZSCAN5A | 1.11 |
| 10005 | 3 | 4 | | | IV-1 | ZNF425 | 1.08 | 10101 | 3 | 4 | | | IV-1 | ZUFSP | 1.48 |
| 10006 | 3 | 4 | | | IV-1 | ZNF426 | 1.11 | 10102 | 3 | 4 | | | IV-1 | ZWINT | 1.43 |
| 10007 | 3 | 4 | | | IV-1 | ZNF432 | 1.41 | 10103 | 3 | 4 | | | IV-1 | ZZZ3 | 1.24 |
| 10008 | 3 | 4 | | | IV-1 | ZNF45 | 1.12 | 10104 | 3 | | | | | A1CF | 1.00 |
| 10009 | 3 | 4 | | | IV-1 | ZNF460 | 1.41 | 10105 | 3 | | | | | A2M | 1.00 |
| 10010 | 3 | 4 | | | IV-1 | ZNF461 | 1.35 | 10106 | 3 | | | | | A2ML1 | 1.00 |
| 10011 | 3 | 4 | | | IV-1 | ZNF467 | 1.22 | 10107 | 3 | | | | | A2MP1 | 1.00 |
| 10012 | 3 | 4 | | | IV-1 | ZNF468 | 1.19 | 10108 | 3 | | | | | A4GALT | 1.00 |
| 10013 | 3 | 4 | | | IV-1 | ZNF470 | 1.18 | 10109 | 3 | | | | | A4GNT | 1.00 |
| 10014 | 3 | 4 | | | IV-1 | ZNF473 | 1.46 | 10110 | 3 | | | | | AA06 | 1.00 |
| 10015 | 3 | 4 | | | IV-1 | ZNF480 | 1.36 | 10111 | 3 | | | | | AAA1 | 1.00 |
| 10016 | 3 | 4 | | | IV-1 | ZNF485 | 1.25 | 10112 | 3 | | | | | AACSP1 | 1.00 |
| 10017 | 3 | 4 | | | IV-1 | ZNF490 | 1.45 | 10113 | 3 | | | | | AADAC | 1.00 |
| 10018 | 3 | 4 | | | IV-1 | ZNF503 | 1.34 | 10114 | 3 | | | | | AADACL2 | 1.00 |
| 10019 | 3 | 4 | | | IV-1 | ZNF507 | 1.40 | 10115 | 3 | | | | | AADACL3 | 1.00 |
| 10020 | 3 | 4 | | | IV-1 | ZNF510 | 1.28 | 10116 | 3 | | | | | AADACL4 | 1.00 |
| 10021 | 3 | 4 | | | IV-1 | ZNF511 | 1.17 | 10117 | 3 | | | | | AADAT | 1.00 |
| 10022 | 3 | 4 | | | IV-1 | ZNF524 | 1.09 | 10118 | 3 | | | | | AATK-AS1 | 1.00 |
| 10023 | 3 | 4 | | | IV-1 | ZNF525 | 1.45 | 10119 | 3 | | | | | ABCA10 | 1.00 |
| 10024 | 3 | 4 | | | IV-1 | ZNF527 | 1.33 | 10120 | 3 | | | | | ABCA12 | 1.00 |
| 10025 | 3 | 4 | | | IV-1 | ZNF530 | 1.24 | 10121 | 3 | | | | | ABCA13 | 1.00 |
| 10026 | 3 | 4 | | | IV-1 | ZNF544 | 1.40 | 10122 | 3 | | | | | ABCA17P | 1.00 |
| 10027 | 3 | 4 | | | IV-1 | ZNF547 | 1.45 | 10123 | 3 | | | | | ABCA3 | 1.00 |
| 10028 | 3 | 4 | | | IV-1 | ZNF551 | 1.19 | 10124 | 3 | | | | | ABCA4 | 1.00 |
| 10029 | 3 | 4 | | | IV-1 | ZNF552 | 1.38 | 10125 | 3 | | | | | ABCA6 | 1.00 |
| 10030 | 3 | 4 | | | IV-1 | ZNF555 | 1.48 | 10126 | 3 | | | | | ABCA8 | 1.00 |
| 10031 | 3 | 4 | | | IV-1 | ZNF557 | 1.50 | 10127 | 3 | | | | | ABCA9 | 1.00 |
| 10032 | 3 | 4 | | | IV-1 | ZNF559 | 1.28 | 10128 | 3 | | | | | ABCB11 | 1.00 |
| 10033 | 3 | 4 | | | IV-1 | ZNF562 | 1.46 | 10129 | 3 | | | | | ABCB4 | 1.00 |
| 10034 | 3 | 4 | | | IV-1 | ZNF565 | 1.38 | 10130 | 3 | | | | | ABCB5 | 1.00 |
| 10035 | 3 | 4 | | | IV-1 | ZNF566 | 1.30 | 10131 | 3 | | | | | ABCB6 | 1.00 |
| 10036 | 3 | 4 | | | IV-1 | ZNF567 | 1.34 | 10132 | 3 | | | | | ABCB9 | 1.00 |
| 10037 | 3 | 4 | | | IV-1 | ZNF568 | 1.40 | 10133 | 3 | | | | | ABCC11 | 1.00 |
| 10038 | 3 | 4 | | | IV-1 | ZNF57 | 1.27 | 10134 | 3 | | | | | ABCC12 | 1.00 |
| 10039 | 3 | 4 | | | IV-1 | ZNF570 | 1.07 | 10135 | 3 | | | | | ABCC2 | 1.00 |
| 10040 | 3 | 4 | | | IV-1 | ZNF571 | 1.14 | 10136 | 3 | | | | | ABCC6P1 | 1.00 |
| 10041 | 3 | 4 | | | IV-1 | ZNF572 | 1.09 | 10137 | 3 | | | | | ABCC8 | 1.00 |
| 10042 | 3 | 4 | | | IV-1 | ZNF573 | 1.22 | 10138 | 3 | | | | | ABCC9 | 1.00 |
| 10043 | 3 | 4 | | | IV-1 | ZNF574 | 1.38 | 10139 | 3 | | | | | ABCG2 | 1.00 |
| 10044 | 3 | 4 | | | IV-1 | ZNF581 | 1.15 | 10140 | 3 | | | | | ABCG4 | 1.00 |
| 10045 | 3 | 4 | | | IV-1 | ZNF583 | 1.15 | 10141 | 3 | | | | | ABCG5 | 1.00 |
| 10046 | 3 | 4 | | | IV-1 | ZNF596 | 1.33 | 10142 | 3 | | | | | ABCG8 | 1.00 |
| 10047 | 3 | 4 | | | IV-1 | ZNF597 | 1.24 | 10143 | 3 | | | | | ABHD1 | 1.00 |
| 10048 | 3 | 4 | | | IV-1 | ZNF607 | 1.30 | 10144 | 3 | | | | | ABHD11-AS1 | 1.00 |
| 10049 | 3 | 4 | | | IV-1 | ZNF613 | 1.02 | 10145 | 3 | | | | | ABHD12B | 1.00 |
| 10050 | 3 | 4 | | | IV-1 | ZNF618 | 1.27 | 10146 | 3 | | | | | ABHD14A-ACY1 | 1.00 |
| 10051 | 3 | 4 | | | IV-1 | ZNF622 | 1.31 | 10147 | 3 | | | | | AB13BP | 1.00 |
| 10052 | 3 | 4 | | | IV-1 | ZNF625 | 1.08 | 10148 | 3 | | | | | ABLIM2 | 1.00 |
| 10053 | 3 | 4 | | | IV-1 | ZNF627 | 1.32 | 10149 | 3 | | | | | ABRA | 1.00 |
| 10054 | 3 | 4 | | | IV-1 | ZNF628 | 1.33 | 10150 | 3 | | | | | ACADL | 1.00 |
| 10055 | 3 | 4 | | | IV-1 | ZNF639 | 1.15 | 10151 | 3 | | | | | ACAN | 1.00 |
| 10056 | 3 | 4 | | | IV-1 | ZNF668 | 1.37 | 10152 | 3 | | | | | ACBD7 | 1.00 |
| 10057 | 3 | 4 | | | IV-1 | ZNF680 | 1.34 | 10153 | 3 | | | | | ACCN1 | 1.00 |
| 10058 | 3 | 4 | | | IV-1 | ZNF688 | 1.01 | 10154 | 3 | | | | | ACCN3 | 1.00 |
| 10059 | 3 | 4 | | | IV-1 | ZNF689 | 1.24 | 10155 | 3 | | | | | ACCN4 | 1.00 |
| 10060 | 3 | 4 | | | IV-1 | ZNF691 | 1.32 | 10156 | 3 | | | | | ACCN5 | 1.00 |
| 10061 | 3 | 4 | | | IV-1 | ZNF699 | 1.12 | 10157 | 3 | | | | | ACCSL | 1.00 |
| 10062 | 3 | 4 | | | IV-1 | ZNF706 | 1.42 | 10158 | 3 | | | | | ACE | 1.00 |
| 10063 | 3 | 4 | | | IV-1 | ZNF708 | 1.35 | 10159 | 3 | | | | | ACE2 | 1.00 |
| 10064 | 3 | 4 | | | IV-1 | ZNF737 | 1.28 | 10160 | 3 | | | | | ACER1 | 1.00 |
| 10065 | 3 | 4 | | | IV-1 | ZNF74 | 1.49 | 10161 | 3 | | | | | ACHE | 1.00 |
| 10066 | 3 | 4 | | | IV-1 | ZNF740 | 1.45 | 10162 | 3 | | | | | ACMSD | 1.00 |
| 10067 | 3 | 4 | | | IV-1 | ZNF747 | 1.34 | 10163 | 3 | | | | | ACOT11 | 1.00 |
| 10068 | 3 | 4 | | | IV-1 | ZNF749 | 1.31 | 10164 | 3 | | | | | ACOT12 | 1.00 |
| 10069 | 3 | 4 | | | IV-1 | ZNF765 | 1.33 | 10165 | 3 | | | | | ACOT6 | 1.00 |
| 10070 | 3 | 4 | | | IV-1 | ZNF77 | 1.25 | 10166 | 3 | | | | | ACOX2 | 1.00 |
| 10071 | 3 | 4 | | | IV-1 | ZNF775 | 1.14 | 10167 | 3 | | | | | ACOXL | 1.00 |
| 10072 | 3 | 4 | | | IV-1 | ZNF781 | 1.03 | 10168 | 3 | | | | | ACPT | 1.00 |
| 10073 | 3 | 4 | | | IV-1 | ZNF786 | 1.35 | 10169 | 3 | | | | | ACR | 1.00 |
| 10074 | 3 | 4 | | | IV-1 | ZNF787 | 1.14 | 10170 | 3 | | | | | ACRV1 | 1.00 |
| 10075 | 3 | 4 | | | IV-1 | ZNF790 | 1.13 | 10171 | 3 | | | | | ACSBG1 | 1.00 |

Fig. 40 - 54

| | | | | | | | | | | | | | | | |
|---|---|---|---|---|---|---|---|---|---|---|---|---|---|---|---|
| 10172 | 3 | | | | | | ACSBG2 | 1.00 | 10268 | 3 | | | | AFAP1-AS1 | 1.00 |
| 10173 | 3 | | | | | | ACSM1 | 1.00 | 10269 | 3 | | | | AFAP1L1 | 1.00 |
| 10174 | 3 | | | | | | ACSM2A | 1.00 | 10270 | 3 | | | | AFF2 | 1.00 |
| 10175 | 3 | | | | | | ACSM2B | 1.00 | 10271 | 3 | | | | AFM | 1.00 |
| 10176 | 3 | | | | | | ACSM4 | 1.00 | 10272 | 3 | | | | AFP | 1.00 |
| 10177 | 3 | | | | | | ACSM5 | 1.00 | 10273 | 3 | | | | AGAP1 | 1.00 |
| 10178 | 3 | | | | | | ACSS3 | 1.00 | 10274 | 3 | | | | AGAP11 | 1.00 |
| 10179 | 3 | | | | | | ACTA1 | 1.00 | 10275 | 3 | | | | AGBL1 | 1.00 |
| 10180 | 3 | | | | | | ACTBL2 | 1.00 | 10276 | 3 | | | | AGBL2 | 1.00 |
| 10181 | 3 | | | | | | ACTC1 | 1.00 | 10277 | 3 | | | | AGBL3 | 1.00 |
| 10182 | 3 | | | | | | ACTG2 | 1.00 | 10278 | 3 | | | | AGBL4 | 1.00 |
| 10183 | 3 | | | | | | ACTL6B | 1.00 | 10279 | 3 | | | | AGMO | 1.00 |
| 10184 | 3 | | | | | | ACTL7A | 1.00 | 10280 | 3 | | | | AGPAT4-IT1 | 1.00 |
| 10185 | 3 | | | | | | ACTL7B | 1.00 | 10281 | 3 | | | | AGPHD1 | 1.00 |
| 10186 | 3 | | | | | | ACTL8 | 1.00 | 10282 | 3 | | | | AGR2 | 1.00 |
| 10187 | 3 | | | | | | ACTL9 | 1.00 | 10283 | 3 | | | | AGR3 | 1.00 |
| 10188 | 3 | | | | | | ACTN2 | 1.00 | 10284 | 3 | | | | AGRP | 1.00 |
| 10189 | 3 | | | | | | ACTN3 | 1.00 | 10285 | 3 | | | | AGSK1 | 1.00 |
| 10190 | 3 | | | | | | ACTR3BP2 | 1.00 | 10286 | 3 | | | | AGT | 1.00 |
| 10191 | 3 | | | | | | ACTR3BP5 | 1.00 | 10287 | 3 | | | | AGTR1 | 1.00 |
| 10192 | 3 | | | | | | ACTR3C | 1.00 | 10288 | 3 | | | | AGTR2 | 1.00 |
| 10193 | 3 | | | | | | ACTRT1 | 1.00 | 10289 | 3 | | | | AGXT | 1.00 |
| 10194 | 3 | | | | | | ACTRT2 | 1.00 | 10290 | 3 | | | | AGXT2 | 1.00 |
| 10195 | 3 | | | | | | ACVR1C | 1.00 | 10291 | 3 | | | | AGXT2L1 | 1.00 |
| 10196 | 3 | | | | | | ACY3 | 1.00 | 10292 | 3 | | | | AHI1 | 1.00 |
| 10197 | 3 | | | | | | ADAD1 | 1.00 | 10293 | 3 | | | | AHNAK2 | 1.00 |
| 10198 | 3 | | | | | | ADAD2 | 1.00 | 10294 | 3 | | | | AHRR | 1.00 |
| 10199 | 3 | | | | | | ADAM11 | 1.00 | 10295 | 3 | | | | AHSG | 1.00 |
| 10200 | 3 | | | | | | ADAM12 | 1.00 | 10296 | 3 | | | | AICDA | 1.00 |
| 10201 | 3 | | | | | | ADAM18 | 1.00 | 10297 | 3 | | | | AIF1L | 1.00 |
| 10202 | 3 | | | | | | ADAM2 | 1.00 | 10298 | 3 | | | | AIM1L | 1.00 |
| 10203 | 3 | | | | | | ADAM20 | 1.00 | 10299 | 3 | | | | AIPL1 | 1.00 |
| 10204 | 3 | | | | | | ADAM21 | 1.00 | 10300 | 3 | | | | AIRE | 1.00 |
| 10205 | 3 | | | | | | ADAM21P1 | 1.00 | 10301 | 3 | | | | AJAP1 | 1.00 |
| 10206 | 3 | | | | | | ADAM22 | 1.00 | 10302 | 3 | | | | AJUBA | 1.00 |
| 10207 | 3 | | | | | | ADAM23 | 1.00 | 10303 | 3 | | | | AK4 | 1.00 |
| 10208 | 3 | | | | | | ADAM29 | 1.00 | 10304 | 3 | | | | AK7 | 1.00 |
| 10209 | 3 | | | | | | ADAM30 | 1.00 | 10305 | 3 | | | | AK8 | 1.00 |
| 10210 | 3 | | | | | | ADAM32 | 1.00 | 10306 | 3 | | | | AKAP14 | 1.00 |
| 10211 | 3 | | | | | | ADAM33 | 1.00 | 10307 | 3 | | | | AKAP3 | 1.00 |
| 10212 | 3 | | | | | | ADAM3A | 1.00 | 10308 | 3 | | | | AKAP4 | 1.00 |
| 10213 | 3 | | | | | | ADAM5P | 1.00 | 10309 | 3 | | | | AKAP6 | 1.00 |
| 10214 | 3 | | | | | | ADAM6 | 1.00 | 10310 | 3 | | | | AKNAD1 | 1.00 |
| 10215 | 3 | | | | | | ADAM7 | 1.00 | 10311 | 3 | | | | AKR1B10 | 1.00 |
| 10216 | 3 | | | | | | ADAMDEC1 | 1.00 | 10312 | 3 | | | | AKR1B15 | 1.00 |
| 10217 | 3 | | | | | | ADAMTS12 | 1.00 | 10313 | 3 | | | | AKR1C1 | 1.00 |
| 10218 | 3 | | | | | | ADAMTS13 | 1.00 | 10314 | 3 | | | | AKR1C2 | 1.00 |
| 10219 | 3 | | | | | | ADAMTS14 | 1.00 | 10315 | 3 | | | | AKR1C4 | 1.00 |
| 10220 | 3 | | | | | | ADAMTS15 | 1.00 | 10316 | 3 | | | | AKR1CL1 | 1.00 |
| 10221 | 3 | | | | | | ADAMTS16 | 1.00 | 10317 | 3 | | | | AKR1D1 | 1.00 |
| 10222 | 3 | | | | | | ADAMTS17 | 1.00 | 10318 | 3 | | | | AKR1E2 | 1.00 |
| 10223 | 3 | | | | | | ADAMTS18 | 1.00 | 10319 | 3 | | | | AKR7A3 | 1.00 |
| 10224 | 3 | | | | | | ADAMTS19 | 1.00 | 10320 | 3 | | | | AKR7L | 1.00 |
| 10225 | 3 | | | | | | ADAMTS2 | 1.00 | 10321 | 3 | | | | ALB | 1.00 |
| 10226 | 3 | | | | | | ADAMTS20 | 1.00 | 10322 | 3 | | | | ALDH1A2 | 1.00 |
| 10227 | 3 | | | | | | ADAMTS3 | 1.00 | 10323 | 3 | | | | ALDH1A3 | 1.00 |
| 10228 | 3 | | | | | | ADAMTS4 | 1.00 | 10324 | 3 | | | | ALDH1L1 | 1.00 |
| 10229 | 3 | | | | | | ADAMTS5 | 1.00 | 10325 | 3 | | | | ALDH1L2 | 1.00 |
| 10230 | 3 | | | | | | ADAMTS6 | 1.00 | 10326 | 3 | | | | ALDH3A1 | 1.00 |
| 10231 | 3 | | | | | | ADAMTS7 | 1.00 | 10327 | 3 | | | | ALDH3B2 | 1.00 |
| 10232 | 3 | | | | | | ADAMTS8 | 1.00 | 10328 | 3 | | | | ALDH7A1 | 1.00 |
| 10233 | 3 | | | | | | ADAMTS9 | 1.00 | 10329 | 3 | | | | ALDH8A1 | 1.00 |
| 10234 | 3 | | | | | | ADAMTS9-AS2 | 1.00 | 10330 | 3 | | | | ALDOB | 1.00 |
| 10235 | 3 | | | | | | ADAMTSL1 | 1.00 | 10331 | 3 | | | | ALG1L | 1.00 |
| 10236 | 3 | | | | | | ADAMTSL2 | 1.00 | 10332 | 3 | | | | ALG1L2 | 1.00 |
| 10237 | 3 | | | | | | ADAMTSL3 | 1.00 | 10333 | 3 | | | | ALK | 1.00 |
| 10238 | 3 | | | | | | ADARB2-AS1 | 1.00 | 10334 | 3 | | | | ALLC | 1.00 |
| 10239 | 3 | | | | | | ADC | 1.00 | 10335 | 3 | | | | ALMS1P | 1.00 |
| 10240 | 3 | | | | | | ADCY1 | 1.00 | 10336 | 3 | | | | ALOX12B | 1.00 |
| 10241 | 3 | | | | | | ADCY10 | 1.00 | 10337 | 3 | | | | ALOX12P2 | 1.00 |
| 10242 | 3 | | | | | | ADCY2 | 1.00 | 10338 | 3 | | | | ALOXE3 | 1.00 |
| 10243 | 3 | | | | | | ADCY5 | 1.00 | 10339 | 3 | | | | ALPI | 1.00 |
| 10244 | 3 | | | | | | ADCY6 | 1.00 | 10340 | 3 | | | | ALPK2 | 1.00 |
| 10245 | 3 | | | | | | ADCY8 | 1.00 | 10341 | 3 | | | | ALPK3 | 1.00 |
| 10246 | 3 | | | | | | ADCYAP1 | 1.00 | 10342 | 3 | | | | ALPP | 1.00 |
| 10247 | 3 | | | | | | ADCYAP1R1 | 1.00 | 10343 | 3 | | | | ALPPL2 | 1.00 |
| 10248 | 3 | | | | | | ADGB | 1.00 | 10344 | 3 | | | | ALS2CR11 | 1.00 |
| 10249 | 3 | | | | | | ADH1A | 1.00 | 10345 | 3 | | | | ALS2CR12 | 1.00 |
| 10250 | 3 | | | | | | ADH1B | 1.00 | 10346 | 3 | | | | ALX1 | 1.00 |
| 10251 | 3 | | | | | | ADH1C | 1.00 | 10347 | 3 | | | | ALX4 | 1.00 |
| 10252 | 3 | | | | | | ADH4 | 1.00 | 10348 | 3 | | | | AMBN | 1.00 |
| 10253 | 3 | | | | | | ADH6 | 1.00 | 10349 | 3 | | | | AMBP | 1.00 |
| 10254 | 3 | | | | | | ADH7 | 1.00 | 10350 | 3 | | | | AMDHD1 | 1.00 |
| 10255 | 3 | | | | | | ADIG | 1.00 | 10351 | 3 | | | | AMELX | 1.00 |
| 10256 | 3 | | | | | | ADIPOQ | 1.00 | 10352 | 3 | | | | AMELY | 1.00 |
| 10257 | 3 | | | | | | ADORA1 | 1.00 | 10353 | 3 | | | | AMH | 1.00 |
| 10258 | 3 | | | | | | ADPRHL1 | 1.00 | 10354 | 3 | | | | AMHR2 | 1.00 |
| 10259 | 3 | | | | | | ADRA1A | 1.00 | 10355 | 3 | | | | AMN | 1.00 |
| 10260 | 3 | | | | | | ADRA1B | 1.00 | 10356 | 3 | | | | AMOTL1 | 1.00 |
| 10261 | 3 | | | | | | ADRA1D | 1.00 | 10357 | 3 | | | | AMOTL2 | 1.00 |
| 10262 | 3 | | | | | | ADRA2A | 1.00 | 10358 | 3 | | | | AMPD1 | 1.00 |
| 10263 | 3 | | | | | | ADRA2B | 1.00 | 10359 | 3 | | | | AMPH | 1.00 |
| 10264 | 3 | | | | | | ADRA2C | 1.00 | 10360 | 3 | | | | AMTN | 1.00 |
| 10265 | 3 | | | | | | ADRB1 | 1.00 | 10361 | 3 | | | | AMY1B | 1.00 |
| 10266 | 3 | | | | | | ADRB3 | 1.00 | 10362 | 3 | | | | AMY1C | 1.00 |
| 10267 | 3 | | | | | | ADSSL1 | 1.00 | 10363 | 3 | | | | AMZ1 | 1.00 |

Fig. 40 - 55

| | | | | | | | |
|---|---|---|---|---|---|---|---|
| 10364 | 3 | | | | ANGPT2 | | 1.00 |
| 10365 | 3 | | | | ANGPT4 | | 1.00 |
| 10366 | 3 | | | | ANGPTL1 | | 1.00 |
| 10367 | 3 | | | | ANGPTL2 | | 1.00 |
| 10368 | 3 | | | | ANGPTL3 | | 1.00 |
| 10369 | 3 | | | | ANGPTL4 | | 1.00 |
| 10370 | 3 | | | | ANGPTL5 | | 1.00 |
| 10371 | 3 | | | | ANGPTL6 | | 1.00 |
| 10372 | 3 | | | | ANGPTL7 | | 1.00 |
| 10373 | 3 | | | | ANK2 | | 1.00 |
| 10374 | 3 | | | | ANKAR | | 1.00 |
| 10375 | 3 | | | | ANKFN1 | | 1.00 |
| 10376 | 3 | | | | ANKK1 | | 1.00 |
| 10377 | 3 | | | | ANKRD1 | | 1.00 |
| 10378 | 3 | | | | ANKRD13B | | 1.00 |
| 10379 | 3 | | | | ANKRD16 | | 1.00 |
| 10380 | 3 | | | | ANKRD18A | | 1.00 |
| 10381 | 3 | | | | ANKRD18B | | 1.00 |
| 10382 | 3 | | | | ANKRD18DP | | 1.00 |
| 10383 | 3 | | | | ANKRD2 | | 1.00 |
| 10384 | 3 | | | | ANKRD20A1 | | 1.00 |
| 10385 | 3 | | | | ANKRD20A11P | | 1.00 |
| 10386 | 3 | | | | ANKRD20A2 | | 1.00 |
| 10387 | 3 | | | | ANKRD20A3 | | 1.00 |
| 10388 | 3 | | | | ANKRD20A4 | | 1.00 |
| 10389 | 3 | | | | ANKRD20A5P | | 1.00 |
| 10390 | 3 | | | | ANKRD20A8P | | 1.00 |
| 10391 | 3 | | | | ANKRD20A9P | | 1.00 |
| 10392 | 3 | | | | ANKRD24 | | 1.00 |
| 10393 | 3 | | | | ANKRD26P1 | | 1.00 |
| 10394 | 3 | | | | ANKRD26P3 | | 1.00 |
| 10395 | 3 | | | | ANKRD29 | | 1.00 |
| 10396 | 3 | | | | ANKRD30A | | 1.00 |
| 10397 | 3 | | | | ANKRD30B | | 1.00 |
| 10398 | 3 | | | | ANKRD30BL | | 1.00 |
| 10399 | 3 | | | | ANKRD30BP2 | | 1.00 |
| 10400 | 3 | | | | ANKRD31 | | 1.00 |
| 10401 | 3 | | | | ANKRD33 | | 1.00 |
| 10402 | 3 | | | | ANKRD34C | | 1.00 |
| 10403 | 3 | | | | ANKRD35 | | 1.00 |
| 10404 | 3 | | | | ANKRD36BP2 | | 1.00 |
| 10405 | 3 | | | | ANKRD37 | | 1.00 |
| 10406 | 3 | | | | ANKRD45 | | 1.00 |
| 10407 | 3 | | | | ANKRD53 | | 1.00 |
| 10408 | 3 | | | | ANKRD62P1-PARP4P3 | | 1.00 |
| 10409 | 3 | | | | ANKRD63 | | 1.00 |
| 10410 | 3 | | | | ANKRD65 | | 1.00 |
| 10411 | 3 | | | | ANKRD7 | | 1.00 |
| 10412 | 3 | | | | ANKS1B | | 1.00 |
| 10413 | 3 | | | | ANKS4B | | 1.00 |
| 10414 | 3 | | | | ANKUB1 | | 1.00 |
| 10415 | 3 | | | | ANLN | | 1.00 |
| 10416 | 3 | | | | ANO1 | | 1.00 |
| 10417 | 3 | | | | ANO2 | | 1.00 |
| 10418 | 3 | | | | ANO3 | | 1.00 |
| 10419 | 3 | | | | ANO4 | | 1.00 |
| 10420 | 3 | | | | ANO5 | | 1.00 |
| 10421 | 3 | | | | ANO7 | | 1.00 |
| 10422 | 3 | | | | ANTXR1 | | 1.00 |
| 10423 | 3 | | | | ANTXRL | | 1.00 |
| 10424 | 3 | | | | ANXA10 | | 1.00 |
| 10425 | 3 | | | | ANXA13 | | 1.00 |
| 10426 | 3 | | | | ANXA8 | | 1.00 |
| 10427 | 3 | | | | ANXA8L1 | | 1.00 |
| 10428 | 3 | | | | ANXA8L2 | | 1.00 |
| 10429 | 3 | | | | AOC4 | | 1.00 |
| 10430 | 3 | | | | AOX1 | | 1.00 |
| 10431 | 3 | | | | AOX2P | | 1.00 |
| 10432 | 3 | | | | AP1B1P1 | | 1.00 |
| 10433 | 3 | | | | AP3B2 | | 1.00 |
| 10434 | 3 | | | | AP8A1 | | 1.00 |
| 10435 | 3 | | | | APBB2 | | 1.00 |
| 10436 | 3 | | | | APC2 | | 1.00 |
| 10437 | 3 | | | | APCDD1L | | 1.00 |
| 10438 | 3 | | | | APCS | | 1.00 |
| 10439 | 3 | | | | APITD1 | | 1.00 |
| 10440 | 3 | | | | APLF | | 1.00 |
| 10441 | 3 | | | | APLN | | 1.00 |
| 10442 | 3 | | | | APLNR | | 1.00 |
| 10443 | 3 | | | | APLP1 | | 1.00 |
| 10444 | 3 | | | | APOA1 | | 1.00 |
| 10445 | 3 | | | | APOA2 | | 1.00 |
| 10446 | 3 | | | | APOA4 | | 1.00 |
| 10447 | 3 | | | | APOA5 | | 1.00 |
| 10448 | 3 | | | | APOB | | 1.00 |
| 10449 | 3 | | | | APOBEC1 | | 1.00 |
| 10450 | 3 | | | | APOBEC2 | | 1.00 |
| 10451 | 3 | | | | APOBEC4 | | 1.00 |
| 10452 | 3 | | | | APOC1 | | 1.00 |
| 10453 | 3 | | | | APOC1P1 | | 1.00 |
| 10454 | 3 | | | | APOC2 | | 1.00 |
| 10455 | 3 | | | | APOC3 | | 1.00 |
| 10456 | 3 | | | | APOC4 | | 1.00 |
| 10457 | 3 | | | | APOC4-APOC2 | | 1.00 |
| 10458 | 3 | | | | APOD | | 1.00 |
| 10459 | 3 | | | | APOE | | 1.00 |
| 10460 | 3 | | | | APOF | | 1.00 |
| 10461 | 3 | | | | APOH | | 1.00 |
| 10462 | 3 | | | | APOL5 | | 1.00 |
| 10463 | 3 | | | | APOLD1 | | 1.00 |
| 10464 | 3 | | | | APOM | | 1.00 |
| 10465 | 3 | | | | AQP11 | | 1.00 |
| 10466 | 3 | | | | AQP12A | | 1.00 |
| 10467 | 3 | | | | AQP12B | | 1.00 |
| 10468 | 3 | | | | AQP2 | | 1.00 |
| 10469 | 3 | | | | AQP4 | | 1.00 |
| 10470 | 3 | | | | AQP5 | | 1.00 |
| 10471 | 3 | | | | AQP6 | | 1.00 |
| 10472 | 3 | | | | AQP7 | | 1.00 |
| 10473 | 3 | | | | AQP7P1 | | 1.00 |
| 10474 | 3 | | | | AQP7P3 | | 1.00 |
| 10475 | 3 | | | | AQP8 | | 1.00 |
| 10476 | 3 | | | | AQPEP | | 1.00 |
| 10477 | 3 | | | | AR | | 1.00 |
| 10478 | 3 | | | | ARC | | 1.00 |
| 10479 | 3 | | | | ARGFX | | 1.00 |
| 10480 | 3 | | | | ARHGAP19-SLIT1 | | 1.00 |
| 10481 | 3 | | | | ARHGAP20 | | 1.00 |
| 10482 | 3 | | | | ARHGAP23 | | 1.00 |
| 10483 | 3 | | | | ARHGAP28 | | 1.00 |
| 10484 | 3 | | | | ARHGAP29 | | 1.00 |
| 10485 | 3 | | | | ARHGAP36 | | 1.00 |
| 10486 | 3 | | | | ARHGAP39 | | 1.00 |
| 10487 | 3 | | | | ARHGAP40 | | 1.00 |
| 10488 | 3 | | | | ARHGAP42 | | 1.00 |
| 10489 | 3 | | | | ARHGAP44 | | 1.00 |
| 10490 | 3 | | | | ARHGAP8 | | 1.00 |
| 10491 | 3 | | | | ARHGDIG | | 1.00 |
| 10492 | 3 | | | | ARHGEF10 | | 1.00 |
| 10493 | 3 | | | | ARHGEF15 | | 1.00 |
| 10494 | 3 | | | | ARHGEF16 | | 1.00 |
| 10495 | 3 | | | | ARHGEF17 | | 1.00 |
| 10496 | 3 | | | | ARHGEF25 | | 1.00 |
| 10497 | 3 | | | | ARHGEF26 | | 1.00 |
| 10498 | 3 | | | | ARHGEF26-AS1 | | 1.00 |
| 10499 | 3 | | | | ARHGEF33 | | 1.00 |
| 10500 | 3 | | | | ARHGEF37 | | 1.00 |
| 10501 | 3 | | | | ARHGEF38 | | 1.00 |
| 10502 | 3 | | | | ARHGEF4 | | 1.00 |
| 10503 | 3 | | | | ARID3C | | 1.00 |
| 10504 | 3 | | | | ARL13A | | 1.00 |
| 10505 | 3 | | | | ARL14 | | 1.00 |
| 10506 | 3 | | | | ARL2-SNX15 | | 1.00 |
| 10507 | 3 | | | | ARL5C | | 1.00 |
| 10508 | 3 | | | | ARL6 | | 1.00 |
| 10509 | 3 | | | | ARL9 | | 1.00 |
| 10510 | 3 | | | | ARMC12 | | 1.00 |
| 10511 | 3 | | | | ARMC3 | | 1.00 |
| 10512 | 3 | | | | ARMC4 | | 1.00 |
| 10513 | 3 | | | | ARMC9 | | 1.00 |
| 10514 | 3 | | | | ARMCX5-GPRASP2 | | 1.00 |
| 10515 | 3 | | | | ARMS2 | | 1.00 |
| 10516 | 3 | | | | ARNT2 | | 1.00 |
| 10517 | 3 | | | | ARNTL2 | | 1.00 |
| 10518 | 3 | | | | ARPM1 | | 1.00 |
| 10519 | 3 | | | | ARPP21 | | 1.00 |
| 10520 | 3 | | | | ARR3 | | 1.00 |
| 10521 | 3 | | | | ARSE | | 1.00 |
| 10522 | 3 | | | | ARSF | | 1.00 |
| 10523 | 3 | | | | ARSH | | 1.00 |
| 10524 | 3 | | | | ARSI | | 1.00 |
| 10525 | 3 | | | | ARSJ | | 1.00 |
| 10526 | 3 | | | | ART1 | | 1.00 |
| 10527 | 3 | | | | ART3 | | 1.00 |
| 10528 | 3 | | | | ART4 | | 1.00 |
| 10529 | 3 | | | | ART5 | | 1.00 |
| 10530 | 3 | | | | ARTN | | 1.00 |
| 10531 | 3 | | | | ARVCF | | 1.00 |
| 10532 | 3 | | | | ARX | | 1.00 |
| 10533 | 3 | | | | AS3MT | | 1.00 |
| 10534 | 3 | | | | ASAH2 | | 1.00 |
| 10535 | 3 | | | | ASAH2B | | 1.00 |
| 10536 | 3 | | | | ASAP1-IT1 | | 1.00 |
| 10537 | 3 | | | | ASAP3 | | 1.00 |
| 10538 | 3 | | | | ASB10 | | 1.00 |
| 10539 | 3 | | | | ASB11 | | 1.00 |
| 10540 | 3 | | | | ASB12 | | 1.00 |
| 10541 | 3 | | | | ASB14 | | 1.00 |
| 10542 | 3 | | | | ASB15 | | 1.00 |
| 10543 | 3 | | | | ASB17 | | 1.00 |
| 10544 | 3 | | | | ASB18 | | 1.00 |
| 10545 | 3 | | | | ASB4 | | 1.00 |
| 10546 | 3 | | | | ASB5 | | 1.00 |
| 10547 | 3 | | | | ASB9 | | 1.00 |
| 10548 | 3 | | | | ASCL1 | | 1.00 |
| 10549 | 3 | | | | ASCL3 | | 1.00 |
| 10550 | 3 | | | | ASCL4 | | 1.00 |
| 10551 | 3 | | | | ASIP | | 1.00 |
| 10552 | 3 | | | | ASMT | | 1.00 |
| 10553 | 3 | | | | ASPA | | 1.00 |
| 10554 | 3 | | | | ASPDH | | 1.00 |

Fig. 40 - 56

| | | | | | | | | | | | | | | |
|---|---|---|---|---|---|---|---|---|---|---|---|---|---|---|
| 10555 | 3 | | | | | ASPG | 1.00 | 10651 | 3 | | | | BCL2L15 | 1.00 |
| 10556 | 3 | | | | | ASPHD1 | 1.00 | 10652 | 3 | | | | BCL6B | 1.00 |
| 10557 | 3 | | | | | ASPM | 1.00 | 10653 | 3 | | | | BCMO1 | 1.00 |
| 10558 | 3 | | | | | ASPN | 1.00 | 10654 | 3 | | | | BCO2 | 1.00 |
| 10559 | 3 | | | | | ASS1 | 1.00 | 10655 | 3 | | | | BCORP1 | 1.00 |
| 10560 | 3 | | | | | ASTL | 1.00 | 10656 | 3 | | | | BCRP2 | 1.00 |
| 10561 | 3 | | | | | ASTN1 | 1.00 | 10657 | 3 | | | | BCYRN1 | 1.00 |
| 10562 | 3 | | | | | ASTN2 | 1.00 | 10658 | 3 | | | | BDAG1 | 1.00 |
| 10563 | 3 | | | | | ASXL3 | 1.00 | 10659 | 3 | | | | BDKRB1 | 1.00 |
| 10564 | 3 | | | | | ASZ1 | 1.00 | 10660 | 3 | | | | BDKRB2 | 1.00 |
| 10565 | 3 | | | | | ATAD3C | 1.00 | 10661 | 3 | | | | BDNF | 1.00 |
| 10566 | 3 | | | | | ATCAY | 1.00 | 10662 | 3 | | | | BDNF-AS1 | 1.00 |
| 10567 | 3 | | | | | ATL1 | 1.00 | 10663 | 3 | | | | BEND3 | 1.00 |
| 10568 | 3 | | | | | ATOH1 | 1.00 | 10664 | 3 | | | | BEND4 | 1.00 |
| 10569 | 3 | | | | | ATOH7 | 1.00 | 10665 | 3 | | | | BEND6 | 1.00 |
| 10570 | 3 | | | | | ATOH8 | 1.00 | 10666 | 3 | | | | BEST2 | 1.00 |
| 10571 | 3 | | | | | ATP10B | 1.00 | 10667 | 3 | | | | BEST3 | 1.00 |
| 10572 | 3 | | | | | ATP12A | 1.00 | 10668 | 3 | | | | BEST4 | 1.00 |
| 10573 | 3 | | | | | ATP13A4 | 1.00 | 10669 | 3 | | | | BEX1 | 1.00 |
| 10574 | 3 | | | | | ATP13A5 | 1.00 | 10670 | 3 | | | | BFSP1 | 1.00 |
| 10575 | 3 | | | | | ATP1A2 | 1.00 | 10671 | 3 | | | | BFSP2 | 1.00 |
| 10576 | 3 | | | | | ATP1A3 | 1.00 | 10672 | 3 | | | | BGLAP | 1.00 |
| 10577 | 3 | | | | | ATP1A4 | 1.00 | 10673 | 3 | | | | BGN | 1.00 |
| 10578 | 3 | | | | | ATP1B2 | 1.00 | 10674 | 3 | | | | BHLHA9 | 1.00 |
| 10579 | 3 | | | | | ATP1B4 | 1.00 | 10675 | 3 | | | | BHLHB9 | 1.00 |
| 10580 | 3 | | | | | ATP2A1 | 1.00 | 10676 | 3 | | | | BHLHE22 | 1.00 |
| 10581 | 3 | | | | | ATP2B2 | 1.00 | 10677 | 3 | | | | BHLHE23 | 1.00 |
| 10582 | 3 | | | | | ATP2B3 | 1.00 | 10678 | 3 | | | | BHMT | 1.00 |
| 10583 | 3 | | | | | ATP2C2 | 1.00 | 10679 | 3 | | | | BHMT2 | 1.00 |
| 10584 | 3 | | | | | ATP4A | 1.00 | 10680 | 3 | | | | BICC1 | 1.00 |
| 10585 | 3 | | | | | ATP4B | 1.00 | 10681 | 3 | | | | BIRC5 | 1.00 |
| 10586 | 3 | | | | | ATP6AP1L | 1.00 | 10682 | 3 | | | | BIRC7 | 1.00 |
| 10587 | 3 | | | | | ATP6V0A4 | 1.00 | 10683 | 3 | | | | BIRC8 | 1.00 |
| 10588 | 3 | | | | | ATP6V0CP3 | 1.00 | 10684 | 3 | | | | BIVM-ERCC5 | 1.00 |
| 10589 | 3 | | | | | ATP6V0D2 | 1.00 | 10685 | 3 | | | | BK250D11 | 1.00 |
| 10590 | 3 | | | | | ATP6V1B1 | 1.00 | 10686 | 3 | | | | BLID | 1.00 |
| 10591 | 3 | | | | | ATP6V1G3 | 1.00 | 10687 | 3 | | | | BMP1 | 1.00 |
| 10592 | 3 | | | | | ATP7B | 1.00 | 10688 | 3 | | | | BMP10 | 1.00 |
| 10593 | 3 | | | | | ATP8A2 | 1.00 | 10689 | 3 | | | | BMP15 | 1.00 |
| 10594 | 3 | | | | | ATP8B1 | 1.00 | 10690 | 3 | | | | BMP3 | 1.00 |
| 10595 | 3 | | | | | ATP8B3 | 1.00 | 10691 | 3 | | | | BMP4 | 1.00 |
| 10596 | 3 | | | | | ATPAF1-AS1 | 1.00 | 10692 | 3 | | | | BMP5 | 1.00 |
| 10597 | 3 | | | | | ATRNL1 | 1.00 | 10693 | 3 | | | | BMP7 | 1.00 |
| 10598 | 3 | | | | | ATXN3L | 1.00 | 10694 | 3 | | | | BMPER | 1.00 |
| 10599 | 3 | | | | | ATXN8OS | 1.00 | 10695 | 3 | | | | BMPR1A | 1.00 |
| 10600 | 3 | | | | | AURKB | 1.00 | 10696 | 3 | | | | BMPR1B | 1.00 |
| 10601 | 3 | | | | | AURKC | 1.00 | 10697 | 3 | | | | BMS1P5 | 1.00 |
| 10602 | 3 | | | | | AVP | 1.00 | 10698 | 3 | | | | BNC1 | 1.00 |
| 10603 | 3 | | | | | AVPR1A | 1.00 | 10699 | 3 | | | | BNC2 | 1.00 |
| 10604 | 3 | | | | | AVPR1B | 1.00 | 10700 | 3 | | | | BOC | 1.00 |
| 10605 | 3 | | | | | AVPR2 | 1.00 | 10701 | 3 | | | | BOD1P | 1.00 |
| 10606 | 3 | | | | | AWAT1 | 1.00 | 10702 | 3 | | | | BOK-AS1 | 1.00 |
| 10607 | 3 | | | | | AWAT2 | 1.00 | 10703 | 3 | | | | BOLA3-AS1 | 1.00 |
| 10608 | 3 | | | | | AXDND1 | 1.00 | 10704 | 3 | | | | BOLL | 1.00 |
| 10609 | 3 | | | | | AXL | 1.00 | 10705 | 3 | | | | BPESC1 | 1.00 |
| 10610 | 3 | | | | | AZGP1 | 1.00 | 10706 | 3 | | | | BPIFA1 | 1.00 |
| 10611 | 3 | | | | | AZGP1P1 | 1.00 | 10707 | 3 | | | | BPIFA2 | 1.00 |
| 10612 | 3 | | | | | B3GALNT1 | 1.00 | 10708 | 3 | | | | BPIFA3 | 1.00 |
| 10613 | 3 | | | | | B3GALT1 | 1.00 | 10709 | 3 | | | | BPIFA4P | 1.00 |
| 10614 | 3 | | | | | B3GALT5 | 1.00 | 10710 | 3 | | | | BPIFB1 | 1.00 |
| 10615 | 3 | | | | | B3GAT2 | 1.00 | 10711 | 3 | | | | BPIFB2 | 1.00 |
| 10616 | 3 | | | | | B3GNT3 | 1.00 | 10712 | 3 | | | | BPIFB3 | 1.00 |
| 10617 | 3 | | | | | B3GNT4 | 1.00 | 10713 | 3 | | | | BPIFB4 | 1.00 |
| 10618 | 3 | | | | | B3GNT6 | 1.00 | 10714 | 3 | | | | BPIFB6 | 1.00 |
| 10619 | 3 | | | | | B4GALNT1 | 1.00 | 10715 | 3 | | | | BPIFC | 1.00 |
| 10620 | 3 | | | | | B4GALNT2 | 1.00 | 10716 | 3 | | | | BPY2 | 1.00 |
| 10621 | 3 | | | | | B4GALNT4 | 1.00 | 10717 | 3 | | | | BPY2B | 1.00 |
| 10622 | 3 | | | | | B7H6 | 1.00 | 10718 | 3 | | | | BRCA2 | 1.00 |
| 10623 | 3 | | | | | B9D1 | 1.00 | 10719 | 3 | | | | BRD7P3 | 1.00 |
| 10624 | 3 | | | | | BAALC | 1.00 | 10720 | 3 | | | | BRDT | 1.00 |
| 10625 | 3 | | | | | BAAT | 1.00 | 10721 | 3 | | | | BRE A2 | 1.00 |
| 10626 | 3 | | | | | BAGE | 1.00 | 10722 | 3 | | | | BRIP1 | 1.00 |
| 10627 | 3 | | | | | BAGE3 | 1.00 | 10723 | 3 | | | | BRS3 | 1.00 |
| 10628 | 3 | | | | | BAGE4 | 1.00 | 10724 | 3 | | | | BRSK1 | 1.00 |
| 10629 | 3 | | | | | BAGE5 | 1.00 | 10725 | 3 | | | | BRSK2 | 1.00 |
| 10630 | 3 | | | | | BAI1 | 1.00 | 10726 | 3 | | | | BRWD1-IT2 | 1.00 |
| 10631 | 3 | | | | | BAI2 | 1.00 | 10727 | 3 | | | | BSN | 1.00 |
| 10632 | 3 | | | | | BAI3 | 1.00 | 10728 | 3 | | | | BSN-AS2 | 1.00 |
| 10633 | 3 | | | | | BAIAP2L1 | 1.00 | 10729 | 3 | | | | BSND | 1.00 |
| 10634 | 3 | | | | | BAIAP2L2 | 1.00 | 10730 | 3 | | | | BSPH1 | 1.00 |
| 10635 | 3 | | | | | BANF2 | 1.00 | 10731 | 3 | | | | BSPRY | 1.00 |
| 10636 | 3 | | | | | BARHL1 | 1.00 | 10732 | 3 | | | | BSX | 1.00 |
| 10637 | 3 | | | | | BARHL2 | 1.00 | 10733 | 3 | | | | BTBD16 | 1.00 |
| 10638 | 3 | | | | | BARX1 | 1.00 | 10734 | 3 | | | | BTBD17 | 1.00 |
| 10639 | 3 | | | | | BARX2 | 1.00 | 10735 | 3 | | | | BTBD18 | 1.00 |
| 10640 | 3 | | | | | BBOX1 | 1.00 | 10736 | 3 | | | | BTBD8 | 1.00 |
| 10641 | 3 | | | | | BBS5 | 1.00 | 10737 | 3 | | | | BTC | 1.00 |
| 10642 | 3 | | | | | BCAM | 1.00 | 10738 | 3 | | | | BTG4 | 1.00 |
| 10643 | 3 | | | | | BCAN | 1.00 | 10739 | 3 | | | | BTN1A1 | 1.00 |
| 10644 | 3 | | | | | BCAR1 | 1.00 | 10740 | 3 | | | | BTNL2 | 1.00 |
| 10645 | 3 | | | | | BCAR3 | 1.00 | 10741 | 3 | | | | BTNL9 | 1.00 |
| 10646 | 3 | | | | | BCAR4 | 1.00 | 10742 | 3 | | | | BUB1 | 1.00 |
| 10647 | 3 | | | | | BCAS1 | 1.00 | 10743 | 3 | | | | BUB1B | 1.00 |
| 10648 | 3 | | | | | BCHE | 1.00 | 10744 | 3 | | | | BVES | 1.00 |
| 10649 | 3 | | | | | BCL2L10 | 1.00 | 10745 | 3 | | | | BVES-AS1 | 1.00 |
| 10650 | 3 | | | | | BCL2L14 | 1.00 | 10746 | 3 | | | | C10orf10 | 1.00 |

Fig. 40 - 57

| | | | | | | | | | | | |
|---|---|---|---|---|---|---|---|---|---|---|---|
| 10747 | 3 | | | | C10orf103 | 1.00 | 10843 | 3 | | C15orf5 | 1.00 |
| 10748 | 3 | | | | C10orf107 | 1.00 | 10844 | 3 | | C15orf53 | 1.00 |
| 10749 | 3 | | | | C10orf108 | 1.00 | 10845 | 3 | | C15orf55 | 1.00 |
| 10750 | 3 | | | | C10orf111 | 1.00 | 10846 | 3 | | C15orf56 | 1.00 |
| 10751 | 3 | | | | C10orf113 | 1.00 | 10847 | 3 | | C15orf59 | 1.00 |
| 10752 | 3 | | | | C10orf114 | 1.00 | 10848 | 3 | | C15orf60 | 1.00 |
| 10753 | 3 | | | | C10orf120 | 1.00 | 10849 | 3 | | C16orf11 | 1.00 |
| 10754 | 3 | | | | C10orf122 | 1.00 | 10850 | 3 | | C16orf3 | 1.00 |
| 10755 | 3 | | | | C10orf129 | 1.00 | 10851 | 3 | | C16orf46 | 1.00 |
| 10756 | 3 | | | | C10orf131 | 1.00 | 10852 | 3 | | C16orf59 | 1.00 |
| 10757 | 3 | | | | C10orf136 | 1.00 | 10853 | 3 | | C16orf71 | 1.00 |
| 10758 | 3 | | | | C10orf140 | 1.00 | 10854 | 3 | | C16orf73 | 1.00 |
| 10759 | 3 | | | | C10orf25 | 1.00 | 10855 | 3 | | C16orf78 | 1.00 |
| 10760 | 3 | | | | C10orf27 | 1.00 | 10856 | 3 | | C16orf82 | 1.00 |
| 10761 | 3 | | | | C10orf32-AS3MT | 1.00 | 10857 | 3 | | C16orf89 | 1.00 |
| 10762 | 3 | | | | C10orf40 | 1.00 | 10858 | 3 | | C16orf90 | 1.00 |
| 10763 | 3 | | | | C10orf53 | 1.00 | 10859 | 3 | | C16orf92 | 1.00 |
| 10764 | 3 | | | | C10orf55 | 1.00 | 10860 | 3 | | C16orf95 | 1.00 |
| 10765 | 3 | | | | C10orf62 | 1.00 | 10861 | 3 | | C16orf96 | 1.00 |
| 10766 | 3 | | | | C10orf67 | 1.00 | 10862 | 3 | | C17orf102 | 1.00 |
| 10767 | 3 | | | | C10orf68 | 1.00 | 10863 | 3 | | C17orf104 | 1.00 |
| 10768 | 3 | | | | C10orf71 | 1.00 | 10864 | 3 | | C17orf105 | 1.00 |
| 10769 | 3 | | | | C10orf81 | 1.00 | 10865 | 3 | | C17orf107 | 1.00 |
| 10770 | 3 | | | | C10orf82 | 1.00 | 10866 | 3 | | C17orf110 | 1.00 |
| 10771 | 3 | | | | C10orf90 | 1.00 | 10867 | 3 | | C17orf28 | 1.00 |
| 10772 | 3 | | | | C10orf91 | 1.00 | 10868 | 3 | | C17orf47 | 1.00 |
| 10773 | 3 | | | | C10orf96 | 1.00 | 10869 | 3 | | C17orf50 | 1.00 |
| 10774 | 3 | | | | C10orf99 | 1.00 | 10870 | 3 | | C17orf53 | 1.00 |
| 10775 | 3 | | | | C11orf16 | 1.00 | 10871 | 3 | | C17orf64 | 1.00 |
| 10776 | 3 | | | | C11orf20 | 1.00 | 10872 | 3 | | C17orf66 | 1.00 |
| 10777 | 3 | | | | C11orf34 | 1.00 | 10873 | 3 | | C17orf74 | 1.00 |
| 10778 | 3 | | | | C11orf36 | 1.00 | 10874 | 3 | | C17orf77 | 1.00 |
| 10779 | 3 | | | | C11orf40 | 1.00 | 10875 | 3 | | C17orf78 | 1.00 |
| 10780 | 3 | | | | C11orf41 | 1.00 | 10876 | 3 | | C17orf82 | 1.00 |
| 10781 | 3 | | | | C11orf42 | 1.00 | 10877 | 3 | | C17orf96 | 1.00 |
| 10782 | 3 | | | | C11orf45 | 1.00 | 10878 | 3 | | C17orf98 | 1.00 |
| 10783 | 3 | | | | C11orf52 | 1.00 | 10879 | 3 | | C17orf99 | 1.00 |
| 10784 | 3 | | | | C11orf53 | 1.00 | 10880 | 3 | | C18orf26 | 1.00 |
| 10785 | 3 | | | | C11orf65 | 1.00 | 10881 | 3 | | C18orf34 | 1.00 |
| 10786 | 3 | | | | C11orf70 | 1.00 | 10882 | 3 | | C18orf42 | 1.00 |
| 10787 | 3 | | | | C11orf80 | 1.00 | 10883 | 3 | | C18orf56 | 1.00 |
| 10788 | 3 | | | | C11orf85 | 1.00 | 10884 | 3 | | C18orf62 | 1.00 |
| 10789 | 3 | | | | C11orf86 | 1.00 | 10885 | 3 | | C18orf63 | 1.00 |
| 10790 | 3 | | | | C11orf87 | 1.00 | 10886 | 3 | | C19orf18 | 1.00 |
| 10791 | 3 | | | | C11orf88 | 1.00 | 10887 | 3 | | C19orf21 | 1.00 |
| 10792 | 3 | | | | C11orf9 | 1.00 | 10888 | 3 | | C19orf26 | 1.00 |
| 10793 | 3 | | | | C11orf91 | 1.00 | 10889 | 3 | | C19orf33 | 1.00 |
| 10794 | 3 | | | | C11orf92 | 1.00 | 10890 | 3 | | C19orf45 | 1.00 |
| 10795 | 3 | | | | C11orf93 | 1.00 | 10891 | 3 | | C19orf46 | 1.00 |
| 10796 | 3 | | | | C11orf94 | 1.00 | 10892 | 3 | | C19orf51 | 1.00 |
| 10797 | 3 | | | | C11orf96 | 1.00 | 10893 | 3 | | C19orf57 | 1.00 |
| 10798 | 3 | | | | C12orf12 | 1.00 | 10894 | 3 | | C19orf69 | 1.00 |
| 10799 | 3 | | | | C12orf33 | 1.00 | 10895 | 3 | | C19orf75 | 1.00 |
| 10800 | 3 | | | | C12orf34 | 1.00 | 10896 | 3 | | C19orf76 | 1.00 |
| 10801 | 3 | | | | C12orf36 | 1.00 | 10897 | 3 | | C19orf80 | 1.00 |
| 10802 | 3 | | | | C12orf37 | 1.00 | 10898 | 3 | | C19orf81 | 1.00 |
| 10803 | 3 | | | | C12orf39 | 1.00 | 10899 | 3 | | C1QL1 | 1.00 |
| 10804 | 3 | | | | C12orf40 | 1.00 | 10900 | 3 | | C1QL2 | 1.00 |
| 10805 | 3 | | | | C12orf50 | 1.00 | 10901 | 3 | | C1QL4 | 1.00 |
| 10806 | 3 | | | | C12orf53 | 1.00 | 10902 | 3 | | C1QTNF1 | 1.00 |
| 10807 | 3 | | | | C12orf54 | 1.00 | 10903 | 3 | | C1QTNF2 | 1.00 |
| 10808 | 3 | | | | C12orf56 | 1.00 | 10904 | 3 | | C1QTNF3-AMACR | 1.00 |
| 10809 | 3 | | | | C12orf59 | 1.00 | 10905 | 3 | | C1QTNF4 | 1.00 |
| 10810 | 3 | | | | C12orf60 | 1.00 | 10906 | 3 | | C1QTNF5 | 1.00 |
| 10811 | 3 | | | | C12orf61 | 1.00 | 10907 | 3 | | C1QTNF7 | 1.00 |
| 10812 | 3 | | | | C12orf68 | 1.00 | 10908 | 3 | | C1QTNF8 | 1.00 |
| 10813 | 3 | | | | C12orf69 | 1.00 | 10909 | 3 | | C1QTNF9 | 1.00 |
| 10814 | 3 | | | | C12orf70 | 1.00 | 10910 | 3 | | C1QTNF9B | 1.00 |
| 10815 | 3 | | | | C12orf71 | 1.00 | 10911 | 3 | | C1QTNF9B-AS1 | 1.00 |
| 10816 | 3 | | | | C12orf74 | 1.00 | 10912 | 3 | | C1S | 1.00 |
| 10817 | 3 | | | | C12orf77 | 1.00 | 10913 | 3 | | C1orf100 | 1.00 |
| 10818 | 3 | | | | C13orf33 | 1.00 | 10914 | 3 | | C1orf101 | 1.00 |
| 10819 | 3 | | | | C13orf35 | 1.00 | 10915 | 3 | | C1orf105 | 1.00 |
| 10820 | 3 | | | | C14orf105 | 1.00 | 10916 | 3 | | C1orf106 | 1.00 |
| 10821 | 3 | | | | C14orf162 | 1.00 | 10917 | 3 | | C1orf110 | 1.00 |
| 10822 | 3 | | | | C14orf165 | 1.00 | 10918 | 3 | | C1orf111 | 1.00 |
| 10823 | 3 | | | | C14orf166B | 1.00 | 10919 | 3 | | C1orf112 | 1.00 |
| 10824 | 3 | | | | C14orf176 | 1.00 | 10920 | 3 | | C1orf114 | 1.00 |
| 10825 | 3 | | | | C14orf177 | 1.00 | 10921 | 3 | | C1orf126 | 1.00 |
| 10826 | 3 | | | | C14orf178 | 1.00 | 10922 | 3 | | C1orf127 | 1.00 |
| 10827 | 3 | | | | C14orf180 | 1.00 | 10923 | 3 | | C1orf129 | 1.00 |
| 10828 | 3 | | | | C14orf183 | 1.00 | 10924 | 3 | | C1orf130 | 1.00 |
| 10829 | 3 | | | | C14orf23 | 1.00 | 10925 | 3 | | C1orf133 | 1.00 |
| 10830 | 3 | | | | C14orf37 | 1.00 | 10926 | 3 | | C1orf135 | 1.00 |
| 10831 | 3 | | | | C14orf38 | 1.00 | 10927 | 3 | | C1orf140 | 1.00 |
| 10832 | 3 | | | | C14orf39 | 1.00 | 10928 | 3 | | C1orf141 | 1.00 |
| 10833 | 3 | | | | C14orf55 | 1.00 | 10929 | 3 | | C1orf146 | 1.00 |
| 10834 | 3 | | | | C14orf79 | 1.00 | 10930 | 3 | | C1orf158 | 1.00 |
| 10835 | 3 | | | | C15orf2 | 1.00 | 10931 | 3 | | C1orf168 | 1.00 |
| 10836 | 3 | | | | C15orf26 | 1.00 | 10932 | 3 | | C1orf170 | 1.00 |
| 10837 | 3 | | | | C15orf27 | 1.00 | 10933 | 3 | | C1orf173 | 1.00 |
| 10838 | 3 | | | | C15orf32 | 1.00 | 10934 | 3 | | C1orf177 | 1.00 |
| 10839 | 3 | | | | C15orf33 | 1.00 | 10935 | 3 | | C1orf180 | 1.00 |
| 10840 | 3 | | | | C15orf42 | 1.00 | 10936 | 3 | | C1orf182 | 1.00 |
| 10841 | 3 | | | | C15orf43 | 1.00 | 10937 | 3 | | C1orf185 | 1.00 |
| 10842 | 3 | | | | C15orf48 | 1.00 | 10938 | 3 | | C1orf187 | 1.00 |

Fig. 40 - 58

| | | | | | | | | | | | | | |
|---|---|---|---|---|---|---|---|---|---|---|---|---|---|
| 10939 | 3 | | | | | C1orf189 | 1.00 | 11035 | 3 | | | C3orf45 | 1.00 |
| 10940 | 3 | | | | | C1orf194 | 1.00 | 11036 | 3 | | | C3orf49 | 1.00 |
| 10941 | 3 | | | | | C1orf210 | 1.00 | 11037 | 3 | | | C3orf51 | 1.00 |
| 10942 | 3 | | | | | C1orf226 | 1.00 | 11038 | 3 | | | C3orf52 | 1.00 |
| 10943 | 3 | | | | | C1orf227 | 1.00 | 11039 | 3 | | | C3orf55 | 1.00 |
| 10944 | 3 | | | | | C1orf229 | 1.00 | 11040 | 3 | | | C3orf65 | 1.00 |
| 10945 | 3 | | | | | C1orf49 | 1.00 | 11041 | 3 | | | C3orf67 | 1.00 |
| 10946 | 3 | | | | | C1orf51 | 1.00 | 11042 | 3 | | | C3orf70 | 1.00 |
| 10947 | 3 | | | | | C1orf53 | 1.00 | 11043 | 3 | | | C3orf72 | 1.00 |
| 10948 | 3 | | | | | C1orf54 | 1.00 | 11044 | 3 | | | C3orf74 | 1.00 |
| 10949 | 3 | | | | | C1orf61 | 1.00 | 11045 | 3 | | | C3orf77 | 1.00 |
| 10950 | 3 | | | | | C1orf64 | 1.00 | 11046 | 3 | | | C3orf79 | 1.00 |
| 10951 | 3 | | | | | C1orf65 | 1.00 | 11047 | 3 | | | C3orf80 | 1.00 |
| 10952 | 3 | | | | | C1orf68 | 1.00 | 11048 | 3 | | | C4B | 1.00 |
| 10953 | 3 | | | | | C1orf87 | 1.00 | 11049 | 3 | | | C4BPB | 1.00 |
| 10954 | 3 | | | | | C1orf88 | 1.00 | 11050 | 3 | | | C4orf17 | 1.00 |
| 10955 | 3 | | | | | C1orf94 | 1.00 | 11051 | 3 | | | C4orf19 | 1.00 |
| 10956 | 3 | | | | | C1orf95 | 1.00 | 11052 | 3 | | | C4orf21 | 1.00 |
| 10957 | 3 | | | | | C1orf98 | 1.00 | 11053 | 3 | | | C4orf22 | 1.00 |
| 10958 | 3 | | | | | C20orf123 | 1.00 | 11054 | 3 | | | C4orf26 | 1.00 |
| 10959 | 3 | | | | | C20orf132 | 1.00 | 11055 | 3 | | | C4orf36 | 1.00 |
| 10960 | 3 | | | | | C20orf141 | 1.00 | 11056 | 3 | | | C4orf37 | 1.00 |
| 10961 | 3 | | | | | C20orf144 | 1.00 | 11057 | 3 | | | C4orf38 | 1.00 |
| 10962 | 3 | | | | | C20orf151 | 1.00 | 11058 | 3 | | | C4orf39 | 1.00 |
| 10963 | 3 | | | | | C20orf152 | 1.00 | 11059 | 3 | | | C4orf40 | 1.00 |
| 10964 | 3 | | | | | C20orf160 | 1.00 | 11060 | 3 | | | C4orf44 | 1.00 |
| 10965 | 3 | | | | | C20orf166 | 1.00 | 11061 | 3 | | | C4orf45 | 1.00 |
| 10966 | 3 | | | | | C20orf166-AS1 | 1.00 | 11062 | 3 | | | C4orf47 | 1.00 |
| 10967 | 3 | | | | | C20orf173 | 1.00 | 11063 | 3 | | | C4orf49 | 1.00 |
| 10968 | 3 | | | | | C20orf195 | 1.00 | 11064 | 3 | | | C4orf51 | 1.00 |
| 10969 | 3 | | | | | C20orf201 | 1.00 | 11065 | 3 | | | C4orf6 | 1.00 |
| 10970 | 3 | | | | | C20orf202 | 1.00 | 11066 | 3 | | | C5orf27 | 1.00 |
| 10971 | 3 | | | | | C20orf203 | 1.00 | 11067 | 3 | | | C5orf34 | 1.00 |
| 10972 | 3 | | | | | C20orf26 | 1.00 | 11068 | 3 | | | C5orf38 | 1.00 |
| 10973 | 3 | | | | | C20orf54 | 1.00 | 11069 | 3 | | | C5orf42 | 1.00 |
| 10974 | 3 | | | | | C20orf7 | 1.00 | 11070 | 3 | | | C5orf45 | 1.00 |
| 10975 | 3 | | | | | C20orf79 | 1.00 | 11071 | 3 | | | C5orf46 | 1.00 |
| 10976 | 3 | | | | | C20orf85 | 1.00 | 11072 | 3 | | | C5orf47 | 1.00 |
| 10977 | 3 | | | | | C21orf128 | 1.00 | 11073 | 3 | | | C5orf48 | 1.00 |
| 10978 | 3 | | | | | C21orf37 | 1.00 | 11074 | 3 | | | C5orf49 | 1.00 |
| 10979 | 3 | | | | | C21orf54 | 1.00 | 11075 | 3 | | | C5orf52 | 1.00 |
| 10980 | 3 | | | | | C21orf62 | 1.00 | 11076 | 3 | | | C5orf54 | 1.00 |
| 10981 | 3 | | | | | C21orf88 | 1.00 | 11077 | 3 | | | C5orf58 | 1.00 |
| 10982 | 3 | | | | | C21orf90 | 1.00 | 11078 | 3 | | | C5orf60 | 1.00 |
| 10983 | 3 | | | | | C21orf91-OT1 | 1.00 | 11079 | 3 | | | C5orf64 | 1.00 |
| 10984 | 3 | | | | | C22orf15 | 1.00 | 11080 | 3 | | | C5orf65 | 1.00 |
| 10985 | 3 | | | | | C22orf24 | 1.00 | 11081 | 3 | | | C6 | 1.00 |
| 10986 | 3 | | | | | C22orf26 | 1.00 | 11082 | 3 | | | C6orf10 | 1.00 |
| 10987 | 3 | | | | | C22orf31 | 1.00 | 11083 | 3 | | | C6orf118 | 1.00 |
| 10988 | 3 | | | | | C22orf42 | 1.00 | 11084 | 3 | | | C6orf123 | 1.00 |
| 10989 | 3 | | | | | C22orf43 | 1.00 | 11085 | 3 | | | C6orf132 | 1.00 |
| 10990 | 3 | | | | | C22orf45 | 1.00 | 11086 | 3 | | | C6orf141 | 1.00 |
| 10991 | 3 | | | | | C2CD4A | 1.00 | 11087 | 3 | | | C6orf147 | 1.00 |
| 10992 | 3 | | | | | C2CD4B | 1.00 | 11088 | 3 | | | C6orf15 | 1.00 |
| 10993 | 3 | | | | | C2CD4C | 1.00 | 11089 | 3 | | | C6orf163 | 1.00 |
| 10994 | 3 | | | | | C2CD4D | 1.00 | 11090 | 3 | | | C6orf164 | 1.00 |
| 10995 | 3 | | | | | C2orf16 | 1.00 | 11091 | 3 | | | C6orf165 | 1.00 |
| 10996 | 3 | | | | | C2orf27A | 1.00 | 11092 | 3 | | | C6orf170 | 1.00 |
| 10997 | 3 | | | | | C2orf27B | 1.00 | 11093 | 3 | | | C6orf174 | 1.00 |
| 10998 | 3 | | | | | C2orf40 | 1.00 | 11094 | 3 | | | C6orf195 | 1.00 |
| 10999 | 3 | | | | | C2orf48 | 1.00 | 11095 | 3 | | | C6orf201 | 1.00 |
| 11000 | 3 | | | | | C2orf50 | 1.00 | 11096 | 3 | | | C6orf221 | 1.00 |
| 11001 | 3 | | | | | C2orf51 | 1.00 | 11097 | 3 | | | C6orf222 | 1.00 |
| 11002 | 3 | | | | | C2orf53 | 1.00 | 11098 | 3 | | | C6orf223 | 1.00 |
| 11003 | 3 | | | | | C2orf54 | 1.00 | 11099 | 3 | | | C6orf225 | 1.00 |
| 11004 | 3 | | | | | C2orf57 | 1.00 | 11100 | 3 | | | C6orf52 | 1.00 |
| 11005 | 3 | | | | | C2orf61 | 1.00 | 11101 | 3 | | | C6orf58 | 1.00 |
| 11006 | 3 | | | | | C2orf62 | 1.00 | 11102 | 3 | | | C6orf7 | 1.00 |
| 11007 | 3 | | | | | C2orf63 | 1.00 | 11103 | 3 | | | C6orf99 | 1.00 |
| 11008 | 3 | | | | | C2orf65 | 1.00 | 11104 | 3 | | | C7 | 1.00 |
| 11009 | 3 | | | | | C2orf66 | 1.00 | 11105 | 3 | | | C7orf10 | 1.00 |
| 11010 | 3 | | | | | C2orf70 | 1.00 | 11106 | 3 | | | C7orf33 | 1.00 |
| 11011 | 3 | | | | | C2orf71 | 1.00 | 11107 | 3 | | | C7orf45 | 1.00 |
| 11012 | 3 | | | | | C2orf72 | 1.00 | 11108 | 3 | | | C7orf57 | 1.00 |
| 11013 | 3 | | | | | C2orf73 | 1.00 | 11109 | 3 | | | C7orf62 | 1.00 |
| 11014 | 3 | | | | | C2orf76 | 1.00 | 11110 | 3 | | | C7orf63 | 1.00 |
| 11015 | 3 | | | | | C2orf77 | 1.00 | 11111 | 3 | | | C7orf65 | 1.00 |
| 11016 | 3 | | | | | C2orf78 | 1.00 | 11112 | 3 | | | C7orf66 | 1.00 |
| 11017 | 3 | | | | | C2orf80 | 1.00 | 11113 | 3 | | | C7orf69 | 1.00 |
| 11018 | 3 | | | | | C2orf82 | 1.00 | 11114 | 3 | | | C7orf71 | 1.00 |
| 11019 | 3 | | | | | C2orf83 | 1.00 | 11115 | 3 | | | C7orf72 | 1.00 |
| 11020 | 3 | | | | | C2orf84 | 1.00 | 11116 | 3 | | | C8A | 1.00 |
| 11021 | 3 | | | | | C2orf91 | 1.00 | 11117 | 3 | | | C8B | 1.00 |
| 11022 | 3 | | | | | C3 | 1.00 | 11118 | 3 | | | C8G | 1.00 |
| 11023 | 3 | | | | | C3P1 | 1.00 | 11119 | 3 | | | C8ORFK29 | 1.00 |
| 11024 | 3 | | | | | C3orf15 | 1.00 | 11120 | 3 | | | C8orf12 | 1.00 |
| 11025 | 3 | | | | | C3orf20 | 1.00 | 11121 | 3 | | | C8orf22 | 1.00 |
| 11026 | 3 | | | | | C3orf22 | 1.00 | 11122 | 3 | | | C8orf31 | 1.00 |
| 11027 | 3 | | | | | C3orf24 | 1.00 | 11123 | 3 | | | C8orf34 | 1.00 |
| 11028 | 3 | | | | | C3orf27 | 1.00 | 11124 | 3 | | | C8orf38 | 1.00 |
| 11029 | 3 | | | | | C3orf30 | 1.00 | 11125 | 3 | | | C8orf4 | 1.00 |
| 11030 | 3 | | | | | C3orf32 | 1.00 | 11126 | 3 | | | C8orf45 | 1.00 |
| 11031 | 3 | | | | | C3orf33 | 1.00 | 11127 | 3 | | | C8orf46 | 1.00 |
| 11032 | 3 | | | | | C3orf35 | 1.00 | 11128 | 3 | | | C8orf47 | 1.00 |
| 11033 | 3 | | | | | C3orf36 | 1.00 | 11129 | 3 | | | C8orf48 | 1.00 |
| 11034 | 3 | | | | | C3orf43 | 1.00 | 11130 | 3 | | | C8orf51 | 1.00 |

Fig. 40 - 59

| | | | | | | | | | | | | | | | |
|---|---|---|---|---|---|---|---|---|---|---|---|---|---|---|---|
| 11131 | 3 | | | | | | C8orf56 | 1.00 | 11227 | 3 | | | | CALML6 | 1.00 |
| 11132 | 3 | | | | | | C8orf69 | 1.00 | 11228 | 3 | | | | CALN1 | 1.00 |
| 11133 | 3 | | | | | | C8orf71 | 1.00 | 11229 | 3 | | | | CALR3 | 1.00 |
| 11134 | 3 | | | | | | C8orf74 | 1.00 | 11230 | 3 | | | | CALY | 1.00 |
| 11135 | 3 | | | | | | C8orf75 | 1.00 | 11231 | 3 | | | | CAMK1G | 1.00 |
| 11136 | 3 | | | | | | C8orf77 | 1.00 | 11232 | 3 | | | | CAMK2A | 1.00 |
| 11137 | 3 | | | | | | C8orf80 | 1.00 | 11233 | 3 | | | | CAMK2B | 1.00 |
| 11138 | 3 | | | | | | C8orf84 | 1.00 | 11234 | 3 | | | | CAMK2N1 | 1.00 |
| 11139 | 3 | | | | | | C8orf85 | 1.00 | 11235 | 3 | | | | CAMK2N2 | 1.00 |
| 11140 | 3 | | | | | | C8orf86 | 1.00 | 11236 | 3 | | | | CAMKV | 1.00 |
| 11141 | 3 | | | | | | C8orf87 | 1.00 | 11237 | 3 | | | | CAMSAP3 | 1.00 |
| 11142 | 3 | | | | | | C9 | 1.00 | 11238 | 3 | | | | CAND2 | 1.00 |
| 11143 | 3 | | | | | | C9orf106 | 1.00 | 11239 | 3 | | | | CAP2 | 1.00 |
| 11144 | 3 | | | | | | C9orf11 | 1.00 | 11240 | 3 | | | | CAPN11 | 1.00 |
| 11145 | 3 | | | | | | C9orf116 | 1.00 | 11241 | 3 | | | | CAPN13 | 1.00 |
| 11146 | 3 | | | | | | C9orf117 | 1.00 | 11242 | 3 | | | | CAPN14 | 1.00 |
| 11147 | 3 | | | | | | C9orf125 | 1.00 | 11243 | 3 | | | | CAPN6 | 1.00 |
| 11148 | 3 | | | | | | C9orf128 | 1.00 | 11244 | 3 | | | | CAPN8 | 1.00 |
| 11149 | 3 | | | | | | C9orf131 | 1.00 | 11245 | 3 | | | | CAPN9 | 1.00 |
| 11150 | 3 | | | | | | C9orf135 | 1.00 | 11246 | 3 | | | | CAPNS2 | 1.00 |
| 11151 | 3 | | | | | | C9orf146 | 1.00 | 11247 | 3 | | | | CAPS2 | 1.00 |
| 11152 | 3 | | | | | | C9orf152 | 1.00 | 11248 | 3 | | | | CAPSL | 1.00 |
| 11153 | 3 | | | | | | C9orf153 | 1.00 | 11249 | 3 | | | | CAPZA3 | 1.00 |
| 11154 | 3 | | | | | | C9orf163 | 1.00 | 11250 | 3 | | | | CARD10 | 1.00 |
| 11155 | 3 | | | | | | C9orf169 | 1.00 | 11251 | 3 | | | | CARD18 | 1.00 |
| 11156 | 3 | | | | | | C9orf170 | 1.00 | 11252 | 3 | | | | CARTPT | 1.00 |
| 11157 | 3 | | | | | | C9orf171 | 1.00 | 11253 | 3 | | | | CASC1 | 1.00 |
| 11158 | 3 | | | | | | C9orf173 | 1.00 | 11254 | 3 | | | | CASC2 | 1.00 |
| 11159 | 3 | | | | | | C9orf174 | 1.00 | 11255 | 3 | | | | CASC5 | 1.00 |
| 11160 | 3 | | | | | | C9orf24 | 1.00 | 11256 | 3 | | | | CASKIN1 | 1.00 |
| 11161 | 3 | | | | | | C9orf29 | 1.00 | 11257 | 3 | | | | CASKIN2 | 1.00 |
| 11162 | 3 | | | | | | C9orf30-TMEFF1 | 1.00 | 11258 | 3 | | | | CASP12 | 1.00 |
| 11163 | 3 | | | | | | C9orf4 | 1.00 | 11259 | 3 | | | | CASP14 | 1.00 |
| 11164 | 3 | | | | | | C9orf43 | 1.00 | 11260 | 3 | | | | CASQ1 | 1.00 |
| 11165 | 3 | | | | | | C9orf47 | 1.00 | 11261 | 3 | | | | CASQ2 | 1.00 |
| 11166 | 3 | | | | | | C9orf50 | 1.00 | 11262 | 3 | | | | CASR | 1.00 |
| 11167 | 3 | | | | | | C9orf53 | 1.00 | 11263 | 3 | | | | CATSPER1 | 1.00 |
| 11168 | 3 | | | | | | C9orf57 | 1.00 | 11264 | 3 | | | | CATSPER2 | 1.00 |
| 11169 | 3 | | | | | | C9orf68 | 1.00 | 11265 | 3 | | | | CATSPER2P1 | 1.00 |
| 11170 | 3 | | | | | | C9orf79 | 1.00 | 11266 | 3 | | | | CATSPER3 | 1.00 |
| 11171 | 3 | | | | | | C9orf84 | 1.00 | 11267 | 3 | | | | CATSPER4 | 1.00 |
| 11172 | 3 | | | | | | C9orf9 | 1.00 | 11268 | 3 | | | | CATSPERB | 1.00 |
| 11173 | 3 | | | | | | C9orf93 | 1.00 | 11269 | 3 | | | | CATSPERD | 1.00 |
| 11174 | 3 | | | | | | C9orf96 | 1.00 | 11270 | 3 | | | | CATSPERG | 1.00 |
| 11175 | 3 | | | | | | CA10 | 1.00 | 11271 | 3 | | | | CAV3 | 1.00 |
| 11176 | 3 | | | | | | CA12 | 1.00 | 11272 | 3 | | | | CBLC | 1.00 |
| 11177 | 3 | | | | | | CA14 | 1.00 | 11273 | 3 | | | | CBLN1 | 1.00 |
| 11178 | 3 | | | | | | CA3 | 1.00 | 11274 | 3 | | | | CBLN2 | 1.00 |
| 11179 | 3 | | | | | | CA5A | 1.00 | 11275 | 3 | | | | CBLN4 | 1.00 |
| 11180 | 3 | | | | | | CA6 | 1.00 | 11276 | 3 | | | | CBX2 | 1.00 |
| 11181 | 3 | | | | | | CA7 | 1.00 | 11277 | 3 | | | | CBY3 | 1.00 |
| 11182 | 3 | | | | | | CA8 | 1.00 | 11278 | 3 | | | | CC2D2A | 1.00 |
| 11183 | 3 | | | | | | CA9 | 1.00 | 11279 | 3 | | | | CC2D2B | 1.00 |
| 11184 | 3 | | | | | | CABLES1 | 1.00 | 11280 | 3 | | | | CCBE1 | 1.00 |
| 11185 | 3 | | | | | | CABP1 | 1.00 | 11281 | 3 | | | | CCBP2 | 1.00 |
| 11186 | 3 | | | | | | CABP2 | 1.00 | 11282 | 3 | | | | CCDC102B | 1.00 |
| 11187 | 3 | | | | | | CABP4 | 1.00 | 11283 | 3 | | | | CCDC103 | 1.00 |
| 11188 | 3 | | | | | | CABP7 | 1.00 | 11284 | 3 | | | | CCDC105 | 1.00 |
| 11189 | 3 | | | | | | CABS1 | 1.00 | 11285 | 3 | | | | CCDC108 | 1.00 |
| 11190 | 3 | | | | | | CABYR | 1.00 | 11286 | 3 | | | | CCDC11 | 1.00 |
| 11191 | 3 | | | | | | CACHD1 | 1.00 | 11287 | 3 | | | | CCDC110 | 1.00 |
| 11192 | 3 | | | | | | CACNA1B | 1.00 | 11288 | 3 | | | | CCDC113 | 1.00 |
| 11193 | 3 | | | | | | CACNA1C | 1.00 | 11289 | 3 | | | | CCDC114 | 1.00 |
| 11194 | 3 | | | | | | CACNA1D | 1.00 | 11290 | 3 | | | | CCDC116 | 1.00 |
| 11195 | 3 | | | | | | CACNA1E | 1.00 | 11291 | 3 | | | | CCDC129 | 1.00 |
| 11196 | 3 | | | | | | CACNA1F | 1.00 | 11292 | 3 | | | | CCDC13 | 1.00 |
| 11197 | 3 | | | | | | CACNA1G | 1.00 | 11293 | 3 | | | | CCDC135 | 1.00 |
| 11198 | 3 | | | | | | CACNA1H | 1.00 | 11294 | 3 | | | | CCDC136 | 1.00 |
| 11199 | 3 | | | | | | CACNA1S | 1.00 | 11295 | 3 | | | | CCDC138 | 1.00 |
| 11200 | 3 | | | | | | CACNA2D1 | 1.00 | 11296 | 3 | | | | CCDC140 | 1.00 |
| 11201 | 3 | | | | | | CACNA2D3 | 1.00 | 11297 | 3 | | | | CCDC141 | 1.00 |
| 11202 | 3 | | | | | | CACNB2 | 1.00 | 11298 | 3 | | | | CCDC144A | 1.00 |
| 11203 | 3 | | | | | | CACNB3 | 1.00 | 11299 | 3 | | | | CCDC144B | 1.00 |
| 11204 | 3 | | | | | | CACNG1 | 1.00 | 11300 | 3 | | | | CCDC144C | 1.00 |
| 11205 | 3 | | | | | | CACNG2 | 1.00 | 11301 | 3 | | | | CCDC144NL | 1.00 |
| 11206 | 3 | | | | | | CACNG3 | 1.00 | 11302 | 3 | | | | CCDC148 | 1.00 |
| 11207 | 3 | | | | | | CACNG4 | 1.00 | 11303 | 3 | | | | CCDC15 | 1.00 |
| 11208 | 3 | | | | | | CACNG5 | 1.00 | 11304 | 3 | | | | CCDC150 | 1.00 |
| 11209 | 3 | | | | | | CACNG7 | 1.00 | 11305 | 3 | | | | CCDC151 | 1.00 |
| 11210 | 3 | | | | | | CACNG8 | 1.00 | 11306 | 3 | | | | CCDC154 | 1.00 |
| 11211 | 3 | | | | | | CADM1 | 1.00 | 11307 | 3 | | | | CCDC155 | 1.00 |
| 11212 | 3 | | | | | | CADM2 | 1.00 | 11308 | 3 | | | | CCDC157 | 1.00 |
| 11213 | 3 | | | | | | CADM3 | 1.00 | 11309 | 3 | | | | CCDC158 | 1.00 |
| 11214 | 3 | | | | | | CADPS | 1.00 | 11310 | 3 | | | | CCDC160 | 1.00 |
| 11215 | 3 | | | | | | CADPS2 | 1.00 | 11311 | 3 | | | | CCDC162P | 1.00 |
| 11216 | 3 | | | | | | CAGE1 | 1.00 | 11312 | 3 | | | | CCDC164 | 1.00 |
| 11217 | 3 | | | | | | CALB1 | 1.00 | 11313 | 3 | | | | CCDC165 | 1.00 |
| 11218 | 3 | | | | | | CALB2 | 1.00 | 11314 | 3 | | | | CCDC166 | 1.00 |
| 11219 | 3 | | | | | | CALCA | 1.00 | 11315 | 3 | | | | CCDC168 | 1.00 |
| 11220 | 3 | | | | | | CALCB | 1.00 | 11316 | 3 | | | | CCDC169 | 1.00 |
| 11221 | 3 | | | | | | CALCR | 1.00 | 11317 | 3 | | | | CCDC169-SOHLH2 | 1.00 |
| 11222 | 3 | | | | | | CALCRL | 1.00 | 11318 | 3 | | | | CCDC27 | 1.00 |
| 11223 | 3 | | | | | | CALHM1 | 1.00 | 11319 | 3 | | | | CCDC3 | 1.00 |
| 11224 | 3 | | | | | | CALHM3 | 1.00 | 11320 | 3 | | | | CCDC30 | 1.00 |
| 11225 | 3 | | | | | | CALML3 | 1.00 | 11321 | 3 | | | | CCDC33 | 1.00 |
| 11226 | 3 | | | | | | CALML5 | 1.00 | 11322 | 3 | | | | CCDC36 | 1.00 |

Fig. 40 - 60

| | | | | | | | | | | | | | | | | |
|---|---|---|---|---|---|---|---|---|---|---|---|---|---|---|---|---|
| 11323 | 3 | | | | | | CCDC37 | 1.00 | 11419 | 3 | | | | | CDH2 | 1.00 |
| 11324 | 3 | | | | | | CCDC38 | 1.00 | 11420 | 3 | | | | | CDH20 | 1.00 |
| 11325 | 3 | | | | | | CCDC40 | 1.00 | 11421 | 3 | | | | | CDH22 | 1.00 |
| 11326 | 3 | | | | | | CCDC41 | 1.00 | 11422 | 3 | | | | | CDH24 | 1.00 |
| 11327 | 3 | | | | | | CCDC42 | 1.00 | 11423 | 3 | | | | | CDH26 | 1.00 |
| 11328 | 3 | | | | | | CCDC48 | 1.00 | 11424 | 3 | | | | | CDH3 | 1.00 |
| 11329 | 3 | | | | | | CCDC54 | 1.00 | 11425 | 3 | | | | | CDH4 | 1.00 |
| 11330 | 3 | | | | | | CCDC60 | 1.00 | 11426 | 3 | | | | | CDH5 | 1.00 |
| 11331 | 3 | | | | | | CCDC62 | 1.00 | 11427 | 3 | | | | | CDH6 | 1.00 |
| 11332 | 3 | | | | | | CCDC63 | 1.00 | 11428 | 3 | | | | | CDH7 | 1.00 |
| 11333 | 3 | | | | | | CCDC64B | 1.00 | 11429 | 3 | | | | | CDH8 | 1.00 |
| 11334 | 3 | | | | | | CCDC67 | 1.00 | 11430 | 3 | | | | | CDH9 | 1.00 |
| 11335 | 3 | | | | | | CCDC68 | 1.00 | 11431 | 3 | | | | | CDHR1 | 1.00 |
| 11336 | 3 | | | | | | CCDC7 | 1.00 | 11432 | 3 | | | | | CDHR2 | 1.00 |
| 11337 | 3 | | | | | | CCDC70 | 1.00 | 11433 | 3 | | | | | CDHR3 | 1.00 |
| 11338 | 3 | | | | | | CCDC73 | 1.00 | 11434 | 3 | | | | | CDHR4 | 1.00 |
| 11339 | 3 | | | | | | CCDC74A | 1.00 | 11435 | 3 | | | | | CDHR5 | 1.00 |
| 11340 | 3 | | | | | | CCDC74B | 1.00 | 11436 | 3 | | | | | CDK1 | 1.00 |
| 11341 | 3 | | | | | | CCDC78 | 1.00 | 11437 | 3 | | | | | CDK15 | 1.00 |
| 11342 | 3 | | | | | | CCDC79 | 1.00 | 11438 | 3 | | | | | CDK5R2 | 1.00 |
| 11343 | 3 | | | | | | CCDC8 | 1.00 | 11439 | 3 | | | | | CDKL2 | 1.00 |
| 11344 | 3 | | | | | | CCDC80 | 1.00 | 11440 | 3 | | | | | CDKL3 | 1.00 |
| 11345 | 3 | | | | | | CCDC81 | 1.00 | 11441 | 3 | | | | | CDKL4 | 1.00 |
| 11346 | 3 | | | | | | CCDC83 | 1.00 | 11442 | 3 | | | | | CDKN2B-AS1 | 1.00 |
| 11347 | 3 | | | | | | CCDC85A | 1.00 | 11443 | 3 | | | | | CDKN3 | 1.00 |
| 11348 | 3 | | | | | | CCDC87 | 1.00 | 11444 | 3 | | | | | CDNF | 1.00 |
| 11349 | 3 | | | | | | CCDC89 | 1.00 | 11445 | 3 | | | | | CDO1 | 1.00 |
| 11350 | 3 | | | | | | CCIN | 1.00 | 11446 | 3 | | | | | CDON | 1.00 |
| 11351 | 3 | | | | | | CCK | 1.00 | 11447 | 3 | | | | | CDR1 | 1.00 |
| 11352 | 3 | | | | | | CCKAR | 1.00 | 11448 | 3 | | | | | CDR2L | 1.00 |
| 11353 | 3 | | | | | | CCKBR | 1.00 | 11449 | 3 | | | | | CDRT1 | 1.00 |
| 11354 | 3 | | | | | | CCL1 | 1.00 | 11450 | 3 | | | | | CDRT15 | 1.00 |
| 11355 | 3 | | | | | | CCL11 | 1.00 | 11451 | 3 | | | | | CDRT15L2 | 1.00 |
| 11356 | 3 | | | | | | CCL13 | 1.00 | 11452 | 3 | | | | | CDRT15P2 | 1.00 |
| 11357 | 3 | | | | | | CCL14 | 1.00 | 11453 | 3 | | | | | CDRT7 | 1.00 |
| 11358 | 3 | | | | | | CCL14-CCL15 | 1.00 | 11454 | 3 | | | | | CDS1 | 1.00 |
| 11359 | 3 | | | | | | CCL15 | 1.00 | 11455 | 3 | | | | | CDSN | 1.00 |
| 11360 | 3 | | | | | | CCL16 | 1.00 | 11456 | 3 | | | | | CDT1 | 1.00 |
| 11361 | 3 | | | | | | CCL17 | 1.00 | 11457 | 3 | | | | | CDX1 | 1.00 |
| 11362 | 3 | | | | | | CCL18 | 1.00 | 11458 | 3 | | | | | CDX2 | 1.00 |
| 11363 | 3 | | | | | | CCL19 | 1.00 | 11459 | 3 | | | | | CDX4 | 1.00 |
| 11364 | 3 | | | | | | CCL20 | 1.00 | 11460 | 3 | | | | | CDY1 | 1.00 |
| 11365 | 3 | | | | | | CCL21 | 1.00 | 11461 | 3 | | | | | CDY1B | 1.00 |
| 11366 | 3 | | | | | | CCL22 | 1.00 | 11462 | 3 | | | | | CDY2A | 1.00 |
| 11367 | 3 | | | | | | CCL24 | 1.00 | 11463 | 3 | | | | | CDY2B | 1.00 |
| 11368 | 3 | | | | | | CCL25 | 1.00 | 11464 | 3 | | | | | CEACAM16 | 1.00 |
| 11369 | 3 | | | | | | CCL26 | 1.00 | 11465 | 3 | | | | | CEACAM18 | 1.00 |
| 11370 | 3 | | | | | | CCL27 | 1.00 | 11466 | 3 | | | | | CEACAM20 | 1.00 |
| 11371 | 3 | | | | | | CCL3L1 | 1.00 | 11467 | 3 | | | | | CEACAM22P | 1.00 |
| 11372 | 3 | | | | | | CCL7 | 1.00 | 11468 | 3 | | | | | CEACAM5 | 1.00 |
| 11373 | 3 | | | | | | CCL8 | 1.00 | 11469 | 3 | | | | | CEACAM6 | 1.00 |
| 11374 | 3 | | | | | | CCNA1 | 1.00 | 11470 | 3 | | | | | CEACAM7 | 1.00 |
| 11375 | 3 | | | | | | CCNB1 | 1.00 | 11471 | 3 | | | | | CECR2 | 1.00 |
| 11376 | 3 | | | | | | CCNB3 | 1.00 | 11472 | 3 | | | | | CECR3 | 1.00 |
| 11377 | 3 | | | | | | CCNE2 | 1.00 | 11473 | 3 | | | | | CECR5-AS1 | 1.00 |
| 11378 | 3 | | | | | | CCNI2 | 1.00 | 11474 | 3 | | | | | CECR7 | 1.00 |
| 11379 | 3 | | | | | | CCNO | 1.00 | 11475 | 3 | | | | | CEL | 1.00 |
| 11380 | 3 | | | | | | CCRL1 | 1.00 | 11476 | 3 | | | | | CELA1 | 1.00 |
| 11381 | 3 | | | | | | CCT6B | 1.00 | 11477 | 3 | | | | | CELA2A | 1.00 |
| 11382 | 3 | | | | | | CCT8L2 | 1.00 | 11478 | 3 | | | | | CELA2B | 1.00 |
| 11383 | 3 | | | | | | CD109 | 1.00 | 11479 | 3 | | | | | CELA3A | 1.00 |
| 11384 | 3 | | | | | | CD163L1 | 1.00 | 11480 | 3 | | | | | CELA3B | 1.00 |
| 11385 | 3 | | | | | | CD164L2 | 1.00 | 11481 | 3 | | | | | CELF3 | 1.00 |
| 11386 | 3 | | | | | | CD1B | 1.00 | 11482 | 3 | | | | | CELF4 | 1.00 |
| 11387 | 3 | | | | | | CD1E | 1.00 | 11483 | 3 | | | | | CELF5 | 1.00 |
| 11388 | 3 | | | | | | CD200R1L | 1.00 | 11484 | 3 | | | | | CELP | 1.00 |
| 11389 | 3 | | | | | | CD207 | 1.00 | 11485 | 3 | | | | | CELSR1 | 1.00 |
| 11390 | 3 | | | | | | CD276 | 1.00 | 11486 | 3 | | | | | CELSR2 | 1.00 |
| 11391 | 3 | | | | | | CD300LG | 1.00 | 11487 | 3 | | | | | CELSR3 | 1.00 |
| 11392 | 3 | | | | | | CD34 | 1.00 | 11488 | 3 | | | | | CEND1 | 1.00 |
| 11393 | 3 | | | | | | CD5L | 1.00 | 11489 | 3 | | | | | CENPA | 1.00 |
| 11394 | 3 | | | | | | CD80 | 1.00 | 11490 | 3 | | | | | CENPE | 1.00 |
| 11395 | 3 | | | | | | CDC20B | 1.00 | 11491 | 3 | | | | | CENPI | 1.00 |
| 11396 | 3 | | | | | | CDC25A | 1.00 | 11492 | 3 | | | | | CENPP | 1.00 |
| 11397 | 3 | | | | | | CDC25C | 1.00 | 11493 | 3 | | | | | CENPQ | 1.00 |
| 11398 | 3 | | | | | | CDC42BPA | 1.00 | 11494 | 3 | | | | | CENPVL1 | 1.00 |
| 11399 | 3 | | | | | | CDC42BPG | 1.00 | 11495 | 3 | | | | | CEP112 | 1.00 |
| 11400 | 3 | | | | | | CDC42EP5 | 1.00 | 11496 | 3 | | | | | CEP128 | 1.00 |
| 11401 | 3 | | | | | | CDC45 | 1.00 | 11497 | 3 | | | | | CEP55 | 1.00 |
| 11402 | 3 | | | | | | CDC6 | 1.00 | 11498 | 3 | | | | | CEP70 | 1.00 |
| 11403 | 3 | | | | | | CDCA2 | 1.00 | 11499 | 3 | | | | | CEP72 | 1.00 |
| 11404 | 3 | | | | | | CDCA3 | 1.00 | 11500 | 3 | | | | | CEP76 | 1.00 |
| 11405 | 3 | | | | | | CDCA5 | 1.00 | 11501 | 3 | | | | | CER1 | 1.00 |
| 11406 | 3 | | | | | | CDCA8 | 1.00 | 11502 | 3 | | | | | CERCAM | 1.00 |
| 11407 | 3 | | | | | | CDCP1 | 1.00 | 11503 | 3 | | | | | CERS1 | 1.00 |
| 11408 | 3 | | | | | | CDCP2 | 1.00 | 11504 | 3 | | | | | CERS3 | 1.00 |
| 11409 | 3 | | | | | | CDH1 | 1.00 | 11505 | 3 | | | | | CES1P1 | 1.00 |
| 11410 | 3 | | | | | | CDH10 | 1.00 | 11506 | 3 | | | | | CES1P2 | 1.00 |
| 11411 | 3 | | | | | | CDH11 | 1.00 | 11507 | 3 | | | | | CES3 | 1.00 |
| 11412 | 3 | | | | | | CDH12 | 1.00 | 11508 | 3 | | | | | CES5A | 1.00 |
| 11413 | 3 | | | | | | CDH13 | 1.00 | 11509 | 3 | | | | | CES5AP1 | 1.00 |
| 11414 | 3 | | | | | | CDH15 | 1.00 | 11510 | 3 | | | | | CETN1 | 1.00 |
| 11415 | 3 | | | | | | CDH16 | 1.00 | 11511 | 3 | | | | | CETN4P | 1.00 |
| 11416 | 3 | | | | | | CDH17 | 1.00 | 11512 | 3 | | | | | CF8 | 1.00 |
| 11417 | 3 | | | | | | CDH18 | 1.00 | 11513 | 3 | | | | | CFC1 | 1.00 |
| 11418 | 3 | | | | | | CDH19 | 1.00 | 11514 | 3 | | | | | CFC1B | 1.00 |

Fig. 40 - 61

| | | | | | | | |
|---|---|---|---|---|---|---|---|
| 11515 | 3 | CFHR1 | 1.00 | 11611 | 3 | CLDN16 | 1.00 |
| 11516 | 3 | CFHR2 | 1.00 | 11612 | 3 | CLDN17 | 1.00 |
| 11517 | 3 | CFHR3 | 1.00 | 11613 | 3 | CLDN18 | 1.00 |
| 11518 | 3 | CFHR4 | 1.00 | 11614 | 3 | CLDN19 | 1.00 |
| 11519 | 3 | CFHR5 | 1.00 | 11615 | 3 | CLDN2 | 1.00 |
| 11520 | 3 | CFI | 1.00 | 11616 | 3 | CLDN20 | 1.00 |
| 11521 | 3 | CFL1P1 | 1.00 | 11617 | 3 | CLDN22 | 1.00 |
| 11522 | 3 | CFTR | 1.00 | 11618 | 3 | CLDN24 | 1.00 |
| 11523 | 3 | CGA | 1.00 | 11619 | 3 | CLDN25 | 1.00 |
| 11524 | 3 | CGB | 1.00 | 11620 | 3 | CLDN3 | 1.00 |
| 11525 | 3 | CGB1 | 1.00 | 11621 | 3 | CLDN4 | 1.00 |
| 11526 | 3 | CGB2 | 1.00 | 11622 | 3 | CLDN6 | 1.00 |
| 11527 | 3 | CGB5 | 1.00 | 11623 | 3 | CLDN8 | 1.00 |
| 11528 | 3 | CGB7 | 1.00 | 11624 | 3 | CLEC14A | 1.00 |
| 11529 | 3 | CGB8 | 1.00 | 11625 | 3 | CLEC18B | 1.00 |
| 11530 | 3 | CGN | 1.00 | 11626 | 3 | CLEC18C | 1.00 |
| 11531 | 3 | CGNL1 | 1.00 | 11627 | 3 | CLEC19A | 1.00 |
| 11532 | 3 | CGREF1 | 1.00 | 11628 | 3 | CLEC2A | 1.00 |
| 11533 | 3 | CH25H | 1.00 | 11629 | 3 | CLEC3A | 1.00 |
| 11534 | 3 | CHAC1 | 1.00 | 11630 | 3 | CLEC4F | 1.00 |
| 11535 | 3 | CHADL | 1.00 | 11631 | 3 | CLEC4GP1 | 1.00 |
| 11536 | 3 | CHAF1B | 1.00 | 11632 | 3 | CLEC4M | 1.00 |
| 11537 | 3 | CHAT | 1.00 | 11633 | 3 | CLGN | 1.00 |
| 11538 | 3 | CHCHD6 | 1.00 | 11634 | 3 | CLIC6 | 1.00 |
| 11539 | 3 | CHD5 | 1.00 | 11635 | 3 | CLIP3 | 1.00 |
| 11540 | 3 | CHDH | 1.00 | 11636 | 3 | CLLU1 | 1.00 |
| 11541 | 3 | CHEK2P2 | 1.00 | 11637 | 3 | CLLU1OS | 1.00 |
| 11542 | 3 | CHGA | 1.00 | 11638 | 3 | CLMP | 1.00 |
| 11543 | 3 | CHGB | 1.00 | 11639 | 3 | CLNK | 1.00 |
| 11544 | 3 | CHIA | 1.00 | 11640 | 3 | CLPS | 1.00 |
| 11545 | 3 | CHIT1 | 1.00 | 11641 | 3 | CLPSL1 | 1.00 |
| 11546 | 3 | CHKB-CPT1B | 1.00 | 11642 | 3 | CLPSL2 | 1.00 |
| 11547 | 3 | CHL1 | 1.00 | 11643 | 3 | CLRN1 | 1.00 |
| 11548 | 3 | CHMP4C | 1.00 | 11644 | 3 | CLRN1-AS1 | 1.00 |
| 11549 | 3 | CHODL | 1.00 | 11645 | 3 | CLRN2 | 1.00 |
| 11550 | 3 | CHODL-AS1 | 1.00 | 11646 | 3 | CLRN3 | 1.00 |
| 11551 | 3 | CHP2 | 1.00 | 11647 | 3 | CLSPN | 1.00 |
| 11552 | 3 | CHRD | 1.00 | 11648 | 3 | CLSTN2 | 1.00 |
| 11553 | 3 | CHRDL1 | 1.00 | 11649 | 3 | CLUL1 | 1.00 |
| 11554 | 3 | CHRDL2 | 1.00 | 11650 | 3 | CLVS1 | 1.00 |
| 11555 | 3 | CHRFAM7A | 1.00 | 11651 | 3 | CLVS2 | 1.00 |
| 11556 | 3 | CHRM1 | 1.00 | 11652 | 3 | CLYBL | 1.00 |
| 11557 | 3 | CHRM2 | 1.00 | 11653 | 3 | CMA1 | 1.00 |
| 11558 | 3 | CHRM3 | 1.00 | 11654 | 3 | CMYA5 | 1.00 |
| 11559 | 3 | CHRM4 | 1.00 | 11655 | 3 | CN5H6.4 | 1.00 |
| 11560 | 3 | CHRM5 | 1.00 | 11656 | 3 | CNBD1 | 1.00 |
| 11561 | 3 | CHRNA1 | 1.00 | 11657 | 3 | CNDP1 | 1.00 |
| 11562 | 3 | CHRNA2 | 1.00 | 11658 | 3 | CNGA1 | 1.00 |
| 11563 | 3 | CHRNA3 | 1.00 | 11659 | 3 | CNGA2 | 1.00 |
| 11564 | 3 | CHRNA4 | 1.00 | 11660 | 3 | CNGA3 | 1.00 |
| 11565 | 3 | CHRNA5 | 1.00 | 11661 | 3 | CNGA4 | 1.00 |
| 11566 | 3 | CHRNA6 | 1.00 | 11662 | 3 | CNGB1 | 1.00 |
| 11567 | 3 | CHRNA7 | 1.00 | 11663 | 3 | CNGB3 | 1.00 |
| 11568 | 3 | CHRNA9 | 1.00 | 11664 | 3 | CNIH2 | 1.00 |
| 11569 | 3 | CHRNB2 | 1.00 | 11665 | 3 | CNIH3 | 1.00 |
| 11570 | 3 | CHRNB3 | 1.00 | 11666 | 3 | CNKSR1 | 1.00 |
| 11571 | 3 | CHRNB4 | 1.00 | 11667 | 3 | CNKSR3 | 1.00 |
| 11572 | 3 | CHRND | 1.00 | 11668 | 3 | CNN1 | 1.00 |
| 11573 | 3 | CHRNG | 1.00 | 11669 | 3 | CNNM1 | 1.00 |
| 11574 | 3 | CHST1 | 1.00 | 11670 | 3 | CNPY1 | 1.00 |
| 11575 | 3 | CHST3 | 1.00 | 11671 | 3 | CNR1 | 1.00 |
| 11576 | 3 | CHST4 | 1.00 | 11672 | 3 | CNRIP1 | 1.00 |
| 11577 | 3 | CHST5 | 1.00 | 11673 | 3 | CNTD2 | 1.00 |
| 11578 | 3 | CHST6 | 1.00 | 11674 | 3 | CNTF | 1.00 |
| 11579 | 3 | CHST8 | 1.00 | 11675 | 3 | CNTFR | 1.00 |
| 11580 | 3 | CHST9 | 1.00 | 11676 | 3 | CNTN1 | 1.00 |
| 11581 | 3 | CHST9-AS1 | 1.00 | 11677 | 3 | CNTN2 | 1.00 |
| 11582 | 3 | CHSY3 | 1.00 | 11678 | 3 | CNTN3 | 1.00 |
| 11583 | 3 | CIB2 | 1.00 | 11679 | 3 | CNTN4 | 1.00 |
| 11584 | 3 | CIB3 | 1.00 | 11680 | 3 | CNTN5 | 1.00 |
| 11585 | 3 | CIB4 | 1.00 | 11681 | 3 | CNTN6 | 1.00 |
| 11586 | 3 | CIDEA | 1.00 | 11682 | 3 | CNTNAP4 | 1.00 |
| 11587 | 3 | CIDEC | 1.00 | 11683 | 3 | CNTNAP5 | 1.00 |
| 11588 | 3 | CILP | 1.00 | 11684 | 3 | COBL | 1.00 |
| 11589 | 3 | CILP2 | 1.00 | 11685 | 3 | COL10A1 | 1.00 |
| 11590 | 3 | CIT | 1.00 | 11686 | 3 | COL11A1 | 1.00 |
| 11591 | 3 | CITED1 | 1.00 | 11687 | 3 | COL11A2 | 1.00 |
| 11592 | 3 | CKAP2L | 1.00 | 11688 | 3 | COL12A1 | 1.00 |
| 11593 | 3 | CKLF-CMTM1 | 1.00 | 11689 | 3 | COL13A1 | 1.00 |
| 11594 | 3 | CKM | 1.00 | 11690 | 3 | COL14A1 | 1.00 |
| 11595 | 3 | CKMT1A | 1.00 | 11691 | 3 | COL15A1 | 1.00 |
| 11596 | 3 | CKMT1B | 1.00 | 11692 | 3 | COL16A1 | 1.00 |
| 11597 | 3 | CKMT2 | 1.00 | 11693 | 3 | COL17A1 | 1.00 |
| 11598 | 3 | CLCA1 | 1.00 | 11694 | 3 | COL18A1-AS1 | 1.00 |
| 11599 | 3 | CLCA2 | 1.00 | 11695 | 3 | COL1A1 | 1.00 |
| 11600 | 3 | CLCA3P | 1.00 | 11696 | 3 | COL1A2 | 1.00 |
| 11601 | 3 | CLCA4 | 1.00 | 11697 | 3 | COL20A1 | 1.00 |
| 11602 | 3 | CLCN1 | 1.00 | 11698 | 3 | COL21A1 | 1.00 |
| 11603 | 3 | CLCN2 | 1.00 | 11699 | 3 | COL22A1 | 1.00 |
| 11604 | 3 | CLCNKA | 1.00 | 11700 | 3 | COL23A1 | 1.00 |
| 11605 | 3 | CLCNKB | 1.00 | 11701 | 3 | COL24A1 | 1.00 |
| 11606 | 3 | CLDN1 | 1.00 | 11702 | 3 | COL25A1 | 1.00 |
| 11607 | 3 | CLDN10 | 1.00 | 11703 | 3 | COL27A1 | 1.00 |
| 11608 | 3 | CLDN11 | 1.00 | 11704 | 3 | COL28A1 | 1.00 |
| 11609 | 3 | CLDN12 | 1.00 | 11705 | 3 | COL2A1 | 1.00 |
| 11610 | 3 | CLDN14 | 1.00 | 11706 | 3 | COL3A1 | 1.00 |

Fig. 40 - 62

| | | | | | | | | | | | | | | |
|---|---|---|---|---|---|---|---|---|---|---|---|---|---|---|
| 11707 | 3 | | | | | COL4A1 | 1.00 | 11803 | 3 | | | | CRYGB | 1.00 |
| 11708 | 3 | | | | | COL4A2 | 1.00 | 11804 | 3 | | | | CRYGC | 1.00 |
| 11709 | 3 | | | | | COL4A3 | 1.00 | 11805 | 3 | | | | CRYGD | 1.00 |
| 11710 | 3 | | | | | COL4A4 | 1.00 | 11806 | 3 | | | | CRYGN | 1.00 |
| 11711 | 3 | | | | | COL4A5 | 1.00 | 11807 | 3 | | | | CRYM | 1.00 |
| 11712 | 3 | | | | | COL4A6 | 1.00 | 11808 | 3 | | | | CRYM-AS1 | 1.00 |
| 11713 | 3 | | | | | COL5A1 | 1.00 | 11809 | 3 | | | | CSAG1 | 1.00 |
| 11714 | 3 | | | | | COL5A2 | 1.00 | 11810 | 3 | | | | CSAG2 | 1.00 |
| 11715 | 3 | | | | | COL5A3 | 1.00 | 11811 | 3 | | | | CSAG3 | 1.00 |
| 11716 | 3 | | | | | COL6A3 | 1.00 | 11812 | 3 | | | | CSDC2 | 1.00 |
| 11717 | 3 | | | | | COL6A4P1 | 1.00 | 11813 | 3 | | | | CSF2 | 1.00 |
| 11718 | 3 | | | | | COL6A4P2 | 1.00 | 11814 | 3 | | | | CSF3 | 1.00 |
| 11719 | 3 | | | | | COL6A5 | 1.00 | 11815 | 3 | | | | CSH1 | 1.00 |
| 11720 | 3 | | | | | COL6A6 | 1.00 | 11816 | 3 | | | | CSH2 | 1.00 |
| 11721 | 3 | | | | | COL7A1 | 1.00 | 11817 | 3 | | | | CSHL1 | 1.00 |
| 11722 | 3 | | | | | COL8A1 | 1.00 | 11818 | 3 | | | | CSMD1 | 1.00 |
| 11723 | 3 | | | | | COL9A1 | 1.00 | 11819 | 3 | | | | CSMD2 | 1.00 |
| 11724 | 3 | | | | | COLEC10 | 1.00 | 11820 | 3 | | | | CSMD3 | 1.00 |
| 11725 | 3 | | | | | COLEC11 | 1.00 | 11821 | 3 | | | | CSN1S1 | 1.00 |
| 11726 | 3 | | | | | COLEC12 | 1.00 | 11822 | 3 | | | | CSN1S2AP | 1.00 |
| 11727 | 3 | | | | | COMP | 1.00 | 11823 | 3 | | | | CSN1S2BP | 1.00 |
| 11728 | 3 | | | | | COPZ2 | 1.00 | 11824 | 3 | | | | CSN2 | 1.00 |
| 11729 | 3 | | | | | CORIN | 1.00 | 11825 | 3 | | | | CSN3 | 1.00 |
| 11730 | 3 | | | | | CORO6 | 1.00 | 11826 | 3 | | | | CSNK1G2-AS1 | 1.00 |
| 11731 | 3 | | | | | CORO7-PAM16 | 1.00 | 11827 | 3 | | | | CSPG4 | 1.00 |
| 11732 | 3 | | | | | CORT | 1.00 | 11828 | 3 | | | | CSPG4P1Y | 1.00 |
| 11733 | 3 | | | | | COX4I2 | 1.00 | 11829 | 3 | | | | CSPG5 | 1.00 |
| 11734 | 3 | | | | | COX6A2 | 1.00 | 11830 | 3 | | | | CSRNP3 | 1.00 |
| 11735 | 3 | | | | | COX6B2 | 1.00 | 11831 | 3 | | | | CSRP2 | 1.00 |
| 11736 | 3 | | | | | COX7A1 | 1.00 | 11832 | 3 | | | | CSRP3 | 1.00 |
| 11737 | 3 | | | | | COX7B2 | 1.00 | 11833 | 3 | | | | CST1 | 1.00 |
| 11738 | 3 | | | | | COX8C | 1.00 | 11834 | 3 | | | | CST11 | 1.00 |
| 11739 | 3 | | | | | CP | 1.00 | 11835 | 3 | | | | CST2 | 1.00 |
| 11740 | 3 | | | | | CPA1 | 1.00 | 11836 | 3 | | | | CST4 | 1.00 |
| 11741 | 3 | | | | | CPA2 | 1.00 | 11837 | 3 | | | | CST5 | 1.00 |
| 11742 | 3 | | | | | CPA4 | 1.00 | 11838 | 3 | | | | CST6 | 1.00 |
| 11743 | 3 | | | | | CPA5 | 1.00 | 11839 | 3 | | | | CST8 | 1.00 |
| 11744 | 3 | | | | | CPA6 | 1.00 | 11840 | 3 | | | | CST9 | 1.00 |
| 11745 | 3 | | | | | CPAMD8 | 1.00 | 11841 | 3 | | | | CST9L | 1.00 |
| 11746 | 3 | | | | | CPB1 | 1.00 | 11842 | 3 | | | | CSTL1 | 1.00 |
| 11747 | 3 | | | | | CPB2 | 1.00 | 11843 | 3 | | | | CSTT | 1.00 |
| 11748 | 3 | | | | | CPE | 1.00 | 11844 | 3 | | | | CT45A1 | 1.00 |
| 11749 | 3 | | | | | CPEB1 | 1.00 | 11845 | 3 | | | | CT45A2 | 1.00 |
| 11750 | 3 | | | | | CPLX1 | 1.00 | 11846 | 3 | | | | CT45A3 | 1.00 |
| 11751 | 3 | | | | | CPLX2 | 1.00 | 11847 | 3 | | | | CT45A4 | 1.00 |
| 11752 | 3 | | | | | CPLX3 | 1.00 | 11848 | 3 | | | | CT45A5 | 1.00 |
| 11753 | 3 | | | | | CPLX4 | 1.00 | 11849 | 3 | | | | CT45A6 | 1.00 |
| 11754 | 3 | | | | | CPN1 | 1.00 | 11850 | 3 | | | | CT47A1 | 1.00 |
| 11755 | 3 | | | | | CPN2 | 1.00 | 11851 | 3 | | | | CT47A10 | 1.00 |
| 11756 | 3 | | | | | CPNE4 | 1.00 | 11852 | 3 | | | | CT47A11 | 1.00 |
| 11757 | 3 | | | | | CPNE6 | 1.00 | 11853 | 3 | | | | CT47A4 | 1.00 |
| 11758 | 3 | | | | | CPNE7 | 1.00 | 11854 | 3 | | | | CT47A5 | 1.00 |
| 11759 | 3 | | | | | CPNE9 | 1.00 | 11855 | 3 | | | | CT47A6 | 1.00 |
| 11760 | 3 | | | | | CPO | 1.00 | 11856 | 3 | | | | CT47A7 | 1.00 |
| 11761 | 3 | | | | | CPS1 | 1.00 | 11857 | 3 | | | | CT47A8 | 1.00 |
| 11762 | 3 | | | | | CPS1-IT1 | 1.00 | 11858 | 3 | | | | CT47B1 | 1.00 |
| 11763 | 3 | | | | | CPSF4L | 1.00 | 11859 | 3 | | | | CT62 | 1.00 |
| 11764 | 3 | | | | | CPT1C | 1.00 | 11860 | 3 | | | | CTAG1A | 1.00 |
| 11765 | 3 | | | | | CPXCR1 | 1.00 | 11861 | 3 | | | | CTAG1B | 1.00 |
| 11766 | 3 | | | | | CPXM1 | 1.00 | 11862 | 3 | | | | CTAG2 | 1.00 |
| 11767 | 3 | | | | | CPXM2 | 1.00 | 11863 | 3 | | | | CTAGE6P | 1.00 |
| 11768 | 3 | | | | | CPZ | 1.00 | 11864 | 3 | | | | CTAGE9 | 1.00 |
| 11769 | 3 | | | | | CR1L | 1.00 | 11865 | 3 | | | | CTCFL | 1.00 |
| 11770 | 3 | | | | | CRABP1 | 1.00 | 11866 | 3 | | | | CTF1 | 1.00 |
| 11771 | 3 | | | | | CRB1 | 1.00 | 11867 | 3 | | | | CTGF | 1.00 |
| 11772 | 3 | | | | | CRB2 | 1.00 | 11868 | 3 | | | | CTH | 1.00 |
| 11773 | 3 | | | | | CRB3 | 1.00 | 11869 | 3 | | | | CTHRC1 | 1.00 |
| 11774 | 3 | | | | | CRCT1 | 1.00 | 11870 | 3 | | | | CTNNA2 | 1.00 |
| 11775 | 3 | | | | | CREB3L1 | 1.00 | 11871 | 3 | | | | CTNNA3 | 1.00 |
| 11776 | 3 | | | | | CREB3L3 | 1.00 | 11872 | 3 | | | | CTNND2 | 1.00 |
| 11777 | 3 | | | | | CREG2 | 1.00 | 11873 | 3 | | | | CTRB1 | 1.00 |
| 11778 | 3 | | | | | CRH | 1.00 | 11874 | 3 | | | | CTRB2 | 1.00 |
| 11779 | 3 | | | | | CRHBP | 1.00 | 11875 | 3 | | | | CTRC | 1.00 |
| 11780 | 3 | | | | | CRHR1 | 1.00 | 11876 | 3 | | | | CTSG | 1.00 |
| 11781 | 3 | | | | | CRHR2 | 1.00 | 11877 | 3 | | | | CTSL1P2 | 1.00 |
| 11782 | 3 | | | | | CRIP3 | 1.00 | 11878 | 3 | | | | CTSL1P8 | 1.00 |
| 11783 | 3 | | | | | CRISP1 | 1.00 | 11879 | 3 | | | | CTSL2 | 1.00 |
| 11784 | 3 | | | | | CRISP2 | 1.00 | 11880 | 3 | | | | CTSL3 | 1.00 |
| 11785 | 3 | | | | | CRISPLD1 | 1.00 | 11881 | 3 | | | | CTTNBP2 | 1.00 |
| 11786 | 3 | | | | | CRLF1 | 1.00 | 11882 | 3 | | | | CTXN1 | 1.00 |
| 11787 | 3 | | | | | CRLF2 | 1.00 | 11883 | 3 | | | | CTXN2 | 1.00 |
| 11788 | 3 | | | | | CRMP1 | 1.00 | 11884 | 3 | | | | CTXN3 | 1.00 |
| 11789 | 3 | | | | | CRNDE | 1.00 | 11885 | 3 | | | | CUBN | 1.00 |
| 11790 | 3 | | | | | CRNN | 1.00 | 11886 | 3 | | | | CUX2 | 1.00 |
| 11791 | 3 | | | | | CRP | 1.00 | 11887 | 3 | | | | CUZD1 | 1.00 |
| 11792 | 3 | | | | | CRTAC1 | 1.00 | 11888 | 3 | | | | CWH43 | 1.00 |
| 11793 | 3 | | | | | CRX | 1.00 | 11889 | 3 | | | | CX3CL1 | 1.00 |
| 11794 | 3 | | | | | CRYAA | 1.00 | 11890 | 3 | | | | CXADR | 1.00 |
| 11795 | 3 | | | | | CRYAB | 1.00 | 11891 | 3 | | | | CXADRP2 | 1.00 |
| 11796 | 3 | | | | | CRYBA1 | 1.00 | 11892 | 3 | | | | CXADRP3 | 1.00 |
| 11797 | 3 | | | | | CRYBA2 | 1.00 | 11893 | 3 | | | | CXCL11 | 1.00 |
| 11798 | 3 | | | | | CRYBA4 | 1.00 | 11894 | 3 | | | | CXCL12 | 1.00 |
| 11799 | 3 | | | | | CRYBB1 | 1.00 | 11895 | 3 | | | | CXCL13 | 1.00 |
| 11800 | 3 | | | | | CRYBB2 | 1.00 | 11896 | 3 | | | | CXCL14 | 1.00 |
| 11801 | 3 | | | | | CRYBB3 | 1.00 | 11897 | 3 | | | | CXCL17 | 1.00 |
| 11802 | 3 | | | | | CRYGA | 1.00 | 11898 | 3 | | | | CXCL2 | 1.00 |

Fig. 40 - 63

| | | | | | | | | | | | | | | |
|---|---|---|---|---|---|---|---|---|---|---|---|---|---|---|
| 11899 | 3 | | | | | | CXCL3 | 1.00 | 11995 | 3 | | | | DAZ1 | 1.00 |
| 11900 | 3 | | | | | | CXCL6 | 1.00 | 11996 | 3 | | | | DAZ2 | 1.00 |
| 11901 | 3 | | | | | | CXCL9 | 1.00 | 11997 | 3 | | | | DAZ3 | 1.00 |
| 11902 | 3 | | | | | | CXXC11 | 1.00 | 11998 | 3 | | | | DAZ4 | 1.00 |
| 11903 | 3 | | | | | | CXXC1P1 | 1.00 | 11999 | 3 | | | | DAZL | 1.00 |
| 11904 | 3 | | | | | | CXXC4 | 1.00 | 12000 | 3 | | | | DBC1 | 1.00 |
| 11905 | 3 | | | | | | CXorf1 | 1.00 | 12001 | 3 | | | | DBIL5P | 1.00 |
| 11906 | 3 | | | | | | CXorf22 | 1.00 | 12002 | 3 | | | | DBIL5P2 | 1.00 |
| 11907 | 3 | | | | | | CXorf27 | 1.00 | 12003 | 3 | | | | DBX1 | 1.00 |
| 11908 | 3 | | | | | | CXorf28 | 1.00 | 12004 | 3 | | | | DBX2 | 1.00 |
| 11909 | 3 | | | | | | CXorf30 | 1.00 | 12005 | 3 | | | | DCAF12L1 | 1.00 |
| 11910 | 3 | | | | | | CXorf31 | 1.00 | 12006 | 3 | | | | DCAF12L2 | 1.00 |
| 11911 | 3 | | | | | | CXorf36 | 1.00 | 12007 | 3 | | | | DCAF4L2 | 1.00 |
| 11912 | 3 | | | | | | CXorf41 | 1.00 | 12008 | 3 | | | | DCAF8L1 | 1.00 |
| 11913 | 3 | | | | | | CXorf48 | 1.00 | 12009 | 3 | | | | DCAF8L2 | 1.00 |
| 11914 | 3 | | | | | | CXorf49B | 1.00 | 12010 | 3 | | | | DCBLD1 | 1.00 |
| 11915 | 3 | | | | | | CXorf51A | 1.00 | 12011 | 3 | | | | DCC | 1.00 |
| 11916 | 3 | | | | | | CXorf58 | 1.00 | 12012 | 3 | | | | DCD | 1.00 |
| 11917 | 3 | | | | | | CXorf59 | 1.00 | 12013 | 3 | | | | DCDC1 | 1.00 |
| 11918 | 3 | | | | | | CXorf61 | 1.00 | 12014 | 3 | | | | DCDC2 | 1.00 |
| 11919 | 3 | | | | | | CXorf64 | 1.00 | 12015 | 3 | | | | DCDC2B | 1.00 |
| 11920 | 3 | | | | | | CXorf66 | 1.00 | 12016 | 3 | | | | DCDC5 | 1.00 |
| 11921 | 3 | | | | | | CXorf68 | 1.00 | 12017 | 3 | | | | DCHS2 | 1.00 |
| 11922 | 3 | | | | | | CXorf69 | 1.00 | 12018 | 3 | | | | DCLK1 | 1.00 |
| 11923 | 3 | | | | | | CYB5R2 | 1.00 | 12019 | 3 | | | | DCLK2 | 1.00 |
| 11924 | 3 | | | | | | CYCSP52 | 1.00 | 12020 | 3 | | | | DCLK3 | 1.00 |
| 11925 | 3 | | | | | | CYGB | 1.00 | 12021 | 3 | | | | DCN | 1.00 |
| 11926 | 3 | | | | | | CYLC1 | 1.00 | 12022 | 3 | | | | DCST1 | 1.00 |
| 11927 | 3 | | | | | | CYLC2 | 1.00 | 12023 | 3 | | | | DCST2 | 1.00 |
| 11928 | 3 | | | | | | CYMP | 1.00 | 12024 | 3 | | | | DCT | 1.00 |
| 11929 | 3 | | | | | | CYP11A1 | 1.00 | 12025 | 3 | | | | DCUN1D5 | 1.00 |
| 11930 | 3 | | | | | | CYP11B1 | 1.00 | 12026 | 3 | | | | DCX | 1.00 |
| 11931 | 3 | | | | | | CYP11B2 | 1.00 | 12027 | 3 | | | | DDAH1 | 1.00 |
| 11932 | 3 | | | | | | CYP17A1 | 1.00 | 12028 | 3 | | | | DDC | 1.00 |
| 11933 | 3 | | | | | | CYP19A1 | 1.00 | 12029 | 3 | | | | DDI1 | 1.00 |
| 11934 | 3 | | | | | | CYP1A1 | 1.00 | 12030 | 3 | | | | DDIT4L | 1.00 |
| 11935 | 3 | | | | | | CYP1A2 | 1.00 | 12031 | 3 | | | | DDN | 1.00 |
| 11936 | 3 | | | | | | CYP21A2 | 1.00 | 12032 | 3 | | | | DDR2 | 1.00 |
| 11937 | 3 | | | | | | CYP24A1 | 1.00 | 12033 | 3 | | | | DDX25 | 1.00 |
| 11938 | 3 | | | | | | CYP26A1 | 1.00 | 12034 | 3 | | | | DDX3Y | 1.00 |
| 11939 | 3 | | | | | | CYP26B1 | 1.00 | 12035 | 3 | | | | DDX4 | 1.00 |
| 11940 | 3 | | | | | | CYP26C1 | 1.00 | 12036 | 3 | | | | DDX43 | 1.00 |
| 11941 | 3 | | | | | | CYP27B1 | 1.00 | 12037 | 3 | | | | DDX53 | 1.00 |
| 11942 | 3 | | | | | | CYP27C1 | 1.00 | 12038 | 3 | | | | 42705 | 1.00 |
| 11943 | 3 | | | | | | CYP2A13 | 1.00 | 12039 | 3 | | | | DEFA1 | 1.00 |
| 11944 | 3 | | | | | | CYP2A6 | 1.00 | 12040 | 3 | | | | DEFA10P | 1.00 |
| 11945 | 3 | | | | | | CYP2A7 | 1.00 | 12041 | 3 | | | | DEFA5 | 1.00 |
| 11946 | 3 | | | | | | CYP2B6 | 1.00 | 12042 | 3 | | | | DEFA6 | 1.00 |
| 11947 | 3 | | | | | | CYP2B7P1 | 1.00 | 12043 | 3 | | | | DEFB1 | 1.00 |
| 11948 | 3 | | | | | | CYP2C18 | 1.00 | 12044 | 3 | | | | DEFB103A | 1.00 |
| 11949 | 3 | | | | | | CYP2C19 | 1.00 | 12045 | 3 | | | | DEFB103B | 1.00 |
| 11950 | 3 | | | | | | CYP2C8 | 1.00 | 12046 | 3 | | | | DEFB104B | 1.00 |
| 11951 | 3 | | | | | | CYP2C9 | 1.00 | 12047 | 3 | | | | DEFB105B | 1.00 |
| 11952 | 3 | | | | | | CYP2E1 | 1.00 | 12048 | 3 | | | | DEFB106B | 1.00 |
| 11953 | 3 | | | | | | CYP2F1 | 1.00 | 12049 | 3 | | | | DEFB107A | 1.00 |
| 11954 | 3 | | | | | | CYP2G1P | 1.00 | 12050 | 3 | | | | DEFB107B | 1.00 |
| 11955 | 3 | | | | | | CYP2J2 | 1.00 | 12051 | 3 | | | | DEFB108B | 1.00 |
| 11956 | 3 | | | | | | CYP2W1 | 1.00 | 12052 | 3 | | | | DEFB109P1B | 1.00 |
| 11957 | 3 | | | | | | CYP39A1 | 1.00 | 12053 | 3 | | | | DEFB110 | 1.00 |
| 11958 | 3 | | | | | | CYP3A4 | 1.00 | 12054 | 3 | | | | DEFB112 | 1.00 |
| 11959 | 3 | | | | | | CYP3A43 | 1.00 | 12055 | 3 | | | | DEFB113 | 1.00 |
| 11960 | 3 | | | | | | CYP3A5 | 1.00 | 12056 | 3 | | | | DEFB114 | 1.00 |
| 11961 | 3 | | | | | | CYP3A7 | 1.00 | 12057 | 3 | | | | DEFB115 | 1.00 |
| 11962 | 3 | | | | | | CYP3A7-CYP3AP1 | 1.00 | 12058 | 3 | | | | DEFB116 | 1.00 |
| 11963 | 3 | | | | | | CYP46A1 | 1.00 | 12059 | 3 | | | | DEFB118 | 1.00 |
| 11964 | 3 | | | | | | CYP4A11 | 1.00 | 12060 | 3 | | | | DEFB119 | 1.00 |
| 11965 | 3 | | | | | | CYP4A22 | 1.00 | 12061 | 3 | | | | DEFB121 | 1.00 |
| 11966 | 3 | | | | | | CYP4B1 | 1.00 | 12062 | 3 | | | | DEFB122 | 1.00 |
| 11967 | 3 | | | | | | CYP4F11 | 1.00 | 12063 | 3 | | | | DEFB123 | 1.00 |
| 11968 | 3 | | | | | | CYP4F12 | 1.00 | 12064 | 3 | | | | DEFB124 | 1.00 |
| 11969 | 3 | | | | | | CYP4F24P | 1.00 | 12065 | 3 | | | | DEFB125 | 1.00 |
| 11970 | 3 | | | | | | CYP4F30P | 1.00 | 12066 | 3 | | | | DEFB126 | 1.00 |
| 11971 | 3 | | | | | | CYP4F35P | 1.00 | 12067 | 3 | | | | DEFB127 | 1.00 |
| 11972 | 3 | | | | | | CYP4F8 | 1.00 | 12068 | 3 | | | | DEFB128 | 1.00 |
| 11973 | 3 | | | | | | CYP4X1 | 1.00 | 12069 | 3 | | | | DEFB129 | 1.00 |
| 11974 | 3 | | | | | | CYP4Z1 | 1.00 | 12070 | 3 | | | | DEFB130 | 1.00 |
| 11975 | 3 | | | | | | CYP4Z2P | 1.00 | 12071 | 3 | | | | DEFB131 | 1.00 |
| 11976 | 3 | | | | | | CYP7A1 | 1.00 | 12072 | 3 | | | | DEFB132 | 1.00 |
| 11977 | 3 | | | | | | CYP7B1 | 1.00 | 12073 | 3 | | | | DEFB133 | 1.00 |
| 11978 | 3 | | | | | | CYP8B1 | 1.00 | 12074 | 3 | | | | DEFB134 | 1.00 |
| 11979 | 3 | | | | | | CYR61 | 1.00 | 12075 | 3 | | | | DEFB135 | 1.00 |
| 11980 | 3 | | | | | | CYS1 | 1.00 | 12076 | 3 | | | | DEFB136 | 1.00 |
| 11981 | 3 | | | | | | CYTL1 | 1.00 | 12077 | 3 | | | | DEFB4A | 1.00 |
| 11982 | 3 | | | | | | CYYR1 | 1.00 | 12078 | 3 | | | | DEFB4B | 1.00 |
| 11983 | 3 | | | | | | D21S2088E | 1.00 | 12079 | 3 | | | | DEFT1P | 1.00 |
| 11984 | 3 | | | | | | DAB1 | 1.00 | 12080 | 3 | | | | DEGS2 | 1.00 |
| 11985 | 3 | | | | | | DAB2IP | 1.00 | 12081 | 3 | | | | DENND2A | 1.00 |
| 11986 | 3 | | | | | | DACH1 | 1.00 | 12082 | 3 | | | | DENND2C | 1.00 |
| 11987 | 3 | | | | | | DACH2 | 1.00 | 12083 | 3 | | | | DEPDC1 | 1.00 |
| 11988 | 3 | | | | | | DACT2 | 1.00 | 12084 | 3 | | | | DEPDC1B | 1.00 |
| 11989 | 3 | | | | | | DACT3 | 1.00 | 12085 | 3 | | | | DEPDC4 | 1.00 |
| 11990 | 3 | | | | | | DAND5 | 1.00 | 12086 | 3 | | | | DEPDC7 | 1.00 |
| 11991 | 3 | | | | | | DAO | 1.00 | 12087 | 3 | | | | DEPTOR | 1.00 |
| 11992 | 3 | | | | | | DAOA | 1.00 | 12088 | 3 | | | | DFNA5 | 1.00 |
| 11993 | 3 | | | | | | DAOA-AS1 | 1.00 | 12089 | 3 | | | | DFNB59 | 1.00 |
| 11994 | 3 | | | | | | DAPL1 | 1.00 | 12090 | 3 | | | | DGAT2L6 | 1.00 |

Fig. 40 - 64

| | | | | | | | | | | | | | | | |
|---|---|---|---|---|---|---|---|---|---|---|---|---|---|---|---|
| 12091 | 3 | | | | | DGCR10 | 1.00 | 12187 | 3 | | | | | DNAJB8 | 1.00 |
| 12092 | 3 | | | | | DGCR5 | 1.00 | 12188 | 3 | | | | | DNAJB8-AS1 | 1.00 |
| 12093 | 3 | | | | | DGCR9 | 1.00 | 12189 | 3 | | | | | DNAJC12 | 1.00 |
| 12094 | 3 | | | | | DGKB | 1.00 | 12190 | 3 | | | | | DNAJC22 | 1.00 |
| 12095 | 3 | | | | | DGKH | 1.00 | 12191 | 3 | | | | | DNAJC25-GNG10 | 1.00 |
| 12096 | 3 | | | | | DGKI | 1.00 | 12192 | 3 | | | | | DNAJC27-AS1 | 1.00 |
| 12097 | 3 | | | | | DGKK | 1.00 | 12193 | 3 | | | | | DNAJC28 | 1.00 |
| 12098 | 3 | | | | | DHDH | 1.00 | 12194 | 3 | | | | | DNAJC5B | 1.00 |
| 12099 | 3 | | | | | DHH | 1.00 | 12195 | 3 | | | | | DNAJC5G | 1.00 |
| 12100 | 3 | | | | | DHRS2 | 1.00 | 12196 | 3 | | | | | DNAJC6 | 1.00 |
| 12101 | 3 | | | | | DHRS4L1 | 1.00 | 12197 | 3 | | | | | DNAI1 | 1.00 |
| 12102 | 3 | | | | | DHRS7C | 1.00 | 12198 | 3 | | | | | DNASE1L3 | 1.00 |
| 12103 | 3 | | | | | DIAPH3 | 1.00 | 12199 | 3 | | | | | DNASE2B | 1.00 |
| 12104 | 3 | | | | | DIO1 | 1.00 | 12200 | 3 | | | | | DNER | 1.00 |
| 12105 | 3 | | | | | DIO2 | 1.00 | 12201 | 3 | | | | | DNM1 | 1.00 |
| 12106 | 3 | | | | | DIO3 | 1.00 | 12202 | 3 | | | | | DNM1P35 | 1.00 |
| 12107 | 3 | | | | | DIO3OS | 1.00 | 12203 | 3 | | | | | DNM1P41 | 1.00 |
| 12108 | 3 | | | | | DIP2C | 1.00 | 12204 | 3 | | | | | DNM1P46 | 1.00 |
| 12109 | 3 | | | | | DIRAS1 | 1.00 | 12205 | 3 | | | | | DNM3OS | 1.00 |
| 12110 | 3 | | | | | DIRAS2 | 1.00 | 12206 | 3 | | | | | DNMBP-AS1 | 1.00 |
| 12111 | 3 | | | | | DIRAS3 | 1.00 | 12207 | 3 | | | | | DNMT3B | 1.00 |
| 12112 | 3 | | | | | DIRC1 | 1.00 | 12208 | 3 | | | | | DNMT3L | 1.00 |
| 12113 | 3 | | | | | DIRC3 | 1.00 | 12209 | 3 | | | | | DNTT | 1.00 |
| 12114 | 3 | | | | | DISC2 | 1.00 | 12210 | 3 | | | | | DOC2A | 1.00 |
| 12115 | 3 | | | | | DISP2 | 1.00 | 12211 | 3 | | | | | DOC2B | 1.00 |
| 12116 | 3 | | | | | DIXDC1 | 1.00 | 12212 | 3 | | | | | DOC2GP | 1.00 |
| 12117 | 3 | | | | | DKFZP434A062 | 1.00 | 12213 | 3 | | | | | DOCK1 | 1.00 |
| 12118 | 3 | | | | | DKFZP434H168 | 1.00 | 12214 | 3 | | | | | DOCK3 | 1.00 |
| 12119 | 3 | | | | | DKFZP434K028 | 1.00 | 12215 | 3 | | | | | DOCK6 | 1.00 |
| 12120 | 3 | | | | | DKFZP434L187 | 1.00 | 12216 | 3 | | | | | DOCK7 | 1.00 |
| 12121 | 3 | | | | | DKFZP564C196 | 1.00 | 12217 | 3 | | | | | DOK5 | 1.00 |
| 12122 | 3 | | | | | DKFZp434J0226 | 1.00 | 12218 | 3 | | | | | DOK6 | 1.00 |
| 12123 | 3 | | | | | DKFZp434L192 | 1.00 | 12219 | 3 | | | | | DOK7 | 1.00 |
| 12124 | 3 | | | | | DKFZp451B082 | 1.00 | 12220 | 3 | | | | | DPCR1 | 1.00 |
| 12125 | 3 | | | | | DKFZp566F0947 | 1.00 | 12221 | 3 | | | | | DPEP1 | 1.00 |
| 12126 | 3 | | | | | DKFZp686D0853 | 1.00 | 12222 | 3 | | | | | DPF1 | 1.00 |
| 12127 | 3 | | | | | DKFZp686K1684 | 1.00 | 12223 | 3 | | | | | DPF3 | 1.00 |
| 12128 | 3 | | | | | DKFZp686O1327 | 1.00 | 12224 | 3 | | | | | DPP10 | 1.00 |
| 12129 | 3 | | | | | DKFZp779M0652 | 1.00 | 12225 | 3 | | | | | DPP6 | 1.00 |
| 12130 | 3 | | | | | DKK1 | 1.00 | 12226 | 3 | | | | | DPPA2 | 1.00 |
| 12131 | 3 | | | | | DKK2 | 1.00 | 12227 | 3 | | | | | DPPA3 | 1.00 |
| 12132 | 3 | | | | | DKK3 | 1.00 | 12228 | 3 | | | | | DPPA4 | 1.00 |
| 12133 | 3 | | | | | DKK4 | 1.00 | 12229 | 3 | | | | | DPPA5 | 1.00 |
| 12134 | 3 | | | | | DKKL1 | 1.00 | 12230 | 3 | | | | | DPRX | 1.00 |
| 12135 | 3 | | | | | DLC1 | 1.00 | 12231 | 3 | | | | | DPRXP4 | 1.00 |
| 12136 | 3 | | | | | DLEC1 | 1.00 | 12232 | 3 | | | | | DPT | 1.00 |
| 12137 | 3 | | | | | DLG2 | 1.00 | 12233 | 3 | | | | | DPY19L1P1 | 1.00 |
| 12138 | 3 | | | | | DLGAP1 | 1.00 | 12234 | 3 | | | | | DPY19L2 | 1.00 |
| 12139 | 3 | | | | | DLGAP2 | 1.00 | 12235 | 3 | | | | | DPY19L2P1 | 1.00 |
| 12140 | 3 | | | | | DLGAP3 | 1.00 | 12236 | 3 | | | | | DPY19L2P2 | 1.00 |
| 12141 | 3 | | | | | DLGAP5 | 1.00 | 12237 | 3 | | | | | DPY19L2P3 | 1.00 |
| 12142 | 3 | | | | | DLK1 | 1.00 | 12238 | 3 | | | | | DPY19L2P4 | 1.00 |
| 12143 | 3 | | | | | DLK2 | 1.00 | 12239 | 3 | | | | | DPYS | 1.00 |
| 12144 | 3 | | | | | DLL3 | 1.00 | 12240 | 3 | | | | | DPYSL3 | 1.00 |
| 12145 | 3 | | | | | DLL4 | 1.00 | 12241 | 3 | | | | | DPYSL4 | 1.00 |
| 12146 | 3 | | | | | DLX1 | 1.00 | 12242 | 3 | | | | | DPYSL5 | 1.00 |
| 12147 | 3 | | | | | DLX2 | 1.00 | 12243 | 3 | | | | | DQX1 | 1.00 |
| 12148 | 3 | | | | | DLX3 | 1.00 | 12244 | 3 | | | | | DRD1 | 1.00 |
| 12149 | 3 | | | | | DLX4 | 1.00 | 12245 | 3 | | | | | DRD2 | 1.00 |
| 12150 | 3 | | | | | DLX5 | 1.00 | 12246 | 3 | | | | | DRD3 | 1.00 |
| 12151 | 3 | | | | | DLX6 | 1.00 | 12247 | 3 | | | | | DRD4 | 1.00 |
| 12152 | 3 | | | | | DLX6-AS1 | 1.00 | 12248 | 3 | | | | | DRD5 | 1.00 |
| 12153 | 3 | | | | | DMBT1 | 1.00 | 12249 | 3 | | | | | DRGX | 1.00 |
| 12154 | 3 | | | | | DMBX1 | 1.00 | 12250 | 3 | | | | | DRP2 | 1.00 |
| 12155 | 3 | | | | | DMC1 | 1.00 | 12251 | 3 | | | | | DSC1 | 1.00 |
| 12156 | 3 | | | | | DMD | 1.00 | 12252 | 3 | | | | | DSC3 | 1.00 |
| 12157 | 3 | | | | | DMGDH | 1.00 | 12253 | 3 | | | | | DSCAM | 1.00 |
| 12158 | 3 | | | | | DMP1 | 1.00 | 12254 | 3 | | | | | DSCAM-AS1 | 1.00 |
| 12159 | 3 | | | | | DMRT1 | 1.00 | 12255 | 3 | | | | | DSCAML1 | 1.00 |
| 12160 | 3 | | | | | DMRT2 | 1.00 | 12256 | 3 | | | | | DSCC1 | 1.00 |
| 12161 | 3 | | | | | DMRT3 | 1.00 | 12257 | 3 | | | | | DSCR10 | 1.00 |
| 12162 | 3 | | | | | DMRTA1 | 1.00 | 12258 | 3 | | | | | DSCR4 | 1.00 |
| 12163 | 3 | | | | | DMRTA2 | 1.00 | 12259 | 3 | | | | | DSCR6 | 1.00 |
| 12164 | 3 | | | | | DMRTB1 | 1.00 | 12260 | 3 | | | | | DSCR8 | 1.00 |
| 12165 | 3 | | | | | DMRTC1B | 1.00 | 12261 | 3 | | | | | DSCR9 | 1.00 |
| 12166 | 3 | | | | | DMRTC2 | 1.00 | 12262 | 3 | | | | | DSEL | 1.00 |
| 12167 | 3 | | | | | DNA2 | 1.00 | 12263 | 3 | | | | | DSG1 | 1.00 |
| 12168 | 3 | | | | | DNAAF1 | 1.00 | 12264 | 3 | | | | | DSG2 | 1.00 |
| 12169 | 3 | | | | | DNAH10 | 1.00 | 12265 | 3 | | | | | DSG3 | 1.00 |
| 12170 | 3 | | | | | DNAH11 | 1.00 | 12266 | 3 | | | | | DSG4 | 1.00 |
| 12171 | 3 | | | | | DNAH12 | 1.00 | 12267 | 3 | | | | | DSPP | 1.00 |
| 12172 | 3 | | | | | DNAH14 | 1.00 | 12268 | 3 | | | | | DST | 1.00 |
| 12173 | 3 | | | | | DNAH17 | 1.00 | 12269 | 3 | | | | | DTL | 1.00 |
| 12174 | 3 | | | | | DNAH2 | 1.00 | 12270 | 3 | | | | | DTNA | 1.00 |
| 12175 | 3 | | | | | DNAH3 | 1.00 | 12271 | 3 | | | | | DUOX1 | 1.00 |
| 12176 | 3 | | | | | DNAH5 | 1.00 | 12272 | 3 | | | | | DUOX2 | 1.00 |
| 12177 | 3 | | | | | DNAH6 | 1.00 | 12273 | 3 | | | | | DUOXA1 | 1.00 |
| 12178 | 3 | | | | | DNAH7 | 1.00 | 12274 | 3 | | | | | DUOXA2 | 1.00 |
| 12179 | 3 | | | | | DNAH8 | 1.00 | 12275 | 3 | | | | | DUPD1 | 1.00 |
| 12180 | 3 | | | | | DNAH9 | 1.00 | 12276 | 3 | | | | | DUSP13 | 1.00 |
| 12181 | 3 | | | | | DNAI1 | 1.00 | 12277 | 3 | | | | | DUSP15 | 1.00 |
| 12182 | 3 | | | | | DNAI2 | 1.00 | 12278 | 3 | | | | | DUSP21 | 1.00 |
| 12183 | 3 | | | | | DNAJA1P5 | 1.00 | 12279 | 3 | | | | | DUSP26 | 1.00 |
| 12184 | 3 | | | | | DNAJB13 | 1.00 | 12280 | 3 | | | | | DUSP27 | 1.00 |
| 12185 | 3 | | | | | DNAJB3 | 1.00 | 12281 | 3 | | | | | DUSP4 | 1.00 |
| 12186 | 3 | | | | | DNAJB7 | 1.00 | 12282 | 3 | | | | | DUSP5P | 1.00 |

Fig. 40 - 65

| | | | | | | | | | | | | | |
|---|---|---|---|---|---|---|---|---|---|---|---|---|---|
| 12283 | 3 | | | | | DUSP9 | 1.00 | 12379 | 3 | | | EML1 | 1.00 |
| 12284 | 3 | | | | | DUX2 | 1.00 | 12380 | 3 | | | EML5 | 1.00 |
| 12285 | 3 | | | | | DUX4 | 1.00 | 12381 | 3 | | | EML6 | 1.00 |
| 12286 | 3 | | | | | DUX4L2 | 1.00 | 12382 | 3 | | | EMP2 | 1.00 |
| 12287 | 3 | | | | | DUX4L3 | 1.00 | 12383 | 3 | | | EMX1 | 1.00 |
| 12288 | 3 | | | | | DUX4L4 | 1.00 | 12384 | 3 | | | EMX2 | 1.00 |
| 12289 | 3 | | | | | DUX4L5 | 1.00 | 12385 | 3 | | | EMX2OS | 1.00 |
| 12290 | 3 | | | | | DUX4L6 | 1.00 | 12386 | 3 | | | EN1 | 1.00 |
| 12291 | 3 | | | | | DUXA | 1.00 | 12387 | 3 | | | EN2 | 1.00 |
| 12292 | 3 | | | | | DYDC1 | 1.00 | 12388 | 3 | | | ENAH | 1.00 |
| 12293 | 3 | | | | | DYDC2 | 1.00 | 12389 | 3 | | | ENAM | 1.00 |
| 12294 | 3 | | | | | DYNC1I1 | 1.00 | 12390 | 3 | | | ENDOU | 1.00 |
| 12295 | 3 | | | | | DYNC2H1 | 1.00 | 12391 | 3 | | | ENO1-AS1 | 1.00 |
| 12296 | 3 | | | | | DYNC2LI1 | 1.00 | 12392 | 3 | | | ENO4 | 1.00 |
| 12297 | 3 | | | | | DYNLRB2 | 1.00 | 12393 | 3 | | | ENOX1 | 1.00 |
| 12298 | 3 | | | | | DYTN | 1.00 | 12394 | 3 | | | ENPEP | 1.00 |
| 12299 | 3 | | | | | DYX1C1 | 1.00 | 12395 | 3 | | | ENPP1 | 1.00 |
| 12300 | 3 | | | | | DYX1C1-CCPG1 | 1.00 | 12396 | 3 | | | ENPP2 | 1.00 |
| 12301 | 3 | | | | | DZANK1 | 1.00 | 12397 | 3 | | | ENPP3 | 1.00 |
| 12302 | 3 | | | | | DZANK1-AS1 | 1.00 | 12398 | 3 | | | ENPP6 | 1.00 |
| 12303 | 3 | | | | | DZIP1 | 1.00 | 12399 | 3 | | | ENPP7 | 1.00 |
| 12304 | 3 | | | | | DZIP1L | 1.00 | 12400 | 3 | | | ENTHD1 | 1.00 |
| 12305 | 3 | | | | | E2F7 | 1.00 | 12401 | 3 | | | ENTPD3 | 1.00 |
| 12306 | 3 | | | | | E2F8 | 1.00 | 12402 | 3 | | | ENTPD3-AS1 | 1.00 |
| 12307 | 3 | | | | | EBF2 | 1.00 | 12403 | 3 | | | ENTPD8 | 1.00 |
| 12308 | 3 | | | | | EBF3 | 1.00 | 12404 | 3 | | | EPB41L1 | 1.00 |
| 12309 | 3 | | | | | EBF4 | 1.00 | 12405 | 3 | | | EPB41L4B | 1.00 |
| 12310 | 3 | | | | | EBI3 | 1.00 | 12406 | 3 | | | EPCAM | 1.00 |
| 12311 | 3 | | | | | EBLN1 | 1.00 | 12407 | 3 | | | EPDR1 | 1.00 |
| 12312 | 3 | | | | | ECEL1 | 1.00 | 12408 | 3 | | | EPGN | 1.00 |
| 12313 | 3 | | | | | ECEL1P2 | 1.00 | 12409 | 3 | | | EPHA10 | 1.00 |
| 12314 | 3 | | | | | ECM1 | 1.00 | 12410 | 3 | | | EPHA2 | 1.00 |
| 12315 | 3 | | | | | ECM2 | 1.00 | 12411 | 3 | | | EPHA3 | 1.00 |
| 12316 | 3 | | | | | ECSCR | 1.00 | 12412 | 3 | | | EPHA5 | 1.00 |
| 12317 | 3 | | | | | ECT2L | 1.00 | 12413 | 3 | | | EPHA6 | 1.00 |
| 12318 | 3 | | | | | EDA | 1.00 | 12414 | 3 | | | EPHA7 | 1.00 |
| 12319 | 3 | | | | | EDDM3A | 1.00 | 12415 | 3 | | | EPHA8 | 1.00 |
| 12320 | 3 | | | | | EDDM3B | 1.00 | 12416 | 3 | | | EPHB3 | 1.00 |
| 12321 | 3 | | | | | EDIL3 | 1.00 | 12417 | 3 | | | EPHX3 | 1.00 |
| 12322 | 3 | | | | | EDN1 | 1.00 | 12418 | 3 | | | EPHX4 | 1.00 |
| 12323 | 3 | | | | | EDN2 | 1.00 | 12419 | 3 | | | EPN3 | 1.00 |
| 12324 | 3 | | | | | EDN3 | 1.00 | 12420 | 3 | | | EPO | 1.00 |
| 12325 | 3 | | | | | EDNRA | 1.00 | 12421 | 3 | | | EPS8L1 | 1.00 |
| 12326 | 3 | | | | | EDNRB | 1.00 | 12422 | 3 | | | EPS8L3 | 1.00 |
| 12327 | 3 | | | | | EEF1A2 | 1.00 | 12423 | 3 | | | EPX | 1.00 |
| 12328 | 3 | | | | | EEF1DP3 | 1.00 | 12424 | 3 | | | EPYC | 1.00 |
| 12329 | 3 | | | | | EFCAB1 | 1.00 | 12425 | 3 | | | ERAS | 1.00 |
| 12330 | 3 | | | | | EFCAB10 | 1.00 | 12426 | 3 | | | ERBB3 | 1.00 |
| 12331 | 3 | | | | | EFCAB11 | 1.00 | 12427 | 3 | | | ERBB4 | 1.00 |
| 12332 | 3 | | | | | EFCAB3 | 1.00 | 12428 | 3 | | | ERC2 | 1.00 |
| 12333 | 3 | | | | | EFCAB5 | 1.00 | 12429 | 3 | | | ERCC2 | 1.00 |
| 12334 | 3 | | | | | EFCAB6 | 1.00 | 12430 | 3 | | | ERCC6L | 1.00 |
| 12335 | 3 | | | | | EFCAB7 | 1.00 | 12431 | 3 | | | EREG | 1.00 |
| 12336 | 3 | | | | | EFCAB9 | 1.00 | 12432 | 3 | | | ERG | 1.00 |
| 12337 | 3 | | | | | EFEMP1 | 1.00 | 12433 | 3 | | | ERN2 | 1.00 |
| 12338 | 3 | | | | | EFHA2 | 1.00 | 12434 | 3 | | | ERRFI1 | 1.00 |
| 12339 | 3 | | | | | EFHB | 1.00 | 12435 | 3 | | | ERVFRD-1 | 1.00 |
| 12340 | 3 | | | | | EFNA2 | 1.00 | 12436 | 3 | | | ERVMER34-1 | 1.00 |
| 12341 | 3 | | | | | EFNA5 | 1.00 | 12437 | 3 | | | ERVV-1 | 1.00 |
| 12342 | 3 | | | | | EFNB2 | 1.00 | 12438 | 3 | | | ERVV-2 | 1.00 |
| 12343 | 3 | | | | | EFNB3 | 1.00 | 12439 | 3 | | | ESCO2 | 1.00 |
| 12344 | 3 | | | | | EFR3B | 1.00 | 12440 | 3 | | | ESM1 | 1.00 |
| 12345 | 3 | | | | | EFS | 1.00 | 12441 | 3 | | | ESPL1 | 1.00 |
| 12346 | 3 | | | | | EGFEM1P | 1.00 | 12442 | 3 | | | ESPNL | 1.00 |
| 12347 | 3 | | | | | EGFL6 | 1.00 | 12443 | 3 | | | ESPNP | 1.00 |
| 12348 | 3 | | | | | EGFLAM | 1.00 | 12444 | 3 | | | ESR1 | 1.00 |
| 12349 | 3 | | | | | EGFLAM-AS4 | 1.00 | 12445 | 3 | | | ESRP1 | 1.00 |
| 12350 | 3 | | | | | EGFR | 1.00 | 12446 | 3 | | | ESRP2 | 1.00 |
| 12351 | 3 | | | | | EGOT | 1.00 | 12447 | 3 | | | ESRRB | 1.00 |
| 12352 | 3 | | | | | EGR4 | 1.00 | 12448 | 3 | | | ESRRG | 1.00 |
| 12353 | 3 | | | | | EHD2 | 1.00 | 12449 | 3 | | | ESX1 | 1.00 |
| 12354 | 3 | | | | | EHF | 1.00 | 12450 | 3 | | | ESYT3 | 1.00 |
| 12355 | 3 | | | | | EHHADH | 1.00 | 12451 | 3 | | | ETNK2 | 1.00 |
| 12356 | 3 | | | | | EIF1AY | 1.00 | 12452 | 3 | | | ETV1 | 1.00 |
| 12357 | 3 | | | | | EIF3CL | 1.00 | 12453 | 3 | | | ETV2 | 1.00 |
| 12358 | 3 | | | | | EIF4E1B | 1.00 | 12454 | 3 | | | ETV3L | 1.00 |
| 12359 | 3 | | | | | ELAVL2 | 1.00 | 12455 | 3 | | | ETV4 | 1.00 |
| 12360 | 3 | | | | | ELAVL3 | 1.00 | 12456 | 3 | | | ETV5 | 1.00 |
| 12361 | 3 | | | | | ELAVL4 | 1.00 | 12457 | 3 | | | EVC | 1.00 |
| 12362 | 3 | | | | | ELF3 | 1.00 | 12458 | 3 | | | EVC2 | 1.00 |
| 12363 | 3 | | | | | ELF5 | 1.00 | 12459 | 3 | | | EVPL | 1.00 |
| 12364 | 3 | | | | | ELFN1 | 1.00 | 12460 | 3 | | | EVPLL | 1.00 |
| 12365 | 3 | | | | | ELFN2 | 1.00 | 12461 | 3 | | | EVX1 | 1.00 |
| 12366 | 3 | | | | | ELMOD1 | 1.00 | 12462 | 3 | | | EVX2 | 1.00 |
| 12367 | 3 | | | | | ELN | 1.00 | 12463 | 3 | | | EXD1 | 1.00 |
| 12368 | 3 | | | | | ELOVL2 | 1.00 | 12464 | 3 | | | EXD3 | 1.00 |
| 12369 | 3 | | | | | ELOVL3 | 1.00 | 12465 | 3 | | | EXO1 | 1.00 |
| 12370 | 3 | | | | | ELOVL4 | 1.00 | 12466 | 3 | | | EXOC3L2 | 1.00 |
| 12371 | 3 | | | | | ELSPBP1 | 1.00 | 12467 | 3 | | | EXOC3L4 | 1.00 |
| 12372 | 3 | | | | | ELTD1 | 1.00 | 12468 | 3 | | | EXOC6B | 1.00 |
| 12373 | 3 | | | | | EMCN | 1.00 | 12469 | 3 | | | EXPH5 | 1.00 |
| 12374 | 3 | | | | | EME1 | 1.00 | 12470 | 3 | | | EXTL1 | 1.00 |
| 12375 | 3 | | | | | EMID1 | 1.00 | 12471 | 3 | | | EYA1 | 1.00 |
| 12376 | 3 | | | | | EMID2 | 1.00 | 12472 | 3 | | | EYA2 | 1.00 |
| 12377 | 3 | | | | | EMILIN1 | 1.00 | 12473 | 3 | | | EYA4 | 1.00 |
| 12378 | 3 | | | | | EMILIN3 | 1.00 | 12474 | 3 | | | EYS | 1.00 |

Fig. 40 - 66

| | | | | | | | | | | | | | |
|---|---|---|---|---|---|---|---|---|---|---|---|---|---|
| 12475 | 3 | | | | | F10 | 1.00 | 12571 | 3 | | | FAM197Y5 | 1.00 |
| 12476 | 3 | | | | | F11 | 1.00 | 12572 | 3 | | | FAM198A | 1.00 |
| 12477 | 3 | | | | | F13B | 1.00 | 12573 | 3 | | | FAM19A1 | 1.00 |
| 12478 | 3 | | | | | F2 | 1.00 | 12574 | 3 | | | FAM19A3 | 1.00 |
| 12479 | 3 | | | | | F2RL2 | 1.00 | 12575 | 3 | | | FAM19A4 | 1.00 |
| 12480 | 3 | | | | | F3 | 1.00 | 12576 | 3 | | | FAM19A5 | 1.00 |
| 12481 | 3 | | | | | F7 | 1.00 | 12577 | 3 | | | FAM201A | 1.00 |
| 12482 | 3 | | | | | F8A2 | 1.00 | 12578 | 3 | | | FAM205A | 1.00 |
| 12483 | 3 | | | | | F9 | 1.00 | 12579 | 3 | | | FAM205B | 1.00 |
| 12484 | 3 | | | | | FA2H | 1.00 | 12580 | 3 | | | FAM20A | 1.00 |
| 12485 | 3 | | | | | FAAH2 | 1.00 | 12581 | 3 | | | FAM211B | 1.00 |
| 12486 | 3 | | | | | FABP1 | 1.00 | 12582 | 3 | | | FAM215A | 1.00 |
| 12487 | 3 | | | | | FABP12 | 1.00 | 12583 | 3 | | | FAM216B | 1.00 |
| 12488 | 3 | | | | | FABP2 | 1.00 | 12584 | 3 | | | FAM217A | 1.00 |
| 12489 | 3 | | | | | FABP3 | 1.00 | 12585 | 3 | | | FAM22F | 1.00 |
| 12490 | 3 | | | | | FABP4 | 1.00 | 12586 | 3 | | | FAM22G | 1.00 |
| 12491 | 3 | | | | | FABP5P3 | 1.00 | 12587 | 3 | | | FAM24A | 1.00 |
| 12492 | 3 | | | | | FABP6 | 1.00 | 12588 | 3 | | | FAM24B-CUZD1 | 1.00 |
| 12493 | 3 | | | | | FABP7 | 1.00 | 12589 | 3 | | | FAM25A | 1.00 |
| 12494 | 3 | | | | | FABP9 | 1.00 | 12590 | 3 | | | FAM25B | 1.00 |
| 12495 | 3 | | | | | FADS6 | 1.00 | 12591 | 3 | | | FAM25C | 1.00 |
| 12496 | 3 | | | | | FAIM2 | 1.00 | 12592 | 3 | | | FAM26D | 1.00 |
| 12497 | 3 | | | | | FAM101A | 1.00 | 12593 | 3 | | | FAM26E | 1.00 |
| 12498 | 3 | | | | | FAM106A | 1.00 | 12594 | 3 | | | FAM27C | 1.00 |
| 12499 | 3 | | | | | FAM106CP | 1.00 | 12595 | 3 | | | FAM27L | 1.00 |
| 12500 | 3 | | | | | FAM107A | 1.00 | 12596 | 3 | | | FAM3B | 1.00 |
| 12501 | 3 | | | | | FAM110B | 1.00 | 12597 | 3 | | | FAM3D | 1.00 |
| 12502 | 3 | | | | | FAM110C | 1.00 | 12598 | 3 | | | FAM40B | 1.00 |
| 12503 | 3 | | | | | FAM110D | 1.00 | 12599 | 3 | | | FAM41AY1 | 1.00 |
| 12504 | 3 | | | | | FAM123A | 1.00 | 12600 | 3 | | | FAM41AY2 | 1.00 |
| 12505 | 3 | | | | | FAM123C | 1.00 | 12601 | 3 | | | FAM41C | 1.00 |
| 12506 | 3 | | | | | FAM124A | 1.00 | 12602 | 3 | | | FAM43B | 1.00 |
| 12507 | 3 | | | | | FAM127C | 1.00 | 12603 | 3 | | | FAM46B | 1.00 |
| 12508 | 3 | | | | | FAM131B | 1.00 | 12604 | 3 | | | FAM46D | 1.00 |
| 12509 | 3 | | | | | FAM131C | 1.00 | 12605 | 3 | | | FAM47A | 1.00 |
| 12510 | 3 | | | | | FAM132A | 1.00 | 12606 | 3 | | | FAM47B | 1.00 |
| 12511 | 3 | | | | | FAM133A | 1.00 | 12607 | 3 | | | FAM47C | 1.00 |
| 12512 | 3 | | | | | FAM135B | 1.00 | 12608 | 3 | | | FAM47E | 1.00 |
| 12513 | 3 | | | | | FAM138A | 1.00 | 12609 | 3 | | | FAM47E-STBD1 | 1.00 |
| 12514 | 3 | | | | | FAM138B | 1.00 | 12610 | 3 | | | FAM48B1 | 1.00 |
| 12515 | 3 | | | | | FAM138C | 1.00 | 12611 | 3 | | | FAM48B2 | 1.00 |
| 12516 | 3 | | | | | FAM138D | 1.00 | 12612 | 3 | | | FAM53A | 1.00 |
| 12517 | 3 | | | | | FAM138E | 1.00 | 12613 | 3 | | | FAM54A | 1.00 |
| 12518 | 3 | | | | | FAM138F | 1.00 | 12614 | 3 | | | FAM55A | 1.00 |
| 12519 | 3 | | | | | FAM13C | 1.00 | 12615 | 3 | | | FAM55B | 1.00 |
| 12520 | 3 | | | | | FAM149A | 1.00 | 12616 | 3 | | | FAM55D | 1.00 |
| 12521 | 3 | | | | | FAM150A | 1.00 | 12617 | 3 | | | FAM57A | 1.00 |
| 12522 | 3 | | | | | FAM150B | 1.00 | 12618 | 3 | | | FAM57B | 1.00 |
| 12523 | 3 | | | | | FAM151A | 1.00 | 12619 | 3 | | | FAM59A | 1.00 |
| 12524 | 3 | | | | | FAM153A | 1.00 | 12620 | 3 | | | FAM59B | 1.00 |
| 12525 | 3 | | | | | FAM154A | 1.00 | 12621 | 3 | | | FAM5B | 1.00 |
| 12526 | 3 | | | | | FAM154B | 1.00 | 12622 | 3 | | | FAM5C | 1.00 |
| 12527 | 3 | | | | | FAM155A | 1.00 | 12623 | 3 | | | FAM64A | 1.00 |
| 12528 | 3 | | | | | FAM155B | 1.00 | 12624 | 3 | | | FAM66A | 1.00 |
| 12529 | 3 | | | | | FAM159B | 1.00 | 12625 | 3 | | | FAM66B | 1.00 |
| 12530 | 3 | | | | | FAM160A1 | 1.00 | 12626 | 3 | | | FAM66C | 1.00 |
| 12531 | 3 | | | | | FAM161A | 1.00 | 12627 | 3 | | | FAM66D | 1.00 |
| 12532 | 3 | | | | | FAM162B | 1.00 | 12628 | 3 | | | FAM66E | 1.00 |
| 12533 | 3 | | | | | FAM163A | 1.00 | 12629 | 3 | | | FAM69C | 1.00 |
| 12534 | 3 | | | | | FAM163B | 1.00 | 12630 | 3 | | | FAM70A | 1.00 |
| 12535 | 3 | | | | | FAM166A | 1.00 | 12631 | 3 | | | FAM70B | 1.00 |
| 12536 | 3 | | | | | FAM166B | 1.00 | 12632 | 3 | | | FAM71A | 1.00 |
| 12537 | 3 | | | | | FAM167B | 1.00 | 12633 | 3 | | | FAM71B | 1.00 |
| 12538 | 3 | | | | | FAM169B | 1.00 | 12634 | 3 | | | FAM71C | 1.00 |
| 12539 | 3 | | | | | FAM170A | 1.00 | 12635 | 3 | | | FAM71D | 1.00 |
| 12540 | 3 | | | | | FAM170B | 1.00 | 12636 | 3 | | | FAM71E2 | 1.00 |
| 12541 | 3 | | | | | FAM171A2 | 1.00 | 12637 | 3 | | | FAM71F1 | 1.00 |
| 12542 | 3 | | | | | FAM171B | 1.00 | 12638 | 3 | | | FAM71F2 | 1.00 |
| 12543 | 3 | | | | | FAM172BP | 1.00 | 12639 | 3 | | | FAM74A1 | 1.00 |
| 12544 | 3 | | | | | FAM176A | 1.00 | 12640 | 3 | | | FAM74A2 | 1.00 |
| 12545 | 3 | | | | | FAM178B | 1.00 | 12641 | 3 | | | FAM74A3 | 1.00 |
| 12546 | 3 | | | | | FAM179A | 1.00 | 12642 | 3 | | | FAM74A4 | 1.00 |
| 12547 | 3 | | | | | FAM180A | 1.00 | 12643 | 3 | | | FAM75A1 | 1.00 |
| 12548 | 3 | | | | | FAM180B | 1.00 | 12644 | 3 | | | FAM75A2 | 1.00 |
| 12549 | 3 | | | | | FAM181A | 1.00 | 12645 | 3 | | | FAM75A3 | 1.00 |
| 12550 | 3 | | | | | FAM181A-AS1 | 1.00 | 12646 | 3 | | | FAM75A4 | 1.00 |
| 12551 | 3 | | | | | FAM181B | 1.00 | 12647 | 3 | | | FAM75A5 | 1.00 |
| 12552 | 3 | | | | | FAM182A | 1.00 | 12648 | 3 | | | FAM75A6 | 1.00 |
| 12553 | 3 | | | | | FAM182B | 1.00 | 12649 | 3 | | | FAM75A7 | 1.00 |
| 12554 | 3 | | | | | FAM183A | 1.00 | 12650 | 3 | | | FAM75C1 | 1.00 |
| 12555 | 3 | | | | | FAM183B | 1.00 | 12651 | 3 | | | FAM75C2 | 1.00 |
| 12556 | 3 | | | | | FAM184A | 1.00 | 12652 | 3 | | | FAM75D1 | 1.00 |
| 12557 | 3 | | | | | FAM186A | 1.00 | 12653 | 3 | | | FAM75D3 | 1.00 |
| 12558 | 3 | | | | | FAM186B | 1.00 | 12654 | 3 | | | FAM75D4 | 1.00 |
| 12559 | 3 | | | | | FAM187B | 1.00 | 12655 | 3 | | | FAM75D5 | 1.00 |
| 12560 | 3 | | | | | FAM188B | 1.00 | 12656 | 3 | | | FAM78B | 1.00 |
| 12561 | 3 | | | | | FAM189A1 | 1.00 | 12657 | 3 | | | FAM81A | 1.00 |
| 12562 | 3 | | | | | FAM189A2 | 1.00 | 12658 | 3 | | | FAM83A | 1.00 |
| 12563 | 3 | | | | | FAM18A | 1.00 | 12659 | 3 | | | FAM83B | 1.00 |
| 12564 | 3 | | | | | FAM18B2-CDRT4 | 1.00 | 12660 | 3 | | | FAM83C | 1.00 |
| 12565 | 3 | | | | | FAM190A | 1.00 | 12661 | 3 | | | FAM83E | 1.00 |
| 12566 | 3 | | | | | FAM194A | 1.00 | 12662 | 3 | | | FAM83F | 1.00 |
| 12567 | 3 | | | | | FAM194B | 1.00 | 12663 | 3 | | | FAM84A | 1.00 |
| 12568 | 3 | | | | | FAM196A | 1.00 | 12664 | 3 | | | FAM86B1 | 1.00 |
| 12569 | 3 | | | | | FAM196B | 1.00 | 12665 | 3 | | | FAM86B2 | 1.00 |
| 12570 | 3 | | | | | FAM197Y2P | 1.00 | 12666 | 3 | | | FAM86C2P | 1.00 |

Fig. 40 - 67

| | | | | | | | | | | | | | | |
|---|---|---|---|---|---|---|---|---|---|---|---|---|---|---|
| 12667 | 3 | | | | | FAM86EP | 1.00 | 12763 | 3 | | | | FGF3 | 1.00 |
| 12668 | 3 | | | | | FAM86FP | 1.00 | 12764 | 3 | | | | FGF4 | 1.00 |
| 12669 | 3 | | | | | FAM86HP | 1.00 | 12765 | 3 | | | | FGF5 | 1.00 |
| 12670 | 3 | | | | | FAM90A1 | 1.00 | 12766 | 3 | | | | FGF6 | 1.00 |
| 12671 | 3 | | | | | FAM90A10 | 1.00 | 12767 | 3 | | | | FGF7 | 1.00 |
| 12672 | 3 | | | | | FAM90A10P | 1.00 | 12768 | 3 | | | | FGF8 | 1.00 |
| 12673 | 3 | | | | | FAM90A14 | 1.00 | 12769 | 3 | | | | FGF9 | 1.00 |
| 12674 | 3 | | | | | FAM90A19 | 1.00 | 12770 | 3 | | | | FGFBP1 | 1.00 |
| 12675 | 3 | | | | | FAM90A20 | 1.00 | 12771 | 3 | | | | FGFR2 | 1.00 |
| 12676 | 3 | | | | | FAM90A25P | 1.00 | 12772 | 3 | | | | FGFR3 | 1.00 |
| 12677 | 3 | | | | | FAM90A27P | 1.00 | 12773 | 3 | | | | FGFR4 | 1.00 |
| 12678 | 3 | | | | | FAM90A2P | 1.00 | 12774 | 3 | | | | FGG | 1.00 |
| 12679 | 3 | | | | | FAM90A5 | 1.00 | 12775 | 3 | | | | FGGY | 1.00 |
| 12680 | 3 | | | | | FAM90A7 | 1.00 | 12776 | 3 | | | | FGL1 | 1.00 |
| 12681 | 3 | | | | | FAM90A7P | 1.00 | 12777 | 3 | | | | FHAD1 | 1.00 |
| 12682 | 3 | | | | | FAM90A8 | 1.00 | 12778 | 3 | | | | FHL5 | 1.00 |
| 12683 | 3 | | | | | FAM90A9 | 1.00 | 12779 | 3 | | | | FHOD3 | 1.00 |
| 12684 | 3 | | | | | FAM92A1 | 1.00 | 12780 | 3 | | | | FIBCD1 | 1.00 |
| 12685 | 3 | | | | | FAM92A3 | 1.00 | 12781 | 3 | | | | FIBIN | 1.00 |
| 12686 | 3 | | | | | FAM92B | 1.00 | 12782 | 3 | | | | FIGF | 1.00 |
| 12687 | 3 | | | | | FAM95B1 | 1.00 | 12783 | 3 | | | | FIGLA | 1.00 |
| 12688 | 3 | | | | | FAM99A | 1.00 | 12784 | 3 | | | | FIGN | 1.00 |
| 12689 | 3 | | | | | FAM99B | 1.00 | 12785 | 3 | | | | FIGNL2 | 1.00 |
| 12690 | 3 | | | | | FAM9A | 1.00 | 12786 | 3 | | | | FILIP1 | 1.00 |
| 12691 | 3 | | | | | FAM9B | 1.00 | 12787 | 3 | | | | FILIP1L | 1.00 |
| 12692 | 3 | | | | | FAM9C | 1.00 | 12788 | 3 | | | | FJX1 | 1.00 |
| 12693 | 3 | | | | | FANCB | 1.00 | 12789 | 3 | | | | FKBP10 | 1.00 |
| 12694 | 3 | | | | | FANCC | 1.00 | 12790 | 3 | | | | FKBP1A-SDCBP2 | 1.00 |
| 12695 | 3 | | | | | FANK1 | 1.00 | 12791 | 3 | | | | FKBP6 | 1.00 |
| 12696 | 3 | | | | | FAP | 1.00 | 12792 | 3 | | | | FKBP7 | 1.00 |
| 12697 | 3 | | | | | FARP1 | 1.00 | 12793 | 3 | | | | FKBP9L | 1.00 |
| 12698 | 3 | | | | | FAS-AS1 | 1.00 | 12794 | 3 | | | | FKSG29 | 1.00 |
| 12699 | 3 | | | | | FAT1 | 1.00 | 12795 | 3 | | | | FLG | 1.00 |
| 12700 | 3 | | | | | FAT2 | 1.00 | 12796 | 3 | | | | FLG2 | 1.00 |
| 12701 | 3 | | | | | FAT3 | 1.00 | 12797 | 3 | | | | FLJ11235 | 1.00 |
| 12702 | 3 | | | | | FAT4 | 1.00 | 12798 | 3 | | | | FLJ12825 | 1.00 |
| 12703 | 3 | | | | | FATE1 | 1.00 | 12799 | 3 | | | | FLJ13224 | 1.00 |
| 12704 | 3 | | | | | FAXC | 1.00 | 12800 | 3 | | | | FLJ14107 | 1.00 |
| 12705 | 3 | | | | | FBLIM1 | 1.00 | 12801 | 3 | | | | FLJ16171 | 1.00 |
| 12706 | 3 | | | | | FBLL1 | 1.00 | 12802 | 3 | | | | FLJ16341 | 1.00 |
| 12707 | 3 | | | | | FBLN1 | 1.00 | 12803 | 3 | | | | FLJ16779 | 1.00 |
| 12708 | 3 | | | | | FBN1 | 1.00 | 12804 | 3 | | | | FLJ20518 | 1.00 |
| 12709 | 3 | | | | | FBN3 | 1.00 | 12805 | 3 | | | | FLJ21408 | 1.00 |
| 12710 | 3 | | | | | FBP2 | 1.00 | 12806 | 3 | | | | FLJ22184 | 1.00 |
| 12711 | 3 | | | | | FBXL2 | 1.00 | 12807 | 3 | | | | FLJ22447 | 1.00 |
| 12712 | 3 | | | | | FBXL21 | 1.00 | 12808 | 3 | | | | FLJ22763 | 1.00 |
| 12713 | 3 | | | | | FBXL22 | 1.00 | 12809 | 3 | | | | FLJ23152 | 1.00 |
| 12714 | 3 | | | | | FBXL7 | 1.00 | 12810 | 3 | | | | FLJ25328 | 1.00 |
| 12715 | 3 | | | | | FBXO15 | 1.00 | 12811 | 3 | | | | FLJ25363 | 1.00 |
| 12716 | 3 | | | | | FBXO16 | 1.00 | 12812 | 3 | | | | FLJ25758 | 1.00 |
| 12717 | 3 | | | | | FBXO17 | 1.00 | 12813 | 3 | | | | FLJ26245 | 1.00 |
| 12718 | 3 | | | | | FBXO24 | 1.00 | 12814 | 3 | | | | FLJ26850 | 1.00 |
| 12719 | 3 | | | | | FBXO27 | 1.00 | 12815 | 3 | | | | FLJ30403 | 1.00 |
| 12720 | 3 | | | | | FBXO36 | 1.00 | 12816 | 3 | | | | FLJ30679 | 1.00 |
| 12721 | 3 | | | | | FBXO40 | 1.00 | 12817 | 3 | | | | FLJ30838 | 1.00 |
| 12722 | 3 | | | | | FBXO43 | 1.00 | 12818 | 3 | | | | FLJ31485 | 1.00 |
| 12723 | 3 | | | | | FBXO47 | 1.00 | 12819 | 3 | | | | FLJ31662 | 1.00 |
| 12724 | 3 | | | | | FBXW10 | 1.00 | 12820 | 3 | | | | FLJ32063 | 1.00 |
| 12725 | 3 | | | | | FBXW12 | 1.00 | 12821 | 3 | | | | FLJ33360 | 1.00 |
| 12726 | 3 | | | | | FCAMR | 1.00 | 12822 | 3 | | | | FLJ33534 | 1.00 |
| 12727 | 3 | | | | | FCN2 | 1.00 | 12823 | 3 | | | | FLJ33581 | 1.00 |
| 12728 | 3 | | | | | FCN3 | 1.00 | 12824 | 3 | | | | FLJ34208 | 1.00 |
| 12729 | 3 | | | | | FCRL4 | 1.00 | 12825 | 3 | | | | FLJ34503 | 1.00 |
| 12730 | 3 | | | | | FDCSP | 1.00 | 12826 | 3 | | | | FLJ34690 | 1.00 |
| 12731 | 3 | | | | | FER | 1.00 | 12827 | 3 | | | | FLJ35024 | 1.00 |
| 12732 | 3 | | | | | FER1L4 | 1.00 | 12828 | 3 | | | | FLJ35282 | 1.00 |
| 12733 | 3 | | | | | FER1L5 | 1.00 | 12829 | 3 | | | | FLJ35424 | 1.00 |
| 12734 | 3 | | | | | FER1L6 | 1.00 | 12830 | 3 | | | | FLJ35946 | 1.00 |
| 12735 | 3 | | | | | FER1L6-AS1 | 1.00 | 12831 | 3 | | | | FLJ36000 | 1.00 |
| 12736 | 3 | | | | | FERD3L | 1.00 | 12832 | 3 | | | | FLJ36777 | 1.00 |
| 12737 | 3 | | | | | FERMT1 | 1.00 | 12833 | 3 | | | | FLJ37035 | 1.00 |
| 12738 | 3 | | | | | FERMT2 | 1.00 | 12834 | 3 | | | | FLJ37201 | 1.00 |
| 12739 | 3 | | | | | FETUB | 1.00 | 12835 | 3 | | | | FLJ37505 | 1.00 |
| 12740 | 3 | | | | | FEV | 1.00 | 12836 | 3 | | | | FLJ38576 | 1.00 |
| 12741 | 3 | | | | | FEZF1 | 1.00 | 12837 | 3 | | | | FLJ39080 | 1.00 |
| 12742 | 3 | | | | | FEZF2 | 1.00 | 12838 | 3 | | | | FLJ39534 | 1.00 |
| 12743 | 3 | | | | | FFAR1 | 1.00 | 12839 | 3 | | | | FLJ40194 | 1.00 |
| 12744 | 3 | | | | | FGA | 1.00 | 12840 | 3 | | | | FLJ40288 | 1.00 |
| 12745 | 3 | | | | | FGB | 1.00 | 12841 | 3 | | | | FLJ40292 | 1.00 |
| 12746 | 3 | | | | | FGD1 | 1.00 | 12842 | 3 | | | | FLJ40434 | 1.00 |
| 12747 | 3 | | | | | FGD5 | 1.00 | 12843 | 3 | | | | FLJ40852 | 1.00 |
| 12748 | 3 | | | | | FGF1 | 1.00 | 12844 | 3 | | | | FLJ41200 | 1.00 |
| 12749 | 3 | | | | | FGF10 | 1.00 | 12845 | 3 | | | | FLJ41278 | 1.00 |
| 12750 | 3 | | | | | FGF11 | 1.00 | 12846 | 3 | | | | FLJ41350 | 1.00 |
| 12751 | 3 | | | | | FGF12 | 1.00 | 12847 | 3 | | | | FLJ41649 | 1.00 |
| 12752 | 3 | | | | | FGF14 | 1.00 | 12848 | 3 | | | | FLJ41941 | 1.00 |
| 12753 | 3 | | | | | FGF14-IT1 | 1.00 | 12849 | 3 | | | | FLJ42102 | 1.00 |
| 12754 | 3 | | | | | FGF16 | 1.00 | 12850 | 3 | | | | FLJ42280 | 1.00 |
| 12755 | 3 | | | | | FGF17 | 1.00 | 12851 | 3 | | | | FLJ42289 | 1.00 |
| 12756 | 3 | | | | | FGF18 | 1.00 | 12852 | 3 | | | | FLJ42351 | 1.00 |
| 12757 | 3 | | | | | FGF19 | 1.00 | 12853 | 3 | | | | FLJ42393 | 1.00 |
| 12758 | 3 | | | | | FGF2 | 1.00 | 12854 | 3 | | | | FLJ42709 | 1.00 |
| 12759 | 3 | | | | | FGF20 | 1.00 | 12855 | 3 | | | | FLJ42875 | 1.00 |
| 12760 | 3 | | | | | FGF21 | 1.00 | 12856 | 3 | | | | FLJ42969 | 1.00 |
| 12761 | 3 | | | | | FGF22 | 1.00 | 12857 | 3 | | | | FLJ43315 | 1.00 |
| 12762 | 3 | | | | | FGF23 | 1.00 | 12858 | 3 | | | | FLJ43390 | 1.00 |

Fig. 40 - 68

| | | | | | | | |
|---|---|---|---|---|---|---|---|
| 12859 | 3 | | FLJ43681 | 1.00 | 12955 | 3 | | FRMPD4 | 1.00 |
| 12860 | 3 | | FLJ43826 | 1.00 | 12956 | 3 | | FRRS1 | 1.00 |
| 12861 | 3 | | FLJ43860 | 1.00 | 12957 | 3 | | FRZB | 1.00 |
| 12862 | 3 | | FLJ43879 | 1.00 | 12958 | 3 | | FSBP | 1.00 |
| 12863 | 3 | | FLJ44054 | 1.00 | 12959 | 3 | | FSCB | 1.00 |
| 12864 | 3 | | FLJ45079 | 1.00 | 12960 | 3 | | FSCN2 | 1.00 |
| 12865 | 3 | | FLJ45974 | 1.00 | 12961 | 3 | | FSCN3 | 1.00 |
| 12866 | 3 | | FLJ45983 | 1.00 | 12962 | 3 | | FSD1 | 1.00 |
| 12867 | 3 | | FLJ46066 | 1.00 | 12963 | 3 | | FSD1L | 1.00 |
| 12868 | 3 | | FLJ46257 | 1.00 | 12964 | 3 | | FSD2 | 1.00 |
| 12869 | 3 | | FLJ46284 | 1.00 | 12965 | 3 | | FSHB | 1.00 |
| 12870 | 3 | | FLJ46300 | 1.00 | 12966 | 3 | | FSHR | 1.00 |
| 12871 | 3 | | FLJ46361 | 1.00 | 12967 | 3 | | FSIP1 | 1.00 |
| 12872 | 3 | | FLJ46446 | 1.00 | 12968 | 3 | | FSIP2 | 1.00 |
| 12873 | 3 | | FLNC | 1.00 | 12969 | 3 | | FST | 1.00 |
| 12874 | 3 | | FLRT1 | 1.00 | 12970 | 3 | | FSTL4 | 1.00 |
| 12875 | 3 | | FLRT2 | 1.00 | 12971 | 3 | | FSTL5 | 1.00 |
| 12876 | 3 | | FLRT3 | 1.00 | 12972 | 3 | | FTCD | 1.00 |
| 12877 | 3 | | FLT1 | 1.00 | 12973 | 3 | | FTHL17 | 1.00 |
| 12878 | 3 | | FLT4 | 1.00 | 12974 | 3 | | FTLP10 | 1.00 |
| 12879 | 3 | | FMN2 | 1.00 | 12975 | 3 | | FTMT | 1.00 |
| 12880 | 3 | | FMO1 | 1.00 | 12976 | 3 | | FUT1 | 1.00 |
| 12881 | 3 | | FMO2 | 1.00 | 12977 | 3 | | FUT2 | 1.00 |
| 12882 | 3 | | FMO3 | 1.00 | 12978 | 3 | | FUT3 | 1.00 |
| 12883 | 3 | | FMO6P | 1.00 | 12979 | 3 | | FUT5 | 1.00 |
| 12884 | 3 | | FMO9P | 1.00 | 12980 | 3 | | FUT6 | 1.00 |
| 12885 | 3 | | FMOD | 1.00 | 12981 | 3 | | FUT9 | 1.00 |
| 12886 | 3 | | FMR1-AS1 | 1.00 | 12982 | 3 | | FXYD1 | 1.00 |
| 12887 | 3 | | FMR1NB | 1.00 | 12983 | 3 | | FXYD3 | 1.00 |
| 12888 | 3 | | FN1 | 1.00 | 12984 | 3 | | FXYD4 | 1.00 |
| 12889 | 3 | | FN3K | 1.00 | 12985 | 3 | | FXYD6-FXYD2 | 1.00 |
| 12890 | 3 | | FNDC1 | 1.00 | 12986 | 3 | | FZD10 | 1.00 |
| 12891 | 3 | | FNDC4 | 1.00 | 12987 | 3 | | FZD3 | 1.00 |
| 12892 | 3 | | FNDC5 | 1.00 | 12988 | 3 | | FZD4 | 1.00 |
| 12893 | 3 | | FNDC7 | 1.00 | 12989 | 3 | | FZD5 | 1.00 |
| 12894 | 3 | | FNDC8 | 1.00 | 12990 | 3 | | FZD7 | 1.00 |
| 12895 | 3 | | FNDC9 | 1.00 | 12991 | 3 | | FZD8 | 1.00 |
| 12896 | 3 | | FOLH1 | 1.00 | 12992 | 3 | | FZD9 | 1.00 |
| 12897 | 3 | | FOLH1B | 1.00 | 12993 | 3 | | G6PC | 1.00 |
| 12898 | 3 | | FOLR1 | 1.00 | 12994 | 3 | | G6PC2 | 1.00 |
| 12899 | 3 | | FOLR4 | 1.00 | 12995 | 3 | | GAB4 | 1.00 |
| 12900 | 3 | | FONG | 1.00 | 12996 | 3 | | GABBR2 | 1.00 |
| 12901 | 3 | | FOSL1 | 1.00 | 12997 | 3 | | GABRA1 | 1.00 |
| 12902 | 3 | | FOXA1 | 1.00 | 12998 | 3 | | GABRA2 | 1.00 |
| 12903 | 3 | | FOXA2 | 1.00 | 12999 | 3 | | GABRA3 | 1.00 |
| 12904 | 3 | | FOXA3 | 1.00 | 13000 | 3 | | GABRA4 | 1.00 |
| 12905 | 3 | | FOXB1 | 1.00 | 13001 | 3 | | GABRA5 | 1.00 |
| 12906 | 3 | | FOXB2 | 1.00 | 13002 | 3 | | GABRA6 | 1.00 |
| 12907 | 3 | | FOXC1 | 1.00 | 13003 | 3 | | GABRB1 | 1.00 |
| 12908 | 3 | | FOXC2 | 1.00 | 13004 | 3 | | GABRB2 | 1.00 |
| 12909 | 3 | | FOXD1 | 1.00 | 13005 | 3 | | GABRB3 | 1.00 |
| 12910 | 3 | | FOXD2 | 1.00 | 13006 | 3 | | GABRD | 1.00 |
| 12911 | 3 | | FOXD3 | 1.00 | 13007 | 3 | | GABRE | 1.00 |
| 12912 | 3 | | FOXD4 | 1.00 | 13008 | 3 | | GABRG1 | 1.00 |
| 12913 | 3 | | FOXD4L1 | 1.00 | 13009 | 3 | | GABRG2 | 1.00 |
| 12914 | 3 | | FOXD4L2 | 1.00 | 13010 | 3 | | GABRG3 | 1.00 |
| 12915 | 3 | | FOXD4L3 | 1.00 | 13011 | 3 | | GABRP | 1.00 |
| 12916 | 3 | | FOXD4L5 | 1.00 | 13012 | 3 | | GABRQ | 1.00 |
| 12917 | 3 | | FOXD4L6 | 1.00 | 13013 | 3 | | GABRR1 | 1.00 |
| 12918 | 3 | | FOXE1 | 1.00 | 13014 | 3 | | GABRR2 | 1.00 |
| 12919 | 3 | | FOXE3 | 1.00 | 13015 | 3 | | GABRR3 | 1.00 |
| 12920 | 3 | | FOXF1 | 1.00 | 13016 | 3 | | GAD1 | 1.00 |
| 12921 | 3 | | FOXF2 | 1.00 | 13017 | 3 | | GAD2 | 1.00 |
| 12922 | 3 | | FOXG1 | 1.00 | 13018 | 3 | | GADL1 | 1.00 |
| 12923 | 3 | | FOXH1 | 1.00 | 13019 | 3 | | GAGE1 | 1.00 |
| 12924 | 3 | | FOXI1 | 1.00 | 13020 | 3 | | GAGE10 | 1.00 |
| 12925 | 3 | | FOXI2 | 1.00 | 13021 | 3 | | GAGE12B | 1.00 |
| 12926 | 3 | | FOXI3 | 1.00 | 13022 | 3 | | GAGE12C | 1.00 |
| 12927 | 3 | | FOXJ1 | 1.00 | 13023 | 3 | | GAGE12D | 1.00 |
| 12928 | 3 | | FOXL1 | 1.00 | 13024 | 3 | | GAGE12E | 1.00 |
| 12929 | 3 | | FOXL2 | 1.00 | 13025 | 3 | | GAGE12F | 1.00 |
| 12930 | 3 | | FOXN1 | 1.00 | 13026 | 3 | | GAGE12H | 1.00 |
| 12931 | 3 | | FOXN4 | 1.00 | 13027 | 3 | | GAGE12I | 1.00 |
| 12932 | 3 | | FOXP2 | 1.00 | 13028 | 3 | | GAGE12J | 1.00 |
| 12933 | 3 | | FOXQ1 | 1.00 | 13029 | 3 | | GAGE13 | 1.00 |
| 12934 | 3 | | FOXR1 | 1.00 | 13030 | 3 | | GAGE2A | 1.00 |
| 12935 | 3 | | FOXR2 | 1.00 | 13031 | 3 | | GAGE2B | 1.00 |
| 12936 | 3 | | FOXS1 | 1.00 | 13032 | 3 | | GAGE2C | 1.00 |
| 12937 | 3 | | FP588 | 1.00 | 13033 | 3 | | GAGE2D | 1.00 |
| 12938 | 3 | | FPGT-TNNI3K | 1.00 | 13034 | 3 | | GAGE2E | 1.00 |
| 12939 | 3 | | FRAS1 | 1.00 | 13035 | 3 | | GAGE4 | 1.00 |
| 12940 | 3 | | FREM1 | 1.00 | 13036 | 3 | | GAGE5 | 1.00 |
| 12941 | 3 | | FREM2 | 1.00 | 13037 | 3 | | GAGE6 | 1.00 |
| 12942 | 3 | | FREM3 | 1.00 | 13038 | 3 | | GAGE7 | 1.00 |
| 12943 | 3 | | FRG2 | 1.00 | 13039 | 3 | | GAGE8 | 1.00 |
| 12944 | 3 | | FRG2B | 1.00 | 13040 | 3 | | GAL | 1.00 |
| 12945 | 3 | | FRG2C | 1.00 | 13041 | 3 | | GAL3ST1 | 1.00 |
| 12946 | 3 | | FRK | 1.00 | 13042 | 3 | | GAL3ST2 | 1.00 |
| 12947 | 3 | | FRMD1 | 1.00 | 13043 | 3 | | GAL3ST3 | 1.00 |
| 12948 | 3 | | FRMD5 | 1.00 | 13044 | 3 | | GALNT13 | 1.00 |
| 12949 | 3 | | FRMD6 | 1.00 | 13045 | 3 | | GALNT14 | 1.00 |
| 12950 | 3 | | FRMD6-AS1 | 1.00 | 13046 | 3 | | GALNT5 | 1.00 |
| 12951 | 3 | | FRMD7 | 1.00 | 13047 | 3 | | GALNT8 | 1.00 |
| 12952 | 3 | | FRMPD1 | 1.00 | 13048 | 3 | | GALNT9 | 1.00 |
| 12953 | 3 | | FRMPD2 | 1.00 | 13049 | 3 | | GALNTL1 | 1.00 |
| 12954 | 3 | | FRMPD2P1 | 1.00 | 13050 | 3 | | GALNTL2 | 1.00 |

Fig. 40 - 69

| | | | | | | | | | | | | | | |
|---|---|---|---|---|---|---|---|---|---|---|---|---|---|---|
| 13051 | 3 | | | | | GALNTL4 | 1.00 | 13147 | 3 | | | | GJD2 | 1.00 |
| 13052 | 3 | | | | | GALNTL5 | 1.00 | 13148 | 3 | | | | GJD3 | 1.00 |
| 13053 | 3 | | | | | GALNTL6 | 1.00 | 13149 | 3 | | | | GJD4 | 1.00 |
| 13054 | 3 | | | | | GALP | 1.00 | 13150 | 3 | | | | GK2 | 1.00 |
| 13055 | 3 | | | | | GALR1 | 1.00 | 13151 | 3 | | | | GKN1 | 1.00 |
| 13056 | 3 | | | | | GALR2 | 1.00 | 13152 | 3 | | | | GKN2 | 1.00 |
| 13057 | 3 | | | | | GALR3 | 1.00 | 13153 | 3 | | | | GLB1L2 | 1.00 |
| 13058 | 3 | | | | | GAN | 1.00 | 13154 | 3 | | | | GLB1L3 | 1.00 |
| 13059 | 3 | | | | | GAP43 | 1.00 | 13155 | 3 | | | | GLDC | 1.00 |
| 13060 | 3 | | | | | GAPDHS | 1.00 | 13156 | 3 | | | | GLDN | 1.00 |
| 13061 | 3 | | | | | GARNL3 | 1.00 | 13157 | 3 | | | | GLI2 | 1.00 |
| 13062 | 3 | | | | | GAS1 | 1.00 | 13158 | 3 | | | | GLI3 | 1.00 |
| 13063 | 3 | | | | | GAS2 | 1.00 | 13159 | 3 | | | | GLIPR1L1 | 1.00 |
| 13064 | 3 | | | | | GAS2L2 | 1.00 | 13160 | 3 | | | | GLIPR1L2 | 1.00 |
| 13065 | 3 | | | | | GAS2L3 | 1.00 | 13161 | 3 | | | | GLIS1 | 1.00 |
| 13066 | 3 | | | | | GAST | 1.00 | 13162 | 3 | | | | GLIS3 | 1.00 |
| 13067 | 3 | | | | | GATA4 | 1.00 | 13163 | 3 | | | | GLIS3-AS1 | 1.00 |
| 13068 | 3 | | | | | GATA5 | 1.00 | 13164 | 3 | | | | GLMN | 1.00 |
| 13069 | 3 | | | | | GATA6 | 1.00 | 13165 | 3 | | | | GLOD5 | 1.00 |
| 13070 | 3 | | | | | GATSL1 | 1.00 | 13166 | 3 | | | | GLP1R | 1.00 |
| 13071 | 3 | | | | | GBA3 | 1.00 | 13167 | 3 | | | | GLP2R | 1.00 |
| 13072 | 3 | | | | | GBP7 | 1.00 | 13168 | 3 | | | | GLRA1 | 1.00 |
| 13073 | 3 | | | | | GBX1 | 1.00 | 13169 | 3 | | | | GLRA2 | 1.00 |
| 13074 | 3 | | | | | GBX2 | 1.00 | 13170 | 3 | | | | GLRA3 | 1.00 |
| 13075 | 3 | | | | | GC | 1.00 | 13171 | 3 | | | | GLRA4 | 1.00 |
| 13076 | 3 | | | | | GCAT | 1.00 | 13172 | 3 | | | | GLRB | 1.00 |
| 13077 | 3 | | | | | GCG | 1.00 | 13173 | 3 | | | | GLS2 | 1.00 |
| 13078 | 3 | | | | | GCGR | 1.00 | 13174 | 3 | | | | GLT25D2 | 1.00 |
| 13079 | 3 | | | | | GCK | 1.00 | 13175 | 3 | | | | GLT6D1 | 1.00 |
| 13080 | 3 | | | | | GCKR | 1.00 | 13176 | 3 | | | | GLT8D2 | 1.00 |
| 13081 | 3 | | | | | GCM2 | 1.00 | 13177 | 3 | | | | GLTPD2 | 1.00 |
| 13082 | 3 | | | | | GCNT3 | 1.00 | 13178 | 3 | | | | GLYAT | 1.00 |
| 13083 | 3 | | | | | GCNT7 | 1.00 | 13179 | 3 | | | | GLYATL1 | 1.00 |
| 13084 | 3 | | | | | GCOM1 | 1.00 | 13180 | 3 | | | | GLYATL2 | 1.00 |
| 13085 | 3 | | | | | GCSH | 1.00 | 13181 | 3 | | | | GLYATL3 | 1.00 |
| 13086 | 3 | | | | | GDA | 1.00 | 13182 | 3 | | | | GLYCAM1 | 1.00 |
| 13087 | 3 | | | | | GDAP1L1 | 1.00 | 13183 | 3 | | | | GM140 | 1.00 |
| 13088 | 3 | | | | | GDEP | 1.00 | 13184 | 3 | | | | GML | 1.00 |
| 13089 | 3 | | | | | GDF10 | 1.00 | 13185 | 3 | | | | GMNC | 1.00 |
| 13090 | 3 | | | | | GDF15 | 1.00 | 13186 | 3 | | | | GNA14 | 1.00 |
| 13091 | 3 | | | | | GDF2 | 1.00 | 13187 | 3 | | | | GNAI1 | 1.00 |
| 13092 | 3 | | | | | GDF3 | 1.00 | 13188 | 3 | | | | GNAS-AS1 | 1.00 |
| 13093 | 3 | | | | | GDF5 | 1.00 | 13189 | 3 | | | | GNAT1 | 1.00 |
| 13094 | 3 | | | | | GDF6 | 1.00 | 13190 | 3 | | | | GNAT2 | 1.00 |
| 13095 | 3 | | | | | GDF7 | 1.00 | 13191 | 3 | | | | GNAT3 | 1.00 |
| 13096 | 3 | | | | | GDF9 | 1.00 | 13192 | 3 | | | | GNB3 | 1.00 |
| 13097 | 3 | | | | | GDNF | 1.00 | 13193 | 3 | | | | GNG12 | 1.00 |
| 13098 | 3 | | | | | GDPD2 | 1.00 | 13194 | 3 | | | | GNG13 | 1.00 |
| 13099 | 3 | | | | | GDPD4 | 1.00 | 13195 | 3 | | | | GNG3 | 1.00 |
| 13100 | 3 | | | | | GEM | 1.00 | 13196 | 3 | | | | GNG4 | 1.00 |
| 13101 | 3 | | | | | GEMIN2 | 1.00 | 13197 | 3 | | | | GNGT1 | 1.00 |
| 13102 | 3 | | | | | GFAP | 1.00 | 13198 | 3 | | | | GNN | 1.00 |
| 13103 | 3 | | | | | GFPT2 | 1.00 | 13199 | 3 | | | | GNRH2 | 1.00 |
| 13104 | 3 | | | | | GFRA1 | 1.00 | 13200 | 3 | | | | GNRHR | 1.00 |
| 13105 | 3 | | | | | GFRA2 | 1.00 | 13201 | 3 | | | | GOLGA2P3Y | 1.00 |
| 13106 | 3 | | | | | GFRA3 | 1.00 | 13202 | 3 | | | | GOLGA6A | 1.00 |
| 13107 | 3 | | | | | GFRA4 | 1.00 | 13203 | 3 | | | | GOLGA6B | 1.00 |
| 13108 | 3 | | | | | GFRAL | 1.00 | 13204 | 3 | | | | GOLGA6C | 1.00 |
| 13109 | 3 | | | | | GGH | 1.00 | 13205 | 3 | | | | GOLGA6D | 1.00 |
| 13110 | 3 | | | | | GGN | 1.00 | 13206 | 3 | | | | GOLGA6L1 | 1.00 |
| 13111 | 3 | | | | | GGNBP1 | 1.00 | 13207 | 3 | | | | GOLGA6L10 | 1.00 |
| 13112 | 3 | | | | | GGT3P | 1.00 | 13208 | 3 | | | | GOLGA6L5 | 1.00 |
| 13113 | 3 | | | | | GGT5 | 1.00 | 13209 | 3 | | | | GOLGA6L6 | 1.00 |
| 13114 | 3 | | | | | GGT6 | 1.00 | 13210 | 3 | | | | GOLGA8C | 1.00 |
| 13115 | 3 | | | | | GGT8P | 1.00 | 13211 | 3 | | | | GOLGA8DP | 1.00 |
| 13116 | 3 | | | | | GGTLC1 | 1.00 | 13212 | 3 | | | | GOLGA8E | 1.00 |
| 13117 | 3 | | | | | GH1 | 1.00 | 13213 | 3 | | | | GOLGA8F | 1.00 |
| 13118 | 3 | | | | | GH2 | 1.00 | 13214 | 3 | | | | GOLGA8G | 1.00 |
| 13119 | 3 | | | | | GHR | 1.00 | 13215 | 3 | | | | GOLGA8IP | 1.00 |
| 13120 | 3 | | | | | GHRH | 1.00 | 13216 | 3 | | | | GOLT1A | 1.00 |
| 13121 | 3 | | | | | GHRHR | 1.00 | 13217 | 3 | | | | GOT1L1 | 1.00 |
| 13122 | 3 | | | | | GHSR | 1.00 | 13218 | 3 | | | | GP2 | 1.00 |
| 13123 | 3 | | | | | GIF | 1.00 | 13219 | 3 | | | | GPAT2 | 1.00 |
| 13124 | 3 | | | | | GINS1 | 1.00 | 13220 | 3 | | | | GPC1 | 1.00 |
| 13125 | 3 | | | | | GINS2 | 1.00 | 13221 | 3 | | | | GPC3 | 1.00 |
| 13126 | 3 | | | | | GINS4 | 1.00 | 13222 | 3 | | | | GPC5 | 1.00 |
| 13127 | 3 | | | | | GIP | 1.00 | 13223 | 3 | | | | GPC6 | 1.00 |
| 13128 | 3 | | | | | GIPC2 | 1.00 | 13224 | 3 | | | | GPCRLTM7 | 1.00 |
| 13129 | 3 | | | | | GIPR | 1.00 | 13225 | 3 | | | | GPD1 | 1.00 |
| 13130 | 3 | | | | | GJA1 | 1.00 | 13226 | 3 | | | | GPHA2 | 1.00 |
| 13131 | 3 | | | | | GJA10 | 1.00 | 13227 | 3 | | | | GPHB5 | 1.00 |
| 13132 | 3 | | | | | GJA3 | 1.00 | 13228 | 3 | | | | GPHN | 1.00 |
| 13133 | 3 | | | | | GJA4 | 1.00 | 13229 | 3 | | | | GPIHBP1 | 1.00 |
| 13134 | 3 | | | | | GJA5 | 1.00 | 13230 | 3 | | | | GPLD1 | 1.00 |
| 13135 | 3 | | | | | GJA8 | 1.00 | 13231 | 3 | | | | GPNMB | 1.00 |
| 13136 | 3 | | | | | GJA9 | 1.00 | 13232 | 3 | | | | GPR1 | 1.00 |
| 13137 | 3 | | | | | GJB1 | 1.00 | 13233 | 3 | | | | GPR101 | 1.00 |
| 13138 | 3 | | | | | GJB2 | 1.00 | 13234 | 3 | | | | GPR110 | 1.00 |
| 13139 | 3 | | | | | GJB3 | 1.00 | 13235 | 3 | | | | GPR111 | 1.00 |
| 13140 | 3 | | | | | GJB4 | 1.00 | 13236 | 3 | | | | GPR112 | 1.00 |
| 13141 | 3 | | | | | GJB5 | 1.00 | 13237 | 3 | | | | GPR113 | 1.00 |
| 13142 | 3 | | | | | GJB6 | 1.00 | 13238 | 3 | | | | GPR115 | 1.00 |
| 13143 | 3 | | | | | GJB7 | 1.00 | 13239 | 3 | | | | GPR116 | 1.00 |
| 13144 | 3 | | | | | GJC1 | 1.00 | 13240 | 3 | | | | GPR119 | 1.00 |
| 13145 | 3 | | | | | GJC2 | 1.00 | 13241 | 3 | | | | GPR12 | 1.00 |
| 13146 | 3 | | | | | GJC3 | 1.00 | 13242 | 3 | | | | GPR123 | 1.00 |

Fig. 40 - 70

| | | | | | | | | | | | | | | | | |
|---|---|---|---|---|---|---|---|---|---|---|---|---|---|---|---|---|
| 13243 | 3 | | | | | GPR125 | 1.00 | | 13339 | 3 | | | | | GRK7 | 1.00 |
| 13244 | 3 | | | | | GPR126 | 1.00 | | 13340 | 3 | | | | | GRM1 | 1.00 |
| 13245 | 3 | | | | | GPR128 | 1.00 | | 13341 | 3 | | | | | GRM2 | 1.00 |
| 13246 | 3 | | | | | GPR135 | 1.00 | | 13342 | 3 | | | | | GRM3 | 1.00 |
| 13247 | 3 | | | | | GPR137C | 1.00 | | 13343 | 3 | | | | | GRM4 | 1.00 |
| 13248 | 3 | | | | | GPR139 | 1.00 | | 13344 | 3 | | | | | GRM5 | 1.00 |
| 13249 | 3 | | | | | GPR142 | 1.00 | | 13345 | 3 | | | | | GRM6 | 1.00 |
| 13250 | 3 | | | | | GPR143 | 1.00 | | 13346 | 3 | | | | | GRM7 | 1.00 |
| 13251 | 3 | | | | | GPR144 | 1.00 | | 13347 | 3 | | | | | GRM8 | 1.00 |
| 13252 | 3 | | | | | GPR148 | 1.00 | | 13348 | 3 | | | | | GRP | 1.00 |
| 13253 | 3 | | | | | GPR149 | 1.00 | | 13349 | 3 | | | | | GRPR | 1.00 |
| 13254 | 3 | | | | | GPR150 | 1.00 | | 13350 | 3 | | | | | GRTP1 | 1.00 |
| 13255 | 3 | | | | | GPR151 | 1.00 | | 13351 | 3 | | | | | GRXCR1 | 1.00 |
| 13256 | 3 | | | | | GPR152 | 1.00 | | 13352 | 3 | | | | | GRXCR2 | 1.00 |
| 13257 | 3 | | | | | GPR156 | 1.00 | | 13353 | 3 | | | | | GSC | 1.00 |
| 13258 | 3 | | | | | GPR158 | 1.00 | | 13354 | 3 | | | | | GSC2 | 1.00 |
| 13259 | 3 | | | | | GPR161 | 1.00 | | 13355 | 3 | | | | | GSDMA | 1.00 |
| 13260 | 3 | | | | | GPR17 | 1.00 | | 13356 | 3 | | | | | GSDMC | 1.00 |
| 13261 | 3 | | | | | GPR172B | 1.00 | | 13357 | 3 | | | | | GSG1 | 1.00 |
| 13262 | 3 | | | | | GPR173 | 1.00 | | 13358 | 3 | | | | | GSG1L | 1.00 |
| 13263 | 3 | | | | | GPR176 | 1.00 | | 13359 | 3 | | | | | GSG2 | 1.00 |
| 13264 | 3 | | | | | GPR179 | 1.00 | | 13360 | 3 | | | | | GSTA1 | 1.00 |
| 13265 | 3 | | | | | GPR182 | 1.00 | | 13361 | 3 | | | | | GSTA2 | 1.00 |
| 13266 | 3 | | | | | GPR19 | 1.00 | | 13362 | 3 | | | | | GSTA3 | 1.00 |
| 13267 | 3 | | | | | GPR20 | 1.00 | | 13363 | 3 | | | | | GSTA4 | 1.00 |
| 13268 | 3 | | | | | GPR21 | 1.00 | | 13364 | 3 | | | | | GSTA5 | 1.00 |
| 13269 | 3 | | | | | GPR22 | 1.00 | | 13365 | 3 | | | | | GSTA7P | 1.00 |
| 13270 | 3 | | | | | GPR26 | 1.00 | | 13366 | 3 | | | | | GSTM5 | 1.00 |
| 13271 | 3 | | | | | GPR3 | 1.00 | | 13367 | 3 | | | | | GSTO2 | 1.00 |
| 13272 | 3 | | | | | GPR31 | 1.00 | | 13368 | 3 | | | | | GSTT2 | 1.00 |
| 13273 | 3 | | | | | GPR32 | 1.00 | | 13369 | 3 | | | | | GSTT2B | 1.00 |
| 13274 | 3 | | | | | GPR33 | 1.00 | | 13370 | 3 | | | | | GSTTP1 | 1.00 |
| 13275 | 3 | | | | | GPR37 | 1.00 | | 13371 | 3 | | | | | GSTTP2 | 1.00 |
| 13276 | 3 | | | | | GPR37L1 | 1.00 | | 13372 | 3 | | | | | GSX1 | 1.00 |
| 13277 | 3 | | | | | GPR39 | 1.00 | | 13373 | 3 | | | | | GSX2 | 1.00 |
| 13278 | 3 | | | | | GPR4 | 1.00 | | 13374 | 3 | | | | | GTF2A1L | 1.00 |
| 13279 | 3 | | | | | GPR45 | 1.00 | | 13375 | 3 | | | | | GTF2IRD1 | 1.00 |
| 13280 | 3 | | | | | GPR50 | 1.00 | | 13376 | 3 | | | | | GTSE1 | 1.00 |
| 13281 | 3 | | | | | GPR52 | 1.00 | | 13377 | 3 | | | | | GTSF1L | 1.00 |
| 13282 | 3 | | | | | GPR6 | 1.00 | | 13378 | 3 | | | | | GUCA1A | 1.00 |
| 13283 | 3 | | | | | GPR61 | 1.00 | | 13379 | 3 | | | | | GUCA1C | 1.00 |
| 13284 | 3 | | | | | GPR62 | 1.00 | | 13380 | 3 | | | | | GUCA2A | 1.00 |
| 13285 | 3 | | | | | GPR63 | 1.00 | | 13381 | 3 | | | | | GUCA2B | 1.00 |
| 13286 | 3 | | | | | GPR64 | 1.00 | | 13382 | 3 | | | | | GUCY1A2 | 1.00 |
| 13287 | 3 | | | | | GPR75-ASB3 | 1.00 | | 13383 | 3 | | | | | GUCY1B2 | 1.00 |
| 13288 | 3 | | | | | GPR78 | 1.00 | | 13384 | 3 | | | | | GUCY2C | 1.00 |
| 13289 | 3 | | | | | GPR83 | 1.00 | | 13385 | 3 | | | | | GUCY2D | 1.00 |
| 13290 | 3 | | | | | GPR85 | 1.00 | | 13386 | 3 | | | | | GUCY2E | 1.00 |
| 13291 | 3 | | | | | GPR87 | 1.00 | | 13387 | 3 | | | | | GUCY2F | 1.00 |
| 13292 | 3 | | | | | GPR88 | 1.00 | | 13388 | 3 | | | | | GUCY2GP | 1.00 |
| 13293 | 3 | | | | | GPR98 | 1.00 | | 13389 | 3 | | | | | GULP1 | 1.00 |
| 13294 | 3 | | | | | GPRASP2 | 1.00 | | 13390 | 3 | | | | | GUSBP10 | 1.00 |
| 13295 | 3 | | | | | GPRC5A | 1.00 | | 13391 | 3 | | | | | GUSBP2 | 1.00 |
| 13296 | 3 | | | | | GPRC5B | 1.00 | | 13392 | 3 | | | | | GUSBP4 | 1.00 |
| 13297 | 3 | | | | | GPRC5C | 1.00 | | 13393 | 3 | | | | | GXYLT2 | 1.00 |
| 13298 | 3 | | | | | GPRC6A | 1.00 | | 13394 | 3 | | | | | GYG2 | 1.00 |
| 13299 | 3 | | | | | GPRIN1 | 1.00 | | 13395 | 3 | | | | | GYG2P1 | 1.00 |
| 13300 | 3 | | | | | GPRIN2 | 1.00 | | 13396 | 3 | | | | | GYPA | 1.00 |
| 13301 | 3 | | | | | GPT | 1.00 | | 13397 | 3 | | | | | GYPE | 1.00 |
| 13302 | 3 | | | | | GPX2 | 1.00 | | 13398 | 3 | | | | | GYS2 | 1.00 |
| 13303 | 3 | | | | | GPX5 | 1.00 | | 13399 | 3 | | | | | H1FNT | 1.00 |
| 13304 | 3 | | | | | GPX6 | 1.00 | | 13400 | 3 | | | | | H1FOO | 1.00 |
| 13305 | 3 | | | | | GPX8 | 1.00 | | 13401 | 3 | | | | | H1FX-AS1 | 1.00 |
| 13306 | 3 | | | | | GRAMD2 | 1.00 | | 13402 | 3 | | | | | H2AFB1 | 1.00 |
| 13307 | 3 | | | | | GRB14 | 1.00 | | 13403 | 3 | | | | | H2AFB3 | 1.00 |
| 13308 | 3 | | | | | GRB7 | 1.00 | | 13404 | 3 | | | | | H2BFM | 1.00 |
| 13309 | 3 | | | | | GREB1 | 1.00 | | 13405 | 3 | | | | | H2BFWT | 1.00 |
| 13310 | 3 | | | | | GREB1L | 1.00 | | 13406 | 3 | | | | | H2BFXP | 1.00 |
| 13311 | 3 | | | | | GREM1 | 1.00 | | 13407 | 3 | | | | | HABP2 | 1.00 |
| 13312 | 3 | | | | | GREM2 | 1.00 | | 13408 | 3 | | | | | HAMP | 1.00 |
| 13313 | 3 | | | | | GRHL2 | 1.00 | | 13409 | 3 | | | | | HAND1 | 1.00 |
| 13314 | 3 | | | | | GRHL3 | 1.00 | | 13410 | 3 | | | | | HAND2 | 1.00 |
| 13315 | 3 | | | | | GRIA1 | 1.00 | | 13411 | 3 | | | | | HAO1 | 1.00 |
| 13316 | 3 | | | | | GRIA2 | 1.00 | | 13412 | 3 | | | | | HAO2 | 1.00 |
| 13317 | 3 | | | | | GRIA3 | 1.00 | | 13413 | 3 | | | | | HAP1 | 1.00 |
| 13318 | 3 | | | | | GRIA4 | 1.00 | | 13414 | 3 | | | | | HAPLN1 | 1.00 |
| 13319 | 3 | | | | | GRID1 | 1.00 | | 13415 | 3 | | | | | HAPLN2 | 1.00 |
| 13320 | 3 | | | | | GRID2 | 1.00 | | 13416 | 3 | | | | | HAPLN4 | 1.00 |
| 13321 | 3 | | | | | GRID2IP | 1.00 | | 13417 | 3 | | | | | HAR1A | 1.00 |
| 13322 | 3 | | | | | GRIK1 | 1.00 | | 13418 | 3 | | | | | HAR1B | 1.00 |
| 13323 | 3 | | | | | GRIK1-AS1 | 1.00 | | 13419 | 3 | | | | | HAS1 | 1.00 |
| 13324 | 3 | | | | | GRIK1-AS2 | 1.00 | | 13420 | 3 | | | | | HAS2 | 1.00 |
| 13325 | 3 | | | | | GRIK2 | 1.00 | | 13421 | 3 | | | | | HAS2-AS1 | 1.00 |
| 13326 | 3 | | | | | GRIK3 | 1.00 | | 13422 | 3 | | | | | HAS3 | 1.00 |
| 13327 | 3 | | | | | GRIK4 | 1.00 | | 13423 | 3 | | | | | HAVCR1 | 1.00 |
| 13328 | 3 | | | | | GRIK5 | 1.00 | | 13424 | 3 | | | | | HBBP1 | 1.00 |
| 13329 | 3 | | | | | GRIN1 | 1.00 | | 13425 | 3 | | | | | HBE1 | 1.00 |
| 13330 | 3 | | | | | GRIN2A | 1.00 | | 13426 | 3 | | | | | HCAR1 | 1.00 |
| 13331 | 3 | | | | | GRIN2B | 1.00 | | 13427 | 3 | | | | | HCG22 | 1.00 |
| 13332 | 3 | | | | | GRIN2C | 1.00 | | 13428 | 3 | | | | | HCG23 | 1.00 |
| 13333 | 3 | | | | | GRIN2D | 1.00 | | 13429 | 3 | | | | | HCG25 | 1.00 |
| 13334 | 3 | | | | | GRIN3B | 1.00 | | 13430 | 3 | | | | | HCG4 | 1.00 |
| 13335 | 3 | | | | | GRIP1 | 1.00 | | 13431 | 3 | | | | | HCG4B | 1.00 |
| 13336 | 3 | | | | | GRIP2 | 1.00 | | 13432 | 3 | | | | | HCG9 | 1.00 |
| 13337 | 3 | | | | | GRK1 | 1.00 | | 13433 | 3 | | | | | HCN1 | 1.00 |
| 13338 | 3 | | | | | GRK4 | 1.00 | | 13434 | 3 | | | | | HCN2 | 1.00 |

Fig. 40 - 71

| | | | | | | | | | | | | | | |
|---|---|---|---|---|---|---|---|---|---|---|---|---|---|---|
| 13435 | 3 | | | | | HCN3 | 1.00 | 13531 | 3 | | | | HNRNPA1P10 | 1.00 |
| 13436 | 3 | | | | | HCN4 | 1.00 | 13532 | 3 | | | | HNRNPA3P1 | 1.00 |
| 13437 | 3 | | | | | HCRT | 1.00 | 13533 | 3 | | | | HNRNPCL1 | 1.00 |
| 13438 | 3 | | | | | HCRTR1 | 1.00 | 13534 | 3 | | | | HOGA1 | 1.00 |
| 13439 | 3 | | | | | HCRTR2 | 1.00 | 13535 | 3 | | | | HOMER1 | 1.00 |
| 13440 | 3 | | | | | HDGFL1 | 1.00 | 13536 | 3 | | | | HORMAD2 | 1.00 |
| 13441 | 3 | | | | | HDX | 1.00 | 13537 | 3 | | | | HOTAIR | 1.00 |
| 13442 | 3 | | | | | HEATR4 | 1.00 | 13538 | 3 | | | | HOTTIP | 1.00 |
| 13443 | 3 | | | | | HEATR7B2 | 1.00 | 13539 | 3 | | | | HOXA-AS3 | 1.00 |
| 13444 | 3 | | | | | HEATR8 | 1.00 | 13540 | 3 | | | | HOXA-AS5 | 1.00 |
| 13445 | 3 | | | | | HEATR8-TTC4 | 1.00 | 13541 | 3 | | | | HOXA10-HOXA9 | 1.00 |
| 13446 | 3 | | | | | HECTD2 | 1.00 | 13542 | 3 | | | | HOXA11 | 1.00 |
| 13447 | 3 | | | | | HECW1 | 1.00 | 13543 | 3 | | | | HOXA13 | 1.00 |
| 13448 | 3 | | | | | HELLS | 1.00 | 13544 | 3 | | | | HOXA2 | 1.00 |
| 13449 | 3 | | | | | HELT | 1.00 | 13545 | 3 | | | | HOXA3 | 1.00 |
| 13450 | 3 | | | | | HEPACAM | 1.00 | 13546 | 3 | | | | HOXA4 | 1.00 |
| 13451 | 3 | | | | | HEPACAM2 | 1.00 | 13547 | 3 | | | | HOXA5 | 1.00 |
| 13452 | 3 | | | | | HEPH | 1.00 | 13548 | 3 | | | | HOXA6 | 1.00 |
| 13453 | 3 | | | | | HEPHL1 | 1.00 | 13549 | 3 | | | | HOXA7 | 1.00 |
| 13454 | 3 | | | | | HEPN1 | 1.00 | 13550 | 3 | | | | HOXB-AS3 | 1.00 |
| 13455 | 3 | | | | | HERC2P4 | 1.00 | 13551 | 3 | | | | HOXB-AS5 | 1.00 |
| 13456 | 3 | | | | | HES2 | 1.00 | 13552 | 3 | | | | HOXB1 | 1.00 |
| 13457 | 3 | | | | | HES3 | 1.00 | 13553 | 3 | | | | HOXB13 | 1.00 |
| 13458 | 3 | | | | | HES5 | 1.00 | 13554 | 3 | | | | HOXB5 | 1.00 |
| 13459 | 3 | | | | | HES7 | 1.00 | 13555 | 3 | | | | HOXB6 | 1.00 |
| 13460 | 3 | | | | | HESX1 | 1.00 | 13556 | 3 | | | | HOXB7 | 1.00 |
| 13461 | 3 | | | | | HEY2 | 1.00 | 13557 | 3 | | | | HOXB8 | 1.00 |
| 13462 | 3 | | | | | HEYL | 1.00 | 13558 | 3 | | | | HOXB9 | 1.00 |
| 13463 | 3 | | | | | HFE2 | 1.00 | 13559 | 3 | | | | HOXC10 | 1.00 |
| 13464 | 3 | | | | | HFM1 | 1.00 | 13560 | 3 | | | | HOXC11 | 1.00 |
| 13465 | 3 | | | | | HGC6.3 | 1.00 | 13561 | 3 | | | | HOXC12 | 1.00 |
| 13466 | 3 | | | | | HGFAC | 1.00 | 13562 | 3 | | | | HOXC13 | 1.00 |
| 13467 | 3 | | | | | HHATL | 1.00 | 13563 | 3 | | | | HOXC5 | 1.00 |
| 13468 | 3 | | | | | HHIP | 1.00 | 13564 | 3 | | | | HOXC6 | 1.00 |
| 13469 | 3 | | | | | HHIPL1 | 1.00 | 13565 | 3 | | | | HOXC8 | 1.00 |
| 13470 | 3 | | | | | HHIPL2 | 1.00 | 13566 | 3 | | | | HOXC9 | 1.00 |
| 13471 | 3 | | | | | HHLA1 | 1.00 | 13567 | 3 | | | | HOXD-AS1 | 1.00 |
| 13472 | 3 | | | | | HHLA2 | 1.00 | 13568 | 3 | | | | HOXD-AS2 | 1.00 |
| 13473 | 3 | | | | | HIF1A-AS2 | 1.00 | 13569 | 3 | | | | HOXD1 | 1.00 |
| 13474 | 3 | | | | | HIF3A | 1.00 | 13570 | 3 | | | | HOXD10 | 1.00 |
| 13475 | 3 | | | | | HIGD1B | 1.00 | 13571 | 3 | | | | HOXD11 | 1.00 |
| 13476 | 3 | | | | | HIGD1C | 1.00 | 13572 | 3 | | | | HOXD12 | 1.00 |
| 13477 | 3 | | | | | HIGD2B | 1.00 | 13573 | 3 | | | | HOXD13 | 1.00 |
| 13478 | 3 | | | | | HILS1 | 1.00 | 13574 | 3 | | | | HOXD3 | 1.00 |
| 13479 | 3 | | | | | HIPK4 | 1.00 | 13575 | 3 | | | | HOXD4 | 1.00 |
| 13480 | 3 | | | | | HIST1H1A | 1.00 | 13576 | 3 | | | | HOXD8 | 1.00 |
| 13481 | 3 | | | | | HIST1H1B | 1.00 | 13577 | 3 | | | | HOXD9 | 1.00 |
| 13482 | 3 | | | | | HIST1H1D | 1.00 | 13578 | 3 | | | | HPCA | 1.00 |
| 13483 | 3 | | | | | HIST1H1E | 1.00 | 13579 | 3 | | | | HPD | 1.00 |
| 13484 | 3 | | | | | HIST1H2AA | 1.00 | 13580 | 3 | | | | HPDL | 1.00 |
| 13485 | 3 | | | | | HIST1H2AB | 1.00 | 13581 | 3 | | | | HPGDS | 1.00 |
| 13486 | 3 | | | | | HIST1H2AH | 1.00 | 13582 | 3 | | | | HPN | 1.00 |
| 13487 | 3 | | | | | HIST1H2AL | 1.00 | 13583 | 3 | | | | HPR | 1.00 |
| 13488 | 3 | | | | | HIST1H2APS1 | 1.00 | 13584 | 3 | | | | HPSE2 | 1.00 |
| 13489 | 3 | | | | | HIST1H2BA | 1.00 | 13585 | 3 | | | | HPVC1 | 1.00 |
| 13490 | 3 | | | | | HIST1H2BB | 1.00 | 13586 | 3 | | | | HPX | 1.00 |
| 13491 | 3 | | | | | HIST1H2BI | 1.00 | 13587 | 3 | | | | HPYR1 | 1.00 |
| 13492 | 3 | | | | | HIST1H2BM | 1.00 | 13588 | 3 | | | | HR | 1.00 |
| 13493 | 3 | | | | | HIST1H3A | 1.00 | 13589 | 3 | | | | HRC | 1.00 |
| 13494 | 3 | | | | | HIST1H3B | 1.00 | 13590 | 3 | | | | HRCT1 | 1.00 |
| 13495 | 3 | | | | | HIST1H3C | 1.00 | 13591 | 3 | | | | HRG | 1.00 |
| 13496 | 3 | | | | | HIST1H3F | 1.00 | 13592 | 3 | | | | HRH1 | 1.00 |
| 13497 | 3 | | | | | HIST1H3G | 1.00 | 13593 | 3 | | | | HRH3 | 1.00 |
| 13498 | 3 | | | | | HIST1H3I | 1.00 | 13594 | 3 | | | | HRK | 1.00 |
| 13499 | 3 | | | | | HIST1H4A | 1.00 | 13595 | 3 | | | | HRNR | 1.00 |
| 13500 | 3 | | | | | HIST1H4B | 1.00 | 13596 | 3 | | | | HS3ST2 | 1.00 |
| 13501 | 3 | | | | | HIST1H4C | 1.00 | 13597 | 3 | | | | HS3ST4 | 1.00 |
| 13502 | 3 | | | | | HIST1H4F | 1.00 | 13598 | 3 | | | | HS3ST5 | 1.00 |
| 13503 | 3 | | | | | HIST1H4G | 1.00 | 13599 | 3 | | | | HS3ST6 | 1.00 |
| 13504 | 3 | | | | | HIST1H4L | 1.00 | 13600 | 3 | | | | HS6ST2 | 1.00 |
| 13505 | 3 | | | | | HIST2H2AB | 1.00 | 13601 | 3 | | | | HS6ST3 | 1.00 |
| 13506 | 3 | | | | | HIST3H3 | 1.00 | 13602 | 3 | | | | HSD11B1 | 1.00 |
| 13507 | 3 | | | | | HJURP | 1.00 | 13603 | 3 | | | | HSD11B1L | 1.00 |
| 13508 | 3 | | | | | HLA-L | 1.00 | 13604 | 3 | | | | HSD11B2 | 1.00 |
| 13509 | 3 | | | | | HLF | 1.00 | 13605 | 3 | | | | HSD17B14 | 1.00 |
| 13510 | 3 | | | | | HMCN1 | 1.00 | 13606 | 3 | | | | HSD17B2 | 1.00 |
| 13511 | 3 | | | | | HMGA1P7 | 1.00 | 13607 | 3 | | | | HSD17B3 | 1.00 |
| 13512 | 3 | | | | | HMGA2 | 1.00 | 13608 | 3 | | | | HSD17B6 | 1.00 |
| 13513 | 3 | | | | | HMGB3 | 1.00 | 13609 | 3 | | | | HSD3B1 | 1.00 |
| 13514 | 3 | | | | | HMGB3P1 | 1.00 | 13610 | 3 | | | | HSD3B2 | 1.00 |
| 13515 | 3 | | | | | HMGB4 | 1.00 | 13611 | 3 | | | | HSD3BP4 | 1.00 |
| 13516 | 3 | | | | | HMGCLL1 | 1.00 | 13612 | 3 | | | | HSDL2 | 1.00 |
| 13517 | 3 | | | | | HMGCS2 | 1.00 | 13613 | 3 | | | | HSF2BP | 1.00 |
| 13518 | 3 | | | | | HMGN2P46 | 1.00 | 13614 | 3 | | | | HSF5 | 1.00 |
| 13519 | 3 | | | | | HMHB1 | 1.00 | 13615 | 3 | | | | HSFX2 | 1.00 |
| 13520 | 3 | | | | | HMMR | 1.00 | 13616 | 3 | | | | HSFY1 | 1.00 |
| 13521 | 3 | | | | | HMP19 | 1.00 | 13617 | 3 | | | | HSFY1P1 | 1.00 |
| 13522 | 3 | | | | | HMSD | 1.00 | 13618 | 3 | | | | HSFY2 | 1.00 |
| 13523 | 3 | | | | | HMX1 | 1.00 | 13619 | 3 | | | | HSP90AB4P | 1.00 |
| 13524 | 3 | | | | | HMX2 | 1.00 | 13620 | 3 | | | | HSPA12A | 1.00 |
| 13525 | 3 | | | | | HMX3 | 1.00 | 13621 | 3 | | | | HSPA12B | 1.00 |
| 13526 | 3 | | | | | HNF1A | 1.00 | 13622 | 3 | | | | HSPA2 | 1.00 |
| 13527 | 3 | | | | | HNF1A-AS1 | 1.00 | 13623 | 3 | | | | HSPA4L | 1.00 |
| 13528 | 3 | | | | | HNF1B | 1.00 | 13624 | 3 | | | | HSPB2 | 1.00 |
| 13529 | 3 | | | | | HNF4A | 1.00 | 13625 | 3 | | | | HSPB2-C11orf52 | 1.00 |
| 13530 | 3 | | | | | HNF4G | 1.00 | 13626 | 3 | | | | HSPB3 | 1.00 |

Fig. 40 - 72

| | | | | | | | | | | | | | |
|---|---|---|---|---|---|---|---|---|---|---|---|---|---|
| 13627 | 3 | | | | | HSPB6 | 1.00 | 13723 | 3 | | | IGSF23 | 1.00 |
| 13628 | 3 | | | | | HSPB7 | 1.00 | 13724 | 3 | | | IGSF3 | 1.00 |
| 13629 | 3 | | | | | HSPB8 | 1.00 | 13725 | 3 | | | IGSF5 | 1.00 |
| 13630 | 3 | | | | | HSPB9 | 1.00 | 13726 | 3 | | | IGSF9 | 1.00 |
| 13631 | 3 | | | | | HSPC072 | 1.00 | 13727 | 3 | | | IGSF9B | 1.00 |
| 13632 | 3 | | | | | HSPG2 | 1.00 | 13728 | 3 | | | IHH | 1.00 |
| 13633 | 3 | | | | | HTA | 1.00 | 13729 | 3 | | | IL10 | 1.00 |
| 13634 | 3 | | | | | HTN1 | 1.00 | 13730 | 3 | | | IL11 | 1.00 |
| 13635 | 3 | | | | | HTN3 | 1.00 | 13731 | 3 | | | IL12A | 1.00 |
| 13636 | 3 | | | | | HTR1A | 1.00 | 13732 | 3 | | | IL12B | 1.00 |
| 13637 | 3 | | | | | HTR1B | 1.00 | 13733 | 3 | | | IL13 | 1.00 |
| 13638 | 3 | | | | | HTR1D | 1.00 | 13734 | 3 | | | IL13RA2 | 1.00 |
| 13639 | 3 | | | | | HTR1E | 1.00 | 13735 | 3 | | | IL17A | 1.00 |
| 13640 | 3 | | | | | HTR1F | 1.00 | 13736 | 3 | | | IL17B | 1.00 |
| 13641 | 3 | | | | | HTR2A | 1.00 | 13737 | 3 | | | IL17C | 1.00 |
| 13642 | 3 | | | | | HTR2B | 1.00 | 13738 | 3 | | | IL17D | 1.00 |
| 13643 | 3 | | | | | HTR2C | 1.00 | 13739 | 3 | | | IL17F | 1.00 |
| 13644 | 3 | | | | | HTR3A | 1.00 | 13740 | 3 | | | IL17RD | 1.00 |
| 13645 | 3 | | | | | HTR3B | 1.00 | 13741 | 3 | | | IL17RE | 1.00 |
| 13646 | 3 | | | | | HTR3C | 1.00 | 13742 | 3 | | | IL17REL | 1.00 |
| 13647 | 3 | | | | | HTR3D | 1.00 | 13743 | 3 | | | IL19 | 1.00 |
| 13648 | 3 | | | | | HTR3E | 1.00 | 13744 | 3 | | | IL1A | 1.00 |
| 13649 | 3 | | | | | HTR4 | 1.00 | 13745 | 3 | | | IL1F10 | 1.00 |
| 13650 | 3 | | | | | HTR5A | 1.00 | 13746 | 3 | | | IL1RAPL1 | 1.00 |
| 13651 | 3 | | | | | HTR6 | 1.00 | 13747 | 3 | | | IL1RAPL2 | 1.00 |
| 13652 | 3 | | | | | HTR7 | 1.00 | 13748 | 3 | | | IL1RL2 | 1.00 |
| 13653 | 3 | | | | | HTRA1 | 1.00 | 13749 | 3 | | | IL2 | 1.00 |
| 13654 | 3 | | | | | HTRA3 | 1.00 | 13750 | 3 | | | IL20 | 1.00 |
| 13655 | 3 | | | | | HTRA4 | 1.00 | 13751 | 3 | | | IL20RA | 1.00 |
| 13656 | 3 | | | | | HTT-AS1 | 1.00 | 13752 | 3 | | | IL20RB | 1.00 |
| 13657 | 3 | | | | | HULC | 1.00 | 13753 | 3 | | | IL21 | 1.00 |
| 13658 | 3 | | | | | HUNK | 1.00 | 13754 | 3 | | | IL22 | 1.00 |
| 13659 | 3 | | | | | HUS1B | 1.00 | 13755 | 3 | | | IL22RA1 | 1.00 |
| 13660 | 3 | | | | | HYAL4 | 1.00 | 13756 | 3 | | | IL22RA2 | 1.00 |
| 13661 | 3 | | | | | HYALP1 | 1.00 | 13757 | 3 | | | IL23R | 1.00 |
| 13662 | 3 | | | | | HYDIN | 1.00 | 13758 | 3 | | | IL25 | 1.00 |
| 13663 | 3 | | | | | HYI | 1.00 | 13759 | 3 | | | IL26 | 1.00 |
| 13664 | 3 | | | | | HYMAI | 1.00 | 13760 | 3 | | | IL28A | 1.00 |
| 13665 | 3 | | | | | IAPP | 1.00 | 13761 | 3 | | | IL28B | 1.00 |
| 13666 | 3 | | | | | I85P | 1.00 | 13762 | 3 | | | IL29 | 1.00 |
| 13667 | 3 | | | | | ICAM5 | 1.00 | 13763 | 3 | | | IL3 | 1.00 |
| 13668 | 3 | | | | | ID1 | 1.00 | 13764 | 3 | | | IL31 | 1.00 |
| 13669 | 3 | | | | | ID4 | 1.00 | 13765 | 3 | | | IL31RA | 1.00 |
| 13670 | 3 | | | | | IDAS | 1.00 | 13766 | 3 | | | IL33 | 1.00 |
| 13671 | 3 | | | | | IDO2 | 1.00 | 13767 | 3 | | | IL34 | 1.00 |
| 13672 | 3 | | | | | IFITM10 | 1.00 | 13768 | 3 | | | IL36A | 1.00 |
| 13673 | 3 | | | | | IFITM5 | 1.00 | 13769 | 3 | | | IL36B | 1.00 |
| 13674 | 3 | | | | | IFLTD1 | 1.00 | 13770 | 3 | | | IL36G | 1.00 |
| 13675 | 3 | | | | | IFNA1 | 1.00 | 13771 | 3 | | | IL36RN | 1.00 |
| 13676 | 3 | | | | | IFNA10 | 1.00 | 13772 | 3 | | | IL37 | 1.00 |
| 13677 | 3 | | | | | IFNA13 | 1.00 | 13773 | 3 | | | IL4 | 1.00 |
| 13678 | 3 | | | | | IFNA14 | 1.00 | 13774 | 3 | | | IL5 | 1.00 |
| 13679 | 3 | | | | | IFNA16 | 1.00 | 13775 | 3 | | | IL6 | 1.00 |
| 13680 | 3 | | | | | IFNA17 | 1.00 | 13776 | 3 | | | IL9 | 1.00 |
| 13681 | 3 | | | | | IFNA2 | 1.00 | 13777 | 3 | | | ILDR1 | 1.00 |
| 13682 | 3 | | | | | IFNA21 | 1.00 | 13778 | 3 | | | ILDR2 | 1.00 |
| 13683 | 3 | | | | | IFNA22P | 1.00 | 13779 | 3 | | | IMMP1L | 1.00 |
| 13684 | 3 | | | | | IFNA4 | 1.00 | 13780 | 3 | | | IMPG1 | 1.00 |
| 13685 | 3 | | | | | IFNA5 | 1.00 | 13781 | 3 | | | IMPG2 | 1.00 |
| 13686 | 3 | | | | | IFNA6 | 1.00 | 13782 | 3 | | | INA | 1.00 |
| 13687 | 3 | | | | | IFNA7 | 1.00 | 13783 | 3 | | | INE2 | 1.00 |
| 13688 | 3 | | | | | IFNA8 | 1.00 | 13784 | 3 | | | INGX | 1.00 |
| 13689 | 3 | | | | | IFNB1 | 1.00 | 13785 | 3 | | | INHA | 1.00 |
| 13690 | 3 | | | | | IFNE | 1.00 | 13786 | 3 | | | INHBA | 1.00 |
| 13691 | 3 | | | | | IFNK | 1.00 | 13787 | 3 | | | INHBB | 1.00 |
| 13692 | 3 | | | | | IFNW1 | 1.00 | 13788 | 3 | | | INHBC | 1.00 |
| 13693 | 3 | | | | | IFT140 | 1.00 | 13789 | 3 | | | INHBE | 1.00 |
| 13694 | 3 | | | | | IFT172 | 1.00 | 13790 | 3 | | | INMT | 1.00 |
| 13695 | 3 | | | | | IFT74 | 1.00 | 13791 | 3 | | | INMT-FAM188B | 1.00 |
| 13696 | 3 | | | | | IFT81 | 1.00 | 13792 | 3 | | | INPP5J | 1.00 |
| 13697 | 3 | | | | | IFT88 | 1.00 | 13793 | 3 | | | INS | 1.00 |
| 13698 | 3 | | | | | IGDCC3 | 1.00 | 13794 | 3 | | | INS-IGF2 | 1.00 |
| 13699 | 3 | | | | | IGDCC4 | 1.00 | 13795 | 3 | | | INSC | 1.00 |
| 13700 | 3 | | | | | IGF1 | 1.00 | 13796 | 3 | | | INSL4 | 1.00 |
| 13701 | 3 | | | | | IGF2 | 1.00 | 13797 | 3 | | | INSL5 | 1.00 |
| 13702 | 3 | | | | | IGF2-AS1 | 1.00 | 13798 | 3 | | | INSL6 | 1.00 |
| 13703 | 3 | | | | | IGF2BP1 | 1.00 | 13799 | 3 | | | INSM1 | 1.00 |
| 13704 | 3 | | | | | IGFALS | 1.00 | 13800 | 3 | | | INSM2 | 1.00 |
| 13705 | 3 | | | | | IGFBP1 | 1.00 | 13801 | 3 | | | INSRR | 1.00 |
| 13706 | 3 | | | | | IGFBP5 | 1.00 | 13802 | 3 | | | INTS4L1 | 1.00 |
| 13707 | 3 | | | | | IGFBP6 | 1.00 | 13803 | 3 | | | INTS4L2 | 1.00 |
| 13708 | 3 | | | | | IGFBPL1 | 1.00 | 13804 | 3 | | | INTU | 1.00 |
| 13709 | 3 | | | | | IGFL1 | 1.00 | 13805 | 3 | | | IP6K3 | 1.00 |
| 13710 | 3 | | | | | IGFL2 | 1.00 | 13806 | 3 | | | IQCA1 | 1.00 |
| 13711 | 3 | | | | | IGFL3 | 1.00 | 13807 | 3 | | | IQCD | 1.00 |
| 13712 | 3 | | | | | IGFL4 | 1.00 | 13808 | 3 | | | IQCF1 | 1.00 |
| 13713 | 3 | | | | | IGFN1 | 1.00 | 13809 | 3 | | | IQCF2 | 1.00 |
| 13714 | 3 | | | | | IGLL1 | 1.00 | 13810 | 3 | | | IQCF3 | 1.00 |
| 13715 | 3 | | | | | IGLL3P | 1.00 | 13811 | 3 | | | IQCF4 | 1.00 |
| 13716 | 3 | | | | | IGLON5 | 1.00 | 13812 | 3 | | | IQCF5 | 1.00 |
| 13717 | 3 | | | | | IGSF1 | 1.00 | 13813 | 3 | | | IQCF6 | 1.00 |
| 13718 | 3 | | | | | IGSF10 | 1.00 | 13814 | 3 | | | IQCH | 1.00 |
| 13719 | 3 | | | | | IGSF11 | 1.00 | 13815 | 3 | | | IQCJ | 1.00 |
| 13720 | 3 | | | | | IGSF11-AS1 | 1.00 | 13816 | 3 | | | IQCJ-SCHIP1 | 1.00 |
| 13721 | 3 | | | | | IGSF21 | 1.00 | 13817 | 3 | | | IQCK | 1.00 |
| 13722 | 3 | | | | | IGSF22 | 1.00 | 13818 | 3 | | | IQGAP3 | 1.00 |

Fig. 40 - 73

| | | | | | | | | | | | | | | | | | |
|---|---|---|---|---|---|---|---|---|---|---|---|---|---|---|---|---|---|
| 13819 | 3 | | | | | | IQSEC3 | 1.00 | 13915 | 3 | | | | | | KCNH8 | 1.00 |
| 13820 | 3 | | | | | | IQUB | 1.00 | 13916 | 3 | | | | | | KCNIP1 | 1.00 |
| 13821 | 3 | | | | | | IRAK1BP1 | 1.00 | 13917 | 3 | | | | | | KCNIP3 | 1.00 |
| 13822 | 3 | | | | | | IRF6 | 1.00 | 13918 | 3 | | | | | | KCNIP4 | 1.00 |
| 13823 | 3 | | | | | | IRGC | 1.00 | 13919 | 3 | | | | | | KCNIP4-IT1 | 1.00 |
| 13824 | 3 | | | | | | IRGM | 1.00 | 13920 | 3 | | | | | | KCNJ1 | 1.00 |
| 13825 | 3 | | | | | | IRS4 | 1.00 | 13921 | 3 | | | | | | KCNJ10 | 1.00 |
| 13826 | 3 | | | | | | IRX1 | 1.00 | 13922 | 3 | | | | | | KCNJ11 | 1.00 |
| 13827 | 3 | | | | | | IRX2 | 1.00 | 13923 | 3 | | | | | | KCNJ12 | 1.00 |
| 13828 | 3 | | | | | | IRX3 | 1.00 | 13924 | 3 | | | | | | KCNJ13 | 1.00 |
| 13829 | 3 | | | | | | IRX4 | 1.00 | 13925 | 3 | | | | | | KCNJ14 | 1.00 |
| 13830 | 3 | | | | | | IRX5 | 1.00 | 13926 | 3 | | | | | | KCNJ16 | 1.00 |
| 13831 | 3 | | | | | | IRX6 | 1.00 | 13927 | 3 | | | | | | KCNJ18 | 1.00 |
| 13832 | 3 | | | | | | ISL1 | 1.00 | 13928 | 3 | | | | | | KCNJ3 | 1.00 |
| 13833 | 3 | | | | | | ISLR | 1.00 | 13929 | 3 | | | | | | KCNJ4 | 1.00 |
| 13834 | 3 | | | | | | ISLR2 | 1.00 | 13930 | 3 | | | | | | KCNJ5 | 1.00 |
| 13835 | 3 | | | | | | ISM2 | 1.00 | 13931 | 3 | | | | | | KCNJ6 | 1.00 |
| 13836 | 3 | | | | | | ISPD | 1.00 | 13932 | 3 | | | | | | KCNJ8 | 1.00 |
| 13837 | 3 | | | | | | ISX | 1.00 | 13933 | 3 | | | | | | KCNJ9 | 1.00 |
| 13838 | 3 | | | | | | ISY1-RAB43 | 1.00 | 13934 | 3 | | | | | | KCNK1 | 1.00 |
| 13839 | 3 | | | | | | ITGA1 | 1.00 | 13935 | 3 | | | | | | KCNK10 | 1.00 |
| 13840 | 3 | | | | | | ITGA10 | 1.00 | 13936 | 3 | | | | | | KCNK12 | 1.00 |
| 13841 | 3 | | | | | | ITGA11 | 1.00 | 13937 | 3 | | | | | | KCNK15 | 1.00 |
| 13842 | 3 | | | | | | ITGA2 | 1.00 | 13938 | 3 | | | | | | KCNK16 | 1.00 |
| 13843 | 3 | | | | | | ITGA3 | 1.00 | 13939 | 3 | | | | | | KCNK17 | 1.00 |
| 13844 | 3 | | | | | | ITGA7 | 1.00 | 13940 | 3 | | | | | | KCNK18 | 1.00 |
| 13845 | 3 | | | | | | ITGA8 | 1.00 | 13941 | 3 | | | | | | KCNK2 | 1.00 |
| 13846 | 3 | | | | | | ITGA9 | 1.00 | 13942 | 3 | | | | | | KCNK3 | 1.00 |
| 13847 | 3 | | | | | | ITGAD | 1.00 | 13943 | 3 | | | | | | KCNK4 | 1.00 |
| 13848 | 3 | | | | | | ITGAE | 1.00 | 13944 | 3 | | | | | | KCNK5 | 1.00 |
| 13849 | 3 | | | | | | ITGB1BP2 | 1.00 | 13945 | 3 | | | | | | KCNK9 | 1.00 |
| 13850 | 3 | | | | | | ITGB1BP3 | 1.00 | 13946 | 3 | | | | | | KCNMA1 | 1.00 |
| 13851 | 3 | | | | | | ITGB4 | 1.00 | 13947 | 3 | | | | | | KCNMB2 | 1.00 |
| 13852 | 3 | | | | | | ITGB6 | 1.00 | 13948 | 3 | | | | | | KCNMB4 | 1.00 |
| 13853 | 3 | | | | | | ITGB8 | 1.00 | 13949 | 3 | | | | | | KCNN1 | 1.00 |
| 13854 | 3 | | | | | | ITGBL1 | 1.00 | 13950 | 3 | | | | | | KCNN2 | 1.00 |
| 13855 | 3 | | | | | | ITIH1 | 1.00 | 13951 | 3 | | | | | | KCNN3 | 1.00 |
| 13856 | 3 | | | | | | ITIH2 | 1.00 | 13952 | 3 | | | | | | KCNQ1DN | 1.00 |
| 13857 | 3 | | | | | | ITIH3 | 1.00 | 13953 | 3 | | | | | | KCNQ1OT1 | 1.00 |
| 13858 | 3 | | | | | | ITIH5 | 1.00 | 13954 | 3 | | | | | | KCNQ2 | 1.00 |
| 13859 | 3 | | | | | | ITIH6 | 1.00 | 13955 | 3 | | | | | | KCNQ3 | 1.00 |
| 13860 | 3 | | | | | | ITLN2 | 1.00 | 13956 | 3 | | | | | | KCNQ4 | 1.00 |
| 13861 | 3 | | | | | | ITPK1-AS1 | 1.00 | 13957 | 3 | | | | | | KCNQ5 | 1.00 |
| 13862 | 3 | | | | | | ITPKA | 1.00 | 13958 | 3 | | | | | | KCNS1 | 1.00 |
| 13863 | 3 | | | | | | IVL | 1.00 | 13959 | 3 | | | | | | KCNS2 | 1.00 |
| 13864 | 3 | | | | | | IYD | 1.00 | 13960 | 3 | | | | | | KCNS3 | 1.00 |
| 13865 | 3 | | | | | | IZUMO1 | 1.00 | 13961 | 3 | | | | | | KCNT1 | 1.00 |
| 13866 | 3 | | | | | | IZUMO2 | 1.00 | 13962 | 3 | | | | | | KCNT2 | 1.00 |
| 13867 | 3 | | | | | | JAG2 | 1.00 | 13963 | 3 | | | | | | KCNU1 | 1.00 |
| 13868 | 3 | | | | | | JAKMIP3 | 1.00 | 13964 | 3 | | | | | | KCNV1 | 1.00 |
| 13869 | 3 | | | | | | JAM2 | 1.00 | 13965 | 3 | | | | | | KCNV2 | 1.00 |
| 13870 | 3 | | | | | | JAZF1-AS1 | 1.00 | 13966 | 3 | | | | | | KCP | 1.00 |
| 13871 | 3 | | | | | | JMJD7-PLA2G4B | 1.00 | 13967 | 3 | | | | | | KCTD1 | 1.00 |
| 13872 | 3 | | | | | | JPH1 | 1.00 | 13968 | 3 | | | | | | KCTD14 | 1.00 |
| 13873 | 3 | | | | | | JPH2 | 1.00 | 13969 | 3 | | | | | | KCTD16 | 1.00 |
| 13874 | 3 | | | | | | JPH3 | 1.00 | 13970 | 3 | | | | | | KCTD19 | 1.00 |
| 13875 | 3 | | | | | | JPH4 | 1.00 | 13971 | 3 | | | | | | KCTD4 | 1.00 |
| 13876 | 3 | | | | | | JSRP1 | 1.00 | 13972 | 3 | | | | | | KCTD8 | 1.00 |
| 13877 | 3 | | | | | | KAAG1 | 1.00 | 13973 | 3 | | | | | | KDELC1 | 1.00 |
| 13878 | 3 | | | | | | KAL1 | 1.00 | 13974 | 3 | | | | | | KDELR3 | 1.00 |
| 13879 | 3 | | | | | | KALRN | 1.00 | 13975 | 3 | | | | | | KDM4D | 1.00 |
| 13880 | 3 | | | | | | KANK3 | 1.00 | 13976 | 3 | | | | | | KDM4DL | 1.00 |
| 13881 | 3 | | | | | | KANK4 | 1.00 | 13977 | 3 | | | | | | KDM5B-AS1 | 1.00 |
| 13882 | 3 | | | | | | KATNAL2 | 1.00 | 13978 | 3 | | | | | | KDM5D | 1.00 |
| 13883 | 3 | | | | | | KAZALD1 | 1.00 | 13979 | 3 | | | | | | KDR | 1.00 |
| 13884 | 3 | | | | | | KBTBD10 | 1.00 | 13980 | 3 | | | | | | KERA | 1.00 |
| 13885 | 3 | | | | | | KBTBD12 | 1.00 | 13981 | 3 | | | | | | KGFLP1 | 1.00 |
| 13886 | 3 | | | | | | KBTBD13 | 1.00 | 13982 | 3 | | | | | | KGFLP2 | 1.00 |
| 13887 | 3 | | | | | | KBTBD5 | 1.00 | 13983 | 3 | | | | | | KHDC1 | 1.00 |
| 13888 | 3 | | | | | | KC6 | 1.00 | 13984 | 3 | | | | | | KHDC1L | 1.00 |
| 13889 | 3 | | | | | | KCNA1 | 1.00 | 13985 | 3 | | | | | | KHDRBS2 | 1.00 |
| 13890 | 3 | | | | | | KCNA10 | 1.00 | 13986 | 3 | | | | | | KHDRBS3 | 1.00 |
| 13891 | 3 | | | | | | KCNA2 | 1.00 | 13987 | 3 | | | | | | KIAA0087 | 1.00 |
| 13892 | 3 | | | | | | KCNA4 | 1.00 | 13988 | 3 | | | | | | KIAA0101 | 1.00 |
| 13893 | 3 | | | | | | KCNA5 | 1.00 | 13989 | 3 | | | | | | KIAA0284 | 1.00 |
| 13894 | 3 | | | | | | KCNA6 | 1.00 | 13990 | 3 | | | | | | KIAA0408 | 1.00 |
| 13895 | 3 | | | | | | KCNA7 | 1.00 | 13991 | 3 | | | | | | KIAA0754 | 1.00 |
| 13896 | 3 | | | | | | KCNAB1 | 1.00 | 13992 | 3 | | | | | | KIAA0895 | 1.00 |
| 13897 | 3 | | | | | | KCNB1 | 1.00 | 13993 | 3 | | | | | | KIAA1024 | 1.00 |
| 13898 | 3 | | | | | | KCNB2 | 1.00 | 13994 | 3 | | | | | | KIAA1045 | 1.00 |
| 13899 | 3 | | | | | | KCNC1 | 1.00 | 13995 | 3 | | | | | | KIAA1161 | 1.00 |
| 13900 | 3 | | | | | | KCNC2 | 1.00 | 13996 | 3 | | | | | | KIAA1199 | 1.00 |
| 13901 | 3 | | | | | | KCND2 | 1.00 | 13997 | 3 | | | | | | KIAA1210 | 1.00 |
| 13902 | 3 | | | | | | KCND3 | 1.00 | 13998 | 3 | | | | | | KIAA1211 | 1.00 |
| 13903 | 3 | | | | | | KCNE1L | 1.00 | 13999 | 3 | | | | | | KIAA1217 | 1.00 |
| 13904 | 3 | | | | | | KCNE2 | 1.00 | 14000 | 3 | | | | | | KIAA1239 | 1.00 |
| 13905 | 3 | | | | | | KCNE4 | 1.00 | 14001 | 3 | | | | | | KIAA1244 | 1.00 |
| 13906 | 3 | | | | | | KCNF1 | 1.00 | 14002 | 3 | | | | | | KIAA1274 | 1.00 |
| 13907 | 3 | | | | | | KCNG2 | 1.00 | 14003 | 3 | | | | | | KIAA1324L | 1.00 |
| 13908 | 3 | | | | | | KCNG3 | 1.00 | 14004 | 3 | | | | | | KIAA1377 | 1.00 |
| 13909 | 3 | | | | | | KCNG4 | 1.00 | 14005 | 3 | | | | | | KIAA1456 | 1.00 |
| 13910 | 3 | | | | | | KCNH1 | 1.00 | 14006 | 3 | | | | | | KIAA1462 | 1.00 |
| 13911 | 3 | | | | | | KCNH4 | 1.00 | 14007 | 3 | | | | | | KIAA1524 | 1.00 |
| 13912 | 3 | | | | | | KCNH5 | 1.00 | 14008 | 3 | | | | | | KIAA1549 | 1.00 |
| 13913 | 3 | | | | | | KCNH6 | 1.00 | 14009 | 3 | | | | | | KIAA1614 | 1.00 |
| 13914 | 3 | | | | | | KCNH7 | 1.00 | 14010 | 3 | | | | | | KIAA1644 | 1.00 |

Fig. 40 - 74

| | | | | | | | | | | | | | | | | |
|---|---|---|---|---|---|---|---|---|---|---|---|---|---|---|---|---|
| 14011 | 3 | | | | | KIAA1656 | 1.00 | 14107 | 3 | | | | | KRT16 | 1.00 |
| 14012 | 3 | | | | | KIAA1751 | 1.00 | 14108 | 3 | | | | | KRT16P2 | 1.00 |
| 14013 | 3 | | | | | KIAA1755 | 1.00 | 14109 | 3 | | | | | KRT16P3 | 1.00 |
| 14014 | 3 | | | | | KIAA1804 | 1.00 | 14110 | 3 | | | | | KRT17 | 1.00 |
| 14015 | 3 | | | | | KIAA1875 | 1.00 | 14111 | 3 | | | | | KRT18P55 | 1.00 |
| 14016 | 3 | | | | | KIAA1984 | 1.00 | 14112 | 3 | | | | | KRT19 | 1.00 |
| 14017 | 3 | | | | | KIAA2022 | 1.00 | 14113 | 3 | | | | | KRT19P2 | 1.00 |
| 14018 | 3 | | | | | KIF11 | 1.00 | 14114 | 3 | | | | | KRT2 | 1.00 |
| 14019 | 3 | | | | | KIF12 | 1.00 | 14115 | 3 | | | | | KRT20 | 1.00 |
| 14020 | 3 | | | | | KIF14 | 1.00 | 14116 | 3 | | | | | KRT222 | 1.00 |
| 14021 | 3 | | | | | KIF15 | 1.00 | 14117 | 3 | | | | | KRT24 | 1.00 |
| 14022 | 3 | | | | | KIF17 | 1.00 | 14118 | 3 | | | | | KRT25 | 1.00 |
| 14023 | 3 | | | | | KIF18A | 1.00 | 14119 | 3 | | | | | KRT26 | 1.00 |
| 14024 | 3 | | | | | KIF18B | 1.00 | 14120 | 3 | | | | | KRT27 | 1.00 |
| 14025 | 3 | | | | | KIF19 | 1.00 | 14121 | 3 | | | | | KRT28 | 1.00 |
| 14026 | 3 | | | | | KIF1A | 1.00 | 14122 | 3 | | | | | KRT3 | 1.00 |
| 14027 | 3 | | | | | KIF20A | 1.00 | 14123 | 3 | | | | | KRT31 | 1.00 |
| 14028 | 3 | | | | | KIF24 | 1.00 | 14124 | 3 | | | | | KRT32 | 1.00 |
| 14029 | 3 | | | | | KIF25 | 1.00 | 14125 | 3 | | | | | KRT33A | 1.00 |
| 14030 | 3 | | | | | KIF26A | 1.00 | 14126 | 3 | | | | | KRT33B | 1.00 |
| 14031 | 3 | | | | | KIF26B | 1.00 | 14127 | 3 | | | | | KRT34 | 1.00 |
| 14032 | 3 | | | | | KIF2B | 1.00 | 14128 | 3 | | | | | KRT35 | 1.00 |
| 14033 | 3 | | | | | KIF2C | 1.00 | 14129 | 3 | | | | | KRT36 | 1.00 |
| 14034 | 3 | | | | | KIF4A | 1.00 | 14130 | 3 | | | | | KRT37 | 1.00 |
| 14035 | 3 | | | | | KIF4B | 1.00 | 14131 | 3 | | | | | KRT38 | 1.00 |
| 14036 | 3 | | | | | KIF5A | 1.00 | 14132 | 3 | | | | | KRT39 | 1.00 |
| 14037 | 3 | | | | | KIF6 | 1.00 | 14133 | 3 | | | | | KRT4 | 1.00 |
| 14038 | 3 | | | | | KIF7 | 1.00 | 14134 | 3 | | | | | KRT40 | 1.00 |
| 14039 | 3 | | | | | KIF9 | 1.00 | 14135 | 3 | | | | | KRT42P | 1.00 |
| 14040 | 3 | | | | | KIFC1 | 1.00 | 14136 | 3 | | | | | KRT6A | 1.00 |
| 14041 | 3 | | | | | KIR2DL5A | 1.00 | 14137 | 3 | | | | | KRT6B | 1.00 |
| 14042 | 3 | | | | | KIR2DL5B | 1.00 | 14138 | 3 | | | | | KRT6C | 1.00 |
| 14043 | 3 | | | | | KIR2DS3 | 1.00 | 14139 | 3 | | | | | KRT7 | 1.00 |
| 14044 | 3 | | | | | KIR2DS5 | 1.00 | 14140 | 3 | | | | | KRT71 | 1.00 |
| 14045 | 3 | | | | | KIR3DL3 | 1.00 | 14141 | 3 | | | | | KRT74 | 1.00 |
| 14046 | 3 | | | | | KIR3DX1 | 1.00 | 14142 | 3 | | | | | KRT75 | 1.00 |
| 14047 | 3 | | | | | KIRREL | 1.00 | 14143 | 3 | | | | | KRT76 | 1.00 |
| 14048 | 3 | | | | | KIRREL2 | 1.00 | 14144 | 3 | | | | | KRT77 | 1.00 |
| 14049 | 3 | | | | | KIRREL3 | 1.00 | 14145 | 3 | | | | | KRT78 | 1.00 |
| 14050 | 3 | | | | | KIRREL3-AS3 | 1.00 | 14146 | 3 | | | | | KRT79 | 1.00 |
| 14051 | 3 | | | | | KISS1 | 1.00 | 14147 | 3 | | | | | KRT8 | 1.00 |
| 14052 | 3 | | | | | KISS1R | 1.00 | 14148 | 3 | | | | | KRT80 | 1.00 |
| 14053 | 3 | | | | | KITLG | 1.00 | 14149 | 3 | | | | | KRT81 | 1.00 |
| 14054 | 3 | | | | | KL | 1.00 | 14150 | 3 | | | | | KRT82 | 1.00 |
| 14055 | 3 | | | | | KLB | 1.00 | 14151 | 3 | | | | | KRT83 | 1.00 |
| 14056 | 3 | | | | | KLF14 | 1.00 | 14152 | 3 | | | | | KRT84 | 1.00 |
| 14057 | 3 | | | | | KLF15 | 1.00 | 14153 | 3 | | | | | KRT85 | 1.00 |
| 14058 | 3 | | | | | KLF17 | 1.00 | 14154 | 3 | | | | | KRT86 | 1.00 |
| 14059 | 3 | | | | | KLHDC7A | 1.00 | 14155 | 3 | | | | | KRT8P41 | 1.00 |
| 14060 | 3 | | | | | KLHDC8A | 1.00 | 14156 | 3 | | | | | KRT9 | 1.00 |
| 14061 | 3 | | | | | KLHDC9 | 1.00 | 14157 | 3 | | | | | KRTAP1-1 | 1.00 |
| 14062 | 3 | | | | | KLHL1 | 1.00 | 14158 | 3 | | | | | KRTAP1-3 | 1.00 |
| 14063 | 3 | | | | | KLHL10 | 1.00 | 14159 | 3 | | | | | KRTAP1-5 | 1.00 |
| 14064 | 3 | | | | | KLHL13 | 1.00 | 14160 | 3 | | | | | KRTAP10-1 | 1.00 |
| 14065 | 3 | | | | | KLHL23 | 1.00 | 14161 | 3 | | | | | KRTAP10-10 | 1.00 |
| 14066 | 3 | | | | | KLHL29 | 1.00 | 14162 | 3 | | | | | KRTAP10-11 | 1.00 |
| 14067 | 3 | | | | | KLHL30 | 1.00 | 14163 | 3 | | | | | KRTAP10-12 | 1.00 |
| 14068 | 3 | | | | | KLHL31 | 1.00 | 14164 | 3 | | | | | KRTAP10-2 | 1.00 |
| 14069 | 3 | | | | | KLHL32 | 1.00 | 14165 | 3 | | | | | KRTAP10-3 | 1.00 |
| 14070 | 3 | | | | | KLHL33 | 1.00 | 14166 | 3 | | | | | KRTAP10-4 | 1.00 |
| 14071 | 3 | | | | | KLHL34 | 1.00 | 14167 | 3 | | | | | KRTAP10-5 | 1.00 |
| 14072 | 3 | | | | | KLHL35 | 1.00 | 14168 | 3 | | | | | KRTAP10-6 | 1.00 |
| 14073 | 3 | | | | | KLHL38 | 1.00 | 14169 | 3 | | | | | KRTAP10-7 | 1.00 |
| 14074 | 3 | | | | | KLHL4 | 1.00 | 14170 | 3 | | | | | KRTAP10-8 | 1.00 |
| 14075 | 3 | | | | | KLHL7-AS1 | 1.00 | 14171 | 3 | | | | | KRTAP10-9 | 1.00 |
| 14076 | 3 | | | | | KLK10 | 1.00 | 14172 | 3 | | | | | KRTAP11-1 | 1.00 |
| 14077 | 3 | | | | | KLK11 | 1.00 | 14173 | 3 | | | | | KRTAP12-1 | 1.00 |
| 14078 | 3 | | | | | KLK12 | 1.00 | 14174 | 3 | | | | | KRTAP12-2 | 1.00 |
| 14079 | 3 | | | | | KLK13 | 1.00 | 14175 | 3 | | | | | KRTAP12-3 | 1.00 |
| 14080 | 3 | | | | | KLK14 | 1.00 | 14176 | 3 | | | | | KRTAP12-4 | 1.00 |
| 14081 | 3 | | | | | KLK15 | 1.00 | 14177 | 3 | | | | | KRTAP13-1 | 1.00 |
| 14082 | 3 | | | | | KLK2 | 1.00 | 14178 | 3 | | | | | KRTAP13-2 | 1.00 |
| 14083 | 3 | | | | | KLK3 | 1.00 | 14179 | 3 | | | | | KRTAP13-3 | 1.00 |
| 14084 | 3 | | | | | KLK4 | 1.00 | 14180 | 3 | | | | | KRTAP13-4 | 1.00 |
| 14085 | 3 | | | | | KLK5 | 1.00 | 14181 | 3 | | | | | KRTAP15-1 | 1.00 |
| 14086 | 3 | | | | | KLK6 | 1.00 | 14182 | 3 | | | | | KRTAP16-1 | 1.00 |
| 14087 | 3 | | | | | KLK7 | 1.00 | 14183 | 3 | | | | | KRTAP17-1 | 1.00 |
| 14088 | 3 | | | | | KLK8 | 1.00 | 14184 | 3 | | | | | KRTAP19-1 | 1.00 |
| 14089 | 3 | | | | | KLK9 | 1.00 | 14185 | 3 | | | | | KRTAP19-2 | 1.00 |
| 14090 | 3 | | | | | KLKB1 | 1.00 | 14186 | 3 | | | | | KRTAP19-3 | 1.00 |
| 14091 | 3 | | | | | KLKP1 | 1.00 | 14187 | 3 | | | | | KRTAP19-4 | 1.00 |
| 14092 | 3 | | | | | KLLN | 1.00 | 14188 | 3 | | | | | KRTAP19-5 | 1.00 |
| 14093 | 3 | | | | | KLRC4-KLRK1 | 1.00 | 14189 | 3 | | | | | KRTAP19-6 | 1.00 |
| 14094 | 3 | | | | | KLRF2 | 1.00 | 14190 | 3 | | | | | KRTAP19-7 | 1.00 |
| 14095 | 3 | | | | | KLRG2 | 1.00 | 14191 | 3 | | | | | KRTAP19-8 | 1.00 |
| 14096 | 3 | | | | | KNCN | 1.00 | 14192 | 3 | | | | | KRTAP2-1 | 1.00 |
| 14097 | 3 | | | | | KNDC1 | 1.00 | 14193 | 3 | | | | | KRTAP2-2 | 1.00 |
| 14098 | 3 | | | | | KNG1 | 1.00 | 14194 | 3 | | | | | KRTAP2-4 | 1.00 |
| 14099 | 3 | | | | | KNTC1 | 1.00 | 14195 | 3 | | | | | KRTAP20-1 | 1.00 |
| 14100 | 3 | | | | | KPNA7 | 1.00 | 14196 | 3 | | | | | KRTAP20-2 | 1.00 |
| 14101 | 3 | | | | | KPRP | 1.00 | 14197 | 3 | | | | | KRTAP20-3 | 1.00 |
| 14102 | 3 | | | | | KRBOX1 | 1.00 | 14198 | 3 | | | | | KRTAP20-4 | 1.00 |
| 14103 | 3 | | | | | KREMEN2 | 1.00 | 14199 | 3 | | | | | KRTAP21-1 | 1.00 |
| 14104 | 3 | | | | | KRT12 | 1.00 | 14200 | 3 | | | | | KRTAP21-2 | 1.00 |
| 14105 | 3 | | | | | KRT13 | 1.00 | 14201 | 3 | | | | | KRTAP21-3 | 1.00 |
| 14106 | 3 | | | | | KRT15 | 1.00 | 14202 | 3 | | | | | KRTAP22-1 | 1.00 |

Fig. 40 - 75

| | | | | | | | | | | | | | | |
|---|---|---|---|---|---|---|---|---|---|---|---|---|---|---|
| 14203 | 3 | | | | | KRTAP22-2 | 1.00 | 14299 | 3 | | | | LCNL1 | 1.00 |
| 14204 | 3 | | | | | KRTAP23-1 | 1.00 | 14300 | 3 | | | | LCT | 1.00 |
| 14205 | 3 | | | | | KRTAP24-1 | 1.00 | 14301 | 3 | | | | LCTL | 1.00 |
| 14206 | 3 | | | | | KRTAP25-1 | 1.00 | 14302 | 3 | | | | LDB2 | 1.00 |
| 14207 | 3 | | | | | KRTAP26-1 | 1.00 | 14303 | 3 | | | | LDB3 | 1.00 |
| 14208 | 3 | | | | | KRTAP27-1 | 1.00 | 14304 | 3 | | | | LDHAL6A | 1.00 |
| 14209 | 3 | | | | | KRTAP3-1 | 1.00 | 14305 | 3 | | | | LDHAL6B | 1.00 |
| 14210 | 3 | | | | | KRTAP3-2 | 1.00 | 14306 | 3 | | | | LDHC | 1.00 |
| 14211 | 3 | | | | | KRTAP3-3 | 1.00 | 14307 | 3 | | | | LDLRAD1 | 1.00 |
| 14212 | 3 | | | | | KRTAP4-1 | 1.00 | 14308 | 3 | | | | LDLRAD2 | 1.00 |
| 14213 | 3 | | | | | KRTAP4-11 | 1.00 | 14309 | 3 | | | | LEAP2 | 1.00 |
| 14214 | 3 | | | | | KRTAP4-12 | 1.00 | 14310 | 3 | | | | LECT1 | 1.00 |
| 14215 | 3 | | | | | KRTAP4-2 | 1.00 | 14311 | 3 | | | | LECT2 | 1.00 |
| 14216 | 3 | | | | | KRTAP4-3 | 1.00 | 14312 | 3 | | | | LEFTY1 | 1.00 |
| 14217 | 3 | | | | | KRTAP4-4 | 1.00 | 14313 | 3 | | | | LEFTY2 | 1.00 |
| 14218 | 3 | | | | | KRTAP4-5 | 1.00 | 14314 | 3 | | | | LEKR1 | 1.00 |
| 14219 | 3 | | | | | KRTAP4-6 | 1.00 | 14315 | 3 | | | | LELP1 | 1.00 |
| 14220 | 3 | | | | | KRTAP4-7 | 1.00 | 14316 | 3 | | | | LEMD1 | 1.00 |
| 14221 | 3 | | | | | KRTAP4-8 | 1.00 | 14317 | 3 | | | | LENEP | 1.00 |
| 14222 | 3 | | | | | KRTAP4-9 | 1.00 | 14318 | 3 | | | | LEP | 1.00 |
| 14223 | 3 | | | | | KRTAP5-10 | 1.00 | 14319 | 3 | | | | LEPREL1 | 1.00 |
| 14224 | 3 | | | | | KRTAP5-11 | 1.00 | 14320 | 3 | | | | LEPREL2 | 1.00 |
| 14225 | 3 | | | | | KRTAP5-2 | 1.00 | 14321 | 3 | | | | LEUTX | 1.00 |
| 14226 | 3 | | | | | KRTAP5-3 | 1.00 | 14322 | 3 | | | | LGALS13 | 1.00 |
| 14227 | 3 | | | | | KRTAP5-4 | 1.00 | 14323 | 3 | | | | LGALS14 | 1.00 |
| 14228 | 3 | | | | | KRTAP5-5 | 1.00 | 14324 | 3 | | | | LGALS16 | 1.00 |
| 14229 | 3 | | | | | KRTAP5-6 | 1.00 | 14325 | 3 | | | | LGALS17A | 1.00 |
| 14230 | 3 | | | | | KRTAP5-7 | 1.00 | 14326 | 3 | | | | LGALS4 | 1.00 |
| 14231 | 3 | | | | | KRTAP5-8 | 1.00 | 14327 | 3 | | | | LGALS7 | 1.00 |
| 14232 | 3 | | | | | KRTAP5-9 | 1.00 | 14328 | 3 | | | | LGALS7B | 1.00 |
| 14233 | 3 | | | | | KRTAP6-1 | 1.00 | 14329 | 3 | | | | LGALS8-AS1 | 1.00 |
| 14234 | 3 | | | | | KRTAP6-2 | 1.00 | 14330 | 3 | | | | LGI1 | 1.00 |
| 14235 | 3 | | | | | KRTAP6-3 | 1.00 | 14331 | 3 | | | | LGI2 | 1.00 |
| 14236 | 3 | | | | | KRTAP7-1 | 1.00 | 14332 | 3 | | | | LGI3 | 1.00 |
| 14237 | 3 | | | | | KRTAP8-1 | 1.00 | 14333 | 3 | | | | LGI4 | 1.00 |
| 14238 | 3 | | | | | KRTAP9-1 | 1.00 | 14334 | 3 | | | | LGR4 | 1.00 |
| 14239 | 3 | | | | | KRTAP9-2 | 1.00 | 14335 | 3 | | | | LGR5 | 1.00 |
| 14240 | 3 | | | | | KRTAP9-3 | 1.00 | 14336 | 3 | | | | LGSN | 1.00 |
| 14241 | 3 | | | | | KRTAP9-4 | 1.00 | 14337 | 3 | | | | LHB | 1.00 |
| 14242 | 3 | | | | | KRTAP9-8 | 1.00 | 14338 | 3 | | | | LHCGR | 1.00 |
| 14243 | 3 | | | | | KRTAP9-9 | 1.00 | 14339 | 3 | | | | LHFP | 1.00 |
| 14244 | 3 | | | | | KRTCAP3 | 1.00 | 14340 | 3 | | | | LHFPL1 | 1.00 |
| 14245 | 3 | | | | | KRTDAP | 1.00 | 14341 | 3 | | | | LHFPL3 | 1.00 |
| 14246 | 3 | | | | | KSR2 | 1.00 | 14342 | 3 | | | | LHFPL4 | 1.00 |
| 14247 | 3 | | | | | KTN1-AS1 | 1.00 | 14343 | 3 | | | | LHFPL5 | 1.00 |
| 14248 | 3 | | | | | L1CAM | 1.00 | 14344 | 3 | | | | LHX1 | 1.00 |
| 14249 | 3 | | | | | L1TD1 | 1.00 | 14345 | 3 | | | | LHX2 | 1.00 |
| 14250 | 3 | | | | | L2HGDH | 1.00 | 14346 | 3 | | | | LHX3 | 1.00 |
| 14251 | 3 | | | | | L3MBTL1 | 1.00 | 14347 | 3 | | | | LHX5 | 1.00 |
| 14252 | 3 | | | | | L3MBTL4 | 1.00 | 14348 | 3 | | | | LHX6 | 1.00 |
| 14253 | 3 | | | | | LACE1 | 1.00 | 14349 | 3 | | | | LHX8 | 1.00 |
| 14254 | 3 | | | | | LACRT | 1.00 | 14350 | 3 | | | | LHX9 | 1.00 |
| 14255 | 3 | | | | | LAD1 | 1.00 | 14351 | 3 | | | | LIF | 1.00 |
| 14256 | 3 | | | | | LALBA | 1.00 | 14352 | 3 | | | | LIFR | 1.00 |
| 14257 | 3 | | | | | LAMA1 | 1.00 | 14353 | 3 | | | | LILRB5 | 1.00 |
| 14258 | 3 | | | | | LAMA2 | 1.00 | 14354 | 3 | | | | LILRP2 | 1.00 |
| 14259 | 3 | | | | | LAMA3 | 1.00 | 14355 | 3 | | | | LIMCH1 | 1.00 |
| 14260 | 3 | | | | | LAMA4 | 1.00 | 14356 | 3 | | | | LIMS3-LOC440895 | 1.00 |
| 14261 | 3 | | | | | LAMA5 | 1.00 | 14357 | 3 | | | | LIN28A | 1.00 |
| 14262 | 3 | | | | | LAMB1 | 1.00 | 14358 | 3 | | | | LIN28B | 1.00 |
| 14263 | 3 | | | | | LAMB2 | 1.00 | 14359 | 3 | | | | LIN9 | 1.00 |
| 14264 | 3 | | | | | LAMB3 | 1.00 | 14360 | 3 | | | | LINC00028 | 1.00 |
| 14265 | 3 | | | | | LAMB4 | 1.00 | 14361 | 3 | | | | LINC00029 | 1.00 |
| 14266 | 3 | | | | | LAMC2 | 1.00 | 14362 | 3 | | | | LINC00032 | 1.00 |
| 14267 | 3 | | | | | LAMC3 | 1.00 | 14363 | 3 | | | | LINC00051 | 1.00 |
| 14268 | 3 | | | | | LARP6 | 1.00 | 14364 | 3 | | | | LINC00052 | 1.00 |
| 14269 | 3 | | | | | LAYN | 1.00 | 14365 | 3 | | | | LINC00086 | 1.00 |
| 14270 | 3 | | | | | LBP | 1.00 | 14366 | 3 | | | | LINC00087 | 1.00 |
| 14271 | 3 | | | | | LBX1 | 1.00 | 14367 | 3 | | | | LINC00102 | 1.00 |
| 14272 | 3 | | | | | LBX2 | 1.00 | 14368 | 3 | | | | LINC00111 | 1.00 |
| 14273 | 3 | | | | | LCA5 | 1.00 | 14369 | 3 | | | | LINC00112 | 1.00 |
| 14274 | 3 | | | | | LCA5L | 1.00 | 14370 | 3 | | | | LINC00113 | 1.00 |
| 14275 | 3 | | | | | LCE1A | 1.00 | 14371 | 3 | | | | LINC00114 | 1.00 |
| 14276 | 3 | | | | | LCE1B | 1.00 | 14372 | 3 | | | | LINC00158 | 1.00 |
| 14277 | 3 | | | | | LCE1C | 1.00 | 14373 | 3 | | | | LINC00159 | 1.00 |
| 14278 | 3 | | | | | LCE1D | 1.00 | 14374 | 3 | | | | LINC00160 | 1.00 |
| 14279 | 3 | | | | | LCE1E | 1.00 | 14375 | 3 | | | | LINC00161 | 1.00 |
| 14280 | 3 | | | | | LCE1F | 1.00 | 14376 | 3 | | | | LINC00162 | 1.00 |
| 14281 | 3 | | | | | LCE2A | 1.00 | 14377 | 3 | | | | LINC00163 | 1.00 |
| 14282 | 3 | | | | | LCE2B | 1.00 | 14378 | 3 | | | | LINC00167 | 1.00 |
| 14283 | 3 | | | | | LCE2C | 1.00 | 14379 | 3 | | | | LINC00176 | 1.00 |
| 14284 | 3 | | | | | LCE2D | 1.00 | 14380 | 3 | | | | LINC00184 | 1.00 |
| 14285 | 3 | | | | | LCE3A | 1.00 | 14381 | 3 | | | | LINC00200 | 1.00 |
| 14286 | 3 | | | | | LCE3B | 1.00 | 14382 | 3 | | | | LINC00202 | 1.00 |
| 14287 | 3 | | | | | LCE3C | 1.00 | 14383 | 3 | | | | LINC00207 | 1.00 |
| 14288 | 3 | | | | | LCE3D | 1.00 | 14384 | 3 | | | | LINC00208 | 1.00 |
| 14289 | 3 | | | | | LCE3E | 1.00 | 14385 | 3 | | | | LINC00221 | 1.00 |
| 14290 | 3 | | | | | LCE4A | 1.00 | 14386 | 3 | | | | LINC00222 | 1.00 |
| 14291 | 3 | | | | | LCE5A | 1.00 | 14387 | 3 | | | | LINC00226 | 1.00 |
| 14292 | 3 | | | | | LCE6A | 1.00 | 14388 | 3 | | | | LINC00229 | 1.00 |
| 14293 | 3 | | | | | LCN1 | 1.00 | 14389 | 3 | | | | LINC00230A | 1.00 |
| 14294 | 3 | | | | | LCN12 | 1.00 | 14390 | 3 | | | | LINC00230B | 1.00 |
| 14295 | 3 | | | | | LCN15 | 1.00 | 14391 | 3 | | | | LINC00235 | 1.00 |
| 14296 | 3 | | | | | LCN6 | 1.00 | 14392 | 3 | | | | LINC00238 | 1.00 |
| 14297 | 3 | | | | | LCN8 | 1.00 | 14393 | 3 | | | | LINC00240 | 1.00 |
| 14298 | 3 | | | | | LCN9 | 1.00 | 14394 | 3 | | | | LINC00242 | 1.00 |

Fig. 40 - 76

| | | | | | | | | | | | | | | | | |
|---|---|---|---|---|---|---|---|---|---|---|---|---|---|---|---|---|
| 14395 | 3 | | | | | LINC00244 | 1.00 | 14491 | 3 | | | | | LNP1 | 1.00 |
| 14396 | 3 | | | | | LINC00251 | 1.00 | 14492 | 3 | | | | | LNX1 | 1.00 |
| 14397 | 3 | | | | | LINC00254 | 1.00 | 14493 | 3 | | | | | LOC100093698 | 1.00 |
| 14398 | 3 | | | | | LINC00261 | 1.00 | 14494 | 3 | | | | | LOC100101266 | 1.00 |
| 14399 | 3 | | | | | LINC00264 | 1.00 | 14495 | 3 | | | | | LOC100125556 | 1.00 |
| 14400 | 3 | | | | | LINC00266-1 | 1.00 | 14496 | 3 | | | | | LOC100126784 | 1.00 |
| 14401 | 3 | | | | | LINC00271 | 1.00 | 14497 | 3 | | | | | LOC100127888 | 1.00 |
| 14402 | 3 | | | | | LINC00272 | 1.00 | 14498 | 3 | | | | | LOC100127983 | 1.00 |
| 14403 | 3 | | | | | LINC00273 | 1.00 | 14499 | 3 | | | | | LOC100128023 | 1.00 |
| 14404 | 3 | | | | | LINC00277 | 1.00 | 14500 | 3 | | | | | LOC100128054 | 1.00 |
| 14405 | 3 | | | | | LINC00281 | 1.00 | 14501 | 3 | | | | | LOC100128076 | 1.00 |
| 14406 | 3 | | | | | LINC00284 | 1.00 | 14502 | 3 | | | | | LOC100128098 | 1.00 |
| 14407 | 3 | | | | | LINC00290 | 1.00 | 14503 | 3 | | | | | LOC100128126 | 1.00 |
| 14408 | 3 | | | | | LINC00293 | 1.00 | 14504 | 3 | | | | | LOC100128164 | 1.00 |
| 14409 | 3 | | | | | LINC00299 | 1.00 | 14505 | 3 | | | | | LOC100128176 | 1.00 |
| 14410 | 3 | | | | | LINC00301 | 1.00 | 14506 | 3 | | | | | LOC100128239 | 1.00 |
| 14411 | 3 | | | | | LINC00303 | 1.00 | 14507 | 3 | | | | | LOC100128264 | 1.00 |
| 14412 | 3 | | | | | LINC00304 | 1.00 | 14508 | 3 | | | | | LOC100128292 | 1.00 |
| 14413 | 3 | | | | | LINC00305 | 1.00 | 14509 | 3 | | | | | LOC100128338 | 1.00 |
| 14414 | 3 | | | | | LINC00307 | 1.00 | 14510 | 3 | | | | | LOC100128361 | 1.00 |
| 14415 | 3 | | | | | LINC00308 | 1.00 | 14511 | 3 | | | | | LOC100128496 | 1.00 |
| 14416 | 3 | | | | | LINC00309 | 1.00 | 14512 | 3 | | | | | LOC100128505 | 1.00 |
| 14417 | 3 | | | | | LINC00310 | 1.00 | 14513 | 3 | | | | | LOC100128511 | 1.00 |
| 14418 | 3 | | | | | LINC00311 | 1.00 | 14514 | 3 | | | | | LOC100128531 | 1.00 |
| 14419 | 3 | | | | | LINC00312 | 1.00 | 14515 | 3 | | | | | LOC100128554 | 1.00 |
| 14420 | 3 | | | | | LINC00313 | 1.00 | 14516 | 3 | | | | | LOC100128568 | 1.00 |
| 14421 | 3 | | | | | LINC00314 | 1.00 | 14517 | 3 | | | | | LOC100128590 | 1.00 |
| 14422 | 3 | | | | | LINC00315 | 1.00 | 14518 | 3 | | | | | LOC100128593 | 1.00 |
| 14423 | 3 | | | | | LINC00317 | 1.00 | 14519 | 3 | | | | | LOC100128640 | 1.00 |
| 14424 | 3 | | | | | LINC00319 | 1.00 | 14520 | 3 | | | | | LOC100128675 | 1.00 |
| 14425 | 3 | | | | | LINC00320 | 1.00 | 14521 | 3 | | | | | LOC100128714 | 1.00 |
| 14426 | 3 | | | | | LINC00323 | 1.00 | 14522 | 3 | | | | | LOC100128750 | 1.00 |
| 14427 | 3 | | | | | LINC00326 | 1.00 | 14523 | 3 | | | | | LOC100128787 | 1.00 |
| 14428 | 3 | | | | | LINC00327 | 1.00 | 14524 | 3 | | | | | LOC100128788 | 1.00 |
| 14429 | 3 | | | | | LINC00330 | 1.00 | 14525 | 3 | | | | | LOC100128811 | 1.00 |
| 14430 | 3 | | | | | LINC00336 | 1.00 | 14526 | 3 | | | | | LOC100128946 | 1.00 |
| 14431 | 3 | | | | | LINC00340 | 1.00 | 14527 | 3 | | | | | LOC100128993 | 1.00 |
| 14432 | 3 | | | | | LINC00346 | 1.00 | 14528 | 3 | | | | | LOC100129027 | 1.00 |
| 14433 | 3 | | | | | LINC00347 | 1.00 | 14529 | 3 | | | | | LOC100129046 | 1.00 |
| 14434 | 3 | | | | | LINC00410 | 1.00 | 14530 | 3 | | | | | LOC100129055 | 1.00 |
| 14435 | 3 | | | | | LINC00421 | 1.00 | 14531 | 3 | | | | | LOC100129083 | 1.00 |
| 14436 | 3 | | | | | LINC00442 | 1.00 | 14532 | 3 | | | | | LOC100129175 | 1.00 |
| 14437 | 3 | | | | | LINC00460 | 1.00 | 14533 | 3 | | | | | LOC100129213 | 1.00 |
| 14438 | 3 | | | | | LINC00461 | 1.00 | 14534 | 3 | | | | | LOC100129216 | 1.00 |
| 14439 | 3 | | | | | LINC00466 | 1.00 | 14535 | 3 | | | | | LOC100129269 | 1.00 |
| 14440 | 3 | | | | | LINC00469 | 1.00 | 14536 | 3 | | | | | LOC100129316 | 1.00 |
| 14441 | 3 | | | | | LINC00470 | 1.00 | 14537 | 3 | | | | | LOC100129345 | 1.00 |
| 14442 | 3 | | | | | LINC00471 | 1.00 | 14538 | 3 | | | | | LOC100129407 | 1.00 |
| 14443 | 3 | | | | | LINC00472 | 1.00 | 14539 | 3 | | | | | LOC100129427 | 1.00 |
| 14444 | 3 | | | | | LINC00473 | 1.00 | 14540 | 3 | | | | | LOC100129480 | 1.00 |
| 14445 | 3 | | | | | LINC00474 | 1.00 | 14541 | 3 | | | | | LOC100129515 | 1.00 |
| 14446 | 3 | | | | | LINC00475 | 1.00 | 14542 | 3 | | | | | LOC100129518 | 1.00 |
| 14447 | 3 | | | | | LINC00477 | 1.00 | 14543 | 3 | | | | | LOC100129520 | 1.00 |
| 14448 | 3 | | | | | LINC00478 | 1.00 | 14544 | 3 | | | | | LOC100129620 | 1.00 |
| 14449 | 3 | | | | | LINC00479 | 1.00 | 14545 | 3 | | | | | LOC100129636 | 1.00 |
| 14450 | 3 | | | | | LINC00483 | 1.00 | 14546 | 3 | | | | | LOC100129662 | 1.00 |
| 14451 | 3 | | | | | LINC00485 | 1.00 | 14547 | 3 | | | | | LOC100129716 | 1.00 |
| 14452 | 3 | | | | | LINC00486 | 1.00 | 14548 | 3 | | | | | LOC100129722 | 1.00 |
| 14453 | 3 | | | | | LINC00488 | 1.00 | 14549 | 3 | | | | | LOC100129794 | 1.00 |
| 14454 | 3 | | | | | LINC00494 | 1.00 | 14550 | 3 | | | | | LOC100129845 | 1.00 |
| 14455 | 3 | | | | | LINC00511 | 1.00 | 14551 | 3 | | | | | LOC100129858 | 1.00 |
| 14456 | 3 | | | | | LINC00514 | 1.00 | 14552 | 3 | | | | | LOC100129924 | 1.00 |
| 14457 | 3 | | | | | LINC00515 | 1.00 | 14553 | 3 | | | | | LOC100129935 | 1.00 |
| 14458 | 3 | | | | | LINC00518 | 1.00 | 14554 | 3 | | | | | LOC100130000 | 1.00 |
| 14459 | 3 | | | | | LINC00520 | 1.00 | 14555 | 3 | | | | | LOC100130015 | 1.00 |
| 14460 | 3 | | | | | LINC00521 | 1.00 | 14556 | 3 | | | | | LOC100130155 | 1.00 |
| 14461 | 3 | | | | | LINC00523 | 1.00 | 14557 | 3 | | | | | LOC100130197 | 1.00 |
| 14462 | 3 | | | | | LINC00525 | 1.00 | 14558 | 3 | | | | | LOC100130238 | 1.00 |
| 14463 | 3 | | | | | LINC00535 | 1.00 | 14559 | 3 | | | | | LOC100130264 | 1.00 |
| 14464 | 3 | | | | | LINC00536 | 1.00 | 14560 | 3 | | | | | LOC100130275 | 1.00 |
| 14465 | 3 | | | | | LINC00538 | 1.00 | 14561 | 3 | | | | | LOC100130301 | 1.00 |
| 14466 | 3 | | | | | LINC00547 | 1.00 | 14562 | 3 | | | | | LOC100130348 | 1.00 |
| 14467 | 3 | | | | | LINC00548 | 1.00 | 14563 | 3 | | | | | LOC100130417 | 1.00 |
| 14468 | 3 | | | | | LINC00550 | 1.00 | 14564 | 3 | | | | | LOC100130451 | 1.00 |
| 14469 | 3 | | | | | LINC00552 | 1.00 | 14565 | 3 | | | | | LOC100130452 | 1.00 |
| 14470 | 3 | | | | | LINC00574 | 1.00 | 14566 | 3 | | | | | LOC100130480 | 1.00 |
| 14471 | 3 | | | | | LINC00575 | 1.00 | 14567 | 3 | | | | | LOC100130522 | 1.00 |
| 14472 | 3 | | | | | LINGO1 | 1.00 | 14568 | 3 | | | | | LOC100130673 | 1.00 |
| 14473 | 3 | | | | | LINGO4 | 1.00 | 14569 | 3 | | | | | LOC100130691 | 1.00 |
| 14474 | 3 | | | | | LIPF | 1.00 | 14570 | 3 | | | | | LOC100130700 | 1.00 |
| 14475 | 3 | | | | | LIPG | 1.00 | 14571 | 3 | | | | | LOC100130705 | 1.00 |
| 14476 | 3 | | | | | LIPH | 1.00 | 14572 | 3 | | | | | LOC100130849 | 1.00 |
| 14477 | 3 | | | | | LIPI | 1.00 | 14573 | 3 | | | | | LOC100130880 | 1.00 |
| 14478 | 3 | | | | | LIPJ | 1.00 | 14574 | 3 | | | | | LOC100130890 | 1.00 |
| 14479 | 3 | | | | | LIPK | 1.00 | 14575 | 3 | | | | | LOC100130894 | 1.00 |
| 14480 | 3 | | | | | LIPM | 1.00 | 14576 | 3 | | | | | LOC100130899 | 1.00 |
| 14481 | 3 | | | | | LIX1 | 1.00 | 14577 | 3 | | | | | LOC100130954 | 1.00 |
| 14482 | 3 | | | | | LMAN1L | 1.00 | 14578 | 3 | | | | | LOC100130964 | 1.00 |
| 14483 | 3 | | | | | LMCD1 | 1.00 | 14579 | 3 | | | | | LOC100130987 | 1.00 |
| 14484 | 3 | | | | | LMO1 | 1.00 | 14580 | 3 | | | | | LOC100131047 | 1.00 |
| 14485 | 3 | | | | | LMO3 | 1.00 | 14581 | 3 | | | | | LOC100131060 | 1.00 |
| 14486 | 3 | | | | | LMOD1 | 1.00 | 14582 | 3 | | | | | LOC100131138 | 1.00 |
| 14487 | 3 | | | | | LMOD2 | 1.00 | 14583 | 3 | | | | | LOC100131208 | 1.00 |
| 14488 | 3 | | | | | LMOD3 | 1.00 | 14584 | 3 | | | | | LOC100131234 | 1.00 |
| 14489 | 3 | | | | | LMX1A | 1.00 | 14585 | 3 | | | | | LOC100131257 | 1.00 |
| 14490 | 3 | | | | | LMX1B | 1.00 | 14586 | 3 | | | | | LOC100131289 | 1.00 |

Fig. 40 - 77

| | | | | | | | | | | | | | | |
|---|---|---|---|---|---|---|---|---|---|---|---|---|---|---|
| 14587 | 3 | | | | | LOC100131320 | 1.00 | 14683 | 3 | | | | LOC100289361 | 1.00 |
| 14588 | 3 | | | | | LOC100131347 | 1.00 | 14684 | 3 | | | | LOC100289495 | 1.00 |
| 14589 | 3 | | | | | LOC100131366 | 1.00 | 14685 | 3 | | | | LOC100289509 | 1.00 |
| 14590 | 3 | | | | | LOC100131496 | 1.00 | 14686 | 3 | | | | LOC100289650 | 1.00 |
| 14591 | 3 | | | | | LOC100131551 | 1.00 | 14687 | 3 | | | | LOC100289656 | 1.00 |
| 14592 | 3 | | | | | LOC100131635 | 1.00 | 14688 | 3 | | | | LOC100289673 | 1.00 |
| 14593 | 3 | | | | | LOC100131691 | 1.00 | 14689 | 3 | | | | LOC100292680 | 1.00 |
| 14594 | 3 | | | | | LOC100131726 | 1.00 | 14690 | 3 | | | | LOC100293534 | 1.00 |
| 14595 | 3 | | | | | LOC100131825 | 1.00 | 14691 | 3 | | | | LOC100302401 | 1.00 |
| 14596 | 3 | | | | | LOC100132078 | 1.00 | 14692 | 3 | | | | LOC100302640 | 1.00 |
| 14597 | 3 | | | | | LOC100132146 | 1.00 | 14693 | 3 | | | | LOC100302650 | 1.00 |
| 14598 | 3 | | | | | LOC100132215 | 1.00 | 14694 | 3 | | | | LOC100303749 | 1.00 |
| 14599 | 3 | | | | | LOC100132354 | 1.00 | 14695 | 3 | | | | LOC100306975 | 1.00 |
| 14600 | 3 | | | | | LOC100132396 | 1.00 | 14696 | 3 | | | | LOC100329135 | 1.00 |
| 14601 | 3 | | | | | LOC100132526 | 1.00 | 14697 | 3 | | | | LOC100422737 | 1.00 |
| 14602 | 3 | | | | | LOC100132735 | 1.00 | 14698 | 3 | | | | LOC100498859 | 1.00 |
| 14603 | 3 | | | | | LOC100132774 | 1.00 | 14699 | 3 | | | | LOC100499183 | 1.00 |
| 14604 | 3 | | | | | LOC100132781 | 1.00 | 14700 | 3 | | | | LOC100499194 | 1.00 |
| 14605 | 3 | | | | | LOC100132891 | 1.00 | 14701 | 3 | | | | LOC100499227 | 1.00 |
| 14606 | 3 | | | | | LOC100132987 | 1.00 | 14702 | 3 | | | | LOC100499467 | 1.00 |
| 14607 | 3 | | | | | LOC100133050 | 1.00 | 14703 | 3 | | | | LOC100499484 | 1.00 |
| 14608 | 3 | | | | | LOC100133123 | 1.00 | 14704 | 3 | | | | LOC100500773 | 1.00 |
| 14609 | 3 | | | | | LOC100133267 | 1.00 | 14705 | 3 | | | | LOC100500938 | 1.00 |
| 14610 | 3 | | | | | LOC100133286 | 1.00 | 14706 | 3 | | | | LOC100505474 | 1.00 |
| 14611 | 3 | | | | | LOC100133308 | 1.00 | 14707 | 3 | | | | LOC100505478 | 1.00 |
| 14612 | 3 | | | | | LOC100133315 | 1.00 | 14708 | 3 | | | | LOC100505495 | 1.00 |
| 14613 | 3 | | | | | LOC100133461 | 1.00 | 14709 | 3 | | | | LOC100505536 | 1.00 |
| 14614 | 3 | | | | | LOC100133612 | 1.00 | 14710 | 3 | | | | LOC100505540 | 1.00 |
| 14615 | 3 | | | | | LOC100133920 | 1.00 | 14711 | 3 | | | | LOC100505545 | 1.00 |
| 14616 | 3 | | | | | LOC100133957 | 1.00 | 14712 | 3 | | | | LOC100505583 | 1.00 |
| 14617 | 3 | | | | | LOC100133985 | 1.00 | 14713 | 3 | | | | LOC100505619 | 1.00 |
| 14618 | 3 | | | | | LOC100134015 | 1.00 | 14714 | 3 | | | | LOC100505624 | 1.00 |
| 14619 | 3 | | | | | LOC100134259 | 1.00 | 14715 | 3 | | | | LOC100505633 | 1.00 |
| 14620 | 3 | | | | | LOC100134317 | 1.00 | 14716 | 3 | | | | LOC100505658 | 1.00 |
| 14621 | 3 | | | | | LOC100134368 | 1.00 | 14717 | 3 | | | | LOC100505659 | 1.00 |
| 14622 | 3 | | | | | LOC100134713 | 1.00 | 14718 | 3 | | | | LOC100505666 | 1.00 |
| 14623 | 3 | | | | | LOC100134868 | 1.00 | 14719 | 3 | | | | LOC100505676 | 1.00 |
| 14624 | 3 | | | | | LOC100144595 | 1.00 | 14720 | 3 | | | | LOC100505678 | 1.00 |
| 14625 | 3 | | | | | LOC100144597 | 1.00 | 14721 | 3 | | | | LOC100505679 | 1.00 |
| 14626 | 3 | | | | | LOC100144602 | 1.00 | 14722 | 3 | | | | LOC100505695 | 1.00 |
| 14627 | 3 | | | | | LOC100144604 | 1.00 | 14723 | 3 | | | | LOC100505716 | 1.00 |
| 14628 | 3 | | | | | LOC100169752 | 1.00 | 14724 | 3 | | | | LOC100505718 | 1.00 |
| 14629 | 3 | | | | | LOC100188947 | 1.00 | 14725 | 3 | | | | LOC100505738 | 1.00 |
| 14630 | 3 | | | | | LOC100189589 | 1.00 | 14726 | 3 | | | | LOC100505768 | 1.00 |
| 14631 | 3 | | | | | LOC100190938 | 1.00 | 14727 | 3 | | | | LOC100505776 | 1.00 |
| 14632 | 3 | | | | | LOC100190940 | 1.00 | 14728 | 3 | | | | LOC100505782 | 1.00 |
| 14633 | 3 | | | | | LOC100192204 | 1.00 | 14729 | 3 | | | | LOC100505795 | 1.00 |
| 14634 | 3 | | | | | LOC100192378 | 1.00 | 14730 | 3 | | | | LOC100505806 | 1.00 |
| 14635 | 3 | | | | | LOC100192426 | 1.00 | 14731 | 3 | | | | LOC100505817 | 1.00 |
| 14636 | 3 | | | | | LOC100216001 | 1.00 | 14732 | 3 | | | | LOC100505826 | 1.00 |
| 14637 | 3 | | | | | LOC100216479 | 1.00 | 14733 | 3 | | | | LOC100505835 | 1.00 |
| 14638 | 3 | | | | | LOC100240734 | 1.00 | 14734 | 3 | | | | LOC100505839 | 1.00 |
| 14639 | 3 | | | | | LOC100240735 | 1.00 | 14735 | 3 | | | | LOC100505841 | 1.00 |
| 14640 | 3 | | | | | LOC100268168 | 1.00 | 14736 | 3 | | | | LOC100505894 | 1.00 |
| 14641 | 3 | | | | | LOC100270679 | 1.00 | 14737 | 3 | | | | LOC100505912 | 1.00 |
| 14642 | 3 | | | | | LOC100270746 | 1.00 | 14738 | 3 | | | | LOC100505918 | 1.00 |
| 14643 | 3 | | | | | LOC100271702 | 1.00 | 14739 | 3 | | | | LOC100505933 | 1.00 |
| 14644 | 3 | | | | | LOC100271832 | 1.00 | 14740 | 3 | | | | LOC100505964 | 1.00 |
| 14645 | 3 | | | | | LOC100272217 | 1.00 | 14741 | 3 | | | | LOC100505967 | 1.00 |
| 14646 | 3 | | | | | LOC100286922 | 1.00 | 14742 | 3 | | | | LOC100505978 | 1.00 |
| 14647 | 3 | | | | | LOC100286938 | 1.00 | 14743 | 3 | | | | LOC100505989 | 1.00 |
| 14648 | 3 | | | | | LOC100286979 | 1.00 | 14744 | 3 | | | | LOC100506012 | 1.00 |
| 14649 | 3 | | | | | LOC100287010 | 1.00 | 14745 | 3 | | | | LOC100506013 | 1.00 |
| 14650 | 3 | | | | | LOC100287015 | 1.00 | 14746 | 3 | | | | LOC100506023 | 1.00 |
| 14651 | 3 | | | | | LOC100287216 | 1.00 | 14747 | 3 | | | | LOC100506025 | 1.00 |
| 14652 | 3 | | | | | LOC100287225 | 1.00 | 14748 | 3 | | | | LOC100506050 | 1.00 |
| 14653 | 3 | | | | | LOC100287314 | 1.00 | 14749 | 3 | | | | LOC100506071 | 1.00 |
| 14654 | 3 | | | | | LOC100287559 | 1.00 | 14750 | 3 | | | | LOC100506083 | 1.00 |
| 14655 | 3 | | | | | LOC100287632 | 1.00 | 14751 | 3 | | | | LOC100506085 | 1.00 |
| 14656 | 3 | | | | | LOC100287718 | 1.00 | 14752 | 3 | | | | LOC100506122 | 1.00 |
| 14657 | 3 | | | | | LOC100287765 | 1.00 | 14753 | 3 | | | | LOC100506134 | 1.00 |
| 14658 | 3 | | | | | LOC100287792 | 1.00 | 14754 | 3 | | | | LOC100506136 | 1.00 |
| 14659 | 3 | | | | | LOC100287814 | 1.00 | 14755 | 3 | | | | LOC100506172 | 1.00 |
| 14660 | 3 | | | | | LOC100287834 | 1.00 | 14756 | 3 | | | | LOC100506178 | 1.00 |
| 14661 | 3 | | | | | LOC100287846 | 1.00 | 14757 | 3 | | | | LOC100506195 | 1.00 |
| 14662 | 3 | | | | | LOC100287879 | 1.00 | 14758 | 3 | | | | LOC100506207 | 1.00 |
| 14663 | 3 | | | | | LOC100287944 | 1.00 | 14759 | 3 | | | | LOC100506241 | 1.00 |
| 14664 | 3 | | | | | LOC100288077 | 1.00 | 14760 | 3 | | | | LOC100506274 | 1.00 |
| 14665 | 3 | | | | | LOC100288079 | 1.00 | 14761 | 3 | | | | LOC100506368 | 1.00 |
| 14666 | 3 | | | | | LOC100288122 | 1.00 | 14762 | 3 | | | | LOC100506384 | 1.00 |
| 14667 | 3 | | | | | LOC100288181 | 1.00 | 14763 | 3 | | | | LOC100506385 | 1.00 |
| 14668 | 3 | | | | | LOC100288198 | 1.00 | 14764 | 3 | | | | LOC100506388 | 1.00 |
| 14669 | 3 | | | | | LOC100288255 | 1.00 | 14765 | 3 | | | | LOC100506393 | 1.00 |
| 14670 | 3 | | | | | LOC100288346 | 1.00 | 14766 | 3 | | | | LOC100506394 | 1.00 |
| 14671 | 3 | | | | | LOC100288428 | 1.00 | 14767 | 3 | | | | LOC100506409 | 1.00 |
| 14672 | 3 | | | | | LOC100288524 | 1.00 | 14768 | 3 | | | | LOC100506421 | 1.00 |
| 14673 | 3 | | | | | LOC100288570 | 1.00 | 14769 | 3 | | | | LOC100506422 | 1.00 |
| 14674 | 3 | | | | | LOC100288748 | 1.00 | 14770 | 3 | | | | LOC100506433 | 1.00 |
| 14675 | 3 | | | | | LOC100288814 | 1.00 | 14771 | 3 | | | | LOC100506451 | 1.00 |
| 14676 | 3 | | | | | LOC100288911 | 1.00 | 14772 | 3 | | | | LOC100506462 | 1.00 |
| 14677 | 3 | | | | | LOC100288974 | 1.00 | 14773 | 3 | | | | LOC100506474 | 1.00 |
| 14678 | 3 | | | | | LOC100289092 | 1.00 | 14774 | 3 | | | | LOC100506497 | 1.00 |
| 14679 | 3 | | | | | LOC100289178 | 1.00 | 14775 | 3 | | | | LOC100506540 | 1.00 |
| 14680 | 3 | | | | | LOC100289187 | 1.00 | 14776 | 3 | | | | LOC100506599 | 1.00 |
| 14681 | 3 | | | | | LOC100289211 | 1.00 | 14777 | 3 | | | | LOC100506650 | 1.00 |
| 14682 | 3 | | | | | LOC100289255 | 1.00 | 14778 | 3 | | | | LOC100506655 | 1.00 |

Fig. 40 - 78

| | | | | | | | | | | | | | | | |
|---|---|---|---|---|---|---|---|---|---|---|---|---|---|---|---|
| 14779 | 3 | | | | | LOC100506660 | 1.00 | 14875 | 3 | | | | | LOC145474 | 1.00 |
| 14780 | 3 | | | | | LOC100506688 | 1.00 | 14876 | 3 | | | | | LOC145663 | 1.00 |
| 14781 | 3 | | | | | LOC100506733 | 1.00 | 14877 | 3 | | | | | LOC145820 | 1.00 |
| 14782 | 3 | | | | | LOC100506746 | 1.00 | 14878 | 3 | | | | | LOC145837 | 1.00 |
| 14783 | 3 | | | | | LOC100506757 | 1.00 | 14879 | 3 | | | | | LOC145845 | 1.00 |
| 14784 | 3 | | | | | LOC100506795 | 1.00 | 14880 | 3 | | | | | LOC146336 | 1.00 |
| 14785 | 3 | | | | | LOC100506804 | 1.00 | 14881 | 3 | | | | | LOC146481 | 1.00 |
| 14786 | 3 | | | | | LOC100506810 | 1.00 | 14882 | 3 | | | | | LOC146513 | 1.00 |
| 14787 | 3 | | | | | LOC100506835 | 1.00 | 14883 | 3 | | | | | LOC147093 | 1.00 |
| 14788 | 3 | | | | | LOC100506874 | 1.00 | 14884 | 3 | | | | | LOC147646 | 1.00 |
| 14789 | 3 | | | | | LOC100506888 | 1.00 | 14885 | 3 | | | | | LOC147670 | 1.00 |
| 14790 | 3 | | | | | LOC100506895 | 1.00 | 14886 | 3 | | | | | LOC148145 | 1.00 |
| 14791 | 3 | | | | | LOC100506939 | 1.00 | 14887 | 3 | | | | | LOC148696 | 1.00 |
| 14792 | 3 | | | | | LOC100506994 | 1.00 | 14888 | 3 | | | | | LOC148709 | 1.00 |
| 14793 | 3 | | | | | LOC100507003 | 1.00 | 14889 | 3 | | | | | LOC148824 | 1.00 |
| 14794 | 3 | | | | | LOC100507032 | 1.00 | 14890 | 3 | | | | | LOC149086 | 1.00 |
| 14795 | 3 | | | | | LOC100507043 | 1.00 | 14891 | 3 | | | | | LOC149134 | 1.00 |
| 14796 | 3 | | | | | LOC100507050 | 1.00 | 14892 | 3 | | | | | LOC149373 | 1.00 |
| 14797 | 3 | | | | | LOC100507053 | 1.00 | 14893 | 3 | | | | | LOC149773 | 1.00 |
| 14798 | 3 | | | | | LOC100507055 | 1.00 | 14894 | 3 | | | | | LOC149950 | 1.00 |
| 14799 | 3 | | | | | LOC100507066 | 1.00 | 14895 | 3 | | | | | LOC150185 | 1.00 |
| 14800 | 3 | | | | | LOC100507086 | 1.00 | 14896 | 3 | | | | | LOC150197 | 1.00 |
| 14801 | 3 | | | | | LOC100507091 | 1.00 | 14897 | 3 | | | | | LOC150381 | 1.00 |
| 14802 | 3 | | | | | LOC100507096 | 1.00 | 14898 | 3 | | | | | LOC150527 | 1.00 |
| 14803 | 3 | | | | | LOC100507127 | 1.00 | 14899 | 3 | | | | | LOC150568 | 1.00 |
| 14804 | 3 | | | | | LOC100507140 | 1.00 | 14900 | 3 | | | | | LOC150622 | 1.00 |
| 14805 | 3 | | | | | LOC100507156 | 1.00 | 14901 | 3 | | | | | LOC150935 | 1.00 |
| 14806 | 3 | | | | | LOC100507173 | 1.00 | 14902 | 3 | | | | | LOC151009 | 1.00 |
| 14807 | 3 | | | | | LOC100507178 | 1.00 | 14903 | 3 | | | | | LOC151171 | 1.00 |
| 14808 | 3 | | | | | LOC100507194 | 1.00 | 14904 | 3 | | | | | LOC151174 | 1.00 |
| 14809 | 3 | | | | | LOC100507203 | 1.00 | 14905 | 3 | | | | | LOC151300 | 1.00 |
| 14810 | 3 | | | | | LOC100507205 | 1.00 | 14906 | 3 | | | | | LOC151475 | 1.00 |
| 14811 | 3 | | | | | LOC100507206 | 1.00 | 14907 | 3 | | | | | LOC151484 | 1.00 |
| 14812 | 3 | | | | | LOC100507240 | 1.00 | 14908 | 3 | | | | | LOC151658 | 1.00 |
| 14813 | 3 | | | | | LOC100507244 | 1.00 | 14909 | 3 | | | | | LOC152024 | 1.00 |
| 14814 | 3 | | | | | LOC100507250 | 1.00 | 14910 | 3 | | | | | LOC152225 | 1.00 |
| 14815 | 3 | | | | | LOC100507254 | 1.00 | 14911 | 3 | | | | | LOC152578 | 1.00 |
| 14816 | 3 | | | | | LOC100507266 | 1.00 | 14912 | 3 | | | | | LOC152742 | 1.00 |
| 14817 | 3 | | | | | LOC100507299 | 1.00 | 14913 | 3 | | | | | LOC153469 | 1.00 |
| 14818 | 3 | | | | | LOC100507300 | 1.00 | 14914 | 3 | | | | | LOC153910 | 1.00 |
| 14819 | 3 | | | | | LOC100507334 | 1.00 | 14915 | 3 | | | | | LOC154092 | 1.00 |
| 14820 | 3 | | | | | LOC100507341 | 1.00 | 14916 | 3 | | | | | LOC154449 | 1.00 |
| 14821 | 3 | | | | | LOC100507346 | 1.00 | 14917 | 3 | | | | | LOC154822 | 1.00 |
| 14822 | 3 | | | | | LOC100507351 | 1.00 | 14918 | 3 | | | | | LOC154860 | 1.00 |
| 14823 | 3 | | | | | LOC100507362 | 1.00 | 14919 | 3 | | | | | LOC154872 | 1.00 |
| 14824 | 3 | | | | | LOC100507377 | 1.00 | 14920 | 3 | | | | | LOC157273 | 1.00 |
| 14825 | 3 | | | | | LOC100507389 | 1.00 | 14921 | 3 | | | | | LOC157381 | 1.00 |
| 14826 | 3 | | | | | LOC100507391 | 1.00 | 14922 | 3 | | | | | LOC157627 | 1.00 |
| 14827 | 3 | | | | | LOC100507401 | 1.00 | 14923 | 3 | | | | | LOC158376 | 1.00 |
| 14828 | 3 | | | | | LOC100507410 | 1.00 | 14924 | 3 | | | | | LOC158434 | 1.00 |
| 14829 | 3 | | | | | LOC100507421 | 1.00 | 14925 | 3 | | | | | LOC158435 | 1.00 |
| 14830 | 3 | | | | | LOC100507423 | 1.00 | 14926 | 3 | | | | | LOC158572 | 1.00 |
| 14831 | 3 | | | | | LOC100507433 | 1.00 | 14927 | 3 | | | | | LOC158696 | 1.00 |
| 14832 | 3 | | | | | LOC100507443 | 1.00 | 14928 | 3 | | | | | LOC170425 | 1.00 |
| 14833 | 3 | | | | | LOC100507462 | 1.00 | 14929 | 3 | | | | | LOC1720 | 1.00 |
| 14834 | 3 | | | | | LOC100507466 | 1.00 | 14930 | 3 | | | | | LOC200261 | 1.00 |
| 14835 | 3 | | | | | LOC100507470 | 1.00 | 14931 | 3 | | | | | LOC200726 | 1.00 |
| 14836 | 3 | | | | | LOC100507472 | 1.00 | 14932 | 3 | | | | | LOC201477 | 1.00 |
| 14837 | 3 | | | | | LOC100507489 | 1.00 | 14933 | 3 | | | | | LOC201617 | 1.00 |
| 14838 | 3 | | | | | LOC100507537 | 1.00 | 14934 | 3 | | | | | LOC201651 | 1.00 |
| 14839 | 3 | | | | | LOC100507547 | 1.00 | 14935 | 3 | | | | | LOC219347 | 1.00 |
| 14840 | 3 | | | | | LOC100507564 | 1.00 | 14936 | 3 | | | | | LOC219731 | 1.00 |
| 14841 | 3 | | | | | LOC100507582 | 1.00 | 14937 | 3 | | | | | LOC221122 | 1.00 |
| 14842 | 3 | | | | | LOC100507584 | 1.00 | 14938 | 3 | | | | | LOC253044 | 1.00 |
| 14843 | 3 | | | | | LOC100507588 | 1.00 | 14939 | 3 | | | | | LOC253573 | 1.00 |
| 14844 | 3 | | | | | LOC100507589 | 1.00 | 14940 | 3 | | | | | LOC253962 | 1.00 |
| 14845 | 3 | | | | | LOC100507600 | 1.00 | 14941 | 3 | | | | | LOC254099 | 1.00 |
| 14846 | 3 | | | | | LOC100507605 | 1.00 | 14942 | 3 | | | | | LOC254312 | 1.00 |
| 14847 | 3 | | | | | LOC100507629 | 1.00 | 14943 | 3 | | | | | LOC255025 | 1.00 |
| 14848 | 3 | | | | | LOC100507651 | 1.00 | 14944 | 3 | | | | | LOC255130 | 1.00 |
| 14849 | 3 | | | | | LOC100509575 | 1.00 | 14945 | 3 | | | | | LOC255167 | 1.00 |
| 14850 | 3 | | | | | LOC100509894 | 1.00 | 14946 | 3 | | | | | LOC255411 | 1.00 |
| 14851 | 3 | | | | | LOC100526771 | 1.00 | 14947 | 3 | | | | | LOC255480 | 1.00 |
| 14852 | 3 | | | | | LOC100616530 | 1.00 | 14948 | 3 | | | | | LOC255654 | 1.00 |
| 14853 | 3 | | | | | LOC100616668 | 1.00 | 14949 | 3 | | | | | LOC256880 | 1.00 |
| 14854 | 3 | | | | | LOC100628307 | 1.00 | 14950 | 3 | | | | | LOC257358 | 1.00 |
| 14855 | 3 | | | | | LOC100631378 | 1.00 | 14951 | 3 | | | | | LOC257396 | 1.00 |
| 14856 | 3 | | | | | LOC100652730 | 1.00 | 14952 | 3 | | | | | LOC282980 | 1.00 |
| 14857 | 3 | | | | | LOC100652739 | 1.00 | 14953 | 3 | | | | | LOC283033 | 1.00 |
| 14858 | 3 | | | | | LOC100652759 | 1.00 | 14954 | 3 | | | | | LOC283038 | 1.00 |
| 14859 | 3 | | | | | LOC100652770 | 1.00 | 14955 | 3 | | | | | LOC283050 | 1.00 |
| 14860 | 3 | | | | | LOC100652791 | 1.00 | 14956 | 3 | | | | | LOC283116 | 1.00 |
| 14861 | 3 | | | | | LOC100652909 | 1.00 | 14957 | 3 | | | | | LOC283143 | 1.00 |
| 14862 | 3 | | | | | LOC100652999 | 1.00 | 14958 | 3 | | | | | LOC283177 | 1.00 |
| 14863 | 3 | | | | | LOC100653515 | 1.00 | 14959 | 3 | | | | | LOC283214 | 1.00 |
| 14864 | 3 | | | | | LOC116437 | 1.00 | 14960 | 3 | | | | | LOC283299 | 1.00 |
| 14865 | 3 | | | | | LOC120824 | 1.00 | 14961 | 3 | | | | | LOC283332 | 1.00 |
| 14866 | 3 | | | | | LOC126536 | 1.00 | 14962 | 3 | | | | | LOC283335 | 1.00 |
| 14867 | 3 | | | | | LOC127841 | 1.00 | 14963 | 3 | | | | | LOC283392 | 1.00 |
| 14868 | 3 | | | | | LOC143188 | 1.00 | 14964 | 3 | | | | | LOC283403 | 1.00 |
| 14869 | 3 | | | | | LOC143666 | 1.00 | 14965 | 3 | | | | | LOC283404 | 1.00 |
| 14870 | 3 | | | | | LOC144481 | 1.00 | 14966 | 3 | | | | | LOC283440 | 1.00 |
| 14871 | 3 | | | | | LOC144486 | 1.00 | 14967 | 3 | | | | | LOC283481 | 1.00 |
| 14872 | 3 | | | | | LOC144571 | 1.00 | 14968 | 3 | | | | | LOC283547 | 1.00 |
| 14873 | 3 | | | | | LOC144742 | 1.00 | 14969 | 3 | | | | | LOC283553 | 1.00 |
| 14874 | 3 | | | | | LOC145216 | 1.00 | 14970 | 3 | | | | | LOC283585 | 1.00 |

Fig. 40 - 79

| | | | | | | | | | | | | | | | | |
|---|---|---|---|---|---|---|---|---|---|---|---|---|---|---|---|---|
| 14971 | 3 | | | | | | LOC283587 | 1.00 | 15067 | 3 | | | | | LOC339505 | 1.00 |
| 14972 | 3 | | | | | | LOC283683 | 1.00 | 15068 | 3 | | | | | LOC339524 | 1.00 |
| 14973 | 3 | | | | | | LOC283688 | 1.00 | 15069 | 3 | | | | | LOC339529 | 1.00 |
| 14974 | 3 | | | | | | LOC283693 | 1.00 | 15070 | 3 | | | | | LOC339535 | 1.00 |
| 14975 | 3 | | | | | | LOC283731 | 1.00 | 15071 | 3 | | | | | LOC339568 | 1.00 |
| 14976 | 3 | | | | | | LOC283738 | 1.00 | 15072 | 3 | | | | | LOC339593 | 1.00 |
| 14977 | 3 | | | | | | LOC283761 | 1.00 | 15073 | 3 | | | | | LOC339622 | 1.00 |
| 14978 | 3 | | | | | | LOC283856 | 1.00 | 15074 | 3 | | | | | LOC339666 | 1.00 |
| 14979 | 3 | | | | | | LOC283867 | 1.00 | 15075 | 3 | | | | | LOC339685 | 1.00 |
| 14980 | 3 | | | | | | LOC283888 | 1.00 | 15076 | 3 | | | | | LOC339788 | 1.00 |
| 14981 | 3 | | | | | | LOC283914 | 1.00 | 15077 | 3 | | | | | LOC339807 | 1.00 |
| 14982 | 3 | | | | | | LOC284009 | 1.00 | 15078 | 3 | | | | | LOC339822 | 1.00 |
| 14983 | 3 | | | | | | LOC284080 | 1.00 | 15079 | 3 | | | | | LOC339862 | 1.00 |
| 14984 | 3 | | | | | | LOC284100 | 1.00 | 15080 | 3 | | | | | LOC339894 | 1.00 |
| 14985 | 3 | | | | | | LOC284215 | 1.00 | 15081 | 3 | | | | | LOC339926 | 1.00 |
| 14986 | 3 | | | | | | LOC284260 | 1.00 | 15082 | 3 | | | | | LOC339975 | 1.00 |
| 14987 | 3 | | | | | | LOC284276 | 1.00 | 15083 | 3 | | | | | LOC340017 | 1.00 |
| 14988 | 3 | | | | | | LOC284294 | 1.00 | 15084 | 3 | | | | | LOC340073 | 1.00 |
| 14989 | 3 | | | | | | LOC284344 | 1.00 | 15085 | 3 | | | | | LOC340074 | 1.00 |
| 14990 | 3 | | | | | | LOC284379 | 1.00 | 15086 | 3 | | | | | LOC340094 | 1.00 |
| 14991 | 3 | | | | | | LOC284385 | 1.00 | 15087 | 3 | | | | | LOC340107 | 1.00 |
| 14992 | 3 | | | | | | LOC284395 | 1.00 | 15088 | 3 | | | | | LOC340113 | 1.00 |
| 14993 | 3 | | | | | | LOC284412 | 1.00 | 15089 | 3 | | | | | LOC340357 | 1.00 |
| 14994 | 3 | | | | | | LOC284551 | 1.00 | 15090 | 3 | | | | | LOC340508 | 1.00 |
| 14995 | 3 | | | | | | LOC284576 | 1.00 | 15091 | 3 | | | | | LOC340515 | 1.00 |
| 14996 | 3 | | | | | | LOC284578 | 1.00 | 15092 | 3 | | | | | LOC344595 | 1.00 |
| 14997 | 3 | | | | | | LOC284581 | 1.00 | 15093 | 3 | | | | | LOC344887 | 1.00 |
| 14998 | 3 | | | | | | LOC284632 | 1.00 | 15094 | 3 | | | | | LOC347411 | 1.00 |
| 14999 | 3 | | | | | | LOC284648 | 1.00 | 15095 | 3 | | | | | LOC348120 | 1.00 |
| 15000 | 3 | | | | | | LOC284661 | 1.00 | 15096 | 3 | | | | | LOC348761 | 1.00 |
| 15001 | 3 | | | | | | LOC284688 | 1.00 | 15097 | 3 | | | | | LOC349160 | 1.00 |
| 15002 | 3 | | | | | | LOC284788 | 1.00 | 15098 | 3 | | | | | LOC349196 | 1.00 |
| 15003 | 3 | | | | | | LOC284798 | 1.00 | 15099 | 3 | | | | | LOC375010 | 1.00 |
| 15004 | 3 | | | | | | LOC284801 | 1.00 | 15100 | 3 | | | | | LOC375196 | 1.00 |
| 15005 | 3 | | | | | | LOC284865 | 1.00 | 15101 | 3 | | | | | LOC375295 | 1.00 |
| 15006 | 3 | | | | | | LOC284933 | 1.00 | 15102 | 3 | | | | | LOC386597 | 1.00 |
| 15007 | 3 | | | | | | LOC284950 | 1.00 | 15103 | 3 | | | | | LOC388152 | 1.00 |
| 15008 | 3 | | | | | | LOC284998 | 1.00 | 15104 | 3 | | | | | LOC388276 | 1.00 |
| 15009 | 3 | | | | | | LOC285000 | 1.00 | 15105 | 3 | | | | | LOC388553 | 1.00 |
| 15010 | 3 | | | | | | LOC285084 | 1.00 | 15106 | 3 | | | | | LOC388630 | 1.00 |
| 15011 | 3 | | | | | | LOC285103 | 1.00 | 15107 | 3 | | | | | LOC388813 | 1.00 |
| 15012 | 3 | | | | | | LOC285205 | 1.00 | 15108 | 3 | | | | | LOC388849 | 1.00 |
| 15013 | 3 | | | | | | LOC285326 | 1.00 | 15109 | 3 | | | | | LOC388906 | 1.00 |
| 15014 | 3 | | | | | | LOC285370 | 1.00 | 15110 | 3 | | | | | LOC388942 | 1.00 |
| 15015 | 3 | | | | | | LOC285375 | 1.00 | 15111 | 3 | | | | | LOC388946 | 1.00 |
| 15016 | 3 | | | | | | LOC285401 | 1.00 | 15112 | 3 | | | | | LOC388948 | 1.00 |
| 15017 | 3 | | | | | | LOC285419 | 1.00 | 15113 | 3 | | | | | LOC389023 | 1.00 |
| 15018 | 3 | | | | | | LOC285441 | 1.00 | 15114 | 3 | | | | | LOC389033 | 1.00 |
| 15019 | 3 | | | | | | LOC285456 | 1.00 | 15115 | 3 | | | | | LOC389043 | 1.00 |
| 15020 | 3 | | | | | | LOC285484 | 1.00 | 15116 | 3 | | | | | LOC389247 | 1.00 |
| 15021 | 3 | | | | | | LOC285501 | 1.00 | 15117 | 3 | | | | | LOC389332 | 1.00 |
| 15022 | 3 | | | | | | LOC285547 | 1.00 | 15118 | 3 | | | | | LOC389458 | 1.00 |
| 15023 | 3 | | | | | | LOC285548 | 1.00 | 15119 | 3 | | | | | LOC389493 | 1.00 |
| 15024 | 3 | | | | | | LOC285577 | 1.00 | 15120 | 3 | | | | | LOC389705 | 1.00 |
| 15025 | 3 | | | | | | LOC285593 | 1.00 | 15121 | 3 | | | | | LOC389791 | 1.00 |
| 15026 | 3 | | | | | | LOC285626 | 1.00 | 15122 | 3 | | | | | LOC390660 | 1.00 |
| 15027 | 3 | | | | | | LOC285627 | 1.00 | 15123 | 3 | | | | | LOC390705 | 1.00 |
| 15028 | 3 | | | | | | LOC285629 | 1.00 | 15124 | 3 | | | | | LOC390858 | 1.00 |
| 15029 | 3 | | | | | | LOC285692 | 1.00 | 15125 | 3 | | | | | LOC392196 | 1.00 |
| 15030 | 3 | | | | | | LOC285696 | 1.00 | 15126 | 3 | | | | | LOC392232 | 1.00 |
| 15031 | 3 | | | | | | LOC285740 | 1.00 | 15127 | 3 | | | | | LOC392364 | 1.00 |
| 15032 | 3 | | | | | | LOC285758 | 1.00 | 15128 | 3 | | | | | LOC399708 | 1.00 |
| 15033 | 3 | | | | | | LOC285762 | 1.00 | 15129 | 3 | | | | | LOC399715 | 1.00 |
| 15034 | 3 | | | | | | LOC285768 | 1.00 | 15130 | 3 | | | | | LOC399815 | 1.00 |
| 15035 | 3 | | | | | | LOC285796 | 1.00 | 15131 | 3 | | | | | LOC399829 | 1.00 |
| 15036 | 3 | | | | | | LOC285847 | 1.00 | 15132 | 3 | | | | | LOC399939 | 1.00 |
| 15037 | 3 | | | | | | LOC285878 | 1.00 | 15133 | 3 | | | | | LOC400043 | 1.00 |
| 15038 | 3 | | | | | | LOC285889 | 1.00 | 15134 | 3 | | | | | LOC400084 | 1.00 |
| 15039 | 3 | | | | | | LOC285954 | 1.00 | 15135 | 3 | | | | | LOC400238 | 1.00 |
| 15040 | 3 | | | | | | LOC285972 | 1.00 | 15136 | 3 | | | | | LOC400456 | 1.00 |
| 15041 | 3 | | | | | | LOC286002 | 1.00 | 15137 | 3 | | | | | LOC400548 | 1.00 |
| 15042 | 3 | | | | | | LOC286083 | 1.00 | 15138 | 3 | | | | | LOC400550 | 1.00 |
| 15043 | 3 | | | | | | LOC286094 | 1.00 | 15139 | 3 | | | | | LOC400558 | 1.00 |
| 15044 | 3 | | | | | | LOC286114 | 1.00 | 15140 | 3 | | | | | LOC400620 | 1.00 |
| 15045 | 3 | | | | | | LOC286135 | 1.00 | 15141 | 3 | | | | | LOC400643 | 1.00 |
| 15046 | 3 | | | | | | LOC286177 | 1.00 | 15142 | 3 | | | | | LOC400654 | 1.00 |
| 15047 | 3 | | | | | | LOC286184 | 1.00 | 15143 | 3 | | | | | LOC400655 | 1.00 |
| 15048 | 3 | | | | | | LOC286186 | 1.00 | 15144 | 3 | | | | | LOC400680 | 1.00 |
| 15049 | 3 | | | | | | LOC286189 | 1.00 | 15145 | 3 | | | | | LOC400684 | 1.00 |
| 15050 | 3 | | | | | | LOC286190 | 1.00 | 15146 | 3 | | | | | LOC400752 | 1.00 |
| 15051 | 3 | | | | | | LOC286238 | 1.00 | 15147 | 3 | | | | | LOC400794 | 1.00 |
| 15052 | 3 | | | | | | LOC286297 | 1.00 | 15148 | 3 | | | | | LOC400891 | 1.00 |
| 15053 | 3 | | | | | | LOC286359 | 1.00 | 15149 | 3 | | | | | LOC400940 | 1.00 |
| 15054 | 3 | | | | | | LOC286370 | 1.00 | 15150 | 3 | | | | | LOC400958 | 1.00 |
| 15055 | 3 | | | | | | LOC286442 | 1.00 | 15151 | 3 | | | | | LOC401052 | 1.00 |
| 15056 | 3 | | | | | | LOC286467 | 1.00 | 15152 | 3 | | | | | LOC401074 | 1.00 |
| 15057 | 3 | | | | | | LOC338579 | 1.00 | 15153 | 3 | | | | | LOC401093 | 1.00 |
| 15058 | 3 | | | | | | LOC338588 | 1.00 | 15154 | 3 | | | | | LOC401109 | 1.00 |
| 15059 | 3 | | | | | | LOC338651 | 1.00 | 15155 | 3 | | | | | LOC401134 | 1.00 |
| 15060 | 3 | | | | | | LOC338739 | 1.00 | 15156 | 3 | | | | | LOC401164 | 1.00 |
| 15061 | 3 | | | | | | LOC338817 | 1.00 | 15157 | 3 | | | | | LOC401177 | 1.00 |
| 15062 | 3 | | | | | | LOC338963 | 1.00 | 15158 | 3 | | | | | LOC401242 | 1.00 |
| 15063 | 3 | | | | | | LOC339166 | 1.00 | 15159 | 3 | | | | | LOC401321 | 1.00 |
| 15064 | 3 | | | | | | LOC339240 | 1.00 | 15160 | 3 | | | | | LOC401324 | 1.00 |
| 15065 | 3 | | | | | | LOC339298 | 1.00 | 15161 | 3 | | | | | LOC401463 | 1.00 |
| 15066 | 3 | | | | | | LOC339442 | 1.00 | 15162 | 3 | | | | | LOC401497 | 1.00 |

Fig. 40 - 80

| | | | | | | | | | | | | | | |
|---|---|---|---|---|---|---|---|---|---|---|---|---|---|---|
| 15163 | 3 | | | | | LOC401557 | 1.00 | 15259 | 3 | | | | LOC645355 | 1.00 |
| 15164 | 3 | | | | | LOC401980 | 1.00 | 15260 | 3 | | | | LOC645431 | 1.00 |
| 15165 | 3 | | | | | LOC402160 | 1.00 | 15261 | 3 | | | | LOC645434 | 1.00 |
| 15166 | 3 | | | | | LOC402779 | 1.00 | 15262 | 3 | | | | LOC645591 | 1.00 |
| 15167 | 3 | | | | | LOC415056 | 1.00 | 15263 | 3 | | | | LOC645752 | 1.00 |
| 15168 | 3 | | | | | LOC439950 | 1.00 | 15264 | 3 | | | | LOC645949 | 1.00 |
| 15169 | 3 | | | | | LOC439990 | 1.00 | 15265 | 3 | | | | LOC646168 | 1.00 |
| 15170 | 3 | | | | | LOC440028 | 1.00 | 15266 | 3 | | | | LOC646268 | 1.00 |
| 15171 | 3 | | | | | LOC440040 | 1.00 | 15267 | 3 | | | | LOC646324 | 1.00 |
| 15172 | 3 | | | | | LOC440041 | 1.00 | 15268 | 3 | | | | LOC646498 | 1.00 |
| 15173 | 3 | | | | | LOC440117 | 1.00 | 15269 | 3 | | | | LOC646508 | 1.00 |
| 15174 | 3 | | | | | LOC440131 | 1.00 | 15270 | 3 | | | | LOC646576 | 1.00 |
| 15175 | 3 | | | | | LOC440173 | 1.00 | 15271 | 3 | | | | LOC646626 | 1.00 |
| 15176 | 3 | | | | | LOC440297 | 1.00 | 15272 | 3 | | | | LOC646627 | 1.00 |
| 15177 | 3 | | | | | LOC440300 | 1.00 | 15273 | 3 | | | | LOC646736 | 1.00 |
| 15178 | 3 | | | | | LOC440335 | 1.00 | 15274 | 3 | | | | LOC646743 | 1.00 |
| 15179 | 3 | | | | | LOC440356 | 1.00 | 15275 | 3 | | | | LOC646762 | 1.00 |
| 15180 | 3 | | | | | LOC440461 | 1.00 | 15276 | 3 | | | | LOC646813 | 1.00 |
| 15181 | 3 | | | | | LOC440518 | 1.00 | 15277 | 3 | | | | LOC646851 | 1.00 |
| 15182 | 3 | | | | | LOC440563 | 1.00 | 15278 | 3 | | | | LOC646862 | 1.00 |
| 15183 | 3 | | | | | LOC440600 | 1.00 | 15279 | 3 | | | | LOC646903 | 1.00 |
| 15184 | 3 | | | | | LOC440700 | 1.00 | 15280 | 3 | | | | LOC646938 | 1.00 |
| 15185 | 3 | | | | | LOC440704 | 1.00 | 15281 | 3 | | | | LOC646999 | 1.00 |
| 15186 | 3 | | | | | LOC440895 | 1.00 | 15282 | 3 | | | | LOC647012 | 1.00 |
| 15187 | 3 | | | | | LOC440896 | 1.00 | 15283 | 3 | | | | LOC647107 | 1.00 |
| 15188 | 3 | | | | | LOC440900 | 1.00 | 15284 | 3 | | | | LOC647323 | 1.00 |
| 15189 | 3 | | | | | LOC440905 | 1.00 | 15285 | 3 | | | | LOC647589 | 1.00 |
| 15190 | 3 | | | | | LOC440910 | 1.00 | 15286 | 3 | | | | LOC647859 | 1.00 |
| 15191 | 3 | | | | | LOC440925 | 1.00 | 15287 | 3 | | | | LOC647946 | 1.00 |
| 15192 | 3 | | | | | LOC440970 | 1.00 | 15288 | 3 | | | | LOC648691 | 1.00 |
| 15193 | 3 | | | | | LOC441009 | 1.00 | 15289 | 3 | | | | LOC648809 | 1.00 |
| 15194 | 3 | | | | | LOC441025 | 1.00 | 15290 | 3 | | | | LOC649133 | 1.00 |
| 15195 | 3 | | | | | LOC441177 | 1.00 | 15291 | 3 | | | | LOC649330 | 1.00 |
| 15196 | 3 | | | | | LOC441204 | 1.00 | 15292 | 3 | | | | LOC650226 | 1.00 |
| 15197 | 3 | | | | | LOC441242 | 1.00 | 15293 | 3 | | | | LOC650293 | 1.00 |
| 15198 | 3 | | | | | LOC441454 | 1.00 | 15294 | 3 | | | | LOC650368 | 1.00 |
| 15199 | 3 | | | | | LOC441461 | 1.00 | 15295 | 3 | | | | LOC653061 | 1.00 |
| 15200 | 3 | | | | | LOC441495 | 1.00 | 15296 | 3 | | | | LOC653486 | 1.00 |
| 15201 | 3 | | | | | LOC441601 | 1.00 | 15297 | 3 | | | | LOC653501 | 1.00 |
| 15202 | 3 | | | | | LOC441666 | 1.00 | 15298 | 3 | | | | LOC653712 | 1.00 |
| 15203 | 3 | | | | | LOC442028 | 1.00 | 15299 | 3 | | | | LOC653786 | 1.00 |
| 15204 | 3 | | | | | LOC442132 | 1.00 | 15300 | 3 | | | | LOC723809 | 1.00 |
| 15205 | 3 | | | | | LOC442421 | 1.00 | 15301 | 3 | | | | LOC727677 | 1.00 |
| 15206 | 3 | | | | | LOC442459 | 1.00 | 15302 | 3 | | | | LOC727710 | 1.00 |
| 15207 | 3 | | | | | LOC442497 | 1.00 | 15303 | 3 | | | | LOC727915 | 1.00 |
| 15208 | 3 | | | | | LOC494141 | 1.00 | 15304 | 3 | | | | LOC727924 | 1.00 |
| 15209 | 3 | | | | | LOC494558 | 1.00 | 15305 | 3 | | | | LOC727982 | 1.00 |
| 15210 | 3 | | | | | LOC503519 | 1.00 | 15306 | 3 | | | | LOC728012 | 1.00 |
| 15211 | 3 | | | | | LOC550113 | 1.00 | 15307 | 3 | | | | LOC728040 | 1.00 |
| 15212 | 3 | | | | | LOC553103 | 1.00 | 15308 | 3 | | | | LOC728218 | 1.00 |
| 15213 | 3 | | | | | LOC554201 | 1.00 | 15309 | 3 | | | | LOC728228 | 1.00 |
| 15214 | 3 | | | | | LOC554223 | 1.00 | 15310 | 3 | | | | LOC728342 | 1.00 |
| 15215 | 3 | | | | | LOC572558 | 1.00 | 15311 | 3 | | | | LOC728369 | 1.00 |
| 15216 | 3 | | | | | LOC574538 | 1.00 | 15312 | 3 | | | | LOC728393 | 1.00 |
| 15217 | 3 | | | | | LOC619207 | 1.00 | 15313 | 3 | | | | LOC728405 | 1.00 |
| 15218 | 3 | | | | | LOC63930 | 1.00 | 15314 | 3 | | | | LOC728407 | 1.00 |
| 15219 | 3 | | | | | LOC641364 | 1.00 | 15315 | 3 | | | | LOC728437 | 1.00 |
| 15220 | 3 | | | | | LOC641365 | 1.00 | 15316 | 3 | | | | LOC728463 | 1.00 |
| 15221 | 3 | | | | | LOC641367 | 1.00 | 15317 | 3 | | | | LOC728537 | 1.00 |
| 15222 | 3 | | | | | LOC641515 | 1.00 | 15318 | 3 | | | | LOC728558 | 1.00 |
| 15223 | 3 | | | | | LOC641746 | 1.00 | 15319 | 3 | | | | LOC728606 | 1.00 |
| 15224 | 3 | | | | | LOC642236 | 1.00 | 15320 | 3 | | | | LOC728640 | 1.00 |
| 15225 | 3 | | | | | LOC642366 | 1.00 | 15321 | 3 | | | | LOC728643 | 1.00 |
| 15226 | 3 | | | | | LOC642426 | 1.00 | 15322 | 3 | | | | LOC728716 | 1.00 |
| 15227 | 3 | | | | | LOC642826 | 1.00 | 15323 | 3 | | | | LOC728723 | 1.00 |
| 15228 | 3 | | | | | LOC642929 | 1.00 | 15324 | 3 | | | | LOC728724 | 1.00 |
| 15229 | 3 | | | | | LOC643037 | 1.00 | 15325 | 3 | | | | LOC728730 | 1.00 |
| 15230 | 3 | | | | | LOC643201 | 1.00 | 15326 | 3 | | | | LOC728819 | 1.00 |
| 15231 | 3 | | | | | LOC643339 | 1.00 | 15327 | 3 | | | | LOC728978 | 1.00 |
| 15232 | 3 | | | | | LOC643401 | 1.00 | 15328 | 3 | | | | LOC729041 | 1.00 |
| 15233 | 3 | | | | | LOC643406 | 1.00 | 15329 | 3 | | | | LOC729059 | 1.00 |
| 15234 | 3 | | | | | LOC643441 | 1.00 | 15330 | 3 | | | | LOC729080 | 1.00 |
| 15235 | 3 | | | | | LOC643486 | 1.00 | 15331 | 3 | | | | LOC729121 | 1.00 |
| 15236 | 3 | | | | | LOC643529 | 1.00 | 15332 | 3 | | | | LOC729156 | 1.00 |
| 15237 | 3 | | | | | LOC643542 | 1.00 | 15333 | 3 | | | | LOC729177 | 1.00 |
| 15238 | 3 | | | | | LOC643623 | 1.00 | 15334 | 3 | | | | LOC729264 | 1.00 |
| 15239 | 3 | | | | | LOC643648 | 1.00 | 15335 | 3 | | | | LOC729444 | 1.00 |
| 15240 | 3 | | | | | LOC643650 | 1.00 | 15336 | 3 | | | | LOC729506 | 1.00 |
| 15241 | 3 | | | | | LOC643669 | 1.00 | 15337 | 3 | | | | LOC729609 | 1.00 |
| 15242 | 3 | | | | | LOC643714 | 1.00 | 15338 | 3 | | | | LOC729668 | 1.00 |
| 15243 | 3 | | | | | LOC643770 | 1.00 | 15339 | 3 | | | | LOC729739 | 1.00 |
| 15244 | 3 | | | | | LOC643923 | 1.00 | 15340 | 3 | | | | LOC729911 | 1.00 |
| 15245 | 3 | | | | | LOC643955 | 1.00 | 15341 | 3 | | | | LOC729950 | 1.00 |
| 15246 | 3 | | | | | LOC644100 | 1.00 | 15342 | 3 | | | | LOC729966 | 1.00 |
| 15247 | 3 | | | | | LOC644145 | 1.00 | 15343 | 3 | | | | LOC729970 | 1.00 |
| 15248 | 3 | | | | | LOC644172 | 1.00 | 15344 | 3 | | | | LOC729987 | 1.00 |
| 15249 | 3 | | | | | LOC644189 | 1.00 | 15345 | 3 | | | | LOC730091 | 1.00 |
| 15250 | 3 | | | | | LOC644242 | 1.00 | 15346 | 3 | | | | LOC730101 | 1.00 |
| 15251 | 3 | | | | | LOC644248 | 1.00 | 15347 | 3 | | | | LOC730159 | 1.00 |
| 15252 | 3 | | | | | LOC644554 | 1.00 | 15348 | 3 | | | | LOC730227 | 1.00 |
| 15253 | 3 | | | | | LOC644669 | 1.00 | 15349 | 3 | | | | LOC730441 | 1.00 |
| 15254 | 3 | | | | | LOC644838 | 1.00 | 15350 | 3 | | | | LOC730668 | 1.00 |
| 15255 | 3 | | | | | LOC644990 | 1.00 | 15351 | 3 | | | | LOC730755 | 1.00 |
| 15256 | 3 | | | | | LOC645166 | 1.00 | 15352 | 3 | | | | LOC730811 | 1.00 |
| 15257 | 3 | | | | | LOC645206 | 1.00 | 15353 | 3 | | | | LOC731223 | 1.00 |
| 15258 | 3 | | | | | LOC645249 | 1.00 | 15354 | 3 | | | | LOC731779 | 1.00 |

Fig. 40 - 81

| | | | | | | | | | | | | | | | | |
|---|---|---|---|---|---|---|---|---|---|---|---|---|---|---|---|---|
| 15355 | 3 | | | | | | LOC731789 | 1.00 | 15451 | 3 | | | | | LRTM2 | 1.00 |
| 15356 | 3 | | | | | | LOC732275 | 1.00 | 15452 | 3 | | | | | LSAMP | 1.00 |
| 15357 | 3 | | | | | | LOC81691 | 1.00 | 15453 | 3 | | | | | LSAMP-AS3 | 1.00 |
| 15358 | 3 | | | | | | LOC84856 | 1.00 | 15454 | 3 | | | | | LTC4S | 1.00 |
| 15359 | 3 | | | | | | LOC84931 | 1.00 | 15455 | 3 | | | | | LUM | 1.00 |
| 15360 | 3 | | | | | | LOC84989 | 1.00 | 15456 | 3 | | | | | LURAP1 | 1.00 |
| 15361 | 3 | | | | | | LOC90246 | 1.00 | 15457 | 3 | | | | | LURAP1L | 1.00 |
| 15362 | 3 | | | | | | LOC90499 | 1.00 | 15458 | 3 | | | | | LUZP2 | 1.00 |
| 15363 | 3 | | | | | | LOC91149 | 1.00 | 15459 | 3 | | | | | LUZP4 | 1.00 |
| 15364 | 3 | | | | | | LOC91450 | 1.00 | 15460 | 3 | | | | | LY6D | 1.00 |
| 15365 | 3 | | | | | | LOC91948 | 1.00 | 15461 | 3 | | | | | LY6G6C | 1.00 |
| 15366 | 3 | | | | | | LOC93432 | 1.00 | 15462 | 3 | | | | | LY6G6D | 1.00 |
| 15367 | 3 | | | | | | LOH12CR2 | 1.00 | 15463 | 3 | | | | | LY6H | 1.00 |
| 15368 | 3 | | | | | | LONRF2 | 1.00 | 15464 | 3 | | | | | LY6K | 1.00 |
| 15369 | 3 | | | | | | LOR | 1.00 | 15465 | 3 | | | | | LY75-CD302 | 1.00 |
| 15370 | 3 | | | | | | LOX | 1.00 | 15466 | 3 | | | | | LY86-AS1 | 1.00 |
| 15371 | 3 | | | | | | LOXL1 | 1.00 | 15467 | 3 | | | | | LYG2 | 1.00 |
| 15372 | 3 | | | | | | LOXL2 | 1.00 | 15468 | 3 | | | | | LYNX1 | 1.00 |
| 15373 | 3 | | | | | | LOXL4 | 1.00 | 15469 | 3 | | | | | LYPD1 | 1.00 |
| 15374 | 3 | | | | | | LPA | 1.00 | 15470 | 3 | | | | | LYPD4 | 1.00 |
| 15375 | 3 | | | | | | LPAL2 | 1.00 | 15471 | 3 | | | | | LYPD5 | 1.00 |
| 15376 | 3 | | | | | | LPAR3 | 1.00 | 15472 | 3 | | | | | LYPD6 | 1.00 |
| 15377 | 3 | | | | | | LPAR4 | 1.00 | 15473 | 3 | | | | | LYPD6B | 1.00 |
| 15378 | 3 | | | | | | LPHN2 | 1.00 | 15474 | 3 | | | | | LYZL1 | 1.00 |
| 15379 | 3 | | | | | | LPHN3 | 1.00 | 15475 | 3 | | | | | LYZL2 | 1.00 |
| 15380 | 3 | | | | | | LPIN3 | 1.00 | 15476 | 3 | | | | | LYZL4 | 1.00 |
| 15381 | 3 | | | | | | LPL | 1.00 | 15477 | 3 | | | | | LYZL6 | 1.00 |
| 15382 | 3 | | | | | | LPO | 1.00 | 15478 | 3 | | | | | LZTS1 | 1.00 |
| 15383 | 3 | | | | | | LPPR1 | 1.00 | 15479 | 3 | | | | | M1 | 1.00 |
| 15384 | 3 | | | | | | LPPR3 | 1.00 | 15480 | 3 | | | | | MAB21L1 | 1.00 |
| 15385 | 3 | | | | | | LPPR4 | 1.00 | 15481 | 3 | | | | | MAB21L2 | 1.00 |
| 15386 | 3 | | | | | | LPPR5 | 1.00 | 15482 | 3 | | | | | MAB21L3 | 1.00 |
| 15387 | 3 | | | | | | LRAT | 1.00 | 15483 | 3 | | | | | MACC1 | 1.00 |
| 15388 | 3 | | | | | | LRCH2 | 1.00 | 15484 | 3 | | | | | MACROD1 | 1.00 |
| 15389 | 3 | | | | | | LRFN2 | 1.00 | 15485 | 3 | | | | | MACROD2-AS1 | 1.00 |
| 15390 | 3 | | | | | | LRFN5 | 1.00 | 15486 | 3 | | | | | MAEL | 1.00 |
| 15391 | 3 | | | | | | LRGUK | 1.00 | 15487 | 3 | | | | | MAFA | 1.00 |
| 15392 | 3 | | | | | | LRIG3 | 1.00 | 15488 | 3 | | | | | MAFG-AS1 | 1.00 |
| 15393 | 3 | | | | | | LRIT1 | 1.00 | 15489 | 3 | | | | | MAG | 1.00 |
| 15394 | 3 | | | | | | LRIT2 | 1.00 | 15490 | 3 | | | | | MAGEA1 | 1.00 |
| 15395 | 3 | | | | | | LRIT3 | 1.00 | 15491 | 3 | | | | | MAGEA10 | 1.00 |
| 15396 | 3 | | | | | | LRP11 | 1.00 | 15492 | 3 | | | | | MAGEA10-MAGEA5 | 1.00 |
| 15397 | 3 | | | | | | LRP1B | 1.00 | 15493 | 3 | | | | | MAGEA11 | 1.00 |
| 15398 | 3 | | | | | | LRP2 | 1.00 | 15494 | 3 | | | | | MAGEA12 | 1.00 |
| 15399 | 3 | | | | | | LRP2BP | 1.00 | 15495 | 3 | | | | | MAGEA2 | 1.00 |
| 15400 | 3 | | | | | | LRP4 | 1.00 | 15496 | 3 | | | | | MAGEA2B | 1.00 |
| 15401 | 3 | | | | | | LRP5 | 1.00 | 15497 | 3 | | | | | MAGEA3 | 1.00 |
| 15402 | 3 | | | | | | LRP6 | 1.00 | 15498 | 3 | | | | | MAGEA4 | 1.00 |
| 15403 | 3 | | | | | | LRRC1 | 1.00 | 15499 | 3 | | | | | MAGEA5 | 1.00 |
| 15404 | 3 | | | | | | LRRC10 | 1.00 | 15500 | 3 | | | | | MAGEA6 | 1.00 |
| 15405 | 3 | | | | | | LRRC10B | 1.00 | 15501 | 3 | | | | | MAGEA8 | 1.00 |
| 15406 | 3 | | | | | | LRRC14B | 1.00 | 15502 | 3 | | | | | MAGEA9 | 1.00 |
| 15407 | 3 | | | | | | LRRC15 | 1.00 | 15503 | 3 | | | | | MAGEA9B | 1.00 |
| 15408 | 3 | | | | | | LRRC16B | 1.00 | 15504 | 3 | | | | | MAGEB1 | 1.00 |
| 15409 | 3 | | | | | | LRRC17 | 1.00 | 15505 | 3 | | | | | MAGEB10 | 1.00 |
| 15410 | 3 | | | | | | LRRC18 | 1.00 | 15506 | 3 | | | | | MAGEB16 | 1.00 |
| 15411 | 3 | | | | | | LRRC19 | 1.00 | 15507 | 3 | | | | | MAGEB18 | 1.00 |
| 15412 | 3 | | | | | | LRRC2 | 1.00 | 15508 | 3 | | | | | MAGEB2 | 1.00 |
| 15413 | 3 | | | | | | LRRC24 | 1.00 | 15509 | 3 | | | | | MAGEB3 | 1.00 |
| 15414 | 3 | | | | | | LRRC26 | 1.00 | 15510 | 3 | | | | | MAGEB4 | 1.00 |
| 15415 | 3 | | | | | | LRRC30 | 1.00 | 15511 | 3 | | | | | MAGEB6 | 1.00 |
| 15416 | 3 | | | | | | LRRC31 | 1.00 | 15512 | 3 | | | | | MAGEC1 | 1.00 |
| 15417 | 3 | | | | | | LRRC32 | 1.00 | 15513 | 3 | | | | | MAGEC2 | 1.00 |
| 15418 | 3 | | | | | | LRRC34 | 1.00 | 15514 | 3 | | | | | MAGEC3 | 1.00 |
| 15419 | 3 | | | | | | LRRC36 | 1.00 | 15515 | 3 | | | | | MAGED4 | 1.00 |
| 15420 | 3 | | | | | | LRRC38 | 1.00 | 15516 | 3 | | | | | MAGED4B | 1.00 |
| 15421 | 3 | | | | | | LRRC39 | 1.00 | 15517 | 3 | | | | | MAGEE2 | 1.00 |
| 15422 | 3 | | | | | | LRRC3B | 1.00 | 15518 | 3 | | | | | MAGEL2 | 1.00 |
| 15423 | 3 | | | | | | LRRC3C | 1.00 | 15519 | 3 | | | | | MAGI1 | 1.00 |
| 15424 | 3 | | | | | | LRRC43 | 1.00 | 15520 | 3 | | | | | MAGI2 | 1.00 |
| 15425 | 3 | | | | | | LRRC46 | 1.00 | 15521 | 3 | | | | | MAGI3 | 1.00 |
| 15426 | 3 | | | | | | LRRC48 | 1.00 | 15522 | 3 | | | | | MAGIX | 1.00 |
| 15427 | 3 | | | | | | LRRC49 | 1.00 | 15523 | 3 | | | | | MAL2 | 1.00 |
| 15428 | 3 | | | | | | LRRC4B | 1.00 | 15524 | 3 | | | | | MALL | 1.00 |
| 15429 | 3 | | | | | | LRRC4C | 1.00 | 15525 | 3 | | | | | MAMDC2 | 1.00 |
| 15430 | 3 | | | | | | LRRC52 | 1.00 | 15526 | 3 | | | | | MAMLD1 | 1.00 |
| 15431 | 3 | | | | | | LRRC55 | 1.00 | 15527 | 3 | | | | | MAMSTR | 1.00 |
| 15432 | 3 | | | | | | LRRC56 | 1.00 | 15528 | 3 | | | | | MANSC4 | 1.00 |
| 15433 | 3 | | | | | | LRRC66 | 1.00 | 15529 | 3 | | | | | MAOA | 1.00 |
| 15434 | 3 | | | | | | LRRC69 | 1.00 | 15530 | 3 | | | | | MAOB | 1.00 |
| 15435 | 3 | | | | | | LRRC7 | 1.00 | 15531 | 3 | | | | | MAP1B | 1.00 |
| 15436 | 3 | | | | | | LRRC71 | 1.00 | 15532 | 3 | | | | | MAP1LC3C | 1.00 |
| 15437 | 3 | | | | | | LRRC72 | 1.00 | 15533 | 3 | | | | | MAP2 | 1.00 |
| 15438 | 3 | | | | | | LRRC73 | 1.00 | 15534 | 3 | | | | | MAP3K15 | 1.00 |
| 15439 | 3 | | | | | | LRRC8E | 1.00 | 15535 | 3 | | | | | MAP3K9 | 1.00 |
| 15440 | 3 | | | | | | LRRD1 | 1.00 | 15536 | 3 | | | | | MAP6 | 1.00 |
| 15441 | 3 | | | | | | LRRIQ1 | 1.00 | 15537 | 3 | | | | | MAP6D1 | 1.00 |
| 15442 | 3 | | | | | | LRRIQ3 | 1.00 | 15538 | 3 | | | | | MAP7D2 | 1.00 |
| 15443 | 3 | | | | | | LRRIQ4 | 1.00 | 15539 | 3 | | | | | MAPK10 | 1.00 |
| 15444 | 3 | | | | | | LRRN4 | 1.00 | 15540 | 3 | | | | | MAPK12 | 1.00 |
| 15445 | 3 | | | | | | LRRN4CL | 1.00 | 15541 | 3 | | | | | MAPK15 | 1.00 |
| 15446 | 3 | | | | | | LRRTM1 | 1.00 | 15542 | 3 | | | | | MAPK4 | 1.00 |
| 15447 | 3 | | | | | | LRRTM2 | 1.00 | 15543 | 3 | | | | | MAPK8IP1 | 1.00 |
| 15448 | 3 | | | | | | LRRTM3 | 1.00 | 15544 | 3 | | | | | MAPK8IP2 | 1.00 |
| 15449 | 3 | | | | | | LRRTM4 | 1.00 | 15545 | 3 | | | | | MAPT | 1.00 |
| 15450 | 3 | | | | | | LRTM1 | 1.00 | | | | | | | | |

Fig. 40 - 82

| | | | | | | | | | | | | | | |
|---|---|---|---|---|---|---|---|---|---|---|---|---|---|---|
| 15546 | 3 | | | | | MAPT-AS1 | 1.00 | 15642 | 3 | | | | MGP | 1.00 |
| 15547 | 3 | | | | | MAPT-IT1 | 1.00 | 15643 | 3 | | | | MIA | 1.00 |
| 15548 | 3 | | | | | 42431 | 1.00 | 15644 | 3 | | | | MIA-RAB4B | 1.00 |
| 15549 | 3 | | | | | 42439 | 1.00 | 15645 | 3 | | | | MIA2 | 1.00 |
| 15550 | 3 | | | | | 42440 | 1.00 | 15646 | 3 | | | | MICALL2 | 1.00 |
| 15551 | 3 | | | | | 42433 | 1.00 | 15647 | 3 | | | | MID1 | 1.00 |
| 15552 | 3 | | | | | MARK1 | 1.00 | 15648 | 3 | | | | MIMT1 | 1.00 |
| 15553 | 3 | | | | | MARK2P9 | 1.00 | 15649 | 3 | | | | MIOX | 1.00 |
| 15554 | 3 | | | | | MARVELD2 | 1.00 | 15650 | 3 | | | | MIP | 1.00 |
| 15555 | 3 | | | | | MARVELD3 | 1.00 | 15651 | 3 | | | | MIPEP | 1.00 |
| 15556 | 3 | | | | | MAS1 | 1.00 | 15652 | 3 | | | | MIPOL1 | 1.00 |
| 15557 | 3 | | | | | MAS1L | 1.00 | 15653 | 3 | | | | MIR1-1 | 1.00 |
| 15558 | 3 | | | | | MASP1 | 1.00 | 15654 | 3 | | | | MIR1-2 | 1.00 |
| 15559 | 3 | | | | | MAST1 | 1.00 | 15655 | 3 | | | | MIR100 | 1.00 |
| 15560 | 3 | | | | | MAT1A | 1.00 | 15656 | 3 | | | | MIR100HG | 1.00 |
| 15561 | 3 | | | | | MATN1 | 1.00 | 15657 | 3 | | | | MIR101-1 | 1.00 |
| 15562 | 3 | | | | | MATN2 | 1.00 | 15658 | 3 | | | | MIR101-2 | 1.00 |
| 15563 | 3 | | | | | MATN3 | 1.00 | 15659 | 3 | | | | MIR103A1 | 1.00 |
| 15564 | 3 | | | | | MATN4 | 1.00 | 15660 | 3 | | | | MIR103A2 | 1.00 |
| 15565 | 3 | | | | | MB | 1.00 | 15661 | 3 | | | | MIR103B1 | 1.00 |
| 15566 | 3 | | | | | MBD3L1 | 1.00 | 15662 | 3 | | | | MIR103B2 | 1.00 |
| 15567 | 3 | | | | | MBD3L2 | 1.00 | 15663 | 3 | | | | MIR105-1 | 1.00 |
| 15568 | 3 | | | | | MBD3L3 | 1.00 | 15664 | 3 | | | | MIR105-2 | 1.00 |
| 15569 | 3 | | | | | MBD3L4 | 1.00 | 15665 | 3 | | | | MIR106A | 1.00 |
| 15570 | 3 | | | | | MBD3L5 | 1.00 | 15666 | 3 | | | | MIR106B | 1.00 |
| 15571 | 3 | | | | | MBL1P | 1.00 | 15667 | 3 | | | | MIR107 | 1.00 |
| 15572 | 3 | | | | | MBL2 | 1.00 | 15668 | 3 | | | | MIR10A | 1.00 |
| 15573 | 3 | | | | | MC2R | 1.00 | 15669 | 3 | | | | MIR10B | 1.00 |
| 15574 | 3 | | | | | MC3R | 1.00 | 15670 | 3 | | | | MIR1178 | 1.00 |
| 15575 | 3 | | | | | MC4R | 1.00 | 15671 | 3 | | | | MIR1179 | 1.00 |
| 15576 | 3 | | | | | MC5R | 1.00 | 15672 | 3 | | | | MIR1180 | 1.00 |
| 15577 | 3 | | | | | MCAM | 1.00 | 15673 | 3 | | | | MIR1181 | 1.00 |
| 15578 | 3 | | | | | MCART3P | 1.00 | 15674 | 3 | | | | MIR1182 | 1.00 |
| 15579 | 3 | | | | | MCART6 | 1.00 | 15675 | 3 | | | | MIR1185-1 | 1.00 |
| 15580 | 3 | | | | | MCCD1 | 1.00 | 15676 | 3 | | | | MIR1185-2 | 1.00 |
| 15581 | 3 | | | | | MCF2 | 1.00 | 15677 | 3 | | | | MIR1193 | 1.00 |
| 15582 | 3 | | | | | MCF2L2 | 1.00 | 15678 | 3 | | | | MIR1197 | 1.00 |
| 15583 | 3 | | | | | MCHR1 | 1.00 | 15679 | 3 | | | | MIR1200 | 1.00 |
| 15584 | 3 | | | | | MCHR2 | 1.00 | 15680 | 3 | | | | MIR1203 | 1.00 |
| 15585 | 3 | | | | | MCM10 | 1.00 | 15681 | 3 | | | | MIR1204 | 1.00 |
| 15586 | 3 | | | | | MCOLN3 | 1.00 | 15682 | 3 | | | | MIR1205 | 1.00 |
| 15587 | 3 | | | | | MDFI | 1.00 | 15683 | 3 | | | | MIR1206 | 1.00 |
| 15588 | 3 | | | | | MDGA2 | 1.00 | 15684 | 3 | | | | MIR1207 | 1.00 |
| 15589 | 3 | | | | | MDH1B | 1.00 | 15685 | 3 | | | | MIR1208 | 1.00 |
| 15590 | 3 | | | | | ME1 | 1.00 | 15686 | 3 | | | | MIR122 | 1.00 |
| 15591 | 3 | | | | | ME3 | 1.00 | 15687 | 3 | | | | MIR1224 | 1.00 |
| 15592 | 3 | | | | | MECOM | 1.00 | 15688 | 3 | | | | MIR1225 | 1.00 |
| 15593 | 3 | | | | | MED12L | 1.00 | 15689 | 3 | | | | MIR1226 | 1.00 |
| 15594 | 3 | | | | | MEF2BNB-MEF2B | 1.00 | 15690 | 3 | | | | MIR1227 | 1.00 |
| 15595 | 3 | | | | | MEG3 | 1.00 | 15691 | 3 | | | | MIR1228 | 1.00 |
| 15596 | 3 | | | | | MEG8 | 1.00 | 15692 | 3 | | | | MIR1229 | 1.00 |
| 15597 | 3 | | | | | MEGF10 | 1.00 | 15693 | 3 | | | | MIR1231 | 1.00 |
| 15598 | 3 | | | | | MEGF11 | 1.00 | 15694 | 3 | | | | MIR1233-1 | 1.00 |
| 15599 | 3 | | | | | MEI1 | 1.00 | 15695 | 3 | | | | MIR1233-2 | 1.00 |
| 15600 | 3 | | | | | MEIG1 | 1.00 | 15696 | 3 | | | | MIR1234 | 1.00 |
| 15601 | 3 | | | | | MEIS2 | 1.00 | 15697 | 3 | | | | MIR1236 | 1.00 |
| 15602 | 3 | | | | | MEIS3 | 1.00 | 15698 | 3 | | | | MIR1237 | 1.00 |
| 15603 | 3 | | | | | MEIS3P1 | 1.00 | 15699 | 3 | | | | MIR1238 | 1.00 |
| 15604 | 3 | | | | | MELK | 1.00 | 15700 | 3 | | | | MIR124-1 | 1.00 |
| 15605 | 3 | | | | | MEOX2 | 1.00 | 15701 | 3 | | | | MIR124-2 | 1.00 |
| 15606 | 3 | | | | | MEP1A | 1.00 | 15702 | 3 | | | | MIR124-3 | 1.00 |
| 15607 | 3 | | | | | MEP1B | 1.00 | 15703 | 3 | | | | MIR1243 | 1.00 |
| 15608 | 3 | | | | | MEPE | 1.00 | 15704 | 3 | | | | MIR1244-1 | 1.00 |
| 15609 | 3 | | | | | MESP1 | 1.00 | 15705 | 3 | | | | MIR1244-2 | 1.00 |
| 15610 | 3 | | | | | MESP2 | 1.00 | 15706 | 3 | | | | MIR1244-3 | 1.00 |
| 15611 | 3 | | | | | MESTIT1 | 1.00 | 15707 | 3 | | | | MIR1245A | 1.00 |
| 15612 | 3 | | | | | MET | 1.00 | 15708 | 3 | | | | MIR1245B | 1.00 |
| 15613 | 3 | | | | | METTL11B | 1.00 | 15709 | 3 | | | | MIR1246 | 1.00 |
| 15614 | 3 | | | | | METTL21C | 1.00 | 15710 | 3 | | | | MIR1247 | 1.00 |
| 15615 | 3 | | | | | METTL21CP1 | 1.00 | 15711 | 3 | | | | MIR1248 | 1.00 |
| 15616 | 3 | | | | | METTL24 | 1.00 | 15712 | 3 | | | | MIR1249 | 1.00 |
| 15617 | 3 | | | | | METTL7B | 1.00 | 15713 | 3 | | | | MIR1250 | 1.00 |
| 15618 | 3 | | | | | MEX3A | 1.00 | 15714 | 3 | | | | MIR1251 | 1.00 |
| 15619 | 3 | | | | | MEX3B | 1.00 | 15715 | 3 | | | | MIR1252 | 1.00 |
| 15620 | 3 | | | | | MFAP2 | 1.00 | 15716 | 3 | | | | MIR1253 | 1.00 |
| 15621 | 3 | | | | | MFAP4 | 1.00 | 15717 | 3 | | | | MIR1256 | 1.00 |
| 15622 | 3 | | | | | MFAP5 | 1.00 | 15718 | 3 | | | | MIR1257 | 1.00 |
| 15623 | 3 | | | | | MFI2 | 1.00 | 15719 | 3 | | | | MIR1258 | 1.00 |
| 15624 | 3 | | | | | MFI2-AS1 | 1.00 | 15720 | 3 | | | | MIR125A | 1.00 |
| 15625 | 3 | | | | | MFSD4 | 1.00 | 15721 | 3 | | | | MIR125B1 | 1.00 |
| 15626 | 3 | | | | | MGAT4C | 1.00 | 15722 | 3 | | | | MIR125B2 | 1.00 |
| 15627 | 3 | | | | | MGAT5B | 1.00 | 15723 | 3 | | | | MIR126 | 1.00 |
| 15628 | 3 | | | | | MGC14436 | 1.00 | 15724 | 3 | | | | MIR1260A | 1.00 |
| 15629 | 3 | | | | | MGC15885 | 1.00 | 15725 | 3 | | | | MIR1260B | 1.00 |
| 15630 | 3 | | | | | MGC16025 | 1.00 | 15726 | 3 | | | | MIR1262 | 1.00 |
| 15631 | 3 | | | | | MGC16121 | 1.00 | 15727 | 3 | | | | MIR1264 | 1.00 |
| 15632 | 3 | | | | | MGC16703 | 1.00 | 15728 | 3 | | | | MIR1265 | 1.00 |
| 15633 | 3 | | | | | MGC23270 | 1.00 | 15729 | 3 | | | | MIR1266 | 1.00 |
| 15634 | 3 | | | | | MGC27382 | 1.00 | 15730 | 3 | | | | MIR127 | 1.00 |
| 15635 | 3 | | | | | MGC2889 | 1.00 | 15731 | 3 | | | | MIR1270-1 | 1.00 |
| 15636 | 3 | | | | | MGC34034 | 1.00 | 15732 | 3 | | | | MIR1272 | 1.00 |
| 15637 | 3 | | | | | MGC3771 | 1.00 | 15733 | 3 | | | | MIR1275 | 1.00 |
| 15638 | 3 | | | | | MGC39584 | 1.00 | 15734 | 3 | | | | MIR1276 | 1.00 |
| 15639 | 3 | | | | | MGC4473 | 1.00 | 15735 | 3 | | | | MIR1277 | 1.00 |
| 15640 | 3 | | | | | MGC45800 | 1.00 | 15736 | 3 | | | | MIR1278 | 1.00 |
| 15641 | 3 | | | | | MGC45922 | 1.00 | 15737 | 3 | | | | MIR1279 | 1.00 |

Fig. 40 - 83

| | | | | | | | | | | | | | | |
|---|---|---|---|---|---|---|---|---|---|---|---|---|---|---|
| 15738 | 3 | | | | | MIR128-1 | 1.00 | 15834 | 3 | | | | MIR1908 | 1.00 |
| 15739 | 3 | | | | | MIR128-2 | 1.00 | 15835 | 3 | | | | MIR191 | 1.00 |
| 15740 | 3 | | | | | MIR1280 | 1.00 | 15836 | 3 | | | | MIR1910 | 1.00 |
| 15741 | 3 | | | | | MIR1281 | 1.00 | 15837 | 3 | | | | MIR1911 | 1.00 |
| 15742 | 3 | | | | | MIR1283-1 | 1.00 | 15838 | 3 | | | | MIR1912 | 1.00 |
| 15743 | 3 | | | | | MIR1283-2 | 1.00 | 15839 | 3 | | | | MIR1913 | 1.00 |
| 15744 | 3 | | | | | MIR1284 | 1.00 | 15840 | 3 | | | | MIR1914 | 1.00 |
| 15745 | 3 | | | | | MIR1286 | 1.00 | 15841 | 3 | | | | MIR1915 | 1.00 |
| 15746 | 3 | | | | | MIR1287 | 1.00 | 15842 | 3 | | | | MIR193A | 1.00 |
| 15747 | 3 | | | | | MIR1288 | 1.00 | 15843 | 3 | | | | MIR193B | 1.00 |
| 15748 | 3 | | | | | MIR1289-2 | 1.00 | 15844 | 3 | | | | MIR194-1 | 1.00 |
| 15749 | 3 | | | | | MIR129-1 | 1.00 | 15845 | 3 | | | | MIR194-2 | 1.00 |
| 15750 | 3 | | | | | MIR129-2 | 1.00 | 15846 | 3 | | | | MIR195 | 1.00 |
| 15751 | 3 | | | | | MIR1291 | 1.00 | 15847 | 3 | | | | MIR196A1 | 1.00 |
| 15752 | 3 | | | | | MIR1292 | 1.00 | 15848 | 3 | | | | MIR196A2 | 1.00 |
| 15753 | 3 | | | | | MIR1293 | 1.00 | 15849 | 3 | | | | MIR196B | 1.00 |
| 15754 | 3 | | | | | MIR1295A | 1.00 | 15850 | 3 | | | | MIR197 | 1.00 |
| 15755 | 3 | | | | | MIR1296 | 1.00 | 15851 | 3 | | | | MIR1972-1 | 1.00 |
| 15756 | 3 | | | | | MIR1297 | 1.00 | 15852 | 3 | | | | MIR1973 | 1.00 |
| 15757 | 3 | | | | | MIR1298 | 1.00 | 15853 | 3 | | | | MIR1976 | 1.00 |
| 15758 | 3 | | | | | MIR1301 | 1.00 | 15854 | 3 | | | | MIR198 | 1.00 |
| 15759 | 3 | | | | | MIR1304 | 1.00 | 15855 | 3 | | | | MIR199A1 | 1.00 |
| 15760 | 3 | | | | | MIR1305 | 1.00 | 15856 | 3 | | | | MIR199A2 | 1.00 |
| 15761 | 3 | | | | | MIR1306 | 1.00 | 15857 | 3 | | | | MIR199B | 1.00 |
| 15762 | 3 | | | | | MIR130A | 1.00 | 15858 | 3 | | | | MIR19A | 1.00 |
| 15763 | 3 | | | | | MIR130B | 1.00 | 15859 | 3 | | | | MIR19B1 | 1.00 |
| 15764 | 3 | | | | | MIR132 | 1.00 | 15860 | 3 | | | | MIR19B2 | 1.00 |
| 15765 | 3 | | | | | MIR1322 | 1.00 | 15861 | 3 | | | | MIR200A | 1.00 |
| 15766 | 3 | | | | | MIR1323 | 1.00 | 15862 | 3 | | | | MIR200B | 1.00 |
| 15767 | 3 | | | | | MIR1324 | 1.00 | 15863 | 3 | | | | MIR200C | 1.00 |
| 15768 | 3 | | | | | MIR133A1 | 1.00 | 15864 | 3 | | | | MIR202 | 1.00 |
| 15769 | 3 | | | | | MIR133A2 | 1.00 | 15865 | 3 | | | | MIR203 | 1.00 |
| 15770 | 3 | | | | | MIR133B | 1.00 | 15866 | 3 | | | | MIR204 | 1.00 |
| 15771 | 3 | | | | | MIR134 | 1.00 | 15867 | 3 | | | | MIR205 | 1.00 |
| 15772 | 3 | | | | | MIR1343 | 1.00 | 15868 | 3 | | | | MIR2052 | 1.00 |
| 15773 | 3 | | | | | MIR135A1 | 1.00 | 15869 | 3 | | | | MIR2053 | 1.00 |
| 15774 | 3 | | | | | MIR135A2 | 1.00 | 15870 | 3 | | | | MIR2054 | 1.00 |
| 15775 | 3 | | | | | MIR135B | 1.00 | 15871 | 3 | | | | MIR205HG | 1.00 |
| 15776 | 3 | | | | | MIR136 | 1.00 | 15872 | 3 | | | | MIR206 | 1.00 |
| 15777 | 3 | | | | | MIR137 | 1.00 | 15873 | 3 | | | | MIR208A | 1.00 |
| 15778 | 3 | | | | | MIR137HG | 1.00 | 15874 | 3 | | | | MIR208B | 1.00 |
| 15779 | 3 | | | | | MIR138-1 | 1.00 | 15875 | 3 | | | | MIR20A | 1.00 |
| 15780 | 3 | | | | | MIR138-2 | 1.00 | 15876 | 3 | | | | MIR20B | 1.00 |
| 15781 | 3 | | | | | MIR139 | 1.00 | 15877 | 3 | | | | MIR21 | 1.00 |
| 15782 | 3 | | | | | MIR140 | 1.00 | 15878 | 3 | | | | MIR210 | 1.00 |
| 15783 | 3 | | | | | MIR141 | 1.00 | 15879 | 3 | | | | MIR210HG | 1.00 |
| 15784 | 3 | | | | | MIR142 | 1.00 | 15880 | 3 | | | | MIR211 | 1.00 |
| 15785 | 3 | | | | | MIR143 | 1.00 | 15881 | 3 | | | | MIR2110 | 1.00 |
| 15786 | 3 | | | | | MIR143HG | 1.00 | 15882 | 3 | | | | MIR2113 | 1.00 |
| 15787 | 3 | | | | | MIR144 | 1.00 | 15883 | 3 | | | | MIR2114 | 1.00 |
| 15788 | 3 | | | | | MIR145 | 1.00 | 15884 | 3 | | | | MIR2116 | 1.00 |
| 15789 | 3 | | | | | MIR1468 | 1.00 | 15885 | 3 | | | | MIR2117 | 1.00 |
| 15790 | 3 | | | | | MIR1469 | 1.00 | 15886 | 3 | | | | MIR212 | 1.00 |
| 15791 | 3 | | | | | MIR146A | 1.00 | 15887 | 3 | | | | MIR214 | 1.00 |
| 15792 | 3 | | | | | MIR146B | 1.00 | 15888 | 3 | | | | MIR215 | 1.00 |
| 15793 | 3 | | | | | MIR1470 | 1.00 | 15889 | 3 | | | | MIR216A | 1.00 |
| 15794 | 3 | | | | | MIR1471 | 1.00 | 15890 | 3 | | | | MIR216B | 1.00 |
| 15795 | 3 | | | | | MIR147A | 1.00 | 15891 | 3 | | | | MIR217 | 1.00 |
| 15796 | 3 | | | | | MIR147B | 1.00 | 15892 | 3 | | | | MIR218-1 | 1.00 |
| 15797 | 3 | | | | | MIR148A | 1.00 | 15893 | 3 | | | | MIR218-2 | 1.00 |
| 15798 | 3 | | | | | MIR148B | 1.00 | 15894 | 3 | | | | MIR219-1 | 1.00 |
| 15799 | 3 | | | | | MIR149 | 1.00 | 15895 | 3 | | | | MIR219-2 | 1.00 |
| 15800 | 3 | | | | | MIR150 | 1.00 | 15896 | 3 | | | | MIR22 | 1.00 |
| 15801 | 3 | | | | | MIR152 | 1.00 | 15897 | 3 | | | | MIR221 | 1.00 |
| 15802 | 3 | | | | | MIR153-1 | 1.00 | 15898 | 3 | | | | MIR222 | 1.00 |
| 15803 | 3 | | | | | MIR153-2 | 1.00 | 15899 | 3 | | | | MIR223 | 1.00 |
| 15804 | 3 | | | | | MIR1537 | 1.00 | 15900 | 3 | | | | MIR2276 | 1.00 |
| 15805 | 3 | | | | | MIR1538 | 1.00 | 15901 | 3 | | | | MIR2277 | 1.00 |
| 15806 | 3 | | | | | MIR1539 | 1.00 | 15902 | 3 | | | | MIR2278 | 1.00 |
| 15807 | 3 | | | | | MIR154 | 1.00 | 15903 | 3 | | | | MIR2355 | 1.00 |
| 15808 | 3 | | | | | MIR155 | 1.00 | 15904 | 3 | | | | MIR2392 | 1.00 |
| 15809 | 3 | | | | | MIR15A | 1.00 | 15905 | 3 | | | | MIR23A | 1.00 |
| 15810 | 3 | | | | | MIR15B | 1.00 | 15906 | 3 | | | | MIR23B | 1.00 |
| 15811 | 3 | | | | | MIR16-1 | 1.00 | 15907 | 3 | | | | MIR23C | 1.00 |
| 15812 | 3 | | | | | MIR16-2 | 1.00 | 15908 | 3 | | | | MIR24-1 | 1.00 |
| 15813 | 3 | | | | | MIR17 | 1.00 | 15909 | 3 | | | | MIR24-2 | 1.00 |
| 15814 | 3 | | | | | MIR181A1 | 1.00 | 15910 | 3 | | | | MIR2467 | 1.00 |
| 15815 | 3 | | | | | MIR181A2 | 1.00 | 15911 | 3 | | | | MIR25 | 1.00 |
| 15816 | 3 | | | | | MIR181A2HG | 1.00 | 15912 | 3 | | | | MIR2681 | 1.00 |
| 15817 | 3 | | | | | MIR181B1 | 1.00 | 15913 | 3 | | | | MIR2682 | 1.00 |
| 15818 | 3 | | | | | MIR181B2 | 1.00 | 15914 | 3 | | | | MIR26A1 | 1.00 |
| 15819 | 3 | | | | | MIR181C | 1.00 | 15915 | 3 | | | | MIR26A2 | 1.00 |
| 15820 | 3 | | | | | MIR181D | 1.00 | 15916 | 3 | | | | MIR26B | 1.00 |
| 15821 | 3 | | | | | MIR182 | 1.00 | 15917 | 3 | | | | MIR27A | 1.00 |
| 15822 | 3 | | | | | MIR1827 | 1.00 | 15918 | 3 | | | | MIR27B | 1.00 |
| 15823 | 3 | | | | | MIR183 | 1.00 | 15919 | 3 | | | | MIR2861 | 1.00 |
| 15824 | 3 | | | | | MIR184 | 1.00 | 15920 | 3 | | | | MIR2909 | 1.00 |
| 15825 | 3 | | | | | MIR185 | 1.00 | 15921 | 3 | | | | MIR296 | 1.00 |
| 15826 | 3 | | | | | MIR186 | 1.00 | 15922 | 3 | | | | MIR2964A | 1.00 |
| 15827 | 3 | | | | | MIR187 | 1.00 | 15923 | 3 | | | | MIR298 | 1.00 |
| 15828 | 3 | | | | | MIR188 | 1.00 | 15924 | 3 | | | | MIR299 | 1.00 |
| 15829 | 3 | | | | | MIR18A | 1.00 | 15925 | 3 | | | | MIR29A | 1.00 |
| 15830 | 3 | | | | | MIR18B | 1.00 | 15926 | 3 | | | | MIR29B1 | 1.00 |
| 15831 | 3 | | | | | MIR1908 | 1.00 | 15927 | 3 | | | | MIR29B2 | 1.00 |
| 15832 | 3 | | | | | MIR1909 | 1.00 | 15928 | 3 | | | | MIR29C | 1.00 |
| 15833 | 3 | | | | | MIR190A | 1.00 | 15929 | 3 | | | | MIR300 | 1.00 |

Fig. 40 - 84

| | | | | | | | | | | | | | |
|---|---|---|---|---|---|---|---|---|---|---|---|---|---|
| 15930 | 3 | | | | | MIR301A | 1.00 | 16026 | 3 | | | MIR32 | 1.00 |
| 15931 | 3 | | | | | MIR301B | 1.00 | 16027 | 3 | | | MIR3200 | 1.00 |
| 15932 | 3 | | | | | MIR302A | 1.00 | 16028 | 3 | | | MIR3201 | 1.00 |
| 15933 | 3 | | | | | MIR302B | 1.00 | 16029 | 3 | | | MIR3202-1 | 1.00 |
| 15934 | 3 | | | | | MIR302C | 1.00 | 16030 | 3 | | | MIR3202-2 | 1.00 |
| 15935 | 3 | | | | | MIR302D | 1.00 | 16031 | 3 | | | MIR320A | 1.00 |
| 15936 | 3 | | | | | MIR302F | 1.00 | 16032 | 3 | | | MIR320B1 | 1.00 |
| 15937 | 3 | | | | | MIR3064 | 1.00 | 16033 | 3 | | | MIR320B2 | 1.00 |
| 15938 | 3 | | | | | MIR3065 | 1.00 | 16034 | 3 | | | MIR320C1 | 1.00 |
| 15939 | 3 | | | | | MIR3074 | 1.00 | 16035 | 3 | | | MIR320C2 | 1.00 |
| 15940 | 3 | | | | | MIR30A | 1.00 | 16036 | 3 | | | MIR320D1 | 1.00 |
| 15941 | 3 | | | | | MIR30B | 1.00 | 16037 | 3 | | | MIR320D2 | 1.00 |
| 15942 | 3 | | | | | MIR30C1 | 1.00 | 16038 | 3 | | | MIR320E | 1.00 |
| 15943 | 3 | | | | | MIR30C2 | 1.00 | 16039 | 3 | | | MIR323A | 1.00 |
| 15944 | 3 | | | | | MIR30D | 1.00 | 16040 | 3 | | | MIR323B | 1.00 |
| 15945 | 3 | | | | | MIR30E | 1.00 | 16041 | 3 | | | MIR324 | 1.00 |
| 15946 | 3 | | | | | MIR31 | 1.00 | 16042 | 3 | | | MIR326 | 1.00 |
| 15947 | 3 | | | | | MIR3115 | 1.00 | 16043 | 3 | | | MIR328 | 1.00 |
| 15948 | 3 | | | | | MIR3117 | 1.00 | 16044 | 3 | | | MIR329-1 | 1.00 |
| 15949 | 3 | | | | | MIR3119-1 | 1.00 | 16045 | 3 | | | MIR329-2 | 1.00 |
| 15950 | 3 | | | | | MIR3120 | 1.00 | 16046 | 3 | | | MIR330 | 1.00 |
| 15951 | 3 | | | | | MIR3121 | 1.00 | 16047 | 3 | | | MIR331 | 1.00 |
| 15952 | 3 | | | | | MIR3122 | 1.00 | 16048 | 3 | | | MIR335 | 1.00 |
| 15953 | 3 | | | | | MIR3123 | 1.00 | 16049 | 3 | | | MIR337 | 1.00 |
| 15954 | 3 | | | | | MIR3124 | 1.00 | 16050 | 3 | | | MIR338 | 1.00 |
| 15955 | 3 | | | | | MIR3125 | 1.00 | 16051 | 3 | | | MIR339 | 1.00 |
| 15956 | 3 | | | | | MIR3126 | 1.00 | 16052 | 3 | | | MIR33A | 1.00 |
| 15957 | 3 | | | | | MIR3127 | 1.00 | 16053 | 3 | | | MIR33B | 1.00 |
| 15958 | 3 | | | | | MIR3128 | 1.00 | 16054 | 3 | | | MIR340 | 1.00 |
| 15959 | 3 | | | | | MIR3129 | 1.00 | 16055 | 3 | | | MIR345 | 1.00 |
| 15960 | 3 | | | | | MIR3130-1 | 1.00 | 16056 | 3 | | | MIR346 | 1.00 |
| 15961 | 3 | | | | | MIR3131 | 1.00 | 16057 | 3 | | | MIR34A | 1.00 |
| 15962 | 3 | | | | | MIR3132 | 1.00 | 16058 | 3 | | | MIR34B | 1.00 |
| 15963 | 3 | | | | | MIR3134 | 1.00 | 16059 | 3 | | | MIR34C | 1.00 |
| 15964 | 3 | | | | | MIR3136 | 1.00 | 16060 | 3 | | | MIR3529 | 1.00 |
| 15965 | 3 | | | | | MIR3138 | 1.00 | 16061 | 3 | | | MIR3545 | 1.00 |
| 15966 | 3 | | | | | MIR3140 | 1.00 | 16062 | 3 | | | MIR3591 | 1.00 |
| 15967 | 3 | | | | | MIR3141 | 1.00 | 16063 | 3 | | | MIR3605 | 1.00 |
| 15968 | 3 | | | | | MIR3142 | 1.00 | 16064 | 3 | | | MIR3606 | 1.00 |
| 15969 | 3 | | | | | MIR3143 | 1.00 | 16065 | 3 | | | MIR3607 | 1.00 |
| 15970 | 3 | | | | | MIR3145 | 1.00 | 16066 | 3 | | | MIR3609 | 1.00 |
| 15971 | 3 | | | | | MIR3146 | 1.00 | 16067 | 3 | | | MIR3610 | 1.00 |
| 15972 | 3 | | | | | MIR3147 | 1.00 | 16068 | 3 | | | MIR3612 | 1.00 |
| 15973 | 3 | | | | | MIR3148 | 1.00 | 16069 | 3 | | | MIR3613 | 1.00 |
| 15974 | 3 | | | | | MIR3150A | 1.00 | 16070 | 3 | | | MIR3614 | 1.00 |
| 15975 | 3 | | | | | MIR3150B | 1.00 | 16071 | 3 | | | MIR3615 | 1.00 |
| 15976 | 3 | | | | | MIR3151 | 1.00 | 16072 | 3 | | | MIR3616 | 1.00 |
| 15977 | 3 | | | | | MIR3152 | 1.00 | 16073 | 3 | | | MIR3618 | 1.00 |
| 15978 | 3 | | | | | MIR3153 | 1.00 | 16074 | 3 | | | MIR3619 | 1.00 |
| 15979 | 3 | | | | | MIR3154 | 1.00 | 16075 | 3 | | | MIR362 | 1.00 |
| 15980 | 3 | | | | | MIR3155A | 1.00 | 16076 | 3 | | | MIR3620 | 1.00 |
| 15981 | 3 | | | | | MIR3155B | 1.00 | 16077 | 3 | | | MIR3621 | 1.00 |
| 15982 | 3 | | | | | MIR3156-1 | 1.00 | 16078 | 3 | | | MIR3622A | 1.00 |
| 15983 | 3 | | | | | MIR3156-2 | 1.00 | 16079 | 3 | | | MIR3622B | 1.00 |
| 15984 | 3 | | | | | MIR3156-3 | 1.00 | 16080 | 3 | | | MIR363 | 1.00 |
| 15985 | 3 | | | | | MIR3157 | 1.00 | 16081 | 3 | | | MIR3646 | 1.00 |
| 15986 | 3 | | | | | MIR3158-2 | 1.00 | 16082 | 3 | | | MIR3649 | 1.00 |
| 15987 | 3 | | | | | MIR3160-1 | 1.00 | 16083 | 3 | | | MIR3650 | 1.00 |
| 15988 | 3 | | | | | MIR3160-2 | 1.00 | 16084 | 3 | | | MIR3651 | 1.00 |
| 15989 | 3 | | | | | MIR3162 | 1.00 | 16085 | 3 | | | MIR3652 | 1.00 |
| 15990 | 3 | | | | | MIR3165 | 1.00 | 16086 | 3 | | | MIR3653 | 1.00 |
| 15991 | 3 | | | | | MIR3167 | 1.00 | 16087 | 3 | | | MIR3654 | 1.00 |
| 15992 | 3 | | | | | MIR3169 | 1.00 | 16088 | 3 | | | MIR3655 | 1.00 |
| 15993 | 3 | | | | | MIR3170 | 1.00 | 16089 | 3 | | | MIR3656 | 1.00 |
| 15994 | 3 | | | | | MIR3173 | 1.00 | 16090 | 3 | | | MIR3658 | 1.00 |
| 15995 | 3 | | | | | MIR3175 | 1.00 | 16091 | 3 | | | MIR3659 | 1.00 |
| 15996 | 3 | | | | | MIR3176 | 1.00 | 16092 | 3 | | | MIR365A | 1.00 |
| 15997 | 3 | | | | | MIR3177 | 1.00 | 16093 | 3 | | | MIR365B | 1.00 |
| 15998 | 3 | | | | | MIR3178 | 1.00 | 16094 | 3 | | | MIR3660 | 1.00 |
| 15999 | 3 | | | | | MIR3179-1 | 1.00 | 16095 | 3 | | | MIR3661 | 1.00 |
| 16000 | 3 | | | | | MIR3179-3 | 1.00 | 16096 | 3 | | | MIR3662 | 1.00 |
| 16001 | 3 | | | | | MIR3180-1 | 1.00 | 16097 | 3 | | | MIR3663 | 1.00 |
| 16002 | 3 | | | | | MIR3180-2 | 1.00 | 16098 | 3 | | | MIR3664 | 1.00 |
| 16003 | 3 | | | | | MIR3180-3 | 1.00 | 16099 | 3 | | | MIR3666 | 1.00 |
| 16004 | 3 | | | | | MIR3180-4 | 1.00 | 16100 | 3 | | | MIR3668 | 1.00 |
| 16005 | 3 | | | | | MIR3180-5 | 1.00 | 16101 | 3 | | | MIR367 | 1.00 |
| 16006 | 3 | | | | | MIR3182 | 1.00 | 16102 | 3 | | | MIR3671 | 1.00 |
| 16007 | 3 | | | | | MIR3183 | 1.00 | 16103 | 3 | | | MIR3675 | 1.00 |
| 16008 | 3 | | | | | MIR3184 | 1.00 | 16104 | 3 | | | MIR3676 | 1.00 |
| 16009 | 3 | | | | | MIR3185 | 1.00 | 16105 | 3 | | | MIR3677 | 1.00 |
| 16010 | 3 | | | | | MIR3186 | 1.00 | 16106 | 3 | | | MIR3678 | 1.00 |
| 16011 | 3 | | | | | MIR3187 | 1.00 | 16107 | 3 | | | MIR3679 | 1.00 |
| 16012 | 3 | | | | | MIR3188 | 1.00 | 16108 | 3 | | | MIR3680-1 | 1.00 |
| 16013 | 3 | | | | | MIR3189 | 1.00 | 16109 | 3 | | | MIR3682 | 1.00 |
| 16014 | 3 | | | | | MIR3190 | 1.00 | 16110 | 3 | | | MIR3684 | 1.00 |
| 16015 | 3 | | | | | MIR3191 | 1.00 | 16111 | 3 | | | MIR3685 | 1.00 |
| 16016 | 3 | | | | | MIR3192 | 1.00 | 16112 | 3 | | | MIR3687 | 1.00 |
| 16017 | 3 | | | | | MIR3193 | 1.00 | 16113 | 3 | | | MIR3688-1 | 1.00 |
| 16018 | 3 | | | | | MIR3194 | 1.00 | 16114 | 3 | | | MIR3688-2 | 1.00 |
| 16019 | 3 | | | | | MIR3196 | 1.00 | 16115 | 3 | | | MIR3689A | 1.00 |
| 16020 | 3 | | | | | MIR3197 | 1.00 | 16116 | 3 | | | MIR3689B | 1.00 |
| 16021 | 3 | | | | | MIR3198-1 | 1.00 | 16117 | 3 | | | MIR3689C | 1.00 |
| 16022 | 3 | | | | | MIR3198-2 | 1.00 | 16118 | 3 | | | MIR3689D1 | 1.00 |
| 16023 | 3 | | | | | MIR3199-1 | 1.00 | 16119 | 3 | | | MIR3689D2 | 1.00 |
| 16024 | 3 | | | | | MIR3199-2 | 1.00 | 16120 | 3 | | | MIR3689E | 1.00 |
| 16025 | 3 | | | | | MIR31HG | 1.00 | 16121 | 3 | | | MIR3689F | 1.00 |

Fig. 40 - 85

| | | | | | | | | | | | | | | | |
|---|---|---|---|---|---|---|---|---|---|---|---|---|---|---|---|
| 16122 | 3 | | | | | MIR369 | 1.00 | 16218 | 3 | | | | | MIR4271 | 1.00 |
| 16123 | 3 | | | | | MIR3690 | 1.00 | 16219 | 3 | | | | | MIR4272 | 1.00 |
| 16124 | 3 | | | | | MIR3691 | 1.00 | 16220 | 3 | | | | | MIR4273 | 1.00 |
| 16125 | 3 | | | | | MIR3692 | 1.00 | 16221 | 3 | | | | | MIR4274 | 1.00 |
| 16126 | 3 | | | | | MIR3714 | 1.00 | 16222 | 3 | | | | | MIR4275 | 1.00 |
| 16127 | 3 | | | | | MIR371A | 1.00 | 16223 | 3 | | | | | MIR4276 | 1.00 |
| 16128 | 3 | | | | | MIR371B | 1.00 | 16224 | 3 | | | | | MIR4277 | 1.00 |
| 16129 | 3 | | | | | MIR372 | 1.00 | 16225 | 3 | | | | | MIR4278 | 1.00 |
| 16130 | 3 | | | | | MIR373 | 1.00 | 16226 | 3 | | | | | MIR4279 | 1.00 |
| 16131 | 3 | | | | | MIR374A | 1.00 | 16227 | 3 | | | | | MIR4280 | 1.00 |
| 16132 | 3 | | | | | MIR374B | 1.00 | 16228 | 3 | | | | | MIR4281 | 1.00 |
| 16133 | 3 | | | | | MIR374C | 1.00 | 16229 | 3 | | | | | MIR4282 | 1.00 |
| 16134 | 3 | | | | | MIR375 | 1.00 | 16230 | 3 | | | | | MIR4283-1 | 1.00 |
| 16135 | 3 | | | | | MIR376A1 | 1.00 | 16231 | 3 | | | | | MIR4283-2 | 1.00 |
| 16136 | 3 | | | | | MIR376A2 | 1.00 | 16232 | 3 | | | | | MIR4284 | 1.00 |
| 16137 | 3 | | | | | MIR376B | 1.00 | 16233 | 3 | | | | | MIR4285 | 1.00 |
| 16138 | 3 | | | | | MIR376C | 1.00 | 16234 | 3 | | | | | MIR4287 | 1.00 |
| 16139 | 3 | | | | | MIR377 | 1.00 | 16235 | 3 | | | | | MIR4288 | 1.00 |
| 16140 | 3 | | | | | MIR378C | 1.00 | 16236 | 3 | | | | | MIR4289 | 1.00 |
| 16141 | 3 | | | | | MIR378D1 | 1.00 | 16237 | 3 | | | | | MIR429 | 1.00 |
| 16142 | 3 | | | | | MIR378D2 | 1.00 | 16238 | 3 | | | | | MIR4290 | 1.00 |
| 16143 | 3 | | | | | MIR378E | 1.00 | 16239 | 3 | | | | | MIR4291 | 1.00 |
| 16144 | 3 | | | | | MIR378F | 1.00 | 16240 | 3 | | | | | MIR4292 | 1.00 |
| 16145 | 3 | | | | | MIR379 | 1.00 | 16241 | 3 | | | | | MIR4294 | 1.00 |
| 16146 | 3 | | | | | MIR380 | 1.00 | 16242 | 3 | | | | | MIR4295 | 1.00 |
| 16147 | 3 | | | | | MIR381 | 1.00 | 16243 | 3 | | | | | MIR4296 | 1.00 |
| 16148 | 3 | | | | | MIR382 | 1.00 | 16244 | 3 | | | | | MIR4297 | 1.00 |
| 16149 | 3 | | | | | MIR383 | 1.00 | 16245 | 3 | | | | | MIR4298 | 1.00 |
| 16150 | 3 | | | | | MIR384 | 1.00 | 16246 | 3 | | | | | MIR4299 | 1.00 |
| 16151 | 3 | | | | | MIR3907 | 1.00 | 16247 | 3 | | | | | MIR4300 | 1.00 |
| 16152 | 3 | | | | | MIR3908 | 1.00 | 16248 | 3 | | | | | MIR4301 | 1.00 |
| 16153 | 3 | | | | | MIR3909 | 1.00 | 16249 | 3 | | | | | MIR4302 | 1.00 |
| 16154 | 3 | | | | | MIR3910-1 | 1.00 | 16250 | 3 | | | | | MIR4303 | 1.00 |
| 16155 | 3 | | | | | MIR3910-2 | 1.00 | 16251 | 3 | | | | | MIR4304 | 1.00 |
| 16156 | 3 | | | | | MIR3911 | 1.00 | 16252 | 3 | | | | | MIR4305 | 1.00 |
| 16157 | 3 | | | | | MIR3912 | 1.00 | 16253 | 3 | | | | | MIR4306 | 1.00 |
| 16158 | 3 | | | | | MIR3913-1 | 1.00 | 16254 | 3 | | | | | MIR4307 | 1.00 |
| 16159 | 3 | | | | | MIR3913-2 | 1.00 | 16255 | 3 | | | | | MIR4308 | 1.00 |
| 16160 | 3 | | | | | MIR3914-1 | 1.00 | 16256 | 3 | | | | | MIR4309 | 1.00 |
| 16161 | 3 | | | | | MIR3914-2 | 1.00 | 16257 | 3 | | | | | MIR431 | 1.00 |
| 16162 | 3 | | | | | MIR3916 | 1.00 | 16258 | 3 | | | | | MIR4310 | 1.00 |
| 16163 | 3 | | | | | MIR3917 | 1.00 | 16259 | 3 | | | | | MIR4311 | 1.00 |
| 16164 | 3 | | | | | MIR3918 | 1.00 | 16260 | 3 | | | | | MIR4312 | 1.00 |
| 16165 | 3 | | | | | MIR3919 | 1.00 | 16261 | 3 | | | | | MIR4314 | 1.00 |
| 16166 | 3 | | | | | MIR3920 | 1.00 | 16262 | 3 | | | | | MIR4315-2 | 1.00 |
| 16167 | 3 | | | | | MIR3921 | 1.00 | 16263 | 3 | | | | | MIR4316 | 1.00 |
| 16168 | 3 | | | | | MIR3922 | 1.00 | 16264 | 3 | | | | | MIR4317 | 1.00 |
| 16169 | 3 | | | | | MIR3924 | 1.00 | 16265 | 3 | | | | | MIR4318 | 1.00 |
| 16170 | 3 | | | | | MIR3925 | 1.00 | 16266 | 3 | | | | | MIR4319 | 1.00 |
| 16171 | 3 | | | | | MIR3926-1 | 1.00 | 16267 | 3 | | | | | MIR432 | 1.00 |
| 16172 | 3 | | | | | MIR3926-2 | 1.00 | 16268 | 3 | | | | | MIR4320 | 1.00 |
| 16173 | 3 | | | | | MIR3928 | 1.00 | 16269 | 3 | | | | | MIR4321 | 1.00 |
| 16174 | 3 | | | | | MIR3935 | 1.00 | 16270 | 3 | | | | | MIR4322 | 1.00 |
| 16175 | 3 | | | | | MIR3936 | 1.00 | 16271 | 3 | | | | | MIR4323 | 1.00 |
| 16176 | 3 | | | | | MIR3938 | 1.00 | 16272 | 3 | | | | | MIR4324 | 1.00 |
| 16177 | 3 | | | | | MIR3939 | 1.00 | 16273 | 3 | | | | | MIR4325 | 1.00 |
| 16178 | 3 | | | | | MIR3940 | 1.00 | 16274 | 3 | | | | | MIR4326 | 1.00 |
| 16179 | 3 | | | | | MIR3941 | 1.00 | 16275 | 3 | | | | | MIR4327 | 1.00 |
| 16180 | 3 | | | | | MIR3942 | 1.00 | 16276 | 3 | | | | | MIR4328 | 1.00 |
| 16181 | 3 | | | | | MIR3943 | 1.00 | 16277 | 3 | | | | | MIR4329 | 1.00 |
| 16182 | 3 | | | | | MIR3944 | 1.00 | 16278 | 3 | | | | | MIR433 | 1.00 |
| 16183 | 3 | | | | | MIR3945 | 1.00 | 16279 | 3 | | | | | MIR4330 | 1.00 |
| 16184 | 3 | | | | | MIR3960 | 1.00 | 16280 | 3 | | | | | MIR4417 | 1.00 |
| 16185 | 3 | | | | | MIR3973 | 1.00 | 16281 | 3 | | | | | MIR4420 | 1.00 |
| 16186 | 3 | | | | | MIR3974 | 1.00 | 16282 | 3 | | | | | MIR4422 | 1.00 |
| 16187 | 3 | | | | | MIR3975 | 1.00 | 16283 | 3 | | | | | MIR4423 | 1.00 |
| 16188 | 3 | | | | | MIR3976 | 1.00 | 16284 | 3 | | | | | MIR4424 | 1.00 |
| 16189 | 3 | | | | | MIR3977 | 1.00 | 16285 | 3 | | | | | MIR4426 | 1.00 |
| 16190 | 3 | | | | | MIR3978 | 1.00 | 16286 | 3 | | | | | MIR4427 | 1.00 |
| 16191 | 3 | | | | | MIR409 | 1.00 | 16287 | 3 | | | | | MIR4429 | 1.00 |
| 16192 | 3 | | | | | MIR410 | 1.00 | 16288 | 3 | | | | | MIR4432 | 1.00 |
| 16193 | 3 | | | | | MIR411 | 1.00 | 16289 | 3 | | | | | MIR4434 | 1.00 |
| 16194 | 3 | | | | | MIR412 | 1.00 | 16290 | 3 | | | | | MIR4435-1 | 1.00 |
| 16195 | 3 | | | | | MIR421 | 1.00 | 16291 | 3 | | | | | MIR4435-2 | 1.00 |
| 16196 | 3 | | | | | MIR423 | 1.00 | 16292 | 3 | | | | | MIR4436A | 1.00 |
| 16197 | 3 | | | | | MIR424 | 1.00 | 16293 | 3 | | | | | MIR4436B1 | 1.00 |
| 16198 | 3 | | | | | MIR425 | 1.00 | 16294 | 3 | | | | | MIR4437 | 1.00 |
| 16199 | 3 | | | | | MIR4251 | 1.00 | 16295 | 3 | | | | | MIR4439 | 1.00 |
| 16200 | 3 | | | | | MIR4252 | 1.00 | 16296 | 3 | | | | | MIR4440 | 1.00 |
| 16201 | 3 | | | | | MIR4253 | 1.00 | 16297 | 3 | | | | | MIR4441 | 1.00 |
| 16202 | 3 | | | | | MIR4254 | 1.00 | 16298 | 3 | | | | | MIR4442 | 1.00 |
| 16203 | 3 | | | | | MIR4255 | 1.00 | 16299 | 3 | | | | | MIR4443 | 1.00 |
| 16204 | 3 | | | | | MIR4256 | 1.00 | 16300 | 3 | | | | | MIR4444-1 | 1.00 |
| 16205 | 3 | | | | | MIR4257 | 1.00 | 16301 | 3 | | | | | MIR4446 | 1.00 |
| 16206 | 3 | | | | | MIR4258 | 1.00 | 16302 | 3 | | | | | MIR4449 | 1.00 |
| 16207 | 3 | | | | | MIR4260 | 1.00 | 16303 | 3 | | | | | MIR4450 | 1.00 |
| 16208 | 3 | | | | | MIR4261 | 1.00 | 16304 | 3 | | | | | MIR4451 | 1.00 |
| 16209 | 3 | | | | | MIR4262 | 1.00 | 16305 | 3 | | | | | MIR4453 | 1.00 |
| 16210 | 3 | | | | | MIR4263 | 1.00 | 16306 | 3 | | | | | MIR4454 | 1.00 |
| 16211 | 3 | | | | | MIR4264 | 1.00 | 16307 | 3 | | | | | MIR4456 | 1.00 |
| 16212 | 3 | | | | | MIR4265 | 1.00 | 16308 | 3 | | | | | MIR4457 | 1.00 |
| 16213 | 3 | | | | | MIR4266 | 1.00 | 16309 | 3 | | | | | MIR4458 | 1.00 |
| 16214 | 3 | | | | | MIR4267 | 1.00 | 16310 | 3 | | | | | MIR4460 | 1.00 |
| 16215 | 3 | | | | | MIR4268 | 1.00 | 16311 | 3 | | | | | MIR4461 | 1.00 |
| 16216 | 3 | | | | | MIR4269 | 1.00 | 16312 | 3 | | | | | MIR4462 | 1.00 |
| 16217 | 3 | | | | | MIR4270 | 1.00 | 16313 | 3 | | | | | MIR4464 | 1.00 |

Fig. 40 - 86

| | | | | | | | | | | | | | | |
|---|---|---|---|---|---|---|---|---|---|---|---|---|---|---|
| 16314 | 3 | | | | | MIR4465 | 1.00 | 16410 | 3 | | | | MIR4655 | 1.00 |
| 16315 | 3 | | | | | MIR4466 | 1.00 | 16411 | 3 | | | | MIR4656 | 1.00 |
| 16316 | 3 | | | | | MIR4467 | 1.00 | 16412 | 3 | | | | MIR4657 | 1.00 |
| 16317 | 3 | | | | | MIR4468 | 1.00 | 16413 | 3 | | | | MIR4658 | 1.00 |
| 16318 | 3 | | | | | MIR4469 | 1.00 | 16414 | 3 | | | | MIR4659A | 1.00 |
| 16319 | 3 | | | | | MIR4470 | 1.00 | 16415 | 3 | | | | MIR4659B | 1.00 |
| 16320 | 3 | | | | | MIR4471 | 1.00 | 16416 | 3 | | | | MIR4660 | 1.00 |
| 16321 | 3 | | | | | MIR4472-1 | 1.00 | 16417 | 3 | | | | MIR4661 | 1.00 |
| 16322 | 3 | | | | | MIR4472-2 | 1.00 | 16418 | 3 | | | | MIR4663 | 1.00 |
| 16323 | 3 | | | | | MIR4473 | 1.00 | 16419 | 3 | | | | MIR4664 | 1.00 |
| 16324 | 3 | | | | | MIR4474 | 1.00 | 16420 | 3 | | | | MIR4665 | 1.00 |
| 16325 | 3 | | | | | MIR4475 | 1.00 | 16421 | 3 | | | | MIR4666A | 1.00 |
| 16326 | 3 | | | | | MIR4476 | 1.00 | 16422 | 3 | | | | MIR4667 | 1.00 |
| 16327 | 3 | | | | | MIR4478 | 1.00 | 16423 | 3 | | | | MIR4668 | 1.00 |
| 16328 | 3 | | | | | MIR4479 | 1.00 | 16424 | 3 | | | | MIR4669 | 1.00 |
| 16329 | 3 | | | | | MIR448 | 1.00 | 16425 | 3 | | | | MIR4670 | 1.00 |
| 16330 | 3 | | | | | MIR4480 | 1.00 | 16426 | 3 | | | | MIR4671 | 1.00 |
| 16331 | 3 | | | | | MIR4482-1 | 1.00 | 16427 | 3 | | | | MIR4672 | 1.00 |
| 16332 | 3 | | | | | MIR4483 | 1.00 | 16428 | 3 | | | | MIR4673 | 1.00 |
| 16333 | 3 | | | | | MIR4484 | 1.00 | 16429 | 3 | | | | MIR4674 | 1.00 |
| 16334 | 3 | | | | | MIR4485 | 1.00 | 16430 | 3 | | | | MIR4675 | 1.00 |
| 16335 | 3 | | | | | MIR4486 | 1.00 | 16431 | 3 | | | | MIR4676 | 1.00 |
| 16336 | 3 | | | | | MIR4488 | 1.00 | 16432 | 3 | | | | MIR4677 | 1.00 |
| 16337 | 3 | | | | | MIR4489 | 1.00 | 16433 | 3 | | | | MIR4678 | 1.00 |
| 16338 | 3 | | | | | MIR4490 | 1.00 | 16434 | 3 | | | | MIR4679-1 | 1.00 |
| 16339 | 3 | | | | | MIR4491 | 1.00 | 16435 | 3 | | | | MIR4679-2 | 1.00 |
| 16340 | 3 | | | | | MIR4492 | 1.00 | 16436 | 3 | | | | MIR4680 | 1.00 |
| 16341 | 3 | | | | | MIR4493 | 1.00 | 16437 | 3 | | | | MIR4681 | 1.00 |
| 16342 | 3 | | | | | MIR4497 | 1.00 | 16438 | 3 | | | | MIR4682 | 1.00 |
| 16343 | 3 | | | | | MIR4498 | 1.00 | 16439 | 3 | | | | MIR4683 | 1.00 |
| 16344 | 3 | | | | | MIR4499 | 1.00 | 16440 | 3 | | | | MIR4684 | 1.00 |
| 16345 | 3 | | | | | MIR449A | 1.00 | 16441 | 3 | | | | MIR4685 | 1.00 |
| 16346 | 3 | | | | | MIR449B | 1.00 | 16442 | 3 | | | | MIR4686 | 1.00 |
| 16347 | 3 | | | | | MIR449C | 1.00 | 16443 | 3 | | | | MIR4687 | 1.00 |
| 16348 | 3 | | | | | MIR4500 | 1.00 | 16444 | 3 | | | | MIR4688 | 1.00 |
| 16349 | 3 | | | | | MIR4500HG | 1.00 | 16445 | 3 | | | | MIR4689 | 1.00 |
| 16350 | 3 | | | | | MIR4503 | 1.00 | 16446 | 3 | | | | MIR4690 | 1.00 |
| 16351 | 3 | | | | | MIR4505 | 1.00 | 16447 | 3 | | | | MIR4691 | 1.00 |
| 16352 | 3 | | | | | MIR4508 | 1.00 | 16448 | 3 | | | | MIR4692 | 1.00 |
| 16353 | 3 | | | | | MIR4509-1 | 1.00 | 16449 | 3 | | | | MIR4693 | 1.00 |
| 16354 | 3 | | | | | MIR450A1 | 1.00 | 16450 | 3 | | | | MIR4694 | 1.00 |
| 16355 | 3 | | | | | MIR450A2 | 1.00 | 16451 | 3 | | | | MIR4695 | 1.00 |
| 16356 | 3 | | | | | MIR450B | 1.00 | 16452 | 3 | | | | MIR4696 | 1.00 |
| 16357 | 3 | | | | | MIR4510 | 1.00 | 16453 | 3 | | | | MIR4697 | 1.00 |
| 16358 | 3 | | | | | MIR4511 | 1.00 | 16454 | 3 | | | | MIR4698 | 1.00 |
| 16359 | 3 | | | | | MIR4513 | 1.00 | 16455 | 3 | | | | MIR4699 | 1.00 |
| 16360 | 3 | | | | | MIR4514 | 1.00 | 16456 | 3 | | | | MIR4700 | 1.00 |
| 16361 | 3 | | | | | MIR4515 | 1.00 | 16457 | 3 | | | | MIR4701 | 1.00 |
| 16362 | 3 | | | | | MIR4516 | 1.00 | 16458 | 3 | | | | MIR4703 | 1.00 |
| 16363 | 3 | | | | | MIR4517 | 1.00 | 16459 | 3 | | | | MIR4705 | 1.00 |
| 16364 | 3 | | | | | MIR4518 | 1.00 | 16460 | 3 | | | | MIR4706 | 1.00 |
| 16365 | 3 | | | | | MIR4519 | 1.00 | 16461 | 3 | | | | MIR4707 | 1.00 |
| 16366 | 3 | | | | | MIR451A | 1.00 | 16462 | 3 | | | | MIR4708 | 1.00 |
| 16367 | 3 | | | | | MIR451B | 1.00 | 16463 | 3 | | | | MIR4709 | 1.00 |
| 16368 | 3 | | | | | MIR452 | 1.00 | 16464 | 3 | | | | MIR4710 | 1.00 |
| 16369 | 3 | | | | | MIR4520A | 1.00 | 16465 | 3 | | | | MIR4711 | 1.00 |
| 16370 | 3 | | | | | MIR4520B | 1.00 | 16466 | 3 | | | | MIR4712 | 1.00 |
| 16371 | 3 | | | | | MIR4521 | 1.00 | 16467 | 3 | | | | MIR4713 | 1.00 |
| 16372 | 3 | | | | | MIR4522 | 1.00 | 16468 | 3 | | | | MIR4714 | 1.00 |
| 16373 | 3 | | | | | MIR4523 | 1.00 | 16469 | 3 | | | | MIR4715 | 1.00 |
| 16374 | 3 | | | | | MIR4524A | 1.00 | 16470 | 3 | | | | MIR4716 | 1.00 |
| 16375 | 3 | | | | | MIR4526 | 1.00 | 16471 | 3 | | | | MIR4717 | 1.00 |
| 16376 | 3 | | | | | MIR4529 | 1.00 | 16472 | 3 | | | | MIR4718 | 1.00 |
| 16377 | 3 | | | | | MIR4530 | 1.00 | 16473 | 3 | | | | MIR4719 | 1.00 |
| 16378 | 3 | | | | | MIR4531 | 1.00 | 16474 | 3 | | | | MIR4720 | 1.00 |
| 16379 | 3 | | | | | MIR4532 | 1.00 | 16475 | 3 | | | | MIR4721 | 1.00 |
| 16380 | 3 | | | | | MIR4533 | 1.00 | 16476 | 3 | | | | MIR4722 | 1.00 |
| 16381 | 3 | | | | | MIR4534 | 1.00 | 16477 | 3 | | | | MIR4723 | 1.00 |
| 16382 | 3 | | | | | MIR4535 | 1.00 | 16478 | 3 | | | | MIR4724 | 1.00 |
| 16383 | 3 | | | | | MIR4536-1 | 1.00 | 16479 | 3 | | | | MIR4725 | 1.00 |
| 16384 | 3 | | | | | MIR454 | 1.00 | 16480 | 3 | | | | MIR4726 | 1.00 |
| 16385 | 3 | | | | | MIR4540 | 1.00 | 16481 | 3 | | | | MIR4727 | 1.00 |
| 16386 | 3 | | | | | MIR455 | 1.00 | 16482 | 3 | | | | MIR4728 | 1.00 |
| 16387 | 3 | | | | | MIR4632 | 1.00 | 16483 | 3 | | | | MIR4729 | 1.00 |
| 16388 | 3 | | | | | MIR4633 | 1.00 | 16484 | 3 | | | | MIR4730 | 1.00 |
| 16389 | 3 | | | | | MIR4634 | 1.00 | 16485 | 3 | | | | MIR4731 | 1.00 |
| 16390 | 3 | | | | | MIR4635 | 1.00 | 16486 | 3 | | | | MIR4732 | 1.00 |
| 16391 | 3 | | | | | MIR4636 | 1.00 | 16487 | 3 | | | | MIR4733 | 1.00 |
| 16392 | 3 | | | | | MIR4637 | 1.00 | 16488 | 3 | | | | MIR4734 | 1.00 |
| 16393 | 3 | | | | | MIR4638 | 1.00 | 16489 | 3 | | | | MIR4735 | 1.00 |
| 16394 | 3 | | | | | MIR4639 | 1.00 | 16490 | 3 | | | | MIR4736 | 1.00 |
| 16395 | 3 | | | | | MIR4640 | 1.00 | 16491 | 3 | | | | MIR4737 | 1.00 |
| 16396 | 3 | | | | | MIR4641 | 1.00 | 16492 | 3 | | | | MIR4738 | 1.00 |
| 16397 | 3 | | | | | MIR4642 | 1.00 | 16493 | 3 | | | | MIR4739 | 1.00 |
| 16398 | 3 | | | | | MIR4643 | 1.00 | 16494 | 3 | | | | MIR4740 | 1.00 |
| 16399 | 3 | | | | | MIR4644 | 1.00 | 16495 | 3 | | | | MIR4741 | 1.00 |
| 16400 | 3 | | | | | MIR4645 | 1.00 | 16496 | 3 | | | | MIR4742 | 1.00 |
| 16401 | 3 | | | | | MIR4646 | 1.00 | 16497 | 3 | | | | MIR4743 | 1.00 |
| 16402 | 3 | | | | | MIR4647 | 1.00 | 16498 | 3 | | | | MIR4744 | 1.00 |
| 16403 | 3 | | | | | MIR4648 | 1.00 | 16499 | 3 | | | | MIR4745 | 1.00 |
| 16404 | 3 | | | | | MIR4649 | 1.00 | 16500 | 3 | | | | MIR4746 | 1.00 |
| 16405 | 3 | | | | | MIR4650-1 | 1.00 | 16501 | 3 | | | | MIR4747 | 1.00 |
| 16406 | 3 | | | | | MIR4651 | 1.00 | 16502 | 3 | | | | MIR4748 | 1.00 |
| 16407 | 3 | | | | | MIR4652 | 1.00 | 16503 | 3 | | | | MIR4749 | 1.00 |
| 16408 | 3 | | | | | MIR4653 | 1.00 | 16504 | 3 | | | | MIR4750 | 1.00 |
| 16409 | 3 | | | | | MIR4654 | 1.00 | 16505 | 3 | | | | MIR4751 | 1.00 |

Fig. 40 - 87

| | | | | | | | | | | | | | | | |
|---|---|---|---|---|---|---|---|---|---|---|---|---|---|---|---|
| 16506 | 3 | | | | | MIR4752 | 1.00 | 16602 | 3 | | | | | MIR516A1 | 1.00 |
| 16507 | 3 | | | | | MIR4753 | 1.00 | 16603 | 3 | | | | | MIR516A2 | 1.00 |
| 16508 | 3 | | | | | MIR4754 | 1.00 | 16604 | 3 | | | | | MIR516B1 | 1.00 |
| 16509 | 3 | | | | | MIR4755 | 1.00 | 16605 | 3 | | | | | MIR516B2 | 1.00 |
| 16510 | 3 | | | | | MIR4756 | 1.00 | 16606 | 3 | | | | | MIR517A | 1.00 |
| 16511 | 3 | | | | | MIR4757 | 1.00 | 16607 | 3 | | | | | MIR517B | 1.00 |
| 16512 | 3 | | | | | MIR4758 | 1.00 | 16608 | 3 | | | | | MIR517C | 1.00 |
| 16513 | 3 | | | | | MIR4759 | 1.00 | 16609 | 3 | | | | | MIR518A1 | 1.00 |
| 16514 | 3 | | | | | MIR4760 | 1.00 | 16610 | 3 | | | | | MIR518A2 | 1.00 |
| 16515 | 3 | | | | | MIR4761 | 1.00 | 16611 | 3 | | | | | MIR518B | 1.00 |
| 16516 | 3 | | | | | MIR4762 | 1.00 | 16612 | 3 | | | | | MIR518C | 1.00 |
| 16517 | 3 | | | | | MIR4763 | 1.00 | 16613 | 3 | | | | | MIR518D | 1.00 |
| 16518 | 3 | | | | | MIR4764 | 1.00 | 16614 | 3 | | | | | MIR518E | 1.00 |
| 16519 | 3 | | | | | MIR4765 | 1.00 | 16615 | 3 | | | | | MIR518F | 1.00 |
| 16520 | 3 | | | | | MIR4766 | 1.00 | 16616 | 3 | | | | | MIR519A1 | 1.00 |
| 16521 | 3 | | | | | MIR4767 | 1.00 | 16617 | 3 | | | | | MIR519A2 | 1.00 |
| 16522 | 3 | | | | | MIR4768 | 1.00 | 16618 | 3 | | | | | MIR519B | 1.00 |
| 16523 | 3 | | | | | MIR4769 | 1.00 | 16619 | 3 | | | | | MIR519C | 1.00 |
| 16524 | 3 | | | | | MIR4770 | 1.00 | 16620 | 3 | | | | | MIR519D | 1.00 |
| 16525 | 3 | | | | | MIR4772 | 1.00 | 16621 | 3 | | | | | MIR519E | 1.00 |
| 16526 | 3 | | | | | MIR4773-2 | 1.00 | 16622 | 3 | | | | | MIR520A | 1.00 |
| 16527 | 3 | | | | | MIR4774 | 1.00 | 16623 | 3 | | | | | MIR520B | 1.00 |
| 16528 | 3 | | | | | MIR4775 | 1.00 | 16624 | 3 | | | | | MIR520C | 1.00 |
| 16529 | 3 | | | | | MIR4776-2 | 1.00 | 16625 | 3 | | | | | MIR520D | 1.00 |
| 16530 | 3 | | | | | MIR4777 | 1.00 | 16626 | 3 | | | | | MIR520E | 1.00 |
| 16531 | 3 | | | | | MIR4778 | 1.00 | 16627 | 3 | | | | | MIR520F | 1.00 |
| 16532 | 3 | | | | | MIR4779 | 1.00 | 16628 | 3 | | | | | MIR520G | 1.00 |
| 16533 | 3 | | | | | MIR4780 | 1.00 | 16629 | 3 | | | | | MIR520H | 1.00 |
| 16534 | 3 | | | | | MIR4781 | 1.00 | 16630 | 3 | | | | | MIR521-1 | 1.00 |
| 16535 | 3 | | | | | MIR4782 | 1.00 | 16631 | 3 | | | | | MIR521-2 | 1.00 |
| 16536 | 3 | | | | | MIR4783 | 1.00 | 16632 | 3 | | | | | MIR522 | 1.00 |
| 16537 | 3 | | | | | MIR4784 | 1.00 | 16633 | 3 | | | | | MIR523 | 1.00 |
| 16538 | 3 | | | | | MIR4785 | 1.00 | 16634 | 3 | | | | | MIR524 | 1.00 |
| 16539 | 3 | | | | | MIR4786 | 1.00 | 16635 | 3 | | | | | MIR525 | 1.00 |
| 16540 | 3 | | | | | MIR4787 | 1.00 | 16636 | 3 | | | | | MIR526A1 | 1.00 |
| 16541 | 3 | | | | | MIR4788 | 1.00 | 16637 | 3 | | | | | MIR526A2 | 1.00 |
| 16542 | 3 | | | | | MIR4789 | 1.00 | 16638 | 3 | | | | | MIR526B | 1.00 |
| 16543 | 3 | | | | | MIR4790 | 1.00 | 16639 | 3 | | | | | MIR527 | 1.00 |
| 16544 | 3 | | | | | MIR4791 | 1.00 | 16640 | 3 | | | | | MIR532 | 1.00 |
| 16545 | 3 | | | | | MIR4792 | 1.00 | 16641 | 3 | | | | | MIR539 | 1.00 |
| 16546 | 3 | | | | | MIR4793 | 1.00 | 16642 | 3 | | | | | MIR541 | 1.00 |
| 16547 | 3 | | | | | MIR4794 | 1.00 | 16643 | 3 | | | | | MIR542 | 1.00 |
| 16548 | 3 | | | | | MIR4795 | 1.00 | 16644 | 3 | | | | | MIR543 | 1.00 |
| 16549 | 3 | | | | | MIR4796 | 1.00 | 16645 | 3 | | | | | MIR545 | 1.00 |
| 16550 | 3 | | | | | MIR4797 | 1.00 | 16646 | 3 | | | | | MIR548A1 | 1.00 |
| 16551 | 3 | | | | | MIR4798 | 1.00 | 16647 | 3 | | | | | MIR548A2 | 1.00 |
| 16552 | 3 | | | | | MIR4799 | 1.00 | 16648 | 3 | | | | | MIR548A3 | 1.00 |
| 16553 | 3 | | | | | MIR4800 | 1.00 | 16649 | 3 | | | | | MIR548AA1 | 1.00 |
| 16554 | 3 | | | | | MIR4801 | 1.00 | 16650 | 3 | | | | | MIR548AA2 | 1.00 |
| 16555 | 3 | | | | | MIR4802 | 1.00 | 16651 | 3 | | | | | MIR548AC | 1.00 |
| 16556 | 3 | | | | | MIR4803 | 1.00 | 16652 | 3 | | | | | MIR548AD | 1.00 |
| 16557 | 3 | | | | | MIR4804 | 1.00 | 16653 | 3 | | | | | MIR548AE2 | 1.00 |
| 16558 | 3 | | | | | MIR483 | 1.00 | 16654 | 3 | | | | | MIR548AI | 1.00 |
| 16559 | 3 | | | | | MIR484 | 1.00 | 16655 | 3 | | | | | MIR548AJ2 | 1.00 |
| 16560 | 3 | | | | | MIR485 | 1.00 | 16656 | 3 | | | | | MIR548AL | 1.00 |
| 16561 | 3 | | | | | MIR486 | 1.00 | 16657 | 3 | | | | | MIR548AN | 1.00 |
| 16562 | 3 | | | | | MIR487A | 1.00 | 16658 | 3 | | | | | MIR548B | 1.00 |
| 16563 | 3 | | | | | MIR487B | 1.00 | 16659 | 3 | | | | | MIR548C | 1.00 |
| 16564 | 3 | | | | | MIR488 | 1.00 | 16660 | 3 | | | | | MIR548D2 | 1.00 |
| 16565 | 3 | | | | | MIR489 | 1.00 | 16661 | 3 | | | | | MIR548F1 | 1.00 |
| 16566 | 3 | | | | | MIR490 | 1.00 | 16662 | 3 | | | | | MIR548F2 | 1.00 |
| 16567 | 3 | | | | | MIR491 | 1.00 | 16663 | 3 | | | | | MIR548F3 | 1.00 |
| 16568 | 3 | | | | | MIR492 | 1.00 | 16664 | 3 | | | | | MIR548F4 | 1.00 |
| 16569 | 3 | | | | | MIR493 | 1.00 | 16665 | 3 | | | | | MIR548F5 | 1.00 |
| 16570 | 3 | | | | | MIR494 | 1.00 | 16666 | 3 | | | | | MIR548G | 1.00 |
| 16571 | 3 | | | | | MIR495 | 1.00 | 16667 | 3 | | | | | MIR548H2 | 1.00 |
| 16572 | 3 | | | | | MIR496 | 1.00 | 16668 | 3 | | | | | MIR548H3 | 1.00 |
| 16573 | 3 | | | | | MIR497 | 1.00 | 16669 | 3 | | | | | MIR548H4 | 1.00 |
| 16574 | 3 | | | | | MIR497HG | 1.00 | 16670 | 3 | | | | | MIR548I1 | 1.00 |
| 16575 | 3 | | | | | MIR498 | 1.00 | 16671 | 3 | | | | | MIR548I2 | 1.00 |
| 16576 | 3 | | | | | MIR499A | 1.00 | 16672 | 3 | | | | | MIR548I3 | 1.00 |
| 16577 | 3 | | | | | MIR499B | 1.00 | 16673 | 3 | | | | | MIR548I4 | 1.00 |
| 16578 | 3 | | | | | MIR500A | 1.00 | 16674 | 3 | | | | | MIR548J | 1.00 |
| 16579 | 3 | | | | | MIR500B | 1.00 | 16675 | 3 | | | | | MIR548K | 1.00 |
| 16580 | 3 | | | | | MIR501 | 1.00 | 16676 | 3 | | | | | MIR548M | 1.00 |
| 16581 | 3 | | | | | MIR502 | 1.00 | 16677 | 3 | | | | | MIR548N | 1.00 |
| 16582 | 3 | | | | | MIR503 | 1.00 | 16678 | 3 | | | | | MIR548O2 | 1.00 |
| 16583 | 3 | | | | | MIR504 | 1.00 | 16679 | 3 | | | | | MIR548Q | 1.00 |
| 16584 | 3 | | | | | MIR5047 | 1.00 | 16680 | 3 | | | | | MIR548T | 1.00 |
| 16585 | 3 | | | | | MIR505 | 1.00 | 16681 | 3 | | | | | MIR548W | 1.00 |
| 16586 | 3 | | | | | MIR506 | 1.00 | 16682 | 3 | | | | | MIR548X | 1.00 |
| 16587 | 3 | | | | | MIR507 | 1.00 | 16683 | 3 | | | | | MIR548Y | 1.00 |
| 16588 | 3 | | | | | MIR508 | 1.00 | 16684 | 3 | | | | | MIR549 | 1.00 |
| 16589 | 3 | | | | | MIR509-1 | 1.00 | 16685 | 3 | | | | | MIR550A3 | 1.00 |
| 16590 | 3 | | | | | MIR509-2 | 1.00 | 16686 | 3 | | | | | MIR550B1 | 1.00 |
| 16591 | 3 | | | | | MIR509-3 | 1.00 | 16687 | 3 | | | | | MIR550B2 | 1.00 |
| 16592 | 3 | | | | | MIR5095 | 1.00 | 16688 | 3 | | | | | MIR551A | 1.00 |
| 16593 | 3 | | | | | MIR510 | 1.00 | 16689 | 3 | | | | | MIR551B | 1.00 |
| 16594 | 3 | | | | | MIR511-2 | 1.00 | 16690 | 3 | | | | | MIR553 | 1.00 |
| 16595 | 3 | | | | | MIR512-1 | 1.00 | 16691 | 3 | | | | | MIR554 | 1.00 |
| 16596 | 3 | | | | | MIR512-2 | 1.00 | 16692 | 3 | | | | | MIR555 | 1.00 |
| 16597 | 3 | | | | | MIR514A1 | 1.00 | 16693 | 3 | | | | | MIR556 | 1.00 |
| 16598 | 3 | | | | | MIR514A3 | 1.00 | 16694 | 3 | | | | | MIR557 | 1.00 |
| 16599 | 3 | | | | | MIR514B | 1.00 | 16695 | 3 | | | | | MIR558 | 1.00 |
| 16600 | 3 | | | | | MIR515-1 | 1.00 | 16696 | 3 | | | | | MIR559 | 1.00 |
| 16601 | 3 | | | | | MIR515-2 | 1.00 | 16697 | 3 | | | | | MIR561 | 1.00 |

Fig. 40 - 88

| | | | | | | | | | | | | | | | | |
|---|---|---|---|---|---|---|---|---|---|---|---|---|---|---|---|---|
| 16698 | 3 | | | | | MIR563 | 1.00 | 16794 | 3 | | | | | MIR759 | 1.00 |
| 16699 | 3 | | | | | MIR564 | 1.00 | 16795 | 3 | | | | | MIR760 | 1.00 |
| 16700 | 3 | | | | | MIR567 | 1.00 | 16796 | 3 | | | | | MIR761 | 1.00 |
| 16701 | 3 | | | | | MIR568 | 1.00 | 16797 | 3 | | | | | MIR762 | 1.00 |
| 16702 | 3 | | | | | MIR569 | 1.00 | 16798 | 3 | | | | | MIR764 | 1.00 |
| 16703 | 3 | | | | | MIR572 | 1.00 | 16799 | 3 | | | | | MIR765 | 1.00 |
| 16704 | 3 | | | | | MIR574 | 1.00 | 16800 | 3 | | | | | MIR766 | 1.00 |
| 16705 | 3 | | | | | MIR575 | 1.00 | 16801 | 3 | | | | | MIR767 | 1.00 |
| 16706 | 3 | | | | | MIR577 | 1.00 | 16802 | 3 | | | | | MIR769 | 1.00 |
| 16707 | 3 | | | | | MIR578 | 1.00 | 16803 | 3 | | | | | MIR770 | 1.00 |
| 16708 | 3 | | | | | MIR580 | 1.00 | 16804 | 3 | | | | | MIR802 | 1.00 |
| 16709 | 3 | | | | | MIR581 | 1.00 | 16805 | 3 | | | | | MIR873 | 1.00 |
| 16710 | 3 | | | | | MIR583 | 1.00 | 16806 | 3 | | | | | MIR874 | 1.00 |
| 16711 | 3 | | | | | MIR585 | 1.00 | 16807 | 3 | | | | | MIR875 | 1.00 |
| 16712 | 3 | | | | | MIR586 | 1.00 | 16808 | 3 | | | | | MIR876 | 1.00 |
| 16713 | 3 | | | | | MIR589 | 1.00 | 16809 | 3 | | | | | MIR877 | 1.00 |
| 16714 | 3 | | | | | MIR590 | 1.00 | 16810 | 3 | | | | | MIR885 | 1.00 |
| 16715 | 3 | | | | | MIR591 | 1.00 | 16811 | 3 | | | | | MIR888 | 1.00 |
| 16716 | 3 | | | | | MIR592 | 1.00 | 16812 | 3 | | | | | MIR889 | 1.00 |
| 16717 | 3 | | | | | MIR593 | 1.00 | 16813 | 3 | | | | | MIR890 | 1.00 |
| 16718 | 3 | | | | | MIR595 | 1.00 | 16814 | 3 | | | | | MIR891A | 1.00 |
| 16719 | 3 | | | | | MIR596 | 1.00 | 16815 | 3 | | | | | MIR891B | 1.00 |
| 16720 | 3 | | | | | MIR597 | 1.00 | 16816 | 3 | | | | | MIR892A | 1.00 |
| 16721 | 3 | | | | | MIR598 | 1.00 | 16817 | 3 | | | | | MIR892B | 1.00 |
| 16722 | 3 | | | | | MIR599 | 1.00 | 16818 | 3 | | | | | MIR9-1 | 1.00 |
| 16723 | 3 | | | | | MIR600 | 1.00 | 16819 | 3 | | | | | MIR9-2 | 1.00 |
| 16724 | 3 | | | | | MIR601 | 1.00 | 16820 | 3 | | | | | MIR9-3 | 1.00 |
| 16725 | 3 | | | | | MIR602 | 1.00 | 16821 | 3 | | | | | MIR920 | 1.00 |
| 16726 | 3 | | | | | MIR603 | 1.00 | 16822 | 3 | | | | | MIR921 | 1.00 |
| 16727 | 3 | | | | | MIR604 | 1.00 | 16823 | 3 | | | | | MIR922 | 1.00 |
| 16728 | 3 | | | | | MIR605 | 1.00 | 16824 | 3 | | | | | MIR92A1 | 1.00 |
| 16729 | 3 | | | | | MIR608 | 1.00 | 16825 | 3 | | | | | MIR92A2 | 1.00 |
| 16730 | 3 | | | | | MIR609 | 1.00 | 16826 | 3 | | | | | MIR92B | 1.00 |
| 16731 | 3 | | | | | MIR610 | 1.00 | 16827 | 3 | | | | | MIR93 | 1.00 |
| 16732 | 3 | | | | | MIR611 | 1.00 | 16828 | 3 | | | | | MIR933 | 1.00 |
| 16733 | 3 | | | | | MIR612 | 1.00 | 16829 | 3 | | | | | MIR934 | 1.00 |
| 16734 | 3 | | | | | MIR613 | 1.00 | 16830 | 3 | | | | | MIR935 | 1.00 |
| 16735 | 3 | | | | | MIR614 | 1.00 | 16831 | 3 | | | | | MIR936 | 1.00 |
| 16736 | 3 | | | | | MIR615 | 1.00 | 16832 | 3 | | | | | MIR937 | 1.00 |
| 16737 | 3 | | | | | MIR617 | 1.00 | 16833 | 3 | | | | | MIR938 | 1.00 |
| 16738 | 3 | | | | | MIR618 | 1.00 | 16834 | 3 | | | | | MIR939 | 1.00 |
| 16739 | 3 | | | | | MIR620 | 1.00 | 16835 | 3 | | | | | MIR940 | 1.00 |
| 16740 | 3 | | | | | MIR621 | 1.00 | 16836 | 3 | | | | | MIR941-1 | 1.00 |
| 16741 | 3 | | | | | MIR622 | 1.00 | 16837 | 3 | | | | | MIR941-2 | 1.00 |
| 16742 | 3 | | | | | MIR623 | 1.00 | 16838 | 3 | | | | | MIR941-3 | 1.00 |
| 16743 | 3 | | | | | MIR624 | 1.00 | 16839 | 3 | | | | | MIR941-4 | 1.00 |
| 16744 | 3 | | | | | MIR626 | 1.00 | 16840 | 3 | | | | | MIR942 | 1.00 |
| 16745 | 3 | | | | | MIR627 | 1.00 | 16841 | 3 | | | | | MIR943 | 1.00 |
| 16746 | 3 | | | | | MIR628 | 1.00 | 16842 | 3 | | | | | MIR944 | 1.00 |
| 16747 | 3 | | | | | MIR629 | 1.00 | 16843 | 3 | | | | | MIR96 | 1.00 |
| 16748 | 3 | | | | | MIR630 | 1.00 | 16844 | 3 | | | | | MIR98 | 1.00 |
| 16749 | 3 | | | | | MIR631 | 1.00 | 16845 | 3 | | | | | MIR99A | 1.00 |
| 16750 | 3 | | | | | MIR632 | 1.00 | 16846 | 3 | | | | | MIR99B | 1.00 |
| 16751 | 3 | | | | | MIR634 | 1.00 | 16847 | 3 | | | | | MIRLET7A1 | 1.00 |
| 16752 | 3 | | | | | MIR635 | 1.00 | 16848 | 3 | | | | | MIRLET7A2 | 1.00 |
| 16753 | 3 | | | | | MIR636 | 1.00 | 16849 | 3 | | | | | MIRLET7A3 | 1.00 |
| 16754 | 3 | | | | | MIR637 | 1.00 | 16850 | 3 | | | | | MIRLET7B | 1.00 |
| 16755 | 3 | | | | | MIR638 | 1.00 | 16851 | 3 | | | | | MIRLET7C | 1.00 |
| 16756 | 3 | | | | | MIR639 | 1.00 | 16852 | 3 | | | | | MIRLET7D | 1.00 |
| 16757 | 3 | | | | | MIR641 | 1.00 | 16853 | 3 | | | | | MIRLET7E | 1.00 |
| 16758 | 3 | | | | | MIR642A | 1.00 | 16854 | 3 | | | | | MIRLET7F1 | 1.00 |
| 16759 | 3 | | | | | MIR642B | 1.00 | 16855 | 3 | | | | | MIRLET7F2 | 1.00 |
| 16760 | 3 | | | | | MIR643 | 1.00 | 16856 | 3 | | | | | MIRLET7G | 1.00 |
| 16761 | 3 | | | | | MIR644A | 1.00 | 16857 | 3 | | | | | MIRLET7I | 1.00 |
| 16762 | 3 | | | | | MIR645 | 1.00 | 16858 | 3 | | | | | MIXL1 | 1.00 |
| 16763 | 3 | | | | | MIR647 | 1.00 | 16859 | 3 | | | | | MKRN3 | 1.00 |
| 16764 | 3 | | | | | MIR648 | 1.00 | 16860 | 3 | | | | | MKRN7P | 1.00 |
| 16765 | 3 | | | | | MIR650 | 1.00 | 16861 | 3 | | | | | MKX | 1.00 |
| 16766 | 3 | | | | | MIR651 | 1.00 | 16862 | 3 | | | | | MLANA | 1.00 |
| 16767 | 3 | | | | | MIR653 | 1.00 | 16863 | 3 | | | | | MLF1 | 1.00 |
| 16768 | 3 | | | | | MIR654 | 1.00 | 16864 | 3 | | | | | MLF1IP | 1.00 |
| 16769 | 3 | | | | | MIR655 | 1.00 | 16865 | 3 | | | | | MLIP | 1.00 |
| 16770 | 3 | | | | | MIR656 | 1.00 | 16866 | 3 | | | | | MLK7-AS1 | 1.00 |
| 16771 | 3 | | | | | MIR657 | 1.00 | 16867 | 3 | | | | | MLLT10P1 | 1.00 |
| 16772 | 3 | | | | | MIR658 | 1.00 | 16868 | 3 | | | | | MLLT4-AS1 | 1.00 |
| 16773 | 3 | | | | | MIR659 | 1.00 | 16869 | 3 | | | | | MLN | 1.00 |
| 16774 | 3 | | | | | MIR660 | 1.00 | 16870 | 3 | | | | | MLNR | 1.00 |
| 16775 | 3 | | | | | MIR661 | 1.00 | 16871 | 3 | | | | | MLPH | 1.00 |
| 16776 | 3 | | | | | MIR662 | 1.00 | 16872 | 3 | | | | | MLXIPL | 1.00 |
| 16777 | 3 | | | | | MIR663A | 1.00 | 16873 | 3 | | | | | MMAB | 1.00 |
| 16778 | 3 | | | | | MIR663B | 1.00 | 16874 | 3 | | | | | MMD2 | 1.00 |
| 16779 | 3 | | | | | MIR664 | 1.00 | 16875 | 3 | | | | | MMEL1 | 1.00 |
| 16780 | 3 | | | | | MIR665 | 1.00 | 16876 | 3 | | | | | MMP1 | 1.00 |
| 16781 | 3 | | | | | MIR668 | 1.00 | 16877 | 3 | | | | | MMP10 | 1.00 |
| 16782 | 3 | | | | | MIR670 | 1.00 | 16878 | 3 | | | | | MMP11 | 1.00 |
| 16783 | 3 | | | | | MIR671 | 1.00 | 16879 | 3 | | | | | MMP12 | 1.00 |
| 16784 | 3 | | | | | MIR675 | 1.00 | 16880 | 3 | | | | | MMP13 | 1.00 |
| 16785 | 3 | | | | | MIR676 | 1.00 | 16881 | 3 | | | | | MMP15 | 1.00 |
| 16786 | 3 | | | | | MIR7-2 | 1.00 | 16882 | 3 | | | | | MMP16 | 1.00 |
| 16787 | 3 | | | | | MIR7-3 | 1.00 | 16883 | 3 | | | | | MMP19 | 1.00 |
| 16788 | 3 | | | | | MIR7-3HG | 1.00 | 16884 | 3 | | | | | MMP2 | 1.00 |
| 16789 | 3 | | | | | MIR708 | 1.00 | 16885 | 3 | | | | | MMP20 | 1.00 |
| 16790 | 3 | | | | | MIR711 | 1.00 | 16886 | 3 | | | | | MMP21 | 1.00 |
| 16791 | 3 | | | | | MIR718 | 1.00 | 16887 | 3 | | | | | MMP23A | 1.00 |
| 16792 | 3 | | | | | MIR744 | 1.00 | 16888 | 3 | | | | | MMP23B | 1.00 |
| 16793 | 3 | | | | | MIR758 | 1.00 | 16889 | 3 | | | | | MMP26 | 1.00 |

Fig. 40 - 89

| | | | | | | | | | | | | | | | |
|---|---|---|---|---|---|---|---|---|---|---|---|---|---|---|---|
| 16890 | 3 | | | | | MMP27 | 1.00 | 16986 | 3 | | | | | MUC12 | 1.00 |
| 16891 | 3 | | | | | MMP3 | 1.00 | 16987 | 3 | | | | | MUC13 | 1.00 |
| 16892 | 3 | | | | | MMP7 | 1.00 | 16988 | 3 | | | | | MUC15 | 1.00 |
| 16893 | 3 | | | | | MMRN2 | 1.00 | 16989 | 3 | | | | | MUC16 | 1.00 |
| 16894 | 3 | | | | | MN1 | 1.00 | 16990 | 3 | | | | | MUC17 | 1.00 |
| 16895 | 3 | | | | | MND1 | 1.00 | 16991 | 3 | | | | | MUC2 | 1.00 |
| 16896 | 3 | | | | | MNS1 | 1.00 | 16992 | 3 | | | | | MUC20 | 1.00 |
| 16897 | 3 | | | | | MNX1 | 1.00 | 16993 | 3 | | | | | MUC21 | 1.00 |
| 16898 | 3 | | | | | MOBP | 1.00 | 16994 | 3 | | | | | MUC22 | 1.00 |
| 16899 | 3 | | | | | MOCOS | 1.00 | 16995 | 3 | | | | | MUC4 | 1.00 |
| 16900 | 3 | | | | | MOCS1 | 1.00 | 16996 | 3 | | | | | MUC5B | 1.00 |
| 16901 | 3 | | | | | MOG | 1.00 | 16997 | 3 | | | | | MUC6 | 1.00 |
| 16902 | 3 | | | | | MOGAT1 | 1.00 | 16998 | 3 | | | | | MUC7 | 1.00 |
| 16903 | 3 | | | | | MOGAT2 | 1.00 | 16999 | 3 | | | | | MUCL1 | 1.00 |
| 16904 | 3 | | | | | MOGAT3 | 1.00 | 17000 | 3 | | | | | MUM1L1 | 1.00 |
| 16905 | 3 | | | | | MOK | 1.00 | 17001 | 3 | | | | | MURC | 1.00 |
| 16906 | 3 | | | | | MORC1 | 1.00 | 17002 | 3 | | | | | MUSK | 1.00 |
| 16907 | 3 | | | | | MORN1 | 1.00 | 17003 | 3 | | | | | MXRA5 | 1.00 |
| 16908 | 3 | | | | | MORN4 | 1.00 | 17004 | 3 | | | | | MYADML | 1.00 |
| 16909 | 3 | | | | | MORN5 | 1.00 | 17005 | 3 | | | | | MYADML2 | 1.00 |
| 16910 | 3 | | | | | MOS | 1.00 | 17006 | 3 | | | | | MYBPC1 | 1.00 |
| 16911 | 3 | | | | | MOV10L1 | 1.00 | 17007 | 3 | | | | | MYBPC2 | 1.00 |
| 16912 | 3 | | | | | MOXD1 | 1.00 | 17008 | 3 | | | | | MYBPH | 1.00 |
| 16913 | 3 | | | | | MOXD2P | 1.00 | 17009 | 3 | | | | | MYBPHL | 1.00 |
| 16914 | 3 | | | | | MPDZ | 1.00 | 17010 | 3 | | | | | MYCBPAP | 1.00 |
| 16915 | 3 | | | | | MPP2 | 1.00 | 17011 | 3 | | | | | MYCN | 1.00 |
| 16916 | 3 | | | | | MPP3 | 1.00 | 17012 | 3 | | | | | MYCNOS | 1.00 |
| 16917 | 3 | | | | | MPP4 | 1.00 | 17013 | 3 | | | | | MYEF2 | 1.00 |
| 16918 | 3 | | | | | MPP6 | 1.00 | 17014 | 3 | | | | | MYF5 | 1.00 |
| 16919 | 3 | | | | | MPPED1 | 1.00 | 17015 | 3 | | | | | MYF6 | 1.00 |
| 16920 | 3 | | | | | MPPED2 | 1.00 | 17016 | 3 | | | | | MYH1 | 1.00 |
| 16921 | 3 | | | | | MPV17L | 1.00 | 17017 | 3 | | | | | MYH10 | 1.00 |
| 16922 | 3 | | | | | MRAP | 1.00 | 17018 | 3 | | | | | MYH13 | 1.00 |
| 16923 | 3 | | | | | MRAP2 | 1.00 | 17019 | 3 | | | | | MYH14 | 1.00 |
| 16924 | 3 | | | | | MRC1 | 1.00 | 17020 | 3 | | | | | MYH15 | 1.00 |
| 16925 | 3 | | | | | MRGPRD | 1.00 | 17021 | 3 | | | | | MYH16 | 1.00 |
| 16926 | 3 | | | | | MRGPRE | 1.00 | 17022 | 3 | | | | | MYH2 | 1.00 |
| 16927 | 3 | | | | | MRGPRF | 1.00 | 17023 | 3 | | | | | MYH4 | 1.00 |
| 16928 | 3 | | | | | MRGPRG | 1.00 | 17024 | 3 | | | | | MYH6 | 1.00 |
| 16929 | 3 | | | | | MRGPRX1 | 1.00 | 17025 | 3 | | | | | MYH7 | 1.00 |
| 16930 | 3 | | | | | MRGPRX2 | 1.00 | 17026 | 3 | | | | | MYH7B | 1.00 |
| 16931 | 3 | | | | | MRGPRX3 | 1.00 | 17027 | 3 | | | | | MYH8 | 1.00 |
| 16932 | 3 | | | | | MRGPRX4 | 1.00 | 17028 | 3 | | | | | MYL1 | 1.00 |
| 16933 | 3 | | | | | MRO | 1.00 | 17029 | 3 | | | | | MYL10 | 1.00 |
| 16934 | 3 | | | | | MRPL23-AS1 | 1.00 | 17030 | 3 | | | | | MYL2 | 1.00 |
| 16935 | 3 | | | | | MRPL45P2 | 1.00 | 17031 | 3 | | | | | MYL3 | 1.00 |
| 16936 | 3 | | | | | MS4A10 | 1.00 | 17032 | 3 | | | | | MYL5 | 1.00 |
| 16937 | 3 | | | | | MS4A12 | 1.00 | 17033 | 3 | | | | | MYL7 | 1.00 |
| 16938 | 3 | | | | | MS4A13 | 1.00 | 17034 | 3 | | | | | MYLK-AS1 | 1.00 |
| 16939 | 3 | | | | | MS4A15 | 1.00 | 17035 | 3 | | | | | MYLK2 | 1.00 |
| 16940 | 3 | | | | | MS4A5 | 1.00 | 17036 | 3 | | | | | MYLK3 | 1.00 |
| 16941 | 3 | | | | | MS4A6E | 1.00 | 17037 | 3 | | | | | MYLK4 | 1.00 |
| 16942 | 3 | | | | | MS4A8B | 1.00 | 17038 | 3 | | | | | MYLPF | 1.00 |
| 16943 | 3 | | | | | MSGN1 | 1.00 | 17039 | 3 | | | | | MYO10 | 1.00 |
| 16944 | 3 | | | | | MSH4 | 1.00 | 17040 | 3 | | | | | MYO15A | 1.00 |
| 16945 | 3 | | | | | MSH5 | 1.00 | 17041 | 3 | | | | | MYO16 | 1.00 |
| 16946 | 3 | | | | | MSI1 | 1.00 | 17042 | 3 | | | | | MYO18B | 1.00 |
| 16947 | 3 | | | | | MSLN | 1.00 | 17043 | 3 | | | | | MYO1A | 1.00 |
| 16948 | 3 | | | | | MSLNL | 1.00 | 17044 | 3 | | | | | MYO1B | 1.00 |
| 16949 | 3 | | | | | MSMB | 1.00 | 17045 | 3 | | | | | MYO1H | 1.00 |
| 16950 | 3 | | | | | MST1 | 1.00 | 17046 | 3 | | | | | MYO3A | 1.00 |
| 16951 | 3 | | | | | MST1P2 | 1.00 | 17047 | 3 | | | | | MYO3B | 1.00 |
| 16952 | 3 | | | | | MST1P9 | 1.00 | 17048 | 3 | | | | | MYO5B | 1.00 |
| 16953 | 3 | | | | | MST1R | 1.00 | 17049 | 3 | | | | | MYO5C | 1.00 |
| 16954 | 3 | | | | | MSTN | 1.00 | 17050 | 3 | | | | | MYO6 | 1.00 |
| 16955 | 3 | | | | | MSX1 | 1.00 | 17051 | 3 | | | | | MYO7A | 1.00 |
| 16956 | 3 | | | | | MSX2 | 1.00 | 17052 | 3 | | | | | MYOC | 1.00 |
| 16957 | 3 | | | | | MT1A | 1.00 | 17053 | 3 | | | | | MYOCD | 1.00 |
| 16958 | 3 | | | | | MT1B | 1.00 | 17054 | 3 | | | | | MYOD1 | 1.00 |
| 16959 | 3 | | | | | MT1DP | 1.00 | 17055 | 3 | | | | | MYOG | 1.00 |
| 16960 | 3 | | | | | MT1G | 1.00 | 17056 | 3 | | | | | MYOM3 | 1.00 |
| 16961 | 3 | | | | | MT1H | 1.00 | 17057 | 3 | | | | | MYOT | 1.00 |
| 16962 | 3 | | | | | MT1IP | 1.00 | 17058 | 3 | | | | | MYOZ1 | 1.00 |
| 16963 | 3 | | | | | MT1JP | 1.00 | 17059 | 3 | | | | | MYOZ2 | 1.00 |
| 16964 | 3 | | | | | MT1L | 1.00 | 17060 | 3 | | | | | MYOZ3 | 1.00 |
| 16965 | 3 | | | | | MT1M | 1.00 | 17061 | 3 | | | | | MYPN | 1.00 |
| 16966 | 3 | | | | | MT3 | 1.00 | 17062 | 3 | | | | | MYRIP | 1.00 |
| 16967 | 3 | | | | | MT4 | 1.00 | 17063 | 3 | | | | | MYT1 | 1.00 |
| 16968 | 3 | | | | | MTBP | 1.00 | 17064 | 3 | | | | | MYT1L | 1.00 |
| 16969 | 3 | | | | | MTHFD1L | 1.00 | 17065 | 3 | | | | | NAA11 | 1.00 |
| 16970 | 3 | | | | | MTMR7 | 1.00 | 17066 | 3 | | | | | NAALAD2 | 1.00 |
| 16971 | 3 | | | | | MTMR8 | 1.00 | 17067 | 3 | | | | | NAALADL2 | 1.00 |
| 16972 | 3 | | | | | MTMR9LP | 1.00 | 17068 | 3 | | | | | NACAD | 1.00 |
| 16973 | 3 | | | | | MTNR1A | 1.00 | 17069 | 3 | | | | | NALCN | 1.00 |
| 16974 | 3 | | | | | MTNR1B | 1.00 | 17070 | 3 | | | | | NANOG | 1.00 |
| 16975 | 3 | | | | | MTRNR2L10 | 1.00 | 17071 | 3 | | | | | NANOGNB | 1.00 |
| 16976 | 3 | | | | | MTRNR2L3 | 1.00 | 17072 | 3 | | | | | NANOS2 | 1.00 |
| 16977 | 3 | | | | | MTRNR2L4 | 1.00 | 17073 | 3 | | | | | NANOS3 | 1.00 |
| 16978 | 3 | | | | | MTRNR2L5 | 1.00 | 17074 | 3 | | | | | NAP1L6 | 1.00 |
| 16979 | 3 | | | | | MTRNR2L6 | 1.00 | 17075 | 3 | | | | | NAT16 | 1.00 |
| 16980 | 3 | | | | | MTRNR2L7 | 1.00 | 17076 | 3 | | | | | NAT2 | 1.00 |
| 16981 | 3 | | | | | MTSS1L | 1.00 | 17077 | 3 | | | | | NAT8 | 1.00 |
| 16982 | 3 | | | | | MTTP | 1.00 | 17078 | 3 | | | | | NAT8L | 1.00 |
| 16983 | 3 | | | | | MTUS2 | 1.00 | 17079 | 3 | | | | | NAV2 | 1.00 |
| 16984 | 3 | | | | | MTVR2 | 1.00 | 17080 | 3 | | | | | NAV2-AS4 | 1.00 |
| 16985 | 3 | | | | | MUC1 | 1.00 | 17081 | 3 | | | | | NAV3 | 1.00 |

Fig. 40 - 90

| | | | | | | | | | | | | | | | | | |
|---|---|---|---|---|---|---|---|---|---|---|---|---|---|---|---|---|---|
| 17082 | 3 | | | | | | NBEA | 1.00 | 17178 | 3 | | | | | | NLRP11 | 1.00 |
| 17083 | 3 | | | | | | NBEAL1 | 1.00 | 17179 | 3 | | | | | | NLRP13 | 1.00 |
| 17084 | 3 | | | | | | NBEAP1 | 1.00 | 17180 | 3 | | | | | | NLRP14 | 1.00 |
| 17085 | 3 | | | | | | NBL1 | 1.00 | 17181 | 3 | | | | | | NLRP4 | 1.00 |
| 17086 | 3 | | | | | | NBLA00301 | 1.00 | 17182 | 3 | | | | | | NLRP5 | 1.00 |
| 17087 | 3 | | | | | | NBPF22P | 1.00 | 17183 | 3 | | | | | | NLRP7 | 1.00 |
| 17088 | 3 | | | | | | NBPF4 | 1.00 | 17184 | 3 | | | | | | NLRP8 | 1.00 |
| 17089 | 3 | | | | | | NBPF6 | 1.00 | 17185 | 3 | | | | | | NLRP9 | 1.00 |
| 17090 | 3 | | | | | | NBPF7 | 1.00 | 17186 | 3 | | | | | | NMBR | 1.00 |
| 17091 | 3 | | | | | | NCAM2 | 1.00 | 17187 | 3 | | | | | | NME1-NME2 | 1.00 |
| 17092 | 3 | | | | | | NCAN | 1.00 | 17188 | 3 | | | | | | NME5 | 1.00 |
| 17093 | 3 | | | | | | NCAPG | 1.00 | 17189 | 3 | | | | | | NME9 | 1.00 |
| 17094 | 3 | | | | | | NCAPG2 | 1.00 | 17190 | 3 | | | | | | NMNAT2 | 1.00 |
| 17095 | 3 | | | | | | NCAPH | 1.00 | 17191 | 3 | | | | | | NMS | 1.00 |
| 17096 | 3 | | | | | | NCCRP1 | 1.00 | 17192 | 3 | | | | | | NMU | 1.00 |
| 17097 | 3 | | | | | | NCKAP1 | 1.00 | 17193 | 3 | | | | | | NMUR2 | 1.00 |
| 17098 | 3 | | | | | | NCKAP5 | 1.00 | 17194 | 3 | | | | | | NNMT | 1.00 |
| 17099 | 3 | | | | | | NCOR1P1 | 1.00 | 17195 | 3 | | | | | | NOBOX | 1.00 |
| 17100 | 3 | | | | | | NCR2 | 1.00 | 17196 | 3 | | | | | | NODAL | 1.00 |
| 17101 | 3 | | | | | | NCRNA00185 | 1.00 | 17197 | 3 | | | | | | NOL4 | 1.00 |
| 17102 | 3 | | | | | | NCRUPAR | 1.00 | 17198 | 3 | | | | | | NOS1 | 1.00 |
| 17103 | 3 | | | | | | NCS1 | 1.00 | 17199 | 3 | | | | | | NOS1AP | 1.00 |
| 17104 | 3 | | | | | | NDFIP2 | 1.00 | 17200 | 3 | | | | | | NOS2 | 1.00 |
| 17105 | 3 | | | | | | NDNF | 1.00 | 17201 | 3 | | | | | | NOS3 | 1.00 |
| 17106 | 3 | | | | | | NDP | 1.00 | 17202 | 3 | | | | | | NOSTRIN | 1.00 |
| 17107 | 3 | | | | | | NDRG4 | 1.00 | 17203 | 3 | | | | | | NOTCH3 | 1.00 |
| 17108 | 3 | | | | | | NDST3 | 1.00 | 17204 | 3 | | | | | | NOTCH4 | 1.00 |
| 17109 | 3 | | | | | | NDST4 | 1.00 | 17205 | 3 | | | | | | NOTO | 1.00 |
| 17110 | 3 | | | | | | NDUFA4L2 | 1.00 | 17206 | 3 | | | | | | NOTUM | 1.00 |
| 17111 | 3 | | | | | | NEB | 1.00 | 17207 | 3 | | | | | | NOVA1 | 1.00 |
| 17112 | 3 | | | | | | NECAB1 | 1.00 | 17208 | 3 | | | | | | NOVA2 | 1.00 |
| 17113 | 3 | | | | | | NEDD4L | 1.00 | 17209 | 3 | | | | | | NOX1 | 1.00 |
| 17114 | 3 | | | | | | NEFM | 1.00 | 17210 | 3 | | | | | | NOX3 | 1.00 |
| 17115 | 3 | | | | | | NEGR1 | 1.00 | 17211 | 3 | | | | | | NOX4 | 1.00 |
| 17116 | 3 | | | | | | NEGR1-IT1 | 1.00 | 17212 | 3 | | | | | | NOX5 | 1.00 |
| 17117 | 3 | | | | | | NEIL3 | 1.00 | 17213 | 3 | | | | | | NOXO1 | 1.00 |
| 17118 | 3 | | | | | | NEK10 | 1.00 | 17214 | 3 | | | | | | NOXRED1 | 1.00 |
| 17119 | 3 | | | | | | NEK11 | 1.00 | 17215 | 3 | | | | | | NPAS1 | 1.00 |
| 17120 | 3 | | | | | | NEK2 | 1.00 | 17216 | 3 | | | | | | NPAS2 | 1.00 |
| 17121 | 3 | | | | | | NEK5 | 1.00 | 17217 | 3 | | | | | | NPAS3 | 1.00 |
| 17122 | 3 | | | | | | NELL1 | 1.00 | 17218 | 3 | | | | | | NPAS4 | 1.00 |
| 17123 | 3 | | | | | | NES | 1.00 | 17219 | 3 | | | | | | NPB | 1.00 |
| 17124 | 3 | | | | | | NETO1 | 1.00 | 17220 | 3 | | | | | | NPBWR2 | 1.00 |
| 17125 | 3 | | | | | | NEU2 | 1.00 | 17221 | 3 | | | | | | NPC1L1 | 1.00 |
| 17126 | 3 | | | | | | NEU4 | 1.00 | 17222 | 3 | | | | | | NPFFR1 | 1.00 |
| 17127 | 3 | | | | | | NEURL1B | 1.00 | 17223 | 3 | | | | | | NPFFR2 | 1.00 |
| 17128 | 3 | | | | | | NEURL2 | 1.00 | 17224 | 3 | | | | | | NPHP1 | 1.00 |
| 17129 | 3 | | | | | | NEURL3 | 1.00 | 17225 | 3 | | | | | | NPHP3-AS1 | 1.00 |
| 17130 | 3 | | | | | | NEUROD1 | 1.00 | 17226 | 3 | | | | | | NPHS1 | 1.00 |
| 17131 | 3 | | | | | | NEUROD2 | 1.00 | 17227 | 3 | | | | | | NPHS2 | 1.00 |
| 17132 | 3 | | | | | | NEUROD4 | 1.00 | 17228 | 3 | | | | | | NPM2 | 1.00 |
| 17133 | 3 | | | | | | NEUROD6 | 1.00 | 17229 | 3 | | | | | | NPNT | 1.00 |
| 17134 | 3 | | | | | | NEUROG1 | 1.00 | 17230 | 3 | | | | | | NPPB | 1.00 |
| 17135 | 3 | | | | | | NEUROG2 | 1.00 | 17231 | 3 | | | | | | NPPC | 1.00 |
| 17136 | 3 | | | | | | NEUROG3 | 1.00 | 17232 | 3 | | | | | | NPR1 | 1.00 |
| 17137 | 3 | | | | | | NF1P2 | 1.00 | 17233 | 3 | | | | | | NPR2 | 1.00 |
| 17138 | 3 | | | | | | NFASC | 1.00 | 17234 | 3 | | | | | | NPR3 | 1.00 |
| 17139 | 3 | | | | | | NFATC4 | 1.00 | 17235 | 3 | | | | | | NPS | 1.00 |
| 17140 | 3 | | | | | | NFIB | 1.00 | 17236 | 3 | | | | | | NPSR1 | 1.00 |
| 17141 | 3 | | | | | | NGB | 1.00 | 17237 | 3 | | | | | | NPTX1 | 1.00 |
| 17142 | 3 | | | | | | NGEF | 1.00 | 17238 | 3 | | | | | | NPTX2 | 1.00 |
| 17143 | 3 | | | | | | NGF | 1.00 | 17239 | 3 | | | | | | NPVF | 1.00 |
| 17144 | 3 | | | | | | NGFR | 1.00 | 17240 | 3 | | | | | | NPW | 1.00 |
| 17145 | 3 | | | | | | NHEG1 | 1.00 | 17241 | 3 | | | | | | NPY | 1.00 |
| 17146 | 3 | | | | | | NHLH1 | 1.00 | 17242 | 3 | | | | | | NPY1R | 1.00 |
| 17147 | 3 | | | | | | NHLH2 | 1.00 | 17243 | 3 | | | | | | NPY2R | 1.00 |
| 17148 | 3 | | | | | | NID2 | 1.00 | 17244 | 3 | | | | | | NPY5R | 1.00 |
| 17149 | 3 | | | | | | NIM1 | 1.00 | 17245 | 3 | | | | | | NPY6R | 1.00 |
| 17150 | 3 | | | | | | NINL | 1.00 | 17246 | 3 | | | | | | NQO1 | 1.00 |
| 17151 | 3 | | | | | | NIPAL1 | 1.00 | 17247 | 3 | | | | | | NR0B1 | 1.00 |
| 17152 | 3 | | | | | | NIPAL4 | 1.00 | 17248 | 3 | | | | | | NR0B2 | 1.00 |
| 17153 | 3 | | | | | | NIPSNAP3B | 1.00 | 17249 | 3 | | | | | | NR1H4 | 1.00 |
| 17154 | 3 | | | | | | NKAIN1 | 1.00 | 17250 | 3 | | | | | | NR1I2 | 1.00 |
| 17155 | 3 | | | | | | NKAIN2 | 1.00 | 17251 | 3 | | | | | | NR1I3 | 1.00 |
| 17156 | 3 | | | | | | NKAIN3 | 1.00 | 17252 | 3 | | | | | | NR2E1 | 1.00 |
| 17157 | 3 | | | | | | NKAIN4 | 1.00 | 17253 | 3 | | | | | | NR2E3 | 1.00 |
| 17158 | 3 | | | | | | NKAPP1 | 1.00 | 17254 | 3 | | | | | | NR2F1 | 1.00 |
| 17159 | 3 | | | | | | NKD1 | 1.00 | 17255 | 3 | | | | | | NR2F2 | 1.00 |
| 17160 | 3 | | | | | | NKD2 | 1.00 | 17256 | 3 | | | | | | NR4A3 | 1.00 |
| 17161 | 3 | | | | | | NKPD1 | 1.00 | 17257 | 3 | | | | | | NR5A1 | 1.00 |
| 17162 | 3 | | | | | | NKX1-2 | 1.00 | 17258 | 3 | | | | | | NR5A2 | 1.00 |
| 17163 | 3 | | | | | | NKX2-1 | 1.00 | 17259 | 3 | | | | | | NRAP | 1.00 |
| 17164 | 3 | | | | | | NKX2-2 | 1.00 | 17260 | 3 | | | | | | NRARP | 1.00 |
| 17165 | 3 | | | | | | NKX2-3 | 1.00 | 17261 | 3 | | | | | | NRCAM | 1.00 |
| 17166 | 3 | | | | | | NKX2-4 | 1.00 | 17262 | 3 | | | | | | NRG2 | 1.00 |
| 17167 | 3 | | | | | | NKX2-5 | 1.00 | 17263 | 3 | | | | | | NRG3 | 1.00 |
| 17168 | 3 | | | | | | NKX2-6 | 1.00 | 17264 | 3 | | | | | | NRIP3 | 1.00 |
| 17169 | 3 | | | | | | NKX2-8 | 1.00 | 17265 | 3 | | | | | | NRK | 1.00 |
| 17170 | 3 | | | | | | NKX3-2 | 1.00 | 17266 | 3 | | | | | | NRON | 1.00 |
| 17171 | 3 | | | | | | NKX6-1 | 1.00 | 17267 | 3 | | | | | | NRP2 | 1.00 |
| 17172 | 3 | | | | | | NKX6-2 | 1.00 | 17268 | 3 | | | | | | NRSN1 | 1.00 |
| 17173 | 3 | | | | | | NKX6-3 | 1.00 | 17269 | 3 | | | | | | NRTN | 1.00 |
| 17174 | 3 | | | | | | NLGN1 | 1.00 | 17270 | 3 | | | | | | NRXN1 | 1.00 |
| 17175 | 3 | | | | | | NLGN4X | 1.00 | 17271 | 3 | | | | | | NRXN2 | 1.00 |
| 17176 | 3 | | | | | | NLGN4Y | 1.00 | 17272 | 3 | | | | | | NRXN3 | 1.00 |
| 17177 | 3 | | | | | | NLRP10 | 1.00 | 17273 | 3 | | | | | | NT5C1A | 1.00 |

Fig. 40 - 91

| | | | | | | | | | | | | | | | |
|---|---|---|---|---|---|---|---|---|---|---|---|---|---|---|---|
| 17274 | 3 | | | | | NT5C1B | 1.00 | 17370 | 3 | | | | | OR10A7 | 1.00 |
| 17275 | 3 | | | | | NT5C1B-RDH14 | 1.00 | 17371 | 3 | | | | | OR10AD1 | 1.00 |
| 17276 | 3 | | | | | NTF3 | 1.00 | 17372 | 3 | | | | | OR10AG1 | 1.00 |
| 17277 | 3 | | | | | NTF4 | 1.00 | 17373 | 3 | | | | | OR10C1 | 1.00 |
| 17278 | 3 | | | | | NTM | 1.00 | 17374 | 3 | | | | | OR10G3 | 1.00 |
| 17279 | 3 | | | | | NTN1 | 1.00 | 17375 | 3 | | | | | OR10G4 | 1.00 |
| 17280 | 3 | | | | | NTN3 | 1.00 | 17376 | 3 | | | | | OR10G7 | 1.00 |
| 17281 | 3 | | | | | NTN4 | 1.00 | 17377 | 3 | | | | | OR10G8 | 1.00 |
| 17282 | 3 | | | | | NTN5 | 1.00 | 17378 | 3 | | | | | OR10G9 | 1.00 |
| 17283 | 3 | | | | | NTNG1 | 1.00 | 17379 | 3 | | | | | OR10H1 | 1.00 |
| 17284 | 3 | | | | | NTRK1 | 1.00 | 17380 | 3 | | | | | OR10H2 | 1.00 |
| 17285 | 3 | | | | | NTRK2 | 1.00 | 17381 | 3 | | | | | OR10H3 | 1.00 |
| 17286 | 3 | | | | | NTRK3 | 1.00 | 17382 | 3 | | | | | OR10H4 | 1.00 |
| 17287 | 3 | | | | | NTS | 1.00 | 17383 | 3 | | | | | OR10H5 | 1.00 |
| 17288 | 3 | | | | | NTSR2 | 1.00 | 17384 | 3 | | | | | OR10J1 | 1.00 |
| 17289 | 3 | | | | | NUAK1 | 1.00 | 17385 | 3 | | | | | OR10J3 | 1.00 |
| 17290 | 3 | | | | | NUDT10 | 1.00 | 17386 | 3 | | | | | OR10J5 | 1.00 |
| 17291 | 3 | | | | | NUDT11 | 1.00 | 17387 | 3 | | | | | OR10K1 | 1.00 |
| 17292 | 3 | | | | | NUDT12 | 1.00 | 17388 | 3 | | | | | OR10K2 | 1.00 |
| 17293 | 3 | | | | | NUDT8 | 1.00 | 17389 | 3 | | | | | OR10P1 | 1.00 |
| 17294 | 3 | | | | | NUDT9P1 | 1.00 | 17390 | 3 | | | | | OR10Q1 | 1.00 |
| 17295 | 3 | | | | | NUF2 | 1.00 | 17391 | 3 | | | | | OR10R2 | 1.00 |
| 17296 | 3 | | | | | NUP210L | 1.00 | 17392 | 3 | | | | | OR10S1 | 1.00 |
| 17297 | 3 | | | | | NUP210P1 | 1.00 | 17393 | 3 | | | | | OR10T2 | 1.00 |
| 17298 | 3 | | | | | NUP62CL | 1.00 | 17394 | 3 | | | | | OR10V1 | 1.00 |
| 17299 | 3 | | | | | NUPR1 | 1.00 | 17395 | 3 | | | | | OR10W1 | 1.00 |
| 17300 | 3 | | | | | NWD1 | 1.00 | 17396 | 3 | | | | | OR10X1 | 1.00 |
| 17301 | 3 | | | | | NXF2 | 1.00 | 17397 | 3 | | | | | OR10Z1 | 1.00 |
| 17302 | 3 | | | | | NXF2B | 1.00 | 17398 | 3 | | | | | OR11A1 | 1.00 |
| 17303 | 3 | | | | | NXF3 | 1.00 | 17399 | 3 | | | | | OR11G2 | 1.00 |
| 17304 | 3 | | | | | NXF4 | 1.00 | 17400 | 3 | | | | | OR11H1 | 1.00 |
| 17305 | 3 | | | | | NXF5 | 1.00 | 17401 | 3 | | | | | OR11H12 | 1.00 |
| 17306 | 3 | | | | | NXN | 1.00 | 17402 | 3 | | | | | OR11H2 | 1.00 |
| 17307 | 3 | | | | | NXNL1 | 1.00 | 17403 | 3 | | | | | OR11H4 | 1.00 |
| 17308 | 3 | | | | | NXNL2 | 1.00 | 17404 | 3 | | | | | OR11H6 | 1.00 |
| 17309 | 3 | | | | | NXPH1 | 1.00 | 17405 | 3 | | | | | OR11L1 | 1.00 |
| 17310 | 3 | | | | | NXPH2 | 1.00 | 17406 | 3 | | | | | OR12D2 | 1.00 |
| 17311 | 3 | | | | | NXPH3 | 1.00 | 17407 | 3 | | | | | OR12D3 | 1.00 |
| 17312 | 3 | | | | | NYAP1 | 1.00 | 17408 | 3 | | | | | OR13A1 | 1.00 |
| 17313 | 3 | | | | | NYAP2 | 1.00 | 17409 | 3 | | | | | OR13C2 | 1.00 |
| 17314 | 3 | | | | | NYNRIN | 1.00 | 17410 | 3 | | | | | OR13C3 | 1.00 |
| 17315 | 3 | | | | | NYX | 1.00 | 17411 | 3 | | | | | OR13C4 | 1.00 |
| 17316 | 3 | | | | | O3FAR1 | 1.00 | 17412 | 3 | | | | | OR13C5 | 1.00 |
| 17317 | 3 | | | | | OBP2A | 1.00 | 17413 | 3 | | | | | OR13C8 | 1.00 |
| 17318 | 3 | | | | | OBP2B | 1.00 | 17414 | 3 | | | | | OR13C9 | 1.00 |
| 17319 | 3 | | | | | OBSL1 | 1.00 | 17415 | 3 | | | | | OR13D1 | 1.00 |
| 17320 | 3 | | | | | OC90 | 1.00 | 17416 | 3 | | | | | OR13F1 | 1.00 |
| 17321 | 3 | | | | | OCA2 | 1.00 | 17417 | 3 | | | | | OR13G1 | 1.00 |
| 17322 | 3 | | | | | OCLN | 1.00 | 17418 | 3 | | | | | OR13H1 | 1.00 |
| 17323 | 3 | | | | | OCM2 | 1.00 | 17419 | 3 | | | | | OR13J1 | 1.00 |
| 17324 | 3 | | | | | ODAM | 1.00 | 17420 | 3 | | | | | OR14A16 | 1.00 |
| 17325 | 3 | | | | | ODF1 | 1.00 | 17421 | 3 | | | | | OR14C36 | 1.00 |
| 17326 | 3 | | | | | ODF3 | 1.00 | 17422 | 3 | | | | | OR14I1 | 1.00 |
| 17327 | 3 | | | | | ODF3L1 | 1.00 | 17423 | 3 | | | | | OR14J1 | 1.00 |
| 17328 | 3 | | | | | ODF3L2 | 1.00 | 17424 | 3 | | | | | OR1A1 | 1.00 |
| 17329 | 3 | | | | | ODF4 | 1.00 | 17425 | 3 | | | | | OR1A2 | 1.00 |
| 17330 | 3 | | | | | ODZ1 | 1.00 | 17426 | 3 | | | | | OR1B1 | 1.00 |
| 17331 | 3 | | | | | ODZ2 | 1.00 | 17427 | 3 | | | | | OR1C1 | 1.00 |
| 17332 | 3 | | | | | ODZ3 | 1.00 | 17428 | 3 | | | | | OR1D2 | 1.00 |
| 17333 | 3 | | | | | ODZ4 | 1.00 | 17429 | 3 | | | | | OR1D4 | 1.00 |
| 17334 | 3 | | | | | OGDHL | 1.00 | 17430 | 3 | | | | | OR1D5 | 1.00 |
| 17335 | 3 | | | | | OGN | 1.00 | 17431 | 3 | | | | | OR1E1 | 1.00 |
| 17336 | 3 | | | | | OIP5 | 1.00 | 17432 | 3 | | | | | OR1E2 | 1.00 |
| 17337 | 3 | | | | | OIT3 | 1.00 | 17433 | 3 | | | | | OR1F1 | 1.00 |
| 17338 | 3 | | | | | OLAH | 1.00 | 17434 | 3 | | | | | OR1F2P | 1.00 |
| 17339 | 3 | | | | | OLFM3 | 1.00 | 17435 | 3 | | | | | OR1G1 | 1.00 |
| 17340 | 3 | | | | | OLFML1 | 1.00 | 17436 | 3 | | | | | OR1I1 | 1.00 |
| 17341 | 3 | | | | | OLFML2A | 1.00 | 17437 | 3 | | | | | OR1J1 | 1.00 |
| 17342 | 3 | | | | | OLFML2B | 1.00 | 17438 | 3 | | | | | OR1J2 | 1.00 |
| 17343 | 3 | | | | | OLFML3 | 1.00 | 17439 | 3 | | | | | OR1J4 | 1.00 |
| 17344 | 3 | | | | | OLIG3 | 1.00 | 17440 | 3 | | | | | OR1K1 | 1.00 |
| 17345 | 3 | | | | | OLR1 | 1.00 | 17441 | 3 | | | | | OR1L1 | 1.00 |
| 17346 | 3 | | | | | OMD | 1.00 | 17442 | 3 | | | | | OR1L3 | 1.00 |
| 17347 | 3 | | | | | OMP | 1.00 | 17443 | 3 | | | | | OR1L4 | 1.00 |
| 17348 | 3 | | | | | ONECUT1 | 1.00 | 17444 | 3 | | | | | OR1L6 | 1.00 |
| 17349 | 3 | | | | | ONECUT2 | 1.00 | 17445 | 3 | | | | | OR1L8 | 1.00 |
| 17350 | 3 | | | | | ONECUT3 | 1.00 | 17446 | 3 | | | | | OR1M1 | 1.00 |
| 17351 | 3 | | | | | OOEP | 1.00 | 17447 | 3 | | | | | OR1N1 | 1.00 |
| 17352 | 3 | | | | | OPALIN | 1.00 | 17448 | 3 | | | | | OR1N2 | 1.00 |
| 17353 | 3 | | | | | OPCML | 1.00 | 17449 | 3 | | | | | OR1Q1 | 1.00 |
| 17354 | 3 | | | | | OPHN1 | 1.00 | 17450 | 3 | | | | | OR1S1 | 1.00 |
| 17355 | 3 | | | | | OPN1LW | 1.00 | 17451 | 3 | | | | | OR1S2 | 1.00 |
| 17356 | 3 | | | | | OPN1MW | 1.00 | 17452 | 3 | | | | | OR2A1 | 1.00 |
| 17357 | 3 | | | | | OPN1MW2 | 1.00 | 17453 | 3 | | | | | OR2A12 | 1.00 |
| 17358 | 3 | | | | | OPN1SW | 1.00 | 17454 | 3 | | | | | OR2A14 | 1.00 |
| 17359 | 3 | | | | | OPN4 | 1.00 | 17455 | 3 | | | | | OR2A2 | 1.00 |
| 17360 | 3 | | | | | OPN5 | 1.00 | 17456 | 3 | | | | | OR2A25 | 1.00 |
| 17361 | 3 | | | | | OPRD1 | 1.00 | 17457 | 3 | | | | | OR2A4 | 1.00 |
| 17362 | 3 | | | | | OPRK1 | 1.00 | 17458 | 3 | | | | | OR2A42 | 1.00 |
| 17363 | 3 | | | | | OPRM1 | 1.00 | 17459 | 3 | | | | | OR2A5 | 1.00 |
| 17364 | 3 | | | | | OPTC | 1.00 | 17460 | 3 | | | | | OR2A7 | 1.00 |
| 17365 | 3 | | | | | OR10A2 | 1.00 | 17461 | 3 | | | | | OR2AE1 | 1.00 |
| 17366 | 3 | | | | | OR10A3 | 1.00 | 17462 | 3 | | | | | OR2AG1 | 1.00 |
| 17367 | 3 | | | | | OR10A4 | 1.00 | 17463 | 3 | | | | | OR2AG2 | 1.00 |
| 17368 | 3 | | | | | OR10A5 | 1.00 | 17464 | 3 | | | | | OR2AK2 | 1.00 |
| 17369 | 3 | | | | | OR10A6 | 1.00 | 17465 | 3 | | | | | OR2AT4 | 1.00 |

Fig. 40 - 92

| | | | | | | | | | | | | | | | | |
|---|---|---|---|---|---|---|---|---|---|---|---|---|---|---|---|---|
| 17466 | 3 | | | | | OR2B11 | 1.00 | | 17562 | 3 | | | | | OR4N5 | 1.00 |
| 17467 | 3 | | | | | OR2B2 | 1.00 | | 17563 | 3 | | | | | OR4P4 | 1.00 |
| 17468 | 3 | | | | | OR2B3 | 1.00 | | 17564 | 3 | | | | | OR4Q3 | 1.00 |
| 17469 | 3 | | | | | OR2C1 | 1.00 | | 17565 | 3 | | | | | OR4S1 | 1.00 |
| 17470 | 3 | | | | | OR2C3 | 1.00 | | 17566 | 3 | | | | | OR4S2 | 1.00 |
| 17471 | 3 | | | | | OR2D2 | 1.00 | | 17567 | 3 | | | | | OR4X1 | 1.00 |
| 17472 | 3 | | | | | OR2D3 | 1.00 | | 17568 | 3 | | | | | OR4X2 | 1.00 |
| 17473 | 3 | | | | | OR2F1 | 1.00 | | 17569 | 3 | | | | | OR51A2 | 1.00 |
| 17474 | 3 | | | | | OR2F2 | 1.00 | | 17570 | 3 | | | | | OR51A4 | 1.00 |
| 17475 | 3 | | | | | OR2G2 | 1.00 | | 17571 | 3 | | | | | OR51A7 | 1.00 |
| 17476 | 3 | | | | | OR2G3 | 1.00 | | 17572 | 3 | | | | | OR51B2 | 1.00 |
| 17477 | 3 | | | | | OR2G6 | 1.00 | | 17573 | 3 | | | | | OR51B4 | 1.00 |
| 17478 | 3 | | | | | OR2H1 | 1.00 | | 17574 | 3 | | | | | OR51B5 | 1.00 |
| 17479 | 3 | | | | | OR2H2 | 1.00 | | 17575 | 3 | | | | | OR51B6 | 1.00 |
| 17480 | 3 | | | | | OR2J2 | 1.00 | | 17576 | 3 | | | | | OR51D1 | 1.00 |
| 17481 | 3 | | | | | OR2J3 | 1.00 | | 17577 | 3 | | | | | OR51E1 | 1.00 |
| 17482 | 3 | | | | | OR2K2 | 1.00 | | 17578 | 3 | | | | | OR51E2 | 1.00 |
| 17483 | 3 | | | | | OR2L13 | 1.00 | | 17579 | 3 | | | | | OR51F1 | 1.00 |
| 17484 | 3 | | | | | OR2L1P | 1.00 | | 17580 | 3 | | | | | OR51F2 | 1.00 |
| 17485 | 3 | | | | | OR2L2 | 1.00 | | 17581 | 3 | | | | | OR51G1 | 1.00 |
| 17486 | 3 | | | | | OR2L3 | 1.00 | | 17582 | 3 | | | | | OR51G2 | 1.00 |
| 17487 | 3 | | | | | OR2L8 | 1.00 | | 17583 | 3 | | | | | OR51I1 | 1.00 |
| 17488 | 3 | | | | | OR2M1P | 1.00 | | 17584 | 3 | | | | | OR51I2 | 1.00 |
| 17489 | 3 | | | | | OR2M2 | 1.00 | | 17585 | 3 | | | | | OR51L1 | 1.00 |
| 17490 | 3 | | | | | OR2M3 | 1.00 | | 17586 | 3 | | | | | OR51M1 | 1.00 |
| 17491 | 3 | | | | | OR2M4 | 1.00 | | 17587 | 3 | | | | | OR51Q1 | 1.00 |
| 17492 | 3 | | | | | OR2M5 | 1.00 | | 17588 | 3 | | | | | OR51S1 | 1.00 |
| 17493 | 3 | | | | | OR2M7 | 1.00 | | 17589 | 3 | | | | | OR51T1 | 1.00 |
| 17494 | 3 | | | | | OR2S2 | 1.00 | | 17590 | 3 | | | | | OR51V1 | 1.00 |
| 17495 | 3 | | | | | OR2T1 | 1.00 | | 17591 | 3 | | | | | OR52A1 | 1.00 |
| 17496 | 3 | | | | | OR2T10 | 1.00 | | 17592 | 3 | | | | | OR52A5 | 1.00 |
| 17497 | 3 | | | | | OR2T11 | 1.00 | | 17593 | 3 | | | | | OR52B2 | 1.00 |
| 17498 | 3 | | | | | OR2T12 | 1.00 | | 17594 | 3 | | | | | OR52B4 | 1.00 |
| 17499 | 3 | | | | | OR2T2 | 1.00 | | 17595 | 3 | | | | | OR52B6 | 1.00 |
| 17500 | 3 | | | | | OR2T27 | 1.00 | | 17596 | 3 | | | | | OR52D1 | 1.00 |
| 17501 | 3 | | | | | OR2T29 | 1.00 | | 17597 | 3 | | | | | OR52E2 | 1.00 |
| 17502 | 3 | | | | | OR2T3 | 1.00 | | 17598 | 3 | | | | | OR52E4 | 1.00 |
| 17503 | 3 | | | | | OR2T33 | 1.00 | | 17599 | 3 | | | | | OR52E6 | 1.00 |
| 17504 | 3 | | | | | OR2T34 | 1.00 | | 17600 | 3 | | | | | OR52E8 | 1.00 |
| 17505 | 3 | | | | | OR2T35 | 1.00 | | 17601 | 3 | | | | | OR52H1 | 1.00 |
| 17506 | 3 | | | | | OR2T4 | 1.00 | | 17602 | 3 | | | | | OR52I1 | 1.00 |
| 17507 | 3 | | | | | OR2T5 | 1.00 | | 17603 | 3 | | | | | OR52I2 | 1.00 |
| 17508 | 3 | | | | | OR2T6 | 1.00 | | 17604 | 3 | | | | | OR52J3 | 1.00 |
| 17509 | 3 | | | | | OR2T8 | 1.00 | | 17605 | 3 | | | | | OR52K2 | 1.00 |
| 17510 | 3 | | | | | OR2V2 | 1.00 | | 17606 | 3 | | | | | OR52L1 | 1.00 |
| 17511 | 3 | | | | | OR2W1 | 1.00 | | 17607 | 3 | | | | | OR52M1 | 1.00 |
| 17512 | 3 | | | | | OR2W5 | 1.00 | | 17608 | 3 | | | | | OR52N1 | 1.00 |
| 17513 | 3 | | | | | OR2Y1 | 1.00 | | 17609 | 3 | | | | | OR52N2 | 1.00 |
| 17514 | 3 | | | | | OR2Z1 | 1.00 | | 17610 | 3 | | | | | OR52N4 | 1.00 |
| 17515 | 3 | | | | | OR3A1 | 1.00 | | 17611 | 3 | | | | | OR52N5 | 1.00 |
| 17516 | 3 | | | | | OR3A2 | 1.00 | | 17612 | 3 | | | | | OR52R1 | 1.00 |
| 17517 | 3 | | | | | OR3A3 | 1.00 | | 17613 | 3 | | | | | OR52W1 | 1.00 |
| 17518 | 3 | | | | | OR3A4P | 1.00 | | 17614 | 3 | | | | | OR56A1 | 1.00 |
| 17519 | 3 | | | | | OR4A15 | 1.00 | | 17615 | 3 | | | | | OR56A3 | 1.00 |
| 17520 | 3 | | | | | OR4A16 | 1.00 | | 17616 | 3 | | | | | OR56A4 | 1.00 |
| 17521 | 3 | | | | | OR4A47 | 1.00 | | 17617 | 3 | | | | | OR56A5 | 1.00 |
| 17522 | 3 | | | | | OR4A5 | 1.00 | | 17618 | 3 | | | | | OR56B1 | 1.00 |
| 17523 | 3 | | | | | OR4B1 | 1.00 | | 17619 | 3 | | | | | OR56B4 | 1.00 |
| 17524 | 3 | | | | | OR4C11 | 1.00 | | 17620 | 3 | | | | | OR5A1 | 1.00 |
| 17525 | 3 | | | | | OR4C12 | 1.00 | | 17621 | 3 | | | | | OR5A2 | 1.00 |
| 17526 | 3 | | | | | OR4C13 | 1.00 | | 17622 | 3 | | | | | OR5AC2 | 1.00 |
| 17527 | 3 | | | | | OR4C15 | 1.00 | | 17623 | 3 | | | | | OR5AK2 | 1.00 |
| 17528 | 3 | | | | | OR4C16 | 1.00 | | 17624 | 3 | | | | | OR5AK4P | 1.00 |
| 17529 | 3 | | | | | OR4C3 | 1.00 | | 17625 | 3 | | | | | OR5AN1 | 1.00 |
| 17530 | 3 | | | | | OR4C45 | 1.00 | | 17626 | 3 | | | | | OR5AP2 | 1.00 |
| 17531 | 3 | | | | | OR4C46 | 1.00 | | 17627 | 3 | | | | | OR5AR1 | 1.00 |
| 17532 | 3 | | | | | OR4C6 | 1.00 | | 17628 | 3 | | | | | OR5AS1 | 1.00 |
| 17533 | 3 | | | | | OR4D1 | 1.00 | | 17629 | 3 | | | | | OR5AU1 | 1.00 |
| 17534 | 3 | | | | | OR4D10 | 1.00 | | 17630 | 3 | | | | | OR5B12 | 1.00 |
| 17535 | 3 | | | | | OR4D11 | 1.00 | | 17631 | 3 | | | | | OR5B17 | 1.00 |
| 17536 | 3 | | | | | OR4D2 | 1.00 | | 17632 | 3 | | | | | OR5B2 | 1.00 |
| 17537 | 3 | | | | | OR4D5 | 1.00 | | 17633 | 3 | | | | | OR5B21 | 1.00 |
| 17538 | 3 | | | | | OR4D6 | 1.00 | | 17634 | 3 | | | | | OR5B3 | 1.00 |
| 17539 | 3 | | | | | OR4D9 | 1.00 | | 17635 | 3 | | | | | OR5C1 | 1.00 |
| 17540 | 3 | | | | | OR4E2 | 1.00 | | 17636 | 3 | | | | | OR5D13 | 1.00 |
| 17541 | 3 | | | | | OR4F15 | 1.00 | | 17637 | 3 | | | | | OR5D14 | 1.00 |
| 17542 | 3 | | | | | OR4F16 | 1.00 | | 17638 | 3 | | | | | OR5D16 | 1.00 |
| 17543 | 3 | | | | | OR4F17 | 1.00 | | 17639 | 3 | | | | | OR5D18 | 1.00 |
| 17544 | 3 | | | | | OR4F21 | 1.00 | | 17640 | 3 | | | | | OR5E1P | 1.00 |
| 17545 | 3 | | | | | OR4F29 | 1.00 | | 17641 | 3 | | | | | OR5F1 | 1.00 |
| 17546 | 3 | | | | | OR4F4 | 1.00 | | 17642 | 3 | | | | | OR5H1 | 1.00 |
| 17547 | 3 | | | | | OR4F5 | 1.00 | | 17643 | 3 | | | | | OR5H14 | 1.00 |
| 17548 | 3 | | | | | OR4F6 | 1.00 | | 17644 | 3 | | | | | OR5H15 | 1.00 |
| 17549 | 3 | | | | | OR4K1 | 1.00 | | 17645 | 3 | | | | | OR5H2 | 1.00 |
| 17550 | 3 | | | | | OR4K13 | 1.00 | | 17646 | 3 | | | | | OR5H6 | 1.00 |
| 17551 | 3 | | | | | OR4K14 | 1.00 | | 17647 | 3 | | | | | OR5I1 | 1.00 |
| 17552 | 3 | | | | | OR4K15 | 1.00 | | 17648 | 3 | | | | | OR5J2 | 1.00 |
| 17553 | 3 | | | | | OR4K17 | 1.00 | | 17649 | 3 | | | | | OR5K1 | 1.00 |
| 17554 | 3 | | | | | OR4K2 | 1.00 | | 17650 | 3 | | | | | OR5K2 | 1.00 |
| 17555 | 3 | | | | | OR4K5 | 1.00 | | 17651 | 3 | | | | | OR5K3 | 1.00 |
| 17556 | 3 | | | | | OR4L1 | 1.00 | | 17652 | 3 | | | | | OR5K4 | 1.00 |
| 17557 | 3 | | | | | OR4M1 | 1.00 | | 17653 | 3 | | | | | OR5L1 | 1.00 |
| 17558 | 3 | | | | | OR4M2 | 1.00 | | 17654 | 3 | | | | | OR5L2 | 1.00 |
| 17559 | 3 | | | | | OR4N2 | 1.00 | | 17655 | 3 | | | | | OR5M1 | 1.00 |
| 17560 | 3 | | | | | OR4N3P | 1.00 | | 17656 | 3 | | | | | OR5M10 | 1.00 |
| 17561 | 3 | | | | | OR4N4 | 1.00 | | 17657 | 3 | | | | | OR5M11 | 1.00 |

Fig. 40 - 93

| | | | | | | | | | | | | | | |
|---|---|---|---|---|---|---|---|---|---|---|---|---|---|---|
| 17658 | 3 | | | | | | OR5M3 | 1.00 | 17754 | 3 | | | | OSR1 | 1.00 |
| 17659 | 3 | | | | | | OR5M8 | 1.00 | 17755 | 3 | | | | OSR2 | 1.00 |
| 17660 | 3 | | | | | | OR5M9 | 1.00 | 17756 | 3 | | | | OSTBETA | 1.00 |
| 17661 | 3 | | | | | | OR5P2 | 1.00 | 17757 | 3 | | | | OSTN | 1.00 |
| 17662 | 3 | | | | | | OR5P3 | 1.00 | 17758 | 3 | | | | OSTalpha | 1.00 |
| 17663 | 3 | | | | | | OR5R1 | 1.00 | 17759 | 3 | | | | OTC | 1.00 |
| 17664 | 3 | | | | | | OR5T1 | 1.00 | 17760 | 3 | | | | OTOA | 1.00 |
| 17665 | 3 | | | | | | OR5T2 | 1.00 | 17761 | 3 | | | | OTOGL | 1.00 |
| 17666 | 3 | | | | | | OR5T3 | 1.00 | 17762 | 3 | | | | OTOL1 | 1.00 |
| 17667 | 3 | | | | | | OR5V1 | 1.00 | 17763 | 3 | | | | OTOP1 | 1.00 |
| 17668 | 3 | | | | | | OR5W2 | 1.00 | 17764 | 3 | | | | OTOP2 | 1.00 |
| 17669 | 3 | | | | | | OR6A2 | 1.00 | 17765 | 3 | | | | OTOP3 | 1.00 |
| 17670 | 3 | | | | | | OR6B1 | 1.00 | 17766 | 3 | | | | OTOR | 1.00 |
| 17671 | 3 | | | | | | OR6B2 | 1.00 | 17767 | 3 | | | | OTOS | 1.00 |
| 17672 | 3 | | | | | | OR6B3 | 1.00 | 17768 | 3 | | | | OTP | 1.00 |
| 17673 | 3 | | | | | | OR6C1 | 1.00 | 17769 | 3 | | | | OTUB2 | 1.00 |
| 17674 | 3 | | | | | | OR6C2 | 1.00 | 17770 | 3 | | | | OTUD6A | 1.00 |
| 17675 | 3 | | | | | | OR6C3 | 1.00 | 17771 | 3 | | | | OTUD7A | 1.00 |
| 17676 | 3 | | | | | | OR6C4 | 1.00 | 17772 | 3 | | | | OTX2 | 1.00 |
| 17677 | 3 | | | | | | OR6C6 | 1.00 | 17773 | 3 | | | | OTX2OS1 | 1.00 |
| 17678 | 3 | | | | | | OR6C65 | 1.00 | 17774 | 3 | | | | OVCH1 | 1.00 |
| 17679 | 3 | | | | | | OR6C68 | 1.00 | 17775 | 3 | | | | OVCH2 | 1.00 |
| 17680 | 3 | | | | | | OR6C70 | 1.00 | 17776 | 3 | | | | OVGP1 | 1.00 |
| 17681 | 3 | | | | | | OR6C74 | 1.00 | 17777 | 3 | | | | OVOL1 | 1.00 |
| 17682 | 3 | | | | | | OR6C75 | 1.00 | 17778 | 3 | | | | OVOL2 | 1.00 |
| 17683 | 3 | | | | | | OR6C76 | 1.00 | 17779 | 3 | | | | OXCT2 | 1.00 |
| 17684 | 3 | | | | | | OR6F1 | 1.00 | 17780 | 3 | | | | OXGR1 | 1.00 |
| 17685 | 3 | | | | | | OR6K2 | 1.00 | 17781 | 3 | | | | OXT | 1.00 |
| 17686 | 3 | | | | | | OR6K3 | 1.00 | 17782 | 3 | | | | OXTR | 1.00 |
| 17687 | 3 | | | | | | OR6K6 | 1.00 | 17783 | 3 | | | | P2RX2 | 1.00 |
| 17688 | 3 | | | | | | OR6M1 | 1.00 | 17784 | 3 | | | | P2RX3 | 1.00 |
| 17689 | 3 | | | | | | OR6N1 | 1.00 | 17785 | 3 | | | | P2RX5-TAX1BP3 | 1.00 |
| 17690 | 3 | | | | | | OR6N2 | 1.00 | 17786 | 3 | | | | P2RX6 | 1.00 |
| 17691 | 3 | | | | | | OR6P1 | 1.00 | 17787 | 3 | | | | P2RX6P | 1.00 |
| 17692 | 3 | | | | | | OR6Q1 | 1.00 | 17788 | 3 | | | | P2RY4 | 1.00 |
| 17693 | 3 | | | | | | OR6S1 | 1.00 | 17789 | 3 | | | | P4HA2 | 1.00 |
| 17694 | 3 | | | | | | OR6T1 | 1.00 | 17790 | 3 | | | | P4HA3 | 1.00 |
| 17695 | 3 | | | | | | OR6V1 | 1.00 | 17791 | 3 | | | | PABPC1L2A | 1.00 |
| 17696 | 3 | | | | | | OR6W1P | 1.00 | 17792 | 3 | | | | PABPC1L2B | 1.00 |
| 17697 | 3 | | | | | | OR6X1 | 1.00 | 17793 | 3 | | | | PABPC1P2 | 1.00 |
| 17698 | 3 | | | | | | OR6Y1 | 1.00 | 17794 | 3 | | | | PABPC4L | 1.00 |
| 17699 | 3 | | | | | | OR7A10 | 1.00 | 17795 | 3 | | | | PABPC5 | 1.00 |
| 17700 | 3 | | | | | | OR7A17 | 1.00 | 17796 | 3 | | | | PABPN1L | 1.00 |
| 17701 | 3 | | | | | | OR7A5 | 1.00 | 17797 | 3 | | | | PACRG | 1.00 |
| 17702 | 3 | | | | | | OR7C1 | 1.00 | 17798 | 3 | | | | PACSIN3 | 1.00 |
| 17703 | 3 | | | | | | OR7C2 | 1.00 | 17799 | 3 | | | | PADI1 | 1.00 |
| 17704 | 3 | | | | | | OR7D2 | 1.00 | 17800 | 3 | | | | PADI3 | 1.00 |
| 17705 | 3 | | | | | | OR7D4 | 1.00 | 17801 | 3 | | | | PADI6 | 1.00 |
| 17706 | 3 | | | | | | OR7E12P | 1.00 | 17802 | 3 | | | | PAEP | 1.00 |
| 17707 | 3 | | | | | | OR7E14P | 1.00 | 17803 | 3 | | | | PAGE1 | 1.00 |
| 17708 | 3 | | | | | | OR7E156P | 1.00 | 17804 | 3 | | | | PAGE2 | 1.00 |
| 17709 | 3 | | | | | | OR7E24 | 1.00 | 17805 | 3 | | | | PAGE3 | 1.00 |
| 17710 | 3 | | | | | | OR7E2P | 1.00 | 17806 | 3 | | | | PAGE4 | 1.00 |
| 17711 | 3 | | | | | | OR7E37P | 1.00 | 17807 | 3 | | | | PAGE5 | 1.00 |
| 17712 | 3 | | | | | | OR7E5P | 1.00 | 17808 | 3 | | | | PAH | 1.00 |
| 17713 | 3 | | | | | | OR7E91P | 1.00 | 17809 | 3 | | | | PAK3 | 1.00 |
| 17714 | 3 | | | | | | OR7G1 | 1.00 | 17810 | 3 | | | | PAK6 | 1.00 |
| 17715 | 3 | | | | | | OR7G2 | 1.00 | 17811 | 3 | | | | PAK7 | 1.00 |
| 17716 | 3 | | | | | | OR7G3 | 1.00 | 17812 | 3 | | | | PALM | 1.00 |
| 17717 | 3 | | | | | | OR8A1 | 1.00 | 17813 | 3 | | | | PALM2 | 1.00 |
| 17718 | 3 | | | | | | OR8B12 | 1.00 | 17814 | 3 | | | | PALM2-AKAP2 | 1.00 |
| 17719 | 3 | | | | | | OR8B2 | 1.00 | 17815 | 3 | | | | PALM3 | 1.00 |
| 17720 | 3 | | | | | | OR8B3 | 1.00 | 17816 | 3 | | | | PALMD | 1.00 |
| 17721 | 3 | | | | | | OR8B4 | 1.00 | 17817 | 3 | | | | PAMR1 | 1.00 |
| 17722 | 3 | | | | | | OR8B8 | 1.00 | 17818 | 3 | | | | PANK1 | 1.00 |
| 17723 | 3 | | | | | | OR8D1 | 1.00 | 17819 | 3 | | | | PANX3 | 1.00 |
| 17724 | 3 | | | | | | OR8D2 | 1.00 | 17820 | 3 | | | | PAPL | 1.00 |
| 17725 | 3 | | | | | | OR8D4 | 1.00 | 17821 | 3 | | | | PAPLN | 1.00 |
| 17726 | 3 | | | | | | OR8G1 | 1.00 | 17822 | 3 | | | | PAPPA | 1.00 |
| 17727 | 3 | | | | | | OR8G2 | 1.00 | 17823 | 3 | | | | PAPPA2 | 1.00 |
| 17728 | 3 | | | | | | OR8G5 | 1.00 | 17824 | 3 | | | | PAQR5 | 1.00 |
| 17729 | 3 | | | | | | OR8H1 | 1.00 | 17825 | 3 | | | | PAQR9 | 1.00 |
| 17730 | 3 | | | | | | OR8H2 | 1.00 | 17826 | 3 | | | | PAR1 | 1.00 |
| 17731 | 3 | | | | | | OR8H3 | 1.00 | 17827 | 3 | | | | PAR4 | 1.00 |
| 17732 | 3 | | | | | | OR8I2 | 1.00 | 17828 | 3 | | | | PARD3B | 1.00 |
| 17733 | 3 | | | | | | OR8J1 | 1.00 | 17829 | 3 | | | | PARD6B | 1.00 |
| 17734 | 3 | | | | | | OR8J3 | 1.00 | 17830 | 3 | | | | PARD6G | 1.00 |
| 17735 | 3 | | | | | | OR8K1 | 1.00 | 17831 | 3 | | | | PARK2 | 1.00 |
| 17736 | 3 | | | | | | OR8K3 | 1.00 | 17832 | 3 | | | | PARPBP | 1.00 |
| 17737 | 3 | | | | | | OR8K5 | 1.00 | 17833 | 3 | | | | PART1 | 1.00 |
| 17738 | 3 | | | | | | OR8S1 | 1.00 | 17834 | 3 | | | | PARVA | 1.00 |
| 17739 | 3 | | | | | | OR8U1 | 1.00 | 17835 | 3 | | | | PASD1 | 1.00 |
| 17740 | 3 | | | | | | OR8U8 | 1.00 | 17836 | 3 | | | | PATE1 | 1.00 |
| 17741 | 3 | | | | | | OR9A2 | 1.00 | 17837 | 3 | | | | PATE2 | 1.00 |
| 17742 | 3 | | | | | | OR9A4 | 1.00 | 17838 | 3 | | | | PATE3 | 1.00 |
| 17743 | 3 | | | | | | OR9G4 | 1.00 | 17839 | 3 | | | | PATE4 | 1.00 |
| 17744 | 3 | | | | | | OR9G9 | 1.00 | 17840 | 3 | | | | PAWR | 1.00 |
| 17745 | 3 | | | | | | OR9I1 | 1.00 | 17841 | 3 | | | | PAX1 | 1.00 |
| 17746 | 3 | | | | | | OR9K2 | 1.00 | 17842 | 3 | | | | PAX2 | 1.00 |
| 17747 | 3 | | | | | | OR9Q1 | 1.00 | 17843 | 3 | | | | PAX3 | 1.00 |
| 17748 | 3 | | | | | | OR9Q2 | 1.00 | 17844 | 3 | | | | PAX4 | 1.00 |
| 17749 | 3 | | | | | | ORC1 | 1.00 | 17845 | 3 | | | | PAX6 | 1.00 |
| 17750 | 3 | | | | | | ORC6 | 1.00 | 17846 | 3 | | | | PAX7 | 1.00 |
| 17751 | 3 | | | | | | OSBPL6 | 1.00 | 17847 | 3 | | | | PAX8 | 1.00 |
| 17752 | 3 | | | | | | OSCP1 | 1.00 | 17848 | 3 | | | | PAX9 | 1.00 |
| 17753 | 3 | | | | | | OSM R | 1.00 | 17849 | 3 | | | | PBK | 1.00 |

Fig. 40 - 94

| | | | | | | | | | | | | | | | | |
|---|---|---|---|---|---|---|---|---|---|---|---|---|---|---|---|---|
| 17850 | 3 | | | | | | PBOV1 | 1.00 | 17946 | 3 | | | | | PDE6C | 1.00 |
| 17851 | 3 | | | | | | PC | 1.00 | 17947 | 3 | | | | | PDE6H | 1.00 |
| 17852 | 3 | | | | | | PCA3 | 1.00 | 17948 | 3 | | | | | PDE7B | 1.00 |
| 17853 | 3 | | | | | | PCAT1 | 1.00 | 17949 | 3 | | | | | PDE8B | 1.00 |
| 17854 | 3 | | | | | | PCBP3 | 1.00 | 17950 | 3 | | | | | PDGFRA | 1.00 |
| 17855 | 3 | | | | | | PCCA | 1.00 | 17951 | 3 | | | | | PDGFRB | 1.00 |
| 17856 | 3 | | | | | | PCDH10 | 1.00 | 17952 | 3 | | | | | PDGFRL | 1.00 |
| 17857 | 3 | | | | | | PCDH11X | 1.00 | 17953 | 3 | | | | | PDIA2 | 1.00 |
| 17858 | 3 | | | | | | PCDH11Y | 1.00 | 17954 | 3 | | | | | PDIA5 | 1.00 |
| 17859 | 3 | | | | | | PCDH15 | 1.00 | 17955 | 3 | | | | | PDILT | 1.00 |
| 17860 | 3 | | | | | | PCDH17 | 1.00 | 17956 | 3 | | | | | PDLIM3 | 1.00 |
| 17861 | 3 | | | | | | PCDH18 | 1.00 | 17957 | 3 | | | | | PDLIM4 | 1.00 |
| 17862 | 3 | | | | | | PCDH19 | 1.00 | 17958 | 3 | | | | | PDPN | 1.00 |
| 17863 | 3 | | | | | | PCDH20 | 1.00 | 17959 | 3 | | | | | PDX1 | 1.00 |
| 17864 | 3 | | | | | | PCDH7 | 1.00 | 17960 | 3 | | | | | PDYN | 1.00 |
| 17865 | 3 | | | | | | PCDH8 | 1.00 | 17961 | 3 | | | | | PDZD2 | 1.00 |
| 17866 | 3 | | | | | | PCDHA1 | 1.00 | 17962 | 3 | | | | | PDZD3 | 1.00 |
| 17867 | 3 | | | | | | PCDHA10 | 1.00 | 17963 | 3 | | | | | PDZD7 | 1.00 |
| 17868 | 3 | | | | | | PCDHA11 | 1.00 | 17964 | 3 | | | | | PDZD9 | 1.00 |
| 17869 | 3 | | | | | | PCDHA12 | 1.00 | 17965 | 3 | | | | | PDZK1 | 1.00 |
| 17870 | 3 | | | | | | PCDHA13 | 1.00 | 17966 | 3 | | | | | PDZK1P1 | 1.00 |
| 17871 | 3 | | | | | | PCDHA2 | 1.00 | 17967 | 3 | | | | | PDZRN3 | 1.00 |
| 17872 | 3 | | | | | | PCDHA3 | 1.00 | 17968 | 3 | | | | | PDZRN4 | 1.00 |
| 17873 | 3 | | | | | | PCDHA4 | 1.00 | 17969 | 3 | | | | | PEBP4 | 1.00 |
| 17874 | 3 | | | | | | PCDHA5 | 1.00 | 17970 | 3 | | | | | PEG10 | 1.00 |
| 17875 | 3 | | | | | | PCDHA6 | 1.00 | 17971 | 3 | | | | | PEG3 | 1.00 |
| 17876 | 3 | | | | | | PCDHA7 | 1.00 | 17972 | 3 | | | | | PEG3-AS1 | 1.00 |
| 17877 | 3 | | | | | | PCDHA8 | 1.00 | 17973 | 3 | | | | | PENK | 1.00 |
| 17878 | 3 | | | | | | PCDHA9 | 1.00 | 17974 | 3 | | | | | PER4 | 1.00 |
| 17879 | 3 | | | | | | PCDHAC1 | 1.00 | 17975 | 3 | | | | | PEX11G | 1.00 |
| 17880 | 3 | | | | | | PCDHAC2 | 1.00 | 17976 | 3 | | | | | PEX5L | 1.00 |
| 17881 | 3 | | | | | | PCDHB1 | 1.00 | 17977 | 3 | | | | | PFKFB1 | 1.00 |
| 17882 | 3 | | | | | | PCDHB10 | 1.00 | 17978 | 3 | | | | | PFN3 | 1.00 |
| 17883 | 3 | | | | | | PCDHB11 | 1.00 | 17979 | 3 | | | | | PFN4 | 1.00 |
| 17884 | 3 | | | | | | PCDHB12 | 1.00 | 17980 | 3 | | | | | PGA3 | 1.00 |
| 17885 | 3 | | | | | | PCDHB13 | 1.00 | 17981 | 3 | | | | | PGA4 | 1.00 |
| 17886 | 3 | | | | | | PCDHB14 | 1.00 | 17982 | 3 | | | | | PGA5 | 1.00 |
| 17887 | 3 | | | | | | PCDHB15 | 1.00 | 17983 | 3 | | | | | PGBD1 | 1.00 |
| 17888 | 3 | | | | | | PCDHB16 | 1.00 | 17984 | 3 | | | | | PGBD5 | 1.00 |
| 17889 | 3 | | | | | | PCDHB17 | 1.00 | 17985 | 3 | | | | | PGC | 1.00 |
| 17890 | 3 | | | | | | PCDHB18 | 1.00 | 17986 | 3 | | | | | PGCP1 | 1.00 |
| 17891 | 3 | | | | | | PCDHB19P | 1.00 | 17987 | 3 | | | | | PGF | 1.00 |
| 17892 | 3 | | | | | | PCDHB2 | 1.00 | 17988 | 3 | | | | | PGK2 | 1.00 |
| 17893 | 3 | | | | | | PCDHB3 | 1.00 | 17989 | 3 | | | | | PGLYRP2 | 1.00 |
| 17894 | 3 | | | | | | PCDHB4 | 1.00 | 17990 | 3 | | | | | PGLYRP3 | 1.00 |
| 17895 | 3 | | | | | | PCDHB5 | 1.00 | 17991 | 3 | | | | | PGLYRP4 | 1.00 |
| 17896 | 3 | | | | | | PCDHB6 | 1.00 | 17992 | 3 | | | | | PGM5P2 | 1.00 |
| 17897 | 3 | | | | | | PCDHB7 | 1.00 | 17993 | 3 | | | | | PGPEP1L | 1.00 |
| 17898 | 3 | | | | | | PCDHB8 | 1.00 | 17994 | 3 | | | | | PGR | 1.00 |
| 17899 | 3 | | | | | | PCDHB9 | 1.00 | 17995 | 3 | | | | | PHACTR3 | 1.00 |
| 17900 | 3 | | | | | | PCDHGA1 | 1.00 | 17996 | 3 | | | | | PHEX | 1.00 |
| 17901 | 3 | | | | | | PCDHGA10 | 1.00 | 17997 | 3 | | | | | PHF16 | 1.00 |
| 17902 | 3 | | | | | | PCDHGA11 | 1.00 | 17998 | 3 | | | | | PHF21B | 1.00 |
| 17903 | 3 | | | | | | PCDHGA12 | 1.00 | 17999 | 3 | | | | | PHF2P1 | 1.00 |
| 17904 | 3 | | | | | | PCDHGA2 | 1.00 | 18000 | 3 | | | | | PHGR1 | 1.00 |
| 17905 | 3 | | | | | | PCDHGA3 | 1.00 | 18001 | 3 | | | | | PHKA1 | 1.00 |
| 17906 | 3 | | | | | | PCDHGA4 | 1.00 | 18002 | 3 | | | | | PHKG1 | 1.00 |
| 17907 | 3 | | | | | | PCDHGA5 | 1.00 | 18003 | 3 | | | | | PHLDA2 | 1.00 |
| 17908 | 3 | | | | | | PCDHGA6 | 1.00 | 18004 | 3 | | | | | PHLDA3 | 1.00 |
| 17909 | 3 | | | | | | PCDHGA7 | 1.00 | 18005 | 3 | | | | | PHLDB1 | 1.00 |
| 17910 | 3 | | | | | | PCDHGA8 | 1.00 | 18006 | 3 | | | | | PHOSPHO2-KLHL2 3 | 1.00 |
| 17911 | 3 | | | | | | PCDHGA9 | 1.00 | 18007 | 3 | | | | | PHOX2A | 1.00 |
| 17912 | 3 | | | | | | PCDHGB1 | 1.00 | 18008 | 3 | | | | | PHOX2B | 1.00 |
| 17913 | 3 | | | | | | PCDHGB2 | 1.00 | 18009 | 3 | | | | | PHYHD1 | 1.00 |
| 17914 | 3 | | | | | | PCDHGB3 | 1.00 | 18010 | 3 | | | | | PHYHIP | 1.00 |
| 17915 | 3 | | | | | | PCDHGB4 | 1.00 | 18011 | 3 | | | | | PHYHIPL | 1.00 |
| 17916 | 3 | | | | | | PCDHGB5 | 1.00 | 18012 | 3 | | | | | PI15 | 1.00 |
| 17917 | 3 | | | | | | PCDHGB6 | 1.00 | 18013 | 3 | | | | | PI2O2 | 1.00 |
| 17918 | 3 | | | | | | PCDHGB7 | 1.00 | 18014 | 3 | | | | | PIF1 | 1.00 |
| 17919 | 3 | | | | | | PCDHGB8P | 1.00 | 18015 | 3 | | | | | PIGR | 1.00 |
| 17920 | 3 | | | | | | PCDHGC3 | 1.00 | 18016 | 3 | | | | | PIGZ | 1.00 |
| 17921 | 3 | | | | | | PCDHGC4 | 1.00 | 18017 | 3 | | | | | PIH1D2 | 1.00 |
| 17922 | 3 | | | | | | PCDHGC5 | 1.00 | 18018 | 3 | | | | | PIK3C2G | 1.00 |
| 17923 | 3 | | | | | | PCDP1 | 1.00 | 18019 | 3 | | | | | PIP | 1.00 |
| 17924 | 3 | | | | | | PCGEM1 | 1.00 | 18020 | 3 | | | | | PIP5K1P1 | 1.00 |
| 17925 | 3 | | | | | | PCGF2 | 1.00 | 18021 | 3 | | | | | PIP5KL1 | 1.00 |
| 17926 | 3 | | | | | | PCK1 | 1.00 | 18022 | 3 | | | | | PIPOX | 1.00 |
| 17927 | 3 | | | | | | PCLO | 1.00 | 18023 | 3 | | | | | PIR | 1.00 |
| 17928 | 3 | | | | | | PCNAP1 | 1.00 | 18024 | 3 | | | | | PIR-FIGF | 1.00 |
| 17929 | 3 | | | | | | PCOLCE | 1.00 | 18025 | 3 | | | | | PIRT | 1.00 |
| 17930 | 3 | | | | | | PCOLCE2 | 1.00 | 18026 | 3 | | | | | PISRT1 | 1.00 |
| 17931 | 3 | | | | | | PCP4 | 1.00 | 18027 | 3 | | | | | PITPNM3 | 1.00 |
| 17932 | 3 | | | | | | PCSK1 | 1.00 | 18028 | 3 | | | | | PITX1 | 1.00 |
| 17933 | 3 | | | | | | PCSK2 | 1.00 | 18029 | 3 | | | | | PITX2 | 1.00 |
| 17934 | 3 | | | | | | PCSK4 | 1.00 | 18030 | 3 | | | | | PITX3 | 1.00 |
| 17935 | 3 | | | | | | PCSK9 | 1.00 | 18031 | 3 | | | | | PIWIL1 | 1.00 |
| 17936 | 3 | | | | | | PDC | 1.00 | 18032 | 3 | | | | | PIWIL2 | 1.00 |
| 17937 | 3 | | | | | | PDCL2 | 1.00 | 18033 | 3 | | | | | PIWIL3 | 1.00 |
| 17938 | 3 | | | | | | PDE10A | 1.00 | 18034 | 3 | | | | | PIWIL4 | 1.00 |
| 17939 | 3 | | | | | | PDE11A | 1.00 | 18035 | 3 | | | | | PKD1L1 | 1.00 |
| 17940 | 3 | | | | | | PDE1A | 1.00 | 18036 | 3 | | | | | PKD1L2 | 1.00 |
| 17941 | 3 | | | | | | PDE1C | 1.00 | 18037 | 3 | | | | | PKD1L3 | 1.00 |
| 17942 | 3 | | | | | | PDE2A | 1.00 | 18038 | 3 | | | | | PKD2L1 | 1.00 |
| 17943 | 3 | | | | | | PDE3A | 1.00 | 18039 | 3 | | | | | PKD2L2 | 1.00 |
| 17944 | 3 | | | | | | PDE4C | 1.00 | 18040 | 3 | | | | | PKDCC | 1.00 |
| 17945 | 3 | | | | | | PDE6A | 1.00 | | | | | | | | |

Fig. 40 - 95

| | | | | | | | | | | | | | | | |
|---|---|---|---|---|---|---|---|---|---|---|---|---|---|---|---|
| 18041 | 3 | | | | | | PKDREJ | 1.00 | 18137 | 3 | | | | POC1A | 1.00 |
| 18042 | 3 | | | | | | PKHD1 | 1.00 | 18138 | 3 | | | | POC1B-GALNT4 | 1.00 |
| 18043 | 3 | | | | | | PKHD1L1 | 1.00 | 18139 | 3 | | | | PODN | 1.00 |
| 18044 | 3 | | | | | | PKIB | 1.00 | 18140 | 3 | | | | PODNL1 | 1.00 |
| 18045 | 3 | | | | | | PKLR | 1.00 | 18141 | 3 | | | | PODXL | 1.00 |
| 18046 | 3 | | | | | | PKMYT1 | 1.00 | 18142 | 3 | | | | POF1B | 1.00 |
| 18047 | 3 | | | | | | PKN3 | 1.00 | 18143 | 3 | | | | POLE2 | 1.00 |
| 18048 | 3 | | | | | | PKNOX2 | 1.00 | 18144 | 3 | | | | POLN | 1.00 |
| 18049 | 3 | | | | | | PKP1 | 1.00 | 18145 | 3 | | | | POLQ | 1.00 |
| 18050 | 3 | | | | | | PKP2 | 1.00 | 18146 | 3 | | | | POM121L10P | 1.00 |
| 18051 | 3 | | | | | | PKP3 | 1.00 | 18147 | 3 | | | | POM121L12 | 1.00 |
| 18052 | 3 | | | | | | PLA1A | 1.00 | 18148 | 3 | | | | POM121L1P | 1.00 |
| 18053 | 3 | | | | | | PLA2G10 | 1.00 | 18149 | 3 | | | | POM121L2 | 1.00 |
| 18054 | 3 | | | | | | PLA2G12B | 1.00 | 18150 | 3 | | | | POM121L4P | 1.00 |
| 18055 | 3 | | | | | | PLA2G1B | 1.00 | 18151 | 3 | | | | POM121L8P | 1.00 |
| 18056 | 3 | | | | | | PLA2G2A | 1.00 | 18152 | 3 | | | | POM121L9P | 1.00 |
| 18057 | 3 | | | | | | PLA2G2C | 1.00 | 18153 | 3 | | | | PON1 | 1.00 |
| 18058 | 3 | | | | | | PLA2G2D | 1.00 | 18154 | 3 | | | | PON3 | 1.00 |
| 18059 | 3 | | | | | | PLA2G2E | 1.00 | 18155 | 3 | | | | POPDC3 | 1.00 |
| 18060 | 3 | | | | | | PLA2G2F | 1.00 | 18156 | 3 | | | | POSTN | 1.00 |
| 18061 | 3 | | | | | | PLA2G3 | 1.00 | 18157 | 3 | | | | POTEA | 1.00 |
| 18062 | 3 | | | | | | PLA2G4D | 1.00 | 18158 | 3 | | | | POTEB | 1.00 |
| 18063 | 3 | | | | | | PLA2G4E | 1.00 | 18159 | 3 | | | | POTEC | 1.00 |
| 18064 | 3 | | | | | | PLA2G4F | 1.00 | 18160 | 3 | | | | POTED | 1.00 |
| 18065 | 3 | | | | | | PLA2G5 | 1.00 | 18161 | 3 | | | | POTEG | 1.00 |
| 18066 | 3 | | | | | | PLA2R1 | 1.00 | 18162 | 3 | | | | POTEH | 1.00 |
| 18067 | 3 | | | | | | PLAC1 | 1.00 | 18163 | 3 | | | | POU1F1 | 1.00 |
| 18068 | 3 | | | | | | PLAC1L | 1.00 | 18164 | 3 | | | | POU2F3 | 1.00 |
| 18069 | 3 | | | | | | PLAC2 | 1.00 | 18165 | 3 | | | | POU3F1 | 1.00 |
| 18070 | 3 | | | | | | PLAC4 | 1.00 | 18166 | 3 | | | | POU3F2 | 1.00 |
| 18071 | 3 | | | | | | PLAC8L1 | 1.00 | 18167 | 3 | | | | POU3F3 | 1.00 |
| 18072 | 3 | | | | | | PLAC9 | 1.00 | 18168 | 3 | | | | POU3F4 | 1.00 |
| 18073 | 3 | | | | | | PLAT | 1.00 | 18169 | 3 | | | | POU4F1 | 1.00 |
| 18074 | 3 | | | | | | PLAU | 1.00 | 18170 | 3 | | | | POU4F2 | 1.00 |
| 18075 | 3 | | | | | | PLCB4 | 1.00 | 18171 | 3 | | | | POU4F3 | 1.00 |
| 18076 | 3 | | | | | | PLCD4 | 1.00 | 18172 | 3 | | | | POU5F1P4 | 1.00 |
| 18077 | 3 | | | | | | PLCE1 | 1.00 | 18173 | 3 | | | | POU5F2 | 1.00 |
| 18078 | 3 | | | | | | PLCH1 | 1.00 | 18174 | 3 | | | | POU6F2 | 1.00 |
| 18079 | 3 | | | | | | PLCXD3 | 1.00 | 18175 | 3 | | | | PP12613 | 1.00 |
| 18080 | 3 | | | | | | PLCZ1 | 1.00 | 18176 | 3 | | | | PP14571 | 1.00 |
| 18081 | 3 | | | | | | PLD5 | 1.00 | 18177 | 3 | | | | PP2D1 | 1.00 |
| 18082 | 3 | | | | | | PLEKHA4 | 1.00 | 18178 | 3 | | | | PPAN-P2RY11 | 1.00 |
| 18083 | 3 | | | | | | PLEKHA5 | 1.00 | 18179 | 3 | | | | PPAP2B | 1.00 |
| 18084 | 3 | | | | | | PLEKHA6 | 1.00 | 18180 | 3 | | | | PPAP2C | 1.00 |
| 18085 | 3 | | | | | | PLEKHA7 | 1.00 | 18181 | 3 | | | | PPAPDC1A | 1.00 |
| 18086 | 3 | | | | | | PLEKHD1 | 1.00 | 18182 | 3 | | | | PPAPDC3 | 1.00 |
| 18087 | 3 | | | | | | PLEKHG4B | 1.00 | 18183 | 3 | | | | PPARG | 1.00 |
| 18088 | 3 | | | | | | PLEKHG5 | 1.00 | 18184 | 3 | | | | PPARGC1A | 1.00 |
| 18089 | 3 | | | | | | PLEKHG6 | 1.00 | 18185 | 3 | | | | PPBPL2 | 1.00 |
| 18090 | 3 | | | | | | PLEKHG7 | 1.00 | 18186 | 3 | | | | PPEF1 | 1.00 |
| 18091 | 3 | | | | | | PLEKHH1 | 1.00 | 18187 | 3 | | | | PPEF2 | 1.00 |
| 18092 | 3 | | | | | | PLEKHH2 | 1.00 | 18188 | 3 | | | | PPFIA2 | 1.00 |
| 18093 | 3 | | | | | | PLEKHH3 | 1.00 | 18189 | 3 | | | | PPFIA3 | 1.00 |
| 18094 | 3 | | | | | | PLEKHN1 | 1.00 | 18190 | 3 | | | | PPFIA4 | 1.00 |
| 18095 | 3 | | | | | | PLG | 1.00 | 18191 | 3 | | | | PPFIBP1 | 1.00 |
| 18096 | 3 | | | | | | PLGLB2 | 1.00 | 18192 | 3 | | | | PPIAL4B | 1.00 |
| 18097 | 3 | | | | | | PLIN1 | 1.00 | 18193 | 3 | | | | PPIAL4C | 1.00 |
| 18098 | 3 | | | | | | PLK2 | 1.00 | 18194 | 3 | | | | PPIAL4E | 1.00 |
| 18099 | 3 | | | | | | PLK4 | 1.00 | 18195 | 3 | | | | PPIAL4G | 1.00 |
| 18100 | 3 | | | | | | PLK5 | 1.00 | 18196 | 3 | | | | PPIC | 1.00 |
| 18101 | 3 | | | | | | PLN | 1.00 | 18197 | 3 | | | | PPIH | 1.00 |
| 18102 | 3 | | | | | | PLOD2 | 1.00 | 18198 | 3 | | | | PPIL6 | 1.00 |
| 18103 | 3 | | | | | | PLP1 | 1.00 | 18199 | 3 | | | | PPM1E | 1.00 |
| 18104 | 3 | | | | | | PLS1 | 1.00 | 18200 | 3 | | | | PPM1J | 1.00 |
| 18105 | 3 | | | | | | PLS3 | 1.00 | 18201 | 3 | | | | PPP1R13L | 1.00 |
| 18106 | 3 | | | | | | PLSCR2 | 1.00 | 18202 | 3 | | | | PPP1R14C | 1.00 |
| 18107 | 3 | | | | | | PLSCR4 | 1.00 | 18203 | 3 | | | | PPP1R14D | 1.00 |
| 18108 | 3 | | | | | | PLSCR5 | 1.00 | 18204 | 3 | | | | PPP1R17 | 1.00 |
| 18109 | 3 | | | | | | PLTP | 1.00 | 18205 | 3 | | | | PPP1R1A | 1.00 |
| 18110 | 3 | | | | | | PLXNA4 | 1.00 | 18206 | 3 | | | | PPP1R1B | 1.00 |
| 18111 | 3 | | | | | | PLXNB1 | 1.00 | 18207 | 3 | | | | PPP1R1C | 1.00 |
| 18112 | 3 | | | | | | PLXNB3 | 1.00 | 18208 | 3 | | | | PPP1R27 | 1.00 |
| 18113 | 3 | | | | | | PM20D1 | 1.00 | 18209 | 3 | | | | PPP1R2P9 | 1.00 |
| 18114 | 3 | | | | | | PMCH | 1.00 | 18210 | 3 | | | | PPP1R32 | 1.00 |
| 18115 | 3 | | | | | | PMCHL1 | 1.00 | 18211 | 3 | | | | PPP1R36 | 1.00 |
| 18116 | 3 | | | | | | PMCHL2 | 1.00 | 18212 | 3 | | | | PPP1R3A | 1.00 |
| 18117 | 3 | | | | | | PMEL | 1.00 | 18213 | 3 | | | | PPP1R3C | 1.00 |
| 18118 | 3 | | | | | | PMF8P1 | 1.00 | 18214 | 3 | | | | PPP1R3G | 1.00 |
| 18119 | 3 | | | | | | PMP2 | 1.00 | 18215 | 3 | | | | PPP1R42 | 1.00 |
| 18120 | 3 | | | | | | PNCK | 1.00 | 18216 | 3 | | | | PPP1R9A | 1.00 |
| 18121 | 3 | | | | | | PNLDC1 | 1.00 | 18217 | 3 | | | | PPP2R2C | 1.00 |
| 18122 | 3 | | | | | | PNLIP | 1.00 | 18218 | 3 | | | | PPP2R3A | 1.00 |
| 18123 | 3 | | | | | | PNLIPRP1 | 1.00 | 18219 | 3 | | | | PPP3R2 | 1.00 |
| 18124 | 3 | | | | | | PNLIPRP2 | 1.00 | 18220 | 3 | | | | PPP4R4 | 1.00 |
| 18125 | 3 | | | | | | PNLIPRP3 | 1.00 | 18221 | 3 | | | | PPT2-EGFL8 | 1.00 |
| 18126 | 3 | | | | | | PNMA2 | 1.00 | 18222 | 3 | | | | PPY | 1.00 |
| 18127 | 3 | | | | | | PNMA5 | 1.00 | 18223 | 3 | | | | PPY2 | 1.00 |
| 18128 | 3 | | | | | | PNMA6A | 1.00 | 18224 | 3 | | | | PPYR1 | 1.00 |
| 18129 | 3 | | | | | | PNMA6C | 1.00 | 18225 | 3 | | | | PRAC | 1.00 |
| 18130 | 3 | | | | | | PNMA6D | 1.00 | 18226 | 3 | | | | PRAME | 1.00 |
| 18131 | 3 | | | | | | PNMAL1 | 1.00 | 18227 | 3 | | | | PRAMEF1 | 1.00 |
| 18132 | 3 | | | | | | PNMAL2 | 1.00 | 18228 | 3 | | | | PRAMEF10 | 1.00 |
| 18133 | 3 | | | | | | PNMT | 1.00 | 18229 | 3 | | | | PRAMEF11 | 1.00 |
| 18134 | 3 | | | | | | PNPLA3 | 1.00 | 18230 | 3 | | | | PRAMEF12 | 1.00 |
| 18135 | 3 | | | | | | PNPLA5 | 1.00 | 18231 | 3 | | | | PRAMEF13 | 1.00 |
| 18136 | 3 | | | | | | PNPLA7 | 1.00 | 18232 | 3 | | | | PRAMEF14 | 1.00 |

Fig. 40 - 96

| | | | | | | | | | | | | | | | |
|---|---|---|---|---|---|---|---|---|---|---|---|---|---|---|---|
| 18233 | 3 | | | | | | PRAMEF15 | 1.00 | 18329 | 3 | | | | PRRG2 | 1.00 |
| 18234 | 3 | | | | | | PRAMEF16 | 1.00 | 18330 | 3 | | | | PRRG3 | 1.00 |
| 18235 | 3 | | | | | | PRAMEF17 | 1.00 | 18331 | 3 | | | | PRRT4 | 1.00 |
| 18236 | 3 | | | | | | PRAMEF18 | 1.00 | 18332 | 3 | | | | PRRX1 | 1.00 |
| 18237 | 3 | | | | | | PRAMEF19 | 1.00 | 18333 | 3 | | | | PRRX2 | 1.00 |
| 18238 | 3 | | | | | | PRAMEF2 | 1.00 | 18334 | 3 | | | | PRSS1 | 1.00 |
| 18239 | 3 | | | | | | PRAMEF20 | 1.00 | 18335 | 3 | | | | PRSS12 | 1.00 |
| 18240 | 3 | | | | | | PRAMEF21 | 1.00 | 18336 | 3 | | | | PRSS16 | 1.00 |
| 18241 | 3 | | | | | | PRAMEF22 | 1.00 | 18337 | 3 | | | | PRSS2 | 1.00 |
| 18242 | 3 | | | | | | PRAMEF3 | 1.00 | 18338 | 3 | | | | PRSS22 | 1.00 |
| 18243 | 3 | | | | | | PRAMEF4 | 1.00 | 18339 | 3 | | | | PRSS27 | 1.00 |
| 18244 | 3 | | | | | | PRAMEF5 | 1.00 | 18340 | 3 | | | | PRSS3 | 1.00 |
| 18245 | 3 | | | | | | PRAMEF6 | 1.00 | 18341 | 3 | | | | PRSS35 | 1.00 |
| 18246 | 3 | | | | | | PRAMEF7 | 1.00 | 18342 | 3 | | | | PRSS36 | 1.00 |
| 18247 | 3 | | | | | | PRAMEF8 | 1.00 | 18343 | 3 | | | | PRSS37 | 1.00 |
| 18248 | 3 | | | | | | PRAMEF9 | 1.00 | 18344 | 3 | | | | PRSS38 | 1.00 |
| 18249 | 3 | | | | | | PRAP1 | 1.00 | 18345 | 3 | | | | PRSS41 | 1.00 |
| 18250 | 3 | | | | | | PRB1 | 1.00 | 18346 | 3 | | | | PRSS42 | 1.00 |
| 18251 | 3 | | | | | | PRB2 | 1.00 | 18347 | 3 | | | | PRSS45 | 1.00 |
| 18252 | 3 | | | | | | PRB3 | 1.00 | 18348 | 3 | | | | PRSS46 | 1.00 |
| 18253 | 3 | | | | | | PRB4 | 1.00 | 18349 | 3 | | | | PRSS48 | 1.00 |
| 18254 | 3 | | | | | | PRCD | 1.00 | 18350 | 3 | | | | PRSS50 | 1.00 |
| 18255 | 3 | | | | | | PRDM11 | 1.00 | 18351 | 3 | | | | PRSS54 | 1.00 |
| 18256 | 3 | | | | | | PRDM12 | 1.00 | 18352 | 3 | | | | PRSS55 | 1.00 |
| 18257 | 3 | | | | | | PRDM13 | 1.00 | 18353 | 3 | | | | PRSS56 | 1.00 |
| 18258 | 3 | | | | | | PRDM14 | 1.00 | 18354 | 3 | | | | PRSS58 | 1.00 |
| 18259 | 3 | | | | | | PRDM16 | 1.00 | 18355 | 3 | | | | PRSS8 | 1.00 |
| 18260 | 3 | | | | | | PRDM6 | 1.00 | 18356 | 3 | | | | PRTFDC1 | 1.00 |
| 18261 | 3 | | | | | | PRDM7 | 1.00 | 18357 | 3 | | | | PRTG | 1.00 |
| 18262 | 3 | | | | | | PRDM9 | 1.00 | 18358 | 3 | | | | PRTN3 | 1.00 |
| 18263 | 3 | | | | | | PRELID2 | 1.00 | 18359 | 3 | | | | PRUNE2 | 1.00 |
| 18264 | 3 | | | | | | PRELP | 1.00 | 18360 | 3 | | | | PRY | 1.00 |
| 18265 | 3 | | | | | | PREX2 | 1.00 | 18361 | 3 | | | | PSAPL1 | 1.00 |
| 18266 | 3 | | | | | | PRG1 | 1.00 | 18362 | 3 | | | | PSCA | 1.00 |
| 18267 | 3 | | | | | | PRG2 | 1.00 | 18363 | 3 | | | | PSD | 1.00 |
| 18268 | 3 | | | | | | PRG3 | 1.00 | 18364 | 3 | | | | PSD2 | 1.00 |
| 18269 | 3 | | | | | | PRG4 | 1.00 | 18365 | 3 | | | | PSD3 | 1.00 |
| 18270 | 3 | | | | | | PRH1 | 1.00 | 18366 | 3 | | | | PSG1 | 1.00 |
| 18271 | 3 | | | | | | PRH1-PRR4 | 1.00 | 18367 | 3 | | | | PSG10P | 1.00 |
| 18272 | 3 | | | | | | PRH2 | 1.00 | 18368 | 3 | | | | PSG11 | 1.00 |
| 18273 | 3 | | | | | | PRHOXNB | 1.00 | 18369 | 3 | | | | PSG2 | 1.00 |
| 18274 | 3 | | | | | | PRICKLE2 | 1.00 | 18370 | 3 | | | | PSG3 | 1.00 |
| 18275 | 3 | | | | | | PRIMA1 | 1.00 | 18371 | 3 | | | | PSG4 | 1.00 |
| 18276 | 3 | | | | | | PRINS | 1.00 | 18372 | 3 | | | | PSG5 | 1.00 |
| 18277 | 3 | | | | | | PRKAA2 | 1.00 | 18373 | 3 | | | | PSG6 | 1.00 |
| 18278 | 3 | | | | | | PRKAG3 | 1.00 | 18374 | 3 | | | | PSG7 | 1.00 |
| 18279 | 3 | | | | | | PRKCG | 1.00 | 18375 | 3 | | | | PSG8 | 1.00 |
| 18280 | 3 | | | | | | PRKD1 | 1.00 | 18376 | 3 | | | | PSG9 | 1.00 |
| 18281 | 3 | | | | | | PRKG1 | 1.00 | 18377 | 3 | | | | PSKH2 | 1.00 |
| 18282 | 3 | | | | | | PRKG2 | 1.00 | 18378 | 3 | | | | PSMA8 | 1.00 |
| 18283 | 3 | | | | | | PRKY | 1.00 | 18379 | 3 | | | | PSMB11 | 1.00 |
| 18284 | 3 | | | | | | PRL | 1.00 | 18380 | 3 | | | | PSMC3IP | 1.00 |
| 18285 | 3 | | | | | | PRLH | 1.00 | 18381 | 3 | | | | PSORS1C1 | 1.00 |
| 18286 | 3 | | | | | | PRLHR | 1.00 | 18382 | 3 | | | | PSORS1C2 | 1.00 |
| 18287 | 3 | | | | | | PRLR | 1.00 | 18383 | 3 | | | | PSORS1C3 | 1.00 |
| 18288 | 3 | | | | | | PRM1 | 1.00 | 18384 | 3 | | | | PSPN | 1.00 |
| 18289 | 3 | | | | | | PRM2 | 1.00 | 18385 | 3 | | | | PSTK | 1.00 |
| 18290 | 3 | | | | | | PRM3 | 1.00 | 18386 | 3 | | | | PTCH2 | 1.00 |
| 18291 | 3 | | | | | | PRMT8 | 1.00 | 18387 | 3 | | | | PTCHD1 | 1.00 |
| 18292 | 3 | | | | | | PRND | 1.00 | 18388 | 3 | | | | PTCHD2 | 1.00 |
| 18293 | 3 | | | | | | PRNT | 1.00 | 18389 | 3 | | | | PTCHD3 | 1.00 |
| 18294 | 3 | | | | | | PRO0611 | 1.00 | 18390 | 3 | | | | PTCHD4 | 1.00 |
| 18295 | 3 | | | | | | PRO1768 | 1.00 | 18391 | 3 | | | | PTF1A | 1.00 |
| 18296 | 3 | | | | | | PROC | 1.00 | 18392 | 3 | | | | PTGER1 | 1.00 |
| 18297 | 3 | | | | | | PRODH | 1.00 | 18393 | 3 | | | | PTGER3 | 1.00 |
| 18298 | 3 | | | | | | PRODH2 | 1.00 | 18394 | 3 | | | | PTGFR | 1.00 |
| 18299 | 3 | | | | | | PROK1 | 1.00 | 18395 | 3 | | | | PTGIS | 1.00 |
| 18300 | 3 | | | | | | PROKR1 | 1.00 | 18396 | 3 | | | | PTGR1 | 1.00 |
| 18301 | 3 | | | | | | PROKR2 | 1.00 | 18397 | 3 | | | | PTH | 1.00 |
| 18302 | 3 | | | | | | PROL1 | 1.00 | 18398 | 3 | | | | PTH1R | 1.00 |
| 18303 | 3 | | | | | | PROM1 | 1.00 | 18399 | 3 | | | | PTH2 | 1.00 |
| 18304 | 3 | | | | | | PROM2 | 1.00 | 18400 | 3 | | | | PTH2R | 1.00 |
| 18305 | 3 | | | | | | PROP1 | 1.00 | 18401 | 3 | | | | PTHLH | 1.00 |
| 18306 | 3 | | | | | | PROX1 | 1.00 | 18402 | 3 | | | | PTK7 | 1.00 |
| 18307 | 3 | | | | | | PROX1-AS1 | 1.00 | 18403 | 3 | | | | PTN | 1.00 |
| 18308 | 3 | | | | | | PROZ | 1.00 | 18404 | 3 | | | | PTPDC1 | 1.00 |
| 18309 | 3 | | | | | | PRPF40B | 1.00 | 18405 | 3 | | | | PTPLA | 1.00 |
| 18310 | 3 | | | | | | PRPH | 1.00 | 18406 | 3 | | | | PTPN13 | 1.00 |
| 18311 | 3 | | | | | | PRPH2 | 1.00 | 18407 | 3 | | | | PTPN14 | 1.00 |
| 18312 | 3 | | | | | | PRPS1L1 | 1.00 | 18408 | 3 | | | | PTPN20A | 1.00 |
| 18313 | 3 | | | | | | PRR15 | 1.00 | 18409 | 3 | | | | PTPN20B | 1.00 |
| 18314 | 3 | | | | | | PRR15L | 1.00 | 18410 | 3 | | | | PTPN21 | 1.00 |
| 18315 | 3 | | | | | | PRR18 | 1.00 | 18411 | 3 | | | | PTPN3 | 1.00 |
| 18316 | 3 | | | | | | PRR19 | 1.00 | 18412 | 3 | | | | PTPN5 | 1.00 |
| 18317 | 3 | | | | | | PRR20B | 1.00 | 18413 | 3 | | | | PTPRB | 1.00 |
| 18318 | 3 | | | | | | PRR20D | 1.00 | 18414 | 3 | | | | PTPRD | 1.00 |
| 18319 | 3 | | | | | | PRR20E | 1.00 | 18415 | 3 | | | | PTPRF | 1.00 |
| 18320 | 3 | | | | | | PRR21 | 1.00 | 18416 | 3 | | | | PTPRG | 1.00 |
| 18321 | 3 | | | | | | PRR22 | 1.00 | 18417 | 3 | | | | PTPRH | 1.00 |
| 18322 | 3 | | | | | | PRR23A | 1.00 | 18418 | 3 | | | | PTPRM | 1.00 |
| 18323 | 3 | | | | | | PRR23B | 1.00 | 18419 | 3 | | | | PTPRN | 1.00 |
| 18324 | 3 | | | | | | PRR23C | 1.00 | 18420 | 3 | | | | PTPRQ | 1.00 |
| 18325 | 3 | | | | | | PRR25 | 1.00 | 18421 | 3 | | | | PTPRR | 1.00 |
| 18326 | 3 | | | | | | PRR5-ARHGAP8 | 1.00 | 18422 | 3 | | | | PTPRT | 1.00 |
| 18327 | 3 | | | | | | PRR9 | 1.00 | 18423 | 3 | | | | PTPRU | 1.00 |
| 18328 | 3 | | | | | | PRRG1 | 1.00 | 18424 | 3 | | | | PTPRVP | 1.00 |

Fig. 40 - 97

| | | | | | | | | | | | | | |
|---|---|---|---|---|---|---|---|---|---|---|---|---|---|
| 18425 | 3 | | | | | PTPRZ1 | 1.00 | 18521 | 3 | | | RBM26-AS1 | 1.00 |
| 18426 | 3 | | | | | PTRF | 1.00 | 18522 | 3 | | | RBM44 | 1.00 |
| 18427 | 3 | | | | | PTX4 | 1.00 | 18523 | 3 | | | RBM46 | 1.00 |
| 18428 | 3 | | | | | PURG | 1.00 | 18524 | 3 | | | RBMS3 | 1.00 |
| 18429 | 3 | | | | | PVRL3 | 1.00 | 18525 | 3 | | | RBMXL2 | 1.00 |
| 18430 | 3 | | | | | PVRL3-AS1 | 1.00 | 18526 | 3 | | | RBMXL3 | 1.00 |
| 18431 | 3 | | | | | PVRL4 | 1.00 | 18527 | 3 | | | RBMY1A1 | 1.00 |
| 18432 | 3 | | | | | PWRN1 | 1.00 | 18528 | 3 | | | RBMY1A3P | 1.00 |
| 18433 | 3 | | | | | PWRN2 | 1.00 | 18529 | 3 | | | RBMY1B | 1.00 |
| 18434 | 3 | | | | | PXDN | 1.00 | 18530 | 3 | | | RBMY1D | 1.00 |
| 18435 | 3 | | | | | PXDNL | 1.00 | 18531 | 3 | | | RBMY1E | 1.00 |
| 18436 | 3 | | | | | PXT1 | 1.00 | 18532 | 3 | | | RBMY1F | 1.00 |
| 18437 | 3 | | | | | PYCR1 | 1.00 | 18533 | 3 | | | RBMY1J | 1.00 |
| 18438 | 3 | | | | | PYDC1 | 1.00 | 18534 | 3 | | | RBMY2EP | 1.00 |
| 18439 | 3 | | | | | PYDC2 | 1.00 | 18535 | 3 | | | RBMY2FP | 1.00 |
| 18440 | 3 | | | | | PYGO1 | 1.00 | 18536 | 3 | | | RBMY3AP | 1.00 |
| 18441 | 3 | | | | | PYY | 1.00 | 18537 | 3 | | | RBP1 | 1.00 |
| 18442 | 3 | | | | | PYY2 | 1.00 | 18538 | 3 | | | RBP2 | 1.00 |
| 18443 | 3 | | | | | PZP | 1.00 | 18539 | 3 | | | RBP3 | 1.00 |
| 18444 | 3 | | | | | QRFP | 1.00 | 18540 | 3 | | | RBP4 | 1.00 |
| 18445 | 3 | | | | | QRFPR | 1.00 | 18541 | 3 | | | RBPJL | 1.00 |
| 18446 | 3 | | | | | QRICH2 | 1.00 | 18542 | 3 | | | RCAN2 | 1.00 |
| 18447 | 3 | | | | | R3HDML | 1.00 | 18543 | 3 | | | RCOR2 | 1.00 |
| 18448 | 3 | | | | | RAB17 | 1.00 | 18544 | 3 | | | RCVRN | 1.00 |
| 18449 | 3 | | | | | RAB19 | 1.00 | 18545 | 3 | | | RD3 | 1.00 |
| 18450 | 3 | | | | | RAB23 | 1.00 | 18546 | 3 | | | RDH12 | 1.00 |
| 18451 | 3 | | | | | RAB25 | 1.00 | 18547 | 3 | | | RDH16 | 1.00 |
| 18452 | 3 | | | | | RAB26 | 1.00 | 18548 | 3 | | | RDH8 | 1.00 |
| 18453 | 3 | | | | | RAB3B | 1.00 | 18549 | 3 | | | RDM1 | 1.00 |
| 18454 | 3 | | | | | RAB3B | 1.00 | 18550 | 3 | | | RECQL4 | 1.00 |
| 18455 | 3 | | | | | RAB3C | 1.00 | 18551 | 3 | | | REEP1 | 1.00 |
| 18456 | 3 | | | | | RAB40A | 1.00 | 18552 | 3 | | | REEP2 | 1.00 |
| 18457 | 3 | | | | | RAB40AL | 1.00 | 18553 | 3 | | | REG1A | 1.00 |
| 18458 | 3 | | | | | RAB41 | 1.00 | 18554 | 3 | | | REG1B | 1.00 |
| 18459 | 3 | | | | | RAB42 | 1.00 | 18555 | 3 | | | REG1P | 1.00 |
| 18460 | 3 | | | | | RAB4B-EGLN2 | 1.00 | 18556 | 3 | | | REG3A | 1.00 |
| 18461 | 3 | | | | | RAB9B | 1.00 | 18557 | 3 | | | REG3G | 1.00 |
| 18462 | 3 | | | | | RAB9BP1 | 1.00 | 18558 | 3 | | | REG4 | 1.00 |
| 18463 | 3 | | | | | RABL5 | 1.00 | 18559 | 3 | | | RELN | 1.00 |
| 18464 | 3 | | | | | RAC3 | 1.00 | 18560 | 3 | | | REM1 | 1.00 |
| 18465 | 3 | | | | | RAD21-AS1 | 1.00 | 18561 | 3 | | | REN | 1.00 |
| 18466 | 3 | | | | | RAD21L1 | 1.00 | 18562 | 3 | | | REP15 | 1.00 |
| 18467 | 3 | | | | | RAD51 | 1.00 | 18563 | 3 | | | RERG | 1.00 |
| 18468 | 3 | | | | | RAD51AP1 | 1.00 | 18564 | 3 | | | RERGL | 1.00 |
| 18469 | 3 | | | | | RAD51AP2 | 1.00 | 18565 | 3 | | | RESP18 | 1.00 |
| 18470 | 3 | | | | | RAD51L3-RFFL | 1.00 | 18566 | 3 | | | RET | 1.00 |
| 18471 | 3 | | | | | RAD54B | 1.00 | 18567 | 3 | | | RETNLB | 1.00 |
| 18472 | 3 | | | | | RAD54L | 1.00 | 18568 | 3 | | | REXO1L1 | 1.00 |
| 18473 | 3 | | | | | RAD9B | 1.00 | 18569 | 3 | | | REXO1L2P | 1.00 |
| 18474 | 3 | | | | | RADIL | 1.00 | 18570 | 3 | | | RFESD | 1.00 |
| 18475 | 3 | | | | | RAET1E | 1.00 | 18571 | 3 | | | RFPL1 | 1.00 |
| 18476 | 3 | | | | | RAET1G | 1.00 | 18572 | 3 | | | RFPL1-AS1 | 1.00 |
| 18477 | 3 | | | | | RAET1K | 1.00 | 18573 | 3 | | | RFPL3 | 1.00 |
| 18478 | 3 | | | | | RAET1L | 1.00 | 18574 | 3 | | | RFPL3-AS1 | 1.00 |
| 18479 | 3 | | | | | RAG1 | 1.00 | 18575 | 3 | | | RFPL4A | 1.00 |
| 18480 | 3 | | | | | RAG2 | 1.00 | 18576 | 3 | | | RFPL4B | 1.00 |
| 18481 | 3 | | | | | RAI14 | 1.00 | 18577 | 3 | | | RFTN2 | 1.00 |
| 18482 | 3 | | | | | RAI2 | 1.00 | 18578 | 3 | | | RFX4 | 1.00 |
| 18483 | 3 | | | | | RALYL | 1.00 | 18579 | 3 | | | RFX6 | 1.00 |
| 18484 | 3 | | | | | RAMP2 | 1.00 | 18580 | 3 | | | RFX8 | 1.00 |
| 18485 | 3 | | | | | RAMP3 | 1.00 | 18581 | 3 | | | RGAG1 | 1.00 |
| 18486 | 3 | | | | | RANBP17 | 1.00 | 18582 | 3 | | | RGL3 | 1.00 |
| 18487 | 3 | | | | | RANBP3L | 1.00 | 18583 | 3 | | | RGMA | 1.00 |
| 18488 | 3 | | | | | RAP1GAP | 1.00 | 18584 | 3 | | | RGN | 1.00 |
| 18489 | 3 | | | | | RAPGEF3 | 1.00 | 18585 | 3 | | | RGNEF | 1.00 |
| 18490 | 3 | | | | | RAPGEF4 | 1.00 | 18586 | 3 | | | RGPD6 | 1.00 |
| 18491 | 3 | | | | | RAPGEF5 | 1.00 | 18587 | 3 | | | RGR | 1.00 |
| 18492 | 3 | | | | | RAPSN | 1.00 | 18588 | 3 | | | RGS11 | 1.00 |
| 18493 | 3 | | | | | RARB | 1.00 | 18589 | 3 | | | RGS13 | 1.00 |
| 18494 | 3 | | | | | RARRES1 | 1.00 | 18590 | 3 | | | RGS16 | 1.00 |
| 18495 | 3 | | | | | RARRES2 | 1.00 | 18591 | 3 | | | RGS17 | 1.00 |
| 18496 | 3 | | | | | RASAL1 | 1.00 | 18592 | 3 | | | RGS20 | 1.00 |
| 18497 | 3 | | | | | RASAL2 | 1.00 | 18593 | 3 | | | RGS21 | 1.00 |
| 18498 | 3 | | | | | RASD1 | 1.00 | 18594 | 3 | | | RGS22 | 1.00 |
| 18499 | 3 | | | | | RASD2 | 1.00 | 18595 | 3 | | | RGS4 | 1.00 |
| 18500 | 3 | | | | | RASEF | 1.00 | 18596 | 3 | | | RGS5 | 1.00 |
| 18501 | 3 | | | | | RASGEF1C | 1.00 | 18597 | 3 | | | RGS6 | 1.00 |
| 18502 | 3 | | | | | RASGRF1 | 1.00 | 18598 | 3 | | | RGS7 | 1.00 |
| 18503 | 3 | | | | | RASIP1 | 1.00 | 18599 | 3 | | | RGS7BP | 1.00 |
| 18504 | 3 | | | | | RASL10A | 1.00 | 18600 | 3 | | | RGS8 | 1.00 |
| 18505 | 3 | | | | | RASL10B | 1.00 | 18601 | 3 | | | RGS9 | 1.00 |
| 18506 | 3 | | | | | RASL11B | 1.00 | 18602 | 3 | | | RGS9BP | 1.00 |
| 18507 | 3 | | | | | RASL12 | 1.00 | 18603 | 3 | | | RGSL1 | 1.00 |
| 18508 | 3 | | | | | RASSF10 | 1.00 | 18604 | 3 | | | RHAG | 1.00 |
| 18509 | 3 | | | | | RASSF6 | 1.00 | 18605 | 3 | | | RHBDF1 | 1.00 |
| 18510 | 3 | | | | | RASSF8 | 1.00 | 18606 | 3 | | | RHBDL1 | 1.00 |
| 18511 | 3 | | | | | RASSF9 | 1.00 | 18607 | 3 | | | RHBDL2 | 1.00 |
| 18512 | 3 | | | | | RAX | 1.00 | 18608 | 3 | | | RHBDL3 | 1.00 |
| 18513 | 3 | | | | | RAX2 | 1.00 | 18609 | 3 | | | RHBG | 1.00 |
| 18514 | 3 | | | | | RBAK-LOC389458 | 1.00 | 18610 | 3 | | | RHCE | 1.00 |
| 18515 | 3 | | | | | RBFOX1 | 1.00 | 18611 | 3 | | | RHCG | 1.00 |
| 18516 | 3 | | | | | RBFOX2 | 1.00 | 18612 | 3 | | | RHO | 1.00 |
| 18517 | 3 | | | | | RBFOX3 | 1.00 | 18613 | 3 | | | RHOBTB3 | 1.00 |
| 18518 | 3 | | | | | RBKS | 1.00 | 18614 | 3 | | | RHOD | 1.00 |
| 18519 | 3 | | | | | RBM20 | 1.00 | 18615 | 3 | | | RHOJ | 1.00 |
| 18520 | 3 | | | | | RBM24 | 1.00 | 18616 | 3 | | | RHOV | 1.00 |

Fig. 40 - 98

| | | | | | | | | | | | | | | |
|---|---|---|---|---|---|---|---|---|---|---|---|---|---|---|
| 18617 | 3 | | | | | | RHOXF1 | 1.00 | 18713 | 3 | | | RPSAPS2 | 1.00 |
| 18618 | 3 | | | | | | RHOXF2 | 1.00 | 18714 | 3 | | | RPTN | 1.00 |
| 18619 | 3 | | | | | | RHOXF2B | 1.00 | 18715 | 3 | | | RRAD | 1.00 |
| 18620 | 3 | | | | | | RHPN2 | 1.00 | 18716 | 3 | | | RRH | 1.00 |
| 18621 | 3 | | | | | | RIBC1 | 1.00 | 18717 | 3 | | | RS1 | 1.00 |
| 18622 | 3 | | | | | | RIBC2 | 1.00 | 18718 | 3 | | | RSPH1 | 1.00 |
| 18623 | 3 | | | | | | RIIAD1 | 1.00 | 18719 | 3 | | | RSPH10B2 | 1.00 |
| 18624 | 3 | | | | | | RIMBP2 | 1.00 | 18720 | 3 | | | RSPH4A | 1.00 |
| 18625 | 3 | | | | | | RIMBP3C | 1.00 | 18721 | 3 | | | RSPH6A | 1.00 |
| 18626 | 3 | | | | | | RIMKLA | 1.00 | 18722 | 3 | | | RSPO1 | 1.00 |
| 18627 | 3 | | | | | | RIMS1 | 1.00 | 18723 | 3 | | | RSPO2 | 1.00 |
| 18628 | 3 | | | | | | RIMS2 | 1.00 | 18724 | 3 | | | RSPO3 | 1.00 |
| 18629 | 3 | | | | | | RIMS4 | 1.00 | 18725 | 3 | | | RSPO4 | 1.00 |
| 18630 | 3 | | | | | | RIPK4 | 1.00 | 18726 | 3 | | | RTBDN | 1.00 |
| 18631 | 3 | | | | | | RIPPLY1 | 1.00 | 18727 | 3 | | | RTDR1 | 1.00 |
| 18632 | 3 | | | | | | RIPPLY2 | 1.00 | 18728 | 3 | | | RTEL1-TNFRSF6B | 1.00 |
| 18633 | 3 | | | | | | RIT2 | 1.00 | 18729 | 3 | | | RTKN | 1.00 |
| 18634 | 3 | | | | | | RLBP1 | 1.00 | 18730 | 3 | | | RTL1 | 1.00 |
| 18635 | 3 | | | | | | RLN1 | 1.00 | 18731 | 3 | | | RTN4RL1 | 1.00 |
| 18636 | 3 | | | | | | RLN3 | 1.00 | 18732 | 3 | | | RTN4RL2 | 1.00 |
| 18637 | 3 | | | | | | RMST | 1.00 | 18733 | 3 | | | RTP1 | 1.00 |
| 18638 | 3 | | | | | | RNASE10 | 1.00 | 18734 | 3 | | | RTP2 | 1.00 |
| 18639 | 3 | | | | | | RNASE11 | 1.00 | 18735 | 3 | | | RTP3 | 1.00 |
| 18640 | 3 | | | | | | RNASE12 | 1.00 | 18736 | 3 | | | RTTN | 1.00 |
| 18641 | 3 | | | | | | RNASE13 | 1.00 | 18737 | 3 | | | RUNDC3B | 1.00 |
| 18642 | 3 | | | | | | RNASE7 | 1.00 | 18738 | 3 | | | RUNX1-IT1 | 1.00 |
| 18643 | 3 | | | | | | RNASE8 | 1.00 | 18739 | 3 | | | RUNX1T1 | 1.00 |
| 18644 | 3 | | | | | | RNASE9 | 1.00 | 18740 | 3 | | | RXFP1 | 1.00 |
| 18645 | 3 | | | | | | RND1 | 1.00 | 18741 | 3 | | | RXFP2 | 1.00 |
| 18646 | 3 | | | | | | RND2 | 1.00 | 18742 | 3 | | | RXFP3 | 1.00 |
| 18647 | 3 | | | | | | RND3 | 1.00 | 18743 | 3 | | | RXFP4 | 1.00 |
| 18648 | 3 | | | | | | RNF112 | 1.00 | 18744 | 3 | | | RXRG | 1.00 |
| 18649 | 3 | | | | | | RNF113B | 1.00 | 18745 | 3 | | | RYR1 | 1.00 |
| 18650 | 3 | | | | | | RNF128 | 1.00 | 18746 | 3 | | | RYR2 | 1.00 |
| 18651 | 3 | | | | | | RNF133 | 1.00 | 18747 | 3 | | | RYR3 | 1.00 |
| 18652 | 3 | | | | | | RNF148 | 1.00 | 18748 | 3 | | | S100A1 | 1.00 |
| 18653 | 3 | | | | | | RNF150 | 1.00 | 18749 | 3 | | | S100A14 | 1.00 |
| 18654 | 3 | | | | | | RNF151 | 1.00 | 18750 | 3 | | | S100A16 | 1.00 |
| 18655 | 3 | | | | | | RNF152 | 1.00 | 18751 | 3 | | | S100A2 | 1.00 |
| 18656 | 3 | | | | | | RNF165 | 1.00 | 18752 | 3 | | | S100A3 | 1.00 |
| 18657 | 3 | | | | | | RNF17 | 1.00 | 18753 | 3 | | | S100A5 | 1.00 |
| 18658 | 3 | | | | | | RNF180 | 1.00 | 18754 | 3 | | | S100A7 | 1.00 |
| 18659 | 3 | | | | | | RNF183 | 1.00 | 18755 | 3 | | | S100A7A | 1.00 |
| 18660 | 3 | | | | | | RNF186 | 1.00 | 18756 | 3 | | | S100A7L2 | 1.00 |
| 18661 | 3 | | | | | | RNF207 | 1.00 | 18757 | 3 | | | S100G | 1.00 |
| 18662 | 3 | | | | | | RNF212 | 1.00 | 18758 | 3 | | | SAA1 | 1.00 |
| 18663 | 3 | | | | | | RNF217 | 1.00 | 18759 | 3 | | | SAA2 | 1.00 |
| 18664 | 3 | | | | | | RNF222 | 1.00 | 18760 | 3 | | | SAA2-SAA4 | 1.00 |
| 18665 | 3 | | | | | | RNF223 | 1.00 | 18761 | 3 | | | SAA3P | 1.00 |
| 18666 | 3 | | | | | | RNF224 | 1.00 | 18762 | 3 | | | SAA4 | 1.00 |
| 18667 | 3 | | | | | | RNF39 | 1.00 | 18763 | 3 | | | SAG | 1.00 |
| 18668 | 3 | | | | | | RNF43 | 1.00 | 18764 | 3 | | | SAGE1 | 1.00 |
| 18669 | 3 | | | | | | RNFT2 | 1.00 | 18765 | 3 | | | SALL1 | 1.00 |
| 18670 | 3 | | | | | | RNLS | 1.00 | 18766 | 3 | | | SALL3 | 1.00 |
| 18671 | 3 | | | | | | RNU12 | 1.00 | 18767 | 3 | | | SALL4 | 1.00 |
| 18672 | 3 | | | | | | RNU4ATAC | 1.00 | 18768 | 3 | | | SAMD11 | 1.00 |
| 18673 | 3 | | | | | | RNU5D-1 | 1.00 | 18769 | 3 | | | SAMD12 | 1.00 |
| 18674 | 3 | | | | | | RNU5E-1 | 1.00 | 18770 | 3 | | | SAMD12-AS1 | 1.00 |
| 18675 | 3 | | | | | | RNU5F-1 | 1.00 | 18771 | 3 | | | SAMD13 | 1.00 |
| 18676 | 3 | | | | | | RNU6 | 1.00 | 18772 | 3 | | | SAMD15 | 1.00 |
| 18677 | 3 | | | | | | RNY4 | 1.00 | 18773 | 3 | | | SAMD5 | 1.00 |
| 18678 | 3 | | | | | | RNY5 | 1.00 | 18774 | 3 | | | SAMD7 | 1.00 |
| 18679 | 3 | | | | | | ROBO1 | 1.00 | 18775 | 3 | | | SATB2 | 1.00 |
| 18680 | 3 | | | | | | ROBO2 | 1.00 | 18776 | 3 | | | SATL1 | 1.00 |
| 18681 | 3 | | | | | | ROBO3 | 1.00 | 18777 | 3 | | | SBK2 | 1.00 |
| 18682 | 3 | | | | | | ROBO4 | 1.00 | 18778 | 3 | | | SBSN | 1.00 |
| 18683 | 3 | | | | | | ROM1 | 1.00 | 18779 | 3 | | | SCAND3 | 1.00 |
| 18684 | 3 | | | | | | ROPN1 | 1.00 | 18780 | 3 | | | SCARA3 | 1.00 |
| 18685 | 3 | | | | | | ROPN1B | 1.00 | 18781 | 3 | | | SCARA5 | 1.00 |
| 18686 | 3 | | | | | | ROR1 | 1.00 | 18782 | 3 | | | SCARF2 | 1.00 |
| 18687 | 3 | | | | | | ROR2 | 1.00 | 18783 | 3 | | | SCARNA1 | 1.00 |
| 18688 | 3 | | | | | | RORB | 1.00 | 18784 | 3 | | | SCARNA11 | 1.00 |
| 18689 | 3 | | | | | | ROS1 | 1.00 | 18785 | 3 | | | SCARNA13 | 1.00 |
| 18690 | 3 | | | | | | RP1 | 1.00 | 18786 | 3 | | | SCARNA14 | 1.00 |
| 18691 | 3 | | | | | | RP1-177G6.2 | 1.00 | 18787 | 3 | | | SCARNA15 | 1.00 |
| 18692 | 3 | | | | | | RP11-165H21 | 1.00 | 18788 | 3 | | | SCARNA18 | 1.00 |
| 18693 | 3 | | | | | | RP1L1 | 1.00 | 18789 | 3 | | | SCARNA20 | 1.00 |
| 18694 | 3 | | | | | | RPA4 | 1.00 | 18790 | 3 | | | SCARNA21 | 1.00 |
| 18695 | 3 | | | | | | RPE65 | 1.00 | 18791 | 3 | | | SCARNA22 | 1.00 |
| 18696 | 3 | | | | | | RPGRIP1L | 1.00 | 18792 | 3 | | | SCARNA23 | 1.00 |
| 18697 | 3 | | | | | | RPL10L | 1.00 | 18793 | 3 | | | SCARNA27 | 1.00 |
| 18698 | 3 | | | | | | RPL13AP17 | 1.00 | 18794 | 3 | | | SCARNA3 | 1.00 |
| 18699 | 3 | | | | | | RPL13AP3 | 1.00 | 18795 | 3 | | | SCARNA5 | 1.00 |
| 18700 | 3 | | | | | | RPL13AP5 | 1.00 | 18796 | 3 | | | SCARNA6 | 1.00 |
| 18701 | 3 | | | | | | RPL23AP32 | 1.00 | 18797 | 3 | | | SCARNA8 | 1.00 |
| 18702 | 3 | | | | | | RPL31P11 | 1.00 | 18798 | 3 | | | SCARNA9L | 1.00 |
| 18703 | 3 | | | | | | RPLP0P2 | 1.00 | 18799 | 3 | | | SCEL | 1.00 |
| 18704 | 3 | | | | | | RPRM | 1.00 | 18800 | 3 | | | SCG2 | 1.00 |
| 18705 | 3 | | | | | | RPRML | 1.00 | 18801 | 3 | | | SCG3 | 1.00 |
| 18706 | 3 | | | | | | RPS16P5 | 1.00 | 18802 | 3 | | | SCG5 | 1.00 |
| 18707 | 3 | | | | | | RPS21 | 1.00 | 18803 | 3 | | | SCGB1A1 | 1.00 |
| 18708 | 3 | | | | | | RPS4Y1 | 1.00 | 18804 | 3 | | | SCGB1B2P | 1.00 |
| 18709 | 3 | | | | | | RPS4Y2 | 1.00 | 18805 | 3 | | | SCGB1D1 | 1.00 |
| 18710 | 3 | | | | | | RPS6KA6 | 1.00 | 18806 | 3 | | | SCGB1D2 | 1.00 |
| 18711 | 3 | | | | | | RPS6KL1 | 1.00 | 18807 | 3 | | | SCGB1D4 | 1.00 |
| 18712 | 3 | | | | | | RPS7P5 | 1.00 | 18808 | 3 | | | SCGB2A1 | 1.00 |

Fig. 40 - 99

| | | | | | | | | | | | | | | |
|---|---|---|---|---|---|---|---|---|---|---|---|---|---|---|
| 18809 | 3 | | | | | | SCGB2A2 | 1.00 | 18905 | 3 | | | | | | SERTAD4 | 1.00 |
| 18810 | 3 | | | | | | SCGB2B2 | 1.00 | 18906 | 3 | | | | | | SERTM1 | 1.00 |
| 18811 | 3 | | | | | | SCGB2B3P | 1.00 | 18907 | 3 | | | | | | SEZ6 | 1.00 |
| 18812 | 3 | | | | | | SCGB3A1 | 1.00 | 18908 | 3 | | | | | | SEZ6L | 1.00 |
| 18813 | 3 | | | | | | SCGN | 1.00 | 18909 | 3 | | | | | | SEZ6L2 | 1.00 |
| 18814 | 3 | | | | | | SCHIP1 | 1.00 | 18910 | 3 | | | | | | SFN | 1.00 |
| 18815 | 3 | | | | | | SCIN | 1.00 | 18911 | 3 | | | | | | SFRP1 | 1.00 |
| 18816 | 3 | | | | | | SCML2 | 1.00 | 18912 | 3 | | | | | | SFRP4 | 1.00 |
| 18817 | 3 | | | | | | SCN10A | 1.00 | 18913 | 3 | | | | | | SFRP5 | 1.00 |
| 18818 | 3 | | | | | | SCN11A | 1.00 | 18914 | 3 | | | | | | SFTA1P | 1.00 |
| 18819 | 3 | | | | | | SCN1A | 1.00 | 18915 | 3 | | | | | | SFTA2 | 1.00 |
| 18820 | 3 | | | | | | SCN2A | 1.00 | 18916 | 3 | | | | | | SFTA3 | 1.00 |
| 18821 | 3 | | | | | | SCN2B | 1.00 | 18917 | 3 | | | | | | SFTPA1 | 1.00 |
| 18822 | 3 | | | | | | SCN3A | 1.00 | 18918 | 3 | | | | | | SFTPA2 | 1.00 |
| 18823 | 3 | | | | | | SCN3B | 1.00 | 18919 | 3 | | | | | | SFTPB | 1.00 |
| 18824 | 3 | | | | | | SCN4A | 1.00 | 18920 | 3 | | | | | | SFTPC | 1.00 |
| 18825 | 3 | | | | | | SCN4B | 1.00 | 18921 | 3 | | | | | | SFTPD | 1.00 |
| 18826 | 3 | | | | | | SCN5A | 1.00 | 18922 | 3 | | | | | | SGCA | 1.00 |
| 18827 | 3 | | | | | | SCN7A | 1.00 | 18923 | 3 | | | | | | SGCD | 1.00 |
| 18828 | 3 | | | | | | SCN8A | 1.00 | 18924 | 3 | | | | | | SGCE | 1.00 |
| 18829 | 3 | | | | | | SCN9A | 1.00 | 18925 | 3 | | | | | | SGCG | 1.00 |
| 18830 | 3 | | | | | | SCNN1A | 1.00 | 18926 | 3 | | | | | | SGCZ | 1.00 |
| 18831 | 3 | | | | | | SCNN1B | 1.00 | 18927 | 3 | | | | | | SGIP1 | 1.00 |
| 18832 | 3 | | | | | | SCNN1D | 1.00 | 18928 | 3 | | | | | | SGK110 | 1.00 |
| 18833 | 3 | | | | | | SCNN1G | 1.00 | 18929 | 3 | | | | | | SGK2 | 1.00 |
| 18834 | 3 | | | | | | SCRG1 | 1.00 | 18930 | 3 | | | | | | SGSM1 | 1.00 |
| 18835 | 3 | | | | | | SCRT1 | 1.00 | 18931 | 3 | | | | | | SH2D4A | 1.00 |
| 18836 | 3 | | | | | | SCRT2 | 1.00 | 18932 | 3 | | | | | | SH2D4B | 1.00 |
| 18837 | 3 | | | | | | SCTR | 1.00 | 18933 | 3 | | | | | | SH2D5 | 1.00 |
| 18838 | 3 | | | | | | SCUBE1 | 1.00 | 18934 | 3 | | | | | | SH2D6 | 1.00 |
| 18839 | 3 | | | | | | SCUBE2 | 1.00 | 18935 | 3 | | | | | | SH2D7 | 1.00 |
| 18840 | 3 | | | | | | SCUBE3 | 1.00 | 18936 | 3 | | | | | | SH3BGR | 1.00 |
| 18841 | 3 | | | | | | SCXA | 1.00 | 18937 | 3 | | | | | | SH3D19 | 1.00 |
| 18842 | 3 | | | | | | SDC1 | 1.00 | 18938 | 3 | | | | | | SH3GL2 | 1.00 |
| 18843 | 3 | | | | | | SDC4P | 1.00 | 18939 | 3 | | | | | | SH3GL3 | 1.00 |
| 18844 | 3 | | | | | | SDK1 | 1.00 | 18940 | 3 | | | | | | SH3PXD2B | 1.00 |
| 18845 | 3 | | | | | | SDK2 | 1.00 | 18941 | 3 | | | | | | SH3RF2 | 1.00 |
| 18846 | 3 | | | | | | SDR16C5 | 1.00 | 18942 | 3 | | | | | | SH3TC2 | 1.00 |
| 18847 | 3 | | | | | | SDR9C7 | 1.00 | 18943 | 3 | | | | | | SHANK1 | 1.00 |
| 18848 | 3 | | | | | | SDS | 1.00 | 18944 | 3 | | | | | | SHANK2 | 1.00 |
| 18849 | 3 | | | | | | SEBOX | 1.00 | 18945 | 3 | | | | | | SHANK3 | 1.00 |
| 18850 | 3 | | | | | | SEC1 | 1.00 | 18946 | 3 | | | | | | SHB | 1.00 |
| 18851 | 3 | | | | | | SEC14L2 | 1.00 | 18947 | 3 | | | | | | SHBG | 1.00 |
| 18852 | 3 | | | | | | SEC14L3 | 1.00 | 18948 | 3 | | | | | | SHC2 | 1.00 |
| 18853 | 3 | | | | | | SEC14L4 | 1.00 | 18949 | 3 | | | | | | SHC3 | 1.00 |
| 18854 | 3 | | | | | | SEC14L6 | 1.00 | 18950 | 3 | | | | | | SHC4 | 1.00 |
| 18855 | 3 | | | | | | SEC16B | 1.00 | 18951 | 3 | | | | | | SHCBP1 | 1.00 |
| 18856 | 3 | | | | | | SEL1L2 | 1.00 | 18952 | 3 | | | | | | SHCBP1L | 1.00 |
| 18857 | 3 | | | | | | SELE | 1.00 | 18953 | 3 | | | | | | SHD | 1.00 |
| 18858 | 3 | | | | | | SELV | 1.00 | 18954 | 3 | | | | | | SHE | 1.00 |
| 18859 | 3 | | | | | | SEMA3A | 1.00 | 18955 | 3 | | | | | | SHF | 1.00 |
| 18860 | 3 | | | | | | SEMA3D | 1.00 | 18956 | 3 | | | | | | SHH | 1.00 |
| 18861 | 3 | | | | | | SEMA3E | 1.00 | 18957 | 3 | | | | | | SHISA2 | 1.00 |
| 18862 | 3 | | | | | | SEMA3F | 1.00 | 18958 | 3 | | | | | | SHISA3 | 1.00 |
| 18863 | 3 | | | | | | SEMA3G | 1.00 | 18959 | 3 | | | | | | SHISA6 | 1.00 |
| 18864 | 3 | | | | | | SEMA5A | 1.00 | 18960 | 3 | | | | | | SHISA7 | 1.00 |
| 18865 | 3 | | | | | | SEMA5B | 1.00 | 18961 | 3 | | | | | | SHISA8 | 1.00 |
| 18866 | 3 | | | | | | SEMA6A | 1.00 | 18962 | 3 | | | | | | SHISA9 | 1.00 |
| 18867 | 3 | | | | | | SEMA6B | 1.00 | 18963 | 3 | | | | | | SHOX | 1.00 |
| 18868 | 3 | | | | | | SEMA6C | 1.00 | 18964 | 3 | | | | | | SHOX2 | 1.00 |
| 18869 | 3 | | | | | | SEMA6D | 1.00 | 18965 | 3 | | | | | | SHROOM2 | 1.00 |
| 18870 | 3 | | | | | | SEMG2 | 1.00 | 18966 | 3 | | | | | | SHROOM3 | 1.00 |
| 18871 | 3 | | | | | | SENP3-EIF4A1 | 1.00 | 18967 | 3 | | | | | | SHROOM4 | 1.00 |
| 18872 | 3 | | | | | | SENP8 | 1.00 | 18968 | 3 | | | | | | SI | 1.00 |
| 18873 | 3 | | | | | | SEPP1 | 1.00 | 18969 | 3 | | | | | | SIAH3 | 1.00 |
| 18874 | 3 | | | | | | 42625 | 1.00 | 18970 | 3 | | | | | | SIGLEC11 | 1.00 |
| 18875 | 3 | | | | | | 42627 | 1.00 | 18971 | 3 | | | | | | SIGLEC15 | 1.00 |
| 18876 | 3 | | | | | | 42616 | 1.00 | 18972 | 3 | | | | | | SIM1 | 1.00 |
| 18877 | 3 | | | | | | SEPT7L | 1.00 | 18973 | 3 | | | | | | SIM2 | 1.00 |
| 18878 | 3 | | | | | | SERF1A | 1.00 | 18974 | 3 | | | | | | SIX1 | 1.00 |
| 18879 | 3 | | | | | | SERF2-C15ORF63 | 1.00 | 18975 | 3 | | | | | | SIX2 | 1.00 |
| 18880 | 3 | | | | | | SERHL | 1.00 | 18976 | 3 | | | | | | SIX3 | 1.00 |
| 18881 | 3 | | | | | | SERHL2 | 1.00 | 18977 | 3 | | | | | | SIX4 | 1.00 |
| 18882 | 3 | | | | | | SERP2 | 1.00 | 18978 | 3 | | | | | | SIX5 | 1.00 |
| 18883 | 3 | | | | | | SERPINA10 | 1.00 | 18979 | 3 | | | | | | SIX6 | 1.00 |
| 18884 | 3 | | | | | | SERPINA11 | 1.00 | 18980 | 3 | | | | | | SKA1 | 1.00 |
| 18885 | 3 | | | | | | SERPINA12 | 1.00 | 18981 | 3 | | | | | | SKA3 | 1.00 |
| 18886 | 3 | | | | | | SERPINA13 | 1.00 | 18982 | 3 | | | | | | SKINTL | 1.00 |
| 18887 | 3 | | | | | | SERPINA3 | 1.00 | 18983 | 3 | | | | | | SKOR1 | 1.00 |
| 18888 | 3 | | | | | | SERPINA4 | 1.00 | 18984 | 3 | | | | | | SLAMF9 | 1.00 |
| 18889 | 3 | | | | | | SERPINA5 | 1.00 | 18985 | 3 | | | | | | SLC10A1 | 1.00 |
| 18890 | 3 | | | | | | SERPINA6 | 1.00 | 18986 | 3 | | | | | | SLC10A2 | 1.00 |
| 18891 | 3 | | | | | | SERPINA7 | 1.00 | 18987 | 3 | | | | | | SLC10A4 | 1.00 |
| 18892 | 3 | | | | | | SERPINA9 | 1.00 | 18988 | 3 | | | | | | SLC10A5 | 1.00 |
| 18893 | 3 | | | | | | SERPINB10 | 1.00 | 18989 | 3 | | | | | | SLC10A6 | 1.00 |
| 18894 | 3 | | | | | | SERPINB11 | 1.00 | 18990 | 3 | | | | | | SLC12A1 | 1.00 |
| 18895 | 3 | | | | | | SERPINB12 | 1.00 | 18991 | 3 | | | | | | SLC12A3 | 1.00 |
| 18896 | 3 | | | | | | SERPINB13 | 1.00 | 18992 | 3 | | | | | | SLC12A5 | 1.00 |
| 18897 | 3 | | | | | | SERPINB3 | 1.00 | 18993 | 3 | | | | | | SLC12A8 | 1.00 |
| 18898 | 3 | | | | | | SERPINB4 | 1.00 | 18994 | 3 | | | | | | SLC13A1 | 1.00 |
| 18899 | 3 | | | | | | SERPINB5 | 1.00 | 18995 | 3 | | | | | | SLC13A2 | 1.00 |
| 18900 | 3 | | | | | | SERPINB7 | 1.00 | 18996 | 3 | | | | | | SLC13A3 | 1.00 |
| 18901 | 3 | | | | | | SERPINC1 | 1.00 | 18997 | 3 | | | | | | SLC13A4 | 1.00 |
| 18902 | 3 | | | | | | SERPIND1 | 1.00 | 18998 | 3 | | | | | | SLC13A5 | 1.00 |
| 18903 | 3 | | | | | | SERPINE3 | 1.00 | 18999 | 3 | | | | | | SLC14A2 | 1.00 |
| 18904 | 3 | | | | | | SERPINI2 | 1.00 | 19000 | 3 | | | | | | SLC15A1 | 1.00 |

Fig. 40 - 100

| | | | | | | | | | | | | | | |
|---|---|---|---|---|---|---|---|---|---|---|---|---|---|---|
| 19001 | 3 | | | | | | SLC15A5 | 1.00 | 19097 | 3 | | | SLC44A3 | 1.00 |
| 19002 | 3 | | | | | | SLC16A10 | 1.00 | 19098 | 3 | | | SLC44A4 | 1.00 |
| 19003 | 3 | | | | | | SLC16A11 | 1.00 | 19099 | 3 | | | SLC44A5 | 1.00 |
| 19004 | 3 | | | | | | SLC16A12 | 1.00 | 19100 | 3 | | | SLC45A1 | 1.00 |
| 19005 | 3 | | | | | | SLC16A14 | 1.00 | 19101 | 3 | | | SLC45A2 | 1.00 |
| 19006 | 3 | | | | | | SLC16A2 | 1.00 | 19102 | 3 | | | SLC47A1 | 1.00 |
| 19007 | 3 | | | | | | SLC16A4 | 1.00 | 19103 | 3 | | | SLC47A2 | 1.00 |
| 19008 | 3 | | | | | | SLC16A8 | 1.00 | 19104 | 3 | | | SLC4A11 | 1.00 |
| 19009 | 3 | | | | | | SLC16A9 | 1.00 | 19105 | 3 | | | SLC4A3 | 1.00 |
| 19010 | 3 | | | | | | SLC17A1 | 1.00 | 19106 | 3 | | | SLC4A4 | 1.00 |
| 19011 | 3 | | | | | | SLC17A2 | 1.00 | 19107 | 3 | | | SLC4A8 | 1.00 |
| 19012 | 3 | | | | | | SLC17A3 | 1.00 | 19108 | 3 | | | SLC4A9 | 1.00 |
| 19013 | 3 | | | | | | SLC17A4 | 1.00 | 19109 | 3 | | | SLC5A1 | 1.00 |
| 19014 | 3 | | | | | | SLC17A6 | 1.00 | 19110 | 3 | | | SLC5A10 | 1.00 |
| 19015 | 3 | | | | | | SLC17A7 | 1.00 | 19111 | 3 | | | SLC5A11 | 1.00 |
| 19016 | 3 | | | | | | SLC17A8 | 1.00 | 19112 | 3 | | | SLC5A12 | 1.00 |
| 19017 | 3 | | | | | | SLC18A1 | 1.00 | 19113 | 3 | | | SLC5A2 | 1.00 |
| 19018 | 3 | | | | | | SLC18A3 | 1.00 | 19114 | 3 | | | SLC5A4 | 1.00 |
| 19019 | 3 | | | | | | SLC19A3 | 1.00 | 19115 | 3 | | | SLC5A5 | 1.00 |
| 19020 | 3 | | | | | | SLC1A1 | 1.00 | 19116 | 3 | | | SLC5A7 | 1.00 |
| 19021 | 3 | | | | | | SLC1A2 | 1.00 | 19117 | 3 | | | SLC5A8 | 1.00 |
| 19022 | 3 | | | | | | SLC1A6 | 1.00 | 19118 | 3 | | | SLC6A1 | 1.00 |
| 19023 | 3 | | | | | | SLC1A7 | 1.00 | 19119 | 3 | | | SLC6A10P | 1.00 |
| 19024 | 3 | | | | | | SLC22A10 | 1.00 | 19120 | 3 | | | SLC6A11 | 1.00 |
| 19025 | 3 | | | | | | SLC22A11 | 1.00 | 19121 | 3 | | | SLC6A13 | 1.00 |
| 19026 | 3 | | | | | | SLC22A12 | 1.00 | 19122 | 3 | | | SLC6A14 | 1.00 |
| 19027 | 3 | | | | | | SLC22A13 | 1.00 | 19123 | 3 | | | SLC6A15 | 1.00 |
| 19028 | 3 | | | | | | SLC22A14 | 1.00 | 19124 | 3 | | | SLC6A17 | 1.00 |
| 19029 | 3 | | | | | | SLC22A18AS | 1.00 | 19125 | 3 | | | SLC6A18 | 1.00 |
| 19030 | 3 | | | | | | SLC22A2 | 1.00 | 19126 | 3 | | | SLC6A19 | 1.00 |
| 19031 | 3 | | | | | | SLC22A20 | 1.00 | 19127 | 3 | | | SLC6A2 | 1.00 |
| 19032 | 3 | | | | | | SLC22A24 | 1.00 | 19128 | 3 | | | SLC6A20 | 1.00 |
| 19033 | 3 | | | | | | SLC22A25 | 1.00 | 19129 | 3 | | | SLC6A3 | 1.00 |
| 19034 | 3 | | | | | | SLC22A3 | 1.00 | 19130 | 3 | | | SLC6A4 | 1.00 |
| 19035 | 3 | | | | | | SLC22A31 | 1.00 | 19131 | 3 | | | SLC6A5 | 1.00 |
| 19036 | 3 | | | | | | SLC22A6 | 1.00 | 19132 | 3 | | | SLC6A7 | 1.00 |
| 19037 | 3 | | | | | | SLC22A7 | 1.00 | 19133 | 3 | | | SLC7A10 | 1.00 |
| 19038 | 3 | | | | | | SLC22A8 | 1.00 | 19134 | 3 | | | SLC7A11 | 1.00 |
| 19039 | 3 | | | | | | SLC22A9 | 1.00 | 19135 | 3 | | | SLC7A13 | 1.00 |
| 19040 | 3 | | | | | | SLC23A1 | 1.00 | 19136 | 3 | | | SLC7A14 | 1.00 |
| 19041 | 3 | | | | | | SLC24A2 | 1.00 | 19137 | 3 | | | SLC7A2 | 1.00 |
| 19042 | 3 | | | | | | SLC24A5 | 1.00 | 19138 | 3 | | | SLC7A3 | 1.00 |
| 19043 | 3 | | | | | | SLC25A10 | 1.00 | 19139 | 3 | | | SLC7A4 | 1.00 |
| 19044 | 3 | | | | | | SLC25A18 | 1.00 | 19140 | 3 | | | SLC7A9 | 1.00 |
| 19045 | 3 | | | | | | SLC25A2 | 1.00 | 19141 | 3 | | | SLC8A2 | 1.00 |
| 19046 | 3 | | | | | | SLC25A21 | 1.00 | 19142 | 3 | | | SLC8A3 | 1.00 |
| 19047 | 3 | | | | | | SLC25A27 | 1.00 | 19143 | 3 | | | SLC9A10 | 1.00 |
| 19048 | 3 | | | | | | SLC25A31 | 1.00 | 19144 | 3 | | | SLC9A11 | 1.00 |
| 19049 | 3 | | | | | | SLC25A41 | 1.00 | 19145 | 3 | | | SLC9A2 | 1.00 |
| 19050 | 3 | | | | | | SLC25A47 | 1.00 | 19146 | 3 | | | SLC9A3 | 1.00 |
| 19051 | 3 | | | | | | SLC25A48 | 1.00 | 19147 | 3 | | | SLC9A4 | 1.00 |
| 19052 | 3 | | | | | | SLC26A10 | 1.00 | 19148 | 3 | | | SLC9A5 | 1.00 |
| 19053 | 3 | | | | | | SLC26A3 | 1.00 | 19149 | 3 | | | SLC9A7 | 1.00 |
| 19054 | 3 | | | | | | SLC26A4 | 1.00 | 19150 | 3 | | | SLC9B1 | 1.00 |
| 19055 | 3 | | | | | | SLC26A5 | 1.00 | 19151 | 3 | | | SLCO1A2 | 1.00 |
| 19056 | 3 | | | | | | SLC26A7 | 1.00 | 19152 | 3 | | | SLCO1B1 | 1.00 |
| 19057 | 3 | | | | | | SLC26A9 | 1.00 | 19153 | 3 | | | SLCO1B3 | 1.00 |
| 19058 | 3 | | | | | | SLC27A2 | 1.00 | 19154 | 3 | | | SLCO1B7 | 1.00 |
| 19059 | 3 | | | | | | SLC27A5 | 1.00 | 19155 | 3 | | | SLCO1C1 | 1.00 |
| 19060 | 3 | | | | | | SLC27A6 | 1.00 | 19156 | 3 | | | SLCO2A1 | 1.00 |
| 19061 | 3 | | | | | | SLC28A1 | 1.00 | 19157 | 3 | | | SLCO2B1 | 1.00 |
| 19062 | 3 | | | | | | SLC28A2 | 1.00 | 19158 | 3 | | | SLCO4A1 | 1.00 |
| 19063 | 3 | | | | | | SLC28A3 | 1.00 | 19159 | 3 | | | SLCO5A1 | 1.00 |
| 19064 | 3 | | | | | | SLC29A4 | 1.00 | 19160 | 3 | | | SLCO6A1 | 1.00 |
| 19065 | 3 | | | | | | SLC2A10 | 1.00 | 19161 | 3 | | | SLED1 | 1.00 |
| 19066 | 3 | | | | | | SLC2A12 | 1.00 | 19162 | 3 | | | SLFNL1 | 1.00 |
| 19067 | 3 | | | | | | SLC2A2 | 1.00 | 19163 | 3 | | | SLIT1 | 1.00 |
| 19068 | 3 | | | | | | SLC2A4 | 1.00 | 19164 | 3 | | | SLIT2 | 1.00 |
| 19069 | 3 | | | | | | SLC2A7 | 1.00 | 19165 | 3 | | | SLIT2-IT1 | 1.00 |
| 19070 | 3 | | | | | | SLC30A10 | 1.00 | 19166 | 3 | | | SLIT3 | 1.00 |
| 19071 | 3 | | | | | | SLC30A2 | 1.00 | 19167 | 3 | | | SLITRK1 | 1.00 |
| 19072 | 3 | | | | | | SLC30A3 | 1.00 | 19168 | 3 | | | SLITRK2 | 1.00 |
| 19073 | 3 | | | | | | SLC30A8 | 1.00 | 19169 | 3 | | | SLITRK3 | 1.00 |
| 19074 | 3 | | | | | | SLC32A1 | 1.00 | 19170 | 3 | | | SLITRK5 | 1.00 |
| 19075 | 3 | | | | | | SLC34A1 | 1.00 | 19171 | 3 | | | SLITRK6 | 1.00 |
| 19076 | 3 | | | | | | SLC34A2 | 1.00 | 19172 | 3 | | | SLMO1 | 1.00 |
| 19077 | 3 | | | | | | SLC34A3 | 1.00 | 19173 | 3 | | | SLMO2-ATP5E | 1.00 |
| 19078 | 3 | | | | | | SLC35D3 | 1.00 | 19174 | 3 | | | SLN | 1.00 |
| 19079 | 3 | | | | | | SLC35F1 | 1.00 | 19175 | 3 | | | SLURP1 | 1.00 |
| 19080 | 3 | | | | | | SLC35F3 | 1.00 | 19176 | 3 | | | SMAD5-AS1 | 1.00 |
| 19081 | 3 | | | | | | SLC35F4 | 1.00 | 19177 | 3 | | | SMAD6 | 1.00 |
| 19082 | 3 | | | | | | SLC35G1 | 1.00 | 19178 | 3 | | | SMAD9 | 1.00 |
| 19083 | 3 | | | | | | SLC35G3 | 1.00 | 19179 | 3 | | | SMARCA1 | 1.00 |
| 19084 | 3 | | | | | | SLC35G5 | 1.00 | 19180 | 3 | | | SMC1B | 1.00 |
| 19085 | 3 | | | | | | SLC35G6 | 1.00 | 19181 | 3 | | | SMCP | 1.00 |
| 19086 | 3 | | | | | | SLC36A2 | 1.00 | 19182 | 3 | | | SMCR5 | 1.00 |
| 19087 | 3 | | | | | | SLC36A3 | 1.00 | 19183 | 3 | | | SMCR9 | 1.00 |
| 19088 | 3 | | | | | | SLC38A11 | 1.00 | 19184 | 3 | | | SMEK3P | 1.00 |
| 19089 | 3 | | | | | | SLC38A3 | 1.00 | 19185 | 3 | | | SMN1 | 1.00 |
| 19090 | 3 | | | | | | SLC38A4 | 1.00 | 19186 | 3 | | | SMO | 1.00 |
| 19091 | 3 | | | | | | SLC38A8 | 1.00 | 19187 | 3 | | | SMOC1 | 1.00 |
| 19092 | 3 | | | | | | SLC39A12 | 1.00 | 19188 | 3 | | | SMOC2 | 1.00 |
| 19093 | 3 | | | | | | SLC39A2 | 1.00 | 19189 | 3 | | | SMPX | 1.00 |
| 19094 | 3 | | | | | | SLC39A5 | 1.00 | 19190 | 3 | | | SMR3A | 1.00 |
| 19095 | 3 | | | | | | SLC3A1 | 1.00 | 19191 | 3 | | | SMR3B | 1.00 |
| 19096 | 3 | | | | | | SLC41A2 | 1.00 | 19192 | 3 | | | SMTN | 1.00 |

Fig. 40 - 101

| | | | | | | | | | | | | | | | |
|---|---|---|---|---|---|---|---|---|---|---|---|---|---|---|---|
| 19193 | 3 | | | | | SMTNL2 | 1.00 | 19289 | 3 | | | | | SNORA72 | 1.00 |
| 19194 | 3 | | | | | SMYD1 | 1.00 | 19290 | 3 | | | | | SNORA74A | 1.00 |
| 19195 | 3 | | | | | SNAI2 | 1.00 | 19291 | 3 | | | | | SNORA74B | 1.00 |
| 19196 | 3 | | | | | SNAP25 | 1.00 | 19292 | 3 | | | | | SNORA76 | 1.00 |
| 19197 | 3 | | | | | SNAP91 | 1.00 | 19293 | 3 | | | | | SNORA77 | 1.00 |
| 19198 | 3 | | | | | SNAR-A1 | 1.00 | 19294 | 3 | | | | | SNORA78 | 1.00 |
| 19199 | 3 | | | | | SNAR-A11 | 1.00 | 19295 | 3 | | | | | SNORA79 | 1.00 |
| 19200 | 3 | | | | | SNAR-A12 | 1.00 | 19296 | 3 | | | | | SNORA7A | 1.00 |
| 19201 | 3 | | | | | SNAR-A13 | 1.00 | 19297 | 3 | | | | | SNORA7B | 1.00 |
| 19202 | 3 | | | | | SNAR-A14 | 1.00 | 19298 | 3 | | | | | SNORA80 | 1.00 |
| 19203 | 3 | | | | | SNAR-A2 | 1.00 | 19299 | 3 | | | | | SNORA80B | 1.00 |
| 19204 | 3 | | | | | SNAR-A3 | 1.00 | 19300 | 3 | | | | | SNORA84 | 1.00 |
| 19205 | 3 | | | | | SNAR-A6 | 1.00 | 19301 | 3 | | | | | SNORA9 | 1.00 |
| 19206 | 3 | | | | | SNAR-A7 | 1.00 | 19302 | 3 | | | | | SNORD10 | 1.00 |
| 19207 | 3 | | | | | SNAR-A8 | 1.00 | 19303 | 3 | | | | | SNORD100 | 1.00 |
| 19208 | 3 | | | | | SNAR-B2 | 1.00 | 19304 | 3 | | | | | SNORD101 | 1.00 |
| 19209 | 3 | | | | | SNAR-C2 | 1.00 | 19305 | 3 | | | | | SNORD102 | 1.00 |
| 19210 | 3 | | | | | SNAR-C3 | 1.00 | 19306 | 3 | | | | | SNORD103A | 1.00 |
| 19211 | 3 | | | | | SNAR-C4 | 1.00 | 19307 | 3 | | | | | SNORD104 | 1.00 |
| 19212 | 3 | | | | | SNAR-C5 | 1.00 | 19308 | 3 | | | | | SNORD105 | 1.00 |
| 19213 | 3 | | | | | SNAR-D | 1.00 | 19309 | 3 | | | | | SNORD105B | 1.00 |
| 19214 | 3 | | | | | SNAR-E | 1.00 | 19310 | 3 | | | | | SNORD107 | 1.00 |
| 19215 | 3 | | | | | SNAR-F | 1.00 | 19311 | 3 | | | | | SNORD108 | 1.00 |
| 19216 | 3 | | | | | SNAR-G1 | 1.00 | 19312 | 3 | | | | | SNORD109B | 1.00 |
| 19217 | 3 | | | | | SNAR-G2 | 1.00 | 19313 | 3 | | | | | SNORD11 | 1.00 |
| 19218 | 3 | | | | | SNAR-H | 1.00 | 19314 | 3 | | | | | SNORD110 | 1.00 |
| 19219 | 3 | | | | | SNAR-I | 1.00 | 19315 | 3 | | | | | SNORD111 | 1.00 |
| 19220 | 3 | | | | | SNCAIP | 1.00 | 19316 | 3 | | | | | SNORD111B | 1.00 |
| 19221 | 3 | | | | | SNCB | 1.00 | 19317 | 3 | | | | | SNORD113-1 | 1.00 |
| 19222 | 3 | | | | | SNCG | 1.00 | 19318 | 3 | | | | | SNORD113-2 | 1.00 |
| 19223 | 3 | | | | | SNED1 | 1.00 | 19319 | 3 | | | | | SNORD113-4 | 1.00 |
| 19224 | 3 | | | | | SNORA1 | 1.00 | 19320 | 3 | | | | | SNORD113-5 | 1.00 |
| 19225 | 3 | | | | | SNORA10 | 1.00 | 19321 | 3 | | | | | SNORD113-6 | 1.00 |
| 19226 | 3 | | | | | SNORA11 | 1.00 | 19322 | 3 | | | | | SNORD113-7 | 1.00 |
| 19227 | 3 | | | | | SNORA11B | 1.00 | 19323 | 3 | | | | | SNORD113-9 | 1.00 |
| 19228 | 3 | | | | | SNORA11C | 1.00 | 19324 | 3 | | | | | SNORD114-1 | 1.00 |
| 19229 | 3 | | | | | SNORA13 | 1.00 | 19325 | 3 | | | | | SNORD114-10 | 1.00 |
| 19230 | 3 | | | | | SNORA14A | 1.00 | 19326 | 3 | | | | | SNORD114-11 | 1.00 |
| 19231 | 3 | | | | | SNORA14B | 1.00 | 19327 | 3 | | | | | SNORD114-12 | 1.00 |
| 19232 | 3 | | | | | SNORA15 | 1.00 | 19328 | 3 | | | | | SNORD114-13 | 1.00 |
| 19233 | 3 | | | | | SNORA16A | 1.00 | 19329 | 3 | | | | | SNORD114-14 | 1.00 |
| 19234 | 3 | | | | | SNORA16B | 1.00 | 19330 | 3 | | | | | SNORD114-15 | 1.00 |
| 19235 | 3 | | | | | SNORA17 | 1.00 | 19331 | 3 | | | | | SNORD114-16 | 1.00 |
| 19236 | 3 | | | | | SNORA18 | 1.00 | 19332 | 3 | | | | | SNORD114-17 | 1.00 |
| 19237 | 3 | | | | | SNORA19 | 1.00 | 19333 | 3 | | | | | SNORD114-18 | 1.00 |
| 19238 | 3 | | | | | SNORA20 | 1.00 | 19334 | 3 | | | | | SNORD114-19 | 1.00 |
| 19239 | 3 | | | | | SNORA22 | 1.00 | 19335 | 3 | | | | | SNORD114-2 | 1.00 |
| 19240 | 3 | | | | | SNORA23 | 1.00 | 19336 | 3 | | | | | SNORD114-20 | 1.00 |
| 19241 | 3 | | | | | SNORA24 | 1.00 | 19337 | 3 | | | | | SNORD114-21 | 1.00 |
| 19242 | 3 | | | | | SNORA25 | 1.00 | 19338 | 3 | | | | | SNORD114-22 | 1.00 |
| 19243 | 3 | | | | | SNORA26 | 1.00 | 19339 | 3 | | | | | SNORD114-23 | 1.00 |
| 19244 | 3 | | | | | SNORA28 | 1.00 | 19340 | 3 | | | | | SNORD114-24 | 1.00 |
| 19245 | 3 | | | | | SNORA2A | 1.00 | 19341 | 3 | | | | | SNORD114-25 | 1.00 |
| 19246 | 3 | | | | | SNORA3 | 1.00 | 19342 | 3 | | | | | SNORD114-26 | 1.00 |
| 19247 | 3 | | | | | SNORA30 | 1.00 | 19343 | 3 | | | | | SNORD114-27 | 1.00 |
| 19248 | 3 | | | | | SNORA32 | 1.00 | 19344 | 3 | | | | | SNORD114-28 | 1.00 |
| 19249 | 3 | | | | | SNORA33 | 1.00 | 19345 | 3 | | | | | SNORD114-29 | 1.00 |
| 19250 | 3 | | | | | SNORA34 | 1.00 | 19346 | 3 | | | | | SNORD114-3 | 1.00 |
| 19251 | 3 | | | | | SNORA35 | 1.00 | 19347 | 3 | | | | | SNORD114-30 | 1.00 |
| 19252 | 3 | | | | | SNORA36A | 1.00 | 19348 | 3 | | | | | SNORD114-31 | 1.00 |
| 19253 | 3 | | | | | SNORA36B | 1.00 | 19349 | 3 | | | | | SNORD114-4 | 1.00 |
| 19254 | 3 | | | | | SNORA36C | 1.00 | 19350 | 3 | | | | | SNORD114-5 | 1.00 |
| 19255 | 3 | | | | | SNORA38 | 1.00 | 19351 | 3 | | | | | SNORD114-6 | 1.00 |
| 19256 | 3 | | | | | SNORA38B | 1.00 | 19352 | 3 | | | | | SNORD114-7 | 1.00 |
| 19257 | 3 | | | | | SNORA41 | 1.00 | 19353 | 3 | | | | | SNORD114-8 | 1.00 |
| 19258 | 3 | | | | | SNORA43 | 1.00 | 19354 | 3 | | | | | SNORD114-9 | 1.00 |
| 19259 | 3 | | | | | SNORA46 | 1.00 | 19355 | 3 | | | | | SNORD115-1 | 1.00 |
| 19260 | 3 | | | | | SNORA47 | 1.00 | 19356 | 3 | | | | | SNORD115-10 | 1.00 |
| 19261 | 3 | | | | | SNORA49 | 1.00 | 19357 | 3 | | | | | SNORD115-11 | 1.00 |
| 19262 | 3 | | | | | SNORA50 | 1.00 | 19358 | 3 | | | | | SNORD115-12 | 1.00 |
| 19263 | 3 | | | | | SNORA51 | 1.00 | 19359 | 3 | | | | | SNORD115-13 | 1.00 |
| 19264 | 3 | | | | | SNORA52 | 1.00 | 19360 | 3 | | | | | SNORD115-14 | 1.00 |
| 19265 | 3 | | | | | SNORA53 | 1.00 | 19361 | 3 | | | | | SNORD115-15 | 1.00 |
| 19266 | 3 | | | | | SNORA54 | 1.00 | 19362 | 3 | | | | | SNORD115-16 | 1.00 |
| 19267 | 3 | | | | | SNORA56 | 1.00 | 19363 | 3 | | | | | SNORD115-17 | 1.00 |
| 19268 | 3 | | | | | SNORA58 | 1.00 | 19364 | 3 | | | | | SNORD115-18 | 1.00 |
| 19269 | 3 | | | | | SNORA59B | 1.00 | 19365 | 3 | | | | | SNORD115-19 | 1.00 |
| 19270 | 3 | | | | | SNORA5B | 1.00 | 19366 | 3 | | | | | SNORD115-2 | 1.00 |
| 19271 | 3 | | | | | SNORA5C | 1.00 | 19367 | 3 | | | | | SNORD115-20 | 1.00 |
| 19272 | 3 | | | | | SNORA60 | 1.00 | 19368 | 3 | | | | | SNORD115-21 | 1.00 |
| 19273 | 3 | | | | | SNORA61 | 1.00 | 19369 | 3 | | | | | SNORD115-22 | 1.00 |
| 19274 | 3 | | | | | SNORA62 | 1.00 | 19370 | 3 | | | | | SNORD115-23 | 1.00 |
| 19275 | 3 | | | | | SNORA64 | 1.00 | 19371 | 3 | | | | | SNORD115-24 | 1.00 |
| 19276 | 3 | | | | | SNORA65 | 1.00 | 19372 | 3 | | | | | SNORD115-25 | 1.00 |
| 19277 | 3 | | | | | SNORA66 | 1.00 | 19373 | 3 | | | | | SNORD115-26 | 1.00 |
| 19278 | 3 | | | | | SNORA69 | 1.00 | 19374 | 3 | | | | | SNORD115-27 | 1.00 |
| 19279 | 3 | | | | | SNORA70B | 1.00 | 19375 | 3 | | | | | SNORD115-28 | 1.00 |
| 19280 | 3 | | | | | SNORA70C | 1.00 | 19376 | 3 | | | | | SNORD115-29 | 1.00 |
| 19281 | 3 | | | | | SNORA70D | 1.00 | 19377 | 3 | | | | | SNORD115-3 | 1.00 |
| 19282 | 3 | | | | | SNORA70E | 1.00 | 19378 | 3 | | | | | SNORD115-30 | 1.00 |
| 19283 | 3 | | | | | SNORA70F | 1.00 | 19379 | 3 | | | | | SNORD115-31 | 1.00 |
| 19284 | 3 | | | | | SNORA70G | 1.00 | 19380 | 3 | | | | | SNORD115-32 | 1.00 |
| 19285 | 3 | | | | | SNORA71A | 1.00 | 19381 | 3 | | | | | SNORD115-33 | 1.00 |
| 19286 | 3 | | | | | SNORA71B | 1.00 | 19382 | 3 | | | | | SNORD115-34 | 1.00 |
| 19287 | 3 | | | | | SNORA71C | 1.00 | 19383 | 3 | | | | | SNORD115-35 | 1.00 |
| 19288 | 3 | | | | | SNORA71D | 1.00 | 19384 | 3 | | | | | SNORD115-37 | 1.00 |

Fig. 40 - 102

| | | | | | | |
|---|---|---|---|---|---|---|
| 19385 | 3 | | SNORD115-38 | 1.00 | 19481 | 3 | | SNORD45B | 1.00 |
| 19386 | 3 | | SNORD115-39 | 1.00 | 19482 | 3 | | SNORD45C | 1.00 |
| 19387 | 3 | | SNORD115-4 | 1.00 | 19483 | 3 | | SNORD46 | 1.00 |
| 19388 | 3 | | SNORD115-40 | 1.00 | 19484 | 3 | | SNORD47 | 1.00 |
| 19389 | 3 | | SNORD115-41 | 1.00 | 19485 | 3 | | SNORD48 | 1.00 |
| 19390 | 3 | | SNORD115-42 | 1.00 | 19486 | 3 | | SNORD49A | 1.00 |
| 19391 | 3 | | SNORD115-44 | 1.00 | 19487 | 3 | | SNORD49B | 1.00 |
| 19392 | 3 | | SNORD115-45 | 1.00 | 19488 | 3 | | SNORD4A | 1.00 |
| 19393 | 3 | | SNORD115-47 | 1.00 | 19489 | 3 | | SNORD4B | 1.00 |
| 19394 | 3 | | SNORD115-48 | 1.00 | 19490 | 3 | | SNORD5 | 1.00 |
| 19395 | 3 | | SNORD115-5 | 1.00 | 19491 | 3 | | SNORD50A | 1.00 |
| 19396 | 3 | | SNORD115-6 | 1.00 | 19492 | 3 | | SNORD50B | 1.00 |
| 19397 | 3 | | SNORD115-7 | 1.00 | 19493 | 3 | | SNORD51 | 1.00 |
| 19398 | 3 | | SNORD115-8 | 1.00 | 19494 | 3 | | SNORD52 | 1.00 |
| 19399 | 3 | | SNORD115-9 | 1.00 | 19495 | 3 | | SNORD53 | 1.00 |
| 19400 | 3 | | SNORD116-1 | 1.00 | 19496 | 3 | | SNORD54 | 1.00 |
| 19401 | 3 | | SNORD116-10 | 1.00 | 19497 | 3 | | SNORD55 | 1.00 |
| 19402 | 3 | | SNORD116-11 | 1.00 | 19498 | 3 | | SNORD56 | 1.00 |
| 19403 | 3 | | SNORD116-12 | 1.00 | 19499 | 3 | | SNORD56B | 1.00 |
| 19404 | 3 | | SNORD116-13 | 1.00 | 19500 | 3 | | SNORD57 | 1.00 |
| 19405 | 3 | | SNORD116-14 | 1.00 | 19501 | 3 | | SNORD58A | 1.00 |
| 19406 | 3 | | SNORD116-15 | 1.00 | 19502 | 3 | | SNORD58B | 1.00 |
| 19407 | 3 | | SNORD116-16 | 1.00 | 19503 | 3 | | SNORD58C | 1.00 |
| 19408 | 3 | | SNORD116-17 | 1.00 | 19504 | 3 | | SNORD59A | 1.00 |
| 19409 | 3 | | SNORD116-18 | 1.00 | 19505 | 3 | | SNORD59B | 1.00 |
| 19410 | 3 | | SNORD116-2 | 1.00 | 19506 | 3 | | SNORD6 | 1.00 |
| 19411 | 3 | | SNORD116-20 | 1.00 | 19507 | 3 | | SNORD60 | 1.00 |
| 19412 | 3 | | SNORD116-21 | 1.00 | 19508 | 3 | | SNORD61 | 1.00 |
| 19413 | 3 | | SNORD116-22 | 1.00 | 19509 | 3 | | SNORD62A | 1.00 |
| 19414 | 3 | | SNORD116-23 | 1.00 | 19510 | 3 | | SNORD63 | 1.00 |
| 19415 | 3 | | SNORD116-24 | 1.00 | 19511 | 3 | | SNORD64 | 1.00 |
| 19416 | 3 | | SNORD116-25 | 1.00 | 19512 | 3 | | SNORD65 | 1.00 |
| 19417 | 3 | | SNORD116-26 | 1.00 | 19513 | 3 | | SNORD66 | 1.00 |
| 19418 | 3 | | SNORD116-27 | 1.00 | 19514 | 3 | | SNORD67 | 1.00 |
| 19419 | 3 | | SNORD116-28 | 1.00 | 19515 | 3 | | SNORD68 | 1.00 |
| 19420 | 3 | | SNORD116-29 | 1.00 | 19516 | 3 | | SNORD69 | 1.00 |
| 19421 | 3 | | SNORD116-3 | 1.00 | 19517 | 3 | | SNORD7 | 1.00 |
| 19422 | 3 | | SNORD116-4 | 1.00 | 19518 | 3 | | SNORD70 | 1.00 |
| 19423 | 3 | | SNORD116-5 | 1.00 | 19519 | 3 | | SNORD71 | 1.00 |
| 19424 | 3 | | SNORD116-6 | 1.00 | 19520 | 3 | | SNORD72 | 1.00 |
| 19425 | 3 | | SNORD116-7 | 1.00 | 19521 | 3 | | SNORD73A | 1.00 |
| 19426 | 3 | | SNORD116-8 | 1.00 | 19522 | 3 | | SNORD74 | 1.00 |
| 19427 | 3 | | SNORD116-9 | 1.00 | 19523 | 3 | | SNORD75 | 1.00 |
| 19428 | 3 | | SNORD117 | 1.00 | 19524 | 3 | | SNORD76 | 1.00 |
| 19429 | 3 | | SNORD119 | 1.00 | 19525 | 3 | | SNORD77 | 1.00 |
| 19430 | 3 | | SNORD11B | 1.00 | 19526 | 3 | | SNORD78 | 1.00 |
| 19431 | 3 | | SNORD12 | 1.00 | 19527 | 3 | | SNORD79 | 1.00 |
| 19432 | 3 | | SNORD121A | 1.00 | 19528 | 3 | | SNORD8 | 1.00 |
| 19433 | 3 | | SNORD121B | 1.00 | 19529 | 3 | | SNORD80 | 1.00 |
| 19434 | 3 | | SNORD123 | 1.00 | 19530 | 3 | | SNORD81 | 1.00 |
| 19435 | 3 | | SNORD124 | 1.00 | 19531 | 3 | | SNORD82 | 1.00 |
| 19436 | 3 | | SNORD125 | 1.00 | 19532 | 3 | | SNORD83A | 1.00 |
| 19437 | 3 | | SNORD126 | 1.00 | 19533 | 3 | | SNORD83B | 1.00 |
| 19438 | 3 | | SNORD127 | 1.00 | 19534 | 3 | | SNORD84 | 1.00 |
| 19439 | 3 | | SNORD12B | 1.00 | 19535 | 3 | | SNORD85 | 1.00 |
| 19440 | 3 | | SNORD12C | 1.00 | 19536 | 3 | | SNORD86 | 1.00 |
| 19441 | 3 | | SNORD16 | 1.00 | 19537 | 3 | | SNORD87 | 1.00 |
| 19442 | 3 | | SNORD18A | 1.00 | 19538 | 3 | | SNORD88A | 1.00 |
| 19443 | 3 | | SNORD18B | 1.00 | 19539 | 3 | | SNORD88B | 1.00 |
| 19444 | 3 | | SNORD18C | 1.00 | 19540 | 3 | | SNORD88C | 1.00 |
| 19445 | 3 | | SNORD19 | 1.00 | 19541 | 3 | | SNORD9 | 1.00 |
| 19446 | 3 | | SNORD19B | 1.00 | 19542 | 3 | | SNORD90 | 1.00 |
| 19447 | 3 | | SNORD1A | 1.00 | 19543 | 3 | | SNORD91A | 1.00 |
| 19448 | 3 | | SNORD1B | 1.00 | 19544 | 3 | | SNORD91B | 1.00 |
| 19449 | 3 | | SNORD1C | 1.00 | 19545 | 3 | | SNORD92 | 1.00 |
| 19450 | 3 | | SNORD2 | 1.00 | 19546 | 3 | | SNORD93 | 1.00 |
| 19451 | 3 | | SNORD20 | 1.00 | 19547 | 3 | | SNORD94 | 1.00 |
| 19452 | 3 | | SNORD21 | 1.00 | 19548 | 3 | | SNORD95 | 1.00 |
| 19453 | 3 | | SNORD22 | 1.00 | 19549 | 3 | | SNORD96A | 1.00 |
| 19454 | 3 | | SNORD23 | 1.00 | 19550 | 3 | | SNORD96B | 1.00 |
| 19455 | 3 | | SNORD24 | 1.00 | 19551 | 3 | | SNORD98 | 1.00 |
| 19456 | 3 | | SNORD25 | 1.00 | 19552 | 3 | | SNORD99 | 1.00 |
| 19457 | 3 | | SNORD26 | 1.00 | 19553 | 3 | | SNRPD2P2 | 1.00 |
| 19458 | 3 | | SNORD27 | 1.00 | 19554 | 3 | | SNTG1 | 1.00 |
| 19459 | 3 | | SNORD28 | 1.00 | 19555 | 3 | | SNTG2 | 1.00 |
| 19460 | 3 | | SNORD29 | 1.00 | 19556 | 3 | | SNTN | 1.00 |
| 19461 | 3 | | SNORD30 | 1.00 | 19557 | 3 | | SNX31 | 1.00 |
| 19462 | 3 | | SNORD31 | 1.00 | 19558 | 3 | | SNX32 | 1.00 |
| 19463 | 3 | | SNORD32A | 1.00 | 19559 | 3 | | SNX7 | 1.00 |
| 19464 | 3 | | SNORD32B | 1.00 | 19560 | 3 | | SOAT2 | 1.00 |
| 19465 | 3 | | SNORD33 | 1.00 | 19561 | 3 | | SOBP | 1.00 |
| 19466 | 3 | | SNORD34 | 1.00 | 19562 | 3 | | SOD3 | 1.00 |
| 19467 | 3 | | SNORD35A | 1.00 | 19563 | 3 | | SOHLH1 | 1.00 |
| 19468 | 3 | | SNORD35B | 1.00 | 19564 | 3 | | SOHLH2 | 1.00 |
| 19469 | 3 | | SNORD36A | 1.00 | 19565 | 3 | | SORBS1 | 1.00 |
| 19470 | 3 | | SNORD36B | 1.00 | 19566 | 3 | | SORBS2 | 1.00 |
| 19471 | 3 | | SNORD36C | 1.00 | 19567 | 3 | | SORCS1 | 1.00 |
| 19472 | 3 | | SNORD37 | 1.00 | 19568 | 3 | | SORCS2 | 1.00 |
| 19473 | 3 | | SNORD38A | 1.00 | 19569 | 3 | | SORCS3 | 1.00 |
| 19474 | 3 | | SNORD38B | 1.00 | 19570 | 3 | | SOST | 1.00 |
| 19475 | 3 | | SNORD41 | 1.00 | 19571 | 3 | | SOSTDC1 | 1.00 |
| 19476 | 3 | | SNORD42A | 1.00 | 19572 | 3 | | SOWAHA | 1.00 |
| 19477 | 3 | | SNORD42B | 1.00 | 19573 | 3 | | SOWAHB | 1.00 |
| 19478 | 3 | | SNORD43 | 1.00 | 19574 | 3 | | SOX1 | 1.00 |
| 19479 | 3 | | SNORD44 | 1.00 | 19575 | 3 | | SOX10 | 1.00 |
| 19480 | 3 | | SNORD45A | 1.00 | 19576 | 3 | | SOX11 | 1.00 |

Fig. 40 - 103

| | | | | | | | | | | | | | | |
|---|---|---|---|---|---|---|---|---|---|---|---|---|---|---|
| 19577 | 3 | | | | | SOX14 | 1.00 | 19673 | 3 | | | | SPON1 | 1.00 |
| 19578 | 3 | | | | | SOX15 | 1.00 | 19674 | 3 | | | | SPP2 | 1.00 |
| 19579 | 3 | | | | | SOX17 | 1.00 | 19675 | 3 | | | | SPPL2C | 1.00 |
| 19580 | 3 | | | | | SOX18 | 1.00 | 19676 | 3 | | | | SPRED3 | 1.00 |
| 19581 | 3 | | | | | SOX2 | 1.00 | 19677 | 3 | | | | SPRNP1 | 1.00 |
| 19582 | 3 | | | | | SOX2-OT | 1.00 | 19678 | 3 | | | | SPRR1A | 1.00 |
| 19583 | 3 | | | | | SOX21 | 1.00 | 19679 | 3 | | | | SPRR1B | 1.00 |
| 19584 | 3 | | | | | SOX3 | 1.00 | 19680 | 3 | | | | SPRR2A | 1.00 |
| 19585 | 3 | | | | | SOX30 | 1.00 | 19681 | 3 | | | | SPRR2B | 1.00 |
| 19586 | 3 | | | | | SOX5 | 1.00 | 19682 | 3 | | | | SPRR2C | 1.00 |
| 19587 | 3 | | | | | SOX6 | 1.00 | 19683 | 3 | | | | SPRR2D | 1.00 |
| 19588 | 3 | | | | | SOX7 | 1.00 | 19684 | 3 | | | | SPRR2E | 1.00 |
| 19589 | 3 | | | | | SOX9 | 1.00 | 19685 | 3 | | | | SPRR2F | 1.00 |
| 19590 | 3 | | | | | SP5 | 1.00 | 19686 | 3 | | | | SPRR2G | 1.00 |
| 19591 | 3 | | | | | SP6 | 1.00 | 19687 | 3 | | | | SPRR3 | 1.00 |
| 19592 | 3 | | | | | SP7 | 1.00 | 19688 | 3 | | | | SPRR4 | 1.00 |
| 19593 | 3 | | | | | SP8 | 1.00 | 19689 | 3 | | | | SPRY3 | 1.00 |
| 19594 | 3 | | | | | SP9 | 1.00 | 19690 | 3 | | | | SPRY4 | 1.00 |
| 19595 | 3 | | | | | SPA17 | 1.00 | 19691 | 3 | | | | SPRYD5 | 1.00 |
| 19596 | 3 | | | | | SPACA1 | 1.00 | 19692 | 3 | | | | SPSB4 | 1.00 |
| 19597 | 3 | | | | | SPACA3 | 1.00 | 19693 | 3 | | | | SPTBN2 | 1.00 |
| 19598 | 3 | | | | | SPACA4 | 1.00 | 19694 | 3 | | | | SPTBN4 | 1.00 |
| 19599 | 3 | | | | | SPACA5 | 1.00 | 19695 | 3 | | | | SPTBN5 | 1.00 |
| 19600 | 3 | | | | | SPACA5B | 1.00 | 19696 | 3 | | | | SPTLC3 | 1.00 |
| 19601 | 3 | | | | | SPACA7 | 1.00 | 19697 | 3 | | | | SPZ1 | 1.00 |
| 19602 | 3 | | | | | SPAG11A | 1.00 | 19698 | 3 | | | | SRCIN1 | 1.00 |
| 19603 | 3 | | | | | SPAG11B | 1.00 | 19699 | 3 | | | | SRCRB4D | 1.00 |
| 19604 | 3 | | | | | SPAG17 | 1.00 | 19700 | 3 | | | | SRD5A2 | 1.00 |
| 19605 | 3 | | | | | SPAG4 | 1.00 | 19701 | 3 | | | | SRG7 | 1.00 |
| 19606 | 3 | | | | | SPAG5 | 1.00 | 19702 | 3 | | | | SRGAP1 | 1.00 |
| 19607 | 3 | | | | | SPAG6 | 1.00 | 19703 | 3 | | | | SRGAP3 | 1.00 |
| 19608 | 3 | | | | | SPAG8 | 1.00 | 19704 | 3 | | | | SRL | 1.00 |
| 19609 | 3 | | | | | SPAM1 | 1.00 | 19705 | 3 | | | | SRMS | 1.00 |
| 19610 | 3 | | | | | SPANXA1 | 1.00 | 19706 | 3 | | | | SRPK3 | 1.00 |
| 19611 | 3 | | | | | SPANXA2 | 1.00 | 19707 | 3 | | | | SRPX | 1.00 |
| 19612 | 3 | | | | | SPANXA2-OT1 | 1.00 | 19708 | 3 | | | | SRPX2 | 1.00 |
| 19613 | 3 | | | | | SPANXB2 | 1.00 | 19709 | 3 | | | | SRRM3 | 1.00 |
| 19614 | 3 | | | | | SPANXC | 1.00 | 19710 | 3 | | | | SRRM4 | 1.00 |
| 19615 | 3 | | | | | SPANXD | 1.00 | 19711 | 3 | | | | SRRM5 | 1.00 |
| 19616 | 3 | | | | | SPANXE | 1.00 | 19712 | 3 | | | | SRSF12 | 1.00 |
| 19617 | 3 | | | | | SPANXN1 | 1.00 | 19713 | 3 | | | | SRY | 1.00 |
| 19618 | 3 | | | | | SPANXN2 | 1.00 | 19714 | 3 | | | | SSC5D | 1.00 |
| 19619 | 3 | | | | | SPANXN3 | 1.00 | 19715 | 3 | | | | SSPO | 1.00 |
| 19620 | 3 | | | | | SPANXN4 | 1.00 | 19716 | 3 | | | | SSR4P1 | 1.00 |
| 19621 | 3 | | | | | SPANXN5 | 1.00 | 19717 | 3 | | | | SST | 1.00 |
| 19622 | 3 | | | | | SPARCL1 | 1.00 | 19718 | 3 | | | | SSTR1 | 1.00 |
| 19623 | 3 | | | | | SPATA12 | 1.00 | 19719 | 3 | | | | SSTR2 | 1.00 |
| 19624 | 3 | | | | | SPATA16 | 1.00 | 19720 | 3 | | | | SSTR4 | 1.00 |
| 19625 | 3 | | | | | SPATA17 | 1.00 | 19721 | 3 | | | | SSTR5 | 1.00 |
| 19626 | 3 | | | | | SPATA18 | 1.00 | 19722 | 3 | | | | SSX1 | 1.00 |
| 19627 | 3 | | | | | SPATA19 | 1.00 | 19723 | 3 | | | | SSX2 | 1.00 |
| 19628 | 3 | | | | | SPATA21 | 1.00 | 19724 | 3 | | | | SSX3 | 1.00 |
| 19629 | 3 | | | | | SPATA22 | 1.00 | 19725 | 3 | | | | SSX4 | 1.00 |
| 19630 | 3 | | | | | SPATA24 | 1.00 | 19726 | 3 | | | | SSX4B | 1.00 |
| 19631 | 3 | | | | | SPATA25 | 1.00 | 19727 | 3 | | | | SSX5 | 1.00 |
| 19632 | 3 | | | | | SPATA3 | 1.00 | 19728 | 3 | | | | SSX6 | 1.00 |
| 19633 | 3 | | | | | SPATA4 | 1.00 | 19729 | 3 | | | | SSX7 | 1.00 |
| 19634 | 3 | | | | | SPATA7 | 1.00 | 19730 | 3 | | | | SSX8 | 1.00 |
| 19635 | 3 | | | | | SPATA8 | 1.00 | 19731 | 3 | | | | ST18 | 1.00 |
| 19636 | 3 | | | | | SPATA9 | 1.00 | 19732 | 3 | | | | ST20-MTHFS | 1.00 |
| 19637 | 3 | | | | | SPATC1 | 1.00 | 19733 | 3 | | | | ST5 | 1.00 |
| 19638 | 3 | | | | | SPATS1 | 1.00 | 19734 | 3 | | | | ST6GAL2 | 1.00 |
| 19639 | 3 | | | | | SPC24 | 1.00 | 19735 | 3 | | | | ST6GALNAC5 | 1.00 |
| 19640 | 3 | | | | | SPC25 | 1.00 | 19736 | 3 | | | | ST7-AS1 | 1.00 |
| 19641 | 3 | | | | | SPDEF | 1.00 | 19737 | 3 | | | | ST7-AS2 | 1.00 |
| 19642 | 3 | | | | | SPDYA | 1.00 | 19738 | 3 | | | | ST7-OT3 | 1.00 |
| 19643 | 3 | | | | | SPDYE3 | 1.00 | 19739 | 3 | | | | ST7-OT4 | 1.00 |
| 19644 | 3 | | | | | SPDYE4 | 1.00 | 19740 | 3 | | | | ST8SIA1 | 1.00 |
| 19645 | 3 | | | | | SPDYE7P | 1.00 | 19741 | 3 | | | | ST8SIA2 | 1.00 |
| 19646 | 3 | | | | | SPDYE8P | 1.00 | 19742 | 3 | | | | ST8SIA3 | 1.00 |
| 19647 | 3 | | | | | SPEF1 | 1.00 | 19743 | 3 | | | | ST8SIA5 | 1.00 |
| 19648 | 3 | | | | | SPEF2 | 1.00 | 19744 | 3 | | | | STAB2 | 1.00 |
| 19649 | 3 | | | | | SPEM1 | 1.00 | 19745 | 3 | | | | STAC | 1.00 |
| 19650 | 3 | | | | | SPERT | 1.00 | 19746 | 3 | | | | STAC2 | 1.00 |
| 19651 | 3 | | | | | SPESP1 | 1.00 | 19747 | 3 | | | | STAG3 | 1.00 |
| 19652 | 3 | | | | | SPG20OS | 1.00 | 19748 | 3 | | | | STAP2 | 1.00 |
| 19653 | 3 | | | | | SPHKAP | 1.00 | 19749 | 3 | | | | STAR | 1.00 |
| 19654 | 3 | | | | | SPIC | 1.00 | 19750 | 3 | | | | STARD13 | 1.00 |
| 19655 | 3 | | | | | SPINK1 | 1.00 | 19751 | 3 | | | | STARD6 | 1.00 |
| 19656 | 3 | | | | | SPINK13 | 1.00 | 19752 | 3 | | | | STARD9 | 1.00 |
| 19657 | 3 | | | | | SPINK14 | 1.00 | 19753 | 3 | | | | STATH | 1.00 |
| 19658 | 3 | | | | | SPINK2 | 1.00 | 19754 | 3 | | | | STC1 | 1.00 |
| 19659 | 3 | | | | | SPINK4 | 1.00 | 19755 | 3 | | | | STC2 | 1.00 |
| 19660 | 3 | | | | | SPINK5 | 1.00 | 19756 | 3 | | | | STEAP1 | 1.00 |
| 19661 | 3 | | | | | SPINK6 | 1.00 | 19757 | 3 | | | | STEAP1B | 1.00 |
| 19662 | 3 | | | | | SPINK7 | 1.00 | 19758 | 3 | | | | STEAP2 | 1.00 |
| 19663 | 3 | | | | | SPINK8 | 1.00 | 19759 | 3 | | | | STH | 1.00 |
| 19664 | 3 | | | | | SPINK9 | 1.00 | 19760 | 3 | | | | STK | 1.00 |
| 19665 | 3 | | | | | SPINLW1 | 1.00 | 19761 | 3 | | | | STK31 | 1.00 |
| 19666 | 3 | | | | | SPINLW1-WFDC6 | 1.00 | 19762 | 3 | | | | STK32A | 1.00 |
| 19667 | 3 | | | | | SPINT3 | 1.00 | 19763 | 3 | | | | STK32B | 1.00 |
| 19668 | 3 | | | | | SPINT4 | 1.00 | 19764 | 3 | | | | STK33 | 1.00 |
| 19669 | 3 | | | | | SPIRE2 | 1.00 | 19765 | 3 | | | | STL | 1.00 |
| 19670 | 3 | | | | | SPO11 | 1.00 | 19766 | 3 | | | | STMN2 | 1.00 |
| 19671 | 3 | | | | | SPOCK1 | 1.00 | 19767 | 3 | | | | STMN4 | 1.00 |
| 19672 | 3 | | | | | SPOCK3 | 1.00 | 19768 | 3 | | | | STOML3 | 1.00 |

Fig. 40 - 104

| | | | | | | | | | | | | | | |
|---|---|---|---|---|---|---|---|---|---|---|---|---|---|---|
| 19769 | 3 | | | | | STON1-GTF2A1L | 1.00 | 19865 | 3 | | | | TAL2 | 1.00 |
| 19770 | 3 | | | | | STOX1 | 1.00 | 19866 | 3 | | | | TANC1 | 1.00 |
| 19771 | 3 | | | | | STOX2 | 1.00 | 19867 | 3 | | | | TARM1 | 1.00 |
| 19772 | 3 | | | | | STRA6 | 1.00 | 19868 | 3 | | | | TAS1R1 | 1.00 |
| 19773 | 3 | | | | | STRA8 | 1.00 | 19869 | 3 | | | | TAS1R2 | 1.00 |
| 19774 | 3 | | | | | STRC | 1.00 | 19870 | 3 | | | | TAS1R3 | 1.00 |
| 19775 | 3 | | | | | STX19 | 1.00 | 19871 | 3 | | | | TAS2R1 | 1.00 |
| 19776 | 3 | | | | | STX1B | 1.00 | 19872 | 3 | | | | TAS2R10 | 1.00 |
| 19777 | 3 | | | | | STXBP1 | 1.00 | 19873 | 3 | | | | TAS2R13 | 1.00 |
| 19778 | 3 | | | | | STXBP4 | 1.00 | 19874 | 3 | | | | TAS2R16 | 1.00 |
| 19779 | 3 | | | | | STXBP5L | 1.00 | 19875 | 3 | | | | TAS2R19 | 1.00 |
| 19780 | 3 | | | | | STXBP6 | 1.00 | 19876 | 3 | | | | TAS2R20 | 1.00 |
| 19781 | 3 | | | | | STYK1 | 1.00 | 19877 | 3 | | | | TAS2R3 | 1.00 |
| 19782 | 3 | | | | | SUGT1P1 | 1.00 | 19878 | 3 | | | | TAS2R30 | 1.00 |
| 19783 | 3 | | | | | SUGT1P3 | 1.00 | 19879 | 3 | | | | TAS2R31 | 1.00 |
| 19784 | 3 | | | | | SULF1 | 1.00 | 19880 | 3 | | | | TAS2R38 | 1.00 |
| 19785 | 3 | | | | | SULT1C2 | 1.00 | 19881 | 3 | | | | TAS2R39 | 1.00 |
| 19786 | 3 | | | | | SULT1C2P1 | 1.00 | 19882 | 3 | | | | TAS2R41 | 1.00 |
| 19787 | 3 | | | | | SULT1C3 | 1.00 | 19883 | 3 | | | | TAS2R42 | 1.00 |
| 19788 | 3 | | | | | SULT1C4 | 1.00 | 19884 | 3 | | | | TAS2R43 | 1.00 |
| 19789 | 3 | | | | | SULT1E1 | 1.00 | 19885 | 3 | | | | TAS2R46 | 1.00 |
| 19790 | 3 | | | | | SULT2A1 | 1.00 | 19886 | 3 | | | | TAS2R50 | 1.00 |
| 19791 | 3 | | | | | SULT2B1 | 1.00 | 19887 | 3 | | | | TAS2R60 | 1.00 |
| 19792 | 3 | | | | | SULT4A1 | 1.00 | 19888 | 3 | | | | TAS2R7 | 1.00 |
| 19793 | 3 | | | | | SULT6B1 | 1.00 | 19889 | 3 | | | | TAS2R8 | 1.00 |
| 19794 | 3 | | | | | SUN3 | 1.00 | 19890 | 3 | | | | TAS2R9 | 1.00 |
| 19795 | 3 | | | | | SUN5 | 1.00 | 19891 | 3 | | | | TAT | 1.00 |
| 19796 | 3 | | | | | SUSD2 | 1.00 | 19892 | 3 | | | | TBC1D16 | 1.00 |
| 19797 | 3 | | | | | SUSD5 | 1.00 | 19893 | 3 | | | | TBC1D19 | 1.00 |
| 19798 | 3 | | | | | SV2A | 1.00 | 19894 | 3 | | | | TBC1D21 | 1.00 |
| 19799 | 3 | | | | | SV2B | 1.00 | 19895 | 3 | | | | TBC1D26 | 1.00 |
| 19800 | 3 | | | | | SV2C | 1.00 | 19896 | 3 | | | | TBC1D28 | 1.00 |
| 19801 | 3 | | | | | SVEP1 | 1.00 | 19897 | 3 | | | | TBC1D29 | 1.00 |
| 19802 | 3 | | | | | SVOP | 1.00 | 19898 | 3 | | | | TBC1D3 | 1.00 |
| 19803 | 3 | | | | | SVOPL | 1.00 | 19899 | 3 | | | | TBC1D30 | 1.00 |
| 19804 | 3 | | | | | SYBU | 1.00 | 19900 | 3 | | | | TBC1D3F1-DHX40P1 | 1.00 |
| 19805 | 3 | | | | | SYCE1 | 1.00 | 19901 | 3 | | | | TBC1D3P2 | 1.00 |
| 19806 | 3 | | | | | SYCE1L | 1.00 | 19902 | 3 | | | | TBC1D3P5 | 1.00 |
| 19807 | 3 | | | | | SYCE2 | 1.00 | 19903 | 3 | | | | TBC1D8B | 1.00 |
| 19808 | 3 | | | | | SYCE3 | 1.00 | 19904 | 3 | | | | TBL1Y | 1.00 |
| 19809 | 3 | | | | | SYCN | 1.00 | 19905 | 3 | | | | TBPL2 | 1.00 |
| 19810 | 3 | | | | | SYCP1 | 1.00 | 19906 | 3 | | | | TBR1 | 1.00 |
| 19811 | 3 | | | | | SYCP2 | 1.00 | 19907 | 3 | | | | TBX1 | 1.00 |
| 19812 | 3 | | | | | SYCP2L | 1.00 | 19908 | 3 | | | | TBX10 | 1.00 |
| 19813 | 3 | | | | | SYCP3 | 1.00 | 19909 | 3 | | | | TBX15 | 1.00 |
| 19814 | 3 | | | | | SYDE1 | 1.00 | 19910 | 3 | | | | TBX18 | 1.00 |
| 19815 | 3 | | | | | SYDE2 | 1.00 | 19911 | 3 | | | | TBX2 | 1.00 |
| 19816 | 3 | | | | | SYN1 | 1.00 | 19912 | 3 | | | | TBX20 | 1.00 |
| 19817 | 3 | | | | | SYN2 | 1.00 | 19913 | 3 | | | | TBX22 | 1.00 |
| 19818 | 3 | | | | | SYN3 | 1.00 | 19914 | 3 | | | | TBX3 | 1.00 |
| 19819 | 3 | | | | | SYNDIG1 | 1.00 | 19915 | 3 | | | | TBX4 | 1.00 |
| 19820 | 3 | | | | | SYNDIG1L | 1.00 | 19916 | 3 | | | | TBX5 | 1.00 |
| 19821 | 3 | | | | | SYNGR3 | 1.00 | 19917 | 3 | | | | TBX6 | 1.00 |
| 19822 | 3 | | | | | SYNGR4 | 1.00 | 19918 | 3 | | | | TCAM1P | 1.00 |
| 19823 | 3 | | | | | SYNJ2BP-COX16 | 1.00 | 19919 | 3 | | | | TCEAL2 | 1.00 |
| 19824 | 3 | | | | | SYNPO2 | 1.00 | 19920 | 3 | | | | TCEAL5 | 1.00 |
| 19825 | 3 | | | | | SYNPO2L | 1.00 | 19921 | 3 | | | | TCEAL6 | 1.00 |
| 19826 | 3 | | | | | SYNPR | 1.00 | 19922 | 3 | | | | TCEAL7 | 1.00 |
| 19827 | 3 | | | | | SVP | 1.00 | 19923 | 3 | | | | TCEB3B | 1.00 |
| 19828 | 3 | | | | | SYPL2 | 1.00 | 19924 | 3 | | | | TCEB3C | 1.00 |
| 19829 | 3 | | | | | SYS1-DBNDD2 | 1.00 | 19925 | 3 | | | | TCEB3CL | 1.00 |
| 19830 | 3 | | | | | SYT1 | 1.00 | 19926 | 3 | | | | TCERG1L | 1.00 |
| 19831 | 3 | | | | | SYT10 | 1.00 | 19927 | 3 | | | | TCF15 | 1.00 |
| 19832 | 3 | | | | | SYT12 | 1.00 | 19928 | 3 | | | | TCF21 | 1.00 |
| 19833 | 3 | | | | | SYT13 | 1.00 | 19929 | 3 | | | | TCF23 | 1.00 |
| 19834 | 3 | | | | | SYT14 | 1.00 | 19930 | 3 | | | | TCF24 | 1.00 |
| 19835 | 3 | | | | | SYT14L | 1.00 | 19931 | 3 | | | | TCHH | 1.00 |
| 19836 | 3 | | | | | SYT15 | 1.00 | 19932 | 3 | | | | TCHHL1 | 1.00 |
| 19837 | 3 | | | | | SYT16 | 1.00 | 19933 | 3 | | | | TCL1B | 1.00 |
| 19838 | 3 | | | | | SYT17 | 1.00 | 19934 | 3 | | | | TCL6 | 1.00 |
| 19839 | 3 | | | | | SYT2 | 1.00 | 19935 | 3 | | | | TCP10 | 1.00 |
| 19840 | 3 | | | | | SYT3 | 1.00 | 19936 | 3 | | | | TCP10L | 1.00 |
| 19841 | 3 | | | | | SYT4 | 1.00 | 19937 | 3 | | | | TCP10L2 | 1.00 |
| 19842 | 3 | | | | | SYT5 | 1.00 | 19938 | 3 | | | | TCP11 | 1.00 |
| 19843 | 3 | | | | | SYT6 | 1.00 | 19939 | 3 | | | | TCTE1 | 1.00 |
| 19844 | 3 | | | | | SYT7 | 1.00 | 19940 | 3 | | | | TCTE3 | 1.00 |
| 19845 | 3 | | | | | SYT8 | 1.00 | 19941 | 3 | | | | TCTEX1D1 | 1.00 |
| 19846 | 3 | | | | | SYT9 | 1.00 | 19942 | 3 | | | | TDGF1 | 1.00 |
| 19847 | 3 | | | | | SYTL5 | 1.00 | 19943 | 3 | | | | TDGF1P3 | 1.00 |
| 19848 | 3 | | | | | T | 1.00 | 19944 | 3 | | | | TDH | 1.00 |
| 19849 | 3 | | | | | TAAR1 | 1.00 | 19945 | 3 | | | | TDO2 | 1.00 |
| 19850 | 3 | | | | | TAAR2 | 1.00 | 19946 | 3 | | | | TDRD1 | 1.00 |
| 19851 | 3 | | | | | TAAR3 | 1.00 | 19947 | 3 | | | | TDRD10 | 1.00 |
| 19852 | 3 | | | | | TAAR5 | 1.00 | 19948 | 3 | | | | TDRD12 | 1.00 |
| 19853 | 3 | | | | | TAAR6 | 1.00 | 19949 | 3 | | | | TDRD5 | 1.00 |
| 19854 | 3 | | | | | TAAR8 | 1.00 | 19950 | 3 | | | | TDRD6 | 1.00 |
| 19855 | 3 | | | | | TAAR9 | 1.00 | 19951 | 3 | | | | TDRD9 | 1.00 |
| 19856 | 3 | | | | | TAC1 | 1.00 | 19952 | 3 | | | | TDRG1 | 1.00 |
| 19857 | 3 | | | | | TAC3 | 1.00 | 19953 | 3 | | | | TEAD1 | 1.00 |
| 19858 | 3 | | | | | TACC2 | 1.00 | 19954 | 3 | | | | TEAD3 | 1.00 |
| 19859 | 3 | | | | | TACR1 | 1.00 | 19955 | 3 | | | | TEAD4 | 1.00 |
| 19860 | 3 | | | | | TACR2 | 1.00 | 19956 | 3 | | | | TECRL | 1.00 |
| 19861 | 3 | | | | | TACR3 | 1.00 | 19957 | 3 | | | | TECTA | 1.00 |
| 19862 | 3 | | | | | TAF7L | 1.00 | 19958 | 3 | | | | TECTB | 1.00 |
| 19863 | 3 | | | | | TAG | 1.00 | 19959 | 3 | | | | TEDDM1 | 1.00 |
| 19864 | 3 | | | | | TAGLN3 | 1.00 | | | | | | | |

Fig. 40 - 105

| | | | | | | | | | | | | | | | |
|---|---|---|---|---|---|---|---|---|---|---|---|---|---|---|---|
| 19960 | 3 | | | | | TEK | 1.00 | 20055 | 3 | | | | | TM6SF2 | 1.00 |
| 19961 | 3 | | | | | TEKT1 | 1.00 | 20056 | 3 | | | | | TM7SF4 | 1.00 |
| 19962 | 3 | | | | | TEKT2 | 1.00 | 20057 | 3 | | | | | TMC1 | 1.00 |
| 19963 | 3 | | | | | TEKT3 | 1.00 | 20058 | 3 | | | | | TMC2 | 1.00 |
| 19964 | 3 | | | | | TEKT4 | 1.00 | 20059 | 3 | | | | | TMC3 | 1.00 |
| 19965 | 3 | | | | | TEKT5 | 1.00 | 20060 | 3 | | | | | TMC5 | 1.00 |
| 19966 | 3 | | | | | TENC1 | 1.00 | 20061 | 3 | | | | | TMC7 | 1.00 |
| 19967 | 3 | | | | | TEPP | 1.00 | 20062 | 3 | | | | | TMCO2 | 1.00 |
| 19968 | 3 | | | | | TERC | 1.00 | 20063 | 3 | | | | | TMCO5A | 1.00 |
| 19969 | 3 | | | | | TERT | 1.00 | 20064 | 3 | | | | | TMCO5B | 1.00 |
| 19970 | 3 | | | | | TET1 | 1.00 | 20065 | 3 | | | | | TMED6 | 1.00 |
| 19971 | 3 | | | | | TEX101 | 1.00 | 20066 | 3 | | | | | TMEFF1 | 1.00 |
| 19972 | 3 | | | | | TEX11 | 1.00 | 20067 | 3 | | | | | TMEFF2 | 1.00 |
| 19973 | 3 | | | | | TEX12 | 1.00 | 20068 | 3 | | | | | TMEM100 | 1.00 |
| 19974 | 3 | | | | | TEX13A | 1.00 | 20069 | 3 | | | | | TMEM105 | 1.00 |
| 19975 | 3 | | | | | TEX13B | 1.00 | 20070 | 3 | | | | | TMEM108 | 1.00 |
| 19976 | 3 | | | | | TEX14 | 1.00 | 20071 | 3 | | | | | TMEM110-MUSTN1 | 1.00 |
| 19977 | 3 | | | | | TEX15 | 1.00 | 20072 | 3 | | | | | TMEM114 | 1.00 |
| 19978 | 3 | | | | | TEX19 | 1.00 | 20073 | 3 | | | | | TMEM117 | 1.00 |
| 19979 | 3 | | | | | TEX21P | 1.00 | 20074 | 3 | | | | | TMEM121 | 1.00 |
| 19980 | 3 | | | | | TEX22 | 1.00 | 20075 | 3 | | | | | TMEM125 | 1.00 |
| 19981 | 3 | | | | | TEX26 | 1.00 | 20076 | 3 | | | | | TMEM130 | 1.00 |
| 19982 | 3 | | | | | TEX26-AS1 | 1.00 | 20077 | 3 | | | | | TMEM132A | 1.00 |
| 19983 | 3 | | | | | TEX28 | 1.00 | 20078 | 3 | | | | | TMEM132B | 1.00 |
| 19984 | 3 | | | | | TEX29 | 1.00 | 20079 | 3 | | | | | TMEM132C | 1.00 |
| 19985 | 3 | | | | | TEX33 | 1.00 | 20080 | 3 | | | | | TMEM132D | 1.00 |
| 19986 | 3 | | | | | TEX9 | 1.00 | 20081 | 3 | | | | | TMEM132E | 1.00 |
| 19987 | 3 | | | | | TF | 1.00 | 20082 | 3 | | | | | TMEM133 | 1.00 |
| 19988 | 3 | | | | | TFAP2A | 1.00 | 20083 | 3 | | | | | TMEM136 | 1.00 |
| 19989 | 3 | | | | | TFAP2B | 1.00 | 20084 | 3 | | | | | TMEM139 | 1.00 |
| 19990 | 3 | | | | | TFAP2C | 1.00 | 20085 | 3 | | | | | TMEM145 | 1.00 |
| 19991 | 3 | | | | | TFAP2D | 1.00 | 20086 | 3 | | | | | TMEM14E | 1.00 |
| 19992 | 3 | | | | | TFCP2L1 | 1.00 | 20087 | 3 | | | | | TMEM150C | 1.00 |
| 19993 | 3 | | | | | TFDP3 | 1.00 | 20088 | 3 | | | | | TMEM151A | 1.00 |
| 19994 | 3 | | | | | TFF1 | 1.00 | 20089 | 3 | | | | | TMEM151B | 1.00 |
| 19995 | 3 | | | | | TFF2 | 1.00 | 20090 | 3 | | | | | TMEM155 | 1.00 |
| 19996 | 3 | | | | | TFF3 | 1.00 | 20091 | 3 | | | | | TMEM163 | 1.00 |
| 19997 | 3 | | | | | TFPI | 1.00 | 20092 | 3 | | | | | TMEM17 | 1.00 |
| 19998 | 3 | | | | | TFPI2 | 1.00 | 20093 | 3 | | | | | TMEM171 | 1.00 |
| 19999 | 3 | | | | | TG | 1.00 | 20094 | 3 | | | | | TMEM174 | 1.00 |
| 20000 | 3 | | | | | TGFB2 | 1.00 | 20095 | 3 | | | | | TMEM178 | 1.00 |
| 20001 | 3 | | | | | TGIF2-C20ORF24 | 1.00 | 20096 | 3 | | | | | TMEM179 | 1.00 |
| 20002 | 3 | | | | | TGIF2LX | 1.00 | 20097 | 3 | | | | | TMEM182 | 1.00 |
| 20003 | 3 | | | | | TGIF2LY | 1.00 | 20098 | 3 | | | | | TMEM184A | 1.00 |
| 20004 | 3 | | | | | TGM1 | 1.00 | 20099 | 3 | | | | | TMEM189-UBE2V1 | 1.00 |
| 20005 | 3 | | | | | TGM4 | 1.00 | 20100 | 3 | | | | | TMEM190 | 1.00 |
| 20006 | 3 | | | | | TGM5 | 1.00 | 20101 | 3 | | | | | TMEM191A | 1.00 |
| 20007 | 3 | | | | | TGM6 | 1.00 | 20102 | 3 | | | | | TMEM191B | 1.00 |
| 20008 | 3 | | | | | TGM7 | 1.00 | 20103 | 3 | | | | | TMEM191C | 1.00 |
| 20009 | 3 | | | | | TH | 1.00 | 20104 | 3 | | | | | TMEM196 | 1.00 |
| 20010 | 3 | | | | | THAP10 | 1.00 | 20105 | 3 | | | | | TMEM198 | 1.00 |
| 20011 | 3 | | | | | THBS2 | 1.00 | 20106 | 3 | | | | | TMEM200A | 1.00 |
| 20012 | 3 | | | | | THBS4 | 1.00 | 20107 | 3 | | | | | TMEM200B | 1.00 |
| 20013 | 3 | | | | | THEG | 1.00 | 20108 | 3 | | | | | TMEM200C | 1.00 |
| 20014 | 3 | | | | | THEG5 | 1.00 | 20109 | 3 | | | | | TMEM202 | 1.00 |
| 20015 | 3 | | | | | THEGL | 1.00 | 20110 | 3 | | | | | TMEM207 | 1.00 |
| 20016 | 3 | | | | | THNSL2 | 1.00 | 20111 | 3 | | | | | TMEM211 | 1.00 |
| 20017 | 3 | | | | | THPO | 1.00 | 20112 | 3 | | | | | TMEM212 | 1.00 |
| 20018 | 3 | | | | | THRB | 1.00 | 20113 | 3 | | | | | TMEM213 | 1.00 |
| 20019 | 3 | | | | | THRSP | 1.00 | 20114 | 3 | | | | | TMEM215 | 1.00 |
| 20020 | 3 | | | | | THSD1 | 1.00 | 20115 | 3 | | | | | TMEM217 | 1.00 |
| 20021 | 3 | | | | | THSD4 | 1.00 | 20116 | 3 | | | | | TMEM22 | 1.00 |
| 20022 | 3 | | | | | THSD7A | 1.00 | 20117 | 3 | | | | | TMEM221 | 1.00 |
| 20023 | 3 | | | | | THSD7B | 1.00 | 20118 | 3 | | | | | TMEM225 | 1.00 |
| 20024 | 3 | | | | | THY1 | 1.00 | 20119 | 3 | | | | | TMEM229A | 1.00 |
| 20025 | 3 | | | | | TIE1 | 1.00 | 20120 | 3 | | | | | TMEM231 | 1.00 |
| 20026 | 3 | | | | | TIGD4 | 1.00 | 20121 | 3 | | | | | TMEM232 | 1.00 |
| 20027 | 3 | | | | | TIMD4 | 1.00 | 20122 | 3 | | | | | TMEM233 | 1.00 |
| 20028 | 3 | | | | | TIMP3 | 1.00 | 20123 | 3 | | | | | TMEM235 | 1.00 |
| 20029 | 3 | | | | | TIMP4 | 1.00 | 20124 | 3 | | | | | TMEM236 | 1.00 |
| 20030 | 3 | | | | | TINAG | 1.00 | 20125 | 3 | | | | | TMEM237 | 1.00 |
| 20031 | 3 | | | | | TINAGL1 | 1.00 | 20126 | 3 | | | | | TMEM239 | 1.00 |
| 20032 | 3 | | | | | TIPARP-AS1 | 1.00 | 20127 | 3 | | | | | TMEM240 | 1.00 |
| 20033 | 3 | | | | | TISP43 | 1.00 | 20128 | 3 | | | | | TMEM244 | 1.00 |
| 20034 | 3 | | | | | TJP1 | 1.00 | 20129 | 3 | | | | | TMEM26 | 1.00 |
| 20035 | 3 | | | | | TKTL2 | 1.00 | 20130 | 3 | | | | | TMEM27 | 1.00 |
| 20036 | 3 | | | | | TLCD1 | 1.00 | 20131 | 3 | | | | | TMEM30C | 1.00 |
| 20037 | 3 | | | | | TLCD2 | 1.00 | 20132 | 3 | | | | | TMEM31 | 1.00 |
| 20038 | 3 | | | | | TLE6 | 1.00 | 20133 | 3 | | | | | TMEM35 | 1.00 |
| 20039 | 3 | | | | | TLL1 | 1.00 | 20134 | 3 | | | | | TMEM37 | 1.00 |
| 20040 | 3 | | | | | TLL2 | 1.00 | 20135 | 3 | | | | | TMEM44 | 1.00 |
| 20041 | 3 | | | | | TLN2 | 1.00 | 20136 | 3 | | | | | TMEM45A | 1.00 |
| 20042 | 3 | | | | | TLR3 | 1.00 | 20137 | 3 | | | | | TMEM47 | 1.00 |
| 20043 | 3 | | | | | TLR8-AS1 | 1.00 | 20138 | 3 | | | | | TMEM52 | 1.00 |
| 20044 | 3 | | | | | TLX1 | 1.00 | 20139 | 3 | | | | | TMEM54 | 1.00 |
| 20045 | 3 | | | | | TLX1NB | 1.00 | 20140 | 3 | | | | | TMEM56 | 1.00 |
| 20046 | 3 | | | | | TLX2 | 1.00 | 20141 | 3 | | | | | TMEM56-RWDD3 | 1.00 |
| 20047 | 3 | | | | | TLX3 | 1.00 | 20142 | 3 | | | | | TMEM59L | 1.00 |
| 20048 | 3 | | | | | TM4SF1 | 1.00 | 20143 | 3 | | | | | TMEM61 | 1.00 |
| 20049 | 3 | | | | | TM4SF18 | 1.00 | 20144 | 3 | | | | | TMEM67 | 1.00 |
| 20050 | 3 | | | | | TM4SF19 | 1.00 | 20145 | 3 | | | | | TMEM72 | 1.00 |
| 20051 | 3 | | | | | TM4SF19-TCTEX1D2 | 1.00 | 20146 | 3 | | | | | TMEM72-AS1 | 1.00 |
| 20052 | 3 | | | | | TM4SF20 | 1.00 | 20147 | 3 | | | | | TMEM74 | 1.00 |
| 20053 | 3 | | | | | TM4SF4 | 1.00 | 20148 | 3 | | | | | TMEM74B | 1.00 |
| 20054 | 3 | | | | | TM4SF5 | 1.00 | | | | | | | | |

Fig. 40 - 106

| | | | | | | | | | | | | | | |
|---|---|---|---|---|---|---|---|---|---|---|---|---|---|---|
| 20149 | 3 | | | | TMEM82 | 1.00 | | 20245 | 3 | | | | TRIM15 | 1.00 |
| 20150 | 3 | | | | TMEM88B | 1.00 | | 20246 | 3 | | | | TRIM2 | 1.00 |
| 20151 | 3 | | | | TMEM89 | 1.00 | | 20247 | 3 | | | | TRIM29 | 1.00 |
| 20152 | 3 | | | | TMEM8C | 1.00 | | 20248 | 3 | | | | TRIM31 | 1.00 |
| 20153 | 3 | | | | TMEM92 | 1.00 | | 20249 | 3 | | | | TRIM36 | 1.00 |
| 20154 | 3 | | | | TMEM95 | 1.00 | | 20250 | 3 | | | | TRIM39-RPP21 | 1.00 |
| 20155 | 3 | | | | TMEM98 | 1.00 | | 20251 | 3 | | | | TRIM42 | 1.00 |
| 20156 | 3 | | | | TMIGD1 | 1.00 | | 20252 | 3 | | | | TRIM43 | 1.00 |
| 20157 | 3 | | | | TMOD4 | 1.00 | | 20253 | 3 | | | | TRIM43B | 1.00 |
| 20158 | 3 | | | | TMPRSS11A | 1.00 | | 20254 | 3 | | | | TRIM45 | 1.00 |
| 20159 | 3 | | | | TMPRSS11B | 1.00 | | 20255 | 3 | | | | TRIM48 | 1.00 |
| 20160 | 3 | | | | TMPRSS11BNL | 1.00 | | 20256 | 3 | | | | TRIM49 | 1.00 |
| 20161 | 3 | | | | TMPRSS11D | 1.00 | | 20257 | 3 | | | | TRIM49L1 | 1.00 |
| 20162 | 3 | | | | TMPRSS11E | 1.00 | | 20258 | 3 | | | | TRIM49L2 | 1.00 |
| 20163 | 3 | | | | TMPRSS11F | 1.00 | | 20259 | 3 | | | | TRIM50 | 1.00 |
| 20164 | 3 | | | | TMPRSS11GP | 1.00 | | 20260 | 3 | | | | TRIM53P | 1.00 |
| 20165 | 3 | | | | TMPRSS12 | 1.00 | | 20261 | 3 | | | | TRIM54 | 1.00 |
| 20166 | 3 | | | | TMPRSS15 | 1.00 | | 20262 | 3 | | | | TRIM55 | 1.00 |
| 20167 | 3 | | | | TMPRSS2 | 1.00 | | 20263 | 3 | | | | TRIM6-TRIM34 | 1.00 |
| 20168 | 3 | | | | TMPRSS3 | 1.00 | | 20264 | 3 | | | | TRIM60 | 1.00 |
| 20169 | 3 | | | | TMPRSS4 | 1.00 | | 20265 | 3 | | | | TRIM61 | 1.00 |
| 20170 | 3 | | | | TMPRSS5 | 1.00 | | 20266 | 3 | | | | TRIM63 | 1.00 |
| 20171 | 3 | | | | TMPRSS6 | 1.00 | | 20267 | 3 | | | | TRIM64 | 1.00 |
| 20172 | 3 | | | | TMPRSS7 | 1.00 | | 20268 | 3 | | | | TRIM64B | 1.00 |
| 20173 | 3 | | | | TMPRSS9 | 1.00 | | 20269 | 3 | | | | TRIM64C | 1.00 |
| 20174 | 3 | | | | TMSB15A | 1.00 | | 20270 | 3 | | | | TRIM67 | 1.00 |
| 20175 | 3 | | | | TMSB15B | 1.00 | | 20271 | 3 | | | | TRIM71 | 1.00 |
| 20176 | 3 | | | | TMSB4Y | 1.00 | | 20272 | 3 | | | | TRIM72 | 1.00 |
| 20177 | 3 | | | | TNC | 1.00 | | 20273 | 3 | | | | TRIM77P | 1.00 |
| 20178 | 3 | | | | TNFAIP8L2-SCNM1 | 1.00 | | 20274 | 3 | | | | TRIM9 | 1.00 |
| 20179 | 3 | | | | TNFAIP8L3 | 1.00 | | 20275 | 3 | | | | TRIML1 | 1.00 |
| 20180 | 3 | | | | TNFRSF11A | 1.00 | | 20276 | 3 | | | | TRIML2 | 1.00 |
| 20181 | 3 | | | | TNFRSF11B | 1.00 | | 20277 | 3 | | | | TRIP13 | 1.00 |
| 20182 | 3 | | | | TNFRSF19 | 1.00 | | 20278 | 3 | | | | TRNP1 | 1.00 |
| 20183 | 3 | | | | TNFSF11 | 1.00 | | 20279 | 3 | | | | TRO | 1.00 |
| 20184 | 3 | | | | TNFSF12-TNFSF13 | 1.00 | | 20280 | 3 | | | | TROAP | 1.00 |
| 20185 | 3 | | | | TNFSF18 | 1.00 | | 20281 | 3 | | | | TRPA1 | 1.00 |
| 20186 | 3 | | | | TNFSF9 | 1.00 | | 20282 | 3 | | | | TRPC1 | 1.00 |
| 20187 | 3 | | | | TNIP3 | 1.00 | | 20283 | 3 | | | | TRPC2 | 1.00 |
| 20188 | 3 | | | | TNMD | 1.00 | | 20284 | 3 | | | | TRPC3 | 1.00 |
| 20189 | 3 | | | | TNN | 1.00 | | 20285 | 3 | | | | TRPC4 | 1.00 |
| 20190 | 3 | | | | TNNC1 | 1.00 | | 20286 | 3 | | | | TRPC5 | 1.00 |
| 20191 | 3 | | | | TNNI1 | 1.00 | | 20287 | 3 | | | | TRPC6 | 1.00 |
| 20192 | 3 | | | | TNNI3 | 1.00 | | 20288 | 3 | | | | TRPC7 | 1.00 |
| 20193 | 3 | | | | TNNI3K | 1.00 | | 20289 | 3 | | | | TRPM1 | 1.00 |
| 20194 | 3 | | | | TNNT2 | 1.00 | | 20290 | 3 | | | | TRPM3 | 1.00 |
| 20195 | 3 | | | | TNP1 | 1.00 | | 20291 | 3 | | | | TRPM4 | 1.00 |
| 20196 | 3 | | | | TNP2 | 1.00 | | 20292 | 3 | | | | TRPM5 | 1.00 |
| 20197 | 3 | | | | TNR | 1.00 | | 20293 | 3 | | | | TRPM8 | 1.00 |
| 20198 | 3 | | | | TNS4 | 1.00 | | 20294 | 3 | | | | TRPV3 | 1.00 |
| 20199 | 3 | | | | TOB2P1 | 1.00 | | 20295 | 3 | | | | TRPV4 | 1.00 |
| 20200 | 3 | | | | TOM1L1 | 1.00 | | 20296 | 3 | | | | TRPV5 | 1.00 |
| 20201 | 3 | | | | TOMM20L | 1.00 | | 20297 | 3 | | | | TRPV6 | 1.00 |
| 20202 | 3 | | | | TONSL | 1.00 | | 20298 | 3 | | | | TRY6 | 1.00 |
| 20203 | 3 | | | | TOP1P2 | 1.00 | | 20299 | 3 | | | | TSC22D1-AS1 | 1.00 |
| 20204 | 3 | | | | TOX2 | 1.00 | | 20300 | 3 | | | | TSG1 | 1.00 |
| 20205 | 3 | | | | TOX3 | 1.00 | | 20301 | 3 | | | | TSGA10 | 1.00 |
| 20206 | 3 | | | | TP53AIP1 | 1.00 | | 20302 | 3 | | | | TSGA10IP | 1.00 |
| 20207 | 3 | | | | TP53TG3 | 1.00 | | 20303 | 3 | | | | TSGA13 | 1.00 |
| 20208 | 3 | | | | TP53TG3B | 1.00 | | 20304 | 3 | | | | TSHB | 1.00 |
| 20209 | 3 | | | | TP53TG3C | 1.00 | | 20305 | 3 | | | | TSHR | 1.00 |
| 20210 | 3 | | | | TP53TG5 | 1.00 | | 20306 | 3 | | | | TSIX | 1.00 |
| 20211 | 3 | | | | TP63 | 1.00 | | 20307 | 3 | | | | TSKS | 1.00 |
| 20212 | 3 | | | | TP73 | 1.00 | | 20308 | 3 | | | | TSKU | 1.00 |
| 20213 | 3 | | | | TPBG | 1.00 | | 20309 | 3 | | | | TSLP | 1.00 |
| 20214 | 3 | | | | TPD52L1 | 1.00 | | 20310 | 3 | | | | TSNAX-DISC1 | 1.00 |
| 20215 | 3 | | | | TPD52L3 | 1.00 | | 20311 | 3 | | | | TSNAXIP1 | 1.00 |
| 20216 | 3 | | | | TPH1 | 1.00 | | 20312 | 3 | | | | TSPAN1 | 1.00 |
| 20217 | 3 | | | | TPH2 | 1.00 | | 20313 | 3 | | | | TSPAN10 | 1.00 |
| 20218 | 3 | | | | TPI1P2 | 1.00 | | 20314 | 3 | | | | TSPAN11 | 1.00 |
| 20219 | 3 | | | | TPI1P3 | 1.00 | | 20315 | 3 | | | | TSPAN12 | 1.00 |
| 20220 | 3 | | | | TPO | 1.00 | | 20316 | 3 | | | | TSPAN15 | 1.00 |
| 20221 | 3 | | | | TPPP2 | 1.00 | | 20317 | 3 | | | | TSPAN19 | 1.00 |
| 20222 | 3 | | | | TPRG1 | 1.00 | | 20318 | 3 | | | | TSPAN6 | 1.00 |
| 20223 | 3 | | | | TPRX1 | 1.00 | | 20319 | 3 | | | | TSPAN8 | 1.00 |
| 20224 | 3 | | | | TPRXL | 1.00 | | 20320 | 3 | | | | TSPEAR | 1.00 |
| 20225 | 3 | | | | TPSAB1 | 1.00 | | 20321 | 3 | | | | TSPO2 | 1.00 |
| 20226 | 3 | | | | TPSB2 | 1.00 | | 20322 | 3 | | | | TSPY1 | 1.00 |
| 20227 | 3 | | | | TPSD1 | 1.00 | | 20323 | 3 | | | | TSPY2 | 1.00 |
| 20228 | 3 | | | | TPSG1 | 1.00 | | 20324 | 3 | | | | TSPY26P | 1.00 |
| 20229 | 3 | | | | TPTE | 1.00 | | 20325 | 3 | | | | TSPY3 | 1.00 |
| 20230 | 3 | | | | TPTE2 | 1.00 | | 20326 | 3 | | | | TSPY4 | 1.00 |
| 20231 | 3 | | | | TPTE2P1 | 1.00 | | 20327 | 3 | | | | TSPY8 | 1.00 |
| 20232 | 3 | | | | TPTE2P3 | 1.00 | | 20328 | 3 | | | | TSPYL6 | 1.00 |
| 20233 | 3 | | | | TPTE2P6 | 1.00 | | 20329 | 3 | | | | TSSK1B | 1.00 |
| 20234 | 3 | | | | TPX2 | 1.00 | | 20330 | 3 | | | | TSSK2 | 1.00 |
| 20235 | 3 | | | | TRAIP | 1.00 | | 20331 | 3 | | | | TTBK1 | 1.00 |
| 20236 | 3 | | | | TRAM1L1 | 1.00 | | 20332 | 3 | | | | TTC12 | 1.00 |
| 20237 | 3 | | | | TRDN | 1.00 | | 20333 | 3 | | | | TTC18 | 1.00 |
| 20238 | 3 | | | | TREH | 1.00 | | 20334 | 3 | | | | TTC23 | 1.00 |
| 20239 | 3 | | | | TREM2 | 1.00 | | 20335 | 3 | | | | TTC23L | 1.00 |
| 20240 | 3 | | | | TREML2P1 | 1.00 | | 20336 | 3 | | | | TTC24 | 1.00 |
| 20241 | 3 | | | | TRH | 1.00 | | 20337 | 3 | | | | TTC28 | 1.00 |
| 20242 | 3 | | | | TRHDE | 1.00 | | 20338 | 3 | | | | TTC29 | 1.00 |
| 20243 | 3 | | | | TRHR | 1.00 | | 20339 | 3 | | | | TTC30A | 1.00 |
| 20244 | 3 | | | | TRIL | 1.00 | | 20340 | 3 | | | | TTC34 | 1.00 |

Fig. 40 - 107

| | | | | | | | | | | | | | | |
|---|---|---|---|---|---|---|---|---|---|---|---|---|---|---|
| 20341 | 3 | | | | | TTC36 | 1.00 | 20437 | 3 | | | | UGT1A3 | 1.00 |
| 20342 | 3 | | | | | TTC39A | 1.00 | 20438 | 3 | | | | UGT1A4 | 1.00 |
| 20343 | 3 | | | | | TTC40 | 1.00 | 20439 | 3 | | | | UGT1A5 | 1.00 |
| 20344 | 3 | | | | | TTC8 | 1.00 | 20440 | 3 | | | | UGT1A6 | 1.00 |
| 20345 | 3 | | | | | TTC9B | 1.00 | 20441 | 3 | | | | UGT1A7 | 1.00 |
| 20346 | 3 | | | | | TTK | 1.00 | 20442 | 3 | | | | UGT1A8 | 1.00 |
| 20347 | 3 | | | | | TTLL10 | 1.00 | 20443 | 3 | | | | UGT1A9 | 1.00 |
| 20348 | 3 | | | | | TTLL13 | 1.00 | 20444 | 3 | | | | UGT2A1 | 1.00 |
| 20349 | 3 | | | | | TTLL2 | 1.00 | 20445 | 3 | | | | UGT2A2 | 1.00 |
| 20350 | 3 | | | | | TTLL6 | 1.00 | 20446 | 3 | | | | UGT2A3 | 1.00 |
| 20351 | 3 | | | | | TTLL7 | 1.00 | 20447 | 3 | | | | UGT2B10 | 1.00 |
| 20352 | 3 | | | | | TTLL9 | 1.00 | 20448 | 3 | | | | UGT2B15 | 1.00 |
| 20353 | 3 | | | | | TTPA | 1.00 | 20449 | 3 | | | | UGT2B17 | 1.00 |
| 20354 | 3 | | | | | TTR | 1.00 | 20450 | 3 | | | | UGT2B28 | 1.00 |
| 20355 | 3 | | | | | TTTY1 | 1.00 | 20451 | 3 | | | | UGT2B4 | 1.00 |
| 20356 | 3 | | | | | TTTY10 | 1.00 | 20452 | 3 | | | | UGT2B7 | 1.00 |
| 20357 | 3 | | | | | TTTY11 | 1.00 | 20453 | 3 | | | | UGT3A1 | 1.00 |
| 20358 | 3 | | | | | TTTY12 | 1.00 | 20454 | 3 | | | | UGT3A2 | 1.00 |
| 20359 | 3 | | | | | TTTY13 | 1.00 | 20455 | 3 | | | | UGT8 | 1.00 |
| 20360 | 3 | | | | | TTTY14 | 1.00 | 20456 | 3 | | | | ULBP1 | 1.00 |
| 20361 | 3 | | | | | TTTY15 | 1.00 | 20457 | 3 | | | | ULBP2 | 1.00 |
| 20362 | 3 | | | | | TTTY16 | 1.00 | 20458 | 3 | | | | ULBP3 | 1.00 |
| 20363 | 3 | | | | | TTTY17A | 1.00 | 20459 | 3 | | | | ULK4 | 1.00 |
| 20364 | 3 | | | | | TTTY18 | 1.00 | 20460 | 3 | | | | ULK4P2 | 1.00 |
| 20365 | 3 | | | | | TTTY19 | 1.00 | 20461 | 3 | | | | ULK4P3 | 1.00 |
| 20366 | 3 | | | | | TTTY1B | 1.00 | 20462 | 3 | | | | UMOD | 1.00 |
| 20367 | 3 | | | | | TTTY2 | 1.00 | 20463 | 3 | | | | UMODL1 | 1.00 |
| 20368 | 3 | | | | | TTTY20 | 1.00 | 20464 | 3 | | | | UNC13A | 1.00 |
| 20369 | 3 | | | | | TTTY21 | 1.00 | 20465 | 3 | | | | UNC13B | 1.00 |
| 20370 | 3 | | | | | TTTY21B | 1.00 | 20466 | 3 | | | | UNC13C | 1.00 |
| 20371 | 3 | | | | | TTTY22 | 1.00 | 20467 | 3 | | | | UNC45B | 1.00 |
| 20372 | 3 | | | | | TTTY23B | 1.00 | 20468 | 3 | | | | UNC5A | 1.00 |
| 20373 | 3 | | | | | TTTY3 | 1.00 | 20469 | 3 | | | | UNC5B | 1.00 |
| 20374 | 3 | | | | | TTTY3B | 1.00 | 20470 | 3 | | | | UNC5C | 1.00 |
| 20375 | 3 | | | | | TTTY4 | 1.00 | 20471 | 3 | | | | UNC5D | 1.00 |
| 20376 | 3 | | | | | TTTY4B | 1.00 | 20472 | 3 | | | | UNC79 | 1.00 |
| 20377 | 3 | | | | | TTTY5 | 1.00 | 20473 | 3 | | | | UNC80 | 1.00 |
| 20378 | 3 | | | | | TTTY6 | 1.00 | 20474 | 3 | | | | UNC93A | 1.00 |
| 20379 | 3 | | | | | TTTY6B | 1.00 | 20475 | 3 | | | | UNCX | 1.00 |
| 20380 | 3 | | | | | TTTY7 | 1.00 | 20476 | 3 | | | | UNQ6494 | 1.00 |
| 20381 | 3 | | | | | TTTY7B | 1.00 | 20477 | 3 | | | | UNQ6975 | 1.00 |
| 20382 | 3 | | | | | TTTY8 | 1.00 | 20478 | 3 | | | | UOX | 1.00 |
| 20383 | 3 | | | | | TTTY8B | 1.00 | 20479 | 3 | | | | UPK1A | 1.00 |
| 20384 | 3 | | | | | TTTY9B | 1.00 | 20480 | 3 | | | | UPK1B | 1.00 |
| 20385 | 3 | | | | | TTYH1 | 1.00 | 20481 | 3 | | | | UPK2 | 1.00 |
| 20386 | 3 | | | | | TUB | 1.00 | 20482 | 3 | | | | UPK3B | 1.00 |
| 20387 | 3 | | | | | TUBA3C | 1.00 | 20483 | 3 | | | | UPP2 | 1.00 |
| 20388 | 3 | | | | | TUBA3D | 1.00 | 20484 | 3 | | | | URGCP-MRPS24 | 1.00 |
| 20389 | 3 | | | | | TUBA3E | 1.00 | 20485 | 3 | | | | UROC1 | 1.00 |
| 20390 | 3 | | | | | TUBA4B | 1.00 | 20486 | 3 | | | | USH1C | 1.00 |
| 20391 | 3 | | | | | TUBAL3 | 1.00 | 20487 | 3 | | | | USH1G | 1.00 |
| 20392 | 3 | | | | | TUBB3 | 1.00 | 20488 | 3 | | | | USH2A | 1.00 |
| 20393 | 3 | | | | | TUBB8 | 1.00 | 20489 | 3 | | | | USHBP1 | 1.00 |
| 20394 | 3 | | | | | TUBB8P5 | 1.00 | 20490 | 3 | | | | USP13 | 1.00 |
| 20395 | 3 | | | | | TULP1 | 1.00 | 20491 | 3 | | | | USP17 | 1.00 |
| 20396 | 3 | | | | | TULP2 | 1.00 | 20492 | 3 | | | | USP17L2 | 1.00 |
| 20397 | 3 | | | | | TUSC1 | 1.00 | 20493 | 3 | | | | USP17L6P | 1.00 |
| 20398 | 3 | | | | | TUSC3 | 1.00 | 20494 | 3 | | | | USP2 | 1.00 |
| 20399 | 3 | | | | | TUSC5 | 1.00 | 20495 | 3 | | | | USP26 | 1.00 |
| 20400 | 3 | | | | | TWIST1 | 1.00 | 20496 | 3 | | | | USP29 | 1.00 |
| 20401 | 3 | | | | | TWIST2 | 1.00 | 20497 | 3 | | | | USP43 | 1.00 |
| 20402 | 3 | | | | | TXLNG2P | 1.00 | 20498 | 3 | | | | USP50 | 1.00 |
| 20403 | 3 | | | | | TXNDC2 | 1.00 | 20499 | 3 | | | | USP51 | 1.00 |
| 20404 | 3 | | | | | TXNDC8 | 1.00 | 20500 | 3 | | | | USP9Y | 1.00 |
| 20405 | 3 | | | | | TXNRD3 | 1.00 | 20501 | 3 | | | | UTF1 | 1.00 |
| 20406 | 3 | | | | | TXNRD3NB | 1.00 | 20502 | 3 | | | | UTS2D | 1.00 |
| 20407 | 3 | | | | | TYR | 1.00 | 20503 | 3 | | | | UTS2R | 1.00 |
| 20408 | 3 | | | | | TYRO3 | 1.00 | 20504 | 3 | | | | UTY | 1.00 |
| 20409 | 3 | | | | | TYRO3P | 1.00 | 20505 | 3 | | | | VANGL2 | 1.00 |
| 20410 | 3 | | | | | TYRP1 | 1.00 | 20506 | 3 | | | | VASH2 | 1.00 |
| 20411 | 3 | | | | | UBAC2-AS1 | 1.00 | 20507 | 3 | | | | VASN | 1.00 |
| 20412 | 3 | | | | | UBAP1L | 1.00 | 20508 | 3 | | | | VAT1L | 1.00 |
| 20413 | 3 | | | | | UBD | 1.00 | 20509 | 3 | | | | VAX1 | 1.00 |
| 20414 | 3 | | | | | UBE2DNL | 1.00 | 20510 | 3 | | | | VAX2 | 1.00 |
| 20415 | 3 | | | | | UBE2F-SCLY | 1.00 | 20511 | 3 | | | | VCAM1 | 1.00 |
| 20416 | 3 | | | | | UBE2Q2P1 | 1.00 | 20512 | 3 | | | | VCX | 1.00 |
| 20417 | 3 | | | | | UBE2Q2P2 | 1.00 | 20513 | 3 | | | | VCX2 | 1.00 |
| 20418 | 3 | | | | | UBE2Q2P3 | 1.00 | 20514 | 3 | | | | VCX3A | 1.00 |
| 20419 | 3 | | | | | UBE2QL1 | 1.00 | 20515 | 3 | | | | VCX3B | 1.00 |
| 20420 | 3 | | | | | UBE2T | 1.00 | 20516 | 3 | | | | VCY | 1.00 |
| 20421 | 3 | | | | | UBE2U | 1.00 | 20517 | 3 | | | | VCY1B | 1.00 |
| 20422 | 3 | | | | | UBE3D | 1.00 | 20518 | 3 | | | | VEGFC | 1.00 |
| 20423 | 3 | | | | | UBL4B | 1.00 | 20519 | 3 | | | | VENTXP1 | 1.00 |
| 20424 | 3 | | | | | UBQLN3 | 1.00 | 20520 | 3 | | | | VGF | 1.00 |
| 20425 | 3 | | | | | UBTFL1 | 1.00 | 20521 | 3 | | | | VGLL1 | 1.00 |
| 20426 | 3 | | | | | UBXN10 | 1.00 | 20522 | 3 | | | | VGLL2 | 1.00 |
| 20427 | 3 | | | | | UCA1 | 1.00 | 20523 | 3 | | | | VGLL3 | 1.00 |
| 20428 | 3 | | | | | UCHL1 | 1.00 | 20524 | 3 | | | | VIL1 | 1.00 |
| 20429 | 3 | | | | | UCMA | 1.00 | 20525 | 3 | | | | VIP | 1.00 |
| 20430 | 3 | | | | | UCN2 | 1.00 | 20526 | 3 | | | | VIPR2 | 1.00 |
| 20431 | 3 | | | | | UCN3 | 1.00 | 20527 | 3 | | | | VIT | 1.00 |
| 20432 | 3 | | | | | UCP1 | 1.00 | 20528 | 3 | | | | VLDLR | 1.00 |
| 20433 | 3 | | | | | UG0898H09 | 1.00 | 20529 | 3 | | | | VN1R1 | 1.00 |
| 20434 | 3 | | | | | UGGT2 | 1.00 | 20530 | 3 | | | | VN1R10P | 1.00 |
| 20435 | 3 | | | | | UGT1A3 | 1.00 | 20531 | 3 | | | | VN1R2 | 1.00 |
| 20436 | 3 | | | | | UGT1A10 | 1.00 | 20532 | 3 | | | | VN1R4 | 1.00 |

Fig. 40 - 108

| | | | | | | | | | | | | | | | | |
|---|---|---|---|---|---|---|---|---|---|---|---|---|---|---|---|---|
| 20533 | 3 | | | | | | VN1R5 | 1.00 | 20629 | 3 | | | | | WSCD1 | 1.00 |
| 20534 | 3 | | | | | | VPREB1 | 1.00 | 20630 | 3 | | | | | WSCD2 | 1.00 |
| 20535 | 3 | | | | | | VPS37D | 1.00 | 20631 | 3 | | | | | WT1 | 1.00 |
| 20536 | 3 | | | | | | VRTN | 1.00 | 20632 | 3 | | | | | WT1-AS | 1.00 |
| 20537 | 3 | | | | | | VSIG10L | 1.00 | 20633 | 3 | | | | | WTIP | 1.00 |
| 20538 | 3 | | | | | | VSIG8 | 1.00 | 20634 | 3 | | | | | WWC1 | 1.00 |
| 20539 | 3 | | | | | | VSNL1 | 1.00 | 20635 | 3 | | | | | WWTR1 | 1.00 |
| 20540 | 3 | | | | | | VSTM2A | 1.00 | 20636 | 3 | | | | | WWTR1-AS1 | 1.00 |
| 20541 | 3 | | | | | | VSTM2B | 1.00 | 20637 | 3 | | | | | XAGE1A | 1.00 |
| 20542 | 3 | | | | | | VSTM2L | 1.00 | 20638 | 3 | | | | | XAGE1C | 1.00 |
| 20543 | 3 | | | | | | VSTM4 | 1.00 | 20639 | 3 | | | | | XAGE1E | 1.00 |
| 20544 | 3 | | | | | | VSTM5 | 1.00 | 20640 | 3 | | | | | XAGE2 | 1.00 |
| 20545 | 3 | | | | | | VSX1 | 1.00 | 20641 | 3 | | | | | XAGE2B | 1.00 |
| 20546 | 3 | | | | | | VSX2 | 1.00 | 20642 | 3 | | | | | XAGE3 | 1.00 |
| 20547 | 3 | | | | | | VTCN1 | 1.00 | 20643 | 3 | | | | | XAGE5 | 1.00 |
| 20548 | 3 | | | | | | VTN | 1.00 | 20644 | 3 | | | | | XDH | 1.00 |
| 20549 | 3 | | | | | | VTRNA1-1 | 1.00 | 20645 | 3 | | | | | XG | 1.00 |
| 20550 | 3 | | | | | | VTRNA1-2 | 1.00 | 20646 | 3 | | | | | XGPY2 | 1.00 |
| 20551 | 3 | | | | | | VTRNA1-3 | 1.00 | 20647 | 3 | | | | | XIRP1 | 1.00 |
| 20552 | 3 | | | | | | VTRNA2-1 | 1.00 | 20648 | 3 | | | | | XIRP2 | 1.00 |
| 20553 | 3 | | | | | | VWA1 | 1.00 | 20649 | 3 | | | | | XKR3 | 1.00 |
| 20554 | 3 | | | | | | VWA2 | 1.00 | 20650 | 3 | | | | | XKR4 | 1.00 |
| 20555 | 3 | | | | | | VWA3A | 1.00 | 20651 | 3 | | | | | XKR5 | 1.00 |
| 20556 | 3 | | | | | | VWA3B | 1.00 | 20652 | 3 | | | | | XKR6 | 1.00 |
| 20557 | 3 | | | | | | VWA5B1 | 1.00 | 20653 | 3 | | | | | XKR7 | 1.00 |
| 20558 | 3 | | | | | | VWA5B2 | 1.00 | 20654 | 3 | | | | | XKR9 | 1.00 |
| 20559 | 3 | | | | | | VWA7 | 1.00 | 20655 | 3 | | | | | XKRX | 1.00 |
| 20560 | 3 | | | | | | VWC2 | 1.00 | 20656 | 3 | | | | | XKRY | 1.00 |
| 20561 | 3 | | | | | | VWC2L | 1.00 | 20657 | 3 | | | | | XKRY2 | 1.00 |
| 20562 | 3 | | | | | | VWDE | 1.00 | 20658 | 3 | | | | | XPNPEP2 | 1.00 |
| 20563 | 3 | | | | | | WASF3 | 1.00 | 20659 | 3 | | | | | XRCC2 | 1.00 |
| 20564 | 3 | | | | | | WBP2NL | 1.00 | 20660 | 3 | | | | | XYLB | 1.00 |
| 20565 | 3 | | | | | | WBSCR17 | 1.00 | 20661 | 3 | | | | | YAP1 | 1.00 |
| 20566 | 3 | | | | | | WBSCR27 | 1.00 | 20662 | 3 | | | | | YBX2 | 1.00 |
| 20567 | 3 | | | | | | WBSCR28 | 1.00 | 20663 | 3 | | | | | YIPF7 | 1.00 |
| 20568 | 3 | | | | | | WDFY3-AS2 | 1.00 | 20664 | 3 | | | | | YSK4 | 1.00 |
| 20569 | 3 | | | | | | WDHD1 | 1.00 | 20665 | 3 | | | | | YY2 | 1.00 |
| 20570 | 3 | | | | | | WDPCP | 1.00 | 20666 | 3 | | | | | ZACN | 1.00 |
| 20571 | 3 | | | | | | WDR16 | 1.00 | 20667 | 3 | | | | | ZAN | 1.00 |
| 20572 | 3 | | | | | | WDR17 | 1.00 | 20668 | 3 | | | | | ZAR1 | 1.00 |
| 20573 | 3 | | | | | | WDR19 | 1.00 | 20669 | 3 | | | | | ZAR1L | 1.00 |
| 20574 | 3 | | | | | | WDR27 | 1.00 | 20670 | 3 | | | | | ZBBX | 1.00 |
| 20575 | 3 | | | | | | WDR31 | 1.00 | 20671 | 3 | | | | | ZBED2 | 1.00 |
| 20576 | 3 | | | | | | WDR38 | 1.00 | 20672 | 3 | | | | | ZBTB20-AS1 | 1.00 |
| 20577 | 3 | | | | | | WDR49 | 1.00 | 20673 | 3 | | | | | ZBTB7C | 1.00 |
| 20578 | 3 | | | | | | WDR62 | 1.00 | 20674 | 3 | | | | | ZBTB8A | 1.00 |
| 20579 | 3 | | | | | | WDR63 | 1.00 | 20675 | 3 | | | | | ZBTB8B | 1.00 |
| 20580 | 3 | | | | | | WDR64 | 1.00 | 20676 | 3 | | | | | ZC2HC1B | 1.00 |
| 20581 | 3 | | | | | | WDR65 | 1.00 | 20677 | 3 | | | | | ZC2HC1C | 1.00 |
| 20582 | 3 | | | | | | WDR66 | 1.00 | 20678 | 3 | | | | | ZC3H12B | 1.00 |
| 20583 | 3 | | | | | | WDR69 | 1.00 | 20679 | 3 | | | | | ZCCHC12 | 1.00 |
| 20584 | 3 | | | | | | WDR72 | 1.00 | 20680 | 3 | | | | | ZCCHC13 | 1.00 |
| 20585 | 3 | | | | | | WDR78 | 1.00 | 20681 | 3 | | | | | ZCCHC16 | 1.00 |
| 20586 | 3 | | | | | | WDR86 | 1.00 | 20682 | 3 | | | | | ZCCHC5 | 1.00 |
| 20587 | 3 | | | | | | WDR87 | 1.00 | 20683 | 3 | | | | | ZCWPW2 | 1.00 |
| 20588 | 3 | | | | | | WDR88 | 1.00 | 20684 | 3 | | | | | ZDHHC1 | 1.00 |
| 20589 | 3 | | | | | | WDR90 | 1.00 | 20685 | 3 | | | | | ZDHHC11 | 1.00 |
| 20590 | 3 | | | | | | WDR93 | 1.00 | 20686 | 3 | | | | | ZDHHC15 | 1.00 |
| 20591 | 3 | | | | | | WDR96 | 1.00 | 20687 | 3 | | | | | ZDHHC22 | 1.00 |
| 20592 | 3 | | | | | | WEE2 | 1.00 | 20688 | 3 | | | | | ZDHHC8P1 | 1.00 |
| 20593 | 3 | | | | | | WFDC1 | 1.00 | 20689 | 3 | | | | | ZEB2-AS1 | 1.00 |
| 20594 | 3 | | | | | | WFDC10A | 1.00 | 20690 | 3 | | | | | ZFAT-AS1 | 1.00 |
| 20595 | 3 | | | | | | WFDC10B | 1.00 | 20691 | 3 | | | | | ZFHX2 | 1.00 |
| 20596 | 3 | | | | | | WFDC11 | 1.00 | 20692 | 3 | | | | | ZFHX4 | 1.00 |
| 20597 | 3 | | | | | | WFDC12 | 1.00 | 20693 | 3 | | | | | ZFP112 | 1.00 |
| 20598 | 3 | | | | | | WFDC13 | 1.00 | 20694 | 3 | | | | | ZFP2 | 1.00 |
| 20599 | 3 | | | | | | WFDC2 | 1.00 | 20695 | 3 | | | | | ZFP42 | 1.00 |
| 20600 | 3 | | | | | | WFDC3 | 1.00 | 20696 | 3 | | | | | ZFP91-CNTF | 1.00 |
| 20601 | 3 | | | | | | WFDC5 | 1.00 | 20697 | 3 | | | | | ZFP92 | 1.00 |
| 20602 | 3 | | | | | | WFDC6 | 1.00 | 20698 | 3 | | | | | ZFPM2 | 1.00 |
| 20603 | 3 | | | | | | WFDC8 | 1.00 | 20699 | 3 | | | | | ZFR2 | 1.00 |
| 20604 | 3 | | | | | | WFDC9 | 1.00 | 20700 | 3 | | | | | ZFY | 1.00 |
| 20605 | 3 | | | | | | WFIKKN1 | 1.00 | 20701 | 3 | | | | | ZFYVE9 | 1.00 |
| 20606 | 3 | | | | | | WFIKKN2 | 1.00 | 20702 | 3 | | | | | ZG16 | 1.00 |
| 20607 | 3 | | | | | | WIF1 | 1.00 | 20703 | 3 | | | | | ZIC1 | 1.00 |
| 20608 | 3 | | | | | | WIPF3 | 1.00 | 20704 | 3 | | | | | ZIC2 | 1.00 |
| 20609 | 3 | | | | | | WISP1 | 1.00 | 20705 | 3 | | | | | ZIC3 | 1.00 |
| 20610 | 3 | | | | | | WISP2 | 1.00 | 20706 | 3 | | | | | ZIC4 | 1.00 |
| 20611 | 3 | | | | | | WISP3 | 1.00 | 20707 | 3 | | | | | ZIC5 | 1.00 |
| 20612 | 3 | | | | | | WNK2 | 1.00 | 20708 | 3 | | | | | ZIM2 | 1.00 |
| 20613 | 3 | | | | | | WNK3 | 1.00 | 20709 | 3 | | | | | ZIM3 | 1.00 |
| 20614 | 3 | | | | | | WNK4 | 1.00 | 20710 | 3 | | | | | ZMAT4 | 1.00 |
| 20615 | 3 | | | | | | WNT1 | 1.00 | 20711 | 3 | | | | | ZMYND10 | 1.00 |
| 20616 | 3 | | | | | | WNT11 | 1.00 | 20712 | 3 | | | | | ZMYND12 | 1.00 |
| 20617 | 3 | | | | | | WNT2 | 1.00 | 20713 | 3 | | | | | ZNF114 | 1.00 |
| 20618 | 3 | | | | | | WNT2B | 1.00 | 20714 | 3 | | | | | ZNF135 | 1.00 |
| 20619 | 3 | | | | | | WNT3 | 1.00 | 20715 | 3 | | | | | ZNF157 | 1.00 |
| 20620 | 3 | | | | | | WNT3A | 1.00 | 20716 | 3 | | | | | ZNF165 | 1.00 |
| 20621 | 3 | | | | | | WNT4 | 1.00 | 20717 | 3 | | | | | ZNF177 | 1.00 |
| 20622 | 3 | | | | | | WNT5A | 1.00 | 20718 | 3 | | | | | ZNF214 | 1.00 |
| 20623 | 3 | | | | | | WNT6 | 1.00 | 20719 | 3 | | | | | ZNF215 | 1.00 |
| 20624 | 3 | | | | | | WNT7B | 1.00 | 20720 | 3 | | | | | ZNF221 | 1.00 |
| 20625 | 3 | | | | | | WNT8A | 1.00 | 20721 | 3 | | | | | ZNF229 | 1.00 |
| 20626 | 3 | | | | | | WNT8B | 1.00 | 20722 | 3 | | | | | ZNF233 | 1.00 |
| 20627 | 3 | | | | | | WNT9A | 1.00 | 20723 | 3 | | | | | ZNF280A | 1.00 |
| 20628 | 3 | | | | | | WNT9B | 1.00 | 20724 | 3 | | | | | ZNF280B | 1.00 |

Fig. 40 - 109

| | | | | | | | | | | | | | |
|---|---|---|---|---|---|---|---|---|---|---|---|---|---|
| 20725 | 3 | | | | | ZNF295-AS1 | 1.00 | 20821 | 3 | | | ZSCAN20 | 1.00 |
| 20726 | 3 | | | | | ZNF300P1 | 1.00 | 20822 | 3 | | | ZSCAN23 | 1.00 |
| 20727 | 3 | | | | | ZNF311 | 1.00 | 20823 | 3 | | | ZSCAN4 | 1.00 |
| 20728 | 3 | | | | | ZNF32-AS3 | 1.00 | 20824 | 3 | | | ZSCAN5B | 1.00 |
| 20729 | 3 | | | | | ZNF323 | 1.00 | 20825 | 3 | | | ZSWIM2 | 1.00 |
| 20730 | 3 | | | | | ZNF334 | 1.00 | 20826 | 3 | | | ZSWIM5 | 1.00 |
| 20731 | 3 | | | | | ZNF385B | 1.00 | 20827 | 3 | | | ZYG11A | 1.00 |
| 20732 | 3 | | | | | ZNF385C | 1.00 | 20828 | 3 | | | tAKR | 1.00 |
| 20733 | 3 | | | | | ZNF391 | 1.00 | | | | | | |
| 20734 | 3 | | | | | ZNF423 | 1.00 | | | | | | |
| 20735 | 3 | | | | | ZNF433 | 1.00 | | | | | | |
| 20736 | 3 | | | | | ZNF442 | 1.00 | | | | | | |
| 20737 | 3 | | | | | ZNF454 | 1.00 | | | | | | |
| 20738 | 3 | | | | | ZNF462 | 1.00 | | | | | | |
| 20739 | 3 | | | | | ZNF469 | 1.00 | | | | | | |
| 20740 | 3 | | | | | ZNF471 | 1.00 | | | | | | |
| 20741 | 3 | | | | | ZNF474 | 1.00 | | | | | | |
| 20742 | 3 | | | | | ZNF479 | 1.00 | | | | | | |
| 20743 | 3 | | | | | ZNF483 | 1.00 | | | | | | |
| 20744 | 3 | | | | | ZNF488 | 1.00 | | | | | | |
| 20745 | 3 | | | | | ZNF491 | 1.00 | | | | | | |
| 20746 | 3 | | | | | ZNF492 | 1.00 | | | | | | |
| 20747 | 3 | | | | | ZNF497 | 1.00 | | | | | | |
| 20748 | 3 | | | | | ZNF503-AS1 | 1.00 | | | | | | |
| 20749 | 3 | | | | | ZNF503-AS2 | 1.00 | | | | | | |
| 20750 | 3 | | | | | ZNF519 | 1.00 | | | | | | |
| 20751 | 3 | | | | | ZNF521 | 1.00 | | | | | | |
| 20752 | 3 | | | | | ZNF534 | 1.00 | | | | | | |
| 20753 | 3 | | | | | ZNF536 | 1.00 | | | | | | |
| 20754 | 3 | | | | | ZNF541 | 1.00 | | | | | | |
| 20755 | 3 | | | | | ZNF556 | 1.00 | | | | | | |
| 20756 | 3 | | | | | ZNF559-ZNF177 | 1.00 | | | | | | |
| 20757 | 3 | | | | | ZNF560 | 1.00 | | | | | | |
| 20758 | 3 | | | | | ZNF578 | 1.00 | | | | | | |
| 20759 | 3 | | | | | ZNF599 | 1.00 | | | | | | |
| 20760 | 3 | | | | | ZNF610 | 1.00 | | | | | | |
| 20761 | 3 | | | | | ZNF625-ZNF20 | 1.00 | | | | | | |
| 20762 | 3 | | | | | ZNF645 | 1.00 | | | | | | |
| 20763 | 3 | | | | | ZNF648 | 1.00 | | | | | | |
| 20764 | 3 | | | | | ZNF660 | 1.00 | | | | | | |
| 20765 | 3 | | | | | ZNF662 | 1.00 | | | | | | |
| 20766 | 3 | | | | | ZNF663 | 1.00 | | | | | | |
| 20767 | 3 | | | | | ZNF664-FAM101A | 1.00 | | | | | | |
| 20768 | 3 | | | | | ZNF665 | 1.00 | | | | | | |
| 20769 | 3 | | | | | ZNF667 | 1.00 | | | | | | |
| 20770 | 3 | | | | | ZNF670 | 1.00 | | | | | | |
| 20771 | 3 | | | | | ZNF670-ZNF695 | 1.00 | | | | | | |
| 20772 | 3 | | | | | ZNF676 | 1.00 | | | | | | |
| 20773 | 3 | | | | | ZNF677 | 1.00 | | | | | | |
| 20774 | 3 | | | | | ZNF679 | 1.00 | | | | | | |
| 20775 | 3 | | | | | ZNF695 | 1.00 | | | | | | |
| 20776 | 3 | | | | | ZNF704 | 1.00 | | | | | | |
| 20777 | 3 | | | | | ZNF705A | 1.00 | | | | | | |
| 20778 | 3 | | | | | ZNF705D | 1.00 | | | | | | |
| 20779 | 3 | | | | | ZNF705G | 1.00 | | | | | | |
| 20780 | 3 | | | | | ZNF711 | 1.00 | | | | | | |
| 20781 | 3 | | | | | ZNF713 | 1.00 | | | | | | |
| 20782 | 3 | | | | | ZNF716 | 1.00 | | | | | | |
| 20783 | 3 | | | | | ZNF717 | 1.00 | | | | | | |
| 20784 | 3 | | | | | ZNF726 | 1.00 | | | | | | |
| 20785 | 3 | | | | | ZNF727 | 1.00 | | | | | | |
| 20786 | 3 | | | | | ZNF729 | 1.00 | | | | | | |
| 20787 | 3 | | | | | ZNF732 | 1.00 | | | | | | |
| 20788 | 3 | | | | | ZNF735 | 1.00 | | | | | | |
| 20789 | 3 | | | | | ZNF750 | 1.00 | | | | | | |
| 20790 | 3 | | | | | ZNF771 | 1.00 | | | | | | |
| 20791 | 3 | | | | | ZNF774 | 1.00 | | | | | | |
| 20792 | 3 | | | | | ZNF788 | 1.00 | | | | | | |
| 20793 | 3 | | | | | ZNF804B | 1.00 | | | | | | |
| 20794 | 3 | | | | | ZNF812 | 1.00 | | | | | | |
| 20795 | 3 | | | | | ZNF816-ZNF321P | 1.00 | | | | | | |
| 20796 | 3 | | | | | ZNF826P | 1.00 | | | | | | |
| 20797 | 3 | | | | | ZNF833P | 1.00 | | | | | | |
| 20798 | 3 | | | | | ZNF843 | 1.00 | | | | | | |
| 20799 | 3 | | | | | ZNF847P | 1.00 | | | | | | |
| 20800 | 3 | | | | | ZNF876P | 1.00 | | | | | | |
| 20801 | 3 | | | | | ZNF878 | 1.00 | | | | | | |
| 20802 | 3 | | | | | ZNF90 | 1.00 | | | | | | |
| 20803 | 3 | | | | | ZNF98 | 1.00 | | | | | | |
| 20804 | 3 | | | | | ZNF99 | 1.00 | | | | | | |
| 20805 | 3 | | | | | ZNRD1-AS1 | 1.00 | | | | | | |
| 20806 | 3 | | | | | ZNRF2P1 | 1.00 | | | | | | |
| 20807 | 3 | | | | | ZNRF2P2 | 1.00 | | | | | | |
| 20808 | 3 | | | | | ZNRF3 | 1.00 | | | | | | |
| 20809 | 3 | | | | | ZNRF4 | 1.00 | | | | | | |
| 20810 | 3 | | | | | ZP1 | 1.00 | | | | | | |
| 20811 | 3 | | | | | ZP2 | 1.00 | | | | | | |
| 20812 | 3 | | | | | ZP4 | 1.00 | | | | | | |
| 20813 | 3 | | | | | ZPBP | 1.00 | | | | | | |
| 20814 | 3 | | | | | ZPBP2 | 1.00 | | | | | | |
| 20815 | 3 | | | | | ZPLD1 | 1.00 | | | | | | |
| 20816 | 3 | | | | | ZRANB2-AS2 | 1.00 | | | | | | |
| 20817 | 3 | | | | | ZRANB3 | 1.00 | | | | | | |
| 20818 | 3 | | | | | ZSCAN1 | 1.00 | | | | | | |
| 20819 | 3 | | | | | ZSCAN10 | 1.00 | | | | | | |
| 20820 | 3 | | | | | ZSCAN12P1 | 1.00 | | | | | | |

Fig. 41 - 1

| Line No. | Group No. | | | | | Sub-Groups | Gene Name | Lung cancer |
|---|---|---|---|---|---|---|---|---|
| 1 | 3 | 4 | 5 | 6 | 7 | VII-2 | LOC283663 | 0.19 |
| 2 | 3 | 4 | 5 | 6 | 7 | VII-2 | SIGLEC14 | 0.10 |
| 3 | 3 | 4 | 5 | 6 | 7 | VII-1 | DDX3Y | 15.80 |
| 4 | 3 | 4 | 5 | 6 | 7 | VII-1 | EIF1AY | 16.14 |
| 5 | 3 | 4 | 5 | 6 | 7 | VII-1 | ELANE | 5.95 |
| 6 | 3 | 4 | 5 | 6 | 7 | VII-1 | GPR84 | 5.19 |
| 7 | 3 | 4 | 5 | 6 | 7 | VII-1 | HIST1H3G | 9.22 |
| 8 | 3 | 4 | 5 | 6 | 7 | VII-1 | HIST1H4B | 21.00 |
| 9 | 3 | 4 | 5 | 6 | 7 | VII-1 | HIST1H4C | 75.10 |
| 10 | 3 | 4 | 5 | 6 | 7 | VII-1 | HIST2H3C | 5.96 |
| 11 | 3 | 4 | 5 | 6 | 7 | VII-1 | HIST4H4 | 7.12 |
| 12 | 3 | 4 | 5 | 6 | 7 | VII-1 | HNRNPH2 | 12.45 |
| 13 | 3 | 4 | 5 | 6 | 7 | VII-1 | HP | 7.57 |
| 14 | 3 | 4 | 5 | 6 | 7 | VII-1 | HTRA1 | 7.28 |
| 15 | 3 | 4 | 5 | 6 | 7 | VII-1 | METTL7B | 18.12 |
| 16 | 3 | 4 | 5 | 6 | 7 | VII-1 | MIR3648 | 32.68 |
| 17 | 3 | 4 | 5 | 6 | 7 | VII-1 | RPS4Y1 | 148.70 |
| 18 | 3 | 4 | 5 | 6 | 7 | VII-1 | SERPINB10 | 6.11 |
| 19 | 3 | 4 | 5 | 6 | 7 | VII-1 | SNORA40 | 11.00 |
| 20 | 3 | 4 | 5 | 6 | 7 | VII-1 | SNORA65 | 7.04 |
| 21 | 3 | 4 | 5 | 6 | 7 | VII-1 | TCN2 | 6.05 |
| 22 | 3 | 4 | 5 | 6 | 7 | VII-1 | TXLNG2P | 6.18 |
| 23 | 3 | 4 | 5 | 6 | 7 | VII-1 | UTS2 | 14.73 |
| 24 | 3 | 4 | 5 | 6 | 7 | VII-1 | UTY | 5.01 |
| 25 | 3 | 4 | 5 | 6 | | VI-2 | ADAM28 | 0.48 |
| 26 | 3 | 4 | 5 | 6 | | VI-2 | AFAP1 | 0.48 |
| 27 | 3 | 4 | 5 | 6 | | VI-2 | C2orf88 | 0.48 |
| 28 | 3 | 4 | 5 | 6 | | VI-2 | CDK5R1 | 0.49 |
| 29 | 3 | 4 | 5 | 6 | | VI-2 | CNR2 | 0.23 |
| 30 | 3 | 4 | 5 | 6 | | VI-2 | DLG3 | 0.42 |
| 31 | 3 | 4 | 5 | 6 | | VI-2 | DUSP14 | 0.41 |
| 32 | 3 | 4 | 5 | 6 | | VI-2 | EPHB1 | 0.47 |
| 33 | 3 | 4 | 5 | 6 | | VI-2 | GATS | 0.48 |
| 34 | 3 | 4 | 5 | 6 | | VI-2 | GUSBP1 | 0.47 |
| 35 | 3 | 4 | 5 | 6 | | VI-2 | HSPB11 | 0.48 |
| 36 | 3 | 4 | 5 | 6 | | VI-2 | ID12-AS1 | 0.44 |
| 37 | 3 | 4 | 5 | 6 | | VI-2 | LOC100499177 | 0.33 |
| 38 | 3 | 4 | 5 | 6 | | VI-2 | LOC282997 | 0.50 |
| 39 | 3 | 4 | 5 | 6 | | VI-2 | LOC728431 | 0.42 |
| 40 | 3 | 4 | 5 | 6 | | VI-2 | MEGF6 | 0.42 |
| 41 | 3 | 4 | 5 | 6 | | VI-2 | PLEK2 | 0.47 |
| 42 | 3 | 4 | 5 | 6 | | VI-2 | PPDPF | 0.39 |
| 43 | 3 | 4 | 5 | 6 | | VI-2 | RAB36 | 0.49 |
| 44 | 3 | 4 | 5 | 6 | | VI-2 | RPL12 | 0.39 |
| 45 | 3 | 4 | 5 | 6 | | VI-2 | RPP21 | 0.42 |
| 46 | 3 | 4 | 5 | 6 | | VI-2 | SDPR | 0.42 |
| 47 | 3 | 4 | 5 | 6 | | VI-2 | SLC25A5-AS1 | 0.45 |
| 48 | 3 | 4 | 5 | 6 | | VI-2 | SNHG1 | 0.46 |
| 49 | 3 | 4 | 5 | 6 | | VI-2 | TMEM40 | 0.45 |
| 50 | 3 | 4 | 5 | 6 | | VI-2 | TPTEP1 | 0.31 |
| 51 | 3 | 4 | 5 | 6 | | VI-2 | TTC32 | 0.47 |
| 52 | 3 | 4 | 5 | 6 | | VI-2 | U2AF1L4 | 0.44 |
| 53 | 3 | 4 | 5 | 6 | | VI-2 | WHAMMP3 | 0.47 |
| 54 | 3 | 4 | 5 | 6 | | VI-2 | ZMAT1 | 0.45 |
| 55 | 3 | 4 | 5 | 6 | | VI-2 | ZNF117 | 0.42 |
| 56 | 3 | 4 | 5 | 6 | | VI-2 | ZSCAN18 | 0.46 |
| 57 | 3 | 4 | 5 | 6 | | VI-1 | AAMP | 2.12 |
| 58 | 3 | 4 | 5 | 6 | | VI-1 | AARS | 2.03 |
| 59 | 3 | 4 | 5 | 6 | | VI-1 | AASDHPPT | 2.06 |
| 60 | 3 | 4 | 5 | 6 | | VI-1 | ABCB10 | 2.24 |
| 61 | 3 | 4 | 5 | 6 | | VI-1 | ABCD1 | 2.01 |
| 62 | 3 | 4 | 5 | 6 | | VI-1 | ACACA | 2.24 |
| 63 | 3 | 4 | 5 | 6 | | VI-1 | ACOT1 | 2.34 |
| 64 | 3 | 4 | 5 | 6 | | VI-1 | ACOX3 | 2.12 |
| 65 | 3 | 4 | 5 | 6 | | VI-1 | ACSS2 | 2.16 |
| 66 | 3 | 4 | 5 | 6 | | VI-1 | ACTR2 | 2.05 |
| 67 | 3 | 4 | 5 | 6 | | VI-1 | ACVR1B | 2.12 |
| 68 | 3 | 4 | 5 | 6 | | VI-1 | ADAM10 | 2.08 |
| 69 | 3 | 4 | 5 | 6 | | VI-1 | ADAM9 | 3.58 |
| 70 | 3 | 4 | 5 | 6 | | VI-1 | ADCY3 | 2.14 |
| 71 | 3 | 4 | 5 | 6 | | VI-1 | ADCY7 | 2.20 |
| 72 | 3 | 4 | 5 | 6 | | VI-1 | ADCY9 | 2.43 |
| 73 | 3 | 4 | 5 | 6 | | VI-1 | ADO | 2.07 |
| 74 | 3 | 4 | 5 | 6 | | VI-1 | ADPRH | 3.16 |
| 75 | 3 | 4 | 5 | 6 | | VI-1 | ADSS | 2.04 |
| 76 | 3 | 4 | 5 | 6 | | VI-1 | AGFG1 | 2.25 |
| 77 | 3 | 4 | 5 | 6 | | VI-1 | AGPAT3 | 2.73 |
| 78 | 3 | 4 | 5 | 6 | | VI-1 | AGPS | 2.93 |
| 79 | 3 | 4 | 5 | 6 | | VI-1 | AIF1 | 2.09 |
| 80 | 3 | 4 | 5 | 6 | | VI-1 | AIFM1 | 2.13 |
| 81 | 3 | 4 | 5 | 6 | | VI-1 | AKR1A1 | 2.57 |
| 82 | 3 | 4 | 5 | 6 | | VI-1 | AKR7A2 | 2.38 |
| 83 | 3 | 4 | 5 | 6 | | VI-1 | AKR7A2P1 | 2.05 |
| 84 | 3 | 4 | 5 | 6 | | VI-1 | ALDH3A2 | 2.20 |
| 85 | 3 | 4 | 5 | 6 | | VI-1 | ALDH4A1 | 2.31 |
| 86 | 3 | 4 | 5 | 6 | | VI-1 | ALG1 | 2.22 |
| 87 | 3 | 4 | 5 | 6 | | VI-1 | ALG8 | 2.52 |
| 88 | 3 | 4 | 5 | 6 | | VI-1 | ALYREF | 2.01 |
| 89 | 3 | 4 | 5 | 6 | | VI-1 | ANKRD12 | 2.00 |
| 90 | 3 | 4 | 5 | 6 | | VI-1 | ANO10 | 2.12 |
| 91 | 3 | 4 | 5 | 6 | | VI-1 | ANPEP | 2.07 |
| 92 | 3 | 4 | 5 | 6 | | VI-1 | ANXA5 | 2.99 |
| 93 | 3 | 4 | 5 | 6 | | VI-1 | AP1AR | 2.25 |
| 94 | 3 | 4 | 5 | 6 | | VI-1 | AP1B1 | 2.28 |
| 95 | 3 | 4 | 5 | 6 | | VI-1 | AP2S1 | 2.06 |
| 96 | 3 | 4 | 5 | 6 | | VI-1 | AP3B1 | 2.11 |
| 97 | 3 | 4 | 5 | 6 | | VI-1 | APLP2 | 2.39 |
| 98 | 3 | 4 | 5 | 6 | | VI-1 | ARG2 | 2.07 |
| 99 | 3 | 4 | 5 | 6 | | VI-1 | ARHGAP18 | 2.18 |
| 100 | 3 | 4 | 5 | 6 | | VI-1 | ARHGEF10 | 2.49 |
| 101 | 3 | 4 | 5 | 6 | | VI-1 | ARL5A | 2.07 |
| 102 | 3 | 4 | 5 | 6 | | VI-1 | ARL8B | 2.27 |
| 103 | 3 | 4 | 5 | 6 | | VI-1 | ARMC10 | 2.27 |
| 104 | 3 | 4 | 5 | 6 | | VI-1 | ARSB | 2.06 |
| 105 | 3 | 4 | 5 | 6 | | VI-1 | ASAH1 | 2.03 |
| 106 | 3 | 4 | 5 | 6 | | VI-1 | ASCC3 | 2.42 |
| 107 | 3 | 4 | 5 | 6 | | VI-1 | ASPH | 2.13 |
| 108 | 3 | 4 | 5 | 6 | | VI-1 | ATF3 | 2.26 |
| 109 | 3 | 4 | 5 | 6 | | VI-1 | ATF7 | 2.02 |
| 110 | 3 | 4 | 5 | 6 | | VI-1 | ATG7 | 2.30 |
| 111 | 3 | 4 | 5 | 6 | | VI-1 | ATL3 | 2.05 |
| 112 | 3 | 4 | 5 | 6 | | VI-1 | ATP13A3 | 2.28 |
| 113 | 3 | 4 | 5 | 6 | | VI-1 | ATP1A1 | 2.41 |
| 114 | 3 | 4 | 5 | 6 | | VI-1 | ATP1B3 | 2.42 |
| 115 | 3 | 4 | 5 | 6 | | VI-1 | ATP2A2 | 2.82 |
| 116 | 3 | 4 | 5 | 6 | | VI-1 | ATP5A1 | 2.14 |
| 117 | 3 | 4 | 5 | 6 | | VI-1 | ATP5B | 2.26 |
| 118 | 3 | 4 | 5 | 6 | | VI-1 | ATP5H | 2.15 |
| 119 | 3 | 4 | 5 | 6 | | VI-1 | ATP6AP2 | 2.51 |
| 120 | 3 | 4 | 5 | 6 | | VI-1 | ATP6V1C2 | 2.08 |
| 121 | 3 | 4 | 5 | 6 | | VI-1 | ATP6V1D | 2.81 |
| 122 | 3 | 4 | 5 | 6 | | VI-1 | ATRX | 2.05 |
| 123 | 3 | 4 | 5 | 6 | | VI-1 | ATXN2 | 2.18 |
| 124 | 3 | 4 | 5 | 6 | | VI-1 | AVEN | 2.62 |
| 125 | 3 | 4 | 5 | 6 | | VI-1 | AZU1 | 2.35 |
| 126 | 3 | 4 | 5 | 6 | | VI-1 | BRE | 2.37 |
| 127 | 3 | 4 | 5 | 6 | | VI-1 | BST2 | 2.24 |
| 128 | 3 | 4 | 5 | 6 | | VI-1 | BYSL | 2.16 |
| 129 | 3 | 4 | 5 | 6 | | VI-1 | C10orf11 | 3.20 |
| 130 | 3 | 4 | 5 | 6 | | VI-1 | C11orf10 | 2.39 |
| 131 | 3 | 4 | 5 | 6 | | VI-1 | C11orf73 | 2.73 |
| 132 | 3 | 4 | 5 | 6 | | VI-1 | C11orf75 | 2.27 |
| 133 | 3 | 4 | 5 | 6 | | VI-1 | C11orf82 | 2.77 |
| 134 | 3 | 4 | 5 | 6 | | VI-1 | C12orf4 | 2.01 |
| 135 | 3 | 4 | 5 | 6 | | VI-1 | C12orf49 | 2.02 |
| 136 | 3 | 4 | 5 | 6 | | VI-1 | C14orf21 | 2.24 |
| 137 | 3 | 4 | 5 | 6 | | VI-1 | C16orf62 | 2.12 |
| 138 | 3 | 4 | 5 | 6 | | VI-1 | C16orf70 | 2.55 |
| 139 | 3 | 4 | 5 | 6 | | VI-1 | C17orf58 | 2.26 |
| 140 | 3 | 4 | 5 | 6 | | VI-1 | C17orf89 | 2.11 |
| 141 | 3 | 4 | 5 | 6 | | VI-1 | C19orf38 | 2.22 |
| 142 | 3 | 4 | 5 | 6 | | VI-1 | C19orf54 | 2.48 |
| 143 | 3 | 4 | 5 | 6 | | VI-1 | C19orf59 | 3.03 |
| 144 | 3 | 4 | 5 | 6 | | VI-1 | C1QA | 4.03 |
| 145 | 3 | 4 | 5 | 6 | | VI-1 | C1QC | 3.96 |
| 146 | 3 | 4 | 5 | 6 | | VI-1 | C1orf115 | 3.95 |
| 147 | 3 | 4 | 5 | 6 | | VI-1 | C1orf162 | 2.29 |
| 148 | 3 | 4 | 5 | 6 | | VI-1 | C2 | 2.40 |
| 149 | 3 | 4 | 5 | 6 | | VI-1 | C20orf118 | 2.32 |
| 150 | 3 | 4 | 5 | 6 | | VI-1 | C20orf194 | 2.09 |
| 151 | 3 | 4 | 5 | 6 | | VI-1 | C20orf4 | 2.02 |
| 152 | 3 | 4 | 5 | 6 | | VI-1 | C22orf23 | 2.04 |
| 153 | 3 | 4 | 5 | 6 | | VI-1 | C22orf28 | 2.01 |
| 154 | 3 | 4 | 5 | 6 | | VI-1 | C2orf18 | 2.32 |
| 155 | 3 | 4 | 5 | 6 | | VI-1 | C2orf81 | 2.75 |
| 156 | 3 | 4 | 5 | 6 | | VI-1 | C3orf14 | 3.29 |
| 157 | 3 | 4 | 5 | 6 | | VI-1 | C4orf32 | 2.19 |
| 158 | 3 | 4 | 5 | 6 | | VI-1 | C5orf43 | 2.31 |
| 159 | 3 | 4 | 5 | 6 | | VI-1 | C9orf167 | 2.60 |
| 160 | 3 | 4 | 5 | 6 | | VI-1 | CALHM2 | 2.04 |
| 161 | 3 | 4 | 5 | 6 | | VI-1 | CALR | 2.10 |
| 162 | 3 | 4 | 5 | 6 | | VI-1 | CAND1 | 2.15 |
| 163 | 3 | 4 | 5 | 6 | | VI-1 | CANX | 2.36 |
| 164 | 3 | 4 | 5 | 6 | | VI-1 | CAPN2 | 2.39 |
| 165 | 3 | 4 | 5 | 6 | | VI-1 | CAPRIN1 | 2.13 |
| 166 | 3 | 4 | 5 | 6 | | VI-1 | CARD6 | 2.08 |
| 167 | 3 | 4 | 5 | 6 | | VI-1 | CBR1 | 2.03 |
| 168 | 3 | 4 | 5 | 6 | | VI-1 | CCAR1 | 2.48 |
| 169 | 3 | 4 | 5 | 6 | | VI-1 | CCDC134 | 2.05 |
| 170 | 3 | 4 | 5 | 6 | | VI-1 | CCDC149 | 2.60 |
| 171 | 3 | 4 | 5 | 6 | | VI-1 | CCDC22 | 2.77 |
| 172 | 3 | 4 | 5 | 6 | | VI-1 | CCDC43 | 2.08 |
| 173 | 3 | 4 | 5 | 6 | | VI-1 | CCDC47 | 2.03 |
| 174 | 3 | 4 | 5 | 6 | | VI-1 | CCDC6 | 2.43 |
| 175 | 3 | 4 | 5 | 6 | | VI-1 | CCR1 | 2.19 |
| 176 | 3 | 4 | 5 | 6 | | VI-1 | CCR8 | 2.07 |
| 177 | 3 | 4 | 5 | 6 | | VI-1 | CCRL2 | 3.05 |
| 178 | 3 | 4 | 5 | 6 | | VI-1 | CCT3 | 2.08 |
| 179 | 3 | 4 | 5 | 6 | | VI-1 | CCT6A | 2.13 |
| 180 | 3 | 4 | 5 | 6 | | VI-1 | CCT8 | 2.61 |
| 181 | 3 | 4 | 5 | 6 | | VI-1 | CD14 | 2.98 |
| 182 | 3 | 4 | 5 | 6 | | VI-1 | CD300C | 3.64 |
| 183 | 3 | 4 | 5 | 6 | | VI-1 | CD44 | 2.25 |
| 184 | 3 | 4 | 5 | 6 | | VI-1 | CD84 | 2.29 |
| 185 | 3 | 4 | 5 | 6 | | VI-1 | CD86 | 2.75 |
| 186 | 3 | 4 | 5 | 6 | | VI-1 | CD93 | 2.53 |
| 187 | 3 | 4 | 5 | 6 | | VI-1 | CDC42EP4 | 2.13 |
| 188 | 3 | 4 | 5 | 6 | | VI-1 | CDV3 | 2.02 |
| 189 | 3 | 4 | 5 | 6 | | VI-1 | CEACAM6 | 2.67 |
| 190 | 3 | 4 | 5 | 6 | | VI-1 | CENPB | 2.01 |

Fig. 41 - 2

| # | | | | | | Gene | Value | # | | | | | | Gene | Value |
|---|---|---|---|---|---|---|---|---|---|---|---|---|---|---|---|
| 191 | 3 | 4 | 5 | 6 | VI-1 | CENPW | 2.68 | 287 | 3 | 4 | 5 | 6 | VI-1 | EIF5B | 2.34 |
| 192 | 3 | 4 | 5 | 6 | VI-1 | CERS6 | 2.75 | 288 | 3 | 4 | 5 | 6 | VI-1 | EML2 | 2.17 |
| 193 | 3 | 4 | 5 | 6 | VI-1 | CFP | 2.07 | 289 | 3 | 4 | 5 | 6 | VI-1 | EMP3 | 2.18 |
| 194 | 3 | 4 | 5 | 6 | VI-1 | CHP | 2.41 | 290 | 3 | 4 | 5 | 6 | VI-1 | ENO1 | 3.09 |
| 195 | 3 | 4 | 5 | 6 | VI-1 | CLCN5 | 2.48 | 291 | 3 | 4 | 5 | 6 | VI-1 | ENTPD7 | 2.03 |
| 196 | 3 | 4 | 5 | 6 | VI-1 | CLCN7 | 2.25 | 292 | 3 | 4 | 5 | 6 | VI-1 | EPHB2 | 2.08 |
| 197 | 3 | 4 | 5 | 6 | VI-1 | CLIC4 | 2.24 | 293 | 3 | 4 | 5 | 6 | VI-1 | ERICH1 | 2.43 |
| 198 | 3 | 4 | 5 | 6 | VI-1 | CLIP4 | 2.63 | 294 | 3 | 4 | 5 | 6 | VI-1 | ERLIN2 | 2.20 |
| 199 | 3 | 4 | 5 | 6 | VI-1 | CLTA | 2.00 | 295 | 3 | 4 | 5 | 6 | VI-1 | ESF1 | 2.15 |
| 200 | 3 | 4 | 5 | 6 | VI-1 | CLTC | 2.71 | 296 | 3 | 4 | 5 | 6 | VI-1 | ETHE1 | 3.05 |
| 201 | 3 | 4 | 5 | 6 | VI-1 | CMAS | 2.02 | 297 | 3 | 4 | 5 | 6 | VI-1 | EXOSC9 | 2.29 |
| 202 | 3 | 4 | 5 | 6 | VI-1 | CMTM3 | 2.11 | 298 | 3 | 4 | 5 | 6 | VI-1 | EXT2 | 2.35 |
| 203 | 3 | 4 | 5 | 6 | VI-1 | CMTM4 | 2.32 | 299 | 3 | 4 | 5 | 6 | VI-1 | F5 | 2.37 |
| 204 | 3 | 4 | 5 | 6 | VI-1 | CNDP2 | 2.34 | 300 | 3 | 4 | 5 | 6 | VI-1 | FAF1 | 2.06 |
| 205 | 3 | 4 | 5 | 6 | VI-1 | CNIH | 2.20 | 301 | 3 | 4 | 5 | 6 | VI-1 | FAHD1 | 2.08 |
| 206 | 3 | 4 | 5 | 6 | VI-1 | CNP | 2.18 | 302 | 3 | 4 | 5 | 6 | VI-1 | FAM102B | 2.09 |
| 207 | 3 | 4 | 5 | 6 | VI-1 | COG7 | 2.03 | 303 | 3 | 4 | 5 | 6 | VI-1 | FAM105A | 2.22 |
| 208 | 3 | 4 | 5 | 6 | VI-1 | COL8A2 | 3.20 | 304 | 3 | 4 | 5 | 6 | VI-1 | FAM108C1 | 3.44 |
| 209 | 3 | 4 | 5 | 6 | VI-1 | COMMD10 | 2.69 | 305 | 3 | 4 | 5 | 6 | VI-1 | FAM114A1 | 2.23 |
| 210 | 3 | 4 | 5 | 6 | VI-1 | COMMD3 | 2.16 | 306 | 3 | 4 | 5 | 6 | VI-1 | FAM120A | 2.01 |
| 211 | 3 | 4 | 5 | 6 | VI-1 | COMMD9 | 2.01 | 307 | 3 | 4 | 5 | 6 | VI-1 | FAM124B | 2.15 |
| 212 | 3 | 4 | 5 | 6 | VI-1 | COMTD1 | 2.04 | 308 | 3 | 4 | 5 | 6 | VI-1 | FAM126A | 2.36 |
| 213 | 3 | 4 | 5 | 6 | VI-1 | COPA | 2.52 | 309 | 3 | 4 | 5 | 6 | VI-1 | FAM127A | 2.00 |
| 214 | 3 | 4 | 5 | 6 | VI-1 | CORO1B | 2.20 | 310 | 3 | 4 | 5 | 6 | VI-1 | FAM13A | 2.33 |
| 215 | 3 | 4 | 5 | 6 | VI-1 | CORO1C | 2.05 | 311 | 3 | 4 | 5 | 6 | VI-1 | FAM151B | 2.72 |
| 216 | 3 | 4 | 5 | 6 | VI-1 | CORO2A | 2.14 | 312 | 3 | 4 | 5 | 6 | VI-1 | FAM173A | 2.27 |
| 217 | 3 | 4 | 5 | 6 | VI-1 | COX7A2L | 2.04 | 313 | 3 | 4 | 5 | 6 | VI-1 | FAM173B | 2.32 |
| 218 | 3 | 4 | 5 | 6 | VI-1 | CPSF3 | 2.13 | 314 | 3 | 4 | 5 | 6 | VI-1 | FAM20A | 4.93 |
| 219 | 3 | 4 | 5 | 6 | VI-1 | CR1 | 2.03 | 315 | 3 | 4 | 5 | 6 | VI-1 | FAM46A | 2.45 |
| 220 | 3 | 4 | 5 | 6 | VI-1 | CREG1 | 2.54 | 316 | 3 | 4 | 5 | 6 | VI-1 | FAR2 | 2.05 |
| 221 | 3 | 4 | 5 | 6 | VI-1 | CSE1L | 2.18 | 317 | 3 | 4 | 5 | 6 | VI-1 | FBP1 | 3.74 |
| 222 | 3 | 4 | 5 | 6 | VI-1 | CSF1R | 3.04 | 318 | 3 | 4 | 5 | 6 | VI-1 | FBXL18 | 2.01 |
| 223 | 3 | 4 | 5 | 6 | VI-1 | CSRP1 | 2.09 | 319 | 3 | 4 | 5 | 6 | VI-1 | FBXO6 | 2.04 |
| 224 | 3 | 4 | 5 | 6 | VI-1 | CSTA | 2.39 | 320 | 3 | 4 | 5 | 6 | VI-1 | FCER1G | 2.17 |
| 225 | 3 | 4 | 5 | 6 | VI-1 | CTIF | 2.30 | 321 | 3 | 4 | 5 | 6 | VI-1 | FCGR1A | 3.74 |
| 226 | 3 | 4 | 5 | 6 | VI-1 | CTNNA1 | 3.04 | 322 | 3 | 4 | 5 | 6 | VI-1 | FCGR1B | 2.30 |
| 227 | 3 | 4 | 5 | 6 | VI-1 | CTR9 | 2.11 | 323 | 3 | 4 | 5 | 6 | VI-1 | FCGR1C | 3.30 |
| 228 | 3 | 4 | 5 | 6 | VI-1 | CTSA | 2.35 | 324 | 3 | 4 | 5 | 6 | VI-1 | FCGR2C | 2.24 |
| 229 | 3 | 4 | 5 | 6 | VI-1 | CTSB | 3.23 | 325 | 3 | 4 | 5 | 6 | VI-1 | FCN1 | 3.05 |
| 230 | 3 | 4 | 5 | 6 | VI-1 | CTSD | 2.89 | 326 | 3 | 4 | 5 | 6 | VI-1 | FEZ2 | 2.01 |
| 231 | 3 | 4 | 5 | 6 | VI-1 | CTSL1 | 4.66 | 327 | 3 | 4 | 5 | 6 | VI-1 | FIG4 | 2.35 |
| 232 | 3 | 4 | 5 | 6 | VI-1 | CTSS | 2.06 | 328 | 3 | 4 | 5 | 6 | VI-1 | FKBP15 | 2.45 |
| 233 | 3 | 4 | 5 | 6 | VI-1 | CTSZ | 2.69 | 329 | 3 | 4 | 5 | 6 | VI-1 | FLT3 | 2.40 |
| 234 | 3 | 4 | 5 | 6 | VI-1 | CTTN8P2NL | 2.83 | 330 | 3 | 4 | 5 | 6 | VI-1 | FNIP2 | 2.20 |
| 235 | 3 | 4 | 5 | 6 | VI-1 | CUL1 | 2.08 | 331 | 3 | 4 | 5 | 6 | VI-1 | FPGT | 2.35 |
| 236 | 3 | 4 | 5 | 6 | VI-1 | CUL4A | 2.06 | 332 | 3 | 4 | 5 | 6 | VI-1 | FSTL3 | 2.37 |
| 237 | 3 | 4 | 5 | 6 | VI-1 | CUX1 | 2.01 | 333 | 3 | 4 | 5 | 6 | VI-1 | FUBP3 | 2.23 |
| 238 | 3 | 4 | 5 | 6 | VI-1 | CYC1 | 2.20 | 334 | 3 | 4 | 5 | 6 | VI-1 | FUT4 | 2.56 |
| 239 | 3 | 4 | 5 | 6 | VI-1 | CYP51A1 | 2.52 | 335 | 3 | 4 | 5 | 6 | VI-1 | GAA | 2.69 |
| 240 | 3 | 4 | 5 | 6 | VI-1 | DACT1 | 3.19 | 336 | 3 | 4 | 5 | 6 | VI-1 | GALC | 2.25 |
| 241 | 3 | 4 | 5 | 6 | VI-1 | D8NDD2 | 2.92 | 337 | 3 | 4 | 5 | 6 | VI-1 | GALK1 | 2.12 |
| 242 | 3 | 4 | 5 | 6 | VI-1 | DCAF7 | 2.05 | 338 | 3 | 4 | 5 | 6 | VI-1 | GALNT10 | 2.03 |
| 243 | 3 | 4 | 5 | 6 | VI-1 | DCP5 | 2.07 | 339 | 3 | 4 | 5 | 6 | VI-1 | GALNT2 | 2.08 |
| 244 | 3 | 4 | 5 | 6 | VI-1 | DDB1 | 2.14 | 340 | 3 | 4 | 5 | 6 | VI-1 | GALNT4 | 2.39 |
| 245 | 3 | 4 | 5 | 6 | VI-1 | DDO | 2.56 | 341 | 3 | 4 | 5 | 6 | VI-1 | GALNT7 | 2.16 |
| 246 | 3 | 4 | 5 | 6 | VI-1 | DDOST | 2.32 | 342 | 3 | 4 | 5 | 6 | VI-1 | GAPDH | 2.01 |
| 247 | 3 | 4 | 5 | 6 | VI-1 | DDX21 | 2.11 | 343 | 3 | 4 | 5 | 6 | VI-1 | GBA | 2.32 |
| 248 | 3 | 4 | 5 | 6 | VI-1 | DDX60 | 2.09 | 344 | 3 | 4 | 5 | 6 | VI-1 | GBAP1 | 2.21 |
| 249 | 3 | 4 | 5 | 6 | VI-1 | DEGS1 | 2.04 | 345 | 3 | 4 | 5 | 6 | VI-1 | GBE1 | 2.13 |
| 250 | 3 | 4 | 5 | 6 | VI-1 | DENND1A | 2.07 | 346 | 3 | 4 | 5 | 6 | VI-1 | GCDH | 2.01 |
| 251 | 3 | 4 | 5 | 6 | VI-1 | DHFR | 2.48 | 347 | 3 | 4 | 5 | 6 | VI-1 | GCH1 | 2.14 |
| 252 | 3 | 4 | 5 | 6 | VI-1 | DHFRL1 | 2.02 | 348 | 3 | 4 | 5 | 6 | VI-1 | GCNT1 | 2.14 |
| 253 | 3 | 4 | 5 | 6 | VI-1 | DHRS4L2 | 2.16 | 349 | 3 | 4 | 5 | 6 | VI-1 | GFM1 | 2.62 |
| 254 | 3 | 4 | 5 | 6 | VI-1 | DHX29 | 2.02 | 350 | 3 | 4 | 5 | 6 | VI-1 | GIMAP1 | 2.02 |
| 255 | 3 | 4 | 5 | 6 | VI-1 | DHX32 | 2.44 | 351 | 3 | 4 | 5 | 6 | VI-1 | GIMAP8 | 2.88 |
| 256 | 3 | 4 | 5 | 6 | VI-1 | DHX36 | 2.12 | 352 | 3 | 4 | 5 | 6 | VI-1 | GLRX2 | 2.50 |
| 257 | 3 | 4 | 5 | 6 | VI-1 | DIAPH2 | 2.49 | 353 | 3 | 4 | 5 | 6 | VI-1 | GLT25D1 | 3.09 |
| 258 | 3 | 4 | 5 | 6 | VI-1 | DLD | 2.22 | 354 | 3 | 4 | 5 | 6 | VI-1 | GLUD1 | 2.24 |
| 259 | 3 | 4 | 5 | 6 | VI-1 | DLG4 | 2.73 | 355 | 3 | 4 | 5 | 6 | VI-1 | GLUD2 | 2.22 |
| 260 | 3 | 4 | 5 | 6 | VI-1 | DMXL2 | 2.16 | 356 | 3 | 4 | 5 | 6 | VI-1 | GMFB | 2.02 |
| 261 | 3 | 4 | 5 | 6 | VI-1 | DNAJB11 | 2.05 | 357 | 3 | 4 | 5 | 6 | VI-1 | GNA11 | 2.13 |
| 262 | 3 | 4 | 5 | 6 | VI-1 | DNAJB4 | 2.00 | 358 | 3 | 4 | 5 | 6 | VI-1 | GNA1S | 2.77 |
| 263 | 3 | 4 | 5 | 6 | VI-1 | DNAJC10 | 2.29 | 359 | 3 | 4 | 5 | 6 | VI-1 | GNPDA1 | 3.15 |
| 264 | 3 | 4 | 5 | 6 | VI-1 | DNAJC11 | 2.14 | 360 | 3 | 4 | 5 | 6 | VI-1 | GNS | 3.74 |
| 265 | 3 | 4 | 5 | 6 | VI-1 | DNAJC13 | 2.17 | 361 | 3 | 4 | 5 | 6 | VI-1 | GPR137B | 3.08 |
| 266 | 3 | 4 | 5 | 6 | VI-1 | DNAJC2 | 2.79 | 362 | 3 | 4 | 5 | 6 | VI-1 | GPR141 | 2.55 |
| 267 | 3 | 4 | 5 | 6 | VI-1 | DNAJC7 | 2.32 | 363 | 3 | 4 | 5 | 6 | VI-1 | GPR171 | 2.24 |
| 268 | 3 | 4 | 5 | 6 | VI-1 | DNM1L | 2.02 | 364 | 3 | 4 | 5 | 6 | VI-1 | GRHPR | 2.31 |
| 269 | 3 | 4 | 5 | 6 | VI-1 | DOHH | 2.39 | 365 | 3 | 4 | 5 | 6 | VI-1 | GRSF1 | 2.36 |
| 270 | 3 | 4 | 5 | 6 | VI-1 | DPAGT1 | 2.13 | 366 | 3 | 4 | 5 | 6 | VI-1 | GSTO1 | 2.00 |
| 271 | 3 | 4 | 5 | 6 | VI-1 | DSE | 2.33 | 367 | 3 | 4 | 5 | 6 | VI-1 | GTF3C4 | 2.22 |
| 272 | 3 | 4 | 5 | 6 | VI-1 | DUSP10 | 2.28 | 368 | 3 | 4 | 5 | 6 | VI-1 | GTF3C6 | 2.33 |
| 273 | 3 | 4 | 5 | 6 | VI-1 | DUSP18 | 2.31 | 369 | 3 | 4 | 5 | 6 | VI-1 | GUSB | 2.42 |
| 274 | 3 | 4 | 5 | 6 | VI-1 | DUSP3 | 3.06 | 370 | 3 | 4 | 5 | 6 | VI-1 | GYG1 | 2.64 |
| 275 | 3 | 4 | 5 | 6 | VI-1 | DUSP6 | 2.28 | 371 | 3 | 4 | 5 | 6 | VI-1 | H2AFY | 2.29 |
| 276 | 3 | 4 | 5 | 6 | VI-1 | DYNC1I2 | 2.51 | 372 | 3 | 4 | 5 | 6 | VI-1 | H2AFZ | 2.26 |
| 277 | 3 | 4 | 5 | 6 | VI-1 | ECHS1 | 2.32 | 373 | 3 | 4 | 5 | 6 | VI-1 | HADHB | 3.01 |
| 278 | 3 | 4 | 5 | 6 | VI-1 | EDARADD | 3.16 | 374 | 3 | 4 | 5 | 6 | VI-1 | HARBI1 | 2.72 |
| 279 | 3 | 4 | 5 | 6 | VI-1 | EEF1E1-MUTED | 3.10 | 375 | 3 | 4 | 5 | 6 | VI-1 | HAUS7 | 2.03 |
| 280 | 3 | 4 | 5 | 6 | VI-1 | EFNB1 | 2.32 | 376 | 3 | 4 | 5 | 6 | VI-1 | HCFC1 | 2.11 |
| 281 | 3 | 4 | 5 | 6 | VI-1 | EFTUD2 | 2.16 | 377 | 3 | 4 | 5 | 6 | VI-1 | HEATR2 | 2.11 |
| 282 | 3 | 4 | 5 | 6 | VI-1 | EHD4 | 2.54 | 378 | 3 | 4 | 5 | 6 | VI-1 | HEBP1 | 2.36 |
| 283 | 3 | 4 | 5 | 6 | VI-1 | EIF2B2 | 2.09 | 379 | 3 | 4 | 5 | 6 | VI-1 | HEXA | 2.17 |
| 284 | 3 | 4 | 5 | 6 | VI-1 | EIF2B4 | 2.41 | 380 | 3 | 4 | 5 | 6 | VI-1 | HGF | 3.14 |
| 285 | 3 | 4 | 5 | 6 | VI-1 | EIF3A | 2.12 | 381 | 3 | 4 | 5 | 6 | VI-1 | HHEX | 2.12 |
| 286 | 3 | 4 | 5 | 6 | VI-1 | EIF4G1 | 2.31 | 382 | 3 | 4 | 5 | 6 | VI-1 | HIATL1 | 2.50 |

Fig. 41 - 3

| | | | | | | | | | | | | | | | | |
|---|---|---|---|---|---|---|---|---|---|---|---|---|---|---|---|---|
| 383 | 3 | 4 | 5 | 6 | | VI-1 | HIST1H1D | 3.90 | 479 | 3 | 4 | 5 | 6 | | VI-1 | LONRF3 | 2.90 |
| 384 | 3 | 4 | 5 | 6 | | VI-1 | HIST1H2BB | 2.80 | 480 | 3 | 4 | 5 | 6 | | VI-1 | LOXL3 | 3.39 |
| 385 | 3 | 4 | 5 | 6 | | VI-1 | HIST1H2BG | 2.22 | 481 | 3 | 4 | 5 | 6 | | VI-1 | LPXN | 2.40 |
| 386 | 3 | 4 | 5 | 6 | | VI-1 | HIST1H3F | 2.26 | 482 | 3 | 4 | 5 | 6 | | VI-1 | LRRC33 | 2.86 |
| 387 | 3 | 4 | 5 | 6 | | VI-1 | HIST1H4A | 2.93 | 483 | 3 | 4 | 5 | 6 | | VI-1 | LRRC41 | 2.02 |
| 388 | 3 | 4 | 5 | 6 | | VI-1 | HIST1H4F | 4.65 | 484 | 3 | 4 | 5 | 6 | | VI-1 | LRRC58 | 2.10 |
| 389 | 3 | 4 | 5 | 6 | | VI-1 | HIST1H4L | 3.39 | 485 | 3 | 4 | 5 | 6 | | VI-1 | LRRC59 | 2.44 |
| 390 | 3 | 4 | 5 | 6 | | VI-1 | HK1 | 2.22 | 486 | 3 | 4 | 5 | 6 | | VI-1 | LRRC8D | 2.06 |
| 391 | 3 | 4 | 5 | 6 | | VI-1 | HK2 | 2.21 | 487 | 3 | 4 | 5 | 6 | | VI-1 | LTBR | 2.44 |
| 392 | 3 | 4 | 5 | 6 | | VI-1 | HK3 | 3.23 | 488 | 3 | 4 | 5 | 6 | | VI-1 | LY6E | 2.11 |
| 393 | 3 | 4 | 5 | 6 | | VI-1 | HMOX1 | 4.27 | 489 | 3 | 4 | 5 | 6 | | VI-1 | LYPD2 | 2.21 |
| 394 | 3 | 4 | 5 | 6 | | VI-1 | HNRNPAB | 2.23 | 490 | 3 | 4 | 5 | 6 | | VI-1 | LZIC | 2.39 |
| 395 | 3 | 4 | 5 | 6 | | VI-1 | HNRNPKP3 | 2.01 | 491 | 3 | 4 | 5 | 6 | | VI-1 | MAFG | 2.43 |
| 396 | 3 | 4 | 5 | 6 | | VI-1 | HNRNPM | 2.71 | 492 | 3 | 4 | 5 | 6 | | VI-1 | MAN1A2 | 2.53 |
| 397 | 3 | 4 | 5 | 6 | | VI-1 | HOMER3 | 4.05 | 493 | 3 | 4 | 5 | 6 | | VI-1 | MANBA | 2.25 |
| 398 | 3 | 4 | 5 | 6 | | VI-1 | HOOK3 | 2.62 | 494 | 3 | 4 | 5 | 6 | | VI-1 | MAP1A | 2.02 |
| 399 | 3 | 4 | 5 | 6 | | VI-1 | HPRT1 | 2.01 | 495 | 3 | 4 | 5 | 6 | | VI-1 | MAP2K1 | 2.41 |
| 400 | 3 | 4 | 5 | 6 | | VI-1 | HPS5 | 2.27 | 496 | 3 | 4 | 5 | 6 | | VI-1 | MAP2K6 | 2.24 |
| 401 | 3 | 4 | 5 | 6 | | VI-1 | HSP90AA1 | 2.81 | 497 | 3 | 4 | 5 | 6 | | VI-1 | MAP3K6 | 2.25 |
| 402 | 3 | 4 | 5 | 6 | | VI-1 | HSP90AA4P | 2.92 | 498 | 3 | 4 | 5 | 6 | | VI-1 | MAP4 | 2.28 |
| 403 | 3 | 4 | 5 | 6 | | VI-1 | HSP90AA6P | 4.83 | 499 | 3 | 4 | 5 | 6 | | VI-1 | MAPRE1 | 2.25 |
| 404 | 3 | 4 | 5 | 6 | | VI-1 | HSP90AB1 | 2.14 | 500 | 3 | 4 | 5 | 6 | | VI-1 | MARCKS | 2.04 |
| 405 | 3 | 4 | 5 | 6 | | VI-1 | HSP90AB3P | 2.12 | 501 | 3 | 4 | 5 | 6 | | VI-1 | MBTPS2 | 2.25 |
| 406 | 3 | 4 | 5 | 6 | | VI-1 | HSP90B1 | 2.27 | 502 | 3 | 4 | 5 | 6 | | VI-1 | MCM8P | 2.00 |
| 407 | 3 | 4 | 5 | 6 | | VI-1 | HSP90B3P | 2.83 | 503 | 3 | 4 | 5 | 6 | | VI-1 | MCTP1 | 2.23 |
| 408 | 3 | 4 | 5 | 6 | | VI-1 | HSPA5 | 2.02 | 504 | 3 | 4 | 5 | 6 | | VI-1 | MERTK | 2.95 |
| 409 | 3 | 4 | 5 | 6 | | VI-1 | HSPA9 | 2.11 | 505 | 3 | 4 | 5 | 6 | | VI-1 | METAP2 | 2.14 |
| 410 | 3 | 4 | 5 | 6 | | VI-1 | HSPD1 | 2.05 | 506 | 3 | 4 | 5 | 6 | | VI-1 | METRN | 2.42 |
| 411 | 3 | 4 | 5 | 6 | | VI-1 | HSPH1 | 2.66 | 507 | 3 | 4 | 5 | 6 | | VI-1 | METTL13 | 2.18 |
| 412 | 3 | 4 | 5 | 6 | | VI-1 | IARS2 | 2.07 | 508 | 3 | 4 | 5 | 6 | | VI-1 | METTL21B | 2.29 |
| 413 | 3 | 4 | 5 | 6 | | VI-1 | IBTK | 2.12 | 509 | 3 | 4 | 5 | 6 | | VI-1 | METTL9 | 2.07 |
| 414 | 3 | 4 | 5 | 6 | | VI-1 | IDE | 2.48 | 510 | 3 | 4 | 5 | 6 | | VI-1 | MFSD1 | 2.63 |
| 415 | 3 | 4 | 5 | 6 | | VI-1 | IDH1 | 3.26 | 511 | 3 | 4 | 5 | 6 | | VI-1 | MGST2 | 3.28 |
| 416 | 3 | 4 | 5 | 6 | | VI-1 | IDH2 | 2.08 | 512 | 3 | 4 | 5 | 6 | | VI-1 | MIER2 | 2.52 |
| 417 | 3 | 4 | 5 | 6 | | VI-1 | IER5L | 2.73 | 513 | 3 | 4 | 5 | 6 | | VI-1 | MITF | 3.34 |
| 418 | 3 | 4 | 5 | 6 | | VI-1 | IFI27L2 | 2.08 | 514 | 3 | 4 | 5 | 6 | | VI-1 | MKI67 | 2.21 |
| 419 | 3 | 4 | 5 | 6 | | VI-1 | IFI30 | 2.54 | 515 | 3 | 4 | 5 | 6 | | VI-1 | MLEC | 2.00 |
| 420 | 3 | 4 | 5 | 6 | | VI-1 | IFI44 | 2.97 | 516 | 3 | 4 | 5 | 6 | | VI-1 | MMAA | 2.27 |
| 421 | 3 | 4 | 5 | 6 | | VI-1 | IL15 | 2.14 | 517 | 3 | 4 | 5 | 6 | | VI-1 | MOB1B | 2.25 |
| 422 | 3 | 4 | 5 | 6 | | VI-1 | IL27RA | 2.28 | 518 | 3 | 4 | 5 | 6 | | VI-1 | MO84 | 2.44 |
| 423 | 3 | 4 | 5 | 6 | | VI-1 | IPO7 | 2.04 | 519 | 3 | 4 | 5 | 6 | | VI-1 | MORF4L1 | 2.02 |
| 424 | 3 | 4 | 5 | 6 | | VI-1 | IRF5 | 2.41 | 520 | 3 | 4 | 5 | 6 | | VI-1 | MPHOSPH6 | 2.06 |
| 425 | 3 | 4 | 5 | 6 | | VI-1 | IRGQ | 2.02 | 521 | 3 | 4 | 5 | 6 | | VI-1 | MPO | 4.37 |
| 426 | 3 | 4 | 5 | 6 | | VI-1 | ITFG1 | 2.41 | 522 | 3 | 4 | 5 | 6 | | VI-1 | MR1 | 2.04 |
| 427 | 3 | 4 | 5 | 6 | | VI-1 | ITGAM | 2.81 | 523 | 3 | 4 | 5 | 6 | | VI-1 | MRPL13 | 2.74 |
| 428 | 3 | 4 | 5 | 6 | | VI-1 | ITGAV | 2.31 | 524 | 3 | 4 | 5 | 6 | | VI-1 | MRPL47 | 2.18 |
| 429 | 3 | 4 | 5 | 6 | | VI-1 | ITPA | 2.44 | 525 | 3 | 4 | 5 | 6 | | VI-1 | MT1X | 2.28 |
| 430 | 3 | 4 | 5 | 6 | | VI-1 | ITPR2 | 2.10 | 526 | 3 | 4 | 5 | 6 | | VI-1 | MTAP | 2.02 |
| 431 | 3 | 4 | 5 | 6 | | VI-1 | ITSN1 | 2.97 | 527 | 3 | 4 | 5 | 6 | | VI-1 | MTDH | 2.41 |
| 432 | 3 | 4 | 5 | 6 | | VI-1 | JOSD2 | 2.09 | 528 | 3 | 4 | 5 | 6 | | VI-1 | MTF1 | 2.11 |
| 433 | 3 | 4 | 5 | 6 | | VI-1 | KCNK6 | 2.28 | 529 | 3 | 4 | 5 | 6 | | VI-1 | MTHFD2 | 2.82 |
| 434 | 3 | 4 | 5 | 6 | | VI-1 | KCTD15 | 2.32 | 530 | 3 | 4 | 5 | 6 | | VI-1 | MTHFR | 2.35 |
| 435 | 3 | 4 | 5 | 6 | | VI-1 | KCTD17 | 2.09 | 531 | 3 | 4 | 5 | 6 | | VI-1 | MTX2 | 2.12 |
| 436 | 3 | 4 | 5 | 6 | | VI-1 | KDELR1 | 2.10 | 532 | 3 | 4 | 5 | 6 | | VI-1 | MYO1G | 2.06 |
| 437 | 3 | 4 | 5 | 6 | | VI-1 | KDELR2 | 2.07 | 533 | 3 | 4 | 5 | 6 | | VI-1 | MYO7A | 2.18 |
| 438 | 3 | 4 | 5 | 6 | | VI-1 | KDM1B | 2.47 | 534 | 3 | 4 | 5 | 6 | | VI-1 | MYOF | 4.90 |
| 439 | 3 | 4 | 5 | 6 | | VI-1 | KDM5D | 2.81 | 535 | 3 | 4 | 5 | 6 | | VI-1 | NACC2 | 2.10 |
| 440 | 3 | 4 | 5 | 6 | | VI-1 | KIAA0196 | 2.22 | 536 | 3 | 4 | 5 | 6 | | VI-1 | NAGPA | 2.41 |
| 441 | 3 | 4 | 5 | 6 | | VI-1 | KIAA1522 | 2.94 | 537 | 3 | 4 | 5 | 6 | | VI-1 | NAIP | 2.72 |
| 442 | 3 | 4 | 5 | 6 | | VI-1 | KLF10 | 2.24 | 538 | 3 | 4 | 5 | 6 | | VI-1 | NARS | 2.39 |
| 443 | 3 | 4 | 5 | 6 | | VI-1 | KLHL9 | 2.24 | 539 | 3 | 4 | 5 | 6 | | VI-1 | NBAS | 2.28 |
| 444 | 3 | 4 | 5 | 6 | | VI-1 | KPNA2 | 2.13 | 540 | 3 | 4 | 5 | 6 | | VI-1 | NCBP1 | 2.50 |
| 445 | 3 | 4 | 5 | 6 | | VI-1 | KPNA3 | 2.16 | 541 | 3 | 4 | 5 | 6 | | VI-1 | NCDN | 2.01 |
| 446 | 3 | 4 | 5 | 6 | | VI-1 | KTN1 | 2.16 | 542 | 3 | 4 | 5 | 6 | | VI-1 | NCKAP1L | 2.52 |
| 447 | 3 | 4 | 5 | 6 | | VI-1 | KYNU | 4.93 | 543 | 3 | 4 | 5 | 6 | | VI-1 | NCKAP5L | 2.18 |
| 448 | 3 | 4 | 5 | 6 | | VI-1 | LACC1 | 3.02 | 544 | 3 | 4 | 5 | 6 | | VI-1 | NCOR1 | 2.08 |
| 449 | 3 | 4 | 5 | 6 | | VI-1 | LACTB | 2.37 | 545 | 3 | 4 | 5 | 6 | | VI-1 | NCOR2 | 2.08 |
| 450 | 3 | 4 | 5 | 6 | | VI-1 | LAMP1 | 2.44 | 546 | 3 | 4 | 5 | 6 | | VI-1 | NCSTN | 2.16 |
| 451 | 3 | 4 | 5 | 6 | | VI-1 | LAPTM4A | 2.49 | 547 | 3 | 4 | 5 | 6 | | VI-1 | NDUFAF1 | 2.08 |
| 452 | 3 | 4 | 5 | 6 | | VI-1 | LAPTM4B | 2.04 | 548 | 3 | 4 | 5 | 6 | | VI-1 | NDUFB1 | 2.03 |
| 453 | 3 | 4 | 5 | 6 | | VI-1 | LARP4 | 2.08 | 549 | 3 | 4 | 5 | 6 | | VI-1 | NDUFB2 | 2.08 |
| 454 | 3 | 4 | 5 | 6 | | VI-1 | LARS | 2.01 | 550 | 3 | 4 | 5 | 6 | | VI-1 | NDUFC1 | 2.01 |
| 455 | 3 | 4 | 5 | 6 | | VI-1 | LDHA | 2.60 | 551 | 3 | 4 | 5 | 6 | | VI-1 | NDUFS1 | 2.26 |
| 456 | 3 | 4 | 5 | 6 | | VI-1 | LDHD | 2.13 | 552 | 3 | 4 | 5 | 6 | | VI-1 | NEK6 | 2.09 |
| 457 | 3 | 4 | 5 | 6 | | VI-1 | LETM1 | 2.01 | 553 | 3 | 4 | 5 | 6 | | VI-1 | NEMF | 2.03 |
| 458 | 3 | 4 | 5 | 6 | | VI-1 | LETMD1 | 2.16 | 554 | 3 | 4 | 5 | 6 | | VI-1 | NHLRC3 | 2.13 |
| 459 | 3 | 4 | 5 | 6 | | VI-1 | LGALS8 | 2.04 | 555 | 3 | 4 | 5 | 6 | | VI-1 | NIPAL2 | 2.03 |
| 460 | 3 | 4 | 5 | 6 | | VI-1 | LGALS9 | 2.48 | 556 | 3 | 4 | 5 | 6 | | VI-1 | NLRC4 | 3.78 |
| 461 | 3 | 4 | 5 | 6 | | VI-1 | LILRB1 | 3.69 | 557 | 3 | 4 | 5 | 6 | | VI-1 | NLRP3 | 2.67 |
| 462 | 3 | 4 | 5 | 6 | | VI-1 | LINC00189 | 2.49 | 558 | 3 | 4 | 5 | 6 | | VI-1 | NNT | 2.67 |
| 463 | 3 | 4 | 5 | 6 | | VI-1 | LIPA | 3.18 | 559 | 3 | 4 | 5 | 6 | | VI-1 | NOL10 | 2.22 |
| 464 | 3 | 4 | 5 | 6 | | VI-1 | LMNB1 | 2.29 | 560 | 3 | 4 | 5 | 6 | | VI-1 | NOM1 | 2.09 |
| 465 | 3 | 4 | 5 | 6 | | VI-1 | LMNB2 | 2.38 | 561 | 3 | 4 | 5 | 6 | | VI-1 | NOMO1 | 2.09 |
| 466 | 3 | 4 | 5 | 6 | | VI-1 | LMO2 | 2.40 | 562 | 3 | 4 | 5 | 6 | | VI-1 | NOMO2 | 2.03 |
| 467 | 3 | 4 | 5 | 6 | | VI-1 | LOC100130331 | 2.05 | 563 | 3 | 4 | 5 | 6 | | VI-1 | NOMO3 | 2.18 |
| 468 | 3 | 4 | 5 | 6 | | VI-1 | LOC100130950 | 2.13 | 564 | 3 | 4 | 5 | 6 | | VI-1 | NPC2 | 2.56 |
| 469 | 3 | 4 | 5 | 6 | | VI-1 | LOC100505702 | 2.65 | 565 | 3 | 4 | 5 | 6 | | VI-1 | NSF | 2.47 |
| 470 | 3 | 4 | 5 | 6 | | VI-1 | LOC100506585 | 3.60 | 566 | 3 | 4 | 5 | 6 | | VI-1 | NSFP1 | 2.23 |
| 471 | 3 | 4 | 5 | 6 | | VI-1 | LOC344967 | 2.06 | 567 | 3 | 4 | 5 | 6 | | VI-1 | NTSR1 | 2.09 |
| 472 | 3 | 4 | 5 | 6 | | VI-1 | LOC387647 | 2.70 | 568 | 3 | 4 | 5 | 6 | | VI-1 | NUDT19 | 2.44 |
| 473 | 3 | 4 | 5 | 6 | | VI-1 | LOC400236 | 2.11 | 569 | 3 | 4 | 5 | 6 | | VI-1 | NUP210 | 2.02 |
| 474 | 3 | 4 | 5 | 6 | | VI-1 | LOC401397 | 2.06 | 570 | 3 | 4 | 5 | 6 | | VI-1 | NUP37 | 2.38 |
| 475 | 3 | 4 | 5 | 6 | | VI-1 | LOC644936 | 2.02 | 571 | 3 | 4 | 5 | 6 | | VI-1 | NUP62 | 2.01 |
| 476 | 3 | 4 | 5 | 6 | | VI-1 | LOC729020 | 2.13 | 572 | 3 | 4 | 5 | 6 | | VI-1 | NUSAP1 | 2.23 |
| 477 | 3 | 4 | 5 | 6 | | VI-1 | LOC80054 | 2.82 | 573 | 3 | 4 | 5 | 6 | | VI-1 | OAS1 | 3.78 |
| 478 | 3 | 4 | 5 | 6 | | VI-1 | LONP2 | 2.01 | 574 | 3 | 4 | 5 | 6 | | VI-1 | OAS2 | 2.92 |

Fig. 41 - 4

| | | | | | | | |
|---|---|---|---|---|---|---|---|
| 575 | 3 | 4 | 5 | 6 | VI-1 | OAS3 | 3.55 |
| 576 | 3 | 4 | 5 | 6 | VI-1 | OASL | 2.19 |
| 577 | 3 | 4 | 5 | 6 | VI-1 | OCRL | 2.41 |
| 578 | 3 | 4 | 5 | 6 | VI-1 | OLFML2B | 4.00 |
| 579 | 3 | 4 | 5 | 6 | VI-1 | OSCAR | 3.30 |
| 580 | 3 | 4 | 5 | 6 | VI-1 | OSTCP1 | 2.57 |
| 581 | 3 | 4 | 5 | 6 | VI-1 | OXA1L | 2.03 |
| 582 | 3 | 4 | 5 | 6 | VI-1 | P4HA1 | 2.30 |
| 583 | 3 | 4 | 5 | 6 | VI-1 | P4HB | 2.10 |
| 584 | 3 | 4 | 5 | 6 | VI-1 | PALLD | 2.50 |
| 585 | 3 | 4 | 5 | 6 | VI-1 | PANK2 | 2.27 |
| 586 | 3 | 4 | 5 | 6 | VI-1 | PANX1 | 2.20 |
| 587 | 3 | 4 | 5 | 6 | VI-1 | PAPSS2 | 2.83 |
| 588 | 3 | 4 | 5 | 6 | VI-1 | PARL | 2.05 |
| 589 | 3 | 4 | 5 | 6 | VI-1 | PBX3 | 2.25 |
| 590 | 3 | 4 | 5 | 6 | VI-1 | PC8D1 | 2.17 |
| 591 | 3 | 4 | 5 | 6 | VI-1 | PCK2 | 2.06 |
| 592 | 3 | 4 | 5 | 6 | VI-1 | PCMT1 | 2.34 |
| 593 | 3 | 4 | 5 | 6 | VI-1 | PCYOX1 | 2.12 |
| 594 | 3 | 4 | 5 | 6 | VI-1 | PCYOX1L | 2.33 |
| 595 | 3 | 4 | 5 | 6 | VI-1 | PDCL3 | 2.34 |
| 596 | 3 | 4 | 5 | 6 | VI-1 | PDHX | 2.21 |
| 597 | 3 | 4 | 5 | 6 | VI-1 | PDIA3 | 2.20 |
| 598 | 3 | 4 | 5 | 6 | VI-1 | PDIA4 | 2.15 |
| 599 | 3 | 4 | 5 | 6 | VI-1 | PDIA6 | 2.31 |
| 600 | 3 | 4 | 5 | 6 | VI-1 | PDLIM5 | 2.31 |
| 601 | 3 | 4 | 5 | 6 | VI-1 | PDSS1 | 2.43 |
| 602 | 3 | 4 | 5 | 6 | VI-1 | PDXK | 2.47 |
| 603 | 3 | 4 | 5 | 6 | VI-1 | PGGT1B | 2.24 |
| 604 | 3 | 4 | 5 | 6 | VI-1 | PHKB | 2.05 |
| 605 | 3 | 4 | 5 | 6 | VI-1 | PIEZO1 | 2.38 |
| 606 | 3 | 4 | 5 | 6 | VI-1 | PIGM | 3.22 |
| 607 | 3 | 4 | 5 | 6 | VI-1 | PIGN | 2.61 |
| 608 | 3 | 4 | 5 | 6 | VI-1 | PIK3R4 | 2.02 |
| 609 | 3 | 4 | 5 | 6 | VI-1 | PKM2 | 2.33 |
| 610 | 3 | 4 | 5 | 6 | VI-1 | PLA2G4A | 2.78 |
| 611 | 3 | 4 | 5 | 6 | VI-1 | PLA2G4C | 2.16 |
| 612 | 3 | 4 | 5 | 6 | VI-1 | PLAA | 2.02 |
| 613 | 3 | 4 | 5 | 6 | VI-1 | PLAC8 | 2.33 |
| 614 | 3 | 4 | 5 | 6 | VI-1 | PLB1 | 2.20 |
| 615 | 3 | 4 | 5 | 6 | VI-1 | PLBD1 | 3.59 |
| 616 | 3 | 4 | 5 | 6 | VI-1 | PLCB3 | 2.18 |
| 617 | 3 | 4 | 5 | 6 | VI-1 | PLD1 | 2.57 |
| 618 | 3 | 4 | 5 | 6 | VI-1 | PLEC | 2.15 |
| 619 | 3 | 4 | 5 | 6 | VI-1 | PLEKHA8P1 | 2.16 |
| 620 | 3 | 4 | 5 | 6 | VI-1 | PLIN2 | 2.22 |
| 621 | 3 | 4 | 5 | 6 | VI-1 | PLIN3 | 2.61 |
| 622 | 3 | 4 | 5 | 6 | VI-1 | PLOD1 | 2.49 |
| 623 | 3 | 4 | 5 | 6 | VI-1 | PLOD3 | 2.90 |
| 624 | 3 | 4 | 5 | 6 | VI-1 | PLSCR1 | 3.46 |
| 625 | 3 | 4 | 5 | 6 | VI-1 | PNPLA6 | 2.19 |
| 626 | 3 | 4 | 5 | 6 | VI-1 | PNPO | 2.01 |
| 627 | 3 | 4 | 5 | 6 | VI-1 | POLR1B | 2.09 |
| 628 | 3 | 4 | 5 | 6 | VI-1 | POLR3A | 2.10 |
| 629 | 3 | 4 | 5 | 6 | VI-1 | POMP | 2.30 |
| 630 | 3 | 4 | 5 | 6 | VI-1 | POR | 2.06 |
| 631 | 3 | 4 | 5 | 6 | VI-1 | PPA2 | 2.03 |
| 632 | 3 | 4 | 5 | 6 | VI-1 | PPARG | 2.07 |
| 633 | 3 | 4 | 5 | 6 | VI-1 | PPARGC1B | 2.18 |
| 634 | 3 | 4 | 5 | 6 | VI-1 | PPP1R26 | 2.74 |
| 635 | 3 | 4 | 5 | 6 | VI-1 | PPP2CB | 2.12 |
| 636 | 3 | 4 | 5 | 6 | VI-1 | PPP2R1B | 2.27 |
| 637 | 3 | 4 | 5 | 6 | VI-1 | PPP2R4 | 2.26 |
| 638 | 3 | 4 | 5 | 6 | VI-1 | PQLC3 | 2.10 |
| 639 | 3 | 4 | 5 | 6 | VI-1 | PRDX1 | 2.51 |
| 640 | 3 | 4 | 5 | 6 | VI-1 | PRDX3 | 2.80 |
| 641 | 3 | 4 | 5 | 6 | VI-1 | PREP | 2.29 |
| 642 | 3 | 4 | 5 | 6 | VI-1 | PREPL | 2.03 |
| 643 | 3 | 4 | 5 | 6 | VI-1 | PRKY | 2.74 |
| 644 | 3 | 4 | 5 | 6 | VI-1 | PROSC | 2.61 |
| 645 | 3 | 4 | 5 | 6 | VI-1 | PRR11 | 2.37 |
| 646 | 3 | 4 | 5 | 6 | VI-1 | PRRC1 | 2.05 |
| 647 | 3 | 4 | 5 | 6 | VI-1 | PRTN3 | 2.04 |
| 648 | 3 | 4 | 5 | 6 | VI-1 | PSAP | 3.09 |
| 649 | 3 | 4 | 5 | 6 | VI-1 | PSAT1 | 3.18 |
| 650 | 3 | 4 | 5 | 6 | VI-1 | PSMA1 | 2.23 |
| 651 | 3 | 4 | 5 | 6 | VI-1 | PSMA3 | 2.04 |
| 652 | 3 | 4 | 5 | 6 | VI-1 | PSMB5 | 2.18 |
| 653 | 3 | 4 | 5 | 6 | VI-1 | PSMB6 | 2.09 |
| 654 | 3 | 4 | 5 | 6 | VI-1 | PSMC6 | 2.01 |
| 655 | 3 | 4 | 5 | 6 | VI-1 | PSMD1 | 2.49 |
| 656 | 3 | 4 | 5 | 6 | VI-1 | PSMD14 | 2.28 |
| 657 | 3 | 4 | 5 | 6 | VI-1 | PSPH | 2.32 |
| 658 | 3 | 4 | 5 | 6 | VI-1 | PTCD1 | 2.20 |
| 659 | 3 | 4 | 5 | 6 | VI-1 | PTDSS1 | 2.06 |
| 660 | 3 | 4 | 5 | 6 | VI-1 | PTGES3 | 2.04 |
| 661 | 3 | 4 | 5 | 6 | VI-1 | PTGFRN | 2.77 |
| 662 | 3 | 4 | 5 | 6 | VI-1 | PTGR2 | 2.04 |
| 663 | 3 | 4 | 5 | 6 | VI-1 | PUM1 | 2.03 |
| 664 | 3 | 4 | 5 | 6 | VI-1 | PUSL1 | 2.05 |
| 665 | 3 | 4 | 5 | 6 | VI-1 | QSOX1 | 2.53 |
| 666 | 3 | 4 | 5 | 6 | VI-1 | QTRTD1 | 2.05 |
| 667 | 3 | 4 | 5 | 6 | VI-1 | RAB10 | 2.35 |
| 668 | 3 | 4 | 5 | 6 | VI-1 | RAB12 | 2.42 |
| 669 | 3 | 4 | 5 | 6 | VI-1 | RAB14 | 2.04 |
| 670 | 3 | 4 | 5 | 6 | VI-1 | RAB32 | 2.37 |
| 671 | 3 | 4 | 5 | 6 | VI-1 | RAB8B | 2.01 |
| 672 | 3 | 4 | 5 | 6 | VI-1 | RABGGTA | 2.05 |
| 673 | 3 | 4 | 5 | 6 | VI-1 | RAC1 | 2.09 |
| 674 | 3 | 4 | 5 | 6 | VI-1 | RAP2B | 2.01 |
| 675 | 3 | 4 | 5 | 6 | VI-1 | RB1 | 2.32 |
| 676 | 3 | 4 | 5 | 6 | VI-1 | RBBP8 | 2.21 |
| 677 | 3 | 4 | 5 | 6 | VI-1 | RBM14-RBM4 | 2.42 |
| 678 | 3 | 4 | 5 | 6 | VI-1 | RBM4S | 2.21 |
| 679 | 3 | 4 | 5 | 6 | VI-1 | RCN1 | 2.10 |
| 680 | 3 | 4 | 5 | 6 | VI-1 | RDX | 2.25 |
| 681 | 3 | 4 | 5 | 6 | VI-1 | REEP4 | 2.38 |
| 682 | 3 | 4 | 5 | 6 | VI-1 | REPS1 | 2.03 |
| 683 | 3 | 4 | 5 | 6 | VI-1 | RGAG4 | 3.67 |
| 684 | 3 | 4 | 5 | 6 | VI-1 | RGL1 | 2.84 |
| 685 | 3 | 4 | 5 | 6 | VI-1 | RHBDF2 | 2.10 |
| 686 | 3 | 4 | 5 | 6 | VI-1 | RHOU | 2.91 |
| 687 | 3 | 4 | 5 | 6 | VI-1 | RNPEP | 2.44 |
| 688 | 3 | 4 | 5 | 6 | VI-1 | RPL18 | 2.79 |
| 689 | 3 | 4 | 5 | 6 | VI-1 | RPN2 | 2.32 |
| 690 | 3 | 4 | 5 | 6 | VI-1 | RPP25 | 2.07 |
| 691 | 3 | 4 | 5 | 6 | VI-1 | RRAS | 3.09 |
| 692 | 3 | 4 | 5 | 6 | VI-1 | RRBP1 | 2.40 |
| 693 | 3 | 4 | 5 | 6 | VI-1 | RREB1 | 2.13 |
| 694 | 3 | 4 | 5 | 6 | VI-1 | RRM2 | 3.58 |
| 695 | 3 | 4 | 5 | 6 | VI-1 | SAAL1 | 2.08 |
| 696 | 3 | 4 | 5 | 6 | VI-1 | SAC3D1 | 2.40 |
| 697 | 3 | 4 | 5 | 6 | VI-1 | SAMHD1 | 3.30 |
| 698 | 3 | 4 | 5 | 6 | VI-1 | SCARB2 | 3.56 |
| 699 | 3 | 4 | 5 | 6 | VI-1 | SCCPDH | 2.05 |
| 700 | 3 | 4 | 5 | 6 | VI-1 | SCO1 | 2.23 |
| 701 | 3 | 4 | 5 | 6 | VI-1 | SDSL | 2.66 |
| 702 | 3 | 4 | 5 | 6 | VI-1 | SEC11A | 2.15 |
| 703 | 3 | 4 | 5 | 6 | VI-1 | SEC24A | 2.05 |
| 704 | 3 | 4 | 5 | 6 | VI-1 | SEC24D | 2.06 |
| 705 | 3 | 4 | 5 | 6 | VI-1 | SEC31A | 2.25 |
| 706 | 3 | 4 | 5 | 6 | VI-1 | SEC61A1 | 2.41 |
| 707 | 3 | 4 | 5 | 6 | VI-1 | SEC61B | 2.12 |
| 708 | 3 | 4 | 5 | 6 | VI-1 | SELRC1 | 2.07 |
| 709 | 3 | 4 | 5 | 6 | VI-1 | SEPN1 | 2.30 |
| 710 | 3 | 4 | 5 | 6 | VI-1 | 42615 | 2.35 |
| 711 | 3 | 4 | 5 | 6 | VI-1 | SERBP1 | 2.00 |
| 712 | 3 | 4 | 5 | 6 | VI-1 | SERPINB8 | 2.14 |
| 713 | 3 | 4 | 5 | 6 | VI-1 | SFPQ | 2.18 |
| 714 | 3 | 4 | 5 | 6 | VI-1 | SH3BGRL | 2.01 |
| 715 | 3 | 4 | 5 | 6 | VI-1 | SIGLEC1 | 3.59 |
| 716 | 3 | 4 | 5 | 6 | VI-1 | SIGLEC11 | 2.20 |
| 717 | 3 | 4 | 5 | 6 | VI-1 | SIGLEC15 | 3.06 |
| 718 | 3 | 4 | 5 | 6 | VI-1 | SIGLEC9 | 2.48 |
| 719 | 3 | 4 | 5 | 6 | VI-1 | SLC10A7 | 2.25 |
| 720 | 3 | 4 | 5 | 6 | VI-1 | SLC16A1 | 2.77 |
| 721 | 3 | 4 | 5 | 6 | VI-1 | SLC16A6 | 2.25 |
| 722 | 3 | 4 | 5 | 6 | VI-1 | SLC16A7 | 2.90 |
| 723 | 3 | 4 | 5 | 6 | VI-1 | SLC1A5 | 2.63 |
| 724 | 3 | 4 | 5 | 6 | VI-1 | SLC22A5 | 2.94 |
| 725 | 3 | 4 | 5 | 6 | VI-1 | SLC25A19 | 2.27 |
| 726 | 3 | 4 | 5 | 6 | VI-1 | SLC25A24 | 3.02 |
| 727 | 3 | 4 | 5 | 6 | VI-1 | SLC25A3 | 2.36 |
| 728 | 3 | 4 | 5 | 6 | VI-1 | SLC25A43 | 2.04 |
| 729 | 3 | 4 | 5 | 6 | VI-1 | SLC26A2 | 2.06 |
| 730 | 3 | 4 | 5 | 6 | VI-1 | SLC27A3 | 2.54 |
| 731 | 3 | 4 | 5 | 6 | VI-1 | SLC30A1 | 3.49 |
| 732 | 3 | 4 | 5 | 6 | VI-1 | SLC31A1 | 2.27 |
| 733 | 3 | 4 | 5 | 6 | VI-1 | SLC35A1 | 2.51 |
| 734 | 3 | 4 | 5 | 6 | VI-1 | SLC35B1 | 2.95 |
| 735 | 3 | 4 | 5 | 6 | VI-1 | SLC35C1 | 2.12 |
| 736 | 3 | 4 | 5 | 6 | VI-1 | SLC35E4 | 2.05 |
| 737 | 3 | 4 | 5 | 6 | VI-1 | SLC38A10 | 2.17 |
| 738 | 3 | 4 | 5 | 6 | VI-1 | SLC38A9 | 2.32 |
| 739 | 3 | 4 | 5 | 6 | VI-1 | SLC39A11 | 2.80 |
| 740 | 3 | 4 | 5 | 6 | VI-1 | SLC39A8 | 2.33 |
| 741 | 3 | 4 | 5 | 6 | VI-1 | SLC3A2 | 2.18 |
| 742 | 3 | 4 | 5 | 6 | VI-1 | SLC46A1 | 3.00 |
| 743 | 3 | 4 | 5 | 6 | VI-1 | SLC4A2 | 2.20 |
| 744 | 3 | 4 | 5 | 6 | VI-1 | SLC9A9 | 2.87 |
| 745 | 3 | 4 | 5 | 6 | VI-1 | SLFN11 | 3.21 |
| 746 | 3 | 4 | 5 | 6 | VI-1 | SLFN12 | 3.37 |
| 747 | 3 | 4 | 5 | 6 | VI-1 | SLITRK4 | 2.56 |
| 748 | 3 | 4 | 5 | 6 | VI-1 | SMAD1 | 4.62 |
| 749 | 3 | 4 | 5 | 6 | VI-1 | SNAPC2 | 2.16 |
| 750 | 3 | 4 | 5 | 6 | VI-1 | SNAPC3 | 2.18 |
| 751 | 3 | 4 | 5 | 6 | VI-1 | SND1 | 2.17 |
| 752 | 3 | 4 | 5 | 6 | VI-1 | SNRPE | 2.01 |
| 753 | 3 | 4 | 5 | 6 | VI-1 | SNTB1 | 2.14 |
| 754 | 3 | 4 | 5 | 6 | VI-1 | SNX21 | 2.05 |
| 755 | 3 | 4 | 5 | 6 | VI-1 | SNX30 | 2.09 |
| 756 | 3 | 4 | 5 | 6 | VI-1 | SOAT1 | 2.46 |
| 757 | 3 | 4 | 5 | 6 | VI-1 | SOCS6 | 2.50 |
| 758 | 3 | 4 | 5 | 6 | VI-1 | SPATS2L | 2.04 |
| 759 | 3 | 4 | 5 | 6 | VI-1 | SPCS2 | 2.31 |
| 760 | 3 | 4 | 5 | 6 | VI-1 | SPECC1 | 2.18 |
| 761 | 3 | 4 | 5 | 6 | VI-1 | SPHK1 | 2.12 |
| 762 | 3 | 4 | 5 | 6 | VI-1 | SPPL2A | 2.17 |
| 763 | 3 | 4 | 5 | 6 | VI-1 | SPRED1 | 2.22 |
| 764 | 3 | 4 | 5 | 6 | VI-1 | SPTLC2 | 2.48 |
| 765 | 3 | 4 | 5 | 6 | VI-1 | SQLE | 2.76 |
| 766 | 3 | 4 | 5 | 6 | VI-1 | SRD5A1P1 | 2.92 |

Fig. 41 - 5

| | | | | | | | | | | | | | | | | |
|---|---|---|---|---|---|---|---|---|---|---|---|---|---|---|---|---|
| 767 | 3 | 4 | 5 | 6 | | VI-1 | SREBF2 | 2.13 | 863 | 3 | 4 | 5 | 6 | | VI-1 | WDR60 | 3.47 |
| 768 | 3 | 4 | 5 | 6 | | VI-1 | SRGAP2 | 2.15 | 864 | 3 | 4 | 5 | 6 | | VI-1 | WDR7 | 2.09 |
| 769 | 3 | 4 | 5 | 6 | | VI-1 | SRGAP2P2 | 2.30 | 865 | 3 | 4 | 5 | 6 | | VI-1 | WDR81 | 2.17 |
| 770 | 3 | 4 | 5 | 6 | | VI-1 | SRP68 | 2.12 | 866 | 3 | 4 | 5 | 6 | | VI-1 | WDYHV1 | 2.01 |
| 771 | 3 | 4 | 5 | 6 | | VI-1 | SSBP3 | 2.03 | 867 | 3 | 4 | 5 | 6 | | VI-1 | XPNPEP1 | 2.12 |
| 772 | 3 | 4 | 5 | 6 | | VI-1 | ST3GAL5 | 2.49 | 868 | 3 | 4 | 5 | 6 | | VI-1 | XRCC5 | 2.19 |
| 773 | 3 | 4 | 5 | 6 | | VI-1 | ST6GALNAC3 | 2.11 | 869 | 3 | 4 | 5 | 6 | | VI-1 | XXYLT1 | 2.43 |
| 774 | 3 | 4 | 5 | 6 | | VI-1 | STAB1 | 4.48 | 870 | 3 | 4 | 5 | 6 | | VI-1 | YARS2 | 2.12 |
| 775 | 3 | 4 | 5 | 6 | | VI-1 | STARD8 | 3.45 | 871 | 3 | 4 | 5 | 6 | | VI-1 | YBEY | 2.46 |
| 776 | 3 | 4 | 5 | 6 | | VI-1 | STBD1 | 2.11 | 872 | 3 | 4 | 5 | 6 | | VI-1 | YIPF4 | 2.08 |
| 777 | 3 | 4 | 5 | 6 | | VI-1 | STEAP3 | 3.85 | 873 | 3 | 4 | 5 | 6 | | VI-1 | YTHDF2 | 2.09 |
| 778 | 3 | 4 | 5 | 6 | | VI-1 | STK3 | 2.58 | 874 | 3 | 4 | 5 | 6 | | VI-1 | YWHAB | 2.38 |
| 779 | 3 | 4 | 5 | 6 | | VI-1 | STT3A | 2.53 | 875 | 3 | 4 | 5 | 6 | | VI-1 | YWHAG | 3.12 |
| 780 | 3 | 4 | 5 | 6 | | VI-1 | STX12 | 2.18 | 876 | 3 | 4 | 5 | 6 | | VI-1 | YWHAH | 2.34 |
| 781 | 3 | 4 | 5 | 6 | | VI-1 | SUCLA2 | 2.62 | 877 | 3 | 4 | 5 | 6 | | VI-1 | ZADH2 | 2.07 |
| 782 | 3 | 4 | 5 | 6 | | VI-1 | SUFU | 2.87 | 878 | 3 | 4 | 5 | 6 | | VI-1 | ZAK | 3.05 |
| 783 | 3 | 4 | 5 | 6 | | VI-1 | SUGT1 | 2.33 | 879 | 3 | 4 | 5 | 6 | | VI-1 | ZBT847 | 2.11 |
| 784 | 3 | 4 | 5 | 6 | | VI-1 | SUMF1 | 2.53 | 880 | 3 | 4 | 5 | 6 | | VI-1 | ZDHHC20 | 2.40 |
| 785 | 3 | 4 | 5 | 6 | | VI-1 | SYNCRIP | 2.04 | 881 | 3 | 4 | 5 | 6 | | VI-1 | ZEB2 | 2.22 |
| 786 | 3 | 4 | 5 | 6 | | VI-1 | SYPL1 | 2.02 | 882 | 3 | 4 | 5 | 6 | | VI-1 | ZFAND5 | 2.27 |
| 787 | 3 | 4 | 5 | 6 | | VI-1 | TAF13 | 2.16 | 883 | 3 | 4 | 5 | 6 | | VI-1 | ZFP106 | 2.05 |
| 788 | 3 | 4 | 5 | 6 | | VI-1 | TAGLN | 2.72 | 884 | 3 | 4 | 5 | 6 | | VI-1 | ZFY | 4.72 |
| 789 | 3 | 4 | 5 | 6 | | VI-1 | TARS | 2.07 | 885 | 3 | 4 | 5 | 6 | | VI-1 | ZNF124 | 2.05 |
| 790 | 3 | 4 | 5 | 6 | | VI-1 | TBC1D2 | 3.47 | 886 | 3 | 4 | 5 | 6 | | VI-1 | ZNF282 | 2.03 |
| 791 | 3 | 4 | 5 | 6 | | VI-1 | TBC1D5 | 2.10 | 887 | 3 | 4 | 5 | 6 | | VI-1 | ZNF366 | 2.12 |
| 792 | 3 | 4 | 5 | 6 | | VI-1 | TBC1D9B | 2.20 | 888 | 3 | 4 | 5 | 6 | | VI-1 | ZNF503 | 2.98 |
| 793 | 3 | 4 | 5 | 6 | | VI-1 | TBCK | 2.13 | 889 | 3 | 4 | 5 | 6 | | VI-1 | ZNF697 | 2.67 |
| 794 | 3 | 4 | 5 | 6 | | VI-1 | TDG | 2.07 | 890 | 3 | 4 | 5 | 6 | | VI-1 | ZSWIM6 | 2.21 |
| 795 | 3 | 4 | 5 | 6 | | VI-1 | TFCP2 | 2.19 | 891 | 3 | 4 | 5 | 6 | | VI-1 | ZWILCH | 2.01 |
| 796 | 3 | 4 | 5 | 6 | | VI-1 | TICAM1 | 2.13 | 892 | 3 | 4 | 5 | | | V-2 | AATK | 0.59 |
| 797 | 3 | 4 | 5 | 6 | | VI-1 | TICAM2 | 3.15 | 893 | 3 | 4 | 5 | | | V-2 | ABCG1 | 0.60 |
| 798 | 3 | 4 | 5 | 6 | | VI-1 | TIMM17A | 2.01 | 894 | 3 | 4 | 5 | | | V-2 | ACRBP | 0.61 |
| 799 | 3 | 4 | 5 | 6 | | VI-1 | TJP2 | 3.22 | 895 | 3 | 4 | 5 | | | V-2 | ACYP1 | 0.63 |
| 800 | 3 | 4 | 5 | 6 | | VI-1 | TK1 | 2.15 | 896 | 3 | 4 | 5 | | | V-2 | AGAP9 | 0.59 |
| 801 | 3 | 4 | 5 | 6 | | VI-1 | TLR5 | 2.47 | 897 | 3 | 4 | 5 | | | V-2 | ANKMY1 | 0.56 |
| 802 | 3 | 4 | 5 | 6 | | VI-1 | TLR8 | 2.09 | 898 | 3 | 4 | 5 | | | V-2 | APPL2 | 0.67 |
| 803 | 3 | 4 | 5 | 6 | | VI-1 | TM9SF1 | 2.03 | 899 | 3 | 4 | 5 | | | V-2 | ATP5J2-PTCD1 | 0.54 |
| 804 | 3 | 4 | 5 | 6 | | VI-1 | TM9SF2 | 2.05 | 900 | 3 | 4 | 5 | | | V-2 | ATP5L2 | 0.57 |
| 805 | 3 | 4 | 5 | 6 | | VI-1 | TM9SF4 | 2.10 | 901 | 3 | 4 | 5 | | | V-2 | BACE2 | 0.51 |
| 806 | 3 | 4 | 5 | 6 | | VI-1 | TMED7 | 2.05 | 902 | 3 | 4 | 5 | | | V-2 | B854 | 0.62 |
| 807 | 3 | 4 | 5 | 6 | | VI-1 | TMEM159 | 2.00 | 903 | 3 | 4 | 5 | | | V-2 | BTN2A1 | 0.59 |
| 808 | 3 | 4 | 5 | 6 | | VI-1 | TMEM165 | 2.05 | 904 | 3 | 4 | 5 | | | V-2 | BTN3A1 | 0.64 |
| 809 | 3 | 4 | 5 | 6 | | VI-1 | TMEM167A | 2.43 | 905 | 3 | 4 | 5 | | | V-2 | BTN3A2 | 0.60 |
| 810 | 3 | 4 | 5 | 6 | | VI-1 | TMEM173 | 2.23 | 906 | 3 | 4 | 5 | | | V-2 | C12orf57 | 0.51 |
| 811 | 3 | 4 | 5 | 6 | | VI-1 | TMEM60 | 2.01 | 907 | 3 | 4 | 5 | | | V-2 | C22orf40 | 0.60 |
| 812 | 3 | 4 | 5 | 6 | | VI-1 | TMEM87B | 2.01 | 908 | 3 | 4 | 5 | | | V-2 | C7orf41 | 0.60 |
| 813 | 3 | 4 | 5 | 6 | | VI-1 | TMEM9B | 2.05 | 909 | 3 | 4 | 5 | | | V-2 | CASS4 | 0.57 |
| 814 | 3 | 4 | 5 | 6 | | VI-1 | TMTC1 | 3.91 | 910 | 3 | 4 | 5 | | | V-2 | CBX7 | 0.56 |
| 815 | 3 | 4 | 5 | 6 | | VI-1 | TMTC2 | 3.46 | 911 | 3 | 4 | 5 | | | V-2 | CCDC57 | 0.61 |
| 816 | 3 | 4 | 5 | 6 | | VI-1 | TMTC4 | 2.05 | 912 | 3 | 4 | 5 | | | V-2 | CCDC58 | 0.52 |
| 817 | 3 | 4 | 5 | 6 | | VI-1 | TMX1 | 2.70 | 913 | 3 | 4 | 5 | | | V-2 | CCDC65 | 0.57 |
| 818 | 3 | 4 | 5 | 6 | | VI-1 | TPGS1 | 2.18 | 914 | 3 | 4 | 5 | | | V-2 | CCL28 | 0.66 |
| 819 | 3 | 4 | 5 | 6 | | VI-1 | TPM1 | 2.10 | 915 | 3 | 4 | 5 | | | V-2 | CCR9 | 0.64 |
| 820 | 3 | 4 | 5 | 6 | | VI-1 | TPP1 | 2.76 | 916 | 3 | 4 | 5 | | | V-2 | CD24 | 0.58 |
| 821 | 3 | 4 | 5 | 6 | | VI-1 | TRAM2 | 2.25 | 917 | 3 | 4 | 5 | | | V-2 | CD3D | 0.65 |
| 822 | 3 | 4 | 5 | 6 | | VI-1 | TRIM14 | 2.39 | 918 | 3 | 4 | 5 | | | V-2 | CD82 | 0.66 |
| 823 | 3 | 4 | 5 | 6 | | VI-1 | TRIM16 | 2.65 | 919 | 3 | 4 | 5 | | | V-2 | CD8B | 0.65 |
| 824 | 3 | 4 | 5 | 6 | | VI-1 | TRIM44 | 2.21 | 920 | 3 | 4 | 5 | | | V-2 | CEMP1 | 0.67 |
| 825 | 3 | 4 | 5 | 6 | | VI-1 | TRMT5 | 2.11 | 921 | 3 | 4 | 5 | | | V-2 | CLDN15 | 0.54 |
| 826 | 3 | 4 | 5 | 6 | | VI-1 | TSHZ2 | 2.36 | 922 | 3 | 4 | 5 | | | V-2 | COMMD3-BMI1 | 0.65 |
| 827 | 3 | 4 | 5 | 6 | | VI-1 | TSHZ3 | 2.48 | 923 | 3 | 4 | 5 | | | V-2 | CREBZF | 0.64 |
| 828 | 3 | 4 | 5 | 6 | | VI-1 | TSPO | 2.26 | 924 | 3 | 4 | 5 | | | V-2 | CSF3R | 0.61 |
| 829 | 3 | 4 | 5 | 6 | | VI-1 | TTLL12 | 2.35 | 925 | 3 | 4 | 5 | | | V-2 | DCUN1D2 | 0.60 |
| 830 | 3 | 4 | 5 | 6 | | VI-1 | TTTY15 | 2.09 | 926 | 3 | 4 | 5 | | | V-2 | DDIT3 | 0.64 |
| 831 | 3 | 4 | 5 | 6 | | VI-1 | TTYH3 | 3.24 | 927 | 3 | 4 | 5 | | | V-2 | DHX34 | 0.63 |
| 832 | 3 | 4 | 5 | 6 | | VI-1 | TUBGCP4 | 2.20 | 928 | 3 | 4 | 5 | | | V-2 | EEF1B2 | 0.61 |
| 833 | 3 | 4 | 5 | 6 | | VI-1 | TXNL4A | 2.13 | 929 | 3 | 4 | 5 | | | V-2 | EFHC2 | 0.67 |
| 834 | 3 | 4 | 5 | 6 | | VI-1 | TYMS | 2.15 | 930 | 3 | 4 | 5 | | | V-2 | ERF | 0.63 |
| 835 | 3 | 4 | 5 | 6 | | VI-1 | UBA6 | 2.16 | 931 | 3 | 4 | 5 | | | V-2 | ERN1 | 0.61 |
| 836 | 3 | 4 | 5 | 6 | | VI-1 | UBASH3B | 2.10 | 932 | 3 | 4 | 5 | | | V-2 | FAM122C | 0.66 |
| 837 | 3 | 4 | 5 | 6 | | VI-1 | UBE2E1 | 2.10 | 933 | 3 | 4 | 5 | | | V-2 | FAM174A | 0.62 |
| 838 | 3 | 4 | 5 | 6 | | VI-1 | UBE3A | 2.02 | 934 | 3 | 4 | 5 | | | V-2 | FAM212A | 0.58 |
| 839 | 3 | 4 | 5 | 6 | | VI-1 | UBFD1 | 2.07 | 935 | 3 | 4 | 5 | | | V-2 | FAM45A | 0.58 |
| 840 | 3 | 4 | 5 | 6 | | VI-1 | UBQLN1 | 2.16 | 936 | 3 | 4 | 5 | | | V-2 | FAM63A | 0.64 |
| 841 | 3 | 4 | 5 | 6 | | VI-1 | UBQLN2 | 2.05 | 937 | 3 | 4 | 5 | | | V-2 | FCHSD1 | 0.59 |
| 842 | 3 | 4 | 5 | 6 | | VI-1 | UBTD2 | 2.35 | 938 | 3 | 4 | 5 | | | V-2 | FLVCR1 | 0.56 |
| 843 | 3 | 4 | 5 | 6 | | VI-1 | UCHL3 | 3.98 | 939 | 3 | 4 | 5 | | | V-2 | FTH1P3 | 0.62 |
| 844 | 3 | 4 | 5 | 6 | | VI-1 | UCP2 | 2.10 | 940 | 3 | 4 | 5 | | | V-2 | FUNDC2 | 0.61 |
| 845 | 3 | 4 | 5 | 6 | | VI-1 | ULK2 | 2.14 | 941 | 3 | 4 | 5 | | | V-2 | GAMT | 0.65 |
| 846 | 3 | 4 | 5 | 6 | | VI-1 | UNC93B1 | 2.34 | 942 | 3 | 4 | 5 | | | V-2 | GIGYF1 | 0.67 |
| 847 | 3 | 4 | 5 | 6 | | VI-1 | UQCRC1 | 2.25 | 943 | 3 | 4 | 5 | | | V-2 | GNG10 | 0.59 |
| 848 | 3 | 4 | 5 | 6 | | VI-1 | UROS | 2.16 | 944 | 3 | 4 | 5 | | | V-2 | GPR77 | 0.65 |
| 849 | 3 | 4 | 5 | 6 | | VI-1 | USO1 | 2.14 | 945 | 3 | 4 | 5 | | | V-2 | GPR89C | 0.66 |
| 850 | 3 | 4 | 5 | 6 | | VI-1 | VAT1 | 2.20 | 946 | 3 | 4 | 5 | | | V-2 | GPX7 | 0.62 |
| 851 | 3 | 4 | 5 | 6 | | VI-1 | VDAC1 | 2.80 | 947 | 3 | 4 | 5 | | | V-2 | GRAP2 | 0.65 |
| 852 | 3 | 4 | 5 | 6 | | VI-1 | VDR | 2.56 | 948 | 3 | 4 | 5 | | | V-2 | HCAR3 | 0.65 |
| 853 | 3 | 4 | 5 | 6 | | VI-1 | VIM | 2.87 | 949 | 3 | 4 | 5 | | | V-2 | HCG26 | 0.65 |
| 854 | 3 | 4 | 5 | 6 | | VI-1 | VPS26A | 2.31 | 950 | 3 | 4 | 5 | | | V-2 | HIP1R | 0.59 |
| 855 | 3 | 4 | 5 | 6 | | VI-1 | VPS35 | 2.05 | 951 | 3 | 4 | 5 | | | V-2 | HIST1H2AC | 0.57 |
| 856 | 3 | 4 | 5 | 6 | | VI-1 | VPS41 | 2.19 | 952 | 3 | 4 | 5 | | | V-2 | HIST1H2BC | 0.54 |
| 857 | 3 | 4 | 5 | 6 | | VI-1 | VPS45 | 2.17 | 953 | 3 | 4 | 5 | | | V-2 | HIST1H2BH | 0.64 |
| 858 | 3 | 4 | 5 | 6 | | VI-1 | VTA1 | 2.01 | 954 | 3 | 4 | 5 | | | V-2 | HIST1H2BJ | 0.59 |
| 859 | 3 | 4 | 5 | 6 | | VI-1 | VWA5A | 3.01 | 955 | 3 | 4 | 5 | | | V-2 | HIST1H2BN | 0.53 |
| 860 | 3 | 4 | 5 | 6 | | VI-1 | WARS2 | 2.22 | 956 | 3 | 4 | 5 | | | V-2 | HIST1H3H | 0.59 |
| 861 | 3 | 4 | 5 | 6 | | VI-1 | WDR11 | 2.02 | 957 | 3 | 4 | 5 | | | V-2 | HKR1 | 0.67 |
| 862 | 3 | 4 | 5 | 6 | | VI-1 | WDR3 | 2.09 | 958 | 3 | 4 | 5 | | | V-2 | HSH2D | 0.50 |

Fig. 41 - 6

| | | | | | | | | | | | | | | | | | |
|---|---|---|---|---|---|---|---|---|---|---|---|---|---|---|---|---|---|
| 959 | 3 | 4 | 5 | | | V-2 | ISG20 | 0.59 | 1055 | 3 | 4 | 5 | | | V-1 | ABHD16B | 1.97 |
| 960 | 3 | 4 | 5 | | | V-2 | KCTD13 | 0.63 | 1056 | 3 | 4 | 5 | | | V-1 | ABHD6 | 1.68 |
| 961 | 3 | 4 | 5 | | | V-2 | KLRB1 | 0.64 | 1057 | 3 | 4 | 5 | | | V-1 | ABHD8 | 1.98 |
| 962 | 3 | 4 | 5 | | | V-2 | LGALSL | 0.51 | 1058 | 3 | 4 | 5 | | | V-1 | ABI3 | 1.76 |
| 963 | 3 | 4 | 5 | | | V-2 | LHPP | 0.56 | 1059 | 3 | 4 | 5 | | | V-1 | ABL2 | 1.79 |
| 964 | 3 | 4 | 5 | | | V-2 | LOC100130744 | 0.60 | 1060 | 3 | 4 | 5 | | | V-1 | ACAA2 | 1.95 |
| 965 | 3 | 4 | 5 | | | V-2 | LOC100132273 | 0.64 | 1061 | 3 | 4 | 5 | | | V-1 | ACAD9 | 1.77 |
| 966 | 3 | 4 | 5 | | | V-2 | LOC100287482 | 0.59 | 1062 | 3 | 4 | 5 | | | V-1 | ACADS | 1.99 |
| 967 | 3 | 4 | 5 | | | V-2 | LOC100505622 | 0.55 | 1063 | 3 | 4 | 5 | | | V-1 | ACADVL | 1.79 |
| 968 | 3 | 4 | 5 | | | V-2 | LOC100506343 | 0.55 | 1064 | 3 | 4 | 5 | | | V-1 | ACAT1 | 1.61 |
| 969 | 3 | 4 | 5 | | | V-2 | LOC100506866 | 0.61 | 1065 | 3 | 4 | 5 | | | V-1 | ACBD3 | 1.57 |
| 970 | 3 | 4 | 5 | | | V-2 | LOC100507495 | 0.57 | 1066 | 3 | 4 | 5 | | | V-1 | ACBD5 | 1.56 |
| 971 | 3 | 4 | 5 | | | V-2 | LOC729799 | 0.66 | 1067 | 3 | 4 | 5 | | | V-1 | ACLY | 1.92 |
| 972 | 3 | 4 | 5 | | | V-2 | LPAR5 | 0.62 | 1068 | 3 | 4 | 5 | | | V-1 | ACO1 | 1.87 |
| 973 | 3 | 4 | 5 | | | V-2 | LRMP | 0.65 | 1069 | 3 | 4 | 5 | | | V-1 | ACO2 | 1.95 |
| 974 | 3 | 4 | 5 | | | V-2 | LRTOMT | 0.59 | 1070 | 3 | 4 | 5 | | | V-1 | ACOT2 | 1.60 |
| 975 | 3 | 4 | 5 | | | V-2 | LY6G5C | 0.63 | 1071 | 3 | 4 | 5 | | | V-1 | ACOT7 | 1.93 |
| 976 | 3 | 4 | 5 | | | V-2 | MAP4K1 | 0.65 | 1072 | 3 | 4 | 5 | | | V-1 | ACOT9 | 1.92 |
| 977 | 3 | 4 | 5 | | | V-2 | METTL21D | 0.64 | 1073 | 3 | 4 | 5 | | | V-1 | ACP2 | 1.88 |
| 978 | 3 | 4 | 5 | | | V-2 | MUTYH | 0.66 | 1074 | 3 | 4 | 5 | | | V-1 | ACP5 | 1.82 |
| 979 | 3 | 4 | 5 | | | V-2 | NAT6 | 0.67 | 1075 | 3 | 4 | 5 | | | V-1 | ACPP | 1.74 |
| 980 | 3 | 4 | 5 | | | V-2 | NDST1 | 0.58 | 1076 | 3 | 4 | 5 | | | V-1 | ACSF3 | 1.69 |
| 981 | 3 | 4 | 5 | | | V-2 | NKTR | 0.64 | 1077 | 3 | 4 | 5 | | | V-1 | ACSL3 | 1.71 |
| 982 | 3 | 4 | 5 | | | V-2 | NLRP1 | 0.56 | 1078 | 3 | 4 | 5 | | | V-1 | ACSL4 | 1.51 |
| 983 | 3 | 4 | 5 | | | V-2 | NPPA-AS1 | 0.63 | 1079 | 3 | 4 | 5 | | | V-1 | ACSL5 | 1.67 |
| 984 | 3 | 4 | 5 | | | V-2 | ODF2L | 0.63 | 1080 | 3 | 4 | 5 | | | V-1 | ACTG1 | 2.00 |
| 985 | 3 | 4 | 5 | | | V-2 | OTX1 | 0.64 | 1081 | 3 | 4 | 5 | | | V-1 | ACTR10 | 1.57 |
| 986 | 3 | 4 | 5 | | | V-2 | P2RY11 | 0.51 | 1082 | 3 | 4 | 5 | | | V-1 | ACTR1A | 1.53 |
| 987 | 3 | 4 | 5 | | | V-2 | PAIP2B | 0.67 | 1083 | 3 | 4 | 5 | | | V-1 | ACTR3 | 1.68 |
| 988 | 3 | 4 | 5 | | | V-2 | PDLIM1 | 0.63 | 1084 | 3 | 4 | 5 | | | V-1 | ACTR8 | 1.53 |
| 989 | 3 | 4 | 5 | | | V-2 | PHACTR1 | 0.60 | 1085 | 3 | 4 | 5 | | | V-1 | ACVR1 | 1.91 |
| 990 | 3 | 4 | 5 | | | V-2 | PLEKHG3 | 0.57 | 1086 | 3 | 4 | 5 | | | V-1 | ACYP2 | 1.87 |
| 991 | 3 | 4 | 5 | | | V-2 | PPP1R12B | 0.52 | 1087 | 3 | 4 | 5 | | | V-1 | ADA | 1.75 |
| 992 | 3 | 4 | 5 | | | V-2 | PPP1R15A | 0.65 | 1088 | 3 | 4 | 5 | | | V-1 | ADAM17 | 1.87 |
| 993 | 3 | 4 | 5 | | | V-2 | PPP1R3E | 0.50 | 1089 | 3 | 4 | 5 | | | V-1 | ADAT3 | 1.51 |
| 994 | 3 | 4 | 5 | | | V-2 | PPT2 | 0.61 | 1090 | 3 | 4 | 5 | | | V-1 | ADCK1 | 1.94 |
| 995 | 3 | 4 | 5 | | | V-2 | PRR7 | 0.53 | 1091 | 3 | 4 | 5 | | | V-1 | ADK | 1.84 |
| 996 | 3 | 4 | 5 | | | V-2 | PTP4A3 | 0.62 | 1092 | 3 | 4 | 5 | | | V-1 | ADNP | 1.50 |
| 997 | 3 | 4 | 5 | | | V-2 | RAB15 | 0.67 | 1093 | 3 | 4 | 5 | | | V-1 | ADNP2 | 1.60 |
| 998 | 3 | 4 | 5 | | | V-2 | RAB37 | 0.56 | 1094 | 3 | 4 | 5 | | | V-1 | ADSL | 1.84 |
| 999 | 3 | 4 | 5 | | | V-2 | RGS18 | 0.63 | 1095 | 3 | 4 | 5 | | | V-1 | AEBP2 | 1.64 |
| 1000 | 3 | 4 | 5 | | | V-2 | RNF19B | 0.65 | 1096 | 3 | 4 | 5 | | | V-1 | AFF4 | 1.51 |
| 1001 | 3 | 4 | 5 | | | V-2 | RPL39 | 0.58 | 1097 | 3 | 4 | 5 | | | V-1 | AFG3L2 | 1.83 |
| 1002 | 3 | 4 | 5 | | | V-2 | RPS10 | 0.53 | 1098 | 3 | 4 | 5 | | | V-1 | AFMID | 1.61 |
| 1003 | 3 | 4 | 5 | | | V-2 | RPS14 | 0.66 | 1099 | 3 | 4 | 5 | | | V-1 | AFTPH | 1.56 |
| 1004 | 3 | 4 | 5 | | | V-2 | RPS17L | 0.64 | 1100 | 3 | 4 | 5 | | | V-1 | AGAP3 | 1.71 |
| 1005 | 3 | 4 | 5 | | | V-2 | RPS27 | 0.64 | 1101 | 3 | 4 | 5 | | | V-1 | AGGF1 | 1.71 |
| 1006 | 3 | 4 | 5 | | | V-2 | RPS4X | 0.59 | 1102 | 3 | 4 | 5 | | | V-1 | AGL | 1.65 |
| 1007 | 3 | 4 | 5 | | | V-2 | RPS6KA2 | 0.66 | 1103 | 3 | 4 | 5 | | | V-1 | AGPAT2 | 1.98 |
| 1008 | 3 | 4 | 5 | | | V-2 | RPS7 | 0.63 | 1104 | 3 | 4 | 5 | | | V-1 | AGPAT5 | 1.50 |
| 1009 | 3 | 4 | 5 | | | V-2 | RWDD2A | 0.53 | 1105 | 3 | 4 | 5 | | | V-1 | AGPAT6 | 1.58 |
| 1010 | 3 | 4 | 5 | | | V-2 | SIGLEC5 | 0.57 | 1106 | 3 | 4 | 5 | | | V-1 | AGPAT9 | 1.61 |
| 1011 | 3 | 4 | 5 | | | V-2 | SLC2A4RG | 0.67 | 1107 | 3 | 4 | 5 | | | V-1 | AGTRAP | 1.67 |
| 1012 | 3 | 4 | 5 | | | V-2 | SLC45A4 | 0.54 | 1108 | 3 | 4 | 5 | | | V-1 | AHCYL1 | 1.62 |
| 1013 | 3 | 4 | 5 | | | V-2 | SNX22 | 0.57 | 1109 | 3 | 4 | 5 | | | V-1 | AHCYL2 | 1.96 |
| 1014 | 3 | 4 | 5 | | | V-2 | SPRY2 | 0.65 | 1110 | 3 | 4 | 5 | | | V-1 | AIM1 | 1.89 |
| 1015 | 3 | 4 | 5 | | | V-2 | TIGD3 | 0.51 | 1111 | 3 | 4 | 5 | | | V-1 | AIMP1 | 1.70 |
| 1016 | 3 | 4 | 5 | | | V-2 | TLR10 | 0.54 | 1112 | 3 | 4 | 5 | | | V-1 | AIMP2 | 1.84 |
| 1017 | 3 | 4 | 5 | | | V-2 | TLR9 | 0.65 | 1113 | 3 | 4 | 5 | | | V-1 | AK2 | 1.78 |
| 1018 | 3 | 4 | 5 | | | V-2 | TMCC1 | 0.52 | 1114 | 3 | 4 | 5 | | | V-1 | AKAP11 | 1.68 |
| 1019 | 3 | 4 | 5 | | | V-2 | TMEM198B | 0.67 | 1115 | 3 | 4 | 5 | | | V-1 | AKAP13 | 1.55 |
| 1020 | 3 | 4 | 5 | | | V-2 | TMEM91 | 0.56 | 1116 | 3 | 4 | 5 | | | V-1 | AKAP9 | 1.80 |
| 1021 | 3 | 4 | 5 | | | V-2 | TNFRSF9 | 0.57 | 1117 | 3 | 4 | 5 | | | V-1 | AKIP1 | 1.87 |
| 1022 | 3 | 4 | 5 | | | V-2 | TPD52 | 0.67 | 1118 | 3 | 4 | 5 | | | V-1 | ALAD | 1.60 |
| 1023 | 3 | 4 | 5 | | | V-2 | TSTD1 | 0.58 | 1119 | 3 | 4 | 5 | | | V-1 | ALDH9A1 | 1.74 |
| 1024 | 3 | 4 | 5 | | | V-2 | UST | 0.67 | 1120 | 3 | 4 | 5 | | | V-1 | ALDOA | 1.58 |
| 1025 | 3 | 4 | 5 | | | V-2 | WASH3P | 0.56 | 1121 | 3 | 4 | 5 | | | V-1 | ALG10 | 1.75 |
| 1026 | 3 | 4 | 5 | | | V-2 | XPO6 | 0.62 | 1122 | 3 | 4 | 5 | | | V-1 | ALG11 | 1.69 |
| 1027 | 3 | 4 | 5 | | | V-2 | YES1 | 0.63 | 1123 | 3 | 4 | 5 | | | V-1 | ALG2 | 1.73 |
| 1028 | 3 | 4 | 5 | | | V-2 | ZDHHC18 | 0.60 | 1124 | 3 | 4 | 5 | | | V-1 | ALG6 | 1.62 |
| 1029 | 3 | 4 | 5 | | | V-2 | ZEB1 | 0.66 | 1125 | 3 | 4 | 5 | | | V-1 | AMBRA1 | 1.59 |
| 1030 | 3 | 4 | 5 | | | V-2 | ZEB1-AS1 | 0.63 | 1126 | 3 | 4 | 5 | | | V-1 | AMFR | 1.70 |
| 1031 | 3 | 4 | 5 | | | V-2 | ZIK1 | 0.63 | 1127 | 3 | 4 | 5 | | | V-1 | AMMECR1 | 1.58 |
| 1032 | 3 | 4 | 5 | | | V-2 | ZNF107 | 0.60 | 1128 | 3 | 4 | 5 | | | V-1 | ANAPC2 | 1.50 |
| 1033 | 3 | 4 | 5 | | | V-2 | ZNF251 | 0.60 | 1129 | 3 | 4 | 5 | | | V-1 | ANKFY1 | 1.97 |
| 1034 | 3 | 4 | 5 | | | V-2 | ZNF329 | 0.53 | 1130 | 3 | 4 | 5 | | | V-1 | ANKHD1 | 1.62 |
| 1035 | 3 | 4 | 5 | | | V-2 | ZNF37BP | 0.61 | 1131 | 3 | 4 | 5 | | | V-1 | ANKIB1 | 1.63 |
| 1036 | 3 | 4 | 5 | | | V-2 | ZNF487P | 0.65 | 1132 | 3 | 4 | 5 | | | V-1 | ANKRD17 | 1.63 |
| 1037 | 3 | 4 | 5 | | | V-2 | ZNF814 | 0.53 | 1133 | 3 | 4 | 5 | | | V-1 | ANKRD32 | 1.85 |
| 1038 | 3 | 4 | 5 | | | V-2 | ZNF853 | 0.64 | 1134 | 3 | 4 | 5 | | | V-1 | ANKRD34B | 1.58 |
| 1039 | 3 | 4 | 5 | | | V-1 | A2LD1 | 1.52 | 1135 | 3 | 4 | 5 | | | V-1 | ANKRD36BP1 | 1.60 |
| 1040 | 3 | 4 | 5 | | | V-1 | AAAS | 1.84 | 1136 | 3 | 4 | 5 | | | V-1 | ANKRD40 | 1.61 |
| 1041 | 3 | 4 | 5 | | | V-1 | AACS | 1.70 | 1137 | 3 | 4 | 5 | | | V-1 | ANKS1A | 1.90 |
| 1042 | 3 | 4 | 5 | | | V-1 | AAGAB | 1.54 | 1138 | 3 | 4 | 5 | | | V-1 | ANO6 | 1.99 |
| 1043 | 3 | 4 | 5 | | | V-1 | AAK1 | 1.50 | 1139 | 3 | 4 | 5 | | | V-1 | ANP32B | 1.78 |
| 1044 | 3 | 4 | 5 | | | V-1 | AASDH | 1.66 | 1140 | 3 | 4 | 5 | | | V-1 | ANP32E | 1.70 |
| 1045 | 3 | 4 | 5 | | | V-1 | AATF | 1.63 | 1141 | 3 | 4 | 5 | | | V-1 | ANXA6 | 1.95 |
| 1046 | 3 | 4 | 5 | | | V-1 | ABCB7 | 1.82 | 1142 | 3 | 4 | 5 | | | V-1 | ANXA7 | 1.70 |
| 1047 | 3 | 4 | 5 | | | V-1 | ABCC1 | 1.62 | 1143 | 3 | 4 | 5 | | | V-1 | AOAH | 1.91 |
| 1048 | 3 | 4 | 5 | | | V-1 | ABCC10 | 1.68 | 1144 | 3 | 4 | 5 | | | V-1 | AP1G1 | 1.69 |
| 1049 | 3 | 4 | 5 | | | V-1 | ABCD3 | 1.87 | 1145 | 3 | 4 | 5 | | | V-1 | AP1M1 | 1.72 |
| 1050 | 3 | 4 | 5 | | | V-1 | ABCF1 | 1.86 | 1146 | 3 | 4 | 5 | | | V-1 | AP1S1 | 1.70 |
| 1051 | 3 | 4 | 5 | | | V-1 | ABCF2 | 1.69 | 1147 | 3 | 4 | 5 | | | V-1 | AP2A1 | 1.82 |
| 1052 | 3 | 4 | 5 | | | V-1 | ABCF3 | 1.50 | 1148 | 3 | 4 | 5 | | | V-1 | AP2A2 | 1.90 |
| 1053 | 3 | 4 | 5 | | | V-1 | ABHD12 | 1.67 | 1149 | 3 | 4 | 5 | | | V-1 | AP2B1 | 1.72 |
| 1054 | 3 | 4 | 5 | | | V-1 | ABHD15 | 1.60 | 1150 | 3 | 4 | 5 | | | V-1 | AP3D1 | 1.73 |

Fig. 41 - 7

| | | | | | | | | | | | | | | | |
|---|---|---|---|---|---|---|---|---|---|---|---|---|---|---|---|
| 1151 | 3 | 4 | 5 | | V-1 | AP3M1 | 1.88 | 1246 | 3 | 4 | 5 | | V-1 | ATXN10 | 1.87 |
| 1152 | 3 | 4 | 5 | | V-1 | AP4B1 | 1.54 | 1247 | 3 | 4 | 5 | | V-1 | ATXN7L1 | 1.73 |
| 1153 | 3 | 4 | 5 | | V-1 | AP4E1 | 1.93 | 1248 | 3 | 4 | 5 | | V-1 | ATXN7L3B | 1.64 |
| 1154 | 3 | 4 | 5 | | V-1 | APBB1IP | 1.83 | 1249 | 3 | 4 | 5 | | V-1 | AVPI1 | 1.67 |
| 1155 | 3 | 4 | 5 | | V-1 | APEH | 1.67 | 1250 | 3 | 4 | 5 | | V-1 | AZI2 | 2.00 |
| 1156 | 3 | 4 | 5 | | V-1 | APH1B | 1.76 | 1251 | 3 | 4 | 5 | | V-1 | B3GALT4 | 1.64 |
| 1157 | 3 | 4 | 5 | | V-1 | API5 | 1.82 | 1252 | 3 | 4 | 5 | | V-1 | B3GALT6 | 1.79 |
| 1158 | 3 | 4 | 5 | | V-1 | APOBEC3C | 1.53 | 1253 | 3 | 4 | 5 | | V-1 | BACH1 | 1.51 |
| 1159 | 3 | 4 | 5 | | V-1 | APOL1 | 1.55 | 1254 | 3 | 4 | 5 | | V-1 | BAG4 | 1.64 |
| 1160 | 3 | 4 | 5 | | V-1 | APOL6 | 1.53 | 1255 | 3 | 4 | 5 | | V-1 | BAHD1 | 1.56 |
| 1161 | 3 | 4 | 5 | | V-1 | APOPT1 | 1.53 | 1256 | 3 | 4 | 5 | | V-1 | BAIAP2 | 1.74 |
| 1162 | 3 | 4 | 5 | | V-1 | APPL1 | 1.77 | 1257 | 3 | 4 | 5 | | V-1 | BATF | 1.70 |
| 1163 | 3 | 4 | 5 | | V-1 | APRT | 1.66 | 1258 | 3 | 4 | 5 | | V-1 | BAX | 1.87 |
| 1164 | 3 | 4 | 5 | | V-1 | APTX | 1.60 | 1259 | 3 | 4 | 5 | | V-1 | BCAP29 | 1.52 |
| 1165 | 3 | 4 | 5 | | V-1 | AQR | 1.81 | 1260 | 3 | 4 | 5 | | V-1 | BCAS2 | 1.57 |
| 1166 | 3 | 4 | 5 | | V-1 | ARCN1 | 1.64 | 1261 | 3 | 4 | 5 | | V-1 | BCAT2 | 1.88 |
| 1167 | 3 | 4 | 5 | | V-1 | ARF1 | 1.57 | 1262 | 3 | 4 | 5 | | V-1 | BCCIP | 1.73 |
| 1168 | 3 | 4 | 5 | | V-1 | ARF3 | 1.59 | 1263 | 3 | 4 | 5 | | V-1 | BCKDK | 1.72 |
| 1169 | 3 | 4 | 5 | | V-1 | ARF4 | 1.51 | 1264 | 3 | 4 | 5 | | V-1 | BCL10 | 1.58 |
| 1170 | 3 | 4 | 5 | | V-1 | ARF6 | 1.79 | 1265 | 3 | 4 | 5 | | V-1 | BCL2L13 | 1.60 |
| 1171 | 3 | 4 | 5 | | V-1 | ARFGAP2 | 1.54 | 1266 | 3 | 4 | 5 | | V-1 | BCL2L2-PABPN1 | 1.75 |
| 1172 | 3 | 4 | 5 | | V-1 | ARFGAP3 | 1.55 | 1267 | 3 | 4 | 5 | | V-1 | BCL9 | 1.59 |
| 1173 | 3 | 4 | 5 | | V-1 | ARFGEF2 | 1.91 | 1268 | 3 | 4 | 5 | | V-1 | BDP1 | 1.50 |
| 1174 | 3 | 4 | 5 | | V-1 | ARFIP1 | 1.65 | 1269 | 3 | 4 | 5 | | V-1 | BECN1 | 1.56 |
| 1175 | 3 | 4 | 5 | | V-1 | ARFRP1 | 1.61 | 1270 | 3 | 4 | 5 | | V-1 | BFAR | 1.62 |
| 1176 | 3 | 4 | 5 | | V-1 | ARHGAP1 | 1.70 | 1271 | 3 | 4 | 5 | | V-1 | BHLHA15 | 1.51 |
| 1177 | 3 | 4 | 5 | | V-1 | ARHGAP11A | 1.74 | 1272 | 3 | 4 | 5 | | V-1 | BIK | 1.92 |
| 1178 | 3 | 4 | 5 | | V-1 | ARHGAP17 | 1.62 | 1273 | 3 | 4 | 5 | | V-1 | BIN1 | 1.51 |
| 1179 | 3 | 4 | 5 | | V-1 | ARHGAP22 | 1.94 | 1274 | 3 | 4 | 5 | | V-1 | BIRC6 | 1.60 |
| 1180 | 3 | 4 | 5 | | V-1 | ARHGAP26 | 1.53 | 1275 | 3 | 4 | 5 | | V-1 | BIVM | 1.57 |
| 1181 | 3 | 4 | 5 | | V-1 | ARHGAP35 | 1.65 | 1276 | 3 | 4 | 5 | | V-1 | BLMH | 1.98 |
| 1182 | 3 | 4 | 5 | | V-1 | ARHGEF11 | 1.87 | 1277 | 3 | 4 | 5 | | V-1 | BLOC1S2 | 1.55 |
| 1183 | 3 | 4 | 5 | | V-1 | ARHGEF6 | 1.58 | 1278 | 3 | 4 | 5 | | V-1 | BMF | 1.79 |
| 1184 | 3 | 4 | 5 | | V-1 | ARHGEF7 | 1.65 | 1279 | 3 | 4 | 5 | | V-1 | BMP2K | 1.74 |
| 1185 | 3 | 4 | 5 | | V-1 | ARID1B | 1.52 | 1280 | 3 | 4 | 5 | | V-1 | BMPR2 | 1.71 |
| 1186 | 3 | 4 | 5 | | V-1 | ARID4B | 1.52 | 1281 | 3 | 4 | 5 | | V-1 | BNIP2 | 1.85 |
| 1187 | 3 | 4 | 5 | | V-1 | ARL15 | 1.56 | 1282 | 3 | 4 | 5 | | V-1 | BNIP3L | 1.93 |
| 1188 | 3 | 4 | 5 | | V-1 | ARL2BP | 1.78 | 1283 | 3 | 4 | 5 | | V-1 | BOLA3 | 1.55 |
| 1189 | 3 | 4 | 5 | | V-1 | ARL6IP1 | 1.72 | 1284 | 3 | 4 | 5 | | V-1 | BOP1 | 1.91 |
| 1190 | 3 | 4 | 5 | | V-1 | ARL6IP5 | 1.51 | 1285 | 3 | 4 | 5 | | V-1 | BORA | 1.58 |
| 1191 | 3 | 4 | 5 | | V-1 | ARMC1 | 1.61 | 1286 | 3 | 4 | 5 | | V-1 | BRAP | 1.50 |
| 1192 | 3 | 4 | 5 | | V-1 | ARMC5 | 1.68 | 1287 | 3 | 4 | 5 | | V-1 | BRCA1 | 1.67 |
| 1193 | 3 | 4 | 5 | | V-1 | ARMC6 | 1.82 | 1288 | 3 | 4 | 5 | | V-1 | BRCC3 | 1.73 |
| 1194 | 3 | 4 | 5 | | V-1 | ARMC8 | 1.57 | 1289 | 3 | 4 | 5 | | V-1 | BRD3 | 1.54 |
| 1195 | 3 | 4 | 5 | | V-1 | ARMCX3 | 1.76 | 1290 | 3 | 4 | 5 | | V-1 | BRD9 | 1.75 |
| 1196 | 3 | 4 | 5 | | V-1 | ARNT | 1.86 | 1291 | 3 | 4 | 5 | | V-1 | BRF1 | 1.55 |
| 1197 | 3 | 4 | 5 | | V-1 | ARPC1A | 1.54 | 1292 | 3 | 4 | 5 | | V-1 | BRI3 | 1.75 |
| 1198 | 3 | 4 | 5 | | V-1 | ARPC1B | 1.91 | 1293 | 3 | 4 | 5 | | V-1 | BROX | 1.65 |
| 1199 | 3 | 4 | 5 | | V-1 | ARPC4 | 1.51 | 1294 | 3 | 4 | 5 | | V-1 | BSCL2 | 1.66 |
| 1200 | 3 | 4 | 5 | | V-1 | ARPC5 | 1.52 | 1295 | 3 | 4 | 5 | | V-1 | BSG | 1.53 |
| 1201 | 3 | 4 | 5 | | V-1 | ASB3 | 1.63 | 1296 | 3 | 4 | 5 | | V-1 | BTBD1 | 1.55 |
| 1202 | 3 | 4 | 5 | | V-1 | ASF1A | 1.50 | 1297 | 3 | 4 | 5 | | V-1 | BTBD9 | 1.82 |
| 1203 | 3 | 4 | 5 | | V-1 | ASH2L | 1.55 | 1298 | 3 | 4 | 5 | | V-1 | BTD | 1.70 |
| 1204 | 3 | 4 | 5 | | V-1 | ASL | 1.70 | 1299 | 3 | 4 | 5 | | V-1 | BTK | 1.88 |
| 1205 | 3 | 4 | 5 | | V-1 | ASPHD2 | 1.83 | 1300 | 3 | 4 | 5 | | V-1 | BTRC | 1.51 |
| 1206 | 3 | 4 | 5 | | V-1 | ASUN | 1.59 | 1301 | 3 | 4 | 5 | | V-1 | BZW1 | 1.94 |
| 1207 | 3 | 4 | 5 | | V-1 | ASXL2 | 1.66 | 1302 | 3 | 4 | 5 | | V-1 | BZW2 | 1.58 |
| 1208 | 3 | 4 | 5 | | V-1 | ATAD2B | 1.69 | 1303 | 3 | 4 | 5 | | V-1 | C10orf32 | 1.69 |
| 1209 | 3 | 4 | 5 | | V-1 | ATF2 | 1.74 | 1304 | 3 | 4 | 5 | | V-1 | C10orf76 | 1.96 |
| 1210 | 3 | 4 | 5 | | V-1 | ATF6 | 1.76 | 1305 | 3 | 4 | 5 | | V-1 | C10orf88 | 1.70 |
| 1211 | 3 | 4 | 5 | | V-1 | ATF6B | 1.58 | 1306 | 3 | 4 | 5 | | V-1 | C11orf24 | 1.56 |
| 1212 | 3 | 4 | 5 | | V-1 | ATF7IP | 1.64 | 1307 | 3 | 4 | 5 | | V-1 | C11orf48 | 1.54 |
| 1213 | 3 | 4 | 5 | | V-1 | ATG4C | 1.66 | 1308 | 3 | 4 | 5 | | V-1 | C11orf58 | 1.73 |
| 1214 | 3 | 4 | 5 | | V-1 | ATMIN | 1.64 | 1309 | 3 | 4 | 5 | | V-1 | C12orf44 | 1.54 |
| 1215 | 3 | 4 | 5 | | V-1 | ATP10A | 1.53 | 1310 | 3 | 4 | 5 | | V-1 | C12orf5 | 1.67 |
| 1216 | 3 | 4 | 5 | | V-1 | ATP10D | 1.64 | 1311 | 3 | 4 | 5 | | V-1 | C14orf102 | 1.85 |
| 1217 | 3 | 4 | 5 | | V-1 | ATP11A | 1.70 | 1312 | 3 | 4 | 5 | | V-1 | C14orf109 | 1.53 |
| 1218 | 3 | 4 | 5 | | V-1 | ATP11C | 1.55 | 1313 | 3 | 4 | 5 | | V-1 | C14orf126 | 1.52 |
| 1219 | 3 | 4 | 5 | | V-1 | ATP13A1 | 1.63 | 1314 | 3 | 4 | 5 | | V-1 | C14orf132 | 1.53 |
| 1220 | 3 | 4 | 5 | | V-1 | ATP13A2 | 1.82 | 1315 | 3 | 4 | 5 | | V-1 | C14orf133 | 1.63 |
| 1221 | 3 | 4 | 5 | | V-1 | ATP2B1 | 1.56 | 1316 | 3 | 4 | 5 | | V-1 | C14orf166 | 1.52 |
| 1222 | 3 | 4 | 5 | | V-1 | ATP2B4 | 1.90 | 1317 | 3 | 4 | 5 | | V-1 | C14orf169 | 1.55 |
| 1223 | 3 | 4 | 5 | | V-1 | ATP2C1 | 1.83 | 1318 | 3 | 4 | 5 | | V-1 | C14orf2 | 1.52 |
| 1224 | 3 | 4 | 5 | | V-1 | ATP5C1 | 1.54 | 1319 | 3 | 4 | 5 | | V-1 | C14orf49 | 1.63 |
| 1225 | 3 | 4 | 5 | | V-1 | ATP5F1 | 1.63 | 1320 | 3 | 4 | 5 | | V-1 | C14orf80 | 1.90 |
| 1226 | 3 | 4 | 5 | | V-1 | ATP5G2 | 1.72 | 1321 | 3 | 4 | 5 | | V-1 | C15orf24 | 1.51 |
| 1227 | 3 | 4 | 5 | | V-1 | ATP5G3 | 1.89 | 1322 | 3 | 4 | 5 | | V-1 | C15orf58 | 1.93 |
| 1228 | 3 | 4 | 5 | | V-1 | ATP5J | 1.79 | 1323 | 3 | 4 | 5 | | V-1 | C16orf87 | 1.65 |
| 1229 | 3 | 4 | 5 | | V-1 | ATP5J2 | 1.93 | 1324 | 3 | 4 | 5 | | V-1 | C16orf88 | 1.83 |
| 1230 | 3 | 4 | 5 | | V-1 | ATP5L | 1.60 | 1325 | 3 | 4 | 5 | | V-1 | C17orf70 | 1.58 |
| 1231 | 3 | 4 | 5 | | V-1 | ATP5SL | 1.52 | 1326 | 3 | 4 | 5 | | V-1 | C18orf21 | 1.75 |
| 1232 | 3 | 4 | 5 | | V-1 | ATP6AP1 | 1.94 | 1327 | 3 | 4 | 5 | | V-1 | C19orf10 | 1.98 |
| 1233 | 3 | 4 | 5 | | V-1 | ATP6V0A1 | 1.65 | 1328 | 3 | 4 | 5 | | V-1 | C19orf42 | 1.87 |
| 1234 | 3 | 4 | 5 | | V-1 | ATP6V0D1 | 1.64 | 1329 | 3 | 4 | 5 | | V-1 | C19orf52 | 1.61 |
| 1235 | 3 | 4 | 5 | | V-1 | ATP6V1A | 1.68 | 1330 | 3 | 4 | 5 | | V-1 | C1GALT1C1 | 1.61 |
| 1236 | 3 | 4 | 5 | | V-1 | ATP6V1B2 | 1.54 | 1331 | 3 | 4 | 5 | | V-1 | C1orf109 | 1.62 |
| 1237 | 3 | 4 | 5 | | V-1 | ATP6V1C1 | 1.67 | 1332 | 3 | 4 | 5 | | V-1 | C1orf122 | 1.70 |
| 1238 | 3 | 4 | 5 | | V-1 | ATP6V1E1 | 1.78 | 1333 | 3 | 4 | 5 | | V-1 | C1orf216 | 1.63 |
| 1239 | 3 | 4 | 5 | | V-1 | ATP6V1E2 | 1.85 | 1334 | 3 | 4 | 5 | | V-1 | C1orf27 | 1.54 |
| 1240 | 3 | 4 | 5 | | V-1 | ATP6V1G2-DDX39B | 1.53 | 1335 | 3 | 4 | 5 | | V-1 | C1orf31 | 1.69 |
| | | | | | | | | 1336 | 3 | 4 | 5 | | V-1 | C1orf35 | 1.71 |
| 1241 | 3 | 4 | 5 | | V-1 | ATP6V1H | 1.89 | 1337 | 3 | 4 | 5 | | V-1 | C1orf38 | 1.55 |
| 1242 | 3 | 4 | 5 | | V-1 | ATPAF1 | 1.87 | 1338 | 3 | 4 | 5 | | V-1 | C20orf11 | 1.51 |
| 1243 | 3 | 4 | 5 | | V-1 | ATPAF2 | 1.82 | 1339 | 3 | 4 | 5 | | V-1 | C20orf29 | 1.85 |
| 1244 | 3 | 4 | 5 | | V-1 | ATPBD4 | 1.65 | 1340 | 3 | 4 | 5 | | V-1 | C20orf3 | 1.56 |
| 1245 | 3 | 4 | 5 | | V-1 | ATR | 1.62 | 1341 | 3 | 4 | 5 | | V-1 | C20orf30 | 1.54 |

Fig. 41 - 8

| | | | | | | | | | | | | | | | |
|---|---|---|---|---|---|---|---|---|---|---|---|---|---|---|---|
| 1342 | 3 | 4 | 5 | | V-1 | C21orf119 | 1.71 | 1438 | 3 | 4 | 5 | | V-1 | CDC40 | 1.80 |
| 1343 | 3 | 4 | 5 | | V-1 | C21orf59 | 1.79 | 1439 | 3 | 4 | 5 | | V-1 | CDC5L | 1.53 |
| 1344 | 3 | 4 | 5 | | V-1 | C2CD2L | 1.60 | 1440 | 3 | 4 | 5 | | V-1 | CDC73 | 1.67 |
| 1345 | 3 | 4 | 5 | | V-1 | C2orf29 | 1.71 | 1441 | 3 | 4 | 5 | | V-1 | CDCA5 | 1.82 |
| 1346 | 3 | 4 | 5 | | V-1 | C2orf42 | 1.54 | 1442 | 3 | 4 | 5 | | V-1 | CDCA7 | 1.73 |
| 1347 | 3 | 4 | 5 | | V-1 | C2orf43 | 1.84 | 1443 | 3 | 4 | 5 | | V-1 | CDK2AP1 | 1.54 |
| 1348 | 3 | 4 | 5 | | V-1 | C2orf47 | 1.56 | 1444 | 3 | 4 | 5 | | V-1 | CDK4 | 1.51 |
| 1349 | 3 | 4 | 5 | | V-1 | C3orf38 | 1.61 | 1445 | 3 | 4 | 5 | | V-1 | CDK5 | 1.57 |
| 1350 | 3 | 4 | 5 | | V-1 | C3orf58 | 1.98 | 1446 | 3 | 4 | 5 | | V-1 | CDK8 | 1.79 |
| 1351 | 3 | 4 | 5 | | V-1 | C4orf33 | 1.64 | 1447 | 3 | 4 | 5 | | V-1 | CDKN2AIPNL | 1.53 |
| 1352 | 3 | 4 | 5 | | V-1 | C5orf15 | 1.52 | 1448 | 3 | 4 | 5 | | V-1 | CDKN2C | 1.61 |
| 1353 | 3 | 4 | 5 | | V-1 | C5orf22 | 1.77 | 1449 | 3 | 4 | 5 | | V-1 | CD52 | 1.58 |
| 1354 | 3 | 4 | 5 | | V-1 | C5orf24 | 1.56 | 1450 | 3 | 4 | 5 | | V-1 | CDYL | 1.63 |
| 1355 | 3 | 4 | 5 | | V-1 | C5orf28 | 1.57 | 1451 | 3 | 4 | 5 | | V-1 | CEBPA | 1.98 |
| 1356 | 3 | 4 | 5 | | V-1 | C6orf108 | 1.74 | 1452 | 3 | 4 | 5 | | V-1 | CEBPG | 1.99 |
| 1357 | 3 | 4 | 5 | | V-1 | C6orf115 | 1.83 | 1453 | 3 | 4 | 5 | | V-1 | CEBPZ | 1.60 |
| 1358 | 3 | 4 | 5 | | V-1 | C6orf120 | 1.91 | 1454 | 3 | 4 | 5 | | V-1 | CECR5 | 1.95 |
| 1359 | 3 | 4 | 5 | | V-1 | C6orf203 | 1.51 | 1455 | 3 | 4 | 5 | | V-1 | CECR6 | 1.74 |
| 1360 | 3 | 4 | 5 | | V-1 | C6orf211 | 1.94 | 1456 | 3 | 4 | 5 | | V-1 | CEP135 | 1.88 |
| 1361 | 3 | 4 | 5 | | V-1 | C6orf226 | 1.95 | 1457 | 3 | 4 | 5 | | V-1 | CEP170 | 1.95 |
| 1362 | 3 | 4 | 5 | | V-1 | C6orf228 | 1.93 | 1458 | 3 | 4 | 5 | | V-1 | CEP350 | 1.59 |
| 1363 | 3 | 4 | 5 | | V-1 | C6orf62 | 1.65 | 1459 | 3 | 4 | 5 | | V-1 | CEP76 | 1.70 |
| 1364 | 3 | 4 | 5 | | V-1 | C6orf72 | 1.78 | 1460 | 3 | 4 | 5 | | V-1 | CEPT1 | 1.70 |
| 1365 | 3 | 4 | 5 | | V-1 | C7orf31 | 1.55 | 1461 | 3 | 4 | 5 | | V-1 | CERS2 | 1.91 |
| 1366 | 3 | 4 | 5 | | V-1 | C7orf42 | 1.55 | 1462 | 3 | 4 | 5 | | V-1 | CES2 | 1.80 |
| 1367 | 3 | 4 | 5 | | V-1 | C7orf73 | 1.56 | 1463 | 3 | 4 | 5 | | V-1 | CFDP1 | 1.76 |
| 1368 | 3 | 4 | 5 | | V-1 | C8orf33 | 1.56 | 1464 | 3 | 4 | 5 | | V-1 | CGRRF1 | 1.61 |
| 1369 | 3 | 4 | 5 | | V-1 | C8orf82 | 1.73 | 1465 | 3 | 4 | 5 | | V-1 | CHAF1A | 1.62 |
| 1370 | 3 | 4 | 5 | | V-1 | C8orf83 | 1.93 | 1466 | 3 | 4 | 5 | | V-1 | CHAMP1 | 1.92 |
| 1371 | 3 | 4 | 5 | | V-1 | C9orf129 | 1.98 | 1467 | 3 | 4 | 5 | | V-1 | CHCHD1 | 1.66 |
| 1372 | 3 | 4 | 5 | | V-1 | C9orf41 | 1.52 | 1468 | 3 | 4 | 5 | | V-1 | CHCHD2 | 1.67 |
| 1373 | 3 | 4 | 5 | | V-1 | C9orf64 | 1.97 | 1469 | 3 | 4 | 5 | | V-1 | CHD4 | 1.72 |
| 1374 | 3 | 4 | 5 | | V-1 | C9orf7 | 1.51 | 1470 | 3 | 4 | 5 | | V-1 | CHM | 1.81 |
| 1375 | 3 | 4 | 5 | | V-1 | C9orf72 | 1.60 | 1471 | 3 | 4 | 5 | | V-1 | CHMP2B | 1.59 |
| 1376 | 3 | 4 | 5 | | V-1 | C9orf78 | 1.67 | 1472 | 3 | 4 | 5 | | V-1 | CHMP4B | 1.70 |
| 1377 | 3 | 4 | 5 | | V-1 | C9orf80 | 1.61 | 1473 | 3 | 4 | 5 | | V-1 | CHMP5 | 1.74 |
| 1378 | 3 | 4 | 5 | | V-1 | C9orf86 | 1.72 | 1474 | 3 | 4 | 5 | | V-1 | CHORDC1 | 1.83 |
| 1379 | 3 | 4 | 5 | | V-1 | CA5BP1 | 1.51 | 1475 | 3 | 4 | 5 | | V-1 | CHPF | 1.54 |
| 1380 | 3 | 4 | 5 | | V-1 | CAB39 | 1.65 | 1476 | 3 | 4 | 5 | | V-1 | CHST14 | 1.78 |
| 1381 | 3 | 4 | 5 | | V-1 | CACNA2D4 | 1.59 | 1477 | 3 | 4 | 5 | | V-1 | CHST15 | 1.54 |
| 1382 | 3 | 4 | 5 | | V-1 | CACYBP | 1.52 | 1478 | 3 | 4 | 5 | | V-1 | CHTF8 | 1.68 |
| 1383 | 3 | 4 | 5 | | V-1 | CAD | 1.89 | 1479 | 3 | 4 | 5 | | V-1 | CIAPIN1 | 1.57 |
| 1384 | 3 | 4 | 5 | | V-1 | CALCOCO2 | 1.69 | 1480 | 3 | 4 | 5 | | V-1 | CIRH1A | 1.88 |
| 1385 | 3 | 4 | 5 | | V-1 | CALM1 | 1.58 | 1481 | 3 | 4 | 5 | | V-1 | CISD1 | 1.69 |
| 1386 | 3 | 4 | 5 | | V-1 | CALM2 | 1.58 | 1482 | 3 | 4 | 5 | | V-1 | CISD2 | 1.53 |
| 1387 | 3 | 4 | 5 | | V-1 | CALU | 1.96 | 1483 | 3 | 4 | 5 | | V-1 | CISH | 1.56 |
| 1388 | 3 | 4 | 5 | | V-1 | CAMK2B | 1.73 | 1484 | 3 | 4 | 5 | | V-1 | CITED2 | 1.55 |
| 1389 | 3 | 4 | 5 | | V-1 | CAMKK2 | 1.80 | 1485 | 3 | 4 | 5 | | V-1 | CKAP2 | 1.58 |
| 1390 | 3 | 4 | 5 | | V-1 | CAP1 | 1.56 | 1486 | 3 | 4 | 5 | | V-1 | CKAP4 | 1.96 |
| 1391 | 3 | 4 | 5 | | V-1 | CAPN1 | 1.66 | 1487 | 3 | 4 | 5 | | V-1 | CLASP2 | 1.92 |
| 1392 | 3 | 4 | 5 | | V-1 | CAPNS1 | 1.99 | 1488 | 3 | 4 | 5 | | V-1 | CLCN3 | 1.94 |
| 1393 | 3 | 4 | 5 | | V-1 | CAPZA1 | 1.51 | 1489 | 3 | 4 | 5 | | V-1 | CLCN6 | 1.76 |
| 1394 | 3 | 4 | 5 | | V-1 | CAPZA2 | 1.63 | 1490 | 3 | 4 | 5 | | V-1 | CLDN23 | 1.75 |
| 1395 | 3 | 4 | 5 | | V-1 | CARD16 | 1.50 | 1491 | 3 | 4 | 5 | | V-1 | CLEC16A | 1.61 |
| 1396 | 3 | 4 | 5 | | V-1 | CASP1 | 1.56 | 1492 | 3 | 4 | 5 | | V-1 | CLEC4G | 1.57 |
| 1397 | 3 | 4 | 5 | | V-1 | CASP10 | 1.98 | 1493 | 3 | 4 | 5 | | V-1 | CLIC2 | 1.60 |
| 1398 | 3 | 4 | 5 | | V-1 | CASP6 | 1.73 | 1494 | 3 | 4 | 5 | | V-1 | CLINT1 | 1.52 |
| 1399 | 3 | 4 | 5 | | V-1 | CASP7 | 1.79 | 1495 | 3 | 4 | 5 | | V-1 | CLIP2 | 1.67 |
| 1400 | 3 | 4 | 5 | | V-1 | CBFB | 1.97 | 1496 | 3 | 4 | 5 | | V-1 | CLN3 | 1.88 |
| 1401 | 3 | 4 | 5 | | V-1 | CBL | 1.55 | 1497 | 3 | 4 | 5 | | V-1 | CLN5 | 1.66 |
| 1402 | 3 | 4 | 5 | | V-1 | CBX3 | 1.57 | 1498 | 3 | 4 | 5 | | V-1 | CLN8 | 1.60 |
| 1403 | 3 | 4 | 5 | | V-1 | CBX6 | 1.80 | 1499 | 3 | 4 | 5 | | V-1 | CLOCK | 1.69 |
| 1404 | 3 | 4 | 5 | | V-1 | CC2D1A | 1.51 | 1500 | 3 | 4 | 5 | | V-1 | CLPTM1L | 1.73 |
| 1405 | 3 | 4 | 5 | | V-1 | CCDC111 | 1.55 | 1501 | 3 | 4 | 5 | | V-1 | CLSTN1 | 1.86 |
| 1406 | 3 | 4 | 5 | | V-1 | CCDC112 | 1.77 | 1502 | 3 | 4 | 5 | | V-1 | CLUAP1 | 1.59 |
| 1407 | 3 | 4 | 5 | | V-1 | CCDC12 | 1.89 | 1503 | 3 | 4 | 5 | | V-1 | CMKLR1 | 1.71 |
| 1408 | 3 | 4 | 5 | | V-1 | CCDC132 | 1.65 | 1504 | 3 | 4 | 5 | | V-1 | CMTM7 | 1.90 |
| 1409 | 3 | 4 | 5 | | V-1 | CCDC142 | 1.66 | 1505 | 3 | 4 | 5 | | V-1 | CNNM4 | 1.60 |
| 1410 | 3 | 4 | 5 | | V-1 | CCDC34 | 1.65 | 1506 | 3 | 4 | 5 | | V-1 | CNOT1 | 1.50 |
| 1411 | 3 | 4 | 5 | | V-1 | CCDC56 | 1.50 | 1507 | 3 | 4 | 5 | | V-1 | CNOT2 | 1.81 |
| 1412 | 3 | 4 | 5 | | V-1 | CCDC77 | 1.60 | 1508 | 3 | 4 | 5 | | V-1 | CNOT4 | 1.60 |
| 1413 | 3 | 4 | 5 | | V-1 | CCDC91 | 1.63 | 1509 | 3 | 4 | 5 | | V-1 | CNOT6 | 1.73 |
| 1414 | 3 | 4 | 5 | | V-1 | CCDC93 | 1.55 | 1510 | 3 | 4 | 5 | | V-1 | CNOT8 | 1.56 |
| 1415 | 3 | 4 | 5 | | V-1 | CCND2 | 1.59 | 1511 | 3 | 4 | 5 | | V-1 | CNTLN | 1.89 |
| 1416 | 3 | 4 | 5 | | V-1 | CCNG1 | 1.55 | 1512 | 3 | 4 | 5 | | V-1 | COG2 | 1.63 |
| 1417 | 3 | 4 | 5 | | V-1 | CCNJ | 1.77 | 1513 | 3 | 4 | 5 | | V-1 | COG5 | 1.64 |
| 1418 | 3 | 4 | 5 | | V-1 | CCNY | 1.59 | 1514 | 3 | 4 | 5 | | V-1 | COG6 | 1.75 |
| 1419 | 3 | 4 | 5 | | V-1 | CCNYL1 | 1.66 | 1515 | 3 | 4 | 5 | | V-1 | COG8 | 1.69 |
| 1420 | 3 | 4 | 5 | | V-1 | CCRN4L | 1.69 | 1516 | 3 | 4 | 5 | | V-1 | COIL | 1.65 |
| 1421 | 3 | 4 | 5 | | V-1 | CCT2 | 1.88 | 1517 | 3 | 4 | 5 | | V-1 | COL4A3BP | 1.98 |
| 1422 | 3 | 4 | 5 | | V-1 | CCT5 | 1.85 | 1518 | 3 | 4 | 5 | | V-1 | COMMD1 | 1.75 |
| 1423 | 3 | 4 | 5 | | V-1 | CD164 | 1.80 | 1519 | 3 | 4 | 5 | | V-1 | COMMD4 | 1.53 |
| 1424 | 3 | 4 | 5 | | V-1 | CD1D | 1.64 | 1520 | 3 | 4 | 5 | | V-1 | COMMD5 | 1.60 |
| 1425 | 3 | 4 | 5 | | V-1 | CD2AP | 1.84 | 1521 | 3 | 4 | 5 | | V-1 | COPB1 | 1.87 |
| 1426 | 3 | 4 | 5 | | V-1 | CD300LB | 1.99 | 1522 | 3 | 4 | 5 | | V-1 | COPB2 | 1.93 |
| 1427 | 3 | 4 | 5 | | V-1 | CD302 | 1.74 | 1523 | 3 | 4 | 5 | | V-1 | COPG1 | 1.93 |
| 1428 | 3 | 4 | 5 | | V-1 | CD52 | 1.76 | 1524 | 3 | 4 | 5 | | V-1 | COPS2 | 1.69 |
| 1429 | 3 | 4 | 5 | | V-1 | CD53 | 1.53 | 1525 | 3 | 4 | 5 | | V-1 | COPS4 | 1.95 |
| 1430 | 3 | 4 | 5 | | V-1 | CD63 | 1.73 | 1526 | 3 | 4 | 5 | | V-1 | COPS6 | 1.78 |
| 1431 | 3 | 4 | 5 | | V-1 | CD81 | 1.78 | 1527 | 3 | 4 | 5 | | V-1 | COPS7A | 1.54 |
| 1432 | 3 | 4 | 5 | | V-1 | CD99 | 1.72 | 1528 | 3 | 4 | 5 | | V-1 | COQ2 | 1.69 |
| 1433 | 3 | 4 | 5 | | V-1 | CD99L2 | 1.87 | 1529 | 3 | 4 | 5 | | V-1 | COQ5 | 1.84 |
| 1434 | 3 | 4 | 5 | | V-1 | CDADC1 | 1.55 | 1530 | 3 | 4 | 5 | | V-1 | COTL1 | 1.53 |
| 1435 | 3 | 4 | 5 | | V-1 | CDC16 | 1.63 | 1531 | 3 | 4 | 5 | | V-1 | COX10 | 1.61 |
| 1436 | 3 | 4 | 5 | | V-1 | CDC23 | 1.58 | 1532 | 3 | 4 | 5 | | V-1 | COX15 | 2.00 |
| 1437 | 3 | 4 | 5 | | V-1 | CDC27 | 1.75 | 1533 | 3 | 4 | 5 | | V-1 | COX16 | 1.63 |

Fig. 41 - 9

| | | | | | | | | | | | | | | | |
|---|---|---|---|---|---|---|---|---|---|---|---|---|---|---|---|
| 1534 | 3 | 4 | 5 | | V-1 | COX17 | 1.50 | 1630 | 3 | 4 | 5 | | V-1 | DHX33 | 1.80 |
| 1535 | 3 | 4 | 5 | | V-1 | COX4NB | 1.93 | 1631 | 3 | 4 | 5 | | V-1 | DHX37 | 1.94 |
| 1536 | 3 | 4 | 5 | | V-1 | COX6B1 | 1.53 | 1632 | 3 | 4 | 5 | | V-1 | DHX38 | 1.61 |
| 1537 | 3 | 4 | 5 | | V-1 | COX8A | 1.69 | 1633 | 3 | 4 | 5 | | V-1 | DHX40 | 1.62 |
| 1538 | 3 | 4 | 5 | | V-1 | CPNE2 | 1.82 | 1634 | 3 | 4 | 5 | | V-1 | DHX58 | 1.64 |
| 1539 | 3 | 4 | 5 | | V-1 | CPNE3 | 1.70 | 1635 | 3 | 4 | 5 | | V-1 | DHX8 | 1.59 |
| 1540 | 3 | 4 | 5 | | V-1 | CPOX | 1.72 | 1636 | 3 | 4 | 5 | | V-1 | DHX9 | 1.74 |
| 1541 | 3 | 4 | 5 | | V-1 | CPSF1 | 1.52 | 1637 | 3 | 4 | 5 | | V-1 | DIAPH1 | 1.67 |
| 1542 | 3 | 4 | 5 | | V-1 | CPSF2 | 1.83 | 1638 | 3 | 4 | 5 | | V-1 | DICER1 | 1.59 |
| 1543 | 3 | 4 | 5 | | V-1 | CPSF3L | 1.69 | 1639 | 3 | 4 | 5 | | V-1 | DIRC2 | 1.93 |
| 1544 | 3 | 4 | 5 | | V-1 | CPSF4 | 1.56 | 1640 | 3 | 4 | 5 | | V-1 | DIS3 | 1.54 |
| 1545 | 3 | 4 | 5 | | V-1 | CPT2 | 1.98 | 1641 | 3 | 4 | 5 | | V-1 | DIS3L2 | 1.82 |
| 1546 | 3 | 4 | 5 | | V-1 | CREBL2 | 1.71 | 1642 | 3 | 4 | 5 | | V-1 | DKC1 | 1.57 |
| 1547 | 3 | 4 | 5 | | V-1 | CRELD2 | 1.73 | 1643 | 3 | 4 | 5 | | V-1 | DLAT | 1.82 |
| 1548 | 3 | 4 | 5 | | V-1 | CRIM1 | 1.76 | 1644 | 3 | 4 | 5 | | V-1 | DNAJA1 | 1.56 |
| 1549 | 3 | 4 | 5 | | V-1 | CRISP3 | 1.90 | 1645 | 3 | 4 | 5 | | V-1 | DNAJC1 | 1.58 |
| 1550 | 3 | 4 | 5 | | V-1 | CRLS1 | 1.81 | 1646 | 3 | 4 | 5 | | V-1 | DNAJC15 | 1.85 |
| 1551 | 3 | 4 | 5 | | V-1 | CRTAP | 1.95 | 1647 | 3 | 4 | 5 | | V-1 | DNAJC16 | 1.85 |
| 1552 | 3 | 4 | 5 | | V-1 | CRTC3 | 1.84 | 1648 | 3 | 4 | 5 | | V-1 | DNAJC3 | 1.58 |
| 1553 | 3 | 4 | 5 | | V-1 | CRYL1 | 1.61 | 1649 | 3 | 4 | 5 | | V-1 | DNAJC5 | 1.78 |
| 1554 | 3 | 4 | 5 | | V-1 | CS | 1.72 | 1650 | 3 | 4 | 5 | | V-1 | DOCK2 | 1.93 |
| 1555 | 3 | 4 | 5 | | V-1 | CSDE1 | 1.70 | 1651 | 3 | 4 | 5 | | V-1 | DOCK8 | 1.67 |
| 1556 | 3 | 4 | 5 | | V-1 | CSK | 1.94 | 1652 | 3 | 4 | 5 | | V-1 | DOK2 | 1.70 |
| 1557 | 3 | 4 | 5 | | V-1 | CSNK1A1 | 1.62 | 1653 | 3 | 4 | 5 | | V-1 | DOLK | 1.92 |
| 1558 | 3 | 4 | 5 | | V-1 | CSNK1A1P1 | 1.62 | 1654 | 3 | 4 | 5 | | V-1 | DOPEY2 | 1.59 |
| 1559 | 3 | 4 | 5 | | V-1 | CSNK1G1 | 1.53 | 1655 | 3 | 4 | 5 | | V-1 | DOT1L | 1.61 |
| 1560 | 3 | 4 | 5 | | V-1 | CSNK2A1P | 1.65 | 1656 | 3 | 4 | 5 | | V-1 | DPP7 | 1.52 |
| 1561 | 3 | 4 | 5 | | V-1 | CSNK2A2 | 1.82 | 1657 | 3 | 4 | 5 | | V-1 | DPP9 | 1.51 |
| 1562 | 3 | 4 | 5 | | V-1 | CSPP1 | 1.83 | 1658 | 3 | 4 | 5 | | V-1 | DPY19L1 | 1.60 |
| 1563 | 3 | 4 | 5 | | V-1 | CSTB | 1.63 | 1659 | 3 | 4 | 5 | | V-1 | DPY19L3 | 1.95 |
| 1564 | 3 | 4 | 5 | | V-1 | CSTF2 | 1.58 | 1660 | 3 | 4 | 5 | | V-1 | DRAM2 | 1.51 |
| 1565 | 3 | 4 | 5 | | V-1 | CSTF2T | 1.65 | 1661 | 3 | 4 | 5 | | V-1 | DSC1 | 1.76 |
| 1566 | 3 | 4 | 5 | | V-1 | CTAGE11P | 1.55 | 1662 | 3 | 4 | 5 | | V-1 | DSTNP2 | 1.91 |
| 1567 | 3 | 4 | 5 | | V-1 | CTDNEP1 | 1.71 | 1663 | 3 | 4 | 5 | | V-1 | DSTYK | 1.97 |
| 1568 | 3 | 4 | 5 | | V-1 | CTDP1 | 1.52 | 1664 | 3 | 4 | 5 | | V-1 | DTWD1 | 1.69 |
| 1569 | 3 | 4 | 5 | | V-1 | CTNNB1 | 1.92 | 1665 | 3 | 4 | 5 | | V-1 | DUSP7 | 1.78 |
| 1570 | 3 | 4 | 5 | | V-1 | CTNNBL1 | 1.73 | 1666 | 3 | 4 | 5 | | V-1 | DVL2 | 1.50 |
| 1571 | 3 | 4 | 5 | | V-1 | CTNS | 1.83 | 1667 | 3 | 4 | 5 | | V-1 | DYM | 1.64 |
| 1572 | 3 | 4 | 5 | | V-1 | CTPS | 1.81 | 1668 | 3 | 4 | 5 | | V-1 | DYNC1H1 | 1.85 |
| 1573 | 3 | 4 | 5 | | V-1 | CTSC | 1.64 | 1669 | 3 | 4 | 5 | | V-1 | DYNLL1 | 1.73 |
| 1574 | 3 | 4 | 5 | | V-1 | CTU1 | 1.69 | 1670 | 3 | 4 | 5 | | V-1 | DYNLL2 | 1.53 |
| 1575 | 3 | 4 | 5 | | V-1 | CUEDC2 | 1.75 | 1671 | 3 | 4 | 5 | | V-1 | DYRK4 | 1.81 |
| 1576 | 3 | 4 | 5 | | V-1 | CUL2 | 1.72 | 1672 | 3 | 4 | 5 | | V-1 | E2F1 | 1.53 |
| 1577 | 3 | 4 | 5 | | V-1 | CUL3 | 1.59 | 1673 | 3 | 4 | 5 | | V-1 | EAF1 | 1.67 |
| 1578 | 3 | 4 | 5 | | V-1 | CWC27 | 1.66 | 1674 | 3 | 4 | 5 | | V-1 | EAF2 | 1.75 |
| 1579 | 3 | 4 | 5 | | V-1 | CWF19L2 | 1.89 | 1675 | 3 | 4 | 5 | | V-1 | EARS2 | 1.74 |
| 1580 | 3 | 4 | 5 | | V-1 | CXorf21 | 1.56 | 1676 | 3 | 4 | 5 | | V-1 | EBNA1BP2 | 1.69 |
| 1581 | 3 | 4 | 5 | | V-1 | CXorf26 | 1.51 | 1677 | 3 | 4 | 5 | | V-1 | EBPL | 1.90 |
| 1582 | 3 | 4 | 5 | | V-1 | CXorf40B | 1.52 | 1678 | 3 | 4 | 5 | | V-1 | ECHDC1 | 1.94 |
| 1583 | 3 | 4 | 5 | | V-1 | CYB561D2 | 1.57 | 1679 | 3 | 4 | 5 | | V-1 | ECI1 | 1.83 |
| 1584 | 3 | 4 | 5 | | V-1 | CYB5B | 1.62 | 1680 | 3 | 4 | 5 | | V-1 | EDA | 1.91 |
| 1585 | 3 | 4 | 5 | | V-1 | CYCS | 1.61 | 1681 | 3 | 4 | 5 | | V-1 | EDC4 | 1.66 |
| 1586 | 3 | 4 | 5 | | V-1 | CYP20A1 | 1.51 | 1682 | 3 | 4 | 5 | | V-1 | EDEM2 | 1.54 |
| 1587 | 3 | 4 | 5 | | V-1 | DAB2 | 1.59 | 1683 | 3 | 4 | 5 | | V-1 | EDEM3 | 1.80 |
| 1588 | 3 | 4 | 5 | | V-1 | DAG1 | 1.82 | 1684 | 3 | 4 | 5 | | V-1 | EEA1 | 1.55 |
| 1589 | 3 | 4 | 5 | | V-1 | DAGLA | 1.80 | 1685 | 3 | 4 | 5 | | V-1 | EED | 1.61 |
| 1590 | 3 | 4 | 5 | | V-1 | DAGLB | 1.77 | 1686 | 3 | 4 | 5 | | V-1 | EEF2 | 1.51 |
| 1591 | 3 | 4 | 5 | | V-1 | DALRD3 | 1.62 | 1687 | 3 | 4 | 5 | | V-1 | EFNA4 | 1.78 |
| 1592 | 3 | 4 | 5 | | V-1 | DARS2 | 1.92 | 1688 | 3 | 4 | 5 | | V-1 | EFR3A | 1.92 |
| 1593 | 3 | 4 | 5 | | V-1 | DAZAP1 | 1.73 | 1689 | 3 | 4 | 5 | | V-1 | EFTUD1 | 1.54 |
| 1594 | 3 | 4 | 5 | | V-1 | DBNL | 1.51 | 1690 | 3 | 4 | 5 | | V-1 | EHHADH | 1.80 |
| 1595 | 3 | 4 | 5 | | V-1 | DBT | 1.89 | 1691 | 3 | 4 | 5 | | V-1 | EI24 | 1.67 |
| 1596 | 3 | 4 | 5 | | V-1 | DCAF10 | 1.51 | 1692 | 3 | 4 | 5 | | V-1 | EID1 | 1.74 |
| 1597 | 3 | 4 | 5 | | V-1 | DCAKD | 1.76 | 1693 | 3 | 4 | 5 | | V-1 | EID2 | 1.71 |
| 1598 | 3 | 4 | 5 | | V-1 | DCHS1 | 1.52 | 1694 | 3 | 4 | 5 | | V-1 | EIF2A | 1.99 |
| 1599 | 3 | 4 | 5 | | V-1 | DCLRE1B | 1.68 | 1695 | 3 | 4 | 5 | | V-1 | EIF2B1 | 1.56 |
| 1600 | 3 | 4 | 5 | | V-1 | DCP1A | 1.59 | 1696 | 3 | 4 | 5 | | V-1 | EIF2B3 | 1.98 |
| 1601 | 3 | 4 | 5 | | V-1 | DCP2 | 1.98 | 1697 | 3 | 4 | 5 | | V-1 | EIF2B5 | 1.56 |
| 1602 | 3 | 4 | 5 | | V-1 | DCTD | 1.55 | 1698 | 3 | 4 | 5 | | V-1 | EIF2C1 | 1.63 |
| 1603 | 3 | 4 | 5 | | V-1 | DCTN2 | 1.51 | 1699 | 3 | 4 | 5 | | V-1 | EIF2S1 | 1.76 |
| 1604 | 3 | 4 | 5 | | V-1 | DCTN4 | 1.66 | 1700 | 3 | 4 | 5 | | V-1 | EIF2S2 | 1.57 |
| 1605 | 3 | 4 | 5 | | V-1 | DCTN6 | 1.54 | 1701 | 3 | 4 | 5 | | V-1 | EIF3B | 1.90 |
| 1606 | 3 | 4 | 5 | | V-1 | DDI2 | 1.50 | 1702 | 3 | 4 | 5 | | V-1 | EIF3C | 1.69 |
| 1607 | 3 | 4 | 5 | | V-1 | DDRGK1 | 1.78 | 1703 | 3 | 4 | 5 | | V-1 | EIF3I | 1.84 |
| 1608 | 3 | 4 | 5 | | V-1 | DDX1 | 1.80 | 1704 | 3 | 4 | 5 | | V-1 | EIF3J | 1.94 |
| 1609 | 3 | 4 | 5 | | V-1 | DDX18 | 1.93 | 1705 | 3 | 4 | 5 | | V-1 | EIF3M | 1.85 |
| 1610 | 3 | 4 | 5 | | V-1 | DDX19A | 1.87 | 1706 | 3 | 4 | 5 | | V-1 | EIF4A1 | 1.83 |
| 1611 | 3 | 4 | 5 | | V-1 | DDX27 | 1.72 | 1707 | 3 | 4 | 5 | | V-1 | EIF4A3 | 1.72 |
| 1612 | 3 | 4 | 5 | | V-1 | DDX39A | 1.83 | 1708 | 3 | 4 | 5 | | V-1 | EIF4G2 | 1.65 |
| 1613 | 3 | 4 | 5 | | V-1 | DDX41 | 1.57 | 1709 | 3 | 4 | 5 | | V-1 | EIF4G3 | 1.97 |
| 1614 | 3 | 4 | 5 | | V-1 | DDX46 | 1.63 | 1710 | 3 | 4 | 5 | | V-1 | EIF4H | 1.84 |
| 1615 | 3 | 4 | 5 | | V-1 | DDX47 | 1.98 | 1711 | 3 | 4 | 5 | | V-1 | EIF6 | 1.78 |
| 1616 | 3 | 4 | 5 | | V-1 | DDX52 | 1.93 | 1712 | 3 | 4 | 5 | | V-1 | ELAVL1 | 1.90 |
| 1617 | 3 | 4 | 5 | | V-1 | DDX56 | 1.58 | 1713 | 3 | 4 | 5 | | V-1 | ELMO2 | 1.80 |
| 1618 | 3 | 4 | 5 | | V-1 | DEAF1 | 1.60 | 1714 | 3 | 4 | 5 | | V-1 | ELOVL1 | 1.66 |
| 1619 | 3 | 4 | 5 | | V-1 | DECR1 | 1.98 | 1715 | 3 | 4 | 5 | | V-1 | ELP2 | 1.77 |
| 1620 | 3 | 4 | 5 | | V-1 | DEK | 1.98 | 1716 | 3 | 4 | 5 | | V-1 | ELP3 | 1.64 |
| 1621 | 3 | 4 | 5 | | V-1 | DENND4C | 1.65 | 1717 | 3 | 4 | 5 | | V-1 | ELP4 | 1.78 |
| 1622 | 3 | 4 | 5 | | V-1 | DERA | 1.66 | 1718 | 3 | 4 | 5 | | V-1 | EMB | 1.55 |
| 1623 | 3 | 4 | 5 | | V-1 | DERL1 | 1.52 | 1719 | 3 | 4 | 5 | | V-1 | EMR2 | 1.56 |
| 1624 | 3 | 4 | 5 | | V-1 | DET1 | 1.94 | 1720 | 3 | 4 | 5 | | V-1 | ENOX2 | 1.55 |
| 1625 | 3 | 4 | 5 | | V-1 | DFFA | 1.97 | 1721 | 3 | 4 | 5 | | V-1 | ENTPD6 | 1.61 |
| 1626 | 3 | 4 | 5 | | V-1 | DGKG | 1.53 | 1722 | 3 | 4 | 5 | | V-1 | EP400 | 1.62 |
| 1627 | 3 | 4 | 5 | | V-1 | DHPS | 1.58 | 1723 | 3 | 4 | 5 | | V-1 | EPGS | 1.58 |
| 1628 | 3 | 4 | 5 | | V-1 | DHRS7B | 1.86 | 1724 | 3 | 4 | 5 | | V-1 | EPN1 | 1.53 |
| 1629 | 3 | 4 | 5 | | V-1 | DHX15 | 1.78 | 1725 | 3 | 4 | 5 | | V-1 | EPRS | 1.86 |

Fig. 41 - 10

| | | | | | | | | | | | | | | | | | |
|---|---|---|---|---|---|---|---|---|---|---|---|---|---|---|---|---|---|
| 1726 | 3 | 4 | 5 | | | V-1 | EPS15 | 1.75 | 1822 | 3 | 4 | 5 | | | V-1 | FKBP3 | 1.87 |
| 1727 | 3 | 4 | 5 | | | V-1 | ERGIC3 | 1.61 | 1823 | 3 | 4 | 5 | | | V-1 | FKBP4 | 1.99 |
| 1728 | 3 | 4 | 5 | | | V-1 | ERH | 1.97 | 1824 | 3 | 4 | 5 | | | V-1 | FLII | 1.81 |
| 1729 | 3 | 4 | 5 | | | V-1 | ERMAP | 1.51 | 1825 | 3 | 4 | 5 | | | V-1 | FLJ42627 | 1.58 |
| 1730 | 3 | 4 | 5 | | | V-1 | ERP44 | 1.52 | 1826 | 3 | 4 | 5 | | | V-1 | FLNA | 1.96 |
| 1731 | 3 | 4 | 5 | | | V-1 | ETF1 | 1.73 | 1827 | 3 | 4 | 5 | | | V-1 | FNDC3A | 1.52 |
| 1732 | 3 | 4 | 5 | | | V-1 | ETFA | 1.78 | 1828 | 3 | 4 | 5 | | | V-1 | FNDC3B | 1.54 |
| 1733 | 3 | 4 | 5 | | | V-1 | ETFB | 1.63 | 1829 | 3 | 4 | 5 | | | V-1 | FNTA | 1.70 |
| 1734 | 3 | 4 | 5 | | | V-1 | ETFDH | 1.77 | 1830 | 3 | 4 | 5 | | | V-1 | FNTB | 1.78 |
| 1735 | 3 | 4 | 5 | | | V-1 | ETNK1 | 1.75 | 1831 | 3 | 4 | 5 | | | V-1 | FOSL2 | 1.53 |
| 1736 | 3 | 4 | 5 | | | V-1 | ETS2 | 1.56 | 1832 | 3 | 4 | 5 | | | V-1 | FOXK2 | 1.74 |
| 1737 | 3 | 4 | 5 | | | V-1 | EVI5 | 1.75 | 1833 | 3 | 4 | 5 | | | V-1 | FOXP1 | 1.55 |
| 1738 | 3 | 4 | 5 | | | V-1 | EXOC1 | 1.51 | 1834 | 3 | 4 | 5 | | | V-1 | FRMD4B | 1.89 |
| 1739 | 3 | 4 | 5 | | | V-1 | EXOC2 | 1.87 | 1835 | 3 | 4 | 5 | | | V-1 | FRYL | 1.52 |
| 1740 | 3 | 4 | 5 | | | V-1 | EXOC3 | 1.73 | 1836 | 3 | 4 | 5 | | | V-1 | FTO | 1.70 |
| 1741 | 3 | 4 | 5 | | | V-1 | EXOC4 | 1.99 | 1837 | 3 | 4 | 5 | | | V-1 | FTSJ1 | 1.77 |
| 1742 | 3 | 4 | 5 | | | V-1 | EXOC5 | 1.60 | 1838 | 3 | 4 | 5 | | | V-1 | FTSJ2 | 1.54 |
| 1743 | 3 | 4 | 5 | | | V-1 | EXOC6 | 1.60 | 1839 | 3 | 4 | 5 | | | V-1 | FTSJ3 | 1.89 |
| 1744 | 3 | 4 | 5 | | | V-1 | EXOC8 | 1.50 | 1840 | 3 | 4 | 5 | | | V-1 | FTSJD2 | 1.50 |
| 1745 | 3 | 4 | 5 | | | V-1 | EXOSC1 | 1.73 | 1841 | 3 | 4 | 5 | | | V-1 | FXR1 | 1.69 |
| 1746 | 3 | 4 | 5 | | | V-1 | EXOSC10 | 1.62 | 1842 | 3 | 4 | 5 | | | V-1 | FXYD5 | 1.53 |
| 1747 | 3 | 4 | 5 | | | V-1 | EXOSC3 | 1.67 | 1843 | 3 | 4 | 5 | | | V-1 | FYB | 1.58 |
| 1748 | 3 | 4 | 5 | | | V-1 | EXOSC4 | 1.69 | 1844 | 3 | 4 | 5 | | | V-1 | FYCO1 | 1.65 |
| 1749 | 3 | 4 | 5 | | | V-1 | EXOSC5 | 1.59 | 1845 | 3 | 4 | 5 | | | V-1 | FYN | 1.57 |
| 1750 | 3 | 4 | 5 | | | V-1 | EXOSC7 | 1.51 | 1846 | 3 | 4 | 5 | | | V-1 | FYTTD1 | 1.79 |
| 1751 | 3 | 4 | 5 | | | V-1 | EXT1 | 1.94 | 1847 | 3 | 4 | 5 | | | V-1 | FZD5 | 1.81 |
| 1752 | 3 | 4 | 5 | | | V-1 | EZR | 1.87 | 1848 | 3 | 4 | 5 | | | V-1 | G3BP1 | 1.99 |
| 1753 | 3 | 4 | 5 | | | V-1 | F13A1 | 1.80 | 1849 | 3 | 4 | 5 | | | V-1 | G3BP2 | 1.50 |
| 1754 | 3 | 4 | 5 | | | V-1 | FAF2 | 1.74 | 1850 | 3 | 4 | 5 | | | V-1 | GABPB1 | 1.51 |
| 1755 | 3 | 4 | 5 | | | V-1 | FAM105B | 1.79 | 1851 | 3 | 4 | 5 | | | V-1 | GALK2 | 1.91 |
| 1756 | 3 | 4 | 5 | | | V-1 | FAM108B1 | 1.54 | 1852 | 3 | 4 | 5 | | | V-1 | GALNS | 1.56 |
| 1757 | 3 | 4 | 5 | | | V-1 | FAM110A | 1.59 | 1853 | 3 | 4 | 5 | | | V-1 | GALNT1 | 1.78 |
| 1758 | 3 | 4 | 5 | | | V-1 | FAM117B | 1.77 | 1854 | 3 | 4 | 5 | | | V-1 | GALNT6 | 1.85 |
| 1759 | 3 | 4 | 5 | | | V-1 | FAM122B | 1.64 | 1855 | 3 | 4 | 5 | | | V-1 | GANAB | 1.79 |
| 1760 | 3 | 4 | 5 | | | V-1 | FAM127B | 1.74 | 1856 | 3 | 4 | 5 | | | V-1 | GANC | 1.65 |
| 1761 | 3 | 4 | 5 | | | V-1 | FAM134B | 1.75 | 1857 | 3 | 4 | 5 | | | V-1 | GAPVD1 | 1.58 |
| 1762 | 3 | 4 | 5 | | | V-1 | FAM135A | 1.79 | 1858 | 3 | 4 | 5 | | | V-1 | GAR1 | 1.70 |
| 1763 | 3 | 4 | 5 | | | V-1 | FAM149B1 | 1.85 | 1859 | 3 | 4 | 5 | | | V-1 | GARS | 1.78 |
| 1764 | 3 | 4 | 5 | | | V-1 | FAM168A | 1.58 | 1860 | 3 | 4 | 5 | | | V-1 | GART | 1.85 |
| 1765 | 3 | 4 | 5 | | | V-1 | FAM175B | 1.93 | 1861 | 3 | 4 | 5 | | | V-1 | GATAD1 | 1.74 |
| 1766 | 3 | 4 | 5 | | | V-1 | FAM178A | 1.81 | 1862 | 3 | 4 | 5 | | | V-1 | GATSL3 | 1.54 |
| 1767 | 3 | 4 | 5 | | | V-1 | FAM189B | 1.65 | 1863 | 3 | 4 | 5 | | | V-1 | GBF1 | 1.75 |
| 1768 | 3 | 4 | 5 | | | V-1 | FAM199X | 1.68 | 1864 | 3 | 4 | 5 | | | V-1 | GBGT1 | 1.76 |
| 1769 | 3 | 4 | 5 | | | V-1 | FAM19A1 | 1.57 | 1865 | 3 | 4 | 5 | | | V-1 | GBP4 | 1.52 |
| 1770 | 3 | 4 | 5 | | | V-1 | FAM203A | 1.53 | 1866 | 3 | 4 | 5 | | | V-1 | GCA | 1.56 |
| 1771 | 3 | 4 | 5 | | | V-1 | FAM208A | 1.57 | 1867 | 3 | 4 | 5 | | | V-1 | GCN1L1 | 1.77 |
| 1772 | 3 | 4 | 5 | | | V-1 | FAM210A | 1.52 | 1868 | 3 | 4 | 5 | | | V-1 | GCNT2 | 1.77 |
| 1773 | 3 | 4 | 5 | | | V-1 | FAM213A | 1.82 | 1869 | 3 | 4 | 5 | | | V-1 | GDAP1 | 1.83 |
| 1774 | 3 | 4 | 5 | | | V-1 | FAM213B | 1.52 | 1870 | 3 | 4 | 5 | | | V-1 | GDAP2 | 1.66 |
| 1775 | 3 | 4 | 5 | | | V-1 | FAM217B | 1.64 | 1871 | 3 | 4 | 5 | | | V-1 | GDI2 | 1.88 |
| 1776 | 3 | 4 | 5 | | | V-1 | FAM21C | 1.58 | 1872 | 3 | 4 | 5 | | | V-1 | GEMIN5 | 1.83 |
| 1777 | 3 | 4 | 5 | | | V-1 | FAM458 | 1.55 | 1873 | 3 | 4 | 5 | | | V-1 | GFM2 | 1.74 |
| 1778 | 3 | 4 | 5 | | | V-1 | FAM49A | 1.68 | 1874 | 3 | 4 | 5 | | | V-1 | GFPT1 | 1.57 |
| 1779 | 3 | 4 | 5 | | | V-1 | FAM50A | 1.52 | 1875 | 3 | 4 | 5 | | | V-1 | GGA2 | 1.78 |
| 1780 | 3 | 4 | 5 | | | V-1 | FAM55C | 1.60 | 1876 | 3 | 4 | 5 | | | V-1 | GGCT | 1.54 |
| 1781 | 3 | 4 | 5 | | | V-1 | FAM63B | 1.89 | 1877 | 3 | 4 | 5 | | | V-1 | GGCX | 1.73 |
| 1782 | 3 | 4 | 5 | | | V-1 | FAM78A | 1.75 | 1878 | 3 | 4 | 5 | | | V-1 | GHDC | 1.96 |
| 1783 | 3 | 4 | 5 | | | V-1 | FAM86A | 1.58 | 1879 | 3 | 4 | 5 | | | V-1 | GHITM | 1.63 |
| 1784 | 3 | 4 | 5 | | | V-1 | FAM98A | 1.78 | 1880 | 3 | 4 | 5 | | | V-1 | GIGYF2 | 1.72 |
| 1785 | 3 | 4 | 5 | | | V-1 | FANCE | 1.52 | 1881 | 3 | 4 | 5 | | | V-1 | GIMAP2 | 1.65 |
| 1786 | 3 | 4 | 5 | | | V-1 | FANCF | 1.50 | 1882 | 3 | 4 | 5 | | | V-1 | GIMAP4 | 1.69 |
| 1787 | 3 | 4 | 5 | | | V-1 | FAR1 | 1.93 | 1883 | 3 | 4 | 5 | | | V-1 | GIMAP6 | 1.57 |
| 1788 | 3 | 4 | 5 | | | V-1 | FARSA | 1.74 | 1884 | 3 | 4 | 5 | | | V-1 | GLA | 1.66 |
| 1789 | 3 | 4 | 5 | | | V-1 | FASTKD1 | 1.73 | 1885 | 3 | 4 | 5 | | | V-1 | GLB1 | 1.95 |
| 1790 | 3 | 4 | 5 | | | V-1 | FASTKD5 | 1.58 | 1886 | 3 | 4 | 5 | | | V-1 | GLCE | 1.93 |
| 1791 | 3 | 4 | 5 | | | V-1 | FBLN7 | 1.81 | 1887 | 3 | 4 | 5 | | | V-1 | GLE1 | 1.72 |
| 1792 | 3 | 4 | 5 | | | V-1 | FBXL15 | 1.98 | 1888 | 3 | 4 | 5 | | | V-1 | GLG1 | 1.95 |
| 1793 | 3 | 4 | 5 | | | V-1 | FBXL19 | 1.83 | 1889 | 3 | 4 | 5 | | | V-1 | GLRX3 | 1.57 |
| 1794 | 3 | 4 | 5 | | | V-1 | FBXO18 | 1.51 | 1890 | 3 | 4 | 5 | | | V-1 | GLT8D1 | 1.52 |
| 1795 | 3 | 4 | 5 | | | V-1 | FBXO21 | 1.77 | 1891 | 3 | 4 | 5 | | | V-1 | GLTP | 1.67 |
| 1796 | 3 | 4 | 5 | | | V-1 | FBXO22 | 1.51 | 1892 | 3 | 4 | 5 | | | V-1 | GLTPD1 | 1.51 |
| 1797 | 3 | 4 | 5 | | | V-1 | FBXO22-AS1 | 1.82 | 1893 | 3 | 4 | 5 | | | V-1 | GMEB1 | 1.50 |
| 1798 | 3 | 4 | 5 | | | V-1 | FBXO28 | 1.72 | 1894 | 3 | 4 | 5 | | | V-1 | GMNN | 1.68 |
| 1799 | 3 | 4 | 5 | | | V-1 | FBXO30 | 1.83 | 1895 | 3 | 4 | 5 | | | V-1 | GMPPB | 1.74 |
| 1800 | 3 | 4 | 5 | | | V-1 | FBXO41 | 1.58 | 1896 | 3 | 4 | 5 | | | V-1 | GMPS | 1.76 |
| 1801 | 3 | 4 | 5 | | | V-1 | FBXO42 | 1.80 | 1897 | 3 | 4 | 5 | | | V-1 | GNA13 | 1.55 |
| 1802 | 3 | 4 | 5 | | | V-1 | FBXO45 | 1.93 | 1898 | 3 | 4 | 5 | | | V-1 | GNAI3 | 1.88 |
| 1803 | 3 | 4 | 5 | | | V-1 | FBXO8 | 1.62 | 1899 | 3 | 4 | 5 | | | V-1 | GNB1 | 1.61 |
| 1804 | 3 | 4 | 5 | | | V-1 | FBXW11 | 1.64 | 1900 | 3 | 4 | 5 | | | V-1 | GNB1L | 1.73 |
| 1805 | 3 | 4 | 5 | | | V-1 | FBXW2 | 1.57 | 1901 | 3 | 4 | 5 | | | V-1 | GNB4 | 1.75 |
| 1806 | 3 | 4 | 5 | | | V-1 | FBXW8 | 1.71 | 1902 | 3 | 4 | 5 | | | V-1 | GNE | 1.57 |
| 1807 | 3 | 4 | 5 | | | V-1 | FCF1 | 1.85 | 1903 | 3 | 4 | 5 | | | V-1 | GNL2 | 1.95 |
| 1808 | 3 | 4 | 5 | | | V-1 | FDFT1 | 1.59 | 1904 | 3 | 4 | 5 | | | V-1 | GNL3L | 1.61 |
| 1809 | 3 | 4 | 5 | | | V-1 | FDX1 | 1.83 | 1905 | 3 | 4 | 5 | | | V-1 | GNPAT | 1.74 |
| 1810 | 3 | 4 | 5 | | | V-1 | FDXACB1 | 1.61 | 1906 | 3 | 4 | 5 | | | V-1 | GNPNAT1 | 1.52 |
| 1811 | 3 | 4 | 5 | | | V-1 | FDXR | 1.77 | 1907 | 3 | 4 | 5 | | | V-1 | GNPTAB | 1.67 |
| 1812 | 3 | 4 | 5 | | | V-1 | FEM1A | 1.63 | 1908 | 3 | 4 | 5 | | | V-1 | GNPTG | 1.76 |
| 1813 | 3 | 4 | 5 | | | V-1 | FEN1 | 1.79 | 1909 | 3 | 4 | 5 | | | V-1 | GOLGA2 | 1.55 |
| 1814 | 3 | 4 | 5 | | | V-1 | FERMT3 | 1.67 | 1910 | 3 | 4 | 5 | | | V-1 | GOLGA3 | 1.69 |
| 1815 | 3 | 4 | 5 | | | V-1 | FES | 1.86 | 1911 | 3 | 4 | 5 | | | V-1 | GOLPH3 | 1.82 |
| 1816 | 3 | 4 | 5 | | | V-1 | FGD4 | 1.93 | 1912 | 3 | 4 | 5 | | | V-1 | GOLT1B | 1.65 |
| 1817 | 3 | 4 | 5 | | | V-1 | FGD5-AS1 | 1.57 | 1913 | 3 | 4 | 5 | | | V-1 | GORASP2 | 1.79 |
| 1818 | 3 | 4 | 5 | | | V-1 | FGL2 | 1.94 | 1914 | 3 | 4 | 5 | | | V-1 | GOSR1 | 1.51 |
| 1819 | 3 | 4 | 5 | | | V-1 | FHOD1 | 1.52 | 1915 | 3 | 4 | 5 | | | V-1 | GOSR2 | 1.74 |
| 1820 | 3 | 4 | 5 | | | V-1 | FIBP | 1.55 | 1916 | 3 | 4 | 5 | | | V-1 | GOT2 | 1.81 |
| 1821 | 3 | 4 | 5 | | | V-1 | FKBP1A | 1.69 | 1917 | 3 | 4 | 5 | | | V-1 | GPAA1 | 1.66 |

Fig. 41 - 11

| | | | | | | | | | | | | | | | |
|---|---|---|---|---|---|---|---|---|---|---|---|---|---|---|---|
| 1918 | 3 | 4 | 5 | | V-1 | GPATCH2 | 1.61 | 2014 | 3 | 4 | 5 | | V-1 | HSD17B10 | 1.83 |
| 1919 | 3 | 4 | 5 | | V-1 | GPATCH3 | 1.64 | 2015 | 3 | 4 | 5 | | V-1 | HSD17B12 | 1.86 |
| 1920 | 3 | 4 | 5 | | V-1 | GPATCH4 | 1.52 | 2016 | 3 | 4 | 5 | | V-1 | HSD3B7 | 1.99 |
| 1921 | 3 | 4 | 5 | | V-1 | GPBAR1 | 1.97 | 2017 | 3 | 4 | 5 | | V-1 | HSF1 | 1.75 |
| 1922 | 3 | 4 | 5 | | V-1 | GPD2 | 1.75 | 2018 | 3 | 4 | 5 | | V-1 | HSP90AB2P | 1.62 |
| 1923 | 3 | 4 | 5 | | V-1 | GPI | 1.91 | 2019 | 3 | 4 | 5 | | V-1 | HSPA14 | 1.79 |
| 1924 | 3 | 4 | 5 | | V-1 | GPN2 | 1.69 | 2020 | 3 | 4 | 5 | | V-1 | HSPA1A | 1.90 |
| 1925 | 3 | 4 | 5 | | V-1 | GPR107 | 1.61 | 2021 | 3 | 4 | 5 | | V-1 | HSPA1B | 1.93 |
| 1926 | 3 | 4 | 5 | | V-1 | GPR132 | 1.58 | 2022 | 3 | 4 | 5 | | V-1 | HTATSF1 | 1.53 |
| 1927 | 3 | 4 | 5 | | V-1 | GPR172A | 1.97 | 2023 | 3 | 4 | 5 | | V-1 | HTT | 1.85 |
| 1928 | 3 | 4 | 5 | | V-1 | GPR65 | 1.81 | 2024 | 3 | 4 | 5 | | V-1 | HUS1 | 1.83 |
| 1929 | 3 | 4 | 5 | | V-1 | GPS1 | 1.73 | 2025 | 3 | 4 | 5 | | V-1 | HYAL2 | 1.77 |
| 1930 | 3 | 4 | 5 | | V-1 | GRAMD4 | 1.98 | 2026 | 3 | 4 | 5 | | V-1 | HYOU1 | 1.69 |
| 1931 | 3 | 4 | 5 | | V-1 | GRINA | 1.55 | 2027 | 3 | 4 | 5 | | V-1 | IARS | 1.71 |
| 1932 | 3 | 4 | 5 | | V-1 | GRPEL1 | 1.92 | 2028 | 3 | 4 | 5 | | V-1 | IBA57 | 1.54 |
| 1933 | 3 | 4 | 5 | | V-1 | GRWD1 | 1.66 | 2029 | 3 | 4 | 5 | | V-1 | ICMT | 1.61 |
| 1934 | 3 | 4 | 5 | | V-1 | GSS | 1.87 | 2030 | 3 | 4 | 5 | | V-1 | IDH3A | 1.69 |
| 1935 | 3 | 4 | 5 | | V-1 | GSTK1 | 1.58 | 2031 | 3 | 4 | 5 | | V-1 | IDH3G | 1.54 |
| 1936 | 3 | 4 | 5 | | V-1 | GTF2E2 | 1.59 | 2032 | 3 | 4 | 5 | | V-1 | IER3IP1 | 1.78 |
| 1937 | 3 | 4 | 5 | | V-1 | GTF2F1 | 1.77 | 2033 | 3 | 4 | 5 | | V-1 | IER5 | 1.51 |
| 1938 | 3 | 4 | 5 | | V-1 | GTF2F2 | 1.85 | 2034 | 3 | 4 | 5 | | V-1 | IFI16 | 1.93 |
| 1939 | 3 | 4 | 5 | | V-1 | GTF2H1 | 1.63 | 2035 | 3 | 4 | 5 | | V-1 | IFI35 | 1.64 |
| 1940 | 3 | 4 | 5 | | V-1 | GTF2H3 | 1.67 | 2036 | 3 | 4 | 5 | | V-1 | IFIH1 | 1.64 |
| 1941 | 3 | 4 | 5 | | V-1 | GTF2H4 | 1.92 | 2037 | 3 | 4 | 5 | | V-1 | IFNGR2 | 1.56 |
| 1942 | 3 | 4 | 5 | | V-1 | GTF3C1 | 1.52 | 2038 | 3 | 4 | 5 | | V-1 | IKBKAP | 1.56 |
| 1943 | 3 | 4 | 5 | | V-1 | GTF3C3 | 1.83 | 2039 | 3 | 4 | 5 | | V-1 | IKBKE | 1.71 |
| 1944 | 3 | 4 | 5 | | V-1 | GTF3C5 | 1.54 | 2040 | 3 | 4 | 5 | | V-1 | IKZF1 | 1.51 |
| 1945 | 3 | 4 | 5 | | V-1 | GTPBP4 | 1.82 | 2041 | 3 | 4 | 5 | | V-1 | IL10RA | 1.74 |
| 1946 | 3 | 4 | 5 | | V-1 | GTPBP8 | 1.61 | 2042 | 3 | 4 | 5 | | V-1 | IL15RA | 1.82 |
| 1947 | 3 | 4 | 5 | | V-1 | GUF1 | 1.69 | 2043 | 3 | 4 | 5 | | V-1 | IL17RA | 1.72 |
| 1948 | 3 | 4 | 5 | | V-1 | GZF1 | 1.51 | 2044 | 3 | 4 | 5 | | V-1 | ILF2 | 1.53 |
| 1949 | 3 | 4 | 5 | | V-1 | H1FX | 1.77 | 2045 | 3 | 4 | 5 | | V-1 | ILF3 | 1.68 |
| 1950 | 3 | 4 | 5 | | V-1 | H2AFJ | 1.83 | 2046 | 3 | 4 | 5 | | V-1 | ILKAP | 1.61 |
| 1951 | 3 | 4 | 5 | | V-1 | H2AFX | 1.81 | 2047 | 3 | 4 | 5 | | V-1 | IMMT | 2.00 |
| 1952 | 3 | 4 | 5 | | V-1 | HADHA | 1.78 | 2048 | 3 | 4 | 5 | | V-1 | IMP3 | 1.51 |
| 1953 | 3 | 4 | 5 | | V-1 | HARS | 1.79 | 2049 | 3 | 4 | 5 | | V-1 | IMP4 | 1.58 |
| 1954 | 3 | 4 | 5 | | V-1 | HAT1 | 1.88 | 2050 | 3 | 4 | 5 | | V-1 | IMPA1 | 1.53 |
| 1955 | 3 | 4 | 5 | | V-1 | HBS1L | 1.50 | 2051 | 3 | 4 | 5 | | V-1 | IMPAD1 | 1.65 |
| 1956 | 3 | 4 | 5 | | V-1 | HBXIP | 1.63 | 2052 | 3 | 4 | 5 | | V-1 | INCENP | 1.64 |
| 1957 | 3 | 4 | 5 | | V-1 | HCCS | 1.83 | 2053 | 3 | 4 | 5 | | V-1 | ING3 | 1.66 |
| 1958 | 3 | 4 | 5 | | V-1 | HCFC1R1 | 1.68 | 2054 | 3 | 4 | 5 | | V-1 | INO80B | 1.55 |
| 1959 | 3 | 4 | 5 | | V-1 | HCG11 | 1.87 | 2055 | 3 | 4 | 5 | | V-1 | INPP5F | 1.76 |
| 1960 | 3 | 4 | 5 | | V-1 | HDAC1 | 1.76 | 2056 | 3 | 4 | 5 | | V-1 | INPPL1 | 1.75 |
| 1961 | 3 | 4 | 5 | | V-1 | HDAC11 | 1.68 | 2057 | 3 | 4 | 5 | | V-1 | INSIG2 | 1.55 |
| 1962 | 3 | 4 | 5 | | V-1 | HDAC2 | 1.65 | 2058 | 3 | 4 | 5 | | V-1 | INTS1 | 1.58 |
| 1963 | 3 | 4 | 5 | | V-1 | HDAC4 | 1.92 | 2059 | 3 | 4 | 5 | | V-1 | INTS2 | 1.77 |
| 1964 | 3 | 4 | 5 | | V-1 | HDAC8 | 1.72 | 2060 | 3 | 4 | 5 | | V-1 | INTS4 | 1.86 |
| 1965 | 3 | 4 | 5 | | V-1 | HDHD2 | 1.56 | 2061 | 3 | 4 | 5 | | V-1 | INTS5 | 1.68 |
| 1966 | 3 | 4 | 5 | | V-1 | HDLBP | 1.84 | 2062 | 3 | 4 | 5 | | V-1 | INTS7 | 1.55 |
| 1967 | 3 | 4 | 5 | | V-1 | HEATR1 | 1.96 | 2063 | 3 | 4 | 5 | | V-1 | INTS8 | 1.51 |
| 1968 | 3 | 4 | 5 | | V-1 | HEATR3 | 1.64 | 2064 | 3 | 4 | 5 | | V-1 | INTS9 | 1.75 |
| 1969 | 3 | 4 | 5 | | V-1 | HEATR5A | 1.56 | 2065 | 3 | 4 | 5 | | V-1 | INVS | 1.63 |
| 1970 | 3 | 4 | 5 | | V-1 | HEATR6 | 1.80 | 2066 | 3 | 4 | 5 | | V-1 | IPO13 | 1.73 |
| 1971 | 3 | 4 | 5 | | V-1 | HECTD1 | 1.85 | 2067 | 3 | 4 | 5 | | V-1 | IPO4 | 1.52 |
| 1972 | 3 | 4 | 5 | | V-1 | HELZ | 1.76 | 2068 | 3 | 4 | 5 | | V-1 | IPO5 | 1.68 |
| 1973 | 3 | 4 | 5 | | V-1 | HERC2 | 1.54 | 2069 | 3 | 4 | 5 | | V-1 | IPO8 | 1.67 |
| 1974 | 3 | 4 | 5 | | V-1 | HERC4 | 1.89 | 2070 | 3 | 4 | 5 | | V-1 | IQGAP1 | 1.81 |
| 1975 | 3 | 4 | 5 | | V-1 | HERPUD1 | 1.63 | 2071 | 3 | 4 | 5 | | V-1 | IQGAP2 | 1.63 |
| 1976 | 3 | 4 | 5 | | V-1 | HEXB | 1.93 | 2072 | 3 | 4 | 5 | | V-1 | IREB2 | 1.89 |
| 1977 | 3 | 4 | 5 | | V-1 | HGSNAT | 1.50 | 2073 | 3 | 4 | 5 | | V-1 | IRF2BP2 | 1.83 |
| 1978 | 3 | 4 | 5 | | V-1 | HHLA3 | 1.55 | 2074 | 3 | 4 | 5 | | V-1 | IST1 | 1.60 |
| 1979 | 3 | 4 | 5 | | V-1 | HIBADH | 1.72 | 2075 | 3 | 4 | 5 | | V-1 | ITFG3 | 1.71 |
| 1980 | 3 | 4 | 5 | | V-1 | HIGD2A | 1.88 | 2076 | 3 | 4 | 5 | | V-1 | ITGA4 | 1.63 |
| 1981 | 3 | 4 | 5 | | V-1 | HINT2 | 1.61 | 2077 | 3 | 4 | 5 | | V-1 | ITGB1 | 1.65 |
| 1982 | 3 | 4 | 5 | | V-1 | HINT3 | 1.72 | 2078 | 3 | 4 | 5 | | V-1 | ITGB2 | 1.73 |
| 1983 | 3 | 4 | 5 | | V-1 | HIPK2 | 1.97 | 2079 | 3 | 4 | 5 | | V-1 | IVD | 1.70 |
| 1984 | 3 | 4 | 5 | | V-1 | HIVEP3 | 1.88 | 2080 | 3 | 4 | 5 | | V-1 | JAGN1 | 1.55 |
| 1985 | 3 | 4 | 5 | | V-1 | HLA-DMA | 1.91 | 2081 | 3 | 4 | 5 | | V-1 | JAK2 | 1.86 |
| 1986 | 3 | 4 | 5 | | V-1 | HLA-DQB2 | 1.86 | 2082 | 3 | 4 | 5 | | V-1 | JKAMP | 1.65 |
| 1987 | 3 | 4 | 5 | | V-1 | HLA-DRA | 1.61 | 2083 | 3 | 4 | 5 | | V-1 | JMJD4 | 1.54 |
| 1988 | 3 | 4 | 5 | | V-1 | HM13 | 1.75 | 2084 | 3 | 4 | 5 | | V-1 | JMY | 1.57 |
| 1989 | 3 | 4 | 5 | | V-1 | HMG20A | 1.52 | 2085 | 3 | 4 | 5 | | V-1 | JRKL | 1.88 |
| 1990 | 3 | 4 | 5 | | V-1 | HMGCR | 1.69 | 2086 | 3 | 4 | 5 | | V-1 | JUN | 1.73 |
| 1991 | 3 | 4 | 5 | | V-1 | HMGCS1 | 1.61 | 2087 | 3 | 4 | 5 | | V-1 | KARS | 1.87 |
| 1992 | 3 | 4 | 5 | | V-1 | HMGX83 | 1.59 | 2088 | 3 | 4 | 5 | | V-1 | KAT5 | 1.51 |
| 1993 | 3 | 4 | 5 | | V-1 | HNRNPA0 | 1.56 | 2089 | 3 | 4 | 5 | | V-1 | KCNQ1 | 1.69 |
| 1994 | 3 | 4 | 5 | | V-1 | HNRNPA1 | 1.80 | 2090 | 3 | 4 | 5 | | V-1 | KCTD11 | 1.58 |
| 1995 | 3 | 4 | 5 | | V-1 | HNRNPA2B1 | 1.96 | 2091 | 3 | 4 | 5 | | V-1 | KCTD20 | 1.52 |
| 1996 | 3 | 4 | 5 | | V-1 | HNRNPA3 | 1.97 | 2092 | 3 | 4 | 5 | | V-1 | KCTD3 | 1.90 |
| 1997 | 3 | 4 | 5 | | V-1 | HNRNPD | 1.90 | 2093 | 3 | 4 | 5 | | V-1 | KCTD5 | 1.61 |
| 1998 | 3 | 4 | 5 | | V-1 | HNRNPF | 1.53 | 2094 | 3 | 4 | 5 | | V-1 | KCTD6 | 1.85 |
| 1999 | 3 | 4 | 5 | | V-1 | HNRNPH3 | 1.50 | 2095 | 3 | 4 | 5 | | V-1 | KDM1A | 1.87 |
| 2000 | 3 | 4 | 5 | | V-1 | HNRNPK | 1.54 | 2096 | 3 | 4 | 5 | | V-1 | KDM2B | 1.52 |
| 2001 | 3 | 4 | 5 | | V-1 | HNRNPR | 1.80 | 2097 | 3 | 4 | 5 | | V-1 | KDM3B | 1.55 |
| 2002 | 3 | 4 | 5 | | V-1 | HNRNPU | 1.89 | 2098 | 3 | 4 | 5 | | V-1 | KDSR | 1.69 |
| 2003 | 3 | 4 | 5 | | V-1 | HNRNPUL2 | 1.87 | 2099 | 3 | 4 | 5 | | V-1 | KEAP1 | 1.67 |
| 2004 | 3 | 4 | 5 | | V-1 | HNRPLL | 1.54 | 2100 | 3 | 4 | 5 | | V-1 | KHDRBS1 | 1.74 |
| 2005 | 3 | 4 | 5 | | V-1 | HOMEZ | 1.84 | 2101 | 3 | 4 | 5 | | V-1 | KHSRP | 1.84 |
| 2006 | 3 | 4 | 5 | | V-1 | HOXA1 | 1.61 | 2102 | 3 | 4 | 5 | | V-1 | KIAA0100 | 1.70 |
| 2007 | 3 | 4 | 5 | | V-1 | HOXA9 | 1.54 | 2103 | 3 | 4 | 5 | | V-1 | KIAA0146 | 1.52 |
| 2008 | 3 | 4 | 5 | | V-1 | HPR | 1.78 | 2104 | 3 | 4 | 5 | | V-1 | KIAA0368 | 1.71 |
| 2009 | 3 | 4 | 5 | | V-1 | HPS3 | 1.69 | 2105 | 3 | 4 | 5 | | V-1 | KIAA0391 | 1.52 |
| 2010 | 3 | 4 | 5 | | V-1 | HPS6 | 1.97 | 2106 | 3 | 4 | 5 | | V-1 | KIAA0494 | 1.61 |
| 2011 | 3 | 4 | 5 | | V-1 | HRAS | 1.91 | 2107 | 3 | 4 | 5 | | V-1 | KIAA0513 | 1.52 |
| 2012 | 3 | 4 | 5 | | V-1 | HS2ST1 | 1.92 | 2108 | 3 | 4 | 5 | | V-1 | KIAA0586 | 1.53 |
| 2013 | 3 | 4 | 5 | | V-1 | HSD17B1 | 1.53 | 2109 | 3 | 4 | 5 | | V-1 | KIAA0664 | 1.80 |

Fig. 41 - 12

| | | | | | | | | | | | | | | | |
|---|---|---|---|---|---|---|---|---|---|---|---|---|---|---|---|
| 2110 | 3 | 4 | 5 | | V-1 | KIAA1009 | 1.61 | 2206 | 3 | 4 | 5 | | V-1 | LOC653566 | 1.82 |
| 2111 | 3 | 4 | 5 | | V-1 | KIAA1033 | 1.79 | 2207 | 3 | 4 | 5 | | V-1 | LOC654342 | 1.65 |
| 2112 | 3 | 4 | 5 | | V-1 | KIAA1279 | 1.85 | 2208 | 3 | 4 | 5 | | V-1 | LOC727896 | 1.56 |
| 2113 | 3 | 4 | 5 | | V-1 | KIAA1383 | 1.62 | 2209 | 3 | 4 | 5 | | V-1 | LOC729852 | 1.51 |
| 2114 | 3 | 4 | 5 | | V-1 | KIAA1429 | 1.78 | 2210 | 3 | 4 | 5 | | V-1 | LONP1 | 1.96 |
| 2115 | 3 | 4 | 5 | | V-1 | KIAA1432 | 1.84 | 2211 | 3 | 4 | 5 | | V-1 | LPCAT3 | 1.82 |
| 2116 | 3 | 4 | 5 | | V-1 | KIAA1467 | 1.56 | 2212 | 3 | 4 | 5 | | V-1 | LRCH1 | 1.59 |
| 2117 | 3 | 4 | 5 | | V-1 | KIAA1609 | 1.50 | 2213 | 3 | 4 | 5 | | V-1 | LRCH3 | 1.65 |
| 2118 | 3 | 4 | 5 | | V-1 | KIAA1715 | 1.60 | 2214 | 3 | 4 | 5 | | V-1 | LRP8 | 1.64 |
| 2119 | 3 | 4 | 5 | | V-1 | KIAA1826 | 1.51 | 2215 | 3 | 4 | 5 | | V-1 | LRPAP1 | 1.75 |
| 2120 | 3 | 4 | 5 | | V-1 | KIAA1967 | 1.76 | 2216 | 3 | 4 | 5 | | V-1 | LRRC25 | 1.80 |
| 2121 | 3 | 4 | 5 | | V-1 | KIAA2026 | 1.55 | 2217 | 3 | 4 | 5 | | V-1 | LRRC40 | 1.68 |
| 2122 | 3 | 4 | 5 | | V-1 | KIDINS220 | 1.90 | 2218 | 3 | 4 | 5 | | V-1 | LRRC45 | 1.74 |
| 2123 | 3 | 4 | 5 | | V-1 | KIF1B | 1.97 | 2219 | 3 | 4 | 5 | | V-1 | LRRC47 | 1.69 |
| 2124 | 3 | 4 | 5 | | V-1 | KIF1C | 1.54 | 2220 | 3 | 4 | 5 | | V-1 | LRRC8B | 1.52 |
| 2125 | 3 | 4 | 5 | | V-1 | KIF20B | 1.53 | 2221 | 3 | 4 | 5 | | V-1 | LRRC8C | 1.90 |
| 2126 | 3 | 4 | 5 | | V-1 | KIF3B | 2.00 | 2222 | 3 | 4 | 5 | | V-1 | LRRFIP1 | 1.56 |
| 2127 | 3 | 4 | 5 | | V-1 | KIF5B | 1.91 | 2223 | 3 | 4 | 5 | | V-1 | LRRK1 | 1.61 |
| 2128 | 3 | 4 | 5 | | V-1 | KIFAP3 | 1.71 | 2224 | 3 | 4 | 5 | | V-1 | LSM14B | 1.71 |
| 2129 | 3 | 4 | 5 | | V-1 | KLF13 | 1.72 | 2225 | 3 | 4 | 5 | | V-1 | LSM4 | 1.73 |
| 2130 | 3 | 4 | 5 | | V-1 | KLF16 | 1.78 | 2226 | 3 | 4 | 5 | | V-1 | LSM5 | 1.70 |
| 2131 | 3 | 4 | 5 | | V-1 | KLHDC5 | 1.64 | 2227 | 3 | 4 | 5 | | V-1 | LTB4R2 | 1.83 |
| 2132 | 3 | 4 | 5 | | V-1 | KLHL15 | 1.70 | 2228 | 3 | 4 | 5 | | V-1 | LTV1 | 1.54 |
| 2133 | 3 | 4 | 5 | | V-1 | KLHL18 | 1.88 | 2229 | 3 | 4 | 5 | | V-1 | LYAR | 1.77 |
| 2134 | 3 | 4 | 5 | | V-1 | KLHL26 | 1.93 | 2230 | 3 | 4 | 5 | | V-1 | LYRM2 | 1.51 |
| 2135 | 3 | 4 | 5 | | V-1 | KLHL5 | 1.65 | 2231 | 3 | 4 | 5 | | V-1 | LZTR1 | 1.62 |
| 2136 | 3 | 4 | 5 | | V-1 | KPNA6 | 1.84 | 2232 | 3 | 4 | 5 | | V-1 | M6PR | 1.72 |
| 2137 | 3 | 4 | 5 | | V-1 | KPTN | 1.62 | 2233 | 3 | 4 | 5 | | V-1 | MAD2L1BP | 1.65 |
| 2138 | 3 | 4 | 5 | | V-1 | KRAS | 1.64 | 2234 | 3 | 4 | 5 | | V-1 | MAF | 1.72 |
| 2139 | 3 | 4 | 5 | | V-1 | KRTCAP2 | 1.52 | 2235 | 3 | 4 | 5 | | V-1 | MAGT1 | 1.50 |
| 2140 | 3 | 4 | 5 | | V-1 | KTI12 | 1.63 | 2236 | 3 | 4 | 5 | | V-1 | MAN1A1 | 1.80 |
| 2141 | 3 | 4 | 5 | | V-1 | L1TD1 | 1.59 | 2237 | 3 | 4 | 5 | | V-1 | MAN2C1 | 1.57 |
| 2142 | 3 | 4 | 5 | | V-1 | L3MBTL2 | 1.73 | 2238 | 3 | 4 | 5 | | V-1 | MANEA | 1.66 |
| 2143 | 3 | 4 | 5 | | V-1 | LAGE3 | 1.65 | 2239 | 3 | 4 | 5 | | V-1 | MANEAL | 1.60 |
| 2144 | 3 | 4 | 5 | | V-1 | LAMP2 | 1.57 | 2240 | 3 | 4 | 5 | | V-1 | MANF | 1.56 |
| 2145 | 3 | 4 | 5 | | V-1 | LAMTOR2 | 1.72 | 2241 | 3 | 4 | 5 | | V-1 | MAP1S | 1.62 |
| 2146 | 3 | 4 | 5 | | V-1 | LANCL2 | 1.87 | 2242 | 3 | 4 | 5 | | V-1 | MAP3K1 | 1.76 |
| 2147 | 3 | 4 | 5 | | V-1 | LAPTM5 | 1.56 | 2243 | 3 | 4 | 5 | | V-1 | MAP3K12 | 1.89 |
| 2148 | 3 | 4 | 5 | | V-1 | LARP1B | 1.65 | 2244 | 3 | 4 | 5 | | V-1 | MAP3K4 | 1.55 |
| 2149 | 3 | 4 | 5 | | V-1 | LARP4B | 1.58 | 2245 | 3 | 4 | 5 | | V-1 | MAP3K8 | 1.58 |
| 2150 | 3 | 4 | 5 | | V-1 | LARP7 | 1.77 | 2246 | 3 | 4 | 5 | | V-1 | MAPK1 | 1.58 |
| 2151 | 3 | 4 | 5 | | V-1 | LARS2 | 1.77 | 2247 | 3 | 4 | 5 | | V-1 | MAPK14 | 1.56 |
| 2152 | 3 | 4 | 5 | | V-1 | LATS1 | 1.60 | 2248 | 3 | 4 | 5 | | V-1 | MAPK1IP1L | 1.77 |
| 2153 | 3 | 4 | 5 | | V-1 | LATS2 | 1.77 | 2249 | 3 | 4 | 5 | | V-1 | MAPK6 | 1.57 |
| 2154 | 3 | 4 | 5 | | V-1 | L8R | 1.65 | 2250 | 3 | 4 | 5 | | V-1 | MAPK9 | 1.53 |
| 2155 | 3 | 4 | 5 | | V-1 | LCORL | 1.70 | 2251 | 3 | 4 | 5 | | V-1 | MAPKAP1 | 1.63 |
| 2156 | 3 | 4 | 5 | | V-1 | LCP1 | 1.51 | 2252 | 3 | 4 | 5 | | V-1 | MAPKAPK3 | 1.95 |
| 2157 | 3 | 4 | 5 | | V-1 | LDOC1L | 1.67 | 2253 | 3 | 4 | 5 | | V-1 | MAPRE2 | 1.63 |
| 2158 | 3 | 4 | 5 | | V-1 | LEO1 | 2.00 | 2254 | 3 | 4 | 5 | | V-1 | MARK4 | 1.76 |
| 2159 | 3 | 4 | 5 | | V-1 | LEPRE1 | 1.92 | 2255 | 3 | 4 | 5 | | V-1 | MAST2 | 1.70 |
| 2160 | 3 | 4 | 5 | | V-1 | LFNG | 1.99 | 2256 | 3 | 4 | 5 | | V-1 | MAT2A | 1.53 |
| 2161 | 3 | 4 | 5 | | V-1 | LILRA1 | 1.72 | 2257 | 3 | 4 | 5 | | V-1 | MATR3 | 1.59 |
| 2162 | 3 | 4 | 5 | | V-1 | LILRB2 | 1.62 | 2258 | 3 | 4 | 5 | | V-1 | MAVS | 1.55 |
| 2163 | 3 | 4 | 5 | | V-1 | LILRB3 | 1.81 | 2259 | 3 | 4 | 5 | | V-1 | MB21D1 | 1.84 |
| 2164 | 3 | 4 | 5 | | V-1 | LIMA1 | 1.63 | 2260 | 3 | 4 | 5 | | V-1 | MB21D2 | 1.63 |
| 2165 | 3 | 4 | 5 | | V-1 | LIMD1 | 1.80 | 2261 | 3 | 4 | 5 | | V-1 | MBD3 | 1.75 |
| 2166 | 3 | 4 | 5 | | V-1 | LIMK1 | 1.62 | 2262 | 3 | 4 | 5 | | V-1 | MBOAT1 | 1.96 |
| 2167 | 3 | 4 | 5 | | V-1 | LINC00265 | 1.82 | 2263 | 3 | 4 | 5 | | V-1 | MBTPS1 | 1.90 |
| 2168 | 3 | 4 | 5 | | V-1 | LINC00294 | 1.57 | 2264 | 3 | 4 | 5 | | V-1 | MCAT | 1.51 |
| 2169 | 3 | 4 | 5 | | V-1 | LINC00341 | 1.87 | 2265 | 3 | 4 | 5 | | V-1 | MCCC2 | 1.60 |
| 2170 | 3 | 4 | 5 | | V-1 | LINC00476 | 1.53 | 2266 | 3 | 4 | 5 | | V-1 | MCFD2 | 1.60 |
| 2171 | 3 | 4 | 5 | | V-1 | LINC00493 | 1.51 | 2267 | 3 | 4 | 5 | | V-1 | MCM3AP | 1.58 |
| 2172 | 3 | 4 | 5 | | V-1 | LLPH | 1.61 | 2268 | 3 | 4 | 5 | | V-1 | MCRS1 | 1.61 |
| 2173 | 3 | 4 | 5 | | V-1 | LMAN1 | 1.74 | 2269 | 3 | 4 | 5 | | V-1 | MDFIC | 1.56 |
| 2174 | 3 | 4 | 5 | | V-1 | LMAN2 | 1.60 | 2270 | 3 | 4 | 5 | | V-1 | MDH1 | 1.76 |
| 2175 | 3 | 4 | 5 | | V-1 | LMAN2L | 1.94 | 2271 | 3 | 4 | 5 | | V-1 | MDH2 | 1.82 |
| 2176 | 3 | 4 | 5 | | V-1 | LMBR1 | 1.59 | 2272 | 3 | 4 | 5 | | V-1 | ME2 | 1.67 |
| 2177 | 3 | 4 | 5 | | V-1 | LMBRD2 | 1.90 | 2273 | 3 | 4 | 5 | | V-1 | MED1 | 1.59 |
| 2178 | 3 | 4 | 5 | | V-1 | LMO4 | 1.72 | 2274 | 3 | 4 | 5 | | V-1 | MED13 | 1.58 |
| 2179 | 3 | 4 | 5 | | V-1 | LOC100009676 | 1.67 | 2275 | 3 | 4 | 5 | | V-1 | MED16 | 1.63 |
| 2180 | 3 | 4 | 5 | | V-1 | LOC100128191 | 1.61 | 2276 | 3 | 4 | 5 | | V-1 | MED17 | 1.61 |
| 2181 | 3 | 4 | 5 | | V-1 | LOC100129361 | 1.58 | 2277 | 3 | 4 | 5 | | V-1 | MED22 | 1.55 |
| 2182 | 3 | 4 | 5 | | V-1 | LOC100132077 | 1.85 | 2278 | 3 | 4 | 5 | | V-1 | MED24 | 1.84 |
| 2183 | 3 | 4 | 5 | | V-1 | LOC100288432 | 1.82 | 2279 | 3 | 4 | 5 | | V-1 | MED27 | 1.77 |
| 2184 | 3 | 4 | 5 | | V-1 | LOC100288846 | 1.98 | 2280 | 3 | 4 | 5 | | V-1 | MED4 | 1.55 |
| 2185 | 3 | 4 | 5 | | V-1 | LOC100329109 | 1.58 | 2281 | 3 | 4 | 5 | | V-1 | MED8 | 1.85 |
| 2186 | 3 | 4 | 5 | | V-1 | LOC100505549 | 1.79 | 2282 | 3 | 4 | 5 | | V-1 | MEF2A | 1.95 |
| 2187 | 3 | 4 | 5 | | V-1 | LOC100506668 | 1.56 | 2283 | 3 | 4 | 5 | | V-1 | MEGF8 | 1.70 |
| 2188 | 3 | 4 | 5 | | V-1 | LOC100507412 | 1.52 | 2284 | 3 | 4 | 5 | | V-1 | MESDC2 | 1.77 |
| 2189 | 3 | 4 | 5 | | V-1 | LOC100507632 | 1.79 | 2285 | 3 | 4 | 5 | | V-1 | METAP1 | 1.73 |
| 2190 | 3 | 4 | 5 | | V-1 | LOC100630923 | 1.79 | 2286 | 3 | 4 | 5 | | V-1 | METRNL | 1.83 |
| 2191 | 3 | 4 | 5 | | V-1 | LOC100859930 | 1.66 | 2287 | 3 | 4 | 5 | | V-1 | METTL10 | 1.60 |
| 2192 | 3 | 4 | 5 | | V-1 | LOC147727 | 1.50 | 2288 | 3 | 4 | 5 | | V-1 | METTL11A | 1.70 |
| 2193 | 3 | 4 | 5 | | V-1 | LOC148189 | 1.71 | 2289 | 3 | 4 | 5 | | V-1 | METTL15 | 1.80 |
| 2194 | 3 | 4 | 5 | | V-1 | LOC153684 | 1.51 | 2290 | 3 | 4 | 5 | | V-1 | METTL16 | 1.75 |
| 2195 | 3 | 4 | 5 | | V-1 | LOC283692 | 1.57 | 2291 | 3 | 4 | 5 | | V-1 | METTL18 | 1.74 |
| 2196 | 3 | 4 | 5 | | V-1 | LOC285033 | 1.52 | 2292 | 3 | 4 | 5 | | V-1 | METTL19 | 1.74 |
| 2197 | 3 | 4 | 5 | | V-1 | LOC341056 | 1.66 | 2293 | 3 | 4 | 5 | | V-1 | METTL2B | 1.64 |
| 2198 | 3 | 4 | 5 | | V-1 | LOC401010 | 1.97 | 2294 | 3 | 4 | 5 | | V-1 | MEX3D | 1.95 |
| 2199 | 3 | 4 | 5 | | V-1 | LOC401127 | 1.53 | 2295 | 3 | 4 | 5 | | V-1 | MFAP3 | 1.71 |
| 2200 | 3 | 4 | 5 | | V-1 | LOC440354 | 1.89 | 2296 | 3 | 4 | 5 | | V-1 | MFSD10 | 1.60 |
| 2201 | 3 | 4 | 5 | | V-1 | LOC613038 | 1.57 | 2297 | 3 | 4 | 5 | | V-1 | MFSD11 | 1.87 |
| 2202 | 3 | 4 | 5 | | V-1 | LOC642361 | 1.89 | 2298 | 3 | 4 | 5 | | V-1 | MFSD3 | 1.94 |
| 2203 | 3 | 4 | 5 | | V-1 | LOC643387 | 1.71 | 2299 | 3 | 4 | 5 | | V-1 | MFSD5 | 1.70 |
| 2204 | 3 | 4 | 5 | | V-1 | LOC647979 | 1.57 | 2300 | 3 | 4 | 5 | | V-1 | MFSD6 | 1.72 |
| 2205 | 3 | 4 | 5 | | V-1 | LOC648987 | 1.76 | 2301 | 3 | 4 | 5 | | V-1 | MGAT1 | 1.67 |

Fig. 41 - 13

| | | | | | | | | | | | | | | | | |
|---|---|---|---|---|---|---|---|---|---|---|---|---|---|---|---|---|
| 2302 | 3 | 4 | 5 | | | V-1 | MGAT2 | 1.83 | 2398 | 3 | 4 | 5 | | | V-1 | NANS | 1.88 |
| 2303 | 3 | 4 | 5 | | | V-1 | MGC12982 | 1.66 | 2399 | 3 | 4 | 5 | | | V-1 | NAP1L1 | 1.77 |
| 2304 | 3 | 4 | 5 | | | V-1 | MGMT | 1.93 | 2400 | 3 | 4 | 5 | | | V-1 | NAPEPLD | 1.78 |
| 2305 | 3 | 4 | 5 | | | V-1 | MGST3 | 1.75 | 2401 | 3 | 4 | 5 | | | V-1 | NARFL | 1.75 |
| 2306 | 3 | 4 | 5 | | | V-1 | MICU1 | 1.91 | 2402 | 3 | 4 | 5 | | | V-1 | NAT1 | 1.57 |
| 2307 | 3 | 4 | 5 | | | V-1 | MIER3 | 1.60 | 2403 | 3 | 4 | 5 | | | V-1 | NAT10 | 1.74 |
| 2308 | 3 | 4 | 5 | | | V-1 | MIIP | 1.54 | 2404 | 3 | 4 | 5 | | | V-1 | NBPF10 | 1.53 |
| 2309 | 3 | 4 | 5 | | | V-1 | MINA | 1.84 | 2405 | 3 | 4 | 5 | | | V-1 | NBR1 | 1.62 |
| 2310 | 3 | 4 | 5 | | | V-1 | MINPP1 | 1.90 | 2406 | 3 | 4 | 5 | | | V-1 | NCAPD2 | 1.63 |
| 2311 | 3 | 4 | 5 | | | V-1 | MIOS | 1.65 | 2407 | 3 | 4 | 5 | | | V-1 | NCBP2 | 1.62 |
| 2312 | 3 | 4 | 5 | | | V-1 | MIS18BP1 | 1.90 | 2408 | 3 | 4 | 5 | | | V-1 | NCKIPSD | 1.71 |
| 2313 | 3 | 4 | 5 | | | V-1 | MKI67IP | 1.79 | 2409 | 3 | 4 | 5 | | | V-1 | NCLN | 1.91 |
| 2314 | 3 | 4 | 5 | | | V-1 | MKL1 | 1.55 | 2410 | 3 | 4 | 5 | | | V-1 | NCOA3 | 1.52 |
| 2315 | 3 | 4 | 5 | | | V-1 | MLXIP | 1.59 | 2411 | 3 | 4 | 5 | | | V-1 | NCOA7 | 1.59 |
| 2316 | 3 | 4 | 5 | | | V-1 | MMADHC | 1.59 | 2412 | 3 | 4 | 5 | | | V-1 | NDFIP1 | 1.66 |
| 2317 | 3 | 4 | 5 | | | V-1 | MMGT1 | 1.92 | 2413 | 3 | 4 | 5 | | | V-1 | NDRG1 | 1.64 |
| 2318 | 3 | 4 | 5 | | | V-1 | MMS19 | 1.65 | 2414 | 3 | 4 | 5 | | | V-1 | NDUFA10 | 1.92 |
| 2319 | 3 | 4 | 5 | | | V-1 | MOB1A | 1.81 | 2415 | 3 | 4 | 5 | | | V-1 | NDUFA12 | 1.93 |
| 2320 | 3 | 4 | 5 | | | V-1 | MOCS1 | 1.86 | 2416 | 3 | 4 | 5 | | | V-1 | NDUFA3 | 1.84 |
| 2321 | 3 | 4 | 5 | | | V-1 | MOCS3 | 1.66 | 2417 | 3 | 4 | 5 | | | V-1 | NDUFA6 | 1.63 |
| 2322 | 3 | 4 | 5 | | | V-1 | MON1A | 1.69 | 2418 | 3 | 4 | 5 | | | V-1 | NDUFA9 | 1.77 |
| 2323 | 3 | 4 | 5 | | | V-1 | MORF4L2 | 1.53 | 2419 | 3 | 4 | 5 | | | V-1 | NDUFAF3 | 1.92 |
| 2324 | 3 | 4 | 5 | | | V-1 | MORN2 | 1.94 | 2420 | 3 | 4 | 5 | | | V-1 | NDUFB3 | 1.58 |
| 2325 | 3 | 4 | 5 | | | V-1 | MOSPD1 | 1.55 | 2421 | 3 | 4 | 5 | | | V-1 | NDUFB5 | 1.61 |
| 2326 | 3 | 4 | 5 | | | V-1 | MOV10 | 1.81 | 2422 | 3 | 4 | 5 | | | V-1 | NDUFS2 | 1.74 |
| 2327 | 3 | 4 | 5 | | | V-1 | MPDU1 | 1.92 | 2423 | 3 | 4 | 5 | | | V-1 | NDUFS6 | 1.99 |
| 2328 | 3 | 4 | 5 | | | V-1 | MPHOSPH8 | 1.57 | 2424 | 3 | 4 | 5 | | | V-1 | NDUFS8 | 1.66 |
| 2329 | 3 | 4 | 5 | | | V-1 | MPND | 1.68 | 2425 | 3 | 4 | 5 | | | V-1 | NDUFV3 | 1.99 |
| 2330 | 3 | 4 | 5 | | | V-1 | MPP7 | 1.60 | 2426 | 3 | 4 | 5 | | | V-1 | NECAP2 | 1.99 |
| 2331 | 3 | 4 | 5 | | | V-1 | MPV17 | 1.65 | 2427 | 3 | 4 | 5 | | | V-1 | NEDD1 | 1.71 |
| 2332 | 3 | 4 | 5 | | | V-1 | MRPL15 | 1.81 | 2428 | 3 | 4 | 5 | | | V-1 | NEDD8 | 1.51 |
| 2333 | 3 | 4 | 5 | | | V-1 | MRPL18 | 1.61 | 2429 | 3 | 4 | 5 | | | V-1 | NEK9 | 1.75 |
| 2334 | 3 | 4 | 5 | | | V-1 | MRPL20 | 1.67 | 2430 | 3 | 4 | 5 | | | V-1 | NET1 | 1.84 |
| 2335 | 3 | 4 | 5 | | | V-1 | MRPL21 | 1.53 | 2431 | 3 | 4 | 5 | | | V-1 | NETO2 | 1.92 |
| 2336 | 3 | 4 | 5 | | | V-1 | MRPL23 | 1.86 | 2432 | 3 | 4 | 5 | | | V-1 | NEU1 | 1.79 |
| 2337 | 3 | 4 | 5 | | | V-1 | MRPL28 | 1.56 | 2433 | 3 | 4 | 5 | | | V-1 | NEU3 | 1.67 |
| 2338 | 3 | 4 | 5 | | | V-1 | MRPL35 | 1.60 | 2434 | 3 | 4 | 5 | | | V-1 | NEXN | 1.57 |
| 2339 | 3 | 4 | 5 | | | V-1 | MRPL37 | 1.78 | 2435 | 3 | 4 | 5 | | | V-1 | NF1 | 1.53 |
| 2340 | 3 | 4 | 5 | | | V-1 | MRPL38 | 1.51 | 2436 | 3 | 4 | 5 | | | V-1 | NF2 | 1.52 |
| 2341 | 3 | 4 | 5 | | | V-1 | MRPL45 | 1.57 | 2437 | 3 | 4 | 5 | | | V-1 | NFE2L1 | 1.88 |
| 2342 | 3 | 4 | 5 | | | V-1 | MRPL46 | 1.51 | 2438 | 3 | 4 | 5 | | | V-1 | NFE2L2 | 1.60 |
| 2343 | 3 | 4 | 5 | | | V-1 | MRPL52 | 1.70 | 2439 | 3 | 4 | 5 | | | V-1 | NFIC | 1.50 |
| 2344 | 3 | 4 | 5 | | | V-1 | MRPS10 | 1.79 | 2440 | 3 | 4 | 5 | | | V-1 | NFKB1 | 1.90 |
| 2345 | 3 | 4 | 5 | | | V-1 | MRPS11 | 1.54 | 2441 | 3 | 4 | 5 | | | V-1 | NFKBIE | 1.76 |
| 2346 | 3 | 4 | 5 | | | V-1 | MRPS12 | 1.68 | 2442 | 3 | 4 | 5 | | | V-1 | NFKBIL1 | 1.66 |
| 2347 | 3 | 4 | 5 | | | V-1 | MRPS18C | 1.99 | 2443 | 3 | 4 | 5 | | | V-1 | NFRKB | 1.66 |
| 2348 | 3 | 4 | 5 | | | V-1 | MRPS21 | 1.61 | 2444 | 3 | 4 | 5 | | | V-1 | NFS1 | 1.84 |
| 2349 | 3 | 4 | 5 | | | V-1 | MRPS22 | 1.58 | 2445 | 3 | 4 | 5 | | | V-1 | NHEJ1 | 1.54 |
| 2350 | 3 | 4 | 5 | | | V-1 | MRPS23 | 1.68 | 2446 | 3 | 4 | 5 | | | V-1 | NHLRC1 | 1.71 |
| 2351 | 3 | 4 | 5 | | | V-1 | MRPS30 | 1.87 | 2447 | 3 | 4 | 5 | | | V-1 | NIPA2 | 1.95 |
| 2352 | 3 | 4 | 5 | | | V-1 | MRPS33 | 1.54 | 2448 | 3 | 4 | 5 | | | V-1 | NIT1 | 1.54 |
| 2353 | 3 | 4 | 5 | | | V-1 | MRPS34 | 1.53 | 2449 | 3 | 4 | 5 | | | V-1 | NKAP | 1.58 |
| 2354 | 3 | 4 | 5 | | | V-1 | MRPS35 | 1.93 | 2450 | 3 | 4 | 5 | | | V-1 | NKIRAS2 | 1.80 |
| 2355 | 3 | 4 | 5 | | | V-1 | MRPS5 | 1.82 | 2451 | 3 | 4 | 5 | | | V-1 | NKRF | 1.52 |
| 2356 | 3 | 4 | 5 | | | V-1 | MRPS7 | 1.69 | 2452 | 3 | 4 | 5 | | | V-1 | NMD3 | 1.54 |
| 2357 | 3 | 4 | 5 | | | V-1 | MRPS9 | 1.63 | 2453 | 3 | 4 | 5 | | | V-1 | NME2 | 1.65 |
| 2358 | 3 | 4 | 5 | | | V-1 | MRRF | 1.95 | 2454 | 3 | 4 | 5 | | | V-1 | NME3 | 1.66 |
| 2359 | 3 | 4 | 5 | | | V-1 | MRS2P2 | 1.71 | 2455 | 3 | 4 | 5 | | | V-1 | NMNAT1 | 1.77 |
| 2360 | 3 | 4 | 5 | | | V-1 | MSH6 | 1.61 | 2456 | 3 | 4 | 5 | | | V-1 | NMNAT3 | 1.63 |
| 2361 | 3 | 4 | 5 | | | V-1 | MSRA | 1.79 | 2457 | 3 | 4 | 5 | | | V-1 | NMT1 | 1.70 |
| 2362 | 3 | 4 | 5 | | | V-1 | MT2A | 1.93 | 2458 | 3 | 4 | 5 | | | V-1 | NOA1 | 1.66 |
| 2363 | 3 | 4 | 5 | | | V-1 | MTA1 | 1.77 | 2459 | 3 | 4 | 5 | | | V-1 | NOB1 | 1.51 |
| 2364 | 3 | 4 | 5 | | | V-1 | MTA2 | 1.70 | 2460 | 3 | 4 | 5 | | | V-1 | NOC2L | 1.97 |
| 2365 | 3 | 4 | 5 | | | V-1 | MTCH2 | 1.94 | 2461 | 3 | 4 | 5 | | | V-1 | NOL11 | 1.59 |
| 2366 | 3 | 4 | 5 | | | V-1 | MTF2 | 1.52 | 2462 | 3 | 4 | 5 | | | V-1 | NOL3 | 1.56 |
| 2367 | 3 | 4 | 5 | | | V-1 | MTG1 | 1.67 | 2463 | 3 | 4 | 5 | | | V-1 | NOL6 | 1.60 |
| 2368 | 3 | 4 | 5 | | | V-1 | MTHFSD | 1.53 | 2464 | 3 | 4 | 5 | | | V-1 | NOL8 | 1.78 |
| 2369 | 3 | 4 | 5 | | | V-1 | MTIF2 | 1.71 | 2465 | 3 | 4 | 5 | | | V-1 | NOL9 | 1.56 |
| 2370 | 3 | 4 | 5 | | | V-1 | MTMR14 | 1.51 | 2466 | 3 | 4 | 5 | | | V-1 | NOLC1 | 1.76 |
| 2371 | 3 | 4 | 5 | | | V-1 | MTMR6 | 1.55 | 2467 | 3 | 4 | 5 | | | V-1 | NOP56 | 1.50 |
| 2372 | 3 | 4 | 5 | | | V-1 | MTMR9 | 1.57 | 2468 | 3 | 4 | 5 | | | V-1 | NOP58 | 1.58 |
| 2373 | 3 | 4 | 5 | | | V-1 | MTOR | 1.54 | 2469 | 3 | 4 | 5 | | | V-1 | NOTCH2 | 2.00 |
| 2374 | 3 | 4 | 5 | | | V-1 | MTP4P | 1.76 | 2470 | 3 | 4 | 5 | | | V-1 | NOTCH2NL | 1.86 |
| 2375 | 3 | 4 | 5 | | | V-1 | MTPN | 1.92 | 2471 | 3 | 4 | 5 | | | V-1 | NPC1 | 1.59 |
| 2376 | 3 | 4 | 5 | | | V-1 | MTRF1L | 1.60 | 2472 | 3 | 4 | 5 | | | V-1 | NPEPL1 | 1.52 |
| 2377 | 3 | 4 | 5 | | | V-1 | MTRR | 1.98 | 2473 | 3 | 4 | 5 | | | V-1 | NPLOC4 | 1.54 |
| 2378 | 3 | 4 | 5 | | | V-1 | MTSS1 | 1.59 | 2474 | 3 | 4 | 5 | | | V-1 | NPTN | 1.76 |
| 2379 | 3 | 4 | 5 | | | V-1 | MUDENG | 1.86 | 2475 | 3 | 4 | 5 | | | V-1 | NQO1 | 1.60 |
| 2380 | 3 | 4 | 5 | | | V-1 | MVP | 1.75 | 2476 | 3 | 4 | 5 | | | V-1 | NQO2 | 1.80 |
| 2381 | 3 | 4 | 5 | | | V-1 | MYCBP2 | 1.76 | 2477 | 3 | 4 | 5 | | | V-1 | NRAS | 1.72 |
| 2382 | 3 | 4 | 5 | | | V-1 | MYD88 | 1.55 | 2478 | 3 | 4 | 5 | | | V-1 | NRIP1 | 1.97 |
| 2383 | 3 | 4 | 5 | | | V-1 | MYEOV2 | 1.82 | 2479 | 3 | 4 | 5 | | | V-1 | NSD1 | 1.62 |
| 2384 | 3 | 4 | 5 | | | V-1 | MYO18A | 1.77 | 2480 | 3 | 4 | 5 | | | V-1 | NSDHL | 1.99 |
| 2385 | 3 | 4 | 5 | | | V-1 | MYO5A | 1.61 | 2481 | 3 | 4 | 5 | | | V-1 | NSMCE1 | 1.72 |
| 2386 | 3 | 4 | 5 | | | V-1 | N4BP2 | 1.51 | 2482 | 3 | 4 | 5 | | | V-1 | NSMCE4A | 1.51 |
| 2387 | 3 | 4 | 5 | | | V-1 | NAA15 | 1.98 | 2483 | 3 | 4 | 5 | | | V-1 | NSRP1 | 1.74 |
| 2388 | 3 | 4 | 5 | | | V-1 | NAA20 | 1.97 | 2484 | 3 | 4 | 5 | | | V-1 | NSUN2 | 1.74 |
| 2389 | 3 | 4 | 5 | | | V-1 | NAA25 | 1.50 | 2485 | 3 | 4 | 5 | | | V-1 | NTHL1 | 1.69 |
| 2390 | 3 | 4 | 5 | | | V-1 | NAA30 | 1.84 | 2486 | 3 | 4 | 5 | | | V-1 | NUBP1 | 1.70 |
| 2391 | 3 | 4 | 5 | | | V-1 | NAA35 | 1.56 | 2487 | 3 | 4 | 5 | | | V-1 | NUBPL | 1.52 |
| 2392 | 3 | 4 | 5 | | | V-1 | NACA2 | 1.99 | 2488 | 3 | 4 | 5 | | | V-1 | NUDC | 1.60 |
| 2393 | 3 | 4 | 5 | | | V-1 | NACAP1 | 1.59 | 2489 | 3 | 4 | 5 | | | V-1 | NUDCD1 | 1.59 |
| 2394 | 3 | 4 | 5 | | | V-1 | NADKD1 | 1.97 | 2490 | 3 | 4 | 5 | | | V-1 | NUDT18 | 1.83 |
| 2395 | 3 | 4 | 5 | | | V-1 | NAGLU | 1.57 | 2491 | 3 | 4 | 5 | | | V-1 | NUDT21 | 1.72 |
| 2396 | 3 | 4 | 5 | | | V-1 | NANOS1 | 1.57 | 2492 | 3 | 4 | 5 | | | V-1 | NUDT4P1 | 1.53 |
| 2397 | 3 | 4 | 5 | | | V-1 | NANP | 1.60 | 2493 | 3 | 4 | 5 | | | V-1 | NUDT7 | 1.67 |

Fig. 41 - 14

| | | | | | | | | | | | | | | | |
|---|---|---|---|---|---|---|---|---|---|---|---|---|---|---|---|
| 2494 | 3 | 4 | 5 | | V-1 | NUDT9 | 2.00 | 2590 | 3 | 4 | 5 | | V-1 | PHF3 | 1.52 |
| 2495 | 3 | 4 | 5 | | V-1 | NUMA1 | 1.52 | 2591 | 3 | 4 | 5 | | V-1 | PHF6 | 1.93 |
| 2496 | 3 | 4 | 5 | | V-1 | NUP133 | 1.57 | 2592 | 3 | 4 | 5 | | V-1 | PHIP | 1.70 |
| 2497 | 3 | 4 | 5 | | V-1 | NUP160 | 1.54 | 2593 | 3 | 4 | 5 | | V-1 | PHYH | 1.66 |
| 2498 | 3 | 4 | 5 | | V-1 | NUP188 | 1.94 | 2594 | 3 | 4 | 5 | | V-1 | PI16 | 1.61 |
| 2499 | 3 | 4 | 5 | | V-1 | NUP205 | 1.65 | 2595 | 3 | 4 | 5 | | V-1 | PI4K2A | 1.75 |
| 2500 | 3 | 4 | 5 | | V-1 | NUP54 | 1.75 | 2596 | 3 | 4 | 5 | | V-1 | PI4KA | 1.52 |
| 2501 | 3 | 4 | 5 | | V-1 | NUP85 | 1.55 | 2597 | 3 | 4 | 5 | | V-1 | PIBF1 | 1.64 |
| 2502 | 3 | 4 | 5 | | V-1 | NUP93 | 1.64 | 2598 | 3 | 4 | 5 | | V-1 | PICALM | 1.61 |
| 2503 | 3 | 4 | 5 | | V-1 | NUPL1 | 1.53 | 2599 | 3 | 4 | 5 | | V-1 | PIGG | 1.51 |
| 2504 | 3 | 4 | 5 | | V-1 | NUS1 | 1.98 | 2600 | 3 | 4 | 5 | | V-1 | PIGH | 1.67 |
| 2505 | 3 | 4 | 5 | | V-1 | O3FAR1 | 1.69 | 2601 | 3 | 4 | 5 | | V-1 | PIGK | 1.80 |
| 2506 | 3 | 4 | 5 | | V-1 | OAT | 1.94 | 2602 | 3 | 4 | 5 | | V-1 | PIGO | 1.61 |
| 2507 | 3 | 4 | 5 | | V-1 | OCEL1 | 1.64 | 2603 | 3 | 4 | 5 | | V-1 | PIGP | 1.58 |
| 2508 | 3 | 4 | 5 | | V-1 | ODF2 | 1.70 | 2604 | 3 | 4 | 5 | | V-1 | PIGS | 1.88 |
| 2509 | 3 | 4 | 5 | | V-1 | OGDH | 1.87 | 2605 | 3 | 4 | 5 | | V-1 | PIK3AP1 | 2.00 |
| 2510 | 3 | 4 | 5 | | V-1 | OGFOD1 | 1.70 | 2606 | 3 | 4 | 5 | | V-1 | PIK3C3 | 1.73 |
| 2511 | 3 | 4 | 5 | | V-1 | OIP5-AS1 | 1.91 | 2607 | 3 | 4 | 5 | | V-1 | PIK3CB | 1.95 |
| 2512 | 3 | 4 | 5 | | V-1 | OLA1 | 1.57 | 2608 | 3 | 4 | 5 | | V-1 | PIK3R2 | 1.92 |
| 2513 | 3 | 4 | 5 | | V-1 | OPA1 | 1.69 | 2609 | 3 | 4 | 5 | | V-1 | PIP4K2B | 1.64 |
| 2514 | 3 | 4 | 5 | | V-1 | OPA3 | 1.52 | 2610 | 3 | 4 | 5 | | V-1 | PIP5K1C | 1.79 |
| 2515 | 3 | 4 | 5 | | V-1 | ORMDL1 | 1.50 | 2611 | 3 | 4 | 5 | | V-1 | PITPNB | 1.54 |
| 2516 | 3 | 4 | 5 | | V-1 | ORMDL2 | 1.79 | 2612 | 3 | 4 | 5 | | V-1 | PITRM1 | 1.74 |
| 2517 | 3 | 4 | 5 | | V-1 | OS9 | 1.55 | 2613 | 3 | 4 | 5 | | V-1 | PJA2 | 1.55 |
| 2518 | 3 | 4 | 5 | | V-1 | OSBP | 1.91 | 2614 | 3 | 4 | 5 | | V-1 | PKD2 | 1.55 |
| 2519 | 3 | 4 | 5 | | V-1 | OSBPL11 | 1.68 | 2615 | 3 | 4 | 5 | | V-1 | PKI55 | 1.70 |
| 2520 | 3 | 4 | 5 | | V-1 | OSTC | 1.63 | 2616 | 3 | 4 | 5 | | V-1 | PKN1 | 1.53 |
| 2521 | 3 | 4 | 5 | | V-1 | OSTM1 | 1.58 | 2617 | 3 | 4 | 5 | | V-1 | PLAGL2 | 1.79 |
| 2522 | 3 | 4 | 5 | | V-1 | OTUD1 | 1.76 | 2618 | 3 | 4 | 5 | | V-1 | PLCB1 | 1.82 |
| 2523 | 3 | 4 | 5 | | V-1 | OTUD4 | 1.53 | 2619 | 3 | 4 | 5 | | V-1 | PLCXD1 | 1.84 |
| 2524 | 3 | 4 | 5 | | V-1 | OXR1 | 1.56 | 2620 | 3 | 4 | 5 | | V-1 | PLD3 | 1.69 |
| 2525 | 3 | 4 | 5 | | V-1 | OXSR1 | 1.55 | 2621 | 3 | 4 | 5 | | V-1 | PLDN | 1.84 |
| 2526 | 3 | 4 | 5 | | V-1 | PA2G4P4 | 1.58 | 2622 | 3 | 4 | 5 | | V-1 | PLEKHB2 | 1.86 |
| 2527 | 3 | 4 | 5 | | V-1 | PABPC1 | 1.71 | 2623 | 3 | 4 | 5 | | V-1 | PLEKHF2 | 1.53 |
| 2528 | 3 | 4 | 5 | | V-1 | PABPC3 | 1.99 | 2624 | 3 | 4 | 5 | | V-1 | PLP2 | 1.88 |
| 2529 | 3 | 4 | 5 | | V-1 | PACRGL | 1.56 | 2625 | 3 | 4 | 5 | | V-1 | PLRG1 | 1.66 |
| 2530 | 3 | 4 | 5 | | V-1 | PAFAH1B1 | 1.90 | 2626 | 3 | 4 | 5 | | V-1 | PLXDC2 | 1.86 |
| 2531 | 3 | 4 | 5 | | V-1 | PAK1IP1 | 1.81 | 2627 | 3 | 4 | 5 | | V-1 | PML | 1.54 |
| 2532 | 3 | 4 | 5 | | V-1 | PAK2 | 1.57 | 2628 | 3 | 4 | 5 | | V-1 | PMM1 | 1.81 |
| 2533 | 3 | 4 | 5 | | V-1 | PANK3 | 1.79 | 2629 | 3 | 4 | 5 | | V-1 | PMPCA | 1.51 |
| 2534 | 3 | 4 | 5 | | V-1 | PAOX | 1.72 | 2630 | 3 | 4 | 5 | | V-1 | PMS2 | 1.62 |
| 2535 | 3 | 4 | 5 | | V-1 | PAPD5 | 1.77 | 2631 | 3 | 4 | 5 | | V-1 | PMVK | 1.81 |
| 2536 | 3 | 4 | 5 | | V-1 | PAPOLA | 1.51 | 2632 | 3 | 4 | 5 | | V-1 | PNKD | 1.70 |
| 2537 | 3 | 4 | 5 | | V-1 | PAPSS1 | 1.88 | 2633 | 3 | 4 | 5 | | V-1 | PNO1 | 1.83 |
| 2538 | 3 | 4 | 5 | | V-1 | PARK7 | 1.63 | 2634 | 3 | 4 | 5 | | V-1 | PNP | 1.96 |
| 2539 | 3 | 4 | 5 | | V-1 | PARN | 1.52 | 2635 | 3 | 4 | 5 | | V-1 | PNPLA8 | 1.77 |
| 2540 | 3 | 4 | 5 | | V-1 | PARP11 | 1.69 | 2636 | 3 | 4 | 5 | | V-1 | POFUT1 | 1.91 |
| 2541 | 3 | 4 | 5 | | V-1 | PARP14 | 1.54 | 2637 | 3 | 4 | 5 | | V-1 | POGK | 1.90 |
| 2542 | 3 | 4 | 5 | | V-1 | PARP4 | 1.66 | 2638 | 3 | 4 | 5 | | V-1 | POLA2 | 1.51 |
| 2543 | 3 | 4 | 5 | | V-1 | PARVB | 1.57 | 2639 | 3 | 4 | 5 | | V-1 | POLD3 | 1.54 |
| 2544 | 3 | 4 | 5 | | V-1 | PBRM1 | 1.85 | 2640 | 3 | 4 | 5 | | V-1 | POLDIP2 | 1.53 |
| 2545 | 3 | 4 | 5 | | V-1 | PCID2 | 1.87 | 2641 | 3 | 4 | 5 | | V-1 | POLDIP3 | 1.68 |
| 2546 | 3 | 4 | 5 | | V-1 | PCM1 | 1.51 | 2642 | 3 | 4 | 5 | | V-1 | POLK | 1.82 |
| 2547 | 3 | 4 | 5 | | V-1 | PCNA | 1.85 | 2643 | 3 | 4 | 5 | | V-1 | POLR2B | 1.54 |
| 2548 | 3 | 4 | 5 | | V-1 | PCSK5 | 1.57 | 2644 | 3 | 4 | 5 | | V-1 | POLR2E | 1.51 |
| 2549 | 3 | 4 | 5 | | V-1 | PDCD11 | 1.83 | 2645 | 3 | 4 | 5 | | V-1 | POLRMT | 1.61 |
| 2550 | 3 | 4 | 5 | | V-1 | PDCD7 | 1.81 | 2646 | 3 | 4 | 5 | | V-1 | POP5 | 1.54 |
| 2551 | 3 | 4 | 5 | | V-1 | PDE12 | 1.90 | 2647 | 3 | 4 | 5 | | V-1 | POTEF | 1.73 |
| 2552 | 3 | 4 | 5 | | V-1 | PDE4A | 1.61 | 2648 | 3 | 4 | 5 | | V-1 | POTEKP | 1.64 |
| 2553 | 3 | 4 | 5 | | V-1 | PDE4DIP | 1.67 | 2649 | 3 | 4 | 5 | | V-1 | POTEM | 1.55 |
| 2554 | 3 | 4 | 5 | | V-1 | PDHA1 | 1.76 | 2650 | 3 | 4 | 5 | | V-1 | POU2F1 | 1.50 |
| 2555 | 3 | 4 | 5 | | V-1 | PDHB | 1.67 | 2651 | 3 | 4 | 5 | | V-1 | PPARA | 1.52 |
| 2556 | 3 | 4 | 5 | | V-1 | PDIA3P | 1.85 | 2652 | 3 | 4 | 5 | | V-1 | PPFIBP2 | 1.51 |
| 2557 | 3 | 4 | 5 | | V-1 | PDIK1L | 1.58 | 2653 | 3 | 4 | 5 | | V-1 | PPIB | 1.65 |
| 2558 | 3 | 4 | 5 | | V-1 | PDK2 | 1.60 | 2654 | 3 | 4 | 5 | | V-1 | PPIP5K2 | 1.77 |
| 2559 | 3 | 4 | 5 | | V-1 | PDP1 | 1.90 | 2655 | 3 | 4 | 5 | | V-1 | PPM1G | 1.68 |
| 2560 | 3 | 4 | 5 | | V-1 | PDPK1 | 1.51 | 2656 | 3 | 4 | 5 | | V-1 | PPM1H | 1.58 |
| 2561 | 3 | 4 | 5 | | V-1 | PDS5A | 1.69 | 2657 | 3 | 4 | 5 | | V-1 | PPME1 | 1.50 |
| 2562 | 3 | 4 | 5 | | V-1 | PDXDC1 | 2.00 | 2658 | 3 | 4 | 5 | | V-1 | PPP1CB | 1.70 |
| 2563 | 3 | 4 | 5 | | V-1 | PEA15 | 1.67 | 2659 | 3 | 4 | 5 | | V-1 | PPP1CC | 1.66 |
| 2564 | 3 | 4 | 5 | | V-1 | PECR | 1.65 | 2660 | 3 | 4 | 5 | | V-1 | PPP1R12A | 1.60 |
| 2565 | 3 | 4 | 5 | | V-1 | PEF1 | 1.55 | 2661 | 3 | 4 | 5 | | V-1 | PPP1R14B | 1.72 |
| 2566 | 3 | 4 | 5 | | V-1 | PEMT | 1.93 | 2662 | 3 | 4 | 5 | | V-1 | PPP1R7 | 1.73 |
| 2567 | 3 | 4 | 5 | | V-1 | PEPD | 1.79 | 2663 | 3 | 4 | 5 | | V-1 | PPP2CA | 1.63 |
| 2568 | 3 | 4 | 5 | | V-1 | PER2 | 1.69 | 2664 | 3 | 4 | 5 | | V-1 | PPP2R1A | 1.79 |
| 2569 | 3 | 4 | 5 | | V-1 | PES1 | 1.73 | 2665 | 3 | 4 | 5 | | V-1 | PPP2R5A | 1.63 |
| 2570 | 3 | 4 | 5 | | V-1 | PET112 | 1.63 | 2666 | 3 | 4 | 5 | | V-1 | PPP2R5D | 1.58 |
| 2571 | 3 | 4 | 5 | | V-1 | PET117 | 1.74 | 2667 | 3 | 4 | 5 | | V-1 | PPP2R5E | 1.86 |
| 2572 | 3 | 4 | 5 | | V-1 | PEX11B | 1.63 | 2668 | 3 | 4 | 5 | | V-1 | PPP3CB | 1.82 |
| 2573 | 3 | 4 | 5 | | V-1 | PEX26 | 1.81 | 2669 | 3 | 4 | 5 | | V-1 | PPP3R1 | 1.52 |
| 2574 | 3 | 4 | 5 | | V-1 | PEX5 | 1.79 | 2670 | 3 | 4 | 5 | | V-1 | PPP4R2 | 1.57 |
| 2575 | 3 | 4 | 5 | | V-1 | PFDN1 | 1.52 | 2671 | 3 | 4 | 5 | | V-1 | PPP6C | 1.56 |
| 2576 | 3 | 4 | 5 | | V-1 | PFDN2 | 1.57 | 2672 | 3 | 4 | 5 | | V-1 | PPPDE2 | 1.51 |
| 2577 | 3 | 4 | 5 | | V-1 | PFKL | 1.93 | 2673 | 3 | 4 | 5 | | V-1 | PQLC2 | 1.80 |
| 2578 | 3 | 4 | 5 | | V-1 | PFKP | 1.72 | 2674 | 3 | 4 | 5 | | V-1 | PRAM1 | 1.62 |
| 2579 | 3 | 4 | 5 | | V-1 | PGA3 | 1.61 | 2675 | 3 | 4 | 5 | | V-1 | PRCP | 1.61 |
| 2580 | 3 | 4 | 5 | | V-1 | PGAM1 | 1.86 | 2676 | 3 | 4 | 5 | | V-1 | PRDM10 | 1.56 |
| 2581 | 3 | 4 | 5 | | V-1 | PGAM4 | 1.69 | 2677 | 3 | 4 | 5 | | V-1 | PRDX4 | 1.76 |
| 2582 | 3 | 4 | 5 | | V-1 | PGD | 1.92 | 2678 | 3 | 4 | 5 | | V-1 | PRICKLE3 | 1.68 |
| 2583 | 3 | 4 | 5 | | V-1 | PGK1 | 1.91 | 2679 | 3 | 4 | 5 | | V-1 | PRIM2 | 1.78 |
| 2584 | 3 | 4 | 5 | | V-1 | PGLS | 1.78 | 2680 | 3 | 4 | 5 | | V-1 | PRKACA | 1.51 |
| 2585 | 3 | 4 | 5 | | V-1 | PGM2L1 | 1.76 | 2681 | 3 | 4 | 5 | | V-1 | PRKAR1A | 1.60 |
| 2586 | 3 | 4 | 5 | | V-1 | PGPEP1 | 1.56 | 2682 | 3 | 4 | 5 | | V-1 | PRKAR2A | 1.63 |
| 2587 | 3 | 4 | 5 | | V-1 | PGRMC2 | 1.78 | 2683 | 3 | 4 | 5 | | V-1 | PRKCI | 1.56 |
| 2588 | 3 | 4 | 5 | | V-1 | PHACTR4 | 1.65 | 2684 | 3 | 4 | 5 | | V-1 | PRKD3 | 1.68 |
| 2589 | 3 | 4 | 5 | | V-1 | PHAX | 1.53 | 2685 | 3 | 4 | 5 | | V-1 | PRMT5 | 1.54 |

Fig. 41 - 15

| | | | | | | | | |
|---|---|---|---|---|---|---|---|---|
| 2686 | 3 | 4 | 5 | | V-1 | PRMT6 | 1.88 |
| 2687 | 3 | 4 | 5 | | V-1 | PRNP | 1.61 |
| 2688 | 3 | 4 | 5 | | V-1 | PROSER1 | 1.89 |
| 2689 | 3 | 4 | 5 | | V-1 | PRPF18 | 1.51 |
| 2690 | 3 | 4 | 5 | | V-1 | PRPF19 | 1.89 |
| 2691 | 3 | 4 | 5 | | V-1 | PRPF31 | 1.56 |
| 2692 | 3 | 4 | 5 | | V-1 | PRPF4 | 1.61 |
| 2693 | 3 | 4 | 5 | | V-1 | PRPF40A | 1.62 |
| 2694 | 3 | 4 | 5 | | V-1 | PRPF4B | 1.53 |
| 2695 | 3 | 4 | 5 | | V-1 | PRPF6 | 1.55 |
| 2696 | 3 | 4 | 5 | | V-1 | PRPF8 | 1.89 |
| 2697 | 3 | 4 | 5 | | V-1 | PRPSAP1 | 1.68 |
| 2698 | 3 | 4 | 5 | | V-1 | PRRC2C | 1.57 |
| 2699 | 3 | 4 | 5 | | V-1 | PRX | 1.66 |
| 2700 | 3 | 4 | 5 | | V-1 | PSEN1 | 1.62 |
| 2701 | 3 | 4 | 5 | | V-1 | PSENEN | 1.64 |
| 2702 | 3 | 4 | 5 | | V-1 | PSIMCT-1 | 1.67 |
| 2703 | 3 | 4 | 5 | | V-1 | PSMA2 | 1.50 |
| 2704 | 3 | 4 | 5 | | V-1 | PSMA5 | 1.54 |
| 2705 | 3 | 4 | 5 | | V-1 | PSMA7 | 1.99 |
| 2706 | 3 | 4 | 5 | | V-1 | PSMB1 | 1.74 |
| 2707 | 3 | 4 | 5 | | V-1 | PSMB10 | 1.77 |
| 2708 | 3 | 4 | 5 | | V-1 | PSMB2 | 1.77 |
| 2709 | 3 | 4 | 5 | | V-1 | PSMB3 | 1.89 |
| 2710 | 3 | 4 | 5 | | V-1 | PSMB4 | 1.56 |
| 2711 | 3 | 4 | 5 | | V-1 | PSMB7 | 1.84 |
| 2712 | 3 | 4 | 5 | | V-1 | PSMC2 | 1.58 |
| 2713 | 3 | 4 | 5 | | V-1 | PSMC3 | 1.76 |
| 2714 | 3 | 4 | 5 | | V-1 | PSMC5 | 1.53 |
| 2715 | 3 | 4 | 5 | | V-1 | PSMD11 | 1.57 |
| 2716 | 3 | 4 | 5 | | V-1 | PSMD12 | 1.84 |
| 2717 | 3 | 4 | 5 | | V-1 | PSMD13 | 1.51 |
| 2718 | 3 | 4 | 5 | | V-1 | PSMD2 | 1.95 |
| 2719 | 3 | 4 | 5 | | V-1 | PSMD3 | 1.78 |
| 2720 | 3 | 4 | 5 | | V-1 | PSMD5 | 1.57 |
| 2721 | 3 | 4 | 5 | | V-1 | PSMD6 | 1.84 |
| 2722 | 3 | 4 | 5 | | V-1 | PSMD8 | 1.54 |
| 2723 | 3 | 4 | 5 | | V-1 | PSME2 | 1.75 |
| 2724 | 3 | 4 | 5 | | V-1 | PSMG2 | 1.94 |
| 2725 | 3 | 4 | 5 | | V-1 | PSTPIP2 | 1.52 |
| 2726 | 3 | 4 | 5 | | V-1 | PTBP1 | 1.87 |
| 2727 | 3 | 4 | 5 | | V-1 | PTDSS2 | 1.51 |
| 2728 | 3 | 4 | 5 | | V-1 | PTER | 1.91 |
| 2729 | 3 | 4 | 5 | | V-1 | PTGER2 | 1.52 |
| 2730 | 3 | 4 | 5 | | V-1 | PTGER4 | 1.54 |
| 2731 | 3 | 4 | 5 | | V-1 | PTPLAD2 | 1.78 |
| 2732 | 3 | 4 | 5 | | V-1 | PTPLB | 1.68 |
| 2733 | 3 | 4 | 5 | | V-1 | PTPMT1 | 1.54 |
| 2734 | 3 | 4 | 5 | | V-1 | PTPN1 | 1.63 |
| 2735 | 3 | 4 | 5 | | V-1 | PTPN11 | 1.85 |
| 2736 | 3 | 4 | 5 | | V-1 | PTPN2 | 1.64 |
| 2737 | 3 | 4 | 5 | | V-1 | PTPN22 | 1.65 |
| 2738 | 3 | 4 | 5 | | V-1 | PTPN9 | 1.90 |
| 2739 | 3 | 4 | 5 | | V-1 | PTPRC | 1.61 |
| 2740 | 3 | 4 | 5 | | V-1 | PTPRE | 1.56 |
| 2741 | 3 | 4 | 5 | | V-1 | PTX3 | 1.66 |
| 2742 | 3 | 4 | 5 | | V-1 | PURA | 1.77 |
| 2743 | 3 | 4 | 5 | | V-1 | PUS3 | 2.00 |
| 2744 | 3 | 4 | 5 | | V-1 | PUS7L | 1.60 |
| 2745 | 3 | 4 | 5 | | V-1 | PWP1 | 1.66 |
| 2746 | 3 | 4 | 5 | | V-1 | PWP2 | 1.54 |
| 2747 | 3 | 4 | 5 | | V-1 | PWWP2B | 1.94 |
| 2748 | 3 | 4 | 5 | | V-1 | PXMP2 | 1.52 |
| 2749 | 3 | 4 | 5 | | V-1 | PYGL | 1.51 |
| 2750 | 3 | 4 | 5 | | V-1 | PYHIN1 | 1.51 |
| 2751 | 3 | 4 | 5 | | V-1 | QKI | 1.77 |
| 2752 | 3 | 4 | 5 | | V-1 | QTRT1 | 1.76 |
| 2753 | 3 | 4 | 5 | | V-1 | RAB11A | 1.56 |
| 2754 | 3 | 4 | 5 | | V-1 | RAB1A | 1.86 |
| 2755 | 3 | 4 | 5 | | V-1 | RAB20 | 1.55 |
| 2756 | 3 | 4 | 5 | | V-1 | RAB21 | 1.65 |
| 2757 | 3 | 4 | 5 | | V-1 | RAB27A | 1.60 |
| 2758 | 3 | 4 | 5 | | V-1 | RAB2A | 1.56 |
| 2759 | 3 | 4 | 5 | | V-1 | RAB31 | 1.63 |
| 2760 | 3 | 4 | 5 | | V-1 | RAB3GAP1 | 1.98 |
| 2761 | 3 | 4 | 5 | | V-1 | RAB3GAP2 | 1.77 |
| 2762 | 3 | 4 | 5 | | V-1 | RAB4A | 1.61 |
| 2763 | 3 | 4 | 5 | | V-1 | RABGAP1 | 1.58 |
| 2764 | 3 | 4 | 5 | | V-1 | RACGAP1 | 1.56 |
| 2765 | 3 | 4 | 5 | | V-1 | RACGAP1P | 1.65 |
| 2766 | 3 | 4 | 5 | | V-1 | RAD23A | 1.71 |
| 2767 | 3 | 4 | 5 | | V-1 | RAD23B | 1.84 |
| 2768 | 3 | 4 | 5 | | V-1 | RAD50 | 1.99 |
| 2769 | 3 | 4 | 5 | | V-1 | RAD51B | 1.61 |
| 2770 | 3 | 4 | 5 | | V-1 | RAD54L2 | 1.52 |
| 2771 | 3 | 4 | 5 | | V-1 | RAI1 | 1.91 |
| 2772 | 3 | 4 | 5 | | V-1 | RALA | 1.87 |
| 2773 | 3 | 4 | 5 | | V-1 | RALGAPA2 | 1.98 |
| 2774 | 3 | 4 | 5 | | V-1 | RAN | 1.58 |
| 2775 | 3 | 4 | 5 | | V-1 | RANBP2 | 1.65 |
| 2776 | 3 | 4 | 5 | | V-1 | RANBP6 | 1.95 |
| 2777 | 3 | 4 | 5 | | V-1 | RANBP9 | 1.56 |
| 2778 | 3 | 4 | 5 | | V-1 | RANGAP1 | 1.97 |
| 2779 | 3 | 4 | 5 | | V-1 | RAP1GDS1 | 1.95 |
| 2780 | 3 | 4 | 5 | | V-1 | RAP2A | 1.76 |
| 2781 | 3 | 4 | 5 | | V-1 | RAPH1 | 1.80 |
| 2782 | 3 | 4 | 5 | | V-1 | RARG | 1.74 |
| 2783 | 3 | 4 | 5 | | V-1 | RARS | 1.89 |
| 2784 | 3 | 4 | 5 | | V-1 | RASA1 | 1.75 |
| 2785 | 3 | 4 | 5 | | V-1 | RBAK | 1.55 |
| 2786 | 3 | 4 | 5 | | V-1 | RBBP4 | 1.66 |
| 2787 | 3 | 4 | 5 | | V-1 | RBM10 | 1.78 |
| 2788 | 3 | 4 | 5 | | V-1 | RBM12 | 1.67 |
| 2789 | 3 | 4 | 5 | | V-1 | RBM14 | 1.61 |
| 2790 | 3 | 4 | 5 | | V-1 | RBM15B | 1.76 |
| 2791 | 3 | 4 | 5 | | V-1 | RBM17 | 1.60 |
| 2792 | 3 | 4 | 5 | | V-1 | RBM27 | 1.59 |
| 2793 | 3 | 4 | 5 | | V-1 | RBM41 | 1.52 |
| 2794 | 3 | 4 | 5 | | V-1 | RBM5 | 1.88 |
| 2795 | 3 | 4 | 5 | | V-1 | RBMX2 | 1.70 |
| 2796 | 3 | 4 | 5 | | V-1 | RBPJ | 1.54 |
| 2797 | 3 | 4 | 5 | | V-1 | RBX1 | 1.64 |
| 2798 | 3 | 4 | 5 | | V-1 | RCBTB2 | 1.79 |
| 2799 | 3 | 4 | 5 | | V-1 | RCC1 | 1.80 |
| 2800 | 3 | 4 | 5 | | V-1 | RCC2 | 1.91 |
| 2801 | 3 | 4 | 5 | | V-1 | RCOR1 | 1.74 |
| 2802 | 3 | 4 | 5 | | V-1 | RDH10 | 1.62 |
| 2803 | 3 | 4 | 5 | | V-1 | RDH11 | 1.99 |
| 2804 | 3 | 4 | 5 | | V-1 | RDH13 | 1.55 |
| 2805 | 3 | 4 | 5 | | V-1 | RECQL | 1.99 |
| 2806 | 3 | 4 | 5 | | V-1 | REEP3 | 1.77 |
| 2807 | 3 | 4 | 5 | | V-1 | REEP5 | 1.88 |
| 2808 | 3 | 4 | 5 | | V-1 | REL | 1.75 |
| 2809 | 3 | 4 | 5 | | V-1 | RELA | 1.63 |
| 2810 | 3 | 4 | 5 | | V-1 | RENBP | 1.60 |
| 2811 | 3 | 4 | 5 | | V-1 | REST | 1.50 |
| 2812 | 3 | 4 | 5 | | V-1 | RETSAT | 1.61 |
| 2813 | 3 | 4 | 5 | | V-1 | RFC2 | 1.54 |
| 2814 | 3 | 4 | 5 | | V-1 | RFK | 1.80 |
| 2815 | 3 | 4 | 5 | | V-1 | RFT1 | 1.71 |
| 2816 | 3 | 4 | 5 | | V-1 | RFWD3 | 1.54 |
| 2817 | 3 | 4 | 5 | | V-1 | RFX1 | 1.55 |
| 2818 | 3 | 4 | 5 | | V-1 | RG9MTD2 | 1.60 |
| 2819 | 3 | 4 | 5 | | V-1 | RGPD4 | 1.69 |
| 2820 | 3 | 4 | 5 | | V-1 | RHOA | 1.85 |
| 2821 | 3 | 4 | 5 | | V-1 | RHOT1 | 1.76 |
| 2822 | 3 | 4 | 5 | | V-1 | RIC8B | 1.58 |
| 2823 | 3 | 4 | 5 | | V-1 | RIOK1 | 1.52 |
| 2824 | 3 | 4 | 5 | | V-1 | RIOK2 | 1.62 |
| 2825 | 3 | 4 | 5 | | V-1 | RIOK3 | 1.93 |
| 2826 | 3 | 4 | 5 | | V-1 | RIPK2 | 1.61 |
| 2827 | 3 | 4 | 5 | | V-1 | RLIM | 1.60 |
| 2828 | 3 | 4 | 5 | | V-1 | RMND1 | 1.66 |
| 2829 | 3 | 4 | 5 | | V-1 | RNASE6 | 1.76 |
| 2830 | 3 | 4 | 5 | | V-1 | RNASEH1 | 1.60 |
| 2831 | 3 | 4 | 5 | | V-1 | RNF135 | 1.86 |
| 2832 | 3 | 4 | 5 | | V-1 | RNF14 | 1.72 |
| 2833 | 3 | 4 | 5 | | V-1 | RNF146 | 1.61 |
| 2834 | 3 | 4 | 5 | | V-1 | RNF168 | 1.89 |
| 2835 | 3 | 4 | 5 | | V-1 | RNF170 | 1.58 |
| 2836 | 3 | 4 | 5 | | V-1 | RNF181 | 1.50 |
| 2837 | 3 | 4 | 5 | | V-1 | RNF20 | 1.97 |
| 2838 | 3 | 4 | 5 | | V-1 | RNF213 | 1.61 |
| 2839 | 3 | 4 | 5 | | V-1 | RNF40 | 1.53 |
| 2840 | 3 | 4 | 5 | | V-1 | RNF6 | 1.59 |
| 2841 | 3 | 4 | 5 | | V-1 | RNF7 | 1.60 |
| 2842 | 3 | 4 | 5 | | V-1 | RNGTT | 1.86 |
| 2843 | 3 | 4 | 5 | | V-1 | RNMT | 1.50 |
| 2844 | 3 | 4 | 5 | | V-1 | ROCK1 | 1.75 |
| 2845 | 3 | 4 | 5 | | V-1 | ROCK1P1 | 1.71 |
| 2846 | 3 | 4 | 5 | | V-1 | ROCK2 | 1.97 |
| 2847 | 3 | 4 | 5 | | V-1 | RP2 | 1.54 |
| 2848 | 3 | 4 | 5 | | V-1 | RPAP2 | 1.53 |
| 2849 | 3 | 4 | 5 | | V-1 | RPE | 1.86 |
| 2850 | 3 | 4 | 5 | | V-1 | RPL13P5 | 1.78 |
| 2851 | 3 | 4 | 5 | | V-1 | RPL22 | 1.90 |
| 2852 | 3 | 4 | 5 | | V-1 | RPL23 | 1.80 |
| 2853 | 3 | 4 | 5 | | V-1 | RPL23P8 | 1.59 |
| 2854 | 3 | 4 | 5 | | V-1 | RPL26L1 | 1.50 |
| 2855 | 3 | 4 | 5 | | V-1 | RPL29P2 | 1.97 |
| 2856 | 3 | 4 | 5 | | V-1 | RPL7L1 | 1.68 |
| 2857 | 3 | 4 | 5 | | V-1 | RPN1 | 1.57 |
| 2858 | 3 | 4 | 5 | | V-1 | RPP14 | 1.55 |
| 2859 | 3 | 4 | 5 | | V-1 | RPP30 | 1.58 |
| 2860 | 3 | 4 | 5 | | V-1 | RPRD2 | 1.74 |
| 2861 | 3 | 4 | 5 | | V-1 | RPS2P32 | 1.64 |
| 2862 | 3 | 4 | 5 | | V-1 | RPS6KA3 | 1.53 |
| 2863 | 3 | 4 | 5 | | V-1 | RPS6KC1 | 1.93 |
| 2864 | 3 | 4 | 5 | | V-1 | RPUSD3 | 1.55 |
| 2865 | 3 | 4 | 5 | | V-1 | RPUSD4 | 1.81 |
| 2866 | 3 | 4 | 5 | | V-1 | RQCD1 | 1.91 |
| 2867 | 3 | 4 | 5 | | V-1 | RRAGA | 1.67 |
| 2868 | 3 | 4 | 5 | | V-1 | RRM1 | 1.53 |
| 2869 | 3 | 4 | 5 | | V-1 | RRN3 | 1.91 |
| 2870 | 3 | 4 | 5 | | V-1 | RRP1 | 1.59 |
| 2871 | 3 | 4 | 5 | | V-1 | RRP7A | 1.76 |
| 2872 | 3 | 4 | 5 | | V-1 | RSBN1L | 1.50 |
| 2873 | 3 | 4 | 5 | | V-1 | RSF1 | 1.89 |
| 2874 | 3 | 4 | 5 | | V-1 | RTCD1 | 1.66 |
| 2875 | 3 | 4 | 5 | | V-1 | RTF1 | 1.64 |
| 2876 | 3 | 4 | 5 | | V-1 | RTN4 | 1.91 |
| 2877 | 3 | 4 | 5 | | V-1 | RUFY3 | 1.57 |

Fig. 41 - 16

| | | | | | | | | | | | | | | | |
|---|---|---|---|---|---|---|---|---|---|---|---|---|---|---|---|
| 2878 | 3 | 4 | 5 | | | V-1 | RUNDC1 | 1.67 | 2974 | 3 | 4 | 5 | | V-1 | SLBP | 1.60 |
| 2879 | 3 | 4 | 5 | | | V-1 | RUNX1 | 1.73 | 2975 | 3 | 4 | 5 | | V-1 | SLC15A3 | 1.66 |
| 2880 | 3 | 4 | 5 | | | V-1 | RUSC1 | 1.57 | 2976 | 3 | 4 | 5 | | V-1 | SLC16A13 | 1.73 |
| 2881 | 3 | 4 | 5 | | | V-1 | RUVBL2 | 1.78 | 2977 | 3 | 4 | 5 | | V-1 | SLC16A3 | 1.53 |
| 2882 | 3 | 4 | 5 | | | V-1 | S100A13 | 1.83 | 2978 | 3 | 4 | 5 | | V-1 | SLC17A5 | 1.89 |
| 2883 | 3 | 4 | 5 | | | V-1 | S1PR2 | 1.57 | 2979 | 3 | 4 | 5 | | V-1 | SLC22A15 | 1.71 |
| 2884 | 3 | 4 | 5 | | | V-1 | SAE1 | 1.58 | 2980 | 3 | 4 | 5 | | V-1 | SLC22A16 | 1.73 |
| 2885 | 3 | 4 | 5 | | | V-1 | SAMD1 | 1.67 | 2981 | 3 | 4 | 5 | | V-1 | SLC24A6 | 1.60 |
| 2886 | 3 | 4 | 5 | | | V-1 | SAMD9 | 1.53 | 2982 | 3 | 4 | 5 | | V-1 | SLC25A11 | 1.72 |
| 2887 | 3 | 4 | 5 | | | V-1 | SAMM50 | 1.63 | 2983 | 3 | 4 | 5 | | V-1 | SLC25A12 | 1.65 |
| 2888 | 3 | 4 | 5 | | | V-1 | SAP30L | 1.61 | 2984 | 3 | 4 | 5 | | V-1 | SLC25A13 | 1.92 |
| 2889 | 3 | 4 | 5 | | | V-1 | SAR1B | 1.70 | 2985 | 3 | 4 | 5 | | V-1 | SLC25A22 | 1.60 |
| 2890 | 3 | 4 | 5 | | | V-1 | SART1 | 1.83 | 2986 | 3 | 4 | 5 | | V-1 | SLC25A30 | 1.69 |
| 2891 | 3 | 4 | 5 | | | V-1 | SART3 | 1.76 | 2987 | 3 | 4 | 5 | | V-1 | SLC25A40 | 1.91 |
| 2892 | 3 | 4 | 5 | | | V-1 | SASH1 | 1.92 | 2988 | 3 | 4 | 5 | | V-1 | SLC25A5 | 1.97 |
| 2893 | 3 | 4 | 5 | | | V-1 | SAT2 | 1.88 | 2989 | 3 | 4 | 5 | | V-1 | SLC25A6 | 1.67 |
| 2894 | 3 | 4 | 5 | | | V-1 | SBNO1 | 1.54 | 2990 | 3 | 4 | 5 | | V-1 | SLC26A6 | 1.64 |
| 2895 | 3 | 4 | 5 | | | V-1 | SCAF11 | 1.52 | 2991 | 3 | 4 | 5 | | V-1 | SLC27A4 | 1.97 |
| 2896 | 3 | 4 | 5 | | | V-1 | SCAF4 | 1.59 | 2992 | 3 | 4 | 5 | | V-1 | SLC30A7 | 1.72 |
| 2897 | 3 | 4 | 5 | | | V-1 | SCAMP1 | 1.80 | 2993 | 3 | 4 | 5 | | V-1 | SLC33A1 | 1.72 |
| 2898 | 3 | 4 | 5 | | | V-1 | SCAMP3 | 1.93 | 2994 | 3 | 4 | 5 | | V-1 | SLC35A5 | 1.65 |
| 2899 | 3 | 4 | 5 | | | V-1 | SCAMP4 | 1.65 | 2995 | 3 | 4 | 5 | | V-1 | SLC35B3 | 1.76 |
| 2900 | 3 | 4 | 5 | | | V-1 | SCAND1 | 1.52 | 2996 | 3 | 4 | 5 | | V-1 | SLC35B4 | 1.99 |
| 2901 | 3 | 4 | 5 | | | V-1 | SCAPER | 1.61 | 2997 | 3 | 4 | 5 | | V-1 | SLC35D2 | 1.59 |
| 2902 | 3 | 4 | 5 | | | V-1 | SCARNA16 | 1.58 | 2998 | 3 | 4 | 5 | | V-1 | SLC35E1 | 1.62 |
| 2903 | 3 | 4 | 5 | | | V-1 | SCFD1 | 1.59 | 2999 | 3 | 4 | 5 | | V-1 | SLC35F5 | 1.89 |
| 2904 | 3 | 4 | 5 | | | V-1 | SCLY | 1.59 | 3000 | 3 | 4 | 5 | | V-1 | SLC36A4 | 2.00 |
| 2905 | 3 | 4 | 5 | | | V-1 | SCP2 | 1.77 | 3001 | 3 | 4 | 5 | | V-1 | SLC38A2 | 1.78 |
| 2906 | 3 | 4 | 5 | | | V-1 | SCRIB | 1.89 | 3002 | 3 | 4 | 5 | | V-1 | SLC39A1 | 1.54 |
| 2907 | 3 | 4 | 5 | | | V-1 | SCYL2 | 1.70 | 3003 | 3 | 4 | 5 | | V-1 | SLC39A10 | 1.74 |
| 2908 | 3 | 4 | 5 | | | V-1 | SDAD1 | 1.53 | 3004 | 3 | 4 | 5 | | V-1 | SLC39A14 | 1.87 |
| 2909 | 3 | 4 | 5 | | | V-1 | SDC3 | 1.54 | 3005 | 3 | 4 | 5 | | V-1 | SLC39A6 | 1.51 |
| 2910 | 3 | 4 | 5 | | | V-1 | SDCBP | 1.61 | 3006 | 3 | 4 | 5 | | V-1 | SLC39A7 | 1.50 |
| 2911 | 3 | 4 | 5 | | | V-1 | SDCCAG8 | 1.76 | 3007 | 3 | 4 | 5 | | V-1 | SLC39A9 | 1.64 |
| 2912 | 3 | 4 | 5 | | | V-1 | SDF2L1 | 1.85 | 3008 | 3 | 4 | 5 | | V-1 | SLC44A1 | 1.95 |
| 2913 | 3 | 4 | 5 | | | V-1 | SDHA | 1.88 | 3009 | 3 | 4 | 5 | | V-1 | SLC4A1AP | 1.63 |
| 2914 | 3 | 4 | 5 | | | V-1 | SDHC | 1.72 | 3010 | 3 | 4 | 5 | | V-1 | SLC5A3 | 1.76 |
| 2915 | 3 | 4 | 5 | | | V-1 | SDHD | 1.66 | 3011 | 3 | 4 | 5 | | V-1 | SLC5A6 | 1.90 |
| 2916 | 3 | 4 | 5 | | | V-1 | SDR39U1 | 1.51 | 3012 | 3 | 4 | 5 | | V-1 | SLC7A1 | 1.75 |
| 2917 | 3 | 4 | 5 | | | V-1 | SEC13 | 1.61 | 3013 | 3 | 4 | 5 | | V-1 | SLC9A6 | 1.89 |
| 2918 | 3 | 4 | 5 | | | V-1 | SEC16A | 1.83 | 3014 | 3 | 4 | 5 | | V-1 | SLX4 | 1.51 |
| 2919 | 3 | 4 | 5 | | | V-1 | SEC22B | 1.67 | 3015 | 3 | 4 | 5 | | V-1 | SMA5 | 1.59 |
| 2920 | 3 | 4 | 5 | | | V-1 | SEC22C | 1.68 | 3016 | 3 | 4 | 5 | | V-1 | SMAD2 | 1.55 |
| 2921 | 3 | 4 | 5 | | | V-1 | SEC23A | 1.93 | 3017 | 3 | 4 | 5 | | V-1 | SMAP1 | 1.71 |
| 2922 | 3 | 4 | 5 | | | V-1 | SEC23B | 2.00 | 3018 | 3 | 4 | 5 | | V-1 | SMARCA2 | 1.62 |
| 2923 | 3 | 4 | 5 | | | V-1 | SEC23IP | 1.59 | 3019 | 3 | 4 | 5 | | V-1 | SMARCA4 | 1.99 |
| 2924 | 3 | 4 | 5 | | | V-1 | SEC24B | 1.50 | 3020 | 3 | 4 | 5 | | V-1 | SMARCA5 | 1.69 |
| 2925 | 3 | 4 | 5 | | | V-1 | SEC62 | 1.90 | 3021 | 3 | 4 | 5 | | V-1 | SMARCAD1 | 1.62 |
| 2926 | 3 | 4 | 5 | | | V-1 | SEC63 | 1.64 | 3022 | 3 | 4 | 5 | | V-1 | SMARCAL1 | 1.96 |
| 2927 | 3 | 4 | 5 | | | V-1 | SEH1L | 1.54 | 3023 | 3 | 4 | 5 | | V-1 | SMARCD2 | 1.72 |
| 2928 | 3 | 4 | 5 | | | V-1 | SEL1L | 1.63 | 3024 | 3 | 4 | 5 | | V-1 | SMC3 | 1.69 |
| 2929 | 3 | 4 | 5 | | | V-1 | SELS | 1.55 | 3025 | 3 | 4 | 5 | | V-1 | SMC4 | 1.68 |
| 2930 | 3 | 4 | 5 | | | V-1 | SEMA3C | 1.96 | 3026 | 3 | 4 | 5 | | V-1 | SMC6 | 1.54 |
| 2931 | 3 | 4 | 5 | | | V-1 | SEPHS2 | 1.81 | 3027 | 3 | 4 | 5 | | V-1 | SMCR7L | 1.76 |
| 2932 | 3 | 4 | 5 | | | V-1 | 42620 | 1.77 | 3028 | 3 | 4 | 5 | | V-1 | SMCR8 | 1.51 |
| 2933 | 3 | 4 | 5 | | | V-1 | SERAC1 | 1.77 | 3029 | 3 | 4 | 5 | | V-1 | SMG8 | 1.84 |
| 2934 | 3 | 4 | 5 | | | V-1 | SERINC1 | 1.53 | 3030 | 3 | 4 | 5 | | V-1 | SMG9 | 1.92 |
| 2935 | 3 | 4 | 5 | | | V-1 | SERINC3 | 1.78 | 3031 | 3 | 4 | 5 | | V-1 | SMN2 | 1.77 |
| 2936 | 3 | 4 | 5 | | | V-1 | SERP1 | 1.62 | 3032 | 3 | 4 | 5 | | V-1 | SMPD4 | 1.63 |
| 2937 | 3 | 4 | 5 | | | V-1 | SERPINB1 | 1.84 | 3033 | 3 | 4 | 5 | | V-1 | SNAP29 | 1.74 |
| 2938 | 3 | 4 | 5 | | | V-1 | SERPINB6 | 1.87 | 3034 | 3 | 4 | 5 | | V-1 | SNAP47 | 1.51 |
| 2939 | 3 | 4 | 5 | | | V-1 | SERPINH1 | 1.59 | 3035 | 3 | 4 | 5 | | V-1 | SNAPIN | 1.51 |
| 2940 | 3 | 4 | 5 | | | V-1 | SERTAD1 | 1.76 | 3036 | 3 | 4 | 5 | | V-1 | SNF8 | 1.62 |
| 2941 | 3 | 4 | 5 | | | V-1 | SESTD1 | 1.99 | 3037 | 3 | 4 | 5 | | V-1 | SNHG7 | 1.53 |
| 2942 | 3 | 4 | 5 | | | V-1 | SET | 1.55 | 3038 | 3 | 4 | 5 | | V-1 | SNIP1 | 1.76 |
| 2943 | 3 | 4 | 5 | | | V-1 | SETD1A | 1.61 | 3039 | 3 | 4 | 5 | | V-1 | SNRNP40 | 1.73 |
| 2944 | 3 | 4 | 5 | | | V-1 | SETMAR | 1.54 | 3040 | 3 | 4 | 5 | | V-1 | SNRPA | 1.54 |
| 2945 | 3 | 4 | 5 | | | V-1 | SF3A3 | 1.52 | 3041 | 3 | 4 | 5 | | V-1 | SNRPA1 | 1.68 |
| 2946 | 3 | 4 | 5 | | | V-1 | SF3B3 | 1.68 | 3042 | 3 | 4 | 5 | | V-1 | SNRPB | 1.71 |
| 2947 | 3 | 4 | 5 | | | V-1 | SFMBT2 | 1.65 | 3043 | 3 | 4 | 5 | | V-1 | SNRPB2 | 1.99 |
| 2948 | 3 | 4 | 5 | | | V-1 | SFR1 | 1.63 | 3044 | 3 | 4 | 5 | | V-1 | SNRPC | 1.53 |
| 2949 | 3 | 4 | 5 | | | V-1 | SFXN3 | 1.53 | 3045 | 3 | 4 | 5 | | V-1 | SNRPD1 | 1.86 |
| 2950 | 3 | 4 | 5 | | | V-1 | SFXN5 | 1.58 | 3046 | 3 | 4 | 5 | | V-1 | SNUPN | 1.93 |
| 2951 | 3 | 4 | 5 | | | V-1 | SGK3 | 1.89 | 3047 | 3 | 4 | 5 | | V-1 | SNX12 | 1.73 |
| 2952 | 3 | 4 | 5 | | | V-1 | SGMS1 | 1.76 | 3048 | 3 | 4 | 5 | | V-1 | SNX14 | 1.85 |
| 2953 | 3 | 4 | 5 | | | V-1 | SGPL1 | 1.63 | 3049 | 3 | 4 | 5 | | V-1 | SNX15 | 1.97 |
| 2954 | 3 | 4 | 5 | | | V-1 | SGSH | 1.79 | 3050 | 3 | 4 | 5 | | V-1 | SNX17 | 1.97 |
| 2955 | 3 | 4 | 5 | | | V-1 | SGTB | 1.62 | 3051 | 3 | 4 | 5 | | V-1 | SNX18 | 1.70 |
| 2956 | 3 | 4 | 5 | | | V-1 | SH2B3 | 1.69 | 3052 | 3 | 4 | 5 | | V-1 | SNX2 | 1.60 |
| 2957 | 3 | 4 | 5 | | | V-1 | SH3BP1 | 1.68 | 3053 | 3 | 4 | 5 | | V-1 | SNX27 | 1.58 |
| 2958 | 3 | 4 | 5 | | | V-1 | SH3BP4 | 1.63 | 3054 | 3 | 4 | 5 | | V-1 | SNX3 | 1.68 |
| 2959 | 3 | 4 | 5 | | | V-1 | SH3GLB1 | 1.51 | 3055 | 3 | 4 | 5 | | V-1 | SNX4 | 1.61 |
| 2960 | 3 | 4 | 5 | | | V-1 | SH3KBP1 | 1.51 | 3056 | 3 | 4 | 5 | | V-1 | SNX5 | 1.88 |
| 2961 | 3 | 4 | 5 | | | V-1 | SH3PXD2B | 1.70 | 3057 | 3 | 4 | 5 | | V-1 | SNX6 | 1.62 |
| 2962 | 3 | 4 | 5 | | | V-1 | SHC1 | 1.55 | 3058 | 3 | 4 | 5 | | V-1 | SOCS4 | 1.57 |
| 2963 | 3 | 4 | 5 | | | V-1 | SHFM1 | 1.53 | 3059 | 3 | 4 | 5 | | V-1 | SOLH | 1.55 |
| 2964 | 3 | 4 | 5 | | | V-1 | SHPK | 1.52 | 3060 | 3 | 4 | 5 | | V-1 | SON | 1.83 |
| 2965 | 3 | 4 | 5 | | | V-1 | SHQ1 | 1.70 | 3061 | 3 | 4 | 5 | | V-1 | SOWAHC | 1.76 |
| 2966 | 3 | 4 | 5 | | | V-1 | SIGLEC7 | 1.76 | 3062 | 3 | 4 | 5 | | V-1 | SP100 | 1.54 |
| 2967 | 3 | 4 | 5 | | | V-1 | SIK2 | 1.79 | 3063 | 3 | 4 | 5 | | V-1 | SPAG7 | 1.78 |
| 2968 | 3 | 4 | 5 | | | V-1 | SIRPA | 1.64 | 3064 | 3 | 4 | 5 | | V-1 | SPATA5L1 | 1.79 |
| 2969 | 3 | 4 | 5 | | | V-1 | SIRT1 | 1.78 | 3065 | 3 | 4 | 5 | | V-1 | SPATA6 | 1.73 |
| 2970 | 3 | 4 | 5 | | | V-1 | SKA2 | 1.76 | 3066 | 3 | 4 | 5 | | V-1 | SPCS1 | 1.72 |
| 2971 | 3 | 4 | 5 | | | V-1 | SKAP2 | 1.80 | 3067 | 3 | 4 | 5 | | V-1 | SPECC1L | 1.53 |
| 2972 | 3 | 4 | 5 | | | V-1 | SKIL | 1.65 | 3068 | 3 | 4 | 5 | | V-1 | SPG11 | 1.67 |
| 2973 | 3 | 4 | 5 | | | V-1 | SKIV2L2 | 1.99 | 3069 | 3 | 4 | 5 | | V-1 | SPG20 | 1.69 |

Fig. 41 - 17

| | | | | | | | | | | | | | |
|---|---|---|---|---|---|---|---|---|---|---|---|---|---|
| 3070 | 3 | 4 | 5 | | | V-1 | SPG21 | 1.96 | 3166 | 3 | 4 | 5 | | | V-1 | TCEA3 | 1.84 |
| 3071 | 3 | 4 | 5 | | | V-1 | SPHAR | 1.59 | 3167 | 3 | 4 | 5 | | | V-1 | TCEB3 | 1.53 |
| 3072 | 3 | 4 | 5 | | | V-1 | SPIN1 | 1.51 | 3168 | 3 | 4 | 5 | | | V-1 | TCF7L2 | 1.86 |
| 3073 | 3 | 4 | 5 | | | V-1 | SPINT2 | 1.69 | 3169 | 3 | 4 | 5 | | | V-1 | TCHP | 1.84 |
| 3074 | 3 | 4 | 5 | | | V-1 | SPNS1 | 1.84 | 3170 | 3 | 4 | 5 | | | V-1 | TCP1 | 1.68 |
| 3075 | 3 | 4 | 5 | | | V-1 | SPPL3 | 1.91 | 3171 | 3 | 4 | 5 | | | V-1 | TCP11L1 | 1.67 |
| 3076 | 3 | 4 | 5 | | | V-1 | SPRED2 | 1.62 | 3172 | 3 | 4 | 5 | | | V-1 | TCTN3 | 1.57 |
| 3077 | 3 | 4 | 5 | | | V-1 | SPSB2 | 1.88 | 3173 | 3 | 4 | 5 | | | V-1 | TEP1 | 1.91 |
| 3078 | 3 | 4 | 5 | | | V-1 | SPTLC1 | 2.00 | 3174 | 3 | 4 | 5 | | | V-1 | TES | 1.57 |
| 3079 | 3 | 4 | 5 | | | V-1 | SPTSSA | 1.84 | 3175 | 3 | 4 | 5 | | | V-1 | TEX10 | 1.73 |
| 3080 | 3 | 4 | 5 | | | V-1 | SPTY2D1 | 1.56 | 3176 | 3 | 4 | 5 | | | V-1 | TFAM | 1.53 |
| 3081 | 3 | 4 | 5 | | | V-1 | SQRDL | 1.94 | 3177 | 3 | 4 | 5 | | | V-1 | TFDP1 | 1.90 |
| 3082 | 3 | 4 | 5 | | | V-1 | SRC | 1.79 | 3178 | 3 | 4 | 5 | | | V-1 | TFRC | 1.55 |
| 3083 | 3 | 4 | 5 | | | V-1 | SREK1 | 1.74 | 3179 | 3 | 4 | 5 | | | V-1 | TGFBRAP1 | 1.73 |
| 3084 | 3 | 4 | 5 | | | V-1 | SREK1IP1 | 1.83 | 3180 | 3 | 4 | 5 | | | V-1 | TGOLN2 | 1.79 |
| 3085 | 3 | 4 | 5 | | | V-1 | SRFBP1 | 1.80 | 3181 | 3 | 4 | 5 | | | V-1 | TH1L | 1.80 |
| 3086 | 3 | 4 | 5 | | | V-1 | SRM | 1.56 | 3182 | 3 | 4 | 5 | | | V-1 | THADA | 1.80 |
| 3087 | 3 | 4 | 5 | | | V-1 | SRP54 | 1.53 | 3183 | 3 | 4 | 5 | | | V-1 | THAP2 | 1.84 |
| 3088 | 3 | 4 | 5 | | | V-1 | SRP72 | 1.59 | 3184 | 3 | 4 | 5 | | | V-1 | THG1L | 1.81 |
| 3089 | 3 | 4 | 5 | | | V-1 | SRSF1 | 1.90 | 3185 | 3 | 4 | 5 | | | V-1 | THOC2 | 1.81 |
| 3090 | 3 | 4 | 5 | | | V-1 | SRSF10 | 1.62 | 3186 | 3 | 4 | 5 | | | V-1 | THUMPD1 | 1.52 |
| 3091 | 3 | 4 | 5 | | | V-1 | SRSF11 | 1.57 | 3187 | 3 | 4 | 5 | | | V-1 | THUMPD2 | 1.78 |
| 3092 | 3 | 4 | 5 | | | V-1 | SRSF7 | 1.53 | 3188 | 3 | 4 | 5 | | | V-1 | THUMPD3 | 1.71 |
| 3093 | 3 | 4 | 5 | | | V-1 | 5S18 | 1.83 | 3189 | 3 | 4 | 5 | | | V-1 | TIAF1 | 1.80 |
| 3094 | 3 | 4 | 5 | | | V-1 | SS18L2 | 1.65 | 3190 | 3 | 4 | 5 | | | V-1 | TIGD5 | 1.81 |
| 3095 | 3 | 4 | 5 | | | V-1 | SSBP4 | 1.64 | 3191 | 3 | 4 | 5 | | | V-1 | TIMELESS | 1.85 |
| 3096 | 3 | 4 | 5 | | | V-1 | SSR1 | 1.85 | 3192 | 3 | 4 | 5 | | | V-1 | TIMM23 | 1.61 |
| 3097 | 3 | 4 | 5 | | | V-1 | SSR3 | 1.73 | 3193 | 3 | 4 | 5 | | | V-1 | TIMM44 | 1.52 |
| 3098 | 3 | 4 | 5 | | | V-1 | SSRP1 | 1.52 | 3194 | 3 | 4 | 5 | | | V-1 | TIMM50 | 1.56 |
| 3099 | 3 | 4 | 5 | | | V-1 | SSSCA1 | 1.71 | 3195 | 3 | 4 | 5 | | | V-1 | TIMP2 | 1.75 |
| 3100 | 3 | 4 | 5 | | | V-1 | ST7L | 1.66 | 3196 | 3 | 4 | 5 | | | V-1 | TIRAP | 1.54 |
| 3101 | 3 | 4 | 5 | | | V-1 | STAM | 1.58 | 3197 | 3 | 4 | 5 | | | V-1 | TKT | 1.55 |
| 3102 | 3 | 4 | 5 | | | V-1 | STARD7 | 1.73 | 3198 | 3 | 4 | 5 | | | V-1 | TLK2 | 1.70 |
| 3103 | 3 | 4 | 5 | | | V-1 | STAT1 | 1.54 | 3199 | 3 | 4 | 5 | | | V-1 | TLN1 | 1.69 |
| 3104 | 3 | 4 | 5 | | | V-1 | STAT2 | 1.93 | 3200 | 3 | 4 | 5 | | | V-1 | TM2D2 | 1.61 |
| 3105 | 3 | 4 | 5 | | | V-1 | STAT3 | 1.50 | 3201 | 3 | 4 | 5 | | | V-1 | TM7SF3 | 1.83 |
| 3106 | 3 | 4 | 5 | | | V-1 | STAT5A | 1.74 | 3202 | 3 | 4 | 5 | | | V-1 | TM9SF3 | 1.87 |
| 3107 | 3 | 4 | 5 | | | V-1 | STAU1 | 1.65 | 3203 | 3 | 4 | 5 | | | V-1 | TMCO1 | 1.66 |
| 3108 | 3 | 4 | 5 | | | V-1 | STIP1 | 1.76 | 3204 | 3 | 4 | 5 | | | V-1 | TMCO3 | 1.52 |
| 3109 | 3 | 4 | 5 | | | V-1 | STK11IP | 1.60 | 3205 | 3 | 4 | 5 | | | V-1 | TMCO7 | 1.78 |
| 3110 | 3 | 4 | 5 | | | V-1 | STK19 | 1.73 | 3206 | 3 | 4 | 5 | | | V-1 | TMED10 | 1.59 |
| 3111 | 3 | 4 | 5 | | | V-1 | STK24 | 1.63 | 3207 | 3 | 4 | 5 | | | V-1 | TMED10P1 | 1.53 |
| 3112 | 3 | 4 | 5 | | | V-1 | STK32B | 1.70 | 3208 | 3 | 4 | 5 | | | V-1 | TMED2 | 1.59 |
| 3113 | 3 | 4 | 5 | | | V-1 | STK38 | 1.52 | 3209 | 3 | 4 | 5 | | | V-1 | TMED3 | 1.54 |
| 3114 | 3 | 4 | 5 | | | V-1 | STK38L | 1.57 | 3210 | 3 | 4 | 5 | | | V-1 | TMED5 | 1.75 |
| 3115 | 3 | 4 | 5 | | | V-1 | STK39 | 1.63 | 3211 | 3 | 4 | 5 | | | V-1 | TMED9 | 1.62 |
| 3116 | 3 | 4 | 5 | | | V-1 | STOM | 1.56 | 3212 | 3 | 4 | 5 | | | V-1 | TMEM101 | 1.58 |
| 3117 | 3 | 4 | 5 | | | V-1 | STOML1 | 1.55 | 3213 | 3 | 4 | 5 | | | V-1 | TMEM102 | 1.85 |
| 3118 | 3 | 4 | 5 | | | V-1 | STRAP | 1.64 | 3214 | 3 | 4 | 5 | | | V-1 | TMEM104 | 1.70 |
| 3119 | 3 | 4 | 5 | | | V-1 | STRN | 1.56 | 3215 | 3 | 4 | 5 | | | V-1 | TMEM107 | 1.55 |
| 3120 | 3 | 4 | 5 | | | V-1 | STRN3 | 1.71 | 3216 | 3 | 4 | 5 | | | V-1 | TMEM110 | 1.82 |
| 3121 | 3 | 4 | 5 | | | V-1 | STT3B | 1.94 | 3217 | 3 | 4 | 5 | | | V-1 | TMEM115 | 1.52 |
| 3122 | 3 | 4 | 5 | | | V-1 | STX6 | 1.73 | 3218 | 3 | 4 | 5 | | | V-1 | TMEM126B | 1.66 |
| 3123 | 3 | 4 | 5 | | | V-1 | STX7 | 1.52 | 3219 | 3 | 4 | 5 | | | V-1 | TMEM131 | 1.75 |
| 3124 | 3 | 4 | 5 | | | V-1 | STXBP3 | 1.62 | 3220 | 3 | 4 | 5 | | | V-1 | TMEM147 | 1.78 |
| 3125 | 3 | 4 | 5 | | | V-1 | STYXL1 | 1.60 | 3221 | 3 | 4 | 5 | | | V-1 | TMEM14C | 1.57 |
| 3126 | 3 | 4 | 5 | | | V-1 | SUCLG1 | 1.57 | 3222 | 3 | 4 | 5 | | | V-1 | TMEM160 | 1.91 |
| 3127 | 3 | 4 | 5 | | | V-1 | SULF2 | 1.62 | 3223 | 3 | 4 | 5 | | | V-1 | TMEM161A | 1.81 |
| 3128 | 3 | 4 | 5 | | | V-1 | SULT1B1 | 1.66 | 3224 | 3 | 4 | 5 | | | V-1 | TMEM167B | 1.60 |
| 3129 | 3 | 4 | 5 | | | V-1 | SUMF2 | 1.54 | 3225 | 3 | 4 | 5 | | | V-1 | TMEM168 | 1.92 |
| 3130 | 3 | 4 | 5 | | | V-1 | SUMO1 | 1.52 | 3226 | 3 | 4 | 5 | | | V-1 | TMEM169 | 1.75 |
| 3131 | 3 | 4 | 5 | | | V-1 | SUMO2 | 1.71 | 3227 | 3 | 4 | 5 | | | V-1 | TMEM180 | 1.81 |
| 3132 | 3 | 4 | 5 | | | V-1 | SUN1 | 1.79 | 3228 | 3 | 4 | 5 | | | V-1 | TMEM184C | 1.58 |
| 3133 | 3 | 4 | 5 | | | V-1 | SUN2 | 1.65 | 3229 | 3 | 4 | 5 | | | V-1 | TMEM185A | 1.63 |
| 3134 | 3 | 4 | 5 | | | V-1 | SUOX | 1.86 | 3230 | 3 | 4 | 5 | | | V-1 | TMEM19 | 1.83 |
| 3135 | 3 | 4 | 5 | | | V-1 | SUPT16H | 1.70 | 3231 | 3 | 4 | 5 | | | V-1 | TMEM192 | 1.91 |
| 3136 | 3 | 4 | 5 | | | V-1 | SUPT5H | 1.51 | 3232 | 3 | 4 | 5 | | | V-1 | TMEM194B | 1.79 |
| 3137 | 3 | 4 | 5 | | | V-1 | SUPV3L1 | 1.60 | 3233 | 3 | 4 | 5 | | | V-1 | TMEM2 | 1.80 |
| 3138 | 3 | 4 | 5 | | | V-1 | SURF4 | 1.63 | 3234 | 3 | 4 | 5 | | | V-1 | TMEM201 | 1.63 |
| 3139 | 3 | 4 | 5 | | | V-1 | SUV39H2 | 1.53 | 3235 | 3 | 4 | 5 | | | V-1 | TMEM209 | 1.96 |
| 3140 | 3 | 4 | 5 | | | V-1 | SYNC | 1.97 | 3236 | 3 | 4 | 5 | | | V-1 | TMEM214 | 1.64 |
| 3141 | 3 | 4 | 5 | | | V-1 | SYNGR2 | 1.75 | 3237 | 3 | 4 | 5 | | | V-1 | TMEM218 | 1.67 |
| 3142 | 3 | 4 | 5 | | | V-1 | SYNJ1 | 1.71 | 3238 | 3 | 4 | 5 | | | V-1 | TMEM238 | 1.96 |
| 3143 | 3 | 4 | 5 | | | V-1 | SYT11 | 1.89 | 3239 | 3 | 4 | 5 | | | V-1 | TMEM30A | 1.66 |
| 3144 | 3 | 4 | 5 | | | V-1 | TA81 | 1.52 | 3240 | 3 | 4 | 5 | | | V-1 | TMEM33 | 1.65 |
| 3145 | 3 | 4 | 5 | | | V-1 | TACC1 | 1.91 | 3241 | 3 | 4 | 5 | | | V-1 | TMEM38B | 1.75 |
| 3146 | 3 | 4 | 5 | | | V-1 | TADA1 | 1.62 | 3242 | 3 | 4 | 5 | | | V-1 | TMEM41A | 1.51 |
| 3147 | 3 | 4 | 5 | | | V-1 | TAF11 | 1.53 | 3243 | 3 | 4 | 5 | | | V-1 | TMEM57 | 1.84 |
| 3148 | 3 | 4 | 5 | | | V-1 | TAF1B | 1.80 | 3244 | 3 | 4 | 5 | | | V-1 | TMEM62 | 1.90 |
| 3149 | 3 | 4 | 5 | | | V-1 | TAF3 | 1.89 | 3245 | 3 | 4 | 5 | | | V-1 | TMEM65 | 1.73 |
| 3150 | 3 | 4 | 5 | | | V-1 | TAF4 | 1.54 | 3246 | 3 | 4 | 5 | | | V-1 | TMEM68 | 1.58 |
| 3151 | 3 | 4 | 5 | | | V-1 | TAF5 | 1.82 | 3247 | 3 | 4 | 5 | | | V-1 | TMEM69 | 1.72 |
| 3152 | 3 | 4 | 5 | | | V-1 | TAF6L | 1.51 | 3248 | 3 | 4 | 5 | | | V-1 | TMEM81 | 1.74 |
| 3153 | 3 | 4 | 5 | | | V-1 | TAMM41 | 1.50 | 3249 | 3 | 4 | 5 | | | V-1 | TMEM86A | 1.73 |
| 3154 | 3 | 4 | 5 | | | V-1 | TAOK1 | 1.56 | 3250 | 3 | 4 | 5 | | | V-1 | TMEM87A | 1.97 |
| 3155 | 3 | 4 | 5 | | | V-1 | TARDBP | 1.60 | 3251 | 3 | 4 | 5 | | | V-1 | TMOD3 | 1.99 |
| 3156 | 3 | 4 | 5 | | | V-1 | TAX1BP3 | 1.54 | 3252 | 3 | 4 | 5 | | | V-1 | TMPO | 1.74 |
| 3157 | 3 | 4 | 5 | | | V-1 | TBC1D1 | 1.73 | 3253 | 3 | 4 | 5 | | | V-1 | TMPPE | 1.72 |
| 3158 | 3 | 4 | 5 | | | V-1 | TBC1D24 | 1.97 | 3254 | 3 | 4 | 5 | | | V-1 | TMSB4Y | 1.69 |
| 3159 | 3 | 4 | 5 | | | V-1 | TBC1D7 | 1.55 | 3255 | 3 | 4 | 5 | | | V-1 | TMX2 | 1.81 |
| 3160 | 3 | 4 | 5 | | | V-1 | TBCEL | 1.81 | 3256 | 3 | 4 | 5 | | | V-1 | TMX3 | 1.77 |
| 3161 | 3 | 4 | 5 | | | V-1 | TBL2 | 1.94 | 3257 | 3 | 4 | 5 | | | V-1 | TNFRSF10B | 1.57 |
| 3162 | 3 | 4 | 5 | | | V-1 | TBL3 | 1.51 | 3258 | 3 | 4 | 5 | | | V-1 | TNFRSF10D | 1.74 |
| 3163 | 3 | 4 | 5 | | | V-1 | TBRG4 | 1.51 | 3259 | 3 | 4 | 5 | | | V-1 | TNFRSF18 | 1.79 |
| 3164 | 3 | 4 | 5 | | | V-1 | TBXAS1 | 1.58 | 3260 | 3 | 4 | 5 | | | V-1 | TNFRSF8 | 1.69 |
| 3165 | 3 | 4 | 5 | | | V-1 | TCEA1 | 1.72 | 3261 | 3 | 4 | 5 | | | V-1 | TNFSF13B | 1.76 |

Fig. 41 - 18

| | | | | | | | | | | | | | | | |
|---|---|---|---|---|---|---|---|---|---|---|---|---|---|---|---|
| 3262 | 3 | 4 | 5 | | | V-1 | TNKS | 1.72 | 3358 | 3 | 4 | 5 | | V-1 | UBXN4 | 1.58 |
| 3263 | 3 | 4 | 5 | | | V-1 | TNKS2 | 1.55 | 3359 | 3 | 4 | 5 | | V-1 | UBXN7 | 1.54 |
| 3264 | 3 | 4 | 5 | | | V-1 | TNPO1 | 1.54 | 3360 | 3 | 4 | 5 | | V-1 | UEVLD | 1.83 |
| 3265 | 3 | 4 | 5 | | | V-1 | TNPO3 | 1.57 | 3361 | 3 | 4 | 5 | | V-1 | UFL1 | 1.67 |
| 3266 | 3 | 4 | 5 | | | V-1 | TNRC6A | 1.71 | 3362 | 3 | 4 | 5 | | V-1 | UFSP2 | 1.61 |
| 3267 | 3 | 4 | 5 | | | V-1 | TOB2 | 1.58 | 3363 | 3 | 4 | 5 | | V-1 | UGGT1 | 1.67 |
| 3268 | 3 | 4 | 5 | | | V-1 | TOLLIP | 1.60 | 3364 | 3 | 4 | 5 | | V-1 | UGP2 | 1.51 |
| 3269 | 3 | 4 | 5 | | | V-1 | TOMM20 | 1.63 | 3365 | 3 | 4 | 5 | | V-1 | UNC45A | 1.85 |
| 3270 | 3 | 4 | 5 | | | V-1 | TOMM40 | 1.63 | 3366 | 3 | 4 | 5 | | V-1 | UNC50 | 1.52 |
| 3271 | 3 | 4 | 5 | | | V-1 | TOMM7 | 1.66 | 3367 | 3 | 4 | 5 | | V-1 | UPF2 | 1.50 |
| 3272 | 3 | 4 | 5 | | | V-1 | TOMM70A | 1.59 | 3368 | 3 | 4 | 5 | | V-1 | UPF3B | 1.63 |
| 3273 | 3 | 4 | 5 | | | V-1 | TOP1 | 1.74 | 3369 | 3 | 4 | 5 | | V-1 | UPRT | 1.58 |
| 3274 | 3 | 4 | 5 | | | V-1 | TOP1P1 | 1.84 | 3370 | 3 | 4 | 5 | | V-1 | UQCRFS1 | 1.54 |
| 3275 | 3 | 4 | 5 | | | V-1 | TOP2B | 1.67 | 3371 | 3 | 4 | 5 | | V-1 | UQCRHL | 1.55 |
| 3276 | 3 | 4 | 5 | | | V-1 | TOR1A | 1.67 | 3372 | 3 | 4 | 5 | | V-1 | UQCRQ | 1.60 |
| 3277 | 3 | 4 | 5 | | | V-1 | TOR1AIP1 | 1.60 | 3373 | 3 | 4 | 5 | | V-1 | URB2 | 1.91 |
| 3278 | 3 | 4 | 5 | | | V-1 | TOR1AIP2 | 1.55 | 3374 | 3 | 4 | 5 | | V-1 | USP12 | 1.50 |
| 3279 | 3 | 4 | 5 | | | V-1 | TOR1B | 1.64 | 3375 | 3 | 4 | 5 | | V-1 | USP14 | 1.83 |
| 3280 | 3 | 4 | 5 | | | V-1 | TOR3A | 1.75 | 3376 | 3 | 4 | 5 | | V-1 | USP16 | 1.69 |
| 3281 | 3 | 4 | 5 | | | V-1 | TP53BP1 | 1.56 | 3377 | 3 | 4 | 5 | | V-1 | USP22 | 1.71 |
| 3282 | 3 | 4 | 5 | | | V-1 | TPCN1 | 1.99 | 3378 | 3 | 4 | 5 | | V-1 | USP27X | 1.61 |
| 3283 | 3 | 4 | 5 | | | V-1 | TPI1 | 1.71 | 3379 | 3 | 4 | 5 | | V-1 | USP3 | 1.52 |
| 3284 | 3 | 4 | 5 | | | V-1 | TPK1 | 1.69 | 3380 | 3 | 4 | 5 | | V-1 | USP33 | 1.68 |
| 3285 | 3 | 4 | 5 | | | V-1 | TPM4 | 1.60 | 3381 | 3 | 4 | 5 | | V-1 | USP37 | 1.55 |
| 3286 | 3 | 4 | 5 | | | V-1 | TPP2 | 1.96 | 3382 | 3 | 4 | 5 | | V-1 | USP38 | 1.73 |
| 3287 | 3 | 4 | 5 | | | V-1 | TRA2B | 1.98 | 3383 | 3 | 4 | 5 | | V-1 | USP40 | 1.69 |
| 3288 | 3 | 4 | 5 | | | V-1 | TRAF3 | 1.68 | 3384 | 3 | 4 | 5 | | V-1 | USP47 | 1.52 |
| 3289 | 3 | 4 | 5 | | | V-1 | TRAF3IP2 | 1.56 | 3385 | 3 | 4 | 5 | | V-1 | USP5 | 1.71 |
| 3290 | 3 | 4 | 5 | | | V-1 | TRAF7 | 1.51 | 3386 | 3 | 4 | 5 | | V-1 | USP7 | 1.64 |
| 3291 | 3 | 4 | 5 | | | V-1 | TRAK1 | 1.72 | 3387 | 3 | 4 | 5 | | V-1 | USP8 | 1.79 |
| 3292 | 3 | 4 | 5 | | | V-1 | TRAPPC11 | 1.89 | 3388 | 3 | 4 | 5 | | V-1 | UTP11L | 1.80 |
| 3293 | 3 | 4 | 5 | | | V-1 | TRAPPC12 | 1.53 | 3389 | 3 | 4 | 5 | | V-1 | UTP14C | 1.54 |
| 3294 | 3 | 4 | 5 | | | V-1 | TREX1 | 1.61 | 3390 | 3 | 4 | 5 | | V-1 | UTP15 | 1.63 |
| 3295 | 3 | 4 | 5 | | | V-1 | TRIAP1 | 1.69 | 3391 | 3 | 4 | 5 | | V-1 | UTP18 | 1.95 |
| 3296 | 3 | 4 | 5 | | | V-1 | TRIM22 | 1.63 | 3392 | 3 | 4 | 5 | | V-1 | UTP23 | 1.61 |
| 3297 | 3 | 4 | 5 | | | V-1 | TRIM26 | 1.53 | 3393 | 3 | 4 | 5 | | V-1 | UTP3 | 1.93 |
| 3298 | 3 | 4 | 5 | | | V-1 | TRIM28 | 1.63 | 3394 | 3 | 4 | 5 | | V-1 | UTP6 | 1.57 |
| 3299 | 3 | 4 | 5 | | | V-1 | TRIM34 | 1.56 | 3395 | 3 | 4 | 5 | | V-1 | UTRN | 1.51 |
| 3300 | 3 | 4 | 5 | | | V-1 | TRIM35 | 1.57 | 3396 | 3 | 4 | 5 | | V-1 | VAC14 | 1.92 |
| 3301 | 3 | 4 | 5 | | | V-1 | TRIM38 | 1.66 | 3397 | 3 | 4 | 5 | | V-1 | VAMP5 | 1.89 |
| 3302 | 3 | 4 | 5 | | | V-1 | TRIM41 | 1.54 | 3398 | 3 | 4 | 5 | | V-1 | VAMP7 | 1.77 |
| 3303 | 3 | 4 | 5 | | | V-1 | TRIM5 | 1.60 | 3399 | 3 | 4 | 5 | | V-1 | VAMP8 | 1.91 |
| 3304 | 3 | 4 | 5 | | | V-1 | TRIM56 | 1.72 | 3400 | 3 | 4 | 5 | | V-1 | VAPA | 1.61 |
| 3305 | 3 | 4 | 5 | | | V-1 | TRIM8 | 1.71 | 3401 | 3 | 4 | 5 | | V-1 | VBP1 | 1.68 |
| 3306 | 3 | 4 | 5 | | | V-1 | TRIP11 | 1.59 | 3402 | 3 | 4 | 5 | | V-1 | VCL | 1.89 |
| 3307 | 3 | 4 | 5 | | | V-1 | TRIP12 | 1.55 | 3403 | 3 | 4 | 5 | | V-1 | VCP | 1.84 |
| 3308 | 3 | 4 | 5 | | | V-1 | TRIP4 | 1.67 | 3404 | 3 | 4 | 5 | | V-1 | VCPIP1 | 1.51 |
| 3309 | 3 | 4 | 5 | | | V-1 | TRIT1 | 1.68 | 3405 | 3 | 4 | 5 | | V-1 | VDAC2 | 1.67 |
| 3310 | 3 | 4 | 5 | | | V-1 | TRMT1L | 1.61 | 3406 | 3 | 4 | 5 | | V-1 | VIPR1 | 1.83 |
| 3311 | 3 | 4 | 5 | | | V-1 | TRMT6 | 1.81 | 3407 | 3 | 4 | 5 | | V-1 | VKORC1 | 1.51 |
| 3312 | 3 | 4 | 5 | | | V-1 | TRNT1 | 1.75 | 3408 | 3 | 4 | 5 | | V-1 | VKORC1L1 | 1.54 |
| 3313 | 3 | 4 | 5 | | | V-1 | TRPV2 | 1.78 | 3409 | 3 | 4 | 5 | | V-1 | VPS11 | 1.56 |
| 3314 | 3 | 4 | 5 | | | V-1 | TRRAP | 1.76 | 3410 | 3 | 4 | 5 | | V-1 | VPS13C | 1.80 |
| 3315 | 3 | 4 | 5 | | | V-1 | TSC2 | 1.50 | 3411 | 3 | 4 | 5 | | V-1 | VPS13D | 1.55 |
| 3316 | 3 | 4 | 5 | | | V-1 | TSC22D2 | 1.55 | 3412 | 3 | 4 | 5 | | V-1 | VPS18 | 1.57 |
| 3317 | 3 | 4 | 5 | | | V-1 | TSHZ1 | 1.54 | 3413 | 3 | 4 | 5 | | V-1 | VPS25 | 1.79 |
| 3318 | 3 | 4 | 5 | | | V-1 | TSN | 1.74 | 3414 | 3 | 4 | 5 | | V-1 | VPS33A | 1.50 |
| 3319 | 3 | 4 | 5 | | | V-1 | TSPAN14 | 1.61 | 3415 | 3 | 4 | 5 | | V-1 | VPS33B | 1.67 |
| 3320 | 3 | 4 | 5 | | | V-1 | TSPAN17 | 1.77 | 3416 | 3 | 4 | 5 | | V-1 | VPS36 | 1.63 |
| 3321 | 3 | 4 | 5 | | | V-1 | TSR1 | 1.93 | 3417 | 3 | 4 | 5 | | V-1 | VPS53 | 1.85 |
| 3322 | 3 | 4 | 5 | | | V-1 | TSSC1 | 1.62 | 3418 | 3 | 4 | 5 | | V-1 | VPS54 | 1.89 |
| 3323 | 3 | 4 | 5 | | | V-1 | TTF1 | 1.61 | 3419 | 3 | 4 | 5 | | V-1 | VRK1 | 1.68 |
| 3324 | 3 | 4 | 5 | | | V-1 | TTF2 | 1.77 | 3420 | 3 | 4 | 5 | | V-1 | VRK2 | 1.66 |
| 3325 | 3 | 4 | 5 | | | V-1 | TTI1 | 1.66 | 3421 | 3 | 4 | 5 | | V-1 | WASF1 | 1.57 |
| 3326 | 3 | 4 | 5 | | | V-1 | TTL | 1.74 | 3422 | 3 | 4 | 5 | | V-1 | WASF2 | 1.69 |
| 3327 | 3 | 4 | 5 | | | V-1 | TTYH2 | 1.94 | 3423 | 3 | 4 | 5 | | V-1 | WASL | 1.80 |
| 3328 | 3 | 4 | 5 | | | V-1 | TUBB | 1.62 | 3424 | 3 | 4 | 5 | | V-1 | WBP4 | 1.68 |
| 3329 | 3 | 4 | 5 | | | V-1 | TUBGCP2 | 1.52 | 3425 | 3 | 4 | 5 | | V-1 | WBSCR16 | 1.86 |
| 3330 | 3 | 4 | 5 | | | V-1 | TUBGCP3 | 1.72 | 3426 | 3 | 4 | 5 | | V-1 | WDFY1 | 1.55 |
| 3331 | 3 | 4 | 5 | | | V-1 | TUG1 | 1.51 | 3427 | 3 | 4 | 5 | | V-1 | WDFY2 | 1.91 |
| 3332 | 3 | 4 | 5 | | | V-1 | TWF2 | 1.65 | 3428 | 3 | 4 | 5 | | V-1 | WDFY3 | 1.59 |
| 3333 | 3 | 4 | 5 | | | V-1 | TXLNA | 1.78 | 3429 | 3 | 4 | 5 | | V-1 | WDFY4 | 1.55 |
| 3334 | 3 | 4 | 5 | | | V-1 | TXNDC15 | 1.96 | 3430 | 3 | 4 | 5 | | V-1 | WDR12 | 1.76 |
| 3335 | 3 | 4 | 5 | | | V-1 | TXNRD1 | 1.63 | 3431 | 3 | 4 | 5 | | V-1 | WDR18 | 1.65 |
| 3336 | 3 | 4 | 5 | | | V-1 | TYW1 | 1.53 | 3432 | 3 | 4 | 5 | | V-1 | WDR36 | 1.89 |
| 3337 | 3 | 4 | 5 | | | V-1 | U2AF2 | 1.52 | 3433 | 3 | 4 | 5 | | V-1 | WDR37 | 1.73 |
| 3338 | 3 | 4 | 5 | | | V-1 | UBA3 | 1.73 | 3434 | 3 | 4 | 5 | | V-1 | WDR4 | 1.62 |
| 3339 | 3 | 4 | 5 | | | V-1 | UBA5 | 1.62 | 3435 | 3 | 4 | 5 | | V-1 | WDR45L | 1.53 |
| 3340 | 3 | 4 | 5 | | | V-1 | UBAC1 | 1.81 | 3436 | 3 | 4 | 5 | | V-1 | WDR46 | 1.52 |
| 3341 | 3 | 4 | 5 | | | V-1 | UBE2D4 | 1.50 | 3437 | 3 | 4 | 5 | | V-1 | WDR61 | 1.77 |
| 3342 | 3 | 4 | 5 | | | V-1 | UBE2F | 1.55 | 3438 | 3 | 4 | 5 | | V-1 | WDR77 | 1.52 |
| 3343 | 3 | 4 | 5 | | | V-1 | UBE2G1 | 1.50 | 3439 | 3 | 4 | 5 | | V-1 | WDR83 | 1.50 |
| 3344 | 3 | 4 | 5 | | | V-1 | UBE2I | 1.51 | 3440 | 3 | 4 | 5 | | V-1 | WDR83OS | 1.94 |
| 3345 | 3 | 4 | 5 | | | V-1 | UBE2J1 | 1.74 | 3441 | 3 | 4 | 5 | | V-1 | WDSUB1 | 1.85 |
| 3346 | 3 | 4 | 5 | | | V-1 | UBE2K | 1.87 | 3442 | 3 | 4 | 5 | | V-1 | WHSC1 | 1.73 |
| 3347 | 3 | 4 | 5 | | | V-1 | UBE2L3 | 1.69 | 3443 | 3 | 4 | 5 | | V-1 | WHSC2 | 1.71 |
| 3348 | 3 | 4 | 5 | | | V-1 | UBE2N | 1.51 | 3444 | 3 | 4 | 5 | | V-1 | WIZ | 1.61 |
| 3349 | 3 | 4 | 5 | | | V-1 | UBE2S | 1.55 | 3445 | 3 | 4 | 5 | | V-1 | WWP1 | 1.57 |
| 3350 | 3 | 4 | 5 | | | V-1 | UBE2V1 | 1.60 | 3446 | 3 | 4 | 5 | | V-1 | XAB2 | 1.55 |
| 3351 | 3 | 4 | 5 | | | V-1 | UBE2V2 | 1.67 | 3447 | 3 | 4 | 5 | | V-1 | XBP1 | 1.89 |
| 3352 | 3 | 4 | 5 | | | V-1 | UBE3C | 1.75 | 3448 | 3 | 4 | 5 | | V-1 | XIAP | 1.51 |
| 3353 | 3 | 4 | 5 | | | V-1 | UBE4A | 1.62 | 3449 | 3 | 4 | 5 | | V-1 | XPO1 | 1.99 |
| 3354 | 3 | 4 | 5 | | | V-1 | UBP1 | 1.79 | 3450 | 3 | 4 | 5 | | V-1 | XPO4 | 1.51 |
| 3355 | 3 | 4 | 5 | | | V-1 | UBR1 | 1.73 | 3451 | 3 | 4 | 5 | | V-1 | XPO7 | 1.68 |
| 3356 | 3 | 4 | 5 | | | V-1 | UBR3 | 1.91 | 3452 | 3 | 4 | 5 | | V-1 | XPOT | 1.62 |
| 3357 | 3 | 4 | 5 | | | V-1 | UBXN2A | 1.55 | 3453 | 3 | 4 | 5 | | V-1 | XPR1 | 1.75 |

Fig. 41 - 19

| | | | | | | | | | | | | | | |
|---|---|---|---|---|---|---|---|---|---|---|---|---|---|---|
| 3454 | 3 | 4 | 5 | | V-1 | XRCC4 | 1.55 | 3550 | 3 | 4 | | | IV-2 | ABHD4 | 0.85 |
| 3455 | 3 | 4 | 5 | | V-1 | XRN2 | 1.81 | 3551 | 3 | 4 | | | IV-2 | ABHD5 | 0.83 |
| 3456 | 3 | 4 | 5 | | V-1 | XYLT1 | 1.87 | 3552 | 3 | 4 | | | IV-2 | ABTB2 | 0.95 |
| 3457 | 3 | 4 | 5 | | V-1 | YEATS2 | 1.56 | 3553 | 3 | 4 | | | IV-2 | ACACB | 0.95 |
| 3458 | 3 | 4 | 5 | | V-1 | YIF1A | 1.61 | 3554 | 3 | 4 | | | IV-2 | ACBD4 | 0.87 |
| 3459 | 3 | 4 | 5 | | V-1 | YIF1B | 1.78 | 3555 | 3 | 4 | | | IV-2 | ACCS | 0.97 |
| 3460 | 3 | 4 | 5 | | V-1 | YIPF5 | 1.81 | 3556 | 3 | 4 | | | IV-2 | ACN9 | 0.92 |
| 3461 | 3 | 4 | 5 | | V-1 | YLPM1 | 1.73 | 3557 | 3 | 4 | | | IV-2 | ACTR3B | 0.83 |
| 3462 | 3 | 4 | 5 | | V-1 | YME1L1 | 1.63 | 3558 | 3 | 4 | | | IV-2 | ADAL | 0.95 |
| 3463 | 3 | 4 | 5 | | V-1 | YPEL2 | 1.53 | 3559 | 3 | 4 | | | IV-2 | ADAM1 | 0.99 |
| 3464 | 3 | 4 | 5 | | V-1 | YTHDC2 | 1.62 | 3560 | 3 | 4 | | | IV-2 | ADAM19 | 0.96 |
| 3465 | 3 | 4 | 5 | | V-1 | YTHDF1 | 1.56 | 3561 | 3 | 4 | | | IV-2 | ADAM8 | 0.91 |
| 3466 | 3 | 4 | 5 | | V-1 | YWHAE | 1.65 | 3562 | 3 | 4 | | | IV-2 | ADAMTS10 | 0.94 |
| 3467 | 3 | 4 | 5 | | V-1 | YWHAQ | 1.54 | 3563 | 3 | 4 | | | IV-2 | ADARB2 | 0.93 |
| 3468 | 3 | 4 | 5 | | V-1 | YWHAZ | 1.56 | 3564 | 3 | 4 | | | IV-2 | ADHFE1 | 0.93 |
| 3469 | 3 | 4 | 5 | | V-1 | YY1 | 1.56 | 3565 | 3 | 4 | | | IV-2 | ADORA2A | 0.90 |
| 3470 | 3 | 4 | 5 | | V-1 | ZBED4 | 1.64 | 3566 | 3 | 4 | | | IV-2 | AEBP1 | 0.82 |
| 3471 | 3 | 4 | 5 | | V-1 | ZBTB26 | 1.62 | 3567 | 3 | 4 | | | IV-2 | AES | 0.86 |
| 3472 | 3 | 4 | 5 | | V-1 | ZBTB33 | 1.59 | 3568 | 3 | 4 | | | IV-2 | AFG3L1P | 0.67 |
| 3473 | 3 | 4 | 5 | | V-1 | ZBTB45 | 1.54 | 3569 | 3 | 4 | | | IV-2 | AGAP5 | 0.89 |
| 3474 | 3 | 4 | 5 | | V-1 | ZBTB7A | 1.77 | 3570 | 3 | 4 | | | IV-2 | AGBL5 | 0.76 |
| 3475 | 3 | 4 | 5 | | V-1 | ZBTB9 | 1.67 | 3571 | 3 | 4 | | | IV-2 | AHCTF1 | 0.89 |
| 3476 | 3 | 4 | 5 | | V-1 | ZC3H13 | 1.91 | 3572 | 3 | 4 | | | IV-2 | AIFM2 | 0.99 |
| 3477 | 3 | 4 | 5 | | V-1 | ZC3H14 | 1.60 | 3573 | 3 | 4 | | | IV-2 | AKAP12 | 0.86 |
| 3478 | 3 | 4 | 5 | | V-1 | ZC3H15 | 1.88 | 3574 | 3 | 4 | | | IV-2 | AKAP17A | 0.83 |
| 3479 | 3 | 4 | 5 | | V-1 | ZC3H18 | 1.52 | 3575 | 3 | 4 | | | IV-2 | AKAP5 | 0.97 |
| 3480 | 3 | 4 | 5 | | V-1 | ZC3H6 | 1.67 | 3576 | 3 | 4 | | | IV-2 | AKT1 | 0.99 |
| 3481 | 3 | 4 | 5 | | V-1 | ZC3H7A | 1.52 | 3577 | 3 | 4 | | | IV-2 | AKT3 | 0.96 |
| 3482 | 3 | 4 | 5 | | V-1 | ZC3H7B | 1.70 | 3578 | 3 | 4 | | | IV-2 | AKTIP | 0.85 |
| 3483 | 3 | 4 | 5 | | V-1 | ZDHHC24 | 1.52 | 3579 | 3 | 4 | | | IV-2 | ALKBH2 | 0.69 |
| 3484 | 3 | 4 | 5 | | V-1 | ZDHHC4 | 1.86 | 3580 | 3 | 4 | | | IV-2 | ALKBH7 | 0.95 |
| 3485 | 3 | 4 | 5 | | V-1 | ZDHHC5 | 1.61 | 3581 | 3 | 4 | | | IV-2 | ALS2CL | 0.98 |
| 3486 | 3 | 4 | 5 | | V-1 | ZDHHC7 | 1.79 | 3582 | 3 | 4 | | | IV-2 | AMACR | 0.68 |
| 3487 | 3 | 4 | 5 | | V-1 | ZFP92 | 1.64 | 3583 | 3 | 4 | | | IV-2 | AMD1 | 0.99 |
| 3488 | 3 | 4 | 5 | | V-1 | ZFR | 1.71 | 3584 | 3 | 4 | | | IV-2 | AMDHD2 | 0.70 |
| 3489 | 3 | 4 | 5 | | V-1 | ZFYVE1 | 1.56 | 3585 | 3 | 4 | | | IV-2 | AMIGO2 | 0.97 |
| 3490 | 3 | 4 | 5 | | V-1 | ZFYVE21 | 1.53 | 3586 | 3 | 4 | | | IV-2 | AMIGO3 | 0.93 |
| 3491 | 3 | 4 | 5 | | V-1 | ZFYVE26 | 1.96 | 3587 | 3 | 4 | | | IV-2 | AMN1 | 0.74 |
| 3492 | 3 | 4 | 5 | | V-1 | ZHX1 | 1.99 | 3588 | 3 | 4 | | | IV-2 | AMT | 0.98 |
| 3493 | 3 | 4 | 5 | | V-1 | ZKSCAN1 | 1.63 | 3589 | 3 | 4 | | | IV-2 | AMZ2 | 0.99 |
| 3494 | 3 | 4 | 5 | | V-1 | ZKSCAN5 | 1.61 | 3590 | 3 | 4 | | | IV-2 | AMZ2P1 | 0.90 |
| 3495 | 3 | 4 | 5 | | V-1 | ZMAT3 | 1.57 | 3591 | 3 | 4 | | | IV-2 | ANGPT1 | 0.81 |
| 3496 | 3 | 4 | 5 | | V-1 | ZMPSTE24 | 1.77 | 3592 | 3 | 4 | | | IV-2 | ANK3 | 0.98 |
| 3497 | 3 | 4 | 5 | | V-1 | ZMYM2 | 1.50 | 3593 | 3 | 4 | | | IV-2 | ANKDD1A | 0.89 |
| 3498 | 3 | 4 | 5 | | V-1 | ZMYM3 | 1.70 | 3594 | 3 | 4 | | | IV-2 | ANKH | 0.92 |
| 3499 | 3 | 4 | 5 | | V-1 | ZMYM4 | 1.71 | 3595 | 3 | 4 | | | IV-2 | ANKHD1-EIF4EBP3 | 0.88 |
| 3500 | 3 | 4 | 5 | | V-1 | ZMYND8 | 1.71 | 3596 | 3 | 4 | | | IV-2 | ANKRA2 | 0.83 |
| 3501 | 3 | 4 | 5 | | V-1 | ZNF146 | 1.60 | 3597 | 3 | 4 | | | IV-2 | ANKRD13A | 0.93 |
| 3502 | 3 | 4 | 5 | | V-1 | ZNF16 | 1.61 | 3598 | 3 | 4 | | | IV-2 | ANKRD13D | 0.73 |
| 3503 | 3 | 4 | 5 | | V-1 | ZNF189 | 1.66 | 3599 | 3 | 4 | | | IV-2 | ANKRD33B | 0.81 |
| 3504 | 3 | 4 | 5 | | V-1 | ZNF197 | 1.78 | 3600 | 3 | 4 | | | IV-2 | ANKRD6 | 0.92 |
| 3505 | 3 | 4 | 5 | | V-1 | ZNF2 | 1.53 | 3601 | 3 | 4 | | | IV-2 | ANKS3 | 0.99 |
| 3506 | 3 | 4 | 5 | | V-1 | ZNF207 | 1.74 | 3602 | 3 | 4 | | | IV-2 | ANKZF1 | 0.86 |
| 3507 | 3 | 4 | 5 | | V-1 | ZNF236 | 1.57 | 3603 | 3 | 4 | | | IV-2 | ANO9 | 0.84 |
| 3508 | 3 | 4 | 5 | | V-1 | ZNF252 | 1.51 | 3604 | 3 | 4 | | | IV-2 | ANP32C | 0.84 |
| 3509 | 3 | 4 | 5 | | V-1 | ZNF259 | 1.52 | 3605 | 3 | 4 | | | IV-2 | AP1M2 | 0.97 |
| 3510 | 3 | 4 | 5 | | V-1 | ZNF271 | 1.61 | 3606 | 3 | 4 | | | IV-2 | APITD1-CORT | 0.87 |
| 3511 | 3 | 4 | 5 | | V-1 | ZNF277 | 1.64 | 3607 | 3 | 4 | | | IV-2 | APOL2 | 0.85 |
| 3512 | 3 | 4 | 5 | | V-1 | ZNF295 | 1.57 | 3608 | 3 | 4 | | | IV-2 | APOO | 0.96 |
| 3513 | 3 | 4 | 5 | | V-1 | ZNF319 | 1.52 | 3609 | 3 | 4 | | | IV-2 | AREG | 0.91 |
| 3514 | 3 | 4 | 5 | | V-1 | ZNF322 | 1.52 | 3610 | 3 | 4 | | | IV-2 | ARGLU1 | 0.91 |
| 3515 | 3 | 4 | 5 | | V-1 | ZNF330 | 1.70 | 3611 | 3 | 4 | | | IV-2 | ARHGAP10 | 0.94 |
| 3516 | 3 | 4 | 5 | | V-1 | ZNF35 | 1.51 | 3612 | 3 | 4 | | | IV-2 | ARHGAP25 | 0.82 |
| 3517 | 3 | 4 | 5 | | V-1 | ZNF407 | 1.58 | 3613 | 3 | 4 | | | IV-2 | ARHGAP27 | 0.97 |
| 3518 | 3 | 4 | 5 | | V-1 | ZNF426 | 1.52 | 3614 | 3 | 4 | | | IV-2 | ARHGAP9 | 0.75 |
| 3519 | 3 | 4 | 5 | | V-1 | ZNF526 | 1.64 | 3615 | 3 | 4 | | | IV-2 | ARHGEF19 | 0.96 |
| 3520 | 3 | 4 | 5 | | V-1 | ZNF532 | 1.54 | 3616 | 3 | 4 | | | IV-2 | ARHGEF5 | 0.97 |
| 3521 | 3 | 4 | 5 | | V-1 | ZNF562 | 1.80 | 3617 | 3 | 4 | | | IV-2 | ARHGEF9 | 0.87 |
| 3522 | 3 | 4 | 5 | | V-1 | ZNF579 | 1.55 | 3618 | 3 | 4 | | | IV-2 | ARID3B | 0.78 |
| 3523 | 3 | 4 | 5 | | V-1 | ZNF581 | 1.72 | 3619 | 3 | 4 | | | IV-2 | ARID5A | 0.81 |
| 3524 | 3 | 4 | 5 | | V-1 | ZNF605 | 1.95 | 3620 | 3 | 4 | | | IV-2 | ARL10 | 0.94 |
| 3525 | 3 | 4 | 5 | | V-1 | ZNF609 | 1.57 | 3621 | 3 | 4 | | | IV-2 | ARL17B | 0.92 |
| 3526 | 3 | 4 | 5 | | V-1 | ZNF611 | 1.67 | 3622 | 3 | 4 | | | IV-2 | ARL3 | 0.89 |
| 3527 | 3 | 4 | 5 | | V-1 | ZNF638 | 1.51 | 3623 | 3 | 4 | | | IV-2 | ARL4D | 0.75 |
| 3528 | 3 | 4 | 5 | | V-1 | ZNF644 | 1.51 | 3624 | 3 | 4 | | | IV-2 | ARRB2 | 0.90 |
| 3529 | 3 | 4 | 5 | | V-1 | ZNF689 | 1.59 | 3625 | 3 | 4 | | | IV-2 | ARSG | 0.93 |
| 3530 | 3 | 4 | 5 | | V-1 | ZNF707 | 1.66 | 3626 | 3 | 4 | | | IV-2 | ASAP2 | 0.90 |
| 3531 | 3 | 4 | 5 | | V-1 | ZNF718 | 1.56 | 3627 | 3 | 4 | | | IV-2 | ASMTL-AS1 | 0.96 |
| 3532 | 3 | 4 | 5 | | V-1 | ZNF765 | 1.59 | 3628 | 3 | 4 | | | IV-2 | ASNSD1 | 0.90 |
| 3533 | 3 | 4 | 5 | | V-1 | ZNF770 | 1.64 | 3629 | 3 | 4 | | | IV-2 | ATF4 | 0.86 |
| 3534 | 3 | 4 | 5 | | V-1 | ZNF772 | 1.70 | 3630 | 3 | 4 | | | IV-2 | ATF7IP2 | 0.79 |
| 3535 | 3 | 4 | 5 | | V-1 | ZNF780A | 1.96 | 3631 | 3 | 4 | | | IV-2 | ATG16L1 | 0.90 |
| 3536 | 3 | 4 | 5 | | V-1 | ZNF784 | 1.58 | 3632 | 3 | 4 | | | IV-2 | ATG2A | 0.89 |
| 3537 | 3 | 4 | 5 | | V-1 | ZNF800 | 1.51 | 3633 | 3 | 4 | | | IV-2 | ATP2A3 | 0.93 |
| 3538 | 3 | 4 | 5 | | V-1 | ZNF81 | 1.62 | 3634 | 3 | 4 | | | IV-2 | ATP5I | 0.68 |
| 3539 | 3 | 4 | 5 | | V-1 | ZNF91 | 1.62 | 3635 | 3 | 4 | | | IV-2 | ATP6V1G1 | 0.96 |
| 3540 | 3 | 4 | 5 | | V-1 | ZNRF1 | 1.75 | 3636 | 3 | 4 | | | IV-2 | ATP8B2 | 0.92 |
| 3541 | 3 | 4 | 5 | | V-1 | ZW10 | 1.71 | 3637 | 3 | 4 | | | IV-2 | ATXN7L2 | 0.86 |
| 3542 | 3 | 4 | 5 | | V-1 | ZWINT | 1.91 | 3638 | 3 | 4 | | | IV-2 | AVIL | 1.00 |
| 3543 | 3 | 4 | 5 | | V-1 | ZYG11B | 1.76 | 3639 | 3 | 4 | | | IV-2 | B2M | 0.81 |
| 3544 | 3 | 4 | | | IV-2 | A1BG-AS1 | 0.93 | 3640 | 3 | 4 | | | IV-2 | B3GALT2 | 0.95 |
| 3545 | 3 | 4 | | | IV-2 | ABAT | 0.95 | 3641 | 3 | 4 | | | IV-2 | B3GNT9 | 0.81 |
| 3546 | 3 | 4 | | | IV-2 | ABCA11P | 0.73 | 3642 | 3 | 4 | | | IV-2 | B4GALNT3 | 0.98 |
| 3547 | 3 | 4 | | | IV-2 | ABCC4 | 0.85 | 3643 | 3 | 4 | | | IV-2 | B4GALT2 | 0.96 |
| 3548 | 3 | 4 | | | IV-2 | ABCC5 | 0.74 | 3644 | 3 | 4 | | | IV-2 | B4GALT3 | 0.95 |
| 3549 | 3 | 4 | | | IV-2 | ABHD14A | 0.99 | 3645 | 3 | 4 | | | IV-2 | B4GALT6 | 0.93 |

Fig. 41 - 20

| | | | | | | | | | | | | | |
|---|---|---|---|---|---|---|---|---|---|---|---|---|---|
| 3646 | 3 | 4 | | | IV-2 | BACE1-AS | 0.94 | 3742 | 3 | 4 | | IV-2 | C9orf89 | 0.84 |
| 3647 | 3 | 4 | | | IV-2 | BAMBI | 0.99 | 3743 | 3 | 4 | | IV-2 | C9orf95 | 0.96 |
| 3648 | 3 | 4 | | | IV-2 | BANP | 0.93 | 3744 | 3 | 4 | | IV-2 | CA11 | 0.81 |
| 3649 | 3 | 4 | | | IV-2 | BAZ2B | 0.78 | 3745 | 3 | 4 | | IV-2 | CABIN1 | 0.77 |
| 3650 | 3 | 4 | | | IV-2 | BBC3 | 0.81 | 3746 | 3 | 4 | | IV-2 | CACNA1I | 0.95 |
| 3651 | 3 | 4 | | | IV-2 | BBIP1 | 0.80 | 3747 | 3 | 4 | | IV-2 | CACNB4 | 0.93 |
| 3652 | 3 | 4 | | | IV-2 | BCKDHB | 0.91 | 3748 | 3 | 4 | | IV-2 | CAHM | 0.93 |
| 3653 | 3 | 4 | | | IV-2 | BDH1 | 0.90 | 3749 | 3 | 4 | | IV-2 | CALCOCO1 | 0.77 |
| 3654 | 3 | 4 | | | IV-2 | BDH2 | 0.87 | 3750 | 3 | 4 | | IV-2 | CAMK2G | 0.78 |
| 3655 | 3 | 4 | | | IV-2 | BEX2 | 0.88 | 3751 | 3 | 4 | | IV-2 | CAPN3 | 0.80 |
| 3656 | 3 | 4 | | | IV-2 | BEX4 | 0.94 | 3752 | 3 | 4 | | IV-2 | CARD11 | 0.97 |
| 3657 | 3 | 4 | | | IV-2 | BHLHE40 | 0.96 | 3753 | 3 | 4 | | IV-2 | CARD8 | 0.72 |
| 3658 | 3 | 4 | | | IV-2 | BHLHE41 | 0.90 | 3754 | 3 | 4 | | IV-2 | CARNS1 | 0.85 |
| 3659 | 3 | 4 | | | IV-2 | BICD1 | 0.99 | 3755 | 3 | 4 | | IV-2 | CASK | 0.98 |
| 3660 | 3 | 4 | | | IV-2 | BIN2 | 0.99 | 3756 | 3 | 4 | | IV-2 | CASP4 | 0.98 |
| 3661 | 3 | 4 | | | IV-2 | BIRC3 | 0.83 | 3757 | 3 | 4 | | IV-2 | CASP8 | 0.72 |
| 3662 | 3 | 4 | | | IV-2 | BLOC1S1-RDH5 | 0.96 | 3758 | 3 | 4 | | IV-2 | CBX3P2 | 0.99 |
| 3663 | 3 | 4 | | | IV-2 | BMP2 | 1.00 | 3759 | 3 | 4 | | IV-2 | CBX4 | 0.97 |
| 3664 | 3 | 4 | | | IV-2 | BOD1 | 0.80 | 3760 | 3 | 4 | | IV-2 | CC2D1B | 0.99 |
| 3665 | 3 | 4 | | | IV-2 | BPHL | 0.78 | 3761 | 3 | 4 | | IV-2 | CCDC104 | 0.93 |
| 3666 | 3 | 4 | | | IV-2 | BRD2 | 0.97 | 3762 | 3 | 4 | | IV-2 | CCDC122 | 0.99 |
| 3667 | 3 | 4 | | | IV-2 | BRD8 | 0.91 | 3763 | 3 | 4 | | IV-2 | CCDC125 | 0.70 |
| 3668 | 3 | 4 | | | IV-2 | BRPF3 | 0.94 | 3764 | 3 | 4 | | IV-2 | CCDC130 | 0.87 |
| 3669 | 3 | 4 | | | IV-2 | BRWD3 | 0.87 | 3765 | 3 | 4 | | IV-2 | CCDC14 | 0.75 |
| 3670 | 3 | 4 | | | IV-2 | BTF3P11 | 0.94 | 3766 | 3 | 4 | | IV-2 | CCDC153 | 0.94 |
| 3671 | 3 | 4 | | | IV-2 | BTG2 | 0.84 | 3767 | 3 | 4 | | IV-2 | CCDC163P | 0.85 |
| 3672 | 3 | 4 | | | IV-2 | BTN2A2 | 0.93 | 3768 | 3 | 4 | | IV-2 | CCDC167 | 0.91 |
| 3673 | 3 | 4 | | | IV-2 | C11orf54 | 0.89 | 3769 | 3 | 4 | | IV-2 | CCDC23 | 0.67 |
| 3674 | 3 | 4 | | | IV-2 | C11orf63 | 0.92 | 3770 | 3 | 4 | | IV-2 | CCDC42B | 1.00 |
| 3675 | 3 | 4 | | | IV-2 | C11orf74 | 0.98 | 3771 | 3 | 4 | | IV-2 | CCDC75 | 0.91 |
| 3676 | 3 | 4 | | | IV-2 | C12orf29 | 0.87 | 3772 | 3 | 4 | | IV-2 | CCDC76 | 0.92 |
| 3677 | 3 | 4 | | | IV-2 | C12orf35 | 0.73 | 3773 | 3 | 4 | | IV-2 | CCDC85C | 0.91 |
| 3678 | 3 | 4 | | | IV-2 | C12orf42 | 1.00 | 3774 | 3 | 4 | | IV-2 | CCDC88B | 0.99 |
| 3679 | 3 | 4 | | | IV-2 | C12orf66 | 0.83 | 3775 | 3 | 4 | | IV-2 | CCDC90A | 0.76 |
| 3680 | 3 | 4 | | | IV-2 | C14orf149 | 0.98 | 3776 | 3 | 4 | | IV-2 | CCDC92 | 0.96 |
| 3681 | 3 | 4 | | | IV-2 | C14orf159 | 0.83 | 3777 | 3 | 4 | | IV-2 | CCL2 | 0.89 |
| 3682 | 3 | 4 | | | IV-2 | C14orf28 | 0.89 | 3778 | 3 | 4 | | IV-2 | CCL23 | 0.97 |
| 3683 | 3 | 4 | | | IV-2 | C14orf93 | 0.85 | 3779 | 3 | 4 | | IV-2 | CCNB1IP1 | 0.82 |
| 3684 | 3 | 4 | | | IV-2 | C15orf17 | 0.91 | 3780 | 3 | 4 | | IV-2 | CCNG2 | 0.84 |
| 3685 | 3 | 4 | | | IV-2 | C15orf23 | 0.98 | 3781 | 3 | 4 | | IV-2 | CCNL1 | 0.69 |
| 3686 | 3 | 4 | | | IV-2 | C15orf40 | 0.98 | 3782 | 3 | 4 | | IV-2 | CCNT2 | 0.93 |
| 3687 | 3 | 4 | | | IV-2 | C15orf50 | 1.00 | 3783 | 3 | 4 | | IV-2 | CCT6P1 | 0.92 |
| 3688 | 3 | 4 | | | IV-2 | C15orf52 | 0.96 | 3784 | 3 | 4 | | IV-2 | CD1C | 1.00 |
| 3689 | 3 | 4 | | | IV-2 | C15orf62 | 0.93 | 3785 | 3 | 4 | | IV-2 | CD2 | 0.89 |
| 3690 | 3 | 4 | | | IV-2 | C16orf45 | 0.87 | 3786 | 3 | 4 | | IV-2 | CD200R1 | 0.90 |
| 3691 | 3 | 4 | | | IV-2 | C16orf5 | 0.95 | 3787 | 3 | 4 | | IV-2 | CD209 | 0.99 |
| 3692 | 3 | 4 | | | IV-2 | C16orf54 | 0.68 | 3788 | 3 | 4 | | IV-2 | CD226 | 0.93 |
| 3693 | 3 | 4 | | | IV-2 | C16orf80 | 0.99 | 3789 | 3 | 4 | | IV-2 | CD247 | 0.94 |
| 3694 | 3 | 4 | | | IV-2 | C17orf48 | 0.94 | 3790 | 3 | 4 | | IV-2 | CD58 | 0.79 |
| 3695 | 3 | 4 | | | IV-2 | C17orf65 | 0.82 | 3791 | 3 | 4 | | IV-2 | CD8A | 0.93 |
| 3696 | 3 | 4 | | | IV-2 | C17orf72 | 0.81 | 3792 | 3 | 4 | | IV-2 | CDC123 | 0.85 |
| 3697 | 3 | 4 | | | IV-2 | C18orf25 | 0.95 | 3793 | 3 | 4 | | IV-2 | CDC14A | 0.99 |
| 3698 | 3 | 4 | | | IV-2 | C19orf25 | 0.99 | 3794 | 3 | 4 | | IV-2 | CDC14C | 0.90 |
| 3699 | 3 | 4 | | | IV-2 | C19orf53 | 0.93 | 3795 | 3 | 4 | | IV-2 | CDC26 | 0.80 |
| 3700 | 3 | 4 | | | IV-2 | C19orf55 | 0.84 | 3796 | 3 | 4 | | IV-2 | CDC37L1 | 0.98 |
| 3701 | 3 | 4 | | | IV-2 | C19orf6 | 1.00 | 3797 | 3 | 4 | | IV-2 | CDC42EP2 | 0.79 |
| 3702 | 3 | 4 | | | IV-2 | C19orf60 | 0.97 | 3798 | 3 | 4 | | IV-2 | CDC42SE1 | 0.99 |
| 3703 | 3 | 4 | | | IV-2 | C19orf66 | 0.97 | 3799 | 3 | 4 | | IV-2 | CDC42SE2 | 0.89 |
| 3704 | 3 | 4 | | | IV-2 | C19orf70 | 0.96 | 3800 | 3 | 4 | | IV-2 | CDCA4 | 0.93 |
| 3705 | 3 | 4 | | | IV-2 | C1QL3 | 0.97 | 3801 | 3 | 4 | | IV-2 | CDH23 | 0.99 |
| 3706 | 3 | 4 | | | IV-2 | C1QTNF6 | 0.88 | 3802 | 3 | 4 | | IV-2 | CDKL5 | 0.96 |
| 3707 | 3 | 4 | | | IV-2 | C1orf116 | 0.99 | 3803 | 3 | 4 | | IV-2 | CDKN1B | 0.93 |
| 3708 | 3 | 4 | | | IV-2 | C1orf150 | 0.70 | 3804 | 3 | 4 | | IV-2 | CDRT4 | 0.83 |
| 3709 | 3 | 4 | | | IV-2 | C1orf151-NBL1 | 0.88 | 3805 | 3 | 4 | | IV-2 | CENPH | 0.73 |
| 3710 | 3 | 4 | | | IV-2 | C1orf159 | 0.93 | 3806 | 3 | 4 | | IV-2 | CENPL | 0.92 |
| 3711 | 3 | 4 | | | IV-2 | C1orf174 | 0.96 | 3807 | 3 | 4 | | IV-2 | CENPM | 0.99 |
| 3712 | 3 | 4 | | | IV-2 | C1orf186 | 0.98 | 3808 | 3 | 4 | | IV-2 | CEP85L | 0.95 |
| 3713 | 3 | 4 | | | IV-2 | C1orf201 | 0.97 | 3809 | 3 | 4 | | IV-2 | CEP95 | 0.88 |
| 3714 | 3 | 4 | | | IV-2 | C1orf56 | 0.77 | 3810 | 3 | 4 | | IV-2 | CETN3 | 0.87 |
| 3715 | 3 | 4 | | | IV-2 | C20orf111 | 0.86 | 3811 | 3 | 4 | | IV-2 | CFH | 0.93 |
| 3716 | 3 | 4 | | | IV-2 | C20orf112 | 0.86 | 3812 | 3 | 4 | | IV-2 | CFL2 | 0.85 |
| 3717 | 3 | 4 | | | IV-2 | C20orf197 | 0.96 | 3813 | 3 | 4 | | IV-2 | CFLAR | 0.98 |
| 3718 | 3 | 4 | | | IV-2 | C21orf58 | 0.99 | 3814 | 3 | 4 | | IV-2 | CG030 | 0.95 |
| 3719 | 3 | 4 | | | IV-2 | C22orf13 | 0.91 | 3815 | 3 | 4 | | IV-2 | CHD7 | 0.97 |
| 3720 | 3 | 4 | | | IV-2 | C2orf55 | 0.95 | 3816 | 3 | 4 | | IV-2 | CHRNE | 0.94 |
| 3721 | 3 | 4 | | | IV-2 | C3orf18 | 0.79 | 3817 | 3 | 4 | | IV-2 | CHST10 | 0.94 |
| 3722 | 3 | 4 | | | IV-2 | C3orf62 | 0.76 | 3818 | 3 | 4 | | IV-2 | CHST11 | 0.95 |
| 3723 | 3 | 4 | | | IV-2 | C4orf29 | 0.75 | 3819 | 3 | 4 | | IV-2 | CIDECP | 0.67 |
| 3724 | 3 | 4 | | | IV-2 | C5orf20 | 0.72 | 3820 | 3 | 4 | | IV-2 | CIR1 | 0.96 |
| 3725 | 3 | 4 | | | IV-2 | C5orf39 | 0.84 | 3821 | 3 | 4 | | IV-2 | CIRBP | 0.89 |
| 3726 | 3 | 4 | | | IV-2 | C5orf63 | 0.98 | 3822 | 3 | 4 | | IV-2 | CIRBP-AS1 | 0.98 |
| 3727 | 3 | 4 | | | IV-2 | C6orf1 | 0.81 | 3823 | 3 | 4 | | IV-2 | CKS1B | 0.82 |
| 3728 | 3 | 4 | | | IV-2 | C6orf192 | 0.74 | 3824 | 3 | 4 | | IV-2 | CLASRP | 0.72 |
| 3729 | 3 | 4 | | | IV-2 | C7orf44 | 0.73 | 3825 | 3 | 4 | | IV-2 | CLCF1 | 0.69 |
| 3730 | 3 | 4 | | | IV-2 | C7orf49 | 0.95 | 3826 | 3 | 4 | | IV-2 | CLDND1 | 0.84 |
| 3731 | 3 | 4 | | | IV-2 | C7orf61 | 0.90 | 3827 | 3 | 4 | | IV-2 | CLEC2B | 0.75 |
| 3732 | 3 | 4 | | | IV-2 | C8orf44 | 1.00 | 3828 | 3 | 4 | | IV-2 | CLEC2D | 0.83 |
| 3733 | 3 | 4 | | | IV-2 | C8orf44-SGK3 | 0.93 | 3829 | 3 | 4 | | IV-2 | CLEC7A | 0.88 |
| 3734 | 3 | 4 | | | IV-2 | C8orf58 | 0.90 | 3830 | 3 | 4 | | IV-2 | CLIC5 | 0.88 |
| 3735 | 3 | 4 | | | IV-2 | C8orf73 | 0.86 | 3831 | 3 | 4 | | IV-2 | CLK2 | 0.87 |
| 3736 | 3 | 4 | | | IV-2 | C9orf100 | 1.00 | 3832 | 3 | 4 | | IV-2 | CLK3 | 0.95 |
| 3737 | 3 | 4 | | | IV-2 | C9orf123 | 0.90 | 3833 | 3 | 4 | | IV-2 | CNFN | 0.95 |
| 3738 | 3 | 4 | | | IV-2 | C9orf16 | 0.99 | 3834 | 3 | 4 | | IV-2 | CNKSR2 | 0.97 |
| 3739 | 3 | 4 | | | IV-2 | C9orf172 | 0.97 | 3835 | 3 | 4 | | IV-2 | CNN3 | 0.89 |
| 3740 | 3 | 4 | | | IV-2 | C9orf25 | 1.00 | 3836 | 3 | 4 | | IV-2 | CNOT3 | 0.98 |
| 3741 | 3 | 4 | | | IV-2 | C9orf46 | 0.82 | 3837 | 3 | 4 | | IV-2 | CNTNAP2 | 0.96 |

Fig. 41 - 21

| | | | | | | | | | | | | | | |
|---|---|---|---|---|---|---|---|---|---|---|---|---|---|---|
| 3838 | 3 | 4 | | | IV-2 | CNTNAP3B | 1.00 | 3933 | 3 | 4 | | | IV-2 | ENY2 | 0.88 |
| 3839 | 3 | 4 | | | IV-2 | COA5 | 0.97 | 3934 | 3 | 4 | | | IV-2 | EPB41 | 0.84 |
| 3840 | 3 | 4 | | | IV-2 | COCH | 0.97 | 3935 | 3 | 4 | | | IV-2 | EPPK1 | 0.99 |
| 3841 | 3 | 4 | | | IV-2 | COQ10A | 1.00 | 3936 | 3 | 4 | | | IV-2 | EPS15L1 | 0.94 |
| 3842 | 3 | 4 | | | IV-2 | COQ3 | 0.94 | 3937 | 3 | 4 | | | IV-2 | EPS8L2 | 0.78 |
| 3843 | 3 | 4 | | | IV-2 | CRIPAK | 0.79 | 3938 | 3 | 4 | | | IV-2 | ERGIC1 | 0.96 |
| 3844 | 3 | 4 | | | IV-2 | CRIPT | 0.83 | 3939 | 3 | 4 | | | IV-2 | EZH1 | 0.68 |
| 3845 | 3 | 4 | | | IV-2 | CROCCP3 | 0.96 | 3940 | 3 | 4 | | | IV-2 | F2RL1 | 0.96 |
| 3846 | 3 | 4 | | | IV-2 | CRTC2 | 0.76 | 3941 | 3 | 4 | | | IV-2 | FAAH | 0.76 |
| 3847 | 3 | 4 | | | IV-2 | CSF2RB | 0.80 | 3942 | 3 | 4 | | | IV-2 | FADS3 | 0.99 |
| 3848 | 3 | 4 | | | IV-2 | CSNK1E | 0.94 | 3943 | 3 | 4 | | | IV-2 | FAM100A | 0.93 |
| 3849 | 3 | 4 | | | IV-2 | CSNK1G2 | 0.97 | 3944 | 3 | 4 | | | IV-2 | FAM100B | 0.81 |
| 3850 | 3 | 4 | | | IV-2 | CTAGE15P | 0.97 | 3945 | 3 | 4 | | | IV-2 | FAM104B | 0.97 |
| 3851 | 3 | 4 | | | IV-2 | CTC1 | 0.89 | 3946 | 3 | 4 | | | IV-2 | FAM108A1 | 0.89 |
| 3852 | 3 | 4 | | | IV-2 | CTNNAL1 | 0.97 | 3947 | 3 | 4 | | | IV-2 | FAM113A | 0.69 |
| 3853 | 3 | 4 | | | IV-2 | CTSE | 0.90 | 3948 | 3 | 4 | | | IV-2 | FAM133B | 0.90 |
| 3854 | 3 | 4 | | | IV-2 | CTSF | 0.77 | 3949 | 3 | 4 | | | IV-2 | FAM162A | 1.00 |
| 3855 | 3 | 4 | | | IV-2 | CTTN | 0.74 | 3950 | 3 | 4 | | | IV-2 | FAM169A | 0.86 |
| 3856 | 3 | 4 | | | IV-2 | CTU2 | 0.89 | 3951 | 3 | 4 | | | IV-2 | FAM177B | 0.97 |
| 3857 | 3 | 4 | | | IV-2 | CXCR1 | 0.80 | 3952 | 3 | 4 | | | IV-2 | FAM188A | 0.96 |
| 3858 | 3 | 4 | | | IV-2 | CXCR2 | 0.78 | 3953 | 3 | 4 | | | IV-2 | FAM195B | 0.97 |
| 3859 | 3 | 4 | | | IV-2 | CXXC5 | 0.87 | 3954 | 3 | 4 | | | IV-2 | FAM19A2 | 0.95 |
| 3860 | 3 | 4 | | | IV-2 | CYB561 | 0.81 | 3955 | 3 | 4 | | | IV-2 | FAM209B | 0.98 |
| 3861 | 3 | 4 | | | IV-2 | CYB5D1 | 0.78 | 3956 | 3 | 4 | | | IV-2 | FAM214A | 0.95 |
| 3862 | 3 | 4 | | | IV-2 | CYB5D2 | 0.87 | 3957 | 3 | 4 | | | IV-2 | FAM27A | 0.91 |
| 3863 | 3 | 4 | | | IV-2 | CYB5RL | 0.99 | 3958 | 3 | 4 | | | IV-2 | FAM27B | 0.91 |
| 3864 | 3 | 4 | | | IV-2 | CYP4F2 | 0.72 | 3959 | 3 | 4 | | | IV-2 | FAM3A | 0.98 |
| 3865 | 3 | 4 | | | IV-2 | CYP4F22 | 0.97 | 3960 | 3 | 4 | | | IV-2 | FAM53C | 0.79 |
| 3866 | 3 | 4 | | | IV-2 | CYTH3 | 0.88 | 3961 | 3 | 4 | | | IV-2 | FAM58BP | 0.84 |
| 3867 | 3 | 4 | | | IV-2 | CYTH4 | 0.95 | 3962 | 3 | 4 | | | IV-2 | FAM73B | 0.86 |
| 3868 | 3 | 4 | | | IV-2 | D2HGDH | 0.89 | 3963 | 3 | 4 | | | IV-2 | FAM83H | 0.98 |
| 3869 | 3 | 4 | | | IV-2 | DANCR | 0.97 | 3964 | 3 | 4 | | | IV-2 | FAM8A1 | 0.76 |
| 3870 | 3 | 4 | | | IV-2 | DBF4 | 0.96 | 3965 | 3 | 4 | | | IV-2 | FAM98C | 0.73 |
| 3871 | 3 | 4 | | | IV-2 | DBN1 | 0.82 | 3966 | 3 | 4 | | | IV-2 | FANCA | 0.85 |
| 3872 | 3 | 4 | | | IV-2 | DCLRE1A | 0.85 | 3967 | 3 | 4 | | | IV-2 | FARP2 | 1.00 |
| 3873 | 3 | 4 | | | IV-2 | DCXR | 0.96 | 3968 | 3 | 4 | | | IV-2 | FARS2 | 0.91 |
| 3874 | 3 | 4 | | | IV-2 | DDB2 | 0.88 | 3969 | 3 | 4 | | | IV-2 | FAU | 0.79 |
| 3875 | 3 | 4 | | | IV-2 | DDX11L9 | 0.92 | 3970 | 3 | 4 | | | IV-2 | FBLN2 | 0.98 |
| 3876 | 3 | 4 | | | IV-2 | DDX17 | 0.99 | 3971 | 3 | 4 | | | IV-2 | FBN2 | 0.98 |
| 3877 | 3 | 4 | | | IV-2 | DEDD2 | 0.94 | 3972 | 3 | 4 | | | IV-2 | FBRS | 0.97 |
| 3878 | 3 | 4 | | | IV-2 | DEF6 | 0.95 | 3973 | 3 | 4 | | | IV-2 | FBXL13 | 0.99 |
| 3879 | 3 | 4 | | | IV-2 | DEFB109P1 | 0.94 | 3974 | 3 | 4 | | | IV-2 | FBXL8 | 0.79 |
| 3880 | 3 | 4 | | | IV-2 | DERL3 | 0.94 | 3975 | 3 | 4 | | | IV-2 | FBXO10 | 0.77 |
| 3881 | 3 | 4 | | | IV-2 | DES | 0.95 | 3976 | 3 | 4 | | | IV-2 | FBXO48 | 0.80 |
| 3882 | 3 | 4 | | | IV-2 | DGAT2 | 0.80 | 3977 | 3 | 4 | | | IV-2 | FCGR2A | 0.89 |
| 3883 | 3 | 4 | | | IV-2 | DGKA | 0.94 | 3978 | 3 | 4 | | | IV-2 | FCHO1 | 0.87 |
| 3884 | 3 | 4 | | | IV-2 | DGKE | 0.87 | 3979 | 3 | 4 | | | IV-2 | FCRL6 | 0.79 |
| 3885 | 3 | 4 | | | IV-2 | DGKQ | 0.71 | 3980 | 3 | 4 | | | IV-2 | FCRLB | 1.00 |
| 3886 | 3 | 4 | | | IV-2 | DHRS3 | 0.78 | 3981 | 3 | 4 | | | IV-2 | FDPSL2A | 0.98 |
| 3887 | 3 | 4 | | | IV-2 | DHTKD1 | 0.98 | 3982 | 3 | 4 | | | IV-2 | FDX1L | 0.88 |
| 3888 | 3 | 4 | | | IV-2 | DICER1-AS1 | 0.91 | 3983 | 3 | 4 | | | IV-2 | FGD3 | 0.95 |
| 3889 | 3 | 4 | | | IV-2 | DLEU2 | 0.98 | 3984 | 3 | 4 | | | IV-2 | FGF13 | 0.85 |
| 3890 | 3 | 4 | | | IV-2 | DLG5 | 1.00 | 3985 | 3 | 4 | | | IV-2 | FGFR1OP | 0.73 |
| 3891 | 3 | 4 | | | IV-2 | DMKN | 1.00 | 3986 | 3 | 4 | | | IV-2 | FHDC1 | 0.95 |
| 3892 | 3 | 4 | | | IV-2 | DMTF1 | 0.74 | 3987 | 3 | 4 | | | IV-2 | FHIT | 0.91 |
| 3893 | 3 | 4 | | | IV-2 | DNAJC25 | 0.94 | 3988 | 3 | 4 | | | IV-2 | FHL2 | 0.91 |
| 3894 | 3 | 4 | | | IV-2 | DNAJC4 | 1.00 | 3989 | 3 | 4 | | | IV-2 | FITM1 | 0.90 |
| 3895 | 3 | 4 | | | IV-2 | DNAJC9 | 0.86 | 3990 | 3 | 4 | | | IV-2 | FKBP11 | 0.71 |
| 3896 | 3 | 4 | | | IV-2 | DNAL4 | 0.85 | 3991 | 3 | 4 | | | IV-2 | FLJ10038 | 0.93 |
| 3897 | 3 | 4 | | | IV-2 | DND1 | 0.89 | 3992 | 3 | 4 | | | IV-2 | FLJ27352 | 0.97 |
| 3898 | 3 | 4 | | | IV-2 | DNM3 | 0.87 | 3993 | 3 | 4 | | | IV-2 | FLJ27354 | 0.92 |
| 3899 | 3 | 4 | | | IV-2 | DNTTIP1 | 0.93 | 3994 | 3 | 4 | | | IV-2 | FLJ31306 | 0.86 |
| 3900 | 3 | 4 | | | IV-2 | DOCK5 | 0.80 | 3995 | 3 | 4 | | | IV-2 | FLJ39639 | 0.75 |
| 3901 | 3 | 4 | | | IV-2 | DPH1 | 0.74 | 3996 | 3 | 4 | | | IV-2 | FLJ44635 | 0.86 |
| 3902 | 3 | 4 | | | IV-2 | DPY30 | 0.96 | 3997 | 3 | 4 | | | IV-2 | FLJ45340 | 0.71 |
| 3903 | 3 | 4 | | | IV-2 | DSN1 | 0.93 | 3998 | 3 | 4 | | | IV-2 | FLT3LG | 0.87 |
| 3904 | 3 | 4 | | | IV-2 | DTX2 | 0.86 | 3999 | 3 | 4 | | | IV-2 | FLYWCH2 | 0.95 |
| 3905 | 3 | 4 | | | IV-2 | DTX2P1-UPK3BP1-PMS2P11 | 0.87 | 4000 | 3 | 4 | | | IV-2 | FMNL1 | 0.93 |
| | | | | | | | | 4001 | 3 | 4 | | | IV-2 | FMNL3 | 0.83 |
| 3906 | 3 | 4 | | | IV-2 | DUSP19 | 0.99 | 4002 | 3 | 4 | | | IV-2 | FNBP4 | 0.73 |
| 3907 | 3 | 4 | | | IV-2 | DUSP2 | 0.73 | 4003 | 3 | 4 | | | IV-2 | FOS | 0.94 |
| 3908 | 3 | 4 | | | IV-2 | DYRK3 | 0.99 | 4004 | 3 | 4 | | | IV-2 | FOXM1 | 0.95 |
| 3909 | 3 | 4 | | | IV-2 | EBF1 | 0.94 | 4005 | 3 | 4 | | | IV-2 | FPGS | 0.98 |
| 3910 | 3 | 4 | | | IV-2 | EEF1D | 0.98 | 4006 | 3 | 4 | | | IV-2 | FPR2 | 0.99 |
| 3911 | 3 | 4 | | | IV-2 | EEF1E1 | 0.89 | 4007 | 3 | 4 | | | IV-2 | FRAT1 | 0.98 |
| 3912 | 3 | 4 | | | IV-2 | EEPD1 | 0.99 | 4008 | 3 | 4 | | | IV-2 | FRS3 | 0.84 |
| 3913 | 3 | 4 | | | IV-2 | EFCAB2 | 0.99 | 4009 | 3 | 4 | | | IV-2 | FTH1 | 0.79 |
| 3914 | 3 | 4 | | | IV-2 | EFCAB4A | 0.97 | 4010 | 3 | 4 | | | IV-2 | FUT10 | 0.75 |
| 3915 | 3 | 4 | | | IV-2 | EFNA1 | 0.92 | 4011 | 3 | 4 | | | IV-2 | FUZ | 0.82 |
| 3916 | 3 | 4 | | | IV-2 | EFNA3 | 0.97 | 4012 | 3 | 4 | | | IV-2 | FXYD2 | 0.99 |
| 3917 | 3 | 4 | | | IV-2 | EGF | 0.94 | 4013 | 3 | 4 | | | IV-2 | FXYD7 | 0.84 |
| 3918 | 3 | 4 | | | IV-2 | EGFL7 | 0.89 | 4014 | 3 | 4 | | | IV-2 | GAB1 | 1.00 |
| 3919 | 3 | 4 | | | IV-2 | EGLN2 | 0.91 | 4015 | 3 | 4 | | | IV-2 | GAB2 | 0.83 |
| 3920 | 3 | 4 | | | IV-2 | EGLN3 | 0.92 | 4016 | 3 | 4 | | | IV-2 | GAB3 | 0.94 |
| 3921 | 3 | 4 | | | IV-2 | EHD1 | 0.88 | 4017 | 3 | 4 | | | IV-2 | GABARAPL1 | 0.82 |
| 3922 | 3 | 4 | | | IV-2 | EIF1AX | 0.99 | 4018 | 3 | 4 | | | IV-2 | GADD45A | 0.89 |
| 3923 | 3 | 4 | | | IV-2 | EIF5A | 0.72 | 4019 | 3 | 4 | | | IV-2 | GALNT12 | 0.97 |
| 3924 | 3 | 4 | | | IV-2 | ELK2AP | 0.91 | 4020 | 3 | 4 | | | IV-2 | GATM | 0.96 |
| 3925 | 3 | 4 | | | IV-2 | ELL2 | 0.93 | 4021 | 3 | 4 | | | IV-2 | GATSL2 | 0.93 |
| 3926 | 3 | 4 | | | IV-2 | ELMOD3 | 0.97 | 4022 | 3 | 4 | | | IV-2 | GBA2 | 1.00 |
| 3927 | 3 | 4 | | | IV-2 | EMBP1 | 0.94 | 4023 | 3 | 4 | | | IV-2 | GBP2 | 1.00 |
| 3928 | 3 | 4 | | | IV-2 | EMR3 | 0.71 | 4024 | 3 | 4 | | | IV-2 | GCET2 | 0.96 |
| 3929 | 3 | 4 | | | IV-2 | ENDOV | 0.98 | 4025 | 3 | 4 | | | IV-2 | GCNT4 | 0.73 |
| 3930 | 3 | 4 | | | IV-2 | ENGASE | 0.69 | 4026 | 3 | 4 | | | IV-2 | GDI1 | 0.97 |
| 3931 | 3 | 4 | | | IV-2 | ENO2 | 0.80 | 4027 | 3 | 4 | | | IV-2 | GFI1 | 0.88 |
| 3932 | 3 | 4 | | | IV-2 | ENTPD1 | 0.99 | 4028 | 3 | 4 | | | IV-2 | GGTA1P | 0.80 |

Fig. 41 - 22

| | | | | | | | | | | | | | |
|---|---|---|---|---|---|---|---|---|---|---|---|---|---|
| 4029 | 3 | 4 | | | IV-2 | GHRLOS | 0.85 | 4125 | 3 | 4 | | IV-2 | IKZF5 | 0.80 |
| 4030 | 3 | 4 | | | IV-2 | GIPC3 | 0.92 | 4126 | 3 | 4 | | IV-2 | IL16 | 0.98 |
| 4031 | 3 | 4 | | | IV-2 | GK | 0.94 | 4127 | 3 | 4 | | IV-2 | IL1R1 | 0.73 |
| 4032 | 3 | 4 | | | IV-2 | GK3P | 0.74 | 4128 | 3 | 4 | | IV-2 | IL28RA | 0.76 |
| 4033 | 3 | 4 | | | IV-2 | GKAP1 | 0.99 | 4129 | 3 | 4 | | IV-2 | IL2RA | 0.99 |
| 4034 | 3 | 4 | | | IV-2 | GLI1 | 0.99 | 4130 | 3 | 4 | | IV-2 | IL2RG | 0.98 |
| 4035 | 3 | 4 | | | IV-2 | GLI4 | 0.83 | 4131 | 3 | 4 | | IV-2 | IL7R | 0.78 |
| 4036 | 3 | 4 | | | IV-2 | GLIS2 | 0.91 | 4132 | 3 | 4 | | IV-2 | IL9R | 0.92 |
| 4037 | 3 | 4 | | | IV-2 | GLYCTK | 0.82 | 4133 | 3 | 4 | | IV-2 | IMMP2L | 0.74 |
| 4038 | 3 | 4 | | | IV-2 | GMCL1P1 | 0.92 | 4134 | 3 | 4 | | IV-2 | ING1 | 0.97 |
| 4039 | 3 | 4 | | | IV-2 | GMIP | 0.91 | 4135 | 3 | 4 | | IV-2 | ING5 | 0.96 |
| 4040 | 3 | 4 | | | IV-2 | GMPR2 | 1.00 | 4136 | 3 | 4 | | IV-2 | INO80B-WBP1 | 0.90 |
| 4041 | 3 | 4 | | | IV-2 | GNAO1 | 0.96 | 4137 | 3 | 4 | | IV-2 | INO80E | 1.00 |
| 4042 | 3 | 4 | | | IV-2 | GNG11 | 0.75 | 4138 | 3 | 4 | | IV-2 | INPP5B | 0.96 |
| 4043 | 3 | 4 | | | IV-2 | GNG8 | 0.90 | 4139 | 3 | 4 | | IV-2 | INPP5E | 0.82 |
| 4044 | 3 | 4 | | | IV-2 | GNPDA2 | 0.71 | 4140 | 3 | 4 | | IV-2 | IP6K2 | 0.97 |
| 4045 | 3 | 4 | | | IV-2 | GNRHR2 | 0.83 | 4141 | 3 | 4 | | IV-2 | IPP | 0.97 |
| 4046 | 3 | 4 | | | IV-2 | GOLGA2P5 | 0.94 | 4142 | 3 | 4 | | IV-2 | IRAK2 | 0.81 |
| 4047 | 3 | 4 | | | IV-2 | GOLGA7B | 0.83 | 4143 | 3 | 4 | | IV-2 | IRF1 | 0.83 |
| 4048 | 3 | 4 | | | IV-2 | GOLPH3L | 0.93 | 4144 | 3 | 4 | | IV-2 | IRF3 | 0.97 |
| 4049 | 3 | 4 | | | IV-2 | GPR133 | 0.99 | 4145 | 3 | 4 | | IV-2 | IRS1 | 0.99 |
| 4050 | 3 | 4 | | | IV-2 | GPR153 | 0.98 | 4146 | 3 | 4 | | IV-2 | ISCA1 | 0.90 |
| 4051 | 3 | 4 | | | IV-2 | GPR157 | 0.80 | 4147 | 3 | 4 | | IV-2 | ISYNA1 | 0.87 |
| 4052 | 3 | 4 | | | IV-2 | GPR183 | 0.95 | 4148 | 3 | 4 | | IV-2 | ITK | 0.97 |
| 4053 | 3 | 4 | | | IV-2 | GPR27 | 0.85 | 4149 | 3 | 4 | | IV-2 | ITLN1 | 0.89 |
| 4054 | 3 | 4 | | | IV-2 | GPR68 | 0.79 | 4150 | 3 | 4 | | IV-2 | ITM2A | 0.93 |
| 4055 | 3 | 4 | | | IV-2 | GPR75 | 0.99 | 4151 | 3 | 4 | | IV-2 | ITM2B | 0.77 |
| 4056 | 3 | 4 | | | IV-2 | GPR82 | 0.90 | 4152 | 3 | 4 | | IV-2 | ITM2C | 0.67 |
| 4057 | 3 | 4 | | | IV-2 | GPS2 | 0.93 | 4153 | 3 | 4 | | IV-2 | ITPR3 | 0.94 |
| 4058 | 3 | 4 | | | IV-2 | GPSM3 | 0.72 | 4154 | 3 | 4 | | IV-2 | ITPRIPL1 | 0.98 |
| 4059 | 3 | 4 | | | IV-2 | GPX4 | 0.90 | 4155 | 3 | 4 | | IV-2 | IVNS1ABP | 0.92 |
| 4060 | 3 | 4 | | | IV-2 | GRAMD1C | 0.84 | 4156 | 3 | 4 | | IV-2 | IZUMO4 | 0.88 |
| 4061 | 3 | 4 | | | IV-2 | GRASP | 0.95 | 4157 | 3 | 4 | | IV-2 | JAKMIP2 | 0.89 |
| 4062 | 3 | 4 | | | IV-2 | GRHL1 | 0.99 | 4158 | 3 | 4 | | IV-2 | JPX | 0.98 |
| 4063 | 3 | 4 | | | IV-2 | GSTCD | 0.97 | 4159 | 3 | 4 | | IV-2 | KAT2B | 0.95 |
| 4064 | 3 | 4 | | | IV-2 | GTDC1 | 0.72 | 4160 | 3 | 4 | | IV-2 | KATNAL1 | 1.00 |
| 4065 | 3 | 4 | | | IV-2 | GTF2A1 | 0.92 | 4161 | 3 | 4 | | IV-2 | KBTBD3 | 0.92 |
| 4066 | 3 | 4 | | | IV-2 | GTF2H2B | 0.82 | 4162 | 3 | 4 | | IV-2 | KCNG1 | 0.89 |
| 4067 | 3 | 4 | | | IV-2 | GTF2IRD2 | 0.84 | 4163 | 3 | 4 | | IV-2 | KCNRG | 0.93 |
| 4068 | 3 | 4 | | | IV-2 | GTF2IRD2B | 0.84 | 4164 | 3 | 4 | | IV-2 | KCTD7 | 0.85 |
| 4069 | 3 | 4 | | | IV-2 | GTF3A | 0.94 | 4165 | 3 | 4 | | IV-2 | KDM4B | 0.91 |
| 4070 | 3 | 4 | | | IV-2 | GTSF1 | 0.92 | 4166 | 3 | 4 | | IV-2 | KDM5C | 0.92 |
| 4071 | 3 | 4 | | | IV-2 | GUSBP5 | 0.99 | 4167 | 3 | 4 | | IV-2 | KDM6A | 0.82 |
| 4072 | 3 | 4 | | | IV-2 | GZMM | 0.75 | 4168 | 3 | 4 | | IV-2 | KEL | 0.99 |
| 4073 | 3 | 4 | | | IV-2 | H19 | 0.99 | 4169 | 3 | 4 | | IV-2 | KIAA0040 | 0.88 |
| 4074 | 3 | 4 | | | IV-2 | H2AFB2 | 0.93 | 4170 | 3 | 4 | | IV-2 | KIAA0247 | 0.94 |
| 4075 | 3 | 4 | | | IV-2 | H2AFY2 | 0.97 | 4171 | 3 | 4 | | IV-2 | KIAA0319 | 0.99 |
| 4076 | 3 | 4 | | | IV-2 | HAL | 0.77 | 4172 | 3 | 4 | | IV-2 | KIAA0753 | 0.95 |
| 4077 | 3 | 4 | | | IV-2 | HAUS5 | 0.75 | 4173 | 3 | 4 | | IV-2 | KIAA0825 | 0.96 |
| 4078 | 3 | 4 | | | IV-2 | HAX1 | 0.85 | 4174 | 3 | 4 | | IV-2 | KIAA0913 | 0.95 |
| 4079 | 3 | 4 | | | IV-2 | HCAR2 | 0.77 | 4175 | 3 | 4 | | IV-2 | KIAA1109 | 0.98 |
| 4080 | 3 | 4 | | | IV-2 | HCG18 | 0.86 | 4176 | 3 | 4 | | IV-2 | KIAA1147 | 0.89 |
| 4081 | 3 | 4 | | | IV-2 | HCP5 | 0.75 | 4177 | 3 | 4 | | IV-2 | KIAA1407 | 0.81 |
| 4082 | 3 | 4 | | | IV-2 | HEMK1 | 0.79 | 4178 | 3 | 4 | | IV-2 | KIAA1468 | 0.90 |
| 4083 | 3 | 4 | | | IV-2 | HERC2P2 | 0.84 | 4179 | 3 | 4 | | IV-2 | KIAA1683 | 0.98 |
| 4084 | 3 | 4 | | | IV-2 | HERC2P3 | 0.94 | 4180 | 3 | 4 | | IV-2 | KIAA1731 | 0.99 |
| 4085 | 3 | 4 | | | IV-2 | HES6 | 0.89 | 4181 | 3 | 4 | | IV-2 | KIF21B | 0.93 |
| 4086 | 3 | 4 | | | IV-2 | HEXIM2 | 0.78 | 4182 | 3 | 4 | | IV-2 | KIF22 | 0.86 |
| 4087 | 3 | 4 | | | IV-2 | HILPDA | 0.95 | 4183 | 3 | 4 | | IV-2 | KIF3A | 0.96 |
| 4088 | 3 | 4 | | | IV-2 | HINFP | 0.96 | 4184 | 3 | 4 | | IV-2 | KIFC3 | 0.92 |
| 4089 | 3 | 4 | | | IV-2 | HIST1H1T | 0.94 | 4185 | 3 | 4 | | IV-2 | KIR2DL4 | 0.96 |
| 4090 | 3 | 4 | | | IV-2 | HIST1H2AJ | 0.99 | 4186 | 3 | 4 | | IV-2 | KLF7 | 0.95 |
| 4091 | 3 | 4 | | | IV-2 | HIST1H2BK | 0.99 | 4187 | 3 | 4 | | IV-2 | KLF8 | 0.99 |
| 4092 | 3 | 4 | | | IV-2 | HIST1H3E | 0.98 | 4188 | 3 | 4 | | IV-2 | KLHL17 | 0.90 |
| 4093 | 3 | 4 | | | IV-2 | HIST1H4I | 0.97 | 4189 | 3 | 4 | | IV-2 | KLHL21 | 0.93 |
| 4094 | 3 | 4 | | | IV-2 | HIST2H2BA | 0.92 | 4190 | 3 | 4 | | IV-2 | KLHL22 | 0.86 |
| 4095 | 3 | 4 | | | IV-2 | HIST2H2BE | 0.88 | 4191 | 3 | 4 | | IV-2 | KLHL3 | 0.92 |
| 4096 | 3 | 4 | | | IV-2 | HIVEP2 | 0.97 | 4192 | 3 | 4 | | IV-2 | KLRAP1 | 0.92 |
| 4097 | 3 | 4 | | | IV-2 | HLA-C | 0.81 | 4193 | 3 | 4 | | IV-2 | KLRD1 | 0.81 |
| 4098 | 3 | 4 | | | IV-2 | HLA-DPB2 | 1.00 | 4194 | 3 | 4 | | IV-2 | KRCC1 | 0.91 |
| 4099 | 3 | 4 | | | IV-2 | HLA-E | 0.79 | 4195 | 3 | 4 | | IV-2 | KRT10 | 0.94 |
| 4100 | 3 | 4 | | | IV-2 | HLA-F | 0.76 | 4196 | 3 | 4 | | IV-2 | KRT18 | 0.99 |
| 4101 | 3 | 4 | | | IV-2 | HLA-G | 0.99 | 4197 | 3 | 4 | | IV-2 | KRT72 | 0.93 |
| 4102 | 3 | 4 | | | IV-2 | HMGN4 | 0.95 | 4198 | 3 | 4 | | IV-2 | KY | 0.99 |
| 4103 | 3 | 4 | | | IV-2 | HMOX2 | 0.92 | 4199 | 3 | 4 | | IV-2 | LAMB2P1 | 0.97 |
| 4104 | 3 | 4 | | | IV-2 | HNRNPUL2-BSCL2 | 0.95 | 4200 | 3 | 4 | | IV-2 | LAMP3 | 0.96 |
| 4105 | 3 | 4 | | | IV-2 | HOOK1 | 0.93 | 4201 | 3 | 4 | | IV-2 | LARGE | 0.94 |
| 4106 | 3 | 4 | | | IV-2 | HOXA10 | 1.00 | 4202 | 3 | 4 | | IV-2 | LAT | 0.91 |
| 4107 | 3 | 4 | | | IV-2 | HPS4 | 0.98 | 4203 | 3 | 4 | | IV-2 | LBH | 0.77 |
| 4108 | 3 | 4 | | | IV-2 | HRASLS | 0.84 | 4204 | 3 | 4 | | IV-2 | LCK | 1.00 |
| 4109 | 3 | 4 | | | IV-2 | HRASLS5 | 0.94 | 4205 | 3 | 4 | | IV-2 | LCOR | 0.98 |
| 4110 | 3 | 4 | | | IV-2 | HS3ST3A1 | 0.87 | 4206 | 3 | 4 | | IV-2 | LDB1 | 0.92 |
| 4111 | 3 | 4 | | | IV-2 | HSD17B7P2 | 0.98 | 4207 | 3 | 4 | | IV-2 | LENG1 | 0.96 |
| 4112 | 3 | 4 | | | IV-2 | HSD17B8 | 0.90 | 4208 | 3 | 4 | | IV-2 | LEPREL4 | 0.94 |
| 4113 | 3 | 4 | | | IV-2 | HSF2 | 0.90 | 4209 | 3 | 4 | | IV-2 | LGALS9B | 0.83 |
| 4114 | 3 | 4 | | | IV-2 | HSPA1L | 0.92 | 4210 | 3 | 4 | | IV-2 | LGMN | 1.00 |
| 4115 | 3 | 4 | | | IV-2 | HSPE1-MOB4 | 0.82 | 4211 | 3 | 4 | | IV-2 | LIM2 | 0.99 |
| 4116 | 3 | 4 | | | IV-2 | HTATIP2 | 0.94 | 4212 | 3 | 4 | | IV-2 | LIMD2 | 0.86 |
| 4117 | 3 | 4 | | | IV-2 | ICA1L | 0.89 | 4213 | 3 | 4 | | IV-2 | LIME1 | 0.96 |
| 4118 | 3 | 4 | | | IV-2 | ICAM3 | 0.92 | 4214 | 3 | 4 | | IV-2 | LIMK2 | 0.84 |
| 4119 | 3 | 4 | | | IV-2 | ID2B | 0.75 | 4215 | 3 | 4 | | IV-2 | LIN37 | 0.79 |
| 4120 | 3 | 4 | | | IV-2 | IDS | 0.78 | 4216 | 3 | 4 | | IV-2 | LIN7B | 0.93 |
| 4121 | 3 | 4 | | | IV-2 | IFRD1 | 0.69 | 4217 | 3 | 4 | | IV-2 | LINC00092 | 0.97 |
| 4122 | 3 | 4 | | | IV-2 | IFT43 | 0.97 | 4218 | 3 | 4 | | IV-2 | LINC00115 | 0.94 |
| 4123 | 3 | 4 | | | IV-2 | IFT46 | 0.94 | 4219 | 3 | 4 | | IV-2 | LINC00239 | 1.00 |
| 4124 | 3 | 4 | | | IV-2 | IGSF6 | 0.95 | 4220 | 3 | 4 | | IV-2 | LINC00263 | 0.85 |

Fig. 41 - 23

| | | | | | | | |
|---|---|---|---|---|---|---|---|
| 4221 | 3 | 4 | | IV-2 | LINC00338 | 0.73 |
| 4222 | 3 | 4 | | IV-2 | LINC00467 | 0.97 |
| 4223 | 3 | 4 | | IV-2 | LINC00526 | 0.86 |
| 4224 | 3 | 4 | | IV-2 | LINGO2 | 0.98 |
| 4225 | 3 | 4 | | IV-2 | LIPC | 0.93 |
| 4226 | 3 | 4 | | IV-2 | LIPT1 | 0.97 |
| 4227 | 3 | 4 | | IV-2 | LOC100128881 | 0.91 |
| 4228 | 3 | 4 | | IV-2 | LOC100129196 | 0.68 |
| 4229 | 3 | 4 | | IV-2 | LOC100129534 | 0.95 |
| 4230 | 3 | 4 | | IV-2 | LOC100129917 | 0.92 |
| 4231 | 3 | 4 | | IV-2 | LOC100130581 | 0.70 |
| 4232 | 3 | 4 | | IV-2 | LOC100131096 | 0.91 |
| 4233 | 3 | 4 | | IV-2 | LOC100131564 | 0.83 |
| 4234 | 3 | 4 | | IV-2 | LOC100132352 | 0.86 |
| 4235 | 3 | 4 | | IV-2 | LOC100133991 | 0.75 |
| 4236 | 3 | 4 | | IV-2 | LOC100170939 | 0.97 |
| 4237 | 3 | 4 | | IV-2 | LOC100233209 | 0.74 |
| 4238 | 3 | 4 | | IV-2 | LOC100287616 | 0.69 |
| 4239 | 3 | 4 | | IV-2 | LOC100287722 | 0.88 |
| 4240 | 3 | 4 | | IV-2 | LOC100288123 | 0.94 |
| 4241 | 3 | 4 | | IV-2 | LOC100288842 | 0.98 |
| 4242 | 3 | 4 | | IV-2 | LOC100289511 | 0.95 |
| 4243 | 3 | 4 | | IV-2 | LOC100505648 | 0.75 |
| 4244 | 3 | 4 | | IV-2 | LOC100505761 | 0.75 |
| 4245 | 3 | 4 | | IV-2 | LOC100505854 | 0.70 |
| 4246 | 3 | 4 | | IV-2 | LOC100506033 | 0.79 |
| 4247 | 3 | 4 | | IV-2 | LOC100506233 | 0.90 |
| 4248 | 3 | 4 | | IV-2 | LOC100506321 | 0.84 |
| 4249 | 3 | 4 | | IV-2 | LOC100506469 | 0.97 |
| 4250 | 3 | 4 | | IV-2 | LOC100506548 | 0.89 |
| 4251 | 3 | 4 | | IV-2 | LOC100506649 | 0.84 |
| 4252 | 3 | 4 | | IV-2 | LOC100506686 | 0.96 |
| 4253 | 3 | 4 | | IV-2 | LOC100506714 | 0.74 |
| 4254 | 3 | 4 | | IV-2 | LOC100506776 | 0.84 |
| 4255 | 3 | 4 | | IV-2 | LOC100506779 | 0.91 |
| 4256 | 3 | 4 | | IV-2 | LOC100506930 | 1.00 |
| 4257 | 3 | 4 | | IV-2 | LOC100506963 | 0.93 |
| 4258 | 3 | 4 | | IV-2 | LOC100507218 | 0.99 |
| 4259 | 3 | 4 | | IV-2 | LOC100507246 | 0.92 |
| 4260 | 3 | 4 | | IV-2 | LOC100507373 | 0.82 |
| 4261 | 3 | 4 | | IV-2 | LOC100507392 | 0.90 |
| 4262 | 3 | 4 | | IV-2 | LOC100507424 | 0.82 |
| 4263 | 3 | 4 | | IV-2 | LOC100507463 | 0.87 |
| 4264 | 3 | 4 | | IV-2 | LOC100527964 | 0.97 |
| 4265 | 3 | 4 | | IV-2 | LOC100652768 | 0.87 |
| 4266 | 3 | 4 | | IV-2 | LOC149837 | 0.97 |
| 4267 | 3 | 4 | | IV-2 | LOC158257 | 0.95 |
| 4268 | 3 | 4 | | IV-2 | LOC200772 | 0.96 |
| 4269 | 3 | 4 | | IV-2 | LOC202181 | 0.80 |
| 4270 | 3 | 4 | | IV-2 | LOC202781 | 0.73 |
| 4271 | 3 | 4 | | IV-2 | LOC254100 | 0.70 |
| 4272 | 3 | 4 | | IV-2 | LOC255512 | 0.92 |
| 4273 | 3 | 4 | | IV-2 | LOC283089 | 0.91 |
| 4274 | 3 | 4 | | IV-2 | LOC283104 | 0.96 |
| 4275 | 3 | 4 | | IV-2 | LOC284023 | 0.85 |
| 4276 | 3 | 4 | | IV-2 | LOC284408 | 0.86 |
| 4277 | 3 | 4 | | IV-2 | LOC284440 | 0.99 |
| 4278 | 3 | 4 | | IV-2 | LOC284757 | 0.95 |
| 4279 | 3 | 4 | | IV-2 | LOC285965 | 0.96 |
| 4280 | 3 | 4 | | IV-2 | LOC340037 | 0.98 |
| 4281 | 3 | 4 | | IV-2 | LOC374443 | 0.95 |
| 4282 | 3 | 4 | | IV-2 | LOC386758 | 0.99 |
| 4283 | 3 | 4 | | IV-2 | LOC387723 | 0.71 |
| 4284 | 3 | 4 | | IV-2 | LOC390940 | 0.94 |
| 4285 | 3 | 4 | | IV-2 | LOC400685 | 0.94 |
| 4286 | 3 | 4 | | IV-2 | LOC400927 | 0.93 |
| 4287 | 3 | 4 | | IV-2 | LOC439949 | 0.78 |
| 4288 | 3 | 4 | | IV-2 | LOC440288 | 0.97 |
| 4289 | 3 | 4 | | IV-2 | LOC493754 | 0.91 |
| 4290 | 3 | 4 | | IV-2 | LOC494127 | 0.99 |
| 4291 | 3 | 4 | | IV-2 | LOC541471 | 0.85 |
| 4292 | 3 | 4 | | IV-2 | LOC641518 | 0.88 |
| 4293 | 3 | 4 | | IV-2 | LOC643723 | 1.00 |
| 4294 | 3 | 4 | | IV-2 | LOC644714 | 0.91 |
| 4295 | 3 | 4 | | IV-2 | LOC645513 | 0.87 |
| 4296 | 3 | 4 | | IV-2 | LOC646329 | 0.97 |
| 4297 | 3 | 4 | | IV-2 | LOC646719 | 0.97 |
| 4298 | 3 | 4 | | IV-2 | LOC727849 | 0.84 |
| 4299 | 3 | 4 | | IV-2 | LOC728323 | 1.00 |
| 4300 | 3 | 4 | | IV-2 | LOC728377 | 1.00 |
| 4301 | 3 | 4 | | IV-2 | LOC728613 | 0.94 |
| 4302 | 3 | 4 | | IV-2 | LOC728752 | 0.96 |
| 4303 | 3 | 4 | | IV-2 | LOC728875 | 0.90 |
| 4304 | 3 | 4 | | IV-2 | LOC729178 | 1.00 |
| 4305 | 3 | 4 | | IV-2 | LOC729234 | 0.91 |
| 4306 | 3 | 4 | | IV-2 | LOC729678 | 0.91 |
| 4307 | 3 | 4 | | IV-2 | LOC729862 | 0.77 |
| 4308 | 3 | 4 | | IV-2 | LPCAT4 | 0.80 |
| 4309 | 3 | 4 | | IV-2 | LPHN1 | 1.00 |
| 4310 | 3 | 4 | | IV-2 | LRP10 | 0.93 |
| 4311 | 3 | 4 | | IV-2 | LRRC16A | 0.97 |
| 4312 | 3 | 4 | | IV-2 | LRRC20 | 0.96 |
| 4313 | 3 | 4 | | IV-2 | LRRC27 | 0.98 |
| 4314 | 3 | 4 | | IV-2 | LRRC37B | 0.79 |
| 4315 | 3 | 4 | | IV-2 | LRRC6 | 0.96 |
| 4316 | 3 | 4 | | IV-2 | LRRC61 | 0.90 |
| 4317 | 3 | 4 | | IV-2 | LRRC70 | 0.93 |
| 4318 | 3 | 4 | | IV-2 | LRRK2 | 0.91 |
| 4319 | 3 | 4 | | IV-2 | LRRN2 | 0.96 |
| 4320 | 3 | 4 | | IV-2 | LRWD1 | 0.97 |
| 4321 | 3 | 4 | | IV-2 | LSM6 | 0.89 |
| 4322 | 3 | 4 | | IV-2 | LSR | 0.97 |
| 4323 | 3 | 4 | | IV-2 | LTB | 0.98 |
| 4324 | 3 | 4 | | IV-2 | LTBP2 | 0.97 |
| 4325 | 3 | 4 | | IV-2 | LTBP4 | 0.94 |
| 4326 | 3 | 4 | | IV-2 | LXN | 0.74 |
| 4327 | 3 | 4 | | IV-2 | LY9 | 0.87 |
| 4328 | 3 | 4 | | IV-2 | LYPD3 | 0.99 |
| 4329 | 3 | 4 | | IV-2 | LYPLAL1 | 0.99 |
| 4330 | 3 | 4 | | IV-2 | LYRM1 | 0.70 |
| 4331 | 3 | 4 | | IV-2 | LYVE1 | 0.99 |
| 4332 | 3 | 4 | | IV-2 | MADCAM1 | 0.92 |
| 4333 | 3 | 4 | | IV-2 | MAGOHB | 0.93 |
| 4334 | 3 | 4 | | IV-2 | MAN2A2 | 0.85 |
| 4335 | 3 | 4 | | IV-2 | MANBAL | 0.93 |
| 4336 | 3 | 4 | | IV-2 | MAP2K7 | 0.97 |
| 4337 | 3 | 4 | | IV-2 | MAP4K2 | 0.81 |
| 4338 | 3 | 4 | | IV-2 | MAPK13 | 0.83 |
| 4339 | 3 | 4 | | IV-2 | MAPK3 | 0.99 |
| 4340 | 3 | 4 | | IV-2 | MAPKAPK2 | 0.98 |
| 4341 | 3 | 4 | | IV-2 | 42432 | 0.99 |
| 4342 | 3 | 4 | | IV-2 | 42436 | 0.98 |
| 4343 | 3 | 4 | | IV-2 | 42438 | 0.87 |
| 4344 | 3 | 4 | | IV-2 | MARCKSL1 | 0.89 |
| 4345 | 3 | 4 | | IV-2 | MATL2963 | 0.93 |
| 4346 | 3 | 4 | | IV-2 | MAX | 0.87 |
| 4347 | 3 | 4 | | IV-2 | MBLAC2 | 0.94 |
| 4348 | 3 | 4 | | IV-2 | MBOAT7 | 0.91 |
| 4349 | 3 | 4 | | IV-2 | MBP | 0.97 |
| 4350 | 3 | 4 | | IV-2 | MC1R | 0.99 |
| 4351 | 3 | 4 | | IV-2 | MCART2 | 0.97 |
| 4352 | 3 | 4 | | IV-2 | MCM3AP-AS1 | 0.96 |
| 4353 | 3 | 4 | | IV-2 | MCOLN2 | 0.77 |
| 4354 | 3 | 4 | | IV-2 | MDM1 | 0.95 |
| 4355 | 3 | 4 | | IV-2 | MDM4 | 0.78 |
| 4356 | 3 | 4 | | IV-2 | MDS2 | 0.84 |
| 4357 | 3 | 4 | | IV-2 | MECP2 | 0.95 |
| 4358 | 3 | 4 | | IV-2 | MECR | 0.94 |
| 4359 | 3 | 4 | | IV-2 | MED11 | 1.00 |
| 4360 | 3 | 4 | | IV-2 | METTL12 | 0.99 |
| 4361 | 3 | 4 | | IV-2 | METTL22 | 0.90 |
| 4362 | 3 | 4 | | IV-2 | METTL4 | 0.96 |
| 4363 | 3 | 4 | | IV-2 | MFGE8 | 0.92 |
| 4364 | 3 | 4 | | IV-2 | MFSD2B | 0.97 |
| 4365 | 3 | 4 | | IV-2 | MFSD6L | 0.95 |
| 4366 | 3 | 4 | | IV-2 | MGC12916 | 0.92 |
| 4367 | 3 | 4 | | IV-2 | MGC39372 | 0.91 |
| 4368 | 3 | 4 | | IV-2 | MIB2 | 0.93 |
| 4369 | 3 | 4 | | IV-2 | MID1IP1 | 0.91 |
| 4370 | 3 | 4 | | IV-2 | MIDN | 0.90 |
| 4371 | 3 | 4 | | IV-2 | MIF | 0.70 |
| 4372 | 3 | 4 | | IV-2 | MIR155HG | 0.99 |
| 4373 | 3 | 4 | | IV-2 | MIRLET7BHG | 0.96 |
| 4374 | 3 | 4 | | IV-2 | MKNK2 | 0.87 |
| 4375 | 3 | 4 | | IV-2 | MKS1 | 0.98 |
| 4376 | 3 | 4 | | IV-2 | MLF2 | 0.82 |
| 4377 | 3 | 4 | | IV-2 | MLH3 | 0.82 |
| 4378 | 3 | 4 | | IV-2 | MLL4 | 0.94 |
| 4379 | 3 | 4 | | IV-2 | MLLT11 | 0.80 |
| 4380 | 3 | 4 | | IV-2 | MLLT6 | 0.83 |
| 4381 | 3 | 4 | | IV-2 | MME | 0.68 |
| 4382 | 3 | 4 | | IV-2 | MMP24 | 0.86 |
| 4383 | 3 | 4 | | IV-2 | MOB3A | 0.96 |
| 4384 | 3 | 4 | | IV-2 | MOB3C | 0.90 |
| 4385 | 3 | 4 | | IV-2 | MORC4 | 0.94 |
| 4386 | 3 | 4 | | IV-2 | MORN3 | 0.91 |
| 4387 | 3 | 4 | | IV-2 | MPPE1 | 0.73 |
| 4388 | 3 | 4 | | IV-2 | MPZL3 | 0.69 |
| 4389 | 3 | 4 | | IV-2 | MREG | 0.79 |
| 4390 | 3 | 4 | | IV-2 | MRFAP1L1 | 0.89 |
| 4391 | 3 | 4 | | IV-2 | MRPL1 | 0.76 |
| 4392 | 3 | 4 | | IV-2 | MRPL49 | 0.82 |
| 4393 | 3 | 4 | | IV-2 | MSI2 | 0.99 |
| 4394 | 3 | 4 | | IV-2 | MSRB3 | 0.81 |
| 4395 | 3 | 4 | | IV-2 | MSTO1 | 0.96 |
| 4396 | 3 | 4 | | IV-2 | MSTO2P | 0.85 |
| 4397 | 3 | 4 | | IV-2 | MTERFD2 | 0.91 |
| 4398 | 3 | 4 | | IV-2 | MTERFD3 | 0.80 |
| 4399 | 3 | 4 | | IV-2 | MTHFS | 0.94 |
| 4400 | 3 | 4 | | IV-2 | MTRF1 | 0.93 |
| 4401 | 3 | 4 | | IV-2 | MTRNR2L1 | 0.98 |
| 4402 | 3 | 4 | | IV-2 | MTUS1 | 0.96 |
| 4403 | 3 | 4 | | IV-2 | MUSTN1 | 0.85 |
| 4404 | 3 | 4 | | IV-2 | MYCT1 | 0.91 |
| 4405 | 3 | 4 | | IV-2 | MYEOV | 0.81 |
| 4406 | 3 | 4 | | IV-2 | MYLIP | 0.94 |
| 4407 | 3 | 4 | | IV-2 | MYO19 | 0.78 |
| 4408 | 3 | 4 | | IV-2 | MYO1D | 0.93 |
| 4409 | 3 | 4 | | IV-2 | MYSM1 | 0.82 |
| 4410 | 3 | 4 | | IV-2 | MZF1 | 0.95 |
| 4411 | 3 | 4 | | IV-2 | N4BP1 | 0.89 |
| 4412 | 3 | 4 | | IV-2 | N4BP2L2 | 0.86 |

Fig. 41 - 24

| | | | | | | | | | | | | | |
|---|---|---|---|---|---|---|---|---|---|---|---|---|---|
| 4413 | 3 | 4 | | | IV-2 | N6AMT1 | 0.96 | 4509 | 3 | 4 | | IV-2 | PDE1B | 0.96 |
| 4414 | 3 | 4 | | | IV-2 | NAA10 | 0.92 | 4510 | 3 | 4 | | IV-2 | PDE3B | 0.92 |
| 4415 | 3 | 4 | | | IV-2 | NAA40 | 0.80 | 4511 | 3 | 4 | | IV-2 | PDE4B | 0.77 |
| 4416 | 3 | 4 | | | IV-2 | NAE1 | 0.89 | 4512 | 3 | 4 | | IV-2 | PDE7A | 0.76 |
| 4417 | 3 | 4 | | | IV-2 | NAMPT | 0.91 | 4513 | 3 | 4 | | IV-2 | PDHA2 | 0.97 |
| 4418 | 3 | 4 | | | IV-2 | NAP1L3 | 0.91 | 4514 | 3 | 4 | | IV-2 | PDK1 | 0.80 |
| 4419 | 3 | 4 | | | IV-2 | NBPF24 | 0.98 | 4515 | 3 | 4 | | IV-2 | PDK3 | 0.94 |
| 4420 | 3 | 4 | | | IV-2 | NCALD | 0.68 | 4516 | 3 | 4 | | IV-2 | PDXDC2P | 0.99 |
| 4421 | 3 | 4 | | | IV-2 | NCAPH2 | 0.85 | 4517 | 3 | 4 | | IV-2 | PDZD8 | 0.90 |
| 4422 | 3 | 4 | | | IV-2 | NCF4 | 0.77 | 4518 | 3 | 4 | | IV-2 | PERP | 0.97 |
| 4423 | 3 | 4 | | | IV-2 | NCK2 | 0.67 | 4519 | 3 | 4 | | IV-2 | PEX11A | 0.99 |
| 4424 | 3 | 4 | | | IV-2 | NCR1 | 0.72 | 4520 | 3 | 4 | | IV-2 | PEX2 | 0.93 |
| 4425 | 3 | 4 | | | IV-2 | NDE1 | 0.73 | 4521 | 3 | 4 | | IV-2 | PGRMC1 | 0.89 |
| 4426 | 3 | 4 | | | IV-2 | NDEL1 | 0.89 | 4522 | 3 | 4 | | IV-2 | PHF12 | 0.85 |
| 4427 | 3 | 4 | | | IV-2 | NDN | 0.97 | 4523 | 3 | 4 | | IV-2 | PHF5A | 0.83 |
| 4428 | 3 | 4 | | | IV-2 | NDUFA1 | 0.76 | 4524 | 3 | 4 | | IV-2 | PHLDA1 | 0.91 |
| 4429 | 3 | 4 | | | IV-2 | NDUFAF2 | 0.89 | 4525 | 3 | 4 | | IV-2 | PHLDB2 | 0.88 |
| 4430 | 3 | 4 | | | IV-2 | NDUFB4 | 0.95 | 4526 | 3 | 4 | | IV-2 | PHOSPHO2 | 0.99 |
| 4431 | 3 | 4 | | | IV-2 | NDUFB6 | 0.96 | 4527 | 3 | 4 | | IV-2 | PI4KAP2 | 0.91 |
| 4432 | 3 | 4 | | | IV-2 | NEDD9 | 0.79 | 4528 | 3 | 4 | | IV-2 | PIAS1 | 0.95 |
| 4433 | 3 | 4 | | | IV-2 | NEIL1 | 0.90 | 4529 | 3 | 4 | | IV-2 | PICK1 | 0.89 |
| 4434 | 3 | 4 | | | IV-2 | NFAT5 | 0.81 | 4530 | 3 | 4 | | IV-2 | PIDD | 0.91 |
| 4435 | 3 | 4 | | | IV-2 | NHSL2 | 0.99 | 4531 | 3 | 4 | | IV-2 | PIGB | 0.78 |
| 4436 | 3 | 4 | | | IV-2 | NIPA1 | 1.00 | 4532 | 3 | 4 | | IV-2 | PIGF | 0.79 |
| 4437 | 3 | 4 | | | IV-2 | NIT2 | 0.99 | 4533 | 3 | 4 | | IV-2 | PIGX | 0.98 |
| 4438 | 3 | 4 | | | IV-2 | NLRC3 | 0.85 | 4534 | 3 | 4 | | IV-2 | PIK3IP1 | 0.84 |
| 4439 | 3 | 4 | | | IV-2 | NLRC5 | 0.81 | 4535 | 3 | 4 | | IV-2 | PIK3R3 | 0.93 |
| 4440 | 3 | 4 | | | IV-2 | NMB | 0.98 | 4536 | 3 | 4 | | IV-2 | PILRA | 0.97 |
| 4441 | 3 | 4 | | | IV-2 | NNAT | 0.96 | 4537 | 3 | 4 | | IV-2 | PION | 0.76 |
| 4442 | 3 | 4 | | | IV-2 | NOSIP | 0.81 | 4538 | 3 | 4 | | IV-2 | PIP5K1B | 0.87 |
| 4443 | 3 | 4 | | | IV-2 | NPBWR1 | 0.99 | 4539 | 3 | 4 | | IV-2 | PISD | 0.94 |
| 4444 | 3 | 4 | | | IV-2 | NPFF | 0.93 | 4540 | 3 | 4 | | IV-2 | PITPNA | 1.00 |
| 4445 | 3 | 4 | | | IV-2 | NPHP3 | 0.92 | 4541 | 3 | 4 | | IV-2 | PKD1P1 | 0.78 |
| 4446 | 3 | 4 | | | IV-2 | NPRL2 | 0.77 | 4542 | 3 | 4 | | IV-2 | PKN2 | 0.90 |
| 4447 | 3 | 4 | | | IV-2 | NR4A2 | 0.97 | 4543 | 3 | 4 | | IV-2 | PLA2G12A | 0.86 |
| 4448 | 3 | 4 | | | IV-2 | NR6A1 | 0.95 | 4544 | 3 | 4 | | IV-2 | PLCD1 | 0.81 |
| 4449 | 3 | 4 | | | IV-2 | NRBF2 | 0.80 | 4545 | 3 | 4 | | IV-2 | PLCL1 | 0.78 |
| 4450 | 3 | 4 | | | IV-2 | NR8P2 | 0.86 | 4546 | 3 | 4 | | IV-2 | PLEKHA1 | 0.93 |
| 4451 | 3 | 4 | | | IV-2 | NRL | 0.99 | 4547 | 3 | 4 | | IV-2 | PLEKHF1 | 0.73 |
| 4452 | 3 | 4 | | | IV-2 | NRP1 | 0.95 | 4548 | 3 | 4 | | IV-2 | PLK1S1 | 0.92 |
| 4453 | 3 | 4 | | | IV-2 | NRSN2 | 0.97 | 4549 | 3 | 4 | | IV-2 | PLK3 | 0.81 |
| 4454 | 3 | 4 | | | IV-2 | NSUN6 | 0.72 | 4550 | 3 | 4 | | IV-2 | PLXDC1 | 0.97 |
| 4455 | 3 | 4 | | | IV-2 | NT5C | 0.97 | 4551 | 3 | 4 | | IV-2 | PLXNA3 | 0.85 |
| 4456 | 3 | 4 | | | IV-2 | NT5C3 | 0.95 | 4552 | 3 | 4 | | IV-2 | PMAIP1 | 0.70 |
| 4457 | 3 | 4 | | | IV-2 | NTAN1 | 0.99 | 4553 | 3 | 4 | | IV-2 | PMS2CL | 0.96 |
| 4458 | 3 | 4 | | | IV-2 | NUAK2 | 0.83 | 4554 | 3 | 4 | | IV-2 | PMS2P3 | 0.77 |
| 4459 | 3 | 4 | | | IV-2 | NUDT14 | 0.75 | 4555 | 3 | 4 | | IV-2 | PNISR | 0.73 |
| 4460 | 3 | 4 | | | IV-2 | NUDT15 | 0.95 | 4556 | 3 | 4 | | IV-2 | PNKP | 0.80 |
| 4461 | 3 | 4 | | | IV-2 | NUDT17 | 0.90 | 4557 | 3 | 4 | | IV-2 | PNRC1 | 0.95 |
| 4462 | 3 | 4 | | | IV-2 | NUDT5 | 0.78 | 4558 | 3 | 4 | | IV-2 | POC5 | 0.86 |
| 4463 | 3 | 4 | | | IV-2 | NUP214 | 0.95 | 4559 | 3 | 4 | | IV-2 | POLB | 0.70 |
| 4464 | 3 | 4 | | | IV-2 | NUTF2 | 0.92 | 4560 | 3 | 4 | | IV-2 | POLM | 0.75 |
| 4465 | 3 | 4 | | | IV-2 | NXF1 | 0.98 | 4561 | 3 | 4 | | IV-2 | POLR2J2 | 0.97 |
| 4466 | 3 | 4 | | | IV-2 | NXPH4 | 1.00 | 4562 | 3 | 4 | | IV-2 | POLR2J4 | 0.94 |
| 4467 | 3 | 4 | | | IV-2 | NXT1 | 0.94 | 4563 | 3 | 4 | | IV-2 | POLR2K | 0.80 |
| 4468 | 3 | 4 | | | IV-2 | OAZ3 | 0.91 | 4564 | 3 | 4 | | IV-2 | POMGNT1 | 0.98 |
| 4469 | 3 | 4 | | | IV-2 | OBFC1 | 0.81 | 4565 | 3 | 4 | | IV-2 | POPDC2 | 0.97 |
| 4470 | 3 | 4 | | | IV-2 | OBFC2A | 0.79 | 4566 | 3 | 4 | | IV-2 | POU6F1 | 0.79 |
| 4471 | 3 | 4 | | | IV-2 | OBSCN | 0.92 | 4567 | 3 | 4 | | IV-2 | PPCDC | 0.72 |
| 4472 | 3 | 4 | | | IV-2 | OCIAD2 | 0.72 | 4568 | 3 | 4 | | IV-2 | PPIEL | 0.95 |
| 4473 | 3 | 4 | | | IV-2 | OCM | 0.93 | 4569 | 3 | 4 | | IV-2 | PPIF | 0.93 |
| 4474 | 3 | 4 | | | IV-2 | OFD1 | 0.76 | 4570 | 3 | 4 | | IV-2 | PPIP5K1 | 0.97 |
| 4475 | 3 | 4 | | | IV-2 | OGFRL1 | 0.94 | 4571 | 3 | 4 | | IV-2 | PPP1R12C | 0.86 |
| 4476 | 3 | 4 | | | IV-2 | OGT | 0.69 | 4572 | 3 | 4 | | IV-2 | PPP1R16B | 0.89 |
| 4477 | 3 | 4 | | | IV-2 | OLFM2 | 0.94 | 4573 | 3 | 4 | | IV-2 | PPP1R2P3 | 0.92 |
| 4478 | 3 | 4 | | | IV-2 | ORAI1 | 0.98 | 4574 | 3 | 4 | | IV-2 | PPP3CC | 0.80 |
| 4479 | 3 | 4 | | | IV-2 | ORAI2 | 0.98 | 4575 | 3 | 4 | | IV-2 | PPP4R1L | 0.81 |
| 4480 | 3 | 4 | | | IV-2 | ORAOV1 | 0.90 | 4576 | 3 | 4 | | IV-2 | PPP6R2 | 0.85 |
| 4481 | 3 | 4 | | | IV-2 | OSGIN2 | 0.89 | 4577 | 3 | 4 | | IV-2 | PRAF2 | 0.81 |
| 4482 | 3 | 4 | | | IV-2 | OTUD3 | 0.95 | 4578 | 3 | 4 | | IV-2 | PRDM1 | 0.91 |
| 4483 | 3 | 4 | | | IV-2 | OTUD5 | 0.88 | 4579 | 3 | 4 | | IV-2 | PRDM5 | 0.92 |
| 4484 | 3 | 4 | | | IV-2 | P2RY13 | 0.95 | 4580 | 3 | 4 | | IV-2 | PRDX2 | 0.90 |
| 4485 | 3 | 4 | | | IV-2 | PA8PC1L | 0.94 | 4581 | 3 | 4 | | IV-2 | PREX1 | 0.94 |
| 4486 | 3 | 4 | | | IV-2 | PACS1 | 0.69 | 4582 | 3 | 4 | | IV-2 | PRKAB2 | 0.96 |
| 4487 | 3 | 4 | | | IV-2 | PACSIN1 | 0.91 | 4583 | 3 | 4 | | IV-2 | PRKD2 | 0.92 |
| 4488 | 3 | 4 | | | IV-2 | PAN2 | 0.98 | 4584 | 3 | 4 | | IV-2 | PRKRIP1 | 0.82 |
| 4489 | 3 | 4 | | | IV-2 | PAN3-AS1 | 0.73 | 4585 | 3 | 4 | | IV-2 | PRMT1 | 0.98 |
| 4490 | 3 | 4 | | | IV-2 | PAQR6 | 0.99 | 4586 | 3 | 4 | | IV-2 | PRMT2 | 0.97 |
| 4491 | 3 | 4 | | | IV-2 | PAR-SN | 0.74 | 4587 | 3 | 4 | | IV-2 | PROCA1 | 0.67 |
| 4492 | 3 | 4 | | | IV-2 | PARD6A | 0.80 | 4588 | 3 | 4 | | IV-2 | PROCR | 0.87 |
| 4493 | 3 | 4 | | | IV-2 | PARM1 | 0.89 | 4589 | 3 | 4 | | IV-2 | PRORSD1P | 0.93 |
| 4494 | 3 | 4 | | | IV-2 | PARP16 | 0.97 | 4590 | 3 | 4 | | IV-2 | PRR14 | 0.75 |
| 4495 | 3 | 4 | | | IV-2 | PARP2 | 0.99 | 4591 | 3 | 4 | | IV-2 | PRR3 | 0.93 |
| 4496 | 3 | 4 | | | IV-2 | PARP6 | 0.74 | 4592 | 3 | 4 | | IV-2 | PRRT3 | 0.93 |
| 4497 | 3 | 4 | | | IV-2 | PARP8 | 0.89 | 4593 | 3 | 4 | | IV-2 | PRSS23 | 0.74 |
| 4498 | 3 | 4 | | | IV-2 | PBX2 | 0.70 | 4594 | 3 | 4 | | IV-2 | PRSS53 | 0.98 |
| 4499 | 3 | 4 | | | IV-2 | PBX4 | 0.98 | 4595 | 3 | 4 | | IV-2 | PSMB9 | 0.91 |
| 4500 | 3 | 4 | | | IV-2 | PBXIP1 | 0.81 | 4596 | 3 | 4 | | IV-2 | PSMG4 | 0.96 |
| 4501 | 3 | 4 | | | IV-2 | PCBP4 | 0.74 | 4597 | 3 | 4 | | IV-2 | PTBP2 | 0.76 |
| 4502 | 3 | 4 | | | IV-2 | PCDH1 | 0.95 | 4598 | 3 | 4 | | IV-2 | PTCH1 | 0.82 |
| 4503 | 3 | 4 | | | IV-2 | PCDH9 | 0.98 | 4599 | 3 | 4 | | IV-2 | PTOV1 | 0.73 |
| 4504 | 3 | 4 | | | IV-2 | PCMTD1 | 0.77 | 4600 | 3 | 4 | | IV-2 | PTPN4 | 0.89 |
| 4505 | 3 | 4 | | | IV-2 | PCNXL2 | 0.91 | 4601 | 3 | 4 | | IV-2 | PTPRCAP | 0.82 |
| 4506 | 3 | 4 | | | IV-2 | PCP2 | 0.93 | 4602 | 3 | 4 | | IV-2 | PTRHD1 | 0.97 |
| 4507 | 3 | 4 | | | IV-2 | PCYT1B | 0.98 | 4603 | 3 | 4 | | IV-2 | PTS | 0.94 |
| 4508 | 3 | 4 | | | IV-2 | PDCD4 | 0.99 | 4604 | 3 | 4 | | IV-2 | PXDC1 | 0.84 |

Fig. 41 - 25

| # | A | B | C | D | E | Type | Gene | Value |
|---|---|---|---|---|---|---|---|---|
| 4605 | 3 | 4 | | | | IV-2 | PYCR1 | 0.74 |
| 4606 | 3 | 4 | | | | IV-2 | PYGM | 0.92 |
| 4607 | 3 | 4 | | | | IV-2 | PYROXD2 | 0.95 |
| 4608 | 3 | 4 | | | | IV-2 | QSOX2 | 0.97 |
| 4609 | 3 | 4 | | | | IV-2 | R3HDM2 | 0.97 |
| 4610 | 3 | 4 | | | | IV-2 | RAB11FIP3 | 0.78 |
| 4611 | 3 | 4 | | | | IV-2 | RAB11FIP4 | 0.90 |
| 4612 | 3 | 4 | | | | IV-2 | RAB24 | 0.87 |
| 4613 | 3 | 4 | | | | IV-2 | RAB33A | 0.97 |
| 4614 | 3 | 4 | | | | IV-2 | RAB40B | 0.96 |
| 4615 | 3 | 4 | | | | IV-2 | RAB5B | 0.85 |
| 4616 | 3 | 4 | | | | IV-2 | RAB5C | 0.99 |
| 4617 | 3 | 4 | | | | IV-2 | RAB6B | 0.85 |
| 4618 | 3 | 4 | | | | IV-2 | RABGAP1L | 0.73 |
| 4619 | 3 | 4 | | | | IV-2 | RABL2A | 0.87 |
| 4620 | 3 | 4 | | | | IV-2 | RAD52 | 0.96 |
| 4621 | 3 | 4 | | | | IV-2 | RAD9A | 0.70 |
| 4622 | 3 | 4 | | | | IV-2 | RAF1 | 0.98 |
| 4623 | 3 | 4 | | | | IV-2 | RALGDS | 0.94 |
| 4624 | 3 | 4 | | | | IV-2 | RALGPS1 | 0.94 |
| 4625 | 3 | 4 | | | | IV-2 | RAPGEF2 | 0.86 |
| 4626 | 3 | 4 | | | | IV-2 | RARA | 0.85 |
| 4627 | 3 | 4 | | | | IV-2 | RARS2 | 0.76 |
| 4628 | 3 | 4 | | | | IV-2 | RASA2 | 0.92 |
| 4629 | 3 | 4 | | | | IV-2 | RASGRP2 | 0.87 |
| 4630 | 3 | 4 | | | | IV-2 | RASSF1 | 0.85 |
| 4631 | 3 | 4 | | | | IV-2 | RASSF2 | 0.85 |
| 4632 | 3 | 4 | | | | IV-2 | RASSF3 | 0.92 |
| 4633 | 3 | 4 | | | | IV-2 | RBL2 | 0.96 |
| 4634 | 3 | 4 | | | | IV-2 | RBM48 | 0.87 |
| 4635 | 3 | 4 | | | | IV-2 | RBM5 | 0.95 |
| 4636 | 3 | 4 | | | | IV-2 | RCL1 | 0.93 |
| 4637 | 3 | 4 | | | | IV-2 | RCN2 | 0.82 |
| 4638 | 3 | 4 | | | | IV-2 | RCOR3 | 0.97 |
| 4639 | 3 | 4 | | | | IV-2 | RDH5 | 0.92 |
| 4640 | 3 | 4 | | | | IV-2 | REC8 | 0.90 |
| 4641 | 3 | 4 | | | | IV-2 | RERE | 0.85 |
| 4642 | 3 | 4 | | | | IV-2 | RFFL | 0.75 |
| 4643 | 3 | 4 | | | | IV-2 | RFPL2 | 0.99 |
| 4644 | 3 | 4 | | | | IV-2 | RFX3 | 0.97 |
| 4645 | 3 | 4 | | | | IV-2 | RGPD1 | 0.96 |
| 4646 | 3 | 4 | | | | IV-2 | RGPD8 | 0.93 |
| 4647 | 3 | 4 | | | | IV-2 | RGS14 | 0.87 |
| 4648 | 3 | 4 | | | | IV-2 | RGS2 | 0.89 |
| 4649 | 3 | 4 | | | | IV-2 | RHD | 1.00 |
| 4650 | 3 | 4 | | | | IV-2 | RHEBL1 | 1.00 |
| 4651 | 3 | 4 | | | | IV-2 | RHOT2 | 0.90 |
| 4652 | 3 | 4 | | | | IV-2 | RICTOR | 0.73 |
| 4653 | 3 | 4 | | | | IV-2 | RIMS3 | 0.96 |
| 4654 | 3 | 4 | | | | IV-2 | RLN2 | 0.95 |
| 4655 | 3 | 4 | | | | IV-2 | RLTPR | 0.83 |
| 4656 | 3 | 4 | | | | IV-2 | RNASEH2C | 0.96 |
| 4657 | 3 | 4 | | | | IV-2 | RNASEK-C17ORF49 | 0.92 |
| 4658 | 3 | 4 | | | | IV-2 | RNF103-CHMP3 | 0.97 |
| 4659 | 3 | 4 | | | | IV-2 | RNF11 | 0.93 |
| 4660 | 3 | 4 | | | | IV-2 | RNF166 | 0.85 |
| 4661 | 3 | 4 | | | | IV-2 | RNF167 | 0.91 |
| 4662 | 3 | 4 | | | | IV-2 | RNF215 | 1.00 |
| 4663 | 3 | 4 | | | | IV-2 | RPA3 | 0.89 |
| 4664 | 3 | 4 | | | | IV-2 | RPH3AL | 0.88 |
| 4665 | 3 | 4 | | | | IV-2 | RPL11 | 0.95 |
| 4666 | 3 | 4 | | | | IV-2 | RPL13 | 0.85 |
| 4667 | 3 | 4 | | | | IV-2 | RPL13AP20 | 0.71 |
| 4668 | 3 | 4 | | | | IV-2 | RPL17 | 0.79 |
| 4669 | 3 | 4 | | | | IV-2 | RPL18A | 0.72 |
| 4670 | 3 | 4 | | | | IV-2 | RPL21P28 | 0.69 |
| 4671 | 3 | 4 | | | | IV-2 | RPL22L1 | 0.84 |
| 4672 | 3 | 4 | | | | IV-2 | RPL24 | 0.84 |
| 4673 | 3 | 4 | | | | IV-2 | RPL27 | 0.81 |
| 4674 | 3 | 4 | | | | IV-2 | RPL27A | 0.73 |
| 4675 | 3 | 4 | | | | IV-2 | RPL29 | 0.87 |
| 4676 | 3 | 4 | | | | IV-2 | RPL3 | 0.91 |
| 4677 | 3 | 4 | | | | IV-2 | RPL30 | 0.96 |
| 4678 | 3 | 4 | | | | IV-2 | RPL32P3 | 0.69 |
| 4679 | 3 | 4 | | | | IV-2 | RPL35 | 0.87 |
| 4680 | 3 | 4 | | | | IV-2 | RPL35A | 0.97 |
| 4681 | 3 | 4 | | | | IV-2 | RPL36 | 0.99 |
| 4682 | 3 | 4 | | | | IV-2 | RPL36A | 0.91 |
| 4683 | 3 | 4 | | | | IV-2 | RPL36A-HNRNPH2 | 0.93 |
| 4684 | 3 | 4 | | | | IV-2 | RPL36AL | 0.84 |
| 4685 | 3 | 4 | | | | IV-2 | RPL37A | 0.84 |
| 4686 | 3 | 4 | | | | IV-2 | RPL38 | 0.81 |
| 4687 | 3 | 4 | | | | IV-2 | RPL6 | 0.78 |
| 4688 | 3 | 4 | | | | IV-2 | RPLP0 | 0.91 |
| 4689 | 3 | 4 | | | | IV-2 | RPLP1 | 0.76 |
| 4690 | 3 | 4 | | | | IV-2 | RPS11 | 0.93 |
| 4691 | 3 | 4 | | | | IV-2 | RPS12 | 0.72 |
| 4692 | 3 | 4 | | | | IV-2 | RPS15 | 0.96 |
| 4693 | 3 | 4 | | | | IV-2 | RPS15A | 0.93 |
| 4694 | 3 | 4 | | | | IV-2 | RPS17 | 0.68 |
| 4695 | 3 | 4 | | | | IV-2 | RPS20 | 0.76 |
| 4696 | 3 | 4 | | | | IV-2 | RPS25 | 0.72 |
| 4697 | 3 | 4 | | | | IV-2 | RPS27L | 0.94 |
| 4698 | 3 | 4 | | | | IV-2 | RPS3 | 0.67 |
| 4699 | 3 | 4 | | | | IV-2 | RPS5 | 0.94 |
| 4700 | 3 | 4 | | | | IV-2 | RPS6 | 0.68 |
| 4701 | 3 | 4 | | | | IV-2 | RPS6KA5 | 0.87 |
| 4702 | 3 | 4 | | | | IV-2 | RPS6KB2 | 0.82 |
| 4703 | 3 | 4 | | | | IV-2 | RPSA | 0.82 |
| 4704 | 3 | 4 | | | | IV-2 | RPSAP58 | 0.95 |
| 4705 | 3 | 4 | | | | IV-2 | RPSAP9 | 0.82 |
| 4706 | 3 | 4 | | | | IV-2 | RRAS2 | 0.81 |
| 4707 | 3 | 4 | | | | IV-2 | RRN3P1 | 0.94 |
| 4708 | 3 | 4 | | | | IV-2 | RRP9 | 0.90 |
| 4709 | 3 | 4 | | | | IV-2 | RUNX2 | 0.76 |
| 4710 | 3 | 4 | | | | IV-2 | RYK | 0.99 |
| 4711 | 3 | 4 | | | | IV-2 | S100A11 | 0.98 |
| 4712 | 3 | 4 | | | | IV-2 | S1PR5 | 0.85 |
| 4713 | 3 | 4 | | | | IV-2 | SALL2 | 0.92 |
| 4714 | 3 | 4 | | | | IV-2 | SAMD10 | 0.74 |
| 4715 | 3 | 4 | | | | IV-2 | SAMD3 | 0.83 |
| 4716 | 3 | 4 | | | | IV-2 | SAMD4B | 0.91 |
| 4717 | 3 | 4 | | | | IV-2 | SARM1 | 0.97 |
| 4718 | 3 | 4 | | | | IV-2 | SASS6 | 0.92 |
| 4719 | 3 | 4 | | | | IV-2 | SBDSP1 | 0.81 |
| 4720 | 3 | 4 | | | | IV-2 | SCAND2 | 0.77 |
| 4721 | 3 | 4 | | | | IV-2 | SCAP | 0.92 |
| 4722 | 3 | 4 | | | | IV-2 | SCARF1 | 0.68 |
| 4723 | 3 | 4 | | | | IV-2 | SCG8IC1 | 0.98 |
| 4724 | 3 | 4 | | | | IV-2 | SCML1 | 0.74 |
| 4725 | 3 | 4 | | | | IV-2 | SCML4 | 0.97 |
| 4726 | 3 | 4 | | | | IV-2 | SCNM1 | 0.93 |
| 4727 | 3 | 4 | | | | IV-2 | SCRN2 | 0.94 |
| 4728 | 3 | 4 | | | | IV-2 | SCT | 0.96 |
| 4729 | 3 | 4 | | | | IV-2 | SCYL3 | 0.95 |
| 4730 | 3 | 4 | | | | IV-2 | SDCCAG3 | 0.92 |
| 4731 | 3 | 4 | | | | IV-2 | SDR42E1 | 0.95 |
| 4732 | 3 | 4 | | | | IV-2 | SEC14L1 | 0.72 |
| 4733 | 3 | 4 | | | | IV-2 | SEC14L5 | 0.87 |
| 4734 | 3 | 4 | | | | IV-2 | SEC31B | 0.92 |
| 4735 | 3 | 4 | | | | IV-2 | SECISBP2 | 0.86 |
| 4736 | 3 | 4 | | | | IV-2 | SELM | 0.85 |
| 4737 | 3 | 4 | | | | IV-2 | SEMA4A | 0.96 |
| 4738 | 3 | 4 | | | | IV-2 | SEMA4C | 0.88 |
| 4739 | 3 | 4 | | | | IV-2 | SEMA4D | 0.97 |
| 4740 | 3 | 4 | | | | IV-2 | SEMA4F | 1.00 |
| 4741 | 3 | 4 | | | | IV-2 | SEMG1 | 0.97 |
| 4742 | 3 | 4 | | | | IV-2 | SENP3 | 0.87 |
| 4743 | 3 | 4 | | | | IV-2 | 42614 | 1.00 |
| 4744 | 3 | 4 | | | | IV-2 | 42619 | 0.81 |
| 4745 | 3 | 4 | | | | IV-2 | SERF1B | 0.69 |
| 4746 | 3 | 4 | | | | IV-2 | SERPINE2 | 0.82 |
| 4747 | 3 | 4 | | | | IV-2 | SETD1B | 0.94 |
| 4748 | 3 | 4 | | | | IV-2 | SETD4 | 0.82 |
| 4749 | 3 | 4 | | | | IV-2 | SETD9 | 0.99 |
| 4750 | 3 | 4 | | | | IV-2 | SGCB | 0.75 |
| 4751 | 3 | 4 | | | | IV-2 | SGK1 | 0.81 |
| 4752 | 3 | 4 | | | | IV-2 | SGK494 | 0.96 |
| 4753 | 3 | 4 | | | | IV-2 | SGPP2 | 0.92 |
| 4754 | 3 | 4 | | | | IV-2 | SH2B1 | 0.75 |
| 4755 | 3 | 4 | | | | IV-2 | SH2D3A | 0.81 |
| 4756 | 3 | 4 | | | | IV-2 | SH3D21 | 0.96 |
| 4757 | 3 | 4 | | | | IV-2 | SH3GL1P2 | 0.92 |
| 4758 | 3 | 4 | | | | IV-2 | SIAH1 | 0.94 |
| 4759 | 3 | 4 | | | | IV-2 | SIGIRR | 0.93 |
| 4760 | 3 | 4 | | | | IV-2 | SIRT3 | 0.93 |
| 4761 | 3 | 4 | | | | IV-2 | SIT1 | 0.77 |
| 4762 | 3 | 4 | | | | IV-2 | SKAP1 | 0.73 |
| 4763 | 3 | 4 | | | | IV-2 | SKP2 | 1.00 |
| 4764 | 3 | 4 | | | | IV-2 | SLAMF6 | 0.83 |
| 4765 | 3 | 4 | | | | IV-2 | SLAMF7 | 0.84 |
| 4766 | 3 | 4 | | | | IV-2 | SLC16A5 | 0.79 |
| 4767 | 3 | 4 | | | | IV-2 | SLC17A9 | 0.77 |
| 4768 | 3 | 4 | | | | IV-2 | SLC19A1 | 0.91 |
| 4769 | 3 | 4 | | | | IV-2 | SLC19A2 | 0.82 |
| 4770 | 3 | 4 | | | | IV-2 | SLC22A17 | 0.95 |
| 4771 | 3 | 4 | | | | IV-2 | SLC25A26 | 0.94 |
| 4772 | 3 | 4 | | | | IV-2 | SLC25A35 | 0.69 |
| 4773 | 3 | 4 | | | | IV-2 | SLC25A38 | 0.91 |
| 4774 | 3 | 4 | | | | IV-2 | SLC25A4 | 0.92 |
| 4775 | 3 | 4 | | | | IV-2 | SLC25A42 | 0.79 |
| 4776 | 3 | 4 | | | | IV-2 | SLC25A44 | 0.91 |
| 4777 | 3 | 4 | | | | IV-2 | SLC25A45 | 0.76 |
| 4778 | 3 | 4 | | | | IV-2 | SLC26A1 | 0.92 |
| 4779 | 3 | 4 | | | | IV-2 | SLC2A1 | 0.73 |
| 4780 | 3 | 4 | | | | IV-2 | SLC2A11 | 0.95 |
| 4781 | 3 | 4 | | | | IV-2 | SLC2A8 | 0.90 |
| 4782 | 3 | 4 | | | | IV-2 | SLC30A4 | 0.94 |
| 4783 | 3 | 4 | | | | IV-2 | SLC38A1 | 0.94 |
| 4784 | 3 | 4 | | | | IV-2 | SLC39A4 | 0.99 |
| 4785 | 3 | 4 | | | | IV-2 | SLC40A1 | 0.93 |
| 4786 | 3 | 4 | | | | IV-2 | SLC44A2 | 0.79 |
| 4787 | 3 | 4 | | | | IV-2 | SLC6A6 | 0.76 |
| 4788 | 3 | 4 | | | | IV-2 | SLC6A9 | 0.92 |
| 4789 | 3 | 4 | | | | IV-2 | SLC9A3R1 | 0.98 |
| 4790 | 3 | 4 | | | | IV-2 | SLC9A8 | 0.88 |
| 4791 | 3 | 4 | | | | IV-2 | SLFN13 | 0.79 |
| 4792 | 3 | 4 | | | | IV-2 | SMA4 | 0.94 |
| 4793 | 3 | 4 | | | | IV-2 | SMAGP | 0.87 |
| 4794 | 3 | 4 | | | | IV-2 | SMCHD1 | 0.82 |
| 4795 | 3 | 4 | | | | IV-2 | SMG5 | 0.97 |

Fig. 41 - 26

| | | | | | | | | | | | | | |
|---|---|---|---|---|---|---|---|---|---|---|---|---|---|
| 4796 | 3 | 4 | | | IV-2 | SMPDL3B | 0.92 | 4892 | 3 | 4 | | IV-2 | THSD1P1 | 0.73 |
| 4797 | 3 | 4 | | | IV-2 | SMYD3 | 0.85 | 4893 | 3 | 4 | | IV-2 | TIFAB | 0.86 |
| 4798 | 3 | 4 | | | IV-2 | SMYD5 | 0.80 | 4894 | 3 | 4 | | IV-2 | TIGD7 | 0.80 |
| 4799 | 3 | 4 | | | IV-2 | SNAI3 | 0.76 | 4895 | 3 | 4 | | IV-2 | TIMM8B | 0.99 |
| 4800 | 3 | 4 | | | IV-2 | SNAPC5 | 0.96 | 4896 | 3 | 4 | | IV-2 | TM2D1 | 0.94 |
| 4801 | 3 | 4 | | | IV-2 | SNHG11 | 0.94 | 4897 | 3 | 4 | | IV-2 | TMC6 | 0.98 |
| 4802 | 3 | 4 | | | IV-2 | SNHG15 | 0.69 | 4898 | 3 | 4 | | IV-2 | TMC8 | 0.96 |
| 4803 | 3 | 4 | | | IV-2 | SNN | 0.85 | 4899 | 3 | 4 | | IV-2 | TMCC3 | 0.74 |
| 4804 | 3 | 4 | | | IV-2 | SNRK | 0.99 | 4900 | 3 | 4 | | IV-2 | TMCO6 | 0.87 |
| 4805 | 3 | 4 | | | IV-2 | SNRPD2 | 0.72 | 4901 | 3 | 4 | | IV-2 | TMEM120B | 0.92 |
| 4806 | 3 | 4 | | | IV-2 | SNTA1 | 1.00 | 4902 | 3 | 4 | | IV-2 | TMEM141 | 0.90 |
| 4807 | 3 | 4 | | | IV-2 | SNURF | 0.94 | 4903 | 3 | 4 | | IV-2 | TMEM143 | 0.88 |
| 4808 | 3 | 4 | | | IV-2 | SOD2 | 0.92 | 4904 | 3 | 4 | | IV-2 | TMEM154 | 0.77 |
| 4809 | 3 | 4 | | | IV-2 | SOX8 | 0.95 | 4905 | 3 | 4 | | IV-2 | TMEM156 | 0.88 |
| 4810 | 3 | 4 | | | IV-2 | SPATS2 | 0.96 | 4906 | 3 | 4 | | IV-2 | TMEM161B | 0.98 |
| 4811 | 3 | 4 | | | IV-2 | SPDYC | 0.99 | 4907 | 3 | 4 | | IV-2 | TMEM175 | 1.00 |
| 4812 | 3 | 4 | | | IV-2 | SPDYE2 | 0.93 | 4908 | 3 | 4 | | IV-2 | TMEM216 | 0.71 |
| 4813 | 3 | 4 | | | IV-2 | SPNS2 | 0.90 | 4909 | 3 | 4 | | IV-2 | TMEM220 | 0.71 |
| 4814 | 3 | 4 | | | IV-2 | SPOCD1 | 0.84 | 4910 | 3 | 4 | | IV-2 | TMEM222 | 0.96 |
| 4815 | 3 | 4 | | | IV-2 | SPRY1 | 0.95 | 4911 | 3 | 4 | | IV-2 | TMEM55A | 0.91 |
| 4816 | 3 | 4 | | | IV-2 | SPRYD7 | 0.96 | 4912 | 3 | 4 | | IV-2 | TMEM55B | 0.89 |
| 4817 | 3 | 4 | | | IV-2 | SPTA1 | 0.99 | 4913 | 3 | 4 | | IV-2 | TMEM63C | 0.92 |
| 4818 | 3 | 4 | | | IV-2 | SRA1 | 0.86 | 4914 | 3 | 4 | | IV-2 | TMEM64 | 0.70 |
| 4819 | 3 | 4 | | | IV-2 | SRGN | 0.86 | 4915 | 3 | 4 | | IV-2 | TMEM71 | 0.82 |
| 4820 | 3 | 4 | | | IV-2 | SRP14 | 0.98 | 4916 | 3 | 4 | | IV-2 | TMEM79 | 0.99 |
| 4821 | 3 | 4 | | | IV-2 | SRRM2 | 0.88 | 4917 | 3 | 4 | | IV-2 | TMEM9 | 0.84 |
| 4822 | 3 | 4 | | | IV-2 | SSPN | 0.82 | 4918 | 3 | 4 | | IV-2 | TMEM99 | 1.00 |
| 4823 | 3 | 4 | | | IV-2 | ST3GAL3 | 0.80 | 4919 | 3 | 4 | | IV-2 | TMIE | 0.94 |
| 4824 | 3 | 4 | | | IV-2 | ST3GAL4 | 0.96 | 4920 | 3 | 4 | | IV-2 | TMX4 | 0.93 |
| 4825 | 3 | 4 | | | IV-2 | ST6GALNAC1 | 0.98 | 4921 | 3 | 4 | | IV-2 | TNFAIP3 | 0.98 |
| 4826 | 3 | 4 | | | IV-2 | ST8SIA6 | 0.93 | 4922 | 3 | 4 | | IV-2 | TNFRSF21 | 0.90 |
| 4827 | 3 | 4 | | | IV-2 | STAG3L1 | 0.82 | 4923 | 3 | 4 | | IV-2 | TNNC2 | 0.99 |
| 4828 | 3 | 4 | | | IV-2 | STAG3L2 | 0.76 | 4924 | 3 | 4 | | IV-2 | TNNI2 | 0.70 |
| 4829 | 3 | 4 | | | IV-2 | STAG3L3 | 0.97 | 4925 | 3 | 4 | | IV-2 | TNXA | 0.98 |
| 4830 | 3 | 4 | | | IV-2 | STAG3L4 | 0.94 | 4926 | 3 | 4 | | IV-2 | TNXB | 0.95 |
| 4831 | 3 | 4 | | | IV-2 | STK16 | 0.91 | 4927 | 3 | 4 | | IV-2 | TOP3B | 0.95 |
| 4832 | 3 | 4 | | | IV-2 | STK17A | 0.83 | 4928 | 3 | 4 | | IV-2 | TOPORS | 0.83 |
| 4833 | 3 | 4 | | | IV-2 | STK40 | 0.81 | 4929 | 3 | 4 | | IV-2 | TOX | 0.95 |
| 4834 | 3 | 4 | | | IV-2 | STRN4 | 0.99 | 4930 | 3 | 4 | | IV-2 | TP53I11 | 0.95 |
| 4835 | 3 | 4 | | | IV-2 | STX1A | 0.88 | 4931 | 3 | 4 | | IV-2 | TP53INP1 | 0.77 |
| 4836 | 3 | 4 | | | IV-2 | STX2 | 0.76 | 4932 | 3 | 4 | | IV-2 | TP53TG1 | 0.92 |
| 4837 | 3 | 4 | | | IV-2 | STXBP5 | 0.87 | 4933 | 3 | 4 | | IV-2 | TPM1 | 1.00 |
| 4838 | 3 | 4 | | | IV-2 | SUGP2 | 0.85 | 4934 | 3 | 4 | | IV-2 | TPRKB | 0.97 |
| 4839 | 3 | 4 | | | IV-2 | SUPT3H | 0.96 | 4935 | 3 | 4 | | IV-2 | TPT1 | 0.78 |
| 4840 | 3 | 4 | | | IV-2 | SUPT4H1 | 0.85 | 4936 | 3 | 4 | | IV-2 | TRAF4 | 0.87 |
| 4841 | 3 | 4 | | | IV-2 | SURF1 | 0.95 | 4937 | 3 | 4 | | IV-2 | TRAF5 | 0.82 |
| 4842 | 3 | 4 | | | IV-2 | SUV39H1 | 0.92 | 4938 | 3 | 4 | | IV-2 | TRANK1 | 0.89 |
| 4843 | 3 | 4 | | | IV-2 | SUV420H2 | 0.86 | 4939 | 3 | 4 | | IV-2 | TRAPPC2 | 0.72 |
| 4844 | 3 | 4 | | | IV-2 | SYNE2 | 0.87 | 4940 | 3 | 4 | | IV-2 | TRAPPC2P1 | 0.94 |
| 4845 | 3 | 4 | | | IV-2 | SYTL1 | 0.72 | 4941 | 3 | 4 | | IV-2 | TREM1 | 0.79 |
| 4846 | 3 | 4 | | | IV-2 | SYTL3 | 0.86 | 4942 | 3 | 4 | | IV-2 | TRERF1 | 0.98 |
| 4847 | 3 | 4 | | | IV-2 | TAF1A | 0.91 | 4943 | 3 | 4 | | IV-2 | TRIM39 | 0.84 |
| 4848 | 3 | 4 | | | IV-2 | TAF1C | 0.96 | 4944 | 3 | 4 | | IV-2 | TRIM40 | 1.00 |
| 4849 | 3 | 4 | | | IV-2 | TAF1D | 0.95 | 4945 | 3 | 4 | | IV-2 | TRIP10 | 1.00 |
| 4850 | 3 | 4 | | | IV-2 | TAF9B | 0.96 | 4946 | 3 | 4 | | IV-2 | TRMT1 | 0.98 |
| 4851 | 3 | 4 | | | IV-2 | TAGAP | 0.72 | 4947 | 3 | 4 | | IV-2 | TRPT1 | 0.70 |
| 4852 | 3 | 4 | | | IV-2 | TAGLN2 | 0.78 | 4948 | 3 | 4 | | IV-2 | TSC22D4 | 0.93 |
| 4853 | 3 | 4 | | | IV-2 | TANC2 | 0.80 | 4949 | 3 | 4 | | IV-2 | TSEN2 | 0.98 |
| 4854 | 3 | 4 | | | IV-2 | TANK | 0.95 | 4950 | 3 | 4 | | IV-2 | TSEN34 | 0.90 |
| 4855 | 3 | 4 | | | IV-2 | TAP1 | 0.90 | 4951 | 3 | 4 | | IV-2 | TSEN54 | 0.90 |
| 4856 | 3 | 4 | | | IV-2 | TAS2R40 | 0.81 | 4952 | 3 | 4 | | IV-2 | TSPAN16 | 0.98 |
| 4857 | 3 | 4 | | | IV-2 | TASP1 | 1.00 | 4953 | 3 | 4 | | IV-2 | TSPAN3 | 0.87 |
| 4858 | 3 | 4 | | | IV-2 | TATDN3 | 0.96 | 4954 | 3 | 4 | | IV-2 | TSPAN7 | 0.93 |
| 4859 | 3 | 4 | | | IV-2 | TAZ | 1.00 | 4955 | 3 | 4 | | IV-2 | TSPYL2 | 0.70 |
| 4860 | 3 | 4 | | | IV-2 | TBC1D10A | 0.98 | 4956 | 3 | 4 | | IV-2 | TSSK4 | 0.92 |
| 4861 | 3 | 4 | | | IV-2 | TBC1D10C | 0.71 | 4957 | 3 | 4 | | IV-2 | TSTA3 | 0.87 |
| 4862 | 3 | 4 | | | IV-2 | TBC1D17 | 0.80 | 4958 | 3 | 4 | | IV-2 | TTC14 | 0.75 |
| 4863 | 3 | 4 | | | IV-2 | TBC1D3G | 0.96 | 4959 | 3 | 4 | | IV-2 | TTC39B | 0.99 |
| 4864 | 3 | 4 | | | IV-2 | TBC1D3H | 0.93 | 4960 | 3 | 4 | | IV-2 | TTC9 | 0.79 |
| 4865 | 3 | 4 | | | IV-2 | TBL1X | 0.93 | 4961 | 3 | 4 | | IV-2 | TTLL5 | 0.99 |
| 4866 | 3 | 4 | | | IV-2 | TBP | 0.89 | 4962 | 3 | 4 | | IV-2 | TUBA1A | 0.98 |
| 4867 | 3 | 4 | | | IV-2 | TBX19 | 1.00 | 4963 | 3 | 4 | | IV-2 | TUBA4A | 0.69 |
| 4868 | 3 | 4 | | | IV-2 | TBXA2R | 0.99 | 4964 | 3 | 4 | | IV-2 | TUBE1 | 1.00 |
| 4869 | 3 | 4 | | | IV-2 | TC2N | 0.81 | 4965 | 3 | 4 | | IV-2 | TUBG2 | 0.89 |
| 4870 | 3 | 4 | | | IV-2 | TCEA2 | 0.86 | 4966 | 3 | 4 | | IV-2 | TUBGCP5 | 0.90 |
| 4871 | 3 | 4 | | | IV-2 | TCEAL1 | 0.92 | 4967 | 3 | 4 | | IV-2 | TUBGCP6 | 0.70 |
| 4872 | 3 | 4 | | | IV-2 | TCEB2 | 0.94 | 4968 | 3 | 4 | | IV-2 | TUFT1 | 0.86 |
| 4873 | 3 | 4 | | | IV-2 | TCP11L2 | 0.80 | 4969 | 3 | 4 | | IV-2 | TUSC2 | 0.91 |
| 4874 | 3 | 4 | | | IV-2 | TCTN1 | 0.96 | 4970 | 3 | 4 | | IV-2 | TXK | 0.81 |
| 4875 | 3 | 4 | | | IV-2 | TCTN2 | 0.97 | 4971 | 3 | 4 | | IV-2 | TXNDC3 | 1.00 |
| 4876 | 3 | 4 | | | IV-2 | TDP2 | 0.90 | 4972 | 3 | 4 | | IV-2 | TXNDC9 | 0.96 |
| 4877 | 3 | 4 | | | IV-2 | TEC | 0.98 | 4973 | 3 | 4 | | IV-2 | UBAP1 | 0.83 |
| 4878 | 3 | 4 | | | IV-2 | TECPR2 | 0.81 | 4974 | 3 | 4 | | IV-2 | UBE2M | 0.93 |
| 4879 | 3 | 4 | | | IV-2 | TESK2 | 0.83 | 4975 | 3 | 4 | | IV-2 | UBL4A | 1.00 |
| 4880 | 3 | 4 | | | IV-2 | TEX30 | 0.90 | 4976 | 3 | 4 | | IV-2 | UBN1 | 0.96 |
| 4881 | 3 | 4 | | | IV-2 | TFAP2E | 0.99 | 4977 | 3 | 4 | | IV-2 | UBR2 | 0.97 |
| 4882 | 3 | 4 | | | IV-2 | TFEB | 0.99 | 4978 | 3 | 4 | | IV-2 | UCP3 | 0.94 |
| 4883 | 3 | 4 | | | IV-2 | TFIP11 | 0.90 | 4979 | 3 | 4 | | IV-2 | UIMC1 | 0.92 |
| 4884 | 3 | 4 | | | IV-2 | TFR2 | 0.95 | 4980 | 3 | 4 | | IV-2 | ULK1 | 0.95 |
| 4885 | 3 | 4 | | | IV-2 | THAP5 | 0.89 | 4981 | 3 | 4 | | IV-2 | ULK3 | 0.76 |
| 4886 | 3 | 4 | | | IV-2 | THAP7-AS1 | 0.70 | 4982 | 3 | 4 | | IV-2 | UNC119 | 0.72 |
| 4887 | 3 | 4 | | | IV-2 | THBD | 0.80 | 4983 | 3 | 4 | | IV-2 | UNKL | 0.91 |
| 4888 | 3 | 4 | | | IV-2 | THEM4 | 0.82 | 4984 | 3 | 4 | | IV-2 | UPB1 | 0.96 |
| 4889 | 3 | 4 | | | IV-2 | THEM5 | 0.88 | 4985 | 3 | 4 | | IV-2 | UQCR10 | 0.93 |
| 4890 | 3 | 4 | | | IV-2 | THOC5 | 0.86 | 4986 | 3 | 4 | | IV-2 | UQCRBP1 | 0.99 |
| 4891 | 3 | 4 | | | IV-2 | THRA | 0.88 | 4987 | 3 | 4 | | IV-2 | USE1 | 0.76 |

Fig. 41 - 27

| | | | | | | | |
|---|---|---|---|---|---|---|---|
| 4988 | 3 | 4 | | | IV-2 | USF1 | 0.98 |
| 4989 | 3 | 4 | | | IV-2 | USF2 | 0.97 |
| 4990 | 3 | 4 | | | IV-2 | USP20 | 0.94 |
| 4991 | 3 | 4 | | | IV-2 | USP32P1 | 0.90 |
| 4992 | 3 | 4 | | | IV-2 | USP44 | 0.99 |
| 4993 | 3 | 4 | | | IV-2 | UXT | 0.93 |
| 4994 | 3 | 4 | | | IV-2 | VEGFB | 0.95 |
| 4995 | 3 | 4 | | | IV-2 | VEPH1 | 0.99 |
| 4996 | 3 | 4 | | | IV-2 | VHLL | 0.92 |
| 4997 | 3 | 4 | | | IV-2 | VMAC | 0.77 |
| 4998 | 3 | 4 | | | IV-2 | VMP1 | 0.74 |
| 4999 | 3 | 4 | | | IV-2 | VNN2 | 0.74 |
| 5000 | 3 | 4 | | | IV-2 | VPS13A | 1.00 |
| 5001 | 3 | 4 | | | IV-2 | VPS37C | 0.96 |
| 5002 | 3 | 4 | | | IV-2 | VRK3 | 0.96 |
| 5003 | 3 | 4 | | | IV-2 | VSIG10 | 0.97 |
| 5004 | 3 | 4 | | | IV-2 | VSIG2 | 0.91 |
| 5005 | 3 | 4 | | | IV-2 | WASH7P | 0.81 |
| 5006 | 3 | 4 | | | IV-2 | WBP1 | 0.94 |
| 5007 | 3 | 4 | | | IV-2 | WDR34 | 0.83 |
| 5008 | 3 | 4 | | | IV-2 | WDR45 | 0.86 |
| 5009 | 3 | 4 | | | IV-2 | WDR73 | 0.84 |
| 5010 | 3 | 4 | | | IV-2 | WDR85 | 0.95 |
| 5011 | 3 | 4 | | | IV-2 | WDTC1 | 0.85 |
| 5012 | 3 | 4 | | | IV-2 | WEE1 | 0.90 |
| 5013 | 3 | 4 | | | IV-2 | WNT10A | 0.93 |
| 5014 | 3 | 4 | | | IV-2 | WRAP53 | 0.95 |
| 5015 | 3 | 4 | | | IV-2 | WWC3 | 0.83 |
| 5016 | 3 | 4 | | | IV-2 | WWOX | 0.93 |
| 5017 | 3 | 4 | | | IV-2 | XCR1 | 0.98 |
| 5018 | 3 | 4 | | | IV-2 | XKR8 | 0.72 |
| 5019 | 3 | 4 | | | IV-2 | YAE1D1 | 0.75 |
| 5020 | 3 | 4 | | | IV-2 | YBX1 | 0.75 |
| 5021 | 3 | 4 | | | IV-2 | YEATS4 | 0.85 |
| 5022 | 3 | 4 | | | IV-2 | YPEL1 | 0.75 |
| 5023 | 3 | 4 | | | IV-2 | ZAP70 | 0.83 |
| 5024 | 3 | 4 | | | IV-2 | ZBP1 | 0.98 |
| 5025 | 3 | 4 | | | IV-2 | ZBTB17 | 0.92 |
| 5026 | 3 | 4 | | | IV-2 | ZBTB25 | 0.92 |
| 5027 | 3 | 4 | | | IV-2 | ZBTB32 | 0.88 |
| 5028 | 3 | 4 | | | IV-2 | ZBTB37 | 0.78 |
| 5029 | 3 | 4 | | | IV-2 | ZBTB46 | 0.99 |
| 5030 | 3 | 4 | | | IV-2 | ZBTB48 | 0.96 |
| 5031 | 3 | 4 | | | IV-2 | ZBTB49 | 0.72 |
| 5032 | 3 | 4 | | | IV-2 | ZC3H8 | 0.78 |
| 5033 | 3 | 4 | | | IV-2 | ZC4H2 | 0.98 |
| 5034 | 3 | 4 | | | IV-2 | ZCCHC18 | 0.95 |
| 5035 | 3 | 4 | | | IV-2 | ZCWPW1 | 0.96 |
| 5036 | 3 | 4 | | | IV-2 | ZDHHC21 | 0.98 |
| 5037 | 3 | 4 | | | IV-2 | ZFAND1 | 0.88 |
| 5038 | 3 | 4 | | | IV-2 | ZFAND2B | 0.68 |
| 5039 | 3 | 4 | | | IV-2 | ZFAND4 | 0.94 |
| 5040 | 3 | 4 | | | IV-2 | ZFP28 | 0.89 |
| 5041 | 3 | 4 | | | IV-2 | ZFP37 | 0.94 |
| 5042 | 3 | 4 | | | IV-2 | ZFP57 | 0.94 |
| 5043 | 3 | 4 | | | IV-2 | ZFPL1 | 0.95 |
| 5044 | 3 | 4 | | | IV-2 | ZFX | 0.84 |
| 5045 | 3 | 4 | | | IV-2 | ZFYVE27 | 0.81 |
| 5046 | 3 | 4 | | | IV-2 | ZFYVE28 | 0.86 |
| 5047 | 3 | 4 | | | IV-2 | ZGLP1 | 0.99 |
| 5048 | 3 | 4 | | | IV-2 | ZHX2 | 0.90 |
| 5049 | 3 | 4 | | | IV-2 | ZMIZ2 | 0.94 |
| 5050 | 3 | 4 | | | IV-2 | ZNF10 | 0.87 |
| 5051 | 3 | 4 | | | IV-2 | ZNF137P | 0.84 |
| 5052 | 3 | 4 | | | IV-2 | ZNF138 | 0.81 |
| 5053 | 3 | 4 | | | IV-2 | ZNF167 | 0.95 |
| 5054 | 3 | 4 | | | IV-2 | ZNF174 | 0.91 |
| 5055 | 3 | 4 | | | IV-2 | ZNF185 | 0.93 |
| 5056 | 3 | 4 | | | IV-2 | ZNF187 | 0.99 |
| 5057 | 3 | 4 | | | IV-2 | ZNF193 | 0.97 |
| 5058 | 3 | 4 | | | IV-2 | ZNF205 | 1.00 |
| 5059 | 3 | 4 | | | IV-2 | ZNF211 | 0.90 |
| 5060 | 3 | 4 | | | IV-2 | ZNF223 | 0.85 |
| 5061 | 3 | 4 | | | IV-2 | ZNF235 | 0.96 |
| 5062 | 3 | 4 | | | IV-2 | ZNF238 | 0.82 |
| 5063 | 3 | 4 | | | IV-2 | ZNF250 | 0.97 |
| 5064 | 3 | 4 | | | IV-2 | ZNF254 | 0.87 |
| 5065 | 3 | 4 | | | IV-2 | ZNF266 | 0.74 |
| 5066 | 3 | 4 | | | IV-2 | ZNF273 | 0.76 |
| 5067 | 3 | 4 | | | IV-2 | ZNF274 | 0.75 |
| 5068 | 3 | 4 | | | IV-2 | ZNF276 | 0.74 |
| 5069 | 3 | 4 | | | IV-2 | ZNF284 | 0.79 |
| 5070 | 3 | 4 | | | IV-2 | ZNF285 | 0.91 |
| 5071 | 3 | 4 | | | IV-2 | ZNF32 | 0.78 |
| 5072 | 3 | 4 | | | IV-2 | ZNF321P | 0.96 |
| 5073 | 3 | 4 | | | IV-2 | ZNF333 | 0.75 |
| 5074 | 3 | 4 | | | IV-2 | ZNF337 | 0.86 |
| 5075 | 3 | 4 | | | IV-2 | ZNF33A | 0.82 |
| 5076 | 3 | 4 | | | IV-2 | ZNF345 | 0.88 |
| 5077 | 3 | 4 | | | IV-2 | ZNF354B | 0.95 |
| 5078 | 3 | 4 | | | IV-2 | ZNF382 | 0.97 |
| 5079 | 3 | 4 | | | IV-2 | ZNF385D | 0.93 |
| 5080 | 3 | 4 | | | IV-2 | ZNF397 | 0.99 |
| 5081 | 3 | 4 | | | IV-2 | ZNF415 | 0.92 |
| 5082 | 3 | 4 | | | IV-2 | ZNF417 | 0.91 |
| 5083 | 3 | 4 | | | IV-2 | ZNF418 | 0.97 |
| 5084 | 3 | 4 | | | IV-2 | ZNF419 | 0.76 |
| 5085 | 3 | 4 | | | IV-2 | ZNF429 | 0.75 |
| 5086 | 3 | 4 | | | IV-2 | ZNF434 | 0.95 |
| 5087 | 3 | 4 | | | IV-2 | ZNF439 | 0.84 |
| 5088 | 3 | 4 | | | IV-2 | ZNF443 | 0.81 |
| 5089 | 3 | 4 | | | IV-2 | ZNF460 | 0.96 |
| 5090 | 3 | 4 | | | IV-2 | ZNF461 | 0.83 |
| 5091 | 3 | 4 | | | IV-2 | ZNF467 | 1.00 |
| 5092 | 3 | 4 | | | IV-2 | ZNF470 | 0.96 |
| 5093 | 3 | 4 | | | IV-2 | ZNF48 | 0.99 |
| 5094 | 3 | 4 | | | IV-2 | ZNF493 | 0.82 |
| 5095 | 3 | 4 | | | IV-2 | ZNF507 | 0.79 |
| 5096 | 3 | 4 | | | IV-2 | ZNF514 | 0.90 |
| 5097 | 3 | 4 | | | IV-2 | ZNF530 | 0.82 |
| 5098 | 3 | 4 | | | IV-2 | ZNF543 | 0.96 |
| 5099 | 3 | 4 | | | IV-2 | ZNF547 | 1.00 |
| 5100 | 3 | 4 | | | IV-2 | ZNF548 | 0.75 |
| 5101 | 3 | 4 | | | IV-2 | ZNF552 | 0.87 |
| 5102 | 3 | 4 | | | IV-2 | ZNF554 | 0.95 |
| 5103 | 3 | 4 | | | IV-2 | ZNF566 | 0.99 |
| 5104 | 3 | 4 | | | IV-2 | ZNF567 | 0.69 |
| 5105 | 3 | 4 | | | IV-2 | ZNF568 | 0.88 |
| 5106 | 3 | 4 | | | IV-2 | ZNF575 | 0.91 |
| 5107 | 3 | 4 | | | IV-2 | ZNF577 | 0.85 |
| 5108 | 3 | 4 | | | IV-2 | ZNF582 | 0.91 |
| 5109 | 3 | 4 | | | IV-2 | ZNF585A | 1.00 |
| 5110 | 3 | 4 | | | IV-2 | ZNF585B | 0.81 |
| 5111 | 3 | 4 | | | IV-2 | ZNF586 | 0.99 |
| 5112 | 3 | 4 | | | IV-2 | ZNF587 | 0.86 |
| 5113 | 3 | 4 | | | IV-2 | ZNF589 | 1.00 |
| 5114 | 3 | 4 | | | IV-2 | ZNF595 | 0.73 |
| 5115 | 3 | 4 | | | IV-2 | ZNF600 | 0.85 |
| 5116 | 3 | 4 | | | IV-2 | ZNF607 | 0.81 |
| 5117 | 3 | 4 | | | IV-2 | ZNF608 | 0.96 |
| 5118 | 3 | 4 | | | IV-2 | ZNF630 | 0.99 |
| 5119 | 3 | 4 | | | IV-2 | ZNF643 | 0.96 |
| 5120 | 3 | 4 | | | IV-2 | ZNF646 | 0.97 |
| 5121 | 3 | 4 | | | IV-2 | ZNF658B | 0.92 |
| 5122 | 3 | 4 | | | IV-2 | ZNF671 | 0.78 |
| 5123 | 3 | 4 | | | IV-2 | ZNF674 | 0.82 |
| 5124 | 3 | 4 | | | IV-2 | ZNF675 | 0.71 |
| 5125 | 3 | 4 | | | IV-2 | ZNF678 | 0.90 |
| 5126 | 3 | 4 | | | IV-2 | ZNF680 | 0.82 |
| 5127 | 3 | 4 | | | IV-2 | ZNF688 | 0.90 |
| 5128 | 3 | 4 | | | IV-2 | ZNF699 | 0.92 |
| 5129 | 3 | 4 | | | IV-2 | ZNF702P | 0.86 |
| 5130 | 3 | 4 | | | IV-2 | ZNF708 | 0.87 |
| 5131 | 3 | 4 | | | IV-2 | ZNF709 | 0.96 |
| 5132 | 3 | 4 | | | IV-2 | ZNF71 | 0.77 |
| 5133 | 3 | 4 | | | IV-2 | ZNF714 | 0.97 |
| 5134 | 3 | 4 | | | IV-2 | ZNF724P | 0.97 |
| 5135 | 3 | 4 | | | IV-2 | ZNF737 | 0.96 |
| 5136 | 3 | 4 | | | IV-2 | ZNF746 | 0.89 |
| 5137 | 3 | 4 | | | IV-2 | ZNF77 | 0.92 |
| 5138 | 3 | 4 | | | IV-2 | ZNF776 | 0.88 |
| 5139 | 3 | 4 | | | IV-2 | ZNF778 | 0.77 |
| 5140 | 3 | 4 | | | IV-2 | ZNF790 | 0.96 |
| 5141 | 3 | 4 | | | IV-2 | ZNF8 | 1.00 |
| 5142 | 3 | 4 | | | IV-2 | ZNF80 | 1.00 |
| 5143 | 3 | 4 | | | IV-2 | ZNF808 | 0.96 |
| 5144 | 3 | 4 | | | IV-2 | ZNF815 | 0.96 |
| 5145 | 3 | 4 | | | IV-2 | ZNF821 | 0.70 |
| 5146 | 3 | 4 | | | IV-2 | ZNF823 | 0.81 |
| 5147 | 3 | 4 | | | IV-2 | ZNF827 | 0.96 |
| 5148 | 3 | 4 | | | IV-2 | ZNF829 | 0.98 |
| 5149 | 3 | 4 | | | IV-2 | ZNF835 | 0.77 |
| 5150 | 3 | 4 | | | IV-2 | ZNF837 | 0.96 |
| 5151 | 3 | 4 | | | IV-2 | ZNF839 | 0.75 |
| 5152 | 3 | 4 | | | IV-2 | ZNF85 | 0.86 |
| 5153 | 3 | 4 | | | IV-2 | ZNF862 | 0.84 |
| 5154 | 3 | 4 | | | IV-2 | ZNF883 | 0.96 |
| 5155 | 3 | 4 | | | IV-2 | ZNF890P | 0.91 |
| 5156 | 3 | 4 | | | IV-2 | ZNF92 | 0.95 |
| 5157 | 3 | 4 | | | IV-2 | ZRANB1 | 0.97 |
| 5158 | 3 | 4 | | | IV-2 | ZRANB2-AS1 | 0.97 |
| 5159 | 3 | 4 | | | IV-2 | ZRSR2 | 1.00 |
| 5160 | 3 | 4 | | | IV-2 | ZSCAN12 | 0.88 |
| 5161 | 3 | 4 | | | IV-2 | ZSCAN30 | 0.75 |
| 5162 | 3 | 4 | | | IV-1 | ABCB8 | 1.47 |
| 5163 | 3 | 4 | | | IV-1 | ABCC6P2 | 1.13 |
| 5164 | 3 | 4 | | | IV-1 | ABCD2 | 1.30 |
| 5165 | 3 | 4 | | | IV-1 | ABCD4 | 1.24 |
| 5166 | 3 | 4 | | | IV-1 | ABCE1 | 1.44 |
| 5167 | 3 | 4 | | | IV-1 | ABHD10 | 1.15 |
| 5168 | 3 | 4 | | | IV-1 | ABHD13 | 1.34 |
| 5169 | 3 | 4 | | | IV-1 | ABHD14B | 1.25 |
| 5170 | 3 | 4 | | | IV-1 | ABHD16A | 1.38 |
| 5171 | 3 | 4 | | | IV-1 | ABHD2 | 1.32 |
| 5172 | 3 | 4 | | | IV-1 | ABHD3 | 1.46 |
| 5173 | 3 | 4 | | | IV-1 | ABI1 | 1.36 |
| 5174 | 3 | 4 | | | IV-1 | ABR | 1.38 |
| 5175 | 3 | 4 | | | IV-1 | ABT1 | 1.08 |
| 5176 | 3 | 4 | | | IV-1 | ACAA1 | 1.48 |
| 5177 | 3 | 4 | | | IV-1 | ACAD10 | 1.38 |
| 5178 | 3 | 4 | | | IV-1 | ACAD8 | 1.42 |
| 5179 | 3 | 4 | | | IV-1 | ACADM | 1.34 |

Fig. 41 - 28

| | | | | | | | | | | | | | |
|---|---|---|---|---|---|---|---|---|---|---|---|---|---|
| 5180 | 3 | 4 | | | IV-1 | ACADSB | 1.09 | 5276 | 3 | 4 | | IV-1 | ANAPC7 | 1.36 |
| 5181 | 3 | 4 | | | IV-1 | ACAP1 | 1.31 | 5277 | 3 | 4 | | IV-1 | ANGEL1 | 1.50 |
| 5182 | 3 | 4 | | | IV-1 | ACAP2 | 1.41 | 5278 | 3 | 4 | | IV-1 | ANGEL2 | 1.17 |
| 5183 | 3 | 4 | | | IV-1 | ACAP3 | 1.10 | 5279 | 3 | 4 | | IV-1 | ANKLE2 | 1.29 |
| 5184 | 3 | 4 | | | IV-1 | ACAT2 | 1.40 | 5280 | 3 | 4 | | IV-1 | ANKMY2 | 1.49 |
| 5185 | 3 | 4 | | | IV-1 | ACBD6 | 1.24 | 5281 | 3 | 4 | | IV-1 | ANKRD10 | 1.13 |
| 5186 | 3 | 4 | | | IV-1 | ACD | 1.10 | 5282 | 3 | 4 | | IV-1 | ANKRD11 | 1.37 |
| 5187 | 3 | 4 | | | IV-1 | ACER2 | 1.34 | 5283 | 3 | 4 | | IV-1 | ANKRD13C | 1.38 |
| 5188 | 3 | 4 | | | IV-1 | ACIN1 | 1.17 | 5284 | 3 | 4 | | IV-1 | ANKRD16 | 1.25 |
| 5189 | 3 | 4 | | | IV-1 | ACOT13 | 1.32 | 5285 | 3 | 4 | | IV-1 | ANKRD19P | 1.12 |
| 5190 | 3 | 4 | | | IV-1 | ACOT4 | 1.21 | 5286 | 3 | 4 | | IV-1 | ANKRD26 | 1.21 |
| 5191 | 3 | 4 | | | IV-1 | ACOT8 | 1.42 | 5287 | 3 | 4 | | IV-1 | ANKRD27 | 1.19 |
| 5192 | 3 | 4 | | | IV-1 | ACOX1 | 1.22 | 5288 | 3 | 4 | | IV-1 | ANKRD28 | 1.09 |
| 5193 | 3 | 4 | | | IV-1 | ACP1 | 1.40 | 5289 | 3 | 4 | | IV-1 | ANKRD39 | 1.15 |
| 5194 | 3 | 4 | | | IV-1 | ACP6 | 1.02 | 5290 | 3 | 4 | | IV-1 | ANKRD44 | 1.18 |
| 5195 | 3 | 4 | | | IV-1 | ACPL2 | 1.37 | 5291 | 3 | 4 | | IV-1 | ANKRD46 | 1.24 |
| 5196 | 3 | 4 | | | IV-1 | ACSF2 | 1.23 | 5292 | 3 | 4 | | IV-1 | ANKRD49 | 1.01 |
| 5197 | 3 | 4 | | | IV-1 | ACSS1 | 1.48 | 5293 | 3 | 4 | | IV-1 | ANKRD5 | 1.17 |
| 5198 | 3 | 4 | | | IV-1 | ACTB | 1.46 | 5294 | 3 | 4 | | IV-1 | ANKRD52 | 1.27 |
| 5199 | 3 | 4 | | | IV-1 | ACTL10 | 1.41 | 5295 | 3 | 4 | | IV-1 | ANKRD54 | 1.49 |
| 5200 | 3 | 4 | | | IV-1 | ACTL6A | 1.48 | 5296 | 3 | 4 | | IV-1 | ANO8 | 1.34 |
| 5201 | 3 | 4 | | | IV-1 | ACTN1 | 1.19 | 5297 | 3 | 4 | | IV-1 | ANP32A | 1.17 |
| 5202 | 3 | 4 | | | IV-1 | ACTN4 | 1.33 | 5298 | 3 | 4 | | IV-1 | ANP32AP1 | 1.35 |
| 5203 | 3 | 4 | | | IV-1 | ACTR1B | 1.24 | 5299 | 3 | 4 | | IV-1 | ANP32D | 1.48 |
| 5204 | 3 | 4 | | | IV-1 | ACTR5 | 1.42 | 5300 | 3 | 4 | | IV-1 | ANTXR2 | 1.23 |
| 5205 | 3 | 4 | | | IV-1 | ACTR6 | 1.24 | 5301 | 3 | 4 | | IV-1 | ANXA11 | 1.12 |
| 5206 | 3 | 4 | | | IV-1 | ACVR2A | 1.08 | 5302 | 3 | 4 | | IV-1 | AP1G2 | 1.22 |
| 5207 | 3 | 4 | | | IV-1 | ACVR2B | 1.06 | 5303 | 3 | 4 | | IV-1 | AP2M1 | 1.39 |
| 5208 | 3 | 4 | | | IV-1 | ACVRL1 | 1.02 | 5304 | 3 | 4 | | IV-1 | AP3M2 | 1.19 |
| 5209 | 3 | 4 | | | IV-1 | ACY1 | 1.27 | 5305 | 3 | 4 | | IV-1 | AP3S1 | 1.48 |
| 5210 | 3 | 4 | | | IV-1 | ADAP1 | 1.30 | 5306 | 3 | 4 | | IV-1 | AP3S2 | 1.44 |
| 5211 | 3 | 4 | | | IV-1 | ADAR | 1.22 | 5307 | 3 | 4 | | IV-1 | AP4M1 | 1.32 |
| 5212 | 3 | 4 | | | IV-1 | ADARB1 | 1.21 | 5308 | 3 | 4 | | IV-1 | AP4S1 | 1.06 |
| 5213 | 3 | 4 | | | IV-1 | ADAT1 | 1.14 | 5309 | 3 | 4 | | IV-1 | AP5B1 | 1.22 |
| 5214 | 3 | 4 | | | IV-1 | ADCK2 | 1.50 | 5310 | 3 | 4 | | IV-1 | APAF1 | 1.36 |
| 5215 | 3 | 4 | | | IV-1 | ADCK3 | 1.02 | 5311 | 3 | 4 | | IV-1 | APBA3 | 1.21 |
| 5216 | 3 | 4 | | | IV-1 | ADCK4 | 1.18 | 5312 | 3 | 4 | | IV-1 | APC | 1.09 |
| 5217 | 3 | 4 | | | IV-1 | ADD1 | 1.33 | 5313 | 3 | 4 | | IV-1 | APEX1 | 1.10 |
| 5218 | 3 | 4 | | | IV-1 | ADD2 | 1.25 | 5314 | 3 | 4 | | IV-1 | APEX2 | 1.48 |
| 5219 | 3 | 4 | | | IV-1 | ADD3 | 1.29 | 5315 | 3 | 4 | | IV-1 | APH1A | 1.34 |
| 5220 | 3 | 4 | | | IV-1 | ADH5 | 1.29 | 5316 | 3 | 4 | | IV-1 | APIP | 1.22 |
| 5221 | 3 | 4 | | | IV-1 | ADI1 | 1.12 | 5317 | 3 | 4 | | IV-1 | APITD1 | 1.00 |
| 5222 | 3 | 4 | | | IV-1 | ADIPOR2 | 1.36 | 5318 | 3 | 4 | | IV-1 | APOA1BP | 1.17 |
| 5223 | 3 | 4 | | | IV-1 | ADM2 | 1.03 | 5319 | 3 | 4 | | IV-1 | APOBEC3D | 1.04 |
| 5224 | 3 | 4 | | | IV-1 | ADPGK | 1.39 | 5320 | 3 | 4 | | IV-1 | APOBEC3F | 1.09 |
| 5225 | 3 | 4 | | | IV-1 | ADPRHL2 | 1.10 | 5321 | 3 | 4 | | IV-1 | APOBEC3G | 1.05 |
| 5226 | 3 | 4 | | | IV-1 | ADRBK1 | 1.15 | 5322 | 3 | 4 | | IV-1 | APOBR | 1.41 |
| 5227 | 3 | 4 | | | IV-1 | ADRM1 | 1.46 | 5323 | 3 | 4 | | IV-1 | APOL3 | 1.32 |
| 5228 | 3 | 4 | | | IV-1 | AEN | 1.27 | 5324 | 3 | 4 | | IV-1 | APPBP2 | 1.37 |
| 5229 | 3 | 4 | | | IV-1 | AFF1 | 1.24 | 5325 | 3 | 4 | | IV-1 | AQP9 | 1.13 |
| 5230 | 3 | 4 | | | IV-1 | AGAP2 | 1.07 | 5326 | 3 | 4 | | IV-1 | ARAF | 1.25 |
| 5231 | 3 | 4 | | | IV-1 | AGFG2 | 1.28 | 5327 | 3 | 4 | | IV-1 | ARAP1 | 1.05 |
| 5232 | 3 | 4 | | | IV-1 | AGK | 1.13 | 5328 | 3 | 4 | | IV-1 | ARAP2 | 1.20 |
| 5233 | 3 | 4 | | | IV-1 | AGPAT1 | 1.05 | 5329 | 3 | 4 | | IV-1 | ARF5 | 1.05 |
| 5234 | 3 | 4 | | | IV-1 | AGPAT4 | 1.39 | 5330 | 3 | 4 | | IV-1 | ARFGAP1 | 1.17 |
| 5235 | 3 | 4 | | | IV-1 | AGTPBP1 | 1.43 | 5331 | 3 | 4 | | IV-1 | ARFGEF1 | 1.49 |
| 5236 | 3 | 4 | | | IV-1 | AGXT2L2 | 1.42 | 5332 | 3 | 4 | | IV-1 | ARFIP2 | 1.14 |
| 5237 | 3 | 4 | | | IV-1 | AHCY | 1.36 | 5333 | 3 | 4 | | IV-1 | ARHGAP12 | 1.02 |
| 5238 | 3 | 4 | | | IV-1 | AHSA1 | 1.47 | 5334 | 3 | 4 | | IV-1 | ARHGAP15 | 1.14 |
| 5239 | 3 | 4 | | | IV-1 | AIDA | 1.35 | 5335 | 3 | 4 | | IV-1 | ARHGAP19 | 1.37 |
| 5240 | 3 | 4 | | | IV-1 | AIG1 | 1.10 | 5336 | 3 | 4 | | IV-1 | ARHGAP30 | 1.37 |
| 5241 | 3 | 4 | | | IV-1 | AIP | 1.13 | 5337 | 3 | 4 | | IV-1 | ARHGAP4 | 1.01 |
| 5242 | 3 | 4 | | | IV-1 | AK3 | 1.24 | 5338 | 3 | 4 | | IV-1 | ARHGDIA | 1.42 |
| 5243 | 3 | 4 | | | IV-1 | AKAP1 | 1.20 | 5339 | 3 | 4 | | IV-1 | ARHGDIB | 1.01 |
| 5244 | 3 | 4 | | | IV-1 | AKAP10 | 1.30 | 5340 | 3 | 4 | | IV-1 | ARHGEF1 | 1.10 |
| 5245 | 3 | 4 | | | IV-1 | AKAP8 | 1.17 | 5341 | 3 | 4 | | IV-1 | ARHGEF18 | 1.48 |
| 5246 | 3 | 4 | | | IV-1 | AKAP8L | 1.32 | 5342 | 3 | 4 | | IV-1 | ARHGEF2 | 1.26 |
| 5247 | 3 | 4 | | | IV-1 | AKIRIN1 | 1.15 | 5343 | 3 | 4 | | IV-1 | ARHGEF3 | 1.44 |
| 5248 | 3 | 4 | | | IV-1 | AKIRIN2 | 1.13 | 5344 | 3 | 4 | | IV-1 | ARHGEF35 | 1.07 |
| 5249 | 3 | 4 | | | IV-1 | AKNA | 1.06 | 5345 | 3 | 4 | | IV-1 | ARHGEF40 | 1.45 |
| 5250 | 3 | 4 | | | IV-1 | AKR1B1 | 1.30 | 5346 | 3 | 4 | | IV-1 | ARID1A | 1.45 |
| 5251 | 3 | 4 | | | IV-1 | AKT1S1 | 1.10 | 5347 | 3 | 4 | | IV-1 | ARID2 | 1.47 |
| 5252 | 3 | 4 | | | IV-1 | AKT2 | 1.06 | 5348 | 3 | 4 | | IV-1 | ARID3A | 1.20 |
| 5253 | 3 | 4 | | | IV-1 | ALAS1 | 1.25 | 5349 | 3 | 4 | | IV-1 | ARID4A | 1.39 |
| 5254 | 3 | 4 | | | IV-1 | ALDH1B1 | 1.36 | 5350 | 3 | 4 | | IV-1 | ARID5B | 1.50 |
| 5255 | 3 | 4 | | | IV-1 | ALDOC | 1.23 | 5351 | 3 | 4 | | IV-1 | ARIH1 | 1.40 |
| 5256 | 3 | 4 | | | IV-1 | ALG12 | 1.45 | 5352 | 3 | 4 | | IV-1 | ARIH2 | 1.03 |
| 5257 | 3 | 4 | | | IV-1 | ALG13 | 1.21 | 5353 | 3 | 4 | | IV-1 | ARL1 | 1.33 |
| 5258 | 3 | 4 | | | IV-1 | ALG9 | 1.08 | 5354 | 3 | 4 | | IV-1 | ARL11 | 1.43 |
| 5259 | 3 | 4 | | | IV-1 | ALKBH1 | 1.50 | 5355 | 3 | 4 | | IV-1 | ARL13B | 1.17 |
| 5260 | 3 | 4 | | | IV-1 | ALKBH3 | 1.13 | 5356 | 3 | 4 | | IV-1 | ARL2 | 1.32 |
| 5261 | 3 | 4 | | | IV-1 | ALKBH4 | 1.46 | 5357 | 3 | 4 | | IV-1 | ARL4C | 1.27 |
| 5262 | 3 | 4 | | | IV-1 | ALKBH5 | 1.29 | 5358 | 3 | 4 | | IV-1 | ARL5B | 1.42 |
| 5263 | 3 | 4 | | | IV-1 | ALKBH6 | 1.07 | 5359 | 3 | 4 | | IV-1 | ARL6IP4 | 1.13 |
| 5264 | 3 | 4 | | | IV-1 | ALKBH8 | 1.42 | 5360 | 3 | 4 | | IV-1 | ARL6IP6 | 1.16 |
| 5265 | 3 | 4 | | | IV-1 | ALOX5 | 1.45 | 5361 | 3 | 4 | | IV-1 | ARL8A | 1.07 |
| 5266 | 3 | 4 | | | IV-1 | ALS2 | 1.21 | 5362 | 3 | 4 | | IV-1 | ARMC7 | 1.44 |
| 5267 | 3 | 4 | | | IV-1 | AMICA1 | 1.23 | 5363 | 3 | 4 | | IV-1 | ARMCX1 | 1.27 |
| 5268 | 3 | 4 | | | IV-1 | AMMECR1L | 1.25 | 5364 | 3 | 4 | | IV-1 | ARMCX2 | 1.37 |
| 5269 | 3 | 4 | | | IV-1 | AMPD3 | 1.39 | 5365 | 3 | 4 | | IV-1 | ARMCX5 | 1.45 |
| 5270 | 3 | 4 | | | IV-1 | ANAPC1 | 1.36 | 5366 | 3 | 4 | | IV-1 | ARMCX6 | 1.27 |
| 5271 | 3 | 4 | | | IV-1 | ANAPC10 | 1.21 | 5367 | 3 | 4 | | IV-1 | ARNTL | 1.03 |
| 5272 | 3 | 4 | | | IV-1 | ANAPC13 | 1.25 | 5368 | 3 | 4 | | IV-1 | ARPC2 | 1.32 |
| 5273 | 3 | 4 | | | IV-1 | ANAPC16 | 1.13 | 5369 | 3 | 4 | | IV-1 | ARPC3 | 1.26 |
| 5274 | 3 | 4 | | | IV-1 | ANAPC4 | 1.28 | 5370 | 3 | 4 | | IV-1 | ARPC5L | 1.50 |
| 5275 | 3 | 4 | | | IV-1 | ANAPC5 | 1.31 | 5371 | 3 | 4 | | IV-1 | ARPP19 | 1.08 |

Fig. 41 - 29

| | | | | | | | | | | | | | | | |
|---|---|---|---|---|---|---|---|---|---|---|---|---|---|---|---|
| 5372 | 3 | 4 | | | IV-1 | ARRB1 | 1.46 | 5468 | 3 | 4 | | | IV-1 | BCAS3 | 1.30 |
| 5373 | 3 | 4 | | | IV-1 | ARRDC1 | 1.25 | 5469 | 3 | 4 | | | IV-1 | BCDIN3D | 1.14 |
| 5374 | 3 | 4 | | | IV-1 | ARRDC2 | 1.13 | 5470 | 3 | 4 | | | IV-1 | BCKDHA | 1.33 |
| 5375 | 3 | 4 | | | IV-1 | ARSA | 1.34 | 5471 | 3 | 4 | | | IV-1 | BCL2 | 1.42 |
| 5376 | 3 | 4 | | | IV-1 | ARSK | 1.05 | 5472 | 3 | 4 | | | IV-1 | BCL2L11 | 1.24 |
| 5377 | 3 | 4 | | | IV-1 | ASAP1 | 1.28 | 5473 | 3 | 4 | | | IV-1 | BCL7B | 1.07 |
| 5378 | 3 | 4 | | | IV-1 | ASB1 | 1.43 | 5474 | 3 | 4 | | | IV-1 | BCL7C | 1.25 |
| 5379 | 3 | 4 | | | IV-1 | ASB6 | 1.21 | 5475 | 3 | 4 | | | IV-1 | BCLAF1 | 1.35 |
| 5380 | 3 | 4 | | | IV-1 | ASB7 | 1.36 | 5476 | 3 | 4 | | | IV-1 | BCORL1 | 1.19 |
| 5381 | 3 | 4 | | | IV-1 | ASB8 | 1.40 | 5477 | 3 | 4 | | | IV-1 | BCR | 1.20 |
| 5382 | 3 | 4 | | | IV-1 | ASCC1 | 1.11 | 5478 | 3 | 4 | | | IV-1 | BCRP3 | 1.12 |
| 5383 | 3 | 4 | | | IV-1 | ASH1L | 1.19 | 5479 | 3 | 4 | | | IV-1 | BCS1L | 1.14 |
| 5384 | 3 | 4 | | | IV-1 | ASMTL | 1.01 | 5480 | 3 | 4 | | | IV-1 | BET1 | 1.44 |
| 5385 | 3 | 4 | | | IV-1 | ASNA1 | 1.19 | 5481 | 3 | 4 | | | IV-1 | BET1L | 1.01 |
| 5386 | 3 | 4 | | | IV-1 | ASNS | 1.30 | 5482 | 3 | 4 | | | IV-1 | BEX5 | 1.12 |
| 5387 | 3 | 4 | | | IV-1 | ASTE1 | 1.26 | 5483 | 3 | 4 | | | IV-1 | BICD2 | 1.36 |
| 5388 | 3 | 4 | | | IV-1 | ASXL1 | 1.26 | 5484 | 3 | 4 | | | IV-1 | BID | 1.01 |
| 5389 | 3 | 4 | | | IV-1 | ATAD1 | 1.44 | 5485 | 3 | 4 | | | IV-1 | BIN3 | 1.31 |
| 5390 | 3 | 4 | | | IV-1 | ATAD3B | 1.16 | 5486 | 3 | 4 | | | IV-1 | BIRC2 | 1.25 |
| 5391 | 3 | 4 | | | IV-1 | ATE1 | 1.35 | 5487 | 3 | 4 | | | IV-1 | BLCAP | 1.26 |
| 5392 | 3 | 4 | | | IV-1 | ATF1 | 1.17 | 5488 | 3 | 4 | | | IV-1 | BLM | 1.27 |
| 5393 | 3 | 4 | | | IV-1 | ATG12 | 1.12 | 5489 | 3 | 4 | | | IV-1 | BLOC1S3 | 1.27 |
| 5394 | 3 | 4 | | | IV-1 | ATG13 | 1.12 | 5490 | 3 | 4 | | | IV-1 | BLZF1 | 1.16 |
| 5395 | 3 | 4 | | | IV-1 | ATG14 | 1.23 | 5491 | 3 | 4 | | | IV-1 | BMP8B | 1.18 |
| 5396 | 3 | 4 | | | IV-1 | ATG2B | 1.22 | 5492 | 3 | 4 | | | IV-1 | BMPR1A | 1.01 |
| 5397 | 3 | 4 | | | IV-1 | ATG3 | 1.47 | 5493 | 3 | 4 | | | IV-1 | BNIP1 | 1.15 |
| 5398 | 3 | 4 | | | IV-1 | ATG4A | 1.36 | 5494 | 3 | 4 | | | IV-1 | BNIP3 | 1.46 |
| 5399 | 3 | 4 | | | IV-1 | ATG4B | 1.06 | 5495 | 3 | 4 | | | IV-1 | BOD1L | 1.35 |
| 5400 | 3 | 4 | | | IV-1 | ATG4D | 1.22 | 5496 | 3 | 4 | | | IV-1 | BOLA1 | 1.20 |
| 5401 | 3 | 4 | | | IV-1 | ATG5 | 1.50 | 5497 | 3 | 4 | | | IV-1 | BOLA2 | 1.38 |
| 5402 | 3 | 4 | | | IV-1 | ATG9A | 1.26 | 5498 | 3 | 4 | | | IV-1 | BPNT1 | 1.37 |
| 5403 | 3 | 4 | | | IV-1 | ATIC | 1.33 | 5499 | 3 | 4 | | | IV-1 | BPTF | 1.48 |
| 5404 | 3 | 4 | | | IV-1 | ATL2 | 1.13 | 5500 | 3 | 4 | | | IV-1 | BRAF | 1.06 |
| 5405 | 3 | 4 | | | IV-1 | ATM | 1.08 | 5501 | 3 | 4 | | | IV-1 | BRAT1 | 1.48 |
| 5406 | 3 | 4 | | | IV-1 | ATN1 | 1.42 | 5502 | 3 | 4 | | | IV-1 | BRD1 | 1.46 |
| 5407 | 3 | 4 | | | IV-1 | ATP11B | 1.21 | 5503 | 3 | 4 | | | IV-1 | BRD4 | 1.23 |
| 5408 | 3 | 4 | | | IV-1 | ATP1A3 | 1.06 | 5504 | 3 | 4 | | | IV-1 | BRD7 | 1.12 |
| 5409 | 3 | 4 | | | IV-1 | ATP5D | 1.42 | 5505 | 3 | 4 | | | IV-1 | BRF2 | 1.44 |
| 5410 | 3 | 4 | | | IV-1 | ATP5EP2 | 1.26 | 5506 | 3 | 4 | | | IV-1 | BRI3BP | 1.48 |
| 5411 | 3 | 4 | | | IV-1 | ATP5G1 | 1.21 | 5507 | 3 | 4 | | | IV-1 | BRIX1 | 1.15 |
| 5412 | 3 | 4 | | | IV-1 | ATP5O | 1.30 | 5508 | 3 | 4 | | | IV-1 | BRK1 | 1.37 |
| 5413 | 3 | 4 | | | IV-1 | ATP5S | 1.49 | 5509 | 3 | 4 | | | IV-1 | BRMS1 | 1.42 |
| 5414 | 3 | 4 | | | IV-1 | ATP6AP1L | 1.15 | 5510 | 3 | 4 | | | IV-1 | BRMS1L | 1.16 |
| 5415 | 3 | 4 | | | IV-1 | ATP6V0A2 | 1.07 | 5511 | 3 | 4 | | | IV-1 | BRP44 | 1.03 |
| 5416 | 3 | 4 | | | IV-1 | ATP6V0C | 1.13 | 5512 | 3 | 4 | | | IV-1 | BRP44L | 1.36 |
| 5417 | 3 | 4 | | | IV-1 | ATP6V0E1 | 1.49 | 5513 | 3 | 4 | | | IV-1 | BRPF1 | 1.42 |
| 5418 | 3 | 4 | | | IV-1 | ATP6V0E2 | 1.04 | 5514 | 3 | 4 | | | IV-1 | BRWD1 | 1.39 |
| 5419 | 3 | 4 | | | IV-1 | ATP6V1F | 1.14 | 5515 | 3 | 4 | | | IV-1 | BSDC1 | 1.05 |
| 5420 | 3 | 4 | | | IV-1 | ATP7A | 1.29 | 5516 | 3 | 4 | | | IV-1 | BTAF1 | 1.35 |
| 5421 | 3 | 4 | | | IV-1 | ATP8A1 | 1.05 | 5517 | 3 | 4 | | | IV-1 | BTBD10 | 1.35 |
| 5422 | 3 | 4 | | | IV-1 | ATP8B5P | 1.19 | 5518 | 3 | 4 | | | IV-1 | BTBD2 | 1.47 |
| 5423 | 3 | 4 | | | IV-1 | ATP9B | 1.21 | 5519 | 3 | 4 | | | IV-1 | BTBD6 | 1.16 |
| 5424 | 3 | 4 | | | IV-1 | ATPIF1 | 1.02 | 5520 | 3 | 4 | | | IV-1 | BTBD7 | 1.27 |
| 5425 | 3 | 4 | | | IV-1 | ATRIP | 1.14 | 5521 | 3 | 4 | | | IV-1 | BTF3 | 1.40 |
| 5426 | 3 | 4 | | | IV-1 | ATXN1 | 1.37 | 5522 | 3 | 4 | | | IV-1 | BTF3L4 | 1.32 |
| 5427 | 3 | 4 | | | IV-1 | ATXN1L | 1.26 | 5523 | 3 | 4 | | | IV-1 | BTG1 | 1.27 |
| 5428 | 3 | 4 | | | IV-1 | ATXN2L | 1.31 | 5524 | 3 | 4 | | | IV-1 | BTN3A3 | 1.06 |
| 5429 | 3 | 4 | | | IV-1 | ATXN3 | 1.46 | 5525 | 3 | 4 | | | IV-1 | BUB3 | 1.31 |
| 5430 | 3 | 4 | | | IV-1 | ATXN7 | 1.08 | 5526 | 3 | 4 | | | IV-1 | BUD13 | 1.41 |
| 5431 | 3 | 4 | | | IV-1 | ATXN7L3 | 1.15 | 5527 | 3 | 4 | | | IV-1 | BUD31 | 1.14 |
| 5432 | 3 | 4 | | | IV-1 | AUH | 1.08 | 5528 | 3 | 4 | | | IV-1 | C10orf118 | 1.03 |
| 5433 | 3 | 4 | | | IV-1 | AUP1 | 1.14 | 5529 | 3 | 4 | | | IV-1 | C10orf12 | 1.19 |
| 5434 | 3 | 4 | | | IV-1 | AURKA | 1.19 | 5530 | 3 | 4 | | | IV-1 | C10orf137 | 1.32 |
| 5435 | 3 | 4 | | | IV-1 | AURKAIP1 | 1.31 | 5531 | 3 | 4 | | | IV-1 | C10orf26 | 1.23 |
| 5436 | 3 | 4 | | | IV-1 | AURKAPS1 | 1.10 | 5532 | 3 | 4 | | | IV-1 | C10orf28 | 1.44 |
| 5437 | 3 | 4 | | | IV-1 | AVL9 | 1.34 | 5533 | 3 | 4 | | | IV-1 | C10orf46 | 1.38 |
| 5438 | 3 | 4 | | | IV-1 | AXIN1 | 1.04 | 5534 | 3 | 4 | | | IV-1 | C10orf47 | 1.44 |
| 5439 | 3 | 4 | | | IV-1 | AZI1 | 1.39 | 5535 | 3 | 4 | | | IV-1 | C10orf54 | 1.29 |
| 5440 | 3 | 4 | | | IV-1 | AZIN1 | 1.50 | 5536 | 3 | 4 | | | IV-1 | C10orf58 | 1.24 |
| 5441 | 3 | 4 | | | IV-1 | B3GALTL | 1.04 | 5537 | 3 | 4 | | | IV-1 | C11orf2 | 1.38 |
| 5442 | 3 | 4 | | | IV-1 | B3GAT3 | 1.38 | 5538 | 3 | 4 | | | IV-1 | C11orf30 | 1.19 |
| 5443 | 3 | 4 | | | IV-1 | B3GNT1 | 1.44 | 5539 | 3 | 4 | | | IV-1 | C11orf31 | 1.39 |
| 5444 | 3 | 4 | | | IV-1 | B3GNT2 | 1.28 | 5540 | 3 | 4 | | | IV-1 | C11orf46 | 1.03 |
| 5445 | 3 | 4 | | | IV-1 | B3GNT5 | 1.03 | 5541 | 3 | 4 | | | IV-1 | C11orf49 | 1.17 |
| 5446 | 3 | 4 | | | IV-1 | B3GNTL1 | 1.02 | 5542 | 3 | 4 | | | IV-1 | C11orf57 | 1.34 |
| 5447 | 3 | 4 | | | IV-1 | B4GALT1 | 1.33 | 5543 | 3 | 4 | | | IV-1 | C11orf61 | 1.30 |
| 5448 | 3 | 4 | | | IV-1 | B4GALT5 | 1.32 | 5544 | 3 | 4 | | | IV-1 | C11orf68 | 1.04 |
| 5449 | 3 | 4 | | | IV-1 | B4GALT7 | 1.15 | 5545 | 3 | 4 | | | IV-1 | C11orf71 | 1.29 |
| 5450 | 3 | 4 | | | IV-1 | BABAM1 | 1.30 | 5546 | 3 | 4 | | | IV-1 | C11orf83 | 1.46 |
| 5451 | 3 | 4 | | | IV-1 | BAD | 1.17 | 5547 | 3 | 4 | | | IV-1 | C11orf84 | 1.08 |
| 5452 | 3 | 4 | | | IV-1 | BAG2 | 1.18 | 5548 | 3 | 4 | | | IV-1 | C11orf95 | 1.02 |
| 5453 | 3 | 4 | | | IV-1 | BAG5 | 1.49 | 5549 | 3 | 4 | | | IV-1 | C12orf10 | 1.40 |
| 5454 | 3 | 4 | | | IV-1 | BAK1 | 1.42 | 5550 | 3 | 4 | | | IV-1 | C12orf23 | 1.03 |
| 5455 | 3 | 4 | | | IV-1 | BANF1 | 1.42 | 5551 | 3 | 4 | | | IV-1 | C12orf26 | 1.10 |
| 5456 | 3 | 4 | | | IV-1 | BAP1 | 1.10 | 5552 | 3 | 4 | | | IV-1 | C12orf32 | 1.39 |
| 5457 | 3 | 4 | | | IV-1 | BARD1 | 1.01 | 5553 | 3 | 4 | | | IV-1 | C12orf43 | 1.43 |
| 5458 | 3 | 4 | | | IV-1 | BAZ1A | 1.36 | 5554 | 3 | 4 | | | IV-1 | C12orf45 | 1.37 |
| 5459 | 3 | 4 | | | IV-1 | BAZ2A | 1.02 | 5555 | 3 | 4 | | | IV-1 | C12orf47 | 1.04 |
| 5460 | 3 | 4 | | | IV-1 | BBS1 | 1.30 | 5556 | 3 | 4 | | | IV-1 | C12orf51 | 1.09 |
| 5461 | 3 | 4 | | | IV-1 | BBS10 | 1.07 | 5557 | 3 | 4 | | | IV-1 | C12orf52 | 1.40 |
| 5462 | 3 | 4 | | | IV-1 | BBS12 | 1.31 | 5558 | 3 | 4 | | | IV-1 | C12orf65 | 1.01 |
| 5463 | 3 | 4 | | | IV-1 | BBS2 | 1.25 | 5559 | 3 | 4 | | | IV-1 | C12orf73 | 1.32 |
| 5464 | 3 | 4 | | | IV-1 | BBS7 | 1.00 | 5560 | 3 | 4 | | | IV-1 | C12orf76 | 1.34 |
| 5465 | 3 | 4 | | | IV-1 | BBS9 | 1.09 | 5561 | 3 | 4 | | | IV-1 | C14orf1 | 1.10 |
| 5466 | 3 | 4 | | | IV-1 | BBX | 1.49 | 5562 | 3 | 4 | | | IV-1 | C14orf101 | 1.49 |
| 5467 | 3 | 4 | | | IV-1 | BCAP31 | 1.37 | 5563 | 3 | 4 | | | IV-1 | C14orf118 | 1.35 |

Fig. 41 - 30

| | | | | | | | | | | | | | | |
|---|---|---|---|---|---|---|---|---|---|---|---|---|---|---|
| 5564 | 3 | 4 | | | IV-1 | C14orf119 | 1.41 | 5660 | 3 | 4 | | | IV-1 | C4orf27 | 1.22 |
| 5565 | 3 | 4 | | | IV-1 | C14orf129 | 1.14 | 5661 | 3 | 4 | | | IV-1 | C4orf3 | 1.35 |
| 5566 | 3 | 4 | | | IV-1 | C14orf135 | 1.47 | 5662 | 3 | 4 | | | IV-1 | C4orf34 | 1.44 |
| 5567 | 3 | 4 | | | IV-1 | C14orf142 | 1.30 | 5663 | 3 | 4 | | | IV-1 | C4orf43 | 1.48 |
| 5568 | 3 | 4 | | | IV-1 | C14orf167 | 1.34 | 5664 | 3 | 4 | | | IV-1 | C4orf46 | 1.00 |
| 5569 | 3 | 4 | | | IV-1 | C14orf43 | 1.21 | 5665 | 3 | 4 | | | IV-1 | C4orf52 | 1.21 |
| 5570 | 3 | 4 | | | IV-1 | C15orf34 | 1.09 | 5666 | 3 | 4 | | | IV-1 | C5AR1 | 1.02 |
| 5571 | 3 | 4 | | | IV-1 | C15orf39 | 1.06 | 5667 | 3 | 4 | | | IV-1 | C5orf41 | 1.09 |
| 5572 | 3 | 4 | | | IV-1 | C15orf41 | 1.10 | 5668 | 3 | 4 | | | IV-1 | C5orf44 | 1.08 |
| 5573 | 3 | 4 | | | IV-1 | C15orf44 | 1.30 | 5669 | 3 | 4 | | | IV-1 | C5orf51 | 1.46 |
| 5574 | 3 | 4 | | | IV-1 | C15orf57 | 1.20 | 5670 | 3 | 4 | | | IV-1 | C5orf62 | 1.15 |
| 5575 | 3 | 4 | | | IV-1 | C15orf61 | 1.18 | 5671 | 3 | 4 | | | IV-1 | C6orf106 | 1.33 |
| 5576 | 3 | 4 | | | IV-1 | C15orf63 | 1.42 | 5672 | 3 | 4 | | | IV-1 | C6orf130 | 1.17 |
| 5577 | 3 | 4 | | | IV-1 | C16orf13 | 1.21 | 5673 | 3 | 4 | | | IV-1 | C6orf47 | 1.42 |
| 5578 | 3 | 4 | | | IV-1 | C16orf42 | 1.27 | 5674 | 3 | 4 | | | IV-1 | C6orf48 | 1.04 |
| 5579 | 3 | 4 | | | IV-1 | C16orf48 | 1.03 | 5675 | 3 | 4 | | | IV-1 | C6orf70 | 1.07 |
| 5580 | 3 | 4 | | | IV-1 | C16orf52 | 1.24 | 5676 | 3 | 4 | | | IV-1 | C6orf89 | 1.31 |
| 5581 | 3 | 4 | | | IV-1 | C16orf53 | 1.29 | 5677 | 3 | 4 | | | IV-1 | C6orf97 | 1.12 |
| 5582 | 3 | 4 | | | IV-1 | C16orf57 | 1.42 | 5678 | 3 | 4 | | | IV-1 | C7orf11 | 1.24 |
| 5583 | 3 | 4 | | | IV-1 | C16orf58 | 1.06 | 5679 | 3 | 4 | | | IV-1 | C7orf23 | 1.28 |
| 5584 | 3 | 4 | | | IV-1 | C16orf72 | 1.26 | 5680 | 3 | 4 | | | IV-1 | C7orf25 | 1.29 |
| 5585 | 3 | 4 | | | IV-1 | C16orf86 | 1.16 | 5681 | 3 | 4 | | | IV-1 | C7orf26 | 1.39 |
| 5586 | 3 | 4 | | | IV-1 | C16orf91 | 1.08 | 5682 | 3 | 4 | | | IV-1 | C7orf29 | 1.01 |
| 5587 | 3 | 4 | | | IV-1 | C17orf101 | 1.32 | 5683 | 3 | 4 | | | IV-1 | C7orf50 | 1.43 |
| 5588 | 3 | 4 | | | IV-1 | C17orf103 | 1.10 | 5684 | 3 | 4 | | | IV-1 | C7orf60 | 1.22 |
| 5589 | 3 | 4 | | | IV-1 | C17orf39 | 1.21 | 5685 | 3 | 4 | | | IV-1 | C7orf70 | 1.27 |
| 5590 | 3 | 4 | | | IV-1 | C17orf49 | 1.11 | 5686 | 3 | 4 | | | IV-1 | C8orf40 | 1.33 |
| 5591 | 3 | 4 | | | IV-1 | C17orf51 | 1.21 | 5687 | 3 | 4 | | | IV-1 | C8orf55 | 1.13 |
| 5592 | 3 | 4 | | | IV-1 | C17orf59 | 1.38 | 5688 | 3 | 4 | | | IV-1 | C8orf80 | 1.10 |
| 5593 | 3 | 4 | | | IV-1 | C17orf62 | 1.23 | 5689 | 3 | 4 | | | IV-1 | C9orf103 | 1.47 |
| 5594 | 3 | 4 | | | IV-1 | C17orf63 | 1.26 | 5690 | 3 | 4 | | | IV-1 | C9orf114 | 1.27 |
| 5595 | 3 | 4 | | | IV-1 | C17orf75 | 1.26 | 5691 | 3 | 4 | | | IV-1 | C9orf142 | 1.08 |
| 5596 | 3 | 4 | | | IV-1 | C17orf80 | 1.46 | 5692 | 3 | 4 | | | IV-1 | C9orf156 | 1.06 |
| 5597 | 3 | 4 | | | IV-1 | C17orf81 | 1.35 | 5693 | 3 | 4 | | | IV-1 | C9orf21 | 1.21 |
| 5598 | 3 | 4 | | | IV-1 | C17orf85 | 1.36 | 5694 | 3 | 4 | | | IV-1 | C9orf23 | 1.19 |
| 5599 | 3 | 4 | | | IV-1 | C17orf90 | 1.09 | 5695 | 3 | 4 | | | IV-1 | C9orf37 | 1.12 |
| 5600 | 3 | 4 | | | IV-1 | C18orf1 | 1.30 | 5696 | 3 | 4 | | | IV-1 | C9orf5 | 1.50 |
| 5601 | 3 | 4 | | | IV-1 | C18orf32 | 1.08 | 5697 | 3 | 4 | | | IV-1 | C9orf66 | 1.26 |
| 5602 | 3 | 4 | | | IV-1 | C18orf8 | 1.30 | 5698 | 3 | 4 | | | IV-1 | C9orf69 | 1.40 |
| 5603 | 3 | 4 | | | IV-1 | C19orf12 | 1.03 | 5699 | 3 | 4 | | | IV-1 | C9orf82 | 1.42 |
| 5604 | 3 | 4 | | | IV-1 | C19orf24 | 1.47 | 5700 | 3 | 4 | | | IV-1 | C9orf85 | 1.10 |
| 5605 | 3 | 4 | | | IV-1 | C19orf29 | 1.24 | 5701 | 3 | 4 | | | IV-1 | C9orf91 | 1.24 |
| 5606 | 3 | 4 | | | IV-1 | C19orf40 | 1.17 | 5702 | 3 | 4 | | | IV-1 | CA4 | 1.03 |
| 5607 | 3 | 4 | | | IV-1 | C19orf43 | 1.01 | 5703 | 3 | 4 | | | IV-1 | CA5B | 1.04 |
| 5608 | 3 | 4 | | | IV-1 | C19orf47 | 1.41 | 5704 | 3 | 4 | | | IV-1 | CAB39L | 1.12 |
| 5609 | 3 | 4 | | | IV-1 | C19orf48 | 1.14 | 5705 | 3 | 4 | | | IV-1 | CABLES2 | 1.24 |
| 5610 | 3 | 4 | | | IV-1 | C19orf63 | 1.31 | 5706 | 3 | 4 | | | IV-1 | CACNB1 | 1.21 |
| 5611 | 3 | 4 | | | IV-1 | C19orf73 | 1.06 | 5707 | 3 | 4 | | | IV-1 | CADM4 | 1.11 |
| 5612 | 3 | 4 | | | IV-1 | C1D | 1.26 | 5708 | 3 | 4 | | | IV-1 | CALD1 | 1.27 |
| 5613 | 3 | 4 | | | IV-1 | C1GALT1 | 1.14 | 5709 | 3 | 4 | | | IV-1 | CALM3 | 1.29 |
| 5614 | 3 | 4 | | | IV-1 | C1QBP | 1.13 | 5710 | 3 | 4 | | | IV-1 | CALML4 | 1.45 |
| 5615 | 3 | 4 | | | IV-1 | C1RL | 1.15 | 5711 | 3 | 4 | | | IV-1 | CAMK1D | 1.08 |
| 5616 | 3 | 4 | | | IV-1 | C1orf123 | 1.50 | 5712 | 3 | 4 | | | IV-1 | CAMK2D | 1.08 |
| 5617 | 3 | 4 | | | IV-1 | C1orf124 | 1.38 | 5713 | 3 | 4 | | | IV-1 | CAMKMT | 1.20 |
| 5618 | 3 | 4 | | | IV-1 | C1orf131 | 1.32 | 5714 | 3 | 4 | | | IV-1 | CAMLG | 1.16 |
| 5619 | 3 | 4 | | | IV-1 | C1orf144 | 1.16 | 5715 | 3 | 4 | | | IV-1 | CAMSAP2 | 1.44 |
| 5620 | 3 | 4 | | | IV-1 | C1orf200 | 1.34 | 5716 | 3 | 4 | | | IV-1 | CAMTA1 | 1.25 |
| 5621 | 3 | 4 | | | IV-1 | C1orf212 | 1.22 | 5717 | 3 | 4 | | | IV-1 | CAMTA2 | 1.33 |
| 5622 | 3 | 4 | | | IV-1 | C1orf43 | 1.45 | 5718 | 3 | 4 | | | IV-1 | CANT1 | 1.12 |
| 5623 | 3 | 4 | | | IV-1 | C1orf50 | 1.23 | 5719 | 3 | 4 | | | IV-1 | CAPN10 | 1.06 |
| 5624 | 3 | 4 | | | IV-1 | C1orf52 | 1.18 | 5720 | 3 | 4 | | | IV-1 | CAPN7 | 1.39 |
| 5625 | 3 | 4 | | | IV-1 | C1orf55 | 1.08 | 5721 | 3 | 4 | | | IV-1 | CAPZB | 1.11 |
| 5626 | 3 | 4 | | | IV-1 | C1orf74 | 1.48 | 5722 | 3 | 4 | | | IV-1 | CARHSP1 | 1.23 |
| 5627 | 3 | 4 | | | IV-1 | C1orf86 | 1.22 | 5723 | 3 | 4 | | | IV-1 | CARKD | 1.42 |
| 5628 | 3 | 4 | | | IV-1 | C1orf9 | 1.39 | 5724 | 3 | 4 | | | IV-1 | CARS | 1.43 |
| 5629 | 3 | 4 | | | IV-1 | C1orf96 | 1.50 | 5725 | 3 | 4 | | | IV-1 | CARS2 | 1.11 |
| 5630 | 3 | 4 | | | IV-1 | C20orf196 | 1.01 | 5726 | 3 | 4 | | | IV-1 | CASC4 | 1.14 |
| 5631 | 3 | 4 | | | IV-1 | C20orf20 | 1.21 | 5727 | 3 | 4 | | | IV-1 | CASD1 | 1.21 |
| 5632 | 3 | 4 | | | IV-1 | C20orf43 | 1.07 | 5728 | 3 | 4 | | | IV-1 | CASP2 | 1.24 |
| 5633 | 3 | 4 | | | IV-1 | C20orf72 | 1.18 | 5729 | 3 | 4 | | | IV-1 | CASP3 | 1.26 |
| 5634 | 3 | 4 | | | IV-1 | C20orf94 | 1.37 | 5730 | 3 | 4 | | | IV-1 | CASP8AP2 | 1.11 |
| 5635 | 3 | 4 | | | IV-1 | C21orf2 | 1.16 | 5731 | 3 | 4 | | | IV-1 | CASP9 | 1.47 |
| 5636 | 3 | 4 | | | IV-1 | C21orf33 | 1.40 | 5732 | 3 | 4 | | | IV-1 | CASZ1 | 1.43 |
| 5637 | 3 | 4 | | | IV-1 | C21orf63 | 1.06 | 5733 | 3 | 4 | | | IV-1 | CAT | 1.21 |
| 5638 | 3 | 4 | | | IV-1 | C21orf91 | 1.14 | 5734 | 3 | 4 | | | IV-1 | CBFA2T2 | 1.20 |
| 5639 | 3 | 4 | | | IV-1 | C22orf29 | 1.38 | 5735 | 3 | 4 | | | IV-1 | CBFA2T3 | 1.23 |
| 5640 | 3 | 4 | | | IV-1 | C22orf39 | 1.02 | 5736 | 3 | 4 | | | IV-1 | CBLB | 1.02 |
| 5641 | 3 | 4 | | | IV-1 | C2CD2 | 1.04 | 5737 | 3 | 4 | | | IV-1 | CBLL1 | 1.30 |
| 5642 | 3 | 4 | | | IV-1 | C2CD3 | 1.09 | 5738 | 3 | 4 | | | IV-1 | CBR4 | 1.37 |
| 5643 | 3 | 4 | | | IV-1 | C2orf28 | 1.10 | 5739 | 3 | 4 | | | IV-1 | CBX1 | 1.24 |
| 5644 | 3 | 4 | | | IV-1 | C2orf44 | 1.13 | 5740 | 3 | 4 | | | IV-1 | CBX8 | 1.38 |
| 5645 | 3 | 4 | | | IV-1 | C2orf49 | 1.02 | 5741 | 3 | 4 | | | IV-1 | CBY1 | 1.15 |
| 5646 | 3 | 4 | | | IV-1 | C2orf56 | 1.12 | 5742 | 3 | 4 | | | IV-1 | CCBL1 | 1.22 |
| 5647 | 3 | 4 | | | IV-1 | C2orf68 | 1.02 | 5743 | 3 | 4 | | | IV-1 | CCBL2 | 1.45 |
| 5648 | 3 | 4 | | | IV-1 | C2orf69 | 1.43 | 5744 | 3 | 4 | | | IV-1 | CCDC101 | 1.23 |
| 5649 | 3 | 4 | | | IV-1 | C2orf74 | 1.34 | 5745 | 3 | 4 | | | IV-1 | CCDC102A | 1.20 |
| 5650 | 3 | 4 | | | IV-1 | C2orf89 | 1.07 | 5746 | 3 | 4 | | | IV-1 | CCDC107 | 1.22 |
| 5651 | 3 | 4 | | | IV-1 | C3orf17 | 1.27 | 5747 | 3 | 4 | | | IV-1 | CCDC109B | 1.47 |
| 5652 | 3 | 4 | | | IV-1 | C3orf19 | 1.17 | 5748 | 3 | 4 | | | IV-1 | CCDC115 | 1.35 |
| 5653 | 3 | 4 | | | IV-1 | C3orf23 | 1.45 | 5749 | 3 | 4 | | | IV-1 | CCDC117 | 1.39 |
| 5654 | 3 | 4 | | | IV-1 | C3orf26 | 1.11 | 5750 | 3 | 4 | | | IV-1 | CCDC120 | 1.06 |
| 5655 | 3 | 4 | | | IV-1 | C3orf37 | 1.26 | 5751 | 3 | 4 | | | IV-1 | CCDC121 | 1.18 |
| 5656 | 3 | 4 | | | IV-1 | C3orf39 | 1.23 | 5752 | 3 | 4 | | | IV-1 | CCDC124 | 1.32 |
| 5657 | 3 | 4 | | | IV-1 | C3orf64 | 1.15 | 5753 | 3 | 4 | | | IV-1 | CCDC126 | 1.04 |
| 5658 | 3 | 4 | | | IV-1 | C3orf71 | 1.06 | 5754 | 3 | 4 | | | IV-1 | CCDC127 | 1.42 |
| 5659 | 3 | 4 | | | IV-1 | C3orf75 | 1.20 | 5755 | 3 | 4 | | | IV-1 | CCDC137 | 1.45 |

Fig. 41 - 31

| | | | | | | | | | | | | | | | |
|---|---|---|---|---|---|---|---|---|---|---|---|---|---|---|---|
| 5756 | 3 | 4 | | | IV-1 | CCDC25 | 1.25 | 5852 | 3 | 4 | | | IV-1 | CEP57 | 1.31 |
| 5757 | 3 | 4 | | | IV-1 | CCDC28A | 1.06 | 5853 | 3 | 4 | | | IV-1 | CEP63 | 1.06 |
| 5758 | 3 | 4 | | | IV-1 | CCDC28B | 1.45 | 5854 | 3 | 4 | | | IV-1 | CEP78 | 1.37 |
| 5759 | 3 | 4 | | | IV-1 | CCDC51 | 1.16 | 5855 | 3 | 4 | | | IV-1 | CEP85 | 1.41 |
| 5760 | 3 | 4 | | | IV-1 | CCDC53 | 1.34 | 5856 | 3 | 4 | | | IV-1 | CEP89 | 1.23 |
| 5761 | 3 | 4 | | | IV-1 | CCDC59 | 1.13 | 5857 | 3 | 4 | | | IV-1 | CEP97 | 1.21 |
| 5762 | 3 | 4 | | | IV-1 | CCDC61 | 1.48 | 5858 | 3 | 4 | | | IV-1 | CERK | 1.12 |
| 5763 | 3 | 4 | | | IV-1 | CCDC69 | 1.16 | 5859 | 3 | 4 | | | IV-1 | CERKL | 1.19 |
| 5764 | 3 | 4 | | | IV-1 | CCDC71 | 1.18 | 5860 | 3 | 4 | | | IV-1 | CERS5 | 1.38 |
| 5765 | 3 | 4 | | | IV-1 | CCDC71L | 1.12 | 5861 | 3 | 4 | | | IV-1 | CETN2 | 1.35 |
| 5766 | 3 | 4 | | | IV-1 | CCDC73 | 1.04 | 5862 | 3 | 4 | | | IV-1 | CFL1 | 1.37 |
| 5767 | 3 | 4 | | | IV-1 | CCDC82 | 1.19 | 5863 | 3 | 4 | | | IV-1 | CGGBP1 | 1.47 |
| 5768 | 3 | 4 | | | IV-1 | CCDC85B | 1.45 | 5864 | 3 | 4 | | | IV-1 | CHAC2 | 1.16 |
| 5769 | 3 | 4 | | | IV-1 | CCDC88C | 1.34 | 5865 | 3 | 4 | | | IV-1 | CHCHD10 | 1.48 |
| 5770 | 3 | 4 | | | IV-1 | CCDC9 | 1.21 | 5866 | 3 | 4 | | | IV-1 | CHCHD3 | 1.39 |
| 5771 | 3 | 4 | | | IV-1 | CCDC90B | 1.44 | 5867 | 3 | 4 | | | IV-1 | CHCHD4 | 1.24 |
| 5772 | 3 | 4 | | | IV-1 | CCDC94 | 1.07 | 5868 | 3 | 4 | | | IV-1 | CHCHD5 | 1.18 |
| 5773 | 3 | 4 | | | IV-1 | CCDC96 | 1.47 | 5869 | 3 | 4 | | | IV-1 | CHCHD7 | 1.05 |
| 5774 | 3 | 4 | | | IV-1 | CCDC97 | 1.27 | 5870 | 3 | 4 | | | IV-1 | CHCHD8 | 1.48 |
| 5775 | 3 | 4 | | | IV-1 | CCDC99 | 1.12 | 5871 | 3 | 4 | | | IV-1 | CHD1 | 1.48 |
| 5776 | 3 | 4 | | | IV-1 | CCHCR1 | 1.20 | 5872 | 3 | 4 | | | IV-1 | CHD1L | 1.06 |
| 5777 | 3 | 4 | | | IV-1 | CCM2 | 1.16 | 5873 | 3 | 4 | | | IV-1 | CHD2 | 1.17 |
| 5778 | 3 | 4 | | | IV-1 | CCNA2 | 1.18 | 5874 | 3 | 4 | | | IV-1 | CHD3 | 1.29 |
| 5779 | 3 | 4 | | | IV-1 | CCNB1 | 1.06 | 5875 | 3 | 4 | | | IV-1 | CHD6 | 1.31 |
| 5780 | 3 | 4 | | | IV-1 | CCNC | 1.33 | 5876 | 3 | 4 | | | IV-1 | CHD8 | 1.33 |
| 5781 | 3 | 4 | | | IV-1 | CCND3 | 1.09 | 5877 | 3 | 4 | | | IV-1 | CHD9 | 1.49 |
| 5782 | 3 | 4 | | | IV-1 | CCNDBP1 | 1.18 | 5878 | 3 | 4 | | | IV-1 | CHEK2 | 1.02 |
| 5783 | 3 | 4 | | | IV-1 | CCNF | 1.33 | 5879 | 3 | 4 | | | IV-1 | CHERP | 1.31 |
| 5784 | 3 | 4 | | | IV-1 | CCNH | 1.24 | 5880 | 3 | 4 | | | IV-1 | CHFR | 1.39 |
| 5785 | 3 | 4 | | | IV-1 | CCNI | 1.19 | 5881 | 3 | 4 | | | IV-1 | CHIC2 | 1.03 |
| 5786 | 3 | 4 | | | IV-1 | CCNK | 1.42 | 5882 | 3 | 4 | | | IV-1 | CHID1 | 1.42 |
| 5787 | 3 | 4 | | | IV-1 | CCNT1 | 1.44 | 5883 | 3 | 4 | | | IV-1 | CHMP1A | 1.27 |
| 5788 | 3 | 4 | | | IV-1 | CCP110 | 1.30 | 5884 | 3 | 4 | | | IV-1 | CHMP1B | 1.17 |
| 5789 | 3 | 4 | | | IV-1 | CCPG1 | 1.22 | 5885 | 3 | 4 | | | IV-1 | CHMP2A | 1.20 |
| 5790 | 3 | 4 | | | IV-1 | CCR10 | 1.14 | 5886 | 3 | 4 | | | IV-1 | CHMP3 | 1.17 |
| 5791 | 3 | 4 | | | IV-1 | CCS | 1.16 | 5887 | 3 | 4 | | | IV-1 | CHMP4A | 1.36 |
| 5792 | 3 | 4 | | | IV-1 | CCT4 | 1.39 | 5888 | 3 | 4 | | | IV-1 | CHMP6 | 1.17 |
| 5793 | 3 | 4 | | | IV-1 | CCT7 | 1.31 | 5889 | 3 | 4 | | | IV-1 | CHMP7 | 1.37 |
| 5794 | 3 | 4 | | | IV-1 | CCZ1 | 1.21 | 5890 | 3 | 4 | | | IV-1 | CHPF2 | 1.40 |
| 5795 | 3 | 4 | | | IV-1 | CD1A | 1.14 | 5891 | 3 | 4 | | | IV-1 | CHRAC1 | 1.24 |
| 5796 | 3 | 4 | | | IV-1 | CD1E | 1.27 | 5892 | 3 | 4 | | | IV-1 | CHRNB1 | 1.38 |
| 5797 | 3 | 4 | | | IV-1 | CD2BP2 | 1.11 | 5893 | 3 | 4 | | | IV-1 | CHST12 | 1.08 |
| 5798 | 3 | 4 | | | IV-1 | CD300A | 1.03 | 5894 | 3 | 4 | | | IV-1 | CHSY1 | 1.35 |
| 5799 | 3 | 4 | | | IV-1 | CD300LF | 1.35 | 5895 | 3 | 4 | | | IV-1 | CHTOP | 1.31 |
| 5800 | 3 | 4 | | | IV-1 | CD37 | 1.16 | 5896 | 3 | 4 | | | IV-1 | CHUK | 1.35 |
| 5801 | 3 | 4 | | | IV-1 | CD38 | 1.08 | 5897 | 3 | 4 | | | IV-1 | CHURC1 | 1.20 |
| 5802 | 3 | 4 | | | IV-1 | CD3EAP | 1.34 | 5898 | 3 | 4 | | | IV-1 | CIAO1 | 1.25 |
| 5803 | 3 | 4 | | | IV-1 | CD46 | 1.34 | 5899 | 3 | 4 | | | IV-1 | CIB1 | 1.15 |
| 5804 | 3 | 4 | | | IV-1 | CD47 | 1.06 | 5900 | 3 | 4 | | | IV-1 | CIC | 1.18 |
| 5805 | 3 | 4 | | | IV-1 | CD48 | 1.09 | 5901 | 3 | 4 | | | IV-1 | CIDEB | 1.45 |
| 5806 | 3 | 4 | | | IV-1 | CD55 | 1.05 | 5902 | 3 | 4 | | | IV-1 | CINP | 1.21 |
| 5807 | 3 | 4 | | | IV-1 | CD59 | 1.14 | 5903 | 3 | 4 | | | IV-1 | CISD3 | 1.23 |
| 5808 | 3 | 4 | | | IV-1 | CD6 | 1.14 | 5904 | 3 | 4 | | | IV-1 | CIZ1 | 1.14 |
| 5809 | 3 | 4 | | | IV-1 | CD7 | 1.03 | 5905 | 3 | 4 | | | IV-1 | CLASP1 | 1.35 |
| 5810 | 3 | 4 | | | IV-1 | CD83 | 1.02 | 5906 | 3 | 4 | | | IV-1 | CLCC1 | 1.49 |
| 5811 | 3 | 4 | | | IV-1 | CD97 | 1.06 | 5907 | 3 | 4 | | | IV-1 | CLEC4A | 1.50 |
| 5812 | 3 | 4 | | | IV-1 | CDA | 1.13 | 5908 | 3 | 4 | | | IV-1 | CLIC1 | 1.24 |
| 5813 | 3 | 4 | | | IV-1 | CDAN1 | 1.13 | 5909 | 3 | 4 | | | IV-1 | CLIP1 | 1.42 |
| 5814 | 3 | 4 | | | IV-1 | CDC20 | 1.09 | 5910 | 3 | 4 | | | IV-1 | CLK2P | 1.13 |
| 5815 | 3 | 4 | | | IV-1 | CDC25B | 1.07 | 5911 | 3 | 4 | | | IV-1 | CLNS1A | 1.44 |
| 5816 | 3 | 4 | | | IV-1 | CDC37 | 1.28 | 5912 | 3 | 4 | | | IV-1 | CLP1 | 1.28 |
| 5817 | 3 | 4 | | | IV-1 | CDC42 | 1.37 | 5913 | 3 | 4 | | | IV-1 | CLPP | 1.35 |
| 5818 | 3 | 4 | | | IV-1 | CDC42EP3 | 1.29 | 5914 | 3 | 4 | | | IV-1 | CLPTM1 | 1.48 |
| 5819 | 3 | 4 | | | IV-1 | CDC7 | 1.45 | 5915 | 3 | 4 | | | IV-1 | CLPX | 1.40 |
| 5820 | 3 | 4 | | | IV-1 | CDIPT | 1.21 | 5916 | 3 | 4 | | | IV-1 | CLSTN3 | 1.17 |
| 5821 | 3 | 4 | | | IV-1 | CDK11A | 1.40 | 5917 | 3 | 4 | | | IV-1 | CLTB | 1.48 |
| 5822 | 3 | 4 | | | IV-1 | CDK11B | 1.12 | 5918 | 3 | 4 | | | IV-1 | CLTCL1 | 1.27 |
| 5823 | 3 | 4 | | | IV-1 | CDK12 | 1.18 | 5919 | 3 | 4 | | | IV-1 | CMC2 | 1.43 |
| 5824 | 3 | 4 | | | IV-1 | CDK13 | 1.36 | 5920 | 3 | 4 | | | IV-1 | CMIP | 1.37 |
| 5825 | 3 | 4 | | | IV-1 | CDK14 | 1.08 | 5921 | 3 | 4 | | | IV-1 | CMPK1 | 1.34 |
| 5826 | 3 | 4 | | | IV-1 | CDK16 | 1.01 | 5922 | 3 | 4 | | | IV-1 | CMTM6 | 1.31 |
| 5827 | 3 | 4 | | | IV-1 | CDK17 | 1.29 | 5923 | 3 | 4 | | | IV-1 | CNBP | 1.49 |
| 5828 | 3 | 4 | | | IV-1 | CDK19 | 1.34 | 5924 | 3 | 4 | | | IV-1 | CNEP1R1 | 1.27 |
| 5829 | 3 | 4 | | | IV-1 | CDK2 | 1.15 | 5925 | 3 | 4 | | | IV-1 | CNIH4 | 1.47 |
| 5830 | 3 | 4 | | | IV-1 | CDK2AP2 | 1.36 | 5926 | 3 | 4 | | | IV-1 | CNN2 | 1.09 |
| 5831 | 3 | 4 | | | IV-1 | CDK5RAP1 | 1.05 | 5927 | 3 | 4 | | | IV-1 | CNNM3 | 1.03 |
| 5832 | 3 | 4 | | | IV-1 | CDK5RAP2 | 1.21 | 5928 | 3 | 4 | | | IV-1 | CNO | 1.44 |
| 5833 | 3 | 4 | | | IV-1 | CDK7 | 1.06 | 5929 | 3 | 4 | | | IV-1 | CNOT10 | 1.42 |
| 5834 | 3 | 4 | | | IV-1 | CDK9 | 1.29 | 5930 | 3 | 4 | | | IV-1 | CNOT6L | 1.22 |
| 5835 | 3 | 4 | | | IV-1 | CDKAL1 | 1.43 | 5931 | 3 | 4 | | | IV-1 | CNOT7 | 1.48 |
| 5836 | 3 | 4 | | | IV-1 | CDKN2A | 1.42 | 5932 | 3 | 4 | | | IV-1 | CNPY2 | 1.33 |
| 5837 | 3 | 4 | | | IV-1 | CDKN2AIP | 1.01 | 5933 | 3 | 4 | | | IV-1 | CNPY3 | 1.17 |
| 5838 | 3 | 4 | | | IV-1 | CDR2 | 1.15 | 5934 | 3 | 4 | | | IV-1 | CNPY4 | 1.47 |
| 5839 | 3 | 4 | | | IV-1 | CDT1 | 1.12 | 5935 | 3 | 4 | | | IV-1 | CNST | 1.05 |
| 5840 | 3 | 4 | | | IV-1 | CELF1 | 1.18 | 5936 | 3 | 4 | | | IV-1 | CNTD1 | 1.16 |
| 5841 | 3 | 4 | | | IV-1 | CELF2 | 1.07 | 5937 | 3 | 4 | | | IV-1 | CNTRL | 1.43 |
| 5842 | 3 | 4 | | | IV-1 | CENPN | 1.48 | 5938 | 3 | 4 | | | IV-1 | CNTROB | 1.44 |
| 5843 | 3 | 4 | | | IV-1 | CENPO | 1.33 | 5939 | 3 | 4 | | | IV-1 | COASY | 1.40 |
| 5844 | 3 | 4 | | | IV-1 | CEP104 | 1.38 | 5940 | 3 | 4 | | | IV-1 | COBRA1 | 1.48 |
| 5845 | 3 | 4 | | | IV-1 | CEP120 | 1.14 | 5941 | 3 | 4 | | | IV-1 | COG1 | 1.36 |
| 5846 | 3 | 4 | | | IV-1 | CEP164 | 1.41 | 5942 | 3 | 4 | | | IV-1 | COG3 | 1.03 |
| 5847 | 3 | 4 | | | IV-1 | CEP170P1 | 1.10 | 5943 | 3 | 4 | | | IV-1 | COG4 | 1.40 |
| 5848 | 3 | 4 | | | IV-1 | CEP192 | 1.20 | 5944 | 3 | 4 | | | IV-1 | COMMD2 | 1.19 |
| 5849 | 3 | 4 | | | IV-1 | CEP250 | 1.49 | 5945 | 3 | 4 | | | IV-1 | COMMD7 | 1.34 |
| 5850 | 3 | 4 | | | IV-1 | CEP44 | 1.02 | 5946 | 3 | 4 | | | IV-1 | COMMD8 | 1.29 |
| 5851 | 3 | 4 | | | IV-1 | CEP55 | 1.08 | 5947 | 3 | 4 | | | IV-1 | COPE | 1.07 |

Fig. 41 - 32

| | | | | | | | | | | | | | | |
|---|---|---|---|---|---|---|---|---|---|---|---|---|---|---|
| 5948 | 3 | 4 | | | IV-1 | COPS3 | 1.29 | 6044 | 3 | 4 | | | IV-1 | CXorf40A | 1.29 |
| 5949 | 3 | 4 | | | IV-1 | COPS5 | 1.34 | 6045 | 3 | 4 | | | IV-1 | CXorf56 | 1.31 |
| 5950 | 3 | 4 | | | IV-1 | COPS7B | 1.03 | 6046 | 3 | 4 | | | IV-1 | CY856ID1 | 1.10 |
| 5951 | 3 | 4 | | | IV-1 | COPS8 | 1.45 | 6047 | 3 | 4 | | | IV-1 | CYB5R1 | 1.48 |
| 5952 | 3 | 4 | | | IV-1 | COPZ1 | 1.33 | 6048 | 3 | 4 | | | IV-1 | CYB5R3 | 1.41 |
| 5953 | 3 | 4 | | | IV-1 | COQ10B | 1.15 | 6049 | 3 | 4 | | | IV-1 | CYB5R4 | 1.27 |
| 5954 | 3 | 4 | | | IV-1 | COQ4 | 1.18 | 6050 | 3 | 4 | | | IV-1 | CYBASC3 | 1.32 |
| 5955 | 3 | 4 | | | IV-1 | COQ6 | 1.15 | 6051 | 3 | 4 | | | IV-1 | CYBRD1 | 1.47 |
| 5956 | 3 | 4 | | | IV-1 | COQ7 | 1.04 | 6052 | 3 | 4 | | | IV-1 | CYFIP2 | 1.20 |
| 5957 | 3 | 4 | | | IV-1 | COQ9 | 1.12 | 6053 | 3 | 4 | | | IV-1 | CYHR1 | 1.10 |
| 5958 | 3 | 4 | | | IV-1 | CORO1A | 1.32 | 6054 | 3 | 4 | | | IV-1 | CYLD | 1.18 |
| 5959 | 3 | 4 | | | IV-1 | CORO7 | 1.27 | 6055 | 3 | 4 | | | IV-1 | CYP2U1 | 1.20 |
| 5960 | 3 | 4 | | | IV-1 | COX11 | 1.29 | 6056 | 3 | 4 | | | IV-1 | CYTH1 | 1.25 |
| 5961 | 3 | 4 | | | IV-1 | COX14 | 1.22 | 6057 | 3 | 4 | | | IV-1 | CYTIP | 1.16 |
| 5962 | 3 | 4 | | | IV-1 | COX18 | 1.21 | 6058 | 3 | 4 | | | IV-1 | DAAM1 | 1.48 |
| 5963 | 3 | 4 | | | IV-1 | COX19 | 1.31 | 6059 | 3 | 4 | | | IV-1 | DACH1 | 1.26 |
| 5964 | 3 | 4 | | | IV-1 | COX20 | 1.37 | 6060 | 3 | 4 | | | IV-1 | DAD1 | 1.25 |
| 5965 | 3 | 4 | | | IV-1 | COX4I1 | 1.27 | 6061 | 3 | 4 | | | IV-1 | DAP | 1.44 |
| 5966 | 3 | 4 | | | IV-1 | COX5A | 1.44 | 6062 | 3 | 4 | | | IV-1 | DAP3 | 1.35 |
| 5967 | 3 | 4 | | | IV-1 | COX5B | 1.29 | 6063 | 3 | 4 | | | IV-1 | DAPK3 | 1.25 |
| 5968 | 3 | 4 | | | IV-1 | COX6A1 | 1.18 | 6064 | 3 | 4 | | | IV-1 | DAPP1 | 1.46 |
| 5969 | 3 | 4 | | | IV-1 | COX6C | 1.37 | 6065 | 3 | 4 | | | IV-1 | DARS | 1.36 |
| 5970 | 3 | 4 | | | IV-1 | COX7C | 1.40 | 6066 | 3 | 4 | | | IV-1 | DAXX | 1.03 |
| 5971 | 3 | 4 | | | IV-1 | CPD | 1.38 | 6067 | 3 | 4 | | | IV-1 | DAZAP2 | 1.13 |
| 5972 | 3 | 4 | | | IV-1 | CPEB2 | 1.08 | 6068 | 3 | 4 | | | IV-1 | DBF4B | 1.06 |
| 5973 | 3 | 4 | | | IV-1 | CPEB3 | 1.47 | 6069 | 3 | 4 | | | IV-1 | DBI | 1.34 |
| 5974 | 3 | 4 | | | IV-1 | CPEB4 | 1.35 | 6070 | 3 | 4 | | | IV-1 | DBP | 1.15 |
| 5975 | 3 | 4 | | | IV-1 | CPNE1 | 1.13 | 6071 | 3 | 4 | | | IV-1 | DBR1 | 1.32 |
| 5976 | 3 | 4 | | | IV-1 | CPPED1 | 1.09 | 6072 | 3 | 4 | | | IV-1 | DCAF11 | 1.19 |
| 5977 | 3 | 4 | | | IV-1 | CPQ | 1.08 | 6073 | 3 | 4 | | | IV-1 | DCAF13 | 1.33 |
| 5978 | 3 | 4 | | | IV-1 | CPSF6 | 1.45 | 6074 | 3 | 4 | | | IV-1 | DCAF15 | 1.09 |
| 5979 | 3 | 4 | | | IV-1 | CPSF7 | 1.00 | 6075 | 3 | 4 | | | IV-1 | DCAF16 | 1.15 |
| 5980 | 3 | 4 | | | IV-1 | CRAMP1L | 1.20 | 6076 | 3 | 4 | | | IV-1 | DCAF17 | 1.09 |
| 5981 | 3 | 4 | | | IV-1 | CRBN | 1.22 | 6077 | 3 | 4 | | | IV-1 | DCAF5 | 1.32 |
| 5982 | 3 | 4 | | | IV-1 | CRCP | 1.00 | 6078 | 3 | 4 | | | IV-1 | DCAF8 | 1.02 |
| 5983 | 3 | 4 | | | IV-1 | CREB1 | 1.15 | 6079 | 3 | 4 | | | IV-1 | DCK | 1.09 |
| 5984 | 3 | 4 | | | IV-1 | CREB3 | 1.36 | 6080 | 3 | 4 | | | IV-1 | DCLRE1C | 1.46 |
| 5985 | 3 | 4 | | | IV-1 | CREB3L4 | 1.28 | 6081 | 3 | 4 | | | IV-1 | DCP1B | 1.13 |
| 5986 | 3 | 4 | | | IV-1 | CREBBP | 1.02 | 6082 | 3 | 4 | | | IV-1 | DCTN1 | 1.48 |
| 5987 | 3 | 4 | | | IV-1 | CRELD1 | 1.19 | 6083 | 3 | 4 | | | IV-1 | DCTN3 | 1.26 |
| 5988 | 3 | 4 | | | IV-1 | CREM | 1.20 | 6084 | 3 | 4 | | | IV-1 | DCTN5 | 1.48 |
| 5989 | 3 | 4 | | | IV-1 | CRK | 1.32 | 6085 | 3 | 4 | | | IV-1 | DCTPP1 | 1.35 |
| 5990 | 3 | 4 | | | IV-1 | CRKL | 1.48 | 6086 | 3 | 4 | | | IV-1 | DCUN1D1 | 1.44 |
| 5991 | 3 | 4 | | | IV-1 | CRLF3 | 1.11 | 6087 | 3 | 4 | | | IV-1 | DCUN1D3 | 1.47 |
| 5992 | 3 | 4 | | | IV-1 | CRNKL1 | 1.46 | 6088 | 3 | 4 | | | IV-1 | DCUN1D4 | 1.32 |
| 5993 | 3 | 4 | | | IV-1 | CROCC | 1.13 | 6089 | 3 | 4 | | | IV-1 | DDA1 | 1.09 |
| 5994 | 3 | 4 | | | IV-1 | CROT | 1.33 | 6090 | 3 | 4 | | | IV-1 | DDAH2 | 1.48 |
| 5995 | 3 | 4 | | | IV-1 | CRSP8P | 1.31 | 6091 | 3 | 4 | | | IV-1 | DDHD1 | 1.08 |
| 5996 | 3 | 4 | | | IV-1 | CRTAM | 1.18 | 6092 | 3 | 4 | | | IV-1 | DDHD2 | 1.06 |
| 5997 | 3 | 4 | | | IV-1 | CRTC1 | 1.14 | 6093 | 3 | 4 | | | IV-1 | DDT | 1.49 |
| 5998 | 3 | 4 | | | IV-1 | CRY1 | 1.07 | 6094 | 3 | 4 | | | IV-1 | DDTL | 1.33 |
| 5999 | 3 | 4 | | | IV-1 | CRY2 | 1.23 | 6095 | 3 | 4 | | | IV-1 | DDX10 | 1.24 |
| 6000 | 3 | 4 | | | IV-1 | CRYZL1 | 1.40 | 6096 | 3 | 4 | | | IV-1 | DDX19B | 1.38 |
| 6001 | 3 | 4 | | | IV-1 | CSGALNACT2 | 1.29 | 6097 | 3 | 4 | | | IV-1 | DDX20 | 1.25 |
| 6002 | 3 | 4 | | | IV-1 | CSNK1A1L | 1.29 | 6098 | 3 | 4 | | | IV-1 | DDX23 | 1.33 |
| 6003 | 3 | 4 | | | IV-1 | CSNK1D | 1.11 | 6099 | 3 | 4 | | | IV-1 | DDX24 | 1.47 |
| 6004 | 3 | 4 | | | IV-1 | CSNK1G3 | 1.38 | 6100 | 3 | 4 | | | IV-1 | DDX26B | 1.01 |
| 6005 | 3 | 4 | | | IV-1 | CSNK2A1 | 1.49 | 6101 | 3 | 4 | | | IV-1 | DDX28 | 1.24 |
| 6006 | 3 | 4 | | | IV-1 | CSNK2B | 1.39 | 6102 | 3 | 4 | | | IV-1 | DDX31 | 1.47 |
| 6007 | 3 | 4 | | | IV-1 | CSRNP1 | 1.06 | 6103 | 3 | 4 | | | IV-1 | DDX39B | 1.34 |
| 6008 | 3 | 4 | | | IV-1 | CSRNP2 | 1.07 | 6104 | 3 | 4 | | | IV-1 | DDX3X | 1.17 |
| 6009 | 3 | 4 | | | IV-1 | CSTF1 | 1.38 | 6105 | 3 | 4 | | | IV-1 | DDX42 | 1.44 |
| 6010 | 3 | 4 | | | IV-1 | CSTF3 | 1.31 | 6106 | 3 | 4 | | | IV-1 | DDX49 | 1.32 |
| 6011 | 3 | 4 | | | IV-1 | CTAGE1 | 1.48 | 6107 | 3 | 4 | | | IV-1 | DDX5 | 1.07 |
| 6012 | 3 | 4 | | | IV-1 | CTAGE10P | 1.50 | 6108 | 3 | 4 | | | IV-1 | DDX50 | 1.29 |
| 6013 | 3 | 4 | | | IV-1 | CTAGE4 | 1.22 | 6109 | 3 | 4 | | | IV-1 | DDX51 | 1.21 |
| 6014 | 3 | 4 | | | IV-1 | CTAGE5 | 1.20 | 6110 | 3 | 4 | | | IV-1 | DDX55 | 1.33 |
| 6015 | 3 | 4 | | | IV-1 | CTAGE7P | 1.36 | 6111 | 3 | 4 | | | IV-1 | DDX59 | 1.25 |
| 6016 | 3 | 4 | | | IV-1 | CTBP1 | 1.42 | 6112 | 3 | 4 | | | IV-1 | DDX6 | 1.19 |
| 6017 | 3 | 4 | | | IV-1 | CTBP2 | 1.47 | 6113 | 3 | 4 | | | IV-1 | DECR2 | 1.43 |
| 6018 | 3 | 4 | | | IV-1 | CTBS | 1.12 | 6114 | 3 | 4 | | | IV-1 | DEDD | 1.09 |
| 6019 | 3 | 4 | | | IV-1 | CTCF | 1.47 | 6115 | 3 | 4 | | | IV-1 | DENND1B | 1.44 |
| 6020 | 3 | 4 | | | IV-1 | CTDSP1 | 1.08 | 6116 | 3 | 4 | | | IV-1 | DENND1C | 1.03 |
| 6021 | 3 | 4 | | | IV-1 | CTDSP2 | 1.21 | 6117 | 3 | 4 | | | IV-1 | DENND2D | 1.30 |
| 6022 | 3 | 4 | | | IV-1 | CTDSPL2 | 1.29 | 6118 | 3 | 4 | | | IV-1 | DENND4A | 1.47 |
| 6023 | 3 | 4 | | | IV-1 | CTLA4 | 1.19 | 6119 | 3 | 4 | | | IV-1 | DENND4B | 1.23 |
| 6024 | 3 | 4 | | | IV-1 | CTNNBIP1 | 1.36 | 6120 | 3 | 4 | | | IV-1 | DENND5A | 1.21 |
| 6025 | 3 | 4 | | | IV-1 | CTPS2 | 1.23 | 6121 | 3 | 4 | | | IV-1 | DENR | 1.46 |
| 6026 | 3 | 4 | | | IV-1 | CTSG | 1.44 | 6122 | 3 | 4 | | | IV-1 | DEPDC5 | 1.36 |
| 6027 | 3 | 4 | | | IV-1 | CTSK | 1.09 | 6123 | 3 | 4 | | | IV-1 | DERL2 | 1.32 |
| 6028 | 3 | 4 | | | IV-1 | CUEDC1 | 1.22 | 6124 | 3 | 4 | | | IV-1 | DEXI | 1.36 |
| 6029 | 3 | 4 | | | IV-1 | CUL4B | 1.34 | 6125 | 3 | 4 | | | IV-1 | DFFB | 1.04 |
| 6030 | 3 | 4 | | | IV-1 | CUL5 | 1.41 | 6126 | 3 | 4 | | | IV-1 | DGAT1 | 1.14 |
| 6031 | 3 | 4 | | | IV-1 | CUL7 | 1.14 | 6127 | 3 | 4 | | | IV-1 | DGCR14 | 1.33 |
| 6032 | 3 | 4 | | | IV-1 | CUL9 | 1.15 | 6128 | 3 | 4 | | | IV-1 | DGCR2 | 1.24 |
| 6033 | 3 | 4 | | | IV-1 | CUTA | 1.38 | 6129 | 3 | 4 | | | IV-1 | DGCR6 | 1.21 |
| 6034 | 3 | 4 | | | IV-1 | CUTC | 1.22 | 6130 | 3 | 4 | | | IV-1 | DGCR6L | 1.31 |
| 6035 | 3 | 4 | | | IV-1 | CWC15 | 1.11 | 6131 | 3 | 4 | | | IV-1 | DGCR8 | 1.45 |
| 6036 | 3 | 4 | | | IV-1 | CWC22 | 1.28 | 6132 | 3 | 4 | | | IV-1 | DGKD | 1.32 |
| 6037 | 3 | 4 | | | IV-1 | CWC25 | 1.24 | 6133 | 3 | 4 | | | IV-1 | DGKZ | 1.23 |
| 6038 | 3 | 4 | | | IV-1 | CWF19L1 | 1.19 | 6134 | 3 | 4 | | | IV-1 | DGUOK | 1.14 |
| 6039 | 3 | 4 | | | IV-1 | CXCL16 | 1.34 | 6135 | 3 | 4 | | | IV-1 | DHCR7 | 1.42 |
| 6040 | 3 | 4 | | | IV-1 | CXCR7 | 1.04 | 6136 | 3 | 4 | | | IV-1 | DHDDS | 1.33 |
| 6041 | 3 | 4 | | | IV-1 | CXXC1 | 1.29 | 6137 | 3 | 4 | | | IV-1 | DHODH | 1.12 |
| 6042 | 3 | 4 | | | IV-1 | CXorf23 | 1.06 | 6138 | 3 | 4 | | | IV-1 | DHRS1 | 1.22 |
| 6043 | 3 | 4 | | | IV-1 | CXorf38 | 1.07 | 6139 | 3 | 4 | | | IV-1 | DHRS11 | 1.15 |

Fig. 41 - 33

| | | | | | | | | | | | | | | |
|---|---|---|---|---|---|---|---|---|---|---|---|---|---|---|
| 6140 | 3 | 4 | | | IV-1 | DHRS13 | 1.06 | 6236 | 3 | 4 | | | IV-1 | ECD | 1.45 |
| 6141 | 3 | 4 | | | IV-1 | DHRS4L1 | 1.20 | 6237 | 3 | 4 | | | IV-1 | ECE1 | 1.37 |
| 6142 | 3 | 4 | | | IV-1 | DHRS7 | 1.08 | 6238 | 3 | 4 | | | IV-1 | ECH1 | 1.35 |
| 6143 | 3 | 4 | | | IV-1 | DHRSX | 1.21 | 6239 | 3 | 4 | | | IV-1 | ECI2 | 1.21 |
| 6144 | 3 | 4 | | | IV-1 | DHX16 | 1.36 | 6240 | 3 | 4 | | | IV-1 | EDC3 | 1.37 |
| 6145 | 3 | 4 | | | IV-1 | DHX30 | 1.43 | 6241 | 3 | 4 | | | IV-1 | EDEM1 | 1.26 |
| 6146 | 3 | 4 | | | IV-1 | DIABLO | 1.17 | 6242 | 3 | 4 | | | IV-1 | EDF1 | 1.14 |
| 6147 | 3 | 4 | | | IV-1 | DIDO1 | 1.13 | 6243 | 3 | 4 | | | IV-1 | EEF1A1 | 1.02 |
| 6148 | 3 | 4 | | | IV-1 | DIEXF | 1.24 | 6244 | 3 | 4 | | | IV-1 | EEF1DP3 | 1.33 |
| 6149 | 3 | 4 | | | IV-1 | DIMT1 | 1.06 | 6245 | 3 | 4 | | | IV-1 | EEF1G | 1.02 |
| 6150 | 3 | 4 | | | IV-1 | DIP2A | 1.07 | 6246 | 3 | 4 | | | IV-1 | EEF2K | 1.30 |
| 6151 | 3 | 4 | | | IV-1 | DIP2B | 1.27 | 6247 | 3 | 4 | | | IV-1 | EFCAB4B | 1.05 |
| 6152 | 3 | 4 | | | IV-1 | DIS3L | 1.32 | 6248 | 3 | 4 | | | IV-1 | EFHA1 | 1.18 |
| 6153 | 3 | 4 | | | IV-1 | DISC1 | 1.34 | 6249 | 3 | 4 | | | IV-1 | EFHD2 | 1.16 |
| 6154 | 3 | 4 | | | IV-1 | DISP1 | 1.12 | 6250 | 3 | 4 | | | IV-1 | EGLN1 | 1.00 |
| 6155 | 3 | 4 | | | IV-1 | DKFZP586I1420 | 1.29 | 6251 | 3 | 4 | | | IV-1 | EHBP1 | 1.29 |
| 6156 | 3 | 4 | | | IV-1 | DLEU1 | 1.34 | 6252 | 3 | 4 | | | IV-1 | EHMT1 | 1.36 |
| 6157 | 3 | 4 | | | IV-1 | DLG1 | 1.37 | 6253 | 3 | 4 | | | IV-1 | EHMT2 | 1.34 |
| 6158 | 3 | 4 | | | IV-1 | DLGAP4 | 1.38 | 6254 | 3 | 4 | | | IV-1 | EID2B | 1.09 |
| 6159 | 3 | 4 | | | IV-1 | DLST | 1.24 | 6255 | 3 | 4 | | | IV-1 | EIF1 | 1.43 |
| 6160 | 3 | 4 | | | IV-1 | DMAP1 | 1.34 | 6256 | 3 | 4 | | | IV-1 | EIF1AD | 1.17 |
| 6161 | 3 | 4 | | | IV-1 | DMWD | 1.22 | 6257 | 3 | 4 | | | IV-1 | EIF1B | 1.08 |
| 6162 | 3 | 4 | | | IV-1 | DNAAF2 | 1.11 | 6258 | 3 | 4 | | | IV-1 | EIF2AK3 | 1.32 |
| 6163 | 3 | 4 | | | IV-1 | DNAJA2 | 1.48 | 6259 | 3 | 4 | | | IV-1 | EIF2C3 | 1.35 |
| 6164 | 3 | 4 | | | IV-1 | DNAJA3 | 1.17 | 6260 | 3 | 4 | | | IV-1 | EIF2C4 | 1.02 |
| 6165 | 3 | 4 | | | IV-1 | DNAJB1 | 1.24 | 6261 | 3 | 4 | | | IV-1 | EIF2D | 1.21 |
| 6166 | 3 | 4 | | | IV-1 | DNAJB12 | 1.40 | 6262 | 3 | 4 | | | IV-1 | EIF2S3 | 1.34 |
| 6167 | 3 | 4 | | | IV-1 | DNAJB14 | 1.41 | 6263 | 3 | 4 | | | IV-1 | EIF3D | 1.41 |
| 6168 | 3 | 4 | | | IV-1 | DNAJB6 | 1.36 | 6264 | 3 | 4 | | | IV-1 | EIF3E | 1.36 |
| 6169 | 3 | 4 | | | IV-1 | DNAJB9 | 1.21 | 6265 | 3 | 4 | | | IV-1 | EIF3F | 1.23 |
| 6170 | 3 | 4 | | | IV-1 | DNAJC14 | 1.33 | 6266 | 3 | 4 | | | IV-1 | EIF3G | 1.15 |
| 6171 | 3 | 4 | | | IV-1 | DNAJC17 | 1.24 | 6267 | 3 | 4 | | | IV-1 | EIF3H | 1.50 |
| 6172 | 3 | 4 | | | IV-1 | DNAJC18 | 1.07 | 6268 | 3 | 4 | | | IV-1 | EIF3IP1 | 1.44 |
| 6173 | 3 | 4 | | | IV-1 | DNAJC19 | 1.10 | 6269 | 3 | 4 | | | IV-1 | EIF3K | 1.07 |
| 6174 | 3 | 4 | | | IV-1 | DNAJC21 | 1.50 | 6270 | 3 | 4 | | | IV-1 | EIF3L | 1.38 |
| 6175 | 3 | 4 | | | IV-1 | DNAJC24 | 1.11 | 6271 | 3 | 4 | | | IV-1 | EIF4A2 | 1.24 |
| 6176 | 3 | 4 | | | IV-1 | DNAJC27 | 1.05 | 6272 | 3 | 4 | | | IV-1 | EIF4B | 1.46 |
| 6177 | 3 | 4 | | | IV-1 | DNAJC8 | 1.28 | 6273 | 3 | 4 | | | IV-1 | EIF4E | 1.20 |
| 6178 | 3 | 4 | | | IV-1 | DNASE1 | 1.18 | 6274 | 3 | 4 | | | IV-1 | EIF4E2 | 1.22 |
| 6179 | 3 | 4 | | | IV-1 | DNM2 | 1.16 | 6275 | 3 | 4 | | | IV-1 | EIF4E3 | 1.47 |
| 6180 | 3 | 4 | | | IV-1 | DNMBP | 1.33 | 6276 | 3 | 4 | | | IV-1 | EIF4EBP2 | 1.34 |
| 6181 | 3 | 4 | | | IV-1 | DNMT3A | 1.27 | 6277 | 3 | 4 | | | IV-1 | EIF4ENIF1 | 1.36 |
| 6182 | 3 | 4 | | | IV-1 | DNPEP | 1.34 | 6278 | 3 | 4 | | | IV-1 | EIF5 | 1.37 |
| 6183 | 3 | 4 | | | IV-1 | DNTTIP2 | 1.43 | 6279 | 3 | 4 | | | IV-1 | EIF5A2 | 1.13 |
| 6184 | 3 | 4 | | | IV-1 | DOCK11 | 1.48 | 6280 | 3 | 4 | | | IV-1 | EIF5AL1 | 1.46 |
| 6185 | 3 | 4 | | | IV-1 | DOK1 | 1.27 | 6281 | 3 | 4 | | | IV-1 | ELAC1 | 1.08 |
| 6186 | 3 | 4 | | | IV-1 | DOK3 | 1.12 | 6282 | 3 | 4 | | | IV-1 | ELF1 | 1.44 |
| 6187 | 3 | 4 | | | IV-1 | DOLPP1 | 1.28 | 6283 | 3 | 4 | | | IV-1 | ELF2 | 1.13 |
| 6188 | 3 | 4 | | | IV-1 | DPF2 | 1.06 | 6284 | 3 | 4 | | | IV-1 | ELF4 | 1.44 |
| 6189 | 3 | 4 | | | IV-1 | DPH2 | 1.25 | 6285 | 3 | 4 | | | IV-1 | ELK1 | 1.35 |
| 6190 | 3 | 4 | | | IV-1 | DPH3 | 1.21 | 6286 | 3 | 4 | | | IV-1 | ELK3 | 1.28 |
| 6191 | 3 | 4 | | | IV-1 | DPH3P1 | 1.30 | 6287 | 3 | 4 | | | IV-1 | ELL | 1.02 |
| 6192 | 3 | 4 | | | IV-1 | DPH5 | 1.04 | 6288 | 3 | 4 | | | IV-1 | ELMO1 | 1.16 |
| 6193 | 3 | 4 | | | IV-1 | DPM1 | 1.32 | 6289 | 3 | 4 | | | IV-1 | ELMOD2 | 1.42 |
| 6194 | 3 | 4 | | | IV-1 | DPP8 | 1.46 | 6290 | 3 | 4 | | | IV-1 | ELOF1 | 1.38 |
| 6195 | 3 | 4 | | | IV-1 | DPY19L4 | 1.21 | 6291 | 3 | 4 | | | IV-1 | ELOVL5 | 1.12 |
| 6196 | 3 | 4 | | | IV-1 | DR1 | 1.46 | 6292 | 3 | 4 | | | IV-1 | EMD | 1.34 |
| 6197 | 3 | 4 | | | IV-1 | DRAP1 | 1.05 | 6293 | 3 | 4 | | | IV-1 | EMG1 | 1.09 |
| 6198 | 3 | 4 | | | IV-1 | DRG1 | 1.40 | 6294 | 3 | 4 | | | IV-1 | EMILIN1 | 1.07 |
| 6199 | 3 | 4 | | | IV-1 | DRG2 | 1.44 | 6295 | 3 | 4 | | | IV-1 | EML3 | 1.18 |
| 6200 | 3 | 4 | | | IV-1 | DSCR3 | 1.43 | 6296 | 3 | 4 | | | IV-1 | EML4 | 1.09 |
| 6201 | 3 | 4 | | | IV-1 | DSTN | 1.39 | 6297 | 3 | 4 | | | IV-1 | ENOPH1 | 1.47 |
| 6202 | 3 | 4 | | | IV-1 | DTD1 | 1.19 | 6298 | 3 | 4 | | | IV-1 | ENPP4 | 1.01 |
| 6203 | 3 | 4 | | | IV-1 | DTNB | 1.33 | 6299 | 3 | 4 | | | IV-1 | ENSA | 1.27 |
| 6204 | 3 | 4 | | | IV-1 | DTNBP1 | 1.50 | 6300 | 3 | 4 | | | IV-1 | ENTPD4 | 1.29 |
| 6205 | 3 | 4 | | | IV-1 | DTWD2 | 1.38 | 6301 | 3 | 4 | | | IV-1 | ENTPD5 | 1.15 |
| 6206 | 3 | 4 | | | IV-1 | DTX3 | 1.01 | 6302 | 3 | 4 | | | IV-1 | EP300 | 1.30 |
| 6207 | 3 | 4 | | | IV-1 | DTX3L | 1.49 | 6303 | 3 | 4 | | | IV-1 | EPB41L4A | 1.11 |
| 6208 | 3 | 4 | | | IV-1 | DTYMK | 1.26 | 6304 | 3 | 4 | | | IV-1 | EPB41L4A-AS1 | 1.05 |
| 6209 | 3 | 4 | | | IV-1 | DUS1L | 1.17 | 6305 | 3 | 4 | | | IV-1 | EPC1 | 1.08 |
| 6210 | 3 | 4 | | | IV-1 | DUS2L | 1.37 | 6306 | 3 | 4 | | | IV-1 | EPC2 | 1.25 |
| 6211 | 3 | 4 | | | IV-1 | DUS3L | 1.32 | 6307 | 3 | 4 | | | IV-1 | EPDR1 | 1.12 |
| 6212 | 3 | 4 | | | IV-1 | DUS4L | 1.31 | 6308 | 3 | 4 | | | IV-1 | EPHB6 | 1.16 |
| 6213 | 3 | 4 | | | IV-1 | DUSP11 | 1.14 | 6309 | 3 | 4 | | | IV-1 | EPM2A | 1.09 |
| 6214 | 3 | 4 | | | IV-1 | DUSP12 | 1.29 | 6310 | 3 | 4 | | | IV-1 | EPM2AIP1 | 1.39 |
| 6215 | 3 | 4 | | | IV-1 | DUSP16 | 1.03 | 6311 | 3 | 4 | | | IV-1 | EPS8 | 1.38 |
| 6216 | 3 | 4 | | | IV-1 | DUSP22 | 1.21 | 6312 | 3 | 4 | | | IV-1 | EPT1 | 1.36 |
| 6217 | 3 | 4 | | | IV-1 | DUSP23 | 1.10 | 6313 | 3 | 4 | | | IV-1 | ERAL1 | 1.41 |
| 6218 | 3 | 4 | | | IV-1 | DUSP28 | 1.01 | 6314 | 3 | 4 | | | IV-1 | ERBB2IP | 1.37 |
| 6219 | 3 | 4 | | | IV-1 | DUT | 1.37 | 6315 | 3 | 4 | | | IV-1 | ERCC1 | 1.42 |
| 6220 | 3 | 4 | | | IV-1 | DVL1 | 1.19 | 6316 | 3 | 4 | | | IV-1 | ERCC2 | 1.27 |
| 6221 | 3 | 4 | | | IV-1 | DVL3 | 1.20 | 6317 | 3 | 4 | | | IV-1 | ERCC3 | 1.18 |
| 6222 | 3 | 4 | | | IV-1 | DYNC1LI1 | 1.24 | 6318 | 3 | 4 | | | IV-1 | ERCC5 | 1.34 |
| 6223 | 3 | 4 | | | IV-1 | DYNC1LI2 | 1.49 | 6319 | 3 | 4 | | | IV-1 | ERCC6 | 1.24 |
| 6224 | 3 | 4 | | | IV-1 | DYNLRB1 | 1.11 | 6320 | 3 | 4 | | | IV-1 | ERCC8 | 1.45 |
| 6225 | 3 | 4 | | | IV-1 | DYNLT3 | 1.26 | 6321 | 3 | 4 | | | IV-1 | ERGIC2 | 1.15 |
| 6226 | 3 | 4 | | | IV-1 | DYRK1A | 1.15 | 6322 | 3 | 4 | | | IV-1 | ERI1 | 1.42 |
| 6227 | 3 | 4 | | | IV-1 | DYRK1B | 1.08 | 6323 | 3 | 4 | | | IV-1 | ERI2 | 1.39 |
| 6228 | 3 | 4 | | | IV-1 | DZIP3 | 1.02 | 6324 | 3 | 4 | | | IV-1 | ERI3 | 1.22 |
| 6229 | 3 | 4 | | | IV-1 | E2F3 | 1.34 | 6325 | 3 | 4 | | | IV-1 | ERLEC1 | 1.31 |
| 6230 | 3 | 4 | | | IV-1 | E2F4 | 1.09 | 6326 | 3 | 4 | | | IV-1 | ERO1L | 1.32 |
| 6231 | 3 | 4 | | | IV-1 | E2F6 | 1.36 | 6327 | 3 | 4 | | | IV-1 | ERO1LB | 1.07 |
| 6232 | 3 | 4 | | | IV-1 | E4F1 | 1.14 | 6328 | 3 | 4 | | | IV-1 | ERP29 | 1.43 |
| 6233 | 3 | 4 | | | IV-1 | EAPP | 1.11 | 6329 | 3 | 4 | | | IV-1 | ESCO1 | 1.06 |
| 6234 | 3 | 4 | | | IV-1 | EBAG9 | 1.07 | 6330 | 3 | 4 | | | IV-1 | ESRRA | 1.31 |
| 6235 | 3 | 4 | | | IV-1 | EBP | 1.19 | 6331 | 3 | 4 | | | IV-1 | ESYT1 | 1.28 |

Fig. 41 - 34

| | | | | | | | | | | | | | | |
|---|---|---|---|---|---|---|---|---|---|---|---|---|---|---|
| 6332 | 3 | 4 | | | IV-1 | ESYT2 | 1.33 | 6428 | 3 | 4 | | | IV-1 | FAM73A | 1.18 |
| 6333 | 3 | 4 | | | IV-1 | ETAA1 | 1.08 | 6429 | 3 | 4 | | | IV-1 | FAM76A | 1.48 |
| 6334 | 3 | 4 | | | IV-1 | ETV3 | 1.37 | 6430 | 3 | 4 | | | IV-1 | FAM76B | 1.24 |
| 6335 | 3 | 4 | | | IV-1 | ETV6 | 1.41 | 6431 | 3 | 4 | | | IV-1 | FAM82A1 | 1.29 |
| 6336 | 3 | 4 | | | IV-1 | EVI2A | 1.11 | 6432 | 3 | 4 | | | IV-1 | FAM82A2 | 1.39 |
| 6337 | 3 | 4 | | | IV-1 | EVI2B | 1.11 | 6433 | 3 | 4 | | | IV-1 | FAM82B | 1.36 |
| 6338 | 3 | 4 | | | IV-1 | EVI5L | 1.43 | 6434 | 3 | 4 | | | IV-1 | FAM83G | 1.20 |
| 6339 | 3 | 4 | | | IV-1 | EVL | 1.04 | 6435 | 3 | 4 | | | IV-1 | FAM89B | 1.04 |
| 6340 | 3 | 4 | | | IV-1 | EWSR1 | 1.16 | 6436 | 3 | 4 | | | IV-1 | FAM91A1 | 1.39 |
| 6341 | 3 | 4 | | | IV-1 | EXD2 | 1.37 | 6437 | 3 | 4 | | | IV-1 | FAM96A | 1.35 |
| 6342 | 3 | 4 | | | IV-1 | EXOC7 | 1.39 | 6438 | 3 | 4 | | | IV-1 | FAM96B | 1.39 |
| 6343 | 3 | 4 | | | IV-1 | EXOG | 1.36 | 6439 | 3 | 4 | | | IV-1 | FAN1 | 1.03 |
| 6344 | 3 | 4 | | | IV-1 | EXOSC2 | 1.08 | 6440 | 3 | 4 | | | IV-1 | FANCG | 1.09 |
| 6345 | 3 | 4 | | | IV-1 | EXOSC6 | 1.40 | 6441 | 3 | 4 | | | IV-1 | FASTK | 1.22 |
| 6346 | 3 | 4 | | | IV-1 | EXOSC8 | 1.24 | 6442 | 3 | 4 | | | IV-1 | FASTKD2 | 1.29 |
| 6347 | 3 | 4 | | | IV-1 | EXTL2 | 1.10 | 6443 | 3 | 4 | | | IV-1 | FASTKD3 | 1.32 |
| 6348 | 3 | 4 | | | IV-1 | EXTL3 | 1.30 | 6444 | 3 | 4 | | | IV-1 | FBL | 1.39 |
| 6349 | 3 | 4 | | | IV-1 | EYA3 | 1.44 | 6445 | 3 | 4 | | | IV-1 | FBRSL1 | 1.00 |
| 6350 | 3 | 4 | | | IV-1 | EZH2 | 1.12 | 6446 | 3 | 4 | | | IV-1 | FBXL12 | 1.39 |
| 6351 | 3 | 4 | | | IV-1 | F11R | 1.22 | 6447 | 3 | 4 | | | IV-1 | FBXL14 | 1.47 |
| 6352 | 3 | 4 | | | IV-1 | F2R | 1.24 | 6448 | 3 | 4 | | | IV-1 | FBXL17 | 1.50 |
| 6353 | 3 | 4 | | | IV-1 | F8 | 1.23 | 6449 | 3 | 4 | | | IV-1 | FBXL20 | 1.06 |
| 6354 | 3 | 4 | | | IV-1 | F8A1 | 1.38 | 6450 | 3 | 4 | | | IV-1 | FBXL3 | 1.04 |
| 6355 | 3 | 4 | | | IV-1 | FADD | 1.42 | 6451 | 3 | 4 | | | IV-1 | FBXL4 | 1.44 |
| 6356 | 3 | 4 | | | IV-1 | FAHD2A | 1.24 | 6452 | 3 | 4 | | | IV-1 | FBXL5 | 1.50 |
| 6357 | 3 | 4 | | | IV-1 | FAHD2B | 1.19 | 6453 | 3 | 4 | | | IV-1 | FBXL6 | 1.44 |
| 6358 | 3 | 4 | | | IV-1 | FAIM | 1.41 | 6454 | 3 | 4 | | | IV-1 | FBXO11 | 1.36 |
| 6359 | 3 | 4 | | | IV-1 | FAM103A1 | 1.43 | 6455 | 3 | 4 | | | IV-1 | FBXO25 | 1.48 |
| 6360 | 3 | 4 | | | IV-1 | FAM104A | 1.29 | 6456 | 3 | 4 | | | IV-1 | FBXO3 | 1.20 |
| 6361 | 3 | 4 | | | IV-1 | FAM107B | 1.27 | 6457 | 3 | 4 | | | IV-1 | FBXO31 | 1.15 |
| 6362 | 3 | 4 | | | IV-1 | FAM111A | 1.27 | 6458 | 3 | 4 | | | IV-1 | FBXO32 | 1.18 |
| 6363 | 3 | 4 | | | IV-1 | FAM111B | 1.05 | 6459 | 3 | 4 | | | IV-1 | FBXO33 | 1.41 |
| 6364 | 3 | 4 | | | IV-1 | FAM114A2 | 1.46 | 6460 | 3 | 4 | | | IV-1 | FBXO34 | 1.25 |
| 6365 | 3 | 4 | | | IV-1 | FAM115C | 1.50 | 6461 | 3 | 4 | | | IV-1 | FBXO38 | 1.25 |
| 6366 | 3 | 4 | | | IV-1 | FAM116A | 1.28 | 6462 | 3 | 4 | | | IV-1 | FBXO44 | 1.31 |
| 6367 | 3 | 4 | | | IV-1 | FAM116B | 1.39 | 6463 | 3 | 4 | | | IV-1 | FBXO46 | 1.29 |
| 6368 | 3 | 4 | | | IV-1 | FAM118A | 1.38 | 6464 | 3 | 4 | | | IV-1 | FBXO5 | 1.23 |
| 6369 | 3 | 4 | | | IV-1 | FAM120AOS | 1.12 | 6465 | 3 | 4 | | | IV-1 | FBXW4 | 1.26 |
| 6370 | 3 | 4 | | | IV-1 | FAM120B | 1.47 | 6466 | 3 | 4 | | | IV-1 | FBXW4P1 | 1.17 |
| 6371 | 3 | 4 | | | IV-1 | FAM120C | 1.06 | 6467 | 3 | 4 | | | IV-1 | FBXW5 | 1.24 |
| 6372 | 3 | 4 | | | IV-1 | FAM122A | 1.19 | 6468 | 3 | 4 | | | IV-1 | FBXW7 | 1.41 |
| 6373 | 3 | 4 | | | IV-1 | FAM123B | 1.32 | 6469 | 3 | 4 | | | IV-1 | FBXW9 | 1.09 |
| 6374 | 3 | 4 | | | IV-1 | FAM125B | 1.34 | 6470 | 3 | 4 | | | IV-1 | FCAR | 1.46 |
| 6375 | 3 | 4 | | | IV-1 | FAM126B | 1.09 | 6471 | 3 | 4 | | | IV-1 | FCGR2B | 1.04 |
| 6376 | 3 | 4 | | | IV-1 | FAM129A | 1.04 | 6472 | 3 | 4 | | | IV-1 | FCGR3A | 1.28 |
| 6377 | 3 | 4 | | | IV-1 | FAM131A | 1.20 | 6473 | 3 | 4 | | | IV-1 | FCGRT | 1.39 |
| 6378 | 3 | 4 | | | IV-1 | FAM131B | 1.08 | 6474 | 3 | 4 | | | IV-1 | FCHSD2 | 1.11 |
| 6379 | 3 | 4 | | | IV-1 | FAM134A | 1.13 | 6475 | 3 | 4 | | | IV-1 | FDPS | 1.22 |
| 6380 | 3 | 4 | | | IV-1 | FAM134C | 1.24 | 6476 | 3 | 4 | | | IV-1 | FEM1B | 1.40 |
| 6381 | 3 | 4 | | | IV-1 | FAM136A | 1.36 | 6477 | 3 | 4 | | | IV-1 | FEM1C | 1.39 |
| 6382 | 3 | 4 | | | IV-1 | FAM13B | 1.22 | 6478 | 3 | 4 | | | IV-1 | FGFR1 | 1.37 |
| 6383 | 3 | 4 | | | IV-1 | FAM156B | 1.32 | 6479 | 3 | 4 | | | IV-1 | FGFR1OP2 | 1.35 |
| 6384 | 3 | 4 | | | IV-1 | FAM158A | 1.03 | 6480 | 3 | 4 | | | IV-1 | FGFRL1 | 1.41 |
| 6385 | 3 | 4 | | | IV-1 | FAM160A2 | 1.26 | 6481 | 3 | 4 | | | IV-1 | FGR | 1.42 |
| 6386 | 3 | 4 | | | IV-1 | FAM160B1 | 1.39 | 6482 | 3 | 4 | | | IV-1 | FICD | 1.32 |
| 6387 | 3 | 4 | | | IV-1 | FAM160B2 | 1.32 | 6483 | 3 | 4 | | | IV-1 | FIGNL1 | 1.12 |
| 6388 | 3 | 4 | | | IV-1 | FAM161B | 1.02 | 6484 | 3 | 4 | | | IV-1 | FILIP1L | 1.01 |
| 6389 | 3 | 4 | | | IV-1 | FAM168B | 1.41 | 6485 | 3 | 4 | | | IV-1 | FIP1L1 | 1.24 |
| 6390 | 3 | 4 | | | IV-1 | FAM172A | 1.13 | 6486 | 3 | 4 | | | IV-1 | FITM2 | 1.44 |
| 6391 | 3 | 4 | | | IV-1 | FAM174B | 1.25 | 6487 | 3 | 4 | | | IV-1 | FIZ1 | 1.45 |
| 6392 | 3 | 4 | | | IV-1 | FAM175A | 1.04 | 6488 | 3 | 4 | | | IV-1 | FKBP1AP1 | 1.33 |
| 6393 | 3 | 4 | | | IV-1 | FAM176B | 1.19 | 6489 | 3 | 4 | | | IV-1 | FKBP2 | 1.17 |
| 6394 | 3 | 4 | | | IV-1 | FAM177A1 | 1.01 | 6490 | 3 | 4 | | | IV-1 | FKBPL | 1.33 |
| 6395 | 3 | 4 | | | IV-1 | FAM179B | 1.19 | 6491 | 3 | 4 | | | IV-1 | FKRP | 1.49 |
| 6396 | 3 | 4 | | | IV-1 | FAM185A | 1.14 | 6492 | 3 | 4 | | | IV-1 | FKTN | 1.20 |
| 6397 | 3 | 4 | | | IV-1 | FAM188B1 | 1.21 | 6493 | 3 | 4 | | | IV-1 | FLAD1 | 1.39 |
| 6398 | 3 | 4 | | | IV-1 | FAM188B2 | 1.27 | 6494 | 3 | 4 | | | IV-1 | FLCN | 1.24 |
| 6399 | 3 | 4 | | | IV-1 | FAM190B | 1.30 | 6495 | 3 | 4 | | | IV-1 | FLII | 1.19 |
| 6400 | 3 | 4 | | | IV-1 | FAM192A | 1.13 | 6496 | 3 | 4 | | | IV-1 | FLJ33065 | 1.02 |
| 6401 | 3 | 4 | | | IV-1 | FAM193A | 1.12 | 6497 | 3 | 4 | | | IV-1 | FLJ33630 | 1.46 |
| 6402 | 3 | 4 | | | IV-1 | FAM195A | 1.33 | 6498 | 3 | 4 | | | IV-1 | FLJ35390 | 1.09 |
| 6403 | 3 | 4 | | | IV-1 | FAM200A | 1.35 | 6499 | 3 | 4 | | | IV-1 | FLJ39653 | 1.15 |
| 6404 | 3 | 4 | | | IV-1 | FAM204A | 1.28 | 6500 | 3 | 4 | | | IV-1 | FLOT2 | 1.19 |
| 6405 | 3 | 4 | | | IV-1 | FAM206A | 1.45 | 6501 | 3 | 4 | | | IV-1 | FLYWCH1 | 1.27 |
| 6406 | 3 | 4 | | | IV-1 | FAM207A | 1.21 | 6502 | 3 | 4 | | | IV-1 | FMN1 | 1.11 |
| 6407 | 3 | 4 | | | IV-1 | FAM208B | 1.43 | 6503 | 3 | 4 | | | IV-1 | FMO4 | 1.14 |
| 6408 | 3 | 4 | | | IV-1 | FAM208 | 1.49 | 6504 | 3 | 4 | | | IV-1 | FMR1 | 1.39 |
| 6409 | 3 | 4 | | | IV-1 | FAM21B | 1.29 | 6505 | 3 | 4 | | | IV-1 | FNBP1 | 1.28 |
| 6410 | 3 | 4 | | | IV-1 | FAM22A | 1.03 | 6506 | 3 | 4 | | | IV-1 | FNIP1 | 1.07 |
| 6411 | 3 | 4 | | | IV-1 | FAM32A | 1.37 | 6507 | 3 | 4 | | | IV-1 | FOPNL | 1.27 |
| 6412 | 3 | 4 | | | IV-1 | FAM35A | 1.40 | 6508 | 3 | 4 | | | IV-1 | FOXI2 | 1.27 |
| 6413 | 3 | 4 | | | IV-1 | FAM35B | 1.08 | 6509 | 3 | 4 | | | IV-1 | FOXJ3 | 1.47 |
| 6414 | 3 | 4 | | | IV-1 | FAM35B2 | 1.28 | 6510 | 3 | 4 | | | IV-1 | FOXN2 | 1.44 |
| 6415 | 3 | 4 | | | IV-1 | FAM40A | 1.19 | 6511 | 3 | 4 | | | IV-1 | FOXN3 | 1.11 |
| 6416 | 3 | 4 | | | IV-1 | FAM43A | 1.06 | 6512 | 3 | 4 | | | IV-1 | FOXO3 | 1.24 |
| 6417 | 3 | 4 | | | IV-1 | FAM48A | 1.15 | 6513 | 3 | 4 | | | IV-1 | FOXO3B | 1.15 |
| 6418 | 3 | 4 | | | IV-1 | FAM49B | 1.26 | 6514 | 3 | 4 | | | IV-1 | FOXRED1 | 1.11 |
| 6419 | 3 | 4 | | | IV-1 | FAM53B | 1.18 | 6515 | 3 | 4 | | | IV-1 | FPR1 | 1.16 |
| 6420 | 3 | 4 | | | IV-1 | FAM54B | 1.21 | 6516 | 3 | 4 | | | IV-1 | FRA10AC1 | 1.31 |
| 6421 | 3 | 4 | | | IV-1 | FAM58A | 1.08 | 6517 | 3 | 4 | | | IV-1 | FRAT2 | 1.10 |
| 6422 | 3 | 4 | | | IV-1 | FAM60A | 1.14 | 6518 | 3 | 4 | | | IV-1 | FRG1 | 1.13 |
| 6423 | 3 | 4 | | | IV-1 | FAM65A | 1.33 | 6519 | 3 | 4 | | | IV-1 | FRMD8 | 1.23 |
| 6424 | 3 | 4 | | | IV-1 | FAM65B | 1.20 | 6520 | 3 | 4 | | | IV-1 | FRMD8P1 | 1.21 |
| 6425 | 3 | 4 | | | IV-1 | FAM69A | 1.13 | 6521 | 3 | 4 | | | IV-1 | FRS2 | 1.28 |
| 6426 | 3 | 4 | | | IV-1 | FAM71E1 | 1.39 | 6522 | 3 | 4 | | | IV-1 | FRY | 1.01 |
| 6427 | 3 | 4 | | | IV-1 | FAM72A | 1.33 | 6523 | 3 | 4 | | | IV-1 | FSD1L | 1.24 |

Fig. 41 - 35

| | | | | | | | | | | | | | | |
|---|---|---|---|---|---|---|---|---|---|---|---|---|---|---|
| 6524 | 3 | 4 | | | IV-1 | FTSJD1 | 1.43 | 6620 | 3 | 4 | | | IV-1 | GPANK1 | 1.04 |
| 6525 | 3 | 4 | | | IV-1 | FTX | 1.29 | 6621 | 3 | 4 | | | IV-1 | GPATCH1 | 1.43 |
| 6526 | 3 | 4 | | | IV-1 | FUBP1 | 1.42 | 6622 | 3 | 4 | | | IV-1 | GPATCH8 | 1.31 |
| 6527 | 3 | 4 | | | IV-1 | FUK | 1.48 | 6623 | 3 | 4 | | | IV-1 | GPBP1 | 1.28 |
| 6528 | 3 | 4 | | | IV-1 | FUNDC1 | 1.22 | 6624 | 3 | 4 | | | IV-1 | GPBP1L1 | 1.14 |
| 6529 | 3 | 4 | | | IV-1 | FUS | 1.30 | 6625 | 3 | 4 | | | IV-1 | GPCPD1 | 1.19 |
| 6530 | 3 | 4 | | | IV-1 | FUT11 | 1.35 | 6626 | 3 | 4 | | | IV-1 | GPD1L | 1.32 |
| 6531 | 3 | 4 | | | IV-1 | FUT8 | 1.44 | 6627 | 3 | 4 | | | IV-1 | GPHN | 1.26 |
| 6532 | 3 | 4 | | | IV-1 | FXC1 | 1.26 | 6628 | 3 | 4 | | | IV-1 | GPKOW | 1.17 |
| 6533 | 3 | 4 | | | IV-1 | FXR2 | 1.37 | 6629 | 3 | 4 | | | IV-1 | GPN1 | 1.44 |
| 6534 | 3 | 4 | | | IV-1 | FZD6 | 1.47 | 6630 | 3 | 4 | | | IV-1 | GPR108 | 1.46 |
| 6535 | 3 | 4 | | | IV-1 | FZR1 | 1.15 | 6631 | 3 | 4 | | | IV-1 | GPR137 | 1.35 |
| 6536 | 3 | 4 | | | IV-1 | G2E3 | 1.16 | 6632 | 3 | 4 | | | IV-1 | GPR155 | 1.06 |
| 6537 | 3 | 4 | | | IV-1 | G6PD | 1.39 | 6633 | 3 | 4 | | | IV-1 | GPR160 | 1.13 |
| 6538 | 3 | 4 | | | IV-1 | GABARAP | 1.24 | 6634 | 3 | 4 | | | IV-1 | GPR55 | 1.41 |
| 6539 | 3 | 4 | | | IV-1 | GABARAPL2 | 1.23 | 6635 | 3 | 4 | | | IV-1 | GPR56 | 1.01 |
| 6540 | 3 | 4 | | | IV-1 | GABPA | 1.43 | 6636 | 3 | 4 | | | IV-1 | GPR89A | 1.03 |
| 6541 | 3 | 4 | | | IV-1 | GABPB2 | 1.03 | 6637 | 3 | 4 | | | IV-1 | GPSM1 | 1.17 |
| 6542 | 3 | 4 | | | IV-1 | GADD45B | 1.02 | 6638 | 3 | 4 | | | IV-1 | GRAMD1A | 1.17 |
| 6543 | 3 | 4 | | | IV-1 | GADD45GIP1 | 1.36 | 6639 | 3 | 4 | | | IV-1 | GRAMD1B | 1.08 |
| 6544 | 3 | 4 | | | IV-1 | GAK | 1.41 | 6640 | 3 | 4 | | | IV-1 | GRAMD3 | 1.00 |
| 6545 | 3 | 4 | | | IV-1 | GALE | 1.30 | 6641 | 3 | 4 | | | IV-1 | GRB2 | 1.45 |
| 6546 | 3 | 4 | | | IV-1 | GALM | 1.19 | 6642 | 3 | 4 | | | IV-1 | GRIPAP1 | 1.46 |
| 6547 | 3 | 4 | | | IV-1 | GALNT11 | 1.22 | 6643 | 3 | 4 | | | IV-1 | GRK5 | 1.04 |
| 6548 | 3 | 4 | | | IV-1 | GALNT3 | 1.43 | 6644 | 3 | 4 | | | IV-1 | GRK6 | 1.09 |
| 6549 | 3 | 4 | | | IV-1 | GALT | 1.18 | 6645 | 3 | 4 | | | IV-1 | GRPEL2 | 1.10 |
| 6550 | 3 | 4 | | | IV-1 | GATAD2A | 1.08 | 6646 | 3 | 4 | | | IV-1 | GSDMD | 1.00 |
| 6551 | 3 | 4 | | | IV-1 | GATAD2B | 1.12 | 6647 | 3 | 4 | | | IV-1 | GSK3A | 1.27 |
| 6552 | 3 | 4 | | | IV-1 | GATC | 1.27 | 6648 | 3 | 4 | | | IV-1 | GSK3B | 1.45 |
| 6553 | 3 | 4 | | | IV-1 | GBAS | 1.47 | 6649 | 3 | 4 | | | IV-1 | GSR | 1.47 |
| 6554 | 3 | 4 | | | IV-1 | GCC1 | 1.35 | 6650 | 3 | 4 | | | IV-1 | GTF2A2 | 1.30 |
| 6555 | 3 | 4 | | | IV-1 | GCC2 | 1.49 | 6651 | 3 | 4 | | | IV-1 | GTF2B | 1.11 |
| 6556 | 3 | 4 | | | IV-1 | GCFC1 | 1.14 | 6652 | 3 | 4 | | | IV-1 | GTF2E1 | 1.10 |
| 6557 | 3 | 4 | | | IV-1 | GCFC1-AS1 | 1.02 | 6653 | 3 | 4 | | | IV-1 | GTF2H5 | 1.48 |
| 6558 | 3 | 4 | | | IV-1 | GCFC2 | 1.36 | 6654 | 3 | 4 | | | IV-1 | GTF2I | 1.39 |
| 6559 | 3 | 4 | | | IV-1 | GCHFR | 1.04 | 6655 | 3 | 4 | | | IV-1 | GTF3C2 | 1.42 |
| 6560 | 3 | 4 | | | IV-1 | GCLC | 1.40 | 6656 | 3 | 4 | | | IV-1 | GTPBP1 | 1.19 |
| 6561 | 3 | 4 | | | IV-1 | GCLM | 1.47 | 6657 | 3 | 4 | | | IV-1 | GTPBP10 | 1.14 |
| 6562 | 3 | 4 | | | IV-1 | GDE1 | 1.13 | 6658 | 3 | 4 | | | IV-1 | GTPBP2 | 1.10 |
| 6563 | 3 | 4 | | | IV-1 | GDF11 | 1.16 | 6659 | 3 | 4 | | | IV-1 | GTPBP3 | 1.14 |
| 6564 | 3 | 4 | | | IV-1 | GEMIN4 | 1.34 | 6660 | 3 | 4 | | | IV-1 | GTPBP5 | 1.11 |
| 6565 | 3 | 4 | | | IV-1 | GEMIN6 | 1.48 | 6661 | 3 | 4 | | | IV-1 | GTPBP6 | 1.15 |
| 6566 | 3 | 4 | | | IV-1 | GEMIN7 | 1.31 | 6662 | 3 | 4 | | | IV-1 | GXYLT1 | 1.46 |
| 6567 | 3 | 4 | | | IV-1 | GEMIN8 | 1.39 | 6663 | 3 | 4 | | | IV-1 | GYS1 | 1.49 |
| 6568 | 3 | 4 | | | IV-1 | GEN1 | 1.05 | 6664 | 3 | 4 | | | IV-1 | H2AFV | 1.33 |
| 6569 | 3 | 4 | | | IV-1 | GET4 | 1.30 | 6665 | 3 | 4 | | | IV-1 | H3F3AP4 | 1.49 |
| 6570 | 3 | 4 | | | IV-1 | GFER | 1.30 | 6666 | 3 | 4 | | | IV-1 | H3F3B | 1.38 |
| 6571 | 3 | 4 | | | IV-1 | GFOD1 | 1.08 | 6667 | 3 | 4 | | | IV-1 | H3F3C | 1.03 |
| 6572 | 3 | 4 | | | IV-1 | GGA1 | 1.19 | 6668 | 3 | 4 | | | IV-1 | HABP4 | 1.07 |
| 6573 | 3 | 4 | | | IV-1 | GGA3 | 1.38 | 6669 | 3 | 4 | | | IV-1 | HACL1 | 1.22 |
| 6574 | 3 | 4 | | | IV-1 | GGNBP2 | 1.46 | 6670 | 3 | 4 | | | IV-1 | HADH | 1.44 |
| 6575 | 3 | 4 | | | IV-1 | GGPS1 | 1.25 | 6671 | 3 | 4 | | | IV-1 | HAPLN3 | 1.07 |
| 6576 | 3 | 4 | | | IV-1 | GGT7 | 1.26 | 6672 | 3 | 4 | | | IV-1 | HARS2 | 1.49 |
| 6577 | 3 | 4 | | | IV-1 | GIMAP5 | 1.18 | 6673 | 3 | 4 | | | IV-1 | HAUS1 | 1.45 |
| 6578 | 3 | 4 | | | IV-1 | GIMAP7 | 1.28 | 6674 | 3 | 4 | | | IV-1 | HAUS2 | 1.37 |
| 6579 | 3 | 4 | | | IV-1 | GIN1 | 1.15 | 6675 | 3 | 4 | | | IV-1 | HAUS3 | 1.01 |
| 6580 | 3 | 4 | | | IV-1 | GINS3 | 1.21 | 6676 | 3 | 4 | | | IV-1 | HAUS4 | 1.29 |
| 6581 | 3 | 4 | | | IV-1 | GIPC1 | 1.13 | 6677 | 3 | 4 | | | IV-1 | HAUS6 | 1.15 |
| 6582 | 3 | 4 | | | IV-1 | GIT1 | 1.30 | 6678 | 3 | 4 | | | IV-1 | HAUS8 | 1.24 |
| 6583 | 3 | 4 | | | IV-1 | GIT2 | 1.34 | 6679 | 3 | 4 | | | IV-1 | HBP1 | 1.21 |
| 6584 | 3 | 4 | | | IV-1 | GK5 | 1.09 | 6680 | 3 | 4 | | | IV-1 | HCFC2 | 1.43 |
| 6585 | 3 | 4 | | | IV-1 | GLCCI1 | 1.17 | 6681 | 3 | 4 | | | IV-1 | HCK | 1.29 |
| 6586 | 3 | 4 | | | IV-1 | GLIPR1 | 1.43 | 6682 | 3 | 4 | | | IV-1 | HCLS1 | 1.37 |
| 6587 | 3 | 4 | | | IV-1 | GLIPR2 | 1.39 | 6683 | 3 | 4 | | | IV-1 | HCST | 1.47 |
| 6588 | 3 | 4 | | | IV-1 | GLO1 | 1.33 | 6684 | 3 | 4 | | | IV-1 | HDAC10 | 1.37 |
| 6589 | 3 | 4 | | | IV-1 | GLOD4 | 1.44 | 6685 | 3 | 4 | | | IV-1 | HDAC3 | 1.20 |
| 6590 | 3 | 4 | | | IV-1 | GLS | 1.27 | 6686 | 3 | 4 | | | IV-1 | HDAC5 | 1.10 |
| 6591 | 3 | 4 | | | IV-1 | GLT1D1 | 1.06 | 6687 | 3 | 4 | | | IV-1 | HDAC6 | 1.33 |
| 6592 | 3 | 4 | | | IV-1 | GLTSCR1 | 1.18 | 6688 | 3 | 4 | | | IV-1 | HDAC7 | 1.19 |
| 6593 | 3 | 4 | | | IV-1 | GLTSCR2 | 1.04 | 6689 | 3 | 4 | | | IV-1 | HDDC2 | 1.25 |
| 6594 | 3 | 4 | | | IV-1 | GLUL | 1.16 | 6690 | 3 | 4 | | | IV-1 | HDDC3 | 1.25 |
| 6595 | 3 | 4 | | | IV-1 | GLYR1 | 1.44 | 6691 | 3 | 4 | | | IV-1 | HDGF | 1.40 |
| 6596 | 3 | 4 | | | IV-1 | GMCL1 | 1.03 | 6692 | 3 | 4 | | | IV-1 | HDGFRP2 | 1.31 |
| 6597 | 3 | 4 | | | IV-1 | GMEB2 | 1.04 | 6693 | 3 | 4 | | | IV-1 | HDHD1 | 1.46 |
| 6598 | 3 | 4 | | | IV-1 | GMFG | 1.04 | 6694 | 3 | 4 | | | IV-1 | HEATR5B | 1.37 |
| 6599 | 3 | 4 | | | IV-1 | GNAI2 | 1.23 | 6695 | 3 | 4 | | | IV-1 | HEATR7A | 1.46 |
| 6600 | 3 | 4 | | | IV-1 | GNAQ | 1.25 | 6696 | 3 | 4 | | | IV-1 | HEBP2 | 1.23 |
| 6601 | 3 | 4 | | | IV-1 | GNB2 | 1.30 | 6697 | 3 | 4 | | | IV-1 | HECA | 1.30 |
| 6602 | 3 | 4 | | | IV-1 | GNB2L1 | 1.12 | 6698 | 3 | 4 | | | IV-1 | HECTD3 | 1.36 |
| 6603 | 3 | 4 | | | IV-1 | GNB5 | 1.01 | 6699 | 3 | 4 | | | IV-1 | HELQ | 1.14 |
| 6604 | 3 | 4 | | | IV-1 | GNG2 | 1.10 | 6700 | 3 | 4 | | | IV-1 | HENMT1 | 1.07 |
| 6605 | 3 | 4 | | | IV-1 | GNG5 | 1.43 | 6701 | 3 | 4 | | | IV-1 | HERC1 | 1.25 |
| 6606 | 3 | 4 | | | IV-1 | GNGT2 | 1.41 | 6702 | 3 | 4 | | | IV-1 | HERC3 | 1.28 |
| 6607 | 3 | 4 | | | IV-1 | GNL1 | 1.17 | 6703 | 3 | 4 | | | IV-1 | HERC6 | 1.47 |
| 6608 | 3 | 4 | | | IV-1 | GNL3 | 1.12 | 6704 | 3 | 4 | | | IV-1 | HERPUD2 | 1.01 |
| 6609 | 3 | 4 | | | IV-1 | GOLGA1 | 1.09 | 6705 | 3 | 4 | | | IV-1 | HEXIM1 | 1.18 |
| 6610 | 3 | 4 | | | IV-1 | GOLGA4 | 1.35 | 6706 | 3 | 4 | | | IV-1 | HGS | 1.13 |
| 6611 | 3 | 4 | | | IV-1 | GOLGA5 | 1.38 | 6707 | 3 | 4 | | | IV-1 | HIAT1 | 1.44 |
| 6612 | 3 | 4 | | | IV-1 | GOLGA7 | 1.07 | 6708 | 3 | 4 | | | IV-1 | HIBCH | 1.38 |
| 6613 | 3 | 4 | | | IV-1 | GOLGB1 | 1.15 | 6709 | 3 | 4 | | | IV-1 | HIF1A | 1.14 |
| 6614 | 3 | 4 | | | IV-1 | GON4L | 1.09 | 6710 | 3 | 4 | | | IV-1 | HIF1AN | 1.43 |
| 6615 | 3 | 4 | | | IV-1 | GOPC | 1.43 | 6711 | 3 | 4 | | | IV-1 | HIGD1A | 1.33 |
| 6616 | 3 | 4 | | | IV-1 | GORAB | 1.29 | 6712 | 3 | 4 | | | IV-1 | HINT1 | 1.06 |
| 6617 | 3 | 4 | | | IV-1 | GORASP1 | 1.26 | 6713 | 3 | 4 | | | IV-1 | HIPK1 | 1.43 |
| 6618 | 3 | 4 | | | IV-1 | GOT1 | 1.47 | 6714 | 3 | 4 | | | IV-1 | HIPK3 | 1.28 |
| 6619 | 3 | 4 | | | IV-1 | GPAM | 1.39 | 6715 | 3 | 4 | | | IV-1 | HIRA | 1.34 |

Fig. 41 - 36

| | | | | | | | | | | | | | | |
|---|---|---|---|---|---|---|---|---|---|---|---|---|---|---|
| 6716 | 3 | 4 | | | IV-1 | HIRIP3 | 1.27 | 6812 | 3 | 4 | | | IV-1 | IL17RC | 1.39 |
| 6717 | 3 | 4 | | | IV-1 | HIST1H2AL | 1.34 | 6813 | 3 | 4 | | | IV-1 | IL18BP | 1.05 |
| 6718 | 3 | 4 | | | IV-1 | HIST1H2BE | 1.00 | 6814 | 3 | 4 | | | IV-1 | IL32 | 1.02 |
| 6719 | 3 | 4 | | | IV-1 | HIST1H2BL | 1.18 | 6815 | 3 | 4 | | | IV-1 | IL4R | 1.31 |
| 6720 | 3 | 4 | | | IV-1 | HIST1H3A | 1.34 | 6816 | 3 | 4 | | | IV-1 | IL6R | 1.14 |
| 6721 | 3 | 4 | | | IV-1 | HIST2H2AA3 | 1.34 | 6817 | 3 | 4 | | | IV-1 | IL6ST | 1.40 |
| 6722 | 3 | 4 | | | IV-1 | HIST2H2AC | 1.39 | 6818 | 3 | 4 | | | IV-1 | ILK | 1.34 |
| 6723 | 3 | 4 | | | IV-1 | HIST2H2BF | 1.17 | 6819 | 3 | 4 | | | IV-1 | ILVBL | 1.28 |
| 6724 | 3 | 4 | | | IV-1 | HIST2H3D | 1.39 | 6820 | 3 | 4 | | | IV-1 | IMPACT | 1.48 |
| 6725 | 3 | 4 | | | IV-1 | HIVEP1 | 1.22 | 6821 | 3 | 4 | | | IV-1 | IMPDH1 | 1.20 |
| 6726 | 3 | 4 | | | IV-1 | HLA-A | 1.28 | 6822 | 3 | 4 | | | IV-1 | IMPDH2 | 1.33 |
| 6727 | 3 | 4 | | | IV-1 | HLA-B | 1.10 | 6823 | 3 | 4 | | | IV-1 | INADL | 1.15 |
| 6728 | 3 | 4 | | | IV-1 | HLA-DMB | 1.22 | 6824 | 3 | 4 | | | IV-1 | ING2 | 1.19 |
| 6729 | 3 | 4 | | | IV-1 | HLA-DPB1 | 1.18 | 6825 | 3 | 4 | | | IV-1 | ING4 | 1.02 |
| 6730 | 3 | 4 | | | IV-1 | HLCS | 1.23 | 6826 | 3 | 4 | | | IV-1 | INO80 | 1.49 |
| 6731 | 3 | 4 | | | IV-1 | HLTF | 1.05 | 6827 | 3 | 4 | | | IV-1 | INO80D | 1.12 |
| 6732 | 3 | 4 | | | IV-1 | HMBOX1 | 1.42 | 6828 | 3 | 4 | | | IV-1 | INPP1 | 1.35 |
| 6733 | 3 | 4 | | | IV-1 | HMG20B | 1.14 | 6829 | 3 | 4 | | | IV-1 | INPP4A | 1.22 |
| 6734 | 3 | 4 | | | IV-1 | HMGA1 | 1.32 | 6830 | 3 | 4 | | | IV-1 | INPP5D | 1.43 |
| 6735 | 3 | 4 | | | IV-1 | HMGB1 | 1.21 | 6831 | 3 | 4 | | | IV-1 | INPP5K | 1.05 |
| 6736 | 3 | 4 | | | IV-1 | HMGB3 | 1.37 | 6832 | 3 | 4 | | | IV-1 | INSIG1 | 1.50 |
| 6737 | 3 | 4 | | | IV-1 | HMGCL | 1.45 | 6833 | 3 | 4 | | | IV-1 | INTS10 | 1.23 |
| 6738 | 3 | 4 | | | IV-1 | HMGN1 | 1.28 | 6834 | 3 | 4 | | | IV-1 | INTS12 | 1.45 |
| 6739 | 3 | 4 | | | IV-1 | HMGN2 | 1.32 | 6835 | 3 | 4 | | | IV-1 | INTS3 | 1.49 |
| 6740 | 3 | 4 | | | IV-1 | HMGN3 | 1.37 | 6836 | 3 | 4 | | | IV-1 | INTS6 | 1.16 |
| 6741 | 3 | 4 | | | IV-1 | HMGXB4 | 1.30 | 6837 | 3 | 4 | | | IV-1 | IP6K1 | 1.00 |
| 6742 | 3 | 4 | | | IV-1 | HMHA1 | 1.26 | 6838 | 3 | 4 | | | IV-1 | IPCEF1 | 1.32 |
| 6743 | 3 | 4 | | | IV-1 | HN1 | 1.16 | 6839 | 3 | 4 | | | IV-1 | IPMK | 1.10 |
| 6744 | 3 | 4 | | | IV-1 | HN1L | 1.40 | 6840 | 3 | 4 | | | IV-1 | IPO11 | 1.30 |
| 6745 | 3 | 4 | | | IV-1 | HNRNPA1L2 | 1.44 | 6841 | 3 | 4 | | | IV-1 | IPO9 | 1.47 |
| 6746 | 3 | 4 | | | IV-1 | HNRNPA3P1 | 1.04 | 6842 | 3 | 4 | | | IV-1 | IPPK | 1.41 |
| 6747 | 3 | 4 | | | IV-1 | HNRNPC | 1.17 | 6843 | 3 | 4 | | | IV-1 | IQCE | 1.42 |
| 6748 | 3 | 4 | | | IV-1 | HNRNPH1 | 1.05 | 6844 | 3 | 4 | | | IV-1 | IQCG | 1.35 |
| 6749 | 3 | 4 | | | IV-1 | HNRNPL | 1.19 | 6845 | 3 | 4 | | | IV-1 | IQSEC1 | 1.33 |
| 6750 | 3 | 4 | | | IV-1 | HNRNPUL1 | 1.27 | 6846 | 3 | 4 | | | IV-1 | IRAK1 | 1.29 |
| 6751 | 3 | 4 | | | IV-1 | HNRPDL | 1.04 | 6847 | 3 | 4 | | | IV-1 | IRAK4 | 1.11 |
| 6752 | 3 | 4 | | | IV-1 | HOXB4 | 1.25 | 6848 | 3 | 4 | | | IV-1 | IRF2 | 1.09 |
| 6753 | 3 | 4 | | | IV-1 | HP1BP3 | 1.36 | 6849 | 3 | 4 | | | IV-1 | IRF2BP1 | 1.44 |
| 6754 | 3 | 4 | | | IV-1 | HPCAL1 | 1.26 | 6850 | 3 | 4 | | | IV-1 | IRF2BPL | 1.09 |
| 6755 | 3 | 4 | | | IV-1 | HRH2 | 1.36 | 6851 | 3 | 4 | | | IV-1 | IRF7 | 1.29 |
| 6756 | 3 | 4 | | | IV-1 | HRSP12 | 1.19 | 6852 | 3 | 4 | | | IV-1 | IRF9 | 1.09 |
| 6757 | 3 | 4 | | | IV-1 | HS1BP3 | 1.49 | 6853 | 3 | 4 | | | IV-1 | ISCA2 | 1.48 |
| 6758 | 3 | 4 | | | IV-1 | HS3ST3B1 | 1.07 | 6854 | 3 | 4 | | | IV-1 | ISCU | 1.04 |
| 6759 | 3 | 4 | | | IV-1 | HS6ST1 | 1.48 | 6855 | 3 | 4 | | | IV-1 | ISG20L2 | 1.29 |
| 6760 | 3 | 4 | | | IV-1 | HS8P1 | 1.29 | 6856 | 3 | 4 | | | IV-1 | ISM1 | 1.21 |
| 6761 | 3 | 4 | | | IV-1 | HSCB | 1.23 | 6857 | 3 | 4 | | | IV-1 | ISOC1 | 1.25 |
| 6762 | 3 | 4 | | | IV-1 | HSD17B11 | 1.48 | 6858 | 3 | 4 | | | IV-1 | ISOC2 | 1.33 |
| 6763 | 3 | 4 | | | IV-1 | HSD17B7 | 1.09 | 6859 | 3 | 4 | | | IV-1 | ISY1 | 1.23 |
| 6764 | 3 | 4 | | | IV-1 | HSDL1 | 1.33 | 6860 | 3 | 4 | | | IV-1 | ITCH | 1.48 |
| 6765 | 3 | 4 | | | IV-1 | HSDL2 | 1.05 | 6861 | 3 | 4 | | | IV-1 | ITFG2 | 1.36 |
| 6766 | 3 | 4 | | | IV-1 | HSPA13 | 1.48 | 6862 | 3 | 4 | | | IV-1 | ITGA5 | 1.43 |
| 6767 | 3 | 4 | | | IV-1 | HSPA7 | 1.21 | 6863 | 3 | 4 | | | IV-1 | ITGA6 | 1.20 |
| 6768 | 3 | 4 | | | IV-1 | HSPA8 | 1.39 | 6864 | 3 | 4 | | | IV-1 | ITGAL | 1.48 |
| 6769 | 3 | 4 | | | IV-1 | HSPBAP1 | 1.34 | 6865 | 3 | 4 | | | IV-1 | ITGB1BP1 | 1.40 |
| 6770 | 3 | 4 | | | IV-1 | HSPBP1 | 1.42 | 6866 | 3 | 4 | | | IV-1 | ITGB7 | 1.40 |
| 6771 | 3 | 4 | | | IV-1 | HUWE1 | 1.46 | 6867 | 3 | 4 | | | IV-1 | ITPK1 | 1.01 |
| 6772 | 3 | 4 | | | IV-1 | HVCN1 | 1.13 | 6868 | 3 | 4 | | | IV-1 | ITPKB | 1.14 |
| 6773 | 3 | 4 | | | IV-1 | HYLS1 | 1.42 | 6869 | 3 | 4 | | | IV-1 | ITPRIP | 1.13 |
| 6774 | 3 | 4 | | | IV-1 | IAH1 | 1.26 | 6870 | 3 | 4 | | | IV-1 | ITSN2 | 1.19 |
| 6775 | 3 | 4 | | | IV-1 | ICA1 | 1.17 | 6871 | 3 | 4 | | | IV-1 | IWS1 | 1.39 |
| 6776 | 3 | 4 | | | IV-1 | ICAM1 | 1.39 | 6872 | 3 | 4 | | | IV-1 | JAG1 | 1.26 |
| 6777 | 3 | 4 | | | IV-1 | ICAM2 | 1.43 | 6873 | 3 | 4 | | | IV-1 | JAK1 | 1.37 |
| 6778 | 3 | 4 | | | IV-1 | ICK | 1.26 | 6874 | 3 | 4 | | | IV-1 | JAK3 | 1.33 |
| 6779 | 3 | 4 | | | IV-1 | ICT1 | 1.40 | 6875 | 3 | 4 | | | IV-1 | JARID2 | 1.25 |
| 6780 | 3 | 4 | | | IV-1 | ID2 | 1.12 | 6876 | 3 | 4 | | | IV-1 | JAZF1 | 1.21 |
| 6781 | 3 | 4 | | | IV-1 | IDH3B | 1.32 | 6877 | 3 | 4 | | | IV-1 | JHDM1D | 1.31 |
| 6782 | 3 | 4 | | | IV-1 | IDI2 | 1.00 | 6878 | 3 | 4 | | | IV-1 | JMJD1C | 1.02 |
| 6783 | 3 | 4 | | | IV-1 | IER2 | 1.13 | 6879 | 3 | 4 | | | IV-1 | JMJD5 | 1.29 |
| 6784 | 3 | 4 | | | IV-1 | IFFO1 | 1.13 | 6880 | 3 | 4 | | | IV-1 | JMJD6 | 1.26 |
| 6785 | 3 | 4 | | | IV-1 | IFI27L1 | 1.04 | 6881 | 3 | 4 | | | IV-1 | JMJD7 | 1.28 |
| 6786 | 3 | 4 | | | IV-1 | IFIT5 | 1.42 | 6882 | 3 | 4 | | | IV-1 | JMJD8 | 1.37 |
| 6787 | 3 | 4 | | | IV-1 | IFNAR1 | 1.39 | 6883 | 3 | 4 | | | IV-1 | JOSD1 | 1.31 |
| 6788 | 3 | 4 | | | IV-1 | IFNAR2 | 1.41 | 6884 | 3 | 4 | | | IV-1 | JPH4 | 1.13 |
| 6789 | 3 | 4 | | | IV-1 | IFRD2 | 1.21 | 6885 | 3 | 4 | | | IV-1 | JRK | 1.43 |
| 6790 | 3 | 4 | | | IV-1 | IFT122 | 1.23 | 6886 | 3 | 4 | | | IV-1 | JTB | 1.22 |
| 6791 | 3 | 4 | | | IV-1 | IFT20 | 1.13 | 6887 | 3 | 4 | | | IV-1 | JUNB | 1.06 |
| 6792 | 3 | 4 | | | IV-1 | IFT27 | 1.46 | 6888 | 3 | 4 | | | IV-1 | JUND | 1.19 |
| 6793 | 3 | 4 | | | IV-1 | IFT52 | 1.18 | 6889 | 3 | 4 | | | IV-1 | KANSL1 | 1.05 |
| 6794 | 3 | 4 | | | IV-1 | IFT57 | 1.02 | 6890 | 3 | 4 | | | IV-1 | KANSL1L | 1.20 |
| 6795 | 3 | 4 | | | IV-1 | IFT80 | 1.08 | 6891 | 3 | 4 | | | IV-1 | KANSL2 | 1.07 |
| 6796 | 3 | 4 | | | IV-1 | IGBP1 | 1.37 | 6892 | 3 | 4 | | | IV-1 | KANSL3 | 1.24 |
| 6797 | 3 | 4 | | | IV-1 | IGBP1P1 | 1.30 | 6893 | 3 | 4 | | | IV-1 | KAT2A | 1.12 |
| 6798 | 3 | 4 | | | IV-1 | IGF2BP3 | 1.45 | 6894 | 3 | 4 | | | IV-1 | KAT6A | 1.21 |
| 6799 | 3 | 4 | | | IV-1 | IGF2R | 1.27 | 6895 | 3 | 4 | | | IV-1 | KAT7 | 1.36 |
| 6800 | 3 | 4 | | | IV-1 | IGFLR1 | 1.13 | 6896 | 3 | 4 | | | IV-1 | KAT8 | 1.08 |
| 6801 | 3 | 4 | | | IV-1 | IGHMBP2 | 1.42 | 6897 | 3 | 4 | | | IV-1 | KATNA1 | 1.27 |
| 6802 | 3 | 4 | | | IV-1 | IGIP | 1.38 | 6898 | 3 | 4 | | | IV-1 | KATNB1 | 1.15 |
| 6803 | 3 | 4 | | | IV-1 | IGSF8 | 1.32 | 6899 | 3 | 4 | | | IV-1 | KBTBD2 | 1.21 |
| 6804 | 3 | 4 | | | IV-1 | IK | 1.12 | 6900 | 3 | 4 | | | IV-1 | KBTBD4 | 1.14 |
| 6805 | 3 | 4 | | | IV-1 | IKBIP | 1.18 | 6901 | 3 | 4 | | | IV-1 | KBTBD6 | 1.23 |
| 6806 | 3 | 4 | | | IV-1 | IKBKB | 1.25 | 6902 | 3 | 4 | | | IV-1 | KBTBD7 | 1.29 |
| 6807 | 3 | 4 | | | IV-1 | IKBKG | 1.37 | 6903 | 3 | 4 | | | IV-1 | KBTBD8 | 1.07 |
| 6808 | 3 | 4 | | | IV-1 | IKZF4 | 1.37 | 6904 | 3 | 4 | | | IV-1 | KCMF1 | 1.23 |
| 6809 | 3 | 4 | | | IV-1 | IL10 | 1.36 | 6905 | 3 | 4 | | | IV-1 | KCNAB2 | 1.43 |
| 6810 | 3 | 4 | | | IV-1 | IL10RB | 1.39 | 6906 | 3 | 4 | | | IV-1 | KCNE3 | 1.34 |
| 6811 | 3 | 4 | | | IV-1 | IL12RB1 | 1.10 | 6907 | 3 | 4 | | | IV-1 | KCNG2 | 1.05 |

Fig. 41 - 37

| | | | | | | | | | | | | | | |
|---|---|---|---|---|---|---|---|---|---|---|---|---|---|---|
| 6908 | 3 | 4 | | | IV-1 | KCNMB3 | 1.28 | 7004 | 3 | 4 | | | IV-1 | LEPROTL1 | 1.17 |
| 6909 | 3 | 4 | | | IV-1 | KCTD1 | 1.34 | 7005 | 3 | 4 | | | IV-1 | LETM2 | 1.25 |
| 6910 | 3 | 4 | | | IV-1 | KCTD10 | 1.15 | 7006 | 3 | 4 | | | IV-1 | LGR6 | 1.38 |
| 6911 | 3 | 4 | | | IV-1 | KCTD18 | 1.21 | 7007 | 3 | 4 | | | IV-1 | LIG1 | 1.26 |
| 6912 | 3 | 4 | | | IV-1 | KCTD2 | 1.39 | 7008 | 3 | 4 | | | IV-1 | LIG3 | 1.45 |
| 6913 | 3 | 4 | | | IV-1 | KCTD21 | 1.24 | 7009 | 3 | 4 | | | IV-1 | LIG4 | 1.37 |
| 6914 | 3 | 4 | | | IV-1 | KCTD9 | 1.28 | 7010 | 3 | 4 | | | IV-1 | LILRA2 | 1.31 |
| 6915 | 3 | 4 | | | IV-1 | KDELC2 | 1.44 | 7011 | 3 | 4 | | | IV-1 | LILRA6 | 1.45 |
| 6916 | 3 | 4 | | | IV-1 | KDM2A | 1.16 | 7012 | 3 | 4 | | | IV-1 | LIMS1 | 1.44 |
| 6917 | 3 | 4 | | | IV-1 | KDM3A | 1.00 | 7013 | 3 | 4 | | | IV-1 | LIMS2 | 1.38 |
| 6918 | 3 | 4 | | | IV-1 | KDM4A | 1.50 | 7014 | 3 | 4 | | | IV-1 | LIMS3L | 1.29 |
| 6919 | 3 | 4 | | | IV-1 | KDM4C | 1.42 | 7015 | 3 | 4 | | | IV-1 | LIN52 | 1.29 |
| 6920 | 3 | 4 | | | IV-1 | KDM5A | 1.33 | 7016 | 3 | 4 | | | IV-1 | LIN54 | 1.25 |
| 6921 | 3 | 4 | | | IV-1 | KDM5B | 1.37 | 7017 | 3 | 4 | | | IV-1 | LIN7C | 1.25 |
| 6922 | 3 | 4 | | | IV-1 | KHK | 1.13 | 7018 | 3 | 4 | | | IV-1 | LINC00094 | 1.41 |
| 6923 | 3 | 4 | | | IV-1 | KHNYN | 1.21 | 7019 | 3 | 4 | | | IV-1 | LINC00116 | 1.15 |
| 6924 | 3 | 4 | | | IV-1 | KIAA0020 | 1.48 | 7020 | 3 | 4 | | | IV-1 | LINC00324 | 1.07 |
| 6925 | 3 | 4 | | | IV-1 | KIAA0101 | 1.06 | 7021 | 3 | 4 | | | IV-1 | LINS | 1.16 |
| 6926 | 3 | 4 | | | IV-1 | KIAA0141 | 1.46 | 7022 | 3 | 4 | | | IV-1 | LIPT2 | 1.19 |
| 6927 | 3 | 4 | | | IV-1 | KIAA0182 | 1.09 | 7023 | 3 | 4 | | | IV-1 | LITAF | 1.03 |
| 6928 | 3 | 4 | | | IV-1 | KIAA0195 | 1.34 | 7024 | 3 | 4 | | | IV-1 | LIX1L | 1.21 |
| 6929 | 3 | 4 | | | IV-1 | KIAA0226 | 1.47 | 7025 | 3 | 4 | | | IV-1 | LLGL1 | 1.27 |
| 6930 | 3 | 4 | | | IV-1 | KIAA0226L | 1.05 | 7026 | 3 | 4 | | | IV-1 | LMBR1L | 1.19 |
| 6931 | 3 | 4 | | | IV-1 | KIAA0232 | 1.15 | 7027 | 3 | 4 | | | IV-1 | LMBRD1 | 1.37 |
| 6932 | 3 | 4 | | | IV-1 | KIAA0240 | 1.22 | 7028 | 3 | 4 | | | IV-1 | LMF1 | 1.09 |
| 6933 | 3 | 4 | | | IV-1 | KIAA0317 | 1.20 | 7029 | 3 | 4 | | | IV-1 | LMF2 | 1.21 |
| 6934 | 3 | 4 | | | IV-1 | KIAA0319L | 1.32 | 7030 | 3 | 4 | | | IV-1 | LMO7 | 1.04 |
| 6935 | 3 | 4 | | | IV-1 | KIAA0355 | 1.01 | 7031 | 3 | 4 | | | IV-1 | LMTK2 | 1.21 |
| 6936 | 3 | 4 | | | IV-1 | KIAA0415 | 1.20 | 7032 | 3 | 4 | | | IV-1 | LNX2 | 1.38 |
| 6937 | 3 | 4 | | | IV-1 | KIAA0528 | 1.47 | 7033 | 3 | 4 | | | IV-1 | LOC100093631 | 1.38 |
| 6938 | 3 | 4 | | | IV-1 | KIAA0556 | 1.14 | 7034 | 3 | 4 | | | IV-1 | LOC100128822 | 1.47 |
| 6939 | 3 | 4 | | | IV-1 | KIAA0754 | 1.11 | 7035 | 3 | 4 | | | IV-1 | LOC100129138 | 1.50 |
| 6940 | 3 | 4 | | | IV-1 | KIAA0907 | 1.18 | 7036 | 3 | 4 | | | IV-1 | LOC100129387 | 1.04 |
| 6941 | 3 | 4 | | | IV-1 | KIAA0922 | 1.35 | 7037 | 3 | 4 | | | IV-1 | LOC100129550 | 1.17 |
| 6942 | 3 | 4 | | | IV-1 | KIAA0947 | 1.48 | 7038 | 3 | 4 | | | IV-1 | LOC100129961 | 1.19 |
| 6943 | 3 | 4 | | | IV-1 | KIAA1143 | 1.10 | 7039 | 3 | 4 | | | IV-1 | LOC100130093 | 1.29 |
| 6944 | 3 | 4 | | | IV-1 | KIAA1191 | 1.14 | 7040 | 3 | 4 | | | IV-1 | LOC100130855 | 1.08 |
| 6945 | 3 | 4 | | | IV-1 | KIAA1430 | 1.34 | 7041 | 3 | 4 | | | IV-1 | LOC100131655 | 1.41 |
| 6946 | 3 | 4 | | | IV-1 | KIAA1586 | 1.48 | 7042 | 3 | 4 | | | IV-1 | LOC100131733 | 1.08 |
| 6947 | 3 | 4 | | | IV-1 | KIAA1671 | 1.37 | 7043 | 3 | 4 | | | IV-1 | LOC100132707 | 1.16 |
| 6948 | 3 | 4 | | | IV-1 | KIAA1704 | 1.21 | 7044 | 3 | 4 | | | IV-1 | LOC100132724 | 1.34 |
| 6949 | 3 | 4 | | | IV-1 | KIAA1737 | 1.01 | 7045 | 3 | 4 | | | IV-1 | LOC100132831 | 1.03 |
| 6950 | 3 | 4 | | | IV-1 | KIAA1797 | 1.49 | 7046 | 3 | 4 | | | IV-1 | LOC100134713 | 1.05 |
| 6951 | 3 | 4 | | | IV-1 | KIAA1908 | 1.23 | 7047 | 3 | 4 | | | IV-1 | LOC100288615 | 1.02 |
| 6952 | 3 | 4 | | | IV-1 | KIAA1919 | 1.36 | 7048 | 3 | 4 | | | IV-1 | LOC100294145 | 1.19 |
| 6953 | 3 | 4 | | | IV-1 | KIAA1958 | 1.47 | 7049 | 3 | 4 | | | IV-1 | LOC100335030 | 1.23 |
| 6954 | 3 | 4 | | | IV-1 | KIAA2013 | 1.45 | 7050 | 3 | 4 | | | IV-1 | LOC100499405 | 1.01 |
| 6955 | 3 | 4 | | | IV-1 | KIAA2018 | 1.16 | 7051 | 3 | 4 | | | IV-1 | LOC100499466 | 1.39 |
| 6956 | 3 | 4 | | | IV-1 | KIF11 | 1.12 | 7052 | 3 | 4 | | | IV-1 | LOC100499489 | 1.19 |
| 6957 | 3 | 4 | | | IV-1 | KIF13A | 1.19 | 7053 | 3 | 4 | | | IV-1 | LOC100505483 | 1.07 |
| 6958 | 3 | 4 | | | IV-1 | KIF21A | 1.36 | 7054 | 3 | 4 | | | IV-1 | LOC100505681 | 1.37 |
| 6959 | 3 | 4 | | | IV-1 | KIF2A | 1.12 | 7055 | 3 | 4 | | | IV-1 | LOC100505687 | 1.46 |
| 6960 | 3 | 4 | | | IV-1 | KIN | 1.12 | 7056 | 3 | 4 | | | IV-1 | LOC100505812 | 1.05 |
| 6961 | 3 | 4 | | | IV-1 | KIR2DL1 | 1.07 | 7057 | 3 | 4 | | | IV-1 | LOC100505876 | 1.39 |
| 6962 | 3 | 4 | | | IV-1 | KLC1 | 1.50 | 7058 | 3 | 4 | | | IV-1 | LOC100506046 | 1.26 |
| 6963 | 3 | 4 | | | IV-1 | KLC4 | 1.07 | 7059 | 3 | 4 | | | IV-1 | LOC100506190 | 1.32 |
| 6964 | 3 | 4 | | | IV-1 | KLF2 | 1.18 | 7060 | 3 | 4 | | | IV-1 | LOC100506710 | 1.06 |
| 6965 | 3 | 4 | | | IV-1 | KLF3 | 1.28 | 7061 | 3 | 4 | | | IV-1 | LOC139201 | 1.05 |
| 6966 | 3 | 4 | | | IV-1 | KLF6 | 1.07 | 7062 | 3 | 4 | | | IV-1 | LOC145783 | 1.25 |
| 6967 | 3 | 4 | | | IV-1 | KLHDC10 | 1.36 | 7063 | 3 | 4 | | | IV-1 | LOC148413 | 1.17 |
| 6968 | 3 | 4 | | | IV-1 | KLHDC2 | 1.34 | 7064 | 3 | 4 | | | IV-1 | LOC150776 | 1.31 |
| 6969 | 3 | 4 | | | IV-1 | KLHDC3 | 1.18 | 7065 | 3 | 4 | | | IV-1 | LOC152217 | 1.43 |
| 6970 | 3 | 4 | | | IV-1 | KLHDC4 | 1.19 | 7066 | 3 | 4 | | | IV-1 | LOC220906 | 1.15 |
| 6971 | 3 | 4 | | | IV-1 | KLHL12 | 1.40 | 7067 | 3 | 4 | | | IV-1 | LOC254128 | 1.28 |
| 6972 | 3 | 4 | | | IV-1 | KLHL20 | 1.14 | 7068 | 3 | 4 | | | IV-1 | LOC254559 | 1.10 |
| 6973 | 3 | 4 | | | IV-1 | KLHL24 | 1.23 | 7069 | 3 | 4 | | | IV-1 | LOC283174 | 1.20 |
| 6974 | 3 | 4 | | | IV-1 | KLHL25 | 1.19 | 7070 | 3 | 4 | | | IV-1 | LOC284385 | 1.35 |
| 6975 | 3 | 4 | | | IV-1 | KLHL28 | 1.26 | 7071 | 3 | 4 | | | IV-1 | LOC284889 | 1.18 |
| 6976 | 3 | 4 | | | IV-1 | KLHL36 | 1.13 | 7072 | 3 | 4 | | | IV-1 | LOC285359 | 1.34 |
| 6977 | 3 | 4 | | | IV-1 | KLHL6 | 1.36 | 7073 | 3 | 4 | | | IV-1 | LOC285540 | 1.02 |
| 6978 | 3 | 4 | | | IV-1 | KLHL7 | 1.16 | 7074 | 3 | 4 | | | IV-1 | LOC286437 | 1.39 |
| 6979 | 3 | 4 | | | IV-1 | KPNA1 | 1.26 | 7075 | 3 | 4 | | | IV-1 | LOC338758 | 1.22 |
| 6980 | 3 | 4 | | | IV-1 | KPNA4 | 1.22 | 7076 | 3 | 4 | | | IV-1 | LOC339290 | 1.24 |
| 6981 | 3 | 4 | | | IV-1 | KPNA5 | 1.20 | 7077 | 3 | 4 | | | IV-1 | LOC339803 | 1.25 |
| 6982 | 3 | 4 | | | IV-1 | KPNB1 | 1.23 | 7078 | 3 | 4 | | | IV-1 | LOC375190 | 1.49 |
| 6983 | 3 | 4 | | | IV-1 | KRBA1 | 1.27 | 7079 | 3 | 4 | | | IV-1 | LOC386597 | 1.13 |
| 6984 | 3 | 4 | | | IV-1 | KRI1 | 1.38 | 7080 | 3 | 4 | | | IV-1 | LOC388499 | 1.26 |
| 6985 | 3 | 4 | | | IV-1 | KRIT1 | 1.13 | 7081 | 3 | 4 | | | IV-1 | LOC389834 | 1.43 |
| 6986 | 3 | 4 | | | IV-1 | KRR1 | 1.37 | 7082 | 3 | 4 | | | IV-1 | LOC400027 | 1.09 |
| 6987 | 3 | 4 | | | IV-1 | KXD1 | 1.08 | 7083 | 3 | 4 | | | IV-1 | LOC400604 | 1.30 |
| 6988 | 3 | 4 | | | IV-1 | L3MBTL3 | 1.46 | 7084 | 3 | 4 | | | IV-1 | LOC400657 | 1.12 |
| 6989 | 3 | 4 | | | IV-1 | LACTB2 | 1.21 | 7085 | 3 | 4 | | | IV-1 | LOC407835 | 1.30 |
| 6990 | 3 | 4 | | | IV-1 | LAMP5 | 1.26 | 7086 | 3 | 4 | | | IV-1 | LOC439994 | 1.44 |
| 6991 | 3 | 4 | | | IV-1 | LAMTOR1 | 1.33 | 7087 | 3 | 4 | | | IV-1 | LOC440434 | 1.44 |
| 6992 | 3 | 4 | | | IV-1 | LAMTOR3 | 1.34 | 7088 | 3 | 4 | | | IV-1 | LOC550643 | 1.44 |
| 6993 | 3 | 4 | | | IV-1 | LANCL1 | 1.32 | 7089 | 3 | 4 | | | IV-1 | LOC595101 | 1.03 |
| 6994 | 3 | 4 | | | IV-1 | LAS1L | 1.46 | 7090 | 3 | 4 | | | IV-1 | LOC606724 | 1.22 |
| 6995 | 3 | 4 | | | IV-1 | LASP1 | 1.26 | 7091 | 3 | 4 | | | IV-1 | LOC641298 | 1.05 |
| 6996 | 3 | 4 | | | IV-1 | LAT2 | 1.07 | 7092 | 3 | 4 | | | IV-1 | LOC641367 | 1.22 |
| 6997 | 3 | 4 | | | IV-1 | LCMT1 | 1.46 | 7093 | 3 | 4 | | | IV-1 | LOC642852 | 1.21 |
| 6998 | 3 | 4 | | | IV-1 | LCP2 | 1.12 | 7094 | 3 | 4 | | | IV-1 | LOC643837 | 1.33 |
| 6999 | 3 | 4 | | | IV-1 | LDHB | 1.28 | 7095 | 3 | 4 | | | IV-1 | LOC645212 | 1.03 |
| 7000 | 3 | 4 | | | IV-1 | LDLRAP1 | 1.00 | 7096 | 3 | 4 | | | IV-1 | LOC646214 | 1.41 |
| 7001 | 3 | 4 | | | IV-1 | LEMD2 | 1.14 | 7097 | 3 | 4 | | | IV-1 | LOC646762 | 1.11 |
| 7002 | 3 | 4 | | | IV-1 | LEMD3 | 1.20 | 7098 | 3 | 4 | | | IV-1 | LOC649395 | 1.38 |
| 7003 | 3 | 4 | | | IV-1 | LEPROT | 1.46 | 7099 | 3 | 4 | | | IV-1 | LOC653486 | 1.05 |

Fig. 41 - 38

| | | | | | | | |
|---|---|---|---|---|---|---|---|
| 7100 | 3 | 4 | | IV-1 | LOC728024 | 1.32 |
| 7101 | 3 | 4 | | IV-1 | LOC728739 | 1.41 |
| 7102 | 3 | 4 | | IV-1 | LOC728758 | 1.09 |
| 7103 | 3 | 4 | | IV-1 | LOC728855 | 1.18 |
| 7104 | 3 | 4 | | IV-1 | LOC729683 | 1.22 |
| 7105 | 3 | 4 | | IV-1 | LOC92249 | 1.09 |
| 7106 | 3 | 4 | | IV-1 | LOC93622 | 1.07 |
| 7107 | 3 | 4 | | IV-1 | LOH12CR1 | 1.36 |
| 7108 | 3 | 4 | | IV-1 | LONRF1 | 1.04 |
| 7109 | 3 | 4 | | IV-1 | LPCAT1 | 1.32 |
| 7110 | 3 | 4 | | IV-1 | LPGAT1 | 1.36 |
| 7111 | 3 | 4 | | IV-1 | LPIN1 | 1.46 |
| 7112 | 3 | 4 | | IV-1 | LPP | 1.32 |
| 7113 | 3 | 4 | | IV-1 | LPP-AS2 | 1.25 |
| 7114 | 3 | 4 | | IV-1 | LRIF1 | 1.04 |
| 7115 | 3 | 4 | | IV-1 | LRIG2 | 1.36 |
| 7116 | 3 | 4 | | IV-1 | LRP11 | 1.31 |
| 7117 | 3 | 4 | | IV-1 | LRP12 | 1.47 |
| 7118 | 3 | 4 | | IV-1 | LRR1 | 1.43 |
| 7119 | 3 | 4 | | IV-1 | LRRC14 | 1.20 |
| 7120 | 3 | 4 | | IV-1 | LRRC23 | 1.26 |
| 7121 | 3 | 4 | | IV-1 | LRRC28 | 1.29 |
| 7122 | 3 | 4 | | IV-1 | LRRC37A4 | 1.03 |
| 7123 | 3 | 4 | | IV-1 | LRRC37BP1 | 1.28 |
| 7124 | 3 | 4 | | IV-1 | LRRC42 | 1.40 |
| 7125 | 3 | 4 | | IV-1 | LRRC57 | 1.39 |
| 7126 | 3 | 4 | | IV-1 | LRRC8A | 1.23 |
| 7127 | 3 | 4 | | IV-1 | LRRCC1 | 1.09 |
| 7128 | 3 | 4 | | IV-1 | LRRFIP2 | 1.48 |
| 7129 | 3 | 4 | | IV-1 | LRSAM1 | 1.47 |
| 7130 | 3 | 4 | | IV-1 | LSG1 | 1.39 |
| 7131 | 3 | 4 | | IV-1 | LSM1 | 1.16 |
| 7132 | 3 | 4 | | IV-1 | LSM10 | 1.04 |
| 7133 | 3 | 4 | | IV-1 | LSM11 | 1.43 |
| 7134 | 3 | 4 | | IV-1 | LSM12 | 1.47 |
| 7135 | 3 | 4 | | IV-1 | LSM14A | 1.33 |
| 7136 | 3 | 4 | | IV-1 | LSM2 | 1.12 |
| 7137 | 3 | 4 | | IV-1 | LSM3 | 1.36 |
| 7138 | 3 | 4 | | IV-1 | LSM7 | 1.18 |
| 7139 | 3 | 4 | | IV-1 | LSP1 | 1.03 |
| 7140 | 3 | 4 | | IV-1 | LSS | 1.13 |
| 7141 | 3 | 4 | | IV-1 | LTN1 | 1.37 |
| 7142 | 3 | 4 | | IV-1 | LUC7L2 | 1.38 |
| 7143 | 3 | 4 | | IV-1 | LUC7L3 | 1.37 |
| 7144 | 3 | 4 | | IV-1 | LYN | 1.22 |
| 7145 | 3 | 4 | | IV-1 | LYNX1 | 1.25 |
| 7146 | 3 | 4 | | IV-1 | LYPLA1 | 1.48 |
| 7147 | 3 | 4 | | IV-1 | LYPLA2 | 1.15 |
| 7148 | 3 | 4 | | IV-1 | LYRM4 | 1.17 |
| 7149 | 3 | 4 | | IV-1 | LYRM5 | 1.22 |
| 7150 | 3 | 4 | | IV-1 | LYRM7 | 1.20 |
| 7151 | 3 | 4 | | IV-1 | LYSMD2 | 1.11 |
| 7152 | 3 | 4 | | IV-1 | LYSMD3 | 1.10 |
| 7153 | 3 | 4 | | IV-1 | LYSMD4 | 1.45 |
| 7154 | 3 | 4 | | IV-1 | LYST | 1.06 |
| 7155 | 3 | 4 | | IV-1 | LZTFL1 | 1.05 |
| 7156 | 3 | 4 | | IV-1 | LZTS2 | 1.25 |
| 7157 | 3 | 4 | | IV-1 | MACF1 | 1.34 |
| 7158 | 3 | 4 | | IV-1 | MAD1L1 | 1.29 |
| 7159 | 3 | 4 | | IV-1 | MAD2L1 | 1.13 |
| 7160 | 3 | 4 | | IV-1 | MAD2L2 | 1.43 |
| 7161 | 3 | 4 | | IV-1 | MAEA | 1.30 |
| 7162 | 3 | 4 | | IV-1 | MAF1 | 1.18 |
| 7163 | 3 | 4 | | IV-1 | MAFK | 1.34 |
| 7164 | 3 | 4 | | IV-1 | MAGED2 | 1.30 |
| 7165 | 3 | 4 | | IV-1 | MAGEH1 | 1.05 |
| 7166 | 3 | 4 | | IV-1 | MAGOH | 1.10 |
| 7167 | 3 | 4 | | IV-1 | MAK16 | 1.27 |
| 7168 | 3 | 4 | | IV-1 | MAL | 1.35 |
| 7169 | 3 | 4 | | IV-1 | MALSU1 | 1.12 |
| 7170 | 3 | 4 | | IV-1 | MALT1 | 1.46 |
| 7171 | 3 | 4 | | IV-1 | MAML1 | 1.28 |
| 7172 | 3 | 4 | | IV-1 | MAML3 | 1.42 |
| 7173 | 3 | 4 | | IV-1 | MAN1B1 | 1.31 |
| 7174 | 3 | 4 | | IV-1 | MAN2B2 | 1.04 |
| 7175 | 3 | 4 | | IV-1 | MAP1LC3B | 1.07 |
| 7176 | 3 | 4 | | IV-1 | MAP1LC3B2 | 1.01 |
| 7177 | 3 | 4 | | IV-1 | MAP2K2 | 1.16 |
| 7178 | 3 | 4 | | IV-1 | MAP2K3 | 1.34 |
| 7179 | 3 | 4 | | IV-1 | MAP2K4 | 1.11 |
| 7180 | 3 | 4 | | IV-1 | MAP2K5 | 1.30 |
| 7181 | 3 | 4 | | IV-1 | MAP3K10 | 1.42 |
| 7182 | 3 | 4 | | IV-1 | MAP3K11 | 1.37 |
| 7183 | 3 | 4 | | IV-1 | MAP3K13 | 1.23 |
| 7184 | 3 | 4 | | IV-1 | MAP3K14 | 1.24 |
| 7185 | 3 | 4 | | IV-1 | MAP3K2 | 1.05 |
| 7186 | 3 | 4 | | IV-1 | MAP3K3 | 1.34 |
| 7187 | 3 | 4 | | IV-1 | MAP3K5 | 1.29 |
| 7188 | 3 | 4 | | IV-1 | MAP3K7 | 1.36 |
| 7189 | 3 | 4 | | IV-1 | MAP4K3 | 1.45 |
| 7190 | 3 | 4 | | IV-1 | MAP4K4 | 1.33 |
| 7191 | 3 | 4 | | IV-1 | MAP4K5 | 1.50 |
| 7192 | 3 | 4 | | IV-1 | MAP7D1 | 1.09 |
| 7193 | 3 | 4 | | IV-1 | MAP7D3 | 1.38 |
| 7194 | 3 | 4 | | IV-1 | MAPK7 | 1.38 |
| 7195 | 3 | 4 | | IV-1 | MAPKAPK5 | 1.14 |
| 7196 | 3 | 4 | | IV-1 | MAPKBP1 | 1.38 |
| 7197 | 3 | 4 | | IV-1 | MAPRE3 | 1.02 |
| 7198 | 3 | 4 | | IV-1 | 42434 | 1.47 |
| 7199 | 3 | 4 | | IV-1 | 42435 | 1.27 |
| 7200 | 3 | 4 | | IV-1 | MARK2 | 1.07 |
| 7201 | 3 | 4 | | IV-1 | MARK3 | 1.16 |
| 7202 | 3 | 4 | | IV-1 | MARS | 1.22 |
| 7203 | 3 | 4 | | IV-1 | MARS2 | 1.08 |
| 7204 | 3 | 4 | | IV-1 | MAST4 | 1.10 |
| 7205 | 3 | 4 | | IV-1 | MAT2B | 1.24 |
| 7206 | 3 | 4 | | IV-1 | MAU2 | 1.12 |
| 7207 | 3 | 4 | | IV-1 | MAZ | 1.17 |
| 7208 | 3 | 4 | | IV-1 | MBD1 | 1.07 |
| 7209 | 3 | 4 | | IV-1 | MBD2 | 1.30 |
| 7210 | 3 | 4 | | IV-1 | MBD4 | 1.20 |
| 7211 | 3 | 4 | | IV-1 | MBD5 | 1.20 |
| 7212 | 3 | 4 | | IV-1 | MBIP | 1.15 |
| 7213 | 3 | 4 | | IV-1 | MBNL1 | 1.26 |
| 7214 | 3 | 4 | | IV-1 | MBNL2 | 1.34 |
| 7215 | 3 | 4 | | IV-1 | MBNL3 | 1.32 |
| 7216 | 3 | 4 | | IV-1 | M8TD1 | 1.06 |
| 7217 | 3 | 4 | | IV-1 | MCART1 | 1.30 |
| 7218 | 3 | 4 | | IV-1 | MCCC1 | 1.37 |
| 7219 | 3 | 4 | | IV-1 | MCL1 | 1.10 |
| 7220 | 3 | 4 | | IV-1 | MCM5 | 1.46 |
| 7221 | 3 | 4 | | IV-1 | MCM7 | 1.08 |
| 7222 | 3 | 4 | | IV-1 | MCM8 | 1.47 |
| 7223 | 3 | 4 | | IV-1 | MCM9 | 1.47 |
| 7224 | 3 | 4 | | IV-1 | MCPH1 | 1.47 |
| 7225 | 3 | 4 | | IV-1 | MCTP2 | 1.00 |
| 7226 | 3 | 4 | | IV-1 | MCTS1 | 1.08 |
| 7227 | 3 | 4 | | IV-1 | MCU | 1.35 |
| 7228 | 3 | 4 | | IV-1 | MDC1 | 1.10 |
| 7229 | 3 | 4 | | IV-1 | MDN1 | 1.06 |
| 7230 | 3 | 4 | | IV-1 | MDP1 | 1.16 |
| 7231 | 3 | 4 | | IV-1 | MEA1 | 1.07 |
| 7232 | 3 | 4 | | IV-1 | MEAF6 | 1.34 |
| 7233 | 3 | 4 | | IV-1 | MED10 | 1.41 |
| 7234 | 3 | 4 | | IV-1 | MED12 | 1.23 |
| 7235 | 3 | 4 | | IV-1 | MED13L | 1.17 |
| 7236 | 3 | 4 | | IV-1 | MED14 | 1.50 |
| 7237 | 3 | 4 | | IV-1 | MED15 | 1.33 |
| 7238 | 3 | 4 | | IV-1 | MED18 | 1.09 |
| 7239 | 3 | 4 | | IV-1 | MED19 | 1.18 |
| 7240 | 3 | 4 | | IV-1 | MED20 | 1.49 |
| 7241 | 3 | 4 | | IV-1 | MED21 | 1.46 |
| 7242 | 3 | 4 | | IV-1 | MED23 | 1.40 |
| 7243 | 3 | 4 | | IV-1 | MED26 | 1.44 |
| 7244 | 3 | 4 | | IV-1 | MED28 | 1.32 |
| 7245 | 3 | 4 | | IV-1 | MED29 | 1.28 |
| 7246 | 3 | 4 | | IV-1 | MED30 | 1.08 |
| 7247 | 3 | 4 | | IV-1 | MED31 | 1.01 |
| 7248 | 3 | 4 | | IV-1 | MED6 | 1.49 |
| 7249 | 3 | 4 | | IV-1 | MED7 | 1.40 |
| 7250 | 3 | 4 | | IV-1 | MED9 | 1.46 |
| 7251 | 3 | 4 | | IV-1 | MEF2BNB | 1.00 |
| 7252 | 3 | 4 | | IV-1 | MEF2D | 1.29 |
| 7253 | 3 | 4 | | IV-1 | MEFV | 1.06 |
| 7254 | 3 | 4 | | IV-1 | MEGF9 | 1.17 |
| 7255 | 3 | 4 | | IV-1 | MEMO1 | 1.39 |
| 7256 | 3 | 4 | | IV-1 | MEN1 | 1.39 |
| 7257 | 3 | 4 | | IV-1 | MEPCE | 1.07 |
| 7258 | 3 | 4 | | IV-1 | MESDC1 | 1.38 |
| 7259 | 3 | 4 | | IV-1 | METTL1 | 1.05 |
| 7260 | 3 | 4 | | IV-1 | METTL14 | 1.50 |
| 7261 | 3 | 4 | | IV-1 | METTL21A | 1.42 |
| 7262 | 3 | 4 | | IV-1 | METTL23 | 1.25 |
| 7263 | 3 | 4 | | IV-1 | METTL2A | 1.11 |
| 7264 | 3 | 4 | | IV-1 | METTL3 | 1.23 |
| 7265 | 3 | 4 | | IV-1 | METTL5 | 1.34 |
| 7266 | 3 | 4 | | IV-1 | METTL6 | 1.43 |
| 7267 | 3 | 4 | | IV-1 | METTL8 | 1.00 |
| 7268 | 3 | 4 | | IV-1 | MEX3C | 1.13 |
| 7269 | 3 | 4 | | IV-1 | MFAP1 | 1.46 |
| 7270 | 3 | 4 | | IV-1 | MFF | 1.39 |
| 7271 | 3 | 4 | | IV-1 | MFN1 | 1.28 |
| 7272 | 3 | 4 | | IV-1 | MFNG | 1.29 |
| 7273 | 3 | 4 | | IV-1 | MFSD12 | 1.36 |
| 7274 | 3 | 4 | | IV-1 | MFSD2A | 1.38 |
| 7275 | 3 | 4 | | IV-1 | MFSD8 | 1.23 |
| 7276 | 3 | 4 | | IV-1 | MGA | 1.45 |
| 7277 | 3 | 4 | | IV-1 | MGAM | 1.19 |
| 7278 | 3 | 4 | | IV-1 | MGAT4A | 1.15 |
| 7279 | 3 | 4 | | IV-1 | MGAT4B | 1.41 |
| 7280 | 3 | 4 | | IV-1 | MGAT5 | 1.17 |
| 7281 | 3 | 4 | | IV-1 | MGC16142 | 1.06 |
| 7282 | 3 | 4 | | IV-1 | MGC23284 | 1.32 |
| 7283 | 3 | 4 | | IV-1 | MGC27345 | 1.16 |
| 7284 | 3 | 4 | | IV-1 | MGC2752 | 1.22 |
| 7285 | 3 | 4 | | IV-1 | MGC72080 | 1.49 |
| 7286 | 3 | 4 | | IV-1 | MGEA5 | 1.06 |
| 7287 | 3 | 4 | | IV-1 | MGRN1 | 1.12 |
| 7288 | 3 | 4 | | IV-1 | MIA3 | 1.38 |
| 7289 | 3 | 4 | | IV-1 | MIB1 | 1.46 |
| 7290 | 3 | 4 | | IV-1 | MICAL3 | 1.10 |
| 7291 | 3 | 4 | | IV-1 | MICALL1 | 1.28 |

Fig. 41 - 39

| | | | | | | | |
|---|---|---|---|---|---|---|---|
| 7292 | 3 | 4 | | | IV-1 | MID2 | 1.10 |
| 7293 | 3 | 4 | | | IV-1 | MIER1 | 1.09 |
| 7294 | 3 | 4 | | | IV-1 | MIF4GD | 1.27 |
| 7295 | 3 | 4 | | | IV-1 | MINK1 | 1.23 |
| 7296 | 3 | 4 | | | IV-1 | MINOS1 | 1.32 |
| 7297 | 3 | 4 | | | IV-1 | MIS12 | 1.15 |
| 7298 | 3 | 4 | | | IV-1 | MIS18A | 1.43 |
| 7299 | 3 | 4 | | | IV-1 | MITD1 | 1.05 |
| 7300 | 3 | 4 | | | IV-1 | MKKS | 1.33 |
| 7301 | 3 | 4 | | | IV-1 | MKL2 | 1.26 |
| 7302 | 3 | 4 | | | IV-1 | MKLN1 | 1.30 |
| 7303 | 3 | 4 | | | IV-1 | MKRN2 | 1.38 |
| 7304 | 3 | 4 | | | IV-1 | MLH1 | 1.45 |
| 7305 | 3 | 4 | | | IV-1 | MLKL | 1.18 |
| 7306 | 3 | 4 | | | IV-1 | MLL2 | 1.01 |
| 7307 | 3 | 4 | | | IV-1 | MLL3 | 1.27 |
| 7308 | 3 | 4 | | | IV-1 | MLL5 | 1.25 |
| 7309 | 3 | 4 | | | IV-1 | MLLT1 | 1.24 |
| 7310 | 3 | 4 | | | IV-1 | MLLT10 | 1.30 |
| 7311 | 3 | 4 | | | IV-1 | MLLT3 | 1.35 |
| 7312 | 3 | 4 | | | IV-1 | MLST8 | 1.40 |
| 7313 | 3 | 4 | | | IV-1 | MLX | 1.28 |
| 7314 | 3 | 4 | | | IV-1 | MLYCD | 1.41 |
| 7315 | 3 | 4 | | | IV-1 | MMACHC | 1.19 |
| 7316 | 3 | 4 | | | IV-1 | MNAT1 | 1.13 |
| 7317 | 3 | 4 | | | IV-1 | MNDA | 1.09 |
| 7318 | 3 | 4 | | | IV-1 | MNF1 | 1.47 |
| 7319 | 3 | 4 | | | IV-1 | MNT | 1.40 |
| 7320 | 3 | 4 | | | IV-1 | MOAP1 | 1.29 |
| 7321 | 3 | 4 | | | IV-1 | MOB2 | 1.30 |
| 7322 | 3 | 4 | | | IV-1 | MOB3B | 1.02 |
| 7323 | 3 | 4 | | | IV-1 | MOCS2 | 1.20 |
| 7324 | 3 | 4 | | | IV-1 | MOGS | 1.45 |
| 7325 | 3 | 4 | | | IV-1 | MON1B | 1.39 |
| 7326 | 3 | 4 | | | IV-1 | MON2 | 1.29 |
| 7327 | 3 | 4 | | | IV-1 | MORC2 | 1.32 |
| 7328 | 3 | 4 | | | IV-1 | MORC3 | 1.49 |
| 7329 | 3 | 4 | | | IV-1 | MOSPD2 | 1.23 |
| 7330 | 3 | 4 | | | IV-1 | MPG | 1.23 |
| 7331 | 3 | 4 | | | IV-1 | MPHOSPH10 | 1.44 |
| 7332 | 3 | 4 | | | IV-1 | MPHOSPH9 | 1.26 |
| 7333 | 3 | 4 | | | IV-1 | MPP5 | 1.44 |
| 7334 | 3 | 4 | | | IV-1 | MPRIP | 1.23 |
| 7335 | 3 | 4 | | | IV-1 | MPST | 1.05 |
| 7336 | 3 | 4 | | | IV-1 | MPV17L2 | 1.39 |
| 7337 | 3 | 4 | | | IV-1 | MRE11A | 1.43 |
| 7338 | 3 | 4 | | | IV-1 | MRFAP1 | 1.40 |
| 7339 | 3 | 4 | | | IV-1 | MRI1 | 1.33 |
| 7340 | 3 | 4 | | | IV-1 | MRM1 | 1.49 |
| 7341 | 3 | 4 | | | IV-1 | MRP63 | 1.13 |
| 7342 | 3 | 4 | | | IV-1 | MRPL10 | 1.37 |
| 7343 | 3 | 4 | | | IV-1 | MRPL11 | 1.46 |
| 7344 | 3 | 4 | | | IV-1 | MRPL12 | 1.49 |
| 7345 | 3 | 4 | | | IV-1 | MRPL14 | 1.34 |
| 7346 | 3 | 4 | | | IV-1 | MRPL16 | 1.47 |
| 7347 | 3 | 4 | | | IV-1 | MRPL17 | 1.14 |
| 7348 | 3 | 4 | | | IV-1 | MRPL2 | 1.18 |
| 7349 | 3 | 4 | | | IV-1 | MRPL22 | 1.08 |
| 7350 | 3 | 4 | | | IV-1 | MRPL24 | 1.35 |
| 7351 | 3 | 4 | | | IV-1 | MRPL3 | 1.50 |
| 7352 | 3 | 4 | | | IV-1 | MRPL30 | 1.46 |
| 7353 | 3 | 4 | | | IV-1 | MRPL32 | 1.16 |
| 7354 | 3 | 4 | | | IV-1 | MRPL34 | 1.07 |
| 7355 | 3 | 4 | | | IV-1 | MRPL36 | 1.27 |
| 7356 | 3 | 4 | | | IV-1 | MRPL39 | 1.17 |
| 7357 | 3 | 4 | | | IV-1 | MRPL40 | 1.08 |
| 7358 | 3 | 4 | | | IV-1 | MRPL42 | 1.33 |
| 7359 | 3 | 4 | | | IV-1 | MRPL42P5 | 1.05 |
| 7360 | 3 | 4 | | | IV-1 | MRPL43 | 1.01 |
| 7361 | 3 | 4 | | | IV-1 | MRPL44 | 1.44 |
| 7362 | 3 | 4 | | | IV-1 | MRPL48 | 1.27 |
| 7363 | 3 | 4 | | | IV-1 | MRPL50 | 1.21 |
| 7364 | 3 | 4 | | | IV-1 | MRPL51 | 1.48 |
| 7365 | 3 | 4 | | | IV-1 | MRPL53 | 1.21 |
| 7366 | 3 | 4 | | | IV-1 | MRPL54 | 1.00 |
| 7367 | 3 | 4 | | | IV-1 | MRPL55 | 1.43 |
| 7368 | 3 | 4 | | | IV-1 | MRPL9 | 1.37 |
| 7369 | 3 | 4 | | | IV-1 | MRPS14 | 1.49 |
| 7370 | 3 | 4 | | | IV-1 | MRPS15 | 1.36 |
| 7371 | 3 | 4 | | | IV-1 | MRPS16 | 1.20 |
| 7372 | 3 | 4 | | | IV-1 | MRPS17 | 1.31 |
| 7373 | 3 | 4 | | | IV-1 | MRPS18A | 1.26 |
| 7374 | 3 | 4 | | | IV-1 | MRPS18B | 1.35 |
| 7375 | 3 | 4 | | | IV-1 | MRPS2 | 1.46 |
| 7376 | 3 | 4 | | | IV-1 | MRPS24 | 1.48 |
| 7377 | 3 | 4 | | | IV-1 | MRPS25 | 1.20 |
| 7378 | 3 | 4 | | | IV-1 | MRPS26 | 1.18 |
| 7379 | 3 | 4 | | | IV-1 | MRPS27 | 1.33 |
| 7380 | 3 | 4 | | | IV-1 | MRPS31 | 1.31 |
| 7381 | 3 | 4 | | | IV-1 | MRPS36 | 1.41 |
| 7382 | 3 | 4 | | | IV-1 | MRPS6 | 1.16 |
| 7383 | 3 | 4 | | | IV-1 | MRS2 | 1.45 |
| 7384 | 3 | 4 | | | IV-1 | MRTO4 | 1.28 |
| 7385 | 3 | 4 | | | IV-1 | MSL2 | 1.20 |
| 7386 | 3 | 4 | | | IV-1 | MSL3 | 1.28 |
| 7387 | 3 | 4 | | | IV-1 | MSL3P1 | 1.08 |
| 7388 | 3 | 4 | | | IV-1 | MSMO1 | 1.34 |
| 7389 | 3 | 4 | | | IV-1 | MSN | 1.37 |
| 7390 | 3 | 4 | | | IV-1 | MST4 | 1.43 |
| 7391 | 3 | 4 | | | IV-1 | MTA3 | 1.06 |
| 7392 | 3 | 4 | | | IV-1 | MTCH1 | 1.00 |
| 7393 | 3 | 4 | | | IV-1 | MTCP1NB | 1.23 |
| 7394 | 3 | 4 | | | IV-1 | MTERF | 1.30 |
| 7395 | 3 | 4 | | | IV-1 | MTERFD1 | 1.29 |
| 7396 | 3 | 4 | | | IV-1 | MTFMT | 1.10 |
| 7397 | 3 | 4 | | | IV-1 | MTFP1 | 1.19 |
| 7398 | 3 | 4 | | | IV-1 | MTFR1 | 1.46 |
| 7399 | 3 | 4 | | | IV-1 | MTIF3 | 1.10 |
| 7400 | 3 | 4 | | | IV-1 | MTL5 | 1.29 |
| 7401 | 3 | 4 | | | IV-1 | MTM1 | 1.45 |
| 7402 | 3 | 4 | | | IV-1 | MTMR1 | 1.19 |
| 7403 | 3 | 4 | | | IV-1 | MTMR10 | 1.09 |
| 7404 | 3 | 4 | | | IV-1 | MTMR12 | 1.48 |
| 7405 | 3 | 4 | | | IV-1 | MTMR2 | 1.40 |
| 7406 | 3 | 4 | | | IV-1 | MTMR3 | 1.12 |
| 7407 | 3 | 4 | | | IV-1 | MTMR4 | 1.21 |
| 7408 | 3 | 4 | | | IV-1 | MTO1 | 1.47 |
| 7409 | 3 | 4 | | | IV-1 | MTX1 | 1.07 |
| 7410 | 3 | 4 | | | IV-1 | MTX3 | 1.06 |
| 7411 | 3 | 4 | | | IV-1 | MUL1 | 1.44 |
| 7412 | 3 | 4 | | | IV-1 | MUM1 | 1.36 |
| 7413 | 3 | 4 | | | IV-1 | MUS81 | 1.34 |
| 7414 | 3 | 4 | | | IV-1 | MUT | 1.39 |
| 7415 | 3 | 4 | | | IV-1 | MUTED | 1.32 |
| 7416 | 3 | 4 | | | IV-1 | MVD | 1.49 |
| 7417 | 3 | 4 | | | IV-1 | MX2 | 1.16 |
| 7418 | 3 | 4 | | | IV-1 | MXD4 | 1.10 |
| 7419 | 3 | 4 | | | IV-1 | MYADM | 1.10 |
| 7420 | 3 | 4 | | | IV-1 | MYCBP | 1.44 |
| 7421 | 3 | 4 | | | IV-1 | MYH9 | 1.45 |
| 7422 | 3 | 4 | | | IV-1 | MYL12A | 1.27 |
| 7423 | 3 | 4 | | | IV-1 | MYL12B | 1.02 |
| 7424 | 3 | 4 | | | IV-1 | MYNN | 1.11 |
| 7425 | 3 | 4 | | | IV-1 | MYO1F | 1.07 |
| 7426 | 3 | 4 | | | IV-1 | MYO9B | 1.20 |
| 7427 | 3 | 4 | | | IV-1 | MYPOP | 1.28 |
| 7428 | 3 | 4 | | | IV-1 | MZT1 | 1.32 |
| 7429 | 3 | 4 | | | IV-1 | MZT2A | 1.45 |
| 7430 | 3 | 4 | | | IV-1 | MZT2B | 1.35 |
| 7431 | 3 | 4 | | | IV-1 | N4BP2L1 | 1.27 |
| 7432 | 3 | 4 | | | IV-1 | NAA16 | 1.03 |
| 7433 | 3 | 4 | | | IV-1 | NAA38 | 1.21 |
| 7434 | 3 | 4 | | | IV-1 | NAA50 | 1.40 |
| 7435 | 3 | 4 | | | IV-1 | NAA60 | 1.01 |
| 7436 | 3 | 4 | | | IV-1 | NAALADL1 | 1.18 |
| 7437 | 3 | 4 | | | IV-1 | NAB1 | 1.03 |
| 7438 | 3 | 4 | | | IV-1 | NAB2 | 1.24 |
| 7439 | 3 | 4 | | | IV-1 | NACA | 1.33 |
| 7440 | 3 | 4 | | | IV-1 | NACC1 | 1.45 |
| 7441 | 3 | 4 | | | IV-1 | NADK | 1.01 |
| 7442 | 3 | 4 | | | IV-1 | NADSYN1 | 1.29 |
| 7443 | 3 | 4 | | | IV-1 | NAGS | 1.15 |
| 7444 | 3 | 4 | | | IV-1 | NAIF1 | 1.30 |
| 7445 | 3 | 4 | | | IV-1 | NAP1L4 | 1.32 |
| 7446 | 3 | 4 | | | IV-1 | NAP1L5 | 1.35 |
| 7447 | 3 | 4 | | | IV-1 | NAPA | 1.06 |
| 7448 | 3 | 4 | | | IV-1 | NAPB | 1.24 |
| 7449 | 3 | 4 | | | IV-1 | NAPG | 1.35 |
| 7450 | 3 | 4 | | | IV-1 | NAPSA | 1.17 |
| 7451 | 3 | 4 | | | IV-1 | NARF | 1.04 |
| 7452 | 3 | 4 | | | IV-1 | NARG2 | 1.18 |
| 7453 | 3 | 4 | | | IV-1 | NARS2 | 1.38 |
| 7454 | 3 | 4 | | | IV-1 | NASP | 1.13 |
| 7455 | 3 | 4 | | | IV-1 | NAT14 | 1.09 |
| 7456 | 3 | 4 | | | IV-1 | NAT9 | 1.41 |
| 7457 | 3 | 4 | | | IV-1 | NAV1 | 1.13 |
| 7458 | 3 | 4 | | | IV-1 | NBN | 1.24 |
| 7459 | 3 | 4 | | | IV-1 | NBPF11 | 1.45 |
| 7460 | 3 | 4 | | | IV-1 | NBPF16 | 1.17 |
| 7461 | 3 | 4 | | | IV-1 | NCAPD3 | 1.22 |
| 7462 | 3 | 4 | | | IV-1 | NCF2 | 1.32 |
| 7463 | 3 | 4 | | | IV-1 | NCK1 | 1.16 |
| 7464 | 3 | 4 | | | IV-1 | NCOA1 | 1.11 |
| 7465 | 3 | 4 | | | IV-1 | NCOA2 | 1.12 |
| 7466 | 3 | 4 | | | IV-1 | NCOA4 | 1.12 |
| 7467 | 3 | 4 | | | IV-1 | NCOA5 | 1.45 |
| 7468 | 3 | 4 | | | IV-1 | NCOA6 | 1.34 |
| 7469 | 3 | 4 | | | IV-1 | NDNL2 | 1.28 |
| 7470 | 3 | 4 | | | IV-1 | NDOR1 | 1.03 |
| 7471 | 3 | 4 | | | IV-1 | NDRG3 | 1.42 |
| 7472 | 3 | 4 | | | IV-1 | NDST2 | 1.41 |
| 7473 | 3 | 4 | | | IV-1 | NDUFA11 | 1.32 |
| 7474 | 3 | 4 | | | IV-1 | NDUFA13 | 1.18 |
| 7475 | 3 | 4 | | | IV-1 | NDUFA4 | 1.06 |
| 7476 | 3 | 4 | | | IV-1 | NDUFA5 | 1.25 |
| 7477 | 3 | 4 | | | IV-1 | NDUFA7 | 1.21 |
| 7478 | 3 | 4 | | | IV-1 | NDUFA8 | 1.38 |
| 7479 | 3 | 4 | | | IV-1 | NDUFB10 | 1.25 |
| 7480 | 3 | 4 | | | IV-1 | NDUFB11 | 1.26 |
| 7481 | 3 | 4 | | | IV-1 | NDUFB7 | 1.02 |
| 7482 | 3 | 4 | | | IV-1 | NDUFB8 | 1.29 |
| 7483 | 3 | 4 | | | IV-1 | NDUFB9 | 1.28 |

Fig. 41 - 40

| | | | | | | | |
|---|---|---|---|---|---|---|---|
| 7484 | 3 | 4 | | | IV-1 | NDUFC2 | 1.25 |
| 7485 | 3 | 4 | | | IV-1 | NDUFS3 | 1.40 |
| 7486 | 3 | 4 | | | IV-1 | NDUFS4 | 1.41 |
| 7487 | 3 | 4 | | | IV-1 | NDUFS5 | 1.47 |
| 7488 | 3 | 4 | | | IV-1 | NDUFS7 | 1.33 |
| 7489 | 3 | 4 | | | IV-1 | NDUFV1 | 1.34 |
| 7490 | 3 | 4 | | | IV-1 | NDUFV2 | 1.09 |
| 7491 | 3 | 4 | | | IV-1 | NECAB3 | 1.48 |
| 7492 | 3 | 4 | | | IV-1 | NECAP1 | 1.27 |
| 7493 | 3 | 4 | | | IV-1 | NEDD4 | 1.23 |
| 7494 | 3 | 4 | | | IV-1 | NEK1 | 1.37 |
| 7495 | 3 | 4 | | | IV-1 | NEK3 | 1.08 |
| 7496 | 3 | 4 | | | IV-1 | NEK7 | 1.05 |
| 7497 | 3 | 4 | | | IV-1 | NEK8 | 1.06 |
| 7498 | 3 | 4 | | | IV-1 | NELF | 1.23 |
| 7499 | 3 | 4 | | | IV-1 | NENF | 1.27 |
| 7500 | 3 | 4 | | | IV-1 | NEURL4 | 1.01 |
| 7501 | 3 | 4 | | | IV-1 | NFAM1 | 1.29 |
| 7502 | 3 | 4 | | | IV-1 | NFATC2IP | 1.09 |
| 7503 | 3 | 4 | | | IV-1 | NFATC3 | 1.40 |
| 7504 | 3 | 4 | | | IV-1 | NFIA | 1.42 |
| 7505 | 3 | 4 | | | IV-1 | NFIL3 | 1.12 |
| 7506 | 3 | 4 | | | IV-1 | NFKB2 | 1.21 |
| 7507 | 3 | 4 | | | IV-1 | NFKBIB | 1.14 |
| 7508 | 3 | 4 | | | IV-1 | NFU1 | 1.08 |
| 7509 | 3 | 4 | | | IV-1 | NFX1 | 1.33 |
| 7510 | 3 | 4 | | | IV-1 | NFYA | 1.29 |
| 7511 | 3 | 4 | | | IV-1 | NFYB | 1.39 |
| 7512 | 3 | 4 | | | IV-1 | NFYC | 1.45 |
| 7513 | 3 | 4 | | | IV-1 | NGDN | 1.32 |
| 7514 | 3 | 4 | | | IV-1 | NGFRAP1 | 1.24 |
| 7515 | 3 | 4 | | | IV-1 | NGLY1 | 1.25 |
| 7516 | 3 | 4 | | | IV-1 | NGRN | 1.19 |
| 7517 | 3 | 4 | | | IV-1 | NHLRC2 | 1.22 |
| 7518 | 3 | 4 | | | IV-1 | NHP2 | 1.12 |
| 7519 | 3 | 4 | | | IV-1 | NHP2L1 | 1.35 |
| 7520 | 3 | 4 | | | IV-1 | NICN1 | 1.49 |
| 7521 | 3 | 4 | | | IV-1 | NIF3L1 | 1.27 |
| 7522 | 3 | 4 | | | IV-1 | NIN | 1.39 |
| 7523 | 3 | 4 | | | IV-1 | NIP7 | 1.33 |
| 7524 | 3 | 4 | | | IV-1 | NIPBL | 1.34 |
| 7525 | 3 | 4 | | | IV-1 | NIPSNAP1 | 1.06 |
| 7526 | 3 | 4 | | | IV-1 | NISCH | 1.44 |
| 7527 | 3 | 4 | | | IV-1 | NLK | 1.39 |
| 7528 | 3 | 4 | | | IV-1 | NLRX1 | 1.39 |
| 7529 | 3 | 4 | | | IV-1 | NME1 | 1.18 |
| 7530 | 3 | 4 | | | IV-1 | NME6 | 1.46 |
| 7531 | 3 | 4 | | | IV-1 | NME7 | 1.17 |
| 7532 | 3 | 4 | | | IV-1 | NMI | 1.32 |
| 7533 | 3 | 4 | | | IV-1 | NMRAL1 | 1.40 |
| 7534 | 3 | 4 | | | IV-1 | NMT2 | 1.38 |
| 7535 | 3 | 4 | | | IV-1 | NOC3L | 1.15 |
| 7536 | 3 | 4 | | | IV-1 | NOC4L | 1.45 |
| 7537 | 3 | 4 | | | IV-1 | NOD1 | 1.32 |
| 7538 | 3 | 4 | | | IV-1 | NOL7 | 1.32 |
| 7539 | 3 | 4 | | | IV-1 | NONO | 1.49 |
| 7540 | 3 | 4 | | | IV-1 | NOP10 | 1.31 |
| 7541 | 3 | 4 | | | IV-1 | NOP14 | 1.45 |
| 7542 | 3 | 4 | | | IV-1 | NOP14-AS1 | 1.15 |
| 7543 | 3 | 4 | | | IV-1 | NOP16 | 1.25 |
| 7544 | 3 | 4 | | | IV-1 | NOP2 | 1.33 |
| 7545 | 3 | 4 | | | IV-1 | NPEPPS | 1.31 |
| 7546 | 3 | 4 | | | IV-1 | NPL | 1.47 |
| 7547 | 3 | 4 | | | IV-1 | NPM1 | 1.10 |
| 7548 | 3 | 4 | | | IV-1 | NPM3 | 1.30 |
| 7549 | 3 | 4 | | | IV-1 | NR1D2 | 1.07 |
| 7550 | 3 | 4 | | | IV-1 | NR1H2 | 1.25 |
| 7551 | 3 | 4 | | | IV-1 | NR1H3 | 1.01 |
| 7552 | 3 | 4 | | | IV-1 | NR2C1 | 1.24 |
| 7553 | 3 | 4 | | | IV-1 | NR2C2 | 1.23 |
| 7554 | 3 | 4 | | | IV-1 | NR2C2AP | 1.11 |
| 7555 | 3 | 4 | | | IV-1 | NR3C1 | 1.13 |
| 7556 | 3 | 4 | | | IV-1 | NRBP1 | 1.24 |
| 7557 | 3 | 4 | | | IV-1 | NRD1 | 1.43 |
| 7558 | 3 | 4 | | | IV-1 | NRF1 | 1.29 |
| 7559 | 3 | 4 | | | IV-1 | NSA2 | 1.10 |
| 7560 | 3 | 4 | | | IV-1 | NSL1 | 1.15 |
| 7561 | 3 | 4 | | | IV-1 | NSMAF | 1.29 |
| 7562 | 3 | 4 | | | IV-1 | NSUN3 | 1.46 |
| 7563 | 3 | 4 | | | IV-1 | NSUN4 | 1.48 |
| 7564 | 3 | 4 | | | IV-1 | NSUN5 | 1.30 |
| 7565 | 3 | 4 | | | IV-1 | NT5C2 | 1.10 |
| 7566 | 3 | 4 | | | IV-1 | NT5DC1 | 1.23 |
| 7567 | 3 | 4 | | | IV-1 | NT5DC2 | 1.33 |
| 7568 | 3 | 4 | | | IV-1 | NUB1 | 1.36 |
| 7569 | 3 | 4 | | | IV-1 | NUBP2 | 1.36 |
| 7570 | 3 | 4 | | | IV-1 | NUCB1 | 1.49 |
| 7571 | 3 | 4 | | | IV-1 | NUCB2 | 1.37 |
| 7572 | 3 | 4 | | | IV-1 | NUDCD2 | 1.22 |
| 7573 | 3 | 4 | | | IV-1 | NUDCD3 | 1.30 |
| 7574 | 3 | 4 | | | IV-1 | NUDT1 | 1.22 |
| 7575 | 3 | 4 | | | IV-1 | NUDT16L1 | 1.25 |
| 7576 | 3 | 4 | | | IV-1 | NUDT22 | 1.46 |
| 7577 | 3 | 4 | | | IV-1 | NUDT3 | 1.28 |
| 7578 | 3 | 4 | | | IV-1 | NUDT4 | 1.19 |
| 7579 | 3 | 4 | | | IV-1 | NUFIP1 | 1.26 |
| 7580 | 3 | 4 | | | IV-1 | NUFIP2 | 1.33 |
| 7581 | 3 | 4 | | | IV-1 | NUMB | 1.16 |
| 7582 | 3 | 4 | | | IV-1 | NUP153 | 1.43 |
| 7583 | 3 | 4 | | | IV-1 | NUP155 | 1.39 |
| 7584 | 3 | 4 | | | IV-1 | NUP43 | 1.33 |
| 7585 | 3 | 4 | | | IV-1 | NUP50 | 1.33 |
| 7586 | 3 | 4 | | | IV-1 | NUP98 | 1.37 |
| 7587 | 3 | 4 | | | IV-1 | NUPL2 | 1.33 |
| 7588 | 3 | 4 | | | IV-1 | NVL | 1.12 |
| 7589 | 3 | 4 | | | IV-1 | NXT2 | 1.49 |
| 7590 | 3 | 4 | | | IV-1 | OAZ1 | 1.02 |
| 7591 | 3 | 4 | | | IV-1 | OBFC2B | 1.43 |
| 7592 | 3 | 4 | | | IV-1 | OCIAD1 | 1.34 |
| 7593 | 3 | 4 | | | IV-1 | OGFOD2 | 1.21 |
| 7594 | 3 | 4 | | | IV-1 | OGFR | 1.29 |
| 7595 | 3 | 4 | | | IV-1 | OGG1 | 1.41 |
| 7596 | 3 | 4 | | | IV-1 | OLR1 | 1.16 |
| 7597 | 3 | 4 | | | IV-1 | OMA1 | 1.32 |
| 7598 | 3 | 4 | | | IV-1 | OPRL1 | 1.35 |
| 7599 | 3 | 4 | | | IV-1 | ORAI3 | 1.17 |
| 7600 | 3 | 4 | | | IV-1 | ORC2 | 1.28 |
| 7601 | 3 | 4 | | | IV-1 | ORC3 | 1.36 |
| 7602 | 3 | 4 | | | IV-1 | ORC4 | 1.45 |
| 7603 | 3 | 4 | | | IV-1 | ORC5 | 1.50 |
| 7604 | 3 | 4 | | | IV-1 | ORMDL3 | 1.07 |
| 7605 | 3 | 4 | | | IV-1 | OSBPL1A | 1.09 |
| 7606 | 3 | 4 | | | IV-1 | OSBPL2 | 1.03 |
| 7607 | 3 | 4 | | | IV-1 | OSBPL3 | 1.10 |
| 7608 | 3 | 4 | | | IV-1 | OSBPL8 | 1.11 |
| 7609 | 3 | 4 | | | IV-1 | OSBPL9 | 1.23 |
| 7610 | 3 | 4 | | | IV-1 | OST4 | 1.04 |
| 7611 | 3 | 4 | | | IV-1 | OSTF1 | 1.26 |
| 7612 | 3 | 4 | | | IV-1 | OTUB1 | 1.10 |
| 7613 | 3 | 4 | | | IV-1 | OTUD6B | 1.41 |
| 7614 | 3 | 4 | | | IV-1 | OTUD7B | 1.12 |
| 7615 | 3 | 4 | | | IV-1 | OVCA2 | 1.34 |
| 7616 | 3 | 4 | | | IV-1 | OXSM | 1.13 |
| 7617 | 3 | 4 | | | IV-1 | P2RY1 | 1.47 |
| 7618 | 3 | 4 | | | IV-1 | P2RY12 | 1.11 |
| 7619 | 3 | 4 | | | IV-1 | P2RY6 | 1.11 |
| 7620 | 3 | 4 | | | IV-1 | P2RY8 | 1.12 |
| 7621 | 3 | 4 | | | IV-1 | P4HTM | 1.43 |
| 7622 | 3 | 4 | | | IV-1 | PA2G4 | 1.40 |
| 7623 | 3 | 4 | | | IV-1 | PAAF1 | 1.49 |
| 7624 | 3 | 4 | | | IV-1 | PABPN1 | 1.01 |
| 7625 | 3 | 4 | | | IV-1 | PACS2 | 1.49 |
| 7626 | 3 | 4 | | | IV-1 | PACSIN2 | 1.13 |
| 7627 | 3 | 4 | | | IV-1 | PAF1 | 1.22 |
| 7628 | 3 | 4 | | | IV-1 | PAFAH1B2 | 1.47 |
| 7629 | 3 | 4 | | | IV-1 | PAFAH1B3 | 1.45 |
| 7630 | 3 | 4 | | | IV-1 | PAFAH2 | 1.03 |
| 7631 | 3 | 4 | | | IV-1 | PAG1 | 1.49 |
| 7632 | 3 | 4 | | | IV-1 | PAICS | 1.48 |
| 7633 | 3 | 4 | | | IV-1 | PAIP1 | 1.11 |
| 7634 | 3 | 4 | | | IV-1 | PAIP2 | 1.06 |
| 7635 | 3 | 4 | | | IV-1 | PAK4 | 1.34 |
| 7636 | 3 | 4 | | | IV-1 | PAL82 | 1.06 |
| 7637 | 3 | 4 | | | IV-1 | PAN3 | 1.13 |
| 7638 | 3 | 4 | | | IV-1 | PANK4 | 1.05 |
| 7639 | 3 | 4 | | | IV-1 | PAPD4 | 1.39 |
| 7640 | 3 | 4 | | | IV-1 | PAPD7 | 1.23 |
| 7641 | 3 | 4 | | | IV-1 | PAPOLB | 1.33 |
| 7642 | 3 | 4 | | | IV-1 | PAPOLG | 1.36 |
| 7643 | 3 | 4 | | | IV-1 | PAQR3 | 1.41 |
| 7644 | 3 | 4 | | | IV-1 | PARS | 1.04 |
| 7645 | 3 | 4 | | | IV-1 | PARG | 1.45 |
| 7646 | 3 | 4 | | | IV-1 | PARP10 | 1.36 |
| 7647 | 3 | 4 | | | IV-1 | PARP12 | 1.39 |
| 7648 | 3 | 4 | | | IV-1 | PARP3 | 1.09 |
| 7649 | 3 | 4 | | | IV-1 | PARP9 | 1.39 |
| 7650 | 3 | 4 | | | IV-1 | PARS2 | 1.06 |
| 7651 | 3 | 4 | | | IV-1 | PARVG | 1.03 |
| 7652 | 3 | 4 | | | IV-1 | PATL1 | 1.35 |
| 7653 | 3 | 4 | | | IV-1 | PATZ1 | 1.33 |
| 7654 | 3 | 4 | | | IV-1 | PAXIP1 | 1.18 |
| 7655 | 3 | 4 | | | IV-1 | PBLD | 1.37 |
| 7656 | 3 | 4 | | | IV-1 | PC | 1.34 |
| 7657 | 3 | 4 | | | IV-1 | PCBD2 | 1.40 |
| 7658 | 3 | 4 | | | IV-1 | PCBP1 | 1.40 |
| 7659 | 3 | 4 | | | IV-1 | PCBP2 | 1.43 |
| 7660 | 3 | 4 | | | IV-1 | PCDH12 | 1.43 |
| 7661 | 3 | 4 | | | IV-1 | PCF11 | 1.29 |
| 7662 | 3 | 4 | | | IV-1 | PCGF3 | 1.11 |
| 7663 | 3 | 4 | | | IV-1 | PCGF6 | 1.34 |
| 7664 | 3 | 4 | | | IV-1 | PCIF1 | 1.09 |
| 7665 | 3 | 4 | | | IV-1 | PCMTD2 | 1.15 |
| 7666 | 3 | 4 | | | IV-1 | PCNP | 1.26 |
| 7667 | 3 | 4 | | | IV-1 | PCNT | 1.06 |
| 7668 | 3 | 4 | | | IV-1 | PCNX | 1.12 |
| 7669 | 3 | 4 | | | IV-1 | PCNXL3 | 1.27 |
| 7670 | 3 | 4 | | | IV-1 | PCSK7 | 1.28 |
| 7671 | 3 | 4 | | | IV-1 | PCTP | 1.07 |
| 7672 | 3 | 4 | | | IV-1 | PCYT1A | 1.20 |
| 7673 | 3 | 4 | | | IV-1 | PCYT2 | 1.18 |
| 7674 | 3 | 4 | | | IV-1 | PDAP1 | 1.14 |
| 7675 | 3 | 4 | | | IV-1 | PDCD1 | 1.04 |

Fig. 41 - 41

| | | | | | | | | | | | | | | | |
|---|---|---|---|---|---|---|---|---|---|---|---|---|---|---|---|
| 7676 | 3 | 4 | | | IV-1 | PDCD10 | 1.38 | 7772 | 3 | 4 | | | IV-1 | PIP4K2A | 1.28 |
| 7677 | 3 | 4 | | | IV-1 | PDCD1LG2 | 1.22 | 7773 | 3 | 4 | | | IV-1 | PIP4K2C | 1.11 |
| 7678 | 3 | 4 | | | IV-1 | PDCD2 | 1.38 | 7774 | 3 | 4 | | | IV-1 | PIP5K1A | 1.13 |
| 7679 | 3 | 4 | | | IV-1 | PDCD2L | 1.25 | 7775 | 3 | 4 | | | IV-1 | PIP5K1P1 | 1.04 |
| 7680 | 3 | 4 | | | IV-1 | PDCD6 | 1.38 | 7776 | 3 | 4 | | | IV-1 | PIPSL | 1.42 |
| 7681 | 3 | 4 | | | IV-1 | PDCD6IP | 1.48 | 7777 | 3 | 4 | | | IV-1 | PITHD1 | 1.16 |
| 7682 | 3 | 4 | | | IV-1 | PDCL | 1.50 | 7778 | 3 | 4 | | | IV-1 | PITPNC1 | 1.25 |
| 7683 | 3 | 4 | | | IV-1 | PDDC1 | 1.15 | 7779 | 3 | 4 | | | IV-1 | PITPNM1 | 1.40 |
| 7684 | 3 | 4 | | | IV-1 | PDE6B | 1.16 | 7780 | 3 | 4 | | | IV-1 | PJA1 | 1.13 |
| 7685 | 3 | 4 | | | IV-1 | PDE6D | 1.22 | 7781 | 3 | 4 | | | IV-1 | PKD1 | 1.49 |
| 7686 | 3 | 4 | | | IV-1 | PDE8A | 1.44 | 7782 | 3 | 4 | | | IV-1 | PKNOX1 | 1.30 |
| 7687 | 3 | 4 | | | IV-1 | PDGFA | 1.12 | 7783 | 3 | 4 | | | IV-1 | PKP2 | 1.12 |
| 7688 | 3 | 4 | | | IV-1 | PDGFRB | 1.19 | 7784 | 3 | 4 | | | IV-1 | PKP4 | 1.15 |
| 7689 | 3 | 4 | | | IV-1 | PDLIM2 | 1.42 | 7785 | 3 | 4 | | | IV-1 | PLAUR | 1.45 |
| 7690 | 3 | 4 | | | IV-1 | PDP2 | 1.20 | 7786 | 3 | 4 | | | IV-1 | PLCD3 | 1.50 |
| 7691 | 3 | 4 | | | IV-1 | PDRG1 | 1.24 | 7787 | 3 | 4 | | | IV-1 | PLCG1 | 1.04 |
| 7692 | 3 | 4 | | | IV-1 | PDS5B | 1.39 | 7788 | 3 | 4 | | | IV-1 | PLCG2 | 1.10 |
| 7693 | 3 | 4 | | | IV-1 | PDSS2 | 1.38 | 7789 | 3 | 4 | | | IV-1 | PLCL2 | 1.26 |
| 7694 | 3 | 4 | | | IV-1 | PDXP | 1.37 | 7790 | 3 | 4 | | | IV-1 | PLCXD2 | 1.07 |
| 7695 | 3 | 4 | | | IV-1 | PDZD11 | 1.43 | 7791 | 3 | 4 | | | IV-1 | PLD6 | 1.24 |
| 7696 | 3 | 4 | | | IV-1 | PEBP1 | 1.14 | 7792 | 3 | 4 | | | IV-1 | PLEK | 1.40 |
| 7697 | 3 | 4 | | | IV-1 | PECAM1 | 1.41 | 7793 | 3 | 4 | | | IV-1 | PLEKHA2 | 1.26 |
| 7698 | 3 | 4 | | | IV-1 | PELI2 | 1.19 | 7794 | 3 | 4 | | | IV-1 | PLEKHA3 | 1.39 |
| 7699 | 3 | 4 | | | IV-1 | PELO | 1.26 | 7795 | 3 | 4 | | | IV-1 | PLEKHA8 | 1.38 |
| 7700 | 3 | 4 | | | IV-1 | PELP1 | 1.40 | 7796 | 3 | 4 | | | IV-1 | PLEKHG2 | 1.48 |
| 7701 | 3 | 4 | | | IV-1 | PEX1 | 1.10 | 7797 | 3 | 4 | | | IV-1 | PLEKHJ1 | 1.20 |
| 7702 | 3 | 4 | | | IV-1 | PEX10 | 1.19 | 7798 | 3 | 4 | | | IV-1 | PLEKHM1 | 1.13 |
| 7703 | 3 | 4 | | | IV-1 | PEX12 | 1.28 | 7799 | 3 | 4 | | | IV-1 | PLEKHM2 | 1.38 |
| 7704 | 3 | 4 | | | IV-1 | PEX13 | 1.46 | 7800 | 3 | 4 | | | IV-1 | PLEKHM3 | 1.24 |
| 7705 | 3 | 4 | | | IV-1 | PEX14 | 1.25 | 7801 | 3 | 4 | | | IV-1 | PLEKHO1 | 1.25 |
| 7706 | 3 | 4 | | | IV-1 | PEX16 | 1.02 | 7802 | 3 | 4 | | | IV-1 | PLEKHO2 | 1.36 |
| 7707 | 3 | 4 | | | IV-1 | PEX19 | 1.27 | 7803 | 3 | 4 | | | IV-1 | PLXNA1 | 1.03 |
| 7708 | 3 | 4 | | | IV-1 | PEX3 | 1.12 | 7804 | 3 | 4 | | | IV-1 | PLXNC1 | 1.24 |
| 7709 | 3 | 4 | | | IV-1 | PEX7 | 1.32 | 7805 | 3 | 4 | | | IV-1 | PM20D2 | 1.38 |
| 7710 | 3 | 4 | | | IV-1 | PFDN4 | 1.01 | 7806 | 3 | 4 | | | IV-1 | PMF1 | 1.01 |
| 7711 | 3 | 4 | | | IV-1 | PFDN6 | 1.24 | 7807 | 3 | 4 | | | IV-1 | PMM2 | 1.36 |
| 7712 | 3 | 4 | | | IV-1 | PFKM | 1.27 | 7808 | 3 | 4 | | | IV-1 | PMPCB | 1.13 |
| 7713 | 3 | 4 | | | IV-1 | PFN1 | 1.37 | 7809 | 3 | 4 | | | IV-1 | PMS1 | 1.28 |
| 7714 | 3 | 4 | | | IV-1 | PGA4 | 1.00 | 7810 | 3 | 4 | | | IV-1 | PMS2P1 | 1.21 |
| 7715 | 3 | 4 | | | IV-1 | PGAM5 | 1.30 | 7811 | 3 | 4 | | | IV-1 | PNMA1 | 1.38 |
| 7716 | 3 | 4 | | | IV-1 | PGAP2 | 1.46 | 7812 | 3 | 4 | | | IV-1 | PNN | 1.08 |
| 7717 | 3 | 4 | | | IV-1 | PGAP3 | 1.13 | 7813 | 3 | 4 | | | IV-1 | PNPLA2 | 1.07 |
| 7718 | 3 | 4 | | | IV-1 | PGBD2 | 1.29 | 7814 | 3 | 4 | | | IV-1 | PNPLA4 | 1.26 |
| 7719 | 3 | 4 | | | IV-1 | PGBD3 | 1.43 | 7815 | 3 | 4 | | | IV-1 | PNPT1 | 1.27 |
| 7720 | 3 | 4 | | | IV-1 | PGM1 | 1.43 | 7816 | 3 | 4 | | | IV-1 | PNRC2 | 1.30 |
| 7721 | 3 | 4 | | | IV-1 | PGM3 | 1.39 | 7817 | 3 | 4 | | | IV-1 | POC1B | 1.07 |
| 7722 | 3 | 4 | | | IV-1 | PGS1 | 1.09 | 7818 | 3 | 4 | | | IV-1 | PODXL2 | 1.30 |
| 7723 | 3 | 4 | | | IV-1 | PHB | 1.15 | 7819 | 3 | 4 | | | IV-1 | POFUT2 | 1.05 |
| 7724 | 3 | 4 | | | IV-1 | PHB2 | 1.14 | 7820 | 3 | 4 | | | IV-1 | POGLUT1 | 1.48 |
| 7725 | 3 | 4 | | | IV-1 | PHC1 | 1.19 | 7821 | 3 | 4 | | | IV-1 | POGZ | 1.33 |
| 7726 | 3 | 4 | | | IV-1 | PHC3 | 1.42 | 7822 | 3 | 4 | | | IV-1 | POLA1 | 1.34 |
| 7727 | 3 | 4 | | | IV-1 | PHF10 | 1.45 | 7823 | 3 | 4 | | | IV-1 | POLD1 | 1.40 |
| 7728 | 3 | 4 | | | IV-1 | PHF11 | 1.32 | 7824 | 3 | 4 | | | IV-1 | POLD2 | 1.42 |
| 7729 | 3 | 4 | | | IV-1 | PHF13 | 1.45 | 7825 | 3 | 4 | | | IV-1 | POLD4 | 1.35 |
| 7730 | 3 | 4 | | | IV-1 | PHF15 | 1.08 | 7826 | 3 | 4 | | | IV-1 | POLE | 1.42 |
| 7731 | 3 | 4 | | | IV-1 | PHF17 | 1.02 | 7827 | 3 | 4 | | | IV-1 | POLE3 | 1.22 |
| 7732 | 3 | 4 | | | IV-1 | PHF19 | 1.25 | 7828 | 3 | 4 | | | IV-1 | POLG | 1.41 |
| 7733 | 3 | 4 | | | IV-1 | PHF2 | 1.27 | 7829 | 3 | 4 | | | IV-1 | POLG2 | 1.06 |
| 7734 | 3 | 4 | | | IV-1 | PHF20 | 1.42 | 7830 | 3 | 4 | | | IV-1 | POLH | 1.39 |
| 7735 | 3 | 4 | | | IV-1 | PHF20L1 | 1.47 | 7831 | 3 | 4 | | | IV-1 | POLI | 1.07 |
| 7736 | 3 | 4 | | | IV-1 | PHF21A | 1.22 | 7832 | 3 | 4 | | | IV-1 | POLR1C | 1.32 |
| 7737 | 3 | 4 | | | IV-1 | PHF23 | 1.14 | 7833 | 3 | 4 | | | IV-1 | POLR1E | 1.21 |
| 7738 | 3 | 4 | | | IV-1 | PHF8 | 1.33 | 7834 | 3 | 4 | | | IV-1 | POLR2A | 1.19 |
| 7739 | 3 | 4 | | | IV-1 | PHKA2 | 1.43 | 7835 | 3 | 4 | | | IV-1 | POLR2C | 1.06 |
| 7740 | 3 | 4 | | | IV-1 | PHKG2 | 1.02 | 7836 | 3 | 4 | | | IV-1 | POLR2D | 1.46 |
| 7741 | 3 | 4 | | | IV-1 | PHLDA3 | 1.16 | 7837 | 3 | 4 | | | IV-1 | POLR2F | 1.03 |
| 7742 | 3 | 4 | | | IV-1 | PHLDB3 | 1.34 | 7838 | 3 | 4 | | | IV-1 | POLR2G | 1.26 |
| 7743 | 3 | 4 | | | IV-1 | PHLPP2 | 1.26 | 7839 | 3 | 4 | | | IV-1 | POLR2H | 1.41 |
| 7744 | 3 | 4 | | | IV-1 | PHPT1 | 1.46 | 7840 | 3 | 4 | | | IV-1 | POLR2J | 1.06 |
| 7745 | 3 | 4 | | | IV-1 | PHRF1 | 1.43 | 7841 | 3 | 4 | | | IV-1 | POLR2L | 1.15 |
| 7746 | 3 | 4 | | | IV-1 | PHTF1 | 1.29 | 7842 | 3 | 4 | | | IV-1 | POLR2M | 1.26 |
| 7747 | 3 | 4 | | | IV-1 | PHTF2 | 1.02 | 7843 | 3 | 4 | | | IV-1 | POLR3B | 1.34 |
| 7748 | 3 | 4 | | | IV-1 | PI4K2B | 1.41 | 7844 | 3 | 4 | | | IV-1 | POLR3C | 1.46 |
| 7749 | 3 | 4 | | | IV-1 | PI4KB | 1.10 | 7845 | 3 | 4 | | | IV-1 | POLR3D | 1.29 |
| 7750 | 3 | 4 | | | IV-1 | PIAS2 | 1.07 | 7846 | 3 | 4 | | | IV-1 | POLR3E | 1.36 |
| 7751 | 3 | 4 | | | IV-1 | PIAS3 | 1.32 | 7847 | 3 | 4 | | | IV-1 | POLR3F | 1.29 |
| 7752 | 3 | 4 | | | IV-1 | PIAS4 | 1.46 | 7848 | 3 | 4 | | | IV-1 | POLR3GL | 1.26 |
| 7753 | 3 | 4 | | | IV-1 | PIGA | 1.20 | 7849 | 3 | 4 | | | IV-1 | POLR3H | 1.07 |
| 7754 | 3 | 4 | | | IV-1 | PIGC | 1.32 | 7850 | 3 | 4 | | | IV-1 | POLR3K | 1.43 |
| 7755 | 3 | 4 | | | IV-1 | PIGQ | 1.21 | 7851 | 3 | 4 | | | IV-1 | POM121 | 1.43 |
| 7756 | 3 | 4 | | | IV-1 | PIGT | 1.39 | 7852 | 3 | 4 | | | IV-1 | POM121C | 1.45 |
| 7757 | 3 | 4 | | | IV-1 | PIGU | 1.14 | 7853 | 3 | 4 | | | IV-1 | POMT1 | 1.04 |
| 7758 | 3 | 4 | | | IV-1 | PIGV | 1.39 | 7854 | 3 | 4 | | | IV-1 | POP1 | 1.29 |
| 7759 | 3 | 4 | | | IV-1 | PIGY | 1.37 | 7855 | 3 | 4 | | | IV-1 | POP4 | 1.30 |
| 7760 | 3 | 4 | | | IV-1 | PIH1D1 | 1.47 | 7856 | 3 | 4 | | | IV-1 | POP7 | 1.23 |
| 7761 | 3 | 4 | | | IV-1 | PIK3C2A | 1.32 | 7857 | 3 | 4 | | | IV-1 | PORCN | 1.00 |
| 7762 | 3 | 4 | | | IV-1 | PIK3CA | 1.15 | 7858 | 3 | 4 | | | IV-1 | POT1 | 1.42 |
| 7763 | 3 | 4 | | | IV-1 | PIK3CD | 1.11 | 7859 | 3 | 4 | | | IV-1 | POTEE | 1.35 |
| 7764 | 3 | 4 | | | IV-1 | PIK3CG | 1.47 | 7860 | 3 | 4 | | | IV-1 | PP7080 | 1.06 |
| 7765 | 3 | 4 | | | IV-1 | PIK3R1 | 1.43 | 7861 | 3 | 4 | | | IV-1 | PPA1 | 1.38 |
| 7766 | 3 | 4 | | | IV-1 | PIK3R5 | 1.01 | 7862 | 3 | 4 | | | IV-1 | PPAN | 1.05 |
| 7767 | 3 | 4 | | | IV-1 | PIKFYVE | 1.26 | 7863 | 3 | 4 | | | IV-1 | PPAPDC2 | 1.40 |
| 7768 | 3 | 4 | | | IV-1 | PIN1 | 1.36 | 7864 | 3 | 4 | | | IV-1 | PPARD | 1.07 |
| 7769 | 3 | 4 | | | IV-1 | PIN1P1 | 1.14 | 7865 | 3 | 4 | | | IV-1 | PPAT | 1.45 |
| 7770 | 3 | 4 | | | IV-1 | PIN4 | 1.06 | 7866 | 3 | 4 | | | IV-1 | PPCS | 1.16 |
| 7771 | 3 | 4 | | | IV-1 | PINX1 | 1.38 | 7867 | 3 | 4 | | | IV-1 | PPFIA1 | 1.24 |

Fig. 41 - 42

| | | | | | | | | | | | | | |
|---|---|---|---|---|---|---|---|---|---|---|---|---|---|
| 7868 | 3 | 4 | | | IV-1 | PPHLN1 | 1.27 | 7964 | 3 | 4 | | IV-1 | PSMA4 | 1.45 |
| 7869 | 3 | 4 | | | IV-1 | PPIA | 1.43 | 7965 | 3 | 4 | | IV-1 | PSMA6 | 1.45 |
| 7870 | 3 | 4 | | | IV-1 | PPIAL4A | 1.10 | 7966 | 3 | 4 | | IV-1 | PSMB8 | 1.35 |
| 7871 | 3 | 4 | | | IV-1 | PPID | 1.41 | 7967 | 3 | 4 | | IV-1 | PSMC1 | 1.33 |
| 7872 | 3 | 4 | | | IV-1 | PPIE | 1.04 | 7968 | 3 | 4 | | IV-1 | PSMC4 | 1.36 |
| 7873 | 3 | 4 | | | IV-1 | PPIG | 1.31 | 7969 | 3 | 4 | | IV-1 | PSMD10 | 1.36 |
| 7874 | 3 | 4 | | | IV-1 | PPIL1 | 1.26 | 7970 | 3 | 4 | | IV-1 | PSMD4 | 1.50 |
| 7875 | 3 | 4 | | | IV-1 | PPIL2 | 1.48 | 7971 | 3 | 4 | | IV-1 | PSMD7 | 1.43 |
| 7876 | 3 | 4 | | | IV-1 | PPIL3 | 1.36 | 7972 | 3 | 4 | | IV-1 | PSMD9 | 1.43 |
| 7877 | 3 | 4 | | | IV-1 | PPIL4 | 1.39 | 7973 | 3 | 4 | | IV-1 | PSME1 | 1.02 |
| 7878 | 3 | 4 | | | IV-1 | PPM1B | 1.34 | 7974 | 3 | 4 | | IV-1 | PSME3 | 1.49 |
| 7879 | 3 | 4 | | | IV-1 | PPM1D | 1.48 | 7975 | 3 | 4 | | IV-1 | PSME4 | 1.24 |
| 7880 | 3 | 4 | | | IV-1 | PPM1K | 1.13 | 7976 | 3 | 4 | | IV-1 | PSMF1 | 1.13 |
| 7881 | 3 | 4 | | | IV-1 | PPM1M | 1.25 | 7977 | 3 | 4 | | IV-1 | PSMG1 | 1.32 |
| 7882 | 3 | 4 | | | IV-1 | PPM1N | 1.02 | 7978 | 3 | 4 | | IV-1 | PSMG3 | 1.27 |
| 7883 | 3 | 4 | | | IV-1 | PPP1CA | 1.36 | 7979 | 3 | 4 | | IV-1 | PSPC1 | 1.48 |
| 7884 | 3 | 4 | | | IV-1 | PPP1R10 | 1.45 | 7980 | 3 | 4 | | IV-1 | PSPN | 1.11 |
| 7885 | 3 | 4 | | | IV-1 | PPP1R11 | 1.28 | 7981 | 3 | 4 | | IV-1 | PSRC1 | 1.05 |
| 7886 | 3 | 4 | | | IV-1 | PPP1R13B | 1.03 | 7982 | 3 | 4 | | IV-1 | PSTPIP1 | 1.17 |
| 7887 | 3 | 4 | | | IV-1 | PPP1R15B | 1.20 | 7983 | 3 | 4 | | IV-1 | PTAFR | 1.07 |
| 7888 | 3 | 4 | | | IV-1 | PPP1R16A | 1.10 | 7984 | 3 | 4 | | IV-1 | PTAR1 | 1.13 |
| 7889 | 3 | 4 | | | IV-1 | PPP1R18 | 1.07 | 7985 | 3 | 4 | | IV-1 | PTBP3 | 1.19 |
| 7890 | 3 | 4 | | | IV-1 | PPP1R2 | 1.07 | 7986 | 3 | 4 | | IV-1 | PTCD2 | 1.24 |
| 7891 | 3 | 4 | | | IV-1 | PPP1R21 | 1.46 | 7987 | 3 | 4 | | IV-1 | PTCD3 | 1.16 |
| 7892 | 3 | 4 | | | IV-1 | PPP1R35 | 1.05 | 7988 | 3 | 4 | | IV-1 | PTEN | 1.28 |
| 7893 | 3 | 4 | | | IV-1 | PPP1R37 | 1.26 | 7989 | 3 | 4 | | IV-1 | PTENP1 | 1.19 |
| 7894 | 3 | 4 | | | IV-1 | PPP1R3D | 1.44 | 7990 | 3 | 4 | | IV-1 | PTGDS | 1.34 |
| 7895 | 3 | 4 | | | IV-1 | PPP1R3F | 1.18 | 7991 | 3 | 4 | | IV-1 | PTGES | 1.18 |
| 7896 | 3 | 4 | | | IV-1 | PPP1R8 | 1.26 | 7992 | 3 | 4 | | IV-1 | PTGES2 | 1.25 |
| 7897 | 3 | 4 | | | IV-1 | PPP1R9B | 1.21 | 7993 | 3 | 4 | | IV-1 | PTK2 | 1.46 |
| 7898 | 3 | 4 | | | IV-1 | PPP2R2A | 1.39 | 7994 | 3 | 4 | | IV-1 | PTK2B | 1.21 |
| 7899 | 3 | 4 | | | IV-1 | PPP2R2B | 1.11 | 7995 | 3 | 4 | | IV-1 | PTMA | 1.09 |
| 7900 | 3 | 4 | | | IV-1 | PPP2R2D | 1.02 | 7996 | 3 | 4 | | IV-1 | PTP4A1 | 1.09 |
| 7901 | 3 | 4 | | | IV-1 | PPP2R3C | 1.15 | 7997 | 3 | 4 | | IV-1 | PTP4A2 | 1.42 |
| 7902 | 3 | 4 | | | IV-1 | PPP2R5C | 1.25 | 7998 | 3 | 4 | | IV-1 | PTPLAD1 | 1.17 |
| 7903 | 3 | 4 | | | IV-1 | PPP3CA | 1.37 | 7999 | 3 | 4 | | IV-1 | PTPN12 | 1.18 |
| 7904 | 3 | 4 | | | IV-1 | PPP4C | 1.11 | 8000 | 3 | 4 | | IV-1 | PTPN18 | 1.38 |
| 7905 | 3 | 4 | | | IV-1 | PPP4R1 | 1.14 | 8001 | 3 | 4 | | IV-1 | PTPN23 | 1.46 |
| 7906 | 3 | 4 | | | IV-1 | PPP5C | 1.39 | 8002 | 3 | 4 | | IV-1 | PTPN6 | 1.25 |
| 7907 | 3 | 4 | | | IV-1 | PPP6R1 | 1.32 | 8003 | 3 | 4 | | IV-1 | PTPN7 | 1.07 |
| 7908 | 3 | 4 | | | IV-1 | PPP6R3 | 1.37 | 8004 | 3 | 4 | | IV-1 | PTPRA | 1.27 |
| 7909 | 3 | 4 | | | IV-1 | PPPDE1 | 1.49 | 8005 | 3 | 4 | | IV-1 | PTPRJ | 1.38 |
| 7910 | 3 | 4 | | | IV-1 | PPRC1 | 1.43 | 8006 | 3 | 4 | | IV-1 | PTRH1 | 1.29 |
| 7911 | 3 | 4 | | | IV-1 | PPTC7 | 1.17 | 8007 | 3 | 4 | | IV-1 | PTTG1IP | 1.46 |
| 7912 | 3 | 4 | | | IV-1 | PPWD1 | 1.40 | 8008 | 3 | 4 | | IV-1 | PTTG3P | 1.42 |
| 7913 | 3 | 4 | | | IV-1 | PQBP1 | 1.10 | 8009 | 3 | 4 | | IV-1 | PUF60 | 1.47 |
| 7914 | 3 | 4 | | | IV-1 | PRADC1 | 1.37 | 8010 | 3 | 4 | | IV-1 | PUM2 | 1.37 |
| 7915 | 3 | 4 | | | IV-1 | PRC1 | 1.08 | 8011 | 3 | 4 | | IV-1 | PURB | 1.24 |
| 7916 | 3 | 4 | | | IV-1 | PRCC | 1.13 | 8012 | 3 | 4 | | IV-1 | PUS1 | 1.49 |
| 7917 | 3 | 4 | | | IV-1 | PRDM15 | 1.30 | 8013 | 3 | 4 | | IV-1 | PUS10 | 1.27 |
| 7918 | 3 | 4 | | | IV-1 | PRDM2 | 1.16 | 8014 | 3 | 4 | | IV-1 | PUS7 | 1.09 |
| 7919 | 3 | 4 | | | IV-1 | PRDM4 | 1.38 | 8015 | 3 | 4 | | IV-1 | PVRIG | 1.03 |
| 7920 | 3 | 4 | | | IV-1 | PRDX6 | 1.03 | 8016 | 3 | 4 | | IV-1 | PVRL1 | 1.44 |
| 7921 | 3 | 4 | | | IV-1 | PREB | 1.44 | 8017 | 3 | 4 | | IV-1 | PWWP2A | 1.25 |
| 7922 | 3 | 4 | | | IV-1 | PRELID1 | 1.18 | 8018 | 3 | 4 | | IV-1 | PXK | 1.48 |
| 7923 | 3 | 4 | | | IV-1 | PRF1 | 1.27 | 8019 | 3 | 4 | | IV-1 | PXMP4 | 1.26 |
| 7924 | 3 | 4 | | | IV-1 | PRIC285 | 1.12 | 8020 | 3 | 4 | | IV-1 | PXN | 1.18 |
| 7925 | 3 | 4 | | | IV-1 | PRICKLE1 | 1.19 | 8021 | 3 | 4 | | IV-1 | PYCR2 | 1.34 |
| 7926 | 3 | 4 | | | IV-1 | PRICKLE4 | 1.34 | 8022 | 3 | 4 | | IV-1 | PYGO2 | 1.25 |
| 7927 | 3 | 4 | | | IV-1 | PRIM1 | 1.36 | 8023 | 3 | 4 | | IV-1 | PYROXD1 | 1.26 |
| 7928 | 3 | 4 | | | IV-1 | PRKAA1 | 1.22 | 8024 | 3 | 4 | | IV-1 | QARS | 1.34 |
| 7929 | 3 | 4 | | | IV-1 | PRKAB1 | 1.46 | 8025 | 3 | 4 | | IV-1 | QRICH1 | 1.28 |
| 7930 | 3 | 4 | | | IV-1 | PRKACB | 1.06 | 8026 | 3 | 4 | | IV-1 | R3HCC1 | 1.24 |
| 7931 | 3 | 4 | | | IV-1 | PRKACG | 1.12 | 8027 | 3 | 4 | | IV-1 | RAB11B | 1.05 |
| 7932 | 3 | 4 | | | IV-1 | PRKAG1 | 1.38 | 8028 | 3 | 4 | | IV-1 | RAB11FIP1 | 1.09 |
| 7933 | 3 | 4 | | | IV-1 | PRKAG2 | 1.04 | 8029 | 3 | 4 | | IV-1 | RAB11FIP2 | 1.16 |
| 7934 | 3 | 4 | | | IV-1 | PRKAR1B | 1.43 | 8030 | 3 | 4 | | IV-1 | RAB11FIP5 | 1.30 |
| 7935 | 3 | 4 | | | IV-1 | PRKCB | 1.21 | 8031 | 3 | 4 | | IV-1 | RAB18 | 1.12 |
| 7936 | 3 | 4 | | | IV-1 | PRKCD | 1.43 | 8032 | 3 | 4 | | IV-1 | RAB19 | 1.30 |
| 7937 | 3 | 4 | | | IV-1 | PRKCH | 1.09 | 8033 | 3 | 4 | | IV-1 | RAB1B | 1.04 |
| 7938 | 3 | 4 | | | IV-1 | PRKCQ | 1.22 | 8034 | 3 | 4 | | IV-1 | RAB22A | 1.31 |
| 7939 | 3 | 4 | | | IV-1 | PRKCSH | 1.30 | 8035 | 3 | 4 | | IV-1 | RAB28 | 1.46 |
| 7940 | 3 | 4 | | | IV-1 | PRKDC | 1.19 | 8036 | 3 | 4 | | IV-1 | RAB2B | 1.19 |
| 7941 | 3 | 4 | | | IV-1 | PRKRA | 1.32 | 8037 | 3 | 4 | | IV-1 | RAB33B | 1.21 |
| 7942 | 3 | 4 | | | IV-1 | PRKRIR | 1.10 | 8038 | 3 | 4 | | IV-1 | RAB35 | 1.17 |
| 7943 | 3 | 4 | | | IV-1 | PRKX | 1.24 | 8039 | 3 | 4 | | IV-1 | RAB39B | 1.10 |
| 7944 | 3 | 4 | | | IV-1 | PRMT10 | 1.47 | 8040 | 3 | 4 | | IV-1 | RAB3A | 1.16 |
| 7945 | 3 | 4 | | | IV-1 | PRPF3 | 1.08 | 8041 | 3 | 4 | | IV-1 | RAB3D | 1.15 |
| 7946 | 3 | 4 | | | IV-1 | PRPF38A | 1.42 | 8042 | 3 | 4 | | IV-1 | RAB3IP | 1.31 |
| 7947 | 3 | 4 | | | IV-1 | PRPF38B | 1.18 | 8043 | 3 | 4 | | IV-1 | RAB40C | 1.41 |
| 7948 | 3 | 4 | | | IV-1 | PRPF39 | 1.15 | 8044 | 3 | 4 | | IV-1 | RAB43 | 1.10 |
| 7949 | 3 | 4 | | | IV-1 | PRPS1 | 1.22 | 8045 | 3 | 4 | | IV-1 | RAB4B | 1.13 |
| 7950 | 3 | 4 | | | IV-1 | PRPS1L1 | 1.21 | 8046 | 3 | 4 | | IV-1 | RAB5A | 1.31 |
| 7951 | 3 | 4 | | | IV-1 | PRPSAP2 | 1.41 | 8047 | 3 | 4 | | IV-1 | RAB6A | 1.32 |
| 7952 | 3 | 4 | | | IV-1 | PRR12 | 1.40 | 8048 | 3 | 4 | | IV-1 | RAB6C | 1.45 |
| 7953 | 3 | 4 | | | IV-1 | PRR13 | 1.28 | 8049 | 3 | 4 | | IV-1 | RAB7A | 1.14 |
| 7954 | 3 | 4 | | | IV-1 | PRR14L | 1.44 | 8050 | 3 | 4 | | IV-1 | RAB7L1 | 1.12 |
| 7955 | 3 | 4 | | | IV-1 | PRR24 | 1.38 | 8051 | 3 | 4 | | IV-1 | RAB8A | 1.29 |
| 7956 | 3 | 4 | | | IV-1 | PRR5L | 1.43 | 8052 | 3 | 4 | | IV-1 | RAB9A | 1.35 |
| 7957 | 3 | 4 | | | IV-1 | PRRC2A | 1.23 | 8053 | 3 | 4 | | IV-1 | RABAC1 | 1.26 |
| 7958 | 3 | 4 | | | IV-1 | PRRG4 | 1.38 | 8054 | 3 | 4 | | IV-1 | RABEP1 | 1.47 |
| 7959 | 3 | 4 | | | IV-1 | PRUNE | 1.18 | 8055 | 3 | 4 | | IV-1 | RABEP2 | 1.17 |
| 7960 | 3 | 4 | | | IV-1 | PSD4 | 1.06 | 8056 | 3 | 4 | | IV-1 | RABEPK | 1.35 |
| 7961 | 3 | 4 | | | IV-1 | PSEN2 | 1.29 | 8057 | 3 | 4 | | IV-1 | RABGEF1 | 1.30 |
| 7962 | 3 | 4 | | | IV-1 | PSIP1 | 1.31 | 8058 | 3 | 4 | | IV-1 | RABGGTB | 1.05 |
| 7963 | 3 | 4 | | | IV-1 | PSKH1 | 1.20 | 8059 | 3 | 4 | | IV-1 | RABIF | 1.23 |

Fig. 41 - 43

| | | | | | | | | | | | | | | | |
|---|---|---|---|---|---|---|---|---|---|---|---|---|---|---|---|
| 8060 | 3 | 4 | | | IV-1 | RABL28 | 1.15 | 8156 | 3 | 4 | | | IV-1 | RHBDD3 | 1.21 |
| 8061 | 3 | 4 | | | IV-1 | RABL3 | 1.28 | 8157 | 3 | 4 | | | IV-1 | RHEB | 1.31 |
| 8062 | 3 | 4 | | | IV-1 | RAC2 | 1.23 | 8158 | 3 | 4 | | | IV-1 | RHOF | 1.04 |
| 8063 | 3 | 4 | | | IV-1 | RAD1 | 1.08 | 8159 | 3 | 4 | | | IV-1 | RHOG | 1.16 |
| 8064 | 3 | 4 | | | IV-1 | RAD17 | 1.07 | 8160 | 3 | 4 | | | IV-1 | RHOH | 1.08 |
| 8065 | 3 | 4 | | | IV-1 | RAD18 | 1.01 | 8161 | 3 | 4 | | | IV-1 | RHOQ | 1.28 |
| 8066 | 3 | 4 | | | IV-1 | RAD21 | 1.34 | 8162 | 3 | 4 | | | IV-1 | RIC8A | 1.29 |
| 8067 | 3 | 4 | | | IV-1 | RAD51C | 1.04 | 8163 | 3 | 4 | | | IV-1 | RIF1 | 1.48 |
| 8068 | 3 | 4 | | | IV-1 | RAD51D | 1.50 | 8164 | 3 | 4 | | | IV-1 | RILPL2 | 1.04 |
| 8069 | 3 | 4 | | | IV-1 | RAE1 | 1.48 | 8165 | 3 | 4 | | | IV-1 | RIMBP3 | 1.26 |
| 8070 | 3 | 4 | | | IV-1 | RALBP1 | 1.09 | 8166 | 3 | 4 | | | IV-1 | RIMBP3B | 1.31 |
| 8071 | 3 | 4 | | | IV-1 | RALGAPA1 | 1.26 | 8167 | 3 | 4 | | | IV-1 | RIN3 | 1.46 |
| 8072 | 3 | 4 | | | IV-1 | RALGAPB | 1.34 | 8168 | 3 | 4 | | | IV-1 | RING1 | 1.48 |
| 8073 | 3 | 4 | | | IV-1 | RALY | 1.23 | 8169 | 3 | 4 | | | IV-1 | RINL | 1.15 |
| 8074 | 3 | 4 | | | IV-1 | RANBP1 | 1.19 | 8170 | 3 | 4 | | | IV-1 | RINT1 | 1.30 |
| 8075 | 3 | 4 | | | IV-1 | RANBP3 | 1.08 | 8171 | 3 | 4 | | | IV-1 | RIPK1 | 1.26 |
| 8076 | 3 | 4 | | | IV-1 | RANGRF | 1.23 | 8172 | 3 | 4 | | | IV-1 | RIPK3 | 1.21 |
| 8077 | 3 | 4 | | | IV-1 | RAP1A | 1.12 | 8173 | 3 | 4 | | | IV-1 | RIT1 | 1.23 |
| 8078 | 3 | 4 | | | IV-1 | RAP1B | 1.40 | 8174 | 3 | 4 | | | IV-1 | RLF | 1.18 |
| 8079 | 3 | 4 | | | IV-1 | RAP1GAP2 | 1.04 | 8175 | 3 | 4 | | | IV-1 | RMI1 | 1.40 |
| 8080 | 3 | 4 | | | IV-1 | RAP2C | 1.22 | 8176 | 3 | 4 | | | IV-1 | RMI2 | 1.37 |
| 8081 | 3 | 4 | | | IV-1 | RAPGEF1 | 1.39 | 8177 | 3 | 4 | | | IV-1 | RMND5A | 1.23 |
| 8082 | 3 | 4 | | | IV-1 | RAPGEF6 | 1.24 | 8178 | 3 | 4 | | | IV-1 | RMND5B | 1.45 |
| 8083 | 3 | 4 | | | IV-1 | RARRES3 | 1.14 | 8179 | 3 | 4 | | | IV-1 | RNASEH2A | 1.46 |
| 8084 | 3 | 4 | | | IV-1 | RASA3 | 1.37 | 8180 | 3 | 4 | | | IV-1 | RNASEH2B | 1.20 |
| 8085 | 3 | 4 | | | IV-1 | RASA4P | 1.33 | 8181 | 3 | 4 | | | IV-1 | RNASEK | 1.32 |
| 8086 | 3 | 4 | | | IV-1 | RASAL3 | 1.02 | 8182 | 3 | 4 | | | IV-1 | RNASEL | 1.23 |
| 8087 | 3 | 4 | | | IV-1 | RASGEF1B | 1.28 | 8183 | 3 | 4 | | | IV-1 | RNF103 | 1.10 |
| 8088 | 3 | 4 | | | IV-1 | RASGRP4 | 1.08 | 8184 | 3 | 4 | | | IV-1 | RNF111 | 1.29 |
| 8089 | 3 | 4 | | | IV-1 | RASSF5 | 1.10 | 8185 | 3 | 4 | | | IV-1 | RNF113A | 1.24 |
| 8090 | 3 | 4 | | | IV-1 | RAVER1 | 1.24 | 8186 | 3 | 4 | | | IV-1 | RNF114 | 1.34 |
| 8091 | 3 | 4 | | | IV-1 | RB1CC1 | 1.24 | 8187 | 3 | 4 | | | IV-1 | RNF115 | 1.19 |
| 8092 | 3 | 4 | | | IV-1 | RBBP5 | 1.42 | 8188 | 3 | 4 | | | IV-1 | RNF121 | 1.37 |
| 8093 | 3 | 4 | | | IV-1 | RBBP6 | 1.40 | 8189 | 3 | 4 | | | IV-1 | RNF125 | 1.40 |
| 8094 | 3 | 4 | | | IV-1 | RBBP7 | 1.50 | 8190 | 3 | 4 | | | IV-1 | RNF126 | 1.18 |
| 8095 | 3 | 4 | | | IV-1 | RBBP9 | 1.08 | 8191 | 3 | 4 | | | IV-1 | RNF126P1 | 1.00 |
| 8096 | 3 | 4 | | | IV-1 | RBCK1 | 1.11 | 8192 | 3 | 4 | | | IV-1 | RNF13 | 1.12 |
| 8097 | 3 | 4 | | | IV-1 | RBFA | 1.00 | 8193 | 3 | 4 | | | IV-1 | RNF130 | 1.48 |
| 8098 | 3 | 4 | | | IV-1 | RBL1 | 1.49 | 8194 | 3 | 4 | | | IV-1 | RNF138 | 1.24 |
| 8099 | 3 | 4 | | | IV-1 | RBM15 | 1.05 | 8195 | 3 | 4 | | | IV-1 | RNF138P1 | 1.42 |
| 8100 | 3 | 4 | | | IV-1 | RBM18 | 1.43 | 8196 | 3 | 4 | | | IV-1 | RNF139 | 1.35 |
| 8101 | 3 | 4 | | | IV-1 | RBM19 | 1.22 | 8197 | 3 | 4 | | | IV-1 | RNF141 | 1.40 |
| 8102 | 3 | 4 | | | IV-1 | RBM22 | 1.26 | 8198 | 3 | 4 | | | IV-1 | RNF144A | 1.04 |
| 8103 | 3 | 4 | | | IV-1 | RBM23 | 1.46 | 8199 | 3 | 4 | | | IV-1 | RNF144B | 1.41 |
| 8104 | 3 | 4 | | | IV-1 | RBM25 | 1.40 | 8200 | 3 | 4 | | | IV-1 | RNF145 | 1.44 |
| 8105 | 3 | 4 | | | IV-1 | RBM26 | 1.29 | 8201 | 3 | 4 | | | IV-1 | RNF149 | 1.30 |
| 8106 | 3 | 4 | | | IV-1 | RBM28 | 1.47 | 8202 | 3 | 4 | | | IV-1 | RNF169 | 1.30 |
| 8107 | 3 | 4 | | | IV-1 | RBM34 | 1.42 | 8203 | 3 | 4 | | | IV-1 | RNF185 | 1.35 |
| 8108 | 3 | 4 | | | IV-1 | RBM39 | 1.31 | 8204 | 3 | 4 | | | IV-1 | RNF187 | 1.39 |
| 8109 | 3 | 4 | | | IV-1 | RBM4 | 1.20 | 8205 | 3 | 4 | | | IV-1 | RNF19A | 1.16 |
| 8110 | 3 | 4 | | | IV-1 | RBM42 | 1.36 | 8206 | 3 | 4 | | | IV-1 | RNF2 | 1.34 |
| 8111 | 3 | 4 | | | IV-1 | RBM43 | 1.38 | 8207 | 3 | 4 | | | IV-1 | RNF214 | 1.36 |
| 8112 | 3 | 4 | | | IV-1 | RBM47 | 1.16 | 8208 | 3 | 4 | | | IV-1 | RNF216 | 1.25 |
| 8113 | 3 | 4 | | | IV-1 | RBM4B | 1.46 | 8209 | 3 | 4 | | | IV-1 | RNF216P1 | 1.40 |
| 8114 | 3 | 4 | | | IV-1 | RBM6 | 1.11 | 8210 | 3 | 4 | | | IV-1 | RNF219 | 1.44 |
| 8115 | 3 | 4 | | | IV-1 | RBM7 | 1.34 | 8211 | 3 | 4 | | | IV-1 | RNF220 | 1.16 |
| 8116 | 3 | 4 | | | IV-1 | RBM8A | 1.23 | 8212 | 3 | 4 | | | IV-1 | RNF25 | 1.12 |
| 8117 | 3 | 4 | | | IV-1 | RBMX | 1.19 | 8213 | 3 | 4 | | | IV-1 | RNF26 | 1.50 |
| 8118 | 3 | 4 | | | IV-1 | RBMXL1 | 1.43 | 8214 | 3 | 4 | | | IV-1 | RNF31 | 1.22 |
| 8119 | 3 | 4 | | | IV-1 | RC3H1 | 1.08 | 8215 | 3 | 4 | | | IV-1 | RNF34 | 1.28 |
| 8120 | 3 | 4 | | | IV-1 | RC3H2 | 1.34 | 8216 | 3 | 4 | | | IV-1 | RNF38 | 1.40 |
| 8121 | 3 | 4 | | | IV-1 | RC8TB1 | 1.23 | 8217 | 3 | 4 | | | IV-1 | RNF4 | 1.26 |
| 8122 | 3 | 4 | | | IV-1 | RCE1 | 1.33 | 8218 | 3 | 4 | | | IV-1 | RNF41 | 1.28 |
| 8123 | 3 | 4 | | | IV-1 | RCHY1 | 1.31 | 8219 | 3 | 4 | | | IV-1 | RNF44 | 1.28 |
| 8124 | 3 | 4 | | | IV-1 | RCSD1 | 1.46 | 8220 | 3 | 4 | | | IV-1 | RNF5P1 | 1.09 |
| 8125 | 3 | 4 | | | IV-1 | RDBP | 1.09 | 8221 | 3 | 4 | | | IV-1 | RNF8 | 1.40 |
| 8126 | 3 | 4 | | | IV-1 | RDH14 | 1.31 | 8222 | 3 | 4 | | | IV-1 | RNFT1 | 1.36 |
| 8127 | 3 | 4 | | | IV-1 | RECK | 1.30 | 8223 | 3 | 4 | | | IV-1 | RNMTL1 | 1.48 |
| 8128 | 3 | 4 | | | IV-1 | RECQL5 | 1.14 | 8224 | 3 | 4 | | | IV-1 | RNPC3 | 1.05 |
| 8129 | 3 | 4 | | | IV-1 | RELB | 1.33 | 8225 | 3 | 4 | | | IV-1 | RNPEPL1 | 1.38 |
| 8130 | 3 | 4 | | | IV-1 | RELT | 1.12 | 8226 | 3 | 4 | | | IV-1 | RNPS1 | 1.19 |
| 8131 | 3 | 4 | | | IV-1 | REPIN1 | 1.15 | 8227 | 3 | 4 | | | IV-1 | ROGDI | 1.01 |
| 8132 | 3 | 4 | | | IV-1 | RER1 | 1.33 | 8228 | 3 | 4 | | | IV-1 | RP9 | 1.31 |
| 8133 | 3 | 4 | | | IV-1 | REV1 | 1.06 | 8229 | 3 | 4 | | | IV-1 | RPA1 | 1.01 |
| 8134 | 3 | 4 | | | IV-1 | REV3L | 1.46 | 8230 | 3 | 4 | | | IV-1 | RPA2 | 1.03 |
| 8135 | 3 | 4 | | | IV-1 | REXO1 | 1.03 | 8231 | 3 | 4 | | | IV-1 | RPAIN | 1.32 |
| 8136 | 3 | 4 | | | IV-1 | REXO2 | 1.20 | 8232 | 3 | 4 | | | IV-1 | RPAP3 | 1.35 |
| 8137 | 3 | 4 | | | IV-1 | REXO4 | 1.48 | 8233 | 3 | 4 | | | IV-1 | RPF1 | 1.28 |
| 8138 | 3 | 4 | | | IV-1 | RFC3 | 1.37 | 8234 | 3 | 4 | | | IV-1 | RPIA | 1.39 |
| 8139 | 3 | 4 | | | IV-1 | RFC4 | 1.40 | 8235 | 3 | 4 | | | IV-1 | RPL10 | 1.41 |
| 8140 | 3 | 4 | | | IV-1 | RFC5 | 1.18 | 8236 | 3 | 4 | | | IV-1 | RPL10A | 1.11 |
| 8141 | 3 | 4 | | | IV-1 | RFNG | 1.16 | 8237 | 3 | 4 | | | IV-1 | RPL13A | 1.17 |
| 8142 | 3 | 4 | | | IV-1 | RFTN1 | 1.47 | 8238 | 3 | 4 | | | IV-1 | RPL13AP6 | 1.21 |
| 8143 | 3 | 4 | | | IV-1 | RFWD2 | 1.13 | 8239 | 3 | 4 | | | IV-1 | RPL14 | 1.05 |
| 8144 | 3 | 4 | | | IV-1 | RFX5 | 1.22 | 8240 | 3 | 4 | | | IV-1 | RPL15 | 1.21 |
| 8145 | 3 | 4 | | | IV-1 | RFXAP | 1.26 | 8241 | 3 | 4 | | | IV-1 | RPL17-C18ORF32 | 1.15 |
| 8146 | 3 | 4 | | | IV-1 | RG9MTD1 | 1.49 | 8242 | 3 | 4 | | | IV-1 | RPL19 | 1.04 |
| 8147 | 3 | 4 | | | IV-1 | RG9MTD3 | 1.10 | 8243 | 3 | 4 | | | IV-1 | RPL19P12 | 1.36 |
| 8148 | 3 | 4 | | | IV-1 | RGP1 | 1.47 | 8244 | 3 | 4 | | | IV-1 | RPL23A | 1.29 |
| 8149 | 3 | 4 | | | IV-1 | RGPD3 | 1.21 | 8245 | 3 | 4 | | | IV-1 | RPL23AP53 | 1.17 |
| 8150 | 3 | 4 | | | IV-1 | RGS10 | 1.16 | 8246 | 3 | 4 | | | IV-1 | RPL26 | 1.21 |
| 8151 | 3 | 4 | | | IV-1 | RGS12 | 1.31 | 8247 | 3 | 4 | | | IV-1 | RPL28 | 1.15 |
| 8152 | 3 | 4 | | | IV-1 | RGS19 | 1.16 | 8248 | 3 | 4 | | | IV-1 | RPL32 | 1.27 |
| 8153 | 3 | 4 | | | IV-1 | RGS3 | 1.17 | 8249 | 3 | 4 | | | IV-1 | RPL34 | 1.46 |
| 8154 | 3 | 4 | | | IV-1 | RHBDD1 | 1.49 | 8250 | 3 | 4 | | | IV-1 | RPL37 | 1.07 |
| 8155 | 3 | 4 | | | IV-1 | RHBDD2 | 1.31 | 8251 | 3 | 4 | | | IV-1 | RPL4 | 1.38 |

Fig. 41 - 44

| | | | | | | | | | | | | | | | |
|---|---|---|---|---|---|---|---|---|---|---|---|---|---|---|---|
| 8252 | 3 | 4 | | | IV-1 | RPL41 | 1.32 | 8348 | 3 | 4 | | | IV-1 | SDF2 | 1.40 |
| 8253 | 3 | 4 | | | IV-1 | RPL5 | 1.12 | 8349 | 3 | 4 | | | IV-1 | SDF4 | 1.49 |
| 8254 | 3 | 4 | | | IV-1 | RPL7 | 1.17 | 8350 | 3 | 4 | | | IV-1 | SDHAF1 | 1.26 |
| 8255 | 3 | 4 | | | IV-1 | RPL7A | 1.13 | 8351 | 3 | 4 | | | IV-1 | SDHAF2 | 1.15 |
| 8256 | 3 | 4 | | | IV-1 | RPL8 | 1.03 | 8352 | 3 | 4 | | | IV-1 | SDHAP2 | 1.04 |
| 8257 | 3 | 4 | | | IV-1 | RPLP2 | 1.50 | 8353 | 3 | 4 | | | IV-1 | SEC11C | 1.04 |
| 8258 | 3 | 4 | | | IV-1 | RPP38 | 1.27 | 8354 | 3 | 4 | | | IV-1 | SEC22A | 1.45 |
| 8259 | 3 | 4 | | | IV-1 | RPRD1A | 1.44 | 8355 | 3 | 4 | | | IV-1 | SEC24C | 1.47 |
| 8260 | 3 | 4 | | | IV-1 | RPRD1B | 1.40 | 8356 | 3 | 4 | | | IV-1 | SECISBP2L | 1.29 |
| 8261 | 3 | 4 | | | IV-1 | RPS10P7 | 1.47 | 8357 | 3 | 4 | | | IV-1 | SECTM1 | 1.38 |
| 8262 | 3 | 4 | | | IV-1 | RPS13 | 1.18 | 8358 | 3 | 4 | | | IV-1 | SELO | 1.09 |
| 8263 | 3 | 4 | | | IV-1 | RPS16 | 1.14 | 8359 | 3 | 4 | | | IV-1 | SELPLG | 1.02 |
| 8264 | 3 | 4 | | | IV-1 | RPS18 | 1.03 | 8360 | 3 | 4 | | | IV-1 | SELT | 1.08 |
| 8265 | 3 | 4 | | | IV-1 | RPS19 | 1.06 | 8361 | 3 | 4 | | | IV-1 | SEMA4B | 1.24 |
| 8266 | 3 | 4 | | | IV-1 | RPS19BP1 | 1.22 | 8362 | 3 | 4 | | | IV-1 | SENP1 | 1.34 |
| 8267 | 3 | 4 | | | IV-1 | RPS2 | 1.06 | 8363 | 3 | 4 | | | IV-1 | SENP2 | 1.12 |
| 8268 | 3 | 4 | | | IV-1 | RPS23 | 1.31 | 8364 | 3 | 4 | | | IV-1 | SENP5 | 1.20 |
| 8269 | 3 | 4 | | | IV-1 | RPS24 | 1.26 | 8365 | 3 | 4 | | | IV-1 | SENP6 | 1.49 |
| 8270 | 3 | 4 | | | IV-1 | RPS27A | 1.07 | 8366 | 3 | 4 | | | IV-1 | SENP7 | 1.12 |
| 8271 | 3 | 4 | | | IV-1 | RPS29 | 1.00 | 8367 | 3 | 4 | | | IV-1 | SENP8 | 1.22 |
| 8272 | 3 | 4 | | | IV-1 | RPS6KA1 | 1.29 | 8368 | 3 | 4 | | | IV-1 | 42628 | 1.23 |
| 8273 | 3 | 4 | | | IV-1 | RPS6KB1 | 1.30 | 8369 | 3 | 4 | | | IV-1 | SEPHS1 | 1.46 |
| 8274 | 3 | 4 | | | IV-1 | RPS8 | 1.01 | 8370 | 3 | 4 | | | IV-1 | SEPSECS | 1.43 |
| 8275 | 3 | 4 | | | IV-1 | RPS9 | 1.19 | 8371 | 3 | 4 | | | IV-1 | 42623 | 1.39 |
| 8276 | 3 | 4 | | | IV-1 | RPUSD1 | 1.24 | 8372 | 3 | 4 | | | IV-1 | 42624 | 1.36 |
| 8277 | 3 | 4 | | | IV-1 | RPUSD2 | 1.04 | 8373 | 3 | 4 | | | IV-1 | 42621 | 1.43 |
| 8278 | 3 | 4 | | | IV-1 | RRAGB | 1.07 | 8374 | 3 | 4 | | | IV-1 | 42622 | 1.42 |
| 8279 | 3 | 4 | | | IV-1 | RRAGC | 1.45 | 8375 | 3 | 4 | | | IV-1 | SEPW1 | 1.01 |
| 8280 | 3 | 4 | | | IV-1 | RRAGD | 1.36 | 8376 | 3 | 4 | | | IV-1 | SERF2 | 1.11 |
| 8281 | 3 | 4 | | | IV-1 | RRM2B | 1.04 | 8377 | 3 | 4 | | | IV-1 | SERGEF | 1.30 |
| 8282 | 3 | 4 | | | IV-1 | RRN3P2 | 1.49 | 8378 | 3 | 4 | | | IV-1 | SERINC5 | 1.38 |
| 8283 | 3 | 4 | | | IV-1 | RRN3P3 | 1.31 | 8379 | 3 | 4 | | | IV-1 | SERPINA1 | 1.43 |
| 8284 | 3 | 4 | | | IV-1 | RRNAD1 | 1.42 | 8380 | 3 | 4 | | | IV-1 | SERPINB9 | 1.48 |
| 8285 | 3 | 4 | | | IV-1 | RRP15 | 1.46 | 8381 | 3 | 4 | | | IV-1 | SERPINF2 | 1.19 |
| 8286 | 3 | 4 | | | IV-1 | RRP36 | 1.42 | 8382 | 3 | 4 | | | IV-1 | SERTAD2 | 1.34 |
| 8287 | 3 | 4 | | | IV-1 | RRP8 | 1.26 | 8383 | 3 | 4 | | | IV-1 | SERTAD3 | 1.50 |
| 8288 | 3 | 4 | | | IV-1 | RSAD1 | 1.13 | 8384 | 3 | 4 | | | IV-1 | SESN2 | 1.48 |
| 8289 | 3 | 4 | | | IV-1 | RSBN1 | 1.38 | 8385 | 3 | 4 | | | IV-1 | SESN3 | 1.43 |
| 8290 | 3 | 4 | | | IV-1 | RSC1A1 | 1.38 | 8386 | 3 | 4 | | | IV-1 | SETD2 | 1.25 |
| 8291 | 3 | 4 | | | IV-1 | RSG1 | 1.27 | 8387 | 3 | 4 | | | IV-1 | SETD3 | 1.49 |
| 8292 | 3 | 4 | | | IV-1 | RSL1D1 | 1.37 | 8388 | 3 | 4 | | | IV-1 | SETD5 | 1.21 |
| 8293 | 3 | 4 | | | IV-1 | RSL24D1 | 1.44 | 8389 | 3 | 4 | | | IV-1 | SETD6 | 1.28 |
| 8294 | 3 | 4 | | | IV-1 | RSPH3 | 1.34 | 8390 | 3 | 4 | | | IV-1 | SETD8 | 1.20 |
| 8295 | 3 | 4 | | | IV-1 | RSPRY1 | 1.31 | 8391 | 3 | 4 | | | IV-1 | SETDB1 | 1.49 |
| 8296 | 3 | 4 | | | IV-1 | RSRC1 | 1.40 | 8392 | 3 | 4 | | | IV-1 | SETDB2 | 1.23 |
| 8297 | 3 | 4 | | | IV-1 | RSRC2 | 1.37 | 8393 | 3 | 4 | | | IV-1 | SETX | 1.38 |
| 8298 | 3 | 4 | | | IV-1 | RSU1 | 1.38 | 8394 | 3 | 4 | | | IV-1 | SF1 | 1.43 |
| 8299 | 3 | 4 | | | IV-1 | RTN3 | 1.42 | 8395 | 3 | 4 | | | IV-1 | SF3A1 | 1.27 |
| 8300 | 3 | 4 | | | IV-1 | RTN4IP1 | 1.39 | 8396 | 3 | 4 | | | IV-1 | SF3A2 | 1.04 |
| 8301 | 3 | 4 | | | IV-1 | RTP4 | 1.35 | 8397 | 3 | 4 | | | IV-1 | SF3B1 | 1.18 |
| 8302 | 3 | 4 | | | IV-1 | RUFY1 | 1.12 | 8398 | 3 | 4 | | | IV-1 | SF3B14 | 1.39 |
| 8303 | 3 | 4 | | | IV-1 | RUFY2 | 1.03 | 8399 | 3 | 4 | | | IV-1 | SF3B2 | 1.34 |
| 8304 | 3 | 4 | | | IV-1 | RUNX3 | 1.30 | 8400 | 3 | 4 | | | IV-1 | SF3B4 | 1.41 |
| 8305 | 3 | 4 | | | IV-1 | RUVBL1 | 1.30 | 8401 | 3 | 4 | | | IV-1 | SF3B5 | 1.30 |
| 8306 | 3 | 4 | | | IV-1 | RWDD1 | 1.22 | 8402 | 3 | 4 | | | IV-1 | SFI1 | 1.03 |
| 8307 | 3 | 4 | | | IV-1 | RWDD3 | 1.32 | 8403 | 3 | 4 | | | IV-1 | SFMBT1 | 1.23 |
| 8308 | 3 | 4 | | | IV-1 | RWDD4 | 1.42 | 8404 | 3 | 4 | | | IV-1 | SFSWAP | 1.34 |
| 8309 | 3 | 4 | | | IV-1 | RXRA | 1.49 | 8405 | 3 | 4 | | | IV-1 | SFT2D3 | 1.36 |
| 8310 | 3 | 4 | | | IV-1 | RXRB | 1.05 | 8406 | 3 | 4 | | | IV-1 | SFXN1 | 1.43 |
| 8311 | 3 | 4 | | | IV-1 | RYBP | 1.03 | 8407 | 3 | 4 | | | IV-1 | SFXN2 | 1.22 |
| 8312 | 3 | 4 | | | IV-1 | S100PBP | 1.37 | 8408 | 3 | 4 | | | IV-1 | SFXN4 | 1.02 |
| 8313 | 3 | 4 | | | IV-1 | S1PR1 | 1.07 | 8409 | 3 | 4 | | | IV-1 | SGOL2 | 1.31 |
| 8314 | 3 | 4 | | | IV-1 | S1PR4 | 1.11 | 8410 | 3 | 4 | | | IV-1 | SGPP1 | 1.39 |
| 8315 | 3 | 4 | | | IV-1 | SACM1L | 1.46 | 8411 | 3 | 4 | | | IV-1 | SGSM2 | 1.04 |
| 8316 | 3 | 4 | | | IV-1 | SACS | 1.24 | 8412 | 3 | 4 | | | IV-1 | SGSM3 | 1.02 |
| 8317 | 3 | 4 | | | IV-1 | SAFB | 1.37 | 8413 | 3 | 4 | | | IV-1 | SGTA | 1.19 |
| 8318 | 3 | 4 | | | IV-1 | SAFB2 | 1.28 | 8414 | 3 | 4 | | | IV-1 | SH2B2 | 1.08 |
| 8319 | 3 | 4 | | | IV-1 | SAMD8 | 1.04 | 8415 | 3 | 4 | | | IV-1 | SH2D3C | 1.33 |
| 8320 | 3 | 4 | | | IV-1 | SAMD9L | 1.39 | 8416 | 3 | 4 | | | IV-1 | SH3BGRL3 | 1.23 |
| 8321 | 3 | 4 | | | IV-1 | SAP130 | 1.14 | 8417 | 3 | 4 | | | IV-1 | SH3BP2 | 1.13 |
| 8322 | 3 | 4 | | | IV-1 | SAP18 | 1.37 | 8418 | 3 | 4 | | | IV-1 | SH3BP5 | 1.35 |
| 8323 | 3 | 4 | | | IV-1 | SAP30BP | 1.25 | 8419 | 3 | 4 | | | IV-1 | SH3BP5L | 1.26 |
| 8324 | 3 | 4 | | | IV-1 | SAR1A | 1.35 | 8420 | 3 | 4 | | | IV-1 | SH3GL1 | 1.15 |
| 8325 | 3 | 4 | | | IV-1 | SARS | 1.48 | 8421 | 3 | 4 | | | IV-1 | SH3GL1P1 | 1.07 |
| 8326 | 3 | 4 | | | IV-1 | SARS2 | 1.42 | 8422 | 3 | 4 | | | IV-1 | SH3RF1 | 1.37 |
| 8327 | 3 | 4 | | | IV-1 | SASH3 | 1.37 | 8423 | 3 | 4 | | | IV-1 | SH3YL1 | 1.43 |
| 8328 | 3 | 4 | | | IV-1 | SAT1 | 1.24 | 8424 | 3 | 4 | | | IV-1 | SHISA5 | 1.31 |
| 8329 | 3 | 4 | | | IV-1 | SATB1 | 1.24 | 8425 | 3 | 4 | | | IV-1 | SHKBP1 | 1.31 |
| 8330 | 3 | 4 | | | IV-1 | SAV1 | 1.16 | 8426 | 3 | 4 | | | IV-1 | SHMT2 | 1.40 |
| 8331 | 3 | 4 | | | IV-1 | SAYSD1 | 1.30 | 8427 | 3 | 4 | | | IV-1 | SHOC2 | 1.32 |
| 8332 | 3 | 4 | | | IV-1 | SBDS | 1.36 | 8428 | 3 | 4 | | | IV-1 | SHPRH | 1.47 |
| 8333 | 3 | 4 | | | IV-1 | SBF1 | 1.18 | 8429 | 3 | 4 | | | IV-1 | SIGLEC16 | 1.48 |
| 8334 | 3 | 4 | | | IV-1 | SBF1P1 | 1.14 | 8430 | 3 | 4 | | | IV-1 | SIGMAR1 | 1.23 |
| 8335 | 3 | 4 | | | IV-1 | SBF2 | 1.41 | 8431 | 3 | 4 | | | IV-1 | SIK3 | 1.09 |
| 8336 | 3 | 4 | | | IV-1 | SC5DL | 1.41 | 8432 | 3 | 4 | | | IV-1 | SIKE1 | 1.03 |
| 8337 | 3 | 4 | | | IV-1 | SCAF1 | 1.38 | 8433 | 3 | 4 | | | IV-1 | SIN3A | 1.27 |
| 8338 | 3 | 4 | | | IV-1 | SCAF8 | 1.20 | 8434 | 3 | 4 | | | IV-1 | SIN3B | 1.26 |
| 8339 | 3 | 4 | | | IV-1 | SCAMP2 | 1.47 | 8435 | 3 | 4 | | | IV-1 | SIPA1 | 1.18 |
| 8340 | 3 | 4 | | | IV-1 | SCARNA2 | 1.50 | 8436 | 3 | 4 | | | IV-1 | SIPA1L1 | 1.34 |
| 8341 | 3 | 4 | | | IV-1 | SCFD2 | 1.10 | 8437 | 3 | 4 | | | IV-1 | SIPA1L2 | 1.08 |
| 8342 | 3 | 4 | | | IV-1 | SCLT1 | 1.11 | 8438 | 3 | 4 | | | IV-1 | SIRT2 | 1.14 |
| 8343 | 3 | 4 | | | IV-1 | SCMH1 | 1.22 | 8439 | 3 | 4 | | | IV-1 | SIRT5 | 1.20 |
| 8344 | 3 | 4 | | | IV-1 | SCO2 | 1.04 | 8440 | 3 | 4 | | | IV-1 | SIRT6 | 1.15 |
| 8345 | 3 | 4 | | | IV-1 | SCOC | 1.41 | 8441 | 3 | 4 | | | IV-1 | SIRT7 | 1.12 |
| 8346 | 3 | 4 | | | IV-1 | SCRN3 | 1.26 | 8442 | 3 | 4 | | | IV-1 | SIVA1 | 1.14 |
| 8347 | 3 | 4 | | | IV-1 | SCYL1 | 1.05 | 8443 | 3 | 4 | | | IV-1 | SKI | 1.02 |

Fig. 41 - 45

| | | | | | | | | | | | | | | | |
|---|---|---|---|---|---|---|---|---|---|---|---|---|---|---|---|
| 8444 | 3 | 4 | | | IV-1 | SKIV2L | 1.07 | 8540 | 3 | 4 | | | IV-1 | SNAPC1 | 1.02 |
| 8445 | 3 | 4 | | | IV-1 | SKP1 | 1.39 | 8541 | 3 | 4 | | | IV-1 | SNAPC4 | 1.05 |
| 8446 | 3 | 4 | | | IV-1 | SKP1P2 | 1.14 | 8542 | 3 | 4 | | | IV-1 | SNHG6 | 1.04 |
| 8447 | 3 | 4 | | | IV-1 | SLA | 1.26 | 8543 | 3 | 4 | | | IV-1 | SNHG8 | 1.03 |
| 8448 | 3 | 4 | | | IV-1 | SLAIN1 | 1.11 | 8544 | 3 | 4 | | | IV-1 | SNRNP200 | 1.44 |
| 8449 | 3 | 4 | | | IV-1 | SLAIN2 | 1.37 | 8545 | 3 | 4 | | | IV-1 | SNRNP27 | 1.26 |
| 8450 | 3 | 4 | | | IV-1 | SLAMF1 | 1.04 | 8546 | 3 | 4 | | | IV-1 | SNRNP35 | 1.41 |
| 8451 | 3 | 4 | | | IV-1 | SLC10A3 | 1.11 | 8547 | 3 | 4 | | | IV-1 | SNRNP48 | 1.00 |
| 8452 | 3 | 4 | | | IV-1 | SLC11A2 | 1.24 | 8548 | 3 | 4 | | | IV-1 | SNRPD3 | 1.46 |
| 8453 | 3 | 4 | | | IV-1 | SLC12A2 | 1.08 | 8549 | 3 | 4 | | | IV-1 | SNRPF | 1.40 |
| 8454 | 3 | 4 | | | IV-1 | SLC12A4 | 1.24 | 8550 | 3 | 4 | | | IV-1 | SNRPG | 1.41 |
| 8455 | 3 | 4 | | | IV-1 | SLC12A6 | 1.16 | 8551 | 3 | 4 | | | IV-1 | SNRPN | 1.13 |
| 8456 | 3 | 4 | | | IV-1 | SLC12A9 | 1.29 | 8552 | 3 | 4 | | | IV-1 | SNTB2 | 1.40 |
| 8457 | 3 | 4 | | | IV-1 | SLC15A4 | 1.13 | 8553 | 3 | 4 | | | IV-1 | SNW1 | 1.49 |
| 8458 | 3 | 4 | | | IV-1 | SLC18A2 | 1.06 | 8554 | 3 | 4 | | | IV-1 | SNX1 | 1.33 |
| 8459 | 3 | 4 | | | IV-1 | SLC20A1 | 1.42 | 8555 | 3 | 4 | | | IV-1 | SNX10 | 1.22 |
| 8460 | 3 | 4 | | | IV-1 | SLC20A2 | 1.33 | 8556 | 3 | 4 | | | IV-1 | SNX11 | 1.16 |
| 8461 | 3 | 4 | | | IV-1 | SLC22A4 | 1.47 | 8557 | 3 | 4 | | | IV-1 | SNX13 | 1.22 |
| 8462 | 3 | 4 | | | IV-1 | SLC23A2 | 1.22 | 8558 | 3 | 4 | | | IV-1 | SNX16 | 1.37 |
| 8463 | 3 | 4 | | | IV-1 | SLC24A1 | 1.11 | 8559 | 3 | 4 | | | IV-1 | SNX19 | 1.35 |
| 8464 | 3 | 4 | | | IV-1 | SLC25A1 | 1.48 | 8560 | 3 | 4 | | | IV-1 | SNX20 | 1.37 |
| 8465 | 3 | 4 | | | IV-1 | SLC25A15 | 1.23 | 8561 | 3 | 4 | | | IV-1 | SNX24 | 1.45 |
| 8466 | 3 | 4 | | | IV-1 | SLC25A16 | 1.26 | 8562 | 3 | 4 | | | IV-1 | SNX25 | 1.27 |
| 8467 | 3 | 4 | | | IV-1 | SLC25A17 | 1.25 | 8563 | 3 | 4 | | | IV-1 | SNX9 | 1.49 |
| 8468 | 3 | 4 | | | IV-1 | SLC25A23 | 1.12 | 8564 | 3 | 4 | | | IV-1 | SOCS5 | 1.22 |
| 8469 | 3 | 4 | | | IV-1 | SLC25A25 | 1.33 | 8565 | 3 | 4 | | | IV-1 | SOCS7 | 1.37 |
| 8470 | 3 | 4 | | | IV-1 | SLC25A28 | 1.02 | 8566 | 3 | 4 | | | IV-1 | SOD1 | 1.20 |
| 8471 | 3 | 4 | | | IV-1 | SLC25A32 | 1.50 | 8567 | 3 | 4 | | | IV-1 | SORBS3 | 1.08 |
| 8472 | 3 | 4 | | | IV-1 | SLC25A33 | 1.23 | 8568 | 3 | 4 | | | IV-1 | SORD | 1.30 |
| 8473 | 3 | 4 | | | IV-1 | SLC25A36 | 1.40 | 8569 | 3 | 4 | | | IV-1 | SORL1 | 1.13 |
| 8474 | 3 | 4 | | | IV-1 | SLC25A46 | 1.44 | 8570 | 3 | 4 | | | IV-1 | SOS1 | 1.47 |
| 8475 | 3 | 4 | | | IV-1 | SLC2A13 | 1.10 | 8571 | 3 | 4 | | | IV-1 | SOS2 | 1.28 |
| 8476 | 3 | 4 | | | IV-1 | SLC2A3 | 1.45 | 8572 | 3 | 4 | | | IV-1 | SOWAHD | 1.22 |
| 8477 | 3 | 4 | | | IV-1 | SLC30A5 | 1.23 | 8573 | 3 | 4 | | | IV-1 | SOX12 | 1.15 |
| 8478 | 3 | 4 | | | IV-1 | SLC30A6 | 1.45 | 8574 | 3 | 4 | | | IV-1 | SP1 | 1.39 |
| 8479 | 3 | 4 | | | IV-1 | SLC30A9 | 1.48 | 8575 | 3 | 4 | | | IV-1 | SP110 | 1.15 |
| 8480 | 3 | 4 | | | IV-1 | SLC35A2 | 1.35 | 8576 | 3 | 4 | | | IV-1 | SP140 | 1.38 |
| 8481 | 3 | 4 | | | IV-1 | SLC35A3 | 1.44 | 8577 | 3 | 4 | | | IV-1 | SP140L | 1.07 |
| 8482 | 3 | 4 | | | IV-1 | SLC35A4 | 1.50 | 8578 | 3 | 4 | | | IV-1 | SP2 | 1.07 |
| 8483 | 3 | 4 | | | IV-1 | SLC35B2 | 1.07 | 8579 | 3 | 4 | | | IV-1 | SP3 | 1.29 |
| 8484 | 3 | 4 | | | IV-1 | SLC35C2 | 1.22 | 8580 | 3 | 4 | | | IV-1 | SP4 | 1.03 |
| 8485 | 3 | 4 | | | IV-1 | SLC35D1 | 1.19 | 8581 | 3 | 4 | | | IV-1 | SPA17 | 1.15 |
| 8486 | 3 | 4 | | | IV-1 | SLC35E2B | 1.29 | 8582 | 3 | 4 | | | IV-1 | SPAG5-AS1 | 1.46 |
| 8487 | 3 | 4 | | | IV-1 | SLC35E3 | 1.08 | 8583 | 3 | 4 | | | IV-1 | SPAG9 | 1.08 |
| 8488 | 3 | 4 | | | IV-1 | SLC35F2 | 1.09 | 8584 | 3 | 4 | | | IV-1 | SPAST | 1.47 |
| 8489 | 3 | 4 | | | IV-1 | SLC37A1 | 1.01 | 8585 | 3 | 4 | | | IV-1 | SPATA13 | 1.31 |
| 8490 | 3 | 4 | | | IV-1 | SLC37A3 | 1.50 | 8586 | 3 | 4 | | | IV-1 | SPATA2 | 1.41 |
| 8491 | 3 | 4 | | | IV-1 | SLC37A4 | 1.22 | 8587 | 3 | 4 | | | IV-1 | SPATA5 | 1.02 |
| 8492 | 3 | 4 | | | IV-1 | SLC39A13 | 1.00 | 8588 | 3 | 4 | | | IV-1 | SPCS3 | 1.29 |
| 8493 | 3 | 4 | | | IV-1 | SLC39A3 | 1.35 | 8589 | 3 | 4 | | | IV-1 | SPEN | 1.33 |
| 8494 | 3 | 4 | | | IV-1 | SLC41A1 | 1.16 | 8590 | 3 | 4 | | | IV-1 | SPESP1 | 1.30 |
| 8495 | 3 | 4 | | | IV-1 | SLC43A1 | 1.40 | 8591 | 3 | 4 | | | IV-1 | SPG7 | 1.42 |
| 8496 | 3 | 4 | | | IV-1 | SLC43A2 | 1.44 | 8592 | 3 | 4 | | | IV-1 | SPI1 | 1.04 |
| 8497 | 3 | 4 | | | IV-1 | SLC46A3 | 1.49 | 8593 | 3 | 4 | | | IV-1 | SPIN2A | 1.10 |
| 8498 | 3 | 4 | | | IV-1 | SLC48A1 | 1.14 | 8594 | 3 | 4 | | | IV-1 | SPIN2B | 1.10 |
| 8499 | 3 | 4 | | | IV-1 | SLC4A5 | 1.42 | 8595 | 3 | 4 | | | IV-1 | SPIN4 | 1.10 |
| 8500 | 3 | 4 | | | IV-1 | SLC4A7 | 1.26 | 8596 | 3 | 4 | | | IV-1 | SPIRE1 | 1.30 |
| 8501 | 3 | 4 | | | IV-1 | SLC50A1 | 1.35 | 8597 | 3 | 4 | | | IV-1 | SPN | 1.42 |
| 8502 | 3 | 4 | | | IV-1 | SLC7A5 | 1.15 | 8598 | 3 | 4 | | | IV-1 | SPOCK1 | 1.35 |
| 8503 | 3 | 4 | | | IV-1 | SLC7A6 | 1.14 | 8599 | 3 | 4 | | | IV-1 | SPOP | 1.40 |
| 8504 | 3 | 4 | | | IV-1 | SLC7A6OS | 1.04 | 8600 | 3 | 4 | | | IV-1 | SPOPL | 1.28 |
| 8505 | 3 | 4 | | | IV-1 | SLC9A1 | 1.28 | 8601 | 3 | 4 | | | IV-1 | SPPL2B | 1.03 |
| 8506 | 3 | 4 | | | IV-1 | SLC9A3R2 | 1.21 | 8602 | 3 | 4 | | | IV-1 | SPRYD3 | 1.23 |
| 8507 | 3 | 4 | | | IV-1 | SLC9B2 | 1.40 | 8603 | 3 | 4 | | | IV-1 | SPSB1 | 1.25 |
| 8508 | 3 | 4 | | | IV-1 | SLCO3A1 | 1.28 | 8604 | 3 | 4 | | | IV-1 | SQSTM1 | 1.43 |
| 8509 | 3 | 4 | | | IV-1 | SLK | 1.28 | 8605 | 3 | 4 | | | IV-1 | SRBD1 | 1.36 |
| 8510 | 3 | 4 | | | IV-1 | SLMAP | 1.27 | 8606 | 3 | 4 | | | IV-1 | SRCAP | 1.23 |
| 8511 | 3 | 4 | | | IV-1 | SLMO2 | 1.13 | 8607 | 3 | 4 | | | IV-1 | SREBF1 | 1.03 |
| 8512 | 3 | 4 | | | IV-1 | SLTM | 1.40 | 8608 | 3 | 4 | | | IV-1 | SRF | 1.48 |
| 8513 | 3 | 4 | | | IV-1 | SLU7 | 1.39 | 8609 | 3 | 4 | | | IV-1 | SRI | 1.35 |
| 8514 | 3 | 4 | | | IV-1 | SMAD3 | 1.25 | 8610 | 3 | 4 | | | IV-1 | SRP19 | 1.09 |
| 8515 | 3 | 4 | | | IV-1 | SMAD4 | 1.33 | 8611 | 3 | 4 | | | IV-1 | SRP9 | 1.41 |
| 8516 | 3 | 4 | | | IV-1 | SMAD5 | 1.47 | 8612 | 3 | 4 | | | IV-1 | SRPK1 | 1.02 |
| 8517 | 3 | 4 | | | IV-1 | SMAD7 | 1.33 | 8613 | 3 | 4 | | | IV-1 | SRPK2 | 1.20 |
| 8518 | 3 | 4 | | | IV-1 | SMARCB1 | 1.23 | 8614 | 3 | 4 | | | IV-1 | SRPR | 1.30 |
| 8519 | 3 | 4 | | | IV-1 | SMARCC1 | 1.49 | 8615 | 3 | 4 | | | IV-1 | SRPRB | 1.39 |
| 8520 | 3 | 4 | | | IV-1 | SMARCC2 | 1.37 | 8616 | 3 | 4 | | | IV-1 | SRRD | 1.45 |
| 8521 | 3 | 4 | | | IV-1 | SMARCD1 | 1.28 | 8617 | 3 | 4 | | | IV-1 | SRRM1 | 1.46 |
| 8522 | 3 | 4 | | | IV-1 | SMARCE1 | 1.37 | 8618 | 3 | 4 | | | IV-1 | SRRT | 1.26 |
| 8523 | 3 | 4 | | | IV-1 | SMC5 | 1.33 | 8619 | 3 | 4 | | | IV-1 | SRSF2 | 1.46 |
| 8524 | 3 | 4 | | | IV-1 | SMCR7 | 1.34 | 8620 | 3 | 4 | | | IV-1 | SRSF3 | 1.35 |
| 8525 | 3 | 4 | | | IV-1 | SMEK1 | 1.37 | 8621 | 3 | 4 | | | IV-1 | SRSF4 | 1.50 |
| 8526 | 3 | 4 | | | IV-1 | SMEK2 | 1.36 | 8622 | 3 | 4 | | | IV-1 | SRSF5 | 1.03 |
| 8527 | 3 | 4 | | | IV-1 | SMG1 | 1.18 | 8623 | 3 | 4 | | | IV-1 | SRSF6 | 1.33 |
| 8528 | 3 | 4 | | | IV-1 | SMG6 | 1.41 | 8624 | 3 | 4 | | | IV-1 | SRSF8 | 1.32 |
| 8529 | 3 | 4 | | | IV-1 | SMG7 | 1.15 | 8625 | 3 | 4 | | | IV-1 | SRSF9 | 1.49 |
| 8530 | 3 | 4 | | | IV-1 | SMNDC1 | 1.41 | 8626 | 3 | 4 | | | IV-1 | SS18L1 | 1.49 |
| 8531 | 3 | 4 | | | IV-1 | SMPD1 | 1.46 | 8627 | 3 | 4 | | | IV-1 | SSB | 1.44 |
| 8532 | 3 | 4 | | | IV-1 | SMPD2 | 1.05 | 8628 | 3 | 4 | | | IV-1 | SSBP1 | 1.20 |
| 8533 | 3 | 4 | | | IV-1 | SMS | 1.50 | 8629 | 3 | 4 | | | IV-1 | SSBP2 | 1.26 |
| 8534 | 3 | 4 | | | IV-1 | SMU1 | 1.36 | 8630 | 3 | 4 | | | IV-1 | SSFA2 | 1.17 |
| 8535 | 3 | 4 | | | IV-1 | SMURF1 | 1.21 | 8631 | 3 | 4 | | | IV-1 | SSH1 | 1.43 |
| 8536 | 3 | 4 | | | IV-1 | SMURF2 | 1.02 | 8632 | 3 | 4 | | | IV-1 | SSH2 | 1.02 |
| 8537 | 3 | 4 | | | IV-1 | SMYD2 | 1.05 | 8633 | 3 | 4 | | | IV-1 | SSNA1 | 1.23 |
| 8538 | 3 | 4 | | | IV-1 | SMYD4 | 1.18 | 8634 | 3 | 4 | | | IV-1 | SSR2 | 1.23 |
| 8539 | 3 | 4 | | | IV-1 | SNAP23 | 1.17 | 8635 | 3 | 4 | | | IV-1 | SSR4 | 1.48 |

Fig. 41 - 46

| | | | | | | | | | | | | | | | |
|---|---|---|---|---|---|---|---|---|---|---|---|---|---|---|---|
| 8636 | 3 | 4 | | | IV-1 | SSX2IP | 1.03 | 8732 | 3 | 4 | | | IV-1 | TATDN2 | 1.24 |
| 8637 | 3 | 4 | | | IV-1 | ST13 | 1.31 | 8733 | 3 | 4 | | | IV-1 | TAX1BP1 | 1.40 |
| 8638 | 3 | 4 | | | IV-1 | ST13P4 | 1.05 | 8734 | 3 | 4 | | | IV-1 | TBC1D10B | 1.29 |
| 8639 | 3 | 4 | | | IV-1 | ST3GAL2 | 1.20 | 8735 | 3 | 4 | | | IV-1 | TBC1D12 | 1.07 |
| 8640 | 3 | 4 | | | IV-1 | ST6GAL1 | 1.04 | 8736 | 3 | 4 | | | IV-1 | TBC1D13 | 1.30 |
| 8641 | 3 | 4 | | | IV-1 | ST8SIA4 | 1.04 | 8737 | 3 | 4 | | | IV-1 | TBC1D14 | 1.07 |
| 8642 | 3 | 4 | | | IV-1 | STAG1 | 1.30 | 8738 | 3 | 4 | | | IV-1 | TBC1D15 | 1.07 |
| 8643 | 3 | 4 | | | IV-1 | STAG2 | 1.36 | 8739 | 3 | 4 | | | IV-1 | TBC1D20 | 1.04 |
| 8644 | 3 | 4 | | | IV-1 | STAM2 | 1.16 | 8740 | 3 | 4 | | | IV-1 | TBC1D22A | 1.01 |
| 8645 | 3 | 4 | | | IV-1 | STAMBP | 1.36 | 8741 | 3 | 4 | | | IV-1 | TBC1D23 | 1.42 |
| 8646 | 3 | 4 | | | IV-1 | STAMBPL1 | 1.09 | 8742 | 3 | 4 | | | IV-1 | TBC1D2B | 1.48 |
| 8647 | 3 | 4 | | | IV-1 | STARD3 | 1.24 | 8743 | 3 | 4 | | | IV-1 | TBCA | 1.40 |
| 8648 | 3 | 4 | | | IV-1 | STARD4 | 1.14 | 8744 | 3 | 4 | | | IV-1 | TBCB | 1.46 |
| 8649 | 3 | 4 | | | IV-1 | STAT4 | 1.34 | 8745 | 3 | 4 | | | IV-1 | TBCC | 1.08 |
| 8650 | 3 | 4 | | | IV-1 | STAT5B | 1.21 | 8746 | 3 | 4 | | | IV-1 | TBCCD1 | 1.06 |
| 8651 | 3 | 4 | | | IV-1 | STAT6 | 1.30 | 8747 | 3 | 4 | | | IV-1 | TBCD | 1.23 |
| 8652 | 3 | 4 | | | IV-1 | STAU2 | 1.43 | 8748 | 3 | 4 | | | IV-1 | TBCE | 1.22 |
| 8653 | 3 | 4 | | | IV-1 | STEAP4 | 1.02 | 8749 | 3 | 4 | | | IV-1 | TBK1 | 1.45 |
| 8654 | 3 | 4 | | | IV-1 | STIM1 | 1.31 | 8750 | 3 | 4 | | | IV-1 | TBL1XR1 | 1.32 |
| 8655 | 3 | 4 | | | IV-1 | STIM2 | 1.13 | 8751 | 3 | 4 | | | IV-1 | TBPL1 | 1.18 |
| 8656 | 3 | 4 | | | IV-1 | STK10 | 1.42 | 8752 | 3 | 4 | | | IV-1 | TBRG1 | 1.19 |
| 8657 | 3 | 4 | | | IV-1 | STK11 | 1.36 | 8753 | 3 | 4 | | | IV-1 | TBX21 | 1.06 |
| 8658 | 3 | 4 | | | IV-1 | STK17B | 1.16 | 8754 | 3 | 4 | | | IV-1 | TCEAL3 | 1.01 |
| 8659 | 3 | 4 | | | IV-1 | STK25 | 1.34 | 8755 | 3 | 4 | | | IV-1 | TCEAL4 | 1.05 |
| 8660 | 3 | 4 | | | IV-1 | STK35 | 1.08 | 8756 | 3 | 4 | | | IV-1 | TCEAL8 | 1.34 |
| 8661 | 3 | 4 | | | IV-1 | STK4 | 1.08 | 8757 | 3 | 4 | | | IV-1 | TCEANC | 1.08 |
| 8662 | 3 | 4 | | | IV-1 | STMN1 | 1.31 | 8758 | 3 | 4 | | | IV-1 | TCEANC2 | 1.12 |
| 8663 | 3 | 4 | | | IV-1 | STOML2 | 1.45 | 8759 | 3 | 4 | | | IV-1 | TCEB1 | 1.27 |
| 8664 | 3 | 4 | | | IV-1 | STRADA | 1.24 | 8760 | 3 | 4 | | | IV-1 | TCERG1 | 1.36 |
| 8665 | 3 | 4 | | | IV-1 | STS | 1.25 | 8761 | 3 | 4 | | | IV-1 | TCF20 | 1.10 |
| 8666 | 3 | 4 | | | IV-1 | STUB1 | 1.24 | 8762 | 3 | 4 | | | IV-1 | TCF25 | 1.41 |
| 8667 | 3 | 4 | | | IV-1 | STX11 | 1.25 | 8763 | 3 | 4 | | | IV-1 | TCF3 | 1.31 |
| 8668 | 3 | 4 | | | IV-1 | STX16 | 1.23 | 8764 | 3 | 4 | | | IV-1 | TCFL5 | 1.05 |
| 8669 | 3 | 4 | | | IV-1 | STX17 | 1.46 | 8765 | 3 | 4 | | | IV-1 | TCTA | 1.31 |
| 8670 | 3 | 4 | | | IV-1 | STX18 | 1.41 | 8766 | 3 | 4 | | | IV-1 | TCTEX1D2 | 1.21 |
| 8671 | 3 | 4 | | | IV-1 | STX4 | 1.26 | 8767 | 3 | 4 | | | IV-1 | TDP1 | 1.26 |
| 8672 | 3 | 4 | | | IV-1 | STX5 | 1.07 | 8768 | 3 | 4 | | | IV-1 | TDRD3 | 1.31 |
| 8673 | 3 | 4 | | | IV-1 | STX8 | 1.18 | 8769 | 3 | 4 | | | IV-1 | TDRD7 | 1.40 |
| 8674 | 3 | 4 | | | IV-1 | STXBP2 | 1.44 | 8770 | 3 | 4 | | | IV-1 | TDRD9 | 1.13 |
| 8675 | 3 | 4 | | | IV-1 | STYX | 1.11 | 8771 | 3 | 4 | | | IV-1 | TDRKH | 1.28 |
| 8676 | 3 | 4 | | | IV-1 | SUB1 | 1.09 | 8772 | 3 | 4 | | | IV-1 | TECPR1 | 1.40 |
| 8677 | 3 | 4 | | | IV-1 | SUCLG2 | 1.43 | 8773 | 3 | 4 | | | IV-1 | TECR | 1.28 |
| 8678 | 3 | 4 | | | IV-1 | SUDS3 | 1.31 | 8774 | 3 | 4 | | | IV-1 | TEN1 | 1.11 |
| 8679 | 3 | 4 | | | IV-1 | SUGP1 | 1.07 | 8775 | 3 | 4 | | | IV-1 | TERF1 | 1.49 |
| 8680 | 3 | 4 | | | IV-1 | SUMO1P1 | 1.35 | 8776 | 3 | 4 | | | IV-1 | TERF2 | 1.42 |
| 8681 | 3 | 4 | | | IV-1 | SUMO1P3 | 1.19 | 8777 | 3 | 4 | | | IV-1 | TERF2IP | 1.31 |
| 8682 | 3 | 4 | | | IV-1 | SUMO3 | 1.49 | 8778 | 3 | 4 | | | IV-1 | TESK1 | 1.44 |
| 8683 | 3 | 4 | | | IV-1 | SUPT6H | 1.39 | 8779 | 3 | 4 | | | IV-1 | TET2 | 1.08 |
| 8684 | 3 | 4 | | | IV-1 | SUPT7L | 1.16 | 8780 | 3 | 4 | | | IV-1 | TET3 | 1.41 |
| 8685 | 3 | 4 | | | IV-1 | SURF2 | 1.23 | 8781 | 3 | 4 | | | IV-1 | TEX2 | 1.37 |
| 8686 | 3 | 4 | | | IV-1 | SURF6 | 1.49 | 8782 | 3 | 4 | | | IV-1 | TEX261 | 1.48 |
| 8687 | 3 | 4 | | | IV-1 | SUSD3 | 1.17 | 8783 | 3 | 4 | | | IV-1 | TEX264 | 1.33 |
| 8688 | 3 | 4 | | | IV-1 | SUV420H1 | 1.23 | 8784 | 3 | 4 | | | IV-1 | TFAMP1 | 1.04 |
| 8689 | 3 | 4 | | | IV-1 | SUZ12 | 1.18 | 8785 | 3 | 4 | | | IV-1 | TFAP4 | 1.12 |
| 8690 | 3 | 4 | | | IV-1 | SVIL | 1.14 | 8786 | 3 | 4 | | | IV-1 | TFB1M | 1.08 |
| 8691 | 3 | 4 | | | IV-1 | SVIP | 1.25 | 8787 | 3 | 4 | | | IV-1 | TFB2M | 1.44 |
| 8692 | 3 | 4 | | | IV-1 | SW15 | 1.32 | 8788 | 3 | 4 | | | IV-1 | TFE3 | 1.12 |
| 8693 | 3 | 4 | | | IV-1 | SWT1 | 1.15 | 8789 | 3 | 4 | | | IV-1 | TFG | 1.47 |
| 8694 | 3 | 4 | | | IV-1 | SYAP1 | 1.23 | 8790 | 3 | 4 | | | IV-1 | TFPT | 1.42 |
| 8695 | 3 | 4 | | | IV-1 | SYF2 | 1.16 | 8791 | 3 | 4 | | | IV-1 | TGDS | 1.30 |
| 8696 | 3 | 4 | | | IV-1 | SYK | 1.45 | 8792 | 3 | 4 | | | IV-1 | TGFB1 | 1.09 |
| 8697 | 3 | 4 | | | IV-1 | SYMPK | 1.36 | 8793 | 3 | 4 | | | IV-1 | TGFBR1 | 1.28 |
| 8698 | 3 | 4 | | | IV-1 | SYNE1 | 1.02 | 8794 | 3 | 4 | | | IV-1 | TGFBR2 | 1.02 |
| 8699 | 3 | 4 | | | IV-1 | SYNJ2 | 1.04 | 8795 | 3 | 4 | | | IV-1 | TGIF1 | 1.22 |
| 8700 | 3 | 4 | | | IV-1 | SYNJ2BP | 1.47 | 8796 | 3 | 4 | | | IV-1 | TGIF2 | 1.02 |
| 8701 | 3 | 4 | | | IV-1 | SYNRG | 1.45 | 8797 | 3 | 4 | | | IV-1 | THAP1 | 1.31 |
| 8702 | 3 | 4 | | | IV-1 | SYS1 | 1.35 | 8798 | 3 | 4 | | | IV-1 | THAP11 | 1.37 |
| 8703 | 3 | 4 | | | IV-1 | SYVN1 | 1.05 | 8799 | 3 | 4 | | | IV-1 | THAP3 | 1.19 |
| 8704 | 3 | 4 | | | IV-1 | SZT2 | 1.03 | 8800 | 3 | 4 | | | IV-1 | THAP4 | 1.18 |
| 8705 | 3 | 4 | | | IV-1 | TAB2 | 1.07 | 8801 | 3 | 4 | | | IV-1 | THAP6 | 1.12 |
| 8706 | 3 | 4 | | | IV-1 | TAB3 | 1.28 | 8802 | 3 | 4 | | | IV-1 | THAP7 | 1.03 |
| 8707 | 3 | 4 | | | IV-1 | TACC3 | 1.14 | 8803 | 3 | 4 | | | IV-1 | THAP8 | 1.45 |
| 8708 | 3 | 4 | | | IV-1 | TACO1 | 1.41 | 8804 | 3 | 4 | | | IV-1 | THAP9 | 1.27 |
| 8709 | 3 | 4 | | | IV-1 | TADA2A | 1.15 | 8805 | 3 | 4 | | | IV-1 | THB53 | 1.13 |
| 8710 | 3 | 4 | | | IV-1 | TADA2B | 1.21 | 8806 | 3 | 4 | | | IV-1 | THEMIS | 1.17 |
| 8711 | 3 | 4 | | | IV-1 | TADA3 | 1.24 | 8807 | 3 | 4 | | | IV-1 | THOC1 | 1.35 |
| 8712 | 3 | 4 | | | IV-1 | TAF1 | 1.28 | 8808 | 3 | 4 | | | IV-1 | THOC7 | 1.17 |
| 8713 | 3 | 4 | | | IV-1 | TAF10 | 1.13 | 8809 | 3 | 4 | | | IV-1 | THOP1 | 1.50 |
| 8714 | 3 | 4 | | | IV-1 | TAF12 | 1.06 | 8810 | 3 | 4 | | | IV-1 | THRAP3 | 1.28 |
| 8715 | 3 | 4 | | | IV-1 | TAF1L | 1.44 | 8811 | 3 | 4 | | | IV-1 | THTPA | 1.02 |
| 8716 | 3 | 4 | | | IV-1 | TAF2 | 1.30 | 8812 | 3 | 4 | | | IV-1 | THYN1 | 1.13 |
| 8717 | 3 | 4 | | | IV-1 | TAF5L | 1.38 | 8813 | 3 | 4 | | | IV-1 | TIA1 | 1.29 |
| 8718 | 3 | 4 | | | IV-1 | TAF6 | 1.08 | 8814 | 3 | 4 | | | IV-1 | TIAL1 | 1.26 |
| 8719 | 3 | 4 | | | IV-1 | TAF7 | 1.13 | 8815 | 3 | 4 | | | IV-1 | TIFA | 1.35 |
| 8720 | 3 | 4 | | | IV-1 | TAF9 | 1.42 | 8816 | 3 | 4 | | | IV-1 | TIGD2 | 1.34 |
| 8721 | 3 | 4 | | | IV-1 | TALDO1 | 1.01 | 8817 | 3 | 4 | | | IV-1 | TIGD6 | 1.38 |
| 8722 | 3 | 4 | | | IV-1 | TAOK2 | 1.20 | 8818 | 3 | 4 | | | IV-1 | TIMM13 | 1.49 |
| 8723 | 3 | 4 | | | IV-1 | TAOK3 | 1.44 | 8819 | 3 | 4 | | | IV-1 | TIMM17B | 1.09 |
| 8724 | 3 | 4 | | | IV-1 | TAP2 | 1.23 | 8820 | 3 | 4 | | | IV-1 | TIMM21 | 1.08 |
| 8725 | 3 | 4 | | | IV-1 | TAPBP | 1.21 | 8821 | 3 | 4 | | | IV-1 | TIMM22 | 1.36 |
| 8726 | 3 | 4 | | | IV-1 | TAPBPL | 1.07 | 8822 | 3 | 4 | | | IV-1 | TIMM8A | 1.35 |
| 8727 | 3 | 4 | | | IV-1 | TAPT1 | 1.24 | 8823 | 3 | 4 | | | IV-1 | TIMM9 | 1.41 |
| 8728 | 3 | 4 | | | IV-1 | TARBP1 | 1.04 | 8824 | 3 | 4 | | | IV-1 | TIMMDC1 | 1.39 |
| 8729 | 3 | 4 | | | IV-1 | TARBP2 | 1.47 | 8825 | 3 | 4 | | | IV-1 | TINF2 | 1.11 |
| 8730 | 3 | 4 | | | IV-1 | TARS2 | 1.32 | 8826 | 3 | 4 | | | IV-1 | TIPARP | 1.30 |
| 8731 | 3 | 4 | | | IV-1 | TATDN1 | 1.10 | 8827 | 3 | 4 | | | IV-1 | TIPIN | 1.10 |

Fig. 41 - 47

| | | | | | | | | | | | | | | |
|---|---|---|---|---|---|---|---|---|---|---|---|---|---|---|
| 8828 | 3 | 4 | | | IV-1 | TIPRL | 1.17 | 8924 | 3 | 4 | | | IV-1 | TNKS1BP1 | 1.46 |
| 8829 | 3 | 4 | | | IV-1 | TJAP1 | 1.28 | 8925 | 3 | 4 | | | IV-1 | TNPO2 | 1.23 |
| 8830 | 3 | 4 | | | IV-1 | TKTL1 | 1.02 | 8926 | 3 | 4 | | | IV-1 | TNRC18 | 1.37 |
| 8831 | 3 | 4 | | | IV-1 | TLE2 | 1.00 | 8927 | 3 | 4 | | | IV-1 | TNRC6B | 1.31 |
| 8832 | 3 | 4 | | | IV-1 | TLE3 | 1.01 | 8928 | 3 | 4 | | | IV-1 | TOB1 | 1.17 |
| 8833 | 3 | 4 | | | IV-1 | TLE4 | 1.36 | 8929 | 3 | 4 | | | IV-1 | TOE1 | 1.20 |
| 8834 | 3 | 4 | | | IV-1 | TLK1 | 1.31 | 8930 | 3 | 4 | | | IV-1 | TOM1 | 1.33 |
| 8835 | 3 | 4 | | | IV-1 | TLR1 | 1.26 | 8931 | 3 | 4 | | | IV-1 | TOM1L2 | 1.02 |
| 8836 | 3 | 4 | | | IV-1 | TLR3 | 1.05 | 8932 | 3 | 4 | | | IV-1 | TOMM22 | 1.30 |
| 8837 | 3 | 4 | | | IV-1 | TLR6 | 1.15 | 8933 | 3 | 4 | | | IV-1 | TOMM34 | 1.27 |
| 8838 | 3 | 4 | | | IV-1 | TM2D3 | 1.45 | 8934 | 3 | 4 | | | IV-1 | TOMM40L | 1.10 |
| 8839 | 3 | 4 | | | IV-1 | TMBIM1 | 1.39 | 8935 | 3 | 4 | | | IV-1 | TOMM5 | 1.33 |
| 8840 | 3 | 4 | | | IV-1 | TMBIM4 | 1.46 | 8936 | 3 | 4 | | | IV-1 | TOMM6 | 1.28 |
| 8841 | 3 | 4 | | | IV-1 | TMBIM6 | 1.46 | 8937 | 3 | 4 | | | IV-1 | TOP2A | 1.15 |
| 8842 | 3 | 4 | | | IV-1 | TMCO4 | 1.30 | 8938 | 3 | 4 | | | IV-1 | TOP3A | 1.47 |
| 8843 | 3 | 4 | | | IV-1 | TMED1 | 1.49 | 8939 | 3 | 4 | | | IV-1 | TOP8P1 | 1.20 |
| 8844 | 3 | 4 | | | IV-1 | TMED4 | 1.31 | 8940 | 3 | 4 | | | IV-1 | TOR2A | 1.40 |
| 8845 | 3 | 4 | | | IV-1 | TMED8 | 1.09 | 8941 | 3 | 4 | | | IV-1 | TOX4 | 1.20 |
| 8846 | 3 | 4 | | | IV-1 | TMEM106B | 1.23 | 8942 | 3 | 4 | | | IV-1 | TP53BP2 | 1.49 |
| 8847 | 3 | 4 | | | IV-1 | TMEM109 | 1.32 | 8943 | 3 | 4 | | | IV-1 | TP53I13 | 1.25 |
| 8848 | 3 | 4 | | | IV-1 | TMEM11 | 1.13 | 8944 | 3 | 4 | | | IV-1 | TP53RK | 1.32 |
| 8849 | 3 | 4 | | | IV-1 | TMEM123 | 1.22 | 8945 | 3 | 4 | | | IV-1 | TP73-AS1 | 1.04 |
| 8850 | 3 | 4 | | | IV-1 | TMEM126A | 1.45 | 8946 | 3 | 4 | | | IV-1 | TPCN2 | 1.42 |
| 8851 | 3 | 4 | | | IV-1 | TMEM127 | 1.46 | 8947 | 3 | 4 | | | IV-1 | TPD52L2 | 1.45 |
| 8852 | 3 | 4 | | | IV-1 | TMEM128 | 1.04 | 8948 | 3 | 4 | | | IV-1 | TPM3 | 1.46 |
| 8853 | 3 | 4 | | | IV-1 | TMEM129 | 1.12 | 8949 | 3 | 4 | | | IV-1 | TPPP3 | 1.43 |
| 8854 | 3 | 4 | | | IV-1 | TMEM134 | 1.07 | 8950 | 3 | 4 | | | IV-1 | TPR | 1.25 |
| 8855 | 3 | 4 | | | IV-1 | TMEM135 | 1.49 | 8951 | 3 | 4 | | | IV-1 | TPRA1 | 1.44 |
| 8856 | 3 | 4 | | | IV-1 | TMEM138 | 1.16 | 8952 | 3 | 4 | | | IV-1 | TPRG1L | 1.11 |
| 8857 | 3 | 4 | | | IV-1 | TMEM14A | 1.35 | 8953 | 3 | 4 | | | IV-1 | TPST2 | 1.34 |
| 8858 | 3 | 4 | | | IV-1 | TMEM14B | 1.19 | 8954 | 3 | 4 | | | IV-1 | TPT1-AS1 | 1.16 |
| 8859 | 3 | 4 | | | IV-1 | TMEM150A | 1.49 | 8955 | 3 | 4 | | | IV-1 | TPX2 | 1.14 |
| 8860 | 3 | 4 | | | IV-1 | TMEM158 | 1.34 | 8956 | 3 | 4 | | | IV-1 | TRA2A | 1.19 |
| 8861 | 3 | 4 | | | IV-1 | TMEM170A | 1.24 | 8957 | 3 | 4 | | | IV-1 | TRABD | 1.16 |
| 8862 | 3 | 4 | | | IV-1 | TMEM179B | 1.29 | 8958 | 3 | 4 | | | IV-1 | TRADD | 1.17 |
| 8863 | 3 | 4 | | | IV-1 | TMEM18 | 1.29 | 8959 | 3 | 4 | | | IV-1 | TRAF2 | 1.23 |
| 8864 | 3 | 4 | | | IV-1 | TMEM181 | 1.41 | 8960 | 3 | 4 | | | IV-1 | TRAF3IP2-AS1 | 1.19 |
| 8865 | 3 | 4 | | | IV-1 | TMEM184B | 1.03 | 8961 | 3 | 4 | | | IV-1 | TRAF3IP3 | 1.16 |
| 8866 | 3 | 4 | | | IV-1 | TMEM185B | 1.47 | 8962 | 3 | 4 | | | IV-1 | TRAF6 | 1.22 |
| 8867 | 3 | 4 | | | IV-1 | TMEM186 | 1.34 | 8963 | 3 | 4 | | | IV-1 | TRAFD1 | 1.21 |
| 8868 | 3 | 4 | | | IV-1 | TMEM187 | 1.15 | 8964 | 3 | 4 | | | IV-1 | TRAK2 | 1.16 |
| 8869 | 3 | 4 | | | IV-1 | TMEM189 | 1.40 | 8965 | 3 | 4 | | | IV-1 | TRAM1 | 1.43 |
| 8870 | 3 | 4 | | | IV-1 | TMEM194A | 1.00 | 8966 | 3 | 4 | | | IV-1 | TRAP1 | 1.15 |
| 8871 | 3 | 4 | | | IV-1 | TMEM199 | 1.41 | 8967 | 3 | 4 | | | IV-1 | TRAPPC1 | 1.23 |
| 8872 | 3 | 4 | | | IV-1 | TMEM203 | 1.17 | 8968 | 3 | 4 | | | IV-1 | TRAPPC10 | 1.06 |
| 8873 | 3 | 4 | | | IV-1 | TMEM206 | 1.33 | 8969 | 3 | 4 | | | IV-1 | TRAPPC2L | 1.21 |
| 8874 | 3 | 4 | | | IV-1 | TMEM219 | 1.10 | 8970 | 3 | 4 | | | IV-1 | TRAPPC3 | 1.33 |
| 8875 | 3 | 4 | | | IV-1 | TMEM223 | 1.09 | 8971 | 3 | 4 | | | IV-1 | TRAPPC4 | 1.24 |
| 8876 | 3 | 4 | | | IV-1 | TMEM229B | 1.23 | 8972 | 3 | 4 | | | IV-1 | TRAPPC5 | 1.13 |
| 8877 | 3 | 4 | | | IV-1 | TMEM234 | 1.03 | 8973 | 3 | 4 | | | IV-1 | TRAPPC6A | 1.02 |
| 8878 | 3 | 4 | | | IV-1 | TMEM241 | 1.37 | 8974 | 3 | 4 | | | IV-1 | TRAPPC6B | 1.14 |
| 8879 | 3 | 4 | | | IV-1 | TMEM242 | 1.31 | 8975 | 3 | 4 | | | IV-1 | TRAPPC8 | 1.49 |
| 8880 | 3 | 4 | | | IV-1 | TMEM308 | 1.13 | 8976 | 3 | 4 | | | IV-1 | TRAPPC9 | 1.47 |
| 8881 | 3 | 4 | | | IV-1 | TMEM39A | 1.27 | 8977 | 3 | 4 | | | IV-1 | TRAT1 | 1.21 |
| 8882 | 3 | 4 | | | IV-1 | TMEM39B | 1.42 | 8978 | 3 | 4 | | | IV-1 | TRDMT1 | 1.00 |
| 8883 | 3 | 4 | | | IV-1 | TMEM41B | 1.04 | 8979 | 3 | 4 | | | IV-1 | TRIB1 | 1.42 |
| 8884 | 3 | 4 | | | IV-1 | TMEM42 | 1.02 | 8980 | 3 | 4 | | | IV-1 | TRIB2 | 1.31 |
| 8885 | 3 | 4 | | | IV-1 | TMEM43 | 1.19 | 8981 | 3 | 4 | | | IV-1 | TRIB3 | 1.31 |
| 8886 | 3 | 4 | | | IV-1 | TMEM45B | 1.01 | 8982 | 3 | 4 | | | IV-1 | TRIM11 | 1.44 |
| 8887 | 3 | 4 | | | IV-1 | TMEM48 | 1.42 | 8983 | 3 | 4 | | | IV-1 | TRIM13 | 1.44 |
| 8888 | 3 | 4 | | | IV-1 | TMEM5 | 1.45 | 8984 | 3 | 4 | | | IV-1 | TRIM16L | 1.01 |
| 8889 | 3 | 4 | | | IV-1 | TMEM50A | 1.22 | 8985 | 3 | 4 | | | IV-1 | TRIM21 | 1.24 |
| 8890 | 3 | 4 | | | IV-1 | TMEM50B | 1.21 | 8986 | 3 | 4 | | | IV-1 | TRIM23 | 1.04 |
| 8891 | 3 | 4 | | | IV-1 | TMEM53 | 1.17 | 8987 | 3 | 4 | | | IV-1 | TRIM24 | 1.42 |
| 8892 | 3 | 4 | | | IV-1 | TMEM59 | 1.30 | 8988 | 3 | 4 | | | IV-1 | TRIM25 | 1.29 |
| 8893 | 3 | 4 | | | IV-1 | TMEM63A | 1.12 | 8989 | 3 | 4 | | | IV-1 | TRIM27 | 1.35 |
| 8894 | 3 | 4 | | | IV-1 | TMEM66 | 1.34 | 8990 | 3 | 4 | | | IV-1 | TRIM3 | 1.25 |
| 8895 | 3 | 4 | | | IV-1 | TMEM70 | 1.41 | 8991 | 3 | 4 | | | IV-1 | TRIM32 | 1.33 |
| 8896 | 3 | 4 | | | IV-1 | TMEM80 | 1.02 | 8992 | 3 | 4 | | | IV-1 | TRIM33 | 1.41 |
| 8897 | 3 | 4 | | | IV-1 | TMEM85 | 1.17 | 8993 | 3 | 4 | | | IV-1 | TRIM37 | 1.21 |
| 8898 | 3 | 4 | | | IV-1 | TMEM8A | 1.13 | 8994 | 3 | 4 | | | IV-1 | TRIM4 | 1.47 |
| 8899 | 3 | 4 | | | IV-1 | TMEM8B | 1.11 | 8995 | 3 | 4 | | | IV-1 | TRIM52 | 1.06 |
| 8900 | 3 | 4 | | | IV-1 | TMEM93 | 1.42 | 8996 | 3 | 4 | | | IV-1 | TRIM59 | 1.27 |
| 8901 | 3 | 4 | | | IV-1 | TMEM97 | 1.09 | 8997 | 3 | 4 | | | IV-1 | TRIM62 | 1.08 |
| 8902 | 3 | 4 | | | IV-1 | TMF1 | 1.37 | 8998 | 3 | 4 | | | IV-1 | TRIM65 | 1.45 |
| 8903 | 3 | 4 | | | IV-1 | TMIGD2 | 1.07 | 8999 | 3 | 4 | | | IV-1 | TRIM68 | 1.33 |
| 8904 | 3 | 4 | | | IV-1 | TMLHE | 1.46 | 9000 | 3 | 4 | | | IV-1 | TRIO8P | 1.19 |
| 8905 | 3 | 4 | | | IV-1 | TMOD2 | 1.29 | 9001 | 3 | 4 | | | IV-1 | TRIP6 | 1.28 |
| 8906 | 3 | 4 | | | IV-1 | TMSB10 | 1.42 | 9002 | 3 | 4 | | | IV-1 | TRMT112 | 1.47 |
| 8907 | 3 | 4 | | | IV-1 | TMSB4X | 1.23 | 9003 | 3 | 4 | | | IV-1 | TRMT2A | 1.40 |
| 8908 | 3 | 4 | | | IV-1 | TMTC3 | 1.32 | 9004 | 3 | 4 | | | IV-1 | TRMT2B | 1.09 |
| 8909 | 3 | 4 | | | IV-1 | TMUB1 | 1.06 | 9005 | 3 | 4 | | | IV-1 | TRMT61A | 1.35 |
| 8910 | 3 | 4 | | | IV-1 | TMUB2 | 1.18 | 9006 | 3 | 4 | | | IV-1 | TRMT61B | 1.29 |
| 8911 | 3 | 4 | | | IV-1 | TNFAIP1 | 1.40 | 9007 | 3 | 4 | | | IV-1 | TRMU | 1.09 |
| 8912 | 3 | 4 | | | IV-1 | TNFAIP8 | 1.36 | 9008 | 3 | 4 | | | IV-1 | TRNAU1AP | 1.13 |
| 8913 | 3 | 4 | | | IV-1 | TNFAIP8L1 | 1.28 | 9009 | 3 | 4 | | | IV-1 | TRNP1 | 1.27 |
| 8914 | 3 | 4 | | | IV-1 | TNFAIP8L2 | 1.35 | 9010 | 3 | 4 | | | IV-1 | TROVE2 | 1.47 |
| 8915 | 3 | 4 | | | IV-1 | TNFRSF10A | 1.29 | 9011 | 3 | 4 | | | IV-1 | TRPC4AP | 1.39 |
| 8916 | 3 | 4 | | | IV-1 | TNFRSF11A | 1.02 | 9012 | 3 | 4 | | | IV-1 | TRPM7 | 1.15 |
| 8917 | 3 | 4 | | | IV-1 | TNFRSF14 | 1.03 | 9013 | 3 | 4 | | | IV-1 | TRUB1 | 1.25 |
| 8918 | 3 | 4 | | | IV-1 | TNFRSF1A | 1.29 | 9014 | 3 | 4 | | | IV-1 | TRUB2 | 1.42 |
| 8919 | 3 | 4 | | | IV-1 | TNFRSF4 | 1.05 | 9015 | 3 | 4 | | | IV-1 | TSC1 | 1.21 |
| 8920 | 3 | 4 | | | IV-1 | TNFSF10 | 1.39 | 9016 | 3 | 4 | | | IV-1 | TSEN15 | 1.23 |
| 8921 | 3 | 4 | | | IV-1 | TNFSF12 | 1.11 | 9017 | 3 | 4 | | | IV-1 | TSFM | 1.08 |
| 8922 | 3 | 4 | | | IV-1 | TNFSF14 | 1.12 | 9018 | 3 | 4 | | | IV-1 | TSG101 | 1.20 |
| 8923 | 3 | 4 | | | IV-1 | TNIP2 | 1.28 | 9019 | 3 | 4 | | | IV-1 | TSNAX | 1.37 |

Fig. 41 - 48

| | | | | | | | | | | | | | | | |
|---|---|---|---|---|---|---|---|---|---|---|---|---|---|---|---|
| 9020 | 3 | 4 | | | IV-1 | TSPAN31 | 1.43 | 9116 | 3 | 4 | | | IV-1 | UBXN1 | 1.19 |
| 9021 | 3 | 4 | | | IV-1 | TSPAN32 | 1.05 | 9117 | 3 | 4 | | | IV-1 | UBXN2B | 1.07 |
| 9022 | 3 | 4 | | | IV-1 | TSPYL1 | 1.31 | 9118 | 3 | 4 | | | IV-1 | UBXN8 | 1.44 |
| 9023 | 3 | 4 | | | IV-1 | TSPYL4 | 1.21 | 9119 | 3 | 4 | | | IV-1 | UCHL5 | 1.29 |
| 9024 | 3 | 4 | | | IV-1 | TSPYL5 | 1.06 | 9120 | 3 | 4 | | | IV-1 | UCK1 | 1.38 |
| 9025 | 3 | 4 | | | IV-1 | TSR2 | 1.35 | 9121 | 3 | 4 | | | IV-1 | UCKL1 | 1.15 |
| 9026 | 3 | 4 | | | IV-1 | TSSC4 | 1.36 | 9122 | 3 | 4 | | | IV-1 | UFC1 | 1.19 |
| 9027 | 3 | 4 | | | IV-1 | TST | 1.03 | 9123 | 3 | 4 | | | IV-1 | UFD1L | 1.12 |
| 9028 | 3 | 4 | | | IV-1 | TSTD2 | 1.37 | 9124 | 3 | 4 | | | IV-1 | UFM1 | 1.33 |
| 9029 | 3 | 4 | | | IV-1 | TTC1 | 1.27 | 9125 | 3 | 4 | | | IV-1 | UFSP1 | 1.20 |
| 9030 | 3 | 4 | | | IV-1 | TTC13 | 1.42 | 9126 | 3 | 4 | | | IV-1 | UGCG | 1.18 |
| 9031 | 3 | 4 | | | IV-1 | TTC17 | 1.37 | 9127 | 3 | 4 | | | IV-1 | UGDH | 1.45 |
| 9032 | 3 | 4 | | | IV-1 | TTC19 | 1.47 | 9128 | 3 | 4 | | | IV-1 | UHMK1 | 1.44 |
| 9033 | 3 | 4 | | | IV-1 | TTC21B | 1.48 | 9129 | 3 | 4 | | | IV-1 | UHRF1 | 1.21 |
| 9034 | 3 | 4 | | | IV-1 | TTC26 | 1.30 | 9130 | 3 | 4 | | | IV-1 | UHRF1BP1L | 1.45 |
| 9035 | 3 | 4 | | | IV-1 | TTC3 | 1.15 | 9131 | 3 | 4 | | | IV-1 | UHRF2 | 1.18 |
| 9036 | 3 | 4 | | | IV-1 | TTC31 | 1.37 | 9132 | 3 | 4 | | | IV-1 | UMPS | 1.37 |
| 9037 | 3 | 4 | | | IV-1 | TTC33 | 1.22 | 9133 | 3 | 4 | | | IV-1 | UNC119B | 1.17 |
| 9038 | 3 | 4 | | | IV-1 | TTC35 | 1.36 | 9134 | 3 | 4 | | | IV-1 | UNC13D | 1.40 |
| 9039 | 3 | 4 | | | IV-1 | TTC37 | 1.24 | 9135 | 3 | 4 | | | IV-1 | UNG | 1.20 |
| 9040 | 3 | 4 | | | IV-1 | TTC38 | 1.33 | 9136 | 3 | 4 | | | IV-1 | UNK | 1.02 |
| 9041 | 3 | 4 | | | IV-1 | TTC39C | 1.24 | 9137 | 3 | 4 | | | IV-1 | UPF1 | 1.34 |
| 9042 | 3 | 4 | | | IV-1 | TTC3P1 | 1.16 | 9138 | 3 | 4 | | | IV-1 | UPF3A | 1.21 |
| 9043 | 3 | 4 | | | IV-1 | TTC4 | 1.45 | 9139 | 3 | 4 | | | IV-1 | UQCC | 1.26 |
| 9044 | 3 | 4 | | | IV-1 | TTC5 | 1.39 | 9140 | 3 | 4 | | | IV-1 | UQCR11 | 1.14 |
| 9045 | 3 | 4 | | | IV-1 | TTC9C | 1.22 | 9141 | 3 | 4 | | | IV-1 | UQCRB | 1.11 |
| 9046 | 3 | 4 | | | IV-1 | TTI2 | 1.33 | 9142 | 3 | 4 | | | IV-1 | UQCRC2 | 1.48 |
| 9047 | 3 | 4 | | | IV-1 | TTLL1 | 1.41 | 9143 | 3 | 4 | | | IV-1 | UQCRH | 1.24 |
| 9048 | 3 | 4 | | | IV-1 | TTLL11 | 1.45 | 9144 | 3 | 4 | | | IV-1 | URB1 | 1.45 |
| 9049 | 3 | 4 | | | IV-1 | TTLL4 | 1.16 | 9145 | 3 | 4 | | | IV-1 | URGCP | 1.47 |
| 9050 | 3 | 4 | | | IV-1 | TTPAL | 1.45 | 9146 | 3 | 4 | | | IV-1 | URI1 | 1.48 |
| 9051 | 3 | 4 | | | IV-1 | TUBA1B | 1.35 | 9147 | 3 | 4 | | | IV-1 | URM1 | 1.37 |
| 9052 | 3 | 4 | | | IV-1 | TUBA1C | 1.42 | 9148 | 3 | 4 | | | IV-1 | UROD | 1.17 |
| 9053 | 3 | 4 | | | IV-1 | TUBB4B | 1.09 | 9149 | 3 | 4 | | | IV-1 | USP1 | 1.40 |
| 9054 | 3 | 4 | | | IV-1 | TUBD1 | 1.25 | 9150 | 3 | 4 | | | IV-1 | USP11 | 1.29 |
| 9055 | 3 | 4 | | | IV-1 | TUBG1 | 1.36 | 9151 | 3 | 4 | | | IV-1 | USP18 | 1.13 |
| 9056 | 3 | 4 | | | IV-1 | TUFM | 1.46 | 9152 | 3 | 4 | | | IV-1 | USP19 | 1.30 |
| 9057 | 3 | 4 | | | IV-1 | TULP3 | 1.24 | 9153 | 3 | 4 | | | IV-1 | USP21 | 1.06 |
| 9058 | 3 | 4 | | | IV-1 | TUT1 | 1.49 | 9154 | 3 | 4 | | | IV-1 | USP24 | 1.49 |
| 9059 | 3 | 4 | | | IV-1 | TWF1 | 1.38 | 9155 | 3 | 4 | | | IV-1 | USP25 | 1.34 |
| 9060 | 3 | 4 | | | IV-1 | TWISTNB | 1.15 | 9156 | 3 | 4 | | | IV-1 | USP28 | 1.05 |
| 9061 | 3 | 4 | | | IV-1 | TWSG1 | 1.13 | 9157 | 3 | 4 | | | IV-1 | USP30 | 1.22 |
| 9062 | 3 | 4 | | | IV-1 | TXN2 | 1.47 | 9158 | 3 | 4 | | | IV-1 | USP31 | 1.49 |
| 9063 | 3 | 4 | | | IV-1 | TXNDC11 | 1.47 | 9159 | 3 | 4 | | | IV-1 | USP32 | 1.12 |
| 9064 | 3 | 4 | | | IV-1 | TXNDC12 | 1.19 | 9160 | 3 | 4 | | | IV-1 | USP34 | 1.11 |
| 9065 | 3 | 4 | | | IV-1 | TXNDC16 | 1.16 | 9161 | 3 | 4 | | | IV-1 | USP35 | 1.43 |
| 9066 | 3 | 4 | | | IV-1 | TXNDC17 | 1.20 | 9162 | 3 | 4 | | | IV-1 | USP36 | 1.15 |
| 9067 | 3 | 4 | | | IV-1 | TXNIP | 1.19 | 9163 | 3 | 4 | | | IV-1 | USP39 | 1.38 |
| 9068 | 3 | 4 | | | IV-1 | TXNL1 | 1.47 | 9164 | 3 | 4 | | | IV-1 | USP4 | 1.29 |
| 9069 | 3 | 4 | | | IV-1 | TXNL4B | 1.15 | 9165 | 3 | 4 | | | IV-1 | USP42 | 1.39 |
| 9070 | 3 | 4 | | | IV-1 | TYK2 | 1.02 | 9166 | 3 | 4 | | | IV-1 | USP46 | 1.29 |
| 9071 | 3 | 4 | | | IV-1 | TYROBP | 1.02 | 9167 | 3 | 4 | | | IV-1 | USP48 | 1.38 |
| 9072 | 3 | 4 | | | IV-1 | TYSND1 | 1.20 | 9168 | 3 | 4 | | | IV-1 | USP6NL | 1.22 |
| 9073 | 3 | 4 | | | IV-1 | TYW1B | 1.17 | 9169 | 3 | 4 | | | IV-1 | USP9X | 1.43 |
| 9074 | 3 | 4 | | | IV-1 | TYW3 | 1.46 | 9170 | 3 | 4 | | | IV-1 | USP9Y | 1.49 |
| 9075 | 3 | 4 | | | IV-1 | TYW5 | 1.06 | 9171 | 3 | 4 | | | IV-1 | USPL1 | 1.02 |
| 9076 | 3 | 4 | | | IV-1 | U2AF1 | 1.27 | 9172 | 3 | 4 | | | IV-1 | UTP14A | 1.22 |
| 9077 | 3 | 4 | | | IV-1 | U2AF2 | 1.23 | 9173 | 3 | 4 | | | IV-1 | UTP20 | 1.16 |
| 9078 | 3 | 4 | | | IV-1 | U2SURP | 1.35 | 9174 | 3 | 4 | | | IV-1 | UVRAG | 1.41 |
| 9079 | 3 | 4 | | | IV-1 | UAP1 | 1.02 | 9175 | 3 | 4 | | | IV-1 | UXS1 | 1.32 |
| 9080 | 3 | 4 | | | IV-1 | UBA1 | 1.39 | 9176 | 3 | 4 | | | IV-1 | VAMP2 | 1.08 |
| 9081 | 3 | 4 | | | IV-1 | UBA7 | 1.45 | 9177 | 3 | 4 | | | IV-1 | VAMP3 | 1.47 |
| 9082 | 3 | 4 | | | IV-1 | UBAC2 | 1.28 | 9178 | 3 | 4 | | | IV-1 | VAMP4 | 1.29 |
| 9083 | 3 | 4 | | | IV-1 | UBAP2 | 1.39 | 9179 | 3 | 4 | | | IV-1 | VANGL1 | 1.37 |
| 9084 | 3 | 4 | | | IV-1 | UBAP2L | 1.27 | 9180 | 3 | 4 | | | IV-1 | VAPB | 1.21 |
| 9085 | 3 | 4 | | | IV-1 | UBC | 1.23 | 9181 | 3 | 4 | | | IV-1 | VASP | 1.09 |
| 9086 | 3 | 4 | | | IV-1 | UBE2A | 1.46 | 9182 | 3 | 4 | | | IV-1 | VAV1 | 1.46 |
| 9087 | 3 | 4 | | | IV-1 | UBE2B | 1.10 | 9183 | 3 | 4 | | | IV-1 | VAV3 | 1.24 |
| 9088 | 3 | 4 | | | IV-1 | UBE2D2 | 1.15 | 9184 | 3 | 4 | | | IV-1 | VDAC3 | 1.44 |
| 9089 | 3 | 4 | | | IV-1 | UBE2D3 | 1.26 | 9185 | 3 | 4 | | | IV-1 | VEGFA | 1.25 |
| 9090 | 3 | 4 | | | IV-1 | UBE2E3 | 1.30 | 9186 | 3 | 4 | | | IV-1 | VEZF1 | 1.35 |
| 9091 | 3 | 4 | | | IV-1 | UBE2G2 | 1.24 | 9187 | 3 | 4 | | | IV-1 | VEZT | 1.33 |
| 9092 | 3 | 4 | | | IV-1 | UBE2H | 1.39 | 9188 | 3 | 4 | | | IV-1 | VGLL4 | 1.44 |
| 9093 | 3 | 4 | | | IV-1 | UBE2J2 | 1.41 | 9189 | 3 | 4 | | | IV-1 | VHL | 1.28 |
| 9094 | 3 | 4 | | | IV-1 | UBE2L6 | 1.30 | 9190 | 3 | 4 | | | IV-1 | VILL | 1.21 |
| 9095 | 3 | 4 | | | IV-1 | UBE2MP1 | 1.09 | 9191 | 3 | 4 | | | IV-1 | VMA21 | 1.36 |
| 9096 | 3 | 4 | | | IV-1 | UBE2NL | 1.47 | 9192 | 3 | 4 | | | IV-1 | VMO1 | 1.40 |
| 9097 | 3 | 4 | | | IV-1 | UBE2Q1 | 1.28 | 9193 | 3 | 4 | | | IV-1 | VOPP1 | 1.15 |
| 9098 | 3 | 4 | | | IV-1 | UBE2Q2 | 1.16 | 9194 | 3 | 4 | | | IV-1 | VPS13B | 1.23 |
| 9099 | 3 | 4 | | | IV-1 | UBE2R2 | 1.41 | 9195 | 3 | 4 | | | IV-1 | VPS16 | 1.40 |
| 9100 | 3 | 4 | | | IV-1 | UBE2W | 1.39 | 9196 | 3 | 4 | | | IV-1 | VPS26B | 1.40 |
| 9101 | 3 | 4 | | | IV-1 | UBE2Z | 1.18 | 9197 | 3 | 4 | | | IV-1 | VPS28 | 1.20 |
| 9102 | 3 | 4 | | | IV-1 | UBE3B | 1.47 | 9198 | 3 | 4 | | | IV-1 | VPS29 | 1.11 |
| 9103 | 3 | 4 | | | IV-1 | UBE4B | 1.49 | 9199 | 3 | 4 | | | IV-1 | VPS37A | 1.14 |
| 9104 | 3 | 4 | | | IV-1 | UBIAD1 | 1.45 | 9200 | 3 | 4 | | | IV-1 | VPS37B | 1.04 |
| 9105 | 3 | 4 | | | IV-1 | UBL3 | 1.43 | 9201 | 3 | 4 | | | IV-1 | VPS39 | 1.29 |
| 9106 | 3 | 4 | | | IV-1 | UBL7 | 1.16 | 9202 | 3 | 4 | | | IV-1 | VPS4A | 1.43 |
| 9107 | 3 | 4 | | | IV-1 | UBLCP1 | 1.34 | 9203 | 3 | 4 | | | IV-1 | VPS4B | 1.38 |
| 9108 | 3 | 4 | | | IV-1 | UBN2 | 1.41 | 9204 | 3 | 4 | | | IV-1 | VPS52 | 1.24 |
| 9109 | 3 | 4 | | | IV-1 | UBOX5 | 1.20 | 9205 | 3 | 4 | | | IV-1 | VPS72 | 1.14 |
| 9110 | 3 | 4 | | | IV-1 | UBQLN4 | 1.20 | 9206 | 3 | 4 | | | IV-1 | VPS8 | 1.17 |
| 9111 | 3 | 4 | | | IV-1 | UBR4 | 1.34 | 9207 | 3 | 4 | | | IV-1 | VTI1A | 1.41 |
| 9112 | 3 | 4 | | | IV-1 | UBR5 | 1.24 | 9208 | 3 | 4 | | | IV-1 | VTI1B | 1.36 |
| 9113 | 3 | 4 | | | IV-1 | UBR7 | 1.45 | 9209 | 3 | 4 | | | IV-1 | WAC | 1.29 |
| 9114 | 3 | 4 | | | IV-1 | UBTD1 | 1.39 | 9210 | 3 | 4 | | | IV-1 | WAPAL | 1.49 |
| 9115 | 3 | 4 | | | IV-1 | UBTF | 1.24 | 9211 | 3 | 4 | | | IV-1 | WAS | 1.10 |

Fig. 41 - 49

| | | | | | | | | | | | | | | |
|---|---|---|---|---|---|---|---|---|---|---|---|---|---|---|
| 9212 | 3 | 4 | | | IV-1 | WBP11 | 1.41 | 9308 | 3 | 4 | | | IV-1 | ZCCHC17 | 1.20 |
| 9213 | 3 | 4 | | | IV-1 | WBP11P1 | 1.31 | 9309 | 3 | 4 | | | IV-1 | ZCCHC2 | 1.29 |
| 9214 | 3 | 4 | | | IV-1 | WBP2 | 1.00 | 9310 | 3 | 4 | | | IV-1 | ZCCHC3 | 1.18 |
| 9215 | 3 | 4 | | | IV-1 | WBP5 | 1.23 | 9311 | 3 | 4 | | | IV-1 | ZCCHC4 | 1.22 |
| 9216 | 3 | 4 | | | IV-1 | WBSCR22 | 1.46 | 9312 | 3 | 4 | | | IV-1 | ZCCHC6 | 1.02 |
| 9217 | 3 | 4 | | | IV-1 | WDR1 | 1.45 | 9313 | 3 | 4 | | | IV-1 | ZCCHC7 | 1.01 |
| 9218 | 3 | 4 | | | IV-1 | WDR20 | 1.18 | 9314 | 3 | 4 | | | IV-1 | ZCCHC8 | 1.44 |
| 9219 | 3 | 4 | | | IV-1 | WDR24 | 1.40 | 9315 | 3 | 4 | | | IV-1 | ZCCHC9 | 1.05 |
| 9220 | 3 | 4 | | | IV-1 | WDR25 | 1.36 | 9316 | 3 | 4 | | | IV-1 | ZCRB1 | 1.23 |
| 9221 | 3 | 4 | | | IV-1 | WDR26 | 1.21 | 9317 | 3 | 4 | | | IV-1 | ZDHHC12 | 1.28 |
| 9222 | 3 | 4 | | | IV-1 | WDR33 | 1.40 | 9318 | 3 | 4 | | | IV-1 | ZDHHC13 | 1.37 |
| 9223 | 3 | 4 | | | IV-1 | WDR43 | 1.31 | 9319 | 3 | 4 | | | IV-1 | ZDHHC14 | 1.03 |
| 9224 | 3 | 4 | | | IV-1 | WDR44 | 1.38 | 9320 | 3 | 4 | | | IV-1 | ZDHHC16 | 1.39 |
| 9225 | 3 | 4 | | | IV-1 | WDR47 | 1.44 | 9321 | 3 | 4 | | | IV-1 | ZDHHC17 | 1.04 |
| 9226 | 3 | 4 | | | IV-1 | WDR48 | 1.45 | 9322 | 3 | 4 | | | IV-1 | ZDHHC2 | 1.21 |
| 9227 | 3 | 4 | | | IV-1 | WDR5 | 1.49 | 9323 | 3 | 4 | | | IV-1 | ZDHHC3 | 1.26 |
| 9228 | 3 | 4 | | | IV-1 | WDR53 | 1.16 | 9324 | 3 | 4 | | | IV-1 | ZDHHC6 | 1.43 |
| 9229 | 3 | 4 | | | IV-1 | WDR55 | 1.36 | 9325 | 3 | 4 | | | IV-1 | ZDHHC8 | 1.11 |
| 9230 | 3 | 4 | | | IV-1 | WDR59 | 1.04 | 9326 | 3 | 4 | | | IV-1 | ZDHHC9 | 1.35 |
| 9231 | 3 | 4 | | | IV-1 | WDR5B | 1.46 | 9327 | 3 | 4 | | | IV-1 | ZFAND2A | 1.22 |
| 9232 | 3 | 4 | | | IV-1 | WDR6 | 1.12 | 9328 | 3 | 4 | | | IV-1 | ZFAND3 | 1.21 |
| 9233 | 3 | 4 | | | IV-1 | WDR70 | 1.34 | 9329 | 3 | 4 | | | IV-1 | ZFAND6 | 1.21 |
| 9234 | 3 | 4 | | | IV-1 | WDR74 | 1.20 | 9330 | 3 | 4 | | | IV-1 | ZFAT | 1.33 |
| 9235 | 3 | 4 | | | IV-1 | WDR75 | 1.44 | 9331 | 3 | 4 | | | IV-1 | ZFC3H1 | 1.17 |
| 9236 | 3 | 4 | | | IV-1 | WDR76 | 1.45 | 9332 | 3 | 4 | | | IV-1 | ZFP14 | 1.02 |
| 9237 | 3 | 4 | | | IV-1 | WDR82 | 1.34 | 9333 | 3 | 4 | | | IV-1 | ZFP161 | 1.21 |
| 9238 | 3 | 4 | | | IV-1 | WDR89 | 1.18 | 9334 | 3 | 4 | | | IV-1 | ZFP3 | 1.18 |
| 9239 | 3 | 4 | | | IV-1 | WDR91 | 1.48 | 9335 | 3 | 4 | | | IV-1 | ZFP30 | 1.07 |
| 9240 | 3 | 4 | | | IV-1 | WDR92 | 1.40 | 9336 | 3 | 4 | | | IV-1 | ZFP36 | 1.11 |
| 9241 | 3 | 4 | | | IV-1 | WFS1 | 1.16 | 9337 | 3 | 4 | | | IV-1 | ZFP36L1 | 1.02 |
| 9242 | 3 | 4 | | | IV-1 | WHAMM | 1.17 | 9338 | 3 | 4 | | | IV-1 | ZFP36L2 | 1.20 |
| 9243 | 3 | 4 | | | IV-1 | WHSC1L1 | 1.23 | 9339 | 3 | 4 | | | IV-1 | ZFP41 | 1.27 |
| 9244 | 3 | 4 | | | IV-1 | WIBG | 1.28 | 9340 | 3 | 4 | | | IV-1 | ZFP62 | 1.25 |
| 9245 | 3 | 4 | | | IV-1 | WIPF1 | 1.09 | 9341 | 3 | 4 | | | IV-1 | ZFP91 | 1.40 |
| 9246 | 3 | 4 | | | IV-1 | WIPF2 | 1.33 | 9342 | 3 | 4 | | | IV-1 | ZFPM1 | 1.01 |
| 9247 | 3 | 4 | | | IV-1 | WIPI1 | 1.17 | 9343 | 3 | 4 | | | IV-1 | ZFYVE16 | 1.27 |
| 9248 | 3 | 4 | | | IV-1 | WIPI2 | 1.47 | 9344 | 3 | 4 | | | IV-1 | ZFYVE19 | 1.05 |
| 9249 | 3 | 4 | | | IV-1 | WNK1 | 1.23 | 9345 | 3 | 4 | | | IV-1 | ZFYVE20 | 1.31 |
| 9250 | 3 | 4 | | | IV-1 | WNT5B | 1.42 | 9346 | 3 | 4 | | | IV-1 | ZGPAT | 1.28 |
| 9251 | 3 | 4 | | | IV-1 | WRAP73 | 1.14 | 9347 | 3 | 4 | | | IV-1 | ZHX3 | 1.50 |
| 9252 | 3 | 4 | | | IV-1 | WRB | 1.00 | 9348 | 3 | 4 | | | IV-1 | ZKSCAN2 | 1.21 |
| 9253 | 3 | 4 | | | IV-1 | WRNIP1 | 1.43 | 9349 | 3 | 4 | | | IV-1 | ZKSCAN3 | 1.31 |
| 9254 | 3 | 4 | | | IV-1 | WSB1 | 1.47 | 9350 | 3 | 4 | | | IV-1 | ZKSCAN4 | 1.18 |
| 9255 | 3 | 4 | | | IV-1 | WSB2 | 1.40 | 9351 | 3 | 4 | | | IV-1 | ZMAT2 | 1.41 |
| 9256 | 3 | 4 | | | IV-1 | WTAP | 1.21 | 9352 | 3 | 4 | | | IV-1 | ZMAT5 | 1.15 |
| 9257 | 3 | 4 | | | IV-1 | WTH3DI | 1.21 | 9353 | 3 | 4 | | | IV-1 | ZMIZ1 | 1.20 |
| 9258 | 3 | 4 | | | IV-1 | WWP2 | 1.34 | 9354 | 3 | 4 | | | IV-1 | ZMYM1 | 1.08 |
| 9259 | 3 | 4 | | | IV-1 | XPA | 1.44 | 9355 | 3 | 4 | | | IV-1 | ZMYM5 | 1.45 |
| 9260 | 3 | 4 | | | IV-1 | XPC | 1.07 | 9356 | 3 | 4 | | | IV-1 | ZMYM6 | 1.26 |
| 9261 | 3 | 4 | | | IV-1 | XPNPEP3 | 1.05 | 9357 | 3 | 4 | | | IV-1 | ZMYM6NB | 1.25 |
| 9262 | 3 | 4 | | | IV-1 | XRCC1 | 1.11 | 9358 | 3 | 4 | | | IV-1 | ZMYND11 | 1.15 |
| 9263 | 3 | 4 | | | IV-1 | XRCC6 | 1.46 | 9359 | 3 | 4 | | | IV-1 | ZMYND19 | 1.46 |
| 9264 | 3 | 4 | | | IV-1 | XRN1 | 1.22 | 9360 | 3 | 4 | | | IV-1 | ZNF101 | 1.17 |
| 9265 | 3 | 4 | | | IV-1 | XYLT2 | 1.25 | 9361 | 3 | 4 | | | IV-1 | ZNF12 | 1.48 |
| 9266 | 3 | 4 | | | IV-1 | YAF2 | 1.01 | 9362 | 3 | 4 | | | IV-1 | ZNF121 | 1.49 |
| 9267 | 3 | 4 | | | IV-1 | YDJC | 1.13 | 9363 | 3 | 4 | | | IV-1 | ZNF131 | 1.04 |
| 9268 | 3 | 4 | | | IV-1 | YIPF1 | 1.26 | 9364 | 3 | 4 | | | IV-1 | ZNF133 | 1.15 |
| 9269 | 3 | 4 | | | IV-1 | YIPF2 | 1.35 | 9365 | 3 | 4 | | | IV-1 | ZNF134 | 1.14 |
| 9270 | 3 | 4 | | | IV-1 | YIPF3 | 1.05 | 9366 | 3 | 4 | | | IV-1 | ZNF136 | 1.35 |
| 9271 | 3 | 4 | | | IV-1 | YIPF6 | 1.36 | 9367 | 3 | 4 | | | IV-1 | ZNF14 | 1.12 |
| 9272 | 3 | 4 | | | IV-1 | YKT6 | 1.33 | 9368 | 3 | 4 | | | IV-1 | ZNF140 | 1.02 |
| 9273 | 3 | 4 | | | IV-1 | YPEL5 | 1.03 | 9369 | 3 | 4 | | | IV-1 | ZNF141 | 1.49 |
| 9274 | 3 | 4 | | | IV-1 | YRDC | 1.35 | 9370 | 3 | 4 | | | IV-1 | ZNF142 | 1.29 |
| 9275 | 3 | 4 | | | IV-1 | YTHDC1 | 1.20 | 9371 | 3 | 4 | | | IV-1 | ZNF143 | 1.43 |
| 9276 | 3 | 4 | | | IV-1 | YTHDF3 | 1.37 | 9372 | 3 | 4 | | | IV-1 | ZNF148 | 1.26 |
| 9277 | 3 | 4 | | | IV-1 | ZBED1 | 1.43 | 9373 | 3 | 4 | | | IV-1 | ZNF160 | 1.15 |
| 9278 | 3 | 4 | | | IV-1 | ZBED3 | 1.33 | 9374 | 3 | 4 | | | IV-1 | ZNF169 | 1.40 |
| 9279 | 3 | 4 | | | IV-1 | ZBED5 | 1.33 | 9375 | 3 | 4 | | | IV-1 | ZNF17 | 1.19 |
| 9280 | 3 | 4 | | | IV-1 | ZBED6 | 1.15 | 9376 | 3 | 4 | | | IV-1 | ZNF175 | 1.33 |
| 9281 | 3 | 4 | | | IV-1 | ZBTB1 | 1.25 | 9377 | 3 | 4 | | | IV-1 | ZNF18 | 1.03 |
| 9282 | 3 | 4 | | | IV-1 | ZBTB11 | 1.46 | 9378 | 3 | 4 | | | IV-1 | ZNF180 | 1.35 |
| 9283 | 3 | 4 | | | IV-1 | ZBTB2 | 1.42 | 9379 | 3 | 4 | | | IV-1 | ZNF181 | 1.16 |
| 9284 | 3 | 4 | | | IV-1 | ZBTB22 | 1.03 | 9380 | 3 | 4 | | | IV-1 | ZNF182 | 1.09 |
| 9285 | 3 | 4 | | | IV-1 | ZBTB3 | 1.43 | 9381 | 3 | 4 | | | IV-1 | ZNF184 | 1.20 |
| 9286 | 3 | 4 | | | IV-1 | ZBTB34 | 1.03 | 9382 | 3 | 4 | | | IV-1 | ZNF192 | 1.23 |
| 9287 | 3 | 4 | | | IV-1 | ZBTB38 | 1.28 | 9383 | 3 | 4 | | | IV-1 | ZNF195 | 1.23 |
| 9288 | 3 | 4 | | | IV-1 | ZBTB4 | 1.12 | 9384 | 3 | 4 | | | IV-1 | ZNF20 | 1.16 |
| 9289 | 3 | 4 | | | IV-1 | ZBTB40 | 1.39 | 9385 | 3 | 4 | | | IV-1 | ZNF200 | 1.49 |
| 9290 | 3 | 4 | | | IV-1 | ZBTB41 | 1.34 | 9386 | 3 | 4 | | | IV-1 | ZNF202 | 1.36 |
| 9291 | 3 | 4 | | | IV-1 | ZBTB42 | 1.19 | 9387 | 3 | 4 | | | IV-1 | ZNF212 | 1.35 |
| 9292 | 3 | 4 | | | IV-1 | ZBTB43 | 1.47 | 9388 | 3 | 4 | | | IV-1 | ZNF213 | 1.40 |
| 9293 | 3 | 4 | | | IV-1 | ZBTB44 | 1.11 | 9389 | 3 | 4 | | | IV-1 | ZNF217 | 1.22 |
| 9294 | 3 | 4 | | | IV-1 | ZBTB5 | 1.05 | 9390 | 3 | 4 | | | IV-1 | ZNF219 | 1.35 |
| 9295 | 3 | 4 | | | IV-1 | ZBTB6 | 1.13 | 9391 | 3 | 4 | | | IV-1 | ZNF22 | 1.18 |
| 9296 | 3 | 4 | | | IV-1 | ZBTB7B | 1.23 | 9392 | 3 | 4 | | | IV-1 | ZNF222 | 1.34 |
| 9297 | 3 | 4 | | | IV-1 | ZC2HC1A | 1.28 | 9393 | 3 | 4 | | | IV-1 | ZNF224 | 1.00 |
| 9298 | 3 | 4 | | | IV-1 | ZC3H10 | 1.37 | 9394 | 3 | 4 | | | IV-1 | ZNF225 | 1.41 |
| 9299 | 3 | 4 | | | IV-1 | ZC3H11A | 1.06 | 9395 | 3 | 4 | | | IV-1 | ZNF226 | 1.43 |
| 9300 | 3 | 4 | | | IV-1 | ZC3H12D | 1.27 | 9396 | 3 | 4 | | | IV-1 | ZNF227 | 1.32 |
| 9301 | 3 | 4 | | | IV-1 | ZC3H3 | 1.14 | 9397 | 3 | 4 | | | IV-1 | ZNF230 | 1.19 |
| 9302 | 3 | 4 | | | IV-1 | ZC3H4 | 1.36 | 9398 | 3 | 4 | | | IV-1 | ZNF232 | 1.09 |
| 9303 | 3 | 4 | | | IV-1 | ZC3HAV1 | 1.44 | 9399 | 3 | 4 | | | IV-1 | ZNF234 | 1.34 |
| 9304 | 3 | 4 | | | IV-1 | ZC3HC1 | 1.24 | 9400 | 3 | 4 | | | IV-1 | ZNF24 | 1.25 |
| 9305 | 3 | 4 | | | IV-1 | ZCCHC10 | 1.30 | 9401 | 3 | 4 | | | IV-1 | ZNF248 | 1.02 |
| 9306 | 3 | 4 | | | IV-1 | ZCCHC11 | 1.18 | 9402 | 3 | 4 | | | IV-1 | ZNF25 | 1.39 |
| 9307 | 3 | 4 | | | IV-1 | ZCCHC14 | 1.18 | 9403 | 3 | 4 | | | IV-1 | ZNF253 | 1.16 |

Fig. 41 - 50

| | | | | | | | |
|---|---|---|---|---|---|---|---|
| 9404 | 3 | 4 | | | IV-1 | ZNF26 | 1.03 |
| 9405 | 3 | 4 | | | IV-1 | ZNF260 | 1.03 |
| 9406 | 3 | 4 | | | IV-1 | ZNF263 | 1.36 |
| 9407 | 3 | 4 | | | IV-1 | ZNF264 | 1.13 |
| 9408 | 3 | 4 | | | IV-1 | ZNF267 | 1.10 |
| 9409 | 3 | 4 | | | IV-1 | ZNF268 | 1.32 |
| 9410 | 3 | 4 | | | IV-1 | ZNF275 | 1.42 |
| 9411 | 3 | 4 | | | IV-1 | ZNF28 | 1.27 |
| 9412 | 3 | 4 | | | IV-1 | ZNF280C | 1.04 |
| 9413 | 3 | 4 | | | IV-1 | ZNF280D | 1.46 |
| 9414 | 3 | 4 | | | IV-1 | ZNF281 | 1.48 |
| 9415 | 3 | 4 | | | IV-1 | ZNF283 | 1.41 |
| 9416 | 3 | 4 | | | IV-1 | ZNF286A | 1.16 |
| 9417 | 3 | 4 | | | IV-1 | ZNF286B | 1.20 |
| 9418 | 3 | 4 | | | IV-1 | ZNF292 | 1.06 |
| 9419 | 3 | 4 | | | IV-1 | ZNF296 | 1.19 |
| 9420 | 3 | 4 | | | IV-1 | ZNF3 | 1.28 |
| 9421 | 3 | 4 | | | IV-1 | ZNF30 | 1.02 |
| 9422 | 3 | 4 | | | IV-1 | ZNF302 | 1.10 |
| 9423 | 3 | 4 | | | IV-1 | ZNF317 | 1.41 |
| 9424 | 3 | 4 | | | IV-1 | ZNF318 | 1.48 |
| 9425 | 3 | 4 | | | IV-1 | ZNF324 | 1.27 |
| 9426 | 3 | 4 | | | IV-1 | ZNF324B | 1.18 |
| 9427 | 3 | 4 | | | IV-1 | ZNF326 | 1.33 |
| 9428 | 3 | 4 | | | IV-1 | ZNF331 | 1.27 |
| 9429 | 3 | 4 | | | IV-1 | ZNF335 | 1.02 |
| 9430 | 3 | 4 | | | IV-1 | ZNF33B | 1.05 |
| 9431 | 3 | 4 | | | IV-1 | ZNF34 | 1.27 |
| 9432 | 3 | 4 | | | IV-1 | ZNF341 | 1.27 |
| 9433 | 3 | 4 | | | IV-1 | ZNF343 | 1.25 |
| 9434 | 3 | 4 | | | IV-1 | ZNF346 | 1.07 |
| 9435 | 3 | 4 | | | IV-1 | ZNF350 | 1.02 |
| 9436 | 3 | 4 | | | IV-1 | ZNF358 | 1.11 |
| 9437 | 3 | 4 | | | IV-1 | ZNF362 | 1.21 |
| 9438 | 3 | 4 | | | IV-1 | ZNF367 | 1.07 |
| 9439 | 3 | 4 | | | IV-1 | ZNF37A | 1.44 |
| 9440 | 3 | 4 | | | IV-1 | ZNF383 | 1.32 |
| 9441 | 3 | 4 | | | IV-1 | ZNF384 | 1.13 |
| 9442 | 3 | 4 | | | IV-1 | ZNF394 | 1.02 |
| 9443 | 3 | 4 | | | IV-1 | ZNF395 | 1.20 |
| 9444 | 3 | 4 | | | IV-1 | ZNF398 | 1.19 |
| 9445 | 3 | 4 | | | IV-1 | ZNF408 | 1.28 |
| 9446 | 3 | 4 | | | IV-1 | ZNF41 | 1.49 |
| 9447 | 3 | 4 | | | IV-1 | ZNF410 | 1.29 |
| 9448 | 3 | 4 | | | IV-1 | ZNF414 | 1.42 |
| 9449 | 3 | 4 | | | IV-1 | ZNF416 | 1.18 |
| 9450 | 3 | 4 | | | IV-1 | ZNF420 | 1.07 |
| 9451 | 3 | 4 | | | IV-1 | ZNF428 | 1.16 |
| 9452 | 3 | 4 | | | IV-1 | ZNF43 | 1.05 |
| 9453 | 3 | 4 | | | IV-1 | ZNF430 | 1.34 |
| 9454 | 3 | 4 | | | IV-1 | ZNF431 | 1.06 |
| 9455 | 3 | 4 | | | IV-1 | ZNF432 | 1.39 |
| 9456 | 3 | 4 | | | IV-1 | ZNF436 | 1.48 |
| 9457 | 3 | 4 | | | IV-1 | ZNF438 | 1.42 |
| 9458 | 3 | 4 | | | IV-1 | ZNF44 | 1.05 |
| 9459 | 3 | 4 | | | IV-1 | ZNF440 | 1.44 |
| 9460 | 3 | 4 | | | IV-1 | ZNF441 | 1.40 |
| 9461 | 3 | 4 | | | IV-1 | ZNF444 | 1.29 |
| 9462 | 3 | 4 | | | IV-1 | ZNF445 | 1.16 |
| 9463 | 3 | 4 | | | IV-1 | ZNF446 | 1.35 |
| 9464 | 3 | 4 | | | IV-1 | ZNF449 | 1.47 |
| 9465 | 3 | 4 | | | IV-1 | ZNF45 | 1.18 |
| 9466 | 3 | 4 | | | IV-1 | ZNF451 | 1.15 |
| 9467 | 3 | 4 | | | IV-1 | ZNF468 | 1.24 |
| 9468 | 3 | 4 | | | IV-1 | ZNF473 | 1.17 |
| 9469 | 3 | 4 | | | IV-1 | ZNF480 | 1.37 |
| 9470 | 3 | 4 | | | IV-1 | ZNF484 | 1.18 |
| 9471 | 3 | 4 | | | IV-1 | ZNF485 | 1.12 |
| 9472 | 3 | 4 | | | IV-1 | ZNF490 | 1.33 |
| 9473 | 3 | 4 | | | IV-1 | ZNF496 | 1.04 |
| 9474 | 3 | 4 | | | IV-1 | ZNF498 | 1.15 |
| 9475 | 3 | 4 | | | IV-1 | ZNF500 | 1.23 |
| 9476 | 3 | 4 | | | IV-1 | ZNF501 | 1.37 |
| 9477 | 3 | 4 | | | IV-1 | ZNF506 | 1.20 |
| 9478 | 3 | 4 | | | IV-1 | ZNF510 | 1.18 |
| 9479 | 3 | 4 | | | IV-1 | ZNF511 | 1.44 |
| 9480 | 3 | 4 | | | IV-1 | ZNF512 | 1.31 |
| 9481 | 3 | 4 | | | IV-1 | ZNF513 | 1.26 |
| 9482 | 3 | 4 | | | IV-1 | ZNF516 | 1.08 |
| 9483 | 3 | 4 | | | IV-1 | ZNF517 | 1.04 |
| 9484 | 3 | 4 | | | IV-1 | ZNF518A | 1.38 |
| 9485 | 3 | 4 | | | IV-1 | ZNF518B | 1.15 |
| 9486 | 3 | 4 | | | IV-1 | ZNF524 | 1.44 |
| 9487 | 3 | 4 | | | IV-1 | ZNF525 | 1.13 |
| 9488 | 3 | 4 | | | IV-1 | ZNF527 | 1.20 |
| 9489 | 3 | 4 | | | IV-1 | ZNF529 | 1.12 |
| 9490 | 3 | 4 | | | IV-1 | ZNF540 | 1.04 |
| 9491 | 3 | 4 | | | IV-1 | ZNF544 | 1.08 |
| 9492 | 3 | 4 | | | IV-1 | ZNF546 | 1.14 |
| 9493 | 3 | 4 | | | IV-1 | ZNF549 | 1.10 |
| 9494 | 3 | 4 | | | IV-1 | ZNF551 | 1.20 |
| 9495 | 3 | 4 | | | IV-1 | ZNF555 | 1.45 |
| 9496 | 3 | 4 | | | IV-1 | ZNF557 | 1.45 |
| 9497 | 3 | 4 | | | IV-1 | ZNF558 | 1.35 |
| 9498 | 3 | 4 | | | IV-1 | ZNF559 | 1.31 |
| 9499 | 3 | 4 | | | IV-1 | ZNF561 | 1.41 |
| 9500 | 3 | 4 | | | IV-1 | ZNF563 | 1.21 |
| 9501 | 3 | 4 | | | IV-1 | ZNF564 | 1.09 |
| 9502 | 3 | 4 | | | IV-1 | ZNF565 | 1.37 |
| 9503 | 3 | 4 | | | IV-1 | ZNF57 | 1.31 |
| 9504 | 3 | 4 | | | IV-1 | ZNF570 | 1.00 |
| 9505 | 3 | 4 | | | IV-1 | ZNF571 | 1.04 |
| 9506 | 3 | 4 | | | IV-1 | ZNF573 | 1.22 |
| 9507 | 3 | 4 | | | IV-1 | ZNF574 | 1.15 |
| 9508 | 3 | 4 | | | IV-1 | ZNF576 | 1.29 |
| 9509 | 3 | 4 | | | IV-1 | ZNF580 | 1.09 |
| 9510 | 3 | 4 | | | IV-1 | ZNF583 | 1.46 |
| 9511 | 3 | 4 | | | IV-1 | ZNF584 | 1.08 |
| 9512 | 3 | 4 | | | IV-1 | ZNF587B | 1.04 |
| 9513 | 3 | 4 | | | IV-1 | ZNF592 | 1.20 |
| 9514 | 3 | 4 | | | IV-1 | ZNF597 | 1.25 |
| 9515 | 3 | 4 | | | IV-1 | ZNF598 | 1.45 |
| 9516 | 3 | 4 | | | IV-1 | ZNF606 | 1.07 |
| 9517 | 3 | 4 | | | IV-1 | ZNF613 | 1.25 |
| 9518 | 3 | 4 | | | IV-1 | ZNF614 | 1.26 |
| 9519 | 3 | 4 | | | IV-1 | ZNF615 | 1.34 |
| 9520 | 3 | 4 | | | IV-1 | ZNF616 | 1.25 |
| 9521 | 3 | 4 | | | IV-1 | ZNF619 | 1.49 |
| 9522 | 3 | 4 | | | IV-1 | ZNF621 | 1.29 |
| 9523 | 3 | 4 | | | IV-1 | ZNF622 | 1.34 |
| 9524 | 3 | 4 | | | IV-1 | ZNF623 | 1.37 |
| 9525 | 3 | 4 | | | IV-1 | ZNF624 | 1.25 |
| 9526 | 3 | 4 | | | IV-1 | ZNF627 | 1.43 |
| 9527 | 3 | 4 | | | IV-1 | ZNF628 | 1.17 |
| 9528 | 3 | 4 | | | IV-1 | ZNF639 | 1.31 |
| 9529 | 3 | 4 | | | IV-1 | ZNF642 | 1.43 |
| 9530 | 3 | 4 | | | IV-1 | ZNF649 | 1.17 |
| 9531 | 3 | 4 | | | IV-1 | ZNF652 | 1.02 |
| 9532 | 3 | 4 | | | IV-1 | ZNF654 | 1.47 |
| 9533 | 3 | 4 | | | IV-1 | ZNF655 | 1.12 |
| 9534 | 3 | 4 | | | IV-1 | ZNF658 | 1.15 |
| 9535 | 3 | 4 | | | IV-1 | ZNF664 | 1.23 |
| 9536 | 3 | 4 | | | IV-1 | ZNF668 | 1.18 |
| 9537 | 3 | 4 | | | IV-1 | ZNF669 | 1.39 |
| 9538 | 3 | 4 | | | IV-1 | ZNF672 | 1.42 |
| 9539 | 3 | 4 | | | IV-1 | ZNF673 | 1.14 |
| 9540 | 3 | 4 | | | IV-1 | ZNF681 | 1.02 |
| 9541 | 3 | 4 | | | IV-1 | ZNF687 | 1.07 |
| 9542 | 3 | 4 | | | IV-1 | ZNF69 | 1.03 |
| 9543 | 3 | 4 | | | IV-1 | ZNF691 | 1.22 |
| 9544 | 3 | 4 | | | IV-1 | ZNF7 | 1.06 |
| 9545 | 3 | 4 | | | IV-1 | ZNF70 | 1.12 |
| 9546 | 3 | 4 | | | IV-1 | ZNF700 | 1.20 |
| 9547 | 3 | 4 | | | IV-1 | ZNF701 | 1.15 |
| 9548 | 3 | 4 | | | IV-1 | ZNF706 | 1.42 |
| 9549 | 3 | 4 | | | IV-1 | ZNF710 | 1.34 |
| 9550 | 3 | 4 | | | IV-1 | ZNF720 | 1.28 |
| 9551 | 3 | 4 | | | IV-1 | ZNF721 | 1.17 |
| 9552 | 3 | 4 | | | IV-1 | ZNF74 | 1.13 |
| 9553 | 3 | 4 | | | IV-1 | ZNF740 | 1.22 |
| 9554 | 3 | 4 | | | IV-1 | ZNF747 | 1.45 |
| 9555 | 3 | 4 | | | IV-1 | ZNF749 | 1.06 |
| 9556 | 3 | 4 | | | IV-1 | ZNF75A | 1.23 |
| 9557 | 3 | 4 | | | IV-1 | ZNF75D | 1.03 |
| 9558 | 3 | 4 | | | IV-1 | ZNF76 | 1.03 |
| 9559 | 3 | 4 | | | IV-1 | ZNF761 | 1.24 |
| 9560 | 3 | 4 | | | IV-1 | ZNF763 | 1.13 |
| 9561 | 3 | 4 | | | IV-1 | ZNF764 | 1.15 |
| 9562 | 3 | 4 | | | IV-1 | ZNF766 | 1.39 |
| 9563 | 3 | 4 | | | IV-1 | ZNF768 | 1.36 |
| 9564 | 3 | 4 | | | IV-1 | ZNF773 | 1.27 |
| 9565 | 3 | 4 | | | IV-1 | ZNF775 | 1.07 |
| 9566 | 3 | 4 | | | IV-1 | ZNF780B | 1.18 |
| 9567 | 3 | 4 | | | IV-1 | ZNF782 | 1.13 |
| 9568 | 3 | 4 | | | IV-1 | ZNF783 | 1.06 |
| 9569 | 3 | 4 | | | IV-1 | ZNF785 | 1.26 |
| 9570 | 3 | 4 | | | IV-1 | ZNF786 | 1.36 |
| 9571 | 3 | 4 | | | IV-1 | ZNF787 | 1.19 |
| 9572 | 3 | 4 | | | IV-1 | ZNF79 | 1.23 |
| 9573 | 3 | 4 | | | IV-1 | ZNF791 | 1.22 |
| 9574 | 3 | 4 | | | IV-1 | ZNF792 | 1.24 |
| 9575 | 3 | 4 | | | IV-1 | ZNF799 | 1.18 |
| 9576 | 3 | 4 | | | IV-1 | ZNF805 | 1.17 |
| 9577 | 3 | 4 | | | IV-1 | ZNF816 | 1.47 |
| 9578 | 3 | 4 | | | IV-1 | ZNF83 | 1.49 |
| 9579 | 3 | 4 | | | IV-1 | ZNF830 | 1.22 |
| 9580 | 3 | 4 | | | IV-1 | ZNF836 | 1.17 |
| 9581 | 3 | 4 | | | IV-1 | ZNF84 | 1.05 |
| 9582 | 3 | 4 | | | IV-1 | ZNF841 | 1.18 |
| 9583 | 3 | 4 | | | IV-1 | ZNF845 | 1.19 |
| 9584 | 3 | 4 | | | IV-1 | ZNF865 | 1.02 |
| 9585 | 3 | 4 | | | IV-1 | ZNF879 | 1.23 |
| 9586 | 3 | 4 | | | IV-1 | ZNF93 | 1.37 |
| 9587 | 3 | 4 | | | IV-1 | ZNFX1 | 1.30 |
| 9588 | 3 | 4 | | | IV-1 | ZNFX1-AS1 | 1.04 |
| 9589 | 3 | 4 | | | IV-1 | ZNHIT1 | 1.41 |
| 9590 | 3 | 4 | | | IV-1 | ZNHIT2 | 1.46 |
| 9591 | 3 | 4 | | | IV-1 | ZNHIT3 | 1.41 |
| 9592 | 3 | 4 | | | IV-1 | ZNRD1 | 1.42 |
| 9593 | 3 | 4 | | | IV-1 | ZNRF2 | 1.35 |
| 9594 | 3 | 4 | | | IV-1 | ZP3 | 1.26 |
| 9595 | 3 | 4 | | | IV-1 | ZRANB2 | 1.24 |

Fig. 41 - 51

| | | | | | | | | | | | | | | | |
|---|---|---|---|---|---|---|---|---|---|---|---|---|---|---|---|
| 9596 | 3 | 4 | | | IV-1 | ZSCAN16 | 1.03 | 9692 | 3 | | | | | ACSM4 | 1.00 |
| 9597 | 3 | 4 | | | IV-1 | ZSCAN2 | 1.25 | 9693 | 3 | | | | | ACSM5 | 1.00 |
| 9598 | 3 | 4 | | | IV-1 | ZSCAN21 | 1.23 | 9694 | 3 | | | | | ACSS3 | 1.00 |
| 9599 | 3 | 4 | | | IV-1 | ZSCAN22 | 1.41 | 9695 | 3 | | | | | ACTA1 | 1.00 |
| 9600 | 3 | 4 | | | IV-1 | ZSCAN29 | 1.26 | 9696 | 3 | | | | | ACTBL2 | 1.00 |
| 9601 | 3 | 4 | | | IV-1 | ZSCAN5A | 1.43 | 9697 | 3 | | | | | ACTC1 | 1.00 |
| 9602 | 3 | 4 | | | IV-1 | ZSWIM1 | 1.28 | 9698 | 3 | | | | | ACTG2 | 1.00 |
| 9603 | 3 | 4 | | | IV-1 | ZSWIM3 | 1.35 | 9699 | 3 | | | | | ACTL6B | 1.00 |
| 9604 | 3 | 4 | | | IV-1 | ZSWIM4 | 1.27 | 9700 | 3 | | | | | ACTL7A | 1.00 |
| 9605 | 3 | 4 | | | IV-1 | ZSWIM7 | 1.26 | 9701 | 3 | | | | | ACTL7B | 1.00 |
| 9606 | 3 | 4 | | | IV-1 | ZUFSP | 1.26 | 9702 | 3 | | | | | ACTL8 | 1.00 |
| 9607 | 3 | 4 | | | IV-1 | ZXDC | 1.11 | 9703 | 3 | | | | | ACTL9 | 1.00 |
| 9608 | 3 | 4 | | | IV-1 | ZZEF1 | 1.30 | 9704 | 3 | | | | | ACTN2 | 1.00 |
| 9609 | 3 | 4 | | | IV-1 | ZZZ3 | 1.37 | 9705 | 3 | | | | | ACTN3 | 1.00 |
| 9610 | 3 | | | | | 1/2-SBSRNA4 | 1.00 | 9706 | 3 | | | | | ACTR3BP2 | 1.00 |
| 9611 | 3 | | | | | A1CF | 1.00 | 9707 | 3 | | | | | ACTR3BP5 | 1.00 |
| 9612 | 3 | | | | | A2M | 1.00 | 9708 | 3 | | | | | ACTR3C | 1.00 |
| 9613 | 3 | | | | | A2ML1 | 1.00 | 9709 | 3 | | | | | ACTRT1 | 1.00 |
| 9614 | 3 | | | | | A2MP1 | 1.00 | 9710 | 3 | | | | | ACTRT2 | 1.00 |
| 9615 | 3 | | | | | A4GALT | 1.00 | 9711 | 3 | | | | | ACVR1C | 1.00 |
| 9616 | 3 | | | | | A4GNT | 1.00 | 9712 | 3 | | | | | ACY3 | 1.00 |
| 9617 | 3 | | | | | AA06 | 1.00 | 9713 | 3 | | | | | ADAD1 | 1.00 |
| 9618 | 3 | | | | | AAA1 | 1.00 | 9714 | 3 | | | | | ADAD2 | 1.00 |
| 9619 | 3 | | | | | AACSP1 | 1.00 | 9715 | 3 | | | | | ADAM11 | 1.00 |
| 9620 | 3 | | | | | AADAC | 1.00 | 9716 | 3 | | | | | ADAM12 | 1.00 |
| 9621 | 3 | | | | | AADACL2 | 1.00 | 9717 | 3 | | | | | ADAM18 | 1.00 |
| 9622 | 3 | | | | | AADACL3 | 1.00 | 9718 | 3 | | | | | ADAM2 | 1.00 |
| 9623 | 3 | | | | | AADACL4 | 1.00 | 9719 | 3 | | | | | ADAM20 | 1.00 |
| 9624 | 3 | | | | | AADAT | 1.00 | 9720 | 3 | | | | | ADAM21 | 1.00 |
| 9625 | 3 | | | | | AANAT | 1.00 | 9721 | 3 | | | | | ADAM21P1 | 1.00 |
| 9626 | 3 | | | | | AARS2 | 1.44 | 9722 | 3 | | | | | ADAM22 | 1.00 |
| 9627 | 3 | | | | | AARSD1 | 1.02 | 9723 | 3 | | | | | ADAM23 | 1.00 |
| 9628 | 3 | | | | | AASS | 1.00 | 9724 | 3 | | | | | ADAM29 | 1.00 |
| 9629 | 3 | | | | | AATK-AS1 | 1.00 | 9725 | 3 | | | | | ADAM30 | 1.00 |
| 9630 | 3 | | | | | ABCA10 | 1.00 | 9726 | 3 | | | | | ADAM32 | 1.00 |
| 9631 | 3 | | | | | ABCA12 | 1.00 | 9727 | 3 | | | | | ADAM33 | 1.00 |
| 9632 | 3 | | | | | ABCA13 | 1.00 | 9728 | 3 | | | | | ADAM3A | 1.00 |
| 9633 | 3 | | | | | ABCA17P | 1.00 | 9729 | 3 | | | | | ADAM5P | 1.00 |
| 9634 | 3 | | | | | ABCA3 | 1.00 | 9730 | 3 | | | | | ADAM6 | 1.00 |
| 9635 | 3 | | | | | ABCA4 | 1.00 | 9731 | 3 | | | | | ADAM7 | 1.00 |
| 9636 | 3 | | | | | ABCA5 | 1.00 | 9732 | 3 | | | | | ADAMDEC1 | 1.00 |
| 9637 | 3 | | | | | ABCA6 | 1.00 | 9733 | 3 | | | | | ADAMTS12 | 1.00 |
| 9638 | 3 | | | | | ABCA8 | 1.00 | 9734 | 3 | | | | | ADAMTS13 | 1.00 |
| 9639 | 3 | | | | | ABCA9 | 1.00 | 9735 | 3 | | | | | ADAMTS14 | 1.00 |
| 9640 | 3 | | | | | ABCB11 | 1.00 | 9736 | 3 | | | | | ADAMTS15 | 1.00 |
| 9641 | 3 | | | | | ABCB4 | 1.00 | 9737 | 3 | | | | | ADAMTS16 | 1.00 |
| 9642 | 3 | | | | | ABCB5 | 1.00 | 9738 | 3 | | | | | ADAMTS17 | 1.00 |
| 9643 | 3 | | | | | ABCB6 | 1.00 | 9739 | 3 | | | | | ADAMTS18 | 1.00 |
| 9644 | 3 | | | | | ABCB9 | 1.00 | 9740 | 3 | | | | | ADAMTS19 | 1.00 |
| 9645 | 3 | | | | | ABCC11 | 1.00 | 9741 | 3 | | | | | ADAMTS2 | 1.00 |
| 9646 | 3 | | | | | ABCC12 | 1.00 | 9742 | 3 | | | | | ADAMTS20 | 1.00 |
| 9647 | 3 | | | | | ABCC2 | 1.00 | 9743 | 3 | | | | | ADAMTS3 | 1.00 |
| 9648 | 3 | | | | | ABCC6P1 | 1.00 | 9744 | 3 | | | | | ADAMTS4 | 1.00 |
| 9649 | 3 | | | | | ABCC8 | 1.00 | 9745 | 3 | | | | | ADAMTS5 | 1.00 |
| 9650 | 3 | | | | | ABCC9 | 1.00 | 9746 | 3 | | | | | ADAMTS6 | 1.00 |
| 9651 | 3 | | | | | ABCG2 | 1.00 | 9747 | 3 | | | | | ADAMTS7 | 1.00 |
| 9652 | 3 | | | | | ABCG4 | 1.00 | 9748 | 3 | | | | | ADAMTS8 | 1.00 |
| 9653 | 3 | | | | | ABCG5 | 1.00 | 9749 | 3 | | | | | ADAMTS9 | 1.00 |
| 9654 | 3 | | | | | ABCG8 | 1.00 | 9750 | 3 | | | | | ADAMTS9-AS2 | 1.00 |
| 9655 | 3 | | | | | ABHD1 | 1.00 | 9751 | 3 | | | | | ADAMTSL1 | 1.00 |
| 9656 | 3 | | | | | ABHD11-AS1 | 1.00 | 9752 | 3 | | | | | ADAMTSL2 | 1.00 |
| 9657 | 3 | | | | | ABHD12B | 1.00 | 9753 | 3 | | | | | ADAMTSL3 | 1.00 |
| 9658 | 3 | | | | | ABHD14A-ACY1 | 1.00 | 9754 | 3 | | | | | ADAMTSL5 | 1.00 |
| 9659 | 3 | | | | | ABI3BP | 1.00 | 9755 | 3 | | | | | ADARB2-AS1 | 1.00 |
| 9660 | 3 | | | | | ABLIM2 | 1.00 | 9756 | 3 | | | | | ADAT2 | 1.00 |
| 9661 | 3 | | | | | ABRA | 1.00 | 9757 | 3 | | | | | ADC | 1.00 |
| 9662 | 3 | | | | | ACAD11 | 1.00 | 9758 | 3 | | | | | ADCK5 | 1.00 |
| 9663 | 3 | | | | | ACADL | 1.00 | 9759 | 3 | | | | | ADCY1 | 1.00 |
| 9664 | 3 | | | | | ACAN | 1.00 | 9760 | 3 | | | | | ADCY10 | 1.00 |
| 9665 | 3 | | | | | ACBD7 | 1.00 | 9761 | 3 | | | | | ADCY2 | 1.00 |
| 9666 | 3 | | | | | ACCN1 | 1.00 | 9762 | 3 | | | | | ADCY4 | 1.00 |
| 9667 | 3 | | | | | ACCN2 | 1.00 | 9763 | 3 | | | | | ADCY5 | 1.00 |
| 9668 | 3 | | | | | ACCN3 | 1.00 | 9764 | 3 | | | | | ADCY6 | 1.00 |
| 9669 | 3 | | | | | ACCN4 | 1.00 | 9765 | 3 | | | | | ADCY8 | 1.00 |
| 9670 | 3 | | | | | ACCN5 | 1.00 | 9766 | 3 | | | | | ADCYAP1 | 1.00 |
| 9671 | 3 | | | | | ACCSL | 1.00 | 9767 | 3 | | | | | ADCYAP1R1 | 1.00 |
| 9672 | 3 | | | | | ACE | 1.00 | 9768 | 3 | | | | | ADGB | 1.00 |
| 9673 | 3 | | | | | ACE2 | 1.00 | 9769 | 3 | | | | | ADH1A | 1.00 |
| 9674 | 3 | | | | | ACER1 | 1.00 | 9770 | 3 | | | | | ADH1B | 1.00 |
| 9675 | 3 | | | | | ACHE | 1.00 | 9771 | 3 | | | | | ADH1C | 1.00 |
| 9676 | 3 | | | | | ACMSD | 1.00 | 9772 | 3 | | | | | ADH4 | 1.00 |
| 9677 | 3 | | | | | ACOT11 | 1.00 | 9773 | 3 | | | | | ADH6 | 1.00 |
| 9678 | 3 | | | | | ACOT12 | 1.00 | 9774 | 3 | | | | | ADH7 | 1.00 |
| 9679 | 3 | | | | | ACOT6 | 1.00 | 9775 | 3 | | | | | ADIG | 1.00 |
| 9680 | 3 | | | | | ACOX2 | 1.00 | 9776 | 3 | | | | | ADIPOQ | 1.00 |
| 9681 | 3 | | | | | ACOXL | 1.00 | 9777 | 3 | | | | | ADORA1 | 1.00 |
| 9682 | 3 | | | | | ACPT | 1.00 | 9778 | 3 | | | | | ADPRHL1 | 1.00 |
| 9683 | 3 | | | | | ACR | 1.00 | 9779 | 3 | | | | | ADRA1A | 1.00 |
| 9684 | 3 | | | | | ACRC | 1.00 | 9780 | 3 | | | | | ADRA1B | 1.00 |
| 9685 | 3 | | | | | ACRV1 | 1.00 | 9781 | 3 | | | | | ADRA1D | 1.00 |
| 9686 | 3 | | | | | ACSBG1 | 1.00 | 9782 | 3 | | | | | ADRA2A | 1.00 |
| 9687 | 3 | | | | | ACSBG2 | 1.00 | 9783 | 3 | | | | | ADRA2B | 1.00 |
| 9688 | 3 | | | | | ACSM1 | 1.00 | 9784 | 3 | | | | | ADRA2C | 1.00 |
| 9689 | 3 | | | | | ACSM2A | 1.00 | 9785 | 3 | | | | | ADRB1 | 1.00 |
| 9690 | 3 | | | | | ACSM2B | 1.00 | 9786 | 3 | | | | | ADRB3 | 1.00 |
| 9691 | 3 | | | | | ACSM3 | 1.00 | 9787 | 3 | | | | | ADSSL1 | 1.00 |

Fig. 41 - 52

| | | | | | | | |
|---|---|---|---|---|---|---|---|
| 9788 | 3 | AFAP1-AS1 | 1.00 | 9884 | 3 | AMOTL1 | 1.00 |
| 9789 | 3 | AFAP1L1 | 1.00 | 9885 | 3 | AMOTL2 | 1.00 |
| 9790 | 3 | AFAP1L2 | 1.00 | 9886 | 3 | AMPD1 | 1.00 |
| 9791 | 3 | AFF2 | 1.00 | 9887 | 3 | AMPH | 1.00 |
| 9792 | 3 | AFM | 1.00 | 9888 | 3 | AMTN | 1.00 |
| 9793 | 3 | AFP | 1.00 | 9889 | 3 | AMY1A | 1.00 |
| 9794 | 3 | AGAP1 | 1.00 | 9890 | 3 | AMY1B | 1.00 |
| 9795 | 3 | AGAP11 | 1.00 | 9891 | 3 | AMY1C | 1.00 |
| 9796 | 3 | AGBL1 | 1.00 | 9892 | 3 | AMY2A | 1.00 |
| 9797 | 3 | AGBL2 | 1.00 | 9893 | 3 | AMY2B | 1.00 |
| 9798 | 3 | AGBL3 | 1.00 | 9894 | 3 | AMZ1 | 1.00 |
| 9799 | 3 | AGBL4 | 1.00 | 9895 | 3 | ANGPT2 | 1.00 |
| 9800 | 3 | AGMO | 1.00 | 9896 | 3 | ANGPT4 | 1.00 |
| 9801 | 3 | AGPAT4-IT1 | 1.00 | 9897 | 3 | ANGPTL1 | 1.00 |
| 9802 | 3 | AGPHD1 | 1.00 | 9898 | 3 | ANGPTL2 | 1.00 |
| 9803 | 3 | AGR2 | 1.00 | 9899 | 3 | ANGPTL3 | 1.00 |
| 9804 | 3 | AGR3 | 1.00 | 9900 | 3 | ANGPTL4 | 1.00 |
| 9805 | 3 | AGRN | 1.00 | 9901 | 3 | ANGPTL5 | 1.00 |
| 9806 | 3 | AGRP | 1.00 | 9902 | 3 | ANGPTL6 | 1.00 |
| 9807 | 3 | AGSK1 | 1.00 | 9903 | 3 | ANGPTL7 | 1.00 |
| 9808 | 3 | AGT | 1.00 | 9904 | 3 | ANK2 | 1.00 |
| 9809 | 3 | AGTR1 | 1.00 | 9905 | 3 | ANKAR | 1.00 |
| 9810 | 3 | AGTR2 | 1.00 | 9906 | 3 | ANKFN1 | 1.00 |
| 9811 | 3 | AGXT | 1.00 | 9907 | 3 | ANKK1 | 1.00 |
| 9812 | 3 | AGXT2 | 1.00 | 9908 | 3 | ANKLE1 | 1.00 |
| 9813 | 3 | AGXT2L1 | 1.00 | 9909 | 3 | ANKRD1 | 1.00 |
| 9814 | 3 | AHI1 | 1.00 | 9910 | 3 | ANKRD13B | 1.00 |
| 9815 | 3 | AHNAK2 | 1.00 | 9911 | 3 | ANKRD18A | 1.00 |
| 9816 | 3 | AHRR | 1.00 | 9912 | 3 | ANKRD18B | 1.00 |
| 9817 | 3 | AHSG | 1.00 | 9913 | 3 | ANKRD18DP | 1.00 |
| 9818 | 3 | AICDA | 1.00 | 9914 | 3 | ANKRD2 | 1.00 |
| 9819 | 3 | AIF1L | 1.00 | 9915 | 3 | ANKRD20A1 | 1.00 |
| 9820 | 3 | AIFM3 | 1.00 | 9916 | 3 | ANKRD20A11P | 1.00 |
| 9821 | 3 | AIM1L | 1.00 | 9917 | 3 | ANKRD20A2 | 1.00 |
| 9822 | 3 | AIPL1 | 1.00 | 9918 | 3 | ANKRD20A3 | 1.00 |
| 9823 | 3 | AIRE | 1.00 | 9919 | 3 | ANKRD20A4 | 1.00 |
| 9824 | 3 | AJAP1 | 1.00 | 9920 | 3 | ANKRD20A5P | 1.00 |
| 9825 | 3 | AJUBA | 1.00 | 9921 | 3 | ANKRD20A8P | 1.00 |
| 9826 | 3 | AK4 | 1.00 | 9922 | 3 | ANKRD20A9P | 1.00 |
| 9827 | 3 | AK7 | 1.00 | 9923 | 3 | ANKRD23 | 1.00 |
| 9828 | 3 | AK8 | 1.00 | 9924 | 3 | ANKRD24 | 1.00 |
| 9829 | 3 | AKAP14 | 1.00 | 9925 | 3 | ANKRD26P1 | 1.00 |
| 9830 | 3 | AKAP3 | 1.00 | 9926 | 3 | ANKRD26P3 | 1.00 |
| 9831 | 3 | AKAP4 | 1.00 | 9927 | 3 | ANKRD29 | 1.00 |
| 9832 | 3 | AKAP6 | 1.00 | 9928 | 3 | ANKRD30A | 1.00 |
| 9833 | 3 | AKD1 | 1.00 | 9929 | 3 | ANKRD30B | 1.00 |
| 9834 | 3 | AKNAD1 | 1.00 | 9930 | 3 | ANKRD30BL | 1.00 |
| 9835 | 3 | AKR1B10 | 1.00 | 9931 | 3 | ANKRD30BP2 | 1.00 |
| 9836 | 3 | AKR1B15 | 1.00 | 9932 | 3 | ANKRD31 | 1.00 |
| 9837 | 3 | AKR1C1 | 1.00 | 9933 | 3 | ANKRD33 | 1.00 |
| 9838 | 3 | AKR1C2 | 1.00 | 9934 | 3 | ANKRD34A | 1.00 |
| 9839 | 3 | AKR1C4 | 1.00 | 9935 | 3 | ANKRD34C | 1.00 |
| 9840 | 3 | AKR1CL1 | 1.00 | 9936 | 3 | ANKRD35 | 1.00 |
| 9841 | 3 | AKR1D1 | 1.00 | 9937 | 3 | ANKRD36 | 1.00 |
| 9842 | 3 | AKR1E2 | 1.00 | 9938 | 3 | ANKRD36B | 1.00 |
| 9843 | 3 | AKR7A3 | 1.00 | 9939 | 3 | ANKRD36BP2 | 1.00 |
| 9844 | 3 | AKR7L | 1.00 | 9940 | 3 | ANKRD37 | 1.00 |
| 9845 | 3 | ALB | 1.00 | 9941 | 3 | ANKRD42 | 1.00 |
| 9846 | 3 | ALDH1A2 | 1.00 | 9942 | 3 | ANKRD45 | 1.00 |
| 9847 | 3 | ALDH1A3 | 1.00 | 9943 | 3 | ANKRD53 | 1.00 |
| 9848 | 3 | ALDH1L1 | 1.00 | 9944 | 3 | ANKRD62P1-PARP4P3 | 1.00 |
| 9849 | 3 | ALDH1L2 | 1.00 | 9945 | 3 | ANKRD63 | 1.00 |
| 9850 | 3 | ALDH3A1 | 1.00 | 9946 | 3 | ANKRD65 | 1.00 |
| 9851 | 3 | ALDH3B2 | 1.00 | 9947 | 3 | ANKRD7 | 1.00 |
| 9852 | 3 | ALDH7A1 | 1.00 | 9948 | 3 | ANKS1B | 1.00 |
| 9853 | 3 | ALDH8A1 | 1.00 | 9949 | 3 | ANKS4B | 1.00 |
| 9854 | 3 | ALDOB | 1.00 | 9950 | 3 | ANKS6 | 1.00 |
| 9855 | 3 | ALG10B | 1.00 | 9951 | 3 | ANKUB1 | 1.00 |
| 9856 | 3 | ALG1L | 1.00 | 9952 | 3 | ANLN | 1.00 |
| 9857 | 3 | ALG1L2 | 1.00 | 9953 | 3 | ANO1 | 1.00 |
| 9858 | 3 | ALK | 1.00 | 9954 | 3 | ANO2 | 1.00 |
| 9859 | 3 | ALLC | 1.00 | 9955 | 3 | ANO3 | 1.00 |
| 9860 | 3 | ALMS1P | 1.00 | 9956 | 3 | ANO4 | 1.00 |
| 9861 | 3 | ALOX12B | 1.00 | 9957 | 3 | ANO5 | 1.00 |
| 9862 | 3 | ALOX12P2 | 1.00 | 9958 | 3 | ANO7 | 1.00 |
| 9863 | 3 | ALOXE3 | 1.00 | 9959 | 3 | ANP32A-IT1 | 1.00 |
| 9864 | 3 | ALPI | 1.00 | 9960 | 3 | ANTXR1 | 1.00 |
| 9865 | 3 | ALPK2 | 1.00 | 9961 | 3 | ANTXRL | 1.00 |
| 9866 | 3 | ALPK3 | 1.00 | 9962 | 3 | ANXA10 | 1.00 |
| 9867 | 3 | ALPP | 1.00 | 9963 | 3 | ANXA13 | 1.00 |
| 9868 | 3 | ALPPL2 | 1.00 | 9964 | 3 | ANXA8 | 1.00 |
| 9869 | 3 | ALS2CR11 | 1.00 | 9965 | 3 | ANXA8L1 | 1.00 |
| 9870 | 3 | ALS2CR12 | 1.00 | 9966 | 3 | ANXA8L2 | 1.00 |
| 9871 | 3 | ALS2CR8 | 1.00 | 9967 | 3 | AOC4 | 1.00 |
| 9872 | 3 | ALX1 | 1.00 | 9968 | 3 | AOX1 | 1.00 |
| 9873 | 3 | ALX3 | 1.00 | 9969 | 3 | AOX2P | 1.00 |
| 9874 | 3 | ALX4 | 1.00 | 9970 | 3 | AP1B1P1 | 1.00 |
| 9875 | 3 | AMBN | 1.00 | 9971 | 3 | AP3B2 | 1.00 |
| 9876 | 3 | AMBP | 1.00 | 9972 | 3 | APBA1 | 1.00 |
| 9877 | 3 | AMDHD1 | 1.00 | 9973 | 3 | APBB2 | 1.00 |
| 9878 | 3 | AMELX | 1.00 | 9974 | 3 | APC2 | 1.00 |
| 9879 | 3 | AMELY | 1.00 | 9975 | 3 | APCDD1L | 1.00 |
| 9880 | 3 | AMH | 1.00 | 9976 | 3 | APCS | 1.00 |
| 9881 | 3 | AMHR2 | 1.00 | 9977 | 3 | APLF | 1.00 |
| 9882 | 3 | AMN | 1.00 | 9978 | 3 | APLN | 1.00 |
| 9883 | 3 | AMOT | 1.00 | | | | |

Fig. 41 - 53

| | | | | | | | | | | | | | | |
|---|---|---|---|---|---|---|---|---|---|---|---|---|---|---|
| 9979 | 3 | | | | | APLNR | 1.00 | 10075 | 3 | | | | ARX | 1.00 |
| 9980 | 3 | | | | | APLP1 | 1.00 | 10076 | 3 | | | | AS3MT | 1.00 |
| 9981 | 3 | | | | | APOA1 | 1.00 | 10077 | 3 | | | | ASAH2 | 1.00 |
| 9982 | 3 | | | | | APOA2 | 1.00 | 10078 | 3 | | | | ASAH2B | 1.00 |
| 9983 | 3 | | | | | APOA4 | 1.00 | 10079 | 3 | | | | ASAP1-IT1 | 1.00 |
| 9984 | 3 | | | | | APOA5 | 1.00 | 10080 | 3 | | | | ASAP3 | 1.00 |
| 9985 | 3 | | | | | APOB | 1.00 | 10081 | 3 | | | | ASB10 | 1.00 |
| 9986 | 3 | | | | | APOBEC1 | 1.00 | 10082 | 3 | | | | ASB11 | 1.00 |
| 9987 | 3 | | | | | APOBEC2 | 1.00 | 10083 | 3 | | | | ASB12 | 1.00 |
| 9988 | 3 | | | | | APOBEC4 | 1.00 | 10084 | 3 | | | | ASB14 | 1.00 |
| 9989 | 3 | | | | | APOC1 | 1.00 | 10085 | 3 | | | | ASB15 | 1.00 |
| 9990 | 3 | | | | | APOC1P1 | 1.00 | 10086 | 3 | | | | ASB16 | 1.00 |
| 9991 | 3 | | | | | APOC2 | 1.00 | 10087 | 3 | | | | ASB17 | 1.00 |
| 9992 | 3 | | | | | APOC3 | 1.00 | 10088 | 3 | | | | ASB18 | 1.00 |
| 9993 | 3 | | | | | APOC4 | 1.00 | 10089 | 3 | | | | ASB4 | 1.00 |
| 9994 | 3 | | | | | APOC4-APOC2 | 1.00 | 10090 | 3 | | | | ASB5 | 1.00 |
| 9995 | 3 | | | | | APOD | 1.00 | 10091 | 3 | | | | ASB9 | 1.00 |
| 9996 | 3 | | | | | APOE | 1.00 | 10092 | 3 | | | | ASB9P1 | 1.00 |
| 9997 | 3 | | | | | APOF | 1.00 | 10093 | 3 | | | | ASCL1 | 1.00 |
| 9998 | 3 | | | | | APOH | 1.00 | 10094 | 3 | | | | ASCL3 | 1.00 |
| 9999 | 3 | | | | | APOL4 | 1.00 | 10095 | 3 | | | | ASCL4 | 1.00 |
| 10000 | 3 | | | | | APOL5 | 1.00 | 10096 | 3 | | | | ASIP | 1.00 |
| 10001 | 3 | | | | | APOLD1 | 1.00 | 10097 | 3 | | | | ASMT | 1.00 |
| 10002 | 3 | | | | | APOM | 1.00 | 10098 | 3 | | | | ASPA | 1.00 |
| 10003 | 3 | | | | | AQP11 | 1.00 | 10099 | 3 | | | | ASPDH | 1.00 |
| 10004 | 3 | | | | | AQP12A | 1.00 | 10100 | 3 | | | | ASPG | 1.00 |
| 10005 | 3 | | | | | AQP12B | 1.00 | 10101 | 3 | | | | ASPHD1 | 1.00 |
| 10006 | 3 | | | | | AQP2 | 1.00 | 10102 | 3 | | | | ASPM | 1.00 |
| 10007 | 3 | | | | | AQP4 | 1.00 | 10103 | 3 | | | | ASPN | 1.00 |
| 10008 | 3 | | | | | AQP5 | 1.00 | 10104 | 3 | | | | ASS1 | 1.00 |
| 10009 | 3 | | | | | AQP6 | 1.00 | 10105 | 3 | | | | ASTL | 1.00 |
| 10010 | 3 | | | | | AQP7 | 1.00 | 10106 | 3 | | | | ASTN1 | 1.00 |
| 10011 | 3 | | | | | AQP7P1 | 1.00 | 10107 | 3 | | | | ASTN2 | 1.00 |
| 10012 | 3 | | | | | AQP7P3 | 1.00 | 10108 | 3 | | | | ASXL3 | 1.00 |
| 10013 | 3 | | | | | AQP8 | 1.00 | 10109 | 3 | | | | ASZ1 | 1.00 |
| 10014 | 3 | | | | | AQPEP | 1.00 | 10110 | 3 | | | | ATAD3C | 1.00 |
| 10015 | 3 | | | | | AR | 1.00 | 10111 | 3 | | | | ATAD5 | 1.00 |
| 10016 | 3 | | | | | ARC | 1.00 | 10112 | 3 | | | | ATAT1 | 1.00 |
| 10017 | 3 | | | | | ARGFX | 1.00 | 10113 | 3 | | | | ATCAY | 1.00 |
| 10018 | 3 | | | | | ARGFXP2 | 1.00 | 10114 | 3 | | | | ATL1 | 1.00 |
| 10019 | 3 | | | | | ARHGAP11B | 1.00 | 10115 | 3 | | | | ATOH1 | 1.00 |
| 10020 | 3 | | | | | ARHGAP19-SLIT1 | 1.00 | 10116 | 3 | | | | ATOH7 | 1.00 |
| 10021 | 3 | | | | | ARHGAP20 | 1.00 | 10117 | 3 | | | | ATOH8 | 1.00 |
| 10022 | 3 | | | | | ARHGAP23 | 1.00 | 10118 | 3 | | | | ATP10B | 1.00 |
| 10023 | 3 | | | | | ARHGAP28 | 1.00 | 10119 | 3 | | | | ATP12A | 1.00 |
| 10024 | 3 | | | | | ARHGAP29 | 1.00 | 10120 | 3 | | | | ATP13A4 | 1.00 |
| 10025 | 3 | | | | | ARHGAP33 | 1.00 | 10121 | 3 | | | | ATP13A5 | 1.00 |
| 10026 | 3 | | | | | ARHGAP36 | 1.00 | 10122 | 3 | | | | ATP1A2 | 1.00 |
| 10027 | 3 | | | | | ARHGAP39 | 1.00 | 10123 | 3 | | | | ATP1A4 | 1.00 |
| 10028 | 3 | | | | | ARHGAP40 | 1.00 | 10124 | 3 | | | | ATP1B2 | 1.00 |
| 10029 | 3 | | | | | ARHGAP42 | 1.00 | 10125 | 3 | | | | ATP1B4 | 1.00 |
| 10030 | 3 | | | | | ARHGAP44 | 1.00 | 10126 | 3 | | | | ATP2A1 | 1.00 |
| 10031 | 3 | | | | | ARHGAP5-AS1 | 1.00 | 10127 | 3 | | | | ATP2B2 | 1.00 |
| 10032 | 3 | | | | | ARHGAP8 | 1.00 | 10128 | 3 | | | | ATP2B3 | 1.00 |
| 10033 | 3 | | | | | ARHGDIG | 1.00 | 10129 | 3 | | | | ATP2C2 | 1.00 |
| 10034 | 3 | | | | | ARHGEF15 | 1.00 | 10130 | 3 | | | | ATP4A | 1.00 |
| 10035 | 3 | | | | | ARHGEF16 | 1.00 | 10131 | 3 | | | | ATP4B | 1.00 |
| 10036 | 3 | | | | | ARHGEF17 | 1.00 | 10132 | 3 | | | | ATP6V0A4 | 1.00 |
| 10037 | 3 | | | | | ARHGEF25 | 1.00 | 10133 | 3 | | | | ATP6V0CP3 | 1.00 |
| 10038 | 3 | | | | | ARHGEF26 | 1.00 | 10134 | 3 | | | | ATP6V0D2 | 1.00 |
| 10039 | 3 | | | | | ARHGEF26-AS1 | 1.00 | 10135 | 3 | | | | ATP6V1B1 | 1.00 |
| 10040 | 3 | | | | | ARHGEF33 | 1.00 | 10136 | 3 | | | | ATP6V1G2 | 1.00 |
| 10041 | 3 | | | | | ARHGEF37 | 1.00 | 10137 | 3 | | | | ATP6V1G3 | 1.00 |
| 10042 | 3 | | | | | ARHGEF38 | 1.00 | 10138 | 3 | | | | ATP7B | 1.00 |
| 10043 | 3 | | | | | ARHGEF4 | 1.00 | 10139 | 3 | | | | ATP8A2 | 1.00 |
| 10044 | 3 | | | | | ARID3C | 1.00 | 10140 | 3 | | | | ATP8B1 | 1.00 |
| 10045 | 3 | | | | | ARL13A | 1.00 | 10141 | 3 | | | | ATP8B3 | 1.00 |
| 10046 | 3 | | | | | ARL14 | 1.00 | 10142 | 3 | | | | ATPAF1-AS1 | 1.00 |
| 10047 | 3 | | | | | ARL2-SNX15 | 1.00 | 10143 | 3 | | | | ATRNL1 | 1.00 |
| 10048 | 3 | | | | | ARL5C | 1.00 | 10144 | 3 | | | | ATXN3L | 1.00 |
| 10049 | 3 | | | | | ARL6 | 1.00 | 10145 | 3 | | | | ATXN8OS | 1.00 |
| 10050 | 3 | | | | | ARL9 | 1.00 | 10146 | 3 | | | | AURKB | 1.00 |
| 10051 | 3 | | | | | ARMC12 | 1.00 | 10147 | 3 | | | | AURKC | 1.00 |
| 10052 | 3 | | | | | ARMC2 | 1.00 | 10148 | 3 | | | | AVP | 1.00 |
| 10053 | 3 | | | | | ARMC3 | 1.00 | 10149 | 3 | | | | AVPR1A | 1.00 |
| 10054 | 3 | | | | | ARMC4 | 1.00 | 10150 | 3 | | | | AVPR1B | 1.00 |
| 10055 | 3 | | | | | ARMC9 | 1.00 | 10151 | 3 | | | | AVPR2 | 1.00 |
| 10056 | 3 | | | | | ARMCX4 | 1.00 | 10152 | 3 | | | | AWAT1 | 1.00 |
| 10057 | 3 | | | | | ARMCX5-GPRASP2 | 1.00 | 10153 | 3 | | | | AWAT2 | 1.00 |
| 10058 | 3 | | | | | ARMS2 | 1.00 | 10154 | 3 | | | | AXDND1 | 1.00 |
| 10059 | 3 | | | | | ARNT2 | 1.00 | 10155 | 3 | | | | AXL | 1.00 |
| 10060 | 3 | | | | | ARNTL2 | 1.00 | 10156 | 3 | | | | AZGP1 | 1.00 |
| 10061 | 3 | | | | | ARPM1 | 1.00 | 10157 | 3 | | | | AZGP1P1 | 1.00 |
| 10062 | 3 | | | | | ARPP21 | 1.00 | 10158 | 3 | | | | B3GALNT1 | 1.00 |
| 10063 | 3 | | | | | ARR3 | 1.00 | 10159 | 3 | | | | B3GALT1 | 1.00 |
| 10064 | 3 | | | | | ARSE | 1.00 | 10160 | 3 | | | | B3GALT5 | 1.00 |
| 10065 | 3 | | | | | ARSF | 1.00 | 10161 | 3 | | | | B3GAT2 | 1.00 |
| 10066 | 3 | | | | | ARSH | 1.00 | 10162 | 3 | | | | B3GNT3 | 1.00 |
| 10067 | 3 | | | | | ARSI | 1.00 | 10163 | 3 | | | | B3GNT4 | 1.00 |
| 10068 | 3 | | | | | ARSJ | 1.00 | 10164 | 3 | | | | B3GNT6 | 1.00 |
| 10069 | 3 | | | | | ART1 | 1.00 | 10165 | 3 | | | | B4GALNT1 | 1.00 |
| 10070 | 3 | | | | | ART3 | 1.00 | 10166 | 3 | | | | B4GALNT2 | 1.00 |
| 10071 | 3 | | | | | ART4 | 1.00 | 10167 | 3 | | | | B4GALNT4 | 1.00 |
| 10072 | 3 | | | | | ART5 | 1.00 | 10168 | 3 | | | | B7H6 | 1.00 |
| 10073 | 3 | | | | | ARTN | 1.00 | 10169 | 3 | | | | B9D1 | 1.00 |
| 10074 | 3 | | | | | ARVCF | 1.00 | 10170 | 3 | | | | BAALC | 1.00 |

Fig. 41 - 54

| | | | | | | | | | | | | | | | |
|---|---|---|---|---|---|---|---|---|---|---|---|---|---|---|---|
| 10171 | 3 | | | | | BAAT | 1.00 | 10267 | 3 | | | | | BPY2B | 1.00 |
| 10172 | 3 | | | | | BAGE | 1.00 | 10268 | 3 | | | | | BRCA2 | 1.00 |
| 10173 | 3 | | | | | BAGE3 | 1.00 | 10269 | 3 | | | | | BRD7P3 | 1.00 |
| 10174 | 3 | | | | | BAGE4 | 1.00 | 10270 | 3 | | | | | BRDT | 1.00 |
| 10175 | 3 | | | | | BAGE5 | 1.00 | 10271 | 3 | | | | | BREA2 | 1.00 |
| 10176 | 3 | | | | | BAHCC1 | 1.00 | 10272 | 3 | | | | | BRIP1 | 1.00 |
| 10177 | 3 | | | | | BAI1 | 1.00 | 10273 | 3 | | | | | BRS3 | 1.00 |
| 10178 | 3 | | | | | BAI2 | 1.00 | 10274 | 3 | | | | | BRSK1 | 1.00 |
| 10179 | 3 | | | | | BAI3 | 1.00 | 10275 | 3 | | | | | BRSK2 | 1.00 |
| 10180 | 3 | | | | | BAIAP2L1 | 1.00 | 10276 | 3 | | | | | BRWD1-IT2 | 1.00 |
| 10181 | 3 | | | | | BAIAP2L2 | 1.00 | 10277 | 3 | | | | | BSN | 1.00 |
| 10182 | 3 | | | | | BANF2 | 1.00 | 10278 | 3 | | | | | BSN-AS2 | 1.00 |
| 10183 | 3 | | | | | BARHL1 | 1.00 | 10279 | 3 | | | | | BSND | 1.00 |
| 10184 | 3 | | | | | BARHL2 | 1.00 | 10280 | 3 | | | | | BSPH1 | 1.00 |
| 10185 | 3 | | | | | BARX1 | 1.00 | 10281 | 3 | | | | | BSPRY | 1.00 |
| 10186 | 3 | | | | | BARX2 | 1.00 | 10282 | 3 | | | | | BSX | 1.00 |
| 10187 | 3 | | | | | BBOX1 | 1.00 | 10283 | 3 | | | | | BTBD16 | 1.00 |
| 10188 | 3 | | | | | BBS5 | 1.00 | 10284 | 3 | | | | | BTBD17 | 1.00 |
| 10189 | 3 | | | | | BCAM | 1.00 | 10285 | 3 | | | | | BTBD18 | 1.00 |
| 10190 | 3 | | | | | BCAN | 1.00 | 10286 | 3 | | | | | BTBD19 | 1.00 |
| 10191 | 3 | | | | | BCAR1 | 1.00 | 10287 | 3 | | | | | BTBD8 | 1.00 |
| 10192 | 3 | | | | | BCAR3 | 1.00 | 10288 | 3 | | | | | BTC | 1.00 |
| 10193 | 3 | | | | | BCAR4 | 1.00 | 10289 | 3 | | | | | BTG4 | 1.00 |
| 10194 | 3 | | | | | BCAS1 | 1.00 | 10290 | 3 | | | | | BTN1A1 | 1.00 |
| 10195 | 3 | | | | | BCHE | 1.00 | 10291 | 3 | | | | | BTN2A3P | 1.00 |
| 10196 | 3 | | | | | BCL2L10 | 1.00 | 10292 | 3 | | | | | BTNL2 | 1.00 |
| 10197 | 3 | | | | | BCL2L14 | 1.00 | 10293 | 3 | | | | | BTNL9 | 1.00 |
| 10198 | 3 | | | | | BCL2L15 | 1.00 | 10294 | 3 | | | | | BUB1 | 1.00 |
| 10199 | 3 | | | | | BCL6B | 1.00 | 10295 | 3 | | | | | BUB1B | 1.00 |
| 10200 | 3 | | | | | BCMO1 | 1.00 | 10296 | 3 | | | | | BVES | 1.00 |
| 10201 | 3 | | | | | BCO2 | 1.00 | 10297 | 3 | | | | | BVES-AS1 | 1.00 |
| 10202 | 3 | | | | | BCORP1 | 1.00 | 10298 | 3 | | | | | C10orf10 | 1.00 |
| 10203 | 3 | | | | | BCRP2 | 1.00 | 10299 | 3 | | | | | C10orf103 | 1.00 |
| 10204 | 3 | | | | | BCYRN1 | 1.00 | 10300 | 3 | | | | | C10orf107 | 1.00 |
| 10205 | 3 | | | | | BDAG1 | 1.00 | 10301 | 3 | | | | | C10orf108 | 1.00 |
| 10206 | 3 | | | | | BDKRB1 | 1.00 | 10302 | 3 | | | | | C10orf111 | 1.00 |
| 10207 | 3 | | | | | BDKRB2 | 1.00 | 10303 | 3 | | | | | C10orf113 | 1.00 |
| 10208 | 3 | | | | | BDNF | 1.00 | 10304 | 3 | | | | | C10orf114 | 1.00 |
| 10209 | 3 | | | | | BDNF-AS1 | 1.00 | 10305 | 3 | | | | | C10orf116 | 1.00 |
| 10210 | 3 | | | | | BEAN1 | 1.00 | 10306 | 3 | | | | | C10orf120 | 1.00 |
| 10211 | 3 | | | | | BEND3 | 1.00 | 10307 | 3 | | | | | C10orf122 | 1.00 |
| 10212 | 3 | | | | | BEND4 | 1.00 | 10308 | 3 | | | | | C10orf129 | 1.00 |
| 10213 | 3 | | | | | BEND6 | 1.00 | 10309 | 3 | | | | | C10orf131 | 1.00 |
| 10214 | 3 | | | | | BEST2 | 1.00 | 10310 | 3 | | | | | C10orf136 | 1.00 |
| 10215 | 3 | | | | | BEST3 | 1.00 | 10311 | 3 | | | | | C10orf140 | 1.00 |
| 10216 | 3 | | | | | BEST4 | 1.00 | 10312 | 3 | | | | | C10orf25 | 1.00 |
| 10217 | 3 | | | | | BEX1 | 1.00 | 10313 | 3 | | | | | C10orf27 | 1.00 |
| 10218 | 3 | | | | | BFSP1 | 1.00 | 10314 | 3 | | | | | C10orf32-AS3MT | 1.00 |
| 10219 | 3 | | | | | BFSP2 | 1.00 | 10315 | 3 | | | | | C10orf40 | 1.00 |
| 10220 | 3 | | | | | BGLAP | 1.00 | 10316 | 3 | | | | | C10orf53 | 1.00 |
| 10221 | 3 | | | | | BGN | 1.00 | 10317 | 3 | | | | | C10orf55 | 1.00 |
| 10222 | 3 | | | | | BHLHA9 | 1.00 | 10318 | 3 | | | | | C10orf62 | 1.00 |
| 10223 | 3 | | | | | BHLHB9 | 1.00 | 10319 | 3 | | | | | C10orf67 | 1.00 |
| 10224 | 3 | | | | | BHLHE22 | 1.00 | 10320 | 3 | | | | | C10orf68 | 1.00 |
| 10225 | 3 | | | | | BHLHE23 | 1.00 | 10321 | 3 | | | | | C10orf71 | 1.00 |
| 10226 | 3 | | | | | BHMT | 1.00 | 10322 | 3 | | | | | C10orf81 | 1.00 |
| 10227 | 3 | | | | | BHMT2 | 1.00 | 10323 | 3 | | | | | C10orf82 | 1.00 |
| 10228 | 3 | | | | | BICC1 | 1.00 | 10324 | 3 | | | | | C10orf90 | 1.00 |
| 10229 | 3 | | | | | BIRC5 | 1.00 | 10325 | 3 | | | | | C10orf91 | 1.00 |
| 10230 | 3 | | | | | BIRC7 | 1.00 | 10326 | 3 | | | | | C10orf95 | 1.00 |
| 10231 | 3 | | | | | BIRC8 | 1.00 | 10327 | 3 | | | | | C10orf96 | 1.00 |
| 10232 | 3 | | | | | BIVM-ERCC5 | 1.00 | 10328 | 3 | | | | | C10orf99 | 1.00 |
| 10233 | 3 | | | | | BK250D11 | 1.00 | 10329 | 3 | | | | | C11orf16 | 1.00 |
| 10234 | 3 | | | | | BLID | 1.00 | 10330 | 3 | | | | | C11orf20 | 1.00 |
| 10235 | 3 | | | | | BMP1 | 1.00 | 10331 | 3 | | | | | C11orf34 | 1.00 |
| 10236 | 3 | | | | | BMP10 | 1.00 | 10332 | 3 | | | | | C11orf35 | 1.00 |
| 10237 | 3 | | | | | BMP15 | 1.00 | 10333 | 3 | | | | | C11orf36 | 1.00 |
| 10238 | 3 | | | | | BMP3 | 1.00 | 10334 | 3 | | | | | C11orf40 | 1.00 |
| 10239 | 3 | | | | | BMP4 | 1.00 | 10335 | 3 | | | | | C11orf41 | 1.00 |
| 10240 | 3 | | | | | BMP5 | 1.00 | 10336 | 3 | | | | | C11orf42 | 1.00 |
| 10241 | 3 | | | | | BMP7 | 1.00 | 10337 | 3 | | | | | C11orf45 | 1.00 |
| 10242 | 3 | | | | | BMP8A | 1.00 | 10338 | 3 | | | | | C11orf52 | 1.00 |
| 10243 | 3 | | | | | BMPER | 1.00 | 10339 | 3 | | | | | C11orf53 | 1.00 |
| 10244 | 3 | | | | | BMPR1B | 1.00 | 10340 | 3 | | | | | C11orf65 | 1.00 |
| 10245 | 3 | | | | | BMS1P4 | 1.00 | 10341 | 3 | | | | | C11orf70 | 1.00 |
| 10246 | 3 | | | | | BMS1P5 | 1.00 | 10342 | 3 | | | | | C11orf80 | 1.00 |
| 10247 | 3 | | | | | BNC1 | 1.00 | 10343 | 3 | | | | | C11orf85 | 1.00 |
| 10248 | 3 | | | | | BNC2 | 1.00 | 10344 | 3 | | | | | C11orf86 | 1.00 |
| 10249 | 3 | | | | | BNIPL | 1.00 | 10345 | 3 | | | | | C11orf87 | 1.00 |
| 10250 | 3 | | | | | BOC | 1.00 | 10346 | 3 | | | | | C11orf88 | 1.00 |
| 10251 | 3 | | | | | BOD1P | 1.00 | 10347 | 3 | | | | | C11orf9 | 1.00 |
| 10252 | 3 | | | | | BOK-AS1 | 1.00 | 10348 | 3 | | | | | C11orf91 | 1.00 |
| 10253 | 3 | | | | | BOLA3-AS1 | 1.00 | 10349 | 3 | | | | | C11orf92 | 1.00 |
| 10254 | 3 | | | | | BOLL | 1.00 | 10350 | 3 | | | | | C11orf93 | 1.00 |
| 10255 | 3 | | | | | BPESC1 | 1.00 | 10351 | 3 | | | | | C11orf94 | 1.00 |
| 10256 | 3 | | | | | BPIFA1 | 1.00 | 10352 | 3 | | | | | C11orf96 | 1.00 |
| 10257 | 3 | | | | | BPIFA2 | 1.00 | 10353 | 3 | | | | | C12orf12 | 1.00 |
| 10258 | 3 | | | | | BPIFA3 | 1.00 | 10354 | 3 | | | | | C12orf33 | 1.00 |
| 10259 | 3 | | | | | BPIFA4P | 1.00 | 10355 | 3 | | | | | C12orf34 | 1.00 |
| 10260 | 3 | | | | | BPIFB1 | 1.00 | 10356 | 3 | | | | | C12orf36 | 1.00 |
| 10261 | 3 | | | | | BPIFB2 | 1.00 | 10357 | 3 | | | | | C12orf37 | 1.00 |
| 10262 | 3 | | | | | BPIFB3 | 1.00 | 10358 | 3 | | | | | C12orf39 | 1.00 |
| 10263 | 3 | | | | | BPIFB4 | 1.00 | 10359 | 3 | | | | | C12orf40 | 1.00 |
| 10264 | 3 | | | | | BPIFB6 | 1.00 | 10360 | 3 | | | | | C12orf50 | 1.00 |
| 10265 | 3 | | | | | BPIFC | 1.00 | 10361 | 3 | | | | | C12orf53 | 1.00 |
| 10266 | 3 | | | | | BPY2 | 1.00 | 10362 | 3 | | | | | C12orf54 | 1.00 |

Fig. 41 - 55

| | | | | | | | | | | | | |
|---|---|---|---|---|---|---|---|---|---|---|---|---|
| 10363 | 3 | | | | C12orf56 | 1.00 | 10459 | 3 | | | C19orf75 | 1.00 |
| 10364 | 3 | | | | C12orf59 | 1.00 | 10460 | 3 | | | C19orf76 | 1.00 |
| 10365 | 3 | | | | C12orf60 | 1.00 | 10461 | 3 | | | C19orf80 | 1.00 |
| 10366 | 3 | | | | C12orf61 | 1.00 | 10462 | 3 | | | C19orf81 | 1.00 |
| 10367 | 3 | | | | C12orf68 | 1.00 | 10463 | 3 | | | C1QL1 | 1.00 |
| 10368 | 3 | | | | C12orf69 | 1.00 | 10464 | 3 | | | C1QL2 | 1.00 |
| 10369 | 3 | | | | C12orf70 | 1.00 | 10465 | 3 | | | C1QL4 | 1.00 |
| 10370 | 3 | | | | C12orf71 | 1.00 | 10466 | 3 | | | C1QTNF1 | 1.00 |
| 10371 | 3 | | | | C12orf74 | 1.00 | 10467 | 3 | | | C1QTNF2 | 1.00 |
| 10372 | 3 | | | | C12orf77 | 1.00 | 10468 | 3 | | | C1QTNF3 | 1.00 |
| 10373 | 3 | | | | C13orf33 | 1.00 | 10469 | 3 | | | C1QTNF3-AMACR | 1.00 |
| 10374 | 3 | | | | C13orf35 | 1.00 | 10470 | 3 | | | C1QTNF4 | 1.00 |
| 10375 | 3 | | | | C14orf105 | 1.00 | 10471 | 3 | | | C1QTNF5 | 1.00 |
| 10376 | 3 | | | | C14orf162 | 1.00 | 10472 | 3 | | | C1QTNF7 | 1.00 |
| 10377 | 3 | | | | C14orf165 | 1.00 | 10473 | 3 | | | C1QTNF8 | 1.00 |
| 10378 | 3 | | | | C14orf166B | 1.00 | 10474 | 3 | | | C1QTNF9 | 1.00 |
| 10379 | 3 | | | | C14orf176 | 1.00 | 10475 | 3 | | | C1QTNF9B | 1.00 |
| 10380 | 3 | | | | C14orf177 | 1.00 | 10476 | 3 | | | C1QTNF9B-AS1 | 1.00 |
| 10381 | 3 | | | | C14orf178 | 1.00 | 10477 | 3 | | | C1R | 1.00 |
| 10382 | 3 | | | | C14orf180 | 1.00 | 10478 | 3 | | | C1S | 1.00 |
| 10383 | 3 | | | | C14orf182 | 1.00 | 10479 | 3 | | | C1orf100 | 1.00 |
| 10384 | 3 | | | | C14orf183 | 1.00 | 10480 | 3 | | | C1orf101 | 1.00 |
| 10385 | 3 | | | | C14orf23 | 1.00 | 10481 | 3 | | | C1orf105 | 1.00 |
| 10386 | 3 | | | | C14orf37 | 1.00 | 10482 | 3 | | | C1orf106 | 1.00 |
| 10387 | 3 | | | | C14orf38 | 1.00 | 10483 | 3 | | | C1orf110 | 1.00 |
| 10388 | 3 | | | | C14orf39 | 1.00 | 10484 | 3 | | | C1orf111 | 1.00 |
| 10389 | 3 | | | | C14orf55 | 1.00 | 10485 | 3 | | | C1orf112 | 1.00 |
| 10390 | 3 | | | | C14orf79 | 1.00 | 10486 | 3 | | | C1orf114 | 1.00 |
| 10391 | 3 | | | | C15orf2 | 1.00 | 10487 | 3 | | | C1orf126 | 1.00 |
| 10392 | 3 | | | | C15orf26 | 1.00 | 10488 | 3 | | | C1orf127 | 1.00 |
| 10393 | 3 | | | | C15orf27 | 1.00 | 10489 | 3 | | | C1orf129 | 1.00 |
| 10394 | 3 | | | | C15orf32 | 1.00 | 10490 | 3 | | | C1orf130 | 1.00 |
| 10395 | 3 | | | | C15orf33 | 1.00 | 10491 | 3 | | | C1orf133 | 1.00 |
| 10396 | 3 | | | | C15orf42 | 1.00 | 10492 | 3 | | | C1orf135 | 1.00 |
| 10397 | 3 | | | | C15orf43 | 1.00 | 10493 | 3 | | | C1orf140 | 1.00 |
| 10398 | 3 | | | | C15orf48 | 1.00 | 10494 | 3 | | | C1orf141 | 1.00 |
| 10399 | 3 | | | | C15orf5 | 1.00 | 10495 | 3 | | | C1orf146 | 1.00 |
| 10400 | 3 | | | | C15orf53 | 1.00 | 10496 | 3 | | | C1orf158 | 1.00 |
| 10401 | 3 | | | | C15orf55 | 1.00 | 10497 | 3 | | | C1orf168 | 1.00 |
| 10402 | 3 | | | | C15orf56 | 1.00 | 10498 | 3 | | | C1orf170 | 1.00 |
| 10403 | 3 | | | | C15orf59 | 1.00 | 10499 | 3 | | | C1orf172 | 1.00 |
| 10404 | 3 | | | | C15orf60 | 1.00 | 10500 | 3 | | | C1orf173 | 1.00 |
| 10405 | 3 | | | | C16orf11 | 1.00 | 10501 | 3 | | | C1orf177 | 1.00 |
| 10406 | 3 | | | | C16orf3 | 1.00 | 10502 | 3 | | | C1orf180 | 1.00 |
| 10407 | 3 | | | | C16orf46 | 1.00 | 10503 | 3 | | | C1orf182 | 1.00 |
| 10408 | 3 | | | | C16orf55 | 1.00 | 10504 | 3 | | | C1orf185 | 1.00 |
| 10409 | 3 | | | | C16orf59 | 1.00 | 10505 | 3 | | | C1orf187 | 1.00 |
| 10410 | 3 | | | | C16orf71 | 1.00 | 10506 | 3 | | | C1orf189 | 1.00 |
| 10411 | 3 | | | | C16orf73 | 1.00 | 10507 | 3 | | | C1orf194 | 1.00 |
| 10412 | 3 | | | | C16orf78 | 1.00 | 10508 | 3 | | | C1orf204 | 1.00 |
| 10413 | 3 | | | | C16orf79 | 1.00 | 10509 | 3 | | | C1orf210 | 1.00 |
| 10414 | 3 | | | | C16orf82 | 1.00 | 10510 | 3 | | | C1orf213 | 1.00 |
| 10415 | 3 | | | | C16orf89 | 1.00 | 10511 | 3 | | | C1orf220 | 1.00 |
| 10416 | 3 | | | | C16orf90 | 1.00 | 10512 | 3 | | | C1orf226 | 1.00 |
| 10417 | 3 | | | | C16orf92 | 1.00 | 10513 | 3 | | | C1orf227 | 1.00 |
| 10418 | 3 | | | | C16orf93 | 1.00 | 10514 | 3 | | | C1orf229 | 1.00 |
| 10419 | 3 | | | | C16orf95 | 1.00 | 10515 | 3 | | | C1orf49 | 1.00 |
| 10420 | 3 | | | | C16orf96 | 1.00 | 10516 | 3 | | | C1orf51 | 1.00 |
| 10421 | 3 | | | | C17orf102 | 1.00 | 10517 | 3 | | | C1orf53 | 1.00 |
| 10422 | 3 | | | | C17orf104 | 1.00 | 10518 | 3 | | | C1orf54 | 1.00 |
| 10423 | 3 | | | | C17orf105 | 1.00 | 10519 | 3 | | | C1orf61 | 1.00 |
| 10424 | 3 | | | | C17orf107 | 1.00 | 10520 | 3 | | | C1orf64 | 1.00 |
| 10425 | 3 | | | | C17orf110 | 1.00 | 10521 | 3 | | | C1orf65 | 1.00 |
| 10426 | 3 | | | | C17orf28 | 1.00 | 10522 | 3 | | | C1orf68 | 1.00 |
| 10427 | 3 | | | | C17orf47 | 1.00 | 10523 | 3 | | | C1orf87 | 1.00 |
| 10428 | 3 | | | | C17orf50 | 1.00 | 10524 | 3 | | | C1orf88 | 1.00 |
| 10429 | 3 | | | | C17orf53 | 1.00 | 10525 | 3 | | | C1orf94 | 1.00 |
| 10430 | 3 | | | | C17orf57 | 1.00 | 10526 | 3 | | | C1orf95 | 1.00 |
| 10431 | 3 | | | | C17orf64 | 1.00 | 10527 | 3 | | | C1orf98 | 1.00 |
| 10432 | 3 | | | | C17orf66 | 1.00 | 10528 | 3 | | | C20orf123 | 1.00 |
| 10433 | 3 | | | | C17orf67 | 1.00 | 10529 | 3 | | | C20orf132 | 1.00 |
| 10434 | 3 | | | | C17orf74 | 1.00 | 10530 | 3 | | | C20orf141 | 1.00 |
| 10435 | 3 | | | | C17orf77 | 1.00 | 10531 | 3 | | | C20orf144 | 1.00 |
| 10436 | 3 | | | | C17orf78 | 1.00 | 10532 | 3 | | | C20orf151 | 1.00 |
| 10437 | 3 | | | | C17orf82 | 1.00 | 10533 | 3 | | | C20orf152 | 1.00 |
| 10438 | 3 | | | | C17orf96 | 1.00 | 10534 | 3 | | | C20orf160 | 1.00 |
| 10439 | 3 | | | | C17orf98 | 1.00 | 10535 | 3 | | | C20orf166 | 1.00 |
| 10440 | 3 | | | | C17orf99 | 1.00 | 10536 | 3 | | | C20orf166-AS1 | 1.00 |
| 10441 | 3 | | | | C18orf26 | 1.00 | 10537 | 3 | | | C20orf173 | 1.00 |
| 10442 | 3 | | | | C18orf34 | 1.00 | 10538 | 3 | | | C20orf195 | 1.00 |
| 10443 | 3 | | | | C18orf42 | 1.00 | 10539 | 3 | | | C20orf201 | 1.00 |
| 10444 | 3 | | | | C18orf54 | 1.00 | 10540 | 3 | | | C20orf202 | 1.00 |
| 10445 | 3 | | | | C18orf56 | 1.00 | 10541 | 3 | | | C20orf203 | 1.00 |
| 10446 | 3 | | | | C18orf62 | 1.00 | 10542 | 3 | | | C20orf26 | 1.00 |
| 10447 | 3 | | | | C18orf63 | 1.00 | 10543 | 3 | | | C20orf54 | 1.00 |
| 10448 | 3 | | | | C19orf18 | 1.00 | 10544 | 3 | | | C20orf7 | 1.00 |
| 10449 | 3 | | | | C19orf21 | 1.00 | 10545 | 3 | | | C20orf79 | 1.00 |
| 10450 | 3 | | | | C19orf26 | 1.00 | 10546 | 3 | | | C20orf85 | 1.00 |
| 10451 | 3 | | | | C19orf29-AS1 | 1.00 | 10547 | 3 | | | C20orf96 | 1.00 |
| 10452 | 3 | | | | C19orf33 | 1.00 | 10548 | 3 | | | C21orf128 | 1.00 |
| 10453 | 3 | | | | C19orf44 | 1.00 | 10549 | 3 | | | C21orf15 | 1.00 |
| 10454 | 3 | | | | C19orf45 | 1.00 | 10550 | 3 | | | C21orf37 | 1.00 |
| 10455 | 3 | | | | C19orf46 | 1.00 | 10551 | 3 | | | C21orf49 | 1.00 |
| 10456 | 3 | | | | C19orf51 | 1.00 | 10552 | 3 | | | C21orf54 | 1.00 |
| 10457 | 3 | | | | C19orf57 | 1.00 | 10553 | 3 | | | C21orf62 | 1.00 |
| 10458 | 3 | | | | C19orf69 | 1.00 | 10554 | 3 | | | C21orf88 | 1.00 |

Fig. 41 - 56

| | | | | | | | | | | | | | | | |
|---|---|---|---|---|---|---|---|---|---|---|---|---|---|---|---|
| 10555 | 3 | | | | | C21orf90 | 1.00 | 10651 | 3 | | | | | C5orf54 | 1.00 |
| 10556 | 3 | | | | | C21orf91-OT1 | 1.00 | 10652 | 3 | | | | | C5orf55 | 1.00 |
| 10557 | 3 | | | | | C22orf15 | 1.00 | 10653 | 3 | | | | | C5orf58 | 1.00 |
| 10558 | 3 | | | | | C22orf24 | 1.00 | 10654 | 3 | | | | | C5orf60 | 1.00 |
| 10559 | 3 | | | | | C22orf26 | 1.00 | 10655 | 3 | | | | | C5orf64 | 1.00 |
| 10560 | 3 | | | | | C22orf31 | 1.00 | 10656 | 3 | | | | | C5orf65 | 1.00 |
| 10561 | 3 | | | | | C22orf42 | 1.00 | 10657 | 3 | | | | | C6 | 1.00 |
| 10562 | 3 | | | | | C22orf43 | 1.00 | 10658 | 3 | | | | | C6orf10 | 1.00 |
| 10563 | 3 | | | | | C22orf45 | 1.00 | 10659 | 3 | | | | | C6orf118 | 1.00 |
| 10564 | 3 | | | | | C2CD4A | 1.00 | 10660 | 3 | | | | | C6orf123 | 1.00 |
| 10565 | 3 | | | | | C2CD4B | 1.00 | 10661 | 3 | | | | | C6orf132 | 1.00 |
| 10566 | 3 | | | | | C2CD4C | 1.00 | 10662 | 3 | | | | | C6orf141 | 1.00 |
| 10567 | 3 | | | | | C2CD4D | 1.00 | 10663 | 3 | | | | | C6orf147 | 1.00 |
| 10568 | 3 | | | | | C2orf16 | 1.00 | 10664 | 3 | | | | | C6orf15 | 1.00 |
| 10569 | 3 | | | | | C2orf27A | 1.00 | 10665 | 3 | | | | | C6orf163 | 1.00 |
| 10570 | 3 | | | | | C2orf27B | 1.00 | 10666 | 3 | | | | | C6orf164 | 1.00 |
| 10571 | 3 | | | | | C2orf40 | 1.00 | 10667 | 3 | | | | | C6orf165 | 1.00 |
| 10572 | 3 | | | | | C2orf48 | 1.00 | 10668 | 3 | | | | | C6orf170 | 1.00 |
| 10573 | 3 | | | | | C2orf50 | 1.00 | 10669 | 3 | | | | | C6orf174 | 1.00 |
| 10574 | 3 | | | | | C2orf51 | 1.00 | 10670 | 3 | | | | | C6orf195 | 1.00 |
| 10575 | 3 | | | | | C2orf53 | 1.00 | 10671 | 3 | | | | | C6orf201 | 1.00 |
| 10576 | 3 | | | | | C2orf54 | 1.00 | 10672 | 3 | | | | | C6orf221 | 1.00 |
| 10577 | 3 | | | | | C2orf57 | 1.00 | 10673 | 3 | | | | | C6orf222 | 1.00 |
| 10578 | 3 | | | | | C2orf61 | 1.00 | 10674 | 3 | | | | | C6orf223 | 1.00 |
| 10579 | 3 | | | | | C2orf62 | 1.00 | 10675 | 3 | | | | | C6orf225 | 1.00 |
| 10580 | 3 | | | | | C2orf63 | 1.00 | 10676 | 3 | | | | | C6orf52 | 1.00 |
| 10581 | 3 | | | | | C2orf65 | 1.00 | 10677 | 3 | | | | | C6orf58 | 1.00 |
| 10582 | 3 | | | | | C2orf66 | 1.00 | 10678 | 3 | | | | | C6orf7 | 1.00 |
| 10583 | 3 | | | | | C2orf70 | 1.00 | 10679 | 3 | | | | | C6orf99 | 1.00 |
| 10584 | 3 | | | | | C2orf71 | 1.00 | 10680 | 3 | | | | | C7 | 1.00 |
| 10585 | 3 | | | | | C2orf72 | 1.00 | 10681 | 3 | | | | | C7orf10 | 1.00 |
| 10586 | 3 | | | | | C2orf73 | 1.00 | 10682 | 3 | | | | | C7orf13 | 1.00 |
| 10587 | 3 | | | | | C2orf76 | 1.00 | 10683 | 3 | | | | | C7orf33 | 1.00 |
| 10588 | 3 | | | | | C2orf77 | 1.00 | 10684 | 3 | | | | | C7orf34 | 1.00 |
| 10589 | 3 | | | | | C2orf78 | 1.00 | 10685 | 3 | | | | | C7orf45 | 1.00 |
| 10590 | 3 | | | | | C2orf80 | 1.00 | 10686 | 3 | | | | | C7orf46 | 1.00 |
| 10591 | 3 | | | | | C2orf82 | 1.00 | 10687 | 3 | | | | | C7orf57 | 1.00 |
| 10592 | 3 | | | | | C2orf83 | 1.00 | 10688 | 3 | | | | | C7orf62 | 1.00 |
| 10593 | 3 | | | | | C2orf84 | 1.00 | 10689 | 3 | | | | | C7orf63 | 1.00 |
| 10594 | 3 | | | | | C2orf91 | 1.00 | 10690 | 3 | | | | | C7orf65 | 1.00 |
| 10595 | 3 | | | | | C3 | 1.00 | 10691 | 3 | | | | | C7orf66 | 1.00 |
| 10596 | 3 | | | | | C3P1 | 1.00 | 10692 | 3 | | | | | C7orf69 | 1.00 |
| 10597 | 3 | | | | | C3orf15 | 1.00 | 10693 | 3 | | | | | C7orf71 | 1.00 |
| 10598 | 3 | | | | | C3orf20 | 1.00 | 10694 | 3 | | | | | C7orf72 | 1.00 |
| 10599 | 3 | | | | | C3orf22 | 1.00 | 10695 | 3 | | | | | C8A | 1.00 |
| 10600 | 3 | | | | | C3orf24 | 1.00 | 10696 | 3 | | | | | C8B | 1.00 |
| 10601 | 3 | | | | | C3orf25 | 1.00 | 10697 | 3 | | | | | C8G | 1.00 |
| 10602 | 3 | | | | | C3orf27 | 1.00 | 10698 | 3 | | | | | C8ORFK29 | 1.00 |
| 10603 | 3 | | | | | C3orf30 | 1.00 | 10699 | 3 | | | | | C8orf12 | 1.00 |
| 10604 | 3 | | | | | C3orf32 | 1.00 | 10700 | 3 | | | | | C8orf22 | 1.00 |
| 10605 | 3 | | | | | C3orf33 | 1.00 | 10701 | 3 | | | | | C8orf31 | 1.00 |
| 10606 | 3 | | | | | C3orf35 | 1.00 | 10702 | 3 | | | | | C8orf34 | 1.00 |
| 10607 | 3 | | | | | C3orf36 | 1.00 | 10703 | 3 | | | | | C8orf37 | 1.00 |
| 10608 | 3 | | | | | C3orf43 | 1.00 | 10704 | 3 | | | | | C8orf38 | 1.00 |
| 10609 | 3 | | | | | C3orf45 | 1.00 | 10705 | 3 | | | | | C8orf39 | 1.00 |
| 10610 | 3 | | | | | C3orf49 | 1.00 | 10706 | 3 | | | | | C8orf4 | 1.00 |
| 10611 | 3 | | | | | C3orf51 | 1.00 | 10707 | 3 | | | | | C8orf45 | 1.00 |
| 10612 | 3 | | | | | C3orf52 | 1.00 | 10708 | 3 | | | | | C8orf46 | 1.00 |
| 10613 | 3 | | | | | C3orf55 | 1.00 | 10709 | 3 | | | | | C8orf47 | 1.00 |
| 10614 | 3 | | | | | C3orf65 | 1.00 | 10710 | 3 | | | | | C8orf48 | 1.00 |
| 10615 | 3 | | | | | C3orf67 | 1.00 | 10711 | 3 | | | | | C8orf51 | 1.00 |
| 10616 | 3 | | | | | C3orf70 | 1.00 | 10712 | 3 | | | | | C8orf56 | 1.00 |
| 10617 | 3 | | | | | C3orf72 | 1.00 | 10713 | 3 | | | | | C8orf69 | 1.00 |
| 10618 | 3 | | | | | C3orf74 | 1.00 | 10714 | 3 | | | | | C8orf71 | 1.00 |
| 10619 | 3 | | | | | C3orf77 | 1.00 | 10715 | 3 | | | | | C8orf74 | 1.00 |
| 10620 | 3 | | | | | C3orf79 | 1.00 | 10716 | 3 | | | | | C8orf75 | 1.00 |
| 10621 | 3 | | | | | C3orf80 | 1.00 | 10717 | 3 | | | | | C8orf77 | 1.00 |
| 10622 | 3 | | | | | C4B | 1.00 | 10718 | 3 | | | | | C8orf84 | 1.00 |
| 10623 | 3 | | | | | C4BPB | 1.00 | 10719 | 3 | | | | | C8orf85 | 1.00 |
| 10624 | 3 | | | | | C4orf17 | 1.00 | 10720 | 3 | | | | | C8orf86 | 1.00 |
| 10625 | 3 | | | | | C4orf19 | 1.00 | 10721 | 3 | | | | | C8orf87 | 1.00 |
| 10626 | 3 | | | | | C4orf21 | 1.00 | 10722 | 3 | | | | | C9 | 1.00 |
| 10627 | 3 | | | | | C4orf22 | 1.00 | 10723 | 3 | | | | | C9orf102 | 1.00 |
| 10628 | 3 | | | | | C4orf26 | 1.00 | 10724 | 3 | | | | | C9orf106 | 1.00 |
| 10629 | 3 | | | | | C4orf36 | 1.00 | 10725 | 3 | | | | | C9orf11 | 1.00 |
| 10630 | 3 | | | | | C4orf37 | 1.00 | 10726 | 3 | | | | | C9orf116 | 1.00 |
| 10631 | 3 | | | | | C4orf38 | 1.00 | 10727 | 3 | | | | | C9orf117 | 1.00 |
| 10632 | 3 | | | | | C4orf39 | 1.00 | 10728 | 3 | | | | | C9orf125 | 1.00 |
| 10633 | 3 | | | | | C4orf40 | 1.00 | 10729 | 3 | | | | | C9orf128 | 1.00 |
| 10634 | 3 | | | | | C4orf44 | 1.00 | 10730 | 3 | | | | | C9orf131 | 1.00 |
| 10635 | 3 | | | | | C4orf45 | 1.00 | 10731 | 3 | | | | | C9orf135 | 1.00 |
| 10636 | 3 | | | | | C4orf47 | 1.00 | 10732 | 3 | | | | | C9orf146 | 1.00 |
| 10637 | 3 | | | | | C4orf49 | 1.00 | 10733 | 3 | | | | | C9orf152 | 1.00 |
| 10638 | 3 | | | | | C4orf51 | 1.00 | 10734 | 3 | | | | | C9orf153 | 1.00 |
| 10639 | 3 | | | | | C4orf6 | 1.00 | 10735 | 3 | | | | | C9orf163 | 1.00 |
| 10640 | 3 | | | | | C5 | 1.00 | 10736 | 3 | | | | | C9orf169 | 1.00 |
| 10641 | 3 | | | | | C5orf27 | 1.00 | 10737 | 3 | | | | | C9orf170 | 1.00 |
| 10642 | 3 | | | | | C5orf34 | 1.00 | 10738 | 3 | | | | | C9orf171 | 1.00 |
| 10643 | 3 | | | | | C5orf38 | 1.00 | 10739 | 3 | | | | | C9orf173 | 1.00 |
| 10644 | 3 | | | | | C5orf42 | 1.00 | 10740 | 3 | | | | | C9orf174 | 1.00 |
| 10645 | 3 | | | | | C5orf45 | 1.00 | 10741 | 3 | | | | | C9orf24 | 1.00 |
| 10646 | 3 | | | | | C5orf46 | 1.00 | 10742 | 3 | | | | | C9orf29 | 1.00 |
| 10647 | 3 | | | | | C5orf47 | 1.00 | 10743 | 3 | | | | | C9orf3 | 1.00 |
| 10648 | 3 | | | | | C5orf48 | 1.00 | 10744 | 3 | | | | | C9orf30-TMEFF1 | 1.00 |
| 10649 | 3 | | | | | C5orf49 | 1.00 | 10745 | 3 | | | | | C9orf4 | 1.00 |
| 10650 | 3 | | | | | C5orf52 | 1.00 | 10746 | 3 | | | | | C9orf43 | 1.00 |

Fig. 41 - 57

| | | | | | | | | |
|---|---|---|---|---|---|---|---|---|
| 10747 | 3 | | | | C9orf47 | 1.00 | | |
| 10748 | 3 | | | | C9orf50 | 1.00 | | |
| 10749 | 3 | | | | C9orf53 | 1.00 | | |
| 10750 | 3 | | | | C9orf57 | 1.00 | | |
| 10751 | 3 | | | | C9orf68 | 1.00 | | |
| 10752 | 3 | | | | C9orf79 | 1.00 | | |
| 10753 | 3 | | | | C9orf84 | 1.00 | | |
| 10754 | 3 | | | | C9orf9 | 1.00 | | |
| 10755 | 3 | | | | C9orf93 | 1.00 | | |
| 10756 | 3 | | | | C9orf96 | 1.00 | | |
| 10757 | 3 | | | | CA10 | 1.00 | | |
| 10758 | 3 | | | | CA12 | 1.00 | | |
| 10759 | 3 | | | | CA13 | 1.00 | | |
| 10760 | 3 | | | | CA14 | 1.00 | | |
| 10761 | 3 | | | | CA3 | 1.00 | | |
| 10762 | 3 | | | | CA5A | 1.00 | | |
| 10763 | 3 | | | | CA6 | 1.00 | | |
| 10764 | 3 | | | | CA7 | 1.00 | | |
| 10765 | 3 | | | | CA8 | 1.00 | | |
| 10766 | 3 | | | | CA9 | 1.00 | | |
| 10767 | 3 | | | | CABLES1 | 1.00 | | |
| 10768 | 3 | | | | CABP1 | 1.00 | | |
| 10769 | 3 | | | | CABP2 | 1.00 | | |
| 10770 | 3 | | | | CABP4 | 1.00 | | |
| 10771 | 3 | | | | CABP7 | 1.00 | | |
| 10772 | 3 | | | | CABS1 | 1.00 | | |
| 10773 | 3 | | | | CABYR | 1.00 | | |
| 10774 | 3 | | | | CACHD1 | 1.00 | | |
| 10775 | 3 | | | | CACNA1A | 1.00 | | |
| 10776 | 3 | | | | CACNA1B | 1.00 | | |
| 10777 | 3 | | | | CACNA1C | 1.00 | | |
| 10778 | 3 | | | | CACNA1D | 1.00 | | |
| 10779 | 3 | | | | CACNA1E | 1.00 | | |
| 10780 | 3 | | | | CACNA1F | 1.00 | | |
| 10781 | 3 | | | | CACNA1G | 1.00 | | |
| 10782 | 3 | | | | CACNA1H | 1.00 | | |
| 10783 | 3 | | | | CACNA1S | 1.00 | | |
| 10784 | 3 | | | | CACNA2D1 | 1.00 | | |
| 10785 | 3 | | | | CACNA2D3 | 1.00 | | |
| 10786 | 3 | | | | CACNB2 | 1.00 | | |
| 10787 | 3 | | | | CACNB3 | 1.00 | | |
| 10788 | 3 | | | | CACNG1 | 1.00 | | |
| 10789 | 3 | | | | CACNG2 | 1.00 | | |
| 10790 | 3 | | | | CACNG3 | 1.00 | | |
| 10791 | 3 | | | | CACNG4 | 1.00 | | |
| 10792 | 3 | | | | CACNG5 | 1.00 | | |
| 10793 | 3 | | | | CACNG7 | 1.00 | | |
| 10794 | 3 | | | | CACNG8 | 1.00 | | |
| 10795 | 3 | | | | CADM1 | 1.00 | | |
| 10796 | 3 | | | | CADM2 | 1.00 | | |
| 10797 | 3 | | | | CADM3 | 1.00 | | |
| 10798 | 3 | | | | CADPS | 1.00 | | |
| 10799 | 3 | | | | CADPS2 | 1.00 | | |
| 10800 | 3 | | | | CAGE1 | 1.00 | | |
| 10801 | 3 | | | | CALB1 | 1.00 | | |
| 10802 | 3 | | | | CALB2 | 1.00 | | |
| 10803 | 3 | | | | CALCA | 1.00 | | |
| 10804 | 3 | | | | CALCB | 1.00 | | |
| 10805 | 3 | | | | CALCR | 1.00 | | |
| 10806 | 3 | | | | CALCRL | 1.00 | | |
| 10807 | 3 | | | | CALHM1 | 1.00 | | |
| 10808 | 3 | | | | CALHM3 | 1.00 | | |
| 10809 | 3 | | | | CALML3 | 1.00 | | |
| 10810 | 3 | | | | CALML5 | 1.00 | | |
| 10811 | 3 | | | | CALML6 | 1.00 | | |
| 10812 | 3 | | | | CALN1 | 1.00 | | |
| 10813 | 3 | | | | CALR3 | 1.00 | | |
| 10814 | 3 | | | | CALY | 1.00 | | |
| 10815 | 3 | | | | CAMK1G | 1.00 | | |
| 10816 | 3 | | | | CAMK2A | 1.00 | | |
| 10817 | 3 | | | | CAMK2N1 | 1.00 | | |
| 10818 | 3 | | | | CAMK2N2 | 1.00 | | |
| 10819 | 3 | | | | CAMKV | 1.00 | | |
| 10820 | 3 | | | | CAMSAP3 | 1.00 | | |
| 10821 | 3 | | | | CAND2 | 1.00 | | |
| 10822 | 3 | | | | CAP2 | 1.00 | | |
| 10823 | 3 | | | | CAPN11 | 1.00 | | |
| 10824 | 3 | | | | CAPN13 | 1.00 | | |
| 10825 | 3 | | | | CAPN14 | 1.00 | | |
| 10826 | 3 | | | | CAPN6 | 1.00 | | |
| 10827 | 3 | | | | CAPN8 | 1.00 | | |
| 10828 | 3 | | | | CAPN9 | 1.00 | | |
| 10829 | 3 | | | | CAPNS2 | 1.00 | | |
| 10830 | 3 | | | | CAPS2 | 1.00 | | |
| 10831 | 3 | | | | CAPSL | 1.00 | | |
| 10832 | 3 | | | | CAPZA3 | 1.00 | | |
| 10833 | 3 | | | | CARD10 | 1.00 | | |
| 10834 | 3 | | | | CARD14 | 1.00 | | |
| 10835 | 3 | | | | CARD18 | 1.00 | | |
| 10836 | 3 | | | | CARTPT | 1.00 | | |
| 10837 | 3 | | | | CASC1 | 1.00 | | |
| 10838 | 3 | | | | CASC2 | 1.00 | | |
| 10839 | 3 | | | | CASC5 | 1.00 | | |
| 10840 | 3 | | | | CASKIN1 | 1.00 | | |
| 10841 | 3 | | | | CASKIN2 | 1.00 | | |
| 10842 | 3 | | | | CASP12 | 1.00 | | |
| 10843 | 3 | | | | CASP14 | 1.00 | | |
| 10844 | 3 | | | | CASQ1 | 1.00 | | |
| 10845 | 3 | | | | CASQ2 | 1.00 | | |
| 10846 | 3 | | | | CASR | 1.00 | | |
| 10847 | 3 | | | | CATSPER1 | 1.00 | | |
| 10848 | 3 | | | | CATSPER2 | 1.00 | | |
| 10849 | 3 | | | | CATSPER2P1 | 1.00 | | |
| 10850 | 3 | | | | CATSPER3 | 1.00 | | |
| 10851 | 3 | | | | CATSPER4 | 1.00 | | |
| 10852 | 3 | | | | CATSPERB | 1.00 | | |
| 10853 | 3 | | | | CATSPERD | 1.00 | | |
| 10854 | 3 | | | | CATSPERG | 1.00 | | |
| 10855 | 3 | | | | CAV1 | 1.00 | | |
| 10856 | 3 | | | | CAV2 | 1.00 | | |
| 10857 | 3 | | | | CAV3 | 1.00 | | |
| 10858 | 3 | | | | CBLC | 1.00 | | |
| 10859 | 3 | | | | CBLN1 | 1.00 | | |
| 10860 | 3 | | | | CBLN2 | 1.00 | | |
| 10861 | 3 | | | | CBLN3 | 1.00 | | |
| 10862 | 3 | | | | CBLN4 | 1.00 | | |
| 10863 | 3 | | | | CBR3-AS1 | 1.00 | | |
| 10864 | 3 | | | | CBX2 | 1.00 | | |
| 10865 | 3 | | | | CBY3 | 1.00 | | |
| 10866 | 3 | | | | CC2D2A | 1.00 | | |
| 10867 | 3 | | | | CC2D2B | 1.00 | | |
| 10868 | 3 | | | | CCBE1 | 1.00 | | |
| 10869 | 3 | | | | CCBP2 | 1.00 | | |
| 10870 | 3 | | | | CCDC102B | 1.00 | | |
| 10871 | 3 | | | | CCDC103 | 1.00 | | |
| 10872 | 3 | | | | CCDC105 | 1.00 | | |
| 10873 | 3 | | | | CCDC108 | 1.00 | | |
| 10874 | 3 | | | | CCDC11 | 1.00 | | |
| 10875 | 3 | | | | CCDC110 | 1.00 | | |
| 10876 | 3 | | | | CCDC113 | 1.00 | | |
| 10877 | 3 | | | | CCDC114 | 1.00 | | |
| 10878 | 3 | | | | CCDC116 | 1.00 | | |
| 10879 | 3 | | | | CCDC129 | 1.00 | | |
| 10880 | 3 | | | | CCDC13 | 1.00 | | |
| 10881 | 3 | | | | CCDC135 | 1.00 | | |
| 10882 | 3 | | | | CCDC136 | 1.00 | | |
| 10883 | 3 | | | | CCDC138 | 1.00 | | |
| 10884 | 3 | | | | CCDC140 | 1.00 | | |
| 10885 | 3 | | | | CCDC141 | 1.00 | | |
| 10886 | 3 | | | | CCDC144A | 1.00 | | |
| 10887 | 3 | | | | CCDC144B | 1.00 | | |
| 10888 | 3 | | | | CCDC144C | 1.00 | | |
| 10889 | 3 | | | | CCDC144NL | 1.00 | | |
| 10890 | 3 | | | | CCDC147 | 1.00 | | |
| 10891 | 3 | | | | CCDC148 | 1.00 | | |
| 10892 | 3 | | | | CCDC15 | 1.00 | | |
| 10893 | 3 | | | | CCDC150 | 1.00 | | |
| 10894 | 3 | | | | CCDC151 | 1.00 | | |
| 10895 | 3 | | | | CCDC152 | 1.00 | | |
| 10896 | 3 | | | | CCDC154 | 1.00 | | |
| 10897 | 3 | | | | CCDC155 | 1.00 | | |
| 10898 | 3 | | | | CCDC157 | 1.00 | | |
| 10899 | 3 | | | | CCDC158 | 1.00 | | |
| 10900 | 3 | | | | CCDC160 | 1.00 | | |
| 10901 | 3 | | | | CCDC162P | 1.00 | | |
| 10902 | 3 | | | | CCDC164 | 1.00 | | |
| 10903 | 3 | | | | CCDC165 | 1.00 | | |
| 10904 | 3 | | | | CCDC166 | 1.00 | | |
| 10905 | 3 | | | | CCDC168 | 1.00 | | |
| 10906 | 3 | | | | CCDC169 | 1.00 | | |
| 10907 | 3 | | | | CCDC169-SOHLH2 | 1.00 | | |
| 10908 | 3 | | | | CCDC17 | 1.00 | | |
| 10909 | 3 | | | | CCDC18 | 1.00 | | |
| 10910 | 3 | | | | CCDC24 | 1.00 | | |
| 10911 | 3 | | | | CCDC27 | 1.00 | | |
| 10912 | 3 | | | | CCDC3 | 1.00 | | |
| 10913 | 3 | | | | CCDC30 | 1.00 | | |
| 10914 | 3 | | | | CCDC33 | 1.00 | | |
| 10915 | 3 | | | | CCDC36 | 1.00 | | |
| 10916 | 3 | | | | CCDC37 | 1.00 | | |
| 10917 | 3 | | | | CCDC38 | 1.00 | | |
| 10918 | 3 | | | | CCDC39 | 1.00 | | |
| 10919 | 3 | | | | CCDC40 | 1.00 | | |
| 10920 | 3 | | | | CCDC41 | 1.00 | | |
| 10921 | 3 | | | | CCDC42 | 1.00 | | |
| 10922 | 3 | | | | CCDC48 | 1.00 | | |
| 10923 | 3 | | | | CCDC54 | 1.00 | | |
| 10924 | 3 | | | | CCDC60 | 1.00 | | |
| 10925 | 3 | | | | CCDC62 | 1.00 | | |
| 10926 | 3 | | | | CCDC63 | 1.00 | | |
| 10927 | 3 | | | | CCDC64B | 1.00 | | |
| 10928 | 3 | | | | CCDC67 | 1.00 | | |
| 10929 | 3 | | | | CCDC68 | 1.00 | | |
| 10930 | 3 | | | | CCDC7 | 1.00 | | |
| 10931 | 3 | | | | CCDC70 | 1.00 | | |
| 10932 | 3 | | | | CCDC74A | 1.00 | | |
| 10933 | 3 | | | | CCDC74B | 1.00 | | |
| 10934 | 3 | | | | CCDC78 | 1.00 | | |
| 10935 | 3 | | | | CCDC79 | 1.00 | | |
| 10936 | 3 | | | | CCDC8 | 1.00 | | |
| 10937 | 3 | | | | CCDC80 | 1.00 | | |
| 10938 | 3 | | | | CCDC81 | 1.00 | | |

Fig. 41 - 58

| | | | | | | | | | | | | | | | | |
|---|---|---|---|---|---|---|---|---|---|---|---|---|---|---|---|---|
| 10939 | 3 | | | | | | CCDC83 | 1.00 | 11035 | 3 | | | | | CDKL1 | 1.00 |
| 10940 | 3 | | | | | | CCDC85A | 1.00 | 11036 | 3 | | | | | CDKL2 | 1.00 |
| 10941 | 3 | | | | | | CCDC87 | 1.00 | 11037 | 3 | | | | | CDKL3 | 1.00 |
| 10942 | 3 | | | | | | CCDC89 | 1.00 | 11038 | 3 | | | | | CDKL4 | 1.00 |
| 10943 | 3 | | | | | | CCIN | 1.00 | 11039 | 3 | | | | | CDKN2B-AS1 | 1.00 |
| 10944 | 3 | | | | | | CCK | 1.00 | 11040 | 3 | | | | | CDKN3 | 1.00 |
| 10945 | 3 | | | | | | CCKAR | 1.00 | 11041 | 3 | | | | | CDNF | 1.00 |
| 10946 | 3 | | | | | | CCKBR | 1.00 | 11042 | 3 | | | | | CDO1 | 1.00 |
| 10947 | 3 | | | | | | CCL1 | 1.00 | 11043 | 3 | | | | | CDON | 1.00 |
| 10948 | 3 | | | | | | CCL11 | 1.00 | 11044 | 3 | | | | | CDR1 | 1.00 |
| 10949 | 3 | | | | | | CCL13 | 1.00 | 11045 | 3 | | | | | CDR2L | 1.00 |
| 10950 | 3 | | | | | | CCL14 | 1.00 | 11046 | 3 | | | | | CDRT1 | 1.00 |
| 10951 | 3 | | | | | | CCL14-CCL15 | 1.00 | 11047 | 3 | | | | | CDRT15 | 1.00 |
| 10952 | 3 | | | | | | CCL15 | 1.00 | 11048 | 3 | | | | | CDRT15L2 | 1.00 |
| 10953 | 3 | | | | | | CCL16 | 1.00 | 11049 | 3 | | | | | CDRT15P1 | 1.00 |
| 10954 | 3 | | | | | | CCL17 | 1.00 | 11050 | 3 | | | | | CDRT15P2 | 1.00 |
| 10955 | 3 | | | | | | CCL18 | 1.00 | 11051 | 3 | | | | | CDRT7 | 1.00 |
| 10956 | 3 | | | | | | CCL19 | 1.00 | 11052 | 3 | | | | | CDS1 | 1.00 |
| 10957 | 3 | | | | | | CCL20 | 1.00 | 11053 | 3 | | | | | CDSN | 1.00 |
| 10958 | 3 | | | | | | CCL21 | 1.00 | 11054 | 3 | | | | | CDX1 | 1.00 |
| 10959 | 3 | | | | | | CCL22 | 1.00 | 11055 | 3 | | | | | CDX2 | 1.00 |
| 10960 | 3 | | | | | | CCL24 | 1.00 | 11056 | 3 | | | | | CDX4 | 1.00 |
| 10961 | 3 | | | | | | CCL25 | 1.00 | 11057 | 3 | | | | | CDY1 | 1.00 |
| 10962 | 3 | | | | | | CCL26 | 1.00 | 11058 | 3 | | | | | CDY1B | 1.00 |
| 10963 | 3 | | | | | | CCL27 | 1.00 | 11059 | 3 | | | | | CDY2A | 1.00 |
| 10964 | 3 | | | | | | CCL3L1 | 1.00 | 11060 | 3 | | | | | CDY2B | 1.00 |
| 10965 | 3 | | | | | | CCL7 | 1.00 | 11061 | 3 | | | | | CEACAM16 | 1.00 |
| 10966 | 3 | | | | | | CCL8 | 1.00 | 11062 | 3 | | | | | CEACAM18 | 1.00 |
| 10967 | 3 | | | | | | CCNA1 | 1.00 | 11063 | 3 | | | | | CEACAM19 | 1.00 |
| 10968 | 3 | | | | | | CCNB3 | 1.00 | 11064 | 3 | | | | | CEACAM20 | 1.00 |
| 10969 | 3 | | | | | | CCND1 | 1.00 | 11065 | 3 | | | | | CEACAM22P | 1.00 |
| 10970 | 3 | | | | | | CCNE1 | 1.00 | 11066 | 3 | | | | | CEACAM5 | 1.00 |
| 10971 | 3 | | | | | | CCNE2 | 1.00 | 11067 | 3 | | | | | CEACAM7 | 1.00 |
| 10972 | 3 | | | | | | CCNI2 | 1.00 | 11068 | 3 | | | | | CECR2 | 1.00 |
| 10973 | 3 | | | | | | CCNO | 1.00 | 11069 | 3 | | | | | CECR3 | 1.00 |
| 10974 | 3 | | | | | | CCRL1 | 1.00 | 11070 | 3 | | | | | CECR5-AS1 | 1.00 |
| 10975 | 3 | | | | | | CCT6B | 1.00 | 11071 | 3 | | | | | CECR7 | 1.00 |
| 10976 | 3 | | | | | | CCT8L2 | 1.00 | 11072 | 3 | | | | | CEL | 1.00 |
| 10977 | 3 | | | | | | CD109 | 1.00 | 11073 | 3 | | | | | CELA1 | 1.00 |
| 10978 | 3 | | | | | | CD163L1 | 1.00 | 11074 | 3 | | | | | CELA2A | 1.00 |
| 10979 | 3 | | | | | | CD164L2 | 1.00 | 11075 | 3 | | | | | CELA2B | 1.00 |
| 10980 | 3 | | | | | | CD1B | 1.00 | 11076 | 3 | | | | | CELA3A | 1.00 |
| 10981 | 3 | | | | | | CD200R1L | 1.00 | 11077 | 3 | | | | | CELA3B | 1.00 |
| 10982 | 3 | | | | | | CD207 | 1.00 | 11078 | 3 | | | | | CELF3 | 1.00 |
| 10983 | 3 | | | | | | CD276 | 1.00 | 11079 | 3 | | | | | CELF4 | 1.00 |
| 10984 | 3 | | | | | | CD300LG | 1.00 | 11080 | 3 | | | | | CELF5 | 1.00 |
| 10985 | 3 | | | | | | CD34 | 1.00 | 11081 | 3 | | | | | CELF6 | 1.00 |
| 10986 | 3 | | | | | | CD5L | 1.00 | 11082 | 3 | | | | | CELP | 1.00 |
| 10987 | 3 | | | | | | CD80 | 1.00 | 11083 | 3 | | | | | CELSR1 | 1.00 |
| 10988 | 3 | | | | | | CD99P1 | 1.00 | 11084 | 3 | | | | | CELSR2 | 1.00 |
| 10989 | 3 | | | | | | CDC20B | 1.00 | 11085 | 3 | | | | | CELSR3 | 1.00 |
| 10990 | 3 | | | | | | CDC25A | 1.00 | 11086 | 3 | | | | | CEND1 | 1.00 |
| 10991 | 3 | | | | | | CDC25C | 1.00 | 11087 | 3 | | | | | CENPA | 1.00 |
| 10992 | 3 | | | | | | CDC42BPA | 1.00 | 11088 | 3 | | | | | CENPE | 1.00 |
| 10993 | 3 | | | | | | CDC42BPG | 1.00 | 11089 | 3 | | | | | CENPF | 1.00 |
| 10994 | 3 | | | | | | CDC42EP5 | 1.00 | 11090 | 3 | | | | | CENPI | 1.00 |
| 10995 | 3 | | | | | | CDC45 | 1.00 | 11091 | 3 | | | | | CENPJ | 1.00 |
| 10996 | 3 | | | | | | CDC6 | 1.00 | 11092 | 3 | | | | | CENPP | 1.00 |
| 10997 | 3 | | | | | | CDCA2 | 1.00 | 11093 | 3 | | | | | CENPQ | 1.00 |
| 10998 | 3 | | | | | | CDCA3 | 1.00 | 11094 | 3 | | | | | CENPVL1 | 1.00 |
| 10999 | 3 | | | | | | CDCA8 | 1.00 | 11095 | 3 | | | | | CEP112 | 1.00 |
| 11000 | 3 | | | | | | CDCP1 | 1.00 | 11096 | 3 | | | | | CEP128 | 1.00 |
| 11001 | 3 | | | | | | CDCP2 | 1.00 | 11097 | 3 | | | | | CEP152 | 1.00 |
| 11002 | 3 | | | | | | CDH1 | 1.00 | 11098 | 3 | | | | | CEP290 | 1.00 |
| 11003 | 3 | | | | | | CDH10 | 1.00 | 11099 | 3 | | | | | CEP57L1 | 1.00 |
| 11004 | 3 | | | | | | CDH11 | 1.00 | 11100 | 3 | | | | | CEP70 | 1.00 |
| 11005 | 3 | | | | | | CDH12 | 1.00 | 11101 | 3 | | | | | CEP72 | 1.00 |
| 11006 | 3 | | | | | | CDH13 | 1.00 | 11102 | 3 | | | | | CER1 | 1.00 |
| 11007 | 3 | | | | | | CDH15 | 1.00 | 11103 | 3 | | | | | CERCAM | 1.00 |
| 11008 | 3 | | | | | | CDH16 | 1.00 | 11104 | 3 | | | | | CERS1 | 1.00 |
| 11009 | 3 | | | | | | CDH17 | 1.00 | 11105 | 3 | | | | | CERS3 | 1.00 |
| 11010 | 3 | | | | | | CDH18 | 1.00 | 11106 | 3 | | | | | CES1P1 | 1.00 |
| 11011 | 3 | | | | | | CDH19 | 1.00 | 11107 | 3 | | | | | CES1P2 | 1.00 |
| 11012 | 3 | | | | | | CDH2 | 1.00 | 11108 | 3 | | | | | CES3 | 1.00 |
| 11013 | 3 | | | | | | CDH20 | 1.00 | 11109 | 3 | | | | | CES4A | 1.00 |
| 11014 | 3 | | | | | | CDH22 | 1.00 | 11110 | 3 | | | | | CES5A | 1.00 |
| 11015 | 3 | | | | | | CDH24 | 1.00 | 11111 | 3 | | | | | CES5AP1 | 1.00 |
| 11016 | 3 | | | | | | CDH26 | 1.00 | 11112 | 3 | | | | | CETN1 | 1.00 |
| 11017 | 3 | | | | | | CDH3 | 1.00 | 11113 | 3 | | | | | CETN4P | 1.00 |
| 11018 | 3 | | | | | | CDH4 | 1.00 | 11114 | 3 | | | | | CETP | 1.00 |
| 11019 | 3 | | | | | | CDH5 | 1.00 | 11115 | 3 | | | | | CFB | 1.00 |
| 11020 | 3 | | | | | | CDH6 | 1.00 | 11116 | 3 | | | | | CFC1 | 1.00 |
| 11021 | 3 | | | | | | CDH7 | 1.00 | 11117 | 3 | | | | | CFC1B | 1.00 |
| 11022 | 3 | | | | | | CDH8 | 1.00 | 11118 | 3 | | | | | CFHR1 | 1.00 |
| 11023 | 3 | | | | | | CDH9 | 1.00 | 11119 | 3 | | | | | CFHR2 | 1.00 |
| 11024 | 3 | | | | | | CDHR1 | 1.00 | 11120 | 3 | | | | | CFHR3 | 1.00 |
| 11025 | 3 | | | | | | CDHR2 | 1.00 | 11121 | 3 | | | | | CFHR4 | 1.00 |
| 11026 | 3 | | | | | | CDHR3 | 1.00 | 11122 | 3 | | | | | CFHR5 | 1.00 |
| 11027 | 3 | | | | | | CDHR4 | 1.00 | 11123 | 3 | | | | | CFI | 1.00 |
| 11028 | 3 | | | | | | CDHR5 | 1.00 | 11124 | 3 | | | | | CFL1P1 | 1.00 |
| 11029 | 3 | | | | | | CDK1 | 1.00 | 11125 | 3 | | | | | CFLAR-AS1 | 1.00 |
| 11030 | 3 | | | | | | CDK15 | 1.00 | 11126 | 3 | | | | | CFTR | 1.00 |
| 11031 | 3 | | | | | | CDK18 | 1.00 | 11127 | 3 | | | | | CGA | 1.00 |
| 11032 | 3 | | | | | | CDK20 | 1.00 | 11128 | 3 | | | | | CGB | 1.00 |
| 11033 | 3 | | | | | | CDK3 | 1.00 | 11129 | 3 | | | | | CGB1 | 1.00 |
| 11034 | 3 | | | | | | CDK5R2 | 1.00 | 11130 | 3 | | | | | CGB2 | 1.00 |

Fig. 41 - 59

| | | | | | | | | | | | | | |
|---|---|---|---|---|---|---|---|---|---|---|---|---|---|
| 11131 | 3 | | | | | CGB5 | 1.00 | 11227 | 3 | | | CLDN22 | 1.00 |
| 11132 | 3 | | | | | CGB7 | 1.00 | 11228 | 3 | | | CLDN24 | 1.00 |
| 11133 | 3 | | | | | CGB8 | 1.00 | 11229 | 3 | | | CLDN25 | 1.00 |
| 11134 | 3 | | | | | CGN | 1.00 | 11230 | 3 | | | CLDN3 | 1.00 |
| 11135 | 3 | | | | | CGNL1 | 1.00 | 11231 | 3 | | | CLDN4 | 1.00 |
| 11136 | 3 | | | | | CGREF1 | 1.00 | 11232 | 3 | | | CLDN6 | 1.00 |
| 11137 | 3 | | | | | CH25H | 1.00 | 11233 | 3 | | | CLDN7 | 1.00 |
| 11138 | 3 | | | | | CHAC1 | 1.00 | 11234 | 3 | | | CLDN8 | 1.00 |
| 11139 | 3 | | | | | CHAD | 1.00 | 11235 | 3 | | | CLEC14A | 1.00 |
| 11140 | 3 | | | | | CHADL | 1.00 | 11236 | 3 | | | CLEC18A | 1.00 |
| 11141 | 3 | | | | | CHAF1B | 1.00 | 11237 | 3 | | | CLEC18B | 1.00 |
| 11142 | 3 | | | | | CHAT | 1.00 | 11238 | 3 | | | CLEC18C | 1.00 |
| 11143 | 3 | | | | | CHCHD6 | 1.00 | 11239 | 3 | | | CLEC19A | 1.00 |
| 11144 | 3 | | | | | CHD5 | 1.00 | 11240 | 3 | | | CLEC1A | 1.00 |
| 11145 | 3 | | | | | CHDH | 1.00 | 11241 | 3 | | | CLEC2A | 1.00 |
| 11146 | 3 | | | | | CHEK1 | 1.00 | 11242 | 3 | | | CLEC3A | 1.00 |
| 11147 | 3 | | | | | CHEK2P2 | 1.00 | 11243 | 3 | | | CLEC4F | 1.00 |
| 11148 | 3 | | | | | CHGA | 1.00 | 11244 | 3 | | | CLEC4GP1 | 1.00 |
| 11149 | 3 | | | | | CHGB | 1.00 | 11245 | 3 | | | CLEC4M | 1.00 |
| 11150 | 3 | | | | | CHIA | 1.00 | 11246 | 3 | | | CLGN | 1.00 |
| 11151 | 3 | | | | | CHIT1 | 1.00 | 11247 | 3 | | | CLIC6 | 1.00 |
| 11152 | 3 | | | | | CHKB-CPT1B | 1.00 | 11248 | 3 | | | CLIP3 | 1.00 |
| 11153 | 3 | | | | | CHL1 | 1.00 | 11249 | 3 | | | CLLU1 | 1.00 |
| 11154 | 3 | | | | | CHMP4C | 1.00 | 11250 | 3 | | | CLLU1OS | 1.00 |
| 11155 | 3 | | | | | CHN1 | 1.00 | 11251 | 3 | | | CLMP | 1.00 |
| 11156 | 3 | | | | | CHODL | 1.00 | 11252 | 3 | | | CLNK | 1.00 |
| 11157 | 3 | | | | | CHODL-AS1 | 1.00 | 11253 | 3 | | | CLPS | 1.00 |
| 11158 | 3 | | | | | CHP2 | 1.00 | 11254 | 3 | | | CLPSL1 | 1.00 |
| 11159 | 3 | | | | | CHRD | 1.00 | 11255 | 3 | | | CLPSL2 | 1.00 |
| 11160 | 3 | | | | | CHRDL1 | 1.00 | 11256 | 3 | | | CLRN1 | 1.00 |
| 11161 | 3 | | | | | CHRDL2 | 1.00 | 11257 | 3 | | | CLRN1-AS1 | 1.00 |
| 11162 | 3 | | | | | CHRFAM7A | 1.00 | 11258 | 3 | | | CLRN2 | 1.00 |
| 11163 | 3 | | | | | CHRM1 | 1.00 | 11259 | 3 | | | CLRN3 | 1.00 |
| 11164 | 3 | | | | | CHRM2 | 1.00 | 11260 | 3 | | | CLSPN | 1.00 |
| 11165 | 3 | | | | | CHRM3 | 1.00 | 11261 | 3 | | | CLSTN2 | 1.00 |
| 11166 | 3 | | | | | CHRM4 | 1.00 | 11262 | 3 | | | CLUL1 | 1.00 |
| 11167 | 3 | | | | | CHRM5 | 1.00 | 11263 | 3 | | | CLVS1 | 1.00 |
| 11168 | 3 | | | | | CHRNA1 | 1.00 | 11264 | 3 | | | CLVS2 | 1.00 |
| 11169 | 3 | | | | | CHRNA10 | 1.00 | 11265 | 3 | | | CLYBL | 1.00 |
| 11170 | 3 | | | | | CHRNA2 | 1.00 | 11266 | 3 | | | CMA1 | 1.00 |
| 11171 | 3 | | | | | CHRNA3 | 1.00 | 11267 | 3 | | | CMYA5 | 1.00 |
| 11172 | 3 | | | | | CHRNA4 | 1.00 | 11268 | 3 | | | CN5H6.4 | 1.00 |
| 11173 | 3 | | | | | CHRNA5 | 1.00 | 11269 | 3 | | | CNBD1 | 1.00 |
| 11174 | 3 | | | | | CHRNA6 | 1.00 | 11270 | 3 | | | CNDP1 | 1.00 |
| 11175 | 3 | | | | | CHRNA7 | 1.00 | 11271 | 3 | | | CNGA1 | 1.00 |
| 11176 | 3 | | | | | CHRNA9 | 1.00 | 11272 | 3 | | | CNGA2 | 1.00 |
| 11177 | 3 | | | | | CHRNB2 | 1.00 | 11273 | 3 | | | CNGA3 | 1.00 |
| 11178 | 3 | | | | | CHRNB3 | 1.00 | 11274 | 3 | | | CNGA4 | 1.00 |
| 11179 | 3 | | | | | CHRNB4 | 1.00 | 11275 | 3 | | | CNGB1 | 1.00 |
| 11180 | 3 | | | | | CHRND | 1.00 | 11276 | 3 | | | CNGB3 | 1.00 |
| 11181 | 3 | | | | | CHRNG | 1.00 | 11277 | 3 | | | CNIH2 | 1.00 |
| 11182 | 3 | | | | | CHST1 | 1.00 | 11278 | 3 | | | CNIH3 | 1.00 |
| 11183 | 3 | | | | | CHST3 | 1.00 | 11279 | 3 | | | CNKSR1 | 1.00 |
| 11184 | 3 | | | | | CHST4 | 1.00 | 11280 | 3 | | | CNKSR3 | 1.00 |
| 11185 | 3 | | | | | CHST5 | 1.00 | 11281 | 3 | | | CNN1 | 1.00 |
| 11186 | 3 | | | | | CHST6 | 1.00 | 11282 | 3 | | | CNNM1 | 1.00 |
| 11187 | 3 | | | | | CHST8 | 1.00 | 11283 | 3 | | | CNPY1 | 1.00 |
| 11188 | 3 | | | | | CHST9 | 1.00 | 11284 | 3 | | | CNR1 | 1.00 |
| 11189 | 3 | | | | | CHST9-AS1 | 1.00 | 11285 | 3 | | | CNRIP1 | 1.00 |
| 11190 | 3 | | | | | CHSY3 | 1.00 | 11286 | 3 | | | CNTD2 | 1.00 |
| 11191 | 3 | | | | | CHTF18 | 1.00 | 11287 | 3 | | | CNTF | 1.00 |
| 11192 | 3 | | | | | CHURC1-FNTB | 1.00 | 11288 | 3 | | | CNTFR | 1.00 |
| 11193 | 3 | | | | | CIB2 | 1.00 | 11289 | 3 | | | CNTN1 | 1.00 |
| 11194 | 3 | | | | | CIB3 | 1.00 | 11290 | 3 | | | CNTN2 | 1.00 |
| 11195 | 3 | | | | | CIB4 | 1.00 | 11291 | 3 | | | CNTN3 | 1.00 |
| 11196 | 3 | | | | | CIDEA | 1.00 | 11292 | 3 | | | CNTN4 | 1.00 |
| 11197 | 3 | | | | | CIDEC | 1.00 | 11293 | 3 | | | CNTN5 | 1.00 |
| 11198 | 3 | | | | | CILP | 1.00 | 11294 | 3 | | | CNTN6 | 1.00 |
| 11199 | 3 | | | | | CILP2 | 1.00 | 11295 | 3 | | | CNTNAP1 | 1.00 |
| 11200 | 3 | | | | | CIT | 1.00 | 11296 | 3 | | | CNTNAP4 | 1.00 |
| 11201 | 3 | | | | | CITED1 | 1.00 | 11297 | 3 | | | CNTNAP5 | 1.00 |
| 11202 | 3 | | | | | CKAP2L | 1.00 | 11298 | 3 | | | COBL | 1.00 |
| 11203 | 3 | | | | | CKLF-CMTM1 | 1.00 | 11299 | 3 | | | COL10A1 | 1.00 |
| 11204 | 3 | | | | | CKM | 1.00 | 11300 | 3 | | | COL11A1 | 1.00 |
| 11205 | 3 | | | | | CKMT1A | 1.00 | 11301 | 3 | | | COL11A2 | 1.00 |
| 11206 | 3 | | | | | CKMT1B | 1.00 | 11302 | 3 | | | COL12A1 | 1.00 |
| 11207 | 3 | | | | | CKMT2 | 1.00 | 11303 | 3 | | | COL13A1 | 1.00 |
| 11208 | 3 | | | | | CLCA1 | 1.00 | 11304 | 3 | | | COL14A1 | 1.00 |
| 11209 | 3 | | | | | CLCA2 | 1.00 | 11305 | 3 | | | COL15A1 | 1.00 |
| 11210 | 3 | | | | | CLCA3P | 1.00 | 11306 | 3 | | | COL16A1 | 1.00 |
| 11211 | 3 | | | | | CLCA4 | 1.00 | 11307 | 3 | | | COL17A1 | 1.00 |
| 11212 | 3 | | | | | CLCN1 | 1.00 | 11308 | 3 | | | COL18A1-AS1 | 1.00 |
| 11213 | 3 | | | | | CLCN2 | 1.00 | 11309 | 3 | | | COL19A1 | 1.00 |
| 11214 | 3 | | | | | CLCNKA | 1.00 | 11310 | 3 | | | COL1A1 | 1.00 |
| 11215 | 3 | | | | | CLCNKB | 1.00 | 11311 | 3 | | | COL1A2 | 1.00 |
| 11216 | 3 | | | | | CLDN1 | 1.00 | 11312 | 3 | | | COL20A1 | 1.00 |
| 11217 | 3 | | | | | CLDN10 | 1.00 | 11313 | 3 | | | COL21A1 | 1.00 |
| 11218 | 3 | | | | | CLDN11 | 1.00 | 11314 | 3 | | | COL22A1 | 1.00 |
| 11219 | 3 | | | | | CLDN12 | 1.00 | 11315 | 3 | | | COL23A1 | 1.00 |
| 11220 | 3 | | | | | CLDN14 | 1.00 | 11316 | 3 | | | COL24A1 | 1.00 |
| 11221 | 3 | | | | | CLDN16 | 1.00 | 11317 | 3 | | | COL25A1 | 1.00 |
| 11222 | 3 | | | | | CLDN17 | 1.00 | 11318 | 3 | | | COL27A1 | 1.00 |
| 11223 | 3 | | | | | CLDN18 | 1.00 | 11319 | 3 | | | COL28A1 | 1.00 |
| 11224 | 3 | | | | | CLDN19 | 1.00 | 11320 | 3 | | | COL2A1 | 1.00 |
| 11225 | 3 | | | | | CLDN2 | 1.00 | 11321 | 3 | | | COL3A1 | 1.00 |
| 11226 | 3 | | | | | CLDN20 | 1.00 | 11322 | 3 | | | COL4A1 | 1.00 |

Fig. 41 - 60

| | | | | | | | | | | | | | | | | |
|---|---|---|---|---|---|---|---|---|---|---|---|---|---|---|---|---|
| 11323 | 3 | | | | | COL4A2 | 1.00 | 11419 | 3 | | | | | CRYBB3 | 1.00 |
| 11324 | 3 | | | | | COL4A3 | 1.00 | 11420 | 3 | | | | | CRYGA | 1.00 |
| 11325 | 3 | | | | | COL4A4 | 1.00 | 11421 | 3 | | | | | CRYGB | 1.00 |
| 11326 | 3 | | | | | COL4A5 | 1.00 | 11422 | 3 | | | | | CRYGC | 1.00 |
| 11327 | 3 | | | | | COL4A6 | 1.00 | 11423 | 3 | | | | | CRYGD | 1.00 |
| 11328 | 3 | | | | | COL5A1 | 1.00 | 11424 | 3 | | | | | CRYGN | 1.00 |
| 11329 | 3 | | | | | COL5A2 | 1.00 | 11425 | 3 | | | | | CRYGS | 1.00 |
| 11330 | 3 | | | | | COL5A3 | 1.00 | 11426 | 3 | | | | | CRYM | 1.00 |
| 11331 | 3 | | | | | COL6A1 | 1.00 | 11427 | 3 | | | | | CRYM-AS1 | 1.00 |
| 11332 | 3 | | | | | COL6A3 | 1.00 | 11428 | 3 | | | | | CSAG1 | 1.00 |
| 11333 | 3 | | | | | COL6A4P1 | 1.00 | 11429 | 3 | | | | | CSAG2 | 1.00 |
| 11334 | 3 | | | | | COL6A4P2 | 1.00 | 11430 | 3 | | | | | CSAG3 | 1.00 |
| 11335 | 3 | | | | | COL6A5 | 1.00 | 11431 | 3 | | | | | CSDC2 | 1.00 |
| 11336 | 3 | | | | | COL6A6 | 1.00 | 11432 | 3 | | | | | CSF2 | 1.00 |
| 11337 | 3 | | | | | COL7A1 | 1.00 | 11433 | 3 | | | | | CSF3 | 1.00 |
| 11338 | 3 | | | | | COL8A1 | 1.00 | 11434 | 3 | | | | | CSH1 | 1.00 |
| 11339 | 3 | | | | | COL9A1 | 1.00 | 11435 | 3 | | | | | CSH2 | 1.00 |
| 11340 | 3 | | | | | COLEC10 | 1.00 | 11436 | 3 | | | | | CSHL1 | 1.00 |
| 11341 | 3 | | | | | COLEC11 | 1.00 | 11437 | 3 | | | | | CSMD1 | 1.00 |
| 11342 | 3 | | | | | COLEC12 | 1.00 | 11438 | 3 | | | | | CSMD2 | 1.00 |
| 11343 | 3 | | | | | COMP | 1.00 | 11439 | 3 | | | | | CSMD3 | 1.00 |
| 11344 | 3 | | | | | COPZ2 | 1.00 | 11440 | 3 | | | | | CSN1S1 | 1.00 |
| 11345 | 3 | | | | | CORIN | 1.00 | 11441 | 3 | | | | | CSN1S2AP | 1.00 |
| 11346 | 3 | | | | | CORO2B | 1.00 | 11442 | 3 | | | | | CSN1S2BP | 1.00 |
| 11347 | 3 | | | | | CORO6 | 1.00 | 11443 | 3 | | | | | CSN2 | 1.00 |
| 11348 | 3 | | | | | CORO7-PAM16 | 1.00 | 11444 | 3 | | | | | CSN3 | 1.00 |
| 11349 | 3 | | | | | CORT | 1.00 | 11445 | 3 | | | | | CSNK1G2-AS1 | 1.00 |
| 11350 | 3 | | | | | COX4I2 | 1.00 | 11446 | 3 | | | | | CSPG4 | 1.00 |
| 11351 | 3 | | | | | COX6A2 | 1.00 | 11447 | 3 | | | | | CSPG4P1Y | 1.00 |
| 11352 | 3 | | | | | COX6B2 | 1.00 | 11448 | 3 | | | | | CSPG5 | 1.00 |
| 11353 | 3 | | | | | COX7A1 | 1.00 | 11449 | 3 | | | | | CSRNP3 | 1.00 |
| 11354 | 3 | | | | | COX7B2 | 1.00 | 11450 | 3 | | | | | CSRP2 | 1.00 |
| 11355 | 3 | | | | | COX8C | 1.00 | 11451 | 3 | | | | | CSRP3 | 1.00 |
| 11356 | 3 | | | | | CP | 1.00 | 11452 | 3 | | | | | CST1 | 1.00 |
| 11357 | 3 | | | | | CPA1 | 1.00 | 11453 | 3 | | | | | CST11 | 1.00 |
| 11358 | 3 | | | | | CPA2 | 1.00 | 11454 | 3 | | | | | CST2 | 1.00 |
| 11359 | 3 | | | | | CPA4 | 1.00 | 11455 | 3 | | | | | CST4 | 1.00 |
| 11360 | 3 | | | | | CPA5 | 1.00 | 11456 | 3 | | | | | CST5 | 1.00 |
| 11361 | 3 | | | | | CPA6 | 1.00 | 11457 | 3 | | | | | CST6 | 1.00 |
| 11362 | 3 | | | | | CPAMD8 | 1.00 | 11458 | 3 | | | | | CST8 | 1.00 |
| 11363 | 3 | | | | | CPB1 | 1.00 | 11459 | 3 | | | | | CST9 | 1.00 |
| 11364 | 3 | | | | | CPB2 | 1.00 | 11460 | 3 | | | | | CST9L | 1.00 |
| 11365 | 3 | | | | | CPE | 1.00 | 11461 | 3 | | | | | CSTL1 | 1.00 |
| 11366 | 3 | | | | | CPEB1 | 1.00 | 11462 | 3 | | | | | CSTT | 1.00 |
| 11367 | 3 | | | | | CPLX1 | 1.00 | 11463 | 3 | | | | | CT45A1 | 1.00 |
| 11368 | 3 | | | | | CPLX2 | 1.00 | 11464 | 3 | | | | | CT45A2 | 1.00 |
| 11369 | 3 | | | | | CPLX3 | 1.00 | 11465 | 3 | | | | | CT45A3 | 1.00 |
| 11370 | 3 | | | | | CPLX4 | 1.00 | 11466 | 3 | | | | | CT45A4 | 1.00 |
| 11371 | 3 | | | | | CPN1 | 1.00 | 11467 | 3 | | | | | CT45A5 | 1.00 |
| 11372 | 3 | | | | | CPN2 | 1.00 | 11468 | 3 | | | | | CT45A6 | 1.00 |
| 11373 | 3 | | | | | CPNE4 | 1.00 | 11469 | 3 | | | | | CT47A1 | 1.00 |
| 11374 | 3 | | | | | CPNE6 | 1.00 | 11470 | 3 | | | | | CT47A10 | 1.00 |
| 11375 | 3 | | | | | CPNE7 | 1.00 | 11471 | 3 | | | | | CT47A11 | 1.00 |
| 11376 | 3 | | | | | CPNE9 | 1.00 | 11472 | 3 | | | | | CT47A4 | 1.00 |
| 11377 | 3 | | | | | CPO | 1.00 | 11473 | 3 | | | | | CT47A5 | 1.00 |
| 11378 | 3 | | | | | CPS1 | 1.00 | 11474 | 3 | | | | | CT47A6 | 1.00 |
| 11379 | 3 | | | | | CPS1-IT1 | 1.00 | 11475 | 3 | | | | | CT47A7 | 1.00 |
| 11380 | 3 | | | | | CPSF4L | 1.00 | 11476 | 3 | | | | | CT47A8 | 1.00 |
| 11381 | 3 | | | | | CPT1C | 1.00 | 11477 | 3 | | | | | CT47B1 | 1.00 |
| 11382 | 3 | | | | | CPXCR1 | 1.00 | 11478 | 3 | | | | | CT62 | 1.00 |
| 11383 | 3 | | | | | CPXM1 | 1.00 | 11479 | 3 | | | | | CTAG1A | 1.00 |
| 11384 | 3 | | | | | CPXM2 | 1.00 | 11480 | 3 | | | | | CTAG1B | 1.00 |
| 11385 | 3 | | | | | CPZ | 1.00 | 11481 | 3 | | | | | CTAG2 | 1.00 |
| 11386 | 3 | | | | | CR1L | 1.00 | 11482 | 3 | | | | | CTAGE6P | 1.00 |
| 11387 | 3 | | | | | CRABP1 | 1.00 | 11483 | 3 | | | | | CTAGE9 | 1.00 |
| 11388 | 3 | | | | | CRABP2 | 1.00 | 11484 | 3 | | | | | CTCFL | 1.00 |
| 11389 | 3 | | | | | CRB1 | 1.00 | 11485 | 3 | | | | | CTF1 | 1.00 |
| 11390 | 3 | | | | | CRB2 | 1.00 | 11486 | 3 | | | | | CTGF | 1.00 |
| 11391 | 3 | | | | | CRB3 | 1.00 | 11487 | 3 | | | | | CTH | 1.00 |
| 11392 | 3 | | | | | CRCT1 | 1.00 | 11488 | 3 | | | | | CTHRC1 | 1.00 |
| 11393 | 3 | | | | | CREB3L1 | 1.00 | 11489 | 3 | | | | | CTNNA2 | 1.00 |
| 11394 | 3 | | | | | CREB3L3 | 1.00 | 11490 | 3 | | | | | CTNNA3 | 1.00 |
| 11395 | 3 | | | | | CREG2 | 1.00 | 11491 | 3 | | | | | CTNND2 | 1.00 |
| 11396 | 3 | | | | | CRH | 1.00 | 11492 | 3 | | | | | CTRB1 | 1.00 |
| 11397 | 3 | | | | | CRHBP | 1.00 | 11493 | 3 | | | | | CTRB2 | 1.00 |
| 11398 | 3 | | | | | CRHR1 | 1.00 | 11494 | 3 | | | | | CTRC | 1.00 |
| 11399 | 3 | | | | | CRHR2 | 1.00 | 11495 | 3 | | | | | CTSL1P2 | 1.00 |
| 11400 | 3 | | | | | CRIP3 | 1.00 | 11496 | 3 | | | | | CTSL1P8 | 1.00 |
| 11401 | 3 | | | | | CRISP1 | 1.00 | 11497 | 3 | | | | | CTSL2 | 1.00 |
| 11402 | 3 | | | | | CRISP2 | 1.00 | 11498 | 3 | | | | | CTSL3 | 1.00 |
| 11403 | 3 | | | | | CRISPLD1 | 1.00 | 11499 | 3 | | | | | CTTNBP2 | 1.00 |
| 11404 | 3 | | | | | CRLF1 | 1.00 | 11500 | 3 | | | | | CTXN1 | 1.00 |
| 11405 | 3 | | | | | CRLF2 | 1.00 | 11501 | 3 | | | | | CTXN2 | 1.00 |
| 11406 | 3 | | | | | CRMP1 | 1.00 | 11502 | 3 | | | | | CTXN3 | 1.00 |
| 11407 | 3 | | | | | CRNDE | 1.00 | 11503 | 3 | | | | | CUBN | 1.00 |
| 11408 | 3 | | | | | CRNN | 1.00 | 11504 | 3 | | | | | CUX2 | 1.00 |
| 11409 | 3 | | | | | CRP | 1.00 | 11505 | 3 | | | | | CUZD1 | 1.00 |
| 11410 | 3 | | | | | CRTAC1 | 1.00 | 11506 | 3 | | | | | CWH43 | 1.00 |
| 11411 | 3 | | | | | CRX | 1.00 | 11507 | 3 | | | | | CX3CL1 | 1.00 |
| 11412 | 3 | | | | | CRYAA | 1.00 | 11508 | 3 | | | | | CXADR | 1.00 |
| 11413 | 3 | | | | | CRYAB | 1.00 | 11509 | 3 | | | | | CXADRP2 | 1.00 |
| 11414 | 3 | | | | | CRYBA1 | 1.00 | 11510 | 3 | | | | | CXADRP3 | 1.00 |
| 11415 | 3 | | | | | CRYBA2 | 1.00 | 11511 | 3 | | | | | CXCL11 | 1.00 |
| 11416 | 3 | | | | | CRYBA4 | 1.00 | 11512 | 3 | | | | | CXCL12 | 1.00 |
| 11417 | 3 | | | | | CRYBB1 | 1.00 | 11513 | 3 | | | | | CXCL13 | 1.00 |
| 11418 | 3 | | | | | CRYBB2 | 1.00 | 11514 | 3 | | | | | CXCL14 | 1.00 |

Fig. 41 - 61

| | | | | | | | | | | | | |
|---|---|---|---|---|---|---|---|---|---|---|---|---|
| 11515 | 3 | | | | | CXCL17 | 1.00 | 11611 | 3 | | DACT2 | 1.00 |
| 11516 | 3 | | | | | CXCL2 | 1.00 | 11612 | 3 | | DACT3 | 1.00 |
| 11517 | 3 | | | | | CXCL3 | 1.00 | 11613 | 3 | | DAND5 | 1.00 |
| 11518 | 3 | | | | | CXCL6 | 1.00 | 11614 | 3 | | DAO | 1.00 |
| 11519 | 3 | | | | | CXCL9 | 1.00 | 11615 | 3 | | DAOA | 1.00 |
| 11520 | 3 | | | | | CXXC11 | 1.00 | 11616 | 3 | | DAOA-AS1 | 1.00 |
| 11521 | 3 | | | | | CXXC1P1 | 1.00 | 11617 | 3 | | DAPL1 | 1.00 |
| 11522 | 3 | | | | | CXXC4 | 1.00 | 11618 | 3 | | DAZ1 | 1.00 |
| 11523 | 3 | | | | | CXorf1 | 1.00 | 11619 | 3 | | DAZ2 | 1.00 |
| 11524 | 3 | | | | | CXorf22 | 1.00 | 11620 | 3 | | DAZ3 | 1.00 |
| 11525 | 3 | | | | | CXorf27 | 1.00 | 11621 | 3 | | DAZ4 | 1.00 |
| 11526 | 3 | | | | | CXorf28 | 1.00 | 11622 | 3 | | DAZL | 1.00 |
| 11527 | 3 | | | | | CXorf30 | 1.00 | 11623 | 3 | | DBC1 | 1.00 |
| 11528 | 3 | | | | | CXorf31 | 1.00 | 11624 | 3 | | DBH | 1.00 |
| 11529 | 3 | | | | | CXorf36 | 1.00 | 11625 | 3 | | DBIL5P | 1.00 |
| 11530 | 3 | | | | | CXorf41 | 1.00 | 11626 | 3 | | DBIL5P2 | 1.00 |
| 11531 | 3 | | | | | CXorf48 | 1.00 | 11627 | 3 | | DBX1 | 1.00 |
| 11532 | 3 | | | | | CXorf49B | 1.00 | 11628 | 3 | | DBX2 | 1.00 |
| 11533 | 3 | | | | | CXorf51A | 1.00 | 11629 | 3 | | DCAF12L1 | 1.00 |
| 11534 | 3 | | | | | CXorf57 | 1.00 | 11630 | 3 | | DCAF12L2 | 1.00 |
| 11535 | 3 | | | | | CXorf58 | 1.00 | 11631 | 3 | | DCAF4L1 | 1.00 |
| 11536 | 3 | | | | | CXorf59 | 1.00 | 11632 | 3 | | DCAF4L2 | 1.00 |
| 11537 | 3 | | | | | CXorf61 | 1.00 | 11633 | 3 | | DCAF8L1 | 1.00 |
| 11538 | 3 | | | | | CXorf64 | 1.00 | 11634 | 3 | | DCAF8L2 | 1.00 |
| 11539 | 3 | | | | | CXorf65 | 1.00 | 11635 | 3 | | DCBLD1 | 1.00 |
| 11540 | 3 | | | | | CXorf66 | 1.00 | 11636 | 3 | | DCBLD2 | 1.00 |
| 11541 | 3 | | | | | CXorf68 | 1.00 | 11637 | 3 | | DCC | 1.00 |
| 11542 | 3 | | | | | CXorf69 | 1.00 | 11638 | 3 | | DCD | 1.00 |
| 11543 | 3 | | | | | CYB5R2 | 1.00 | 11639 | 3 | | DCDC1 | 1.00 |
| 11544 | 3 | | | | | CYCSP52 | 1.00 | 11640 | 3 | | DCDC2 | 1.00 |
| 11545 | 3 | | | | | CYGB | 1.00 | 11641 | 3 | | DCDC2B | 1.00 |
| 11546 | 3 | | | | | CYLC1 | 1.00 | 11642 | 3 | | DCDC5 | 1.00 |
| 11547 | 3 | | | | | CYLC2 | 1.00 | 11643 | 3 | | DCHS2 | 1.00 |
| 11548 | 3 | | | | | CYMP | 1.00 | 11644 | 3 | | DCLK1 | 1.00 |
| 11549 | 3 | | | | | CYP11A1 | 1.00 | 11645 | 3 | | DCLK2 | 1.00 |
| 11550 | 3 | | | | | CYP11B1 | 1.00 | 11646 | 3 | | DCLK3 | 1.00 |
| 11551 | 3 | | | | | CYP11B2 | 1.00 | 11647 | 3 | | DCN | 1.00 |
| 11552 | 3 | | | | | CYP17A1 | 1.00 | 11648 | 3 | | DCST1 | 1.00 |
| 11553 | 3 | | | | | CYP19A1 | 1.00 | 11649 | 3 | | DCST2 | 1.00 |
| 11554 | 3 | | | | | CYP1A1 | 1.00 | 11650 | 3 | | DCT | 1.00 |
| 11555 | 3 | | | | | CYP1A2 | 1.00 | 11651 | 3 | | DCUN1D5 | 1.00 |
| 11556 | 3 | | | | | CYP1B1-AS1 | 1.00 | 11652 | 3 | | DCX | 1.00 |
| 11557 | 3 | | | | | CYP21A1P | 1.00 | 11653 | 3 | | DDAH1 | 1.00 |
| 11558 | 3 | | | | | CYP21A2 | 1.00 | 11654 | 3 | | DDC | 1.00 |
| 11559 | 3 | | | | | CYP24A1 | 1.00 | 11655 | 3 | | DDI1 | 1.00 |
| 11560 | 3 | | | | | CYP26A1 | 1.00 | 11656 | 3 | | DDIT4L | 1.00 |
| 11561 | 3 | | | | | CYP26B1 | 1.00 | 11657 | 3 | | DDN | 1.00 |
| 11562 | 3 | | | | | CYP26C1 | 1.00 | 11658 | 3 | | DDR1 | 1.00 |
| 11563 | 3 | | | | | CYP27B1 | 1.00 | 11659 | 3 | | DDR2 | 1.00 |
| 11564 | 3 | | | | | CYP27C1 | 1.00 | 11660 | 3 | | DDX12P | 1.00 |
| 11565 | 3 | | | | | CYP2A13 | 1.00 | 11661 | 3 | | DDX25 | 1.00 |
| 11566 | 3 | | | | | CYP2A6 | 1.00 | 11662 | 3 | | DDX4 | 1.00 |
| 11567 | 3 | | | | | CYP2A7 | 1.00 | 11663 | 3 | | DDX43 | 1.00 |
| 11568 | 3 | | | | | CYP2B6 | 1.00 | 11664 | 3 | | DDX53 | 1.00 |
| 11569 | 3 | | | | | CYP2B7P1 | 1.00 | 11665 | 3 | | 42705 | 1.00 |
| 11570 | 3 | | | | | CYP2C18 | 1.00 | 11666 | 3 | | DEFA1 | 1.00 |
| 11571 | 3 | | | | | CYP2C19 | 1.00 | 11667 | 3 | | DEFA10P | 1.00 |
| 11572 | 3 | | | | | CYP2C8 | 1.00 | 11668 | 3 | | DEFA5 | 1.00 |
| 11573 | 3 | | | | | CYP2C9 | 1.00 | 11669 | 3 | | DEFA6 | 1.00 |
| 11574 | 3 | | | | | CYP2D6 | 1.00 | 11670 | 3 | | DEFB1 | 1.00 |
| 11575 | 3 | | | | | CYP2D7P1 | 1.00 | 11671 | 3 | | DEFB103A | 1.00 |
| 11576 | 3 | | | | | CYP2E1 | 1.00 | 11672 | 3 | | DEFB103B | 1.00 |
| 11577 | 3 | | | | | CYP2F1 | 1.00 | 11673 | 3 | | DEFB104B | 1.00 |
| 11578 | 3 | | | | | CYP2G1P | 1.00 | 11674 | 3 | | DEFB105B | 1.00 |
| 11579 | 3 | | | | | CYP2J2 | 1.00 | 11675 | 3 | | DEFB106B | 1.00 |
| 11580 | 3 | | | | | CYP2W1 | 1.00 | 11676 | 3 | | DEFB107A | 1.00 |
| 11581 | 3 | | | | | CYP39A1 | 1.00 | 11677 | 3 | | DEFB107B | 1.00 |
| 11582 | 3 | | | | | CYP3A4 | 1.00 | 11678 | 3 | | DEFB108B | 1.00 |
| 11583 | 3 | | | | | CYP3A43 | 1.00 | 11679 | 3 | | DEFB109P1B | 1.00 |
| 11584 | 3 | | | | | CYP3A5 | 1.00 | 11680 | 3 | | DEFB110 | 1.00 |
| 11585 | 3 | | | | | CYP3A7 | 1.00 | 11681 | 3 | | DEFB112 | 1.00 |
| 11586 | 3 | | | | | CYP3A7-CYP3AP1 | 1.00 | 11682 | 3 | | DEFB113 | 1.00 |
| 11587 | 3 | | | | | CYP46A1 | 1.00 | 11683 | 3 | | DEFB114 | 1.00 |
| 11588 | 3 | | | | | CYP4A11 | 1.00 | 11684 | 3 | | DEFB115 | 1.00 |
| 11589 | 3 | | | | | CYP4A22 | 1.00 | 11685 | 3 | | DEFB116 | 1.00 |
| 11590 | 3 | | | | | CYP4B1 | 1.00 | 11686 | 3 | | DEFB118 | 1.00 |
| 11591 | 3 | | | | | CYP4F11 | 1.00 | 11687 | 3 | | DEFB119 | 1.00 |
| 11592 | 3 | | | | | CYP4F12 | 1.00 | 11688 | 3 | | DEFB121 | 1.00 |
| 11593 | 3 | | | | | CYP4F24P | 1.00 | 11689 | 3 | | DEFB122 | 1.00 |
| 11594 | 3 | | | | | CYP4F30P | 1.00 | 11690 | 3 | | DEFB123 | 1.00 |
| 11595 | 3 | | | | | CYP4F35P | 1.00 | 11691 | 3 | | DEFB124 | 1.00 |
| 11596 | 3 | | | | | CYP4F8 | 1.00 | 11692 | 3 | | DEFB125 | 1.00 |
| 11597 | 3 | | | | | CYP4X1 | 1.00 | 11693 | 3 | | DEFB126 | 1.00 |
| 11598 | 3 | | | | | CYP4Z1 | 1.00 | 11694 | 3 | | DEFB127 | 1.00 |
| 11599 | 3 | | | | | CYP4Z2P | 1.00 | 11695 | 3 | | DEFB128 | 1.00 |
| 11600 | 3 | | | | | CYP7A1 | 1.00 | 11696 | 3 | | DEFB129 | 1.00 |
| 11601 | 3 | | | | | CYP7B1 | 1.00 | 11697 | 3 | | DEFB130 | 1.00 |
| 11602 | 3 | | | | | CYP8B1 | 1.00 | 11698 | 3 | | DEFB131 | 1.00 |
| 11603 | 3 | | | | | CYR61 | 1.00 | 11699 | 3 | | DEFB132 | 1.00 |
| 11604 | 3 | | | | | CYS1 | 1.00 | 11700 | 3 | | DEFB133 | 1.00 |
| 11605 | 3 | | | | | CYTL1 | 1.00 | 11701 | 3 | | DEFB134 | 1.00 |
| 11606 | 3 | | | | | CYYR1 | 1.00 | 11702 | 3 | | DEFB135 | 1.00 |
| 11607 | 3 | | | | | D21S2088E | 1.00 | 11703 | 3 | | DEFB136 | 1.00 |
| 11608 | 3 | | | | | DAB1 | 1.00 | 11704 | 3 | | DEFB4A | 1.00 |
| 11609 | 3 | | | | | DAB2IP | 1.00 | 11705 | 3 | | DEFB4B | 1.00 |
| 11610 | 3 | | | | | DACH2 | 1.00 | 11706 | 3 | | DEFT1P | 1.00 |

Fig. 41 - 62

| | | | | | | | | | | | | | | | | |
|---|---|---|---|---|---|---|---|---|---|---|---|---|---|---|---|---|
| 11707 | 3 | | | | | DEGS2 | 1.00 | 11803 | 3 | | | | | DNAH14 | 1.00 |
| 11708 | 3 | | | | | DENND2A | 1.00 | 11804 | 3 | | | | | DNAH17 | 1.00 |
| 11709 | 3 | | | | | DENND2C | 1.00 | 11805 | 3 | | | | | DNAH2 | 1.00 |
| 11710 | 3 | | | | | DENND5B | 1.00 | 11806 | 3 | | | | | DNAH3 | 1.00 |
| 11711 | 3 | | | | | DEPDC1 | 1.00 | 11807 | 3 | | | | | DNAH5 | 1.00 |
| 11712 | 3 | | | | | DEPDC1B | 1.00 | 11808 | 3 | | | | | DNAH6 | 1.00 |
| 11713 | 3 | | | | | DEPDC4 | 1.00 | 11809 | 3 | | | | | DNAH7 | 1.00 |
| 11714 | 3 | | | | | DEPDC7 | 1.00 | 11810 | 3 | | | | | DNAH8 | 1.00 |
| 11715 | 3 | | | | | DEPTOR | 1.00 | 11811 | 3 | | | | | DNAH9 | 1.00 |
| 11716 | 3 | | | | | DFNA5 | 1.00 | 11812 | 3 | | | | | DNAI1 | 1.00 |
| 11717 | 3 | | | | | DFNB59 | 1.00 | 11813 | 3 | | | | | DNAI2 | 1.00 |
| 11718 | 3 | | | | | DGAT2L6 | 1.00 | 11814 | 3 | | | | | DNAJA1P5 | 1.00 |
| 11719 | 3 | | | | | DGCR10 | 1.00 | 11815 | 3 | | | | | DNAJB13 | 1.00 |
| 11720 | 3 | | | | | DGCR5 | 1.00 | 11816 | 3 | | | | | DNAJB3 | 1.00 |
| 11721 | 3 | | | | | DGCR9 | 1.00 | 11817 | 3 | | | | | DNAJB7 | 1.00 |
| 11722 | 3 | | | | | DGKB | 1.00 | 11818 | 3 | | | | | DNAJB8 | 1.00 |
| 11723 | 3 | | | | | DGKH | 1.00 | 11819 | 3 | | | | | DNAJB8-AS1 | 1.00 |
| 11724 | 3 | | | | | DGKI | 1.00 | 11820 | 3 | | | | | DNAJC12 | 1.00 |
| 11725 | 3 | | | | | DGKK | 1.00 | 11821 | 3 | | | | | DNAJC22 | 1.00 |
| 11726 | 3 | | | | | DHDH | 1.00 | 11822 | 3 | | | | | DNAJC25-GNG10 | 1.00 |
| 11727 | 3 | | | | | DHH | 1.00 | 11823 | 3 | | | | | DNAJC27-AS1 | 1.00 |
| 11728 | 3 | | | | | DHRS2 | 1.00 | 11824 | 3 | | | | | DNAJC28 | 1.00 |
| 11729 | 3 | | | | | DHRS7C | 1.00 | 11825 | 3 | | | | | DNAJC5B | 1.00 |
| 11730 | 3 | | | | | DIAPH3 | 1.00 | 11826 | 3 | | | | | DNAJC5G | 1.00 |
| 11731 | 3 | | | | | DIO1 | 1.00 | 11827 | 3 | | | | | DNAJC6 | 1.00 |
| 11732 | 3 | | | | | DIO2 | 1.00 | 11828 | 3 | | | | | DNAL1 | 1.00 |
| 11733 | 3 | | | | | DIO3 | 1.00 | 11829 | 3 | | | | | DNALI1 | 1.00 |
| 11734 | 3 | | | | | DIO3OS | 1.00 | 11830 | 3 | | | | | DNASE1L2 | 1.00 |
| 11735 | 3 | | | | | DIP2C | 1.00 | 11831 | 3 | | | | | DNASE1L3 | 1.00 |
| 11736 | 3 | | | | | DIRAS1 | 1.00 | 11832 | 3 | | | | | DNASE2B | 1.00 |
| 11737 | 3 | | | | | DIRAS2 | 1.00 | 11833 | 3 | | | | | DNER | 1.00 |
| 11738 | 3 | | | | | DIRAS3 | 1.00 | 11834 | 3 | | | | | DNHD1 | 1.00 |
| 11739 | 3 | | | | | DIRC1 | 1.00 | 11835 | 3 | | | | | DNM1 | 1.00 |
| 11740 | 3 | | | | | DIRC3 | 1.00 | 11836 | 3 | | | | | DNM1P35 | 1.00 |
| 11741 | 3 | | | | | DISC2 | 1.00 | 11837 | 3 | | | | | DNM1P41 | 1.00 |
| 11742 | 3 | | | | | DISP2 | 1.00 | 11838 | 3 | | | | | DNM1P46 | 1.00 |
| 11743 | 3 | | | | | DIXDC1 | 1.00 | 11839 | 3 | | | | | DNM3OS | 1.00 |
| 11744 | 3 | | | | | DKFZP434A062 | 1.00 | 11840 | 3 | | | | | DNM8P-AS1 | 1.00 |
| 11745 | 3 | | | | | DKFZP434H168 | 1.00 | 11841 | 3 | | | | | DNMT3B | 1.00 |
| 11746 | 3 | | | | | DKFZP434I0714 | 1.00 | 11842 | 3 | | | | | DNMT3L | 1.00 |
| 11747 | 3 | | | | | DKFZP434K028 | 1.00 | 11843 | 3 | | | | | DNTT | 1.00 |
| 11748 | 3 | | | | | DKFZP434L187 | 1.00 | 11844 | 3 | | | | | DOC2A | 1.00 |
| 11749 | 3 | | | | | DKFZP564C196 | 1.00 | 11845 | 3 | | | | | DOC2B | 1.00 |
| 11750 | 3 | | | | | DKFZp434J0226 | 1.00 | 11846 | 3 | | | | | DOC2GP | 1.00 |
| 11751 | 3 | | | | | DKFZp434L192 | 1.00 | 11847 | 3 | | | | | DOCK1 | 1.00 |
| 11752 | 3 | | | | | DKFZp451B082 | 1.00 | 11848 | 3 | | | | | DOCK3 | 1.00 |
| 11753 | 3 | | | | | DKFZp566F0947 | 1.00 | 11849 | 3 | | | | | DOCK4 | 1.00 |
| 11754 | 3 | | | | | DKFZp686D0853 | 1.00 | 11850 | 3 | | | | | DOCK6 | 1.00 |
| 11755 | 3 | | | | | DKFZp686K1684 | 1.00 | 11851 | 3 | | | | | DOCK7 | 1.00 |
| 11756 | 3 | | | | | DKFZp686O1327 | 1.00 | 11852 | 3 | | | | | DOK5 | 1.00 |
| 11757 | 3 | | | | | DKFZp779M0652 | 1.00 | 11853 | 3 | | | | | DOK6 | 1.00 |
| 11758 | 3 | | | | | DKK1 | 1.00 | 11854 | 3 | | | | | DOK7 | 1.00 |
| 11759 | 3 | | | | | DKK2 | 1.00 | 11855 | 3 | | | | | DONSON | 1.00 |
| 11760 | 3 | | | | | DKK3 | 1.00 | 11856 | 3 | | | | | DPCR1 | 1.00 |
| 11761 | 3 | | | | | DKK4 | 1.00 | 11857 | 3 | | | | | DPEP1 | 1.00 |
| 11762 | 3 | | | | | DKKL1 | 1.00 | 11858 | 3 | | | | | DPF1 | 1.00 |
| 11763 | 3 | | | | | DLC1 | 1.00 | 11859 | 3 | | | | | DPF3 | 1.00 |
| 11764 | 3 | | | | | DLEC1 | 1.00 | 11860 | 3 | | | | | DPP10 | 1.00 |
| 11765 | 3 | | | | | DLEU2L | 1.00 | 11861 | 3 | | | | | DPP6 | 1.00 |
| 11766 | 3 | | | | | DLG2 | 1.00 | 11862 | 3 | | | | | DPPA2 | 1.00 |
| 11767 | 3 | | | | | DLGAP1 | 1.00 | 11863 | 3 | | | | | DPPA3 | 1.00 |
| 11768 | 3 | | | | | DLGAP2 | 1.00 | 11864 | 3 | | | | | DPPA4 | 1.00 |
| 11769 | 3 | | | | | DLGAP3 | 1.00 | 11865 | 3 | | | | | DPPA5 | 1.00 |
| 11770 | 3 | | | | | DLGAP5 | 1.00 | 11866 | 3 | | | | | DPRX | 1.00 |
| 11771 | 3 | | | | | DLK1 | 1.00 | 11867 | 3 | | | | | DPRXP4 | 1.00 |
| 11772 | 3 | | | | | DLK2 | 1.00 | 11868 | 3 | | | | | DPT | 1.00 |
| 11773 | 3 | | | | | DLL1 | 1.00 | 11869 | 3 | | | | | DPY19L1P1 | 1.00 |
| 11774 | 3 | | | | | DLL3 | 1.00 | 11870 | 3 | | | | | DPY19L2 | 1.00 |
| 11775 | 3 | | | | | DLL4 | 1.00 | 11871 | 3 | | | | | DPY19L2P1 | 1.00 |
| 11776 | 3 | | | | | DLX1 | 1.00 | 11872 | 3 | | | | | DPY19L2P2 | 1.00 |
| 11777 | 3 | | | | | DLX2 | 1.00 | 11873 | 3 | | | | | DPY19L2P3 | 1.00 |
| 11778 | 3 | | | | | DLX3 | 1.00 | 11874 | 3 | | | | | DPY19L2P4 | 1.00 |
| 11779 | 3 | | | | | DLX4 | 1.00 | 11875 | 3 | | | | | DPYS | 1.00 |
| 11780 | 3 | | | | | DLX5 | 1.00 | 11876 | 3 | | | | | DPYSL3 | 1.00 |
| 11781 | 3 | | | | | DLX6 | 1.00 | 11877 | 3 | | | | | DPYSL4 | 1.00 |
| 11782 | 3 | | | | | DLX6-AS1 | 1.00 | 11878 | 3 | | | | | DPYSL5 | 1.00 |
| 11783 | 3 | | | | | DMBT1 | 1.00 | 11879 | 3 | | | | | DQX1 | 1.00 |
| 11784 | 3 | | | | | DMBX1 | 1.00 | 11880 | 3 | | | | | DRD1 | 1.00 |
| 11785 | 3 | | | | | DMC1 | 1.00 | 11881 | 3 | | | | | DRD2 | 1.00 |
| 11786 | 3 | | | | | DMD | 1.00 | 11882 | 3 | | | | | DRD3 | 1.00 |
| 11787 | 3 | | | | | DMGDH | 1.00 | 11883 | 3 | | | | | DRD4 | 1.00 |
| 11788 | 3 | | | | | DMP1 | 1.00 | 11884 | 3 | | | | | DRD5 | 1.00 |
| 11789 | 3 | | | | | DMRT1 | 1.00 | 11885 | 3 | | | | | DRGX | 1.00 |
| 11790 | 3 | | | | | DMRT2 | 1.00 | 11886 | 3 | | | | | DRP2 | 1.00 |
| 11791 | 3 | | | | | DMRT3 | 1.00 | 11887 | 3 | | | | | DSC3 | 1.00 |
| 11792 | 3 | | | | | DMRTA1 | 1.00 | 11888 | 3 | | | | | DSCAM | 1.00 |
| 11793 | 3 | | | | | DMRTA2 | 1.00 | 11889 | 3 | | | | | DSCAM-AS1 | 1.00 |
| 11794 | 3 | | | | | DMRTB1 | 1.00 | 11890 | 3 | | | | | DSCAML1 | 1.00 |
| 11795 | 3 | | | | | DMRTC1B | 1.00 | 11891 | 3 | | | | | DSCC1 | 1.00 |
| 11796 | 3 | | | | | DMRTC2 | 1.00 | 11892 | 3 | | | | | DSCR10 | 1.00 |
| 11797 | 3 | | | | | DNA2 | 1.00 | 11893 | 3 | | | | | DSCR4 | 1.00 |
| 11798 | 3 | | | | | DNAAF1 | 1.00 | 11894 | 3 | | | | | DSCR6 | 1.00 |
| 11799 | 3 | | | | | DNAH1 | 1.00 | 11895 | 3 | | | | | DSCR8 | 1.00 |
| 11800 | 3 | | | | | DNAH10 | 1.00 | 11896 | 3 | | | | | DSCR9 | 1.00 |
| 11801 | 3 | | | | | DNAH11 | 1.00 | 11897 | 3 | | | | | DSEL | 1.00 |
| 11802 | 3 | | | | | DNAH12 | 1.00 | 11898 | 3 | | | | | DSG1 | 1.00 |

Fig. 41 - 63

| | | | | | | | | | | | | | |
|---|---|---|---|---|---|---|---|---|---|---|---|---|---|
| 11899 | 3 | | | | | DSG2 | 1.00 | 11995 | 3 | | | EGR3 | 1.00 |
| 11900 | 3 | | | | | DSG3 | 1.00 | 11996 | 3 | | | EGR4 | 1.00 |
| 11901 | 3 | | | | | DSG4 | 1.00 | 11997 | 3 | | | EHD2 | 1.00 |
| 11902 | 3 | | | | | DSP | 1.00 | 11998 | 3 | | | EHF | 1.00 |
| 11903 | 3 | | | | | DSPP | 1.00 | 11999 | 3 | | | EIF3CL | 1.00 |
| 11904 | 3 | | | | | DST | 1.00 | 12000 | 3 | | | EIF4E1B | 1.00 |
| 11905 | 3 | | | | | DTL | 1.00 | 12001 | 3 | | | ELAVL2 | 1.00 |
| 11906 | 3 | | | | | DTNA | 1.00 | 12002 | 3 | | | ELAVL3 | 1.00 |
| 11907 | 3 | | | | | DUOX1 | 1.00 | 12003 | 3 | | | ELAVL4 | 1.00 |
| 11908 | 3 | | | | | DUOX2 | 1.00 | 12004 | 3 | | | ELF3 | 1.00 |
| 11909 | 3 | | | | | DUOXA1 | 1.00 | 12005 | 3 | | | ELF5 | 1.00 |
| 11910 | 3 | | | | | DUOXA2 | 1.00 | 12006 | 3 | | | ELFN1 | 1.00 |
| 11911 | 3 | | | | | DUPD1 | 1.00 | 12007 | 3 | | | ELFN2 | 1.00 |
| 11912 | 3 | | | | | DUSP13 | 1.00 | 12008 | 3 | | | ELL3 | 1.00 |
| 11913 | 3 | | | | | DUSP15 | 1.00 | 12009 | 3 | | | ELMO3 | 1.00 |
| 11914 | 3 | | | | | DUSP21 | 1.00 | 12010 | 3 | | | ELMOD1 | 1.00 |
| 11915 | 3 | | | | | DUSP26 | 1.00 | 12011 | 3 | | | ELN | 1.00 |
| 11916 | 3 | | | | | DUSP27 | 1.00 | 12012 | 3 | | | ELOVL2 | 1.00 |
| 11917 | 3 | | | | | DUSP4 | 1.00 | 12013 | 3 | | | ELOVL3 | 1.00 |
| 11918 | 3 | | | | | DUSP5P | 1.00 | 12014 | 3 | | | ELOVL4 | 1.00 |
| 11919 | 3 | | | | | DUSP8 | 1.00 | 12015 | 3 | | | ELSPBP1 | 1.00 |
| 11920 | 3 | | | | | DUSP9 | 1.00 | 12016 | 3 | | | ELTD1 | 1.00 |
| 11921 | 3 | | | | | DUX2 | 1.00 | 12017 | 3 | | | EMCN | 1.00 |
| 11922 | 3 | | | | | DUX4 | 1.00 | 12018 | 3 | | | EME1 | 1.00 |
| 11923 | 3 | | | | | DUX4L2 | 1.00 | 12019 | 3 | | | EME2 | 1.00 |
| 11924 | 3 | | | | | DUX4L3 | 1.00 | 12020 | 3 | | | EMID1 | 1.00 |
| 11925 | 3 | | | | | DUX4L4 | 1.00 | 12021 | 3 | | | EMID2 | 1.00 |
| 11926 | 3 | | | | | DUX4L5 | 1.00 | 12022 | 3 | | | EMILIN3 | 1.00 |
| 11927 | 3 | | | | | DUX4L6 | 1.00 | 12023 | 3 | | | EML1 | 1.00 |
| 11928 | 3 | | | | | DUXA | 1.00 | 12024 | 3 | | | EML5 | 1.00 |
| 11929 | 3 | | | | | DYDC1 | 1.00 | 12025 | 3 | | | EML6 | 1.00 |
| 11930 | 3 | | | | | DYDC2 | 1.00 | 12026 | 3 | | | EMP2 | 1.00 |
| 11931 | 3 | | | | | DYNC1I1 | 1.00 | 12027 | 3 | | | EMX1 | 1.00 |
| 11932 | 3 | | | | | DYNC2H1 | 1.00 | 12028 | 3 | | | EMX2 | 1.00 |
| 11933 | 3 | | | | | DYNC2LI1 | 1.00 | 12029 | 3 | | | EMX2OS | 1.00 |
| 11934 | 3 | | | | | DYNLRB2 | 1.00 | 12030 | 3 | | | EN1 | 1.00 |
| 11935 | 3 | | | | | DYTN | 1.00 | 12031 | 3 | | | EN2 | 1.00 |
| 11936 | 3 | | | | | DYX1C1 | 1.00 | 12032 | 3 | | | ENAH | 1.00 |
| 11937 | 3 | | | | | DYX1C1-CCPG1 | 1.00 | 12033 | 3 | | | ENAM | 1.00 |
| 11938 | 3 | | | | | DZANK1 | 1.00 | 12034 | 3 | | | ENDOU | 1.00 |
| 11939 | 3 | | | | | DZANK1-AS1 | 1.00 | 12035 | 3 | | | ENO1-AS1 | 1.00 |
| 11940 | 3 | | | | | DZIP1 | 1.00 | 12036 | 3 | | | ENO3 | 1.00 |
| 11941 | 3 | | | | | DZIP1L | 1.00 | 12037 | 3 | | | ENO4 | 1.00 |
| 11942 | 3 | | | | | E2F7 | 1.00 | 12038 | 3 | | | ENOSF1 | 1.00 |
| 11943 | 3 | | | | | E2F8 | 1.00 | 12039 | 3 | | | ENOX1 | 1.00 |
| 11944 | 3 | | | | | EBF2 | 1.00 | 12040 | 3 | | | ENPEP | 1.00 |
| 11945 | 3 | | | | | EBF3 | 1.00 | 12041 | 3 | | | ENPP1 | 1.00 |
| 11946 | 3 | | | | | EBF4 | 1.00 | 12042 | 3 | | | ENPP2 | 1.00 |
| 11947 | 3 | | | | | EBI3 | 1.00 | 12043 | 3 | | | ENPP3 | 1.00 |
| 11948 | 3 | | | | | EBLN1 | 1.00 | 12044 | 3 | | | ENPP6 | 1.00 |
| 11949 | 3 | | | | | EBLN2 | 1.00 | 12045 | 3 | | | ENPP7 | 1.00 |
| 11950 | 3 | | | | | ECE1 | 1.00 | 12046 | 3 | | | ENTHD1 | 1.00 |
| 11951 | 3 | | | | | ECE1P2 | 1.00 | 12047 | 3 | | | ENTPD3 | 1.00 |
| 11952 | 3 | | | | | ECM1 | 1.00 | 12048 | 3 | | | ENTPD3-AS1 | 1.00 |
| 11953 | 3 | | | | | ECM2 | 1.00 | 12049 | 3 | | | ENTPD8 | 1.00 |
| 11954 | 3 | | | | | ECSCR | 1.00 | 12050 | 3 | | | EP400NL | 1.00 |
| 11955 | 3 | | | | | ECT2 | 1.00 | 12051 | 3 | | | EPB41L1 | 1.00 |
| 11956 | 3 | | | | | ECT2L | 1.00 | 12052 | 3 | | | EPB41L4B | 1.00 |
| 11957 | 3 | | | | | EDA2R | 1.00 | 12053 | 3 | | | EPB41L5 | 1.00 |
| 11958 | 3 | | | | | EDDM3A | 1.00 | 12054 | 3 | | | EPCAM | 1.00 |
| 11959 | 3 | | | | | EDDM3B | 1.00 | 12055 | 3 | | | EPGN | 1.00 |
| 11960 | 3 | | | | | EDIL3 | 1.00 | 12056 | 3 | | | EPHA10 | 1.00 |
| 11961 | 3 | | | | | EDN1 | 1.00 | 12057 | 3 | | | EPHA2 | 1.00 |
| 11962 | 3 | | | | | EDN2 | 1.00 | 12058 | 3 | | | EPHA3 | 1.00 |
| 11963 | 3 | | | | | EDN3 | 1.00 | 12059 | 3 | | | EPHA5 | 1.00 |
| 11964 | 3 | | | | | EDNRA | 1.00 | 12060 | 3 | | | EPHA6 | 1.00 |
| 11965 | 3 | | | | | EDNRB | 1.00 | 12061 | 3 | | | EPHA7 | 1.00 |
| 11966 | 3 | | | | | EEF1A2 | 1.00 | 12062 | 3 | | | EPHA8 | 1.00 |
| 11967 | 3 | | | | | EFCAB1 | 1.00 | 12063 | 3 | | | EPHB3 | 1.00 |
| 11968 | 3 | | | | | EFCAB10 | 1.00 | 12064 | 3 | | | EPHX3 | 1.00 |
| 11969 | 3 | | | | | EFCAB11 | 1.00 | 12065 | 3 | | | EPHX4 | 1.00 |
| 11970 | 3 | | | | | EFCAB3 | 1.00 | 12066 | 3 | | | EPN3 | 1.00 |
| 11971 | 3 | | | | | EFCAB5 | 1.00 | 12067 | 3 | | | EPO | 1.00 |
| 11972 | 3 | | | | | EFCAB6 | 1.00 | 12068 | 3 | | | EPS8L1 | 1.00 |
| 11973 | 3 | | | | | EFCAB7 | 1.00 | 12069 | 3 | | | EPS8L3 | 1.00 |
| 11974 | 3 | | | | | EFCAB9 | 1.00 | 12070 | 3 | | | EPX | 1.00 |
| 11975 | 3 | | | | | EFEMP1 | 1.00 | 12071 | 3 | | | EPYC | 1.00 |
| 11976 | 3 | | | | | EFEMP2 | 1.00 | 12072 | 3 | | | ERAS | 1.00 |
| 11977 | 3 | | | | | EFHA2 | 1.00 | 12073 | 3 | | | ERBB3 | 1.00 |
| 11978 | 3 | | | | | EFHB | 1.00 | 12074 | 3 | | | ERBB4 | 1.00 |
| 11979 | 3 | | | | | EFHC1 | 1.00 | 12075 | 3 | | | ERC2 | 1.00 |
| 11980 | 3 | | | | | EFHD1 | 1.00 | 12076 | 3 | | | ERCC6L | 1.00 |
| 11981 | 3 | | | | | EFNA2 | 1.00 | 12077 | 3 | | | EREG | 1.00 |
| 11982 | 3 | | | | | EFNA5 | 1.00 | 12078 | 3 | | | ERG | 1.00 |
| 11983 | 3 | | | | | EFNB2 | 1.00 | 12079 | 3 | | | ERMN | 1.00 |
| 11984 | 3 | | | | | EFNB3 | 1.00 | 12080 | 3 | | | ERN2 | 1.00 |
| 11985 | 3 | | | | | EFR3B | 1.00 | 12081 | 3 | | | ERRFI1 | 1.00 |
| 11986 | 3 | | | | | EFS | 1.00 | 12082 | 3 | | | ERVFRD-1 | 1.00 |
| 11987 | 3 | | | | | EGFEM1P | 1.00 | 12083 | 3 | | | ERVK13-1 | 1.00 |
| 11988 | 3 | | | | | EGFL6 | 1.00 | 12084 | 3 | | | ERVMER34-1 | 1.00 |
| 11989 | 3 | | | | | EGFL8 | 1.00 | 12085 | 3 | | | ERVV-1 | 1.00 |
| 11990 | 3 | | | | | EGFLAM | 1.00 | 12086 | 3 | | | ERVV-2 | 1.00 |
| 11991 | 3 | | | | | EGFLAM-AS4 | 1.00 | 12087 | 3 | | | ESCO2 | 1.00 |
| 11992 | 3 | | | | | EGFR | 1.00 | 12088 | 3 | | | ESM1 | 1.00 |
| 11993 | 3 | | | | | EGOT | 1.00 | 12089 | 3 | | | ESPL1 | 1.00 |
| 11994 | 3 | | | | | EGR2 | 1.00 | 12090 | 3 | | | ESPN | 1.00 |

Fig. 41 - 64

| | | | | | | | | | | | | | |
|---|---|---|---|---|---|---|---|---|---|---|---|---|---|
| 12091 | 3 | | | | | ESPNP | 1.00 | 12187 | 3 | | | FAM166A | 1.00 |
| 12092 | 3 | | | | | ESR1 | 1.00 | 12188 | 3 | | | FAM166B | 1.00 |
| 12093 | 3 | | | | | ESR2 | 1.00 | 12189 | 3 | | | FAM167B | 1.00 |
| 12094 | 3 | | | | | ESRP1 | 1.00 | 12190 | 3 | | | FAM169B | 1.00 |
| 12095 | 3 | | | | | ESRP2 | 1.00 | 12191 | 3 | | | FAM170A | 1.00 |
| 12096 | 3 | | | | | ESRRB | 1.00 | 12192 | 3 | | | FAM170B | 1.00 |
| 12097 | 3 | | | | | ESRRG | 1.00 | 12193 | 3 | | | FAM171A2 | 1.00 |
| 12098 | 3 | | | | | ESX1 | 1.00 | 12194 | 3 | | | FAM171B | 1.00 |
| 12099 | 3 | | | | | ESYT3 | 1.00 | 12195 | 3 | | | FAM172BP | 1.00 |
| 12100 | 3 | | | | | ETNK2 | 1.00 | 12196 | 3 | | | FAM176A | 1.00 |
| 12101 | 3 | | | | | ETV1 | 1.00 | 12197 | 3 | | | FAM178B | 1.00 |
| 12102 | 3 | | | | | ETV2 | 1.00 | 12198 | 3 | | | FAM179A | 1.00 |
| 12103 | 3 | | | | | ETV3L | 1.00 | 12199 | 3 | | | FAM180A | 1.00 |
| 12104 | 3 | | | | | ETV4 | 1.00 | 12200 | 3 | | | FAM180B | 1.00 |
| 12105 | 3 | | | | | ETV5 | 1.00 | 12201 | 3 | | | FAM181A | 1.00 |
| 12106 | 3 | | | | | EVC | 1.00 | 12202 | 3 | | | FAM181A-AS1 | 1.00 |
| 12107 | 3 | | | | | EVC2 | 1.00 | 12203 | 3 | | | FAM181B | 1.00 |
| 12108 | 3 | | | | | EVPL | 1.00 | 12204 | 3 | | | FAM182A | 1.00 |
| 12109 | 3 | | | | | EVPLL | 1.00 | 12205 | 3 | | | FAM182B | 1.00 |
| 12110 | 3 | | | | | EVX1 | 1.00 | 12206 | 3 | | | FAM183A | 1.00 |
| 12111 | 3 | | | | | EVX2 | 1.00 | 12207 | 3 | | | FAM183B | 1.00 |
| 12112 | 3 | | | | | EXD1 | 1.00 | 12208 | 3 | | | FAM184A | 1.00 |
| 12113 | 3 | | | | | EXD3 | 1.00 | 12209 | 3 | | | FAM184B | 1.00 |
| 12114 | 3 | | | | | EXO1 | 1.00 | 12210 | 3 | | | FAM186A | 1.00 |
| 12115 | 3 | | | | | EXOC3L1 | 1.00 | 12211 | 3 | | | FAM186B | 1.00 |
| 12116 | 3 | | | | | EXOC3L2 | 1.00 | 12212 | 3 | | | FAM187B | 1.00 |
| 12117 | 3 | | | | | EXOC3L4 | 1.00 | 12213 | 3 | | | FAM188B | 1.00 |
| 12118 | 3 | | | | | EXOC6B | 1.00 | 12214 | 3 | | | FAM189A1 | 1.00 |
| 12119 | 3 | | | | | EXPH5 | 1.00 | 12215 | 3 | | | FAM189A2 | 1.00 |
| 12120 | 3 | | | | | EXTL1 | 1.00 | 12216 | 3 | | | FAM18A | 1.00 |
| 12121 | 3 | | | | | EYA1 | 1.00 | 12217 | 3 | | | FAM18B2-CDRT4 | 1.00 |
| 12122 | 3 | | | | | EYA2 | 1.00 | 12218 | 3 | | | FAM190A | 1.00 |
| 12123 | 3 | | | | | EYA4 | 1.00 | 12219 | 3 | | | FAM194A | 1.00 |
| 12124 | 3 | | | | | EYS | 1.00 | 12220 | 3 | | | FAM194B | 1.00 |
| 12125 | 3 | | | | | F10 | 1.00 | 12221 | 3 | | | FAM196A | 1.00 |
| 12126 | 3 | | | | | F11 | 1.00 | 12222 | 3 | | | FAM196B | 1.00 |
| 12127 | 3 | | | | | F12 | 1.00 | 12223 | 3 | | | FAM197Y2P | 1.00 |
| 12128 | 3 | | | | | F13B | 1.00 | 12224 | 3 | | | FAM197Y5 | 1.00 |
| 12129 | 3 | | | | | F2 | 1.00 | 12225 | 3 | | | FAM198A | 1.00 |
| 12130 | 3 | | | | | F2RL2 | 1.00 | 12226 | 3 | | | FAM19A3 | 1.00 |
| 12131 | 3 | | | | | F3 | 1.00 | 12227 | 3 | | | FAM19A4 | 1.00 |
| 12132 | 3 | | | | | F7 | 1.00 | 12228 | 3 | | | FAM19A5 | 1.00 |
| 12133 | 3 | | | | | F8A2 | 1.00 | 12229 | 3 | | | FAM201A | 1.00 |
| 12134 | 3 | | | | | F9 | 1.00 | 12230 | 3 | | | FAM205A | 1.00 |
| 12135 | 3 | | | | | FA2H | 1.00 | 12231 | 3 | | | FAM205B | 1.00 |
| 12136 | 3 | | | | | FAAH2 | 1.00 | 12232 | 3 | | | FAM209A | 1.00 |
| 12137 | 3 | | | | | FABP1 | 1.00 | 12233 | 3 | | | FAM211B | 1.00 |
| 12138 | 3 | | | | | FABP12 | 1.00 | 12234 | 3 | | | FAM215A | 1.00 |
| 12139 | 3 | | | | | FABP2 | 1.00 | 12235 | 3 | | | FAM216B | 1.00 |
| 12140 | 3 | | | | | FABP3 | 1.00 | 12236 | 3 | | | FAM217A | 1.00 |
| 12141 | 3 | | | | | FABP4 | 1.00 | 12237 | 3 | | | FAM22D | 1.00 |
| 12142 | 3 | | | | | FABP5P3 | 1.00 | 12238 | 3 | | | FAM22F | 1.00 |
| 12143 | 3 | | | | | FABP6 | 1.00 | 12239 | 3 | | | FAM22G | 1.00 |
| 12144 | 3 | | | | | FABP7 | 1.00 | 12240 | 3 | | | FAM24A | 1.00 |
| 12145 | 3 | | | | | FABP9 | 1.00 | 12241 | 3 | | | FAM24B-CUZD1 | 1.00 |
| 12146 | 3 | | | | | FADS6 | 1.00 | 12242 | 3 | | | FAM25A | 1.00 |
| 12147 | 3 | | | | | FAIM2 | 1.00 | 12243 | 3 | | | FAM25B | 1.00 |
| 12148 | 3 | | | | | FAM101A | 1.00 | 12244 | 3 | | | FAM25C | 1.00 |
| 12149 | 3 | | | | | FAM106A | 1.00 | 12245 | 3 | | | FAM26D | 1.00 |
| 12150 | 3 | | | | | FAM106CP | 1.00 | 12246 | 3 | | | FAM26E | 1.00 |
| 12151 | 3 | | | | | FAM107A | 1.00 | 12247 | 3 | | | FAM27C | 1.00 |
| 12152 | 3 | | | | | FAM110B | 1.00 | 12248 | 3 | | | FAM27L | 1.00 |
| 12153 | 3 | | | | | FAM110C | 1.00 | 12249 | 3 | | | FAM3B | 1.00 |
| 12154 | 3 | | | | | FAM110D | 1.00 | 12250 | 3 | | | FAM3D | 1.00 |
| 12155 | 3 | | | | | FAM123A | 1.00 | 12251 | 3 | | | FAM40B | 1.00 |
| 12156 | 3 | | | | | FAM123C | 1.00 | 12252 | 3 | | | FAM41AY1 | 1.00 |
| 12157 | 3 | | | | | FAM124A | 1.00 | 12253 | 3 | | | FAM41AY2 | 1.00 |
| 12158 | 3 | | | | | FAM127C | 1.00 | 12254 | 3 | | | FAM41C | 1.00 |
| 12159 | 3 | | | | | FAM131C | 1.00 | 12255 | 3 | | | FAM43B | 1.00 |
| 12160 | 3 | | | | | FAM132A | 1.00 | 12256 | 3 | | | FAM46B | 1.00 |
| 12161 | 3 | | | | | FAM133A | 1.00 | 12257 | 3 | | | FAM46D | 1.00 |
| 12162 | 3 | | | | | FAM135B | 1.00 | 12258 | 3 | | | FAM47A | 1.00 |
| 12163 | 3 | | | | | FAM138A | 1.00 | 12259 | 3 | | | FAM47B | 1.00 |
| 12164 | 3 | | | | | FAM138B | 1.00 | 12260 | 3 | | | FAM47C | 1.00 |
| 12165 | 3 | | | | | FAM138C | 1.00 | 12261 | 3 | | | FAM47E | 1.00 |
| 12166 | 3 | | | | | FAM138D | 1.00 | 12262 | 3 | | | FAM47E-STBD1 | 1.00 |
| 12167 | 3 | | | | | FAM138E | 1.00 | 12263 | 3 | | | FAM48B1 | 1.00 |
| 12168 | 3 | | | | | FAM138F | 1.00 | 12264 | 3 | | | FAM48B2 | 1.00 |
| 12169 | 3 | | | | | FAM13C | 1.00 | 12265 | 3 | | | FAM53A | 1.00 |
| 12170 | 3 | | | | | FAM149A | 1.00 | 12266 | 3 | | | FAM54A | 1.00 |
| 12171 | 3 | | | | | FAM150A | 1.00 | 12267 | 3 | | | FAM55A | 1.00 |
| 12172 | 3 | | | | | FAM150B | 1.00 | 12268 | 3 | | | FAM55B | 1.00 |
| 12173 | 3 | | | | | FAM151A | 1.00 | 12269 | 3 | | | FAM55D | 1.00 |
| 12174 | 3 | | | | | FAM153A | 1.00 | 12270 | 3 | | | FAM57A | 1.00 |
| 12175 | 3 | | | | | FAM153B | 1.00 | 12271 | 3 | | | FAM57B | 1.00 |
| 12176 | 3 | | | | | FAM153C | 1.00 | 12272 | 3 | | | FAM59A | 1.00 |
| 12177 | 3 | | | | | FAM154A | 1.00 | 12273 | 3 | | | FAM59B | 1.00 |
| 12178 | 3 | | | | | FAM154B | 1.00 | 12274 | 3 | | | FAM5B | 1.00 |
| 12179 | 3 | | | | | FAM155A | 1.00 | 12275 | 3 | | | FAM5C | 1.00 |
| 12180 | 3 | | | | | FAM155B | 1.00 | 12276 | 3 | | | FAM64A | 1.00 |
| 12181 | 3 | | | | | FAM159B | 1.00 | 12277 | 3 | | | FAM65C | 1.00 |
| 12182 | 3 | | | | | FAM160A1 | 1.00 | 12278 | 3 | | | FAM66A | 1.00 |
| 12183 | 3 | | | | | FAM161A | 1.00 | 12279 | 3 | | | FAM66B | 1.00 |
| 12184 | 3 | | | | | FAM162B | 1.00 | 12280 | 3 | | | FAM66C | 1.00 |
| 12185 | 3 | | | | | FAM163A | 1.00 | 12281 | 3 | | | FAM66D | 1.00 |
| 12186 | 3 | | | | | FAM163B | 1.00 | 12282 | 3 | | | FAM66E | 1.00 |

Fig. 41 - 65

| | | | | | | | | | | | | | | |
|---|---|---|---|---|---|---|---|---|---|---|---|---|---|---|
| 12283 | 3 | | | | | FAM69C | 1.00 | 12379 | 3 | | | | FBXO15 | 1.00 |
| 12284 | 3 | | | | | FAM70A | 1.00 | 12380 | 3 | | | | FBXO16 | 1.00 |
| 12285 | 3 | | | | | FAM70B | 1.00 | 12381 | 3 | | | | FBXO17 | 1.00 |
| 12286 | 3 | | | | | FAM71A | 1.00 | 12382 | 3 | | | | FBXO24 | 1.00 |
| 12287 | 3 | | | | | FAM71B | 1.00 | 12383 | 3 | | | | FBXO27 | 1.00 |
| 12288 | 3 | | | | | FAM71C | 1.00 | 12384 | 3 | | | | FBXO36 | 1.00 |
| 12289 | 3 | | | | | FAM71D | 1.00 | 12385 | 3 | | | | FBXO39 | 1.00 |
| 12290 | 3 | | | | | FAM71E2 | 1.00 | 12386 | 3 | | | | FBXO40 | 1.00 |
| 12291 | 3 | | | | | FAM71F1 | 1.00 | 12387 | 3 | | | | FBXO43 | 1.00 |
| 12292 | 3 | | | | | FAM71F2 | 1.00 | 12388 | 3 | | | | FBXO47 | 1.00 |
| 12293 | 3 | | | | | FAM72B | 1.00 | 12389 | 3 | | | | FBXW10 | 1.00 |
| 12294 | 3 | | | | | FAM72D | 1.00 | 12390 | 3 | | | | FBXW12 | 1.00 |
| 12295 | 3 | | | | | FAM74A1 | 1.00 | 12391 | 3 | | | | FCAMR | 1.00 |
| 12296 | 3 | | | | | FAM74A2 | 1.00 | 12392 | 3 | | | | FCN2 | 1.00 |
| 12297 | 3 | | | | | FAM74A3 | 1.00 | 12393 | 3 | | | | FCN3 | 1.00 |
| 12298 | 3 | | | | | FAM74A4 | 1.00 | 12394 | 3 | | | | FCRL4 | 1.00 |
| 12299 | 3 | | | | | FAM75A1 | 1.00 | 12395 | 3 | | | | FDCSP | 1.00 |
| 12300 | 3 | | | | | FAM75A2 | 1.00 | 12396 | 3 | | | | FER | 1.00 |
| 12301 | 3 | | | | | FAM75A3 | 1.00 | 12397 | 3 | | | | FER1L4 | 1.00 |
| 12302 | 3 | | | | | FAM75A4 | 1.00 | 12398 | 3 | | | | FER1L5 | 1.00 |
| 12303 | 3 | | | | | FAM75A5 | 1.00 | 12399 | 3 | | | | FER1L6 | 1.00 |
| 12304 | 3 | | | | | FAM75A6 | 1.00 | 12400 | 3 | | | | FER1L6-AS1 | 1.00 |
| 12305 | 3 | | | | | FAM75A7 | 1.00 | 12401 | 3 | | | | FERD3L | 1.00 |
| 12306 | 3 | | | | | FAM75C1 | 1.00 | 12402 | 3 | | | | FERMT1 | 1.00 |
| 12307 | 3 | | | | | FAM75C2 | 1.00 | 12403 | 3 | | | | FERMT2 | 1.00 |
| 12308 | 3 | | | | | FAM75D1 | 1.00 | 12404 | 3 | | | | FETUB | 1.00 |
| 12309 | 3 | | | | | FAM75D3 | 1.00 | 12405 | 3 | | | | FEV | 1.00 |
| 12310 | 3 | | | | | FAM75D4 | 1.00 | 12406 | 3 | | | | FEZF1 | 1.00 |
| 12311 | 3 | | | | | FAM75D5 | 1.00 | 12407 | 3 | | | | FEZF2 | 1.00 |
| 12312 | 3 | | | | | FAM78B | 1.00 | 12408 | 3 | | | | FFAR1 | 1.00 |
| 12313 | 3 | | | | | FAM81A | 1.00 | 12409 | 3 | | | | FGA | 1.00 |
| 12314 | 3 | | | | | FAM81B | 1.00 | 12410 | 3 | | | | FGB | 1.00 |
| 12315 | 3 | | | | | FAM83A | 1.00 | 12411 | 3 | | | | FGD1 | 1.00 |
| 12316 | 3 | | | | | FAM83B | 1.00 | 12412 | 3 | | | | FGD5 | 1.00 |
| 12317 | 3 | | | | | FAM83C | 1.00 | 12413 | 3 | | | | FGF1 | 1.00 |
| 12318 | 3 | | | | | FAM83D | 1.00 | 12414 | 3 | | | | FGF10 | 1.00 |
| 12319 | 3 | | | | | FAM83E | 1.00 | 12415 | 3 | | | | FGF11 | 1.00 |
| 12320 | 3 | | | | | FAM83F | 1.00 | 12416 | 3 | | | | FGF12 | 1.00 |
| 12321 | 3 | | | | | FAM84A | 1.00 | 12417 | 3 | | | | FGF14 | 1.00 |
| 12322 | 3 | | | | | FAM86B1 | 1.00 | 12418 | 3 | | | | FGF14-IT1 | 1.00 |
| 12323 | 3 | | | | | FAM86B2 | 1.00 | 12419 | 3 | | | | FGF16 | 1.00 |
| 12324 | 3 | | | | | FAM86C2P | 1.00 | 12420 | 3 | | | | FGF17 | 1.00 |
| 12325 | 3 | | | | | FAM86EP | 1.00 | 12421 | 3 | | | | FGF18 | 1.00 |
| 12326 | 3 | | | | | FAM86FP | 1.00 | 12422 | 3 | | | | FGF19 | 1.00 |
| 12327 | 3 | | | | | FAM86HP | 1.00 | 12423 | 3 | | | | FGF2 | 1.00 |
| 12328 | 3 | | | | | FAM90A1 | 1.00 | 12424 | 3 | | | | FGF20 | 1.00 |
| 12329 | 3 | | | | | FAM90A10 | 1.00 | 12425 | 3 | | | | FGF21 | 1.00 |
| 12330 | 3 | | | | | FAM90A10P | 1.00 | 12426 | 3 | | | | FGF22 | 1.00 |
| 12331 | 3 | | | | | FAM90A14 | 1.00 | 12427 | 3 | | | | FGF23 | 1.00 |
| 12332 | 3 | | | | | FAM90A19 | 1.00 | 12428 | 3 | | | | FGF3 | 1.00 |
| 12333 | 3 | | | | | FAM90A20 | 1.00 | 12429 | 3 | | | | FGF4 | 1.00 |
| 12334 | 3 | | | | | FAM90A25P | 1.00 | 12430 | 3 | | | | FGF5 | 1.00 |
| 12335 | 3 | | | | | FAM90A27P | 1.00 | 12431 | 3 | | | | FGF6 | 1.00 |
| 12336 | 3 | | | | | FAM90A2P | 1.00 | 12432 | 3 | | | | FGF7 | 1.00 |
| 12337 | 3 | | | | | FAM90A5 | 1.00 | 12433 | 3 | | | | FGF8 | 1.00 |
| 12338 | 3 | | | | | FAM90A7 | 1.00 | 12434 | 3 | | | | FGF9 | 1.00 |
| 12339 | 3 | | | | | FAM90A7P | 1.00 | 12435 | 3 | | | | FGFBP1 | 1.00 |
| 12340 | 3 | | | | | FAM90A8 | 1.00 | 12436 | 3 | | | | FGFBP3 | 1.00 |
| 12341 | 3 | | | | | FAM90A9 | 1.00 | 12437 | 3 | | | | FGFR2 | 1.00 |
| 12342 | 3 | | | | | FAM92A1 | 1.00 | 12438 | 3 | | | | FGFR3 | 1.00 |
| 12343 | 3 | | | | | FAM92A3 | 1.00 | 12439 | 3 | | | | FGFR4 | 1.00 |
| 12344 | 3 | | | | | FAM92B | 1.00 | 12440 | 3 | | | | FGG | 1.00 |
| 12345 | 3 | | | | | FAM95B1 | 1.00 | 12441 | 3 | | | | FGGY | 1.00 |
| 12346 | 3 | | | | | FAM99A | 1.00 | 12442 | 3 | | | | FGL1 | 1.00 |
| 12347 | 3 | | | | | FAM99B | 1.00 | 12443 | 3 | | | | FHAD1 | 1.00 |
| 12348 | 3 | | | | | FAM9A | 1.00 | 12444 | 3 | | | | FHL5 | 1.00 |
| 12349 | 3 | | | | | FAM9B | 1.00 | 12445 | 3 | | | | FHOD3 | 1.00 |
| 12350 | 3 | | | | | FAM9C | 1.00 | 12446 | 3 | | | | FIBCD1 | 1.00 |
| 12351 | 3 | | | | | FANCB | 1.00 | 12447 | 3 | | | | FIBIN | 1.00 |
| 12352 | 3 | | | | | FANCC | 1.00 | 12448 | 3 | | | | FIGF | 1.00 |
| 12353 | 3 | | | | | FANCD2 | 1.00 | 12449 | 3 | | | | FIGLA | 1.00 |
| 12354 | 3 | | | | | FANCI | 1.00 | 12450 | 3 | | | | FIGN | 1.00 |
| 12355 | 3 | | | | | FANCL | 1.00 | 12451 | 3 | | | | FIGNL2 | 1.00 |
| 12356 | 3 | | | | | FANCM | 1.00 | 12452 | 3 | | | | FILIP1 | 1.00 |
| 12357 | 3 | | | | | FANK1 | 1.00 | 12453 | 3 | | | | FJX1 | 1.00 |
| 12358 | 3 | | | | | FAP | 1.00 | 12454 | 3 | | | | FKBP10 | 1.00 |
| 12359 | 3 | | | | | FARP1 | 1.00 | 12455 | 3 | | | | FKBP14 | 1.00 |
| 12360 | 3 | | | | | FAS-AS1 | 1.00 | 12456 | 3 | | | | FKBP1A-SDCBP2 | 1.00 |
| 12361 | 3 | | | | | FAT1 | 1.00 | 12457 | 3 | | | | FKBP6 | 1.00 |
| 12362 | 3 | | | | | FAT2 | 1.00 | 12458 | 3 | | | | FKBP7 | 1.00 |
| 12363 | 3 | | | | | FAT3 | 1.00 | 12459 | 3 | | | | FKBP9L | 1.00 |
| 12364 | 3 | | | | | FAT4 | 1.00 | 12460 | 3 | | | | FKSG29 | 1.00 |
| 12365 | 3 | | | | | FATE1 | 1.00 | 12461 | 3 | | | | FLG | 1.00 |
| 12366 | 3 | | | | | FAXC | 1.00 | 12462 | 3 | | | | FLG2 | 1.00 |
| 12367 | 3 | | | | | FBF1 | 1.00 | 12463 | 3 | | | | FLJ11235 | 1.00 |
| 12368 | 3 | | | | | FBLIM1 | 1.00 | 12464 | 3 | | | | FLJ12334 | 1.00 |
| 12369 | 3 | | | | | FBLL1 | 1.00 | 12465 | 3 | | | | FLJ12825 | 1.00 |
| 12370 | 3 | | | | | FBLN1 | 1.00 | 12466 | 3 | | | | FLJ13224 | 1.00 |
| 12371 | 3 | | | | | FBN1 | 1.00 | 12467 | 3 | | | | FLJ14107 | 1.00 |
| 12372 | 3 | | | | | FBN3 | 1.00 | 12468 | 3 | | | | FLJ16171 | 1.00 |
| 12373 | 3 | | | | | FBP2 | 1.00 | 12469 | 3 | | | | FLJ16341 | 1.00 |
| 12374 | 3 | | | | | FBXL19-AS1 | 1.00 | 12470 | 3 | | | | FLJ16779 | 1.00 |
| 12375 | 3 | | | | | FBXL2 | 1.00 | 12471 | 3 | | | | FLJ20518 | 1.00 |
| 12376 | 3 | | | | | FBXL21 | 1.00 | 12472 | 3 | | | | FLJ21408 | 1.00 |
| 12377 | 3 | | | | | FBXL22 | 1.00 | 12473 | 3 | | | | FLJ22184 | 1.00 |
| 12378 | 3 | | | | | FBXL7 | 1.00 | 12474 | 3 | | | | FLJ22447 | 1.00 |

Fig. 41 - 66

| | | | | | | | | | | | | | | |
|---|---|---|---|---|---|---|---|---|---|---|---|---|---|---|
| 12475 | 3 | | | | | | FLJ22763 | 1.00 | 12571 | 3 | | | | FOLH1B | 1.00 |
| 12476 | 3 | | | | | | FLJ23152 | 1.00 | 12572 | 3 | | | | FOLR1 | 1.00 |
| 12477 | 3 | | | | | | FLJ25328 | 1.00 | 12573 | 3 | | | | FOLR4 | 1.00 |
| 12478 | 3 | | | | | | FLJ25363 | 1.00 | 12574 | 3 | | | | FONG | 1.00 |
| 12479 | 3 | | | | | | FLJ25758 | 1.00 | 12575 | 3 | | | | FOSL1 | 1.00 |
| 12480 | 3 | | | | | | FLJ26245 | 1.00 | 12576 | 3 | | | | FOXA1 | 1.00 |
| 12481 | 3 | | | | | | FLJ26850 | 1.00 | 12577 | 3 | | | | FOXA2 | 1.00 |
| 12482 | 3 | | | | | | FLJ30403 | 1.00 | 12578 | 3 | | | | FOXA3 | 1.00 |
| 12483 | 3 | | | | | | FLJ30679 | 1.00 | 12579 | 3 | | | | FOXB1 | 1.00 |
| 12484 | 3 | | | | | | FLJ30838 | 1.00 | 12580 | 3 | | | | FOXB2 | 1.00 |
| 12485 | 3 | | | | | | FLJ31485 | 1.00 | 12581 | 3 | | | | FOXC1 | 1.00 |
| 12486 | 3 | | | | | | FLJ31662 | 1.00 | 12582 | 3 | | | | FOXC2 | 1.00 |
| 12487 | 3 | | | | | | FLJ31813 | 1.00 | 12583 | 3 | | | | FOXD1 | 1.00 |
| 12488 | 3 | | | | | | FLJ32063 | 1.00 | 12584 | 3 | | | | FOXD2 | 1.00 |
| 12489 | 3 | | | | | | FLJ33360 | 1.00 | 12585 | 3 | | | | FOXD3 | 1.00 |
| 12490 | 3 | | | | | | FLJ33534 | 1.00 | 12586 | 3 | | | | FOXD4 | 1.00 |
| 12491 | 3 | | | | | | FLJ33581 | 1.00 | 12587 | 3 | | | | FOXD4L1 | 1.00 |
| 12492 | 3 | | | | | | FLJ34208 | 1.00 | 12588 | 3 | | | | FOXD4L2 | 1.00 |
| 12493 | 3 | | | | | | FLJ34503 | 1.00 | 12589 | 3 | | | | FOXD4L3 | 1.00 |
| 12494 | 3 | | | | | | FLJ34690 | 1.00 | 12590 | 3 | | | | FOXD4L5 | 1.00 |
| 12495 | 3 | | | | | | FLJ35024 | 1.00 | 12591 | 3 | | | | FOXD4L6 | 1.00 |
| 12496 | 3 | | | | | | FLJ35282 | 1.00 | 12592 | 3 | | | | FOXE1 | 1.00 |
| 12497 | 3 | | | | | | FLJ35424 | 1.00 | 12593 | 3 | | | | FOXE3 | 1.00 |
| 12498 | 3 | | | | | | FLJ35946 | 1.00 | 12594 | 3 | | | | FOXF1 | 1.00 |
| 12499 | 3 | | | | | | FLJ36000 | 1.00 | 12595 | 3 | | | | FOXF2 | 1.00 |
| 12500 | 3 | | | | | | FLJ36777 | 1.00 | 12596 | 3 | | | | FOXG1 | 1.00 |
| 12501 | 3 | | | | | | FLJ37035 | 1.00 | 12597 | 3 | | | | FOXH1 | 1.00 |
| 12502 | 3 | | | | | | FLJ37201 | 1.00 | 12598 | 3 | | | | FOXI1 | 1.00 |
| 12503 | 3 | | | | | | FLJ37505 | 1.00 | 12599 | 3 | | | | FOXI2 | 1.00 |
| 12504 | 3 | | | | | | FLJ38109 | 1.00 | 12600 | 3 | | | | FOXI3 | 1.00 |
| 12505 | 3 | | | | | | FLJ38576 | 1.00 | 12601 | 3 | | | | FOXJ1 | 1.00 |
| 12506 | 3 | | | | | | FLJ39080 | 1.00 | 12602 | 3 | | | | FOXL1 | 1.00 |
| 12507 | 3 | | | | | | FLJ39534 | 1.00 | 12603 | 3 | | | | FOXL2 | 1.00 |
| 12508 | 3 | | | | | | FLJ40194 | 1.00 | 12604 | 3 | | | | FOXN1 | 1.00 |
| 12509 | 3 | | | | | | FLJ40288 | 1.00 | 12605 | 3 | | | | FOXN4 | 1.00 |
| 12510 | 3 | | | | | | FLJ40292 | 1.00 | 12606 | 3 | | | | FOXP2 | 1.00 |
| 12511 | 3 | | | | | | FLJ40434 | 1.00 | 12607 | 3 | | | | FOXQ1 | 1.00 |
| 12512 | 3 | | | | | | FLJ40852 | 1.00 | 12608 | 3 | | | | FOXR1 | 1.00 |
| 12513 | 3 | | | | | | FLJ41200 | 1.00 | 12609 | 3 | | | | FOXR2 | 1.00 |
| 12514 | 3 | | | | | | FLJ41278 | 1.00 | 12610 | 3 | | | | FOXS1 | 1.00 |
| 12515 | 3 | | | | | | FLJ41350 | 1.00 | 12611 | 3 | | | | FP588 | 1.00 |
| 12516 | 3 | | | | | | FLJ41484 | 1.00 | 12612 | 3 | | | | FPGT-TNNI3K | 1.00 |
| 12517 | 3 | | | | | | FLJ41649 | 1.00 | 12613 | 3 | | | | FRAS1 | 1.00 |
| 12518 | 3 | | | | | | FLJ41941 | 1.00 | 12614 | 3 | | | | FREM1 | 1.00 |
| 12519 | 3 | | | | | | FLJ42102 | 1.00 | 12615 | 3 | | | | FREM2 | 1.00 |
| 12520 | 3 | | | | | | FLJ42280 | 1.00 | 12616 | 3 | | | | FREM3 | 1.00 |
| 12521 | 3 | | | | | | FLJ42289 | 1.00 | 12617 | 3 | | | | FRG2 | 1.00 |
| 12522 | 3 | | | | | | FLJ42351 | 1.00 | 12618 | 3 | | | | FRG2B | 1.00 |
| 12523 | 3 | | | | | | FLJ42393 | 1.00 | 12619 | 3 | | | | FRG2C | 1.00 |
| 12524 | 3 | | | | | | FLJ42709 | 1.00 | 12620 | 3 | | | | FRK | 1.00 |
| 12525 | 3 | | | | | | FLJ42875 | 1.00 | 12621 | 3 | | | | FRMD1 | 1.00 |
| 12526 | 3 | | | | | | FLJ42969 | 1.00 | 12622 | 3 | | | | FRMD5 | 1.00 |
| 12527 | 3 | | | | | | FLJ43315 | 1.00 | 12623 | 3 | | | | FRMD6 | 1.00 |
| 12528 | 3 | | | | | | FLJ43390 | 1.00 | 12624 | 3 | | | | FRMD6-AS1 | 1.00 |
| 12529 | 3 | | | | | | FLJ43681 | 1.00 | 12625 | 3 | | | | FRMD7 | 1.00 |
| 12530 | 3 | | | | | | FLJ43826 | 1.00 | 12626 | 3 | | | | FRMPD1 | 1.00 |
| 12531 | 3 | | | | | | FLJ43860 | 1.00 | 12627 | 3 | | | | FRMPD2 | 1.00 |
| 12532 | 3 | | | | | | FLJ43879 | 1.00 | 12628 | 3 | | | | FRMPD2P1 | 1.00 |
| 12533 | 3 | | | | | | FLJ44054 | 1.00 | 12629 | 3 | | | | FRMPD4 | 1.00 |
| 12534 | 3 | | | | | | FLJ45079 | 1.00 | 12630 | 3 | | | | FRRS1 | 1.00 |
| 12535 | 3 | | | | | | FLJ45513 | 1.00 | 12631 | 3 | | | | FRZB | 1.00 |
| 12536 | 3 | | | | | | FLJ45974 | 1.00 | 12632 | 3 | | | | FSBP | 1.00 |
| 12537 | 3 | | | | | | FLJ45983 | 1.00 | 12633 | 3 | | | | FSCB | 1.00 |
| 12538 | 3 | | | | | | FLJ46066 | 1.00 | 12634 | 3 | | | | FSCN2 | 1.00 |
| 12539 | 3 | | | | | | FLJ46257 | 1.00 | 12635 | 3 | | | | FSCN3 | 1.00 |
| 12540 | 3 | | | | | | FLJ46284 | 1.00 | 12636 | 3 | | | | FSD1 | 1.00 |
| 12541 | 3 | | | | | | FLJ46300 | 1.00 | 12637 | 3 | | | | FSD2 | 1.00 |
| 12542 | 3 | | | | | | FLJ46361 | 1.00 | 12638 | 3 | | | | FSHB | 1.00 |
| 12543 | 3 | | | | | | FLJ46446 | 1.00 | 12639 | 3 | | | | FSHR | 1.00 |
| 12544 | 3 | | | | | | FLJ46906 | 1.00 | 12640 | 3 | | | | FSIP1 | 1.00 |
| 12545 | 3 | | | | | | FLNC | 1.00 | 12641 | 3 | | | | FSIP2 | 1.00 |
| 12546 | 3 | | | | | | FLRT1 | 1.00 | 12642 | 3 | | | | FST | 1.00 |
| 12547 | 3 | | | | | | FLRT2 | 1.00 | 12643 | 3 | | | | FSTL4 | 1.00 |
| 12548 | 3 | | | | | | FLRT3 | 1.00 | 12644 | 3 | | | | FSTL5 | 1.00 |
| 12549 | 3 | | | | | | FLT1 | 1.00 | 12645 | 3 | | | | FTCD | 1.00 |
| 12550 | 3 | | | | | | FLT4 | 1.00 | 12646 | 3 | | | | FTHL17 | 1.00 |
| 12551 | 3 | | | | | | FMN2 | 1.00 | 12647 | 3 | | | | FTLP10 | 1.00 |
| 12552 | 3 | | | | | | FMNL2 | 1.00 | 12648 | 3 | | | | FTMT | 1.00 |
| 12553 | 3 | | | | | | FMO1 | 1.00 | 12649 | 3 | | | | FUT1 | 1.00 |
| 12554 | 3 | | | | | | FMO2 | 1.00 | 12650 | 3 | | | | FUT2 | 1.00 |
| 12555 | 3 | | | | | | FMO3 | 1.00 | 12651 | 3 | | | | FUT3 | 1.00 |
| 12556 | 3 | | | | | | FMO6P | 1.00 | 12652 | 3 | | | | FUT5 | 1.00 |
| 12557 | 3 | | | | | | FMO9P | 1.00 | 12653 | 3 | | | | FUT6 | 1.00 |
| 12558 | 3 | | | | | | FMOD | 1.00 | 12654 | 3 | | | | FUT9 | 1.00 |
| 12559 | 3 | | | | | | FMR1-AS1 | 1.00 | 12655 | 3 | | | | FXYD1 | 1.00 |
| 12560 | 3 | | | | | | FMR1NB | 1.00 | 12656 | 3 | | | | FXYD3 | 1.00 |
| 12561 | 3 | | | | | | FN1 | 1.00 | 12657 | 3 | | | | FXYD4 | 1.00 |
| 12562 | 3 | | | | | | FN3K | 1.00 | 12658 | 3 | | | | FXYD6-FXYD2 | 1.00 |
| 12563 | 3 | | | | | | FNBP1L | 1.00 | 12659 | 3 | | | | FZD10 | 1.00 |
| 12564 | 3 | | | | | | FNDC1 | 1.00 | 12660 | 3 | | | | FZD3 | 1.00 |
| 12565 | 3 | | | | | | FNDC4 | 1.00 | 12661 | 3 | | | | FZD4 | 1.00 |
| 12566 | 3 | | | | | | FNDC5 | 1.00 | 12662 | 3 | | | | FZD7 | 1.00 |
| 12567 | 3 | | | | | | FNDC7 | 1.00 | 12663 | 3 | | | | FZD8 | 1.00 |
| 12568 | 3 | | | | | | FNDC8 | 1.00 | 12664 | 3 | | | | FZD9 | 1.00 |
| 12569 | 3 | | | | | | FNDC9 | 1.00 | 12665 | 3 | | | | G6PC | 1.00 |
| 12570 | 3 | | | | | | FOLH1 | 1.00 | 12666 | 3 | | | | G6PC2 | 1.00 |

Fig. 41 - 67

| | | | | | | | | | | | | | | |
|---|---|---|---|---|---|---|---|---|---|---|---|---|---|---|
| 12667 | 3 | | | | | GAB4 | 1.00 | 12763 | 3 | | | | GDAP1L1 | 1.00 |
| 12668 | 3 | | | | | GABBR2 | 1.00 | 12764 | 3 | | | | GDEP | 1.00 |
| 12669 | 3 | | | | | GABRA1 | 1.00 | 12765 | 3 | | | | GDF10 | 1.00 |
| 12670 | 3 | | | | | GABRA2 | 1.00 | 12766 | 3 | | | | GDF15 | 1.00 |
| 12671 | 3 | | | | | GABRA3 | 1.00 | 12767 | 3 | | | | GDF2 | 1.00 |
| 12672 | 3 | | | | | GABRA4 | 1.00 | 12768 | 3 | | | | GDF3 | 1.00 |
| 12673 | 3 | | | | | GABRA5 | 1.00 | 12769 | 3 | | | | GDF5 | 1.00 |
| 12674 | 3 | | | | | GABRA6 | 1.00 | 12770 | 3 | | | | GDF6 | 1.00 |
| 12675 | 3 | | | | | GABRB1 | 1.00 | 12771 | 3 | | | | GDF7 | 1.00 |
| 12676 | 3 | | | | | GABRB2 | 1.00 | 12772 | 3 | | | | GDF9 | 1.00 |
| 12677 | 3 | | | | | GABRB3 | 1.00 | 12773 | 3 | | | | GDNF | 1.00 |
| 12678 | 3 | | | | | GABRD | 1.00 | 12774 | 3 | | | | GDPD1 | 1.00 |
| 12679 | 3 | | | | | GABRE | 1.00 | 12775 | 3 | | | | GDPD2 | 1.00 |
| 12680 | 3 | | | | | GABRG1 | 1.00 | 12776 | 3 | | | | GDPD4 | 1.00 |
| 12681 | 3 | | | | | GABRG2 | 1.00 | 12777 | 3 | | | | GEM | 1.00 |
| 12682 | 3 | | | | | GABRG3 | 1.00 | 12778 | 3 | | | | GEMIN2 | 1.00 |
| 12683 | 3 | | | | | GABRP | 1.00 | 12779 | 3 | | | | GEMIN8P4 | 1.00 |
| 12684 | 3 | | | | | GABRQ | 1.00 | 12780 | 3 | | | | GFAP | 1.00 |
| 12685 | 3 | | | | | GABRR1 | 1.00 | 12781 | 3 | | | | GFPT2 | 1.00 |
| 12686 | 3 | | | | | GABRR2 | 1.00 | 12782 | 3 | | | | GFRA1 | 1.00 |
| 12687 | 3 | | | | | GABRR3 | 1.00 | 12783 | 3 | | | | GFRA2 | 1.00 |
| 12688 | 3 | | | | | GAD1 | 1.00 | 12784 | 3 | | | | GFRA3 | 1.00 |
| 12689 | 3 | | | | | GAD2 | 1.00 | 12785 | 3 | | | | GFRA4 | 1.00 |
| 12690 | 3 | | | | | GADL1 | 1.00 | 12786 | 3 | | | | GFRAL | 1.00 |
| 12691 | 3 | | | | | GAGE1 | 1.00 | 12787 | 3 | | | | GGH | 1.00 |
| 12692 | 3 | | | | | GAGE10 | 1.00 | 12788 | 3 | | | | GGN | 1.00 |
| 12693 | 3 | | | | | GAGE12B | 1.00 | 12789 | 3 | | | | GGNBP1 | 1.00 |
| 12694 | 3 | | | | | GAGE12C | 1.00 | 12790 | 3 | | | | GGT3P | 1.00 |
| 12695 | 3 | | | | | GAGE12D | 1.00 | 12791 | 3 | | | | GGT5 | 1.00 |
| 12696 | 3 | | | | | GAGE12E | 1.00 | 12792 | 3 | | | | GGT6 | 1.00 |
| 12697 | 3 | | | | | GAGE12F | 1.00 | 12793 | 3 | | | | GGT8P | 1.00 |
| 12698 | 3 | | | | | GAGE12H | 1.00 | 12794 | 3 | | | | GGTLC1 | 1.00 |
| 12699 | 3 | | | | | GAGE12I | 1.00 | 12795 | 3 | | | | GH1 | 1.00 |
| 12700 | 3 | | | | | GAGE12J | 1.00 | 12796 | 3 | | | | GH2 | 1.00 |
| 12701 | 3 | | | | | GAGE13 | 1.00 | 12797 | 3 | | | | GHR | 1.00 |
| 12702 | 3 | | | | | GAGE2A | 1.00 | 12798 | 3 | | | | GHRH | 1.00 |
| 12703 | 3 | | | | | GAGE2B | 1.00 | 12799 | 3 | | | | GHRHR | 1.00 |
| 12704 | 3 | | | | | GAGE2C | 1.00 | 12800 | 3 | | | | GHSR | 1.00 |
| 12705 | 3 | | | | | GAGE2D | 1.00 | 12801 | 3 | | | | GIF | 1.00 |
| 12706 | 3 | | | | | GAGE2E | 1.00 | 12802 | 3 | | | | GINS1 | 1.00 |
| 12707 | 3 | | | | | GAGE4 | 1.00 | 12803 | 3 | | | | GINS2 | 1.00 |
| 12708 | 3 | | | | | GAGE5 | 1.00 | 12804 | 3 | | | | GINS4 | 1.00 |
| 12709 | 3 | | | | | GAGE6 | 1.00 | 12805 | 3 | | | | GIP | 1.00 |
| 12710 | 3 | | | | | GAGE7 | 1.00 | 12806 | 3 | | | | GIPC2 | 1.00 |
| 12711 | 3 | | | | | GAGE8 | 1.00 | 12807 | 3 | | | | GIPR | 1.00 |
| 12712 | 3 | | | | | GAL | 1.00 | 12808 | 3 | | | | GJA1 | 1.00 |
| 12713 | 3 | | | | | GAL3ST1 | 1.00 | 12809 | 3 | | | | GJA10 | 1.00 |
| 12714 | 3 | | | | | GAL3ST2 | 1.00 | 12810 | 3 | | | | GJA3 | 1.00 |
| 12715 | 3 | | | | | GAL3ST3 | 1.00 | 12811 | 3 | | | | GJA4 | 1.00 |
| 12716 | 3 | | | | | GALNT13 | 1.00 | 12812 | 3 | | | | GJA5 | 1.00 |
| 12717 | 3 | | | | | GALNT14 | 1.00 | 12813 | 3 | | | | GJA8 | 1.00 |
| 12718 | 3 | | | | | GALNT5 | 1.00 | 12814 | 3 | | | | GJA9 | 1.00 |
| 12719 | 3 | | | | | GALNT8 | 1.00 | 12815 | 3 | | | | GJA9-MYCBP | 1.00 |
| 12720 | 3 | | | | | GALNT9 | 1.00 | 12816 | 3 | | | | GJB1 | 1.00 |
| 12721 | 3 | | | | | GALNTL1 | 1.00 | 12817 | 3 | | | | GJB2 | 1.00 |
| 12722 | 3 | | | | | GALNTL2 | 1.00 | 12818 | 3 | | | | GJB3 | 1.00 |
| 12723 | 3 | | | | | GALNTL4 | 1.00 | 12819 | 3 | | | | GJB4 | 1.00 |
| 12724 | 3 | | | | | GALNTL5 | 1.00 | 12820 | 3 | | | | GJB5 | 1.00 |
| 12725 | 3 | | | | | GALNTL6 | 1.00 | 12821 | 3 | | | | GJB6 | 1.00 |
| 12726 | 3 | | | | | GALP | 1.00 | 12822 | 3 | | | | GJB7 | 1.00 |
| 12727 | 3 | | | | | GALR1 | 1.00 | 12823 | 3 | | | | GJC1 | 1.00 |
| 12728 | 3 | | | | | GALR2 | 1.00 | 12824 | 3 | | | | GJC2 | 1.00 |
| 12729 | 3 | | | | | GALR3 | 1.00 | 12825 | 3 | | | | GJC3 | 1.00 |
| 12730 | 3 | | | | | GAN | 1.00 | 12826 | 3 | | | | GJD2 | 1.00 |
| 12731 | 3 | | | | | GAP43 | 1.00 | 12827 | 3 | | | | GJD3 | 1.00 |
| 12732 | 3 | | | | | GAPDHS | 1.00 | 12828 | 3 | | | | GJD4 | 1.00 |
| 12733 | 3 | | | | | GARNL3 | 1.00 | 12829 | 3 | | | | GK2 | 1.00 |
| 12734 | 3 | | | | | GAS1 | 1.00 | 12830 | 3 | | | | GKN1 | 1.00 |
| 12735 | 3 | | | | | GAS2 | 1.00 | 12831 | 3 | | | | GKN2 | 1.00 |
| 12736 | 3 | | | | | GAS2L2 | 1.00 | 12832 | 3 | | | | GLB1L | 1.00 |
| 12737 | 3 | | | | | GAS2L3 | 1.00 | 12833 | 3 | | | | GLB1L2 | 1.00 |
| 12738 | 3 | | | | | GAS8 | 1.00 | 12834 | 3 | | | | GLB1L3 | 1.00 |
| 12739 | 3 | | | | | GAST | 1.00 | 12835 | 3 | | | | GLDC | 1.00 |
| 12740 | 3 | | | | | GATA4 | 1.00 | 12836 | 3 | | | | GLDN | 1.00 |
| 12741 | 3 | | | | | GATA5 | 1.00 | 12837 | 3 | | | | GLI2 | 1.00 |
| 12742 | 3 | | | | | GATA6 | 1.00 | 12838 | 3 | | | | GLI3 | 1.00 |
| 12743 | 3 | | | | | GATSL1 | 1.00 | 12839 | 3 | | | | GLIPR1L1 | 1.00 |
| 12744 | 3 | | | | | GBA3 | 1.00 | 12840 | 3 | | | | GLIPR1L2 | 1.00 |
| 12745 | 3 | | | | | GBP1P1 | 1.00 | 12841 | 3 | | | | GLIS1 | 1.00 |
| 12746 | 3 | | | | | GBP6 | 1.00 | 12842 | 3 | | | | GLIS3 | 1.00 |
| 12747 | 3 | | | | | GBP7 | 1.00 | 12843 | 3 | | | | GLIS3-AS1 | 1.00 |
| 12748 | 3 | | | | | GBX1 | 1.00 | 12844 | 3 | | | | GLMN | 1.00 |
| 12749 | 3 | | | | | GBX2 | 1.00 | 12845 | 3 | | | | GLOD5 | 1.00 |
| 12750 | 3 | | | | | GC | 1.00 | 12846 | 3 | | | | GLP1R | 1.00 |
| 12751 | 3 | | | | | GCAT | 1.00 | 12847 | 3 | | | | GLP2R | 1.00 |
| 12752 | 3 | | | | | GCG | 1.00 | 12848 | 3 | | | | GLRA1 | 1.00 |
| 12753 | 3 | | | | | GCGR | 1.00 | 12849 | 3 | | | | GLRA2 | 1.00 |
| 12754 | 3 | | | | | GCK | 1.00 | 12850 | 3 | | | | GLRA3 | 1.00 |
| 12755 | 3 | | | | | GCKR | 1.00 | 12851 | 3 | | | | GLRA4 | 1.00 |
| 12756 | 3 | | | | | GCM1 | 1.00 | 12852 | 3 | | | | GLRB | 1.00 |
| 12757 | 3 | | | | | GCM2 | 1.00 | 12853 | 3 | | | | GLS2 | 1.00 |
| 12758 | 3 | | | | | GCNT3 | 1.00 | 12854 | 3 | | | | GLT25D2 | 1.00 |
| 12759 | 3 | | | | | GCNT7 | 1.00 | 12855 | 3 | | | | GLT6D1 | 1.00 |
| 12760 | 3 | | | | | GCOM1 | 1.00 | 12856 | 3 | | | | GLT8D2 | 1.00 |
| 12761 | 3 | | | | | GCSH | 1.00 | 12857 | 3 | | | | GLTPD2 | 1.00 |
| 12762 | 3 | | | | | GDA | 1.00 | 12858 | 3 | | | | GLYAT | 1.00 |

Fig. 41 - 68

| | | | | | | | | | | | | |
|---|---|---|---|---|---|---|---|---|---|---|---|---|
| 12859 | 3 | | | | | GLYATL1 | 1.00 | 12955 | 3 | | GPR22 | 1.00 |
| 12860 | 3 | | | | | GLYATL2 | 1.00 | 12956 | 3 | | GPR26 | 1.00 |
| 12861 | 3 | | | | | GLYATL3 | 1.00 | 12957 | 3 | | GPR3 | 1.00 |
| 12862 | 3 | | | | | GLYCAM1 | 1.00 | 12958 | 3 | | GPR31 | 1.00 |
| 12863 | 3 | | | | | GM140 | 1.00 | 12959 | 3 | | GPR32 | 1.00 |
| 12864 | 3 | | | | | GML | 1.00 | 12960 | 3 | | GPR33 | 1.00 |
| 12865 | 3 | | | | | GMNC | 1.00 | 12961 | 3 | | GPR37 | 1.00 |
| 12866 | 3 | | | | | GNA14 | 1.00 | 12962 | 3 | | GPR37L1 | 1.00 |
| 12867 | 3 | | | | | GNAI1 | 1.00 | 12963 | 3 | | GPR39 | 1.00 |
| 12868 | 3 | | | | | GNAL | 1.00 | 12964 | 3 | | GPR4 | 1.00 |
| 12869 | 3 | | | | | GNAS-AS1 | 1.00 | 12965 | 3 | | GPR45 | 1.00 |
| 12870 | 3 | | | | | GNAT1 | 1.00 | 12966 | 3 | | GPR50 | 1.00 |
| 12871 | 3 | | | | | GNAT2 | 1.00 | 12967 | 3 | | GPR52 | 1.00 |
| 12872 | 3 | | | | | GNAT3 | 1.00 | 12968 | 3 | | GPR6 | 1.00 |
| 12873 | 3 | | | | | GNB3 | 1.00 | 12969 | 3 | | GPR61 | 1.00 |
| 12874 | 3 | | | | | GNG12 | 1.00 | 12970 | 3 | | GPR62 | 1.00 |
| 12875 | 3 | | | | | GNG13 | 1.00 | 12971 | 3 | | GPR63 | 1.00 |
| 12876 | 3 | | | | | GNG3 | 1.00 | 12972 | 3 | | GPR64 | 1.00 |
| 12877 | 3 | | | | | GNG4 | 1.00 | 12973 | 3 | | GPR75-AS83 | 1.00 |
| 12878 | 3 | | | | | GNGT1 | 1.00 | 12974 | 3 | | GPR78 | 1.00 |
| 12879 | 3 | | | | | GNMT | 1.00 | 12975 | 3 | | GPR83 | 1.00 |
| 12880 | 3 | | | | | GNN | 1.00 | 12976 | 3 | | GPR85 | 1.00 |
| 12881 | 3 | | | | | GNRH2 | 1.00 | 12977 | 3 | | GPR87 | 1.00 |
| 12882 | 3 | | | | | GNRHR | 1.00 | 12978 | 3 | | GPR88 | 1.00 |
| 12883 | 3 | | | | | GOLGA2P3Y | 1.00 | 12979 | 3 | | GPR98 | 1.00 |
| 12884 | 3 | | | | | GOLGA6A | 1.00 | 12980 | 3 | | GPRASP2 | 1.00 |
| 12885 | 3 | | | | | GOLGA6B | 1.00 | 12981 | 3 | | GPRC5A | 1.00 |
| 12886 | 3 | | | | | GOLGA6C | 1.00 | 12982 | 3 | | GPRC5B | 1.00 |
| 12887 | 3 | | | | | GOLGA6D | 1.00 | 12983 | 3 | | GPRC5C | 1.00 |
| 12888 | 3 | | | | | GOLGA6L1 | 1.00 | 12984 | 3 | | GPRC5D | 1.00 |
| 12889 | 3 | | | | | GOLGA6L10 | 1.00 | 12985 | 3 | | GPRC6A | 1.00 |
| 12890 | 3 | | | | | GOLGA6L5 | 1.00 | 12986 | 3 | | GPRIN1 | 1.00 |
| 12891 | 3 | | | | | GOLGA6L6 | 1.00 | 12987 | 3 | | GPRIN2 | 1.00 |
| 12892 | 3 | | | | | GOLGA6L9 | 1.00 | 12988 | 3 | | GPT | 1.00 |
| 12893 | 3 | | | | | GOLGA8C | 1.00 | 12989 | 3 | | GPT2 | 1.00 |
| 12894 | 3 | | | | | GOLGA8DP | 1.00 | 12990 | 3 | | GPX2 | 1.00 |
| 12895 | 3 | | | | | GOLGA8E | 1.00 | 12991 | 3 | | GPX5 | 1.00 |
| 12896 | 3 | | | | | GOLGA8F | 1.00 | 12992 | 3 | | GPX6 | 1.00 |
| 12897 | 3 | | | | | GOLGA8G | 1.00 | 12993 | 3 | | GPX8 | 1.00 |
| 12898 | 3 | | | | | GOLGA8IP | 1.00 | 12994 | 3 | | GRAMD2 | 1.00 |
| 12899 | 3 | | | | | GOLT1A | 1.00 | 12995 | 3 | | GRB14 | 1.00 |
| 12900 | 3 | | | | | GOT1L1 | 1.00 | 12996 | 3 | | GRB7 | 1.00 |
| 12901 | 3 | | | | | GP2 | 1.00 | 12997 | 3 | | GREB1 | 1.00 |
| 12902 | 3 | | | | | GPAT2 | 1.00 | 12998 | 3 | | GREB3L | 1.00 |
| 12903 | 3 | | | | | GPC1 | 1.00 | 12999 | 3 | | GREM1 | 1.00 |
| 12904 | 3 | | | | | GPC2 | 1.00 | 13000 | 3 | | GREM2 | 1.00 |
| 12905 | 3 | | | | | GPC3 | 1.00 | 13001 | 3 | | GRHL2 | 1.00 |
| 12906 | 3 | | | | | GPC4 | 1.00 | 13002 | 3 | | GRHL3 | 1.00 |
| 12907 | 3 | | | | | GPC5 | 1.00 | 13003 | 3 | | GRIA1 | 1.00 |
| 12908 | 3 | | | | | GPC6 | 1.00 | 13004 | 3 | | GRIA2 | 1.00 |
| 12909 | 3 | | | | | GPCRLTM7 | 1.00 | 13005 | 3 | | GRIA3 | 1.00 |
| 12910 | 3 | | | | | GPD1 | 1.00 | 13006 | 3 | | GRIA4 | 1.00 |
| 12911 | 3 | | | | | GPHA2 | 1.00 | 13007 | 3 | | GRID1 | 1.00 |
| 12912 | 3 | | | | | GPHBS | 1.00 | 13008 | 3 | | GRID2 | 1.00 |
| 12913 | 3 | | | | | GPIHBP1 | 1.00 | 13009 | 3 | | GRID2IP | 1.00 |
| 12914 | 3 | | | | | GPLD1 | 1.00 | 13010 | 3 | | GRIK1 | 1.00 |
| 12915 | 3 | | | | | GPM6B | 1.00 | 13011 | 3 | | GRIK1-AS1 | 1.00 |
| 12916 | 3 | | | | | GPNMB | 1.00 | 13012 | 3 | | GRIK1-AS2 | 1.00 |
| 12917 | 3 | | | | | GPR1 | 1.00 | 13013 | 3 | | GRIK2 | 1.00 |
| 12918 | 3 | | | | | GPR101 | 1.00 | 13014 | 3 | | GRIK3 | 1.00 |
| 12919 | 3 | | | | | GPR110 | 1.00 | 13015 | 3 | | GRIK4 | 1.00 |
| 12920 | 3 | | | | | GPR111 | 1.00 | 13016 | 3 | | GRIK5 | 1.00 |
| 12921 | 3 | | | | | GPR112 | 1.00 | 13017 | 3 | | GRIN1 | 1.00 |
| 12922 | 3 | | | | | GPR113 | 1.00 | 13018 | 3 | | GRIN2A | 1.00 |
| 12923 | 3 | | | | | GPR115 | 1.00 | 13019 | 3 | | GRIN2B | 1.00 |
| 12924 | 3 | | | | | GPR116 | 1.00 | 13020 | 3 | | GRIN2C | 1.00 |
| 12925 | 3 | | | | | GPR119 | 1.00 | 13021 | 3 | | GRIN2D | 1.00 |
| 12926 | 3 | | | | | GPR12 | 1.00 | 13022 | 3 | | GRIN3A | 1.00 |
| 12927 | 3 | | | | | GPR123 | 1.00 | 13023 | 3 | | GRIN3B | 1.00 |
| 12928 | 3 | | | | | GPR125 | 1.00 | 13024 | 3 | | GRIP1 | 1.00 |
| 12929 | 3 | | | | | GPR126 | 1.00 | 13025 | 3 | | GRIP2 | 1.00 |
| 12930 | 3 | | | | | GPR128 | 1.00 | 13026 | 3 | | GRK1 | 1.00 |
| 12931 | 3 | | | | | GPR135 | 1.00 | 13027 | 3 | | GRK4 | 1.00 |
| 12932 | 3 | | | | | GPR137C | 1.00 | 13028 | 3 | | GRK7 | 1.00 |
| 12933 | 3 | | | | | GPR139 | 1.00 | 13029 | 3 | | GRM1 | 1.00 |
| 12934 | 3 | | | | | GPR142 | 1.00 | 13030 | 3 | | GRM2 | 1.00 |
| 12935 | 3 | | | | | GPR143 | 1.00 | 13031 | 3 | | GRM3 | 1.00 |
| 12936 | 3 | | | | | GPR144 | 1.00 | 13032 | 3 | | GRM4 | 1.00 |
| 12937 | 3 | | | | | GPR148 | 1.00 | 13033 | 3 | | GRM5 | 1.00 |
| 12938 | 3 | | | | | GPR149 | 1.00 | 13034 | 3 | | GRM6 | 1.00 |
| 12939 | 3 | | | | | GPR150 | 1.00 | 13035 | 3 | | GRM7 | 1.00 |
| 12940 | 3 | | | | | GPR151 | 1.00 | 13036 | 3 | | GRM8 | 1.00 |
| 12941 | 3 | | | | | GPR152 | 1.00 | 13037 | 3 | | GRP | 1.00 |
| 12942 | 3 | | | | | GPR156 | 1.00 | 13038 | 3 | | GRPR | 1.00 |
| 12943 | 3 | | | | | GPR158 | 1.00 | 13039 | 3 | | GRTP1 | 1.00 |
| 12944 | 3 | | | | | GPR161 | 1.00 | 13040 | 3 | | GRXCR1 | 1.00 |
| 12945 | 3 | | | | | GPR17 | 1.00 | 13041 | 3 | | GRXCR2 | 1.00 |
| 12946 | 3 | | | | | GPR172B | 1.00 | 13042 | 3 | | GSC | 1.00 |
| 12947 | 3 | | | | | GPR173 | 1.00 | 13043 | 3 | | GSC2 | 1.00 |
| 12948 | 3 | | | | | GPR176 | 1.00 | 13044 | 3 | | GSDMA | 1.00 |
| 12949 | 3 | | | | | GPR179 | 1.00 | 13045 | 3 | | GSDMC | 1.00 |
| 12950 | 3 | | | | | GPR180 | 1.00 | 13046 | 3 | | GSG1 | 1.00 |
| 12951 | 3 | | | | | GPR182 | 1.00 | 13047 | 3 | | GSG1L | 1.00 |
| 12952 | 3 | | | | | GPR19 | 1.00 | 13048 | 3 | | GSG2 | 1.00 |
| 12953 | 3 | | | | | GPR20 | 1.00 | 13049 | 3 | | GSTA1 | 1.00 |
| 12954 | 3 | | | | | GPR21 | 1.00 | 13050 | 3 | | GSTA2 | 1.00 |

Fig. 41 - 69

| | | | | | | | | | | | | | | |
|---|---|---|---|---|---|---|---|---|---|---|---|---|---|---|
| 13051 | 3 | | | | | GSTA3 | 1.00 | 13147 | 3 | | | | HEPACAM2 | 1.00 |
| 13052 | 3 | | | | | GSTA4 | 1.00 | 13148 | 3 | | | | HEPH | 1.00 |
| 13053 | 3 | | | | | GSTA5 | 1.00 | 13149 | 3 | | | | HEPHL1 | 1.00 |
| 13054 | 3 | | | | | GSTA7P | 1.00 | 13150 | 3 | | | | HEPN1 | 1.00 |
| 13055 | 3 | | | | | GSTM5 | 1.00 | 13151 | 3 | | | | HERC2P4 | 1.00 |
| 13056 | 3 | | | | | GSTO2 | 1.00 | 13152 | 3 | | | | HERC2P7 | 1.00 |
| 13057 | 3 | | | | | GSTT2 | 1.00 | 13153 | 3 | | | | HES2 | 1.00 |
| 13058 | 3 | | | | | GSTT2B | 1.00 | 13154 | 3 | | | | HES3 | 1.00 |
| 13059 | 3 | | | | | GSTTP1 | 1.00 | 13155 | 3 | | | | HES4 | 1.00 |
| 13060 | 3 | | | | | GSTTP2 | 1.00 | 13156 | 3 | | | | HES5 | 1.00 |
| 13061 | 3 | | | | | GSX1 | 1.00 | 13157 | 3 | | | | HES7 | 1.00 |
| 13062 | 3 | | | | | GSX2 | 1.00 | 13158 | 3 | | | | HESX1 | 1.00 |
| 13063 | 3 | | | | | GTF2A1L | 1.00 | 13159 | 3 | | | | HEY2 | 1.00 |
| 13064 | 3 | | | | | GTF2H2D | 1.00 | 13160 | 3 | | | | HEYL | 1.00 |
| 13065 | 3 | | | | | GTF2IRD1 | 1.00 | 13161 | 3 | | | | HFE2 | 1.00 |
| 13066 | 3 | | | | | GTF2IRD2P1 | 1.00 | 13162 | 3 | | | | HFM1 | 1.00 |
| 13067 | 3 | | | | | GTSE1 | 1.00 | 13163 | 3 | | | | HGC6.3 | 1.00 |
| 13068 | 3 | | | | | GTSF1L | 1.00 | 13164 | 3 | | | | HGD | 1.00 |
| 13069 | 3 | | | | | GUCA1A | 1.00 | 13165 | 3 | | | | HGFAC | 1.00 |
| 13070 | 3 | | | | | GUCA1B | 1.00 | 13166 | 3 | | | | HHAT | 1.00 |
| 13071 | 3 | | | | | GUCA1C | 1.00 | 13167 | 3 | | | | HHATL | 1.00 |
| 13072 | 3 | | | | | GUCA2A | 1.00 | 13168 | 3 | | | | HHIP | 1.00 |
| 13073 | 3 | | | | | GUCA2B | 1.00 | 13169 | 3 | | | | HHIPL1 | 1.00 |
| 13074 | 3 | | | | | GUCY1A2 | 1.00 | 13170 | 3 | | | | HHIPL2 | 1.00 |
| 13075 | 3 | | | | | GUCY1B2 | 1.00 | 13171 | 3 | | | | HHLA1 | 1.00 |
| 13076 | 3 | | | | | GUCY2C | 1.00 | 13172 | 3 | | | | HHLA2 | 1.00 |
| 13077 | 3 | | | | | GUCY2D | 1.00 | 13173 | 3 | | | | HIF1A-AS2 | 1.00 |
| 13078 | 3 | | | | | GUCY2E | 1.00 | 13174 | 3 | | | | HIF3A | 1.00 |
| 13079 | 3 | | | | | GUCY2F | 1.00 | 13175 | 3 | | | | HIGD1B | 1.00 |
| 13080 | 3 | | | | | GUCY2GP | 1.00 | 13176 | 3 | | | | HIGD1C | 1.00 |
| 13081 | 3 | | | | | GULP1 | 1.00 | 13177 | 3 | | | | HIGD2B | 1.00 |
| 13082 | 3 | | | | | GUSBP10 | 1.00 | 13178 | 3 | | | | HILS1 | 1.00 |
| 13083 | 3 | | | | | GUSBP2 | 1.00 | 13179 | 3 | | | | HIPK4 | 1.00 |
| 13084 | 3 | | | | | GUSBP3 | 1.00 | 13180 | 3 | | | | HIST1H1A | 1.00 |
| 13085 | 3 | | | | | GUSBP4 | 1.00 | 13181 | 3 | | | | HIST1H1B | 1.00 |
| 13086 | 3 | | | | | GXYLT2 | 1.00 | 13182 | 3 | | | | HIST1H1E | 1.00 |
| 13087 | 3 | | | | | GYG2 | 1.00 | 13183 | 3 | | | | HIST1H2AA | 1.00 |
| 13088 | 3 | | | | | GYG2P1 | 1.00 | 13184 | 3 | | | | HIST1H2AB | 1.00 |
| 13089 | 3 | | | | | GYPA | 1.00 | 13185 | 3 | | | | HIST1H2AH | 1.00 |
| 13090 | 3 | | | | | GYPE | 1.00 | 13186 | 3 | | | | HIST1H2APS1 | 1.00 |
| 13091 | 3 | | | | | GYS2 | 1.00 | 13187 | 3 | | | | HIST1H2BA | 1.00 |
| 13092 | 3 | | | | | H1FNT | 1.00 | 13188 | 3 | | | | HIST1H2BI | 1.00 |
| 13093 | 3 | | | | | H1FOO | 1.00 | 13189 | 3 | | | | HIST1H2BM | 1.00 |
| 13094 | 3 | | | | | H1FX-AS1 | 1.00 | 13190 | 3 | | | | HIST1H3B | 1.00 |
| 13095 | 3 | | | | | H2AFB1 | 1.00 | 13191 | 3 | | | | HIST1H3C | 1.00 |
| 13096 | 3 | | | | | H2AFB3 | 1.00 | 13192 | 3 | | | | HIST1H3I | 1.00 |
| 13097 | 3 | | | | | H2BFM | 1.00 | 13193 | 3 | | | | HIST1H3J | 1.00 |
| 13098 | 3 | | | | | H2BFWT | 1.00 | 13194 | 3 | | | | HIST1H4G | 1.00 |
| 13099 | 3 | | | | | H2BFXP | 1.00 | 13195 | 3 | | | | HIST2H2AB | 1.00 |
| 13100 | 3 | | | | | HABP2 | 1.00 | 13196 | 3 | | | | HIST3H2BB | 1.00 |
| 13101 | 3 | | | | | HACE1 | 1.00 | 13197 | 3 | | | | HIST3H3 | 1.00 |
| 13102 | 3 | | | | | HAGHL | 1.00 | 13198 | 3 | | | | HJURP | 1.00 |
| 13103 | 3 | | | | | HAMP | 1.00 | 13199 | 3 | | | | HKDC1 | 1.00 |
| 13104 | 3 | | | | | HAND1 | 1.00 | 13200 | 3 | | | | HLA-J | 1.00 |
| 13105 | 3 | | | | | HAND2 | 1.00 | 13201 | 3 | | | | HLA-L | 1.00 |
| 13106 | 3 | | | | | HAO1 | 1.00 | 13202 | 3 | | | | HLF | 1.00 |
| 13107 | 3 | | | | | HAO2 | 1.00 | 13203 | 3 | | | | HMCN1 | 1.00 |
| 13108 | 3 | | | | | HAP1 | 1.00 | 13204 | 3 | | | | HMGA1P7 | 1.00 |
| 13109 | 3 | | | | | HAPLN1 | 1.00 | 13205 | 3 | | | | HMGA2 | 1.00 |
| 13110 | 3 | | | | | HAPLN2 | 1.00 | 13206 | 3 | | | | HMGB3P1 | 1.00 |
| 13111 | 3 | | | | | HAPLN4 | 1.00 | 13207 | 3 | | | | HMGB4 | 1.00 |
| 13112 | 3 | | | | | HAR1A | 1.00 | 13208 | 3 | | | | HMGCLL1 | 1.00 |
| 13113 | 3 | | | | | HAR1B | 1.00 | 13209 | 3 | | | | HMGCS2 | 1.00 |
| 13114 | 3 | | | | | HAS1 | 1.00 | 13210 | 3 | | | | HMGN2P46 | 1.00 |
| 13115 | 3 | | | | | HAS2 | 1.00 | 13211 | 3 | | | | HMGN5 | 1.00 |
| 13116 | 3 | | | | | HAS2-AS1 | 1.00 | 13212 | 3 | | | | HMHB1 | 1.00 |
| 13117 | 3 | | | | | HAS3 | 1.00 | 13213 | 3 | | | | HMMR | 1.00 |
| 13118 | 3 | | | | | HAVCR1 | 1.00 | 13214 | 3 | | | | HMP19 | 1.00 |
| 13119 | 3 | | | | | HBBP1 | 1.00 | 13215 | 3 | | | | HMSD | 1.00 |
| 13120 | 3 | | | | | HBE1 | 1.00 | 13216 | 3 | | | | HMX1 | 1.00 |
| 13121 | 3 | | | | | HBEGF | 1.00 | 13217 | 3 | | | | HMX2 | 1.00 |
| 13122 | 3 | | | | | HCAR1 | 1.00 | 13218 | 3 | | | | HMX3 | 1.00 |
| 13123 | 3 | | | | | HCG22 | 1.00 | 13219 | 3 | | | | HNF1A | 1.00 |
| 13124 | 3 | | | | | HCG23 | 1.00 | 13220 | 3 | | | | HNF1A-AS1 | 1.00 |
| 13125 | 3 | | | | | HCG25 | 1.00 | 13221 | 3 | | | | HNF1B | 1.00 |
| 13126 | 3 | | | | | HCG4 | 1.00 | 13222 | 3 | | | | HNF4A | 1.00 |
| 13127 | 3 | | | | | HCG4B | 1.00 | 13223 | 3 | | | | HNF4G | 1.00 |
| 13128 | 3 | | | | | HCG9 | 1.00 | 13224 | 3 | | | | HNRNPA1P10 | 1.00 |
| 13129 | 3 | | | | | HCN1 | 1.00 | 13225 | 3 | | | | HNRNPCL1 | 1.00 |
| 13130 | 3 | | | | | HCN2 | 1.00 | 13226 | 3 | | | | HOGA1 | 1.00 |
| 13131 | 3 | | | | | HCN3 | 1.00 | 13227 | 3 | | | | HOMER1 | 1.00 |
| 13132 | 3 | | | | | HCN4 | 1.00 | 13228 | 3 | | | | HOOK2 | 1.00 |
| 13133 | 3 | | | | | HCRT | 1.00 | 13229 | 3 | | | | HORMAD1 | 1.00 |
| 13134 | 3 | | | | | HCRTR1 | 1.00 | 13230 | 3 | | | | HORMAD2 | 1.00 |
| 13135 | 3 | | | | | HCRTR2 | 1.00 | 13231 | 3 | | | | HOTAIR | 1.00 |
| 13136 | 3 | | | | | HDGFL1 | 1.00 | 13232 | 3 | | | | HOTTIP | 1.00 |
| 13137 | 3 | | | | | HDX | 1.00 | 13233 | 3 | | | | HOXA-AS3 | 1.00 |
| 13138 | 3 | | | | | HEATR4 | 1.00 | 13234 | 3 | | | | HOXA-AS5 | 1.00 |
| 13139 | 3 | | | | | HEATR7B2 | 1.00 | 13235 | 3 | | | | HOXA10-HOXA9 | 1.00 |
| 13140 | 3 | | | | | HEATR8 | 1.00 | 13236 | 3 | | | | HOXA11 | 1.00 |
| 13141 | 3 | | | | | HEATR8-TTC4 | 1.00 | 13237 | 3 | | | | HOXA13 | 1.00 |
| 13142 | 3 | | | | | HECTD2 | 1.00 | 13238 | 3 | | | | HOXA2 | 1.00 |
| 13143 | 3 | | | | | HECW1 | 1.00 | 13239 | 3 | | | | HOXA3 | 1.00 |
| 13144 | 3 | | | | | HELLS | 1.00 | 13240 | 3 | | | | HOXA4 | 1.00 |
| 13145 | 3 | | | | | HELT | 1.00 | 13241 | 3 | | | | HOXA5 | 1.00 |
| 13146 | 3 | | | | | HEPACAM | 1.00 | 13242 | 3 | | | | HOXA6 | 1.00 |

Fig. 41 - 70

| | | | | | | | | | | | | | | |
|---|---|---|---|---|---|---|---|---|---|---|---|---|---|---|
| 13243 | 3 | | | | | HOXA7 | 1.00 | 13339 | 3 | | | | HTR2A | 1.00 |
| 13244 | 3 | | | | | HOXB-AS3 | 1.00 | 13340 | 3 | | | | HTR2B | 1.00 |
| 13245 | 3 | | | | | HOXB-AS5 | 1.00 | 13341 | 3 | | | | HTR2C | 1.00 |
| 13246 | 3 | | | | | HOXB1 | 1.00 | 13342 | 3 | | | | HTR3A | 1.00 |
| 13247 | 3 | | | | | HOXB13 | 1.00 | 13343 | 3 | | | | HTR3B | 1.00 |
| 13248 | 3 | | | | | HOXB3 | 1.00 | 13344 | 3 | | | | HTR3C | 1.00 |
| 13249 | 3 | | | | | HOXB5 | 1.00 | 13345 | 3 | | | | HTR3D | 1.00 |
| 13250 | 3 | | | | | HOXB6 | 1.00 | 13346 | 3 | | | | HTR3E | 1.00 |
| 13251 | 3 | | | | | HOXB7 | 1.00 | 13347 | 3 | | | | HTR4 | 1.00 |
| 13252 | 3 | | | | | HOXB8 | 1.00 | 13348 | 3 | | | | HTR5A | 1.00 |
| 13253 | 3 | | | | | HOXB9 | 1.00 | 13349 | 3 | | | | HTR6 | 1.00 |
| 13254 | 3 | | | | | HOXC10 | 1.00 | 13350 | 3 | | | | HTR7 | 1.00 |
| 13255 | 3 | | | | | HOXC11 | 1.00 | 13351 | 3 | | | | HTRA3 | 1.00 |
| 13256 | 3 | | | | | HOXC12 | 1.00 | 13352 | 3 | | | | HTRA4 | 1.00 |
| 13257 | 3 | | | | | HOXC13 | 1.00 | 13353 | 3 | | | | HTT-AS1 | 1.00 |
| 13258 | 3 | | | | | HOXC5 | 1.00 | 13354 | 3 | | | | HULC | 1.00 |
| 13259 | 3 | | | | | HOXC6 | 1.00 | 13355 | 3 | | | | HUNK | 1.00 |
| 13260 | 3 | | | | | HOXC8 | 1.00 | 13356 | 3 | | | | HUS1B | 1.00 |
| 13261 | 3 | | | | | HOXC9 | 1.00 | 13357 | 3 | | | | HYAL1 | 1.00 |
| 13262 | 3 | | | | | HOXD-AS1 | 1.00 | 13358 | 3 | | | | HYAL4 | 1.00 |
| 13263 | 3 | | | | | HOXD-AS2 | 1.00 | 13359 | 3 | | | | HYALP1 | 1.00 |
| 13264 | 3 | | | | | HOXD1 | 1.00 | 13360 | 3 | | | | HYDIN | 1.00 |
| 13265 | 3 | | | | | HOXD10 | 1.00 | 13361 | 3 | | | | HYI | 1.00 |
| 13266 | 3 | | | | | HOXD11 | 1.00 | 13362 | 3 | | | | HYMAI | 1.00 |
| 13267 | 3 | | | | | HOXD12 | 1.00 | 13363 | 3 | | | | IAPP | 1.00 |
| 13268 | 3 | | | | | HOXD13 | 1.00 | 13364 | 3 | | | | IBSP | 1.00 |
| 13269 | 3 | | | | | HOXD3 | 1.00 | 13365 | 3 | | | | ICAM5 | 1.00 |
| 13270 | 3 | | | | | HOXD4 | 1.00 | 13366 | 3 | | | | ID1 | 1.00 |
| 13271 | 3 | | | | | HOXD8 | 1.00 | 13367 | 3 | | | | ID4 | 1.00 |
| 13272 | 3 | | | | | HOXD9 | 1.00 | 13368 | 3 | | | | IDAS | 1.00 |
| 13273 | 3 | | | | | HPCA | 1.00 | 13369 | 3 | | | | IDO2 | 1.00 |
| 13274 | 3 | | | | | HPD | 1.00 | 13370 | 3 | | | | IFITM10 | 1.00 |
| 13275 | 3 | | | | | HPDL | 1.00 | 13371 | 3 | | | | IFITM5 | 1.00 |
| 13276 | 3 | | | | | HPGDS | 1.00 | 13372 | 3 | | | | IFLTD1 | 1.00 |
| 13277 | 3 | | | | | HPN | 1.00 | 13373 | 3 | | | | IFNA1 | 1.00 |
| 13278 | 3 | | | | | HPSE2 | 1.00 | 13374 | 3 | | | | IFNA10 | 1.00 |
| 13279 | 3 | | | | | HPVC1 | 1.00 | 13375 | 3 | | | | IFNA13 | 1.00 |
| 13280 | 3 | | | | | HPX | 1.00 | 13376 | 3 | | | | IFNA14 | 1.00 |
| 13281 | 3 | | | | | HPYR1 | 1.00 | 13377 | 3 | | | | IFNA16 | 1.00 |
| 13282 | 3 | | | | | HR | 1.00 | 13378 | 3 | | | | IFNA17 | 1.00 |
| 13283 | 3 | | | | | HRASLS2 | 1.00 | 13379 | 3 | | | | IFNA2 | 1.00 |
| 13284 | 3 | | | | | HRC | 1.00 | 13380 | 3 | | | | IFNA21 | 1.00 |
| 13285 | 3 | | | | | HRCT1 | 1.00 | 13381 | 3 | | | | IFNA22P | 1.00 |
| 13286 | 3 | | | | | HRG | 1.00 | 13382 | 3 | | | | IFNA4 | 1.00 |
| 13287 | 3 | | | | | HRH1 | 1.00 | 13383 | 3 | | | | IFNA5 | 1.00 |
| 13288 | 3 | | | | | HRH3 | 1.00 | 13384 | 3 | | | | IFNA6 | 1.00 |
| 13289 | 3 | | | | | HRK | 1.00 | 13385 | 3 | | | | IFNA7 | 1.00 |
| 13290 | 3 | | | | | HRNR | 1.00 | 13386 | 3 | | | | IFNA8 | 1.00 |
| 13291 | 3 | | | | | HS3ST2 | 1.00 | 13387 | 3 | | | | IFNB1 | 1.00 |
| 13292 | 3 | | | | | HS3ST4 | 1.00 | 13388 | 3 | | | | IFNE | 1.00 |
| 13293 | 3 | | | | | HS3ST5 | 1.00 | 13389 | 3 | | | | IFNK | 1.00 |
| 13294 | 3 | | | | | HS3ST6 | 1.00 | 13390 | 3 | | | | IFNW1 | 1.00 |
| 13295 | 3 | | | | | HS6ST2 | 1.00 | 13391 | 3 | | | | IFT140 | 1.00 |
| 13296 | 3 | | | | | HS6ST3 | 1.00 | 13392 | 3 | | | | IFT172 | 1.00 |
| 13297 | 3 | | | | | HSD11B1 | 1.00 | 13393 | 3 | | | | IFT74 | 1.00 |
| 13298 | 3 | | | | | HSD11B1L | 1.00 | 13394 | 3 | | | | IFT81 | 1.00 |
| 13299 | 3 | | | | | HSD11B2 | 1.00 | 13395 | 3 | | | | IFT88 | 1.00 |
| 13300 | 3 | | | | | HSD17B13 | 1.00 | 13396 | 3 | | | | IGDCC3 | 1.00 |
| 13301 | 3 | | | | | HSD17B14 | 1.00 | 13397 | 3 | | | | IGDCC4 | 1.00 |
| 13302 | 3 | | | | | HSD17B2 | 1.00 | 13398 | 3 | | | | IGF1 | 1.00 |
| 13303 | 3 | | | | | HSD17B3 | 1.00 | 13399 | 3 | | | | IGF2 | 1.00 |
| 13304 | 3 | | | | | HSD17B6 | 1.00 | 13400 | 3 | | | | IGF2-AS1 | 1.00 |
| 13305 | 3 | | | | | HSD3B1 | 1.00 | 13401 | 3 | | | | IGF2BP1 | 1.00 |
| 13306 | 3 | | | | | HSD3B2 | 1.00 | 13402 | 3 | | | | IGFALS | 1.00 |
| 13307 | 3 | | | | | HSD3BP4 | 1.00 | 13403 | 3 | | | | IGFBP1 | 1.00 |
| 13308 | 3 | | | | | HSD52 | 1.00 | 13404 | 3 | | | | IGFBP5 | 1.00 |
| 13309 | 3 | | | | | HSF2BP | 1.00 | 13405 | 3 | | | | IGFBP6 | 1.00 |
| 13310 | 3 | | | | | HSF4 | 1.00 | 13406 | 3 | | | | IGFBPL1 | 1.00 |
| 13311 | 3 | | | | | HSF5 | 1.00 | 13407 | 3 | | | | IGFL1 | 1.00 |
| 13312 | 3 | | | | | HSFX1 | 1.00 | 13408 | 3 | | | | IGFL2 | 1.00 |
| 13313 | 3 | | | | | HSFX2 | 1.00 | 13409 | 3 | | | | IGFL3 | 1.00 |
| 13314 | 3 | | | | | HSFY1 | 1.00 | 13410 | 3 | | | | IGFL4 | 1.00 |
| 13315 | 3 | | | | | HSFY1P1 | 1.00 | 13411 | 3 | | | | IGFN1 | 1.00 |
| 13316 | 3 | | | | | HSFY2 | 1.00 | 13412 | 3 | | | | IGLL1 | 1.00 |
| 13317 | 3 | | | | | HSP90AB4P | 1.00 | 13413 | 3 | | | | IGLL3P | 1.00 |
| 13318 | 3 | | | | | HSPA12A | 1.00 | 13414 | 3 | | | | IGLON5 | 1.00 |
| 13319 | 3 | | | | | HSPA12B | 1.00 | 13415 | 3 | | | | IGSF1 | 1.00 |
| 13320 | 3 | | | | | HSPA2 | 1.00 | 13416 | 3 | | | | IGSF10 | 1.00 |
| 13321 | 3 | | | | | HSPA4L | 1.00 | 13417 | 3 | | | | IGSF11 | 1.00 |
| 13322 | 3 | | | | | HSPB2 | 1.00 | 13418 | 3 | | | | IGSF11-AS1 | 1.00 |
| 13323 | 3 | | | | | HSPB2-C11orf52 | 1.00 | 13419 | 3 | | | | IGSF21 | 1.00 |
| 13324 | 3 | | | | | HSPB3 | 1.00 | 13420 | 3 | | | | IGSF22 | 1.00 |
| 13325 | 3 | | | | | HSPB6 | 1.00 | 13421 | 3 | | | | IGSF23 | 1.00 |
| 13326 | 3 | | | | | HSPB7 | 1.00 | 13422 | 3 | | | | IGSF3 | 1.00 |
| 13327 | 3 | | | | | HSPB8 | 1.00 | 13423 | 3 | | | | IGSF5 | 1.00 |
| 13328 | 3 | | | | | HSPB9 | 1.00 | 13424 | 3 | | | | IGSF9 | 1.00 |
| 13329 | 3 | | | | | HSPC072 | 1.00 | 13425 | 3 | | | | IGSF9B | 1.00 |
| 13330 | 3 | | | | | HSPG2 | 1.00 | 13426 | 3 | | | | IHH | 1.00 |
| 13331 | 3 | | | | | HTA | 1.00 | 13427 | 3 | | | | IL11 | 1.00 |
| 13332 | 3 | | | | | HTN1 | 1.00 | 13428 | 3 | | | | IL12A | 1.00 |
| 13333 | 3 | | | | | HTN3 | 1.00 | 13429 | 3 | | | | IL12B | 1.00 |
| 13334 | 3 | | | | | HTR1A | 1.00 | 13430 | 3 | | | | IL13 | 1.00 |
| 13335 | 3 | | | | | HTR1B | 1.00 | 13431 | 3 | | | | IL13RA2 | 1.00 |
| 13336 | 3 | | | | | HTR1D | 1.00 | 13432 | 3 | | | | IL17A | 1.00 |
| 13337 | 3 | | | | | HTR1E | 1.00 | 13433 | 3 | | | | IL17B | 1.00 |
| 13338 | 3 | | | | | HTR1F | 1.00 | 13434 | 3 | | | | IL17C | 1.00 |

Fig. 41 - 71

| | | | | | | | | | | | | | | |
|---|---|---|---|---|---|---|---|---|---|---|---|---|---|---|
| 13435 | 3 | | | | | IL17D | 1.00 | 13531 | 3 | | | | IRX3 | 1.00 |
| 13436 | 3 | | | | | IL17F | 1.00 | 13532 | 3 | | | | IRX4 | 1.00 |
| 13437 | 3 | | | | | IL17RD | 1.00 | 13533 | 3 | | | | IRX5 | 1.00 |
| 13438 | 3 | | | | | IL17RE | 1.00 | 13534 | 3 | | | | IRX6 | 1.00 |
| 13439 | 3 | | | | | IL17REL | 1.00 | 13535 | 3 | | | | ISL1 | 1.00 |
| 13440 | 3 | | | | | IL19 | 1.00 | 13536 | 3 | | | | ISLR | 1.00 |
| 13441 | 3 | | | | | IL1A | 1.00 | 13537 | 3 | | | | ISLR2 | 1.00 |
| 13442 | 3 | | | | | IL1F10 | 1.00 | 13538 | 3 | | | | ISM2 | 1.00 |
| 13443 | 3 | | | | | IL1RAPL1 | 1.00 | 13539 | 3 | | | | ISPD | 1.00 |
| 13444 | 3 | | | | | IL1RAPL2 | 1.00 | 13540 | 3 | | | | ISX | 1.00 |
| 13445 | 3 | | | | | IL1RL2 | 1.00 | 13541 | 3 | | | | ISY1-RAB43 | 1.00 |
| 13446 | 3 | | | | | IL2 | 1.00 | 13542 | 3 | | | | ITGA1 | 1.00 |
| 13447 | 3 | | | | | IL20 | 1.00 | 13543 | 3 | | | | ITGA10 | 1.00 |
| 13448 | 3 | | | | | IL20RA | 1.00 | 13544 | 3 | | | | ITGA11 | 1.00 |
| 13449 | 3 | | | | | IL20RB | 1.00 | 13545 | 3 | | | | ITGA2 | 1.00 |
| 13450 | 3 | | | | | IL21 | 1.00 | 13546 | 3 | | | | ITGA3 | 1.00 |
| 13451 | 3 | | | | | IL22 | 1.00 | 13547 | 3 | | | | ITGA7 | 1.00 |
| 13452 | 3 | | | | | IL22RA1 | 1.00 | 13548 | 3 | | | | ITGA8 | 1.00 |
| 13453 | 3 | | | | | IL22RA2 | 1.00 | 13549 | 3 | | | | ITGA9 | 1.00 |
| 13454 | 3 | | | | | IL23R | 1.00 | 13550 | 3 | | | | ITGAD | 1.00 |
| 13455 | 3 | | | | | IL25 | 1.00 | 13551 | 3 | | | | ITGAE | 1.00 |
| 13456 | 3 | | | | | IL26 | 1.00 | 13552 | 3 | | | | ITGB1BP2 | 1.00 |
| 13457 | 3 | | | | | IL27 | 1.00 | 13553 | 3 | | | | ITGB1BP3 | 1.00 |
| 13458 | 3 | | | | | IL28A | 1.00 | 13554 | 3 | | | | ITGB4 | 1.00 |
| 13459 | 3 | | | | | IL28B | 1.00 | 13555 | 3 | | | | ITGB6 | 1.00 |
| 13460 | 3 | | | | | IL29 | 1.00 | 13556 | 3 | | | | ITGB8 | 1.00 |
| 13461 | 3 | | | | | IL3 | 1.00 | 13557 | 3 | | | | ITGBL1 | 1.00 |
| 13462 | 3 | | | | | IL31 | 1.00 | 13558 | 3 | | | | ITIH1 | 1.00 |
| 13463 | 3 | | | | | IL31RA | 1.00 | 13559 | 3 | | | | ITIH2 | 1.00 |
| 13464 | 3 | | | | | IL33 | 1.00 | 13560 | 3 | | | | ITIH3 | 1.00 |
| 13465 | 3 | | | | | IL34 | 1.00 | 13561 | 3 | | | | ITIH4 | 1.00 |
| 13466 | 3 | | | | | IL36A | 1.00 | 13562 | 3 | | | | ITIH5 | 1.00 |
| 13467 | 3 | | | | | IL36B | 1.00 | 13563 | 3 | | | | ITIH6 | 1.00 |
| 13468 | 3 | | | | | IL36G | 1.00 | 13564 | 3 | | | | ITLN2 | 1.00 |
| 13469 | 3 | | | | | IL36RN | 1.00 | 13565 | 3 | | | | ITPK1-AS1 | 1.00 |
| 13470 | 3 | | | | | IL37 | 1.00 | 13566 | 3 | | | | ITPKA | 1.00 |
| 13471 | 3 | | | | | IL4 | 1.00 | 13567 | 3 | | | | IVL | 1.00 |
| 13472 | 3 | | | | | IL4I1 | 1.00 | 13568 | 3 | | | | IYD | 1.00 |
| 13473 | 3 | | | | | IL5 | 1.00 | 13569 | 3 | | | | IZUMO1 | 1.00 |
| 13474 | 3 | | | | | IL6 | 1.00 | 13570 | 3 | | | | IZUMO2 | 1.00 |
| 13475 | 3 | | | | | IL7 | 1.00 | 13571 | 3 | | | | JAG2 | 1.00 |
| 13476 | 3 | | | | | IL9 | 1.00 | 13572 | 3 | | | | JAKMIP3 | 1.00 |
| 13477 | 3 | | | | | ILDR1 | 1.00 | 13573 | 3 | | | | JAM2 | 1.00 |
| 13478 | 3 | | | | | ILDR2 | 1.00 | 13574 | 3 | | | | JAZF1-AS1 | 1.00 |
| 13479 | 3 | | | | | IMMP1L | 1.00 | 13575 | 3 | | | | JMJD7-PLA2G4B | 1.00 |
| 13480 | 3 | | | | | IMPG1 | 1.00 | 13576 | 3 | | | | JPH1 | 1.00 |
| 13481 | 3 | | | | | IMPG2 | 1.00 | 13577 | 3 | | | | JPH2 | 1.00 |
| 13482 | 3 | | | | | INA | 1.00 | 13578 | 3 | | | | JPH3 | 1.00 |
| 13483 | 3 | | | | | INCA1 | 1.00 | 13579 | 3 | | | | JSRP1 | 1.00 |
| 13484 | 3 | | | | | INE2 | 1.00 | 13580 | 3 | | | | KAAG1 | 1.00 |
| 13485 | 3 | | | | | INGX | 1.00 | 13581 | 3 | | | | KAL1 | 1.00 |
| 13486 | 3 | | | | | INHA | 1.00 | 13582 | 3 | | | | KALRN | 1.00 |
| 13487 | 3 | | | | | INHBA | 1.00 | 13583 | 3 | | | | KANK3 | 1.00 |
| 13488 | 3 | | | | | INHBB | 1.00 | 13584 | 3 | | | | KANK4 | 1.00 |
| 13489 | 3 | | | | | INHBC | 1.00 | 13585 | 3 | | | | KATNAL2 | 1.00 |
| 13490 | 3 | | | | | INHBE | 1.00 | 13586 | 3 | | | | KAZALD1 | 1.00 |
| 13491 | 3 | | | | | INMT | 1.00 | 13587 | 3 | | | | KBTBD10 | 1.00 |
| 13492 | 3 | | | | | INMT-FAM188B | 1.00 | 13588 | 3 | | | | KBTBD12 | 1.00 |
| 13493 | 3 | | | | | INPP5J | 1.00 | 13589 | 3 | | | | KBTBD13 | 1.00 |
| 13494 | 3 | | | | | INS | 1.00 | 13590 | 3 | | | | KBTBD5 | 1.00 |
| 13495 | 3 | | | | | INS-IGF2 | 1.00 | 13591 | 3 | | | | KC6 | 1.00 |
| 13496 | 3 | | | | | INSC | 1.00 | 13592 | 3 | | | | KCNA1 | 1.00 |
| 13497 | 3 | | | | | INSL4 | 1.00 | 13593 | 3 | | | | KCNA10 | 1.00 |
| 13498 | 3 | | | | | INSL5 | 1.00 | 13594 | 3 | | | | KCNA2 | 1.00 |
| 13499 | 3 | | | | | INSL6 | 1.00 | 13595 | 3 | | | | KCNA4 | 1.00 |
| 13500 | 3 | | | | | INSM1 | 1.00 | 13596 | 3 | | | | KCNA5 | 1.00 |
| 13501 | 3 | | | | | INSM2 | 1.00 | 13597 | 3 | | | | KCNA6 | 1.00 |
| 13502 | 3 | | | | | INSRR | 1.00 | 13598 | 3 | | | | KCNA7 | 1.00 |
| 13503 | 3 | | | | | INTS4L1 | 1.00 | 13599 | 3 | | | | KCNAB1 | 1.00 |
| 13504 | 3 | | | | | INTS4L2 | 1.00 | 13600 | 3 | | | | KCNAB3 | 1.00 |
| 13505 | 3 | | | | | INTU | 1.00 | 13601 | 3 | | | | KCNB1 | 1.00 |
| 13506 | 3 | | | | | IP6K3 | 1.00 | 13602 | 3 | | | | KCNB2 | 1.00 |
| 13507 | 3 | | | | | IPW | 1.00 | 13603 | 3 | | | | KCNC1 | 1.00 |
| 13508 | 3 | | | | | IQCA1 | 1.00 | 13604 | 3 | | | | KCNC2 | 1.00 |
| 13509 | 3 | | | | | IQCC | 1.00 | 13605 | 3 | | | | KCNC3 | 1.00 |
| 13510 | 3 | | | | | IQCD | 1.00 | 13606 | 3 | | | | KCNC4 | 1.00 |
| 13511 | 3 | | | | | IQCF1 | 1.00 | 13607 | 3 | | | | KCND1 | 1.00 |
| 13512 | 3 | | | | | IQCF2 | 1.00 | 13608 | 3 | | | | KCND2 | 1.00 |
| 13513 | 3 | | | | | IQCF3 | 1.00 | 13609 | 3 | | | | KCND3 | 1.00 |
| 13514 | 3 | | | | | IQCF4 | 1.00 | 13610 | 3 | | | | KCNE1L | 1.00 |
| 13515 | 3 | | | | | IQCF5 | 1.00 | 13611 | 3 | | | | KCNE2 | 1.00 |
| 13516 | 3 | | | | | IQCF6 | 1.00 | 13612 | 3 | | | | KCNE4 | 1.00 |
| 13517 | 3 | | | | | IQCH | 1.00 | 13613 | 3 | | | | KCNF1 | 1.00 |
| 13518 | 3 | | | | | IQCJ | 1.00 | 13614 | 3 | | | | KCNG3 | 1.00 |
| 13519 | 3 | | | | | IQCJ-SCHIP1 | 1.00 | 13615 | 3 | | | | KCNG4 | 1.00 |
| 13520 | 3 | | | | | IQCK | 1.00 | 13616 | 3 | | | | KCNH1 | 1.00 |
| 13521 | 3 | | | | | IQGAP3 | 1.00 | 13617 | 3 | | | | KCNH4 | 1.00 |
| 13522 | 3 | | | | | IQSEC3 | 1.00 | 13618 | 3 | | | | KCNH5 | 1.00 |
| 13523 | 3 | | | | | IQUB | 1.00 | 13619 | 3 | | | | KCNH6 | 1.00 |
| 13524 | 3 | | | | | IRAK1BP1 | 1.00 | 13620 | 3 | | | | KCNH7 | 1.00 |
| 13525 | 3 | | | | | IRF6 | 1.00 | 13621 | 3 | | | | KCNH8 | 1.00 |
| 13526 | 3 | | | | | IRGC | 1.00 | 13622 | 3 | | | | KCNIP1 | 1.00 |
| 13527 | 3 | | | | | IRGM | 1.00 | 13623 | 3 | | | | KCNIP2 | 1.00 |
| 13528 | 3 | | | | | IRS4 | 1.00 | 13624 | 3 | | | | KCNIP3 | 1.00 |
| 13529 | 3 | | | | | IRX1 | 1.00 | 13625 | 3 | | | | KCNIP4 | 1.00 |
| 13530 | 3 | | | | | IRX2 | 1.00 | 13626 | 3 | | | | KCNIP4-IT1 | 1.00 |

Fig. 41 - 72

| | | | | | | | | | | | | | |
|---|---|---|---|---|---|---|---|---|---|---|---|---|---|
| 13627 | 3 | | | | | KCNJ1 | 1.00 | 13723 | 3 | | | KIAA1875 | 1.00 |
| 13628 | 3 | | | | | KCNJ10 | 1.00 | 13724 | 3 | | | KIAA1984 | 1.00 |
| 13629 | 3 | | | | | KCNJ11 | 1.00 | 13725 | 3 | | | KIAA2022 | 1.00 |
| 13630 | 3 | | | | | KCNJ12 | 1.00 | 13726 | 3 | | | KIF12 | 1.00 |
| 13631 | 3 | | | | | KCNJ13 | 1.00 | 13727 | 3 | | | KIF14 | 1.00 |
| 13632 | 3 | | | | | KCNJ14 | 1.00 | 13728 | 3 | | | KIF15 | 1.00 |
| 13633 | 3 | | | | | KCNJ16 | 1.00 | 13729 | 3 | | | KIF17 | 1.00 |
| 13634 | 3 | | | | | KCNJ18 | 1.00 | 13730 | 3 | | | KIF18A | 1.00 |
| 13635 | 3 | | | | | KCNJ3 | 1.00 | 13731 | 3 | | | KIF18B | 1.00 |
| 13636 | 3 | | | | | KCNJ4 | 1.00 | 13732 | 3 | | | KIF19 | 1.00 |
| 13637 | 3 | | | | | KCNJ5 | 1.00 | 13733 | 3 | | | KIF1A | 1.00 |
| 13638 | 3 | | | | | KCNJ6 | 1.00 | 13734 | 3 | | | KIF20A | 1.00 |
| 13639 | 3 | | | | | KCNJ8 | 1.00 | 13735 | 3 | | | KIF23 | 1.00 |
| 13640 | 3 | | | | | KCNJ9 | 1.00 | 13736 | 3 | | | KIF24 | 1.00 |
| 13641 | 3 | | | | | KCNK1 | 1.00 | 13737 | 3 | | | KIF25 | 1.00 |
| 13642 | 3 | | | | | KCNK10 | 1.00 | 13738 | 3 | | | KIF26A | 1.00 |
| 13643 | 3 | | | | | KCNK12 | 1.00 | 13739 | 3 | | | KIF26B | 1.00 |
| 13644 | 3 | | | | | KCNK15 | 1.00 | 13740 | 3 | | | KIF2B | 1.00 |
| 13645 | 3 | | | | | KCNK16 | 1.00 | 13741 | 3 | | | KIF2C | 1.00 |
| 13646 | 3 | | | | | KCNK17 | 1.00 | 13742 | 3 | | | KIF4A | 1.00 |
| 13647 | 3 | | | | | KCNK18 | 1.00 | 13743 | 3 | | | KIF4B | 1.00 |
| 13648 | 3 | | | | | KCNK2 | 1.00 | 13744 | 3 | | | KIF5A | 1.00 |
| 13649 | 3 | | | | | KCNK3 | 1.00 | 13745 | 3 | | | KIF5C | 1.00 |
| 13650 | 3 | | | | | KCNK4 | 1.00 | 13746 | 3 | | | KIF6 | 1.00 |
| 13651 | 3 | | | | | KCNK5 | 1.00 | 13747 | 3 | | | KIF7 | 1.00 |
| 13652 | 3 | | | | | KCNK9 | 1.00 | 13748 | 3 | | | KIF9 | 1.00 |
| 13653 | 3 | | | | | KCNMA1 | 1.00 | 13749 | 3 | | | KIFC1 | 1.00 |
| 13654 | 3 | | | | | KCNMB2 | 1.00 | 13750 | 3 | | | KIR2DL5A | 1.00 |
| 13655 | 3 | | | | | KCNMB4 | 1.00 | 13751 | 3 | | | KIR2DL5B | 1.00 |
| 13656 | 3 | | | | | KCNN1 | 1.00 | 13752 | 3 | | | KIR2DS3 | 1.00 |
| 13657 | 3 | | | | | KCNN2 | 1.00 | 13753 | 3 | | | KIR2DS5 | 1.00 |
| 13658 | 3 | | | | | KCNN3 | 1.00 | 13754 | 3 | | | KIR3DL3 | 1.00 |
| 13659 | 3 | | | | | KCNQ1DN | 1.00 | 13755 | 3 | | | KIR3DX1 | 1.00 |
| 13660 | 3 | | | | | KCNQ1OT1 | 1.00 | 13756 | 3 | | | KIRREL | 1.00 |
| 13661 | 3 | | | | | KCNQ2 | 1.00 | 13757 | 3 | | | KIRREL2 | 1.00 |
| 13662 | 3 | | | | | KCNQ3 | 1.00 | 13758 | 3 | | | KIRREL3 | 1.00 |
| 13663 | 3 | | | | | KCNQ4 | 1.00 | 13759 | 3 | | | KIRREL3-AS3 | 1.00 |
| 13664 | 3 | | | | | KCNQ5 | 1.00 | 13760 | 3 | | | KISS1 | 1.00 |
| 13665 | 3 | | | | | KCNS1 | 1.00 | 13761 | 3 | | | KISS1R | 1.00 |
| 13666 | 3 | | | | | KCNS2 | 1.00 | 13762 | 3 | | | KITLG | 1.00 |
| 13667 | 3 | | | | | KCNS3 | 1.00 | 13763 | 3 | | | KL | 1.00 |
| 13668 | 3 | | | | | KCNT1 | 1.00 | 13764 | 3 | | | KLB | 1.00 |
| 13669 | 3 | | | | | KCNT2 | 1.00 | 13765 | 3 | | | KLF14 | 1.00 |
| 13670 | 3 | | | | | KCNU1 | 1.00 | 13766 | 3 | | | KLF15 | 1.00 |
| 13671 | 3 | | | | | KCNV1 | 1.00 | 13767 | 3 | | | KLF17 | 1.00 |
| 13672 | 3 | | | | | KCNV2 | 1.00 | 13768 | 3 | | | KLHDC1 | 1.00 |
| 13673 | 3 | | | | | KCP | 1.00 | 13769 | 3 | | | KLHDC7A | 1.00 |
| 13674 | 3 | | | | | KCTD14 | 1.00 | 13770 | 3 | | | KLHDC8A | 1.00 |
| 13675 | 3 | | | | | KCTD16 | 1.00 | 13771 | 3 | | | KLHDC9 | 1.00 |
| 13676 | 3 | | | | | KCTD19 | 1.00 | 13772 | 3 | | | KLHL1 | 1.00 |
| 13677 | 3 | | | | | KCTD4 | 1.00 | 13773 | 3 | | | KLHL10 | 1.00 |
| 13678 | 3 | | | | | KCTD8 | 1.00 | 13774 | 3 | | | KLHL13 | 1.00 |
| 13679 | 3 | | | | | KDELC1 | 1.00 | 13775 | 3 | | | KLHL23 | 1.00 |
| 13680 | 3 | | | | | KDELR3 | 1.00 | 13776 | 3 | | | KLHL29 | 1.00 |
| 13681 | 3 | | | | | KDM4D | 1.00 | 13777 | 3 | | | KLHL30 | 1.00 |
| 13682 | 3 | | | | | KDM4DL | 1.00 | 13778 | 3 | | | KLHL31 | 1.00 |
| 13683 | 3 | | | | | KDM5B-AS1 | 1.00 | 13779 | 3 | | | KLHL32 | 1.00 |
| 13684 | 3 | | | | | KDR | 1.00 | 13780 | 3 | | | KLHL33 | 1.00 |
| 13685 | 3 | | | | | KERA | 1.00 | 13781 | 3 | | | KLHL34 | 1.00 |
| 13686 | 3 | | | | | KGFLP1 | 1.00 | 13782 | 3 | | | KLHL35 | 1.00 |
| 13687 | 3 | | | | | KGFLP2 | 1.00 | 13783 | 3 | | | KLHL38 | 1.00 |
| 13688 | 3 | | | | | KHDC1 | 1.00 | 13784 | 3 | | | KLHL4 | 1.00 |
| 13689 | 3 | | | | | KHDC1L | 1.00 | 13785 | 3 | | | KLHL7-AS1 | 1.00 |
| 13690 | 3 | | | | | KHDRBS2 | 1.00 | 13786 | 3 | | | KLK10 | 1.00 |
| 13691 | 3 | | | | | KHDRBS3 | 1.00 | 13787 | 3 | | | KLK11 | 1.00 |
| 13692 | 3 | | | | | KIAA0087 | 1.00 | 13788 | 3 | | | KLK12 | 1.00 |
| 13693 | 3 | | | | | KIAA0284 | 1.00 | 13789 | 3 | | | KLK13 | 1.00 |
| 13694 | 3 | | | | | KIAA0408 | 1.00 | 13790 | 3 | | | KLK14 | 1.00 |
| 13695 | 3 | | | | | KIAA0664L3 | 1.00 | 13791 | 3 | | | KLK15 | 1.00 |
| 13696 | 3 | | | | | KIAA0895 | 1.00 | 13792 | 3 | | | KLK2 | 1.00 |
| 13697 | 3 | | | | | KIAA0895L | 1.00 | 13793 | 3 | | | KLK3 | 1.00 |
| 13698 | 3 | | | | | KIAA1024 | 1.00 | 13794 | 3 | | | KLK4 | 1.00 |
| 13699 | 3 | | | | | KIAA1045 | 1.00 | 13795 | 3 | | | KLK5 | 1.00 |
| 13700 | 3 | | | | | KIAA1107 | 1.00 | 13796 | 3 | | | KLK6 | 1.00 |
| 13701 | 3 | | | | | KIAA1161 | 1.00 | 13797 | 3 | | | KLK7 | 1.00 |
| 13702 | 3 | | | | | KIAA1199 | 1.00 | 13798 | 3 | | | KLK8 | 1.00 |
| 13703 | 3 | | | | | KIAA1210 | 1.00 | 13799 | 3 | | | KLK9 | 1.00 |
| 13704 | 3 | | | | | KIAA1211 | 1.00 | 13800 | 3 | | | KLKB1 | 1.00 |
| 13705 | 3 | | | | | KIAA1217 | 1.00 | 13801 | 3 | | | KLKP1 | 1.00 |
| 13706 | 3 | | | | | KIAA1239 | 1.00 | 13802 | 3 | | | KLLN | 1.00 |
| 13707 | 3 | | | | | KIAA1244 | 1.00 | 13803 | 3 | | | KLRC4-KLRK1 | 1.00 |
| 13708 | 3 | | | | | KIAA1274 | 1.00 | 13804 | 3 | | | KLRF2 | 1.00 |
| 13709 | 3 | | | | | KIAA1324L | 1.00 | 13805 | 3 | | | KLRG2 | 1.00 |
| 13710 | 3 | | | | | KIAA1328 | 1.00 | 13806 | 3 | | | KNCN | 1.00 |
| 13711 | 3 | | | | | KIAA1377 | 1.00 | 13807 | 3 | | | KNDC1 | 1.00 |
| 13712 | 3 | | | | | KIAA1456 | 1.00 | 13808 | 3 | | | KNG1 | 1.00 |
| 13713 | 3 | | | | | KIAA1462 | 1.00 | 13809 | 3 | | | KNTC1 | 1.00 |
| 13714 | 3 | | | | | KIAA1524 | 1.00 | 13810 | 3 | | | KPNA7 | 1.00 |
| 13715 | 3 | | | | | KIAA1549 | 1.00 | 13811 | 3 | | | KPRP | 1.00 |
| 13716 | 3 | | | | | KIAA1614 | 1.00 | 13812 | 3 | | | KRBOX1 | 1.00 |
| 13717 | 3 | | | | | KIAA1644 | 1.00 | 13813 | 3 | | | KREMEN2 | 1.00 |
| 13718 | 3 | | | | | KIAA1656 | 1.00 | 13814 | 3 | | | KRT12 | 1.00 |
| 13719 | 3 | | | | | KIAA1751 | 1.00 | 13815 | 3 | | | KRT13 | 1.00 |
| 13720 | 3 | | | | | KIAA1755 | 1.00 | 13816 | 3 | | | KRT15 | 1.00 |
| 13721 | 3 | | | | | KIAA1804 | 1.00 | 13817 | 3 | | | KRT16 | 1.00 |
| 13722 | 3 | | | | | KIAA1841 | 1.00 | 13818 | 3 | | | KRT16P2 | 1.00 |

Fig. 41 - 73

| | | | | | | | | | | | | | |
|---|---|---|---|---|---|---|---|---|---|---|---|---|---|
| 13819 | 3 | | | | | KRT16P3 | 1.00 | 13915 | 3 | | | KRTAP23-1 | 1.00 |
| 13820 | 3 | | | | | KRT17 | 1.00 | 13916 | 3 | | | KRTAP24-1 | 1.00 |
| 13821 | 3 | | | | | KRT18P55 | 1.00 | 13917 | 3 | | | KRTAP25-1 | 1.00 |
| 13822 | 3 | | | | | KRT19 | 1.00 | 13918 | 3 | | | KRTAP26-1 | 1.00 |
| 13823 | 3 | | | | | KRT19P2 | 1.00 | 13919 | 3 | | | KRTAP27-1 | 1.00 |
| 13824 | 3 | | | | | KRT2 | 1.00 | 13920 | 3 | | | KRTAP3-1 | 1.00 |
| 13825 | 3 | | | | | KRT20 | 1.00 | 13921 | 3 | | | KRTAP3-2 | 1.00 |
| 13826 | 3 | | | | | KRT222 | 1.00 | 13922 | 3 | | | KRTAP3-3 | 1.00 |
| 13827 | 3 | | | | | KRT24 | 1.00 | 13923 | 3 | | | KRTAP4-1 | 1.00 |
| 13828 | 3 | | | | | KRT25 | 1.00 | 13924 | 3 | | | KRTAP4-11 | 1.00 |
| 13829 | 3 | | | | | KRT26 | 1.00 | 13925 | 3 | | | KRTAP4-12 | 1.00 |
| 13830 | 3 | | | | | KRT27 | 1.00 | 13926 | 3 | | | KRTAP4-2 | 1.00 |
| 13831 | 3 | | | | | KRT28 | 1.00 | 13927 | 3 | | | KRTAP4-3 | 1.00 |
| 13832 | 3 | | | | | KRT3 | 1.00 | 13928 | 3 | | | KRTAP4-4 | 1.00 |
| 13833 | 3 | | | | | KRT31 | 1.00 | 13929 | 3 | | | KRTAP4-5 | 1.00 |
| 13834 | 3 | | | | | KRT32 | 1.00 | 13930 | 3 | | | KRTAP4-6 | 1.00 |
| 13835 | 3 | | | | | KRT33A | 1.00 | 13931 | 3 | | | KRTAP4-7 | 1.00 |
| 13836 | 3 | | | | | KRT33B | 1.00 | 13932 | 3 | | | KRTAP4-8 | 1.00 |
| 13837 | 3 | | | | | KRT34 | 1.00 | 13933 | 3 | | | KRTAP4-9 | 1.00 |
| 13838 | 3 | | | | | KRT35 | 1.00 | 13934 | 3 | | | KRTAP5-1 | 1.00 |
| 13839 | 3 | | | | | KRT36 | 1.00 | 13935 | 3 | | | KRTAP5-10 | 1.00 |
| 13840 | 3 | | | | | KRT37 | 1.00 | 13936 | 3 | | | KRTAP5-11 | 1.00 |
| 13841 | 3 | | | | | KRT38 | 1.00 | 13937 | 3 | | | KRTAP5-2 | 1.00 |
| 13842 | 3 | | | | | KRT39 | 1.00 | 13938 | 3 | | | KRTAP5-3 | 1.00 |
| 13843 | 3 | | | | | KRT4 | 1.00 | 13939 | 3 | | | KRTAP5-4 | 1.00 |
| 13844 | 3 | | | | | KRT40 | 1.00 | 13940 | 3 | | | KRTAP5-5 | 1.00 |
| 13845 | 3 | | | | | KRT42P | 1.00 | 13941 | 3 | | | KRTAP5-6 | 1.00 |
| 13846 | 3 | | | | | KRT6A | 1.00 | 13942 | 3 | | | KRTAP5-7 | 1.00 |
| 13847 | 3 | | | | | KRT6B | 1.00 | 13943 | 3 | | | KRTAP5-8 | 1.00 |
| 13848 | 3 | | | | | KRT6C | 1.00 | 13944 | 3 | | | KRTAP5-9 | 1.00 |
| 13849 | 3 | | | | | KRT7 | 1.00 | 13945 | 3 | | | KRTAP6-1 | 1.00 |
| 13850 | 3 | | | | | KRT71 | 1.00 | 13946 | 3 | | | KRTAP6-2 | 1.00 |
| 13851 | 3 | | | | | KRT73 | 1.00 | 13947 | 3 | | | KRTAP6-3 | 1.00 |
| 13852 | 3 | | | | | KRT74 | 1.00 | 13948 | 3 | | | KRTAP7-1 | 1.00 |
| 13853 | 3 | | | | | KRT75 | 1.00 | 13949 | 3 | | | KRTAP8-1 | 1.00 |
| 13854 | 3 | | | | | KRT76 | 1.00 | 13950 | 3 | | | KRTAP9-1 | 1.00 |
| 13855 | 3 | | | | | KRT77 | 1.00 | 13951 | 3 | | | KRTAP9-2 | 1.00 |
| 13856 | 3 | | | | | KRT78 | 1.00 | 13952 | 3 | | | KRTAP9-3 | 1.00 |
| 13857 | 3 | | | | | KRT79 | 1.00 | 13953 | 3 | | | KRTAP9-4 | 1.00 |
| 13858 | 3 | | | | | KRT8 | 1.00 | 13954 | 3 | | | KRTAP9-8 | 1.00 |
| 13859 | 3 | | | | | KRT80 | 1.00 | 13955 | 3 | | | KRTAP9-9 | 1.00 |
| 13860 | 3 | | | | | KRT81 | 1.00 | 13956 | 3 | | | KRTCAP3 | 1.00 |
| 13861 | 3 | | | | | KRT82 | 1.00 | 13957 | 3 | | | KRTDAP | 1.00 |
| 13862 | 3 | | | | | KRT83 | 1.00 | 13958 | 3 | | | KSR2 | 1.00 |
| 13863 | 3 | | | | | KRT84 | 1.00 | 13959 | 3 | | | KTN1-AS1 | 1.00 |
| 13864 | 3 | | | | | KRT85 | 1.00 | 13960 | 3 | | | L1CAM | 1.00 |
| 13865 | 3 | | | | | KRT86 | 1.00 | 13961 | 3 | | | L2HGDH | 1.00 |
| 13866 | 3 | | | | | KRT8P41 | 1.00 | 13962 | 3 | | | L3MBTL1 | 1.00 |
| 13867 | 3 | | | | | KRT9 | 1.00 | 13963 | 3 | | | L3MBTL4 | 1.00 |
| 13868 | 3 | | | | | KRTAP1-1 | 1.00 | 13964 | 3 | | | LACE1 | 1.00 |
| 13869 | 3 | | | | | KRTAP1-3 | 1.00 | 13965 | 3 | | | LACRT | 1.00 |
| 13870 | 3 | | | | | KRTAP1-5 | 1.00 | 13966 | 3 | | | LAD1 | 1.00 |
| 13871 | 3 | | | | | KRTAP10-1 | 1.00 | 13967 | 3 | | | LALBA | 1.00 |
| 13872 | 3 | | | | | KRTAP10-10 | 1.00 | 13968 | 3 | | | LAMA1 | 1.00 |
| 13873 | 3 | | | | | KRTAP10-11 | 1.00 | 13969 | 3 | | | LAMA2 | 1.00 |
| 13874 | 3 | | | | | KRTAP10-12 | 1.00 | 13970 | 3 | | | LAMA3 | 1.00 |
| 13875 | 3 | | | | | KRTAP10-2 | 1.00 | 13971 | 3 | | | LAMA4 | 1.00 |
| 13876 | 3 | | | | | KRTAP10-3 | 1.00 | 13972 | 3 | | | LAMA5 | 1.00 |
| 13877 | 3 | | | | | KRTAP10-4 | 1.00 | 13973 | 3 | | | LAMB1 | 1.00 |
| 13878 | 3 | | | | | KRTAP10-5 | 1.00 | 13974 | 3 | | | LAMB2 | 1.00 |
| 13879 | 3 | | | | | KRTAP10-6 | 1.00 | 13975 | 3 | | | LAMB3 | 1.00 |
| 13880 | 3 | | | | | KRTAP10-7 | 1.00 | 13976 | 3 | | | LAMB4 | 1.00 |
| 13881 | 3 | | | | | KRTAP10-8 | 1.00 | 13977 | 3 | | | LAMC1 | 1.00 |
| 13882 | 3 | | | | | KRTAP10-9 | 1.00 | 13978 | 3 | | | LAMC2 | 1.00 |
| 13883 | 3 | | | | | KRTAP11-1 | 1.00 | 13979 | 3 | | | LAMC3 | 1.00 |
| 13884 | 3 | | | | | KRTAP12-1 | 1.00 | 13980 | 3 | | | LANCL3 | 1.00 |
| 13885 | 3 | | | | | KRTAP12-2 | 1.00 | 13981 | 3 | | | LARP6 | 1.00 |
| 13886 | 3 | | | | | KRTAP12-3 | 1.00 | 13982 | 3 | | | LAYN | 1.00 |
| 13887 | 3 | | | | | KRTAP12-4 | 1.00 | 13983 | 3 | | | LBP | 1.00 |
| 13888 | 3 | | | | | KRTAP13-1 | 1.00 | 13984 | 3 | | | LBX1 | 1.00 |
| 13889 | 3 | | | | | KRTAP13-2 | 1.00 | 13985 | 3 | | | LBX2 | 1.00 |
| 13890 | 3 | | | | | KRTAP13-3 | 1.00 | 13986 | 3 | | | LCA5 | 1.00 |
| 13891 | 3 | | | | | KRTAP13-4 | 1.00 | 13987 | 3 | | | LCA5L | 1.00 |
| 13892 | 3 | | | | | KRTAP15-1 | 1.00 | 13988 | 3 | | | LCE1A | 1.00 |
| 13893 | 3 | | | | | KRTAP16-1 | 1.00 | 13989 | 3 | | | LCE1B | 1.00 |
| 13894 | 3 | | | | | KRTAP17-1 | 1.00 | 13990 | 3 | | | LCE1C | 1.00 |
| 13895 | 3 | | | | | KRTAP19-1 | 1.00 | 13991 | 3 | | | LCE1D | 1.00 |
| 13896 | 3 | | | | | KRTAP19-2 | 1.00 | 13992 | 3 | | | LCE1E | 1.00 |
| 13897 | 3 | | | | | KRTAP19-3 | 1.00 | 13993 | 3 | | | LCE1F | 1.00 |
| 13898 | 3 | | | | | KRTAP19-4 | 1.00 | 13994 | 3 | | | LCE2A | 1.00 |
| 13899 | 3 | | | | | KRTAP19-5 | 1.00 | 13995 | 3 | | | LCE2B | 1.00 |
| 13900 | 3 | | | | | KRTAP19-6 | 1.00 | 13996 | 3 | | | LCE2C | 1.00 |
| 13901 | 3 | | | | | KRTAP19-7 | 1.00 | 13997 | 3 | | | LCE2D | 1.00 |
| 13902 | 3 | | | | | KRTAP19-8 | 1.00 | 13998 | 3 | | | LCE3A | 1.00 |
| 13903 | 3 | | | | | KRTAP2-1 | 1.00 | 13999 | 3 | | | LCE3B | 1.00 |
| 13904 | 3 | | | | | KRTAP2-2 | 1.00 | 14000 | 3 | | | LCE3C | 1.00 |
| 13905 | 3 | | | | | KRTAP2-4 | 1.00 | 14001 | 3 | | | LCE3D | 1.00 |
| 13906 | 3 | | | | | KRTAP20-1 | 1.00 | 14002 | 3 | | | LCE3E | 1.00 |
| 13907 | 3 | | | | | KRTAP20-2 | 1.00 | 14003 | 3 | | | LCE4A | 1.00 |
| 13908 | 3 | | | | | KRTAP20-3 | 1.00 | 14004 | 3 | | | LCE5A | 1.00 |
| 13909 | 3 | | | | | KRTAP20-4 | 1.00 | 14005 | 3 | | | LCE6A | 1.00 |
| 13910 | 3 | | | | | KRTAP21-1 | 1.00 | 14006 | 3 | | | LCN1 | 1.00 |
| 13911 | 3 | | | | | KRTAP21-2 | 1.00 | 14007 | 3 | | | LCN12 | 1.00 |
| 13912 | 3 | | | | | KRTAP21-3 | 1.00 | 14008 | 3 | | | LCN15 | 1.00 |
| 13913 | 3 | | | | | KRTAP22-1 | 1.00 | 14009 | 3 | | | LCN6 | 1.00 |
| 13914 | 3 | | | | | KRTAP22-2 | 1.00 | 14010 | 3 | | | LCN8 | 1.00 |

Fig. 41 - 74

| | | | | | | | | | | | | | | | | |
|---|---|---|---|---|---|---|---|---|---|---|---|---|---|---|---|---|
| 14011 | 3 | | | | | LCN9 | 1.00 | 14107 | 3 | | | | | LINC00238 | 1.00 |
| 14012 | 3 | | | | | LCNL1 | 1.00 | 14108 | 3 | | | | | LINC00240 | 1.00 |
| 14013 | 3 | | | | | LCT | 1.00 | 14109 | 3 | | | | | LINC00242 | 1.00 |
| 14014 | 3 | | | | | LCTL | 1.00 | 14110 | 3 | | | | | LINC00244 | 1.00 |
| 14015 | 3 | | | | | LDB2 | 1.00 | 14111 | 3 | | | | | LINC00246A | 1.00 |
| 14016 | 3 | | | | | LDB3 | 1.00 | 14112 | 3 | | | | | LINC00251 | 1.00 |
| 14017 | 3 | | | | | LDHAL6A | 1.00 | 14113 | 3 | | | | | LINC00254 | 1.00 |
| 14018 | 3 | | | | | LDHAL6B | 1.00 | 14114 | 3 | | | | | LINC00256A | 1.00 |
| 14019 | 3 | | | | | LDHC | 1.00 | 14115 | 3 | | | | | LINC00256B | 1.00 |
| 14020 | 3 | | | | | LDLRAD1 | 1.00 | 14116 | 3 | | | | | LINC00260 | 1.00 |
| 14021 | 3 | | | | | LDLRAD2 | 1.00 | 14117 | 3 | | | | | LINC00261 | 1.00 |
| 14022 | 3 | | | | | LEAP2 | 1.00 | 14118 | 3 | | | | | LINC00264 | 1.00 |
| 14023 | 3 | | | | | LECT1 | 1.00 | 14119 | 3 | | | | | LINC00266-1 | 1.00 |
| 14024 | 3 | | | | | LECT2 | 1.00 | 14120 | 3 | | | | | LINC00271 | 1.00 |
| 14025 | 3 | | | | | LEFTY1 | 1.00 | 14121 | 3 | | | | | LINC00272 | 1.00 |
| 14026 | 3 | | | | | LEFTY2 | 1.00 | 14122 | 3 | | | | | LINC00273 | 1.00 |
| 14027 | 3 | | | | | LEKR1 | 1.00 | 14123 | 3 | | | | | LINC00277 | 1.00 |
| 14028 | 3 | | | | | LELP1 | 1.00 | 14124 | 3 | | | | | LINC00281 | 1.00 |
| 14029 | 3 | | | | | LEMD1 | 1.00 | 14125 | 3 | | | | | LINC00284 | 1.00 |
| 14030 | 3 | | | | | LENEP | 1.00 | 14126 | 3 | | | | | LINC00290 | 1.00 |
| 14031 | 3 | | | | | LEP | 1.00 | 14127 | 3 | | | | | LINC00293 | 1.00 |
| 14032 | 3 | | | | | LEPREL1 | 1.00 | 14128 | 3 | | | | | LINC00299 | 1.00 |
| 14033 | 3 | | | | | LEPREL2 | 1.00 | 14129 | 3 | | | | | LINC00301 | 1.00 |
| 14034 | 3 | | | | | LEUTX | 1.00 | 14130 | 3 | | | | | LINC00303 | 1.00 |
| 14035 | 3 | | | | | LGALS13 | 1.00 | 14131 | 3 | | | | | LINC00304 | 1.00 |
| 14036 | 3 | | | | | LGALS14 | 1.00 | 14132 | 3 | | | | | LINC00305 | 1.00 |
| 14037 | 3 | | | | | LGALS16 | 1.00 | 14133 | 3 | | | | | LINC00307 | 1.00 |
| 14038 | 3 | | | | | LGALS17A | 1.00 | 14134 | 3 | | | | | LINC00308 | 1.00 |
| 14039 | 3 | | | | | LGALS4 | 1.00 | 14135 | 3 | | | | | LINC00309 | 1.00 |
| 14040 | 3 | | | | | LGALS7 | 1.00 | 14136 | 3 | | | | | LINC00310 | 1.00 |
| 14041 | 3 | | | | | LGALS7B | 1.00 | 14137 | 3 | | | | | LINC00311 | 1.00 |
| 14042 | 3 | | | | | LGALS8-AS1 | 1.00 | 14138 | 3 | | | | | LINC00312 | 1.00 |
| 14043 | 3 | | | | | LGI1 | 1.00 | 14139 | 3 | | | | | LINC00313 | 1.00 |
| 14044 | 3 | | | | | LGI2 | 1.00 | 14140 | 3 | | | | | LINC00314 | 1.00 |
| 14045 | 3 | | | | | LGI3 | 1.00 | 14141 | 3 | | | | | LINC00315 | 1.00 |
| 14046 | 3 | | | | | LGI4 | 1.00 | 14142 | 3 | | | | | LINC00317 | 1.00 |
| 14047 | 3 | | | | | LGR4 | 1.00 | 14143 | 3 | | | | | LINC00319 | 1.00 |
| 14048 | 3 | | | | | LGR5 | 1.00 | 14144 | 3 | | | | | LINC00320 | 1.00 |
| 14049 | 3 | | | | | LGSN | 1.00 | 14145 | 3 | | | | | LINC00323 | 1.00 |
| 14050 | 3 | | | | | LHB | 1.00 | 14146 | 3 | | | | | LINC00326 | 1.00 |
| 14051 | 3 | | | | | LHCGR | 1.00 | 14147 | 3 | | | | | LINC00327 | 1.00 |
| 14052 | 3 | | | | | LHFP | 1.00 | 14148 | 3 | | | | | LINC00330 | 1.00 |
| 14053 | 3 | | | | | LHFPL1 | 1.00 | 14149 | 3 | | | | | LINC00336 | 1.00 |
| 14054 | 3 | | | | | LHFPL3 | 1.00 | 14150 | 3 | | | | | LINC00340 | 1.00 |
| 14055 | 3 | | | | | LHFPL4 | 1.00 | 14151 | 3 | | | | | LINC00346 | 1.00 |
| 14056 | 3 | | | | | LHFPL5 | 1.00 | 14152 | 3 | | | | | LINC00347 | 1.00 |
| 14057 | 3 | | | | | LHX1 | 1.00 | 14153 | 3 | | | | | LINC00410 | 1.00 |
| 14058 | 3 | | | | | LHX2 | 1.00 | 14154 | 3 | | | | | LINC00421 | 1.00 |
| 14059 | 3 | | | | | LHX3 | 1.00 | 14155 | 3 | | | | | LINC00442 | 1.00 |
| 14060 | 3 | | | | | LHX4 | 1.00 | 14156 | 3 | | | | | LINC00460 | 1.00 |
| 14061 | 3 | | | | | LHX5 | 1.00 | 14157 | 3 | | | | | LINC00461 | 1.00 |
| 14062 | 3 | | | | | LHX6 | 1.00 | 14158 | 3 | | | | | LINC00466 | 1.00 |
| 14063 | 3 | | | | | LHX8 | 1.00 | 14159 | 3 | | | | | LINC00469 | 1.00 |
| 14064 | 3 | | | | | LHX9 | 1.00 | 14160 | 3 | | | | | LINC00470 | 1.00 |
| 14065 | 3 | | | | | LIF | 1.00 | 14161 | 3 | | | | | LINC00471 | 1.00 |
| 14066 | 3 | | | | | LIFR | 1.00 | 14162 | 3 | | | | | LINC00472 | 1.00 |
| 14067 | 3 | | | | | LILRB5 | 1.00 | 14163 | 3 | | | | | LINC00473 | 1.00 |
| 14068 | 3 | | | | | LILRP2 | 1.00 | 14164 | 3 | | | | | LINC00474 | 1.00 |
| 14069 | 3 | | | | | LIMCH1 | 1.00 | 14165 | 3 | | | | | LINC00475 | 1.00 |
| 14070 | 3 | | | | | LIM53-LOC440895 | 1.00 | 14166 | 3 | | | | | LINC00477 | 1.00 |
| 14071 | 3 | | | | | LIN28A | 1.00 | 14167 | 3 | | | | | LINC00478 | 1.00 |
| 14072 | 3 | | | | | LIN28B | 1.00 | 14168 | 3 | | | | | LINC00479 | 1.00 |
| 14073 | 3 | | | | | LIN9 | 1.00 | 14169 | 3 | | | | | LINC00482 | 1.00 |
| 14074 | 3 | | | | | LINC00028 | 1.00 | 14170 | 3 | | | | | LINC00483 | 1.00 |
| 14075 | 3 | | | | | LINC00029 | 1.00 | 14171 | 3 | | | | | LINC00485 | 1.00 |
| 14076 | 3 | | | | | LINC00032 | 1.00 | 14172 | 3 | | | | | LINC00486 | 1.00 |
| 14077 | 3 | | | | | LINC00051 | 1.00 | 14173 | 3 | | | | | LINC00487 | 1.00 |
| 14078 | 3 | | | | | LINC00052 | 1.00 | 14174 | 3 | | | | | LINC00488 | 1.00 |
| 14079 | 3 | | | | | LINC00085 | 1.00 | 14175 | 3 | | | | | LINC00494 | 1.00 |
| 14080 | 3 | | | | | LINC00086 | 1.00 | 14176 | 3 | | | | | LINC00511 | 1.00 |
| 14081 | 3 | | | | | LINC00087 | 1.00 | 14177 | 3 | | | | | LINC00514 | 1.00 |
| 14082 | 3 | | | | | LINC00102 | 1.00 | 14178 | 3 | | | | | LINC00515 | 1.00 |
| 14083 | 3 | | | | | LINC00111 | 1.00 | 14179 | 3 | | | | | LINC00518 | 1.00 |
| 14084 | 3 | | | | | LINC00112 | 1.00 | 14180 | 3 | | | | | LINC00520 | 1.00 |
| 14085 | 3 | | | | | LINC00113 | 1.00 | 14181 | 3 | | | | | LINC00521 | 1.00 |
| 14086 | 3 | | | | | LINC00114 | 1.00 | 14182 | 3 | | | | | LINC00523 | 1.00 |
| 14087 | 3 | | | | | LINC00158 | 1.00 | 14183 | 3 | | | | | LINC00525 | 1.00 |
| 14088 | 3 | | | | | LINC00159 | 1.00 | 14184 | 3 | | | | | LINC00535 | 1.00 |
| 14089 | 3 | | | | | LINC00160 | 1.00 | 14185 | 3 | | | | | LINC00536 | 1.00 |
| 14090 | 3 | | | | | LINC00161 | 1.00 | 14186 | 3 | | | | | LINC00538 | 1.00 |
| 14091 | 3 | | | | | LINC00162 | 1.00 | 14187 | 3 | | | | | LINC00547 | 1.00 |
| 14092 | 3 | | | | | LINC00163 | 1.00 | 14188 | 3 | | | | | LINC00548 | 1.00 |
| 14093 | 3 | | | | | LINC00167 | 1.00 | 14189 | 3 | | | | | LINC00550 | 1.00 |
| 14094 | 3 | | | | | LINC00176 | 1.00 | 14190 | 3 | | | | | LINC00552 | 1.00 |
| 14095 | 3 | | | | | LINC00184 | 1.00 | 14191 | 3 | | | | | LINC00574 | 1.00 |
| 14096 | 3 | | | | | LINC00200 | 1.00 | 14192 | 3 | | | | | LINC00575 | 1.00 |
| 14097 | 3 | | | | | LINC00202 | 1.00 | 14193 | 3 | | | | | LINGO1 | 1.00 |
| 14098 | 3 | | | | | LINC00207 | 1.00 | 14194 | 3 | | | | | LINGO4 | 1.00 |
| 14099 | 3 | | | | | LINC00208 | 1.00 | 14195 | 3 | | | | | LIPF | 1.00 |
| 14100 | 3 | | | | | LINC00221 | 1.00 | 14196 | 3 | | | | | LIPG | 1.00 |
| 14101 | 3 | | | | | LINC00222 | 1.00 | 14197 | 3 | | | | | LIPH | 1.00 |
| 14102 | 3 | | | | | LINC00226 | 1.00 | 14198 | 3 | | | | | LIPI | 1.00 |
| 14103 | 3 | | | | | LINC00229 | 1.00 | 14199 | 3 | | | | | LIPJ | 1.00 |
| 14104 | 3 | | | | | LINC00230A | 1.00 | 14200 | 3 | | | | | LIPK | 1.00 |
| 14105 | 3 | | | | | LINC00230B | 1.00 | 14201 | 3 | | | | | LIPM | 1.00 |
| 14106 | 3 | | | | | LINC00235 | 1.00 | 14202 | 3 | | | | | LIX1 | 1.00 |

Fig. 41 - 75

| | | | | | | | | | | | | | |
|---|---|---|---|---|---|---|---|---|---|---|---|---|---|
| 14203 | 3 | | | | LMAN1L | 1.00 | 14299 | 3 | | | | LOC100130480 | 1.00 |
| 14204 | 3 | | | | LMCD1 | 1.00 | 14300 | 3 | | | | LOC100130522 | 1.00 |
| 14205 | 3 | | | | LMLN | 1.00 | 14301 | 3 | | | | LOC100130557 | 1.00 |
| 14206 | 3 | | | | LMO1 | 1.00 | 14302 | 3 | | | | LOC100130673 | 1.00 |
| 14207 | 3 | | | | LMO3 | 1.00 | 14303 | 3 | | | | LOC100130691 | 1.00 |
| 14208 | 3 | | | | LMOD1 | 1.00 | 14304 | 3 | | | | LOC100130700 | 1.00 |
| 14209 | 3 | | | | LMOD2 | 1.00 | 14305 | 3 | | | | LOC100130705 | 1.00 |
| 14210 | 3 | | | | LMOD3 | 1.00 | 14306 | 3 | | | | LOC100130849 | 1.00 |
| 14211 | 3 | | | | LMTK3 | 1.00 | 14307 | 3 | | | | LOC100130880 | 1.00 |
| 14212 | 3 | | | | LMX1A | 1.00 | 14308 | 3 | | | | LOC100130890 | 1.00 |
| 14213 | 3 | | | | LMX1B | 1.00 | 14309 | 3 | | | | LOC100130894 | 1.00 |
| 14214 | 3 | | | | LNP1 | 1.00 | 14310 | 3 | | | | LOC100130899 | 1.00 |
| 14215 | 3 | | | | LNX1 | 1.00 | 14311 | 3 | | | | LOC100130954 | 1.00 |
| 14216 | 3 | | | | LOC100093698 | 1.00 | 14312 | 3 | | | | LOC100130964 | 1.00 |
| 14217 | 3 | | | | LOC100101266 | 1.00 | 14313 | 3 | | | | LOC100130987 | 1.00 |
| 14218 | 3 | | | | LOC100124692 | 1.00 | 14314 | 3 | | | | LOC100130992 | 1.00 |
| 14219 | 3 | | | | LOC100125556 | 1.00 | 14315 | 3 | | | | LOC100131047 | 1.00 |
| 14220 | 3 | | | | LOC100126784 | 1.00 | 14316 | 3 | | | | LOC100131060 | 1.00 |
| 14221 | 3 | | | | LOC100127888 | 1.00 | 14317 | 3 | | | | LOC100131094 | 1.00 |
| 14222 | 3 | | | | LOC100127983 | 1.00 | 14318 | 3 | | | | LOC100131138 | 1.00 |
| 14223 | 3 | | | | LOC100128023 | 1.00 | 14319 | 3 | | | | LOC100131193 | 1.00 |
| 14224 | 3 | | | | LOC100128054 | 1.00 | 14320 | 3 | | | | LOC100131208 | 1.00 |
| 14225 | 3 | | | | LOC100128071 | 1.00 | 14321 | 3 | | | | LOC100131234 | 1.00 |
| 14226 | 3 | | | | LOC100128076 | 1.00 | 14322 | 3 | | | | LOC100131257 | 1.00 |
| 14227 | 3 | | | | LOC100128098 | 1.00 | 14323 | 3 | | | | LOC100131289 | 1.00 |
| 14228 | 3 | | | | LOC100128126 | 1.00 | 14324 | 3 | | | | LOC100131320 | 1.00 |
| 14229 | 3 | | | | LOC100128164 | 1.00 | 14325 | 3 | | | | LOC100131347 | 1.00 |
| 14230 | 3 | | | | LOC100128176 | 1.00 | 14326 | 3 | | | | LOC100131366 | 1.00 |
| 14231 | 3 | | | | LOC100128239 | 1.00 | 14327 | 3 | | | | LOC100131434 | 1.00 |
| 14232 | 3 | | | | LOC100128264 | 1.00 | 14328 | 3 | | | | LOC100131496 | 1.00 |
| 14233 | 3 | | | | LOC100128288 | 1.00 | 14329 | 3 | | | | LOC100131551 | 1.00 |
| 14234 | 3 | | | | LOC100128292 | 1.00 | 14330 | 3 | | | | LOC100131635 | 1.00 |
| 14235 | 3 | | | | LOC100128338 | 1.00 | 14331 | 3 | | | | LOC100131691 | 1.00 |
| 14236 | 3 | | | | LOC100128361 | 1.00 | 14332 | 3 | | | | LOC100131726 | 1.00 |
| 14237 | 3 | | | | LOC100128398 | 1.00 | 14333 | 3 | | | | LOC100131825 | 1.00 |
| 14238 | 3 | | | | LOC100128496 | 1.00 | 14334 | 3 | | | | LOC100132078 | 1.00 |
| 14239 | 3 | | | | LOC100128505 | 1.00 | 14335 | 3 | | | | LOC100132146 | 1.00 |
| 14240 | 3 | | | | LOC100128511 | 1.00 | 14336 | 3 | | | | LOC100132163 | 1.00 |
| 14241 | 3 | | | | LOC100128531 | 1.00 | 14337 | 3 | | | | LOC100132215 | 1.00 |
| 14242 | 3 | | | | LOC100128554 | 1.00 | 14338 | 3 | | | | LOC100132354 | 1.00 |
| 14243 | 3 | | | | LOC100128568 | 1.00 | 14339 | 3 | | | | LOC100132396 | 1.00 |
| 14244 | 3 | | | | LOC100128573 | 1.00 | 14340 | 3 | | | | LOC100132526 | 1.00 |
| 14245 | 3 | | | | LOC100128590 | 1.00 | 14341 | 3 | | | | LOC100132735 | 1.00 |
| 14246 | 3 | | | | LOC100128593 | 1.00 | 14342 | 3 | | | | LOC100132774 | 1.00 |
| 14247 | 3 | | | | LOC100128640 | 1.00 | 14343 | 3 | | | | LOC100132781 | 1.00 |
| 14248 | 3 | | | | LOC100128675 | 1.00 | 14344 | 3 | | | | LOC100132832 | 1.00 |
| 14249 | 3 | | | | LOC100128682 | 1.00 | 14345 | 3 | | | | LOC100132891 | 1.00 |
| 14250 | 3 | | | | LOC100128714 | 1.00 | 14346 | 3 | | | | LOC100132987 | 1.00 |
| 14251 | 3 | | | | LOC100128750 | 1.00 | 14347 | 3 | | | | LOC100133050 | 1.00 |
| 14252 | 3 | | | | LOC100128787 | 1.00 | 14348 | 3 | | | | LOC100133091 | 1.00 |
| 14253 | 3 | | | | LOC100128788 | 1.00 | 14349 | 3 | | | | LOC100133123 | 1.00 |
| 14254 | 3 | | | | LOC100128811 | 1.00 | 14350 | 3 | | | | LOC100133267 | 1.00 |
| 14255 | 3 | | | | LOC100128946 | 1.00 | 14351 | 3 | | | | LOC100133286 | 1.00 |
| 14256 | 3 | | | | LOC100128993 | 1.00 | 14352 | 3 | | | | LOC100133308 | 1.00 |
| 14257 | 3 | | | | LOC100129027 | 1.00 | 14353 | 3 | | | | LOC100133315 | 1.00 |
| 14258 | 3 | | | | LOC100129046 | 1.00 | 14354 | 3 | | | | LOC100133461 | 1.00 |
| 14259 | 3 | | | | LOC100129055 | 1.00 | 14355 | 3 | | | | LOC100133612 | 1.00 |
| 14260 | 3 | | | | LOC100129083 | 1.00 | 14356 | 3 | | | | LOC100133669 | 1.00 |
| 14261 | 3 | | | | LOC100129175 | 1.00 | 14357 | 3 | | | | LOC100133920 | 1.00 |
| 14262 | 3 | | | | LOC100129213 | 1.00 | 14358 | 3 | | | | LOC100133957 | 1.00 |
| 14263 | 3 | | | | LOC100129216 | 1.00 | 14359 | 3 | | | | LOC100133985 | 1.00 |
| 14264 | 3 | | | | LOC100129269 | 1.00 | 14360 | 3 | | | | LOC100134015 | 1.00 |
| 14265 | 3 | | | | LOC100129316 | 1.00 | 14361 | 3 | | | | LOC100134259 | 1.00 |
| 14266 | 3 | | | | LOC100129345 | 1.00 | 14362 | 3 | | | | LOC100134317 | 1.00 |
| 14267 | 3 | | | | LOC100129407 | 1.00 | 14363 | 3 | | | | LOC100134368 | 1.00 |
| 14268 | 3 | | | | LOC100129427 | 1.00 | 14364 | 3 | | | | LOC100134868 | 1.00 |
| 14269 | 3 | | | | LOC100129480 | 1.00 | 14365 | 3 | | | | LOC100144595 | 1.00 |
| 14270 | 3 | | | | LOC100129515 | 1.00 | 14366 | 3 | | | | LOC100144597 | 1.00 |
| 14271 | 3 | | | | LOC100129518 | 1.00 | 14367 | 3 | | | | LOC100144602 | 1.00 |
| 14272 | 3 | | | | LOC100129520 | 1.00 | 14368 | 3 | | | | LOC100144603 | 1.00 |
| 14273 | 3 | | | | LOC100129617 | 1.00 | 14369 | 3 | | | | LOC100144604 | 1.00 |
| 14274 | 3 | | | | LOC100129620 | 1.00 | 14370 | 3 | | | | LOC100169752 | 1.00 |
| 14275 | 3 | | | | LOC100129636 | 1.00 | 14371 | 3 | | | | LOC100188947 | 1.00 |
| 14276 | 3 | | | | LOC100129662 | 1.00 | 14372 | 3 | | | | LOC100189589 | 1.00 |
| 14277 | 3 | | | | LOC100129716 | 1.00 | 14373 | 3 | | | | LOC100190938 | 1.00 |
| 14278 | 3 | | | | LOC100129722 | 1.00 | 14374 | 3 | | | | LOC100190940 | 1.00 |
| 14279 | 3 | | | | LOC100129726 | 1.00 | 14375 | 3 | | | | LOC100192204 | 1.00 |
| 14280 | 3 | | | | LOC100129794 | 1.00 | 14376 | 3 | | | | LOC100192378 | 1.00 |
| 14281 | 3 | | | | LOC100129845 | 1.00 | 14377 | 3 | | | | LOC100192426 | 1.00 |
| 14282 | 3 | | | | LOC100129858 | 1.00 | 14378 | 3 | | | | LOC100216001 | 1.00 |
| 14283 | 3 | | | | LOC100129924 | 1.00 | 14379 | 3 | | | | LOC100216479 | 1.00 |
| 14284 | 3 | | | | LOC100129931 | 1.00 | 14380 | 3 | | | | LOC100216546 | 1.00 |
| 14285 | 3 | | | | LOC100129935 | 1.00 | 14381 | 3 | | | | LOC100240734 | 1.00 |
| 14286 | 3 | | | | LOC100130000 | 1.00 | 14382 | 3 | | | | LOC100240735 | 1.00 |
| 14287 | 3 | | | | LOC100130015 | 1.00 | 14383 | 3 | | | | LOC100268168 | 1.00 |
| 14288 | 3 | | | | LOC100130155 | 1.00 | 14384 | 3 | | | | LOC100270679 | 1.00 |
| 14289 | 3 | | | | LOC100130197 | 1.00 | 14385 | 3 | | | | LOC100270746 | 1.00 |
| 14290 | 3 | | | | LOC100130238 | 1.00 | 14386 | 3 | | | | LOC100270804 | 1.00 |
| 14291 | 3 | | | | LOC100130264 | 1.00 | 14387 | 3 | | | | LOC100271702 | 1.00 |
| 14292 | 3 | | | | LOC100130275 | 1.00 | 14388 | 3 | | | | LOC100271832 | 1.00 |
| 14293 | 3 | | | | LOC100130301 | 1.00 | 14389 | 3 | | | | LOC100272217 | 1.00 |
| 14294 | 3 | | | | LOC100130348 | 1.00 | 14390 | 3 | | | | LOC100272228 | 1.00 |
| 14295 | 3 | | | | LOC100130357 | 1.00 | 14391 | 3 | | | | LOC100286844 | 1.00 |
| 14296 | 3 | | | | LOC100130417 | 1.00 | 14392 | 3 | | | | LOC100286922 | 1.00 |
| 14297 | 3 | | | | LOC100130451 | 1.00 | 14393 | 3 | | | | LOC100286938 | 1.00 |
| 14298 | 3 | | | | LOC100130452 | 1.00 | 14394 | 3 | | | | LOC100286979 | 1.00 |

Fig. 41 - 76

| | | | | | | | | | | | | | | |
|---|---|---|---|---|---|---|---|---|---|---|---|---|---|---|
| 14395 | 3 | | | | | LOC100287010 | 1.00 | 14491 | 3 | | | | LOC100505918 | 1.00 |
| 14396 | 3 | | | | | LOC100287015 | 1.00 | 14492 | 3 | | | | LOC100505933 | 1.00 |
| 14397 | 3 | | | | | LOC100287042 | 1.00 | 14493 | 3 | | | | LOC100505964 | 1.00 |
| 14398 | 3 | | | | | LOC100287216 | 1.00 | 14494 | 3 | | | | LOC100505967 | 1.00 |
| 14399 | 3 | | | | | LOC100287225 | 1.00 | 14495 | 3 | | | | LOC100505978 | 1.00 |
| 14400 | 3 | | | | | LOC100287314 | 1.00 | 14496 | 3 | | | | LOC100505989 | 1.00 |
| 14401 | 3 | | | | | LOC100287559 | 1.00 | 14497 | 3 | | | | LOC100506012 | 1.00 |
| 14402 | 3 | | | | | LOC100287632 | 1.00 | 14498 | 3 | | | | LOC100506013 | 1.00 |
| 14403 | 3 | | | | | LOC100287718 | 1.00 | 14499 | 3 | | | | LOC100506023 | 1.00 |
| 14404 | 3 | | | | | LOC100287765 | 1.00 | 14500 | 3 | | | | LOC100506025 | 1.00 |
| 14405 | 3 | | | | | LOC100287792 | 1.00 | 14501 | 3 | | | | LOC100506050 | 1.00 |
| 14406 | 3 | | | | | LOC100287814 | 1.00 | 14502 | 3 | | | | LOC100506068 | 1.00 |
| 14407 | 3 | | | | | LOC100287834 | 1.00 | 14503 | 3 | | | | LOC100506071 | 1.00 |
| 14408 | 3 | | | | | LOC100287846 | 1.00 | 14504 | 3 | | | | LOC100506083 | 1.00 |
| 14409 | 3 | | | | | LOC100287879 | 1.00 | 14505 | 3 | | | | LOC100506085 | 1.00 |
| 14410 | 3 | | | | | LOC100287944 | 1.00 | 14506 | 3 | | | | LOC100506122 | 1.00 |
| 14411 | 3 | | | | | LOC100288077 | 1.00 | 14507 | 3 | | | | LOC100506124 | 1.00 |
| 14412 | 3 | | | | | LOC100288079 | 1.00 | 14508 | 3 | | | | LOC100506134 | 1.00 |
| 14413 | 3 | | | | | LOC100288122 | 1.00 | 14509 | 3 | | | | LOC100506136 | 1.00 |
| 14414 | 3 | | | | | LOC100288181 | 1.00 | 14510 | 3 | | | | LOC100506172 | 1.00 |
| 14415 | 3 | | | | | LOC100288198 | 1.00 | 14511 | 3 | | | | LOC100506178 | 1.00 |
| 14416 | 3 | | | | | LOC100288255 | 1.00 | 14512 | 3 | | | | LOC100506195 | 1.00 |
| 14417 | 3 | | | | | LOC100288346 | 1.00 | 14513 | 3 | | | | LOC100506207 | 1.00 |
| 14418 | 3 | | | | | LOC100288428 | 1.00 | 14514 | 3 | | | | LOC100506241 | 1.00 |
| 14419 | 3 | | | | | LOC100288524 | 1.00 | 14515 | 3 | | | | LOC100506274 | 1.00 |
| 14420 | 3 | | | | | LOC100288570 | 1.00 | 14516 | 3 | | | | LOC100506368 | 1.00 |
| 14421 | 3 | | | | | LOC100288637 | 1.00 | 14517 | 3 | | | | LOC100506384 | 1.00 |
| 14422 | 3 | | | | | LOC100288748 | 1.00 | 14518 | 3 | | | | LOC100506385 | 1.00 |
| 14423 | 3 | | | | | LOC100288814 | 1.00 | 14519 | 3 | | | | LOC100506388 | 1.00 |
| 14424 | 3 | | | | | LOC100288911 | 1.00 | 14520 | 3 | | | | LOC100506393 | 1.00 |
| 14425 | 3 | | | | | LOC100288974 | 1.00 | 14521 | 3 | | | | LOC100506394 | 1.00 |
| 14426 | 3 | | | | | LOC100289092 | 1.00 | 14522 | 3 | | | | LOC100506409 | 1.00 |
| 14427 | 3 | | | | | LOC100289178 | 1.00 | 14523 | 3 | | | | LOC100506421 | 1.00 |
| 14428 | 3 | | | | | LOC100289187 | 1.00 | 14524 | 3 | | | | LOC100506422 | 1.00 |
| 14429 | 3 | | | | | LOC100289211 | 1.00 | 14525 | 3 | | | | LOC100506433 | 1.00 |
| 14430 | 3 | | | | | LOC100289255 | 1.00 | 14526 | 3 | | | | LOC100506451 | 1.00 |
| 14431 | 3 | | | | | LOC100289361 | 1.00 | 14527 | 3 | | | | LOC100506462 | 1.00 |
| 14432 | 3 | | | | | LOC100289495 | 1.00 | 14528 | 3 | | | | LOC100506472 | 1.00 |
| 14433 | 3 | | | | | LOC100289509 | 1.00 | 14529 | 3 | | | | LOC100506474 | 1.00 |
| 14434 | 3 | | | | | LOC100289650 | 1.00 | 14530 | 3 | | | | LOC100506497 | 1.00 |
| 14435 | 3 | | | | | LOC100289656 | 1.00 | 14531 | 3 | | | | LOC100506540 | 1.00 |
| 14436 | 3 | | | | | LOC100289673 | 1.00 | 14532 | 3 | | | | LOC100506599 | 1.00 |
| 14437 | 3 | | | | | LOC100292680 | 1.00 | 14533 | 3 | | | | LOC100506650 | 1.00 |
| 14438 | 3 | | | | | LOC100293534 | 1.00 | 14534 | 3 | | | | LOC100506655 | 1.00 |
| 14439 | 3 | | | | | LOC100294362 | 1.00 | 14535 | 3 | | | | LOC100506660 | 1.00 |
| 14440 | 3 | | | | | LOC100302401 | 1.00 | 14536 | 3 | | | | LOC100506688 | 1.00 |
| 14441 | 3 | | | | | LOC100302640 | 1.00 | 14537 | 3 | | | | LOC100506730 | 1.00 |
| 14442 | 3 | | | | | LOC100302650 | 1.00 | 14538 | 3 | | | | LOC100506733 | 1.00 |
| 14443 | 3 | | | | | LOC100303749 | 1.00 | 14539 | 3 | | | | LOC100506746 | 1.00 |
| 14444 | 3 | | | | | LOC100306975 | 1.00 | 14540 | 3 | | | | LOC100506757 | 1.00 |
| 14445 | 3 | | | | | LOC100329135 | 1.00 | 14541 | 3 | | | | LOC100506795 | 1.00 |
| 14446 | 3 | | | | | LOC100379224 | 1.00 | 14542 | 3 | | | | LOC100506801 | 1.00 |
| 14447 | 3 | | | | | LOC100422737 | 1.00 | 14543 | 3 | | | | LOC100506804 | 1.00 |
| 14448 | 3 | | | | | LOC100498859 | 1.00 | 14544 | 3 | | | | LOC100506810 | 1.00 |
| 14449 | 3 | | | | | LOC100499183 | 1.00 | 14545 | 3 | | | | LOC100506835 | 1.00 |
| 14450 | 3 | | | | | LOC100499194 | 1.00 | 14546 | 3 | | | | LOC100506874 | 1.00 |
| 14451 | 3 | | | | | LOC100499227 | 1.00 | 14547 | 3 | | | | LOC100506888 | 1.00 |
| 14452 | 3 | | | | | LOC100499467 | 1.00 | 14548 | 3 | | | | LOC100506895 | 1.00 |
| 14453 | 3 | | | | | LOC100499484 | 1.00 | 14549 | 3 | | | | LOC100506939 | 1.00 |
| 14454 | 3 | | | | | LOC100500773 | 1.00 | 14550 | 3 | | | | LOC100506994 | 1.00 |
| 14455 | 3 | | | | | LOC100500938 | 1.00 | 14551 | 3 | | | | LOC100507003 | 1.00 |
| 14456 | 3 | | | | | LOC100505474 | 1.00 | 14552 | 3 | | | | LOC100507032 | 1.00 |
| 14457 | 3 | | | | | LOC100505478 | 1.00 | 14553 | 3 | | | | LOC100507034 | 1.00 |
| 14458 | 3 | | | | | LOC100505495 | 1.00 | 14554 | 3 | | | | LOC100507043 | 1.00 |
| 14459 | 3 | | | | | LOC100505536 | 1.00 | 14555 | 3 | | | | LOC100507050 | 1.00 |
| 14460 | 3 | | | | | LOC100505540 | 1.00 | 14556 | 3 | | | | LOC100507053 | 1.00 |
| 14461 | 3 | | | | | LOC100505545 | 1.00 | 14557 | 3 | | | | LOC100507055 | 1.00 |
| 14462 | 3 | | | | | LOC100505576 | 1.00 | 14558 | 3 | | | | LOC100507066 | 1.00 |
| 14463 | 3 | | | | | LOC100505583 | 1.00 | 14559 | 3 | | | | LOC100507086 | 1.00 |
| 14464 | 3 | | | | | LOC100505619 | 1.00 | 14560 | 3 | | | | LOC100507091 | 1.00 |
| 14465 | 3 | | | | | LOC100505624 | 1.00 | 14561 | 3 | | | | LOC100507096 | 1.00 |
| 14466 | 3 | | | | | LOC100505633 | 1.00 | 14562 | 3 | | | | LOC100507117 | 1.00 |
| 14467 | 3 | | | | | LOC100505658 | 1.00 | 14563 | 3 | | | | LOC100507127 | 1.00 |
| 14468 | 3 | | | | | LOC100505659 | 1.00 | 14564 | 3 | | | | LOC100507140 | 1.00 |
| 14469 | 3 | | | | | LOC100505666 | 1.00 | 14565 | 3 | | | | LOC100507156 | 1.00 |
| 14470 | 3 | | | | | LOC100505676 | 1.00 | 14566 | 3 | | | | LOC100507173 | 1.00 |
| 14471 | 3 | | | | | LOC100505678 | 1.00 | 14567 | 3 | | | | LOC100507178 | 1.00 |
| 14472 | 3 | | | | | LOC100505679 | 1.00 | 14568 | 3 | | | | LOC100507194 | 1.00 |
| 14473 | 3 | | | | | LOC100505695 | 1.00 | 14569 | 3 | | | | LOC100507203 | 1.00 |
| 14474 | 3 | | | | | LOC100505715 | 1.00 | 14570 | 3 | | | | LOC100507205 | 1.00 |
| 14475 | 3 | | | | | LOC100505716 | 1.00 | 14571 | 3 | | | | LOC100507206 | 1.00 |
| 14476 | 3 | | | | | LOC100505718 | 1.00 | 14572 | 3 | | | | LOC100507240 | 1.00 |
| 14477 | 3 | | | | | LOC100505738 | 1.00 | 14573 | 3 | | | | LOC100507244 | 1.00 |
| 14478 | 3 | | | | | LOC100505768 | 1.00 | 14574 | 3 | | | | LOC100507250 | 1.00 |
| 14479 | 3 | | | | | LOC100505776 | 1.00 | 14575 | 3 | | | | LOC100507254 | 1.00 |
| 14480 | 3 | | | | | LOC100505782 | 1.00 | 14576 | 3 | | | | LOC100507266 | 1.00 |
| 14481 | 3 | | | | | LOC100505795 | 1.00 | 14577 | 3 | | | | LOC100507299 | 1.00 |
| 14482 | 3 | | | | | LOC100505806 | 1.00 | 14578 | 3 | | | | LOC100507300 | 1.00 |
| 14483 | 3 | | | | | LOC100505817 | 1.00 | 14579 | 3 | | | | LOC100507334 | 1.00 |
| 14484 | 3 | | | | | LOC100505826 | 1.00 | 14580 | 3 | | | | LOC100507341 | 1.00 |
| 14485 | 3 | | | | | LOC100505835 | 1.00 | 14581 | 3 | | | | LOC100507346 | 1.00 |
| 14486 | 3 | | | | | LOC100505839 | 1.00 | 14582 | 3 | | | | LOC100507351 | 1.00 |
| 14487 | 3 | | | | | LOC100505841 | 1.00 | 14583 | 3 | | | | LOC100507362 | 1.00 |
| 14488 | 3 | | | | | LOC100505875 | 1.00 | 14584 | 3 | | | | LOC100507377 | 1.00 |
| 14489 | 3 | | | | | LOC100505894 | 1.00 | 14585 | 3 | | | | LOC100507387 | 1.00 |
| 14490 | 3 | | | | | LOC100505912 | 1.00 | 14586 | 3 | | | | LOC100507389 | 1.00 |

Fig. 41 - 77

| | | | | | | | | | | | | | | |
|---|---|---|---|---|---|---|---|---|---|---|---|---|---|---|
| 14587 | 3 | | | | | LOC100507391 | 1.00 | 14683 | 3 | | | | LOC154449 | 1.00 |
| 14588 | 3 | | | | | LOC100507401 | 1.00 | 14684 | 3 | | | | LOC154822 | 1.00 |
| 14589 | 3 | | | | | LOC100507410 | 1.00 | 14685 | 3 | | | | LOC154860 | 1.00 |
| 14590 | 3 | | | | | LOC100507421 | 1.00 | 14686 | 3 | | | | LOC154872 | 1.00 |
| 14591 | 3 | | | | | LOC100507423 | 1.00 | 14687 | 3 | | | | LOC155060 | 1.00 |
| 14592 | 3 | | | | | LOC100507433 | 1.00 | 14688 | 3 | | | | LOC157273 | 1.00 |
| 14593 | 3 | | | | | LOC100507443 | 1.00 | 14689 | 3 | | | | LOC157381 | 1.00 |
| 14594 | 3 | | | | | LOC100507462 | 1.00 | 14690 | 3 | | | | LOC157627 | 1.00 |
| 14595 | 3 | | | | | LOC100507466 | 1.00 | 14691 | 3 | | | | LOC158376 | 1.00 |
| 14596 | 3 | | | | | LOC100507470 | 1.00 | 14692 | 3 | | | | LOC158434 | 1.00 |
| 14597 | 3 | | | | | LOC100507472 | 1.00 | 14693 | 3 | | | | LOC158435 | 1.00 |
| 14598 | 3 | | | | | LOC100507489 | 1.00 | 14694 | 3 | | | | LOC158572 | 1.00 |
| 14599 | 3 | | | | | LOC100507501 | 1.00 | 14695 | 3 | | | | LOC158696 | 1.00 |
| 14600 | 3 | | | | | LOC100507537 | 1.00 | 14696 | 3 | | | | LOC170425 | 1.00 |
| 14601 | 3 | | | | | LOC100507547 | 1.00 | 14697 | 3 | | | | LOC1720 | 1.00 |
| 14602 | 3 | | | | | LOC100507557 | 1.00 | 14698 | 3 | | | | LOC200261 | 1.00 |
| 14603 | 3 | | | | | LOC100507564 | 1.00 | 14699 | 3 | | | | LOC200726 | 1.00 |
| 14604 | 3 | | | | | LOC100507582 | 1.00 | 14700 | 3 | | | | LOC201477 | 1.00 |
| 14605 | 3 | | | | | LOC100507584 | 1.00 | 14701 | 3 | | | | LOC201617 | 1.00 |
| 14606 | 3 | | | | | LOC100507588 | 1.00 | 14702 | 3 | | | | LOC201651 | 1.00 |
| 14607 | 3 | | | | | LOC100507589 | 1.00 | 14703 | 3 | | | | LOC219347 | 1.00 |
| 14608 | 3 | | | | | LOC100507600 | 1.00 | 14704 | 3 | | | | LOC219731 | 1.00 |
| 14609 | 3 | | | | | LOC100507605 | 1.00 | 14705 | 3 | | | | LOC221122 | 1.00 |
| 14610 | 3 | | | | | LOC100507629 | 1.00 | 14706 | 3 | | | | LOC221442 | 1.00 |
| 14611 | 3 | | | | | LOC100507634 | 1.00 | 14707 | 3 | | | | LOC253044 | 1.00 |
| 14612 | 3 | | | | | LOC100507651 | 1.00 | 14708 | 3 | | | | LOC253573 | 1.00 |
| 14613 | 3 | | | | | LOC100508120 | 1.00 | 14709 | 3 | | | | LOC253962 | 1.00 |
| 14614 | 3 | | | | | LOC100509575 | 1.00 | 14710 | 3 | | | | LOC254099 | 1.00 |
| 14615 | 3 | | | | | LOC100509894 | 1.00 | 14711 | 3 | | | | LOC254312 | 1.00 |
| 14616 | 3 | | | | | LOC100526771 | 1.00 | 14712 | 3 | | | | LOC255025 | 1.00 |
| 14617 | 3 | | | | | LOC100616530 | 1.00 | 14713 | 3 | | | | LOC255130 | 1.00 |
| 14618 | 3 | | | | | LOC100616668 | 1.00 | 14714 | 3 | | | | LOC255167 | 1.00 |
| 14619 | 3 | | | | | LOC100628307 | 1.00 | 14715 | 3 | | | | LOC255411 | 1.00 |
| 14620 | 3 | | | | | LOC100630918 | 1.00 | 14716 | 3 | | | | LOC255480 | 1.00 |
| 14621 | 3 | | | | | LOC100631378 | 1.00 | 14717 | 3 | | | | LOC255654 | 1.00 |
| 14622 | 3 | | | | | LOC100652730 | 1.00 | 14718 | 3 | | | | LOC256021 | 1.00 |
| 14623 | 3 | | | | | LOC100652739 | 1.00 | 14719 | 3 | | | | LOC256880 | 1.00 |
| 14624 | 3 | | | | | LOC100652759 | 1.00 | 14720 | 3 | | | | LOC257358 | 1.00 |
| 14625 | 3 | | | | | LOC100652770 | 1.00 | 14721 | 3 | | | | LOC257396 | 1.00 |
| 14626 | 3 | | | | | LOC100652791 | 1.00 | 14722 | 3 | | | | LOC282980 | 1.00 |
| 14627 | 3 | | | | | LOC100652846 | 1.00 | 14723 | 3 | | | | LOC283033 | 1.00 |
| 14628 | 3 | | | | | LOC100652909 | 1.00 | 14724 | 3 | | | | LOC283038 | 1.00 |
| 14629 | 3 | | | | | LOC100652999 | 1.00 | 14725 | 3 | | | | LOC283050 | 1.00 |
| 14630 | 3 | | | | | LOC100653515 | 1.00 | 14726 | 3 | | | | LOC283116 | 1.00 |
| 14631 | 3 | | | | | LOC116437 | 1.00 | 14727 | 3 | | | | LOC283143 | 1.00 |
| 14632 | 3 | | | | | LOC120824 | 1.00 | 14728 | 3 | | | | LOC283177 | 1.00 |
| 14633 | 3 | | | | | LOC126536 | 1.00 | 14729 | 3 | | | | LOC283194 | 1.00 |
| 14634 | 3 | | | | | LOC127841 | 1.00 | 14730 | 3 | | | | LOC283214 | 1.00 |
| 14635 | 3 | | | | | LOC143188 | 1.00 | 14731 | 3 | | | | LOC283299 | 1.00 |
| 14636 | 3 | | | | | LOC143666 | 1.00 | 14732 | 3 | | | | LOC283332 | 1.00 |
| 14637 | 3 | | | | | LOC144481 | 1.00 | 14733 | 3 | | | | LOC283335 | 1.00 |
| 14638 | 3 | | | | | LOC144486 | 1.00 | 14734 | 3 | | | | LOC283392 | 1.00 |
| 14639 | 3 | | | | | LOC144571 | 1.00 | 14735 | 3 | | | | LOC283403 | 1.00 |
| 14640 | 3 | | | | | LOC144742 | 1.00 | 14736 | 3 | | | | LOC283404 | 1.00 |
| 14641 | 3 | | | | | LOC145216 | 1.00 | 14737 | 3 | | | | LOC283440 | 1.00 |
| 14642 | 3 | | | | | LOC145474 | 1.00 | 14738 | 3 | | | | LOC283481 | 1.00 |
| 14643 | 3 | | | | | LOC145663 | 1.00 | 14739 | 3 | | | | LOC283547 | 1.00 |
| 14644 | 3 | | | | | LOC145820 | 1.00 | 14740 | 3 | | | | LOC283553 | 1.00 |
| 14645 | 3 | | | | | LOC145837 | 1.00 | 14741 | 3 | | | | LOC283585 | 1.00 |
| 14646 | 3 | | | | | LOC145845 | 1.00 | 14742 | 3 | | | | LOC283587 | 1.00 |
| 14647 | 3 | | | | | LOC146336 | 1.00 | 14743 | 3 | | | | LOC283683 | 1.00 |
| 14648 | 3 | | | | | LOC146481 | 1.00 | 14744 | 3 | | | | LOC283688 | 1.00 |
| 14649 | 3 | | | | | LOC146513 | 1.00 | 14745 | 3 | | | | LOC283693 | 1.00 |
| 14650 | 3 | | | | | LOC147093 | 1.00 | 14746 | 3 | | | | LOC283710 | 1.00 |
| 14651 | 3 | | | | | LOC147646 | 1.00 | 14747 | 3 | | | | LOC283731 | 1.00 |
| 14652 | 3 | | | | | LOC147670 | 1.00 | 14748 | 3 | | | | LOC283738 | 1.00 |
| 14653 | 3 | | | | | LOC148145 | 1.00 | 14749 | 3 | | | | LOC283761 | 1.00 |
| 14654 | 3 | | | | | LOC148696 | 1.00 | 14750 | 3 | | | | LOC283856 | 1.00 |
| 14655 | 3 | | | | | LOC148709 | 1.00 | 14751 | 3 | | | | LOC283867 | 1.00 |
| 14656 | 3 | | | | | LOC148824 | 1.00 | 14752 | 3 | | | | LOC283888 | 1.00 |
| 14657 | 3 | | | | | LOC149086 | 1.00 | 14753 | 3 | | | | LOC283914 | 1.00 |
| 14658 | 3 | | | | | LOC149134 | 1.00 | 14754 | 3 | | | | LOC284009 | 1.00 |
| 14659 | 3 | | | | | LOC149373 | 1.00 | 14755 | 3 | | | | LOC284080 | 1.00 |
| 14660 | 3 | | | | | LOC149773 | 1.00 | 14756 | 3 | | | | LOC284100 | 1.00 |
| 14661 | 3 | | | | | LOC149950 | 1.00 | 14757 | 3 | | | | LOC284215 | 1.00 |
| 14662 | 3 | | | | | LOC150185 | 1.00 | 14758 | 3 | | | | LOC284260 | 1.00 |
| 14663 | 3 | | | | | LOC150197 | 1.00 | 14759 | 3 | | | | LOC284276 | 1.00 |
| 14664 | 3 | | | | | LOC150381 | 1.00 | 14760 | 3 | | | | LOC284294 | 1.00 |
| 14665 | 3 | | | | | LOC150527 | 1.00 | 14761 | 3 | | | | LOC284344 | 1.00 |
| 14666 | 3 | | | | | LOC150568 | 1.00 | 14762 | 3 | | | | LOC284379 | 1.00 |
| 14667 | 3 | | | | | LOC150622 | 1.00 | 14763 | 3 | | | | LOC284395 | 1.00 |
| 14668 | 3 | | | | | LOC150935 | 1.00 | 14764 | 3 | | | | LOC284412 | 1.00 |
| 14669 | 3 | | | | | LOC151009 | 1.00 | 14765 | 3 | | | | LOC284551 | 1.00 |
| 14670 | 3 | | | | | LOC151171 | 1.00 | 14766 | 3 | | | | LOC284576 | 1.00 |
| 14671 | 3 | | | | | LOC151174 | 1.00 | 14767 | 3 | | | | LOC284578 | 1.00 |
| 14672 | 3 | | | | | LOC151300 | 1.00 | 14768 | 3 | | | | LOC284581 | 1.00 |
| 14673 | 3 | | | | | LOC151475 | 1.00 | 14769 | 3 | | | | LOC284632 | 1.00 |
| 14674 | 3 | | | | | LOC151484 | 1.00 | 14770 | 3 | | | | LOC284648 | 1.00 |
| 14675 | 3 | | | | | LOC151658 | 1.00 | 14771 | 3 | | | | LOC284661 | 1.00 |
| 14676 | 3 | | | | | LOC152024 | 1.00 | 14772 | 3 | | | | LOC284688 | 1.00 |
| 14677 | 3 | | | | | LOC152225 | 1.00 | 14773 | 3 | | | | LOC284788 | 1.00 |
| 14678 | 3 | | | | | LOC152578 | 1.00 | 14774 | 3 | | | | LOC284798 | 1.00 |
| 14679 | 3 | | | | | LOC152742 | 1.00 | 14775 | 3 | | | | LOC284801 | 1.00 |
| 14680 | 3 | | | | | LOC153469 | 1.00 | 14776 | 3 | | | | LOC284865 | 1.00 |
| 14681 | 3 | | | | | LOC153910 | 1.00 | 14777 | 3 | | | | LOC284933 | 1.00 |
| 14682 | 3 | | | | | LOC154092 | 1.00 | 14778 | 3 | | | | LOC284950 | 1.00 |

Fig. 41 - 78

| | | | | | | | | | | | | | | |
|---|---|---|---|---|---|---|---|---|---|---|---|---|---|---|
| 14779 | 3 | | | | | LOC284998 | 1.00 | 14875 | 3 | | | | LOC375010 | 1.00 |
| 14780 | 3 | | | | | LOC285000 | 1.00 | 14876 | 3 | | | | LOC375196 | 1.00 |
| 14781 | 3 | | | | | LOC285084 | 1.00 | 14877 | 3 | | | | LOC375295 | 1.00 |
| 14782 | 3 | | | | | LOC285103 | 1.00 | 14878 | 3 | | | | LOC387646 | 1.00 |
| 14783 | 3 | | | | | LOC285205 | 1.00 | 14879 | 3 | | | | LOC388152 | 1.00 |
| 14784 | 3 | | | | | LOC285326 | 1.00 | 14880 | 3 | | | | LOC388276 | 1.00 |
| 14785 | 3 | | | | | LOC285370 | 1.00 | 14881 | 3 | | | | LOC388387 | 1.00 |
| 14786 | 3 | | | | | LOC285375 | 1.00 | 14882 | 3 | | | | LOC388553 | 1.00 |
| 14787 | 3 | | | | | LOC285401 | 1.00 | 14883 | 3 | | | | LOC388630 | 1.00 |
| 14788 | 3 | | | | | LOC285419 | 1.00 | 14884 | 3 | | | | LOC388813 | 1.00 |
| 14789 | 3 | | | | | LOC285441 | 1.00 | 14885 | 3 | | | | LOC388849 | 1.00 |
| 14790 | 3 | | | | | LOC285456 | 1.00 | 14886 | 3 | | | | LOC388906 | 1.00 |
| 14791 | 3 | | | | | LOC285484 | 1.00 | 14887 | 3 | | | | LOC388942 | 1.00 |
| 14792 | 3 | | | | | LOC285501 | 1.00 | 14888 | 3 | | | | LOC388946 | 1.00 |
| 14793 | 3 | | | | | LOC285547 | 1.00 | 14889 | 3 | | | | LOC388948 | 1.00 |
| 14794 | 3 | | | | | LOC285548 | 1.00 | 14890 | 3 | | | | LOC389023 | 1.00 |
| 14795 | 3 | | | | | LOC285577 | 1.00 | 14891 | 3 | | | | LOC389033 | 1.00 |
| 14796 | 3 | | | | | LOC285593 | 1.00 | 14892 | 3 | | | | LOC389043 | 1.00 |
| 14797 | 3 | | | | | LOC285626 | 1.00 | 14893 | 3 | | | | LOC389247 | 1.00 |
| 14798 | 3 | | | | | LOC285627 | 1.00 | 14894 | 3 | | | | LOC389332 | 1.00 |
| 14799 | 3 | | | | | LOC285629 | 1.00 | 14895 | 3 | | | | LOC389458 | 1.00 |
| 14800 | 3 | | | | | LOC285692 | 1.00 | 14896 | 3 | | | | LOC389493 | 1.00 |
| 14801 | 3 | | | | | LOC285696 | 1.00 | 14897 | 3 | | | | LOC389705 | 1.00 |
| 14802 | 3 | | | | | LOC285740 | 1.00 | 14898 | 3 | | | | LOC389765 | 1.00 |
| 14803 | 3 | | | | | LOC285758 | 1.00 | 14899 | 3 | | | | LOC389791 | 1.00 |
| 14804 | 3 | | | | | LOC285762 | 1.00 | 14900 | 3 | | | | LOC390660 | 1.00 |
| 14805 | 3 | | | | | LOC285768 | 1.00 | 14901 | 3 | | | | LOC390705 | 1.00 |
| 14806 | 3 | | | | | LOC285796 | 1.00 | 14902 | 3 | | | | LOC390858 | 1.00 |
| 14807 | 3 | | | | | LOC285819 | 1.00 | 14903 | 3 | | | | LOC391322 | 1.00 |
| 14808 | 3 | | | | | LOC285847 | 1.00 | 14904 | 3 | | | | LOC392196 | 1.00 |
| 14809 | 3 | | | | | LOC285878 | 1.00 | 14905 | 3 | | | | LOC392232 | 1.00 |
| 14810 | 3 | | | | | LOC285889 | 1.00 | 14906 | 3 | | | | LOC392364 | 1.00 |
| 14811 | 3 | | | | | LOC285954 | 1.00 | 14907 | 3 | | | | LOC399708 | 1.00 |
| 14812 | 3 | | | | | LOC285972 | 1.00 | 14908 | 3 | | | | LOC399715 | 1.00 |
| 14813 | 3 | | | | | LOC286002 | 1.00 | 14909 | 3 | | | | LOC399744 | 1.00 |
| 14814 | 3 | | | | | LOC286059 | 1.00 | 14910 | 3 | | | | LOC399753 | 1.00 |
| 14815 | 3 | | | | | LOC286083 | 1.00 | 14911 | 3 | | | | LOC399815 | 1.00 |
| 14816 | 3 | | | | | LOC286094 | 1.00 | 14912 | 3 | | | | LOC399829 | 1.00 |
| 14817 | 3 | | | | | LOC286114 | 1.00 | 14913 | 3 | | | | LOC399939 | 1.00 |
| 14818 | 3 | | | | | LOC286135 | 1.00 | 14914 | 3 | | | | LOC399940 | 1.00 |
| 14819 | 3 | | | | | LOC286177 | 1.00 | 14915 | 3 | | | | LOC400043 | 1.00 |
| 14820 | 3 | | | | | LOC286184 | 1.00 | 14916 | 3 | | | | LOC400084 | 1.00 |
| 14821 | 3 | | | | | LOC286186 | 1.00 | 14917 | 3 | | | | LOC400238 | 1.00 |
| 14822 | 3 | | | | | LOC286189 | 1.00 | 14918 | 3 | | | | LOC400456 | 1.00 |
| 14823 | 3 | | | | | LOC286190 | 1.00 | 14919 | 3 | | | | LOC400548 | 1.00 |
| 14824 | 3 | | | | | LOC286238 | 1.00 | 14920 | 3 | | | | LOC400550 | 1.00 |
| 14825 | 3 | | | | | LOC286297 | 1.00 | 14921 | 3 | | | | LOC400558 | 1.00 |
| 14826 | 3 | | | | | LOC286359 | 1.00 | 14922 | 3 | | | | LOC400620 | 1.00 |
| 14827 | 3 | | | | | LOC286367 | 1.00 | 14923 | 3 | | | | LOC400643 | 1.00 |
| 14828 | 3 | | | | | LOC286370 | 1.00 | 14924 | 3 | | | | LOC400654 | 1.00 |
| 14829 | 3 | | | | | LOC286442 | 1.00 | 14925 | 3 | | | | LOC400655 | 1.00 |
| 14830 | 3 | | | | | LOC286467 | 1.00 | 14926 | 3 | | | | LOC400680 | 1.00 |
| 14831 | 3 | | | | | LOC338579 | 1.00 | 14927 | 3 | | | | LOC400684 | 1.00 |
| 14832 | 3 | | | | | LOC338588 | 1.00 | 14928 | 3 | | | | LOC400752 | 1.00 |
| 14833 | 3 | | | | | LOC338651 | 1.00 | 14929 | 3 | | | | LOC400794 | 1.00 |
| 14834 | 3 | | | | | LOC338739 | 1.00 | 14930 | 3 | | | | LOC400891 | 1.00 |
| 14835 | 3 | | | | | LOC338817 | 1.00 | 14931 | 3 | | | | LOC400940 | 1.00 |
| 14836 | 3 | | | | | LOC338963 | 1.00 | 14932 | 3 | | | | LOC400958 | 1.00 |
| 14837 | 3 | | | | | LOC339166 | 1.00 | 14933 | 3 | | | | LOC401052 | 1.00 |
| 14838 | 3 | | | | | LOC339240 | 1.00 | 14934 | 3 | | | | LOC401074 | 1.00 |
| 14839 | 3 | | | | | LOC339298 | 1.00 | 14935 | 3 | | | | LOC401093 | 1.00 |
| 14840 | 3 | | | | | LOC339442 | 1.00 | 14936 | 3 | | | | LOC401109 | 1.00 |
| 14841 | 3 | | | | | LOC339505 | 1.00 | 14937 | 3 | | | | LOC401134 | 1.00 |
| 14842 | 3 | | | | | LOC339524 | 1.00 | 14938 | 3 | | | | LOC401164 | 1.00 |
| 14843 | 3 | | | | | LOC339529 | 1.00 | 14939 | 3 | | | | LOC401177 | 1.00 |
| 14844 | 3 | | | | | LOC339535 | 1.00 | 14940 | 3 | | | | LOC401242 | 1.00 |
| 14845 | 3 | | | | | LOC339568 | 1.00 | 14941 | 3 | | | | LOC401321 | 1.00 |
| 14846 | 3 | | | | | LOC339593 | 1.00 | 14942 | 3 | | | | LOC401324 | 1.00 |
| 14847 | 3 | | | | | LOC339622 | 1.00 | 14943 | 3 | | | | LOC401431 | 1.00 |
| 14848 | 3 | | | | | LOC339666 | 1.00 | 14944 | 3 | | | | LOC401463 | 1.00 |
| 14849 | 3 | | | | | LOC339685 | 1.00 | 14945 | 3 | | | | LOC401497 | 1.00 |
| 14850 | 3 | | | | | LOC339788 | 1.00 | 14946 | 3 | | | | LOC401557 | 1.00 |
| 14851 | 3 | | | | | LOC339807 | 1.00 | 14947 | 3 | | | | LOC401588 | 1.00 |
| 14852 | 3 | | | | | LOC339822 | 1.00 | 14948 | 3 | | | | LOC401980 | 1.00 |
| 14853 | 3 | | | | | LOC339862 | 1.00 | 14949 | 3 | | | | LOC402160 | 1.00 |
| 14854 | 3 | | | | | LOC339874 | 1.00 | 14950 | 3 | | | | LOC402779 | 1.00 |
| 14855 | 3 | | | | | LOC339894 | 1.00 | 14951 | 3 | | | | LOC415056 | 1.00 |
| 14856 | 3 | | | | | LOC339926 | 1.00 | 14952 | 3 | | | | LOC439950 | 1.00 |
| 14857 | 3 | | | | | LOC339975 | 1.00 | 14953 | 3 | | | | LOC439990 | 1.00 |
| 14858 | 3 | | | | | LOC340017 | 1.00 | 14954 | 3 | | | | LOC440028 | 1.00 |
| 14859 | 3 | | | | | LOC340073 | 1.00 | 14955 | 3 | | | | LOC440040 | 1.00 |
| 14860 | 3 | | | | | LOC340074 | 1.00 | 14956 | 3 | | | | LOC440041 | 1.00 |
| 14861 | 3 | | | | | LOC340094 | 1.00 | 14957 | 3 | | | | LOC440117 | 1.00 |
| 14862 | 3 | | | | | LOC340107 | 1.00 | 14958 | 3 | | | | LOC440131 | 1.00 |
| 14863 | 3 | | | | | LOC340113 | 1.00 | 14959 | 3 | | | | LOC440173 | 1.00 |
| 14864 | 3 | | | | | LOC340357 | 1.00 | 14960 | 3 | | | | LOC440297 | 1.00 |
| 14865 | 3 | | | | | LOC340508 | 1.00 | 14961 | 3 | | | | LOC440300 | 1.00 |
| 14866 | 3 | | | | | LOC340515 | 1.00 | 14962 | 3 | | | | LOC440335 | 1.00 |
| 14867 | 3 | | | | | LOC340544 | 1.00 | 14963 | 3 | | | | LOC440356 | 1.00 |
| 14868 | 3 | | | | | LOC344595 | 1.00 | 14964 | 3 | | | | LOC440461 | 1.00 |
| 14869 | 3 | | | | | LOC344887 | 1.00 | 14965 | 3 | | | | LOC440518 | 1.00 |
| 14870 | 3 | | | | | LOC347411 | 1.00 | 14966 | 3 | | | | LOC440563 | 1.00 |
| 14871 | 3 | | | | | LOC348120 | 1.00 | 14967 | 3 | | | | LOC440600 | 1.00 |
| 14872 | 3 | | | | | LOC348761 | 1.00 | 14968 | 3 | | | | LOC440700 | 1.00 |
| 14873 | 3 | | | | | LOC349160 | 1.00 | 14969 | 3 | | | | LOC440704 | 1.00 |
| 14874 | 3 | | | | | LOC349196 | 1.00 | 14970 | 3 | | | | LOC440894 | 1.00 |

Fig. 41 - 79

| | | | | | | | | | | | | | | | | |
|---|---|---|---|---|---|---|---|---|---|---|---|---|---|---|---|---|
| 14971 | 3 | | | | | LOC440895 | 1.00 | | 15067 | 3 | | | | | LOC646903 | 1.00 |
| 14972 | 3 | | | | | LOC440896 | 1.00 | | 15068 | 3 | | | | | LOC646938 | 1.00 |
| 14973 | 3 | | | | | LOC440900 | 1.00 | | 15069 | 3 | | | | | LOC646999 | 1.00 |
| 14974 | 3 | | | | | LOC440905 | 1.00 | | 15070 | 3 | | | | | LOC647012 | 1.00 |
| 14975 | 3 | | | | | LOC440910 | 1.00 | | 15071 | 3 | | | | | LOC647107 | 1.00 |
| 14976 | 3 | | | | | LOC440925 | 1.00 | | 15072 | 3 | | | | | LOC647323 | 1.00 |
| 14977 | 3 | | | | | LOC440970 | 1.00 | | 15073 | 3 | | | | | LOC647589 | 1.00 |
| 14978 | 3 | | | | | LOC441009 | 1.00 | | 15074 | 3 | | | | | LOC647859 | 1.00 |
| 14979 | 3 | | | | | LOC441025 | 1.00 | | 15075 | 3 | | | | | LOC647946 | 1.00 |
| 14980 | 3 | | | | | LOC441177 | 1.00 | | 15076 | 3 | | | | | LOC648691 | 1.00 |
| 14981 | 3 | | | | | LOC441204 | 1.00 | | 15077 | 3 | | | | | LOC648809 | 1.00 |
| 14982 | 3 | | | | | LOC441242 | 1.00 | | 15078 | 3 | | | | | LOC649133 | 1.00 |
| 14983 | 3 | | | | | LOC441454 | 1.00 | | 15079 | 3 | | | | | LOC649330 | 1.00 |
| 14984 | 3 | | | | | LOC441461 | 1.00 | | 15080 | 3 | | | | | LOC650226 | 1.00 |
| 14985 | 3 | | | | | LOC441495 | 1.00 | | 15081 | 3 | | | | | LOC650293 | 1.00 |
| 14986 | 3 | | | | | LOC441601 | 1.00 | | 15082 | 3 | | | | | LOC650368 | 1.00 |
| 14987 | 3 | | | | | LOC441666 | 1.00 | | 15083 | 3 | | | | | LOC650623 | 1.00 |
| 14988 | 3 | | | | | LOC442028 | 1.00 | | 15084 | 3 | | | | | LOC653061 | 1.00 |
| 14989 | 3 | | | | | LOC442132 | 1.00 | | 15085 | 3 | | | | | LOC653075 | 1.00 |
| 14990 | 3 | | | | | LOC442421 | 1.00 | | 15086 | 3 | | | | | LOC653501 | 1.00 |
| 14991 | 3 | | | | | LOC442459 | 1.00 | | 15087 | 3 | | | | | LOC653513 | 1.00 |
| 14992 | 3 | | | | | LOC442497 | 1.00 | | 15088 | 3 | | | | | LOC653712 | 1.00 |
| 14993 | 3 | | | | | LOC494141 | 1.00 | | 15089 | 3 | | | | | LOC653786 | 1.00 |
| 14994 | 3 | | | | | LOC494558 | 1.00 | | 15090 | 3 | | | | | LOC723809 | 1.00 |
| 14995 | 3 | | | | | LOC503519 | 1.00 | | 15091 | 3 | | | | | LOC727677 | 1.00 |
| 14996 | 3 | | | | | LOC541473 | 1.00 | | 15092 | 3 | | | | | LOC727710 | 1.00 |
| 14997 | 3 | | | | | LOC550113 | 1.00 | | 15093 | 3 | | | | | LOC727915 | 1.00 |
| 14998 | 3 | | | | | LOC553103 | 1.00 | | 15094 | 3 | | | | | LOC727924 | 1.00 |
| 14999 | 3 | | | | | LOC554201 | 1.00 | | 15095 | 3 | | | | | LOC727982 | 1.00 |
| 15000 | 3 | | | | | LOC554223 | 1.00 | | 15096 | 3 | | | | | LOC728012 | 1.00 |
| 15001 | 3 | | | | | LOC572558 | 1.00 | | 15097 | 3 | | | | | LOC728040 | 1.00 |
| 15002 | 3 | | | | | LOC574538 | 1.00 | | 15098 | 3 | | | | | LOC728084 | 1.00 |
| 15003 | 3 | | | | | LOC619207 | 1.00 | | 15099 | 3 | | | | | LOC728175 | 1.00 |
| 15004 | 3 | | | | | LOC63930 | 1.00 | | 15100 | 3 | | | | | LOC728218 | 1.00 |
| 15005 | 3 | | | | | LOC641364 | 1.00 | | 15101 | 3 | | | | | LOC728228 | 1.00 |
| 15006 | 3 | | | | | LOC641365 | 1.00 | | 15102 | 3 | | | | | LOC728342 | 1.00 |
| 15007 | 3 | | | | | LOC641515 | 1.00 | | 15103 | 3 | | | | | LOC728369 | 1.00 |
| 15008 | 3 | | | | | LOC641746 | 1.00 | | 15104 | 3 | | | | | LOC728393 | 1.00 |
| 15009 | 3 | | | | | LOC642236 | 1.00 | | 15105 | 3 | | | | | LOC728405 | 1.00 |
| 15010 | 3 | | | | | LOC642366 | 1.00 | | 15106 | 3 | | | | | LOC728407 | 1.00 |
| 15011 | 3 | | | | | LOC642426 | 1.00 | | 15107 | 3 | | | | | LOC728437 | 1.00 |
| 15012 | 3 | | | | | LOC642826 | 1.00 | | 15108 | 3 | | | | | LOC728463 | 1.00 |
| 15013 | 3 | | | | | LOC642846 | 1.00 | | 15109 | 3 | | | | | LOC728537 | 1.00 |
| 15014 | 3 | | | | | LOC642929 | 1.00 | | 15110 | 3 | | | | | LOC728558 | 1.00 |
| 15015 | 3 | | | | | LOC643037 | 1.00 | | 15111 | 3 | | | | | LOC728606 | 1.00 |
| 15016 | 3 | | | | | LOC643201 | 1.00 | | 15112 | 3 | | | | | LOC728640 | 1.00 |
| 15017 | 3 | | | | | LOC643339 | 1.00 | | 15113 | 3 | | | | | LOC728643 | 1.00 |
| 15018 | 3 | | | | | LOC643401 | 1.00 | | 15114 | 3 | | | | | LOC728716 | 1.00 |
| 15019 | 3 | | | | | LOC643406 | 1.00 | | 15115 | 3 | | | | | LOC728723 | 1.00 |
| 15020 | 3 | | | | | LOC643441 | 1.00 | | 15116 | 3 | | | | | LOC728724 | 1.00 |
| 15021 | 3 | | | | | LOC643486 | 1.00 | | 15117 | 3 | | | | | LOC728730 | 1.00 |
| 15022 | 3 | | | | | LOC643529 | 1.00 | | 15118 | 3 | | | | | LOC728819 | 1.00 |
| 15023 | 3 | | | | | LOC643542 | 1.00 | | 15119 | 3 | | | | | LOC728978 | 1.00 |
| 15024 | 3 | | | | | LOC643623 | 1.00 | | 15120 | 3 | | | | | LOC729041 | 1.00 |
| 15025 | 3 | | | | | LOC643648 | 1.00 | | 15121 | 3 | | | | | LOC729059 | 1.00 |
| 15026 | 3 | | | | | LOC643650 | 1.00 | | 15122 | 3 | | | | | LOC729080 | 1.00 |
| 15027 | 3 | | | | | LOC643669 | 1.00 | | 15123 | 3 | | | | | LOC729121 | 1.00 |
| 15028 | 3 | | | | | LOC643714 | 1.00 | | 15124 | 3 | | | | | LOC729156 | 1.00 |
| 15029 | 3 | | | | | LOC643770 | 1.00 | | 15125 | 3 | | | | | LOC729177 | 1.00 |
| 15030 | 3 | | | | | LOC643923 | 1.00 | | 15126 | 3 | | | | | LOC729264 | 1.00 |
| 15031 | 3 | | | | | LOC643955 | 1.00 | | 15127 | 3 | | | | | LOC729444 | 1.00 |
| 15032 | 3 | | | | | LOC644100 | 1.00 | | 15128 | 3 | | | | | LOC729506 | 1.00 |
| 15033 | 3 | | | | | LOC644145 | 1.00 | | 15129 | 3 | | | | | LOC729513 | 1.00 |
| 15034 | 3 | | | | | LOC644172 | 1.00 | | 15130 | 3 | | | | | LOC729609 | 1.00 |
| 15035 | 3 | | | | | LOC644189 | 1.00 | | 15131 | 3 | | | | | LOC729668 | 1.00 |
| 15036 | 3 | | | | | LOC644242 | 1.00 | | 15132 | 3 | | | | | LOC729739 | 1.00 |
| 15037 | 3 | | | | | LOC644248 | 1.00 | | 15133 | 3 | | | | | LOC729911 | 1.00 |
| 15038 | 3 | | | | | LOC644554 | 1.00 | | 15134 | 3 | | | | | LOC729950 | 1.00 |
| 15039 | 3 | | | | | LOC644656 | 1.00 | | 15135 | 3 | | | | | LOC729966 | 1.00 |
| 15040 | 3 | | | | | LOC644669 | 1.00 | | 15136 | 3 | | | | | LOC729970 | 1.00 |
| 15041 | 3 | | | | | LOC644838 | 1.00 | | 15137 | 3 | | | | | LOC729987 | 1.00 |
| 15042 | 3 | | | | | LOC644990 | 1.00 | | 15138 | 3 | | | | | LOC730091 | 1.00 |
| 15043 | 3 | | | | | LOC645166 | 1.00 | | 15139 | 3 | | | | | LOC730101 | 1.00 |
| 15044 | 3 | | | | | LOC645206 | 1.00 | | 15140 | 3 | | | | | LOC730159 | 1.00 |
| 15045 | 3 | | | | | LOC645249 | 1.00 | | 15141 | 3 | | | | | LOC730227 | 1.00 |
| 15046 | 3 | | | | | LOC645355 | 1.00 | | 15142 | 3 | | | | | LOC730441 | 1.00 |
| 15047 | 3 | | | | | LOC645431 | 1.00 | | 15143 | 3 | | | | | LOC730668 | 1.00 |
| 15048 | 3 | | | | | LOC645434 | 1.00 | | 15144 | 3 | | | | | LOC730755 | 1.00 |
| 15049 | 3 | | | | | LOC645591 | 1.00 | | 15145 | 3 | | | | | LOC730811 | 1.00 |
| 15050 | 3 | | | | | LOC645676 | 1.00 | | 15146 | 3 | | | | | LOC731223 | 1.00 |
| 15051 | 3 | | | | | LOC645752 | 1.00 | | 15147 | 3 | | | | | LOC731779 | 1.00 |
| 15052 | 3 | | | | | LOC645949 | 1.00 | | 15148 | 3 | | | | | LOC731789 | 1.00 |
| 15053 | 3 | | | | | LOC646168 | 1.00 | | 15149 | 3 | | | | | LOC732275 | 1.00 |
| 15054 | 3 | | | | | LOC646268 | 1.00 | | 15150 | 3 | | | | | LOC81691 | 1.00 |
| 15055 | 3 | | | | | LOC646278 | 1.00 | | 15151 | 3 | | | | | LOC84856 | 1.00 |
| 15056 | 3 | | | | | LOC646324 | 1.00 | | 15152 | 3 | | | | | LOC84931 | 1.00 |
| 15057 | 3 | | | | | LOC646498 | 1.00 | | 15153 | 3 | | | | | LOC84989 | 1.00 |
| 15058 | 3 | | | | | LOC646508 | 1.00 | | 15154 | 3 | | | | | LOC90246 | 1.00 |
| 15059 | 3 | | | | | LOC646576 | 1.00 | | 15155 | 3 | | | | | LOC90499 | 1.00 |
| 15060 | 3 | | | | | LOC646626 | 1.00 | | 15156 | 3 | | | | | LOC90834 | 1.00 |
| 15061 | 3 | | | | | LOC646627 | 1.00 | | 15157 | 3 | | | | | LOC91149 | 1.00 |
| 15062 | 3 | | | | | LOC646736 | 1.00 | | 15158 | 3 | | | | | LOC91450 | 1.00 |
| 15063 | 3 | | | | | LOC646743 | 1.00 | | 15159 | 3 | | | | | LOC91948 | 1.00 |
| 15064 | 3 | | | | | LOC646813 | 1.00 | | 15160 | 3 | | | | | LOC93432 | 1.00 |
| 15065 | 3 | | | | | LOC646851 | 1.00 | | 15161 | 3 | | | | | LOH12CR2 | 1.00 |
| 15066 | 3 | | | | | LOC646862 | 1.00 | | 15162 | 3 | | | | | LONRF2 | 1.00 |

Fig. 41 - 80

| | | | | | | | | | | | | | | | |
|---|---|---|---|---|---|---|---|---|---|---|---|---|---|---|---|
| 15163 | 3 | | | | | LOR | 1.00 | 15259 | 3 | | | | | LY6G6C | 1.00 |
| 15164 | 3 | | | | | LOX | 1.00 | 15260 | 3 | | | | | LY6G6D | 1.00 |
| 15165 | 3 | | | | | LOXHD1 | 1.00 | 15261 | 3 | | | | | LY6H | 1.00 |
| 15166 | 3 | | | | | LOXL1 | 1.00 | 15262 | 3 | | | | | LY6K | 1.00 |
| 15167 | 3 | | | | | LOXL2 | 1.00 | 15263 | 3 | | | | | LY75-CD302 | 1.00 |
| 15168 | 3 | | | | | LOXL4 | 1.00 | 15264 | 3 | | | | | LY86-AS1 | 1.00 |
| 15169 | 3 | | | | | LPA | 1.00 | 15265 | 3 | | | | | LYG1 | 1.00 |
| 15170 | 3 | | | | | LPAL2 | 1.00 | 15266 | 3 | | | | | LYG2 | 1.00 |
| 15171 | 3 | | | | | LPAR3 | 1.00 | 15267 | 3 | | | | | LYPD1 | 1.00 |
| 15172 | 3 | | | | | LPAR4 | 1.00 | 15268 | 3 | | | | | LYPD4 | 1.00 |
| 15173 | 3 | | | | | LPHN2 | 1.00 | 15269 | 3 | | | | | LYPD5 | 1.00 |
| 15174 | 3 | | | | | LPHN3 | 1.00 | 15270 | 3 | | | | | LYPD6 | 1.00 |
| 15175 | 3 | | | | | LPIN3 | 1.00 | 15271 | 3 | | | | | LYPD6B | 1.00 |
| 15176 | 3 | | | | | LPL | 1.00 | 15272 | 3 | | | | | LYZL1 | 1.00 |
| 15177 | 3 | | | | | LPO | 1.00 | 15273 | 3 | | | | | LYZL2 | 1.00 |
| 15178 | 3 | | | | | LPPR1 | 1.00 | 15274 | 3 | | | | | LYZL4 | 1.00 |
| 15179 | 3 | | | | | LPPR3 | 1.00 | 15275 | 3 | | | | | LYZL6 | 1.00 |
| 15180 | 3 | | | | | LPPR4 | 1.00 | 15276 | 3 | | | | | LZTS1 | 1.00 |
| 15181 | 3 | | | | | LPPR5 | 1.00 | 15277 | 3 | | | | | M1 | 1.00 |
| 15182 | 3 | | | | | LRAT | 1.00 | 15278 | 3 | | | | | MAB21L1 | 1.00 |
| 15183 | 3 | | | | | LRCH2 | 1.00 | 15279 | 3 | | | | | MAB21L2 | 1.00 |
| 15184 | 3 | | | | | LRFN2 | 1.00 | 15280 | 3 | | | | | MAB21L3 | 1.00 |
| 15185 | 3 | | | | | LRFN5 | 1.00 | 15281 | 3 | | | | | MACC1 | 1.00 |
| 15186 | 3 | | | | | LRGUK | 1.00 | 15282 | 3 | | | | | MACROD1 | 1.00 |
| 15187 | 3 | | | | | LRIG3 | 1.00 | 15283 | 3 | | | | | MACROD2-AS1 | 1.00 |
| 15188 | 3 | | | | | LRIT1 | 1.00 | 15284 | 3 | | | | | MAEL | 1.00 |
| 15189 | 3 | | | | | LRIT2 | 1.00 | 15285 | 3 | | | | | MAFA | 1.00 |
| 15190 | 3 | | | | | LRIT3 | 1.00 | 15286 | 3 | | | | | MAFG-AS1 | 1.00 |
| 15191 | 3 | | | | | LRP1B | 1.00 | 15287 | 3 | | | | | MAG | 1.00 |
| 15192 | 3 | | | | | LRP2 | 1.00 | 15288 | 3 | | | | | MAGEA1 | 1.00 |
| 15193 | 3 | | | | | LRP2BP | 1.00 | 15289 | 3 | | | | | MAGEA10 | 1.00 |
| 15194 | 3 | | | | | LRP4 | 1.00 | 15290 | 3 | | | | | MAGEA10-MAGEA5 | 1.00 |
| 15195 | 3 | | | | | LRP5 | 1.00 | | | | | | | | |
| 15196 | 3 | | | | | LRP6 | 1.00 | 15291 | 3 | | | | | MAGEA11 | 1.00 |
| 15197 | 3 | | | | | LRRC1 | 1.00 | 15292 | 3 | | | | | MAGEA12 | 1.00 |
| 15198 | 3 | | | | | LRRC10 | 1.00 | 15293 | 3 | | | | | MAGEA2 | 1.00 |
| 15199 | 3 | | | | | LRRC10B | 1.00 | 15294 | 3 | | | | | MAGEA2B | 1.00 |
| 15200 | 3 | | | | | LRRC14B | 1.00 | 15295 | 3 | | | | | MAGEA3 | 1.00 |
| 15201 | 3 | | | | | LRRC15 | 1.00 | 15296 | 3 | | | | | MAGEA4 | 1.00 |
| 15202 | 3 | | | | | LRRC16B | 1.00 | 15297 | 3 | | | | | MAGEA5 | 1.00 |
| 15203 | 3 | | | | | LRRC17 | 1.00 | 15298 | 3 | | | | | MAGEA6 | 1.00 |
| 15204 | 3 | | | | | LRRC18 | 1.00 | 15299 | 3 | | | | | MAGEA8 | 1.00 |
| 15205 | 3 | | | | | LRRC19 | 1.00 | 15300 | 3 | | | | | MAGEA9 | 1.00 |
| 15206 | 3 | | | | | LRRC2 | 1.00 | 15301 | 3 | | | | | MAGEA9B | 1.00 |
| 15207 | 3 | | | | | LRRC24 | 1.00 | 15302 | 3 | | | | | MAGEB1 | 1.00 |
| 15208 | 3 | | | | | LRRC26 | 1.00 | 15303 | 3 | | | | | MAGEB10 | 1.00 |
| 15209 | 3 | | | | | LRRC29 | 1.00 | 15304 | 3 | | | | | MAGEB16 | 1.00 |
| 15210 | 3 | | | | | LRRC3 | 1.00 | 15305 | 3 | | | | | MAGEB18 | 1.00 |
| 15211 | 3 | | | | | LRRC30 | 1.00 | 15306 | 3 | | | | | MAGEB2 | 1.00 |
| 15212 | 3 | | | | | LRRC31 | 1.00 | 15307 | 3 | | | | | MAGEB3 | 1.00 |
| 15213 | 3 | | | | | LRRC32 | 1.00 | 15308 | 3 | | | | | MAGEB4 | 1.00 |
| 15214 | 3 | | | | | LRRC34 | 1.00 | 15309 | 3 | | | | | MAGEB6 | 1.00 |
| 15215 | 3 | | | | | LRRC36 | 1.00 | 15310 | 3 | | | | | MAGEC1 | 1.00 |
| 15216 | 3 | | | | | LRRC37A3 | 1.00 | 15311 | 3 | | | | | MAGEC2 | 1.00 |
| 15217 | 3 | | | | | LRRC38 | 1.00 | 15312 | 3 | | | | | MAGEC3 | 1.00 |
| 15218 | 3 | | | | | LRRC39 | 1.00 | 15313 | 3 | | | | | MAGED4 | 1.00 |
| 15219 | 3 | | | | | LRRC3B | 1.00 | 15314 | 3 | | | | | MAGED4B | 1.00 |
| 15220 | 3 | | | | | LRRC3C | 1.00 | 15315 | 3 | | | | | MAGEE2 | 1.00 |
| 15221 | 3 | | | | | LRRC43 | 1.00 | 15316 | 3 | | | | | MAGEL2 | 1.00 |
| 15222 | 3 | | | | | LRRC46 | 1.00 | 15317 | 3 | | | | | MAGI1 | 1.00 |
| 15223 | 3 | | | | | LRRC48 | 1.00 | 15318 | 3 | | | | | MAGI2 | 1.00 |
| 15224 | 3 | | | | | LRRC49 | 1.00 | 15319 | 3 | | | | | MAGI2-AS3 | 1.00 |
| 15225 | 3 | | | | | LRRC4B | 1.00 | 15320 | 3 | | | | | MAGI3 | 1.00 |
| 15226 | 3 | | | | | LRRC4C | 1.00 | 15321 | 3 | | | | | MAGIX | 1.00 |
| 15227 | 3 | | | | | LRRC52 | 1.00 | 15322 | 3 | | | | | MAL2 | 1.00 |
| 15228 | 3 | | | | | LRRC55 | 1.00 | 15323 | 3 | | | | | MALL | 1.00 |
| 15229 | 3 | | | | | LRRC56 | 1.00 | 15324 | 3 | | | | | MAMDC2 | 1.00 |
| 15230 | 3 | | | | | LRRC66 | 1.00 | 15325 | 3 | | | | | MAMDC4 | 1.00 |
| 15231 | 3 | | | | | LRRC69 | 1.00 | 15326 | 3 | | | | | MAMLD1 | 1.00 |
| 15232 | 3 | | | | | LRRC7 | 1.00 | 15327 | 3 | | | | | MAMSTR | 1.00 |
| 15233 | 3 | | | | | LRRC71 | 1.00 | 15328 | 3 | | | | | MANSC4 | 1.00 |
| 15234 | 3 | | | | | LRRC72 | 1.00 | 15329 | 3 | | | | | MAOA | 1.00 |
| 15235 | 3 | | | | | LRRC73 | 1.00 | 15330 | 3 | | | | | MAOB | 1.00 |
| 15236 | 3 | | | | | LRRC8E | 1.00 | 15331 | 3 | | | | | MAP1B | 1.00 |
| 15237 | 3 | | | | | LRRD1 | 1.00 | 15332 | 3 | | | | | MAP1LC3C | 1.00 |
| 15238 | 3 | | | | | LRRIQ1 | 1.00 | 15333 | 3 | | | | | MAP2 | 1.00 |
| 15239 | 3 | | | | | LRRIQ3 | 1.00 | 15334 | 3 | | | | | MAP3K15 | 1.00 |
| 15240 | 3 | | | | | LRRIQ4 | 1.00 | 15335 | 3 | | | | | MAP3K9 | 1.00 |
| 15241 | 3 | | | | | LRRN4 | 1.00 | 15336 | 3 | | | | | MAP6 | 1.00 |
| 15242 | 3 | | | | | LRRN4CL | 1.00 | 15337 | 3 | | | | | MAP6D1 | 1.00 |
| 15243 | 3 | | | | | LRRTM1 | 1.00 | 15338 | 3 | | | | | MAP7D2 | 1.00 |
| 15244 | 3 | | | | | LRRTM2 | 1.00 | 15339 | 3 | | | | | MAP9 | 1.00 |
| 15245 | 3 | | | | | LRRTM3 | 1.00 | 15340 | 3 | | | | | MAPK10 | 1.00 |
| 15246 | 3 | | | | | LRRTM4 | 1.00 | 15341 | 3 | | | | | MAPK11 | 1.00 |
| 15247 | 3 | | | | | LRTM1 | 1.00 | 15342 | 3 | | | | | MAPK12 | 1.00 |
| 15248 | 3 | | | | | LRTM2 | 1.00 | 15343 | 3 | | | | | MAPK15 | 1.00 |
| 15249 | 3 | | | | | LSAMP | 1.00 | 15344 | 3 | | | | | MAPK4 | 1.00 |
| 15250 | 3 | | | | | LSAMP-AS3 | 1.00 | 15345 | 3 | | | | | MAPK8IP1 | 1.00 |
| 15251 | 3 | | | | | LTC4S | 1.00 | 15346 | 3 | | | | | MAPK8IP2 | 1.00 |
| 15252 | 3 | | | | | LTK | 1.00 | 15347 | 3 | | | | | MAPT | 1.00 |
| 15253 | 3 | | | | | LUM | 1.00 | 15348 | 3 | | | | | MAPT-AS1 | 1.00 |
| 15254 | 3 | | | | | LURAP1 | 1.00 | 15349 | 3 | | | | | MAPT-IT1 | 1.00 |
| 15255 | 3 | | | | | LURAP1L | 1.00 | 15350 | 3 | | | | | 42431 | 1.00 |
| 15256 | 3 | | | | | LUZP2 | 1.00 | 15351 | 3 | | | | | 42439 | 1.00 |
| 15257 | 3 | | | | | LUZP4 | 1.00 | 15352 | 3 | | | | | 42440 | 1.00 |
| 15258 | 3 | | | | | LY6D | 1.00 | 15353 | 3 | | | | | 42433 | 1.00 |

Fig. 41 - 81

| | | | | | | | | | | | | | | | | |
|---|---|---|---|---|---|---|---|---|---|---|---|---|---|---|---|---|
| 15354 | 3 | | | | | MARK1 | 1.00 | 15450 | 3 | | | | | MGC4473 | 1.00 |
| 15355 | 3 | | | | | MARK2P9 | 1.00 | 15451 | 3 | | | | | MGC45800 | 1.00 |
| 15356 | 3 | | | | | MARVELD2 | 1.00 | 15452 | 3 | | | | | MGC45922 | 1.00 |
| 15357 | 3 | | | | | MARVELD3 | 1.00 | 15453 | 3 | | | | | MGP | 1.00 |
| 15358 | 3 | | | | | MAS1 | 1.00 | 15454 | 3 | | | | | MIA | 1.00 |
| 15359 | 3 | | | | | MAS1L | 1.00 | 15455 | 3 | | | | | MIA-RAB4B | 1.00 |
| 15360 | 3 | | | | | MASP1 | 1.00 | 15456 | 3 | | | | | MIA2 | 1.00 |
| 15361 | 3 | | | | | MAST1 | 1.00 | 15457 | 3 | | | | | MICALL2 | 1.00 |
| 15362 | 3 | | | | | MAT1A | 1.00 | 15458 | 3 | | | | | MID1 | 1.00 |
| 15363 | 3 | | | | | MATN1 | 1.00 | 15459 | 3 | | | | | MIMT1 | 1.00 |
| 15364 | 3 | | | | | MATN2 | 1.00 | 15460 | 3 | | | | | MIOX | 1.00 |
| 15365 | 3 | | | | | MATN3 | 1.00 | 15461 | 3 | | | | | MIP | 1.00 |
| 15366 | 3 | | | | | MATN4 | 1.00 | 15462 | 3 | | | | | MIPEP | 1.00 |
| 15367 | 3 | | | | | MB | 1.00 | 15463 | 3 | | | | | MIPOL1 | 1.00 |
| 15368 | 3 | | | | | MBD3L1 | 1.00 | 15464 | 3 | | | | | MIR1-1 | 1.00 |
| 15369 | 3 | | | | | MBD3L2 | 1.00 | 15465 | 3 | | | | | MIR1-2 | 1.00 |
| 15370 | 3 | | | | | MBD3L3 | 1.00 | 15466 | 3 | | | | | MIR100 | 1.00 |
| 15371 | 3 | | | | | MBD3L4 | 1.00 | 15467 | 3 | | | | | MIR100HG | 1.00 |
| 15372 | 3 | | | | | MBD3L5 | 1.00 | 15468 | 3 | | | | | MIR101-1 | 1.00 |
| 15373 | 3 | | | | | MBL1P | 1.00 | 15469 | 3 | | | | | MIR101-2 | 1.00 |
| 15374 | 3 | | | | | MBL2 | 1.00 | 15470 | 3 | | | | | MIR103A1 | 1.00 |
| 15375 | 3 | | | | | MBLAC1 | 1.00 | 15471 | 3 | | | | | MIR103A2 | 1.00 |
| 15376 | 3 | | | | | MBOAT4 | 1.00 | 15472 | 3 | | | | | MIR103B1 | 1.00 |
| 15377 | 3 | | | | | MC2R | 1.00 | 15473 | 3 | | | | | MIR103B2 | 1.00 |
| 15378 | 3 | | | | | MC3R | 1.00 | 15474 | 3 | | | | | MIR105-1 | 1.00 |
| 15379 | 3 | | | | | MC4R | 1.00 | 15475 | 3 | | | | | MIR105-2 | 1.00 |
| 15380 | 3 | | | | | MC5R | 1.00 | 15476 | 3 | | | | | MIR106A | 1.00 |
| 15381 | 3 | | | | | MCAM | 1.00 | 15477 | 3 | | | | | MIR106B | 1.00 |
| 15382 | 3 | | | | | MCART3P | 1.00 | 15478 | 3 | | | | | MIR107 | 1.00 |
| 15383 | 3 | | | | | MCART6 | 1.00 | 15479 | 3 | | | | | MIR10A | 1.00 |
| 15384 | 3 | | | | | MCC | 1.00 | 15480 | 3 | | | | | MIR10B | 1.00 |
| 15385 | 3 | | | | | MCCD1 | 1.00 | 15481 | 3 | | | | | MIR1178 | 1.00 |
| 15386 | 3 | | | | | MCF2 | 1.00 | 15482 | 3 | | | | | MIR1179 | 1.00 |
| 15387 | 3 | | | | | MCF2L | 1.00 | 15483 | 3 | | | | | MIR1180 | 1.00 |
| 15388 | 3 | | | | | MCF2L-AS1 | 1.00 | 15484 | 3 | | | | | MIR1181 | 1.00 |
| 15389 | 3 | | | | | MCF2L2 | 1.00 | 15485 | 3 | | | | | MIR1182 | 1.00 |
| 15390 | 3 | | | | | MCHR1 | 1.00 | 15486 | 3 | | | | | MIR1184-3 | 1.00 |
| 15391 | 3 | | | | | MCHR2 | 1.00 | 15487 | 3 | | | | | MIR1185-1 | 1.00 |
| 15392 | 3 | | | | | MCM10 | 1.00 | 15488 | 3 | | | | | MIR1185-2 | 1.00 |
| 15393 | 3 | | | | | MCOLN3 | 1.00 | 15489 | 3 | | | | | MIR1193 | 1.00 |
| 15394 | 3 | | | | | MDFI | 1.00 | 15490 | 3 | | | | | MIR1197 | 1.00 |
| 15395 | 3 | | | | | MDGA1 | 1.00 | 15491 | 3 | | | | | MIR1200 | 1.00 |
| 15396 | 3 | | | | | MDGA2 | 1.00 | 15492 | 3 | | | | | MIR1203 | 1.00 |
| 15397 | 3 | | | | | MDH1B | 1.00 | 15493 | 3 | | | | | MIR1204 | 1.00 |
| 15398 | 3 | | | | | MDK | 1.00 | 15494 | 3 | | | | | MIR1205 | 1.00 |
| 15399 | 3 | | | | | ME1 | 1.00 | 15495 | 3 | | | | | MIR1206 | 1.00 |
| 15400 | 3 | | | | | ME3 | 1.00 | 15496 | 3 | | | | | MIR1207 | 1.00 |
| 15401 | 3 | | | | | MECOM | 1.00 | 15497 | 3 | | | | | MIR1208 | 1.00 |
| 15402 | 3 | | | | | MED12L | 1.00 | 15498 | 3 | | | | | MIR122 | 1.00 |
| 15403 | 3 | | | | | MEF2BNB-MEF2B | 1.00 | 15499 | 3 | | | | | MIR1224 | 1.00 |
| 15404 | 3 | | | | | MEG3 | 1.00 | 15500 | 3 | | | | | MIR1225 | 1.00 |
| 15405 | 3 | | | | | MEG8 | 1.00 | 15501 | 3 | | | | | MIR1226 | 1.00 |
| 15406 | 3 | | | | | MEGF10 | 1.00 | 15502 | 3 | | | | | MIR1227 | 1.00 |
| 15407 | 3 | | | | | MEGF11 | 1.00 | 15503 | 3 | | | | | MIR1228 | 1.00 |
| 15408 | 3 | | | | | MEI1 | 1.00 | 15504 | 3 | | | | | MIR1229 | 1.00 |
| 15409 | 3 | | | | | MEIG1 | 1.00 | 15505 | 3 | | | | | MIR1231 | 1.00 |
| 15410 | 3 | | | | | MEIS2 | 1.00 | 15506 | 3 | | | | | MIR1233-1 | 1.00 |
| 15411 | 3 | | | | | MEIS3 | 1.00 | 15507 | 3 | | | | | MIR1233-2 | 1.00 |
| 15412 | 3 | | | | | MEIS3P1 | 1.00 | 15508 | 3 | | | | | MIR1234 | 1.00 |
| 15413 | 3 | | | | | MELK | 1.00 | 15509 | 3 | | | | | MIR1236 | 1.00 |
| 15414 | 3 | | | | | MEOX2 | 1.00 | 15510 | 3 | | | | | MIR1237 | 1.00 |
| 15415 | 3 | | | | | MEP1A | 1.00 | 15511 | 3 | | | | | MIR1238 | 1.00 |
| 15416 | 3 | | | | | MEP1B | 1.00 | 15512 | 3 | | | | | MIR124-1 | 1.00 |
| 15417 | 3 | | | | | MEPE | 1.00 | 15513 | 3 | | | | | MIR124-2 | 1.00 |
| 15418 | 3 | | | | | MESP1 | 1.00 | 15514 | 3 | | | | | MIR124-3 | 1.00 |
| 15419 | 3 | | | | | MESP2 | 1.00 | 15515 | 3 | | | | | MIR1243 | 1.00 |
| 15420 | 3 | | | | | MESTIT1 | 1.00 | 15516 | 3 | | | | | MIR1244-1 | 1.00 |
| 15421 | 3 | | | | | MET | 1.00 | 15517 | 3 | | | | | MIR1244-2 | 1.00 |
| 15422 | 3 | | | | | METAP1D | 1.00 | 15518 | 3 | | | | | MIR1244-3 | 1.00 |
| 15423 | 3 | | | | | METTL11B | 1.00 | 15519 | 3 | | | | | MIR1245A | 1.00 |
| 15424 | 3 | | | | | METTL20 | 1.00 | 15520 | 3 | | | | | MIR1245B | 1.00 |
| 15425 | 3 | | | | | METTL21C | 1.00 | 15521 | 3 | | | | | MIR1246 | 1.00 |
| 15426 | 3 | | | | | METTL21CP1 | 1.00 | 15522 | 3 | | | | | MIR1247 | 1.00 |
| 15427 | 3 | | | | | METTL24 | 1.00 | 15523 | 3 | | | | | MIR1248 | 1.00 |
| 15428 | 3 | | | | | MEX3A | 1.00 | 15524 | 3 | | | | | MIR1249 | 1.00 |
| 15429 | 3 | | | | | MEX3B | 1.00 | 15525 | 3 | | | | | MIR1250 | 1.00 |
| 15430 | 3 | | | | | MFAP2 | 1.00 | 15526 | 3 | | | | | MIR1251 | 1.00 |
| 15431 | 3 | | | | | MFAP4 | 1.00 | 15527 | 3 | | | | | MIR1252 | 1.00 |
| 15432 | 3 | | | | | MFAP5 | 1.00 | 15528 | 3 | | | | | MIR1253 | 1.00 |
| 15433 | 3 | | | | | MFI2 | 1.00 | 15529 | 3 | | | | | MIR1256 | 1.00 |
| 15434 | 3 | | | | | MFI2-AS1 | 1.00 | 15530 | 3 | | | | | MIR1257 | 1.00 |
| 15435 | 3 | | | | | MFSD4 | 1.00 | 15531 | 3 | | | | | MIR1258 | 1.00 |
| 15436 | 3 | | | | | MGAT4C | 1.00 | 15532 | 3 | | | | | MIR125A | 1.00 |
| 15437 | 3 | | | | | MGAT5B | 1.00 | 15533 | 3 | | | | | MIR125B1 | 1.00 |
| 15438 | 3 | | | | | MGC14436 | 1.00 | 15534 | 3 | | | | | MIR125B2 | 1.00 |
| 15439 | 3 | | | | | MGC15885 | 1.00 | 15535 | 3 | | | | | MIR126 | 1.00 |
| 15440 | 3 | | | | | MGC16025 | 1.00 | 15536 | 3 | | | | | MIR1260A | 1.00 |
| 15441 | 3 | | | | | MGC16121 | 1.00 | 15537 | 3 | | | | | MIR1260B | 1.00 |
| 15442 | 3 | | | | | MGC16703 | 1.00 | 15538 | 3 | | | | | MIR1262 | 1.00 |
| 15443 | 3 | | | | | MGC21881 | 1.00 | 15539 | 3 | | | | | MIR1264 | 1.00 |
| 15444 | 3 | | | | | MGC23270 | 1.00 | 15540 | 3 | | | | | MIR1265 | 1.00 |
| 15445 | 3 | | | | | MGC27382 | 1.00 | 15541 | 3 | | | | | MIR1266 | 1.00 |
| 15446 | 3 | | | | | MGC2889 | 1.00 | 15542 | 3 | | | | | MIR127 | 1.00 |
| 15447 | 3 | | | | | MGC34034 | 1.00 | 15543 | 3 | | | | | MIR1270-1 | 1.00 |
| 15448 | 3 | | | | | MGC3771 | 1.00 | 15544 | 3 | | | | | MIR1272 | 1.00 |
| 15449 | 3 | | | | | MGC39584 | 1.00 | 15545 | 3 | | | | | MIR1275 | 1.00 |

Fig. 41 - 82

| | | | | | | | | | | | | |
|---|---|---|---|---|---|---|---|---|---|---|---|---|
| 15546 | 3 | | | | MIR1276 | 1.00 | 15642 | 3 | | | MIR18A | 1.00 |
| 15547 | 3 | | | | MIR1277 | 1.00 | 15643 | 3 | | | MIR18B | 1.00 |
| 15548 | 3 | | | | MIR1278 | 1.00 | 15644 | 3 | | | MIR1908 | 1.00 |
| 15549 | 3 | | | | MIR1279 | 1.00 | 15645 | 3 | | | MIR1909 | 1.00 |
| 15550 | 3 | | | | MIR128-1 | 1.00 | 15646 | 3 | | | MIR190A | 1.00 |
| 15551 | 3 | | | | MIR128-2 | 1.00 | 15647 | 3 | | | MIR190B | 1.00 |
| 15552 | 3 | | | | MIR1280 | 1.00 | 15648 | 3 | | | MIR191 | 1.00 |
| 15553 | 3 | | | | MIR1281 | 1.00 | 15649 | 3 | | | MIR1910 | 1.00 |
| 15554 | 3 | | | | MIR1283-1 | 1.00 | 15650 | 3 | | | MIR1911 | 1.00 |
| 15555 | 3 | | | | MIR1283-2 | 1.00 | 15651 | 3 | | | MIR1912 | 1.00 |
| 15556 | 3 | | | | MIR1284 | 1.00 | 15652 | 3 | | | MIR1913 | 1.00 |
| 15557 | 3 | | | | MIR1286 | 1.00 | 15653 | 3 | | | MIR1914 | 1.00 |
| 15558 | 3 | | | | MIR1287 | 1.00 | 15654 | 3 | | | MIR1915 | 1.00 |
| 15559 | 3 | | | | MIR1288 | 1.00 | 15655 | 3 | | | MIR193A | 1.00 |
| 15560 | 3 | | | | MIR1289-2 | 1.00 | 15656 | 3 | | | MIR193B | 1.00 |
| 15561 | 3 | | | | MIR129-1 | 1.00 | 15657 | 3 | | | MIR194-1 | 1.00 |
| 15562 | 3 | | | | MIR129-2 | 1.00 | 15658 | 3 | | | MIR194-2 | 1.00 |
| 15563 | 3 | | | | MIR1291 | 1.00 | 15659 | 3 | | | MIR195 | 1.00 |
| 15564 | 3 | | | | MIR1292 | 1.00 | 15660 | 3 | | | MIR196A1 | 1.00 |
| 15565 | 3 | | | | MIR1293 | 1.00 | 15661 | 3 | | | MIR196A2 | 1.00 |
| 15566 | 3 | | | | MIR1295A | 1.00 | 15662 | 3 | | | MIR196B | 1.00 |
| 15567 | 3 | | | | MIR1296 | 1.00 | 15663 | 3 | | | MIR197 | 1.00 |
| 15568 | 3 | | | | MIR1297 | 1.00 | 15664 | 3 | | | MIR1972-1 | 1.00 |
| 15569 | 3 | | | | MIR1298 | 1.00 | 15665 | 3 | | | MIR1973 | 1.00 |
| 15570 | 3 | | | | MIR1301 | 1.00 | 15666 | 3 | | | MIR1976 | 1.00 |
| 15571 | 3 | | | | MIR1304 | 1.00 | 15667 | 3 | | | MIR198 | 1.00 |
| 15572 | 3 | | | | MIR1305 | 1.00 | 15668 | 3 | | | MIR199A1 | 1.00 |
| 15573 | 3 | | | | MIR1306 | 1.00 | 15669 | 3 | | | MIR199A2 | 1.00 |
| 15574 | 3 | | | | MIR130A | 1.00 | 15670 | 3 | | | MIR199B | 1.00 |
| 15575 | 3 | | | | MIR130B | 1.00 | 15671 | 3 | | | MIR19A | 1.00 |
| 15576 | 3 | | | | MIR132 | 1.00 | 15672 | 3 | | | MIR19B1 | 1.00 |
| 15577 | 3 | | | | MIR1322 | 1.00 | 15673 | 3 | | | MIR19B2 | 1.00 |
| 15578 | 3 | | | | MIR1323 | 1.00 | 15674 | 3 | | | MIR200A | 1.00 |
| 15579 | 3 | | | | MIR1324 | 1.00 | 15675 | 3 | | | MIR200B | 1.00 |
| 15580 | 3 | | | | MIR133A1 | 1.00 | 15676 | 3 | | | MIR200C | 1.00 |
| 15581 | 3 | | | | MIR133A2 | 1.00 | 15677 | 3 | | | MIR202 | 1.00 |
| 15582 | 3 | | | | MIR133B | 1.00 | 15678 | 3 | | | MIR203 | 1.00 |
| 15583 | 3 | | | | MIR134 | 1.00 | 15679 | 3 | | | MIR204 | 1.00 |
| 15584 | 3 | | | | MIR1343 | 1.00 | 15680 | 3 | | | MIR205 | 1.00 |
| 15585 | 3 | | | | MIR135A1 | 1.00 | 15681 | 3 | | | MIR2052 | 1.00 |
| 15586 | 3 | | | | MIR135A2 | 1.00 | 15682 | 3 | | | MIR2053 | 1.00 |
| 15587 | 3 | | | | MIR135B | 1.00 | 15683 | 3 | | | MIR2054 | 1.00 |
| 15588 | 3 | | | | MIR136 | 1.00 | 15684 | 3 | | | MIR205HG | 1.00 |
| 15589 | 3 | | | | MIR137 | 1.00 | 15685 | 3 | | | MIR206 | 1.00 |
| 15590 | 3 | | | | MIR137HG | 1.00 | 15686 | 3 | | | MIR208A | 1.00 |
| 15591 | 3 | | | | MIR138-1 | 1.00 | 15687 | 3 | | | MIR208B | 1.00 |
| 15592 | 3 | | | | MIR138-2 | 1.00 | 15688 | 3 | | | MIR20A | 1.00 |
| 15593 | 3 | | | | MIR139 | 1.00 | 15689 | 3 | | | MIR20B | 1.00 |
| 15594 | 3 | | | | MIR140 | 1.00 | 15690 | 3 | | | MIR21 | 1.00 |
| 15595 | 3 | | | | MIR141 | 1.00 | 15691 | 3 | | | MIR210 | 1.00 |
| 15596 | 3 | | | | MIR142 | 1.00 | 15692 | 3 | | | MIR210HG | 1.00 |
| 15597 | 3 | | | | MIR143 | 1.00 | 15693 | 3 | | | MIR211 | 1.00 |
| 15598 | 3 | | | | MIR143HG | 1.00 | 15694 | 3 | | | MIR2110 | 1.00 |
| 15599 | 3 | | | | MIR144 | 1.00 | 15695 | 3 | | | MIR2113 | 1.00 |
| 15600 | 3 | | | | MIR145 | 1.00 | 15696 | 3 | | | MIR2114 | 1.00 |
| 15601 | 3 | | | | MIR1468 | 1.00 | 15697 | 3 | | | MIR2116 | 1.00 |
| 15602 | 3 | | | | MIR1469 | 1.00 | 15698 | 3 | | | MIR2117 | 1.00 |
| 15603 | 3 | | | | MIR146A | 1.00 | 15699 | 3 | | | MIR212 | 1.00 |
| 15604 | 3 | | | | MIR146B | 1.00 | 15700 | 3 | | | MIR214 | 1.00 |
| 15605 | 3 | | | | MIR1470 | 1.00 | 15701 | 3 | | | MIR215 | 1.00 |
| 15606 | 3 | | | | MIR1471 | 1.00 | 15702 | 3 | | | MIR216A | 1.00 |
| 15607 | 3 | | | | MIR147A | 1.00 | 15703 | 3 | | | MIR216B | 1.00 |
| 15608 | 3 | | | | MIR147B | 1.00 | 15704 | 3 | | | MIR217 | 1.00 |
| 15609 | 3 | | | | MIR148A | 1.00 | 15705 | 3 | | | MIR218-1 | 1.00 |
| 15610 | 3 | | | | MIR148B | 1.00 | 15706 | 3 | | | MIR218-2 | 1.00 |
| 15611 | 3 | | | | MIR149 | 1.00 | 15707 | 3 | | | MIR219-1 | 1.00 |
| 15612 | 3 | | | | MIR150 | 1.00 | 15708 | 3 | | | MIR219-2 | 1.00 |
| 15613 | 3 | | | | MIR152 | 1.00 | 15709 | 3 | | | MIR22 | 1.00 |
| 15614 | 3 | | | | MIR153-1 | 1.00 | 15710 | 3 | | | MIR221 | 1.00 |
| 15615 | 3 | | | | MIR153-2 | 1.00 | 15711 | 3 | | | MIR222 | 1.00 |
| 15616 | 3 | | | | MIR1537 | 1.00 | 15712 | 3 | | | MIR223 | 1.00 |
| 15617 | 3 | | | | MIR1538 | 1.00 | 15713 | 3 | | | MIR2276 | 1.00 |
| 15618 | 3 | | | | MIR1539 | 1.00 | 15714 | 3 | | | MIR2277 | 1.00 |
| 15619 | 3 | | | | MIR154 | 1.00 | 15715 | 3 | | | MIR2278 | 1.00 |
| 15620 | 3 | | | | MIR155 | 1.00 | 15716 | 3 | | | MIR2355 | 1.00 |
| 15621 | 3 | | | | MIR15A | 1.00 | 15717 | 3 | | | MIR2392 | 1.00 |
| 15622 | 3 | | | | MIR158 | 1.00 | 15718 | 3 | | | MIR23A | 1.00 |
| 15623 | 3 | | | | MIR16-1 | 1.00 | 15719 | 3 | | | MIR23B | 1.00 |
| 15624 | 3 | | | | MIR16-2 | 1.00 | 15720 | 3 | | | MIR23C | 1.00 |
| 15625 | 3 | | | | MIR17 | 1.00 | 15721 | 3 | | | MIR24-1 | 1.00 |
| 15626 | 3 | | | | MIR17HG | 1.00 | 15722 | 3 | | | MIR24-2 | 1.00 |
| 15627 | 3 | | | | MIR181A1 | 1.00 | 15723 | 3 | | | MIR2467 | 1.00 |
| 15628 | 3 | | | | MIR181A2 | 1.00 | 15724 | 3 | | | MIR25 | 1.00 |
| 15629 | 3 | | | | MIR181A2HG | 1.00 | 15725 | 3 | | | MIR2681 | 1.00 |
| 15630 | 3 | | | | MIR181B1 | 1.00 | 15726 | 3 | | | MIR2682 | 1.00 |
| 15631 | 3 | | | | MIR181B2 | 1.00 | 15727 | 3 | | | MIR26A1 | 1.00 |
| 15632 | 3 | | | | MIR181C | 1.00 | 15728 | 3 | | | MIR26A2 | 1.00 |
| 15633 | 3 | | | | MIR181D | 1.00 | 15729 | 3 | | | MIR26B | 1.00 |
| 15634 | 3 | | | | MIR182 | 1.00 | 15730 | 3 | | | MIR27A | 1.00 |
| 15635 | 3 | | | | MIR1827 | 1.00 | 15731 | 3 | | | MIR27B | 1.00 |
| 15636 | 3 | | | | MIR183 | 1.00 | 15732 | 3 | | | MIR2861 | 1.00 |
| 15637 | 3 | | | | MIR184 | 1.00 | 15733 | 3 | | | MIR2909 | 1.00 |
| 15638 | 3 | | | | MIR185 | 1.00 | 15734 | 3 | | | MIR296 | 1.00 |
| 15639 | 3 | | | | MIR186 | 1.00 | 15735 | 3 | | | MIR2964A | 1.00 |
| 15640 | 3 | | | | MIR187 | 1.00 | 15736 | 3 | | | MIR298 | 1.00 |
| 15641 | 3 | | | | MIR188 | 1.00 | 15737 | 3 | | | MIR299 | 1.00 |

Fig. 41 - 83

| | | | | | | | | | | | | | | | |
|---|---|---|---|---|---|---|---|---|---|---|---|---|---|---|---|
| 15738 | 3 | | | | | MIR29A | 1.00 | 15834 | 3 | | | | | MIR3198-1 | 1.00 |
| 15739 | 3 | | | | | MIR29B1 | 1.00 | 15835 | 3 | | | | | MIR3198-2 | 1.00 |
| 15740 | 3 | | | | | MIR29B2 | 1.00 | 15836 | 3 | | | | | MIR3199-1 | 1.00 |
| 15741 | 3 | | | | | MIR29C | 1.00 | 15837 | 3 | | | | | MIR3199-2 | 1.00 |
| 15742 | 3 | | | | | MIR300 | 1.00 | 15838 | 3 | | | | | MIR31HG | 1.00 |
| 15743 | 3 | | | | | MIR301A | 1.00 | 15839 | 3 | | | | | MIR32 | 1.00 |
| 15744 | 3 | | | | | MIR301B | 1.00 | 15840 | 3 | | | | | MIR3200 | 1.00 |
| 15745 | 3 | | | | | MIR302A | 1.00 | 15841 | 3 | | | | | MIR3201 | 1.00 |
| 15746 | 3 | | | | | MIR302B | 1.00 | 15842 | 3 | | | | | MIR3202-1 | 1.00 |
| 15747 | 3 | | | | | MIR302C | 1.00 | 15843 | 3 | | | | | MIR3202-2 | 1.00 |
| 15748 | 3 | | | | | MIR302D | 1.00 | 15844 | 3 | | | | | MIR320A | 1.00 |
| 15749 | 3 | | | | | MIR302F | 1.00 | 15845 | 3 | | | | | MIR320B1 | 1.00 |
| 15750 | 3 | | | | | MIR3064 | 1.00 | 15846 | 3 | | | | | MIR320B2 | 1.00 |
| 15751 | 3 | | | | | MIR3065 | 1.00 | 15847 | 3 | | | | | MIR320C1 | 1.00 |
| 15752 | 3 | | | | | MIR3074 | 1.00 | 15848 | 3 | | | | | MIR320C2 | 1.00 |
| 15753 | 3 | | | | | MIR30A | 1.00 | 15849 | 3 | | | | | MIR320D1 | 1.00 |
| 15754 | 3 | | | | | MIR30B | 1.00 | 15850 | 3 | | | | | MIR320D2 | 1.00 |
| 15755 | 3 | | | | | MIR30C1 | 1.00 | 15851 | 3 | | | | | MIR320E | 1.00 |
| 15756 | 3 | | | | | MIR30C2 | 1.00 | 15852 | 3 | | | | | MIR323A | 1.00 |
| 15757 | 3 | | | | | MIR30D | 1.00 | 15853 | 3 | | | | | MIR323B | 1.00 |
| 15758 | 3 | | | | | MIR30E | 1.00 | 15854 | 3 | | | | | MIR324 | 1.00 |
| 15759 | 3 | | | | | MIR31 | 1.00 | 15855 | 3 | | | | | MIR326 | 1.00 |
| 15760 | 3 | | | | | MIR3115 | 1.00 | 15856 | 3 | | | | | MIR328 | 1.00 |
| 15761 | 3 | | | | | MIR3117 | 1.00 | 15857 | 3 | | | | | MIR329-1 | 1.00 |
| 15762 | 3 | | | | | MIR3119-1 | 1.00 | 15858 | 3 | | | | | MIR329-2 | 1.00 |
| 15763 | 3 | | | | | MIR3120 | 1.00 | 15859 | 3 | | | | | MIR330 | 1.00 |
| 15764 | 3 | | | | | MIR3121 | 1.00 | 15860 | 3 | | | | | MIR331 | 1.00 |
| 15765 | 3 | | | | | MIR3122 | 1.00 | 15861 | 3 | | | | | MIR335 | 1.00 |
| 15766 | 3 | | | | | MIR3123 | 1.00 | 15862 | 3 | | | | | MIR337 | 1.00 |
| 15767 | 3 | | | | | MIR3124 | 1.00 | 15863 | 3 | | | | | MIR338 | 1.00 |
| 15768 | 3 | | | | | MIR3125 | 1.00 | 15864 | 3 | | | | | MIR339 | 1.00 |
| 15769 | 3 | | | | | MIR3126 | 1.00 | 15865 | 3 | | | | | MIR33A | 1.00 |
| 15770 | 3 | | | | | MIR3127 | 1.00 | 15866 | 3 | | | | | MIR33B | 1.00 |
| 15771 | 3 | | | | | MIR3128 | 1.00 | 15867 | 3 | | | | | MIR340 | 1.00 |
| 15772 | 3 | | | | | MIR3129 | 1.00 | 15868 | 3 | | | | | MIR345 | 1.00 |
| 15773 | 3 | | | | | MIR3130-1 | 1.00 | 15869 | 3 | | | | | MIR346 | 1.00 |
| 15774 | 3 | | | | | MIR3131 | 1.00 | 15870 | 3 | | | | | MIR34A | 1.00 |
| 15775 | 3 | | | | | MIR3132 | 1.00 | 15871 | 3 | | | | | MIR34B | 1.00 |
| 15776 | 3 | | | | | MIR3134 | 1.00 | 15872 | 3 | | | | | MIR34C | 1.00 |
| 15777 | 3 | | | | | MIR3136 | 1.00 | 15873 | 3 | | | | | MIR3529 | 1.00 |
| 15778 | 3 | | | | | MIR3138 | 1.00 | 15874 | 3 | | | | | MIR3545 | 1.00 |
| 15779 | 3 | | | | | MIR3140 | 1.00 | 15875 | 3 | | | | | MIR3591 | 1.00 |
| 15780 | 3 | | | | | MIR3141 | 1.00 | 15876 | 3 | | | | | MIR3605 | 1.00 |
| 15781 | 3 | | | | | MIR3142 | 1.00 | 15877 | 3 | | | | | MIR3606 | 1.00 |
| 15782 | 3 | | | | | MIR3143 | 1.00 | 15878 | 3 | | | | | MIR3607 | 1.00 |
| 15783 | 3 | | | | | MIR3145 | 1.00 | 15879 | 3 | | | | | MIR3609 | 1.00 |
| 15784 | 3 | | | | | MIR3146 | 1.00 | 15880 | 3 | | | | | MIR3610 | 1.00 |
| 15785 | 3 | | | | | MIR3147 | 1.00 | 15881 | 3 | | | | | MIR3612 | 1.00 |
| 15786 | 3 | | | | | MIR3148 | 1.00 | 15882 | 3 | | | | | MIR3613 | 1.00 |
| 15787 | 3 | | | | | MIR3150A | 1.00 | 15883 | 3 | | | | | MIR3614 | 1.00 |
| 15788 | 3 | | | | | MIR3150B | 1.00 | 15884 | 3 | | | | | MIR3615 | 1.00 |
| 15789 | 3 | | | | | MIR3151 | 1.00 | 15885 | 3 | | | | | MIR3616 | 1.00 |
| 15790 | 3 | | | | | MIR3152 | 1.00 | 15886 | 3 | | | | | MIR3618 | 1.00 |
| 15791 | 3 | | | | | MIR3153 | 1.00 | 15887 | 3 | | | | | MIR3619 | 1.00 |
| 15792 | 3 | | | | | MIR3154 | 1.00 | 15888 | 3 | | | | | MIR362 | 1.00 |
| 15793 | 3 | | | | | MIR3155A | 1.00 | 15889 | 3 | | | | | MIR3620 | 1.00 |
| 15794 | 3 | | | | | MIR3155B | 1.00 | 15890 | 3 | | | | | MIR3621 | 1.00 |
| 15795 | 3 | | | | | MIR3156-1 | 1.00 | 15891 | 3 | | | | | MIR3622A | 1.00 |
| 15796 | 3 | | | | | MIR3156-2 | 1.00 | 15892 | 3 | | | | | MIR3622B | 1.00 |
| 15797 | 3 | | | | | MIR3156-3 | 1.00 | 15893 | 3 | | | | | MIR363 | 1.00 |
| 15798 | 3 | | | | | MIR3157 | 1.00 | 15894 | 3 | | | | | MIR3646 | 1.00 |
| 15799 | 3 | | | | | MIR3158-2 | 1.00 | 15895 | 3 | | | | | MIR3649 | 1.00 |
| 15800 | 3 | | | | | MIR3160-1 | 1.00 | 15896 | 3 | | | | | MIR3650 | 1.00 |
| 15801 | 3 | | | | | MIR3160-2 | 1.00 | 15897 | 3 | | | | | MIR3651 | 1.00 |
| 15802 | 3 | | | | | MIR3162 | 1.00 | 15898 | 3 | | | | | MIR3652 | 1.00 |
| 15803 | 3 | | | | | MIR3165 | 1.00 | 15899 | 3 | | | | | MIR3653 | 1.00 |
| 15804 | 3 | | | | | MIR3167 | 1.00 | 15900 | 3 | | | | | MIR3654 | 1.00 |
| 15805 | 3 | | | | | MIR3169 | 1.00 | 15901 | 3 | | | | | MIR3655 | 1.00 |
| 15806 | 3 | | | | | MIR3170 | 1.00 | 15902 | 3 | | | | | MIR3656 | 1.00 |
| 15807 | 3 | | | | | MIR3173 | 1.00 | 15903 | 3 | | | | | MIR3658 | 1.00 |
| 15808 | 3 | | | | | MIR3175 | 1.00 | 15904 | 3 | | | | | MIR3659 | 1.00 |
| 15809 | 3 | | | | | MIR3176 | 1.00 | 15905 | 3 | | | | | MIR365A | 1.00 |
| 15810 | 3 | | | | | MIR3177 | 1.00 | 15906 | 3 | | | | | MIR365B | 1.00 |
| 15811 | 3 | | | | | MIR3178 | 1.00 | 15907 | 3 | | | | | MIR3660 | 1.00 |
| 15812 | 3 | | | | | MIR3179-1 | 1.00 | 15908 | 3 | | | | | MIR3661 | 1.00 |
| 15813 | 3 | | | | | MIR3179-3 | 1.00 | 15909 | 3 | | | | | MIR3662 | 1.00 |
| 15814 | 3 | | | | | MIR3180-1 | 1.00 | 15910 | 3 | | | | | MIR3663 | 1.00 |
| 15815 | 3 | | | | | MIR3180-2 | 1.00 | 15911 | 3 | | | | | MIR3664 | 1.00 |
| 15816 | 3 | | | | | MIR3180-3 | 1.00 | 15912 | 3 | | | | | MIR3665 | 1.00 |
| 15817 | 3 | | | | | MIR3180-4 | 1.00 | 15913 | 3 | | | | | MIR3666 | 1.00 |
| 15818 | 3 | | | | | MIR3180-5 | 1.00 | 15914 | 3 | | | | | MIR3668 | 1.00 |
| 15819 | 3 | | | | | MIR3182 | 1.00 | 15915 | 3 | | | | | MIR367 | 1.00 |
| 15820 | 3 | | | | | MIR3183 | 1.00 | 15916 | 3 | | | | | MIR3671 | 1.00 |
| 15821 | 3 | | | | | MIR3184 | 1.00 | 15917 | 3 | | | | | MIR3675 | 1.00 |
| 15822 | 3 | | | | | MIR3185 | 1.00 | 15918 | 3 | | | | | MIR3676 | 1.00 |
| 15823 | 3 | | | | | MIR3186 | 1.00 | 15919 | 3 | | | | | MIR3677 | 1.00 |
| 15824 | 3 | | | | | MIR3187 | 1.00 | 15920 | 3 | | | | | MIR3678 | 1.00 |
| 15825 | 3 | | | | | MIR3188 | 1.00 | 15921 | 3 | | | | | MIR3679 | 1.00 |
| 15826 | 3 | | | | | MIR3189 | 1.00 | 15922 | 3 | | | | | MIR3680-1 | 1.00 |
| 15827 | 3 | | | | | MIR3190 | 1.00 | 15923 | 3 | | | | | MIR3682 | 1.00 |
| 15828 | 3 | | | | | MIR3191 | 1.00 | 15924 | 3 | | | | | MIR3684 | 1.00 |
| 15829 | 3 | | | | | MIR3192 | 1.00 | 15925 | 3 | | | | | MIR3685 | 1.00 |
| 15830 | 3 | | | | | MIR3193 | 1.00 | 15926 | 3 | | | | | MIR3687 | 1.00 |
| 15831 | 3 | | | | | MIR3194 | 1.00 | 15927 | 3 | | | | | MIR3688-1 | 1.00 |
| 15832 | 3 | | | | | MIR3196 | 1.00 | 15928 | 3 | | | | | MIR3688-2 | 1.00 |
| 15833 | 3 | | | | | MIR3197 | 1.00 | 15929 | 3 | | | | | MIR3689A | 1.00 |

Fig. 41 - 84

| | | | | | | | | | | | | | | | |
|---|---|---|---|---|---|---|---|---|---|---|---|---|---|---|---|
| 15930 | 3 | | | | | MIR3689B | 1.00 | 16026 | 3 | | | | | MIR4265 | 1.00 |
| 15931 | 3 | | | | | MIR3689C | 1.00 | 16027 | 3 | | | | | MIR4266 | 1.00 |
| 15932 | 3 | | | | | MIR3689D1 | 1.00 | 16028 | 3 | | | | | MIR4267 | 1.00 |
| 15933 | 3 | | | | | MIR3689D2 | 1.00 | 16029 | 3 | | | | | MIR4268 | 1.00 |
| 15934 | 3 | | | | | MIR3689E | 1.00 | 16030 | 3 | | | | | MIR4269 | 1.00 |
| 15935 | 3 | | | | | MIR3689F | 1.00 | 16031 | 3 | | | | | MIR4270 | 1.00 |
| 15936 | 3 | | | | | MIR369 | 1.00 | 16032 | 3 | | | | | MIR4271 | 1.00 |
| 15937 | 3 | | | | | MIR3690 | 1.00 | 16033 | 3 | | | | | MIR4272 | 1.00 |
| 15938 | 3 | | | | | MIR3691 | 1.00 | 16034 | 3 | | | | | MIR4273 | 1.00 |
| 15939 | 3 | | | | | MIR3692 | 1.00 | 16035 | 3 | | | | | MIR4274 | 1.00 |
| 15940 | 3 | | | | | MIR3714 | 1.00 | 16036 | 3 | | | | | MIR4275 | 1.00 |
| 15941 | 3 | | | | | MIR371A | 1.00 | 16037 | 3 | | | | | MIR4276 | 1.00 |
| 15942 | 3 | | | | | MIR371B | 1.00 | 16038 | 3 | | | | | MIR4277 | 1.00 |
| 15943 | 3 | | | | | MIR372 | 1.00 | 16039 | 3 | | | | | MIR4278 | 1.00 |
| 15944 | 3 | | | | | MIR373 | 1.00 | 16040 | 3 | | | | | MIR4279 | 1.00 |
| 15945 | 3 | | | | | MIR374A | 1.00 | 16041 | 3 | | | | | MIR4280 | 1.00 |
| 15946 | 3 | | | | | MIR374B | 1.00 | 16042 | 3 | | | | | MIR4281 | 1.00 |
| 15947 | 3 | | | | | MIR374C | 1.00 | 16043 | 3 | | | | | MIR4282 | 1.00 |
| 15948 | 3 | | | | | MIR375 | 1.00 | 16044 | 3 | | | | | MIR4283-1 | 1.00 |
| 15949 | 3 | | | | | MIR376A1 | 1.00 | 16045 | 3 | | | | | MIR4283-2 | 1.00 |
| 15950 | 3 | | | | | MIR376A2 | 1.00 | 16046 | 3 | | | | | MIR4284 | 1.00 |
| 15951 | 3 | | | | | MIR376B | 1.00 | 16047 | 3 | | | | | MIR4285 | 1.00 |
| 15952 | 3 | | | | | MIR376C | 1.00 | 16048 | 3 | | | | | MIR4287 | 1.00 |
| 15953 | 3 | | | | | MIR377 | 1.00 | 16049 | 3 | | | | | MIR4288 | 1.00 |
| 15954 | 3 | | | | | MIR378C | 1.00 | 16050 | 3 | | | | | MIR4289 | 1.00 |
| 15955 | 3 | | | | | MIR378D1 | 1.00 | 16051 | 3 | | | | | MIR429 | 1.00 |
| 15956 | 3 | | | | | MIR378D2 | 1.00 | 16052 | 3 | | | | | MIR4290 | 1.00 |
| 15957 | 3 | | | | | MIR378E | 1.00 | 16053 | 3 | | | | | MIR4291 | 1.00 |
| 15958 | 3 | | | | | MIR378F | 1.00 | 16054 | 3 | | | | | MIR4292 | 1.00 |
| 15959 | 3 | | | | | MIR379 | 1.00 | 16055 | 3 | | | | | MIR4294 | 1.00 |
| 15960 | 3 | | | | | MIR380 | 1.00 | 16056 | 3 | | | | | MIR4295 | 1.00 |
| 15961 | 3 | | | | | MIR381 | 1.00 | 16057 | 3 | | | | | MIR4296 | 1.00 |
| 15962 | 3 | | | | | MIR382 | 1.00 | 16058 | 3 | | | | | MIR4297 | 1.00 |
| 15963 | 3 | | | | | MIR383 | 1.00 | 16059 | 3 | | | | | MIR4298 | 1.00 |
| 15964 | 3 | | | | | MIR384 | 1.00 | 16060 | 3 | | | | | MIR4299 | 1.00 |
| 15965 | 3 | | | | | MIR3907 | 1.00 | 16061 | 3 | | | | | MIR4300 | 1.00 |
| 15966 | 3 | | | | | MIR3908 | 1.00 | 16062 | 3 | | | | | MIR4301 | 1.00 |
| 15967 | 3 | | | | | MIR3909 | 1.00 | 16063 | 3 | | | | | MIR4302 | 1.00 |
| 15968 | 3 | | | | | MIR3910-1 | 1.00 | 16064 | 3 | | | | | MIR4303 | 1.00 |
| 15969 | 3 | | | | | MIR3910-2 | 1.00 | 16065 | 3 | | | | | MIR4304 | 1.00 |
| 15970 | 3 | | | | | MIR3911 | 1.00 | 16066 | 3 | | | | | MIR4305 | 1.00 |
| 15971 | 3 | | | | | MIR3912 | 1.00 | 16067 | 3 | | | | | MIR4306 | 1.00 |
| 15972 | 3 | | | | | MIR3913-1 | 1.00 | 16068 | 3 | | | | | MIR4307 | 1.00 |
| 15973 | 3 | | | | | MIR3913-2 | 1.00 | 16069 | 3 | | | | | MIR4308 | 1.00 |
| 15974 | 3 | | | | | MIR3914-1 | 1.00 | 16070 | 3 | | | | | MIR4309 | 1.00 |
| 15975 | 3 | | | | | MIR3914-2 | 1.00 | 16071 | 3 | | | | | MIR431 | 1.00 |
| 15976 | 3 | | | | | MIR3916 | 1.00 | 16072 | 3 | | | | | MIR4310 | 1.00 |
| 15977 | 3 | | | | | MIR3917 | 1.00 | 16073 | 3 | | | | | MIR4311 | 1.00 |
| 15978 | 3 | | | | | MIR3918 | 1.00 | 16074 | 3 | | | | | MIR4312 | 1.00 |
| 15979 | 3 | | | | | MIR3919 | 1.00 | 16075 | 3 | | | | | MIR4313 | 1.00 |
| 15980 | 3 | | | | | MIR3920 | 1.00 | 16076 | 3 | | | | | MIR4314 | 1.00 |
| 15981 | 3 | | | | | MIR3921 | 1.00 | 16077 | 3 | | | | | MIR4315-2 | 1.00 |
| 15982 | 3 | | | | | MIR3922 | 1.00 | 16078 | 3 | | | | | MIR4316 | 1.00 |
| 15983 | 3 | | | | | MIR3924 | 1.00 | 16079 | 3 | | | | | MIR4317 | 1.00 |
| 15984 | 3 | | | | | MIR3925 | 1.00 | 16080 | 3 | | | | | MIR4318 | 1.00 |
| 15985 | 3 | | | | | MIR3926-1 | 1.00 | 16081 | 3 | | | | | MIR4319 | 1.00 |
| 15986 | 3 | | | | | MIR3926-2 | 1.00 | 16082 | 3 | | | | | MIR432 | 1.00 |
| 15987 | 3 | | | | | MIR3928 | 1.00 | 16083 | 3 | | | | | MIR4320 | 1.00 |
| 15988 | 3 | | | | | MIR3935 | 1.00 | 16084 | 3 | | | | | MIR4321 | 1.00 |
| 15989 | 3 | | | | | MIR3936 | 1.00 | 16085 | 3 | | | | | MIR4322 | 1.00 |
| 15990 | 3 | | | | | MIR3938 | 1.00 | 16086 | 3 | | | | | MIR4323 | 1.00 |
| 15991 | 3 | | | | | MIR3939 | 1.00 | 16087 | 3 | | | | | MIR4324 | 1.00 |
| 15992 | 3 | | | | | MIR3940 | 1.00 | 16088 | 3 | | | | | MIR4325 | 1.00 |
| 15993 | 3 | | | | | MIR3941 | 1.00 | 16089 | 3 | | | | | MIR4326 | 1.00 |
| 15994 | 3 | | | | | MIR3942 | 1.00 | 16090 | 3 | | | | | MIR4327 | 1.00 |
| 15995 | 3 | | | | | MIR3943 | 1.00 | 16091 | 3 | | | | | MIR4328 | 1.00 |
| 15996 | 3 | | | | | MIR3944 | 1.00 | 16092 | 3 | | | | | MIR4329 | 1.00 |
| 15997 | 3 | | | | | MIR3945 | 1.00 | 16093 | 3 | | | | | MIR433 | 1.00 |
| 15998 | 3 | | | | | MIR3960 | 1.00 | 16094 | 3 | | | | | MIR4330 | 1.00 |
| 15999 | 3 | | | | | MIR3973 | 1.00 | 16095 | 3 | | | | | MIR4417 | 1.00 |
| 16000 | 3 | | | | | MIR3974 | 1.00 | 16096 | 3 | | | | | MIR4420 | 1.00 |
| 16001 | 3 | | | | | MIR3975 | 1.00 | 16097 | 3 | | | | | MIR4422 | 1.00 |
| 16002 | 3 | | | | | MIR3976 | 1.00 | 16098 | 3 | | | | | MIR4423 | 1.00 |
| 16003 | 3 | | | | | MIR3977 | 1.00 | 16099 | 3 | | | | | MIR4424 | 1.00 |
| 16004 | 3 | | | | | MIR3978 | 1.00 | 16100 | 3 | | | | | MIR4426 | 1.00 |
| 16005 | 3 | | | | | MIR409 | 1.00 | 16101 | 3 | | | | | MIR4427 | 1.00 |
| 16006 | 3 | | | | | MIR410 | 1.00 | 16102 | 3 | | | | | MIR4429 | 1.00 |
| 16007 | 3 | | | | | MIR411 | 1.00 | 16103 | 3 | | | | | MIR4432 | 1.00 |
| 16008 | 3 | | | | | MIR412 | 1.00 | 16104 | 3 | | | | | MIR4434 | 1.00 |
| 16009 | 3 | | | | | MIR421 | 1.00 | 16105 | 3 | | | | | MIR4435-1 | 1.00 |
| 16010 | 3 | | | | | MIR423 | 1.00 | 16106 | 3 | | | | | MIR4435-2 | 1.00 |
| 16011 | 3 | | | | | MIR424 | 1.00 | 16107 | 3 | | | | | MIR4436A | 1.00 |
| 16012 | 3 | | | | | MIR425 | 1.00 | 16108 | 3 | | | | | MIR4436B1 | 1.00 |
| 16013 | 3 | | | | | MIR4251 | 1.00 | 16109 | 3 | | | | | MIR4437 | 1.00 |
| 16014 | 3 | | | | | MIR4252 | 1.00 | 16110 | 3 | | | | | MIR4439 | 1.00 |
| 16015 | 3 | | | | | MIR4253 | 1.00 | 16111 | 3 | | | | | MIR4440 | 1.00 |
| 16016 | 3 | | | | | MIR4254 | 1.00 | 16112 | 3 | | | | | MIR4441 | 1.00 |
| 16017 | 3 | | | | | MIR4255 | 1.00 | 16113 | 3 | | | | | MIR4442 | 1.00 |
| 16018 | 3 | | | | | MIR4256 | 1.00 | 16114 | 3 | | | | | MIR4443 | 1.00 |
| 16019 | 3 | | | | | MIR4257 | 1.00 | 16115 | 3 | | | | | MIR4444-1 | 1.00 |
| 16020 | 3 | | | | | MIR4258 | 1.00 | 16116 | 3 | | | | | MIR4446 | 1.00 |
| 16021 | 3 | | | | | MIR4260 | 1.00 | 16117 | 3 | | | | | MIR4449 | 1.00 |
| 16022 | 3 | | | | | MIR4261 | 1.00 | 16118 | 3 | | | | | MIR4450 | 1.00 |
| 16023 | 3 | | | | | MIR4262 | 1.00 | 16119 | 3 | | | | | MIR4451 | 1.00 |
| 16024 | 3 | | | | | MIR4263 | 1.00 | 16120 | 3 | | | | | MIR4453 | 1.00 |
| 16025 | 3 | | | | | MIR4264 | 1.00 | 16121 | 3 | | | | | MIR4454 | 1.00 |

Fig. 41 - 85

| | | | | | | | | |
|---|---|---|---|---|---|---|---|---|
| 16122 | 3 | | | | | MIR4456 | 1.00 |
| 16123 | 3 | | | | | MIR4457 | 1.00 |
| 16124 | 3 | | | | | MIR4458 | 1.00 |
| 16125 | 3 | | | | | MIR4460 | 1.00 |
| 16126 | 3 | | | | | MIR4461 | 1.00 |
| 16127 | 3 | | | | | MIR4462 | 1.00 |
| 16128 | 3 | | | | | MIR4464 | 1.00 |
| 16129 | 3 | | | | | MIR4465 | 1.00 |
| 16130 | 3 | | | | | MIR4466 | 1.00 |
| 16131 | 3 | | | | | MIR4467 | 1.00 |
| 16132 | 3 | | | | | MIR4468 | 1.00 |
| 16133 | 3 | | | | | MIR4469 | 1.00 |
| 16134 | 3 | | | | | MIR4470 | 1.00 |
| 16135 | 3 | | | | | MIR4471 | 1.00 |
| 16136 | 3 | | | | | MIR4472-1 | 1.00 |
| 16137 | 3 | | | | | MIR4472-2 | 1.00 |
| 16138 | 3 | | | | | MIR4473 | 1.00 |
| 16139 | 3 | | | | | MIR4474 | 1.00 |
| 16140 | 3 | | | | | MIR4475 | 1.00 |
| 16141 | 3 | | | | | MIR4476 | 1.00 |
| 16142 | 3 | | | | | MIR4478 | 1.00 |
| 16143 | 3 | | | | | MIR4479 | 1.00 |
| 16144 | 3 | | | | | MIR448 | 1.00 |
| 16145 | 3 | | | | | MIR4480 | 1.00 |
| 16146 | 3 | | | | | MIR4482-1 | 1.00 |
| 16147 | 3 | | | | | MIR4483 | 1.00 |
| 16148 | 3 | | | | | MIR4484 | 1.00 |
| 16149 | 3 | | | | | MIR4485 | 1.00 |
| 16150 | 3 | | | | | MIR4486 | 1.00 |
| 16151 | 3 | | | | | MIR4488 | 1.00 |
| 16152 | 3 | | | | | MIR4489 | 1.00 |
| 16153 | 3 | | | | | MIR4490 | 1.00 |
| 16154 | 3 | | | | | MIR4491 | 1.00 |
| 16155 | 3 | | | | | MIR4492 | 1.00 |
| 16156 | 3 | | | | | MIR4493 | 1.00 |
| 16157 | 3 | | | | | MIR4497 | 1.00 |
| 16158 | 3 | | | | | MIR4498 | 1.00 |
| 16159 | 3 | | | | | MIR4499 | 1.00 |
| 16160 | 3 | | | | | MIR449A | 1.00 |
| 16161 | 3 | | | | | MIR449B | 1.00 |
| 16162 | 3 | | | | | MIR449C | 1.00 |
| 16163 | 3 | | | | | MIR4500 | 1.00 |
| 16164 | 3 | | | | | MIR4500HG | 1.00 |
| 16165 | 3 | | | | | MIR4503 | 1.00 |
| 16166 | 3 | | | | | MIR4505 | 1.00 |
| 16167 | 3 | | | | | MIR4508 | 1.00 |
| 16168 | 3 | | | | | MIR4509-1 | 1.00 |
| 16169 | 3 | | | | | MIR450A1 | 1.00 |
| 16170 | 3 | | | | | MIR450A2 | 1.00 |
| 16171 | 3 | | | | | MIR450B | 1.00 |
| 16172 | 3 | | | | | MIR4510 | 1.00 |
| 16173 | 3 | | | | | MIR4511 | 1.00 |
| 16174 | 3 | | | | | MIR4513 | 1.00 |
| 16175 | 3 | | | | | MIR4514 | 1.00 |
| 16176 | 3 | | | | | MIR4515 | 1.00 |
| 16177 | 3 | | | | | MIR4516 | 1.00 |
| 16178 | 3 | | | | | MIR4517 | 1.00 |
| 16179 | 3 | | | | | MIR4518 | 1.00 |
| 16180 | 3 | | | | | MIR4519 | 1.00 |
| 16181 | 3 | | | | | MIR451A | 1.00 |
| 16182 | 3 | | | | | MIR451B | 1.00 |
| 16183 | 3 | | | | | MIR452 | 1.00 |
| 16184 | 3 | | | | | MIR4520A | 1.00 |
| 16185 | 3 | | | | | MIR4520B | 1.00 |
| 16186 | 3 | | | | | MIR4521 | 1.00 |
| 16187 | 3 | | | | | MIR4522 | 1.00 |
| 16188 | 3 | | | | | MIR4523 | 1.00 |
| 16189 | 3 | | | | | MIR4524A | 1.00 |
| 16190 | 3 | | | | | MIR4526 | 1.00 |
| 16191 | 3 | | | | | MIR4529 | 1.00 |
| 16192 | 3 | | | | | MIR4530 | 1.00 |
| 16193 | 3 | | | | | MIR4531 | 1.00 |
| 16194 | 3 | | | | | MIR4532 | 1.00 |
| 16195 | 3 | | | | | MIR4533 | 1.00 |
| 16196 | 3 | | | | | MIR4534 | 1.00 |
| 16197 | 3 | | | | | MIR4535 | 1.00 |
| 16198 | 3 | | | | | MIR4536-1 | 1.00 |
| 16199 | 3 | | | | | MIR454 | 1.00 |
| 16200 | 3 | | | | | MIR4540 | 1.00 |
| 16201 | 3 | | | | | MIR455 | 1.00 |
| 16202 | 3 | | | | | MIR4632 | 1.00 |
| 16203 | 3 | | | | | MIR4633 | 1.00 |
| 16204 | 3 | | | | | MIR4634 | 1.00 |
| 16205 | 3 | | | | | MIR4635 | 1.00 |
| 16206 | 3 | | | | | MIR4636 | 1.00 |
| 16207 | 3 | | | | | MIR4637 | 1.00 |
| 16208 | 3 | | | | | MIR4638 | 1.00 |
| 16209 | 3 | | | | | MIR4639 | 1.00 |
| 16210 | 3 | | | | | MIR4640 | 1.00 |
| 16211 | 3 | | | | | MIR4641 | 1.00 |
| 16212 | 3 | | | | | MIR4642 | 1.00 |
| 16213 | 3 | | | | | MIR4643 | 1.00 |
| 16214 | 3 | | | | | MIR4644 | 1.00 |
| 16215 | 3 | | | | | MIR4645 | 1.00 |
| 16216 | 3 | | | | | MIR4646 | 1.00 |
| 16217 | 3 | | | | | MIR4647 | 1.00 |
| 16218 | 3 | | | | | MIR4648 | 1.00 |
| 16219 | 3 | | | | | MIR4649 | 1.00 |
| 16220 | 3 | | | | | MIR4650-1 | 1.00 |
| 16221 | 3 | | | | | MIR4651 | 1.00 |
| 16222 | 3 | | | | | MIR4652 | 1.00 |
| 16223 | 3 | | | | | MIR4653 | 1.00 |
| 16224 | 3 | | | | | MIR4654 | 1.00 |
| 16225 | 3 | | | | | MIR4655 | 1.00 |
| 16226 | 3 | | | | | MIR4656 | 1.00 |
| 16227 | 3 | | | | | MIR4657 | 1.00 |
| 16228 | 3 | | | | | MIR4658 | 1.00 |
| 16229 | 3 | | | | | MIR4659A | 1.00 |
| 16230 | 3 | | | | | MIR4659B | 1.00 |
| 16231 | 3 | | | | | MIR4660 | 1.00 |
| 16232 | 3 | | | | | MIR4661 | 1.00 |
| 16233 | 3 | | | | | MIR4663 | 1.00 |
| 16234 | 3 | | | | | MIR4664 | 1.00 |
| 16235 | 3 | | | | | MIR4665 | 1.00 |
| 16236 | 3 | | | | | MIR4666A | 1.00 |
| 16237 | 3 | | | | | MIR4667 | 1.00 |
| 16238 | 3 | | | | | MIR4668 | 1.00 |
| 16239 | 3 | | | | | MIR4669 | 1.00 |
| 16240 | 3 | | | | | MIR4670 | 1.00 |
| 16241 | 3 | | | | | MIR4671 | 1.00 |
| 16242 | 3 | | | | | MIR4672 | 1.00 |
| 16243 | 3 | | | | | MIR4673 | 1.00 |
| 16244 | 3 | | | | | MIR4674 | 1.00 |
| 16245 | 3 | | | | | MIR4675 | 1.00 |
| 16246 | 3 | | | | | MIR4676 | 1.00 |
| 16247 | 3 | | | | | MIR4677 | 1.00 |
| 16248 | 3 | | | | | MIR4678 | 1.00 |
| 16249 | 3 | | | | | MIR4679-1 | 1.00 |
| 16250 | 3 | | | | | MIR4679-2 | 1.00 |
| 16251 | 3 | | | | | MIR4680 | 1.00 |
| 16252 | 3 | | | | | MIR4681 | 1.00 |
| 16253 | 3 | | | | | MIR4682 | 1.00 |
| 16254 | 3 | | | | | MIR4683 | 1.00 |
| 16255 | 3 | | | | | MIR4684 | 1.00 |
| 16256 | 3 | | | | | MIR4685 | 1.00 |
| 16257 | 3 | | | | | MIR4686 | 1.00 |
| 16258 | 3 | | | | | MIR4687 | 1.00 |
| 16259 | 3 | | | | | MIR4688 | 1.00 |
| 16260 | 3 | | | | | MIR4689 | 1.00 |
| 16261 | 3 | | | | | MIR4690 | 1.00 |
| 16262 | 3 | | | | | MIR4691 | 1.00 |
| 16263 | 3 | | | | | MIR4692 | 1.00 |
| 16264 | 3 | | | | | MIR4693 | 1.00 |
| 16265 | 3 | | | | | MIR4694 | 1.00 |
| 16266 | 3 | | | | | MIR4695 | 1.00 |
| 16267 | 3 | | | | | MIR4696 | 1.00 |
| 16268 | 3 | | | | | MIR4697 | 1.00 |
| 16269 | 3 | | | | | MIR4698 | 1.00 |
| 16270 | 3 | | | | | MIR4699 | 1.00 |
| 16271 | 3 | | | | | MIR4700 | 1.00 |
| 16272 | 3 | | | | | MIR4701 | 1.00 |
| 16273 | 3 | | | | | MIR4703 | 1.00 |
| 16274 | 3 | | | | | MIR4705 | 1.00 |
| 16275 | 3 | | | | | MIR4706 | 1.00 |
| 16276 | 3 | | | | | MIR4707 | 1.00 |
| 16277 | 3 | | | | | MIR4708 | 1.00 |
| 16278 | 3 | | | | | MIR4709 | 1.00 |
| 16279 | 3 | | | | | MIR4710 | 1.00 |
| 16280 | 3 | | | | | MIR4711 | 1.00 |
| 16281 | 3 | | | | | MIR4712 | 1.00 |
| 16282 | 3 | | | | | MIR4713 | 1.00 |
| 16283 | 3 | | | | | MIR4714 | 1.00 |
| 16284 | 3 | | | | | MIR4715 | 1.00 |
| 16285 | 3 | | | | | MIR4716 | 1.00 |
| 16286 | 3 | | | | | MIR4717 | 1.00 |
| 16287 | 3 | | | | | MIR4718 | 1.00 |
| 16288 | 3 | | | | | MIR4719 | 1.00 |
| 16289 | 3 | | | | | MIR4720 | 1.00 |
| 16290 | 3 | | | | | MIR4721 | 1.00 |
| 16291 | 3 | | | | | MIR4722 | 1.00 |
| 16292 | 3 | | | | | MIR4723 | 1.00 |
| 16293 | 3 | | | | | MIR4724 | 1.00 |
| 16294 | 3 | | | | | MIR4725 | 1.00 |
| 16295 | 3 | | | | | MIR4726 | 1.00 |
| 16296 | 3 | | | | | MIR4727 | 1.00 |
| 16297 | 3 | | | | | MIR4728 | 1.00 |
| 16298 | 3 | | | | | MIR4729 | 1.00 |
| 16299 | 3 | | | | | MIR4730 | 1.00 |
| 16300 | 3 | | | | | MIR4731 | 1.00 |
| 16301 | 3 | | | | | MIR4732 | 1.00 |
| 16302 | 3 | | | | | MIR4733 | 1.00 |
| 16303 | 3 | | | | | MIR4734 | 1.00 |
| 16304 | 3 | | | | | MIR4735 | 1.00 |
| 16305 | 3 | | | | | MIR4736 | 1.00 |
| 16306 | 3 | | | | | MIR4737 | 1.00 |
| 16307 | 3 | | | | | MIR4738 | 1.00 |
| 16308 | 3 | | | | | MIR4739 | 1.00 |
| 16309 | 3 | | | | | MIR4740 | 1.00 |
| 16310 | 3 | | | | | MIR4741 | 1.00 |
| 16311 | 3 | | | | | MIR4742 | 1.00 |
| 16312 | 3 | | | | | MIR4743 | 1.00 |
| 16313 | 3 | | | | | MIR4744 | 1.00 |

Fig. 41 - 86

| | | | | | | | | | | | | | | | |
|---|---|---|---|---|---|---|---|---|---|---|---|---|---|---|---|
| 16314 | 3 | | | | | MIR4745 | 1.00 | 16410 | 3 | | | | | MIR512-1 | 1.00 |
| 16315 | 3 | | | | | MIR4746 | 1.00 | 16411 | 3 | | | | | MIR512-2 | 1.00 |
| 16316 | 3 | | | | | MIR4747 | 1.00 | 16412 | 3 | | | | | MIR514A1 | 1.00 |
| 16317 | 3 | | | | | MIR4748 | 1.00 | 16413 | 3 | | | | | MIR514A3 | 1.00 |
| 16318 | 3 | | | | | MIR4749 | 1.00 | 16414 | 3 | | | | | MIR514B | 1.00 |
| 16319 | 3 | | | | | MIR4750 | 1.00 | 16415 | 3 | | | | | MIR515-1 | 1.00 |
| 16320 | 3 | | | | | MIR4751 | 1.00 | 16416 | 3 | | | | | MIR515-2 | 1.00 |
| 16321 | 3 | | | | | MIR4752 | 1.00 | 16417 | 3 | | | | | MIR516A1 | 1.00 |
| 16322 | 3 | | | | | MIR4753 | 1.00 | 16418 | 3 | | | | | MIR516A2 | 1.00 |
| 16323 | 3 | | | | | MIR4754 | 1.00 | 16419 | 3 | | | | | MIR516B1 | 1.00 |
| 16324 | 3 | | | | | MIR4755 | 1.00 | 16420 | 3 | | | | | MIR516B2 | 1.00 |
| 16325 | 3 | | | | | MIR4756 | 1.00 | 16421 | 3 | | | | | MIR517A | 1.00 |
| 16326 | 3 | | | | | MIR4757 | 1.00 | 16422 | 3 | | | | | MIR517B | 1.00 |
| 16327 | 3 | | | | | MIR4758 | 1.00 | 16423 | 3 | | | | | MIR517C | 1.00 |
| 16328 | 3 | | | | | MIR4759 | 1.00 | 16424 | 3 | | | | | MIR518A1 | 1.00 |
| 16329 | 3 | | | | | MIR4760 | 1.00 | 16425 | 3 | | | | | MIR518A2 | 1.00 |
| 16330 | 3 | | | | | MIR4761 | 1.00 | 16426 | 3 | | | | | MIR518B | 1.00 |
| 16331 | 3 | | | | | MIR4762 | 1.00 | 16427 | 3 | | | | | MIR518C | 1.00 |
| 16332 | 3 | | | | | MIR4763 | 1.00 | 16428 | 3 | | | | | MIR518D | 1.00 |
| 16333 | 3 | | | | | MIR4764 | 1.00 | 16429 | 3 | | | | | MIR518E | 1.00 |
| 16334 | 3 | | | | | MIR4765 | 1.00 | 16430 | 3 | | | | | MIR518F | 1.00 |
| 16335 | 3 | | | | | MIR4766 | 1.00 | 16431 | 3 | | | | | MIR519A1 | 1.00 |
| 16336 | 3 | | | | | MIR4767 | 1.00 | 16432 | 3 | | | | | MIR519A2 | 1.00 |
| 16337 | 3 | | | | | MIR4768 | 1.00 | 16433 | 3 | | | | | MIR519B | 1.00 |
| 16338 | 3 | | | | | MIR4769 | 1.00 | 16434 | 3 | | | | | MIR519C | 1.00 |
| 16339 | 3 | | | | | MIR4770 | 1.00 | 16435 | 3 | | | | | MIR519D | 1.00 |
| 16340 | 3 | | | | | MIR4772 | 1.00 | 16436 | 3 | | | | | MIR519E | 1.00 |
| 16341 | 3 | | | | | MIR4773-2 | 1.00 | 16437 | 3 | | | | | MIR520A | 1.00 |
| 16342 | 3 | | | | | MIR4774 | 1.00 | 16438 | 3 | | | | | MIR520B | 1.00 |
| 16343 | 3 | | | | | MIR4775 | 1.00 | 16439 | 3 | | | | | MIR520C | 1.00 |
| 16344 | 3 | | | | | MIR4776-2 | 1.00 | 16440 | 3 | | | | | MIR520D | 1.00 |
| 16345 | 3 | | | | | MIR4777 | 1.00 | 16441 | 3 | | | | | MIR520E | 1.00 |
| 16346 | 3 | | | | | MIR4778 | 1.00 | 16442 | 3 | | | | | MIR520F | 1.00 |
| 16347 | 3 | | | | | MIR4779 | 1.00 | 16443 | 3 | | | | | MIR520G | 1.00 |
| 16348 | 3 | | | | | MIR4780 | 1.00 | 16444 | 3 | | | | | MIR520H | 1.00 |
| 16349 | 3 | | | | | MIR4781 | 1.00 | 16445 | 3 | | | | | MIR521-1 | 1.00 |
| 16350 | 3 | | | | | MIR4782 | 1.00 | 16446 | 3 | | | | | MIR521-2 | 1.00 |
| 16351 | 3 | | | | | MIR4783 | 1.00 | 16447 | 3 | | | | | MIR522 | 1.00 |
| 16352 | 3 | | | | | MIR4784 | 1.00 | 16448 | 3 | | | | | MIR523 | 1.00 |
| 16353 | 3 | | | | | MIR4785 | 1.00 | 16449 | 3 | | | | | MIR524 | 1.00 |
| 16354 | 3 | | | | | MIR4786 | 1.00 | 16450 | 3 | | | | | MIR525 | 1.00 |
| 16355 | 3 | | | | | MIR4787 | 1.00 | 16451 | 3 | | | | | MIR526A1 | 1.00 |
| 16356 | 3 | | | | | MIR4788 | 1.00 | 16452 | 3 | | | | | MIR526A2 | 1.00 |
| 16357 | 3 | | | | | MIR4789 | 1.00 | 16453 | 3 | | | | | MIR526B | 1.00 |
| 16358 | 3 | | | | | MIR4790 | 1.00 | 16454 | 3 | | | | | MIR527 | 1.00 |
| 16359 | 3 | | | | | MIR4791 | 1.00 | 16455 | 3 | | | | | MIR532 | 1.00 |
| 16360 | 3 | | | | | MIR4792 | 1.00 | 16456 | 3 | | | | | MIR539 | 1.00 |
| 16361 | 3 | | | | | MIR4793 | 1.00 | 16457 | 3 | | | | | MIR541 | 1.00 |
| 16362 | 3 | | | | | MIR4794 | 1.00 | 16458 | 3 | | | | | MIR542 | 1.00 |
| 16363 | 3 | | | | | MIR4795 | 1.00 | 16459 | 3 | | | | | MIR543 | 1.00 |
| 16364 | 3 | | | | | MIR4796 | 1.00 | 16460 | 3 | | | | | MIR545 | 1.00 |
| 16365 | 3 | | | | | MIR4797 | 1.00 | 16461 | 3 | | | | | MIR548A1 | 1.00 |
| 16366 | 3 | | | | | MIR4798 | 1.00 | 16462 | 3 | | | | | MIR548A2 | 1.00 |
| 16367 | 3 | | | | | MIR4799 | 1.00 | 16463 | 3 | | | | | MIR548A3 | 1.00 |
| 16368 | 3 | | | | | MIR4800 | 1.00 | 16464 | 3 | | | | | MIR548AA1 | 1.00 |
| 16369 | 3 | | | | | MIR4801 | 1.00 | 16465 | 3 | | | | | MIR548AA2 | 1.00 |
| 16370 | 3 | | | | | MIR4802 | 1.00 | 16466 | 3 | | | | | MIR548AC | 1.00 |
| 16371 | 3 | | | | | MIR4803 | 1.00 | 16467 | 3 | | | | | MIR548AD | 1.00 |
| 16372 | 3 | | | | | MIR4804 | 1.00 | 16468 | 3 | | | | | MIR548AE2 | 1.00 |
| 16373 | 3 | | | | | MIR483 | 1.00 | 16469 | 3 | | | | | MIR548AI | 1.00 |
| 16374 | 3 | | | | | MIR484 | 1.00 | 16470 | 3 | | | | | MIR548AJ2 | 1.00 |
| 16375 | 3 | | | | | MIR485 | 1.00 | 16471 | 3 | | | | | MIR548AL | 1.00 |
| 16376 | 3 | | | | | MIR486 | 1.00 | 16472 | 3 | | | | | MIR548AN | 1.00 |
| 16377 | 3 | | | | | MIR487A | 1.00 | 16473 | 3 | | | | | MIR548B | 1.00 |
| 16378 | 3 | | | | | MIR487B | 1.00 | 16474 | 3 | | | | | MIR548C | 1.00 |
| 16379 | 3 | | | | | MIR488 | 1.00 | 16475 | 3 | | | | | MIR548D2 | 1.00 |
| 16380 | 3 | | | | | MIR489 | 1.00 | 16476 | 3 | | | | | MIR548F1 | 1.00 |
| 16381 | 3 | | | | | MIR490 | 1.00 | 16477 | 3 | | | | | MIR548F2 | 1.00 |
| 16382 | 3 | | | | | MIR491 | 1.00 | 16478 | 3 | | | | | MIR548F3 | 1.00 |
| 16383 | 3 | | | | | MIR492 | 1.00 | 16479 | 3 | | | | | MIR548F4 | 1.00 |
| 16384 | 3 | | | | | MIR493 | 1.00 | 16480 | 3 | | | | | MIR548F5 | 1.00 |
| 16385 | 3 | | | | | MIR494 | 1.00 | 16481 | 3 | | | | | MIR548G | 1.00 |
| 16386 | 3 | | | | | MIR495 | 1.00 | 16482 | 3 | | | | | MIR548H2 | 1.00 |
| 16387 | 3 | | | | | MIR496 | 1.00 | 16483 | 3 | | | | | MIR548H3 | 1.00 |
| 16388 | 3 | | | | | MIR497 | 1.00 | 16484 | 3 | | | | | MIR548H4 | 1.00 |
| 16389 | 3 | | | | | MIR497HG | 1.00 | 16485 | 3 | | | | | MIR548I1 | 1.00 |
| 16390 | 3 | | | | | MIR498 | 1.00 | 16486 | 3 | | | | | MIR548I2 | 1.00 |
| 16391 | 3 | | | | | MIR499A | 1.00 | 16487 | 3 | | | | | MIR548I3 | 1.00 |
| 16392 | 3 | | | | | MIR499B | 1.00 | 16488 | 3 | | | | | MIR548I4 | 1.00 |
| 16393 | 3 | | | | | MIR500A | 1.00 | 16489 | 3 | | | | | MIR548J | 1.00 |
| 16394 | 3 | | | | | MIR500B | 1.00 | 16490 | 3 | | | | | MIR548K | 1.00 |
| 16395 | 3 | | | | | MIR501 | 1.00 | 16491 | 3 | | | | | MIR548M | 1.00 |
| 16396 | 3 | | | | | MIR502 | 1.00 | 16492 | 3 | | | | | MIR548N | 1.00 |
| 16397 | 3 | | | | | MIR503 | 1.00 | 16493 | 3 | | | | | MIR548O2 | 1.00 |
| 16398 | 3 | | | | | MIR504 | 1.00 | 16494 | 3 | | | | | MIR548Q | 1.00 |
| 16399 | 3 | | | | | MIR5047 | 1.00 | 16495 | 3 | | | | | MIR548T | 1.00 |
| 16400 | 3 | | | | | MIR505 | 1.00 | 16496 | 3 | | | | | MIR548W | 1.00 |
| 16401 | 3 | | | | | MIR506 | 1.00 | 16497 | 3 | | | | | MIR548X | 1.00 |
| 16402 | 3 | | | | | MIR507 | 1.00 | 16498 | 3 | | | | | MIR548Y | 1.00 |
| 16403 | 3 | | | | | MIR508 | 1.00 | 16499 | 3 | | | | | MIR549 | 1.00 |
| 16404 | 3 | | | | | MIR509-1 | 1.00 | 16500 | 3 | | | | | MIR550A3 | 1.00 |
| 16405 | 3 | | | | | MIR509-2 | 1.00 | 16501 | 3 | | | | | MIR550B1 | 1.00 |
| 16406 | 3 | | | | | MIR509-3 | 1.00 | 16502 | 3 | | | | | MIR550B2 | 1.00 |
| 16407 | 3 | | | | | MIR509S | 1.00 | 16503 | 3 | | | | | MIR551A | 1.00 |
| 16408 | 3 | | | | | MIR510 | 1.00 | 16504 | 3 | | | | | MIR551B | 1.00 |
| 16409 | 3 | | | | | MIR511-2 | 1.00 | 16505 | 3 | | | | | MIR553 | 1.00 |

Fig. 41 - 87

| | | | | | | | |
|---|---|---|---|---|---|---|---|
| 16506 | 3 | | | | MIR554 | | 1.00 |
| 16507 | 3 | | | | MIR555 | | 1.00 |
| 16508 | 3 | | | | MIR556 | | 1.00 |
| 16509 | 3 | | | | MIR557 | | 1.00 |
| 16510 | 3 | | | | MIR558 | | 1.00 |
| 16511 | 3 | | | | MIR559 | | 1.00 |
| 16512 | 3 | | | | MIR561 | | 1.00 |
| 16513 | 3 | | | | MIR563 | | 1.00 |
| 16514 | 3 | | | | MIR564 | | 1.00 |
| 16515 | 3 | | | | MIR567 | | 1.00 |
| 16516 | 3 | | | | MIR568 | | 1.00 |
| 16517 | 3 | | | | MIR569 | | 1.00 |
| 16518 | 3 | | | | MIR572 | | 1.00 |
| 16519 | 3 | | | | MIR573 | | 1.00 |
| 16520 | 3 | | | | MIR574 | | 1.00 |
| 16521 | 3 | | | | MIR575 | | 1.00 |
| 16522 | 3 | | | | MIR577 | | 1.00 |
| 16523 | 3 | | | | MIR578 | | 1.00 |
| 16524 | 3 | | | | MIR580 | | 1.00 |
| 16525 | 3 | | | | MIR581 | | 1.00 |
| 16526 | 3 | | | | MIR583 | | 1.00 |
| 16527 | 3 | | | | MIR585 | | 1.00 |
| 16528 | 3 | | | | MIR586 | | 1.00 |
| 16529 | 3 | | | | MIR589 | | 1.00 |
| 16530 | 3 | | | | MIR590 | | 1.00 |
| 16531 | 3 | | | | MIR591 | | 1.00 |
| 16532 | 3 | | | | MIR592 | | 1.00 |
| 16533 | 3 | | | | MIR593 | | 1.00 |
| 16534 | 3 | | | | MIR595 | | 1.00 |
| 16535 | 3 | | | | MIR596 | | 1.00 |
| 16536 | 3 | | | | MIR597 | | 1.00 |
| 16537 | 3 | | | | MIR598 | | 1.00 |
| 16538 | 3 | | | | MIR599 | | 1.00 |
| 16539 | 3 | | | | MIR600 | | 1.00 |
| 16540 | 3 | | | | MIR601 | | 1.00 |
| 16541 | 3 | | | | MIR602 | | 1.00 |
| 16542 | 3 | | | | MIR603 | | 1.00 |
| 16543 | 3 | | | | MIR604 | | 1.00 |
| 16544 | 3 | | | | MIR605 | | 1.00 |
| 16545 | 3 | | | | MIR608 | | 1.00 |
| 16546 | 3 | | | | MIR609 | | 1.00 |
| 16547 | 3 | | | | MIR610 | | 1.00 |
| 16548 | 3 | | | | MIR611 | | 1.00 |
| 16549 | 3 | | | | MIR612 | | 1.00 |
| 16550 | 3 | | | | MIR613 | | 1.00 |
| 16551 | 3 | | | | MIR614 | | 1.00 |
| 16552 | 3 | | | | MIR615 | | 1.00 |
| 16553 | 3 | | | | MIR617 | | 1.00 |
| 16554 | 3 | | | | MIR618 | | 1.00 |
| 16555 | 3 | | | | MIR620 | | 1.00 |
| 16556 | 3 | | | | MIR621 | | 1.00 |
| 16557 | 3 | | | | MIR622 | | 1.00 |
| 16558 | 3 | | | | MIR623 | | 1.00 |
| 16559 | 3 | | | | MIR624 | | 1.00 |
| 16560 | 3 | | | | MIR626 | | 1.00 |
| 16561 | 3 | | | | MIR627 | | 1.00 |
| 16562 | 3 | | | | MIR628 | | 1.00 |
| 16563 | 3 | | | | MIR629 | | 1.00 |
| 16564 | 3 | | | | MIR630 | | 1.00 |
| 16565 | 3 | | | | MIR631 | | 1.00 |
| 16566 | 3 | | | | MIR632 | | 1.00 |
| 16567 | 3 | | | | MIR634 | | 1.00 |
| 16568 | 3 | | | | MIR635 | | 1.00 |
| 16569 | 3 | | | | MIR636 | | 1.00 |
| 16570 | 3 | | | | MIR637 | | 1.00 |
| 16571 | 3 | | | | MIR638 | | 1.00 |
| 16572 | 3 | | | | MIR639 | | 1.00 |
| 16573 | 3 | | | | MIR641 | | 1.00 |
| 16574 | 3 | | | | MIR642A | | 1.00 |
| 16575 | 3 | | | | MIR642B | | 1.00 |
| 16576 | 3 | | | | MIR643 | | 1.00 |
| 16577 | 3 | | | | MIR644A | | 1.00 |
| 16578 | 3 | | | | MIR645 | | 1.00 |
| 16579 | 3 | | | | MIR647 | | 1.00 |
| 16580 | 3 | | | | MIR648 | | 1.00 |
| 16581 | 3 | | | | MIR650 | | 1.00 |
| 16582 | 3 | | | | MIR651 | | 1.00 |
| 16583 | 3 | | | | MIR653 | | 1.00 |
| 16584 | 3 | | | | MIR654 | | 1.00 |
| 16585 | 3 | | | | MIR655 | | 1.00 |
| 16586 | 3 | | | | MIR656 | | 1.00 |
| 16587 | 3 | | | | MIR657 | | 1.00 |
| 16588 | 3 | | | | MIR658 | | 1.00 |
| 16589 | 3 | | | | MIR659 | | 1.00 |
| 16590 | 3 | | | | MIR660 | | 1.00 |
| 16591 | 3 | | | | MIR661 | | 1.00 |
| 16592 | 3 | | | | MIR662 | | 1.00 |
| 16593 | 3 | | | | MIR663A | | 1.00 |
| 16594 | 3 | | | | MIR663B | | 1.00 |
| 16595 | 3 | | | | MIR664 | | 1.00 |
| 16596 | 3 | | | | MIR665 | | 1.00 |
| 16597 | 3 | | | | MIR668 | | 1.00 |
| 16598 | 3 | | | | MIR670 | | 1.00 |
| 16599 | 3 | | | | MIR671 | | 1.00 |
| 16600 | 3 | | | | MIR675 | | 1.00 |
| 16601 | 3 | | | | MIR676 | | 1.00 |
| 16602 | 3 | | | | MIR7-2 | | 1.00 |
| 16603 | 3 | | | | MIR7-3 | | 1.00 |
| 16604 | 3 | | | | MIR7-3HG | | 1.00 |
| 16605 | 3 | | | | MIR708 | | 1.00 |
| 16606 | 3 | | | | MIR711 | | 1.00 |
| 16607 | 3 | | | | MIR718 | | 1.00 |
| 16608 | 3 | | | | MIR744 | | 1.00 |
| 16609 | 3 | | | | MIR758 | | 1.00 |
| 16610 | 3 | | | | MIR759 | | 1.00 |
| 16611 | 3 | | | | MIR760 | | 1.00 |
| 16612 | 3 | | | | MIR761 | | 1.00 |
| 16613 | 3 | | | | MIR762 | | 1.00 |
| 16614 | 3 | | | | MIR764 | | 1.00 |
| 16615 | 3 | | | | MIR765 | | 1.00 |
| 16616 | 3 | | | | MIR766 | | 1.00 |
| 16617 | 3 | | | | MIR767 | | 1.00 |
| 16618 | 3 | | | | MIR769 | | 1.00 |
| 16619 | 3 | | | | MIR770 | | 1.00 |
| 16620 | 3 | | | | MIR802 | | 1.00 |
| 16621 | 3 | | | | MIR873 | | 1.00 |
| 16622 | 3 | | | | MIR874 | | 1.00 |
| 16623 | 3 | | | | MIR875 | | 1.00 |
| 16624 | 3 | | | | MIR876 | | 1.00 |
| 16625 | 3 | | | | MIR877 | | 1.00 |
| 16626 | 3 | | | | MIR885 | | 1.00 |
| 16627 | 3 | | | | MIR888 | | 1.00 |
| 16628 | 3 | | | | MIR889 | | 1.00 |
| 16629 | 3 | | | | MIR890 | | 1.00 |
| 16630 | 3 | | | | MIR891A | | 1.00 |
| 16631 | 3 | | | | MIR891B | | 1.00 |
| 16632 | 3 | | | | MIR892A | | 1.00 |
| 16633 | 3 | | | | MIR892B | | 1.00 |
| 16634 | 3 | | | | MIR9-1 | | 1.00 |
| 16635 | 3 | | | | MIR9-2 | | 1.00 |
| 16636 | 3 | | | | MIR9-3 | | 1.00 |
| 16637 | 3 | | | | MIR920 | | 1.00 |
| 16638 | 3 | | | | MIR921 | | 1.00 |
| 16639 | 3 | | | | MIR922 | | 1.00 |
| 16640 | 3 | | | | MIR92A1 | | 1.00 |
| 16641 | 3 | | | | MIR92A2 | | 1.00 |
| 16642 | 3 | | | | MIR92B | | 1.00 |
| 16643 | 3 | | | | MIR93 | | 1.00 |
| 16644 | 3 | | | | MIR933 | | 1.00 |
| 16645 | 3 | | | | MIR934 | | 1.00 |
| 16646 | 3 | | | | MIR935 | | 1.00 |
| 16647 | 3 | | | | MIR936 | | 1.00 |
| 16648 | 3 | | | | MIR937 | | 1.00 |
| 16649 | 3 | | | | MIR938 | | 1.00 |
| 16650 | 3 | | | | MIR939 | | 1.00 |
| 16651 | 3 | | | | MIR940 | | 1.00 |
| 16652 | 3 | | | | MIR941-1 | | 1.00 |
| 16653 | 3 | | | | MIR941-2 | | 1.00 |
| 16654 | 3 | | | | MIR941-3 | | 1.00 |
| 16655 | 3 | | | | MIR941-4 | | 1.00 |
| 16656 | 3 | | | | MIR942 | | 1.00 |
| 16657 | 3 | | | | MIR943 | | 1.00 |
| 16658 | 3 | | | | MIR944 | | 1.00 |
| 16659 | 3 | | | | MIR96 | | 1.00 |
| 16660 | 3 | | | | MIR98 | | 1.00 |
| 16661 | 3 | | | | MIR99A | | 1.00 |
| 16662 | 3 | | | | MIR99B | | 1.00 |
| 16663 | 3 | | | | MIRLET7A1 | | 1.00 |
| 16664 | 3 | | | | MIRLET7A2 | | 1.00 |
| 16665 | 3 | | | | MIRLET7A3 | | 1.00 |
| 16666 | 3 | | | | MIRLET7B | | 1.00 |
| 16667 | 3 | | | | MIRLET7C | | 1.00 |
| 16668 | 3 | | | | MIRLET7D | | 1.00 |
| 16669 | 3 | | | | MIRLET7E | | 1.00 |
| 16670 | 3 | | | | MIRLET7F1 | | 1.00 |
| 16671 | 3 | | | | MIRLET7F2 | | 1.00 |
| 16672 | 3 | | | | MIRLET7G | | 1.00 |
| 16673 | 3 | | | | MIRLET7I | | 1.00 |
| 16674 | 3 | | | | MIXL1 | | 1.00 |
| 16675 | 3 | | | | MKRN3 | | 1.00 |
| 16676 | 3 | | | | MKRN7P | | 1.00 |
| 16677 | 3 | | | | MKX | | 1.00 |
| 16678 | 3 | | | | MLANA | | 1.00 |
| 16679 | 3 | | | | MLF1 | | 1.00 |
| 16680 | 3 | | | | MLF1IP | | 1.00 |
| 16681 | 3 | | | | MLIP | | 1.00 |
| 16682 | 3 | | | | MLK7-AS1 | | 1.00 |
| 16683 | 3 | | | | MLLT10P1 | | 1.00 |
| 16684 | 3 | | | | MLLT4-AS1 | | 1.00 |
| 16685 | 3 | | | | MLN | | 1.00 |
| 16686 | 3 | | | | MLNR | | 1.00 |
| 16687 | 3 | | | | MLPH | | 1.00 |
| 16688 | 3 | | | | MLXIPL | | 1.00 |
| 16689 | 3 | | | | MMAB | | 1.00 |
| 16690 | 3 | | | | MMD2 | | 1.00 |
| 16691 | 3 | | | | MMEL1 | | 1.00 |
| 16692 | 3 | | | | MMP1 | | 1.00 |
| 16693 | 3 | | | | MMP10 | | 1.00 |
| 16694 | 3 | | | | MMP11 | | 1.00 |
| 16695 | 3 | | | | MMP12 | | 1.00 |
| 16696 | 3 | | | | MMP13 | | 1.00 |
| 16697 | 3 | | | | MMP15 | | 1.00 |

Fig. 41 - 88

| | | | | | | | | | | | | | | | | | | |
|---|---|---|---|---|---|---|---|---|---|---|---|---|---|---|---|---|---|---|
| 16698 | 3 | | | | | | | MMP16 | 1.00 | 16794 | 3 | | | | | | MTNR1A | 1.00 |
| 16699 | 3 | | | | | | | MMP19 | 1.00 | 16795 | 3 | | | | | | MTNR1B | 1.00 |
| 16700 | 3 | | | | | | | MMP2 | 1.00 | 16796 | 3 | | | | | | MTRNR2L10 | 1.00 |
| 16701 | 3 | | | | | | | MMP20 | 1.00 | 16797 | 3 | | | | | | MTRNR2L3 | 1.00 |
| 16702 | 3 | | | | | | | MMP21 | 1.00 | 16798 | 3 | | | | | | MTRNR2L4 | 1.00 |
| 16703 | 3 | | | | | | | MMP23A | 1.00 | 16799 | 3 | | | | | | MTRNR2L5 | 1.00 |
| 16704 | 3 | | | | | | | MMP23B | 1.00 | 16800 | 3 | | | | | | MTRNR2L6 | 1.00 |
| 16705 | 3 | | | | | | | MMP26 | 1.00 | 16801 | 3 | | | | | | MTRNR2L7 | 1.00 |
| 16706 | 3 | | | | | | | MMP27 | 1.00 | 16802 | 3 | | | | | | MTSS1L | 1.00 |
| 16707 | 3 | | | | | | | MMP3 | 1.00 | 16803 | 3 | | | | | | MTTP | 1.00 |
| 16708 | 3 | | | | | | | MMP7 | 1.00 | 16804 | 3 | | | | | | MTUS2 | 1.00 |
| 16709 | 3 | | | | | | | MMRN2 | 1.00 | 16805 | 3 | | | | | | MTVR2 | 1.00 |
| 16710 | 3 | | | | | | | MMS22L | 1.00 | 16806 | 3 | | | | | | MUC1 | 1.00 |
| 16711 | 3 | | | | | | | MN1 | 1.00 | 16807 | 3 | | | | | | MUC12 | 1.00 |
| 16712 | 3 | | | | | | | MND1 | 1.00 | 16808 | 3 | | | | | | MUC13 | 1.00 |
| 16713 | 3 | | | | | | | MNS1 | 1.00 | 16809 | 3 | | | | | | MUC15 | 1.00 |
| 16714 | 3 | | | | | | | MNX1 | 1.00 | 16810 | 3 | | | | | | MUC16 | 1.00 |
| 16715 | 3 | | | | | | | MOBP | 1.00 | 16811 | 3 | | | | | | MUC17 | 1.00 |
| 16716 | 3 | | | | | | | MOCOS | 1.00 | 16812 | 3 | | | | | | MUC2 | 1.00 |
| 16717 | 3 | | | | | | | MOG | 1.00 | 16813 | 3 | | | | | | MUC20 | 1.00 |
| 16718 | 3 | | | | | | | MOGAT1 | 1.00 | 16814 | 3 | | | | | | MUC21 | 1.00 |
| 16719 | 3 | | | | | | | MOGAT2 | 1.00 | 16815 | 3 | | | | | | MUC22 | 1.00 |
| 16720 | 3 | | | | | | | MOGAT3 | 1.00 | 16816 | 3 | | | | | | MUC4 | 1.00 |
| 16721 | 3 | | | | | | | MOK | 1.00 | 16817 | 3 | | | | | | MUC5B | 1.00 |
| 16722 | 3 | | | | | | | MORC1 | 1.00 | 16818 | 3 | | | | | | MUC6 | 1.00 |
| 16723 | 3 | | | | | | | MORN1 | 1.00 | 16819 | 3 | | | | | | MUC7 | 1.00 |
| 16724 | 3 | | | | | | | MORN4 | 1.00 | 16820 | 3 | | | | | | MUCL1 | 1.00 |
| 16725 | 3 | | | | | | | MORN5 | 1.00 | 16821 | 3 | | | | | | MUM1L1 | 1.00 |
| 16726 | 3 | | | | | | | MOS | 1.00 | 16822 | 3 | | | | | | MURC | 1.00 |
| 16727 | 3 | | | | | | | MOV10L1 | 1.00 | 16823 | 3 | | | | | | MUSK | 1.00 |
| 16728 | 3 | | | | | | | MOXD1 | 1.00 | 16824 | 3 | | | | | | MUTED-TXNDC5 | 1.00 |
| 16729 | 3 | | | | | | | MOXD2P | 1.00 | 16825 | 3 | | | | | | MXRA5 | 1.00 |
| 16730 | 3 | | | | | | | MPO2 | 1.00 | 16826 | 3 | | | | | | MXRA8 | 1.00 |
| 16731 | 3 | | | | | | | MPL | 1.00 | 16827 | 3 | | | | | | MYADML | 1.00 |
| 16732 | 3 | | | | | | | MPP2 | 1.00 | 16828 | 3 | | | | | | MYADML2 | 1.00 |
| 16733 | 3 | | | | | | | MPP3 | 1.00 | 16829 | 3 | | | | | | MYBPC1 | 1.00 |
| 16734 | 3 | | | | | | | MPP4 | 1.00 | 16830 | 3 | | | | | | MYBPC2 | 1.00 |
| 16735 | 3 | | | | | | | MPP6 | 1.00 | 16831 | 3 | | | | | | MYBPC3 | 1.00 |
| 16736 | 3 | | | | | | | MPPED1 | 1.00 | 16832 | 3 | | | | | | MYBPH | 1.00 |
| 16737 | 3 | | | | | | | MPPED2 | 1.00 | 16833 | 3 | | | | | | MYBPHL | 1.00 |
| 16738 | 3 | | | | | | | MPV17L | 1.00 | 16834 | 3 | | | | | | MYCBPAP | 1.00 |
| 16739 | 3 | | | | | | | MRAP | 1.00 | 16835 | 3 | | | | | | MYCN | 1.00 |
| 16740 | 3 | | | | | | | MRAP2 | 1.00 | 16836 | 3 | | | | | | MYCNOS | 1.00 |
| 16741 | 3 | | | | | | | MRC1 | 1.00 | 16837 | 3 | | | | | | MYEF2 | 1.00 |
| 16742 | 3 | | | | | | | MRGPRD | 1.00 | 16838 | 3 | | | | | | MYF5 | 1.00 |
| 16743 | 3 | | | | | | | MRGPRE | 1.00 | 16839 | 3 | | | | | | MYF6 | 1.00 |
| 16744 | 3 | | | | | | | MRGPRF | 1.00 | 16840 | 3 | | | | | | MYH1 | 1.00 |
| 16745 | 3 | | | | | | | MRGPRG | 1.00 | 16841 | 3 | | | | | | MYH10 | 1.00 |
| 16746 | 3 | | | | | | | MRGPRX1 | 1.00 | 16842 | 3 | | | | | | MYH11 | 1.00 |
| 16747 | 3 | | | | | | | MRGPRX2 | 1.00 | 16843 | 3 | | | | | | MYH13 | 1.00 |
| 16748 | 3 | | | | | | | MRGPRX3 | 1.00 | 16844 | 3 | | | | | | MYH14 | 1.00 |
| 16749 | 3 | | | | | | | MRGPRX4 | 1.00 | 16845 | 3 | | | | | | MYH15 | 1.00 |
| 16750 | 3 | | | | | | | MRO | 1.00 | 16846 | 3 | | | | | | MYH16 | 1.00 |
| 16751 | 3 | | | | | | | MRPL23-AS1 | 1.00 | 16847 | 3 | | | | | | MYH2 | 1.00 |
| 16752 | 3 | | | | | | | MRPL45P2 | 1.00 | 16848 | 3 | | | | | | MYH3 | 1.00 |
| 16753 | 3 | | | | | | | MS4A10 | 1.00 | 16849 | 3 | | | | | | MYH4 | 1.00 |
| 16754 | 3 | | | | | | | MS4A12 | 1.00 | 16850 | 3 | | | | | | MYH6 | 1.00 |
| 16755 | 3 | | | | | | | MS4A13 | 1.00 | 16851 | 3 | | | | | | MYH7 | 1.00 |
| 16756 | 3 | | | | | | | MS4A15 | 1.00 | 16852 | 3 | | | | | | MYH7B | 1.00 |
| 16757 | 3 | | | | | | | MS4A5 | 1.00 | 16853 | 3 | | | | | | MYH8 | 1.00 |
| 16758 | 3 | | | | | | | MS4A6E | 1.00 | 16854 | 3 | | | | | | MYL1 | 1.00 |
| 16759 | 3 | | | | | | | MS4A8B | 1.00 | 16855 | 3 | | | | | | MYL10 | 1.00 |
| 16760 | 3 | | | | | | | MSGN1 | 1.00 | 16856 | 3 | | | | | | MYL2 | 1.00 |
| 16761 | 3 | | | | | | | MSH4 | 1.00 | 16857 | 3 | | | | | | MYL3 | 1.00 |
| 16762 | 3 | | | | | | | MSH5 | 1.00 | 16858 | 3 | | | | | | MYL5 | 1.00 |
| 16763 | 3 | | | | | | | MSH5-SAPCD1 | 1.00 | 16859 | 3 | | | | | | MYL7 | 1.00 |
| 16764 | 3 | | | | | | | MSI1 | 1.00 | 16860 | 3 | | | | | | MYLK-AS1 | 1.00 |
| 16765 | 3 | | | | | | | MSLN | 1.00 | 16861 | 3 | | | | | | MYLK2 | 1.00 |
| 16766 | 3 | | | | | | | MSLNL | 1.00 | 16862 | 3 | | | | | | MYLK3 | 1.00 |
| 16767 | 3 | | | | | | | MSMB | 1.00 | 16863 | 3 | | | | | | MYLK4 | 1.00 |
| 16768 | 3 | | | | | | | MSS51 | 1.00 | 16864 | 3 | | | | | | MYLPF | 1.00 |
| 16769 | 3 | | | | | | | MST1 | 1.00 | 16865 | 3 | | | | | | MYO10 | 1.00 |
| 16770 | 3 | | | | | | | MST1P2 | 1.00 | 16866 | 3 | | | | | | MYO15A | 1.00 |
| 16771 | 3 | | | | | | | MST1P9 | 1.00 | 16867 | 3 | | | | | | MYO16 | 1.00 |
| 16772 | 3 | | | | | | | MST1R | 1.00 | 16868 | 3 | | | | | | MYO18B | 1.00 |
| 16773 | 3 | | | | | | | MSTN | 1.00 | 16869 | 3 | | | | | | MYO1A | 1.00 |
| 16774 | 3 | | | | | | | MSX1 | 1.00 | 16870 | 3 | | | | | | MYO1B | 1.00 |
| 16775 | 3 | | | | | | | MSX2 | 1.00 | 16871 | 3 | | | | | | MYO1H | 1.00 |
| 16776 | 3 | | | | | | | MT1A | 1.00 | 16872 | 3 | | | | | | MYO3A | 1.00 |
| 16777 | 3 | | | | | | | MT1B | 1.00 | 16873 | 3 | | | | | | MYO3B | 1.00 |
| 16778 | 3 | | | | | | | MT1DP | 1.00 | 16874 | 3 | | | | | | MYO5B | 1.00 |
| 16779 | 3 | | | | | | | MT1G | 1.00 | 16875 | 3 | | | | | | MYO5C | 1.00 |
| 16780 | 3 | | | | | | | MT1H | 1.00 | 16876 | 3 | | | | | | MYO6 | 1.00 |
| 16781 | 3 | | | | | | | MT1IP | 1.00 | 16877 | 3 | | | | | | MYOC | 1.00 |
| 16782 | 3 | | | | | | | MT1JP | 1.00 | 16878 | 3 | | | | | | MYOCD | 1.00 |
| 16783 | 3 | | | | | | | MT1L | 1.00 | 16879 | 3 | | | | | | MYOD1 | 1.00 |
| 16784 | 3 | | | | | | | MT1M | 1.00 | 16880 | 3 | | | | | | MYOG | 1.00 |
| 16785 | 3 | | | | | | | MT3 | 1.00 | 16881 | 3 | | | | | | MYOM1 | 1.00 |
| 16786 | 3 | | | | | | | MT4 | 1.00 | 16882 | 3 | | | | | | MYOM3 | 1.00 |
| 16787 | 3 | | | | | | | MTBP | 1.00 | 16883 | 3 | | | | | | MYOT | 1.00 |
| 16788 | 3 | | | | | | | MTCP1 | 1.00 | 16884 | 3 | | | | | | MYOZ1 | 1.00 |
| 16789 | 3 | | | | | | | MTHFD1L | 1.00 | 16885 | 3 | | | | | | MYOZ2 | 1.00 |
| 16790 | 3 | | | | | | | MTHFD2L | 1.00 | 16886 | 3 | | | | | | MYOZ3 | 1.00 |
| 16791 | 3 | | | | | | | MTMR7 | 1.00 | 16887 | 3 | | | | | | MYPN | 1.00 |
| 16792 | 3 | | | | | | | MTMR8 | 1.00 | 16888 | 3 | | | | | | MYRIP | 1.00 |
| 16793 | 3 | | | | | | | MTMR9LP | 1.00 | 16889 | 3 | | | | | | MYT1 | 1.00 |

Fig. 41 - 89

| | | | | | | | | | | | | | | |
|---|---|---|---|---|---|---|---|---|---|---|---|---|---|---|
| 16890 | 3 | | | | | MYT1L | 1.00 | 16986 | 3 | | | | NKAIN1 | 1.00 |
| 16891 | 3 | | | | | NAA11 | 1.00 | 16987 | 3 | | | | NKAIN2 | 1.00 |
| 16892 | 3 | | | | | NAALAD2 | 1.00 | 16988 | 3 | | | | NKAIN3 | 1.00 |
| 16893 | 3 | | | | | NAALADL2 | 1.00 | 16989 | 3 | | | | NKAIN4 | 1.00 |
| 16894 | 3 | | | | | NACAD | 1.00 | 16990 | 3 | | | | NKAPP1 | 1.00 |
| 16895 | 3 | | | | | NALCN | 1.00 | 16991 | 3 | | | | NKD1 | 1.00 |
| 16896 | 3 | | | | | NANOG | 1.00 | 16992 | 3 | | | | NKD2 | 1.00 |
| 16897 | 3 | | | | | NANOGNB | 1.00 | 16993 | 3 | | | | NKPD1 | 1.00 |
| 16898 | 3 | | | | | NANOS2 | 1.00 | 16994 | 3 | | | | NKX1-2 | 1.00 |
| 16899 | 3 | | | | | NANOS3 | 1.00 | 16995 | 3 | | | | NKX2-1 | 1.00 |
| 16900 | 3 | | | | | NAP1L6 | 1.00 | 16996 | 3 | | | | NKX2-2 | 1.00 |
| 16901 | 3 | | | | | NAT16 | 1.00 | 16997 | 3 | | | | NKX2-3 | 1.00 |
| 16902 | 3 | | | | | NAT2 | 1.00 | 16998 | 3 | | | | NKX2-4 | 1.00 |
| 16903 | 3 | | | | | NAT8 | 1.00 | 16999 | 3 | | | | NKX2-5 | 1.00 |
| 16904 | 3 | | | | | NAT8L | 1.00 | 17000 | 3 | | | | NKX2-6 | 1.00 |
| 16905 | 3 | | | | | NAV2 | 1.00 | 17001 | 3 | | | | NKX2-8 | 1.00 |
| 16906 | 3 | | | | | NAV2-AS4 | 1.00 | 17002 | 3 | | | | NKX3-2 | 1.00 |
| 16907 | 3 | | | | | NAV3 | 1.00 | 17003 | 3 | | | | NKX6-1 | 1.00 |
| 16908 | 3 | | | | | NBEA | 1.00 | 17004 | 3 | | | | NKX6-2 | 1.00 |
| 16909 | 3 | | | | | NBEAL1 | 1.00 | 17005 | 3 | | | | NKX6-3 | 1.00 |
| 16910 | 3 | | | | | NBEAP1 | 1.00 | 17006 | 3 | | | | NLGN1 | 1.00 |
| 16911 | 3 | | | | | NBL1 | 1.00 | 17007 | 3 | | | | NLGN2 | 1.00 |
| 16912 | 3 | | | | | NBLA00301 | 1.00 | 17008 | 3 | | | | NLGN4X | 1.00 |
| 16913 | 3 | | | | | NBPF22P | 1.00 | 17009 | 3 | | | | NLGN4Y | 1.00 |
| 16914 | 3 | | | | | NBPF4 | 1.00 | 17010 | 3 | | | | NLRP10 | 1.00 |
| 16915 | 3 | | | | | NBPF6 | 1.00 | 17011 | 3 | | | | NLRP11 | 1.00 |
| 16916 | 3 | | | | | NBPF7 | 1.00 | 17012 | 3 | | | | NLRP13 | 1.00 |
| 16917 | 3 | | | | | NCAM2 | 1.00 | 17013 | 3 | | | | NLRP14 | 1.00 |
| 16918 | 3 | | | | | NCAN | 1.00 | 17014 | 3 | | | | NLRP4 | 1.00 |
| 16919 | 3 | | | | | NCAPG | 1.00 | 17015 | 3 | | | | NLRP5 | 1.00 |
| 16920 | 3 | | | | | NCAPG2 | 1.00 | 17016 | 3 | | | | NLRP7 | 1.00 |
| 16921 | 3 | | | | | NCAPH | 1.00 | 17017 | 3 | | | | NLRP8 | 1.00 |
| 16922 | 3 | | | | | NCCRP1 | 1.00 | 17018 | 3 | | | | NLRP9 | 1.00 |
| 16923 | 3 | | | | | NCKAP1 | 1.00 | 17019 | 3 | | | | NM8R | 1.00 |
| 16924 | 3 | | | | | NCKAP5 | 1.00 | 17020 | 3 | | | | NME1-NME2 | 1.00 |
| 16925 | 3 | | | | | NCOR1P1 | 1.00 | 17021 | 3 | | | | NME5 | 1.00 |
| 16926 | 3 | | | | | NCR2 | 1.00 | 17022 | 3 | | | | NME9 | 1.00 |
| 16927 | 3 | | | | | NCRNA00185 | 1.00 | 17023 | 3 | | | | NMNAT2 | 1.00 |
| 16928 | 3 | | | | | NCRUPAR | 1.00 | 17024 | 3 | | | | NMS | 1.00 |
| 16929 | 3 | | | | | NCS1 | 1.00 | 17025 | 3 | | | | NMU | 1.00 |
| 16930 | 3 | | | | | NDC80 | 1.00 | 17026 | 3 | | | | NMUR2 | 1.00 |
| 16931 | 3 | | | | | NDFIP2 | 1.00 | 17027 | 3 | | | | NNMT | 1.00 |
| 16932 | 3 | | | | | NDNF | 1.00 | 17028 | 3 | | | | NOBOX | 1.00 |
| 16933 | 3 | | | | | NDP | 1.00 | 17029 | 3 | | | | NODAL | 1.00 |
| 16934 | 3 | | | | | NDRG4 | 1.00 | 17030 | 3 | | | | NOL4 | 1.00 |
| 16935 | 3 | | | | | NDST3 | 1.00 | 17031 | 3 | | | | NOS1 | 1.00 |
| 16936 | 3 | | | | | NDST4 | 1.00 | 17032 | 3 | | | | NOS1AP | 1.00 |
| 16937 | 3 | | | | | NDUFA4L2 | 1.00 | 17033 | 3 | | | | NOS2 | 1.00 |
| 16938 | 3 | | | | | NDUFC2-KCTD14 | 1.00 | 17034 | 3 | | | | NOS3 | 1.00 |
| 16939 | 3 | | | | | NEB | 1.00 | 17035 | 3 | | | | NOSTRIN | 1.00 |
| 16940 | 3 | | | | | NECAB1 | 1.00 | 17036 | 3 | | | | NOTCH3 | 1.00 |
| 16941 | 3 | | | | | NEDD4L | 1.00 | 17037 | 3 | | | | NOTCH4 | 1.00 |
| 16942 | 3 | | | | | NEDD8-MDP1 | 1.00 | 17038 | 3 | | | | NOTO | 1.00 |
| 16943 | 3 | | | | | NEFH | 1.00 | 17039 | 3 | | | | NOTUM | 1.00 |
| 16944 | 3 | | | | | NEFM | 1.00 | 17040 | 3 | | | | NOVA1 | 1.00 |
| 16945 | 3 | | | | | NEGR1 | 1.00 | 17041 | 3 | | | | NOVA2 | 1.00 |
| 16946 | 3 | | | | | NEGR1-IT1 | 1.00 | 17042 | 3 | | | | NOX1 | 1.00 |
| 16947 | 3 | | | | | NEIL3 | 1.00 | 17043 | 3 | | | | NOX3 | 1.00 |
| 16948 | 3 | | | | | NEK10 | 1.00 | 17044 | 3 | | | | NOX4 | 1.00 |
| 16949 | 3 | | | | | NEK11 | 1.00 | 17045 | 3 | | | | NOX5 | 1.00 |
| 16950 | 3 | | | | | NEK2 | 1.00 | 17046 | 3 | | | | NOXA1 | 1.00 |
| 16951 | 3 | | | | | NEK5 | 1.00 | 17047 | 3 | | | | NOXO1 | 1.00 |
| 16952 | 3 | | | | | NELL1 | 1.00 | 17048 | 3 | | | | NOXRED1 | 1.00 |
| 16953 | 3 | | | | | NES | 1.00 | 17049 | 3 | | | | NPAS1 | 1.00 |
| 16954 | 3 | | | | | NETO1 | 1.00 | 17050 | 3 | | | | NPAS2 | 1.00 |
| 16955 | 3 | | | | | NEU2 | 1.00 | 17051 | 3 | | | | NPAS3 | 1.00 |
| 16956 | 3 | | | | | NEU4 | 1.00 | 17052 | 3 | | | | NPAS4 | 1.00 |
| 16957 | 3 | | | | | NEURL1B | 1.00 | 17053 | 3 | | | | NPB | 1.00 |
| 16958 | 3 | | | | | NEURL2 | 1.00 | 17054 | 3 | | | | NPBWR2 | 1.00 |
| 16959 | 3 | | | | | NEURL3 | 1.00 | 17055 | 3 | | | | NPC1L1 | 1.00 |
| 16960 | 3 | | | | | NEUROD1 | 1.00 | 17056 | 3 | | | | NPFFR1 | 1.00 |
| 16961 | 3 | | | | | NEUROD2 | 1.00 | 17057 | 3 | | | | NPFFR2 | 1.00 |
| 16962 | 3 | | | | | NEUROD4 | 1.00 | 17058 | 3 | | | | NPHP1 | 1.00 |
| 16963 | 3 | | | | | NEUROD6 | 1.00 | 17059 | 3 | | | | NPHP3-ACAD11 | 1.00 |
| 16964 | 3 | | | | | NEUROG1 | 1.00 | 17060 | 3 | | | | NPHP3-AS1 | 1.00 |
| 16965 | 3 | | | | | NEUROG2 | 1.00 | 17061 | 3 | | | | NPHP4 | 1.00 |
| 16966 | 3 | | | | | NEUROG3 | 1.00 | 17062 | 3 | | | | NPHS1 | 1.00 |
| 16967 | 3 | | | | | NF1P2 | 1.00 | 17063 | 3 | | | | NPHS2 | 1.00 |
| 16968 | 3 | | | | | NFASC | 1.00 | 17064 | 3 | | | | NPM2 | 1.00 |
| 16969 | 3 | | | | | NFATC4 | 1.00 | 17065 | 3 | | | | NPNT | 1.00 |
| 16970 | 3 | | | | | NFIB | 1.00 | 17066 | 3 | | | | NPPA | 1.00 |
| 16971 | 3 | | | | | NGB | 1.00 | 17067 | 3 | | | | NPPB | 1.00 |
| 16972 | 3 | | | | | NGEF | 1.00 | 17068 | 3 | | | | NPPC | 1.00 |
| 16973 | 3 | | | | | NGF | 1.00 | 17069 | 3 | | | | NPR1 | 1.00 |
| 16974 | 3 | | | | | NGFR | 1.00 | 17070 | 3 | | | | NPR2 | 1.00 |
| 16975 | 3 | | | | | NHEG1 | 1.00 | 17071 | 3 | | | | NPR3 | 1.00 |
| 16976 | 3 | | | | | NHLH1 | 1.00 | 17072 | 3 | | | | NPS | 1.00 |
| 16977 | 3 | | | | | NHLH2 | 1.00 | 17073 | 3 | | | | NPSR1 | 1.00 |
| 16978 | 3 | | | | | NHLRC4 | 1.00 | 17074 | 3 | | | | NPTX1 | 1.00 |
| 16979 | 3 | | | | | NHSL1 | 1.00 | 17075 | 3 | | | | NPTX2 | 1.00 |
| 16980 | 3 | | | | | NID2 | 1.00 | 17076 | 3 | | | | NPVF | 1.00 |
| 16981 | 3 | | | | | NIM1 | 1.00 | 17077 | 3 | | | | NPW | 1.00 |
| 16982 | 3 | | | | | NINL | 1.00 | 17078 | 3 | | | | NPY | 1.00 |
| 16983 | 3 | | | | | NIPAL1 | 1.00 | 17079 | 3 | | | | NPY1R | 1.00 |
| 16984 | 3 | | | | | NIPAL4 | 1.00 | 17080 | 3 | | | | NPY2R | 1.00 |
| 16985 | 3 | | | | | NIPSNAP3B | 1.00 | 17081 | 3 | | | | NPY5R | 1.00 |

Fig. 41 - 90

| | | | | | | | | | | | | | | |
|---|---|---|---|---|---|---|---|---|---|---|---|---|---|---|
| 17082 | 3 | | | | | NPY6R | 1.00 | 17178 | 3 | | | | ODZ4 | 1.00 |
| 17083 | 3 | | | | | NR0B1 | 1.00 | 17179 | 3 | | | | OGDHL | 1.00 |
| 17084 | 3 | | | | | NR0B2 | 1.00 | 17180 | 3 | | | | OGN | 1.00 |
| 17085 | 3 | | | | | NR1H4 | 1.00 | 17181 | 3 | | | | OIP5 | 1.00 |
| 17086 | 3 | | | | | NR1I2 | 1.00 | 17182 | 3 | | | | OIT3 | 1.00 |
| 17087 | 3 | | | | | NR1I3 | 1.00 | 17183 | 3 | | | | OLAH | 1.00 |
| 17088 | 3 | | | | | NR2E1 | 1.00 | 17184 | 3 | | | | OLFM3 | 1.00 |
| 17089 | 3 | | | | | NR2E3 | 1.00 | 17185 | 3 | | | | OLFML1 | 1.00 |
| 17090 | 3 | | | | | NR2F1 | 1.00 | 17186 | 3 | | | | OLFML2A | 1.00 |
| 17091 | 3 | | | | | NR2F2 | 1.00 | 17187 | 3 | | | | OLFML3 | 1.00 |
| 17092 | 3 | | | | | NR4A3 | 1.00 | 17188 | 3 | | | | OLIG3 | 1.00 |
| 17093 | 3 | | | | | NR5A1 | 1.00 | 17189 | 3 | | | | OMD | 1.00 |
| 17094 | 3 | | | | | NR5A2 | 1.00 | 17190 | 3 | | | | OMG | 1.00 |
| 17095 | 3 | | | | | NRADDP | 1.00 | 17191 | 3 | | | | OMP | 1.00 |
| 17096 | 3 | | | | | NRAP | 1.00 | 17192 | 3 | | | | ONECUT1 | 1.00 |
| 17097 | 3 | | | | | NRARP | 1.00 | 17193 | 3 | | | | ONECUT2 | 1.00 |
| 17098 | 3 | | | | | NRCAM | 1.00 | 17194 | 3 | | | | ONECUT3 | 1.00 |
| 17099 | 3 | | | | | NRG2 | 1.00 | 17195 | 3 | | | | OOEP | 1.00 |
| 17100 | 3 | | | | | NRG3 | 1.00 | 17196 | 3 | | | | OPALIN | 1.00 |
| 17101 | 3 | | | | | NRG4 | 1.00 | 17197 | 3 | | | | OPCML | 1.00 |
| 17102 | 3 | | | | | NRIP2 | 1.00 | 17198 | 3 | | | | OPHN1 | 1.00 |
| 17103 | 3 | | | | | NRIP3 | 1.00 | 17199 | 3 | | | | OPLAH | 1.00 |
| 17104 | 3 | | | | | NRK | 1.00 | 17200 | 3 | | | | OPN1LW | 1.00 |
| 17105 | 3 | | | | | NRN1 | 1.00 | 17201 | 3 | | | | OPN1MW | 1.00 |
| 17106 | 3 | | | | | NRN1L | 1.00 | 17202 | 3 | | | | OPN1MW2 | 1.00 |
| 17107 | 3 | | | | | NRON | 1.00 | 17203 | 3 | | | | OPN1SW | 1.00 |
| 17108 | 3 | | | | | NRP2 | 1.00 | 17204 | 3 | | | | OPN4 | 1.00 |
| 17109 | 3 | | | | | NRSN1 | 1.00 | 17205 | 3 | | | | OPN5 | 1.00 |
| 17110 | 3 | | | | | NRTN | 1.00 | 17206 | 3 | | | | OPRD1 | 1.00 |
| 17111 | 3 | | | | | NRXN1 | 1.00 | 17207 | 3 | | | | OPRK1 | 1.00 |
| 17112 | 3 | | | | | NRXN2 | 1.00 | 17208 | 3 | | | | OPRM1 | 1.00 |
| 17113 | 3 | | | | | NRXN3 | 1.00 | 17209 | 3 | | | | OPTC | 1.00 |
| 17114 | 3 | | | | | NT5C1A | 1.00 | 17210 | 3 | | | | OR10A2 | 1.00 |
| 17115 | 3 | | | | | NT5C1B | 1.00 | 17211 | 3 | | | | OR10A3 | 1.00 |
| 17116 | 3 | | | | | NT5C1B-RDH14 | 1.00 | 17212 | 3 | | | | OR10A4 | 1.00 |
| 17117 | 3 | | | | | NT5DC3 | 1.00 | 17213 | 3 | | | | OR10A5 | 1.00 |
| 17118 | 3 | | | | | NTF3 | 1.00 | 17214 | 3 | | | | OR10A6 | 1.00 |
| 17119 | 3 | | | | | NTF4 | 1.00 | 17215 | 3 | | | | OR10A7 | 1.00 |
| 17120 | 3 | | | | | NTM | 1.00 | 17216 | 3 | | | | OR10AD1 | 1.00 |
| 17121 | 3 | | | | | NTN1 | 1.00 | 17217 | 3 | | | | OR10AG1 | 1.00 |
| 17122 | 3 | | | | | NTN3 | 1.00 | 17218 | 3 | | | | OR10C1 | 1.00 |
| 17123 | 3 | | | | | NTN4 | 1.00 | 17219 | 3 | | | | OR10G2 | 1.00 |
| 17124 | 3 | | | | | NTN5 | 1.00 | 17220 | 3 | | | | OR10G3 | 1.00 |
| 17125 | 3 | | | | | NTNG1 | 1.00 | 17221 | 3 | | | | OR10G4 | 1.00 |
| 17126 | 3 | | | | | NTRK1 | 1.00 | 17222 | 3 | | | | OR10G7 | 1.00 |
| 17127 | 3 | | | | | NTRK2 | 1.00 | 17223 | 3 | | | | OR10G8 | 1.00 |
| 17128 | 3 | | | | | NTRK3 | 1.00 | 17224 | 3 | | | | OR10G9 | 1.00 |
| 17129 | 3 | | | | | NTS | 1.00 | 17225 | 3 | | | | OR10H1 | 1.00 |
| 17130 | 3 | | | | | NTSR2 | 1.00 | 17226 | 3 | | | | OR10H2 | 1.00 |
| 17131 | 3 | | | | | NUAK1 | 1.00 | 17227 | 3 | | | | OR10H3 | 1.00 |
| 17132 | 3 | | | | | NUDT10 | 1.00 | 17228 | 3 | | | | OR10H4 | 1.00 |
| 17133 | 3 | | | | | NUDT11 | 1.00 | 17229 | 3 | | | | OR10H5 | 1.00 |
| 17134 | 3 | | | | | NUDT12 | 1.00 | 17230 | 3 | | | | OR10J1 | 1.00 |
| 17135 | 3 | | | | | NUDT13 | 1.00 | 17231 | 3 | | | | OR10J3 | 1.00 |
| 17136 | 3 | | | | | NUDT6 | 1.00 | 17232 | 3 | | | | OR10J5 | 1.00 |
| 17137 | 3 | | | | | NUDT8 | 1.00 | 17233 | 3 | | | | OR10K1 | 1.00 |
| 17138 | 3 | | | | | NUDT9P1 | 1.00 | 17234 | 3 | | | | OR10K2 | 1.00 |
| 17139 | 3 | | | | | NUF2 | 1.00 | 17235 | 3 | | | | OR10P1 | 1.00 |
| 17140 | 3 | | | | | NUM8L | 1.00 | 17236 | 3 | | | | OR10Q1 | 1.00 |
| 17141 | 3 | | | | | NUP210L | 1.00 | 17237 | 3 | | | | OR10R2 | 1.00 |
| 17142 | 3 | | | | | NUP210P1 | 1.00 | 17238 | 3 | | | | OR10S1 | 1.00 |
| 17143 | 3 | | | | | NUP62CL | 1.00 | 17239 | 3 | | | | OR10T2 | 1.00 |
| 17144 | 3 | | | | | NUPR1 | 1.00 | 17240 | 3 | | | | OR10V1 | 1.00 |
| 17145 | 3 | | | | | NWD1 | 1.00 | 17241 | 3 | | | | OR10V2P | 1.00 |
| 17146 | 3 | | | | | NXF2 | 1.00 | 17242 | 3 | | | | OR10W1 | 1.00 |
| 17147 | 3 | | | | | NXF2B | 1.00 | 17243 | 3 | | | | OR10X1 | 1.00 |
| 17148 | 3 | | | | | NXF3 | 1.00 | 17244 | 3 | | | | OR10Z1 | 1.00 |
| 17149 | 3 | | | | | NXF4 | 1.00 | 17245 | 3 | | | | OR11A1 | 1.00 |
| 17150 | 3 | | | | | NXF5 | 1.00 | 17246 | 3 | | | | OR11G2 | 1.00 |
| 17151 | 3 | | | | | NXN | 1.00 | 17247 | 3 | | | | OR11H1 | 1.00 |
| 17152 | 3 | | | | | NXNL1 | 1.00 | 17248 | 3 | | | | OR11H12 | 1.00 |
| 17153 | 3 | | | | | NXNL2 | 1.00 | 17249 | 3 | | | | OR11H2 | 1.00 |
| 17154 | 3 | | | | | NXPH1 | 1.00 | 17250 | 3 | | | | OR11H4 | 1.00 |
| 17155 | 3 | | | | | NXPH2 | 1.00 | 17251 | 3 | | | | OR11H6 | 1.00 |
| 17156 | 3 | | | | | NXPH3 | 1.00 | 17252 | 3 | | | | OR11L1 | 1.00 |
| 17157 | 3 | | | | | NYAP1 | 1.00 | 17253 | 3 | | | | OR12D2 | 1.00 |
| 17158 | 3 | | | | | NYAP2 | 1.00 | 17254 | 3 | | | | OR12D3 | 1.00 |
| 17159 | 3 | | | | | NYNRIN | 1.00 | 17255 | 3 | | | | OR13A1 | 1.00 |
| 17160 | 3 | | | | | NYX | 1.00 | 17256 | 3 | | | | OR13C2 | 1.00 |
| 17161 | 3 | | | | | OBP2A | 1.00 | 17257 | 3 | | | | OR13C3 | 1.00 |
| 17162 | 3 | | | | | OBP2B | 1.00 | 17258 | 3 | | | | OR13C4 | 1.00 |
| 17163 | 3 | | | | | OBSL1 | 1.00 | 17259 | 3 | | | | OR13C5 | 1.00 |
| 17164 | 3 | | | | | OC90 | 1.00 | 17260 | 3 | | | | OR13C8 | 1.00 |
| 17165 | 3 | | | | | OCA2 | 1.00 | 17261 | 3 | | | | OR13C9 | 1.00 |
| 17166 | 3 | | | | | OCLM | 1.00 | 17262 | 3 | | | | OR13D1 | 1.00 |
| 17167 | 3 | | | | | OCLN | 1.00 | 17263 | 3 | | | | OR13F1 | 1.00 |
| 17168 | 3 | | | | | OCM2 | 1.00 | 17264 | 3 | | | | OR13G1 | 1.00 |
| 17169 | 3 | | | | | ODAM | 1.00 | 17265 | 3 | | | | OR13H1 | 1.00 |
| 17170 | 3 | | | | | ODF1 | 1.00 | 17266 | 3 | | | | OR13J1 | 1.00 |
| 17171 | 3 | | | | | ODF3 | 1.00 | 17267 | 3 | | | | OR14A16 | 1.00 |
| 17172 | 3 | | | | | ODF3L1 | 1.00 | 17268 | 3 | | | | OR14C36 | 1.00 |
| 17173 | 3 | | | | | ODF3L2 | 1.00 | 17269 | 3 | | | | OR14I1 | 1.00 |
| 17174 | 3 | | | | | ODF4 | 1.00 | 17270 | 3 | | | | OR14J1 | 1.00 |
| 17175 | 3 | | | | | ODZ1 | 1.00 | 17271 | 3 | | | | OR1A1 | 1.00 |
| 17176 | 3 | | | | | ODZ2 | 1.00 | 17272 | 3 | | | | OR1A2 | 1.00 |
| 17177 | 3 | | | | | ODZ3 | 1.00 | 17273 | 3 | | | | OR1B1 | 1.00 |

Fig. 41 - 91

| | | | | | | | | | | | | | | |
|---|---|---|---|---|---|---|---|---|---|---|---|---|---|---|
| 17274 | 3 | | | | | OR1C1 | 1.00 | 17370 | 3 | | | | OR4A5 | 1.00 |
| 17275 | 3 | | | | | OR1D2 | 1.00 | 17371 | 3 | | | | OR4B1 | 1.00 |
| 17276 | 3 | | | | | OR1D4 | 1.00 | 17372 | 3 | | | | OR4C11 | 1.00 |
| 17277 | 3 | | | | | OR1D5 | 1.00 | 17373 | 3 | | | | OR4C12 | 1.00 |
| 17278 | 3 | | | | | OR1E1 | 1.00 | 17374 | 3 | | | | OR4C13 | 1.00 |
| 17279 | 3 | | | | | OR1E2 | 1.00 | 17375 | 3 | | | | OR4C15 | 1.00 |
| 17280 | 3 | | | | | OR1F1 | 1.00 | 17376 | 3 | | | | OR4C16 | 1.00 |
| 17281 | 3 | | | | | OR1F2P | 1.00 | 17377 | 3 | | | | OR4C3 | 1.00 |
| 17282 | 3 | | | | | OR1G1 | 1.00 | 17378 | 3 | | | | OR4C45 | 1.00 |
| 17283 | 3 | | | | | OR1I1 | 1.00 | 17379 | 3 | | | | OR4C46 | 1.00 |
| 17284 | 3 | | | | | OR1J1 | 1.00 | 17380 | 3 | | | | OR4C6 | 1.00 |
| 17285 | 3 | | | | | OR1J2 | 1.00 | 17381 | 3 | | | | OR4D1 | 1.00 |
| 17286 | 3 | | | | | OR1J4 | 1.00 | 17382 | 3 | | | | OR4D10 | 1.00 |
| 17287 | 3 | | | | | OR1K1 | 1.00 | 17383 | 3 | | | | OR4D11 | 1.00 |
| 17288 | 3 | | | | | OR1L1 | 1.00 | 17384 | 3 | | | | OR4D2 | 1.00 |
| 17289 | 3 | | | | | OR1L3 | 1.00 | 17385 | 3 | | | | OR4D5 | 1.00 |
| 17290 | 3 | | | | | OR1L4 | 1.00 | 17386 | 3 | | | | OR4D6 | 1.00 |
| 17291 | 3 | | | | | OR1L6 | 1.00 | 17387 | 3 | | | | OR4D9 | 1.00 |
| 17292 | 3 | | | | | OR1L8 | 1.00 | 17388 | 3 | | | | OR4E2 | 1.00 |
| 17293 | 3 | | | | | OR1M1 | 1.00 | 17389 | 3 | | | | OR4F15 | 1.00 |
| 17294 | 3 | | | | | OR1N1 | 1.00 | 17390 | 3 | | | | OR4F16 | 1.00 |
| 17295 | 3 | | | | | OR1N2 | 1.00 | 17391 | 3 | | | | OR4F17 | 1.00 |
| 17296 | 3 | | | | | OR1Q1 | 1.00 | 17392 | 3 | | | | OR4F21 | 1.00 |
| 17297 | 3 | | | | | OR1S1 | 1.00 | 17393 | 3 | | | | OR4F29 | 1.00 |
| 17298 | 3 | | | | | OR1S2 | 1.00 | 17394 | 3 | | | | OR4F4 | 1.00 |
| 17299 | 3 | | | | | OR2A1 | 1.00 | 17395 | 3 | | | | OR4F5 | 1.00 |
| 17300 | 3 | | | | | OR2A12 | 1.00 | 17396 | 3 | | | | OR4F6 | 1.00 |
| 17301 | 3 | | | | | OR2A14 | 1.00 | 17397 | 3 | | | | OR4K1 | 1.00 |
| 17302 | 3 | | | | | OR2A2 | 1.00 | 17398 | 3 | | | | OR4K13 | 1.00 |
| 17303 | 3 | | | | | OR2A25 | 1.00 | 17399 | 3 | | | | OR4K14 | 1.00 |
| 17304 | 3 | | | | | OR2A4 | 1.00 | 17400 | 3 | | | | OR4K15 | 1.00 |
| 17305 | 3 | | | | | OR2A42 | 1.00 | 17401 | 3 | | | | OR4K17 | 1.00 |
| 17306 | 3 | | | | | OR2A5 | 1.00 | 17402 | 3 | | | | OR4K2 | 1.00 |
| 17307 | 3 | | | | | OR2A7 | 1.00 | 17403 | 3 | | | | OR4K5 | 1.00 |
| 17308 | 3 | | | | | OR2AE1 | 1.00 | 17404 | 3 | | | | OR4L1 | 1.00 |
| 17309 | 3 | | | | | OR2AG1 | 1.00 | 17405 | 3 | | | | OR4M1 | 1.00 |
| 17310 | 3 | | | | | OR2AG2 | 1.00 | 17406 | 3 | | | | OR4M2 | 1.00 |
| 17311 | 3 | | | | | OR2AK2 | 1.00 | 17407 | 3 | | | | OR4N2 | 1.00 |
| 17312 | 3 | | | | | OR2AT4 | 1.00 | 17408 | 3 | | | | OR4N3P | 1.00 |
| 17313 | 3 | | | | | OR2B11 | 1.00 | 17409 | 3 | | | | OR4N4 | 1.00 |
| 17314 | 3 | | | | | OR2B2 | 1.00 | 17410 | 3 | | | | OR4N5 | 1.00 |
| 17315 | 3 | | | | | OR2B3 | 1.00 | 17411 | 3 | | | | OR4P4 | 1.00 |
| 17316 | 3 | | | | | OR2B6 | 1.00 | 17412 | 3 | | | | OR4Q3 | 1.00 |
| 17317 | 3 | | | | | OR2C1 | 1.00 | 17413 | 3 | | | | OR4S1 | 1.00 |
| 17318 | 3 | | | | | OR2C3 | 1.00 | 17414 | 3 | | | | OR4S2 | 1.00 |
| 17319 | 3 | | | | | OR2D2 | 1.00 | 17415 | 3 | | | | OR4X1 | 1.00 |
| 17320 | 3 | | | | | OR2D3 | 1.00 | 17416 | 3 | | | | OR4X2 | 1.00 |
| 17321 | 3 | | | | | OR2F1 | 1.00 | 17417 | 3 | | | | OR51A2 | 1.00 |
| 17322 | 3 | | | | | OR2F2 | 1.00 | 17418 | 3 | | | | OR51A4 | 1.00 |
| 17323 | 3 | | | | | OR2G2 | 1.00 | 17419 | 3 | | | | OR51A7 | 1.00 |
| 17324 | 3 | | | | | OR2G3 | 1.00 | 17420 | 3 | | | | OR51B2 | 1.00 |
| 17325 | 3 | | | | | OR2G6 | 1.00 | 17421 | 3 | | | | OR51B4 | 1.00 |
| 17326 | 3 | | | | | OR2H1 | 1.00 | 17422 | 3 | | | | OR51B5 | 1.00 |
| 17327 | 3 | | | | | OR2H2 | 1.00 | 17423 | 3 | | | | OR51B6 | 1.00 |
| 17328 | 3 | | | | | OR2J2 | 1.00 | 17424 | 3 | | | | OR51D1 | 1.00 |
| 17329 | 3 | | | | | OR2J3 | 1.00 | 17425 | 3 | | | | OR51E1 | 1.00 |
| 17330 | 3 | | | | | OR2K2 | 1.00 | 17426 | 3 | | | | OR51E2 | 1.00 |
| 17331 | 3 | | | | | OR2L13 | 1.00 | 17427 | 3 | | | | OR51F1 | 1.00 |
| 17332 | 3 | | | | | OR2L1P | 1.00 | 17428 | 3 | | | | OR51F2 | 1.00 |
| 17333 | 3 | | | | | OR2L2 | 1.00 | 17429 | 3 | | | | OR51G1 | 1.00 |
| 17334 | 3 | | | | | OR2L3 | 1.00 | 17430 | 3 | | | | OR51G2 | 1.00 |
| 17335 | 3 | | | | | OR2L8 | 1.00 | 17431 | 3 | | | | OR51I1 | 1.00 |
| 17336 | 3 | | | | | OR2M1P | 1.00 | 17432 | 3 | | | | OR51I2 | 1.00 |
| 17337 | 3 | | | | | OR2M2 | 1.00 | 17433 | 3 | | | | OR51L1 | 1.00 |
| 17338 | 3 | | | | | OR2M3 | 1.00 | 17434 | 3 | | | | OR51M1 | 1.00 |
| 17339 | 3 | | | | | OR2M4 | 1.00 | 17435 | 3 | | | | OR51Q1 | 1.00 |
| 17340 | 3 | | | | | OR2M5 | 1.00 | 17436 | 3 | | | | OR51S1 | 1.00 |
| 17341 | 3 | | | | | OR2M7 | 1.00 | 17437 | 3 | | | | OR51T1 | 1.00 |
| 17342 | 3 | | | | | OR2S2 | 1.00 | 17438 | 3 | | | | OR51V1 | 1.00 |
| 17343 | 3 | | | | | OR2T1 | 1.00 | 17439 | 3 | | | | OR52A1 | 1.00 |
| 17344 | 3 | | | | | OR2T10 | 1.00 | 17440 | 3 | | | | OR52A5 | 1.00 |
| 17345 | 3 | | | | | OR2T11 | 1.00 | 17441 | 3 | | | | OR52B2 | 1.00 |
| 17346 | 3 | | | | | OR2T12 | 1.00 | 17442 | 3 | | | | OR52B4 | 1.00 |
| 17347 | 3 | | | | | OR2T2 | 1.00 | 17443 | 3 | | | | OR52B6 | 1.00 |
| 17348 | 3 | | | | | OR2T27 | 1.00 | 17444 | 3 | | | | OR52D1 | 1.00 |
| 17349 | 3 | | | | | OR2T29 | 1.00 | 17445 | 3 | | | | OR52E2 | 1.00 |
| 17350 | 3 | | | | | OR2T3 | 1.00 | 17446 | 3 | | | | OR52E4 | 1.00 |
| 17351 | 3 | | | | | OR2T33 | 1.00 | 17447 | 3 | | | | OR52E6 | 1.00 |
| 17352 | 3 | | | | | OR2T34 | 1.00 | 17448 | 3 | | | | OR52E8 | 1.00 |
| 17353 | 3 | | | | | OR2T35 | 1.00 | 17449 | 3 | | | | OR52H1 | 1.00 |
| 17354 | 3 | | | | | OR2T4 | 1.00 | 17450 | 3 | | | | OR52I1 | 1.00 |
| 17355 | 3 | | | | | OR2T5 | 1.00 | 17451 | 3 | | | | OR52I2 | 1.00 |
| 17356 | 3 | | | | | OR2T6 | 1.00 | 17452 | 3 | | | | OR52J3 | 1.00 |
| 17357 | 3 | | | | | OR2T8 | 1.00 | 17453 | 3 | | | | OR52K1 | 1.00 |
| 17358 | 3 | | | | | OR2V2 | 1.00 | 17454 | 3 | | | | OR52K2 | 1.00 |
| 17359 | 3 | | | | | OR2W1 | 1.00 | 17455 | 3 | | | | OR52L1 | 1.00 |
| 17360 | 3 | | | | | OR2W5 | 1.00 | 17456 | 3 | | | | OR52M1 | 1.00 |
| 17361 | 3 | | | | | OR2Y1 | 1.00 | 17457 | 3 | | | | OR52N1 | 1.00 |
| 17362 | 3 | | | | | OR2Z1 | 1.00 | 17458 | 3 | | | | OR52N2 | 1.00 |
| 17363 | 3 | | | | | OR3A1 | 1.00 | 17459 | 3 | | | | OR52N4 | 1.00 |
| 17364 | 3 | | | | | OR3A2 | 1.00 | 17460 | 3 | | | | OR52N5 | 1.00 |
| 17365 | 3 | | | | | OR3A3 | 1.00 | 17461 | 3 | | | | OR52R1 | 1.00 |
| 17366 | 3 | | | | | OR3A4P | 1.00 | 17462 | 3 | | | | OR52W1 | 1.00 |
| 17367 | 3 | | | | | OR4A15 | 1.00 | 17463 | 3 | | | | OR56A1 | 1.00 |
| 17368 | 3 | | | | | OR4A16 | 1.00 | 17464 | 3 | | | | OR56A3 | 1.00 |
| 17369 | 3 | | | | | OR4A47 | 1.00 | 17465 | 3 | | | | OR56A4 | 1.00 |

Fig. 41 - 92

| | | | | | | | | | | | | | | | | |
|---|---|---|---|---|---|---|---|---|---|---|---|---|---|---|---|---|
| 17466 | 3 | | | | | | OR56A5 | 1.00 | 17562 | 3 | | | | | OR7E91P | 1.00 |
| 17467 | 3 | | | | | | OR56B1 | 1.00 | 17563 | 3 | | | | | OR7G1 | 1.00 |
| 17468 | 3 | | | | | | OR56B4 | 1.00 | 17564 | 3 | | | | | OR7G2 | 1.00 |
| 17469 | 3 | | | | | | OR5A1 | 1.00 | 17565 | 3 | | | | | OR7G3 | 1.00 |
| 17470 | 3 | | | | | | OR5A2 | 1.00 | 17566 | 3 | | | | | OR8A1 | 1.00 |
| 17471 | 3 | | | | | | OR5AC2 | 1.00 | 17567 | 3 | | | | | OR8B12 | 1.00 |
| 17472 | 3 | | | | | | OR5AK2 | 1.00 | 17568 | 3 | | | | | OR8B2 | 1.00 |
| 17473 | 3 | | | | | | OR5AK4P | 1.00 | 17569 | 3 | | | | | OR8B3 | 1.00 |
| 17474 | 3 | | | | | | OR5AN1 | 1.00 | 17570 | 3 | | | | | OR8B4 | 1.00 |
| 17475 | 3 | | | | | | OR5AP2 | 1.00 | 17571 | 3 | | | | | OR8B8 | 1.00 |
| 17476 | 3 | | | | | | OR5AR1 | 1.00 | 17572 | 3 | | | | | OR8D1 | 1.00 |
| 17477 | 3 | | | | | | OR5AS1 | 1.00 | 17573 | 3 | | | | | OR8D2 | 1.00 |
| 17478 | 3 | | | | | | OR5AU1 | 1.00 | 17574 | 3 | | | | | OR8D4 | 1.00 |
| 17479 | 3 | | | | | | OR5B12 | 1.00 | 17575 | 3 | | | | | OR8G1 | 1.00 |
| 17480 | 3 | | | | | | OR5B17 | 1.00 | 17576 | 3 | | | | | OR8G2 | 1.00 |
| 17481 | 3 | | | | | | OR5B2 | 1.00 | 17577 | 3 | | | | | OR8G5 | 1.00 |
| 17482 | 3 | | | | | | OR5B21 | 1.00 | 17578 | 3 | | | | | OR8H1 | 1.00 |
| 17483 | 3 | | | | | | OR5B3 | 1.00 | 17579 | 3 | | | | | OR8H2 | 1.00 |
| 17484 | 3 | | | | | | OR5C1 | 1.00 | 17580 | 3 | | | | | OR8H3 | 1.00 |
| 17485 | 3 | | | | | | OR5D13 | 1.00 | 17581 | 3 | | | | | OR8I2 | 1.00 |
| 17486 | 3 | | | | | | OR5D14 | 1.00 | 17582 | 3 | | | | | OR8J1 | 1.00 |
| 17487 | 3 | | | | | | OR5D16 | 1.00 | 17583 | 3 | | | | | OR8J3 | 1.00 |
| 17488 | 3 | | | | | | OR5D18 | 1.00 | 17584 | 3 | | | | | OR8K1 | 1.00 |
| 17489 | 3 | | | | | | OR5E1P | 1.00 | 17585 | 3 | | | | | OR8K3 | 1.00 |
| 17490 | 3 | | | | | | OR5F1 | 1.00 | 17586 | 3 | | | | | OR8K5 | 1.00 |
| 17491 | 3 | | | | | | OR5H1 | 1.00 | 17587 | 3 | | | | | OR8S1 | 1.00 |
| 17492 | 3 | | | | | | OR5H14 | 1.00 | 17588 | 3 | | | | | OR8U1 | 1.00 |
| 17493 | 3 | | | | | | OR5H15 | 1.00 | 17589 | 3 | | | | | OR8U8 | 1.00 |
| 17494 | 3 | | | | | | OR5H2 | 1.00 | 17590 | 3 | | | | | OR9A2 | 1.00 |
| 17495 | 3 | | | | | | OR5H6 | 1.00 | 17591 | 3 | | | | | OR9A4 | 1.00 |
| 17496 | 3 | | | | | | OR5I1 | 1.00 | 17592 | 3 | | | | | OR9G4 | 1.00 |
| 17497 | 3 | | | | | | OR5J2 | 1.00 | 17593 | 3 | | | | | OR9G9 | 1.00 |
| 17498 | 3 | | | | | | OR5K1 | 1.00 | 17594 | 3 | | | | | OR9I1 | 1.00 |
| 17499 | 3 | | | | | | OR5K2 | 1.00 | 17595 | 3 | | | | | OR9K2 | 1.00 |
| 17500 | 3 | | | | | | OR5K3 | 1.00 | 17596 | 3 | | | | | OR9Q1 | 1.00 |
| 17501 | 3 | | | | | | OR5K4 | 1.00 | 17597 | 3 | | | | | OR9Q2 | 1.00 |
| 17502 | 3 | | | | | | OR5L1 | 1.00 | 17598 | 3 | | | | | ORC1 | 1.00 |
| 17503 | 3 | | | | | | OR5L2 | 1.00 | 17599 | 3 | | | | | ORC6 | 1.00 |
| 17504 | 3 | | | | | | OR5M1 | 1.00 | 17600 | 3 | | | | | OSBPL6 | 1.00 |
| 17505 | 3 | | | | | | OR5M10 | 1.00 | 17601 | 3 | | | | | OSCP1 | 1.00 |
| 17506 | 3 | | | | | | OR5M11 | 1.00 | 17602 | 3 | | | | | OSGEPL1 | 1.00 |
| 17507 | 3 | | | | | | OR5M3 | 1.00 | 17603 | 3 | | | | | OSMR | 1.00 |
| 17508 | 3 | | | | | | OR5M8 | 1.00 | 17604 | 3 | | | | | OSR1 | 1.00 |
| 17509 | 3 | | | | | | OR5M9 | 1.00 | 17605 | 3 | | | | | OSR2 | 1.00 |
| 17510 | 3 | | | | | | OR5P2 | 1.00 | 17606 | 3 | | | | | OSTBETA | 1.00 |
| 17511 | 3 | | | | | | OR5P3 | 1.00 | 17607 | 3 | | | | | OSTN | 1.00 |
| 17512 | 3 | | | | | | OR5R1 | 1.00 | 17608 | 3 | | | | | OSTalpha | 1.00 |
| 17513 | 3 | | | | | | OR5T1 | 1.00 | 17609 | 3 | | | | | OTC | 1.00 |
| 17514 | 3 | | | | | | OR5T2 | 1.00 | 17610 | 3 | | | | | OTOA | 1.00 |
| 17515 | 3 | | | | | | OR5T3 | 1.00 | 17611 | 3 | | | | | OTOF | 1.00 |
| 17516 | 3 | | | | | | OR5V1 | 1.00 | 17612 | 3 | | | | | OTOGL | 1.00 |
| 17517 | 3 | | | | | | OR5W2 | 1.00 | 17613 | 3 | | | | | OTOL1 | 1.00 |
| 17518 | 3 | | | | | | OR6A2 | 1.00 | 17614 | 3 | | | | | OTOP1 | 1.00 |
| 17519 | 3 | | | | | | OR6B1 | 1.00 | 17615 | 3 | | | | | OTOP2 | 1.00 |
| 17520 | 3 | | | | | | OR6B2 | 1.00 | 17616 | 3 | | | | | OTOP3 | 1.00 |
| 17521 | 3 | | | | | | OR6B3 | 1.00 | 17617 | 3 | | | | | OTOR | 1.00 |
| 17522 | 3 | | | | | | OR6C1 | 1.00 | 17618 | 3 | | | | | OTOS | 1.00 |
| 17523 | 3 | | | | | | OR6C2 | 1.00 | 17619 | 3 | | | | | OTP | 1.00 |
| 17524 | 3 | | | | | | OR6C3 | 1.00 | 17620 | 3 | | | | | OTUB2 | 1.00 |
| 17525 | 3 | | | | | | OR6C4 | 1.00 | 17621 | 3 | | | | | OTUD6A | 1.00 |
| 17526 | 3 | | | | | | OR6C6 | 1.00 | 17622 | 3 | | | | | OTUD7A | 1.00 |
| 17527 | 3 | | | | | | OR6C65 | 1.00 | 17623 | 3 | | | | | OTX2 | 1.00 |
| 17528 | 3 | | | | | | OR6C68 | 1.00 | 17624 | 3 | | | | | OTX2OS1 | 1.00 |
| 17529 | 3 | | | | | | OR6C70 | 1.00 | 17625 | 3 | | | | | OVCH1 | 1.00 |
| 17530 | 3 | | | | | | OR6C74 | 1.00 | 17626 | 3 | | | | | OVCH2 | 1.00 |
| 17531 | 3 | | | | | | OR6C75 | 1.00 | 17627 | 3 | | | | | OVGP1 | 1.00 |
| 17532 | 3 | | | | | | OR6C76 | 1.00 | 17628 | 3 | | | | | OVOL1 | 1.00 |
| 17533 | 3 | | | | | | OR6F1 | 1.00 | 17629 | 3 | | | | | OVOL2 | 1.00 |
| 17534 | 3 | | | | | | OR6K2 | 1.00 | 17630 | 3 | | | | | OXCT2 | 1.00 |
| 17535 | 3 | | | | | | OR6K3 | 1.00 | 17631 | 3 | | | | | OXGR1 | 1.00 |
| 17536 | 3 | | | | | | OR6K6 | 1.00 | 17632 | 3 | | | | | OXT | 1.00 |
| 17537 | 3 | | | | | | OR6M1 | 1.00 | 17633 | 3 | | | | | OXTR | 1.00 |
| 17538 | 3 | | | | | | OR6N1 | 1.00 | 17634 | 3 | | | | | P2RX2 | 1.00 |
| 17539 | 3 | | | | | | OR6N2 | 1.00 | 17635 | 3 | | | | | P2RX3 | 1.00 |
| 17540 | 3 | | | | | | OR6P1 | 1.00 | 17636 | 3 | | | | | P2RX5-TAX1BP3 | 1.00 |
| 17541 | 3 | | | | | | OR6Q1 | 1.00 | 17637 | 3 | | | | | P2RX6 | 1.00 |
| 17542 | 3 | | | | | | OR6S1 | 1.00 | 17638 | 3 | | | | | P2RX6P | 1.00 |
| 17543 | 3 | | | | | | OR6T1 | 1.00 | 17639 | 3 | | | | | P2RY4 | 1.00 |
| 17544 | 3 | | | | | | OR6V1 | 1.00 | 17640 | 3 | | | | | P4HA2 | 1.00 |
| 17545 | 3 | | | | | | OR6W1P | 1.00 | 17641 | 3 | | | | | P4HA3 | 1.00 |
| 17546 | 3 | | | | | | OR6X1 | 1.00 | 17642 | 3 | | | | | PABPC1L2A | 1.00 |
| 17547 | 3 | | | | | | OR6Y1 | 1.00 | 17643 | 3 | | | | | PABPC1L2B | 1.00 |
| 17548 | 3 | | | | | | OR7A10 | 1.00 | 17644 | 3 | | | | | PABPC1P2 | 1.00 |
| 17549 | 3 | | | | | | OR7A17 | 1.00 | 17645 | 3 | | | | | PABPC4L | 1.00 |
| 17550 | 3 | | | | | | OR7A5 | 1.00 | 17646 | 3 | | | | | PABPC5 | 1.00 |
| 17551 | 3 | | | | | | OR7C1 | 1.00 | 17647 | 3 | | | | | PABPN1L | 1.00 |
| 17552 | 3 | | | | | | OR7C2 | 1.00 | 17648 | 3 | | | | | PACRG | 1.00 |
| 17553 | 3 | | | | | | OR7D2 | 1.00 | 17649 | 3 | | | | | PACSIN3 | 1.00 |
| 17554 | 3 | | | | | | OR7D4 | 1.00 | 17650 | 3 | | | | | PADI1 | 1.00 |
| 17555 | 3 | | | | | | OR7E12P | 1.00 | 17651 | 3 | | | | | PADI3 | 1.00 |
| 17556 | 3 | | | | | | OR7E14P | 1.00 | 17652 | 3 | | | | | PADI6 | 1.00 |
| 17557 | 3 | | | | | | OR7E156P | 1.00 | 17653 | 3 | | | | | PAEP | 1.00 |
| 17558 | 3 | | | | | | OR7E24 | 1.00 | 17654 | 3 | | | | | PAGE1 | 1.00 |
| 17559 | 3 | | | | | | OR7E2P | 1.00 | 17655 | 3 | | | | | PAGE2 | 1.00 |
| 17560 | 3 | | | | | | OR7E37P | 1.00 | 17656 | 3 | | | | | PAGE3 | 1.00 |
| 17561 | 3 | | | | | | OR7E5P | 1.00 | 17657 | 3 | | | | | PAGE4 | 1.00 |

Fig. 41 - 93

| | | | | | | | | | | | | | | |
|---|---|---|---|---|---|---|---|---|---|---|---|---|---|---|
| 17658 | 3 | | | | | PAGE5 | 1.00 | 17754 | 3 | | | | PCDHGA12 | 1.00 |
| 17659 | 3 | | | | | PAH | 1.00 | 17755 | 3 | | | | PCDHGA2 | 1.00 |
| 17660 | 3 | | | | | PAK3 | 1.00 | 17756 | 3 | | | | PCDHGA3 | 1.00 |
| 17661 | 3 | | | | | PAK6 | 1.00 | 17757 | 3 | | | | PCDHGA4 | 1.00 |
| 17662 | 3 | | | | | PAK7 | 1.00 | 17758 | 3 | | | | PCDHGA5 | 1.00 |
| 17663 | 3 | | | | | PALM | 1.00 | 17759 | 3 | | | | PCDHGA6 | 1.00 |
| 17664 | 3 | | | | | PALM2 | 1.00 | 17760 | 3 | | | | PCDHGA7 | 1.00 |
| 17665 | 3 | | | | | PALM2-AKAP2 | 1.00 | 17761 | 3 | | | | PCDHGA8 | 1.00 |
| 17666 | 3 | | | | | PALM3 | 1.00 | 17762 | 3 | | | | PCDHGA9 | 1.00 |
| 17667 | 3 | | | | | PALMD | 1.00 | 17763 | 3 | | | | PCDHGB1 | 1.00 |
| 17668 | 3 | | | | | PAMR1 | 1.00 | 17764 | 3 | | | | PCDHGB2 | 1.00 |
| 17669 | 3 | | | | | PANK1 | 1.00 | 17765 | 3 | | | | PCDHGB3 | 1.00 |
| 17670 | 3 | | | | | PANX3 | 1.00 | 17766 | 3 | | | | PCDHGB4 | 1.00 |
| 17671 | 3 | | | | | PAPL | 1.00 | 17767 | 3 | | | | PCDHGB5 | 1.00 |
| 17672 | 3 | | | | | PAPLN | 1.00 | 17768 | 3 | | | | PCDHGB6 | 1.00 |
| 17673 | 3 | | | | | PAPPA | 1.00 | 17769 | 3 | | | | PCDHGB7 | 1.00 |
| 17674 | 3 | | | | | PAPPA2 | 1.00 | 17770 | 3 | | | | PCDHGB8P | 1.00 |
| 17675 | 3 | | | | | PAQR5 | 1.00 | 17771 | 3 | | | | PCDHGC3 | 1.00 |
| 17676 | 3 | | | | | PAQR9 | 1.00 | 17772 | 3 | | | | PCDHGC4 | 1.00 |
| 17677 | 3 | | | | | PAR1 | 1.00 | 17773 | 3 | | | | PCDHGC5 | 1.00 |
| 17678 | 3 | | | | | PAR4 | 1.00 | 17774 | 3 | | | | PCDP1 | 1.00 |
| 17679 | 3 | | | | | PARD3 | 1.00 | 17775 | 3 | | | | PCGEM1 | 1.00 |
| 17680 | 3 | | | | | PARD3B | 1.00 | 17776 | 3 | | | | PCGF2 | 1.00 |
| 17681 | 3 | | | | | PARD6B | 1.00 | 17777 | 3 | | | | PCK1 | 1.00 |
| 17682 | 3 | | | | | PARD6G | 1.00 | 17778 | 3 | | | | PCLO | 1.00 |
| 17683 | 3 | | | | | PARK2 | 1.00 | 17779 | 3 | | | | PCNAP1 | 1.00 |
| 17684 | 3 | | | | | PARPBP | 1.00 | 17780 | 3 | | | | PCOLCE | 1.00 |
| 17685 | 3 | | | | | PART1 | 1.00 | 17781 | 3 | | | | PCOLCE2 | 1.00 |
| 17686 | 3 | | | | | PARVA | 1.00 | 17782 | 3 | | | | PCP4 | 1.00 |
| 17687 | 3 | | | | | PASD1 | 1.00 | 17783 | 3 | | | | PCP4L1 | 1.00 |
| 17688 | 3 | | | | | PATE1 | 1.00 | 17784 | 3 | | | | PCSK1 | 1.00 |
| 17689 | 3 | | | | | PATE2 | 1.00 | 17785 | 3 | | | | PCSK2 | 1.00 |
| 17690 | 3 | | | | | PATE3 | 1.00 | 17786 | 3 | | | | PCSK4 | 1.00 |
| 17691 | 3 | | | | | PATE4 | 1.00 | 17787 | 3 | | | | PCSK9 | 1.00 |
| 17692 | 3 | | | | | PAWR | 1.00 | 17788 | 3 | | | | PDC | 1.00 |
| 17693 | 3 | | | | | PAX1 | 1.00 | 17789 | 3 | | | | PDCL2 | 1.00 |
| 17694 | 3 | | | | | PAX2 | 1.00 | 17790 | 3 | | | | PDE10A | 1.00 |
| 17695 | 3 | | | | | PAX3 | 1.00 | 17791 | 3 | | | | PDE11A | 1.00 |
| 17696 | 3 | | | | | PAX4 | 1.00 | 17792 | 3 | | | | PDE1A | 1.00 |
| 17697 | 3 | | | | | PAX6 | 1.00 | 17793 | 3 | | | | PDE1C | 1.00 |
| 17698 | 3 | | | | | PAX7 | 1.00 | 17794 | 3 | | | | PDE2A | 1.00 |
| 17699 | 3 | | | | | PAX8 | 1.00 | 17795 | 3 | | | | PDE3A | 1.00 |
| 17700 | 3 | | | | | PAX9 | 1.00 | 17796 | 3 | | | | PDE4C | 1.00 |
| 17701 | 3 | | | | | PBK | 1.00 | 17797 | 3 | | | | PDE6A | 1.00 |
| 17702 | 3 | | | | | PBOV1 | 1.00 | 17798 | 3 | | | | PDE6C | 1.00 |
| 17703 | 3 | | | | | PCA3 | 1.00 | 17799 | 3 | | | | PDE6H | 1.00 |
| 17704 | 3 | | | | | PCAT1 | 1.00 | 17800 | 3 | | | | PDE7B | 1.00 |
| 17705 | 3 | | | | | PCBP3 | 1.00 | 17801 | 3 | | | | PDE8B | 1.00 |
| 17706 | 3 | | | | | PCCA | 1.00 | 17802 | 3 | | | | PDE9A | 1.00 |
| 17707 | 3 | | | | | PCDH10 | 1.00 | 17803 | 3 | | | | PDGFRA | 1.00 |
| 17708 | 3 | | | | | PCDH11X | 1.00 | 17804 | 3 | | | | PDGFRL | 1.00 |
| 17709 | 3 | | | | | PCDH11Y | 1.00 | 17805 | 3 | | | | PDIA2 | 1.00 |
| 17710 | 3 | | | | | PCDH15 | 1.00 | 17806 | 3 | | | | PDIA5 | 1.00 |
| 17711 | 3 | | | | | PCDH17 | 1.00 | 17807 | 3 | | | | PDILT | 1.00 |
| 17712 | 3 | | | | | PCDH18 | 1.00 | 17808 | 3 | | | | PDLIM3 | 1.00 |
| 17713 | 3 | | | | | PCDH19 | 1.00 | 17809 | 3 | | | | PDLIM4 | 1.00 |
| 17714 | 3 | | | | | PCDH20 | 1.00 | 17810 | 3 | | | | PDPN | 1.00 |
| 17715 | 3 | | | | | PCDH7 | 1.00 | 17811 | 3 | | | | PDX1 | 1.00 |
| 17716 | 3 | | | | | PCDH8 | 1.00 | 17812 | 3 | | | | PDYN | 1.00 |
| 17717 | 3 | | | | | PCDHA1 | 1.00 | 17813 | 3 | | | | PDZD2 | 1.00 |
| 17718 | 3 | | | | | PCDHA10 | 1.00 | 17814 | 3 | | | | PDZD3 | 1.00 |
| 17719 | 3 | | | | | PCDHA11 | 1.00 | 17815 | 3 | | | | PDZD7 | 1.00 |
| 17720 | 3 | | | | | PCDHA12 | 1.00 | 17816 | 3 | | | | PDZD9 | 1.00 |
| 17721 | 3 | | | | | PCDHA13 | 1.00 | 17817 | 3 | | | | PDZK1 | 1.00 |
| 17722 | 3 | | | | | PCDHA2 | 1.00 | 17818 | 3 | | | | PDZK1P1 | 1.00 |
| 17723 | 3 | | | | | PCDHA3 | 1.00 | 17819 | 3 | | | | PDZRN3 | 1.00 |
| 17724 | 3 | | | | | PCDHA4 | 1.00 | 17820 | 3 | | | | PDZRN4 | 1.00 |
| 17725 | 3 | | | | | PCDHA5 | 1.00 | 17821 | 3 | | | | PEBP4 | 1.00 |
| 17726 | 3 | | | | | PCDHA6 | 1.00 | 17822 | 3 | | | | PEG10 | 1.00 |
| 17727 | 3 | | | | | PCDHA7 | 1.00 | 17823 | 3 | | | | PEG3 | 1.00 |
| 17728 | 3 | | | | | PCDHA8 | 1.00 | 17824 | 3 | | | | PEG3-AS1 | 1.00 |
| 17729 | 3 | | | | | PCDHA9 | 1.00 | 17825 | 3 | | | | PENK | 1.00 |
| 17730 | 3 | | | | | PCDHAC1 | 1.00 | 17826 | 3 | | | | PER4 | 1.00 |
| 17731 | 3 | | | | | PCDHAC2 | 1.00 | 17827 | 3 | | | | PEX11G | 1.00 |
| 17732 | 3 | | | | | PCDHB1 | 1.00 | 17828 | 3 | | | | PEX5L | 1.00 |
| 17733 | 3 | | | | | PCDHB10 | 1.00 | 17829 | 3 | | | | PFKFB1 | 1.00 |
| 17734 | 3 | | | | | PCDHB11 | 1.00 | 17830 | 3 | | | | PFN1P2 | 1.00 |
| 17735 | 3 | | | | | PCDHB12 | 1.00 | 17831 | 3 | | | | PFN3 | 1.00 |
| 17736 | 3 | | | | | PCDHB13 | 1.00 | 17832 | 3 | | | | PFN4 | 1.00 |
| 17737 | 3 | | | | | PCDHB14 | 1.00 | 17833 | 3 | | | | PGA5 | 1.00 |
| 17738 | 3 | | | | | PCDHB15 | 1.00 | 17834 | 3 | | | | PGAP1 | 1.00 |
| 17739 | 3 | | | | | PCDHB16 | 1.00 | 17835 | 3 | | | | PGBD1 | 1.00 |
| 17740 | 3 | | | | | PCDHB17 | 1.00 | 17836 | 3 | | | | PGBD4 | 1.00 |
| 17741 | 3 | | | | | PCDHB18 | 1.00 | 17837 | 3 | | | | PGBD5 | 1.00 |
| 17742 | 3 | | | | | PCDHB19P | 1.00 | 17838 | 3 | | | | PGC | 1.00 |
| 17743 | 3 | | | | | PCDHB2 | 1.00 | 17839 | 3 | | | | PGCP1 | 1.00 |
| 17744 | 3 | | | | | PCDHB3 | 1.00 | 17840 | 3 | | | | PGF | 1.00 |
| 17745 | 3 | | | | | PCDHB4 | 1.00 | 17841 | 3 | | | | PGK2 | 1.00 |
| 17746 | 3 | | | | | PCDHB5 | 1.00 | 17842 | 3 | | | | PGLYRP2 | 1.00 |
| 17747 | 3 | | | | | PCDHB6 | 1.00 | 17843 | 3 | | | | PGLYRP3 | 1.00 |
| 17748 | 3 | | | | | PCDHB7 | 1.00 | 17844 | 3 | | | | PGLYRP4 | 1.00 |
| 17749 | 3 | | | | | PCDHB8 | 1.00 | 17845 | 3 | | | | PGM5P2 | 1.00 |
| 17750 | 3 | | | | | PCDHB9 | 1.00 | 17846 | 3 | | | | PGPEP1L | 1.00 |
| 17751 | 3 | | | | | PCDHGA1 | 1.00 | 17847 | 3 | | | | PGR | 1.00 |
| 17752 | 3 | | | | | PCDHGA10 | 1.00 | 17848 | 3 | | | | PHACTR3 | 1.00 |
| 17753 | 3 | | | | | PCDHGA11 | 1.00 | 17849 | 3 | | | | PHEX | 1.00 |

Fig. 41 - 94

| | | | | | | | |
|---|---|---|---|---|---|---|---|
| 17850 | 3 | | | | PHF16 | | 1.00 |
| 17851 | 3 | | | | PHF21B | | 1.00 |
| 17852 | 3 | | | | PHF2P1 | | 1.00 |
| 17853 | 3 | | | | PHGR1 | | 1.00 |
| 17854 | 3 | | | | PHKA1 | | 1.00 |
| 17855 | 3 | | | | PHKG1 | | 1.00 |
| 17856 | 3 | | | | PHLDA2 | | 1.00 |
| 17857 | 3 | | | | PHLDB1 | | 1.00 |
| 17858 | 3 | | | | PHOSPHO2-KLHL23 | | 1.00 |
| 17859 | 3 | | | | PHOX2A | | 1.00 |
| 17860 | 3 | | | | PHOX2B | | 1.00 |
| 17861 | 3 | | | | PHYHD1 | | 1.00 |
| 17862 | 3 | | | | PHYHIP | | 1.00 |
| 17863 | 3 | | | | PHYHIPL | | 1.00 |
| 17864 | 3 | | | | PI15 | | 1.00 |
| 17865 | 3 | | | | PIEZO2 | | 1.00 |
| 17866 | 3 | | | | PIF1 | | 1.00 |
| 17867 | 3 | | | | PIGR | | 1.00 |
| 17868 | 3 | | | | PIGZ | | 1.00 |
| 17869 | 3 | | | | PIH1D2 | | 1.00 |
| 17870 | 3 | | | | PIK3C2G | | 1.00 |
| 17871 | 3 | | | | PIP | | 1.00 |
| 17872 | 3 | | | | PIPSKL1 | | 1.00 |
| 17873 | 3 | | | | PIPOX | | 1.00 |
| 17874 | 3 | | | | PIR | | 1.00 |
| 17875 | 3 | | | | PIR-FIGF | | 1.00 |
| 17876 | 3 | | | | PIRT | | 1.00 |
| 17877 | 3 | | | | PISRT1 | | 1.00 |
| 17878 | 3 | | | | PITPNM3 | | 1.00 |
| 17879 | 3 | | | | PITX1 | | 1.00 |
| 17880 | 3 | | | | PITX2 | | 1.00 |
| 17881 | 3 | | | | PITX3 | | 1.00 |
| 17882 | 3 | | | | PIWIL1 | | 1.00 |
| 17883 | 3 | | | | PIWIL2 | | 1.00 |
| 17884 | 3 | | | | PIWIL3 | | 1.00 |
| 17885 | 3 | | | | PIWIL4 | | 1.00 |
| 17886 | 3 | | | | PKD1L1 | | 1.00 |
| 17887 | 3 | | | | PKD1L2 | | 1.00 |
| 17888 | 3 | | | | PKD1L3 | | 1.00 |
| 17889 | 3 | | | | PKD2L1 | | 1.00 |
| 17890 | 3 | | | | PKD2L2 | | 1.00 |
| 17891 | 3 | | | | PKDCC | | 1.00 |
| 17892 | 3 | | | | PKDREJ | | 1.00 |
| 17893 | 3 | | | | PKHD1 | | 1.00 |
| 17894 | 3 | | | | PKHD1L1 | | 1.00 |
| 17895 | 3 | | | | PKIB | | 1.00 |
| 17896 | 3 | | | | PKLR | | 1.00 |
| 17897 | 3 | | | | PKMYT1 | | 1.00 |
| 17898 | 3 | | | | PKN3 | | 1.00 |
| 17899 | 3 | | | | PKNOX2 | | 1.00 |
| 17900 | 3 | | | | PKP1 | | 1.00 |
| 17901 | 3 | | | | PKP3 | | 1.00 |
| 17902 | 3 | | | | PLA1A | | 1.00 |
| 17903 | 3 | | | | PLA2G10 | | 1.00 |
| 17904 | 3 | | | | PLA2G12B | | 1.00 |
| 17905 | 3 | | | | PLA2G1B | | 1.00 |
| 17906 | 3 | | | | PLA2G2A | | 1.00 |
| 17907 | 3 | | | | PLA2G2C | | 1.00 |
| 17908 | 3 | | | | PLA2G2D | | 1.00 |
| 17909 | 3 | | | | PLA2G2E | | 1.00 |
| 17910 | 3 | | | | PLA2G2F | | 1.00 |
| 17911 | 3 | | | | PLA2G3 | | 1.00 |
| 17912 | 3 | | | | PLA2G4D | | 1.00 |
| 17913 | 3 | | | | PLA2G4E | | 1.00 |
| 17914 | 3 | | | | PLA2G4F | | 1.00 |
| 17915 | 3 | | | | PLA2G5 | | 1.00 |
| 17916 | 3 | | | | PLA2R1 | | 1.00 |
| 17917 | 3 | | | | PLAC1 | | 1.00 |
| 17918 | 3 | | | | PLAC1L | | 1.00 |
| 17919 | 3 | | | | PLAC2 | | 1.00 |
| 17920 | 3 | | | | PLAC4 | | 1.00 |
| 17921 | 3 | | | | PLAC8L1 | | 1.00 |
| 17922 | 3 | | | | PLAC9 | | 1.00 |
| 17923 | 3 | | | | PLAT | | 1.00 |
| 17924 | 3 | | | | PLAU | | 1.00 |
| 17925 | 3 | | | | PLCB4 | | 1.00 |
| 17926 | 3 | | | | PLCD4 | | 1.00 |
| 17927 | 3 | | | | PLCE1 | | 1.00 |
| 17928 | 3 | | | | PLCH1 | | 1.00 |
| 17929 | 3 | | | | PLCH2 | | 1.00 |
| 17930 | 3 | | | | PLCXD3 | | 1.00 |
| 17931 | 3 | | | | PLCZ1 | | 1.00 |
| 17932 | 3 | | | | PLD5 | | 1.00 |
| 17933 | 3 | | | | PLEKHA4 | | 1.00 |
| 17934 | 3 | | | | PLEKHA5 | | 1.00 |
| 17935 | 3 | | | | PLEKHA6 | | 1.00 |
| 17936 | 3 | | | | PLEKHA7 | | 1.00 |
| 17937 | 3 | | | | PLEKHD1 | | 1.00 |
| 17938 | 3 | | | | PLEKHG4 | | 1.00 |
| 17939 | 3 | | | | PLEKHG4B | | 1.00 |
| 17940 | 3 | | | | PLEKHG5 | | 1.00 |
| 17941 | 3 | | | | PLEKHG6 | | 1.00 |
| 17942 | 3 | | | | PLEKHG7 | | 1.00 |
| 17943 | 3 | | | | PLEKHH1 | | 1.00 |
| 17944 | 3 | | | | PLEKHH2 | | 1.00 |
| 17945 | 3 | | | | PLEKHH3 | | 1.00 |
| 17946 | 3 | | | | PLEKHN1 | | 1.00 |
| 17947 | 3 | | | | PLG | | 1.00 |
| 17948 | 3 | | | | PLGLA | | 1.00 |
| 17949 | 3 | | | | PLGLB1 | | 1.00 |
| 17950 | 3 | | | | PLGLB2 | | 1.00 |
| 17951 | 3 | | | | PLIN1 | | 1.00 |
| 17952 | 3 | | | | PLK1 | | 1.00 |
| 17953 | 3 | | | | PLK2 | | 1.00 |
| 17954 | 3 | | | | PLK4 | | 1.00 |
| 17955 | 3 | | | | PLK5 | | 1.00 |
| 17956 | 3 | | | | PLLP | | 1.00 |
| 17957 | 3 | | | | PLN | | 1.00 |
| 17958 | 3 | | | | PLOD2 | | 1.00 |
| 17959 | 3 | | | | PLP1 | | 1.00 |
| 17960 | 3 | | | | PLS1 | | 1.00 |
| 17961 | 3 | | | | PLS3 | | 1.00 |
| 17962 | 3 | | | | PLSCR2 | | 1.00 |
| 17963 | 3 | | | | PLSCR4 | | 1.00 |
| 17964 | 3 | | | | PLSCR5 | | 1.00 |
| 17965 | 3 | | | | PLTP | | 1.00 |
| 17966 | 3 | | | | PLXNA2 | | 1.00 |
| 17967 | 3 | | | | PLXNA4 | | 1.00 |
| 17968 | 3 | | | | PLXNB1 | | 1.00 |
| 17969 | 3 | | | | PLXNB3 | | 1.00 |
| 17970 | 3 | | | | PM20D1 | | 1.00 |
| 17971 | 3 | | | | PMCH | | 1.00 |
| 17972 | 3 | | | | PMCHL1 | | 1.00 |
| 17973 | 3 | | | | PMCHL2 | | 1.00 |
| 17974 | 3 | | | | PMEL | | 1.00 |
| 17975 | 3 | | | | PMFBP1 | | 1.00 |
| 17976 | 3 | | | | PMP2 | | 1.00 |
| 17977 | 3 | | | | PMS2P4 | | 1.00 |
| 17978 | 3 | | | | PMS2P5 | | 1.00 |
| 17979 | 3 | | | | PNCK | | 1.00 |
| 17980 | 3 | | | | PNLDC1 | | 1.00 |
| 17981 | 3 | | | | PNLIP | | 1.00 |
| 17982 | 3 | | | | PNLIPRP1 | | 1.00 |
| 17983 | 3 | | | | PNLIPRP2 | | 1.00 |
| 17984 | 3 | | | | PNLIPRP3 | | 1.00 |
| 17985 | 3 | | | | PNMA2 | | 1.00 |
| 17986 | 3 | | | | PNMA3 | | 1.00 |
| 17987 | 3 | | | | PNMA5 | | 1.00 |
| 17988 | 3 | | | | PNMA6A | | 1.00 |
| 17989 | 3 | | | | PNMA6C | | 1.00 |
| 17990 | 3 | | | | PNMA6D | | 1.00 |
| 17991 | 3 | | | | PNMAL1 | | 1.00 |
| 17992 | 3 | | | | PNMAL2 | | 1.00 |
| 17993 | 3 | | | | PNMT | | 1.00 |
| 17994 | 3 | | | | PNPLA3 | | 1.00 |
| 17995 | 3 | | | | PNPLA5 | | 1.00 |
| 17996 | 3 | | | | PNPLA7 | | 1.00 |
| 17997 | 3 | | | | POC1A | | 1.00 |
| 17998 | 3 | | | | POC1B-GALNT4 | | 1.00 |
| 17999 | 3 | | | | PODN | | 1.00 |
| 18000 | 3 | | | | PODNL1 | | 1.00 |
| 18001 | 3 | | | | PODXL | | 1.00 |
| 18002 | 3 | | | | POF1B | | 1.00 |
| 18003 | 3 | | | | POLE2 | | 1.00 |
| 18004 | 3 | | | | POLN | | 1.00 |
| 18005 | 3 | | | | POLQ | | 1.00 |
| 18006 | 3 | | | | POLR3G | | 1.00 |
| 18007 | 3 | | | | POM121L10P | | 1.00 |
| 18008 | 3 | | | | POM121L12 | | 1.00 |
| 18009 | 3 | | | | POM121L1P | | 1.00 |
| 18010 | 3 | | | | POM121L2 | | 1.00 |
| 18011 | 3 | | | | POM121L4P | | 1.00 |
| 18012 | 3 | | | | POM121L8P | | 1.00 |
| 18013 | 3 | | | | POM121L9P | | 1.00 |
| 18014 | 3 | | | | POMT2 | | 1.00 |
| 18015 | 3 | | | | PON1 | | 1.00 |
| 18016 | 3 | | | | PON3 | | 1.00 |
| 18017 | 3 | | | | POPDC3 | | 1.00 |
| 18018 | 3 | | | | POSTN | | 1.00 |
| 18019 | 3 | | | | POTEA | | 1.00 |
| 18020 | 3 | | | | POTEB | | 1.00 |
| 18021 | 3 | | | | POTEC | | 1.00 |
| 18022 | 3 | | | | POTED | | 1.00 |
| 18023 | 3 | | | | POTEG | | 1.00 |
| 18024 | 3 | | | | POTEH | | 1.00 |
| 18025 | 3 | | | | POU1F1 | | 1.00 |
| 18026 | 3 | | | | POU2F3 | | 1.00 |
| 18027 | 3 | | | | POU3F1 | | 1.00 |
| 18028 | 3 | | | | POU3F2 | | 1.00 |
| 18029 | 3 | | | | POU3F3 | | 1.00 |
| 18030 | 3 | | | | POU3F4 | | 1.00 |
| 18031 | 3 | | | | POU4F1 | | 1.00 |
| 18032 | 3 | | | | POU4F2 | | 1.00 |
| 18033 | 3 | | | | POU4F3 | | 1.00 |
| 18034 | 3 | | | | POU5F1 | | 1.00 |
| 18035 | 3 | | | | POU5F1B | | 1.00 |
| 18036 | 3 | | | | POU5F1P4 | | 1.00 |
| 18037 | 3 | | | | POU5F2 | | 1.00 |
| 18038 | 3 | | | | POU6F2 | | 1.00 |
| 18039 | 3 | | | | PP12613 | | 1.00 |
| 18040 | 3 | | | | PP14571 | | 1.00 |

Fig. 41 - 95

| | | | | | | | | | | | | |
|---|---|---|---|---|---|---|---|---|---|---|---|---|
| 18041 | 3 | | | | | PP2D1 | 1.00 | 18137 | 3 | | PRH1-PRR4 | 1.00 |
| 18042 | 3 | | | | | PPAN-P2RY11 | 1.00 | 18138 | 3 | | PRH2 | 1.00 |
| 18043 | 3 | | | | | PPAP2B | 1.00 | 18139 | 3 | | PRHOXNB | 1.00 |
| 18044 | 3 | | | | | PPAP2C | 1.00 | 18140 | 3 | | PRICKLE2 | 1.00 |
| 18045 | 3 | | | | | PPAPDC1A | 1.00 | 18141 | 3 | | PRIMA1 | 1.00 |
| 18046 | 3 | | | | | PPAPDC3 | 1.00 | 18142 | 3 | | PRINS | 1.00 |
| 18047 | 3 | | | | | PPARGC1A | 1.00 | 18143 | 3 | | PRKAA2 | 1.00 |
| 18048 | 3 | | | | | PPBPL2 | 1.00 | 18144 | 3 | | PRKAG3 | 1.00 |
| 18049 | 3 | | | | | PPEF1 | 1.00 | 18145 | 3 | | PRKCG | 1.00 |
| 18050 | 3 | | | | | PPEF2 | 1.00 | 18146 | 3 | | PRKD1 | 1.00 |
| 18051 | 3 | | | | | PPFIA2 | 1.00 | 18147 | 3 | | PRKG1 | 1.00 |
| 18052 | 3 | | | | | PPFIA3 | 1.00 | 18148 | 3 | | PRKG2 | 1.00 |
| 18053 | 3 | | | | | PPFIA4 | 1.00 | 18149 | 3 | | PRL | 1.00 |
| 18054 | 3 | | | | | PPFIBP1 | 1.00 | 18150 | 3 | | PRLH | 1.00 |
| 18055 | 3 | | | | | PPIAL4B | 1.00 | 18151 | 3 | | PRLHR | 1.00 |
| 18056 | 3 | | | | | PPIAL4C | 1.00 | 18152 | 3 | | PRLR | 1.00 |
| 18057 | 3 | | | | | PPIAL4D | 1.00 | 18153 | 3 | | PRM1 | 1.00 |
| 18058 | 3 | | | | | PPIAL4E | 1.00 | 18154 | 3 | | PRM2 | 1.00 |
| 18059 | 3 | | | | | PPIAL4G | 1.00 | 18155 | 3 | | PRM3 | 1.00 |
| 18060 | 3 | | | | | PPIC | 1.00 | 18156 | 3 | | PRMT8 | 1.00 |
| 18061 | 3 | | | | | PPIH | 1.00 | 18157 | 3 | | PRND | 1.00 |
| 18062 | 3 | | | | | PPIL6 | 1.00 | 18158 | 3 | | PRNT | 1.00 |
| 18063 | 3 | | | | | PPL | 1.00 | 18159 | 3 | | PRO0611 | 1.00 |
| 18064 | 3 | | | | | PPM1E | 1.00 | 18160 | 3 | | PRO1768 | 1.00 |
| 18065 | 3 | | | | | PPM1J | 1.00 | 18161 | 3 | | PROC | 1.00 |
| 18066 | 3 | | | | | PPP1R13L | 1.00 | 18162 | 3 | | PRODH | 1.00 |
| 18067 | 3 | | | | | PPP1R14C | 1.00 | 18163 | 3 | | PRODH2 | 1.00 |
| 18068 | 3 | | | | | PPP1R14D | 1.00 | 18164 | 3 | | PROK1 | 1.00 |
| 18069 | 3 | | | | | PPP1R17 | 1.00 | 18165 | 3 | | PROKR1 | 1.00 |
| 18070 | 3 | | | | | PPP1R1A | 1.00 | 18166 | 3 | | PROKR2 | 1.00 |
| 18071 | 3 | | | | | PPP1R1B | 1.00 | 18167 | 3 | | PROL1 | 1.00 |
| 18072 | 3 | | | | | PPP1R1C | 1.00 | 18168 | 3 | | PROM1 | 1.00 |
| 18073 | 3 | | | | | PPP1R27 | 1.00 | 18169 | 3 | | PROM2 | 1.00 |
| 18074 | 3 | | | | | PPP1R2P9 | 1.00 | 18170 | 3 | | PROP1 | 1.00 |
| 18075 | 3 | | | | | PPP1R32 | 1.00 | 18171 | 3 | | PROX1 | 1.00 |
| 18076 | 3 | | | | | PPP1R36 | 1.00 | 18172 | 3 | | PROX1-AS1 | 1.00 |
| 18077 | 3 | | | | | PPP1R3A | 1.00 | 18173 | 3 | | PROX2 | 1.00 |
| 18078 | 3 | | | | | PPP1R3C | 1.00 | 18174 | 3 | | PROZ | 1.00 |
| 18079 | 3 | | | | | PPP1R3G | 1.00 | 18175 | 3 | | PRPF40B | 1.00 |
| 18080 | 3 | | | | | PPP1R42 | 1.00 | 18176 | 3 | | PRPH | 1.00 |
| 18081 | 3 | | | | | PPP1R9A | 1.00 | 18177 | 3 | | PRPH2 | 1.00 |
| 18082 | 3 | | | | | PPP2R2C | 1.00 | 18178 | 3 | | PRR15 | 1.00 |
| 18083 | 3 | | | | | PPP2R3A | 1.00 | 18179 | 3 | | PRR15L | 1.00 |
| 18084 | 3 | | | | | PPP2R3B | 1.00 | 18180 | 3 | | PRR16 | 1.00 |
| 18085 | 3 | | | | | PPP3R2 | 1.00 | 18181 | 3 | | PRR18 | 1.00 |
| 18086 | 3 | | | | | PPP4R4 | 1.00 | 18182 | 3 | | PRR19 | 1.00 |
| 18087 | 3 | | | | | PPT2-EGFL8 | 1.00 | 18183 | 3 | | PRR20B | 1.00 |
| 18088 | 3 | | | | | PPY | 1.00 | 18184 | 3 | | PRR20D | 1.00 |
| 18089 | 3 | | | | | PPY2 | 1.00 | 18185 | 3 | | PRR20E | 1.00 |
| 18090 | 3 | | | | | PPYR1 | 1.00 | 18186 | 3 | | PRR21 | 1.00 |
| 18091 | 3 | | | | | PRAC | 1.00 | 18187 | 3 | | PRR22 | 1.00 |
| 18092 | 3 | | | | | PRAME | 1.00 | 18188 | 3 | | PRR23A | 1.00 |
| 18093 | 3 | | | | | PRAMEF1 | 1.00 | 18189 | 3 | | PRR23B | 1.00 |
| 18094 | 3 | | | | | PRAMEF10 | 1.00 | 18190 | 3 | | PRR23C | 1.00 |
| 18095 | 3 | | | | | PRAMEF11 | 1.00 | 18191 | 3 | | PRR25 | 1.00 |
| 18096 | 3 | | | | | PRAMEF12 | 1.00 | 18192 | 3 | | PRR5-ARHGAP8 | 1.00 |
| 18097 | 3 | | | | | PRAMEF13 | 1.00 | 18193 | 3 | | PRR9 | 1.00 |
| 18098 | 3 | | | | | PRAMEF14 | 1.00 | 18194 | 3 | | PRRG1 | 1.00 |
| 18099 | 3 | | | | | PRAMEF15 | 1.00 | 18195 | 3 | | PRRG2 | 1.00 |
| 18100 | 3 | | | | | PRAMEF16 | 1.00 | 18196 | 3 | | PRRG3 | 1.00 |
| 18101 | 3 | | | | | PRAMEF17 | 1.00 | 18197 | 3 | | PRRT1 | 1.00 |
| 18102 | 3 | | | | | PRAMEF18 | 1.00 | 18198 | 3 | | PRRT2 | 1.00 |
| 18103 | 3 | | | | | PRAMEF19 | 1.00 | 18199 | 3 | | PRRT4 | 1.00 |
| 18104 | 3 | | | | | PRAMEF2 | 1.00 | 18200 | 3 | | PRRX1 | 1.00 |
| 18105 | 3 | | | | | PRAMEF20 | 1.00 | 18201 | 3 | | PRRX2 | 1.00 |
| 18106 | 3 | | | | | PRAMEF21 | 1.00 | 18202 | 3 | | PRSS1 | 1.00 |
| 18107 | 3 | | | | | PRAMEF22 | 1.00 | 18203 | 3 | | PRSS12 | 1.00 |
| 18108 | 3 | | | | | PRAMEF3 | 1.00 | 18204 | 3 | | PRSS16 | 1.00 |
| 18109 | 3 | | | | | PRAMEF4 | 1.00 | 18205 | 3 | | PRSS2 | 1.00 |
| 18110 | 3 | | | | | PRAMEF5 | 1.00 | 18206 | 3 | | PRSS22 | 1.00 |
| 18111 | 3 | | | | | PRAMEF6 | 1.00 | 18207 | 3 | | PRSS27 | 1.00 |
| 18112 | 3 | | | | | PRAMEF7 | 1.00 | 18208 | 3 | | PRSS3 | 1.00 |
| 18113 | 3 | | | | | PRAMEF8 | 1.00 | 18209 | 3 | | PRSS35 | 1.00 |
| 18114 | 3 | | | | | PRAMEF9 | 1.00 | 18210 | 3 | | PRSS36 | 1.00 |
| 18115 | 3 | | | | | PRAP1 | 1.00 | 18211 | 3 | | PRSS37 | 1.00 |
| 18116 | 3 | | | | | PRB1 | 1.00 | 18212 | 3 | | PRSS38 | 1.00 |
| 18117 | 3 | | | | | PRB2 | 1.00 | 18213 | 3 | | PRSS41 | 1.00 |
| 18118 | 3 | | | | | PRB3 | 1.00 | 18214 | 3 | | PRSS42 | 1.00 |
| 18119 | 3 | | | | | PRB4 | 1.00 | 18215 | 3 | | PRSS45 | 1.00 |
| 18120 | 3 | | | | | PRCD | 1.00 | 18216 | 3 | | PRSS46 | 1.00 |
| 18121 | 3 | | | | | PRDM11 | 1.00 | 18217 | 3 | | PRSS48 | 1.00 |
| 18122 | 3 | | | | | PRDM12 | 1.00 | 18218 | 3 | | PRSS50 | 1.00 |
| 18123 | 3 | | | | | PRDM13 | 1.00 | 18219 | 3 | | PRSS54 | 1.00 |
| 18124 | 3 | | | | | PRDM14 | 1.00 | 18220 | 3 | | PRSS55 | 1.00 |
| 18125 | 3 | | | | | PRDM16 | 1.00 | 18221 | 3 | | PRSS56 | 1.00 |
| 18126 | 3 | | | | | PRDM6 | 1.00 | 18222 | 3 | | PRSS58 | 1.00 |
| 18127 | 3 | | | | | PRDM7 | 1.00 | 18223 | 3 | | PRSS8 | 1.00 |
| 18128 | 3 | | | | | PRDM9 | 1.00 | 18224 | 3 | | PRTFDC1 | 1.00 |
| 18129 | 3 | | | | | PRELID2 | 1.00 | 18225 | 3 | | PRTG | 1.00 |
| 18130 | 3 | | | | | PRELP | 1.00 | 18226 | 3 | | PRUNE2 | 1.00 |
| 18131 | 3 | | | | | PREX2 | 1.00 | 18227 | 3 | | PRY | 1.00 |
| 18132 | 3 | | | | | PRG1 | 1.00 | 18228 | 3 | | PSAPL1 | 1.00 |
| 18133 | 3 | | | | | PRG2 | 1.00 | 18229 | 3 | | PSCA | 1.00 |
| 18134 | 3 | | | | | PRG3 | 1.00 | 18230 | 3 | | PSD | 1.00 |
| 18135 | 3 | | | | | PRG4 | 1.00 | 18231 | 3 | | PSD2 | 1.00 |
| 18136 | 3 | | | | | PRH1 | 1.00 | 18232 | 3 | | PSD3 | 1.00 |

Fig. 41 - 96

| | | | | | | | | |
|---|---|---|---|---|---|---|---|---|
| 18233 | 3 | | | | | PSG1 | 1.00 |
| 18234 | 3 | | | | | PSG10P | 1.00 |
| 18235 | 3 | | | | | PSG11 | 1.00 |
| 18236 | 3 | | | | | PSG2 | 1.00 |
| 18237 | 3 | | | | | PSG3 | 1.00 |
| 18238 | 3 | | | | | PSG4 | 1.00 |
| 18239 | 3 | | | | | PSG5 | 1.00 |
| 18240 | 3 | | | | | PSG6 | 1.00 |
| 18241 | 3 | | | | | PSG7 | 1.00 |
| 18242 | 3 | | | | | PSG8 | 1.00 |
| 18243 | 3 | | | | | PSG9 | 1.00 |
| 18244 | 3 | | | | | PSKH2 | 1.00 |
| 18245 | 3 | | | | | PSMA8 | 1.00 |
| 18246 | 3 | | | | | PSMB11 | 1.00 |
| 18247 | 3 | | | | | PSMC3IP | 1.00 |
| 18248 | 3 | | | | | PSORS1C1 | 1.00 |
| 18249 | 3 | | | | | PSORS1C2 | 1.00 |
| 18250 | 3 | | | | | PSORS1C3 | 1.00 |
| 18251 | 3 | | | | | PSTK | 1.00 |
| 18252 | 3 | | | | | PTCH2 | 1.00 |
| 18253 | 3 | | | | | PTCHD1 | 1.00 |
| 18254 | 3 | | | | | PTCHD2 | 1.00 |
| 18255 | 3 | | | | | PTCHD3 | 1.00 |
| 18256 | 3 | | | | | PTCHD4 | 1.00 |
| 18257 | 3 | | | | | PTF1A | 1.00 |
| 18258 | 3 | | | | | PTGER1 | 1.00 |
| 18259 | 3 | | | | | PTGER3 | 1.00 |
| 18260 | 3 | | | | | PTGFR | 1.00 |
| 18261 | 3 | | | | | PTGIS | 1.00 |
| 18262 | 3 | | | | | PTGR1 | 1.00 |
| 18263 | 3 | | | | | PTH | 1.00 |
| 18264 | 3 | | | | | PTH1R | 1.00 |
| 18265 | 3 | | | | | PTH2 | 1.00 |
| 18266 | 3 | | | | | PTH2R | 1.00 |
| 18267 | 3 | | | | | PTHLH | 1.00 |
| 18268 | 3 | | | | | PTK6 | 1.00 |
| 18269 | 3 | | | | | PTK7 | 1.00 |
| 18270 | 3 | | | | | PTN | 1.00 |
| 18271 | 3 | | | | | PTPDC1 | 1.00 |
| 18272 | 3 | | | | | PTPLA | 1.00 |
| 18273 | 3 | | | | | PTPN13 | 1.00 |
| 18274 | 3 | | | | | PTPN14 | 1.00 |
| 18275 | 3 | | | | | PTPN20A | 1.00 |
| 18276 | 3 | | | | | PTPN20B | 1.00 |
| 18277 | 3 | | | | | PTPN21 | 1.00 |
| 18278 | 3 | | | | | PTPN3 | 1.00 |
| 18279 | 3 | | | | | PTPN5 | 1.00 |
| 18280 | 3 | | | | | PTPRB | 1.00 |
| 18281 | 3 | | | | | PTPRD | 1.00 |
| 18282 | 3 | | | | | PTPRF | 1.00 |
| 18283 | 3 | | | | | PTPRG | 1.00 |
| 18284 | 3 | | | | | PTPRH | 1.00 |
| 18285 | 3 | | | | | PTPRK | 1.00 |
| 18286 | 3 | | | | | PTPRM | 1.00 |
| 18287 | 3 | | | | | PTPRN | 1.00 |
| 18288 | 3 | | | | | PTPRQ | 1.00 |
| 18289 | 3 | | | | | PTPRR | 1.00 |
| 18290 | 3 | | | | | PTPRS | 1.00 |
| 18291 | 3 | | | | | PTPRT | 1.00 |
| 18292 | 3 | | | | | PTPRU | 1.00 |
| 18293 | 3 | | | | | PTPRVP | 1.00 |
| 18294 | 3 | | | | | PTPRZ1 | 1.00 |
| 18295 | 3 | | | | | PTRF | 1.00 |
| 18296 | 3 | | | | | PTX4 | 1.00 |
| 18297 | 3 | | | | | PURG | 1.00 |
| 18298 | 3 | | | | | PVRL3 | 1.00 |
| 18299 | 3 | | | | | PVRL3-AS1 | 1.00 |
| 18300 | 3 | | | | | PVRL4 | 1.00 |
| 18301 | 3 | | | | | PWRN1 | 1.00 |
| 18302 | 3 | | | | | PWRN2 | 1.00 |
| 18303 | 3 | | | | | PXDN | 1.00 |
| 18304 | 3 | | | | | PXDNL | 1.00 |
| 18305 | 3 | | | | | PXT1 | 1.00 |
| 18306 | 3 | | | | | PYCR1 | 1.00 |
| 18307 | 3 | | | | | PYDC1 | 1.00 |
| 18308 | 3 | | | | | PYDC2 | 1.00 |
| 18309 | 3 | | | | | PYGO1 | 1.00 |
| 18310 | 3 | | | | | PYY | 1.00 |
| 18311 | 3 | | | | | PYY2 | 1.00 |
| 18312 | 3 | | | | | PZP | 1.00 |
| 18313 | 3 | | | | | ProSAPiP1 | 1.00 |
| 18314 | 3 | | | | | QPCTL | 1.00 |
| 18315 | 3 | | | | | QPRT | 1.00 |
| 18316 | 3 | | | | | QRFP | 1.00 |
| 18317 | 3 | | | | | QRFPR | 1.00 |
| 18318 | 3 | | | | | QRICH2 | 1.00 |
| 18319 | 3 | | | | | R3HDML | 1.00 |
| 18320 | 3 | | | | | RAB17 | 1.00 |
| 18321 | 3 | | | | | RAB23 | 1.00 |
| 18322 | 3 | | | | | RAB25 | 1.00 |
| 18323 | 3 | | | | | RAB26 | 1.00 |
| 18324 | 3 | | | | | RAB3B | 1.00 |
| 18325 | 3 | | | | | RAB38 | 1.00 |
| 18326 | 3 | | | | | RAB3C | 1.00 |
| 18327 | 3 | | | | | RAB40A | 1.00 |
| 18328 | 3 | | | | | RAB40AL | 1.00 |
| 18329 | 3 | | | | | RAB41 | 1.00 |
| 18330 | 3 | | | | | RAB42 | 1.00 |
| 18331 | 3 | | | | | RAB4B-EGLN2 | 1.00 |
| 18332 | 3 | | | | | RAB9B | 1.00 |
| 18333 | 3 | | | | | RAB9BP1 | 1.00 |
| 18334 | 3 | | | | | RABL5 | 1.00 |
| 18335 | 3 | | | | | RAC3 | 1.00 |
| 18336 | 3 | | | | | RAD21-AS1 | 1.00 |
| 18337 | 3 | | | | | RAD21L1 | 1.00 |
| 18338 | 3 | | | | | RAD51 | 1.00 |
| 18339 | 3 | | | | | RAD51AP1 | 1.00 |
| 18340 | 3 | | | | | RAD51AP2 | 1.00 |
| 18341 | 3 | | | | | RAD51L3-RFFL | 1.00 |
| 18342 | 3 | | | | | RAD54B | 1.00 |
| 18343 | 3 | | | | | RAD54L | 1.00 |
| 18344 | 3 | | | | | RAD9B | 1.00 |
| 18345 | 3 | | | | | RADIL | 1.00 |
| 18346 | 3 | | | | | RAET1E | 1.00 |
| 18347 | 3 | | | | | RAET1G | 1.00 |
| 18348 | 3 | | | | | RAET1K | 1.00 |
| 18349 | 3 | | | | | RAET1L | 1.00 |
| 18350 | 3 | | | | | RAG1 | 1.00 |
| 18351 | 3 | | | | | RAG2 | 1.00 |
| 18352 | 3 | | | | | RAI14 | 1.00 |
| 18353 | 3 | | | | | RAI2 | 1.00 |
| 18354 | 3 | | | | | RALYL | 1.00 |
| 18355 | 3 | | | | | RAMP2 | 1.00 |
| 18356 | 3 | | | | | RAMP3 | 1.00 |
| 18357 | 3 | | | | | RANBP17 | 1.00 |
| 18358 | 3 | | | | | RANBP3L | 1.00 |
| 18359 | 3 | | | | | RAP1GAP | 1.00 |
| 18360 | 3 | | | | | RAPGEF3 | 1.00 |
| 18361 | 3 | | | | | RAPGEF4 | 1.00 |
| 18362 | 3 | | | | | RAPGEF5 | 1.00 |
| 18363 | 3 | | | | | RAPSN | 1.00 |
| 18364 | 3 | | | | | RARB | 1.00 |
| 18365 | 3 | | | | | RARRES1 | 1.00 |
| 18366 | 3 | | | | | RARRES2 | 1.00 |
| 18367 | 3 | | | | | RASAL1 | 1.00 |
| 18368 | 3 | | | | | RASAL2 | 1.00 |
| 18369 | 3 | | | | | RASD1 | 1.00 |
| 18370 | 3 | | | | | RASD2 | 1.00 |
| 18371 | 3 | | | | | RASEF | 1.00 |
| 18372 | 3 | | | | | RASGEF1C | 1.00 |
| 18373 | 3 | | | | | RASGRF1 | 1.00 |
| 18374 | 3 | | | | | RASIP1 | 1.00 |
| 18375 | 3 | | | | | RASL10A | 1.00 |
| 18376 | 3 | | | | | RASL10B | 1.00 |
| 18377 | 3 | | | | | RASL11B | 1.00 |
| 18378 | 3 | | | | | RASL12 | 1.00 |
| 18379 | 3 | | | | | RASSF10 | 1.00 |
| 18380 | 3 | | | | | RASSF6 | 1.00 |
| 18381 | 3 | | | | | RASSF8 | 1.00 |
| 18382 | 3 | | | | | RASSF9 | 1.00 |
| 18383 | 3 | | | | | RAVER2 | 1.00 |
| 18384 | 3 | | | | | RAX | 1.00 |
| 18385 | 3 | | | | | RAX2 | 1.00 |
| 18386 | 3 | | | | | RBAK-LOC389458 | 1.00 |
| 18387 | 3 | | | | | RBFOX1 | 1.00 |
| 18388 | 3 | | | | | RBFOX2 | 1.00 |
| 18389 | 3 | | | | | RBFOX3 | 1.00 |
| 18390 | 3 | | | | | RBKS | 1.00 |
| 18391 | 3 | | | | | RBM11 | 1.00 |
| 18392 | 3 | | | | | RBM20 | 1.00 |
| 18393 | 3 | | | | | RBM24 | 1.00 |
| 18394 | 3 | | | | | RBM26-AS1 | 1.00 |
| 18395 | 3 | | | | | RBM44 | 1.00 |
| 18396 | 3 | | | | | RBM46 | 1.00 |
| 18397 | 3 | | | | | RBMS3 | 1.00 |
| 18398 | 3 | | | | | RBMXL2 | 1.00 |
| 18399 | 3 | | | | | RBMXL3 | 1.00 |
| 18400 | 3 | | | | | RBMY1A1 | 1.00 |
| 18401 | 3 | | | | | RBMY1A3P | 1.00 |
| 18402 | 3 | | | | | RBMY1B | 1.00 |
| 18403 | 3 | | | | | RBMY1D | 1.00 |
| 18404 | 3 | | | | | RBMY1E | 1.00 |
| 18405 | 3 | | | | | RBMY1F | 1.00 |
| 18406 | 3 | | | | | RBMY1J | 1.00 |
| 18407 | 3 | | | | | RBMY2EP | 1.00 |
| 18408 | 3 | | | | | RBMY2FP | 1.00 |
| 18409 | 3 | | | | | RBMY3AP | 1.00 |
| 18410 | 3 | | | | | RBP1 | 1.00 |
| 18411 | 3 | | | | | RBP2 | 1.00 |
| 18412 | 3 | | | | | RBP3 | 1.00 |
| 18413 | 3 | | | | | RBP4 | 1.00 |
| 18414 | 3 | | | | | RBP5 | 1.00 |
| 18415 | 3 | | | | | RBPJL | 1.00 |
| 18416 | 3 | | | | | RBPMS | 1.00 |
| 18417 | 3 | | | | | RCAN2 | 1.00 |
| 18418 | 3 | | | | | RCCD1 | 1.00 |
| 18419 | 3 | | | | | RCOR2 | 1.00 |
| 18420 | 3 | | | | | RCVRN | 1.00 |
| 18421 | 3 | | | | | RD3 | 1.00 |
| 18422 | 3 | | | | | RDH12 | 1.00 |
| 18423 | 3 | | | | | RDH16 | 1.00 |
| 18424 | 3 | | | | | RDH8 | 1.00 |

Fig. 41 - 97

| | | | | | | | | | | | | | | |
|---|---|---|---|---|---|---|---|---|---|---|---|---|---|---|
| 18425 | 3 | | | | | | RDM1 | 1.00 | 18521 | 3 | | | RNASE13 | 1.00 |
| 18426 | 3 | | | | | | RECQL4 | 1.00 | 18522 | 3 | | | RNASE7 | 1.00 |
| 18427 | 3 | | | | | | REEP1 | 1.00 | 18523 | 3 | | | RNASE8 | 1.00 |
| 18428 | 3 | | | | | | REEP2 | 1.00 | 18524 | 3 | | | RNASE9 | 1.00 |
| 18429 | 3 | | | | | | REG1A | 1.00 | 18525 | 3 | | | RND1 | 1.00 |
| 18430 | 3 | | | | | | REG1B | 1.00 | 18526 | 3 | | | RND2 | 1.00 |
| 18431 | 3 | | | | | | REG1P | 1.00 | 18527 | 3 | | | RND3 | 1.00 |
| 18432 | 3 | | | | | | REG3A | 1.00 | 18528 | 3 | | | RNF112 | 1.00 |
| 18433 | 3 | | | | | | REG3G | 1.00 | 18529 | 3 | | | RNF113B | 1.00 |
| 18434 | 3 | | | | | | REG4 | 1.00 | 18530 | 3 | | | RNF128 | 1.00 |
| 18435 | 3 | | | | | | RELN | 1.00 | 18531 | 3 | | | RNF133 | 1.00 |
| 18436 | 3 | | | | | | REM1 | 1.00 | 18532 | 3 | | | RNF148 | 1.00 |
| 18437 | 3 | | | | | | REN | 1.00 | 18533 | 3 | | | RNF150 | 1.00 |
| 18438 | 3 | | | | | | REP15 | 1.00 | 18534 | 3 | | | RNF151 | 1.00 |
| 18439 | 3 | | | | | | RERG | 1.00 | 18535 | 3 | | | RNF152 | 1.00 |
| 18440 | 3 | | | | | | RERGL | 1.00 | 18536 | 3 | | | RNF165 | 1.00 |
| 18441 | 3 | | | | | | RESP18 | 1.00 | 18537 | 3 | | | RNF17 | 1.00 |
| 18442 | 3 | | | | | | RET | 1.00 | 18538 | 3 | | | RNF180 | 1.00 |
| 18443 | 3 | | | | | | RETNLB | 1.00 | 18539 | 3 | | | RNF183 | 1.00 |
| 18444 | 3 | | | | | | REXO1L1 | 1.00 | 18540 | 3 | | | RNF186 | 1.00 |
| 18445 | 3 | | | | | | REXO1L2P | 1.00 | 18541 | 3 | | | RNF207 | 1.00 |
| 18446 | 3 | | | | | | RFESD | 1.00 | 18542 | 3 | | | RNF212 | 1.00 |
| 18447 | 3 | | | | | | RFPL1 | 1.00 | 18543 | 3 | | | RNF217 | 1.00 |
| 18448 | 3 | | | | | | RFPL1-AS1 | 1.00 | 18544 | 3 | | | RNF222 | 1.00 |
| 18449 | 3 | | | | | | RFPL3 | 1.00 | 18545 | 3 | | | RNF223 | 1.00 |
| 18450 | 3 | | | | | | RFPL3-AS1 | 1.00 | 18546 | 3 | | | RNF224 | 1.00 |
| 18451 | 3 | | | | | | RFPL4A | 1.00 | 18547 | 3 | | | RNF32 | 1.00 |
| 18452 | 3 | | | | | | RFPL4B | 1.00 | 18548 | 3 | | | RNF39 | 1.00 |
| 18453 | 3 | | | | | | RFTN2 | 1.00 | 18549 | 3 | | | RNF43 | 1.00 |
| 18454 | 3 | | | | | | RFX4 | 1.00 | 18550 | 3 | | | RNFT2 | 1.00 |
| 18455 | 3 | | | | | | RFX6 | 1.00 | 18551 | 3 | | | RNLS | 1.00 |
| 18456 | 3 | | | | | | RFX8 | 1.00 | 18552 | 3 | | | RNU12 | 1.00 |
| 18457 | 3 | | | | | | RGAG1 | 1.00 | 18553 | 3 | | | RNU4ATAC | 1.00 |
| 18458 | 3 | | | | | | RGL3 | 1.00 | 18554 | 3 | | | RNU5D-1 | 1.00 |
| 18459 | 3 | | | | | | RGMA | 1.00 | 18555 | 3 | | | RNU5E-1 | 1.00 |
| 18460 | 3 | | | | | | RGN | 1.00 | 18556 | 3 | | | RNU5F-1 | 1.00 |
| 18461 | 3 | | | | | | RGNEF | 1.00 | 18557 | 3 | | | RNU86 | 1.00 |
| 18462 | 3 | | | | | | RGPD2 | 1.00 | 18558 | 3 | | | RNY4 | 1.00 |
| 18463 | 3 | | | | | | RGPD6 | 1.00 | 18559 | 3 | | | RNY5 | 1.00 |
| 18464 | 3 | | | | | | RGR | 1.00 | 18560 | 3 | | | ROBO1 | 1.00 |
| 18465 | 3 | | | | | | RGS11 | 1.00 | 18561 | 3 | | | ROBO2 | 1.00 |
| 18466 | 3 | | | | | | RGS13 | 1.00 | 18562 | 3 | | | ROBO3 | 1.00 |
| 18467 | 3 | | | | | | RGS16 | 1.00 | 18563 | 3 | | | ROBO4 | 1.00 |
| 18468 | 3 | | | | | | RGS17 | 1.00 | 18564 | 3 | | | ROM1 | 1.00 |
| 18469 | 3 | | | | | | RGS20 | 1.00 | 18565 | 3 | | | ROPN1 | 1.00 |
| 18470 | 3 | | | | | | RGS21 | 1.00 | 18566 | 3 | | | ROPN1B | 1.00 |
| 18471 | 3 | | | | | | RGS22 | 1.00 | 18567 | 3 | | | ROR1 | 1.00 |
| 18472 | 3 | | | | | | RGS4 | 1.00 | 18568 | 3 | | | ROR2 | 1.00 |
| 18473 | 3 | | | | | | RGS5 | 1.00 | 18569 | 3 | | | RORB | 1.00 |
| 18474 | 3 | | | | | | RGS6 | 1.00 | 18570 | 3 | | | ROS1 | 1.00 |
| 18475 | 3 | | | | | | RGS7 | 1.00 | 18571 | 3 | | | RP1 | 1.00 |
| 18476 | 3 | | | | | | RGS7BP | 1.00 | 18572 | 3 | | | RP1-177G6.2 | 1.00 |
| 18477 | 3 | | | | | | RGS8 | 1.00 | 18573 | 3 | | | RP11-165H21 | 1.00 |
| 18478 | 3 | | | | | | RGS9 | 1.00 | 18574 | 3 | | | RP1L1 | 1.00 |
| 18479 | 3 | | | | | | RGS9BP | 1.00 | 18575 | 3 | | | RPA4 | 1.00 |
| 18480 | 3 | | | | | | RGSL1 | 1.00 | 18576 | 3 | | | RPE65 | 1.00 |
| 18481 | 3 | | | | | | RHAG | 1.00 | 18577 | 3 | | | RPGRIP1L | 1.00 |
| 18482 | 3 | | | | | | RHBDF1 | 1.00 | 18578 | 3 | | | RPL10L | 1.00 |
| 18483 | 3 | | | | | | RHBDL1 | 1.00 | 18579 | 3 | | | RPL13AP17 | 1.00 |
| 18484 | 3 | | | | | | RHBDL2 | 1.00 | 18580 | 3 | | | RPL13AP3 | 1.00 |
| 18485 | 3 | | | | | | RHBDL3 | 1.00 | 18581 | 3 | | | RPL13AP5 | 1.00 |
| 18486 | 3 | | | | | | RHBG | 1.00 | 18582 | 3 | | | RPL21P44 | 1.00 |
| 18487 | 3 | | | | | | RHCE | 1.00 | 18583 | 3 | | | RPL23AP32 | 1.00 |
| 18488 | 3 | | | | | | RHCG | 1.00 | 18584 | 3 | | | RPL31P11 | 1.00 |
| 18489 | 3 | | | | | | RHO | 1.00 | 18585 | 3 | | | RPLP0P2 | 1.00 |
| 18490 | 3 | | | | | | RHOBTB3 | 1.00 | 18586 | 3 | | | RPP40 | 1.00 |
| 18491 | 3 | | | | | | RHOD | 1.00 | 18587 | 3 | | | RPRM | 1.00 |
| 18492 | 3 | | | | | | RHOJ | 1.00 | 18588 | 3 | | | RPRML | 1.00 |
| 18493 | 3 | | | | | | RHOV | 1.00 | 18589 | 3 | | | RPS15AP10 | 1.00 |
| 18494 | 3 | | | | | | RHOXF1 | 1.00 | 18590 | 3 | | | RPS16P5 | 1.00 |
| 18495 | 3 | | | | | | RHOXF2 | 1.00 | 18591 | 3 | | | RPS21 | 1.00 |
| 18496 | 3 | | | | | | RHOXF2B | 1.00 | 18592 | 3 | | | RPS4Y2 | 1.00 |
| 18497 | 3 | | | | | | RHPN1 | 1.00 | 18593 | 3 | | | RPS6KA6 | 1.00 |
| 18498 | 3 | | | | | | RHPN2 | 1.00 | 18594 | 3 | | | RPS6KL1 | 1.00 |
| 18499 | 3 | | | | | | RIBC1 | 1.00 | 18595 | 3 | | | RPS7P5 | 1.00 |
| 18500 | 3 | | | | | | RIBC2 | 1.00 | 18596 | 3 | | | RPSAP52 | 1.00 |
| 18501 | 3 | | | | | | RIC3 | 1.00 | 18597 | 3 | | | RPTN | 1.00 |
| 18502 | 3 | | | | | | RIIAD1 | 1.00 | 18598 | 3 | | | RRAD | 1.00 |
| 18503 | 3 | | | | | | RIMBP2 | 1.00 | 18599 | 3 | | | RRH | 1.00 |
| 18504 | 3 | | | | | | RIMBP3C | 1.00 | 18600 | 3 | | | RS1 | 1.00 |
| 18505 | 3 | | | | | | RIMKLA | 1.00 | 18601 | 3 | | | RSPH1 | 1.00 |
| 18506 | 3 | | | | | | RIMKLB | 1.00 | 18602 | 3 | | | RSPH10B2 | 1.00 |
| 18507 | 3 | | | | | | RIMS1 | 1.00 | 18603 | 3 | | | RSPH4A | 1.00 |
| 18508 | 3 | | | | | | RIMS2 | 1.00 | 18604 | 3 | | | RSPH6A | 1.00 |
| 18509 | 3 | | | | | | RIMS4 | 1.00 | 18605 | 3 | | | RSPH9 | 1.00 |
| 18510 | 3 | | | | | | RIPK4 | 1.00 | 18606 | 3 | | | RSPO1 | 1.00 |
| 18511 | 3 | | | | | | RIPPLY1 | 1.00 | 18607 | 3 | | | RSPO2 | 1.00 |
| 18512 | 3 | | | | | | RIPPLY2 | 1.00 | 18608 | 3 | | | RSPO3 | 1.00 |
| 18513 | 3 | | | | | | RIT2 | 1.00 | 18609 | 3 | | | RSPO4 | 1.00 |
| 18514 | 3 | | | | | | RLBP1 | 1.00 | 18610 | 3 | | | RTBDN | 1.00 |
| 18515 | 3 | | | | | | RLN1 | 1.00 | 18611 | 3 | | | RTDR1 | 1.00 |
| 18516 | 3 | | | | | | RLN3 | 1.00 | 18612 | 3 | | | RTEL1 | 1.00 |
| 18517 | 3 | | | | | | RMST | 1.00 | 18613 | 3 | | | RTEL1-TNFRSF6B | 1.00 |
| 18518 | 3 | | | | | | RNASE10 | 1.00 | 18614 | 3 | | | RTKN | 1.00 |
| 18519 | 3 | | | | | | RNASE11 | 1.00 | 18615 | 3 | | | RTL1 | 1.00 |
| 18520 | 3 | | | | | | RNASE12 | 1.00 | 18616 | 3 | | | RTN4RL1 | 1.00 |

Fig. 41 - 98

| | | | | | | | | | | | | | | | |
|---|---|---|---|---|---|---|---|---|---|---|---|---|---|---|---|
| 18617 | 3 | | | | | | RTN4RL2 | 1.00 | 18713 | 3 | | | | SCN1A | 1.00 |
| 18618 | 3 | | | | | | RTP1 | 1.00 | 18714 | 3 | | | | SCN2A | 1.00 |
| 18619 | 3 | | | | | | RTP2 | 1.00 | 18715 | 3 | | | | SCN2B | 1.00 |
| 18620 | 3 | | | | | | RTP3 | 1.00 | 18716 | 3 | | | | SCN3A | 1.00 |
| 18621 | 3 | | | | | | RTTN | 1.00 | 18717 | 3 | | | | SCN3B | 1.00 |
| 18622 | 3 | | | | | | RUFY4 | 1.00 | 18718 | 3 | | | | SCN4A | 1.00 |
| 18623 | 3 | | | | | | RUNDC3B | 1.00 | 18719 | 3 | | | | SCN4B | 1.00 |
| 18624 | 3 | | | | | | RUNX1-IT1 | 1.00 | 18720 | 3 | | | | SCN5A | 1.00 |
| 18625 | 3 | | | | | | RUNX1T1 | 1.00 | 18721 | 3 | | | | SCN7A | 1.00 |
| 18626 | 3 | | | | | | RUSC1-AS1 | 1.00 | 18722 | 3 | | | | SCN8A | 1.00 |
| 18627 | 3 | | | | | | RXFP1 | 1.00 | 18723 | 3 | | | | SCN9A | 1.00 |
| 18628 | 3 | | | | | | RXFP2 | 1.00 | 18724 | 3 | | | | SCNN1A | 1.00 |
| 18629 | 3 | | | | | | RXFP3 | 1.00 | 18725 | 3 | | | | SCNN1B | 1.00 |
| 18630 | 3 | | | | | | RXFP4 | 1.00 | 18726 | 3 | | | | SCNN1D | 1.00 |
| 18631 | 3 | | | | | | RXRG | 1.00 | 18727 | 3 | | | | SCNN1G | 1.00 |
| 18632 | 3 | | | | | | RYR1 | 1.00 | 18728 | 3 | | | | SCRG1 | 1.00 |
| 18633 | 3 | | | | | | RYR2 | 1.00 | 18729 | 3 | | | | SCRT1 | 1.00 |
| 18634 | 3 | | | | | | RYR3 | 1.00 | 18730 | 3 | | | | SCRT2 | 1.00 |
| 18635 | 3 | | | | | | S100A1 | 1.00 | 18731 | 3 | | | | SCTR | 1.00 |
| 18636 | 3 | | | | | | S100A14 | 1.00 | 18732 | 3 | | | | SCUBE1 | 1.00 |
| 18637 | 3 | | | | | | S100A16 | 1.00 | 18733 | 3 | | | | SCUBE2 | 1.00 |
| 18638 | 3 | | | | | | S100A2 | 1.00 | 18734 | 3 | | | | SCUBE3 | 1.00 |
| 18639 | 3 | | | | | | S100A3 | 1.00 | 18735 | 3 | | | | SCXA | 1.00 |
| 18640 | 3 | | | | | | S100A5 | 1.00 | 18736 | 3 | | | | SDC1 | 1.00 |
| 18641 | 3 | | | | | | S100A7 | 1.00 | 18737 | 3 | | | | SDC4P | 1.00 |
| 18642 | 3 | | | | | | S100A7A | 1.00 | 18738 | 3 | | | | SDCBP2 | 1.00 |
| 18643 | 3 | | | | | | S100A7L2 | 1.00 | 18739 | 3 | | | | SDK1 | 1.00 |
| 18644 | 3 | | | | | | S100G | 1.00 | 18740 | 3 | | | | SDK2 | 1.00 |
| 18645 | 3 | | | | | | SAA1 | 1.00 | 18741 | 3 | | | | SDR16C5 | 1.00 |
| 18646 | 3 | | | | | | SAA2 | 1.00 | 18742 | 3 | | | | SDR9C7 | 1.00 |
| 18647 | 3 | | | | | | SAA2-SAA4 | 1.00 | 18743 | 3 | | | | SDS | 1.00 |
| 18648 | 3 | | | | | | SAA3P | 1.00 | 18744 | 3 | | | | SEBOX | 1.00 |
| 18649 | 3 | | | | | | SAA4 | 1.00 | 18745 | 3 | | | | SEC1 | 1.00 |
| 18650 | 3 | | | | | | SAG | 1.00 | 18746 | 3 | | | | SEC14L2 | 1.00 |
| 18651 | 3 | | | | | | SAGE1 | 1.00 | 18747 | 3 | | | | SEC14L3 | 1.00 |
| 18652 | 3 | | | | | | SALL1 | 1.00 | 18748 | 3 | | | | SEC14L4 | 1.00 |
| 18653 | 3 | | | | | | SALL3 | 1.00 | 18749 | 3 | | | | SEC14L6 | 1.00 |
| 18654 | 3 | | | | | | SALL4 | 1.00 | 18750 | 3 | | | | SEC16B | 1.00 |
| 18655 | 3 | | | | | | SAMD11 | 1.00 | 18751 | 3 | | | | SEL1L2 | 1.00 |
| 18656 | 3 | | | | | | SAMD12 | 1.00 | 18752 | 3 | | | | SELE | 1.00 |
| 18657 | 3 | | | | | | SAMD12-AS1 | 1.00 | 18753 | 3 | | | | SELV | 1.00 |
| 18658 | 3 | | | | | | SAMD13 | 1.00 | 18754 | 3 | | | | SEMA3A | 1.00 |
| 18659 | 3 | | | | | | SAMD15 | 1.00 | 18755 | 3 | | | | SEMA3B | 1.00 |
| 18660 | 3 | | | | | | SAMD4A | 1.00 | 18756 | 3 | | | | SEMA3D | 1.00 |
| 18661 | 3 | | | | | | SAMD5 | 1.00 | 18757 | 3 | | | | SEMA3E | 1.00 |
| 18662 | 3 | | | | | | SAMD7 | 1.00 | 18758 | 3 | | | | SEMA3F | 1.00 |
| 18663 | 3 | | | | | | SAPCD1 | 1.00 | 18759 | 3 | | | | SEMA3G | 1.00 |
| 18664 | 3 | | | | | | SARDH | 1.00 | 18760 | 3 | | | | SEMA4G | 1.00 |
| 18665 | 3 | | | | | | SATB2 | 1.00 | 18761 | 3 | | | | SEMA5A | 1.00 |
| 18666 | 3 | | | | | | SATL1 | 1.00 | 18762 | 3 | | | | SEMA5B | 1.00 |
| 18667 | 3 | | | | | | SBK2 | 1.00 | 18763 | 3 | | | | SEMA6A | 1.00 |
| 18668 | 3 | | | | | | SBSN | 1.00 | 18764 | 3 | | | | SEMA6B | 1.00 |
| 18669 | 3 | | | | | | SCAI | 1.00 | 18765 | 3 | | | | SEMA6C | 1.00 |
| 18670 | 3 | | | | | | SCAND3 | 1.00 | 18766 | 3 | | | | SEMA6D | 1.00 |
| 18671 | 3 | | | | | | SCARA3 | 1.00 | 18767 | 3 | | | | SEMG2 | 1.00 |
| 18672 | 3 | | | | | | SCARA5 | 1.00 | 18768 | 3 | | | | SENP3-EIF4A1 | 1.00 |
| 18673 | 3 | | | | | | SCARF2 | 1.00 | 18769 | 3 | | | | SEPP1 | 1.00 |
| 18674 | 3 | | | | | | SCARNA1 | 1.00 | 18770 | 3 | | | | 42625 | 1.00 |
| 18675 | 3 | | | | | | SCARNA10 | 1.00 | 18771 | 3 | | | | 42627 | 1.00 |
| 18676 | 3 | | | | | | SCARNA11 | 1.00 | 18772 | 3 | | | | 42616 | 1.00 |
| 18677 | 3 | | | | | | SCARNA13 | 1.00 | 18773 | 3 | | | | 42617 | 1.00 |
| 18678 | 3 | | | | | | SCARNA14 | 1.00 | 18774 | 3 | | | | SEPT7L | 1.00 |
| 18679 | 3 | | | | | | SCARNA15 | 1.00 | 18775 | 3 | | | | SEPT7P2 | 1.00 |
| 18680 | 3 | | | | | | SCARNA18 | 1.00 | 18776 | 3 | | | | SERF1A | 1.00 |
| 18681 | 3 | | | | | | SCARNA20 | 1.00 | 18777 | 3 | | | | SERF2-C15ORF63 | 1.00 |
| 18682 | 3 | | | | | | SCARNA21 | 1.00 | 18778 | 3 | | | | SERHL | 1.00 |
| 18683 | 3 | | | | | | SCARNA22 | 1.00 | 18779 | 3 | | | | SERHL2 | 1.00 |
| 18684 | 3 | | | | | | SCARNA23 | 1.00 | 18780 | 3 | | | | SERINC4 | 1.00 |
| 18685 | 3 | | | | | | SCARNA27 | 1.00 | 18781 | 3 | | | | SERP2 | 1.00 |
| 18686 | 3 | | | | | | SCARNA3 | 1.00 | 18782 | 3 | | | | SERPINA10 | 1.00 |
| 18687 | 3 | | | | | | SCARNA4 | 1.00 | 18783 | 3 | | | | SERPINA11 | 1.00 |
| 18688 | 3 | | | | | | SCARNA5 | 1.00 | 18784 | 3 | | | | SERPINA12 | 1.00 |
| 18689 | 3 | | | | | | SCARNA6 | 1.00 | 18785 | 3 | | | | SERPINA13 | 1.00 |
| 18690 | 3 | | | | | | SCARNA8 | 1.00 | 18786 | 3 | | | | SERPINA3 | 1.00 |
| 18691 | 3 | | | | | | SCARNA9L | 1.00 | 18787 | 3 | | | | SERPINA4 | 1.00 |
| 18692 | 3 | | | | | | SCEL | 1.00 | 18788 | 3 | | | | SERPINA5 | 1.00 |
| 18693 | 3 | | | | | | SCG2 | 1.00 | 18789 | 3 | | | | SERPINA6 | 1.00 |
| 18694 | 3 | | | | | | SCG3 | 1.00 | 18790 | 3 | | | | SERPINA7 | 1.00 |
| 18695 | 3 | | | | | | SCG5 | 1.00 | 18791 | 3 | | | | SERPINA9 | 1.00 |
| 18696 | 3 | | | | | | SCGB1A1 | 1.00 | 18792 | 3 | | | | SERPINB11 | 1.00 |
| 18697 | 3 | | | | | | SCGB1B2P | 1.00 | 18793 | 3 | | | | SERPINB12 | 1.00 |
| 18698 | 3 | | | | | | SCGB1D1 | 1.00 | 18794 | 3 | | | | SERPINB13 | 1.00 |
| 18699 | 3 | | | | | | SCGB1D2 | 1.00 | 18795 | 3 | | | | SERPINB3 | 1.00 |
| 18700 | 3 | | | | | | SCGB1D4 | 1.00 | 18796 | 3 | | | | SERPINB4 | 1.00 |
| 18701 | 3 | | | | | | SCGB2A1 | 1.00 | 18797 | 3 | | | | SERPINB5 | 1.00 |
| 18702 | 3 | | | | | | SCGB2A2 | 1.00 | 18798 | 3 | | | | SERPINB7 | 1.00 |
| 18703 | 3 | | | | | | SCGB2B2 | 1.00 | 18799 | 3 | | | | SERPINC1 | 1.00 |
| 18704 | 3 | | | | | | SCGB2B3P | 1.00 | 18800 | 3 | | | | SERPIND1 | 1.00 |
| 18705 | 3 | | | | | | SCGB3A1 | 1.00 | 18801 | 3 | | | | SERPINE1 | 1.00 |
| 18706 | 3 | | | | | | SCGB3A2 | 1.00 | 18802 | 3 | | | | SERPINE3 | 1.00 |
| 18707 | 3 | | | | | | SCGN | 1.00 | 18803 | 3 | | | | SERPINI2 | 1.00 |
| 18708 | 3 | | | | | | SCHIP1 | 1.00 | 18804 | 3 | | | | SERTAD4 | 1.00 |
| 18709 | 3 | | | | | | SCIN | 1.00 | 18805 | 3 | | | | SERTM1 | 1.00 |
| 18710 | 3 | | | | | | SCML2 | 1.00 | 18806 | 3 | | | | SEZ6 | 1.00 |
| 18711 | 3 | | | | | | SCN10A | 1.00 | 18807 | 3 | | | | SEZ6L | 1.00 |
| 18712 | 3 | | | | | | SCN11A | 1.00 | 18808 | 3 | | | | SEZ6L2 | 1.00 |

Fig. 41 - 99

| | | | | | | | | | | | | | | |
|---|---|---|---|---|---|---|---|---|---|---|---|---|---|---|
| 18809 | 3 | | | | | SFN | 1.00 | 18905 | 3 | | | | SLC16A14 | 1.00 |
| 18810 | 3 | | | | | SFRP1 | 1.00 | 18906 | 3 | | | | SLC16A2 | 1.00 |
| 18811 | 3 | | | | | SFRP4 | 1.00 | 18907 | 3 | | | | SLC16A4 | 1.00 |
| 18812 | 3 | | | | | SFRP5 | 1.00 | 18908 | 3 | | | | SLC16A8 | 1.00 |
| 18813 | 3 | | | | | SFTA1P | 1.00 | 18909 | 3 | | | | SLC16A9 | 1.00 |
| 18814 | 3 | | | | | SFTA2 | 1.00 | 18910 | 3 | | | | SLC17A1 | 1.00 |
| 18815 | 3 | | | | | SFTA3 | 1.00 | 18911 | 3 | | | | SLC17A2 | 1.00 |
| 18816 | 3 | | | | | SFTPA1 | 1.00 | 18912 | 3 | | | | SLC17A3 | 1.00 |
| 18817 | 3 | | | | | SFTPA2 | 1.00 | 18913 | 3 | | | | SLC17A4 | 1.00 |
| 18818 | 3 | | | | | SFTPB | 1.00 | 18914 | 3 | | | | SLC17A6 | 1.00 |
| 18819 | 3 | | | | | SFTPC | 1.00 | 18915 | 3 | | | | SLC17A7 | 1.00 |
| 18820 | 3 | | | | | SFTPD | 1.00 | 18916 | 3 | | | | SLC17A8 | 1.00 |
| 18821 | 3 | | | | | SGCA | 1.00 | 18917 | 3 | | | | SLC18A1 | 1.00 |
| 18822 | 3 | | | | | SGCD | 1.00 | 18918 | 3 | | | | SLC18A3 | 1.00 |
| 18823 | 3 | | | | | SGCE | 1.00 | 18919 | 3 | | | | SLC19A3 | 1.00 |
| 18824 | 3 | | | | | SGCG | 1.00 | 18920 | 3 | | | | SLC1A1 | 1.00 |
| 18825 | 3 | | | | | SGCZ | 1.00 | 18921 | 3 | | | | SLC1A2 | 1.00 |
| 18826 | 3 | | | | | SGIP1 | 1.00 | 18922 | 3 | | | | SLC1A6 | 1.00 |
| 18827 | 3 | | | | | SGK110 | 1.00 | 18923 | 3 | | | | SLC1A7 | 1.00 |
| 18828 | 3 | | | | | SGK2 | 1.00 | 18924 | 3 | | | | SLC22A1 | 1.00 |
| 18829 | 3 | | | | | SGOL1 | 1.00 | 18925 | 3 | | | | SLC22A10 | 1.00 |
| 18830 | 3 | | | | | SGSM1 | 1.00 | 18926 | 3 | | | | SLC22A11 | 1.00 |
| 18831 | 3 | | | | | SH2D4A | 1.00 | 18927 | 3 | | | | SLC22A12 | 1.00 |
| 18832 | 3 | | | | | SH2D4B | 1.00 | 18928 | 3 | | | | SLC22A13 | 1.00 |
| 18833 | 3 | | | | | SH2D5 | 1.00 | 18929 | 3 | | | | SLC22A14 | 1.00 |
| 18834 | 3 | | | | | SH2D6 | 1.00 | 18930 | 3 | | | | SLC22A18AS | 1.00 |
| 18835 | 3 | | | | | SH2D7 | 1.00 | 18931 | 3 | | | | SLC22A2 | 1.00 |
| 18836 | 3 | | | | | SH3BGR | 1.00 | 18932 | 3 | | | | SLC22A20 | 1.00 |
| 18837 | 3 | | | | | SH3D19 | 1.00 | 18933 | 3 | | | | SLC22A24 | 1.00 |
| 18838 | 3 | | | | | SH3GL2 | 1.00 | 18934 | 3 | | | | SLC22A25 | 1.00 |
| 18839 | 3 | | | | | SH3GL3 | 1.00 | 18935 | 3 | | | | SLC22A3 | 1.00 |
| 18840 | 3 | | | | | SH3RF2 | 1.00 | 18936 | 3 | | | | SLC22A31 | 1.00 |
| 18841 | 3 | | | | | SH3TC2 | 1.00 | 18937 | 3 | | | | SLC22A6 | 1.00 |
| 18842 | 3 | | | | | SHANK1 | 1.00 | 18938 | 3 | | | | SLC22A7 | 1.00 |
| 18843 | 3 | | | | | SHANK2 | 1.00 | 18939 | 3 | | | | SLC22A8 | 1.00 |
| 18844 | 3 | | | | | SHANK3 | 1.00 | 18940 | 3 | | | | SLC22A9 | 1.00 |
| 18845 | 3 | | | | | SHB | 1.00 | 18941 | 3 | | | | SLC23A1 | 1.00 |
| 18846 | 3 | | | | | SHBG | 1.00 | 18942 | 3 | | | | SLC23A3 | 1.00 |
| 18847 | 3 | | | | | SHC2 | 1.00 | 18943 | 3 | | | | SLC24A2 | 1.00 |
| 18848 | 3 | | | | | SHC3 | 1.00 | 18944 | 3 | | | | SLC24A5 | 1.00 |
| 18849 | 3 | | | | | SHC4 | 1.00 | 18945 | 3 | | | | SLC25A10 | 1.00 |
| 18850 | 3 | | | | | SHCBP1 | 1.00 | 18946 | 3 | | | | SLC25A18 | 1.00 |
| 18851 | 3 | | | | | SHCBP1L | 1.00 | 18947 | 3 | | | | SLC25A2 | 1.00 |
| 18852 | 3 | | | | | SHD | 1.00 | 18948 | 3 | | | | SLC25A21 | 1.00 |
| 18853 | 3 | | | | | SHE | 1.00 | 18949 | 3 | | | | SLC25A27 | 1.00 |
| 18854 | 3 | | | | | SHF | 1.00 | 18950 | 3 | | | | SLC25A31 | 1.00 |
| 18855 | 3 | | | | | SHH | 1.00 | 18951 | 3 | | | | SLC25A34 | 1.00 |
| 18856 | 3 | | | | | SHISA2 | 1.00 | 18952 | 3 | | | | SLC25A41 | 1.00 |
| 18857 | 3 | | | | | SHISA3 | 1.00 | 18953 | 3 | | | | SLC25A47 | 1.00 |
| 18858 | 3 | | | | | SHISA6 | 1.00 | 18954 | 3 | | | | SLC25A48 | 1.00 |
| 18859 | 3 | | | | | SHISA7 | 1.00 | 18955 | 3 | | | | SLC26A10 | 1.00 |
| 18860 | 3 | | | | | SHISA8 | 1.00 | 18956 | 3 | | | | SLC26A3 | 1.00 |
| 18861 | 3 | | | | | SHISA9 | 1.00 | 18957 | 3 | | | | SLC26A4 | 1.00 |
| 18862 | 3 | | | | | SHOX | 1.00 | 18958 | 3 | | | | SLC26A5 | 1.00 |
| 18863 | 3 | | | | | SHOX2 | 1.00 | 18959 | 3 | | | | SLC26A7 | 1.00 |
| 18864 | 3 | | | | | SHROOM2 | 1.00 | 18960 | 3 | | | | SLC26A9 | 1.00 |
| 18865 | 3 | | | | | SHROOM3 | 1.00 | 18961 | 3 | | | | SLC27A2 | 1.00 |
| 18866 | 3 | | | | | SHROOM4 | 1.00 | 18962 | 3 | | | | SLC27A5 | 1.00 |
| 18867 | 3 | | | | | SI | 1.00 | 18963 | 3 | | | | SLC27A6 | 1.00 |
| 18868 | 3 | | | | | SIAH3 | 1.00 | 18964 | 3 | | | | SLC28A1 | 1.00 |
| 18869 | 3 | | | | | SIGLEC12 | 1.00 | 18965 | 3 | | | | SLC28A2 | 1.00 |
| 18870 | 3 | | | | | SIM1 | 1.00 | 18966 | 3 | | | | SLC28A3 | 1.00 |
| 18871 | 3 | | | | | SIM2 | 1.00 | 18967 | 3 | | | | SLC29A2 | 1.00 |
| 18872 | 3 | | | | | SIRT4 | 1.00 | 18968 | 3 | | | | SLC29A4 | 1.00 |
| 18873 | 3 | | | | | SIX1 | 1.00 | 18969 | 3 | | | | SLC2A10 | 1.00 |
| 18874 | 3 | | | | | SIX2 | 1.00 | 18970 | 3 | | | | SLC2A12 | 1.00 |
| 18875 | 3 | | | | | SIX3 | 1.00 | 18971 | 3 | | | | SLC2A2 | 1.00 |
| 18876 | 3 | | | | | SIX4 | 1.00 | 18972 | 3 | | | | SLC2A4 | 1.00 |
| 18877 | 3 | | | | | SIX5 | 1.00 | 18973 | 3 | | | | SLC2A5 | 1.00 |
| 18878 | 3 | | | | | SIX6 | 1.00 | 18974 | 3 | | | | SLC2A7 | 1.00 |
| 18879 | 3 | | | | | SKA1 | 1.00 | 18975 | 3 | | | | SLC30A10 | 1.00 |
| 18880 | 3 | | | | | SKA3 | 1.00 | 18976 | 3 | | | | SLC30A2 | 1.00 |
| 18881 | 3 | | | | | SKINTL | 1.00 | 18977 | 3 | | | | SLC30A3 | 1.00 |
| 18882 | 3 | | | | | SKOR1 | 1.00 | 18978 | 3 | | | | SLC30A8 | 1.00 |
| 18883 | 3 | | | | | SLAMF9 | 1.00 | 18979 | 3 | | | | SLC32A1 | 1.00 |
| 18884 | 3 | | | | | SLC10A1 | 1.00 | 18980 | 3 | | | | SLC34A1 | 1.00 |
| 18885 | 3 | | | | | SLC10A2 | 1.00 | 18981 | 3 | | | | SLC34A2 | 1.00 |
| 18886 | 3 | | | | | SLC10A4 | 1.00 | 18982 | 3 | | | | SLC34A3 | 1.00 |
| 18887 | 3 | | | | | SLC10A5 | 1.00 | 18983 | 3 | | | | SLC35D3 | 1.00 |
| 18888 | 3 | | | | | SLC10A6 | 1.00 | 18984 | 3 | | | | SLC35F1 | 1.00 |
| 18889 | 3 | | | | | SLC12A1 | 1.00 | 18985 | 3 | | | | SLC35F3 | 1.00 |
| 18890 | 3 | | | | | SLC12A3 | 1.00 | 18986 | 3 | | | | SLC35F4 | 1.00 |
| 18891 | 3 | | | | | SLC12A5 | 1.00 | 18987 | 3 | | | | SLC35G1 | 1.00 |
| 18892 | 3 | | | | | SLC12A8 | 1.00 | 18988 | 3 | | | | SLC35G3 | 1.00 |
| 18893 | 3 | | | | | SLC13A1 | 1.00 | 18989 | 3 | | | | SLC35G5 | 1.00 |
| 18894 | 3 | | | | | SLC13A2 | 1.00 | 18990 | 3 | | | | SLC35G6 | 1.00 |
| 18895 | 3 | | | | | SLC13A3 | 1.00 | 18991 | 3 | | | | SLC36A2 | 1.00 |
| 18896 | 3 | | | | | SLC13A4 | 1.00 | 18992 | 3 | | | | SLC36A3 | 1.00 |
| 18897 | 3 | | | | | SLC13A5 | 1.00 | 18993 | 3 | | | | SLC38A11 | 1.00 |
| 18898 | 3 | | | | | SLC14A2 | 1.00 | 18994 | 3 | | | | SLC38A3 | 1.00 |
| 18899 | 3 | | | | | SLC15A1 | 1.00 | 18995 | 3 | | | | SLC38A4 | 1.00 |
| 18900 | 3 | | | | | SLC15A2 | 1.00 | 18996 | 3 | | | | SLC38A6 | 1.00 |
| 18901 | 3 | | | | | SLC15A5 | 1.00 | 18997 | 3 | | | | SLC38A8 | 1.00 |
| 18902 | 3 | | | | | SLC16A10 | 1.00 | 18998 | 3 | | | | SLC39A12 | 1.00 |
| 18903 | 3 | | | | | SLC16A11 | 1.00 | 18999 | 3 | | | | SLC39A2 | 1.00 |
| 18904 | 3 | | | | | SLC16A12 | 1.00 | 19000 | 3 | | | | SLC39A5 | 1.00 |

Fig. 41 - 100

| | | | | | | | | | | | | | | |
|---|---|---|---|---|---|---|---|---|---|---|---|---|---|---|
| 19001 | 3 | | | | | | SLC3A1 | 1.00 | 19097 | 3 | | | SMPX | 1.00 |
| 19002 | 3 | | | | | | SLC41A2 | 1.00 | 19098 | 3 | | | SMR3A | 1.00 |
| 19003 | 3 | | | | | | SLC44A3 | 1.00 | 19099 | 3 | | | SMR3B | 1.00 |
| 19004 | 3 | | | | | | SLC44A4 | 1.00 | 19100 | 3 | | | SMTN | 1.00 |
| 19005 | 3 | | | | | | SLC44A5 | 1.00 | 19101 | 3 | | | SMTNL1 | 1.00 |
| 19006 | 3 | | | | | | SLC45A1 | 1.00 | 19102 | 3 | | | SMTNL2 | 1.00 |
| 19007 | 3 | | | | | | SLC45A2 | 1.00 | 19103 | 3 | | | SMYD1 | 1.00 |
| 19008 | 3 | | | | | | SLC47A1 | 1.00 | 19104 | 3 | | | SNAI1 | 1.00 |
| 19009 | 3 | | | | | | SLC47A2 | 1.00 | 19105 | 3 | | | SNAI2 | 1.00 |
| 19010 | 3 | | | | | | SLC4A11 | 1.00 | 19106 | 3 | | | SNAP25 | 1.00 |
| 19011 | 3 | | | | | | SLC4A3 | 1.00 | 19107 | 3 | | | SNAP91 | 1.00 |
| 19012 | 3 | | | | | | SLC4A4 | 1.00 | 19108 | 3 | | | SNAR-A1 | 1.00 |
| 19013 | 3 | | | | | | SLC4A8 | 1.00 | 19109 | 3 | | | SNAR-A11 | 1.00 |
| 19014 | 3 | | | | | | SLC4A9 | 1.00 | 19110 | 3 | | | SNAR-A12 | 1.00 |
| 19015 | 3 | | | | | | SLC5A1 | 1.00 | 19111 | 3 | | | SNAR-A13 | 1.00 |
| 19016 | 3 | | | | | | SLC5A10 | 1.00 | 19112 | 3 | | | SNAR-A14 | 1.00 |
| 19017 | 3 | | | | | | SLC5A11 | 1.00 | 19113 | 3 | | | SNAR-A2 | 1.00 |
| 19018 | 3 | | | | | | SLC5A12 | 1.00 | 19114 | 3 | | | SNAR-A3 | 1.00 |
| 19019 | 3 | | | | | | SLC5A2 | 1.00 | 19115 | 3 | | | SNAR-A6 | 1.00 |
| 19020 | 3 | | | | | | SLC5A4 | 1.00 | 19116 | 3 | | | SNAR-A7 | 1.00 |
| 19021 | 3 | | | | | | SLC5A5 | 1.00 | 19117 | 3 | | | SNAR-A8 | 1.00 |
| 19022 | 3 | | | | | | SLC5A7 | 1.00 | 19118 | 3 | | | SNAR-B2 | 1.00 |
| 19023 | 3 | | | | | | SLC5A8 | 1.00 | 19119 | 3 | | | SNAR-C2 | 1.00 |
| 19024 | 3 | | | | | | SLC6A1 | 1.00 | 19120 | 3 | | | SNAR-C3 | 1.00 |
| 19025 | 3 | | | | | | SLC6A10P | 1.00 | 19121 | 3 | | | SNAR-C4 | 1.00 |
| 19026 | 3 | | | | | | SLC6A11 | 1.00 | 19122 | 3 | | | SNAR-C5 | 1.00 |
| 19027 | 3 | | | | | | SLC6A13 | 1.00 | 19123 | 3 | | | SNAR-D | 1.00 |
| 19028 | 3 | | | | | | SLC6A14 | 1.00 | 19124 | 3 | | | SNAR-E | 1.00 |
| 19029 | 3 | | | | | | SLC6A15 | 1.00 | 19125 | 3 | | | SNAR-F | 1.00 |
| 19030 | 3 | | | | | | SLC6A16 | 1.00 | 19126 | 3 | | | SNAR-G1 | 1.00 |
| 19031 | 3 | | | | | | SLC6A17 | 1.00 | 19127 | 3 | | | SNAR-G2 | 1.00 |
| 19032 | 3 | | | | | | SLC6A18 | 1.00 | 19128 | 3 | | | SNAR-H | 1.00 |
| 19033 | 3 | | | | | | SLC6A19 | 1.00 | 19129 | 3 | | | SNAR-I | 1.00 |
| 19034 | 3 | | | | | | SLC6A2 | 1.00 | 19130 | 3 | | | SNCAIP | 1.00 |
| 19035 | 3 | | | | | | SLC6A20 | 1.00 | 19131 | 3 | | | SNCB | 1.00 |
| 19036 | 3 | | | | | | SLC6A3 | 1.00 | 19132 | 3 | | | SNCG | 1.00 |
| 19037 | 3 | | | | | | SLC6A4 | 1.00 | 19133 | 3 | | | SND1-IT1 | 1.00 |
| 19038 | 3 | | | | | | SLC6A5 | 1.00 | 19134 | 3 | | | SNED1 | 1.00 |
| 19039 | 3 | | | | | | SLC6A7 | 1.00 | 19135 | 3 | | | SNHG4 | 1.00 |
| 19040 | 3 | | | | | | SLC7A10 | 1.00 | 19136 | 3 | | | SNORA1 | 1.00 |
| 19041 | 3 | | | | | | SLC7A11 | 1.00 | 19137 | 3 | | | SNORA10 | 1.00 |
| 19042 | 3 | | | | | | SLC7A13 | 1.00 | 19138 | 3 | | | SNORA11 | 1.00 |
| 19043 | 3 | | | | | | SLC7A14 | 1.00 | 19139 | 3 | | | SNORA11B | 1.00 |
| 19044 | 3 | | | | | | SLC7A2 | 1.00 | 19140 | 3 | | | SNORA11C | 1.00 |
| 19045 | 3 | | | | | | SLC7A3 | 1.00 | 19141 | 3 | | | SNORA11D | 1.00 |
| 19046 | 3 | | | | | | SLC7A4 | 1.00 | 19142 | 3 | | | SNORA11E | 1.00 |
| 19047 | 3 | | | | | | SLC7A5P2 | 1.00 | 19143 | 3 | | | SNORA13 | 1.00 |
| 19048 | 3 | | | | | | SLC7A9 | 1.00 | 19144 | 3 | | | SNORA14A | 1.00 |
| 19049 | 3 | | | | | | SLC8A2 | 1.00 | 19145 | 3 | | | SNORA14B | 1.00 |
| 19050 | 3 | | | | | | SLC8A3 | 1.00 | 19146 | 3 | | | SNORA15 | 1.00 |
| 19051 | 3 | | | | | | SLC9A10 | 1.00 | 19147 | 3 | | | SNORA16A | 1.00 |
| 19052 | 3 | | | | | | SLC9A11 | 1.00 | 19148 | 3 | | | SNORA16B | 1.00 |
| 19053 | 3 | | | | | | SLC9A2 | 1.00 | 19149 | 3 | | | SNORA17 | 1.00 |
| 19054 | 3 | | | | | | SLC9A3 | 1.00 | 19150 | 3 | | | SNORA18 | 1.00 |
| 19055 | 3 | | | | | | SLC9A4 | 1.00 | 19151 | 3 | | | SNORA19 | 1.00 |
| 19056 | 3 | | | | | | SLC9A5 | 1.00 | 19152 | 3 | | | SNORA20 | 1.00 |
| 19057 | 3 | | | | | | SLC9A7 | 1.00 | 19153 | 3 | | | SNORA22 | 1.00 |
| 19058 | 3 | | | | | | SLC9B1 | 1.00 | 19154 | 3 | | | SNORA23 | 1.00 |
| 19059 | 3 | | | | | | SLCO1A2 | 1.00 | 19155 | 3 | | | SNORA24 | 1.00 |
| 19060 | 3 | | | | | | SLCO1B1 | 1.00 | 19156 | 3 | | | SNORA25 | 1.00 |
| 19061 | 3 | | | | | | SLCO1B3 | 1.00 | 19157 | 3 | | | SNORA26 | 1.00 |
| 19062 | 3 | | | | | | SLCO1B7 | 1.00 | 19158 | 3 | | | SNORA28 | 1.00 |
| 19063 | 3 | | | | | | SLCO1C1 | 1.00 | 19159 | 3 | | | SNORA2A | 1.00 |
| 19064 | 3 | | | | | | SLCO2A1 | 1.00 | 19160 | 3 | | | SNORA3 | 1.00 |
| 19065 | 3 | | | | | | SLCO2B1 | 1.00 | 19161 | 3 | | | SNORA30 | 1.00 |
| 19066 | 3 | | | | | | SLCO4A1 | 1.00 | 19162 | 3 | | | SNORA32 | 1.00 |
| 19067 | 3 | | | | | | SLCO5A1 | 1.00 | 19163 | 3 | | | SNORA33 | 1.00 |
| 19068 | 3 | | | | | | SLCO6A1 | 1.00 | 19164 | 3 | | | SNORA34 | 1.00 |
| 19069 | 3 | | | | | | SLED1 | 1.00 | 19165 | 3 | | | SNORA35 | 1.00 |
| 19070 | 3 | | | | | | SLFNL1 | 1.00 | 19166 | 3 | | | SNORA36A | 1.00 |
| 19071 | 3 | | | | | | SLIT1 | 1.00 | 19167 | 3 | | | SNORA36B | 1.00 |
| 19072 | 3 | | | | | | SLIT2 | 1.00 | 19168 | 3 | | | SNORA36C | 1.00 |
| 19073 | 3 | | | | | | SLIT2-IT1 | 1.00 | 19169 | 3 | | | SNORA37 | 1.00 |
| 19074 | 3 | | | | | | SLIT3 | 1.00 | 19170 | 3 | | | SNORA38 | 1.00 |
| 19075 | 3 | | | | | | SLITRK1 | 1.00 | 19171 | 3 | | | SNORA38B | 1.00 |
| 19076 | 3 | | | | | | SLITRK2 | 1.00 | 19172 | 3 | | | SNORA41 | 1.00 |
| 19077 | 3 | | | | | | SLITRK3 | 1.00 | 19173 | 3 | | | SNORA42 | 1.00 |
| 19078 | 3 | | | | | | SLITRK5 | 1.00 | 19174 | 3 | | | SNORA43 | 1.00 |
| 19079 | 3 | | | | | | SLITRK6 | 1.00 | 19175 | 3 | | | SNORA44 | 1.00 |
| 19080 | 3 | | | | | | SLMO1 | 1.00 | 19176 | 3 | | | SNORA46 | 1.00 |
| 19081 | 3 | | | | | | SLMO2-ATP5E | 1.00 | 19177 | 3 | | | SNORA47 | 1.00 |
| 19082 | 3 | | | | | | SLN | 1.00 | 19178 | 3 | | | SNORA49 | 1.00 |
| 19083 | 3 | | | | | | SLURP1 | 1.00 | 19179 | 3 | | | SNORA50 | 1.00 |
| 19084 | 3 | | | | | | SMAD5-AS1 | 1.00 | 19180 | 3 | | | SNORA51 | 1.00 |
| 19085 | 3 | | | | | | SMAD6 | 1.00 | 19181 | 3 | | | SNORA52 | 1.00 |
| 19086 | 3 | | | | | | SMAD9 | 1.00 | 19182 | 3 | | | SNORA53 | 1.00 |
| 19087 | 3 | | | | | | SMARCA1 | 1.00 | 19183 | 3 | | | SNORA54 | 1.00 |
| 19088 | 3 | | | | | | SMC1B | 1.00 | 19184 | 3 | | | SNORA55 | 1.00 |
| 19089 | 3 | | | | | | SMCP | 1.00 | 19185 | 3 | | | SNORA56 | 1.00 |
| 19090 | 3 | | | | | | SMCR5 | 1.00 | 19186 | 3 | | | SNORA58 | 1.00 |
| 19091 | 3 | | | | | | SMCR9 | 1.00 | 19187 | 3 | | | SNORA59B | 1.00 |
| 19092 | 3 | | | | | | SMEK3P | 1.00 | 19188 | 3 | | | SNORA5A | 1.00 |
| 19093 | 3 | | | | | | SMN1 | 1.00 | 19189 | 3 | | | SNORA5B | 1.00 |
| 19094 | 3 | | | | | | SMO | 1.00 | 19190 | 3 | | | SNORA5C | 1.00 |
| 19095 | 3 | | | | | | SMOC1 | 1.00 | 19191 | 3 | | | SNORA6 | 1.00 |
| 19096 | 3 | | | | | | SMOC2 | 1.00 | 19192 | 3 | | | SNORA60 | 1.00 |

Fig. 41 - 101

| | | | | | | | | | | | | | | |
|---|---|---|---|---|---|---|---|---|---|---|---|---|---|---|
| 19193 | 3 | | | | | SNORA61 | 1.00 | 19289 | 3 | | | | SNORD115-23 | 1.00 |
| 19194 | 3 | | | | | SNORA62 | 1.00 | 19290 | 3 | | | | SNORD115-24 | 1.00 |
| 19195 | 3 | | | | | SNORA64 | 1.00 | 19291 | 3 | | | | SNORD115-25 | 1.00 |
| 19196 | 3 | | | | | SNORA66 | 1.00 | 19292 | 3 | | | | SNORD115-26 | 1.00 |
| 19197 | 3 | | | | | SNORA69 | 1.00 | 19293 | 3 | | | | SNORD115-27 | 1.00 |
| 19198 | 3 | | | | | SNORA70B | 1.00 | 19294 | 3 | | | | SNORD115-28 | 1.00 |
| 19199 | 3 | | | | | SNORA70C | 1.00 | 19295 | 3 | | | | SNORD115-29 | 1.00 |
| 19200 | 3 | | | | | SNORA70D | 1.00 | 19296 | 3 | | | | SNORD115-3 | 1.00 |
| 19201 | 3 | | | | | SNORA70E | 1.00 | 19297 | 3 | | | | SNORD115-30 | 1.00 |
| 19202 | 3 | | | | | SNORA70F | 1.00 | 19298 | 3 | | | | SNORD115-31 | 1.00 |
| 19203 | 3 | | | | | SNORA70G | 1.00 | 19299 | 3 | | | | SNORD115-32 | 1.00 |
| 19204 | 3 | | | | | SNORA71A | 1.00 | 19300 | 3 | | | | SNORD115-33 | 1.00 |
| 19205 | 3 | | | | | SNORA71B | 1.00 | 19301 | 3 | | | | SNORD115-34 | 1.00 |
| 19206 | 3 | | | | | SNORA71C | 1.00 | 19302 | 3 | | | | SNORD115-35 | 1.00 |
| 19207 | 3 | | | | | SNORA71D | 1.00 | 19303 | 3 | | | | SNORD115-37 | 1.00 |
| 19208 | 3 | | | | | SNORA72 | 1.00 | 19304 | 3 | | | | SNORD115-38 | 1.00 |
| 19209 | 3 | | | | | SNORA74A | 1.00 | 19305 | 3 | | | | SNORD115-39 | 1.00 |
| 19210 | 3 | | | | | SNORA74B | 1.00 | 19306 | 3 | | | | SNORD115-4 | 1.00 |
| 19211 | 3 | | | | | SNORA76 | 1.00 | 19307 | 3 | | | | SNORD115-40 | 1.00 |
| 19212 | 3 | | | | | SNORA77 | 1.00 | 19308 | 3 | | | | SNORD115-41 | 1.00 |
| 19213 | 3 | | | | | SNORA78 | 1.00 | 19309 | 3 | | | | SNORD115-42 | 1.00 |
| 19214 | 3 | | | | | SNORA79 | 1.00 | 19310 | 3 | | | | SNORD115-44 | 1.00 |
| 19215 | 3 | | | | | SNORA7A | 1.00 | 19311 | 3 | | | | SNORD115-45 | 1.00 |
| 19216 | 3 | | | | | SNORA7B | 1.00 | 19312 | 3 | | | | SNORD115-47 | 1.00 |
| 19217 | 3 | | | | | SNORA80 | 1.00 | 19313 | 3 | | | | SNORD115-48 | 1.00 |
| 19218 | 3 | | | | | SNORA80B | 1.00 | 19314 | 3 | | | | SNORD115-5 | 1.00 |
| 19219 | 3 | | | | | SNORA84 | 1.00 | 19315 | 3 | | | | SNORD115-6 | 1.00 |
| 19220 | 3 | | | | | SNORA9 | 1.00 | 19316 | 3 | | | | SNORD115-7 | 1.00 |
| 19221 | 3 | | | | | SNORD10 | 1.00 | 19317 | 3 | | | | SNORD115-8 | 1.00 |
| 19222 | 3 | | | | | SNORD100 | 1.00 | 19318 | 3 | | | | SNORD115-9 | 1.00 |
| 19223 | 3 | | | | | SNORD101 | 1.00 | 19319 | 3 | | | | SNORD116-1 | 1.00 |
| 19224 | 3 | | | | | SNORD102 | 1.00 | 19320 | 3 | | | | SNORD116-10 | 1.00 |
| 19225 | 3 | | | | | SNORD103A | 1.00 | 19321 | 3 | | | | SNORD116-11 | 1.00 |
| 19226 | 3 | | | | | SNORD104 | 1.00 | 19322 | 3 | | | | SNORD116-12 | 1.00 |
| 19227 | 3 | | | | | SNORD105 | 1.00 | 19323 | 3 | | | | SNORD116-13 | 1.00 |
| 19228 | 3 | | | | | SNORD105B | 1.00 | 19324 | 3 | | | | SNORD116-14 | 1.00 |
| 19229 | 3 | | | | | SNORD107 | 1.00 | 19325 | 3 | | | | SNORD116-15 | 1.00 |
| 19230 | 3 | | | | | SNORD108 | 1.00 | 19326 | 3 | | | | SNORD116-16 | 1.00 |
| 19231 | 3 | | | | | SNORD109B | 1.00 | 19327 | 3 | | | | SNORD116-17 | 1.00 |
| 19232 | 3 | | | | | SNORD11 | 1.00 | 19328 | 3 | | | | SNORD116-18 | 1.00 |
| 19233 | 3 | | | | | SNORD110 | 1.00 | 19329 | 3 | | | | SNORD116-2 | 1.00 |
| 19234 | 3 | | | | | SNORD111 | 1.00 | 19330 | 3 | | | | SNORD116-20 | 1.00 |
| 19235 | 3 | | | | | SNORD111B | 1.00 | 19331 | 3 | | | | SNORD116-21 | 1.00 |
| 19236 | 3 | | | | | SNORD113-1 | 1.00 | 19332 | 3 | | | | SNORD116-22 | 1.00 |
| 19237 | 3 | | | | | SNORD113-2 | 1.00 | 19333 | 3 | | | | SNORD116-23 | 1.00 |
| 19238 | 3 | | | | | SNORD113-4 | 1.00 | 19334 | 3 | | | | SNORD116-24 | 1.00 |
| 19239 | 3 | | | | | SNORD113-5 | 1.00 | 19335 | 3 | | | | SNORD116-25 | 1.00 |
| 19240 | 3 | | | | | SNORD113-6 | 1.00 | 19336 | 3 | | | | SNORD116-26 | 1.00 |
| 19241 | 3 | | | | | SNORD113-7 | 1.00 | 19337 | 3 | | | | SNORD116-27 | 1.00 |
| 19242 | 3 | | | | | SNORD113-9 | 1.00 | 19338 | 3 | | | | SNORD116-28 | 1.00 |
| 19243 | 3 | | | | | SNORD114-1 | 1.00 | 19339 | 3 | | | | SNORD116-29 | 1.00 |
| 19244 | 3 | | | | | SNORD114-10 | 1.00 | 19340 | 3 | | | | SNORD116-3 | 1.00 |
| 19245 | 3 | | | | | SNORD114-11 | 1.00 | 19341 | 3 | | | | SNORD116-4 | 1.00 |
| 19246 | 3 | | | | | SNORD114-12 | 1.00 | 19342 | 3 | | | | SNORD116-5 | 1.00 |
| 19247 | 3 | | | | | SNORD114-13 | 1.00 | 19343 | 3 | | | | SNORD116-6 | 1.00 |
| 19248 | 3 | | | | | SNORD114-14 | 1.00 | 19344 | 3 | | | | SNORD116-7 | 1.00 |
| 19249 | 3 | | | | | SNORD114-15 | 1.00 | 19345 | 3 | | | | SNORD116-8 | 1.00 |
| 19250 | 3 | | | | | SNORD114-16 | 1.00 | 19346 | 3 | | | | SNORD116-9 | 1.00 |
| 19251 | 3 | | | | | SNORD114-17 | 1.00 | 19347 | 3 | | | | SNORD117 | 1.00 |
| 19252 | 3 | | | | | SNORD114-18 | 1.00 | 19348 | 3 | | | | SNORD119 | 1.00 |
| 19253 | 3 | | | | | SNORD114-19 | 1.00 | 19349 | 3 | | | | SNORD118 | 1.00 |
| 19254 | 3 | | | | | SNORD114-2 | 1.00 | 19350 | 3 | | | | SNORD12 | 1.00 |
| 19255 | 3 | | | | | SNORD114-20 | 1.00 | 19351 | 3 | | | | SNORD121A | 1.00 |
| 19256 | 3 | | | | | SNORD114-21 | 1.00 | 19352 | 3 | | | | SNORD121B | 1.00 |
| 19257 | 3 | | | | | SNORD114-22 | 1.00 | 19353 | 3 | | | | SNORD123 | 1.00 |
| 19258 | 3 | | | | | SNORD114-23 | 1.00 | 19354 | 3 | | | | SNORD124 | 1.00 |
| 19259 | 3 | | | | | SNORD114-24 | 1.00 | 19355 | 3 | | | | SNORD125 | 1.00 |
| 19260 | 3 | | | | | SNORD114-25 | 1.00 | 19356 | 3 | | | | SNORD126 | 1.00 |
| 19261 | 3 | | | | | SNORD114-26 | 1.00 | 19357 | 3 | | | | SNORD127 | 1.00 |
| 19262 | 3 | | | | | SNORD114-27 | 1.00 | 19358 | 3 | | | | SNORD128 | 1.00 |
| 19263 | 3 | | | | | SNORD114-28 | 1.00 | 19359 | 3 | | | | SNORD12C | 1.00 |
| 19264 | 3 | | | | | SNORD114-29 | 1.00 | 19360 | 3 | | | | SNORD16 | 1.00 |
| 19265 | 3 | | | | | SNORD114-3 | 1.00 | 19361 | 3 | | | | SNORD18A | 1.00 |
| 19266 | 3 | | | | | SNORD114-30 | 1.00 | 19362 | 3 | | | | SNORD18B | 1.00 |
| 19267 | 3 | | | | | SNORD114-31 | 1.00 | 19363 | 3 | | | | SNORD18C | 1.00 |
| 19268 | 3 | | | | | SNORD114-4 | 1.00 | 19364 | 3 | | | | SNORD19 | 1.00 |
| 19269 | 3 | | | | | SNORD114-5 | 1.00 | 19365 | 3 | | | | SNORD19B | 1.00 |
| 19270 | 3 | | | | | SNORD114-6 | 1.00 | 19366 | 3 | | | | SNORD1A | 1.00 |
| 19271 | 3 | | | | | SNORD114-7 | 1.00 | 19367 | 3 | | | | SNORD1B | 1.00 |
| 19272 | 3 | | | | | SNORD114-8 | 1.00 | 19368 | 3 | | | | SNORD1C | 1.00 |
| 19273 | 3 | | | | | SNORD114-9 | 1.00 | 19369 | 3 | | | | SNORD2 | 1.00 |
| 19274 | 3 | | | | | SNORD115-1 | 1.00 | 19370 | 3 | | | | SNORD20 | 1.00 |
| 19275 | 3 | | | | | SNORD115-10 | 1.00 | 19371 | 3 | | | | SNORD21 | 1.00 |
| 19276 | 3 | | | | | SNORD115-11 | 1.00 | 19372 | 3 | | | | SNORD22 | 1.00 |
| 19277 | 3 | | | | | SNORD115-12 | 1.00 | 19373 | 3 | | | | SNORD23 | 1.00 |
| 19278 | 3 | | | | | SNORD115-13 | 1.00 | 19374 | 3 | | | | SNORD24 | 1.00 |
| 19279 | 3 | | | | | SNORD115-14 | 1.00 | 19375 | 3 | | | | SNORD25 | 1.00 |
| 19280 | 3 | | | | | SNORD115-15 | 1.00 | 19376 | 3 | | | | SNORD26 | 1.00 |
| 19281 | 3 | | | | | SNORD115-16 | 1.00 | 19377 | 3 | | | | SNORD27 | 1.00 |
| 19282 | 3 | | | | | SNORD115-17 | 1.00 | 19378 | 3 | | | | SNORD28 | 1.00 |
| 19283 | 3 | | | | | SNORD115-18 | 1.00 | 19379 | 3 | | | | SNORD29 | 1.00 |
| 19284 | 3 | | | | | SNORD115-19 | 1.00 | 19380 | 3 | | | | SNORD30 | 1.00 |
| 19285 | 3 | | | | | SNORD115-2 | 1.00 | 19381 | 3 | | | | SNORD31 | 1.00 |
| 19286 | 3 | | | | | SNORD115-20 | 1.00 | 19382 | 3 | | | | SNORD32A | 1.00 |
| 19287 | 3 | | | | | SNORD115-21 | 1.00 | 19383 | 3 | | | | SNORD32B | 1.00 |
| 19288 | 3 | | | | | SNORD115-22 | 1.00 | 19384 | 3 | | | | SNORD33 | 1.00 |

Fig. 41 - 102

| | | | | | | | | | | | | | | | |
|---|---|---|---|---|---|---|---|---|---|---|---|---|---|---|---|
| 19385 | 3 | | | | | SNORD34 | 1.00 | 19481 | 3 | | | | | SOD3 | 1.00 |
| 19386 | 3 | | | | | SNORD35A | 1.00 | 19482 | 3 | | | | | SOHLH1 | 1.00 |
| 19387 | 3 | | | | | SNORD35B | 1.00 | 19483 | 3 | | | | | SOHLH2 | 1.00 |
| 19388 | 3 | | | | | SNORD36A | 1.00 | 19484 | 3 | | | | | SORBS1 | 1.00 |
| 19389 | 3 | | | | | SNORD36B | 1.00 | 19485 | 3 | | | | | SORBS2 | 1.00 |
| 19390 | 3 | | | | | SNORD36C | 1.00 | 19486 | 3 | | | | | SORCS1 | 1.00 |
| 19391 | 3 | | | | | SNORD37 | 1.00 | 19487 | 3 | | | | | SORCS2 | 1.00 |
| 19392 | 3 | | | | | SNORD38A | 1.00 | 19488 | 3 | | | | | SORCS3 | 1.00 |
| 19393 | 3 | | | | | SNORD38B | 1.00 | 19489 | 3 | | | | | SOST | 1.00 |
| 19394 | 3 | | | | | SNORD41 | 1.00 | 19490 | 3 | | | | | SOSTDC1 | 1.00 |
| 19395 | 3 | | | | | SNORD42A | 1.00 | 19491 | 3 | | | | | SOWAHA | 1.00 |
| 19396 | 3 | | | | | SNORD42B | 1.00 | 19492 | 3 | | | | | SOWAHB | 1.00 |
| 19397 | 3 | | | | | SNORD43 | 1.00 | 19493 | 3 | | | | | SOX1 | 1.00 |
| 19398 | 3 | | | | | SNORD44 | 1.00 | 19494 | 3 | | | | | SOX10 | 1.00 |
| 19399 | 3 | | | | | SNORD45A | 1.00 | 19495 | 3 | | | | | SOX11 | 1.00 |
| 19400 | 3 | | | | | SNORD45B | 1.00 | 19496 | 3 | | | | | SOX14 | 1.00 |
| 19401 | 3 | | | | | SNORD45C | 1.00 | 19497 | 3 | | | | | SOX15 | 1.00 |
| 19402 | 3 | | | | | SNORD46 | 1.00 | 19498 | 3 | | | | | SOX17 | 1.00 |
| 19403 | 3 | | | | | SNORD47 | 1.00 | 19499 | 3 | | | | | SOX18 | 1.00 |
| 19404 | 3 | | | | | SNORD48 | 1.00 | 19500 | 3 | | | | | SOX2 | 1.00 |
| 19405 | 3 | | | | | SNORD49A | 1.00 | 19501 | 3 | | | | | SOX2-OT | 1.00 |
| 19406 | 3 | | | | | SNORD49B | 1.00 | 19502 | 3 | | | | | SOX21 | 1.00 |
| 19407 | 3 | | | | | SNORD4A | 1.00 | 19503 | 3 | | | | | SOX3 | 1.00 |
| 19408 | 3 | | | | | SNORD4B | 1.00 | 19504 | 3 | | | | | SOX30 | 1.00 |
| 19409 | 3 | | | | | SNORD5 | 1.00 | 19505 | 3 | | | | | SOX5 | 1.00 |
| 19410 | 3 | | | | | SNORD50A | 1.00 | 19506 | 3 | | | | | SOX6 | 1.00 |
| 19411 | 3 | | | | | SNORD50B | 1.00 | 19507 | 3 | | | | | SOX7 | 1.00 |
| 19412 | 3 | | | | | SNORD51 | 1.00 | 19508 | 3 | | | | | SOX9 | 1.00 |
| 19413 | 3 | | | | | SNORD52 | 1.00 | 19509 | 3 | | | | | SP5 | 1.00 |
| 19414 | 3 | | | | | SNORD53 | 1.00 | 19510 | 3 | | | | | SP6 | 1.00 |
| 19415 | 3 | | | | | SNORD54 | 1.00 | 19511 | 3 | | | | | SP7 | 1.00 |
| 19416 | 3 | | | | | SNORD55 | 1.00 | 19512 | 3 | | | | | SP8 | 1.00 |
| 19417 | 3 | | | | | SNORD56 | 1.00 | 19513 | 3 | | | | | SP9 | 1.00 |
| 19418 | 3 | | | | | SNORD56B | 1.00 | 19514 | 3 | | | | | SPACA1 | 1.00 |
| 19419 | 3 | | | | | SNORD57 | 1.00 | 19515 | 3 | | | | | SPACA3 | 1.00 |
| 19420 | 3 | | | | | SNORD58A | 1.00 | 19516 | 3 | | | | | SPACA4 | 1.00 |
| 19421 | 3 | | | | | SNORD58B | 1.00 | 19517 | 3 | | | | | SPACA5 | 1.00 |
| 19422 | 3 | | | | | SNORD58C | 1.00 | 19518 | 3 | | | | | SPACA5B | 1.00 |
| 19423 | 3 | | | | | SNORD59A | 1.00 | 19519 | 3 | | | | | SPACA7 | 1.00 |
| 19424 | 3 | | | | | SNORD59B | 1.00 | 19520 | 3 | | | | | SPAG11A | 1.00 |
| 19425 | 3 | | | | | SNORD6 | 1.00 | 19521 | 3 | | | | | SPAG11B | 1.00 |
| 19426 | 3 | | | | | SNORD60 | 1.00 | 19522 | 3 | | | | | SPAG17 | 1.00 |
| 19427 | 3 | | | | | SNORD61 | 1.00 | 19523 | 3 | | | | | SPAG4 | 1.00 |
| 19428 | 3 | | | | | SNORD62A | 1.00 | 19524 | 3 | | | | | SPAG5 | 1.00 |
| 19429 | 3 | | | | | SNORD63 | 1.00 | 19525 | 3 | | | | | SPAG6 | 1.00 |
| 19430 | 3 | | | | | SNORD64 | 1.00 | 19526 | 3 | | | | | SPAG8 | 1.00 |
| 19431 | 3 | | | | | SNORD65 | 1.00 | 19527 | 3 | | | | | SPAM1 | 1.00 |
| 19432 | 3 | | | | | SNORD66 | 1.00 | 19528 | 3 | | | | | SPANXA1 | 1.00 |
| 19433 | 3 | | | | | SNORD67 | 1.00 | 19529 | 3 | | | | | SPANXA2 | 1.00 |
| 19434 | 3 | | | | | SNORD68 | 1.00 | 19530 | 3 | | | | | SPANXA2-OT1 | 1.00 |
| 19435 | 3 | | | | | SNORD69 | 1.00 | 19531 | 3 | | | | | SPANXB2 | 1.00 |
| 19436 | 3 | | | | | SNORD7 | 1.00 | 19532 | 3 | | | | | SPANXC | 1.00 |
| 19437 | 3 | | | | | SNORD70 | 1.00 | 19533 | 3 | | | | | SPANXD | 1.00 |
| 19438 | 3 | | | | | SNORD71 | 1.00 | 19534 | 3 | | | | | SPANXE | 1.00 |
| 19439 | 3 | | | | | SNORD72 | 1.00 | 19535 | 3 | | | | | SPANXN1 | 1.00 |
| 19440 | 3 | | | | | SNORD73A | 1.00 | 19536 | 3 | | | | | SPANXN2 | 1.00 |
| 19441 | 3 | | | | | SNORD74 | 1.00 | 19537 | 3 | | | | | SPANXN3 | 1.00 |
| 19442 | 3 | | | | | SNORD75 | 1.00 | 19538 | 3 | | | | | SPANXN4 | 1.00 |
| 19443 | 3 | | | | | SNORD76 | 1.00 | 19539 | 3 | | | | | SPANXN5 | 1.00 |
| 19444 | 3 | | | | | SNORD77 | 1.00 | 19540 | 3 | | | | | SPARCL1 | 1.00 |
| 19445 | 3 | | | | | SNORD78 | 1.00 | 19541 | 3 | | | | | SPATA12 | 1.00 |
| 19446 | 3 | | | | | SNORD79 | 1.00 | 19542 | 3 | | | | | SPATA16 | 1.00 |
| 19447 | 3 | | | | | SNORD8 | 1.00 | 19543 | 3 | | | | | SPATA17 | 1.00 |
| 19448 | 3 | | | | | SNORD80 | 1.00 | 19544 | 3 | | | | | SPATA18 | 1.00 |
| 19449 | 3 | | | | | SNORD81 | 1.00 | 19545 | 3 | | | | | SPATA19 | 1.00 |
| 19450 | 3 | | | | | SNORD82 | 1.00 | 19546 | 3 | | | | | SPATA21 | 1.00 |
| 19451 | 3 | | | | | SNORD83A | 1.00 | 19547 | 3 | | | | | SPATA22 | 1.00 |
| 19452 | 3 | | | | | SNORD83B | 1.00 | 19548 | 3 | | | | | SPATA24 | 1.00 |
| 19453 | 3 | | | | | SNORD84 | 1.00 | 19549 | 3 | | | | | SPATA25 | 1.00 |
| 19454 | 3 | | | | | SNORD85 | 1.00 | 19550 | 3 | | | | | SPATA3 | 1.00 |
| 19455 | 3 | | | | | SNORD86 | 1.00 | 19551 | 3 | | | | | SPATA4 | 1.00 |
| 19456 | 3 | | | | | SNORD87 | 1.00 | 19552 | 3 | | | | | SPATA7 | 1.00 |
| 19457 | 3 | | | | | SNORD88A | 1.00 | 19553 | 3 | | | | | SPATA8 | 1.00 |
| 19458 | 3 | | | | | SNORD88B | 1.00 | 19554 | 3 | | | | | SPATA9 | 1.00 |
| 19459 | 3 | | | | | SNORD88C | 1.00 | 19555 | 3 | | | | | SPATC1 | 1.00 |
| 19460 | 3 | | | | | SNORD9 | 1.00 | 19556 | 3 | | | | | SPATS1 | 1.00 |
| 19461 | 3 | | | | | SNORD90 | 1.00 | 19557 | 3 | | | | | SPC24 | 1.00 |
| 19462 | 3 | | | | | SNORD91A | 1.00 | 19558 | 3 | | | | | SPC25 | 1.00 |
| 19463 | 3 | | | | | SNORD91B | 1.00 | 19559 | 3 | | | | | SPDEF | 1.00 |
| 19464 | 3 | | | | | SNORD92 | 1.00 | 19560 | 3 | | | | | SPDYA | 1.00 |
| 19465 | 3 | | | | | SNORD93 | 1.00 | 19561 | 3 | | | | | SPDYE1 | 1.00 |
| 19466 | 3 | | | | | SNORD94 | 1.00 | 19562 | 3 | | | | | SPDYE3 | 1.00 |
| 19467 | 3 | | | | | SNORD95 | 1.00 | 19563 | 3 | | | | | SPDYE4 | 1.00 |
| 19468 | 3 | | | | | SNORD96A | 1.00 | 19564 | 3 | | | | | SPDYE5 | 1.00 |
| 19469 | 3 | | | | | SNORD96B | 1.00 | 19565 | 3 | | | | | SPDYE6 | 1.00 |
| 19470 | 3 | | | | | SNORD98 | 1.00 | 19566 | 3 | | | | | SPDYE7P | 1.00 |
| 19471 | 3 | | | | | SNORD99 | 1.00 | 19567 | 3 | | | | | SPDYE8P | 1.00 |
| 19472 | 3 | | | | | SNRPD2P2 | 1.00 | 19568 | 3 | | | | | SPEF1 | 1.00 |
| 19473 | 3 | | | | | SNTG1 | 1.00 | 19569 | 3 | | | | | SPEF2 | 1.00 |
| 19474 | 3 | | | | | SNTG2 | 1.00 | 19570 | 3 | | | | | SPEG | 1.00 |
| 19475 | 3 | | | | | SNTN | 1.00 | 19571 | 3 | | | | | SPEM1 | 1.00 |
| 19476 | 3 | | | | | SNX31 | 1.00 | 19572 | 3 | | | | | SPERT | 1.00 |
| 19477 | 3 | | | | | SNX32 | 1.00 | 19573 | 3 | | | | | SPG20OS | 1.00 |
| 19478 | 3 | | | | | SNX7 | 1.00 | 19574 | 3 | | | | | SPHKAP | 1.00 |
| 19479 | 3 | | | | | SOAT2 | 1.00 | 19575 | 3 | | | | | SPIC | 1.00 |
| 19480 | 3 | | | | | SOBP | 1.00 | 19576 | 3 | | | | | SPICE1 | 1.00 |

Fig. 41 - 103

| | | | | | | | | | | | | | | |
|---|---|---|---|---|---|---|---|---|---|---|---|---|---|---|
| 19577 | 3 | | | | | SPINK1 | 1.00 | 19673 | 3 | | | | STARD6 | 1.00 |
| 19578 | 3 | | | | | SPINK13 | 1.00 | 19674 | 3 | | | | STARD9 | 1.00 |
| 19579 | 3 | | | | | SPINK14 | 1.00 | 19675 | 3 | | | | STATH | 1.00 |
| 19580 | 3 | | | | | SPINK2 | 1.00 | 19676 | 3 | | | | STC1 | 1.00 |
| 19581 | 3 | | | | | SPINK4 | 1.00 | 19677 | 3 | | | | STC2 | 1.00 |
| 19582 | 3 | | | | | SPINK5 | 1.00 | 19678 | 3 | | | | STEAP1 | 1.00 |
| 19583 | 3 | | | | | SPINK6 | 1.00 | 19679 | 3 | | | | STEAP1B | 1.00 |
| 19584 | 3 | | | | | SPINK7 | 1.00 | 19680 | 3 | | | | STEAP2 | 1.00 |
| 19585 | 3 | | | | | SPINK8 | 1.00 | 19681 | 3 | | | | STH | 1.00 |
| 19586 | 3 | | | | | SPINK9 | 1.00 | 19682 | 3 | | | | STIL | 1.00 |
| 19587 | 3 | | | | | SPINLW1 | 1.00 | 19683 | 3 | | | | STK31 | 1.00 |
| 19588 | 3 | | | | | SPINLW1-WFDC6 | 1.00 | 19684 | 3 | | | | STK32A | 1.00 |
| 19589 | 3 | | | | | SPINT3 | 1.00 | 19685 | 3 | | | | STK33 | 1.00 |
| 19590 | 3 | | | | | SPINT4 | 1.00 | 19686 | 3 | | | | STK36 | 1.00 |
| 19591 | 3 | | | | | SPIRE2 | 1.00 | 19687 | 3 | | | | STL | 1.00 |
| 19592 | 3 | | | | | SPO11 | 1.00 | 19688 | 3 | | | | STMN2 | 1.00 |
| 19593 | 3 | | | | | SPOCK3 | 1.00 | 19689 | 3 | | | | STMN4 | 1.00 |
| 19594 | 3 | | | | | SPON1 | 1.00 | 19690 | 3 | | | | STOML3 | 1.00 |
| 19595 | 3 | | | | | SPP2 | 1.00 | 19691 | 3 | | | | STON1 | 1.00 |
| 19596 | 3 | | | | | SPPL2C | 1.00 | 19692 | 3 | | | | STON1-GTF2A1L | 1.00 |
| 19597 | 3 | | | | | SPRED3 | 1.00 | 19693 | 3 | | | | STOX1 | 1.00 |
| 19598 | 3 | | | | | SPRN | 1.00 | 19694 | 3 | | | | STOX2 | 1.00 |
| 19599 | 3 | | | | | SPRNP1 | 1.00 | 19695 | 3 | | | | STRA6 | 1.00 |
| 19600 | 3 | | | | | SPRR1A | 1.00 | 19696 | 3 | | | | STRA8 | 1.00 |
| 19601 | 3 | | | | | SPRR1B | 1.00 | 19697 | 3 | | | | STRC | 1.00 |
| 19602 | 3 | | | | | SPRR2A | 1.00 | 19698 | 3 | | | | STX16-NPEPL1 | 1.00 |
| 19603 | 3 | | | | | SPRR2B | 1.00 | 19699 | 3 | | | | STX19 | 1.00 |
| 19604 | 3 | | | | | SPRR2C | 1.00 | 19700 | 3 | | | | STX18 | 1.00 |
| 19605 | 3 | | | | | SPRR2D | 1.00 | 19701 | 3 | | | | STXBP1 | 1.00 |
| 19606 | 3 | | | | | SPRR2E | 1.00 | 19702 | 3 | | | | STXBP4 | 1.00 |
| 19607 | 3 | | | | | SPRR2F | 1.00 | 19703 | 3 | | | | STXBP5L | 1.00 |
| 19608 | 3 | | | | | SPRR2G | 1.00 | 19704 | 3 | | | | STXBP6 | 1.00 |
| 19609 | 3 | | | | | SPRR3 | 1.00 | 19705 | 3 | | | | STYK1 | 1.00 |
| 19610 | 3 | | | | | SPRR4 | 1.00 | 19706 | 3 | | | | SUCNR1 | 1.00 |
| 19611 | 3 | | | | | SPRY3 | 1.00 | 19707 | 3 | | | | SUGT1P1 | 1.00 |
| 19612 | 3 | | | | | SPRY4 | 1.00 | 19708 | 3 | | | | SUGT1P3 | 1.00 |
| 19613 | 3 | | | | | SPRYD5 | 1.00 | 19709 | 3 | | | | SULF1 | 1.00 |
| 19614 | 3 | | | | | SPSB4 | 1.00 | 19710 | 3 | | | | SULT1C2 | 1.00 |
| 19615 | 3 | | | | | SPTBN2 | 1.00 | 19711 | 3 | | | | SULT1C2P1 | 1.00 |
| 19616 | 3 | | | | | SPTBN4 | 1.00 | 19712 | 3 | | | | SULT1C3 | 1.00 |
| 19617 | 3 | | | | | SPTBN5 | 1.00 | 19713 | 3 | | | | SULT1C4 | 1.00 |
| 19618 | 3 | | | | | SPTLC3 | 1.00 | 19714 | 3 | | | | SULT1E1 | 1.00 |
| 19619 | 3 | | | | | SPZ1 | 1.00 | 19715 | 3 | | | | SULT2A1 | 1.00 |
| 19620 | 3 | | | | | SRCIN1 | 1.00 | 19716 | 3 | | | | SULT2B1 | 1.00 |
| 19621 | 3 | | | | | SRCRB4D | 1.00 | 19717 | 3 | | | | SULT4A1 | 1.00 |
| 19622 | 3 | | | | | SRD5A2 | 1.00 | 19718 | 3 | | | | SULT6B1 | 1.00 |
| 19623 | 3 | | | | | SRG7 | 1.00 | 19719 | 3 | | | | SUMO4 | 1.00 |
| 19624 | 3 | | | | | SRGAP1 | 1.00 | 19720 | 3 | | | | SUN3 | 1.00 |
| 19625 | 3 | | | | | SRGAP3 | 1.00 | 19721 | 3 | | | | SUN5 | 1.00 |
| 19626 | 3 | | | | | SRL | 1.00 | 19722 | 3 | | | | SUSD2 | 1.00 |
| 19627 | 3 | | | | | SRMS | 1.00 | 19723 | 3 | | | | SUSD4 | 1.00 |
| 19628 | 3 | | | | | SRPK3 | 1.00 | 19724 | 3 | | | | SUSD5 | 1.00 |
| 19629 | 3 | | | | | SRPX | 1.00 | 19725 | 3 | | | | SUZ12P | 1.00 |
| 19630 | 3 | | | | | SRPX2 | 1.00 | 19726 | 3 | | | | SV2A | 1.00 |
| 19631 | 3 | | | | | SRRM3 | 1.00 | 19727 | 3 | | | | SV2B | 1.00 |
| 19632 | 3 | | | | | SRRM4 | 1.00 | 19728 | 3 | | | | SV2C | 1.00 |
| 19633 | 3 | | | | | SRRM5 | 1.00 | 19729 | 3 | | | | SVEP1 | 1.00 |
| 19634 | 3 | | | | | SRSF12 | 1.00 | 19730 | 3 | | | | SVOP | 1.00 |
| 19635 | 3 | | | | | SRY | 1.00 | 19731 | 3 | | | | SVOPL | 1.00 |
| 19636 | 3 | | | | | SSC5D | 1.00 | 19732 | 3 | | | | SYBU | 1.00 |
| 19637 | 3 | | | | | SSPO | 1.00 | 19733 | 3 | | | | SYCE1 | 1.00 |
| 19638 | 3 | | | | | SSR4P1 | 1.00 | 19734 | 3 | | | | SYCE1L | 1.00 |
| 19639 | 3 | | | | | SST | 1.00 | 19735 | 3 | | | | SYCE2 | 1.00 |
| 19640 | 3 | | | | | SSTR1 | 1.00 | 19736 | 3 | | | | SYCE3 | 1.00 |
| 19641 | 3 | | | | | SSTR2 | 1.00 | 19737 | 3 | | | | SYCN | 1.00 |
| 19642 | 3 | | | | | SSTR4 | 1.00 | 19738 | 3 | | | | SYCP1 | 1.00 |
| 19643 | 3 | | | | | SSTR5 | 1.00 | 19739 | 3 | | | | SYCP2 | 1.00 |
| 19644 | 3 | | | | | SSX1 | 1.00 | 19740 | 3 | | | | SYCP2L | 1.00 |
| 19645 | 3 | | | | | SSX2 | 1.00 | 19741 | 3 | | | | SYCP3 | 1.00 |
| 19646 | 3 | | | | | SSX3 | 1.00 | 19742 | 3 | | | | SYDE1 | 1.00 |
| 19647 | 3 | | | | | SSX4 | 1.00 | 19743 | 3 | | | | SYDE2 | 1.00 |
| 19648 | 3 | | | | | SSX4B | 1.00 | 19744 | 3 | | | | SYN1 | 1.00 |
| 19649 | 3 | | | | | SSX5 | 1.00 | 19745 | 3 | | | | SYN2 | 1.00 |
| 19650 | 3 | | | | | SSX6 | 1.00 | 19746 | 3 | | | | SYN3 | 1.00 |
| 19651 | 3 | | | | | SSX7 | 1.00 | 19747 | 3 | | | | SYNDIG1 | 1.00 |
| 19652 | 3 | | | | | SSX8 | 1.00 | 19748 | 3 | | | | SYNDIG1L | 1.00 |
| 19653 | 3 | | | | | ST18 | 1.00 | 19749 | 3 | | | | SYNGR3 | 1.00 |
| 19654 | 3 | | | | | ST20-MTHFS | 1.00 | 19750 | 3 | | | | SYNGR4 | 1.00 |
| 19655 | 3 | | | | | ST5 | 1.00 | 19751 | 3 | | | | SYNJ2BP-COX16 | 1.00 |
| 19656 | 3 | | | | | ST6GAL2 | 1.00 | 19752 | 3 | | | | SYNPO2 | 1.00 |
| 19657 | 3 | | | | | ST6GALNAC5 | 1.00 | 19753 | 3 | | | | SYNPO2L | 1.00 |
| 19658 | 3 | | | | | ST7-AS1 | 1.00 | 19754 | 3 | | | | SYNPR | 1.00 |
| 19659 | 3 | | | | | ST7-AS2 | 1.00 | 19755 | 3 | | | | SYP | 1.00 |
| 19660 | 3 | | | | | ST7-OT3 | 1.00 | 19756 | 3 | | | | SYPL2 | 1.00 |
| 19661 | 3 | | | | | ST7-OT4 | 1.00 | 19757 | 3 | | | | SYS1-DBNDD2 | 1.00 |
| 19662 | 3 | | | | | ST8SIA1 | 1.00 | 19758 | 3 | | | | SYT1 | 1.00 |
| 19663 | 3 | | | | | ST8SIA2 | 1.00 | 19759 | 3 | | | | SYT10 | 1.00 |
| 19664 | 3 | | | | | ST8SIA3 | 1.00 | 19760 | 3 | | | | SYT12 | 1.00 |
| 19665 | 3 | | | | | ST8SIA5 | 1.00 | 19761 | 3 | | | | SYT13 | 1.00 |
| 19666 | 3 | | | | | STAB2 | 1.00 | 19762 | 3 | | | | SYT14 | 1.00 |
| 19667 | 3 | | | | | STAC | 1.00 | 19763 | 3 | | | | SYT14L | 1.00 |
| 19668 | 3 | | | | | STAC2 | 1.00 | 19764 | 3 | | | | SYT15 | 1.00 |
| 19669 | 3 | | | | | STAG3 | 1.00 | 19765 | 3 | | | | SYT16 | 1.00 |
| 19670 | 3 | | | | | STAP2 | 1.00 | 19766 | 3 | | | | SYT17 | 1.00 |
| 19671 | 3 | | | | | STAR | 1.00 | 19767 | 3 | | | | SYT2 | 1.00 |
| 19672 | 3 | | | | | STARD13 | 1.00 | 19768 | 3 | | | | SYT3 | 1.00 |

Fig. 41 - 104

| | | | | | | | | | | | | | |
|---|---|---|---|---|---|---|---|---|---|---|---|---|---|
| 19769 | 3 | | | | | SYT4 | 1.00 | 19864 | 3 | | | TCF24 | 1.00 |
| 19770 | 3 | | | | | SYT5 | 1.00 | 19865 | 3 | | | TCF7L1 | 1.00 |
| 19771 | 3 | | | | | SYT6 | 1.00 | 19866 | 3 | | | TCHH | 1.00 |
| 19772 | 3 | | | | | SYT7 | 1.00 | 19867 | 3 | | | TCHHL1 | 1.00 |
| 19773 | 3 | | | | | SYT8 | 1.00 | 19868 | 3 | | | TCL1B | 1.00 |
| 19774 | 3 | | | | | SYT9 | 1.00 | 19869 | 3 | | | TCL6 | 1.00 |
| 19775 | 3 | | | | | SYTL4 | 1.00 | 19870 | 3 | | | TCP10 | 1.00 |
| 19776 | 3 | | | | | SYTL5 | 1.00 | 19871 | 3 | | | TCP10L | 1.00 |
| 19777 | 3 | | | | | T | 1.00 | 19872 | 3 | | | TCP10L2 | 1.00 |
| 19778 | 3 | | | | | TAAR1 | 1.00 | 19873 | 3 | | | TCP11 | 1.00 |
| 19779 | 3 | | | | | TAAR2 | 1.00 | 19874 | 3 | | | TCTE1 | 1.00 |
| 19780 | 3 | | | | | TAAR3 | 1.00 | 19875 | 3 | | | TCTE3 | 1.00 |
| 19781 | 3 | | | | | TAAR5 | 1.00 | 19876 | 3 | | | TCTEX1D1 | 1.00 |
| 19782 | 3 | | | | | TAAR6 | 1.00 | 19877 | 3 | | | TCTEX1D4 | 1.00 |
| 19783 | 3 | | | | | TAAR8 | 1.00 | 19878 | 3 | | | TDGF1 | 1.00 |
| 19784 | 3 | | | | | TAAR9 | 1.00 | 19879 | 3 | | | TDGF1P3 | 1.00 |
| 19785 | 3 | | | | | TAC1 | 1.00 | 19880 | 3 | | | TDH | 1.00 |
| 19786 | 3 | | | | | TAC3 | 1.00 | 19881 | 3 | | | TDO2 | 1.00 |
| 19787 | 3 | | | | | TAC4 | 1.00 | 19882 | 3 | | | TDRD1 | 1.00 |
| 19788 | 3 | | | | | TACC2 | 1.00 | 19883 | 3 | | | TDRD10 | 1.00 |
| 19789 | 3 | | | | | TACR1 | 1.00 | 19884 | 3 | | | TDRD12 | 1.00 |
| 19790 | 3 | | | | | TACR2 | 1.00 | 19885 | 3 | | | TDRD5 | 1.00 |
| 19791 | 3 | | | | | TACR3 | 1.00 | 19886 | 3 | | | TDRD6 | 1.00 |
| 19792 | 3 | | | | | TAF7L | 1.00 | 19887 | 3 | | | TDRG1 | 1.00 |
| 19793 | 3 | | | | | TAG | 1.00 | 19888 | 3 | | | TEAD1 | 1.00 |
| 19794 | 3 | | | | | TAGLN3 | 1.00 | 19889 | 3 | | | TEAD2 | 1.00 |
| 19795 | 3 | | | | | TAL2 | 1.00 | 19890 | 3 | | | TEAD3 | 1.00 |
| 19796 | 3 | | | | | TANC1 | 1.00 | 19891 | 3 | | | TEAD4 | 1.00 |
| 19797 | 3 | | | | | TARM1 | 1.00 | 19892 | 3 | | | TECRL | 1.00 |
| 19798 | 3 | | | | | TAS1R1 | 1.00 | 19893 | 3 | | | TECTA | 1.00 |
| 19799 | 3 | | | | | TAS1R2 | 1.00 | 19894 | 3 | | | TECTB | 1.00 |
| 19800 | 3 | | | | | TAS1R3 | 1.00 | 19895 | 3 | | | TEDDM1 | 1.00 |
| 19801 | 3 | | | | | TAS2R1 | 1.00 | 19896 | 3 | | | TEK | 1.00 |
| 19802 | 3 | | | | | TAS2R10 | 1.00 | 19897 | 3 | | | TEKT1 | 1.00 |
| 19803 | 3 | | | | | TAS2R13 | 1.00 | 19898 | 3 | | | TEKT2 | 1.00 |
| 19804 | 3 | | | | | TAS2R14 | 1.00 | 19899 | 3 | | | TEKT3 | 1.00 |
| 19805 | 3 | | | | | TAS2R16 | 1.00 | 19900 | 3 | | | TEKT4 | 1.00 |
| 19806 | 3 | | | | | TAS2R19 | 1.00 | 19901 | 3 | | | TEKT5 | 1.00 |
| 19807 | 3 | | | | | TAS2R20 | 1.00 | 19902 | 3 | | | TEN1-CDK3 | 1.00 |
| 19808 | 3 | | | | | TAS2R3 | 1.00 | 19903 | 3 | | | TENC1 | 1.00 |
| 19809 | 3 | | | | | TAS2R30 | 1.00 | 19904 | 3 | | | TEPP | 1.00 |
| 19810 | 3 | | | | | TAS2R31 | 1.00 | 19905 | 3 | | | TERC | 1.00 |
| 19811 | 3 | | | | | TAS2R38 | 1.00 | 19906 | 3 | | | TERT | 1.00 |
| 19812 | 3 | | | | | TAS2R39 | 1.00 | 19907 | 3 | | | TET1 | 1.00 |
| 19813 | 3 | | | | | TAS2R4 | 1.00 | 19908 | 3 | | | TEX101 | 1.00 |
| 19814 | 3 | | | | | TAS2R41 | 1.00 | 19909 | 3 | | | TEX11 | 1.00 |
| 19815 | 3 | | | | | TAS2R42 | 1.00 | 19910 | 3 | | | TEX12 | 1.00 |
| 19816 | 3 | | | | | TAS2R43 | 1.00 | 19911 | 3 | | | TEX13A | 1.00 |
| 19817 | 3 | | | | | TAS2R46 | 1.00 | 19912 | 3 | | | TEX13B | 1.00 |
| 19818 | 3 | | | | | TAS2R5 | 1.00 | 19913 | 3 | | | TEX14 | 1.00 |
| 19819 | 3 | | | | | TAS2R50 | 1.00 | 19914 | 3 | | | TEX15 | 1.00 |
| 19820 | 3 | | | | | TAS2R60 | 1.00 | 19915 | 3 | | | TEX19 | 1.00 |
| 19821 | 3 | | | | | TAS2R7 | 1.00 | 19916 | 3 | | | TEX21P | 1.00 |
| 19822 | 3 | | | | | TAS2R8 | 1.00 | 19917 | 3 | | | TEX22 | 1.00 |
| 19823 | 3 | | | | | TAS2R9 | 1.00 | 19918 | 3 | | | TEX26 | 1.00 |
| 19824 | 3 | | | | | TAT | 1.00 | 19919 | 3 | | | TEX26-AS1 | 1.00 |
| 19825 | 3 | | | | | TBC1D16 | 1.00 | 19920 | 3 | | | TEX28 | 1.00 |
| 19826 | 3 | | | | | TBC1D19 | 1.00 | 19921 | 3 | | | TEX29 | 1.00 |
| 19827 | 3 | | | | | TBC1D21 | 1.00 | 19922 | 3 | | | TEX33 | 1.00 |
| 19828 | 3 | | | | | TBC1D26 | 1.00 | 19923 | 3 | | | TEX34 | 1.00 |
| 19829 | 3 | | | | | TBC1D28 | 1.00 | 19924 | 3 | | | TEX9 | 1.00 |
| 19830 | 3 | | | | | TBC1D29 | 1.00 | 19925 | 3 | | | TF | 1.00 |
| 19831 | 3 | | | | | TBC1D3 | 1.00 | 19926 | 3 | | | TFAP2A | 1.00 |
| 19832 | 3 | | | | | TBC1D30 | 1.00 | 19927 | 3 | | | TFAP2B | 1.00 |
| 19833 | 3 | | | | | TBC1D3P1-DHX40P1 | 1.00 | 19928 | 3 | | | TFAP2C | 1.00 |
| | | | | | | | | 19929 | 3 | | | TFAP2D | 1.00 |
| 19834 | 3 | | | | | TBC1D3P2 | 1.00 | 19930 | 3 | | | TFCP2L1 | 1.00 |
| 19835 | 3 | | | | | TBC1D3P5 | 1.00 | 19931 | 3 | | | TFDP3 | 1.00 |
| 19836 | 3 | | | | | TBC1D8B | 1.00 | 19932 | 3 | | | TFF1 | 1.00 |
| 19837 | 3 | | | | | TBL1Y | 1.00 | 19933 | 3 | | | TFF2 | 1.00 |
| 19838 | 3 | | | | | TBPL2 | 1.00 | 19934 | 3 | | | TFF3 | 1.00 |
| 19839 | 3 | | | | | TBR1 | 1.00 | 19935 | 3 | | | TFPI | 1.00 |
| 19840 | 3 | | | | | TBX1 | 1.00 | 19936 | 3 | | | TFPI2 | 1.00 |
| 19841 | 3 | | | | | TBX10 | 1.00 | 19937 | 3 | | | TG | 1.00 |
| 19842 | 3 | | | | | TBX15 | 1.00 | 19938 | 3 | | | TGFB1I1 | 1.00 |
| 19843 | 3 | | | | | TBX18 | 1.00 | 19939 | 3 | | | TGFB2 | 1.00 |
| 19844 | 3 | | | | | TBX2 | 1.00 | 19940 | 3 | | | TGFB3 | 1.00 |
| 19845 | 3 | | | | | TBX20 | 1.00 | 19941 | 3 | | | TGIF2-C20ORF24 | 1.00 |
| 19846 | 3 | | | | | TBX22 | 1.00 | 19942 | 3 | | | TGIF2LX | 1.00 |
| 19847 | 3 | | | | | TBX3 | 1.00 | 19943 | 3 | | | TGIF2LY | 1.00 |
| 19848 | 3 | | | | | TBX4 | 1.00 | 19944 | 3 | | | TGM1 | 1.00 |
| 19849 | 3 | | | | | TBX5 | 1.00 | 19945 | 3 | | | TGM4 | 1.00 |
| 19850 | 3 | | | | | TBX6 | 1.00 | 19946 | 3 | | | TGM5 | 1.00 |
| 19851 | 3 | | | | | TCAM1P | 1.00 | 19947 | 3 | | | TGM6 | 1.00 |
| 19852 | 3 | | | | | TCAP | 1.00 | 19948 | 3 | | | TGM7 | 1.00 |
| 19853 | 3 | | | | | TCEAL2 | 1.00 | 19949 | 3 | | | TH | 1.00 |
| 19854 | 3 | | | | | TCEAL5 | 1.00 | 19950 | 3 | | | THAP10 | 1.00 |
| 19855 | 3 | | | | | TCEAL6 | 1.00 | 19951 | 3 | | | THBS2 | 1.00 |
| 19856 | 3 | | | | | TCEAL7 | 1.00 | 19952 | 3 | | | THBS4 | 1.00 |
| 19857 | 3 | | | | | TCEB3B | 1.00 | 19953 | 3 | | | THEG | 1.00 |
| 19858 | 3 | | | | | TCEB3C | 1.00 | 19954 | 3 | | | THEG5 | 1.00 |
| 19859 | 3 | | | | | TCEB3CL | 1.00 | 19955 | 3 | | | THEGL | 1.00 |
| 19860 | 3 | | | | | TCERG1L | 1.00 | 19956 | 3 | | | THNSL2 | 1.00 |
| 19861 | 3 | | | | | TCF15 | 1.00 | 19957 | 3 | | | THPO | 1.00 |
| 19862 | 3 | | | | | TCF21 | 1.00 | 19958 | 3 | | | THRB | 1.00 |
| 19863 | 3 | | | | | TCF23 | 1.00 | 19959 | 3 | | | THRSP | 1.00 |

Fig. 41 - 105

| | | | | | | | | | | | | | | |
|---|---|---|---|---|---|---|---|---|---|---|---|---|---|---|
| 19960 | 3 | | | | | THSD1 | 1.00 | 20053 | 3 | | | | TMEM207 | 1.00 |
| 19961 | 3 | | | | | THSD4 | 1.00 | 20054 | 3 | | | | TMEM211 | 1.00 |
| 19962 | 3 | | | | | THSD7A | 1.00 | 20055 | 3 | | | | TMEM212 | 1.00 |
| 19963 | 3 | | | | | THSD7B | 1.00 | 20056 | 3 | | | | TMEM213 | 1.00 |
| 19964 | 3 | | | | | THY1 | 1.00 | 20057 | 3 | | | | TMEM215 | 1.00 |
| 19965 | 3 | | | | | TIE1 | 1.00 | 20058 | 3 | | | | TMEM217 | 1.00 |
| 19966 | 3 | | | | | TIGD4 | 1.00 | 20059 | 3 | | | | TMEM22 | 1.00 |
| 19967 | 3 | | | | | TIMD4 | 1.00 | 20060 | 3 | | | | TMEM221 | 1.00 |
| 19968 | 3 | | | | | TIMP3 | 1.00 | 20061 | 3 | | | | TMEM225 | 1.00 |
| 19969 | 3 | | | | | TIMP4 | 1.00 | 20062 | 3 | | | | TMEM229A | 1.00 |
| 19970 | 3 | | | | | TINAG | 1.00 | 20063 | 3 | | | | TMEM231 | 1.00 |
| 19971 | 3 | | | | | TINAGL1 | 1.00 | 20064 | 3 | | | | TMEM232 | 1.00 |
| 19972 | 3 | | | | | TIPARP-AS1 | 1.00 | 20065 | 3 | | | | TMEM233 | 1.00 |
| 19973 | 3 | | | | | TISP43 | 1.00 | 20066 | 3 | | | | TMEM235 | 1.00 |
| 19974 | 3 | | | | | TJP1 | 1.00 | 20067 | 3 | | | | TMEM236 | 1.00 |
| 19975 | 3 | | | | | TJP3 | 1.00 | 20068 | 3 | | | | TMEM237 | 1.00 |
| 19976 | 3 | | | | | TKTL2 | 1.00 | 20069 | 3 | | | | TMEM239 | 1.00 |
| 19977 | 3 | | | | | TLCD1 | 1.00 | 20070 | 3 | | | | TMEM240 | 1.00 |
| 19978 | 3 | | | | | TLCD2 | 1.00 | 20071 | 3 | | | | TMEM244 | 1.00 |
| 19979 | 3 | | | | | TLE6 | 1.00 | 20072 | 3 | | | | TMEM26 | 1.00 |
| 19980 | 3 | | | | | TLL1 | 1.00 | 20073 | 3 | | | | TMEM27 | 1.00 |
| 19981 | 3 | | | | | TLL2 | 1.00 | 20074 | 3 | | | | TMEM30C | 1.00 |
| 19982 | 3 | | | | | TLN2 | 1.00 | 20075 | 3 | | | | TMEM31 | 1.00 |
| 19983 | 3 | | | | | TLR8-AS1 | 1.00 | 20076 | 3 | | | | TMEM35 | 1.00 |
| 19984 | 3 | | | | | TLX1 | 1.00 | 20077 | 3 | | | | TMEM37 | 1.00 |
| 19985 | 3 | | | | | TLX1NB | 1.00 | 20078 | 3 | | | | TMEM44 | 1.00 |
| 19986 | 3 | | | | | TLX2 | 1.00 | 20079 | 3 | | | | TMEM45A | 1.00 |
| 19987 | 3 | | | | | TLX3 | 1.00 | 20080 | 3 | | | | TMEM47 | 1.00 |
| 19988 | 3 | | | | | TM4SF1 | 1.00 | 20081 | 3 | | | | TMEM52 | 1.00 |
| 19989 | 3 | | | | | TM4SF18 | 1.00 | 20082 | 3 | | | | TMEM54 | 1.00 |
| 19990 | 3 | | | | | TM4SF19 | 1.00 | 20083 | 3 | | | | TMEM56 | 1.00 |
| 19991 | 3 | | | | | TM4SF19-TCTEX1D2 | 1.00 | 20084 | 3 | | | | TMEM56-RWDD3 | 1.00 |
| | | | | | | | | 20085 | 3 | | | | TMEM59L | 1.00 |
| 19992 | 3 | | | | | TM4SF20 | 1.00 | 20086 | 3 | | | | TMEM61 | 1.00 |
| 19993 | 3 | | | | | TM4SF4 | 1.00 | 20087 | 3 | | | | TMEM67 | 1.00 |
| 19994 | 3 | | | | | TM4SF5 | 1.00 | 20088 | 3 | | | | TMEM72 | 1.00 |
| 19995 | 3 | | | | | TM6SF2 | 1.00 | 20089 | 3 | | | | TMEM72-AS1 | 1.00 |
| 19996 | 3 | | | | | TM7SF4 | 1.00 | 20090 | 3 | | | | TMEM74 | 1.00 |
| 19997 | 3 | | | | | TMC1 | 1.00 | 20091 | 3 | | | | TMEM74B | 1.00 |
| 19998 | 3 | | | | | TMC2 | 1.00 | 20092 | 3 | | | | TMEM82 | 1.00 |
| 19999 | 3 | | | | | TMC3 | 1.00 | 20093 | 3 | | | | TMEM88B | 1.00 |
| 20000 | 3 | | | | | TMC4 | 1.00 | 20094 | 3 | | | | TMEM89 | 1.00 |
| 20001 | 3 | | | | | TMC5 | 1.00 | 20095 | 3 | | | | TMEM8C | 1.00 |
| 20002 | 3 | | | | | TMC7 | 1.00 | 20096 | 3 | | | | TMEM92 | 1.00 |
| 20003 | 3 | | | | | TMCO2 | 1.00 | 20097 | 3 | | | | TMEM95 | 1.00 |
| 20004 | 3 | | | | | TMCO5A | 1.00 | 20098 | 3 | | | | TMEM98 | 1.00 |
| 20005 | 3 | | | | | TMCO5B | 1.00 | 20099 | 3 | | | | TMIGD1 | 1.00 |
| 20006 | 3 | | | | | TMED11P | 1.00 | 20100 | 3 | | | | TMOD4 | 1.00 |
| 20007 | 3 | | | | | TMED6 | 1.00 | 20101 | 3 | | | | TMPRSS11A | 1.00 |
| 20008 | 3 | | | | | TMEFF1 | 1.00 | 20102 | 3 | | | | TMPRSS11B | 1.00 |
| 20009 | 3 | | | | | TMEFF2 | 1.00 | 20103 | 3 | | | | TMPRSS11BNL | 1.00 |
| 20010 | 3 | | | | | TMEM100 | 1.00 | 20104 | 3 | | | | TMPRSS11D | 1.00 |
| 20011 | 3 | | | | | TMEM105 | 1.00 | 20105 | 3 | | | | TMPRSS11E | 1.00 |
| 20012 | 3 | | | | | TMEM108 | 1.00 | 20106 | 3 | | | | TMPRSS11F | 1.00 |
| 20013 | 3 | | | | | TMEM110-MUSTN1 | 1.00 | 20107 | 3 | | | | TMPRSS11GP | 1.00 |
| | | | | | | | | 20108 | 3 | | | | TMPRSS12 | 1.00 |
| 20014 | 3 | | | | | TMEM114 | 1.00 | 20109 | 3 | | | | TMPRSS13 | 1.00 |
| 20015 | 3 | | | | | TMEM117 | 1.00 | 20110 | 3 | | | | TMPRSS15 | 1.00 |
| 20016 | 3 | | | | | TMEM121 | 1.00 | 20111 | 3 | | | | TMPRSS2 | 1.00 |
| 20017 | 3 | | | | | TMEM125 | 1.00 | 20112 | 3 | | | | TMPRSS3 | 1.00 |
| 20018 | 3 | | | | | TMEM130 | 1.00 | 20113 | 3 | | | | TMPRSS4 | 1.00 |
| 20019 | 3 | | | | | TMEM132A | 1.00 | 20114 | 3 | | | | TMPRSS5 | 1.00 |
| 20020 | 3 | | | | | TMEM132B | 1.00 | 20115 | 3 | | | | TMPRSS6 | 1.00 |
| 20021 | 3 | | | | | TMEM132C | 1.00 | 20116 | 3 | | | | TMPRSS7 | 1.00 |
| 20022 | 3 | | | | | TMEM132D | 1.00 | 20117 | 3 | | | | TMPRSS9 | 1.00 |
| 20023 | 3 | | | | | TMEM132E | 1.00 | 20118 | 3 | | | | TMSB15A | 1.00 |
| 20024 | 3 | | | | | TMEM133 | 1.00 | 20119 | 3 | | | | TMSB15B | 1.00 |
| 20025 | 3 | | | | | TMEM136 | 1.00 | 20120 | 3 | | | | TNC | 1.00 |
| 20026 | 3 | | | | | TMEM139 | 1.00 | 20121 | 3 | | | | TNFAIP8L2-SCNM1 | 1.00 |
| 20027 | 3 | | | | | TMEM144 | 1.00 | 20122 | 3 | | | | TNFAIP8L3 | 1.00 |
| 20028 | 3 | | | | | TMEM145 | 1.00 | 20123 | 3 | | | | TNFRSF11B | 1.00 |
| 20029 | 3 | | | | | TMEM14E | 1.00 | 20124 | 3 | | | | TNFRSF19 | 1.00 |
| 20030 | 3 | | | | | TMEM150C | 1.00 | 20125 | 3 | | | | TNFRSF6B | 1.00 |
| 20031 | 3 | | | | | TMEM151A | 1.00 | 20126 | 3 | | | | TNFSF11 | 1.00 |
| 20032 | 3 | | | | | TMEM151B | 1.00 | 20127 | 3 | | | | TNFSF12-TNFSF13 | 1.00 |
| 20033 | 3 | | | | | TMEM155 | 1.00 | 20128 | 3 | | | | TNFSF15 | 1.00 |
| 20034 | 3 | | | | | TMEM163 | 1.00 | 20129 | 3 | | | | TNFSF18 | 1.00 |
| 20035 | 3 | | | | | TMEM17 | 1.00 | 20130 | 3 | | | | TNFSF9 | 1.00 |
| 20036 | 3 | | | | | TMEM171 | 1.00 | 20131 | 3 | | | | TNIP3 | 1.00 |
| 20037 | 3 | | | | | TMEM174 | 1.00 | 20132 | 3 | | | | TNK1 | 1.00 |
| 20038 | 3 | | | | | TMEM178 | 1.00 | 20133 | 3 | | | | TNMD | 1.00 |
| 20039 | 3 | | | | | TMEM179 | 1.00 | 20134 | 3 | | | | TNN | 1.00 |
| 20040 | 3 | | | | | TMEM182 | 1.00 | 20135 | 3 | | | | TNNC1 | 1.00 |
| 20041 | 3 | | | | | TMEM184A | 1.00 | 20136 | 3 | | | | TNNI1 | 1.00 |
| 20042 | 3 | | | | | TMEM189-UBE2V1 | 1.00 | 20137 | 3 | | | | TNNI3 | 1.00 |
| | | | | | | | | 20138 | 3 | | | | TNNI3K | 1.00 |
| 20043 | 3 | | | | | TMEM190 | 1.00 | 20139 | 3 | | | | TNNT2 | 1.00 |
| 20044 | 3 | | | | | TMEM191A | 1.00 | 20140 | 3 | | | | TNNT3 | 1.00 |
| 20045 | 3 | | | | | TMEM191B | 1.00 | 20141 | 3 | | | | TNP1 | 1.00 |
| 20046 | 3 | | | | | TMEM191C | 1.00 | 20142 | 3 | | | | TNP2 | 1.00 |
| 20047 | 3 | | | | | TMEM196 | 1.00 | 20143 | 3 | | | | TNR | 1.00 |
| 20048 | 3 | | | | | TMEM198 | 1.00 | 20144 | 3 | | | | TNS4 | 1.00 |
| 20049 | 3 | | | | | TMEM200A | 1.00 | 20145 | 3 | | | | TOB2P1 | 1.00 |
| 20050 | 3 | | | | | TMEM200B | 1.00 | 20146 | 3 | | | | TOM1L1 | 1.00 |
| 20051 | 3 | | | | | TMEM200C | 1.00 | 20147 | 3 | | | | TOMM20L | 1.00 |
| 20052 | 3 | | | | | TMEM202 | 1.00 | 20148 | 3 | | | | TONSL | 1.00 |

Fig. 41 - 106

| | | | | | | | | | | | |
|---|---|---|---|---|---|---|---|---|---|---|---|
| 20149 | 3 | | | | TOP1P2 | 1.00 | 20245 | 3 | | TRPM4 | 1.00 |
| 20150 | 3 | | | | TOX2 | 1.00 | 20246 | 3 | | TRPM5 | 1.00 |
| 20151 | 3 | | | | TOX3 | 1.00 | 20247 | 3 | | TRPM8 | 1.00 |
| 20152 | 3 | | | | TP53AIP1 | 1.00 | 20248 | 3 | | TRPV1 | 1.00 |
| 20153 | 3 | | | | TP53TG3 | 1.00 | 20249 | 3 | | TRPV3 | 1.00 |
| 20154 | 3 | | | | TP53TG3B | 1.00 | 20250 | 3 | | TRPV4 | 1.00 |
| 20155 | 3 | | | | TP53TG3C | 1.00 | 20251 | 3 | | TRPV5 | 1.00 |
| 20156 | 3 | | | | TP53TG5 | 1.00 | 20252 | 3 | | TRPV6 | 1.00 |
| 20157 | 3 | | | | TP63 | 1.00 | 20253 | 3 | | TRY6 | 1.00 |
| 20158 | 3 | | | | TP73 | 1.00 | 20254 | 3 | | TSC22D1-AS1 | 1.00 |
| 20159 | 3 | | | | TPBG | 1.00 | 20255 | 3 | | TSG1 | 1.00 |
| 20160 | 3 | | | | TPD52L1 | 1.00 | 20256 | 3 | | TSGA10 | 1.00 |
| 20161 | 3 | | | | TPD52L3 | 1.00 | 20257 | 3 | | TSGA10IP | 1.00 |
| 20162 | 3 | | | | TPH1 | 1.00 | 20258 | 3 | | TSGA13 | 1.00 |
| 20163 | 3 | | | | TPH2 | 1.00 | 20259 | 3 | | TSHB | 1.00 |
| 20164 | 3 | | | | TPI1P2 | 1.00 | 20260 | 3 | | TSHR | 1.00 |
| 20165 | 3 | | | | TPI1P3 | 1.00 | 20261 | 3 | | TSIX | 1.00 |
| 20166 | 3 | | | | TPO | 1.00 | 20262 | 3 | | TSKS | 1.00 |
| 20167 | 3 | | | | TPPP | 1.00 | 20263 | 3 | | TSKU | 1.00 |
| 20168 | 3 | | | | TPPP2 | 1.00 | 20264 | 3 | | TSLP | 1.00 |
| 20169 | 3 | | | | TPRG1 | 1.00 | 20265 | 3 | | TSNARE1 | 1.00 |
| 20170 | 3 | | | | TPRX1 | 1.00 | 20266 | 3 | | TSNAX-DISC1 | 1.00 |
| 20171 | 3 | | | | TPRXL | 1.00 | 20267 | 3 | | TSNAXIP1 | 1.00 |
| 20172 | 3 | | | | TPSAB1 | 1.00 | 20268 | 3 | | TSPAN1 | 1.00 |
| 20173 | 3 | | | | TPSB2 | 1.00 | 20269 | 3 | | TSPAN10 | 1.00 |
| 20174 | 3 | | | | TPSD1 | 1.00 | 20270 | 3 | | TSPAN11 | 1.00 |
| 20175 | 3 | | | | TPSG1 | 1.00 | 20271 | 3 | | TSPAN12 | 1.00 |
| 20176 | 3 | | | | TPTE | 1.00 | 20272 | 3 | | TSPAN15 | 1.00 |
| 20177 | 3 | | | | TPTE2 | 1.00 | 20273 | 3 | | TSPAN19 | 1.00 |
| 20178 | 3 | | | | TPTE2P1 | 1.00 | 20274 | 3 | | TSPAN6 | 1.00 |
| 20179 | 3 | | | | TPTE2P3 | 1.00 | 20275 | 3 | | TSPAN8 | 1.00 |
| 20180 | 3 | | | | TPTE2P6 | 1.00 | 20276 | 3 | | TSPEAR | 1.00 |
| 20181 | 3 | | | | TRAIP | 1.00 | 20277 | 3 | | TSPO2 | 1.00 |
| 20182 | 3 | | | | TRAM1L1 | 1.00 | 20278 | 3 | | TSPY1 | 1.00 |
| 20183 | 3 | | | | TRDN | 1.00 | 20279 | 3 | | TSPY2 | 1.00 |
| 20184 | 3 | | | | TREH | 1.00 | 20280 | 3 | | TSPY26P | 1.00 |
| 20185 | 3 | | | | TREM2 | 1.00 | 20281 | 3 | | TSPY3 | 1.00 |
| 20186 | 3 | | | | TREML2P1 | 1.00 | 20282 | 3 | | TSPY4 | 1.00 |
| 20187 | 3 | | | | TREML4 | 1.00 | 20283 | 3 | | TSPY8 | 1.00 |
| 20188 | 3 | | | | TREX2 | 1.00 | 20284 | 3 | | TSPYL6 | 1.00 |
| 20189 | 3 | | | | TRH | 1.00 | 20285 | 3 | | TSSK1B | 1.00 |
| 20190 | 3 | | | | TRHDE | 1.00 | 20286 | 3 | | TSSK2 | 1.00 |
| 20191 | 3 | | | | TRHR | 1.00 | 20287 | 3 | | TTBK1 | 1.00 |
| 20192 | 3 | | | | TRIL | 1.00 | 20288 | 3 | | TTC12 | 1.00 |
| 20193 | 3 | | | | TRIM15 | 1.00 | 20289 | 3 | | TTC18 | 1.00 |
| 20194 | 3 | | | | TRIM17 | 1.00 | 20290 | 3 | | TTC21A | 1.00 |
| 20195 | 3 | | | | TRIM2 | 1.00 | 20291 | 3 | | TTC23 | 1.00 |
| 20196 | 3 | | | | TRIM29 | 1.00 | 20292 | 3 | | TTC23L | 1.00 |
| 20197 | 3 | | | | TRIM31 | 1.00 | 20293 | 3 | | TTC24 | 1.00 |
| 20198 | 3 | | | | TRIM36 | 1.00 | 20294 | 3 | | TTC28 | 1.00 |
| 20199 | 3 | | | | TRIM39-RPP21 | 1.00 | 20295 | 3 | | TTC29 | 1.00 |
| 20200 | 3 | | | | TRIM42 | 1.00 | 20296 | 3 | | TTC30A | 1.00 |
| 20201 | 3 | | | | TRIM43 | 1.00 | 20297 | 3 | | TTC34 | 1.00 |
| 20202 | 3 | | | | TRIM43B | 1.00 | 20298 | 3 | | TTC36 | 1.00 |
| 20203 | 3 | | | | TRIM45 | 1.00 | 20299 | 3 | | TTC39A | 1.00 |
| 20204 | 3 | | | | TRIM46 | 1.00 | 20300 | 3 | | TTC40 | 1.00 |
| 20205 | 3 | | | | TRIM48 | 1.00 | 20301 | 3 | | TTC8 | 1.00 |
| 20206 | 3 | | | | TRIM49 | 1.00 | 20302 | 3 | | TTC9B | 1.00 |
| 20207 | 3 | | | | TRIM49L1 | 1.00 | 20303 | 3 | | TTK | 1.00 |
| 20208 | 3 | | | | TRIM49L2 | 1.00 | 20304 | 3 | | TTLL10 | 1.00 |
| 20209 | 3 | | | | TRIM50 | 1.00 | 20305 | 3 | | TTLL13 | 1.00 |
| 20210 | 3 | | | | TRIM53P | 1.00 | 20306 | 3 | | TTLL2 | 1.00 |
| 20211 | 3 | | | | TRIM54 | 1.00 | 20307 | 3 | | TTLL6 | 1.00 |
| 20212 | 3 | | | | TRIM55 | 1.00 | 20308 | 3 | | TTLL7 | 1.00 |
| 20213 | 3 | | | | TRIM6 | 1.00 | 20309 | 3 | | TTLL9 | 1.00 |
| 20214 | 3 | | | | TRIM6-TRIM34 | 1.00 | 20310 | 3 | | TTN | 1.00 |
| 20215 | 3 | | | | TRIM60 | 1.00 | 20311 | 3 | | TTPA | 1.00 |
| 20216 | 3 | | | | TRIM61 | 1.00 | 20312 | 3 | | TTR | 1.00 |
| 20217 | 3 | | | | TRIM63 | 1.00 | 20313 | 3 | | TTTY1 | 1.00 |
| 20218 | 3 | | | | TRIM64 | 1.00 | 20314 | 3 | | TTTY10 | 1.00 |
| 20219 | 3 | | | | TRIM64B | 1.00 | 20315 | 3 | | TTTY11 | 1.00 |
| 20220 | 3 | | | | TRIM64C | 1.00 | 20316 | 3 | | TTTY12 | 1.00 |
| 20221 | 3 | | | | TRIM67 | 1.00 | 20317 | 3 | | TTTY13 | 1.00 |
| 20222 | 3 | | | | TRIM69 | 1.00 | 20318 | 3 | | TTTY14 | 1.00 |
| 20223 | 3 | | | | TRIM71 | 1.00 | 20319 | 3 | | TTTY16 | 1.00 |
| 20224 | 3 | | | | TRIM72 | 1.00 | 20320 | 3 | | TTTY17A | 1.00 |
| 20225 | 3 | | | | TRIM74 | 1.00 | 20321 | 3 | | TTTY18 | 1.00 |
| 20226 | 3 | | | | TRIM77P | 1.00 | 20322 | 3 | | TTTY19 | 1.00 |
| 20227 | 3 | | | | TRIM78P | 1.00 | 20323 | 3 | | TTTY1B | 1.00 |
| 20228 | 3 | | | | TRIM9 | 1.00 | 20324 | 3 | | TTTY2 | 1.00 |
| 20229 | 3 | | | | TRIML1 | 1.00 | 20325 | 3 | | TTTY20 | 1.00 |
| 20230 | 3 | | | | TRIML2 | 1.00 | 20326 | 3 | | TTTY21 | 1.00 |
| 20231 | 3 | | | | TRIP13 | 1.00 | 20327 | 3 | | TTTY21B | 1.00 |
| 20232 | 3 | | | | TRMT11 | 1.00 | 20328 | 3 | | TTTY22 | 1.00 |
| 20233 | 3 | | | | TRO | 1.00 | 20329 | 3 | | TTTY23B | 1.00 |
| 20234 | 3 | | | | TROAP | 1.00 | 20330 | 3 | | TTTY3 | 1.00 |
| 20235 | 3 | | | | TRPA1 | 1.00 | 20331 | 3 | | TTTY3B | 1.00 |
| 20236 | 3 | | | | TRPC1 | 1.00 | 20332 | 3 | | TTTY4 | 1.00 |
| 20237 | 3 | | | | TRPC2 | 1.00 | 20333 | 3 | | TTTY4B | 1.00 |
| 20238 | 3 | | | | TRPC3 | 1.00 | 20334 | 3 | | TTTY5 | 1.00 |
| 20239 | 3 | | | | TRPC4 | 1.00 | 20335 | 3 | | TTTY6 | 1.00 |
| 20240 | 3 | | | | TRPC5 | 1.00 | 20336 | 3 | | TTTY6B | 1.00 |
| 20241 | 3 | | | | TRPC6 | 1.00 | 20337 | 3 | | TTTY7 | 1.00 |
| 20242 | 3 | | | | TRPC7 | 1.00 | 20338 | 3 | | TTTY7B | 1.00 |
| 20243 | 3 | | | | TRPM1 | 1.00 | 20339 | 3 | | TTTY8 | 1.00 |
| 20244 | 3 | | | | TRPM3 | 1.00 | 20340 | 3 | | TTTY8B | 1.00 |

Fig. 41 - 107

| | | | | | | | | | | | | | | |
|---|---|---|---|---|---|---|---|---|---|---|---|---|---|---|
| 20341 | 3 | | | | | TTY9B | 1.00 | 20437 | 3 | | | | UNC80 | 1.00 |
| 20342 | 3 | | | | | TTYH1 | 1.00 | 20438 | 3 | | | | UNC93A | 1.00 |
| 20343 | 3 | | | | | TUB | 1.00 | 20439 | 3 | | | | UNCX | 1.00 |
| 20344 | 3 | | | | | TUBA3C | 1.00 | 20440 | 3 | | | | UNQ6494 | 1.00 |
| 20345 | 3 | | | | | TUBA3D | 1.00 | 20441 | 3 | | | | UNQ6975 | 1.00 |
| 20346 | 3 | | | | | TUBA3E | 1.00 | 20442 | 3 | | | | UOX | 1.00 |
| 20347 | 3 | | | | | TUBA4B | 1.00 | 20443 | 3 | | | | UPK1A | 1.00 |
| 20348 | 3 | | | | | TUBAL3 | 1.00 | 20444 | 3 | | | | UPK1B | 1.00 |
| 20349 | 3 | | | | | TUBB3 | 1.00 | 20445 | 3 | | | | UPK2 | 1.00 |
| 20350 | 3 | | | | | TUBB8 | 1.00 | 20446 | 3 | | | | UPK3B | 1.00 |
| 20351 | 3 | | | | | TUBBP5 | 1.00 | 20447 | 3 | | | | UPP2 | 1.00 |
| 20352 | 3 | | | | | TULP1 | 1.00 | 20448 | 3 | | | | URGCP-MRPS24 | 1.00 |
| 20353 | 3 | | | | | TULP2 | 1.00 | 20449 | 3 | | | | UROC1 | 1.00 |
| 20354 | 3 | | | | | TUSC1 | 1.00 | 20450 | 3 | | | | USH1C | 1.00 |
| 20355 | 3 | | | | | TUSC3 | 1.00 | 20451 | 3 | | | | USH1G | 1.00 |
| 20356 | 3 | | | | | TUSC5 | 1.00 | 20452 | 3 | | | | USH2A | 1.00 |
| 20357 | 3 | | | | | TWIST1 | 1.00 | 20453 | 3 | | | | USHBP1 | 1.00 |
| 20358 | 3 | | | | | TWIST2 | 1.00 | 20454 | 3 | | | | USP13 | 1.00 |
| 20359 | 3 | | | | | TXLNB | 1.00 | 20455 | 3 | | | | USP17 | 1.00 |
| 20360 | 3 | | | | | TXNDC2 | 1.00 | 20456 | 3 | | | | USP17L2 | 1.00 |
| 20361 | 3 | | | | | TXNDC8 | 1.00 | 20457 | 3 | | | | USP17L6P | 1.00 |
| 20362 | 3 | | | | | TXNRD3 | 1.00 | 20458 | 3 | | | | USP2 | 1.00 |
| 20363 | 3 | | | | | TXNRD3NB | 1.00 | 20459 | 3 | | | | USP26 | 1.00 |
| 20364 | 3 | | | | | TYR | 1.00 | 20460 | 3 | | | | USP29 | 1.00 |
| 20365 | 3 | | | | | TYRO3 | 1.00 | 20461 | 3 | | | | USP32P2 | 1.00 |
| 20366 | 3 | | | | | TYRO3P | 1.00 | 20462 | 3 | | | | USP43 | 1.00 |
| 20367 | 3 | | | | | TYRP1 | 1.00 | 20463 | 3 | | | | USP45 | 1.00 |
| 20368 | 3 | | | | | UACA | 1.00 | 20464 | 3 | | | | USP49 | 1.00 |
| 20369 | 3 | | | | | UBAC2-AS1 | 1.00 | 20465 | 3 | | | | USP50 | 1.00 |
| 20370 | 3 | | | | | UBAP1L | 1.00 | 20466 | 3 | | | | USP51 | 1.00 |
| 20371 | 3 | | | | | UBD | 1.00 | 20467 | 3 | | | | USP54 | 1.00 |
| 20372 | 3 | | | | | UBE2C | 1.00 | 20468 | 3 | | | | USP6 | 1.00 |
| 20373 | 3 | | | | | UBE2DNL | 1.00 | 20469 | 3 | | | | UTF1 | 1.00 |
| 20374 | 3 | | | | | UBE2F-SCLY | 1.00 | 20470 | 3 | | | | UTS2D | 1.00 |
| 20375 | 3 | | | | | UBE2Q2P1 | 1.00 | 20471 | 3 | | | | UTS2R | 1.00 |
| 20376 | 3 | | | | | UBE2Q2P2 | 1.00 | 20472 | 3 | | | | VANGL2 | 1.00 |
| 20377 | 3 | | | | | UBE2Q2P3 | 1.00 | 20473 | 3 | | | | VARS2 | 1.00 |
| 20378 | 3 | | | | | UBE2QL1 | 1.00 | 20474 | 3 | | | | VASH2 | 1.00 |
| 20379 | 3 | | | | | UBE2T | 1.00 | 20475 | 3 | | | | VASN | 1.00 |
| 20380 | 3 | | | | | UBE2U | 1.00 | 20476 | 3 | | | | VAT1L | 1.00 |
| 20381 | 3 | | | | | UBE3D | 1.00 | 20477 | 3 | | | | VAX1 | 1.00 |
| 20382 | 3 | | | | | UBL4B | 1.00 | 20478 | 3 | | | | VAX2 | 1.00 |
| 20383 | 3 | | | | | UBQLN3 | 1.00 | 20479 | 3 | | | | VCAM1 | 1.00 |
| 20384 | 3 | | | | | UBQLNL | 1.00 | 20480 | 3 | | | | VCX | 1.00 |
| 20385 | 3 | | | | | UBTFL1 | 1.00 | 20481 | 3 | | | | VCX2 | 1.00 |
| 20386 | 3 | | | | | UBXN10 | 1.00 | 20482 | 3 | | | | VCX3A | 1.00 |
| 20387 | 3 | | | | | UCA1 | 1.00 | 20483 | 3 | | | | VCX3B | 1.00 |
| 20388 | 3 | | | | | UCHL1 | 1.00 | 20484 | 3 | | | | VCY | 1.00 |
| 20389 | 3 | | | | | UCKL1-AS1 | 1.00 | 20485 | 3 | | | | VCY1B | 1.00 |
| 20390 | 3 | | | | | UCMA | 1.00 | 20486 | 3 | | | | VEGFC | 1.00 |
| 20391 | 3 | | | | | UCN | 1.00 | 20487 | 3 | | | | VENTXP1 | 1.00 |
| 20392 | 3 | | | | | UCN2 | 1.00 | 20488 | 3 | | | | VENTXP7 | 1.00 |
| 20393 | 3 | | | | | UCN3 | 1.00 | 20489 | 3 | | | | VGF | 1.00 |
| 20394 | 3 | | | | | UCP1 | 1.00 | 20490 | 3 | | | | VGLL1 | 1.00 |
| 20395 | 3 | | | | | UG0898H09 | 1.00 | 20491 | 3 | | | | VGLL2 | 1.00 |
| 20396 | 3 | | | | | UGGT2 | 1.00 | 20492 | 3 | | | | VGLL3 | 1.00 |
| 20397 | 3 | | | | | UGT1A1 | 1.00 | 20493 | 3 | | | | VIL1 | 1.00 |
| 20398 | 3 | | | | | UGT1A10 | 1.00 | 20494 | 3 | | | | VIP | 1.00 |
| 20399 | 3 | | | | | UGT1A3 | 1.00 | 20495 | 3 | | | | VIPR2 | 1.00 |
| 20400 | 3 | | | | | UGT1A4 | 1.00 | 20496 | 3 | | | | VIT | 1.00 |
| 20401 | 3 | | | | | UGT1A5 | 1.00 | 20497 | 3 | | | | VLDLR | 1.00 |
| 20402 | 3 | | | | | UGT1A6 | 1.00 | 20498 | 3 | | | | VN1R1 | 1.00 |
| 20403 | 3 | | | | | UGT1A7 | 1.00 | 20499 | 3 | | | | VN1R10P | 1.00 |
| 20404 | 3 | | | | | UGT1A8 | 1.00 | 20500 | 3 | | | | VN1R2 | 1.00 |
| 20405 | 3 | | | | | UGT1A9 | 1.00 | 20501 | 3 | | | | VN1R4 | 1.00 |
| 20406 | 3 | | | | | UGT2A1 | 1.00 | 20502 | 3 | | | | VN1R5 | 1.00 |
| 20407 | 3 | | | | | UGT2A2 | 1.00 | 20503 | 3 | | | | VPREB1 | 1.00 |
| 20408 | 3 | | | | | UGT2A3 | 1.00 | 20504 | 3 | | | | VPS37D | 1.00 |
| 20409 | 3 | | | | | UGT2B10 | 1.00 | 20505 | 3 | | | | VRTN | 1.00 |
| 20410 | 3 | | | | | UGT2B11 | 1.00 | 20506 | 3 | | | | VSIG10L | 1.00 |
| 20411 | 3 | | | | | UGT2B15 | 1.00 | 20507 | 3 | | | | VSIG8 | 1.00 |
| 20412 | 3 | | | | | UGT2B17 | 1.00 | 20508 | 3 | | | | VSNL1 | 1.00 |
| 20413 | 3 | | | | | UGT2B28 | 1.00 | 20509 | 3 | | | | VSTM2A | 1.00 |
| 20414 | 3 | | | | | UGT2B4 | 1.00 | 20510 | 3 | | | | VSTM2B | 1.00 |
| 20415 | 3 | | | | | UGT2B7 | 1.00 | 20511 | 3 | | | | VSTM2L | 1.00 |
| 20416 | 3 | | | | | UGT3A1 | 1.00 | 20512 | 3 | | | | VSTM4 | 1.00 |
| 20417 | 3 | | | | | UGT3A2 | 1.00 | 20513 | 3 | | | | VSTM5 | 1.00 |
| 20418 | 3 | | | | | UGT8 | 1.00 | 20514 | 3 | | | | VSX1 | 1.00 |
| 20419 | 3 | | | | | ULBP1 | 1.00 | 20515 | 3 | | | | VSX2 | 1.00 |
| 20420 | 3 | | | | | ULBP2 | 1.00 | 20516 | 3 | | | | VTCN1 | 1.00 |
| 20421 | 3 | | | | | ULBP3 | 1.00 | 20517 | 3 | | | | VTN | 1.00 |
| 20422 | 3 | | | | | ULK4 | 1.00 | 20518 | 3 | | | | VTRNA1-1 | 1.00 |
| 20423 | 3 | | | | | ULK4P2 | 1.00 | 20519 | 3 | | | | VTRNA1-2 | 1.00 |
| 20424 | 3 | | | | | ULK4P3 | 1.00 | 20520 | 3 | | | | VTRNA1-3 | 1.00 |
| 20425 | 3 | | | | | UMOD | 1.00 | 20521 | 3 | | | | VTRNA2-1 | 1.00 |
| 20426 | 3 | | | | | UMODL1 | 1.00 | 20522 | 3 | | | | VWA1 | 1.00 |
| 20427 | 3 | | | | | UNC13A | 1.00 | 20523 | 3 | | | | VWA2 | 1.00 |
| 20428 | 3 | | | | | UNC13B | 1.00 | 20524 | 3 | | | | VWA3A | 1.00 |
| 20429 | 3 | | | | | UNC13C | 1.00 | 20525 | 3 | | | | VWA3B | 1.00 |
| 20430 | 3 | | | | | UNC45B | 1.00 | 20526 | 3 | | | | VWA5B1 | 1.00 |
| 20431 | 3 | | | | | UNC5A | 1.00 | 20527 | 3 | | | | VWA5B2 | 1.00 |
| 20432 | 3 | | | | | UNC5B | 1.00 | 20528 | 3 | | | | VWA7 | 1.00 |
| 20433 | 3 | | | | | UNC5C | 1.00 | 20529 | 3 | | | | VWC2 | 1.00 |
| 20434 | 3 | | | | | UNC5CL | 1.00 | 20530 | 3 | | | | VWC2L | 1.00 |
| 20435 | 3 | | | | | UNC5D | 1.00 | 20531 | 3 | | | | VWDE | 1.00 |
| 20436 | 3 | | | | | UNC79 | 1.00 | 20532 | 3 | | | | VWF | 1.00 |

Fig. 41 - 108

| | | | | | | | |
|---|---|---|---|---|---|---|---|
| 20533 | 3 | | WASF3 | 1.00 | 20629 | 3 | | XKR9 | 1.00 |
| 20534 | 3 | | WBP2NL | 1.00 | 20630 | 3 | | XKRX | 1.00 |
| 20535 | 3 | | WBSCR17 | 1.00 | 20631 | 3 | | XKRY | 1.00 |
| 20536 | 3 | | WBSCR27 | 1.00 | 20632 | 3 | | XKRY2 | 1.00 |
| 20537 | 3 | | WBSCR28 | 1.00 | 20633 | 3 | | XPNPEP2 | 1.00 |
| 20538 | 3 | | WDFY3-AS2 | 1.00 | 20634 | 3 | | XRCC2 | 1.00 |
| 20539 | 3 | | WDHD1 | 1.00 | 20635 | 3 | | XYLB | 1.00 |
| 20540 | 3 | | WDPCP | 1.00 | 20636 | 3 | | YAP1 | 1.00 |
| 20541 | 3 | | WDR16 | 1.00 | 20637 | 3 | | YBX2 | 1.00 |
| 20542 | 3 | | WDR17 | 1.00 | 20638 | 3 | | YIPF7 | 1.00 |
| 20543 | 3 | | WDR19 | 1.00 | 20639 | 3 | | YJEFN3 | 1.00 |
| 20544 | 3 | | WDR27 | 1.00 | 20640 | 3 | | YSK4 | 1.00 |
| 20545 | 3 | | WDR31 | 1.00 | 20641 | 3 | | YY2 | 1.00 |
| 20546 | 3 | | WDR35 | 1.00 | 20642 | 3 | | ZACN | 1.00 |
| 20547 | 3 | | WDR38 | 1.00 | 20643 | 3 | | ZAN | 1.00 |
| 20548 | 3 | | WDR49 | 1.00 | 20644 | 3 | | ZAR1 | 1.00 |
| 20549 | 3 | | WDR52 | 1.00 | 20645 | 3 | | ZAR1L | 1.00 |
| 20550 | 3 | | WDR62 | 1.00 | 20646 | 3 | | ZBBX | 1.00 |
| 20551 | 3 | | WDR63 | 1.00 | 20647 | 3 | | ZBED2 | 1.00 |
| 20552 | 3 | | WDR64 | 1.00 | 20648 | 3 | | ZBTB12 | 1.00 |
| 20553 | 3 | | WDR65 | 1.00 | 20649 | 3 | | ZBTB20 | 1.00 |
| 20554 | 3 | | WDR66 | 1.00 | 20650 | 3 | | ZBTB20-AS1 | 1.00 |
| 20555 | 3 | | WDR69 | 1.00 | 20651 | 3 | | ZBTB7C | 1.00 |
| 20556 | 3 | | WDR72 | 1.00 | 20652 | 3 | | ZBTB8A | 1.00 |
| 20557 | 3 | | WDR78 | 1.00 | 20653 | 3 | | ZBTB8B | 1.00 |
| 20558 | 3 | | WDR86 | 1.00 | 20654 | 3 | | ZC2HC1B | 1.00 |
| 20559 | 3 | | WDR87 | 1.00 | 20655 | 3 | | ZC2HC1C | 1.00 |
| 20560 | 3 | | WDR88 | 1.00 | 20656 | 3 | | ZC3H12B | 1.00 |
| 20561 | 3 | | WDR90 | 1.00 | 20657 | 3 | | ZC3H12C | 1.00 |
| 20562 | 3 | | WDR93 | 1.00 | 20658 | 3 | | ZC3HAV1L | 1.00 |
| 20563 | 3 | | WDR96 | 1.00 | 20659 | 3 | | ZCCHC12 | 1.00 |
| 20564 | 3 | | WEE2 | 1.00 | 20660 | 3 | | ZCCHC13 | 1.00 |
| 20565 | 3 | | WFDC1 | 1.00 | 20661 | 3 | | ZCCHC16 | 1.00 |
| 20566 | 3 | | WFDC10A | 1.00 | 20662 | 3 | | ZCCHC5 | 1.00 |
| 20567 | 3 | | WFDC10B | 1.00 | 20663 | 3 | | ZCWPW2 | 1.00 |
| 20568 | 3 | | WFDC11 | 1.00 | 20664 | 3 | | ZDBF2 | 1.00 |
| 20569 | 3 | | WFDC12 | 1.00 | 20665 | 3 | | ZDHHC1 | 1.00 |
| 20570 | 3 | | WFDC13 | 1.00 | 20666 | 3 | | ZDHHC11 | 1.00 |
| 20571 | 3 | | WFDC2 | 1.00 | 20667 | 3 | | ZDHHC15 | 1.00 |
| 20572 | 3 | | WFDC3 | 1.00 | 20668 | 3 | | ZDHHC22 | 1.00 |
| 20573 | 3 | | WFDC5 | 1.00 | 20669 | 3 | | ZDHHC23 | 1.00 |
| 20574 | 3 | | WFDC6 | 1.00 | 20670 | 3 | | ZDHHC8P1 | 1.00 |
| 20575 | 3 | | WFDC8 | 1.00 | 20671 | 3 | | ZEB2-AS1 | 1.00 |
| 20576 | 3 | | WFDC9 | 1.00 | 20672 | 3 | | ZFAT-AS1 | 1.00 |
| 20577 | 3 | | WFIKKN1 | 1.00 | 20673 | 3 | | ZFHX2 | 1.00 |
| 20578 | 3 | | WFIKKN2 | 1.00 | 20674 | 3 | | ZFHX4 | 1.00 |
| 20579 | 3 | | WIF1 | 1.00 | 20675 | 3 | | ZFP112 | 1.00 |
| 20580 | 3 | | WIPF3 | 1.00 | 20676 | 3 | | ZFP2 | 1.00 |
| 20581 | 3 | | WISP1 | 1.00 | 20677 | 3 | | ZFP42 | 1.00 |
| 20582 | 3 | | WISP2 | 1.00 | 20678 | 3 | | ZFP91-CNTF | 1.00 |
| 20583 | 3 | | WISP3 | 1.00 | 20679 | 3 | | ZFPM2 | 1.00 |
| 20584 | 3 | | WNK2 | 1.00 | 20680 | 3 | | ZFR2 | 1.00 |
| 20585 | 3 | | WNK3 | 1.00 | 20681 | 3 | | ZFYVE9 | 1.00 |
| 20586 | 3 | | WNK4 | 1.00 | 20682 | 3 | | ZG16 | 1.00 |
| 20587 | 3 | | WNT1 | 1.00 | 20683 | 3 | | ZIC1 | 1.00 |
| 20588 | 3 | | WNT10B | 1.00 | 20684 | 3 | | ZIC2 | 1.00 |
| 20589 | 3 | | WNT11 | 1.00 | 20685 | 3 | | ZIC3 | 1.00 |
| 20590 | 3 | | WNT2 | 1.00 | 20686 | 3 | | ZIC4 | 1.00 |
| 20591 | 3 | | WNT2B | 1.00 | 20687 | 3 | | ZIC5 | 1.00 |
| 20592 | 3 | | WNT3 | 1.00 | 20688 | 3 | | ZIM2 | 1.00 |
| 20593 | 3 | | WNT3A | 1.00 | 20689 | 3 | | ZIM3 | 1.00 |
| 20594 | 3 | | WNT4 | 1.00 | 20690 | 3 | | ZMAT4 | 1.00 |
| 20595 | 3 | | WNT5A | 1.00 | 20691 | 3 | | ZMYND10 | 1.00 |
| 20596 | 3 | | WNT6 | 1.00 | 20692 | 3 | | ZMYND12 | 1.00 |
| 20597 | 3 | | WNT7B | 1.00 | 20693 | 3 | | ZMYND15 | 1.00 |
| 20598 | 3 | | WNT8A | 1.00 | 20694 | 3 | | ZNF114 | 1.00 |
| 20599 | 3 | | WNT8B | 1.00 | 20695 | 3 | | ZNF135 | 1.00 |
| 20600 | 3 | | WNT9A | 1.00 | 20696 | 3 | | ZNF157 | 1.00 |
| 20601 | 3 | | WNT9B | 1.00 | 20697 | 3 | | ZNF165 | 1.00 |
| 20602 | 3 | | WRN | 1.00 | 20698 | 3 | | ZNF177 | 1.00 |
| 20603 | 3 | | WSCD1 | 1.00 | 20699 | 3 | | ZNF19 | 1.00 |
| 20604 | 3 | | WSCD2 | 1.00 | 20700 | 3 | | ZNF208 | 1.00 |
| 20605 | 3 | | WT1 | 1.00 | 20701 | 3 | | ZNF214 | 1.00 |
| 20606 | 3 | | WT1-AS | 1.00 | 20702 | 3 | | ZNF215 | 1.00 |
| 20607 | 3 | | WTIP | 1.00 | 20703 | 3 | | ZNF221 | 1.00 |
| 20608 | 3 | | WWC1 | 1.00 | 20704 | 3 | | ZNF229 | 1.00 |
| 20609 | 3 | | WWC2 | 1.00 | 20705 | 3 | | ZNF233 | 1.00 |
| 20610 | 3 | | WWTR1 | 1.00 | 20706 | 3 | | ZNF257 | 1.00 |
| 20611 | 3 | | WWTR1-AS1 | 1.00 | 20707 | 3 | | ZNF280A | 1.00 |
| 20612 | 3 | | XAGE1A | 1.00 | 20708 | 3 | | ZNF280B | 1.00 |
| 20613 | 3 | | XAGE1C | 1.00 | 20709 | 3 | | ZNF287 | 1.00 |
| 20614 | 3 | | XAGE1E | 1.00 | 20710 | 3 | | ZNF295-AS1 | 1.00 |
| 20615 | 3 | | XAGE2 | 1.00 | 20711 | 3 | | ZNF300 | 1.00 |
| 20616 | 3 | | XAGE2B | 1.00 | 20712 | 3 | | ZNF300P1 | 1.00 |
| 20617 | 3 | | XAGE3 | 1.00 | 20713 | 3 | | ZNF311 | 1.00 |
| 20618 | 3 | | XAGE5 | 1.00 | 20714 | 3 | | ZNF32-AS3 | 1.00 |
| 20619 | 3 | | XDH | 1.00 | 20715 | 3 | | ZNF323 | 1.00 |
| 20620 | 3 | | XG | 1.00 | 20716 | 3 | | ZNF334 | 1.00 |
| 20621 | 3 | | XGPY2 | 1.00 | 20717 | 3 | | ZNF385B | 1.00 |
| 20622 | 3 | | XIRP1 | 1.00 | 20718 | 3 | | ZNF385C | 1.00 |
| 20623 | 3 | | XIRP2 | 1.00 | 20719 | 3 | | ZNF391 | 1.00 |
| 20624 | 3 | | XKR3 | 1.00 | 20720 | 3 | | ZNF404 | 1.00 |
| 20625 | 3 | | XKR4 | 1.00 | 20721 | 3 | | ZNF423 | 1.00 |
| 20626 | 3 | | XKR5 | 1.00 | 20722 | 3 | | ZNF425 | 1.00 |
| 20627 | 3 | | XKR6 | 1.00 | 20723 | 3 | | ZNF433 | 1.00 |
| 20628 | 3 | | XKR7 | 1.00 | 20724 | 3 | | ZNF442 | 1.00 |

Fig. 41 - 109

| | | | | | | | |
|---|---|---|---|---|---|---|---|
| 20725 | 3 | | | | | ZNF454 | 1.00 |
| 20726 | 3 | | | | | ZNF462 | 1.00 |
| 20727 | 3 | | | | | ZNF469 | 1.00 |
| 20728 | 3 | | | | | ZNF471 | 1.00 |
| 20729 | 3 | | | | | ZNF474 | 1.00 |
| 20730 | 3 | | | | | ZNF479 | 1.00 |
| 20731 | 3 | | | | | ZNF483 | 1.00 |
| 20732 | 3 | | | | | ZNF488 | 1.00 |
| 20733 | 3 | | | | | ZNF491 | 1.00 |
| 20734 | 3 | | | | | ZNF492 | 1.00 |
| 20735 | 3 | | | | | ZNF497 | 1.00 |
| 20736 | 3 | | | | | ZNF503-AS1 | 1.00 |
| 20737 | 3 | | | | | ZNF503-AS2 | 1.00 |
| 20738 | 3 | | | | | ZNF519 | 1.00 |
| 20739 | 3 | | | | | ZNF521 | 1.00 |
| 20740 | 3 | | | | | ZNF534 | 1.00 |
| 20741 | 3 | | | | | ZNF536 | 1.00 |
| 20742 | 3 | | | | | ZNF541 | 1.00 |
| 20743 | 3 | | | | | ZNF556 | 1.00 |
| 20744 | 3 | | | | | ZNF559-ZNF177 | 1.00 |
| 20745 | 3 | | | | | ZNF560 | 1.00 |
| 20746 | 3 | | | | | ZNF572 | 1.00 |
| 20747 | 3 | | | | | ZNF578 | 1.00 |
| 20748 | 3 | | | | | ZNF594 | 1.00 |
| 20749 | 3 | | | | | ZNF596 | 1.00 |
| 20750 | 3 | | | | | ZNF599 | 1.00 |
| 20751 | 3 | | | | | ZNF610 | 1.00 |
| 20752 | 3 | | | | | ZNF618 | 1.00 |
| 20753 | 3 | | | | | ZNF620 | 1.00 |
| 20754 | 3 | | | | | ZNF625 | 1.00 |
| 20755 | 3 | | | | | ZNF625-ZNF20 | 1.00 |
| 20756 | 3 | | | | | ZNF645 | 1.00 |
| 20757 | 3 | | | | | ZNF648 | 1.00 |
| 20758 | 3 | | | | | ZNF660 | 1.00 |
| 20759 | 3 | | | | | ZNF662 | 1.00 |
| 20760 | 3 | | | | | ZNF663 | 1.00 |
| 20761 | 3 | | | | | ZNF664-FAM101A | 1.00 |
| 20762 | 3 | | | | | ZNF665 | 1.00 |
| 20763 | 3 | | | | | ZNF667 | 1.00 |
| 20764 | 3 | | | | | ZNF670 | 1.00 |
| 20765 | 3 | | | | | ZNF670-ZNF695 | 1.00 |
| 20766 | 3 | | | | | ZNF676 | 1.00 |
| 20767 | 3 | | | | | ZNF677 | 1.00 |
| 20768 | 3 | | | | | ZNF679 | 1.00 |
| 20769 | 3 | | | | | ZNF682 | 1.00 |
| 20770 | 3 | | | | | ZNF695 | 1.00 |
| 20771 | 3 | | | | | ZNF704 | 1.00 |
| 20772 | 3 | | | | | ZNF705A | 1.00 |
| 20773 | 3 | | | | | ZNF705D | 1.00 |
| 20774 | 3 | | | | | ZNF705G | 1.00 |
| 20775 | 3 | | | | | ZNF711 | 1.00 |
| 20776 | 3 | | | | | ZNF713 | 1.00 |
| 20777 | 3 | | | | | ZNF716 | 1.00 |
| 20778 | 3 | | | | | ZNF717 | 1.00 |
| 20779 | 3 | | | | | ZNF726 | 1.00 |
| 20780 | 3 | | | | | ZNF727 | 1.00 |
| 20781 | 3 | | | | | ZNF729 | 1.00 |
| 20782 | 3 | | | | | ZNF732 | 1.00 |
| 20783 | 3 | | | | | ZNF735 | 1.00 |
| 20784 | 3 | | | | | ZNF738 | 1.00 |
| 20785 | 3 | | | | | ZNF750 | 1.00 |
| 20786 | 3 | | | | | ZNF771 | 1.00 |
| 20787 | 3 | | | | | ZNF774 | 1.00 |
| 20788 | 3 | | | | | ZNF781 | 1.00 |
| 20789 | 3 | | | | | ZNF788 | 1.00 |
| 20790 | 3 | | | | | ZNF793 | 1.00 |
| 20791 | 3 | | | | | ZNF804B | 1.00 |
| 20792 | 3 | | | | | ZNF812 | 1.00 |
| 20793 | 3 | | | | | ZNF816-ZNF321P | 1.00 |
| 20794 | 3 | | | | | ZNF826P | 1.00 |
| 20795 | 3 | | | | | ZNF833P | 1.00 |
| 20796 | 3 | | | | | ZNF843 | 1.00 |
| 20797 | 3 | | | | | ZNF846 | 1.00 |
| 20798 | 3 | | | | | ZNF847P | 1.00 |
| 20799 | 3 | | | | | ZNF850 | 1.00 |
| 20800 | 3 | | | | | ZNF876P | 1.00 |
| 20801 | 3 | | | | | ZNF878 | 1.00 |
| 20802 | 3 | | | | | ZNF90 | 1.00 |
| 20803 | 3 | | | | | ZNF98 | 1.00 |
| 20804 | 3 | | | | | ZNF99 | 1.00 |
| 20805 | 3 | | | | | ZNRD1-AS1 | 1.00 |
| 20806 | 3 | | | | | ZNRF2P1 | 1.00 |
| 20807 | 3 | | | | | ZNRF2P2 | 1.00 |
| 20808 | 3 | | | | | ZNRF3 | 1.00 |
| 20809 | 3 | | | | | ZNRF4 | 1.00 |
| 20810 | 3 | | | | | ZP1 | 1.00 |
| 20811 | 3 | | | | | ZP2 | 1.00 |
| 20812 | 3 | | | | | ZP4 | 1.00 |
| 20813 | 3 | | | | | ZPBP | 1.00 |
| 20814 | 3 | | | | | ZPBP2 | 1.00 |
| 20815 | 3 | | | | | ZPLD1 | 1.00 |
| 20816 | 3 | | | | | ZRANB2-AS2 | 1.00 |
| 20817 | 3 | | | | | ZRANB3 | 1.00 |
| 20818 | 3 | | | | | ZSCAN1 | 1.00 |
| 20819 | 3 | | | | | ZSCAN10 | 1.00 |
| 20820 | 3 | | | | | ZSCAN12P1 | 1.00 |
| 20821 | 3 | | | | | ZSCAN20 | 1.00 |
| 20822 | 3 | | | | | ZSCAN23 | 1.00 |
| 20823 | 3 | | | | | ZSCAN4 | 1.00 |
| 20824 | 3 | | | | | ZSCAN5B | 1.00 |
| 20825 | 3 | | | | | ZSWIM2 | 1.00 |
| 20826 | 3 | | | | | ZSWIM5 | 1.00 |
| 20827 | 3 | | | | | ZYG11A | 1.00 |
| 20828 | 3 | | | | | tAKR | 1.00 |

Fig. 42 - 1

| Metabolite | Plasma | Skeletal muscle | Brown fat | Heart | Lung | Thymus | Kidney |
|---|---|---|---|---|---|---|---|
| 2-Hydroxybutyric acid | 0.4 | 0.4 | 0.5 | 0.5 | 0.6 | 0.6 | 0.4 |
| 2-Oxoglutaric acid | N.A. | N.A. | N.A. | N.A. | N.A. | N.A. | N.A. |
| 2-Oxoisovaleric acid | 0.7 | 0.9 | N.A. | N.A. | <1 | N.A. | N.A. |
| 2-Phosphoglyceric acid | N.A. | N.A. | N.A. | N.A. | N.A. | N.A. | N.A. |
| 3-Hydroxybutyric acid | 0.3 | 0.3 | 0.4 | 0.4 | 0.3 | 0.4 | 0.3 |
| 3-Phosphoglyceric acid | N.A. | N.A. | 1.4 | N.A. | 0.8 | N.A. | N.A. |
| 6-Phosphogluconic acid | N.A. | N.A. | 1< | 0.7 | N.A. | 1.5 | 1.0 |
| Acetyl CoA_divalent | N.A. | N.A. | 0.8 | 1.3 | N.A. | 1.0 | 0.9 |
| Adenine | N.A. | 1.2 | 1.2 | 1.1 | 1.0 | 1.2 | 0.9 |
| Adenosine | 0.8 | 1.1 | 1.1 | 1.0 | 1.5 | 1.6 | 1.2 |
| ADP | 1.6 | 1.0 | 1.2 | 1.0 | 1.1 | 0.9 | 1.0 |
| Ala | 0.8 | 1.1 | 0.8 | 1.0 | 0.8 | 1.0 | 0.9 |
| AMP | 1.6 | 0.9 | 0.8 | 1.0 | 1.1 | 1.3 | 0.8 |
| Anthranilic acid | N.A. | N.A. | N.A. | N.A. | N.A. | N.A. | N.A. |
| Arg | 0.8 | 1.3 | 0.9 | 0.8 | 0.9 | 1.0 | 1.1 |
| Asn | 0.9 | 0.9 | 0.9 | 0.9 | 1.1 | 0.9 | 1.0 |
| Asp | 0.6 | 0.9 | 1.0 | 0.8 | 0.9 | 1.1 | 0.9 |
| ATP | 1.0 | 2.2 | 1.7 | 1.2 | 1.2 | 0.6 | 1.2 |
| Betaine | 0.8 | 0.9 | 1.1 | 0.8 | 1.0 | 1.0 | 1.2 |
| Betaine aldehyde +H$_2$O | N.A. | 1< | 0.9 | N.A. | 1.1 | 1.1 | 0.8 |
| cAMP | N.A. | N.A. | 1.1 | N.A. | 2.1 | 0.9 | N.A. |
| Carnosine | N.A. | 1.0 | 1.9 | 1.0 | 1.0 | 1.4 | 0.9 |
| CDP | N.A. | 0.9 | 1.3 | 1.6 | 1.2 | 0.7 | N.A. |
| cGMP | N.A. | N.A. | N.A. | <1 | N.A. | N.A. | N.A. |
| Choline | 1.0 | 1.2 | 0.6 | 0.9 | 1.2 | 1.1 | 0.9 |
| cis-Aconitic acid | 0.8 | N.A. | 1.4 | N.A. | 1.1 | 1.5 | N.A. |
| Citric acid | 0.9 | 0.9 | 1.3 | 0.8 | 1.1 | 1.4 | 1.4 |
| Citrulline | 1.2 | 1.1 | 1.0 | 1.0 | 1.1 | 1.1 | 1.5 |
| CMP | N.A. | 0.9 | 1.1 | 1.2 | 1.2 | 0.9 | 1.1 |
| CoA_divalent | N.A. | 1.2 | 1.1 | 1.2 | 1.2 | 1.3 | 0.8 |
| Creatine | 0.8 | 1.0 | 1.4 | 1.1 | 1.2 | 1.3 | 1.4 |
| Creatinine | 0.6 | 1.0 | 1.3 | 0.9 | 0.7 | 0.9 | 0.7 |
| CTP | N.A. | 1< | 1.8 | 2.4 | N.A. | 0.5 | N.A. |
| Cys | N.A. | 1.1 | 0.8 | 1.2 | 0.9 | 1.3 | 1.0 |
| Cytidine | 0.7 | 0.9 | 1.1 | 0.9 | 1.1 | 0.8 | 1.2 |
| Cytosine | N.A. | N.A. | N.A. | N.A. | N.A. | 0.9 | N.A. |
| dATP | N.A. | N.A. | N.A. | N.A. | N.A. | 0.4 | N.A. |
| dCTP | N.A. | N.A. | N.A. | N.A. | N.A. | 0.4 | N.A. |
| Dihydroxyacetone phosphate | N.A. | N.A. | 1.7 | 1.2 | 1.0 | 1.2 | N.A. |
| dTDP | N.A. | N.A. | N.A. | 0.9 | N.A. | 0.5 | N.A. |
| dTMP | N.A. | N.A. | 0.9 | N.A. | N.A. | 0.9 | N.A. |
| dTTP | N.A. | N.A. | N.A. | N.A. | N.A. | 0.4 | N.A. |
| Erythrose 4-phosphate | 1.0 | N.A. | N.A. | N.A. | N.A. | N.A. | N.A. |
| Fructose 1,6-diphosphate | N.A. | N.A. | 1< | 0.5 | 1.2 | 0.8 | N.A. |
| Fructose 6-phosphate | N.A. | 2.8 | 4.0 | 1.1 | 1.1 | 1.0 | 1.0 |
| Fumaric acid | <1 | 1.0 | 1.2 | 1.0 | 1.0 | 1.1 | 1.0 |
| GABA | N.A. | 1.0 | 1.0 | 0.7 | 1.3 | 1.5 | 0.5 |
| GDP | N.A. | 1.0 | 0.9 | 1.1 | 1.1 | 0.9 | 1.1 |
| Gln | 1.1 | 1.0 | 0.9 | 0.9 | 1.0 | 1.0 | 1.4 |
| Glu | 0.6 | 0.6 | 0.7 | 0.8 | 1.0 | 0.8 | 0.9 |
| Gluconic acid | 0.8 | 0.9 | 1.0 | 0.8 | 1.1 | 1.5 | 1.0 |
| Glucose 1-phosphate | N.A. | 1.7 | 2.4 | 1.3 | 0.9 | 1.0 | 0.8 |
| Glucose 6-phosphate | 1.1 | 4.2 | 5.6 | 1.1 | 1.0 | 0.9 | 1.0 |
| Glutathione (GSH) | N.A. | 1.0 | 0.9 | 1.0 | 0.7 | 1.1 | <1 |
| Glutathione (GSSG)_divalent | 1.3 | 1.0 | 0.8 | 0.9 | 1.1 | 1.1 | N.A. |
| Gly | 0.8 | 1.1 | 0.9 | 0.9 | 1.0 | 1.2 | 1.0 |
| Glyceraldehyde 3-phosphate | N.A. | N.A. | N.A. | N.A. | N.A. | N.A. | N.A. |
| Glycerol 3-phosphate | 0.5 | 0.8 | 0.9 | 0.9 | 1.1 | 1.0 | 1.0 |
| Glycolic acid | N.A. | N.A. | N.A. | N.A. | N.A. | N.A. | N.A. |
| Glyoxylic acid | N.A. | N.A. | N.A. | N.A. | N.A. | N.A. | N.A. |
| GMP | N.A. | 0.8 | 0.9 | 1.0 | 1.1 | 1.2 | 0.8 |
| GTP | N.A. | 1.4 | 1.4 | 1.2 | 1.1 | 0.6 | 1.2 |

Fig. 42 - 2

| Metabolite | Liver | Colon | Stomach | Adipose tissue | Testis | Pancreas | Spleen | Brain |
|---|---|---|---|---|---|---|---|---|
| 2-Hydroxybutyric acid | 1.2 | 0.5 | 0.5 | 0.8 | <1 | 0.6 | 0.5 | 0.6 |
| 2-Oxoglutaric acid | N.A. | N.A. | N.A. | N.A. | N.A. | N.A. | N.A. | N.A. |
| 2-Oxoisovaleric acid | N.A. | N.A. | N.A. | 1< | N.A. | 1< | N.A. | N.A. |
| 2-Phosphoglyceric acid | 1.1 | N.A. | N.A. | 0.8 | N.A. | N.A. | N.A. | N.A. |
| 3-Hydroxybutyric acid | 0.6 | 0.4 | 0.3 | 0.4 | 0.4 | 0.7 | 0.3 | 0.4 |
| 3-Phosphoglyceric acid | 0.9 | 0.7 | N.A. | 0.8 | 0.5 | N.A. | N.A. | N.A. |
| 6-Phosphogluconic acid | 0.9 | N.A. | 1.0 | 0.8 | N.A. | 1.2 | 1.3 | 0.7 |
| Acetyl CoA_divalent | 0.8 | N.A. | 1.1 | 1.0 | N.A. | N.A. | N.A. | N.A. |
| Adenine | 1.2 | 0.9 | 0.9 | 0.9 | 1.1 | 0.7 | 0.9 | 1.0 |
| Adenosine | 1.3 | 1.0 | 1.3 | 0.7 | 0.9 | 1.1 | 1.1 | 1.2 |
| ADP | 1.3 | 0.8 | 0.9 | 0.9 | 1.0 | 1.1 | 1.1 | 0.7 |
| Ala | 0.7 | 0.8 | 0.8 | 0.7 | 0.5 | 0.9 | 0.8 | 0.7 |
| AMP | 0.9 | 0.8 | 0.8 | 0.8 | 1.0 | 0.8 | 0.9 | 0.9 |
| Anthranilic acid | 0.9 | N.A. | N.A. | N.A. | N.A. | N.A. | N.A. | N.A. |
| Arg | 1.6 | 1.0 | 0.9 | 0.8 | 1.1 | 0.8 | 0.9 | 0.9 |
| Asn | 0.7 | 0.8 | 0.8 | 1.0 | 1.0 | 0.4 | 0.9 | 0.7 |
| Asp | 0.9 | 0.8 | 0.9 | 0.9 | 1.1 | 1.1 | 0.9 | 1.0 |
| ATP | 2.2 | 0.9 | 1.1 | 1.7 | 1.1 | 1.7 | 1.2 | 0.5 |
| Betaine | 1.0 | 1.1 | 1.0 | 0.8 | 1.0 | 1.1 | 0.8 | 0.9 |
| Betaine aldehyde_+H$_2$O | 0.9 | 1.2 | 1.6 | 0.7 | 1.0 | 1.0 | N.A. | N.A. |
| cAMP | N.A. | 1.4 | 1.2 | 1.7 | N.A. | N.A. | 1.4 | N.A. |
| Carnosine | 1.1 | 0.7 | 0.9 | 3.7 | 1.2 | 0.8 | 1.2 | 1.0 |
| CDP | 1.7 | 0.8 | 0.8 | 0.7 | 0.8 | 1.1 | 1.5 | N.A. |
| cGMP | N.A. | N.A. | N.A. | N.A. | N.A. | N.A. | 1< | N.A. |
| Choline | 0.6 | 0.9 | 0.8 | 0.8 | 1.0 | 1.0 | 0.9 | 1.2 |
| cis-Aconitic acid | N.A. | <1 | 0.9 | N.A. | N.A. | 0.9 | 1.0 | N.A. |
| Citric acid | 1.7 | 0.8 | 1.0 | 0.8 | 0.9 | 1.0 | 1.0 | 0.9 |
| Citrulline | 0.9 | 0.9 | 1.0 | 1.0 | 0.6 | 0.8 | 1.0 | 0.9 |
| CMP | 1.2 | 0.8 | 1.1 | 0.8 | 1.1 | 1.2 | 1.1 | 0.9 |
| CoA_divalent | 1.1 | 0.9 | 1.2 | 0.8 | 1.0 | 0.9 | 1.0 | 0.9 |
| Creatine | 1.1 | 1.0 | 1.0 | 1.2 | 1.0 | 1.1 | 1.0 | 1.0 |
| Creatinine | 0.8 | 0.8 | 0.6 | 0.7 | 0.9 | 0.9 | 0.9 | 0.9 |
| CTP | N.A. | 1.0 | N.A. | 1< | 1.0 | 2.1 | N.A. | N.A. |
| Cys | 1.1 | 0.6 | 0.6 | 0.6 | 0.4 | 0.6 | 0.8 | 2.2 |
| Cytidine | 1.5 | 1.1 | 1.1 | 0.8 | 0.9 | 0.8 | 1.0 | 1.0 |
| Cytosine | N.A. | N.A. | N.A. | N.A. | N.A. | N.A. | N.A. | N.A. |
| dATP | N.A. | N.A. | N.A. | N.A. | N.A. | N.A. | N.A. | N.A. |
| dCTP | N.A. | N.A. | N.A. | N.A. | N.A. | N.A. | N.A. | N.A. |
| Dihydroxyacetone phosphate | 1< | 1.0 | 0.9 | 0.9 | 0.7 | N.A. | 1.2 | <1 |
| dTDP | N.A. | N.A. | N.A. | N.A. | N.A. | N.A. | 1.3 | N.A. |
| dTMP | N.A. | N.A. | N.A. | N.A. | 1.1 | N.A. | 1.1 | N.A. |
| dTTP | N.A. | N.A. | N.A. | N.A. | N.A. | N.A. | <1 | N.A. |
| Erythrose 4-phosphate | N.A. | N.A. | N.A. | N.A. | N.A. | N.A. | N.A. | N.A. |
| Fructose 1,6-diphosphate | N.A. | 0.4 | 1.1 | 0.9 | N.A. | 1.8 | 1.1 | 1.0 |
| Fructose 6-phosphate | 1.7 | 0.7 | 1.0 | 0.8 | 0.8 | 1.0 | 1.1 | 0.7 |
| Fumaric acid | 1.2 | 0.8 | 0.8 | 0.8 | 0.5 | 1.1 | 0.9 | 0.8 |
| GABA | 1.4 | 0.7 | 1.3 | 0.5 | 1.1 | 0.8 | 0.9 | 0.9 |
| GDP | 1.1 | 1.0 | 1.0 | 0.8 | 0.9 | 0.8 | 1.1 | 1.0 |
| Gln | 1.3 | 0.9 | 1.0 | 0.9 | 1.2 | 0.8 | 1.0 | 1.0 |
| Glu | 1.0 | 0.8 | 0.7 | 0.6 | 0.8 | 0.9 | 0.7 | 0.9 |
| Gluconic acid | 1.1 | 1.0 | 0.8 | 0.9 | 0.9 | 1.1 | 1.0 | N.A. |
| Glucose 1-phosphate | 1.5 | 0.8 | 0.8 | 0.8 | 0.8 | 0.9 | 1.2 | 0.7 |
| Glucose 6-phosphate | 1.6 | 0.8 | 0.9 | 0.8 | 0.7 | 1.1 | 1.2 | 0.6 |
| Glutathione (GSH) | 1.3 | 0.7 | 0.9 | 0.6 | 1.0 | 0.9 | 0.8 | 0.8 |
| Glutathione (GSSG)_divalent | 1.3 | 1.2 | 0.9 | 0.9 | 1.2 | 1.3 | 1.0 | 1.2 |
| Gly | 0.8 | 0.9 | 0.9 | 0.9 | 1.0 | 0.8 | 0.9 | 1.0 |
| Glyceraldehyde 3-phosphate | N.A. | N.A. | N.A. | N.A. | N.A. | N.A. | N.A. | N.A. |
| Glycerol 3-phosphate | 1.0 | 1.0 | 0.8 | 0.9 | 0.6 | 0.9 | 0.8 | 0.9 |
| Glycolic acid | N.A. | N.A. | N.A. | N.A. | N.A. | N.A. | N.A. | N.A. |
| Glyoxylic acid | N.A. | N.A. | N.A. | N.A. | N.A. | N.A. | N.A. | N.A. |
| GMP | 0.9 | 0.8 | 0.8 | 0.8 | 1.0 | 0.9 | 0.9 | 0.9 |
| GTP | 1.6 | 1.3 | 1.3 | 0.8 | 1.0 | 1.1 | 1.3 | 0.7 |

Fig. 42 – 3

| Metabolite | Plasma | Skeletal muscle | Brown fat | Heart | Lung | Thymus | Kidney |
|---|---|---|---|---|---|---|---|
| Guanine | N.A. | N.A. | 1.9 | 1.2 | N.A. | 0.7 | 1.0 |
| Guanosine | N.A. | 1.1 | 1.3 | 1.1 | 1.7 | 1.5 | 1.0 |
| His | 0.9 | 1.0 | 0.9 | 1.1 | 1.0 | 1.0 | 1.1 |
| Homoserine | N.A. | N.A. | 0.9 | 0.9 | 0.9 | N.A. | N.A. |
| Hydroxyproline | 0.7 | 1.1 | 1.0 | 1.0 | 0.9 | 0.9 | 0.8 |
| Hypoxanthine | N.A. | 1.2 | 1.4 | 1.0 | 1.3 | 1.0 | 1.0 |
| Ile | 0.8 | 0.8 | 0.7 | 0.7 | 0.8 | 1.0 | 0.8 |
| IMP | N.A. | 1.0 | 1.0 | 1.2 | 1.8 | 1.5 | 0.8 |
| Inosine | N.A. | 1.1 | 1.6 | 1.2 | 1.4 | 1.7 | 1.0 |
| Isocitric acid | 0.9 | N.A. | N.A. | N.A. | N.A. | 1.0 | N.A. |
| Lactic acid | 0.7 | 1.1 | 1.6 | 1.1 | 0.8 | 0.9 | 0.8 |
| Leu | 1.0 | 0.9 | 0.8 | 0.8 | 0.9 | 1.0 | 1.0 |
| Lys | 1.0 | 1.5 | 1.1 | 1.0 | 0.9 | 1.1 | 1.5 |
| Malic acid | 0.7 | 1.0 | 1.6 | 0.9 | 0.9 | 1.1 | 1.0 |
| Malonyl CoA divalent | N.A. | N.A. | N.A. | N.A. | N.A. | N.A. | N.A. |
| Met | 0.8 | 0.9 | 0.8 | 0.7 | 1.0 | 0.9 | 0.9 |
| $N,N$-Dimethylglycine | 0.8 | 1.0 | 0.9 | 0.8 | 0.9 | 1.1 | 1.1 |
| $NAD^+$ | N.A. | 1.1 | 1.0 | 1.1 | 0.9 | 0.9 | 0.7 |
| $NADP^+$ | N.A. | 1< | 0.9 | 1.0 | 1.1 | 0.9 | 1.0 |
| Ornithine | 1.1 | 1.0 | 1.1 | 0.9 | 0.8 | 1.1 | 2.0 |
| Phe | 1.1 | 1.0 | 0.9 | 0.9 | 1.0 | 1.0 | 1.0 |
| Phosphoenolpyruvic acid | 1< | N.A. | 1.4 | 0.5 | 0.9 | 0.9 | N.A. |
| Pro | 1.0 | 1.1 | 0.9 | 0.9 | 1.0 | 1.0 | 1.0 |
| PRPP | N.A. | N.A. | 1< | 2.2 | 1.4 | 0.8 | N.A. |
| Putrescine | 0.7 | 1.6 | 1.5 | 1.4 | 1.2 | 2.7 | 1.3 |
| Pyruvic acid | 1.2 | 1.3 | 1.3 | 1.0 | N.A. | N.A. | N.A. |
| Ribose 5-phosphate | N.A. | 0.7 | 1.3 | 1.1 | 1.0 | 2.0 | 0.8 |
| Ribulose 5-phosphate | 1.1 | 1.1 | 1.2 | 1.0 | 1.1 | 1.4 | 1.0 |
| $S$-Adenosylmethionine | N.A. | 0.9 | 0.9 | 1.0 | 1.1 | 1.0 | 1.0 |
| Sarcosine | 1.0 | 1.4 | 0.8 | 0.9 | 0.9 | 1.0 | 1.2 |
| Sedoheptulose 7-phosphate | N.A. | 1.2 | 1.7 | 1.0 | 0.9 | 1.6 | 1.2 |
| Ser | 0.9 | 0.9 | 0.9 | 0.8 | 1.0 | 1.0 | 1.1 |
| Spermidine | 0.8 | 1.1 | 1.1 | 0.9 | 0.6 | 0.8 | 0.9 |
| Spermine | N.A. | N.A. | 1.2 | 0.4 | 0.6 | 0.8 | 0.7 |
| Succinic acid | N.A. | 0.8 | 1.2 | 1.0 | 1.1 | 1.0 | 0.7 |
| Thr | 0.9 | 0.9 | 0.8 | 0.9 | 1.1 | 1.0 | 1.1 |
| Thymidine | 0.6 | 0.9 | 0.8 | N.A. | 0.9 | 0.8 | N.A. |
| Thymine | N.A. | N.A. | N.A. | N.A. | N.A. | N.A. | N.A. |
| Trp | 0.9 | 0.9 | 0.8 | 0.8 | 0.8 | 1.0 | 0.9 |
| Tyr | 0.9 | 0.9 | 0.9 | 0.7 | 0.9 | 0.9 | 1.0 |
| Tyramine | N.A. | N.A. | N.A. | N.A. | N.A. | N.A. | N.A. |
| UDP | 1< | 1.1 | 1.2 | 1.5 | 1.2 | 1.0 | 1.1 |
| UMP | N.A. | 0.9 | 1.0 | 1.2 | 1.2 | 1.3 | 0.9 |
| Uracil | 0.7 | N.A. | 0.8 | 1.1 | 0.9 | 1.1 | 1.1 |
| Uridine | 0.7 | 1.0 | 1.0 | 1.0 | 1.3 | 1.0 | 1.1 |
| UTP | N.A. | 1.8 | 1.8 | 2.9 | 1.2 | 0.7 | 1.4 |
| Val | 1.0 | 0.9 | 0.8 | 0.8 | 0.9 | 1.0 | 0.9 |
| β-Ala | 0.8 | 1.0 | 1.2 | 1.1 | 1.5 | 1.6 | 0.9 |

1<: SAMR1 in SAMP8/SAMR1 is below the detection limit.
<1: SAMRP8 in SAMP8/SAMR1 is below the detection limit.

Fig. 42 – 4

| Metabolite | Liver | Colon | Stomach | Adipose tissue | Testis | Pancreas | Spleen | Brain |
|---|---|---|---|---|---|---|---|---|
| Guanine | 1.2 | 1.0 | 0.8 | 0.9 | 0.8 | N.A. | 1.2 | 1.1 |
| Guanosine | 1.2 | 1.0 | 1.0 | 0.9 | 0.9 | 1.2 | 1.1 | 1.3 |
| His | 1.1 | 0.9 | 1.0 | 0.9 | 1.0 | 1.1 | 1.0 | 1.0 |
| Homoserine | 1.2 | 1.0 | 0.9 | N.A. | 1.0 | 0.6 | N.A. | 0.8 |
| Hydroxyproline | 0.8 | 0.7 | 0.8 | 0.8 | 0.7 | 0.5 | 0.8 | 0.8 |
| Hypoxanthine | 1.1 | 1.0 | 0.9 | 1.0 | 1.0 | 0.9 | 1.1 | 1.1 |
| Ile | 0.8 | 0.9 | 0.8 | 0.9 | 0.7 | 0.4 | 0.8 | 0.8 |
| IMP | 1.0 | 1.2 | 1.0 | 1.4 | 1.2 | 2.0 | 1.3 | 1.3 |
| Inosine | 1.1 | 1.1 | 1.0 | 0.9 | 1.1 | 1.1 | 1.1 | 1.1 |
| Isocitric acid | N.A. | N.A. | N.A. | 1.0 | N.A. | N.A. | <1 | N.A. |
| Lactic acid | 1.0 | 0.7 | 0.7 | 0.9 | 0.5 | 0.9 | 0.8 | 0.6 |
| Leu | 0.9 | 1.0 | 0.9 | 1.0 | 0.8 | 0.5 | 0.9 | 0.9 |
| Lys | 1.0 | 0.9 | 1.0 | 1.0 | 1.0 | 0.8 | 1.0 | 1.0 |
| Malic acid | 1.5 | 0.8 | 0.7 | 0.7 | 0.5 | 1.1 | 0.9 | 0.7 |
| Malonyl CoA divalent | N.A. | N.A. | N.A. | N.A. | N.A. | N.A. | N.A. | N.A. |
| Met | 0.5 | 0.8 | 0.9 | 0.8 | 0.8 | 0.8 | 0.7 | 0.8 |
| $N,N$-Dimethylglycine | 0.9 | 0.8 | 1.0 | 0.7 | 1.1 | 0.9 | 1.0 | N.A. |
| NAD$^+$ | 0.5 | 0.8 | 1.0 | 0.8 | 0.9 | 0.7 | 0.7 | 1.0 |
| NADP$^+$ | 0.7 | 0.6 | 1.2 | 0.7 | 1.0 | 0.8 | 1.1 | 1.0 |
| Ornithine | 1.0 | 1.0 | 0.9 | 1.1 | 0.9 | 0.8 | 1.0 | 0.9 |
| Phe | 0.7 | 1.0 | 0.9 | 0.9 | 1.0 | 1.2 | 1.0 | 1.0 |
| Phosphoenolpyruvic acid | 1.0 | N.A. | 1.1 | 1.2 | <1 | 1.0 | 1.1 | N.A. |
| Pro | 0.9 | 0.9 | 0.9 | 0.9 | 1.0 | 0.9 | 0.9 | 1.1 |
| PRPP | 1.0 | N.A. | N.A. | N.A. | 1.1 | 1.4 | 1.7 | 0.9 |
| Putrescine | 1.8 | 1.0 | 1.3 | 0.9 | 1.2 | 0.9 | 1.6 | 1.0 |
| Pyruvic acid | N.A. | 1< | N.A. | N.A. | N.A. | N.A. | N.A. | N.A. |
| Ribose 5-phosphate | 1.2 | 1.1 | 0.8 | 1.1 | 1.1 | 1< | 1.3 | 1.3 |
| Ribulose 5-phosphate | 1.1 | 1.0 | 1.0 | 1.0 | 1.0 | 1.0 | 0.9 | 1.0 |
| $S$-Adenosylmethionine | 2.0 | 0.8 | 0.9 | 0.8 | 0.9 | 1.2 | 1.0 | 0.8 |
| Sarcosine | 0.8 | 1.6 | 1.1 | 1< | 0.9 | 1.0 | 1.1 | N.A. |
| Sedoheptulose 7-phosphate | 1.3 | 1.0 | 0.9 | 0.9 | 1.0 | 1.1 | 1.3 | 1.1 |
| Ser | 0.9 | 0.9 | 0.9 | 0.9 | 1.0 | 0.8 | 0.9 | 0.9 |
| Spermidine | 1.2 | 0.8 | 0.8 | 0.7 | 0.9 | 0.9 | 1.0 | 0.9 |
| Spermine | 1.0 | 0.7 | 2.1 | 0.8 | 1.2 | 1.1 | 0.9 | 0.8 |
| Succinic acid | 0.8 | 0.6 | 0.7 | 0.9 | 0.8 | 1.0 | 0.9 | 0.8 |
| Thr | 0.9 | 0.9 | 1.0 | 0.9 | 1.0 | 0.6 | 0.9 | 1.1 |
| Thymidine | 0.9 | 0.9 | 0.8 | N.A. | 0.9 | 0.8 | 0.6 | 0.8 |
| Thymine | N.A. | N.A. | N.A. | N.A. | N.A. | N.A. | N.A. | N.A. |
| Trp | 0.7 | 0.8 | 0.9 | 0.8 | 0.9 | 0.6 | 0.9 | 0.9 |
| Tyr | 0.7 | 0.9 | 0.8 | 0.9 | 0.8 | 0.8 | 0.8 | 0.9 |
| Tyramine | N.A. | N.A. | 1< | N.A. | N.A. | 1.0 | N.A. | N.A. |
| UDP | 1.4 | 1.3 | 0.9 | 0.8 | 1.1 | 0.9 | 1.4 | 0.6 |
| UMP | 1.1 | 0.9 | 0.9 | 0.9 | 0.9 | 1.1 | 1.1 | 1.0 |
| Uracil | 1.5 | 1.0 | 1.0 | <1 | 0.9 | 1.0 | 0.9 | 1.0 |
| Uridine | 1.4 | 1.0 | 1.2 | 0.8 | 0.9 | 1.0 | 1.0 | 1.2 |
| UTP | 2.3 | 1.6 | 1.0 | 1.2 | 1.2 | 1.5 | 1.7 | 0.5 |
| Val | 1.0 | 0.9 | 0.9 | 1.0 | 0.8 | 0.6 | 0.9 | 0.9 |
| β-Ala | 0.8 | 1.0 | 1.1 | 1.0 | 0.9 | 1.3 | 1.3 | 1.1 |

1<: SAMR1 in SAMP8/SAMR1 is below the detection limit.
<1: SAMRP8 in SAMP8/SAMR1 is below the detection limit.

Fig. 43 - 1

| Line No. | Group | | | | | | Sub-Group | Gene_id |
|---|---|---|---|---|---|---|---|---|
| 1 | 3 | 4 | 5 | 6 | 7 | 8 | VIII | Apoa1 |
| 2 | 3 | 4 | 5 | 6 | 7 | 8 | VIII | Apoa2 |
| 3 | 3 | 4 | 5 | 6 | 7 | 8 | VIII | Cdkn1a |
| 4 | 3 | 4 | 5 | 6 | 7 | 8 | VIII | Ces2e |
| 5 | 3 | 4 | 5 | 6 | 7 | 8 | VIII | Cfd |
| 6 | 3 | 4 | 5 | 6 | 7 | 8 | VIII | Cidec |
| 7 | 3 | 4 | 5 | 6 | 7 | 8 | VIII | Cyp27b1 |
| 8 | 3 | 4 | 5 | 6 | 7 | 8 | VIII | Cyp8b1 |
| 9 | 3 | 4 | 5 | 6 | 7 | 8 | VIII | Eda2r |
| 10 | 3 | 4 | 5 | 6 | 7 | 8 | VIII | Gdf15 |
| 11 | 3 | 4 | 5 | 6 | 7 | 8 | VIII | Hamp |
| 12 | 3 | 4 | 5 | 6 | 7 | 8 | VIII | Hmox1 |
| 13 | 3 | 4 | 5 | 6 | 7 | 8 | VIII | Isg15 |
| 14 | 3 | 4 | 5 | 6 | 7 | 8 | VIII | Klf7 |
| 15 | 3 | 4 | 5 | 6 | 7 | 8 | VIII | Krt16 |
| 16 | 3 | 4 | 5 | 6 | 7 | 8 | VIII | Krt20 |
| 17 | 3 | 4 | 5 | 6 | 7 | 8 | VIII | Lcn2 |
| 18 | 3 | 4 | 5 | 6 | 7 | 8 | VIII | Lgals3 |
| 19 | 3 | 4 | 5 | 6 | 7 | 8 | VIII | Mgmt |
| 20 | 3 | 4 | 5 | 6 | 7 | 8 | VIII | Myl7 |
| 21 | 3 | 4 | 5 | 6 | 7 | 8 | VIII | Phlda3 |
| 22 | 3 | 4 | 5 | 6 | 7 | 8 | VIII | Prss3 |
| 23 | 3 | 4 | 5 | 6 | 7 | 8 | VIII | Reg2 |
| 24 | 3 | 4 | 5 | 6 | 7 | 8 | VIII | Reg3a |
| 25 | 3 | 4 | 5 | 6 | 7 | 8 | VIII | Reg3d |
| 26 | 3 | 4 | 5 | 6 | 7 | 8 | VIII | Saa1 |
| 27 | 3 | 4 | 5 | 6 | 7 | 8 | VIII | Saa2 |
| 28 | 3 | 4 | 5 | 6 | 7 | 8 | VIII | Saa3 |
| 29 | 3 | 4 | 5 | 6 | 7 | 8 | VIII | Serpina7 |
| 30 | 3 | 4 | 5 | 6 | 7 | 8 | VIII | Serpine1 |
| 31 | 3 | 4 | 5 | 6 | 7 | 8 | VIII | Sln |
| 32 | 3 | 4 | 5 | 6 | 7 | | VII-2 | 1700003E24Rik |
| 33 | 3 | 4 | 5 | 6 | 7 | | VII-2 | 1700003F12Rik |
| 34 | 3 | 4 | 5 | 6 | 7 | | VII-2 | 1700008K24Rik |
| 35 | 3 | 4 | 5 | 6 | 7 | | VII-2 | 1700009N14Rik |
| 36 | 3 | 4 | 5 | 6 | 7 | | VII-2 | 1700011H14Rik |
| 37 | 3 | 4 | 5 | 6 | 7 | | VII-2 | 1700013G24Rik |
| 38 | 3 | 4 | 5 | 6 | 7 | | VII-2 | 1700016K19Rik |
| 39 | 3 | 4 | 5 | 6 | 7 | | VII-2 | 1700019D03Rik |
| 40 | 3 | 4 | 5 | 6 | 7 | | VII-2 | 1700019M22Rik |
| 41 | 3 | 4 | 5 | 6 | 7 | | VII-2 | 1700024P04Rik |
| 42 | 3 | 4 | 5 | 6 | 7 | | VII-2 | 1700029F12Rik |
| 43 | 3 | 4 | 5 | 6 | 7 | | VII-2 | 1700034O15Rik |
| 44 | 3 | 4 | 5 | 6 | 7 | | VII-2 | 1700123L14Rik |
| 45 | 3 | 4 | 5 | 6 | 7 | | VII-2 | 4922502D21Rik |
| 46 | 3 | 4 | 5 | 6 | 7 | | VII-2 | 4933411K16Rik |
| 47 | 3 | 4 | 5 | 6 | 7 | | VII-2 | 9930111J21Rik1 |
| 48 | 3 | 4 | 5 | 6 | 7 | | VII-2 | 9930111J21Rik2 |
| 49 | 3 | 4 | 5 | 6 | 7 | | VII-2 | A630007B06Rik |
| 50 | 3 | 4 | 5 | 6 | 7 | | VII-2 | Actl7b |
| 51 | 3 | 4 | 5 | 6 | 7 | | VII-2 | Actl9 |
| 52 | 3 | 4 | 5 | 6 | 7 | | VII-2 | Actrt2 |
| 53 | 3 | 4 | 5 | 6 | 7 | | VII-2 | Ago2 |
| 54 | 3 | 4 | 5 | 6 | 7 | | VII-2 | Akap12 |
| 55 | 3 | 4 | 5 | 6 | 7 | | VII-2 | Akap4 |
| 56 | 3 | 4 | 5 | 6 | 7 | | VII-2 | Apol9a |
| 57 | 3 | 4 | 5 | 6 | 7 | | VII-2 | Apol9b |
| 58 | 3 | 4 | 5 | 6 | 7 | | VII-2 | Arid5b |
| 59 | 3 | 4 | 5 | 6 | 7 | | VII-2 | AY761185 |
| 60 | 3 | 4 | 5 | 6 | 7 | | VII-2 | BB031773 |
| 61 | 3 | 4 | 5 | 6 | 7 | | VII-2 | BC048679 |
| 62 | 3 | 4 | 5 | 6 | 7 | | VII-2 | BC051142 |
| 63 | 3 | 4 | 5 | 6 | 7 | | VII-2 | Bspry |
| 64 | 3 | 4 | 5 | 6 | 7 | | VII-2 | Calml3 |
| 65 | 3 | 4 | 5 | 6 | 7 | | VII-2 | Cbl |
| 66 | 3 | 4 | 5 | 6 | 7 | | VII-2 | Cd72 |
| 67 | 3 | 4 | 5 | 6 | 7 | | VII-2 | Ceacam10 |
| 68 | 3 | 4 | 5 | 6 | 7 | | VII-2 | Cep85l |
| 69 | 3 | 4 | 5 | 6 | 7 | | VII-2 | Ces5a |
| 70 | 3 | 4 | 5 | 6 | 7 | | VII-2 | Cetn1 |
| 71 | 3 | 4 | 5 | 6 | 7 | | VII-2 | Chrm2 |
| 72 | 3 | 4 | 5 | 6 | 7 | | VII-2 | Cmtm2a |
| 73 | 3 | 4 | 5 | 6 | 7 | | VII-2 | Cmtm2b |
| 74 | 3 | 4 | 5 | 6 | 7 | | VII-2 | Cnga1 |
| 75 | 3 | 4 | 5 | 6 | 7 | | VII-2 | Cox8c |
| 76 | 3 | 4 | 5 | 6 | 7 | | VII-2 | Cpa2 |
| 77 | 3 | 4 | 5 | 6 | 7 | | VII-2 | Cplx2 |
| 78 | 3 | 4 | 5 | 6 | 7 | | VII-2 | Cpm |
| 79 | 3 | 4 | 5 | 6 | 7 | | VII-2 | Crisp1 |
| 80 | 3 | 4 | 5 | 6 | 7 | | VII-2 | Crisp2 |
| 81 | 3 | 4 | 5 | 6 | 7 | | VII-2 | Cypt2 |
| 82 | 3 | 4 | 5 | 6 | 7 | | VII-2 | Cypt4 |
| 83 | 3 | 4 | 5 | 6 | 7 | | VII-2 | D830031N03Rik |
| 84 | 3 | 4 | 5 | 6 | 7 | | VII-2 | D930015M05Rik |
| 85 | 3 | 4 | 5 | 6 | 7 | | VII-2 | Dbil5 |
| 86 | 3 | 4 | 5 | 6 | 7 | | VII-2 | Dct |
| 87 | 3 | 4 | 5 | 6 | 7 | | VII-2 | Defa21 |
| 88 | 3 | 4 | 5 | 6 | 7 | | VII-2 | Defb11 |
| 89 | 3 | 4 | 5 | 6 | 7 | | VII-2 | Defb19 |
| 90 | 3 | 4 | 5 | 6 | 7 | | VII-2 | Defb2 |
| 91 | 3 | 4 | 5 | 6 | 7 | | VII-2 | Defb22 |
| 92 | 3 | 4 | 5 | 6 | 7 | | VII-2 | Defb23 |
| 93 | 3 | 4 | 5 | 6 | 7 | | VII-2 | Defb28 |
| 94 | 3 | 4 | 5 | 6 | 7 | | VII-2 | Defb37 |
| 95 | 3 | 4 | 5 | 6 | 7 | | VII-2 | Defb38 |
| 96 | 3 | 4 | 5 | 6 | 7 | | VII-2 | Defb39 |
| 97 | 3 | 4 | 5 | 6 | 7 | | VII-2 | Defb42 |
| 98 | 3 | 4 | 5 | 6 | 7 | | VII-2 | Defb43 |
| 99 | 3 | 4 | 5 | 6 | 7 | | VII-2 | Defb9 |
| 100 | 3 | 4 | 5 | 6 | 7 | | VII-2 | Dkkl1 |
| 101 | 3 | 4 | 5 | 6 | 7 | | VII-2 | Dnajb8 |
| 102 | 3 | 4 | 5 | 6 | 7 | | VII-2 | Dynlrb2 |
| 103 | 3 | 4 | 5 | 6 | 7 | | VII-2 | Eddm3b |
| 104 | 3 | 4 | 5 | 6 | 7 | | VII-2 | Efcab4b |
| 105 | 3 | 4 | 5 | 6 | 7 | | VII-2 | Eif3j1 |
| 106 | 3 | 4 | 5 | 6 | 7 | | VII-2 | Epcam |
| 107 | 3 | 4 | 5 | 6 | 7 | | VII-2 | Fabp9 |
| 108 | 3 | 4 | 5 | 6 | 7 | | VII-2 | Fam129c |
| 109 | 3 | 4 | 5 | 6 | 7 | | VII-2 | Fam13a |
| 110 | 3 | 4 | 5 | 6 | 7 | | VII-2 | Fbp1 |
| 111 | 3 | 4 | 5 | 6 | 7 | | VII-2 | Fhl4 |
| 112 | 3 | 4 | 5 | 6 | 7 | | VII-2 | Foxn3 |
| 113 | 3 | 4 | 5 | 6 | 7 | | VII-2 | Gatad2b |
| 114 | 3 | 4 | 5 | 6 | 7 | | VII-2 | Gdap10 |
| 115 | 3 | 4 | 5 | 6 | 7 | | VII-2 | Gm12250 |
| 116 | 3 | 4 | 5 | 6 | 7 | | VII-2 | Gm128 |
| 117 | 3 | 4 | 5 | 6 | 7 | | VII-2 | Gm3417 |
| 118 | 3 | 4 | 5 | 6 | 7 | | VII-2 | Gm5431 |
| 119 | 3 | 4 | 5 | 6 | 7 | | VII-2 | Gm6644 |
| 120 | 3 | 4 | 5 | 6 | 7 | | VII-2 | Gp2 |
| 121 | 3 | 4 | 5 | 6 | 7 | | VII-2 | Gsg1 |
| 122 | 3 | 4 | 5 | 6 | 7 | | VII-2 | Gstm6 |
| 123 | 3 | 4 | 5 | 6 | 7 | | VII-2 | Gstm7 |
| 124 | 3 | 4 | 5 | 6 | 7 | | VII-2 | Gtsf1l |
| 125 | 3 | 4 | 5 | 6 | 7 | | VII-2 | H1fnt |
| 126 | 3 | 4 | 5 | 6 | 7 | | VII-2 | H2afb1 |
| 127 | 3 | 4 | 5 | 6 | 7 | | VII-2 | Hamp2 |
| 128 | 3 | 4 | 5 | 6 | 7 | | VII-2 | Hils1 |
| 129 | 3 | 4 | 5 | 6 | 7 | | VII-2 | Hipk2 |
| 130 | 3 | 4 | 5 | 6 | 7 | | VII-2 | Hmbox1 |
| 131 | 3 | 4 | 5 | 6 | 7 | | VII-2 | Hmgb4 |
| 132 | 3 | 4 | 5 | 6 | 7 | | VII-2 | Hpgd |
| 133 | 3 | 4 | 5 | 6 | 7 | | VII-2 | Hspb9 |
| 134 | 3 | 4 | 5 | 6 | 7 | | VII-2 | Iapp |
| 135 | 3 | 4 | 5 | 6 | 7 | | VII-2 | Ifi44 |
| 136 | 3 | 4 | 5 | 6 | 7 | | VII-2 | Ifit1 |
| 137 | 3 | 4 | 5 | 6 | 7 | | VII-2 | Igfbp1 |
| 138 | 3 | 4 | 5 | 6 | 7 | | VII-2 | Igll1 |
| 139 | 3 | 4 | 5 | 6 | 7 | | VII-2 | Ins1 |
| 140 | 3 | 4 | 5 | 6 | 7 | | VII-2 | Ins2 |
| 141 | 3 | 4 | 5 | 6 | 7 | | VII-2 | Irf4 |
| 142 | 3 | 4 | 5 | 6 | 7 | | VII-2 | Irgc1 |
| 143 | 3 | 4 | 5 | 6 | 7 | | VII-2 | Klf2b |
| 144 | 3 | 4 | 5 | 6 | 7 | | VII-2 | Klk1b26 |
| 145 | 3 | 4 | 5 | 6 | 7 | | VII-2 | Ldhal6b |
| 146 | 3 | 4 | 5 | 6 | 7 | | VII-2 | Ldhc |
| 147 | 3 | 4 | 5 | 6 | 7 | | VII-2 | Lelp1 |
| 148 | 3 | 4 | 5 | 6 | 7 | | VII-2 | Lrrc18 |
| 149 | 3 | 4 | 5 | 6 | 7 | | VII-2 | Lrrc46 |
| 150 | 3 | 4 | 5 | 6 | 7 | | VII-2 | Ltf |
| 151 | 3 | 4 | 5 | 6 | 7 | | VII-2 | Ly6f |
| 152 | 3 | 4 | 5 | 6 | 7 | | VII-2 | Meig1 |
| 153 | 3 | 4 | 5 | 6 | 7 | | VII-2 | Mia |
| 154 | 3 | 4 | 5 | 6 | 7 | | VII-2 | Mir1199 |
| 155 | 3 | 4 | 5 | 6 | 7 | | VII-2 | Mir1291 |
| 156 | 3 | 4 | 5 | 6 | 7 | | VII-2 | Mir142b |
| 157 | 3 | 4 | 5 | 6 | 7 | | VII-2 | Mir223 |
| 158 | 3 | 4 | 5 | 6 | 7 | | VII-2 | Mir6340 |
| 159 | 3 | 4 | 5 | 6 | 7 | | VII-2 | Mir6357 |
| 160 | 3 | 4 | 5 | 6 | 7 | | VII-2 | Mir6363 |
| 161 | 3 | 4 | 5 | 6 | 7 | | VII-2 | Mir6390 |
| 162 | 3 | 4 | 5 | 6 | 7 | | VII-2 | Mir7060 |
| 163 | 3 | 4 | 5 | 6 | 7 | | VII-2 | Mir7-1 |
| 164 | 3 | 4 | 5 | 6 | 7 | | VII-2 | Mir8112 |
| 165 | 3 | 4 | 5 | 6 | 7 | | VII-2 | Mir8120 |
| 166 | 3 | 4 | 5 | 6 | 7 | | VII-2 | Mup17 |
| 167 | 3 | 4 | 5 | 6 | 7 | | VII-2 | Mup5 |
| 168 | 3 | 4 | 5 | 6 | 7 | | VII-2 | Myl4 |

Fig. 43 - 2

| 169 | 3 | 4 | 5 | 6 | 7 | | VII-2 | Mzb1 |
|---|---|---|---|---|---|---|---|---|
| 170 | 3 | 4 | 5 | 6 | 7 | | VII-2 | Neil1 |
| 171 | 3 | 4 | 5 | 6 | 7 | | VII-2 | Npy |
| 172 | 3 | 4 | 5 | 6 | 7 | | VII-2 | Oas2 |
| 173 | 3 | 4 | 5 | 6 | 7 | | VII-2 | Oas3 |
| 174 | 3 | 4 | 5 | 6 | 7 | | VII-2 | Oasl2 |
| 175 | 3 | 4 | 5 | 6 | 7 | | VII-2 | Oaz3 |
| 176 | 3 | 4 | 5 | 6 | 7 | | VII-2 | Odf1 |
| 177 | 3 | 4 | 5 | 6 | 7 | | VII-2 | Olfml2a |
| 178 | 3 | 4 | 5 | 6 | 7 | | VII-2 | Pdzk1ip1 |
| 179 | 3 | 4 | 5 | 6 | 7 | | VII-2 | Pgk2 |
| 180 | 3 | 4 | 5 | 6 | 7 | | VII-2 | Pip |
| 181 | 3 | 4 | 5 | 6 | 7 | | VII-2 | Pnlip |
| 182 | 3 | 4 | 5 | 6 | 7 | | VII-2 | Ppp1r3g |
| 183 | 3 | 4 | 5 | 6 | 7 | | VII-2 | Prm1 |
| 184 | 3 | 4 | 5 | 6 | 7 | | VII-2 | Prm3 |
| 185 | 3 | 4 | 5 | 6 | 7 | | VII-2 | Prom2 |
| 186 | 3 | 4 | 5 | 6 | 7 | | VII-2 | Ptgds |
| 187 | 3 | 4 | 5 | 6 | 7 | | VII-2 | Rag1 |
| 188 | 3 | 4 | 5 | 6 | 7 | | VII-2 | Rag2 |
| 189 | 3 | 4 | 5 | 6 | 7 | | VII-2 | Ramp3 |
| 190 | 3 | 4 | 5 | 6 | 7 | | VII-2 | Rbakdn |
| 191 | 3 | 4 | 5 | 6 | 7 | | VII-2 | Rnase12 |
| 192 | 3 | 4 | 5 | 6 | 7 | | VII-2 | Rnase9 |
| 193 | 3 | 4 | 5 | 6 | 7 | | VII-2 | Ropn1l |
| 194 | 3 | 4 | 5 | 6 | 7 | | VII-2 | Rpph1 |
| 195 | 3 | 4 | 5 | 6 | 7 | | VII-2 | Rsph1 |
| 196 | 3 | 4 | 5 | 6 | 7 | | VII-2 | Scgb2b27 |
| 197 | 3 | 4 | 5 | 6 | 7 | | VII-2 | Serpina1b |
| 198 | 3 | 4 | 5 | 6 | 7 | | VII-2 | Serpina1f |
| 199 | 3 | 4 | 5 | 6 | 7 | | VII-2 | Shroom4 |
| 200 | 3 | 4 | 5 | 6 | 7 | | VII-2 | Slc35f2 |
| 201 | 3 | 4 | 5 | 6 | 7 | | VII-2 | Smcp |
| 202 | 3 | 4 | 5 | 6 | 7 | | VII-2 | Snora31 |
| 203 | 3 | 4 | 5 | 6 | 7 | | VII-2 | Snora44 |
| 204 | 3 | 4 | 5 | 6 | 7 | | VII-2 | Snora7a |
| 205 | 3 | 4 | 5 | 6 | 7 | | VII-2 | Spa17 |
| 206 | 3 | 4 | 5 | 6 | 7 | | VII-2 | Spata18 |
| 207 | 3 | 4 | 5 | 6 | 7 | | VII-2 | Spata3 |
| 208 | 3 | 4 | 5 | 6 | 7 | | VII-2 | Spata4 |
| 209 | 3 | 4 | 5 | 6 | 7 | | VII-2 | Spem1 |
| 210 | 3 | 4 | 5 | 6 | 7 | | VII-2 | Spert |
| 211 | 3 | 4 | 5 | 6 | 7 | | VII-2 | Spink7 |
| 212 | 3 | 4 | 5 | 6 | 7 | | VII-2 | Spink8 |
| 213 | 3 | 4 | 5 | 6 | 7 | | VII-2 | Spint3 |
| 214 | 3 | 4 | 5 | 6 | 7 | | VII-2 | Spz1 |
| 215 | 3 | 4 | 5 | 6 | 7 | | VII-2 | Sult1d1 |
| 216 | 3 | 4 | 5 | 6 | 7 | | VII-2 | Tcp11 |
| 217 | 3 | 4 | 5 | 6 | 7 | | VII-2 | Tcte3 |
| 218 | 3 | 4 | 5 | 6 | 7 | | VII-2 | Tex33 |
| 219 | 3 | 4 | 5 | 6 | 7 | | VII-2 | Tgoln2 |
| 220 | 3 | 4 | 5 | 6 | 7 | | VII-2 | Tmco2 |
| 221 | 3 | 4 | 5 | 6 | 7 | | VII-2 | Tmem212 |
| 222 | 3 | 4 | 5 | 6 | 7 | | VII-2 | Tmem254c |
| 223 | 3 | 4 | 5 | 6 | 7 | | VII-2 | Tmsb15l |
| 224 | 3 | 4 | 5 | 6 | 7 | | VII-2 | Tnp1 |
| 225 | 3 | 4 | 5 | 6 | 7 | | VII-2 | Trim36 |
| 226 | 3 | 4 | 5 | 6 | 7 | | VII-2 | Tssk1 |
| 227 | 3 | 4 | 5 | 6 | 7 | | VII-2 | Tssk2 |
| 228 | 3 | 4 | 5 | 6 | 7 | | VII-2 | Tuba3a |
| 229 | 3 | 4 | 5 | 6 | 7 | | VII-2 | Tuba3b |
| 230 | 3 | 4 | 5 | 6 | 7 | | VII-2 | Tube1 |
| 231 | 3 | 4 | 5 | 6 | 7 | | VII-2 | Txndc2 |
| 232 | 3 | 4 | 5 | 6 | 7 | | VII-2 | Tyrp1 |
| 233 | 3 | 4 | 5 | 6 | 7 | | VII-2 | Uchl1 |
| 234 | 3 | 4 | 5 | 6 | 7 | | VII-2 | Uhmk1 |
| 235 | 3 | 4 | 5 | 6 | 7 | | VII-2 | Usp18 |
| 236 | 3 | 4 | 5 | 6 | 7 | | VII-2 | Vpreb1 |
| 237 | 3 | 4 | 5 | 6 | 7 | | VII-2 | Vpreb3 |
| 238 | 3 | 4 | 5 | 6 | 7 | | VII-2 | Wfdc10 |
| 239 | 3 | 4 | 5 | 6 | 7 | | VII-2 | Wfdc13 |
| 240 | 3 | 4 | 5 | 6 | 7 | | VII-2 | Wfdc15b |
| 241 | 3 | 4 | 5 | 6 | 7 | | VII-2 | Wfdc16 |
| 242 | 3 | 4 | 5 | 6 | 7 | | VII-2 | Wisp3 |
| 243 | 3 | 4 | 5 | 6 | 7 | | VII-2 | Zbed6 |
| 244 | 3 | 4 | 5 | 6 | 7 | | VII-2 | Zfp366 |
| 245 | 3 | 4 | 5 | 6 | 7 | | VII-2 | Znrf4 |
| 246 | 3 | 4 | 5 | 6 | 7 | | VII-1 | 1700007K13Rik |
| 247 | 3 | 4 | 5 | 6 | 7 | | VII-1 | 1810009J06Rik |
| 248 | 3 | 4 | 5 | 6 | 7 | | VII-1 | 2210010C04Rik |
| 249 | 3 | 4 | 5 | 6 | 7 | | VII-1 | 3425401B19Rik |
| 250 | 3 | 4 | 5 | 6 | 7 | | VII-1 | 9030617O03Rik |
| 251 | 3 | 4 | 5 | 6 | 7 | | VII-1 | 9030619P08Rik |
| 252 | 3 | 4 | 5 | 6 | 7 | | VII-1 | A530016L24Rik |
| 253 | 3 | 4 | 5 | 6 | 7 | | VII-1 | A930001C03Rik |
| 254 | 3 | 4 | 5 | 6 | 7 | | VII-1 | A930016O22Rik |
| 255 | 3 | 4 | 5 | 6 | 7 | | VII-1 | Abra |
| 256 | 3 | 4 | 5 | 6 | 7 | | VII-1 | Acta1 |
| 257 | 3 | 4 | 5 | 6 | 7 | | VII-1 | Actn2 |
| 258 | 3 | 4 | 5 | 6 | 7 | | VII-1 | Actn3 |
| 259 | 3 | 4 | 5 | 6 | 7 | | VII-1 | Adssl1 |
| 260 | 3 | 4 | 5 | 6 | 7 | | VII-1 | Alpk3 |
| 261 | 3 | 4 | 5 | 6 | 7 | | VII-1 | Amd1 |
| 262 | 3 | 4 | 5 | 6 | 7 | | VII-1 | Amd2 |
| 263 | 3 | 4 | 5 | 6 | 7 | | VII-1 | Ampd1 |
| 264 | 3 | 4 | 5 | 6 | 7 | | VII-1 | Amy2a5 |
| 265 | 3 | 4 | 5 | 6 | 7 | | VII-1 | Amy2b |
| 266 | 3 | 4 | 5 | 6 | 7 | | VII-1 | Ankrd2 |
| 267 | 3 | 4 | 5 | 6 | 7 | | VII-1 | Ankrd23 |
| 268 | 3 | 4 | 5 | 6 | 7 | | VII-1 | Apobec2 |
| 269 | 3 | 4 | 5 | 6 | 7 | | VII-1 | Art1 |
| 270 | 3 | 4 | 5 | 6 | 7 | | VII-1 | Art5 |
| 271 | 3 | 4 | 5 | 6 | 7 | | VII-1 | Asb11 |
| 272 | 3 | 4 | 5 | 6 | 7 | | VII-1 | Asb12 |
| 273 | 3 | 4 | 5 | 6 | 7 | | VII-1 | Asb2 |
| 274 | 3 | 4 | 5 | 6 | 7 | | VII-1 | Asb5 |
| 275 | 3 | 4 | 5 | 6 | 7 | | VII-1 | Asprv1 |
| 276 | 3 | 4 | 5 | 6 | 7 | | VII-1 | Atcayos |
| 277 | 3 | 4 | 5 | 6 | 7 | | VII-1 | Atp2a1 |
| 278 | 3 | 4 | 5 | 6 | 7 | | VII-1 | B3galt2 |
| 279 | 3 | 4 | 5 | 6 | 7 | | VII-1 | BC021614 |
| 280 | 3 | 4 | 5 | 6 | 7 | | VII-1 | Bex4 |
| 281 | 3 | 4 | 5 | 6 | 7 | | VII-1 | Bmp10 |
| 282 | 3 | 4 | 5 | 6 | 7 | | VII-1 | Btg3 |
| 283 | 3 | 4 | 5 | 6 | 7 | | VII-1 | C2cd4a |
| 284 | 3 | 4 | 5 | 6 | 7 | | VII-1 | C6 |
| 285 | 3 | 4 | 5 | 6 | 7 | | VII-1 | Cacna1s |
| 286 | 3 | 4 | 5 | 6 | 7 | | VII-1 | Cacng1 |
| 287 | 3 | 4 | 5 | 6 | 7 | | VII-1 | Calm4 |
| 288 | 3 | 4 | 5 | 6 | 7 | | VII-1 | Cap2 |
| 289 | 3 | 4 | 5 | 6 | 7 | | VII-1 | Car3 |
| 290 | 3 | 4 | 5 | 6 | 7 | | VII-1 | Car9 |
| 291 | 3 | 4 | 5 | 6 | 7 | | VII-1 | Casq1 |
| 292 | 3 | 4 | 5 | 6 | 7 | | VII-1 | Cav3 |
| 293 | 3 | 4 | 5 | 6 | 7 | | VII-1 | Ccl21a |
| 294 | 3 | 4 | 5 | 6 | 7 | | VII-1 | Ccl8 |
| 295 | 3 | 4 | 5 | 6 | 7 | | VII-1 | Ccng1 |
| 296 | 3 | 4 | 5 | 6 | 7 | | VII-1 | Cd300lf |
| 297 | 3 | 4 | 5 | 6 | 7 | | VII-1 | Cel |
| 298 | 3 | 4 | 5 | 6 | 7 | | VII-1 | Cela2a |
| 299 | 3 | 4 | 5 | 6 | 7 | | VII-1 | Cela3b |
| 300 | 3 | 4 | 5 | 6 | 7 | | VII-1 | Cish |
| 301 | 3 | 4 | 5 | 6 | 7 | | VII-1 | Ckm |
| 302 | 3 | 4 | 5 | 6 | 7 | | VII-1 | Ckmt2 |
| 303 | 3 | 4 | 5 | 6 | 7 | | VII-1 | Clps |
| 304 | 3 | 4 | 5 | 6 | 7 | | VII-1 | Cmya5 |
| 305 | 3 | 4 | 5 | 6 | 7 | | VII-1 | Cnksr1 |
| 306 | 3 | 4 | 5 | 6 | 7 | | VII-1 | Col1a1 |
| 307 | 3 | 4 | 5 | 6 | 7 | | VII-1 | Col3a1 |
| 308 | 3 | 4 | 5 | 6 | 7 | | VII-1 | Cox6a2 |
| 309 | 3 | 4 | 5 | 6 | 7 | | VII-1 | Cox6b2 |
| 310 | 3 | 4 | 5 | 6 | 7 | | VII-1 | Cpa1 |
| 311 | 3 | 4 | 5 | 6 | 7 | | VII-1 | Cpb1 |
| 312 | 3 | 4 | 5 | 6 | 7 | | VII-1 | Cryab |
| 313 | 3 | 4 | 5 | 6 | 7 | | VII-1 | Csf3r |
| 314 | 3 | 4 | 5 | 6 | 7 | | VII-1 | Csrp3 |
| 315 | 3 | 4 | 5 | 6 | 7 | | VII-1 | Ctrb1 |
| 316 | 3 | 4 | 5 | 6 | 7 | | VII-1 | Ctrl |
| 317 | 3 | 4 | 5 | 6 | 7 | | VII-1 | Ctxn3 |
| 318 | 3 | 4 | 5 | 6 | 7 | | VII-1 | Cuzd1 |
| 319 | 3 | 4 | 5 | 6 | 7 | | VII-1 | Cxcl9 |
| 320 | 3 | 4 | 5 | 6 | 7 | | VII-1 | Dcn |
| 321 | 3 | 4 | 5 | 6 | 7 | | VII-1 | Defa24 |
| 322 | 3 | 4 | 5 | 6 | 7 | | VII-1 | Des |
| 323 | 3 | 4 | 5 | 6 | 7 | | VII-1 | Dhrs9 |
| 324 | 3 | 4 | 5 | 6 | 7 | | VII-1 | Dusp27 |
| 325 | 3 | 4 | 5 | 6 | 7 | | VII-1 | Ear3 |
| 326 | 3 | 4 | 5 | 6 | 7 | | VII-1 | Eef1a2 |
| 327 | 3 | 4 | 5 | 6 | 7 | | VII-1 | Egfbp2 |
| 328 | 3 | 4 | 5 | 6 | 7 | | VII-1 | Egln3 |
| 329 | 3 | 4 | 5 | 6 | 7 | | VII-1 | Elovl3 |
| 330 | 3 | 4 | 5 | 6 | 7 | | VII-1 | Eno3 |
| 331 | 3 | 4 | 5 | 6 | 7 | | VII-1 | Fabp3 |
| 332 | 3 | 4 | 5 | 6 | 7 | | VII-1 | Fam132a |
| 333 | 3 | 4 | 5 | 6 | 7 | | VII-1 | Fam132b |
| 334 | 3 | 4 | 5 | 6 | 7 | | VII-1 | Fitm1 |
| 335 | 3 | 4 | 5 | 6 | 7 | | VII-1 | Flnc |
| 336 | 3 | 4 | 5 | 6 | 7 | | VII-1 | G0s2 |
| 337 | 3 | 4 | 5 | 6 | 7 | | VII-1 | Gdf3 |
| 338 | 3 | 4 | 5 | 6 | 7 | | VII-1 | Gh |

Fig. 43 - 3

| | | | | | | | | | | | | | | | |
|---|---|---|---|---|---|---|---|---|---|---|---|---|---|---|---|
| 339 | 3 | 4 | 5 | 6 | 7 | | VII-1 | Glycam1 | | 424 | 3 | 4 | 5 | 6 | 7 | | VII-1 | Myh2 |
| 340 | 3 | 4 | 5 | 6 | 7 | | VII-1 | Gm10094 | | 425 | 3 | 4 | 5 | 6 | 7 | | VII-1 | Myh4 |
| 341 | 3 | 4 | 5 | 6 | 7 | | VII-1 | Gm10334 | | 426 | 3 | 4 | 5 | 6 | 7 | | VII-1 | Myh7 |
| 342 | 3 | 4 | 5 | 6 | 7 | | VII-1 | Gm12191 | | 427 | 3 | 4 | 5 | 6 | 7 | | VII-1 | Myh8 |
| 343 | 3 | 4 | 5 | 6 | 7 | | VII-1 | Gm13363 | | 428 | 3 | 4 | 5 | 6 | 7 | | VII-1 | Myl1 |
| 344 | 3 | 4 | 5 | 6 | 7 | | VII-1 | Gm1987 | | 429 | 3 | 4 | 5 | 6 | 7 | | VII-1 | Myl2 |
| 345 | 3 | 4 | 5 | 6 | 7 | | VII-1 | Gm2663 | | 430 | 3 | 4 | 5 | 6 | 7 | | VII-1 | Myl3 |
| 346 | 3 | 4 | 5 | 6 | 7 | | VII-1 | Gm5483 | | 431 | 3 | 4 | 5 | 6 | 7 | | VII-1 | Myl6b |
| 347 | 3 | 4 | 5 | 6 | 7 | | VII-1 | Gm5771 | | 432 | 3 | 4 | 5 | 6 | 7 | | VII-1 | Mylk2 |
| 348 | 3 | 4 | 5 | 6 | 7 | | VII-1 | Gm7334 | | 433 | 3 | 4 | 5 | 6 | 7 | | VII-1 | Mylpf |
| 349 | 3 | 4 | 5 | 6 | 7 | | VII-1 | Gpd1 | | 434 | 3 | 4 | 5 | 6 | 7 | | VII-1 | Myo18b |
| 350 | 3 | 4 | 5 | 6 | 7 | | VII-1 | Gstm3 | | 435 | 3 | 4 | 5 | 6 | 7 | | VII-1 | Myoc |
| 351 | 3 | 4 | 5 | 6 | 7 | | VII-1 | H19 | | 436 | 3 | 4 | 5 | 6 | 7 | | VII-1 | Myom1 |
| 352 | 3 | 4 | 5 | 6 | 7 | | VII-1 | H2-Q6 | | 437 | 3 | 4 | 5 | 6 | 7 | | VII-1 | Myom2 |
| 353 | 3 | 4 | 5 | 6 | 7 | | VII-1 | H2-Q8 | | 438 | 3 | 4 | 5 | 6 | 7 | | VII-1 | Myom3 |
| 354 | 3 | 4 | 5 | 6 | 7 | | VII-1 | H2-Q9 | | 439 | 3 | 4 | 5 | 6 | 7 | | VII-1 | Myot |
| 355 | 3 | 4 | 5 | 6 | 7 | | VII-1 | Hba-a2 | | 440 | 3 | 4 | 5 | 6 | 7 | | VII-1 | Myoz1 |
| 356 | 3 | 4 | 5 | 6 | 7 | | VII-1 | Hbb-bs | | 441 | 3 | 4 | 5 | 6 | 7 | | VII-1 | Myoz2 |
| 357 | 3 | 4 | 5 | 6 | 7 | | VII-1 | Hcar2 | | 442 | 3 | 4 | 5 | 6 | 7 | | VII-1 | Mypn |
| 358 | 3 | 4 | 5 | 6 | 7 | | VII-1 | Hfe2 | | 443 | 3 | 4 | 5 | 6 | 7 | | VII-1 | Nctc1 |
| 359 | 3 | 4 | 5 | 6 | 7 | | VII-1 | Hist2h2aa2 | | 444 | 3 | 4 | 5 | 6 | 7 | | VII-1 | Neb |
| 360 | 3 | 4 | 5 | 6 | 7 | | VII-1 | Hoxc10 | | 445 | 3 | 4 | 5 | 6 | 7 | | VII-1 | Neurl1a |
| 361 | 3 | 4 | 5 | 6 | 7 | | VII-1 | Hrc | | 446 | 3 | 4 | 5 | 6 | 7 | | VII-1 | Nexn |
| 362 | 3 | 4 | 5 | 6 | 7 | | VII-1 | Hspa1b | | 447 | 3 | 4 | 5 | 6 | 7 | | VII-1 | Nol3 |
| 363 | 3 | 4 | 5 | 6 | 7 | | VII-1 | Hspb6 | | 448 | 3 | 4 | 5 | 6 | 7 | | VII-1 | Nrap |
| 364 | 3 | 4 | 5 | 6 | 7 | | VII-1 | Hspb7 | | 449 | 3 | 4 | 5 | 6 | 7 | | VII-1 | Oaz1-ps |
| 365 | 3 | 4 | 5 | 6 | 7 | | VII-1 | Ifitm6 | | 450 | 3 | 4 | 5 | 6 | 7 | | VII-1 | Obscn |
| 366 | 3 | 4 | 5 | 6 | 7 | | VII-1 | Igfn1 | | 451 | 3 | 4 | 5 | 6 | 7 | | VII-1 | Orm2 |
| 367 | 3 | 4 | 5 | 6 | 7 | | VII-1 | Ip6k3 | | 452 | 3 | 4 | 5 | 6 | 7 | | VII-1 | Pcp4l1 |
| 368 | 3 | 4 | 5 | 6 | 7 | | VII-1 | Itgb1bp2 | | 453 | 3 | 4 | 5 | 6 | 7 | | VII-1 | Pde4dip |
| 369 | 3 | 4 | 5 | 6 | 7 | | VII-1 | Jph1 | | 454 | 3 | 4 | 5 | 6 | 7 | | VII-1 | Pdlim3 |
| 370 | 3 | 4 | 5 | 6 | 7 | | VII-1 | Jsrp1 | | 455 | 3 | 4 | 5 | 6 | 7 | | VII-1 | Perm1 |
| 371 | 3 | 4 | 5 | 6 | 7 | | VII-1 | Kap | | 456 | 3 | 4 | 5 | 6 | 7 | | VII-1 | Pfkm |
| 372 | 3 | 4 | 5 | 6 | 7 | | VII-1 | Kcna7 | | 457 | 3 | 4 | 5 | 6 | 7 | | VII-1 | Pgc |
| 373 | 3 | 4 | 5 | 6 | 7 | | VII-1 | Kcnj11 | | 458 | 3 | 4 | 5 | 6 | 7 | | VII-1 | Pklr |
| 374 | 3 | 4 | 5 | 6 | 7 | | VII-1 | Klhl31 | | 459 | 3 | 4 | 5 | 6 | 7 | | VII-1 | Pla2g1b |
| 375 | 3 | 4 | 5 | 6 | 7 | | VII-1 | Klhl38 | | 460 | 3 | 4 | 5 | 6 | 7 | | VII-1 | Plek2 |
| 376 | 3 | 4 | 5 | 6 | 7 | | VII-1 | Klhl40 | | 461 | 3 | 4 | 5 | 6 | 7 | | VII-1 | Pnliprp1 |
| 377 | 3 | 4 | 5 | 6 | 7 | | VII-1 | Klhl41 | | 462 | 3 | 4 | 5 | 6 | 7 | | VII-1 | Podxl |
| 378 | 3 | 4 | 5 | 6 | 7 | | VII-1 | Klk1 | | 463 | 3 | 4 | 5 | 6 | 7 | | VII-1 | Popdc3 |
| 379 | 3 | 4 | 5 | 6 | 7 | | VII-1 | Krt1 | | 464 | 3 | 4 | 5 | 6 | 7 | | VII-1 | Ppp1r27 |
| 380 | 3 | 4 | 5 | 6 | 7 | | VII-1 | Krt10 | | 465 | 3 | 4 | 5 | 6 | 7 | | VII-1 | Prm2 |
| 381 | 3 | 4 | 5 | 6 | 7 | | VII-1 | Krt14 | | 466 | 3 | 4 | 5 | 6 | 7 | | VII-1 | Prob1 |
| 382 | 3 | 4 | 5 | 6 | 7 | | VII-1 | Krt15 | | 467 | 3 | 4 | 5 | 6 | 7 | | VII-1 | Prol1 |
| 383 | 3 | 4 | 5 | 6 | 7 | | VII-1 | Krt5 | | 468 | 3 | 4 | 5 | 6 | 7 | | VII-1 | Prss2 |
| 384 | 3 | 4 | 5 | 6 | 7 | | VII-1 | Krt77 | | 469 | 3 | 4 | 5 | 6 | 7 | | VII-1 | Psrc1 |
| 385 | 3 | 4 | 5 | 6 | 7 | | VII-1 | Krtap8-1 | | 470 | 3 | 4 | 5 | 6 | 7 | | VII-1 | Pvalb |
| 386 | 3 | 4 | 5 | 6 | 7 | | VII-1 | Lce1m | | 471 | 3 | 4 | 5 | 6 | 7 | | VII-1 | Pygm |
| 387 | 3 | 4 | 5 | 6 | 7 | | VII-1 | Ldb3 | | 472 | 3 | 4 | 5 | 6 | 7 | | VII-1 | Rbfox1 |
| 388 | 3 | 4 | 5 | 6 | 7 | | VII-1 | Lgals7 | | 473 | 3 | 4 | 5 | 6 | 7 | | VII-1 | Rbm24 |
| 389 | 3 | 4 | 5 | 6 | 7 | | VII-1 | Lmod2 | | 474 | 3 | 4 | 5 | 6 | 7 | | VII-1 | Reep6 |
| 390 | 3 | 4 | 5 | 6 | 7 | | VII-1 | Lmod3 | | 475 | 3 | 4 | 5 | 6 | 7 | | VII-1 | Reg1 |
| 391 | 3 | 4 | 5 | 6 | 7 | | VII-1 | LOC100048884 | | 476 | 3 | 4 | 5 | 6 | 7 | | VII-1 | Reg3b |
| 392 | 3 | 4 | 5 | 6 | 7 | | VII-1 | Lor | | 477 | 3 | 4 | 5 | 6 | 7 | | VII-1 | Reg3g |
| 393 | 3 | 4 | 5 | 6 | 7 | | VII-1 | Lrrc2 | | 478 | 3 | 4 | 5 | 6 | 7 | | VII-1 | Retnlg |
| 394 | 3 | 4 | 5 | 6 | 7 | | VII-1 | Lrrc30 | | 479 | 3 | 4 | 5 | 6 | 7 | | VII-1 | Rnase1 |
| 395 | 3 | 4 | 5 | 6 | 7 | | VII-1 | Lrrc52 | | 480 | 3 | 4 | 5 | 6 | 7 | | VII-1 | Rpl3l |
| 396 | 3 | 4 | 5 | 6 | 7 | | VII-1 | Mat1a | | 481 | 3 | 4 | 5 | 6 | 7 | | VII-1 | Ryr1 |
| 397 | 3 | 4 | 5 | 6 | 7 | | VII-1 | Mb | | 482 | 3 | 4 | 5 | 6 | 7 | | VII-1 | S100a8 |
| 398 | 3 | 4 | 5 | 6 | 7 | | VII-1 | Mir1957b | | 483 | 3 | 4 | 5 | 6 | 7 | | VII-1 | S100a9 |
| 399 | 3 | 4 | 5 | 6 | 7 | | VII-1 | Mir214 | | 484 | 3 | 4 | 5 | 6 | 7 | | VII-1 | S100g |
| 400 | 3 | 4 | 5 | 6 | 7 | | VII-1 | Mir6236 | | 485 | 3 | 4 | 5 | 6 | 7 | | VII-1 | Sap25 |
| 401 | 3 | 4 | 5 | 6 | 7 | | VII-1 | Mir682 | | 486 | 3 | 4 | 5 | 6 | 7 | | VII-1 | Sbsn |
| 402 | 3 | 4 | 5 | 6 | 7 | | VII-1 | Mir703 | | 487 | 3 | 4 | 5 | 6 | 7 | | VII-1 | Scgb1a1 |
| 403 | 3 | 4 | 5 | 6 | 7 | | VII-1 | Mir8091 | | 488 | 3 | 4 | 5 | 6 | 7 | | VII-1 | Scgb1b27 |
| 404 | 3 | 4 | 5 | 6 | 7 | | VII-1 | Mir8094 | | 489 | 3 | 4 | 5 | 6 | 7 | | VII-1 | Sec14l2 |
| 405 | 3 | 4 | 5 | 6 | 7 | | VII-1 | Mir8098 | | 490 | 3 | 4 | 5 | 6 | 7 | | VII-1 | Serpina3n |
| 406 | 3 | 4 | 5 | 6 | 7 | | VII-1 | Mir8099-1 | | 491 | 3 | 4 | 5 | 6 | 7 | | VII-1 | Sesn2 |
| 407 | 3 | 4 | 5 | 6 | 7 | | VII-1 | Mir8102 | | 492 | 3 | 4 | 5 | 6 | 7 | | VII-1 | Sftpc |
| 408 | 3 | 4 | 5 | 6 | 7 | | VII-1 | Mir8108 | | 493 | 3 | 4 | 5 | 6 | 7 | | VII-1 | Sgca |
| 409 | 3 | 4 | 5 | 6 | 7 | | VII-1 | Mirlet7d | | 494 | 3 | 4 | 5 | 6 | 7 | | VII-1 | Sgcg |
| 410 | 3 | 4 | 5 | 6 | 7 | | VII-1 | Mmp8 | | 495 | 3 | 4 | 5 | 6 | 7 | | VII-1 | Shisa4 |
| 411 | 3 | 4 | 5 | 6 | 7 | | VII-1 | Mpz | | 496 | 3 | 4 | 5 | 6 | 7 | | VII-1 | Slfn4 |
| 412 | 3 | 4 | 5 | 6 | 7 | | VII-1 | Ms4a4c | | 497 | 3 | 4 | 5 | 6 | 7 | | VII-1 | Slurp1 |
| 413 | 3 | 4 | 5 | 6 | 7 | | VII-1 | Mss51 | | 498 | 3 | 4 | 5 | 6 | 7 | | VII-1 | Smpx |
| 414 | 3 | 4 | 5 | 6 | 7 | | VII-1 | Mstn | | 499 | 3 | 4 | 5 | 6 | 7 | | VII-1 | Smtnl1 |
| 415 | 3 | 4 | 5 | 6 | 7 | | VII-1 | Mt2 | | 500 | 3 | 4 | 5 | 6 | 7 | | VII-1 | Smyd1 |
| 416 | 3 | 4 | 5 | 6 | 7 | | VII-1 | Mup15 | | 501 | 3 | 4 | 5 | 6 | 7 | | VII-1 | Snora16a |
| 417 | 3 | 4 | 5 | 6 | 7 | | VII-1 | Murc | | 502 | 3 | 4 | 5 | 6 | 7 | | VII-1 | Snora17 |
| 418 | 3 | 4 | 5 | 6 | 7 | | VII-1 | Myadml2 | | 503 | 3 | 4 | 5 | 6 | 7 | | VII-1 | Snora21 |
| 419 | 3 | 4 | 5 | 6 | 7 | | VII-1 | Mybpc1 | | 504 | 3 | 4 | 5 | 6 | 7 | | VII-1 | Snora28 |
| 420 | 3 | 4 | 5 | 6 | 7 | | VII-1 | Mybpc2 | | 505 | 3 | 4 | 5 | 6 | 7 | | VII-1 | Snora3 |
| 421 | 3 | 4 | 5 | 6 | 7 | | VII-1 | Mybph | | 506 | 3 | 4 | 5 | 6 | 7 | | VII-1 | Snora30 |
| 422 | 3 | 4 | 5 | 6 | 7 | | VII-1 | Myf6 | | 507 | 3 | 4 | 5 | 6 | 7 | | VII-1 | Snora34 |
| 423 | 3 | 4 | 5 | 6 | 7 | | VII-1 | Myh1 | | 508 | 3 | 4 | 5 | 6 | 7 | | VII-1 | Snora41 |

Fig. 43 - 4

| | | | | | | | | | | | | | | | | |
|---|---|---|---|---|---|---|---|---|---|---|---|---|---|---|---|---|
| 509 | 3 | 4 | 5 | 6 | 7 | | VII-1 | Snora43 | 594 | 3 | 4 | 5 | 6 | | VI-2 | 1700039E15Rik |
| 510 | 3 | 4 | 5 | 6 | 7 | | VII-1 | Snora52 | 595 | 3 | 4 | 5 | 6 | | VI-2 | 1700045H11Rik |
| 511 | 3 | 4 | 5 | 6 | 7 | | VII-1 | Snora64 | 596 | 3 | 4 | 5 | 6 | | VI-2 | 1700047I14Rik |
| 512 | 3 | 4 | 5 | 6 | 7 | | VII-1 | Snora65 | 597 | 3 | 4 | 5 | 6 | | VI-2 | 1700047M11Rik |
| 513 | 3 | 4 | 5 | 6 | 7 | | VII-1 | Snora70 | 598 | 3 | 4 | 5 | 6 | | VI-2 | 1700048M11Rik |
| 514 | 3 | 4 | 5 | 6 | 7 | | VII-1 | Snora78 | 599 | 3 | 4 | 5 | 6 | | VI-2 | 1700048O20Rik |
| 515 | 3 | 4 | 5 | 6 | 7 | | VII-1 | Snora81 | 600 | 3 | 4 | 5 | 6 | | VI-2 | 1700049L16Rik |
| 516 | 3 | 4 | 5 | 6 | 7 | | VII-1 | Snord15a | 601 | 3 | 4 | 5 | 6 | | VI-2 | 1700086L19Rik |
| 517 | 3 | 4 | 5 | 6 | 7 | | VII-1 | Snord15b | 602 | 3 | 4 | 5 | 6 | | VI-2 | 1700092M07Rik |
| 518 | 3 | 4 | 5 | 6 | 7 | | VII-1 | Snord22 | 603 | 3 | 4 | 5 | 6 | | VI-2 | 1700101I11Rik |
| 519 | 3 | 4 | 5 | 6 | 7 | | VII-1 | Snord23 | 604 | 3 | 4 | 5 | 6 | | VI-2 | 1700102P08Rik |
| 520 | 3 | 4 | 5 | 6 | 7 | | VII-1 | Sprr1b | 605 | 3 | 4 | 5 | 6 | | VI-2 | 1700108J01Rik |
| 521 | 3 | 4 | 5 | 6 | 7 | | VII-1 | Sprr2e | 606 | 3 | 4 | 5 | 6 | | VI-2 | 1700129C05Rik |
| 522 | 3 | 4 | 5 | 6 | 7 | | VII-1 | Sprr2f | 607 | 3 | 4 | 5 | 6 | | VI-2 | 1810008I18Rik |
| 523 | 3 | 4 | 5 | 6 | 7 | | VII-1 | Sprr2h | 608 | 3 | 4 | 5 | 6 | | VI-2 | 1810014B01Rik |
| 524 | 3 | 4 | 5 | 6 | 7 | | VII-1 | Spt1 | 609 | 3 | 4 | 5 | 6 | | VI-2 | 1810018F18Rik |
| 525 | 3 | 4 | 5 | 6 | 7 | | VII-1 | Sptb | 610 | 3 | 4 | 5 | 6 | | VI-2 | 1810062O18Rik |
| 526 | 3 | 4 | 5 | 6 | 7 | | VII-1 | Srl | 611 | 3 | 4 | 5 | 6 | | VI-2 | 2010002M12Rik |
| 527 | 3 | 4 | 5 | 6 | 7 | | VII-1 | Stfa2l1 | 612 | 3 | 4 | 5 | 6 | | VI-2 | 2010015L04Rik |
| 528 | 3 | 4 | 5 | 6 | 7 | | VII-1 | Stfa3 | 613 | 3 | 4 | 5 | 6 | | VI-2 | 2210018M11Rik |
| 529 | 3 | 4 | 5 | 6 | 7 | | VII-1 | Sult2a1 | 614 | 3 | 4 | 5 | 6 | | VI-2 | 2310001H17Rik |
| 530 | 3 | 4 | 5 | 6 | 7 | | VII-1 | Sult2a2 | 615 | 3 | 4 | 5 | 6 | | VI-2 | 2310009A05Rik |
| 531 | 3 | 4 | 5 | 6 | 7 | | VII-1 | Sycn | 616 | 3 | 4 | 5 | 6 | | VI-2 | 2310010J17Rik |
| 532 | 3 | 4 | 5 | 6 | 7 | | VII-1 | Synpo2l | 617 | 3 | 4 | 5 | 6 | | VI-2 | 2410004N09Rik |
| 533 | 3 | 4 | 5 | 6 | 7 | | VII-1 | Sypl2 | 618 | 3 | 4 | 5 | 6 | | VI-2 | 2410004P03Rik |
| 534 | 3 | 4 | 5 | 6 | 7 | | VII-1 | Tbx15 | 619 | 3 | 4 | 5 | 6 | | VI-2 | 2410006H16Rik |
| 535 | 3 | 4 | 5 | 6 | 7 | | VII-1 | Tcap | 620 | 3 | 4 | 5 | 6 | | VI-2 | 2410076I21Rik |
| 536 | 3 | 4 | 5 | 6 | 7 | | VII-1 | Tff1 | 621 | 3 | 4 | 5 | 6 | | VI-2 | 2410127L17Rik |
| 537 | 3 | 4 | 5 | 6 | 7 | | VII-1 | Tfr2 | 622 | 3 | 4 | 5 | 6 | | VI-2 | 2610005L07Rik |
| 538 | 3 | 4 | 5 | 6 | 7 | | VII-1 | Tmem38a | 623 | 3 | 4 | 5 | 6 | | VI-2 | 2610035D17Rik |
| 539 | 3 | 4 | 5 | 6 | 7 | | VII-1 | Tmem56 | 624 | 3 | 4 | 5 | 6 | | VI-2 | 2610306M01Rik |
| 540 | 3 | 4 | 5 | 6 | 7 | | VII-1 | Tmod4 | 625 | 3 | 4 | 5 | 6 | | VI-2 | 2610307P16Rik |
| 541 | 3 | 4 | 5 | 6 | 7 | | VII-1 | Tnnc1 | 626 | 3 | 4 | 5 | 6 | | VI-2 | 2810002D19Rik |
| 542 | 3 | 4 | 5 | 6 | 7 | | VII-1 | Tnnc2 | 627 | 3 | 4 | 5 | 6 | | VI-2 | 2810021J22Rik |
| 543 | 3 | 4 | 5 | 6 | 7 | | VII-1 | Tnni1 | 628 | 3 | 4 | 5 | 6 | | VI-2 | 2810029C07Rik |
| 544 | 3 | 4 | 5 | 6 | 7 | | VII-1 | Tnni2 | 629 | 3 | 4 | 5 | 6 | | VI-2 | 2810474O19Rik |
| 545 | 3 | 4 | 5 | 6 | 7 | | VII-1 | Tnnt1 | 630 | 3 | 4 | 5 | 6 | | VI-2 | 2900026A02Rik |
| 546 | 3 | 4 | 5 | 6 | 7 | | VII-1 | Tnnt3 | 631 | 3 | 4 | 5 | 6 | | VI-2 | 2900041M22Rik |
| 547 | 3 | 4 | 5 | 6 | 7 | | VII-1 | Tnp2 | 632 | 3 | 4 | 5 | 6 | | VI-2 | 2900079G21Rik |
| 548 | 3 | 4 | 5 | 6 | 7 | | VII-1 | Tpm2 | 633 | 3 | 4 | 5 | 6 | | VI-2 | 3000002C10Rik |
| 549 | 3 | 4 | 5 | 6 | 7 | | VII-1 | Trdn | 634 | 3 | 4 | 5 | 6 | | VI-2 | 3110009F21Rik |
| 550 | 3 | 4 | 5 | 6 | 7 | | VII-1 | Trim54 | 635 | 3 | 4 | 5 | 6 | | VI-2 | 3110021N24Rik |
| 551 | 3 | 4 | 5 | 6 | 7 | | VII-1 | Trim63 | 636 | 3 | 4 | 5 | 6 | | VI-2 | 3110099E03Rik |
| 552 | 3 | 4 | 5 | 6 | 7 | | VII-1 | Trim72 | 637 | 3 | 4 | 5 | 6 | | VI-2 | 4632428C04Rik |
| 553 | 3 | 4 | 5 | 6 | 7 | | VII-1 | Try10 | 638 | 3 | 4 | 5 | 6 | | VI-2 | 4732416N19Rik |
| 554 | 3 | 4 | 5 | 6 | 7 | | VII-1 | Try4 | 639 | 3 | 4 | 5 | 6 | | VI-2 | 4833411C07Rik |
| 555 | 3 | 4 | 5 | 6 | 7 | | VII-1 | Try5 | 640 | 3 | 4 | 5 | 6 | | VI-2 | 4921507P07Rik |
| 556 | 3 | 4 | 5 | 6 | 7 | | VII-1 | Ttn | 641 | 3 | 4 | 5 | 6 | | VI-2 | 4921525O09Rik |
| 557 | 3 | 4 | 5 | 6 | 7 | | VII-1 | Txnb | 642 | 3 | 4 | 5 | 6 | | VI-2 | 4921533I20Rik |
| 558 | 3 | 4 | 5 | 6 | 7 | | VII-1 | Usp13 | 643 | 3 | 4 | 5 | 6 | | VI-2 | 4930402H24Rik |
| 559 | 3 | 4 | 5 | 6 | 7 | | VII-1 | Vgll2 | 644 | 3 | 4 | 5 | 6 | | VI-2 | 4930412C18Rik |
| 560 | 3 | 4 | 5 | 6 | 7 | | VII-1 | Wfdc17 | 645 | 3 | 4 | 5 | 6 | | VI-2 | 4930415O20Rik |
| 561 | 3 | 4 | 5 | 6 | 7 | | VII-1 | Xirp1 | 646 | 3 | 4 | 5 | 6 | | VI-2 | 4930417O13Rik |
| 562 | 3 | 4 | 5 | 6 | 7 | | VII-1 | Xirp2 | 647 | 3 | 4 | 5 | 6 | | VI-2 | 4930426D05Rik |
| 563 | 3 | 4 | 5 | 6 | | | VI-2 | 0610009L18Rik | 648 | 3 | 4 | 5 | 6 | | VI-2 | 4930430J02Rik |
| 564 | 3 | 4 | 5 | 6 | | | VI-2 | 0610010B08Rik | 649 | 3 | 4 | 5 | 6 | | VI-2 | 4930441I16Rik |
| 565 | 3 | 4 | 5 | 6 | | | VI-2 | 0610037L13Rik | 650 | 3 | 4 | 5 | 6 | | VI-2 | 4930448H16Rik |
| 566 | 3 | 4 | 5 | 6 | | | VI-2 | 1110002L01Rik | 651 | 3 | 4 | 5 | 6 | | VI-2 | 4930471G03Rik |
| 567 | 3 | 4 | 5 | 6 | | | VI-2 | 1110017D15Rik | 652 | 3 | 4 | 5 | 6 | | VI-2 | 4930486L24Rik |
| 568 | 3 | 4 | 5 | 6 | | | VI-2 | 1110020A21Rik | 653 | 3 | 4 | 5 | 6 | | VI-2 | 4930487D11Rik |
| 569 | 3 | 4 | 5 | 6 | | | VI-2 | 1110034G24Rik | 654 | 3 | 4 | 5 | 6 | | VI-2 | 4930487H11Rik |
| 570 | 3 | 4 | 5 | 6 | | | VI-2 | 1110038B12Rik | 655 | 3 | 4 | 5 | 6 | | VI-2 | 4930503B20Rik |
| 571 | 3 | 4 | 5 | 6 | | | VI-2 | 1190005I06Rik | 656 | 3 | 4 | 5 | 6 | | VI-2 | 4930503L19Rik |
| 572 | 3 | 4 | 5 | 6 | | | VI-2 | 1500012F01Rik | 657 | 3 | 4 | 5 | 6 | | VI-2 | 4930527G23Rik |
| 573 | 3 | 4 | 5 | 6 | | | VI-2 | 1600020E01Rik | 658 | 3 | 4 | 5 | 6 | | VI-2 | 4930539J05Rik |
| 574 | 3 | 4 | 5 | 6 | | | VI-2 | 1700001C02Rik | 659 | 3 | 4 | 5 | 6 | | VI-2 | 4930544G11Rik |
| 575 | 3 | 4 | 5 | 6 | | | VI-2 | 1700001K19Rik | 660 | 3 | 4 | 5 | 6 | | VI-2 | 4930558C23Rik |
| 576 | 3 | 4 | 5 | 6 | | | VI-2 | 1700003E16Rik | 661 | 3 | 4 | 5 | 6 | | VI-2 | 4930562C15Rik |
| 577 | 3 | 4 | 5 | 6 | | | VI-2 | 1700009P17Rik | 662 | 3 | 4 | 5 | 6 | | VI-2 | 4930571K23Rik |
| 578 | 3 | 4 | 5 | 6 | | | VI-2 | 1700010B08Rik | 663 | 3 | 4 | 5 | 6 | | VI-2 | 4930578C19Rik |
| 579 | 3 | 4 | 5 | 6 | | | VI-2 | 1700010D01Rik | 664 | 3 | 4 | 5 | 6 | | VI-2 | 4930578I06Rik |
| 580 | 3 | 4 | 5 | 6 | | | VI-2 | 1700010I02Rik | 665 | 3 | 4 | 5 | 6 | | VI-2 | 4930579K19Rik |
| 581 | 3 | 4 | 5 | 6 | | | VI-2 | 1700010I14Rik | 666 | 3 | 4 | 5 | 6 | | VI-2 | 4930598F16Rik |
| 582 | 3 | 4 | 5 | 6 | | | VI-2 | 1700015E13Rik | 667 | 3 | 4 | 5 | 6 | | VI-2 | 4932411E22Rik |
| 583 | 3 | 4 | 5 | 6 | | | VI-2 | 1700016H13Rik | 668 | 3 | 4 | 5 | 6 | | VI-2 | 4932418E24Rik |
| 584 | 3 | 4 | 5 | 6 | | | VI-2 | 1700019N19Rik | 669 | 3 | 4 | 5 | 6 | | VI-2 | 4932702P03Rik |
| 585 | 3 | 4 | 5 | 6 | | | VI-2 | 1700020D05Rik | 670 | 3 | 4 | 5 | 6 | | VI-2 | 4933402J07Rik |
| 586 | 3 | 4 | 5 | 6 | | | VI-2 | 1700021F05Rik | 671 | 3 | 4 | 5 | 6 | | VI-2 | 4933402P03Rik |
| 587 | 3 | 4 | 5 | 6 | | | VI-2 | 1700026L06Rik | 672 | 3 | 4 | 5 | 6 | | VI-2 | 4933404O12Rik |
| 588 | 3 | 4 | 5 | 6 | | | VI-2 | 1700027A15Rik | 673 | 3 | 4 | 5 | 6 | | VI-2 | 4933407L21Rik |
| 589 | 3 | 4 | 5 | 6 | | | VI-2 | 1700028J19Rik | 674 | 3 | 4 | 5 | 6 | | VI-2 | 4933415F23Rik |
| 590 | 3 | 4 | 5 | 6 | | | VI-2 | 1700029J07Rik | 675 | 3 | 4 | 5 | 6 | | VI-2 | 4933439C10Rik |
| 591 | 3 | 4 | 5 | 6 | | | VI-2 | 1700029P11Rik | 676 | 3 | 4 | 5 | 6 | | VI-2 | 5330426P16Rik |
| 592 | 3 | 4 | 5 | 6 | | | VI-2 | 1700030J22Rik | 677 | 3 | 4 | 5 | 6 | | VI-2 | 5530601H04Rik |
| 593 | 3 | 4 | 5 | 6 | | | VI-2 | 1700030K09Rik | 678 | 3 | 4 | 5 | 6 | | VI-2 | 5730422E09Rik |

Fig. 43 - 5

| | | | | | | | | |
|---|---|---|---|---|---|---|---|---|
| 679 | 3 | 4 | 5 | 6 | | VI-2 | 5830416P10Rik |
| 680 | 3 | 4 | 5 | 6 | | VI-2 | 5830418P13Rik |
| 681 | 3 | 4 | 5 | 6 | | VI-2 | 5830432E09Rik |
| 682 | 3 | 4 | 5 | 6 | | VI-2 | 6030408B16Rik |
| 683 | 3 | 4 | 5 | 6 | | VI-2 | 6330409D20Rik |
| 684 | 3 | 4 | 5 | 6 | | VI-2 | 6530402F18Rik |
| 685 | 3 | 4 | 5 | 6 | | VI-2 | 8030462N17Rik |
| 686 | 3 | 4 | 5 | 6 | | VI-2 | 8430419L09Rik |
| 687 | 3 | 4 | 5 | 6 | | VI-2 | 8430426J06Rik |
| 688 | 3 | 4 | 5 | 6 | | VI-2 | 9130230L23Rik |
| 689 | 3 | 4 | 5 | 6 | | VI-2 | 9130401M01Rik |
| 690 | 3 | 4 | 5 | 6 | | VI-2 | 9230110C19Rik |
| 691 | 3 | 4 | 5 | 6 | | VI-2 | 9430020K01Rik |
| 692 | 3 | 4 | 5 | 6 | | VI-2 | 9430069I07Rik |
| 693 | 3 | 4 | 5 | 6 | | VI-2 | 9430083A17Rik |
| 694 | 3 | 4 | 5 | 6 | | VI-2 | 9530026P05Rik |
| 695 | 3 | 4 | 5 | 6 | | VI-2 | 9830147E19Rik |
| 696 | 3 | 4 | 5 | 6 | | VI-2 | 9930021J03Rik |
| 697 | 3 | 4 | 5 | 6 | | VI-2 | A230056P14Rik |
| 698 | 3 | 4 | 5 | 6 | | VI-2 | A230072C01Rik |
| 699 | 3 | 4 | 5 | 6 | | VI-2 | A330040F15Rik |
| 700 | 3 | 4 | 5 | 6 | | VI-2 | A330069E16Rik |
| 701 | 3 | 4 | 5 | 6 | | VI-2 | A3galt2 |
| 702 | 3 | 4 | 5 | 6 | | VI-2 | A430005L14Rik |
| 703 | 3 | 4 | 5 | 6 | | VI-2 | A430035B10Rik |
| 704 | 3 | 4 | 5 | 6 | | VI-2 | A430078G23Rik |
| 705 | 3 | 4 | 5 | 6 | | VI-2 | A530032D15Rik |
| 706 | 3 | 4 | 5 | 6 | | VI-2 | A530050N04Rik |
| 707 | 3 | 4 | 5 | 6 | | VI-2 | A630023P12Rik |
| 708 | 3 | 4 | 5 | 6 | | VI-2 | A630077J23Rik |
| 709 | 3 | 4 | 5 | 6 | | VI-2 | A930003A15Rik |
| 710 | 3 | 4 | 5 | 6 | | VI-2 | A930006K02Rik |
| 711 | 3 | 4 | 5 | 6 | | VI-2 | A930012L18Rik |
| 712 | 3 | 4 | 5 | 6 | | VI-2 | A930013F10Rik |
| 713 | 3 | 4 | 5 | 6 | | VI-2 | A930024E05Rik |
| 714 | 3 | 4 | 5 | 6 | | VI-2 | AA388235 |
| 715 | 3 | 4 | 5 | 6 | | VI-2 | AA465934 |
| 716 | 3 | 4 | 5 | 6 | | VI-2 | Aacs |
| 717 | 3 | 4 | 5 | 6 | | VI-2 | Aadac |
| 718 | 3 | 4 | 5 | 6 | | VI-2 | Aaed1 |
| 719 | 3 | 4 | 5 | 6 | | VI-2 | Aard |
| 720 | 3 | 4 | 5 | 6 | | VI-2 | Aatf |
| 721 | 3 | 4 | 5 | 6 | | VI-2 | AB041803 |
| 722 | 3 | 4 | 5 | 6 | | VI-2 | Abca9 |
| 723 | 3 | 4 | 5 | 6 | | VI-2 | Abcc5 |
| 724 | 3 | 4 | 5 | 6 | | VI-2 | Abcd4 |
| 725 | 3 | 4 | 5 | 6 | | VI-2 | Abcg2 |
| 726 | 3 | 4 | 5 | 6 | | VI-2 | Abhd14b |
| 727 | 3 | 4 | 5 | 6 | | VI-2 | Ablim1 |
| 728 | 3 | 4 | 5 | 6 | | VI-2 | Acaa1a |
| 729 | 3 | 4 | 5 | 6 | | VI-2 | Acaa1b |
| 730 | 3 | 4 | 5 | 6 | | VI-2 | Acacb |
| 731 | 3 | 4 | 5 | 6 | | VI-2 | Acbd7 |
| 732 | 3 | 4 | 5 | 6 | | VI-2 | Ackr2 |
| 733 | 3 | 4 | 5 | 6 | | VI-2 | Acot3 |
| 734 | 3 | 4 | 5 | 6 | | VI-2 | Acrbp |
| 735 | 3 | 4 | 5 | 6 | | VI-2 | Acrv1 |
| 736 | 3 | 4 | 5 | 6 | | VI-2 | Acsbg1 |
| 737 | 3 | 4 | 5 | 6 | | VI-2 | Acsm5 |
| 738 | 3 | 4 | 5 | 6 | | VI-2 | Acss3 |
| 739 | 3 | 4 | 5 | 6 | | VI-2 | Actg1 |
| 740 | 3 | 4 | 5 | 6 | | VI-2 | Actg2 |
| 741 | 3 | 4 | 5 | 6 | | VI-2 | Actl7a |
| 742 | 3 | 4 | 5 | 6 | | VI-2 | Actr8 |
| 743 | 3 | 4 | 5 | 6 | | VI-2 | Acvr2b |
| 744 | 3 | 4 | 5 | 6 | | VI-2 | Acy1 |
| 745 | 3 | 4 | 5 | 6 | | VI-2 | Acyp1 |
| 746 | 3 | 4 | 5 | 6 | | VI-2 | Adam5 |
| 747 | 3 | 4 | 5 | 6 | | VI-2 | Adam6b |
| 748 | 3 | 4 | 5 | 6 | | VI-2 | Adam7 |
| 749 | 3 | 4 | 5 | 6 | | VI-2 | Adap2 |
| 750 | 3 | 4 | 5 | 6 | | VI-2 | Adck1 |
| 751 | 3 | 4 | 5 | 6 | | VI-2 | Adck3 |
| 752 | 3 | 4 | 5 | 6 | | VI-2 | Adora1 |
| 753 | 3 | 4 | 5 | 6 | | VI-2 | Adora2a |
| 754 | 3 | 4 | 5 | 6 | | VI-2 | Adra1a |
| 755 | 3 | 4 | 5 | 6 | | VI-2 | Aff3 |
| 756 | 3 | 4 | 5 | 6 | | VI-2 | Agmo |
| 757 | 3 | 4 | 5 | 6 | | VI-2 | Ahcy |
| 758 | 3 | 4 | 5 | 6 | | VI-2 | Ahdc1 |
| 759 | 3 | 4 | 5 | 6 | | VI-2 | Ahsa2 |
| 760 | 3 | 4 | 5 | 6 | | VI-2 | AI467606 |
| 761 | 3 | 4 | 5 | 6 | | VI-2 | AI507597 |
| 762 | 3 | 4 | 5 | 6 | | VI-2 | AI848285 |
| 763 | 3 | 4 | 5 | 6 | | VI-2 | Aicda |
| 764 | 3 | 4 | 5 | 6 | | VI-2 | Aim |
| 765 | 3 | 4 | 5 | 6 | | VI-2 | AK129341 |
| 766 | 3 | 4 | 5 | 6 | | VI-2 | Ak6 |
| 767 | 3 | 4 | 5 | 6 | | VI-2 | Ak8 |
| 768 | 3 | 4 | 5 | 6 | | VI-2 | Akap3 |
| 769 | 3 | 4 | 5 | 6 | | VI-2 | Akip1 |
| 770 | 3 | 4 | 5 | 6 | | VI-2 | Akr1c19 |
| 771 | 3 | 4 | 5 | 6 | | VI-2 | Akr7a5 |
| 772 | 3 | 4 | 5 | 6 | | VI-2 | Alas2 |
| 773 | 3 | 4 | 5 | 6 | | VI-2 | Aldoc |
| 774 | 3 | 4 | 5 | 6 | | VI-2 | Alpk1 |
| 775 | 3 | 4 | 5 | 6 | | VI-2 | Amhr2 |
| 776 | 3 | 4 | 5 | 6 | | VI-2 | Amica1 |
| 777 | 3 | 4 | 5 | 6 | | VI-2 | Amigo2 |
| 778 | 3 | 4 | 5 | 6 | | VI-2 | Arnt |
| 779 | 3 | 4 | 5 | 6 | | VI-2 | Anapc11 |
| 780 | 3 | 4 | 5 | 6 | | VI-2 | Ang4 |
| 781 | 3 | 4 | 5 | 6 | | VI-2 | Angptl4 |
| 782 | 3 | 4 | 5 | 6 | | VI-2 | Ankdd1b |
| 783 | 3 | 4 | 5 | 6 | | VI-2 | Ankhd1 |
| 784 | 3 | 4 | 5 | 6 | | VI-2 | Ankrd52 |
| 785 | 3 | 4 | 5 | 6 | | VI-2 | Ap5m1 |
| 786 | 3 | 4 | 5 | 6 | | VI-2 | Apeh |
| 787 | 3 | 4 | 5 | 6 | | VI-2 | Aplnr |
| 788 | 3 | 4 | 5 | 6 | | VI-2 | Apoa5 |
| 789 | 3 | 4 | 5 | 6 | | VI-2 | Apoe |
| 790 | 3 | 4 | 5 | 6 | | VI-2 | Apopt1 |
| 791 | 3 | 4 | 5 | 6 | | VI-2 | Appbp2 |
| 792 | 3 | 4 | 5 | 6 | | VI-2 | Aqp9 |
| 793 | 3 | 4 | 5 | 6 | | VI-2 | Arap2 |
| 794 | 3 | 4 | 5 | 6 | | VI-2 | Arhgap20 |
| 795 | 3 | 4 | 5 | 6 | | VI-2 | Arhgap31 |
| 796 | 3 | 4 | 5 | 6 | | VI-2 | Arhgap5 |
| 797 | 3 | 4 | 5 | 6 | | VI-2 | Arhgef16 |
| 798 | 3 | 4 | 5 | 6 | | VI-2 | Arl4d |
| 799 | 3 | 4 | 5 | 6 | | VI-2 | Armc10 |
| 800 | 3 | 4 | 5 | 6 | | VI-2 | Arntl |
| 801 | 3 | 4 | 5 | 6 | | VI-2 | Arpp21 |
| 802 | 3 | 4 | 5 | 6 | | VI-2 | Arrb1 |
| 803 | 3 | 4 | 5 | 6 | | VI-2 | Arrb2 |
| 804 | 3 | 4 | 5 | 6 | | VI-2 | Arrdc5 |
| 805 | 3 | 4 | 5 | 6 | | VI-2 | Arsi |
| 806 | 3 | 4 | 5 | 6 | | VI-2 | Arvcf |
| 807 | 3 | 4 | 5 | 6 | | VI-2 | Ascc1 |
| 808 | 3 | 4 | 5 | 6 | | VI-2 | Ascl1 |
| 809 | 3 | 4 | 5 | 6 | | VI-2 | Ascl3 |
| 810 | 3 | 4 | 5 | 6 | | VI-2 | Ash1l |
| 811 | 3 | 4 | 5 | 6 | | VI-2 | Asic5 |
| 812 | 3 | 4 | 5 | 6 | | VI-2 | Asi |
| 813 | 3 | 4 | 5 | 6 | | VI-2 | Atf7 |
| 814 | 3 | 4 | 5 | 6 | | VI-2 | Atf7ip |
| 815 | 3 | 4 | 5 | 6 | | VI-2 | Atg16l2 |
| 816 | 3 | 4 | 5 | 6 | | VI-2 | Atl2 |
| 817 | 3 | 4 | 5 | 6 | | VI-2 | Atoh8 |
| 818 | 3 | 4 | 5 | 6 | | VI-2 | Atp1b1 |
| 819 | 3 | 4 | 5 | 6 | | VI-2 | Atp2c2 |
| 820 | 3 | 4 | 5 | 6 | | VI-2 | Atp6v0c-ps2 |
| 821 | 3 | 4 | 5 | 6 | | VI-2 | Atp6v1e2 |
| 822 | 3 | 4 | 5 | 6 | | VI-2 | Atp8b3 |
| 823 | 3 | 4 | 5 | 6 | | VI-2 | AU021092 |
| 824 | 3 | 4 | 5 | 6 | | VI-2 | AU022252 |
| 825 | 3 | 4 | 5 | 6 | | VI-2 | Avil |
| 826 | 3 | 4 | 5 | 6 | | VI-2 | B230217O12Rik |
| 827 | 3 | 4 | 5 | 6 | | VI-2 | B3galt4 |
| 828 | 3 | 4 | 5 | 6 | | VI-2 | B3gnt3 |
| 829 | 3 | 4 | 5 | 6 | | VI-2 | B4galnt2 |
| 830 | 3 | 4 | 5 | 6 | | VI-2 | B930003M22Rik |
| 831 | 3 | 4 | 5 | 6 | | VI-2 | Bace1 |
| 832 | 3 | 4 | 5 | 6 | | VI-2 | Bach2 |
| 833 | 3 | 4 | 5 | 6 | | VI-2 | Bad |
| 834 | 3 | 4 | 5 | 6 | | VI-2 | Bambi-ps1 |
| 835 | 3 | 4 | 5 | 6 | | VI-2 | Basp1 |
| 836 | 3 | 4 | 5 | 6 | | VI-2 | BB014433 |
| 837 | 3 | 4 | 5 | 6 | | VI-2 | Bbox1 |
| 838 | 3 | 4 | 5 | 6 | | VI-2 | Bbs9 |
| 839 | 3 | 4 | 5 | 6 | | VI-2 | BC005561 |
| 840 | 3 | 4 | 5 | 6 | | VI-2 | BC028528 |
| 841 | 3 | 4 | 5 | 6 | | VI-2 | BC049635 |
| 842 | 3 | 4 | 5 | 6 | | VI-2 | BC049762 |
| 843 | 3 | 4 | 5 | 6 | | VI-2 | BC051226 |
| 844 | 3 | 4 | 5 | 6 | | VI-2 | BC051537 |
| 845 | 3 | 4 | 5 | 6 | | VI-2 | BC051628 |
| 846 | 3 | 4 | 5 | 6 | | VI-2 | BC053749 |
| 847 | 3 | 4 | 5 | 6 | | VI-2 | BC068281 |
| 848 | 3 | 4 | 5 | 6 | | VI-2 | BC100451 |

Fig. 43 - 6

| | | | | | | | | | | | | | | | |
|---|---|---|---|---|---|---|---|---|---|---|---|---|---|---|---|
| 849 | 3 | 4 | 5 | 6 | | | VI-2 | Bcl6 | | 934 | 3 | 4 | 5 | 6 | | | VI-2 | Cd28 |
| 850 | 3 | 4 | 5 | 6 | | | VI-2 | Bcl7a | | 935 | 3 | 4 | 5 | 6 | | | VI-2 | Cd300c |
| 851 | 3 | 4 | 5 | 6 | | | VI-2 | Bcl7c | | 936 | 3 | 4 | 5 | 6 | | | VI-2 | Cd36 |
| 852 | 3 | 4 | 5 | 6 | | | VI-2 | Bcl9l | | 937 | 3 | 4 | 5 | 6 | | | VI-2 | Cd40 |
| 853 | 3 | 4 | 5 | 6 | | | VI-2 | Bcorl1 | | 938 | 3 | 4 | 5 | 6 | | | VI-2 | Cd74 |
| 854 | 3 | 4 | 5 | 6 | | | VI-2 | Bend5 | | 939 | 3 | 4 | 5 | 6 | | | VI-2 | Cd79a |
| 855 | 3 | 4 | 5 | 6 | | | VI-2 | Bex1 | | 940 | 3 | 4 | 5 | 6 | | | VI-2 | Cd79b |
| 856 | 3 | 4 | 5 | 6 | | | VI-2 | Bfsp2 | | 941 | 3 | 4 | 5 | 6 | | | VI-2 | Cd83 |
| 857 | 3 | 4 | 5 | 6 | | | VI-2 | Bhlha15 | | 942 | 3 | 4 | 5 | 6 | | | VI-2 | Cd8a |
| 858 | 3 | 4 | 5 | 6 | | | VI-2 | Bicc1 | | 943 | 3 | 4 | 5 | 6 | | | VI-2 | Cd93 |
| 859 | 3 | 4 | 5 | 6 | | | VI-2 | Blk | | 944 | 3 | 4 | 5 | 6 | | | VI-2 | Cdc42ep5 |
| 860 | 3 | 4 | 5 | 6 | | | VI-2 | Blnk | | 945 | 3 | 4 | 5 | 6 | | | VI-2 | Cdcp1 |
| 861 | 3 | 4 | 5 | 6 | | | VI-2 | Bloc1s2 | | 946 | 3 | 4 | 5 | 6 | | | VI-2 | Cdh1 |
| 862 | 3 | 4 | 5 | 6 | | | VI-2 | Bmf | | 947 | 3 | 4 | 5 | 6 | | | VI-2 | Cdh13 |
| 863 | 3 | 4 | 5 | 6 | | | VI-2 | Bod1l | | 948 | 3 | 4 | 5 | 6 | | | VI-2 | Cdh16 |
| 864 | 3 | 4 | 5 | 6 | | | VI-2 | Bok | | 949 | 3 | 4 | 5 | 6 | | | VI-2 | Cdh24 |
| 865 | 3 | 4 | 5 | 6 | | | VI-2 | Bola3 | | 950 | 3 | 4 | 5 | 6 | | | VI-2 | Cdhr5 |
| 866 | 3 | 4 | 5 | 6 | | | VI-2 | Bphl | | 951 | 3 | 4 | 5 | 6 | | | VI-2 | Cdk14 |
| 867 | 3 | 4 | 5 | 6 | | | VI-2 | Bptf | | 952 | 3 | 4 | 5 | 6 | | | VI-2 | Cdk6 |
| 868 | 3 | 4 | 5 | 6 | | | VI-2 | Btbd2 | | 953 | 3 | 4 | 5 | 6 | | | VI-2 | Cdkl5 |
| 869 | 3 | 4 | 5 | 6 | | | VI-2 | Btbd6 | | 954 | 3 | 4 | 5 | 6 | | | VI-2 | Cdkn2b |
| 870 | 3 | 4 | 5 | 6 | | | VI-2 | Btbd7 | | 955 | 3 | 4 | 5 | 6 | | | VI-2 | Cdr2 |
| 871 | 3 | 4 | 5 | 6 | | | VI-2 | Btg2 | | 956 | 3 | 4 | 5 | 6 | | | VI-2 | Cdrt4 |
| 872 | 3 | 4 | 5 | 6 | | | VI-2 | Btla | | 957 | 3 | 4 | 5 | 6 | | | VI-2 | Cebpzos |
| 873 | 3 | 4 | 5 | 6 | | | VI-2 | C030016D13Rik | | 958 | 3 | 4 | 5 | 6 | | | VI-2 | Cecr2 |
| 874 | 3 | 4 | 5 | 6 | | | VI-2 | C030034L19Rik | | 959 | 3 | 4 | 5 | 6 | | | VI-2 | Cemip |
| 875 | 3 | 4 | 5 | 6 | | | VI-2 | C130046K22Rik | | 960 | 3 | 4 | 5 | 6 | | | VI-2 | Cep104 |
| 876 | 3 | 4 | 5 | 6 | | | VI-2 | C2cd4d | | 961 | 3 | 4 | 5 | 6 | | | VI-2 | Cep112 |
| 877 | 3 | 4 | 5 | 6 | | | VI-2 | C4bp | | 962 | 3 | 4 | 5 | 6 | | | VI-2 | Cep68 |
| 878 | 3 | 4 | 5 | 6 | | | VI-2 | C530005A16Rik | | 963 | 3 | 4 | 5 | 6 | | | VI-2 | Cers6 |
| 879 | 3 | 4 | 5 | 6 | | | VI-2 | C78339 | | 964 | 3 | 4 | 5 | 6 | | | VI-2 | Ces1e |
| 880 | 3 | 4 | 5 | 6 | | | VI-2 | Cab39l | | 965 | 3 | 4 | 5 | 6 | | | VI-2 | Ces3b |
| 881 | 3 | 4 | 5 | 6 | | | VI-2 | Cables1 | | 966 | 3 | 4 | 5 | 6 | | | VI-2 | Cetn4 |
| 882 | 3 | 4 | 5 | 6 | | | VI-2 | Cabs1 | | 967 | 3 | 4 | 5 | 6 | | | VI-2 | Chac2 |
| 883 | 3 | 4 | 5 | 6 | | | VI-2 | Cacna1e | | 968 | 3 | 4 | 5 | 6 | | | VI-2 | Chad |
| 884 | 3 | 4 | 5 | 6 | | | VI-2 | Cacna1i | | 969 | 3 | 4 | 5 | 6 | | | VI-2 | Chadl |
| 885 | 3 | 4 | 5 | 6 | | | VI-2 | Calca | | 970 | 3 | 4 | 5 | 6 | | | VI-2 | Chga |
| 886 | 3 | 4 | 5 | 6 | | | VI-2 | Camk2n1 | | 971 | 3 | 4 | 5 | 6 | | | VI-2 | Chia1 |
| 887 | 3 | 4 | 5 | 6 | | | VI-2 | Camk4 | | 972 | 3 | 4 | 5 | 6 | | | VI-2 | Chmp4c |
| 888 | 3 | 4 | 5 | 6 | | | VI-2 | Camkk1 | | 973 | 3 | 4 | 5 | 6 | | | VI-2 | Chrm4 |
| 889 | 3 | 4 | 5 | 6 | | | VI-2 | Capn10 | | 974 | 3 | 4 | 5 | 6 | | | VI-2 | Chrna10 |
| 890 | 3 | 4 | 5 | 6 | | | VI-2 | Capn15 | | 975 | 3 | 4 | 5 | 6 | | | VI-2 | Chrna2 |
| 891 | 3 | 4 | 5 | 6 | | | VI-2 | Capn3 | | 976 | 3 | 4 | 5 | 6 | | | VI-2 | Chrna9 |
| 892 | 3 | 4 | 5 | 6 | | | VI-2 | Capsl | | 977 | 3 | 4 | 5 | 6 | | | VI-2 | Chst10 |
| 893 | 3 | 4 | 5 | 6 | | | VI-2 | Capza3 | | 978 | 3 | 4 | 5 | 6 | | | VI-2 | Chst3 |
| 894 | 3 | 4 | 5 | 6 | | | VI-2 | Car14 | | 979 | 3 | 4 | 5 | 6 | | | VI-2 | Cib4 |
| 895 | 3 | 4 | 5 | 6 | | | VI-2 | Car15 | | 980 | 3 | 4 | 5 | 6 | | | VI-2 | Ciita |
| 896 | 3 | 4 | 5 | 6 | | | VI-2 | Car4 | | 981 | 3 | 4 | 5 | 6 | | | VI-2 | Cisd3 |
| 897 | 3 | 4 | 5 | 6 | | | VI-2 | Car6 | | 982 | 3 | 4 | 5 | 6 | | | VI-2 | Clcf1 |
| 898 | 3 | 4 | 5 | 6 | | | VI-2 | Card11 | | 983 | 3 | 4 | 5 | 6 | | | VI-2 | Clcn6 |
| 899 | 3 | 4 | 5 | 6 | | | VI-2 | Ccbl2 | | 984 | 3 | 4 | 5 | 6 | | | VI-2 | Cldn13 |
| 900 | 3 | 4 | 5 | 6 | | | VI-2 | Ccdc101 | | 985 | 3 | 4 | 5 | 6 | | | VI-2 | Cldn22 |
| 901 | 3 | 4 | 5 | 6 | | | VI-2 | Ccdc108 | | 986 | 3 | 4 | 5 | 6 | | | VI-2 | Cldn23 |
| 902 | 3 | 4 | 5 | 6 | | | VI-2 | Ccdc114 | | 987 | 3 | 4 | 5 | 6 | | | VI-2 | Cldn3 |
| 903 | 3 | 4 | 5 | 6 | | | VI-2 | Ccdc12 | | 988 | 3 | 4 | 5 | 6 | | | VI-2 | Cldn4 |
| 904 | 3 | 4 | 5 | 6 | | | VI-2 | Ccdc136 | | 989 | 3 | 4 | 5 | 6 | | | VI-2 | Cldn7 |
| 905 | 3 | 4 | 5 | 6 | | | VI-2 | Ccdc153 | | 990 | 3 | 4 | 5 | 6 | | | VI-2 | Cldn8 |
| 906 | 3 | 4 | 5 | 6 | | | VI-2 | Ccdc170 | | 991 | 3 | 4 | 5 | 6 | | | VI-2 | Clec1a |
| 907 | 3 | 4 | 5 | 6 | | | VI-2 | Ccdc185 | | 992 | 3 | 4 | 5 | 6 | | | VI-2 | Clec2h |
| 908 | 3 | 4 | 5 | 6 | | | VI-2 | Ccdc22 | | 993 | 3 | 4 | 5 | 6 | | | VI-2 | Clec4b2 |
| 909 | 3 | 4 | 5 | 6 | | | VI-2 | Ccdc28a | | 994 | 3 | 4 | 5 | 6 | | | VI-2 | Clic3 |
| 910 | 3 | 4 | 5 | 6 | | | VI-2 | Ccdc30 | | 995 | 3 | 4 | 5 | 6 | | | VI-2 | Clic6 |
| 911 | 3 | 4 | 5 | 6 | | | VI-2 | Ccdc39 | | 996 | 3 | 4 | 5 | 6 | | | VI-2 | Clk3 |
| 912 | 3 | 4 | 5 | 6 | | | VI-2 | Ccdc54 | | 997 | 3 | 4 | 5 | 6 | | | VI-2 | Clmn |
| 913 | 3 | 4 | 5 | 6 | | | VI-2 | Ccdc85b | | 998 | 3 | 4 | 5 | 6 | | | VI-2 | Cluap1 |
| 914 | 3 | 4 | 5 | 6 | | | VI-2 | Ccdc85c | | 999 | 3 | 4 | 5 | 6 | | | VI-2 | Cma1 |
| 915 | 3 | 4 | 5 | 6 | | | VI-2 | Ccdc88c | | 1000 | 3 | 4 | 5 | 6 | | | VI-2 | Cmbl |
| 916 | 3 | 4 | 5 | 6 | | | VI-2 | Ccdc89 | | 1001 | 3 | 4 | 5 | 6 | | | VI-2 | Cmpk2 |
| 917 | 3 | 4 | 5 | 6 | | | VI-2 | Ccdc92 | | 1002 | 3 | 4 | 5 | 6 | | | VI-2 | Cmss1 |
| 918 | 3 | 4 | 5 | 6 | | | VI-2 | Ccdc93 | | 1003 | 3 | 4 | 5 | 6 | | | VI-2 | Cmtm8 |
| 919 | 3 | 4 | 5 | 6 | | | VI-2 | Ccer1 | | 1004 | 3 | 4 | 5 | 6 | | | VI-2 | Cnga3 |
| 920 | 3 | 4 | 5 | 6 | | | VI-2 | Ccin | | 1005 | 3 | 4 | 5 | 6 | | | VI-2 | Cnnm3 |
| 921 | 3 | 4 | 5 | 6 | | | VI-2 | Ccl1 | | 1006 | 3 | 4 | 5 | 6 | | | VI-2 | Cnp |
| 922 | 3 | 4 | 5 | 6 | | | VI-2 | Ccl25 | | 1007 | 3 | 4 | 5 | 6 | | | VI-2 | Cntf |
| 923 | 3 | 4 | 5 | 6 | | | VI-2 | Ccl27a | | 1008 | 3 | 4 | 5 | 6 | | | VI-2 | Coa4 |
| 924 | 3 | 4 | 5 | 6 | | | VI-2 | Ccl28 | | 1009 | 3 | 4 | 5 | 6 | | | VI-2 | Coa6 |
| 925 | 3 | 4 | 5 | 6 | | | VI-2 | Ccr10 | | 1010 | 3 | 4 | 5 | 6 | | | VI-2 | Col4a4 |
| 926 | 3 | 4 | 5 | 6 | | | VI-2 | Ccr4 | | 1011 | 3 | 4 | 5 | 6 | | | VI-2 | Copz2 |
| 927 | 3 | 4 | 5 | 6 | | | VI-2 | Ccr6 | | 1012 | 3 | 4 | 5 | 6 | | | VI-2 | Coro6 |
| 928 | 3 | 4 | 5 | 6 | | | VI-2 | Ccr9 | | 1013 | 3 | 4 | 5 | 6 | | | VI-2 | Cox4i2 |
| 929 | 3 | 4 | 5 | 6 | | | VI-2 | Cd19 | | 1014 | 3 | 4 | 5 | 6 | | | VI-2 | Cox7b2 |
| 930 | 3 | 4 | 5 | 6 | | | VI-2 | Cd2 | | 1015 | 3 | 4 | 5 | 6 | | | VI-2 | Cpeb3 |
| 931 | 3 | 4 | 5 | 6 | | | VI-2 | Cd200 | | 1016 | 3 | 4 | 5 | 6 | | | VI-2 | Cped1 |
| 932 | 3 | 4 | 5 | 6 | | | VI-2 | Cd209a | | 1017 | 3 | 4 | 5 | 6 | | | VI-2 | Cpn1 |
| 933 | 3 | 4 | 5 | 6 | | | VI-2 | Cd22 | | 1018 | 3 | 4 | 5 | 6 | | | VI-2 | Crabp1 |

Fig. 43 - 7

| | | | | | | | | |
|---|---|---|---|---|---|---|---|---|
| 1019 | 3 | 4 | 5 | 6 | | VI-2 | Crb3 |
| 1020 | 3 | 4 | 5 | 6 | | VI-2 | Creb3l2 |
| 1021 | 3 | 4 | 5 | 6 | | VI-2 | Creb5 |
| 1022 | 3 | 4 | 5 | 6 | | VI-2 | Crebbp |
| 1023 | 3 | 4 | 5 | 6 | | VI-2 | Creld2 |
| 1024 | 3 | 4 | 5 | 6 | | VI-2 | Crem |
| 1025 | 3 | 4 | 5 | 6 | | VI-2 | Crybb1 |
| 1026 | 3 | 4 | 5 | 6 | | VI-2 | Csnk2a2 |
| 1027 | 3 | 4 | 5 | 6 | | VI-2 | Csnk2ip |
| 1028 | 3 | 4 | 5 | 6 | | VI-2 | Cst8 |
| 1029 | 3 | 4 | 5 | 6 | | VI-2 | Cst9 |
| 1030 | 3 | 4 | 5 | 6 | | VI-2 | Ctgf |
| 1031 | 3 | 4 | 5 | 6 | | VI-2 | Ctnnbip1 |
| 1032 | 3 | 4 | 5 | 6 | | VI-2 | Ctsw |
| 1033 | 3 | 4 | 5 | 6 | | VI-2 | Cutal |
| 1034 | 3 | 4 | 5 | 6 | | VI-2 | Cwh43 |
| 1035 | 3 | 4 | 5 | 6 | | VI-2 | Cx3cr1 |
| 1036 | 3 | 4 | 5 | 6 | | VI-2 | Cxcl3 |
| 1037 | 3 | 4 | 5 | 6 | | VI-2 | Cxcr5 |
| 1038 | 3 | 4 | 5 | 6 | | VI-2 | Cxcr6 |
| 1039 | 3 | 4 | 5 | 6 | | VI-2 | Cxxc5 |
| 1040 | 3 | 4 | 5 | 6 | | VI-2 | Cyb5d1 |
| 1041 | 3 | 4 | 5 | 6 | | VI-2 | Cyct |
| 1042 | 3 | 4 | 5 | 6 | | VI-2 | Cyp17a1 |
| 1043 | 3 | 4 | 5 | 6 | | VI-2 | Cyp26b1 |
| 1044 | 3 | 4 | 5 | 6 | | VI-2 | Cyp2c69 |
| 1045 | 3 | 4 | 5 | 6 | | VI-2 | Cyp2d37-ps |
| 1046 | 3 | 4 | 5 | 6 | | VI-2 | Cyp4a12b |
| 1047 | 3 | 4 | 5 | 6 | | VI-2 | Cyp4b1-ps2 |
| 1048 | 3 | 4 | 5 | 6 | | VI-2 | Cyp4f15 |
| 1049 | 3 | 4 | 5 | 6 | | VI-2 | Cyp8 |
| 1050 | 3 | 4 | 5 | 6 | | VI-2 | Cyyr1 |
| 1051 | 3 | 4 | 5 | 6 | | VI-2 | D030028A08Rik |
| 1052 | 3 | 4 | 5 | 6 | | VI-2 | D1Pas1 |
| 1053 | 3 | 4 | 5 | 6 | | VI-2 | D7Ertd143e |
| 1054 | 3 | 4 | 5 | 6 | | VI-2 | Dao |
| 1055 | 3 | 4 | 5 | 6 | | VI-2 | Dbndd1 |
| 1056 | 3 | 4 | 5 | 6 | | VI-2 | Dcdc2a |
| 1057 | 3 | 4 | 5 | 6 | | VI-2 | Dctn2 |
| 1058 | 3 | 4 | 5 | 6 | | VI-2 | Ddah1 |
| 1059 | 3 | 4 | 5 | 6 | | VI-2 | Ddah2 |
| 1060 | 3 | 4 | 5 | 6 | | VI-2 | Ddi1 |
| 1061 | 3 | 4 | 5 | 6 | | VI-2 | Ddit4 |
| 1062 | 3 | 4 | 5 | 6 | | VI-2 | Ddx54 |
| 1063 | 3 | 4 | 5 | 6 | | VI-2 | Ddx60 |
| 1064 | 3 | 4 | 5 | 6 | | VI-2 | Decr2 |
| 1065 | 3 | 4 | 5 | 6 | | VI-2 | Defa17 |
| 1066 | 3 | 4 | 5 | 6 | | VI-2 | Defa20 |
| 1067 | 3 | 4 | 5 | 6 | | VI-2 | Defa23 |
| 1068 | 3 | 4 | 5 | 6 | | VI-2 | Defa4 |
| 1069 | 3 | 4 | 5 | 6 | | VI-2 | Defb1 |
| 1070 | 3 | 4 | 5 | 6 | | VI-2 | Defb15 |
| 1071 | 3 | 4 | 5 | 6 | | VI-2 | Defb25 |
| 1072 | 3 | 4 | 5 | 6 | | VI-2 | Defb26 |
| 1073 | 3 | 4 | 5 | 6 | | VI-2 | Defb40 |
| 1074 | 3 | 4 | 5 | 6 | | VI-2 | Degs2 |
| 1075 | 3 | 4 | 5 | 6 | | VI-2 | Depdc7 |
| 1076 | 3 | 4 | 5 | 6 | | VI-2 | Desi1 |
| 1077 | 3 | 4 | 5 | 6 | | VI-2 | Det1 |
| 1078 | 3 | 4 | 5 | 6 | | VI-2 | Dgke |
| 1079 | 3 | 4 | 5 | 6 | | VI-2 | Dgkeos |
| 1080 | 3 | 4 | 5 | 6 | | VI-2 | Dgkg |
| 1081 | 3 | 4 | 5 | 6 | | VI-2 | Dhdh |
| 1082 | 3 | 4 | 5 | 6 | | VI-2 | Dhrs13 |
| 1083 | 3 | 4 | 5 | 6 | | VI-2 | Dhtkd1 |
| 1084 | 3 | 4 | 5 | 6 | | VI-2 | Dio3os |
| 1085 | 3 | 4 | 5 | 6 | | VI-2 | Dixdc1 |
| 1086 | 3 | 4 | 5 | 6 | | VI-2 | Dleu2 |
| 1087 | 3 | 4 | 5 | 6 | | VI-2 | Dll4 |
| 1088 | 3 | 4 | 5 | 6 | | VI-2 | Dmrtb1 |
| 1089 | 3 | 4 | 5 | 6 | | VI-2 | Dnaaf1 |
| 1090 | 3 | 4 | 5 | 6 | | VI-2 | Dnah10 |
| 1091 | 3 | 4 | 5 | 6 | | VI-2 | Dnah6 |
| 1092 | 3 | 4 | 5 | 6 | | VI-2 | Dnajb13 |
| 1093 | 3 | 4 | 5 | 6 | | VI-2 | Dnajb2 |
| 1094 | 3 | 4 | 5 | 6 | | VI-2 | Dnajb7 |
| 1095 | 3 | 4 | 5 | 6 | | VI-2 | Dnajc19 |
| 1096 | 3 | 4 | 5 | 6 | | VI-2 | Dnajc22 |
| 1097 | 3 | 4 | 5 | 6 | | VI-2 | Dnajc28 |
| 1098 | 3 | 4 | 5 | 6 | | VI-2 | Dnajc5b |
| 1099 | 3 | 4 | 5 | 6 | | VI-2 | Dnali1 |
| 1100 | 3 | 4 | 5 | 6 | | VI-2 | Dnase1 |
| 1101 | 3 | 4 | 5 | 6 | | VI-2 | Dnase1l2 |
| 1102 | 3 | 4 | 5 | 6 | | VI-2 | Dnpep |
| 1103 | 3 | 4 | 5 | 6 | | VI-2 | Dntt |
| 1104 | 3 | 4 | 5 | 6 | | VI-2 | Dnttip1 |
| 1105 | 3 | 4 | 5 | 6 | | VI-2 | Dok3 |
| 1106 | 3 | 4 | 5 | 6 | | VI-2 | Dopey1 |
| 1107 | 3 | 4 | 5 | 6 | | VI-2 | Dpp4 |
| 1108 | 3 | 4 | 5 | 6 | | VI-2 | Dpp9 |
| 1109 | 3 | 4 | 5 | 6 | | VI-2 | Dpy19l4 |
| 1110 | 3 | 4 | 5 | 6 | | VI-2 | Dpyd |
| 1111 | 3 | 4 | 5 | 6 | | VI-2 | Dtnb |
| 1112 | 3 | 4 | 5 | 6 | | VI-2 | Dtnbp1 |
| 1113 | 3 | 4 | 5 | 6 | | VI-2 | Dtwd1 |
| 1114 | 3 | 4 | 5 | 6 | | VI-2 | Dtwd2 |
| 1115 | 3 | 4 | 5 | 6 | | VI-2 | Dtx1 |
| 1116 | 3 | 4 | 5 | 6 | | VI-2 | Dusp2 |
| 1117 | 3 | 4 | 5 | 6 | | VI-2 | Dusp4 |
| 1118 | 3 | 4 | 5 | 6 | | VI-2 | Dusp5 |
| 1119 | 3 | 4 | 5 | 6 | | VI-2 | Dynll1 |
| 1120 | 3 | 4 | 5 | 6 | | VI-2 | E030030I06Rik |
| 1121 | 3 | 4 | 5 | 6 | | VI-2 | E130309D14Rik |
| 1122 | 3 | 4 | 5 | 6 | | VI-2 | E130310I04Rik |
| 1123 | 3 | 4 | 5 | 6 | | VI-2 | E230008N13Rik |
| 1124 | 3 | 4 | 5 | 6 | | VI-2 | E230029C05Rik |
| 1125 | 3 | 4 | 5 | 6 | | VI-2 | E330020D12Rik |
| 1126 | 3 | 4 | 5 | 6 | | VI-2 | E330033B04Rik |
| 1127 | 3 | 4 | 5 | 6 | | VI-2 | Eaf2 |
| 1128 | 3 | 4 | 5 | 6 | | VI-2 | Ear1 |
| 1129 | 3 | 4 | 5 | 6 | | VI-2 | Ear2 |
| 1130 | 3 | 4 | 5 | 6 | | VI-2 | Ebf1 |
| 1131 | 3 | 4 | 5 | 6 | | VI-2 | Ece2 |
| 1132 | 3 | 4 | 5 | 6 | | VI-2 | Eci2 |
| 1133 | 3 | 4 | 5 | 6 | | VI-2 | Edaradd |
| 1134 | 3 | 4 | 5 | 6 | | VI-2 | Edem1 |
| 1135 | 3 | 4 | 5 | 6 | | VI-2 | Efcab2 |
| 1136 | 3 | 4 | 5 | 6 | | VI-2 | Efcc1 |
| 1137 | 3 | 4 | 5 | 6 | | VI-2 | Efhc1 |
| 1138 | 3 | 4 | 5 | 6 | | VI-2 | Efs |
| 1139 | 3 | 4 | 5 | 6 | | VI-2 | Egfl6 |
| 1140 | 3 | 4 | 5 | 6 | | VI-2 | Egfl8 |
| 1141 | 3 | 4 | 5 | 6 | | VI-2 | Ehd2 |
| 1142 | 3 | 4 | 5 | 6 | | VI-2 | Ehf |
| 1143 | 3 | 4 | 5 | 6 | | VI-2 | Eif2ak3 |
| 1144 | 3 | 4 | 5 | 6 | | VI-2 | Eif4ebp3 |
| 1145 | 3 | 4 | 5 | 6 | | VI-2 | Eif3 |
| 1146 | 3 | 4 | 5 | 6 | | VI-2 | Ell3 |
| 1147 | 3 | 4 | 5 | 6 | | VI-2 | Elovl2 |
| 1148 | 3 | 4 | 5 | 6 | | VI-2 | Elp6 |
| 1149 | 3 | 4 | 5 | 6 | | VI-2 | Emid1 |
| 1150 | 3 | 4 | 5 | 6 | | VI-2 | Enc1 |
| 1151 | 3 | 4 | 5 | 6 | | VI-2 | Enkur |
| 1152 | 3 | 4 | 5 | 6 | | VI-2 | Epb4.1l4b |
| 1153 | 3 | 4 | 5 | 6 | | VI-2 | Epha2 |
| 1154 | 3 | 4 | 5 | 6 | | VI-2 | Ephb6 |
| 1155 | 3 | 4 | 5 | 6 | | VI-2 | Eppin |
| 1156 | 3 | 4 | 5 | 6 | | VI-2 | Eps8l2 |
| 1157 | 3 | 4 | 5 | 6 | | VI-2 | Eral1 |
| 1158 | 3 | 4 | 5 | 6 | | VI-2 | Erbb3 |
| 1159 | 3 | 4 | 5 | 6 | | VI-2 | Erdr1 |
| 1160 | 3 | 4 | 5 | 6 | | VI-2 | Esr2 |
| 1161 | 3 | 4 | 5 | 6 | | VI-2 | Esrp2 |
| 1162 | 3 | 4 | 5 | 6 | | VI-2 | Ethe1 |
| 1163 | 3 | 4 | 5 | 6 | | VI-2 | Etv1 |
| 1164 | 3 | 4 | 5 | 6 | | VI-2 | Evi5l |
| 1165 | 3 | 4 | 5 | 6 | | VI-2 | Exosc6 |
| 1166 | 3 | 4 | 5 | 6 | | VI-2 | F13a1 |
| 1167 | 3 | 4 | 5 | 6 | | VI-2 | F3 |
| 1168 | 3 | 4 | 5 | 6 | | VI-2 | F420014N23Rik |
| 1169 | 3 | 4 | 5 | 6 | | VI-2 | F830002L21Rik |
| 1170 | 3 | 4 | 5 | 6 | | VI-2 | Faah |
| 1171 | 3 | 4 | 5 | 6 | | VI-2 | Fabp1 |
| 1172 | 3 | 4 | 5 | 6 | | VI-2 | Faim3 |
| 1173 | 3 | 4 | 5 | 6 | | VI-2 | Fam107a |
| 1174 | 3 | 4 | 5 | 6 | | VI-2 | Fam115a |
| 1175 | 3 | 4 | 5 | 6 | | VI-2 | Fam124b |
| 1176 | 3 | 4 | 5 | 6 | | VI-2 | Fam136a |
| 1177 | 3 | 4 | 5 | 6 | | VI-2 | Fam13b |
| 1178 | 3 | 4 | 5 | 6 | | VI-2 | Fam167b |
| 1179 | 3 | 4 | 5 | 6 | | VI-2 | Fam183b |
| 1180 | 3 | 4 | 5 | 6 | | VI-2 | Fam187b |
| 1181 | 3 | 4 | 5 | 6 | | VI-2 | Fam188b |
| 1182 | 3 | 4 | 5 | 6 | | VI-2 | Fam189a2 |
| 1183 | 3 | 4 | 5 | 6 | | VI-2 | Fam214a |
| 1184 | 3 | 4 | 5 | 6 | | VI-2 | Fam217a |
| 1185 | 3 | 4 | 5 | 6 | | VI-2 | Fam217b |
| 1186 | 3 | 4 | 5 | 6 | | VI-2 | Fam220a |
| 1187 | 3 | 4 | 5 | 6 | | VI-2 | Fam222a |
| 1188 | 3 | 4 | 5 | 6 | | VI-2 | Fam229a |

Fig. 43 - 8

| | | | | | | | | | | | | | | | | | |
|---|---|---|---|---|---|---|---|---|---|---|---|---|---|---|---|---|---|
| 1189 | 3 | 4 | 5 | 6 | | | VI-2 | Fam229b | | 1274 | 3 | 4 | 5 | 6 | | VI-2 | Gm10804 |
| 1190 | 3 | 4 | 5 | 6 | | | VI-2 | Fam24a | | 1275 | 3 | 4 | 5 | 6 | | VI-2 | Gm11346 |
| 1191 | 3 | 4 | 5 | 6 | | | VI-2 | Fam50b | | 1276 | 3 | 4 | 5 | 6 | | VI-2 | Gm11837 |
| 1192 | 3 | 4 | 5 | 6 | | | VI-2 | Fam57b | | 1277 | 3 | 4 | 5 | 6 | | VI-2 | Gm11944 |
| 1193 | 3 | 4 | 5 | 6 | | | VI-2 | Fam71e1 | | 1278 | 3 | 4 | 5 | 6 | | VI-2 | Gm12060 |
| 1194 | 3 | 4 | 5 | 6 | | | VI-2 | Fam71f1 | | 1279 | 3 | 4 | 5 | 6 | | VI-2 | Gm12942 |
| 1195 | 3 | 4 | 5 | 6 | | | VI-2 | Fam71f2 | | 1280 | 3 | 4 | 5 | 6 | | VI-2 | Gm13034 |
| 1196 | 3 | 4 | 5 | 6 | | | VI-2 | Fam83g | | 1281 | 3 | 4 | 5 | 6 | | VI-2 | Gm13298 |
| 1197 | 3 | 4 | 5 | 6 | | | VI-2 | Fam86 | | 1282 | 3 | 4 | 5 | 6 | | VI-2 | Gm13304 |
| 1198 | 3 | 4 | 5 | 6 | | | VI-2 | Fam89a | | 1283 | 3 | 4 | 5 | 6 | | VI-2 | Gm13546 |
| 1199 | 3 | 4 | 5 | 6 | | | VI-2 | Fam98c | | 1284 | 3 | 4 | 5 | 6 | | VI-2 | Gm14005 |
| 1200 | 3 | 4 | 5 | 6 | | | VI-2 | Fan1 | | 1285 | 3 | 4 | 5 | 6 | | VI-2 | Gm14085 |
| 1201 | 3 | 4 | 5 | 6 | | | VI-2 | Fbxl12 | | 1286 | 3 | 4 | 5 | 6 | | VI-2 | Gm14305 |
| 1202 | 3 | 4 | 5 | 6 | | | VI-2 | Fbxo27 | | 1287 | 3 | 4 | 5 | 6 | | VI-2 | Gm14393 |
| 1203 | 3 | 4 | 5 | 6 | | | VI-2 | Fbxo31 | | 1288 | 3 | 4 | 5 | 6 | | VI-2 | Gm14431 |
| 1204 | 3 | 4 | 5 | 6 | | | VI-2 | Fbxw10 | | 1289 | 3 | 4 | 5 | 6 | | VI-2 | Gm14436 |
| 1205 | 3 | 4 | 5 | 6 | | | VI-2 | Fbxw4 | | 1290 | 3 | 4 | 5 | 6 | | VI-2 | Gm14440 |
| 1206 | 3 | 4 | 5 | 6 | | | VI-2 | Fcamr | | 1291 | 3 | 4 | 5 | 6 | | VI-2 | Gm14478 |
| 1207 | 3 | 4 | 5 | 6 | | | VI-2 | Fcer2a | | 1292 | 3 | 4 | 5 | 6 | | VI-2 | Gm15093 |
| 1208 | 3 | 4 | 5 | 6 | | | VI-2 | Fcgr2b | | 1293 | 3 | 4 | 5 | 6 | | VI-2 | Gm15308 |
| 1209 | 3 | 4 | 5 | 6 | | | VI-2 | Fcrl1 | | 1294 | 3 | 4 | 5 | 6 | | VI-2 | Gm15441 |
| 1210 | 3 | 4 | 5 | 6 | | | VI-2 | Fcrla | | 1295 | 3 | 4 | 5 | 6 | | VI-2 | Gm15471 |
| 1211 | 3 | 4 | 5 | 6 | | | VI-2 | Fdft1 | | 1296 | 3 | 4 | 5 | 6 | | VI-2 | Gm15663 |
| 1212 | 3 | 4 | 5 | 6 | | | VI-2 | Fermt1 | | 1297 | 3 | 4 | 5 | 6 | | VI-2 | Gm15787 |
| 1213 | 3 | 4 | 5 | 6 | | | VI-2 | Fert2 | | 1298 | 3 | 4 | 5 | 6 | | VI-2 | Gm16023 |
| 1214 | 3 | 4 | 5 | 6 | | | VI-2 | Fga | | 1299 | 3 | 4 | 5 | 6 | | VI-2 | Gm16062 |
| 1215 | 3 | 4 | 5 | 6 | | | VI-2 | Fgd6 | | 1300 | 3 | 4 | 5 | 6 | | VI-2 | Gm16740 |
| 1216 | 3 | 4 | 5 | 6 | | | VI-2 | Fhdc1 | | 1301 | 3 | 4 | 5 | 6 | | VI-2 | Gm16861 |
| 1217 | 3 | 4 | 5 | 6 | | | VI-2 | Fitm2 | | 1302 | 3 | 4 | 5 | 6 | | VI-2 | Gm17252 |
| 1218 | 3 | 4 | 5 | 6 | | | VI-2 | Fkbp11 | | 1303 | 3 | 4 | 5 | 6 | | VI-2 | Gm17455 |
| 1219 | 3 | 4 | 5 | 6 | | | VI-2 | Fkbp3 | | 1304 | 3 | 4 | 5 | 6 | | VI-2 | Gm17745 |
| 1220 | 3 | 4 | 5 | 6 | | | VI-2 | Fktn | | 1305 | 3 | 4 | 5 | 6 | | VI-2 | Gm19897 |
| 1221 | 3 | 4 | 5 | 6 | | | VI-2 | Flywch2 | | 1306 | 3 | 4 | 5 | 6 | | VI-2 | Gm20098 |
| 1222 | 3 | 4 | 5 | 6 | | | VI-2 | Fmo5 | | 1307 | 3 | 4 | 5 | 6 | | VI-2 | Gm20139 |
| 1223 | 3 | 4 | 5 | 6 | | | VI-2 | Fn3k | | 1308 | 3 | 4 | 5 | 6 | | VI-2 | Gm20319 |
| 1224 | 3 | 4 | 5 | 6 | | | VI-2 | Fndc7 | | 1309 | 3 | 4 | 5 | 6 | | VI-2 | Gm20554 |
| 1225 | 3 | 4 | 5 | 6 | | | VI-2 | Fndc9 | | 1310 | 3 | 4 | 5 | 6 | | VI-2 | Gm20604 |
| 1226 | 3 | 4 | 5 | 6 | | | VI-2 | Folr1 | | 1311 | 3 | 4 | 5 | 6 | | VI-2 | Gm21002 |
| 1227 | 3 | 4 | 5 | 6 | | | VI-2 | Fosl1 | | 1312 | 3 | 4 | 5 | 6 | | VI-2 | Gm3086 |
| 1228 | 3 | 4 | 5 | 6 | | | VI-2 | Foxa3 | | 1313 | 3 | 4 | 5 | 6 | | VI-2 | Gm3258 |
| 1229 | 3 | 4 | 5 | 6 | | | VI-2 | Foxj1 | | 1314 | 3 | 4 | 5 | 6 | | VI-2 | Gm3415 |
| 1230 | 3 | 4 | 5 | 6 | | | VI-2 | Foxo1 | | 1315 | 3 | 4 | 5 | 6 | | VI-2 | Gm4532 |
| 1231 | 3 | 4 | 5 | 6 | | | VI-2 | Foxq1 | | 1316 | 3 | 4 | 5 | 6 | | VI-2 | Gm4956 |
| 1232 | 3 | 4 | 5 | 6 | | | VI-2 | Fra10ac1 | | 1317 | 3 | 4 | 5 | 6 | | VI-2 | Gm5113 |
| 1233 | 3 | 4 | 5 | 6 | | | VI-2 | Ftsj2 | | 1318 | 3 | 4 | 5 | 6 | | VI-2 | Gm5142 |
| 1234 | 3 | 4 | 5 | 6 | | | VI-2 | Fv1 | | 1319 | 3 | 4 | 5 | 6 | | VI-2 | Gm5176 |
| 1235 | 3 | 4 | 5 | 6 | | | VI-2 | Fxyd2 | | 1320 | 3 | 4 | 5 | 6 | | VI-2 | Gm525 |
| 1236 | 3 | 4 | 5 | 6 | | | VI-2 | Fxyd3 | | 1321 | 3 | 4 | 5 | 6 | | VI-2 | Gm5441 |
| 1237 | 3 | 4 | 5 | 6 | | | VI-2 | Fyco1 | | 1322 | 3 | 4 | 5 | 6 | | VI-2 | Gm5512 |
| 1238 | 3 | 4 | 5 | 6 | | | VI-2 | Fzd10 | | 1323 | 3 | 4 | 5 | 6 | | VI-2 | Gm5535 |
| 1239 | 3 | 4 | 5 | 6 | | | VI-2 | Fzr1 | | 1324 | 3 | 4 | 5 | 6 | | VI-2 | Gm5547 |
| 1240 | 3 | 4 | 5 | 6 | | | VI-2 | G630025P09Rik | | 1325 | 3 | 4 | 5 | 6 | | VI-2 | Gm561 |
| 1241 | 3 | 4 | 5 | 6 | | | VI-2 | G630090E17Rik | | 1326 | 3 | 4 | 5 | 6 | | VI-2 | Gm5741 |
| 1242 | 3 | 4 | 5 | 6 | | | VI-2 | G6pc | | 1327 | 3 | 4 | 5 | 6 | | VI-2 | Gm6026 |
| 1243 | 3 | 4 | 5 | 6 | | | VI-2 | G6pc2 | | 1328 | 3 | 4 | 5 | 6 | | VI-2 | Gm6277 |
| 1244 | 3 | 4 | 5 | 6 | | | VI-2 | Gabarapl1 | | 1329 | 3 | 4 | 5 | 6 | | VI-2 | Gm6525 |
| 1245 | 3 | 4 | 5 | 6 | | | VI-2 | Gadd45b | | 1330 | 3 | 4 | 5 | 6 | | VI-2 | Gm6710 |
| 1246 | 3 | 4 | 5 | 6 | | | VI-2 | Galnt12 | | 1331 | 3 | 4 | 5 | 6 | | VI-2 | Gm6760 |
| 1247 | 3 | 4 | 5 | 6 | | | VI-2 | Galnt4 | | 1332 | 3 | 4 | 5 | 6 | | VI-2 | Gm773 |
| 1248 | 3 | 4 | 5 | 6 | | | VI-2 | Galnt6 | | 1333 | 3 | 4 | 5 | 6 | | VI-2 | Gm7849 |
| 1249 | 3 | 4 | 5 | 6 | | | VI-2 | Gan | | 1334 | 3 | 4 | 5 | 6 | | VI-2 | Gm8884 |
| 1250 | 3 | 4 | 5 | 6 | | | VI-2 | Gapdhs | | 1335 | 3 | 4 | 5 | 6 | | VI-2 | Gm8898 |
| 1251 | 3 | 4 | 5 | 6 | | | VI-2 | Gas2l1 | | 1336 | 3 | 4 | 5 | 6 | | VI-2 | Gm9199 |
| 1252 | 3 | 4 | 5 | 6 | | | VI-2 | Gbp11 | | 1337 | 3 | 4 | 5 | 6 | | VI-2 | Gm9958 |
| 1253 | 3 | 4 | 5 | 6 | | | VI-2 | Gch1 | | 1338 | 3 | 4 | 5 | 6 | | VI-2 | Gmfg |
| 1254 | 3 | 4 | 5 | 6 | | | VI-2 | Gdf11 | | 1339 | 3 | 4 | 5 | 6 | | VI-2 | Golga3 |
| 1255 | 3 | 4 | 5 | 6 | | | VI-2 | Gdpgp1 | | 1340 | 3 | 4 | 5 | 6 | | VI-2 | Gp6 |
| 1256 | 3 | 4 | 5 | 6 | | | VI-2 | Gfod2 | | 1341 | 3 | 4 | 5 | 6 | | VI-2 | Gpam |
| 1257 | 3 | 4 | 5 | 6 | | | VI-2 | Gfra2 | | 1342 | 3 | 4 | 5 | 6 | | VI-2 | Gpatch4 |
| 1258 | 3 | 4 | 5 | 6 | | | VI-2 | Ggn | | 1343 | 3 | 4 | 5 | 6 | | VI-2 | Gpm6a |
| 1259 | 3 | 4 | 5 | 6 | | | VI-2 | Gimap1 | | 1344 | 3 | 4 | 5 | 6 | | VI-2 | Gpr162 |
| 1260 | 3 | 4 | 5 | 6 | | | VI-2 | Gimap8 | | 1345 | 3 | 4 | 5 | 6 | | VI-2 | Gpr17 |
| 1261 | 3 | 4 | 5 | 6 | | | VI-2 | Gin1 | | 1346 | 3 | 4 | 5 | 6 | | VI-2 | Gpr171 |
| 1262 | 3 | 4 | 5 | 6 | | | VI-2 | Gins4 | | 1347 | 3 | 4 | 5 | 6 | | VI-2 | Gpr18 |
| 1263 | 3 | 4 | 5 | 6 | | | VI-2 | Gipc2 | | 1348 | 3 | 4 | 5 | 6 | | VI-2 | Gramd1b |
| 1264 | 3 | 4 | 5 | 6 | | | VI-2 | Gkap1 | | 1349 | 3 | 4 | 5 | 6 | | VI-2 | Grap |
| 1265 | 3 | 4 | 5 | 6 | | | VI-2 | Gkn1 | | 1350 | 3 | 4 | 5 | 6 | | VI-2 | Grb7 |
| 1266 | 3 | 4 | 5 | 6 | | | VI-2 | Glcci1 | | 1351 | 3 | 4 | 5 | 6 | | VI-2 | Grik5 |
| 1267 | 3 | 4 | 5 | 6 | | | VI-2 | Glis3 | | 1352 | 3 | 4 | 5 | 6 | | VI-2 | Griplos2 |
| 1268 | 3 | 4 | 5 | 6 | | | VI-2 | Glp1r | | 1353 | 3 | 4 | 5 | 6 | | VI-2 | Gse1 |
| 1269 | 3 | 4 | 5 | 6 | | | VI-2 | Glyat | | 1354 | 3 | 4 | 5 | 6 | | VI-2 | Gsg2 |
| 1270 | 3 | 4 | 5 | 6 | | | VI-2 | Gm10319 | | 1355 | 3 | 4 | 5 | 6 | | VI-2 | Gstt4 |
| 1271 | 3 | 4 | 5 | 6 | | | VI-2 | Gm1045 | | 1356 | 3 | 4 | 5 | 6 | | VI-2 | Gtf2h4 |
| 1272 | 3 | 4 | 5 | 6 | | | VI-2 | Gm10638 | | 1357 | 3 | 4 | 5 | 6 | | VI-2 | Gykl1 |
| 1273 | 3 | 4 | 5 | 6 | | | VI-2 | Gm10785 | | 1358 | 3 | 4 | 5 | 6 | | VI-2 | Gys2 |

Fig. 43 - 9

| | | | | | | | | |
|---|---|---|---|---|---|---|---|---|
| 1359 | 3 | 4 | 5 | 6 | | | VI-2 | H2-Aa |
| 1360 | 3 | 4 | 5 | 6 | | | VI-2 | H2-Ab1 |
| 1361 | 3 | 4 | 5 | 6 | | | VI-2 | H2-DMb2 |
| 1362 | 3 | 4 | 5 | 6 | | | VI-2 | H2-Eb1 |
| 1363 | 3 | 4 | 5 | 6 | | | VI-2 | H2-Eb2 |
| 1364 | 3 | 4 | 5 | 6 | | | VI-2 | H2-Ob |
| 1365 | 3 | 4 | 5 | 6 | | | VI-2 | H2-T24 |
| 1366 | 3 | 4 | 5 | 6 | | | VI-2 | H6pd |
| 1367 | 3 | 4 | 5 | 6 | | | VI-2 | Hadha |
| 1368 | 3 | 4 | 5 | 6 | | | VI-2 | Hadhb |
| 1369 | 3 | 4 | 5 | 6 | | | VI-2 | Hba-a1 |
| 1370 | 3 | 4 | 5 | 6 | | | VI-2 | Hbb-b1 |
| 1371 | 3 | 4 | 5 | 6 | | | VI-2 | Hbb-bt |
| 1372 | 3 | 4 | 5 | 6 | | | VI-2 | Hbq1a |
| 1373 | 3 | 4 | 5 | 6 | | | VI-2 | Hbq1b |
| 1374 | 3 | 4 | 5 | 6 | | | VI-2 | Hdac11 |
| 1375 | 3 | 4 | 5 | 6 | | | VI-2 | Hdac4 |
| 1376 | 3 | 4 | 5 | 6 | | | VI-2 | Hecw2 |
| 1377 | 3 | 4 | 5 | 6 | | | VI-2 | Helz |
| 1378 | 3 | 4 | 5 | 6 | | | VI-2 | Hepacam2 |
| 1379 | 3 | 4 | 5 | 6 | | | VI-2 | Heph |
| 1380 | 3 | 4 | 5 | 6 | | | VI-2 | Herc6 |
| 1381 | 3 | 4 | 5 | 6 | | | VI-2 | Hes5 |
| 1382 | 3 | 4 | 5 | 6 | | | VI-2 | Hgf |
| 1383 | 3 | 4 | 5 | 6 | | | VI-2 | Hhipl1 |
| 1384 | 3 | 4 | 5 | 6 | | | VI-2 | Hist1h2ae |
| 1385 | 3 | 4 | 5 | 6 | | | VI-2 | Hist1h4k |
| 1386 | 3 | 4 | 5 | 6 | | | VI-2 | Hist2h2bb |
| 1387 | 3 | 4 | 5 | 6 | | | VI-2 | Hist2h4 |
| 1388 | 3 | 4 | 5 | 6 | | | VI-2 | Hist3h2a |
| 1389 | 3 | 4 | 5 | 6 | | | VI-2 | Hist3h2ba |
| 1390 | 3 | 4 | 5 | 6 | | | VI-2 | Hivep2 |
| 1391 | 3 | 4 | 5 | 6 | | | VI-2 | Hmga1 |
| 1392 | 3 | 4 | 5 | 6 | | | VI-2 | Hmgcs2 |
| 1393 | 3 | 4 | 5 | 6 | | | VI-2 | Hnf4a |
| 1394 | 3 | 4 | 5 | 6 | | | VI-2 | Hoxb6 |
| 1395 | 3 | 4 | 5 | 6 | | | VI-2 | Hoxb8 |
| 1396 | 3 | 4 | 5 | 6 | | | VI-2 | Hoxc6 |
| 1397 | 3 | 4 | 5 | 6 | | | VI-2 | Hoxd3 |
| 1398 | 3 | 4 | 5 | 6 | | | VI-2 | Hrasls5 |
| 1399 | 3 | 4 | 5 | 6 | | | VI-2 | Hscb |
| 1400 | 3 | 4 | 5 | 6 | | | VI-2 | Hsd11 |
| 1401 | 3 | 4 | 5 | 6 | | | VI-2 | Hsfy2 |
| 1402 | 3 | 4 | 5 | 6 | | | VI-2 | Hspa2 |
| 1403 | 3 | 4 | 5 | 6 | | | VI-2 | Hspa4l |
| 1404 | 3 | 4 | 5 | 6 | | | VI-2 | Hspa8 |
| 1405 | 3 | 4 | 5 | 6 | | | VI-2 | Hsph1 |
| 1406 | 3 | 4 | 5 | 6 | | | VI-2 | Hyal1 |
| 1407 | 3 | 4 | 5 | 6 | | | VI-2 | Hyi |
| 1408 | 3 | 4 | 5 | 6 | | | VI-2 | Hyls1 |
| 1409 | 3 | 4 | 5 | 6 | | | VI-2 | Id3 |
| 1410 | 3 | 4 | 5 | 6 | | | VI-2 | Ier5l |
| 1411 | 3 | 4 | 5 | 6 | | | VI-2 | Ifi35 |
| 1412 | 3 | 4 | 5 | 6 | | | VI-2 | Ifnlr1 |
| 1413 | 3 | 4 | 5 | 6 | | | VI-2 | Ifrd1 |
| 1414 | 3 | 4 | 5 | 6 | | | VI-2 | Ift172 |
| 1415 | 3 | 4 | 5 | 6 | | | VI-2 | Ift27 |
| 1416 | 3 | 4 | 5 | 6 | | | VI-2 | Ift43 |
| 1417 | 3 | 4 | 5 | 6 | | | VI-2 | Igfbp2 |
| 1418 | 3 | 4 | 5 | 6 | | | VI-2 | Igip |
| 1419 | 3 | 4 | 5 | 6 | | | VI-2 | Igj |
| 1420 | 3 | 4 | 5 | 6 | | | VI-2 | Igsf11 |
| 1421 | 3 | 4 | 5 | 6 | | | VI-2 | Igtp |
| 1422 | 3 | 4 | 5 | 6 | | | VI-2 | Ihh |
| 1423 | 3 | 4 | 5 | 6 | | | VI-2 | Ikzf3 |
| 1424 | 3 | 4 | 5 | 6 | | | VI-2 | Il11 |
| 1425 | 3 | 4 | 5 | 6 | | | VI-2 | Il17d |
| 1426 | 3 | 4 | 5 | 6 | | | VI-2 | Il17rc |
| 1427 | 3 | 4 | 5 | 6 | | | VI-2 | Il17rd |
| 1428 | 3 | 4 | 5 | 6 | | | VI-2 | Il2ra |
| 1429 | 3 | 4 | 5 | 6 | | | VI-2 | Il4 |
| 1430 | 3 | 4 | 5 | 6 | | | VI-2 | Il4i1 |
| 1431 | 3 | 4 | 5 | 6 | | | VI-2 | Il7r |
| 1432 | 3 | 4 | 5 | 6 | | | VI-2 | Impdh1 |
| 1433 | 3 | 4 | 5 | 6 | | | VI-2 | Inha |
| 1434 | 3 | 4 | 5 | 6 | | | VI-2 | Inmt |
| 1435 | 3 | 4 | 5 | 6 | | | VI-2 | Inpp4b |
| 1436 | 3 | 4 | 5 | 6 | | | VI-2 | Inppl1 |
| 1437 | 3 | 4 | 5 | 6 | | | VI-2 | Insl5 |
| 1438 | 3 | 4 | 5 | 6 | | | VI-2 | Ipo7 |
| 1439 | 3 | 4 | 5 | 6 | | | VI-2 | Iqcd |
| 1440 | 3 | 4 | 5 | 6 | | | VI-2 | Iqcf1 |
| 1441 | 3 | 4 | 5 | 6 | | | VI-2 | Iqcf3 |
| 1442 | 3 | 4 | 5 | 6 | | | VI-2 | Iqcf4 |
| 1443 | 3 | 4 | 5 | 6 | | | VI-2 | Iqcf5 |
| 1444 | 3 | 4 | 5 | 6 | | | VI-2 | Iqcg |
| 1445 | 3 | 4 | 5 | 6 | | | VI-2 | Irf2bp1 |
| 1446 | 3 | 4 | 5 | 6 | | | VI-2 | Irf6 |
| 1447 | 3 | 4 | 5 | 6 | | | VI-2 | Irgm2 |
| 1448 | 3 | 4 | 5 | 6 | | | VI-2 | Irs1 |
| 1449 | 3 | 4 | 5 | 6 | | | VI-2 | Irs3 |
| 1450 | 3 | 4 | 5 | 6 | | | VI-2 | Isoc2b |
| 1451 | 3 | 4 | 5 | 6 | | | VI-2 | Itga1 |
| 1452 | 3 | 4 | 5 | 6 | | | VI-2 | Itpka |
| 1453 | 3 | 4 | 5 | 6 | | | VI-2 | Itpripl2 |
| 1454 | 3 | 4 | 5 | 6 | | | VI-2 | Ivd |
| 1455 | 3 | 4 | 5 | 6 | | | VI-2 | Jakmip1 |
| 1456 | 3 | 4 | 5 | 6 | | | VI-2 | Jmjd4 |
| 1457 | 3 | 4 | 5 | 6 | | | VI-2 | Kairn |
| 1458 | 3 | 4 | 5 | 6 | | | VI-2 | Kat6a |
| 1459 | 3 | 4 | 5 | 6 | | | VI-2 | Kat8 |
| 1460 | 3 | 4 | 5 | 6 | | | VI-2 | Katnal1 |
| 1461 | 3 | 4 | 5 | 6 | | | VI-2 | Kazald1 |
| 1462 | 3 | 4 | 5 | 6 | | | VI-2 | Kcna3 |
| 1463 | 3 | 4 | 5 | 6 | | | VI-2 | Kcnb1 |
| 1464 | 3 | 4 | 5 | 6 | | | VI-2 | Kcnh2 |
| 1465 | 3 | 4 | 5 | 6 | | | VI-2 | Kcnj16 |
| 1466 | 3 | 4 | 5 | 6 | | | VI-2 | Kcnk1 |
| 1467 | 3 | 4 | 5 | 6 | | | VI-2 | Kcnmb4os1 |
| 1468 | 3 | 4 | 5 | 6 | | | VI-2 | Kcnq5 |
| 1469 | 3 | 4 | 5 | 6 | | | VI-2 | Kctd15 |
| 1470 | 3 | 4 | 5 | 6 | | | VI-2 | Kctd21 |
| 1471 | 3 | 4 | 5 | 6 | | | VI-2 | Khdc1a |
| 1472 | 3 | 4 | 5 | 6 | | | VI-2 | Khk |
| 1473 | 3 | 4 | 5 | 6 | | | VI-2 | Khnyn |
| 1474 | 3 | 4 | 5 | 6 | | | VI-2 | Kif13b |
| 1475 | 3 | 4 | 5 | 6 | | | VI-2 | Kif3c |
| 1476 | 3 | 4 | 5 | 6 | | | VI-2 | Klc3 |
| 1477 | 3 | 4 | 5 | 6 | | | VI-2 | Kif12 |
| 1478 | 3 | 4 | 5 | 6 | | | VI-2 | Kif16 |
| 1479 | 3 | 4 | 5 | 6 | | | VI-2 | Kif3 |
| 1480 | 3 | 4 | 5 | 6 | | | VI-2 | Kif5 |
| 1481 | 3 | 4 | 5 | 6 | | | VI-2 | Kif9 |
| 1482 | 3 | 4 | 5 | 6 | | | VI-2 | Klhl10 |
| 1483 | 3 | 4 | 5 | 6 | | | VI-2 | Klhl11 |
| 1484 | 3 | 4 | 5 | 6 | | | VI-2 | Klhl14 |
| 1485 | 3 | 4 | 5 | 6 | | | VI-2 | Klhl21 |
| 1486 | 3 | 4 | 5 | 6 | | | VI-2 | Klhl24 |
| 1487 | 3 | 4 | 5 | 6 | | | VI-2 | Klhl28 |
| 1488 | 3 | 4 | 5 | 6 | | | VI-2 | Klk1b11 |
| 1489 | 3 | 4 | 5 | 6 | | | VI-2 | Klk1b24 |
| 1490 | 3 | 4 | 5 | 6 | | | VI-2 | Klk1b7-ps |
| 1491 | 3 | 4 | 5 | 6 | | | VI-2 | Klk1b8 |
| 1492 | 3 | 4 | 5 | 6 | | | VI-2 | Klra18 |
| 1493 | 3 | 4 | 5 | 6 | | | VI-2 | Klra23 |
| 1494 | 3 | 4 | 5 | 6 | | | VI-2 | Klrb1b |
| 1495 | 3 | 4 | 5 | 6 | | | VI-2 | Klre1 |
| 1496 | 3 | 4 | 5 | 6 | | | VI-2 | Kmt2a |
| 1497 | 3 | 4 | 5 | 6 | | | VI-2 | Kmt2d |
| 1498 | 3 | 4 | 5 | 6 | | | VI-2 | Kptn |
| 1499 | 3 | 4 | 5 | 6 | | | VI-2 | Krt18 |
| 1500 | 3 | 4 | 5 | 6 | | | VI-2 | Krt23 |
| 1501 | 3 | 4 | 5 | 6 | | | VI-2 | Krtap3-2 |
| 1502 | 3 | 4 | 5 | 6 | | | VI-2 | Krtap3-3 |
| 1503 | 3 | 4 | 5 | 6 | | | VI-2 | Lace1 |
| 1504 | 3 | 4 | 5 | 6 | | | VI-2 | Lama3 |
| 1505 | 3 | 4 | 5 | 6 | | | VI-2 | Lamc3 |
| 1506 | 3 | 4 | 5 | 6 | | | VI-2 | Lancl3 |
| 1507 | 3 | 4 | 5 | 6 | | | VI-2 | Lat |
| 1508 | 3 | 4 | 5 | 6 | | | VI-2 | Lce3e |
| 1509 | 3 | 4 | 5 | 6 | | | VI-2 | Lck |
| 1510 | 3 | 4 | 5 | 6 | | | VI-2 | Ldlrad1 |
| 1511 | 3 | 4 | 5 | 6 | | | VI-2 | Ldlrad4 |
| 1512 | 3 | 4 | 5 | 6 | | | VI-2 | Lemd2 |
| 1513 | 3 | 4 | 5 | 6 | | | VI-2 | Leprel1 |
| 1514 | 3 | 4 | 5 | 6 | | | VI-2 | Lgals4 |
| 1515 | 3 | 4 | 5 | 6 | | | VI-2 | Lhpp |
| 1516 | 3 | 4 | 5 | 6 | | | VI-2 | Lig4 |
| 1517 | 3 | 4 | 5 | 6 | | | VI-2 | Lipg |
| 1518 | 3 | 4 | 5 | 6 | | | VI-2 | Lmbrd2 |
| 1519 | 3 | 4 | 5 | 6 | | | VI-2 | Lnpep |
| 1520 | 3 | 4 | 5 | 6 | | | VI-2 | LOC100503676 |
| 1521 | 3 | 4 | 5 | 6 | | | VI-2 | Loxl4 |
| 1522 | 3 | 4 | 5 | 6 | | | VI-2 | Lpar6 |
| 1523 | 3 | 4 | 5 | 6 | | | VI-2 | Lpcat1 |
| 1524 | 3 | 4 | 5 | 6 | | | VI-2 | Lpcat3 |
| 1525 | 3 | 4 | 5 | 6 | | | VI-2 | Lphn3 |
| 1526 | 3 | 4 | 5 | 6 | | | VI-2 | Lrat |
| 1527 | 3 | 4 | 5 | 6 | | | VI-2 | Lrfn3 |
| 1528 | 3 | 4 | 5 | 6 | | | VI-2 | Lrp2 |

Fig. 43 - 10

| | | | | | | | | |
|---|---|---|---|---|---|---|---|---|
| 1529 | 3 | 4 | 5 | 6 | | VI-2 | Lrrc23 |
| 1530 | 3 | 4 | 5 | 6 | | VI-2 | Lrrc4 |
| 1531 | 3 | 4 | 5 | 6 | | VI-2 | Lrrc43 |
| 1532 | 3 | 4 | 5 | 6 | | VI-2 | Lrrc51 |
| 1533 | 3 | 4 | 5 | 6 | | VI-2 | Lrrc71 |
| 1534 | 3 | 4 | 5 | 6 | | VI-2 | Lrrc75a |
| 1535 | 3 | 4 | 5 | 6 | | VI-2 | Ltbp4 |
| 1536 | 3 | 4 | 5 | 6 | | VI-2 | Ly6d |
| 1537 | 3 | 4 | 5 | 6 | | VI-2 | Ly6g6f |
| 1538 | 3 | 4 | 5 | 6 | | VI-2 | Lypd4 |
| 1539 | 3 | 4 | 5 | 6 | | VI-2 | Lypd8 |
| 1540 | 3 | 4 | 5 | 6 | | VI-2 | Lyst |
| 1541 | 3 | 4 | 5 | 6 | | VI-2 | Mad1l1 |
| 1542 | 3 | 4 | 5 | 6 | | VI-2 | Mael |
| 1543 | 3 | 4 | 5 | 6 | | VI-2 | Maf1 |
| 1544 | 3 | 4 | 5 | 6 | | VI-2 | Maff |
| 1545 | 3 | 4 | 5 | 6 | | VI-2 | Mafg |
| 1546 | 3 | 4 | 5 | 6 | | VI-2 | Mageb2 |
| 1547 | 3 | 4 | 5 | 6 | | VI-2 | Mamld1 |
| 1548 | 3 | 4 | 5 | 6 | | VI-2 | Man2c1os |
| 1549 | 3 | 4 | 5 | 6 | | VI-2 | Map1a |
| 1550 | 3 | 4 | 5 | 6 | | VI-2 | Map3k19 |
| 1551 | 3 | 4 | 5 | 6 | | VI-2 | Mapk11 |
| 1552 | 3 | 4 | 5 | 6 | | VI-2 | March10 |
| 1553 | 3 | 4 | 5 | 6 | | VI-2 | March11 |
| 1554 | 3 | 4 | 5 | 6 | | VI-2 | March3 |
| 1555 | 3 | 4 | 5 | 6 | | VI-2 | Marcksl1-ps4 |
| 1556 | 3 | 4 | 5 | 6 | | VI-2 | Marveld3 |
| 1557 | 3 | 4 | 5 | 6 | | VI-2 | Mast1 |
| 1558 | 3 | 4 | 5 | 6 | | VI-2 | Mast4 |
| 1559 | 3 | 4 | 5 | 6 | | VI-2 | Mau2 |
| 1560 | 3 | 4 | 5 | 6 | | VI-2 | Maz |
| 1561 | 3 | 4 | 5 | 6 | | VI-2 | Mbd1 |
| 1562 | 3 | 4 | 5 | 6 | | VI-2 | Mbd5 |
| 1563 | 3 | 4 | 5 | 6 | | VI-2 | Mboat1 |
| 1564 | 3 | 4 | 5 | 6 | | VI-2 | Mboat2 |
| 1565 | 3 | 4 | 5 | 6 | | VI-2 | Mcc |
| 1566 | 3 | 4 | 5 | 6 | | VI-2 | Mcoin2 |
| 1567 | 3 | 4 | 5 | 6 | | VI-2 | Mcoin3 |
| 1568 | 3 | 4 | 5 | 6 | | VI-2 | Med12 |
| 1569 | 3 | 4 | 5 | 6 | | VI-2 | Medag |
| 1570 | 3 | 4 | 5 | 6 | | VI-2 | Mertk |
| 1571 | 3 | 4 | 5 | 6 | | VI-2 | Mettl1 |
| 1572 | 3 | 4 | 5 | 6 | | VI-2 | Mettl23 |
| 1573 | 3 | 4 | 5 | 6 | | VI-2 | Mettl4 |
| 1574 | 3 | 4 | 5 | 6 | | VI-2 | Mettl5 |
| 1575 | 3 | 4 | 5 | 6 | | VI-2 | Mettl7a3 |
| 1576 | 3 | 4 | 5 | 6 | | VI-2 | Mettl8 |
| 1577 | 3 | 4 | 5 | 6 | | VI-2 | Mfap3l |
| 1578 | 3 | 4 | 5 | 6 | | VI-2 | Mfsd11 |
| 1579 | 3 | 4 | 5 | 6 | | VI-2 | Mgat5 |
| 1580 | 3 | 4 | 5 | 6 | | VI-2 | Mgst2 |
| 1581 | 3 | 4 | 5 | 6 | | VI-2 | Mid1 |
| 1582 | 3 | 4 | 5 | 6 | | VI-2 | Mif4gd |
| 1583 | 3 | 4 | 5 | 6 | | VI-2 | Mki67 |
| 1584 | 3 | 4 | 5 | 6 | | VI-2 | Mlph |
| 1585 | 3 | 4 | 5 | 6 | | VI-2 | Mlycd |
| 1586 | 3 | 4 | 5 | 6 | | VI-2 | Mmp10 |
| 1587 | 3 | 4 | 5 | 6 | | VI-2 | Mmp15 |
| 1588 | 3 | 4 | 5 | 6 | | VI-2 | Mmp28 |
| 1589 | 3 | 4 | 5 | 6 | | VI-2 | Mmp3 |
| 1590 | 3 | 4 | 5 | 6 | | VI-2 | Mmp7 |
| 1591 | 3 | 4 | 5 | 6 | | VI-2 | Mocs3 |
| 1592 | 3 | 4 | 5 | 6 | | VI-2 | Morn5 |
| 1593 | 3 | 4 | 5 | 6 | | VI-2 | Mospd4 |
| 1594 | 3 | 4 | 5 | 6 | | VI-2 | Mpp7 |
| 1595 | 3 | 4 | 5 | 6 | | VI-2 | Mrgpre |
| 1596 | 3 | 4 | 5 | 6 | | VI-2 | Mrgprg |
| 1597 | 3 | 4 | 5 | 6 | | VI-2 | Mrpl24 |
| 1598 | 3 | 4 | 5 | 6 | | VI-2 | Mrpl38 |
| 1599 | 3 | 4 | 5 | 6 | | VI-2 | Mrps6 |
| 1600 | 3 | 4 | 5 | 6 | | VI-2 | Ms4a1 |
| 1601 | 3 | 4 | 5 | 6 | | VI-2 | Msc |
| 1602 | 3 | 4 | 5 | 6 | | VI-2 | Mt3 |
| 1603 | 3 | 4 | 5 | 6 | | VI-2 | Mtss1 |
| 1604 | 3 | 4 | 5 | 6 | | VI-2 | Mturn |
| 1605 | 3 | 4 | 5 | 6 | | VI-2 | Muc2 |
| 1606 | 3 | 4 | 5 | 6 | | VI-2 | Muc4 |
| 1607 | 3 | 4 | 5 | 6 | | VI-2 | Muc5b |
| 1608 | 3 | 4 | 5 | 6 | | VI-2 | Mug1 |
| 1609 | 3 | 4 | 5 | 6 | | VI-2 | Mug2 |
| 1610 | 3 | 4 | 5 | 6 | | VI-2 | Mum1l1 |
| 1611 | 3 | 4 | 5 | 6 | | VI-2 | Mup11 |
| 1612 | 3 | 4 | 5 | 6 | | VI-2 | Mup3 |
| 1613 | 3 | 4 | 5 | 6 | | VI-2 | Mustn1 |
| 1614 | 3 | 4 | 5 | 6 | | VI-2 | Mxd4 |
| 1615 | 3 | 4 | 5 | 6 | | VI-2 | Myb |
| 1616 | 3 | 4 | 5 | 6 | | VI-2 | Myc |
| 1617 | 3 | 4 | 5 | 6 | | VI-2 | Mycbpap |
| 1618 | 3 | 4 | 5 | 6 | | VI-2 | Mycl |
| 1619 | 3 | 4 | 5 | 6 | | VI-2 | Myct1 |
| 1620 | 3 | 4 | 5 | 6 | | VI-2 | Mvg1 |
| 1621 | 3 | 4 | 5 | 6 | | VI-2 | Myl10 |
| 1622 | 3 | 4 | 5 | 6 | | VI-2 | Mylk3 |
| 1623 | 3 | 4 | 5 | 6 | | VI-2 | Myo1e |
| 1624 | 3 | 4 | 5 | 6 | | VI-2 | Myzap |
| 1625 | 3 | 4 | 5 | 6 | | VI-2 | N4bp2 |
| 1626 | 3 | 4 | 5 | 6 | | VI-2 | N4bp3 |
| 1627 | 3 | 4 | 5 | 6 | | VI-2 | Nat9 |
| 1628 | 3 | 4 | 5 | 6 | | VI-2 | Nav1 |
| 1629 | 3 | 4 | 5 | 6 | | VI-2 | Nbeal1 |
| 1630 | 3 | 4 | 5 | 6 | | VI-2 | Ncln |
| 1631 | 3 | 4 | 5 | 6 | | VI-2 | Ndufa7 |
| 1632 | 3 | 4 | 5 | 6 | | VI-2 | Ndufaf6 |
| 1633 | 3 | 4 | 5 | 6 | | VI-2 | Nebl |
| 1634 | 3 | 4 | 5 | 6 | | VI-2 | Neil2 |
| 1635 | 3 | 4 | 5 | 6 | | VI-2 | Nek3 |
| 1636 | 3 | 4 | 5 | 6 | | VI-2 | Neto2 |
| 1637 | 3 | 4 | 5 | 6 | | VI-2 | Nfatc3 |
| 1638 | 3 | 4 | 5 | 6 | | VI-2 | Nfkbil1 |
| 1639 | 3 | 4 | 5 | 6 | | VI-2 | Ngef |
| 1640 | 3 | 4 | 5 | 6 | | VI-2 | Nhlrc2 |
| 1641 | 3 | 4 | 5 | 6 | | VI-2 | Nhlrc3 |
| 1642 | 3 | 4 | 5 | 6 | | VI-2 | Nhsl2 |
| 1643 | 3 | 4 | 5 | 6 | | VI-2 | Nim1k |
| 1644 | 3 | 4 | 5 | 6 | | VI-2 | Nit2 |
| 1645 | 3 | 4 | 5 | 6 | | VI-2 | Nkd2 |
| 1646 | 3 | 4 | 5 | 6 | | VI-2 | Nlrp12 |
| 1647 | 3 | 4 | 5 | 6 | | VI-2 | Nmd3 |
| 1648 | 3 | 4 | 5 | 6 | | VI-2 | Nme5 |
| 1649 | 3 | 4 | 5 | 6 | | VI-2 | Nnat |
| 1650 | 3 | 4 | 5 | 6 | | VI-2 | Notum |
| 1651 | 3 | 4 | 5 | 6 | | VI-2 | Npff |
| 1652 | 3 | 4 | 5 | 6 | | VI-2 | Npm1 |
| 1653 | 3 | 4 | 5 | 6 | | VI-2 | Npm3 |
| 1654 | 3 | 4 | 5 | 6 | | VI-2 | Nr1h4 |
| 1655 | 3 | 4 | 5 | 6 | | VI-2 | Nr3c2 |
| 1656 | 3 | 4 | 5 | 6 | | VI-2 | Nr4a1 |
| 1657 | 3 | 4 | 5 | 6 | | VI-2 | Nrn1l |
| 1658 | 3 | 4 | 5 | 6 | | VI-2 | Nron |
| 1659 | 3 | 4 | 5 | 6 | | VI-2 | Nsun5 |
| 1660 | 3 | 4 | 5 | 6 | | VI-2 | Nt5c1b |
| 1661 | 3 | 4 | 5 | 6 | | VI-2 | Ntf3 |
| 1662 | 3 | 4 | 5 | 6 | | VI-2 | Nthl1 |
| 1663 | 3 | 4 | 5 | 6 | | VI-2 | Ntn1 |
| 1664 | 3 | 4 | 5 | 6 | | VI-2 | Ntn4 |
| 1665 | 3 | 4 | 5 | 6 | | VI-2 | Ntrk2 |
| 1666 | 3 | 4 | 5 | 6 | | VI-2 | Ntrk3 |
| 1667 | 3 | 4 | 5 | 6 | | VI-2 | Nudt12 |
| 1668 | 3 | 4 | 5 | 6 | | VI-2 | Nupr1 |
| 1669 | 3 | 4 | 5 | 6 | | VI-2 | Nutf2 |
| 1670 | 3 | 4 | 5 | 6 | | VI-2 | Nwd1 |
| 1671 | 3 | 4 | 5 | 6 | | VI-2 | Nxnl1 |
| 1672 | 3 | 4 | 5 | 6 | | VI-2 | Nxt1 |
| 1673 | 3 | 4 | 5 | 6 | | VI-2 | Nyap1 |
| 1674 | 3 | 4 | 5 | 6 | | VI-2 | Oas1b |
| 1675 | 3 | 4 | 5 | 6 | | VI-2 | Odf3b |
| 1676 | 3 | 4 | 5 | 6 | | VI-2 | Ogfod2 |
| 1677 | 3 | 4 | 5 | 6 | | VI-2 | Olfr1034 |
| 1678 | 3 | 4 | 5 | 6 | | VI-2 | Olfr164 |
| 1679 | 3 | 4 | 5 | 6 | | VI-2 | Olig3 |
| 1680 | 3 | 4 | 5 | 6 | | VI-2 | Omd |
| 1681 | 3 | 4 | 5 | 6 | | VI-2 | Opn3 |
| 1682 | 3 | 4 | 5 | 6 | | VI-2 | Ormdl2 |
| 1683 | 3 | 4 | 5 | 6 | | VI-2 | Osmr |
| 1684 | 3 | 4 | 5 | 6 | | VI-2 | Otub2 |
| 1685 | 3 | 4 | 5 | 6 | | VI-2 | Ovca2 |
| 1686 | 3 | 4 | 5 | 6 | | VI-2 | Ovol1 |
| 1687 | 3 | 4 | 5 | 6 | | VI-2 | P2rx1 |
| 1688 | 3 | 4 | 5 | 6 | | VI-2 | P2rx3 |
| 1689 | 3 | 4 | 5 | 6 | | VI-2 | P2rx4 |
| 1690 | 3 | 4 | 5 | 6 | | VI-2 | P2ry10 |
| 1691 | 3 | 4 | 5 | 6 | | VI-2 | Pabpc2 |
| 1692 | 3 | 4 | 5 | 6 | | VI-2 | Pacrg |
| 1693 | 3 | 4 | 5 | 6 | | VI-2 | Pacsin1 |
| 1694 | 3 | 4 | 5 | 6 | | VI-2 | Pafah1b3 |
| 1695 | 3 | 4 | 5 | 6 | | VI-2 | Pappa |
| 1696 | 3 | 4 | 5 | 6 | | VI-2 | Paqr3 |
| 1697 | 3 | 4 | 5 | 6 | | VI-2 | Parn |
| 1698 | 3 | 4 | 5 | 6 | | VI-2 | Parp14 |

Fig. 43 - 11

| | | | | | | | | |
|---|---|---|---|---|---|---|---|---|
| 1699 | 3 | 4 | 5 | 6 | | VI-2 | Pate2 |
| 1700 | 3 | 4 | 5 | 6 | | VI-2 | Pax5 |
| 1701 | 3 | 4 | 5 | 6 | | VI-2 | Pax8 |
| 1702 | 3 | 4 | 5 | 6 | | VI-2 | Pbld1 |
| 1703 | 3 | 4 | 5 | 6 | | VI-2 | Pcdh12 |
| 1704 | 3 | 4 | 5 | 6 | | VI-2 | Pcdh17 |
| 1705 | 3 | 4 | 5 | 6 | | VI-2 | Pcdhac2 |
| 1706 | 3 | 4 | 5 | 6 | | VI-2 | Pcgf3 |
| 1707 | 3 | 4 | 5 | 6 | | VI-2 | Pcx |
| 1708 | 3 | 4 | 5 | 6 | | VI-2 | Pdcd1 |
| 1709 | 3 | 4 | 5 | 6 | | VI-2 | Pdcd2 |
| 1710 | 3 | 4 | 5 | 6 | | VI-2 | Pdcd2l |
| 1711 | 3 | 4 | 5 | 6 | | VI-2 | Pdcl2 |
| 1712 | 3 | 4 | 5 | 6 | | VI-2 | Pddc1 |
| 1713 | 3 | 4 | 5 | 6 | | VI-2 | Pde3a |
| 1714 | 3 | 4 | 5 | 6 | | VI-2 | Pdgfd |
| 1715 | 3 | 4 | 5 | 6 | | VI-2 | Pdk2 |
| 1716 | 3 | 4 | 5 | 6 | | VI-2 | Pdp2 |
| 1717 | 3 | 4 | 5 | 6 | | VI-2 | Pds5a |
| 1718 | 3 | 4 | 5 | 6 | | VI-2 | Pdzd2 |
| 1719 | 3 | 4 | 5 | 6 | | VI-2 | Pdzd4 |
| 1720 | 3 | 4 | 5 | 6 | | VI-2 | Pdzd7 |
| 1721 | 3 | 4 | 5 | 6 | | VI-2 | Pdzk1 |
| 1722 | 3 | 4 | 5 | 6 | | VI-2 | Peak1 |
| 1723 | 3 | 4 | 5 | 6 | | VI-2 | Peli3 |
| 1724 | 3 | 4 | 5 | 6 | | VI-2 | Pex13 |
| 1725 | 3 | 4 | 5 | 6 | | VI-2 | Pggt1b |
| 1726 | 3 | 4 | 5 | 6 | | VI-2 | Pgm2l1 |
| 1727 | 3 | 4 | 5 | 6 | | VI-2 | Phf11c |
| 1728 | 3 | 4 | 5 | 6 | | VI-2 | Phgdh |
| 1729 | 3 | 4 | 5 | 6 | | VI-2 | Phldb3 |
| 1730 | 3 | 4 | 5 | 6 | | VI-2 | Phyhipl |
| 1731 | 3 | 4 | 5 | 6 | | VI-2 | Piezo1 |
| 1732 | 3 | 4 | 5 | 6 | | VI-2 | Piezo2 |
| 1733 | 3 | 4 | 5 | 6 | | VI-2 | Pigf |
| 1734 | 3 | 4 | 5 | 6 | | VI-2 | Pigyl |
| 1735 | 3 | 4 | 5 | 6 | | VI-2 | Pim2 |
| 1736 | 3 | 4 | 5 | 6 | | VI-2 | Pipox |
| 1737 | 3 | 4 | 5 | 6 | | VI-2 | Pithd1 |
| 1738 | 3 | 4 | 5 | 6 | | VI-2 | Pkd1 |
| 1739 | 3 | 4 | 5 | 6 | | VI-2 | Plag1 |
| 1740 | 3 | 4 | 5 | 6 | | VI-2 | Plau |
| 1741 | 3 | 4 | 5 | 6 | | VI-2 | Plcb4 |
| 1742 | 3 | 4 | 5 | 6 | | VI-2 | Plcg1 |
| 1743 | 3 | 4 | 5 | 6 | | VI-2 | Plcl1 |
| 1744 | 3 | 4 | 5 | 6 | | VI-2 | Plekha5 |
| 1745 | 3 | 4 | 5 | 6 | | VI-2 | Plekhh3 |
| 1746 | 3 | 4 | 5 | 6 | | VI-2 | Plekhm3 |
| 1747 | 3 | 4 | 5 | 6 | | VI-2 | Plet1 |
| 1748 | 3 | 4 | 5 | 6 | | VI-2 | Plet1os |
| 1749 | 3 | 4 | 5 | 6 | | VI-2 | Plin5 |
| 1750 | 3 | 4 | 5 | 6 | | VI-2 | Pln |
| 1751 | 3 | 4 | 5 | 6 | | VI-2 | Plxnd1 |
| 1752 | 3 | 4 | 5 | 6 | | VI-2 | Pnpla7 |
| 1753 | 3 | 4 | 5 | 6 | | VI-2 | Pogk |
| 1754 | 3 | 4 | 5 | 6 | | VI-2 | Poll |
| 1755 | 3 | 4 | 5 | 6 | | VI-2 | Polr2e |
| 1756 | 3 | 4 | 5 | 6 | | VI-2 | Polr2g |
| 1757 | 3 | 4 | 5 | 6 | | VI-2 | Polr2i |
| 1758 | 3 | 4 | 5 | 6 | | VI-2 | Polr3gl |
| 1759 | 3 | 4 | 5 | 6 | | VI-2 | Pomc |
| 1760 | 3 | 4 | 5 | 6 | | VI-2 | Pomgnt2 |
| 1761 | 3 | 4 | 5 | 6 | | VI-2 | Pou2af1 |
| 1762 | 3 | 4 | 5 | 6 | | VI-2 | Pou2f2 |
| 1763 | 3 | 4 | 5 | 6 | | VI-2 | Pou3f3 |
| 1764 | 3 | 4 | 5 | 6 | | VI-2 | Ppil3 |
| 1765 | 3 | 4 | 5 | 6 | | VI-2 | Ppm1e |
| 1766 | 3 | 4 | 5 | 6 | | VI-2 | Ppm1l |
| 1767 | 3 | 4 | 5 | 6 | | VI-2 | Ppp1r12a |
| 1768 | 3 | 4 | 5 | 6 | | VI-2 | Ppp1r13l |
| 1769 | 3 | 4 | 5 | 6 | | VI-2 | Ppp1r14a |
| 1770 | 3 | 4 | 5 | 6 | | VI-2 | Ppp1r16a |
| 1771 | 3 | 4 | 5 | 6 | | VI-2 | Ppp1r16b |
| 1772 | 3 | 4 | 5 | 6 | | VI-2 | Ppp1r1b |
| 1773 | 3 | 4 | 5 | 6 | | VI-2 | Ppp2r2b |
| 1774 | 3 | 4 | 5 | 6 | | VI-2 | Ppp3r2 |
| 1775 | 3 | 4 | 5 | 6 | | VI-2 | Ppy |
| 1776 | 3 | 4 | 5 | 6 | | VI-2 | Prdm1 |
| 1777 | 3 | 4 | 5 | 6 | | VI-2 | Prickle1 |
| 1778 | 3 | 4 | 5 | 6 | | VI-2 | Prickle4 |
| 1779 | 3 | 4 | 5 | 6 | | VI-2 | Prkcg |
| 1780 | 3 | 4 | 5 | 6 | | VI-2 | Prl |
| 1781 | 3 | 4 | 5 | 6 | | VI-2 | Prmt3 |
| 1782 | 3 | 4 | 5 | 6 | | VI-2 | Prodh |
| 1783 | 3 | 4 | 5 | 6 | | VI-2 | Prodh2 |

| | | | | | | | | |
|---|---|---|---|---|---|---|---|---|
| 1784 | 3 | 4 | 5 | 6 | | VI-2 | Prom1 |
| 1785 | 3 | 4 | 5 | 6 | | VI-2 | Proz |
| 1786 | 3 | 4 | 5 | 6 | | VI-2 | Prpf4b |
| 1787 | 3 | 4 | 5 | 6 | | VI-2 | Prps1l1 |
| 1788 | 3 | 4 | 5 | 6 | | VI-2 | Prr15l |
| 1789 | 3 | 4 | 5 | 6 | | VI-2 | Prr30 |
| 1790 | 3 | 4 | 5 | 6 | | VI-2 | Prr5 |
| 1791 | 3 | 4 | 5 | 6 | | VI-2 | Prrc2a |
| 1792 | 3 | 4 | 5 | 6 | | VI-2 | Prrt1 |
| 1793 | 3 | 4 | 5 | 6 | | VI-2 | Prrt2 |
| 1794 | 3 | 4 | 5 | 6 | | VI-2 | Prss39 |
| 1795 | 3 | 4 | 5 | 6 | | VI-2 | Prss53 |
| 1796 | 3 | 4 | 5 | 6 | | VI-2 | Prss8 |
| 1797 | 3 | 4 | 5 | 6 | | VI-2 | Psca |
| 1798 | 3 | 4 | 5 | 6 | | VI-2 | Psmd5 |
| 1799 | 3 | 4 | 5 | 6 | | VI-2 | Ptch1 |
| 1800 | 3 | 4 | 5 | 6 | | VI-2 | Ptdss2 |
| 1801 | 3 | 4 | 5 | 6 | | VI-2 | Ptov1 |
| 1802 | 3 | 4 | 5 | 6 | | VI-2 | Ptprb |
| 1803 | 3 | 4 | 5 | 6 | | VI-2 | Ptpro |
| 1804 | 3 | 4 | 5 | 6 | | VI-2 | Ptrh1 |
| 1805 | 3 | 4 | 5 | 6 | | VI-2 | Pts |
| 1806 | 3 | 4 | 5 | 6 | | VI-2 | Pwwp2b |
| 1807 | 3 | 4 | 5 | 6 | | VI-2 | Pyy |
| 1808 | 3 | 4 | 5 | 6 | | VI-2 | Rab11fip4 |
| 1809 | 3 | 4 | 5 | 6 | | VI-2 | Rab17 |
| 1810 | 3 | 4 | 5 | 6 | | VI-2 | Rab25 |
| 1811 | 3 | 4 | 5 | 6 | | VI-2 | Rab26os |
| 1812 | 3 | 4 | 5 | 6 | | VI-2 | Rab3a |
| 1813 | 3 | 4 | 5 | 6 | | VI-2 | Rab6b |
| 1814 | 3 | 4 | 5 | 6 | | VI-2 | Rab9 |
| 1815 | 3 | 4 | 5 | 6 | | VI-2 | Rabl2 |
| 1816 | 3 | 4 | 5 | 6 | | VI-2 | Rad52 |
| 1817 | 3 | 4 | 5 | 6 | | VI-2 | Ralgps2 |
| 1818 | 3 | 4 | 5 | 6 | | VI-2 | Ramp2 |
| 1819 | 3 | 4 | 5 | 6 | | VI-2 | Rapgef1 |
| 1820 | 3 | 4 | 5 | 6 | | VI-2 | Raph1 |
| 1821 | 3 | 4 | 5 | 6 | | VI-2 | Rasal2 |
| 1822 | 3 | 4 | 5 | 6 | | VI-2 | Rasgrp1 |
| 1823 | 3 | 4 | 5 | 6 | | VI-2 | Rasgrp2 |
| 1824 | 3 | 4 | 5 | 6 | | VI-2 | Rassf7 |
| 1825 | 3 | 4 | 5 | 6 | | VI-2 | Rassf8 |
| 1826 | 3 | 4 | 5 | 6 | | VI-2 | Rbm12b2 |
| 1827 | 3 | 4 | 5 | 6 | | VI-2 | Rbm15 |
| 1828 | 3 | 4 | 5 | 6 | | VI-2 | Rbm4 |
| 1829 | 3 | 4 | 5 | 6 | | VI-2 | Rbm8a |
| 1830 | 3 | 4 | 5 | 6 | | VI-2 | Rbp2 |
| 1831 | 3 | 4 | 5 | 6 | | VI-2 | Rbp7 |
| 1832 | 3 | 4 | 5 | 6 | | VI-2 | Rcor1 |
| 1833 | 3 | 4 | 5 | 6 | | VI-2 | Rcsd1 |
| 1834 | 3 | 4 | 5 | 6 | | VI-2 | Rdh5 |
| 1835 | 3 | 4 | 5 | 6 | | VI-2 | Rel |
| 1836 | 3 | 4 | 5 | 6 | | VI-2 | Rem1 |
| 1837 | 3 | 4 | 5 | 6 | | VI-2 | Resp18 |
| 1838 | 3 | 4 | 5 | 6 | | VI-2 | Rest |
| 1839 | 3 | 4 | 5 | 6 | | VI-2 | Retnla |
| 1840 | 3 | 4 | 5 | 6 | | VI-2 | Rfc2 |
| 1841 | 3 | 4 | 5 | 6 | | VI-2 | Rgs13 |
| 1842 | 3 | 4 | 5 | 6 | | VI-2 | Rgs16 |
| 1843 | 3 | 4 | 5 | 6 | | VI-2 | Rhbdl1 |
| 1844 | 3 | 4 | 5 | 6 | | VI-2 | Rhoh |
| 1845 | 3 | 4 | 5 | 6 | | VI-2 | Rhox5 |
| 1846 | 3 | 4 | 5 | 6 | | VI-2 | Ring1 |
| 1847 | 3 | 4 | 5 | 6 | | VI-2 | Ritpr |
| 1848 | 3 | 4 | 5 | 6 | | VI-2 | Rmdn2 |
| 1849 | 3 | 4 | 5 | 6 | | VI-2 | Rmnd1 |
| 1850 | 3 | 4 | 5 | 6 | | VI-2 | Rmnd5a |
| 1851 | 3 | 4 | 5 | 6 | | VI-2 | Rnf122 |
| 1852 | 3 | 4 | 5 | 6 | | VI-2 | Rnf125 |
| 1853 | 3 | 4 | 5 | 6 | | VI-2 | Rnf133 |
| 1854 | 3 | 4 | 5 | 6 | | VI-2 | Rnf141 |
| 1855 | 3 | 4 | 5 | 6 | | VI-2 | Rnf151 |
| 1856 | 3 | 4 | 5 | 6 | | VI-2 | Rnf32 |
| 1857 | 3 | 4 | 5 | 6 | | VI-2 | Rnpep |
| 1858 | 3 | 4 | 5 | 6 | | VI-2 | Rnpepl1 |
| 1859 | 3 | 4 | 5 | 6 | | VI-2 | Ropn1 |
| 1860 | 3 | 4 | 5 | 6 | | VI-2 | Rorc |
| 1861 | 3 | 4 | 5 | 6 | | VI-2 | Rpgrip1 |
| 1862 | 3 | 4 | 5 | 6 | | VI-2 | Rpl10l |
| 1863 | 3 | 4 | 5 | 6 | | VI-2 | Rpl24 |
| 1864 | 3 | 4 | 5 | 6 | | VI-2 | Rpl28 |
| 1865 | 3 | 4 | 5 | 6 | | VI-2 | Rpl35a |
| 1866 | 3 | 4 | 5 | 6 | | VI-2 | Rpl36 |
| 1867 | 3 | 4 | 5 | 6 | | VI-2 | Rpl37 |
| 1868 | 3 | 4 | 5 | 6 | | VI-2 | Rpl37a |

Fig. 43 - 12

| | | | | | | | |
|---|---|---|---|---|---|---|---|
| 1869 | 3 | 4 | 5 | 6 | VI-2 | Rpl38 |
| 1870 | 3 | 4 | 5 | 6 | VI-2 | Rpl39l |
| 1871 | 3 | 4 | 5 | 6 | VI-2 | Rpl9 |
| 1872 | 3 | 4 | 5 | 6 | VI-2 | Rplp2 |
| 1873 | 3 | 4 | 5 | 6 | VI-2 | Rpp21 |
| 1874 | 3 | 4 | 5 | 6 | VI-2 | Rpp38 |
| 1875 | 3 | 4 | 5 | 6 | VI-2 | Rprml |
| 1876 | 3 | 4 | 5 | 6 | VI-2 | Rps12 |
| 1877 | 3 | 4 | 5 | 6 | VI-2 | Rps17 |
| 1878 | 3 | 4 | 5 | 6 | VI-2 | Rps28 |
| 1879 | 3 | 4 | 5 | 6 | VI-2 | Rps4l |
| 1880 | 3 | 4 | 5 | 6 | VI-2 | Rptoros |
| 1881 | 3 | 4 | 5 | 6 | VI-2 | Rpusd4 |
| 1882 | 3 | 4 | 5 | 6 | VI-2 | Rsad2 |
| 1883 | 3 | 4 | 5 | 6 | VI-2 | Rsc1a1 |
| 1884 | 3 | 4 | 5 | 6 | VI-2 | Rslcan18 |
| 1885 | 3 | 4 | 5 | 6 | VI-2 | Rsph4a |
| 1886 | 3 | 4 | 5 | 6 | VI-2 | Rsph9 |
| 1887 | 3 | 4 | 5 | 6 | VI-2 | Rtp3 |
| 1888 | 3 | 4 | 5 | 6 | VI-2 | Rufy1 |
| 1889 | 3 | 4 | 5 | 6 | VI-2 | Rufy4 |
| 1890 | 3 | 4 | 5 | 6 | VI-2 | Rundc3a |
| 1891 | 3 | 4 | 5 | 6 | VI-2 | Rusc1 |
| 1892 | 3 | 4 | 5 | 6 | VI-2 | Rwdd3 |
| 1893 | 3 | 4 | 5 | 6 | VI-2 | Rxrb |
| 1894 | 3 | 4 | 5 | 6 | VI-2 | S100a13 |
| 1895 | 3 | 4 | 5 | 6 | VI-2 | S100a2 |
| 1896 | 3 | 4 | 5 | 6 | VI-2 | S100pbp |
| 1897 | 3 | 4 | 5 | 6 | VI-2 | S1pr1 |
| 1898 | 3 | 4 | 5 | 6 | VI-2 | Samd1 |
| 1899 | 3 | 4 | 5 | 6 | VI-2 | Samd11 |
| 1900 | 3 | 4 | 5 | 6 | VI-2 | Samd5 |
| 1901 | 3 | 4 | 5 | 6 | VI-2 | Satb1 |
| 1902 | 3 | 4 | 5 | 6 | VI-2 | Saysd1 |
| 1903 | 3 | 4 | 5 | 6 | VI-2 | Shk1 |
| 1904 | 3 | 4 | 5 | 6 | VI-2 | Scd3 |
| 1905 | 3 | 4 | 5 | 6 | VI-2 | Scg2 |
| 1906 | 3 | 4 | 5 | 6 | VI-2 | Scin |
| 1907 | 3 | 4 | 5 | 6 | VI-2 | Sco2 |
| 1908 | 3 | 4 | 5 | 6 | VI-2 | Scp2d1 |
| 1909 | 3 | 4 | 5 | 6 | VI-2 | Scube2 |
| 1910 | 3 | 4 | 5 | 6 | VI-2 | Sdc4 |
| 1911 | 3 | 4 | 5 | 6 | VI-2 | Sdf2 |
| 1912 | 3 | 4 | 5 | 6 | VI-2 | Sectm1b |
| 1913 | 3 | 4 | 5 | 6 | VI-2 | Selo |
| 1914 | 3 | 4 | 5 | 6 | VI-2 | Sema5a |
| 1915 | 3 | 4 | 5 | 6 | VI-2 | Sept1 |
| 1916 | 3 | 4 | 5 | 6 | VI-2 | Serf1 |
| 1917 | 3 | 4 | 5 | 6 | VI-2 | Serinc5 |
| 1918 | 3 | 4 | 5 | 6 | VI-2 | Serpina1a |
| 1919 | 3 | 4 | 5 | 6 | VI-2 | Serpina1c |
| 1920 | 3 | 4 | 5 | 6 | VI-2 | Serpina1d |
| 1921 | 3 | 4 | 5 | 6 | VI-2 | Serpina1e |
| 1922 | 3 | 4 | 5 | 6 | VI-2 | Serpinf2 |
| 1923 | 3 | 4 | 5 | 6 | VI-2 | Sertad4 |
| 1924 | 3 | 4 | 5 | 6 | VI-2 | Sesn3 |
| 1925 | 3 | 4 | 5 | 6 | VI-2 | Setbp1 |
| 1926 | 3 | 4 | 5 | 6 | VI-2 | Setd7 |
| 1927 | 3 | 4 | 5 | 6 | VI-2 | Setdb2 |
| 1928 | 3 | 4 | 5 | 6 | VI-2 | Sftpd |
| 1929 | 3 | 4 | 5 | 6 | VI-2 | Sgcd |
| 1930 | 3 | 4 | 5 | 6 | VI-2 | Sgtb |
| 1931 | 3 | 4 | 5 | 6 | VI-2 | Sh2b2 |
| 1932 | 3 | 4 | 5 | 6 | VI-2 | Sh2d1a |
| 1933 | 3 | 4 | 5 | 6 | VI-2 | Sh2d4a |
| 1934 | 3 | 4 | 5 | 6 | VI-2 | Sh3d21 |
| 1935 | 3 | 4 | 5 | 6 | VI-2 | Sh3pxd2a |
| 1936 | 3 | 4 | 5 | 6 | VI-2 | Sh3yl1 |
| 1937 | 3 | 4 | 5 | 6 | VI-2 | Shank2 |
| 1938 | 3 | 4 | 5 | 6 | VI-2 | Shf |
| 1939 | 3 | 4 | 5 | 6 | VI-2 | Siglecg |
| 1940 | 3 | 4 | 5 | 6 | VI-2 | Sik1 |
| 1941 | 3 | 4 | 5 | 6 | VI-2 | Sik2 |
| 1942 | 3 | 4 | 5 | 6 | VI-2 | Sipa1l1 |
| 1943 | 3 | 4 | 5 | 6 | VI-2 | Sirt3 |
| 1944 | 3 | 4 | 5 | 6 | VI-2 | Sit1 |
| 1945 | 3 | 4 | 5 | 6 | VI-2 | Six4 |
| 1946 | 3 | 4 | 5 | 6 | VI-2 | Sla2 |
| 1947 | 3 | 4 | 5 | 6 | VI-2 | Slain1 |
| 1948 | 3 | 4 | 5 | 6 | VI-2 | Slamf1 |
| 1949 | 3 | 4 | 5 | 6 | VI-2 | Slamf6 |
| 1950 | 3 | 4 | 5 | 6 | VI-2 | Slamf7 |
| 1951 | 3 | 4 | 5 | 6 | VI-2 | Slc10a5 |
| 1952 | 3 | 4 | 5 | 6 | VI-2 | Slc12a7 |
| 1953 | 3 | 4 | 5 | 6 | VI-2 | Slc12a9 |
| 1954 | 3 | 4 | 5 | 6 | VI-2 | Slc15a2 |
| 1955 | 3 | 4 | 5 | 6 | VI-2 | Slc16a11 |
| 1956 | 3 | 4 | 5 | 6 | VI-2 | Slc16a7 |
| 1957 | 3 | 4 | 5 | 6 | VI-2 | Slc24a4 |
| 1958 | 3 | 4 | 5 | 6 | VI-2 | Slc25a27 |
| 1959 | 3 | 4 | 5 | 6 | VI-2 | Slc25a33 |
| 1960 | 3 | 4 | 5 | 6 | VI-2 | Slc25a34 |
| 1961 | 3 | 4 | 5 | 6 | VI-2 | Slc25a36 |
| 1962 | 3 | 4 | 5 | 6 | VI-2 | Slc25a37 |
| 1963 | 3 | 4 | 5 | 6 | VI-2 | Slc25a53 |
| 1964 | 3 | 4 | 5 | 6 | VI-2 | Slc27a4 |
| 1965 | 3 | 4 | 5 | 6 | VI-2 | Slc29a1 |
| 1966 | 3 | 4 | 5 | 6 | VI-2 | Slc30a3 |
| 1967 | 3 | 4 | 5 | 6 | VI-2 | Slc34a3 |
| 1968 | 3 | 4 | 5 | 6 | VI-2 | Slc37a2 |
| 1969 | 3 | 4 | 5 | 6 | VI-2 | Slc39a3 |
| 1970 | 3 | 4 | 5 | 6 | VI-2 | Slc43a1 |
| 1971 | 3 | 4 | 5 | 6 | VI-2 | Slc5a12 |
| 1972 | 3 | 4 | 5 | 6 | VI-2 | Slc6a19 |
| 1973 | 3 | 4 | 5 | 6 | VI-2 | Slc7a4 |
| 1974 | 3 | 4 | 5 | 6 | VI-2 | Slc9a3r2 |
| 1975 | 3 | 4 | 5 | 6 | VI-2 | Slco4c1 |
| 1976 | 3 | 4 | 5 | 6 | VI-2 | Slfn14 |
| 1977 | 3 | 4 | 5 | 6 | VI-2 | Slfn5 |
| 1978 | 3 | 4 | 5 | 6 | VI-2 | Slfnl1 |
| 1979 | 3 | 4 | 5 | 6 | VI-2 | Smagp |
| 1980 | 3 | 4 | 5 | 6 | VI-2 | Smarce1 |
| 1981 | 3 | 4 | 5 | 6 | VI-2 | Smim11 |
| 1982 | 3 | 4 | 5 | 6 | VI-2 | Smim24 |
| 1983 | 3 | 4 | 5 | 6 | VI-2 | Smim5 |
| 1984 | 3 | 4 | 5 | 6 | VI-2 | Smoc1 |
| 1985 | 3 | 4 | 5 | 6 | VI-2 | Snca |
| 1986 | 3 | 4 | 5 | 6 | VI-2 | Sned1 |
| 1987 | 3 | 4 | 5 | 6 | VI-2 | Snhg12 |
| 1988 | 3 | 4 | 5 | 6 | VI-2 | Snhg7 |
| 1989 | 3 | 4 | 5 | 6 | VI-2 | Sno |
| 1990 | 3 | 4 | 5 | 6 | VI-2 | Snrpc |
| 1991 | 3 | 4 | 5 | 6 | VI-2 | Sntg2 |
| 1992 | 3 | 4 | 5 | 6 | VI-2 | Sntn |
| 1993 | 3 | 4 | 5 | 6 | VI-2 | Snx29 |
| 1994 | 3 | 4 | 5 | 6 | VI-2 | Socs5 |
| 1995 | 3 | 4 | 5 | 6 | VI-2 | Sowaha |
| 1996 | 3 | 4 | 5 | 6 | VI-2 | Spaca4 |
| 1997 | 3 | 4 | 5 | 6 | VI-2 | Spag6 |
| 1998 | 3 | 4 | 5 | 6 | VI-2 | Spata20 |
| 1999 | 3 | 4 | 5 | 6 | VI-2 | Spata21 |
| 2000 | 3 | 4 | 5 | 6 | VI-2 | Spata33 |
| 2001 | 3 | 4 | 5 | 6 | VI-2 | Spata5l1 |
| 2002 | 3 | 4 | 5 | 6 | VI-2 | Spatc1l |
| 2003 | 3 | 4 | 5 | 6 | VI-2 | Spdef |
| 2004 | 3 | 4 | 5 | 6 | VI-2 | Spdya |
| 2005 | 3 | 4 | 5 | 6 | VI-2 | Spef1 |
| 2006 | 3 | 4 | 5 | 6 | VI-2 | Spib |
| 2007 | 3 | 4 | 5 | 6 | VI-2 | Spink10 |
| 2008 | 3 | 4 | 5 | 6 | VI-2 | Spink2 |
| 2009 | 3 | 4 | 5 | 6 | VI-2 | Spint1 |
| 2010 | 3 | 4 | 5 | 6 | VI-2 | Spint2 |
| 2011 | 3 | 4 | 5 | 6 | VI-2 | Spo11 |
| 2012 | 3 | 4 | 5 | 6 | VI-2 | Spp2 |
| 2013 | 3 | 4 | 5 | 6 | VI-2 | Sppl2b |
| 2014 | 3 | 4 | 5 | 6 | VI-2 | Sppl2c |
| 2015 | 3 | 4 | 5 | 6 | VI-2 | Sprr2a1 |
| 2016 | 3 | 4 | 5 | 6 | VI-2 | Sptbn2 |
| 2017 | 3 | 4 | 5 | 6 | VI-2 | Sptlc3 |
| 2018 | 3 | 4 | 5 | 6 | VI-2 | Sqrdl |
| 2019 | 3 | 4 | 5 | 6 | VI-2 | Srcin1 |
| 2020 | 3 | 4 | 5 | 6 | VI-2 | Srd5a1 |
| 2021 | 3 | 4 | 5 | 6 | VI-2 | Srpk3 |
| 2022 | 3 | 4 | 5 | 6 | VI-2 | Ssmem1 |
| 2023 | 3 | 4 | 5 | 6 | VI-2 | Sst |
| 2024 | 3 | 4 | 5 | 6 | VI-2 | St5 |
| 2025 | 3 | 4 | 5 | 6 | VI-2 | St6gal1 |
| 2026 | 3 | 4 | 5 | 6 | VI-2 | St6galnac2 |
| 2027 | 3 | 4 | 5 | 6 | VI-2 | St8sia3os |
| 2028 | 3 | 4 | 5 | 6 | VI-2 | St8sia5 |
| 2029 | 3 | 4 | 5 | 6 | VI-2 | St8sia6 |
| 2030 | 3 | 4 | 5 | 6 | VI-2 | Stac2 |
| 2031 | 3 | 4 | 5 | 6 | VI-2 | Stamos |
| 2032 | 3 | 4 | 5 | 6 | VI-2 | Stap1 |
| 2033 | 3 | 4 | 5 | 6 | VI-2 | Stard10 |
| 2034 | 3 | 4 | 5 | 6 | VI-2 | Stard3 |
| 2035 | 3 | 4 | 5 | 6 | VI-2 | Stard8 |
| 2036 | 3 | 4 | 5 | 6 | VI-2 | Stbd1 |
| 2037 | 3 | 4 | 5 | 6 | VI-2 | Strada |
| 2038 | 3 | 4 | 5 | 6 | VI-2 | Strn |

Fig. 43 - 13

| | | | | | | | | | |
|---|---|---|---|---|---|---|---|---|---|
| 2039 | 3 | 4 | 5 | 6 | | VI-2 | Sugct |
| 2040 | 3 | 4 | 5 | 6 | | VI-2 | Suprt20 |
| 2041 | 3 | 4 | 5 | 6 | | VI-2 | Susd3 |
| 2042 | 3 | 4 | 5 | 6 | | VI-2 | Susd4 |
| 2043 | 3 | 4 | 5 | 6 | | VI-2 | Syde2 |
| 2044 | 3 | 4 | 5 | 6 | | VI-2 | Syne3 |
| 2045 | 3 | 4 | 5 | 6 | | VI-2 | Syngap1 |
| 2046 | 3 | 4 | 5 | 6 | | VI-2 | Syngr4 |
| 2047 | 3 | 4 | 5 | 6 | | VI-2 | Syt13 |
| 2048 | 3 | 4 | 5 | 6 | | VI-2 | Syt17 |
| 2049 | 3 | 4 | 5 | 6 | | VI-2 | Syt3 |
| 2050 | 3 | 4 | 5 | 6 | | VI-2 | Tango2 |
| 2051 | 3 | 4 | 5 | 6 | | VI-2 | Tarbp2 |
| 2052 | 3 | 4 | 5 | 6 | | VI-2 | Taspl |
| 2053 | 3 | 4 | 5 | 6 | | VI-2 | Tbc1d10b |
| 2054 | 3 | 4 | 5 | 6 | | VI-2 | Tbc1d17 |
| 2055 | 3 | 4 | 5 | 6 | | VI-2 | Tbc1d22a |
| 2056 | 3 | 4 | 5 | 6 | | VI-2 | Tbce |
| 2057 | 3 | 4 | 5 | 6 | | VI-2 | Tbx19 |
| 2058 | 3 | 4 | 5 | 6 | | VI-2 | Tbx6 |
| 2059 | 3 | 4 | 5 | 6 | | VI-2 | Tbxa2r |
| 2060 | 3 | 4 | 5 | 6 | | VI-2 | Tceal6 |
| 2061 | 3 | 4 | 5 | 6 | | VI-2 | Tcf23 |
| 2062 | 3 | 4 | 5 | 6 | | VI-2 | Tcf7 |
| 2063 | 3 | 4 | 5 | 6 | | VI-2 | Tcte1 |
| 2064 | 3 | 4 | 5 | 6 | | VI-2 | Tcte2 |
| 2065 | 3 | 4 | 5 | 6 | | VI-2 | Tctex1d1 |
| 2066 | 3 | 4 | 5 | 6 | | VI-2 | Tdrd5 |
| 2067 | 3 | 4 | 5 | 6 | | VI-2 | Tdrkh |
| 2068 | 3 | 4 | 5 | 6 | | VI-2 | Tead2 |
| 2069 | 3 | 4 | 5 | 6 | | VI-2 | Tead4 |
| 2070 | 3 | 4 | 5 | 6 | | VI-2 | Tekt1 |
| 2071 | 3 | 4 | 5 | 6 | | VI-2 | Tekt2 |
| 2072 | 3 | 4 | 5 | 6 | | VI-2 | Terc |
| 2073 | 3 | 4 | 5 | 6 | | VI-2 | Tert |
| 2074 | 3 | 4 | 5 | 6 | | VI-2 | Tesc1 |
| 2075 | 3 | 4 | 5 | 6 | | VI-2 | Tex101 |
| 2076 | 3 | 4 | 5 | 6 | | VI-2 | Tex22 |
| 2077 | 3 | 4 | 5 | 6 | | VI-2 | Tfb1m |
| 2078 | 3 | 4 | 5 | 6 | | VI-2 | Thap2 |
| 2079 | 3 | 4 | 5 | 6 | | VI-2 | Thbd |
| 2080 | 3 | 4 | 5 | 6 | | VI-2 | Thbs1 |
| 2081 | 3 | 4 | 5 | 6 | | VI-2 | Them7 |
| 2082 | 3 | 4 | 5 | 6 | | VI-2 | Themis |
| 2083 | 3 | 4 | 5 | 6 | | VI-2 | Thrsp |
| 2084 | 3 | 4 | 5 | 6 | | VI-2 | Tifa |
| 2085 | 3 | 4 | 5 | 6 | | VI-2 | Tigd5 |
| 2086 | 3 | 4 | 5 | 6 | | VI-2 | Timm50 |
| 2087 | 3 | 4 | 5 | 6 | | VI-2 | Timm9 |
| 2088 | 3 | 4 | 5 | 6 | | VI-2 | Tjp3 |
| 2089 | 3 | 4 | 5 | 6 | | VI-2 | Tle2 |
| 2090 | 3 | 4 | 5 | 6 | | VI-2 | Tle6 |
| 2091 | 3 | 4 | 5 | 6 | | VI-2 | Tln2 |
| 2092 | 3 | 4 | 5 | 6 | | VI-2 | Tlr4 |
| 2093 | 3 | 4 | 5 | 6 | | VI-2 | Tlr5 |
| 2094 | 3 | 4 | 5 | 6 | | VI-2 | Tm6sf1 |
| 2095 | 3 | 4 | 5 | 6 | | VI-2 | Tmcc2 |
| 2096 | 3 | 4 | 5 | 6 | | VI-2 | Tmed1 |
| 2097 | 3 | 4 | 5 | 6 | | VI-2 | Tmem101 |
| 2098 | 3 | 4 | 5 | 6 | | VI-2 | Tmem106c |
| 2099 | 3 | 4 | 5 | 6 | | VI-2 | Tmem126b |
| 2100 | 3 | 4 | 5 | 6 | | VI-2 | Tmem136 |
| 2101 | 3 | 4 | 5 | 6 | | VI-2 | Tmem140 |
| 2102 | 3 | 4 | 5 | 6 | | VI-2 | Tmem150c |
| 2103 | 3 | 4 | 5 | 6 | | VI-2 | Tmem163 |
| 2104 | 3 | 4 | 5 | 6 | | VI-2 | Tmem17 |
| 2105 | 3 | 4 | 5 | 6 | | VI-2 | Tmem170 |
| 2106 | 3 | 4 | 5 | 6 | | VI-2 | Tmem179b |
| 2107 | 3 | 4 | 5 | 6 | | VI-2 | Tmem185b |
| 2108 | 3 | 4 | 5 | 6 | | VI-2 | Tmem218 |
| 2109 | 3 | 4 | 5 | 6 | | VI-2 | Tmem245 |
| 2110 | 3 | 4 | 5 | 6 | | VI-2 | Tmem247 |
| 2111 | 3 | 4 | 5 | 6 | | VI-2 | Tmem26 |
| 2112 | 3 | 4 | 5 | 6 | | VI-2 | Tmem30b |
| 2113 | 3 | 4 | 5 | 6 | | VI-2 | Tmem5 |
| 2114 | 3 | 4 | 5 | 6 | | VI-2 | Tmem82 |
| 2115 | 3 | 4 | 5 | 6 | | VI-2 | Tmem86b |
| 2116 | 3 | 4 | 5 | 6 | | VI-2 | Tmod2 |
| 2117 | 3 | 4 | 5 | 6 | | VI-2 | Tmtc1 |
| 2118 | 3 | 4 | 5 | 6 | | VI-2 | Tnfrsf13b |
| 2119 | 3 | 4 | 5 | 6 | | VI-2 | Tnfrsf13c |
| 2120 | 3 | 4 | 5 | 6 | | VI-2 | Tnfrsf14 |
| 2121 | 3 | 4 | 5 | 6 | | VI-2 | Tnfrsf17 |
| 2122 | 3 | 4 | 5 | 6 | | VI-2 | Tnfrsf19 |
| 2123 | 3 | 4 | 5 | 6 | | VI-2 | Tnfrsf22 |
| 2124 | 3 | 4 | 5 | 6 | | VI-2 | Tnfrsf25 |
| 2125 | 3 | 4 | 5 | 6 | | VI-2 | Tnfsf10 |
| 2126 | 3 | 4 | 5 | 6 | | VI-2 | Tnk2 |
| 2127 | 3 | 4 | 5 | 6 | | VI-2 | Tnrc6b |
| 2128 | 3 | 4 | 5 | 6 | | VI-2 | Tomm40 |
| 2129 | 3 | 4 | 5 | 6 | | VI-2 | Tppp2 |
| 2130 | 3 | 4 | 5 | 6 | | VI-2 | Tppp3 |
| 2131 | 3 | 4 | 5 | 6 | | VI-2 | Tpra1 |
| 2132 | 3 | 4 | 5 | 6 | | VI-2 | Traf4 |
| 2133 | 3 | 4 | 5 | 6 | | VI-2 | Traf5 |
| 2134 | 3 | 4 | 5 | 6 | | VI-2 | Trat1 |
| 2135 | 3 | 4 | 5 | 6 | | VI-2 | Trib2 |
| 2136 | 3 | 4 | 5 | 6 | | VI-2 | Trim17 |
| 2137 | 3 | 4 | 5 | 6 | | VI-2 | Trim27 |
| 2138 | 3 | 4 | 5 | 6 | | VI-2 | Trim36 |
| 2139 | 3 | 4 | 5 | 6 | | VI-2 | Trim47 |
| 2140 | 3 | 4 | 5 | 6 | | VI-2 | Trim50 |
| 2141 | 3 | 4 | 5 | 6 | | VI-2 | Trim65 |
| 2142 | 3 | 4 | 5 | 6 | | VI-2 | Trmt11 |
| 2143 | 3 | 4 | 5 | 6 | | VI-2 | Trp53i11 |
| 2144 | 3 | 4 | 5 | 6 | | VI-2 | Trpc1 |
| 2145 | 3 | 4 | 5 | 6 | | VI-2 | Trpm4 |
| 2146 | 3 | 4 | 5 | 6 | | VI-2 | Tsacc |
| 2147 | 3 | 4 | 5 | 6 | | VI-2 | Tsfm |
| 2148 | 3 | 4 | 5 | 6 | | VI-2 | Tsga8 |
| 2149 | 3 | 4 | 5 | 6 | | VI-2 | Tssk3 |
| 2150 | 3 | 4 | 5 | 6 | | VI-2 | Tssk6 |
| 2151 | 3 | 4 | 5 | 6 | | VI-2 | Ttc21a |
| 2152 | 3 | 4 | 5 | 6 | | VI-2 | Ttc25 |
| 2153 | 3 | 4 | 5 | 6 | | VI-2 | Ttc28 |
| 2154 | 3 | 4 | 5 | 6 | | VI-2 | Ttc33 |
| 2155 | 3 | 4 | 5 | 6 | | VI-2 | Ttc7 |
| 2156 | 3 | 4 | 5 | 6 | | VI-2 | Ttll4 |
| 2157 | 3 | 4 | 5 | 6 | | VI-2 | Ttll8 |
| 2158 | 3 | 4 | 5 | 6 | | VI-2 | Tubgcp6 |
| 2159 | 3 | 4 | 5 | 6 | | VI-2 | Tulp2 |
| 2160 | 3 | 4 | 5 | 6 | | VI-2 | Twf2 |
| 2161 | 3 | 4 | 5 | 6 | | VI-2 | Tyk2 |
| 2162 | 3 | 4 | 5 | 6 | | VI-2 | Tyro3 |
| 2163 | 3 | 4 | 5 | 6 | | VI-2 | Tysnd1 |
| 2164 | 3 | 4 | 5 | 6 | | VI-2 | Tyw1 |
| 2165 | 3 | 4 | 5 | 6 | | VI-2 | Ubald2 |
| 2166 | 3 | 4 | 5 | 6 | | VI-2 | Ubd |
| 2167 | 3 | 4 | 5 | 6 | | VI-2 | Ube2d1 |
| 2168 | 3 | 4 | 5 | 6 | | VI-2 | Ube2d2b |
| 2169 | 3 | 4 | 5 | 6 | | VI-2 | Ube3a |
| 2170 | 3 | 4 | 5 | 6 | | VI-2 | Ubl4b |
| 2171 | 3 | 4 | 5 | 6 | | VI-2 | Ubl5 |
| 2172 | 3 | 4 | 5 | 6 | | VI-2 | Ubqln3 |
| 2173 | 3 | 4 | 5 | 6 | | VI-2 | Ubxn1 |
| 2174 | 3 | 4 | 5 | 6 | | VI-2 | Ubxn10 |
| 2175 | 3 | 4 | 5 | 6 | | VI-2 | Ubxn2b |
| 2176 | 3 | 4 | 5 | 6 | | VI-2 | Unc119 |
| 2177 | 3 | 4 | 5 | 6 | | VI-2 | Unc5cl |
| 2178 | 3 | 4 | 5 | 6 | | VI-2 | Upk2 |
| 2179 | 3 | 4 | 5 | 6 | | VI-2 | Upp2 |
| 2180 | 3 | 4 | 5 | 6 | | VI-2 | Uprt |
| 2181 | 3 | 4 | 5 | 6 | | VI-2 | Uros |
| 2182 | 3 | 4 | 5 | 6 | | VI-2 | Usp34 |
| 2183 | 3 | 4 | 5 | 6 | | VI-2 | Usp49 |
| 2184 | 3 | 4 | 5 | 6 | | VI-2 | Utp3 |
| 2185 | 3 | 4 | 5 | 6 | | VI-2 | Vamp1 |
| 2186 | 3 | 4 | 5 | 6 | | VI-2 | Vangl2 |
| 2187 | 3 | 4 | 5 | 6 | | VI-2 | Vav2 |
| 2188 | 3 | 4 | 5 | 6 | | VI-2 | Vegfc |
| 2189 | 3 | 4 | 5 | 6 | | VI-2 | Vgll4 |
| 2190 | 3 | 4 | 5 | 6 | | VI-2 | Vnn1 |
| 2191 | 3 | 4 | 5 | 6 | | VI-2 | Vnn3 |
| 2192 | 3 | 4 | 5 | 6 | | VI-2 | Vpreb2 |
| 2193 | 3 | 4 | 5 | 6 | | VI-2 | Vps13c |
| 2194 | 3 | 4 | 5 | 6 | | VI-2 | Vrk3 |
| 2195 | 3 | 4 | 5 | 6 | | VI-2 | Wasf3 |
| 2196 | 3 | 4 | 5 | 6 | | VI-2 | Wdr12 |
| 2197 | 3 | 4 | 5 | 6 | | VI-2 | Wdr45 |
| 2198 | 3 | 4 | 5 | 6 | | VI-2 | Wdr52 |
| 2199 | 3 | 4 | 5 | 6 | | VI-2 | Wdr74 |
| 2200 | 3 | 4 | 5 | 6 | | VI-2 | Wdr78 |
| 2201 | 3 | 4 | 5 | 6 | | VI-2 | Wdsub1 |
| 2202 | 3 | 4 | 5 | 6 | | VI-2 | Wfdc2 |
| 2203 | 3 | 4 | 5 | 6 | | VI-2 | Wfdc6b |
| 2204 | 3 | 4 | 5 | 6 | | VI-2 | Wfdc8 |
| 2205 | 3 | 4 | 5 | 6 | | VI-2 | Wfdc9 |
| 2206 | 3 | 4 | 5 | 6 | | VI-2 | Wnt2b |
| 2207 | 3 | 4 | 5 | 6 | | VI-2 | Wwc2 |
| 2208 | 3 | 4 | 5 | 6 | | VI-2 | Wwox |

Fig. 43 - 14

| | | | | | | | |
|---|---|---|---|---|---|---|---|
| 2209 | 3 | 4 | 5 | 6 | VI-2 | Xk |
| 2210 | 3 | 4 | 5 | 6 | VI-2 | Xkrx |
| 2211 | 3 | 4 | 5 | 6 | VI-2 | Xlr3b |
| 2212 | 3 | 4 | 5 | 6 | VI-2 | Xpnpep3 |
| 2213 | 3 | 4 | 5 | 6 | VI-2 | Xpo7 |
| 2214 | 3 | 4 | 5 | 6 | VI-2 | Xrcc1 |
| 2215 | 3 | 4 | 5 | 6 | VI-2 | Xrcc6 |
| 2216 | 3 | 4 | 5 | 6 | VI-2 | Xrn1 |
| 2217 | 3 | 4 | 5 | 6 | VI-2 | Xrra1 |
| 2218 | 3 | 4 | 5 | 6 | VI-2 | Xylb |
| 2219 | 3 | 4 | 5 | 6 | VI-2 | Xylt2 |
| 2220 | 3 | 4 | 5 | 6 | VI-2 | Ybx2 |
| 2221 | 3 | 4 | 5 | 6 | VI-2 | Ylpm1 |
| 2222 | 3 | 4 | 5 | 6 | VI-2 | Yod1 |
| 2223 | 3 | 4 | 5 | 6 | VI-2 | Ypel4 |
| 2224 | 3 | 4 | 5 | 6 | VI-2 | Zbtb16 |
| 2225 | 3 | 4 | 5 | 6 | VI-2 | Zbtb26 |
| 2226 | 3 | 4 | 5 | 6 | VI-2 | Zbtb32 |
| 2227 | 3 | 4 | 5 | 6 | VI-2 | Zbtb38 |
| 2228 | 3 | 4 | 5 | 6 | VI-2 | Zbtb46 |
| 2229 | 3 | 4 | 5 | 6 | VI-2 | Zcchc18 |
| 2230 | 3 | 4 | 5 | 6 | VI-2 | Zdhhc12 |
| 2231 | 3 | 4 | 5 | 6 | VI-2 | Zdhhc16 |
| 2232 | 3 | 4 | 5 | 6 | VI-2 | Zdhhc23 |
| 2233 | 3 | 4 | 5 | 6 | VI-2 | Zf12 |
| 2234 | 3 | 4 | 5 | 6 | VI-2 | Zfand1 |
| 2235 | 3 | 4 | 5 | 6 | VI-2 | Zfand4 |
| 2236 | 3 | 4 | 5 | 6 | VI-2 | Zfa-ps |
| 2237 | 3 | 4 | 5 | 6 | VI-2 | Zfp109 |
| 2238 | 3 | 4 | 5 | 6 | VI-2 | Zfp119a |
| 2239 | 3 | 4 | 5 | 6 | VI-2 | Zfp169 |
| 2240 | 3 | 4 | 5 | 6 | VI-2 | Zfp189 |
| 2241 | 3 | 4 | 5 | 6 | VI-2 | Zfp213 |
| 2242 | 3 | 4 | 5 | 6 | VI-2 | Zfp287 |
| 2243 | 3 | 4 | 5 | 6 | VI-2 | Zfp329 |
| 2244 | 3 | 4 | 5 | 6 | VI-2 | Zfp354a |
| 2245 | 3 | 4 | 5 | 6 | VI-2 | Zfp369 |
| 2246 | 3 | 4 | 5 | 6 | VI-2 | Zfp36l2 |
| 2247 | 3 | 4 | 5 | 6 | VI-2 | Zfp385b |
| 2248 | 3 | 4 | 5 | 6 | VI-2 | Zfp398 |
| 2249 | 3 | 4 | 5 | 6 | VI-2 | Zfp428 |
| 2250 | 3 | 4 | 5 | 6 | VI-2 | Zfp523 |
| 2251 | 3 | 4 | 5 | 6 | VI-2 | Zfp524 |
| 2252 | 3 | 4 | 5 | 6 | VI-2 | Zfp526 |
| 2253 | 3 | 4 | 5 | 6 | VI-2 | Zfp553 |
| 2254 | 3 | 4 | 5 | 6 | VI-2 | Zfp560 |
| 2255 | 3 | 4 | 5 | 6 | VI-2 | Zfp563 |
| 2256 | 3 | 4 | 5 | 6 | VI-2 | Zfp568 |
| 2257 | 3 | 4 | 5 | 6 | VI-2 | Zfp595 |
| 2258 | 3 | 4 | 5 | 6 | VI-2 | Zfp607 |
| 2259 | 3 | 4 | 5 | 6 | VI-2 | Zfp661 |
| 2260 | 3 | 4 | 5 | 6 | VI-2 | Zfp667 |
| 2261 | 3 | 4 | 5 | 6 | VI-2 | Zfp69 |
| 2262 | 3 | 4 | 5 | 6 | VI-2 | Zfp704 |
| 2263 | 3 | 4 | 5 | 6 | VI-2 | Zfp712 |
| 2264 | 3 | 4 | 5 | 6 | VI-2 | Zfp72 |
| 2265 | 3 | 4 | 5 | 6 | VI-2 | Zfp759 |
| 2266 | 3 | 4 | 5 | 6 | VI-2 | Zfp780b |
| 2267 | 3 | 4 | 5 | 6 | VI-2 | Zfp874b |
| 2268 | 3 | 4 | 5 | 6 | VI-2 | Zfp882 |
| 2269 | 3 | 4 | 5 | 6 | VI-2 | Zfp931 |
| 2270 | 3 | 4 | 5 | 6 | VI-2 | Zfp933 |
| 2271 | 3 | 4 | 5 | 6 | VI-2 | Zfp954 |
| 2272 | 3 | 4 | 5 | 6 | VI-2 | Zfyve28 |
| 2273 | 3 | 4 | 5 | 6 | VI-2 | Zgpat |
| 2274 | 3 | 4 | 5 | 6 | VI-2 | Zhx2 |
| 2275 | 3 | 4 | 5 | 6 | VI-2 | Zhx3 |
| 2276 | 3 | 4 | 5 | 6 | VI-2 | Zim1 |
| 2277 | 3 | 4 | 5 | 6 | VI-2 | Zkscan17 |
| 2278 | 3 | 4 | 5 | 6 | VI-2 | Zkscan7 |
| 2279 | 3 | 4 | 5 | 6 | VI-2 | Zmym1 |
| 2280 | 3 | 4 | 5 | 6 | VI-2 | Zmynd10 |
| 2281 | 3 | 4 | 5 | 6 | VI-2 | Znrd1as |
| 2282 | 3 | 4 | 5 | 6 | VI-2 | Zpbp2 |
| 2283 | 3 | 4 | 5 | 6 | VI-2 | Zpr1 |
| 2284 | 3 | 4 | 5 | 6 | VI-2 | Zranb3 |
| 2285 | 3 | 4 | 5 | 6 | VI-2 | Zscan20 |
| 2286 | 3 | 4 | 5 | 6 | VI-1 | 0610031O16Rik |
| 2287 | 3 | 4 | 5 | 6 | VI-1 | 0610039K10Rik |
| 2288 | 3 | 4 | 5 | 6 | VI-1 | 0610040B10Rik |
| 2289 | 3 | 4 | 5 | 6 | VI-1 | 0610040J01Rik |
| 2290 | 3 | 4 | 5 | 6 | VI-1 | 0610043K17Rik |
| 2291 | 3 | 4 | 5 | 6 | VI-1 | 1110006O24Rik |
| 2292 | 3 | 4 | 5 | 6 | VI-1 | 1110046J04Rik |
| 2293 | 3 | 4 | 5 | 6 | VI-1 | 1190002F15Rik |

| | | | | | | | |
|---|---|---|---|---|---|---|---|
| 2294 | 3 | 4 | 5 | 6 | VI-1 | 1700001J03Rik |
| 2295 | 3 | 4 | 5 | 6 | VI-1 | 1700010K23Rik |
| 2296 | 3 | 4 | 5 | 6 | VI-1 | 1700012B09Rik |
| 2297 | 3 | 4 | 5 | 6 | VI-1 | 1700012D14Rik |
| 2298 | 3 | 4 | 5 | 6 | VI-1 | 1700018L02Rik |
| 2299 | 3 | 4 | 5 | 6 | VI-1 | 1700024P16Rik |
| 2300 | 3 | 4 | 5 | 6 | VI-1 | 1700025N23Rik |
| 2301 | 3 | 4 | 5 | 6 | VI-1 | 1700030C10Rik |
| 2302 | 3 | 4 | 5 | 6 | VI-1 | 1700071M16Rik |
| 2303 | 3 | 4 | 5 | 6 | VI-1 | 1700084C01Rik |
| 2304 | 3 | 4 | 5 | 6 | VI-1 | 1700084E18Rik |
| 2305 | 3 | 4 | 5 | 6 | VI-1 | 1700086O06Rik |
| 2306 | 3 | 4 | 5 | 6 | VI-1 | 1700097N02Rik |
| 2307 | 3 | 4 | 5 | 6 | VI-1 | 1700110K17Rik |
| 2308 | 3 | 4 | 5 | 6 | VI-1 | 1700120C14Rik |
| 2309 | 3 | 4 | 5 | 6 | VI-1 | 1700120K04Rik |
| 2310 | 3 | 4 | 5 | 6 | VI-1 | 1700124L16Rik |
| 2311 | 3 | 4 | 5 | 6 | VI-1 | 1810013A23Rik |
| 2312 | 3 | 4 | 5 | 6 | VI-1 | 1810019D21Rik |
| 2313 | 3 | 4 | 5 | 6 | VI-1 | 1810021B22Rik |
| 2314 | 3 | 4 | 5 | 6 | VI-1 | 1810022K09Rik |
| 2315 | 3 | 4 | 5 | 6 | VI-1 | 1810034E14Rik |
| 2316 | 3 | 4 | 5 | 6 | VI-1 | 1810055G02Rik |
| 2317 | 3 | 4 | 5 | 6 | VI-1 | 1810062G17Rik |
| 2318 | 3 | 4 | 5 | 6 | VI-1 | 2010003K11Rik |
| 2319 | 3 | 4 | 5 | 6 | VI-1 | 2010010A06Rik |
| 2320 | 3 | 4 | 5 | 6 | VI-1 | 2010204K13Rik |
| 2321 | 3 | 4 | 5 | 6 | VI-1 | 2210011C24Rik |
| 2322 | 3 | 4 | 5 | 6 | VI-1 | 2210013O21Rik |
| 2323 | 3 | 4 | 5 | 6 | VI-1 | 2210408F21Rik |
| 2324 | 3 | 4 | 5 | 6 | VI-1 | 2210414B05Rik |
| 2325 | 3 | 4 | 5 | 6 | VI-1 | 2300005B03Rik |
| 2326 | 3 | 4 | 5 | 6 | VI-1 | 2300009A05Rik |
| 2327 | 3 | 4 | 5 | 6 | VI-1 | 2310001K24Rik |
| 2328 | 3 | 4 | 5 | 6 | VI-1 | 2310002L09Rik |
| 2329 | 3 | 4 | 5 | 6 | VI-1 | 2310009B15Rik |
| 2330 | 3 | 4 | 5 | 6 | VI-1 | 2310015B20Rik |
| 2331 | 3 | 4 | 5 | 6 | VI-1 | 2310040G24Rik |
| 2332 | 3 | 4 | 5 | 6 | VI-1 | 2310050C09Rik |
| 2333 | 3 | 4 | 5 | 6 | VI-1 | 2310068J16Rik |
| 2334 | 3 | 4 | 5 | 6 | VI-1 | 2310069B03Rik |
| 2335 | 3 | 4 | 5 | 6 | VI-1 | 2610028H24Rik |
| 2336 | 3 | 4 | 5 | 6 | VI-1 | 2610318N02Rik |
| 2337 | 3 | 4 | 5 | 6 | VI-1 | 2610524H06Rik |
| 2338 | 3 | 4 | 5 | 6 | VI-1 | 2610528A11Rik |
| 2339 | 3 | 4 | 5 | 6 | VI-1 | 2610528J11Rik |
| 2340 | 3 | 4 | 5 | 6 | VI-1 | 2700099C18Rik |
| 2341 | 3 | 4 | 5 | 6 | VI-1 | 2810008D09Rik |
| 2342 | 3 | 4 | 5 | 6 | VI-1 | 2810403D21Rik |
| 2343 | 3 | 4 | 5 | 6 | VI-1 | 2810408I11Rik |
| 2344 | 3 | 4 | 5 | 6 | VI-1 | 2810428I15Rik |
| 2345 | 3 | 4 | 5 | 6 | VI-1 | 2900076A07Rik |
| 2346 | 3 | 4 | 5 | 6 | VI-1 | 3010033K07Rik |
| 2347 | 3 | 4 | 5 | 6 | VI-1 | 3110043O21Rik |
| 2348 | 3 | 4 | 5 | 6 | VI-1 | 3110070M22Rik |
| 2349 | 3 | 4 | 5 | 6 | VI-1 | 4631405J19Rik |
| 2350 | 3 | 4 | 5 | 6 | VI-1 | 4632434I11Rik |
| 2351 | 3 | 4 | 5 | 6 | VI-1 | 4732471J01Rik |
| 2352 | 3 | 4 | 5 | 6 | VI-1 | 4833418N02Rik |
| 2353 | 3 | 4 | 5 | 6 | VI-1 | 4833427F10Rik |
| 2354 | 3 | 4 | 5 | 6 | VI-1 | 4921531C22Rik |
| 2355 | 3 | 4 | 5 | 6 | VI-1 | 4930404N11Rik |
| 2356 | 3 | 4 | 5 | 6 | VI-1 | 4930413G21Rik |
| 2357 | 3 | 4 | 5 | 6 | VI-1 | 4930429F24Rik |
| 2358 | 3 | 4 | 5 | 6 | VI-1 | 4930455C13Rik |
| 2359 | 3 | 4 | 5 | 6 | VI-1 | 4930474M22Rik |
| 2360 | 3 | 4 | 5 | 6 | VI-1 | 4930519F09Rik |
| 2361 | 3 | 4 | 5 | 6 | VI-1 | 4931408D14Rik |
| 2362 | 3 | 4 | 5 | 6 | VI-1 | 4931431B13Rik |
| 2363 | 3 | 4 | 5 | 6 | VI-1 | 4932438H23Rik |
| 2364 | 3 | 4 | 5 | 6 | VI-1 | 4933431E20Rik |
| 2365 | 3 | 4 | 5 | 6 | VI-1 | 5031434O11Rik |
| 2366 | 3 | 4 | 5 | 6 | VI-1 | 5730405O15Rik |
| 2367 | 3 | 4 | 5 | 6 | VI-1 | 5730408K05Rik |
| 2368 | 3 | 4 | 5 | 6 | VI-1 | 5730480H06Rik |
| 2369 | 3 | 4 | 5 | 6 | VI-1 | 5730559C18Rik |
| 2370 | 3 | 4 | 5 | 6 | VI-1 | 5830454E08Rik |
| 2371 | 3 | 4 | 5 | 6 | VI-1 | 6330418K02Rik |
| 2372 | 3 | 4 | 5 | 6 | VI-1 | 8430408G22Rik |
| 2373 | 3 | 4 | 5 | 6 | VI-1 | 9130409I23Rik |
| 2374 | 3 | 4 | 5 | 6 | VI-1 | 9230114K14Rik |
| 2375 | 3 | 4 | 5 | 6 | VI-1 | 9330133O14Rik |
| 2376 | 3 | 4 | 5 | 6 | VI-1 | 9330159F19Rik |
| 2377 | 3 | 4 | 5 | 6 | VI-1 | 9530077C05Rik |
| 2378 | 3 | 4 | 5 | 6 | VI-1 | 9930012K11Rik |

Fig. 43 - 15

| | | | | | | | | |
|---|---|---|---|---|---|---|---|---|
| 2379 | 3 | 4 | 5 | 6 | | VI-1 | A430105J19Rik |
| 2380 | 3 | 4 | 5 | 6 | | VI-1 | A530013C23Rik |
| 2381 | 3 | 4 | 5 | 6 | | VI-1 | A530064D06Rik |
| 2382 | 3 | 4 | 5 | 6 | | VI-1 | A730008H23Rik |
| 2383 | 3 | 4 | 5 | 6 | | VI-1 | AA413626 |
| 2384 | 3 | 4 | 5 | 6 | | VI-1 | AA467197 |
| 2385 | 3 | 4 | 5 | 6 | | VI-1 | Aaas |
| 2386 | 3 | 4 | 5 | 6 | | VI-1 | AB124611 |
| 2387 | 3 | 4 | 5 | 6 | | VI-1 | Abca6 |
| 2388 | 3 | 4 | 5 | 6 | | VI-1 | Abcb4 |
| 2389 | 3 | 4 | 5 | 6 | | VI-1 | Abcg4 |
| 2390 | 3 | 4 | 5 | 6 | | VI-1 | Abhd11os |
| 2391 | 3 | 4 | 5 | 6 | | VI-1 | Abhd15 |
| 2392 | 3 | 4 | 5 | 6 | | VI-1 | Abhd2 |
| 2393 | 3 | 4 | 5 | 6 | | VI-1 | Abhd3 |
| 2394 | 3 | 4 | 5 | 6 | | VI-1 | Acer2 |
| 2395 | 3 | 4 | 5 | 6 | | VI-1 | Ackr1 |
| 2396 | 3 | 4 | 5 | 6 | | VI-1 | Ackr3 |
| 2397 | 3 | 4 | 5 | 6 | | VI-1 | Ackr4 |
| 2398 | 3 | 4 | 5 | 6 | | VI-1 | Acot1 |
| 2399 | 3 | 4 | 5 | 6 | | VI-1 | Acot11 |
| 2400 | 3 | 4 | 5 | 6 | | VI-1 | Acot2 |
| 2401 | 3 | 4 | 5 | 6 | | VI-1 | Acot5 |
| 2402 | 3 | 4 | 5 | 6 | | VI-1 | Acp5 |
| 2403 | 3 | 4 | 5 | 6 | | VI-1 | Acp6 |
| 2404 | 3 | 4 | 5 | 6 | | VI-1 | Acr |
| 2405 | 3 | 4 | 5 | 6 | | VI-1 | Acsl1 |
| 2406 | 3 | 4 | 5 | 6 | | VI-1 | Acta2 |
| 2407 | 3 | 4 | 5 | 6 | | VI-1 | Actc1 |
| 2408 | 3 | 4 | 5 | 6 | | VI-1 | Acvr1b |
| 2409 | 3 | 4 | 5 | 6 | | VI-1 | Acyp2 |
| 2410 | 3 | 4 | 5 | 6 | | VI-1 | Ada |
| 2411 | 3 | 4 | 5 | 6 | | VI-1 | Adam12 |
| 2412 | 3 | 4 | 5 | 6 | | VI-1 | Adamts15 |
| 2413 | 3 | 4 | 5 | 6 | | VI-1 | Adamts3 |
| 2414 | 3 | 4 | 5 | 6 | | VI-1 | Adamts4 |
| 2415 | 3 | 4 | 5 | 6 | | VI-1 | Adamts8 |
| 2416 | 3 | 4 | 5 | 6 | | VI-1 | Adar |
| 2417 | 3 | 4 | 5 | 6 | | VI-1 | Adcy3 |
| 2418 | 3 | 4 | 5 | 6 | | VI-1 | Adcyap1r1 |
| 2419 | 3 | 4 | 5 | 6 | | VI-1 | Add2 |
| 2420 | 3 | 4 | 5 | 6 | | VI-1 | Adh1 |
| 2421 | 3 | 4 | 5 | 6 | | VI-1 | Adipoq |
| 2422 | 3 | 4 | 5 | 6 | | VI-1 | Adm |
| 2423 | 3 | 4 | 5 | 6 | | VI-1 | Adprhl1 |
| 2424 | 3 | 4 | 5 | 6 | | VI-1 | Adra2a |
| 2425 | 3 | 4 | 5 | 6 | | VI-1 | Aen |
| 2426 | 3 | 4 | 5 | 6 | | VI-1 | AF251705 |
| 2427 | 3 | 4 | 5 | 6 | | VI-1 | Agl |
| 2428 | 3 | 4 | 5 | 6 | | VI-1 | Agpat2 |
| 2429 | 3 | 4 | 5 | 6 | | VI-1 | Agt |
| 2430 | 3 | 4 | 5 | 6 | | VI-1 | Ahsg |
| 2431 | 3 | 4 | 5 | 6 | | VI-1 | AI427809 |
| 2432 | 3 | 4 | 5 | 6 | | VI-1 | AI464131 |
| 2433 | 3 | 4 | 5 | 6 | | VI-1 | AI506816 |
| 2434 | 3 | 4 | 5 | 6 | | VI-1 | AI607873 |
| 2435 | 3 | 4 | 5 | 6 | | VI-1 | AI646519 |
| 2436 | 3 | 4 | 5 | 6 | | VI-1 | Ak1 |
| 2437 | 3 | 4 | 5 | 6 | | VI-1 | Akap2 |
| 2438 | 3 | 4 | 5 | 6 | | VI-1 | Akr1b3 |
| 2439 | 3 | 4 | 5 | 6 | | VI-1 | Akr1b8 |
| 2440 | 3 | 4 | 5 | 6 | | VI-1 | Akr1c12 |
| 2441 | 3 | 4 | 5 | 6 | | VI-1 | Akr1c20 |
| 2442 | 3 | 4 | 5 | 6 | | VI-1 | Alb |
| 2443 | 3 | 4 | 5 | 6 | | VI-1 | Aldh1a1 |
| 2444 | 3 | 4 | 5 | 6 | | VI-1 | Aldh1a7 |
| 2445 | 3 | 4 | 5 | 6 | | VI-1 | Aldh1b1 |
| 2446 | 3 | 4 | 5 | 6 | | VI-1 | Aldh1l2 |
| 2447 | 3 | 4 | 5 | 6 | | VI-1 | Aldh3b2 |
| 2448 | 3 | 4 | 5 | 6 | | VI-1 | Aldoa |
| 2449 | 3 | 4 | 5 | 6 | | VI-1 | Aldoart1 |
| 2450 | 3 | 4 | 5 | 6 | | VI-1 | Aldoart2 |
| 2451 | 3 | 4 | 5 | 6 | | VI-1 | Aldob |
| 2452 | 3 | 4 | 5 | 6 | | VI-1 | Atg10b |
| 2453 | 3 | 4 | 5 | 6 | | VI-1 | Alox12 |
| 2454 | 3 | 4 | 5 | 6 | | VI-1 | Alox5 |
| 2455 | 3 | 4 | 5 | 6 | | VI-1 | Alox5ap |
| 2456 | 3 | 4 | 5 | 6 | | VI-1 | Alpi |
| 2457 | 3 | 4 | 5 | 6 | | VI-1 | Alx1 |
| 2458 | 3 | 4 | 5 | 6 | | VI-1 | Alx4 |
| 2459 | 3 | 4 | 5 | 6 | | VI-1 | Ammecr1 |
| 2460 | 3 | 4 | 5 | 6 | | VI-1 | Amot |
| 2461 | 3 | 4 | 5 | 6 | | VI-1 | Amotl1 |
| 2462 | 3 | 4 | 5 | 6 | | VI-1 | Ampd2 |
| 2463 | 3 | 4 | 5 | 6 | | VI-1 | Amy1 |
| 2464 | 3 | 4 | 5 | 6 | | VI-1 | Amy2a2 |
| 2465 | 3 | 4 | 5 | 6 | | VI-1 | Anapc15 |
| 2466 | 3 | 4 | 5 | 6 | | VI-1 | Angptl1 |
| 2467 | 3 | 4 | 5 | 6 | | VI-1 | Angptl2 |
| 2468 | 3 | 4 | 5 | 6 | | VI-1 | Angptl7 |
| 2469 | 3 | 4 | 5 | 6 | | VI-1 | Ank3 |
| 2470 | 3 | 4 | 5 | 6 | | VI-1 | Ankrd1 |
| 2471 | 3 | 4 | 5 | 6 | | VI-1 | Ankrd11 |
| 2472 | 3 | 4 | 5 | 6 | | VI-1 | Ankrd33b |
| 2473 | 3 | 4 | 5 | 6 | | VI-1 | Ankrd37 |
| 2474 | 3 | 4 | 5 | 6 | | VI-1 | Ankrd61 |
| 2475 | 3 | 4 | 5 | 6 | | VI-1 | Ankrd63 |
| 2476 | 3 | 4 | 5 | 6 | | VI-1 | Anxa1 |
| 2477 | 3 | 4 | 5 | 6 | | VI-1 | Anxa8 |
| 2478 | 3 | 4 | 5 | 6 | | VI-1 | Aoc2 |
| 2479 | 3 | 4 | 5 | 6 | | VI-1 | Aox1 |
| 2480 | 3 | 4 | 5 | 6 | | VI-1 | Apcdd1 |
| 2481 | 3 | 4 | 5 | 6 | | VI-1 | Apcs |
| 2482 | 3 | 4 | 5 | 6 | | VI-1 | Apex1 |
| 2483 | 3 | 4 | 5 | 6 | | VI-1 | Apln |
| 2484 | 3 | 4 | 5 | 6 | | VI-1 | Apoa4 |
| 2485 | 3 | 4 | 5 | 6 | | VI-1 | Apobr |
| 2486 | 3 | 4 | 5 | 6 | | VI-1 | Apoc1 |
| 2487 | 3 | 4 | 5 | 6 | | VI-1 | Apoc2 |
| 2488 | 3 | 4 | 5 | 6 | | VI-1 | Apoc3 |
| 2489 | 3 | 4 | 5 | 6 | | VI-1 | Apoc4 |
| 2490 | 3 | 4 | 5 | 6 | | VI-1 | Apod |
| 2491 | 3 | 4 | 5 | 6 | | VI-1 | Apol6 |
| 2492 | 3 | 4 | 5 | 6 | | VI-1 | Apol7a |
| 2493 | 3 | 4 | 5 | 6 | | VI-1 | Apoo |
| 2494 | 3 | 4 | 5 | 6 | | VI-1 | Aqp11 |
| 2495 | 3 | 4 | 5 | 6 | | VI-1 | Aqp12 |
| 2496 | 3 | 4 | 5 | 6 | | VI-1 | Arc |
| 2497 | 3 | 4 | 5 | 6 | | VI-1 | Arg1 |
| 2498 | 3 | 4 | 5 | 6 | | VI-1 | Arg2 |
| 2499 | 3 | 4 | 5 | 6 | | VI-1 | Arhgap11a |
| 2500 | 3 | 4 | 5 | 6 | | VI-1 | Arhgap15 |
| 2501 | 3 | 4 | 5 | 6 | | VI-1 | Arhgdig |
| 2502 | 3 | 4 | 5 | 6 | | VI-1 | Arhgef19 |
| 2503 | 3 | 4 | 5 | 6 | | VI-1 | Arl5b |
| 2504 | 3 | 4 | 5 | 6 | | VI-1 | Arl5c |
| 2505 | 3 | 4 | 5 | 6 | | VI-1 | Arxes1 |
| 2506 | 3 | 4 | 5 | 6 | | VI-1 | Arxes2 |
| 2507 | 3 | 4 | 5 | 6 | | VI-1 | As3mt |
| 2508 | 3 | 4 | 5 | 6 | | VI-1 | Asb17 |
| 2509 | 3 | 4 | 5 | 6 | | VI-1 | Asb17os |
| 2510 | 3 | 4 | 5 | 6 | | VI-1 | Asf1b |
| 2511 | 3 | 4 | 5 | 6 | | VI-1 | Asns |
| 2512 | 3 | 4 | 5 | 6 | | VI-1 | Aspg |
| 2513 | 3 | 4 | 5 | 6 | | VI-1 | Ass1 |
| 2514 | 3 | 4 | 5 | 6 | | VI-1 | Atf3 |
| 2515 | 3 | 4 | 5 | 6 | | VI-1 | Atf5 |
| 2516 | 3 | 4 | 5 | 6 | | VI-1 | Atp1b2 |
| 2517 | 3 | 4 | 5 | 6 | | VI-1 | Atp5e |
| 2518 | 3 | 4 | 5 | 6 | | VI-1 | Atp5k |
| 2519 | 3 | 4 | 5 | 6 | | VI-1 | Atp6v1g2 |
| 2520 | 3 | 4 | 5 | 6 | | VI-1 | Atp7b |
| 2521 | 3 | 4 | 5 | 6 | | VI-1 | Atpif1 |
| 2522 | 3 | 4 | 5 | 6 | | VI-1 | Atxn1l |
| 2523 | 3 | 4 | 5 | 6 | | VI-1 | AW011738 |
| 2524 | 3 | 4 | 5 | 6 | | VI-1 | AY358078 |
| 2525 | 3 | 4 | 5 | 6 | | VI-1 | B230208H11Rik |
| 2526 | 3 | 4 | 5 | 6 | | VI-1 | B430010I23Rik |
| 2527 | 3 | 4 | 5 | 6 | | VI-1 | B430306N03Rik |
| 2528 | 3 | 4 | 5 | 6 | | VI-1 | B4galt6 |
| 2529 | 3 | 4 | 5 | 6 | | VI-1 | B930025P03Rik |
| 2530 | 3 | 4 | 5 | 6 | | VI-1 | Bag2 |
| 2531 | 3 | 4 | 5 | 6 | | VI-1 | Bax |
| 2532 | 3 | 4 | 5 | 6 | | VI-1 | Bbx |
| 2533 | 3 | 4 | 5 | 6 | | VI-1 | BC022687 |
| 2534 | 3 | 4 | 5 | 6 | | VI-1 | BC037704 |
| 2535 | 3 | 4 | 5 | 6 | | VI-1 | BC049352 |
| 2536 | 3 | 4 | 5 | 6 | | VI-1 | BC064078 |
| 2537 | 3 | 4 | 5 | 6 | | VI-1 | BC100530 |
| 2538 | 3 | 4 | 5 | 6 | | VI-1 | Bcl2a1b |
| 2539 | 3 | 4 | 5 | 6 | | VI-1 | Bcmo1 |
| 2540 | 3 | 4 | 5 | 6 | | VI-1 | Bdh1 |
| 2541 | 3 | 4 | 5 | 6 | | VI-1 | Bex2 |
| 2542 | 3 | 4 | 5 | 6 | | VI-1 | Bglap |
| 2543 | 3 | 4 | 5 | 6 | | VI-1 | Bglap2 |
| 2544 | 3 | 4 | 5 | 6 | | VI-1 | Bhmt |
| 2545 | 3 | 4 | 5 | 6 | | VI-1 | Bik |
| 2546 | 3 | 4 | 5 | 6 | | VI-1 | Birc5 |
| 2547 | 3 | 4 | 5 | 6 | | VI-1 | Bst1 |
| 2548 | 3 | 4 | 5 | 6 | | VI-1 | Bst2 |

Fig. 43 - 16

| | | | | | | | | |
|---|---|---|---|---|---|---|---|---|
| 2549 | 3 | 4 | 5 | 6 | | VI-1 | Btbd3 |
| 2550 | 3 | 4 | 5 | 6 | | VI-1 | Btnl9 |
| 2551 | 3 | 4 | 5 | 6 | | VI-1 | Bves |
| 2552 | 3 | 4 | 5 | 6 | | VI-1 | C130080G10Rik |
| 2553 | 3 | 4 | 5 | 6 | | VI-1 | C130083M11Rik |
| 2554 | 3 | 4 | 5 | 6 | | VI-1 | C1galt1 |
| 2555 | 3 | 4 | 5 | 6 | | VI-1 | C1qbp |
| 2556 | 3 | 4 | 5 | 6 | | VI-1 | C1qtnf2 |
| 2557 | 3 | 4 | 5 | 6 | | VI-1 | C1qtnf4 |
| 2558 | 3 | 4 | 5 | 6 | | VI-1 | C1qtnf6 |
| 2559 | 3 | 4 | 5 | 6 | | VI-1 | C1ra |
| 2560 | 3 | 4 | 5 | 6 | | VI-1 | C1rb |
| 2561 | 3 | 4 | 5 | 6 | | VI-1 | C230035I16Rik |
| 2562 | 3 | 4 | 5 | 6 | | VI-1 | C3 |
| 2563 | 3 | 4 | 5 | 6 | | VI-1 | C4a |
| 2564 | 3 | 4 | 5 | 6 | | VI-1 | C4b |
| 2565 | 3 | 4 | 5 | 6 | | VI-1 | C730036E19Rik |
| 2566 | 3 | 4 | 5 | 6 | | VI-1 | C920025E04Rik |
| 2567 | 3 | 4 | 5 | 6 | | VI-1 | Cabyr |
| 2568 | 3 | 4 | 5 | 6 | | VI-1 | Cacna2d1 |
| 2569 | 3 | 4 | 5 | 6 | | VI-1 | Cacnb1 |
| 2570 | 3 | 4 | 5 | 6 | | VI-1 | Cacng6 |
| 2571 | 3 | 4 | 5 | 6 | | VI-1 | Cacng7 |
| 2572 | 3 | 4 | 5 | 6 | | VI-1 | Cad |
| 2573 | 3 | 4 | 5 | 6 | | VI-1 | Cadm4 |
| 2574 | 3 | 4 | 5 | 6 | | VI-1 | Calml4 |
| 2575 | 3 | 4 | 5 | 6 | | VI-1 | Camk1d |
| 2576 | 3 | 4 | 5 | 6 | | VI-1 | Camk2a |
| 2577 | 3 | 4 | 5 | 6 | | VI-1 | Camp |
| 2578 | 3 | 4 | 5 | 6 | | VI-1 | Cand2 |
| 2579 | 3 | 4 | 5 | 6 | | VI-1 | Car1 |
| 2580 | 3 | 4 | 5 | 6 | | VI-1 | Card6 |
| 2581 | 3 | 4 | 5 | 6 | | VI-1 | Casq2 |
| 2582 | 3 | 4 | 5 | 6 | | VI-1 | Cav1 |
| 2583 | 3 | 4 | 5 | 6 | | VI-1 | Cbln1 |
| 2584 | 3 | 4 | 5 | 6 | | VI-1 | Cbr1 |
| 2585 | 3 | 4 | 5 | 6 | | VI-1 | Cbr3 |
| 2586 | 3 | 4 | 5 | 6 | | VI-1 | Ccdc120 |
| 2587 | 3 | 4 | 5 | 6 | | VI-1 | Ccdc122 |
| 2588 | 3 | 4 | 5 | 6 | | VI-1 | Ccdc167 |
| 2589 | 3 | 4 | 5 | 6 | | VI-1 | Ccdc80 |
| 2590 | 3 | 4 | 5 | 6 | | VI-1 | Ccl17 |
| 2591 | 3 | 4 | 5 | 6 | | VI-1 | Ccl2 |
| 2592 | 3 | 4 | 5 | 6 | | VI-1 | Ccl21b |
| 2593 | 3 | 4 | 5 | 6 | | VI-1 | Ccl22 |
| 2594 | 3 | 4 | 5 | 6 | | VI-1 | Ccl3 |
| 2595 | 3 | 4 | 5 | 6 | | VI-1 | Ccl5 |
| 2596 | 3 | 4 | 5 | 6 | | VI-1 | Ccl7 |
| 2597 | 3 | 4 | 5 | 6 | | VI-1 | Ccm2l |
| 2598 | 3 | 4 | 5 | 6 | | VI-1 | Ccnb2 |
| 2599 | 3 | 4 | 5 | 6 | | VI-1 | Ccnd1 |
| 2600 | 3 | 4 | 5 | 6 | | VI-1 | Ccnd2 |
| 2601 | 3 | 4 | 5 | 6 | | VI-1 | Ccne2 |
| 2602 | 3 | 4 | 5 | 6 | | VI-1 | Ccnt1 |
| 2603 | 3 | 4 | 5 | 6 | | VI-1 | Ccr1 |
| 2604 | 3 | 4 | 5 | 6 | | VI-1 | Ccr2 |
| 2605 | 3 | 4 | 5 | 6 | | VI-1 | Ccr5 |
| 2606 | 3 | 4 | 5 | 6 | | VI-1 | Ccrn4l |
| 2607 | 3 | 4 | 5 | 6 | | VI-1 | Cd177 |
| 2608 | 3 | 4 | 5 | 6 | | VI-1 | Cd180 |
| 2609 | 3 | 4 | 5 | 6 | | VI-1 | Cd1d1 |
| 2610 | 3 | 4 | 5 | 6 | | VI-1 | Cd200r4 |
| 2611 | 3 | 4 | 5 | 6 | | VI-1 | Cd247 |
| 2612 | 3 | 4 | 5 | 6 | | VI-1 | Cd248 |
| 2613 | 3 | 4 | 5 | 6 | | VI-1 | Cd274 |
| 2614 | 3 | 4 | 5 | 6 | | VI-1 | Cd300lb |
| 2615 | 3 | 4 | 5 | 6 | | VI-1 | Cd300ld |
| 2616 | 3 | 4 | 5 | 6 | | VI-1 | Cd300lh |
| 2617 | 3 | 4 | 5 | 6 | | VI-1 | Cd33 |
| 2618 | 3 | 4 | 5 | 6 | | VI-1 | Cd52 |
| 2619 | 3 | 4 | 5 | 6 | | VI-1 | Cd5l |
| 2620 | 3 | 4 | 5 | 6 | | VI-1 | Cd63 |
| 2621 | 3 | 4 | 5 | 6 | | VI-1 | Cd68 |
| 2622 | 3 | 4 | 5 | 6 | | VI-1 | Cd80 |
| 2623 | 3 | 4 | 5 | 6 | | VI-1 | Cd8b1 |
| 2624 | 3 | 4 | 5 | 6 | | VI-1 | Cda |
| 2625 | 3 | 4 | 5 | 6 | | VI-1 | Cdc20 |
| 2626 | 3 | 4 | 5 | 6 | | VI-1 | Cdca7l |
| 2627 | 3 | 4 | 5 | 6 | | VI-1 | Cdk1 |
| 2628 | 3 | 4 | 5 | 6 | | VI-1 | Cdkl2 |
| 2629 | 3 | 4 | 5 | 6 | | VI-1 | Cdo1 |
| 2630 | 3 | 4 | 5 | 6 | | VI-1 | Cdsn |
| 2631 | 3 | 4 | 5 | 6 | | VI-1 | Cdt1 |
| 2632 | 3 | 4 | 5 | 6 | | VI-1 | Cebpe |
| 2633 | 3 | 4 | 5 | 6 | | VI-1 | Cela1 |
| 2634 | 3 | 4 | 5 | 6 | | VI-1 | Cend1 |
| 2635 | 3 | 4 | 5 | 6 | | VI-1 | Cenpl |
| 2636 | 3 | 4 | 5 | 6 | | VI-1 | Cenpv |
| 2637 | 3 | 4 | 5 | 6 | | VI-1 | Cenpw |
| 2638 | 3 | 4 | 5 | 6 | | VI-1 | Cep55 |
| 2639 | 3 | 4 | 5 | 6 | | VI-1 | Ces2g |
| 2640 | 3 | 4 | 5 | 6 | | VI-1 | Cfb |
| 2641 | 3 | 4 | 5 | 6 | | VI-1 | Cfi |
| 2642 | 3 | 4 | 5 | 6 | | VI-1 | Chac1 |
| 2643 | 3 | 4 | 5 | 6 | | VI-1 | Chaf1a |
| 2644 | 3 | 4 | 5 | 6 | | VI-1 | Chchd6 |
| 2645 | 3 | 4 | 5 | 6 | | VI-1 | Chil1 |
| 2646 | 3 | 4 | 5 | 6 | | VI-1 | Chil3 |
| 2647 | 3 | 4 | 5 | 6 | | VI-1 | Chrd |
| 2648 | 3 | 4 | 5 | 6 | | VI-1 | Chtf18 |
| 2649 | 3 | 4 | 5 | 6 | | VI-1 | Ciapin1 |
| 2650 | 3 | 4 | 5 | 6 | | VI-1 | Ciart |
| 2651 | 3 | 4 | 5 | 6 | | VI-1 | Cib2 |
| 2652 | 3 | 4 | 5 | 6 | | VI-1 | Cilp |
| 2653 | 3 | 4 | 5 | 6 | | VI-1 | Cirbp |
| 2654 | 3 | 4 | 5 | 6 | | VI-1 | Cited1 |
| 2655 | 3 | 4 | 5 | 6 | | VI-1 | Cited4 |
| 2656 | 3 | 4 | 5 | 6 | | VI-1 | Ckap2 |
| 2657 | 3 | 4 | 5 | 6 | | VI-1 | Ckap2l |
| 2658 | 3 | 4 | 5 | 6 | | VI-1 | Cks2 |
| 2659 | 3 | 4 | 5 | 6 | | VI-1 | Clca1 |
| 2660 | 3 | 4 | 5 | 6 | | VI-1 | Clcn2 |
| 2661 | 3 | 4 | 5 | 6 | | VI-1 | Cldn2 |
| 2662 | 3 | 4 | 5 | 6 | | VI-1 | Cldn5 |
| 2663 | 3 | 4 | 5 | 6 | | VI-1 | Clec10a |
| 2664 | 3 | 4 | 5 | 6 | | VI-1 | Clec11a |
| 2665 | 3 | 4 | 5 | 6 | | VI-1 | Clec12a |
| 2666 | 3 | 4 | 5 | 6 | | VI-1 | Clec1b |
| 2667 | 3 | 4 | 5 | 6 | | VI-1 | Clec3b |
| 2668 | 3 | 4 | 5 | 6 | | VI-1 | Clec4d |
| 2669 | 3 | 4 | 5 | 6 | | VI-1 | Clec4e |
| 2670 | 3 | 4 | 5 | 6 | | VI-1 | Clpb |
| 2671 | 3 | 4 | 5 | 6 | | VI-1 | Clu |
| 2672 | 3 | 4 | 5 | 6 | | VI-1 | Cml1 |
| 2673 | 3 | 4 | 5 | 6 | | VI-1 | Cml2 |
| 2674 | 3 | 4 | 5 | 6 | | VI-1 | Cml5 |
| 2675 | 3 | 4 | 5 | 6 | | VI-1 | Cnr2 |
| 2676 | 3 | 4 | 5 | 6 | | VI-1 | Col12a1 |
| 2677 | 3 | 4 | 5 | 6 | | VI-1 | Col15a1 |
| 2678 | 3 | 4 | 5 | 6 | | VI-1 | Col1a2 |
| 2679 | 3 | 4 | 5 | 6 | | VI-1 | Colq |
| 2680 | 3 | 4 | 5 | 6 | | VI-1 | Commd3 |
| 2681 | 3 | 4 | 5 | 6 | | VI-1 | Cox5b |
| 2682 | 3 | 4 | 5 | 6 | | VI-1 | Cox8b |
| 2683 | 3 | 4 | 5 | 6 | | VI-1 | Cpd |
| 2684 | 3 | 4 | 5 | 6 | | VI-1 | Cpeb4 |
| 2685 | 3 | 4 | 5 | 6 | | VI-1 | Cpn2 |
| 2686 | 3 | 4 | 5 | 6 | | VI-1 | Cpne2 |
| 2687 | 3 | 4 | 5 | 6 | | VI-1 | Cpox |
| 2688 | 3 | 4 | 5 | 6 | | VI-1 | Cpt1b |
| 2689 | 3 | 4 | 5 | 6 | | VI-1 | Cpxm1 |
| 2690 | 3 | 4 | 5 | 6 | | VI-1 | Crct1 |
| 2691 | 3 | 4 | 5 | 6 | | VI-1 | Crispld2 |
| 2692 | 3 | 4 | 5 | 6 | | VI-1 | Cth |
| 2693 | 3 | 4 | 5 | 6 | | VI-1 | Ctla2a |
| 2694 | 3 | 4 | 5 | 6 | | VI-1 | Ctsc |
| 2695 | 3 | 4 | 5 | 6 | | VI-1 | Ctsg |
| 2696 | 3 | 4 | 5 | 6 | | VI-1 | Ctss |
| 2697 | 3 | 4 | 5 | 6 | | VI-1 | Ctu2 |
| 2698 | 3 | 4 | 5 | 6 | | VI-1 | Cxcl1 |
| 2699 | 3 | 4 | 5 | 6 | | VI-1 | Cxcl10 |
| 2700 | 3 | 4 | 5 | 6 | | VI-1 | Cxcl13 |
| 2701 | 3 | 4 | 5 | 6 | | VI-1 | Cxcl2 |
| 2702 | 3 | 4 | 5 | 6 | | VI-1 | Cxcr2 |
| 2703 | 3 | 4 | 5 | 6 | | VI-1 | Cxcr4 |
| 2704 | 3 | 4 | 5 | 6 | | VI-1 | Cyb561 |
| 2705 | 3 | 4 | 5 | 6 | | VI-1 | Cyp1a1 |
| 2706 | 3 | 4 | 5 | 6 | | VI-1 | Cyp27a1 |
| 2707 | 3 | 4 | 5 | 6 | | VI-1 | Cyp2a22 |
| 2708 | 3 | 4 | 5 | 6 | | VI-1 | Cyp2b10 |
| 2709 | 3 | 4 | 5 | 6 | | VI-1 | Cyp2c70 |
| 2710 | 3 | 4 | 5 | 6 | | VI-1 | Cyp2d26 |
| 2711 | 3 | 4 | 5 | 6 | | VI-1 | Cyp2e1 |
| 2712 | 3 | 4 | 5 | 6 | | VI-1 | Cyp2f2 |
| 2713 | 3 | 4 | 5 | 6 | | VI-1 | Cyp4a10 |
| 2714 | 3 | 4 | 5 | 6 | | VI-1 | Cyp4a14 |
| 2715 | 3 | 4 | 5 | 6 | | VI-1 | Cyp4f17 |
| 2716 | 3 | 4 | 5 | 6 | | VI-1 | Cyr61 |
| 2717 | 3 | 4 | 5 | 6 | | VI-1 | D10Bwg1379e |
| 2718 | 3 | 4 | 5 | 6 | | VI-1 | D330041H03Rik |

Fig. 43 - 17

| | | | | | | | | | | | | | | | | | |
|---|---|---|---|---|---|---|---|---|---|---|---|---|---|---|---|---|---|
| 2719 | 3 | 4 | 5 | 6 | | | VI-1 | D7Ertd715e | | 2804 | 3 | 4 | 5 | 6 | | VI-1 | Ephx1 |
| 2720 | 3 | 4 | 5 | 6 | | | VI-1 | D830013O20Rik | | 2805 | 3 | 4 | 5 | 6 | | VI-1 | Epm2a |
| 2721 | 3 | 4 | 5 | 6 | | | VI-1 | D930048N14Rik | | 2806 | 3 | 4 | 5 | 6 | | VI-1 | Epm2aip1 |
| 2722 | 3 | 4 | 5 | 6 | | | VI-1 | Dact2 | | 2807 | 3 | 4 | 5 | 6 | | VI-1 | Epn3 |
| 2723 | 3 | 4 | 5 | 6 | | | VI-1 | Dapl1 | | 2808 | 3 | 4 | 5 | 6 | | VI-1 | Epo |
| 2724 | 3 | 4 | 5 | 6 | | | VI-1 | Dbp | | 2809 | 3 | 4 | 5 | 6 | | VI-1 | Epsti1 |
| 2725 | 3 | 4 | 5 | 6 | | | VI-1 | Dcaf12l1 | | 2810 | 3 | 4 | 5 | 6 | | VI-1 | Epx |
| 2726 | 3 | 4 | 5 | 6 | | | VI-1 | Dck | | 2811 | 3 | 4 | 5 | 6 | | VI-1 | Erich5 |
| 2727 | 3 | 4 | 5 | 6 | | | VI-1 | Dcxr | | 2812 | 3 | 4 | 5 | 6 | | VI-1 | Ern1 |
| 2728 | 3 | 4 | 5 | 6 | | | VI-1 | Ddc | | 2813 | 3 | 4 | 5 | 6 | | VI-1 | Ero1l |
| 2729 | 3 | 4 | 5 | 6 | | | VI-1 | Ddi2 | | 2814 | 3 | 4 | 5 | 6 | | VI-1 | Erp27 |
| 2730 | 3 | 4 | 5 | 6 | | | VI-1 | Def6 | | 2815 | 3 | 4 | 5 | 6 | | VI-1 | Esd |
| 2731 | 3 | 4 | 5 | 6 | | | VI-1 | Defa2 | | 2816 | 3 | 4 | 5 | 6 | | VI-1 | Esp8 |
| 2732 | 3 | 4 | 5 | 6 | | | VI-1 | Defa22 | | 2817 | 3 | 4 | 5 | 6 | | VI-1 | Etohd2 |
| 2733 | 3 | 4 | 5 | 6 | | | VI-1 | Defb8 | | 2818 | 3 | 4 | 5 | 6 | | VI-1 | Etohi1 |
| 2734 | 3 | 4 | 5 | 6 | | | VI-1 | Derl3 | | 2819 | 3 | 4 | 5 | 6 | | VI-1 | Ets1 |
| 2735 | 3 | 4 | 5 | 6 | | | VI-1 | Desi2 | | 2820 | 3 | 4 | 5 | 6 | | VI-1 | Evi2a |
| 2736 | 3 | 4 | 5 | 6 | | | VI-1 | Dgat2 | | 2821 | 3 | 4 | 5 | 6 | | VI-1 | Exoc4 |
| 2737 | 3 | 4 | 5 | 6 | | | VI-1 | Dhcr24 | | 2822 | 3 | 4 | 5 | 6 | | VI-1 | Exosc8 |
| 2738 | 3 | 4 | 5 | 6 | | | VI-1 | Dhrs7c | | 2823 | 3 | 4 | 5 | 6 | | VI-1 | Extl1 |
| 2739 | 3 | 4 | 5 | 6 | | | VI-1 | Dhx58 | | 2824 | 3 | 4 | 5 | 6 | | VI-1 | Extl2 |
| 2740 | 3 | 4 | 5 | 6 | | | VI-1 | Dio2 | | 2825 | 3 | 4 | 5 | 6 | | VI-1 | F11 |
| 2741 | 3 | 4 | 5 | 6 | | | VI-1 | Diras2 | | 2826 | 3 | 4 | 5 | 6 | | VI-1 | F2rl2 |
| 2742 | 3 | 4 | 5 | 6 | | | VI-1 | Dis3 | | 2827 | 3 | 4 | 5 | 6 | | VI-1 | F5 |
| 2743 | 3 | 4 | 5 | 6 | | | VI-1 | Disp2 | | 2828 | 3 | 4 | 5 | 6 | | VI-1 | Fabp4 |
| 2744 | 3 | 4 | 5 | 6 | | | VI-1 | Dkk2 | | 2829 | 3 | 4 | 5 | 6 | | VI-1 | Fabp5 |
| 2745 | 3 | 4 | 5 | 6 | | | VI-1 | Dkk3 | | 2830 | 3 | 4 | 5 | 6 | | VI-1 | Fabp6 |
| 2746 | 3 | 4 | 5 | 6 | | | VI-1 | Dmbt1 | | 2831 | 3 | 4 | 5 | 6 | | VI-1 | Fads2 |
| 2747 | 3 | 4 | 5 | 6 | | | VI-1 | Dmkn | | 2832 | 3 | 4 | 5 | 6 | | VI-1 | Fads6 |
| 2748 | 3 | 4 | 5 | 6 | | | VI-1 | Dnajb1 | | 2833 | 3 | 4 | 5 | 6 | | VI-1 | Faim |
| 2749 | 3 | 4 | 5 | 6 | | | VI-1 | Dnajb3 | | 2834 | 3 | 4 | 5 | 6 | | VI-1 | Fam110a |
| 2750 | 3 | 4 | 5 | 6 | | | VI-1 | Dnajc12 | | 2835 | 3 | 4 | 5 | 6 | | VI-1 | Fam110b |
| 2751 | 3 | 4 | 5 | 6 | | | VI-1 | Dnajc15 | | 2836 | 3 | 4 | 5 | 6 | | VI-1 | Fam118a |
| 2752 | 3 | 4 | 5 | 6 | | | VI-1 | Dnajc4 | | 2837 | 3 | 4 | 5 | 6 | | VI-1 | Fam129a |
| 2753 | 3 | 4 | 5 | 6 | | | VI-1 | Dnajc6 | | 2838 | 3 | 4 | 5 | 6 | | VI-1 | Fam134b |
| 2754 | 3 | 4 | 5 | 6 | | | VI-1 | Dnase1l3 | | 2839 | 3 | 4 | 5 | 6 | | VI-1 | Fam167a |
| 2755 | 3 | 4 | 5 | 6 | | | VI-1 | Dnd1 | | 2840 | 3 | 4 | 5 | 6 | | VI-1 | Fam169b |
| 2756 | 3 | 4 | 5 | 6 | | | VI-1 | Dnph1 | | 2841 | 3 | 4 | 5 | 6 | | VI-1 | Fam180a |
| 2757 | 3 | 4 | 5 | 6 | | | VI-1 | Dok2 | | 2842 | 3 | 4 | 5 | 6 | | VI-1 | Fam195a |
| 2758 | 3 | 4 | 5 | 6 | | | VI-1 | Dot1l | | 2843 | 3 | 4 | 5 | 6 | | VI-1 | Fam209 |
| 2759 | 3 | 4 | 5 | 6 | | | VI-1 | Dpcr1 | | 2844 | 3 | 4 | 5 | 6 | | VI-1 | Fam212a |
| 2760 | 3 | 4 | 5 | 6 | | | VI-1 | Dpep2 | | 2845 | 3 | 4 | 5 | 6 | | VI-1 | Fam212b |
| 2761 | 3 | 4 | 5 | 6 | | | VI-1 | Dph1 | | 2846 | 3 | 4 | 5 | 6 | | VI-1 | Fam219aos |
| 2762 | 3 | 4 | 5 | 6 | | | VI-1 | Dpt | | 2847 | 3 | 4 | 5 | 6 | | VI-1 | Fam25c |
| 2763 | 3 | 4 | 5 | 6 | | | VI-1 | Drap1 | | 2848 | 3 | 4 | 5 | 6 | | VI-1 | Fam26f |
| 2764 | 3 | 4 | 5 | 6 | | | VI-1 | Drd4 | | 2849 | 3 | 4 | 5 | 6 | | VI-1 | Fam46b |
| 2765 | 3 | 4 | 5 | 6 | | | VI-1 | Drp2 | | 2850 | 3 | 4 | 5 | 6 | | VI-1 | Fam46c |
| 2766 | 3 | 4 | 5 | 6 | | | VI-1 | Dscc1 | | 2851 | 3 | 4 | 5 | 6 | | VI-1 | Fam47e |
| 2767 | 3 | 4 | 5 | 6 | | | VI-1 | Dsg1c | | 2852 | 3 | 4 | 5 | 6 | | VI-1 | Fam57a |
| 2768 | 3 | 4 | 5 | 6 | | | VI-1 | Dsp | | 2853 | 3 | 4 | 5 | 6 | | VI-1 | Fam64a |
| 2769 | 3 | 4 | 5 | 6 | | | VI-1 | Dtl | | 2854 | 3 | 4 | 5 | 6 | | VI-1 | Fam69b |
| 2770 | 3 | 4 | 5 | 6 | | | VI-1 | Dtna | | 2855 | 3 | 4 | 5 | 6 | | VI-1 | Fam73b |
| 2771 | 3 | 4 | 5 | 6 | | | VI-1 | Dupd1 | | 2856 | 3 | 4 | 5 | 6 | | VI-1 | Fam78a |
| 2772 | 3 | 4 | 5 | 6 | | | VI-1 | Dusp15 | | 2857 | 3 | 4 | 5 | 6 | | VI-1 | Far2 |
| 2773 | 3 | 4 | 5 | 6 | | | VI-1 | Dut | | 2858 | 3 | 4 | 5 | 6 | | VI-1 | Fat1 |
| 2774 | 3 | 4 | 5 | 6 | | | VI-1 | Dvl3 | | 2859 | 3 | 4 | 5 | 6 | | VI-1 | Fat2 |
| 2775 | 3 | 4 | 5 | 6 | | | VI-1 | Dynlt1f | | 2860 | 3 | 4 | 5 | 6 | | VI-1 | Fau |
| 2776 | 3 | 4 | 5 | 6 | | | VI-1 | Dyrk2 | | 2861 | 3 | 4 | 5 | 6 | | VI-1 | Fbln1 |
| 2777 | 3 | 4 | 5 | 6 | | | VI-1 | Dyrk3 | | 2862 | 3 | 4 | 5 | 6 | | VI-1 | Fbxl18 |
| 2778 | 3 | 4 | 5 | 6 | | | VI-1 | Dzip1l | | 2863 | 3 | 4 | 5 | 6 | | VI-1 | Fbxl22 |
| 2779 | 3 | 4 | 5 | 6 | | | VI-1 | E030011O05Rik | | 2864 | 3 | 4 | 5 | 6 | | VI-1 | Fbxo32 |
| 2780 | 3 | 4 | 5 | 6 | | | VI-1 | E030018B13Rik | | 2865 | 3 | 4 | 5 | 6 | | VI-1 | Fbxo36 |
| 2781 | 3 | 4 | 5 | 6 | | | VI-1 | E130317F20Rik | | 2866 | 3 | 4 | 5 | 6 | | VI-1 | Fbxo40 |
| 2782 | 3 | 4 | 5 | 6 | | | VI-1 | E2f1 | | 2867 | 3 | 4 | 5 | 6 | | VI-1 | Fcgr1 |
| 2783 | 3 | 4 | 5 | 6 | | | VI-1 | E330009J07Rik | | 2868 | 3 | 4 | 5 | 6 | | VI-1 | Fcgr4 |
| 2784 | 3 | 4 | 5 | 6 | | | VI-1 | Ear6 | | 2869 | 3 | 4 | 5 | 6 | | VI-1 | Fcna |
| 2785 | 3 | 4 | 5 | 6 | | | VI-1 | Ear7 | | 2870 | 3 | 4 | 5 | 6 | | VI-1 | Fdps |
| 2786 | 3 | 4 | 5 | 6 | | | VI-1 | Egr1 | | 2871 | 3 | 4 | 5 | 6 | | VI-1 | Fem1c |
| 2787 | 3 | 4 | 5 | 6 | | | VI-1 | Eid3 | | 2872 | 3 | 4 | 5 | 6 | | VI-1 | Fen1 |
| 2788 | 3 | 4 | 5 | 6 | | | VI-1 | Eif3j2 | | 2873 | 3 | 4 | 5 | 6 | | VI-1 | Fez2 |
| 2789 | 3 | 4 | 5 | 6 | | | VI-1 | Eif4ebp2 | | 2874 | 3 | 4 | 5 | 6 | | VI-1 | Ffar4 |
| 2790 | 3 | 4 | 5 | 6 | | | VI-1 | Elk4 | | 2875 | 3 | 4 | 5 | 6 | | VI-1 | Fgb |
| 2791 | 3 | 4 | 5 | 6 | | | VI-1 | Elovl4 | | 2876 | 3 | 4 | 5 | 6 | | VI-1 | Fgf1 |
| 2792 | 3 | 4 | 5 | 6 | | | VI-1 | Emc9 | | 2877 | 3 | 4 | 5 | 6 | | VI-1 | Fgf13 |
| 2793 | 3 | 4 | 5 | 6 | | | VI-1 | Emcn | | 2878 | 3 | 4 | 5 | 6 | | VI-1 | Fgf16 |
| 2794 | 3 | 4 | 5 | 6 | | | VI-1 | Emilin2 | | 2879 | 3 | 4 | 5 | 6 | | VI-1 | Fgl1 |
| 2795 | 3 | 4 | 5 | 6 | | | VI-1 | Emp1 | | 2880 | 3 | 4 | 5 | 6 | | VI-1 | Fgl2 |
| 2796 | 3 | 4 | 5 | 6 | | | VI-1 | Emp3 | | 2881 | 3 | 4 | 5 | 6 | | VI-1 | Fgr |
| 2797 | 3 | 4 | 5 | 6 | | | VI-1 | Endou | | 2882 | 3 | 4 | 5 | 6 | | VI-1 | Fhit |
| 2798 | 3 | 4 | 5 | 6 | | | VI-1 | Enkd1 | | 2883 | 3 | 4 | 5 | 6 | | VI-1 | Fhl1 |
| 2799 | 3 | 4 | 5 | 6 | | | VI-1 | Eno1 | | 2884 | 3 | 4 | 5 | 6 | | VI-1 | Fhl3 |
| 2800 | 3 | 4 | 5 | 6 | | | VI-1 | Enpp2 | | 2885 | 3 | 4 | 5 | 6 | | VI-1 | Figf |
| 2801 | 3 | 4 | 5 | 6 | | | VI-1 | Eomes | | 2886 | 3 | 4 | 5 | 6 | | VI-1 | Filip1 |
| 2802 | 3 | 4 | 5 | 6 | | | VI-1 | Epdr1 | | 2887 | 3 | 4 | 5 | 6 | | VI-1 | Fkbp1b |
| 2803 | 3 | 4 | 5 | 6 | | | VI-1 | Ephb3 | | 2888 | 3 | 4 | 5 | 6 | | VI-1 | Fndc5 |

Fig. 43 - 18

| | | | | | | | | |
|---|---|---|---|---|---|---|---|---|
| 2889 | 3 | 4 | 5 | 6 | | VI-1 | Fos |
| 2890 | 3 | 4 | 5 | 6 | | VI-1 | Foxo3 |
| 2891 | 3 | 4 | 5 | 6 | | VI-1 | Foxo6 |
| 2892 | 3 | 4 | 5 | 6 | | VI-1 | Fpr1 |
| 2893 | 3 | 4 | 5 | 6 | | VI-1 | Fpr2 |
| 2894 | 3 | 4 | 5 | 6 | | VI-1 | Frrs1 |
| 2895 | 3 | 4 | 5 | 6 | | VI-1 | Frzb |
| 2896 | 3 | 4 | 5 | 6 | | VI-1 | Fscn2 |
| 2897 | 3 | 4 | 5 | 6 | | VI-1 | Ftcd |
| 2898 | 3 | 4 | 5 | 6 | | VI-1 | Fut1 |
| 2899 | 3 | 4 | 5 | 6 | | VI-1 | Fut4 |
| 2900 | 3 | 4 | 5 | 6 | | VI-1 | Fxyd7 |
| 2901 | 3 | 4 | 5 | 6 | | VI-1 | Fzd4 |
| 2902 | 3 | 4 | 5 | 6 | | VI-1 | Fzd9 |
| 2903 | 3 | 4 | 5 | 6 | | VI-1 | Gabrr2 |
| 2904 | 3 | 4 | 5 | 6 | | VI-1 | Gadd45a |
| 2905 | 3 | 4 | 5 | 6 | | VI-1 | Gadl1 |
| 2906 | 3 | 4 | 5 | 6 | | VI-1 | Gal3st3 |
| 2907 | 3 | 4 | 5 | 6 | | VI-1 | Galnt15 |
| 2908 | 3 | 4 | 5 | 6 | | VI-1 | Gapdh |
| 2909 | 3 | 4 | 5 | 6 | | VI-1 | Garem |
| 2910 | 3 | 4 | 5 | 6 | | VI-1 | Gas1 |
| 2911 | 3 | 4 | 5 | 6 | | VI-1 | Gas2 |
| 2912 | 3 | 4 | 5 | 6 | | VI-1 | Gata1 |
| 2913 | 3 | 4 | 5 | 6 | | VI-1 | Gatm |
| 2914 | 3 | 4 | 5 | 6 | | VI-1 | Gatsl2 |
| 2915 | 3 | 4 | 5 | 6 | | VI-1 | Gatsl3 |
| 2916 | 3 | 4 | 5 | 6 | | VI-1 | Gbgt1 |
| 2917 | 3 | 4 | 5 | 6 | | VI-1 | Gbp10 |
| 2918 | 3 | 4 | 5 | 6 | | VI-1 | Gbp3 |
| 2919 | 3 | 4 | 5 | 6 | | VI-1 | Gbp6 |
| 2920 | 3 | 4 | 5 | 6 | | VI-1 | Gbp9 |
| 2921 | 3 | 4 | 5 | 6 | | VI-1 | Gc |
| 2922 | 3 | 4 | 5 | 6 | | VI-1 | Gcat |
| 2923 | 3 | 4 | 5 | 6 | | VI-1 | Gck |
| 2924 | 3 | 4 | 5 | 6 | | VI-1 | Gclc |
| 2925 | 3 | 4 | 5 | 6 | | VI-1 | Gda |
| 2926 | 3 | 4 | 5 | 6 | | VI-1 | Gdf5 |
| 2927 | 3 | 4 | 5 | 6 | | VI-1 | Gfi1b |
| 2928 | 3 | 4 | 5 | 6 | | VI-1 | Gfra1 |
| 2929 | 3 | 4 | 5 | 6 | | VI-1 | Gfra4 |
| 2930 | 3 | 4 | 5 | 6 | | VI-1 | Ggct |
| 2931 | 3 | 4 | 5 | 6 | | VI-1 | Ggt1 |
| 2932 | 3 | 4 | 5 | 6 | | VI-1 | Gimap3 |
| 2933 | 3 | 4 | 5 | 6 | | VI-1 | Gimap4 |
| 2934 | 3 | 4 | 5 | 6 | | VI-1 | Gimap7 |
| 2935 | 3 | 4 | 5 | 6 | | VI-1 | Gins1 |
| 2936 | 3 | 4 | 5 | 6 | | VI-1 | Gja1 |
| 2937 | 3 | 4 | 5 | 6 | | VI-1 | Gjb2 |
| 2938 | 3 | 4 | 5 | 6 | | VI-1 | Gk2 |
| 2939 | 3 | 4 | 5 | 6 | | VI-1 | Gkn2 |
| 2940 | 3 | 4 | 5 | 6 | | VI-1 | Gla |
| 2941 | 3 | 4 | 5 | 6 | | VI-1 | Glg1 |
| 2942 | 3 | 4 | 5 | 6 | | VI-1 | Glipr1 |
| 2943 | 3 | 4 | 5 | 6 | | VI-1 | Gm10058 |
| 2944 | 3 | 4 | 5 | 6 | | VI-1 | Gm10560 |
| 2945 | 3 | 4 | 5 | 6 | | VI-1 | Gm10872 |
| 2946 | 3 | 4 | 5 | 6 | | VI-1 | Gm11517 |
| 2947 | 3 | 4 | 5 | 6 | | VI-1 | Gm11974 |
| 2948 | 3 | 4 | 5 | 6 | | VI-1 | Gm12070 |
| 2949 | 3 | 4 | 5 | 6 | | VI-1 | Gm12185 |
| 2950 | 3 | 4 | 5 | 6 | | VI-1 | Gm12216 |
| 2951 | 3 | 4 | 5 | 6 | | VI-1 | Gm13124 |
| 2952 | 3 | 4 | 5 | 6 | | VI-1 | Gm13251 |
| 2953 | 3 | 4 | 5 | 6 | | VI-1 | Gm13306 |
| 2954 | 3 | 4 | 5 | 6 | | VI-1 | Gm13710 |
| 2955 | 3 | 4 | 5 | 6 | | VI-1 | Gm13889 |
| 2956 | 3 | 4 | 5 | 6 | | VI-1 | Gm14288 |
| 2957 | 3 | 4 | 5 | 6 | | VI-1 | Gm14391 |
| 2958 | 3 | 4 | 5 | 6 | | VI-1 | Gm14446 |
| 2959 | 3 | 4 | 5 | 6 | | VI-1 | Gm14548 |
| 2960 | 3 | 4 | 5 | 6 | | VI-1 | Gm15133 |
| 2961 | 3 | 4 | 5 | 6 | | VI-1 | Gm15408 |
| 2962 | 3 | 4 | 5 | 6 | | VI-1 | Gm15706 |
| 2963 | 3 | 4 | 5 | 6 | | VI-1 | Gm15915 |
| 2964 | 3 | 4 | 5 | 6 | | VI-1 | Gm15987 |
| 2965 | 3 | 4 | 5 | 6 | | VI-1 | Gm16548 |
| 2966 | 3 | 4 | 5 | 6 | | VI-1 | Gm16793 |
| 2967 | 3 | 4 | 5 | 6 | | VI-1 | Gm16907 |
| 2968 | 3 | 4 | 5 | 6 | | VI-1 | Gm18853 |
| 2969 | 3 | 4 | 5 | 6 | | VI-1 | Gm19705 |
| 2970 | 3 | 4 | 5 | 6 | | VI-1 | Gm20823 |
| 2971 | 3 | 4 | 5 | 6 | | VI-1 | Gm2083 |
| 2972 | 3 | 4 | 5 | 6 | | VI-1 | Gm20878 |
| 2973 | 3 | 4 | 5 | 6 | | VI-1 | Gm21498 |
| 2974 | 3 | 4 | 5 | 6 | | VI-1 | Gm21541 |
| 2975 | 3 | 4 | 5 | 6 | | VI-1 | Gm2373 |
| 2976 | 3 | 4 | 5 | 6 | | VI-1 | Gm3646 |
| 2977 | 3 | 4 | 5 | 6 | | VI-1 | Gm3776 |
| 2978 | 3 | 4 | 5 | 6 | | VI-1 | Gm4013 |
| 2979 | 3 | 4 | 5 | 6 | | VI-1 | Gm4841 |
| 2980 | 3 | 4 | 5 | 6 | | VI-1 | Gm4951 |
| 2981 | 3 | 4 | 5 | 6 | | VI-1 | Gm4980 |
| 2982 | 3 | 4 | 5 | 6 | | VI-1 | Gm5105 |
| 2983 | 3 | 4 | 5 | 6 | | VI-1 | Gm5108 |
| 2984 | 3 | 4 | 5 | 6 | | VI-1 | Gm5124 |
| 2985 | 3 | 4 | 5 | 6 | | VI-1 | Gm5150 |
| 2986 | 3 | 4 | 5 | 6 | | VI-1 | Gm5294 |
| 2987 | 3 | 4 | 5 | 6 | | VI-1 | Gm5424 |
| 2988 | 3 | 4 | 5 | 6 | | VI-1 | Gm5617 |
| 2989 | 3 | 4 | 5 | 6 | | VI-1 | Gm5634 |
| 2990 | 3 | 4 | 5 | 6 | | VI-1 | Gm5643 |
| 2991 | 3 | 4 | 5 | 6 | | VI-1 | Gm6297 |
| 2992 | 3 | 4 | 5 | 6 | | VI-1 | Gm6484 |
| 2993 | 3 | 4 | 5 | 6 | | VI-1 | Gm6607 |
| 2994 | 3 | 4 | 5 | 6 | | VI-1 | Gm694 |
| 2995 | 3 | 4 | 5 | 6 | | VI-1 | Gm715 |
| 2996 | 3 | 4 | 5 | 6 | | VI-1 | Gm7325 |
| 2997 | 3 | 4 | 5 | 6 | | VI-1 | Gm7694 |
| 2998 | 3 | 4 | 5 | 6 | | VI-1 | Gm7861 |
| 2999 | 3 | 4 | 5 | 6 | | VI-1 | Gm904 |
| 3000 | 3 | 4 | 5 | 6 | | VI-1 | Gm9733 |
| 3001 | 3 | 4 | 5 | 6 | | VI-1 | Gm9895 |
| 3002 | 3 | 4 | 5 | 6 | | VI-1 | Gm9992 |
| 3003 | 3 | 4 | 5 | 6 | | VI-1 | Gmds |
| 3004 | 3 | 4 | 5 | 6 | | VI-1 | Gna12 |
| 3005 | 3 | 4 | 5 | 6 | | VI-1 | Gnat1 |
| 3006 | 3 | 4 | 5 | 6 | | VI-1 | Gng11 |
| 3007 | 3 | 4 | 5 | 6 | | VI-1 | Got1 |
| 3008 | 3 | 4 | 5 | 6 | | VI-1 | Gp1bb |
| 3009 | 3 | 4 | 5 | 6 | | VI-1 | Gp49a |
| 3010 | 3 | 4 | 5 | 6 | | VI-1 | Gp5 |
| 3011 | 3 | 4 | 5 | 6 | | VI-1 | Gp9 |
| 3012 | 3 | 4 | 5 | 6 | | VI-1 | Gpatch3 |
| 3013 | 3 | 4 | 5 | 6 | | VI-1 | Gpc1 |
| 3014 | 3 | 4 | 5 | 6 | | VI-1 | Gpld1 |
| 3015 | 3 | 4 | 5 | 6 | | VI-1 | Gpnmb |
| 3016 | 3 | 4 | 5 | 6 | | VI-1 | Gpr137b-ps |
| 3017 | 3 | 4 | 5 | 6 | | VI-1 | Gpr141 |
| 3018 | 3 | 4 | 5 | 6 | | VI-1 | Gpr150 |
| 3019 | 3 | 4 | 5 | 6 | | VI-1 | Gpr35 |
| 3020 | 3 | 4 | 5 | 6 | | VI-1 | Gprin1 |
| 3021 | 3 | 4 | 5 | 6 | | VI-1 | Gpx2 |
| 3022 | 3 | 4 | 5 | 6 | | VI-1 | Grem1 |
| 3023 | 3 | 4 | 5 | 6 | | VI-1 | Gria3 |
| 3024 | 3 | 4 | 5 | 6 | | VI-1 | Gsdmc |
| 3025 | 3 | 4 | 5 | 6 | | VI-1 | Gsta3 |
| 3026 | 3 | 4 | 5 | 6 | | VI-1 | Gstm1 |
| 3027 | 3 | 4 | 5 | 6 | | VI-1 | Gstm2 |
| 3028 | 3 | 4 | 5 | 6 | | VI-1 | Gstm5 |
| 3029 | 3 | 4 | 5 | 6 | | VI-1 | Gstp1 |
| 3030 | 3 | 4 | 5 | 6 | | VI-1 | Gstp2 |
| 3031 | 3 | 4 | 5 | 6 | | VI-1 | Gstt3 |
| 3032 | 3 | 4 | 5 | 6 | | VI-1 | Gtse1 |
| 3033 | 3 | 4 | 5 | 6 | | VI-1 | Gvin1 |
| 3034 | 3 | 4 | 5 | 6 | | VI-1 | Gyk |
| 3035 | 3 | 4 | 5 | 6 | | VI-1 | Gzma |
| 3036 | 3 | 4 | 5 | 6 | | VI-1 | Gzmb |
| 3037 | 3 | 4 | 5 | 6 | | VI-1 | H2-M3 |
| 3038 | 3 | 4 | 5 | 6 | | VI-1 | H2-Q4 |
| 3039 | 3 | 4 | 5 | 6 | | VI-1 | H2-Q5 |
| 3040 | 3 | 4 | 5 | 6 | | VI-1 | H2-Q7 |
| 3041 | 3 | 4 | 5 | 6 | | VI-1 | H2-T10 |
| 3042 | 3 | 4 | 5 | 6 | | VI-1 | H2-T22 |
| 3043 | 3 | 4 | 5 | 6 | | VI-1 | Hao1 |
| 3044 | 3 | 4 | 5 | 6 | | VI-1 | Haus7 |
| 3045 | 3 | 4 | 5 | 6 | | VI-1 | Havcr1 |
| 3046 | 3 | 4 | 5 | 6 | | VI-1 | Hbegf |
| 3047 | 3 | 4 | 5 | 6 | | VI-1 | Hck |
| 3048 | 3 | 4 | 5 | 6 | | VI-1 | Hcn2 |
| 3049 | 3 | 4 | 5 | 6 | | VI-1 | Hcst |
| 3050 | 3 | 4 | 5 | 6 | | VI-1 | Hdc |
| 3051 | 3 | 4 | 5 | 6 | | VI-1 | Hddc2 |
| 3052 | 3 | 4 | 5 | 6 | | VI-1 | Hdhd3 |
| 3053 | 3 | 4 | 5 | 6 | | VI-1 | Heg1 |
| 3054 | 3 | 4 | 5 | 6 | | VI-1 | Helz2 |
| 3055 | 3 | 4 | 5 | 6 | | VI-1 | Hey1 |
| 3056 | 3 | 4 | 5 | 6 | | VI-1 | Hhatl |
| 3057 | 3 | 4 | 5 | 6 | | VI-1 | Hint2 |
| 3058 | 3 | 4 | 5 | 6 | | VI-1 | Hist1h1c |

Fig. 43 - 19

| | | | | | | | | | | | | | | | | |
|---|---|---|---|---|---|---|---|---|---|---|---|---|---|---|---|---|
| 3059 | 3 | 4 | 5 | 6 | | | VI-1 | Hist1h1d | | 3144 | 3 | 4 | 5 | 6 | | | VI-1 | Il1r2 |
| 3060 | 3 | 4 | 5 | 6 | | | VI-1 | Hist1h1e | | 3145 | 3 | 4 | 5 | 6 | | | VI-1 | Il1rl1 |
| 3061 | 3 | 4 | 5 | 6 | | | VI-1 | Hist1h2ac | | 3146 | 3 | 4 | 5 | 6 | | | VI-1 | Il1rl2 |
| 3062 | 3 | 4 | 5 | 6 | | | VI-1 | Hist1h2af | | 3147 | 3 | 4 | 5 | 6 | | | VI-1 | Il1rn |
| 3063 | 3 | 4 | 5 | 6 | | | VI-1 | Hist1h2ag | | 3148 | 3 | 4 | 5 | 6 | | | VI-1 | Il2rg |
| 3064 | 3 | 4 | 5 | 6 | | | VI-1 | Hist1h2ah | | 3149 | 3 | 4 | 5 | 6 | | | VI-1 | Il31ra |
| 3065 | 3 | 4 | 5 | 6 | | | VI-1 | Hist1h2ai | | 3150 | 3 | 4 | 5 | 6 | | | VI-1 | Il33 |
| 3066 | 3 | 4 | 5 | 6 | | | VI-1 | Hist1h2ap | | 3151 | 3 | 4 | 5 | 6 | | | VI-1 | Il6ra |
| 3067 | 3 | 4 | 5 | 6 | | | VI-1 | Hist1h2ba | | 3152 | 3 | 4 | 5 | 6 | | | VI-1 | Impad1 |
| 3068 | 3 | 4 | 5 | 6 | | | VI-1 | Hist1h2be | | 3153 | 3 | 4 | 5 | 6 | | | VI-1 | Inhbb |
| 3069 | 3 | 4 | 5 | 6 | | | VI-1 | Hist1h2bf | | 3154 | 3 | 4 | 5 | 6 | | | VI-1 | Inhbe |
| 3070 | 3 | 4 | 5 | 6 | | | VI-1 | Hist1h2bg | | 3155 | 3 | 4 | 5 | 6 | | | VI-1 | Insc |
| 3071 | 3 | 4 | 5 | 6 | | | VI-1 | Hist1h2bj | | 3156 | 3 | 4 | 5 | 6 | | | VI-1 | Insl3 |
| 3072 | 3 | 4 | 5 | 6 | | | VI-1 | Hist1h2bk | | 3157 | 3 | 4 | 5 | 6 | | | VI-1 | Ipo13 |
| 3073 | 3 | 4 | 5 | 6 | | | VI-1 | Hist1h2bl | | 3158 | 3 | 4 | 5 | 6 | | | VI-1 | Irf7 |
| 3074 | 3 | 4 | 5 | 6 | | | VI-1 | Hist1h2bm | | 3159 | 3 | 4 | 5 | 6 | | | VI-1 | Irg1 |
| 3075 | 3 | 4 | 5 | 6 | | | VI-1 | Hist1h2bn | | 3160 | 3 | 4 | 5 | 6 | | | VI-1 | Irs2 |
| 3076 | 3 | 4 | 5 | 6 | | | VI-1 | Hist1h2bp | | 3161 | 3 | 4 | 5 | 6 | | | VI-1 | Irx1 |
| 3077 | 3 | 4 | 5 | 6 | | | VI-1 | Hist1h2bq | | 3162 | 3 | 4 | 5 | 6 | | | VI-1 | Isg20 |
| 3078 | 3 | 4 | 5 | 6 | | | VI-1 | Hist1h3a | | 3163 | 3 | 4 | 5 | 6 | | | VI-1 | Isl2 |
| 3079 | 3 | 4 | 5 | 6 | | | VI-1 | Hist1h3c | | 3164 | 3 | 4 | 5 | 6 | | | VI-1 | Itga7 |
| 3080 | 3 | 4 | 5 | 6 | | | VI-1 | Hist1h3d | | 3165 | 3 | 4 | 5 | 6 | | | VI-1 | Itgam |
| 3081 | 3 | 4 | 5 | 6 | | | VI-1 | Hist1h3h | | 3166 | 3 | 4 | 5 | 6 | | | VI-1 | Itgb6 |
| 3082 | 3 | 4 | 5 | 6 | | | VI-1 | Hist1h3i | | 3167 | 3 | 4 | 5 | 6 | | | VI-1 | Itih2 |
| 3083 | 3 | 4 | 5 | 6 | | | VI-1 | Hist1h4b | | 3168 | 3 | 4 | 5 | 6 | | | VI-1 | Itih4 |
| 3084 | 3 | 4 | 5 | 6 | | | VI-1 | Hist1h4c | | 3169 | 3 | 4 | 5 | 6 | | | VI-1 | Itpkb |
| 3085 | 3 | 4 | 5 | 6 | | | VI-1 | Hist1h4d | | 3170 | 3 | 4 | 5 | 6 | | | VI-1 | Itpripl1 |
| 3086 | 3 | 4 | 5 | 6 | | | VI-1 | Hist1h4f | | 3171 | 3 | 4 | 5 | 6 | | | VI-1 | Izumo4 |
| 3087 | 3 | 4 | 5 | 6 | | | VI-1 | Hist1h4j | | 3172 | 3 | 4 | 5 | 6 | | | VI-1 | Jph2 |
| 3088 | 3 | 4 | 5 | 6 | | | VI-1 | Hist1h4m | | 3173 | 3 | 4 | 5 | 6 | | | VI-1 | Kcnc3 |
| 3089 | 3 | 4 | 5 | 6 | | | VI-1 | Hist1h4n | | 3174 | 3 | 4 | 5 | 6 | | | VI-1 | Kcnc4 |
| 3090 | 3 | 4 | 5 | 6 | | | VI-1 | Hist2h2ab | | 3175 | 3 | 4 | 5 | 6 | | | VI-1 | Kcne1l |
| 3091 | 3 | 4 | 5 | 6 | | | VI-1 | Hist2h3b | | 3176 | 3 | 4 | 5 | 6 | | | VI-1 | Kcnh1 |
| 3092 | 3 | 4 | 5 | 6 | | | VI-1 | Hist2h3c1 | | 3177 | 3 | 4 | 5 | 6 | | | VI-1 | Kcnip1 |
| 3093 | 3 | 4 | 5 | 6 | | | VI-1 | Hist2h3c2 | | 3178 | 3 | 4 | 5 | 6 | | | VI-1 | Kcnip2 |
| 3094 | 3 | 4 | 5 | 6 | | | VI-1 | Hivep1 | | 3179 | 3 | 4 | 5 | 6 | | | VI-1 | Kcnip3 |
| 3095 | 3 | 4 | 5 | 6 | | | VI-1 | Hlf | | 3180 | 3 | 4 | 5 | 6 | | | VI-1 | Kcnj12 |
| 3096 | 3 | 4 | 5 | 6 | | | VI-1 | Hmgb3 | | 3181 | 3 | 4 | 5 | 6 | | | VI-1 | Kcnj2 |
| 3097 | 3 | 4 | 5 | 6 | | | VI-1 | Hmgn2 | | 3182 | 3 | 4 | 5 | 6 | | | VI-1 | Kcnn3 |
| 3098 | 3 | 4 | 5 | 6 | | | VI-1 | Hmmr | | 3183 | 3 | 4 | 5 | 6 | | | VI-1 | Kif21a |
| 3099 | 3 | 4 | 5 | 6 | | | VI-1 | Hnrnpa1 | | 3184 | 3 | 4 | 5 | 6 | | | VI-1 | Kifc1 |
| 3100 | 3 | 4 | 5 | 6 | | | VI-1 | Hoxa10 | | 3185 | 3 | 4 | 5 | 6 | | | VI-1 | Kit |
| 3101 | 3 | 4 | 5 | 6 | | | VI-1 | Hoxa3 | | 3186 | 3 | 4 | 5 | 6 | | | VI-1 | Kitl |
| 3102 | 3 | 4 | 5 | 6 | | | VI-1 | Hoxa7 | | 3187 | 3 | 4 | 5 | 6 | | | VI-1 | Klhl30 |
| 3103 | 3 | 4 | 5 | 6 | | | VI-1 | Hoxc11 | | 3188 | 3 | 4 | 5 | 6 | | | VI-1 | Klhl33 |
| 3104 | 3 | 4 | 5 | 6 | | | VI-1 | Hp | | 3189 | 3 | 4 | 5 | 6 | | | VI-1 | Klhl6 |
| 3105 | 3 | 4 | 5 | 6 | | | VI-1 | Hpn | | 3190 | 3 | 4 | 5 | 6 | | | VI-1 | Klk12 |
| 3106 | 3 | 4 | 5 | 6 | | | VI-1 | Hpx | | 3191 | 3 | 4 | 5 | 6 | | | VI-1 | Klk6 |
| 3107 | 3 | 4 | 5 | 6 | | | VI-1 | Hs3st6 | | 3192 | 3 | 4 | 5 | 6 | | | VI-1 | Klra13-ps |
| 3108 | 3 | 4 | 5 | 6 | | | VI-1 | Hsd17b12 | | 3193 | 3 | 4 | 5 | 6 | | | VI-1 | Klra2 |
| 3109 | 3 | 4 | 5 | 6 | | | VI-1 | Hsd17b7 | | 3194 | 3 | 4 | 5 | 6 | | | VI-1 | Klrd1 |
| 3110 | 3 | 4 | 5 | 6 | | | VI-1 | Hsd3b2 | | 3195 | 3 | 4 | 5 | 6 | | | VI-1 | Krt13 |
| 3111 | 3 | 4 | 5 | 6 | | | VI-1 | Hspa1a | | 3196 | 3 | 4 | 5 | 6 | | | VI-1 | Krt17 |
| 3112 | 3 | 4 | 5 | 6 | | | VI-1 | Hspb1 | | 3197 | 3 | 4 | 5 | 6 | | | VI-1 | Krt25 |
| 3113 | 3 | 4 | 5 | 6 | | | VI-1 | Hspb11 | | 3198 | 3 | 4 | 5 | 6 | | | VI-1 | Krt4 |
| 3114 | 3 | 4 | 5 | 6 | | | VI-1 | Hspb2 | | 3199 | 3 | 4 | 5 | 6 | | | VI-1 | Krt6a |
| 3115 | 3 | 4 | 5 | 6 | | | VI-1 | Hspb3 | | 3200 | 3 | 4 | 5 | 6 | | | VI-1 | Krt6b |
| 3116 | 3 | 4 | 5 | 6 | | | VI-1 | Hspb8 | | 3201 | 3 | 4 | 5 | 6 | | | VI-1 | Krt71 |
| 3117 | 3 | 4 | 5 | 6 | | | VI-1 | Htra1 | | 3202 | 3 | 4 | 5 | 6 | | | VI-1 | Krt75 |
| 3118 | 3 | 4 | 5 | 6 | | | VI-1 | Hypk | | 3203 | 3 | 4 | 5 | 6 | | | VI-1 | Krt79 |
| 3119 | 3 | 4 | 5 | 6 | | | VI-1 | I830012O16Rik | | 3204 | 3 | 4 | 5 | 6 | | | VI-1 | Krtap16-3 |
| 3120 | 3 | 4 | 5 | 6 | | | VI-1 | I830077J02Rik | | 3205 | 3 | 4 | 5 | 6 | | | VI-1 | Krtap17-1 |
| 3121 | 3 | 4 | 5 | 6 | | | VI-1 | Icam1 | | 3206 | 3 | 4 | 5 | 6 | | | VI-1 | Krtap19-3 |
| 3122 | 3 | 4 | 5 | 6 | | | VI-1 | Id2 | | 3207 | 3 | 4 | 5 | 6 | | | VI-1 | Krtap22-2 |
| 3123 | 3 | 4 | 5 | 6 | | | VI-1 | Idi1 | | 3208 | 3 | 4 | 5 | 6 | | | VI-1 | Krtap6-1 |
| 3124 | 3 | 4 | 5 | 6 | | | VI-1 | Ier3 | | 3209 | 3 | 4 | 5 | 6 | | | VI-1 | Krtap7-1 |
| 3125 | 3 | 4 | 5 | 6 | | | VI-1 | Ifi204 | | 3210 | 3 | 4 | 5 | 6 | | | VI-1 | Krtap9-3 |
| 3126 | 3 | 4 | 5 | 6 | | | VI-1 | Ifi27l2a | | 3211 | 3 | 4 | 5 | 6 | | | VI-1 | Ky |
| 3127 | 3 | 4 | 5 | 6 | | | VI-1 | Ifi27l2b | | 3212 | 3 | 4 | 5 | 6 | | | VI-1 | Lair1 |
| 3128 | 3 | 4 | 5 | 6 | | | VI-1 | Ifi47 | | 3213 | 3 | 4 | 5 | 6 | | | VI-1 | Lamb3 |
| 3129 | 3 | 4 | 5 | 6 | | | VI-1 | Ifit2 | | 3214 | 3 | 4 | 5 | 6 | | | VI-1 | Lamtor4 |
| 3130 | 3 | 4 | 5 | 6 | | | VI-1 | Ifit3 | | 3215 | 3 | 4 | 5 | 6 | | | VI-1 | Laptm5 |
| 3131 | 3 | 4 | 5 | 6 | | | VI-1 | Ifitm3 | | 3216 | 3 | 4 | 5 | 6 | | | VI-1 | Larp4 |
| 3132 | 3 | 4 | 5 | 6 | | | VI-1 | Ifitm7 | | 3217 | 3 | 4 | 5 | 6 | | | VI-1 | Lat2 |
| 3133 | 3 | 4 | 5 | 6 | | | VI-1 | Ift22 | | 3218 | 3 | 4 | 5 | 6 | | | VI-1 | Lax1 |
| 3134 | 3 | 4 | 5 | 6 | | | VI-1 | Igdcc4 | | 3219 | 3 | 4 | 5 | 6 | | | VI-1 | Lbh |
| 3135 | 3 | 4 | 5 | 6 | | | VI-1 | Igfbp5 | | 3220 | 3 | 4 | 5 | 6 | | | VI-1 | Lce1a1 |
| 3136 | 3 | 4 | 5 | 6 | | | VI-1 | Igsf23 | | 3221 | 3 | 4 | 5 | 6 | | | VI-1 | Lce1b |
| 3137 | 3 | 4 | 5 | 6 | | | VI-1 | Ilgp1 | | 3222 | 3 | 4 | 5 | 6 | | | VI-1 | Lce1f |
| 3138 | 3 | 4 | 5 | 6 | | | VI-1 | Ikbke | | 3223 | 3 | 4 | 5 | 6 | | | VI-1 | Lce3d |
| 3139 | 3 | 4 | 5 | 6 | | | VI-1 | Il13ra1 | | 3224 | 3 | 4 | 5 | 6 | | | VI-1 | Ldhb |
| 3140 | 3 | 4 | 5 | 6 | | | VI-1 | Il15 | | 3225 | 3 | 4 | 5 | 6 | | | VI-1 | Ldhd |
| 3141 | 3 | 4 | 5 | 6 | | | VI-1 | Il18bp | | 3226 | 3 | 4 | 5 | 6 | | | VI-1 | Ldlr |
| 3142 | 3 | 4 | 5 | 6 | | | VI-1 | Il18rap | | 3227 | 3 | 4 | 5 | 6 | | | VI-1 | Leap2 |
| 3143 | 3 | 4 | 5 | 6 | | | VI-1 | Il1f9 | | 3228 | 3 | 4 | 5 | 6 | | | VI-1 | Lect2 |

Fig. 43 - 20

| | | | | | | | | |
|---|---|---|---|---|---|---|---|---|
| 3229 | 3 | 4 | 5 | 6 | | VI-1 | Lenep |
| 3230 | 3 | 4 | 5 | 6 | | VI-1 | Lepr |
| 3231 | 3 | 4 | 5 | 6 | | VI-1 | Lgals1 |
| 3232 | 3 | 4 | 5 | 6 | | VI-1 | Lgals12 |
| 3233 | 3 | 4 | 5 | 6 | | VI-1 | Lgals3bp |
| 3234 | 3 | 4 | 5 | 6 | | VI-1 | Lgals9 |
| 3235 | 3 | 4 | 5 | 6 | | VI-1 | Lgi2 |
| 3236 | 3 | 4 | 5 | 6 | | VI-1 | Lgr6 |
| 3237 | 3 | 4 | 5 | 6 | | VI-1 | Lhfpl2 |
| 3238 | 3 | 4 | 5 | 6 | | VI-1 | Lilrb4 |
| 3239 | 3 | 4 | 5 | 6 | | VI-1 | Lmcd1 |
| 3240 | 3 | 4 | 5 | 6 | | VI-1 | LOC100038947 |
| 3241 | 3 | 4 | 5 | 6 | | VI-1 | LOC100503496 |
| 3242 | 3 | 4 | 5 | 6 | | VI-1 | LOC100504703 |
| 3243 | 3 | 4 | 5 | 6 | | VI-1 | LOC102632430 |
| 3244 | 3 | 4 | 5 | 6 | | VI-1 | LOC106740 |
| 3245 | 3 | 4 | 5 | 6 | | VI-1 | Loxl1 |
| 3246 | 3 | 4 | 5 | 6 | | VI-1 | Lpcat2 |
| 3247 | 3 | 4 | 5 | 6 | | VI-1 | Lpin3 |
| 3248 | 3 | 4 | 5 | 6 | | VI-1 | Lpl |
| 3249 | 3 | 4 | 5 | 6 | | VI-1 | Lpp |
| 3250 | 3 | 4 | 5 | 6 | | VI-1 | Lrch4 |
| 3251 | 3 | 4 | 5 | 6 | | VI-1 | Lrg1 |
| 3252 | 3 | 4 | 5 | 6 | | VI-1 | Lrmp |
| 3253 | 3 | 4 | 5 | 6 | | VI-1 | Lrrc14b |
| 3254 | 3 | 4 | 5 | 6 | | VI-1 | Lrrc15 |
| 3255 | 3 | 4 | 5 | 6 | | VI-1 | Lrrc25 |
| 3256 | 3 | 4 | 5 | 6 | | VI-1 | Lrrc27 |
| 3257 | 3 | 4 | 5 | 6 | | VI-1 | Lrrc29 |
| 3258 | 3 | 4 | 5 | 6 | | VI-1 | Lrrc32 |
| 3259 | 3 | 4 | 5 | 6 | | VI-1 | Lrrc39 |
| 3260 | 3 | 4 | 5 | 6 | | VI-1 | Lrrc4b |
| 3261 | 3 | 4 | 5 | 6 | | VI-1 | Lrrc8b |
| 3262 | 3 | 4 | 5 | 6 | | VI-1 | Lrrn1 |
| 3263 | 3 | 4 | 5 | 6 | | VI-1 | Lrtm1 |
| 3264 | 3 | 4 | 5 | 6 | | VI-1 | Lsm2 |
| 3265 | 3 | 4 | 5 | 6 | | VI-1 | Lsm5 |
| 3266 | 3 | 4 | 5 | 6 | | VI-1 | Lsmem1 |
| 3267 | 3 | 4 | 5 | 6 | | VI-1 | Lst1 |
| 3268 | 3 | 4 | 5 | 6 | | VI-1 | Ltb |
| 3269 | 3 | 4 | 5 | 6 | | VI-1 | Ltb4r1 |
| 3270 | 3 | 4 | 5 | 6 | | VI-1 | Ltbp2 |
| 3271 | 3 | 4 | 5 | 6 | | VI-1 | Ltc4s |
| 3272 | 3 | 4 | 5 | 6 | | VI-1 | Lum |
| 3273 | 3 | 4 | 5 | 6 | | VI-1 | Luzp1 |
| 3274 | 3 | 4 | 5 | 6 | | VI-1 | Ly6g6c |
| 3275 | 3 | 4 | 5 | 6 | | VI-1 | Ly6g6e |
| 3276 | 3 | 4 | 5 | 6 | | VI-1 | Ly86 |
| 3277 | 3 | 4 | 5 | 6 | | VI-1 | Lyg1 |
| 3278 | 3 | 4 | 5 | 6 | | VI-1 | Lyl1 |
| 3279 | 3 | 4 | 5 | 6 | | VI-1 | Lynx1 |
| 3280 | 3 | 4 | 5 | 6 | | VI-1 | Lypd2 |
| 3281 | 3 | 4 | 5 | 6 | | VI-1 | Lyplal1 |
| 3282 | 3 | 4 | 5 | 6 | | VI-1 | Lyrm4 |
| 3283 | 3 | 4 | 5 | 6 | | VI-1 | Mab21l3 |
| 3284 | 3 | 4 | 5 | 6 | | VI-1 | Mageb1 |
| 3285 | 3 | 4 | 5 | 6 | | VI-1 | Maged2 |
| 3286 | 3 | 4 | 5 | 6 | | VI-1 | Magohb |
| 3287 | 3 | 4 | 5 | 6 | | VI-1 | Malat1 |
| 3288 | 3 | 4 | 5 | 6 | | VI-1 | Man2b2 |
| 3289 | 3 | 4 | 5 | 6 | | VI-1 | Manf |
| 3290 | 3 | 4 | 5 | 6 | | VI-1 | Map2k3os |
| 3291 | 3 | 4 | 5 | 6 | | VI-1 | Map6 |
| 3292 | 3 | 4 | 5 | 6 | | VI-1 | Marcksl1 |
| 3293 | 3 | 4 | 5 | 6 | | VI-1 | Marco |
| 3294 | 3 | 4 | 5 | 6 | | VI-1 | Mbl2 |
| 3295 | 3 | 4 | 5 | 6 | | VI-1 | Mbp |
| 3296 | 3 | 4 | 5 | 6 | | VI-1 | Mcemp1 |
| 3297 | 3 | 4 | 5 | 6 | | VI-1 | Mcm10 |
| 3298 | 3 | 4 | 5 | 6 | | VI-1 | Mcm3 |
| 3299 | 3 | 4 | 5 | 6 | | VI-1 | Mcm5 |
| 3300 | 3 | 4 | 5 | 6 | | VI-1 | Mcm8 |
| 3301 | 3 | 4 | 5 | 6 | | VI-1 | Mdm1 |
| 3302 | 3 | 4 | 5 | 6 | | VI-1 | Mdm2 |
| 3303 | 3 | 4 | 5 | 6 | | VI-1 | Mdm4 |
| 3304 | 3 | 4 | 5 | 6 | | VI-1 | Mecr |
| 3305 | 3 | 4 | 5 | 6 | | VI-1 | Med9os |
| 3306 | 3 | 4 | 5 | 6 | | VI-1 | Mef2c |
| 3307 | 3 | 4 | 5 | 6 | | VI-1 | Megf6 |
| 3308 | 3 | 4 | 5 | 6 | | VI-1 | Megf9 |
| 3309 | 3 | 4 | 5 | 6 | | VI-1 | Mettl22 |
| 3310 | 3 | 4 | 5 | 6 | | VI-1 | Mettl7b |
| 3311 | 3 | 4 | 5 | 6 | | VI-1 | Mfrp |
| 3312 | 3 | 4 | 5 | 6 | | VI-1 | Mfsd12 |
| 3313 | 3 | 4 | 5 | 6 | | VI-1 | Mfsd2a |
| 3314 | 3 | 4 | 5 | 6 | | VI-1 | Mfsd4 |
| 3315 | 3 | 4 | 5 | 6 | | VI-1 | Mgp |
| 3316 | 3 | 4 | 5 | 6 | | VI-1 | Mgst1 |
| 3317 | 3 | 4 | 5 | 6 | | VI-1 | Mia2 |
| 3318 | 3 | 4 | 5 | 6 | | VI-1 | Mib1 |
| 3319 | 3 | 4 | 5 | 6 | | VI-1 | Mill2 |
| 3320 | 3 | 4 | 5 | 6 | | VI-1 | Minpp1 |
| 3321 | 3 | 4 | 5 | 6 | | VI-1 | Mir8113 |
| 3322 | 3 | 4 | 5 | 6 | | VI-1 | Mira |
| 3323 | 3 | 4 | 5 | 6 | | VI-1 | Mlip |
| 3324 | 3 | 4 | 5 | 6 | | VI-1 | Mlkl |
| 3325 | 3 | 4 | 5 | 6 | | VI-1 | Mmd2 |
| 3326 | 3 | 4 | 5 | 6 | | VI-1 | Mmp13 |
| 3327 | 3 | 4 | 5 | 6 | | VI-1 | Mmp2 |
| 3328 | 3 | 4 | 5 | 6 | | VI-1 | Mmp9 |
| 3329 | 3 | 4 | 5 | 6 | | VI-1 | Mn1 |
| 3330 | 3 | 4 | 5 | 6 | | VI-1 | Mnda |
| 3331 | 3 | 4 | 5 | 6 | | VI-1 | Mns1 |
| 3332 | 3 | 4 | 5 | 6 | | VI-1 | Moap1 |
| 3333 | 3 | 4 | 5 | 6 | | VI-1 | Mob1a |
| 3334 | 3 | 4 | 5 | 6 | | VI-1 | Mob1b |
| 3335 | 3 | 4 | 5 | 6 | | VI-1 | Morn2 |
| 3336 | 3 | 4 | 5 | 6 | | VI-1 | Moxd1 |
| 3337 | 3 | 4 | 5 | 6 | | VI-1 | Mpeg1 |
| 3338 | 3 | 4 | 5 | 6 | | VI-1 | Mphosph6 |
| 3339 | 3 | 4 | 5 | 6 | | VI-1 | Mreg |
| 3340 | 3 | 4 | 5 | 6 | | VI-1 | Mrgprf |
| 3341 | 3 | 4 | 5 | 6 | | VI-1 | Mroh7 |
| 3342 | 3 | 4 | 5 | 6 | | VI-1 | Mrpl23 |
| 3343 | 3 | 4 | 5 | 6 | | VI-1 | Mrpl33 |
| 3344 | 3 | 4 | 5 | 6 | | VI-1 | Mrpl47 |
| 3345 | 3 | 4 | 5 | 6 | | VI-1 | Mrpl52 |
| 3346 | 3 | 4 | 5 | 6 | | VI-1 | Mrpl54 |
| 3347 | 3 | 4 | 5 | 6 | | VI-1 | Mrps11 |
| 3348 | 3 | 4 | 5 | 6 | | VI-1 | Mrps18c |
| 3349 | 3 | 4 | 5 | 6 | | VI-1 | Mrps25 |
| 3350 | 3 | 4 | 5 | 6 | | VI-1 | Mrs2 |
| 3351 | 3 | 4 | 5 | 6 | | VI-1 | Mrto4 |
| 3352 | 3 | 4 | 5 | 6 | | VI-1 | Ms4a3 |
| 3353 | 3 | 4 | 5 | 6 | | VI-1 | Ms4a4b |
| 3354 | 3 | 4 | 5 | 6 | | VI-1 | Ms4a4d |
| 3355 | 3 | 4 | 5 | 6 | | VI-1 | Ms4a8a |
| 3356 | 3 | 4 | 5 | 6 | | VI-1 | Msln |
| 3357 | 3 | 4 | 5 | 6 | | VI-1 | Msmo1 |
| 3358 | 3 | 4 | 5 | 6 | | VI-1 | Msr1 |
| 3359 | 3 | 4 | 5 | 6 | | VI-1 | Mt1 |
| 3360 | 3 | 4 | 5 | 6 | | VI-1 | Mta3 |
| 3361 | 3 | 4 | 5 | 6 | | VI-1 | Mtag2 |
| 3362 | 3 | 4 | 5 | 6 | | VI-1 | Mterfd3 |
| 3363 | 3 | 4 | 5 | 6 | | VI-1 | Mthfd1 |
| 3364 | 3 | 4 | 5 | 6 | | VI-1 | Mthfd1l |
| 3365 | 3 | 4 | 5 | 6 | | VI-1 | Mthfd2 |
| 3366 | 3 | 4 | 5 | 6 | | VI-1 | Mtmr9 |
| 3367 | 3 | 4 | 5 | 6 | | VI-1 | Mup1 |
| 3368 | 3 | 4 | 5 | 6 | | VI-1 | Mup10 |
| 3369 | 3 | 4 | 5 | 6 | | VI-1 | Mup13 |
| 3370 | 3 | 4 | 5 | 6 | | VI-1 | Mup19 |
| 3371 | 3 | 4 | 5 | 6 | | VI-1 | Mup2 |
| 3372 | 3 | 4 | 5 | 6 | | VI-1 | Mup20 |
| 3373 | 3 | 4 | 5 | 6 | | VI-1 | Mup8 |
| 3374 | 3 | 4 | 5 | 6 | | VI-1 | Mup9 |
| 3375 | 3 | 4 | 5 | 6 | | VI-1 | Musk |
| 3376 | 3 | 4 | 5 | 6 | | VI-1 | Mvd |
| 3377 | 3 | 4 | 5 | 6 | | VI-1 | Mx1 |
| 3378 | 3 | 4 | 5 | 6 | | VI-1 | Mybphl |
| 3379 | 3 | 4 | 5 | 6 | | VI-1 | Myh10 |
| 3380 | 3 | 4 | 5 | 6 | | VI-1 | Myh13 |
| 3381 | 3 | 4 | 5 | 6 | | VI-1 | Myh14 |
| 3382 | 3 | 4 | 5 | 6 | | VI-1 | Mylk4 |
| 3383 | 3 | 4 | 5 | 6 | | VI-1 | Myod1 |
| 3384 | 3 | 4 | 5 | 6 | | VI-1 | Myoz3 |
| 3385 | 3 | 4 | 5 | 6 | | VI-1 | Naa38 |
| 3386 | 3 | 4 | 5 | 6 | | VI-1 | Naaa |
| 3387 | 3 | 4 | 5 | 6 | | VI-1 | Nags |
| 3388 | 3 | 4 | 5 | 6 | | VI-1 | Napb |
| 3389 | 3 | 4 | 5 | 6 | | VI-1 | Nat2 |
| 3390 | 3 | 4 | 5 | 6 | | VI-1 | Ncaph |
| 3391 | 3 | 4 | 5 | 6 | | VI-1 | Ncmap |
| 3392 | 3 | 4 | 5 | 6 | | VI-1 | Ndst1 |
| 3393 | 3 | 4 | 5 | 6 | | VI-1 | Ndufa11 |
| 3394 | 3 | 4 | 5 | 6 | | VI-1 | Ndufa12 |
| 3395 | 3 | 4 | 5 | 6 | | VI-1 | Ndufa3 |
| 3396 | 3 | 4 | 5 | 6 | | VI-1 | Ndufa4 |
| 3397 | 3 | 4 | 5 | 6 | | VI-1 | Ndufaf7 |
| 3398 | 3 | 4 | 5 | 6 | | VI-1 | Ndufb6 |

Fig. 43 - 21

| 3399 | 3 | 4 | 5 | 6 | | | VI-1 | Ndufb7 |
|---|---|---|---|---|---|---|---|---|
| 3400 | 3 | 4 | 5 | 6 | | | VI-1 | Ndufc1 |
| 3401 | 3 | 4 | 5 | 6 | | | VI-1 | Neu2 |
| 3402 | 3 | 4 | 5 | 6 | | | VI-1 | Neurl2 |
| 3403 | 3 | 4 | 5 | 6 | | | VI-1 | Neurl3 |
| 3404 | 3 | 4 | 5 | 6 | | | VI-1 | Ngp |
| 3405 | 3 | 4 | 5 | 6 | | | VI-1 | Nhp2 |
| 3406 | 3 | 4 | 5 | 6 | | | VI-1 | Nid2 |
| 3407 | 3 | 4 | 5 | 6 | | | VI-1 | Nkg7 |
| 3408 | 3 | 4 | 5 | 6 | | | VI-1 | Nmb |
| 3409 | 3 | 4 | 5 | 6 | | | VI-1 | Nme1 |
| 3410 | 3 | 4 | 5 | 6 | | | VI-1 | Nme2 |
| 3411 | 3 | 4 | 5 | 6 | | | VI-1 | Nme4 |
| 3412 | 3 | 4 | 5 | 6 | | | VI-1 | Nmi |
| 3413 | 3 | 4 | 5 | 6 | | | VI-1 | Nmrk2 |
| 3414 | 3 | 4 | 5 | 6 | | | VI-1 | Nnmt |
| 3415 | 3 | 4 | 5 | 6 | | | VI-1 | Nol12 |
| 3416 | 3 | 4 | 5 | 6 | | | VI-1 | Nom1 |
| 3417 | 3 | 4 | 5 | 6 | | | VI-1 | Npas4 |
| 3418 | 3 | 4 | 5 | 6 | | | VI-1 | Npb |
| 3419 | 3 | 4 | 5 | 6 | | | VI-1 | Npcd |
| 3420 | 3 | 4 | 5 | 6 | | | VI-1 | Nphp1 |
| 3421 | 3 | 4 | 5 | 6 | | | VI-1 | Npl |
| 3422 | 3 | 4 | 5 | 6 | | | VI-1 | Nppa |
| 3423 | 3 | 4 | 5 | 6 | | | VI-1 | Nptxr |
| 3424 | 3 | 4 | 5 | 6 | | | VI-1 | Npw |
| 3425 | 3 | 4 | 5 | 6 | | | VI-1 | Npy6r |
| 3426 | 3 | 4 | 5 | 6 | | | VI-1 | Nqo1 |
| 3427 | 3 | 4 | 5 | 6 | | | VI-1 | Nr1d1 |
| 3428 | 3 | 4 | 5 | 6 | | | VI-1 | Nr2c2 |
| 3429 | 3 | 4 | 5 | 6 | | | VI-1 | Nr4a3 |
| 3430 | 3 | 4 | 5 | 6 | | | VI-1 | Nrg1 |
| 3431 | 3 | 4 | 5 | 6 | | | VI-1 | Nrg4 |
| 3432 | 3 | 4 | 5 | 6 | | | VI-1 | Nrip1 |
| 3433 | 3 | 4 | 5 | 6 | | | VI-1 | Nrtn |
| 3434 | 3 | 4 | 5 | 6 | | | VI-1 | Nsg1 |
| 3435 | 3 | 4 | 5 | 6 | | | VI-1 | Ntng2 |
| 3436 | 3 | 4 | 5 | 6 | | | VI-1 | Nudt10 |
| 3437 | 3 | 4 | 5 | 6 | | | VI-1 | Nupr1l |
| 3438 | 3 | 4 | 5 | 6 | | | VI-1 | Nusap1 |
| 3439 | 3 | 4 | 5 | 6 | | | VI-1 | Nxpe2 |
| 3440 | 3 | 4 | 5 | 6 | | | VI-1 | Oacyl |
| 3441 | 3 | 4 | 5 | 6 | | | VI-1 | Oaf |
| 3442 | 3 | 4 | 5 | 6 | | | VI-1 | Oas1a |
| 3443 | 3 | 4 | 5 | 6 | | | VI-1 | Oas1c |
| 3444 | 3 | 4 | 5 | 6 | | | VI-1 | Oas1g |
| 3445 | 3 | 4 | 5 | 6 | | | VI-1 | Oasl1 |
| 3446 | 3 | 4 | 5 | 6 | | | VI-1 | Ociad2 |
| 3447 | 3 | 4 | 5 | 6 | | | VI-1 | Olfr1396 |
| 3448 | 3 | 4 | 5 | 6 | | | VI-1 | Olfr543 |
| 3449 | 3 | 4 | 5 | 6 | | | VI-1 | Onecut1 |
| 3450 | 3 | 4 | 5 | 6 | | | VI-1 | Orc1 |
| 3451 | 3 | 4 | 5 | 6 | | | VI-1 | Orm1 |
| 3452 | 3 | 4 | 5 | 6 | | | VI-1 | Osbpl10 |
| 3453 | 3 | 4 | 5 | 6 | | | VI-1 | Oscp1 |
| 3454 | 3 | 4 | 5 | 6 | | | VI-1 | Osgin1 |
| 3455 | 3 | 4 | 5 | 6 | | | VI-1 | Ott |
| 3456 | 3 | 4 | 5 | 6 | | | VI-1 | Oxld1 |
| 3457 | 3 | 4 | 5 | 6 | | | VI-1 | P2ry13 |
| 3458 | 3 | 4 | 5 | 6 | | | VI-1 | Pag1 |
| 3459 | 3 | 4 | 5 | 6 | | | VI-1 | Pak4 |
| 3460 | 3 | 4 | 5 | 6 | | | VI-1 | Papln |
| 3461 | 3 | 4 | 5 | 6 | | | VI-1 | Paqr9 |
| 3462 | 3 | 4 | 5 | 6 | | | VI-1 | Parp2 |
| 3463 | 3 | 4 | 5 | 6 | | | VI-1 | Pax1 |
| 3464 | 3 | 4 | 5 | 6 | | | VI-1 | Pcbd1 |
| 3465 | 3 | 4 | 5 | 6 | | | VI-1 | Pcdh7 |
| 3466 | 3 | 4 | 5 | 6 | | | VI-1 | Pck1 |
| 3467 | 3 | 4 | 5 | 6 | | | VI-1 | Pde4b |
| 3468 | 3 | 4 | 5 | 6 | | | VI-1 | Pde7b |
| 3469 | 3 | 4 | 5 | 6 | | | VI-1 | Pdia2 |
| 3470 | 3 | 4 | 5 | 6 | | | VI-1 | Pdk4 |
| 3471 | 3 | 4 | 5 | 6 | | | VI-1 | Pdlim5 |
| 3472 | 3 | 4 | 5 | 6 | | | VI-1 | Pdlim7 |
| 3473 | 3 | 4 | 5 | 6 | | | VI-1 | Pdpr |
| 3474 | 3 | 4 | 5 | 6 | | | VI-1 | Pdss1 |
| 3475 | 3 | 4 | 5 | 6 | | | VI-1 | Pdxk |
| 3476 | 3 | 4 | 5 | 6 | | | VI-1 | Pdzrn3 |
| 3477 | 3 | 4 | 5 | 6 | | | VI-1 | Peg3 |
| 3478 | 3 | 4 | 5 | 6 | | | VI-1 | Peg3os |
| 3479 | 3 | 4 | 5 | 6 | | | VI-1 | Pemt |
| 3480 | 3 | 4 | 5 | 6 | | | VI-1 | Per2 |
| 3481 | 3 | 4 | 5 | 6 | | | VI-1 | Per3 |
| 3482 | 3 | 4 | 5 | 6 | | | VI-1 | Perp |
| 3483 | 3 | 4 | 5 | 6 | | | VI-1 | Pex11g |

| 3484 | 3 | 4 | 5 | 6 | | | VI-1 | Pf4 |
|---|---|---|---|---|---|---|---|---|
| 3485 | 3 | 4 | 5 | 6 | | | VI-1 | Pfkp |
| 3486 | 3 | 4 | 5 | 6 | | | VI-1 | Pgam2 |
| 3487 | 3 | 4 | 5 | 6 | | | VI-1 | Pgf |
| 3488 | 3 | 4 | 5 | 6 | | | VI-1 | Pglyrp1 |
| 3489 | 3 | 4 | 5 | 6 | | | VI-1 | Pgpep1l |
| 3490 | 3 | 4 | 5 | 6 | | | VI-1 | Phf10 |
| 3491 | 3 | 4 | 5 | 6 | | | VI-1 | Phf11a |
| 3492 | 3 | 4 | 5 | 6 | | | VI-1 | Phf11b |
| 3493 | 3 | 4 | 5 | 6 | | | VI-1 | Phf11d |
| 3494 | 3 | 4 | 5 | 6 | | | VI-1 | Phgr1 |
| 3495 | 3 | 4 | 5 | 6 | | | VI-1 | Phkg1 |
| 3496 | 3 | 4 | 5 | 6 | | | VI-1 | Phlda2 |
| 3497 | 3 | 4 | 5 | 6 | | | VI-1 | Phtf1os |
| 3498 | 3 | 4 | 5 | 6 | | | VI-1 | Phtf2 |
| 3499 | 3 | 4 | 5 | 6 | | | VI-1 | Phyhip |
| 3500 | 3 | 4 | 5 | 6 | | | VI-1 | Pigr |
| 3501 | 3 | 4 | 5 | 6 | | | VI-1 | Pik3ap1 |
| 3502 | 3 | 4 | 5 | 6 | | | VI-1 | Pin4 |
| 3503 | 3 | 4 | 5 | 6 | | | VI-1 | Pinx1 |
| 3504 | 3 | 4 | 5 | 6 | | | VI-1 | Pip5k1a |
| 3505 | 3 | 4 | 5 | 6 | | | VI-1 | Pira11 |
| 3506 | 3 | 4 | 5 | 6 | | | VI-1 | Pira2 |
| 3507 | 3 | 4 | 5 | 6 | | | VI-1 | Pirb |
| 3508 | 3 | 4 | 5 | 6 | | | VI-1 | Pkia |
| 3509 | 3 | 4 | 5 | 6 | | | VI-1 | Pkm |
| 3510 | 3 | 4 | 5 | 6 | | | VI-1 | Pla1a |
| 3511 | 3 | 4 | 5 | 6 | | | VI-1 | Pla2g12a |
| 3512 | 3 | 4 | 5 | 6 | | | VI-1 | Pla2g4c |
| 3513 | 3 | 4 | 5 | 6 | | | VI-1 | Pla2g4d |
| 3514 | 3 | 4 | 5 | 6 | | | VI-1 | Pla2g4e |
| 3515 | 3 | 4 | 5 | 6 | | | VI-1 | Pla2g7 |
| 3516 | 3 | 4 | 5 | 6 | | | VI-1 | Plac8 |
| 3517 | 3 | 4 | 5 | 6 | | | VI-1 | Plac9a |
| 3518 | 3 | 4 | 5 | 6 | | | VI-1 | Plac9b |
| 3519 | 3 | 4 | 5 | 6 | | | VI-1 | Plagl1 |
| 3520 | 3 | 4 | 5 | 6 | | | VI-1 | Plbd1 |
| 3521 | 3 | 4 | 5 | 6 | | | VI-1 | Plcd4 |
| 3522 | 3 | 4 | 5 | 6 | | | VI-1 | Pld1 |
| 3523 | 3 | 4 | 5 | 6 | | | VI-1 | Plek |
| 3524 | 3 | 4 | 5 | 6 | | | VI-1 | Plekha4 |
| 3525 | 3 | 4 | 5 | 6 | | | VI-1 | Plin1 |
| 3526 | 3 | 4 | 5 | 6 | | | VI-1 | Plin4 |
| 3527 | 3 | 4 | 5 | 6 | | | VI-1 | Plk2 |
| 3528 | 3 | 4 | 5 | 6 | | | VI-1 | Plk3 |
| 3529 | 3 | 4 | 5 | 6 | | | VI-1 | Plp1 |
| 3530 | 3 | 4 | 5 | 6 | | | VI-1 | Pmaip1 |
| 3531 | 3 | 4 | 5 | 6 | | | VI-1 | Pmepa1 |
| 3532 | 3 | 4 | 5 | 6 | | | VI-1 | Pmf1 |
| 3533 | 3 | 4 | 5 | 6 | | | VI-1 | Pnliprp2 |
| 3534 | 3 | 4 | 5 | 6 | | | VI-1 | Pnmt |
| 3535 | 3 | 4 | 5 | 6 | | | VI-1 | Pnoc |
| 3536 | 3 | 4 | 5 | 6 | | | VI-1 | Poc1a |
| 3537 | 3 | 4 | 5 | 6 | | | VI-1 | Podn |
| 3538 | 3 | 4 | 5 | 6 | | | VI-1 | Polb |
| 3539 | 3 | 4 | 5 | 6 | | | VI-1 | Polk |
| 3540 | 3 | 4 | 5 | 6 | | | VI-1 | Polr2h |
| 3541 | 3 | 4 | 5 | 6 | | | VI-1 | Polr2k |
| 3542 | 3 | 4 | 5 | 6 | | | VI-1 | Pon1 |
| 3543 | 3 | 4 | 5 | 6 | | | VI-1 | Popdc2 |
| 3544 | 3 | 4 | 5 | 6 | | | VI-1 | Ppa1 |
| 3545 | 3 | 4 | 5 | 6 | | | VI-1 | Ppargc1a |
| 3546 | 3 | 4 | 5 | 6 | | | VI-1 | Ppbp |
| 3547 | 3 | 4 | 5 | 6 | | | VI-1 | Ppifos |
| 3548 | 3 | 4 | 5 | 6 | | | VI-1 | Ppih |
| 3549 | 3 | 4 | 5 | 6 | | | VI-1 | Ppil1 |
| 3550 | 3 | 4 | 5 | 6 | | | VI-1 | Ppp1r12b |
| 3551 | 3 | 4 | 5 | 6 | | | VI-1 | Ppp1r14c |
| 3552 | 3 | 4 | 5 | 6 | | | VI-1 | Ppp1r14d |
| 3553 | 3 | 4 | 5 | 6 | | | VI-1 | Ppp1r3a |
| 3554 | 3 | 4 | 5 | 6 | | | VI-1 | Ppp1r3b |
| 3555 | 3 | 4 | 5 | 6 | | | VI-1 | Ppp1r3c |
| 3556 | 3 | 4 | 5 | 6 | | | VI-1 | Ppp1r3d |
| 3557 | 3 | 4 | 5 | 6 | | | VI-1 | Ppp1r3e |
| 3558 | 3 | 4 | 5 | 6 | | | VI-1 | Pram1 |
| 3559 | 3 | 4 | 5 | 6 | | | VI-1 | Prelp |
| 3560 | 3 | 4 | 5 | 6 | | | VI-1 | Prg2 |
| 3561 | 3 | 4 | 5 | 6 | | | VI-1 | Prkag3 |
| 3562 | 3 | 4 | 5 | 6 | | | VI-1 | Prkar2b |
| 3563 | 3 | 4 | 5 | 6 | | | VI-1 | Prkcdbp |
| 3564 | 3 | 4 | 5 | 6 | | | VI-1 | Prkce |
| 3565 | 3 | 4 | 5 | 6 | | | VI-1 | Prkcq |
| 3566 | 3 | 4 | 5 | 6 | | | VI-1 | Procr |
| 3567 | 3 | 4 | 5 | 6 | | | VI-1 | Prpf40a |
| 3568 | 3 | 4 | 5 | 6 | | | VI-1 | Prr11 |

Fig. 43 - 22

| | | | | | | | | |
|---|---|---|---|---|---|---|---|---|
| 3569 | 3 | 4 | 5 | 6 | | VI-1 | Prr15 |
| 3570 | 3 | 4 | 5 | 6 | | VI-1 | Prr33 |
| 3571 | 3 | 4 | 5 | 6 | | VI-1 | Prr7 |
| 3572 | 3 | 4 | 5 | 6 | | VI-1 | Prr9 |
| 3573 | 3 | 4 | 5 | 6 | | VI-1 | Prss1 |
| 3574 | 3 | 4 | 5 | 6 | | VI-1 | Prss50 |
| 3575 | 3 | 4 | 5 | 6 | | VI-1 | Prtn3 |
| 3576 | 3 | 4 | 5 | 6 | | VI-1 | Prune2 |
| 3577 | 3 | 4 | 5 | 6 | | VI-1 | Psap1 |
| 3578 | 3 | 4 | 5 | 6 | | VI-1 | Psat1 |
| 3579 | 3 | 4 | 5 | 6 | | VI-1 | Psmb7 |
| 3580 | 3 | 4 | 5 | 6 | | VI-1 | Psmb9 |
| 3581 | 3 | 4 | 5 | 6 | | VI-1 | Psmc3ip |
| 3582 | 3 | 4 | 5 | 6 | | VI-1 | Psors1c2 |
| 3583 | 3 | 4 | 5 | 6 | | VI-1 | Psph |
| 3584 | 3 | 4 | 5 | 6 | | VI-1 | Pstpip2 |
| 3585 | 3 | 4 | 5 | 6 | | VI-1 | Ptger3 |
| 3586 | 3 | 4 | 5 | 6 | | VI-1 | Ptp4a3 |
| 3587 | 3 | 4 | 5 | 6 | | VI-1 | Ptpla |
| 3588 | 3 | 4 | 5 | 6 | | VI-1 | Ptplb |
| 3589 | 3 | 4 | 5 | 6 | | VI-1 | Ptprcap |
| 3590 | 3 | 4 | 5 | 6 | | VI-1 | Ptx3 |
| 3591 | 3 | 4 | 5 | 6 | | VI-1 | Pxmp2 |
| 3592 | 3 | 4 | 5 | 6 | | VI-1 | Pycr1 |
| 3593 | 3 | 4 | 5 | 6 | | VI-1 | Qrsl1 |
| 3594 | 3 | 4 | 5 | 6 | | VI-1 | Rad51 |
| 3595 | 3 | 4 | 5 | 6 | | VI-1 | Rai1 |
| 3596 | 3 | 4 | 5 | 6 | | VI-1 | Rangrf |
| 3597 | 3 | 4 | 5 | 6 | | VI-1 | Rap2b |
| 3598 | 3 | 4 | 5 | 6 | | VI-1 | Rapgef5 |
| 3599 | 3 | 4 | 5 | 6 | | VI-1 | Rarres1 |
| 3600 | 3 | 4 | 5 | 6 | | VI-1 | Rarres2 |
| 3601 | 3 | 4 | 5 | 6 | | VI-1 | Rasl11b |
| 3602 | 3 | 4 | 5 | 6 | | VI-1 | Rbks |
| 3603 | 3 | 4 | 5 | 6 | | VI-1 | Rbm14-rbm4 |
| 3604 | 3 | 4 | 5 | 6 | | VI-1 | Rbm3 |
| 3605 | 3 | 4 | 5 | 6 | | VI-1 | Rbm43 |
| 3606 | 3 | 4 | 5 | 6 | | VI-1 | Rbmx |
| 3607 | 3 | 4 | 5 | 6 | | VI-1 | Rbp1 |
| 3608 | 3 | 4 | 5 | 6 | | VI-1 | Rcan1 |
| 3609 | 3 | 4 | 5 | 6 | | VI-1 | Rdh12 |
| 3610 | 3 | 4 | 5 | 6 | | VI-1 | Rdm1 |
| 3611 | 3 | 4 | 5 | 6 | | VI-1 | Relt |
| 3612 | 3 | 4 | 5 | 6 | | VI-1 | Ren1 |
| 3613 | 3 | 4 | 5 | 6 | | VI-1 | Retn |
| 3614 | 3 | 4 | 5 | 6 | | VI-1 | Retsat |
| 3615 | 3 | 4 | 5 | 6 | | VI-1 | Rev1 |
| 3616 | 3 | 4 | 5 | 6 | | VI-1 | Rfc4 |
| 3617 | 3 | 4 | 5 | 6 | | VI-1 | Rfc5 |
| 3618 | 3 | 4 | 5 | 6 | | VI-1 | Rgn |
| 3619 | 3 | 4 | 5 | 6 | | VI-1 | Rgs5 |
| 3620 | 3 | 4 | 5 | 6 | | VI-1 | Rian |
| 3621 | 3 | 4 | 5 | 6 | | VI-1 | Rilpl1 |
| 3622 | 3 | 4 | 5 | 6 | | VI-1 | Rlf |
| 3623 | 3 | 4 | 5 | 6 | | VI-1 | Rmrp |
| 3624 | 3 | 4 | 5 | 6 | | VI-1 | Rn4.5s |
| 3625 | 3 | 4 | 5 | 6 | | VI-1 | Rnase2b |
| 3626 | 3 | 4 | 5 | 6 | | VI-1 | Rnase6 |
| 3627 | 3 | 4 | 5 | 6 | | VI-1 | Rnaseh2b |
| 3628 | 3 | 4 | 5 | 6 | | VI-1 | Rnaset2a |
| 3629 | 3 | 4 | 5 | 6 | | VI-1 | Rnd2 |
| 3630 | 3 | 4 | 5 | 6 | | VI-1 | Rnf128 |
| 3631 | 3 | 4 | 5 | 6 | | VI-1 | Rnf224 |
| 3632 | 3 | 4 | 5 | 6 | | VI-1 | Rnf24 |
| 3633 | 3 | 4 | 5 | 6 | | VI-1 | Rnmtl1 |
| 3634 | 3 | 4 | 5 | 6 | | VI-1 | Rogdi |
| 3635 | 3 | 4 | 5 | 6 | | VI-1 | Romo1 |
| 3636 | 3 | 4 | 5 | 6 | | VI-1 | Ror1 |
| 3637 | 3 | 4 | 5 | 6 | | VI-1 | Rpl22l1 |
| 3638 | 3 | 4 | 5 | 6 | | VI-1 | Rpl39 |
| 3639 | 3 | 4 | 5 | 6 | | VI-1 | Rps16 |
| 3640 | 3 | 4 | 5 | 6 | | VI-1 | Rps19bp1 |
| 3641 | 3 | 4 | 5 | 6 | | VI-1 | Rps27l |
| 3642 | 3 | 4 | 5 | 6 | | VI-1 | Rps6ka2 |
| 3643 | 3 | 4 | 5 | 6 | | VI-1 | Rptn |
| 3644 | 3 | 4 | 5 | 6 | | VI-1 | Rrad |
| 3645 | 3 | 4 | 5 | 6 | | VI-1 | Rragd |
| 3646 | 3 | 4 | 5 | 6 | | VI-1 | Rrp12 |
| 3647 | 3 | 4 | 5 | 6 | | VI-1 | Rtn2 |
| 3648 | 3 | 4 | 5 | 6 | | VI-1 | Rtn4r |
| 3649 | 3 | 4 | 5 | 6 | | VI-1 | Rtp4 |
| 3650 | 3 | 4 | 5 | 6 | | VI-1 | Rxfp2 |
| 3651 | 3 | 4 | 5 | 6 | | VI-1 | Rxrg |
| 3652 | 3 | 4 | 5 | 6 | | VI-1 | Ryk |
| 3653 | 3 | 4 | 5 | 6 | | VI-1 | S100a14 |
| 3654 | 3 | 4 | 5 | 6 | | VI-1 | S100a16 |
| 3655 | 3 | 4 | 5 | 6 | | VI-1 | S100a4 |
| 3656 | 3 | 4 | 5 | 6 | | VI-1 | S100a6 |
| 3657 | 3 | 4 | 5 | 6 | | VI-1 | Samp |
| 3658 | 3 | 4 | 5 | 6 | | VI-1 | Sat2 |
| 3659 | 3 | 4 | 5 | 6 | | VI-1 | Sbk3 |
| 3660 | 3 | 4 | 5 | 6 | | VI-1 | Scara3 |
| 3661 | 3 | 4 | 5 | 6 | | VI-1 | Scarna13 |
| 3662 | 3 | 4 | 5 | 6 | | VI-1 | Scd1 |
| 3663 | 3 | 4 | 5 | 6 | | VI-1 | Scd2 |
| 3664 | 3 | 4 | 5 | 6 | | VI-1 | Scimp |
| 3665 | 3 | 4 | 5 | 6 | | VI-1 | Scml4 |
| 3666 | 3 | 4 | 5 | 6 | | VI-1 | Scn1b |
| 3667 | 3 | 4 | 5 | 6 | | VI-1 | Scn4a |
| 3668 | 3 | 4 | 5 | 6 | | VI-1 | Scn4b |
| 3669 | 3 | 4 | 5 | 6 | | VI-1 | Scnn1g |
| 3670 | 3 | 4 | 5 | 6 | | VI-1 | Scx |
| 3671 | 3 | 4 | 5 | 6 | | VI-1 | Sdc3 |
| 3672 | 3 | 4 | 5 | 6 | | VI-1 | Sdcbp2 |
| 3673 | 3 | 4 | 5 | 6 | | VI-1 | Sdf2l1 |
| 3674 | 3 | 4 | 5 | 6 | | VI-1 | Sdr16c6 |
| 3675 | 3 | 4 | 5 | 6 | | VI-1 | Sdr9c7 |
| 3676 | 3 | 4 | 5 | 6 | | VI-1 | Sds |
| 3677 | 3 | 4 | 5 | 6 | | VI-1 | Sdsl |
| 3678 | 3 | 4 | 5 | 6 | | VI-1 | Sec61b |
| 3679 | 3 | 4 | 5 | 6 | | VI-1 | Selenbp1 |
| 3680 | 3 | 4 | 5 | 6 | | VI-1 | Selenbp2 |
| 3681 | 3 | 4 | 5 | 6 | | VI-1 | Sell |
| 3682 | 3 | 4 | 5 | 6 | | VI-1 | Selp |
| 3683 | 3 | 4 | 5 | 6 | | VI-1 | Sema3c |
| 3684 | 3 | 4 | 5 | 6 | | VI-1 | Sept8 |
| 3685 | 3 | 4 | 5 | 6 | | VI-1 | Serpina10 |
| 3686 | 3 | 4 | 5 | 6 | | VI-1 | Serpina3b |
| 3687 | 3 | 4 | 5 | 6 | | VI-1 | Serpina3c |
| 3688 | 3 | 4 | 5 | 6 | | VI-1 | Serpina3g |
| 3689 | 3 | 4 | 5 | 6 | | VI-1 | Serpina3k |
| 3690 | 3 | 4 | 5 | 6 | | VI-1 | Serpina3m |
| 3691 | 3 | 4 | 5 | 6 | | VI-1 | Serpina6 |
| 3692 | 3 | 4 | 5 | 6 | | VI-1 | Serpinb1a |
| 3693 | 3 | 4 | 5 | 6 | | VI-1 | Serpinb3c |
| 3694 | 3 | 4 | 5 | 6 | | VI-1 | Serpine2 |
| 3695 | 3 | 4 | 5 | 6 | | VI-1 | Serpinf1 |
| 3696 | 3 | 4 | 5 | 6 | | VI-1 | Serpini2 |
| 3697 | 3 | 4 | 5 | 6 | | VI-1 | Sfn |
| 3698 | 3 | 4 | 5 | 6 | | VI-1 | Sfrp2 |
| 3699 | 3 | 4 | 5 | 6 | | VI-1 | Sfrp4 |
| 3700 | 3 | 4 | 5 | 6 | | VI-1 | Sfrp5 |
| 3701 | 3 | 4 | 5 | 6 | | VI-1 | Sgk2 |
| 3702 | 3 | 4 | 5 | 6 | | VI-1 | Sh3bgr |
| 3703 | 3 | 4 | 5 | 6 | | VI-1 | Sh3kbp1 |
| 3704 | 3 | 4 | 5 | 6 | | VI-1 | Sh3rf2 |
| 3705 | 3 | 4 | 5 | 6 | | VI-1 | Shisa2 |
| 3706 | 3 | 4 | 5 | 6 | | VI-1 | Shq1 |
| 3707 | 3 | 4 | 5 | 6 | | VI-1 | Siglec1 |
| 3708 | 3 | 4 | 5 | 6 | | VI-1 | Sirpb1a |
| 3709 | 3 | 4 | 5 | 6 | | VI-1 | Sirpb1b |
| 3710 | 3 | 4 | 5 | 6 | | VI-1 | Siva1 |
| 3711 | 3 | 4 | 5 | 6 | | VI-1 | Slamf9 |
| 3712 | 3 | 4 | 5 | 6 | | VI-1 | Slc10a7 |
| 3713 | 3 | 4 | 5 | 6 | | VI-1 | Slc11a1 |
| 3714 | 3 | 4 | 5 | 6 | | VI-1 | Slc13a3 |
| 3715 | 3 | 4 | 5 | 6 | | VI-1 | Slc15a3 |
| 3716 | 3 | 4 | 5 | 6 | | VI-1 | Slc16a3 |
| 3717 | 3 | 4 | 5 | 6 | | VI-1 | Slc16a5 |
| 3718 | 3 | 4 | 5 | 6 | | VI-1 | Slc16a6 |
| 3719 | 3 | 4 | 5 | 6 | | VI-1 | Slc16a9 |
| 3720 | 3 | 4 | 5 | 6 | | VI-1 | Slc17a7 |
| 3721 | 3 | 4 | 5 | 6 | | VI-1 | Slc1a4 |
| 3722 | 3 | 4 | 5 | 6 | | VI-1 | Slc23a3 |
| 3723 | 3 | 4 | 5 | 6 | | VI-1 | Slc25a14 |
| 3724 | 3 | 4 | 5 | 6 | | VI-1 | Slc25a21 |
| 3725 | 3 | 4 | 5 | 6 | | VI-1 | Slc26a2 |
| 3726 | 3 | 4 | 5 | 6 | | VI-1 | Slc27a2 |
| 3727 | 3 | 4 | 5 | 6 | | VI-1 | Slc2a12 |
| 3728 | 3 | 4 | 5 | 6 | | VI-1 | Slc2a3 |
| 3729 | 3 | 4 | 5 | 6 | | VI-1 | Slc34a2 |
| 3730 | 3 | 4 | 5 | 6 | | VI-1 | Slc35g1 |
| 3731 | 3 | 4 | 5 | 6 | | VI-1 | Slc36a4 |
| 3732 | 3 | 4 | 5 | 6 | | VI-1 | Slc38a1 |
| 3733 | 3 | 4 | 5 | 6 | | VI-1 | Slc38a4 |
| 3734 | 3 | 4 | 5 | 6 | | VI-1 | Slc38a5 |
| 3735 | 3 | 4 | 5 | 6 | | VI-1 | Slc39a4 |
| 3736 | 3 | 4 | 5 | 6 | | VI-1 | Slc39a8 |
| 3737 | 3 | 4 | 5 | 6 | | VI-1 | Slc3a1 |
| 3738 | 3 | 4 | 5 | 6 | | VI-1 | Slc41a2 |

Fig. 43 - 23

| | | | | | | | | |
|---|---|---|---|---|---|---|---|---|
| 3739 | 3 | 4 | 5 | 6 | | VI-1 | Slc43a2 |
| 3740 | 3 | 4 | 5 | 6 | | VI-1 | Slc47a1 |
| 3741 | 3 | 4 | 5 | 6 | | VI-1 | Slc5a6 |
| 3742 | 3 | 4 | 5 | 6 | | VI-1 | Slc7a1 |
| 3743 | 3 | 4 | 5 | 6 | | VI-1 | Slc7a11 |
| 3744 | 3 | 4 | 5 | 6 | | VI-1 | Slc7a3 |
| 3745 | 3 | 4 | 5 | 6 | | VI-1 | Slc7a5 |
| 3746 | 3 | 4 | 5 | 6 | | VI-1 | Slco4a1 |
| 3747 | 3 | 4 | 5 | 6 | | VI-1 | Slfn1 |
| 3748 | 3 | 4 | 5 | 6 | | VI-1 | Slfn2 |
| 3749 | 3 | 4 | 5 | 6 | | VI-1 | Slfn3 |
| 3750 | 3 | 4 | 5 | 6 | | VI-1 | Slirp |
| 3751 | 3 | 4 | 5 | 6 | | VI-1 | Slpi |
| 3752 | 3 | 4 | 5 | 6 | | VI-1 | Smcr8 |
| 3753 | 3 | 4 | 5 | 6 | | VI-1 | Smim4 |
| 3754 | 3 | 4 | 5 | 6 | | VI-1 | Smpd3 |
| 3755 | 3 | 4 | 5 | 6 | | VI-1 | Smtn2 |
| 3756 | 3 | 4 | 5 | 6 | | VI-1 | Snai3 |
| 3757 | 3 | 4 | 5 | 6 | | VI-1 | Snap25 |
| 3758 | 3 | 4 | 5 | 6 | | VI-1 | Snhg10 |
| 3759 | 3 | 4 | 5 | 6 | | VI-1 | Snhg3 |
| 3760 | 3 | 4 | 5 | 6 | | VI-1 | Snhg4 |
| 3761 | 3 | 4 | 5 | 6 | | VI-1 | Snhg6 |
| 3762 | 3 | 4 | 5 | 6 | | VI-1 | Snora23 |
| 3763 | 3 | 4 | 5 | 6 | | VI-1 | Snora74a |
| 3764 | 3 | 4 | 5 | 6 | | VI-1 | Snord17 |
| 3765 | 3 | 4 | 5 | 6 | | VI-1 | Snrnp25 |
| 3766 | 3 | 4 | 5 | 6 | | VI-1 | Snrpf |
| 3767 | 3 | 4 | 5 | 6 | | VI-1 | Snrpg |
| 3768 | 3 | 4 | 5 | 6 | | VI-1 | Snta1 |
| 3769 | 3 | 4 | 5 | 6 | | VI-1 | Sntb1 |
| 3770 | 3 | 4 | 5 | 6 | | VI-1 | Sntb2 |
| 3771 | 3 | 4 | 5 | 6 | | VI-1 | Socs1 |
| 3772 | 3 | 4 | 5 | 6 | | VI-1 | Socs3 |
| 3773 | 3 | 4 | 5 | 6 | | VI-1 | Socs4 |
| 3774 | 3 | 4 | 5 | 6 | | VI-1 | Sorl1 |
| 3775 | 3 | 4 | 5 | 6 | | VI-1 | Sox4 |
| 3776 | 3 | 4 | 5 | 6 | | VI-1 | Sox9 |
| 3777 | 3 | 4 | 5 | 6 | | VI-1 | Sparc |
| 3778 | 3 | 4 | 5 | 6 | | VI-1 | Spata24 |
| 3779 | 3 | 4 | 5 | 6 | | VI-1 | Spc24 |
| 3780 | 3 | 4 | 5 | 6 | | VI-1 | Spc25 |
| 3781 | 3 | 4 | 5 | 6 | | VI-1 | Speer7-ps1 |
| 3782 | 3 | 4 | 5 | 6 | | VI-1 | Spen |
| 3783 | 3 | 4 | 5 | 6 | | VI-1 | Sphk1 |
| 3784 | 3 | 4 | 5 | 6 | | VI-1 | Spi1 |
| 3785 | 3 | 4 | 5 | 6 | | VI-1 | Spink5 |
| 3786 | 3 | 4 | 5 | 6 | | VI-1 | Spon1 |
| 3787 | 3 | 4 | 5 | 6 | | VI-1 | Spon2 |
| 3788 | 3 | 4 | 5 | 6 | | VI-1 | Spp1 |
| 3789 | 3 | 4 | 5 | 6 | | VI-1 | Spred2 |
| 3790 | 3 | 4 | 5 | 6 | | VI-1 | Sprr1a |
| 3791 | 3 | 4 | 5 | 6 | | VI-1 | Sprr2d |
| 3792 | 3 | 4 | 5 | 6 | | VI-1 | Sprr2g |
| 3793 | 3 | 4 | 5 | 6 | | VI-1 | Sprr2i |
| 3794 | 3 | 4 | 5 | 6 | | VI-1 | Sprr2j-ps |
| 3795 | 3 | 4 | 5 | 6 | | VI-1 | Sprr3 |
| 3796 | 3 | 4 | 5 | 6 | | VI-1 | Sprtn |
| 3797 | 3 | 4 | 5 | 6 | | VI-1 | Sqle |
| 3798 | 3 | 4 | 5 | 6 | | VI-1 | Srebf1 |
| 3799 | 3 | 4 | 5 | 6 | | VI-1 | Srp54c |
| 3800 | 3 | 4 | 5 | 6 | | VI-1 | Srpx |
| 3801 | 3 | 4 | 5 | 6 | | VI-1 | Srrm2 |
| 3802 | 3 | 4 | 5 | 6 | | VI-1 | Srxn1 |
| 3803 | 3 | 4 | 5 | 6 | | VI-1 | Ssh2 |
| 3804 | 3 | 4 | 5 | 6 | | VI-1 | Sssca1 |
| 3805 | 3 | 4 | 5 | 6 | | VI-1 | Ssx2ip |
| 3806 | 3 | 4 | 5 | 6 | | VI-1 | St3gal5 |
| 3807 | 3 | 4 | 5 | 6 | | VI-1 | Stac3 |
| 3808 | 3 | 4 | 5 | 6 | | VI-1 | Stard4 |
| 3809 | 3 | 4 | 5 | 6 | | VI-1 | Stc2 |
| 3810 | 3 | 4 | 5 | 6 | | VI-1 | Steap3 |
| 3811 | 3 | 4 | 5 | 6 | | VI-1 | Steap4 |
| 3812 | 3 | 4 | 5 | 6 | | VI-1 | Stfa1 |
| 3813 | 3 | 4 | 5 | 6 | | VI-1 | Stfa2 |
| 3814 | 3 | 4 | 5 | 6 | | VI-1 | Ston1 |
| 3815 | 3 | 4 | 5 | 6 | | VI-1 | Stx19 |
| 3816 | 3 | 4 | 5 | 6 | | VI-1 | Suchr1 |
| 3817 | 3 | 4 | 5 | 6 | | VI-1 | Sulf2 |
| 3818 | 3 | 4 | 5 | 6 | | VI-1 | Sult1e1 |
| 3819 | 3 | 4 | 5 | 6 | | VI-1 | Sult2a6 |
| 3820 | 3 | 4 | 5 | 6 | | VI-1 | Sult2a7 |
| 3821 | 3 | 4 | 5 | 6 | | VI-1 | Svep1 |
| 3822 | 3 | 4 | 5 | 6 | | VI-1 | Syce2 |
| 3823 | 3 | 4 | 5 | 6 | | VI-1 | Sync |

| | | | | | | | | |
|---|---|---|---|---|---|---|---|---|
| 3824 | 3 | 4 | 5 | 6 | | VI-1 | Syngr1 |
| 3825 | 3 | 4 | 5 | 6 | | VI-1 | Synm |
| 3826 | 3 | 4 | 5 | 6 | | VI-1 | Synpo |
| 3827 | 3 | 4 | 5 | 6 | | VI-1 | Synpo2 |
| 3828 | 3 | 4 | 5 | 6 | | VI-1 | Syt12 |
| 3829 | 3 | 4 | 5 | 6 | | VI-1 | Tacc2 |
| 3830 | 3 | 4 | 5 | 6 | | VI-1 | Tagln3 |
| 3831 | 3 | 4 | 5 | 6 | | VI-1 | Tamm41 |
| 3832 | 3 | 4 | 5 | 6 | | VI-1 | Tap1 |
| 3833 | 3 | 4 | 5 | 6 | | VI-1 | Tat |
| 3834 | 3 | 4 | 5 | 6 | | VI-1 | Tbc1d1 |
| 3835 | 3 | 4 | 5 | 6 | | VI-1 | Tbc1d30 |
| 3836 | 3 | 4 | 5 | 6 | | VI-1 | Tbca |
| 3837 | 3 | 4 | 5 | 6 | | VI-1 | Tbl1x |
| 3838 | 3 | 4 | 5 | 6 | | VI-1 | Tbx3 |
| 3839 | 3 | 4 | 5 | 6 | | VI-1 | Tcea3 |
| 3840 | 3 | 4 | 5 | 6 | | VI-1 | Tceal5 |
| 3841 | 3 | 4 | 5 | 6 | | VI-1 | Tchh |
| 3842 | 3 | 4 | 5 | 6 | | VI-1 | Tctex1d2 |
| 3843 | 3 | 4 | 5 | 6 | | VI-1 | Tdg |
| 3844 | 3 | 4 | 5 | 6 | | VI-1 | Tdh |
| 3845 | 3 | 4 | 5 | 6 | | VI-1 | Tekt5 |
| 3846 | 3 | 4 | 5 | 6 | | VI-1 | Tex40 |
| 3847 | 3 | 4 | 5 | 6 | | VI-1 | Tff2 |
| 3848 | 3 | 4 | 5 | 6 | | VI-1 | Tfrc |
| 3849 | 3 | 4 | 5 | 6 | | VI-1 | Tg |
| 3850 | 3 | 4 | 5 | 6 | | VI-1 | Tgm1 |
| 3851 | 3 | 4 | 5 | 6 | | VI-1 | Tgm5 |
| 3852 | 3 | 4 | 5 | 6 | | VI-1 | Thbs4 |
| 3853 | 3 | 4 | 5 | 6 | | VI-1 | Them6 |
| 3854 | 3 | 4 | 5 | 6 | | VI-1 | Themis2 |
| 3855 | 3 | 4 | 5 | 6 | | VI-1 | Thra |
| 3856 | 3 | 4 | 5 | 6 | | VI-1 | Thy1 |
| 3857 | 3 | 4 | 5 | 6 | | VI-1 | Thyn1 |
| 3858 | 3 | 4 | 5 | 6 | | VI-1 | Tigd3 |
| 3859 | 3 | 4 | 5 | 6 | | VI-1 | Tigit |
| 3860 | 3 | 4 | 5 | 6 | | VI-1 | Timp1 |
| 3861 | 3 | 4 | 5 | 6 | | VI-1 | Timp4 |
| 3862 | 3 | 4 | 5 | 6 | | VI-1 | Tlr1 |
| 3863 | 3 | 4 | 5 | 6 | | VI-1 | Tlr13 |
| 3864 | 3 | 4 | 5 | 6 | | VI-1 | Tlr6 |
| 3865 | 3 | 4 | 5 | 6 | | VI-1 | Tlr8 |
| 3866 | 3 | 4 | 5 | 6 | | VI-1 | Tlr9 |
| 3867 | 3 | 4 | 5 | 6 | | VI-1 | Tmed11 |
| 3868 | 3 | 4 | 5 | 6 | | VI-1 | Tmed6 |
| 3869 | 3 | 4 | 5 | 6 | | VI-1 | Tmem106a |
| 3870 | 3 | 4 | 5 | 6 | | VI-1 | Tmem107 |
| 3871 | 3 | 4 | 5 | 6 | | VI-1 | Tmem119 |
| 3872 | 3 | 4 | 5 | 6 | | VI-1 | Tmem120a |
| 3873 | 3 | 4 | 5 | 6 | | VI-1 | Tmem139 |
| 3874 | 3 | 4 | 5 | 6 | | VI-1 | Tmem14a |
| 3875 | 3 | 4 | 5 | 6 | | VI-1 | Tmem164 |
| 3876 | 3 | 4 | 5 | 6 | | VI-1 | Tmem171 |
| 3877 | 3 | 4 | 5 | 6 | | VI-1 | Tmem176a |
| 3878 | 3 | 4 | 5 | 6 | | VI-1 | Tmem176b |
| 3879 | 3 | 4 | 5 | 6 | | VI-1 | Tmem179 |
| 3880 | 3 | 4 | 5 | 6 | | VI-1 | Tmem182 |
| 3881 | 3 | 4 | 5 | 6 | | VI-1 | Tmem184c |
| 3882 | 3 | 4 | 5 | 6 | | VI-1 | Tmem25 |
| 3883 | 3 | 4 | 5 | 6 | | VI-1 | Tmem252 |
| 3884 | 3 | 4 | 5 | 6 | | VI-1 | Tmem27 |
| 3885 | 3 | 4 | 5 | 6 | | VI-1 | Tmem37 |
| 3886 | 3 | 4 | 5 | 6 | | VI-1 | Tmem40 |
| 3887 | 3 | 4 | 5 | 6 | | VI-1 | Tmem43 |
| 3888 | 3 | 4 | 5 | 6 | | VI-1 | Tmem52 |
| 3889 | 3 | 4 | 5 | 6 | | VI-1 | Tmem86a |
| 3890 | 3 | 4 | 5 | 6 | | VI-1 | Tmsb15b1 |
| 3891 | 3 | 4 | 5 | 6 | | VI-1 | Tmsb15b2 |
| 3892 | 3 | 4 | 5 | 6 | | VI-1 | Tnc |
| 3893 | 3 | 4 | 5 | 6 | | VI-1 | Tnfaip6 |
| 3894 | 3 | 4 | 5 | 6 | | VI-1 | Tnfrsf10b |
| 3895 | 3 | 4 | 5 | 6 | | VI-1 | Tnfrsf12a |
| 3896 | 3 | 4 | 5 | 6 | | VI-1 | Tnfsf13b |
| 3897 | 3 | 4 | 5 | 6 | | VI-1 | Tnks |
| 3898 | 3 | 4 | 5 | 6 | | VI-1 | Tnpo1 |
| 3899 | 3 | 4 | 5 | 6 | | VI-1 | Tns3 |
| 3900 | 3 | 4 | 5 | 6 | | VI-1 | Top2a |
| 3901 | 3 | 4 | 5 | 6 | | VI-1 | Toporsos |
| 3902 | 3 | 4 | 5 | 6 | | VI-1 | Tpd52l1 |
| 3903 | 3 | 4 | 5 | 6 | | VI-1 | Tpi1 |
| 3904 | 3 | 4 | 5 | 6 | | VI-1 | Tpm1 |
| 3905 | 3 | 4 | 5 | 6 | | VI-1 | Treh |
| 3906 | 3 | 4 | 5 | 6 | | VI-1 | Trem2 |
| 3907 | 3 | 4 | 5 | 6 | | VI-1 | Trem3 |
| 3908 | 3 | 4 | 5 | 6 | | VI-1 | Treml1 |

Fig. 43 - 24

| | | | | | | | |
|---|---|---|---|---|---|---|---|
| 3909 | 3 | 4 | 5 | 6 | | VI-1 | Treml4 |
| 3910 | 3 | 4 | 5 | 6 | | VI-1 | Trib3 |
| 3911 | 3 | 4 | 5 | 6 | | VI-1 | Trim29 |
| 3912 | 3 | 4 | 5 | 6 | | VI-1 | Trim30a |
| 3913 | 3 | 4 | 5 | 6 | | VI-1 | Trim30d |
| 3914 | 3 | 4 | 5 | 6 | | VI-1 | Trim6 |
| 3915 | 3 | 4 | 5 | 6 | | VI-1 | Trim7 |
| 3916 | 3 | 4 | 5 | 6 | | VI-1 | Trip11 |
| 3917 | 3 | 4 | 5 | 6 | | VI-1 | Trmt61b |
| 3918 | 3 | 4 | 5 | 6 | | VI-1 | Trpv6 |
| 3919 | 3 | 4 | 5 | 6 | | VI-1 | Tsc22d1 |
| 3920 | 3 | 4 | 5 | 6 | | VI-1 | Tsku |
| 3921 | 3 | 4 | 5 | 6 | | VI-1 | Tspan8 |
| 3922 | 3 | 4 | 5 | 6 | | VI-1 | Tspyl4 |
| 3923 | 3 | 4 | 5 | 6 | | VI-1 | Tsta3 |
| 3924 | 3 | 4 | 5 | 6 | | VI-1 | Tstd1 |
| 3925 | 3 | 4 | 5 | 6 | | VI-1 | Ttc36 |
| 3926 | 3 | 4 | 5 | 6 | | VI-1 | Ttpa |
| 3927 | 3 | 4 | 5 | 6 | | VI-1 | Tuba8 |
| 3928 | 3 | 4 | 5 | 6 | | VI-1 | Tyrobp |
| 3929 | 3 | 4 | 5 | 6 | | VI-1 | Ube2c |
| 3930 | 3 | 4 | 5 | 6 | | VI-1 | Ube2l6 |
| 3931 | 3 | 4 | 5 | 6 | | VI-1 | Uchl3 |
| 3932 | 3 | 4 | 5 | 6 | | VI-1 | Ucp1 |
| 3933 | 3 | 4 | 5 | 6 | | VI-1 | Ufsp1 |
| 3934 | 3 | 4 | 5 | 6 | | VI-1 | Ugt1a2 |
| 3935 | 3 | 4 | 5 | 6 | | VI-1 | Ugt1a6a |
| 3936 | 3 | 4 | 5 | 6 | | VI-1 | Uhrf1 |
| 3937 | 3 | 4 | 5 | 6 | | VI-1 | Umod |
| 3938 | 3 | 4 | 5 | 6 | | VI-1 | Upk3b |
| 3939 | 3 | 4 | 5 | 6 | | VI-1 | Upp1 |
| 3940 | 3 | 4 | 5 | 6 | | VI-1 | Uqcc2 |
| 3941 | 3 | 4 | 5 | 6 | | VI-1 | Urah |
| 3942 | 3 | 4 | 5 | 6 | | VI-1 | Usmg5 |
| 3943 | 3 | 4 | 5 | 6 | | VI-1 | Usp6nl |
| 3944 | 3 | 4 | 5 | 6 | | VI-1 | Vcam1 |
| 3945 | 3 | 4 | 5 | 6 | | VI-1 | Vdr |
| 3946 | 3 | 4 | 5 | 6 | | VI-1 | Vldlr |
| 3947 | 3 | 4 | 5 | 6 | | VI-1 | Vwa1 |
| 3948 | 3 | 4 | 5 | 6 | | VI-1 | Wasf2 |
| 3949 | 3 | 4 | 5 | 6 | | VI-1 | Wbscr17 |
| 3950 | 3 | 4 | 5 | 6 | | VI-1 | Wdfy2 |
| 3951 | 3 | 4 | 5 | 6 | | VI-1 | Wdhd1 |
| 3952 | 3 | 4 | 5 | 6 | | VI-1 | Wdr34 |
| 3953 | 3 | 4 | 5 | 6 | | VI-1 | Wee1 |
| 3954 | 3 | 4 | 5 | 6 | | VI-1 | Wfdc1 |
| 3955 | 3 | 4 | 5 | 6 | | VI-1 | Wfdc12 |
| 3956 | 3 | 4 | 5 | 6 | | VI-1 | Wfdc6a |
| 3957 | 3 | 4 | 5 | 6 | | VI-1 | Wfikkn1 |
| 3958 | 3 | 4 | 5 | 6 | | VI-1 | Wisp2 |
| 3959 | 3 | 4 | 5 | 6 | | VI-1 | Wnt5a |
| 3960 | 3 | 4 | 5 | 6 | | VI-1 | Xaf1 |
| 3961 | 3 | 4 | 5 | 6 | | VI-1 | Xcl1 |
| 3962 | 3 | 4 | 5 | 6 | | VI-1 | Xkr9 |
| 3963 | 3 | 4 | 5 | 6 | | VI-1 | Xlr4c |
| 3964 | 3 | 4 | 5 | 6 | | VI-1 | Xrcc3 |
| 3965 | 3 | 4 | 5 | 6 | | VI-1 | Xrcc6bp1 |
| 3966 | 3 | 4 | 5 | 6 | | VI-1 | Ydjc |
| 3967 | 3 | 4 | 5 | 6 | | VI-1 | Yipf7 |
| 3968 | 3 | 4 | 5 | 6 | | VI-1 | Zak |
| 3969 | 3 | 4 | 5 | 6 | | VI-1 | Zbp1 |
| 3970 | 3 | 4 | 5 | 6 | | VI-1 | Zbtb8os |
| 3971 | 3 | 4 | 5 | 6 | | VI-1 | Zeb2os |
| 3972 | 3 | 4 | 5 | 6 | | VI-1 | Zfp185 |
| 3973 | 3 | 4 | 5 | 6 | | VI-1 | Zfp503 |
| 3974 | 3 | 4 | 5 | 6 | | VI-1 | Zfp609 |
| 3975 | 3 | 4 | 5 | 6 | | VI-1 | Zfp652 |
| 3976 | 3 | 4 | 5 | 6 | | VI-1 | Zfp750 |
| 3977 | 3 | 4 | 5 | 6 | | VI-1 | Zg16 |
| 3978 | 3 | 4 | 5 | 6 | | VI-1 | Zmat3 |
| 3979 | 3 | 4 | 5 | 6 | | VI-1 | Zswim7 |
| 3980 | 3 | 4 | 5 | | | V-2 | 0610005C13Rik |
| 3981 | 3 | 4 | 5 | | | V-2 | 0610007P14Rik |
| 3982 | 3 | 4 | 5 | | | V-2 | 0610009B22Rik |
| 3983 | 3 | 4 | 5 | | | V-2 | 0610009O20Rik |
| 3984 | 3 | 4 | 5 | | | V-2 | 0610030E20Rik |
| 3985 | 3 | 4 | 5 | | | V-2 | 0610038B21Rik |
| 3986 | 3 | 4 | 5 | | | V-2 | 1110004E09Rik |
| 3987 | 3 | 4 | 5 | | | V-2 | 1110008L16Rik |
| 3988 | 3 | 4 | 5 | | | V-2 | 1110019D14Rik |
| 3989 | 3 | 4 | 5 | | | V-2 | 1110032A03Rik |
| 3990 | 3 | 4 | 5 | | | V-2 | 1110054M08Rik |
| 3991 | 3 | 4 | 5 | | | V-2 | 1110057K04Rik |
| 3992 | 3 | 4 | 5 | | | V-2 | 1300002E11Rik |
| 3993 | 3 | 4 | 5 | | | V-2 | 1300017J02Rik |

| | | | | | | | |
|---|---|---|---|---|---|---|---|
| 3994 | 3 | 4 | 5 | | | V-2 | 1500004A13Rik |
| 3995 | 3 | 4 | 5 | | | V-2 | 1500009C09Rik |
| 3996 | 3 | 4 | 5 | | | V-2 | 1500015D10Rik |
| 3997 | 3 | 4 | 5 | | | V-2 | 1500017E21Rik |
| 3998 | 3 | 4 | 5 | | | V-2 | 1600002H07Rik |
| 3999 | 3 | 4 | 5 | | | V-2 | 1600002K03Rik |
| 4000 | 3 | 4 | 5 | | | V-2 | 1600012H06Rik |
| 4001 | 3 | 4 | 5 | | | V-2 | 1600023N17Rik |
| 4002 | 3 | 4 | 5 | | | V-2 | 1600029I14Rik |
| 4003 | 3 | 4 | 5 | | | V-2 | 1700001C19Rik |
| 4004 | 3 | 4 | 5 | | | V-2 | 1700001J11Rik |
| 4005 | 3 | 4 | 5 | | | V-2 | 1700003D09Rik |
| 4006 | 3 | 4 | 5 | | | V-2 | 1700003M02Rik |
| 4007 | 3 | 4 | 5 | | | V-2 | 1700011E24Rik |
| 4008 | 3 | 4 | 5 | | | V-2 | 1700012A03Rik |
| 4009 | 3 | 4 | 5 | | | V-2 | 1700012B07Rik |
| 4010 | 3 | 4 | 5 | | | V-2 | 1700013D24Rik |
| 4011 | 3 | 4 | 5 | | | V-2 | 1700017B05Rik |
| 4012 | 3 | 4 | 5 | | | V-2 | 1700018C11Rik |
| 4013 | 3 | 4 | 5 | | | V-2 | 1700019A02Rik |
| 4014 | 3 | 4 | 5 | | | V-2 | 1700020I14Rik |
| 4015 | 3 | 4 | 5 | | | V-2 | 1700020L24Rik |
| 4016 | 3 | 4 | 5 | | | V-2 | 1700021K19Rik |
| 4017 | 3 | 4 | 5 | | | V-2 | 1700022A21Rik |
| 4018 | 3 | 4 | 5 | | | V-2 | 1700027F09Rik |
| 4019 | 3 | 4 | 5 | | | V-2 | 1700028P15Rik |
| 4020 | 3 | 4 | 5 | | | V-2 | 1700029H14Rik |
| 4021 | 3 | 4 | 5 | | | V-2 | 1700031P21Rik |
| 4022 | 3 | 4 | 5 | | | V-2 | 1700034E13Rik |
| 4023 | 3 | 4 | 5 | | | V-2 | 1700034J05Rik |
| 4024 | 3 | 4 | 5 | | | V-2 | 1700037C18Rik |
| 4025 | 3 | 4 | 5 | | | V-2 | 1700040L02Rik |
| 4026 | 3 | 4 | 5 | | | V-2 | 1700042G07Rik |
| 4027 | 3 | 4 | 5 | | | V-2 | 1700049G17Rik |
| 4028 | 3 | 4 | 5 | | | V-2 | 1700052N19Rik |
| 4029 | 3 | 4 | 5 | | | V-2 | 1700065J11Rik |
| 4030 | 3 | 4 | 5 | | | V-2 | 1700066M21Rik |
| 4031 | 3 | 4 | 5 | | | V-2 | 1700067P10Rik |
| 4032 | 3 | 4 | 5 | | | V-2 | 1700072O05Rik |
| 4033 | 3 | 4 | 5 | | | V-2 | 1700092C02Rik |
| 4034 | 3 | 4 | 5 | | | V-2 | 1700101E01Rik |
| 4035 | 3 | 4 | 5 | | | V-2 | 1700109G15Rik |
| 4036 | 3 | 4 | 5 | | | V-2 | 1810011H11Rik |
| 4037 | 3 | 4 | 5 | | | V-2 | 1810065E05Rik |
| 4038 | 3 | 4 | 5 | | | V-2 | 2010012O05Rik |
| 4039 | 3 | 4 | 5 | | | V-2 | 2010016I18Rik |
| 4040 | 3 | 4 | 5 | | | V-2 | 2010107G23Rik |
| 4041 | 3 | 4 | 5 | | | V-2 | 2010109A12Rik |
| 4042 | 3 | 4 | 5 | | | V-2 | 2010111I01Rik |
| 4043 | 3 | 4 | 5 | | | V-2 | 2010300C02Rik |
| 4044 | 3 | 4 | 5 | | | V-2 | 2210039B01Rik |
| 4045 | 3 | 4 | 5 | | | V-2 | 2210408I21Rik |
| 4046 | 3 | 4 | 5 | | | V-2 | 2210416O15Rik |
| 4047 | 3 | 4 | 5 | | | V-2 | 2310003H01Rik |
| 4048 | 3 | 4 | 5 | | | V-2 | 2310047M10Rik |
| 4049 | 3 | 4 | 5 | | | V-2 | 2310081J21Rik |
| 4050 | 3 | 4 | 5 | | | V-2 | 2410004B18Rik |
| 4051 | 3 | 4 | 5 | | | V-2 | 2410089E03Rik |
| 4052 | 3 | 4 | 5 | | | V-2 | 2410131K14Rik |
| 4053 | 3 | 4 | 5 | | | V-2 | 2500004C02Rik |
| 4054 | 3 | 4 | 5 | | | V-2 | 2510003E04Rik |
| 4055 | 3 | 4 | 5 | | | V-2 | 2510039O18Rik |
| 4056 | 3 | 4 | 5 | | | V-2 | 2610008E11Rik |
| 4057 | 3 | 4 | 5 | | | V-2 | 2610015P09Rik |
| 4058 | 3 | 4 | 5 | | | V-2 | 2610020H08Rik |
| 4059 | 3 | 4 | 5 | | | V-2 | 2610206C17Rik |
| 4060 | 3 | 4 | 5 | | | V-2 | 2610507B11Rik |
| 4061 | 3 | 4 | 5 | | | V-2 | 2700029M09Rik |
| 4062 | 3 | 4 | 5 | | | V-2 | 2700049A03Rik |
| 4063 | 3 | 4 | 5 | | | V-2 | 2700054A10Rik |
| 4064 | 3 | 4 | 5 | | | V-2 | 2700081O15Rik |
| 4065 | 3 | 4 | 5 | | | V-2 | 2700086A05Rik |
| 4066 | 3 | 4 | 5 | | | V-2 | 2810006K23Rik |
| 4067 | 3 | 4 | 5 | | | V-2 | 2810007J24Rik |
| 4068 | 3 | 4 | 5 | | | V-2 | 2810025M15Rik |
| 4069 | 3 | 4 | 5 | | | V-2 | 2810408A11Rik |
| 4070 | 3 | 4 | 5 | | | V-2 | 2810408M09Rik |
| 4071 | 3 | 4 | 5 | | | V-2 | 2810442I21Rik |
| 4072 | 3 | 4 | 5 | | | V-2 | 2810468N07Rik |
| 4073 | 3 | 4 | 5 | | | V-2 | 3110001I22Rik |
| 4074 | 3 | 4 | 5 | | | V-2 | 3110002H16Rik |
| 4075 | 3 | 4 | 5 | | | V-2 | 3110007F17Rik |
| 4076 | 3 | 4 | 5 | | | V-2 | 3110009E18Rik |
| 4077 | 3 | 4 | 5 | | | V-2 | 3110015C05Rik |
| 4078 | 3 | 4 | 5 | | | V-2 | 3110052M02Rik |

Fig. 43 - 25

| | | | | | | | |
|---|---|---|---|---|---|---|---|
| 4079 | 3 | 4 | 5 | | | V-2 | 3110056K07Rik |
| 4080 | 3 | 4 | 5 | | | V-2 | 3110057O12Rik |
| 4081 | 3 | 4 | 5 | | | V-2 | 3110062M04Rik |
| 4082 | 3 | 4 | 5 | | | V-2 | 3632451O06Rik |
| 4083 | 3 | 4 | 5 | | | V-2 | 4430402I18Rik |
| 4084 | 3 | 4 | 5 | | | V-2 | 4831440E17Rik |
| 4085 | 3 | 4 | 5 | | | V-2 | 4833422C13Rik |
| 4086 | 3 | 4 | 5 | | | V-2 | 4921530L21Rik |
| 4087 | 3 | 4 | 5 | | | V-2 | 4930402F06Rik |
| 4088 | 3 | 4 | 5 | | | V-2 | 4930402F11Rik |
| 4089 | 3 | 4 | 5 | | | V-2 | 4930405L22Rik |
| 4090 | 3 | 4 | 5 | | | V-2 | 4930413M19Rik |
| 4091 | 3 | 4 | 5 | | | V-2 | 4930426L09Rik |
| 4092 | 3 | 4 | 5 | | | V-2 | 4930430F08Rik |
| 4093 | 3 | 4 | 5 | | | V-2 | 4930432K21Rik |
| 4094 | 3 | 4 | 5 | | | V-2 | 4930440I19Rik |
| 4095 | 3 | 4 | 5 | | | V-2 | 4930451C15Rik |
| 4096 | 3 | 4 | 5 | | | V-2 | 4930480G23Rik |
| 4097 | 3 | 4 | 5 | | | V-2 | 4930481A15Rik |
| 4098 | 3 | 4 | 5 | | | V-2 | 4930486I03Rik |
| 4099 | 3 | 4 | 5 | | | V-2 | 4930502E09Rik |
| 4100 | 3 | 4 | 5 | | | V-2 | 4930505A04Rik |
| 4101 | 3 | 4 | 5 | | | V-2 | 4930506M07Rik |
| 4102 | 3 | 4 | 5 | | | V-2 | 4930511M06Rik |
| 4103 | 3 | 4 | 5 | | | V-2 | 4930513N10Rik |
| 4104 | 3 | 4 | 5 | | | V-2 | 4930526I15Rik |
| 4105 | 3 | 4 | 5 | | | V-2 | 4930526L06Rik |
| 4106 | 3 | 4 | 5 | | | V-2 | 4930533B01Rik |
| 4107 | 3 | 4 | 5 | | | V-2 | 4930557A04Rik |
| 4108 | 3 | 4 | 5 | | | V-2 | 4930563D23Rik |
| 4109 | 3 | 4 | 5 | | | V-2 | 4931414P19Rik |
| 4110 | 3 | 4 | 5 | | | V-2 | 4931420L22Rik |
| 4111 | 3 | 4 | 5 | | | V-2 | 4931428F04Rik |
| 4112 | 3 | 4 | 5 | | | V-2 | 4931428L18Rik |
| 4113 | 3 | 4 | 5 | | | V-2 | 4933407K13Rik |
| 4114 | 3 | 4 | 5 | | | V-2 | 4933412E12Rik |
| 4115 | 3 | 4 | 5 | | | V-2 | 4933417E11Rik |
| 4116 | 3 | 4 | 5 | | | V-2 | 4933421O10Rik |
| 4117 | 3 | 4 | 5 | | | V-2 | 4933426M11Rik |
| 4118 | 3 | 4 | 5 | | | V-2 | 4933427I22Rik |
| 4119 | 3 | 4 | 5 | | | V-2 | 4933430N04Rik |
| 4120 | 3 | 4 | 5 | | | V-2 | 4933432K03Rik |
| 4121 | 3 | 4 | 5 | | | V-2 | 5031414D18Rik |
| 4122 | 3 | 4 | 5 | | | V-2 | 5031425E22Rik |
| 4123 | 3 | 4 | 5 | | | V-2 | 5031439G07Rik |
| 4124 | 3 | 4 | 5 | | | V-2 | 5430405H02Rik |
| 4125 | 3 | 4 | 5 | | | V-2 | 5430416O09Rik |
| 4126 | 3 | 4 | 5 | | | V-2 | 5430427M07Rik |
| 4127 | 3 | 4 | 5 | | | V-2 | 5830417I10Rik |
| 4128 | 3 | 4 | 5 | | | V-2 | 5830418K08Rik |
| 4129 | 3 | 4 | 5 | | | V-2 | 5830428M24Rik |
| 4130 | 3 | 4 | 5 | | | V-2 | 5830444B04Rik |
| 4131 | 3 | 4 | 5 | | | V-2 | 5930412G12Rik |
| 4132 | 3 | 4 | 5 | | | V-2 | 6030458C11Rik |
| 4133 | 3 | 4 | 5 | | | V-2 | 6330408A02Rik |
| 4134 | 3 | 4 | 5 | | | V-2 | 6430562O15Rik |
| 4135 | 3 | 4 | 5 | | | V-2 | 9230102O04Rik |
| 4136 | 3 | 4 | 5 | | | V-2 | 9330020H09Rik |
| 4137 | 3 | 4 | 5 | | | V-2 | 9330102E08Rik |
| 4138 | 3 | 4 | 5 | | | V-2 | 9430015G10Rik |
| 4139 | 3 | 4 | 5 | | | V-2 | 9430091E24Rik |
| 4140 | 3 | 4 | 5 | | | V-2 | A230057D06Rik |
| 4141 | 3 | 4 | 5 | | | V-2 | A230103J11Rik |
| 4142 | 3 | 4 | 5 | | | V-2 | A330009N23Rik |
| 4143 | 3 | 4 | 5 | | | V-2 | A330023F24Rik |
| 4144 | 3 | 4 | 5 | | | V-2 | A330070K13Rik |
| 4145 | 3 | 4 | 5 | | | V-2 | A430107P09Rik |
| 4146 | 3 | 4 | 5 | | | V-2 | A530054K11Rik |
| 4147 | 3 | 4 | 5 | | | V-2 | A530088E08Rik |
| 4148 | 3 | 4 | 5 | | | V-2 | A630033H20Rik |
| 4149 | 3 | 4 | 5 | | | V-2 | A630089N07Rik |
| 4150 | 3 | 4 | 5 | | | V-2 | A730017L22Rik |
| 4151 | 3 | 4 | 5 | | | V-2 | A730020M07Rik |
| 4152 | 3 | 4 | 5 | | | V-2 | A730098P11Rik |
| 4153 | 3 | 4 | 5 | | | V-2 | A830010M20Rik |
| 4154 | 3 | 4 | 5 | | | V-2 | AA415398 |
| 4155 | 3 | 4 | 5 | | | V-2 | AA986860 |
| 4156 | 3 | 4 | 5 | | | V-2 | AA987161 |
| 4157 | 3 | 4 | 5 | | | V-2 | Aadacl2 |
| 4158 | 3 | 4 | 5 | | | V-2 | Aamp |
| 4159 | 3 | 4 | 5 | | | V-2 | Aars2 |
| 4160 | 3 | 4 | 5 | | | V-2 | Aasdh |
| 4161 | 3 | 4 | 5 | | | V-2 | Abca3 |
| 4162 | 3 | 4 | 5 | | | V-2 | Abcb9 |
| 4163 | 3 | 4 | 5 | | | V-2 | Abcc4 |
| 4164 | 3 | 4 | 5 | | | V-2 | Abcd1 |
| 4165 | 3 | 4 | 5 | | | V-2 | Abcf3 |
| 4166 | 3 | 4 | 5 | | | V-2 | Abcg3 |
| 4167 | 3 | 4 | 5 | | | V-2 | Abhd14a |
| 4168 | 3 | 4 | 5 | | | V-2 | Abhd4 |
| 4169 | 3 | 4 | 5 | | | V-2 | Abhd8 |
| 4170 | 3 | 4 | 5 | | | V-2 | Abi3 |
| 4171 | 3 | 4 | 5 | | | V-2 | Abt1 |
| 4172 | 3 | 4 | 5 | | | V-2 | Abtb1 |
| 4173 | 3 | 4 | 5 | | | V-2 | Acaa2 |
| 4174 | 3 | 4 | 5 | | | V-2 | Acaca |
| 4175 | 3 | 4 | 5 | | | V-2 | Acad11 |
| 4176 | 3 | 4 | 5 | | | V-2 | Acad12 |
| 4177 | 3 | 4 | 5 | | | V-2 | Acad8 |
| 4178 | 3 | 4 | 5 | | | V-2 | Acadl |
| 4179 | 3 | 4 | 5 | | | V-2 | Acadm |
| 4180 | 3 | 4 | 5 | | | V-2 | Acads |
| 4181 | 3 | 4 | 5 | | | V-2 | Acap1 |
| 4182 | 3 | 4 | 5 | | | V-2 | Acbd4 |
| 4183 | 3 | 4 | 5 | | | V-2 | Ache |
| 4184 | 3 | 4 | 5 | | | V-2 | Acn9 |
| 4185 | 3 | 4 | 5 | | | V-2 | Acpp |
| 4186 | 3 | 4 | 5 | | | V-2 | Acsf2 |
| 4187 | 3 | 4 | 5 | | | V-2 | Acsf3 |
| 4188 | 3 | 4 | 5 | | | V-2 | Adam19 |
| 4189 | 3 | 4 | 5 | | | V-2 | Adam1a |
| 4190 | 3 | 4 | 5 | | | V-2 | Adam1b |
| 4191 | 3 | 4 | 5 | | | V-2 | Adamts12 |
| 4192 | 3 | 4 | 5 | | | V-2 | Adamts17 |
| 4193 | 3 | 4 | 5 | | | V-2 | Adamtsl3 |
| 4194 | 3 | 4 | 5 | | | V-2 | Adat1 |
| 4195 | 3 | 4 | 5 | | | V-2 | Adat3 |
| 4196 | 3 | 4 | 5 | | | V-2 | Adck2 |
| 4197 | 3 | 4 | 5 | | | V-2 | Adcy6 |
| 4198 | 3 | 4 | 5 | | | V-2 | Adcy8 |
| 4199 | 3 | 4 | 5 | | | V-2 | Adcy9 |
| 4200 | 3 | 4 | 5 | | | V-2 | Adh5 |
| 4201 | 3 | 4 | 5 | | | V-2 | Adnp2 |
| 4202 | 3 | 4 | 5 | | | V-2 | Adora3 |
| 4203 | 3 | 4 | 5 | | | V-2 | Adra1d |
| 4204 | 3 | 4 | 5 | | | V-2 | Adrbk2 |
| 4205 | 3 | 4 | 5 | | | V-2 | Adss |
| 4206 | 3 | 4 | 5 | | | V-2 | Aff1 |
| 4207 | 3 | 4 | 5 | | | V-2 | Agap1 |
| 4208 | 3 | 4 | 5 | | | V-2 | Agap3 |
| 4209 | 3 | 4 | 5 | | | V-2 | Agfg2 |
| 4210 | 3 | 4 | 5 | | | V-2 | Ago1 |
| 4211 | 3 | 4 | 5 | | | V-2 | Ago3 |
| 4212 | 3 | 4 | 5 | | | V-2 | Ago4 |
| 4213 | 3 | 4 | 5 | | | V-2 | Agpat5 |
| 4214 | 3 | 4 | 5 | | | V-2 | Agtrap |
| 4215 | 3 | 4 | 5 | | | V-2 | Ahsa1 |
| 4216 | 3 | 4 | 5 | | | V-2 | AI314278 |
| 4217 | 3 | 4 | 5 | | | V-2 | AI317395 |
| 4218 | 3 | 4 | 5 | | | V-2 | AI504432 |
| 4219 | 3 | 4 | 5 | | | V-2 | AI662270 |
| 4220 | 3 | 4 | 5 | | | V-2 | AI837181 |
| 4221 | 3 | 4 | 5 | | | V-2 | AI846148 |
| 4222 | 3 | 4 | 5 | | | V-2 | AI847159 |
| 4223 | 3 | 4 | 5 | | | V-2 | Aim1l |
| 4224 | 3 | 4 | 5 | | | V-2 | Aimp1 |
| 4225 | 3 | 4 | 5 | | | V-2 | AK010878 |
| 4226 | 3 | 4 | 5 | | | V-2 | Ak7 |
| 4227 | 3 | 4 | 5 | | | V-2 | Akap10 |
| 4228 | 3 | 4 | 5 | | | V-2 | Akap14 |
| 4229 | 3 | 4 | 5 | | | V-2 | Akr1d1 |
| 4230 | 3 | 4 | 5 | | | V-2 | Akr1e1 |
| 4231 | 3 | 4 | 5 | | | V-2 | Akt1s1 |
| 4232 | 3 | 4 | 5 | | | V-2 | Akt3 |
| 4233 | 3 | 4 | 5 | | | V-2 | Aktip |
| 4234 | 3 | 4 | 5 | | | V-2 | Alad |
| 4235 | 3 | 4 | 5 | | | V-2 | Aldh16a1 |
| 4236 | 3 | 4 | 5 | | | V-2 | Aldh3a2 |
| 4237 | 3 | 4 | 5 | | | V-2 | Aldh8a1 |
| 4238 | 3 | 4 | 5 | | | V-2 | Aldh9a1 |
| 4239 | 3 | 4 | 5 | | | V-2 | Alg14 |
| 4240 | 3 | 4 | 5 | | | V-2 | Alms1 |
| 4241 | 3 | 4 | 5 | | | V-2 | Alox15 |
| 4242 | 3 | 4 | 5 | | | V-2 | Als2 |
| 4243 | 3 | 4 | 5 | | | V-2 | Amacr |
| 4244 | 3 | 4 | 5 | | | V-2 | Amigo1 |
| 4245 | 3 | 4 | 5 | | | V-2 | Amn1 |
| 4246 | 3 | 4 | 5 | | | V-2 | Amph |
| 4247 | 3 | 4 | 5 | | | V-2 | Amz1 |
| 4248 | 3 | 4 | 5 | | | V-2 | Anapc10 |

Fig. 43 - 26

| | | | | | | | |
|---|---|---|---|---|---|---|---|
| 4249 | 3 | 4 | 5 | | | V-2 | Anapc16 |
| 4250 | 3 | 4 | 5 | | | V-2 | Anapc2 |
| 4251 | 3 | 4 | 5 | | | V-2 | Anapc7 |
| 4252 | 3 | 4 | 5 | | | V-2 | Angel1 |
| 4253 | 3 | 4 | 5 | | | V-2 | Angptl6 |
| 4254 | 3 | 4 | 5 | | | V-2 | Ankle1 |
| 4255 | 3 | 4 | 5 | | | V-2 | Ankrd12 |
| 4256 | 3 | 4 | 5 | | | V-2 | Ankrd13d |
| 4257 | 3 | 4 | 5 | | | V-2 | Ankrd17 |
| 4258 | 3 | 4 | 5 | | | V-2 | Ankrd22 |
| 4259 | 3 | 4 | 5 | | | V-2 | Ankrd24 |
| 4260 | 3 | 4 | 5 | | | V-2 | Ankrd26 |
| 4261 | 3 | 4 | 5 | | | V-2 | Ankrd27 |
| 4262 | 3 | 4 | 5 | | | V-2 | Ankrd29 |
| 4263 | 3 | 4 | 5 | | | V-2 | Ankrd39 |
| 4264 | 3 | 4 | 5 | | | V-2 | Ankrd42 |
| 4265 | 3 | 4 | 5 | | | V-2 | Ankrd50 |
| 4266 | 3 | 4 | 5 | | | V-2 | Ankrd54 |
| 4267 | 3 | 4 | 5 | | | V-2 | Ankrd55 |
| 4268 | 3 | 4 | 5 | | | V-2 | Ankrd66 |
| 4269 | 3 | 4 | 5 | | | V-2 | Anks6 |
| 4270 | 3 | 4 | 5 | | | V-2 | Ano1 |
| 4271 | 3 | 4 | 5 | | | V-2 | Aox3 |
| 4272 | 3 | 4 | 5 | | | V-2 | Ap1m1 |
| 4273 | 3 | 4 | 5 | | | V-2 | Ap1m2 |
| 4274 | 3 | 4 | 5 | | | V-2 | Ap1s3 |
| 4275 | 3 | 4 | 5 | | | V-2 | Ap4b1 |
| 4276 | 3 | 4 | 5 | | | V-2 | Ap4m1 |
| 4277 | 3 | 4 | 5 | | | V-2 | Ap5b1 |
| 4278 | 3 | 4 | 5 | | | V-2 | Ap5z1 |
| 4279 | 3 | 4 | 5 | | | V-2 | Apba3 |
| 4280 | 3 | 4 | 5 | | | V-2 | Aplf |
| 4281 | 3 | 4 | 5 | | | V-2 | Apoh |
| 4282 | 3 | 4 | 5 | | | V-2 | Apobec1 |
| 4283 | 3 | 4 | 5 | | | V-2 | Apobec3 |
| 4284 | 3 | 4 | 5 | | | V-2 | Apoh |
| 4285 | 3 | 4 | 5 | | | V-2 | Apol7e |
| 4286 | 3 | 4 | 5 | | | V-2 | Apom |
| 4287 | 3 | 4 | 5 | | | V-2 | Appl1 |
| 4288 | 3 | 4 | 5 | | | V-2 | Aqp2 |
| 4289 | 3 | 4 | 5 | | | V-2 | Aqp4 |
| 4290 | 3 | 4 | 5 | | | V-2 | Aqp7 |
| 4291 | 3 | 4 | 5 | | | V-2 | Arfrp1 |
| 4292 | 3 | 4 | 5 | | | V-2 | Arhgap21 |
| 4293 | 3 | 4 | 5 | | | V-2 | Arhgap26 |
| 4294 | 3 | 4 | 5 | | | V-2 | Arhgap27os3 |
| 4295 | 3 | 4 | 5 | | | V-2 | Arhgap32 |
| 4296 | 3 | 4 | 5 | | | V-2 | Arhgap35 |
| 4297 | 3 | 4 | 5 | | | V-2 | Arhgap6 |
| 4298 | 3 | 4 | 5 | | | V-2 | Arhgef10 |
| 4299 | 3 | 4 | 5 | | | V-2 | Arhgef10l |
| 4300 | 3 | 4 | 5 | | | V-2 | Arhgef11 |
| 4301 | 3 | 4 | 5 | | | V-2 | Arhgef12 |
| 4302 | 3 | 4 | 5 | | | V-2 | Arhgef15 |
| 4303 | 3 | 4 | 5 | | | V-2 | Arhgef17 |
| 4304 | 3 | 4 | 5 | | | V-2 | Arhgef18 |
| 4305 | 3 | 4 | 5 | | | V-2 | Arhgef40 |
| 4306 | 3 | 4 | 5 | | | V-2 | Arhgef6 |
| 4307 | 3 | 4 | 5 | | | V-2 | Arid1a |
| 4308 | 3 | 4 | 5 | | | V-2 | Arid2 |
| 4309 | 3 | 4 | 5 | | | V-2 | Arid3a |
| 4310 | 3 | 4 | 5 | | | V-2 | Arid3b |
| 4311 | 3 | 4 | 5 | | | V-2 | Arid4a |
| 4312 | 3 | 4 | 5 | | | V-2 | Arl10 |
| 4313 | 3 | 4 | 5 | | | V-2 | Arl13b |
| 4314 | 3 | 4 | 5 | | | V-2 | Arl3 |
| 4315 | 3 | 4 | 5 | | | V-2 | Arl6 |
| 4316 | 3 | 4 | 5 | | | V-2 | Arl6ip6 |
| 4317 | 3 | 4 | 5 | | | V-2 | Armc12 |
| 4318 | 3 | 4 | 5 | | | V-2 | Armc2 |
| 4319 | 3 | 4 | 5 | | | V-2 | Armc5 |
| 4320 | 3 | 4 | 5 | | | V-2 | Armc6 |
| 4321 | 3 | 4 | 5 | | | V-2 | Armc9 |
| 4322 | 3 | 4 | 5 | | | V-2 | Arrdc2 |
| 4323 | 3 | 4 | 5 | | | V-2 | Arsa |
| 4324 | 3 | 4 | 5 | | | V-2 | Arsk |
| 4325 | 3 | 4 | 5 | | | V-2 | Art2b |
| 4326 | 3 | 4 | 5 | | | V-2 | Asah1 |
| 4327 | 3 | 4 | 5 | | | V-2 | Asb1 |
| 4328 | 3 | 4 | 5 | | | V-2 | Asb13 |
| 4329 | 3 | 4 | 5 | | | V-2 | Asb15 |
| 4330 | 3 | 4 | 5 | | | V-2 | Asb3 |
| 4331 | 3 | 4 | 5 | | | V-2 | Asb4 |
| 4332 | 3 | 4 | 5 | | | V-2 | Asb6 |
| 4333 | 3 | 4 | 5 | | | V-2 | Asf1a |
| 4334 | 3 | 4 | 5 | | | V-2 | Aspdh |
| 4335 | 3 | 4 | 5 | | | V-2 | Asun |
| 4336 | 3 | 4 | 5 | | | V-2 | Atad2b |
| 4337 | 3 | 4 | 5 | | | V-2 | Atg101 |
| 4338 | 3 | 4 | 5 | | | V-2 | Atg14 |
| 4339 | 3 | 4 | 5 | | | V-2 | Atg4d |
| 4340 | 3 | 4 | 5 | | | V-2 | Atg5 |
| 4341 | 3 | 4 | 5 | | | V-2 | Atp10a |
| 4342 | 3 | 4 | 5 | | | V-2 | Atp11b |
| 4343 | 3 | 4 | 5 | | | V-2 | Atp2b4 |
| 4344 | 3 | 4 | 5 | | | V-2 | Atp5sl |
| 4345 | 3 | 4 | 5 | | | V-2 | Atp6v0a4 |
| 4346 | 3 | 4 | 5 | | | V-2 | Atp6v0b |
| 4347 | 3 | 4 | 5 | | | V-2 | Atp6v0d1 |
| 4348 | 3 | 4 | 5 | | | V-2 | Atp6v0e |
| 4349 | 3 | 4 | 5 | | | V-2 | Atp6v1e1 |
| 4350 | 3 | 4 | 5 | | | V-2 | Atp7a |
| 4351 | 3 | 4 | 5 | | | V-2 | Atp8a1 |
| 4352 | 3 | 4 | 5 | | | V-2 | Atp8b2 |
| 4353 | 3 | 4 | 5 | | | V-2 | Atxn10 |
| 4354 | 3 | 4 | 5 | | | V-2 | Atxn3 |
| 4355 | 3 | 4 | 5 | | | V-2 | Auh |
| 4356 | 3 | 4 | 5 | | | V-2 | AV051173 |
| 4357 | 3 | 4 | 5 | | | V-2 | Avl9 |
| 4358 | 3 | 4 | 5 | | | V-2 | Avpr2 |
| 4359 | 3 | 4 | 5 | | | V-2 | AW046200 |
| 4360 | 3 | 4 | 5 | | | V-2 | AW146154 |
| 4361 | 3 | 4 | 5 | | | V-2 | AW549877 |
| 4362 | 3 | 4 | 5 | | | V-2 | AY074887 |
| 4363 | 3 | 4 | 5 | | | V-2 | B130034C11Rik |
| 4364 | 3 | 4 | 5 | | | V-2 | B230206H07Rik |
| 4365 | 3 | 4 | 5 | | | V-2 | B230219D22Rik |
| 4366 | 3 | 4 | 5 | | | V-2 | B330016D10Rik |
| 4367 | 3 | 4 | 5 | | | V-2 | B3gat3 |
| 4368 | 3 | 4 | 5 | | | V-2 | B3gnt4 |
| 4369 | 3 | 4 | 5 | | | V-2 | B3gnt5 |
| 4370 | 3 | 4 | 5 | | | V-2 | B3gnt8 |
| 4371 | 3 | 4 | 5 | | | V-2 | B4galt3 |
| 4372 | 3 | 4 | 5 | | | V-2 | B4galt4 |
| 4373 | 3 | 4 | 5 | | | V-2 | Baat |
| 4374 | 3 | 4 | 5 | | | V-2 | Bach1 |
| 4375 | 3 | 4 | 5 | | | V-2 | Bach2os |
| 4376 | 3 | 4 | 5 | | | V-2 | Bag5 |
| 4377 | 3 | 4 | 5 | | | V-2 | Bahcc1 |
| 4378 | 3 | 4 | 5 | | | V-2 | Bahd1 |
| 4379 | 3 | 4 | 5 | | | V-2 | Baiap2l1 |
| 4380 | 3 | 4 | 5 | | | V-2 | Banf1 |
| 4381 | 3 | 4 | 5 | | | V-2 | Bank1 |
| 4382 | 3 | 4 | 5 | | | V-2 | Banp |
| 4383 | 3 | 4 | 5 | | | V-2 | Barx1 |
| 4384 | 3 | 4 | 5 | | | V-2 | Baz1a |
| 4385 | 3 | 4 | 5 | | | V-2 | Baz1b |
| 4386 | 3 | 4 | 5 | | | V-2 | Baz2b |
| 4387 | 3 | 4 | 5 | | | V-2 | Bbs10 |
| 4388 | 3 | 4 | 5 | | | V-2 | Bbs5 |
| 4389 | 3 | 4 | 5 | | | V-2 | BC005624 |
| 4390 | 3 | 4 | 5 | | | V-2 | BC020402 |
| 4391 | 3 | 4 | 5 | | | V-2 | BC021891 |
| 4392 | 3 | 4 | 5 | | | V-2 | BC024386 |
| 4393 | 3 | 4 | 5 | | | V-2 | BC030307 |
| 4394 | 3 | 4 | 5 | | | V-2 | BC030499 |
| 4395 | 3 | 4 | 5 | | | V-2 | BC039966 |
| 4396 | 3 | 4 | 5 | | | V-2 | BC049715 |
| 4397 | 3 | 4 | 5 | | | V-2 | BC052040 |
| 4398 | 3 | 4 | 5 | | | V-2 | BC065397 |
| 4399 | 3 | 4 | 5 | | | V-2 | BC089491 |
| 4400 | 3 | 4 | 5 | | | V-2 | BC089597 |
| 4401 | 3 | 4 | 5 | | | V-2 | BC147527 |
| 4402 | 3 | 4 | 5 | | | V-2 | Bcap31 |
| 4403 | 3 | 4 | 5 | | | V-2 | Bcdin3d |
| 4404 | 3 | 4 | 5 | | | V-2 | Bckdha |
| 4405 | 3 | 4 | 5 | | | V-2 | Bcl10 |
| 4406 | 3 | 4 | 5 | | | V-2 | Bcl11b |
| 4407 | 3 | 4 | 5 | | | V-2 | Bcl2 |
| 4408 | 3 | 4 | 5 | | | V-2 | Bcl2l1 |
| 4409 | 3 | 4 | 5 | | | V-2 | Bcl2l14 |
| 4410 | 3 | 4 | 5 | | | V-2 | Bcl2l2 |
| 4411 | 3 | 4 | 5 | | | V-2 | Bcor |
| 4412 | 3 | 4 | 5 | | | V-2 | Bcr |
| 4413 | 3 | 4 | 5 | | | V-2 | Bdp1 |
| 4414 | 3 | 4 | 5 | | | V-2 | Bend7 |
| 4415 | 3 | 4 | 5 | | | V-2 | Best1 |
| 4416 | 3 | 4 | 5 | | | V-2 | Bicd2 |
| 4417 | 3 | 4 | 5 | | | V-2 | Bivm |
| 4418 | 3 | 4 | 5 | | | V-2 | Blmh |

Fig. 43 - 27

| | | | | | | | | | | | | | | | | | |
|---|---|---|---|---|---|---|---|---|---|---|---|---|---|---|---|---|---|
| 4419 | 3 | 4 | 5 | | | V-2 | Bloc1s3 | | 4504 | 3 | 4 | 5 | | | V-2 | Ccdc157 |
| 4420 | 3 | 4 | 5 | | | V-2 | Bloc1s4 | | 4505 | 3 | 4 | 5 | | | V-2 | Ccdc160 |
| 4421 | 3 | 4 | 5 | | | V-2 | Bmp2 | | 4506 | 3 | 4 | 5 | | | V-2 | Ccdc173 |
| 4422 | 3 | 4 | 5 | | | V-2 | Bmp8a | | 4507 | 3 | 4 | 5 | | | V-2 | Ccdc181 |
| 4423 | 3 | 4 | 5 | | | V-2 | Bmp8b | | 4508 | 3 | 4 | 5 | | | V-2 | Ccdc19 |
| 4424 | 3 | 4 | 5 | | | V-2 | Bmper | | 4509 | 3 | 4 | 5 | | | V-2 | Ccdc28b |
| 4425 | 3 | 4 | 5 | | | V-2 | Bod1 | | 4510 | 3 | 4 | 5 | | | V-2 | Ccdc3 |
| 4426 | 3 | 4 | 5 | | | V-2 | Bpgm | | 4511 | 3 | 4 | 5 | | | V-2 | Ccdc34 |
| 4427 | 3 | 4 | 5 | | | V-2 | Brd3 | | 4512 | 3 | 4 | 5 | | | V-2 | Ccdc42b |
| 4428 | 3 | 4 | 5 | | | V-2 | Bri3 | | 4513 | 3 | 4 | 5 | | | V-2 | Ccdc53 |
| 4429 | 3 | 4 | 5 | | | V-2 | Bri3bp | | 4514 | 3 | 4 | 5 | | | V-2 | Ccdc58 |
| 4430 | 3 | 4 | 5 | | | V-2 | Brinp3 | | 4515 | 3 | 4 | 5 | | | V-2 | Ccdc60 |
| 4431 | 3 | 4 | 5 | | | V-2 | Brk1 | | 4516 | 3 | 4 | 5 | | | V-2 | Ccdc61 |
| 4432 | 3 | 4 | 5 | | | V-2 | Brpf3 | | 4517 | 3 | 4 | 5 | | | V-2 | Ccdc70 |
| 4433 | 3 | 4 | 5 | | | V-2 | Brwd3 | | 4518 | 3 | 4 | 5 | | | V-2 | Ccdc77 |
| 4434 | 3 | 4 | 5 | | | V-2 | Bsdc1 | | 4519 | 3 | 4 | 5 | | | V-2 | Ccdc85a |
| 4435 | 3 | 4 | 5 | | | V-2 | Bsph2 | | 4520 | 3 | 4 | 5 | | | V-2 | Ccdc90b |
| 4436 | 3 | 4 | 5 | | | V-2 | Btbd9 | | 4521 | 3 | 4 | 5 | | | V-2 | Ccdc96 |
| 4437 | 3 | 4 | 5 | | | V-2 | Btg1 | | 4522 | 3 | 4 | 5 | | | V-2 | Ccl20 |
| 4438 | 3 | 4 | 5 | | | V-2 | Btnl2 | | 4523 | 3 | 4 | 5 | | | V-2 | Ccm2 |
| 4439 | 3 | 4 | 5 | | | V-2 | Btrc | | 4524 | 3 | 4 | 5 | | | V-2 | Ccnd3 |
| 4440 | 3 | 4 | 5 | | | V-2 | C030018K13Rik | | 4525 | 3 | 4 | 5 | | | V-2 | Ccndbp1 |
| 4441 | 3 | 4 | 5 | | | V-2 | C030034I22Rik | | 4526 | 3 | 4 | 5 | | | V-2 | Ccng2 |
| 4442 | 3 | 4 | 5 | | | V-2 | C030046E11Rik | | 4527 | 3 | 4 | 5 | | | V-2 | Ccnj |
| 4443 | 3 | 4 | 5 | | | V-2 | C1qtnf9 | | 4528 | 3 | 4 | 5 | | | V-2 | Ccp110 |
| 4444 | 3 | 4 | 5 | | | V-2 | C230037L18Rik | | 4529 | 3 | 4 | 5 | | | V-2 | Ccr3 |
| 4445 | 3 | 4 | 5 | | | V-2 | C230052I12Rik | | 4530 | 3 | 4 | 5 | | | V-2 | Ccr8 |
| 4446 | 3 | 4 | 5 | | | V-2 | C230091D08Rik | | 4531 | 3 | 4 | 5 | | | V-2 | Ccser1 |
| 4447 | 3 | 4 | 5 | | | V-2 | C2cd2 | | 4532 | 3 | 4 | 5 | | | V-2 | Ccser2 |
| 4448 | 3 | 4 | 5 | | | V-2 | C2cd2l | | 4533 | 3 | 4 | 5 | | | V-2 | Cct4 |
| 4449 | 3 | 4 | 5 | | | V-2 | C2cd3 | | 4534 | 3 | 4 | 5 | | | V-2 | Cd101 |
| 4450 | 3 | 4 | 5 | | | V-2 | C330022C24Rik | | 4535 | 3 | 4 | 5 | | | V-2 | Cd209f |
| 4451 | 3 | 4 | 5 | | | V-2 | C330027C09Rik | | 4536 | 3 | 4 | 5 | | | V-2 | Cd226 |
| 4452 | 3 | 4 | 5 | | | V-2 | C4bp-ps1 | | 4537 | 3 | 4 | 5 | | | V-2 | Cd24a |
| 4453 | 3 | 4 | 5 | | | V-2 | C530008M17Rik | | 4538 | 3 | 4 | 5 | | | V-2 | Cd27 |
| 4454 | 3 | 4 | 5 | | | V-2 | C530044C16Rik | | 4539 | 3 | 4 | 5 | | | V-2 | Cd3e |
| 4455 | 3 | 4 | 5 | | | V-2 | C77080 | | 4540 | 3 | 4 | 5 | | | V-2 | Cd3eap |
| 4456 | 3 | 4 | 5 | | | V-2 | C920009B18Rik | | 4541 | 3 | 4 | 5 | | | V-2 | Cd3g |
| 4457 | 3 | 4 | 5 | | | V-2 | Cacfd1 | | 4542 | 3 | 4 | 5 | | | V-2 | Cd4 |
| 4458 | 3 | 4 | 5 | | | V-2 | Cacna1d | | 4543 | 3 | 4 | 5 | | | V-2 | Cd48 |
| 4459 | 3 | 4 | 5 | | | V-2 | Cacna2d4 | | 4544 | 3 | 4 | 5 | | | V-2 | Cd5 |
| 4460 | 3 | 4 | 5 | | | V-2 | Cage1 | | 4545 | 3 | 4 | 5 | | | V-2 | Cd59a |
| 4461 | 3 | 4 | 5 | | | V-2 | Calb2 | | 4546 | 3 | 4 | 5 | | | V-2 | Cd7 |
| 4462 | 3 | 4 | 5 | | | V-2 | Calcb | | 4547 | 3 | 4 | 5 | | | V-2 | Cd82 |
| 4463 | 3 | 4 | 5 | | | V-2 | Calcoco1 | | 4548 | 3 | 4 | 5 | | | V-2 | Cd96 |
| 4464 | 3 | 4 | 5 | | | V-2 | Calcrl | | 4549 | 3 | 4 | 5 | | | V-2 | Cdadc1 |
| 4465 | 3 | 4 | 5 | | | V-2 | Calhm2 | | 4550 | 3 | 4 | 5 | | | V-2 | Cdc16 |
| 4466 | 3 | 4 | 5 | | | V-2 | Camk1 | | 4551 | 3 | 4 | 5 | | | V-2 | Cdc25b |
| 4467 | 3 | 4 | 5 | | | V-2 | Camkmt | | 4552 | 3 | 4 | 5 | | | V-2 | Cdc26 |
| 4468 | 3 | 4 | 5 | | | V-2 | Camkv | | 4553 | 3 | 4 | 5 | | | V-2 | Cdc37l1 |
| 4469 | 3 | 4 | 5 | | | V-2 | Camsap1 | | 4554 | 3 | 4 | 5 | | | V-2 | Cdc42bpa |
| 4470 | 3 | 4 | 5 | | | V-2 | Camsap2 | | 4555 | 3 | 4 | 5 | | | V-2 | Cdc42ep3 |
| 4471 | 3 | 4 | 5 | | | V-2 | Cant1 | | 4556 | 3 | 4 | 5 | | | V-2 | Cdc5l |
| 4472 | 3 | 4 | 5 | | | V-2 | Capn5 | | 4557 | 3 | 4 | 5 | | | V-2 | Cdc7 |
| 4473 | 3 | 4 | 5 | | | V-2 | Card10 | | 4558 | 3 | 4 | 5 | | | V-2 | Cdh17 |
| 4474 | 3 | 4 | 5 | | | V-2 | Carm1 | | 4559 | 3 | 4 | 5 | | | V-2 | Cdh19 |
| 4475 | 3 | 4 | 5 | | | V-2 | Cars2 | | 4560 | 3 | 4 | 5 | | | V-2 | Cdk17 |
| 4476 | 3 | 4 | 5 | | | V-2 | Casc5 | | 4561 | 3 | 4 | 5 | | | V-2 | Cdk2 |
| 4477 | 3 | 4 | 5 | | | V-2 | Casp1 | | 4562 | 3 | 4 | 5 | | | V-2 | Cdk2ap2 |
| 4478 | 3 | 4 | 5 | | | V-2 | Casp6 | | 4563 | 3 | 4 | 5 | | | V-2 | Cdk5 |
| 4479 | 3 | 4 | 5 | | | V-2 | Casp8ap2 | | 4564 | 3 | 4 | 5 | | | V-2 | Cdk7 |
| 4480 | 3 | 4 | 5 | | | V-2 | Casp9 | | 4565 | 3 | 4 | 5 | | | V-2 | Cdk9 |
| 4481 | 3 | 4 | 5 | | | V-2 | Cass4 | | 4566 | 3 | 4 | 5 | | | V-2 | Cdkl1 |
| 4482 | 3 | 4 | 5 | | | V-2 | Cat | | 4567 | 3 | 4 | 5 | | | V-2 | Cdkl3 |
| 4483 | 3 | 4 | 5 | | | V-2 | Cbfa2t3 | | 4568 | 3 | 4 | 5 | | | V-2 | Cdkn1b |
| 4484 | 3 | 4 | 5 | | | V-2 | Cbic | | 4569 | 3 | 4 | 5 | | | V-2 | Cdkn2aipnl |
| 4485 | 3 | 4 | 5 | | | V-2 | Cbr4 | | 4570 | 3 | 4 | 5 | | | V-2 | Cdkn3 |
| 4486 | 3 | 4 | 5 | | | V-2 | Cbs | | 4571 | 3 | 4 | 5 | | | V-2 | Cdnf |
| 4487 | 3 | 4 | 5 | | | V-2 | Cbx1 | | 4572 | 3 | 4 | 5 | | | V-2 | Cdpf1 |
| 4488 | 3 | 4 | 5 | | | V-2 | Cbx2 | | 4573 | 3 | 4 | 5 | | | V-2 | Cds1 |
| 4489 | 3 | 4 | 5 | | | V-2 | Cbx5 | | 4574 | 3 | 4 | 5 | | | V-2 | Ceacam1 |
| 4490 | 3 | 4 | 5 | | | V-2 | Cbx7 | | 4575 | 3 | 4 | 5 | | | V-2 | Cebpg |
| 4491 | 3 | 4 | 5 | | | V-2 | Cbx8 | | 4576 | 3 | 4 | 5 | | | V-2 | Cecr5 |
| 4492 | 3 | 4 | 5 | | | V-2 | Cc2d1a | | 4577 | 3 | 4 | 5 | | | V-2 | Celf4 |
| 4493 | 3 | 4 | 5 | | | V-2 | Cc2d1b | | 4578 | 3 | 4 | 5 | | | V-2 | Celsr2 |
| 4494 | 3 | 4 | 5 | | | V-2 | Cc2d2a | | 4579 | 3 | 4 | 5 | | | V-2 | Cep128 |
| 4495 | 3 | 4 | 5 | | | V-2 | Ccar1 | | 4580 | 3 | 4 | 5 | | | V-2 | Cep131 |
| 4496 | 3 | 4 | 5 | | | V-2 | Ccbe1 | | 4581 | 3 | 4 | 5 | | | V-2 | Cep135 |
| 4497 | 3 | 4 | 5 | | | V-2 | Ccdc102a | | 4582 | 3 | 4 | 5 | | | V-2 | Cep162 |
| 4498 | 3 | 4 | 5 | | | V-2 | Ccdc112 | | 4583 | 3 | 4 | 5 | | | V-2 | Cep170 |
| 4499 | 3 | 4 | 5 | | | V-2 | Ccdc129 | | 4584 | 3 | 4 | 5 | | | V-2 | Cep19 |
| 4500 | 3 | 4 | 5 | | | V-2 | Ccdc134 | | 4585 | 3 | 4 | 5 | | | V-2 | Cep250 |
| 4501 | 3 | 4 | 5 | | | V-2 | Ccdc137 | | 4586 | 3 | 4 | 5 | | | V-2 | Cep350 |
| 4502 | 3 | 4 | 5 | | | V-2 | Ccdc138 | | 4587 | 3 | 4 | 5 | | | V-2 | Cep72 |
| 4503 | 3 | 4 | 5 | | | V-2 | Ccdc141 | | 4588 | 3 | 4 | 5 | | | V-2 | Cep95 |

Fig. 43 - 28

| | | | | | | | | |
|---|---|---|---|---|---|---|---|---|
| 4589 | 3 | 4 | 5 | | | V-2 | Cep97 |
| 4590 | 3 | 4 | 5 | | | V-2 | Cerk |
| 4591 | 3 | 4 | 5 | | | V-2 | Cers4 |
| 4592 | 3 | 4 | 5 | | | V-2 | Ces1d |
| 4593 | 3 | 4 | 5 | | | V-2 | Cfdp1 |
| 4594 | 3 | 4 | 5 | | | V-2 | Cflar |
| 4595 | 3 | 4 | 5 | | | V-2 | Cftr |
| 4596 | 3 | 4 | 5 | | | V-2 | Cgrrf1 |
| 4597 | 3 | 4 | 5 | | | V-2 | Chchd1 |
| 4598 | 3 | 4 | 5 | | | V-2 | Chchd7 |
| 4599 | 3 | 4 | 5 | | | V-2 | Chd1 |
| 4600 | 3 | 4 | 5 | | | V-2 | Chd9 |
| 4601 | 3 | 4 | 5 | | | V-2 | Chdh |
| 4602 | 3 | 4 | 5 | | | V-2 | Chgb |
| 4603 | 3 | 4 | 5 | | | V-2 | Chid1 |
| 4604 | 3 | 4 | 5 | | | V-2 | Chml |
| 4605 | 3 | 4 | 5 | | | V-2 | Chmp5 |
| 4606 | 3 | 4 | 5 | | | V-2 | Chmp6 |
| 4607 | 3 | 4 | 5 | | | V-2 | Chn1 |
| 4608 | 3 | 4 | 5 | | | V-2 | Chn2 |
| 4609 | 3 | 4 | 5 | | | V-2 | Chordc1 |
| 4610 | 3 | 4 | 5 | | | V-2 | Chpf |
| 4611 | 3 | 4 | 5 | | | V-2 | Chrac1 |
| 4612 | 3 | 4 | 5 | | | V-2 | Chrdl1 |
| 4613 | 3 | 4 | 5 | | | V-2 | Chrm1 |
| 4614 | 3 | 4 | 5 | | | V-2 | Chrm3 |
| 4615 | 3 | 4 | 5 | | | V-2 | Chrna3 |
| 4616 | 3 | 4 | 5 | | | V-2 | Chrnb2 |
| 4617 | 3 | 4 | 5 | | | V-2 | Chst15 |
| 4618 | 3 | 4 | 5 | | | V-2 | Chst4 |
| 4619 | 3 | 4 | 5 | | | V-2 | Chtf8 |
| 4620 | 3 | 4 | 5 | | | V-2 | Ciao1 |
| 4621 | 3 | 4 | 5 | | | V-2 | Cinp |
| 4622 | 3 | 4 | 5 | | | V-2 | Cir1 |
| 4623 | 3 | 4 | 5 | | | V-2 | Cited2 |
| 4624 | 3 | 4 | 5 | | | V-2 | Ckap4 |
| 4625 | 3 | 4 | 5 | | | V-2 | Clca2 |
| 4626 | 3 | 4 | 5 | | | V-2 | Cldn1 |
| 4627 | 3 | 4 | 5 | | | V-2 | Cldn10 |
| 4628 | 3 | 4 | 5 | | | V-2 | Cldn11 |
| 4629 | 3 | 4 | 5 | | | V-2 | Cldn15 |
| 4630 | 3 | 4 | 5 | | | V-2 | Cldn9 |
| 4631 | 3 | 4 | 5 | | | V-2 | Clec18a |
| 4632 | 3 | 4 | 5 | | | V-2 | Clec2d |
| 4633 | 3 | 4 | 5 | | | V-2 | Clec2e |
| 4634 | 3 | 4 | 5 | | | V-2 | Clec4b1 |
| 4635 | 3 | 4 | 5 | | | V-2 | Clec9a |
| 4636 | 3 | 4 | 5 | | | V-2 | Clgn |
| 4637 | 3 | 4 | 5 | | | V-2 | Clip1 |
| 4638 | 3 | 4 | 5 | | | V-2 | Clk1 |
| 4639 | 3 | 4 | 5 | | | V-2 | Cln3 |
| 4640 | 3 | 4 | 5 | | | V-2 | Cln8 |
| 4641 | 3 | 4 | 5 | | | V-2 | Clock |
| 4642 | 3 | 4 | 5 | | | V-2 | Clta |
| 4643 | 3 | 4 | 5 | | | V-2 | Cmah |
| 4644 | 3 | 4 | 5 | | | V-2 | Cmas |
| 4645 | 3 | 4 | 5 | | | V-2 | Cmc1 |
| 4646 | 3 | 4 | 5 | | | V-2 | Cmtm4 |
| 4647 | 3 | 4 | 5 | | | V-2 | Cmtm7 |
| 4648 | 3 | 4 | 5 | | | V-2 | Cndp1 |
| 4649 | 3 | 4 | 5 | | | V-2 | Cnep1r1 |
| 4650 | 3 | 4 | 5 | | | V-2 | Cnih2 |
| 4651 | 3 | 4 | 5 | | | V-2 | Cnnm4 |
| 4652 | 3 | 4 | 5 | | | V-2 | Cnot2 |
| 4653 | 3 | 4 | 5 | | | V-2 | Cnot6 |
| 4654 | 3 | 4 | 5 | | | V-2 | Cnot8 |
| 4655 | 3 | 4 | 5 | | | V-2 | Cnppd1 |
| 4656 | 3 | 4 | 5 | | | V-2 | Cnpy3 |
| 4657 | 3 | 4 | 5 | | | V-2 | Cnpy4 |
| 4658 | 3 | 4 | 5 | | | V-2 | Cntrl |
| 4659 | 3 | 4 | 5 | | | V-2 | Cntrob |
| 4660 | 3 | 4 | 5 | | | V-2 | Coa7 |
| 4661 | 3 | 4 | 5 | | | V-2 | Cog8 |
| 4662 | 3 | 4 | 5 | | | V-2 | Col11a2 |
| 4663 | 3 | 4 | 5 | | | V-2 | Col13a1 |
| 4664 | 3 | 4 | 5 | | | V-2 | Col28a1 |
| 4665 | 3 | 4 | 5 | | | V-2 | Col4a3 |
| 4666 | 3 | 4 | 5 | | | V-2 | Colec10 |
| 4667 | 3 | 4 | 5 | | | V-2 | Colec12 |
| 4668 | 3 | 4 | 5 | | | V-2 | Commd6 |
| 4669 | 3 | 4 | 5 | | | V-2 | Commd7 |
| 4670 | 3 | 4 | 5 | | | V-2 | Coq4 |
| 4671 | 3 | 4 | 5 | | | V-2 | Coq9 |
| 4672 | 3 | 4 | 5 | | | V-2 | Coro1b |
| 4673 | 3 | 4 | 5 | | | V-2 | Coro2b |
| 4674 | 3 | 4 | 5 | | | V-2 | Cpa3 |
| 4675 | 3 | 4 | 5 | | | V-2 | Cplx4 |
| 4676 | 3 | 4 | 5 | | | V-2 | Cpne1 |
| 4677 | 3 | 4 | 5 | | | V-2 | Cpq |
| 4678 | 3 | 4 | 5 | | | V-2 | Cpsf4 |
| 4679 | 3 | 4 | 5 | | | V-2 | Cpsf4l |
| 4680 | 3 | 4 | 5 | | | V-2 | Cpsf6 |
| 4681 | 3 | 4 | 5 | | | V-2 | Cr2 |
| 4682 | 3 | 4 | 5 | | | V-2 | Crabp2 |
| 4683 | 3 | 4 | 5 | | | V-2 | Cramp1l |
| 4684 | 3 | 4 | 5 | | | V-2 | Crb1 |
| 4685 | 3 | 4 | 5 | | | V-2 | Crcp |
| 4686 | 3 | 4 | 5 | | | V-2 | Creb1 |
| 4687 | 3 | 4 | 5 | | | V-2 | Creb3 |
| 4688 | 3 | 4 | 5 | | | V-2 | Creb3l4 |
| 4689 | 3 | 4 | 5 | | | V-2 | Crebl2 |
| 4690 | 3 | 4 | 5 | | | V-2 | Cript |
| 4691 | 3 | 4 | 5 | | | V-2 | Crnkl1 |
| 4692 | 3 | 4 | 5 | | | V-2 | Crp |
| 4693 | 3 | 4 | 5 | | | V-2 | Crybb3 |
| 4694 | 3 | 4 | 5 | | | V-2 | Crybg3 |
| 4695 | 3 | 4 | 5 | | | V-2 | Csad |
| 4696 | 3 | 4 | 5 | | | V-2 | Cse1l |
| 4697 | 3 | 4 | 5 | | | V-2 | Csgalnact1 |
| 4698 | 3 | 4 | 5 | | | V-2 | Csk |
| 4699 | 3 | 4 | 5 | | | V-2 | Csnk1e |
| 4700 | 3 | 4 | 5 | | | V-2 | Csrp1 |
| 4701 | 3 | 4 | 5 | | | V-2 | Csrp2 |
| 4702 | 3 | 4 | 5 | | | V-2 | Csrp2bp |
| 4703 | 3 | 4 | 5 | | | V-2 | Cst12 |
| 4704 | 3 | 4 | 5 | | | V-2 | Cst13 |
| 4705 | 3 | 4 | 5 | | | V-2 | Cstad |
| 4706 | 3 | 4 | 5 | | | V-2 | Cstf1 |
| 4707 | 3 | 4 | 5 | | | V-2 | Cstl1 |
| 4708 | 3 | 4 | 5 | | | V-2 | Ctbp2 |
| 4709 | 3 | 4 | 5 | | | V-2 | Ctcfl |
| 4710 | 3 | 4 | 5 | | | V-2 | Ctdsp1 |
| 4711 | 3 | 4 | 5 | | | V-2 | Ctf1 |
| 4712 | 3 | 4 | 5 | | | V-2 | Ctnna3 |
| 4713 | 3 | 4 | 5 | | | V-2 | Ctse |
| 4714 | 3 | 4 | 5 | | | V-2 | Ctu1 |
| 4715 | 3 | 4 | 5 | | | V-2 | Cul4a |
| 4716 | 3 | 4 | 5 | | | V-2 | Cul9 |
| 4717 | 3 | 4 | 5 | | | V-2 | Cutc |
| 4718 | 3 | 4 | 5 | | | V-2 | Cux1 |
| 4719 | 3 | 4 | 5 | | | V-2 | Cyb561a3 |
| 4720 | 3 | 4 | 5 | | | V-2 | Cyb561d2 |
| 4721 | 3 | 4 | 5 | | | V-2 | Cyb5d2 |
| 4722 | 3 | 4 | 5 | | | V-2 | Cyb5r2 |
| 4723 | 3 | 4 | 5 | | | V-2 | Cyb5r4 |
| 4724 | 3 | 4 | 5 | | | V-2 | Cybrd1 |
| 4725 | 3 | 4 | 5 | | | V-2 | Cyhr1 |
| 4726 | 3 | 4 | 5 | | | V-2 | Cylc2 |
| 4727 | 3 | 4 | 5 | | | V-2 | Cyp21a1 |
| 4728 | 3 | 4 | 5 | | | V-2 | Cyp2a5 |
| 4729 | 3 | 4 | 5 | | | V-2 | Cyp2c37 |
| 4730 | 3 | 4 | 5 | | | V-2 | Cyp2c39 |
| 4731 | 3 | 4 | 5 | | | V-2 | Cyp2c40 |
| 4732 | 3 | 4 | 5 | | | V-2 | Cyp2c44 |
| 4733 | 3 | 4 | 5 | | | V-2 | Cyp2c54 |
| 4734 | 3 | 4 | 5 | | | V-2 | Cyp2c66 |
| 4735 | 3 | 4 | 5 | | | V-2 | Cyp2c68 |
| 4736 | 3 | 4 | 5 | | | V-2 | Cyp2d12 |
| 4737 | 3 | 4 | 5 | | | V-2 | Cyp2j12 |
| 4738 | 3 | 4 | 5 | | | V-2 | Cyp39a1 |
| 4739 | 3 | 4 | 5 | | | V-2 | Cyp4a32 |
| 4740 | 3 | 4 | 5 | | | V-2 | Cyp4f41-ps |
| 4741 | 3 | 4 | 5 | | | V-2 | Cyp7a1 |
| 4742 | 3 | 4 | 5 | | | V-2 | Cypt3 |
| 4743 | 3 | 4 | 5 | | | V-2 | Cypt9 |
| 4744 | 3 | 4 | 5 | | | V-2 | Cyth2 |
| 4745 | 3 | 4 | 5 | | | V-2 | Cyth3 |
| 4746 | 3 | 4 | 5 | | | V-2 | Cytl1 |
| 4747 | 3 | 4 | 5 | | | V-2 | D030056L22Rik |
| 4748 | 3 | 4 | 5 | | | V-2 | D11Wsu47e |
| 4749 | 3 | 4 | 5 | | | V-2 | D130020L05Rik |
| 4750 | 3 | 4 | 5 | | | V-2 | D16Ertd472e |
| 4751 | 3 | 4 | 5 | | | V-2 | D17H6S53E |
| 4752 | 3 | 4 | 5 | | | V-2 | D1Ertd622e |
| 4753 | 3 | 4 | 5 | | | V-2 | D230025D16Rik |
| 4754 | 3 | 4 | 5 | | | V-2 | D2hgdh |
| 4755 | 3 | 4 | 5 | | | V-2 | D3Ertd254e |
| 4756 | 3 | 4 | 5 | | | V-2 | D430020J02Rik |
| 4757 | 3 | 4 | 5 | | | V-2 | D430036J16Rik |
| 4758 | 3 | 4 | 5 | | | V-2 | D430042O09Rik |

Fig. 43 - 29

| | | | | | | | |
|---|---|---|---|---|---|---|---|
| 4759 | 3 | 4 | 5 | | | V-2 | D630039A03Rik |
| 4760 | 3 | 4 | 5 | | | V-2 | D630045J12Rik |
| 4761 | 3 | 4 | 5 | | | V-2 | D730005E14Rik |
| 4762 | 3 | 4 | 5 | | | V-2 | D7Ertd443e |
| 4763 | 3 | 4 | 5 | | | V-2 | D830005E20Rik |
| 4764 | 3 | 4 | 5 | | | V-2 | D8Ertd82e |
| 4765 | 3 | 4 | 5 | | | V-2 | D930015E06Rik |
| 4766 | 3 | 4 | 5 | | | V-2 | D930016D06Rik |
| 4767 | 3 | 4 | 5 | | | V-2 | D930028M14Rik |
| 4768 | 3 | 4 | 5 | | | V-2 | Daam1 |
| 4769 | 3 | 4 | 5 | | | V-2 | Daf2 |
| 4770 | 3 | 4 | 5 | | | V-2 | Daird3 |
| 4771 | 3 | 4 | 5 | | | V-2 | Dand5 |
| 4772 | 3 | 4 | 5 | | | V-2 | Dapk1 |
| 4773 | 3 | 4 | 5 | | | V-2 | Dapk3 |
| 4774 | 3 | 4 | 5 | | | V-2 | Dcaf12 |
| 4775 | 3 | 4 | 5 | | | V-2 | Dcaf17 |
| 4776 | 3 | 4 | 5 | | | V-2 | Dcaf6 |
| 4777 | 3 | 4 | 5 | | | V-2 | Dcakd |
| 4778 | 3 | 4 | 5 | | | V-2 | Dcbld1 |
| 4779 | 3 | 4 | 5 | | | V-2 | Dchs1 |
| 4780 | 3 | 4 | 5 | | | V-2 | Dcik2 |
| 4781 | 3 | 4 | 5 | | | V-2 | Dcp1a |
| 4782 | 3 | 4 | 5 | | | V-2 | Dcp2 |
| 4783 | 3 | 4 | 5 | | | V-2 | Dcpp1 |
| 4784 | 3 | 4 | 5 | | | V-2 | Dcps |
| 4785 | 3 | 4 | 5 | | | V-2 | Dctn5 |
| 4786 | 3 | 4 | 5 | | | V-2 | Dctn6 |
| 4787 | 3 | 4 | 5 | | | V-2 | Dcun1d2 |
| 4788 | 3 | 4 | 5 | | | V-2 | Ddn |
| 4789 | 3 | 4 | 5 | | | V-2 | Ddo |
| 4790 | 3 | 4 | 5 | | | V-2 | Ddr1 |
| 4791 | 3 | 4 | 5 | | | V-2 | Ddt |
| 4792 | 3 | 4 | 5 | | | V-2 | Ddx10 |
| 4793 | 3 | 4 | 5 | | | V-2 | Ddx17 |
| 4794 | 3 | 4 | 5 | | | V-2 | Ddx26b |
| 4795 | 3 | 4 | 5 | | | V-2 | Ddx28 |
| 4796 | 3 | 4 | 5 | | | V-2 | Ddx31 |
| 4797 | 3 | 4 | 5 | | | V-2 | Ddx41 |
| 4798 | 3 | 4 | 5 | | | V-2 | Ddx51 |
| 4799 | 3 | 4 | 5 | | | V-2 | Ddx58 |
| 4800 | 3 | 4 | 5 | | | V-2 | Deaf1 |
| 4801 | 3 | 4 | 5 | | | V-2 | Dennd2a |
| 4802 | 3 | 4 | 5 | | | V-2 | Dennd2c |
| 4803 | 3 | 4 | 5 | | | V-2 | Dennd2d |
| 4804 | 3 | 4 | 5 | | | V-2 | Dennd4c |
| 4805 | 3 | 4 | 5 | | | V-2 | Dennd5a |
| 4806 | 3 | 4 | 5 | | | V-2 | Dennd5b |
| 4807 | 3 | 4 | 5 | | | V-2 | Dffa |
| 4808 | 3 | 4 | 5 | | | V-2 | Dgcr6 |
| 4809 | 3 | 4 | 5 | | | V-2 | Dgkd |
| 4810 | 3 | 4 | 5 | | | V-2 | Dguok |
| 4811 | 3 | 4 | 5 | | | V-2 | Dhrs3 |
| 4812 | 3 | 4 | 5 | | | V-2 | Dhrs4 |
| 4813 | 3 | 4 | 5 | | | V-2 | Dhrs7b |
| 4814 | 3 | 4 | 5 | | | V-2 | Dhx34 |
| 4815 | 3 | 4 | 5 | | | V-2 | Dhx37 |
| 4816 | 3 | 4 | 5 | | | V-2 | Dhx40 |
| 4817 | 3 | 4 | 5 | | | V-2 | Dhx57 |
| 4818 | 3 | 4 | 5 | | | V-2 | Diap2 |
| 4819 | 3 | 4 | 5 | | | V-2 | Diexf |
| 4820 | 3 | 4 | 5 | | | V-2 | Dio1 |
| 4821 | 3 | 4 | 5 | | | V-2 | Dirc2 |
| 4822 | 3 | 4 | 5 | | | V-2 | Dkc1 |
| 4823 | 3 | 4 | 5 | | | V-2 | Dlec1 |
| 4824 | 3 | 4 | 5 | | | V-2 | Dlg4 |
| 4825 | 3 | 4 | 5 | | | V-2 | Dlg5 |
| 4826 | 3 | 4 | 5 | | | V-2 | Dlgap4 |
| 4827 | 3 | 4 | 5 | | | V-2 | Dmpk |
| 4828 | 3 | 4 | 5 | | | V-2 | Dmtf1 |
| 4829 | 3 | 4 | 5 | | | V-2 | Dmtn |
| 4830 | 3 | 4 | 5 | | | V-2 | Dmxl1 |
| 4831 | 3 | 4 | 5 | | | V-2 | Dmxl2 |
| 4832 | 3 | 4 | 5 | | | V-2 | Dnah8 |
| 4833 | 3 | 4 | 5 | | | V-2 | Dnah9 |
| 4834 | 3 | 4 | 5 | | | V-2 | Dnaja1 |
| 4835 | 3 | 4 | 5 | | | V-2 | Dnaja2 |
| 4836 | 3 | 4 | 5 | | | V-2 | Dnaja4 |
| 4837 | 3 | 4 | 5 | | | V-2 | Dnajb14 |
| 4838 | 3 | 4 | 5 | | | V-2 | Dnajb4 |
| 4839 | 3 | 4 | 5 | | | V-2 | Dnajc1 |
| 4840 | 3 | 4 | 5 | | | V-2 | Dnajc21 |
| 4841 | 3 | 4 | 5 | | | V-2 | Dnajc27 |
| 4842 | 3 | 4 | 5 | | | V-2 | Dnajc30 |
| 4843 | 3 | 4 | 5 | | | V-2 | Dnajc7 |
| 4844 | 3 | 4 | 5 | | | V-2 | Dnal1 |
| 4845 | 3 | 4 | 5 | | | V-2 | Dnal4 |
| 4846 | 3 | 4 | 5 | | | V-2 | Dnmbp |
| 4847 | 3 | 4 | 5 | | | V-2 | Dnmt3a |
| 4848 | 3 | 4 | 5 | | | V-2 | Dohh |
| 4849 | 3 | 4 | 5 | | | V-2 | Dok7 |
| 4850 | 3 | 4 | 5 | | | V-2 | Dopey2 |
| 4851 | 3 | 4 | 5 | | | V-2 | Dos |
| 4852 | 3 | 4 | 5 | | | V-2 | Dph2 |
| 4853 | 3 | 4 | 5 | | | V-2 | Dpp7 |
| 4854 | 3 | 4 | 5 | | | V-2 | Dpp8 |
| 4855 | 3 | 4 | 5 | | | V-2 | Dpys |
| 4856 | 3 | 4 | 5 | | | V-2 | Dqx1 |
| 4857 | 3 | 4 | 5 | | | V-2 | Draxin |
| 4858 | 3 | 4 | 5 | | | V-2 | Drd5 |
| 4859 | 3 | 4 | 5 | | | V-2 | Drg1 |
| 4860 | 3 | 4 | 5 | | | V-2 | Drg2 |
| 4861 | 3 | 4 | 5 | | | V-2 | Dsel |
| 4862 | 3 | 4 | 5 | | | V-2 | Dsg2 |
| 4863 | 3 | 4 | 5 | | | V-2 | Dst |
| 4864 | 3 | 4 | 5 | | | V-2 | Dtd1 |
| 4865 | 3 | 4 | 5 | | | V-2 | Dtx2 |
| 4866 | 3 | 4 | 5 | | | V-2 | Dusp11 |
| 4867 | 3 | 4 | 5 | | | V-2 | Dusp12 |
| 4868 | 3 | 4 | 5 | | | V-2 | Dusp19 |
| 4869 | 3 | 4 | 5 | | | V-2 | Dusp22 |
| 4870 | 3 | 4 | 5 | | | V-2 | Dusp23 |
| 4871 | 3 | 4 | 5 | | | V-2 | Dusp26 |
| 4872 | 3 | 4 | 5 | | | V-2 | Dvl1 |
| 4873 | 3 | 4 | 5 | | | V-2 | Dxo |
| 4874 | 3 | 4 | 5 | | | V-2 | Dync1h1 |
| 4875 | 3 | 4 | 5 | | | V-2 | Dyrk1b |
| 4876 | 3 | 4 | 5 | | | V-2 | Dzip1 |
| 4877 | 3 | 4 | 5 | | | V-2 | Dzip3 |
| 4878 | 3 | 4 | 5 | | | V-2 | E030003E18Rik |
| 4879 | 3 | 4 | 5 | | | V-2 | E030044B06Rik |
| 4880 | 3 | 4 | 5 | | | V-2 | E130008D07Rik |
| 4881 | 3 | 4 | 5 | | | V-2 | E130218I03Rik |
| 4882 | 3 | 4 | 5 | | | V-2 | E130309D02Rik |
| 4883 | 3 | 4 | 5 | | | V-2 | E2f2 |
| 4884 | 3 | 4 | 5 | | | V-2 | E2f5 |
| 4885 | 3 | 4 | 5 | | | V-2 | E430016F16Rik |
| 4886 | 3 | 4 | 5 | | | V-2 | E430018J23Rik |
| 4887 | 3 | 4 | 5 | | | V-2 | E530001F21Rik |
| 4888 | 3 | 4 | 5 | | | V-2 | Ear10 |
| 4889 | 3 | 4 | 5 | | | V-2 | Ech1 |
| 4890 | 3 | 4 | 5 | | | V-2 | Echdc3 |
| 4891 | 3 | 4 | 5 | | | V-2 | Eci1 |
| 4892 | 3 | 4 | 5 | | | V-2 | Eda |
| 4893 | 3 | 4 | 5 | | | V-2 | Edc3 |
| 4894 | 3 | 4 | 5 | | | V-2 | Edil3 |
| 4895 | 3 | 4 | 5 | | | V-2 | Eed |
| 4896 | 3 | 4 | 5 | | | V-2 | Eef1d |
| 4897 | 3 | 4 | 5 | | | V-2 | Efcab1 |
| 4898 | 3 | 4 | 5 | | | V-2 | Efcab11 |
| 4899 | 3 | 4 | 5 | | | V-2 | Efcab12 |
| 4900 | 3 | 4 | 5 | | | V-2 | Efcab6 |
| 4901 | 3 | 4 | 5 | | | V-2 | Efcab9 |
| 4902 | 3 | 4 | 5 | | | V-2 | Efhb |
| 4903 | 3 | 4 | 5 | | | V-2 | Efhd1 |
| 4904 | 3 | 4 | 5 | | | V-2 | Egf |
| 4905 | 3 | 4 | 5 | | | V-2 | Egln2 |
| 4906 | 3 | 4 | 5 | | | V-2 | Egr2 |
| 4907 | 3 | 4 | 5 | | | V-2 | Egr3 |
| 4908 | 3 | 4 | 5 | | | V-2 | Ehmt2 |
| 4909 | 3 | 4 | 5 | | | V-2 | Eid1 |
| 4910 | 3 | 4 | 5 | | | V-2 | Eif1ax |
| 4911 | 3 | 4 | 5 | | | V-2 | Eif2ak1 |
| 4912 | 3 | 4 | 5 | | | V-2 | Eif2ak4 |
| 4913 | 3 | 4 | 5 | | | V-2 | Eif2s3y |
| 4914 | 3 | 4 | 5 | | | V-2 | Eif3d |
| 4915 | 3 | 4 | 5 | | | V-2 | Eif3e |
| 4916 | 3 | 4 | 5 | | | V-2 | Eif3h |
| 4917 | 3 | 4 | 5 | | | V-2 | Eif3m |
| 4918 | 3 | 4 | 5 | | | V-2 | Eif4a2 |
| 4919 | 3 | 4 | 5 | | | V-2 | Eif4b |
| 4920 | 3 | 4 | 5 | | | V-2 | Eif4e3 |
| 4921 | 3 | 4 | 5 | | | V-2 | Eif4ebp1 |
| 4922 | 3 | 4 | 5 | | | V-2 | Eif5b |
| 4923 | 3 | 4 | 5 | | | V-2 | Elavl1 |
| 4924 | 3 | 4 | 5 | | | V-2 | Elfn1 |
| 4925 | 3 | 4 | 5 | | | V-2 | Elk1 |
| 4926 | 3 | 4 | 5 | | | V-2 | Ell |
| 4927 | 3 | 4 | 5 | | | V-2 | Ell2 |
| 4928 | 3 | 4 | 5 | | | V-2 | Elmo1 |

Fig. 43 - 30

| | | | | | | | | |
|---|---|---|---|---|---|---|---|---|
| 4929 | 3 | 4 | 5 | | | V-2 | Elmod1 |
| 4930 | 3 | 4 | 5 | | | V-2 | Elmod3 |
| 4931 | 3 | 4 | 5 | | | V-2 | Eltd1 |
| 4932 | 3 | 4 | 5 | | | V-2 | Emd |
| 4933 | 3 | 4 | 5 | | | V-2 | Emg1 |
| 4934 | 3 | 4 | 5 | | | V-2 | Emx2 |
| 4935 | 3 | 4 | 5 | | | V-2 | Enpp3 |
| 4936 | 3 | 4 | 5 | | | V-2 | Eogt |
| 4937 | 3 | 4 | 5 | | | V-2 | Ep300 |
| 4938 | 3 | 4 | 5 | | | V-2 | Epb4.1 |
| 4939 | 3 | 4 | 5 | | | V-2 | Epb4.2 |
| 4940 | 3 | 4 | 5 | | | V-2 | Epg5 |
| 4941 | 3 | 4 | 5 | | | V-2 | Epha4 |
| 4942 | 3 | 4 | 5 | | | V-2 | Epn1 |
| 4943 | 3 | 4 | 5 | | | V-2 | Erap1 |
| 4944 | 3 | 4 | 5 | | | V-2 | Erbb2 |
| 4945 | 3 | 4 | 5 | | | V-2 | Erc1 |
| 4946 | 3 | 4 | 5 | | | V-2 | Ercc2 |
| 4947 | 3 | 4 | 5 | | | V-2 | Ercc6l2 |
| 4948 | 3 | 4 | 5 | | | V-2 | Ercc8 |
| 4949 | 3 | 4 | 5 | | | V-2 | Ereg |
| 4950 | 3 | 4 | 5 | | | V-2 | Erg |
| 4951 | 3 | 4 | 5 | | | V-2 | Erich2 |
| 4952 | 3 | 4 | 5 | | | V-2 | Erich3 |
| 4953 | 3 | 4 | 5 | | | V-2 | Erlin1 |
| 4954 | 3 | 4 | 5 | | | V-2 | Esam |
| 4955 | 3 | 4 | 5 | | | V-2 | Esm1 |
| 4956 | 3 | 4 | 5 | | | V-2 | Espn |
| 4957 | 3 | 4 | 5 | | | V-2 | Esrp1 |
| 4958 | 3 | 4 | 5 | | | V-2 | Etfdh |
| 4959 | 3 | 4 | 5 | | | V-2 | Etnppl |
| 4960 | 3 | 4 | 5 | | | V-2 | Eva1a |
| 4961 | 3 | 4 | 5 | | | V-2 | Eva1b |
| 4962 | 3 | 4 | 5 | | | V-2 | Exd1 |
| 4963 | 3 | 4 | 5 | | | V-2 | Exo5 |
| 4964 | 3 | 4 | 5 | | | V-2 | Exoc3l |
| 4965 | 3 | 4 | 5 | | | V-2 | Exoc3l4 |
| 4966 | 3 | 4 | 5 | | | V-2 | Exoc8 |
| 4967 | 3 | 4 | 5 | | | V-2 | Exosc1 |
| 4968 | 3 | 4 | 5 | | | V-2 | Exosc3 |
| 4969 | 3 | 4 | 5 | | | V-2 | Exosc5 |
| 4970 | 3 | 4 | 5 | | | V-2 | Exph5 |
| 4971 | 3 | 4 | 5 | | | V-2 | Ext2 |
| 4972 | 3 | 4 | 5 | | | V-2 | Extl3 |
| 4973 | 3 | 4 | 5 | | | V-2 | Ezh1 |
| 4974 | 3 | 4 | 5 | | | V-2 | Ezh2 |
| 4975 | 3 | 4 | 5 | | | V-2 | Ezr |
| 4976 | 3 | 4 | 5 | | | V-2 | F13b |
| 4977 | 3 | 4 | 5 | | | V-2 | F2rl1 |
| 4978 | 3 | 4 | 5 | | | V-2 | F2rl3 |
| 4979 | 3 | 4 | 5 | | | V-2 | F8a |
| 4980 | 3 | 4 | 5 | | | V-2 | Fa2h |
| 4981 | 3 | 4 | 5 | | | V-2 | Fabp7 |
| 4982 | 3 | 4 | 5 | | | V-2 | Fadd |
| 4983 | 3 | 4 | 5 | | | V-2 | Fahd2a |
| 4984 | 3 | 4 | 5 | | | V-2 | Fam104a |
| 4985 | 3 | 4 | 5 | | | V-2 | Fam109a |
| 4986 | 3 | 4 | 5 | | | V-2 | Fam114a2 |
| 4987 | 3 | 4 | 5 | | | V-2 | Fam117a |
| 4988 | 3 | 4 | 5 | | | V-2 | Fam120c |
| 4989 | 3 | 4 | 5 | | | V-2 | Fam129b |
| 4990 | 3 | 4 | 5 | | | V-2 | Fam131a |
| 4991 | 3 | 4 | 5 | | | V-2 | Fam134a |
| 4992 | 3 | 4 | 5 | | | V-2 | Fam154b |
| 4993 | 3 | 4 | 5 | | | V-2 | Fam166b |
| 4994 | 3 | 4 | 5 | | | V-2 | Fam168a |
| 4995 | 3 | 4 | 5 | | | V-2 | Fam173b |
| 4996 | 3 | 4 | 5 | | | V-2 | Fam174b |
| 4997 | 3 | 4 | 5 | | | V-2 | Fam178a |
| 4998 | 3 | 4 | 5 | | | V-2 | Fam184a |
| 4999 | 3 | 4 | 5 | | | V-2 | Fam189b |
| 5000 | 3 | 4 | 5 | | | V-2 | Fam193b |
| 5001 | 3 | 4 | 5 | | | V-2 | Fam203a |
| 5002 | 3 | 4 | 5 | | | V-2 | Fam206a |
| 5003 | 3 | 4 | 5 | | | V-2 | Fam208a |
| 5004 | 3 | 4 | 5 | | | V-2 | Fam20a |
| 5005 | 3 | 4 | 5 | | | V-2 | Fam20c |
| 5006 | 3 | 4 | 5 | | | V-2 | Fam210a |
| 5007 | 3 | 4 | 5 | | | V-2 | Fam213a |
| 5008 | 3 | 4 | 5 | | | V-2 | Fam221b |
| 5009 | 3 | 4 | 5 | | | V-2 | Fam3a |
| 5010 | 3 | 4 | 5 | | | V-2 | Fam3b |
| 5011 | 3 | 4 | 5 | | | V-2 | Fam43a |
| 5012 | 3 | 4 | 5 | | | V-2 | Fam45a |
| 5013 | 3 | 4 | 5 | | | V-2 | Fam60a |
| 5014 | 3 | 4 | 5 | | | V-2 | Fam63b |
| 5015 | 3 | 4 | 5 | | | V-2 | Fam65a |
| 5016 | 3 | 4 | 5 | | | V-2 | Fam69a |
| 5017 | 3 | 4 | 5 | | | V-2 | Fam71b |
| 5018 | 3 | 4 | 5 | | | V-2 | Fam71d |
| 5019 | 3 | 4 | 5 | | | V-2 | Fam71e2 |
| 5020 | 3 | 4 | 5 | | | V-2 | Fam73a |
| 5021 | 3 | 4 | 5 | | | V-2 | Fam78b |
| 5022 | 3 | 4 | 5 | | | V-2 | Fam83a |
| 5023 | 3 | 4 | 5 | | | V-2 | Fam83b |
| 5024 | 3 | 4 | 5 | | | V-2 | Fam83e |
| 5025 | 3 | 4 | 5 | | | V-2 | Fam89b |
| 5026 | 3 | 4 | 5 | | | V-2 | Fance |
| 5027 | 3 | 4 | 5 | | | V-2 | Fancg |
| 5028 | 3 | 4 | 5 | | | V-2 | Fanci |
| 5029 | 3 | 4 | 5 | | | V-2 | Farp2 |
| 5030 | 3 | 4 | 5 | | | V-2 | Fasn |
| 5031 | 3 | 4 | 5 | | | V-2 | Fastkd3 |
| 5032 | 3 | 4 | 5 | | | V-2 | Fastkd5 |
| 5033 | 3 | 4 | 5 | | | V-2 | Fat4 |
| 5034 | 3 | 4 | 5 | | | V-2 | Fbln5 |
| 5035 | 3 | 4 | 5 | | | V-2 | Fbxl12os |
| 5036 | 3 | 4 | 5 | | | V-2 | Fbxl2 |
| 5037 | 3 | 4 | 5 | | | V-2 | Fbxl20 |
| 5038 | 3 | 4 | 5 | | | V-2 | Fbxl6 |
| 5039 | 3 | 4 | 5 | | | V-2 | Fbxl8 |
| 5040 | 3 | 4 | 5 | | | V-2 | Fbxo24 |
| 5041 | 3 | 4 | 5 | | | V-2 | Fbxo30 |
| 5042 | 3 | 4 | 5 | | | V-2 | Fbxo4 |
| 5043 | 3 | 4 | 5 | | | V-2 | Fbxo9 |
| 5044 | 3 | 4 | 5 | | | V-2 | Fbxw13 |
| 5045 | 3 | 4 | 5 | | | V-2 | Fbxw18 |
| 5046 | 3 | 4 | 5 | | | V-2 | Fchsd1 |
| 5047 | 3 | 4 | 5 | | | V-2 | Fchsd2 |
| 5048 | 3 | 4 | 5 | | | V-2 | Fcrl5 |
| 5049 | 3 | 4 | 5 | | | V-2 | Fcrls |
| 5050 | 3 | 4 | 5 | | | V-2 | Fdxr |
| 5051 | 3 | 4 | 5 | | | V-2 | Ffar1 |
| 5052 | 3 | 4 | 5 | | | V-2 | Ffar3 |
| 5053 | 3 | 4 | 5 | | | V-2 | Fgd5 |
| 5054 | 3 | 4 | 5 | | | V-2 | Fgf2 |
| 5055 | 3 | 4 | 5 | | | V-2 | Fgf21 |
| 5056 | 3 | 4 | 5 | | | V-2 | Fgf3 |
| 5057 | 3 | 4 | 5 | | | V-2 | Fgfrl1 |
| 5058 | 3 | 4 | 5 | | | V-2 | Fggy |
| 5059 | 3 | 4 | 5 | | | V-2 | Fhad1 |
| 5060 | 3 | 4 | 5 | | | V-2 | Fhl5 |
| 5061 | 3 | 4 | 5 | | | V-2 | Fhod1 |
| 5062 | 3 | 4 | 5 | | | V-2 | Figla |
| 5063 | 3 | 4 | 5 | | | V-2 | Fkbp2 |
| 5064 | 3 | 4 | 5 | | | V-2 | Fkbp4 |
| 5065 | 3 | 4 | 5 | | | V-2 | Fkbp5 |
| 5066 | 3 | 4 | 5 | | | V-2 | Fkbpl |
| 5067 | 3 | 4 | 5 | | | V-2 | Fli1 |
| 5068 | 3 | 4 | 5 | | | V-2 | Flnb |
| 5069 | 3 | 4 | 5 | | | V-2 | Flrt2 |
| 5070 | 3 | 4 | 5 | | | V-2 | Flt1 |
| 5071 | 3 | 4 | 5 | | | V-2 | Fmnl1 |
| 5072 | 3 | 4 | 5 | | | V-2 | Fmo1 |
| 5073 | 3 | 4 | 5 | | | V-2 | Fmo4 |
| 5074 | 3 | 4 | 5 | | | V-2 | Fnbp1l |
| 5075 | 3 | 4 | 5 | | | V-2 | Fndc4 |
| 5076 | 3 | 4 | 5 | | | V-2 | Fnip2 |
| 5077 | 3 | 4 | 5 | | | V-2 | Fnta |
| 5078 | 3 | 4 | 5 | | | V-2 | Folr4 |
| 5079 | 3 | 4 | 5 | | | V-2 | Fosb |
| 5080 | 3 | 4 | 5 | | | V-2 | Foxa2 |
| 5081 | 3 | 4 | 5 | | | V-2 | Foxd2os |
| 5082 | 3 | 4 | 5 | | | V-2 | Foxk1 |
| 5083 | 3 | 4 | 5 | | | V-2 | Foxn2 |
| 5084 | 3 | 4 | 5 | | | V-2 | Foxp1 |
| 5085 | 3 | 4 | 5 | | | V-2 | Foxp4 |
| 5086 | 3 | 4 | 5 | | | V-2 | Foxs1 |
| 5087 | 3 | 4 | 5 | | | V-2 | Frg1 |
| 5088 | 3 | 4 | 5 | | | V-2 | Frs3 |
| 5089 | 3 | 4 | 5 | | | V-2 | Fsd1l |
| 5090 | 3 | 4 | 5 | | | V-2 | Fstl4 |
| 5091 | 3 | 4 | 5 | | | V-2 | Ftl1 |
| 5092 | 3 | 4 | 5 | | | V-2 | Fubp1 |
| 5093 | 3 | 4 | 5 | | | V-2 | Fuk |
| 5094 | 3 | 4 | 5 | | | V-2 | Fuom |
| 5095 | 3 | 4 | 5 | | | V-2 | Fut10 |
| 5096 | 3 | 4 | 5 | | | V-2 | Fut11 |
| 5097 | 3 | 4 | 5 | | | V-2 | Fut8 |
| 5098 | 3 | 4 | 5 | | | V-2 | Fuz |

Fig. 43 - 31

| | | | | | | | | |
|---|---|---|---|---|---|---|---|---|
| 5099 | 3 | 4 | 5 | | | V-2 | Fxr2 |
| 5100 | 3 | 4 | 5 | | | V-2 | Fzd1 |
| 5101 | 3 | 4 | 5 | | | V-2 | Fzd2 |
| 5102 | 3 | 4 | 5 | | | V-2 | G2e3 |
| 5103 | 3 | 4 | 5 | | | V-2 | G6b |
| 5104 | 3 | 4 | 5 | | | V-2 | Gab3 |
| 5105 | 3 | 4 | 5 | | | V-2 | Gabarapl2 |
| 5106 | 3 | 4 | 5 | | | V-2 | Gabbr1 |
| 5107 | 3 | 4 | 5 | | | V-2 | Gabpb2 |
| 5108 | 3 | 4 | 5 | | | V-2 | Gad1 |
| 5109 | 3 | 4 | 5 | | | V-2 | Gal |
| 5110 | 3 | 4 | 5 | | | V-2 | Galk2 |
| 5111 | 3 | 4 | 5 | | | V-2 | Galm |
| 5112 | 3 | 4 | 5 | | | V-2 | Galnt10 |
| 5113 | 3 | 4 | 5 | | | V-2 | Galnt11 |
| 5114 | 3 | 4 | 5 | | | V-2 | Galnt3 |
| 5115 | 3 | 4 | 5 | | | V-2 | Galnt9 |
| 5116 | 3 | 4 | 5 | | | V-2 | Ganc |
| 5117 | 3 | 4 | 5 | | | V-2 | Gapt |
| 5118 | 3 | 4 | 5 | | | V-2 | Gapvd1 |
| 5119 | 3 | 4 | 5 | | | V-2 | Gas8 |
| 5120 | 3 | 4 | 5 | | | V-2 | Gatad1 |
| 5121 | 3 | 4 | 5 | | | V-2 | Gba2 |
| 5122 | 3 | 4 | 5 | | | V-2 | Gbp8 |
| 5123 | 3 | 4 | 5 | | | V-2 | Gcfc2 |
| 5124 | 3 | 4 | 5 | | | V-2 | Gcgr |
| 5125 | 3 | 4 | 5 | | | V-2 | Gclm |
| 5126 | 3 | 4 | 5 | | | V-2 | Gcnt4 |
| 5127 | 3 | 4 | 5 | | | V-2 | Gdf9 |
| 5128 | 3 | 4 | 5 | | | V-2 | Gdi1 |
| 5129 | 3 | 4 | 5 | | | V-2 | Gdpd5 |
| 5130 | 3 | 4 | 5 | | | V-2 | Gem |
| 5131 | 3 | 4 | 5 | | | V-2 | Gemin5 |
| 5132 | 3 | 4 | 5 | | | V-2 | Gemin8 |
| 5133 | 3 | 4 | 5 | | | V-2 | Gfi1 |
| 5134 | 3 | 4 | 5 | | | V-2 | Gfpt1 |
| 5135 | 3 | 4 | 5 | | | V-2 | Gfpt2 |
| 5136 | 3 | 4 | 5 | | | V-2 | Gga3 |
| 5137 | 3 | 4 | 5 | | | V-2 | Ggcx |
| 5138 | 3 | 4 | 5 | | | V-2 | Ggps1 |
| 5139 | 3 | 4 | 5 | | | V-2 | Ggta1 |
| 5140 | 3 | 4 | 5 | | | V-2 | Ghdc |
| 5141 | 3 | 4 | 5 | | | V-2 | Ghitm |
| 5142 | 3 | 4 | 5 | | | V-2 | Ghrl |
| 5143 | 3 | 4 | 5 | | | V-2 | Gimap5 |
| 5144 | 3 | 4 | 5 | | | V-2 | Gimap6 |
| 5145 | 3 | 4 | 5 | | | V-2 | Gimap9 |
| 5146 | 3 | 4 | 5 | | | V-2 | Gipc3 |
| 5147 | 3 | 4 | 5 | | | V-2 | Gja5 |
| 5148 | 3 | 4 | 5 | | | V-2 | Gjb1 |
| 5149 | 3 | 4 | 5 | | | V-2 | Gjd3 |
| 5150 | 3 | 4 | 5 | | | V-2 | Glb1 |
| 5151 | 3 | 4 | 5 | | | V-2 | Glce |
| 5152 | 3 | 4 | 5 | | | V-2 | Gldc |
| 5153 | 3 | 4 | 5 | | | V-2 | Gle1 |
| 5154 | 3 | 4 | 5 | | | V-2 | Glmn |
| 5155 | 3 | 4 | 5 | | | V-2 | Glo1 |
| 5156 | 3 | 4 | 5 | | | V-2 | Glod4 |
| 5157 | 3 | 4 | 5 | | | V-2 | Glrx2 |
| 5158 | 3 | 4 | 5 | | | V-2 | Gls2 |
| 5159 | 3 | 4 | 5 | | | V-2 | Gltscr1 |
| 5160 | 3 | 4 | 5 | | | V-2 | Gltscr1l |
| 5161 | 3 | 4 | 5 | | | V-2 | Gm10336 |
| 5162 | 3 | 4 | 5 | | | V-2 | Gm10487 |
| 5163 | 3 | 4 | 5 | | | V-2 | Gm10516 |
| 5164 | 3 | 4 | 5 | | | V-2 | Gm10548 |
| 5165 | 3 | 4 | 5 | | | V-2 | Gm10591 |
| 5166 | 3 | 4 | 5 | | | V-2 | Gm10639 |
| 5167 | 3 | 4 | 5 | | | V-2 | Gm10681 |
| 5168 | 3 | 4 | 5 | | | V-2 | Gm10767 |
| 5169 | 3 | 4 | 5 | | | V-2 | Gm10768 |
| 5170 | 3 | 4 | 5 | | | V-2 | Gm10778 |
| 5171 | 3 | 4 | 5 | | | V-2 | Gm10941 |
| 5172 | 3 | 4 | 5 | | | V-2 | Gm11110 |
| 5173 | 3 | 4 | 5 | | | V-2 | Gm11149 |
| 5174 | 3 | 4 | 5 | | | V-2 | Gm11190 |
| 5175 | 3 | 4 | 5 | | | V-2 | Gm11780 |
| 5176 | 3 | 4 | 5 | | | V-2 | Gm12359 |
| 5177 | 3 | 4 | 5 | | | V-2 | Gm12522 |
| 5178 | 3 | 4 | 5 | | | V-2 | Gm12992 |
| 5179 | 3 | 4 | 5 | | | V-2 | Gm13212 |
| 5180 | 3 | 4 | 5 | | | V-2 | Gm13238 |
| 5181 | 3 | 4 | 5 | | | V-2 | Gm14169 |
| 5182 | 3 | 4 | 5 | | | V-2 | Gm14308 |
| 5183 | 3 | 4 | 5 | | | V-2 | Gm14325 |
| 5184 | 3 | 4 | 5 | | | V-2 | Gm14327 |
| 5185 | 3 | 4 | 5 | | | V-2 | Gm15179 |
| 5186 | 3 | 4 | 5 | | | V-2 | Gm15446 |
| 5187 | 3 | 4 | 5 | | | V-2 | Gm15455 |
| 5188 | 3 | 4 | 5 | | | V-2 | Gm15708 |
| 5189 | 3 | 4 | 5 | | | V-2 | Gm15772 |
| 5190 | 3 | 4 | 5 | | | V-2 | Gm15800 |
| 5191 | 3 | 4 | 5 | | | V-2 | Gm16515 |
| 5192 | 3 | 4 | 5 | | | V-2 | Gm16551 |
| 5193 | 3 | 4 | 5 | | | V-2 | Gm16617 |
| 5194 | 3 | 4 | 5 | | | V-2 | Gm16845 |
| 5195 | 3 | 4 | 5 | | | V-2 | Gm16973 |
| 5196 | 3 | 4 | 5 | | | V-2 | Gm17296 |
| 5197 | 3 | 4 | 5 | | | V-2 | Gm19557 |
| 5198 | 3 | 4 | 5 | | | V-2 | Gm19710 |
| 5199 | 3 | 4 | 5 | | | V-2 | Gm20063 |
| 5200 | 3 | 4 | 5 | | | V-2 | Gm20300 |
| 5201 | 3 | 4 | 5 | | | V-2 | Gm20748 |
| 5202 | 3 | 4 | 5 | | | V-2 | Gm2848 |
| 5203 | 3 | 4 | 5 | | | V-2 | Gm3317 |
| 5204 | 3 | 4 | 5 | | | V-2 | Gm3336 |
| 5205 | 3 | 4 | 5 | | | V-2 | Gm3414 |
| 5206 | 3 | 4 | 5 | | | V-2 | Gm3435 |
| 5207 | 3 | 4 | 5 | | | V-2 | Gm3500 |
| 5208 | 3 | 4 | 5 | | | V-2 | Gm3706 |
| 5209 | 3 | 4 | 5 | | | V-2 | Gm4477 |
| 5210 | 3 | 4 | 5 | | | V-2 | Gm4598 |
| 5211 | 3 | 4 | 5 | | | V-2 | Gm4724 |
| 5212 | 3 | 4 | 5 | | | V-2 | Gm4787 |
| 5213 | 3 | 4 | 5 | | | V-2 | Gm5 |
| 5214 | 3 | 4 | 5 | | | V-2 | Gm5088 |
| 5215 | 3 | 4 | 5 | | | V-2 | Gm5141 |
| 5216 | 3 | 4 | 5 | | | V-2 | Gm527 |
| 5217 | 3 | 4 | 5 | | | V-2 | Gm5434 |
| 5218 | 3 | 4 | 5 | | | V-2 | Gm5801 |
| 5219 | 3 | 4 | 5 | | | V-2 | Gm5941 |
| 5220 | 3 | 4 | 5 | | | V-2 | Gm614 |
| 5221 | 3 | 4 | 5 | | | V-2 | Gm6455 |
| 5222 | 3 | 4 | 5 | | | V-2 | Gm6460 |
| 5223 | 3 | 4 | 5 | | | V-2 | Gm6524 |
| 5224 | 3 | 4 | 5 | | | V-2 | Gm6568 |
| 5225 | 3 | 4 | 5 | | | V-2 | Gm7102 |
| 5226 | 3 | 4 | 5 | | | V-2 | Gm7120 |
| 5227 | 3 | 4 | 5 | | | V-2 | Gm7444 |
| 5228 | 3 | 4 | 5 | | | V-2 | Gm8633 |
| 5229 | 3 | 4 | 5 | | | V-2 | Gm867 |
| 5230 | 3 | 4 | 5 | | | V-2 | Gm8994 |
| 5231 | 3 | 4 | 5 | | | V-2 | Gm9125 |
| 5232 | 3 | 4 | 5 | | | V-2 | Gm9833 |
| 5233 | 3 | 4 | 5 | | | V-2 | Gm9899 |
| 5234 | 3 | 4 | 5 | | | V-2 | Gm9994 |
| 5235 | 3 | 4 | 5 | | | V-2 | Gna14 |
| 5236 | 3 | 4 | 5 | | | V-2 | Gnal |
| 5237 | 3 | 4 | 5 | | | V-2 | Gnao1 |
| 5238 | 3 | 4 | 5 | | | V-2 | Gnaq |
| 5239 | 3 | 4 | 5 | | | V-2 | Gnaz |
| 5240 | 3 | 4 | 5 | | | V-2 | Gne |
| 5241 | 3 | 4 | 5 | | | V-2 | Gng5 |
| 5242 | 3 | 4 | 5 | | | V-2 | Gngt2 |
| 5243 | 3 | 4 | 5 | | | V-2 | Gnpda2 |
| 5244 | 3 | 4 | 5 | | | V-2 | Golgb1 |
| 5245 | 3 | 4 | 5 | | | V-2 | Gpaa1 |
| 5246 | 3 | 4 | 5 | | | V-2 | Gpatch11 |
| 5247 | 3 | 4 | 5 | | | V-2 | Gpatch2 |
| 5248 | 3 | 4 | 5 | | | V-2 | Gpatch2l |
| 5249 | 3 | 4 | 5 | | | V-2 | Gpatch8 |
| 5250 | 3 | 4 | 5 | | | V-2 | Gpcpd1 |
| 5251 | 3 | 4 | 5 | | | V-2 | Gphn |
| 5252 | 3 | 4 | 5 | | | V-2 | Gpi1 |
| 5253 | 3 | 4 | 5 | | | V-2 | Gpihbp1 |
| 5254 | 3 | 4 | 5 | | | V-2 | Gpn2 |
| 5255 | 3 | 4 | 5 | | | V-2 | Gpr1 |
| 5256 | 3 | 4 | 5 | | | V-2 | Gpr114 |
| 5257 | 3 | 4 | 5 | | | V-2 | Gpr116 |
| 5258 | 3 | 4 | 5 | | | V-2 | Gpr126 |
| 5259 | 3 | 4 | 5 | | | V-2 | Gpr137c |
| 5260 | 3 | 4 | 5 | | | V-2 | Gpr146 |
| 5261 | 3 | 4 | 5 | | | V-2 | Gpr155 |
| 5262 | 3 | 4 | 5 | | | V-2 | Gpr174 |
| 5263 | 3 | 4 | 5 | | | V-2 | Gpr179 |
| 5264 | 3 | 4 | 5 | | | V-2 | Gpr183 |
| 5265 | 3 | 4 | 5 | | | V-2 | Gpr27 |
| 5266 | 3 | 4 | 5 | | | V-2 | Gpr34 |
| 5267 | 3 | 4 | 5 | | | V-2 | Gpr4 |
| 5268 | 3 | 4 | 5 | | | V-2 | Gpr55 |

Fig. 43 - 32

| | | | | | | | | | | | | | | | |
|---|---|---|---|---|---|---|---|---|---|---|---|---|---|---|---|
| 5269 | 3 | 4 | 5 | | | V-2 | Gpr56 | 5354 | 3 | 4 | 5 | | | V-2 | Hist2h2ac |
| 5270 | 3 | 4 | 5 | | | V-2 | Gpr89 | 5355 | 3 | 4 | 5 | | | V-2 | Hist2h2be |
| 5271 | 3 | 4 | 5 | | | V-2 | Gprasp2 | 5356 | 3 | 4 | 5 | | | V-2 | Hist3h2bb-ps |
| 5272 | 3 | 4 | 5 | | | V-2 | Gprc5a | 5357 | 3 | 4 | 5 | | | V-2 | Hjurp |
| 5273 | 3 | 4 | 5 | | | V-2 | Gps1 | 5358 | 3 | 4 | 5 | | | V-2 | Hmcn1 |
| 5274 | 3 | 4 | 5 | | | V-2 | Gps2 | 5359 | 3 | 4 | 5 | | | V-2 | Hmgcl |
| 5275 | 3 | 4 | 5 | | | V-2 | Gpsm1 | 5360 | 3 | 4 | 5 | | | V-2 | Hmx2 |
| 5276 | 3 | 4 | 5 | | | V-2 | Gpx1 | 5361 | 3 | 4 | 5 | | | V-2 | Hnf1b |
| 5277 | 3 | 4 | 5 | | | V-2 | Gramd1a | 5362 | 3 | 4 | 5 | | | V-2 | Hnmt |
| 5278 | 3 | 4 | 5 | | | V-2 | Gramd1c | 5363 | 3 | 4 | 5 | | | V-2 | Hnrnph3 |
| 5279 | 3 | 4 | 5 | | | V-2 | Gramd2 | 5364 | 3 | 4 | 5 | | | V-2 | Hnrnpl |
| 5280 | 3 | 4 | 5 | | | V-2 | Grap2 | 5365 | 3 | 4 | 5 | | | V-2 | Hnrnpul1 |
| 5281 | 3 | 4 | 5 | | | V-2 | Grcc10 | 5366 | 3 | 4 | 5 | | | V-2 | Homer1 |
| 5282 | 3 | 4 | 5 | | | V-2 | Grhl1 | 5367 | 3 | 4 | 5 | | | V-2 | Homer3 |
| 5283 | 3 | 4 | 5 | | | V-2 | Grin1os | 5368 | 3 | 4 | 5 | | | V-2 | Hook3 |
| 5284 | 3 | 4 | 5 | | | V-2 | Grk4 | 5369 | 3 | 4 | 5 | | | V-2 | Hoxb4 |
| 5285 | 3 | 4 | 5 | | | V-2 | Grk5 | 5370 | 3 | 4 | 5 | | | V-2 | Hoxb5 |
| 5286 | 3 | 4 | 5 | | | V-2 | Grpel1 | 5371 | 3 | 4 | 5 | | | V-2 | Hoxb7 |
| 5287 | 3 | 4 | 5 | | | V-2 | Grpel2 | 5372 | 3 | 4 | 5 | | | V-2 | Hoxd4 |
| 5288 | 3 | 4 | 5 | | | V-2 | Grsf1 | 5373 | 3 | 4 | 5 | | | V-2 | Hpca |
| 5289 | 3 | 4 | 5 | | | V-2 | Grtp1 | 5374 | 3 | 4 | 5 | | | V-2 | Hpcal1 |
| 5290 | 3 | 4 | 5 | | | V-2 | Gt(ROSA)26Sor | 5375 | 3 | 4 | 5 | | | V-2 | Hpd |
| 5291 | 3 | 4 | 5 | | | V-2 | Gtf2e1 | 5376 | 3 | 4 | 5 | | | V-2 | Hpdl |
| 5292 | 3 | 4 | 5 | | | V-2 | Gtf2e2 | 5377 | 3 | 4 | 5 | | | V-2 | Hpgds |
| 5293 | 3 | 4 | 5 | | | V-2 | Gtf2f2 | 5378 | 3 | 4 | 5 | | | V-2 | Hps1 |
| 5294 | 3 | 4 | 5 | | | V-2 | Gtf2h3 | 5379 | 3 | 4 | 5 | | | V-2 | Hps4 |
| 5295 | 3 | 4 | 5 | | | V-2 | Gtf2h5 | 5380 | 3 | 4 | 5 | | | V-2 | Hr |
| 5296 | 3 | 4 | 5 | | | V-2 | Gtf2i | 5381 | 3 | 4 | 5 | | | V-2 | Hrh3 |
| 5297 | 3 | 4 | 5 | | | V-2 | Gtf2ird2 | 5382 | 3 | 4 | 5 | | | V-2 | Hrh4 |
| 5298 | 3 | 4 | 5 | | | V-2 | Gtf3a | 5383 | 3 | 4 | 5 | | | V-2 | Hrk |
| 5299 | 3 | 4 | 5 | | | V-2 | Gtf3c4 | 5384 | 3 | 4 | 5 | | | V-2 | Hrsp12 |
| 5300 | 3 | 4 | 5 | | | V-2 | Gtf3c5 | 5385 | 3 | 4 | 5 | | | V-2 | Hs1bp3 |
| 5301 | 3 | 4 | 5 | | | V-2 | Gtl3 | 5386 | 3 | 4 | 5 | | | V-2 | Hs3st1 |
| 5302 | 3 | 4 | 5 | | | V-2 | Gtpbp2 | 5387 | 3 | 4 | 5 | | | V-2 | Hs3st2 |
| 5303 | 3 | 4 | 5 | | | V-2 | Gtpbp4 | 5388 | 3 | 4 | 5 | | | V-2 | Hs3st3a1 |
| 5304 | 3 | 4 | 5 | | | V-2 | Gtpbp6 | 5389 | 3 | 4 | 5 | | | V-2 | Hs6st2 |
| 5305 | 3 | 4 | 5 | | | V-2 | Gtpbp8 | 5390 | 3 | 4 | 5 | | | V-2 | Hsbp1 |
| 5306 | 3 | 4 | 5 | | | V-2 | Guca1b | 5391 | 3 | 4 | 5 | | | V-2 | Hsd17b10 |
| 5307 | 3 | 4 | 5 | | | V-2 | Gucd1 | 5392 | 3 | 4 | 5 | | | V-2 | Hsd17b11 |
| 5308 | 3 | 4 | 5 | | | V-2 | Gucy1a2 | 5393 | 3 | 4 | 5 | | | V-2 | Hsd17b2 |
| 5309 | 3 | 4 | 5 | | | V-2 | Gucy1b3 | 5394 | 3 | 4 | 5 | | | V-2 | Hsd17b3 |
| 5310 | 3 | 4 | 5 | | | V-2 | Gypa | 5395 | 3 | 4 | 5 | | | V-2 | Hsf1 |
| 5311 | 3 | 4 | 5 | | | V-2 | H2afv | 5396 | 3 | 4 | 5 | | | V-2 | Hspa12b |
| 5312 | 3 | 4 | 5 | | | V-2 | H2afy2 | 5397 | 3 | 4 | 5 | | | V-2 | Hspbap1 |
| 5313 | 3 | 4 | 5 | | | V-2 | H2-DMa | 5398 | 3 | 4 | 5 | | | V-2 | Htatip2 |
| 5314 | 3 | 4 | 5 | | | V-2 | H2-M5 | 5399 | 3 | 4 | 5 | | | V-2 | Hvcn1 |
| 5315 | 3 | 4 | 5 | | | V-2 | H2-Oa | 5400 | 3 | 4 | 5 | | | V-2 | Hydin |
| 5316 | 3 | 4 | 5 | | | V-2 | H2-Q2 | 5401 | 3 | 4 | 5 | | | V-2 | Hykk |
| 5317 | 3 | 4 | 5 | | | V-2 | Hace1 | 5402 | 3 | 4 | 5 | | | V-2 | Iba57 |
| 5318 | 3 | 4 | 5 | | | V-2 | Hadh | 5403 | 3 | 4 | 5 | | | V-2 | Ibsp |
| 5319 | 3 | 4 | 5 | | | V-2 | Harbi1 | 5404 | 3 | 4 | 5 | | | V-2 | Icam2 |
| 5320 | 3 | 4 | 5 | | | V-2 | Haus3 | 5405 | 3 | 4 | 5 | | | V-2 | Ict1 |
| 5321 | 3 | 4 | 5 | | | V-2 | Hax1 | 5406 | 3 | 4 | 5 | | | V-2 | Id4 |
| 5322 | 3 | 4 | 5 | | | V-2 | Hba-x | 5407 | 3 | 4 | 5 | | | V-2 | Idh3b |
| 5323 | 3 | 4 | 5 | | | V-2 | Hbs1l | 5408 | 3 | 4 | 5 | | | V-2 | Idnk |
| 5324 | 3 | 4 | 5 | | | V-2 | Hc | 5409 | 3 | 4 | 5 | | | V-2 | Ido2 |
| 5325 | 3 | 4 | 5 | | | V-2 | Hcfc1r1 | 5410 | 3 | 4 | 5 | | | V-2 | Ifrd2 |
| 5326 | 3 | 4 | 5 | | | V-2 | Hcfc2 | 5411 | 3 | 4 | 5 | | | V-2 | Ift140 |
| 5327 | 3 | 4 | 5 | | | V-2 | Hdac10 | 5412 | 3 | 4 | 5 | | | V-2 | Ift46 |
| 5328 | 3 | 4 | 5 | | | V-2 | Hdac5 | 5413 | 3 | 4 | 5 | | | V-2 | Ift80 |
| 5329 | 3 | 4 | 5 | | | V-2 | Hdac6 | 5414 | 3 | 4 | 5 | | | V-2 | Ift88 |
| 5330 | 3 | 4 | 5 | | | V-2 | Hdac9 | 5415 | 3 | 4 | 5 | | | V-2 | Igf1r |
| 5331 | 3 | 4 | 5 | | | V-2 | Hddc3 | 5416 | 3 | 4 | 5 | | | V-2 | Igf2bp2 |
| 5332 | 3 | 4 | 5 | | | V-2 | Heatr1 | 5417 | 3 | 4 | 5 | | | V-2 | Igf2bp3 |
| 5333 | 3 | 4 | 5 | | | V-2 | Heatr5b | 5418 | 3 | 4 | 5 | | | V-2 | Igflr1 |
| 5334 | 3 | 4 | 5 | | | V-2 | Heca | 5419 | 3 | 4 | 5 | | | V-2 | Igsf10 |
| 5335 | 3 | 4 | 5 | | | V-2 | Hemk1 | 5420 | 3 | 4 | 5 | | | V-2 | Igsf21 |
| 5336 | 3 | 4 | 5 | | | V-2 | Herc1 | 5421 | 3 | 4 | 5 | | | V-2 | Igsf3 |
| 5337 | 3 | 4 | 5 | | | V-2 | Herc2 | 5422 | 3 | 4 | 5 | | | V-2 | Igsf5 |
| 5338 | 3 | 4 | 5 | | | V-2 | Herpud1 | 5423 | 3 | 4 | 5 | | | V-2 | Ikzf2 |
| 5339 | 3 | 4 | 5 | | | V-2 | Herpud2 | 5424 | 3 | 4 | 5 | | | V-2 | Il11ra2 |
| 5340 | 3 | 4 | 5 | | | V-2 | Hexim1 | 5425 | 3 | 4 | 5 | | | V-2 | Il12a |
| 5341 | 3 | 4 | 5 | | | V-2 | Hexim2 | 5426 | 3 | 4 | 5 | | | V-2 | Il12rb1 |
| 5342 | 3 | 4 | 5 | | | V-2 | Hgd | 5427 | 3 | 4 | 5 | | | V-2 | Il16 |
| 5343 | 3 | 4 | 5 | | | V-2 | Hgs | 5428 | 3 | 4 | 5 | | | V-2 | Il2 |
| 5344 | 3 | 4 | 5 | | | V-2 | Hibch | 5429 | 3 | 4 | 5 | | | V-2 | Il22ra2 |
| 5345 | 3 | 4 | 5 | | | V-2 | Hif3a | 5430 | 3 | 4 | 5 | | | V-2 | Il27ra |
| 5346 | 3 | 4 | 5 | | | V-2 | Higd1a | 5431 | 3 | 4 | 5 | | | V-2 | Il5ra |
| 5347 | 3 | 4 | 5 | | | V-2 | Hinfp | 5432 | 3 | 4 | 5 | | | V-2 | Immp2l |
| 5348 | 3 | 4 | 5 | | | V-2 | Hip1r | 5433 | 3 | 4 | 5 | | | V-2 | Imp3 |
| 5349 | 3 | 4 | 5 | | | V-2 | Hipk1 | 5434 | 3 | 4 | 5 | | | V-2 | Impa2 |
| 5350 | 3 | 4 | 5 | | | V-2 | Hipk3 | 5435 | 3 | 4 | 5 | | | V-2 | Inadl |
| 5351 | 3 | 4 | 5 | | | V-2 | Hist1h2an | 5436 | 3 | 4 | 5 | | | V-2 | Ing2 |
| 5352 | 3 | 4 | 5 | | | V-2 | Hist1h2bb | 5437 | 3 | 4 | 5 | | | V-2 | Ing4 |
| 5353 | 3 | 4 | 5 | | | V-2 | Hist1h3b | 5438 | 3 | 4 | 5 | | | V-2 | Ino80b |

Fig. 43 - 33

| | | | | | | | |
|---|---|---|---|---|---|---|---|
| 5439 | 3 | 4 | 5 | | | V-2 | ino80d |
| 5440 | 3 | 4 | 5 | | | V-2 | Inpp1 |
| 5441 | 3 | 4 | 5 | | | V-2 | Insig2 |
| 5442 | 3 | 4 | 5 | | | V-2 | Insrr |
| 5443 | 3 | 4 | 5 | | | V-2 | Ints3 |
| 5444 | 3 | 4 | 5 | | | V-2 | Ints6 |
| 5445 | 3 | 4 | 5 | | | V-2 | Ints8 |
| 5446 | 3 | 4 | 5 | | | V-2 | Invs |
| 5447 | 3 | 4 | 5 | | | V-2 | Ip6k2 |
| 5448 | 3 | 4 | 5 | | | V-2 | Ipmk |
| 5449 | 3 | 4 | 5 | | | V-2 | Iqcb1 |
| 5450 | 3 | 4 | 5 | | | V-2 | Iqub |
| 5451 | 3 | 4 | 5 | | | V-2 | Irf3 |
| 5452 | 3 | 4 | 5 | | | V-2 | Irf9 |
| 5453 | 3 | 4 | 5 | | | V-2 | Irgq |
| 5454 | 3 | 4 | 5 | | | V-2 | Irx5 |
| 5455 | 3 | 4 | 5 | | | V-2 | Isca1 |
| 5456 | 3 | 4 | 5 | | | V-2 | Isy1 |
| 5457 | 3 | 4 | 5 | | | V-2 | Isyna1 |
| 5458 | 3 | 4 | 5 | | | V-2 | Itga10 |
| 5459 | 3 | 4 | 5 | | | V-2 | Itga11 |
| 5460 | 3 | 4 | 5 | | | V-2 | Itgb1bp1 |
| 5461 | 3 | 4 | 5 | | | V-2 | Itgb3 |
| 5462 | 3 | 4 | 5 | | | V-2 | Itgb4 |
| 5463 | 3 | 4 | 5 | | | V-2 | Itgbl1 |
| 5464 | 3 | 4 | 5 | | | V-2 | Itih5 |
| 5465 | 3 | 4 | 5 | | | V-2 | Itpk1 |
| 5466 | 3 | 4 | 5 | | | V-2 | Itpkc |
| 5467 | 3 | 4 | 5 | | | V-2 | Itpr1 |
| 5468 | 3 | 4 | 5 | | | V-2 | Itpr2 |
| 5469 | 3 | 4 | 5 | | | V-2 | Itpr3 |
| 5470 | 3 | 4 | 5 | | | V-2 | Itsn2 |
| 5471 | 3 | 4 | 5 | | | V-2 | Ivns1abp |
| 5472 | 3 | 4 | 5 | | | V-2 | Jade1 |
| 5473 | 3 | 4 | 5 | | | V-2 | Jade3 |
| 5474 | 3 | 4 | 5 | | | V-2 | Jagn1 |
| 5475 | 3 | 4 | 5 | | | V-2 | Jak1 |
| 5476 | 3 | 4 | 5 | | | V-2 | Jmjd8 |
| 5477 | 3 | 4 | 5 | | | V-2 | Jmy |
| 5478 | 3 | 4 | 5 | | | V-2 | Jph4 |
| 5479 | 3 | 4 | 5 | | | V-2 | Jrk |
| 5480 | 3 | 4 | 5 | | | V-2 | Jtb |
| 5481 | 3 | 4 | 5 | | | V-2 | Jun |
| 5482 | 3 | 4 | 5 | | | V-2 | Junb |
| 5483 | 3 | 4 | 5 | | | V-2 | Kank4 |
| 5484 | 3 | 4 | 5 | | | V-2 | Kansl1l |
| 5485 | 3 | 4 | 5 | | | V-2 | Kat2a |
| 5486 | 3 | 4 | 5 | | | V-2 | Kat5 |
| 5487 | 3 | 4 | 5 | | | V-2 | Kat6b |
| 5488 | 3 | 4 | 5 | | | V-2 | Kbtbd11 |
| 5489 | 3 | 4 | 5 | | | V-2 | Kbtbd12 |
| 5490 | 3 | 4 | 5 | | | V-2 | Kbtbd4 |
| 5491 | 3 | 4 | 5 | | | V-2 | Kbtbd8 |
| 5492 | 3 | 4 | 5 | | | V-2 | Kcna2 |
| 5493 | 3 | 4 | 5 | | | V-2 | Kcna5 |
| 5494 | 3 | 4 | 5 | | | V-2 | Kcnab1 |
| 5495 | 3 | 4 | 5 | | | V-2 | Kcnh3 |
| 5496 | 3 | 4 | 5 | | | V-2 | Kcnj9 |
| 5497 | 3 | 4 | 5 | | | V-2 | Kcnk2 |
| 5498 | 3 | 4 | 5 | | | V-2 | Kcnk6 |
| 5499 | 3 | 4 | 5 | | | V-2 | Kcnmb1 |
| 5500 | 3 | 4 | 5 | | | V-2 | Kcnn1 |
| 5501 | 3 | 4 | 5 | | | V-2 | Kcnn2 |
| 5502 | 3 | 4 | 5 | | | V-2 | Kcnn4 |
| 5503 | 3 | 4 | 5 | | | V-2 | Kcnq4 |
| 5504 | 3 | 4 | 5 | | | V-2 | Kcnrg |
| 5505 | 3 | 4 | 5 | | | V-2 | Kctd12b |
| 5506 | 3 | 4 | 5 | | | V-2 | Kctd13 |
| 5507 | 3 | 4 | 5 | | | V-2 | Kctd14 |
| 5508 | 3 | 4 | 5 | | | V-2 | Kctd20 |
| 5509 | 3 | 4 | 5 | | | V-2 | Kctd3 |
| 5510 | 3 | 4 | 5 | | | V-2 | Kdelr2 |
| 5511 | 3 | 4 | 5 | | | V-2 | Kdm1a |
| 5512 | 3 | 4 | 5 | | | V-2 | Kdm1b |
| 5513 | 3 | 4 | 5 | | | V-2 | Kdm2a |
| 5514 | 3 | 4 | 5 | | | V-2 | Kdm2b |
| 5515 | 3 | 4 | 5 | | | V-2 | Kdm3b |
| 5516 | 3 | 4 | 5 | | | V-2 | Kdm4c |
| 5517 | 3 | 4 | 5 | | | V-2 | Kdm5c |
| 5518 | 3 | 4 | 5 | | | V-2 | Kdm5d |
| 5519 | 3 | 4 | 5 | | | V-2 | Kdm6a |
| 5520 | 3 | 4 | 5 | | | V-2 | Keap1 |
| 5521 | 3 | 4 | 5 | | | V-2 | Keg1 |
| 5522 | 3 | 4 | 5 | | | V-2 | Khdc3 |
| 5523 | 3 | 4 | 5 | | | V-2 | Kif1a |
| 5524 | 3 | 4 | 5 | | | V-2 | Kif1b |
| 5525 | 3 | 4 | 5 | | | V-2 | Kif26a |
| 5526 | 3 | 4 | 5 | | | V-2 | Kif27 |
| 5527 | 3 | 4 | 5 | | | V-2 | Kif2a |
| 5528 | 3 | 4 | 5 | | | V-2 | Kif5a |
| 5529 | 3 | 4 | 5 | | | V-2 | Kifc2 |
| 5530 | 3 | 4 | 5 | | | V-2 | Kifc3 |
| 5531 | 3 | 4 | 5 | | | V-2 | Kin |
| 5532 | 3 | 4 | 5 | | | V-2 | Kitl |
| 5533 | 3 | 4 | 5 | | | V-2 | Kiz |
| 5534 | 3 | 4 | 5 | | | V-2 | Klf11 |
| 5535 | 3 | 4 | 5 | | | V-2 | Klf2 |
| 5536 | 3 | 4 | 5 | | | V-2 | Klf8 |
| 5537 | 3 | 4 | 5 | | | V-2 | Klhdc1 |
| 5538 | 3 | 4 | 5 | | | V-2 | Klhdc3 |
| 5539 | 3 | 4 | 5 | | | V-2 | Klhl25 |
| 5540 | 3 | 4 | 5 | | | V-2 | Klhl42 |
| 5541 | 3 | 4 | 5 | | | V-2 | Klhl8 |
| 5542 | 3 | 4 | 5 | | | V-2 | Klk15 |
| 5543 | 3 | 4 | 5 | | | V-2 | Klk1b21 |
| 5544 | 3 | 4 | 5 | | | V-2 | Klk1b3 |
| 5545 | 3 | 4 | 5 | | | V-2 | Klk8 |
| 5546 | 3 | 4 | 5 | | | V-2 | Klra1 |
| 5547 | 3 | 4 | 5 | | | V-2 | Klra14-ps |
| 5548 | 3 | 4 | 5 | | | V-2 | Kmo |
| 5549 | 3 | 4 | 5 | | | V-2 | Kmt2c |
| 5550 | 3 | 4 | 5 | | | V-2 | Kpna4 |
| 5551 | 3 | 4 | 5 | | | V-2 | Krcc1 |
| 5552 | 3 | 4 | 5 | | | V-2 | Kremen1 |
| 5553 | 3 | 4 | 5 | | | V-2 | Krt32 |
| 5554 | 3 | 4 | 5 | | | V-2 | Krt7 |
| 5555 | 3 | 4 | 5 | | | V-2 | Ksr1 |
| 5556 | 3 | 4 | 5 | | | V-2 | Kxd1 |
| 5557 | 3 | 4 | 5 | | | V-2 | Kynu |
| 5558 | 3 | 4 | 5 | | | V-2 | L1cam |
| 5559 | 3 | 4 | 5 | | | V-2 | L3hypdh |
| 5560 | 3 | 4 | 5 | | | V-2 | L3mbtl3 |
| 5561 | 3 | 4 | 5 | | | V-2 | l7Rn6 |
| 5562 | 3 | 4 | 5 | | | V-2 | Lama2 |
| 5563 | 3 | 4 | 5 | | | V-2 | Lamc1 |
| 5564 | 3 | 4 | 5 | | | V-2 | Lamp3 |
| 5565 | 3 | 4 | 5 | | | V-2 | Lamtor5 |
| 5566 | 3 | 4 | 5 | | | V-2 | Lancl1 |
| 5567 | 3 | 4 | 5 | | | V-2 | Lancl2 |
| 5568 | 3 | 4 | 5 | | | V-2 | Larp1b |
| 5569 | 3 | 4 | 5 | | | V-2 | Larp4b |
| 5570 | 3 | 4 | 5 | | | V-2 | Lbr |
| 5571 | 3 | 4 | 5 | | | V-2 | Lbx2 |
| 5572 | 3 | 4 | 5 | | | V-2 | Lca5 |
| 5573 | 3 | 4 | 5 | | | V-2 | Lca5l |
| 5574 | 3 | 4 | 5 | | | V-2 | Lce3f |
| 5575 | 3 | 4 | 5 | | | V-2 | Lcmt1 |
| 5576 | 3 | 4 | 5 | | | V-2 | Lcorl |
| 5577 | 3 | 4 | 5 | | | V-2 | Ldb1 |
| 5578 | 3 | 4 | 5 | | | V-2 | Ldlrad3 |
| 5579 | 3 | 4 | 5 | | | V-2 | Ldlrap1 |
| 5580 | 3 | 4 | 5 | | | V-2 | Ldoc1l |
| 5581 | 3 | 4 | 5 | | | V-2 | Lekr1 |
| 5582 | 3 | 4 | 5 | | | V-2 | Leng9 |
| 5583 | 3 | 4 | 5 | | | V-2 | Leprel1 |
| 5584 | 3 | 4 | 5 | | | V-2 | Leprel4 |
| 5585 | 3 | 4 | 5 | | | V-2 | Letm2 |
| 5586 | 3 | 4 | 5 | | | V-2 | Lfng |
| 5587 | 3 | 4 | 5 | | | V-2 | Lgals2 |
| 5588 | 3 | 4 | 5 | | | V-2 | Lifr |
| 5589 | 3 | 4 | 5 | | | V-2 | Limd1 |
| 5590 | 3 | 4 | 5 | | | V-2 | Lin37 |
| 5591 | 3 | 4 | 5 | | | V-2 | Lins |
| 5592 | 3 | 4 | 5 | | | V-2 | Lipc |
| 5593 | 3 | 4 | 5 | | | V-2 | Lipt2 |
| 5594 | 3 | 4 | 5 | | | V-2 | Lix1 |
| 5595 | 3 | 4 | 5 | | | V-2 | Lkaaear1 |
| 5596 | 3 | 4 | 5 | | | V-2 | Llgl2 |
| 5597 | 3 | 4 | 5 | | | V-2 | Lman2l |
| 5598 | 3 | 4 | 5 | | | V-2 | Lmbr1l |
| 5599 | 3 | 4 | 5 | | | V-2 | Lmln |
| 5600 | 3 | 4 | 5 | | | V-2 | Lmo1 |
| 5601 | 3 | 4 | 5 | | | V-2 | Lmod1 |
| 5602 | 3 | 4 | 5 | | | V-2 | Lmtk2 |
| 5603 | 3 | 4 | 5 | | | V-2 | Lnx2 |
| 5604 | 3 | 4 | 5 | | | V-2 | LOC100504608 |
| 5605 | 3 | 4 | 5 | | | V-2 | LOC101056136 |
| 5606 | 3 | 4 | 5 | | | V-2 | LOC102636514 |
| 5607 | 3 | 4 | 5 | | | V-2 | Lonp2 |
| 5608 | 3 | 4 | 5 | | | V-2 | Lpar2 |

Fig. 43 - 34

| | | | | | | | |
|---|---|---|---|---|---|---|---|
| 5609 | 3 | 4 | 5 | | | V-2 | Lpin1 |
| 5610 | 3 | 4 | 5 | | | V-2 | Lrch1 |
| 5611 | 3 | 4 | 5 | | | V-2 | Lrch3 |
| 5612 | 3 | 4 | 5 | | | V-2 | Lrit2 |
| 5613 | 3 | 4 | 5 | | | V-2 | Lrp10 |
| 5614 | 3 | 4 | 5 | | | V-2 | Lrp5 |
| 5615 | 3 | 4 | 5 | | | V-2 | Lrp6 |
| 5616 | 3 | 4 | 5 | | | V-2 | Lrrc1 |
| 5617 | 3 | 4 | 5 | | | V-2 | Lrrc16a |
| 5618 | 3 | 4 | 5 | | | V-2 | Lrrc24 |
| 5619 | 3 | 4 | 5 | | | V-2 | Lrrc3 |
| 5620 | 3 | 4 | 5 | | | V-2 | Lrrc34 |
| 5621 | 3 | 4 | 5 | | | V-2 | Lrrc36 |
| 5622 | 3 | 4 | 5 | | | V-2 | Lrrc42 |
| 5623 | 3 | 4 | 5 | | | V-2 | Lrrc57 |
| 5624 | 3 | 4 | 5 | | | V-2 | Lrrc61 |
| 5625 | 3 | 4 | 5 | | | V-2 | Lrrc8a |
| 5626 | 3 | 4 | 5 | | | V-2 | Lrrfip2 |
| 5627 | 3 | 4 | 5 | | | V-2 | Lrrk2 |
| 5628 | 3 | 4 | 5 | | | V-2 | Lrrn3 |
| 5629 | 3 | 4 | 5 | | | V-2 | Lsm10 |
| 5630 | 3 | 4 | 5 | | | V-2 | Lsm11 |
| 5631 | 3 | 4 | 5 | | | V-2 | Ltk |
| 5632 | 3 | 4 | 5 | | | V-2 | Ltn1 |
| 5633 | 3 | 4 | 5 | | | V-2 | Luc7l3 |
| 5634 | 3 | 4 | 5 | | | V-2 | Lurap1l |
| 5635 | 3 | 4 | 5 | | | V-2 | Lypd6b |
| 5636 | 3 | 4 | 5 | | | V-2 | Lysmd1 |
| 5637 | 3 | 4 | 5 | | | V-2 | Lzic |
| 5638 | 3 | 4 | 5 | | | V-2 | Lztfl1 |
| 5639 | 3 | 4 | 5 | | | V-2 | Lztr1 |
| 5640 | 3 | 4 | 5 | | | V-2 | Lzts1 |
| 5641 | 3 | 4 | 5 | | | V-2 | Lzts3 |
| 5642 | 3 | 4 | 5 | | | V-2 | Macc1 |
| 5643 | 3 | 4 | 5 | | | V-2 | Macrod1 |
| 5644 | 3 | 4 | 5 | | | V-2 | Mageb3 |
| 5645 | 3 | 4 | 5 | | | V-2 | Magi1 |
| 5646 | 3 | 4 | 5 | | | V-2 | Magi3 |
| 5647 | 3 | 4 | 5 | | | V-2 | Magix |
| 5648 | 3 | 4 | 5 | | | V-2 | Magoh |
| 5649 | 3 | 4 | 5 | | | V-2 | Maml3 |
| 5650 | 3 | 4 | 5 | | | V-2 | Man1a |
| 5651 | 3 | 4 | 5 | | | V-2 | Man1b1 |
| 5652 | 3 | 4 | 5 | | | V-2 | Man2a2 |
| 5653 | 3 | 4 | 5 | | | V-2 | Maob |
| 5654 | 3 | 4 | 5 | | | V-2 | Map1lc3a |
| 5655 | 3 | 4 | 5 | | | V-2 | Map2 |
| 5656 | 3 | 4 | 5 | | | V-2 | Map2k2 |
| 5657 | 3 | 4 | 5 | | | V-2 | Map2k5 |
| 5658 | 3 | 4 | 5 | | | V-2 | Map2k6 |
| 5659 | 3 | 4 | 5 | | | V-2 | Map3k1 |
| 5660 | 3 | 4 | 5 | | | V-2 | Map3k10 |
| 5661 | 3 | 4 | 5 | | | V-2 | Map3k12 |
| 5662 | 3 | 4 | 5 | | | V-2 | Map3k14 |
| 5663 | 3 | 4 | 5 | | | V-2 | Map3k4 |
| 5664 | 3 | 4 | 5 | | | V-2 | Map3k8 |
| 5665 | 3 | 4 | 5 | | | V-2 | Map4k1 |
| 5666 | 3 | 4 | 5 | | | V-2 | Map4k2 |
| 5667 | 3 | 4 | 5 | | | V-2 | Map7 |
| 5668 | 3 | 4 | 5 | | | V-2 | Mapk15 |
| 5669 | 3 | 4 | 5 | | | V-2 | Mapk1ip1 |
| 5670 | 3 | 4 | 5 | | | V-2 | Mapk3 |
| 5671 | 3 | 4 | 5 | | | V-2 | Mapk8ip2 |
| 5672 | 3 | 4 | 5 | | | V-2 | Mapkap1 |
| 5673 | 3 | 4 | 5 | | | V-2 | Marc2 |
| 5674 | 3 | 4 | 5 | | | V-2 | March2 |
| 5675 | 3 | 4 | 5 | | | V-2 | March4 |
| 5676 | 3 | 4 | 5 | | | V-2 | March9 |
| 5677 | 3 | 4 | 5 | | | V-2 | Marf1 |
| 5678 | 3 | 4 | 5 | | | V-2 | Marveld2 |
| 5679 | 3 | 4 | 5 | | | V-2 | Matk |
| 5680 | 3 | 4 | 5 | | | V-2 | Mbd3l1 |
| 5681 | 3 | 4 | 5 | | | V-2 | Mblac1 |
| 5682 | 3 | 4 | 5 | | | V-2 | Mbtd1 |
| 5683 | 3 | 4 | 5 | | | V-2 | Mbtps1 |
| 5684 | 3 | 4 | 5 | | | V-2 | Mc5r |
| 5685 | 3 | 4 | 5 | | | V-2 | Mcat |
| 5686 | 3 | 4 | 5 | | | V-2 | Mcf2l |
| 5687 | 3 | 4 | 5 | | | V-2 | Mcm3ap |
| 5688 | 3 | 4 | 5 | | | V-2 | Mcmbp |
| 5689 | 3 | 4 | 5 | | | V-2 | Mcph1 |
| 5690 | 3 | 4 | 5 | | | V-2 | Mcpt1 |
| 5691 | 3 | 4 | 5 | | | V-2 | Mcpt4 |
| 5692 | 3 | 4 | 5 | | | V-2 | Mctp1 |
| 5693 | 3 | 4 | 5 | | | V-2 | Mcts1 |

| | | | | | | | |
|---|---|---|---|---|---|---|---|
| 5694 | 3 | 4 | 5 | | | V-2 | Mdc1 |
| 5695 | 3 | 4 | 5 | | | V-2 | Mdfi |
| 5696 | 3 | 4 | 5 | | | V-2 | Me3 |
| 5697 | 3 | 4 | 5 | | | V-2 | Meaf6 |
| 5698 | 3 | 4 | 5 | | | V-2 | Mecp2 |
| 5699 | 3 | 4 | 5 | | | V-2 | Med11 |
| 5700 | 3 | 4 | 5 | | | V-2 | Med13l |
| 5701 | 3 | 4 | 5 | | | V-2 | Med18 |
| 5702 | 3 | 4 | 5 | | | V-2 | Med27 |
| 5703 | 3 | 4 | 5 | | | V-2 | Med28 |
| 5704 | 3 | 4 | 5 | | | V-2 | Med29 |
| 5705 | 3 | 4 | 5 | | | V-2 | Med9 |
| 5706 | 3 | 4 | 5 | | | V-2 | Meis1 |
| 5707 | 3 | 4 | 5 | | | V-2 | Meox1 |
| 5708 | 3 | 4 | 5 | | | V-2 | Mesp1 |
| 5709 | 3 | 4 | 5 | | | V-2 | Met |
| 5710 | 3 | 4 | 5 | | | V-2 | Metap1d |
| 5711 | 3 | 4 | 5 | | | V-2 | Metap2 |
| 5712 | 3 | 4 | 5 | | | V-2 | Metrnl |
| 5713 | 3 | 4 | 5 | | | V-2 | Mettl13 |
| 5714 | 3 | 4 | 5 | | | V-2 | Mettl18 |
| 5715 | 3 | 4 | 5 | | | V-2 | Mettl2 |
| 5716 | 3 | 4 | 5 | | | V-2 | Mettl20 |
| 5717 | 3 | 4 | 5 | | | V-2 | Mettl3 |
| 5718 | 3 | 4 | 5 | | | V-2 | Mettl7a1 |
| 5719 | 3 | 4 | 5 | | | V-2 | Mettl7a2 |
| 5720 | 3 | 4 | 5 | | | V-2 | Mex3a |
| 5721 | 3 | 4 | 5 | | | V-2 | Mex3b |
| 5722 | 3 | 4 | 5 | | | V-2 | Mfap2 |
| 5723 | 3 | 4 | 5 | | | V-2 | Mfap4 |
| 5724 | 3 | 4 | 5 | | | V-2 | Mfge8 |
| 5725 | 3 | 4 | 5 | | | V-2 | Mfhas1 |
| 5726 | 3 | 4 | 5 | | | V-2 | Mfng |
| 5727 | 3 | 4 | 5 | | | V-2 | Mfsd3 |
| 5728 | 3 | 4 | 5 | | | V-2 | Mfsd6 |
| 5729 | 3 | 4 | 5 | | | V-2 | Mfsd7c |
| 5730 | 3 | 4 | 5 | | | V-2 | Mga |
| 5731 | 3 | 4 | 5 | | | V-2 | Mgme1 |
| 5732 | 3 | 4 | 5 | | | V-2 | Mgrn1 |
| 5733 | 3 | 4 | 5 | | | V-2 | Mib2 |
| 5734 | 3 | 4 | 5 | | | V-2 | Mical3 |
| 5735 | 3 | 4 | 5 | | | V-2 | Micalcl |
| 5736 | 3 | 4 | 5 | | | V-2 | Micu2 |
| 5737 | 3 | 4 | 5 | | | V-2 | Micu3 |
| 5738 | 3 | 4 | 5 | | | V-2 | Mier1 |
| 5739 | 3 | 4 | 5 | | | V-2 | Mier2 |
| 5740 | 3 | 4 | 5 | | | V-2 | Mina |
| 5741 | 3 | 4 | 5 | | | V-2 | Mios |
| 5742 | 3 | 4 | 5 | | | V-2 | Miox |
| 5743 | 3 | 4 | 5 | | | V-2 | Mir17hg |
| 5744 | 3 | 4 | 5 | | | V-2 | Mirg |
| 5745 | 3 | 4 | 5 | | | V-2 | Mkl2 |
| 5746 | 3 | 4 | 5 | | | V-2 | Mknk2 |
| 5747 | 3 | 4 | 5 | | | V-2 | Mkrn1 |
| 5748 | 3 | 4 | 5 | | | V-2 | Mkx |
| 5749 | 3 | 4 | 5 | | | V-2 | Mlec |
| 5750 | 3 | 4 | 5 | | | V-2 | Mllt1 |
| 5751 | 3 | 4 | 5 | | | V-2 | Mllt6 |
| 5752 | 3 | 4 | 5 | | | V-2 | Mlxip |
| 5753 | 3 | 4 | 5 | | | V-2 | Mmaa |
| 5754 | 3 | 4 | 5 | | | V-2 | Mmgt2 |
| 5755 | 3 | 4 | 5 | | | V-2 | Mmp11 |
| 5756 | 3 | 4 | 5 | | | V-2 | Mmp17 |
| 5757 | 3 | 4 | 5 | | | V-2 | Mms19 |
| 5758 | 3 | 4 | 5 | | | V-2 | Mndal |
| 5759 | 3 | 4 | 5 | | | V-2 | Mob3a |
| 5760 | 3 | 4 | 5 | | | V-2 | Mogat1 |
| 5761 | 3 | 4 | 5 | | | V-2 | Morf4l1 |
| 5762 | 3 | 4 | 5 | | | V-2 | Morn4 |
| 5763 | 3 | 4 | 5 | | | V-2 | Mpc2 |
| 5764 | 3 | 4 | 5 | | | V-2 | Mpl |
| 5765 | 3 | 4 | 5 | | | V-2 | Mplkip |
| 5766 | 3 | 4 | 5 | | | V-2 | Mpp2 |
| 5767 | 3 | 4 | 5 | | | V-2 | Mpst |
| 5768 | 3 | 4 | 5 | | | V-2 | Mras |
| 5769 | 3 | 4 | 5 | | | V-2 | Mrc1 |
| 5770 | 3 | 4 | 5 | | | V-2 | Mrm1 |
| 5771 | 3 | 4 | 5 | | | V-2 | Mrpl15 |
| 5772 | 3 | 4 | 5 | | | V-2 | Mrpl21 |
| 5773 | 3 | 4 | 5 | | | V-2 | Mrpl27 |
| 5774 | 3 | 4 | 5 | | | V-2 | Mrpl30 |
| 5775 | 3 | 4 | 5 | | | V-2 | Mrpl32 |
| 5776 | 3 | 4 | 5 | | | V-2 | Mrpl34 |
| 5777 | 3 | 4 | 5 | | | V-2 | Mrpl36 |
| 5778 | 3 | 4 | 5 | | | V-2 | Mrpl43 |

Fig. 43 - 35

| | | | | | | | |
|---|---|---|---|---|---|---|---|
| 5779 | 3 | 4 | 5 | | | V-2 | Mrpl9 |
| 5780 | 3 | 4 | 5 | | | V-2 | Mrps15 |
| 5781 | 3 | 4 | 5 | | | V-2 | Mrps27 |
| 5782 | 3 | 4 | 5 | | | V-2 | Mrps35 |
| 5783 | 3 | 4 | 5 | | | V-2 | Mrps9 |
| 5784 | 3 | 4 | 5 | | | V-2 | Msh6 |
| 5785 | 3 | 4 | 5 | | | V-2 | Msl3 |
| 5786 | 3 | 4 | 5 | | | V-2 | Msmp |
| 5787 | 3 | 4 | 5 | | | V-2 | Mtch1 |
| 5788 | 3 | 4 | 5 | | | V-2 | Mterf1a |
| 5789 | 3 | 4 | 5 | | | V-2 | Mterf1b |
| 5790 | 3 | 4 | 5 | | | V-2 | Mterfd1 |
| 5791 | 3 | 4 | 5 | | | V-2 | Mterfd2 |
| 5792 | 3 | 4 | 5 | | | V-2 | Mtf1 |
| 5793 | 3 | 4 | 5 | | | V-2 | Mtf2 |
| 5794 | 3 | 4 | 5 | | | V-2 | Mtg2 |
| 5795 | 3 | 4 | 5 | | | V-2 | Mthfd2l |
| 5796 | 3 | 4 | 5 | | | V-2 | Mthfs |
| 5797 | 3 | 4 | 5 | | | V-2 | Mthfsd |
| 5798 | 3 | 4 | 5 | | | V-2 | Mtif3 |
| 5799 | 3 | 4 | 5 | | | V-2 | Mtmr14 |
| 5800 | 3 | 4 | 5 | | | V-2 | Mtr |
| 5801 | 3 | 4 | 5 | | | V-2 | Mtrf1l |
| 5802 | 3 | 4 | 5 | | | V-2 | Mtx2 |
| 5803 | 3 | 4 | 5 | | | V-2 | Mug-ps1 |
| 5804 | 3 | 4 | 5 | | | V-2 | Mum1 |
| 5805 | 3 | 4 | 5 | | | V-2 | Mup7 |
| 5806 | 3 | 4 | 5 | | | V-2 | Mus81 |
| 5807 | 3 | 4 | 5 | | | V-2 | Mxd3 |
| 5808 | 3 | 4 | 5 | | | V-2 | Myd88 |
| 5809 | 3 | 4 | 5 | | | V-2 | Myl12a |
| 5810 | 3 | 4 | 5 | | | V-2 | Mylip |
| 5811 | 3 | 4 | 5 | | | V-2 | Mylk |
| 5812 | 3 | 4 | 5 | | | V-2 | Myo5c |
| 5813 | 3 | 4 | 5 | | | V-2 | Mypop |
| 5814 | 3 | 4 | 5 | | | V-2 | N4bp1 |
| 5815 | 3 | 4 | 5 | | | V-2 | N4bp2l1 |
| 5816 | 3 | 4 | 5 | | | V-2 | Naa25 |
| 5817 | 3 | 4 | 5 | | | V-2 | Naa35 |
| 5818 | 3 | 4 | 5 | | | V-2 | Nab2 |
| 5819 | 3 | 4 | 5 | | | V-2 | Nacad |
| 5820 | 3 | 4 | 5 | | | V-2 | Nacc2 |
| 5821 | 3 | 4 | 5 | | | V-2 | Nadsyn1 |
| 5822 | 3 | 4 | 5 | | | V-2 | Nae1 |
| 5823 | 3 | 4 | 5 | | | V-2 | Nagk |
| 5824 | 3 | 4 | 5 | | | V-2 | Nagpa |
| 5825 | 3 | 4 | 5 | | | V-2 | Naif1 |
| 5826 | 3 | 4 | 5 | | | V-2 | Nampt |
| 5827 | 3 | 4 | 5 | | | V-2 | Nanos1 |
| 5828 | 3 | 4 | 5 | | | V-2 | Nanos3 |
| 5829 | 3 | 4 | 5 | | | V-2 | Nanp |
| 5830 | 3 | 4 | 5 | | | V-2 | Nap1l3 |
| 5831 | 3 | 4 | 5 | | | V-2 | Nat14 |
| 5832 | 3 | 4 | 5 | | | V-2 | Nav2 |
| 5833 | 3 | 4 | 5 | | | V-2 | Nbeal2 |
| 5834 | 3 | 4 | 5 | | | V-2 | Ncald |
| 5835 | 3 | 4 | 5 | | | V-2 | Ncapg |
| 5836 | 3 | 4 | 5 | | | V-2 | Ncbp2 |
| 5837 | 3 | 4 | 5 | | | V-2 | Nck1 |
| 5838 | 3 | 4 | 5 | | | V-2 | Nckap5 |
| 5839 | 3 | 4 | 5 | | | V-2 | Ncoa2 |
| 5840 | 3 | 4 | 5 | | | V-2 | Ncoa3 |
| 5841 | 3 | 4 | 5 | | | V-2 | Ncoa7 |
| 5842 | 3 | 4 | 5 | | | V-2 | Ncor1 |
| 5843 | 3 | 4 | 5 | | | V-2 | Ncr1 |
| 5844 | 3 | 4 | 5 | | | V-2 | Ndel1 |
| 5845 | 3 | 4 | 5 | | | V-2 | Ndnl2 |
| 5846 | 3 | 4 | 5 | | | V-2 | Ndrg1 |
| 5847 | 3 | 4 | 5 | | | V-2 | Neat1 |
| 5848 | 3 | 4 | 5 | | | V-2 | Nedd1 |
| 5849 | 3 | 4 | 5 | | | V-2 | Nefm |
| 5850 | 3 | 4 | 5 | | | V-2 | Nek1 |
| 5851 | 3 | 4 | 5 | | | V-2 | Nek4 |
| 5852 | 3 | 4 | 5 | | | V-2 | Nek7 |
| 5853 | 3 | 4 | 5 | | | V-2 | Nelfa |
| 5854 | 3 | 4 | 5 | | | V-2 | Nelfb |
| 5855 | 3 | 4 | 5 | | | V-2 | Nepn |
| 5856 | 3 | 4 | 5 | | | V-2 | Nes |
| 5857 | 3 | 4 | 5 | | | V-2 | Neurl4 |
| 5858 | 3 | 4 | 5 | | | V-2 | Nfat5 |
| 5859 | 3 | 4 | 5 | | | V-2 | Nfe2l3 |
| 5860 | 3 | 4 | 5 | | | V-2 | Nfil3 |
| 5861 | 3 | 4 | 5 | | | V-2 | Nfkb2 |
| 5862 | 3 | 4 | 5 | | | V-2 | Nfkbib |
| 5863 | 3 | 4 | 5 | | | V-2 | Nfkbid |
| 5864 | 3 | 4 | 5 | | | V-2 | Ngfr |
| 5865 | 3 | 4 | 5 | | | V-2 | Nhsl1 |
| 5866 | 3 | 4 | 5 | | | V-2 | Nicn1 |
| 5867 | 3 | 4 | 5 | | | V-2 | Nid1 |
| 5868 | 3 | 4 | 5 | | | V-2 | Ninl |
| 5869 | 3 | 4 | 5 | | | V-2 | Nip7 |
| 5870 | 3 | 4 | 5 | | | V-2 | Nipal1 |
| 5871 | 3 | 4 | 5 | | | V-2 | Nipal3 |
| 5872 | 3 | 4 | 5 | | | V-2 | Nipbl |
| 5873 | 3 | 4 | 5 | | | V-2 | Nkx3-1 |
| 5874 | 3 | 4 | 5 | | | V-2 | Nle1 |
| 5875 | 3 | 4 | 5 | | | V-2 | Nlrc3 |
| 5876 | 3 | 4 | 5 | | | V-2 | Nlrp6 |
| 5877 | 3 | 4 | 5 | | | V-2 | Nmt1 |
| 5878 | 3 | 4 | 5 | | | V-2 | Noa1 |
| 5879 | 3 | 4 | 5 | | | V-2 | Noc2l |
| 5880 | 3 | 4 | 5 | | | V-2 | Nog |
| 5881 | 3 | 4 | 5 | | | V-2 | Nol8 |
| 5882 | 3 | 4 | 5 | | | V-2 | Nop16 |
| 5883 | 3 | 4 | 5 | | | V-2 | Nop2 |
| 5884 | 3 | 4 | 5 | | | V-2 | Nop9 |
| 5885 | 3 | 4 | 5 | | | V-2 | Nos1 |
| 5886 | 3 | 4 | 5 | | | V-2 | Notch2 |
| 5887 | 3 | 4 | 5 | | | V-2 | Notch3 |
| 5888 | 3 | 4 | 5 | | | V-2 | Notch4 |
| 5889 | 3 | 4 | 5 | | | V-2 | Npc1 |
| 5890 | 3 | 4 | 5 | | | V-2 | Npepl1 |
| 5891 | 3 | 4 | 5 | | | V-2 | Nphs2 |
| 5892 | 3 | 4 | 5 | | | V-2 | Npm3-ps1 |
| 5893 | 3 | 4 | 5 | | | V-2 | Nprl2 |
| 5894 | 3 | 4 | 5 | | | V-2 | Nprl3 |
| 5895 | 3 | 4 | 5 | | | V-2 | Npy1r |
| 5896 | 3 | 4 | 5 | | | V-2 | Nr1h2 |
| 5897 | 3 | 4 | 5 | | | V-2 | Nr2c1 |
| 5898 | 3 | 4 | 5 | | | V-2 | Nr2f6 |
| 5899 | 3 | 4 | 5 | | | V-2 | Nrbp1 |
| 5900 | 3 | 4 | 5 | | | V-2 | Nrd1 |
| 5901 | 3 | 4 | 5 | | | V-2 | Nrf1 |
| 5902 | 3 | 4 | 5 | | | V-2 | Nrg2 |
| 5903 | 3 | 4 | 5 | | | V-2 | Nrp1 |
| 5904 | 3 | 4 | 5 | | | V-2 | Nrxn1 |
| 5905 | 3 | 4 | 5 | | | V-2 | Nsd1 |
| 5906 | 3 | 4 | 5 | | | V-2 | Nsg2 |
| 5907 | 3 | 4 | 5 | | | V-2 | Nsmaf |
| 5908 | 3 | 4 | 5 | | | V-2 | Nsmf |
| 5909 | 3 | 4 | 5 | | | V-2 | Nsun6 |
| 5910 | 3 | 4 | 5 | | | V-2 | Nt5c3b |
| 5911 | 3 | 4 | 5 | | | V-2 | Nt5m |
| 5912 | 3 | 4 | 5 | | | V-2 | Nubpl |
| 5913 | 3 | 4 | 5 | | | V-2 | Nudt13 |
| 5914 | 3 | 4 | 5 | | | V-2 | Nudt14 |
| 5915 | 3 | 4 | 5 | | | V-2 | Nudt8 |
| 5916 | 3 | 4 | 5 | | | V-2 | Nudt9 |
| 5917 | 3 | 4 | 5 | | | V-2 | Numa1 |
| 5918 | 3 | 4 | 5 | | | V-2 | Nup160 |
| 5919 | 3 | 4 | 5 | | | V-2 | Nup188 |
| 5920 | 3 | 4 | 5 | | | V-2 | Nup214 |
| 5921 | 3 | 4 | 5 | | | V-2 | Nup35 |
| 5922 | 3 | 4 | 5 | | | V-2 | Nup85 |
| 5923 | 3 | 4 | 5 | | | V-2 | Nvl |
| 5924 | 3 | 4 | 5 | | | V-2 | Nxn |
| 5925 | 3 | 4 | 5 | | | V-2 | Nxpe3 |
| 5926 | 3 | 4 | 5 | | | V-2 | Nxpe4 |
| 5927 | 3 | 4 | 5 | | | V-2 | Nynrin |
| 5928 | 3 | 4 | 5 | | | V-2 | Nyx |
| 5929 | 3 | 4 | 5 | | | V-2 | Oaz2 |
| 5930 | 3 | 4 | 5 | | | V-2 | Obfc1 |
| 5931 | 3 | 4 | 5 | | | V-2 | Obsl1 |
| 5932 | 3 | 4 | 5 | | | V-2 | Odf2l |
| 5933 | 3 | 4 | 5 | | | V-2 | Ogfod3 |
| 5934 | 3 | 4 | 5 | | | V-2 | Ogt |
| 5935 | 3 | 4 | 5 | | | V-2 | Oit3 |
| 5936 | 3 | 4 | 5 | | | V-2 | Olfm4 |
| 5937 | 3 | 4 | 5 | | | V-2 | Olfr1033 |
| 5938 | 3 | 4 | 5 | | | V-2 | Olfr1420 |
| 5939 | 3 | 4 | 5 | | | V-2 | Olfr20 |
| 5940 | 3 | 4 | 5 | | | V-2 | Olfr23 |
| 5941 | 3 | 4 | 5 | | | V-2 | Olfr550 |
| 5942 | 3 | 4 | 5 | | | V-2 | Olfr558 |
| 5943 | 3 | 4 | 5 | | | V-2 | Olig1 |
| 5944 | 3 | 4 | 5 | | | V-2 | Oma1 |
| 5945 | 3 | 4 | 5 | | | V-2 | Ooep |
| 5946 | 3 | 4 | 5 | | | V-2 | Oosp1 |
| 5947 | 3 | 4 | 5 | | | V-2 | Opa3 |
| 5948 | 3 | 4 | 5 | | | V-2 | Ophn1 |

Fig. 43 - 36

| | | | | | | | |
|---|---|---|---|---|---|---|---|
| 5949 | 3 | 4 | 5 | | | V-2 | Orai1 |
| 5950 | 3 | 4 | 5 | | | V-2 | Orc2 |
| 5951 | 3 | 4 | 5 | | | V-2 | Orc5 |
| 5952 | 3 | 4 | 5 | | | V-2 | Osbpl11 |
| 5953 | 3 | 4 | 5 | | | V-2 | Osbpl5 |
| 5954 | 3 | 4 | 5 | | | V-2 | Oser1 |
| 5955 | 3 | 4 | 5 | | | V-2 | Ost4 |
| 5956 | 3 | 4 | 5 | | | V-2 | Otos |
| 5957 | 3 | 4 | 5 | | | V-2 | Otud1 |
| 5958 | 3 | 4 | 5 | | | V-2 | Otud3 |
| 5959 | 3 | 4 | 5 | | | V-2 | Otud5 |
| 5960 | 3 | 4 | 5 | | | V-2 | Otud7b |
| 5961 | 3 | 4 | 5 | | | V-2 | Otulin |
| 5962 | 3 | 4 | 5 | | | V-2 | Otx2 |
| 5963 | 3 | 4 | 5 | | | V-2 | Oxa1l |
| 5964 | 3 | 4 | 5 | | | V-2 | Oxct2b |
| 5965 | 3 | 4 | 5 | | | V-2 | Oxnad1 |
| 5966 | 3 | 4 | 5 | | | V-2 | P4ha1 |
| 5967 | 3 | 4 | 5 | | | V-2 | P4ha2 |
| 5968 | 3 | 4 | 5 | | | V-2 | Pabpc4 |
| 5969 | 3 | 4 | 5 | | | V-2 | Pacrgl |
| 5970 | 3 | 4 | 5 | | | V-2 | Padi2 |
| 5971 | 3 | 4 | 5 | | | V-2 | Paf1 |
| 5972 | 3 | 4 | 5 | | | V-2 | Pagr1a |
| 5973 | 3 | 4 | 5 | | | V-2 | Pah |
| 5974 | 3 | 4 | 5 | | | V-2 | Paip2 |
| 5975 | 3 | 4 | 5 | | | V-2 | Pamr1 |
| 5976 | 3 | 4 | 5 | | | V-2 | Pan3 |
| 5977 | 3 | 4 | 5 | | | V-2 | Pank1 |
| 5978 | 3 | 4 | 5 | | | V-2 | Pank2 |
| 5979 | 3 | 4 | 5 | | | V-2 | Papola |
| 5980 | 3 | 4 | 5 | | | V-2 | Papolg |
| 5981 | 3 | 4 | 5 | | | V-2 | Paqr8 |
| 5982 | 3 | 4 | 5 | | | V-2 | Pard3 |
| 5983 | 3 | 4 | 5 | | | V-2 | Pard3b |
| 5984 | 3 | 4 | 5 | | | V-2 | Pard6a |
| 5985 | 3 | 4 | 5 | | | V-2 | Parm1 |
| 5986 | 3 | 4 | 5 | | | V-2 | Parp11 |
| 5987 | 3 | 4 | 5 | | | V-2 | Parp6 |
| 5988 | 3 | 4 | 5 | | | V-2 | Parvb |
| 5989 | 3 | 4 | 5 | | | V-2 | Patz1 |
| 5990 | 3 | 4 | 5 | | | V-2 | Pax2 |
| 5991 | 3 | 4 | 5 | | | V-2 | Paxip1 |
| 5992 | 3 | 4 | 5 | | | V-2 | Pbp2 |
| 5993 | 3 | 4 | 5 | | | V-2 | Pcbp2 |
| 5994 | 3 | 4 | 5 | | | V-2 | Pcca |
| 5995 | 3 | 4 | 5 | | | V-2 | Pcdh1 |
| 5996 | 3 | 4 | 5 | | | V-2 | Pcdh18 |
| 5997 | 3 | 4 | 5 | | | V-2 | Pcdha1 |
| 5998 | 3 | 4 | 5 | | | V-2 | Pcdhga11 |
| 5999 | 3 | 4 | 5 | | | V-2 | Pcdhga12 |
| 6000 | 3 | 4 | 5 | | | V-2 | Pcdhga5 |
| 6001 | 3 | 4 | 5 | | | V-2 | Pcdhgb1 |
| 6002 | 3 | 4 | 5 | | | V-2 | Pcgf1 |
| 6003 | 3 | 4 | 5 | | | V-2 | Pcgf6 |
| 6004 | 3 | 4 | 5 | | | V-2 | Pck2 |
| 6005 | 3 | 4 | 5 | | | V-2 | Pcmtd2 |
| 6006 | 3 | 4 | 5 | | | V-2 | Pcnx |
| 6007 | 3 | 4 | 5 | | | V-2 | Pcsk1n |
| 6008 | 3 | 4 | 5 | | | V-2 | Pcsk2 |
| 6009 | 3 | 4 | 5 | | | V-2 | Pcsk6 |
| 6010 | 3 | 4 | 5 | | | V-2 | Pcyox1l |
| 6011 | 3 | 4 | 5 | | | V-2 | Pcyt1b |
| 6012 | 3 | 4 | 5 | | | V-2 | Pdcd4 |
| 6013 | 3 | 4 | 5 | | | V-2 | Pde10a |
| 6014 | 3 | 4 | 5 | | | V-2 | Pde1a |
| 6015 | 3 | 4 | 5 | | | V-2 | Pde1b |
| 6016 | 3 | 4 | 5 | | | V-2 | Pde3b |
| 6017 | 3 | 4 | 5 | | | V-2 | Pde4c |
| 6018 | 3 | 4 | 5 | | | V-2 | Pde4d |
| 6019 | 3 | 4 | 5 | | | V-2 | Pde5a |
| 6020 | 3 | 4 | 5 | | | V-2 | Pde7a |
| 6021 | 3 | 4 | 5 | | | V-2 | Pde8b |
| 6022 | 3 | 4 | 5 | | | V-2 | Pdf |
| 6023 | 3 | 4 | 5 | | | V-2 | Pdha2 |
| 6024 | 3 | 4 | 5 | | | V-2 | Pdia5 |
| 6025 | 3 | 4 | 5 | | | V-2 | Pdlim2 |
| 6026 | 3 | 4 | 5 | | | V-2 | Pdpk1 |
| 6027 | 3 | 4 | 5 | | | V-2 | Pdrg1 |
| 6028 | 3 | 4 | 5 | | | V-2 | Pdx1 |
| 6029 | 3 | 4 | 5 | | | V-2 | Pear1 |
| 6030 | 3 | 4 | 5 | | | V-2 | Pecam1 |
| 6031 | 3 | 4 | 5 | | | V-2 | Pef1 |
| 6032 | 3 | 4 | 5 | | | V-2 | Peg13 |
| 6033 | 3 | 4 | 5 | | | V-2 | Peli2 |
| 6034 | 3 | 4 | 5 | | | V-2 | Pepd |
| 6035 | 3 | 4 | 5 | | | V-2 | Pet112 |
| 6036 | 3 | 4 | 5 | | | V-2 | Pex1 |
| 6037 | 3 | 4 | 5 | | | V-2 | Pex10 |
| 6038 | 3 | 4 | 5 | | | V-2 | Pex11b |
| 6039 | 3 | 4 | 5 | | | V-2 | Pex14 |
| 6040 | 3 | 4 | 5 | | | V-2 | Pex16 |
| 6041 | 3 | 4 | 5 | | | V-2 | Pex6 |
| 6042 | 3 | 4 | 5 | | | V-2 | Pfn3 |
| 6043 | 3 | 4 | 5 | | | V-2 | Pgap1 |
| 6044 | 3 | 4 | 5 | | | V-2 | Pgbd1 |
| 6045 | 3 | 4 | 5 | | | V-2 | Pgis |
| 6046 | 3 | 4 | 5 | | | V-2 | Pgm5 |
| 6047 | 3 | 4 | 5 | | | V-2 | Phactr2 |
| 6048 | 3 | 4 | 5 | | | V-2 | Phax |
| 6049 | 3 | 4 | 5 | | | V-2 | Phb2 |
| 6050 | 3 | 4 | 5 | | | V-2 | Phf1 |
| 6051 | 3 | 4 | 5 | | | V-2 | Phf13 |
| 6052 | 3 | 4 | 5 | | | V-2 | Phf14 |
| 6053 | 3 | 4 | 5 | | | V-2 | Phf2 |
| 6054 | 3 | 4 | 5 | | | V-2 | Phf23 |
| 6055 | 3 | 4 | 5 | | | V-2 | Phf3 |
| 6056 | 3 | 4 | 5 | | | V-2 | Phf7 |
| 6057 | 3 | 4 | 5 | | | V-2 | Phka2 |
| 6058 | 3 | 4 | 5 | | | V-2 | Phlda1 |
| 6059 | 3 | 4 | 5 | | | V-2 | Phldb1 |
| 6060 | 3 | 4 | 5 | | | V-2 | Phlpp1 |
| 6061 | 3 | 4 | 5 | | | V-2 | Phlpp2 |
| 6062 | 3 | 4 | 5 | | | V-2 | Phyhd1 |
| 6063 | 3 | 4 | 5 | | | V-2 | Pi4ka |
| 6064 | 3 | 4 | 5 | | | V-2 | Pid1 |
| 6065 | 3 | 4 | 5 | | | V-2 | Pigh |
| 6066 | 3 | 4 | 5 | | | V-2 | Pigl |
| 6067 | 3 | 4 | 5 | | | V-2 | Pigv |
| 6068 | 3 | 4 | 5 | | | V-2 | Pik3c2b |
| 6069 | 3 | 4 | 5 | | | V-2 | Pik3c2g |
| 6070 | 3 | 4 | 5 | | | V-2 | Pik3ca |
| 6071 | 3 | 4 | 5 | | | V-2 | Pik3cg |
| 6072 | 3 | 4 | 5 | | | V-2 | Pik3ip1 |
| 6073 | 3 | 4 | 5 | | | V-2 | Pik3r2 |
| 6074 | 3 | 4 | 5 | | | V-2 | Pik3r6 |
| 6075 | 3 | 4 | 5 | | | V-2 | Pink1 |
| 6076 | 3 | 4 | 5 | | | V-2 | Pip5k1b |
| 6077 | 3 | 4 | 5 | | | V-2 | Pir |
| 6078 | 3 | 4 | 5 | | | V-2 | Pisd-ps2 |
| 6079 | 3 | 4 | 5 | | | V-2 | Pitpnc1 |
| 6080 | 3 | 4 | 5 | | | V-2 | Pitpnm2 |
| 6081 | 3 | 4 | 5 | | | V-2 | Pitpnm3 |
| 6082 | 3 | 4 | 5 | | | V-2 | Pkdcc |
| 6083 | 3 | 4 | 5 | | | V-2 | Pkhd1l1 |
| 6084 | 3 | 4 | 5 | | | V-2 | Pkig |
| 6085 | 3 | 4 | 5 | | | V-2 | Pkn1 |
| 6086 | 3 | 4 | 5 | | | V-2 | Pknox1 |
| 6087 | 3 | 4 | 5 | | | V-2 | Pkp2 |
| 6088 | 3 | 4 | 5 | | | V-2 | Pla2g15 |
| 6089 | 3 | 4 | 5 | | | V-2 | Pla2g16 |
| 6090 | 3 | 4 | 5 | | | V-2 | Pla2g2d |
| 6091 | 3 | 4 | 5 | | | V-2 | Pla2g4b |
| 6092 | 3 | 4 | 5 | | | V-2 | Pla2g4f |
| 6093 | 3 | 4 | 5 | | | V-2 | Pla2r1 |
| 6094 | 3 | 4 | 5 | | | V-2 | Plbd2 |
| 6095 | 3 | 4 | 5 | | | V-2 | Plcb1 |
| 6096 | 3 | 4 | 5 | | | V-2 | Plcb2 |
| 6097 | 3 | 4 | 5 | | | V-2 | Plcb3 |
| 6098 | 3 | 4 | 5 | | | V-2 | Plcxd1 |
| 6099 | 3 | 4 | 5 | | | V-2 | Plcxd2 |
| 6100 | 3 | 4 | 5 | | | V-2 | Pld3 |
| 6101 | 3 | 4 | 5 | | | V-2 | Plekha2 |
| 6102 | 3 | 4 | 5 | | | V-2 | Plekhd1os |
| 6103 | 3 | 4 | 5 | | | V-2 | Plekhg1 |
| 6104 | 3 | 4 | 5 | | | V-2 | Plekhg2 |
| 6105 | 3 | 4 | 5 | | | V-2 | Plekhg5 |
| 6106 | 3 | 4 | 5 | | | V-2 | Plekhh2 |
| 6107 | 3 | 4 | 5 | | | V-2 | Plekhm2 |
| 6108 | 3 | 4 | 5 | | | V-2 | Plekhn1 |
| 6109 | 3 | 4 | 5 | | | V-2 | Plekho1 |
| 6110 | 3 | 4 | 5 | | | V-2 | Plin3 |
| 6111 | 3 | 4 | 5 | | | V-2 | Plp |
| 6112 | 3 | 4 | 5 | | | V-2 | Plod3 |
| 6113 | 3 | 4 | 5 | | | V-2 | Plrg1 |
| 6114 | 3 | 4 | 5 | | | V-2 | Pls1 |
| 6115 | 3 | 4 | 5 | | | V-2 | Plxdc1 |
| 6116 | 3 | 4 | 5 | | | V-2 | Plxna1 |
| 6117 | 3 | 4 | 5 | | | V-2 | Plxna3 |
| 6118 | 3 | 4 | 5 | | | V-2 | Plxna4 |

Fig. 43 - 37

| | | | | | | | |
|---|---|---|---|---|---|---|---|
| 6119 | 3 | 4 | 5 | | V-2 | Plxnb1 |
| 6120 | 3 | 4 | 5 | | V-2 | Pmel |
| 6121 | 3 | 4 | 5 | | V-2 | Pms1 |
| 6122 | 3 | 4 | 5 | | V-2 | Pnck |
| 6123 | 3 | 4 | 5 | | V-2 | Pnkd |
| 6124 | 3 | 4 | 5 | | V-2 | Pnma1 |
| 6125 | 3 | 4 | 5 | | V-2 | Pnmal1 |
| 6126 | 3 | 4 | 5 | | V-2 | Pnpla2 |
| 6127 | 3 | 4 | 5 | | V-2 | Pnpo |
| 6128 | 3 | 4 | 5 | | V-2 | Pnrc1 |
| 6129 | 3 | 4 | 5 | | V-2 | Poc1b |
| 6130 | 3 | 4 | 5 | | V-2 | Pold3 |
| 6131 | 3 | 4 | 5 | | V-2 | Pold4 |
| 6132 | 3 | 4 | 5 | | V-2 | Poldip2 |
| 6133 | 3 | 4 | 5 | | V-2 | Pole4 |
| 6134 | 3 | 4 | 5 | | V-2 | Polg |
| 6135 | 3 | 4 | 5 | | V-2 | Poli |
| 6136 | 3 | 4 | 5 | | V-2 | Polm |
| 6137 | 3 | 4 | 5 | | V-2 | Polr1c |
| 6138 | 3 | 4 | 5 | | V-2 | Polrmt |
| 6139 | 3 | 4 | 5 | | V-2 | Pomt2 |
| 6140 | 3 | 4 | 5 | | V-2 | Pon3 |
| 6141 | 3 | 4 | 5 | | V-2 | Por |
| 6142 | 3 | 4 | 5 | | V-2 | Pot1a |
| 6143 | 3 | 4 | 5 | | V-2 | Pou2f1 |
| 6144 | 3 | 4 | 5 | | V-2 | Pou3f3os |
| 6145 | 3 | 4 | 5 | | V-2 | Pou6f1 |
| 6146 | 3 | 4 | 5 | | V-2 | Pou6f2 |
| 6147 | 3 | 4 | 5 | | V-2 | Ppapdc1a |
| 6148 | 3 | 4 | 5 | | V-2 | Ppara |
| 6149 | 3 | 4 | 5 | | V-2 | Ppdpf |
| 6150 | 3 | 4 | 5 | | V-2 | Ppfibp2 |
| 6151 | 3 | 4 | 5 | | V-2 | Ppil6 |
| 6152 | 3 | 4 | 5 | | V-2 | Ppm1d |
| 6153 | 3 | 4 | 5 | | V-2 | Ppm1f |
| 6154 | 3 | 4 | 5 | | V-2 | Ppm1g |
| 6155 | 3 | 4 | 5 | | V-2 | Ppp1ca |
| 6156 | 3 | 4 | 5 | | V-2 | Ppp1r10 |
| 6157 | 3 | 4 | 5 | | V-2 | Ppp1r11 |
| 6158 | 3 | 4 | 5 | | V-2 | Ppp1r12c |
| 6159 | 3 | 4 | 5 | | V-2 | Ppp1r13b |
| 6160 | 3 | 4 | 5 | | V-2 | Ppp1r15a |
| 6161 | 3 | 4 | 5 | | V-2 | Ppp1r21 |
| 6162 | 3 | 4 | 5 | | V-2 | Ppp1r26 |
| 6163 | 3 | 4 | 5 | | V-2 | Ppp1r35 |
| 6164 | 3 | 4 | 5 | | V-2 | Ppp1r36 |
| 6165 | 3 | 4 | 5 | | V-2 | Ppp1r37 |
| 6166 | 3 | 4 | 5 | | V-2 | Ppp1r9b |
| 6167 | 3 | 4 | 5 | | V-2 | Ppp2cb |
| 6168 | 3 | 4 | 5 | | V-2 | Ppp2r2d |
| 6169 | 3 | 4 | 5 | | V-2 | Ppp2r4 |
| 6170 | 3 | 4 | 5 | | V-2 | Ppp2r5a |
| 6171 | 3 | 4 | 5 | | V-2 | Ppp2r5b |
| 6172 | 3 | 4 | 5 | | V-2 | Ppp4r4 |
| 6173 | 3 | 4 | 5 | | V-2 | Pprc1 |
| 6174 | 3 | 4 | 5 | | V-2 | Pqlc1 |
| 6175 | 3 | 4 | 5 | | V-2 | Prap1 |
| 6176 | 3 | 4 | 5 | | V-2 | Prcc |
| 6177 | 3 | 4 | 5 | | V-2 | Prdm11 |
| 6178 | 3 | 4 | 5 | | V-2 | Prdm15 |
| 6179 | 3 | 4 | 5 | | V-2 | Prdm16 |
| 6180 | 3 | 4 | 5 | | V-2 | Prdm5 |
| 6181 | 3 | 4 | 5 | | V-2 | Prelid1 |
| 6182 | 3 | 4 | 5 | | V-2 | Prep |
| 6183 | 3 | 4 | 5 | | V-2 | Prex2 |
| 6184 | 3 | 4 | 5 | | V-2 | Prickle2 |
| 6185 | 3 | 4 | 5 | | V-2 | Prima1 |
| 6186 | 3 | 4 | 5 | | V-2 | Prkab2 |
| 6187 | 3 | 4 | 5 | | V-2 | Prkca |
| 6188 | 3 | 4 | 5 | | V-2 | Prkcb |
| 6189 | 3 | 4 | 5 | | V-2 | Prkcsh |
| 6190 | 3 | 4 | 5 | | V-2 | Prkcz |
| 6191 | 3 | 4 | 5 | | V-2 | Prkd2 |
| 6192 | 3 | 4 | 5 | | V-2 | Prkra |
| 6193 | 3 | 4 | 5 | | V-2 | Prkx |
| 6194 | 3 | 4 | 5 | | V-2 | Prmt2 |
| 6195 | 3 | 4 | 5 | | V-2 | Prmt7 |
| 6196 | 3 | 4 | 5 | | V-2 | Prorsd1 |
| 6197 | 3 | 4 | 5 | | V-2 | Prr14l |
| 6198 | 3 | 4 | 5 | | V-2 | Prr18 |
| 6199 | 3 | 4 | 5 | | V-2 | Prr22 |
| 6200 | 3 | 4 | 5 | | V-2 | Prr27 |
| 6201 | 3 | 4 | 5 | | V-2 | Prrc1 |
| 6202 | 3 | 4 | 5 | | V-2 | Prrg1 |
| 6203 | 3 | 4 | 5 | | V-2 | Prrg2 |
| 6204 | 3 | 4 | 5 | | V-2 | Prrg3 |
| 6205 | 3 | 4 | 5 | | V-2 | Prrt4 |
| 6206 | 3 | 4 | 5 | | V-2 | Prss22 |
| 6207 | 3 | 4 | 5 | | V-2 | Prss23 |
| 6208 | 3 | 4 | 5 | | V-2 | Prss52 |
| 6209 | 3 | 4 | 5 | | V-2 | Psen2 |
| 6210 | 3 | 4 | 5 | | V-2 | Psip1 |
| 6211 | 3 | 4 | 5 | | V-2 | Psmd11 |
| 6212 | 3 | 4 | 5 | | V-2 | Psmd4 |
| 6213 | 3 | 4 | 5 | | V-2 | Ptcd1 |
| 6214 | 3 | 4 | 5 | | V-2 | Ptcra |
| 6215 | 3 | 4 | 5 | | V-2 | Ptf1a |
| 6216 | 3 | 4 | 5 | | V-2 | Ptger2 |
| 6217 | 3 | 4 | 5 | | V-2 | Ptges3 |
| 6218 | 3 | 4 | 5 | | V-2 | Ptgfr |
| 6219 | 3 | 4 | 5 | | V-2 | Ptgs2 |
| 6220 | 3 | 4 | 5 | | V-2 | Pth2 |
| 6221 | 3 | 4 | 5 | | V-2 | Ptms |
| 6222 | 3 | 4 | 5 | | V-2 | Ptpn13 |
| 6223 | 3 | 4 | 5 | | V-2 | Ptpn14 |
| 6224 | 3 | 4 | 5 | | V-2 | Ptpn4 |
| 6225 | 3 | 4 | 5 | | V-2 | Ptpre |
| 6226 | 3 | 4 | 5 | | V-2 | Ptprg |
| 6227 | 3 | 4 | 5 | | V-2 | Ptrhd1 |
| 6228 | 3 | 4 | 5 | | V-2 | Pttg1 |
| 6229 | 3 | 4 | 5 | | V-2 | Ptx4 |
| 6230 | 3 | 4 | 5 | | V-2 | Purg |
| 6231 | 3 | 4 | 5 | | V-2 | Pus1 |
| 6232 | 3 | 4 | 5 | | V-2 | Pusl1 |
| 6233 | 3 | 4 | 5 | | V-2 | Pvr |
| 6234 | 3 | 4 | 5 | | V-2 | Pvrl3 |
| 6235 | 3 | 4 | 5 | | V-2 | Pwp1 |
| 6236 | 3 | 4 | 5 | | V-2 | Pwwp2a |
| 6237 | 3 | 4 | 5 | | V-2 | Pxdc1 |
| 6238 | 3 | 4 | 5 | | V-2 | Pxmp4 |
| 6239 | 3 | 4 | 5 | | V-2 | Pxylp1 |
| 6240 | 3 | 4 | 5 | | V-2 | Pycr1 |
| 6241 | 3 | 4 | 5 | | V-2 | Pygo1 |
| 6242 | 3 | 4 | 5 | | V-2 | R74862 |
| 6243 | 3 | 4 | 5 | | V-2 | Rab11fip4os2 |
| 6244 | 3 | 4 | 5 | | V-2 | Rab11fip5 |
| 6245 | 3 | 4 | 5 | | V-2 | Rab2b |
| 6246 | 3 | 4 | 5 | | V-2 | Rab30 |
| 6247 | 3 | 4 | 5 | | V-2 | Rab36 |
| 6248 | 3 | 4 | 5 | | V-2 | Rab3ip |
| 6249 | 3 | 4 | 5 | | V-2 | Rab40b |
| 6250 | 3 | 4 | 5 | | V-2 | Rab43 |
| 6251 | 3 | 4 | 5 | | V-2 | Rabep2 |
| 6252 | 3 | 4 | 5 | | V-2 | Rabggta |
| 6253 | 3 | 4 | 5 | | V-2 | Rabl6 |
| 6254 | 3 | 4 | 5 | | V-2 | Rac3 |
| 6255 | 3 | 4 | 5 | | V-2 | Rad1 |
| 6256 | 3 | 4 | 5 | | V-2 | Rad23a |
| 6257 | 3 | 4 | 5 | | V-2 | Rad51c |
| 6258 | 3 | 4 | 5 | | V-2 | Rad54l2 |
| 6259 | 3 | 4 | 5 | | V-2 | Rad9a |
| 6260 | 3 | 4 | 5 | | V-2 | Raet1d |
| 6261 | 3 | 4 | 5 | | V-2 | Ralgds |
| 6262 | 3 | 4 | 5 | | V-2 | Raly |
| 6263 | 3 | 4 | 5 | | V-2 | Ramp1 |
| 6264 | 3 | 4 | 5 | | V-2 | Ranbp3 |
| 6265 | 3 | 4 | 5 | | V-2 | Ranbp6 |
| 6266 | 3 | 4 | 5 | | V-2 | Rap1gap |
| 6267 | 3 | 4 | 5 | | V-2 | Rapgef2 |
| 6268 | 3 | 4 | 5 | | V-2 | Rapgef3 |
| 6269 | 3 | 4 | 5 | | V-2 | Rapgef4 |
| 6270 | 3 | 4 | 5 | | V-2 | Rarg |
| 6271 | 3 | 4 | 5 | | V-2 | Rasa2 |
| 6272 | 3 | 4 | 5 | | V-2 | Rasa3 |
| 6273 | 3 | 4 | 5 | | V-2 | Rasal3 |
| 6274 | 3 | 4 | 5 | | V-2 | Rasgrp3 |
| 6275 | 3 | 4 | 5 | | V-2 | Rasgrp4 |
| 6276 | 3 | 4 | 5 | | V-2 | Rasl10a |
| 6277 | 3 | 4 | 5 | | V-2 | Rasl2-9 |
| 6278 | 3 | 4 | 5 | | V-2 | Rassf2 |
| 6279 | 3 | 4 | 5 | | V-2 | Rassf4 |
| 6280 | 3 | 4 | 5 | | V-2 | Rassf6 |
| 6281 | 3 | 4 | 5 | | V-2 | Rb1cc1 |
| 6282 | 3 | 4 | 5 | | V-2 | Rbfox3 |
| 6283 | 3 | 4 | 5 | | V-2 | Rbm10 |
| 6284 | 3 | 4 | 5 | | V-2 | Rbm12b1 |
| 6285 | 3 | 4 | 5 | | V-2 | Rbm14 |
| 6286 | 3 | 4 | 5 | | V-2 | Rbm15b |
| 6287 | 3 | 4 | 5 | | V-2 | Rbm33 |
| 6288 | 3 | 4 | 5 | | V-2 | Rbm38 |

Fig. 43 - 38

| | | | | | | | |
|---|---|---|---|---|---|---|---|
| 6289 | 3 | 4 | 5 | | | V-2 | Rbm41 |
| 6290 | 3 | 4 | 5 | | | V-2 | Rbm5 |
| 6291 | 3 | 4 | 5 | | | V-2 | Rbm6 |
| 6292 | 3 | 4 | 5 | | | V-2 | Rbms3 |
| 6293 | 3 | 4 | 5 | | | V-2 | Rbpms |
| 6294 | 3 | 4 | 5 | | | V-2 | Rc3h1 |
| 6295 | 3 | 4 | 5 | | | V-2 | Rcc1 |
| 6296 | 3 | 4 | 5 | | | V-2 | Rcl1 |
| 6297 | 3 | 4 | 5 | | | V-2 | Rcor3 |
| 6298 | 3 | 4 | 5 | | | V-2 | Rdh11 |
| 6299 | 3 | 4 | 5 | | | V-2 | Rdh14 |
| 6300 | 3 | 4 | 5 | | | V-2 | Rdh16 |
| 6301 | 3 | 4 | 5 | | | V-2 | Rec8 |
| 6302 | 3 | 4 | 5 | | | V-2 | Rela |
| 6303 | 3 | 4 | 5 | | | V-2 | Reln |
| 6304 | 3 | 4 | 5 | | | V-2 | Rep15 |
| 6305 | 3 | 4 | 5 | | | V-2 | Reps2 |
| 6306 | 3 | 4 | 5 | | | V-2 | Rer1 |
| 6307 | 3 | 4 | 5 | | | V-2 | Rfx1 |
| 6308 | 3 | 4 | 5 | | | V-2 | Rfx3 |
| 6309 | 3 | 4 | 5 | | | V-2 | Rgag4 |
| 6310 | 3 | 4 | 5 | | | V-2 | Rgl3 |
| 6311 | 3 | 4 | 5 | | | V-2 | Rgs14 |
| 6312 | 3 | 4 | 5 | | | V-2 | Rgs19 |
| 6313 | 3 | 4 | 5 | | | V-2 | Rgs2 |
| 6314 | 3 | 4 | 5 | | | V-2 | Rgs22 |
| 6315 | 3 | 4 | 5 | | | V-2 | Rgs3 |
| 6316 | 3 | 4 | 5 | | | V-2 | Rgs7bp |
| 6317 | 3 | 4 | 5 | | | V-2 | Rgs9bp |
| 6318 | 3 | 4 | 5 | | | V-2 | Rhbdd3 |
| 6319 | 3 | 4 | 5 | | | V-2 | Rhbg |
| 6320 | 3 | 4 | 5 | | | V-2 | Rhd |
| 6321 | 3 | 4 | 5 | | | V-2 | Rhobtb2 |
| 6322 | 3 | 4 | 5 | | | V-2 | Rhoq |
| 6323 | 3 | 4 | 5 | | | V-2 | Rhox3g |
| 6324 | 3 | 4 | 5 | | | V-2 | Rhpn2 |
| 6325 | 3 | 4 | 5 | | | V-2 | Ric8 |
| 6326 | 3 | 4 | 5 | | | V-2 | Rictor |
| 6327 | 3 | 4 | 5 | | | V-2 | Rif1 |
| 6328 | 3 | 4 | 5 | | | V-2 | Riipl2 |
| 6329 | 3 | 4 | 5 | | | V-2 | Ripk1 |
| 6330 | 3 | 4 | 5 | | | V-2 | Ripk2 |
| 6331 | 3 | 4 | 5 | | | V-2 | Rit1 |
| 6332 | 3 | 4 | 5 | | | V-2 | Rita1 |
| 6333 | 3 | 4 | 5 | | | V-2 | Rmi2 |
| 6334 | 3 | 4 | 5 | | | V-2 | Rn45s |
| 6335 | 3 | 4 | 5 | | | V-2 | Rnd1 |
| 6336 | 3 | 4 | 5 | | | V-2 | Rnf10 |
| 6337 | 3 | 4 | 5 | | | V-2 | Rnf114 |
| 6338 | 3 | 4 | 5 | | | V-2 | Rnf126 |
| 6339 | 3 | 4 | 5 | | | V-2 | Rnf144a |
| 6340 | 3 | 4 | 5 | | | V-2 | Rnf152 |
| 6341 | 3 | 4 | 5 | | | V-2 | Rnf157 |
| 6342 | 3 | 4 | 5 | | | V-2 | Rnf167 |
| 6343 | 3 | 4 | 5 | | | V-2 | Rnf214 |
| 6344 | 3 | 4 | 5 | | | V-2 | Rnf25 |
| 6345 | 3 | 4 | 5 | | | V-2 | Rnf31 |
| 6346 | 3 | 4 | 5 | | | V-2 | Rnf39 |
| 6347 | 3 | 4 | 5 | | | V-2 | Rnpc3 |
| 6348 | 3 | 4 | 5 | | | V-2 | Rp9 |
| 6349 | 3 | 4 | 5 | | | V-2 | Rpa3 |
| 6350 | 3 | 4 | 5 | | | V-2 | Rpap3 |
| 6351 | 3 | 4 | 5 | | | V-2 | Rpf1 |
| 6352 | 3 | 4 | 5 | | | V-2 | Rpgr |
| 6353 | 3 | 4 | 5 | | | V-2 | Rpl13a |
| 6354 | 3 | 4 | 5 | | | V-2 | Rpl22 |
| 6355 | 3 | 4 | 5 | | | V-2 | Rpl23a |
| 6356 | 3 | 4 | 5 | | | V-2 | Rpl27a |
| 6357 | 3 | 4 | 5 | | | V-2 | Rpl31 |
| 6358 | 3 | 4 | 5 | | | V-2 | Rpl34-ps1 |
| 6359 | 3 | 4 | 5 | | | V-2 | Rpp40 |
| 6360 | 3 | 4 | 5 | | | V-2 | Rprd1a |
| 6361 | 3 | 4 | 5 | | | V-2 | Rprd2 |
| 6362 | 3 | 4 | 5 | | | V-2 | Rps10 |
| 6363 | 3 | 4 | 5 | | | V-2 | Rps11 |
| 6364 | 3 | 4 | 5 | | | V-2 | Rps15a-ps4 |
| 6365 | 3 | 4 | 5 | | | V-2 | Rps26 |
| 6366 | 3 | 4 | 5 | | | V-2 | Rps6kb1 |
| 6367 | 3 | 4 | 5 | | | V-2 | Rps6kl1 |
| 6368 | 3 | 4 | 5 | | | V-2 | Rptor |
| 6369 | 3 | 4 | 5 | | | V-2 | Rpusd1 |
| 6370 | 3 | 4 | 5 | | | V-2 | Rragb |
| 6371 | 3 | 4 | 5 | | | V-2 | Rras2 |
| 6372 | 3 | 4 | 5 | | | V-2 | Rrm2b |
| 6373 | 3 | 4 | 5 | | | V-2 | Rrp36 |
| 6374 | 3 | 4 | 5 | | | V-2 | Rrp7a |
| 6375 | 3 | 4 | 5 | | | V-2 | Rsbn1 |
| 6376 | 3 | 4 | 5 | | | V-2 | Rsl1 |
| 6377 | 3 | 4 | 5 | | | V-2 | Rsph3a |
| 6378 | 3 | 4 | 5 | | | V-2 | Rtkn |
| 6379 | 3 | 4 | 5 | | | V-2 | Rtkn2 |
| 6380 | 3 | 4 | 5 | | | V-2 | Rtn1 |
| 6381 | 3 | 4 | 5 | | | V-2 | Rttn |
| 6382 | 3 | 4 | 5 | | | V-2 | Rusc2 |
| 6383 | 3 | 4 | 5 | | | V-2 | Ruvbl1 |
| 6384 | 3 | 4 | 5 | | | V-2 | Rwdd1 |
| 6385 | 3 | 4 | 5 | | | V-2 | S1pr2 |
| 6386 | 3 | 4 | 5 | | | V-2 | S1pr4 |
| 6387 | 3 | 4 | 5 | | | V-2 | Sag |
| 6388 | 3 | 4 | 5 | | | V-2 | Sall1 |
| 6389 | 3 | 4 | 5 | | | V-2 | Samd10 |
| 6390 | 3 | 4 | 5 | | | V-2 | Samd12 |
| 6391 | 3 | 4 | 5 | | | V-2 | Samd4b |
| 6392 | 3 | 4 | 5 | | | V-2 | Samd9l |
| 6393 | 3 | 4 | 5 | | | V-2 | Samhd1 |
| 6394 | 3 | 4 | 5 | | | V-2 | Sap30l |
| 6395 | 3 | 4 | 5 | | | V-2 | Sapcd2 |
| 6396 | 3 | 4 | 5 | | | V-2 | Sart1 |
| 6397 | 3 | 4 | 5 | | | V-2 | Scai |
| 6398 | 3 | 4 | 5 | | | V-2 | Scamp3 |
| 6399 | 3 | 4 | 5 | | | V-2 | Scaper |
| 6400 | 3 | 4 | 5 | | | V-2 | Scarb1 |
| 6401 | 3 | 4 | 5 | | | V-2 | Sccpdh |
| 6402 | 3 | 4 | 5 | | | V-2 | Scd4 |
| 6403 | 3 | 4 | 5 | | | V-2 | Scg3 |
| 6404 | 3 | 4 | 5 | | | V-2 | Scn2b |
| 6405 | 3 | 4 | 5 | | | V-2 | Scn3a |
| 6406 | 3 | 4 | 5 | | | V-2 | Scrib |
| 6407 | 3 | 4 | 5 | | | V-2 | Sctr |
| 6408 | 3 | 4 | 5 | | | V-2 | Sdccag8 |
| 6409 | 3 | 4 | 5 | | | V-2 | Sec11a |
| 6410 | 3 | 4 | 5 | | | V-2 | Sec16a |
| 6411 | 3 | 4 | 5 | | | V-2 | Sec24b |
| 6412 | 3 | 4 | 5 | | | V-2 | Sec61g |
| 6413 | 3 | 4 | 5 | | | V-2 | Sema4b |
| 6414 | 3 | 4 | 5 | | | V-2 | Sema6a |
| 6415 | 3 | 4 | 5 | | | V-2 | Senp7 |
| 6416 | 3 | 4 | 5 | | | V-2 | Senp8 |
| 6417 | 3 | 4 | 5 | | | V-2 | Sept4 |
| 6418 | 3 | 4 | 5 | | | V-2 | Sept6 |
| 6419 | 3 | 4 | 5 | | | V-2 | Serac1 |
| 6420 | 3 | 4 | 5 | | | V-2 | Serpina11 |
| 6421 | 3 | 4 | 5 | | | V-2 | Serpina9 |
| 6422 | 3 | 4 | 5 | | | V-2 | Serpinb10 |
| 6423 | 3 | 4 | 5 | | | V-2 | Serpinb13 |
| 6424 | 3 | 4 | 5 | | | V-2 | Serpinb6a |
| 6425 | 3 | 4 | 5 | | | V-2 | Serpinb9 |
| 6426 | 3 | 4 | 5 | | | V-2 | Serpind1 |
| 6427 | 3 | 4 | 5 | | | V-2 | Serpini1 |
| 6428 | 3 | 4 | 5 | | | V-2 | Sesn1 |
| 6429 | 3 | 4 | 5 | | | V-2 | Setd1b |
| 6430 | 3 | 4 | 5 | | | V-2 | Sf3a2 |
| 6431 | 3 | 4 | 5 | | | V-2 | Sfi1 |
| 6432 | 3 | 4 | 5 | | | V-2 | Sfpq |
| 6433 | 3 | 4 | 5 | | | V-2 | Sgms1 |
| 6434 | 3 | 4 | 5 | | | V-2 | Sgpp2 |
| 6435 | 3 | 4 | 5 | | | V-2 | Sgsm2 |
| 6436 | 3 | 4 | 5 | | | V-2 | Sh2d2a |
| 6437 | 3 | 4 | 5 | | | V-2 | Sh2d4b |
| 6438 | 3 | 4 | 5 | | | V-2 | Sh3bgrl2 |
| 6439 | 3 | 4 | 5 | | | V-2 | Sh3d19 |
| 6440 | 3 | 4 | 5 | | | V-2 | Sh3gl2 |
| 6441 | 3 | 4 | 5 | | | V-2 | Sh3gl3 |
| 6442 | 3 | 4 | 5 | | | V-2 | Sh3tc1 |
| 6443 | 3 | 4 | 5 | | | V-2 | Shank3 |
| 6444 | 3 | 4 | 5 | | | V-2 | Shmt1 |
| 6445 | 3 | 4 | 5 | | | V-2 | Shprh |
| 6446 | 3 | 4 | 5 | | | V-2 | Shroom1 |
| 6447 | 3 | 4 | 5 | | | V-2 | Siah1b |
| 6448 | 3 | 4 | 5 | | | V-2 | Sigirr |
| 6449 | 3 | 4 | 5 | | | V-2 | Siglech |
| 6450 | 3 | 4 | 5 | | | V-2 | Sigmar1 |
| 6451 | 3 | 4 | 5 | | | V-2 | Sil1 |
| 6452 | 3 | 4 | 5 | | | V-2 | Simc1 |
| 6453 | 3 | 4 | 5 | | | V-2 | Sipa1l2 |
| 6454 | 3 | 4 | 5 | | | V-2 | Sirt2 |
| 6455 | 3 | 4 | 5 | | | V-2 | Skap1 |
| 6456 | 3 | 4 | 5 | | | V-2 | Skap2 |
| 6457 | 3 | 4 | 5 | | | V-2 | Sla |
| 6458 | 3 | 4 | 5 | | | V-2 | Slbp |

Fig. 43 - 39

| | | | | | | | | | | | | | | | | | | |
|---|---|---|---|---|---|---|---|---|---|---|---|---|---|---|---|---|---|---|
| 6459 | 3 | 4 | 5 | | | V-2 | Slc10a3 | | 6544 | 3 | 4 | 5 | | | V-2 | Smim13 | | |
| 6460 | 3 | 4 | 5 | | | V-2 | Slc12a6 | | 6545 | 3 | 4 | 5 | | | V-2 | Smox | | |
| 6461 | 3 | 4 | 5 | | | V-2 | Slc12a8 | | 6546 | 3 | 4 | 5 | | | V-2 | Smpd2 | | |
| 6462 | 3 | 4 | 5 | | | V-2 | Slc13a1 | | 6547 | 3 | 4 | 5 | | | V-2 | Smyd3 | | |
| 6463 | 3 | 4 | 5 | | | V-2 | Slc15a4 | | 6548 | 3 | 4 | 5 | | | V-2 | Snai1 | | |
| 6464 | 3 | 4 | 5 | | | V-2 | Slc17a1 | | 6549 | 3 | 4 | 5 | | | V-2 | Snap29 | | |
| 6465 | 3 | 4 | 5 | | | V-2 | Slc17a2 | | 6550 | 3 | 4 | 5 | | | V-2 | Snap91 | | |
| 6466 | 3 | 4 | 5 | | | V-2 | Slc17a5 | | 6551 | 3 | 4 | 5 | | | V-2 | Snapc1 | | |
| 6467 | 3 | 4 | 5 | | | V-2 | Slc18a2 | | 6552 | 3 | 4 | 5 | | | V-2 | Snapc2 | | |
| 6468 | 3 | 4 | 5 | | | V-2 | Slc1a2 | | 6553 | 3 | 4 | 5 | | | V-2 | Snapc3 | | |
| 6469 | 3 | 4 | 5 | | | V-2 | Slc22a26 | | 6554 | 3 | 4 | 5 | | | V-2 | Sncb | | |
| 6470 | 3 | 4 | 5 | | | V-2 | Slc22a5 | | 6555 | 3 | 4 | 5 | | | V-2 | Snrk | | |
| 6471 | 3 | 4 | 5 | | | V-2 | Slc24a5 | | 6556 | 3 | 4 | 5 | | | V-2 | Snrnp27 | | |
| 6472 | 3 | 4 | 5 | | | V-2 | Slc25a18 | | 6557 | 3 | 4 | 5 | | | V-2 | Snrnp35 | | |
| 6473 | 3 | 4 | 5 | | | V-2 | Slc25a19 | | 6558 | 3 | 4 | 5 | | | V-2 | Snrpa | | |
| 6474 | 3 | 4 | 5 | | | V-2 | Slc25a20 | | 6559 | 3 | 4 | 5 | | | V-2 | Snx1 | | |
| 6475 | 3 | 4 | 5 | | | V-2 | Slc25a23 | | 6560 | 3 | 4 | 5 | | | V-2 | Snx15 | | |
| 6476 | 3 | 4 | 5 | | | V-2 | Slc25a26 | | 6561 | 3 | 4 | 5 | | | V-2 | Snx16 | | |
| 6477 | 3 | 4 | 5 | | | V-2 | Slc25a30 | | 6562 | 3 | 4 | 5 | | | V-2 | Snx17 | | |
| 6478 | 3 | 4 | 5 | | | V-2 | Slc25a32 | | 6563 | 3 | 4 | 5 | | | V-2 | Snx2 | | |
| 6479 | 3 | 4 | 5 | | | V-2 | Slc25a39 | | 6564 | 3 | 4 | 5 | | | V-2 | Snx21 | | |
| 6480 | 3 | 4 | 5 | | | V-2 | Slc25a45 | | 6565 | 3 | 4 | 5 | | | V-2 | Snx25 | | |
| 6481 | 3 | 4 | 5 | | | V-2 | Slc25a51 | | 6566 | 3 | 4 | 5 | | | V-2 | Snx3 | | |
| 6482 | 3 | 4 | 5 | | | V-2 | Slc26a1 | | 6567 | 3 | 4 | 5 | | | V-2 | Snx32 | | |
| 6483 | 3 | 4 | 5 | | | V-2 | Slc26a10 | | 6568 | 3 | 4 | 5 | | | V-2 | Snx6 | | |
| 6484 | 3 | 4 | 5 | | | V-2 | Slc26a11 | | 6569 | 3 | 4 | 5 | | | V-2 | Snx8 | | |
| 6485 | 3 | 4 | 5 | | | V-2 | Slc27a1 | | 6570 | 3 | 4 | 5 | | | V-2 | Soat1 | | |
| 6486 | 3 | 4 | 5 | | | V-2 | Slc28a2 | | 6571 | 3 | 4 | 5 | | | V-2 | Socs7 | | |
| 6487 | 3 | 4 | 5 | | | V-2 | Slc29a2 | | 6572 | 3 | 4 | 5 | | | V-2 | Sod1 | | |
| 6488 | 3 | 4 | 5 | | | V-2 | Slc2a10 | | 6573 | 3 | 4 | 5 | | | V-2 | Soga1 | | |
| 6489 | 3 | 4 | 5 | | | V-2 | Slc2a13 | | 6574 | 3 | 4 | 5 | | | V-2 | Sorbs3 | | |
| 6490 | 3 | 4 | 5 | | | V-2 | Slc2a4rg-ps | | 6575 | 3 | 4 | 5 | | | V-2 | Sorcs2 | | |
| 6491 | 3 | 4 | 5 | | | V-2 | Slc2a5 | | 6576 | 3 | 4 | 5 | | | V-2 | Sord | | |
| 6492 | 3 | 4 | 5 | | | V-2 | Slc30a1 | | 6577 | 3 | 4 | 5 | | | V-2 | Sort1 | | |
| 6493 | 3 | 4 | 5 | | | V-2 | Slc30a10 | | 6578 | 3 | 4 | 5 | | | V-2 | Sowahc | | |
| 6494 | 3 | 4 | 5 | | | V-2 | Slc30a4 | | 6579 | 3 | 4 | 5 | | | V-2 | Sox18 | | |
| 6495 | 3 | 4 | 5 | | | V-2 | Slc35b2 | | 6580 | 3 | 4 | 5 | | | V-2 | Sox5 | | |
| 6496 | 3 | 4 | 5 | | | V-2 | Slc35c2 | | 6581 | 3 | 4 | 5 | | | V-2 | Sox6 | | |
| 6497 | 3 | 4 | 5 | | | V-2 | Slc35d3 | | 6582 | 3 | 4 | 5 | | | V-2 | Sp1 | | |
| 6498 | 3 | 4 | 5 | | | V-2 | Slc35e2 | | 6583 | 3 | 4 | 5 | | | V-2 | Sp5 | | |
| 6499 | 3 | 4 | 5 | | | V-2 | Slc35f5 | | 6584 | 3 | 4 | 5 | | | V-2 | Spaca1 | | |
| 6500 | 3 | 4 | 5 | | | V-2 | Slc35g2 | | 6585 | 3 | 4 | 5 | | | V-2 | Spag1 | | |
| 6501 | 3 | 4 | 5 | | | V-2 | Slc37a1 | | 6586 | 3 | 4 | 5 | | | V-2 | Spag11a | | |
| 6502 | 3 | 4 | 5 | | | V-2 | Slc37a4 | | 6587 | 3 | 4 | 5 | | | V-2 | Spag16 | | |
| 6503 | 3 | 4 | 5 | | | V-2 | Slc38a10 | | 6588 | 3 | 4 | 5 | | | V-2 | Spag17 | | |
| 6504 | 3 | 4 | 5 | | | V-2 | Slc38a2 | | 6589 | 3 | 4 | 5 | | | V-2 | Spag8 | | |
| 6505 | 3 | 4 | 5 | | | V-2 | Slc38a9 | | 6590 | 3 | 4 | 5 | | | V-2 | Sparcl1 | | |
| 6506 | 3 | 4 | 5 | | | V-2 | Slc39a5 | | 6591 | 3 | 4 | 5 | | | V-2 | Spata16 | | |
| 6507 | 3 | 4 | 5 | | | V-2 | Slc39a6 | | 6592 | 3 | 4 | 5 | | | V-2 | Spata45 | | |
| 6508 | 3 | 4 | 5 | | | V-2 | Slc39a9 | | 6593 | 3 | 4 | 5 | | | V-2 | Spata9 | | |
| 6509 | 3 | 4 | 5 | | | V-2 | Slc3a2 | | 6594 | 3 | 4 | 5 | | | V-2 | Spdl1 | | |
| 6510 | 3 | 4 | 5 | | | V-2 | Slc40a1 | | 6595 | 3 | 4 | 5 | | | V-2 | Specc1 | | |
| 6511 | 3 | 4 | 5 | | | V-2 | Slc41a1 | | 6596 | 3 | 4 | 5 | | | V-2 | Speer1-ps1 | | |
| 6512 | 3 | 4 | 5 | | | V-2 | Slc45a3 | | 6597 | 3 | 4 | 5 | | | V-2 | Spg11 | | |
| 6513 | 3 | 4 | 5 | | | V-2 | Slc45a4 | | 6598 | 3 | 4 | 5 | | | V-2 | Spice1 | | |
| 6514 | 3 | 4 | 5 | | | V-2 | Slc46a1 | | 6599 | 3 | 4 | 5 | | | V-2 | Spint5 | | |
| 6515 | 3 | 4 | 5 | | | V-2 | Slc4a1 | | 6600 | 3 | 4 | 5 | | | V-2 | Spn-ps | | |
| 6516 | 3 | 4 | 5 | | | V-2 | Slc4a8 | | 6601 | 3 | 4 | 5 | | | V-2 | Spns1 | | |
| 6517 | 3 | 4 | 5 | | | V-2 | Slc51b | | 6602 | 3 | 4 | 5 | | | V-2 | Spr | | |
| 6518 | 3 | 4 | 5 | | | V-2 | Slc52a3 | | 6603 | 3 | 4 | 5 | | | V-2 | Sprr2a2 | | |
| 6519 | 3 | 4 | 5 | | | V-2 | Slc5a10 | | 6604 | 3 | 4 | 5 | | | V-2 | Spsb2 | | |
| 6520 | 3 | 4 | 5 | | | V-2 | Slc5a2 | | 6605 | 3 | 4 | 5 | | | V-2 | Sptlc1 | | |
| 6521 | 3 | 4 | 5 | | | V-2 | Slc5a3 | | 6606 | 3 | 4 | 5 | | | V-2 | Src | | |
| 6522 | 3 | 4 | 5 | | | V-2 | Slc5a7 | | 6607 | 3 | 4 | 5 | | | V-2 | Srd5a2 | | |
| 6523 | 3 | 4 | 5 | | | V-2 | Slc6a2 | | 6608 | 3 | 4 | 5 | | | V-2 | Srf | | |
| 6524 | 3 | 4 | 5 | | | V-2 | Slc6a20a | | 6609 | 3 | 4 | 5 | | | V-2 | Srgap2 | | |
| 6525 | 3 | 4 | 5 | | | V-2 | Slc6a4 | | 6610 | 3 | 4 | 5 | | | V-2 | Srpk1 | | |
| 6526 | 3 | 4 | 5 | | | V-2 | Slc7a6 | | 6611 | 3 | 4 | 5 | | | V-2 | Srsf7 | | |
| 6527 | 3 | 4 | 5 | | | V-2 | Slc7a7 | | 6612 | 3 | 4 | 5 | | | V-2 | Ssbp1 | | |
| 6528 | 3 | 4 | 5 | | | V-2 | Slc7a8 | | 6613 | 3 | 4 | 5 | | | V-2 | Ssbp2 | | |
| 6529 | 3 | 4 | 5 | | | V-2 | Slc7a9 | | 6614 | 3 | 4 | 5 | | | V-2 | Sstr4 | | |
| 6530 | 3 | 4 | 5 | | | V-2 | Slc9a7 | | 6615 | 3 | 4 | 5 | | | V-2 | Ssxb2 | | |
| 6531 | 3 | 4 | 5 | | | V-2 | Slc9a9 | | 6616 | 3 | 4 | 5 | | | V-2 | St13 | | |
| 6532 | 3 | 4 | 5 | | | V-2 | Slfn5os | | 6617 | 3 | 4 | 5 | | | V-2 | St14 | | |
| 6533 | 3 | 4 | 5 | | | V-2 | Slit2 | | 6618 | 3 | 4 | 5 | | | V-2 | St18 | | |
| 6534 | 3 | 4 | 5 | | | V-2 | Slitrk6 | | 6619 | 3 | 4 | 5 | | | V-2 | St3gal2 | | |
| 6535 | 3 | 4 | 5 | | | V-2 | Slmap | | 6620 | 3 | 4 | 5 | | | V-2 | St3gal6 | | |
| 6536 | 3 | 4 | 5 | | | V-2 | Six1b | | 6621 | 3 | 4 | 5 | | | V-2 | St6galnac3 | | |
| 6537 | 3 | 4 | 5 | | | V-2 | Six4ip | | 6622 | 3 | 4 | 5 | | | V-2 | St8sia2 | | |
| 6538 | 3 | 4 | 5 | | | V-2 | Smarca4 | | 6623 | 3 | 4 | 5 | | | V-2 | St8sia4 | | |
| 6539 | 3 | 4 | 5 | | | V-2 | Smarcd2 | | 6624 | 3 | 4 | 5 | | | V-2 | Stag2 | | |
| 6540 | 3 | 4 | 5 | | | V-2 | Smc2os | | 6625 | 3 | 4 | 5 | | | V-2 | Stambp | | |
| 6541 | 3 | 4 | 5 | | | V-2 | Smc4 | | 6626 | 3 | 4 | 5 | | | V-2 | Stambpl1 | | |
| 6542 | 3 | 4 | 5 | | | V-2 | Smco4 | | 6627 | 3 | 4 | 5 | | | V-2 | Star | | |
| 6543 | 3 | 4 | 5 | | | V-2 | Smg1 | | 6628 | 3 | 4 | 5 | | | V-2 | Stard13 | | |

Fig. 43 - 40

| | | | | | | | | |
|---|---|---|---|---|---|---|---|---|
| 6629 | 3 | 4 | 5 | | | V-2 | Stard3nl |
| 6630 | 3 | 4 | 5 | | | V-2 | Stat1 |
| 6631 | 3 | 4 | 5 | | | V-2 | Stat5b |
| 6632 | 3 | 4 | 5 | | | V-2 | Stim1 |
| 6633 | 3 | 4 | 5 | | | V-2 | Stk16 |
| 6634 | 3 | 4 | 5 | | | V-2 | Stk33 |
| 6635 | 3 | 4 | 5 | | | V-2 | Stk38l |
| 6636 | 3 | 4 | 5 | | | V-2 | Stk40 |
| 6637 | 3 | 4 | 5 | | | V-2 | Stmn1 |
| 6638 | 3 | 4 | 5 | | | V-2 | Stmn3 |
| 6639 | 3 | 4 | 5 | | | V-2 | Ston2 |
| 6640 | 3 | 4 | 5 | | | V-2 | Stox1 |
| 6641 | 3 | 4 | 5 | | | V-2 | Stox2 |
| 6642 | 3 | 4 | 5 | | | V-2 | Stpg1 |
| 6643 | 3 | 4 | 5 | | | V-2 | Stra13 |
| 6644 | 3 | 4 | 5 | | | V-2 | Stradb |
| 6645 | 3 | 4 | 5 | | | V-2 | Strbp |
| 6646 | 3 | 4 | 5 | | | V-2 | Stx18 |
| 6647 | 3 | 4 | 5 | | | V-2 | Stx1a |
| 6648 | 3 | 4 | 5 | | | V-2 | Stx5a |
| 6649 | 3 | 4 | 5 | | | V-2 | Stx6 |
| 6650 | 3 | 4 | 5 | | | V-2 | Stxbp1 |
| 6651 | 3 | 4 | 5 | | | V-2 | Stxbp3a |
| 6652 | 3 | 4 | 5 | | | V-2 | Stxbp4 |
| 6653 | 3 | 4 | 5 | | | V-2 | Suclg2 |
| 6654 | 3 | 4 | 5 | | | V-2 | Suds3 |
| 6655 | 3 | 4 | 5 | | | V-2 | Sufu |
| 6656 | 3 | 4 | 5 | | | V-2 | Sugp2 |
| 6657 | 3 | 4 | 5 | | | V-2 | Sult1a1 |
| 6658 | 3 | 4 | 5 | | | V-2 | Sumf2 |
| 6659 | 3 | 4 | 5 | | | V-2 | Sumo2 |
| 6660 | 3 | 4 | 5 | | | V-2 | Sun2 |
| 6661 | 3 | 4 | 5 | | | V-2 | Suox |
| 6662 | 3 | 4 | 5 | | | V-2 | Supt3 |
| 6663 | 3 | 4 | 5 | | | V-2 | Suv420h1 |
| 6664 | 3 | 4 | 5 | | | V-2 | Svs5 |
| 6665 | 3 | 4 | 5 | | | V-2 | Swi5 |
| 6666 | 3 | 4 | 5 | | | V-2 | Swt1 |
| 6667 | 3 | 4 | 5 | | | V-2 | Sybu |
| 6668 | 3 | 4 | 5 | | | V-2 | Syce1 |
| 6669 | 3 | 4 | 5 | | | V-2 | Sycp3 |
| 6670 | 3 | 4 | 5 | | | V-2 | Syne2 |
| 6671 | 3 | 4 | 5 | | | V-2 | Synj2bp |
| 6672 | 3 | 4 | 5 | | | V-2 | Synrg |
| 6673 | 3 | 4 | 5 | | | V-2 | Syt11 |
| 6674 | 3 | 4 | 5 | | | V-2 | Syt7 |
| 6675 | 3 | 4 | 5 | | | V-2 | Sytl2 |
| 6676 | 3 | 4 | 5 | | | V-2 | Syvn1 |
| 6677 | 3 | 4 | 5 | | | V-2 | Tab1 |
| 6678 | 3 | 4 | 5 | | | V-2 | Tacc1 |
| 6679 | 3 | 4 | 5 | | | V-2 | Tada3 |
| 6680 | 3 | 4 | 5 | | | V-2 | Taf10 |
| 6681 | 3 | 4 | 5 | | | V-2 | Taf11 |
| 6682 | 3 | 4 | 5 | | | V-2 | Taf12 |
| 6683 | 3 | 4 | 5 | | | V-2 | Taf1c |
| 6684 | 3 | 4 | 5 | | | V-2 | Taf5 |
| 6685 | 3 | 4 | 5 | | | V-2 | Taf6 |
| 6686 | 3 | 4 | 5 | | | V-2 | Tanc2 |
| 6687 | 3 | 4 | 5 | | | V-2 | Taok2 |
| 6688 | 3 | 4 | 5 | | | V-2 | Tax1bp1 |
| 6689 | 3 | 4 | 5 | | | V-2 | Taz |
| 6690 | 3 | 4 | 5 | | | V-2 | Tbata |
| 6691 | 3 | 4 | 5 | | | V-2 | Tbc1d16 |
| 6692 | 3 | 4 | 5 | | | V-2 | Tbc1d19 |
| 6693 | 3 | 4 | 5 | | | V-2 | Tbc1d20 |
| 6694 | 3 | 4 | 5 | | | V-2 | Tbc1d25 |
| 6695 | 3 | 4 | 5 | | | V-2 | Tbc1d4 |
| 6696 | 3 | 4 | 5 | | | V-2 | Tbc1d8 |
| 6697 | 3 | 4 | 5 | | | V-2 | Tbc1d9b |
| 6698 | 3 | 4 | 5 | | | V-2 | Tbxas1 |
| 6699 | 3 | 4 | 5 | | | V-2 | Tceal1 |
| 6700 | 3 | 4 | 5 | | | V-2 | Tceanc2 |
| 6701 | 3 | 4 | 5 | | | V-2 | Tcf12 |
| 6702 | 3 | 4 | 5 | | | V-2 | Tcf15 |
| 6703 | 3 | 4 | 5 | | | V-2 | Tcf3 |
| 6704 | 3 | 4 | 5 | | | V-2 | Tcn2 |
| 6705 | 3 | 4 | 5 | | | V-2 | Tcof1 |
| 6706 | 3 | 4 | 5 | | | V-2 | Tcp10b |
| 6707 | 3 | 4 | 5 | | | V-2 | Tcp10c |
| 6708 | 3 | 4 | 5 | | | V-2 | Tcp11l2 |
| 6709 | 3 | 4 | 5 | | | V-2 | Tcta |
| 6710 | 3 | 4 | 5 | | | V-2 | Tdp1 |
| 6711 | 3 | 4 | 5 | | | V-2 | Tdp2 |
| 6712 | 3 | 4 | 5 | | | V-2 | Tdrd3 |
| 6713 | 3 | 4 | 5 | | | V-2 | Tdrp |
| 6714 | 3 | 4 | 5 | | | V-2 | Tead1 |
| 6715 | 3 | 4 | 5 | | | V-2 | Tec |
| 6716 | 3 | 4 | 5 | | | V-2 | Tecpr1 |
| 6717 | 3 | 4 | 5 | | | V-2 | Tecpr2 |
| 6718 | 3 | 4 | 5 | | | V-2 | Tefm |
| 6719 | 3 | 4 | 5 | | | V-2 | Tekt4 |
| 6720 | 3 | 4 | 5 | | | V-2 | Ten1 |
| 6721 | 3 | 4 | 5 | | | V-2 | Tep1 |
| 6722 | 3 | 4 | 5 | | | V-2 | Terf1 |
| 6723 | 3 | 4 | 5 | | | V-2 | Terf2ip |
| 6724 | 3 | 4 | 5 | | | V-2 | Tesk1 |
| 6725 | 3 | 4 | 5 | | | V-2 | Tespa1 |
| 6726 | 3 | 4 | 5 | | | V-2 | Tet1 |
| 6727 | 3 | 4 | 5 | | | V-2 | Tet3 |
| 6728 | 3 | 4 | 5 | | | V-2 | Tex15 |
| 6729 | 3 | 4 | 5 | | | V-2 | Tex264 |
| 6730 | 3 | 4 | 5 | | | V-2 | Tex36 |
| 6731 | 3 | 4 | 5 | | | V-2 | Tex37 |
| 6732 | 3 | 4 | 5 | | | V-2 | Tex9 |
| 6733 | 3 | 4 | 5 | | | V-2 | Tfb2m |
| 6734 | 3 | 4 | 5 | | | V-2 | Tfcp2 |
| 6735 | 3 | 4 | 5 | | | V-2 | Tfdp2 |
| 6736 | 3 | 4 | 5 | | | V-2 | Tfeb |
| 6737 | 3 | 4 | 5 | | | V-2 | Tgfa |
| 6738 | 3 | 4 | 5 | | | V-2 | Tgif1 |
| 6739 | 3 | 4 | 5 | | | V-2 | Tha1 |
| 6740 | 3 | 4 | 5 | | | V-2 | Thada |
| 6741 | 3 | 4 | 5 | | | V-2 | Thap11 |
| 6742 | 3 | 4 | 5 | | | V-2 | Thap3 |
| 6743 | 3 | 4 | 5 | | | V-2 | Thap4 |
| 6744 | 3 | 4 | 5 | | | V-2 | Thap7 |
| 6745 | 3 | 4 | 5 | | | V-2 | Them4 |
| 6746 | 3 | 4 | 5 | | | V-2 | Thnsl2 |
| 6747 | 3 | 4 | 5 | | | V-2 | Thrb |
| 6748 | 3 | 4 | 5 | | | V-2 | Thsd1 |
| 6749 | 3 | 4 | 5 | | | V-2 | Tia1 |
| 6750 | 3 | 4 | 5 | | | V-2 | Tiam2 |
| 6751 | 3 | 4 | 5 | | | V-2 | Timm44 |
| 6752 | 3 | 4 | 5 | | | V-2 | Tinagl1 |
| 6753 | 3 | 4 | 5 | | | V-2 | Tldc1 |
| 6754 | 3 | 4 | 5 | | | V-2 | Tlk2 |
| 6755 | 3 | 4 | 5 | | | V-2 | Tlr12 |
| 6756 | 3 | 4 | 5 | | | V-2 | Tm4sf20 |
| 6757 | 3 | 4 | 5 | | | V-2 | Tm4sf4 |
| 6758 | 3 | 4 | 5 | | | V-2 | Tm7sf2 |
| 6759 | 3 | 4 | 5 | | | V-2 | Tmbim1 |
| 6760 | 3 | 4 | 5 | | | V-2 | Tmc4 |
| 6761 | 3 | 4 | 5 | | | V-2 | Tmc5 |
| 6762 | 3 | 4 | 5 | | | V-2 | Tmcc1 |
| 6763 | 3 | 4 | 5 | | | V-2 | Tmco1 |
| 6764 | 3 | 4 | 5 | | | V-2 | Tmco6 |
| 6765 | 3 | 4 | 5 | | | V-2 | Tmed3 |
| 6766 | 3 | 4 | 5 | | | V-2 | Tmed8 |
| 6767 | 3 | 4 | 5 | | | V-2 | Tmeff1 |
| 6768 | 3 | 4 | 5 | | | V-2 | Tmem106b |
| 6769 | 3 | 4 | 5 | | | V-2 | Tmem115 |
| 6770 | 3 | 4 | 5 | | | V-2 | Tmem132d |
| 6771 | 3 | 4 | 5 | | | V-2 | Tmem134 |
| 6772 | 3 | 4 | 5 | | | V-2 | Tmem138 |
| 6773 | 3 | 4 | 5 | | | V-2 | Tmem144 |
| 6774 | 3 | 4 | 5 | | | V-2 | Tmem161a |
| 6775 | 3 | 4 | 5 | | | V-2 | Tmem180 |
| 6776 | 3 | 4 | 5 | | | V-2 | Tmem181b-ps |
| 6777 | 3 | 4 | 5 | | | V-2 | Tmem181c-ps |
| 6778 | 3 | 4 | 5 | | | V-2 | Tmem184a |
| 6779 | 3 | 4 | 5 | | | V-2 | Tmem191c |
| 6780 | 3 | 4 | 5 | | | V-2 | Tmem194b |
| 6781 | 3 | 4 | 5 | | | V-2 | Tmem200a |
| 6782 | 3 | 4 | 5 | | | V-2 | Tmem202 |
| 6783 | 3 | 4 | 5 | | | V-2 | Tmem206 |
| 6784 | 3 | 4 | 5 | | | V-2 | Tmem221 |
| 6785 | 3 | 4 | 5 | | | V-2 | Tmem231 |
| 6786 | 3 | 4 | 5 | | | V-2 | Tmem237 |
| 6787 | 3 | 4 | 5 | | | V-2 | Tmem44 |
| 6788 | 3 | 4 | 5 | | | V-2 | Tmem50a |
| 6789 | 3 | 4 | 5 | | | V-2 | Tmem55a |
| 6790 | 3 | 4 | 5 | | | V-2 | Tmem66 |
| 6791 | 3 | 4 | 5 | | | V-2 | Tmem70 |
| 6792 | 3 | 4 | 5 | | | V-2 | Tmem71 |
| 6793 | 3 | 4 | 5 | | | V-2 | Tmem81 |
| 6794 | 3 | 4 | 5 | | | V-2 | Tmem87a |
| 6795 | 3 | 4 | 5 | | | V-2 | Tmppe |
| 6796 | 3 | 4 | 5 | | | V-2 | Tmprss2 |
| 6797 | 3 | 4 | 5 | | | V-2 | Tmtc2 |
| 6798 | 3 | 4 | 5 | | | V-2 | Tmtc3 |

Fig. 43 - 41

| | | | | | | | |
|---|---|---|---|---|---|---|---|
| 6799 | 3 | 4 | 5 | | | V-2 | Tmtc4 |
| 6800 | 3 | 4 | 5 | | | V-2 | Tmub1 |
| 6801 | 3 | 4 | 5 | | | V-2 | Tnf |
| 6802 | 3 | 4 | 5 | | | V-2 | Tnfaip8 |
| 6803 | 3 | 4 | 5 | | | V-2 | Tnfaip8l2 |
| 6804 | 3 | 4 | 5 | | | V-2 | Tnfrsf8 |
| 6805 | 3 | 4 | 5 | | | V-2 | Tnfsf11 |
| 6806 | 3 | 4 | 5 | | | V-2 | Tnik |
| 6807 | 3 | 4 | 5 | | | V-2 | Tnip1 |
| 6808 | 3 | 4 | 5 | | | V-2 | Tnpo2 |
| 6809 | 3 | 4 | 5 | | | V-2 | Tnrc18 |
| 6810 | 3 | 4 | 5 | | | V-2 | Tnrc6a |
| 6811 | 3 | 4 | 5 | | | V-2 | Tnrc6c |
| 6812 | 3 | 4 | 5 | | | V-2 | Tns1 |
| 6813 | 3 | 4 | 5 | | | V-2 | Tom1 |
| 6814 | 3 | 4 | 5 | | | V-2 | Tom1l2 |
| 6815 | 3 | 4 | 5 | | | V-2 | Tomt |
| 6816 | 3 | 4 | 5 | | | V-2 | Top2b |
| 6817 | 3 | 4 | 5 | | | V-2 | Tor2a |
| 6818 | 3 | 4 | 5 | | | V-2 | Tox3 |
| 6819 | 3 | 4 | 5 | | | V-2 | Tpcn1 |
| 6820 | 3 | 4 | 5 | | | V-2 | Tpmt |
| 6821 | 3 | 4 | 5 | | | V-2 | Tppp |
| 6822 | 3 | 4 | 5 | | | V-2 | Tpr |
| 6823 | 3 | 4 | 5 | | | V-2 | Tprgl |
| 6824 | 3 | 4 | 5 | | | V-2 | Tprkb |
| 6825 | 3 | 4 | 5 | | | V-2 | Tpsab1 |
| 6826 | 3 | 4 | 5 | | | V-2 | Tpsb2 |
| 6827 | 3 | 4 | 5 | | | V-2 | Tpst2 |
| 6828 | 3 | 4 | 5 | | | V-2 | Tra2a |
| 6829 | 3 | 4 | 5 | | | V-2 | Trabd |
| 6830 | 3 | 4 | 5 | | | V-2 | Tradd |
| 6831 | 3 | 4 | 5 | | | V-2 | Traf1 |
| 6832 | 3 | 4 | 5 | | | V-2 | Traf3ip2 |
| 6833 | 3 | 4 | 5 | | | V-2 | Traf3ip3 |
| 6834 | 3 | 4 | 5 | | | V-2 | Trappc2 |
| 6835 | 3 | 4 | 5 | | | V-2 | Trappc5 |
| 6836 | 3 | 4 | 5 | | | V-2 | Triap1 |
| 6837 | 3 | 4 | 5 | | | V-2 | Tril |
| 6838 | 3 | 4 | 5 | | | V-2 | Trim10 |
| 6839 | 3 | 4 | 5 | | | V-2 | Trim11 |
| 6840 | 3 | 4 | 5 | | | V-2 | Trim26 |
| 6841 | 3 | 4 | 5 | | | V-2 | Trim28 |
| 6842 | 3 | 4 | 5 | | | V-2 | Trim37 |
| 6843 | 3 | 4 | 5 | | | V-2 | Trim38 |
| 6844 | 3 | 4 | 5 | | | V-2 | Trim39 |
| 6845 | 3 | 4 | 5 | | | V-2 | Trim58 |
| 6846 | 3 | 4 | 5 | | | V-2 | Trim61 |
| 6847 | 3 | 4 | 5 | | | V-2 | Trim62 |
| 6848 | 3 | 4 | 5 | | | V-2 | Trio |
| 6849 | 3 | 4 | 5 | | | V-2 | Trip10 |
| 6850 | 3 | 4 | 5 | | | V-2 | Trip6 |
| 6851 | 3 | 4 | 5 | | | V-2 | Trit1 |
| 6852 | 3 | 4 | 5 | | | V-2 | Trmt1 |
| 6853 | 3 | 4 | 5 | | | V-2 | Trmt10b |
| 6854 | 3 | 4 | 5 | | | V-2 | Trmt1l |
| 6855 | 3 | 4 | 5 | | | V-2 | Trmt44 |
| 6856 | 3 | 4 | 5 | | | V-2 | Trmt5 |
| 6857 | 3 | 4 | 5 | | | V-2 | Trmt61a |
| 6858 | 3 | 4 | 5 | | | V-2 | Trnt1 |
| 6859 | 3 | 4 | 5 | | | V-2 | Tro |
| 6860 | 3 | 4 | 5 | | | V-2 | Trp53 |
| 6861 | 3 | 4 | 5 | | | V-2 | Trp53bp1 |
| 6862 | 3 | 4 | 5 | | | V-2 | Trp53tg5 |
| 6863 | 3 | 4 | 5 | | | V-2 | Trpc2 |
| 6864 | 3 | 4 | 5 | | | V-2 | Trpc4ap |
| 6865 | 3 | 4 | 5 | | | V-2 | Trpm8 |
| 6866 | 3 | 4 | 5 | | | V-2 | Trps1 |
| 6867 | 3 | 4 | 5 | | | V-2 | Trpv4 |
| 6868 | 3 | 4 | 5 | | | V-2 | Tsc1 |
| 6869 | 3 | 4 | 5 | | | V-2 | Tsc22d3 |
| 6870 | 3 | 4 | 5 | | | V-2 | Tsen34 |
| 6871 | 3 | 4 | 5 | | | V-2 | Tsen54 |
| 6872 | 3 | 4 | 5 | | | V-2 | Tsga10 |
| 6873 | 3 | 4 | 5 | | | V-2 | Tshz2 |
| 6874 | 3 | 4 | 5 | | | V-2 | Tshz3 |
| 6875 | 3 | 4 | 5 | | | V-2 | Tsks |
| 6876 | 3 | 4 | 5 | | | V-2 | Tspan10 |
| 6877 | 3 | 4 | 5 | | | V-2 | Tspan13 |
| 6878 | 3 | 4 | 5 | | | V-2 | Tspan2 |
| 6879 | 3 | 4 | 5 | | | V-2 | Tspan33 |
| 6880 | 3 | 4 | 5 | | | V-2 | Tspo2 |
| 6881 | 3 | 4 | 5 | | | V-2 | Tspyl5 |
| 6882 | 3 | 4 | 5 | | | V-2 | Tsr1 |
| 6883 | 3 | 4 | 5 | | | V-2 | Tssk4 |
| 6884 | 3 | 4 | 5 | | | V-2 | Ttbk2 |
| 6885 | 3 | 4 | 5 | | | V-2 | Ttc14 |
| 6886 | 3 | 4 | 5 | | | V-2 | Ttc16 |
| 6887 | 3 | 4 | 5 | | | V-2 | Ttc18 |
| 6888 | 3 | 4 | 5 | | | V-2 | Ttc21b |
| 6889 | 3 | 4 | 5 | | | V-2 | Ttc3 |
| 6890 | 3 | 4 | 5 | | | V-2 | Ttc30b |
| 6891 | 3 | 4 | 5 | | | V-2 | Ttc32 |
| 6892 | 3 | 4 | 5 | | | V-2 | Ttc37 |
| 6893 | 3 | 4 | 5 | | | V-2 | Ttc39d |
| 6894 | 3 | 4 | 5 | | | V-2 | Ttf1 |
| 6895 | 3 | 4 | 5 | | | V-2 | Tti1 |
| 6896 | 3 | 4 | 5 | | | V-2 | Ttll3 |
| 6897 | 3 | 4 | 5 | | | V-2 | Ttll5 |
| 6898 | 3 | 4 | 5 | | | V-2 | Ttpal |
| 6899 | 3 | 4 | 5 | | | V-2 | Tubb4a |
| 6900 | 3 | 4 | 5 | | | V-2 | Tubgcp4 |
| 6901 | 3 | 4 | 5 | | | V-2 | Tulp3 |
| 6902 | 3 | 4 | 5 | | | V-2 | Tusc2 |
| 6903 | 3 | 4 | 5 | | | V-2 | Tusc5 |
| 6904 | 3 | 4 | 5 | | | V-2 | Txk |
| 6905 | 3 | 4 | 5 | | | V-2 | Txlng |
| 6906 | 3 | 4 | 5 | | | V-2 | Txndc15 |
| 6907 | 3 | 4 | 5 | | | V-2 | Txndc5 |
| 6908 | 3 | 4 | 5 | | | V-2 | Txnip |
| 6909 | 3 | 4 | 5 | | | V-2 | Tymp |
| 6910 | 3 | 4 | 5 | | | V-2 | Tyw3 |
| 6911 | 3 | 4 | 5 | | | V-2 | Tyw5 |
| 6912 | 3 | 4 | 5 | | | V-2 | U2af1l4 |
| 6913 | 3 | 4 | 5 | | | V-2 | Uba6 |
| 6914 | 3 | 4 | 5 | | | V-2 | Uba7 |
| 6915 | 3 | 4 | 5 | | | V-2 | Ubac1 |
| 6916 | 3 | 4 | 5 | | | V-2 | Ubald1 |
| 6917 | 3 | 4 | 5 | | | V-2 | Ubash3a |
| 6918 | 3 | 4 | 5 | | | V-2 | Ube2a |
| 6919 | 3 | 4 | 5 | | | V-2 | Ube2b |
| 6920 | 3 | 4 | 5 | | | V-2 | Ube2cbp |
| 6921 | 3 | 4 | 5 | | | V-2 | Ube2f |
| 6922 | 3 | 4 | 5 | | | V-2 | Ube2h |
| 6923 | 3 | 4 | 5 | | | V-2 | Ube2o |
| 6924 | 3 | 4 | 5 | | | V-2 | Ube2r2 |
| 6925 | 3 | 4 | 5 | | | V-2 | Ube3b |
| 6926 | 3 | 4 | 5 | | | V-2 | Ubfd1 |
| 6927 | 3 | 4 | 5 | | | V-2 | Ublcp1 |
| 6928 | 3 | 4 | 5 | | | V-2 | Ubn2 |
| 6929 | 3 | 4 | 5 | | | V-2 | Ubqln4 |
| 6930 | 3 | 4 | 5 | | | V-2 | Ubqlnl |
| 6931 | 3 | 4 | 5 | | | V-2 | Ubr4 |
| 6932 | 3 | 4 | 5 | | | V-2 | Ubxn6 |
| 6933 | 3 | 4 | 5 | | | V-2 | Uck1 |
| 6934 | 3 | 4 | 5 | | | V-2 | Ucp3 |
| 6935 | 3 | 4 | 5 | | | V-2 | Ugt3a1 |
| 6936 | 3 | 4 | 5 | | | V-2 | Ugt3a2 |
| 6937 | 3 | 4 | 5 | | | V-2 | Uhrf1bp1l |
| 6938 | 3 | 4 | 5 | | | V-2 | Uhrf2 |
| 6939 | 3 | 4 | 5 | | | V-2 | Unc50 |
| 6940 | 3 | 4 | 5 | | | V-2 | Upf3a |
| 6941 | 3 | 4 | 5 | | | V-2 | Upf3b |
| 6942 | 3 | 4 | 5 | | | V-2 | Upk3a |
| 6943 | 3 | 4 | 5 | | | V-2 | Upk3bl |
| 6944 | 3 | 4 | 5 | | | V-2 | Urb2 |
| 6945 | 3 | 4 | 5 | | | V-2 | Urm1 |
| 6946 | 3 | 4 | 5 | | | V-2 | Usf1 |
| 6947 | 3 | 4 | 5 | | | V-2 | Ushbp1 |
| 6948 | 3 | 4 | 5 | | | V-2 | Usp3 |
| 6949 | 3 | 4 | 5 | | | V-2 | Usp30 |
| 6950 | 3 | 4 | 5 | | | V-2 | Usp31 |
| 6951 | 3 | 4 | 5 | | | V-2 | Usp40 |
| 6952 | 3 | 4 | 5 | | | V-2 | Usp54 |
| 6953 | 3 | 4 | 5 | | | V-2 | Usp9x |
| 6954 | 3 | 4 | 5 | | | V-2 | Uspl1 |
| 6955 | 3 | 4 | 5 | | | V-2 | Ust |
| 6956 | 3 | 4 | 5 | | | V-2 | Utp11l |
| 6957 | 3 | 4 | 5 | | | V-2 | Utp14a |
| 6958 | 3 | 4 | 5 | | | V-2 | Utp14b |
| 6959 | 3 | 4 | 5 | | | V-2 | Uty |
| 6960 | 3 | 4 | 5 | | | V-2 | Uxt |
| 6961 | 3 | 4 | 5 | | | V-2 | Vamp8 |
| 6962 | 3 | 4 | 5 | | | V-2 | Vars2 |
| 6963 | 3 | 4 | 5 | | | V-2 | Vaultrc5 |
| 6964 | 3 | 4 | 5 | | | V-2 | Vdac1 |
| 6965 | 3 | 4 | 5 | | | V-2 | Vdac2 |
| 6966 | 3 | 4 | 5 | | | V-2 | Vdac3 |
| 6967 | 3 | 4 | 5 | | | V-2 | Vegfb |
| 6968 | 3 | 4 | 5 | | | V-2 | Vipr1 |

Fig. 43 - 42

| | | | | | | | | |
|---|---|---|---|---|---|---|---|---|
| 6969 | 3 | 4 | 5 | | | V-2 | Vmn2r29 |
| 6970 | 3 | 4 | 5 | | | V-2 | Vmn2r84 |
| 6971 | 3 | 4 | 5 | | | V-2 | Vprbp |
| 6972 | 3 | 4 | 5 | | | V-2 | Vps13d |
| 6973 | 3 | 4 | 5 | | | V-2 | Vps33a |
| 6974 | 3 | 4 | 5 | | | V-2 | Vps36 |
| 6975 | 3 | 4 | 5 | | | V-2 | Vps37a |
| 6976 | 3 | 4 | 5 | | | V-2 | Vps45 |
| 6977 | 3 | 4 | 5 | | | V-2 | Vps4a |
| 6978 | 3 | 4 | 5 | | | V-2 | Vps51 |
| 6979 | 3 | 4 | 5 | | | V-2 | Vps72 |
| 6980 | 3 | 4 | 5 | | | V-2 | Vps9d1 |
| 6981 | 3 | 4 | 5 | | | V-2 | Vstm4 |
| 6982 | 3 | 4 | 5 | | | V-2 | Vwa2 |
| 6983 | 3 | 4 | 5 | | | V-2 | Vwa3a |
| 6984 | 3 | 4 | 5 | | | V-2 | Vwce |
| 6985 | 3 | 4 | 5 | | | V-2 | Wapal |
| 6986 | 3 | 4 | 5 | | | V-2 | Wars2 |
| 6987 | 3 | 4 | 5 | | | V-2 | Wash |
| 6988 | 3 | 4 | 5 | | | V-2 | Wbp5 |
| 6989 | 3 | 4 | 5 | | | V-2 | Wbscr16 |
| 6990 | 3 | 4 | 5 | | | V-2 | Wbscr22 |
| 6991 | 3 | 4 | 5 | | | V-2 | Wbscr27 |
| 6992 | 3 | 4 | 5 | | | V-2 | Wdpcp |
| 6993 | 3 | 4 | 5 | | | V-2 | Wdr20rt |
| 6994 | 3 | 4 | 5 | | | V-2 | Wdr53 |
| 6995 | 3 | 4 | 5 | | | V-2 | Wdr8 |
| 6996 | 3 | 4 | 5 | | | V-2 | Wdr81 |
| 6997 | 3 | 4 | 5 | | | V-2 | Wdr91 |
| 6998 | 3 | 4 | 5 | | | V-2 | Wdtc1 |
| 6999 | 3 | 4 | 5 | | | V-2 | Wfdc18 |
| 7000 | 3 | 4 | 5 | | | V-2 | Whsc1l1 |
| 7001 | 3 | 4 | 5 | | | V-2 | Wipi1 |
| 7002 | 3 | 4 | 5 | | | V-2 | Wiz |
| 7003 | 3 | 4 | 5 | | | V-2 | Wnk4 |
| 7004 | 3 | 4 | 5 | | | V-2 | Wnt10b |
| 7005 | 3 | 4 | 5 | | | V-2 | Wnt11 |
| 7006 | 3 | 4 | 5 | | | V-2 | Wnt8b |
| 7007 | 3 | 4 | 5 | | | V-2 | Wrn |
| 7008 | 3 | 4 | 5 | | | V-2 | Wrnip1 |
| 7009 | 3 | 4 | 5 | | | V-2 | Wwc1 |
| 7010 | 3 | 4 | 5 | | | V-2 | Xbp1 |
| 7011 | 3 | 4 | 5 | | | V-2 | Xiap |
| 7012 | 3 | 4 | 5 | | | V-2 | Xkr8 |
| 7013 | 3 | 4 | 5 | | | V-2 | Xlr3a |
| 7014 | 3 | 4 | 5 | | | V-2 | Xlr4a |
| 7015 | 3 | 4 | 5 | | | V-2 | Xpa |
| 7016 | 3 | 4 | 5 | | | V-2 | Xpc |
| 7017 | 3 | 4 | 5 | | | V-2 | Xylt1 |
| 7018 | 3 | 4 | 5 | | | V-2 | Yaf2 |
| 7019 | 3 | 4 | 5 | | | V-2 | Ybey |
| 7020 | 3 | 4 | 5 | | | V-2 | Yeats2 |
| 7021 | 3 | 4 | 5 | | | V-2 | Yif1a |
| 7022 | 3 | 4 | 5 | | | V-2 | Yipf1 |
| 7023 | 3 | 4 | 5 | | | V-2 | Yipf3 |
| 7024 | 3 | 4 | 5 | | | V-2 | Yipf4 |
| 7025 | 3 | 4 | 5 | | | V-2 | Ypel1 |
| 7026 | 3 | 4 | 5 | | | V-2 | Ypel2 |
| 7027 | 3 | 4 | 5 | | | V-2 | Ypel3 |
| 7028 | 3 | 4 | 5 | | | V-2 | Ywhaq |
| 7029 | 3 | 4 | 5 | | | V-2 | Zap70 |
| 7030 | 3 | 4 | 5 | | | V-2 | Zbed4 |
| 7031 | 3 | 4 | 5 | | | V-2 | Zbtb1 |
| 7032 | 3 | 4 | 5 | | | V-2 | Zbtb10 |
| 7033 | 3 | 4 | 5 | | | V-2 | Zbtb11 |
| 7034 | 3 | 4 | 5 | | | V-2 | Zbtb12 |
| 7035 | 3 | 4 | 5 | | | V-2 | Zbtb17 |
| 7036 | 3 | 4 | 5 | | | V-2 | Zbtb18 |
| 7037 | 3 | 4 | 5 | | | V-2 | Zbtb34 |
| 7038 | 3 | 4 | 5 | | | V-2 | Zbtb39 |
| 7039 | 3 | 4 | 5 | | | V-2 | Zbtb4 |
| 7040 | 3 | 4 | 5 | | | V-2 | Zbtb40 |
| 7041 | 3 | 4 | 5 | | | V-2 | Zbtb44 |
| 7042 | 3 | 4 | 5 | | | V-2 | Zbtb45 |
| 7043 | 3 | 4 | 5 | | | V-2 | Zbtb9 |
| 7044 | 3 | 4 | 5 | | | V-2 | Zc2hc1b |
| 7045 | 3 | 4 | 5 | | | V-2 | Zc3h12c |
| 7046 | 3 | 4 | 5 | | | V-2 | Zc3h12d |
| 7047 | 3 | 4 | 5 | | | V-2 | Zc3h8 |
| 7048 | 3 | 4 | 5 | | | V-2 | Zc3hav1l |
| 7049 | 3 | 4 | 5 | | | V-2 | Zc4h2 |
| 7050 | 3 | 4 | 5 | | | V-2 | Zcchc10 |
| 7051 | 3 | 4 | 5 | | | V-2 | Zcchc12 |
| 7052 | 3 | 4 | 5 | | | V-2 | Zcchc14 |
| 7053 | 3 | 4 | 5 | | | V-2 | Zcchc24 |
| 7054 | 3 | 4 | 5 | | | V-2 | Zcchc8 |
| 7055 | 3 | 4 | 5 | | | V-2 | Zcchc9 |
| 7056 | 3 | 4 | 5 | | | V-2 | Zcrb1 |
| 7057 | 3 | 4 | 5 | | | V-2 | Zcwpw1 |
| 7058 | 3 | 4 | 5 | | | V-2 | Zdhhc14 |
| 7059 | 3 | 4 | 5 | | | V-2 | Zdhhc24 |
| 7060 | 3 | 4 | 5 | | | V-2 | Zdhhc8 |
| 7061 | 3 | 4 | 5 | | | V-2 | Zeb1 |
| 7062 | 3 | 4 | 5 | | | V-2 | Zeb2 |
| 7063 | 3 | 4 | 5 | | | V-2 | Zfand6 |
| 7064 | 3 | 4 | 5 | | | V-2 | Zfat |
| 7065 | 3 | 4 | 5 | | | V-2 | Zfc3h1 |
| 7066 | 3 | 4 | 5 | | | V-2 | Zfhx2 |
| 7067 | 3 | 4 | 5 | | | V-2 | Zfhx3 |
| 7068 | 3 | 4 | 5 | | | V-2 | Zfml |
| 7069 | 3 | 4 | 5 | | | V-2 | Zfp1 |
| 7070 | 3 | 4 | 5 | | | V-2 | Zfp101 |
| 7071 | 3 | 4 | 5 | | | V-2 | Zfp108 |
| 7072 | 3 | 4 | 5 | | | V-2 | Zfp111 |
| 7073 | 3 | 4 | 5 | | | V-2 | Zfp113 |
| 7074 | 3 | 4 | 5 | | | V-2 | Zfp119b |
| 7075 | 3 | 4 | 5 | | | V-2 | Zfp12 |
| 7076 | 3 | 4 | 5 | | | V-2 | Zfp133-ps |
| 7077 | 3 | 4 | 5 | | | V-2 | Zfp14 |
| 7078 | 3 | 4 | 5 | | | V-2 | Zfp142 |
| 7079 | 3 | 4 | 5 | | | V-2 | Zfp180 |
| 7080 | 3 | 4 | 5 | | | V-2 | Zfp182 |
| 7081 | 3 | 4 | 5 | | | V-2 | Zfp235 |
| 7082 | 3 | 4 | 5 | | | V-2 | Zfp236 |
| 7083 | 3 | 4 | 5 | | | V-2 | Zfp248 |
| 7084 | 3 | 4 | 5 | | | V-2 | Zfp260 |
| 7085 | 3 | 4 | 5 | | | V-2 | Zfp277 |
| 7086 | 3 | 4 | 5 | | | V-2 | Zfp280d |
| 7087 | 3 | 4 | 5 | | | V-2 | Zfp286 |
| 7088 | 3 | 4 | 5 | | | V-2 | Zfp296 |
| 7089 | 3 | 4 | 5 | | | V-2 | Zfp30 |
| 7090 | 3 | 4 | 5 | | | V-2 | Zfp318 |
| 7091 | 3 | 4 | 5 | | | V-2 | Zfp319 |
| 7092 | 3 | 4 | 5 | | | V-2 | Zfp322a |
| 7093 | 3 | 4 | 5 | | | V-2 | Zfp324 |
| 7094 | 3 | 4 | 5 | | | V-2 | Zfp326 |
| 7095 | 3 | 4 | 5 | | | V-2 | Zfp334 |
| 7096 | 3 | 4 | 5 | | | V-2 | Zfp335 |
| 7097 | 3 | 4 | 5 | | | V-2 | Zfp341 |
| 7098 | 3 | 4 | 5 | | | V-2 | Zfp346 |
| 7099 | 3 | 4 | 5 | | | V-2 | Zfp354b |
| 7100 | 3 | 4 | 5 | | | V-2 | Zfp354c |
| 7101 | 3 | 4 | 5 | | | V-2 | Zfp36 |
| 7102 | 3 | 4 | 5 | | | V-2 | Zfp36l1 |
| 7103 | 3 | 4 | 5 | | | V-2 | Zfp39 |
| 7104 | 3 | 4 | 5 | | | V-2 | Zfp397 |
| 7105 | 3 | 4 | 5 | | | V-2 | Zfp418 |
| 7106 | 3 | 4 | 5 | | | V-2 | Zfp420 |
| 7107 | 3 | 4 | 5 | | | V-2 | Zfp426 |
| 7108 | 3 | 4 | 5 | | | V-2 | Zfp429 |
| 7109 | 3 | 4 | 5 | | | V-2 | Zfp444 |
| 7110 | 3 | 4 | 5 | | | V-2 | Zfp451 |
| 7111 | 3 | 4 | 5 | | | V-2 | Zfp456 |
| 7112 | 3 | 4 | 5 | | | V-2 | Zfp459 |
| 7113 | 3 | 4 | 5 | | | V-2 | Zfp462 |
| 7114 | 3 | 4 | 5 | | | V-2 | Zfp467 |
| 7115 | 3 | 4 | 5 | | | V-2 | Zfp474 |
| 7116 | 3 | 4 | 5 | | | V-2 | Zfp493 |
| 7117 | 3 | 4 | 5 | | | V-2 | Zfp516 |
| 7118 | 3 | 4 | 5 | | | V-2 | Zfp518a |
| 7119 | 3 | 4 | 5 | | | V-2 | Zfp566 |
| 7120 | 3 | 4 | 5 | | | V-2 | Zfp57 |
| 7121 | 3 | 4 | 5 | | | V-2 | Zfp579 |
| 7122 | 3 | 4 | 5 | | | V-2 | Zfp58 |
| 7123 | 3 | 4 | 5 | | | V-2 | Zfp583 |
| 7124 | 3 | 4 | 5 | | | V-2 | Zfp59 |
| 7125 | 3 | 4 | 5 | | | V-2 | Zfp592 |
| 7126 | 3 | 4 | 5 | | | V-2 | Zfp593 |
| 7127 | 3 | 4 | 5 | | | V-2 | Zfp598 |
| 7128 | 3 | 4 | 5 | | | V-2 | Zfp60 |
| 7129 | 3 | 4 | 5 | | | V-2 | Zfp605 |
| 7130 | 3 | 4 | 5 | | | V-2 | Zfp606 |
| 7131 | 3 | 4 | 5 | | | V-2 | Zfp61 |
| 7132 | 3 | 4 | 5 | | | V-2 | Zfp612 |
| 7133 | 3 | 4 | 5 | | | V-2 | Zfp619 |
| 7134 | 3 | 4 | 5 | | | V-2 | Zfp622 |
| 7135 | 3 | 4 | 5 | | | V-2 | Zfp629 |
| 7136 | 3 | 4 | 5 | | | V-2 | Zfp637 |
| 7137 | 3 | 4 | 5 | | | V-2 | Zfp639 |
| 7138 | 3 | 4 | 5 | | | V-2 | Zfp644 |

Fig. 43 - 43

| | | | | | | | |
|---|---|---|---|---|---|---|---|
| 7139 | 3 | 4 | 5 | | | V-2 | Zfp647 |
| 7140 | 3 | 4 | 5 | | | V-2 | Zfp65 |
| 7141 | 3 | 4 | 5 | | | V-2 | Zfp652os |
| 7142 | 3 | 4 | 5 | | | V-2 | Zfp658 |
| 7143 | 3 | 4 | 5 | | | V-2 | Zfp668 |
| 7144 | 3 | 4 | 5 | | | V-2 | Zfp697 |
| 7145 | 3 | 4 | 5 | | | V-2 | Zfp7 |
| 7146 | 3 | 4 | 5 | | | V-2 | Zfp707 |
| 7147 | 3 | 4 | 5 | | | V-2 | Zfp708 |
| 7148 | 3 | 4 | 5 | | | V-2 | Zfp709 |
| 7149 | 3 | 4 | 5 | | | V-2 | Zfp715 |
| 7150 | 3 | 4 | 5 | | | V-2 | Zfp74 |
| 7151 | 3 | 4 | 5 | | | V-2 | Zfp747 |
| 7152 | 3 | 4 | 5 | | | V-2 | Zfp748 |
| 7153 | 3 | 4 | 5 | | | V-2 | Zfp758 |
| 7154 | 3 | 4 | 5 | | | V-2 | Zfp760 |
| 7155 | 3 | 4 | 5 | | | V-2 | Zfp764 |
| 7156 | 3 | 4 | 5 | | | V-2 | Zfp768 |
| 7157 | 3 | 4 | 5 | | | V-2 | Zfp770 |
| 7158 | 3 | 4 | 5 | | | V-2 | Zfp773 |
| 7159 | 3 | 4 | 5 | | | V-2 | Zfp775 |
| 7160 | 3 | 4 | 5 | | | V-2 | Zfp787 |
| 7161 | 3 | 4 | 5 | | | V-2 | Zfp790 |
| 7162 | 3 | 4 | 5 | | | V-2 | Zfp799 |
| 7163 | 3 | 4 | 5 | | | V-2 | Zfp808 |
| 7164 | 3 | 4 | 5 | | | V-2 | Zfp82 |
| 7165 | 3 | 4 | 5 | | | V-2 | Zfp821 |
| 7166 | 3 | 4 | 5 | | | V-2 | Zfp831 |
| 7167 | 3 | 4 | 5 | | | V-2 | Zfp84 |
| 7168 | 3 | 4 | 5 | | | V-2 | Zfp846 |
| 7169 | 3 | 4 | 5 | | | V-2 | Zfp85 |
| 7170 | 3 | 4 | 5 | | | V-2 | Zfp850 |
| 7171 | 3 | 4 | 5 | | | V-2 | Zfp862-ps |
| 7172 | 3 | 4 | 5 | | | V-2 | Zfp865 |
| 7173 | 3 | 4 | 5 | | | V-2 | Zfp87 |
| 7174 | 3 | 4 | 5 | | | V-2 | Zfp873 |
| 7175 | 3 | 4 | 5 | | | V-2 | Zfp874a |
| 7176 | 3 | 4 | 5 | | | V-2 | Zfp93 |
| 7177 | 3 | 4 | 5 | | | V-2 | Zfp932 |
| 7178 | 3 | 4 | 5 | | | V-2 | Zfp935 |
| 7179 | 3 | 4 | 5 | | | V-2 | Zfp939 |
| 7180 | 3 | 4 | 5 | | | V-2 | Zfp94 |
| 7181 | 3 | 4 | 5 | | | V-2 | Zfp940 |
| 7182 | 3 | 4 | 5 | | | V-2 | Zfp944 |
| 7183 | 3 | 4 | 5 | | | V-2 | Zfp945 |
| 7184 | 3 | 4 | 5 | | | V-2 | Zfp946 |
| 7185 | 3 | 4 | 5 | | | V-2 | Zfp948 |
| 7186 | 3 | 4 | 5 | | | V-2 | Zfp951 |
| 7187 | 3 | 4 | 5 | | | V-2 | Zfp952 |
| 7188 | 3 | 4 | 5 | | | V-2 | Zfp953 |
| 7189 | 3 | 4 | 5 | | | V-2 | Zfp960 |
| 7190 | 3 | 4 | 5 | | | V-2 | Zfp963 |
| 7191 | 3 | 4 | 5 | | | V-2 | Zfp964 |
| 7192 | 3 | 4 | 5 | | | V-2 | Zfp97 |
| 7193 | 3 | 4 | 5 | | | V-2 | Zfpm2 |
| 7194 | 3 | 4 | 5 | | | V-2 | Zfyve1 |
| 7195 | 3 | 4 | 5 | | | V-2 | Zfyve16 |
| 7196 | 3 | 4 | 5 | | | V-2 | Zfyve21 |
| 7197 | 3 | 4 | 5 | | | V-2 | Zfyve26 |
| 7198 | 3 | 4 | 5 | | | V-2 | Zik1 |
| 7199 | 3 | 4 | 5 | | | V-2 | Zkscan4 |
| 7200 | 3 | 4 | 5 | | | V-2 | Zkscan8 |
| 7201 | 3 | 4 | 5 | | | V-2 | Zmat5 |
| 7202 | 3 | 4 | 5 | | | V-2 | Zmiz1 |
| 7203 | 3 | 4 | 5 | | | V-2 | Znhit1 |
| 7204 | 3 | 4 | 5 | | | V-2 | Znhit6 |
| 7205 | 3 | 4 | 5 | | | V-2 | Znrf1 |
| 7206 | 3 | 4 | 5 | | | V-2 | Zrsr1 |
| 7207 | 3 | 4 | 5 | | | V-2 | Zscan10 |
| 7208 | 3 | 4 | 5 | | | V-2 | Zscan18 |
| 7209 | 3 | 4 | 5 | | | V-2 | Zscan2 |
| 7210 | 3 | 4 | 5 | | | V-2 | Zscan22 |
| 7211 | 3 | 4 | 5 | | | V-2 | Zswim3 |
| 7212 | 3 | 4 | 5 | | | V-2 | Zswim4 |
| 7213 | 3 | 4 | 5 | | | V-2 | Zswim5 |
| 7214 | 3 | 4 | 5 | | | V-2 | Zufsp |
| 7215 | 3 | 4 | 5 | | | V-2 | Zw10 |
| 7216 | 3 | 4 | 5 | | | V-2 | Zxda |
| 7217 | 3 | 4 | 5 | | | V-2 | Zyg11b |
| 7218 | 3 | 4 | 5 | | | V-1 | 0610010K14Rik |
| 7219 | 3 | 4 | 5 | | | V-1 | 0610011F06Rik |
| 7220 | 3 | 4 | 5 | | | V-1 | 0610040F04Rik |
| 7221 | 3 | 4 | 5 | | | V-1 | 1010001N08Rik |
| 7222 | 3 | 4 | 5 | | | V-1 | 1100001G20Rik |
| 7223 | 3 | 4 | 5 | | | V-1 | 1110001J03Rik |
| 7224 | 3 | 4 | 5 | | | V-1 | 1110007C09Rik |
| 7225 | 3 | 4 | 5 | | | V-1 | 1110008F13Rik |
| 7226 | 3 | 4 | 5 | | | V-1 | 1110008P14Rik |
| 7227 | 3 | 4 | 5 | | | V-1 | 1110058L19Rik |
| 7228 | 3 | 4 | 5 | | | V-1 | 1110059G10Rik |
| 7229 | 3 | 4 | 5 | | | V-1 | 1110065P20Rik |
| 7230 | 3 | 4 | 5 | | | V-1 | 1190007J07Rik |
| 7231 | 3 | 4 | 5 | | | V-1 | 1300002K09Rik |
| 7232 | 3 | 4 | 5 | | | V-1 | 1500011B03Rik |
| 7233 | 3 | 4 | 5 | | | V-1 | 1500011K16Rik |
| 7234 | 3 | 4 | 5 | | | V-1 | 1500012K07Rik |
| 7235 | 3 | 4 | 5 | | | V-1 | 1500015A07Rik |
| 7236 | 3 | 4 | 5 | | | V-1 | 1600010M07Rik |
| 7237 | 3 | 4 | 5 | | | V-1 | 1600014C10Rik |
| 7238 | 3 | 4 | 5 | | | V-1 | 1600016N20Rik |
| 7239 | 3 | 4 | 5 | | | V-1 | 1600025M17Rik |
| 7240 | 3 | 4 | 5 | | | V-1 | 1700001L05Rik |
| 7241 | 3 | 4 | 5 | | | V-1 | 1700001L19Rik |
| 7242 | 3 | 4 | 5 | | | V-1 | 1700001O22Rik |
| 7243 | 3 | 4 | 5 | | | V-1 | 1700007L15Rik |
| 7244 | 3 | 4 | 5 | | | V-1 | 1700008J07Rik |
| 7245 | 3 | 4 | 5 | | | V-1 | 1700009J07Rik |
| 7246 | 3 | 4 | 5 | | | V-1 | 1700012D01Rik |
| 7247 | 3 | 4 | 5 | | | V-1 | 1700019O03Rik |
| 7248 | 3 | 4 | 5 | | | V-1 | 1700019G17Rik |
| 7249 | 3 | 4 | 5 | | | V-1 | 1700023L04Rik |
| 7250 | 3 | 4 | 5 | | | V-1 | 1700025G04Rik |
| 7251 | 3 | 4 | 5 | | | V-1 | 1700028K03Rik |
| 7252 | 3 | 4 | 5 | | | V-1 | 1700030A11Rik |
| 7253 | 3 | 4 | 5 | | | V-1 | 1700037H04Rik |
| 7254 | 3 | 4 | 5 | | | V-1 | 1700052K11Rik |
| 7255 | 3 | 4 | 5 | | | V-1 | 1700056E22Rik |
| 7256 | 3 | 4 | 5 | | | V-1 | 1700088E04Rik |
| 7257 | 3 | 4 | 5 | | | V-1 | 1700093K21Rik |
| 7258 | 3 | 4 | 5 | | | V-1 | 1700096K18Rik |
| 7259 | 3 | 4 | 5 | | | V-1 | 1700102H20Rik |
| 7260 | 3 | 4 | 5 | | | V-1 | 1700109K24Rik |
| 7261 | 3 | 4 | 5 | | | V-1 | 1700113A16Rik |
| 7262 | 3 | 4 | 5 | | | V-1 | 1700119H24Rik |
| 7263 | 3 | 4 | 5 | | | V-1 | 1700123M08Rik |
| 7264 | 3 | 4 | 5 | | | V-1 | 1810009A15Rik |
| 7265 | 3 | 4 | 5 | | | V-1 | 1810010D01Rik |
| 7266 | 3 | 4 | 5 | | | V-1 | 1810010H24Rik |
| 7267 | 3 | 4 | 5 | | | V-1 | 1810032O08Rik |
| 7268 | 3 | 4 | 5 | | | V-1 | 1810037I17Rik |
| 7269 | 3 | 4 | 5 | | | V-1 | 1810041L15Rik |
| 7270 | 3 | 4 | 5 | | | V-1 | 1810043H04Rik |
| 7271 | 3 | 4 | 5 | | | V-1 | 1810044D09Rik |
| 7272 | 3 | 4 | 5 | | | V-1 | 1810053B23Rik |
| 7273 | 3 | 4 | 5 | | | V-1 | 1810058I24Rik |
| 7274 | 3 | 4 | 5 | | | V-1 | 2010107E04Rik |
| 7275 | 3 | 4 | 5 | | | V-1 | 2010320M18Rik |
| 7276 | 3 | 4 | 5 | | | V-1 | 2200002D01Rik |
| 7277 | 3 | 4 | 5 | | | V-1 | 2210407C18Rik |
| 7278 | 3 | 4 | 5 | | | V-1 | 2210409E12Rik |
| 7279 | 3 | 4 | 5 | | | V-1 | 2300002M23Rik |
| 7280 | 3 | 4 | 5 | | | V-1 | 2310007L24Rik |
| 7281 | 3 | 4 | 5 | | | V-1 | 2310015A10Rik |
| 7282 | 3 | 4 | 5 | | | V-1 | 2310034G01Rik |
| 7283 | 3 | 4 | 5 | | | V-1 | 2310036O22Rik |
| 7284 | 3 | 4 | 5 | | | V-1 | 2310039H08Rik |
| 7285 | 3 | 4 | 5 | | | V-1 | 2310039L15Rik |
| 7286 | 3 | 4 | 5 | | | V-1 | 2310045N01Rik |
| 7287 | 3 | 4 | 5 | | | V-1 | 2310057M21Rik |
| 7288 | 3 | 4 | 5 | | | V-1 | 2310061J03Rik |
| 7289 | 3 | 4 | 5 | | | V-1 | 2410015M20Rik |
| 7290 | 3 | 4 | 5 | | | V-1 | 2510002D24Rik |
| 7291 | 3 | 4 | 5 | | | V-1 | 2610002J02Rik |
| 7292 | 3 | 4 | 5 | | | V-1 | 2610016A17Rik |
| 7293 | 3 | 4 | 5 | | | V-1 | 2610018G03Rik |
| 7294 | 3 | 4 | 5 | | | V-1 | 2610020C07Rik |
| 7295 | 3 | 4 | 5 | | | V-1 | 2610034B18Rik |
| 7296 | 3 | 4 | 5 | | | V-1 | 2610044O15Rik8 |
| 7297 | 3 | 4 | 5 | | | V-1 | 2610203C20Rik |
| 7298 | 3 | 4 | 5 | | | V-1 | 2700038G22Rik |
| 7299 | 3 | 4 | 5 | | | V-1 | 2700046A07Rik |
| 7300 | 3 | 4 | 5 | | | V-1 | 2700046G09Rik |
| 7301 | 3 | 4 | 5 | | | V-1 | 2700060E02Rik |
| 7302 | 3 | 4 | 5 | | | V-1 | 2700062C07Rik |
| 7303 | 3 | 4 | 5 | | | V-1 | 2700097O09Rik |
| 7304 | 3 | 4 | 5 | | | V-1 | 2810001G20Rik |
| 7305 | 3 | 4 | 5 | | | V-1 | 2810405F15Rik |
| 7306 | 3 | 4 | 5 | | | V-1 | 2810417H13Rik |
| 7307 | 3 | 4 | 5 | | | V-1 | 2900005J15Rik |
| 7308 | 3 | 4 | 5 | | | V-1 | 2900009J06Rik |

Fig. 43 - 44

| | | | | | | | | | | | | | | | |
|---|---|---|---|---|---|---|---|---|---|---|---|---|---|---|---|
| 7309 | 3 | 4 | 5 | | | V-1 | 2900092D14Rik | 7394 | 3 | 4 | 5 | | | V-1 | Aatk |
| 7310 | 3 | 4 | 5 | | | V-1 | 3010026O09Rik | 7395 | 3 | 4 | 5 | | | V-1 | Abat |
| 7311 | 3 | 4 | 5 | | | V-1 | 3110040N11Rik | 7396 | 3 | 4 | 5 | | | V-1 | Abca1 |
| 7312 | 3 | 4 | 5 | | | V-1 | 3110082I17Rik | 7397 | 3 | 4 | 5 | | | V-1 | Abca13 |
| 7313 | 3 | 4 | 5 | | | V-1 | 4632415L05Rik | 7398 | 3 | 4 | 5 | | | V-1 | Abca5 |
| 7314 | 3 | 4 | 5 | | | V-1 | 4833403I15Rik | 7399 | 3 | 4 | 5 | | | V-1 | Abca8a |
| 7315 | 3 | 4 | 5 | | | V-1 | 4833419F23Rik | 7400 | 3 | 4 | 5 | | | V-1 | Abcb1a |
| 7316 | 3 | 4 | 5 | | | V-1 | 4833420G17Rik | 7401 | 3 | 4 | 5 | | | V-1 | Abcb6 |
| 7317 | 3 | 4 | 5 | | | V-1 | 4833439L19Rik | 7402 | 3 | 4 | 5 | | | V-1 | Abcb8 |
| 7318 | 3 | 4 | 5 | | | V-1 | 4921504A21Rik | 7403 | 3 | 4 | 5 | | | V-1 | Abcc10 |
| 7319 | 3 | 4 | 5 | | | V-1 | 4930401O12Rik | 7404 | 3 | 4 | 5 | | | V-1 | Abcc3 |
| 7320 | 3 | 4 | 5 | | | V-1 | 4930404H11Rik | 7405 | 3 | 4 | 5 | | | V-1 | Abcd2 |
| 7321 | 3 | 4 | 5 | | | V-1 | 4930404I05Rik | 7406 | 3 | 4 | 5 | | | V-1 | Abce1 |
| 7322 | 3 | 4 | 5 | | | V-1 | 4930427A07Rik | 7407 | 3 | 4 | 5 | | | V-1 | Abcg1 |
| 7323 | 3 | 4 | 5 | | | V-1 | 4930428E07Rik | 7408 | 3 | 4 | 5 | | | V-1 | Abcg5 |
| 7324 | 3 | 4 | 5 | | | V-1 | 4930467E23Rik | 7409 | 3 | 4 | 5 | | | V-1 | Abhd10 |
| 7325 | 3 | 4 | 5 | | | V-1 | 4930479D17Rik | 7410 | 3 | 4 | 5 | | | V-1 | Abhd11 |
| 7326 | 3 | 4 | 5 | | | V-1 | 4930503E24Rik | 7411 | 3 | 4 | 5 | | | V-1 | Abhd16a |
| 7327 | 3 | 4 | 5 | | | V-1 | 4930506C21Rik | 7412 | 3 | 4 | 5 | | | V-1 | Abhd6 |
| 7328 | 3 | 4 | 5 | | | V-1 | 4930520O04Rik | 7413 | 3 | 4 | 5 | | | V-1 | Abi2 |
| 7329 | 3 | 4 | 5 | | | V-1 | 4930539E08Rik | 7414 | 3 | 4 | 5 | | | V-1 | Abi3bp |
| 7330 | 3 | 4 | 5 | | | V-1 | 4930556M19Rik | 7415 | 3 | 4 | 5 | | | V-1 | Abl2 |
| 7331 | 3 | 4 | 5 | | | V-1 | 4930562F07Rik | 7416 | 3 | 4 | 5 | | | V-1 | Ablim2 |
| 7332 | 3 | 4 | 5 | | | V-1 | 4930565N06Rik | 7417 | 3 | 4 | 5 | | | V-1 | Abracl |
| 7333 | 3 | 4 | 5 | | | V-1 | 4930577N17Rik | 7418 | 3 | 4 | 5 | | | V-1 | Abtb2 |
| 7334 | 3 | 4 | 5 | | | V-1 | 4930579G24Rik | 7419 | 3 | 4 | 5 | | | V-1 | Acap2 |
| 7335 | 3 | 4 | 5 | | | V-1 | 4930581F22Rik | 7420 | 3 | 4 | 5 | | | V-1 | Acat2 |
| 7336 | 3 | 4 | 5 | | | V-1 | 4930594C11Rik | 7421 | 3 | 4 | 5 | | | V-1 | Acat3 |
| 7337 | 3 | 4 | 5 | | | V-1 | 4930599N23Rik | 7422 | 3 | 4 | 5 | | | V-1 | Ace |
| 7338 | 3 | 4 | 5 | | | V-1 | 4931403E22Rik | 7423 | 3 | 4 | 5 | | | V-1 | Ace2 |
| 7339 | 3 | 4 | 5 | | | V-1 | 4931406C07Rik | 7424 | 3 | 4 | 5 | | | V-1 | Acer3 |
| 7340 | 3 | 4 | 5 | | | V-1 | 4931406P16Rik | 7425 | 3 | 4 | 5 | | | V-1 | Acnat1 |
| 7341 | 3 | 4 | 5 | | | V-1 | 4931440P22Rik | 7426 | 3 | 4 | 5 | | | V-1 | Acnat2 |
| 7342 | 3 | 4 | 5 | | | V-1 | 4932416H05Rik | 7427 | 3 | 4 | 5 | | | V-1 | Acot12 |
| 7343 | 3 | 4 | 5 | | | V-1 | 4933406I18Rik | 7428 | 3 | 4 | 5 | | | V-1 | Acot4 |
| 7344 | 3 | 4 | 5 | | | V-1 | 4933417G07Rik | 7429 | 3 | 4 | 5 | | | V-1 | Acot6 |
| 7345 | 3 | 4 | 5 | | | V-1 | 4933427G17Rik | 7430 | 3 | 4 | 5 | | | V-1 | Acot7 |
| 7346 | 3 | 4 | 5 | | | V-1 | 5430416N02Rik | 7431 | 3 | 4 | 5 | | | V-1 | Acot9 |
| 7347 | 3 | 4 | 5 | | | V-1 | 5430419D17Rik | 7432 | 3 | 4 | 5 | | | V-1 | Acpt |
| 7348 | 3 | 4 | 5 | | | V-1 | 5430425K12Rik | 7433 | 3 | 4 | 5 | | | V-1 | Acsl4 |
| 7349 | 3 | 4 | 5 | | | V-1 | 5730409E04Rik | 7434 | 3 | 4 | 5 | | | V-1 | Acsl5 |
| 7350 | 3 | 4 | 5 | | | V-1 | 5730416F02Rik | 7435 | 3 | 4 | 5 | | | V-1 | Acsl6 |
| 7351 | 3 | 4 | 5 | | | V-1 | 5730420D15Rik | 7436 | 3 | 4 | 5 | | | V-1 | Acsm1 |
| 7352 | 3 | 4 | 5 | | | V-1 | 5830415F09Rik | 7437 | 3 | 4 | 5 | | | V-1 | Acss1 |
| 7353 | 3 | 4 | 5 | | | V-1 | 5830473C10Rik | 7438 | 3 | 4 | 5 | | | V-1 | Actb |
| 7354 | 3 | 4 | 5 | | | V-1 | 5930403L14Rik | 7439 | 3 | 4 | 5 | | | V-1 | Actl6a |
| 7355 | 3 | 4 | 5 | | | V-1 | 6030419C18Rik | 7440 | 3 | 4 | 5 | | | V-1 | Actr6 |
| 7356 | 3 | 4 | 5 | | | V-1 | 6030468B19Rik | 7441 | 3 | 4 | 5 | | | V-1 | Acvrl1 |
| 7357 | 3 | 4 | 5 | | | V-1 | 6230400D17Rik | 7442 | 3 | 4 | 5 | | | V-1 | Acy3 |
| 7358 | 3 | 4 | 5 | | | V-1 | 6430548M08Rik | 7443 | 3 | 4 | 5 | | | V-1 | Adam22 |
| 7359 | 3 | 4 | 5 | | | V-1 | 6430550D23Rik | 7444 | 3 | 4 | 5 | | | V-1 | Adam28 |
| 7360 | 3 | 4 | 5 | | | V-1 | 6430571L13Rik | 7445 | 3 | 4 | 5 | | | V-1 | Adam8 |
| 7361 | 3 | 4 | 5 | | | V-1 | 6430573F11Rik | 7446 | 3 | 4 | 5 | | | V-1 | Adamdec1 |
| 7362 | 3 | 4 | 5 | | | V-1 | 6720468P15Rik | 7447 | 3 | 4 | 5 | | | V-1 | Adamts1 |
| 7363 | 3 | 4 | 5 | | | V-1 | 6820431F20Rik | 7448 | 3 | 4 | 5 | | | V-1 | Adamts2 |
| 7364 | 3 | 4 | 5 | | | V-1 | 9030025P20Rik | 7449 | 3 | 4 | 5 | | | V-1 | Adamts5 |
| 7365 | 3 | 4 | 5 | | | V-1 | 9130008F23Rik | 7450 | 3 | 4 | 5 | | | V-1 | Adamts7 |
| 7366 | 3 | 4 | 5 | | | V-1 | 9130023H24Rik | 7451 | 3 | 4 | 5 | | | V-1 | Adamts9 |
| 7367 | 3 | 4 | 5 | | | V-1 | 9230116N13Rik | 7452 | 3 | 4 | 5 | | | V-1 | Adamtsl1 |
| 7368 | 3 | 4 | 5 | | | V-1 | 9330159M07Rik | 7453 | 3 | 4 | 5 | | | V-1 | Adamtsl2 |
| 7369 | 3 | 4 | 5 | | | V-1 | 9330179D12Rik | 7454 | 3 | 4 | 5 | | | V-1 | Adamtsl4 |
| 7370 | 3 | 4 | 5 | | | V-1 | 9430008C03Rik | 7455 | 3 | 4 | 5 | | | V-1 | Adamtsl5 |
| 7371 | 3 | 4 | 5 | | | V-1 | 9430038I01Rik | 7456 | 3 | 4 | 5 | | | V-1 | Adap1 |
| 7372 | 3 | 4 | 5 | | | V-1 | 9530027J09Rik | 7457 | 3 | 4 | 5 | | | V-1 | Adarb1 |
| 7373 | 3 | 4 | 5 | | | V-1 | 9530080O11Rik | 7458 | 3 | 4 | 5 | | | V-1 | Adat2 |
| 7374 | 3 | 4 | 5 | | | V-1 | 9530082P21Rik | 7459 | 3 | 4 | 5 | | | V-1 | Adck5 |
| 7375 | 3 | 4 | 5 | | | V-1 | 9630033F20Rik | 7460 | 3 | 4 | 5 | | | V-1 | Adcy2 |
| 7376 | 3 | 4 | 5 | | | V-1 | 9830166K06Rik | 7461 | 3 | 4 | 5 | | | V-1 | Adcy5 |
| 7377 | 3 | 4 | 5 | | | V-1 | 9930104L06Rik | 7462 | 3 | 4 | 5 | | | V-1 | Adhfe1 |
| 7378 | 3 | 4 | 5 | | | V-1 | A130077B15Rik | 7463 | 3 | 4 | 5 | | | V-1 | Adk |
| 7379 | 3 | 4 | 5 | | | V-1 | A330035P11Rik | 7464 | 3 | 4 | 5 | | | V-1 | Adm2 |
| 7380 | 3 | 4 | 5 | | | V-1 | A330076C08Rik | 7465 | 3 | 4 | 5 | | | V-1 | Adora2b |
| 7381 | 3 | 4 | 5 | | | V-1 | A4gnt | 7466 | 3 | 4 | 5 | | | V-1 | Adprh |
| 7382 | 3 | 4 | 5 | | | V-1 | A630001G21Rik | 7467 | 3 | 4 | 5 | | | V-1 | Adra1b |
| 7383 | 3 | 4 | 5 | | | V-1 | A630066F11Rik | 7468 | 3 | 4 | 5 | | | V-1 | Adrb1 |
| 7384 | 3 | 4 | 5 | | | V-1 | A830080D01Rik | 7469 | 3 | 4 | 5 | | | V-1 | Adrb2 |
| 7385 | 3 | 4 | 5 | | | V-1 | A930004D18Rik | 7470 | 3 | 4 | 5 | | | V-1 | Adrb3 |
| 7386 | 3 | 4 | 5 | | | V-1 | A930005H10Rik | 7471 | 3 | 4 | 5 | | | V-1 | Adrm1 |
| 7387 | 3 | 4 | 5 | | | V-1 | A930015D03Rik | 7472 | 3 | 4 | 5 | | | V-1 | Adsl |
| 7388 | 3 | 4 | 5 | | | V-1 | A930018P22Rik | 7473 | 3 | 4 | 5 | | | V-1 | Adtrp |
| 7389 | 3 | 4 | 5 | | | V-1 | AA414768 | 7474 | 3 | 4 | 5 | | | V-1 | Aebp1 |
| 7390 | 3 | 4 | 5 | | | V-1 | Aadacl3 | 7475 | 3 | 4 | 5 | | | V-1 | Afmid |
| 7391 | 3 | 4 | 5 | | | V-1 | Aak1 | 7476 | 3 | 4 | 5 | | | V-1 | Aga |
| 7392 | 3 | 4 | 5 | | | V-1 | Aars | 7477 | 3 | 4 | 5 | | | V-1 | Agbl3 |
| 7393 | 3 | 4 | 5 | | | V-1 | Aarsd1 | 7478 | 3 | 4 | 5 | | | V-1 | Ager |

Fig. 43 - 45

| | | | | | | | | |
|---|---|---|---|---|---|---|---|---|
| 7479 | 3 | 4 | 5 | | | V-1 | Agpat9 |
| 7480 | 3 | 4 | 5 | | | V-1 | Agrp |
| 7481 | 3 | 4 | 5 | | | V-1 | Agxt2 |
| 7482 | 3 | 4 | 5 | | | V-1 | Ahi1 |
| 7483 | 3 | 4 | 5 | | | V-1 | Ahnak |
| 7484 | 3 | 4 | 5 | | | V-1 | Ahr |
| 7485 | 3 | 4 | 5 | | | V-1 | AI413582 |
| 7486 | 3 | 4 | 5 | | | V-1 | AI414108 |
| 7487 | 3 | 4 | 5 | | | V-1 | AI429214 |
| 7488 | 3 | 4 | 5 | | | V-1 | AI450353 |
| 7489 | 3 | 4 | 5 | | | V-1 | AI462493 |
| 7490 | 3 | 4 | 5 | | | V-1 | AI839979 |
| 7491 | 3 | 4 | 5 | | | V-1 | Aif1 |
| 7492 | 3 | 4 | 5 | | | V-1 | Aif1l |
| 7493 | 3 | 4 | 5 | | | V-1 | Aig1 |
| 7494 | 3 | 4 | 5 | | | V-1 | Aim2 |
| 7495 | 3 | 4 | 5 | | | V-1 | Ak2 |
| 7496 | 3 | 4 | 5 | | | V-1 | Ak4 |
| 7497 | 3 | 4 | 5 | | | V-1 | Ak5 |
| 7498 | 3 | 4 | 5 | | | V-1 | Akap1 |
| 7499 | 3 | 4 | 5 | | | V-1 | Akap11 |
| 7500 | 3 | 4 | 5 | | | V-1 | Akap13 |
| 7501 | 3 | 4 | 5 | | | V-1 | Akap17b |
| 7502 | 3 | 4 | 5 | | | V-1 | Akap9 |
| 7503 | 3 | 4 | 5 | | | V-1 | Akr1a1 |
| 7504 | 3 | 4 | 5 | | | V-1 | Akr1b10 |
| 7505 | 3 | 4 | 5 | | | V-1 | Akr1b7 |
| 7506 | 3 | 4 | 5 | | | V-1 | Akr1c13 |
| 7507 | 3 | 4 | 5 | | | V-1 | Akr1c14 |
| 7508 | 3 | 4 | 5 | | | V-1 | Alas1 |
| 7509 | 3 | 4 | 5 | | | V-1 | Alcam |
| 7510 | 3 | 4 | 5 | | | V-1 | Aldh18a1 |
| 7511 | 3 | 4 | 5 | | | V-1 | Aldh1a2 |
| 7512 | 3 | 4 | 5 | | | V-1 | Aldh1a3 |
| 7513 | 3 | 4 | 5 | | | V-1 | Aldh1l1 |
| 7514 | 3 | 4 | 5 | | | V-1 | Aldh3a1 |
| 7515 | 3 | 4 | 5 | | | V-1 | Aldh3b1 |
| 7516 | 3 | 4 | 5 | | | V-1 | Aldh5a1 |
| 7517 | 3 | 4 | 5 | | | V-1 | Aldh6a1 |
| 7518 | 3 | 4 | 5 | | | V-1 | Aldh7a1 |
| 7519 | 3 | 4 | 5 | | | V-1 | Alg6 |
| 7520 | 3 | 4 | 5 | | | V-1 | Alg8 |
| 7521 | 3 | 4 | 5 | | | V-1 | Alkbh2 |
| 7522 | 3 | 4 | 5 | | | V-1 | Alkbh3 |
| 7523 | 3 | 4 | 5 | | | V-1 | Alkbh6 |
| 7524 | 3 | 4 | 5 | | | V-1 | Alkbh7 |
| 7525 | 3 | 4 | 5 | | | V-1 | Alkbh8 |
| 7526 | 3 | 4 | 5 | | | V-1 | Alox12b |
| 7527 | 3 | 4 | 5 | | | V-1 | Als2cr12 |
| 7528 | 3 | 4 | 5 | | | V-1 | Alyref |
| 7529 | 3 | 4 | 5 | | | V-1 | Amdhd2 |
| 7530 | 3 | 4 | 5 | | | V-1 | Amer1 |
| 7531 | 3 | 4 | 5 | | | V-1 | Amigo3 |
| 7532 | 3 | 4 | 5 | | | V-1 | Anapc1 |
| 7533 | 3 | 4 | 5 | | | V-1 | Anapc13 |
| 7534 | 3 | 4 | 5 | | | V-1 | Ang |
| 7535 | 3 | 4 | 5 | | | V-1 | Angpt1 |
| 7536 | 3 | 4 | 5 | | | V-1 | Angpt2 |
| 7537 | 3 | 4 | 5 | | | V-1 | Ank2 |
| 7538 | 3 | 4 | 5 | | | V-1 | Ankfy1 |
| 7539 | 3 | 4 | 5 | | | V-1 | Ankrd13b |
| 7540 | 3 | 4 | 5 | | | V-1 | Ankrd28 |
| 7541 | 3 | 4 | 5 | | | V-1 | Ankrd35 |
| 7542 | 3 | 4 | 5 | | | V-1 | Anks4b |
| 7543 | 3 | 4 | 5 | | | V-1 | Ano6 |
| 7544 | 3 | 4 | 5 | | | V-1 | Anpep |
| 7545 | 3 | 4 | 5 | | | V-1 | Antxr1 |
| 7546 | 3 | 4 | 5 | | | V-1 | Anxa11 |
| 7547 | 3 | 4 | 5 | | | V-1 | Anxa13 |
| 7548 | 3 | 4 | 5 | | | V-1 | Anxa2 |
| 7549 | 3 | 4 | 5 | | | V-1 | Anxa3 |
| 7550 | 3 | 4 | 5 | | | V-1 | Anxa4 |
| 7551 | 3 | 4 | 5 | | | V-1 | Anxa5 |
| 7552 | 3 | 4 | 5 | | | V-1 | Anxa9 |
| 7553 | 3 | 4 | 5 | | | V-1 | Aoah |
| 7554 | 3 | 4 | 5 | | | V-1 | Aoc1 |
| 7555 | 3 | 4 | 5 | | | V-1 | Ap1s1 |
| 7556 | 3 | 4 | 5 | | | V-1 | Ap2s1 |
| 7557 | 3 | 4 | 5 | | | V-1 | Ap3m1 |
| 7558 | 3 | 4 | 5 | | | V-1 | Ap3s1 |
| 7559 | 3 | 4 | 5 | | | V-1 | Ap4s1 |
| 7560 | 3 | 4 | 5 | | | V-1 | Ap5s1 |
| 7561 | 3 | 4 | 5 | | | V-1 | Apaf1 |
| 7562 | 3 | 4 | 5 | | | V-1 | Apbb1ip |
| 7563 | 3 | 4 | 5 | | | V-1 | Apbb3 |
| 7564 | 3 | 4 | 5 | | | V-1 | Apc |
| 7565 | 3 | 4 | 5 | | | V-1 | Apex2 |
| 7566 | 3 | 4 | 5 | | | V-1 | Aph1b |
| 7567 | 3 | 4 | 5 | | | V-1 | Apip |
| 7568 | 3 | 4 | 5 | | | V-1 | Apitd1 |
| 7569 | 3 | 4 | 5 | | | V-1 | Aplp1 |
| 7570 | 3 | 4 | 5 | | | V-1 | Apmap |
| 7571 | 3 | 4 | 5 | | | V-1 | Apoa1bp |
| 7572 | 3 | 4 | 5 | | | V-1 | Apof |
| 7573 | 3 | 4 | 5 | | | V-1 | Apol10b |
| 7574 | 3 | 4 | 5 | | | V-1 | Apol8 |
| 7575 | 3 | 4 | 5 | | | V-1 | Apold1 |
| 7576 | 3 | 4 | 5 | | | V-1 | Apool |
| 7577 | 3 | 4 | 5 | | | V-1 | Aprt |
| 7578 | 3 | 4 | 5 | | | V-1 | Aqp3 |
| 7579 | 3 | 4 | 5 | | | V-1 | Aqp5 |
| 7580 | 3 | 4 | 5 | | | V-1 | Areg |
| 7581 | 3 | 4 | 5 | | | V-1 | Arel1 |
| 7582 | 3 | 4 | 5 | | | V-1 | Arf5 |
| 7583 | 3 | 4 | 5 | | | V-1 | Arhgap19 |
| 7584 | 3 | 4 | 5 | | | V-1 | Arhgap20os |
| 7585 | 3 | 4 | 5 | | | V-1 | Arhgap22 |
| 7586 | 3 | 4 | 5 | | | V-1 | Arhgap23 |
| 7587 | 3 | 4 | 5 | | | V-1 | Arhgap24 |
| 7588 | 3 | 4 | 5 | | | V-1 | Arhgap30 |
| 7589 | 3 | 4 | 5 | | | V-1 | Arhgap4 |
| 7590 | 3 | 4 | 5 | | | V-1 | Arhgap8 |
| 7591 | 3 | 4 | 5 | | | V-1 | Arhgap9 |
| 7592 | 3 | 4 | 5 | | | V-1 | Arhgdib |
| 7593 | 3 | 4 | 5 | | | V-1 | Arhgef37 |
| 7594 | 3 | 4 | 5 | | | V-1 | Arhgef5 |
| 7595 | 3 | 4 | 5 | | | V-1 | Arhgef9 |
| 7596 | 3 | 4 | 5 | | | V-1 | Arid5a |
| 7597 | 3 | 4 | 5 | | | V-1 | Arl14ep |
| 7598 | 3 | 4 | 5 | | | V-1 | Arl2 |
| 7599 | 3 | 4 | 5 | | | V-1 | Arl2bp |
| 7600 | 3 | 4 | 5 | | | V-1 | Arl4c |
| 7601 | 3 | 4 | 5 | | | V-1 | Armcx4 |
| 7602 | 3 | 4 | 5 | | | V-1 | Armcx5 |
| 7603 | 3 | 4 | 5 | | | V-1 | Armcx6 |
| 7604 | 3 | 4 | 5 | | | V-1 | Arpc2 |
| 7605 | 3 | 4 | 5 | | | V-1 | Arpc4 |
| 7606 | 3 | 4 | 5 | | | V-1 | Arpc5l |
| 7607 | 3 | 4 | 5 | | | V-1 | Arpp19 |
| 7608 | 3 | 4 | 5 | | | V-1 | Arrdc3 |
| 7609 | 3 | 4 | 5 | | | V-1 | Arrdc4 |
| 7610 | 3 | 4 | 5 | | | V-1 | Arsb |
| 7611 | 3 | 4 | 5 | | | V-1 | Arsg |
| 7612 | 3 | 4 | 5 | | | V-1 | Art3 |
| 7613 | 3 | 4 | 5 | | | V-1 | Art4 |
| 7614 | 3 | 4 | 5 | | | V-1 | Arv1 |
| 7615 | 3 | 4 | 5 | | | V-1 | Arx |
| 7616 | 3 | 4 | 5 | | | V-1 | Asah2 |
| 7617 | 3 | 4 | 5 | | | V-1 | Asap2 |
| 7618 | 3 | 4 | 5 | | | V-1 | Asap3 |
| 7619 | 3 | 4 | 5 | | | V-1 | Asb14 |
| 7620 | 3 | 4 | 5 | | | V-1 | Asb16 |
| 7621 | 3 | 4 | 5 | | | V-1 | Asb7 |
| 7622 | 3 | 4 | 5 | | | V-1 | Aspa |
| 7623 | 3 | 4 | 5 | | | V-1 | Asph |
| 7624 | 3 | 4 | 5 | | | V-1 | Asrgl1 |
| 7625 | 3 | 4 | 5 | | | V-1 | Asxl2 |
| 7626 | 3 | 4 | 5 | | | V-1 | Atad3a |
| 7627 | 3 | 4 | 5 | | | V-1 | Atad5 |
| 7628 | 3 | 4 | 5 | | | V-1 | Atat1 |
| 7629 | 3 | 4 | 5 | | | V-1 | Atg10 |
| 7630 | 3 | 4 | 5 | | | V-1 | Atg4a |
| 7631 | 3 | 4 | 5 | | | V-1 | Atg9b |
| 7632 | 3 | 4 | 5 | | | V-1 | Atl1 |
| 7633 | 3 | 4 | 5 | | | V-1 | Atl3 |
| 7634 | 3 | 4 | 5 | | | V-1 | Atox1 |
| 7635 | 3 | 4 | 5 | | | V-1 | Atp10d |
| 7636 | 3 | 4 | 5 | | | V-1 | Atp13a2 |
| 7637 | 3 | 4 | 5 | | | V-1 | Atp1a1 |
| 7638 | 3 | 4 | 5 | | | V-1 | Atp1a3 |
| 7639 | 3 | 4 | 5 | | | V-1 | Atp2a2 |
| 7640 | 3 | 4 | 5 | | | V-1 | Atp5g1 |
| 7641 | 3 | 4 | 5 | | | V-1 | Atp5g2 |
| 7642 | 3 | 4 | 5 | | | V-1 | Atp5g3 |
| 7643 | 3 | 4 | 5 | | | V-1 | Atp5h |
| 7644 | 3 | 4 | 5 | | | V-1 | Atp5j2 |
| 7645 | 3 | 4 | 5 | | | V-1 | Atp5l |
| 7646 | 3 | 4 | 5 | | | V-1 | Atp5o |
| 7647 | 3 | 4 | 5 | | | V-1 | Atp6v0d2 |
| 7648 | 3 | 4 | 5 | | | V-1 | Atp6v1a |

Fig. 43 - 46

| | | | | | | | | |
|---|---|---|---|---|---|---|---|---|
| 7649 | 3 | 4 | 5 | | | V-1 | Atp6v1d |
| 7650 | 3 | 4 | 5 | | | V-1 | Atp8b1 |
| 7651 | 3 | 4 | 5 | | | V-1 | Atp8b4 |
| 7652 | 3 | 4 | 5 | | | V-1 | Atpaf2 |
| 7653 | 3 | 4 | 5 | | | V-1 | Atraid |
| 7654 | 3 | 4 | 5 | | | V-1 | Atrip |
| 7655 | 3 | 4 | 5 | | | V-1 | Atrn |
| 7656 | 3 | 4 | 5 | | | V-1 | Atrx |
| 7657 | 3 | 4 | 5 | | | V-1 | Atxn1 |
| 7658 | 3 | 4 | 5 | | | V-1 | Atxn2l |
| 7659 | 3 | 4 | 5 | | | V-1 | Atxn7 |
| 7660 | 3 | 4 | 5 | | | V-1 | Atxn7l1 |
| 7661 | 3 | 4 | 5 | | | V-1 | AU015791 |
| 7662 | 3 | 4 | 5 | | | V-1 | AU040972 |
| 7663 | 3 | 4 | 5 | | | V-1 | AU041133 |
| 7664 | 3 | 4 | 5 | | | V-1 | Aurkaip1 |
| 7665 | 3 | 4 | 5 | | | V-1 | Aurkb |
| 7666 | 3 | 4 | 5 | | | V-1 | AV039307 |
| 7667 | 3 | 4 | 5 | | | V-1 | Avpi1 |
| 7668 | 3 | 4 | 5 | | | V-1 | AW112010 |
| 7669 | 3 | 4 | 5 | | | V-1 | AW549542 |
| 7670 | 3 | 4 | 5 | | | V-1 | Axin2 |
| 7671 | 3 | 4 | 5 | | | V-1 | Axl |
| 7672 | 3 | 4 | 5 | | | V-1 | AY761184 |
| 7673 | 3 | 4 | 5 | | | V-1 | Azgp1 |
| 7674 | 3 | 4 | 5 | | | V-1 | Azin1 |
| 7675 | 3 | 4 | 5 | | | V-1 | 2230118H07Rik |
| 7676 | 3 | 4 | 5 | | | V-1 | 2230216G23Rik |
| 7677 | 3 | 4 | 5 | | | V-1 | 2230216N24Rik |
| 7678 | 3 | 4 | 5 | | | V-1 | B2m |
| 7679 | 3 | 4 | 5 | | | V-1 | B3galnt1 |
| 7680 | 3 | 4 | 5 | | | V-1 | B3galt1 |
| 7681 | 3 | 4 | 5 | | | V-1 | B3glct |
| 7682 | 3 | 4 | 5 | | | V-1 | B3gnt9 |
| 7683 | 3 | 4 | 5 | | | V-1 | B4galnt1 |
| 7684 | 3 | 4 | 5 | | | V-1 | B4galnt3 |
| 7685 | 3 | 4 | 5 | | | V-1 | B4galt5 |
| 7686 | 3 | 4 | 5 | | | V-1 | B830017H08Rik |
| 7687 | 3 | 4 | 5 | | | V-1 | B930041F14Rik |
| 7688 | 3 | 4 | 5 | | | V-1 | B930059L03Rik |
| 7689 | 3 | 4 | 5 | | | V-1 | B9d2 |
| 7690 | 3 | 4 | 5 | | | V-1 | Baiap2l2 |
| 7691 | 3 | 4 | 5 | | | V-1 | Bak1 |
| 7692 | 3 | 4 | 5 | | | V-1 | Barx2 |
| 7693 | 3 | 4 | 5 | | | V-1 | Batf |
| 7694 | 3 | 4 | 5 | | | V-1 | Batf2 |
| 7695 | 3 | 4 | 5 | | | V-1 | BB123696 |
| 7696 | 3 | 4 | 5 | | | V-1 | Bbc3 |
| 7697 | 3 | 4 | 5 | | | V-1 | Bbs1 |
| 7698 | 3 | 4 | 5 | | | V-1 | Bbs12 |
| 7699 | 3 | 4 | 5 | | | V-1 | Bbs2 |
| 7700 | 3 | 4 | 5 | | | V-1 | Bbs4 |
| 7701 | 3 | 4 | 5 | | | V-1 | Bbs7 |
| 7702 | 3 | 4 | 5 | | | V-1 | BC002163 |
| 7703 | 3 | 4 | 5 | | | V-1 | BC005537 |
| 7704 | 3 | 4 | 5 | | | V-1 | BC005764 |
| 7705 | 3 | 4 | 5 | | | V-1 | BC018242 |
| 7706 | 3 | 4 | 5 | | | V-1 | BC018507 |
| 7707 | 3 | 4 | 5 | | | V-1 | BC021767 |
| 7708 | 3 | 4 | 5 | | | V-1 | BC024139 |
| 7709 | 3 | 4 | 5 | | | V-1 | BC024978 |
| 7710 | 3 | 4 | 5 | | | V-1 | BC026585 |
| 7711 | 3 | 4 | 5 | | | V-1 | BC029214 |
| 7712 | 3 | 4 | 5 | | | V-1 | BC030867 |
| 7713 | 3 | 4 | 5 | | | V-1 | BC048507 |
| 7714 | 3 | 4 | 5 | | | V-1 | BC055324 |
| 7715 | 3 | 4 | 5 | | | V-1 | BC094916 |
| 7716 | 3 | 4 | 5 | | | V-1 | Bcam |
| 7717 | 3 | 4 | 5 | | | V-1 | Bcap29 |
| 7718 | 3 | 4 | 5 | | | V-1 | Bcar3 |
| 7719 | 3 | 4 | 5 | | | V-1 | Bcas2 |
| 7720 | 3 | 4 | 5 | | | V-1 | Bche |
| 7721 | 3 | 4 | 5 | | | V-1 | Bcl11a |
| 7722 | 3 | 4 | 5 | | | V-1 | Bcl2a1a |
| 7723 | 3 | 4 | 5 | | | V-1 | Bcl2a1d |
| 7724 | 3 | 4 | 5 | | | V-1 | Bcl2l11 |
| 7725 | 3 | 4 | 5 | | | V-1 | Bcl2l12 |
| 7726 | 3 | 4 | 5 | | | V-1 | Bcl3 |
| 7727 | 3 | 4 | 5 | | | V-1 | Bcl6b |
| 7728 | 3 | 4 | 5 | | | V-1 | Bco2 |
| 7729 | 3 | 4 | 5 | | | V-1 | Bdh2 |
| 7730 | 3 | 4 | 5 | | | V-1 | Bdkrb1 |
| 7731 | 3 | 4 | 5 | | | V-1 | Best3 |
| 7732 | 3 | 4 | 5 | | | V-1 | Bet1l |
| 7733 | 3 | 4 | 5 | | | V-1 | Bex6 |
| 7734 | 3 | 4 | 5 | | | V-1 | Bfsp1 |
| 7735 | 3 | 4 | 5 | | | V-1 | Bglap3 |
| 7736 | 3 | 4 | 5 | | | V-1 | Bhlhe40 |
| 7737 | 3 | 4 | 5 | | | V-1 | Bhlhe41 |
| 7738 | 3 | 4 | 5 | | | V-1 | Bhmt2 |
| 7739 | 3 | 4 | 5 | | | V-1 | Bicd1 |
| 7740 | 3 | 4 | 5 | | | V-1 | Bid |
| 7741 | 3 | 4 | 5 | | | V-1 | Bin1 |
| 7742 | 3 | 4 | 5 | | | V-1 | Bin2 |
| 7743 | 3 | 4 | 5 | | | V-1 | Blm |
| 7744 | 3 | 4 | 5 | | | V-1 | Bloc1s1 |
| 7745 | 3 | 4 | 5 | | | V-1 | Bloc1s5 |
| 7746 | 3 | 4 | 5 | | | V-1 | Blvra |
| 7747 | 3 | 4 | 5 | | | V-1 | Blvrb |
| 7748 | 3 | 4 | 5 | | | V-1 | Bmp3 |
| 7749 | 3 | 4 | 5 | | | V-1 | Bmp4 |
| 7750 | 3 | 4 | 5 | | | V-1 | Bmp5 |
| 7751 | 3 | 4 | 5 | | | V-1 | Bmp7 |
| 7752 | 3 | 4 | 5 | | | V-1 | Bmpr1a |
| 7753 | 3 | 4 | 5 | | | V-1 | Bmyc |
| 7754 | 3 | 4 | 5 | | | V-1 | Bnc1 |
| 7755 | 3 | 4 | 5 | | | V-1 | Bnip1 |
| 7756 | 3 | 4 | 5 | | | V-1 | Bnip3 |
| 7757 | 3 | 4 | 5 | | | V-1 | Bnipl |
| 7758 | 3 | 4 | 5 | | | V-1 | Boc |
| 7759 | 3 | 4 | 5 | | | V-1 | Bola1 |
| 7760 | 3 | 4 | 5 | | | V-1 | Bola2 |
| 7761 | 3 | 4 | 5 | | | V-1 | Bora |
| 7762 | 3 | 4 | 5 | | | V-1 | Braf |
| 7763 | 3 | 4 | 5 | | | V-1 | Brcc3 |
| 7764 | 3 | 4 | 5 | | | V-1 | Brdt |
| 7765 | 3 | 4 | 5 | | | V-1 | Bre |
| 7766 | 3 | 4 | 5 | | | V-1 | Brf2 |
| 7767 | 3 | 4 | 5 | | | V-1 | Brinp2 |
| 7768 | 3 | 4 | 5 | | | V-1 | Brms1 |
| 7769 | 3 | 4 | 5 | | | V-1 | Bscl2 |
| 7770 | 3 | 4 | 5 | | | V-1 | Bsg |
| 7771 | 3 | 4 | 5 | | | V-1 | Btbd19 |
| 7772 | 3 | 4 | 5 | | | V-1 | Btf3 |
| 7773 | 3 | 4 | 5 | | | V-1 | Btn2a2 |
| 7774 | 3 | 4 | 5 | | | V-1 | Btnl4 |
| 7775 | 3 | 4 | 5 | | | V-1 | Bub1b |
| 7776 | 3 | 4 | 5 | | | V-1 | Bud31 |
| 7777 | 3 | 4 | 5 | | | V-1 | Bysl |
| 7778 | 3 | 4 | 5 | | | V-1 | Bzrap1 |
| 7779 | 3 | 4 | 5 | | | V-1 | Bzw2 |
| 7780 | 3 | 4 | 5 | | | V-1 | C030006K11Rik |
| 7781 | 3 | 4 | 5 | | | V-1 | C030037D09Rik |
| 7782 | 3 | 4 | 5 | | | V-1 | C130026L21Rik |
| 7783 | 3 | 4 | 5 | | | V-1 | C1d |
| 7784 | 3 | 4 | 5 | | | V-1 | C1qa |
| 7785 | 3 | 4 | 5 | | | V-1 | C1qb |
| 7786 | 3 | 4 | 5 | | | V-1 | C1qc |
| 7787 | 3 | 4 | 5 | | | V-1 | C1qtnf1 |
| 7788 | 3 | 4 | 5 | | | V-1 | C1qtnf3 |
| 7789 | 3 | 4 | 5 | | | V-1 | C1qtnf5 |
| 7790 | 3 | 4 | 5 | | | V-1 | C1rl |
| 7791 | 3 | 4 | 5 | | | V-1 | C1s2 |
| 7792 | 3 | 4 | 5 | | | V-1 | C2 |
| 7793 | 3 | 4 | 5 | | | V-1 | C2cd4b |
| 7794 | 3 | 4 | 5 | | | V-1 | C330013E15Rik |
| 7795 | 3 | 4 | 5 | | | V-1 | C3ar1 |
| 7796 | 3 | 4 | 5 | | | V-1 | C630043F03Rik |
| 7797 | 3 | 4 | 5 | | | V-1 | C7 |
| 7798 | 3 | 4 | 5 | | | V-1 | C730027H18Rik |
| 7799 | 3 | 4 | 5 | | | V-1 | C8g |
| 7800 | 3 | 4 | 5 | | | V-1 | C920006O11Rik |
| 7801 | 3 | 4 | 5 | | | V-1 | C920021L13Rik |
| 7802 | 3 | 4 | 5 | | | V-1 | Caap1 |
| 7803 | 3 | 4 | 5 | | | V-1 | Cachd1 |
| 7804 | 3 | 4 | 5 | | | V-1 | Cacna1h |
| 7805 | 3 | 4 | 5 | | | V-1 | Cacnb2 |
| 7806 | 3 | 4 | 5 | | | V-1 | Cacybp |
| 7807 | 3 | 4 | 5 | | | V-1 | Calm1 |
| 7808 | 3 | 4 | 5 | | | V-1 | Calm2 |
| 7809 | 3 | 4 | 5 | | | V-1 | Calr |
| 7810 | 3 | 4 | 5 | | | V-1 | Calr3 |
| 7811 | 3 | 4 | 5 | | | V-1 | Camk2b |
| 7812 | 3 | 4 | 5 | | | V-1 | Camk2n2 |
| 7813 | 3 | 4 | 5 | | | V-1 | Camta1 |
| 7814 | 3 | 4 | 5 | | | V-1 | Capg |
| 7815 | 3 | 4 | 5 | | | V-1 | Capns1 |
| 7816 | 3 | 4 | 5 | | | V-1 | Capns2 |
| 7817 | 3 | 4 | 5 | | | V-1 | Car12 |
| 7818 | 3 | 4 | 5 | | | V-1 | Car13 |

Fig. 43 - 47

| | | | | | | | |
|---|---|---|---|---|---|---|---|
| 7819 | 3 | 4 | 5 | | | V-1 | Carns1 |
| 7820 | 3 | 4 | 5 | | | V-1 | Cars |
| 7821 | 3 | 4 | 5 | | | V-1 | Casc4 |
| 7822 | 3 | 4 | 5 | | | V-1 | Casp12 |
| 7823 | 3 | 4 | 5 | | | V-1 | Casp3 |
| 7824 | 3 | 4 | 5 | | | V-1 | Casp7 |
| 7825 | 3 | 4 | 5 | | | V-1 | Casp8 |
| 7826 | 3 | 4 | 5 | | | V-1 | Casz1 |
| 7827 | 3 | 4 | 5 | | | V-1 | Catip |
| 7828 | 3 | 4 | 5 | | | V-1 | Cav2 |
| 7829 | 3 | 4 | 5 | | | V-1 | Cbr2 |
| 7830 | 3 | 4 | 5 | | | V-1 | Cbx4 |
| 7831 | 3 | 4 | 5 | | | V-1 | Cby1 |
| 7832 | 3 | 4 | 5 | | | V-1 | Ccdc103 |
| 7833 | 3 | 4 | 5 | | | V-1 | Ccdc104 |
| 7834 | 3 | 4 | 5 | | | V-1 | Ccdc106 |
| 7835 | 3 | 4 | 5 | | | V-1 | Ccdc107 |
| 7836 | 3 | 4 | 5 | | | V-1 | Ccdc115 |
| 7837 | 3 | 4 | 5 | | | V-1 | Ccdc116 |
| 7838 | 3 | 4 | 5 | | | V-1 | Ccdc124 |
| 7839 | 3 | 4 | 5 | | | V-1 | Ccdc125 |
| 7840 | 3 | 4 | 5 | | | V-1 | Ccdc14 |
| 7841 | 3 | 4 | 5 | | | V-1 | Ccdc17 |
| 7842 | 3 | 4 | 5 | | | V-1 | Ccdc176 |
| 7843 | 3 | 4 | 5 | | | V-1 | Ccdc23 |
| 7844 | 3 | 4 | 5 | | | V-1 | Ccdc57 |
| 7845 | 3 | 4 | 5 | | | V-1 | Ccdc69 |
| 7846 | 3 | 4 | 5 | | | V-1 | Ccdc8 |
| 7847 | 3 | 4 | 5 | | | V-1 | Ccdc82 |
| 7848 | 3 | 4 | 5 | | | V-1 | Ccdc84 |
| 7849 | 3 | 4 | 5 | | | V-1 | Ccdc86 |
| 7850 | 3 | 4 | 5 | | | V-1 | Ccdc88b |
| 7851 | 3 | 4 | 5 | | | V-1 | Cck |
| 7852 | 3 | 4 | 5 | | | V-1 | Cckar |
| 7853 | 3 | 4 | 5 | | | V-1 | Ccl12 |
| 7854 | 3 | 4 | 5 | | | V-1 | Ccl19 |
| 7855 | 3 | 4 | 5 | | | V-1 | Ccl21c |
| 7856 | 3 | 4 | 5 | | | V-1 | Ccl24 |
| 7857 | 3 | 4 | 5 | | | V-1 | Ccl4 |
| 7858 | 3 | 4 | 5 | | | V-1 | Ccl6 |
| 7859 | 3 | 4 | 5 | | | V-1 | Ccl9 |
| 7860 | 3 | 4 | 5 | | | V-1 | Ccna2 |
| 7861 | 3 | 4 | 5 | | | V-1 | Ccne1 |
| 7862 | 3 | 4 | 5 | | | V-1 | Ccno |
| 7863 | 3 | 4 | 5 | | | V-1 | Ccnt2 |
| 7864 | 3 | 4 | 5 | | | V-1 | Ccpg1os |
| 7865 | 3 | 4 | 5 | | | V-1 | Ccr7 |
| 7866 | 3 | 4 | 5 | | | V-1 | Ccrl2 |
| 7867 | 3 | 4 | 5 | | | V-1 | Cct3 |
| 7868 | 3 | 4 | 5 | | | V-1 | Cct6a |
| 7869 | 3 | 4 | 5 | | | V-1 | Ccz1 |
| 7870 | 3 | 4 | 5 | | | V-1 | Cd109 |
| 7871 | 3 | 4 | 5 | | | V-1 | Cd14 |
| 7872 | 3 | 4 | 5 | | | V-1 | Cd163 |
| 7873 | 3 | 4 | 5 | | | V-1 | Cd164l2 |
| 7874 | 3 | 4 | 5 | | | V-1 | Cd209b |
| 7875 | 3 | 4 | 5 | | | V-1 | Cd244 |
| 7876 | 3 | 4 | 5 | | | V-1 | Cd276 |
| 7877 | 3 | 4 | 5 | | | V-1 | Cd300a |
| 7878 | 3 | 4 | 5 | | | V-1 | Cd302 |
| 7879 | 3 | 4 | 5 | | | V-1 | Cd320 |
| 7880 | 3 | 4 | 5 | | | V-1 | Cd34 |
| 7881 | 3 | 4 | 5 | | | V-1 | Cd37 |
| 7882 | 3 | 4 | 5 | | | V-1 | Cd38 |
| 7883 | 3 | 4 | 5 | | | V-1 | Cd3d |
| 7884 | 3 | 4 | 5 | | | V-1 | Cd44 |
| 7885 | 3 | 4 | 5 | | | V-1 | Cd47 |
| 7886 | 3 | 4 | 5 | | | V-1 | Cd53 |
| 7887 | 3 | 4 | 5 | | | V-1 | Cd55 |
| 7888 | 3 | 4 | 5 | | | V-1 | Cd69 |
| 7889 | 3 | 4 | 5 | | | V-1 | Cd84 |
| 7890 | 3 | 4 | 5 | | | V-1 | Cd9 |
| 7891 | 3 | 4 | 5 | | | V-1 | Cdc23 |
| 7892 | 3 | 4 | 5 | | | V-1 | Cdc34 |
| 7893 | 3 | 4 | 5 | | | V-1 | Cdc42bpg |
| 7894 | 3 | 4 | 5 | | | V-1 | Cdc6 |
| 7895 | 3 | 4 | 5 | | | V-1 | Cdca3 |
| 7896 | 3 | 4 | 5 | | | V-1 | Cdca5 |
| 7897 | 3 | 4 | 5 | | | V-1 | Cdca7 |
| 7898 | 3 | 4 | 5 | | | V-1 | Cdca8 |
| 7899 | 3 | 4 | 5 | | | V-1 | Cdh3 |
| 7900 | 3 | 4 | 5 | | | V-1 | Cdh4 |
| 7901 | 3 | 4 | 5 | | | V-1 | Cdh6 |
| 7902 | 3 | 4 | 5 | | | V-1 | Cdhr2 |
| 7903 | 3 | 4 | 5 | | | V-1 | Cdk10 |
| 7904 | 3 | 4 | 5 | | | V-1 | Cdk12 |
| 7905 | 3 | 4 | 5 | | | V-1 | Cdk18 |
| 7906 | 3 | 4 | 5 | | | V-1 | Cdk2ap1 |
| 7907 | 3 | 4 | 5 | | | V-1 | Cdk5rap2 |
| 7908 | 3 | 4 | 5 | | | V-1 | Cdkal1 |
| 7909 | 3 | 4 | 5 | | | V-1 | Cdon |
| 7910 | 3 | 4 | 5 | | | V-1 | Cds2 |
| 7911 | 3 | 4 | 5 | | | V-1 | Ceacam16 |
| 7912 | 3 | 4 | 5 | | | V-1 | Ceacam-ps1 |
| 7913 | 3 | 4 | 5 | | | V-1 | Cebpa |
| 7914 | 3 | 4 | 5 | | | V-1 | Celf2 |
| 7915 | 3 | 4 | 5 | | | V-1 | Cenpa |
| 7916 | 3 | 4 | 5 | | | V-1 | Cenpk |
| 7917 | 3 | 4 | 5 | | | V-1 | Cenpm |
| 7918 | 3 | 4 | 5 | | | V-1 | Cenpn |
| 7919 | 3 | 4 | 5 | | | V-1 | Cenpo |
| 7920 | 3 | 4 | 5 | | | V-1 | Cenpp |
| 7921 | 3 | 4 | 5 | | | V-1 | Cenpu |
| 7922 | 3 | 4 | 5 | | | V-1 | Cep152 |
| 7923 | 3 | 4 | 5 | | | V-1 | Cep44 |
| 7924 | 3 | 4 | 5 | | | V-1 | Cep70 |
| 7925 | 3 | 4 | 5 | | | V-1 | Cep78 |
| 7926 | 3 | 4 | 5 | | | V-1 | Cep83os |
| 7927 | 3 | 4 | 5 | | | V-1 | Cep85 |
| 7928 | 3 | 4 | 5 | | | V-1 | Cercam |
| 7929 | 3 | 4 | 5 | | | V-1 | Cers3 |
| 7930 | 3 | 4 | 5 | | | V-1 | Ces1b |
| 7931 | 3 | 4 | 5 | | | V-1 | Ces1f |
| 7932 | 3 | 4 | 5 | | | V-1 | Ces1g |
| 7933 | 3 | 4 | 5 | | | V-1 | Ces2c |
| 7934 | 3 | 4 | 5 | | | V-1 | Ces2f |
| 7935 | 3 | 4 | 5 | | | V-1 | Cetn3 |
| 7936 | 3 | 4 | 5 | | | V-1 | Cfhr2 |
| 7937 | 3 | 4 | 5 | | | V-1 | Cfl1 |
| 7938 | 3 | 4 | 5 | | | V-1 | Cfl2 |
| 7939 | 3 | 4 | 5 | | | V-1 | Cfp |
| 7940 | 3 | 4 | 5 | | | V-1 | Cgn |
| 7941 | 3 | 4 | 5 | | | V-1 | Cgnl1 |
| 7942 | 3 | 4 | 5 | | | V-1 | Cgref1 |
| 7943 | 3 | 4 | 5 | | | V-1 | Chaf1b |
| 7944 | 3 | 4 | 5 | | | V-1 | Chchd10 |
| 7945 | 3 | 4 | 5 | | | V-1 | Chchd2 |
| 7946 | 3 | 4 | 5 | | | V-1 | Chchd4 |
| 7947 | 3 | 4 | 5 | | | V-1 | Chd1l |
| 7948 | 3 | 4 | 5 | | | V-1 | Chd3 |
| 7949 | 3 | 4 | 5 | | | V-1 | Chd6 |
| 7950 | 3 | 4 | 5 | | | V-1 | Chd7 |
| 7951 | 3 | 4 | 5 | | | V-1 | Chek1 |
| 7952 | 3 | 4 | 5 | | | V-1 | Chic1 |
| 7953 | 3 | 4 | 5 | | | V-1 | Chit1 |
| 7954 | 3 | 4 | 5 | | | V-1 | Chmp2a |
| 7955 | 3 | 4 | 5 | | | V-1 | Chmp4b |
| 7956 | 3 | 4 | 5 | | | V-1 | Chodl |
| 7957 | 3 | 4 | 5 | | | V-1 | Chpf2 |
| 7958 | 3 | 4 | 5 | | | V-1 | Chrnb1 |
| 7959 | 3 | 4 | 5 | | | V-1 | Chrne |
| 7960 | 3 | 4 | 5 | | | V-1 | Chst11 |
| 7961 | 3 | 4 | 5 | | | V-1 | Chst14 |
| 7962 | 3 | 4 | 5 | | | V-1 | Chst2 |
| 7963 | 3 | 4 | 5 | | | V-1 | Chst8 |
| 7964 | 3 | 4 | 5 | | | V-1 | Chsy1 |
| 7965 | 3 | 4 | 5 | | | V-1 | Churc1 |
| 7966 | 3 | 4 | 5 | | | V-1 | Cib1 |
| 7967 | 3 | 4 | 5 | | | V-1 | Cidea |
| 7968 | 3 | 4 | 5 | | | V-1 | Cirh1a |
| 7969 | 3 | 4 | 5 | | | V-1 | Ckb |
| 7970 | 3 | 4 | 5 | | | V-1 | Cklf |
| 7971 | 3 | 4 | 5 | | | V-1 | Cks1b |
| 7972 | 3 | 4 | 5 | | | V-1 | Clasrp |
| 7973 | 3 | 4 | 5 | | | V-1 | Clca5 |
| 7974 | 3 | 4 | 5 | | | V-1 | Cldn12 |
| 7975 | 3 | 4 | 5 | | | V-1 | Cldn20 |
| 7976 | 3 | 4 | 5 | | | V-1 | Clec12b |
| 7977 | 3 | 4 | 5 | | | V-1 | Clec14a |
| 7978 | 3 | 4 | 5 | | | V-1 | Clec2g |
| 7979 | 3 | 4 | 5 | | | V-1 | Clec2i |
| 7980 | 3 | 4 | 5 | | | V-1 | Clec4a1 |
| 7981 | 3 | 4 | 5 | | | V-1 | Clec4a2 |
| 7982 | 3 | 4 | 5 | | | V-1 | Clec4a3 |
| 7983 | 3 | 4 | 5 | | | V-1 | Clec4n |
| 7984 | 3 | 4 | 5 | | | V-1 | Clec7a |
| 7985 | 3 | 4 | 5 | | | V-1 | Clhc1 |
| 7986 | 3 | 4 | 5 | | | V-1 | Clic1 |
| 7987 | 3 | 4 | 5 | | | V-1 | Clic4 |
| 7988 | 3 | 4 | 5 | | | V-1 | Clic5 |

Fig. 43 - 48

| | | | | | | | | | | | | | | | |
|---|---|---|---|---|---|---|---|---|---|---|---|---|---|---|---|
| 7989 | 3 | 4 | 5 | | | V-1 | Clkp4 | 8074 | 3 | 4 | 5 | | | V-1 | Cry1 |
| 7990 | 3 | 4 | 5 | | | V-1 | Clmp | 8075 | 3 | 4 | 5 | | | V-1 | Cryba4 |
| 7991 | 3 | 4 | 5 | | | V-1 | Clns1a | 8076 | 3 | 4 | 5 | | | V-1 | Cryga |
| 7992 | 3 | 4 | 5 | | | V-1 | Clpp | 8077 | 3 | 4 | 5 | | | V-1 | Cryl1 |
| 7993 | 3 | 4 | 5 | | | V-1 | Clstn3 | 8078 | 3 | 4 | 5 | | | V-1 | Crym |
| 7994 | 3 | 4 | 5 | | | V-1 | Cltb | 8079 | 3 | 4 | 5 | | | V-1 | Csf1 |
| 7995 | 3 | 4 | 5 | | | V-1 | Clybl | 8080 | 3 | 4 | 5 | | | V-1 | Csf1r |
| 7996 | 3 | 4 | 5 | | | V-1 | Cmc2 | 8081 | 3 | 4 | 5 | | | V-1 | Csf2rb |
| 7997 | 3 | 4 | 5 | | | V-1 | Cmklr1 | 8082 | 3 | 4 | 5 | | | V-1 | Csf2rb2 |
| 7998 | 3 | 4 | 5 | | | V-1 | Cnbp | 8083 | 3 | 4 | 5 | | | V-1 | Csl |
| 7999 | 3 | 4 | 5 | | | V-1 | Cngb3 | 8084 | 3 | 4 | 5 | | | V-1 | Csnk1g1 |
| 8000 | 3 | 4 | 5 | | | V-1 | Cnih1 | 8085 | 3 | 4 | 5 | | | V-1 | Cspg4 |
| 8001 | 3 | 4 | 5 | | | V-1 | Cnksr3 | 8086 | 3 | 4 | 5 | | | V-1 | Csrnp2 |
| 8002 | 3 | 4 | 5 | | | V-1 | Cnn1 | 8087 | 3 | 4 | 5 | | | V-1 | Csrp1 |
| 8003 | 3 | 4 | 5 | | | V-1 | Cnn2 | 8088 | 3 | 4 | 5 | | | V-1 | Cst6 |
| 8004 | 3 | 4 | 5 | | | V-1 | Cnnm2 | 8089 | 3 | 4 | 5 | | | V-1 | Cst7 |
| 8005 | 3 | 4 | 5 | | | V-1 | Cnot1 | 8090 | 3 | 4 | 5 | | | V-1 | Cstb |
| 8006 | 3 | 4 | 5 | | | V-1 | Cnot3 | 8091 | 3 | 4 | 5 | | | V-1 | Cstf3 |
| 8007 | 3 | 4 | 5 | | | V-1 | Coa3 | 8092 | 3 | 4 | 5 | | | V-1 | Ctla2b |
| 8008 | 3 | 4 | 5 | | | V-1 | Cobl | 8093 | 3 | 4 | 5 | | | V-1 | Ctla4 |
| 8009 | 3 | 4 | 5 | | | V-1 | Cobll1 | 8094 | 3 | 4 | 5 | | | V-1 | Ctnnal1 |
| 8010 | 3 | 4 | 5 | | | V-1 | Coch | 8095 | 3 | 4 | 5 | | | V-1 | Ctps |
| 8011 | 3 | 4 | 5 | | | V-1 | Col14a1 | 8096 | 3 | 4 | 5 | | | V-1 | Ctsb |
| 8012 | 3 | 4 | 5 | | | V-1 | Col16a1 | 8097 | 3 | 4 | 5 | | | V-1 | Ctsf |
| 8013 | 3 | 4 | 5 | | | V-1 | Col17a1 | 8098 | 3 | 4 | 5 | | | V-1 | Ctsh |
| 8014 | 3 | 4 | 5 | | | V-1 | Col18a1 | 8099 | 3 | 4 | 5 | | | V-1 | Ctsj |
| 8015 | 3 | 4 | 5 | | | V-1 | Col27a1 | 8100 | 3 | 4 | 5 | | | V-1 | Ctsk |
| 8016 | 3 | 4 | 5 | | | V-1 | Col4a5 | 8101 | 3 | 4 | 5 | | | V-1 | Ctsl |
| 8017 | 3 | 4 | 5 | | | V-1 | Col6a1 | 8102 | 3 | 4 | 5 | | | V-1 | Ctsz |
| 8018 | 3 | 4 | 5 | | | V-1 | Col6a3 | 8103 | 3 | 4 | 5 | | | V-1 | Cttnbp2nl |
| 8019 | 3 | 4 | 5 | | | V-1 | Col8a1 | 8104 | 3 | 4 | 5 | | | V-1 | Cuta |
| 8020 | 3 | 4 | 5 | | | V-1 | Col8a2 | 8105 | 3 | 4 | 5 | | | V-1 | Cux2 |
| 8021 | 3 | 4 | 5 | | | V-1 | Commd1 | 8106 | 3 | 4 | 5 | | | V-1 | Cwc27 |
| 8022 | 3 | 4 | 5 | | | V-1 | Commd2 | 8107 | 3 | 4 | 5 | | | V-1 | Cwf19l1 |
| 8023 | 3 | 4 | 5 | | | V-1 | Commd4 | 8108 | 3 | 4 | 5 | | | V-1 | Cx3cl1 |
| 8024 | 3 | 4 | 5 | | | V-1 | Comt | 8109 | 3 | 4 | 5 | | | V-1 | Cxadr |
| 8025 | 3 | 4 | 5 | | | V-1 | Comtd1 | 8110 | 3 | 4 | 5 | | | V-1 | Cxcl11 |
| 8026 | 3 | 4 | 5 | | | V-1 | Cope | 8111 | 3 | 4 | 5 | | | V-1 | Cxcl12 |
| 8027 | 3 | 4 | 5 | | | V-1 | Coprs | 8112 | 3 | 4 | 5 | | | V-1 | Cxcl14 |
| 8028 | 3 | 4 | 5 | | | V-1 | Cops4 | 8113 | 3 | 4 | 5 | | | V-1 | Cxcl17 |
| 8029 | 3 | 4 | 5 | | | V-1 | Cops6 | 8114 | 3 | 4 | 5 | | | V-1 | Cxcr3 |
| 8030 | 3 | 4 | 5 | | | V-1 | Coq2 | 8115 | 3 | 4 | 5 | | | V-1 | Cxx1b |
| 8031 | 3 | 4 | 5 | | | V-1 | Coq5 | 8116 | 3 | 4 | 5 | | | V-1 | Cxx1c |
| 8032 | 3 | 4 | 5 | | | V-1 | Coq7 | 8117 | 3 | 4 | 5 | | | V-1 | Cyb5r1 |
| 8033 | 3 | 4 | 5 | | | V-1 | Coro1a | 8118 | 3 | 4 | 5 | | | V-1 | Cyba |
| 8034 | 3 | 4 | 5 | | | V-1 | Coro1c | 8119 | 3 | 4 | 5 | | | V-1 | Cybb |
| 8035 | 3 | 4 | 5 | | | V-1 | Coro7 | 8120 | 3 | 4 | 5 | | | V-1 | Cycs |
| 8036 | 3 | 4 | 5 | | | V-1 | Cotl1 | 8121 | 3 | 4 | 5 | | | V-1 | Cyp1a2 |
| 8037 | 3 | 4 | 5 | | | V-1 | Cox10 | 8122 | 3 | 4 | 5 | | | V-1 | Cyp1b1 |
| 8038 | 3 | 4 | 5 | | | V-1 | Cox11 | 8123 | 3 | 4 | 5 | | | V-1 | Cyp20a1 |
| 8039 | 3 | 4 | 5 | | | V-1 | Cox14 | 8124 | 3 | 4 | 5 | | | V-1 | Cyp24a1 |
| 8040 | 3 | 4 | 5 | | | V-1 | Cox15 | 8125 | 3 | 4 | 5 | | | V-1 | Cyp2a12 |
| 8041 | 3 | 4 | 5 | | | V-1 | Cox17 | 8126 | 3 | 4 | 5 | | | V-1 | Cyp2a4 |
| 8042 | 3 | 4 | 5 | | | V-1 | Cox18 | 8127 | 3 | 4 | 5 | | | V-1 | Cyp2ab1 |
| 8043 | 3 | 4 | 5 | | | V-1 | Cox19 | 8128 | 3 | 4 | 5 | | | V-1 | Cyp2c67 |
| 8044 | 3 | 4 | 5 | | | V-1 | Cox20 | 8129 | 3 | 4 | 5 | | | V-1 | Cyp2d22 |
| 8045 | 3 | 4 | 5 | | | V-1 | Cox4i1 | 8130 | 3 | 4 | 5 | | | V-1 | Cyp2j6 |
| 8046 | 3 | 4 | 5 | | | V-1 | Cox5a | 8131 | 3 | 4 | 5 | | | V-1 | Cyp2j9 |
| 8047 | 3 | 4 | 5 | | | V-1 | Cox6a1 | 8132 | 3 | 4 | 5 | | | V-1 | Cyp2s1 |
| 8048 | 3 | 4 | 5 | | | V-1 | Cox6b1 | 8133 | 3 | 4 | 5 | | | V-1 | Cyp2u1 |
| 8049 | 3 | 4 | 5 | | | V-1 | Cox7a1 | 8134 | 3 | 4 | 5 | | | V-1 | Cyp46a1 |
| 8050 | 3 | 4 | 5 | | | V-1 | Cox7a2 | 8135 | 3 | 4 | 5 | | | V-1 | Cyp4a31 |
| 8051 | 3 | 4 | 5 | | | V-1 | Cox7b | 8136 | 3 | 4 | 5 | | | V-1 | Cyp4b1 |
| 8052 | 3 | 4 | 5 | | | V-1 | Cox7c | 8137 | 3 | 4 | 5 | | | V-1 | Cyp4f13 |
| 8053 | 3 | 4 | 5 | | | V-1 | Cox8a | 8138 | 3 | 4 | 5 | | | V-1 | Cyp4f16 |
| 8054 | 3 | 4 | 5 | | | V-1 | Cp | 8139 | 3 | 4 | 5 | | | V-1 | Cyp4f18 |
| 8055 | 3 | 4 | 5 | | | V-1 | Cpb2 | 8140 | 3 | 4 | 5 | | | V-1 | Cyp4x1 |
| 8056 | 3 | 4 | 5 | | | V-1 | Cpeb1 | 8141 | 3 | 4 | 5 | | | V-1 | Cyp51 |
| 8057 | 3 | 4 | 5 | | | V-1 | Cphx1 | 8142 | 3 | 4 | 5 | | | V-1 | Cyp7b1 |
| 8058 | 3 | 4 | 5 | | | V-1 | Cpne8 | 8143 | 3 | 4 | 5 | | | V-1 | Cysltr1 |
| 8059 | 3 | 4 | 5 | | | V-1 | Cpped1 | 8144 | 3 | 4 | 5 | | | V-1 | Cystm1 |
| 8060 | 3 | 4 | 5 | | | V-1 | Cps1 | 8145 | 3 | 4 | 5 | | | V-1 | Cyth4 |
| 8061 | 3 | 4 | 5 | | | V-1 | Cpt1a | 8146 | 3 | 4 | 5 | | | V-1 | D130017N08Rik |
| 8062 | 3 | 4 | 5 | | | V-1 | Cpt1c | 8147 | 3 | 4 | 5 | | | V-1 | D2Wsu81e |
| 8063 | 3 | 4 | 5 | | | V-1 | Cpxm2 | 8148 | 3 | 4 | 5 | | | V-1 | D330023K18Rik |
| 8064 | 3 | 4 | 5 | | | V-1 | Cradd | 8149 | 3 | 4 | 5 | | | V-1 | D330050I16Rik |
| 8065 | 3 | 4 | 5 | | | V-1 | Creb3l1 | 8150 | 3 | 4 | 5 | | | V-1 | D3Ertd562e |
| 8066 | 3 | 4 | 5 | | | V-1 | Creg1 | 8151 | 3 | 4 | 5 | | | V-1 | D5Ertd579e |
| 8067 | 3 | 4 | 5 | | | V-1 | Crhr2 | 8152 | 3 | 4 | 5 | | | V-1 | D5Ertd605e |
| 8068 | 3 | 4 | 5 | | | V-1 | Crim1 | 8153 | 3 | 4 | 5 | | | V-1 | D630023F18Rik |
| 8069 | 3 | 4 | 5 | | | V-1 | Crip1 | 8154 | 3 | 4 | 5 | | | V-1 | D630032N06Rik |
| 8070 | 3 | 4 | 5 | | | V-1 | Crip2 | 8155 | 3 | 4 | 5 | | | V-1 | D630045M09Rik |
| 8071 | 3 | 4 | 5 | | | V-1 | Crlf2 | 8156 | 3 | 4 | 5 | | | V-1 | D6Ertd527e |
| 8072 | 3 | 4 | 5 | | | V-1 | Crls1 | 8157 | 3 | 4 | 5 | | | V-1 | D830015G02Rik |
| 8073 | 3 | 4 | 5 | | | V-1 | Crtam | 8158 | 3 | 4 | 5 | | | V-1 | D830026I12Rik |

Fig. 43 - 49

| | | | | | | | |
|---|---|---|---|---|---|---|---|
| 8159 | 3 | 4 | 5 | | V-1 | D8Ertd738e |
| 8160 | 3 | 4 | 5 | | V-1 | Daam2 |
| 8161 | 3 | 4 | 5 | | V-1 | Dab2 |
| 8162 | 3 | 4 | 5 | | V-1 | Dach1 |
| 8163 | 3 | 4 | 5 | | V-1 | Dag1 |
| 8164 | 3 | 4 | 5 | | V-1 | Dagla |
| 8165 | 3 | 4 | 5 | | V-1 | Dak |
| 8166 | 3 | 4 | 5 | | V-1 | Dancr |
| 8167 | 3 | 4 | 5 | | V-1 | Dap |
| 8168 | 3 | 4 | 5 | | V-1 | Dapk2 |
| 8169 | 3 | 4 | 5 | | V-1 | Daw1 |
| 8170 | 3 | 4 | 5 | | V-1 | Daxx |
| 8171 | 3 | 4 | 5 | | V-1 | Dbf4 |
| 8172 | 3 | 4 | 5 | | V-1 | Dbi |
| 8173 | 3 | 4 | 5 | | V-1 | Dbnl |
| 8174 | 3 | 4 | 5 | | V-1 | Dbr1 |
| 8175 | 3 | 4 | 5 | | V-1 | Dcaf13 |
| 8176 | 3 | 4 | 5 | | V-1 | Dcaf4 |
| 8177 | 3 | 4 | 5 | | V-1 | Dcire1a |
| 8178 | 3 | 4 | 5 | | V-1 | Dcpp3 |
| 8179 | 3 | 4 | 5 | | V-1 | Dctd |
| 8180 | 3 | 4 | 5 | | V-1 | Dctn3 |
| 8181 | 3 | 4 | 5 | | V-1 | Dctpp1 |
| 8182 | 3 | 4 | 5 | | V-1 | Ddb2 |
| 8183 | 3 | 4 | 5 | | V-1 | Ddit3 |
| 8184 | 3 | 4 | 5 | | V-1 | Ddit4l |
| 8185 | 3 | 4 | 5 | | V-1 | Ddost |
| 8186 | 3 | 4 | 5 | | V-1 | Ddx1 |
| 8187 | 3 | 4 | 5 | | V-1 | Ddx18 |
| 8188 | 3 | 4 | 5 | | V-1 | Ddx19b |
| 8189 | 3 | 4 | 5 | | V-1 | Ddx21 |
| 8190 | 3 | 4 | 5 | | V-1 | Ddx39 |
| 8191 | 3 | 4 | 5 | | V-1 | Ddx39b |
| 8192 | 3 | 4 | 5 | | V-1 | Ddx55 |
| 8193 | 3 | 4 | 5 | | V-1 | Deb1 |
| 8194 | 3 | 4 | 5 | | V-1 | Defa3 |
| 8195 | 3 | 4 | 5 | | V-1 | Defb6 |
| 8196 | 3 | 4 | 5 | | V-1 | Dennd1c |
| 8197 | 3 | 4 | 5 | | V-1 | Dennd4a |
| 8198 | 3 | 4 | 5 | | V-1 | Dennd4b |
| 8199 | 3 | 4 | 5 | | V-1 | Dennd6b |
| 8200 | 3 | 4 | 5 | | V-1 | Denr |
| 8201 | 3 | 4 | 5 | | V-1 | Deptor |
| 8202 | 3 | 4 | 5 | | V-1 | Dera |
| 8203 | 3 | 4 | 5 | | V-1 | Dfna5 |
| 8204 | 3 | 4 | 5 | | V-1 | Dgat1 |
| 8205 | 3 | 4 | 5 | | V-1 | Dgkh |
| 8206 | 3 | 4 | 5 | | V-1 | Dgkq |
| 8207 | 3 | 4 | 5 | | V-1 | Dhcr7 |
| 8208 | 3 | 4 | 5 | | V-1 | Dhfr |
| 8209 | 3 | 4 | 5 | | V-1 | Dhodh |
| 8210 | 3 | 4 | 5 | | V-1 | Dhrs11 |
| 8211 | 3 | 4 | 5 | | V-1 | Dhrsx |
| 8212 | 3 | 4 | 5 | | V-1 | Dido1 |
| 8213 | 3 | 4 | 5 | | V-1 | Dip2a |
| 8214 | 3 | 4 | 5 | | V-1 | Dis3l2 |
| 8215 | 3 | 4 | 5 | | V-1 | Dlat |
| 8216 | 3 | 4 | 5 | | V-1 | Dlc1 |
| 8217 | 3 | 4 | 5 | | V-1 | Dld |
| 8218 | 3 | 4 | 5 | | V-1 | Dlg2 |
| 8219 | 3 | 4 | 5 | | V-1 | Dlk1 |
| 8220 | 3 | 4 | 5 | | V-1 | Dmap1 |
| 8221 | 3 | 4 | 5 | | V-1 | Dmd |
| 8222 | 3 | 4 | 5 | | V-1 | Dmrt2 |
| 8223 | 3 | 4 | 5 | | V-1 | Dmrta1 |
| 8224 | 3 | 4 | 5 | | V-1 | Dna2 |
| 8225 | 3 | 4 | 5 | | V-1 | Dnaaf2 |
| 8226 | 3 | 4 | 5 | | V-1 | Dnaaf3 |
| 8227 | 3 | 4 | 5 | | V-1 | Dnajb11 |
| 8228 | 3 | 4 | 5 | | V-1 | Dnajc16 |
| 8229 | 3 | 4 | 5 | | V-1 | Dnajc25 |
| 8230 | 3 | 4 | 5 | | V-1 | Dnajc5 |
| 8231 | 3 | 4 | 5 | | V-1 | Dnajc8 |
| 8232 | 3 | 4 | 5 | | V-1 | Dnajc9 |
| 8233 | 3 | 4 | 5 | | V-1 | Dnase1l1 |
| 8234 | 3 | 4 | 5 | | V-1 | Dnase2a |
| 8235 | 3 | 4 | 5 | | V-1 | Dnm1 |
| 8236 | 3 | 4 | 5 | | V-1 | Dnm3os |
| 8237 | 3 | 4 | 5 | | V-1 | Doc2b |
| 8238 | 3 | 4 | 5 | | V-1 | Doc2g |
| 8239 | 3 | 4 | 5 | | V-1 | Dock1 |
| 8240 | 3 | 4 | 5 | | V-1 | Dock4 |
| 8241 | 3 | 4 | 5 | | V-1 | Dock5 |
| 8242 | 3 | 4 | 5 | | V-1 | Dock8 |
| 8243 | 3 | 4 | 5 | | V-1 | Dok1 |
| 8244 | 3 | 4 | 5 | | V-1 | Dpep1 |
| 8245 | 3 | 4 | 5 | | V-1 | Dpep3 |
| 8246 | 3 | 4 | 5 | | V-1 | Dph5 |
| 8247 | 3 | 4 | 5 | | V-1 | Dpm3 |
| 8248 | 3 | 4 | 5 | | V-1 | Dpy19l1 |
| 8249 | 3 | 4 | 5 | | V-1 | Dpy30 |
| 8250 | 3 | 4 | 5 | | V-1 | Dpysl2 |
| 8251 | 3 | 4 | 5 | | V-1 | Dpysl4 |
| 8252 | 3 | 4 | 5 | | V-1 | Dram1 |
| 8253 | 3 | 4 | 5 | | V-1 | Dsc2 |
| 8254 | 3 | 4 | 5 | | V-1 | Dsc3 |
| 8255 | 3 | 4 | 5 | | V-1 | Dse |
| 8256 | 3 | 4 | 5 | | V-1 | Dsg1a |
| 8257 | 3 | 4 | 5 | | V-1 | Dsg1b |
| 8258 | 3 | 4 | 5 | | V-1 | Dtx3l |
| 8259 | 3 | 4 | 5 | | V-1 | Dtymk |
| 8260 | 3 | 4 | 5 | | V-1 | Duoxa1 |
| 8261 | 3 | 4 | 5 | | V-1 | Dus2 |
| 8262 | 3 | 4 | 5 | | V-1 | Dusp10 |
| 8263 | 3 | 4 | 5 | | V-1 | Dusp14 |
| 8264 | 3 | 4 | 5 | | V-1 | Dusp18 |
| 8265 | 3 | 4 | 5 | | V-1 | Dusp28 |
| 8266 | 3 | 4 | 5 | | V-1 | Dusp6 |
| 8267 | 3 | 4 | 5 | | V-1 | Dusp8 |
| 8268 | 3 | 4 | 5 | | V-1 | Dync2li1 |
| 8269 | 3 | 4 | 5 | | V-1 | Dynll2 |
| 8270 | 3 | 4 | 5 | | V-1 | Dysf |
| 8271 | 3 | 4 | 5 | | V-1 | E030024N20Rik |
| 8272 | 3 | 4 | 5 | | V-1 | E130012A19Rik |
| 8273 | 3 | 4 | 5 | | V-1 | E130102H24Rik |
| 8274 | 3 | 4 | 5 | | V-1 | E130112N10Rik |
| 8275 | 3 | 4 | 5 | | V-1 | E130201H02Rik |
| 8276 | 3 | 4 | 5 | | V-1 | E130215H24Rik |
| 8277 | 3 | 4 | 5 | | V-1 | E130311K13Rik |
| 8278 | 3 | 4 | 5 | | V-1 | E230016K23Rik |
| 8279 | 3 | 4 | 5 | | V-1 | E2f6 |
| 8280 | 3 | 4 | 5 | | V-1 | E2f7 |
| 8281 | 3 | 4 | 5 | | V-1 | E2f8 |
| 8282 | 3 | 4 | 5 | | V-1 | E330011O21Rik |
| 8283 | 3 | 4 | 5 | | V-1 | E330017L17Rik |
| 8284 | 3 | 4 | 5 | | V-1 | Eaf1 |
| 8285 | 3 | 4 | 5 | | V-1 | Ears2 |
| 8286 | 3 | 4 | 5 | | V-1 | Ebi3 |
| 8287 | 3 | 4 | 5 | | V-1 | Echdc1 |
| 8288 | 3 | 4 | 5 | | V-1 | Ecm1 |
| 8289 | 3 | 4 | 5 | | V-1 | Ecscr |
| 8290 | 3 | 4 | 5 | | V-1 | Ect2 |
| 8291 | 3 | 4 | 5 | | V-1 | Edar |
| 8292 | 3 | 4 | 5 | | V-1 | Edem3 |
| 8293 | 3 | 4 | 5 | | V-1 | Edf1 |
| 8294 | 3 | 4 | 5 | | V-1 | Edn1 |
| 8295 | 3 | 4 | 5 | | V-1 | Ednra |
| 8296 | 3 | 4 | 5 | | V-1 | Eef1e1 |
| 8297 | 3 | 4 | 5 | | V-1 | Eef2k |
| 8298 | 3 | 4 | 5 | | V-1 | Eepd1 |
| 8299 | 3 | 4 | 5 | | V-1 | Efcab4a |
| 8300 | 3 | 4 | 5 | | V-1 | Efemp1 |
| 8301 | 3 | 4 | 5 | | V-1 | Efemp2 |
| 8302 | 3 | 4 | 5 | | V-1 | Efna2 |
| 8303 | 3 | 4 | 5 | | V-1 | Efna3 |
| 8304 | 3 | 4 | 5 | | V-1 | Efnb3 |
| 8305 | 3 | 4 | 5 | | V-1 | Egflam |
| 8306 | 3 | 4 | 5 | | V-1 | Egln1 |
| 8307 | 3 | 4 | 5 | | V-1 | Ehd3 |
| 8308 | 3 | 4 | 5 | | V-1 | Ehhadh |
| 8309 | 3 | 4 | 5 | | V-1 | Ei24 |
| 8310 | 3 | 4 | 5 | | V-1 | Eid2 |
| 8311 | 3 | 4 | 5 | | V-1 | Eif2b1 |
| 8312 | 3 | 4 | 5 | | V-1 | Eif2b3 |
| 8313 | 3 | 4 | 5 | | V-1 | Eif2b4 |
| 8314 | 3 | 4 | 5 | | V-1 | Eif2d |
| 8315 | 3 | 4 | 5 | | V-1 | Eif2s1 |
| 8316 | 3 | 4 | 5 | | V-1 | Eif2s2 |
| 8317 | 3 | 4 | 5 | | V-1 | Eif3g |
| 8318 | 3 | 4 | 5 | | V-1 | Eif4a1 |
| 8319 | 3 | 4 | 5 | | V-1 | Eif4a3 |
| 8320 | 3 | 4 | 5 | | V-1 | Eif5a |
| 8321 | 3 | 4 | 5 | | V-1 | Eif5a2 |
| 8322 | 3 | 4 | 5 | | V-1 | Eif6 |
| 8323 | 3 | 4 | 5 | | V-1 | Elane |
| 8324 | 3 | 4 | 5 | | V-1 | Elf4 |
| 8325 | 3 | 4 | 5 | | V-1 | Elk3 |
| 8326 | 3 | 4 | 5 | | V-1 | Elmod2 |
| 8327 | 3 | 4 | 5 | | V-1 | Elmsan1 |
| 8328 | 3 | 4 | 5 | | V-1 | Eln |

Fig. 43 - 50

| 8329 | 3 | 4 | 5 | | | V-1 | Elovl5 |
|---|---|---|---|---|---|---|---|
| 8330 | 3 | 4 | 5 | | | V-1 | Elovl6 |
| 8331 | 3 | 4 | 5 | | | V-1 | Elp4 |
| 8332 | 3 | 4 | 5 | | | V-1 | Emc2 |
| 8333 | 3 | 4 | 5 | | | V-1 | Emc6 |
| 8334 | 3 | 4 | 5 | | | V-1 | Emc8 |
| 8335 | 3 | 4 | 5 | | | V-1 | Eme2 |
| 8336 | 3 | 4 | 5 | | | V-1 | Emilin1 |
| 8337 | 3 | 4 | 5 | | | V-1 | Eml1 |
| 8338 | 3 | 4 | 5 | | | V-1 | Eml2 |
| 8339 | 3 | 4 | 5 | | | V-1 | Emp2 |
| 8340 | 3 | 4 | 5 | | | V-1 | Emr1 |
| 8341 | 3 | 4 | 5 | | | V-1 | Enah |
| 8342 | 3 | 4 | 5 | | | V-1 | Endog |
| 8343 | 3 | 4 | 5 | | | V-1 | Enho |
| 8344 | 3 | 4 | 5 | | | V-1 | Enpep |
| 8345 | 3 | 4 | 5 | | | V-1 | Enpp1 |
| 8346 | 3 | 4 | 5 | | | V-1 | Enpp4 |
| 8347 | 3 | 4 | 5 | | | V-1 | Enpp5 |
| 8348 | 3 | 4 | 5 | | | V-1 | Entpd1 |
| 8349 | 3 | 4 | 5 | | | V-1 | Entpd3 |
| 8350 | 3 | 4 | 5 | | | V-1 | Entpd5 |
| 8351 | 3 | 4 | 5 | | | V-1 | Epb4.1l1 |
| 8352 | 3 | 4 | 5 | | | V-1 | Epb4.1l2 |
| 8353 | 3 | 4 | 5 | | | V-1 | Ephx2 |
| 8354 | 3 | 4 | 5 | | | V-1 | Ephx4 |
| 8355 | 3 | 4 | 5 | | | V-1 | Epor |
| 8356 | 3 | 4 | 5 | | | V-1 | Eppk1 |
| 8357 | 3 | 4 | 5 | | | V-1 | Eprs |
| 8358 | 3 | 4 | 5 | | | V-1 | Erh |
| 8359 | 3 | 4 | 5 | | | V-1 | Eri3 |
| 8360 | 3 | 4 | 5 | | | V-1 | Erich1 |
| 8361 | 3 | 4 | 5 | | | V-1 | Ermap |
| 8362 | 3 | 4 | 5 | | | V-1 | Ermard |
| 8363 | 3 | 4 | 5 | | | V-1 | Ermp1 |
| 8364 | 3 | 4 | 5 | | | V-1 | Ero1lb |
| 8365 | 3 | 4 | 5 | | | V-1 | Esf1 |
| 8366 | 3 | 4 | 5 | | | V-1 | Espl1 |
| 8367 | 3 | 4 | 5 | | | V-1 | Esrra |
| 8368 | 3 | 4 | 5 | | | V-1 | Esrrb |
| 8369 | 3 | 4 | 5 | | | V-1 | Esrrg |
| 8370 | 3 | 4 | 5 | | | V-1 | Etfa |
| 8371 | 3 | 4 | 5 | | | V-1 | Etfb |
| 8372 | 3 | 4 | 5 | | | V-1 | Etl4 |
| 8373 | 3 | 4 | 5 | | | V-1 | Etnk1 |
| 8374 | 3 | 4 | 5 | | | V-1 | Ets2 |
| 8375 | 3 | 4 | 5 | | | V-1 | Etv4 |
| 8376 | 3 | 4 | 5 | | | V-1 | Etv5 |
| 8377 | 3 | 4 | 5 | | | V-1 | Eva1c |
| 8378 | 3 | 4 | 5 | | | V-1 | Evc |
| 8379 | 3 | 4 | 5 | | | V-1 | Evc2 |
| 8380 | 3 | 4 | 5 | | | V-1 | Evi2b |
| 8381 | 3 | 4 | 5 | | | V-1 | Evl |
| 8382 | 3 | 4 | 5 | | | V-1 | Ewsr1 |
| 8383 | 3 | 4 | 5 | | | V-1 | Exoc1 |
| 8384 | 3 | 4 | 5 | | | V-1 | Exoc2 |
| 8385 | 3 | 4 | 5 | | | V-1 | Exog |
| 8386 | 3 | 4 | 5 | | | V-1 | Exosc7 |
| 8387 | 3 | 4 | 5 | | | V-1 | Exosc9 |
| 8388 | 3 | 4 | 5 | | | V-1 | Ext1 |
| 8389 | 3 | 4 | 5 | | | V-1 | Eya1 |
| 8390 | 3 | 4 | 5 | | | V-1 | Eya4 |
| 8391 | 3 | 4 | 5 | | | V-1 | F10 |
| 8392 | 3 | 4 | 5 | | | V-1 | F630028O10Rik |
| 8393 | 3 | 4 | 5 | | | V-1 | F830016B08Rik |
| 8394 | 3 | 4 | 5 | | | V-1 | Fads3 |
| 8395 | 3 | 4 | 5 | | | V-1 | Fah |
| 8396 | 3 | 4 | 5 | | | V-1 | Fahd1 |
| 8397 | 3 | 4 | 5 | | | V-1 | Fam102a |
| 8398 | 3 | 4 | 5 | | | V-1 | Fam107b |
| 8399 | 3 | 4 | 5 | | | V-1 | Fam110c |
| 8400 | 3 | 4 | 5 | | | V-1 | Fam118b |
| 8401 | 3 | 4 | 5 | | | V-1 | Fam120aos |
| 8402 | 3 | 4 | 5 | | | V-1 | Fam122b |
| 8403 | 3 | 4 | 5 | | | V-1 | Fam126b |
| 8404 | 3 | 4 | 5 | | | V-1 | Fam131c |
| 8405 | 3 | 4 | 5 | | | V-1 | Fam13c |
| 8406 | 3 | 4 | 5 | | | V-1 | Fam151a |
| 8407 | 3 | 4 | 5 | | | V-1 | Fam151b |
| 8408 | 3 | 4 | 5 | | | V-1 | Fam160b1 |
| 8409 | 3 | 4 | 5 | | | V-1 | Fam161a |
| 8410 | 3 | 4 | 5 | | | V-1 | Fam162b |
| 8411 | 3 | 4 | 5 | | | V-1 | Fam171a1 |
| 8412 | 3 | 4 | 5 | | | V-1 | Fam173a |
| 8413 | 3 | 4 | 5 | | | V-1 | Fam175a |
| 8414 | 3 | 4 | 5 | | | V-1 | Fam179a |
| 8415 | 3 | 4 | 5 | | | V-1 | Fam195b |
| 8416 | 3 | 4 | 5 | | | V-1 | Fam198b |
| 8417 | 3 | 4 | 5 | | | V-1 | Fam199x |
| 8418 | 3 | 4 | 5 | | | V-1 | Fam208b |
| 8419 | 3 | 4 | 5 | | | V-1 | Fam213b |
| 8420 | 3 | 4 | 5 | | | V-1 | Fam216a |
| 8421 | 3 | 4 | 5 | | | V-1 | Fam219a |
| 8422 | 3 | 4 | 5 | | | V-1 | Fam26e |
| 8423 | 3 | 4 | 5 | | | V-1 | Fam46a |
| 8424 | 3 | 4 | 5 | | | V-1 | Fam49b |
| 8425 | 3 | 4 | 5 | | | V-1 | Fam53b |
| 8426 | 3 | 4 | 5 | | | V-1 | Fam53c |
| 8427 | 3 | 4 | 5 | | | V-1 | Fam65b |
| 8428 | 3 | 4 | 5 | | | V-1 | Fam83f |
| 8429 | 3 | 4 | 5 | | | V-1 | Fam84a |
| 8430 | 3 | 4 | 5 | | | V-1 | Fam84b |
| 8431 | 3 | 4 | 5 | | | V-1 | Fam92a |
| 8432 | 3 | 4 | 5 | | | V-1 | Fam96b |
| 8433 | 3 | 4 | 5 | | | V-1 | Fam98b |
| 8434 | 3 | 4 | 5 | | | V-1 | Fancf |
| 8435 | 3 | 4 | 5 | | | V-1 | Fanci |
| 8436 | 3 | 4 | 5 | | | V-1 | Farp1 |
| 8437 | 3 | 4 | 5 | | | V-1 | Fas |
| 8438 | 3 | 4 | 5 | | | V-1 | Fastkd1 |
| 8439 | 3 | 4 | 5 | | | V-1 | Fastkd2 |
| 8440 | 3 | 4 | 5 | | | V-1 | Fbl |
| 8441 | 3 | 4 | 5 | | | V-1 | Fbp2 |
| 8442 | 3 | 4 | 5 | | | V-1 | Fbxl15 |
| 8443 | 3 | 4 | 5 | | | V-1 | Fbxl16 |
| 8444 | 3 | 4 | 5 | | | V-1 | Fbxl21 |
| 8445 | 3 | 4 | 5 | | | V-1 | Fbxo10 |
| 8446 | 3 | 4 | 5 | | | V-1 | Fbxo17 |
| 8447 | 3 | 4 | 5 | | | V-1 | Fbxo21 |
| 8448 | 3 | 4 | 5 | | | V-1 | Fbxo5 |
| 8449 | 3 | 4 | 5 | | | V-1 | Fbxw7 |
| 8450 | 3 | 4 | 5 | | | V-1 | Fbxw9 |
| 8451 | 3 | 4 | 5 | | | V-1 | Fcer1g |
| 8452 | 3 | 4 | 5 | | | V-1 | Fcf1 |
| 8453 | 3 | 4 | 5 | | | V-1 | Fcgrt |
| 8454 | 3 | 4 | 5 | | | V-1 | Fdx1l |
| 8455 | 3 | 4 | 5 | | | V-1 | Fdxacb1 |
| 8456 | 3 | 4 | 5 | | | V-1 | Fem1a |
| 8457 | 3 | 4 | 5 | | | V-1 | Fermt3 |
| 8458 | 3 | 4 | 5 | | | V-1 | Fes |
| 8459 | 3 | 4 | 5 | | | V-1 | Fetub |
| 8460 | 3 | 4 | 5 | | | V-1 | Ffar2 |
| 8461 | 3 | 4 | 5 | | | V-1 | Fgd2 |
| 8462 | 3 | 4 | 5 | | | V-1 | Fgd3 |
| 8463 | 3 | 4 | 5 | | | V-1 | Fgd4 |
| 8464 | 3 | 4 | 5 | | | V-1 | Fgf10 |
| 8465 | 3 | 4 | 5 | | | V-1 | Fgf11 |
| 8466 | 3 | 4 | 5 | | | V-1 | Fgf18 |
| 8467 | 3 | 4 | 5 | | | V-1 | Fgf22 |
| 8468 | 3 | 4 | 5 | | | V-1 | Fgf7 |
| 8469 | 3 | 4 | 5 | | | V-1 | Fgfbp3 |
| 8470 | 3 | 4 | 5 | | | V-1 | Fgfr2 |
| 8471 | 3 | 4 | 5 | | | V-1 | Fgfr4 |
| 8472 | 3 | 4 | 5 | | | V-1 | Fgg |
| 8473 | 3 | 4 | 5 | | | V-1 | Fhl2 |
| 8474 | 3 | 4 | 5 | | | V-1 | Fibin |
| 8475 | 3 | 4 | 5 | | | V-1 | Fibp |
| 8476 | 3 | 4 | 5 | | | V-1 | Fign |
| 8477 | 3 | 4 | 5 | | | V-1 | Fignl1 |
| 8478 | 3 | 4 | 5 | | | V-1 | Fignl2 |
| 8479 | 3 | 4 | 5 | | | V-1 | Filip1l |
| 8480 | 3 | 4 | 5 | | | V-1 | Fis1 |
| 8481 | 3 | 4 | 5 | | | V-1 | Fjx1 |
| 8482 | 3 | 4 | 5 | | | V-1 | Fkbp10 |
| 8483 | 3 | 4 | 5 | | | V-1 | Fkbp6 |
| 8484 | 3 | 4 | 5 | | | V-1 | Fkbp7 |
| 8485 | 3 | 4 | 5 | | | V-1 | Flna |
| 8486 | 3 | 4 | 5 | | | V-1 | Flot1 |
| 8487 | 3 | 4 | 5 | | | V-1 | Flt3l |
| 8488 | 3 | 4 | 5 | | | V-1 | Fmo2 |
| 8489 | 3 | 4 | 5 | | | V-1 | Fmo3 |
| 8490 | 3 | 4 | 5 | | | V-1 | Fn3krp |
| 8491 | 3 | 4 | 5 | | | V-1 | Fnbp1 |
| 8492 | 3 | 4 | 5 | | | V-1 | Fndc1 |
| 8493 | 3 | 4 | 5 | | | V-1 | Focad |
| 8494 | 3 | 4 | 5 | | | V-1 | Folr2 |
| 8495 | 3 | 4 | 5 | | | V-1 | Fosl2 |
| 8496 | 3 | 4 | 5 | | | V-1 | Foxc1 |
| 8497 | 3 | 4 | 5 | | | V-1 | Foxf1 |
| 8498 | 3 | 4 | 5 | | | V-1 | Foxm1 |

Fig. 43 - 51

| | | | | | | | | |
|---|---|---|---|---|---|---|---|---|
| 8499 | 3 | 4 | 5 | | | V-1 | Foxo4 |
| 8500 | 3 | 4 | 5 | | | V-1 | Fpgs |
| 8501 | 3 | 4 | 5 | | | V-1 | Frmd6 |
| 8502 | 3 | 4 | 5 | | | V-1 | Frs2 |
| 8503 | 3 | 4 | 5 | | | V-1 | Fryl |
| 8504 | 3 | 4 | 5 | | | V-1 | Fscn1 |
| 8505 | 3 | 4 | 5 | | | V-1 | Fsd2 |
| 8506 | 3 | 4 | 5 | | | V-1 | Fst |
| 8507 | 3 | 4 | 5 | | | V-1 | Fstl1 |
| 8508 | 3 | 4 | 5 | | | V-1 | Fstl3 |
| 8509 | 3 | 4 | 5 | | | V-1 | Fth1 |
| 8510 | 3 | 4 | 5 | | | V-1 | Ftsj3 |
| 8511 | 3 | 4 | 5 | | | V-1 | Ftx |
| 8512 | 3 | 4 | 5 | | | V-1 | Fuca2 |
| 8513 | 3 | 4 | 5 | | | V-1 | Furin |
| 8514 | 3 | 4 | 5 | | | V-1 | Fus |
| 8515 | 3 | 4 | 5 | | | V-1 | Fxn |
| 8516 | 3 | 4 | 5 | | | V-1 | Fxyd1 |
| 8517 | 3 | 4 | 5 | | | V-1 | Fxyd4 |
| 8518 | 3 | 4 | 5 | | | V-1 | Fxyd5 |
| 8519 | 3 | 4 | 5 | | | V-1 | Fxyd6 |
| 8520 | 3 | 4 | 5 | | | V-1 | Fyb |
| 8521 | 3 | 4 | 5 | | | V-1 | Fzd3 |
| 8522 | 3 | 4 | 5 | | | V-1 | Fzd6 |
| 8523 | 3 | 4 | 5 | | | V-1 | Fzd7 |
| 8524 | 3 | 4 | 5 | | | V-1 | G6pc3 |
| 8525 | 3 | 4 | 5 | | | V-1 | G6pd2 |
| 8526 | 3 | 4 | 5 | | | V-1 | G6pdx |
| 8527 | 3 | 4 | 5 | | | V-1 | Gaa |
| 8528 | 3 | 4 | 5 | | | V-1 | Gab1 |
| 8529 | 3 | 4 | 5 | | | V-1 | Gab2 |
| 8530 | 3 | 4 | 5 | | | V-1 | Gabre |
| 8531 | 3 | 4 | 5 | | | V-1 | Gadd45g |
| 8532 | 3 | 4 | 5 | | | V-1 | Gadd45gip1 |
| 8533 | 3 | 4 | 5 | | | V-1 | Gal3st1 |
| 8534 | 3 | 4 | 5 | | | V-1 | Gale |
| 8535 | 3 | 4 | 5 | | | V-1 | Galns |
| 8536 | 3 | 4 | 5 | | | V-1 | Galnt16 |
| 8537 | 3 | 4 | 5 | | | V-1 | Galnt18 |
| 8538 | 3 | 4 | 5 | | | V-1 | Galnt6 |
| 8539 | 3 | 4 | 5 | | | V-1 | Gamt |
| 8540 | 3 | 4 | 5 | | | V-1 | Gar1 |
| 8541 | 3 | 4 | 5 | | | V-1 | Gars |
| 8542 | 3 | 4 | 5 | | | V-1 | Gart |
| 8543 | 3 | 4 | 5 | | | V-1 | Gas2l3 |
| 8544 | 3 | 4 | 5 | | | V-1 | Gas6 |
| 8545 | 3 | 4 | 5 | | | V-1 | Gas7 |
| 8546 | 3 | 4 | 5 | | | V-1 | Gata3 |
| 8547 | 3 | 4 | 5 | | | V-1 | Gbe1 |
| 8548 | 3 | 4 | 5 | | | V-1 | Gbp2 |
| 8549 | 3 | 4 | 5 | | | V-1 | Gbp4 |
| 8550 | 3 | 4 | 5 | | | V-1 | Gbp5 |
| 8551 | 3 | 4 | 5 | | | V-1 | Gbp7 |
| 8552 | 3 | 4 | 5 | | | V-1 | Gcg |
| 8553 | 3 | 4 | 5 | | | V-1 | Gchfr |
| 8554 | 3 | 4 | 5 | | | V-1 | Gcnt1 |
| 8555 | 3 | 4 | 5 | | | V-1 | Gcnt2 |
| 8556 | 3 | 4 | 5 | | | V-1 | Gcsh |
| 8557 | 3 | 4 | 5 | | | V-1 | Gde1 |
| 8558 | 3 | 4 | 5 | | | V-1 | Gdf10 |
| 8559 | 3 | 4 | 5 | | | V-1 | Gdpd3 |
| 8560 | 3 | 4 | 5 | | | V-1 | Gemin2 |
| 8561 | 3 | 4 | 5 | | | V-1 | Gemin6 |
| 8562 | 3 | 4 | 5 | | | V-1 | Gfap |
| 8563 | 3 | 4 | 5 | | | V-1 | Gfer |
| 8564 | 3 | 4 | 5 | | | V-1 | Gfm1 |
| 8565 | 3 | 4 | 5 | | | V-1 | Ggact |
| 8566 | 3 | 4 | 5 | | | V-1 | Ggh |
| 8567 | 3 | 4 | 5 | | | V-1 | Ggnbp1 |
| 8568 | 3 | 4 | 5 | | | V-1 | Ggt5 |
| 8569 | 3 | 4 | 5 | | | V-1 | Ggt6 |
| 8570 | 3 | 4 | 5 | | | V-1 | Ghr |
| 8571 | 3 | 4 | 5 | | | V-1 | Gins2 |
| 8572 | 3 | 4 | 5 | | | V-1 | Gip |
| 8573 | 3 | 4 | 5 | | | V-1 | Gja3 |
| 8574 | 3 | 4 | 5 | | | V-1 | Gja4 |
| 8575 | 3 | 4 | 5 | | | V-1 | Gjb3 |
| 8576 | 3 | 4 | 5 | | | V-1 | Gjb6 |
| 8577 | 3 | 4 | 5 | | | V-1 | Gjc1 |
| 8578 | 3 | 4 | 5 | | | V-1 | Glb1l2 |
| 8579 | 3 | 4 | 5 | | | V-1 | Gli2 |
| 8580 | 3 | 4 | 5 | | | V-1 | Glipr2 |
| 8581 | 3 | 4 | 5 | | | V-1 | Glis2 |
| 8582 | 3 | 4 | 5 | | | V-1 | Glrb |
| 8583 | 3 | 4 | 5 | | | V-1 | Glrx |

| | | | | | | | | |
|---|---|---|---|---|---|---|---|---|
| 8584 | 3 | 4 | 5 | | | V-1 | Glrx3 |
| 8585 | 3 | 4 | 5 | | | V-1 | Glrx5 |
| 8586 | 3 | 4 | 5 | | | V-1 | Glt1d1 |
| 8587 | 3 | 4 | 5 | | | V-1 | Glt8d2 |
| 8588 | 3 | 4 | 5 | | | V-1 | Gm10012 |
| 8589 | 3 | 4 | 5 | | | V-1 | Gm10033 |
| 8590 | 3 | 4 | 5 | | | V-1 | Gm10069 |
| 8591 | 3 | 4 | 5 | | | V-1 | Gm10125 |
| 8592 | 3 | 4 | 5 | | | V-1 | Gm10406 |
| 8593 | 3 | 4 | 5 | | | V-1 | Gm10509 |
| 8594 | 3 | 4 | 5 | | | V-1 | Gm10653 |
| 8595 | 3 | 4 | 5 | | | V-1 | Gm10857 |
| 8596 | 3 | 4 | 5 | | | V-1 | Gm10865 |
| 8597 | 3 | 4 | 5 | | | V-1 | Gm1110 |
| 8598 | 3 | 4 | 5 | | | V-1 | Gm11127 |
| 8599 | 3 | 4 | 5 | | | V-1 | Gm11240 |
| 8600 | 3 | 4 | 5 | | | V-1 | Gm11627 |
| 8601 | 3 | 4 | 5 | | | V-1 | Gm11710 |
| 8602 | 3 | 4 | 5 | | | V-1 | Gm11992 |
| 8603 | 3 | 4 | 5 | | | V-1 | Gm12338 |
| 8604 | 3 | 4 | 5 | | | V-1 | Gm12504 |
| 8605 | 3 | 4 | 5 | | | V-1 | Gm13003 |
| 8606 | 3 | 4 | 5 | | | V-1 | Gm13139 |
| 8607 | 3 | 4 | 5 | | | V-1 | Gm13152 |
| 8608 | 3 | 4 | 5 | | | V-1 | Gm13375 |
| 8609 | 3 | 4 | 5 | | | V-1 | Gm13807 |
| 8610 | 3 | 4 | 5 | | | V-1 | Gm13826 |
| 8611 | 3 | 4 | 5 | | | V-1 | Gm14207 |
| 8612 | 3 | 4 | 5 | | | V-1 | Gm14295 |
| 8613 | 3 | 4 | 5 | | | V-1 | Gm14326 |
| 8614 | 3 | 4 | 5 | | | V-1 | Gm14346 |
| 8615 | 3 | 4 | 5 | | | V-1 | Gm14378 |
| 8616 | 3 | 4 | 5 | | | V-1 | Gm14420 |
| 8617 | 3 | 4 | 5 | | | V-1 | Gm14920 |
| 8618 | 3 | 4 | 5 | | | V-1 | Gm15284 |
| 8619 | 3 | 4 | 5 | | | V-1 | Gm15401 |
| 8620 | 3 | 4 | 5 | | | V-1 | Gm15417 |
| 8621 | 3 | 4 | 5 | | | V-1 | Gm15421 |
| 8622 | 3 | 4 | 5 | | | V-1 | Gm15760 |
| 8623 | 3 | 4 | 5 | | | V-1 | Gm1604b |
| 8624 | 3 | 4 | 5 | | | V-1 | Gm16381 |
| 8625 | 3 | 4 | 5 | | | V-1 | Gm16576 |
| 8626 | 3 | 4 | 5 | | | V-1 | Gm166 |
| 8627 | 3 | 4 | 5 | | | V-1 | Gm16675 |
| 8628 | 3 | 4 | 5 | | | V-1 | Gm1673 |
| 8629 | 3 | 4 | 5 | | | V-1 | Gm16894 |
| 8630 | 3 | 4 | 5 | | | V-1 | Gm16897 |
| 8631 | 3 | 4 | 5 | | | V-1 | Gm17066 |
| 8632 | 3 | 4 | 5 | | | V-1 | Gm17757 |
| 8633 | 3 | 4 | 5 | | | V-1 | Gm19345 |
| 8634 | 3 | 4 | 5 | | | V-1 | Gm1943 |
| 8635 | 3 | 4 | 5 | | | V-1 | Gm19619 |
| 8636 | 3 | 4 | 5 | | | V-1 | Gm1966 |
| 8637 | 3 | 4 | 5 | | | V-1 | Gm1976 |
| 8638 | 3 | 4 | 5 | | | V-1 | Gm2027 |
| 8639 | 3 | 4 | 5 | | | V-1 | Gm20324 |
| 8640 | 3 | 4 | 5 | | | V-1 | Gm20743 |
| 8641 | 3 | 4 | 5 | | | V-1 | Gm21221 |
| 8642 | 3 | 4 | 5 | | | V-1 | Gm3219 |
| 8643 | 3 | 4 | 5 | | | V-1 | Gm3264 |
| 8644 | 3 | 4 | 5 | | | V-1 | Gm3402 |
| 8645 | 3 | 4 | 5 | | | V-1 | Gm4070 |
| 8646 | 3 | 4 | 5 | | | V-1 | Gm4285 |
| 8647 | 3 | 4 | 5 | | | V-1 | Gm4907 |
| 8648 | 3 | 4 | 5 | | | V-1 | Gm4952 |
| 8649 | 3 | 4 | 5 | | | V-1 | Gm5065 |
| 8650 | 3 | 4 | 5 | | | V-1 | Gm5111 |
| 8651 | 3 | 4 | 5 | | | V-1 | Gm5148 |
| 8652 | 3 | 4 | 5 | | | V-1 | Gm5544 |
| 8653 | 3 | 4 | 5 | | | V-1 | Gm5549 |
| 8654 | 3 | 4 | 5 | | | V-1 | Gm572 |
| 8655 | 3 | 4 | 5 | | | V-1 | Gm5779 |
| 8656 | 3 | 4 | 5 | | | V-1 | Gm5803 |
| 8657 | 3 | 4 | 5 | | | V-1 | Gm5860 |
| 8658 | 3 | 4 | 5 | | | V-1 | Gm608 |
| 8659 | 3 | 4 | 5 | | | V-1 | Gm6083 |
| 8660 | 3 | 4 | 5 | | | V-1 | Gm6377 |
| 8661 | 3 | 4 | 5 | | | V-1 | Gm6654 |
| 8662 | 3 | 4 | 5 | | | V-1 | Gm6682 |
| 8663 | 3 | 4 | 5 | | | V-1 | Gm6756 |
| 8664 | 3 | 4 | 5 | | | V-1 | Gm684 |
| 8665 | 3 | 4 | 5 | | | V-1 | Gm7030 |
| 8666 | 3 | 4 | 5 | | | V-1 | Gm7244 |
| 8667 | 3 | 4 | 5 | | | V-1 | Gm7609 |
| 8668 | 3 | 4 | 5 | | | V-1 | Gm826 |

Fig. 43 - 52

| | | | | | | | | | | | | | | | | |
|---|---|---|---|---|---|---|---|---|---|---|---|---|---|---|---|---|
| 8669 | 3 | 4 | 5 | | | V-1 | Gm8369 | | 8754 | 3 | 4 | 5 | | | V-1 | Gsta4 |
| 8670 | 3 | 4 | 5 | | | V-1 | Gm8615 | | 8755 | 3 | 4 | 5 | | | V-1 | Gstcd |
| 8671 | 3 | 4 | 5 | | | V-1 | Gm8801 | | 8756 | 3 | 4 | 5 | | | V-1 | Gstm4 |
| 8672 | 3 | 4 | 5 | | | V-1 | Gm8883 | | 8757 | 3 | 4 | 5 | | | V-1 | Gstt1 |
| 8673 | 3 | 4 | 5 | | | V-1 | Gm8909 | | 8758 | 3 | 4 | 5 | | | V-1 | Gtf2a2 |
| 8674 | 3 | 4 | 5 | | | V-1 | Gm8979 | | 8759 | 3 | 4 | 5 | | | V-1 | Gtf2f1 |
| 8675 | 3 | 4 | 5 | | | V-1 | Gm906 | | 8760 | 3 | 4 | 5 | | | V-1 | Gtf2h2 |
| 8676 | 3 | 4 | 5 | | | V-1 | Gm9776 | | 8761 | 3 | 4 | 5 | | | V-1 | Gtf2ird1 |
| 8677 | 3 | 4 | 5 | | | V-1 | Gm9855 | | 8762 | 3 | 4 | 5 | | | V-1 | Gtpbp10 |
| 8678 | 3 | 4 | 5 | | | V-1 | Gmip | | 8763 | 3 | 4 | 5 | | | V-1 | Guk1 |
| 8679 | 3 | 4 | 5 | | | V-1 | Gmnn | | 8764 | 3 | 4 | 5 | | | V-1 | Gulo |
| 8680 | 3 | 4 | 5 | | | V-1 | Gmppb | | 8765 | 3 | 4 | 5 | | | V-1 | Gusb |
| 8681 | 3 | 4 | 5 | | | V-1 | Gmpr | | 8766 | 3 | 4 | 5 | | | V-1 | Gyg |
| 8682 | 3 | 4 | 5 | | | V-1 | Gmps | | 8767 | 3 | 4 | 5 | | | V-1 | Gyltl1b |
| 8683 | 3 | 4 | 5 | | | V-1 | Gna15 | | 8768 | 3 | 4 | 5 | | | V-1 | Gys1 |
| 8684 | 3 | 4 | 5 | | | V-1 | Gnai1 | | 8769 | 3 | 4 | 5 | | | V-1 | H1f0 |
| 8685 | 3 | 4 | 5 | | | V-1 | Gnb1l | | 8770 | 3 | 4 | 5 | | | V-1 | H1fx |
| 8686 | 3 | 4 | 5 | | | V-1 | Gnb3 | | 8771 | 3 | 4 | 5 | | | V-1 | H2afj |
| 8687 | 3 | 4 | 5 | | | V-1 | Gnb5 | | 8772 | 3 | 4 | 5 | | | V-1 | H2afz |
| 8688 | 3 | 4 | 5 | | | V-1 | Gng10 | | 8773 | 3 | 4 | 5 | | | V-1 | H2-D1 |
| 8689 | 3 | 4 | 5 | | | V-1 | Gng13 | | 8774 | 3 | 4 | 5 | | | V-1 | H2-DMb1 |
| 8690 | 3 | 4 | 5 | | | V-1 | Gng2 | | 8775 | 3 | 4 | 5 | | | V-1 | H2-K1 |
| 8691 | 3 | 4 | 5 | | | V-1 | Gng3 | | 8776 | 3 | 4 | 5 | | | V-1 | H2-K2 |
| 8692 | 3 | 4 | 5 | | | V-1 | Gng7 | | 8777 | 3 | 4 | 5 | | | V-1 | H2-Ke6 |
| 8693 | 3 | 4 | 5 | | | V-1 | Gnl3 | | 8778 | 3 | 4 | 5 | | | V-1 | H2-Q1 |
| 8694 | 3 | 4 | 5 | | | V-1 | Gnmt | | 8779 | 3 | 4 | 5 | | | V-1 | H2-Q10 |
| 8695 | 3 | 4 | 5 | | | V-1 | Gnptab | | 8780 | 3 | 4 | 5 | | | V-1 | H2-T23 |
| 8696 | 3 | 4 | 5 | | | V-1 | Gnptg | | 8781 | 3 | 4 | 5 | | | V-1 | H2-T9 |
| 8697 | 3 | 4 | 5 | | | V-1 | Gnrh1 | | 8782 | 3 | 4 | 5 | | | V-1 | H3f3a |
| 8698 | 3 | 4 | 5 | | | V-1 | Gns | | 8783 | 3 | 4 | 5 | | | V-1 | H3f3b |
| 8699 | 3 | 4 | 5 | | | V-1 | Golga4 | | 8784 | 3 | 4 | 5 | | | V-1 | Hacl1 |
| 8700 | 3 | 4 | 5 | | | V-1 | Golim4 | | 8785 | 3 | 4 | 5 | | | V-1 | Haghl |
| 8701 | 3 | 4 | 5 | | | V-1 | Gorab | | 8786 | 3 | 4 | 5 | | | V-1 | Hap1 |
| 8702 | 3 | 4 | 5 | | | V-1 | Gp1ba | | 8787 | 3 | 4 | 5 | | | V-1 | Hapln1 |
| 8703 | 3 | 4 | 5 | | | V-1 | Gpc3 | | 8788 | 3 | 4 | 5 | | | V-1 | Hapln4 |
| 8704 | 3 | 4 | 5 | | | V-1 | Gpc4 | | 8789 | 3 | 4 | 5 | | | V-1 | Hars |
| 8705 | 3 | 4 | 5 | | | V-1 | Gper1 | | 8790 | 3 | 4 | 5 | | | V-1 | Has3 |
| 8706 | 3 | 4 | 5 | | | V-1 | Gpm6b | | 8791 | 3 | 4 | 5 | | | V-1 | Hat1 |
| 8707 | 3 | 4 | 5 | | | V-1 | Gpr132 | | 8792 | 3 | 4 | 5 | | | V-1 | Haus1 |
| 8708 | 3 | 4 | 5 | | | V-1 | Gpr133 | | 8793 | 3 | 4 | 5 | | | V-1 | Haus8 |
| 8709 | 3 | 4 | 5 | | | V-1 | Gpr135 | | 8794 | 3 | 4 | 5 | | | V-1 | Hccs |
| 8710 | 3 | 4 | 5 | | | V-1 | Gpr15 | | 8795 | 3 | 4 | 5 | | | V-1 | Hcfc1 |
| 8711 | 3 | 4 | 5 | | | V-1 | Gpr153 | | 8796 | 3 | 4 | 5 | | | V-1 | Hcls1 |
| 8712 | 3 | 4 | 5 | | | V-1 | Gpr157 | | 8797 | 3 | 4 | 5 | | | V-1 | Hdac1 |
| 8713 | 3 | 4 | 5 | | | V-1 | Gpr161 | | 8798 | 3 | 4 | 5 | | | V-1 | Hdac3 |
| 8714 | 3 | 4 | 5 | | | V-1 | Gpr180 | | 8799 | 3 | 4 | 5 | | | V-1 | Hdac7 |
| 8715 | 3 | 4 | 5 | | | V-1 | Gpr182 | | 8800 | 3 | 4 | 5 | | | V-1 | Hdgf |
| 8716 | 3 | 4 | 5 | | | V-1 | Gpr22 | | 8801 | 3 | 4 | 5 | | | V-1 | Heatr3 |
| 8717 | 3 | 4 | 5 | | | V-1 | Gpr39 | | 8802 | 3 | 4 | 5 | | | V-1 | Hebp1 |
| 8718 | 3 | 4 | 5 | | | V-1 | Gpr50 | | 8803 | 3 | 4 | 5 | | | V-1 | Heils |
| 8719 | 3 | 4 | 5 | | | V-1 | Gpr61 | | 8804 | 3 | 4 | 5 | | | V-1 | Herc3 |
| 8720 | 3 | 4 | 5 | | | V-1 | Gpr64 | | 8805 | 3 | 4 | 5 | | | V-1 | Hes1 |
| 8721 | 3 | 4 | 5 | | | V-1 | Gpr65 | | 8806 | 3 | 4 | 5 | | | V-1 | Hes6 |
| 8722 | 3 | 4 | 5 | | | V-1 | Gprasp1 | | 8807 | 3 | 4 | 5 | | | V-1 | Hes7 |
| 8723 | 3 | 4 | 5 | | | V-1 | Gprc5b | | 8808 | 3 | 4 | 5 | | | V-1 | Hexb |
| 8724 | 3 | 4 | 5 | | | V-1 | Gprc5c | | 8809 | 3 | 4 | 5 | | | V-1 | Hfe |
| 8725 | 3 | 4 | 5 | | | V-1 | Gprin3 | | 8810 | 3 | 4 | 5 | | | V-1 | Hhex |
| 8726 | 3 | 4 | 5 | | | V-1 | Gpsm2 | | 8811 | 3 | 4 | 5 | | | V-1 | Hilpda |
| 8727 | 3 | 4 | 5 | | | V-1 | Gpsm3 | | 8812 | 3 | 4 | 5 | | | V-1 | Hint1 |
| 8728 | 3 | 4 | 5 | | | V-1 | Gpt | | 8813 | 3 | 4 | 5 | | | V-1 | Hint3 |
| 8729 | 3 | 4 | 5 | | | V-1 | Gpt2 | | 8814 | 3 | 4 | 5 | | | V-1 | Hip1 |
| 8730 | 3 | 4 | 5 | | | V-1 | Gpx2-ps1 | | 8815 | 3 | 4 | 5 | | | V-1 | Hirip3 |
| 8731 | 3 | 4 | 5 | | | V-1 | Gpx3 | | 8816 | 3 | 4 | 5 | | | V-1 | Hist1h2aa |
| 8732 | 3 | 4 | 5 | | | V-1 | Gpx4 | | 8817 | 3 | 4 | 5 | | | V-1 | Hist1h2ab |
| 8733 | 3 | 4 | 5 | | | V-1 | Gpx7 | | 8818 | 3 | 4 | 5 | | | V-1 | Hist1h2bc |
| 8734 | 3 | 4 | 5 | | | V-1 | Gpx8 | | 8819 | 3 | 4 | 5 | | | V-1 | Hist1h2bh |
| 8735 | 3 | 4 | 5 | | | V-1 | Grb10 | | 8820 | 3 | 4 | 5 | | | V-1 | Hist1h4a |
| 8736 | 3 | 4 | 5 | | | V-1 | Grb14 | | 8821 | 3 | 4 | 5 | | | V-1 | Hist1h4h |
| 8737 | 3 | 4 | 5 | | | V-1 | Greb1l | | 8822 | 3 | 4 | 5 | | | V-1 | Hist1h4i |
| 8738 | 3 | 4 | 5 | | | V-1 | Grhpr | | 8823 | 3 | 4 | 5 | | | V-1 | Hist2h2aa1 |
| 8739 | 3 | 4 | 5 | | | V-1 | Grip1 | | 8824 | 3 | 4 | 5 | | | V-1 | Hk1 |
| 8740 | 3 | 4 | 5 | | | V-1 | Grip2 | | 8825 | 3 | 4 | 5 | | | V-1 | Hk1os |
| 8741 | 3 | 4 | 5 | | | V-1 | Grn | | 8826 | 3 | 4 | 5 | | | V-1 | Hk2 |
| 8742 | 3 | 4 | 5 | | | V-1 | Grpr | | 8827 | 3 | 4 | 5 | | | V-1 | Hk3 |
| 8743 | 3 | 4 | 5 | | | V-1 | Grrp1 | | 8828 | 3 | 4 | 5 | | | V-1 | Hmbs |
| 8744 | 3 | 4 | 5 | | | V-1 | Grwd1 | | 8829 | 3 | 4 | 5 | | | V-1 | Hmga1-rs1 |
| 8745 | 3 | 4 | 5 | | | V-1 | Gsc | | 8830 | 3 | 4 | 5 | | | V-1 | Hmga2-ps1 |
| 8746 | 3 | 4 | 5 | | | V-1 | Gsdmd | | 8831 | 3 | 4 | 5 | | | V-1 | Hmgb2 |
| 8747 | 3 | 4 | 5 | | | V-1 | Gsk3b | | 8832 | 3 | 4 | 5 | | | V-1 | Hmgcs1 |
| 8748 | 3 | 4 | 5 | | | V-1 | Gspt1 | | 8833 | 3 | 4 | 5 | | | V-1 | Hmgn1 |
| 8749 | 3 | 4 | 5 | | | V-1 | Gspt2 | | 8834 | 3 | 4 | 5 | | | V-1 | Hmgn3 |
| 8750 | 3 | 4 | 5 | | | V-1 | Gsr | | 8835 | 3 | 4 | 5 | | | V-1 | Hmgn5 |
| 8751 | 3 | 4 | 5 | | | V-1 | Gss | | 8836 | 3 | 4 | 5 | | | V-1 | Hmha1 |
| 8752 | 3 | 4 | 5 | | | V-1 | Gsta1 | | 8837 | 3 | 4 | 5 | | | V-1 | Hn1 |
| 8753 | 3 | 4 | 5 | | | V-1 | Gsta2 | | 8838 | 3 | 4 | 5 | | | V-1 | Hn1l |

Fig. 43 - 53

| | | | | | | | | |
|---|---|---|---|---|---|---|---|---|
| 8839 | 3 | 4 | 5 | | | V-1 | Hnf1a |
| 8840 | 3 | 4 | 5 | | | V-1 | Hnrnpdl |
| 8841 | 3 | 4 | 5 | | | V-1 | Hnrnpll |
| 8842 | 3 | 4 | 5 | | | V-1 | Hoga1 |
| 8843 | 3 | 4 | 5 | | | V-1 | Hook1 |
| 8844 | 3 | 4 | 5 | | | V-1 | Hook2 |
| 8845 | 3 | 4 | 5 | | | V-1 | Hoxa1 |
| 8846 | 3 | 4 | 5 | | | V-1 | Hoxa11os |
| 8847 | 3 | 4 | 5 | | | V-1 | Hoxa2 |
| 8848 | 3 | 4 | 5 | | | V-1 | Hoxa4 |
| 8849 | 3 | 4 | 5 | | | V-1 | Hoxa6 |
| 8850 | 3 | 4 | 5 | | | V-1 | Hoxb2 |
| 8851 | 3 | 4 | 5 | | | V-1 | Hoxc4 |
| 8852 | 3 | 4 | 5 | | | V-1 | Hoxc5 |
| 8853 | 3 | 4 | 5 | | | V-1 | Hoxd10 |
| 8854 | 3 | 4 | 5 | | | V-1 | Hoxd8 |
| 8855 | 3 | 4 | 5 | | | V-1 | Hpcal4 |
| 8856 | 3 | 4 | 5 | | | V-1 | Hprt |
| 8857 | 3 | 4 | 5 | | | V-1 | Hpse |
| 8858 | 3 | 4 | 5 | | | V-1 | Hras |
| 8859 | 3 | 4 | 5 | | | V-1 | Hrct1 |
| 8860 | 3 | 4 | 5 | | | V-1 | Hrh2 |
| 8861 | 3 | 4 | 5 | | | V-1 | Hsd11b1 |
| 8862 | 3 | 4 | 5 | | | V-1 | Hsd11b2 |
| 8863 | 3 | 4 | 5 | | | V-1 | Hsd3b3 |
| 8864 | 3 | 4 | 5 | | | V-1 | Hsf2bp |
| 8865 | 3 | 4 | 5 | | | V-1 | Hsh2d |
| 8866 | 3 | 4 | 5 | | | V-1 | Hsp90aa1 |
| 8867 | 3 | 4 | 5 | | | V-1 | Hsp90b1 |
| 8868 | 3 | 4 | 5 | | | V-1 | Hspa12a |
| 8869 | 3 | 4 | 5 | | | V-1 | Hspa14 |
| 8870 | 3 | 4 | 5 | | | V-1 | Hspa1l |
| 8871 | 3 | 4 | 5 | | | V-1 | Hspa5 |
| 8872 | 3 | 4 | 5 | | | V-1 | Hspa9 |
| 8873 | 3 | 4 | 5 | | | V-1 | Hspbp1 |
| 8874 | 3 | 4 | 5 | | | V-1 | Hspd1 |
| 8875 | 3 | 4 | 5 | | | V-1 | Hspe1 |
| 8876 | 3 | 4 | 5 | | | V-1 | Htr2b |
| 8877 | 3 | 4 | 5 | | | V-1 | Htra3 |
| 8878 | 3 | 4 | 5 | | | V-1 | Htra4 |
| 8879 | 3 | 4 | 5 | | | V-1 | Htt |
| 8880 | 3 | 4 | 5 | | | V-1 | Hunk |
| 8881 | 3 | 4 | 5 | | | V-1 | Huwe1 |
| 8882 | 3 | 4 | 5 | | | V-1 | Hyou1 |
| 8883 | 3 | 4 | 5 | | | V-1 | I730030J21Rik |
| 8884 | 3 | 4 | 5 | | | V-1 | Iah1 |
| 8885 | 3 | 4 | 5 | | | V-1 | Iars |
| 8886 | 3 | 4 | 5 | | | V-1 | Ibtk |
| 8887 | 3 | 4 | 5 | | | V-1 | Ica1 |
| 8888 | 3 | 4 | 5 | | | V-1 | Icam4 |
| 8889 | 3 | 4 | 5 | | | V-1 | Icosl |
| 8890 | 3 | 4 | 5 | | | V-1 | Id1 |
| 8891 | 3 | 4 | 5 | | | V-1 | Idh1 |
| 8892 | 3 | 4 | 5 | | | V-1 | Idh2 |
| 8893 | 3 | 4 | 5 | | | V-1 | Idh3a |
| 8894 | 3 | 4 | 5 | | | V-1 | Idh3g |
| 8895 | 3 | 4 | 5 | | | V-1 | Ier2 |
| 8896 | 3 | 4 | 5 | | | V-1 | Ier5 |
| 8897 | 3 | 4 | 5 | | | V-1 | Ifi203 |
| 8898 | 3 | 4 | 5 | | | V-1 | Ifi205 |
| 8899 | 3 | 4 | 5 | | | V-1 | Ifi27 |
| 8900 | 3 | 4 | 5 | | | V-1 | Ifi30 |
| 8901 | 3 | 4 | 5 | | | V-1 | Ifih1 |
| 8902 | 3 | 4 | 5 | | | V-1 | Ifitm1 |
| 8903 | 3 | 4 | 5 | | | V-1 | Ifitm2 |
| 8904 | 3 | 4 | 5 | | | V-1 | Ifitm5 |
| 8905 | 3 | 4 | 5 | | | V-1 | Ift74 |
| 8906 | 3 | 4 | 5 | | | V-1 | Igfals |
| 8907 | 3 | 4 | 5 | | | V-1 | Igfbp4 |
| 8908 | 3 | 4 | 5 | | | V-1 | Igfbp6 |
| 8909 | 3 | 4 | 5 | | | V-1 | Igsf6 |
| 8910 | 3 | 4 | 5 | | | V-1 | Ikzf1 |
| 8911 | 3 | 4 | 5 | | | V-1 | Il10ra |
| 8912 | 3 | 4 | 5 | | | V-1 | Il11ra1 |
| 8913 | 3 | 4 | 5 | | | V-1 | Il15ra |
| 8914 | 3 | 4 | 5 | | | V-1 | Il17ra |
| 8915 | 3 | 4 | 5 | | | V-1 | Il17rb |
| 8916 | 3 | 4 | 5 | | | V-1 | Il18r1 |
| 8917 | 3 | 4 | 5 | | | V-1 | Il1a |
| 8918 | 3 | 4 | 5 | | | V-1 | Il1b |
| 8919 | 3 | 4 | 5 | | | V-1 | Il1bos |
| 8920 | 3 | 4 | 5 | | | V-1 | Il1r1 |
| 8921 | 3 | 4 | 5 | | | V-1 | Il1rap |
| 8922 | 3 | 4 | 5 | | | V-1 | Il20rb |
| 8923 | 3 | 4 | 5 | | | V-1 | Il21r |
| 8924 | 3 | 4 | 5 | | | V-1 | Il27 |
| 8925 | 3 | 4 | 5 | | | V-1 | Il2rb |
| 8926 | 3 | 4 | 5 | | | V-1 | Il34 |
| 8927 | 3 | 4 | 5 | | | V-1 | Il4ra |
| 8928 | 3 | 4 | 5 | | | V-1 | Il6st |
| 8929 | 3 | 4 | 5 | | | V-1 | Il7 |
| 8930 | 3 | 4 | 5 | | | V-1 | Ildr2 |
| 8931 | 3 | 4 | 5 | | | V-1 | Ilf2 |
| 8932 | 3 | 4 | 5 | | | V-1 | Immp1l |
| 8933 | 3 | 4 | 5 | | | V-1 | Impa1 |
| 8934 | 3 | 4 | 5 | | | V-1 | Impdh2 |
| 8935 | 3 | 4 | 5 | | | V-1 | Inca1 |
| 8936 | 3 | 4 | 5 | | | V-1 | Incenp |
| 8937 | 3 | 4 | 5 | | | V-1 | Ino80c |
| 8938 | 3 | 4 | 5 | | | V-1 | Inpp5d |
| 8939 | 3 | 4 | 5 | | | V-1 | Insig1 |
| 8940 | 3 | 4 | 5 | | | V-1 | Insl6 |
| 8941 | 3 | 4 | 5 | | | V-1 | Ints2 |
| 8942 | 3 | 4 | 5 | | | V-1 | Ipo5 |
| 8943 | 3 | 4 | 5 | | | V-1 | Iqck |
| 8944 | 3 | 4 | 5 | | | V-1 | Iqsec2 |
| 8945 | 3 | 4 | 5 | | | V-1 | Irf1 |
| 8946 | 3 | 4 | 5 | | | V-1 | Irf5 |
| 8947 | 3 | 4 | 5 | | | V-1 | Irf8 |
| 8948 | 3 | 4 | 5 | | | V-1 | Irgm1 |
| 8949 | 3 | 4 | 5 | | | V-1 | Irx4 |
| 8950 | 3 | 4 | 5 | | | V-1 | Isca2 |
| 8951 | 3 | 4 | 5 | | | V-1 | Iscu |
| 8952 | 3 | 4 | 5 | | | V-1 | Isl1 |
| 8953 | 3 | 4 | 5 | | | V-1 | Islr |
| 8954 | 3 | 4 | 5 | | | V-1 | Islr2 |
| 8955 | 3 | 4 | 5 | | | V-1 | Isoc1 |
| 8956 | 3 | 4 | 5 | | | V-1 | Itfg2 |
| 8957 | 3 | 4 | 5 | | | V-1 | Itga2b |
| 8958 | 3 | 4 | 5 | | | V-1 | Itga4 |
| 8959 | 3 | 4 | 5 | | | V-1 | Itga5 |
| 8960 | 3 | 4 | 5 | | | V-1 | Itga6 |
| 8961 | 3 | 4 | 5 | | | V-1 | Itgad |
| 8962 | 3 | 4 | 5 | | | V-1 | Itgal |
| 8963 | 3 | 4 | 5 | | | V-1 | Itgb2 |
| 8964 | 3 | 4 | 5 | | | V-1 | Itk |
| 8965 | 3 | 4 | 5 | | | V-1 | Itm2a |
| 8966 | 3 | 4 | 5 | | | V-1 | Itpa |
| 8967 | 3 | 4 | 5 | | | V-1 | Iws1 |
| 8968 | 3 | 4 | 5 | | | V-1 | Jam3 |
| 8969 | 3 | 4 | 5 | | | V-1 | Jdp2 |
| 8970 | 3 | 4 | 5 | | | V-1 | Jmjd1c |
| 8971 | 3 | 4 | 5 | | | V-1 | Jmjd7 |
| 8972 | 3 | 4 | 5 | | | V-1 | Josd2 |
| 8973 | 3 | 4 | 5 | | | V-1 | Jund |
| 8974 | 3 | 4 | 5 | | | V-1 | Kank1 |
| 8975 | 3 | 4 | 5 | | | V-1 | Kank3 |
| 8976 | 3 | 4 | 5 | | | V-1 | Kansl1 |
| 8977 | 3 | 4 | 5 | | | V-1 | Kbtbd3 |
| 8978 | 3 | 4 | 5 | | | V-1 | Kcna1 |
| 8979 | 3 | 4 | 5 | | | V-1 | Kcnc1 |
| 8980 | 3 | 4 | 5 | | | V-1 | Kcnc2 |
| 8981 | 3 | 4 | 5 | | | V-1 | Kcne3 |
| 8982 | 3 | 4 | 5 | | | V-1 | Kcne4 |
| 8983 | 3 | 4 | 5 | | | V-1 | Kcng2 |
| 8984 | 3 | 4 | 5 | | | V-1 | Kcnh7 |
| 8985 | 3 | 4 | 5 | | | V-1 | Kcnip4 |
| 8986 | 3 | 4 | 5 | | | V-1 | Kcnj10 |
| 8987 | 3 | 4 | 5 | | | V-1 | Kcnj15 |
| 8988 | 3 | 4 | 5 | | | V-1 | Kcnj8 |
| 8989 | 3 | 4 | 5 | | | V-1 | Kcnk13 |
| 8990 | 3 | 4 | 5 | | | V-1 | Kcnk3 |
| 8991 | 3 | 4 | 5 | | | V-1 | Kcnk7 |
| 8992 | 3 | 4 | 5 | | | V-1 | Kcnq1 |
| 8993 | 3 | 4 | 5 | | | V-1 | Kctd1 |
| 8994 | 3 | 4 | 5 | | | V-1 | Kctd12 |
| 8995 | 3 | 4 | 5 | | | V-1 | Kctd17 |
| 8996 | 3 | 4 | 5 | | | V-1 | Kctd2 |
| 8997 | 3 | 4 | 5 | | | V-1 | Kctd9 |
| 8998 | 3 | 4 | 5 | | | V-1 | Kdelc1 |
| 8999 | 3 | 4 | 5 | | | V-1 | Kdelr3 |
| 9000 | 3 | 4 | 5 | | | V-1 | Kdf1 |
| 9001 | 3 | 4 | 5 | | | V-1 | Kdm4a |
| 9002 | 3 | 4 | 5 | | | V-1 | Kdm5a |
| 9003 | 3 | 4 | 5 | | | V-1 | Kdm6b |
| 9004 | 3 | 4 | 5 | | | V-1 | Kdm7a |
| 9005 | 3 | 4 | 5 | | | V-1 | Kdm8 |
| 9006 | 3 | 4 | 5 | | | V-1 | Kdr |
| 9007 | 3 | 4 | 5 | | | V-1 | Khdrbs3 |
| 9008 | 3 | 4 | 5 | | | V-1 | Kif20a |

Fig. 43 - 54

| | | | | | | | | | | | | | | | | |
|---|---|---|---|---|---|---|---|---|---|---|---|---|---|---|---|---|
| 9009 | 3 | 4 | 5 | | | V-1 | Kif21b | | 9094 | 3 | 4 | 5 | | | V-1 | Lipe |
| 9010 | 3 | 4 | 5 | | | V-1 | Kif22 | | 9095 | 3 | 4 | 5 | | | V-1 | Lipt1 |
| 9011 | 3 | 4 | 5 | | | V-1 | Kif5c | | 9096 | 3 | 4 | 5 | | | V-1 | Lmna |
| 9012 | 3 | 4 | 5 | | | V-1 | Kirrel | | 9097 | 3 | 4 | 5 | | | V-1 | Lmnb1 |
| 9013 | 3 | 4 | 5 | | | V-1 | Kiss1 | | 9098 | 3 | 4 | 5 | | | V-1 | Lmnb2 |
| 9014 | 3 | 4 | 5 | | | V-1 | Kit | | 9099 | 3 | 4 | 5 | | | V-1 | Lmo2 |
| 9015 | 3 | 4 | 5 | | | V-1 | Klf15 | | 9100 | 3 | 4 | 5 | | | V-1 | Lmo7 |
| 9016 | 3 | 4 | 5 | | | V-1 | Klhdc7a | | 9101 | 3 | 4 | 5 | | | V-1 | LOC100861978 |
| 9017 | 3 | 4 | 5 | | | V-1 | Klhdc8a | | 9102 | 3 | 4 | 5 | | | V-1 | LOC101669761 |
| 9018 | 3 | 4 | 5 | | | V-1 | Klhdc8b | | 9103 | 3 | 4 | 5 | | | V-1 | LOC102631757 |
| 9019 | 3 | 4 | 5 | | | V-1 | Klhl15 | | 9104 | 3 | 4 | 5 | | | V-1 | LOC666331 |
| 9020 | 3 | 4 | 5 | | | V-1 | Klhl23 | | 9105 | 3 | 4 | 5 | | | V-1 | Lonp1 |
| 9021 | 3 | 4 | 5 | | | V-1 | Klhl29 | | 9106 | 3 | 4 | 5 | | | V-1 | Lox |
| 9022 | 3 | 4 | 5 | | | V-1 | Klk10 | | 9107 | 3 | 4 | 5 | | | V-1 | Loxl2 |
| 9023 | 3 | 4 | 5 | | | V-1 | Klk11 | | 9108 | 3 | 4 | 5 | | | V-1 | Lpar3 |
| 9024 | 3 | 4 | 5 | | | V-1 | Klk14 | | 9109 | 3 | 4 | 5 | | | V-1 | Lpar5 |
| 9025 | 3 | 4 | 5 | | | V-1 | Klk1b27 | | 9110 | 3 | 4 | 5 | | | V-1 | Lpgat1 |
| 9026 | 3 | 4 | 5 | | | V-1 | Klk1b4 | | 9111 | 3 | 4 | 5 | | | V-1 | Lpo |
| 9027 | 3 | 4 | 5 | | | V-1 | Klk1b9 | | 9112 | 3 | 4 | 5 | | | V-1 | Lpxn |
| 9028 | 3 | 4 | 5 | | | V-1 | Klk7 | | 9113 | 3 | 4 | 5 | | | V-1 | Lrba |
| 9029 | 3 | 4 | 5 | | | V-1 | Klk9 | | 9114 | 3 | 4 | 5 | | | V-1 | Lrif1 |
| 9030 | 3 | 4 | 5 | | | V-1 | Klra7 | | 9115 | 3 | 4 | 5 | | | V-1 | Lrig3 |
| 9031 | 3 | 4 | 5 | | | V-1 | Klrb1c | | 9116 | 3 | 4 | 5 | | | V-1 | Lrp1 |
| 9032 | 3 | 4 | 5 | | | V-1 | Klrg2 | | 9117 | 3 | 4 | 5 | | | V-1 | Lrp11 |
| 9033 | 3 | 4 | 5 | | | V-1 | Klrk1 | | 9118 | 3 | 4 | 5 | | | V-1 | Lrp3 |
| 9034 | 3 | 4 | 5 | | | V-1 | Kmt2b | | 9119 | 3 | 4 | 5 | | | V-1 | Lrp8 |
| 9035 | 3 | 4 | 5 | | | V-1 | Kmt2e | | 9120 | 3 | 4 | 5 | | | V-1 | Lrrc10b |
| 9036 | 3 | 4 | 5 | | | V-1 | Kng2 | | 9121 | 3 | 4 | 5 | | | V-1 | Lrrc17 |
| 9037 | 3 | 4 | 5 | | | V-1 | Knstrn | | 9122 | 3 | 4 | 5 | | | V-1 | Lrrc20 |
| 9038 | 3 | 4 | 5 | | | V-1 | Kpna2 | | 9123 | 3 | 4 | 5 | | | V-1 | Lrrc26 |
| 9039 | 3 | 4 | 5 | | | V-1 | Kremen2 | | 9124 | 3 | 4 | 5 | | | V-1 | Lrrc40 |
| 9040 | 3 | 4 | 5 | | | V-1 | Kri1 | | 9125 | 3 | 4 | 5 | | | V-1 | Lrrc75b |
| 9041 | 3 | 4 | 5 | | | V-1 | Krt19 | | 9126 | 3 | 4 | 5 | | | V-1 | Lrrc8c |
| 9042 | 3 | 4 | 5 | | | V-1 | Krt27 | | 9127 | 3 | 4 | 5 | | | V-1 | Lrrc8d |
| 9043 | 3 | 4 | 5 | | | V-1 | Krt8 | | 9128 | 3 | 4 | 5 | | | V-1 | Lrrn2 |
| 9044 | 3 | 4 | 5 | | | V-1 | Krt80 | | 9129 | 3 | 4 | 5 | | | V-1 | Lrrn4 |
| 9045 | 3 | 4 | 5 | | | V-1 | Krtap14 | | 9130 | 3 | 4 | 5 | | | V-1 | Lrrn4cl |
| 9046 | 3 | 4 | 5 | | | V-1 | Krtap19-4 | | 9131 | 3 | 4 | 5 | | | V-1 | Lrwd1 |
| 9047 | 3 | 4 | 5 | | | V-1 | Krtap4-7 | | 9132 | 3 | 4 | 5 | | | V-1 | Lsg1 |
| 9048 | 3 | 4 | 5 | | | V-1 | Krtcap2 | | 9133 | 3 | 4 | 5 | | | V-1 | Lsm3 |
| 9049 | 3 | 4 | 5 | | | V-1 | L2hgdh | | 9134 | 3 | 4 | 5 | | | V-1 | Lsm4 |
| 9050 | 3 | 4 | 5 | | | V-1 | L3mbtl2 | | 9135 | 3 | 4 | 5 | | | V-1 | Lsm6 |
| 9051 | 3 | 4 | 5 | | | V-1 | Lacc1 | | 9136 | 3 | 4 | 5 | | | V-1 | Lsm7 |
| 9052 | 3 | 4 | 5 | | | V-1 | Lag3 | | 9137 | 3 | 4 | 5 | | | V-1 | Lsm8 |
| 9053 | 3 | 4 | 5 | | | V-1 | Lage3 | | 9138 | 3 | 4 | 5 | | | V-1 | Lsp1 |
| 9054 | 3 | 4 | 5 | | | V-1 | Lama4 | | 9139 | 3 | 4 | 5 | | | V-1 | Lsr |
| 9055 | 3 | 4 | 5 | | | V-1 | Lama5 | | 9140 | 3 | 4 | 5 | | | V-1 | Lss |
| 9056 | 3 | 4 | 5 | | | V-1 | Lamb1 | | 9141 | 3 | 4 | 5 | | | V-1 | Ltb4r2 |
| 9057 | 3 | 4 | 5 | | | V-1 | Lamtor1 | | 9142 | 3 | 4 | 5 | | | V-1 | Ltbp1 |
| 9058 | 3 | 4 | 5 | | | V-1 | Lap3 | | 9143 | 3 | 4 | 5 | | | V-1 | Ltbp3 |
| 9059 | 3 | 4 | 5 | | | V-1 | Larp7 | | 9144 | 3 | 4 | 5 | | | V-1 | Ltbr |
| 9060 | 3 | 4 | 5 | | | V-1 | Lars2 | | 9145 | 3 | 4 | 5 | | | V-1 | Lurap1 |
| 9061 | 3 | 4 | 5 | | | V-1 | Lasp1 | | 9146 | 3 | 4 | 5 | | | V-1 | Lxn |
| 9062 | 3 | 4 | 5 | | | V-1 | Layn | | 9147 | 3 | 4 | 5 | | | V-1 | Ly6a |
| 9063 | 3 | 4 | 5 | | | V-1 | Lbp | | 9148 | 3 | 4 | 5 | | | V-1 | Ly6c1 |
| 9064 | 3 | 4 | 5 | | | V-1 | Lce1a2 | | 9149 | 3 | 4 | 5 | | | V-1 | Ly6c2 |
| 9065 | 3 | 4 | 5 | | | V-1 | Lce1c | | 9150 | 3 | 4 | 5 | | | V-1 | Ly6g5b |
| 9066 | 3 | 4 | 5 | | | V-1 | Lce3a | | 9151 | 3 | 4 | 5 | | | V-1 | Ly6g6d |
| 9067 | 3 | 4 | 5 | | | V-1 | Lce3b | | 9152 | 3 | 4 | 5 | | | V-1 | Ly6h |
| 9068 | 3 | 4 | 5 | | | V-1 | Lce3c | | 9153 | 3 | 4 | 5 | | | V-1 | Ly6k |
| 9069 | 3 | 4 | 5 | | | V-1 | Lce6a | | 9154 | 3 | 4 | 5 | | | V-1 | Ly9 |
| 9070 | 3 | 4 | 5 | | | V-1 | Lclat1 | | 9155 | 3 | 4 | 5 | | | V-1 | Ly96 |
| 9071 | 3 | 4 | 5 | | | V-1 | Lcp1 | | 9156 | 3 | 4 | 5 | | | V-1 | Lyar |
| 9072 | 3 | 4 | 5 | | | V-1 | Lcp2 | | 9157 | 3 | 4 | 5 | | | V-1 | Lyn |
| 9073 | 3 | 4 | 5 | | | V-1 | Ldb2 | | 9158 | 3 | 4 | 5 | | | V-1 | Lyrm1 |
| 9074 | 3 | 4 | 5 | | | V-1 | Ldha | | 9159 | 3 | 4 | 5 | | | V-1 | Lyrm7 |
| 9075 | 3 | 4 | 5 | | | V-1 | Lef1 | | 9160 | 3 | 4 | 5 | | | V-1 | Lyrm7os |
| 9076 | 3 | 4 | 5 | | | V-1 | Lefty1 | | 9161 | 3 | 4 | 5 | | | V-1 | Lyrm9 |
| 9077 | 3 | 4 | 5 | | | V-1 | Leng8 | | 9162 | 3 | 4 | 5 | | | V-1 | Lysmd2 |
| 9078 | 3 | 4 | 5 | | | V-1 | Lgals1 | | 9163 | 3 | 4 | 5 | | | V-1 | Lysmd3 |
| 9079 | 3 | 4 | 5 | | | V-1 | Lgi4 | | 9164 | 3 | 4 | 5 | | | V-1 | Lyve1 |
| 9080 | 3 | 4 | 5 | | | V-1 | Lgmn | | 9165 | 3 | 4 | 5 | | | V-1 | Lyz1 |
| 9081 | 3 | 4 | 5 | | | V-1 | Lgr4 | | 9166 | 3 | 4 | 5 | | | V-1 | Mad2l1 |
| 9082 | 3 | 4 | 5 | | | V-1 | Lhx6 | | 9167 | 3 | 4 | 5 | | | V-1 | Mad2l2 |
| 9083 | 3 | 4 | 5 | | | V-1 | Lias | | 9168 | 3 | 4 | 5 | | | V-1 | Madcam1 |
| 9084 | 3 | 4 | 5 | | | V-1 | Lig1 | | 9169 | 3 | 4 | 5 | | | V-1 | Maf |
| 9085 | 3 | 4 | 5 | | | V-1 | Lig3 | | 9170 | 3 | 4 | 5 | | | V-1 | Mafa |
| 9086 | 3 | 4 | 5 | | | V-1 | Lilra6 | | 9171 | 3 | 4 | 5 | | | V-1 | Mafb |
| 9087 | 3 | 4 | 5 | | | V-1 | Lima1 | | 9172 | 3 | 4 | 5 | | | V-1 | Mageh1 |
| 9088 | 3 | 4 | 5 | | | V-1 | Limch1 | | 9173 | 3 | 4 | 5 | | | V-1 | Mal |
| 9089 | 3 | 4 | 5 | | | V-1 | Lin54 | | 9174 | 3 | 4 | 5 | | | V-1 | Mal2 |
| 9090 | 3 | 4 | 5 | | | V-1 | Lin9 | | 9175 | 3 | 4 | 5 | | | V-1 | Malsu1 |
| 9091 | 3 | 4 | 5 | | | V-1 | Lingo1 | | 9176 | 3 | 4 | 5 | | | V-1 | Mamstr |
| 9092 | 3 | 4 | 5 | | | V-1 | Lingo3 | | 9177 | 3 | 4 | 5 | | | V-1 | Man2a1 |
| 9093 | 3 | 4 | 5 | | | V-1 | Lipa | | 9178 | 3 | 4 | 5 | | | V-1 | Manba |

Fig. 43 - 55

| | | | | | | | | |
|---|---|---|---|---|---|---|---|---|
| 9179 | 3 | 4 | 5 | | | V-1 | Manscl |
| 9180 | 3 | 4 | 5 | | | V-1 | Maoa |
| 9181 | 3 | 4 | 5 | | | V-1 | Map1b |
| 9182 | 3 | 4 | 5 | | | V-1 | Map2k3 |
| 9183 | 3 | 4 | 5 | | | V-1 | Map3k13 |
| 9184 | 3 | 4 | 5 | | | V-1 | Map3k2 |
| 9185 | 3 | 4 | 5 | | | V-1 | Map3k3 |
| 9186 | 3 | 4 | 5 | | | V-1 | Map3k5 |
| 9187 | 3 | 4 | 5 | | | V-1 | Map3k6 |
| 9188 | 3 | 4 | 5 | | | V-1 | Map3k7cl |
| 9189 | 3 | 4 | 5 | | | V-1 | Mapk10 |
| 9190 | 3 | 4 | 5 | | | V-1 | Mapk12 |
| 9191 | 3 | 4 | 5 | | | V-1 | Mapk13 |
| 9192 | 3 | 4 | 5 | | | V-1 | Mapk4 |
| 9193 | 3 | 4 | 5 | | | V-1 | Mapk6 |
| 9194 | 3 | 4 | 5 | | | V-1 | Mapk8ip1 |
| 9195 | 3 | 4 | 5 | | | V-1 | Mapkapk3 |
| 9196 | 3 | 4 | 5 | | | V-1 | Mapkbp1 |
| 9197 | 3 | 4 | 5 | | | V-1 | Mapre2 |
| 9198 | 3 | 4 | 5 | | | V-1 | Mapt |
| 9199 | 3 | 4 | 5 | | | V-1 | Marc1 |
| 9200 | 3 | 4 | 5 | | | V-1 | March1 |
| 9201 | 3 | 4 | 5 | | | V-1 | March7 |
| 9202 | 3 | 4 | 5 | | | V-1 | Mars2 |
| 9203 | 3 | 4 | 5 | | | V-1 | Mast2 |
| 9204 | 3 | 4 | 5 | | | V-1 | Matn2 |
| 9205 | 3 | 4 | 5 | | | V-1 | Matn4 |
| 9206 | 3 | 4 | 5 | | | V-1 | Mbd6 |
| 9207 | 3 | 4 | 5 | | | V-1 | Mbip |
| 9208 | 3 | 4 | 5 | | | V-1 | Mbl1 |
| 9209 | 3 | 4 | 5 | | | V-1 | Mbnl2 |
| 9210 | 3 | 4 | 5 | | | V-1 | Mccc2 |
| 9211 | 3 | 4 | 5 | | | V-1 | Mcee |
| 9212 | 3 | 4 | 5 | | | V-1 | Mchr1 |
| 9213 | 3 | 4 | 5 | | | V-1 | Mcm2 |
| 9214 | 3 | 4 | 5 | | | V-1 | Mcm4 |
| 9215 | 3 | 4 | 5 | | | V-1 | Mcm6 |
| 9216 | 3 | 4 | 5 | | | V-1 | Mcm9 |
| 9217 | 3 | 4 | 5 | | | V-1 | Mcoin1 |
| 9218 | 3 | 4 | 5 | | | V-1 | Mcpt2 |
| 9219 | 3 | 4 | 5 | | | V-1 | Mcpt8 |
| 9220 | 3 | 4 | 5 | | | V-1 | Mcrs1 |
| 9221 | 3 | 4 | 5 | | | V-1 | Mctp2 |
| 9222 | 3 | 4 | 5 | | | V-1 | Mcts2 |
| 9223 | 3 | 4 | 5 | | | V-1 | Mdh1 |
| 9224 | 3 | 4 | 5 | | | V-1 | Mdh2 |
| 9225 | 3 | 4 | 5 | | | V-1 | Med10 |
| 9226 | 3 | 4 | 5 | | | V-1 | Med13 |
| 9227 | 3 | 4 | 5 | | | V-1 | Med14 |
| 9228 | 3 | 4 | 5 | | | V-1 | Med19 |
| 9229 | 3 | 4 | 5 | | | V-1 | Med21 |
| 9230 | 3 | 4 | 5 | | | V-1 | Med30 |
| 9231 | 3 | 4 | 5 | | | V-1 | Med31 |
| 9232 | 3 | 4 | 5 | | | V-1 | Med4 |
| 9233 | 3 | 4 | 5 | | | V-1 | Med6 |
| 9234 | 3 | 4 | 5 | | | V-1 | Mef2b |
| 9235 | 3 | 4 | 5 | | | V-1 | Mef2d |
| 9236 | 3 | 4 | 5 | | | V-1 | Mefv |
| 9237 | 3 | 4 | 5 | | | V-1 | Meg3 |
| 9238 | 3 | 4 | 5 | | | V-1 | Megf8 |
| 9239 | 3 | 4 | 5 | | | V-1 | Mest |
| 9240 | 3 | 4 | 5 | | | V-1 | Metrn |
| 9241 | 3 | 4 | 5 | | | V-1 | Mettl10 |
| 9242 | 3 | 4 | 5 | | | V-1 | Mettl17 |
| 9243 | 3 | 4 | 5 | | | V-1 | Mettl21c |
| 9244 | 3 | 4 | 5 | | | V-1 | Mettl24 |
| 9245 | 3 | 4 | 5 | | | V-1 | Mfap5 |
| 9246 | 3 | 4 | 5 | | | V-1 | Mfsd2b |
| 9247 | 3 | 4 | 5 | | | V-1 | Mfsd7a |
| 9248 | 3 | 4 | 5 | | | V-1 | Mfsd9 |
| 9249 | 3 | 4 | 5 | | | V-1 | Mgam |
| 9250 | 3 | 4 | 5 | | | V-1 | Mgat3 |
| 9251 | 3 | 4 | 5 | | | V-1 | Mgat4a |
| 9252 | 3 | 4 | 5 | | | V-1 | Mgll |
| 9253 | 3 | 4 | 5 | | | V-1 | Mgst3 |
| 9254 | 3 | 4 | 5 | | | V-1 | Mical2 |
| 9255 | 3 | 4 | 5 | | | V-1 | Micall2 |
| 9256 | 3 | 4 | 5 | | | V-1 | Mid1ip1 |
| 9257 | 3 | 4 | 5 | | | V-1 | Mid2 |
| 9258 | 3 | 4 | 5 | | | V-1 | Mien1 |
| 9259 | 3 | 4 | 5 | | | V-1 | Mif |
| 9260 | 3 | 4 | 5 | | | V-1 | Milr1 |
| 9261 | 3 | 4 | 5 | | | V-1 | Minos1 |
| 9262 | 3 | 4 | 5 | | | V-1 | Mipol1 |
| 9263 | 3 | 4 | 5 | | | V-1 | Mir143hg |
| 9264 | 3 | 4 | 5 | | | V-1 | Mir22hg |
| 9265 | 3 | 4 | 5 | | | V-1 | Mirlet7bhg |
| 9266 | 3 | 4 | 5 | | | V-1 | Mitd1 |
| 9267 | 3 | 4 | 5 | | | V-1 | Mkln1os |
| 9268 | 3 | 4 | 5 | | | V-1 | Mks1 |
| 9269 | 3 | 4 | 5 | | | V-1 | Mlf1 |
| 9270 | 3 | 4 | 5 | | | V-1 | Mllt11 |
| 9271 | 3 | 4 | 5 | | | V-1 | Mllt3 |
| 9272 | 3 | 4 | 5 | | | V-1 | Mllt4 |
| 9273 | 3 | 4 | 5 | | | V-1 | Mlxipl |
| 9274 | 3 | 4 | 5 | | | V-1 | Mmachc |
| 9275 | 3 | 4 | 5 | | | V-1 | Mmp14 |
| 9276 | 3 | 4 | 5 | | | V-1 | Mmp19 |
| 9277 | 3 | 4 | 5 | | | V-1 | Mmp23 |
| 9278 | 3 | 4 | 5 | | | V-1 | Mmrn1 |
| 9279 | 3 | 4 | 5 | | | V-1 | Mmrn2 |
| 9280 | 3 | 4 | 5 | | | V-1 | Mnat1 |
| 9281 | 3 | 4 | 5 | | | V-1 | Mnd1 |
| 9282 | 3 | 4 | 5 | | | V-1 | Mnd1-ps |
| 9283 | 3 | 4 | 5 | | | V-1 | Mocos |
| 9284 | 3 | 4 | 5 | | | V-1 | Mocs2 |
| 9285 | 3 | 4 | 5 | | | V-1 | Morc4 |
| 9286 | 3 | 4 | 5 | | | V-1 | Morn3 |
| 9287 | 3 | 4 | 5 | | | V-1 | Mospd1 |
| 9288 | 3 | 4 | 5 | | | V-1 | Mov10l1 |
| 9289 | 3 | 4 | 5 | | | V-1 | Mpc1 |
| 9290 | 3 | 4 | 5 | | | V-1 | Mpg |
| 9291 | 3 | 4 | 5 | | | V-1 | Mphosph8 |
| 9292 | 3 | 4 | 5 | | | V-1 | Mpi |
| 9293 | 3 | 4 | 5 | | | V-1 | Mpo |
| 9294 | 3 | 4 | 5 | | | V-1 | Mpp3 |
| 9295 | 3 | 4 | 5 | | | V-1 | Mpp6 |
| 9296 | 3 | 4 | 5 | | | V-1 | Mppe1 |
| 9297 | 3 | 4 | 5 | | | V-1 | Mpv17l |
| 9298 | 3 | 4 | 5 | | | V-1 | Mpv17l2 |
| 9299 | 3 | 4 | 5 | | | V-1 | Mpzl1 |
| 9300 | 3 | 4 | 5 | | | V-1 | Mpzl2 |
| 9301 | 3 | 4 | 5 | | | V-1 | Mpzl3 |
| 9302 | 3 | 4 | 5 | | | V-1 | Mr1 |
| 9303 | 3 | 4 | 5 | | | V-1 | Mrap |
| 9304 | 3 | 4 | 5 | | | V-1 | Mrc2 |
| 9305 | 3 | 4 | 5 | | | V-1 | Mrpl12 |
| 9306 | 3 | 4 | 5 | | | V-1 | Mrpl13 |
| 9307 | 3 | 4 | 5 | | | V-1 | Mrpl14 |
| 9308 | 3 | 4 | 5 | | | V-1 | Mrpl16 |
| 9309 | 3 | 4 | 5 | | | V-1 | Mrpl18 |
| 9310 | 3 | 4 | 5 | | | V-1 | Mrpl2 |
| 9311 | 3 | 4 | 5 | | | V-1 | Mrpl20 |
| 9312 | 3 | 4 | 5 | | | V-1 | Mrpl22 |
| 9313 | 3 | 4 | 5 | | | V-1 | Mrpl28 |
| 9314 | 3 | 4 | 5 | | | V-1 | Mrpl3 |
| 9315 | 3 | 4 | 5 | | | V-1 | Mrpl4 |
| 9316 | 3 | 4 | 5 | | | V-1 | Mrpl40 |
| 9317 | 3 | 4 | 5 | | | V-1 | Mrpl41 |
| 9318 | 3 | 4 | 5 | | | V-1 | Mrpl42 |
| 9319 | 3 | 4 | 5 | | | V-1 | Mrpl45 |
| 9320 | 3 | 4 | 5 | | | V-1 | Mrpl46 |
| 9321 | 3 | 4 | 5 | | | V-1 | Mrpl48 |
| 9322 | 3 | 4 | 5 | | | V-1 | Mrpl51 |
| 9323 | 3 | 4 | 5 | | | V-1 | Mrpl53 |
| 9324 | 3 | 4 | 5 | | | V-1 | Mrpl55 |
| 9325 | 3 | 4 | 5 | | | V-1 | Mrps10 |
| 9326 | 3 | 4 | 5 | | | V-1 | Mrps12 |
| 9327 | 3 | 4 | 5 | | | V-1 | Mrps14 |
| 9328 | 3 | 4 | 5 | | | V-1 | Mrps16 |
| 9329 | 3 | 4 | 5 | | | V-1 | Mrps18a |
| 9330 | 3 | 4 | 5 | | | V-1 | Mrps18b |
| 9331 | 3 | 4 | 5 | | | V-1 | Mrps21 |
| 9332 | 3 | 4 | 5 | | | V-1 | Mrps22 |
| 9333 | 3 | 4 | 5 | | | V-1 | Mrps23 |
| 9334 | 3 | 4 | 5 | | | V-1 | Mrps24 |
| 9335 | 3 | 4 | 5 | | | V-1 | Mrps26 |
| 9336 | 3 | 4 | 5 | | | V-1 | Mrps28 |
| 9337 | 3 | 4 | 5 | | | V-1 | Mrps34 |
| 9338 | 3 | 4 | 5 | | | V-1 | Mrps36 |
| 9339 | 3 | 4 | 5 | | | V-1 | Mrps5 |
| 9340 | 3 | 4 | 5 | | | V-1 | Mrps7 |
| 9341 | 3 | 4 | 5 | | | V-1 | Mrvi1 |
| 9342 | 3 | 4 | 5 | | | V-1 | Ms4a18 |
| 9343 | 3 | 4 | 5 | | | V-1 | Ms4a6b |
| 9344 | 3 | 4 | 5 | | | V-1 | Ms4a6c |
| 9345 | 3 | 4 | 5 | | | V-1 | Ms4a6d |
| 9346 | 3 | 4 | 5 | | | V-1 | Msantd3 |
| 9347 | 3 | 4 | 5 | | | V-1 | Msi2 |
| 9348 | 3 | 4 | 5 | | | V-1 | Msl3l2 |

Fig. 43 - 56

| | | | | | | | | |
|---|---|---|---|---|---|---|---|---|
| 9349 | 3 | 4 | 5 | | | V-1 | Msn | |
| 9350 | 3 | 4 | 5 | | | V-1 | Msra | |
| 9351 | 3 | 4 | 5 | | | V-1 | Msrb1 | |
| 9352 | 3 | 4 | 5 | | | V-1 | Msrb2 | |
| 9353 | 3 | 4 | 5 | | | V-1 | Msto1 | |
| 9354 | 3 | 4 | 5 | | | V-1 | Msx1 | |
| 9355 | 3 | 4 | 5 | | | V-1 | Mtbp | |
| 9356 | 3 | 4 | 5 | | | V-1 | Mtfp1 | |
| 9357 | 3 | 4 | 5 | | | V-1 | Mtfr2 | |
| 9358 | 3 | 4 | 5 | | | V-1 | Mtg1 | |
| 9359 | 3 | 4 | 5 | | | V-1 | Mtm1 | |
| 9360 | 3 | 4 | 5 | | | V-1 | Mtmr11 | |
| 9361 | 3 | 4 | 5 | | | V-1 | Mtmr7 | |
| 9362 | 3 | 4 | 5 | | | V-1 | Mtrf1 | |
| 9363 | 3 | 4 | 5 | | | V-1 | Mtss1l | |
| 9364 | 3 | 4 | 5 | | | V-1 | Mtus1 | |
| 9365 | 3 | 4 | 5 | | | V-1 | Mtx1 | |
| 9366 | 3 | 4 | 5 | | | V-1 | Muc1 | |
| 9367 | 3 | 4 | 5 | | | V-1 | Muc13 | |
| 9368 | 3 | 4 | 5 | | | V-1 | Mup12 | |
| 9369 | 3 | 4 | 5 | | | V-1 | Mvb12a | |
| 9370 | 3 | 4 | 5 | | | V-1 | Mx2 | |
| 9371 | 3 | 4 | 5 | | | V-1 | Mxd1 | |
| 9372 | 3 | 4 | 5 | | | V-1 | Mxra8 | |
| 9373 | 3 | 4 | 5 | | | V-1 | Mybl1 | |
| 9374 | 3 | 4 | 5 | | | V-1 | Mybl2 | |
| 9375 | 3 | 4 | 5 | | | V-1 | Mycbp2 | |
| 9376 | 3 | 4 | 5 | | | V-1 | Myeov2 | |
| 9377 | 3 | 4 | 5 | | | V-1 | Myh6 | |
| 9378 | 3 | 4 | 5 | | | V-1 | Myl6 | |
| 9379 | 3 | 4 | 5 | | | V-1 | Myl9 | |
| 9380 | 3 | 4 | 5 | | | V-1 | Myo18a | |
| 9381 | 3 | 4 | 5 | | | V-1 | Myo1c | |
| 9382 | 3 | 4 | 5 | | | V-1 | Myo1d | |
| 9383 | 3 | 4 | 5 | | | V-1 | Myo1f | |
| 9384 | 3 | 4 | 5 | | | V-1 | Myo1g | |
| 9385 | 3 | 4 | 5 | | | V-1 | Myof | |
| 9386 | 3 | 4 | 5 | | | V-1 | Myrip | |
| 9387 | 3 | 4 | 5 | | | V-1 | Mysm1 | |
| 9388 | 3 | 4 | 5 | | | V-1 | Mzt2 | |
| 9389 | 3 | 4 | 5 | | | V-1 | N28178 | |
| 9390 | 3 | 4 | 5 | | | V-1 | N6amt2 | |
| 9391 | 3 | 4 | 5 | | | V-1 | Naa10 | |
| 9392 | 3 | 4 | 5 | | | V-1 | Naa20 | |
| 9393 | 3 | 4 | 5 | | | V-1 | Naa50 | |
| 9394 | 3 | 4 | 5 | | | V-1 | Nabp1 | |
| 9395 | 3 | 4 | 5 | | | V-1 | Nabp2 | |
| 9396 | 3 | 4 | 5 | | | V-1 | Naca | |
| 9397 | 3 | 4 | 5 | | | V-1 | Naf1 | |
| 9398 | 3 | 4 | 5 | | | V-1 | Naglu | |
| 9399 | 3 | 4 | 5 | | | V-1 | Naip2 | |
| 9400 | 3 | 4 | 5 | | | V-1 | Naip5 | |
| 9401 | 3 | 4 | 5 | | | V-1 | Naip6 | |
| 9402 | 3 | 4 | 5 | | | V-1 | Nans | |
| 9403 | 3 | 4 | 5 | | | V-1 | Nap1l5 | |
| 9404 | 3 | 4 | 5 | | | V-1 | Napa | |
| 9405 | 3 | 4 | 5 | | | V-1 | Naprt1 | |
| 9406 | 3 | 4 | 5 | | | V-1 | Napsa | |
| 9407 | 3 | 4 | 5 | | | V-1 | Narf | |
| 9408 | 3 | 4 | 5 | | | V-1 | Nars | |
| 9409 | 3 | 4 | 5 | | | V-1 | Nasp | |
| 9410 | 3 | 4 | 5 | | | V-1 | Nat8 | |
| 9411 | 3 | 4 | 5 | | | V-1 | Nbl1 | |
| 9412 | 3 | 4 | 5 | | | V-1 | Nbn | |
| 9413 | 3 | 4 | 5 | | | V-1 | Ncapd2 | |
| 9414 | 3 | 4 | 5 | | | V-1 | Ncapg2 | |
| 9415 | 3 | 4 | 5 | | | V-1 | Nceh1 | |
| 9416 | 3 | 4 | 5 | | | V-1 | Ncf2 | |
| 9417 | 3 | 4 | 5 | | | V-1 | Ncf4 | |
| 9418 | 3 | 4 | 5 | | | V-1 | Nckap1 | |
| 9419 | 3 | 4 | 5 | | | V-1 | Nci | |
| 9420 | 3 | 4 | 5 | | | V-1 | Ncoa6 | |
| 9421 | 3 | 4 | 5 | | | V-1 | Ncor2 | |
| 9422 | 3 | 4 | 5 | | | V-1 | Ndc1 | |
| 9423 | 3 | 4 | 5 | | | V-1 | Ndfip2 | |
| 9424 | 3 | 4 | 5 | | | V-1 | Ndrg4 | |
| 9425 | 3 | 4 | 5 | | | V-1 | Ndst2 | |
| 9426 | 3 | 4 | 5 | | | V-1 | Ndufa1 | |
| 9427 | 3 | 4 | 5 | | | V-1 | Ndufa10 | |
| 9428 | 3 | 4 | 5 | | | V-1 | Ndufa13 | |
| 9429 | 3 | 4 | 5 | | | V-1 | Ndufa2 | |
| 9430 | 3 | 4 | 5 | | | V-1 | Ndufa4l2 | |
| 9431 | 3 | 4 | 5 | | | V-1 | Ndufa5 | |
| 9432 | 3 | 4 | 5 | | | V-1 | Ndufa6 | |
| 9433 | 3 | 4 | 5 | | | V-1 | Ndufa8 | |
| 9434 | 3 | 4 | 5 | | | V-1 | Ndufab1 | |
| 9435 | 3 | 4 | 5 | | | V-1 | Ndufaf3 | |
| 9436 | 3 | 4 | 5 | | | V-1 | Ndufaf4 | |
| 9437 | 3 | 4 | 5 | | | V-1 | Ndufb10 | |
| 9438 | 3 | 4 | 5 | | | V-1 | Ndufb2 | |
| 9439 | 3 | 4 | 5 | | | V-1 | Ndufb3 | |
| 9440 | 3 | 4 | 5 | | | V-1 | Ndufb4 | |
| 9441 | 3 | 4 | 5 | | | V-1 | Ndufb5 | |
| 9442 | 3 | 4 | 5 | | | V-1 | Ndufb8 | |
| 9443 | 3 | 4 | 5 | | | V-1 | Ndufb9 | |
| 9444 | 3 | 4 | 5 | | | V-1 | Ndufc2 | |
| 9445 | 3 | 4 | 5 | | | V-1 | Ndufs3 | |
| 9446 | 3 | 4 | 5 | | | V-1 | Ndufs4 | |
| 9447 | 3 | 4 | 5 | | | V-1 | Ndufs6 | |
| 9448 | 3 | 4 | 5 | | | V-1 | Ndufs7 | |
| 9449 | 3 | 4 | 5 | | | V-1 | Ndufs8 | |
| 9450 | 3 | 4 | 5 | | | V-1 | Ndufv2 | |
| 9451 | 3 | 4 | 5 | | | V-1 | Nedd9 | |
| 9452 | 3 | 4 | 5 | | | V-1 | Nefh | |
| 9453 | 3 | 4 | 5 | | | V-1 | Neil3 | |
| 9454 | 3 | 4 | 5 | | | V-1 | Nek6 | |
| 9455 | 3 | 4 | 5 | | | V-1 | Nelfcd | |
| 9456 | 3 | 4 | 5 | | | V-1 | Nenf | |
| 9457 | 3 | 4 | 5 | | | V-1 | Neo1 | |
| 9458 | 3 | 4 | 5 | | | V-1 | Net1 | |
| 9459 | 3 | 4 | 5 | | | V-1 | Neu3 | |
| 9460 | 3 | 4 | 5 | | | V-1 | Nfam1 | |
| 9461 | 3 | 4 | 5 | | | V-1 | Nfasc | |
| 9462 | 3 | 4 | 5 | | | V-1 | Nfatc2 | |
| 9463 | 3 | 4 | 5 | | | V-1 | Nfe2 | |
| 9464 | 3 | 4 | 5 | | | V-1 | Nfib | |
| 9465 | 3 | 4 | 5 | | | V-1 | Nfic | |
| 9466 | 3 | 4 | 5 | | | V-1 | Nfix | |
| 9467 | 3 | 4 | 5 | | | V-1 | Nfkbie | |
| 9468 | 3 | 4 | 5 | | | V-1 | Nfkbiz | |
| 9469 | 3 | 4 | 5 | | | V-1 | Nfrkb | |
| 9470 | 3 | 4 | 5 | | | V-1 | Nfs1 | |
| 9471 | 3 | 4 | 5 | | | V-1 | Nfu1 | |
| 9472 | 3 | 4 | 5 | | | V-1 | Ngdn | |
| 9473 | 3 | 4 | 5 | | | V-1 | Ngf | |
| 9474 | 3 | 4 | 5 | | | V-1 | Ngfrap1 | |
| 9475 | 3 | 4 | 5 | | | V-1 | Nhej1 | |
| 9476 | 3 | 4 | 5 | | | V-1 | Ninj1 | |
| 9477 | 3 | 4 | 5 | | | V-1 | Nipa1 | |
| 9478 | 3 | 4 | 5 | | | V-1 | Nipal4 | |
| 9479 | 3 | 4 | 5 | | | V-1 | Nipsnap1 | |
| 9480 | 3 | 4 | 5 | | | V-1 | Nktr | |
| 9481 | 3 | 4 | 5 | | | V-1 | Nkx6-2 | |
| 9482 | 3 | 4 | 5 | | | V-1 | Nlk | |
| 9483 | 3 | 4 | 5 | | | V-1 | Nlrc4 | |
| 9484 | 3 | 4 | 5 | | | V-1 | Nlrc5 | |
| 9485 | 3 | 4 | 5 | | | V-1 | Nlrp1b | |
| 9486 | 3 | 4 | 5 | | | V-1 | Nme3 | |
| 9487 | 3 | 4 | 5 | | | V-1 | Nme6 | |
| 9488 | 3 | 4 | 5 | | | V-1 | Nmnat1 | |
| 9489 | 3 | 4 | 5 | | | V-1 | Nmnat3 | |
| 9490 | 3 | 4 | 5 | | | V-1 | Nmral1 | |
| 9491 | 3 | 4 | 5 | | | V-1 | Nmrk1 | |
| 9492 | 3 | 4 | 5 | | | V-1 | Nob1 | |
| 9493 | 3 | 4 | 5 | | | V-1 | Noc4l | |
| 9494 | 3 | 4 | 5 | | | V-1 | Nod1 | |
| 9495 | 3 | 4 | 5 | | | V-1 | Nol10 | |
| 9496 | 3 | 4 | 5 | | | V-1 | Nol7 | |
| 9497 | 3 | 4 | 5 | | | V-1 | Nolc1 | |
| 9498 | 3 | 4 | 5 | | | V-1 | Nop10 | |
| 9499 | 3 | 4 | 5 | | | V-1 | Nop58 | |
| 9500 | 3 | 4 | 5 | | | V-1 | Noslap | |
| 9501 | 3 | 4 | 5 | | | V-1 | Nov | |
| 9502 | 3 | 4 | 5 | | | V-1 | Npas2 | |
| 9503 | 3 | 4 | 5 | | | V-1 | Npdc1 | |
| 9504 | 3 | 4 | 5 | | | V-1 | Nphp3 | |
| 9505 | 3 | 4 | 5 | | | V-1 | Npnt | |
| 9506 | 3 | 4 | 5 | | | V-1 | Npr2 | |
| 9507 | 3 | 4 | 5 | | | V-1 | Nqo2 | |
| 9508 | 3 | 4 | 5 | | | V-1 | Nr0b2 | |
| 9509 | 3 | 4 | 5 | | | V-1 | Nr1i3 | |
| 9510 | 3 | 4 | 5 | | | V-1 | Nr2c2ap | |
| 9511 | 3 | 4 | 5 | | | V-1 | Nr2f1 | |
| 9512 | 3 | 4 | 5 | | | V-1 | Nr3c1 | |
| 9513 | 3 | 4 | 5 | | | V-1 | Nr4a2 | |
| 9514 | 3 | 4 | 5 | | | V-1 | Nr5a2 | |
| 9515 | 3 | 4 | 5 | | | V-1 | Nradd | |
| 9516 | 3 | 4 | 5 | | | V-1 | Nrarp | |
| 9517 | 3 | 4 | 5 | | | V-1 | Nrbp2 | |
| 9518 | 3 | 4 | 5 | | | V-1 | Nrep | |

Fig. 43 - 57

| | | | | | | | | | | | | | | | |
|---|---|---|---|---|---|---|---|---|---|---|---|---|---|---|---|
| 9519 | 3 | 4 | 5 | | | | V-1 | Nrgn | 9603 | 3 | 4 | 5 | | V-1 | P2ry6 |
| 9520 | 3 | 4 | 5 | | | | V-1 | Nrip2 | 9604 | 3 | 4 | 5 | | V-1 | P4htm |
| 9521 | 3 | 4 | 5 | | | | V-1 | Nrip3 | 9605 | 3 | 4 | 5 | | V-1 | Pa2g4 |
| 9522 | 3 | 4 | 5 | | | | V-1 | Nrm | 9606 | 3 | 4 | 5 | | V-1 | Pacsin3 |
| 9523 | 3 | 4 | 5 | | | | V-1 | Nrxn2 | 9607 | 3 | 4 | 5 | | V-1 | Pafah1b2 |
| 9524 | 3 | 4 | 5 | | | | V-1 | Nsdhl | 9608 | 3 | 4 | 5 | | V-1 | Pak1ip1 |
| 9525 | 3 | 4 | 5 | | | | V-1 | Nsl1 | 9609 | 3 | 4 | 5 | | V-1 | Pald |
| 9526 | 3 | 4 | 5 | | | | V-1 | Nsmce4a | 9610 | 3 | 4 | 5 | | V-1 | Palm3 |
| 9527 | 3 | 4 | 5 | | | | V-1 | Nsun3 | 9611 | 3 | 4 | 5 | | V-1 | Pam |
| 9528 | 3 | 4 | 5 | | | | V-1 | Nt5c | 9612 | 3 | 4 | 5 | | V-1 | Pam16 |
| 9529 | 3 | 4 | 5 | | | | V-1 | Nt5c2 | 9613 | 3 | 4 | 5 | | V-1 | Pank3 |
| 9530 | 3 | 4 | 5 | | | | V-1 | Nt5c3 | 9614 | 3 | 4 | 5 | | V-1 | Panx1 |
| 9531 | 3 | 4 | 5 | | | | V-1 | Nt5dc2 | 9615 | 3 | 4 | 5 | | V-1 | Paox |
| 9532 | 3 | 4 | 5 | | | | V-1 | Nt5dc3 | 9616 | 3 | 4 | 5 | | V-1 | Papd4 |
| 9533 | 3 | 4 | 5 | | | | V-1 | Ntmt1 | 9617 | 3 | 4 | 5 | | V-1 | Papolb |
| 9534 | 3 | 4 | 5 | | | | V-1 | Nts | 9618 | 3 | 4 | 5 | | V-1 | Papss2 |
| 9535 | 3 | 4 | 5 | | | | V-1 | Ntsr2 | 9619 | 3 | 4 | 5 | | V-1 | Paqr5 |
| 9536 | 3 | 4 | 5 | | | | V-1 | Nuak1 | 9620 | 3 | 4 | 5 | | V-1 | Paqr7 |
| 9537 | 3 | 4 | 5 | | | | V-1 | Nuak2 | 9621 | 3 | 4 | 5 | | V-1 | Pard6b |
| 9538 | 3 | 4 | 5 | | | | V-1 | Nucb2 | 9622 | 3 | 4 | 5 | | V-1 | Park7 |
| 9539 | 3 | 4 | 5 | | | | V-1 | Nudcd1 | 9623 | 3 | 4 | 5 | | V-1 | Parl |
| 9540 | 3 | 4 | 5 | | | | V-1 | Nudcd2 | 9624 | 3 | 4 | 5 | | V-1 | Parp10 |
| 9541 | 3 | 4 | 5 | | | | V-1 | Nudt18 | 9625 | 3 | 4 | 5 | | V-1 | Parp12 |
| 9542 | 3 | 4 | 5 | | | | V-1 | Nudt19 | 9626 | 3 | 4 | 5 | | V-1 | Parp3 |
| 9543 | 3 | 4 | 5 | | | | V-1 | Nudt2 | 9627 | 3 | 4 | 5 | | V-1 | Parp8 |
| 9544 | 3 | 4 | 5 | | | | V-1 | Nudt4 | 9628 | 3 | 4 | 5 | | V-1 | Parp9 |
| 9545 | 3 | 4 | 5 | | | | V-1 | Nudt5 | 9629 | 3 | 4 | 5 | | V-1 | Parvg |
| 9546 | 3 | 4 | 5 | | | | V-1 | Nudt6 | 9630 | 3 | 4 | 5 | | V-1 | Pask |
| 9547 | 3 | 4 | 5 | | | | V-1 | Nudt7 | 9631 | 3 | 4 | 5 | | V-1 | Pawr |
| 9548 | 3 | 4 | 5 | | | | V-1 | Nup107 | 9632 | 3 | 4 | 5 | | V-1 | Pbdc1 |
| 9549 | 3 | 4 | 5 | | | | V-1 | Nup210 | 9633 | 3 | 4 | 5 | | V-1 | Pbk |
| 9550 | 3 | 4 | 5 | | | | V-1 | Nup43 | 9634 | 3 | 4 | 5 | | V-1 | Pbld2 |
| 9551 | 3 | 4 | 5 | | | | V-1 | Nup62 | 9635 | 3 | 4 | 5 | | V-1 | Pbx1 |
| 9552 | 3 | 4 | 5 | | | | V-1 | Nup88 | 9636 | 3 | 4 | 5 | | V-1 | Pbx4 |
| 9553 | 3 | 4 | 5 | | | | V-1 | Nup93 | 9637 | 3 | 4 | 5 | | V-1 | Pbxip1 |
| 9554 | 3 | 4 | 5 | | | | V-1 | Nupl1 | 9638 | 3 | 4 | 5 | | V-1 | Pcbd2 |
| 9555 | 3 | 4 | 5 | | | | V-1 | Nutf2-ps1 | 9639 | 3 | 4 | 5 | | V-1 | Pcbp3 |
| 9556 | 3 | 4 | 5 | | | | V-1 | Nxpe5 | 9640 | 3 | 4 | 5 | | V-1 | Pcdhb22 |
| 9557 | 3 | 4 | 5 | | | | V-1 | Nxph3 | 9641 | 3 | 4 | 5 | | V-1 | Pcdhga1 |
| 9558 | 3 | 4 | 5 | | | | V-1 | Oard1 | 9642 | 3 | 4 | 5 | | V-1 | Pcdhga10 |
| 9559 | 3 | 4 | 5 | | | | V-1 | Oaz1 | 9643 | 3 | 4 | 5 | | V-1 | Pcdhgb4 |
| 9560 | 3 | 4 | 5 | | | | V-1 | Ocel1 | 9644 | 3 | 4 | 5 | | V-1 | Pcdhgb7 |
| 9561 | 3 | 4 | 5 | | | | V-1 | Odc1 | 9645 | 3 | 4 | 5 | | V-1 | Pcdhgc3 |
| 9562 | 3 | 4 | 5 | | | | V-1 | Ofd1 | 9646 | 3 | 4 | 5 | | V-1 | Pcnt |
| 9563 | 3 | 4 | 5 | | | | V-1 | Ogfod1 | 9647 | 3 | 4 | 5 | | V-1 | Pcolce |
| 9564 | 3 | 4 | 5 | | | | V-1 | Ogg1 | 9648 | 3 | 4 | 5 | | V-1 | Pcolce2 |
| 9565 | 3 | 4 | 5 | | | | V-1 | Ogn | 9649 | 3 | 4 | 5 | | V-1 | Pcp4 |
| 9566 | 3 | 4 | 5 | | | | V-1 | Oip5 | 9650 | 3 | 4 | 5 | | V-1 | Pcsk4 |
| 9567 | 3 | 4 | 5 | | | | V-1 | Oit1 | 9651 | 3 | 4 | 5 | | V-1 | Pcyox1 |
| 9568 | 3 | 4 | 5 | | | | V-1 | Ola1 | 9652 | 3 | 4 | 5 | | V-1 | Pdcd10 |
| 9569 | 3 | 4 | 5 | | | | V-1 | Olfm1 | 9653 | 3 | 4 | 5 | | V-1 | Pdcd5 |
| 9570 | 3 | 4 | 5 | | | | V-1 | Olfml1 | 9654 | 3 | 4 | 5 | | V-1 | Pde12 |
| 9571 | 3 | 4 | 5 | | | | V-1 | Olfml2b | 9655 | 3 | 4 | 5 | | V-1 | Pde6h |
| 9572 | 3 | 4 | 5 | | | | V-1 | Olfml3 | 9656 | 3 | 4 | 5 | | V-1 | Pde8a |
| 9573 | 3 | 4 | 5 | | | | V-1 | Olfr1372-ps1 | 9657 | 3 | 4 | 5 | | V-1 | Pdgfa |
| 9574 | 3 | 4 | 5 | | | | V-1 | Olfr1393 | 9658 | 3 | 4 | 5 | | V-1 | Pdgfc |
| 9575 | 3 | 4 | 5 | | | | V-1 | Olfr165 | 9659 | 3 | 4 | 5 | | V-1 | Pdhb |
| 9576 | 3 | 4 | 5 | | | | V-1 | Olfr287 | 9660 | 3 | 4 | 5 | | V-1 | Pdia3 |
| 9577 | 3 | 4 | 5 | | | | V-1 | Olfr56 | 9661 | 3 | 4 | 5 | | V-1 | Pdia4 |
| 9578 | 3 | 4 | 5 | | | | V-1 | Olfr78 | 9662 | 3 | 4 | 5 | | V-1 | Pdia6 |
| 9579 | 3 | 4 | 5 | | | | V-1 | Olfr920 | 9663 | 3 | 4 | 5 | | V-1 | Pdk3 |
| 9580 | 3 | 4 | 5 | | | | V-1 | Oplah | 9664 | 3 | 4 | 5 | | V-1 | Pdlim1 |
| 9581 | 3 | 4 | 5 | | | | V-1 | Orai2 | 9665 | 3 | 4 | 5 | | V-1 | Pdlim4 |
| 9582 | 3 | 4 | 5 | | | | V-1 | Orai3 | 9666 | 3 | 4 | 5 | | V-1 | Pdpn |
| 9583 | 3 | 4 | 5 | | | | V-1 | Orc3 | 9667 | 3 | 4 | 5 | | V-1 | Pdzd11 |
| 9584 | 3 | 4 | 5 | | | | V-1 | Orc6 | 9668 | 3 | 4 | 5 | | V-1 | Pdzrn4 |
| 9585 | 3 | 4 | 5 | | | | V-1 | Orm3 | 9669 | 3 | 4 | 5 | | V-1 | Pebp1 |
| 9586 | 3 | 4 | 5 | | | | V-1 | Ormdl1 | 9670 | 3 | 4 | 5 | | V-1 | Pecr |
| 9587 | 3 | 4 | 5 | | | | V-1 | Osbpl1a | 9671 | 3 | 4 | 5 | | V-1 | Peg10 |
| 9588 | 3 | 4 | 5 | | | | V-1 | Osbpl6 | 9672 | 3 | 4 | 5 | | V-1 | Pelo |
| 9589 | 3 | 4 | 5 | | | | V-1 | Osgin2 | 9673 | 3 | 4 | 5 | | V-1 | Penk |
| 9590 | 3 | 4 | 5 | | | | V-1 | Osm | 9674 | 3 | 4 | 5 | | V-1 | Pes1 |
| 9591 | 3 | 4 | 5 | | | | V-1 | Osr1 | 9675 | 3 | 4 | 5 | | V-1 | Pet117 |
| 9592 | 3 | 4 | 5 | | | | V-1 | Ostc | 9676 | 3 | 4 | 5 | | V-1 | Pex11a |
| 9593 | 3 | 4 | 5 | | | | V-1 | Ostf1 | 9677 | 3 | 4 | 5 | | V-1 | Pfas |
| 9594 | 3 | 4 | 5 | | | | V-1 | Otop1 | 9678 | 3 | 4 | 5 | | V-1 | Pfdn1 |
| 9595 | 3 | 4 | 5 | | | | V-1 | Otop2 | 9679 | 3 | 4 | 5 | | V-1 | Pfdn4 |
| 9596 | 3 | 4 | 5 | | | | V-1 | OTTMUSG000000 16609 | 9680 | 3 | 4 | 5 | | V-1 | Pfdn5 |
| 9597 | 3 | 4 | 5 | | | | V-1 | Otub1 | 9681 | 3 | 4 | 5 | | V-1 | Pfkfb2 |
| 9598 | 3 | 4 | 5 | | | | V-1 | Ovol2 | 9682 | 3 | 4 | 5 | | V-1 | Pfkfb4 |
| 9599 | 3 | 4 | 5 | | | | V-1 | P2rx5 | 9683 | 3 | 4 | 5 | | V-1 | Pfkl |
| 9600 | 3 | 4 | 5 | | | | V-1 | P2rx7 | 9684 | 3 | 4 | 5 | | V-1 | Pfn1 |
| 9601 | 3 | 4 | 5 | | | | V-1 | P2ry12 | 9685 | 3 | 4 | 5 | | V-1 | Pfn2 |
| 9602 | 3 | 4 | 5 | | | | V-1 | P2ry2 | 9686 | 3 | 4 | 5 | | V-1 | Pgam1 |
| | | | | | | | | | 9687 | 3 | 4 | 5 | | V-1 | Pgap2 |

Fig. 43 - 58

| | | | | | | | | |
|---|---|---|---|---|---|---|---|---|
| 9688 | 3 | 4 | 5 | | | V-1 | Pgd |
| 9689 | 3 | 4 | 5 | | | V-1 | Pgk1 |
| 9690 | 3 | 4 | 5 | | | V-1 | Pgm1 |
| 9691 | 3 | 4 | 5 | | | V-1 | Pgpep1 |
| 9692 | 3 | 4 | 5 | | | V-1 | Pgrmc1 |
| 9693 | 3 | 4 | 5 | | | V-1 | Phactr1 |
| 9694 | 3 | 4 | 5 | | | V-1 | Phc3 |
| 9695 | 3 | 4 | 5 | | | V-1 | Phf19 |
| 9696 | 3 | 4 | 5 | | | V-1 | Phf5a |
| 9697 | 3 | 4 | 5 | | | V-1 | Phka1 |
| 9698 | 3 | 4 | 5 | | | V-1 | Phldb2 |
| 9699 | 3 | 4 | 5 | | | V-1 | Phox2a |
| 9700 | 3 | 4 | 5 | | | V-1 | Phpt1 |
| 9701 | 3 | 4 | 5 | | | V-1 | Phyh |
| 9702 | 3 | 4 | 5 | | | V-1 | Phykpl |
| 9703 | 3 | 4 | 5 | | | V-1 | Pi15 |
| 9704 | 3 | 4 | 5 | | | V-1 | Pi16 |
| 9705 | 3 | 4 | 5 | | | V-1 | Pias4 |
| 9706 | 3 | 4 | 5 | | | V-1 | Pidd1 |
| 9707 | 3 | 4 | 5 | | | V-1 | Piga |
| 9708 | 3 | 4 | 5 | | | V-1 | Pigb |
| 9709 | 3 | 4 | 5 | | | V-1 | Pigp |
| 9710 | 3 | 4 | 5 | | | V-1 | Pigt |
| 9711 | 3 | 4 | 5 | | | V-1 | Pigu |
| 9712 | 3 | 4 | 5 | | | V-1 | Pigx |
| 9713 | 3 | 4 | 5 | | | V-1 | Pigz |
| 9714 | 3 | 4 | 5 | | | V-1 | Pih1d1 |
| 9715 | 3 | 4 | 5 | | | V-1 | Pik3r1 |
| 9716 | 3 | 4 | 5 | | | V-1 | Pilra |
| 9717 | 3 | 4 | 5 | | | V-1 | Pim1 |
| 9718 | 3 | 4 | 5 | | | V-1 | Pim3 |
| 9719 | 3 | 4 | 5 | | | V-1 | Pin1rt1 |
| 9720 | 3 | 4 | 5 | | | V-1 | Pip4k2a |
| 9721 | 3 | 4 | 5 | | | V-1 | Pip4k2b |
| 9722 | 3 | 4 | 5 | | | V-1 | Pira6 |
| 9723 | 3 | 4 | 5 | | | V-1 | Pirt |
| 9724 | 3 | 4 | 5 | | | V-1 | Pisd-ps1 |
| 9725 | 3 | 4 | 5 | | | V-1 | Pitpnm1 |
| 9726 | 3 | 4 | 5 | | | V-1 | Pitx2 |
| 9727 | 3 | 4 | 5 | | | V-1 | Pitx3 |
| 9728 | 3 | 4 | 5 | | | V-1 | Pkd1l3 |
| 9729 | 3 | 4 | 5 | | | V-1 | Pkmyt1 |
| 9730 | 3 | 4 | 5 | | | V-1 | Pknox2 |
| 9731 | 3 | 4 | 5 | | | V-1 | Pkp1 |
| 9732 | 3 | 4 | 5 | | | V-1 | Pkp3 |
| 9733 | 3 | 4 | 5 | | | V-1 | Pla2g10os |
| 9734 | 3 | 4 | 5 | | | V-1 | Pla2g5 |
| 9735 | 3 | 4 | 5 | | | V-1 | Plat |
| 9736 | 3 | 4 | 5 | | | V-1 | Plaur |
| 9737 | 3 | 4 | 5 | | | V-1 | Plb1 |
| 9738 | 3 | 4 | 5 | | | V-1 | Plcd1 |
| 9739 | 3 | 4 | 5 | | | V-1 | Plcd3 |
| 9740 | 3 | 4 | 5 | | | V-1 | Plce1 |
| 9741 | 3 | 4 | 5 | | | V-1 | Plcg2 |
| 9742 | 3 | 4 | 5 | | | V-1 | Plch2 |
| 9743 | 3 | 4 | 5 | | | V-1 | Plcl2 |
| 9744 | 3 | 4 | 5 | | | V-1 | Pld4 |
| 9745 | 3 | 4 | 5 | | | V-1 | Plec |
| 9746 | 3 | 4 | 5 | | | V-1 | Plekha6 |
| 9747 | 3 | 4 | 5 | | | V-1 | Plekha7 |
| 9748 | 3 | 4 | 5 | | | V-1 | Plekhb1 |
| 9749 | 3 | 4 | 5 | | | V-1 | Plekhg6 |
| 9750 | 3 | 4 | 5 | | | V-1 | Plekhm1 |
| 9751 | 3 | 4 | 5 | | | V-1 | Plgrkt |
| 9752 | 3 | 4 | 5 | | | V-1 | Plin2 |
| 9753 | 3 | 4 | 5 | | | V-1 | Plk1 |
| 9754 | 3 | 4 | 5 | | | V-1 | Plk4 |
| 9755 | 3 | 4 | 5 | | | V-1 | Plscr2 |
| 9756 | 3 | 4 | 5 | | | V-1 | Plscr3 |
| 9757 | 3 | 4 | 5 | | | V-1 | Plscr4 |
| 9758 | 3 | 4 | 5 | | | V-1 | Pltp |
| 9759 | 3 | 4 | 5 | | | V-1 | Plxna2 |
| 9760 | 3 | 4 | 5 | | | V-1 | Plxnb2 |
| 9761 | 3 | 4 | 5 | | | V-1 | Pm20d1 |
| 9762 | 3 | 4 | 5 | | | V-1 | Pm20d2 |
| 9763 | 3 | 4 | 5 | | | V-1 | Pml |
| 9764 | 3 | 4 | 5 | | | V-1 | Pmm1 |
| 9765 | 3 | 4 | 5 | | | V-1 | Pmp2 |
| 9766 | 3 | 4 | 5 | | | V-1 | Pmp22 |
| 9767 | 3 | 4 | 5 | | | V-1 | Pmpca |
| 9768 | 3 | 4 | 5 | | | V-1 | Pmvk |
| 9769 | 3 | 4 | 5 | | | V-1 | Pnkp |
| 9770 | 3 | 4 | 5 | | | V-1 | Pno1 |
| 9771 | 3 | 4 | 5 | | | V-1 | Pnp |
| 9772 | 3 | 4 | 5 | | | V-1 | Pnp2 |

| | | | | | | | | |
|---|---|---|---|---|---|---|---|---|
| 9773 | 3 | 4 | 5 | | | V-1 | Pnpla3 |
| 9774 | 3 | 4 | 5 | | | V-1 | Pnpt1 |
| 9775 | 3 | 4 | 5 | | | V-1 | Podxl2 |
| 9776 | 3 | 4 | 5 | | | V-1 | Pola1 |
| 9777 | 3 | 4 | 5 | | | V-1 | Pola2 |
| 9778 | 3 | 4 | 5 | | | V-1 | Pold1 |
| 9779 | 3 | 4 | 5 | | | V-1 | Pold2 |
| 9780 | 3 | 4 | 5 | | | V-1 | Pole |
| 9781 | 3 | 4 | 5 | | | V-1 | Pole2 |
| 9782 | 3 | 4 | 5 | | | V-1 | Pole3 |
| 9783 | 3 | 4 | 5 | | | V-1 | Polg2 |
| 9784 | 3 | 4 | 5 | | | V-1 | Polh |
| 9785 | 3 | 4 | 5 | | | V-1 | Poln |
| 9786 | 3 | 4 | 5 | | | V-1 | Polr1d |
| 9787 | 3 | 4 | 5 | | | V-1 | Polr2d |
| 9788 | 3 | 4 | 5 | | | V-1 | Polr2f |
| 9789 | 3 | 4 | 5 | | | V-1 | Polr2j |
| 9790 | 3 | 4 | 5 | | | V-1 | Polr2l |
| 9791 | 3 | 4 | 5 | | | V-1 | Polr3d |
| 9792 | 3 | 4 | 5 | | | V-1 | Polr3g |
| 9793 | 3 | 4 | 5 | | | V-1 | Polr3h |
| 9794 | 3 | 4 | 5 | | | V-1 | Polr3k |
| 9795 | 3 | 4 | 5 | | | V-1 | Pom121 |
| 9796 | 3 | 4 | 5 | | | V-1 | Pomp |
| 9797 | 3 | 4 | 5 | | | V-1 | Pop1 |
| 9798 | 3 | 4 | 5 | | | V-1 | Pop4 |
| 9799 | 3 | 4 | 5 | | | V-1 | Pop5 |
| 9800 | 3 | 4 | 5 | | | V-1 | Pop7 |
| 9801 | 3 | 4 | 5 | | | V-1 | Postn |
| 9802 | 3 | 4 | 5 | | | V-1 | Pou2f3 |
| 9803 | 3 | 4 | 5 | | | V-1 | Pou3f1 |
| 9804 | 3 | 4 | 5 | | | V-1 | Ppa2 |
| 9805 | 3 | 4 | 5 | | | V-1 | Ppan |
| 9806 | 3 | 4 | 5 | | | V-1 | Ppap2a |
| 9807 | 3 | 4 | 5 | | | V-1 | Ppap2c |
| 9808 | 3 | 4 | 5 | | | V-1 | Ppapdc1b |
| 9809 | 3 | 4 | 5 | | | V-1 | Ppapdc2 |
| 9810 | 3 | 4 | 5 | | | V-1 | Ppapdc3 |
| 9811 | 3 | 4 | 5 | | | V-1 | Ppat |
| 9812 | 3 | 4 | 5 | | | V-1 | Ppcs |
| 9813 | 3 | 4 | 5 | | | V-1 | Ppia |
| 9814 | 3 | 4 | 5 | | | V-1 | Ppib |
| 9815 | 3 | 4 | 5 | | | V-1 | Ppic |
| 9816 | 3 | 4 | 5 | | | V-1 | Ppid |
| 9817 | 3 | 4 | 5 | | | V-1 | Ppie |
| 9818 | 3 | 4 | 5 | | | V-1 | Ppm1k |
| 9819 | 3 | 4 | 5 | | | V-1 | Ppox |
| 9820 | 3 | 4 | 5 | | | V-1 | Ppp1r14b |
| 9821 | 3 | 4 | 5 | | | V-1 | Ppp1r15b |
| 9822 | 3 | 4 | 5 | | | V-1 | Ppp1r18 |
| 9823 | 3 | 4 | 5 | | | V-1 | Ppp1r1c |
| 9824 | 3 | 4 | 5 | | | V-1 | Ppp1r2-ps3 |
| 9825 | 3 | 4 | 5 | | | V-1 | Ppp1r3f |
| 9826 | 3 | 4 | 5 | | | V-1 | Ppp1r9a |
| 9827 | 3 | 4 | 5 | | | V-1 | Ppp2r1b |
| 9828 | 3 | 4 | 5 | | | V-1 | Ppp3cc |
| 9829 | 3 | 4 | 5 | | | V-1 | Ppp4c |
| 9830 | 3 | 4 | 5 | | | V-1 | Ppp6r2 |
| 9831 | 3 | 4 | 5 | | | V-1 | Pqlc3 |
| 9832 | 3 | 4 | 5 | | | V-1 | Praf2 |
| 9833 | 3 | 4 | 5 | | | V-1 | Prc1 |
| 9834 | 3 | 4 | 5 | | | V-1 | Prdm2 |
| 9835 | 3 | 4 | 5 | | | V-1 | Prdm9 |
| 9836 | 3 | 4 | 5 | | | V-1 | Prdx1 |
| 9837 | 3 | 4 | 5 | | | V-1 | Prdx2 |
| 9838 | 3 | 4 | 5 | | | V-1 | Prdx4 |
| 9839 | 3 | 4 | 5 | | | V-1 | Prdx5 |
| 9840 | 3 | 4 | 5 | | | V-1 | Prdx6 |
| 9841 | 3 | 4 | 5 | | | V-1 | Prelid2 |
| 9842 | 3 | 4 | 5 | | | V-1 | Prex1 |
| 9843 | 3 | 4 | 5 | | | V-1 | Prf1 |
| 9844 | 3 | 4 | 5 | | | V-1 | Prg3 |
| 9845 | 3 | 4 | 5 | | | V-1 | Prg4 |
| 9846 | 3 | 4 | 5 | | | V-1 | Prim1 |
| 9847 | 3 | 4 | 5 | | | V-1 | Prim2 |
| 9848 | 3 | 4 | 5 | | | V-1 | Prkaa2 |
| 9849 | 3 | 4 | 5 | | | V-1 | Prkar1b |
| 9850 | 3 | 4 | 5 | | | V-1 | Prkar2a |
| 9851 | 3 | 4 | 5 | | | V-1 | Prkch |
| 9852 | 3 | 4 | 5 | | | V-1 | Prkd1 |
| 9853 | 3 | 4 | 5 | | | V-1 | Prkg1 |
| 9854 | 3 | 4 | 5 | | | V-1 | Prmt1 |
| 9855 | 3 | 4 | 5 | | | V-1 | Prmt10 |
| 9856 | 3 | 4 | 5 | | | V-1 | Prnd |
| 9857 | 3 | 4 | 5 | | | V-1 | Prnp |

Fig. 43 - 59

| | | | | | | | | |
|---|---|---|---|---|---|---|---|---|
| 9858 | 3 | 4 | 5 | | | V-1 | Proc | |
| 9859 | 3 | 4 | 5 | | | V-1 | Proser1 | |
| 9860 | 3 | 4 | 5 | | | V-1 | Prox2 | |
| 9861 | 3 | 4 | 5 | | | V-1 | Prpf8 | |
| 9862 | 3 | 4 | 5 | | | V-1 | Prps2 | |
| 9863 | 3 | 4 | 5 | | | V-1 | Prpsap2 | |
| 9864 | 3 | 4 | 5 | | | V-1 | Prr16 | |
| 9865 | 3 | 4 | 5 | | | V-1 | Prr5l | |
| 9866 | 3 | 4 | 5 | | | V-1 | Prrc2c | |
| 9867 | 3 | 4 | 5 | | | V-1 | Prrg4 | |
| 9868 | 3 | 4 | 5 | | | V-1 | Prrx1 | |
| 9869 | 3 | 4 | 5 | | | V-1 | Prss16 | |
| 9870 | 3 | 4 | 5 | | | V-1 | Prss30 | |
| 9871 | 3 | 4 | 5 | | | V-1 | Prune | |
| 9872 | 3 | 4 | 5 | | | V-1 | Prx | |
| 9873 | 3 | 4 | 5 | | | V-1 | Psd3 | |
| 9874 | 3 | 4 | 5 | | | V-1 | Psd4 | |
| 9875 | 3 | 4 | 5 | | | V-1 | Psenen | |
| 9876 | 3 | 4 | 5 | | | V-1 | Psg16 | |
| 9877 | 3 | 4 | 5 | | | V-1 | Psma1 | |
| 9878 | 3 | 4 | 5 | | | V-1 | Psma2 | |
| 9879 | 3 | 4 | 5 | | | V-1 | Psma4 | |
| 9880 | 3 | 4 | 5 | | | V-1 | Psma5 | |
| 9881 | 3 | 4 | 5 | | | V-1 | Psma7 | |
| 9882 | 3 | 4 | 5 | | | V-1 | Psmb1 | |
| 9883 | 3 | 4 | 5 | | | V-1 | Psmb10 | |
| 9884 | 3 | 4 | 5 | | | V-1 | Psmb3 | |
| 9885 | 3 | 4 | 5 | | | V-1 | Psmb4 | |
| 9886 | 3 | 4 | 5 | | | V-1 | Psmb5 | |
| 9887 | 3 | 4 | 5 | | | V-1 | Psmb6 | |
| 9888 | 3 | 4 | 5 | | | V-1 | Psmb8 | |
| 9889 | 3 | 4 | 5 | | | V-1 | Psmc1 | |
| 9890 | 3 | 4 | 5 | | | V-1 | Psmc2 | |
| 9891 | 3 | 4 | 5 | | | V-1 | Psmc4 | |
| 9892 | 3 | 4 | 5 | | | V-1 | Psmd1 | |
| 9893 | 3 | 4 | 5 | | | V-1 | Psmd10 | |
| 9894 | 3 | 4 | 5 | | | V-1 | Psmd13 | |
| 9895 | 3 | 4 | 5 | | | V-1 | Psmd14 | |
| 9896 | 3 | 4 | 5 | | | V-1 | Psme1 | |
| 9897 | 3 | 4 | 5 | | | V-1 | Psme2b | |
| 9898 | 3 | 4 | 5 | | | V-1 | Psmf1 | |
| 9899 | 3 | 4 | 5 | | | V-1 | Psmg1 | |
| 9900 | 3 | 4 | 5 | | | V-1 | Psmg2 | |
| 9901 | 3 | 4 | 5 | | | V-1 | Psmg3 | |
| 9902 | 3 | 4 | 5 | | | V-1 | Psmg4 | |
| 9903 | 3 | 4 | 5 | | | V-1 | Pspc1 | |
| 9904 | 3 | 4 | 5 | | | V-1 | Pstk | |
| 9905 | 3 | 4 | 5 | | | V-1 | Pstpip1 | |
| 9906 | 3 | 4 | 5 | | | V-1 | Ptafr | |
| 9907 | 3 | 4 | 5 | | | V-1 | Ptar1 | |
| 9908 | 3 | 4 | 5 | | | V-1 | Pter | |
| 9909 | 3 | 4 | 5 | | | V-1 | Ptgdr | |
| 9910 | 3 | 4 | 5 | | | V-1 | Ptger1 | |
| 9911 | 3 | 4 | 5 | | | V-1 | Ptges | |
| 9912 | 3 | 4 | 5 | | | V-1 | Ptges3l | |
| 9913 | 3 | 4 | 5 | | | V-1 | Ptgfrn | |
| 9914 | 3 | 4 | 5 | | | V-1 | Ptgis | |
| 9915 | 3 | 4 | 5 | | | V-1 | Ptgr1 | |
| 9916 | 3 | 4 | 5 | | | V-1 | Pth1r | |
| 9917 | 3 | 4 | 5 | | | V-1 | Pthlh | |
| 9918 | 3 | 4 | 5 | | | V-1 | Ptk6 | |
| 9919 | 3 | 4 | 5 | | | V-1 | Ptk7 | |
| 9920 | 3 | 4 | 5 | | | V-1 | Ptma | |
| 9921 | 3 | 4 | 5 | | | V-1 | Ptn | |
| 9922 | 3 | 4 | 5 | | | V-1 | Ptp4a1 | |
| 9923 | 3 | 4 | 5 | | | V-1 | Ptpdc1 | |
| 9924 | 3 | 4 | 5 | | | V-1 | Ptplad2 | |
| 9925 | 3 | 4 | 5 | | | V-1 | Ptpmt1 | |
| 9926 | 3 | 4 | 5 | | | V-1 | Ptpn18 | |
| 9927 | 3 | 4 | 5 | | | V-1 | Ptpn2 | |
| 9928 | 3 | 4 | 5 | | | V-1 | Ptpn22 | |
| 9929 | 3 | 4 | 5 | | | V-1 | Ptpn3 | |
| 9930 | 3 | 4 | 5 | | | V-1 | Ptpn7 | |
| 9931 | 3 | 4 | 5 | | | V-1 | Ptpn9 | |
| 9932 | 3 | 4 | 5 | | | V-1 | Ptprc | |
| 9933 | 3 | 4 | 5 | | | V-1 | Ptprj | |
| 9934 | 3 | 4 | 5 | | | V-1 | Ptprs | |
| 9935 | 3 | 4 | 5 | | | V-1 | Pus7 | |
| 9936 | 3 | 4 | 5 | | | V-1 | Pvrl4 | |
| 9937 | 3 | 4 | 5 | | | V-1 | Pvt1 | |
| 9938 | 3 | 4 | 5 | | | V-1 | Pycard | |
| 9939 | 3 | 4 | 5 | | | V-1 | Pycr2 | |
| 9940 | 3 | 4 | 5 | | | V-1 | Pydc3 | |
| 9941 | 3 | 4 | 5 | | | V-1 | Pydc4 | |
| 9942 | 3 | 4 | 5 | | | V-1 | Pygl | |
| 9943 | 3 | 4 | 5 | | | V-1 | Pyhin1 | |
| 9944 | 3 | 4 | 5 | | | V-1 | Qdpr | |
| 9945 | 3 | 4 | 5 | | | V-1 | Qpct | |
| 9946 | 3 | 4 | 5 | | | V-1 | Qprt | |
| 9947 | 3 | 4 | 5 | | | V-1 | Qrfp | |
| 9948 | 3 | 4 | 5 | | | V-1 | Qser1 | |
| 9949 | 3 | 4 | 5 | | | V-1 | Qtrt1 | |
| 9950 | 3 | 4 | 5 | | | V-1 | Rab10os | |
| 9951 | 3 | 4 | 5 | | | V-1 | Rab13 | |
| 9952 | 3 | 4 | 5 | | | V-1 | Rab15 | |
| 9953 | 3 | 4 | 5 | | | V-1 | Rab20 | |
| 9954 | 3 | 4 | 5 | | | V-1 | Rab32 | |
| 9955 | 3 | 4 | 5 | | | V-1 | Rab34 | |
| 9956 | 3 | 4 | 5 | | | V-1 | Rab37 | |
| 9957 | 3 | 4 | 5 | | | V-1 | Rab38 | |
| 9958 | 3 | 4 | 5 | | | V-1 | Rab39 | |
| 9959 | 3 | 4 | 5 | | | V-1 | Rab3il1 | |
| 9960 | 3 | 4 | 5 | | | V-1 | Rab42 | |
| 9961 | 3 | 4 | 5 | | | V-1 | Rab4a | |
| 9962 | 3 | 4 | 5 | | | V-1 | Rab7 | |
| 9963 | 3 | 4 | 5 | | | V-1 | Rab8b | |
| 9964 | 3 | 4 | 5 | | | V-1 | Rabac1 | |
| 9965 | 3 | 4 | 5 | | | V-1 | Rabgap1l | |
| 9966 | 3 | 4 | 5 | | | V-1 | Rabggtb | |
| 9967 | 3 | 4 | 5 | | | V-1 | Rabl3 | |
| 9968 | 3 | 4 | 5 | | | V-1 | Rac2 | |
| 9969 | 3 | 4 | 5 | | | V-1 | Racgap1 | |
| 9970 | 3 | 4 | 5 | | | V-1 | Rad18 | |
| 9971 | 3 | 4 | 5 | | | V-1 | Rad51ap1 | |
| 9972 | 3 | 4 | 5 | | | V-1 | Rad54l | |
| 9973 | 3 | 4 | 5 | | | V-1 | Rae1 | |
| 9974 | 3 | 4 | 5 | | | V-1 | Rai2 | |
| 9975 | 3 | 4 | 5 | | | V-1 | Ralgps1 | |
| 9976 | 3 | 4 | 5 | | | V-1 | Ran | |
| 9977 | 3 | 4 | 5 | | | V-1 | Ranbp1 | |
| 9978 | 3 | 4 | 5 | | | V-1 | Rap1a | |
| 9979 | 3 | 4 | 5 | | | V-1 | Rapsn | |
| 9980 | 3 | 4 | 5 | | | V-1 | Rarb | |
| 9981 | 3 | 4 | 5 | | | V-1 | Rasa4 | |
| 9982 | 3 | 4 | 5 | | | V-1 | Rasd2 | |
| 9983 | 3 | 4 | 5 | | | V-1 | Rasef | |
| 9984 | 3 | 4 | 5 | | | V-1 | Rasgef1b | |
| 9985 | 3 | 4 | 5 | | | V-1 | Rasgef1c | |
| 9986 | 3 | 4 | 5 | | | V-1 | Rasl11a | |
| 9987 | 3 | 4 | 5 | | | V-1 | Rasl12 | |
| 9988 | 3 | 4 | 5 | | | V-1 | Rassf10 | |
| 9989 | 3 | 4 | 5 | | | V-1 | Rassf5 | |
| 9990 | 3 | 4 | 5 | | | V-1 | Rassf9 | |
| 9991 | 3 | 4 | 5 | | | V-1 | Rbbp8 | |
| 9992 | 3 | 4 | 5 | | | V-1 | Rbfa | |
| 9993 | 3 | 4 | 5 | | | V-1 | Rbfox2 | |
| 9994 | 3 | 4 | 5 | | | V-1 | Rbm20 | |
| 9995 | 3 | 4 | 5 | | | V-1 | Rbm26 | |
| 9996 | 3 | 4 | 5 | | | V-1 | Rbms1 | |
| 9997 | 3 | 4 | 5 | | | V-1 | Rbmx2 | |
| 9998 | 3 | 4 | 5 | | | V-1 | Rbp4 | |
| 9999 | 3 | 4 | 5 | | | V-1 | Rbpms2 | |
| 10000 | 3 | 4 | 5 | | | V-1 | Rce1 | |
| 10001 | 3 | 4 | 5 | | | V-1 | Rchy1 | |
| 10002 | 3 | 4 | 5 | | | V-1 | Rcn3 | |
| 10003 | 3 | 4 | 5 | | | V-1 | Rcor2 | |
| 10004 | 3 | 4 | 5 | | | V-1 | Rdh13 | |
| 10005 | 3 | 4 | 5 | | | V-1 | Rdh9 | |
| 10006 | 3 | 4 | 5 | | | V-1 | Recql | |
| 10007 | 3 | 4 | 5 | | | V-1 | Recql4 | |
| 10008 | 3 | 4 | 5 | | | V-1 | Recql5 | |
| 10009 | 3 | 4 | 5 | | | V-1 | Redrum | |
| 10010 | 3 | 4 | 5 | | | V-1 | Reep1 | |
| 10011 | 3 | 4 | 5 | | | V-1 | Reep2 | |
| 10012 | 3 | 4 | 5 | | | V-1 | Reep5 | |
| 10013 | 3 | 4 | 5 | | | V-1 | Relb | |
| 10014 | 3 | 4 | 5 | | | V-1 | Rell1 | |
| 10015 | 3 | 4 | 5 | | | V-1 | Rerg | |
| 10016 | 3 | 4 | 5 | | | V-1 | Rexo2 | |
| 10017 | 3 | 4 | 5 | | | V-1 | Rfc3 | |
| 10018 | 3 | 4 | 5 | | | V-1 | Rft1 | |
| 10019 | 3 | 4 | 5 | | | V-1 | Rfx2 | |
| 10020 | 3 | 4 | 5 | | | V-1 | Rfx7 | |
| 10021 | 3 | 4 | 5 | | | V-1 | Rgma | |
| 10022 | 3 | 4 | 5 | | | V-1 | Rgs1 | |
| 10023 | 3 | 4 | 5 | | | V-1 | Rgs10 | |
| 10024 | 3 | 4 | 5 | | | V-1 | Rgs12 | |
| 10025 | 3 | 4 | 5 | | | V-1 | Rgs18 | |
| 10026 | 3 | 4 | 5 | | | V-1 | Rhbdf1 | |
| 10027 | 3 | 4 | 5 | | | V-1 | Rhebl1 | |

Fig. 43 - 60

| | | | | | | | |
|---|---|---|---|---|---|---|---|
| 10028 | 3 | 4 | 5 | | | V-1 | Rhod |
| 10029 | 3 | 4 | 5 | | | V-1 | Rhof |
| 10030 | 3 | 4 | 5 | | | V-1 | Rhoj |
| 10031 | 3 | 4 | 5 | | | V-1 | Rhou |
| 10032 | 3 | 4 | 5 | | | V-1 | Rhov |
| 10033 | 3 | 4 | 5 | | | V-1 | Riip |
| 10034 | 3 | 4 | 5 | | | V-1 | Rimklb |
| 10035 | 3 | 4 | 5 | | | V-1 | Rin1 |
| 10036 | 3 | 4 | 5 | | | V-1 | Rin2 |
| 10037 | 3 | 4 | 5 | | | V-1 | Riok1 |
| 10038 | 3 | 4 | 5 | | | V-1 | Ripk3 |
| 10039 | 3 | 4 | 5 | | | V-1 | Ripk4 |
| 10040 | 3 | 4 | 5 | | | V-1 | Rmdn3 |
| 10041 | 3 | 4 | 5 | | | V-1 | Rmnd5b |
| 10042 | 3 | 4 | 5 | | | V-1 | Rnaseh2c |
| 10043 | 3 | 4 | 5 | | | V-1 | Rnasek |
| 10044 | 3 | 4 | 5 | | | V-1 | Rnaset2b |
| 10045 | 3 | 4 | 5 | | | V-1 | Rnd3 |
| 10046 | 3 | 4 | 5 | | | V-1 | Rnf113a1 |
| 10047 | 3 | 4 | 5 | | | V-1 | Rnf121 |
| 10048 | 3 | 4 | 5 | | | V-1 | Rnf123 |
| 10049 | 3 | 4 | 5 | | | V-1 | Rnf138rt1 |
| 10050 | 3 | 4 | 5 | | | V-1 | Rnf144b |
| 10051 | 3 | 4 | 5 | | | V-1 | Rnf150 |
| 10052 | 3 | 4 | 5 | | | V-1 | Rnf181 |
| 10053 | 3 | 4 | 5 | | | V-1 | Rnf186 |
| 10054 | 3 | 4 | 5 | | | V-1 | Rnf208 |
| 10055 | 3 | 4 | 5 | | | V-1 | Rnf217 |
| 10056 | 3 | 4 | 5 | | | V-1 | Rnf222 |
| 10057 | 3 | 4 | 5 | | | V-1 | Rnf43 |
| 10058 | 3 | 4 | 5 | | | V-1 | Rnls |
| 10059 | 3 | 4 | 5 | | | V-1 | Robo1 |
| 10060 | 3 | 4 | 5 | | | V-1 | Ror2 |
| 10061 | 3 | 4 | 5 | | | V-1 | Rora |
| 10062 | 3 | 4 | 5 | | | V-1 | Rpa1 |
| 10063 | 3 | 4 | 5 | | | V-1 | Rpa2 |
| 10064 | 3 | 4 | 5 | | | V-1 | Rpain |
| 10065 | 3 | 4 | 5 | | | V-1 | Rpf2 |
| 10066 | 3 | 4 | 5 | | | V-1 | Rph3al |
| 10067 | 3 | 4 | 5 | | | V-1 | Rpl10 |
| 10068 | 3 | 4 | 5 | | | V-1 | Rpl10a |
| 10069 | 3 | 4 | 5 | | | V-1 | Rpl12 |
| 10070 | 3 | 4 | 5 | | | V-1 | Rpl13 |
| 10071 | 3 | 4 | 5 | | | V-1 | Rpl14 |
| 10072 | 3 | 4 | 5 | | | V-1 | Rpl17 |
| 10073 | 3 | 4 | 5 | | | V-1 | Rpl18 |
| 10074 | 3 | 4 | 5 | | | V-1 | Rpl19 |
| 10075 | 3 | 4 | 5 | | | V-1 | Rpl21 |
| 10076 | 3 | 4 | 5 | | | V-1 | Rpl23 |
| 10077 | 3 | 4 | 5 | | | V-1 | Rpl27 |
| 10078 | 3 | 4 | 5 | | | V-1 | Rpl29 |
| 10079 | 3 | 4 | 5 | | | V-1 | Rpl3 |
| 10080 | 3 | 4 | 5 | | | V-1 | Rpl30 |
| 10081 | 3 | 4 | 5 | | | V-1 | Rpl31-ps12 |
| 10082 | 3 | 4 | 5 | | | V-1 | Rpl32 |
| 10083 | 3 | 4 | 5 | | | V-1 | Rpl34 |
| 10084 | 3 | 4 | 5 | | | V-1 | Rpl35 |
| 10085 | 3 | 4 | 5 | | | V-1 | Rpl36a |
| 10086 | 3 | 4 | 5 | | | V-1 | Rpl36al |
| 10087 | 3 | 4 | 5 | | | V-1 | Rpl41 |
| 10088 | 3 | 4 | 5 | | | V-1 | Rpl8 |
| 10089 | 3 | 4 | 5 | | | V-1 | Rplp1 |
| 10090 | 3 | 4 | 5 | | | V-1 | Rplp2-ps1 |
| 10091 | 3 | 4 | 5 | | | V-1 | Rpn1 |
| 10092 | 3 | 4 | 5 | | | V-1 | Rpp25 |
| 10093 | 3 | 4 | 5 | | | V-1 | Rpp25l |
| 10094 | 3 | 4 | 5 | | | V-1 | Rpp30 |
| 10095 | 3 | 4 | 5 | | | V-1 | Rps13 |
| 10096 | 3 | 4 | 5 | | | V-1 | Rps14 |
| 10097 | 3 | 4 | 5 | | | V-1 | Rps15 |
| 10098 | 3 | 4 | 5 | | | V-1 | Rps15a-ps6 |
| 10099 | 3 | 4 | 5 | | | V-1 | Rps18 |
| 10100 | 3 | 4 | 5 | | | V-1 | Rps19 |
| 10101 | 3 | 4 | 5 | | | V-1 | Rps19-ps3 |
| 10102 | 3 | 4 | 5 | | | V-1 | Rps2 |
| 10103 | 3 | 4 | 5 | | | V-1 | Rps20 |
| 10104 | 3 | 4 | 5 | | | V-1 | Rps23 |
| 10105 | 3 | 4 | 5 | | | V-1 | Rps24 |
| 10106 | 3 | 4 | 5 | | | V-1 | Rps25 |
| 10107 | 3 | 4 | 5 | | | V-1 | Rps27 |
| 10108 | 3 | 4 | 5 | | | V-1 | Rps27a |
| 10109 | 3 | 4 | 5 | | | V-1 | Rps29 |
| 10110 | 3 | 4 | 5 | | | V-1 | Rps3a1 |
| 10111 | 3 | 4 | 5 | | | V-1 | Rps4x |
| 10112 | 3 | 4 | 5 | | | V-1 | Rps5 |
| 10113 | 3 | 4 | 5 | | | V-1 | Rps6 |
| 10114 | 3 | 4 | 5 | | | V-1 | Rps6ka5 |
| 10115 | 3 | 4 | 5 | | | V-1 | Rps7 |
| 10116 | 3 | 4 | 5 | | | V-1 | Rps8 |
| 10117 | 3 | 4 | 5 | | | V-1 | Rps9 |
| 10118 | 3 | 4 | 5 | | | V-1 | Rpsa |
| 10119 | 3 | 4 | 5 | | | V-1 | Rpusd2 |
| 10120 | 3 | 4 | 5 | | | V-1 | Rpusd3 |
| 10121 | 3 | 4 | 5 | | | V-1 | Rrbp1 |
| 10122 | 3 | 4 | 5 | | | V-1 | Rreb1 |
| 10123 | 3 | 4 | 5 | | | V-1 | Rrm1 |
| 10124 | 3 | 4 | 5 | | | V-1 | Rrm2 |
| 10125 | 3 | 4 | 5 | | | V-1 | Rrp15 |
| 10126 | 3 | 4 | 5 | | | V-1 | Rrp1b |
| 10127 | 3 | 4 | 5 | | | V-1 | Rrp9 |
| 10128 | 3 | 4 | 5 | | | V-1 | Rsl1d1 |
| 10129 | 3 | 4 | 5 | | | V-1 | Rtca |
| 10130 | 3 | 4 | 5 | | | V-1 | Rtn4 |
| 10131 | 3 | 4 | 5 | | | V-1 | Rtn4ip1 |
| 10132 | 3 | 4 | 5 | | | V-1 | Rtn4rl1 |
| 10133 | 3 | 4 | 5 | | | V-1 | Rtn4rl2 |
| 10134 | 3 | 4 | 5 | | | V-1 | Runx1 |
| 10135 | 3 | 4 | 5 | | | V-1 | Rwdd2a |
| 10136 | 3 | 4 | 5 | | | V-1 | Rwdd2b |
| 10137 | 3 | 4 | 5 | | | V-1 | Rxra |
| 10138 | 3 | 4 | 5 | | | V-1 | S100a1 |
| 10139 | 3 | 4 | 5 | | | V-1 | S100a10 |
| 10140 | 3 | 4 | 5 | | | V-1 | S100a11 |
| 10141 | 3 | 4 | 5 | | | V-1 | S100a3 |
| 10142 | 3 | 4 | 5 | | | V-1 | S100a5 |
| 10143 | 3 | 4 | 5 | | | V-1 | S100a7a |
| 10144 | 3 | 4 | 5 | | | V-1 | S100b |
| 10145 | 3 | 4 | 5 | | | V-1 | S1pr5 |
| 10146 | 3 | 4 | 5 | | | V-1 | Saa4 |
| 10147 | 3 | 4 | 5 | | | V-1 | Sac3d1 |
| 10148 | 3 | 4 | 5 | | | V-1 | Samd14 |
| 10149 | 3 | 4 | 5 | | | V-1 | Samd4 |
| 10150 | 3 | 4 | 5 | | | V-1 | Samm50 |
| 10151 | 3 | 4 | 5 | | | V-1 | Samsn1 |
| 10152 | 3 | 4 | 5 | | | V-1 | Sap30 |
| 10153 | 3 | 4 | 5 | | | V-1 | Sapcd1 |
| 10154 | 3 | 4 | 5 | | | V-1 | Sar1b |
| 10155 | 3 | 4 | 5 | | | V-1 | Sars2 |
| 10156 | 3 | 4 | 5 | | | V-1 | Sash1 |
| 10157 | 3 | 4 | 5 | | | V-1 | Sash3 |
| 10158 | 3 | 4 | 5 | | | V-1 | Sat1 |
| 10159 | 3 | 4 | 5 | | | V-1 | Sbk2 |
| 10160 | 3 | 4 | 5 | | | V-1 | Sbno2 |
| 10161 | 3 | 4 | 5 | | | V-1 | Sc5d |
| 10162 | 3 | 4 | 5 | | | V-1 | Scamp5 |
| 10163 | 3 | 4 | 5 | | | V-1 | Scand1 |
| 10164 | 3 | 4 | 5 | | | V-1 | Scara5 |
| 10165 | 3 | 4 | 5 | | | V-1 | Scarf2 |
| 10166 | 3 | 4 | 5 | | | V-1 | Scarna6 |
| 10167 | 3 | 4 | 5 | | | V-1 | Scfd1 |
| 10168 | 3 | 4 | 5 | | | V-1 | Scg5 |
| 10169 | 3 | 4 | 5 | | | V-1 | Scgb3a1 |
| 10170 | 3 | 4 | 5 | | | V-1 | Sclt1 |
| 10171 | 3 | 4 | 5 | | | V-1 | Scly |
| 10172 | 3 | 4 | 5 | | | V-1 | Scnm1 |
| 10173 | 3 | 4 | 5 | | | V-1 | Scnn1a |
| 10174 | 3 | 4 | 5 | | | V-1 | Scnn1b |
| 10175 | 3 | 4 | 5 | | | V-1 | Sco1 |
| 10176 | 3 | 4 | 5 | | | V-1 | Scoc |
| 10177 | 3 | 4 | 5 | | | V-1 | Scrg1 |
| 10178 | 3 | 4 | 5 | | | V-1 | Scrn1 |
| 10179 | 3 | 4 | 5 | | | V-1 | Scrn2 |
| 10180 | 3 | 4 | 5 | | | V-1 | Sct |
| 10181 | 3 | 4 | 5 | | | V-1 | Scyl3 |
| 10182 | 3 | 4 | 5 | | | V-1 | Sdc1 |
| 10183 | 3 | 4 | 5 | | | V-1 | Sdhaf1 |
| 10184 | 3 | 4 | 5 | | | V-1 | Sdhb |
| 10185 | 3 | 4 | 5 | | | V-1 | Sdhc |
| 10186 | 3 | 4 | 5 | | | V-1 | Sdr42e1 |
| 10187 | 3 | 4 | 5 | | | V-1 | Sec11c |
| 10188 | 3 | 4 | 5 | | | V-1 | Sec14l4 |
| 10189 | 3 | 4 | 5 | | | V-1 | Sec14l5 |
| 10190 | 3 | 4 | 5 | | | V-1 | Sec16b |
| 10191 | 3 | 4 | 5 | | | V-1 | Sec24a |
| 10192 | 3 | 4 | 5 | | | V-1 | Sectm1a |
| 10193 | 3 | 4 | 5 | | | V-1 | Sel1l |
| 10194 | 3 | 4 | 5 | | | V-1 | Selk |
| 10195 | 3 | 4 | 5 | | | V-1 | Selm |
| 10196 | 3 | 4 | 5 | | | V-1 | Selplg |
| 10197 | 3 | 4 | 5 | | | V-1 | Sema3f |

Fig. 43 - 61

| | | | | | | | |
|---|---|---|---|---|---|---|---|
| 10198 | 3 | 4 | 5 | | | V-1 | Sema3g |
| 10199 | 3 | 4 | 5 | | | V-1 | Sema4d |
| 10200 | 3 | 4 | 5 | | | V-1 | Sema6b |
| 10201 | 3 | 4 | 5 | | | V-1 | Sema6c |
| 10202 | 3 | 4 | 5 | | | V-1 | Sepsecs |
| 10203 | 3 | 4 | 5 | | | V-1 | Sept11 |
| 10204 | 3 | 4 | 5 | | | V-1 | Sergef |
| 10205 | 3 | 4 | 5 | | | V-1 | Serhl |
| 10206 | 3 | 4 | 5 | | | V-1 | Serp2 |
| 10207 | 3 | 4 | 5 | | | V-1 | Serpina3f |
| 10208 | 3 | 4 | 5 | | | V-1 | Serpina3h |
| 10209 | 3 | 4 | 5 | | | V-1 | Serpina3i |
| 10210 | 3 | 4 | 5 | | | V-1 | Serpina3j |
| 10211 | 3 | 4 | 5 | | | V-1 | Serpina4-ps1 |
| 10212 | 3 | 4 | 5 | | | V-1 | Serpinb11 |
| 10213 | 3 | 4 | 5 | | | V-1 | Serpinb12 |
| 10214 | 3 | 4 | 5 | | | V-1 | Serpinb2 |
| 10215 | 3 | 4 | 5 | | | V-1 | Serpinb3a |
| 10216 | 3 | 4 | 5 | | | V-1 | Serpinb6b |
| 10217 | 3 | 4 | 5 | | | V-1 | Serpinb6c |
| 10218 | 3 | 4 | 5 | | | V-1 | Serpinb8 |
| 10219 | 3 | 4 | 5 | | | V-1 | Serpinb9b |
| 10220 | 3 | 4 | 5 | | | V-1 | Serping1 |
| 10221 | 3 | 4 | 5 | | | V-1 | Serpinh1 |
| 10222 | 3 | 4 | 5 | | | V-1 | Sertad1 |
| 10223 | 3 | 4 | 5 | | | V-1 | Sertad2 |
| 10224 | 3 | 4 | 5 | | | V-1 | Sertad3 |
| 10225 | 3 | 4 | 5 | | | V-1 | Setd1a |
| 10226 | 3 | 4 | 5 | | | V-1 | Setd2 |
| 10227 | 3 | 4 | 5 | | | V-1 | Setd4 |
| 10228 | 3 | 4 | 5 | | | V-1 | Setd5 |
| 10229 | 3 | 4 | 5 | | | V-1 | Setd6 |
| 10230 | 3 | 4 | 5 | | | V-1 | Sez6l |
| 10231 | 3 | 4 | 5 | | | V-1 | Sf3a3 |
| 10232 | 3 | 4 | 5 | | | V-1 | Sf3b5 |
| 10233 | 3 | 4 | 5 | | | V-1 | Sf3b6 |
| 10234 | 3 | 4 | 5 | | | V-1 | Sfrp1 |
| 10235 | 3 | 4 | 5 | | | V-1 | Sft2d1 |
| 10236 | 3 | 4 | 5 | | | V-1 | Sft2d2 |
| 10237 | 3 | 4 | 5 | | | V-1 | Sfta2 |
| 10238 | 3 | 4 | 5 | | | V-1 | Sftpa1 |
| 10239 | 3 | 4 | 5 | | | V-1 | Sfxn1 |
| 10240 | 3 | 4 | 5 | | | V-1 | Sfxn5 |
| 10241 | 3 | 4 | 5 | | | V-1 | Sgce |
| 10242 | 3 | 4 | 5 | | | V-1 | Sgk1 |
| 10243 | 3 | 4 | 5 | | | V-1 | Sgk3 |
| 10244 | 3 | 4 | 5 | | | V-1 | Sgol2 |
| 10245 | 3 | 4 | 5 | | | V-1 | Sgsm3 |
| 10246 | 3 | 4 | 5 | | | V-1 | Sh2b3 |
| 10247 | 3 | 4 | 5 | | | V-1 | Sh2d7 |
| 10248 | 3 | 4 | 5 | | | V-1 | Sh3bgrl3 |
| 10249 | 3 | 4 | 5 | | | V-1 | Sh3bp2 |
| 10250 | 3 | 4 | 5 | | | V-1 | Sh3bp4 |
| 10251 | 3 | 4 | 5 | | | V-1 | Sh3pxd2b |
| 10252 | 3 | 4 | 5 | | | V-1 | Sh3tc2 |
| 10253 | 3 | 4 | 5 | | | V-1 | Shb |
| 10254 | 3 | 4 | 5 | | | V-1 | Shd |
| 10255 | 3 | 4 | 5 | | | V-1 | Shfm1 |
| 10256 | 3 | 4 | 5 | | | V-1 | Shh |
| 10257 | 3 | 4 | 5 | | | V-1 | Shisa5 |
| 10258 | 3 | 4 | 5 | | | V-1 | Shkbp1 |
| 10259 | 3 | 4 | 5 | | | V-1 | Shmt2 |
| 10260 | 3 | 4 | 5 | | | V-1 | Shpk |
| 10261 | 3 | 4 | 5 | | | V-1 | Shroom2 |
| 10262 | 3 | 4 | 5 | | | V-1 | Shroom3 |
| 10263 | 3 | 4 | 5 | | | V-1 | Siae |
| 10264 | 3 | 4 | 5 | | | V-1 | Siglece |
| 10265 | 3 | 4 | 5 | | | V-1 | Sim2 |
| 10266 | 3 | 4 | 5 | | | V-1 | Sipa1l3 |
| 10267 | 3 | 4 | 5 | | | V-1 | Sirpa |
| 10268 | 3 | 4 | 5 | | | V-1 | Sirt5 |
| 10269 | 3 | 4 | 5 | | | V-1 | Sirt6 |
| 10270 | 3 | 4 | 5 | | | V-1 | Six1 |
| 10271 | 3 | 4 | 5 | | | V-1 | Six5 |
| 10272 | 3 | 4 | 5 | | | V-1 | Ska2 |
| 10273 | 3 | 4 | 5 | | | V-1 | Skil |
| 10274 | 3 | 4 | 5 | | | V-1 | Skint10 |
| 10275 | 3 | 4 | 5 | | | V-1 | Skp1a |
| 10276 | 3 | 4 | 5 | | | V-1 | Slc10a2 |
| 10277 | 3 | 4 | 5 | | | V-1 | Slc10a6 |
| 10278 | 3 | 4 | 5 | | | V-1 | Slc11a2 |
| 10279 | 3 | 4 | 5 | | | V-1 | Slc12a2 |
| 10280 | 3 | 4 | 5 | | | V-1 | Slc14a1 |
| 10281 | 3 | 4 | 5 | | | V-1 | Slc15a1 |
| 10282 | 3 | 4 | 5 | | | V-1 | Slc16a1 |
| 10283 | 3 | 4 | 5 | | | V-1 | Slc16a10 |
| 10284 | 3 | 4 | 5 | | | V-1 | Slc16a12 |
| 10285 | 3 | 4 | 5 | | | V-1 | Slc16a2 |
| 10286 | 3 | 4 | 5 | | | V-1 | Slc17a3 |
| 10287 | 3 | 4 | 5 | | | V-1 | Slc17a9 |
| 10288 | 3 | 4 | 5 | | | V-1 | Slc18b1 |
| 10289 | 3 | 4 | 5 | | | V-1 | Slc19a1 |
| 10290 | 3 | 4 | 5 | | | V-1 | Slc19a2 |
| 10291 | 3 | 4 | 5 | | | V-1 | Slc1a1 |
| 10292 | 3 | 4 | 5 | | | V-1 | Slc1a3 |
| 10293 | 3 | 4 | 5 | | | V-1 | Slc1a5 |
| 10294 | 3 | 4 | 5 | | | V-1 | Slc20a1 |
| 10295 | 3 | 4 | 5 | | | V-1 | Slc20a2 |
| 10296 | 3 | 4 | 5 | | | V-1 | Slc22a1 |
| 10297 | 3 | 4 | 5 | | | V-1 | Slc22a17 |
| 10298 | 3 | 4 | 5 | | | V-1 | Slc22a18 |
| 10299 | 3 | 4 | 5 | | | V-1 | Slc22a2 |
| 10300 | 3 | 4 | 5 | | | V-1 | Slc22a21 |
| 10301 | 3 | 4 | 5 | | | V-1 | Slc22a28 |
| 10302 | 3 | 4 | 5 | | | V-1 | Slc22a30 |
| 10303 | 3 | 4 | 5 | | | V-1 | Slc23a1 |
| 10304 | 3 | 4 | 5 | | | V-1 | Slc23a2 |
| 10305 | 3 | 4 | 5 | | | V-1 | Slc24a3 |
| 10306 | 3 | 4 | 5 | | | V-1 | Slc25a10 |
| 10307 | 3 | 4 | 5 | | | V-1 | Slc25a12 |
| 10308 | 3 | 4 | 5 | | | V-1 | Slc25a25 |
| 10309 | 3 | 4 | 5 | | | V-1 | Slc25a28 |
| 10310 | 3 | 4 | 5 | | | V-1 | Slc25a35 |
| 10311 | 3 | 4 | 5 | | | V-1 | Slc25a4 |
| 10312 | 3 | 4 | 5 | | | V-1 | Slc25a42 |
| 10313 | 3 | 4 | 5 | | | V-1 | Slc25a47 |
| 10314 | 3 | 4 | 5 | | | V-1 | Slc25a48 |
| 10315 | 3 | 4 | 5 | | | V-1 | Slc26a6 |
| 10316 | 3 | 4 | 5 | | | V-1 | Slc29a3 |
| 10317 | 3 | 4 | 5 | | | V-1 | Slc2a1 |
| 10318 | 3 | 4 | 5 | | | V-1 | Slc2a2 |
| 10319 | 3 | 4 | 5 | | | V-1 | Slc2a4 |
| 10320 | 3 | 4 | 5 | | | V-1 | Slc2a6 |
| 10321 | 3 | 4 | 5 | | | V-1 | Slc2a9 |
| 10322 | 3 | 4 | 5 | | | V-1 | Slc30a2 |
| 10323 | 3 | 4 | 5 | | | V-1 | Slc30a7 |
| 10324 | 3 | 4 | 5 | | | V-1 | Slc33a1 |
| 10325 | 3 | 4 | 5 | | | V-1 | Slc34a1 |
| 10326 | 3 | 4 | 5 | | | V-1 | Slc35a3 |
| 10327 | 3 | 4 | 5 | | | V-1 | Slc35a4 |
| 10328 | 3 | 4 | 5 | | | V-1 | Slc35b1 |
| 10329 | 3 | 4 | 5 | | | V-1 | Slc35d1 |
| 10330 | 3 | 4 | 5 | | | V-1 | Slc35d2 |
| 10331 | 3 | 4 | 5 | | | V-1 | Slc36a1 |
| 10332 | 3 | 4 | 5 | | | V-1 | Slc38a3 |
| 10333 | 3 | 4 | 5 | | | V-1 | Slc39a10 |
| 10334 | 3 | 4 | 5 | | | V-1 | Slc39a14 |
| 10335 | 3 | 4 | 5 | | | V-1 | Slc39a2 |
| 10336 | 3 | 4 | 5 | | | V-1 | Slc41a3 |
| 10337 | 3 | 4 | 5 | | | V-1 | Slc44a1 |
| 10338 | 3 | 4 | 5 | | | V-1 | Slc44a3 |
| 10339 | 3 | 4 | 5 | | | V-1 | Slc4a11 |
| 10340 | 3 | 4 | 5 | | | V-1 | Slc4a1ap |
| 10341 | 3 | 4 | 5 | | | V-1 | Slc4a4 |
| 10342 | 3 | 4 | 5 | | | V-1 | Slc50a1 |
| 10343 | 3 | 4 | 5 | | | V-1 | Slc51a |
| 10344 | 3 | 4 | 5 | | | V-1 | Slc52a2 |
| 10345 | 3 | 4 | 5 | | | V-1 | Slc6a13 |
| 10346 | 3 | 4 | 5 | | | V-1 | Slc6a6 |
| 10347 | 3 | 4 | 5 | | | V-1 | Slc6a8 |
| 10348 | 3 | 4 | 5 | | | V-1 | Slc6a9 |
| 10349 | 3 | 4 | 5 | | | V-1 | Slc7a10 |
| 10350 | 3 | 4 | 5 | | | V-1 | Slc7a2 |
| 10351 | 3 | 4 | 5 | | | V-1 | Slc8a1 |
| 10352 | 3 | 4 | 5 | | | V-1 | Slc8b1 |
| 10353 | 3 | 4 | 5 | | | V-1 | Slc9a3r1 |
| 10354 | 3 | 4 | 5 | | | V-1 | Slco1a1 |
| 10355 | 3 | 4 | 5 | | | V-1 | Slco1a4 |
| 10356 | 3 | 4 | 5 | | | V-1 | Slco2a1 |
| 10357 | 3 | 4 | 5 | | | V-1 | Slfn8 |
| 10358 | 3 | 4 | 5 | | | V-1 | Slfn9 |
| 10359 | 3 | 4 | 5 | | | V-1 | Slmo1 |
| 10360 | 3 | 4 | 5 | | | V-1 | Slx4 |
| 10361 | 3 | 4 | 5 | | | V-1 | Smad3 |
| 10362 | 3 | 4 | 5 | | | V-1 | Smad6 |
| 10363 | 3 | 4 | 5 | | | V-1 | Smad7 |
| 10364 | 3 | 4 | 5 | | | V-1 | Smarcb1 |
| 10365 | 3 | 4 | 5 | | | V-1 | Smc2 |
| 10366 | 3 | 4 | 5 | | | V-1 | Smco1 |
| 10367 | 3 | 4 | 5 | | | V-1 | Smdt1 |

Fig. 43 - 62

| | | | | | | | | | | | | | | | | |
|---|---|---|---|---|---|---|---|---|---|---|---|---|---|---|---|---|
| 10368 | 3 | 4 | 5 | | | V-1 | Smim1 | | 10453 | 3 | 4 | 5 | | | V-1 | Srp9 |
| 10369 | 3 | 4 | 5 | | | V-1 | Smim19 | | 10454 | 3 | 4 | 5 | | | V-1 | Srpx2 |
| 10370 | 3 | 4 | 5 | | | V-1 | Smim20 | | 10455 | 3 | 4 | 5 | | | V-1 | Srrd |
| 10371 | 3 | 4 | 5 | | | V-1 | Smim22 | | 10456 | 3 | 4 | 5 | | | V-1 | Srsf3 |
| 10372 | 3 | 4 | 5 | | | V-1 | Smim3 | | 10457 | 3 | 4 | 5 | | | V-1 | Srsf5 |
| 10373 | 3 | 4 | 5 | | | V-1 | Smim6 | | 10458 | 3 | 4 | 5 | | | V-1 | Ssb |
| 10374 | 3 | 4 | 5 | | | V-1 | Smim8 | | 10459 | 3 | 4 | 5 | | | V-1 | Ssbp4 |
| 10375 | 3 | 4 | 5 | | | V-1 | Smo | | 10460 | 3 | 4 | 5 | | | V-1 | Ssc5d |
| 10376 | 3 | 4 | 5 | | | V-1 | Smoc2 | | 10461 | 3 | 4 | 5 | | | V-1 | Ssh1 |
| 10377 | 3 | 4 | 5 | | | V-1 | Smpd1 | | 10462 | 3 | 4 | 5 | | | V-1 | Ssh3 |
| 10378 | 3 | 4 | 5 | | | V-1 | Smpd4 | | 10463 | 3 | 4 | 5 | | | V-1 | Sspn |
| 10379 | 3 | 4 | 5 | | | V-1 | Smpd5 | | 10464 | 3 | 4 | 5 | | | V-1 | Ssr1 |
| 10380 | 3 | 4 | 5 | | | V-1 | Smpdl3b | | 10465 | 3 | 4 | 5 | | | V-1 | Ssr2 |
| 10381 | 3 | 4 | 5 | | | V-1 | Sms | | 10466 | 3 | 4 | 5 | | | V-1 | Ssr4 |
| 10382 | 3 | 4 | 5 | | | V-1 | Smyd2 | | 10467 | 3 | 4 | 5 | | | V-1 | Sstr3 |
| 10383 | 3 | 4 | 5 | | | V-1 | Smyd5 | | 10468 | 3 | 4 | 5 | | | V-1 | St3gal1 |
| 10384 | 3 | 4 | 5 | | | V-1 | Snapc4 | | 10469 | 3 | 4 | 5 | | | V-1 | St3gal4 |
| 10385 | 3 | 4 | 5 | | | V-1 | Sncaip | | 10470 | 3 | 4 | 5 | | | V-1 | St6galnac5 |
| 10386 | 3 | 4 | 5 | | | V-1 | Sncg | | 10471 | 3 | 4 | 5 | | | V-1 | St7 |
| 10387 | 3 | 4 | 5 | | | V-1 | Snf8 | | 10472 | 3 | 4 | 5 | | | V-1 | St8sia1 |
| 10388 | 3 | 4 | 5 | | | V-1 | Snhg11 | | 10473 | 3 | 4 | 5 | | | V-1 | Stab1 |
| 10389 | 3 | 4 | 5 | | | V-1 | Snhg5 | | 10474 | 3 | 4 | 5 | | | V-1 | Stab2 |
| 10390 | 3 | 4 | 5 | | | V-1 | Snhg8 | | 10475 | 3 | 4 | 5 | | | V-1 | Stap2 |
| 10391 | 3 | 4 | 5 | | | V-1 | Snrnp200 | | 10476 | 3 | 4 | 5 | | | V-1 | Stard5 |
| 10392 | 3 | 4 | 5 | | | V-1 | Snrnp40 | | 10477 | 3 | 4 | 5 | | | V-1 | Stat2 |
| 10393 | 3 | 4 | 5 | | | V-1 | Snrpa1 | | 10478 | 3 | 4 | 5 | | | V-1 | Stc1 |
| 10394 | 3 | 4 | 5 | | | V-1 | Snrpb | | 10479 | 3 | 4 | 5 | | | V-1 | Stk32c |
| 10395 | 3 | 4 | 5 | | | V-1 | Snrpb2 | | 10480 | 3 | 4 | 5 | | | V-1 | Stk35 |
| 10396 | 3 | 4 | 5 | | | V-1 | Snrpd1 | | 10481 | 3 | 4 | 5 | | | V-1 | Stk39 |
| 10397 | 3 | 4 | 5 | | | V-1 | Snrpd2 | | 10482 | 3 | 4 | 5 | | | V-1 | Stmn2 |
| 10398 | 3 | 4 | 5 | | | V-1 | Snrpe | | 10483 | 3 | 4 | 5 | | | V-1 | Stom |
| 10399 | 3 | 4 | 5 | | | V-1 | Snurf | | 10484 | 3 | 4 | 5 | | | V-1 | Strip2 |
| 10400 | 3 | 4 | 5 | | | V-1 | Snx20 | | 10485 | 3 | 4 | 5 | | | V-1 | Stx11 |
| 10401 | 3 | 4 | 5 | | | V-1 | Snx22 | | 10486 | 3 | 4 | 5 | | | V-1 | Stx17 |
| 10402 | 3 | 4 | 5 | | | V-1 | Snx24 | | 10487 | 3 | 4 | 5 | | | V-1 | Stx1b |
| 10403 | 3 | 4 | 5 | | | V-1 | Snx30 | | 10488 | 3 | 4 | 5 | | | V-1 | Stx4a |
| 10404 | 3 | 4 | 5 | | | V-1 | Snx33 | | 10489 | 3 | 4 | 5 | | | V-1 | Stx8 |
| 10405 | 3 | 4 | 5 | | | V-1 | Snx7 | | 10490 | 3 | 4 | 5 | | | V-1 | Stxbp3b |
| 10406 | 3 | 4 | 5 | | | V-1 | Soat2 | | 10491 | 3 | 4 | 5 | | | V-1 | Sub1 |
| 10407 | 3 | 4 | 5 | | | V-1 | Socs2 | | 10492 | 3 | 4 | 5 | | | V-1 | Sucig1 |
| 10408 | 3 | 4 | 5 | | | V-1 | Socs6 | | 10493 | 3 | 4 | 5 | | | V-1 | Sult2b1 |
| 10409 | 3 | 4 | 5 | | | V-1 | Sod3 | | 10494 | 3 | 4 | 5 | | | V-1 | Sult5a1 |
| 10410 | 3 | 4 | 5 | | | V-1 | Son | | 10495 | 3 | 4 | 5 | | | V-1 | Supt4a |
| 10411 | 3 | 4 | 5 | | | V-1 | Sorbs1 | | 10496 | 3 | 4 | 5 | | | V-1 | Supv3l1 |
| 10412 | 3 | 4 | 5 | | | V-1 | Sost | | 10497 | 3 | 4 | 5 | | | V-1 | Susd2 |
| 10413 | 3 | 4 | 5 | | | V-1 | Sostdc1 | | 10498 | 3 | 4 | 5 | | | V-1 | Suv420h2 |
| 10414 | 3 | 4 | 5 | | | V-1 | Sowahb | | 10499 | 3 | 4 | 5 | | | V-1 | Sv2b |
| 10415 | 3 | 4 | 5 | | | V-1 | Sox12 | | 10500 | 3 | 4 | 5 | | | V-1 | Svil |
| 10416 | 3 | 4 | 5 | | | V-1 | Sox15 | | 10501 | 3 | 4 | 5 | | | V-1 | Svip |
| 10417 | 3 | 4 | 5 | | | V-1 | Sox7 | | 10502 | 3 | 4 | 5 | | | V-1 | Swsap1 |
| 10418 | 3 | 4 | 5 | | | V-1 | Sp100 | | 10503 | 3 | 4 | 5 | | | V-1 | Syde1 |
| 10419 | 3 | 4 | 5 | | | V-1 | Sp140 | | 10504 | 3 | 4 | 5 | | | V-1 | Syk |
| 10420 | 3 | 4 | 5 | | | V-1 | Sp3os | | 10505 | 3 | 4 | 5 | | | V-1 | Syn2 |
| 10421 | 3 | 4 | 5 | | | V-1 | Spaca6 | | 10506 | 3 | 4 | 5 | | | V-1 | Syndig1l |
| 10422 | 3 | 4 | 5 | | | V-1 | Spag9 | | 10507 | 3 | 4 | 5 | | | V-1 | Syne1 |
| 10423 | 3 | 4 | 5 | | | V-1 | Spata13 | | 10508 | 3 | 4 | 5 | | | V-1 | Syne4 |
| 10424 | 3 | 4 | 5 | | | V-1 | Spata25 | | 10509 | 3 | 4 | 5 | | | V-1 | Synj2 |
| 10425 | 3 | 4 | 5 | | | V-1 | Spata21 | | 10510 | 3 | 4 | 5 | | | V-1 | Syp |
| 10426 | 3 | 4 | 5 | | | V-1 | Spata5 | | 10511 | 3 | 4 | 5 | | | V-1 | Sys1 |
| 10427 | 3 | 4 | 5 | | | V-1 | Spatc1 | | 10512 | 3 | 4 | 5 | | | V-1 | Syt8 |
| 10428 | 3 | 4 | 5 | | | V-1 | Spats2 | | 10513 | 3 | 4 | 5 | | | V-1 | Sytl1 |
| 10429 | 3 | 4 | 5 | | | V-1 | Spcs1 | | 10514 | 3 | 4 | 5 | | | V-1 | Sytl3 |
| 10430 | 3 | 4 | 5 | | | V-1 | Spcs3 | | 10515 | 3 | 4 | 5 | | | V-1 | Sytl4 |
| 10431 | 3 | 4 | 5 | | | V-1 | Spidr | | 10516 | 3 | 4 | 5 | | | V-1 | Tac2 |
| 10432 | 3 | 4 | 5 | | | V-1 | Spin2d | | 10517 | 3 | 4 | 5 | | | V-1 | Tacc3 |
| 10433 | 3 | 4 | 5 | | | V-1 | Spin4 | | 10518 | 3 | 4 | 5 | | | V-1 | Taco1 |
| 10434 | 3 | 4 | 5 | | | V-1 | Spink12 | | 10519 | 3 | 4 | 5 | | | V-1 | Tacr2 |
| 10435 | 3 | 4 | 5 | | | V-1 | Spns2 | | 10520 | 3 | 4 | 5 | | | V-1 | Tacstd2 |
| 10436 | 3 | 4 | 5 | | | V-1 | Spock2 | | 10521 | 3 | 4 | 5 | | | V-1 | Tada1 |
| 10437 | 3 | 4 | 5 | | | V-1 | Spred3 | | 10522 | 3 | 4 | 5 | | | V-1 | Tada2a |
| 10438 | 3 | 4 | 5 | | | V-1 | Sprr2b | | 10523 | 3 | 4 | 5 | | | V-1 | Taf13 |
| 10439 | 3 | 4 | 5 | | | V-1 | Sprr4 | | 10524 | 3 | 4 | 5 | | | V-1 | Taf4b |
| 10440 | 3 | 4 | 5 | | | V-1 | Spry4 | | 10525 | 3 | 4 | 5 | | | V-1 | Taf6l |
| 10441 | 3 | 4 | 5 | | | V-1 | Spryd7 | | 10526 | 3 | 4 | 5 | | | V-1 | Taf9 |
| 10442 | 3 | 4 | 5 | | | V-1 | Spsb1 | | 10527 | 3 | 4 | 5 | | | V-1 | Tal1 |
| 10443 | 3 | 4 | 5 | | | V-1 | Sptan1 | | 10528 | 3 | 4 | 5 | | | V-1 | Taldo1 |
| 10444 | 3 | 4 | 5 | | | V-1 | Sptbn1 | | 10529 | 3 | 4 | 5 | | | V-1 | Tango6 |
| 10445 | 3 | 4 | 5 | | | V-1 | Sptssb | | 10530 | 3 | 4 | 5 | | | V-1 | Taok1 |
| 10446 | 3 | 4 | 5 | | | V-1 | Sra1 | | 10531 | 3 | 4 | 5 | | | V-1 | Tapt1 |
| 10447 | 3 | 4 | 5 | | | V-1 | Srgap3 | | 10532 | 3 | 4 | 5 | | | V-1 | Tarsl2 |
| 10448 | 3 | 4 | 5 | | | V-1 | Srgn | | 10533 | 3 | 4 | 5 | | | V-1 | Tatdn3 |
| 10449 | 3 | 4 | 5 | | | V-1 | Srm | | 10534 | 3 | 4 | 5 | | | V-1 | Tbc1d10c |
| 10450 | 3 | 4 | 5 | | | V-1 | Srms | | 10535 | 3 | 4 | 5 | | | V-1 | Tbc1d24 |
| 10451 | 3 | 4 | 5 | | | V-1 | Srp14 | | 10536 | 3 | 4 | 5 | | | V-1 | Tbc1d31 |
| 10452 | 3 | 4 | 5 | | | V-1 | Srp19 | | 10537 | 3 | 4 | 5 | | | V-1 | Tbc1d7 |

Fig. 43 - 63

| | | | | | | | | |
|---|---|---|---|---|---|---|---|---|
| 10538 | 3 | 4 | 5 | | | V-1 | Tbcb |
| 10539 | 3 | 4 | 5 | | | V-1 | Tbcc |
| 10540 | 3 | 4 | 5 | | | V-1 | Tbcel |
| 10541 | 3 | 4 | 5 | | | V-1 | Tbck |
| 10542 | 3 | 4 | 5 | | | V-1 | Tbkbp1 |
| 10543 | 3 | 4 | 5 | | | V-1 | Tbl1xr1 |
| 10544 | 3 | 4 | 5 | | | V-1 | Tbl3 |
| 10545 | 3 | 4 | 5 | | | V-1 | Tbrg1 |
| 10546 | 3 | 4 | 5 | | | V-1 | Tc2n |
| 10547 | 3 | 4 | 5 | | | V-1 | Tcea2 |
| 10548 | 3 | 4 | 5 | | | V-1 | Tceal3 |
| 10549 | 3 | 4 | 5 | | | V-1 | Tceal8 |
| 10550 | 3 | 4 | 5 | | | V-1 | Tceb2 |
| 10551 | 3 | 4 | 5 | | | V-1 | Tcf19 |
| 10552 | 3 | 4 | 5 | | | V-1 | Tcf20 |
| 10553 | 3 | 4 | 5 | | | V-1 | Tcf24 |
| 10554 | 3 | 4 | 5 | | | V-1 | Tchhl1 |
| 10555 | 3 | 4 | 5 | | | V-1 | Tctex1d4 |
| 10556 | 3 | 4 | 5 | | | V-1 | Tctn2 |
| 10557 | 3 | 4 | 5 | | | V-1 | Tctn3 |
| 10558 | 3 | 4 | 5 | | | V-1 | Tdrd7 |
| 10559 | 3 | 4 | 5 | | | V-1 | Tead3 |
| 10560 | 3 | 4 | 5 | | | V-1 | Tectb |
| 10561 | 3 | 4 | 5 | | | V-1 | Tef |
| 10562 | 3 | 4 | 5 | | | V-1 | Telo2 |
| 10563 | 3 | 4 | 5 | | | V-1 | Tenc1 |
| 10564 | 3 | 4 | 5 | | | V-1 | Tenm3 |
| 10565 | 3 | 4 | 5 | | | V-1 | Tenm4 |
| 10566 | 3 | 4 | 5 | | | V-1 | Tes |
| 10567 | 3 | 4 | 5 | | | V-1 | Tesc |
| 10568 | 3 | 4 | 5 | | | V-1 | Tet2 |
| 10569 | 3 | 4 | 5 | | | V-1 | Tex30 |
| 10570 | 3 | 4 | 5 | | | V-1 | Tex38 |
| 10571 | 3 | 4 | 5 | | | V-1 | Tfap2a |
| 10572 | 3 | 4 | 5 | | | V-1 | Tfap2c |
| 10573 | 3 | 4 | 5 | | | V-1 | Tfap4 |
| 10574 | 3 | 4 | 5 | | | V-1 | Tfcp2l1 |
| 10575 | 3 | 4 | 5 | | | V-1 | Tff3 |
| 10576 | 3 | 4 | 5 | | | V-1 | Tfpi2 |
| 10577 | 3 | 4 | 5 | | | V-1 | Tgds |
| 10578 | 3 | 4 | 5 | | | V-1 | Tgfbi |
| 10579 | 3 | 4 | 5 | | | V-1 | Tgfbr2 |
| 10580 | 3 | 4 | 5 | | | V-1 | Tgfbr3 |
| 10581 | 3 | 4 | 5 | | | V-1 | Tgfbrap1 |
| 10582 | 3 | 4 | 5 | | | V-1 | Tgm2 |
| 10583 | 3 | 4 | 5 | | | V-1 | Tgm3 |
| 10584 | 3 | 4 | 5 | | | V-1 | Tgm4 |
| 10585 | 3 | 4 | 5 | | | V-1 | Tgtp1 |
| 10586 | 3 | 4 | 5 | | | V-1 | Tgtp2 |
| 10587 | 3 | 4 | 5 | | | V-1 | Thap1 |
| 10588 | 3 | 4 | 5 | | | V-1 | Thbs2 |
| 10589 | 3 | 4 | 5 | | | V-1 | Thbs3 |
| 10590 | 3 | 4 | 5 | | | V-1 | Thg1l |
| 10591 | 3 | 4 | 5 | | | V-1 | Thoc1 |
| 10592 | 3 | 4 | 5 | | | V-1 | Thoc2 |
| 10593 | 3 | 4 | 5 | | | V-1 | Thoc6 |
| 10594 | 3 | 4 | 5 | | | V-1 | Thoc7 |
| 10595 | 3 | 4 | 5 | | | V-1 | Thop1 |
| 10596 | 3 | 4 | 5 | | | V-1 | Thsd4 |
| 10597 | 3 | 4 | 5 | | | V-1 | Tiam1 |
| 10598 | 3 | 4 | 5 | | | V-1 | Timeless |
| 10599 | 3 | 4 | 5 | | | V-1 | Timm10 |
| 10600 | 3 | 4 | 5 | | | V-1 | Timm13 |
| 10601 | 3 | 4 | 5 | | | V-1 | Timm17a |
| 10602 | 3 | 4 | 5 | | | V-1 | Timm17b |
| 10603 | 3 | 4 | 5 | | | V-1 | Timm23 |
| 10604 | 3 | 4 | 5 | | | V-1 | Timm8a1 |
| 10605 | 3 | 4 | 5 | | | V-1 | Timm8b |
| 10606 | 3 | 4 | 5 | | | V-1 | Tinf2 |
| 10607 | 3 | 4 | 5 | | | V-1 | Tipin |
| 10608 | 3 | 4 | 5 | | | V-1 | Tjp1 |
| 10609 | 3 | 4 | 5 | | | V-1 | Tk1 |
| 10610 | 3 | 4 | 5 | | | V-1 | Tlcd2 |
| 10611 | 3 | 4 | 5 | | | V-1 | Tldc2 |
| 10612 | 3 | 4 | 5 | | | V-1 | Tle1 |
| 10613 | 3 | 4 | 5 | | | V-1 | Tle4 |
| 10614 | 3 | 4 | 5 | | | V-1 | Tlr3 |
| 10615 | 3 | 4 | 5 | | | V-1 | Tlr7 |
| 10616 | 3 | 4 | 5 | | | V-1 | Tlx3 |
| 10617 | 3 | 4 | 5 | | | V-1 | Tm2d1 |
| 10618 | 3 | 4 | 5 | | | V-1 | Tm2d3 |
| 10619 | 3 | 4 | 5 | | | V-1 | Tm7sf3 |
| 10620 | 3 | 4 | 5 | | | V-1 | Tma16 |
| 10621 | 3 | 4 | 5 | | | V-1 | Tma7 |
| 10622 | 3 | 4 | 5 | | | V-1 | Tmbim4 |
| 10623 | 3 | 4 | 5 | | | V-1 | Tmc8 |
| 10624 | 3 | 4 | 5 | | | V-1 | Tmcc4 |
| 10625 | 3 | 4 | 5 | | | V-1 | Tmem102 |
| 10626 | 3 | 4 | 5 | | | V-1 | Tmem108 |
| 10627 | 3 | 4 | 5 | | | V-1 | Tmem11 |
| 10628 | 3 | 4 | 5 | | | V-1 | Tmem117 |
| 10629 | 3 | 4 | 5 | | | V-1 | Tmem120b |
| 10630 | 3 | 4 | 5 | | | V-1 | Tmem125 |
| 10631 | 3 | 4 | 5 | | | V-1 | Tmem126a |
| 10632 | 3 | 4 | 5 | | | V-1 | Tmem132a |
| 10633 | 3 | 4 | 5 | | | V-1 | Tmem141 |
| 10634 | 3 | 4 | 5 | | | V-1 | Tmem147 |
| 10635 | 3 | 4 | 5 | | | V-1 | Tmem14c |
| 10636 | 3 | 4 | 5 | | | V-1 | Tmem150a |
| 10637 | 3 | 4 | 5 | | | V-1 | Tmem151a |
| 10638 | 3 | 4 | 5 | | | V-1 | Tmem154 |
| 10639 | 3 | 4 | 5 | | | V-1 | Tmem159 |
| 10640 | 3 | 4 | 5 | | | V-1 | Tmem160 |
| 10641 | 3 | 4 | 5 | | | V-1 | Tmem161b |
| 10642 | 3 | 4 | 5 | | | V-1 | Tmem169 |
| 10643 | 3 | 4 | 5 | | | V-1 | Tmem173 |
| 10644 | 3 | 4 | 5 | | | V-1 | Tmem181a |
| 10645 | 3 | 4 | 5 | | | V-1 | Tmem19 |
| 10646 | 3 | 4 | 5 | | | V-1 | Tmem192 |
| 10647 | 3 | 4 | 5 | | | V-1 | Tmem200b |
| 10648 | 3 | 4 | 5 | | | V-1 | Tmem203 |
| 10649 | 3 | 4 | 5 | | | V-1 | Tmem205 |
| 10650 | 3 | 4 | 5 | | | V-1 | Tmem208 |
| 10651 | 3 | 4 | 5 | | | V-1 | Tmem216 |
| 10652 | 3 | 4 | 5 | | | V-1 | Tmem220 |
| 10653 | 3 | 4 | 5 | | | V-1 | Tmem222 |
| 10654 | 3 | 4 | 5 | | | V-1 | Tmem223 |
| 10655 | 3 | 4 | 5 | | | V-1 | Tmem238 |
| 10656 | 3 | 4 | 5 | | | V-1 | Tmem243 |
| 10657 | 3 | 4 | 5 | | | V-1 | Tmem246 |
| 10658 | 3 | 4 | 5 | | | V-1 | Tmem251 |
| 10659 | 3 | 4 | 5 | | | V-1 | Tmem253 |
| 10660 | 3 | 4 | 5 | | | V-1 | Tmem254a |
| 10661 | 3 | 4 | 5 | | | V-1 | Tmem254b |
| 10662 | 3 | 4 | 5 | | | V-1 | Tmem255b |
| 10663 | 3 | 4 | 5 | | | V-1 | Tmem256 |
| 10664 | 3 | 4 | 5 | | | V-1 | Tmem258 |
| 10665 | 3 | 4 | 5 | | | V-1 | Tmem261 |
| 10666 | 3 | 4 | 5 | | | V-1 | Tmem35 |
| 10667 | 3 | 4 | 5 | | | V-1 | Tmem38b |
| 10668 | 3 | 4 | 5 | | | V-1 | Tmem39b |
| 10669 | 3 | 4 | 5 | | | V-1 | Tmem41a |
| 10670 | 3 | 4 | 5 | | | V-1 | Tmem45a |
| 10671 | 3 | 4 | 5 | | | V-1 | Tmem51 |
| 10672 | 3 | 4 | 5 | | | V-1 | Tmem53 |
| 10673 | 3 | 4 | 5 | | | V-1 | Tmem54 |
| 10674 | 3 | 4 | 5 | | | V-1 | Tmem59l |
| 10675 | 3 | 4 | 5 | | | V-1 | Tmem60 |
| 10676 | 3 | 4 | 5 | | | V-1 | Tmem67 |
| 10677 | 3 | 4 | 5 | | | V-1 | Tmem79 |
| 10678 | 3 | 4 | 5 | | | V-1 | Tmem87b |
| 10679 | 3 | 4 | 5 | | | V-1 | Tmem88b |
| 10680 | 3 | 4 | 5 | | | V-1 | Tmem8b |
| 10681 | 3 | 4 | 5 | | | V-1 | Tmem9 |
| 10682 | 3 | 4 | 5 | | | V-1 | Tmem97 |
| 10683 | 3 | 4 | 5 | | | V-1 | Tmevpg1 |
| 10684 | 3 | 4 | 5 | | | V-1 | Tmie |
| 10685 | 3 | 4 | 5 | | | V-1 | Tmigd1 |
| 10686 | 3 | 4 | 5 | | | V-1 | Tmod1 |
| 10687 | 3 | 4 | 5 | | | V-1 | Tmprss11a |
| 10688 | 3 | 4 | 5 | | | V-1 | Tmprss11bnl |
| 10689 | 3 | 4 | 5 | | | V-1 | Tmprss11d |
| 10690 | 3 | 4 | 5 | | | V-1 | Tmprss11f |
| 10691 | 3 | 4 | 5 | | | V-1 | Tmprss11g |
| 10692 | 3 | 4 | 5 | | | V-1 | Tmprss13 |
| 10693 | 3 | 4 | 5 | | | V-1 | Tmprss3 |
| 10694 | 3 | 4 | 5 | | | V-1 | Tmprss4 |
| 10695 | 3 | 4 | 5 | | | V-1 | Tmsb10 |
| 10696 | 3 | 4 | 5 | | | V-1 | Tmsb4x |
| 10697 | 3 | 4 | 5 | | | V-1 | Tmx1 |
| 10698 | 3 | 4 | 5 | | | V-1 | Tmx2 |
| 10699 | 3 | 4 | 5 | | | V-1 | Tmx4 |
| 10700 | 3 | 4 | 5 | | | V-1 | Tnfaip2 |
| 10701 | 3 | 4 | 5 | | | V-1 | Tnfaip3 |
| 10702 | 3 | 4 | 5 | | | V-1 | Tnfrsf11a |
| 10703 | 3 | 4 | 5 | | | V-1 | Tnfrsf18 |
| 10704 | 3 | 4 | 5 | | | V-1 | Tnfrsf1b |
| 10705 | 3 | 4 | 5 | | | V-1 | Tnfrsf23 |
| 10706 | 3 | 4 | 5 | | | V-1 | Tnfrsf4 |
| 10707 | 3 | 4 | 5 | | | V-1 | Tnfsf13 |

Fig. 43 - 64

| | | | | | | | |
|---|---|---|---|---|---|---|---|
| 10708 | 3 | 4 | 5 | | | V-1 | Tnfsf14 |
| 10709 | 3 | 4 | 5 | | | V-1 | Tnfsf8 |
| 10710 | 3 | 4 | 5 | | | V-1 | Tnfsf9 |
| 10711 | 3 | 4 | 5 | | | V-1 | Tnni3 |
| 10712 | 3 | 4 | 5 | | | V-1 | Tnni3k |
| 10713 | 3 | 4 | 5 | | | V-1 | Tnnt2 |
| 10714 | 3 | 4 | 5 | | | V-1 | Tns4 |
| 10715 | 3 | 4 | 5 | | | V-1 | Tnxb |
| 10716 | 3 | 4 | 5 | | | V-1 | Tob1 |
| 10717 | 3 | 4 | 5 | | | V-1 | Tomm22 |
| 10718 | 3 | 4 | 5 | | | V-1 | Tomm40l |
| 10719 | 3 | 4 | 5 | | | V-1 | Tomm6 |
| 10720 | 3 | 4 | 5 | | | V-1 | Tomm6os |
| 10721 | 3 | 4 | 5 | | | V-1 | Tomm7 |
| 10722 | 3 | 4 | 5 | | | V-1 | Top1mt |
| 10723 | 3 | 4 | 5 | | | V-1 | Topbp1 |
| 10724 | 3 | 4 | 5 | | | V-1 | Tor3a |
| 10725 | 3 | 4 | 5 | | | V-1 | Tox2 |
| 10726 | 3 | 4 | 5 | | | V-1 | Tpcn2 |
| 10727 | 3 | 4 | 5 | | | V-1 | Tpgs1 |
| 10728 | 3 | 4 | 5 | | | V-1 | Tpgs2 |
| 10729 | 3 | 4 | 5 | | | V-1 | Tpk1 |
| 10730 | 3 | 4 | 5 | | | V-1 | Traf3 |
| 10731 | 3 | 4 | 5 | | | V-1 | Traf6 |
| 10732 | 3 | 4 | 5 | | | V-1 | Trafd1 |
| 10733 | 3 | 4 | 5 | | | V-1 | Traip |
| 10734 | 3 | 4 | 5 | | | V-1 | Trak2 |
| 10735 | 3 | 4 | 5 | | | V-1 | Tram1 |
| 10736 | 3 | 4 | 5 | | | V-1 | Tram2 |
| 10737 | 3 | 4 | 5 | | | V-1 | Trappc1 |
| 10738 | 3 | 4 | 5 | | | V-1 | Trappc2l |
| 10739 | 3 | 4 | 5 | | | V-1 | Trappc4 |
| 10740 | 3 | 4 | 5 | | | V-1 | Trappc6a |
| 10741 | 3 | 4 | 5 | | | V-1 | Trerf1 |
| 10742 | 3 | 4 | 5 | | | V-1 | Trex1 |
| 10743 | 3 | 4 | 5 | | | V-1 | Trib1 |
| 10744 | 3 | 4 | 5 | | | V-1 | Trim12c |
| 10745 | 3 | 4 | 5 | | | V-1 | Trim13 |
| 10746 | 3 | 4 | 5 | | | V-1 | Trim14 |
| 10747 | 3 | 4 | 5 | | | V-1 | Trim16 |
| 10748 | 3 | 4 | 5 | | | V-1 | Trim2 |
| 10749 | 3 | 4 | 5 | | | V-1 | Trim30b |
| 10750 | 3 | 4 | 5 | | | V-1 | Trim44 |
| 10751 | 3 | 4 | 5 | | | V-1 | Trim67 |
| 10752 | 3 | 4 | 5 | | | V-1 | Trim68 |
| 10753 | 3 | 4 | 5 | | | V-1 | Trmt112 |
| 10754 | 3 | 4 | 5 | | | V-1 | Trmt6 |
| 10755 | 3 | 4 | 5 | | | V-1 | Trnp1 |
| 10756 | 3 | 4 | 5 | | | V-1 | Trp53inp1 |
| 10757 | 3 | 4 | 5 | | | V-1 | Trp53inp2 |
| 10758 | 3 | 4 | 5 | | | V-1 | Trp63 |
| 10759 | 3 | 4 | 5 | | | V-1 | Trpm6 |
| 10760 | 3 | 4 | 5 | | | V-1 | Trpt1 |
| 10761 | 3 | 4 | 5 | | | V-1 | Trpv2 |
| 10762 | 3 | 4 | 5 | | | V-1 | Tsen15 |
| 10763 | 3 | 4 | 5 | | | V-1 | Tsen2 |
| 10764 | 3 | 4 | 5 | | | V-1 | Tsg101 |
| 10765 | 3 | 4 | 5 | | | V-1 | Tshz1 |
| 10766 | 3 | 4 | 5 | | | V-1 | Tslp |
| 10767 | 3 | 4 | 5 | | | V-1 | Tspan12 |
| 10768 | 3 | 4 | 5 | | | V-1 | Tspan15 |
| 10769 | 3 | 4 | 5 | | | V-1 | Tspan32 |
| 10770 | 3 | 4 | 5 | | | V-1 | Tspan4 |
| 10771 | 3 | 4 | 5 | | | V-1 | Tspan6 |
| 10772 | 3 | 4 | 5 | | | V-1 | Tspan7 |
| 10773 | 3 | 4 | 5 | | | V-1 | Tspo |
| 10774 | 3 | 4 | 5 | | | V-1 | Tsr3 |
| 10775 | 3 | 4 | 5 | | | V-1 | Tst |
| 10776 | 3 | 4 | 5 | | | V-1 | Tstd3 |
| 10777 | 3 | 4 | 5 | | | V-1 | Ttc22 |
| 10778 | 3 | 4 | 5 | | | V-1 | Ttc23 |
| 10779 | 3 | 4 | 5 | | | V-1 | Ttc27 |
| 10780 | 3 | 4 | 5 | | | V-1 | Ttc30a2 |
| 10781 | 3 | 4 | 5 | | | V-1 | Ttc38 |
| 10782 | 3 | 4 | 5 | | | V-1 | Ttc39a |
| 10783 | 3 | 4 | 5 | | | V-1 | Ttc39b |
| 10784 | 3 | 4 | 5 | | | V-1 | Ttc39c |
| 10785 | 3 | 4 | 5 | | | V-1 | Ttc8 |
| 10786 | 3 | 4 | 5 | | | V-1 | Ttc9 |
| 10787 | 3 | 4 | 5 | | | V-1 | Tti2 |
| 10788 | 3 | 4 | 5 | | | V-1 | Ttll1 |
| 10789 | 3 | 4 | 5 | | | V-1 | Ttll10 |
| 10790 | 3 | 4 | 5 | | | V-1 | Ttll11 |
| 10791 | 3 | 4 | 5 | | | V-1 | Ttll12 |
| 10792 | 3 | 4 | 5 | | | V-1 | Ttll7 |

| | | | | | | | |
|---|---|---|---|---|---|---|---|
| 10793 | 3 | 4 | 5 | | | V-1 | Ttr |
| 10794 | 3 | 4 | 5 | | | V-1 | Ttyh2 |
| 10795 | 3 | 4 | 5 | | | V-1 | Ttyh3 |
| 10796 | 3 | 4 | 5 | | | V-1 | Tuba1a |
| 10797 | 3 | 4 | 5 | | | V-1 | Tuba1c |
| 10798 | 3 | 4 | 5 | | | V-1 | Tuba4a |
| 10799 | 3 | 4 | 5 | | | V-1 | Tubb1 |
| 10800 | 3 | 4 | 5 | | | V-1 | Tubb2a-ps2 |
| 10801 | 3 | 4 | 5 | | | V-1 | Tubb2b |
| 10802 | 3 | 4 | 5 | | | V-1 | Tubb4b |
| 10803 | 3 | 4 | 5 | | | V-1 | Tubd1 |
| 10804 | 3 | 4 | 5 | | | V-1 | Tubg1 |
| 10805 | 3 | 4 | 5 | | | V-1 | Tufm |
| 10806 | 3 | 4 | 5 | | | V-1 | Tuft1 |
| 10807 | 3 | 4 | 5 | | | V-1 | Tulp4 |
| 10808 | 3 | 4 | 5 | | | V-1 | Tusc1 |
| 10809 | 3 | 4 | 5 | | | V-1 | Tusc3 |
| 10810 | 3 | 4 | 5 | | | V-1 | Tvp23a |
| 10811 | 3 | 4 | 5 | | | V-1 | Txn1 |
| 10812 | 3 | 4 | 5 | | | V-1 | Txndc11 |
| 10813 | 3 | 4 | 5 | | | V-1 | Txndc17 |
| 10814 | 3 | 4 | 5 | | | V-1 | Txnrd1 |
| 10815 | 3 | 4 | 5 | | | V-1 | Txnrd3 |
| 10816 | 3 | 4 | 5 | | | V-1 | Tyms |
| 10817 | 3 | 4 | 5 | | | V-1 | U2af1 |
| 10818 | 3 | 4 | 5 | | | V-1 | Uaca |
| 10819 | 3 | 4 | 5 | | | V-1 | Uap1l1 |
| 10820 | 3 | 4 | 5 | | | V-1 | Uba52 |
| 10821 | 3 | 4 | 5 | | | V-1 | Ubash3b |
| 10822 | 3 | 4 | 5 | | | V-1 | Ubc |
| 10823 | 3 | 4 | 5 | | | V-1 | Ube2e2 |
| 10824 | 3 | 4 | 5 | | | V-1 | Ube2e3 |
| 10825 | 3 | 4 | 5 | | | V-1 | Ube2j2 |
| 10826 | 3 | 4 | 5 | | | V-1 | Ube2m |
| 10827 | 3 | 4 | 5 | | | V-1 | Ube2ql1 |
| 10828 | 3 | 4 | 5 | | | V-1 | Ube2s |
| 10829 | 3 | 4 | 5 | | | V-1 | Ube2t |
| 10830 | 3 | 4 | 5 | | | V-1 | Ubr2 |
| 10831 | 3 | 4 | 5 | | | V-1 | Ubr5 |
| 10832 | 3 | 4 | 5 | | | V-1 | Ubxn2a |
| 10833 | 3 | 4 | 5 | | | V-1 | Uchl5 |
| 10834 | 3 | 4 | 5 | | | V-1 | Uck2 |
| 10835 | 3 | 4 | 5 | | | V-1 | Uckl1os |
| 10836 | 3 | 4 | 5 | | | V-1 | Ucma |
| 10837 | 3 | 4 | 5 | | | V-1 | Ucn |
| 10838 | 3 | 4 | 5 | | | V-1 | Ucn2 |
| 10839 | 3 | 4 | 5 | | | V-1 | Ufc1 |
| 10840 | 3 | 4 | 5 | | | V-1 | Ugp2 |
| 10841 | 3 | 4 | 5 | | | V-1 | Ugt1a6b |
| 10842 | 3 | 4 | 5 | | | V-1 | Ugt1a7c |
| 10843 | 3 | 4 | 5 | | | V-1 | Ugt2b34 |
| 10844 | 3 | 4 | 5 | | | V-1 | Ugt2b35 |
| 10845 | 3 | 4 | 5 | | | V-1 | Ugt2b37 |
| 10846 | 3 | 4 | 5 | | | V-1 | Ugt2b38 |
| 10847 | 3 | 4 | 5 | | | V-1 | Uhrf1bp1 |
| 10848 | 3 | 4 | 5 | | | V-1 | Unc5a |
| 10849 | 3 | 4 | 5 | | | V-1 | Unc5b |
| 10850 | 3 | 4 | 5 | | | V-1 | Unc93a |
| 10851 | 3 | 4 | 5 | | | V-1 | Unc93b1 |
| 10852 | 3 | 4 | 5 | | | V-1 | Ung |
| 10853 | 3 | 4 | 5 | | | V-1 | Upk1a |
| 10854 | 3 | 4 | 5 | | | V-1 | Upk1b |
| 10855 | 3 | 4 | 5 | | | V-1 | Uqcr11 |
| 10856 | 3 | 4 | 5 | | | V-1 | Uqcrb |
| 10857 | 3 | 4 | 5 | | | V-1 | Uqcrh |
| 10858 | 3 | 4 | 5 | | | V-1 | Uqcrq |
| 10859 | 3 | 4 | 5 | | | V-1 | Urad |
| 10860 | 3 | 4 | 5 | | | V-1 | Urod |
| 10861 | 3 | 4 | 5 | | | V-1 | Use1 |
| 10862 | 3 | 4 | 5 | | | V-1 | Usp2 |
| 10863 | 3 | 4 | 5 | | | V-1 | Usp28 |
| 10864 | 3 | 4 | 5 | | | V-1 | Usp46 |
| 10865 | 3 | 4 | 5 | | | V-1 | Usp5 |
| 10866 | 3 | 4 | 5 | | | V-1 | Usp53 |
| 10867 | 3 | 4 | 5 | | | V-1 | Utf1 |
| 10868 | 3 | 4 | 5 | | | V-1 | Uts2r |
| 10869 | 3 | 4 | 5 | | | V-1 | Uxs1 |
| 10870 | 3 | 4 | 5 | | | V-1 | Vash1 |
| 10871 | 3 | 4 | 5 | | | V-1 | Vasn |
| 10872 | 3 | 4 | 5 | | | V-1 | Vat1 |
| 10873 | 3 | 4 | 5 | | | V-1 | Vat1l |
| 10874 | 3 | 4 | 5 | | | V-1 | Vav3 |
| 10875 | 3 | 4 | 5 | | | V-1 | Vcan |
| 10876 | 3 | 4 | 5 | | | V-1 | Vcpip1 |
| 10877 | 3 | 4 | 5 | | | V-1 | Vcpkmt |

Fig. 43 - 65

| | | | | | | | | | | | | | | | |
|---|---|---|---|---|---|---|---|---|---|---|---|---|---|---|---|
| 10878 | 3 | 4 | 5 | | | V-1 | Vegfa | 10963 | 3 | 4 | 5 | | | V-1 | Zfp275 |
| 10879 | 3 | 4 | 5 | | | V-1 | Vgf | 10964 | 3 | 4 | 5 | | | V-1 | Zfp280c |
| 10880 | 3 | 4 | 5 | | | V-1 | Vgll3 | 10965 | 3 | 4 | 5 | | | V-1 | Zfp281 |
| 10881 | 3 | 4 | 5 | | | V-1 | Vim | 10966 | 3 | 4 | 5 | | | V-1 | Zfp292 |
| 10882 | 3 | 4 | 5 | | | V-1 | Vipr2 | 10967 | 3 | 4 | 5 | | | V-1 | Zfp3 |
| 10883 | 3 | 4 | 5 | | | V-1 | Vit | 10968 | 3 | 4 | 5 | | | V-1 | Zfp316 |
| 10884 | 3 | 4 | 5 | | | V-1 | Vma21 | 10969 | 3 | 4 | 5 | | | V-1 | Zfp358 |
| 10885 | 3 | 4 | 5 | | | V-1 | Vmp1 | 10970 | 3 | 4 | 5 | | | V-1 | Zfp385a |
| 10886 | 3 | 4 | 5 | | | V-1 | Vopp1 | 10971 | 3 | 4 | 5 | | | V-1 | Zfp40 |
| 10887 | 3 | 4 | 5 | | | V-1 | Vps25 | 10972 | 3 | 4 | 5 | | | V-1 | Zfp407 |
| 10888 | 3 | 4 | 5 | | | V-1 | Vps28 | 10973 | 3 | 4 | 5 | | | V-1 | Zfp423 |
| 10889 | 3 | 4 | 5 | | | V-1 | Vps37d | 10974 | 3 | 4 | 5 | | | V-1 | Zfp445 |
| 10890 | 3 | 4 | 5 | | | V-1 | Vrk2 | 10975 | 3 | 4 | 5 | | | V-1 | Zfp449 |
| 10891 | 3 | 4 | 5 | | | V-1 | Vsig2 | 10976 | 3 | 4 | 5 | | | V-1 | Zfp46 |
| 10892 | 3 | 4 | 5 | | | V-1 | Vsig4 | 10977 | 3 | 4 | 5 | | | V-1 | Zfp507 |
| 10893 | 3 | 4 | 5 | | | V-1 | Vsig8 | 10978 | 3 | 4 | 5 | | | V-1 | Zfp518b |
| 10894 | 3 | 4 | 5 | | | V-1 | Vsnl1 | 10979 | 3 | 4 | 5 | | | V-1 | Zfp52 |
| 10895 | 3 | 4 | 5 | | | V-1 | Vstm5 | 10980 | 3 | 4 | 5 | | | V-1 | Zfp532 |
| 10896 | 3 | 4 | 5 | | | V-1 | Vtcn1 | 10981 | 3 | 4 | 5 | | | V-1 | Zfp54 |
| 10897 | 3 | 4 | 5 | | | V-1 | Vwf | 10982 | 3 | 4 | 5 | | | V-1 | Zfp580 |
| 10898 | 3 | 4 | 5 | | | V-1 | Wdfy3 | 10983 | 3 | 4 | 5 | | | V-1 | Zfp608 |
| 10899 | 3 | 4 | 5 | | | V-1 | Wdr19 | 10984 | 3 | 4 | 5 | | | V-1 | Zfp641 |
| 10900 | 3 | 4 | 5 | | | V-1 | Wdr24 | 10985 | 3 | 4 | 5 | | | V-1 | Zfp646 |
| 10901 | 3 | 4 | 5 | | | V-1 | Wdr43 | 10986 | 3 | 4 | 5 | | | V-1 | Zfp651 |
| 10902 | 3 | 4 | 5 | | | V-1 | Wdr46 | 10987 | 3 | 4 | 5 | | | V-1 | Zfp687 |
| 10903 | 3 | 4 | 5 | | | V-1 | Wdr55 | 10988 | 3 | 4 | 5 | | | V-1 | Zfp688 |
| 10904 | 3 | 4 | 5 | | | V-1 | Wdr6 | 10989 | 3 | 4 | 5 | | | V-1 | Zfp691 |
| 10905 | 3 | 4 | 5 | | | V-1 | Wdr60 | 10990 | 3 | 4 | 5 | | | V-1 | Zfp771 |
| 10906 | 3 | 4 | 5 | | | V-1 | Wdr61 | 10991 | 3 | 4 | 5 | | | V-1 | Zfp777 |
| 10907 | 3 | 4 | 5 | | | V-1 | Wdr62 | 10992 | 3 | 4 | 5 | | | V-1 | Zfp783 |
| 10908 | 3 | 4 | 5 | | | V-1 | Wdr75 | 10993 | 3 | 4 | 5 | | | V-1 | Zfp791 |
| 10909 | 3 | 4 | 5 | | | V-1 | Wdr83 | 10994 | 3 | 4 | 5 | | | V-1 | Zfp809 |
| 10910 | 3 | 4 | 5 | | | V-1 | Wdr83os | 10995 | 3 | 4 | 5 | | | V-1 | Zfp81 |
| 10911 | 3 | 4 | 5 | | | V-1 | Wdr86 | 10996 | 3 | 4 | 5 | | | V-1 | Zfp810 |
| 10912 | 3 | 4 | 5 | | | V-1 | Wdr92 | 10997 | 3 | 4 | 5 | | | V-1 | Zfp820 |
| 10913 | 3 | 4 | 5 | | | V-1 | Wfdc3 | 10998 | 3 | 4 | 5 | | | V-1 | Zfp866 |
| 10914 | 3 | 4 | 5 | | | V-1 | Wfikkn2 | 10999 | 3 | 4 | 5 | | | V-1 | Zfp871 |
| 10915 | 3 | 4 | 5 | | | V-1 | Whrn | 11000 | 3 | 4 | 5 | | | V-1 | Zfp9 |
| 10916 | 3 | 4 | 5 | | | V-1 | Wibg | 11001 | 3 | 4 | 5 | | | V-1 | Zfp90 |
| 10917 | 3 | 4 | 5 | | | V-1 | Wif1 | 11002 | 3 | 4 | 5 | | | V-1 | Zfp930 |
| 10918 | 3 | 4 | 5 | | | V-1 | Wipf1 | 11003 | 3 | 4 | 5 | | | V-1 | Zfp955a |
| 10919 | 3 | 4 | 5 | | | V-1 | Wipf3 | 11004 | 3 | 4 | 5 | | | V-1 | Zfp956 |
| 10920 | 3 | 4 | 5 | | | V-1 | Wnk2 | 11005 | 3 | 4 | 5 | | | V-1 | Zfp958 |
| 10921 | 3 | 4 | 5 | | | V-1 | Wnt2 | 11006 | 3 | 4 | 5 | | | V-1 | Zfp959 |
| 10922 | 3 | 4 | 5 | | | V-1 | Wnt4 | 11007 | 3 | 4 | 5 | | | V-1 | Zfp961 |
| 10923 | 3 | 4 | 5 | | | V-1 | Wscd1 | 11008 | 3 | 4 | 5 | | | V-1 | Zfpm1 |
| 10924 | 3 | 4 | 5 | | | V-1 | Xdh | 11009 | 3 | 4 | 5 | | | V-1 | Zkscan6 |
| 10925 | 3 | 4 | 5 | | | V-1 | Xkr5 | 11010 | 3 | 4 | 5 | | | V-1 | Zmpste24 |
| 10926 | 3 | 4 | 5 | | | V-1 | Xkr7 | 11011 | 3 | 4 | 5 | | | V-1 | Zmym6 |
| 10927 | 3 | 4 | 5 | | | V-1 | Xlr | 11012 | 3 | 4 | 5 | | | V-1 | Zmynd12 |
| 10928 | 3 | 4 | 5 | | | V-1 | Xlr4b | 11013 | 3 | 4 | 5 | | | V-1 | Zmynd19 |
| 10929 | 3 | 4 | 5 | | | V-1 | Xpnpep1 | 11014 | 3 | 4 | 5 | | | V-1 | Znfx1 |
| 10930 | 3 | 4 | 5 | | | V-1 | Xpo1 | 11015 | 3 | 4 | 5 | | | V-1 | Znhit2 |
| 10931 | 3 | 4 | 5 | | | V-1 | Xpo4 | 11016 | 3 | 4 | 5 | | | V-1 | Znhit3 |
| 10932 | 3 | 4 | 5 | | | V-1 | Xpo5 | 11017 | 3 | 4 | 5 | | | V-1 | Znrd1 |
| 10933 | 3 | 4 | 5 | | | V-1 | Xrcc2 | 11018 | 3 | 4 | 5 | | | V-1 | Zranb1 |
| 10934 | 3 | 4 | 5 | | | V-1 | Xrcc5 | 11019 | 3 | 4 | 5 | | | V-1 | Zscan25 |
| 10935 | 3 | 4 | 5 | | | V-1 | Yars | 11020 | 3 | 4 | 5 | | | V-1 | Zswim1 |
| 10936 | 3 | 4 | 5 | | | V-1 | Yars2 | 11021 | 3 | 4 | 5 | | | V-1 | Zwilch |
| 10937 | 3 | 4 | 5 | | | V-1 | Yif1b | 11022 | 3 | 4 | 5 | | | V-1 | Zwint |
| 10938 | 3 | 4 | 5 | | | V-1 | Yipf2 | 11023 | 3 | 4 | 5 | | | V-1 | Zzef1 |
| 10939 | 3 | 4 | 5 | | | V-1 | Yrdc | 11024 | 3 | 4 | | | | IV-2 | 1110028F18Rik |
| 10940 | 3 | 4 | 5 | | | V-1 | Ythdc2 | 11025 | 3 | 4 | | | | IV-2 | 1110036E04Rik |
| 10941 | 3 | 4 | 5 | | | V-1 | Yy2 | 11026 | 3 | 4 | | | | IV-2 | 1110037F02Rik |
| 10942 | 3 | 4 | 5 | | | V-1 | Zadh2 | 11027 | 3 | 4 | | | | IV-2 | 1600027J07Rik |
| 10943 | 3 | 4 | 5 | | | V-1 | Zbtb20 | 11028 | 3 | 4 | | | | IV-2 | 1600029O15Rik |
| 10944 | 3 | 4 | 5 | | | V-1 | Zbtb49 | 11029 | 3 | 4 | | | | IV-2 | 1700001F09Rik |
| 10945 | 3 | 4 | 5 | | | V-1 | Zbtb7a | 11030 | 3 | 4 | | | | IV-2 | 1700001K23Rik |
| 10946 | 3 | 4 | 5 | | | V-1 | Zbtb7b | 11031 | 3 | 4 | | | | IV-2 | 1700003C15Rik |
| 10947 | 3 | 4 | 5 | | | V-1 | Zbtb7c | 11032 | 3 | 4 | | | | IV-2 | 1700003G13Rik |
| 10948 | 3 | 4 | 5 | | | V-1 | Zc3h13 | 11033 | 3 | 4 | | | | IV-2 | 1700003P14Rik |
| 10949 | 3 | 4 | 5 | | | V-1 | Zc3h6 | 11034 | 3 | 4 | | | | IV-2 | 1700006F04Rik |
| 10950 | 3 | 4 | 5 | | | V-1 | Zc3hav1 | 11035 | 3 | 4 | | | | IV-2 | 1700007J10Rik |
| 10951 | 3 | 4 | 5 | | | V-1 | Zcchc2 | 11036 | 3 | 4 | | | | IV-2 | 1700008I05Rik |
| 10952 | 3 | 4 | 5 | | | V-1 | Zcchc3 | 11037 | 3 | 4 | | | | IV-2 | 1700008P02Rik |
| 10953 | 3 | 4 | 5 | | | V-1 | Zcchc6 | 11038 | 3 | 4 | | | | IV-2 | 1700009C05Rik |
| 10954 | 3 | 4 | 5 | | | V-1 | Zdhhc4 | 11039 | 3 | 4 | | | | IV-2 | 1700011A15Rik |
| 10955 | 3 | 4 | 5 | | | V-1 | Zfand2a | 11040 | 3 | 4 | | | | IV-2 | 1700011B04Rik |
| 10956 | 3 | 4 | 5 | | | V-1 | Zfand2b | 11041 | 3 | 4 | | | | IV-2 | 1700012P22Rik |
| 10957 | 3 | 4 | 5 | | | V-1 | Zfand5 | 11042 | 3 | 4 | | | | IV-2 | 1700013H16Rik |
| 10958 | 3 | 4 | 5 | | | V-1 | Zfp106 | 11043 | 3 | 4 | | | | IV-2 | 1700015G11Rik |
| 10959 | 3 | 4 | 5 | | | V-1 | Zfp112 | 11044 | 3 | 4 | | | | IV-2 | 1700016C15Rik |
| 10960 | 3 | 4 | 5 | | | V-1 | Zfp13 | 11045 | 3 | 4 | | | | IV-2 | 1700016D06Rik |
| 10961 | 3 | 4 | 5 | | | V-1 | Zfp217 | 11046 | 3 | 4 | | | | IV-2 | 1700016G22Rik |
| 10962 | 3 | 4 | 5 | | | V-1 | Zfp251 | 11047 | 3 | 4 | | | | IV-2 | 1700016L04Rik |

Fig. 43 - 66

| | | | | | | | | | | | | | |
|---|---|---|---|---|---|---|---|---|---|---|---|---|---|
| 11048 | 3 | 4 | | | | IV-2 | 1700016P04Rik | 11133 | 3 | 4 | | | IV-2 | 3110039M20Rik |
| 11049 | 3 | 4 | | | | IV-2 | 1700017D01Rik | 11134 | 3 | 4 | | | IV-2 | 3632454L22Rik |
| 11050 | 3 | 4 | | | | IV-2 | 1700018A04Rik | 11135 | 3 | 4 | | | IV-2 | 3830403N18Rik |
| 11051 | 3 | 4 | | | | IV-2 | 1700018G05Rik | 11136 | 3 | 4 | | | IV-2 | 4833417C18Rik |
| 11052 | 3 | 4 | | | | IV-2 | 1700019G24Rik | 11137 | 3 | 4 | | | IV-2 | 4833423E24Rik |
| 11053 | 3 | 4 | | | | IV-2 | 1700019O17Rik | 11138 | 3 | 4 | | | IV-2 | 4921507L20Rik |
| 11054 | 3 | 4 | | | | IV-2 | 1700020M21Rik | 11139 | 3 | 4 | | | IV-2 | 4921508D12Rik |
| 11055 | 3 | 4 | | | | IV-2 | 1700020N01Rik | 11140 | 3 | 4 | | | IV-2 | 4921509O07Rik |
| 11056 | 3 | 4 | | | | IV-2 | 1700022H16Rik | 11141 | 3 | 4 | | | IV-2 | 4921511C20Rik |
| 11057 | 3 | 4 | | | | IV-2 | 1700023E05Rik | 11142 | 3 | 4 | | | IV-2 | 4921511M17Rik |
| 11058 | 3 | 4 | | | | IV-2 | 1700024B18Rik | 11143 | 3 | 4 | | | IV-2 | 4921513I03Rik |
| 11059 | 3 | 4 | | | | IV-2 | 1700025C18Rik | 11144 | 3 | 4 | | | IV-2 | 4921515E04Rik |
| 11060 | 3 | 4 | | | | IV-2 | 1700025M24Rik | 11145 | 3 | 4 | | | IV-2 | 4921524J17Rik |
| 11061 | 3 | 4 | | | | IV-2 | 1700026D08Rik | 11146 | 3 | 4 | | | IV-2 | 4921524L21Rik |
| 11062 | 3 | 4 | | | | IV-2 | 1700026D11Rik | 11147 | 3 | 4 | | | IV-2 | 4921529L05Rik |
| 11063 | 3 | 4 | | | | IV-2 | 1700028E10Rik | 11148 | 3 | 4 | | | IV-2 | 4921534H16Rik |
| 11064 | 3 | 4 | | | | IV-2 | 1700028I16Rik | 11149 | 3 | 4 | | | IV-2 | 4921536K21Rik |
| 11065 | 3 | 4 | | | | IV-2 | 1700029I03Rik | 11150 | 3 | 4 | | | IV-2 | 4921539E11Rik |
| 11066 | 3 | 4 | | | | IV-2 | 1700029M20Rik | 11151 | 3 | 4 | | | IV-2 | 4922502H24Rik |
| 11067 | 3 | 4 | | | | IV-2 | 1700030O20Rik | 11152 | 3 | 4 | | | IV-2 | 4930401C15Rik |
| 11068 | 3 | 4 | | | | IV-2 | 1700034F02Rik | 11153 | 3 | 4 | | | IV-2 | 4930402K13Rik |
| 11069 | 3 | 4 | | | | IV-2 | 1700034I23Rik | 11154 | 3 | 4 | | | IV-2 | 4930404A05Rik |
| 11070 | 3 | 4 | | | | IV-2 | 1700034K08Rik | 11155 | 3 | 4 | | | IV-2 | 4930405A10Rik |
| 11071 | 3 | 4 | | | | IV-2 | 1700034P13Rik | 11156 | 3 | 4 | | | IV-2 | 4930405O11Rik |
| 11072 | 3 | 4 | | | | IV-2 | 1700041C23Rik | 11157 | 3 | 4 | | | IV-2 | 4930407I10Rik |
| 11073 | 3 | 4 | | | | IV-2 | 1700044C05Rik | 11158 | 3 | 4 | | | IV-2 | 4930412O23Rik |
| 11074 | 3 | 4 | | | | IV-2 | 1700046C09Rik | 11159 | 3 | 4 | | | IV-2 | 4930412O13Rik |
| 11075 | 3 | 4 | | | | IV-2 | 1700047E10Rik | 11160 | 3 | 4 | | | IV-2 | 4930413E15Rik |
| 11076 | 3 | 4 | | | | IV-2 | 1700047G03Rik | 11161 | 3 | 4 | | | IV-2 | 4930413F20Rik |
| 11077 | 3 | 4 | | | | IV-2 | 1700047I17Rik2 | 11162 | 3 | 4 | | | IV-2 | 4930415F15Rik |
| 11078 | 3 | 4 | | | | IV-2 | 1700049E15Rik | 11163 | 3 | 4 | | | IV-2 | 4930419G24Rik |
| 11079 | 3 | 4 | | | | IV-2 | 1700054O13Rik | 11164 | 3 | 4 | | | IV-2 | 4930423M02Rik |
| 11080 | 3 | 4 | | | | IV-2 | 1700057G04Rik | 11165 | 3 | 4 | | | IV-2 | 4930425K10Rik |
| 11081 | 3 | 4 | | | | IV-2 | 1700060C16Rik | 11166 | 3 | 4 | | | IV-2 | 4930428D18Rik |
| 11082 | 3 | 4 | | | | IV-2 | 1700063D05Rik | 11167 | 3 | 4 | | | IV-2 | 4930428G15Rik |
| 11083 | 3 | 4 | | | | IV-2 | 1700064J06Rik | 11168 | 3 | 4 | | | IV-2 | 4930429F11Rik |
| 11084 | 3 | 4 | | | | IV-2 | 1700064M15Rik | 11169 | 3 | 4 | | | IV-2 | 4930430D24Rik |
| 11085 | 3 | 4 | | | | IV-2 | 1700065I16Rik | 11170 | 3 | 4 | | | IV-2 | 4930430F21Rik |
| 11086 | 3 | 4 | | | | IV-2 | 1700065O20Rik | 11171 | 3 | 4 | | | IV-2 | 4930434J06Rik |
| 11087 | 3 | 4 | | | | IV-2 | 1700066N21Rik | 11172 | 3 | 4 | | | IV-2 | 4930438E09Rik |
| 11088 | 3 | 4 | | | | IV-2 | 1700069P05Rik | 11173 | 3 | 4 | | | IV-2 | 4930440C22Rik |
| 11089 | 3 | 4 | | | | IV-2 | 1700071K01Rik | 11174 | 3 | 4 | | | IV-2 | 4930442J19Rik |
| 11090 | 3 | 4 | | | | IV-2 | 1700073E17Rik | 11175 | 3 | 4 | | | IV-2 | 4930442L01Rik |
| 11091 | 3 | 4 | | | | IV-2 | 1700074P13Rik | 11176 | 3 | 4 | | | IV-2 | 4930444M15Rik |
| 11092 | 3 | 4 | | | | IV-2 | 1700080N15Rik | 11177 | 3 | 4 | | | IV-2 | 4930444P10Rik |
| 11093 | 3 | 4 | | | | IV-2 | 1700080O16Rik | 11178 | 3 | 4 | | | IV-2 | 4930447C04Rik |
| 11094 | 3 | 4 | | | | IV-2 | 1700084F23Rik | 11179 | 3 | 4 | | | IV-2 | 4930447K03Rik |
| 11095 | 3 | 4 | | | | IV-2 | 1700092C10Rik | 11180 | 3 | 4 | | | IV-2 | 4930447N08Rik |
| 11096 | 3 | 4 | | | | IV-2 | 1700094M24Rik | 11181 | 3 | 4 | | | IV-2 | 4930451I11Rik |
| 11097 | 3 | 4 | | | | IV-2 | 1700100L14Rik | 11182 | 3 | 4 | | | IV-2 | 4930452B06Rik |
| 11098 | 3 | 4 | | | | IV-2 | 1700104L18Rik | 11183 | 3 | 4 | | | IV-2 | 4930452N14Rik |
| 11099 | 3 | 4 | | | | IV-2 | 1700105P06Rik | 11184 | 3 | 4 | | | IV-2 | 4930453L07Rik |
| 11100 | 3 | 4 | | | | IV-2 | 1700109G14Rik | 11185 | 3 | 4 | | | IV-2 | 4930455D15Rik |
| 11101 | 3 | 4 | | | | IV-2 | 1700110C19Rik | 11186 | 3 | 4 | | | IV-2 | 4930456L15Rik |
| 11102 | 3 | 4 | | | | IV-2 | 1700110I01Rik | 11187 | 3 | 4 | | | IV-2 | 4930459L07Rik |
| 11103 | 3 | 4 | | | | IV-2 | 1700112E06Rik | 11188 | 3 | 4 | | | IV-2 | 4930461G14Rik |
| 11104 | 3 | 4 | | | | IV-2 | 1700112J05Rik | 11189 | 3 | 4 | | | IV-2 | 4930465K10Rik |
| 11105 | 3 | 4 | | | | IV-2 | 1700120E14Rik | 11190 | 3 | 4 | | | IV-2 | 4930467D21Rik |
| 11106 | 3 | 4 | | | | IV-2 | 1700120G07Rik | 11191 | 3 | 4 | | | IV-2 | 4930469G21Rik |
| 11107 | 3 | 4 | | | | IV-2 | 1700121L16Rik | 11192 | 3 | 4 | | | IV-2 | 4930473A02Rik |
| 11108 | 3 | 4 | | | | IV-2 | 1700123I01Rik | 11193 | 3 | 4 | | | IV-2 | 4930473O22Rik |
| 11109 | 3 | 4 | | | | IV-2 | 1700123O20Rik | 11194 | 3 | 4 | | | IV-2 | 4930474G06Rik |
| 11110 | 3 | 4 | | | | IV-2 | 1700125H03Rik | 11195 | 3 | 4 | | | IV-2 | 4930474N05Rik |
| 11111 | 3 | 4 | | | | IV-2 | 1700126H18Rik | 11196 | 3 | 4 | | | IV-2 | 4930478P22Rik |
| 11112 | 3 | 4 | | | | IV-2 | 1700128F08Rik | 11197 | 3 | 4 | | | IV-2 | 4930480K15Rik |
| 11113 | 3 | 4 | | | | IV-2 | 1810006J02Rik | 11198 | 3 | 4 | | | IV-2 | 4930483J18Rik |
| 11114 | 3 | 4 | | | | IV-2 | 1810007C17Rik | 11199 | 3 | 4 | | | IV-2 | 4930483K19Rik |
| 11115 | 3 | 4 | | | | IV-2 | 2010106E10Rik | 11200 | 3 | 4 | | | IV-2 | 4930483O08Rik |
| 11116 | 3 | 4 | | | | IV-2 | 2010109I03Rik | 11201 | 3 | 4 | | | IV-2 | 4930488B22Rik |
| 11117 | 3 | 4 | | | | IV-2 | 2010310C07Rik | 11202 | 3 | 4 | | | IV-2 | 4930500F04Rik |
| 11118 | 3 | 4 | | | | IV-2 | 2310002F09Rik | 11203 | 3 | 4 | | | IV-2 | 4930503H13Rik |
| 11119 | 3 | 4 | | | | IV-2 | 2310033P09Rik | 11204 | 3 | 4 | | | IV-2 | 4930504O13Rik |
| 11120 | 3 | 4 | | | | IV-2 | 2310035C23Rik | 11205 | 3 | 4 | | | IV-2 | 4930507D10Rik |
| 11121 | 3 | 4 | | | | IV-2 | 2310057N15Rik | 11206 | 3 | 4 | | | IV-2 | 4930513D17Rik |
| 11122 | 3 | 4 | | | | IV-2 | 2310065F04Rik | 11207 | 3 | 4 | | | IV-2 | 4930515B02Rik |
| 11123 | 3 | 4 | | | | IV-2 | 2310079G19Rik | 11208 | 3 | 4 | | | IV-2 | 4930515G16Rik |
| 11124 | 3 | 4 | | | | IV-2 | 2410007B07Rik | 11209 | 3 | 4 | | | IV-2 | 4930515L19Rik |
| 11125 | 3 | 4 | | | | IV-2 | 2410021H03Rik | 11210 | 3 | 4 | | | IV-2 | 4930517E11Rik |
| 11126 | 3 | 4 | | | | IV-2 | 2410114N07Rik | 11211 | 3 | 4 | | | IV-2 | 4930521E06Rik |
| 11127 | 3 | 4 | | | | IV-2 | 2410137M14Rik | 11212 | 3 | 4 | | | IV-2 | 4930522O17Rik |
| 11128 | 3 | 4 | | | | IV-2 | 2610207O16Rik | 11213 | 3 | 4 | | | IV-2 | 4930524C18Rik |
| 11129 | 3 | 4 | | | | IV-2 | 2810032G03Rik | 11214 | 3 | 4 | | | IV-2 | 4930524N10Rik |
| 11130 | 3 | 4 | | | | IV-2 | 2810404M03Rik | 11215 | 3 | 4 | | | IV-2 | 4930525O18Rik |
| 11131 | 3 | 4 | | | | IV-2 | 2900057B20Rik | 11216 | 3 | 4 | | | IV-2 | 4930525M21Rik |
| 11132 | 3 | 4 | | | | IV-2 | 2900097C17Rik | 11217 | 3 | 4 | | | IV-2 | 4930528D03Rik |

Fig. 43 - 67

| | | | | | | | |
|---|---|---|---|---|---|---|---|
| 11218 | 3 | 4 | | | | IV-2 | 4930529K09Rik |
| 11219 | 3 | 4 | | | | IV-2 | 4930529L06Rik |
| 11220 | 3 | 4 | | | | IV-2 | 4930539M17Rik |
| 11221 | 3 | 4 | | | | IV-2 | 4930539N22Rik |
| 11222 | 3 | 4 | | | | IV-2 | 4930542C21Rik |
| 11223 | 3 | 4 | | | | IV-2 | 4930544M13Rik |
| 11224 | 3 | 4 | | | | IV-2 | 4930545E07Rik |
| 11225 | 3 | 4 | | | | IV-2 | 4930545H06Rik |
| 11226 | 3 | 4 | | | | IV-2 | 4930545L23Rik |
| 11227 | 3 | 4 | | | | IV-2 | 4930548H24Rik |
| 11228 | 3 | 4 | | | | IV-2 | 4930548J01Rik |
| 11229 | 3 | 4 | | | | IV-2 | 4930549C01Rik |
| 11230 | 3 | 4 | | | | IV-2 | 4930549G23Rik |
| 11231 | 3 | 4 | | | | IV-2 | 4930550L24Rik |
| 11232 | 3 | 4 | | | | IV-2 | 4930552N02Rik |
| 11233 | 3 | 4 | | | | IV-2 | 4930555G01Rik |
| 11234 | 3 | 4 | | | | IV-2 | 4930556J02Rik |
| 11235 | 3 | 4 | | | | IV-2 | 4930557J02Rik |
| 11236 | 3 | 4 | | | | IV-2 | 4930563E18Rik |
| 11237 | 3 | 4 | | | | IV-2 | 4930567H17Rik |
| 11238 | 3 | 4 | | | | IV-2 | 4930567J20Rik |
| 11239 | 3 | 4 | | | | IV-2 | 4930567K20Rik |
| 11240 | 3 | 4 | | | | IV-2 | 4930570G19Rik |
| 11241 | 3 | 4 | | | | IV-2 | 4930572O03Rik |
| 11242 | 3 | 4 | | | | IV-2 | 4930583P06Rik |
| 11243 | 3 | 4 | | | | IV-2 | 4930592A05Rik |
| 11244 | 3 | 4 | | | | IV-2 | 4930593A02Rik |
| 11245 | 3 | 4 | | | | IV-2 | 4930593C16Rik |
| 11246 | 3 | 4 | | | | IV-2 | 4930596I21Rik |
| 11247 | 3 | 4 | | | | IV-2 | 4931402G19Rik |
| 11248 | 3 | 4 | | | | IV-2 | 4931406B18Rik |
| 11249 | 3 | 4 | | | | IV-2 | 4931419H13Rik |
| 11250 | 3 | 4 | | | | IV-2 | 4931429I11Rik |
| 11251 | 3 | 4 | | | | IV-2 | 4931429L15Rik |
| 11252 | 3 | 4 | | | | IV-2 | 4931429P17Rik |
| 11253 | 3 | 4 | | | | IV-2 | 4931431F19Rik |
| 11254 | 3 | 4 | | | | IV-2 | 4931440L10Rik |
| 11255 | 3 | 4 | | | | IV-2 | 4932411N23Rik |
| 11256 | 3 | 4 | | | | IV-2 | 4932412D23Rik |
| 11257 | 3 | 4 | | | | IV-2 | 4932413F04Rik |
| 11258 | 3 | 4 | | | | IV-2 | 4932414J04Rik |
| 11259 | 3 | 4 | | | | IV-2 | 4932416K20Rik |
| 11260 | 3 | 4 | | | | IV-2 | 4932438A13Rik |
| 11261 | 3 | 4 | | | | IV-2 | 4932443I19Rik |
| 11262 | 3 | 4 | | | | IV-2 | 4933400A11Rik |
| 11263 | 3 | 4 | | | | IV-2 | 4933400F21Rik |
| 11264 | 3 | 4 | | | | IV-2 | 4933401D09Rik |
| 11265 | 3 | 4 | | | | IV-2 | 4933402C06Rik |
| 11266 | 3 | 4 | | | | IV-2 | 4933402D24Rik |
| 11267 | 3 | 4 | | | | IV-2 | 4933402E13Rik |
| 11268 | 3 | 4 | | | | IV-2 | 4933402J15Rik |
| 11269 | 3 | 4 | | | | IV-2 | 4933402N03Rik |
| 11270 | 3 | 4 | | | | IV-2 | 4933403O08Rik |
| 11271 | 3 | 4 | | | | IV-2 | 4933404G15Rik |
| 11272 | 3 | 4 | | | | IV-2 | 4933404K08Rik |
| 11273 | 3 | 4 | | | | IV-2 | 4933405E24Rik |
| 11274 | 3 | 4 | | | | IV-2 | 4933406O20Rik |
| 11275 | 3 | 4 | | | | IV-2 | 4933406G16Rik |
| 11276 | 3 | 4 | | | | IV-2 | 4933406M09Rik |
| 11277 | 3 | 4 | | | | IV-2 | 4933408N05Rik |
| 11278 | 3 | 4 | | | | IV-2 | 4933411E08Rik |
| 11279 | 3 | 4 | | | | IV-2 | 4933411G11Rik |
| 11280 | 3 | 4 | | | | IV-2 | 4933411K20Rik |
| 11281 | 3 | 4 | | | | IV-2 | 4933412E24Rik |
| 11282 | 3 | 4 | | | | IV-2 | 4933413G19Rik |
| 11283 | 3 | 4 | | | | IV-2 | 4933416C03Rik |
| 11284 | 3 | 4 | | | | IV-2 | 4933416E03Rik |
| 11285 | 3 | 4 | | | | IV-2 | 4933417A18Rik |
| 11286 | 3 | 4 | | | | IV-2 | 4933417O13Rik |
| 11287 | 3 | 4 | | | | IV-2 | 4933427D14Rik |
| 11288 | 3 | 4 | | | | IV-2 | 4933427E13Rik |
| 11289 | 3 | 4 | | | | IV-2 | 4933429O19Rik |
| 11290 | 3 | 4 | | | | IV-2 | 4933430M04Rik |
| 11291 | 3 | 4 | | | | IV-2 | 4933431G14Rik |
| 11292 | 3 | 4 | | | | IV-2 | 4933433G08Rik |
| 11293 | 3 | 4 | | | | IV-2 | 4933433G15Rik |
| 11294 | 3 | 4 | | | | IV-2 | 4933433G19Rik |
| 11295 | 3 | 4 | | | | IV-2 | 4933433H22Rik |
| 11296 | 3 | 4 | | | | IV-2 | 4933434E20Rik |
| 11297 | 3 | 4 | | | | IV-2 | 4933434J20Rik |
| 11298 | 3 | 4 | | | | IV-2 | 4933438B17Rik |
| 11299 | 3 | 4 | | | | IV-2 | 4933440M02Rik |
| 11300 | 3 | 4 | | | | IV-2 | 5031410I06Rik |
| 11301 | 3 | 4 | | | | IV-2 | 5031426D15Rik |
| 11302 | 3 | 4 | | | | IV-2 | 5031434C07Rik |
| 11303 | 3 | 4 | | | | IV-2 | 5033404E19Rik |
| 11304 | 3 | 4 | | | | IV-2 | 5033406O09Rik |
| 11305 | 3 | 4 | | | | IV-2 | 5430421F17Rik |
| 11306 | 3 | 4 | | | | IV-2 | 5530401A14Rik |
| 11307 | 3 | 4 | | | | IV-2 | 5730412P04Rik |
| 11308 | 3 | 4 | | | | IV-2 | 5730488B01Rik |
| 11309 | 3 | 4 | | | | IV-2 | 5730507C01Rik |
| 11310 | 3 | 4 | | | | IV-2 | 6030440G07Rik |
| 11311 | 3 | 4 | | | | IV-2 | 6030498E09Rik |
| 11312 | 3 | 4 | | | | IV-2 | 6330403K07Rik |
| 11313 | 3 | 4 | | | | IV-2 | 6430411K18Rik |
| 11314 | 3 | 4 | | | | IV-2 | 6430503K07Rik |
| 11315 | 3 | 4 | | | | IV-2 | 7420700N18Rik |
| 11316 | 3 | 4 | | | | IV-2 | 8030423J24Rik |
| 11317 | 3 | 4 | | | | IV-2 | 8030442B05Rik |
| 11318 | 3 | 4 | | | | IV-2 | 8430423G03Rik |
| 11319 | 3 | 4 | | | | IV-2 | 8430436N08Rik |
| 11320 | 3 | 4 | | | | IV-2 | 8430437L04Rik |
| 11321 | 3 | 4 | | | | IV-2 | 9030612E09Rik |
| 11322 | 3 | 4 | | | | IV-2 | 9030624J02Rik |
| 11323 | 3 | 4 | | | | IV-2 | 9230112D13Rik |
| 11324 | 3 | 4 | | | | IV-2 | 9230112J17Rik |
| 11325 | 3 | 4 | | | | IV-2 | 9330182O14Rik |
| 11326 | 3 | 4 | | | | IV-2 | 9430007A20Rik |
| 11327 | 3 | 4 | | | | IV-2 | 9430041J12Rik |
| 11328 | 3 | 4 | | | | IV-2 | 9430060I03Rik |
| 11329 | 3 | 4 | | | | IV-2 | 9530003J23Rik |
| 11330 | 3 | 4 | | | | IV-2 | 9530052E02Rik |
| 11331 | 3 | 4 | | | | IV-2 | 9530053A07Rik |
| 11332 | 3 | 4 | | | | IV-2 | A1bg |
| 11333 | 3 | 4 | | | | IV-2 | A230056J06Rik |
| 11334 | 3 | 4 | | | | IV-2 | A230072E10Rik |
| 11335 | 3 | 4 | | | | IV-2 | A330021E22Rik |
| 11336 | 3 | 4 | | | | IV-2 | A330033J07Rik |
| 11337 | 3 | 4 | | | | IV-2 | A330048O09Rik |
| 11338 | 3 | 4 | | | | IV-2 | A330049N07Rik |
| 11339 | 3 | 4 | | | | IV-2 | A330050F15Rik |
| 11340 | 3 | 4 | | | | IV-2 | A330076H08Rik |
| 11341 | 3 | 4 | | | | IV-2 | A330093E20Rik |
| 11342 | 3 | 4 | | | | IV-2 | A430089I19Rik |
| 11343 | 3 | 4 | | | | IV-2 | A4galt |
| 11344 | 3 | 4 | | | | IV-2 | A530006G24Rik |
| 11345 | 3 | 4 | | | | IV-2 | A530053G22Rik |
| 11346 | 3 | 4 | | | | IV-2 | A630010A05Rik |
| 11347 | 3 | 4 | | | | IV-2 | A630072M18Rik |
| 11348 | 3 | 4 | | | | IV-2 | A630073D07Rik |
| 11349 | 3 | 4 | | | | IV-2 | A730006G06Rik |
| 11350 | 3 | 4 | | | | IV-2 | A730018C14Rik |
| 11351 | 3 | 4 | | | | IV-2 | A730090N16Rik |
| 11352 | 3 | 4 | | | | IV-2 | A830018L16Rik |
| 11353 | 3 | 4 | | | | IV-2 | A830019L24Rik |
| 11354 | 3 | 4 | | | | IV-2 | A830052D11Rik |
| 11355 | 3 | 4 | | | | IV-2 | A830082K12Rik |
| 11356 | 3 | 4 | | | | IV-2 | A930017M01Rik |
| 11357 | 3 | 4 | | | | IV-2 | Aamdc |
| 11358 | 3 | 4 | | | | IV-2 | Abcb7 |
| 11359 | 3 | 4 | | | | IV-2 | Abcc8 |
| 11360 | 3 | 4 | | | | IV-2 | Acbd3 |
| 11361 | 3 | 4 | | | | IV-2 | Ace3 |
| 11362 | 3 | 4 | | | | IV-2 | Acsl3 |
| 11363 | 3 | 4 | | | | IV-2 | Acss2os |
| 11364 | 3 | 4 | | | | IV-2 | Actn1 |
| 11365 | 3 | 4 | | | | IV-2 | Actn4 |
| 11366 | 3 | 4 | | | | IV-2 | Actr1a |
| 11367 | 3 | 4 | | | | IV-2 | Acvr2a |
| 11368 | 3 | 4 | | | | IV-2 | Adam15 |
| 11369 | 3 | 4 | | | | IV-2 | Adam23 |
| 11370 | 3 | 4 | | | | IV-2 | Adam25 |
| 11371 | 3 | 4 | | | | IV-2 | Adam26a |
| 11372 | 3 | 4 | | | | IV-2 | Adam26b |
| 11373 | 3 | 4 | | | | IV-2 | Adam3 |
| 11374 | 3 | 4 | | | | IV-2 | Adam30 |
| 11375 | 3 | 4 | | | | IV-2 | Adam32 |
| 11376 | 3 | 4 | | | | IV-2 | Adam33 |
| 11377 | 3 | 4 | | | | IV-2 | Adam39 |
| 11378 | 3 | 4 | | | | IV-2 | Adam4 |
| 11379 | 3 | 4 | | | | IV-2 | Adam6a |
| 11380 | 3 | 4 | | | | IV-2 | Adam9 |
| 11381 | 3 | 4 | | | | IV-2 | Adamts10 |
| 11382 | 3 | 4 | | | | IV-2 | Adamts6 |
| 11383 | 3 | 4 | | | | IV-2 | Adcy7 |
| 11384 | 3 | 4 | | | | IV-2 | Add3 |
| 11385 | 3 | 4 | | | | IV-2 | Adh7 |
| 11386 | 3 | 4 | | | | IV-2 | Af357426 |
| 11387 | 3 | 4 | | | | IV-2 | AF529169 |

Fig. 43 - 68

| | | | | | | | | |
|---|---|---|---|---|---|---|---|---|
| 11388 | 3 | 4 | | | | | IV-2 | Afap1 |
| 11389 | 3 | 4 | | | | | IV-2 | Afap1l1 |
| 11390 | 3 | 4 | | | | | IV-2 | Afap1l2 |
| 11391 | 3 | 4 | | | | | IV-2 | Aff2 |
| 11392 | 3 | 4 | | | | | IV-2 | Agfg1 |
| 11393 | 3 | 4 | | | | | IV-2 | Agtr1b |
| 11394 | 3 | 4 | | | | | IV-2 | AI182371 |
| 11395 | 3 | 4 | | | | | IV-2 | AI854517 |
| 11396 | 3 | 4 | | | | | IV-2 | Aida |
| 11397 | 3 | 4 | | | | | IV-2 | Aifm1 |
| 11398 | 3 | 4 | | | | | IV-2 | Akap8l |
| 11399 | 3 | 4 | | | | | IV-2 | Akt1 |
| 11400 | 3 | 4 | | | | | IV-2 | Alpi |
| 11401 | 3 | 4 | | | | | IV-2 | Alx3 |
| 11402 | 3 | 4 | | | | | IV-2 | Alyref2 |
| 11403 | 3 | 4 | | | | | IV-2 | Ambp |
| 11404 | 3 | 4 | | | | | IV-2 | Amz2 |
| 11405 | 3 | 4 | | | | | IV-2 | Angpt4 |
| 11406 | 3 | 4 | | | | | IV-2 | Ankib1 |
| 11407 | 3 | 4 | | | | | IV-2 | Ankle2 |
| 11408 | 3 | 4 | | | | | IV-2 | Ankrd36 |
| 11409 | 3 | 4 | | | | | IV-2 | Ankrd45 |
| 11410 | 3 | 4 | | | | | IV-2 | Ankrd7 |
| 11411 | 3 | 4 | | | | | IV-2 | Ano9 |
| 11412 | 3 | 4 | | | | | IV-2 | Anp32a |
| 11413 | 3 | 4 | | | | | IV-2 | Api5 |
| 11414 | 3 | 4 | | | | | IV-2 | Aqp8 |
| 11415 | 3 | 4 | | | | | IV-2 | Arhgap33 |
| 11416 | 3 | 4 | | | | | IV-2 | Arhgap42 |
| 11417 | 3 | 4 | | | | | IV-2 | Arhgef7 |
| 11418 | 3 | 4 | | | | | IV-2 | Arih2 |
| 11419 | 3 | 4 | | | | | IV-2 | Arl16 |
| 11420 | 3 | 4 | | | | | IV-2 | Armc4 |
| 11421 | 3 | 4 | | | | | IV-2 | Armcx1 |
| 11422 | 3 | 4 | | | | | IV-2 | Ash2l |
| 11423 | 3 | 4 | | | | | IV-2 | Asnsd1 |
| 11424 | 3 | 4 | | | | | IV-2 | Aspn |
| 11425 | 3 | 4 | | | | | IV-2 | Asxl3 |
| 11426 | 3 | 4 | | | | | IV-2 | Atg16l1 |
| 11427 | 3 | 4 | | | | | IV-2 | Atp11a |
| 11428 | 3 | 4 | | | | | IV-2 | Atp5f1 |
| 11429 | 3 | 4 | | | | | IV-2 | Atp6v1b1 |
| 11430 | 3 | 4 | | | | | IV-2 | AU019823 |
| 11431 | 3 | 4 | | | | | IV-2 | AU022751 |
| 11432 | 3 | 4 | | | | | IV-2 | AU022793 |
| 11433 | 3 | 4 | | | | | IV-2 | AU023762 |
| 11434 | 3 | 4 | | | | | IV-2 | Aurka |
| 11435 | 3 | 4 | | | | | IV-2 | Avpr1a |
| 11436 | 3 | 4 | | | | | IV-2 | Awat1 |
| 11437 | 3 | 4 | | | | | IV-2 | Aym1 |
| 11438 | 3 | 4 | | | | | IV-2 | Azi2 |
| 11439 | 3 | 4 | | | | | IV-2 | B020004J07Rik |
| 11440 | 3 | 4 | | | | | IV-2 | B130024G19Rik |
| 11441 | 3 | 4 | | | | | IV-2 | B230112J18Rik |
| 11442 | 3 | 4 | | | | | IV-2 | B230214G05Rik |
| 11443 | 3 | 4 | | | | | IV-2 | B230312C02Rik |
| 11444 | 3 | 4 | | | | | IV-2 | B4galt2 |
| 11445 | 3 | 4 | | | | | IV-2 | Batf3 |
| 11446 | 3 | 4 | | | | | IV-2 | BB557941 |
| 11447 | 3 | 4 | | | | | IV-2 | Bbip1 |
| 11448 | 3 | 4 | | | | | IV-2 | BC033916 |
| 11449 | 3 | 4 | | | | | IV-2 | BC035044 |
| 11450 | 3 | 4 | | | | | IV-2 | BC037034 |
| 11451 | 3 | 4 | | | | | IV-2 | BC048403 |
| 11452 | 3 | 4 | | | | | IV-2 | BC048602 |
| 11453 | 3 | 4 | | | | | IV-2 | BC061194 |
| 11454 | 3 | 4 | | | | | IV-2 | BC061195 |
| 11455 | 3 | 4 | | | | | IV-2 | BC061237 |
| 11456 | 3 | 4 | | | | | IV-2 | BC117090 |
| 11457 | 3 | 4 | | | | | IV-2 | Bcar1 |
| 11458 | 3 | 4 | | | | | IV-2 | Bhlha9 |
| 11459 | 3 | 4 | | | | | IV-2 | Bmx |
| 11460 | 3 | 4 | | | | | IV-2 | Bpifb3 |
| 11461 | 3 | 4 | | | | | IV-2 | Bpifb4 |
| 11462 | 3 | 4 | | | | | IV-2 | Bpifb5 |
| 11463 | 3 | 4 | | | | | IV-2 | Bpifb9b |
| 11464 | 3 | 4 | | | | | IV-2 | Bpifc |
| 11465 | 3 | 4 | | | | | IV-2 | Bpnt1 |
| 11466 | 3 | 4 | | | | | IV-2 | Brap |
| 11467 | 3 | 4 | | | | | IV-2 | Brat1 |
| 11468 | 3 | 4 | | | | | IV-2 | Btaf1 |
| 11469 | 3 | 4 | | | | | IV-2 | Btbd1 |
| 11470 | 3 | 4 | | | | | IV-2 | Btbd17 |
| 11471 | 3 | 4 | | | | | IV-2 | Btnl10 |
| 11472 | 3 | 4 | | | | | IV-2 | Btnl5-ps |
| 11473 | 3 | 4 | | | | | IV-2 | Bub1 |
| 11474 | 3 | 4 | | | | | IV-2 | C030039L03Rik |
| 11475 | 3 | 4 | | | | | IV-2 | C130021I20Rik |
| 11476 | 3 | 4 | | | | | IV-2 | C130036L24Rik |
| 11477 | 3 | 4 | | | | | IV-2 | C130071C03Rik |
| 11478 | 3 | 4 | | | | | IV-2 | C330024C12Rik |
| 11479 | 3 | 4 | | | | | IV-2 | C430002E04Rik |
| 11480 | 3 | 4 | | | | | IV-2 | C430002N11Rik |
| 11481 | 3 | 4 | | | | | IV-2 | C87977 |
| 11482 | 3 | 4 | | | | | IV-2 | C8a |
| 11483 | 3 | 4 | | | | | IV-2 | C8b |
| 11484 | 3 | 4 | | | | | IV-2 | Cacna1a |
| 11485 | 3 | 4 | | | | | IV-2 | Cacng8 |
| 11486 | 3 | 4 | | | | | IV-2 | Cactin |
| 11487 | 3 | 4 | | | | | IV-2 | Calm5 |
| 11488 | 3 | 4 | | | | | IV-2 | Calr4 |
| 11489 | 3 | 4 | | | | | IV-2 | Carkd |
| 11490 | 3 | 4 | | | | | IV-2 | Catsper2 |
| 11491 | 3 | 4 | | | | | IV-2 | Catsperb |
| 11492 | 3 | 4 | | | | | IV-2 | Cbfb |
| 11493 | 3 | 4 | | | | | IV-2 | Ccdc117 |
| 11494 | 3 | 4 | | | | | IV-2 | Ccdc150 |
| 11495 | 3 | 4 | | | | | IV-2 | Ccdc151 |
| 11496 | 3 | 4 | | | | | IV-2 | Ccdc183 |
| 11497 | 3 | 4 | | | | | IV-2 | Ccdc24 |
| 11498 | 3 | 4 | | | | | IV-2 | Ccdc27 |
| 11499 | 3 | 4 | | | | | IV-2 | Ccdc33 |
| 11500 | 3 | 4 | | | | | IV-2 | Ccdc42 |
| 11501 | 3 | 4 | | | | | IV-2 | Ccdc50 |
| 11502 | 3 | 4 | | | | | IV-2 | Ccdc51 |
| 11503 | 3 | 4 | | | | | IV-2 | Ccdc65 |
| 11504 | 3 | 4 | | | | | IV-2 | Ccdc78 |
| 11505 | 3 | 4 | | | | | IV-2 | Ccdc83 |
| 11506 | 3 | 4 | | | | | IV-2 | Ccdc87 |
| 11507 | 3 | 4 | | | | | IV-2 | Ccdc94 |
| 11508 | 3 | 4 | | | | | IV-2 | Ccnl1 |
| 11509 | 3 | 4 | | | | | IV-2 | Cd160 |
| 11510 | 3 | 4 | | | | | IV-2 | Cdh15 |
| 11511 | 3 | 4 | | | | | IV-2 | Cdh22 |
| 11512 | 3 | 4 | | | | | IV-2 | Cdipt |
| 11513 | 3 | 4 | | | | | IV-2 | Cdk11b |
| 11514 | 3 | 4 | | | | | IV-2 | Cdk20 |
| 11515 | 3 | 4 | | | | | IV-2 | Cdx1 |
| 11516 | 3 | 4 | | | | | IV-2 | Ceacam12 |
| 11517 | 3 | 4 | | | | | IV-2 | Ceacam14 |
| 11518 | 3 | 4 | | | | | IV-2 | Ceacam18 |
| 11519 | 3 | 4 | | | | | IV-2 | Ceacam2 |
| 11520 | 3 | 4 | | | | | IV-2 | Ceacam20 |
| 11521 | 3 | 4 | | | | | IV-2 | Ceacam3 |
| 11522 | 3 | 4 | | | | | IV-2 | Cebpd |
| 11523 | 3 | 4 | | | | | IV-2 | Celsr3 |
| 11524 | 3 | 4 | | | | | IV-2 | Ces2b |
| 11525 | 3 | 4 | | | | | IV-2 | Cetn2 |
| 11526 | 3 | 4 | | | | | IV-2 | Cfc1 |
| 11527 | 3 | 4 | | | | | IV-2 | Ch25h |
| 11528 | 3 | 4 | | | | | IV-2 | Chchd5 |
| 11529 | 3 | 4 | | | | | IV-2 | Chm |
| 11530 | 3 | 4 | | | | | IV-2 | Chrna1 |
| 11531 | 3 | 4 | | | | | IV-2 | Chrnd |
| 11532 | 3 | 4 | | | | | IV-2 | Chuk |
| 11533 | 3 | 4 | | | | | IV-2 | Clcn4-2 |
| 11534 | 3 | 4 | | | | | IV-2 | Clec3a |
| 11535 | 3 | 4 | | | | | IV-2 | Clrn3 |
| 11536 | 3 | 4 | | | | | IV-2 | Cmip |
| 11537 | 3 | 4 | | | | | IV-2 | Cnrip1 |
| 11538 | 3 | 4 | | | | | IV-2 | Cntnap1 |
| 11539 | 3 | 4 | | | | | IV-2 | Cntnap3 |
| 11540 | 3 | 4 | | | | | IV-2 | Cntnap5a |
| 11541 | 3 | 4 | | | | | IV-2 | Coa5 |
| 11542 | 3 | 4 | | | | | IV-2 | Col24a1 |
| 11543 | 3 | 4 | | | | | IV-2 | Col5a2 |
| 11544 | 3 | 4 | | | | | IV-2 | Colgalt2 |
| 11545 | 3 | 4 | | | | | IV-2 | Commd10 |
| 11546 | 3 | 4 | | | | | IV-2 | Cox16 |
| 11547 | 3 | 4 | | | | | IV-2 | Cpne3 |
| 11548 | 3 | 4 | | | | | IV-2 | Cpsf2 |
| 11549 | 3 | 4 | | | | | IV-2 | Crispld1 |
| 11550 | 3 | 4 | | | | | IV-2 | Crkl |
| 11551 | 3 | 4 | | | | | IV-2 | Crtc3 |
| 11552 | 3 | 4 | | | | | IV-2 | Cryba1 |
| 11553 | 3 | 4 | | | | | IV-2 | Cryba2 |
| 11554 | 3 | 4 | | | | | IV-2 | Crygs |
| 11555 | 3 | 4 | | | | | IV-2 | Cryz |
| 11556 | 3 | 4 | | | | | IV-2 | Cryzl1 |
| 11557 | 3 | 4 | | | | | IV-2 | Cs |

Fig. 43 - 69

| | | | | | | | |
|---|---|---|---|---|---|---|---|
| 11558 | 3 | 4 | | | | IV-2 | Csmd1 |
| 11559 | 3 | 4 | | | | IV-2 | Csn2 |
| 11560 | 3 | 4 | | | | IV-2 | Csn3 |
| 11561 | 3 | 4 | | | | IV-2 | Csta1 |
| 11562 | 3 | 4 | | | | IV-2 | Ctc1 |
| 11563 | 3 | 4 | | | | IV-2 | Ctcf |
| 11564 | 3 | 4 | | | | IV-2 | Ctsd |
| 11565 | 3 | 4 | | | | IV-2 | Cttnbp2 |
| 11566 | 3 | 4 | | | | IV-2 | Cxx1a |
| 11567 | 3 | 4 | | | | IV-2 | Cxxc4 |
| 11568 | 3 | 4 | | | | IV-2 | Cyp11b2 |
| 11569 | 3 | 4 | | | | IV-2 | Cyp2c38 |
| 11570 | 3 | 4 | | | | IV-2 | Cyp2c50 |
| 11571 | 3 | 4 | | | | IV-2 | Cyp2c53-ps |
| 11572 | 3 | 4 | | | | IV-2 | Cyp2c55 |
| 11573 | 3 | 4 | | | | IV-2 | Cyp2c65 |
| 11574 | 3 | 4 | | | | IV-2 | Cyp2d13 |
| 11575 | 3 | 4 | | | | IV-2 | Cyp2t4 |
| 11576 | 3 | 4 | | | | IV-2 | Cyp3a16 |
| 11577 | 3 | 4 | | | | IV-2 | Cyp3a41a |
| 11578 | 3 | 4 | | | | IV-2 | Cyp3a44 |
| 11579 | 3 | 4 | | | | IV-2 | Cyp4a29 |
| 11580 | 3 | 4 | | | | IV-2 | Cyp4f14 |
| 11581 | 3 | 4 | | | | IV-2 | Cypt15 |
| 11582 | 3 | 4 | | | | IV-2 | Cypt7 |
| 11583 | 3 | 4 | | | | IV-2 | Cyth1 |
| 11584 | 3 | 4 | | | | IV-2 | D030045P18Rik |
| 11585 | 3 | 4 | | | | IV-2 | D030047H15Rik |
| 11586 | 3 | 4 | | | | IV-2 | D14Ertd670e |
| 11587 | 3 | 4 | | | | IV-2 | D17Wsu104e |
| 11588 | 3 | 4 | | | | IV-2 | D330050G23Rik |
| 11589 | 3 | 4 | | | | IV-2 | D430019H16Rik |
| 11590 | 3 | 4 | | | | IV-2 | D630010B17Rik |
| 11591 | 3 | 4 | | | | IV-2 | D630013N20Rik |
| 11592 | 3 | 4 | | | | IV-2 | D630033O11Rik |
| 11593 | 3 | 4 | | | | IV-2 | D730001G18Rik |
| 11594 | 3 | 4 | | | | IV-2 | D730048I06Rik |
| 11595 | 3 | 4 | | | | IV-2 | D830032E09Rik |
| 11596 | 3 | 4 | | | | IV-2 | Dab2ip |
| 11597 | 3 | 4 | | | | IV-2 | Dbn1 |
| 11598 | 3 | 4 | | | | IV-2 | Dbndd2 |
| 11599 | 3 | 4 | | | | IV-2 | Dcaf12l2 |
| 11600 | 3 | 4 | | | | IV-2 | Dctn4 |
| 11601 | 3 | 4 | | | | IV-2 | Ddx49 |
| 11602 | 3 | 4 | | | | IV-2 | Defa-ps1 |
| 11603 | 3 | 4 | | | | IV-2 | Defa-rs1 |
| 11604 | 3 | 4 | | | | IV-2 | Defa-rs7 |
| 11605 | 3 | 4 | | | | IV-2 | Defb10 |
| 11606 | 3 | 4 | | | | IV-2 | Defb12 |
| 11607 | 3 | 4 | | | | IV-2 | Defb13 |
| 11608 | 3 | 4 | | | | IV-2 | Defb14 |
| 11609 | 3 | 4 | | | | IV-2 | Defb18 |
| 11610 | 3 | 4 | | | | IV-2 | Defb20 |
| 11611 | 3 | 4 | | | | IV-2 | Defb3 |
| 11612 | 3 | 4 | | | | IV-2 | Defb30 |
| 11613 | 3 | 4 | | | | IV-2 | Defb33 |
| 11614 | 3 | 4 | | | | IV-2 | Defb34 |
| 11615 | 3 | 4 | | | | IV-2 | Defb35 |
| 11616 | 3 | 4 | | | | IV-2 | Defb41 |
| 11617 | 3 | 4 | | | | IV-2 | Defb50 |
| 11618 | 3 | 4 | | | | IV-2 | Defb7 |
| 11619 | 3 | 4 | | | | IV-2 | Degs1 |
| 11620 | 3 | 4 | | | | IV-2 | Dennd1a |
| 11621 | 3 | 4 | | | | IV-2 | Dhdds |
| 11622 | 3 | 4 | | | | IV-2 | Dll3 |
| 11623 | 3 | 4 | | | | IV-2 | Dlx6as2 |
| 11624 | 3 | 4 | | | | IV-2 | Dnah17 |
| 11625 | 3 | 4 | | | | IV-2 | Dnah7b |
| 11626 | 3 | 4 | | | | IV-2 | Dnaja3 |
| 11627 | 3 | 4 | | | | IV-2 | Dnajc13 |
| 11628 | 3 | 4 | | | | IV-2 | Dnajc24 |
| 11629 | 3 | 4 | | | | IV-2 | Dnajc5g |
| 11630 | 3 | 4 | | | | IV-2 | Dnm2 |
| 11631 | 3 | 4 | | | | IV-2 | Dpy19l2 |
| 11632 | 3 | 4 | | | | IV-2 | Dpy19l3 |
| 11633 | 3 | 4 | | | | IV-2 | DQ267101 |
| 11634 | 3 | 4 | | | | IV-2 | Dram2 |
| 11635 | 3 | 4 | | | | IV-2 | Dthd1 |
| 11636 | 3 | 4 | | | | IV-2 | Dydc1 |
| 11637 | 3 | 4 | | | | IV-2 | Dync1i2 |
| 11638 | 3 | 4 | | | | IV-2 | Dync2h1 |
| 11639 | 3 | 4 | | | | IV-2 | E030019B13Rik |
| 11640 | 3 | 4 | | | | IV-2 | E030018N17Rik |
| 11641 | 3 | 4 | | | | IV-2 | E130114P18Rik |
| 11642 | 3 | 4 | | | | IV-2 | E2f4 |
| 11643 | 3 | 4 | | | | IV-2 | E330034G19Rik |
| 11644 | 3 | 4 | | | | IV-2 | E430025E21Rik |
| 11645 | 3 | 4 | | | | IV-2 | Ebf2 |
| 11646 | 3 | 4 | | | | IV-2 | Edc4 |
| 11647 | 3 | 4 | | | | IV-2 | Efcab8 |
| 11648 | 3 | 4 | | | | IV-2 | Eif4enif1 |
| 11649 | 3 | 4 | | | | IV-2 | Eng |
| 11650 | 3 | 4 | | | | IV-2 | Epgn |
| 11651 | 3 | 4 | | | | IV-2 | Ergic3 |
| 11652 | 3 | 4 | | | | IV-2 | Esp3 |
| 11653 | 3 | 4 | | | | IV-2 | Esp31 |
| 11654 | 3 | 4 | | | | IV-2 | Esp34 |
| 11655 | 3 | 4 | | | | IV-2 | Esp36 |
| 11656 | 3 | 4 | | | | IV-2 | Esp38 |
| 11657 | 3 | 4 | | | | IV-2 | Esp4 |
| 11658 | 3 | 4 | | | | IV-2 | Esp5 |
| 11659 | 3 | 4 | | | | IV-2 | Esp6 |
| 11660 | 3 | 4 | | | | IV-2 | Espnl |
| 11661 | 3 | 4 | | | | IV-2 | Esr1 |
| 11662 | 3 | 4 | | | | IV-2 | Esx1 |
| 11663 | 3 | 4 | | | | IV-2 | Exosc4 |
| 11664 | 3 | 4 | | | | IV-2 | F8 |
| 11665 | 3 | 4 | | | | IV-2 | Fabp2 |
| 11666 | 3 | 4 | | | | IV-2 | Faf1 |
| 11667 | 3 | 4 | | | | IV-2 | Fam133b |
| 11668 | 3 | 4 | | | | IV-2 | Fam155a |
| 11669 | 3 | 4 | | | | IV-2 | Fam161b |
| 11670 | 3 | 4 | | | | IV-2 | Fam169a |
| 11671 | 3 | 4 | | | | IV-2 | Fam19a2 |
| 11672 | 3 | 4 | | | | IV-2 | Fam19a4 |
| 11673 | 3 | 4 | | | | IV-2 | Fam21 |
| 11674 | 3 | 4 | | | | IV-2 | Fam53a |
| 11675 | 3 | 4 | | | | IV-2 | Fam58b |
| 11676 | 3 | 4 | | | | IV-2 | Fam72a |
| 11677 | 3 | 4 | | | | IV-2 | Fam76b |
| 11678 | 3 | 4 | | | | IV-2 | Fancm |
| 11679 | 3 | 4 | | | | IV-2 | Fars2 |
| 11680 | 3 | 4 | | | | IV-2 | Farsa |
| 11681 | 3 | 4 | | | | IV-2 | Fbxw17 |
| 11682 | 3 | 4 | | | | IV-2 | Fbxw19 |
| 11683 | 3 | 4 | | | | IV-2 | Fbxw2 |
| 11684 | 3 | 4 | | | | IV-2 | Fbxw20 |
| 11685 | 3 | 4 | | | | IV-2 | Fbxw21 |
| 11686 | 3 | 4 | | | | IV-2 | Fbxw24 |
| 11687 | 3 | 4 | | | | IV-2 | Fbxw26 |
| 11688 | 3 | 4 | | | | IV-2 | Fbxw5 |
| 11689 | 3 | 4 | | | | IV-2 | Fbxw8 |
| 11690 | 3 | 4 | | | | IV-2 | Fgd1 |
| 11691 | 3 | 4 | | | | IV-2 | Fgf5 |
| 11692 | 3 | 4 | | | | IV-2 | Fgfbp1 |
| 11693 | 3 | 4 | | | | IV-2 | Fgfr1op2 |
| 11694 | 3 | 4 | | | | IV-2 | Ficd |
| 11695 | 3 | 4 | | | | IV-2 | Fip1l1 |
| 11696 | 3 | 4 | | | | IV-2 | Fmn2 |
| 11697 | 3 | 4 | | | | IV-2 | Fnip1 |
| 11698 | 3 | 4 | | | | IV-2 | Fntb |
| 11699 | 3 | 4 | | | | IV-2 | Foxc2 |
| 11700 | 3 | 4 | | | | IV-2 | Foxd2 |
| 11701 | 3 | 4 | | | | IV-2 | Foxd3 |
| 11702 | 3 | 4 | | | | IV-2 | Foxk2 |
| 11703 | 3 | 4 | | | | IV-2 | Foxl1 |
| 11704 | 3 | 4 | | | | IV-2 | Foxn4 |
| 11705 | 3 | 4 | | | | IV-2 | Foxp2 |
| 11706 | 3 | 4 | | | | IV-2 | Foxred2 |
| 11707 | 3 | 4 | | | | IV-2 | Frat2 |
| 11708 | 3 | 4 | | | | IV-2 | Frem1 |
| 11709 | 3 | 4 | | | | IV-2 | Frem2 |
| 11710 | 3 | 4 | | | | IV-2 | Frmd5 |
| 11711 | 3 | 4 | | | | IV-2 | Frs3os |
| 11712 | 3 | 4 | | | | IV-2 | Fsip1 |
| 11713 | 3 | 4 | | | | IV-2 | Fxr1 |
| 11714 | 3 | 4 | | | | IV-2 | Gabrg1 |
| 11715 | 3 | 4 | | | | IV-2 | Gad2 |
| 11716 | 3 | 4 | | | | IV-2 | Galr3 |
| 11717 | 3 | 4 | | | | IV-2 | Galt |
| 11718 | 3 | 4 | | | | IV-2 | Garnl3 |
| 11719 | 3 | 4 | | | | IV-2 | Gast |
| 11720 | 3 | 4 | | | | IV-2 | Gata5os |
| 11721 | 3 | 4 | | | | IV-2 | Gatc |
| 11722 | 3 | 4 | | | | IV-2 | Gcc2 |
| 11723 | 3 | 4 | | | | IV-2 | Gcnt7 |
| 11724 | 3 | 4 | | | | IV-2 | Gdap1 |
| 11725 | 3 | 4 | | | | IV-2 | Gdpd2 |
| 11726 | 3 | 4 | | | | IV-2 | Gif |
| 11727 | 3 | 4 | | | | IV-2 | Gigyf1 |

Fig. 43 - 70

| | | | | | | | |
|---|---|---|---|---|---|---|---|
| 11728 | 3 | 4 | | | | IV-2 | Gja6 |
| 11729 | 3 | 4 | | | | IV-2 | Gkn3 |
| 11730 | 3 | 4 | | | | IV-2 | Gm10024 |
| 11731 | 3 | 4 | | | | IV-2 | Gm10057 |
| 11732 | 3 | 4 | | | | IV-2 | Gm10096 |
| 11733 | 3 | 4 | | | | IV-2 | Gm101 |
| 11734 | 3 | 4 | | | | IV-2 | Gm10220 |
| 11735 | 3 | 4 | | | | IV-2 | Gm10228 |
| 11736 | 3 | 4 | | | | IV-2 | Gm10230 |
| 11737 | 3 | 4 | | | | IV-2 | Gm10248 |
| 11738 | 3 | 4 | | | | IV-2 | Gm10272 |
| 11739 | 3 | 4 | | | | IV-2 | Gm10324 |
| 11740 | 3 | 4 | | | | IV-2 | Gm10354 |
| 11741 | 3 | 4 | | | | IV-2 | Gm10364 |
| 11742 | 3 | 4 | | | | IV-2 | Gm10375 |
| 11743 | 3 | 4 | | | | IV-2 | Gm10400 |
| 11744 | 3 | 4 | | | | IV-2 | Gm10408 |
| 11745 | 3 | 4 | | | | IV-2 | Gm10474 |
| 11746 | 3 | 4 | | | | IV-2 | Gm10532 |
| 11747 | 3 | 4 | | | | IV-2 | Gm10536 |
| 11748 | 3 | 4 | | | | IV-2 | Gm10549 |
| 11749 | 3 | 4 | | | | IV-2 | Gm10578 |
| 11750 | 3 | 4 | | | | IV-2 | Gm10658 |
| 11751 | 3 | 4 | | | | IV-2 | Gm10666 |
| 11752 | 3 | 4 | | | | IV-2 | Gm10684 |
| 11753 | 3 | 4 | | | | IV-2 | Gm10714 |
| 11754 | 3 | 4 | | | | IV-2 | Gm10754 |
| 11755 | 3 | 4 | | | | IV-2 | Gm10787 |
| 11756 | 3 | 4 | | | | IV-2 | Gm10825 |
| 11757 | 3 | 4 | | | | IV-2 | Gm10863 |
| 11758 | 3 | 4 | | | | IV-2 | Gm1123 |
| 11759 | 3 | 4 | | | | IV-2 | Gm11351 |
| 11760 | 3 | 4 | | | | IV-2 | Gm11413 |
| 11761 | 3 | 4 | | | | IV-2 | Gm11437 |
| 11762 | 3 | 4 | | | | IV-2 | Gm11487 |
| 11763 | 3 | 4 | | | | IV-2 | Gm11538 |
| 11764 | 3 | 4 | | | | IV-2 | Gm11544 |
| 11765 | 3 | 4 | | | | IV-2 | Gm11549 |
| 11766 | 3 | 4 | | | | IV-2 | Gm11559 |
| 11767 | 3 | 4 | | | | IV-2 | Gm11564 |
| 11768 | 3 | 4 | | | | IV-2 | Gm11568 |
| 11769 | 3 | 4 | | | | IV-2 | Gm11570 |
| 11770 | 3 | 4 | | | | IV-2 | Gm11595 |
| 11771 | 3 | 4 | | | | IV-2 | Gm11596 |
| 11772 | 3 | 4 | | | | IV-2 | Gm11651 |
| 11773 | 3 | 4 | | | | IV-2 | Gm11747 |
| 11774 | 3 | 4 | | | | IV-2 | Gm11985 |
| 11775 | 3 | 4 | | | | IV-2 | Gm12 |
| 11776 | 3 | 4 | | | | IV-2 | Gm12130 |
| 11777 | 3 | 4 | | | | IV-2 | Gm12429 |
| 11778 | 3 | 4 | | | | IV-2 | Gm12505 |
| 11779 | 3 | 4 | | | | IV-2 | Gm12695 |
| 11780 | 3 | 4 | | | | IV-2 | Gm12709 |
| 11781 | 3 | 4 | | | | IV-2 | Gm12789 |
| 11782 | 3 | 4 | | | | IV-2 | Gm12830 |
| 11783 | 3 | 4 | | | | IV-2 | Gm12887 |
| 11784 | 3 | 4 | | | | IV-2 | Gm13011 |
| 11785 | 3 | 4 | | | | IV-2 | Gm13051 |
| 11786 | 3 | 4 | | | | IV-2 | Gm13078 |
| 11787 | 3 | 4 | | | | IV-2 | Gm13084 |
| 11788 | 3 | 4 | | | | IV-2 | Gm13088 |
| 11789 | 3 | 4 | | | | IV-2 | Gm13102 |
| 11790 | 3 | 4 | | | | IV-2 | Gm13103 |
| 11791 | 3 | 4 | | | | IV-2 | Gm13119 |
| 11792 | 3 | 4 | | | | IV-2 | Gm13125 |
| 11793 | 3 | 4 | | | | IV-2 | Gm13177 |
| 11794 | 3 | 4 | | | | IV-2 | Gm13283 |
| 11795 | 3 | 4 | | | | IV-2 | Gm13286 |
| 11796 | 3 | 4 | | | | IV-2 | Gm13290 |
| 11797 | 3 | 4 | | | | IV-2 | Gm13547 |
| 11798 | 3 | 4 | | | | IV-2 | Gm13580 |
| 11799 | 3 | 4 | | | | IV-2 | Gm136 |
| 11800 | 3 | 4 | | | | IV-2 | Gm13749 |
| 11801 | 3 | 4 | | | | IV-2 | Gm13769 |
| 11802 | 3 | 4 | | | | IV-2 | Gm14023 |
| 11803 | 3 | 4 | | | | IV-2 | Gm14137 |
| 11804 | 3 | 4 | | | | IV-2 | Gm14204 |
| 11805 | 3 | 4 | | | | IV-2 | Gm14345 |
| 11806 | 3 | 4 | | | | IV-2 | Gm14405 |
| 11807 | 3 | 4 | | | | IV-2 | Gm14479 |
| 11808 | 3 | 4 | | | | IV-2 | Gm14482 |
| 11809 | 3 | 4 | | | | IV-2 | Gm14483 |
| 11810 | 3 | 4 | | | | IV-2 | Gm14484 |
| 11811 | 3 | 4 | | | | IV-2 | Gm14499 |
| 11812 | 3 | 4 | | | | IV-2 | Gm14625 |
| 11813 | 3 | 4 | | | | IV-2 | Gm14634 |
| 11814 | 3 | 4 | | | | IV-2 | Gm14635 |
| 11815 | 3 | 4 | | | | IV-2 | Gm14718 |
| 11816 | 3 | 4 | | | | IV-2 | Gm14744 |
| 11817 | 3 | 4 | | | | IV-2 | Gm14812 |
| 11818 | 3 | 4 | | | | IV-2 | Gm14819 |
| 11819 | 3 | 4 | | | | IV-2 | Gm14827 |
| 11820 | 3 | 4 | | | | IV-2 | Gm14850 |
| 11821 | 3 | 4 | | | | IV-2 | Gm14851 |
| 11822 | 3 | 4 | | | | IV-2 | Gm14858 |
| 11823 | 3 | 4 | | | | IV-2 | Gm15008 |
| 11824 | 3 | 4 | | | | IV-2 | Gm15023 |
| 11825 | 3 | 4 | | | | IV-2 | Gm15097 |
| 11826 | 3 | 4 | | | | IV-2 | Gm15104 |
| 11827 | 3 | 4 | | | | IV-2 | Gm15114 |
| 11828 | 3 | 4 | | | | IV-2 | Gm15348 |
| 11829 | 3 | 4 | | | | IV-2 | Gm15850 |
| 11830 | 3 | 4 | | | | IV-2 | Gm16157 |
| 11831 | 3 | 4 | | | | IV-2 | Gm1631 |
| 11832 | 3 | 4 | | | | IV-2 | Gm16325 |
| 11833 | 3 | 4 | | | | IV-2 | Gm16367 |
| 11834 | 3 | 4 | | | | IV-2 | Gm16386 |
| 11835 | 3 | 4 | | | | IV-2 | Gm16390 |
| 11836 | 3 | 4 | | | | IV-2 | Gm16404 |
| 11837 | 3 | 4 | | | | IV-2 | Gm16405 |
| 11838 | 3 | 4 | | | | IV-2 | Gm16451 |
| 11839 | 3 | 4 | | | | IV-2 | Gm16497 |
| 11840 | 3 | 4 | | | | IV-2 | Gm16501 |
| 11841 | 3 | 4 | | | | IV-2 | Gm16523 |
| 11842 | 3 | 4 | | | | IV-2 | Gm1653 |
| 11843 | 3 | 4 | | | | IV-2 | Gm16982 |
| 11844 | 3 | 4 | | | | IV-2 | Gm17660 |
| 11845 | 3 | 4 | | | | IV-2 | Gm17689 |
| 11846 | 3 | 4 | | | | IV-2 | Gm17727 |
| 11847 | 3 | 4 | | | | IV-2 | Gm17746 |
| 11848 | 3 | 4 | | | | IV-2 | Gm17751 |
| 11849 | 3 | 4 | | | | IV-2 | Gm17762 |
| 11850 | 3 | 4 | | | | IV-2 | Gm17769 |
| 11851 | 3 | 4 | | | | IV-2 | Gm17821 |
| 11852 | 3 | 4 | | | | IV-2 | Gm17830 |
| 11853 | 3 | 4 | | | | IV-2 | Gm19276 |
| 11854 | 3 | 4 | | | | IV-2 | Gm19277 |
| 11855 | 3 | 4 | | | | IV-2 | Gm19299 |
| 11856 | 3 | 4 | | | | IV-2 | Gm19402 |
| 11857 | 3 | 4 | | | | IV-2 | Gm19434 |
| 11858 | 3 | 4 | | | | IV-2 | Gm19522 |
| 11859 | 3 | 4 | | | | IV-2 | Gm2002 |
| 11860 | 3 | 4 | | | | IV-2 | Gm2016 |
| 11861 | 3 | 4 | | | | IV-2 | Gm20257 |
| 11862 | 3 | 4 | | | | IV-2 | Gm20362 |
| 11863 | 3 | 4 | | | | IV-2 | Gm20597 |
| 11864 | 3 | 4 | | | | IV-2 | Gm20605 |
| 11865 | 3 | 4 | | | | IV-2 | Gm20736 |
| 11866 | 3 | 4 | | | | IV-2 | Gm20745 |
| 11867 | 3 | 4 | | | | IV-2 | Gm20747 |
| 11868 | 3 | 4 | | | | IV-2 | Gm20753 |
| 11869 | 3 | 4 | | | | IV-2 | Gm20767 |
| 11870 | 3 | 4 | | | | IV-2 | Gm20809 |
| 11871 | 3 | 4 | | | | IV-2 | Gm20815 |
| 11872 | 3 | 4 | | | | IV-2 | Gm20816 |
| 11873 | 3 | 4 | | | | IV-2 | Gm20822 |
| 11874 | 3 | 4 | | | | IV-2 | Gm20831 |
| 11875 | 3 | 4 | | | | IV-2 | Gm20917 |
| 11876 | 3 | 4 | | | | IV-2 | Gm20939 |
| 11877 | 3 | 4 | | | | IV-2 | Gm21057 |
| 11878 | 3 | 4 | | | | IV-2 | Gm21276 |
| 11879 | 3 | 4 | | | | IV-2 | Gm21671 |
| 11880 | 3 | 4 | | | | IV-2 | Gm2447 |
| 11881 | 3 | 4 | | | | IV-2 | Gm2696 |
| 11882 | 3 | 4 | | | | IV-2 | Gm2721 |
| 11883 | 3 | 4 | | | | IV-2 | Gm2927 |
| 11884 | 3 | 4 | | | | IV-2 | Gm3143 |
| 11885 | 3 | 4 | | | | IV-2 | Gm3230 |
| 11886 | 3 | 4 | | | | IV-2 | Gm3286 |
| 11887 | 3 | 4 | | | | IV-2 | Gm3404 |
| 11888 | 3 | 4 | | | | IV-2 | Gm3409 |
| 11889 | 3 | 4 | | | | IV-2 | Gm3434 |
| 11890 | 3 | 4 | | | | IV-2 | Gm3488 |
| 11891 | 3 | 4 | | | | IV-2 | Gm3558 |
| 11892 | 3 | 4 | | | | IV-2 | Gm364 |
| 11893 | 3 | 4 | | | | IV-2 | Gm3716 |
| 11894 | 3 | 4 | | | | IV-2 | Gm4133 |
| 11895 | 3 | 4 | | | | IV-2 | Gm4224 |
| 11896 | 3 | 4 | | | | IV-2 | Gm4251 |
| 11897 | 3 | 4 | | | | IV-2 | Gm4265 |

Fig. 43 - 71

| | | | | | | | |
|---|---|---|---|---|---|---|---|
| 11898 | 3 | 4 | | | | IV-2 | Gm428 |
| 11899 | 3 | 4 | | | | IV-2 | Gm4297 |
| 11900 | 3 | 4 | | | | IV-2 | Gm4303 |
| 11901 | 3 | 4 | | | | IV-2 | Gm4307 |
| 11902 | 3 | 4 | | | | IV-2 | Gm4340 |
| 11903 | 3 | 4 | | | | IV-2 | Gm4349 |
| 11904 | 3 | 4 | | | | IV-2 | Gm436 |
| 11905 | 3 | 4 | | | | IV-2 | Gm4371 |
| 11906 | 3 | 4 | | | | IV-2 | Gm438 |
| 11907 | 3 | 4 | | | | IV-2 | Gm4432 |
| 11908 | 3 | 4 | | | | IV-2 | Gm4559 |
| 11909 | 3 | 4 | | | | IV-2 | Gm4566 |
| 11910 | 3 | 4 | | | | IV-2 | Gm4736 |
| 11911 | 3 | 4 | | | | IV-2 | Gm4791 |
| 11912 | 3 | 4 | | | | IV-2 | Gm4792 |
| 11913 | 3 | 4 | | | | IV-2 | Gm4872 |
| 11914 | 3 | 4 | | | | IV-2 | Gm4890 |
| 11915 | 3 | 4 | | | | IV-2 | Gm4922 |
| 11916 | 3 | 4 | | | | IV-2 | Gm5083 |
| 11917 | 3 | 4 | | | | IV-2 | Gm5122 |
| 11918 | 3 | 4 | | | | IV-2 | Gm5166 |
| 11919 | 3 | 4 | | | | IV-2 | Gm53 |
| 11920 | 3 | 4 | | | | IV-2 | Gm5334 |
| 11921 | 3 | 4 | | | | IV-2 | Gm5415 |
| 11922 | 3 | 4 | | | | IV-2 | Gm5476 |
| 11923 | 3 | 4 | | | | IV-2 | Gm5478 |
| 11924 | 3 | 4 | | | | IV-2 | Gm5523 |
| 11925 | 3 | 4 | | | | IV-2 | Gm5531 |
| 11926 | 3 | 4 | | | | IV-2 | Gm5577 |
| 11927 | 3 | 4 | | | | IV-2 | Gm5591 |
| 11928 | 3 | 4 | | | | IV-2 | Gm5725 |
| 11929 | 3 | 4 | | | | IV-2 | Gm5766 |
| 11930 | 3 | 4 | | | | IV-2 | Gm5820 |
| 11931 | 3 | 4 | | | | IV-2 | Gm5862 |
| 11932 | 3 | 4 | | | | IV-2 | Gm5885 |
| 11933 | 3 | 4 | | | | IV-2 | Gm5901 |
| 11934 | 3 | 4 | | | | IV-2 | Gm5916 |
| 11935 | 3 | 4 | | | | IV-2 | Gm5925 |
| 11936 | 3 | 4 | | | | IV-2 | Gm5935 |
| 11937 | 3 | 4 | | | | IV-2 | Gm5938 |
| 11938 | 3 | 4 | | | | IV-2 | Gm595 |
| 11939 | 3 | 4 | | | | IV-2 | Gm6040 |
| 11940 | 3 | 4 | | | | IV-2 | Gm6121 |
| 11941 | 3 | 4 | | | | IV-2 | Gm6164 |
| 11942 | 3 | 4 | | | | IV-2 | Gm6194 |
| 11943 | 3 | 4 | | | | IV-2 | Gm6213 |
| 11944 | 3 | 4 | | | | IV-2 | Gm6225 |
| 11945 | 3 | 4 | | | | IV-2 | Gm6329 |
| 11946 | 3 | 4 | | | | IV-2 | Gm6408 |
| 11947 | 3 | 4 | | | | IV-2 | Gm648 |
| 11948 | 3 | 4 | | | | IV-2 | Gm6537 |
| 11949 | 3 | 4 | | | | IV-2 | Gm6567 |
| 11950 | 3 | 4 | | | | IV-2 | Gm6578 |
| 11951 | 3 | 4 | | | | IV-2 | Gm6602 |
| 11952 | 3 | 4 | | | | IV-2 | Gm6634 |
| 11953 | 3 | 4 | | | | IV-2 | Gm6642 |
| 11954 | 3 | 4 | | | | IV-2 | Gm6792 |
| 11955 | 3 | 4 | | | | IV-2 | Gm6815 |
| 11956 | 3 | 4 | | | | IV-2 | Gm6880 |
| 11957 | 3 | 4 | | | | IV-2 | Gm6890 |
| 11958 | 3 | 4 | | | | IV-2 | Gm6902 |
| 11959 | 3 | 4 | | | | IV-2 | Gm6936 |
| 11960 | 3 | 4 | | | | IV-2 | Gm6981 |
| 11961 | 3 | 4 | | | | IV-2 | Gm7008 |
| 11962 | 3 | 4 | | | | IV-2 | Gm7056 |
| 11963 | 3 | 4 | | | | IV-2 | Gm7173 |
| 11964 | 3 | 4 | | | | IV-2 | Gm7257 |
| 11965 | 3 | 4 | | | | IV-2 | Gm7367 |
| 11966 | 3 | 4 | | | | IV-2 | Gm7714 |
| 11967 | 3 | 4 | | | | IV-2 | Gm7854 |
| 11968 | 3 | 4 | | | | IV-2 | Gm7903 |
| 11969 | 3 | 4 | | | | IV-2 | Gm7904 |
| 11970 | 3 | 4 | | | | IV-2 | Gm805 |
| 11971 | 3 | 4 | | | | IV-2 | Gm8096 |
| 11972 | 3 | 4 | | | | IV-2 | Gm813 |
| 11973 | 3 | 4 | | | | IV-2 | Gm8179 |
| 11974 | 3 | 4 | | | | IV-2 | Gm8221 |
| 11975 | 3 | 4 | | | | IV-2 | Gm8267 |
| 11976 | 3 | 4 | | | | IV-2 | Gm8300 |
| 11977 | 3 | 4 | | | | IV-2 | Gm833 |
| 11978 | 3 | 4 | | | | IV-2 | Gm8439 |
| 11979 | 3 | 4 | | | | IV-2 | Gm853 |
| 11980 | 3 | 4 | | | | IV-2 | Gm8579 |
| 11981 | 3 | 4 | | | | IV-2 | Gm8817 |
| 11982 | 3 | 4 | | | | IV-2 | Gm973 |
| 11983 | 3 | 4 | | | | IV-2 | Gm996 |
| 11984 | 3 | 4 | | | | IV-2 | Gmfb |
| 11985 | 3 | 4 | | | | IV-2 | Gnb2l1 |
| 11986 | 3 | 4 | | | | IV-2 | Gpr113 |
| 11987 | 3 | 4 | | | | IV-2 | Gpr115 |
| 11988 | 3 | 4 | | | | IV-2 | Gpr12 |
| 11989 | 3 | 4 | | | | IV-2 | Gpr128 |
| 11990 | 3 | 4 | | | | IV-2 | Gpr151 |
| 11991 | 3 | 4 | | | | IV-2 | Gpr152 |
| 11992 | 3 | 4 | | | | IV-2 | Gpr20 |
| 11993 | 3 | 4 | | | | IV-2 | Gpr26 |
| 11994 | 3 | 4 | | | | IV-2 | Gpr63 |
| 11995 | 3 | 4 | | | | IV-2 | Gpr88 |
| 11996 | 3 | 4 | | | | IV-2 | Gpr97 |
| 11997 | 3 | 4 | | | | IV-2 | Grin1 |
| 11998 | 3 | 4 | | | | IV-2 | Grk6 |
| 11999 | 3 | 4 | | | | IV-2 | Grm3 |
| 12000 | 3 | 4 | | | | IV-2 | Gsdma3 |
| 12001 | 3 | 4 | | | | IV-2 | Gsdmc3 |
| 12002 | 3 | 4 | | | | IV-2 | Gsdmcl1 |
| 12003 | 3 | 4 | | | | IV-2 | Gsdmcl2 |
| 12004 | 3 | 4 | | | | IV-2 | Gsg1l |
| 12005 | 3 | 4 | | | | IV-2 | Gsn |
| 12006 | 3 | 4 | | | | IV-2 | Gtf2a1 |
| 12007 | 3 | 4 | | | | IV-2 | Gtf2b |
| 12008 | 3 | 4 | | | | IV-2 | Gucy1b2 |
| 12009 | 3 | 4 | | | | IV-2 | Gucy2g |
| 12010 | 3 | 4 | | | | IV-2 | Gulp1 |
| 12011 | 3 | 4 | | | | IV-2 | Gzf1 |
| 12012 | 3 | 4 | | | | IV-2 | Gzmm |
| 12013 | 3 | 4 | | | | IV-2 | Gzmn |
| 12014 | 3 | 4 | | | | IV-2 | H13 |
| 12015 | 3 | 4 | | | | IV-2 | H2afy |
| 12016 | 3 | 4 | | | | IV-2 | H2-M10.6 |
| 12017 | 3 | 4 | | | | IV-2 | H2-M11 |
| 12018 | 3 | 4 | | | | IV-2 | Haus4 |
| 12019 | 3 | 4 | | | | IV-2 | Hbb-y |
| 12020 | 3 | 4 | | | | IV-2 | Heatr2 |
| 12021 | 3 | 4 | | | | IV-2 | Heatr6 |
| 12022 | 3 | 4 | | | | IV-2 | Hhat |
| 12023 | 3 | 4 | | | | IV-2 | Hic1 |
| 12024 | 3 | 4 | | | | IV-2 | Hic2 |
| 12025 | 3 | 4 | | | | IV-2 | Hmgcr |
| 12026 | 3 | 4 | | | | IV-2 | Hmgxb4 |
| 12027 | 3 | 4 | | | | IV-2 | Hnf4aos |
| 12028 | 3 | 4 | | | | IV-2 | Hoxa13 |
| 12029 | 3 | 4 | | | | IV-2 | Hoxc9 |
| 12030 | 3 | 4 | | | | IV-2 | Hp1bp3 |
| 12031 | 3 | 4 | | | | IV-2 | Hsd3b7 |
| 12032 | 3 | 4 | | | | IV-2 | Hsp90ab1 |
| 12033 | 3 | 4 | | | | IV-2 | Htr2c |
| 12034 | 3 | 4 | | | | IV-2 | Htr3a |
| 12035 | 3 | 4 | | | | IV-2 | Htr4 |
| 12036 | 3 | 4 | | | | IV-2 | Htra2 |
| 12037 | 3 | 4 | | | | IV-2 | I730028E13Rik |
| 12038 | 3 | 4 | | | | IV-2 | Ifna15 |
| 12039 | 3 | 4 | | | | IV-2 | Ifna16 |
| 12040 | 3 | 4 | | | | IV-2 | Ifna2 |
| 12041 | 3 | 4 | | | | IV-2 | Ifna4 |
| 12042 | 3 | 4 | | | | IV-2 | Ifna5 |
| 12043 | 3 | 4 | | | | IV-2 | Ifna6 |
| 12044 | 3 | 4 | | | | IV-2 | Ifna7 |
| 12045 | 3 | 4 | | | | IV-2 | Ifna9 |
| 12046 | 3 | 4 | | | | IV-2 | Ifnab |
| 12047 | 3 | 4 | | | | IV-2 | Ifnar2 |
| 12048 | 3 | 4 | | | | IV-2 | Ifnb1 |
| 12049 | 3 | 4 | | | | IV-2 | Ifne |
| 12050 | 3 | 4 | | | | IV-2 | Ifng |
| 12051 | 3 | 4 | | | | IV-2 | Ifngr1 |
| 12052 | 3 | 4 | | | | IV-2 | Ifnl3 |
| 12053 | 3 | 4 | | | | IV-2 | Ift122 |
| 12054 | 3 | 4 | | | | IV-2 | Ift20 |
| 12055 | 3 | 4 | | | | IV-2 | Il12rb2 |
| 12056 | 3 | 4 | | | | IV-2 | Il1f6 |
| 12057 | 3 | 4 | | | | IV-2 | Il22 |
| 12058 | 3 | 4 | | | | IV-2 | Il23r |
| 12059 | 3 | 4 | | | | IV-2 | Il3 |
| 12060 | 3 | 4 | | | | IV-2 | Il9r |
| 12061 | 3 | 4 | | | | IV-2 | Ilk |
| 12062 | 3 | 4 | | | | IV-2 | Imp4 |
| 12063 | 3 | 4 | | | | IV-2 | Inf2 |
| 12064 | 3 | 4 | | | | IV-2 | Ing1 |
| 12065 | 3 | 4 | | | | IV-2 | Inpp5j |
| 12066 | 3 | 4 | | | | IV-2 | Ints12 |
| 12067 | 3 | 4 | | | | IV-2 | Ipo11 |

Fig. 43 - 72

| | | | | | | | |
|---|---|---|---|---|---|---|---|
| 12068 | 3 | 4 | | | IV-2 | Iqcj |
| 12069 | 3 | 4 | | | IV-2 | Iqgap1 |
| 12070 | 3 | 4 | | | IV-2 | Iqgap2 |
| 12071 | 3 | 4 | | | IV-2 | Iqsec1 |
| 12072 | 3 | 4 | | | IV-2 | Irak4 |
| 12073 | 3 | 4 | | | IV-2 | Ireb2 |
| 12074 | 3 | 4 | | | IV-2 | Isg20l2 |
| 12075 | 3 | 4 | | | IV-2 | Isx |
| 12076 | 3 | 4 | | | IV-2 | Itfg3 |
| 12077 | 3 | 4 | | | IV-2 | Jag1 |
| 12078 | 3 | 4 | | | IV-2 | Jag2 |
| 12079 | 3 | 4 | | | IV-2 | Jkamp |
| 12080 | 3 | 4 | | | IV-2 | Kcnh5 |
| 12081 | 3 | 4 | | | IV-2 | Kcnj5 |
| 12082 | 3 | 4 | | | IV-2 | Kcnk16 |
| 12083 | 3 | 4 | | | IV-2 | Kcnk5 |
| 12084 | 3 | 4 | | | IV-2 | Kcns1 |
| 12085 | 3 | 4 | | | IV-2 | Kctd8 |
| 12086 | 3 | 4 | | | IV-2 | Khdrbs1 |
| 12087 | 3 | 4 | | | IV-2 | Kif4-ps |
| 12088 | 3 | 4 | | | IV-2 | Kif9 |
| 12089 | 3 | 4 | | | IV-2 | Kiss1r |
| 12090 | 3 | 4 | | | IV-2 | Kl |
| 12091 | 3 | 4 | | | IV-2 | Klf4 |
| 12092 | 3 | 4 | | | IV-2 | Klhl17 |
| 12093 | 3 | 4 | | | IV-2 | Klhl4 |
| 12094 | 3 | 4 | | | IV-2 | Klk1b5 |
| 12095 | 3 | 4 | | | IV-2 | Klkb1 |
| 12096 | 3 | 4 | | | IV-2 | Klra17 |
| 12097 | 3 | 4 | | | IV-2 | Klra19 |
| 12098 | 3 | 4 | | | IV-2 | Klra21 |
| 12099 | 3 | 4 | | | IV-2 | Klra33 |
| 12100 | 3 | 4 | | | IV-2 | Klra5 |
| 12101 | 3 | 4 | | | IV-2 | Klra6 |
| 12102 | 3 | 4 | | | IV-2 | Klra9 |
| 12103 | 3 | 4 | | | IV-2 | Klrb1 |
| 12104 | 3 | 4 | | | IV-2 | Klrb1a |
| 12105 | 3 | 4 | | | IV-2 | Klrb1-ps1 |
| 12106 | 3 | 4 | | | IV-2 | Klrc1 |
| 12107 | 3 | 4 | | | IV-2 | Klrc2 |
| 12108 | 3 | 4 | | | IV-2 | Klrg1 |
| 12109 | 3 | 4 | | | IV-2 | Klri2 |
| 12110 | 3 | 4 | | | IV-2 | Krt33b |
| 12111 | 3 | 4 | | | IV-2 | Krt35 |
| 12112 | 3 | 4 | | | IV-2 | Krt39 |
| 12113 | 3 | 4 | | | IV-2 | Krt40 |
| 12114 | 3 | 4 | | | IV-2 | Krt42 |
| 12115 | 3 | 4 | | | IV-2 | Krt72 |
| 12116 | 3 | 4 | | | IV-2 | Krt9 |
| 12117 | 3 | 4 | | | IV-2 | Krtap13-1 |
| 12118 | 3 | 4 | | | IV-2 | Krtap19-5 |
| 12119 | 3 | 4 | | | IV-2 | Krtap21-1 |
| 12120 | 3 | 4 | | | IV-2 | Krtap3-1 |
| 12121 | 3 | 4 | | | IV-2 | Krtap4-16 |
| 12122 | 3 | 4 | | | IV-2 | Krtap4-6 |
| 12123 | 3 | 4 | | | IV-2 | Krtap4-8 |
| 12124 | 3 | 4 | | | IV-2 | Larp1 |
| 12125 | 3 | 4 | | | IV-2 | Lcn5 |
| 12126 | 3 | 4 | | | IV-2 | Lcn6 |
| 12127 | 3 | 4 | | | IV-2 | Lcn8 |
| 12128 | 3 | 4 | | | IV-2 | Lcor |
| 12129 | 3 | 4 | | | IV-2 | Lct |
| 12130 | 3 | 4 | | | IV-2 | Lctl |
| 12131 | 3 | 4 | | | IV-2 | Leprot |
| 12132 | 3 | 4 | | | IV-2 | Lgr5 |
| 12133 | 3 | 4 | | | IV-2 | Lhfpl3 |
| 12134 | 3 | 4 | | | IV-2 | Lhfpl5 |
| 12135 | 3 | 4 | | | IV-2 | Lhx4 |
| 12136 | 3 | 4 | | | IV-2 | Lif |
| 12137 | 3 | 4 | | | IV-2 | Limk1 |
| 12138 | 3 | 4 | | | IV-2 | Lin28b |
| 12139 | 3 | 4 | | | IV-2 | Lipk |
| 12140 | 3 | 4 | | | IV-2 | Lipn |
| 12141 | 3 | 4 | | | IV-2 | Lman2 |
| 12142 | 3 | 4 | | | IV-2 | LOC100040786 |
| 12143 | 3 | 4 | | | IV-2 | LOC100505025 |
| 12144 | 3 | 4 | | | IV-2 | LOC100862015 |
| 12145 | 3 | 4 | | | IV-2 | LOC101055863 |
| 12146 | 3 | 4 | | | IV-2 | LOC101056149 |
| 12147 | 3 | 4 | | | IV-2 | LOC101056236 |
| 12148 | 3 | 4 | | | IV-2 | LOC101243624 |
| 12149 | 3 | 4 | | | IV-2 | LOC102632423 |
| 12150 | 3 | 4 | | | IV-2 | LOC102633035 |
| 12151 | 3 | 4 | | | IV-2 | LOC102634101 |
| 12152 | 3 | 4 | | | IV-2 | LOC102635087 |
| 12153 | 3 | 4 | | | IV-2 | LOC381967 |
| 12154 | 3 | 4 | | | IV-2 | Lonrf2 |
| 12155 | 3 | 4 | | | IV-2 | Lrp12 |
| 12156 | 3 | 4 | | | IV-2 | Lrp1b |
| 12157 | 3 | 4 | | | IV-2 | Lrrc73 |
| 12158 | 3 | 4 | | | IV-2 | Lrrc74 |
| 12159 | 3 | 4 | | | IV-2 | Lrrig3 |
| 12160 | 3 | 4 | | | IV-2 | Lrrk1 |
| 12161 | 3 | 4 | | | IV-2 | Lrtm2 |
| 12162 | 3 | 4 | | | IV-2 | Lsamp |
| 12163 | 3 | 4 | | | IV-2 | Luzp4 |
| 12164 | 3 | 4 | | | IV-2 | Ly6i |
| 12165 | 3 | 4 | | | IV-2 | Lypd3 |
| 12166 | 3 | 4 | | | IV-2 | Lypla2 |
| 12167 | 3 | 4 | | | IV-2 | Mad2l1bp |
| 12168 | 3 | 4 | | | IV-2 | Magea6 |
| 12169 | 3 | 4 | | | IV-2 | Mageb16 |
| 12170 | 3 | 4 | | | IV-2 | Mageb18 |
| 12171 | 3 | 4 | | | IV-2 | Mageb5 |
| 12172 | 3 | 4 | | | IV-2 | Maged1 |
| 12173 | 3 | 4 | | | IV-2 | Magee1 |
| 12174 | 3 | 4 | | | IV-2 | Magee2 |
| 12175 | 3 | 4 | | | IV-2 | Map6d1 |
| 12176 | 3 | 4 | | | IV-2 | March6 |
| 12177 | 3 | 4 | | | IV-2 | Mark4 |
| 12178 | 3 | 4 | | | IV-2 | Mc1r |
| 12179 | 3 | 4 | | | IV-2 | Mccc1 |
| 12180 | 3 | 4 | | | IV-2 | Mcfd2 |
| 12181 | 3 | 4 | | | IV-2 | Mcpt9 |
| 12182 | 3 | 4 | | | IV-2 | Mcu |
| 12183 | 3 | 4 | | | IV-2 | Mdn1 |
| 12184 | 3 | 4 | | | IV-2 | Melk |
| 12185 | 3 | 4 | | | IV-2 | Mex3c |
| 12186 | 3 | 4 | | | IV-2 | Mir101b |
| 12187 | 3 | 4 | | | IV-2 | Mir105 |
| 12188 | 3 | 4 | | | IV-2 | Mir106a |
| 12189 | 3 | 4 | | | IV-2 | Mir106b |
| 12190 | 3 | 4 | | | IV-2 | Mir107 |
| 12191 | 3 | 4 | | | IV-2 | Mir10a |
| 12192 | 3 | 4 | | | IV-2 | Mir10b |
| 12193 | 3 | 4 | | | IV-2 | Mir1187 |
| 12194 | 3 | 4 | | | IV-2 | Mir1188 |
| 12195 | 3 | 4 | | | IV-2 | Mir1190 |
| 12196 | 3 | 4 | | | IV-2 | Mir1191 |
| 12197 | 3 | 4 | | | IV-2 | Mir1191b |
| 12198 | 3 | 4 | | | IV-2 | Mir1192 |
| 12199 | 3 | 4 | | | IV-2 | Mir1193 |
| 12200 | 3 | 4 | | | IV-2 | Mir1195 |
| 12201 | 3 | 4 | | | IV-2 | Mir1197 |
| 12202 | 3 | 4 | | | IV-2 | Mir1198 |
| 12203 | 3 | 4 | | | IV-2 | Mir1224 |
| 12204 | 3 | 4 | | | IV-2 | Mir122a |
| 12205 | 3 | 4 | | | IV-2 | Mir1231 |
| 12206 | 3 | 4 | | | IV-2 | Mir1249 |
| 12207 | 3 | 4 | | | IV-2 | Mir124a-1 |
| 12208 | 3 | 4 | | | IV-2 | Mir124a-2 |
| 12209 | 3 | 4 | | | IV-2 | Mir124a-3 |
| 12210 | 3 | 4 | | | IV-2 | Mir1251 |
| 12211 | 3 | 4 | | | IV-2 | Mir1258 |
| 12212 | 3 | 4 | | | IV-2 | Mir125a |
| 12213 | 3 | 4 | | | IV-2 | Mir125b-1 |
| 12214 | 3 | 4 | | | IV-2 | Mir126 |
| 12215 | 3 | 4 | | | IV-2 | Mir1264 |
| 12216 | 3 | 4 | | | IV-2 | Mir136 |
| 12217 | 3 | 4 | | | IV-2 | Mir150 |
| 12218 | 3 | 4 | | | IV-2 | Mir186 |
| 12219 | 3 | 4 | | | IV-2 | Mir188 |
| 12220 | 3 | 4 | | | IV-2 | Mir1912 |
| 12221 | 3 | 4 | | | IV-2 | Mir29c |
| 12222 | 3 | 4 | | | IV-2 | Mir300 |
| 12223 | 3 | 4 | | | IV-2 | Mir6370 |
| 12224 | 3 | 4 | | | IV-2 | Mir6384 |
| 12225 | 3 | 4 | | | IV-2 | Mir6398 |
| 12226 | 3 | 4 | | | IV-2 | Mir6404 |
| 12227 | 3 | 4 | | | IV-2 | Mir6540 |
| 12228 | 3 | 4 | | | IV-2 | Mir692-2b |
| 12229 | 3 | 4 | | | IV-2 | Mir7063 |
| 12230 | 3 | 4 | | | IV-2 | Mir7094-2 |
| 12231 | 3 | 4 | | | IV-2 | Mir7235 |
| 12232 | 3 | 4 | | | IV-2 | Mir880 |
| 12233 | 3 | 4 | | | IV-2 | Mir883a |
| 12234 | 3 | 4 | | | IV-2 | Mir92-1 |
| 12235 | 3 | 4 | | | IV-2 | Mir92-2 |
| 12236 | 3 | 4 | | | IV-2 | Mirlet7g |
| 12237 | 3 | 4 | | | IV-2 | Mmp16 |

Fig. 43 - 73

| | | | | | | | |
|---|---|---|---|---|---|---|---|
| 12238 | 3 | 4 | | | | IV-2 | Mmp24 |
| 12239 | 3 | 4 | | | | IV-2 | Mmp25 |
| 12240 | 3 | 4 | | | | IV-2 | Morf4l2 |
| 12241 | 3 | 4 | | | | IV-2 | Mpped2 |
| 12242 | 3 | 4 | | | | IV-2 | Mrfap1 |
| 12243 | 3 | 4 | | | | IV-2 | Mrgprb3 |
| 12244 | 3 | 4 | | | | IV-2 | Mrgprb5 |
| 12245 | 3 | 4 | | | | IV-2 | Mrgprb8 |
| 12246 | 3 | 4 | | | | IV-2 | Mrgprd |
| 12247 | 3 | 4 | | | | IV-2 | Mrgprh |
| 12248 | 3 | 4 | | | | IV-2 | Mrgprx2 |
| 12249 | 3 | 4 | | | | IV-2 | Mroh2a |
| 12250 | 3 | 4 | | | | IV-2 | Mroh2b |
| 12251 | 3 | 4 | | | | IV-2 | Mroh9 |
| 12252 | 3 | 4 | | | | IV-2 | Mrpl10 |
| 12253 | 3 | 4 | | | | IV-2 | Msantd1 |
| 12254 | 3 | 4 | | | | IV-2 | Msi1 |
| 12255 | 3 | 4 | | | | IV-2 | Msi2 |
| 12256 | 3 | 4 | | | | IV-2 | Msrb3 |
| 12257 | 3 | 4 | | | | IV-2 | Mta1 |
| 12258 | 3 | 4 | | | | IV-2 | Mta2 |
| 12259 | 3 | 4 | | | | IV-2 | Muc6 |
| 12260 | 3 | 4 | | | | IV-2 | Mul1 |
| 12261 | 3 | 4 | | | | IV-2 | Mup4 |
| 12262 | 3 | 4 | | | | IV-2 | Myef2 |
| 12263 | 3 | 4 | | | | IV-2 | Myh7b |
| 12264 | 3 | 4 | | | | IV-2 | Myo1b |
| 12265 | 3 | 4 | | | | IV-2 | Myo6 |
| 12266 | 3 | 4 | | | | IV-2 | Myo7a |
| 12267 | 3 | 4 | | | | IV-2 | Naa11 |
| 12268 | 3 | 4 | | | | IV-2 | Nap1l1 |
| 12269 | 3 | 4 | | | | IV-2 | Nckipsd |
| 12270 | 3 | 4 | | | | IV-2 | Ndufv3 |
| 12271 | 3 | 4 | | | | IV-2 | Neu1 |
| 12272 | 3 | 4 | | | | IV-2 | Neurod1 |
| 12273 | 3 | 4 | | | | IV-2 | Nipal2 |
| 12274 | 3 | 4 | | | | IV-2 | Nkx2-4 |
| 12275 | 3 | 4 | | | | IV-2 | Nkx2-5 |
| 12276 | 3 | 4 | | | | IV-2 | Nkx6-1 |
| 12277 | 3 | 4 | | | | IV-2 | Nkx6-3 |
| 12278 | 3 | 4 | | | | IV-2 | Nln |
| 12279 | 3 | 4 | | | | IV-2 | Nlrp1a |
| 12280 | 3 | 4 | | | | IV-2 | Nlrp3 |
| 12281 | 3 | 4 | | | | IV-2 | Nlrp4a |
| 12282 | 3 | 4 | | | | IV-2 | Nlrp4b |
| 12283 | 3 | 4 | | | | IV-2 | Nlrp4e |
| 12284 | 3 | 4 | | | | IV-2 | Nlrp4f |
| 12285 | 3 | 4 | | | | IV-2 | Nlrp9a |
| 12286 | 3 | 4 | | | | IV-2 | Nlrp9c |
| 12287 | 3 | 4 | | | | IV-2 | Nlrx1 |
| 12288 | 3 | 4 | | | | IV-2 | Nol4 |
| 12289 | 3 | 4 | | | | IV-2 | Npas1 |
| 12290 | 3 | 4 | | | | IV-2 | Npc1l1 |
| 12291 | 3 | 4 | | | | IV-2 | Nphs1os |
| 12292 | 3 | 4 | | | | IV-2 | Nppc |
| 12293 | 3 | 4 | | | | IV-2 | Nps |
| 12294 | 3 | 4 | | | | IV-2 | Npy5r |
| 12295 | 3 | 4 | | | | IV-2 | Nrp |
| 12296 | 3 | 4 | | | | IV-2 | Nrsn2 |
| 12297 | 3 | 4 | | | | IV-2 | Nsa2 |
| 12298 | 3 | 4 | | | | IV-2 | Nup153 |
| 12299 | 3 | 4 | | | | IV-2 | Nxf3 |
| 12300 | 3 | 4 | | | | IV-2 | Nyap2 |
| 12301 | 3 | 4 | | | | IV-2 | Obox6 |
| 12302 | 3 | 4 | | | | IV-2 | Obp2a |
| 12303 | 3 | 4 | | | | IV-2 | Oc90 |
| 12304 | 3 | 4 | | | | IV-2 | Oca2 |
| 12305 | 3 | 4 | | | | IV-2 | Ociad1 |
| 12306 | 3 | 4 | | | | IV-2 | Ocm |
| 12307 | 3 | 4 | | | | IV-2 | Odf2 |
| 12308 | 3 | 4 | | | | IV-2 | Olfr1008 |
| 12309 | 3 | 4 | | | | IV-2 | Olfr1009 |
| 12310 | 3 | 4 | | | | IV-2 | Olfr1010 |
| 12311 | 3 | 4 | | | | IV-2 | Olfr1012 |
| 12312 | 3 | 4 | | | | IV-2 | Olfr1014 |
| 12313 | 3 | 4 | | | | IV-2 | Olfr1016 |
| 12314 | 3 | 4 | | | | IV-2 | Olfr1018 |
| 12315 | 3 | 4 | | | | IV-2 | Olfr1019 |
| 12316 | 3 | 4 | | | | IV-2 | Olfr102 |
| 12317 | 3 | 4 | | | | IV-2 | Olfr1020 |
| 12318 | 3 | 4 | | | | IV-2 | Olfr1022 |
| 12319 | 3 | 4 | | | | IV-2 | Olfr1023 |
| 12320 | 3 | 4 | | | | IV-2 | Olfr1024 |
| 12321 | 3 | 4 | | | | IV-2 | Olfr1026 |
| 12322 | 3 | 4 | | | | IV-2 | Olfr1028 |
| 12323 | 3 | 4 | | | | IV-2 | Olfr1029 |
| 12324 | 3 | 4 | | | | IV-2 | Olfr103 |
| 12325 | 3 | 4 | | | | IV-2 | Olfr1030 |
| 12326 | 3 | 4 | | | | IV-2 | Olfr1031 |
| 12327 | 3 | 4 | | | | IV-2 | Olfr1032 |
| 12328 | 3 | 4 | | | | IV-2 | Olfr1036 |
| 12329 | 3 | 4 | | | | IV-2 | Olfr1037 |
| 12330 | 3 | 4 | | | | IV-2 | Olfr1038-ps |
| 12331 | 3 | 4 | | | | IV-2 | Olfr1039 |
| 12332 | 3 | 4 | | | | IV-2 | Olfr1043 |
| 12333 | 3 | 4 | | | | IV-2 | Olfr1089 |
| 12334 | 3 | 4 | | | | IV-2 | Olfr109 |
| 12335 | 3 | 4 | | | | IV-2 | Olfr1155 |
| 12336 | 3 | 4 | | | | IV-2 | Olfr1163 |
| 12337 | 3 | 4 | | | | IV-2 | Olfr1300-ps1 |
| 12338 | 3 | 4 | | | | IV-2 | Olfr1309 |
| 12339 | 3 | 4 | | | | IV-2 | Olfr1320 |
| 12340 | 3 | 4 | | | | IV-2 | Olfr1387 |
| 12341 | 3 | 4 | | | | IV-2 | Olfr1419 |
| 12342 | 3 | 4 | | | | IV-2 | Olfr1443 |
| 12343 | 3 | 4 | | | | IV-2 | Olfr1447 |
| 12344 | 3 | 4 | | | | IV-2 | Olfr147 |
| 12345 | 3 | 4 | | | | IV-2 | Olfr168 |
| 12346 | 3 | 4 | | | | IV-2 | Olfr183 |
| 12347 | 3 | 4 | | | | IV-2 | Olfr205 |
| 12348 | 3 | 4 | | | | IV-2 | Olfr239 |
| 12349 | 3 | 4 | | | | IV-2 | Olfr267 |
| 12350 | 3 | 4 | | | | IV-2 | Olfr298 |
| 12351 | 3 | 4 | | | | IV-2 | Olfr328 |
| 12352 | 3 | 4 | | | | IV-2 | Olfr329-ps |
| 12353 | 3 | 4 | | | | IV-2 | Olfr348 |
| 12354 | 3 | 4 | | | | IV-2 | Olfr355 |
| 12355 | 3 | 4 | | | | IV-2 | Olfr47 |
| 12356 | 3 | 4 | | | | IV-2 | Olfr532 |
| 12357 | 3 | 4 | | | | IV-2 | Olfr596 |
| 12358 | 3 | 4 | | | | IV-2 | Olfr6 |
| 12359 | 3 | 4 | | | | IV-2 | Olfr603 |
| 12360 | 3 | 4 | | | | IV-2 | Olfr74 |
| 12361 | 3 | 4 | | | | IV-2 | Olfr744 |
| 12362 | 3 | 4 | | | | IV-2 | Olfr782 |
| 12363 | 3 | 4 | | | | IV-2 | Olfr804 |
| 12364 | 3 | 4 | | | | IV-2 | Olfr823 |
| 12365 | 3 | 4 | | | | IV-2 | Oog4 |
| 12366 | 3 | 4 | | | | IV-2 | Oraov1 |
| 12367 | 3 | 4 | | | | IV-2 | Otol1 |
| 12368 | 3 | 4 | | | | IV-2 | Otor |
| 12369 | 3 | 4 | | | | IV-2 | Otp |
| 12370 | 3 | 4 | | | | IV-2 | Ovol3 |
| 12371 | 3 | 4 | | | | IV-2 | Oxct1 |
| 12372 | 3 | 4 | | | | IV-2 | Oxt |
| 12373 | 3 | 4 | | | | IV-2 | Pacs1 |
| 12374 | 3 | 4 | | | | IV-2 | Pacs2 |
| 12375 | 3 | 4 | | | | IV-2 | Pacsin2 |
| 12376 | 3 | 4 | | | | IV-2 | Pan2 |
| 12377 | 3 | 4 | | | | IV-2 | Papl |
| 12378 | 3 | 4 | | | | IV-2 | Pax3 |
| 12379 | 3 | 4 | | | | IV-2 | Pax9 |
| 12380 | 3 | 4 | | | | IV-2 | Pcdh8 |
| 12381 | 3 | 4 | | | | IV-2 | Pcdha2 |
| 12382 | 3 | 4 | | | | IV-2 | Pcdha4 |
| 12383 | 3 | 4 | | | | IV-2 | Pcdhac1 |
| 12384 | 3 | 4 | | | | IV-2 | Pcdhb1 |
| 12385 | 3 | 4 | | | | IV-2 | Pcdhb11 |
| 12386 | 3 | 4 | | | | IV-2 | Pcdhb12 |
| 12387 | 3 | 4 | | | | IV-2 | Pcdhb15 |
| 12388 | 3 | 4 | | | | IV-2 | Pcdhb16 |
| 12389 | 3 | 4 | | | | IV-2 | Pcdhb17 |
| 12390 | 3 | 4 | | | | IV-2 | Pcdhb19 |
| 12391 | 3 | 4 | | | | IV-2 | Pcdhb5 |
| 12392 | 3 | 4 | | | | IV-2 | Pcdhb9 |
| 12393 | 3 | 4 | | | | IV-2 | Pcdhgb6 |
| 12394 | 3 | 4 | | | | IV-2 | Pcsk9 |
| 12395 | 3 | 4 | | | | IV-2 | Pctp |
| 12396 | 3 | 4 | | | | IV-2 | Pdcd6ip |
| 12397 | 3 | 4 | | | | IV-2 | Pde9a |
| 12398 | 3 | 4 | | | | IV-2 | Pea15b |
| 12399 | 3 | 4 | | | | IV-2 | Pgap3 |
| 12400 | 3 | 4 | | | | IV-2 | Pgm3 |
| 12401 | 3 | 4 | | | | IV-2 | Phactr3 |
| 12402 | 3 | 4 | | | | IV-2 | Phkb |
| 12403 | 3 | 4 | | | | IV-2 | Pira4 |
| 12404 | 3 | 4 | | | | IV-2 | Pisd-ps3 |
| 12405 | 3 | 4 | | | | IV-2 | Pkd1l2 |
| 12406 | 3 | 4 | | | | IV-2 | Pkd2 |
| 12407 | 3 | 4 | | | | IV-2 | Pkdrej |

Fig. 43 - 74

| | | | | | | | | | | | | | | |
|---|---|---|---|---|---|---|---|---|---|---|---|---|---|---|
| 12408 | 3 | 4 | | | | IV-2 | Pld6 | 12493 | 3 | 4 | | | IV-2 | Rhox3c |
| 12409 | 3 | 4 | | | | IV-2 | Plekha1 | 12494 | 3 | 4 | | | IV-2 | Rhox3f |
| 12410 | 3 | 4 | | | | IV-2 | Pmch | 12495 | 3 | 4 | | | IV-2 | Rhox3h |
| 12411 | 3 | 4 | | | | IV-2 | Pnn | 12496 | 3 | 4 | | | IV-2 | Rhox4a |
| 12412 | 3 | 4 | | | | IV-2 | Pou3f2 | 12497 | 3 | 4 | | | IV-2 | Rhox4b |
| 12413 | 3 | 4 | | | | IV-2 | Pou4f3 | 12498 | 3 | 4 | | | IV-2 | Rhox4c |
| 12414 | 3 | 4 | | | | IV-2 | Pou5f1 | 12499 | 3 | 4 | | | IV-2 | Rhox4d |
| 12415 | 3 | 4 | | | | IV-2 | Pou5f2 | 12500 | 3 | 4 | | | IV-2 | Rhox4e |
| 12416 | 3 | 4 | | | | IV-2 | Pp2d1 | 12501 | 3 | 4 | | | IV-2 | Rhox4f |
| 12417 | 3 | 4 | | | | IV-2 | Ppap2b | 12502 | 3 | 4 | | | IV-2 | Rhox7 |
| 12418 | 3 | 4 | | | | IV-2 | Ppp5c | 12503 | 3 | 4 | | | IV-2 | Rhox8 |
| 12419 | 3 | 4 | | | | IV-2 | Pramel4 | 12504 | 3 | 4 | | | IV-2 | Rhox9 |
| 12420 | 3 | 4 | | | | IV-2 | Pramel5 | 12505 | 3 | 4 | | | IV-2 | Rhpn1 |
| 12421 | 3 | 4 | | | | IV-2 | Pramel6 | 12506 | 3 | 4 | | | IV-2 | Ribc1 |
| 12422 | 3 | 4 | | | | IV-2 | Prb1 | 12507 | 3 | 4 | | | IV-2 | Ric3 |
| 12423 | 3 | 4 | | | | IV-2 | Prcp | 12508 | 3 | 4 | | | IV-2 | Rlbp1 |
| 12424 | 3 | 4 | | | | IV-2 | Prdm4 | 12509 | 3 | 4 | | | IV-2 | Rln3 |
| 12425 | 3 | 4 | | | | IV-2 | Prdm6 | 12510 | 3 | 4 | | | IV-2 | Rmi1 |
| 12426 | 3 | 4 | | | | IV-2 | Prkg2 | 12511 | 3 | 4 | | | IV-2 | Rnaseh1 |
| 12427 | 3 | 4 | | | | IV-2 | Prl2c4 | 12512 | 3 | 4 | | | IV-2 | Rnf165 |
| 12428 | 3 | 4 | | | | IV-2 | Prl2c5 | 12513 | 3 | 4 | | | IV-2 | Rnf168 |
| 12429 | 3 | 4 | | | | IV-2 | Prl3a1 | 12514 | 3 | 4 | | | IV-2 | Rnf170 |
| 12430 | 3 | 4 | | | | IV-2 | Prl3b1 | 12515 | 3 | 4 | | | IV-2 | Rnf185 |
| 12431 | 3 | 4 | | | | IV-2 | Prl3c1 | 12516 | 3 | 4 | | | IV-2 | Rnf19b |
| 12432 | 3 | 4 | | | | IV-2 | Prl3d2 | 12517 | 3 | 4 | | | IV-2 | Robo2 |
| 12433 | 3 | 4 | | | | IV-2 | Prl3d3 | 12518 | 3 | 4 | | | IV-2 | Robo3 |
| 12434 | 3 | 4 | | | | IV-2 | Prl4a1 | 12519 | 3 | 4 | | | IV-2 | Robo4 |
| 12435 | 3 | 4 | | | | IV-2 | Prl5a1 | 12520 | 3 | 4 | | | IV-2 | Rock1 |
| 12436 | 3 | 4 | | | | IV-2 | Prl6a1 | 12521 | 3 | 4 | | | IV-2 | Rock2 |
| 12437 | 3 | 4 | | | | IV-2 | Prl7a1 | 12522 | 3 | 4 | | | IV-2 | Rpl11 |
| 12438 | 3 | 4 | | | | IV-2 | Prl7a2 | 12523 | 3 | 4 | | | IV-2 | Rrp1 |
| 12439 | 3 | 4 | | | | IV-2 | Prl7b1 | 12524 | 3 | 4 | | | IV-2 | Rsf1 |
| 12440 | 3 | 4 | | | | IV-2 | Prl7c1 | 12525 | 3 | 4 | | | IV-2 | Rspry1 |
| 12441 | 3 | 4 | | | | IV-2 | Prl7d1 | 12526 | 3 | 4 | | | IV-2 | Rtfdc1 |
| 12442 | 3 | 4 | | | | IV-2 | Prl8a1 | 12527 | 3 | 4 | | | IV-2 | Rufy2 |
| 12443 | 3 | 4 | | | | IV-2 | Prl8a2 | 12528 | 3 | 4 | | | IV-2 | Saal1 |
| 12444 | 3 | 4 | | | | IV-2 | Prl8a6 | 12529 | 3 | 4 | | | IV-2 | Sall2 |
| 12445 | 3 | 4 | | | | IV-2 | Prl8a8 | 12530 | 3 | 4 | | | IV-2 | Sap30bp |
| 12446 | 3 | 4 | | | | IV-2 | Prl8a9 | 12531 | 3 | 4 | | | IV-2 | Scaf4 |
| 12447 | 3 | 4 | | | | IV-2 | Prlh | 12532 | 3 | 4 | | | IV-2 | Scarna3b |
| 12448 | 3 | 4 | | | | IV-2 | Prlhr | 12533 | 3 | 4 | | | IV-2 | Scarna9 |
| 12449 | 3 | 4 | | | | IV-2 | Prlr | 12534 | 3 | 4 | | | IV-2 | Scel |
| 12450 | 3 | 4 | | | | IV-2 | Prpf38b | 12535 | 3 | 4 | | | IV-2 | Scgb1b3 |
| 12451 | 3 | 4 | | | | IV-2 | Prpsap1 | 12536 | 3 | 4 | | | IV-2 | Scgb1b30 |
| 12452 | 3 | 4 | | | | IV-2 | Prr12 | 12537 | 3 | 4 | | | IV-2 | Scgb1b7 |
| 12453 | 3 | 4 | | | | IV-2 | Prr3 | 12538 | 3 | 4 | | | IV-2 | Scgb1c1 |
| 12454 | 3 | 4 | | | | IV-2 | Prss34 | 12539 | 3 | 4 | | | IV-2 | Scgb2b15 |
| 12455 | 3 | 4 | | | | IV-2 | Prss38 | 12540 | 3 | 4 | | | IV-2 | Scgb2b17 |
| 12456 | 3 | 4 | | | | IV-2 | Prss43 | 12541 | 3 | 4 | | | IV-2 | Scgb2b19 |
| 12457 | 3 | 4 | | | | IV-2 | Prss45 | 12542 | 3 | 4 | | | IV-2 | Scgb2b2 |
| 12458 | 3 | 4 | | | | IV-2 | Prss57 | 12543 | 3 | 4 | | | IV-2 | Scgb2b26 |
| 12459 | 3 | 4 | | | | IV-2 | Prss58 | 12544 | 3 | 4 | | | IV-2 | Scgb3a2 |
| 12460 | 3 | 4 | | | | IV-2 | Psg28 | 12545 | 3 | 4 | | | IV-2 | Scn2a1 |
| 12461 | 3 | 4 | | | | IV-2 | Psg29 | 12546 | 3 | 4 | | | IV-2 | Scube3 |
| 12462 | 3 | 4 | | | | IV-2 | Psg-ps1 | 12547 | 3 | 4 | | | IV-2 | Sept5 |
| 12463 | 3 | 4 | | | | IV-2 | Pskh1 | 12548 | 3 | 4 | | | IV-2 | Serpina12 |
| 12464 | 3 | 4 | | | | IV-2 | Psma3 | 12549 | 3 | 4 | | | IV-2 | Serpina3a |
| 12465 | 3 | 4 | | | | IV-2 | Pten | 12550 | 3 | 4 | | | IV-2 | Serpinb6e |
| 12466 | 3 | 4 | | | | IV-2 | Ptk2 | 12551 | 3 | 4 | | | IV-2 | Serpinb9d |
| 12467 | 3 | 4 | | | | IV-2 | Ptk2b | 12552 | 3 | 4 | | | IV-2 | Serpine3 |
| 12468 | 3 | 4 | | | | IV-2 | Ptpn5 | 12553 | 3 | 4 | | | IV-2 | Six3os1 |
| 12469 | 3 | 4 | | | | IV-2 | Ptprv | 12554 | 3 | 4 | | | IV-2 | Ska3 |
| 12470 | 3 | 4 | | | | IV-2 | Ptrh2 | 12555 | 3 | 4 | | | IV-2 | Ski |
| 12471 | 3 | 4 | | | | IV-2 | Qtrtd1 | 12556 | 3 | 4 | | | IV-2 | Skint7 |
| 12472 | 3 | 4 | | | | IV-2 | Rab11b | 12557 | 3 | 4 | | | IV-2 | Skiv2l |
| 12473 | 3 | 4 | | | | IV-2 | Rai14 | 12558 | 3 | 4 | | | IV-2 | Skiv2l2 |
| 12474 | 3 | 4 | | | | IV-2 | Ralb | 12559 | 3 | 4 | | | IV-2 | Skor1 |
| 12475 | 3 | 4 | | | | IV-2 | Ralbp1 | 12560 | 3 | 4 | | | IV-2 | Skp2 |
| 12476 | 3 | 4 | | | | IV-2 | Ranbp10 | 12561 | 3 | 4 | | | IV-2 | Slc12a1 |
| 12477 | 3 | 4 | | | | IV-2 | Rbbp5 | 12562 | 3 | 4 | | | IV-2 | Slc16a14 |
| 12478 | 3 | 4 | | | | IV-2 | Rbm17 | 12563 | 3 | 4 | | | IV-2 | Slc17a8 |
| 12479 | 3 | 4 | | | | IV-2 | Rbm18 | 12564 | 3 | 4 | | | IV-2 | Slc18a3 |
| 12480 | 3 | 4 | | | | IV-2 | Rbpj | 12565 | 3 | 4 | | | IV-2 | Slc22a4 |
| 12481 | 3 | 4 | | | | IV-2 | Ren2 | 12566 | 3 | 4 | | | IV-2 | Slc24a2 |
| 12482 | 3 | 4 | | | | IV-2 | Rfwd2 | 12567 | 3 | 4 | | | IV-2 | Slc26a9 |
| 12483 | 3 | 4 | | | | IV-2 | Rfwd3 | 12568 | 3 | 4 | | | IV-2 | Slc39a13 |
| 12484 | 3 | 4 | | | | IV-2 | Rgs7 | 12569 | 3 | 4 | | | IV-2 | Slc46a2 |
| 12485 | 3 | 4 | | | | IV-2 | Rhag | 12570 | 3 | 4 | | | IV-2 | Slc5a4b |
| 12486 | 3 | 4 | | | | IV-2 | Rhbdd2 | 12571 | 3 | 4 | | | IV-2 | Slc6a11 |
| 12487 | 3 | 4 | | | | IV-2 | Rhbdf2 | 12572 | 3 | 4 | | | IV-2 | Slc7a6os |
| 12488 | 3 | 4 | | | | IV-2 | Rhoc | 12573 | 3 | 4 | | | IV-2 | Slco1a6 |
| 12489 | 3 | 4 | | | | IV-2 | Rhox2b | 12574 | 3 | 4 | | | IV-2 | Slco1b2 |
| 12490 | 3 | 4 | | | | IV-2 | Rhox2e | 12575 | 3 | 4 | | | IV-2 | Slco1c1 |
| 12491 | 3 | 4 | | | | IV-2 | Rhox2h | 12576 | 3 | 4 | | | IV-2 | Slco5a1 |
| 12492 | 3 | 4 | | | | IV-2 | Rhox3a | 12577 | 3 | 4 | | | IV-2 | Slitrk2 |

Fig. 43 - 75

| | | | | | | | |
|---|---|---|---|---|---|---|---|
| 12578 | 3 | 4 | | | | IV-2 | Smad1 |
| 12579 | 3 | 4 | | | | IV-2 | Smad5 |
| 12580 | 3 | 4 | | | | IV-2 | Smek1 |
| 12581 | 3 | 4 | | | | IV-2 | Smim15 |
| 12582 | 3 | 4 | | | | IV-2 | Smim7 |
| 12583 | 3 | 4 | | | | IV-2 | Smu1 |
| 12584 | 3 | 4 | | | | IV-2 | Snora19 |
| 12585 | 3 | 4 | | | | IV-2 | Snora2b |
| 12586 | 3 | 4 | | | | IV-2 | Snora33 |
| 12587 | 3 | 4 | | | | IV-2 | Snora35 |
| 12588 | 3 | 4 | | | | IV-2 | Snora5c |
| 12589 | 3 | 4 | | | | IV-2 | Snora69 |
| 12590 | 3 | 4 | | | | IV-2 | Snord111 |
| 12591 | 3 | 4 | | | | IV-2 | Snord116l2 |
| 12592 | 3 | 4 | | | | IV-2 | Snord118 |
| 12593 | 3 | 4 | | | | IV-2 | Snord14a |
| 12594 | 3 | 4 | | | | IV-2 | Snord2 |
| 12595 | 3 | 4 | | | | IV-2 | Snord35a |
| 12596 | 3 | 4 | | | | IV-2 | Snord42a |
| 12597 | 3 | 4 | | | | IV-2 | Snord42b |
| 12598 | 3 | 4 | | | | IV-2 | Snord45b |
| 12599 | 3 | 4 | | | | IV-2 | Snord45c |
| 12600 | 3 | 4 | | | | IV-2 | Snord47 |
| 12601 | 3 | 4 | | | | IV-2 | Snord7 |
| 12602 | 3 | 4 | | | | IV-2 | Snord71 |
| 12603 | 3 | 4 | | | | IV-2 | Snord85 |
| 12604 | 3 | 4 | | | | IV-2 | Sorbs2os |
| 12605 | 3 | 4 | | | | IV-2 | Sox14 |
| 12606 | 3 | 4 | | | | IV-2 | Sox2ot |
| 12607 | 3 | 4 | | | | IV-2 | Spag4 |
| 12608 | 3 | 4 | | | | IV-2 | Spag7 |
| 12609 | 3 | 4 | | | | IV-2 | Spata2 |
| 12610 | 3 | 4 | | | | IV-2 | Spata22 |
| 12611 | 3 | 4 | | | | IV-2 | Spata31d1a |
| 12612 | 3 | 4 | | | | IV-2 | Spata32 |
| 12613 | 3 | 4 | | | | IV-2 | Spcs2 |
| 12614 | 3 | 4 | | | | IV-2 | Speer4a |
| 12615 | 3 | 4 | | | | IV-2 | Speer4d |
| 12616 | 3 | 4 | | | | IV-2 | Speer4e |
| 12617 | 3 | 4 | | | | IV-2 | Speer6-ps1 |
| 12618 | 3 | 4 | | | | IV-2 | Speg |
| 12619 | 3 | 4 | | | | IV-2 | Spg21 |
| 12620 | 3 | 4 | | | | IV-2 | Sphk2 |
| 12621 | 3 | 4 | | | | IV-2 | Spink14 |
| 12622 | 3 | 4 | | | | IV-2 | Spint4 |
| 12623 | 3 | 4 | | | | IV-2 | Spire1 |
| 12624 | 3 | 4 | | | | IV-2 | Spop |
| 12625 | 3 | 4 | | | | IV-2 | Sprn |
| 12626 | 3 | 4 | | | | IV-2 | Spty2d1 |
| 12627 | 3 | 4 | | | | IV-2 | Srsf11 |
| 12628 | 3 | 4 | | | | IV-2 | Ssbp3 |
| 12629 | 3 | 4 | | | | IV-2 | Ssr3 |
| 12630 | 3 | 4 | | | | IV-2 | Ssx9 |
| 12631 | 3 | 4 | | | | IV-2 | Ssxb6 |
| 12632 | 3 | 4 | | | | IV-2 | Ssxb8 |
| 12633 | 3 | 4 | | | | IV-2 | Ssxb9 |
| 12634 | 3 | 4 | | | | IV-2 | St3gal3 |
| 12635 | 3 | 4 | | | | IV-2 | Stat4 |
| 12636 | 3 | 4 | | | | IV-2 | Stk36 |
| 12637 | 3 | 4 | | | | IV-2 | Stoml1 |
| 12638 | 3 | 4 | | | | IV-2 | Stpg2 |
| 12639 | 3 | 4 | | | | IV-2 | Strap |
| 12640 | 3 | 4 | | | | IV-2 | Strc |
| 12641 | 3 | 4 | | | | IV-2 | Strip1 |
| 12642 | 3 | 4 | | | | IV-2 | Stt3a |
| 12643 | 3 | 4 | | | | IV-2 | Sucla2 |
| 12644 | 3 | 4 | | | | IV-2 | Sult2a3 |
| 12645 | 3 | 4 | | | | IV-2 | Sult3a1 |
| 12646 | 3 | 4 | | | | IV-2 | Sult4a1 |
| 12647 | 3 | 4 | | | | IV-2 | Sumo1 |
| 12648 | 3 | 4 | | | | IV-2 | Supt5 |
| 12649 | 3 | 4 | | | | IV-2 | Svop |
| 12650 | 3 | 4 | | | | IV-2 | Svopl |
| 12651 | 3 | 4 | | | | IV-2 | Svs1 |
| 12652 | 3 | 4 | | | | IV-2 | Svs6 |
| 12653 | 3 | 4 | | | | IV-2 | Swap70 |
| 12654 | 3 | 4 | | | | IV-2 | Syap1 |
| 12655 | 3 | 4 | | | | IV-2 | Syf2 |
| 12656 | 3 | 4 | | | | IV-2 | Sympk |
| 12657 | 3 | 4 | | | | IV-2 | Taar1 |
| 12658 | 3 | 4 | | | | IV-2 | Taar7a |
| 12659 | 3 | 4 | | | | IV-2 | Taar7b |
| 12660 | 3 | 4 | | | | IV-2 | Taar7d |
| 12661 | 3 | 4 | | | | IV-2 | Taar7e |
| 12662 | 3 | 4 | | | | IV-2 | Taar7f |
| 12663 | 3 | 4 | | | | IV-2 | Taar8a |
| 12664 | 3 | 4 | | | | IV-2 | Taar8c |
| 12665 | 3 | 4 | | | | IV-2 | Taar9 |
| 12666 | 3 | 4 | | | | IV-2 | Tab2 |
| 12667 | 3 | 4 | | | | IV-2 | Tab3 |
| 12668 | 3 | 4 | | | | IV-2 | Tac1 |
| 12669 | 3 | 4 | | | | IV-2 | Tac4 |
| 12670 | 3 | 4 | | | | IV-2 | Taf1 |
| 12671 | 3 | 4 | | | | IV-2 | Tas2r105 |
| 12672 | 3 | 4 | | | | IV-2 | Tas2r106 |
| 12673 | 3 | 4 | | | | IV-2 | Tas2r108 |
| 12674 | 3 | 4 | | | | IV-2 | Tas2r109 |
| 12675 | 3 | 4 | | | | IV-2 | Tas2r110 |
| 12676 | 3 | 4 | | | | IV-2 | Tas2r113 |
| 12677 | 3 | 4 | | | | IV-2 | Tas2r114 |
| 12678 | 3 | 4 | | | | IV-2 | Tas2r115 |
| 12679 | 3 | 4 | | | | IV-2 | Tas2r117 |
| 12680 | 3 | 4 | | | | IV-2 | Tas2r118 |
| 12681 | 3 | 4 | | | | IV-2 | Tas2r119 |
| 12682 | 3 | 4 | | | | IV-2 | Tas2r120 |
| 12683 | 3 | 4 | | | | IV-2 | Tas2r121 |
| 12684 | 3 | 4 | | | | IV-2 | Tas2r122 |
| 12685 | 3 | 4 | | | | IV-2 | Tas2r124 |
| 12686 | 3 | 4 | | | | IV-2 | Tas2r125 |
| 12687 | 3 | 4 | | | | IV-2 | Tas2r126 |
| 12688 | 3 | 4 | | | | IV-2 | Tas2r129 |
| 12689 | 3 | 4 | | | | IV-2 | Tas2r130 |
| 12690 | 3 | 4 | | | | IV-2 | Tas2r131 |
| 12691 | 3 | 4 | | | | IV-2 | Tas2r134 |
| 12692 | 3 | 4 | | | | IV-2 | Tas2r135 |
| 12693 | 3 | 4 | | | | IV-2 | Tas2r136 |
| 12694 | 3 | 4 | | | | IV-2 | Tas2r137 |
| 12695 | 3 | 4 | | | | IV-2 | Tas2r138 |
| 12696 | 3 | 4 | | | | IV-2 | Tas2r139 |
| 12697 | 3 | 4 | | | | IV-2 | Tas2r140 |
| 12698 | 3 | 4 | | | | IV-2 | Tas2r143 |
| 12699 | 3 | 4 | | | | IV-2 | Tas2r144 |
| 12700 | 3 | 4 | | | | IV-2 | Tatdn1 |
| 12701 | 3 | 4 | | | | IV-2 | Tbx10 |
| 12702 | 3 | 4 | | | | IV-2 | Tbx3os2 |
| 12703 | 3 | 4 | | | | IV-2 | Tcaim |
| 12704 | 3 | 4 | | | | IV-2 | Tcp1 |
| 12705 | 3 | 4 | | | | IV-2 | Tcp10a |
| 12706 | 3 | 4 | | | | IV-2 | Tcstv1 |
| 12707 | 3 | 4 | | | | IV-2 | Tcstv3 |
| 12708 | 3 | 4 | | | | IV-2 | Tekt3 |
| 12709 | 3 | 4 | | | | IV-2 | Tenm1 |
| 12710 | 3 | 4 | | | | IV-2 | Tex19.1 |
| 12711 | 3 | 4 | | | | IV-2 | Tex2 |
| 12712 | 3 | 4 | | | | IV-2 | Tex29 |
| 12713 | 3 | 4 | | | | IV-2 | Tfam |
| 12714 | 3 | 4 | | | | IV-2 | Tfap2d |
| 12715 | 3 | 4 | | | | IV-2 | Tgm6 |
| 12716 | 3 | 4 | | | | IV-2 | Th |
| 12717 | 3 | 4 | | | | IV-2 | Thoc3 |
| 12718 | 3 | 4 | | | | IV-2 | Tie1 |
| 12719 | 3 | 4 | | | | IV-2 | Timp3 |
| 12720 | 3 | 4 | | | | IV-2 | Tirap |
| 12721 | 3 | 4 | | | | IV-2 | Tm9sf1 |
| 12722 | 3 | 4 | | | | IV-2 | Tmc6 |
| 12723 | 3 | 4 | | | | IV-2 | Tmc7 |
| 12724 | 3 | 4 | | | | IV-2 | Tmed2 |
| 12725 | 3 | 4 | | | | IV-2 | Tmem198 |
| 12726 | 3 | 4 | | | | IV-2 | Tmem213 |
| 12727 | 3 | 4 | | | | IV-2 | Tmem217 |
| 12728 | 3 | 4 | | | | IV-2 | Tmem233 |
| 12729 | 3 | 4 | | | | IV-2 | Tmem39a |
| 12730 | 3 | 4 | | | | IV-2 | Tmem55b |
| 12731 | 3 | 4 | | | | IV-2 | Tmem57 |
| 12732 | 3 | 4 | | | | IV-2 | Tmprss5 |
| 12733 | 3 | 4 | | | | IV-2 | Tmprss7 |
| 12734 | 3 | 4 | | | | IV-2 | Tnfrsf21 |
| 12735 | 3 | 4 | | | | IV-2 | Tnfsf4 |
| 12736 | 3 | 4 | | | | IV-2 | Tnip2 |
| 12737 | 3 | 4 | | | | IV-2 | Tpd52l2 |
| 12738 | 3 | 4 | | | | IV-2 | Tpm3 |
| 12739 | 3 | 4 | | | | IV-2 | Tpm4 |
| 12740 | 3 | 4 | | | | IV-2 | Tpte |
| 12741 | 3 | 4 | | | | IV-2 | Trappc9 |
| 12742 | 3 | 4 | | | | IV-2 | Trim15 |
| 12743 | 3 | 4 | | | | IV-2 | Trim35 |
| 12744 | 3 | 4 | | | | IV-2 | Trim43b |
| 12745 | 3 | 4 | | | | IV-2 | Trim46 |
| 12746 | 3 | 4 | | | | IV-2 | Trim71 |
| 12747 | 3 | 4 | | | | IV-2 | Trim9 |

Fig. 43 - 76

| | | | | | | | | |
|---|---|---|---|---|---|---|---|---|
| 12748 | 3 | 4 | | | | IV-2 | Triobp |
| 12749 | 3 | 4 | | | | IV-2 | Trip12 |
| 12750 | 3 | 4 | | | | IV-2 | Trip13 |
| 12751 | 3 | 4 | | | | IV-2 | Trpc3 |
| 12752 | 3 | 4 | | | | IV-2 | Trpc5 |
| 12753 | 3 | 4 | | | | IV-2 | Trpm2 |
| 12754 | 3 | 4 | | | | IV-2 | Trrap |
| 12755 | 3 | 4 | | | | IV-2 | Tsnaxip1 |
| 12756 | 3 | 4 | | | | IV-2 | Tspan1 |
| 12757 | 3 | 4 | | | | IV-2 | Tspan14 |
| 12758 | 3 | 4 | | | | IV-2 | Tspan17 |
| 12759 | 3 | 4 | | | | IV-2 | Tspan18 |
| 12760 | 3 | 4 | | | | IV-2 | Tspan5 |
| 12761 | 3 | 4 | | | | IV-2 | Tspy-ps |
| 12762 | 3 | 4 | | | | IV-2 | Ttc23l |
| 12763 | 3 | 4 | | | | IV-2 | Ttc30a1 |
| 12764 | 3 | 4 | | | | IV-2 | Txnl4a |
| 12765 | 3 | 4 | | | | IV-2 | Uba2 |
| 12766 | 3 | 4 | | | | IV-2 | Ube2g1 |
| 12767 | 3 | 4 | | | | IV-2 | Ubox5 |
| 12768 | 3 | 4 | | | | IV-2 | Ubr7 |
| 12769 | 3 | 4 | | | | IV-2 | Ubxn4 |
| 12770 | 3 | 4 | | | | IV-2 | Ufd1l |
| 12771 | 3 | 4 | | | | IV-2 | Ugt2a2 |
| 12772 | 3 | 4 | | | | IV-2 | Ugt2b36 |
| 12773 | 3 | 4 | | | | IV-2 | Ulk4 |
| 12774 | 3 | 4 | | | | IV-2 | Unk |
| 12775 | 3 | 4 | | | | IV-2 | Unkl |
| 12776 | 3 | 4 | | | | IV-2 | Upf1 |
| 12777 | 3 | 4 | | | | IV-2 | Uqcr10 |
| 12778 | 3 | 4 | | | | IV-2 | Usp11 |
| 12779 | 3 | 4 | | | | IV-2 | Usp19 |
| 12780 | 3 | 4 | | | | IV-2 | Usp20 |
| 12781 | 3 | 4 | | | | IV-2 | Usp21 |
| 12782 | 3 | 4 | | | | IV-2 | Usp22 |
| 12783 | 3 | 4 | | | | IV-2 | Usp8 |
| 12784 | 3 | 4 | | | | IV-2 | Vamp2 |
| 12785 | 3 | 4 | | | | IV-2 | Vamp3 |
| 12786 | 3 | 4 | | | | IV-2 | Vamp4 |
| 12787 | 3 | 4 | | | | IV-2 | Vamp5 |
| 12788 | 3 | 4 | | | | IV-2 | Vax2os |
| 12789 | 3 | 4 | | | | IV-2 | Vcl |
| 12790 | 3 | 4 | | | | IV-2 | Vill |
| 12791 | 3 | 4 | | | | IV-2 | Vkorc1l1 |
| 12792 | 3 | 4 | | | | IV-2 | Vmn1r107 |
| 12793 | 3 | 4 | | | | IV-2 | Vmn1r11 |
| 12794 | 3 | 4 | | | | IV-2 | Vmn1r112 |
| 12795 | 3 | 4 | | | | IV-2 | Vmn1r113 |
| 12796 | 3 | 4 | | | | IV-2 | Vmn1r114 |
| 12797 | 3 | 4 | | | | IV-2 | Vmn1r115 |
| 12798 | 3 | 4 | | | | IV-2 | Vmn1r116 |
| 12799 | 3 | 4 | | | | IV-2 | Vmn1r117 |
| 12800 | 3 | 4 | | | | IV-2 | Vmn1r118 |
| 12801 | 3 | 4 | | | | IV-2 | Vmn1r12 |
| 12802 | 3 | 4 | | | | IV-2 | Vmn1r120 |
| 12803 | 3 | 4 | | | | IV-2 | Vmn1r123 |
| 12804 | 3 | 4 | | | | IV-2 | Vmn1r124 |
| 12805 | 3 | 4 | | | | IV-2 | Vmn1r125 |
| 12806 | 3 | 4 | | | | IV-2 | Vmn1r126 |
| 12807 | 3 | 4 | | | | IV-2 | Vmn1r127 |
| 12808 | 3 | 4 | | | | IV-2 | Vmn1r128 |
| 12809 | 3 | 4 | | | | IV-2 | Vmn1r129 |
| 12810 | 3 | 4 | | | | IV-2 | Vmn1r13 |
| 12811 | 3 | 4 | | | | IV-2 | Vmn1r130 |
| 12812 | 3 | 4 | | | | IV-2 | Vmn1r132 |
| 12813 | 3 | 4 | | | | IV-2 | Vmn1r135 |
| 12814 | 3 | 4 | | | | IV-2 | Vmn1r137 |
| 12815 | 3 | 4 | | | | IV-2 | Vmn1r138 |
| 12816 | 3 | 4 | | | | IV-2 | Vmn1r139 |
| 12817 | 3 | 4 | | | | IV-2 | Vmn1r14 |
| 12818 | 3 | 4 | | | | IV-2 | Vmn1r142 |
| 12819 | 3 | 4 | | | | IV-2 | Vmn1r148 |
| 12820 | 3 | 4 | | | | IV-2 | Vmn1r15 |
| 12821 | 3 | 4 | | | | IV-2 | Vmn1r217 |
| 12822 | 3 | 4 | | | | IV-2 | Vmn2r63 |
| 12823 | 3 | 4 | | | | IV-2 | Vmo1 |
| 12824 | 3 | 4 | | | | IV-2 | Vtn |
| 12825 | 3 | 4 | | | | IV-2 | Vwa8 |
| 12826 | 3 | 4 | | | | IV-2 | Vwa9 |
| 12827 | 3 | 4 | | | | IV-2 | Wap |
| 12828 | 3 | 4 | | | | IV-2 | Wbscr25 |
| 12829 | 3 | 4 | | | | IV-2 | Wdr36 |
| 12830 | 3 | 4 | | | | IV-2 | Wee2 |
| 12831 | 3 | 4 | | | | IV-2 | Wfdc15a |
| 12832 | 3 | 4 | | | | IV-2 | Whsc1 |
| 12833 | 3 | 4 | | | | IV-2 | Wt1os |
| 12834 | 3 | 4 | | | | IV-2 | Xndc1 |
| 12835 | 3 | 4 | | | | IV-2 | Xpnpep2 |
| 12836 | 3 | 4 | | | | IV-2 | Zfp114 |
| 12837 | 3 | 4 | | | | IV-2 | Zfp143 |
| 12838 | 3 | 4 | | | | IV-2 | Zfp362 |
| 12839 | 3 | 4 | | | | IV-2 | Zfp433 |
| 12840 | 3 | 4 | | | | IV-2 | Zfp472 |
| 12841 | 3 | 4 | | | | IV-2 | Zfp51 |
| 12842 | 3 | 4 | | | | IV-2 | Zfp512 |
| 12843 | 3 | 4 | | | | IV-2 | Zfp513 |
| 12844 | 3 | 4 | | | | IV-2 | Zfp572 |
| 12845 | 3 | 4 | | | | IV-2 | Zfp574 |
| 12846 | 3 | 4 | | | | IV-2 | Zfp653 |
| 12847 | 3 | 4 | | | | IV-2 | Zfp655 |
| 12848 | 3 | 4 | | | | IV-2 | Zfp663 |
| 12849 | 3 | 4 | | | | IV-2 | Zfp68 |
| 12850 | 3 | 4 | | | | IV-2 | Zfp819 |
| 12851 | 3 | 4 | | | | IV-2 | Zfp830 |
| 12852 | 3 | 4 | | | | IV-2 | Zfp869 |
| 12853 | 3 | 4 | | | | IV-2 | Zfp934 |
| 12854 | 3 | 4 | | | | IV-2 | Zfp941 |
| 12855 | 3 | 4 | | | | IV-2 | Zfp942 |
| 12856 | 3 | 4 | | | | IV-2 | Zic2 |
| 12857 | 3 | 4 | | | | IV-2 | Zkscan14 |
| 12858 | 3 | 4 | | | | IV-2 | Zkscan16 |
| 12859 | 3 | 4 | | | | IV-2 | Zkscan2 |
| 12860 | 3 | 4 | | | | IV-2 | Zkscan3 |
| 12861 | 3 | 4 | | | | IV-2 | Zpld1 |
| 12862 | 3 | 4 | | | | IV-2 | Zranb2 |
| 12863 | 3 | 4 | | | | IV-2 | Zrsr2 |
| 12864 | 3 | 4 | | | | IV-2 | Zscan5b |
| 12865 | 3 | 4 | | | | IV-2 | Zswim2 |
| 12866 | 3 | 4 | | | | IV-1 | 0610010F05Rik |
| 12867 | 3 | 4 | | | | IV-1 | 0610012G03Rik |
| 12868 | 3 | 4 | | | | IV-1 | 0610031J06Rik |
| 12869 | 3 | 4 | | | | IV-1 | 1110004F10Rik |
| 12870 | 3 | 4 | | | | IV-1 | 1110012L19Rik |
| 12871 | 3 | 4 | | | | IV-1 | 1110015O18Rik |
| 12872 | 3 | 4 | | | | IV-1 | 1110025L11Rik |
| 12873 | 3 | 4 | | | | IV-1 | 1110028F11Rik |
| 12874 | 3 | 4 | | | | IV-1 | 1110032F04Rik |
| 12875 | 3 | 4 | | | | IV-1 | 1110038F14Rik |
| 12876 | 3 | 4 | | | | IV-1 | 1110051M20Rik |
| 12877 | 3 | 4 | | | | IV-1 | 1110059E24Rik |
| 12878 | 3 | 4 | | | | IV-1 | 1190002N15Rik |
| 12879 | 3 | 4 | | | | IV-1 | 1190003K10Rik |
| 12880 | 3 | 4 | | | | IV-1 | 1200014J11Rik |
| 12881 | 3 | 4 | | | | IV-1 | 1500009L16Rik |
| 12882 | 3 | 4 | | | | IV-1 | 1500015L24Rik |
| 12883 | 3 | 4 | | | | IV-1 | 1600002D24Rik |
| 12884 | 3 | 4 | | | | IV-1 | 1600014K23Rik |
| 12885 | 3 | 4 | | | | IV-1 | 1600015I10Rik |
| 12886 | 3 | 4 | | | | IV-1 | 1600019K03Rik |
| 12887 | 3 | 4 | | | | IV-1 | 1700001D01Rik |
| 12888 | 3 | 4 | | | | IV-1 | 1700001G11Rik |
| 12889 | 3 | 4 | | | | IV-1 | 1700001G17Rik |
| 12890 | 3 | 4 | | | | IV-1 | 1700001P01Rik |
| 12891 | 3 | 4 | | | | IV-1 | 1700003G18Rik |
| 12892 | 3 | 4 | | | | IV-1 | 1700003H04Rik |
| 12893 | 3 | 4 | | | | IV-1 | 1700003L19Rik |
| 12894 | 3 | 4 | | | | IV-1 | 1700003M07Rik |
| 12895 | 3 | 4 | | | | IV-1 | 1700006A11Rik |
| 12896 | 3 | 4 | | | | IV-1 | 1700007B14Rik |
| 12897 | 3 | 4 | | | | IV-1 | 1700007G11Rik |
| 12898 | 3 | 4 | | | | IV-1 | 1700007K09Rik |
| 12899 | 3 | 4 | | | | IV-1 | 1700008F21Rik |
| 12900 | 3 | 4 | | | | IV-1 | 1700008O03Rik |
| 12901 | 3 | 4 | | | | IV-1 | 1700011L22Rik |
| 12902 | 3 | 4 | | | | IV-1 | 1700011M02Rik |
| 12903 | 3 | 4 | | | | IV-1 | 1700012I11Rik |
| 12904 | 3 | 4 | | | | IV-1 | 1700013F07Rik |
| 12905 | 3 | 4 | | | | IV-1 | 1700015F17Rik |
| 12906 | 3 | 4 | | | | IV-1 | 1700016L21Rik |
| 12907 | 3 | 4 | | | | IV-1 | 1700017G19Rik |
| 12908 | 3 | 4 | | | | IV-1 | 1700017J07Rik |
| 12909 | 3 | 4 | | | | IV-1 | 1700017N19Rik |
| 12910 | 3 | 4 | | | | IV-1 | 1700018B08Rik |
| 12911 | 3 | 4 | | | | IV-1 | 1700018F24Rik |
| 12912 | 3 | 4 | | | | IV-1 | 1700019B21Rik |
| 12913 | 3 | 4 | | | | IV-1 | 1700019E08Rik |
| 12914 | 3 | 4 | | | | IV-1 | 1700019L03Rik |
| 12915 | 3 | 4 | | | | IV-1 | 1700020A23Rik |
| 12916 | 3 | 4 | | | | IV-1 | 1700020G17Rik |
| 12917 | 3 | 4 | | | | IV-1 | 1700020N15Rik |

Fig. 43 - 77

| | | | | | | | | | | | | | | |
|---|---|---|---|---|---|---|---|---|---|---|---|---|---|---|
| 12918 | 3 | 4 | | | | IV-1 | 1700020N18Rik | 13003 | 3 | 4 | | | IV-1 | 2010308F09Rik |
| 12919 | 3 | 4 | | | | IV-1 | 1700021F07Rik | 13004 | 3 | 4 | | | IV-1 | 2010315B03Rik |
| 12920 | 3 | 4 | | | | IV-1 | 1700021N21Rik | 13005 | 3 | 4 | | | IV-1 | 2200002J24Rik |
| 12921 | 3 | 4 | | | | IV-1 | 1700022A22Rik | 13006 | 3 | 4 | | | IV-1 | 2210015D19Rik |
| 12922 | 3 | 4 | | | | IV-1 | 1700022E09Rik | 13007 | 3 | 4 | | | IV-1 | 2210016F16Rik |
| 12923 | 3 | 4 | | | | IV-1 | 1700022I11Rik | 13008 | 3 | 4 | | | IV-1 | 2210016L21Rik |
| 12924 | 3 | 4 | | | | IV-1 | 1700023F02Rik | 13009 | 3 | 4 | | | IV-1 | 2210019I11Rik |
| 12925 | 3 | 4 | | | | IV-1 | 1700025B11Rik | 13010 | 3 | 4 | | | IV-1 | 2210404O09Rik |
| 12926 | 3 | 4 | | | | IV-1 | 1700025F22Rik | 13011 | 3 | 4 | | | IV-1 | 2210417A02Rik |
| 12927 | 3 | 4 | | | | IV-1 | 1700025F24Rik | 13012 | 3 | 4 | | | IV-1 | 2210420H20Rik |
| 12928 | 3 | 4 | | | | IV-1 | 1700025K24Rik | 13013 | 3 | 4 | | | IV-1 | 2300003K06Rik |
| 12929 | 3 | 4 | | | | IV-1 | 1700026F02Rik | 13014 | 3 | 4 | | | IV-1 | 2310002D06Rik |
| 12930 | 3 | 4 | | | | IV-1 | 1700027H10Rik | 13015 | 3 | 4 | | | IV-1 | 2310002J15Rik |
| 12931 | 3 | 4 | | | | IV-1 | 1700027I24Rik | 13016 | 3 | 4 | | | IV-1 | 2310005A03Rik |
| 12932 | 3 | 4 | | | | IV-1 | 1700028B04Rik | 13017 | 3 | 4 | | | IV-1 | 2310005E17Rik |
| 12933 | 3 | 4 | | | | IV-1 | 1700028M03Rik | 13018 | 3 | 4 | | | IV-1 | 2310007B03Rik |
| 12934 | 3 | 4 | | | | IV-1 | 1700029I15Rik | 13019 | 3 | 4 | | | IV-1 | 2310008N11Rik |
| 12935 | 3 | 4 | | | | IV-1 | 1700030F04Rik | 13020 | 3 | 4 | | | IV-1 | 2310011J03Rik |
| 12936 | 3 | 4 | | | | IV-1 | 1700030F18Rik | 13021 | 3 | 4 | | | IV-1 | 2310014L17Rik |
| 12937 | 3 | 4 | | | | IV-1 | 1700030L20Rik | 13022 | 3 | 4 | | | IV-1 | 2310015D24Rik |
| 12938 | 3 | 4 | | | | IV-1 | 1700030M09Rik | 13023 | 3 | 4 | | | IV-1 | 2310016D03Rik |
| 12939 | 3 | 4 | | | | IV-1 | 1700031A10Rik | 13024 | 3 | 4 | | | IV-1 | 2310020H05Rik |
| 12940 | 3 | 4 | | | | IV-1 | 1700031F05Rik | 13025 | 3 | 4 | | | IV-1 | 2310022A10Rik |
| 12941 | 3 | 4 | | | | IV-1 | 1700034G24Rik | 13026 | 3 | 4 | | | IV-1 | 2310022B05Rik |
| 12942 | 3 | 4 | | | | IV-1 | 1700036G14Rik | 13027 | 3 | 4 | | | IV-1 | 2310030A07Rik |
| 12943 | 3 | 4 | | | | IV-1 | 1700039E22Rik | 13028 | 3 | 4 | | | IV-1 | 2310030G06Rik |
| 12944 | 3 | 4 | | | | IV-1 | 1700041M19Rik | 13029 | 3 | 4 | | | IV-1 | 2310034C09Rik |
| 12945 | 3 | 4 | | | | IV-1 | 1700042B14Rik | 13030 | 3 | 4 | | | IV-1 | 2310034O05Rik |
| 12946 | 3 | 4 | | | | IV-1 | 1700042O10Rik | 13031 | 3 | 4 | | | IV-1 | 2310042E22Rik |
| 12947 | 3 | 4 | | | | IV-1 | 1700047A11Rik | 13032 | 3 | 4 | | | IV-1 | 2310043L19Rik |
| 12948 | 3 | 4 | | | | IV-1 | 1700049E22Rik | 13033 | 3 | 4 | | | IV-1 | 2310043O21Rik |
| 12949 | 3 | 4 | | | | IV-1 | 1700051A21Rik | 13034 | 3 | 4 | | | IV-1 | 2310057J18Rik |
| 12950 | 3 | 4 | | | | IV-1 | 1700052I22Rik | 13035 | 3 | 4 | | | IV-1 | 2310061I04Rik |
| 12951 | 3 | 4 | | | | IV-1 | 1700054A03Rik | 13036 | 3 | 4 | | | IV-1 | 2310061N02Rik |
| 12952 | 3 | 4 | | | | IV-1 | 1700054K19Rik | 13037 | 3 | 4 | | | IV-1 | 2310067B10Rik |
| 12953 | 3 | 4 | | | | IV-1 | 1700054M17Rik | 13038 | 3 | 4 | | | IV-1 | 2310069G16Rik |
| 12954 | 3 | 4 | | | | IV-1 | 1700055C04Rik | 13039 | 3 | 4 | | | IV-1 | 2410002F23Rik |
| 12955 | 3 | 4 | | | | IV-1 | 1700055N04Rik | 13040 | 3 | 4 | | | IV-1 | 2410003L11Rik |
| 12956 | 3 | 4 | | | | IV-1 | 1700057H15Rik | 13041 | 3 | 4 | | | IV-1 | 2410004I01Rik |
| 12957 | 3 | 4 | | | | IV-1 | 1700060C20Rik | 13042 | 3 | 4 | | | IV-1 | 2410012E07Rik |
| 12958 | 3 | 4 | | | | IV-1 | 1700061F12Rik | 13043 | 3 | 4 | | | IV-1 | 2410012M07Rik |
| 12959 | 3 | 4 | | | | IV-1 | 1700061G19Rik | 13044 | 3 | 4 | | | IV-1 | 2410016O06Rik |
| 12960 | 3 | 4 | | | | IV-1 | 1700061I17Rik | 13045 | 3 | 4 | | | IV-1 | 2410017I17Rik |
| 12961 | 3 | 4 | | | | IV-1 | 1700065D16Rik | 13046 | 3 | 4 | | | IV-1 | 2410088K16Rik |
| 12962 | 3 | 4 | | | | IV-1 | 1700066B17Rik | 13047 | 3 | 4 | | | IV-1 | 2410124H12Rik |
| 12963 | 3 | 4 | | | | IV-1 | 1700066B19Rik | 13048 | 3 | 4 | | | IV-1 | 2410141K09Rik |
| 12964 | 3 | 4 | | | | IV-1 | 1700066O22Rik | 13049 | 3 | 4 | | | IV-1 | 2510009E07Rik |
| 12965 | 3 | 4 | | | | IV-1 | 1700069L16Rik | 13050 | 3 | 4 | | | IV-1 | 2510049J12Rik |
| 12966 | 3 | 4 | | | | IV-1 | 1700072B07Rik | 13051 | 3 | 4 | | | IV-3 | 2610001J05Rik |
| 12967 | 3 | 4 | | | | IV-1 | 1700080E11Rik | 13052 | 3 | 4 | | | IV-1 | 2610002M06Rik |
| 12968 | 3 | 4 | | | | IV-1 | 1700084J12Rik | 13053 | 3 | 4 | | | IV-1 | 2610027K06Rik |
| 12969 | 3 | 4 | | | | IV-1 | 1700085C21Rik | 13054 | 3 | 4 | | | IV-1 | 2610028E06Rik |
| 12970 | 3 | 4 | | | | IV-1 | 1700092E19Rik | 13055 | 3 | 4 | | | IV-1 | 2610034M16Rik |
| 12971 | 3 | 4 | | | | IV-1 | 1700092K14Rik | 13056 | 3 | 4 | | | IV-1 | 2610035F20Rik |
| 12972 | 3 | 4 | | | | IV-1 | 1700095A21Rik | 13057 | 3 | 4 | | | IV-1 | 2610100L16Rik |
| 12973 | 3 | 4 | | | | IV-1 | 1700095B10Rik | 13058 | 3 | 4 | | | IV-1 | 2610203C22Rik |
| 12974 | 3 | 4 | | | | IV-1 | 1700096J18Rik | 13059 | 3 | 4 | | | IV-1 | 2610301B20Rik |
| 12975 | 3 | 4 | | | | IV-1 | 1700106I16Rik | 13060 | 3 | 4 | | | IV-1 | 2610305D13Rik |
| 12976 | 3 | 4 | | | | IV-1 | 1700108F19Rik | 13061 | 3 | 4 | | | IV-1 | 2610316D01Rik |
| 12977 | 3 | 4 | | | | IV-1 | 1700111N16Rik | 13062 | 3 | 4 | | | IV-1 | 2610507I01Rik |
| 12978 | 3 | 4 | | | | IV-1 | 1700112H15Rik | 13063 | 3 | 4 | | | IV-1 | 2700069I18Rik |
| 12979 | 3 | 4 | | | | IV-1 | 1700113H08Rik | 13064 | 3 | 4 | | | IV-1 | 2700070H01Rik |
| 12980 | 3 | 4 | | | | IV-1 | 1700121N20Rik | 13065 | 3 | 4 | | | IV-1 | 2700089E24Rik |
| 12981 | 3 | 4 | | | | IV-1 | 1700122O11Rik | 13066 | 3 | 4 | | | IV-1 | 2700089I24Rik |
| 12982 | 3 | 4 | | | | IV-1 | 1700123O12Rik | 13067 | 3 | 4 | | | IV-1 | 2700094K13Rik |
| 12983 | 3 | 4 | | | | IV-1 | 1700123O21Rik | 13068 | 3 | 4 | | | IV-1 | 2810013P06Rik |
| 12984 | 3 | 4 | | | | IV-1 | 1700125G22Rik | 13069 | 3 | 4 | | | IV-1 | 2810047C21Rik1 |
| 12985 | 3 | 4 | | | | IV-1 | 1700125H20Rik | 13070 | 3 | 4 | | | IV-1 | 2810049E08Rik |
| 12986 | 3 | 4 | | | | IV-1 | 1700128A07Rik | 13071 | 3 | 4 | | | IV-1 | 2810055G20Rik |
| 12987 | 3 | 4 | | | | IV-1 | 1810011O10Rik | 13072 | 3 | 4 | | | IV-1 | 2810403A07Rik |
| 12988 | 3 | 4 | | | | IV-1 | 1810012K16Rik | 13073 | 3 | 4 | | | IV-1 | 2810410L24Rik |
| 12989 | 3 | 4 | | | | IV-1 | 1810013L24Rik | 13074 | 3 | 4 | | | IV-1 | 2810429I04Rik |
| 12990 | 3 | 4 | | | | IV-1 | 1810020O05Rik | 13075 | 3 | 4 | | | IV-1 | 2810433D01Rik |
| 12991 | 3 | 4 | | | | IV-1 | 1810024B03Rik | 13076 | 3 | 4 | | | IV-1 | 2810442N19Rik |
| 12992 | 3 | 4 | | | | IV-1 | 1810026B05Rik | 13077 | 3 | 4 | | | IV-1 | 2810454H06Rik |
| 12993 | 3 | 4 | | | | IV-1 | 1810026J23Rik | 13078 | 3 | 4 | | | IV-1 | 2810459M11Rik |
| 12994 | 3 | 4 | | | | IV-1 | 1810030O07Rik | 13079 | 3 | 4 | | | IV-1 | 2810471M01Rik |
| 12995 | 3 | 4 | | | | IV-1 | 1810043G02Rik | 13080 | 3 | 4 | | | IV-1 | 2900008C10Rik |
| 12996 | 3 | 4 | | | | IV-1 | 1810046K07Rik | 13081 | 3 | 4 | | | IV-1 | 2900011O08Rik |
| 12997 | 3 | 4 | | | | IV-1 | 1810064F22Rik | 13082 | 3 | 4 | | | IV-1 | 2900052N01Rik |
| 12998 | 3 | 4 | | | | IV-1 | 2010001E11Rik | 13083 | 3 | 4 | | | IV-1 | 2900055J20Rik |
| 12999 | 3 | 4 | | | | IV-1 | 2010005H15Rik | 13084 | 3 | 4 | | | IV-1 | 2900056M20Rik |
| 13000 | 3 | 4 | | | | IV-1 | 2010009K17Rik | 13085 | 3 | 4 | | | IV-1 | 2900060B14Rik |
| 13001 | 3 | 4 | | | | IV-1 | 2010106C02Rik | 13086 | 3 | 4 | | | IV-1 | 2900092C05Rik |
| 13002 | 3 | 4 | | | | IV-1 | 2010107G12Rik | 13087 | 3 | 4 | | | IV-1 | 3010001F23Rik |

Fig. 43 - 78

| | | | | | | | |
|---|---|---|---|---|---|---|---|
| 13088 | 3 | 4 | | | IV-1 | 3100003L05Rik |
| 13089 | 3 | 4 | | | IV-1 | 3110021A11Rik |
| 13090 | 3 | 4 | | | IV-1 | 3110035E14Rik |
| 13091 | 3 | 4 | | | IV-1 | 3110039I08Rik |
| 13092 | 3 | 4 | | | IV-1 | 3110045C21Rik |
| 13093 | 3 | 4 | | | IV-1 | 3110079O15Rik |
| 13094 | 3 | 4 | | | IV-1 | 3110082J24Rik |
| 13095 | 3 | 4 | | | IV-1 | 3200001D21Rik |
| 13096 | 3 | 4 | | | IV-1 | 3300002I08Rik |
| 13097 | 3 | 4 | | | IV-1 | 3300005D01Rik |
| 13098 | 3 | 4 | | | IV-1 | 3830406C13Rik |
| 13099 | 3 | 4 | | | IV-1 | 3830408C21Rik |
| 13100 | 3 | 4 | | | IV-1 | 3830417A13Rik |
| 13101 | 3 | 4 | | | IV-1 | 3930402G23Rik |
| 13102 | 3 | 4 | | | IV-1 | 4632427E13Rik |
| 13103 | 3 | 4 | | | IV-1 | 4632428N05Rik |
| 13104 | 3 | 4 | | | IV-1 | 4732456N10Rik |
| 13105 | 3 | 4 | | | IV-1 | 4732490B19Rik |
| 13106 | 3 | 4 | | | IV-1 | 4732491K20Rik |
| 13107 | 3 | 4 | | | IV-1 | 4833412C05Rik |
| 13108 | 3 | 4 | | | IV-1 | 4833424O15Rik |
| 13109 | 3 | 4 | | | IV-1 | 4833427G06Rik |
| 13110 | 3 | 4 | | | IV-1 | 4833428L15Rik |
| 13111 | 3 | 4 | | | IV-1 | 4921501E09Rik |
| 13112 | 3 | 4 | | | IV-1 | 4921504E06Rik |
| 13113 | 3 | 4 | | | IV-1 | 4921506M07Rik |
| 13114 | 3 | 4 | | | IV-1 | 4921509C19Rik |
| 13115 | 3 | 4 | | | IV-1 | 4921511C10Rik |
| 13116 | 3 | 4 | | | IV-1 | 4921511H03Rik |
| 13117 | 3 | 4 | | | IV-1 | 4921517D22Rik |
| 13118 | 3 | 4 | | | IV-1 | 4921531P14Rik |
| 13119 | 3 | 4 | | | IV-1 | 4922502N22Rik |
| 13120 | 3 | 4 | | | IV-1 | 4930401O10Rik |
| 13121 | 3 | 4 | | | IV-1 | 4930404A10Rik |
| 13122 | 3 | 4 | | | IV-1 | 4930405J17Rik |
| 13123 | 3 | 4 | | | IV-1 | 4930406D18Rik |
| 13124 | 3 | 4 | | | IV-1 | 4930412B13Rik |
| 13125 | 3 | 4 | | | IV-1 | 4930414L22Rik |
| 13126 | 3 | 4 | | | IV-1 | 4930414N06Rik |
| 13127 | 3 | 4 | | | IV-1 | 4930415L06Rik |
| 13128 | 3 | 4 | | | IV-1 | 4930417O22Rik |
| 13129 | 3 | 4 | | | IV-1 | 4930425O10Rik |
| 13130 | 3 | 4 | | | IV-1 | 4930428O21Rik |
| 13131 | 3 | 4 | | | IV-1 | 4930429B21Rik |
| 13132 | 3 | 4 | | | IV-1 | 4930429D17Rik |
| 13133 | 3 | 4 | | | IV-1 | 4930430A15Rik |
| 13134 | 3 | 4 | | | IV-1 | 4930431F12Rik |
| 13135 | 3 | 4 | | | IV-1 | 4930431P03Rik |
| 13136 | 3 | 4 | | | IV-1 | 4930432J09Rik |
| 13137 | 3 | 4 | | | IV-1 | 4930432M17Rik |
| 13138 | 3 | 4 | | | IV-1 | 4930433I11Rik |
| 13139 | 3 | 4 | | | IV-1 | 4930433N12Rik |
| 13140 | 3 | 4 | | | IV-1 | 4930435E12Rik |
| 13141 | 3 | 4 | | | IV-1 | 4930443O20Rik |
| 13142 | 3 | 4 | | | IV-1 | 4930444F02Rik |
| 13143 | 3 | 4 | | | IV-1 | 4930447A16Rik |
| 13144 | 3 | 4 | | | IV-1 | 4930447J18Rik |
| 13145 | 3 | 4 | | | IV-1 | 4930448C13Rik |
| 13146 | 3 | 4 | | | IV-1 | 4930449E01Rik |
| 13147 | 3 | 4 | | | IV-1 | 4930452G13Rik |
| 13148 | 3 | 4 | | | IV-1 | 4930453H23Rik |
| 13149 | 3 | 4 | | | IV-1 | 4930455H04Rik |
| 13150 | 3 | 4 | | | IV-1 | 4930455J16Rik |
| 13151 | 3 | 4 | | | IV-1 | 4930459C07Rik |
| 13152 | 3 | 4 | | | IV-1 | 4930465M20Rik |
| 13153 | 3 | 4 | | | IV-1 | 4930467K11Rik |
| 13154 | 3 | 4 | | | IV-1 | 4930468A15Rik |
| 13155 | 3 | 4 | | | IV-1 | 4930470P17Rik |
| 13156 | 3 | 4 | | | IV-1 | 4930471C04Rik |
| 13157 | 3 | 4 | | | IV-1 | 4930471M09Rik |
| 13158 | 3 | 4 | | | IV-1 | 4930474N09Rik |
| 13159 | 3 | 4 | | | IV-1 | 4930478L05Rik |
| 13160 | 3 | 4 | | | IV-1 | 4930480E11Rik |
| 13161 | 3 | 4 | | | IV-1 | 4930482G09Rik |
| 13162 | 3 | 4 | | | IV-1 | 4930500J02Rik |
| 13163 | 3 | 4 | | | IV-1 | 4930503E14Rik |
| 13164 | 3 | 4 | | | IV-1 | 4930503O07Rik |
| 13165 | 3 | 4 | | | IV-1 | 4930505G20Rik |
| 13166 | 3 | 4 | | | IV-1 | 4930509J09Rik |
| 13167 | 3 | 4 | | | IV-1 | 4930509K18Rik |
| 13168 | 3 | 4 | | | IV-1 | 4930511A02Rik |
| 13169 | 3 | 4 | | | IV-1 | 4930511E03Rik |
| 13170 | 3 | 4 | | | IV-1 | 4930512B01Rik |
| 13171 | 3 | 4 | | | IV-1 | 4930515L03Rik |
| 13172 | 3 | 4 | | | IV-1 | 4930518P08Rik |
| 13173 | 3 | 4 | | | IV-1 | 4930519D14Rik |
| 13174 | 3 | 4 | | | IV-1 | 4930519H02Rik |
| 13175 | 3 | 4 | | | IV-1 | 4930520P13Rik |
| 13176 | 3 | 4 | | | IV-1 | 4930522H14Rik |
| 13177 | 3 | 4 | | | IV-1 | 4930523O13Rik |
| 13178 | 3 | 4 | | | IV-1 | 4930524B15Rik |
| 13179 | 3 | 4 | | | IV-1 | 4930524O08Rik |
| 13180 | 3 | 4 | | | IV-1 | 4930525G20Rik |
| 13181 | 3 | 4 | | | IV-1 | 4930528P14Rik |
| 13182 | 3 | 4 | | | IV-1 | 4930532M18Rik |
| 13183 | 3 | 4 | | | IV-1 | 4930540M03Rik |
| 13184 | 3 | 4 | | | IV-1 | 4930542D17Rik |
| 13185 | 3 | 4 | | | IV-1 | 4930543E12Rik |
| 13186 | 3 | 4 | | | IV-1 | 4930544D05Rik |
| 13187 | 3 | 4 | | | IV-1 | 4930546K05Rik |
| 13188 | 3 | 4 | | | IV-1 | 4930547E14Rik |
| 13189 | 3 | 4 | | | IV-1 | 4930548G14Rik |
| 13190 | 3 | 4 | | | IV-1 | 4930548K13Rik |
| 13191 | 3 | 4 | | | IV-1 | 4930554C24Rik |
| 13192 | 3 | 4 | | | IV-1 | 4930555B11Rik |
| 13193 | 3 | 4 | | | IV-1 | 4930556C24Rik |
| 13194 | 3 | 4 | | | IV-1 | 4930556G01Rik |
| 13195 | 3 | 4 | | | IV-1 | 4930556N09Rik |
| 13196 | 3 | 4 | | | IV-1 | 4930558J18Rik |
| 13197 | 3 | 4 | | | IV-1 | 4930558K02Rik |
| 13198 | 3 | 4 | | | IV-1 | 4930563E22Rik |
| 13199 | 3 | 4 | | | IV-1 | 4930563M20Rik |
| 13200 | 3 | 4 | | | IV-1 | 4930564B18Rik |
| 13201 | 3 | 4 | | | IV-1 | 4930564C03Rik |
| 13202 | 3 | 4 | | | IV-1 | 4930567H12Rik |
| 13203 | 3 | 4 | | | IV-1 | 4930568E12Rik |
| 13204 | 3 | 4 | | | IV-1 | 4930572O13Rik |
| 13205 | 3 | 4 | | | IV-1 | 4930573O16Rik |
| 13206 | 3 | 4 | | | IV-1 | 4930578E11Rik |
| 13207 | 3 | 4 | | | IV-1 | 4930578M01Rik |
| 13208 | 3 | 4 | | | IV-1 | 4930579F01Rik |
| 13209 | 3 | 4 | | | IV-1 | 4930579G18Rik |
| 13210 | 3 | 4 | | | IV-1 | 4930583K01Rik |
| 13211 | 3 | 4 | | | IV-1 | 4930584F24Rik |
| 13212 | 3 | 4 | | | IV-1 | 4930590J08Rik |
| 13213 | 3 | 4 | | | IV-1 | 4930590L20Rik |
| 13214 | 3 | 4 | | | IV-1 | 4930591A17Rik |
| 13215 | 3 | 4 | | | IV-1 | 4930592I03Rik |
| 13216 | 3 | 4 | | | IV-1 | 4930595M18Rik |
| 13217 | 3 | 4 | | | IV-1 | 4930596D02Rik |
| 13218 | 3 | 4 | | | IV-1 | 4930597G03Rik |
| 13219 | 3 | 4 | | | IV-1 | 4931406H21Rik |
| 13220 | 3 | 4 | | | IV-1 | 4931408C20Rik |
| 13221 | 3 | 4 | | | IV-1 | 4931412M21 |
| 13222 | 3 | 4 | | | IV-1 | 4931417E11Rik |
| 13223 | 3 | 4 | | | IV-1 | 4931423N10Rik |
| 13224 | 3 | 4 | | | IV-1 | 4931430N09Rik |
| 13225 | 3 | 4 | | | IV-1 | 4931431C16Rik |
| 13226 | 3 | 4 | | | IV-1 | 4932414N04Rik |
| 13227 | 3 | 4 | | | IV-1 | 4932415M13Rik |
| 13228 | 3 | 4 | | | IV-1 | 4932429P05Rik |
| 13229 | 3 | 4 | | | IV-1 | 4933400B14Rik |
| 13230 | 3 | 4 | | | IV-1 | 4933400C23Rik |
| 13231 | 3 | 4 | | | IV-1 | 4933400L20Rik |
| 13232 | 3 | 4 | | | IV-1 | 4933401B06Rik |
| 13233 | 3 | 4 | | | IV-1 | 4933402J10Rik |
| 13234 | 3 | 4 | | | IV-1 | 4933402N22Rik |
| 13235 | 3 | 4 | | | IV-1 | 4933405D12Rik |
| 13236 | 3 | 4 | | | IV-1 | 4933405L10Rik |
| 13237 | 3 | 4 | | | IV-1 | 4933406D12Rik |
| 13238 | 3 | 4 | | | IV-1 | 4933406F09Rik |
| 13239 | 3 | 4 | | | IV-1 | 4933406J08Rik |
| 13240 | 3 | 4 | | | IV-1 | 4933406J10Rik |
| 13241 | 3 | 4 | | | IV-1 | 4933406K04Rik |
| 13242 | 3 | 4 | | | IV-1 | 4933407E24Rik |
| 13243 | 3 | 4 | | | IV-1 | 4933407G14Rik |
| 13244 | 3 | 4 | | | IV-1 | 4933409G03Rik |
| 13245 | 3 | 4 | | | IV-1 | 4933409K07Rik |
| 13246 | 3 | 4 | | | IV-1 | 4933411G06Rik |
| 13247 | 3 | 4 | | | IV-1 | 4933413J09Rik |
| 13248 | 3 | 4 | | | IV-1 | 4933413L06Rik |
| 13249 | 3 | 4 | | | IV-1 | 4933416I08Rik |
| 13250 | 3 | 4 | | | IV-1 | 4933416M07Rik |
| 13251 | 3 | 4 | | | IV-1 | 4933422A05Rik |
| 13252 | 3 | 4 | | | IV-1 | 4933424G05Rik |
| 13253 | 3 | 4 | | | IV-1 | 4933424G06Rik |
| 13254 | 3 | 4 | | | IV-1 | 4933425B07Rik |
| 13255 | 3 | 4 | | | IV-1 | 4933425L06Rik |
| 13256 | 3 | 4 | | | IV-1 | 4933427D06Rik |
| 13257 | 3 | 4 | | | IV-1 | 4933427E11Rik |

Fig. 43 - 79

| | | | | | | | |
|---|---|---|---|---|---|---|---|
| 13258 | 3 | 4 | | | | IV-1 | 4933428G20Rik |
| 13259 | 3 | 4 | | | | IV-1 | 4933429K18Rik |
| 13260 | 3 | 4 | | | | IV-1 | 4933430H16Rik |
| 13261 | 3 | 4 | | | | IV-1 | 4933430I17Rik |
| 13262 | 3 | 4 | | | | IV-1 | 4933432G23Rik |
| 13263 | 3 | 4 | | | | IV-1 | 4933432I03Rik |
| 13264 | 3 | 4 | | | | IV-1 | 4933432I09Rik |
| 13265 | 3 | 4 | | | | IV-1 | 4933433C11Rik |
| 13266 | 3 | 4 | | | | IV-1 | 4933433F19Rik |
| 13267 | 3 | 4 | | | | IV-1 | 4933436H12Rik |
| 13268 | 3 | 4 | | | | IV-1 | 4933436I01Rik |
| 13269 | 3 | 4 | | | | IV-1 | 4933438K21Rik |
| 13270 | 3 | 4 | | | | IV-1 | 5031425F14Rik |
| 13271 | 3 | 4 | | | | IV-1 | 5033403H07Rik |
| 13272 | 3 | 4 | | | | IV-1 | 5330411J11Rik |
| 13273 | 3 | 4 | | | | IV-1 | 5330413P13Rik |
| 13274 | 3 | 4 | | | | IV-1 | 5330417C22Rik |
| 13275 | 3 | 4 | | | | IV-1 | 5330434G04Rik |
| 13276 | 3 | 4 | | | | IV-1 | 5430402E10Rik |
| 13277 | 3 | 4 | | | | IV-1 | 5430402O13Rik |
| 13278 | 3 | 4 | | | | IV-1 | 5430403N17Rik |
| 13279 | 3 | 4 | | | | IV-1 | 5430421N21Rik |
| 13280 | 3 | 4 | | | | IV-1 | 5430427O19Rik |
| 13281 | 3 | 4 | | | | IV-1 | 5430428K19Rik |
| 13282 | 3 | 4 | | | | IV-1 | 5430434I15Rik |
| 13283 | 3 | 4 | | | | IV-1 | 5430435G22Rik |
| 13284 | 3 | 4 | | | | IV-1 | 5430437J10Rik |
| 13285 | 3 | 4 | | | | IV-1 | 5430440P10Rik |
| 13286 | 3 | 4 | | | | IV-1 | 5530400C23Rik |
| 13287 | 3 | 4 | | | | IV-1 | 5730403I07Rik |
| 13288 | 3 | 4 | | | | IV-1 | 5730435O14Rik |
| 13289 | 3 | 4 | | | | IV-1 | 5730455P16Rik |
| 13290 | 3 | 4 | | | | IV-1 | 5730460C07Rik |
| 13291 | 3 | 4 | | | | IV-1 | 5730508B09Rik |
| 13292 | 3 | 4 | | | | IV-1 | 5830403L16Rik |
| 13293 | 3 | 4 | | | | IV-1 | 5830416I19Rik |
| 13294 | 3 | 4 | | | | IV-1 | 5930438M14Rik |
| 13295 | 3 | 4 | | | | IV-1 | 6030407O03Rik |
| 13296 | 3 | 4 | | | | IV-1 | 6030443J06Rik |
| 13297 | 3 | 4 | | | | IV-1 | 6030466F02Rik |
| 13298 | 3 | 4 | | | | IV-1 | 6030469F06Rik |
| 13299 | 3 | 4 | | | | IV-1 | 6330403A02Rik |
| 13300 | 3 | 4 | | | | IV-1 | 6330407A03Rik |
| 13301 | 3 | 4 | | | | IV-1 | 6330410L21Rik |
| 13302 | 3 | 4 | | | | IV-1 | 6330415B21Rik |
| 13303 | 3 | 4 | | | | IV-1 | 6330416G13Rik |
| 13304 | 3 | 4 | | | | IV-1 | 6330419J24Rik |
| 13305 | 3 | 4 | | | | IV-1 | 6330549D23Rik |
| 13306 | 3 | 4 | | | | IV-1 | 6430531B16Rik |
| 13307 | 3 | 4 | | | | IV-1 | 6430584L05Rik |
| 13308 | 3 | 4 | | | | IV-1 | 6430706D22Rik |
| 13309 | 3 | 4 | | | | IV-1 | 6430710C18Rik |
| 13310 | 3 | 4 | | | | IV-1 | 6530411M01Rik |
| 13311 | 3 | 4 | | | | IV-1 | 6720416L17Rik |
| 13312 | 3 | 4 | | | | IV-1 | 6720483E21Rik |
| 13313 | 3 | 4 | | | | IV-1 | 6820408C15Rik |
| 13314 | 3 | 4 | | | | IV-1 | 7420426K07Rik |
| 13315 | 3 | 4 | | | | IV-1 | 7420461P10Rik |
| 13316 | 3 | 4 | | | | IV-1 | 7420701I03Rik |
| 13317 | 3 | 4 | | | | IV-1 | 7530416G11Rik |
| 13318 | 3 | 4 | | | | IV-1 | 7630403G23Rik |
| 13319 | 3 | 4 | | | | IV-1 | 8030423F21Rik |
| 13320 | 3 | 4 | | | | IV-1 | 8430427H17Rik |
| 13321 | 3 | 4 | | | | IV-1 | 8430429K09Rik |
| 13322 | 3 | 4 | | | | IV-1 | 8430431K14Rik |
| 13323 | 3 | 4 | | | | IV-1 | 9030204H09Rik |
| 13324 | 3 | 4 | | | | IV-1 | 9030404E10Rik |
| 13325 | 3 | 4 | | | | IV-1 | 9030624G23Rik |
| 13326 | 3 | 4 | | | | IV-1 | 9030625G05Rik |
| 13327 | 3 | 4 | | | | IV-1 | 9130011E15Rik |
| 13328 | 3 | 4 | | | | IV-1 | 9130015A21Rik |
| 13329 | 3 | 4 | | | | IV-1 | 9130019O22Rik |
| 13330 | 3 | 4 | | | | IV-1 | 9130019P16Rik |
| 13331 | 3 | 4 | | | | IV-1 | 9130024F11Rik |
| 13332 | 3 | 4 | | | | IV-1 | 9130221F21Rik |
| 13333 | 3 | 4 | | | | IV-1 | 9130221H12Rik |
| 13334 | 3 | 4 | | | | IV-1 | 9130227L01Rik |
| 13335 | 3 | 4 | | | | IV-1 | 9230102K24Rik |
| 13336 | 3 | 4 | | | | IV-1 | 9230104J09Rik |
| 13337 | 3 | 4 | | | | IV-1 | 9230105E05Rik |
| 13338 | 3 | 4 | | | | IV-1 | 9330111N05Rik |
| 13339 | 3 | 4 | | | | IV-1 | 9330117O12Rik |
| 13340 | 3 | 4 | | | | IV-1 | 9330151L19Rik |
| 13341 | 3 | 4 | | | | IV-1 | 9330158H04Rik |
| 13342 | 3 | 4 | | | | IV-1 | 9330162O12Rik |
| 13343 | 3 | 4 | | | | IV-1 | 9330162B11Rik |
| 13344 | 3 | 4 | | | | IV-1 | 9330175E14Rik |
| 13345 | 3 | 4 | | | | IV-1 | 9330175M20Rik |
| 13346 | 3 | 4 | | | | IV-1 | 9330178D15Rik |
| 13347 | 3 | 4 | | | | IV-1 | 9330182L06Rik |
| 13348 | 3 | 4 | | | | IV-1 | 9330188P03Rik |
| 13349 | 3 | 4 | | | | IV-1 | 9430014N10Rik |
| 13350 | 3 | 4 | | | | IV-1 | 9430018G01Rik |
| 13351 | 3 | 4 | | | | IV-1 | 9430019J16Rik |
| 13352 | 3 | 4 | | | | IV-1 | 9430037G07Rik |
| 13353 | 3 | 4 | | | | IV-1 | 9430076C15Rik |
| 13354 | 3 | 4 | | | | IV-1 | 9530002B09Rik |
| 13355 | 3 | 4 | | | | IV-1 | 9530026F06Rik |
| 13356 | 3 | 4 | | | | IV-1 | 9530036O11Rik |
| 13357 | 3 | 4 | | | | IV-1 | 9530059O14Rik |
| 13358 | 3 | 4 | | | | IV-1 | 9530068E07Rik |
| 13359 | 3 | 4 | | | | IV-1 | 9530091C08Rik |
| 13360 | 3 | 4 | | | | IV-1 | 9630013A20Rik |
| 13361 | 3 | 4 | | | | IV-1 | 9630028B13Rik |
| 13362 | 3 | 4 | | | | IV-1 | 9630028H03Rik |
| 13363 | 3 | 4 | | | | IV-1 | 9830107B12Rik |
| 13364 | 3 | 4 | | | | IV-1 | 9930014A18Rik |
| 13365 | 3 | 4 | | | | IV-1 | 9930111H07Rik |
| 13366 | 3 | 4 | | | | IV-1 | a |
| 13367 | 3 | 4 | | | | IV-1 | A130010J15Rik |
| 13368 | 3 | 4 | | | | IV-1 | A1cf |
| 13369 | 3 | 4 | | | | IV-1 | A230001M10Rik |
| 13370 | 3 | 4 | | | | IV-1 | A230009B12Rik |
| 13371 | 3 | 4 | | | | IV-1 | A230020J21Rik |
| 13372 | 3 | 4 | | | | IV-1 | A230028O05Rik |
| 13373 | 3 | 4 | | | | IV-1 | A230050P20Rik |
| 13374 | 3 | 4 | | | | IV-1 | A230070E04Rik |
| 13375 | 3 | 4 | | | | IV-1 | A230073K19Rik |
| 13376 | 3 | 4 | | | | IV-1 | A230077H06Rik |
| 13377 | 3 | 4 | | | | IV-1 | A2m |
| 13378 | 3 | 4 | | | | IV-1 | A330032B11Rik |
| 13379 | 3 | 4 | | | | IV-1 | A330041J22Rik |
| 13380 | 3 | 4 | | | | IV-1 | A330074K22Rik |
| 13381 | 3 | 4 | | | | IV-1 | A330102I10Rik |
| 13382 | 3 | 4 | | | | IV-1 | A430033K04Rik |
| 13383 | 3 | 4 | | | | IV-1 | A430088P11Rik |
| 13384 | 3 | 4 | | | | IV-1 | A430090L17Rik |
| 13385 | 3 | 4 | | | | IV-1 | A430093F15Rik |
| 13386 | 3 | 4 | | | | IV-1 | A530046M15Rik |
| 13387 | 3 | 4 | | | | IV-1 | A530058N18Rik |
| 13388 | 3 | 4 | | | | IV-1 | A530072M11Rik |
| 13389 | 3 | 4 | | | | IV-1 | A530099J19Rik |
| 13390 | 3 | 4 | | | | IV-1 | A630012P03Rik |
| 13391 | 3 | 4 | | | | IV-1 | A630019I02Rik |
| 13392 | 3 | 4 | | | | IV-1 | A630020A06 |
| 13393 | 3 | 4 | | | | IV-1 | A630023A22Rik |
| 13394 | 3 | 4 | | | | IV-1 | A630075F10Rik |
| 13395 | 3 | 4 | | | | IV-1 | A630076J17Rik |
| 13396 | 3 | 4 | | | | IV-1 | A630095E13Rik |
| 13397 | 3 | 4 | | | | IV-1 | A630095N17Rik |
| 13398 | 3 | 4 | | | | IV-1 | A730017C20Rik |
| 13399 | 3 | 4 | | | | IV-1 | A730020E08Rik |
| 13400 | 3 | 4 | | | | IV-1 | A730036I17Rik |
| 13401 | 3 | 4 | | | | IV-1 | A730043L09Rik |
| 13402 | 3 | 4 | | | | IV-1 | A730046J19Rik |
| 13403 | 3 | 4 | | | | IV-1 | A730082K24Rik |
| 13404 | 3 | 4 | | | | IV-1 | A730085K08Rik |
| 13405 | 3 | 4 | | | | IV-1 | A730090H04Rik |
| 13406 | 3 | 4 | | | | IV-1 | A830009L08Rik |
| 13407 | 3 | 4 | | | | IV-1 | A830082N09Rik |
| 13408 | 3 | 4 | | | | IV-1 | A930001A20Rik |
| 13409 | 3 | 4 | | | | IV-1 | A930003O13Rik |
| 13410 | 3 | 4 | | | | IV-1 | A930006I01Rik |
| 13411 | 3 | 4 | | | | IV-1 | A930009A15Rik |
| 13412 | 3 | 4 | | | | IV-1 | A930011G23Rik |
| 13413 | 3 | 4 | | | | IV-1 | A930011O12Rik |
| 13414 | 3 | 4 | | | | IV-1 | A930041C12Rik |
| 13415 | 3 | 4 | | | | IV-1 | AA387883 |
| 13416 | 3 | 4 | | | | IV-1 | AA474331 |
| 13417 | 3 | 4 | | | | IV-1 | AA536875 |
| 13418 | 3 | 4 | | | | IV-1 | AA543186 |
| 13419 | 3 | 4 | | | | IV-1 | AA543401 |
| 13420 | 3 | 4 | | | | IV-1 | AA545190 |
| 13421 | 3 | 4 | | | | IV-1 | AA619741 |
| 13422 | 3 | 4 | | | | IV-1 | AA792892 |
| 13423 | 3 | 4 | | | | IV-1 | Aadat |
| 13424 | 3 | 4 | | | | IV-1 | Aagab |
| 13425 | 3 | 4 | | | | IV-1 | Aanat |
| 13426 | 3 | 4 | | | | IV-1 | Aar2 |
| 13427 | 3 | 4 | | | | IV-1 | Aasdhppt |

Fig. 43 - 80

| | | | | | | | |
|---|---|---|---|---|---|---|---|
| 13428 | 3 | 4 | | | | IV-1 | Aass |
| 13429 | 3 | 4 | | | | IV-1 | Abca12 |
| 13430 | 3 | 4 | | | | IV-1 | Abca14 |
| 13431 | 3 | 4 | | | | IV-1 | Abca15 |
| 13432 | 3 | 4 | | | | IV-1 | Abca16 |
| 13433 | 3 | 4 | | | | IV-1 | Abca17 |
| 13434 | 3 | 4 | | | | IV-1 | Abca2 |
| 13435 | 3 | 4 | | | | IV-1 | Abca7 |
| 13436 | 3 | 4 | | | | IV-1 | Abca8b |
| 13437 | 3 | 4 | | | | IV-1 | Abcb10 |
| 13438 | 3 | 4 | | | | IV-1 | Abcb11 |
| 13439 | 3 | 4 | | | | IV-1 | Abcb1b |
| 13440 | 3 | 4 | | | | IV-1 | Abcb5 |
| 13441 | 3 | 4 | | | | IV-1 | Abcc1 |
| 13442 | 3 | 4 | | | | IV-1 | Abcc12 |
| 13443 | 3 | 4 | | | | IV-1 | Abcc2 |
| 13444 | 3 | 4 | | | | IV-1 | Abcc6 |
| 13445 | 3 | 4 | | | | IV-1 | Abcc9 |
| 13446 | 3 | 4 | | | | IV-1 | Abcd3 |
| 13447 | 3 | 4 | | | | IV-1 | Abcf1 |
| 13448 | 3 | 4 | | | | IV-1 | Abcf2 |
| 13449 | 3 | 4 | | | | IV-1 | Abcg8 |
| 13450 | 3 | 4 | | | | IV-1 | Abhd1 |
| 13451 | 3 | 4 | | | | IV-1 | Abhd12 |
| 13452 | 3 | 4 | | | | IV-1 | Abhd12b |
| 13453 | 3 | 4 | | | | IV-1 | Abhd13 |
| 13454 | 3 | 4 | | | | IV-1 | Abhd16b |
| 13455 | 3 | 4 | | | | IV-1 | Abhd17a |
| 13456 | 3 | 4 | | | | IV-1 | Abhd17b |
| 13457 | 3 | 4 | | | | IV-1 | Abhd17c |
| 13458 | 3 | 4 | | | | IV-1 | Abhd5 |
| 13459 | 3 | 4 | | | | IV-1 | Abi1 |
| 13460 | 3 | 4 | | | | IV-1 | Abl1 |
| 13461 | 3 | 4 | | | | IV-1 | Ablim3 |
| 13462 | 3 | 4 | | | | IV-1 | Abo |
| 13463 | 3 | 4 | | | | IV-1 | Abr |
| 13464 | 3 | 4 | | | | IV-1 | Acad10 |
| 13465 | 3 | 4 | | | | IV-1 | Acad9 |
| 13466 | 3 | 4 | | | | IV-1 | Acadsb |
| 13467 | 3 | 4 | | | | IV-1 | Acadvl |
| 13468 | 3 | 4 | | | | IV-1 | Acan |
| 13469 | 3 | 4 | | | | IV-1 | Acap3 |
| 13470 | 3 | 4 | | | | IV-1 | Acat1 |
| 13471 | 3 | 4 | | | | IV-1 | Acbd5 |
| 13472 | 3 | 4 | | | | IV-1 | Acbd6 |
| 13473 | 3 | 4 | | | | IV-1 | Accs |
| 13474 | 3 | 4 | | | | IV-1 | Accsl |
| 13475 | 3 | 4 | | | | IV-1 | Acd |
| 13476 | 3 | 4 | | | | IV-1 | Acer1 |
| 13477 | 3 | 4 | | | | IV-1 | Acin1 |
| 13478 | 3 | 4 | | | | IV-1 | Acly |
| 13479 | 3 | 4 | | | | IV-1 | Acmsd |
| 13480 | 3 | 4 | | | | IV-1 | Aco1 |
| 13481 | 3 | 4 | | | | IV-1 | Aco2 |
| 13482 | 3 | 4 | | | | IV-1 | Acot10 |
| 13483 | 3 | 4 | | | | IV-1 | Acot13 |
| 13484 | 3 | 4 | | | | IV-1 | Acot8 |
| 13485 | 3 | 4 | | | | IV-1 | Acox1 |
| 13486 | 3 | 4 | | | | IV-1 | Acox2 |
| 13487 | 3 | 4 | | | | IV-1 | Acox3 |
| 13488 | 3 | 4 | | | | IV-1 | Acoxl |
| 13489 | 3 | 4 | | | | IV-1 | Acp1 |
| 13490 | 3 | 4 | | | | IV-1 | Acp2 |
| 13491 | 3 | 4 | | | | IV-1 | Acsbg2 |
| 13492 | 3 | 4 | | | | IV-1 | Acsm2 |
| 13493 | 3 | 4 | | | | IV-1 | Acsm3 |
| 13494 | 3 | 4 | | | | IV-1 | Acsm4 |
| 13495 | 3 | 4 | | | | IV-1 | Acss2 |
| 13496 | 3 | 4 | | | | IV-1 | Actbl2 |
| 13497 | 3 | 4 | | | | IV-1 | Actl10 |
| 13498 | 3 | 4 | | | | IV-1 | Actl11 |
| 13499 | 3 | 4 | | | | IV-1 | Actl6b |
| 13500 | 3 | 4 | | | | IV-1 | Actr10 |
| 13501 | 3 | 4 | | | | IV-1 | Actr1b |
| 13502 | 3 | 4 | | | | IV-1 | Actr2 |
| 13503 | 3 | 4 | | | | IV-1 | Actr3 |
| 13504 | 3 | 4 | | | | IV-1 | Actr3b |
| 13505 | 3 | 4 | | | | IV-1 | Actr5 |
| 13506 | 3 | 4 | | | | IV-1 | Actrt1 |
| 13507 | 3 | 4 | | | | IV-1 | Actrt3 |
| 13508 | 3 | 4 | | | | IV-1 | Acvr1 |
| 13509 | 3 | 4 | | | | IV-1 | Acvr1c |
| 13510 | 3 | 4 | | | | IV-1 | Adad1 |
| 13511 | 3 | 4 | | | | IV-1 | Adad2 |
| 13512 | 3 | 4 | | | | IV-1 | Adal |
| 13513 | 3 | 4 | | | | IV-1 | Adam10 |
| 13514 | 3 | 4 | | | | IV-1 | Adam11 |
| 13515 | 3 | 4 | | | | IV-1 | Adam17 |
| 13516 | 3 | 4 | | | | IV-1 | Adam18 |
| 13517 | 3 | 4 | | | | IV-1 | Adam2 |
| 13518 | 3 | 4 | | | | IV-1 | Adam20 |
| 13519 | 3 | 4 | | | | IV-1 | Adam21 |
| 13520 | 3 | 4 | | | | IV-1 | Adam24 |
| 13521 | 3 | 4 | | | | IV-1 | Adam29 |
| 13522 | 3 | 4 | | | | IV-1 | Adam34 |
| 13523 | 3 | 4 | | | | IV-1 | Adamts13 |
| 13524 | 3 | 4 | | | | IV-1 | Adamts14 |
| 13525 | 3 | 4 | | | | IV-1 | Adamts16 |
| 13526 | 3 | 4 | | | | IV-1 | Adamts18 |
| 13527 | 3 | 4 | | | | IV-1 | Adamts20 |
| 13528 | 3 | 4 | | | | IV-1 | Adarb2 |
| 13529 | 3 | 4 | | | | IV-1 | Adc |
| 13530 | 3 | 4 | | | | IV-1 | Adck4 |
| 13531 | 3 | 4 | | | | IV-1 | Adcy1 |
| 13532 | 3 | 4 | | | | IV-1 | Adcy10 |
| 13533 | 3 | 4 | | | | IV-1 | Adcy4 |
| 13534 | 3 | 4 | | | | IV-1 | Adcyap1 |
| 13535 | 3 | 4 | | | | IV-1 | Add1 |
| 13536 | 3 | 4 | | | | IV-1 | Adgb |
| 13537 | 3 | 4 | | | | IV-1 | Adh4 |
| 13538 | 3 | 4 | | | | IV-1 | Adh6a |
| 13539 | 3 | 4 | | | | IV-1 | Adh6-ps1 |
| 13540 | 3 | 4 | | | | IV-1 | Adi1 |
| 13541 | 3 | 4 | | | | IV-1 | Adig |
| 13542 | 3 | 4 | | | | IV-1 | Adipor1 |
| 13543 | 3 | 4 | | | | IV-1 | Adipor2 |
| 13544 | 3 | 4 | | | | IV-1 | Adnp |
| 13545 | 3 | 4 | | | | IV-1 | Ado |
| 13546 | 3 | 4 | | | | IV-1 | Adpgk |
| 13547 | 3 | 4 | | | | IV-1 | Adprhl2 |
| 13548 | 3 | 4 | | | | IV-1 | Adprm |
| 13549 | 3 | 4 | | | | IV-1 | Adra2b |
| 13550 | 3 | 4 | | | | IV-1 | Adra2c |
| 13551 | 3 | 4 | | | | IV-1 | Adrbk1 |
| 13552 | 3 | 4 | | | | IV-1 | Aebp2 |
| 13553 | 3 | 4 | | | | IV-1 | Aes |
| 13554 | 3 | 4 | | | | IV-1 | AF067061 |
| 13555 | 3 | 4 | | | | IV-1 | AF067063 |
| 13556 | 3 | 4 | | | | IV-1 | AF357355 |
| 13557 | 3 | 4 | | | | IV-1 | AF357359 |
| 13558 | 3 | 4 | | | | IV-1 | AF357399 |
| 13559 | 3 | 4 | | | | IV-1 | AF357425 |
| 13560 | 3 | 4 | | | | IV-1 | AF366264 |
| 13561 | 3 | 4 | | | | IV-1 | Aff4 |
| 13562 | 3 | 4 | | | | IV-1 | Afg3l1 |
| 13563 | 3 | 4 | | | | IV-1 | Afg3l2 |
| 13564 | 3 | 4 | | | | IV-1 | Afm |
| 13565 | 3 | 4 | | | | IV-1 | Afp |
| 13566 | 3 | 4 | | | | IV-1 | Aftph |
| 13567 | 3 | 4 | | | | IV-1 | Agap2 |
| 13568 | 3 | 4 | | | | IV-1 | Agbl1 |
| 13569 | 3 | 4 | | | | IV-1 | Agbl2 |
| 13570 | 3 | 4 | | | | IV-1 | Agbl4 |
| 13571 | 3 | 4 | | | | IV-1 | Agbl5 |
| 13572 | 3 | 4 | | | | IV-1 | Aggf1 |
| 13573 | 3 | 4 | | | | IV-1 | Agk |
| 13574 | 3 | 4 | | | | IV-1 | Agmat |
| 13575 | 3 | 4 | | | | IV-1 | Agpat1 |
| 13576 | 3 | 4 | | | | IV-1 | Agpat3 |
| 13577 | 3 | 4 | | | | IV-1 | Agpat4 |
| 13578 | 3 | 4 | | | | IV-1 | Agpat6 |
| 13579 | 3 | 4 | | | | IV-1 | Agps |
| 13580 | 3 | 4 | | | | IV-1 | Agr2 |
| 13581 | 3 | 4 | | | | IV-1 | Agr3 |
| 13582 | 3 | 4 | | | | IV-1 | Agrn |
| 13583 | 3 | 4 | | | | IV-1 | Agtpbp1 |
| 13584 | 3 | 4 | | | | IV-1 | Agtr1a |
| 13585 | 3 | 4 | | | | IV-1 | Agtr2 |
| 13586 | 3 | 4 | | | | IV-1 | Agxt |
| 13587 | 3 | 4 | | | | IV-1 | Ahctf1 |
| 13588 | 3 | 4 | | | | IV-1 | Ahcyl1 |
| 13589 | 3 | 4 | | | | IV-1 | Ahcyl2 |
| 13590 | 3 | 4 | | | | IV-1 | Ahrr |
| 13591 | 3 | 4 | | | | IV-1 | AI115009 |
| 13592 | 3 | 4 | | | | IV-1 | AI118078 |
| 13593 | 3 | 4 | | | | IV-1 | AI197445 |
| 13594 | 3 | 4 | | | | IV-1 | AI314180 |
| 13595 | 3 | 4 | | | | IV-1 | AI463170 |
| 13596 | 3 | 4 | | | | IV-1 | AI593442 |
| 13597 | 3 | 4 | | | | IV-1 | AI597479 |

Fig. 43 - 81

| | | | | | | | |
|---|---|---|---|---|---|---|---|
| 13598 | 3 | 4 | | | | IV-1 | AI606473 |
| 13599 | 3 | 4 | | | | IV-1 | AI661453 |
| 13600 | 3 | 4 | | | | IV-1 | AI747448 |
| 13601 | 3 | 4 | | | | IV-1 | AI854703 |
| 13602 | 3 | 4 | | | | IV-1 | AI987944 |
| 13603 | 3 | 4 | | | | IV-1 | Aifm2 |
| 13604 | 3 | 4 | | | | IV-1 | Aim1 |
| 13605 | 3 | 4 | | | | IV-1 | Aimp2 |
| 13606 | 3 | 4 | | | | IV-1 | Aip |
| 13607 | 3 | 4 | | | | IV-1 | Aipl1 |
| 13608 | 3 | 4 | | | | IV-1 | Aire |
| 13609 | 3 | 4 | | | | IV-1 | Ajap1 |
| 13610 | 3 | 4 | | | | IV-1 | Ajuba |
| 13611 | 3 | 4 | | | | IV-1 | Ak3 |
| 13612 | 3 | 4 | | | | IV-1 | Akap5 |
| 13613 | 3 | 4 | | | | IV-1 | Akap6 |
| 13614 | 3 | 4 | | | | IV-1 | Akap7 |
| 13615 | 3 | 4 | | | | IV-1 | Akap8 |
| 13616 | 3 | 4 | | | | IV-1 | Akirin1 |
| 13617 | 3 | 4 | | | | IV-1 | Akirin2 |
| 13618 | 3 | 4 | | | | IV-1 | Akna |
| 13619 | 3 | 4 | | | | IV-1 | Aknad1 |
| 13620 | 3 | 4 | | | | IV-1 | Akp3 |
| 13621 | 3 | 4 | | | | IV-1 | Akr1c18 |
| 13622 | 3 | 4 | | | | IV-1 | Akr1c21 |
| 13623 | 3 | 4 | | | | IV-1 | Akr1c6 |
| 13624 | 3 | 4 | | | | IV-1 | Akr1cl |
| 13625 | 3 | 4 | | | | IV-1 | Akt2 |
| 13626 | 3 | 4 | | | | IV-1 | Aldh2 |
| 13627 | 3 | 4 | | | | IV-1 | Aldh4a1 |
| 13628 | 3 | 4 | | | | IV-1 | Alg1 |
| 13629 | 3 | 4 | | | | IV-1 | Alg11 |
| 13630 | 3 | 4 | | | | IV-1 | Alg12 |
| 13631 | 3 | 4 | | | | IV-1 | Alg13 |
| 13632 | 3 | 4 | | | | IV-1 | Alg2 |
| 13633 | 3 | 4 | | | | IV-1 | Alg3 |
| 13634 | 3 | 4 | | | | IV-1 | Alg5 |
| 13635 | 3 | 4 | | | | IV-1 | Alg9 |
| 13636 | 3 | 4 | | | | IV-1 | Alk |
| 13637 | 3 | 4 | | | | IV-1 | Alkbh1 |
| 13638 | 3 | 4 | | | | IV-1 | Alkbh4 |
| 13639 | 3 | 4 | | | | IV-1 | Alkbh5 |
| 13640 | 3 | 4 | | | | IV-1 | Allc |
| 13641 | 3 | 4 | | | | IV-1 | Alms1-ps2 |
| 13642 | 3 | 4 | | | | IV-1 | Alox12e |
| 13643 | 3 | 4 | | | | IV-1 | Alox8 |
| 13644 | 3 | 4 | | | | IV-1 | Aloxe3 |
| 13645 | 3 | 4 | | | | IV-1 | Alpk2 |
| 13646 | 3 | 4 | | | | IV-1 | Alppl2 |
| 13647 | 3 | 4 | | | | IV-1 | Als2cl |
| 13648 | 3 | 4 | | | | IV-1 | Als2cr11 |
| 13649 | 3 | 4 | | | | IV-1 | Ambn |
| 13650 | 3 | 4 | | | | IV-1 | Ambra1 |
| 13651 | 3 | 4 | | | | IV-1 | Amdhd1 |
| 13652 | 3 | 4 | | | | IV-1 | Amelx |
| 13653 | 3 | 4 | | | | IV-1 | Amer2 |
| 13654 | 3 | 4 | | | | IV-1 | Amer3 |
| 13655 | 3 | 4 | | | | IV-1 | Amfr |
| 13656 | 3 | 4 | | | | IV-1 | Amh |
| 13657 | 3 | 4 | | | | IV-1 | Ammecr1l |
| 13658 | 3 | 4 | | | | IV-1 | Amn |
| 13659 | 3 | 4 | | | | IV-1 | Amotl2 |
| 13660 | 3 | 4 | | | | IV-1 | Ampd3 |
| 13661 | 3 | 4 | | | | IV-1 | Amtn |
| 13662 | 3 | 4 | | | | IV-1 | Anapc4 |
| 13663 | 3 | 4 | | | | IV-1 | Anapc5 |
| 13664 | 3 | 4 | | | | IV-1 | Ang2 |
| 13665 | 3 | 4 | | | | IV-1 | Ang3 |
| 13666 | 3 | 4 | | | | IV-1 | Ang5 |
| 13667 | 3 | 4 | | | | IV-1 | Ang6 |
| 13668 | 3 | 4 | | | | IV-1 | Angel2 |
| 13669 | 3 | 4 | | | | IV-1 | Angptl3 |
| 13670 | 3 | 4 | | | | IV-1 | Ank |
| 13671 | 3 | 4 | | | | IV-1 | Ank1 |
| 13672 | 3 | 4 | | | | IV-1 | Ankar |
| 13673 | 3 | 4 | | | | IV-1 | Ankef1 |
| 13674 | 3 | 4 | | | | IV-1 | Ankfn1 |
| 13675 | 3 | 4 | | | | IV-1 | Ankk1 |
| 13676 | 3 | 4 | | | | IV-1 | Ankmy1 |
| 13677 | 3 | 4 | | | | IV-1 | Ankmy2 |
| 13678 | 3 | 4 | | | | IV-1 | Ankra2 |
| 13679 | 3 | 4 | | | | IV-1 | Ankrd10 |
| 13680 | 3 | 4 | | | | IV-1 | Ankrd13a |
| 13681 | 3 | 4 | | | | IV-1 | Ankrd13c |
| 13682 | 3 | 4 | | | | IV-1 | Ankrd16 |
| 13683 | 3 | 4 | | | | IV-1 | Ankrd32 |
| 13684 | 3 | 4 | | | | IV-1 | Ankrd33 |
| 13685 | 3 | 4 | | | | IV-1 | Ankrd34a |
| 13686 | 3 | 4 | | | | IV-1 | Ankrd34b |
| 13687 | 3 | 4 | | | | IV-1 | Ankrd34c |
| 13688 | 3 | 4 | | | | IV-1 | Ankrd40 |
| 13689 | 3 | 4 | | | | IV-1 | Ankrd44 |
| 13690 | 3 | 4 | | | | IV-1 | Ankrd46 |
| 13691 | 3 | 4 | | | | IV-1 | Ankrd49 |
| 13692 | 3 | 4 | | | | IV-1 | Ankrd53 |
| 13693 | 3 | 4 | | | | IV-1 | Ankrd6 |
| 13694 | 3 | 4 | | | | IV-1 | Ankrd60 |
| 13695 | 3 | 4 | | | | IV-1 | Ankrd9 |
| 13696 | 3 | 4 | | | | IV-1 | Anks1 |
| 13697 | 3 | 4 | | | | IV-1 | Anks1b |
| 13698 | 3 | 4 | | | | IV-1 | Anks3 |
| 13699 | 3 | 4 | | | | IV-1 | Ankub1 |
| 13700 | 3 | 4 | | | | IV-1 | Ankzf1 |
| 13701 | 3 | 4 | | | | IV-1 | Anln |
| 13702 | 3 | 4 | | | | IV-1 | Ano10 |
| 13703 | 3 | 4 | | | | IV-1 | Ano2 |
| 13704 | 3 | 4 | | | | IV-1 | Ano4 |
| 13705 | 3 | 4 | | | | IV-1 | Ano5 |
| 13706 | 3 | 4 | | | | IV-1 | Ano7 |
| 13707 | 3 | 4 | | | | IV-1 | Ano8 |
| 13708 | 3 | 4 | | | | IV-1 | Anp32b |
| 13709 | 3 | 4 | | | | IV-1 | Anp32e |
| 13710 | 3 | 4 | | | | IV-1 | Antxr2 |
| 13711 | 3 | 4 | | | | IV-1 | Antxrl |
| 13712 | 3 | 4 | | | | IV-1 | Anxa10 |
| 13713 | 3 | 4 | | | | IV-1 | Anxa6 |
| 13714 | 3 | 4 | | | | IV-1 | Anxa7 |
| 13715 | 3 | 4 | | | | IV-1 | Aoc3 |
| 13716 | 3 | 4 | | | | IV-1 | Aox2 |
| 13717 | 3 | 4 | | | | IV-1 | Aox4 |
| 13718 | 3 | 4 | | | | IV-1 | Ap1ar |
| 13719 | 3 | 4 | | | | IV-1 | Ap1b1 |
| 13720 | 3 | 4 | | | | IV-1 | Ap1g1 |
| 13721 | 3 | 4 | | | | IV-1 | Ap1s2 |
| 13722 | 3 | 4 | | | | IV-1 | Ap2a1 |
| 13723 | 3 | 4 | | | | IV-1 | Ap2a2 |
| 13724 | 3 | 4 | | | | IV-1 | Ap2b1 |
| 13725 | 3 | 4 | | | | IV-1 | Ap2m1 |
| 13726 | 3 | 4 | | | | IV-1 | Ap3b1 |
| 13727 | 3 | 4 | | | | IV-1 | Ap3b2 |
| 13728 | 3 | 4 | | | | IV-1 | Ap3d1 |
| 13729 | 3 | 4 | | | | IV-1 | Ap3m2 |
| 13730 | 3 | 4 | | | | IV-1 | Ap3s2 |
| 13731 | 3 | 4 | | | | IV-1 | Ap4e1 |
| 13732 | 3 | 4 | | | | IV-1 | Apba1 |
| 13733 | 3 | 4 | | | | IV-1 | Apba2 |
| 13734 | 3 | 4 | | | | IV-1 | Apbb1 |
| 13735 | 3 | 4 | | | | IV-1 | Apbb2 |
| 13736 | 3 | 4 | | | | IV-1 | Apc2 |
| 13737 | 3 | 4 | | | | IV-1 | Apela |
| 13738 | 3 | 4 | | | | IV-1 | Aph1a |
| 13739 | 3 | 4 | | | | IV-1 | Aph1c |
| 13740 | 3 | 4 | | | | IV-1 | Aplp2 |
| 13741 | 3 | 4 | | | | IV-1 | Apobec4 |
| 13742 | 3 | 4 | | | | IV-1 | Apol10a |
| 13743 | 3 | 4 | | | | IV-1 | Apol11a |
| 13744 | 3 | 4 | | | | IV-1 | Apol11b |
| 13745 | 3 | 4 | | | | IV-1 | Apol7b |
| 13746 | 3 | 4 | | | | IV-1 | Apol7c |
| 13747 | 3 | 4 | | | | IV-1 | Apol7d |
| 13748 | 3 | 4 | | | | IV-1 | Apon |
| 13749 | 3 | 4 | | | | IV-1 | Apoo-ps |
| 13750 | 3 | 4 | | | | IV-1 | App |
| 13751 | 3 | 4 | | | | IV-1 | Appl2 |
| 13752 | 3 | 4 | | | | IV-1 | Aptx |
| 13753 | 3 | 4 | | | | IV-1 | Aqp1 |
| 13754 | 3 | 4 | | | | IV-1 | Aqp6 |
| 13755 | 3 | 4 | | | | IV-1 | Aqr |
| 13756 | 3 | 4 | | | | IV-1 | Ar |
| 13757 | 3 | 4 | | | | IV-1 | Araf |
| 13758 | 3 | 4 | | | | IV-1 | Arap1 |
| 13759 | 3 | 4 | | | | IV-1 | Arap3 |
| 13760 | 3 | 4 | | | | IV-1 | Arcn1 |
| 13761 | 3 | 4 | | | | IV-1 | Arf1 |
| 13762 | 3 | 4 | | | | IV-1 | Arf2 |
| 13763 | 3 | 4 | | | | IV-1 | Arf3 |
| 13764 | 3 | 4 | | | | IV-1 | Arf4 |
| 13765 | 3 | 4 | | | | IV-1 | Arf6 |
| 13766 | 3 | 4 | | | | IV-1 | Arfgap1 |
| 13767 | 3 | 4 | | | | IV-1 | Arfgap2 |

Fig. 43 - 82

| | | | | | | | |
|---|---|---|---|---|---|---|---|
| 13768 | 3 | 4 | | | IV-1 | Arfgap3 |
| 13769 | 3 | 4 | | | IV-1 | Arfgef1 |
| 13770 | 3 | 4 | | | IV-1 | Arfgef2 |
| 13771 | 3 | 4 | | | IV-1 | Arfip1 |
| 13772 | 3 | 4 | | | IV-1 | Arfip2 |
| 13773 | 3 | 4 | | | IV-1 | Arglu1 |
| 13774 | 3 | 4 | | | IV-1 | Arhgap1 |
| 13775 | 3 | 4 | | | IV-1 | Arhgap10 |
| 13776 | 3 | 4 | | | IV-1 | Arhgap12 |
| 13777 | 3 | 4 | | | IV-1 | Arhgap15os |
| 13778 | 3 | 4 | | | IV-1 | Arhgap17 |
| 13779 | 3 | 4 | | | IV-1 | Arhgap18 |
| 13780 | 3 | 4 | | | IV-1 | Arhgap25 |
| 13781 | 3 | 4 | | | IV-1 | Arhgap27 |
| 13782 | 3 | 4 | | | IV-1 | Arhgap28 |
| 13783 | 3 | 4 | | | IV-1 | Arhgap29 |
| 13784 | 3 | 4 | | | IV-1 | Arhgap33os |
| 13785 | 3 | 4 | | | IV-1 | Arhgap36 |
| 13786 | 3 | 4 | | | IV-1 | Arhgap39 |
| 13787 | 3 | 4 | | | IV-1 | Arhgap40 |
| 13788 | 3 | 4 | | | IV-1 | Arhgap44 |
| 13789 | 3 | 4 | | | IV-1 | Arhgdia |
| 13790 | 3 | 4 | | | IV-1 | Arhgef1 |
| 13791 | 3 | 4 | | | IV-1 | Arhgef2 |
| 13792 | 3 | 4 | | | IV-1 | Arhgef25 |
| 13793 | 3 | 4 | | | IV-1 | Arhgef26 |
| 13794 | 3 | 4 | | | IV-1 | Arhgef28 |
| 13795 | 3 | 4 | | | IV-1 | Arhgef3 |
| 13796 | 3 | 4 | | | IV-1 | Arhgef33 |
| 13797 | 3 | 4 | | | IV-1 | Arhgef38 |
| 13798 | 3 | 4 | | | IV-1 | Arhgef39 |
| 13799 | 3 | 4 | | | IV-1 | Arhgef4 |
| 13800 | 3 | 4 | | | IV-1 | Arid1b |
| 13801 | 3 | 4 | | | IV-1 | Arid3c |
| 13802 | 3 | 4 | | | IV-1 | Arid4b |
| 13803 | 3 | 4 | | | IV-1 | Arih1 |
| 13804 | 3 | 4 | | | IV-1 | Arl1 |
| 13805 | 3 | 4 | | | IV-1 | Arl11 |
| 13806 | 3 | 4 | | | IV-1 | Arl13a |
| 13807 | 3 | 4 | | | IV-1 | Arl14 |
| 13808 | 3 | 4 | | | IV-1 | Arl14ep1 |
| 13809 | 3 | 4 | | | IV-1 | Arl15 |
| 13810 | 3 | 4 | | | IV-1 | Arl4a |
| 13811 | 3 | 4 | | | IV-1 | Arl5a |
| 13812 | 3 | 4 | | | IV-1 | Arl6ip1 |
| 13813 | 3 | 4 | | | IV-1 | Arl6ip4 |
| 13814 | 3 | 4 | | | IV-1 | Arl6ip5 |
| 13815 | 3 | 4 | | | IV-1 | Arl8a |
| 13816 | 3 | 4 | | | IV-1 | Arl8b |
| 13817 | 3 | 4 | | | IV-1 | Arl9 |
| 13818 | 3 | 4 | | | IV-1 | Armc1 |
| 13819 | 3 | 4 | | | IV-1 | Armc3 |
| 13820 | 3 | 4 | | | IV-1 | Armc7 |
| 13821 | 3 | 4 | | | IV-1 | Armc8 |
| 13822 | 3 | 4 | | | IV-1 | Armcx2 |
| 13823 | 3 | 4 | | | IV-1 | Armcx3 |
| 13824 | 3 | 4 | | | IV-1 | Arnt |
| 13825 | 3 | 4 | | | IV-1 | Arnt2 |
| 13826 | 3 | 4 | | | IV-1 | Arntl2 |
| 13827 | 3 | 4 | | | IV-1 | Arpc1a |
| 13828 | 3 | 4 | | | IV-1 | Arpc1b |
| 13829 | 3 | 4 | | | IV-1 | Arpc3 |
| 13830 | 3 | 4 | | | IV-1 | Arpc5 |
| 13831 | 3 | 4 | | | IV-1 | Arr3 |
| 13832 | 3 | 4 | | | IV-1 | Arrdc1 |
| 13833 | 3 | 4 | | | IV-1 | Arsj |
| 13834 | 3 | 4 | | | IV-1 | Art2a-ps |
| 13835 | 3 | 4 | | | IV-1 | Artn |
| 13836 | 3 | 4 | | | IV-1 | Asap1 |
| 13837 | 3 | 4 | | | IV-1 | Asb10 |
| 13838 | 3 | 4 | | | IV-1 | Asb18 |
| 13839 | 3 | 4 | | | IV-1 | Asb8 |
| 13840 | 3 | 4 | | | IV-1 | Asb9 |
| 13841 | 3 | 4 | | | IV-1 | Ascc2 |
| 13842 | 3 | 4 | | | IV-1 | Ascc3 |
| 13843 | 3 | 4 | | | IV-1 | Ascl2 |
| 13844 | 3 | 4 | | | IV-1 | Ascl4 |
| 13845 | 3 | 4 | | | IV-1 | Ascl5 |
| 13846 | 3 | 4 | | | IV-1 | Asgr1 |
| 13847 | 3 | 4 | | | IV-1 | Asgr2 |
| 13848 | 3 | 4 | | | IV-1 | Asic1 |
| 13849 | 3 | 4 | | | IV-1 | Asic2 |
| 13850 | 3 | 4 | | | IV-1 | Asic3 |
| 13851 | 3 | 4 | | | IV-1 | Asic4 |
| 13852 | 3 | 4 | | | IV-1 | Asmt |
| 13853 | 3 | 4 | | | IV-1 | Asna1 |
| 13854 | 3 | 4 | | | IV-1 | Asphd1 |
| 13855 | 3 | 4 | | | IV-1 | Asphd2 |
| 13856 | 3 | 4 | | | IV-1 | Aspm |
| 13857 | 3 | 4 | | | IV-1 | Aspscr1 |
| 13858 | 3 | 4 | | | IV-1 | Aste1 |
| 13859 | 3 | 4 | | | IV-1 | Astl |
| 13860 | 3 | 4 | | | IV-1 | Astn1 |
| 13861 | 3 | 4 | | | IV-1 | Astn2 |
| 13862 | 3 | 4 | | | IV-1 | Asxl1 |
| 13863 | 3 | 4 | | | IV-1 | Asz1 |
| 13864 | 3 | 4 | | | IV-1 | Atad1 |
| 13865 | 3 | 4 | | | IV-1 | Atad2 |
| 13866 | 3 | 4 | | | IV-1 | Atad3aos |
| 13867 | 3 | 4 | | | IV-1 | Atcay |
| 13868 | 3 | 4 | | | IV-1 | Ate1 |
| 13869 | 3 | 4 | | | IV-1 | Atf1 |
| 13870 | 3 | 4 | | | IV-1 | Atf2 |
| 13871 | 3 | 4 | | | IV-1 | Atf4 |
| 13872 | 3 | 4 | | | IV-1 | Atf6 |
| 13873 | 3 | 4 | | | IV-1 | Atf6b |
| 13874 | 3 | 4 | | | IV-1 | Atf7ip2 |
| 13875 | 3 | 4 | | | IV-1 | Atg12 |
| 13876 | 3 | 4 | | | IV-1 | Atg13 |
| 13877 | 3 | 4 | | | IV-1 | Atg2a |
| 13878 | 3 | 4 | | | IV-1 | Atg2b |
| 13879 | 3 | 4 | | | IV-1 | Atg3 |
| 13880 | 3 | 4 | | | IV-1 | Atg4b |
| 13881 | 3 | 4 | | | IV-1 | Atg4c |
| 13882 | 3 | 4 | | | IV-1 | Atg7 |
| 13883 | 3 | 4 | | | IV-1 | Atg9a |
| 13884 | 3 | 4 | | | IV-1 | Athl1 |
| 13885 | 3 | 4 | | | IV-1 | Atic |
| 13886 | 3 | 4 | | | IV-1 | Atm |
| 13887 | 3 | 4 | | | IV-1 | Atmin |
| 13888 | 3 | 4 | | | IV-1 | Atn1 |
| 13889 | 3 | 4 | | | IV-1 | Atoh1 |
| 13890 | 3 | 4 | | | IV-1 | Atoh7 |
| 13891 | 3 | 4 | | | IV-1 | Atp10b |
| 13892 | 3 | 4 | | | IV-1 | Atp11c |
| 13893 | 3 | 4 | | | IV-1 | Atp12a |
| 13894 | 3 | 4 | | | IV-1 | Atp13a1 |
| 13895 | 3 | 4 | | | IV-1 | Atp13a3 |
| 13896 | 3 | 4 | | | IV-1 | Atp13a4 |
| 13897 | 3 | 4 | | | IV-1 | Atp13a5 |
| 13898 | 3 | 4 | | | IV-1 | Atp1a2 |
| 13899 | 3 | 4 | | | IV-1 | Atp1a4 |
| 13900 | 3 | 4 | | | IV-1 | Atp1b3 |
| 13901 | 3 | 4 | | | IV-1 | Atp1b4 |
| 13902 | 3 | 4 | | | IV-1 | Atp2a3 |
| 13903 | 3 | 4 | | | IV-1 | Atp2b1 |
| 13904 | 3 | 4 | | | IV-1 | Atp2b2 |
| 13905 | 3 | 4 | | | IV-1 | Atp2b3 |
| 13906 | 3 | 4 | | | IV-1 | Atp2c1 |
| 13907 | 3 | 4 | | | IV-1 | Atp4a |
| 13908 | 3 | 4 | | | IV-1 | Atp4b |
| 13909 | 3 | 4 | | | IV-1 | Atp5a1 |
| 13910 | 3 | 4 | | | IV-1 | Atp5b |
| 13911 | 3 | 4 | | | IV-1 | Atp5c1 |
| 13912 | 3 | 4 | | | IV-1 | Atp5d |
| 13913 | 3 | 4 | | | IV-1 | Atp5j |
| 13914 | 3 | 4 | | | IV-1 | Atp5s |
| 13915 | 3 | 4 | | | IV-1 | Atp6ap1 |
| 13916 | 3 | 4 | | | IV-1 | Atp6ap1l |
| 13917 | 3 | 4 | | | IV-1 | Atp6ap2 |
| 13918 | 3 | 4 | | | IV-1 | Atp6v0a1 |
| 13919 | 3 | 4 | | | IV-1 | Atp6v0a2 |
| 13920 | 3 | 4 | | | IV-1 | Atp6v0c |
| 13921 | 3 | 4 | | | IV-1 | Atp6v0e2 |
| 13922 | 3 | 4 | | | IV-1 | Atp6v1b2 |
| 13923 | 3 | 4 | | | IV-1 | Atp6v1c1 |
| 13924 | 3 | 4 | | | IV-1 | Atp6v1c2 |
| 13925 | 3 | 4 | | | IV-1 | Atp6v1f |
| 13926 | 3 | 4 | | | IV-1 | Atp6v1g1 |
| 13927 | 3 | 4 | | | IV-1 | Atp6v1g3 |
| 13928 | 3 | 4 | | | IV-1 | Atp6v1h |
| 13929 | 3 | 4 | | | IV-1 | Atp8a2 |
| 13930 | 3 | 4 | | | IV-1 | Atp8b5 |
| 13931 | 3 | 4 | | | IV-1 | Atp9a |
| 13932 | 3 | 4 | | | IV-1 | Atp9b |
| 13933 | 3 | 4 | | | IV-1 | Atpaf1 |
| 13934 | 3 | 4 | | | IV-1 | Atr |
| 13935 | 3 | 4 | | | IV-1 | Atrnl1 |
| 13936 | 3 | 4 | | | IV-1 | Atxn2 |
| 13937 | 3 | 4 | | | IV-1 | Atxn7l2 |

Fig. 43 - 83

| | | | | | | | |
|---|---|---|---|---|---|---|---|
| 13938 | 3 | 4 | | | | IV-1 | Atxn7l3 |
| 13939 | 3 | 4 | | | | IV-1 | Atxn7l3b |
| 13940 | 3 | 4 | | | | IV-1 | AU015228 |
| 13941 | 3 | 4 | | | | IV-1 | AU015836 |
| 13942 | 3 | 4 | | | | IV-1 | AU016765 |
| 13943 | 3 | 4 | | | | IV-1 | AU018091 |
| 13944 | 3 | 4 | | | | IV-1 | AU018829 |
| 13945 | 3 | 4 | | | | IV-1 | AU019990 |
| 13946 | 3 | 4 | | | | IV-1 | AU021063 |
| 13947 | 3 | 4 | | | | IV-1 | AU022754 |
| 13948 | 3 | 4 | | | | IV-1 | AU040320 |
| 13949 | 3 | 4 | | | | IV-1 | Aup1 |
| 13950 | 3 | 4 | | | | IV-1 | Aurkc |
| 13951 | 3 | 4 | | | | IV-1 | Auts2 |
| 13952 | 3 | 4 | | | | IV-1 | AV320801 |
| 13953 | 3 | 4 | | | | IV-1 | Aven |
| 13954 | 3 | 4 | | | | IV-1 | Avp |
| 13955 | 3 | 4 | | | | IV-1 | Avpr1b |
| 13956 | 3 | 4 | | | | IV-1 | AW495222 |
| 13957 | 3 | 4 | | | | IV-1 | AW551984 |
| 13958 | 3 | 4 | | | | IV-1 | AW554918 |
| 13959 | 3 | 4 | | | | IV-1 | AW822252 |
| 13960 | 3 | 4 | | | | IV-1 | Awat2 |
| 13961 | 3 | 4 | | | | IV-1 | Axin1 |
| 13962 | 3 | 4 | | | | IV-1 | AY512915 |
| 13963 | 3 | 4 | | | | IV-1 | AY512931 |
| 13964 | 3 | 4 | | | | IV-1 | B020004C17Rik |
| 13965 | 3 | 4 | | | | IV-1 | B020014A21Rik |
| 13966 | 3 | 4 | | | | IV-1 | B020018J22Rik |
| 13967 | 3 | 4 | | | | IV-1 | B020031M17Rik |
| 13968 | 3 | 4 | | | | IV-1 | B130006D01Rik |
| 13969 | 3 | 4 | | | | IV-1 | B230209E15Rik |
| 13970 | 3 | 4 | | | | IV-1 | B230217C12Rik |
| 13971 | 3 | 4 | | | | IV-1 | B230319C09Rik |
| 13972 | 3 | 4 | | | | IV-1 | B230323A14Rik |
| 13973 | 3 | 4 | | | | IV-1 | B3galnt2 |
| 13974 | 3 | 4 | | | | IV-1 | B3galt5 |
| 13975 | 3 | 4 | | | | IV-1 | B3galt6 |
| 13976 | 3 | 4 | | | | IV-1 | B3gat1 |
| 13977 | 3 | 4 | | | | IV-1 | B3gat2 |
| 13978 | 3 | 4 | | | | IV-1 | B3gnt1 |
| 13979 | 3 | 4 | | | | IV-1 | B3gnt2 |
| 13980 | 3 | 4 | | | | IV-1 | B3gnt6 |
| 13981 | 3 | 4 | | | | IV-1 | B3gnt7 |
| 13982 | 3 | 4 | | | | IV-1 | B3gntl |
| 13983 | 3 | 4 | | | | IV-1 | B430212C06Rik |
| 13984 | 3 | 4 | | | | IV-1 | B430319G15Rik |
| 13985 | 3 | 4 | | | | IV-1 | B4galnt4 |
| 13986 | 3 | 4 | | | | IV-1 | B4galt1 |
| 13987 | 3 | 4 | | | | IV-1 | B4galt7 |
| 13988 | 3 | 4 | | | | IV-1 | B630005N14Rik |
| 13989 | 3 | 4 | | | | IV-1 | B630019K06Rik |
| 13990 | 3 | 4 | | | | IV-1 | B930018H19Rik |
| 13991 | 3 | 4 | | | | IV-1 | B930092H01Rik |
| 13992 | 3 | 4 | | | | IV-1 | B9d1 |
| 13993 | 3 | 4 | | | | IV-1 | Baalc |
| 13994 | 3 | 4 | | | | IV-1 | Babam1 |
| 13995 | 3 | 4 | | | | IV-1 | Bace2 |
| 13996 | 3 | 4 | | | | IV-1 | Bag1 |
| 13997 | 3 | 4 | | | | IV-1 | Bag3 |
| 13998 | 3 | 4 | | | | IV-1 | Bag4 |
| 13999 | 3 | 4 | | | | IV-1 | Bag6 |
| 14000 | 3 | 4 | | | | IV-1 | Bai1 |
| 14001 | 3 | 4 | | | | IV-1 | Bai2 |
| 14002 | 3 | 4 | | | | IV-1 | Bai3 |
| 14003 | 3 | 4 | | | | IV-1 | Baiap2 |
| 14004 | 3 | 4 | | | | IV-1 | Baiap3 |
| 14005 | 3 | 4 | | | | IV-1 | Bambi |
| 14006 | 3 | 4 | | | | IV-1 | Banf2 |
| 14007 | 3 | 4 | | | | IV-1 | Bap1 |
| 14008 | 3 | 4 | | | | IV-1 | Bard1 |
| 14009 | 3 | 4 | | | | IV-1 | Barhl1 |
| 14010 | 3 | 4 | | | | IV-1 | Barhl2 |
| 14011 | 3 | 4 | | | | IV-1 | Baz2a |
| 14012 | 3 | 4 | | | | IV-1 | BB019430 |
| 14013 | 3 | 4 | | | | IV-1 | BB283400 |
| 14014 | 3 | 4 | | | | IV-1 | BB287469 |
| 14015 | 3 | 4 | | | | IV-1 | BC003331 |
| 14016 | 3 | 4 | | | | IV-1 | BC003965 |
| 14017 | 3 | 4 | | | | IV-1 | BC004004 |
| 14018 | 3 | 4 | | | | IV-1 | BC006965 |
| 14019 | 3 | 4 | | | | IV-1 | BC016579 |
| 14020 | 3 | 4 | | | | IV-1 | BC017158 |
| 14021 | 3 | 4 | | | | IV-1 | BC017643 |
| 14022 | 3 | 4 | | | | IV-1 | BC018473 |
| 14023 | 3 | 4 | | | | IV-1 | BC021785 |
| 14024 | 3 | 4 | | | | IV-1 | BC023829 |
| 14025 | 3 | 4 | | | | IV-1 | BC025920 |
| 14026 | 3 | 4 | | | | IV-1 | BC027072 |
| 14027 | 3 | 4 | | | | IV-1 | BC027231 |
| 14028 | 3 | 4 | | | | IV-1 | BC029722 |
| 14029 | 3 | 4 | | | | IV-1 | BC030336 |
| 14030 | 3 | 4 | | | | IV-1 | BC030500 |
| 14031 | 3 | 4 | | | | IV-1 | BC030870 |
| 14032 | 3 | 4 | | | | IV-1 | BC031181 |
| 14033 | 3 | 4 | | | | IV-1 | BC031361 |
| 14034 | 3 | 4 | | | | IV-1 | BC037032 |
| 14035 | 3 | 4 | | | | IV-1 | BC039771 |
| 14036 | 3 | 4 | | | | IV-1 | BC048502 |
| 14037 | 3 | 4 | | | | IV-1 | BC048546 |
| 14038 | 3 | 4 | | | | IV-1 | BC048609 |
| 14039 | 3 | 4 | | | | IV-1 | BC048644 |
| 14040 | 3 | 4 | | | | IV-1 | BC048671 |
| 14041 | 3 | 4 | | | | IV-1 | BC049730 |
| 14042 | 3 | 4 | | | | IV-1 | BC051019 |
| 14043 | 3 | 4 | | | | IV-1 | BC051665 |
| 14044 | 3 | 4 | | | | IV-1 | BC052688 |
| 14045 | 3 | 4 | | | | IV-1 | BC053393 |
| 14046 | 3 | 4 | | | | IV-1 | BC055111 |
| 14047 | 3 | 4 | | | | IV-1 | BC055402 |
| 14048 | 3 | 4 | | | | IV-1 | BC061212 |
| 14049 | 3 | 4 | | | | IV-1 | BC068157 |
| 14050 | 3 | 4 | | | | IV-1 | Bc1 |
| 14051 | 3 | 4 | | | | IV-1 | BC107364 |
| 14052 | 3 | 4 | | | | IV-1 | Bcan |
| 14053 | 3 | 4 | | | | IV-1 | Bcas1 |
| 14054 | 3 | 4 | | | | IV-1 | Bcas1os2 |
| 14055 | 3 | 4 | | | | IV-1 | Bcas3 |
| 14056 | 3 | 4 | | | | IV-1 | Bcas3os1 |
| 14057 | 3 | 4 | | | | IV-1 | Bcas3os2 |
| 14058 | 3 | 4 | | | | IV-1 | Bcat1 |
| 14059 | 3 | 4 | | | | IV-1 | Bcat2 |
| 14060 | 3 | 4 | | | | IV-1 | Bccip |
| 14061 | 3 | 4 | | | | IV-1 | Bckdhb |
| 14062 | 3 | 4 | | | | IV-1 | Bckdk |
| 14063 | 3 | 4 | | | | IV-1 | Bcl2a1c |
| 14064 | 3 | 4 | | | | IV-1 | Bcl2l10 |
| 14065 | 3 | 4 | | | | IV-1 | Bcl2l15 |
| 14066 | 3 | 4 | | | | IV-1 | Bcl7b |
| 14067 | 3 | 4 | | | | IV-1 | Bcl9 |
| 14068 | 3 | 4 | | | | IV-1 | Bclaf1 |
| 14069 | 3 | 4 | | | | IV-1 | Bcs1l |
| 14070 | 3 | 4 | | | | IV-1 | Bdkrb2 |
| 14071 | 3 | 4 | | | | IV-1 | Bdnf |
| 14072 | 3 | 4 | | | | IV-1 | Bean1 |
| 14073 | 3 | 4 | | | | IV-1 | Becn1 |
| 14074 | 3 | 4 | | | | IV-1 | Becn2 |
| 14075 | 3 | 4 | | | | IV-1 | Begain |
| 14076 | 3 | 4 | | | | IV-1 | Bend3 |
| 14077 | 3 | 4 | | | | IV-1 | Bend4 |
| 14078 | 3 | 4 | | | | IV-1 | Bend6 |
| 14079 | 3 | 4 | | | | IV-1 | Best2 |
| 14080 | 3 | 4 | | | | IV-1 | Bet1 |
| 14081 | 3 | 4 | | | | IV-1 | Bfar |
| 14082 | 3 | 4 | | | | IV-1 | Bgn |
| 14083 | 3 | 4 | | | | IV-1 | Bhlhb9 |
| 14084 | 3 | 4 | | | | IV-1 | Bhlhe22 |
| 14085 | 3 | 4 | | | | IV-1 | Bhlhe23 |
| 14086 | 3 | 4 | | | | IV-1 | Bin3 |
| 14087 | 3 | 4 | | | | IV-1 | Birc2 |
| 14088 | 3 | 4 | | | | IV-1 | Birc3 |
| 14089 | 3 | 4 | | | | IV-1 | Birc6 |
| 14090 | 3 | 4 | | | | IV-1 | Birc7 |
| 14091 | 3 | 4 | | | | IV-1 | Blcap |
| 14092 | 3 | 4 | | | | IV-1 | Bloc1s6 |
| 14093 | 3 | 4 | | | | IV-1 | Blzf1 |
| 14094 | 3 | 4 | | | | IV-1 | Bmi1 |
| 14095 | 3 | 4 | | | | IV-1 | Bmp1 |
| 14096 | 3 | 4 | | | | IV-1 | Bmp15 |
| 14097 | 3 | 4 | | | | IV-1 | Bmp2k |
| 14098 | 3 | 4 | | | | IV-1 | Bmp6 |
| 14099 | 3 | 4 | | | | IV-1 | Bmpr1b |
| 14100 | 3 | 4 | | | | IV-1 | Bmpr2 |
| 14101 | 3 | 4 | | | | IV-1 | Bms1 |
| 14102 | 3 | 4 | | | | IV-1 | Bnc2 |
| 14103 | 3 | 4 | | | | IV-1 | Bnip2 |
| 14104 | 3 | 4 | | | | IV-1 | Bnip3l |
| 14105 | 3 | 4 | | | | IV-1 | Boll |
| 14106 | 3 | 4 | | | | IV-1 | Bop1 |
| 14107 | 3 | 4 | | | | IV-1 | Bpi |

Fig. 43 - 84

| | | | | | | | |
|---|---|---|---|---|---|---|---|
| 14108 | 3 | 4 | | | | IV-1 | Bpifa1 |
| 14109 | 3 | 4 | | | | IV-1 | Bpifa2 |
| 14110 | 3 | 4 | | | | IV-1 | Bpifa3 |
| 14111 | 3 | 4 | | | | IV-1 | Bpifa5 |
| 14112 | 3 | 4 | | | | IV-1 | Bpifa6 |
| 14113 | 3 | 4 | | | | IV-1 | Bpifb1 |
| 14114 | 3 | 4 | | | | IV-1 | Bpifb2 |
| 14115 | 3 | 4 | | | | IV-1 | Bpifb6 |
| 14116 | 3 | 4 | | | | IV-1 | Bpifb9a |
| 14117 | 3 | 4 | | | | IV-1 | Brca1 |
| 14118 | 3 | 4 | | | | IV-1 | Brca2 |
| 14119 | 3 | 4 | | | | IV-1 | Brd1 |
| 14120 | 3 | 4 | | | | IV-1 | Brd2 |
| 14121 | 3 | 4 | | | | IV-1 | Brd4 |
| 14122 | 3 | 4 | | | | IV-1 | Brd7 |
| 14123 | 3 | 4 | | | | IV-1 | Brd8 |
| 14124 | 3 | 4 | | | | IV-1 | Brd9 |
| 14125 | 3 | 4 | | | | IV-1 | Brf1 |
| 14126 | 3 | 4 | | | | IV-1 | Bricd5 |
| 14127 | 3 | 4 | | | | IV-1 | Brinp1 |
| 14128 | 3 | 4 | | | | IV-1 | Brip1 |
| 14129 | 3 | 4 | | | | IV-1 | Brix1 |
| 14130 | 3 | 4 | | | | IV-1 | Brms1l |
| 14131 | 3 | 4 | | | | IV-1 | Brpf1 |
| 14132 | 3 | 4 | | | | IV-1 | Brs3 |
| 14133 | 3 | 4 | | | | IV-1 | Brsk1 |
| 14134 | 3 | 4 | | | | IV-1 | Brsk2 |
| 14135 | 3 | 4 | | | | IV-1 | Brwd1 |
| 14136 | 3 | 4 | | | | IV-1 | Bsn |
| 14137 | 3 | 4 | | | | IV-1 | Bsnd |
| 14138 | 3 | 4 | | | | IV-1 | Bsph1 |
| 14139 | 3 | 4 | | | | IV-1 | Bsx |
| 14140 | 3 | 4 | | | | IV-1 | Btbd10 |
| 14141 | 3 | 4 | | | | IV-1 | Btbd11 |
| 14142 | 3 | 4 | | | | IV-1 | Btbd16 |
| 14143 | 3 | 4 | | | | IV-1 | Btbd18 |
| 14144 | 3 | 4 | | | | IV-1 | Btbd8 |
| 14145 | 3 | 4 | | | | IV-1 | Btc |
| 14146 | 3 | 4 | | | | IV-1 | Btd |
| 14147 | 3 | 4 | | | | IV-1 | Btf3l4 |
| 14148 | 3 | 4 | | | | IV-1 | Btg4 |
| 14149 | 3 | 4 | | | | IV-1 | Btk |
| 14150 | 3 | 4 | | | | IV-1 | Btn1a1 |
| 14151 | 3 | 4 | | | | IV-1 | Btnl1 |
| 14152 | 3 | 4 | | | | IV-1 | Btnl6 |
| 14153 | 3 | 4 | | | | IV-1 | Bub3 |
| 14154 | 3 | 4 | | | | IV-1 | Bud13 |
| 14155 | 3 | 4 | | | | IV-1 | Bzw1 |
| 14156 | 3 | 4 | | | | IV-1 | C030007H22Rik |
| 14157 | 3 | 4 | | | | IV-1 | C030013G03Rik |
| 14158 | 3 | 4 | | | | IV-1 | C030023E24Rik |
| 14159 | 3 | 4 | | | | IV-1 | C030029H02Rik |
| 14160 | 3 | 4 | | | | IV-1 | C130026I21Rik |
| 14161 | 3 | 4 | | | | IV-1 | C130030K03Rik |
| 14162 | 3 | 4 | | | | IV-1 | C130060K24Rik |
| 14163 | 3 | 4 | | | | IV-1 | C130074G19Rik |
| 14164 | 3 | 4 | | | | IV-1 | C130079G13Rik |
| 14165 | 3 | 4 | | | | IV-1 | C1galt1c1 |
| 14166 | 3 | 4 | | | | IV-1 | C1ql1 |
| 14167 | 3 | 4 | | | | IV-1 | C1ql2 |
| 14168 | 3 | 4 | | | | IV-1 | C1ql3 |
| 14169 | 3 | 4 | | | | IV-1 | C1ql4 |
| 14170 | 3 | 4 | | | | IV-1 | C1qtnf7 |
| 14171 | 3 | 4 | | | | IV-1 | C1s1 |
| 14172 | 3 | 4 | | | | IV-1 | C230004F18Rik |
| 14173 | 3 | 4 | | | | IV-1 | C230024C17Rik |
| 14174 | 3 | 4 | | | | IV-1 | C230029M16 |
| 14175 | 3 | 4 | | | | IV-1 | C230079O03Rik |
| 14176 | 3 | 4 | | | | IV-1 | C2cd4c |
| 14177 | 3 | 4 | | | | IV-1 | C2cd5 |
| 14178 | 3 | 4 | | | | IV-1 | C330006A16Rik |
| 14179 | 3 | 4 | | | | IV-1 | C330007P06Rik |
| 14180 | 3 | 4 | | | | IV-1 | C330011F03Rik |
| 14181 | 3 | 4 | | | | IV-1 | C330013F16Rik |
| 14182 | 3 | 4 | | | | IV-1 | C330018D20Rik |
| 14183 | 3 | 4 | | | | IV-1 | C330021F23Rik |
| 14184 | 3 | 4 | | | | IV-1 | C330024D21Rik |
| 14185 | 3 | 4 | | | | IV-1 | C330046G13Rik |
| 14186 | 3 | 4 | | | | IV-1 | C5ar1 |
| 14187 | 3 | 4 | | | | IV-1 | C5ar2 |
| 14188 | 3 | 4 | | | | IV-1 | C630028M04Rik |
| 14189 | 3 | 4 | | | | IV-1 | C630031E19Rik |
| 14190 | 3 | 4 | | | | IV-1 | C730002L08Rik |
| 14191 | 3 | 4 | | | | IV-1 | C77370 |
| 14192 | 3 | 4 | | | | IV-1 | C86187 |
| 14193 | 3 | 4 | | | | IV-1 | C86695 |
| 14194 | 3 | 4 | | | | IV-1 | C87198 |
| 14195 | 3 | 4 | | | | IV-1 | C87414 |
| 14196 | 3 | 4 | | | | IV-1 | C87436 |
| 14197 | 3 | 4 | | | | IV-1 | C87499 |
| 14198 | 3 | 4 | | | | IV-1 | C9 |
| 14199 | 3 | 4 | | | | IV-1 | Cab39 |
| 14200 | 3 | 4 | | | | IV-1 | Cabin1 |
| 14201 | 3 | 4 | | | | IV-1 | Cables2 |
| 14202 | 3 | 4 | | | | IV-1 | Cabp1 |
| 14203 | 3 | 4 | | | | IV-1 | Cabp2 |
| 14204 | 3 | 4 | | | | IV-1 | Cabp4 |
| 14205 | 3 | 4 | | | | IV-1 | Cabp5 |
| 14206 | 3 | 4 | | | | IV-1 | Cabp7 |
| 14207 | 3 | 4 | | | | IV-1 | Cacna1b |
| 14208 | 3 | 4 | | | | IV-1 | Cacna1f |
| 14209 | 3 | 4 | | | | IV-1 | Cacna1g |
| 14210 | 3 | 4 | | | | IV-1 | Cacna2d3 |
| 14211 | 3 | 4 | | | | IV-1 | Cacnb3 |
| 14212 | 3 | 4 | | | | IV-1 | Cacnb4 |
| 14213 | 3 | 4 | | | | IV-1 | Cacng2 |
| 14214 | 3 | 4 | | | | IV-1 | Cacng3 |
| 14215 | 3 | 4 | | | | IV-1 | Cacng4 |
| 14216 | 3 | 4 | | | | IV-1 | Cacng5 |
| 14217 | 3 | 4 | | | | IV-1 | Cacul1 |
| 14218 | 3 | 4 | | | | IV-1 | Cadm1 |
| 14219 | 3 | 4 | | | | IV-1 | Cadm2 |
| 14220 | 3 | 4 | | | | IV-1 | Cadm3 |
| 14221 | 3 | 4 | | | | IV-1 | Cadps |
| 14222 | 3 | 4 | | | | IV-1 | Cadps2 |
| 14223 | 3 | 4 | | | | IV-1 | Calb1 |
| 14224 | 3 | 4 | | | | IV-1 | Calcoco2 |
| 14225 | 3 | 4 | | | | IV-1 | Calcr |
| 14226 | 3 | 4 | | | | IV-1 | Cald1 |
| 14227 | 3 | 4 | | | | IV-1 | Calhm1 |
| 14228 | 3 | 4 | | | | IV-1 | Calm3 |
| 14229 | 3 | 4 | | | | IV-1 | Caln1 |
| 14230 | 3 | 4 | | | | IV-1 | Calu |
| 14231 | 3 | 4 | | | | IV-1 | Caly |
| 14232 | 3 | 4 | | | | IV-1 | Camk1g |
| 14233 | 3 | 4 | | | | IV-1 | Camk2d |
| 14234 | 3 | 4 | | | | IV-1 | Camk2g |
| 14235 | 3 | 4 | | | | IV-1 | Camkk2 |
| 14236 | 3 | 4 | | | | IV-1 | Caml |
| 14237 | 3 | 4 | | | | IV-1 | Camsap3 |
| 14238 | 3 | 4 | | | | IV-1 | Camta2 |
| 14239 | 3 | 4 | | | | IV-1 | Cand1 |
| 14240 | 3 | 4 | | | | IV-1 | Canx |
| 14241 | 3 | 4 | | | | IV-1 | Cap1 |
| 14242 | 3 | 4 | | | | IV-1 | Capn1 |
| 14243 | 3 | 4 | | | | IV-1 | Capn11 |
| 14244 | 3 | 4 | | | | IV-1 | Capn12 |
| 14245 | 3 | 4 | | | | IV-1 | Capn13 |
| 14246 | 3 | 4 | | | | IV-1 | Capn2 |
| 14247 | 3 | 4 | | | | IV-1 | Capn6 |
| 14248 | 3 | 4 | | | | IV-1 | Capn7 |
| 14249 | 3 | 4 | | | | IV-1 | Capn8 |
| 14250 | 3 | 4 | | | | IV-1 | Capn9 |
| 14251 | 3 | 4 | | | | IV-1 | Caprin1 |
| 14252 | 3 | 4 | | | | IV-1 | Caprin2 |
| 14253 | 3 | 4 | | | | IV-1 | Caps2 |
| 14254 | 3 | 4 | | | | IV-1 | Capza1 |
| 14255 | 3 | 4 | | | | IV-1 | Capza2 |
| 14256 | 3 | 4 | | | | IV-1 | Capzb |
| 14257 | 3 | 4 | | | | IV-1 | Car10 |
| 14258 | 3 | 4 | | | | IV-1 | Car11 |
| 14259 | 3 | 4 | | | | IV-1 | Car2 |
| 14260 | 3 | 4 | | | | IV-1 | Car5a |
| 14261 | 3 | 4 | | | | IV-1 | Car5b |
| 14262 | 3 | 4 | | | | IV-1 | Car7 |
| 14263 | 3 | 4 | | | | IV-1 | Car8 |
| 14264 | 3 | 4 | | | | IV-1 | Card14 |
| 14265 | 3 | 4 | | | | IV-1 | Card9 |
| 14266 | 3 | 4 | | | | IV-1 | Carf |
| 14267 | 3 | 4 | | | | IV-1 | Carhsp1 |
| 14268 | 3 | 4 | | | | IV-1 | Cartpt |
| 14269 | 3 | 4 | | | | IV-1 | Casc1 |
| 14270 | 3 | 4 | | | | IV-1 | Casc3 |
| 14271 | 3 | 4 | | | | IV-1 | Casd1 |
| 14272 | 3 | 4 | | | | IV-1 | Cask |
| 14273 | 3 | 4 | | | | IV-1 | Caskin1 |
| 14274 | 3 | 4 | | | | IV-1 | Caskin2 |
| 14275 | 3 | 4 | | | | IV-1 | Casp14 |
| 14276 | 3 | 4 | | | | IV-1 | Casp2 |
| 14277 | 3 | 4 | | | | IV-1 | Casp4 |

Fig. 43 - 85

| | | | | | | | | | |
|---|---|---|---|---|---|---|---|---|---|
| 14278 | 3 | 4 | | | | | IV-1 | Casr | |
| 14279 | 3 | 4 | | | | | IV-1 | Cast | |
| 14280 | 3 | 4 | | | | | IV-1 | Catsper1 | |
| 14281 | 3 | 4 | | | | | IV-1 | Catsper3 | |
| 14282 | 3 | 4 | | | | | IV-1 | Catsper4 | |
| 14283 | 3 | 4 | | | | | IV-1 | Catsperd | |
| 14284 | 3 | 4 | | | | | IV-1 | Catsperg1 | |
| 14285 | 3 | 4 | | | | | IV-1 | Catsperg2 | |
| 14286 | 3 | 4 | | | | | IV-1 | Cbfa2t2 | |
| 14287 | 3 | 4 | | | | | IV-1 | Cblb | |
| 14288 | 3 | 4 | | | | | IV-1 | Cbll1 | |
| 14289 | 3 | 4 | | | | | IV-1 | Cbln2 | |
| 14290 | 3 | 4 | | | | | IV-1 | Cbln3 | |
| 14291 | 3 | 4 | | | | | IV-1 | Cbln4 | |
| 14292 | 3 | 4 | | | | | IV-1 | Cbwd1 | |
| 14293 | 3 | 4 | | | | | IV-1 | Cbx3 | |
| 14294 | 3 | 4 | | | | | IV-1 | Cbx6 | |
| 14295 | 3 | 4 | | | | | IV-1 | Ccar2 | |
| 14296 | 3 | 4 | | | | | IV-1 | Ccbl1 | |
| 14297 | 3 | 4 | | | | | IV-1 | Ccdc105 | |
| 14298 | 3 | 4 | | | | | IV-1 | Ccdc109b | |
| 14299 | 3 | 4 | | | | | IV-1 | Ccdc11 | |
| 14300 | 3 | 4 | | | | | IV-1 | Ccdc110 | |
| 14301 | 3 | 4 | | | | | IV-1 | Ccdc113 | |
| 14302 | 3 | 4 | | | | | IV-1 | Ccdc121 | |
| 14303 | 3 | 4 | | | | | IV-1 | Ccdc126 | |
| 14304 | 3 | 4 | | | | | IV-1 | Ccdc127 | |
| 14305 | 3 | 4 | | | | | IV-1 | Ccdc13 | |
| 14306 | 3 | 4 | | | | | IV-1 | Ccdc130 | |
| 14307 | 3 | 4 | | | | | IV-1 | Ccdc132 | |
| 14308 | 3 | 4 | | | | | IV-1 | Ccdc135 | |
| 14309 | 3 | 4 | | | | | IV-1 | Ccdc142 | |
| 14310 | 3 | 4 | | | | | IV-1 | Ccdc144b | |
| 14311 | 3 | 4 | | | | | IV-1 | Ccdc146 | |
| 14312 | 3 | 4 | | | | | IV-1 | Ccdc147 | |
| 14313 | 3 | 4 | | | | | IV-1 | Ccdc148 | |
| 14314 | 3 | 4 | | | | | IV-1 | Ccdc149 | |
| 14315 | 3 | 4 | | | | | IV-1 | Ccdc15 | |
| 14316 | 3 | 4 | | | | | IV-1 | Ccdc152 | |
| 14317 | 3 | 4 | | | | | IV-1 | Ccdc154 | |
| 14318 | 3 | 4 | | | | | IV-1 | Ccdc155 | |
| 14319 | 3 | 4 | | | | | IV-1 | Ccdc158 | |
| 14320 | 3 | 4 | | | | | IV-1 | Ccdc159 | |
| 14321 | 3 | 4 | | | | | IV-1 | Ccdc162 | |
| 14322 | 3 | 4 | | | | | IV-1 | Ccdc163 | |
| 14323 | 3 | 4 | | | | | IV-1 | Ccdc166 | |
| 14324 | 3 | 4 | | | | | IV-1 | Ccdc169 | |
| 14325 | 3 | 4 | | | | | IV-1 | Ccdc171 | |
| 14326 | 3 | 4 | | | | | IV-1 | Ccdc172 | |
| 14327 | 3 | 4 | | | | | IV-1 | Ccdc174 | |
| 14328 | 3 | 4 | | | | | IV-1 | Ccdc175 | |
| 14329 | 3 | 4 | | | | | IV-1 | Ccdc177 | |
| 14330 | 3 | 4 | | | | | IV-1 | Ccdc178 | |
| 14331 | 3 | 4 | | | | | IV-1 | Ccdc18 | |
| 14332 | 3 | 4 | | | | | IV-1 | Ccdc184 | |
| 14333 | 3 | 4 | | | | | IV-1 | Ccdc25 | |
| 14334 | 3 | 4 | | | | | IV-1 | Ccdc32 | |
| 14335 | 3 | 4 | | | | | IV-1 | Ccdc34os | |
| 14336 | 3 | 4 | | | | | IV-1 | Ccdc36 | |
| 14337 | 3 | 4 | | | | | IV-1 | Ccdc37 | |
| 14338 | 3 | 4 | | | | | IV-1 | Ccdc38 | |
| 14339 | 3 | 4 | | | | | IV-1 | Ccdc40 | |
| 14340 | 3 | 4 | | | | | IV-1 | Ccdc43 | |
| 14341 | 3 | 4 | | | | | IV-1 | Ccdc55 | |
| 14342 | 3 | 4 | | | | | IV-1 | Ccdc59 | |
| 14343 | 3 | 4 | | | | | IV-1 | Ccdc6 | |
| 14344 | 3 | 4 | | | | | IV-1 | Ccdc62 | |
| 14345 | 3 | 4 | | | | | IV-1 | Ccdc63 | |
| 14346 | 3 | 4 | | | | | IV-1 | Ccdc64 | |
| 14347 | 3 | 4 | | | | | IV-1 | Ccdc64b | |
| 14348 | 3 | 4 | | | | | IV-1 | Ccdc66 | |
| 14349 | 3 | 4 | | | | | IV-1 | Ccdc67 | |
| 14350 | 3 | 4 | | | | | IV-1 | Ccdc68 | |
| 14351 | 3 | 4 | | | | | IV-1 | Ccdc7 | |
| 14352 | 3 | 4 | | | | | IV-1 | Ccdc71 | |
| 14353 | 3 | 4 | | | | | IV-1 | Ccdc71l | |
| 14354 | 3 | 4 | | | | | IV-1 | Ccdc73 | |
| 14355 | 3 | 4 | | | | | IV-1 | Ccdc74a | |
| 14356 | 3 | 4 | | | | | IV-1 | Ccdc79 | |
| 14357 | 3 | 4 | | | | | IV-1 | Ccdc81 | |
| 14358 | 3 | 4 | | | | | IV-1 | Ccdc88a | |
| 14359 | 3 | 4 | | | | | IV-1 | Ccdc9 | |
| 14360 | 3 | 4 | | | | | IV-1 | Ccdc91 | |
| 14361 | 3 | 4 | | | | | IV-1 | Ccdc97 | |
| 14362 | 3 | 4 | | | | | IV-1 | Cchcr1 | |
| 14363 | 3 | 4 | | | | | IV-1 | Cckbr | |
| 14364 | 3 | 4 | | | | | IV-1 | Ccl11 | |
| 14365 | 3 | 4 | | | | | IV-1 | Ccl26 | |
| 14366 | 3 | 4 | | | | | IV-1 | Ccl27b | |
| 14367 | 3 | 4 | | | | | IV-1 | Ccna1 | |
| 14368 | 3 | 4 | | | | | IV-1 | Ccnb1 | |
| 14369 | 3 | 4 | | | | | IV-1 | Ccnb1ip1 | |
| 14370 | 3 | 4 | | | | | IV-1 | Ccnb3 | |
| 14371 | 3 | 4 | | | | | IV-1 | Ccnc | |
| 14372 | 3 | 4 | | | | | IV-1 | Ccnf | |
| 14373 | 3 | 4 | | | | | IV-1 | Ccnh | |
| 14374 | 3 | 4 | | | | | IV-1 | Ccni | |
| 14375 | 3 | 4 | | | | | IV-1 | Ccnjl | |
| 14376 | 3 | 4 | | | | | IV-1 | Ccnk | |
| 14377 | 3 | 4 | | | | | IV-1 | Ccnl2 | |
| 14378 | 3 | 4 | | | | | IV-1 | Ccny | |
| 14379 | 3 | 4 | | | | | IV-1 | Ccnyl1 | |
| 14380 | 3 | 4 | | | | | IV-1 | Ccpg1 | |
| 14381 | 3 | 4 | | | | | IV-1 | Ccr1l1 | |
| 14382 | 3 | 4 | | | | | IV-1 | Ccs | |
| 14383 | 3 | 4 | | | | | IV-1 | Ccsap | |
| 14384 | 3 | 4 | | | | | IV-1 | Cct2 | |
| 14385 | 3 | 4 | | | | | IV-1 | Cct5 | |
| 14386 | 3 | 4 | | | | | IV-1 | Cct6b | |
| 14387 | 3 | 4 | | | | | IV-1 | Cct7 | |
| 14388 | 3 | 4 | | | | | IV-1 | Cct8 | |
| 14389 | 3 | 4 | | | | | IV-1 | Cct8l1 | |
| 14390 | 3 | 4 | | | | | IV-1 | Cd151 | |
| 14391 | 3 | 4 | | | | | IV-1 | Cd163l1 | |
| 14392 | 3 | 4 | | | | | IV-1 | Cd164 | |
| 14393 | 3 | 4 | | | | | IV-1 | Cd1d2 | |
| 14394 | 3 | 4 | | | | | IV-1 | Cd200r1 | |
| 14395 | 3 | 4 | | | | | IV-1 | Cd200r2 | |
| 14396 | 3 | 4 | | | | | IV-1 | Cd200r3 | |
| 14397 | 3 | 4 | | | | | IV-1 | Cd207 | |
| 14398 | 3 | 4 | | | | | IV-1 | Cd209c | |
| 14399 | 3 | 4 | | | | | IV-1 | Cd209d | |
| 14400 | 3 | 4 | | | | | IV-1 | Cd209e | |
| 14401 | 3 | 4 | | | | | IV-1 | Cd209g | |
| 14402 | 3 | 4 | | | | | IV-1 | Cd2ap | |
| 14403 | 3 | 4 | | | | | IV-1 | Cd2bp2 | |
| 14404 | 3 | 4 | | | | | IV-1 | Cd300e | |
| 14405 | 3 | 4 | | | | | IV-1 | Cd300lg | |
| 14406 | 3 | 4 | | | | | IV-1 | Cd40lg | |
| 14407 | 3 | 4 | | | | | IV-1 | Cd46 | |
| 14408 | 3 | 4 | | | | | IV-1 | Cd59b | |
| 14409 | 3 | 4 | | | | | IV-1 | Cd6 | |
| 14410 | 3 | 4 | | | | | IV-1 | Cd70 | |
| 14411 | 3 | 4 | | | | | IV-1 | Cd81 | |
| 14412 | 3 | 4 | | | | | IV-1 | Cd86 | |
| 14413 | 3 | 4 | | | | | IV-1 | Cd97 | |
| 14414 | 3 | 4 | | | | | IV-1 | Cd99l2 | |
| 14415 | 3 | 4 | | | | | IV-1 | Cdan1 | |
| 14416 | 3 | 4 | | | | | IV-1 | Cdc123 | |
| 14417 | 3 | 4 | | | | | IV-1 | Cdc14a | |
| 14418 | 3 | 4 | | | | | IV-1 | Cdc14b | |
| 14419 | 3 | 4 | | | | | IV-1 | Cdc20b | |
| 14420 | 3 | 4 | | | | | IV-1 | Cdc25a | |
| 14421 | 3 | 4 | | | | | IV-1 | Cdc25c | |
| 14422 | 3 | 4 | | | | | IV-1 | Cdc27 | |
| 14423 | 3 | 4 | | | | | IV-1 | Cdc37 | |
| 14424 | 3 | 4 | | | | | IV-1 | Cdc40 | |
| 14425 | 3 | 4 | | | | | IV-1 | Cdc42 | |
| 14426 | 3 | 4 | | | | | IV-1 | Cdc42bpb | |
| 14427 | 3 | 4 | | | | | IV-1 | Cdc42ep1 | |
| 14428 | 3 | 4 | | | | | IV-1 | Cdc42ep2 | |
| 14429 | 3 | 4 | | | | | IV-1 | Cdc42ep4 | |
| 14430 | 3 | 4 | | | | | IV-1 | Cdc42se1 | |
| 14431 | 3 | 4 | | | | | IV-1 | Cdc42se2 | |
| 14432 | 3 | 4 | | | | | IV-1 | Cdc45 | |
| 14433 | 3 | 4 | | | | | IV-1 | Cdc73 | |
| 14434 | 3 | 4 | | | | | IV-1 | Cdca2 | |
| 14435 | 3 | 4 | | | | | IV-1 | Cdca4 | |
| 14436 | 3 | 4 | | | | | IV-1 | Cdcp2 | |
| 14437 | 3 | 4 | | | | | IV-1 | Cdh10 | |
| 14438 | 3 | 4 | | | | | IV-1 | Cdh11 | |
| 14439 | 3 | 4 | | | | | IV-1 | Cdh12 | |
| 14440 | 3 | 4 | | | | | IV-1 | Cdh18 | |
| 14441 | 3 | 4 | | | | | IV-1 | Cdh2 | |
| 14442 | 3 | 4 | | | | | IV-1 | Cdh20 | |
| 14443 | 3 | 4 | | | | | IV-1 | Cdh23 | |
| 14444 | 3 | 4 | | | | | IV-1 | Cdh26 | |
| 14445 | 3 | 4 | | | | | IV-1 | Cdh5 | |
| 14446 | 3 | 4 | | | | | IV-1 | Cdh7 | |
| 14447 | 3 | 4 | | | | | IV-1 | Cdh8 | |

Fig. 43 - 86

| | | | | | | | |
|---|---|---|---|---|---|---|---|
| 14448 | 3 | 4 | | | | IV-1 | Cdh9 |
| 14449 | 3 | 4 | | | | IV-1 | Cdhr1 |
| 14450 | 3 | 4 | | | | IV-1 | Cdhr3 |
| 14451 | 3 | 4 | | | | IV-1 | Cdip1 |
| 14452 | 3 | 4 | | | | IV-1 | Cdk13 |
| 14453 | 3 | 4 | | | | IV-1 | Cdk15 |
| 14454 | 3 | 4 | | | | IV-1 | Cdk16 |
| 14455 | 3 | 4 | | | | IV-1 | Cdk19 |
| 14456 | 3 | 4 | | | | IV-1 | Cdk3-ps |
| 14457 | 3 | 4 | | | | IV-1 | Cdk4 |
| 14458 | 3 | 4 | | | | IV-1 | Cdk5r1 |
| 14459 | 3 | 4 | | | | IV-1 | Cdk5r2 |
| 14460 | 3 | 4 | | | | IV-1 | Cdk5rap1 |
| 14461 | 3 | 4 | | | | IV-1 | Cdk5rap3 |
| 14462 | 3 | 4 | | | | IV-1 | Cdkl4 |
| 14463 | 3 | 4 | | | | IV-1 | Cdkn1c |
| 14464 | 3 | 4 | | | | IV-1 | Cdkn2a |
| 14465 | 3 | 4 | | | | IV-1 | Cdkn2aip |
| 14466 | 3 | 4 | | | | IV-1 | Cdkn2c |
| 14467 | 3 | 4 | | | | IV-1 | Cdkn2d |
| 14468 | 3 | 4 | | | | IV-1 | Cdr1 |
| 14469 | 3 | 4 | | | | IV-1 | Cdr2l |
| 14470 | 3 | 4 | | | | IV-1 | Cdv3 |
| 14471 | 3 | 4 | | | | IV-1 | Cdx2 |
| 14472 | 3 | 4 | | | | IV-1 | Cdx4 |
| 14473 | 3 | 4 | | | | IV-1 | Cdyl |
| 14474 | 3 | 4 | | | | IV-1 | Cdyl2 |
| 14475 | 3 | 4 | | | | IV-1 | Ceacam11 |
| 14476 | 3 | 4 | | | | IV-1 | Ceacam13 |
| 14477 | 3 | 4 | | | | IV-1 | Ceacam15 |
| 14478 | 3 | 4 | | | | IV-1 | Ceacam19 |
| 14479 | 3 | 4 | | | | IV-1 | Ceacam5 |
| 14480 | 3 | 4 | | | | IV-1 | Ceacam9 |
| 14481 | 3 | 4 | | | | IV-1 | Cebpb |
| 14482 | 3 | 4 | | | | IV-1 | Cebpz |
| 14483 | 3 | 4 | | | | IV-1 | Cecr6 |
| 14484 | 3 | 4 | | | | IV-1 | Celf1 |
| 14485 | 3 | 4 | | | | IV-1 | Celf3 |
| 14486 | 3 | 4 | | | | IV-1 | Celf5 |
| 14487 | 3 | 4 | | | | IV-1 | Celf6 |
| 14488 | 3 | 4 | | | | IV-1 | Celrr |
| 14489 | 3 | 4 | | | | IV-1 | Celsr1 |
| 14490 | 3 | 4 | | | | IV-1 | Cenpb |
| 14491 | 3 | 4 | | | | IV-1 | Cenpc1 |
| 14492 | 3 | 4 | | | | IV-1 | Cenpe |
| 14493 | 3 | 4 | | | | IV-1 | Cenpf |
| 14494 | 3 | 4 | | | | IV-1 | Cenph |
| 14495 | 3 | 4 | | | | IV-1 | Cenpi |
| 14496 | 3 | 4 | | | | IV-1 | Cenpj |
| 14497 | 3 | 4 | | | | IV-1 | Cenpq |
| 14498 | 3 | 4 | | | | IV-1 | Cenpt |
| 14499 | 3 | 4 | | | | IV-1 | Cep120 |
| 14500 | 3 | 4 | | | | IV-1 | Cep164 |
| 14501 | 3 | 4 | | | | IV-1 | Cep170b |
| 14502 | 3 | 4 | | | | IV-1 | Cep192 |
| 14503 | 3 | 4 | | | | IV-1 | Cep290 |
| 14504 | 3 | 4 | | | | IV-1 | Cep41 |
| 14505 | 3 | 4 | | | | IV-1 | Cep57 |
| 14506 | 3 | 4 | | | | IV-1 | Cep57l1 |
| 14507 | 3 | 4 | | | | IV-1 | Cep63 |
| 14508 | 3 | 4 | | | | IV-1 | Cep76 |
| 14509 | 3 | 4 | | | | IV-1 | Cep83 |
| 14510 | 3 | 4 | | | | IV-1 | Cep89 |
| 14511 | 3 | 4 | | | | IV-1 | Cept1 |
| 14512 | 3 | 4 | | | | IV-1 | Cer1 |
| 14513 | 3 | 4 | | | | IV-1 | Cerkl |
| 14514 | 3 | 4 | | | | IV-1 | Cers1 |
| 14515 | 3 | 4 | | | | IV-1 | Cers2 |
| 14516 | 3 | 4 | | | | IV-1 | Cers5 |
| 14517 | 3 | 4 | | | | IV-1 | Ces1a |
| 14518 | 3 | 4 | | | | IV-1 | Ces1c |
| 14519 | 3 | 4 | | | | IV-1 | Ces2a |
| 14520 | 3 | 4 | | | | IV-1 | Ces2d-ps |
| 14521 | 3 | 4 | | | | IV-1 | Ces2h |
| 14522 | 3 | 4 | | | | IV-1 | Ces3a |
| 14523 | 3 | 4 | | | | IV-1 | Ces4a |
| 14524 | 3 | 4 | | | | IV-1 | Cfh |
| 14525 | 3 | 4 | | | | IV-1 | Cfhr1 |
| 14526 | 3 | 4 | | | | IV-1 | Cga |
| 14527 | 3 | 4 | | | | IV-1 | Cggbp1 |
| 14528 | 3 | 4 | | | | IV-1 | Champ1 |
| 14529 | 3 | 4 | | | | IV-1 | Chat |
| 14530 | 3 | 4 | | | | IV-1 | Chchd3 |
| 14531 | 3 | 4 | | | | IV-1 | Chd2 |
| 14532 | 3 | 4 | | | | IV-1 | Chd3os |
| 14533 | 3 | 4 | | | | IV-1 | Chd4 |
| 14534 | 3 | 4 | | | | IV-1 | Chd5 |
| 14535 | 3 | 4 | | | | IV-1 | Chd8 |
| 14536 | 3 | 4 | | | | IV-1 | Chek2 |
| 14537 | 3 | 4 | | | | IV-1 | Cherp |
| 14538 | 3 | 4 | | | | IV-1 | Chfr |
| 14539 | 3 | 4 | | | | IV-1 | Chic2 |
| 14540 | 3 | 4 | | | | IV-1 | Chil4 |
| 14541 | 3 | 4 | | | | IV-1 | Chil6 |
| 14542 | 3 | 4 | | | | IV-1 | Chka |
| 14543 | 3 | 4 | | | | IV-1 | Chkb |
| 14544 | 3 | 4 | | | | IV-1 | ChkbCpt1b |
| 14545 | 3 | 4 | | | | IV-1 | Chl1 |
| 14546 | 3 | 4 | | | | IV-1 | Chmp1a |
| 14547 | 3 | 4 | | | | IV-1 | Chmp1b |
| 14548 | 3 | 4 | | | | IV-1 | Chmp2b |
| 14549 | 3 | 4 | | | | IV-1 | Chmp3 |
| 14550 | 3 | 4 | | | | IV-1 | Chmp7 |
| 14551 | 3 | 4 | | | | IV-1 | Chnlos3 |
| 14552 | 3 | 4 | | | | IV-1 | Chp1 |
| 14553 | 3 | 4 | | | | IV-1 | Chp2 |
| 14554 | 3 | 4 | | | | IV-1 | Chpt1 |
| 14555 | 3 | 4 | | | | IV-1 | Chrdl2 |
| 14556 | 3 | 4 | | | | IV-1 | Chrm5 |
| 14557 | 3 | 4 | | | | IV-1 | Chrna4 |
| 14558 | 3 | 4 | | | | IV-1 | Chrna6 |
| 14559 | 3 | 4 | | | | IV-1 | Chrna7 |
| 14560 | 3 | 4 | | | | IV-1 | Chrnb3 |
| 14561 | 3 | 4 | | | | IV-1 | Chrnb4 |
| 14562 | 3 | 4 | | | | IV-1 | Chrng |
| 14563 | 3 | 4 | | | | IV-1 | Chst1 |
| 14564 | 3 | 4 | | | | IV-1 | Chst12 |
| 14565 | 3 | 4 | | | | IV-1 | Chst13 |
| 14566 | 3 | 4 | | | | IV-1 | Chst5 |
| 14567 | 3 | 4 | | | | IV-1 | Chst7 |
| 14568 | 3 | 4 | | | | IV-1 | Chst9 |
| 14569 | 3 | 4 | | | | IV-1 | Chsy3 |
| 14570 | 3 | 4 | | | | IV-1 | Chtop |
| 14571 | 3 | 4 | | | | IV-1 | Cib3 |
| 14572 | 3 | 4 | | | | IV-1 | Cic |
| 14573 | 3 | 4 | | | | IV-1 | Cideb |
| 14574 | 3 | 4 | | | | IV-1 | Cilp2 |
| 14575 | 3 | 4 | | | | IV-1 | Cipc |
| 14576 | 3 | 4 | | | | IV-1 | Cisd1 |
| 14577 | 3 | 4 | | | | IV-1 | Cisd2 |
| 14578 | 3 | 4 | | | | IV-1 | Cistr-act |
| 14579 | 3 | 4 | | | | IV-1 | Cit |
| 14580 | 3 | 4 | | | | IV-1 | Ciz1 |
| 14581 | 3 | 4 | | | | IV-1 | Ckap5 |
| 14582 | 3 | 4 | | | | IV-1 | Ckmt1 |
| 14583 | 3 | 4 | | | | IV-1 | Cks1brt |
| 14584 | 3 | 4 | | | | IV-1 | Clasp1 |
| 14585 | 3 | 4 | | | | IV-1 | Clasp2 |
| 14586 | 3 | 4 | | | | IV-1 | Clca3 |
| 14587 | 3 | 4 | | | | IV-1 | Clca4 |
| 14588 | 3 | 4 | | | | IV-1 | Clca6 |
| 14589 | 3 | 4 | | | | IV-1 | Clcc1 |
| 14590 | 3 | 4 | | | | IV-1 | Clcn1 |
| 14591 | 3 | 4 | | | | IV-1 | Clcn3 |
| 14592 | 3 | 4 | | | | IV-1 | Clcn5 |
| 14593 | 3 | 4 | | | | IV-1 | Clcn7 |
| 14594 | 3 | 4 | | | | IV-1 | Clcnka |
| 14595 | 3 | 4 | | | | IV-1 | Clcnkb |
| 14596 | 3 | 4 | | | | IV-1 | Cldn14 |
| 14597 | 3 | 4 | | | | IV-1 | Cldn16 |
| 14598 | 3 | 4 | | | | IV-1 | Cldn17 |
| 14599 | 3 | 4 | | | | IV-1 | Cldn18 |
| 14600 | 3 | 4 | | | | IV-1 | Cldn19 |
| 14601 | 3 | 4 | | | | IV-1 | Cldn24 |
| 14602 | 3 | 4 | | | | IV-1 | Cldn25 |
| 14603 | 3 | 4 | | | | IV-1 | Cldn26 |
| 14604 | 3 | 4 | | | | IV-1 | Cldn6 |
| 14605 | 3 | 4 | | | | IV-1 | Cldnd2 |
| 14606 | 3 | 4 | | | | IV-1 | Clec16a |
| 14607 | 3 | 4 | | | | IV-1 | Clec2f |
| 14608 | 3 | 4 | | | | IV-1 | Clec2i |
| 14609 | 3 | 4 | | | | IV-1 | Clec4a4 |
| 14610 | 3 | 4 | | | | IV-1 | Clec4f |
| 14611 | 3 | 4 | | | | IV-1 | Clec4g |
| 14612 | 3 | 4 | | | | IV-1 | Clint1 |
| 14613 | 3 | 4 | | | | IV-1 | Clip2 |
| 14614 | 3 | 4 | | | | IV-1 | Clip3 |
| 14615 | 3 | 4 | | | | IV-1 | Clk2 |
| 14616 | 3 | 4 | | | | IV-1 | Clk4 |
| 14617 | 3 | 4 | | | | IV-1 | Cln5 |

Fig. 43 - 87

| | | | | | | | | |
|---|---|---|---|---|---|---|---|---|
| 14618 | 3 | 4 | | | | | IV-1 | Clns6 |
| 14619 | 3 | 4 | | | | | IV-1 | Clnk |
| 14620 | 3 | 4 | | | | | IV-1 | Clp1 |
| 14621 | 3 | 4 | | | | | IV-1 | Clpsl2 |
| 14622 | 3 | 4 | | | | | IV-1 | Clptm1 |
| 14623 | 3 | 4 | | | | | IV-1 | Clptm1l |
| 14624 | 3 | 4 | | | | | IV-1 | Clpx |
| 14625 | 3 | 4 | | | | | IV-1 | Clrn1 |
| 14626 | 3 | 4 | | | | | IV-1 | Clrn2 |
| 14627 | 3 | 4 | | | | | IV-1 | Clspn |
| 14628 | 3 | 4 | | | | | IV-1 | Clstn1 |
| 14629 | 3 | 4 | | | | | IV-1 | Clstn2 |
| 14630 | 3 | 4 | | | | | IV-1 | Cltc |
| 14631 | 3 | 4 | | | | | IV-1 | Cluh |
| 14632 | 3 | 4 | | | | | IV-1 | Clvs1 |
| 14633 | 3 | 4 | | | | | IV-1 | Clvs2 |
| 14634 | 3 | 4 | | | | | IV-1 | Cma2 |
| 14635 | 3 | 4 | | | | | IV-1 | Cml3 |
| 14636 | 3 | 4 | | | | | IV-1 | Cmpk1 |
| 14637 | 3 | 4 | | | | | IV-1 | Cmtm1 |
| 14638 | 3 | 4 | | | | | IV-1 | Cmtm3 |
| 14639 | 3 | 4 | | | | | IV-1 | Cmtm5 |
| 14640 | 3 | 4 | | | | | IV-1 | Cmtm6 |
| 14641 | 3 | 4 | | | | | IV-1 | Cmtr1 |
| 14642 | 3 | 4 | | | | | IV-1 | Cmtr2 |
| 14643 | 3 | 4 | | | | | IV-1 | Cnbd2 |
| 14644 | 3 | 4 | | | | | IV-1 | Cndp2 |
| 14645 | 3 | 4 | | | | | IV-1 | Cnfn |
| 14646 | 3 | 4 | | | | | IV-1 | Cnga2 |
| 14647 | 3 | 4 | | | | | IV-1 | Cnga4 |
| 14648 | 3 | 4 | | | | | IV-1 | Cngb1 |
| 14649 | 3 | 4 | | | | | IV-1 | Cnih3 |
| 14650 | 3 | 4 | | | | | IV-1 | Cnih4 |
| 14651 | 3 | 4 | | | | | IV-1 | Cnksr2 |
| 14652 | 3 | 4 | | | | | IV-1 | Cnn3 |
| 14653 | 3 | 4 | | | | | IV-1 | Cnnm1 |
| 14654 | 3 | 4 | | | | | IV-1 | Cnot10 |
| 14655 | 3 | 4 | | | | | IV-1 | Cnot11 |
| 14656 | 3 | 4 | | | | | IV-1 | Cnot4 |
| 14657 | 3 | 4 | | | | | IV-1 | Cnot6l |
| 14658 | 3 | 4 | | | | | IV-1 | Cnot7 |
| 14659 | 3 | 4 | | | | | IV-1 | Cnpy1 |
| 14660 | 3 | 4 | | | | | IV-1 | Cnpy2 |
| 14661 | 3 | 4 | | | | | IV-1 | Cnr1 |
| 14662 | 3 | 4 | | | | | IV-1 | Cnst |
| 14663 | 3 | 4 | | | | | IV-1 | Cntd1 |
| 14664 | 3 | 4 | | | | | IV-1 | Cntfr |
| 14665 | 3 | 4 | | | | | IV-1 | Cntln |
| 14666 | 3 | 4 | | | | | IV-1 | Cntn1 |
| 14667 | 3 | 4 | | | | | IV-1 | Cntn2 |
| 14668 | 3 | 4 | | | | | IV-1 | Cntn3 |
| 14669 | 3 | 4 | | | | | IV-1 | Cntn4 |
| 14670 | 3 | 4 | | | | | IV-1 | Cntn5 |
| 14671 | 3 | 4 | | | | | IV-1 | Cntn6 |
| 14672 | 3 | 4 | | | | | IV-1 | Cntnap2 |
| 14673 | 3 | 4 | | | | | IV-1 | Cntnap4 |
| 14674 | 3 | 4 | | | | | IV-1 | Cntnap5b |
| 14675 | 3 | 4 | | | | | IV-1 | Cntnap5c |
| 14676 | 3 | 4 | | | | | IV-1 | Coasy |
| 14677 | 3 | 4 | | | | | IV-1 | Cog1 |
| 14678 | 3 | 4 | | | | | IV-1 | Cog2 |
| 14679 | 3 | 4 | | | | | IV-1 | Cog3 |
| 14680 | 3 | 4 | | | | | IV-1 | Cog4 |
| 14681 | 3 | 4 | | | | | IV-1 | Cog5 |
| 14682 | 3 | 4 | | | | | IV-1 | Cog6 |
| 14683 | 3 | 4 | | | | | IV-1 | Cog7 |
| 14684 | 3 | 4 | | | | | IV-1 | Coil |
| 14685 | 3 | 4 | | | | | IV-1 | Col10a1 |
| 14686 | 3 | 4 | | | | | IV-1 | Col11a1 |
| 14687 | 3 | 4 | | | | | IV-1 | Col19a1 |
| 14688 | 3 | 4 | | | | | IV-1 | Col20a1 |
| 14689 | 3 | 4 | | | | | IV-1 | Col22a1 |
| 14690 | 3 | 4 | | | | | IV-1 | Col23a1 |
| 14691 | 3 | 4 | | | | | IV-1 | Col25a1 |
| 14692 | 3 | 4 | | | | | IV-1 | Col26a1 |
| 14693 | 3 | 4 | | | | | IV-1 | Col2a1 |
| 14694 | 3 | 4 | | | | | IV-1 | Col4a1 |
| 14695 | 3 | 4 | | | | | IV-1 | Col4a2 |
| 14696 | 3 | 4 | | | | | IV-1 | Col4a3bp |
| 14697 | 3 | 4 | | | | | IV-1 | Col4a6 |
| 14698 | 3 | 4 | | | | | IV-1 | Col5a1 |
| 14699 | 3 | 4 | | | | | IV-1 | Col5a3 |
| 14700 | 3 | 4 | | | | | IV-1 | Col6a2 |
| 14701 | 3 | 4 | | | | | IV-1 | Col6a4 |
| 14702 | 3 | 4 | | | | | IV-1 | Col6a5 |
| 14703 | 3 | 4 | | | | | IV-1 | Col6a6 |
| 14704 | 3 | 4 | | | | | IV-1 | Col7a1 |
| 14705 | 3 | 4 | | | | | IV-1 | Col9a1 |
| 14706 | 3 | 4 | | | | | IV-1 | Col9a2 |
| 14707 | 3 | 4 | | | | | IV-1 | Col9a3 |
| 14708 | 3 | 4 | | | | | IV-1 | Colec11 |
| 14709 | 3 | 4 | | | | | IV-1 | Commd5 |
| 14710 | 3 | 4 | | | | | IV-1 | Commd8 |
| 14711 | 3 | 4 | | | | | IV-1 | Commd9 |
| 14712 | 3 | 4 | | | | | IV-1 | Comp |
| 14713 | 3 | 4 | | | | | IV-1 | Copa |
| 14714 | 3 | 4 | | | | | IV-1 | Copb1 |
| 14715 | 3 | 4 | | | | | IV-1 | Copb2 |
| 14716 | 3 | 4 | | | | | IV-1 | Copg1 |
| 14717 | 3 | 4 | | | | | IV-1 | Copg2 |
| 14718 | 3 | 4 | | | | | IV-1 | Cops2 |
| 14719 | 3 | 4 | | | | | IV-1 | Cops3 |
| 14720 | 3 | 4 | | | | | IV-1 | Cops5 |
| 14721 | 3 | 4 | | | | | IV-1 | Cops7a |
| 14722 | 3 | 4 | | | | | IV-1 | Cops7b |
| 14723 | 3 | 4 | | | | | IV-1 | Cops8 |
| 14724 | 3 | 4 | | | | | IV-1 | Copz1 |
| 14725 | 3 | 4 | | | | | IV-1 | Coq10a |
| 14726 | 3 | 4 | | | | | IV-1 | Coq10b |
| 14727 | 3 | 4 | | | | | IV-1 | Coq3 |
| 14728 | 3 | 4 | | | | | IV-1 | Coq6 |
| 14729 | 3 | 4 | | | | | IV-1 | Corin |
| 14730 | 3 | 4 | | | | | IV-1 | Coro2a |
| 14731 | 3 | 4 | | | | | IV-1 | Cort |
| 14732 | 3 | 4 | | | | | IV-1 | Cox6c |
| 14733 | 3 | 4 | | | | | IV-1 | Cox7a2l |
| 14734 | 3 | 4 | | | | | IV-1 | Cpa4 |
| 14735 | 3 | 4 | | | | | IV-1 | Cpa5 |
| 14736 | 3 | 4 | | | | | IV-1 | Cpa6 |
| 14737 | 3 | 4 | | | | | IV-1 | Cpe |
| 14738 | 3 | 4 | | | | | IV-1 | Cpeb2 |
| 14739 | 3 | 4 | | | | | IV-1 | Cphx2 |
| 14740 | 3 | 4 | | | | | IV-1 | Cplx1 |
| 14741 | 3 | 4 | | | | | IV-1 | Cplx3 |
| 14742 | 3 | 4 | | | | | IV-1 | Cpne4 |
| 14743 | 3 | 4 | | | | | IV-1 | Cpne5 |
| 14744 | 3 | 4 | | | | | IV-1 | Cpne6 |
| 14745 | 3 | 4 | | | | | IV-1 | Cpne7 |
| 14746 | 3 | 4 | | | | | IV-1 | Cpne9 |
| 14747 | 3 | 4 | | | | | IV-1 | Cpsf1 |
| 14748 | 3 | 4 | | | | | IV-1 | Cpsf3 |
| 14749 | 3 | 4 | | | | | IV-1 | Cpsf3l |
| 14750 | 3 | 4 | | | | | IV-1 | Cpsf7 |
| 14751 | 3 | 4 | | | | | IV-1 | Cpt2 |
| 14752 | 3 | 4 | | | | | IV-1 | Cpvl |
| 14753 | 3 | 4 | | | | | IV-1 | Cpxcr1 |
| 14754 | 3 | 4 | | | | | IV-1 | Cpz |
| 14755 | 3 | 4 | | | | | IV-1 | Cr1l |
| 14756 | 3 | 4 | | | | | IV-1 | Crat |
| 14757 | 3 | 4 | | | | | IV-1 | Crb2 |
| 14758 | 3 | 4 | | | | | IV-1 | Crbn |
| 14759 | 3 | 4 | | | | | IV-1 | Creb3l3 |
| 14760 | 3 | 4 | | | | | IV-1 | Crebrf |
| 14761 | 3 | 4 | | | | | IV-1 | Crebzf |
| 14762 | 3 | 4 | | | | | IV-1 | Creg2 |
| 14763 | 3 | 4 | | | | | IV-1 | Creld1 |
| 14764 | 3 | 4 | | | | | IV-1 | Crh |
| 14765 | 3 | 4 | | | | | IV-1 | Crhbp |
| 14766 | 3 | 4 | | | | | IV-1 | Crhr1 |
| 14767 | 3 | 4 | | | | | IV-1 | Crip3 |
| 14768 | 3 | 4 | | | | | IV-1 | Crisp3 |
| 14769 | 3 | 4 | | | | | IV-1 | Crisp4 |
| 14770 | 3 | 4 | | | | | IV-1 | Crk |
| 14771 | 3 | 4 | | | | | IV-1 | Crlf1 |
| 14772 | 3 | 4 | | | | | IV-1 | Crlf3 |
| 14773 | 3 | 4 | | | | | IV-1 | Crmp1 |
| 14774 | 3 | 4 | | | | | IV-1 | Crnde |
| 14775 | 3 | 4 | | | | | IV-1 | Crnn |
| 14776 | 3 | 4 | | | | | IV-1 | Crocc |
| 14777 | 3 | 4 | | | | | IV-1 | Crot |
| 14778 | 3 | 4 | | | | | IV-1 | Crtac1 |
| 14779 | 3 | 4 | | | | | IV-1 | Crtap |
| 14780 | 3 | 4 | | | | | IV-1 | Crtc1 |
| 14781 | 3 | 4 | | | | | IV-1 | Crtc2 |
| 14782 | 3 | 4 | | | | | IV-1 | Crxos |
| 14783 | 3 | 4 | | | | | IV-1 | Cry2 |
| 14784 | 3 | 4 | | | | | IV-1 | Cryaa |
| 14785 | 3 | 4 | | | | | IV-1 | Crybb2 |
| 14786 | 3 | 4 | | | | | IV-1 | Crygb |
| 14787 | 3 | 4 | | | | | IV-1 | Cryge |

Fig. 43 - 88

| | | | | | | | |
|---|---|---|---|---|---|---|---|
| 14788 | 3 | 4 | | | | IV-1 | Crygf |
| 14789 | 3 | 4 | | | | IV-1 | Crygn |
| 14790 | 3 | 4 | | | | IV-1 | Csdc2 |
| 14791 | 3 | 4 | | | | IV-1 | Csde1 |
| 14792 | 3 | 4 | | | | IV-1 | Csf2 |
| 14793 | 3 | 4 | | | | IV-1 | Csf2ra |
| 14794 | 3 | 4 | | | | IV-1 | Csf3 |
| 14795 | 3 | 4 | | | | IV-1 | Csgalnact2 |
| 14796 | 3 | 4 | | | | IV-1 | Csmd2 |
| 14797 | 3 | 4 | | | | IV-1 | Csmd2os |
| 14798 | 3 | 4 | | | | IV-1 | Csmd3 |
| 14799 | 3 | 4 | | | | IV-1 | Csn1s1 |
| 14800 | 3 | 4 | | | | IV-1 | Csn1s2a |
| 14801 | 3 | 4 | | | | IV-1 | Csn1s2b |
| 14802 | 3 | 4 | | | | IV-1 | Csnk1a1 |
| 14803 | 3 | 4 | | | | IV-1 | Csnk1g2 |
| 14804 | 3 | 4 | | | | IV-1 | Csnk2a1 |
| 14805 | 3 | 4 | | | | IV-1 | Csnk2b |
| 14806 | 3 | 4 | | | | IV-1 | Cspg5 |
| 14807 | 3 | 4 | | | | IV-1 | Cspp1 |
| 14808 | 3 | 4 | | | | IV-1 | Csprs |
| 14809 | 3 | 4 | | | | IV-1 | Csrnp3 |
| 14810 | 3 | 4 | | | | IV-1 | Cst10 |
| 14811 | 3 | 4 | | | | IV-1 | Cst11 |
| 14812 | 3 | 4 | | | | IV-1 | Cst3 |
| 14813 | 3 | 4 | | | | IV-1 | Cstf2 |
| 14814 | 3 | 4 | | | | IV-1 | Cstf2t |
| 14815 | 3 | 4 | | | | IV-1 | Ctag2 |
| 14816 | 3 | 4 | | | | IV-1 | Ctage5 |
| 14817 | 3 | 4 | | | | IV-1 | Ctbp1 |
| 14818 | 3 | 4 | | | | IV-1 | Ctbs |
| 14819 | 3 | 4 | | | | IV-1 | Ctcflos |
| 14820 | 3 | 4 | | | | IV-1 | Ctdnep1 |
| 14821 | 3 | 4 | | | | IV-1 | Ctdp1 |
| 14822 | 3 | 4 | | | | IV-1 | Ctdsp2 |
| 14823 | 3 | 4 | | | | IV-1 | Ctdspl |
| 14824 | 3 | 4 | | | | IV-1 | Ctdspl2 |
| 14825 | 3 | 4 | | | | IV-1 | Ctf2 |
| 14826 | 3 | 4 | | | | IV-1 | Cthrc1 |
| 14827 | 3 | 4 | | | | IV-1 | Ctif |
| 14828 | 3 | 4 | | | | IV-1 | Ctnna1 |
| 14829 | 3 | 4 | | | | IV-1 | Ctnna2 |
| 14830 | 3 | 4 | | | | IV-1 | Ctnnb1 |
| 14831 | 3 | 4 | | | | IV-1 | Ctnnbl1 |
| 14832 | 3 | 4 | | | | IV-1 | Ctnnd1 |
| 14833 | 3 | 4 | | | | IV-1 | Ctnnd2 |
| 14834 | 3 | 4 | | | | IV-1 | Ctns |
| 14835 | 3 | 4 | | | | IV-1 | Ctps2 |
| 14836 | 3 | 4 | | | | IV-1 | Ctr9 |
| 14837 | 3 | 4 | | | | IV-1 | Ctrc |
| 14838 | 3 | 4 | | | | IV-1 | Ctrcos |
| 14839 | 3 | 4 | | | | IV-1 | Cts3 |
| 14840 | 3 | 4 | | | | IV-1 | Cts6 |
| 14841 | 3 | 4 | | | | IV-1 | Cts7 |
| 14842 | 3 | 4 | | | | IV-1 | Cts8 |
| 14843 | 3 | 4 | | | | IV-1 | Cts8-ps |
| 14844 | 3 | 4 | | | | IV-1 | Ctsa |
| 14845 | 3 | 4 | | | | IV-1 | Ctsll3 |
| 14846 | 3 | 4 | | | | IV-1 | Ctsm |
| 14847 | 3 | 4 | | | | IV-1 | Ctso |
| 14848 | 3 | 4 | | | | IV-1 | Ctsq |
| 14849 | 3 | 4 | | | | IV-1 | Ctsr |
| 14850 | 3 | 4 | | | | IV-1 | Cttn |
| 14851 | 3 | 4 | | | | IV-1 | Ctxn1 |
| 14852 | 3 | 4 | | | | IV-1 | Ctxn2 |
| 14853 | 3 | 4 | | | | IV-1 | Cubn |
| 14854 | 3 | 4 | | | | IV-1 | Cuedc1 |
| 14855 | 3 | 4 | | | | IV-1 | Cuedc2 |
| 14856 | 3 | 4 | | | | IV-1 | Cul1 |
| 14857 | 3 | 4 | | | | IV-1 | Cul3 |
| 14858 | 3 | 4 | | | | IV-1 | Cul4b |
| 14859 | 3 | 4 | | | | IV-1 | Cul5 |
| 14860 | 3 | 4 | | | | IV-1 | Cul7 |
| 14861 | 3 | 4 | | | | IV-1 | Cwc15 |
| 14862 | 3 | 4 | | | | IV-1 | Cwc22 |
| 14863 | 3 | 4 | | | | IV-1 | Cwc25 |
| 14864 | 3 | 4 | | | | IV-1 | Cwf19l2 |
| 14865 | 3 | 4 | | | | IV-1 | Cxcl15 |
| 14866 | 3 | 4 | | | | IV-1 | Cxcl16 |
| 14867 | 3 | 4 | | | | IV-1 | Cxcl5 |
| 14868 | 3 | 4 | | | | IV-1 | Cxcr1 |
| 14869 | 3 | 4 | | | | IV-1 | Cxxc1 |
| 14870 | 3 | 4 | | | | IV-1 | Cyb5 |
| 14871 | 3 | 4 | | | | IV-1 | Cyb561d1 |
| 14872 | 3 | 4 | | | | IV-1 | Cyb5b |
| 14873 | 3 | 4 | | | | IV-1 | Cyb5r1 |
| 14874 | 3 | 4 | | | | IV-1 | Cyb5r3 |
| 14875 | 3 | 4 | | | | IV-1 | Cyc1 |
| 14876 | 3 | 4 | | | | IV-1 | Cyfip1 |
| 14877 | 3 | 4 | | | | IV-1 | Cyfip2 |
| 14878 | 3 | 4 | | | | IV-1 | Cygb |
| 14879 | 3 | 4 | | | | IV-1 | Cylc1 |
| 14880 | 3 | 4 | | | | IV-1 | Cyld |
| 14881 | 3 | 4 | | | | IV-1 | Cym |
| 14882 | 3 | 4 | | | | IV-1 | Cyp11a1 |
| 14883 | 3 | 4 | | | | IV-1 | Cyp11b1 |
| 14884 | 3 | 4 | | | | IV-1 | Cyp19a1 |
| 14885 | 3 | 4 | | | | IV-1 | Cyp26a1 |
| 14886 | 3 | 4 | | | | IV-1 | Cyp26c1 |
| 14887 | 3 | 4 | | | | IV-1 | Cyp2b13 |
| 14888 | 3 | 4 | | | | IV-1 | Cyp2b19 |
| 14889 | 3 | 4 | | | | IV-1 | Cyp2b23 |
| 14890 | 3 | 4 | | | | IV-1 | Cyp2b9 |
| 14891 | 3 | 4 | | | | IV-1 | Cyp2c29 |
| 14892 | 3 | 4 | | | | IV-1 | Cyp2d34 |
| 14893 | 3 | 4 | | | | IV-1 | Cyp2d40 |
| 14894 | 3 | 4 | | | | IV-1 | Cyp2d9 |
| 14895 | 3 | 4 | | | | IV-1 | Cyp2g1 |
| 14896 | 3 | 4 | | | | IV-1 | Cyp2j11 |
| 14897 | 3 | 4 | | | | IV-1 | Cyp2j13 |
| 14898 | 3 | 4 | | | | IV-1 | Cyp2j5 |
| 14899 | 3 | 4 | | | | IV-1 | Cyp2j8 |
| 14900 | 3 | 4 | | | | IV-1 | Cyp2r1 |
| 14901 | 3 | 4 | | | | IV-1 | Cyp2w1 |
| 14902 | 3 | 4 | | | | IV-1 | Cyp3a11 |
| 14903 | 3 | 4 | | | | IV-1 | Cyp3a13 |
| 14904 | 3 | 4 | | | | IV-1 | Cyp3a25 |
| 14905 | 3 | 4 | | | | IV-1 | Cyp3a41b |
| 14906 | 3 | 4 | | | | IV-1 | Cyp3a57 |
| 14907 | 3 | 4 | | | | IV-1 | Cyp4a30b |
| 14908 | 3 | 4 | | | | IV-1 | Cyp4f37 |
| 14909 | 3 | 4 | | | | IV-1 | Cyp4f39 |
| 14910 | 3 | 4 | | | | IV-1 | Cyp4f40 |
| 14911 | 3 | 4 | | | | IV-1 | Cyp4v3 |
| 14912 | 3 | 4 | | | | IV-1 | Cypt1 |
| 14913 | 3 | 4 | | | | IV-1 | Cypt14 |
| 14914 | 3 | 4 | | | | IV-1 | Cypt2 |
| 14915 | 3 | 4 | | | | IV-1 | Cys1 |
| 14916 | 3 | 4 | | | | IV-1 | Cysltr2 |
| 14917 | 3 | 4 | | | | IV-1 | Cytip |
| 14918 | 3 | 4 | | | | IV-1 | D030018L15Rik |
| 14919 | 3 | 4 | | | | IV-1 | D030024E09Rik |
| 14920 | 3 | 4 | | | | IV-1 | D030025E07Rik |
| 14921 | 3 | 4 | | | | IV-1 | D030025P21Rik |
| 14922 | 3 | 4 | | | | IV-1 | D030040B21Rik |
| 14923 | 3 | 4 | | | | IV-1 | D10Jhu81e |
| 14924 | 3 | 4 | | | | IV-1 | D10Wsu102e |
| 14925 | 3 | 4 | | | | IV-1 | D130009I18Rik |
| 14926 | 3 | 4 | | | | IV-1 | D130040H23Rik |
| 14927 | 3 | 4 | | | | IV-1 | D130043K22Rik |
| 14928 | 3 | 4 | | | | IV-1 | D130058E03 |
| 14929 | 3 | 4 | | | | IV-1 | D15Ertd621e |
| 14930 | 3 | 4 | | | | IV-1 | D16Ertd519e |
| 14931 | 3 | 4 | | | | IV-1 | D17Ertd648e |
| 14932 | 3 | 4 | | | | IV-1 | D17Wsu92e |
| 14933 | 3 | 4 | | | | IV-1 | D19Bwg1357e |
| 14934 | 3 | 4 | | | | IV-1 | D230030E09Rik |
| 14935 | 3 | 4 | | | | IV-1 | D330045A20Rik |
| 14936 | 3 | 4 | | | | IV-1 | D3Ertd751e |
| 14937 | 3 | 4 | | | | IV-1 | D430041D05Rik |
| 14938 | 3 | 4 | | | | IV-1 | D4Ertd617e |
| 14939 | 3 | 4 | | | | IV-1 | D530049I02Rik |
| 14940 | 3 | 4 | | | | IV-1 | D5Ertd577e |
| 14941 | 3 | 4 | | | | IV-1 | D630003M21Rik |
| 14942 | 3 | 4 | | | | IV-1 | D630024D03Rik |
| 14943 | 3 | 4 | | | | IV-1 | D630029K05Rik |
| 14944 | 3 | 4 | | | | IV-1 | D630041G03Rik |
| 14945 | 3 | 4 | | | | IV-1 | D6Ertd474e |
| 14946 | 3 | 4 | | | | IV-1 | D6Wsu163e |
| 14947 | 3 | 4 | | | | IV-1 | D730045A05Rik |
| 14948 | 3 | 4 | | | | IV-1 | D730050B12Rik |
| 14949 | 3 | 4 | | | | IV-1 | D830030K20Rik |
| 14950 | 3 | 4 | | | | IV-1 | D830046C22Rik |
| 14951 | 3 | 4 | | | | IV-1 | D930020B18Rik |
| 14952 | 3 | 4 | | | | IV-1 | Dab1 |
| 14953 | 3 | 4 | | | | IV-1 | Dach2 |
| 14954 | 3 | 4 | | | | IV-1 | Dact1 |
| 14955 | 3 | 4 | | | | IV-1 | Dact3 |
| 14956 | 3 | 4 | | | | IV-1 | Dad1 |
| 14957 | 3 | 4 | | | | IV-1 | Daglb |

Fig. 43 - 89

| | | | | | | | |
|---|---|---|---|---|---|---|---|
| 14958 | 3 | 4 | | | | IV-1 | Dap3 |
| 14959 | 3 | 4 | | | | IV-1 | Dapp1 |
| 14960 | 3 | 4 | | | | IV-1 | Dars |
| 14961 | 3 | 4 | | | | IV-1 | Dars2 |
| 14962 | 3 | 4 | | | | IV-1 | Dazap1 |
| 14963 | 3 | 4 | | | | IV-1 | Dazap2 |
| 14964 | 3 | 4 | | | | IV-1 | Dazl |
| 14965 | 3 | 4 | | | | IV-1 | Dbh |
| 14966 | 3 | 4 | | | | IV-1 | Dbhos |
| 14967 | 3 | 4 | | | | IV-1 | Dbpht2 |
| 14968 | 3 | 4 | | | | IV-1 | Dbt |
| 14969 | 3 | 4 | | | | IV-1 | Dbx1 |
| 14970 | 3 | 4 | | | | IV-1 | Dbx2 |
| 14971 | 3 | 4 | | | | IV-1 | Dcaf10 |
| 14972 | 3 | 4 | | | | IV-1 | Dcaf11 |
| 14973 | 3 | 4 | | | | IV-1 | Dcaf15 |
| 14974 | 3 | 4 | | | | IV-1 | Dcaf5 |
| 14975 | 3 | 4 | | | | IV-1 | Dcaf7 |
| 14976 | 3 | 4 | | | | IV-1 | Dcaf8 |
| 14977 | 3 | 4 | | | | IV-1 | Dcbld2 |
| 14978 | 3 | 4 | | | | IV-1 | Dcc |
| 14979 | 3 | 4 | | | | IV-1 | Dcdc2b |
| 14980 | 3 | 4 | | | | IV-1 | Dcdc2c |
| 14981 | 3 | 4 | | | | IV-1 | Dclk1 |
| 14982 | 3 | 4 | | | | IV-1 | Dclk3 |
| 14983 | 3 | 4 | | | | IV-1 | Dclre1b |
| 14984 | 3 | 4 | | | | IV-1 | Dclre1c |
| 14985 | 3 | 4 | | | | IV-1 | Dcp1b |
| 14986 | 3 | 4 | | | | IV-1 | Dcpp2 |
| 14987 | 3 | 4 | | | | IV-1 | Dcst1 |
| 14988 | 3 | 4 | | | | IV-1 | Dcstamp |
| 14989 | 3 | 4 | | | | IV-1 | Dctn1 |
| 14990 | 3 | 4 | | | | IV-1 | Dcun1d1 |
| 14991 | 3 | 4 | | | | IV-1 | Dcun1d3 |
| 14992 | 3 | 4 | | | | IV-1 | Dcun1d4 |
| 14993 | 3 | 4 | | | | IV-1 | Dcun1d5 |
| 14994 | 3 | 4 | | | | IV-1 | Dcx |
| 14995 | 3 | 4 | | | | IV-1 | Dda1 |
| 14996 | 3 | 4 | | | | IV-1 | Ddb1 |
| 14997 | 3 | 4 | | | | IV-1 | Ddhd1 |
| 14998 | 3 | 4 | | | | IV-1 | Ddhd2 |
| 14999 | 3 | 4 | | | | IV-1 | Ddr2 |
| 15000 | 3 | 4 | | | | IV-1 | Ddrgk1 |
| 15001 | 3 | 4 | | | | IV-1 | Ddx11 |
| 15002 | 3 | 4 | | | | IV-1 | Ddx19a |
| 15003 | 3 | 4 | | | | IV-1 | Ddx20 |
| 15004 | 3 | 4 | | | | IV-1 | Ddx23 |
| 15005 | 3 | 4 | | | | IV-1 | Ddx24 |
| 15006 | 3 | 4 | | | | IV-1 | Ddx25 |
| 15007 | 3 | 4 | | | | IV-1 | Ddx27 |
| 15008 | 3 | 4 | | | | IV-1 | Ddx3x |
| 15009 | 3 | 4 | | | | IV-1 | Ddx3y |
| 15010 | 3 | 4 | | | | IV-1 | Ddx4 |
| 15011 | 3 | 4 | | | | IV-1 | Ddx42 |
| 15012 | 3 | 4 | | | | IV-1 | Ddx43 |
| 15013 | 3 | 4 | | | | IV-1 | Ddx46 |
| 15014 | 3 | 4 | | | | IV-1 | Ddx47 |
| 15015 | 3 | 4 | | | | IV-1 | Ddx5 |
| 15016 | 3 | 4 | | | | IV-1 | Ddx50 |
| 15017 | 3 | 4 | | | | IV-1 | Ddx52 |
| 15018 | 3 | 4 | | | | IV-1 | Ddx56 |
| 15019 | 3 | 4 | | | | IV-1 | Ddx59 |
| 15020 | 3 | 4 | | | | IV-1 | Ddx6 |
| 15021 | 3 | 4 | | | | IV-1 | Dear1 |
| 15022 | 3 | 4 | | | | IV-1 | Decr1 |
| 15023 | 3 | 4 | | | | IV-1 | Dedd |
| 15024 | 3 | 4 | | | | IV-1 | Dedd2 |
| 15025 | 3 | 4 | | | | IV-1 | Def8 |
| 15026 | 3 | 4 | | | | IV-1 | Defa25 |
| 15027 | 3 | 4 | | | | IV-1 | Defa26 |
| 15028 | 3 | 4 | | | | IV-1 | Defa5 |
| 15029 | 3 | 4 | | | | IV-1 | Defa6 |
| 15030 | 3 | 4 | | | | IV-1 | Defa-ps13 |
| 15031 | 3 | 4 | | | | IV-1 | Defb21 |
| 15032 | 3 | 4 | | | | IV-1 | Defb29 |
| 15033 | 3 | 4 | | | | IV-1 | Defb36 |
| 15034 | 3 | 4 | | | | IV-1 | Defb45 |
| 15035 | 3 | 4 | | | | IV-1 | Defb48 |
| 15036 | 3 | 4 | | | | IV-1 | Dek |
| 15037 | 3 | 4 | | | | IV-1 | Dennd1b |
| 15038 | 3 | 4 | | | | IV-1 | Dennd3 |
| 15039 | 3 | 4 | | | | IV-1 | Dennd6a |
| 15040 | 3 | 4 | | | | IV-1 | Depdc1a |
| 15041 | 3 | 4 | | | | IV-1 | Depdc1b |
| 15042 | 3 | 4 | | | | IV-1 | Depdc5 |
| 15043 | 3 | 4 | | | | IV-1 | Derl1 |
| 15044 | 3 | 4 | | | | IV-1 | Derl2 |
| 15045 | 3 | 4 | | | | IV-1 | Dexi |
| 15046 | 3 | 4 | | | | IV-1 | Dffb |
| 15047 | 3 | 4 | | | | IV-1 | Dfnb59 |
| 15048 | 3 | 4 | | | | IV-1 | Dgat2l6 |
| 15049 | 3 | 4 | | | | IV-1 | Dgcr14 |
| 15050 | 3 | 4 | | | | IV-1 | Dgcr2 |
| 15051 | 3 | 4 | | | | IV-1 | Dgcr8 |
| 15052 | 3 | 4 | | | | IV-1 | Dgka |
| 15053 | 3 | 4 | | | | IV-1 | Dgkb |
| 15054 | 3 | 4 | | | | IV-1 | Dgki |
| 15055 | 3 | 4 | | | | IV-1 | Dgkk |
| 15056 | 3 | 4 | | | | IV-1 | Dgkz |
| 15057 | 3 | 4 | | | | IV-1 | Dhh |
| 15058 | 3 | 4 | | | | IV-1 | Dhps |
| 15059 | 3 | 4 | | | | IV-1 | Dhrs1 |
| 15060 | 3 | 4 | | | | IV-1 | Dhrs2 |
| 15061 | 3 | 4 | | | | IV-1 | Dhrs7 |
| 15062 | 3 | 4 | | | | IV-1 | Dhx15 |
| 15063 | 3 | 4 | | | | IV-1 | Dhx16 |
| 15064 | 3 | 4 | | | | IV-1 | Dhx29 |
| 15065 | 3 | 4 | | | | IV-1 | Dhx30 |
| 15066 | 3 | 4 | | | | IV-1 | Dhx32 |
| 15067 | 3 | 4 | | | | IV-1 | Dhx33 |
| 15068 | 3 | 4 | | | | IV-1 | Dhx35 |
| 15069 | 3 | 4 | | | | IV-1 | Dhx36 |
| 15070 | 3 | 4 | | | | IV-1 | Dhx38 |
| 15071 | 3 | 4 | | | | IV-1 | Dhx8 |
| 15072 | 3 | 4 | | | | IV-1 | Dhx9 |
| 15073 | 3 | 4 | | | | IV-1 | Diablo |
| 15074 | 3 | 4 | | | | IV-1 | Diap1 |
| 15075 | 3 | 4 | | | | IV-1 | Diap3 |
| 15076 | 3 | 4 | | | | IV-1 | Dicer1 |
| 15077 | 3 | 4 | | | | IV-1 | Dimt1 |
| 15078 | 3 | 4 | | | | IV-1 | Dio3 |
| 15079 | 3 | 4 | | | | IV-1 | Dip2b |
| 15080 | 3 | 4 | | | | IV-1 | Dip2c |
| 15081 | 3 | 4 | | | | IV-1 | Diras1 |
| 15082 | 3 | 4 | | | | IV-1 | Dis3l |
| 15083 | 3 | 4 | | | | IV-1 | Disc1 |
| 15084 | 3 | 4 | | | | IV-1 | Disp1 |
| 15085 | 3 | 4 | | | | IV-1 | Dkk1 |
| 15086 | 3 | 4 | | | | IV-1 | Dkk4 |
| 15087 | 3 | 4 | | | | IV-1 | Dleu7 |
| 15088 | 3 | 4 | | | | IV-1 | Dlg1 |
| 15089 | 3 | 4 | | | | IV-1 | Dlg3 |
| 15090 | 3 | 4 | | | | IV-1 | Dlgap1 |
| 15091 | 3 | 4 | | | | IV-1 | Dlgap2 |
| 15092 | 3 | 4 | | | | IV-1 | Dlgap3 |
| 15093 | 3 | 4 | | | | IV-1 | Dlgap5 |
| 15094 | 3 | 4 | | | | IV-1 | Dlk2 |
| 15095 | 3 | 4 | | | | IV-1 | Dll1 |
| 15096 | 3 | 4 | | | | IV-1 | Dlst |
| 15097 | 3 | 4 | | | | IV-1 | Dlx1 |
| 15098 | 3 | 4 | | | | IV-1 | Dlx1as |
| 15099 | 3 | 4 | | | | IV-1 | Dlx2 |
| 15100 | 3 | 4 | | | | IV-1 | Dlx3 |
| 15101 | 3 | 4 | | | | IV-1 | Dlx4 |
| 15102 | 3 | 4 | | | | IV-1 | Dlx5 |
| 15103 | 3 | 4 | | | | IV-1 | Dlx6 |
| 15104 | 3 | 4 | | | | IV-1 | Dlx6os1 |
| 15105 | 3 | 4 | | | | IV-1 | Dmbx1 |
| 15106 | 3 | 4 | | | | IV-1 | Dmc1 |
| 15107 | 3 | 4 | | | | IV-1 | Dmgdh |
| 15108 | 3 | 4 | | | | IV-1 | Dmp1 |
| 15109 | 3 | 4 | | | | IV-1 | Dmr |
| 15110 | 3 | 4 | | | | IV-1 | Dmrt1 |
| 15111 | 3 | 4 | | | | IV-1 | Dmrt3 |
| 15112 | 3 | 4 | | | | IV-1 | Dmrta2 |
| 15113 | 3 | 4 | | | | IV-1 | Dmrtc1a |
| 15114 | 3 | 4 | | | | IV-1 | Dmrtc1b |
| 15115 | 3 | 4 | | | | IV-1 | Dmrtc1c2 |
| 15116 | 3 | 4 | | | | IV-1 | Dmrtc2 |
| 15117 | 3 | 4 | | | | IV-1 | Dmwd |
| 15118 | 3 | 4 | | | | IV-1 | Dnah1 |
| 15119 | 3 | 4 | | | | IV-1 | Dnah11 |
| 15120 | 3 | 4 | | | | IV-1 | Dnah2 |
| 15121 | 3 | 4 | | | | IV-1 | Dnah5 |
| 15122 | 3 | 4 | | | | IV-1 | Dnah7a |
| 15123 | 3 | 4 | | | | IV-1 | Dnajb12 |
| 15124 | 3 | 4 | | | | IV-1 | Dnajb5 |
| 15125 | 3 | 4 | | | | IV-1 | Dnajb6 |
| 15126 | 3 | 4 | | | | IV-1 | Dnajb9 |
| 15127 | 3 | 4 | | | | IV-1 | Dnajc10 |

Fig. 43 - 90

| | | | | | | | |
|---|---|---|---|---|---|---|---|
| 15128 | 3 | 4 | | | | IV-1 | Dnajc11 |
| 15129 | 3 | 4 | | | | IV-1 | Dnajc14 |
| 15130 | 3 | 4 | | | | IV-1 | Dnajc17 |
| 15131 | 3 | 4 | | | | IV-1 | Dnajc18 |
| 15132 | 3 | 4 | | | | IV-1 | Dnajc2 |
| 15133 | 3 | 4 | | | | IV-1 | Dnajc3 |
| 15134 | 3 | 4 | | | | IV-1 | Dnase2b |
| 15135 | 3 | 4 | | | | IV-1 | Dner |
| 15136 | 3 | 4 | | | | IV-1 | Dnlz |
| 15137 | 3 | 4 | | | | IV-1 | Dnm1l |
| 15138 | 3 | 4 | | | | IV-1 | Dnm3 |
| 15139 | 3 | 4 | | | | IV-1 | Dnmt1 |
| 15140 | 3 | 4 | | | | IV-1 | Dnmt3aos |
| 15141 | 3 | 4 | | | | IV-1 | Dnmt3b |
| 15142 | 3 | 4 | | | | IV-1 | Dnmt3l |
| 15143 | 3 | 4 | | | | IV-1 | Dnttip2 |
| 15144 | 3 | 4 | | | | IV-1 | Doc2a |
| 15145 | 3 | 4 | | | | IV-1 | Dock10 |
| 15146 | 3 | 4 | | | | IV-1 | Dock11 |
| 15147 | 3 | 4 | | | | IV-1 | Dock2 |
| 15148 | 3 | 4 | | | | IV-1 | Dock3 |
| 15149 | 3 | 4 | | | | IV-1 | Dock6 |
| 15150 | 3 | 4 | | | | IV-1 | Dock7 |
| 15151 | 3 | 4 | | | | IV-1 | Dock9 |
| 15152 | 3 | 4 | | | | IV-1 | Dok4 |
| 15153 | 3 | 4 | | | | IV-1 | Dok5 |
| 15154 | 3 | 4 | | | | IV-1 | Dok6 |
| 15155 | 3 | 4 | | | | IV-1 | Dolk |
| 15156 | 3 | 4 | | | | IV-1 | Dolpp1 |
| 15157 | 3 | 4 | | | | IV-1 | Donson |
| 15158 | 3 | 4 | | | | IV-1 | Doxl2 |
| 15159 | 3 | 4 | | | | IV-1 | Dpagt1 |
| 15160 | 3 | 4 | | | | IV-1 | Dpcd |
| 15161 | 3 | 4 | | | | IV-1 | Dpf1 |
| 15162 | 3 | 4 | | | | IV-1 | Dpf2 |
| 15163 | 3 | 4 | | | | IV-1 | Dpf3 |
| 15164 | 3 | 4 | | | | IV-1 | Dph3 |
| 15165 | 3 | 4 | | | | IV-1 | Dph6 |
| 15166 | 3 | 4 | | | | IV-1 | Dph7 |
| 15167 | 3 | 4 | | | | IV-1 | Dpm1 |
| 15168 | 3 | 4 | | | | IV-1 | Dpm2 |
| 15169 | 3 | 4 | | | | IV-1 | Dpp10 |
| 15170 | 3 | 4 | | | | IV-1 | Dpp3 |
| 15171 | 3 | 4 | | | | IV-1 | Dpp6 |
| 15172 | 3 | 4 | | | | IV-1 | Dppa1 |
| 15173 | 3 | 4 | | | | IV-1 | Dppa2 |
| 15174 | 3 | 4 | | | | IV-1 | Dppa3 |
| 15175 | 3 | 4 | | | | IV-1 | Dppa4 |
| 15176 | 3 | 4 | | | | IV-1 | Dppa5a |
| 15177 | 3 | 4 | | | | IV-1 | Dpysl3 |
| 15178 | 3 | 4 | | | | IV-1 | Dpysl5 |
| 15179 | 3 | 4 | | | | IV-1 | DQ267100 |
| 15180 | 3 | 4 | | | | IV-1 | DQ267102 |
| 15181 | 3 | 4 | | | | IV-1 | Dr1 |
| 15182 | 3 | 4 | | | | IV-1 | Drc1 |
| 15183 | 3 | 4 | | | | IV-1 | Drd1a |
| 15184 | 3 | 4 | | | | IV-1 | Drd2 |
| 15185 | 3 | 4 | | | | IV-1 | Drd3 |
| 15186 | 3 | 4 | | | | IV-1 | Dreh |
| 15187 | 3 | 4 | | | | IV-1 | Drosha |
| 15188 | 3 | 4 | | | | IV-1 | Dsc1 |
| 15189 | 3 | 4 | | | | IV-1 | Dscam |
| 15190 | 3 | 4 | | | | IV-1 | Dscaml1 |
| 15191 | 3 | 4 | | | | IV-1 | Dscr3 |
| 15192 | 3 | 4 | | | | IV-1 | Dsg3 |
| 15193 | 3 | 4 | | | | IV-1 | Dsg4 |
| 15194 | 3 | 4 | | | | IV-1 | Dsn1 |
| 15195 | 3 | 4 | | | | IV-1 | Dspp |
| 15196 | 3 | 4 | | | | IV-1 | Dstn |
| 15197 | 3 | 4 | | | | IV-1 | Dtd2 |
| 15198 | 3 | 4 | | | | IV-1 | Dtx3 |
| 15199 | 3 | 4 | | | | IV-1 | Dtx4 |
| 15200 | 3 | 4 | | | | IV-1 | Duox1 |
| 15201 | 3 | 4 | | | | IV-1 | Duox2 |
| 15202 | 3 | 4 | | | | IV-1 | Duoxa2 |
| 15203 | 3 | 4 | | | | IV-1 | Dus1l |
| 15204 | 3 | 4 | | | | IV-1 | Dus3l |
| 15205 | 3 | 4 | | | | IV-1 | Dus4l |
| 15206 | 3 | 4 | | | | IV-1 | Dusp1 |
| 15207 | 3 | 4 | | | | IV-1 | Dusp13 |
| 15208 | 3 | 4 | | | | IV-1 | Dusp16 |
| 15209 | 3 | 4 | | | | IV-1 | Dusp21 |
| 15210 | 3 | 4 | | | | IV-1 | Dusp3 |
| 15211 | 3 | 4 | | | | IV-1 | Dusp7 |
| 15212 | 3 | 4 | | | | IV-1 | Dusp9 |
| 15213 | 3 | 4 | | | | IV-1 | Dux |
| 15214 | 3 | 4 | | | | IV-1 | Duxbl1 |
| 15215 | 3 | 4 | | | | IV-1 | Duxbl2 |
| 15216 | 3 | 4 | | | | IV-1 | Duxbl3 |
| 15217 | 3 | 4 | | | | IV-1 | Dvl2 |
| 15218 | 3 | 4 | | | | IV-1 | Dydc2 |
| 15219 | 3 | 4 | | | | IV-1 | Dym |
| 15220 | 3 | 4 | | | | IV-1 | Dynap |
| 15221 | 3 | 4 | | | | IV-1 | Dync1i1 |
| 15222 | 3 | 4 | | | | IV-1 | Dync1li1 |
| 15223 | 3 | 4 | | | | IV-1 | Dync1li2 |
| 15224 | 3 | 4 | | | | IV-1 | Dynlrb1 |
| 15225 | 3 | 4 | | | | IV-1 | Dynlt1b |
| 15226 | 3 | 4 | | | | IV-1 | Dynlt1c |
| 15227 | 3 | 4 | | | | IV-1 | Dynlt3 |
| 15228 | 3 | 4 | | | | IV-1 | Dyrk1a |
| 15229 | 3 | 4 | | | | IV-1 | Dyrk4 |
| 15230 | 3 | 4 | | | | IV-1 | Dytn |
| 15231 | 3 | 4 | | | | IV-1 | Dyx1c1 |
| 15232 | 3 | 4 | | | | IV-1 | Dzank1 |
| 15233 | 3 | 4 | | | | IV-1 | E030013I19Rik |
| 15234 | 3 | 4 | | | | IV-1 | E030019B06Rik |
| 15235 | 3 | 4 | | | | IV-1 | E030025P04Rik |
| 15236 | 3 | 4 | | | | IV-1 | E130006D01Rik |
| 15237 | 3 | 4 | | | | IV-1 | E130304I02Rik |
| 15238 | 3 | 4 | | | | IV-1 | E130307A14Rik |
| 15239 | 3 | 4 | | | | IV-1 | E130308A19Rik |
| 15240 | 3 | 4 | | | | IV-1 | E130309F12Rik |
| 15241 | 3 | 4 | | | | IV-1 | E230019M04Rik |
| 15242 | 3 | 4 | | | | IV-1 | E230025N22Rik |
| 15243 | 3 | 4 | | | | IV-1 | E2f3 |
| 15244 | 3 | 4 | | | | IV-1 | E330012B07Rik |
| 15245 | 3 | 4 | | | | IV-1 | E330013P04Rik |
| 15246 | 3 | 4 | | | | IV-1 | E330014E10Rik |
| 15247 | 3 | 4 | | | | IV-1 | E330017A01Rik |
| 15248 | 3 | 4 | | | | IV-1 | E330023G01Rik |
| 15249 | 3 | 4 | | | | IV-1 | E530011L22Rik |
| 15250 | 3 | 4 | | | | IV-1 | Eapp |
| 15251 | 3 | 4 | | | | IV-1 | Ear14 |
| 15252 | 3 | 4 | | | | IV-1 | Ear4 |
| 15253 | 3 | 4 | | | | IV-1 | Ebag9 |
| 15254 | 3 | 4 | | | | IV-1 | Ebf3 |
| 15255 | 3 | 4 | | | | IV-1 | Ebf4 |
| 15256 | 3 | 4 | | | | IV-1 | Ebna1bp2 |
| 15257 | 3 | 4 | | | | IV-1 | Ebp |
| 15258 | 3 | 4 | | | | IV-1 | Ebpl |
| 15259 | 3 | 4 | | | | IV-1 | Ecd |
| 15260 | 3 | 4 | | | | IV-1 | Ece1 |
| 15261 | 3 | 4 | | | | IV-1 | Ecel1 |
| 15262 | 3 | 4 | | | | IV-1 | Echdc2 |
| 15263 | 3 | 4 | | | | IV-1 | Echs1 |
| 15264 | 3 | 4 | | | | IV-1 | Eci3 |
| 15265 | 3 | 4 | | | | IV-1 | Ecm2 |
| 15266 | 3 | 4 | | | | IV-1 | Ecsit |
| 15267 | 3 | 4 | | | | IV-1 | Ect2l |
| 15268 | 3 | 4 | | | | IV-1 | Edem2 |
| 15269 | 3 | 4 | | | | IV-1 | Edn2 |
| 15270 | 3 | 4 | | | | IV-1 | Edn3 |
| 15271 | 3 | 4 | | | | IV-1 | Ednrb |
| 15272 | 3 | 4 | | | | IV-1 | Edrf1 |
| 15273 | 3 | 4 | | | | IV-1 | Eea1 |
| 15274 | 3 | 4 | | | | IV-1 | Eef1a1 |
| 15275 | 3 | 4 | | | | IV-1 | Eef1b2 |
| 15276 | 3 | 4 | | | | IV-1 | Eef1g |
| 15277 | 3 | 4 | | | | IV-1 | Eef2 |
| 15278 | 3 | 4 | | | | IV-1 | Eefsec |
| 15279 | 3 | 4 | | | | IV-1 | Efcab10 |
| 15280 | 3 | 4 | | | | IV-1 | Efcab14 |
| 15281 | 3 | 4 | | | | IV-1 | Efcab3 |
| 15282 | 3 | 4 | | | | IV-1 | Efcab5 |
| 15283 | 3 | 4 | | | | IV-1 | Efcab7 |
| 15284 | 3 | 4 | | | | IV-1 | Efhc2 |
| 15285 | 3 | 4 | | | | IV-1 | Efhd2 |
| 15286 | 3 | 4 | | | | IV-1 | Efna1 |
| 15287 | 3 | 4 | | | | IV-1 | Efna4 |
| 15288 | 3 | 4 | | | | IV-1 | Efna5 |
| 15289 | 3 | 4 | | | | IV-1 | Efnb1 |
| 15290 | 3 | 4 | | | | IV-1 | Efnb2 |
| 15291 | 3 | 4 | | | | IV-1 | Efr3a |
| 15292 | 3 | 4 | | | | IV-1 | Efr3b |
| 15293 | 3 | 4 | | | | IV-1 | Eftud1 |
| 15294 | 3 | 4 | | | | IV-1 | Eftud2 |
| 15295 | 3 | 4 | | | | IV-1 | Egfem1 |
| 15296 | 3 | 4 | | | | IV-1 | Egfl7 |
| 15297 | 3 | 4 | | | | IV-1 | Egfr |

Fig. 43 - 91

| | | | | | | | |
|---|---|---|---|---|---|---|---|
| 15298 | 3 | 4 | | | | IV-1 | Egr4 |
| 15299 | 3 | 4 | | | | IV-1 | Ehbp1 |
| 15300 | 3 | 4 | | | | IV-1 | Ehbp1l1 |
| 15301 | 3 | 4 | | | | IV-1 | Ehd1 |
| 15302 | 3 | 4 | | | | IV-1 | Ehd4 |
| 15303 | 3 | 4 | | | | IV-1 | Ehmt1 |
| 15304 | 3 | 4 | | | | IV-1 | Eid2b |
| 15305 | 3 | 4 | | | | IV-1 | Eif1 |
| 15306 | 3 | 4 | | | | IV-1 | Eif1a |
| 15307 | 3 | 4 | | | | IV-1 | Eif1ad |
| 15308 | 3 | 4 | | | | IV-1 | Eif1b |
| 15309 | 3 | 4 | | | | IV-1 | Eif2a |
| 15310 | 3 | 4 | | | | IV-1 | Eif2ak2 |
| 15311 | 3 | 4 | | | | IV-1 | Eif2b2 |
| 15312 | 3 | 4 | | | | IV-1 | Eif2b5 |
| 15313 | 3 | 4 | | | | IV-1 | Eif2s3x |
| 15314 | 3 | 4 | | | | IV-1 | Eif3a |
| 15315 | 3 | 4 | | | | IV-1 | Eif3b |
| 15316 | 3 | 4 | | | | IV-1 | Eif3c |
| 15317 | 3 | 4 | | | | IV-1 | Eif3f |
| 15318 | 3 | 4 | | | | IV-1 | Eif3i |
| 15319 | 3 | 4 | | | | IV-1 | Eif3k |
| 15320 | 3 | 4 | | | | IV-1 | Eif3l |
| 15321 | 3 | 4 | | | | IV-1 | Eif4e |
| 15322 | 3 | 4 | | | | IV-1 | Eif4e1b |
| 15323 | 3 | 4 | | | | IV-1 | Eif4e2 |
| 15324 | 3 | 4 | | | | IV-1 | Eif4g1 |
| 15325 | 3 | 4 | | | | IV-1 | Eif4g2 |
| 15326 | 3 | 4 | | | | IV-1 | Eif4g3 |
| 15327 | 3 | 4 | | | | IV-1 | Eif4h |
| 15328 | 3 | 4 | | | | IV-1 | Eif5 |
| 15329 | 3 | 4 | | | | IV-1 | Elac1 |
| 15330 | 3 | 4 | | | | IV-1 | Elac2 |
| 15331 | 3 | 4 | | | | IV-1 | Elavl2 |
| 15332 | 3 | 4 | | | | IV-1 | Elavl3 |
| 15333 | 3 | 4 | | | | IV-1 | Elavl4 |
| 15334 | 3 | 4 | | | | IV-1 | Elf1 |
| 15335 | 3 | 4 | | | | IV-1 | Elf2 |
| 15336 | 3 | 4 | | | | IV-1 | Elf5 |
| 15337 | 3 | 4 | | | | IV-1 | Elfn2 |
| 15338 | 3 | 4 | | | | IV-1 | Elmo2 |
| 15339 | 3 | 4 | | | | IV-1 | Elmo3 |
| 15340 | 3 | 4 | | | | IV-1 | Elof1 |
| 15341 | 3 | 4 | | | | IV-1 | Elovl1 |
| 15342 | 3 | 4 | | | | IV-1 | Elovl7 |
| 15343 | 3 | 4 | | | | IV-1 | Elp2 |
| 15344 | 3 | 4 | | | | IV-1 | Elp3 |
| 15345 | 3 | 4 | | | | IV-1 | Elp5 |
| 15346 | 3 | 4 | | | | IV-1 | Emb |
| 15347 | 3 | 4 | | | | IV-1 | Emc1 |
| 15348 | 3 | 4 | | | | IV-1 | Emc10 |
| 15349 | 3 | 4 | | | | IV-1 | Emc3 |
| 15350 | 3 | 4 | | | | IV-1 | Emc4 |
| 15351 | 3 | 4 | | | | IV-1 | Emc7 |
| 15352 | 3 | 4 | | | | IV-1 | Emel |
| 15353 | 3 | 4 | | | | IV-1 | Emilin3 |
| 15354 | 3 | 4 | | | | IV-1 | Eml3 |
| 15355 | 3 | 4 | | | | IV-1 | Eml4 |
| 15356 | 3 | 4 | | | | IV-1 | Eml5 |
| 15357 | 3 | 4 | | | | IV-1 | Eml6 |
| 15358 | 3 | 4 | | | | IV-1 | Emr4 |
| 15359 | 3 | 4 | | | | IV-1 | Emx1 |
| 15360 | 3 | 4 | | | | IV-1 | Emx2os |
| 15361 | 3 | 4 | | | | IV-1 | En1 |
| 15362 | 3 | 4 | | | | IV-1 | En2 |
| 15363 | 3 | 4 | | | | IV-1 | Enam |
| 15364 | 3 | 4 | | | | IV-1 | Endod1 |
| 15365 | 3 | 4 | | | | IV-1 | Endov |
| 15366 | 3 | 4 | | | | IV-1 | Engase |
| 15367 | 3 | 4 | | | | IV-1 | Eno1b |
| 15368 | 3 | 4 | | | | IV-1 | Eno2 |
| 15369 | 3 | 4 | | | | IV-1 | Eno4 |
| 15370 | 3 | 4 | | | | IV-1 | Enoph1 |
| 15371 | 3 | 4 | | | | IV-1 | Enox1 |
| 15372 | 3 | 4 | | | | IV-1 | Enox2 |
| 15373 | 3 | 4 | | | | IV-1 | Enpp6 |
| 15374 | 3 | 4 | | | | IV-1 | Enpp7 |
| 15375 | 3 | 4 | | | | IV-1 | Ensa |
| 15376 | 3 | 4 | | | | IV-1 | Enthd1 |
| 15377 | 3 | 4 | | | | IV-1 | Enthd2 |
| 15378 | 3 | 4 | | | | IV-1 | Entpd2 |
| 15379 | 3 | 4 | | | | IV-1 | Entpd4 |
| 15380 | 3 | 4 | | | | IV-1 | Entpd6 |
| 15381 | 3 | 4 | | | | IV-1 | Entpd7 |
| 15382 | 3 | 4 | | | | IV-1 | Entpd8 |
| 15383 | 3 | 4 | | | | IV-1 | Eny2 |
| 15384 | 3 | 4 | | | | IV-1 | Ep400 |
| 15385 | 3 | 4 | | | | IV-1 | Epas1 |
| 15386 | 3 | 4 | | | | IV-1 | Epb4.1l3 |
| 15387 | 3 | 4 | | | | IV-1 | Epb4.1l4a |
| 15388 | 3 | 4 | | | | IV-1 | Epb4.1l5 |
| 15389 | 3 | 4 | | | | IV-1 | Epc1 |
| 15390 | 3 | 4 | | | | IV-1 | Epc2 |
| 15391 | 3 | 4 | | | | IV-1 | Epha1 |
| 15392 | 3 | 4 | | | | IV-1 | Epha10 |
| 15393 | 3 | 4 | | | | IV-1 | Epha3 |
| 15394 | 3 | 4 | | | | IV-1 | Epha5 |
| 15395 | 3 | 4 | | | | IV-1 | Epha6 |
| 15396 | 3 | 4 | | | | IV-1 | Epha7 |
| 15397 | 3 | 4 | | | | IV-1 | Epha8 |
| 15398 | 3 | 4 | | | | IV-1 | Ephb1 |
| 15399 | 3 | 4 | | | | IV-1 | Ephb2 |
| 15400 | 3 | 4 | | | | IV-1 | Ephb4 |
| 15401 | 3 | 4 | | | | IV-1 | Ephx3 |
| 15402 | 3 | 4 | | | | IV-1 | Epn2 |
| 15403 | 3 | 4 | | | | IV-1 | Eps15 |
| 15404 | 3 | 4 | | | | IV-1 | Eps15l1 |
| 15405 | 3 | 4 | | | | IV-1 | Eps8 |
| 15406 | 3 | 4 | | | | IV-1 | Eps8l1 |
| 15407 | 3 | 4 | | | | IV-1 | Eps8l3 |
| 15408 | 3 | 4 | | | | IV-1 | Ept1 |
| 15409 | 3 | 4 | | | | IV-1 | Epyc |
| 15410 | 3 | 4 | | | | IV-1 | Eqtn |
| 15411 | 3 | 4 | | | | IV-1 | Eras |
| 15412 | 3 | 4 | | | | IV-1 | Erbb2ip |
| 15413 | 3 | 4 | | | | IV-1 | Erbb4 |
| 15414 | 3 | 4 | | | | IV-1 | Ercc1 |
| 15415 | 3 | 4 | | | | IV-1 | Ercc3 |
| 15416 | 3 | 4 | | | | IV-1 | Ercc4 |
| 15417 | 3 | 4 | | | | IV-1 | Ercc5 |
| 15418 | 3 | 4 | | | | IV-1 | Ercc6 |
| 15419 | 3 | 4 | | | | IV-1 | Ercc6l |
| 15420 | 3 | 4 | | | | IV-1 | Erf |
| 15421 | 3 | 4 | | | | IV-1 | Ergic1 |
| 15422 | 3 | 4 | | | | IV-1 | Ergic2 |
| 15423 | 3 | 4 | | | | IV-1 | Eri1 |
| 15424 | 3 | 4 | | | | IV-1 | Eri2 |
| 15425 | 3 | 4 | | | | IV-1 | Erich4 |
| 15426 | 3 | 4 | | | | IV-1 | Erich6 |
| 15427 | 3 | 4 | | | | IV-1 | Erlec1 |
| 15428 | 3 | 4 | | | | IV-1 | Erlin2 |
| 15429 | 3 | 4 | | | | IV-1 | Ern2 |
| 15430 | 3 | 4 | | | | IV-1 | Erp29 |
| 15431 | 3 | 4 | | | | IV-1 | Erp44 |
| 15432 | 3 | 4 | | | | IV-1 | Errfi1 |
| 15433 | 3 | 4 | | | | IV-1 | Erv3 |
| 15434 | 3 | 4 | | | | IV-1 | Esco1 |
| 15435 | 3 | 4 | | | | IV-1 | Esco2 |
| 15436 | 3 | 4 | | | | IV-1 | Esp1 |
| 15437 | 3 | 4 | | | | IV-1 | Esp15 |
| 15438 | 3 | 4 | | | | IV-1 | Esp16 |
| 15439 | 3 | 4 | | | | IV-1 | Esp18 |
| 15440 | 3 | 4 | | | | IV-1 | Esp23 |
| 15441 | 3 | 4 | | | | IV-1 | Esp24 |
| 15442 | 3 | 4 | | | | IV-1 | Esyt1 |
| 15443 | 3 | 4 | | | | IV-1 | Esyt2 |
| 15444 | 3 | 4 | | | | IV-1 | Esyt3 |
| 15445 | 3 | 4 | | | | IV-1 | Etaa1 |
| 15446 | 3 | 4 | | | | IV-1 | Etd |
| 15447 | 3 | 4 | | | | IV-1 | Etf1 |
| 15448 | 3 | 4 | | | | IV-1 | Etnk2 |
| 15449 | 3 | 4 | | | | IV-1 | Etv2 |
| 15450 | 3 | 4 | | | | IV-1 | Etv3 |
| 15451 | 3 | 4 | | | | IV-1 | Etv6 |
| 15452 | 3 | 4 | | | | IV-1 | EU599041 |
| 15453 | 3 | 4 | | | | IV-1 | Evi2a-evi2b |
| 15454 | 3 | 4 | | | | IV-1 | Evi5 |
| 15455 | 3 | 4 | | | | IV-1 | Evpl |
| 15456 | 3 | 4 | | | | IV-1 | Evx2 |
| 15457 | 3 | 4 | | | | IV-1 | Exd2 |
| 15458 | 3 | 4 | | | | IV-1 | Exo1 |
| 15459 | 3 | 4 | | | | IV-1 | Exoc3 |
| 15460 | 3 | 4 | | | | IV-1 | Exoc5 |
| 15461 | 3 | 4 | | | | IV-1 | Exoc6 |
| 15462 | 3 | 4 | | | | IV-1 | Exoc6b |
| 15463 | 3 | 4 | | | | IV-1 | Exoc7 |
| 15464 | 3 | 4 | | | | IV-1 | Exosc10 |
| 15465 | 3 | 4 | | | | IV-1 | Exosc2 |
| 15466 | 3 | 4 | | | | IV-1 | Eya2 |
| 15467 | 3 | 4 | | | | IV-1 | Eya3 |

Fig. 43 - 92

| | | | | | | | |
|---|---|---|---|---|---|---|---|
| 15468 | 3 | 4 | | | | IV-1 | F11r |
| 15469 | 3 | 4 | | | | IV-1 | F12 |
| 15470 | 3 | 4 | | | | IV-1 | F2 |
| 15471 | 3 | 4 | | | | IV-1 | F2r |
| 15472 | 3 | 4 | | | | IV-1 | F630042I09Rik |
| 15473 | 3 | 4 | | | | IV-1 | F630111L10Rik |
| 15474 | 3 | 4 | | | | IV-1 | F630206G17Rik |
| 15475 | 3 | 4 | | | | IV-1 | F7 |
| 15476 | 3 | 4 | | | | IV-1 | F730035M05Rik |
| 15477 | 3 | 4 | | | | IV-1 | F730043M19Rik |
| 15478 | 3 | 4 | | | | IV-1 | F830045P16Rik |
| 15479 | 3 | 4 | | | | IV-1 | F9 |
| 15480 | 3 | 4 | | | | IV-1 | F930015N05Rik |
| 15481 | 3 | 4 | | | | IV-1 | Fabp12 |
| 15482 | 3 | 4 | | | | IV-1 | Fads1 |
| 15483 | 3 | 4 | | | | IV-1 | Faf2 |
| 15484 | 3 | 4 | | | | IV-1 | Faim2 |
| 15485 | 3 | 4 | | | | IV-1 | Fam101a |
| 15486 | 3 | 4 | | | | IV-1 | Fam101b |
| 15487 | 3 | 4 | | | | IV-1 | Fam102b |
| 15488 | 3 | 4 | | | | IV-1 | Fam103a1 |
| 15489 | 3 | 4 | | | | IV-1 | Fam105a |
| 15490 | 3 | 4 | | | | IV-1 | Fam109b |
| 15491 | 3 | 4 | | | | IV-1 | Fam111a |
| 15492 | 3 | 4 | | | | IV-1 | Fam114a1 |
| 15493 | 3 | 4 | | | | IV-1 | Fam115c |
| 15494 | 3 | 4 | | | | IV-1 | Fam115e |
| 15495 | 3 | 4 | | | | IV-1 | Fam117b |
| 15496 | 3 | 4 | | | | IV-1 | Fam120a |
| 15497 | 3 | 4 | | | | IV-1 | Fam120b |
| 15498 | 3 | 4 | | | | IV-1 | Fam122a |
| 15499 | 3 | 4 | | | | IV-1 | Fam122c |
| 15500 | 3 | 4 | | | | IV-1 | Fam124a |
| 15501 | 3 | 4 | | | | IV-1 | Fam126a |
| 15502 | 3 | 4 | | | | IV-1 | Fam131b |
| 15503 | 3 | 4 | | | | IV-1 | Fam134c |
| 15504 | 3 | 4 | | | | IV-1 | Fam135a |
| 15505 | 3 | 4 | | | | IV-1 | Fam135b |
| 15506 | 3 | 4 | | | | IV-1 | Fam149a |
| 15507 | 3 | 4 | | | | IV-1 | Fam149b |
| 15508 | 3 | 4 | | | | IV-1 | Fam150a |
| 15509 | 3 | 4 | | | | IV-1 | Fam150b |
| 15510 | 3 | 4 | | | | IV-1 | Fam154a |
| 15511 | 3 | 4 | | | | IV-1 | Fam159a |
| 15512 | 3 | 4 | | | | IV-1 | Fam159b |
| 15513 | 3 | 4 | | | | IV-1 | Fam160a1 |
| 15514 | 3 | 4 | | | | IV-1 | Fam160a2 |
| 15515 | 3 | 4 | | | | IV-1 | Fam160b2 |
| 15516 | 3 | 4 | | | | IV-1 | Fam162a |
| 15517 | 3 | 4 | | | | IV-1 | Fam163a |
| 15518 | 3 | 4 | | | | IV-1 | Fam163b |
| 15519 | 3 | 4 | | | | IV-1 | Fam166a |
| 15520 | 3 | 4 | | | | IV-1 | Fam168b |
| 15521 | 3 | 4 | | | | IV-1 | Fam170a |
| 15522 | 3 | 4 | | | | IV-1 | Fam170b |
| 15523 | 3 | 4 | | | | IV-1 | Fam171a2 |
| 15524 | 3 | 4 | | | | IV-1 | Fam171b |
| 15525 | 3 | 4 | | | | IV-1 | Fam172a |
| 15526 | 3 | 4 | | | | IV-1 | Fam174a |
| 15527 | 3 | 4 | | | | IV-1 | Fam175b |
| 15528 | 3 | 4 | | | | IV-1 | Fam178b |
| 15529 | 3 | 4 | | | | IV-1 | Fam179b |
| 15530 | 3 | 4 | | | | IV-1 | Fam181a |
| 15531 | 3 | 4 | | | | IV-1 | Fam181b |
| 15532 | 3 | 4 | | | | IV-1 | Fam184b |
| 15533 | 3 | 4 | | | | IV-1 | Fam185a |
| 15534 | 3 | 4 | | | | IV-1 | Fam186b |
| 15535 | 3 | 4 | | | | IV-1 | Fam187a |
| 15536 | 3 | 4 | | | | IV-1 | Fam188a |
| 15537 | 3 | 4 | | | | IV-1 | Fam189a1 |
| 15538 | 3 | 4 | | | | IV-1 | Fam192a |
| 15539 | 3 | 4 | | | | IV-1 | Fam193a |
| 15540 | 3 | 4 | | | | IV-1 | Fam196a |
| 15541 | 3 | 4 | | | | IV-1 | Fam196b |
| 15542 | 3 | 4 | | | | IV-1 | Fam198a |
| 15543 | 3 | 4 | | | | IV-1 | Fam19a1 |
| 15544 | 3 | 4 | | | | IV-1 | Fam19a3 |
| 15545 | 3 | 4 | | | | IV-1 | Fam19a5 |
| 15546 | 3 | 4 | | | | IV-1 | Fam204a |
| 15547 | 3 | 4 | | | | IV-1 | Fam207a |
| 15548 | 3 | 4 | | | | IV-1 | Fam20b |
| 15549 | 3 | 4 | | | | IV-1 | Fam210b |
| 15550 | 3 | 4 | | | | IV-1 | Fam214b |
| 15551 | 3 | 4 | | | | IV-1 | Fam216b |
| 15552 | 3 | 4 | | | | IV-1 | Fam219b |
| 15553 | 3 | 4 | | | | IV-1 | Fam221a |
| 15554 | 3 | 4 | | | | IV-1 | Fam222b |
| 15555 | 3 | 4 | | | | IV-1 | Fam227a |
| 15556 | 3 | 4 | | | | IV-1 | Fam227b |
| 15557 | 3 | 4 | | | | IV-1 | Fam228a |
| 15558 | 3 | 4 | | | | IV-1 | Fam26d |
| 15559 | 3 | 4 | | | | IV-1 | Fam32a |
| 15560 | 3 | 4 | | | | IV-1 | Fam35a |
| 15561 | 3 | 4 | | | | IV-1 | Fam3c |
| 15562 | 3 | 4 | | | | IV-1 | Fam43b |
| 15563 | 3 | 4 | | | | IV-1 | Fam46d |
| 15564 | 3 | 4 | | | | IV-1 | Fam47c |
| 15565 | 3 | 4 | | | | IV-1 | Fam49a |
| 15566 | 3 | 4 | | | | IV-1 | Fam50a |
| 15567 | 3 | 4 | | | | IV-1 | Fam63a |
| 15568 | 3 | 4 | | | | IV-1 | Fam65c |
| 15569 | 3 | 4 | | | | IV-1 | Fam69c |
| 15570 | 3 | 4 | | | | IV-1 | Fam71a |
| 15571 | 3 | 4 | | | | IV-1 | Fam81a |
| 15572 | 3 | 4 | | | | IV-1 | Fam83c |
| 15573 | 3 | 4 | | | | IV-1 | Fam83d |
| 15574 | 3 | 4 | | | | IV-1 | Fam83h |
| 15575 | 3 | 4 | | | | IV-1 | Fam92b |
| 15576 | 3 | 4 | | | | IV-1 | Fam96a |
| 15577 | 3 | 4 | | | | IV-1 | Fam98a |
| 15578 | 3 | 4 | | | | IV-1 | Fanca |
| 15579 | 3 | 4 | | | | IV-1 | Fancb |
| 15580 | 3 | 4 | | | | IV-1 | Fancc |
| 15581 | 3 | 4 | | | | IV-1 | Fancd2 |
| 15582 | 3 | 4 | | | | IV-1 | Fancd2os |
| 15583 | 3 | 4 | | | | IV-1 | Fank1 |
| 15584 | 3 | 4 | | | | IV-1 | Fap |
| 15585 | 3 | 4 | | | | IV-1 | Far1 |
| 15586 | 3 | 4 | | | | IV-1 | Farsb |
| 15587 | 3 | 4 | | | | IV-1 | Fasl |
| 15588 | 3 | 4 | | | | IV-1 | Fastk |
| 15589 | 3 | 4 | | | | IV-1 | Fat3 |
| 15590 | 3 | 4 | | | | IV-1 | Fate1 |
| 15591 | 3 | 4 | | | | IV-1 | Faxc |
| 15592 | 3 | 4 | | | | IV-1 | Fbf1 |
| 15593 | 3 | 4 | | | | IV-1 | Fblim1 |
| 15594 | 3 | 4 | | | | IV-1 | Fbln2 |
| 15595 | 3 | 4 | | | | IV-1 | Fbln7 |
| 15596 | 3 | 4 | | | | IV-1 | Fbn1 |
| 15597 | 3 | 4 | | | | IV-1 | Fbn2 |
| 15598 | 3 | 4 | | | | IV-1 | Fbrs |
| 15599 | 3 | 4 | | | | IV-1 | Fbrsl1 |
| 15600 | 3 | 4 | | | | IV-1 | Fbxl13 |
| 15601 | 3 | 4 | | | | IV-1 | Fbxl14 |
| 15602 | 3 | 4 | | | | IV-1 | Fbxl17 |
| 15603 | 3 | 4 | | | | IV-1 | Fbxl19 |
| 15604 | 3 | 4 | | | | IV-1 | Fbxl3 |
| 15605 | 3 | 4 | | | | IV-1 | Fbxl4 |
| 15606 | 3 | 4 | | | | IV-1 | Fbxl5 |
| 15607 | 3 | 4 | | | | IV-1 | Fbxl7 |
| 15608 | 3 | 4 | | | | IV-1 | Fbxo11 |
| 15609 | 3 | 4 | | | | IV-1 | Fbxo15 |
| 15610 | 3 | 4 | | | | IV-1 | Fbxo16 |
| 15611 | 3 | 4 | | | | IV-1 | Fbxo18 |
| 15612 | 3 | 4 | | | | IV-1 | Fbxo2 |
| 15613 | 3 | 4 | | | | IV-1 | Fbxo25 |
| 15614 | 3 | 4 | | | | IV-1 | Fbxo28 |
| 15615 | 3 | 4 | | | | IV-1 | Fbxo3 |
| 15616 | 3 | 4 | | | | IV-1 | Fbxo33 |
| 15617 | 3 | 4 | | | | IV-1 | Fbxo34 |
| 15618 | 3 | 4 | | | | IV-1 | Fbxo38 |
| 15619 | 3 | 4 | | | | IV-1 | Fbxo39 |
| 15620 | 3 | 4 | | | | IV-1 | Fbxo41 |
| 15621 | 3 | 4 | | | | IV-1 | Fbxo42 |
| 15622 | 3 | 4 | | | | IV-1 | Fbxo43 |
| 15623 | 3 | 4 | | | | IV-1 | Fbxo44 |
| 15624 | 3 | 4 | | | | IV-1 | Fbxo45 |
| 15625 | 3 | 4 | | | | IV-1 | Fbxo46 |
| 15626 | 3 | 4 | | | | IV-1 | Fbxo47 |
| 15627 | 3 | 4 | | | | IV-1 | Fbxo48 |
| 15628 | 3 | 4 | | | | IV-1 | Fbxo6 |
| 15629 | 3 | 4 | | | | IV-1 | Fbxo7 |
| 15630 | 3 | 4 | | | | IV-1 | Fbxo8 |
| 15631 | 3 | 4 | | | | IV-1 | Fbxw11 |
| 15632 | 3 | 4 | | | | IV-1 | Fbxw14 |
| 15633 | 3 | 4 | | | | IV-1 | Fbxw15 |
| 15634 | 3 | 4 | | | | IV-1 | Fbxw16 |
| 15635 | 3 | 4 | | | | IV-1 | Fbxw22 |
| 15636 | 3 | 4 | | | | IV-1 | Fbxw28 |
| 15637 | 3 | 4 | | | | IV-1 | Fcer1a |

Fig. 43 - 93

| | | | | | | | |
|---|---|---|---|---|---|---|---|
| 15638 | 3 | 4 | | | | IV-1 | Fcgbp |
| 15639 | 3 | 4 | | | | IV-1 | Fcgr3 |
| 15640 | 3 | 4 | | | | IV-1 | Fcho1 |
| 15641 | 3 | 4 | | | | IV-1 | Fcho2 |
| 15642 | 3 | 4 | | | | IV-1 | Fcnb |
| 15643 | 3 | 4 | | | | IV-1 | Fcrl6 |
| 15644 | 3 | 4 | | | | IV-1 | Fcrlb |
| 15645 | 3 | 4 | | | | IV-1 | Fech |
| 15646 | 3 | 4 | | | | IV-1 | Fem1b |
| 15647 | 3 | 4 | | | | IV-1 | Fendrr |
| 15648 | 3 | 4 | | | | IV-1 | Fer1l4 |
| 15649 | 3 | 4 | | | | IV-1 | Fer1l5 |
| 15650 | 3 | 4 | | | | IV-1 | Ferd3l |
| 15651 | 3 | 4 | | | | IV-1 | Fermt2 |
| 15652 | 3 | 4 | | | | IV-1 | Fev |
| 15653 | 3 | 4 | | | | IV-1 | Fez1 |
| 15654 | 3 | 4 | | | | IV-1 | Fezf1 |
| 15655 | 3 | 4 | | | | IV-1 | Fezf2 |
| 15656 | 3 | 4 | | | | IV-1 | Fgf12 |
| 15657 | 3 | 4 | | | | IV-1 | Fgf14 |
| 15658 | 3 | 4 | | | | IV-1 | Fgf15 |
| 15659 | 3 | 4 | | | | IV-1 | Fgf17 |
| 15660 | 3 | 4 | | | | IV-1 | Fgf20 |
| 15661 | 3 | 4 | | | | IV-1 | Fgf4 |
| 15662 | 3 | 4 | | | | IV-1 | Fgf6 |
| 15663 | 3 | 4 | | | | IV-1 | Fgf8 |
| 15664 | 3 | 4 | | | | IV-1 | Fgf9 |
| 15665 | 3 | 4 | | | | IV-1 | Fgfr1op |
| 15666 | 3 | 4 | | | | IV-1 | Fgfr3 |
| 15667 | 3 | 4 | | | | IV-1 | Fh1 |
| 15668 | 3 | 4 | | | | IV-1 | Fhad1os1 |
| 15669 | 3 | 4 | | | | IV-1 | Fhod3 |
| 15670 | 3 | 4 | | | | IV-1 | Fibcd1 |
| 15671 | 3 | 4 | | | | IV-1 | Fig4 |
| 15672 | 3 | 4 | | | | IV-1 | Firre |
| 15673 | 3 | 4 | | | | IV-1 | Fiz1 |
| 15674 | 3 | 4 | | | | IV-1 | Fkbp14 |
| 15675 | 3 | 4 | | | | IV-1 | Fkbp15 |
| 15676 | 3 | 4 | | | | IV-1 | Fkbp1a |
| 15677 | 3 | 4 | | | | IV-1 | Fkbp8 |
| 15678 | 3 | 4 | | | | IV-1 | Fkbp9 |
| 15679 | 3 | 4 | | | | IV-1 | Fkrp |
| 15680 | 3 | 4 | | | | IV-1 | Flad1 |
| 15681 | 3 | 4 | | | | IV-1 | Flcn |
| 15682 | 3 | 4 | | | | IV-1 | Flg2 |
| 15683 | 3 | 4 | | | | IV-1 | Flii |
| 15684 | 3 | 4 | | | | IV-1 | Flot2 |
| 15685 | 3 | 4 | | | | IV-1 | Flrt1 |
| 15686 | 3 | 4 | | | | IV-1 | Flrt3 |
| 15687 | 3 | 4 | | | | IV-1 | Flt3 |
| 15688 | 3 | 4 | | | | IV-1 | Flt4 |
| 15689 | 3 | 4 | | | | IV-1 | Flywch1 |
| 15690 | 3 | 4 | | | | IV-1 | Fmn1 |
| 15691 | 3 | 4 | | | | IV-1 | Fmnl2 |
| 15692 | 3 | 4 | | | | IV-1 | Fmnl3 |
| 15693 | 3 | 4 | | | | IV-1 | Fmo6 |
| 15694 | 3 | 4 | | | | IV-1 | Fmo9 |
| 15695 | 3 | 4 | | | | IV-1 | Fmod |
| 15696 | 3 | 4 | | | | IV-1 | Fmr1 |
| 15697 | 3 | 4 | | | | IV-1 | Fmr1nb |
| 15698 | 3 | 4 | | | | IV-1 | Fn1 |
| 15699 | 3 | 4 | | | | IV-1 | Fnbp4 |
| 15700 | 3 | 4 | | | | IV-1 | Fnd3c2 |
| 15701 | 3 | 4 | | | | IV-1 | Fndc3a |
| 15702 | 3 | 4 | | | | IV-1 | Fndc3b |
| 15703 | 3 | 4 | | | | IV-1 | Fndc3c1 |
| 15704 | 3 | 4 | | | | IV-1 | Fndc8 |
| 15705 | 3 | 4 | | | | IV-1 | Folh1 |
| 15706 | 3 | 4 | | | | IV-1 | Fopnl |
| 15707 | 3 | 4 | | | | IV-1 | Foxa1 |
| 15708 | 3 | 4 | | | | IV-1 | Foxb1 |
| 15709 | 3 | 4 | | | | IV-1 | Foxd1 |
| 15710 | 3 | 4 | | | | IV-1 | Foxd4 |
| 15711 | 3 | 4 | | | | IV-1 | Foxe1 |
| 15712 | 3 | 4 | | | | IV-1 | Foxe3 |
| 15713 | 3 | 4 | | | | IV-1 | Foxf2 |
| 15714 | 3 | 4 | | | | IV-1 | Foxg1 |
| 15715 | 3 | 4 | | | | IV-1 | Foxh1 |
| 15716 | 3 | 4 | | | | IV-1 | Foxi1 |
| 15717 | 3 | 4 | | | | IV-1 | Foxi2 |
| 15718 | 3 | 4 | | | | IV-1 | Foxi3 |
| 15719 | 3 | 4 | | | | IV-1 | Foxj2 |
| 15720 | 3 | 4 | | | | IV-1 | Foxj3 |
| 15721 | 3 | 4 | | | | IV-1 | Foxl2 |
| 15722 | 3 | 4 | | | | IV-1 | Foxl2os |
| 15723 | 3 | 4 | | | | IV-1 | Foxn1 |
| 15724 | 3 | 4 | | | | IV-1 | Foxp3 |
| 15725 | 3 | 4 | | | | IV-1 | Foxr1 |
| 15726 | 3 | 4 | | | | IV-1 | Foxr2 |
| 15727 | 3 | 4 | | | | IV-1 | Foxred1 |
| 15728 | 3 | 4 | | | | IV-1 | Fpr3 |
| 15729 | 3 | 4 | | | | IV-1 | Fpr-rs3 |
| 15730 | 3 | 4 | | | | IV-1 | Fpr-rs4 |
| 15731 | 3 | 4 | | | | IV-1 | Fpr-rs6 |
| 15732 | 3 | 4 | | | | IV-1 | Fras1 |
| 15733 | 3 | 4 | | | | IV-1 | Frem3 |
| 15734 | 3 | 4 | | | | IV-1 | Frk |
| 15735 | 3 | 4 | | | | IV-1 | Frmd3 |
| 15736 | 3 | 4 | | | | IV-1 | Frmd4a |
| 15737 | 3 | 4 | | | | IV-1 | Frmd4b |
| 15738 | 3 | 4 | | | | IV-1 | Frmd7 |
| 15739 | 3 | 4 | | | | IV-1 | Frmd8 |
| 15740 | 3 | 4 | | | | IV-1 | Frmpd1 |
| 15741 | 3 | 4 | | | | IV-1 | Frmpd1os |
| 15742 | 3 | 4 | | | | IV-1 | Frmpd3 |
| 15743 | 3 | 4 | | | | IV-1 | Frmpd4 |
| 15744 | 3 | 4 | | | | IV-1 | Frrs1l |
| 15745 | 3 | 4 | | | | IV-1 | Fry |
| 15746 | 3 | 4 | | | | IV-1 | Fsbp |
| 15747 | 3 | 4 | | | | IV-1 | Fscb |
| 15748 | 3 | 4 | | | | IV-1 | Fscn3 |
| 15749 | 3 | 4 | | | | IV-1 | Fsd1 |
| 15750 | 3 | 4 | | | | IV-1 | Fshb |
| 15751 | 3 | 4 | | | | IV-1 | Fshr |
| 15752 | 3 | 4 | | | | IV-1 | Fstl5 |
| 15753 | 3 | 4 | | | | IV-1 | Fthl17 |
| 15754 | 3 | 4 | | | | IV-1 | Ftmt |
| 15755 | 3 | 4 | | | | IV-1 | Fto |
| 15756 | 3 | 4 | | | | IV-1 | Ftsj1 |
| 15757 | 3 | 4 | | | | IV-1 | Fubp3 |
| 15758 | 3 | 4 | | | | IV-1 | Fuca1 |
| 15759 | 3 | 4 | | | | IV-1 | Fundc1 |
| 15760 | 3 | 4 | | | | IV-1 | Fundc2 |
| 15761 | 3 | 4 | | | | IV-1 | Fut2 |
| 15762 | 3 | 4 | | | | IV-1 | Fut4-ps1 |
| 15763 | 3 | 4 | | | | IV-1 | Fut7 |
| 15764 | 3 | 4 | | | | IV-1 | Fut9 |
| 15765 | 3 | 4 | | | | IV-1 | Fyn |
| 15766 | 3 | 4 | | | | IV-1 | Fyttd1 |
| 15767 | 3 | 4 | | | | IV-1 | Fzd5 |
| 15768 | 3 | 4 | | | | IV-1 | Fzd8 |
| 15769 | 3 | 4 | | | | IV-1 | G3bp1 |
| 15770 | 3 | 4 | | | | IV-1 | G3bp2 |
| 15771 | 3 | 4 | | | | IV-1 | G530011O06Rik |
| 15772 | 3 | 4 | | | | IV-1 | G630055G22Rik |
| 15773 | 3 | 4 | | | | IV-1 | G630071F17Rik |
| 15774 | 3 | 4 | | | | IV-1 | G630093K05Rik |
| 15775 | 3 | 4 | | | | IV-1 | G6bos |
| 15776 | 3 | 4 | | | | IV-1 | G730013B05Rik |
| 15777 | 3 | 4 | | | | IV-1 | Gabarap |
| 15778 | 3 | 4 | | | | IV-1 | Gabbr2 |
| 15779 | 3 | 4 | | | | IV-1 | Gabpa |
| 15780 | 3 | 4 | | | | IV-1 | Gabpb1 |
| 15781 | 3 | 4 | | | | IV-1 | Gabra1 |
| 15782 | 3 | 4 | | | | IV-1 | Gabra2 |
| 15783 | 3 | 4 | | | | IV-1 | Gabra3 |
| 15784 | 3 | 4 | | | | IV-1 | Gabra4 |
| 15785 | 3 | 4 | | | | IV-1 | Gabra5 |
| 15786 | 3 | 4 | | | | IV-1 | Gabra6 |
| 15787 | 3 | 4 | | | | IV-1 | Gabrb1 |
| 15788 | 3 | 4 | | | | IV-1 | Gabrb2 |
| 15789 | 3 | 4 | | | | IV-1 | Gabrb3 |
| 15790 | 3 | 4 | | | | IV-1 | Gabrd |
| 15791 | 3 | 4 | | | | IV-1 | Gabrg2 |
| 15792 | 3 | 4 | | | | IV-1 | Gabrg3 |
| 15793 | 3 | 4 | | | | IV-1 | Gabrp |
| 15794 | 3 | 4 | | | | IV-1 | Gabrq |
| 15795 | 3 | 4 | | | | IV-1 | Gabrr1 |
| 15796 | 3 | 4 | | | | IV-1 | Gabrr3 |
| 15797 | 3 | 4 | | | | IV-1 | Gad1os |
| 15798 | 3 | 4 | | | | IV-1 | Gak |
| 15799 | 3 | 4 | | | | IV-1 | Gal3st2 |
| 15800 | 3 | 4 | | | | IV-1 | Gal3st4 |
| 15801 | 3 | 4 | | | | IV-1 | Galc |
| 15802 | 3 | 4 | | | | IV-1 | Galk1 |
| 15803 | 3 | 4 | | | | IV-1 | Galnt1 |
| 15804 | 3 | 4 | | | | IV-1 | Galnt13 |
| 15805 | 3 | 4 | | | | IV-1 | Galnt14 |
| 15806 | 3 | 4 | | | | IV-1 | Galnt2 |
| 15807 | 3 | 4 | | | | IV-1 | Galnt5 |

Fig. 43 - 94

| | | | | | | | |
|---|---|---|---|---|---|---|---|
| 15808 | 3 | 4 | | | | IV-1 | Galnt7 |
| 15809 | 3 | 4 | | | | IV-1 | Galntl6 |
| 15810 | 3 | 4 | | | | IV-1 | Galp |
| 15811 | 3 | 4 | | | | IV-1 | Galr1 |
| 15812 | 3 | 4 | | | | IV-1 | Galr2 |
| 15813 | 3 | 4 | | | | IV-1 | Gap43 |
| 15814 | 3 | 4 | | | | IV-1 | Gareml |
| 15815 | 3 | 4 | | | | IV-1 | Gas2l2 |
| 15816 | 3 | 4 | | | | IV-1 | Gas5 |
| 15817 | 3 | 4 | | | | IV-1 | Gata2 |
| 15818 | 3 | 4 | | | | IV-1 | Gata4 |
| 15819 | 3 | 4 | | | | IV-1 | Gata5 |
| 15820 | 3 | 4 | | | | IV-1 | Gata6 |
| 15821 | 3 | 4 | | | | IV-1 | Gatad2a |
| 15822 | 3 | 4 | | | | IV-1 | Gba |
| 15823 | 3 | 4 | | | | IV-1 | Gbas |
| 15824 | 3 | 4 | | | | IV-1 | Gbf1 |
| 15825 | 3 | 4 | | | | IV-1 | Gbp2b |
| 15826 | 3 | 4 | | | | IV-1 | Gbx1 |
| 15827 | 3 | 4 | | | | IV-1 | Gbx2 |
| 15828 | 3 | 4 | | | | IV-1 | Gca |
| 15829 | 3 | 4 | | | | IV-1 | Gcc1 |
| 15830 | 3 | 4 | | | | IV-1 | Gcdh |
| 15831 | 3 | 4 | | | | IV-1 | Gckr |
| 15832 | 3 | 4 | | | | IV-1 | Gcm1 |
| 15833 | 3 | 4 | | | | IV-1 | Gcm2 |
| 15834 | 3 | 4 | | | | IV-1 | Gcn1l1 |
| 15835 | 3 | 4 | | | | IV-1 | Gcnt3 |
| 15836 | 3 | 4 | | | | IV-1 | Gcsam |
| 15837 | 3 | 4 | | | | IV-1 | Gdap2 |
| 15838 | 3 | 4 | | | | IV-1 | Gdf1 |
| 15839 | 3 | 4 | | | | IV-1 | Gdf2 |
| 15840 | 3 | 4 | | | | IV-1 | Gdf6 |
| 15841 | 3 | 4 | | | | IV-1 | Gdf7 |
| 15842 | 3 | 4 | | | | IV-1 | Gdi2 |
| 15843 | 3 | 4 | | | | IV-1 | Gdnf |
| 15844 | 3 | 4 | | | | IV-1 | Gdpd1 |
| 15845 | 3 | 4 | | | | IV-1 | Gdpd4 |
| 15846 | 3 | 4 | | | | IV-1 | Gemin4 |
| 15847 | 3 | 4 | | | | IV-1 | Gemin7 |
| 15848 | 3 | 4 | | | | IV-1 | Gen1 |
| 15849 | 3 | 4 | | | | IV-1 | Get4 |
| 15850 | 3 | 4 | | | | IV-1 | Gfm2 |
| 15851 | 3 | 4 | | | | IV-1 | Gfod1 |
| 15852 | 3 | 4 | | | | IV-1 | Gfra3 |
| 15853 | 3 | 4 | | | | IV-1 | Gfral |
| 15854 | 3 | 4 | | | | IV-1 | Gfy |
| 15855 | 3 | 4 | | | | IV-1 | Gga1 |
| 15856 | 3 | 4 | | | | IV-1 | Gga2 |
| 15857 | 3 | 4 | | | | IV-1 | Ggnbp2 |
| 15858 | 3 | 4 | | | | IV-1 | Ggt7 |
| 15859 | 3 | 4 | | | | IV-1 | Ghrh |
| 15860 | 3 | 4 | | | | IV-1 | Ghrhr |
| 15861 | 3 | 4 | | | | IV-1 | Ghsr |
| 15862 | 3 | 4 | | | | IV-1 | Gid4 |
| 15863 | 3 | 4 | | | | IV-1 | Gid8 |
| 15864 | 3 | 4 | | | | IV-1 | Gigyf2 |
| 15865 | 3 | 4 | | | | IV-1 | Ginm1 |
| 15866 | 3 | 4 | | | | IV-1 | Gins3 |
| 15867 | 3 | 4 | | | | IV-1 | Gipc1 |
| 15868 | 3 | 4 | | | | IV-1 | Gipr |
| 15869 | 3 | 4 | | | | IV-1 | Git1 |
| 15870 | 3 | 4 | | | | IV-1 | Git2 |
| 15871 | 3 | 4 | | | | IV-1 | Gja10 |
| 15872 | 3 | 4 | | | | IV-1 | Gja8 |
| 15873 | 3 | 4 | | | | IV-1 | Gjb4 |
| 15874 | 3 | 4 | | | | IV-1 | Gjc2 |
| 15875 | 3 | 4 | | | | IV-1 | Gjc3 |
| 15876 | 3 | 4 | | | | IV-1 | Gjd2 |
| 15877 | 3 | 4 | | | | IV-1 | Gjd4 |
| 15878 | 3 | 4 | | | | IV-1 | Gje1 |
| 15879 | 3 | 4 | | | | IV-1 | Gk5 |
| 15880 | 3 | 4 | | | | IV-1 | Glb1l |
| 15881 | 3 | 4 | | | | IV-1 | Glb1l3 |
| 15882 | 3 | 4 | | | | IV-1 | Gldn |
| 15883 | 3 | 4 | | | | IV-1 | Gldnos |
| 15884 | 3 | 4 | | | | IV-1 | Gli1 |
| 15885 | 3 | 4 | | | | IV-1 | Glipr1l1 |
| 15886 | 3 | 4 | | | | IV-1 | Glipr1l2 |
| 15887 | 3 | 4 | | | | IV-1 | Glis1 |
| 15888 | 3 | 4 | | | | IV-1 | Glod5 |
| 15889 | 3 | 4 | | | | IV-1 | Glp2r |
| 15890 | 3 | 4 | | | | IV-1 | Glra1 |
| 15891 | 3 | 4 | | | | IV-1 | Glra2 |
| 15892 | 3 | 4 | | | | IV-1 | Glra3 |
| 15893 | 3 | 4 | | | | IV-1 | Glra4 |
| 15894 | 3 | 4 | | | | IV-1 | Glrp1 |
| 15895 | 3 | 4 | | | | IV-1 | Gls |
| 15896 | 3 | 4 | | | | IV-1 | Glt25d1 |
| 15897 | 3 | 4 | | | | IV-1 | Glt28d2 |
| 15898 | 3 | 4 | | | | IV-1 | Glt6d1 |
| 15899 | 3 | 4 | | | | IV-1 | Glt8d1 |
| 15900 | 3 | 4 | | | | IV-1 | Gltp |
| 15901 | 3 | 4 | | | | IV-1 | Gltpd1 |
| 15902 | 3 | 4 | | | | IV-1 | Gltpd2 |
| 15903 | 3 | 4 | | | | IV-1 | Gltscr2 |
| 15904 | 3 | 4 | | | | IV-1 | Glud1 |
| 15905 | 3 | 4 | | | | IV-1 | Glul |
| 15906 | 3 | 4 | | | | IV-1 | Glvatl3 |
| 15907 | 3 | 4 | | | | IV-1 | Glyctk |
| 15908 | 3 | 4 | | | | IV-1 | Glyr1 |
| 15909 | 3 | 4 | | | | IV-1 | Gm10007 |
| 15910 | 3 | 4 | | | | IV-1 | Gm10046 |
| 15911 | 3 | 4 | | | | IV-1 | Gm10052 |
| 15912 | 3 | 4 | | | | IV-1 | Gm10081 |
| 15913 | 3 | 4 | | | | IV-1 | Gm10100 |
| 15914 | 3 | 4 | | | | IV-1 | Gm10104 |
| 15915 | 3 | 4 | | | | IV-1 | Gm10142 |
| 15916 | 3 | 4 | | | | IV-1 | Gm10147 |
| 15917 | 3 | 4 | | | | IV-1 | Gm10190 |
| 15918 | 3 | 4 | | | | IV-1 | Gm10229 |
| 15919 | 3 | 4 | | | | IV-1 | Gm10267 |
| 15920 | 3 | 4 | | | | IV-1 | Gm10280 |
| 15921 | 3 | 4 | | | | IV-1 | Gm10318 |
| 15922 | 3 | 4 | | | | IV-1 | Gm10377 |
| 15923 | 3 | 4 | | | | IV-1 | Gm10389 |
| 15924 | 3 | 4 | | | | IV-1 | Gm10421 |
| 15925 | 3 | 4 | | | | IV-1 | Gm10433 |
| 15926 | 3 | 4 | | | | IV-1 | Gm10436 |
| 15927 | 3 | 4 | | | | IV-1 | Gm10440 |
| 15928 | 3 | 4 | | | | IV-1 | Gm10445 |
| 15929 | 3 | 4 | | | | IV-1 | Gm10451 |
| 15930 | 3 | 4 | | | | IV-1 | Gm10488 |
| 15931 | 3 | 4 | | | | IV-1 | Gm10538 |
| 15932 | 3 | 4 | | | | IV-1 | Gm10556 |
| 15933 | 3 | 4 | | | | IV-1 | Gm10584 |
| 15934 | 3 | 4 | | | | IV-1 | Gm10636 |
| 15935 | 3 | 4 | | | | IV-1 | Gm10640 |
| 15936 | 3 | 4 | | | | IV-1 | Gm10649 |
| 15937 | 3 | 4 | | | | IV-1 | Gm10662 |
| 15938 | 3 | 4 | | | | IV-1 | Gm10665 |
| 15939 | 3 | 4 | | | | IV-1 | Gm10677 |
| 15940 | 3 | 4 | | | | IV-1 | Gm10789 |
| 15941 | 3 | 4 | | | | IV-1 | Gm10790 |
| 15942 | 3 | 4 | | | | IV-1 | Gm10791 |
| 15943 | 3 | 4 | | | | IV-1 | Gm10814 |
| 15944 | 3 | 4 | | | | IV-1 | Gm11128 |
| 15945 | 3 | 4 | | | | IV-1 | Gm11166 |
| 15946 | 3 | 4 | | | | IV-1 | Gm11186 |
| 15947 | 3 | 4 | | | | IV-1 | Gm11201 |
| 15948 | 3 | 4 | | | | IV-1 | Gm1141 |
| 15949 | 3 | 4 | | | | IV-1 | Gm11426 |
| 15950 | 3 | 4 | | | | IV-1 | Gm11541 |
| 15951 | 3 | 4 | | | | IV-1 | Gm11548 |
| 15952 | 3 | 4 | | | | IV-1 | Gm11562 |
| 15953 | 3 | 4 | | | | IV-1 | Gm11563 |
| 15954 | 3 | 4 | | | | IV-1 | Gm11565 |
| 15955 | 3 | 4 | | | | IV-1 | Gm11744 |
| 15956 | 3 | 4 | | | | IV-1 | Gm11757 |
| 15957 | 3 | 4 | | | | IV-1 | Gm11762 |
| 15958 | 3 | 4 | | | | IV-1 | Gm11961 |
| 15959 | 3 | 4 | | | | IV-1 | Gm11978 |
| 15960 | 3 | 4 | | | | IV-1 | Gm11981 |
| 15961 | 3 | 4 | | | | IV-1 | Gm12169 |
| 15962 | 3 | 4 | | | | IV-1 | Gm12295 |
| 15963 | 3 | 4 | | | | IV-1 | Gm12298 |
| 15964 | 3 | 4 | | | | IV-1 | Gm12409 |
| 15965 | 3 | 4 | | | | IV-1 | Gm12530 |
| 15966 | 3 | 4 | | | | IV-1 | Gm12603 |
| 15967 | 3 | 4 | | | | IV-1 | Gm12633 |
| 15968 | 3 | 4 | | | | IV-1 | Gm12657 |
| 15969 | 3 | 4 | | | | IV-1 | Gm12669 |
| 15970 | 3 | 4 | | | | IV-1 | Gm12794 |
| 15971 | 3 | 4 | | | | IV-1 | Gm12886 |
| 15972 | 3 | 4 | | | | IV-1 | Gm13031 |
| 15973 | 3 | 4 | | | | IV-1 | Gm13032 |
| 15974 | 3 | 4 | | | | IV-1 | Gm13040 |
| 15975 | 3 | 4 | | | | IV-1 | Gm13043 |
| 15976 | 3 | 4 | | | | IV-1 | Gm13083 |
| 15977 | 3 | 4 | | | | IV-1 | Gm13157 |

Fig. 43 - 95

| | | | | | | | |
|---|---|---|---|---|---|---|---|
| 15978 | 3 | 4 | | | | IV-1 | Gm1322 |
| 15979 | 3 | 4 | | | | IV-1 | Gm13242 |
| 15980 | 3 | 4 | | | | IV-1 | Gm13271 |
| 15981 | 3 | 4 | | | | IV-1 | Gm13275 |
| 15982 | 3 | 4 | | | | IV-1 | Gm13277 |
| 15983 | 3 | 4 | | | | IV-1 | Gm13278 |
| 15984 | 3 | 4 | | | | IV-1 | Gm13315 |
| 15985 | 3 | 4 | | | | IV-1 | Gm13446 |
| 15986 | 3 | 4 | | | | IV-1 | Gm13483 |
| 15987 | 3 | 4 | | | | IV-1 | Gm13490 |
| 15988 | 3 | 4 | | | | IV-1 | Gm13497 |
| 15989 | 3 | 4 | | | | IV-1 | Gm13498 |
| 15990 | 3 | 4 | | | | IV-1 | Gm13539 |
| 15991 | 3 | 4 | | | | IV-1 | Gm13544 |
| 15992 | 3 | 4 | | | | IV-1 | Gm13582 |
| 15993 | 3 | 4 | | | | IV-1 | Gm13871 |
| 15994 | 3 | 4 | | | | IV-1 | Gm14015 |
| 15995 | 3 | 4 | | | | IV-1 | Gm14057 |
| 15996 | 3 | 4 | | | | IV-1 | Gm14092 |
| 15997 | 3 | 4 | | | | IV-1 | Gm14124 |
| 15998 | 3 | 4 | | | | IV-1 | Gm14139 |
| 15999 | 3 | 4 | | | | IV-1 | Gm14151 |
| 16000 | 3 | 4 | | | | IV-1 | Gm14164 |
| 16001 | 3 | 4 | | | | IV-1 | Gm14322 |
| 16002 | 3 | 4 | | | | IV-1 | Gm14347 |
| 16003 | 3 | 4 | | | | IV-1 | Gm14351 |
| 16004 | 3 | 4 | | | | IV-1 | Gm14374 |
| 16005 | 3 | 4 | | | | IV-1 | Gm14403 |
| 16006 | 3 | 4 | | | | IV-1 | Gm14458 |
| 16007 | 3 | 4 | | | | IV-1 | Gm14459 |
| 16008 | 3 | 4 | | | | IV-1 | Gm14461 |
| 16009 | 3 | 4 | | | | IV-1 | Gm14474 |
| 16010 | 3 | 4 | | | | IV-1 | Gm14475 |
| 16011 | 3 | 4 | | | | IV-1 | Gm14476 |
| 16012 | 3 | 4 | | | | IV-1 | Gm14477 |
| 16013 | 3 | 4 | | | | IV-1 | Gm14496 |
| 16014 | 3 | 4 | | | | IV-1 | Gm14501 |
| 16015 | 3 | 4 | | | | IV-1 | Gm14511 |
| 16016 | 3 | 4 | | | | IV-1 | Gm14525 |
| 16017 | 3 | 4 | | | | IV-1 | Gm14632 |
| 16018 | 3 | 4 | | | | IV-1 | Gm14692 |
| 16019 | 3 | 4 | | | | IV-1 | Gm14743 |
| 16020 | 3 | 4 | | | | IV-1 | Gm14781 |
| 16021 | 3 | 4 | | | | IV-1 | Gm15056 |
| 16022 | 3 | 4 | | | | IV-1 | Gm15127 |
| 16023 | 3 | 4 | | | | IV-1 | Gm15217 |
| 16024 | 3 | 4 | | | | IV-1 | Gm15292 |
| 16025 | 3 | 4 | | | | IV-1 | Gm15293 |
| 16026 | 3 | 4 | | | | IV-1 | Gm15299 |
| 16027 | 3 | 4 | | | | IV-1 | Gm15319 |
| 16028 | 3 | 4 | | | | IV-1 | Gm15386 |
| 16029 | 3 | 4 | | | | IV-1 | Gm15412 |
| 16030 | 3 | 4 | | | | IV-1 | Gm15413 |
| 16031 | 3 | 4 | | | | IV-1 | Gm1553 |
| 16032 | 3 | 4 | | | | IV-1 | Gm15545 |
| 16033 | 3 | 4 | | | | IV-1 | Gm156 |
| 16034 | 3 | 4 | | | | IV-1 | Gm15612 |
| 16035 | 3 | 4 | | | | IV-1 | Gm1564 |
| 16036 | 3 | 4 | | | | IV-1 | Gm15645 |
| 16037 | 3 | 4 | | | | IV-1 | Gm15679 |
| 16038 | 3 | 4 | | | | IV-1 | Gm15713 |
| 16039 | 3 | 4 | | | | IV-1 | Gm15816 |
| 16040 | 3 | 4 | | | | IV-1 | Gm1587 |
| 16041 | 3 | 4 | | | | IV-1 | Gm15880 |
| 16042 | 3 | 4 | | | | IV-1 | Gm15881 |
| 16043 | 3 | 4 | | | | IV-1 | Gm15910 |
| 16044 | 3 | 4 | | | | IV-1 | Gm15997 |
| 16045 | 3 | 4 | | | | IV-1 | Gm16063 |
| 16046 | 3 | 4 | | | | IV-1 | Gm16287 |
| 16047 | 3 | 4 | | | | IV-1 | Gm16291 |
| 16048 | 3 | 4 | | | | IV-1 | Gm16294 |
| 16049 | 3 | 4 | | | | IV-1 | Gm16336 |
| 16050 | 3 | 4 | | | | IV-1 | Gm16432 |
| 16051 | 3 | 4 | | | | IV-1 | Gm16445 |
| 16052 | 3 | 4 | | | | IV-1 | Gm1647 |
| 16053 | 3 | 4 | | | | IV-1 | Gm1661 |
| 16054 | 3 | 4 | | | | IV-1 | Gm16677 |
| 16055 | 3 | 4 | | | | IV-1 | Gm16701 |
| 16056 | 3 | 4 | | | | IV-1 | Gm16702 |
| 16057 | 3 | 4 | | | | IV-1 | Gm16712 |
| 16058 | 3 | 4 | | | | IV-1 | Gm16853 |
| 16059 | 3 | 4 | | | | IV-1 | Gm16863 |
| 16060 | 3 | 4 | | | | IV-1 | Gm16938 |
| 16061 | 3 | 4 | | | | IV-1 | Gm16998 |
| 16062 | 3 | 4 | | | | IV-1 | Gm17019 |
| 16063 | 3 | 4 | | | | IV-1 | Gm1715 |
| 16064 | 3 | 4 | | | | IV-1 | Gm1720 |
| 16065 | 3 | 4 | | | | IV-1 | Gm17359 |
| 16066 | 3 | 4 | | | | IV-1 | Gm17365 |
| 16067 | 3 | 4 | | | | IV-1 | Gm17677 |
| 16068 | 3 | 4 | | | | IV-1 | Gm17801 |
| 16069 | 3 | 4 | | | | IV-1 | Gm1821 |
| 16070 | 3 | 4 | | | | IV-1 | Gm19303 |
| 16071 | 3 | 4 | | | | IV-1 | Gm19395 |
| 16072 | 3 | 4 | | | | IV-1 | Gm19424 |
| 16073 | 3 | 4 | | | | IV-1 | Gm19461 |
| 16074 | 3 | 4 | | | | IV-1 | Gm19589 |
| 16075 | 3 | 4 | | | | IV-1 | Gm1965 |
| 16076 | 3 | 4 | | | | IV-1 | Gm19668 |
| 16077 | 3 | 4 | | | | IV-1 | Gm19757 |
| 16078 | 3 | 4 | | | | IV-1 | Gm1979 |
| 16079 | 3 | 4 | | | | IV-1 | Gm1993 |
| 16080 | 3 | 4 | | | | IV-1 | Gm2011 |
| 16081 | 3 | 4 | | | | IV-1 | Gm20110 |
| 16082 | 3 | 4 | | | | IV-1 | Gm2012 |
| 16083 | 3 | 4 | | | | IV-1 | Gm20125 |
| 16084 | 3 | 4 | | | | IV-1 | Gm20172 |
| 16085 | 3 | 4 | | | | IV-1 | Gm20199 |
| 16086 | 3 | 4 | | | | IV-1 | Gm20356 |
| 16087 | 3 | 4 | | | | IV-1 | Gm2042 |
| 16088 | 3 | 4 | | | | IV-1 | Gm20556 |
| 16089 | 3 | 4 | | | | IV-1 | Gm20594 |
| 16090 | 3 | 4 | | | | IV-1 | Gm2061 |
| 16091 | 3 | 4 | | | | IV-1 | Gm20735 |
| 16092 | 3 | 4 | | | | IV-1 | Gm20738 |
| 16093 | 3 | 4 | | | | IV-1 | Gm20740 |
| 16094 | 3 | 4 | | | | IV-1 | Gm20741 |
| 16095 | 3 | 4 | | | | IV-1 | Gm20751 |
| 16096 | 3 | 4 | | | | IV-1 | Gm20754 |
| 16097 | 3 | 4 | | | | IV-1 | Gm20755 |
| 16098 | 3 | 4 | | | | IV-1 | Gm20757 |
| 16099 | 3 | 4 | | | | IV-1 | Gm20759 |
| 16100 | 3 | 4 | | | | IV-1 | Gm20765 |
| 16101 | 3 | 4 | | | | IV-1 | Gm20858 |
| 16102 | 3 | 4 | | | | IV-1 | Gm20865 |
| 16103 | 3 | 4 | | | | IV-1 | Gm20867 |
| 16104 | 3 | 4 | | | | IV-1 | Gm2087 |
| 16105 | 3 | 4 | | | | IV-1 | Gm20871 |
| 16106 | 3 | 4 | | | | IV-1 | Gm21119 |
| 16107 | 3 | 4 | | | | IV-1 | Gm21269 |
| 16108 | 3 | 4 | | | | IV-1 | Gm21284 |
| 16109 | 3 | 4 | | | | IV-1 | Gm21293 |
| 16110 | 3 | 4 | | | | IV-1 | Gm21304 |
| 16111 | 3 | 4 | | | | IV-1 | Gm21312 |
| 16112 | 3 | 4 | | | | IV-1 | Gm21319 |
| 16113 | 3 | 4 | | | | IV-1 | Gm21708 |
| 16114 | 3 | 4 | | | | IV-1 | Gm2176 |
| 16115 | 3 | 4 | | | | IV-1 | Gm21949 |
| 16116 | 3 | 4 | | | | IV-1 | Gm21950 |
| 16117 | 3 | 4 | | | | IV-1 | Gm21951 |
| 16118 | 3 | 4 | | | | IV-1 | Gm2381 |
| 16119 | 3 | 4 | | | | IV-1 | Gm2516 |
| 16120 | 3 | 4 | | | | IV-1 | Gm2518 |
| 16121 | 3 | 4 | | | | IV-1 | Gm266 |
| 16122 | 3 | 4 | | | | IV-1 | Gm2694 |
| 16123 | 3 | 4 | | | | IV-1 | Gm2762 |
| 16124 | 3 | 4 | | | | IV-1 | Gm2799 |
| 16125 | 3 | 4 | | | | IV-1 | Gm2825 |
| 16126 | 3 | 4 | | | | IV-1 | Gm2837 |
| 16127 | 3 | 4 | | | | IV-1 | Gm2a |
| 16128 | 3 | 4 | | | | IV-1 | Gm3020 |
| 16129 | 3 | 4 | | | | IV-1 | Gm3139 |
| 16130 | 3 | 4 | | | | IV-1 | Gm3279 |
| 16131 | 3 | 4 | | | | IV-1 | Gm3285 |
| 16132 | 3 | 4 | | | | IV-1 | Gm3383 |
| 16133 | 3 | 4 | | | | IV-1 | Gm3428 |
| 16134 | 3 | 4 | | | | IV-1 | Gm3458 |
| 16135 | 3 | 4 | | | | IV-1 | Gm362 |
| 16136 | 3 | 4 | | | | IV-1 | Gm3696 |
| 16137 | 3 | 4 | | | | IV-1 | Gm3701 |
| 16138 | 3 | 4 | | | | IV-1 | Gm3763 |
| 16139 | 3 | 4 | | | | IV-1 | Gm3985 |
| 16140 | 3 | 4 | | | | IV-1 | Gm4027 |
| 16141 | 3 | 4 | | | | IV-1 | Gm4201 |
| 16142 | 3 | 4 | | | | IV-1 | Gm4214 |
| 16143 | 3 | 4 | | | | IV-1 | Gm4216 |
| 16144 | 3 | 4 | | | | IV-1 | Gm4301 |
| 16145 | 3 | 4 | | | | IV-1 | Gm4312 |
| 16146 | 3 | 4 | | | | IV-1 | Gm4461 |
| 16147 | 3 | 4 | | | | IV-1 | Gm4567 |

Fig. 43 - 96

| | | | | | | | |
|---|---|---|---|---|---|---|---|
| 16148 | 3 | 4 | | | | IV-1 | Gm4710 |
| 16149 | 3 | 4 | | | | IV-1 | Gm4776 |
| 16150 | 3 | 4 | | | | IV-1 | Gm4814 |
| 16151 | 3 | 4 | | | | IV-1 | Gm4832 |
| 16152 | 3 | 4 | | | | IV-1 | Gm4861 |
| 16153 | 3 | 4 | | | | IV-1 | Gm4871 |
| 16154 | 3 | 4 | | | | IV-1 | Gm4926 |
| 16155 | 3 | 4 | | | | IV-1 | Gm4971 |
| 16156 | 3 | 4 | | | | IV-1 | Gm4975 |
| 16157 | 3 | 4 | | | | IV-1 | Gm4981 |
| 16158 | 3 | 4 | | | | IV-1 | Gm4984 |
| 16159 | 3 | 4 | | | | IV-1 | Gm5069 |
| 16160 | 3 | 4 | | | | IV-1 | Gm5084 |
| 16161 | 3 | 4 | | | | IV-1 | Gm5086 |
| 16162 | 3 | 4 | | | | IV-1 | Gm5087 |
| 16163 | 3 | 4 | | | | IV-1 | Gm5091 |
| 16164 | 3 | 4 | | | | IV-1 | Gm5095 |
| 16165 | 3 | 4 | | | | IV-1 | Gm5114 |
| 16166 | 3 | 4 | | | | IV-1 | Gm5126 |
| 16167 | 3 | 4 | | | | IV-1 | Gm5127 |
| 16168 | 3 | 4 | | | | IV-1 | Gm5129 |
| 16169 | 3 | 4 | | | | IV-1 | Gm5132 |
| 16170 | 3 | 4 | | | | IV-1 | Gm5136 |
| 16171 | 3 | 4 | | | | IV-1 | Gm5169 |
| 16172 | 3 | 4 | | | | IV-1 | Gm5177 |
| 16173 | 3 | 4 | | | | IV-1 | Gm5382 |
| 16174 | 3 | 4 | | | | IV-1 | Gm5409 |
| 16175 | 3 | 4 | | | | IV-1 | Gm5414 |
| 16176 | 3 | 4 | | | | IV-1 | Gm5420 |
| 16177 | 3 | 4 | | | | IV-1 | Gm5458 |
| 16178 | 3 | 4 | | | | IV-1 | Gm5464 |
| 16179 | 3 | 4 | | | | IV-1 | Gm5468 |
| 16180 | 3 | 4 | | | | IV-1 | Gm5475 |
| 16181 | 3 | 4 | | | | IV-1 | Gm5485 |
| 16182 | 3 | 4 | | | | IV-1 | Gm5538 |
| 16183 | 3 | 4 | | | | IV-1 | Gm5592 |
| 16184 | 3 | 4 | | | | IV-1 | Gm5595 |
| 16185 | 3 | 4 | | | | IV-1 | Gm5607 |
| 16186 | 3 | 4 | | | | IV-1 | Gm5615 |
| 16187 | 3 | 4 | | | | IV-1 | Gm5622 |
| 16188 | 3 | 4 | | | | IV-1 | Gm5627 |
| 16189 | 3 | 4 | | | | IV-1 | Gm5635 |
| 16190 | 3 | 4 | | | | IV-1 | Gm5726 |
| 16191 | 3 | 4 | | | | IV-1 | Gm5728 |
| 16192 | 3 | 4 | | | | IV-1 | Gm5800 |
| 16193 | 3 | 4 | | | | IV-1 | Gm5868 |
| 16194 | 3 | 4 | | | | IV-1 | Gm5878 |
| 16195 | 3 | 4 | | | | IV-1 | Gm5891 |
| 16196 | 3 | 4 | | | | IV-1 | Gm590 |
| 16197 | 3 | 4 | | | | IV-1 | Gm5936 |
| 16198 | 3 | 4 | | | | IV-1 | Gm6034 |
| 16199 | 3 | 4 | | | | IV-1 | Gm6042 |
| 16200 | 3 | 4 | | | | IV-1 | Gm609 |
| 16201 | 3 | 4 | | | | IV-1 | Gm6150 |
| 16202 | 3 | 4 | | | | IV-1 | Gm6249 |
| 16203 | 3 | 4 | | | | IV-1 | Gm6268 |
| 16204 | 3 | 4 | | | | IV-1 | Gm6289 |
| 16205 | 3 | 4 | | | | IV-1 | Gm6300 |
| 16206 | 3 | 4 | | | | IV-1 | Gm6370 |
| 16207 | 3 | 4 | | | | IV-1 | Gm6402 |
| 16208 | 3 | 4 | | | | IV-1 | Gm6498 |
| 16209 | 3 | 4 | | | | IV-1 | Gm6559 |
| 16210 | 3 | 4 | | | | IV-1 | Gm6583 |
| 16211 | 3 | 4 | | | | IV-1 | Gm6588 |
| 16212 | 3 | 4 | | | | IV-1 | Gm6614 |
| 16213 | 3 | 4 | | | | IV-1 | Gm6623 |
| 16214 | 3 | 4 | | | | IV-1 | Gm6763 |
| 16215 | 3 | 4 | | | | IV-1 | Gm6787 |
| 16216 | 3 | 4 | | | | IV-1 | Gm6793 |
| 16217 | 3 | 4 | | | | IV-1 | Gm6812 |
| 16218 | 3 | 4 | | | | IV-1 | Gm6878 |
| 16219 | 3 | 4 | | | | IV-1 | Gm6927 |
| 16220 | 3 | 4 | | | | IV-1 | Gm6938 |
| 16221 | 3 | 4 | | | | IV-1 | Gm7073 |
| 16222 | 3 | 4 | | | | IV-1 | Gm7157 |
| 16223 | 3 | 4 | | | | IV-1 | Gm7168 |
| 16224 | 3 | 4 | | | | IV-1 | Gm7271 |
| 16225 | 3 | 4 | | | | IV-1 | Gm7337 |
| 16226 | 3 | 4 | | | | IV-1 | Gm7457 |
| 16227 | 3 | 4 | | | | IV-1 | Gm7534 |
| 16228 | 3 | 4 | | | | IV-1 | Gm7538 |
| 16229 | 3 | 4 | | | | IV-1 | Gm7550 |
| 16230 | 3 | 4 | | | | IV-1 | Gm7977 |
| 16231 | 3 | 4 | | | | IV-1 | Gm7978 |
| 16232 | 3 | 4 | | | | IV-1 | Gm806 |
| 16233 | 3 | 4 | | | | IV-1 | Gm8234 |
| 16234 | 3 | 4 | | | | IV-1 | Gm8363 |
| 16235 | 3 | 4 | | | | IV-1 | Gm8580 |
| 16236 | 3 | 4 | | | | IV-1 | Gm8677 |
| 16237 | 3 | 4 | | | | IV-1 | Gm8765 |
| 16238 | 3 | 4 | | | | IV-1 | Gm8787 |
| 16239 | 3 | 4 | | | | IV-1 | Gm8882 |
| 16240 | 3 | 4 | | | | IV-1 | Gm9047 |
| 16241 | 3 | 4 | | | | IV-1 | Gm9054 |
| 16242 | 3 | 4 | | | | IV-1 | Gm9079 |
| 16243 | 3 | 4 | | | | IV-1 | Gm9112 |
| 16244 | 3 | 4 | | | | IV-1 | Gm9268 |
| 16245 | 3 | 4 | | | | IV-1 | Gm933 |
| 16246 | 3 | 4 | | | | IV-1 | Gm9376 |
| 16247 | 3 | 4 | | | | IV-1 | Gm9573 |
| 16248 | 3 | 4 | | | | IV-1 | Gm9731 |
| 16249 | 3 | 4 | | | | IV-1 | Gm9839 |
| 16250 | 3 | 4 | | | | IV-1 | Gm9866 |
| 16251 | 3 | 4 | | | | IV-1 | Gm9926 |
| 16252 | 3 | 4 | | | | IV-1 | Gm9961 |
| 16253 | 3 | 4 | | | | IV-1 | Gm9962 |
| 16254 | 3 | 4 | | | | IV-1 | Gmcl1 |
| 16255 | 3 | 4 | | | | IV-1 | Gmeb1 |
| 16256 | 3 | 4 | | | | IV-1 | Gmeb2 |
| 16257 | 3 | 4 | | | | IV-1 | Gml |
| 16258 | 3 | 4 | | | | IV-1 | Gmnc |
| 16259 | 3 | 4 | | | | IV-1 | Gmppa |
| 16260 | 3 | 4 | | | | IV-1 | Gmpr2 |
| 16261 | 3 | 4 | | | | IV-1 | Gna11 |
| 16262 | 3 | 4 | | | | IV-1 | Gna13 |
| 16263 | 3 | 4 | | | | IV-1 | Gnai2 |
| 16264 | 3 | 4 | | | | IV-1 | Gnai3 |
| 16265 | 3 | 4 | | | | IV-1 | Gnas |
| 16266 | 3 | 4 | | | | IV-1 | Gnat2 |
| 16267 | 3 | 4 | | | | IV-1 | Gnat3 |
| 16268 | 3 | 4 | | | | IV-1 | Gnb1 |
| 16269 | 3 | 4 | | | | IV-1 | Gnb2 |
| 16270 | 3 | 4 | | | | IV-1 | Gnb4 |
| 16271 | 3 | 4 | | | | IV-1 | Gng12 |
| 16272 | 3 | 4 | | | | IV-1 | Gng4 |
| 16273 | 3 | 4 | | | | IV-1 | Gng8 |
| 16274 | 3 | 4 | | | | IV-1 | Gngt1 |
| 16275 | 3 | 4 | | | | IV-1 | Gnl1 |
| 16276 | 3 | 4 | | | | IV-1 | Gnl2 |
| 16277 | 3 | 4 | | | | IV-1 | Gnl3l |
| 16278 | 3 | 4 | | | | IV-1 | Gnpat |
| 16279 | 3 | 4 | | | | IV-1 | Gnpda1 |
| 16280 | 3 | 4 | | | | IV-1 | Gnpnat1 |
| 16281 | 3 | 4 | | | | IV-1 | Gnrhr |
| 16282 | 3 | 4 | | | | IV-1 | Golga1 |
| 16283 | 3 | 4 | | | | IV-1 | Golga2 |
| 16284 | 3 | 4 | | | | IV-1 | Golga5 |
| 16285 | 3 | 4 | | | | IV-1 | Golga7 |
| 16286 | 3 | 4 | | | | IV-1 | Golga7b |
| 16287 | 3 | 4 | | | | IV-1 | Golm1 |
| 16288 | 3 | 4 | | | | IV-1 | Golph3 |
| 16289 | 3 | 4 | | | | IV-1 | Golph3l |
| 16290 | 3 | 4 | | | | IV-1 | Golt1a |
| 16291 | 3 | 4 | | | | IV-1 | Golt1b |
| 16292 | 3 | 4 | | | | IV-1 | Gon4l |
| 16293 | 3 | 4 | | | | IV-1 | Gopc |
| 16294 | 3 | 4 | | | | IV-1 | Gorasp1 |
| 16295 | 3 | 4 | | | | IV-1 | Gorasp2 |
| 16296 | 3 | 4 | | | | IV-1 | Gosr1 |
| 16297 | 3 | 4 | | | | IV-1 | Gosr2 |
| 16298 | 3 | 4 | | | | IV-1 | Got1l1 |
| 16299 | 3 | 4 | | | | IV-1 | Got2 |
| 16300 | 3 | 4 | | | | IV-1 | Gpa33 |
| 16301 | 3 | 4 | | | | IV-1 | Gpalpp1 |
| 16302 | 3 | 4 | | | | IV-1 | Gpank1 |
| 16303 | 3 | 4 | | | | IV-1 | Gpat2 |
| 16304 | 3 | 4 | | | | IV-1 | Gpatch1 |
| 16305 | 3 | 4 | | | | IV-1 | Gpbar1 |
| 16306 | 3 | 4 | | | | IV-1 | Gpbp1 |
| 16307 | 3 | 4 | | | | IV-1 | Gpbp1l1 |
| 16308 | 3 | 4 | | | | IV-1 | Gpc2 |
| 16309 | 3 | 4 | | | | IV-1 | Gpc5 |
| 16310 | 3 | 4 | | | | IV-1 | Gpc6 |
| 16311 | 3 | 4 | | | | IV-1 | Gpd1l |
| 16312 | 3 | 4 | | | | IV-1 | Gpd2 |
| 16313 | 3 | 4 | | | | IV-1 | Gpha2 |
| 16314 | 3 | 4 | | | | IV-1 | Gphb5 |
| 16315 | 3 | 4 | | | | IV-1 | Gpkow |
| 16316 | 3 | 4 | | | | IV-1 | Gpn1 |
| 16317 | 3 | 4 | | | | IV-1 | Gpn3 |

Fig. 43 - 97

| | | | | | | | |
|---|---|---|---|---|---|---|---|
| 16318 | 3 | 4 | | | | IV-1 | Gpr101 |
| 16319 | 3 | 4 | | | | IV-1 | Gpr107 |
| 16320 | 3 | 4 | | | | IV-1 | Gpr108 |
| 16321 | 3 | 4 | | | | IV-1 | Gpr110 |
| 16322 | 3 | 4 | | | | IV-1 | Gpr111 |
| 16323 | 3 | 4 | | | | IV-1 | Gpr119 |
| 16324 | 3 | 4 | | | | IV-1 | Gpr123 |
| 16325 | 3 | 4 | | | | IV-1 | Gpr124 |
| 16326 | 3 | 4 | | | | IV-1 | Gpr125 |
| 16327 | 3 | 4 | | | | IV-1 | Gpr137 |
| 16328 | 3 | 4 | | | | IV-1 | Gpr137b |
| 16329 | 3 | 4 | | | | IV-1 | Gpr139 |
| 16330 | 3 | 4 | | | | IV-1 | Gpr142 |
| 16331 | 3 | 4 | | | | IV-1 | Gpr143 |
| 16332 | 3 | 4 | | | | IV-1 | Gpr149 |
| 16333 | 3 | 4 | | | | IV-1 | Gpr156 |
| 16334 | 3 | 4 | | | | IV-1 | Gpr158 |
| 16335 | 3 | 4 | | | | IV-1 | Gpr165 |
| 16336 | 3 | 4 | | | | IV-1 | Gpr173 |
| 16337 | 3 | 4 | | | | IV-1 | Gpr176 |
| 16338 | 3 | 4 | | | | IV-1 | Gpr19 |
| 16339 | 3 | 4 | | | | IV-1 | Gpr21 |
| 16340 | 3 | 4 | | | | IV-1 | Gpr25 |
| 16341 | 3 | 4 | | | | IV-1 | Gpr3 |
| 16342 | 3 | 4 | | | | IV-1 | Gpr31b |
| 16343 | 3 | 4 | | | | IV-1 | Gpr33 |
| 16344 | 3 | 4 | | | | IV-1 | Gpr37 |
| 16345 | 3 | 4 | | | | IV-1 | Gpr37l1 |
| 16346 | 3 | 4 | | | | IV-1 | Gpr45 |
| 16347 | 3 | 4 | | | | IV-1 | Gpr52 |
| 16348 | 3 | 4 | | | | IV-1 | Gpr6 |
| 16349 | 3 | 4 | | | | IV-1 | Gpr62 |
| 16350 | 3 | 4 | | | | IV-1 | Gpr68 |
| 16351 | 3 | 4 | | | | IV-1 | Gpr75 |
| 16352 | 3 | 4 | | | | IV-1 | Gpr82 |
| 16353 | 3 | 4 | | | | IV-1 | Gpr83 |
| 16354 | 3 | 4 | | | | IV-1 | Gpr84 |
| 16355 | 3 | 4 | | | | IV-1 | Gpr85 |
| 16356 | 3 | 4 | | | | IV-1 | Gpr87 |
| 16357 | 3 | 4 | | | | IV-1 | Gpr98 |
| 16358 | 3 | 4 | | | | IV-1 | Gprc5d |
| 16359 | 3 | 4 | | | | IV-1 | Gprc6a |
| 16360 | 3 | 4 | | | | IV-1 | Gprin2 |
| 16361 | 3 | 4 | | | | IV-1 | Gpx5 |
| 16362 | 3 | 4 | | | | IV-1 | Gpx6 |
| 16363 | 3 | 4 | | | | IV-1 | Gramd3 |
| 16364 | 3 | 4 | | | | IV-1 | Gramd4 |
| 16365 | 3 | 4 | | | | IV-1 | Grasp |
| 16366 | 3 | 4 | | | | IV-1 | Grb2 |
| 16367 | 3 | 4 | | | | IV-1 | Greb1 |
| 16368 | 3 | 4 | | | | IV-1 | Grem2 |
| 16369 | 3 | 4 | | | | IV-1 | Grhl2 |
| 16370 | 3 | 4 | | | | IV-1 | Grhl3 |
| 16371 | 3 | 4 | | | | IV-1 | Gria1 |
| 16372 | 3 | 4 | | | | IV-1 | Gria2 |
| 16373 | 3 | 4 | | | | IV-1 | Gria4 |
| 16374 | 3 | 4 | | | | IV-1 | Grid1 |
| 16375 | 3 | 4 | | | | IV-1 | Grid2 |
| 16376 | 3 | 4 | | | | IV-1 | Grid2ip |
| 16377 | 3 | 4 | | | | IV-1 | Grifin |
| 16378 | 3 | 4 | | | | IV-1 | Grik1 |
| 16379 | 3 | 4 | | | | IV-1 | Grik2 |
| 16380 | 3 | 4 | | | | IV-1 | Grik3 |
| 16381 | 3 | 4 | | | | IV-1 | Grik4 |
| 16382 | 3 | 4 | | | | IV-1 | Grin2a |
| 16383 | 3 | 4 | | | | IV-1 | Grin2b |
| 16384 | 3 | 4 | | | | IV-1 | Grin2c |
| 16385 | 3 | 4 | | | | IV-1 | Grin2d |
| 16386 | 3 | 4 | | | | IV-1 | Grin3a |
| 16387 | 3 | 4 | | | | IV-1 | Grin3b |
| 16388 | 3 | 4 | | | | IV-1 | Grina |
| 16389 | 3 | 4 | | | | IV-1 | Gripap1 |
| 16390 | 3 | 4 | | | | IV-1 | Grk1 |
| 16391 | 3 | 4 | | | | IV-1 | Grm1 |
| 16392 | 3 | 4 | | | | IV-1 | Grm2 |
| 16393 | 3 | 4 | | | | IV-1 | Grm4 |
| 16394 | 3 | 4 | | | | IV-1 | Grm5 |
| 16395 | 3 | 4 | | | | IV-1 | Grm6 |
| 16396 | 3 | 4 | | | | IV-1 | Grm7 |
| 16397 | 3 | 4 | | | | IV-1 | Grm8 |
| 16398 | 3 | 4 | | | | IV-1 | Grp |
| 16399 | 3 | 4 | | | | IV-1 | Grxcr1 |
| 16400 | 3 | 4 | | | | IV-1 | Grxcr2 |
| 16401 | 3 | 4 | | | | IV-1 | Gsap |
| 16402 | 3 | 4 | | | | IV-1 | Gsc2 |
| 16403 | 3 | 4 | | | | IV-1 | Gsdma |
| 16404 | 3 | 4 | | | | IV-1 | Gsdmc2 |
| 16405 | 3 | 4 | | | | IV-1 | Gsdmc4 |
| 16406 | 3 | 4 | | | | IV-1 | Gsdmcl-ps |
| 16407 | 3 | 4 | | | | IV-1 | Gsk3a |
| 16408 | 3 | 4 | | | | IV-1 | Gskip |
| 16409 | 3 | 4 | | | | IV-1 | Gstk1 |
| 16410 | 3 | 4 | | | | IV-1 | Gsto1 |
| 16411 | 3 | 4 | | | | IV-1 | Gsto2 |
| 16412 | 3 | 4 | | | | IV-1 | Gstt2 |
| 16413 | 3 | 4 | | | | IV-1 | Gstz1 |
| 16414 | 3 | 4 | | | | IV-1 | Gsx1 |
| 16415 | 3 | 4 | | | | IV-1 | Gsx2 |
| 16416 | 3 | 4 | | | | IV-1 | Gtdc1 |
| 16417 | 3 | 4 | | | | IV-1 | Gtf2a1l |
| 16418 | 3 | 4 | | | | IV-1 | Gtf2h1 |
| 16419 | 3 | 4 | | | | IV-1 | Gtf3c1 |
| 16420 | 3 | 4 | | | | IV-1 | Gtf3c2 |
| 16421 | 3 | 4 | | | | IV-1 | Gtf3c3 |
| 16422 | 3 | 4 | | | | IV-1 | Gtf3c6 |
| 16423 | 3 | 4 | | | | IV-1 | Gtpbp1 |
| 16424 | 3 | 4 | | | | IV-1 | Gtpbp3 |
| 16425 | 3 | 4 | | | | IV-1 | Gtsf1 |
| 16426 | 3 | 4 | | | | IV-1 | Guca1a |
| 16427 | 3 | 4 | | | | IV-1 | Guca2a |
| 16428 | 3 | 4 | | | | IV-1 | Guca2b |
| 16429 | 3 | 4 | | | | IV-1 | Gucy1a3 |
| 16430 | 3 | 4 | | | | IV-1 | Gucy2c |
| 16431 | 3 | 4 | | | | IV-1 | Gucy2d |
| 16432 | 3 | 4 | | | | IV-1 | Gucy2e |
| 16433 | 3 | 4 | | | | IV-1 | Gucy2f |
| 16434 | 3 | 4 | | | | IV-1 | Guf1 |
| 16435 | 3 | 4 | | | | IV-1 | Gxylt1 |
| 16436 | 3 | 4 | | | | IV-1 | Gxylt2 |
| 16437 | 3 | 4 | | | | IV-1 | Gypc |
| 16438 | 3 | 4 | | | | IV-1 | Gzmc |
| 16439 | 3 | 4 | | | | IV-1 | Gzmd |
| 16440 | 3 | 4 | | | | IV-1 | Gzme |
| 16441 | 3 | 4 | | | | IV-1 | Gzmf |
| 16442 | 3 | 4 | | | | IV-1 | Gzmg |
| 16443 | 3 | 4 | | | | IV-1 | Gzmk |
| 16444 | 3 | 4 | | | | IV-1 | H1foo |
| 16445 | 3 | 4 | | | | IV-1 | H2afx |
| 16446 | 3 | 4 | | | | IV-1 | H2afy3 |
| 16447 | 3 | 4 | | | | IV-1 | H2bfm |
| 16448 | 3 | 4 | | | | IV-1 | H2-Bl |
| 16449 | 3 | 4 | | | | IV-1 | H2-Ea-ps |
| 16450 | 3 | 4 | | | | IV-1 | H2-Ke2 |
| 16451 | 3 | 4 | | | | IV-1 | H2-L |
| 16452 | 3 | 4 | | | | IV-1 | H2-M10.1 |
| 16453 | 3 | 4 | | | | IV-1 | H2-M10.2 |
| 16454 | 3 | 4 | | | | IV-1 | H2-M10.3 |
| 16455 | 3 | 4 | | | | IV-1 | H2-M10.4 |
| 16456 | 3 | 4 | | | | IV-1 | H2-M9 |
| 16457 | 3 | 4 | | | | IV-1 | H2-T3 |
| 16458 | 3 | 4 | | | | IV-1 | H60b |
| 16459 | 3 | 4 | | | | IV-1 | H60c |
| 16460 | 3 | 4 | | | | IV-1 | Haao |
| 16461 | 3 | 4 | | | | IV-1 | Habp2 |
| 16462 | 3 | 4 | | | | IV-1 | Habp4 |
| 16463 | 3 | 4 | | | | IV-1 | Hagh |
| 16464 | 3 | 4 | | | | IV-1 | Hal |
| 16465 | 3 | 4 | | | | IV-1 | Hand1 |
| 16466 | 3 | 4 | | | | IV-1 | Hand2 |
| 16467 | 3 | 4 | | | | IV-1 | Hao2 |
| 16468 | 3 | 4 | | | | IV-1 | Hapln2 |
| 16469 | 3 | 4 | | | | IV-1 | Hapln3 |
| 16470 | 3 | 4 | | | | IV-1 | Hars2 |
| 16471 | 3 | 4 | | | | IV-1 | Has1 |
| 16472 | 3 | 4 | | | | IV-1 | Has2 |
| 16473 | 3 | 4 | | | | IV-1 | Has2os |
| 16474 | 3 | 4 | | | | IV-1 | Haus2 |
| 16475 | 3 | 4 | | | | IV-1 | Haus5 |
| 16476 | 3 | 4 | | | | IV-1 | Haus6 |
| 16477 | 3 | 4 | | | | IV-1 | Havcr2 |
| 16478 | 3 | 4 | | | | IV-1 | Hbb-bh1 |
| 16479 | 3 | 4 | | | | IV-1 | Hbb-bh2 |
| 16480 | 3 | 4 | | | | IV-1 | Hcar1 |
| 16481 | 3 | 4 | | | | IV-1 | Hcn1 |
| 16482 | 3 | 4 | | | | IV-1 | Hcn3 |
| 16483 | 3 | 4 | | | | IV-1 | Hcn4 |
| 16484 | 3 | 4 | | | | IV-1 | Hcrt |
| 16485 | 3 | 4 | | | | IV-1 | Hcrtr1 |
| 16486 | 3 | 4 | | | | IV-1 | Hcrtr2 |
| 16487 | 3 | 4 | | | | IV-1 | Hdac2 |

Fig. 43 - 98

| | | | | | | | |
|---|---|---|---|---|---|---|---|
| 16488 | 3 | 4 | | | | IV-1 | Hdac8 |
| 16489 | 3 | 4 | | | | IV-1 | Hdgfl1 |
| 16490 | 3 | 4 | | | | IV-1 | Hdgfrp2 |
| 16491 | 3 | 4 | | | | IV-1 | Hdgfrp3 |
| 16492 | 3 | 4 | | | | IV-1 | Hdhd1a |
| 16493 | 3 | 4 | | | | IV-1 | Hdhd2 |
| 16494 | 3 | 4 | | | | IV-1 | Hdlbp |
| 16495 | 3 | 4 | | | | IV-1 | Hdx |
| 16496 | 3 | 4 | | | | IV-1 | Heatr5a |
| 16497 | 3 | 4 | | | | IV-1 | Heatr9 |
| 16498 | 3 | 4 | | | | IV-1 | Hebp2 |
| 16499 | 3 | 4 | | | | IV-1 | Hectd1 |
| 16500 | 3 | 4 | | | | IV-1 | Hectd2 |
| 16501 | 3 | 4 | | | | IV-1 | Hectd3 |
| 16502 | 3 | 4 | | | | IV-1 | Hecw1 |
| 16503 | 3 | 4 | | | | IV-1 | Helb |
| 16504 | 3 | 4 | | | | IV-1 | Helq |
| 16505 | 3 | 4 | | | | IV-1 | Helt |
| 16506 | 3 | 4 | | | | IV-1 | Hemgn |
| 16507 | 3 | 4 | | | | IV-1 | Hemt1 |
| 16508 | 3 | 4 | | | | IV-1 | Henmt1 |
| 16509 | 3 | 4 | | | | IV-1 | Hepacam |
| 16510 | 3 | 4 | | | | IV-1 | Hephl1 |
| 16511 | 3 | 4 | | | | IV-1 | Herc4 |
| 16512 | 3 | 4 | | | | IV-1 | Hes2 |
| 16513 | 3 | 4 | | | | IV-1 | Hes3 |
| 16514 | 3 | 4 | | | | IV-1 | Hesx1 |
| 16515 | 3 | 4 | | | | IV-1 | Hexa |
| 16516 | 3 | 4 | | | | IV-1 | Hexdc |
| 16517 | 3 | 4 | | | | IV-1 | Hey2 |
| 16518 | 3 | 4 | | | | IV-1 | Heyl |
| 16519 | 3 | 4 | | | | IV-1 | Hfm1 |
| 16520 | 3 | 4 | | | | IV-1 | Hgfac |
| 16521 | 3 | 4 | | | | IV-1 | Hgsnat |
| 16522 | 3 | 4 | | | | IV-1 | Hhip |
| 16523 | 3 | 4 | | | | IV-1 | Hhipl2 |
| 16524 | 3 | 4 | | | | IV-1 | Hhla1 |
| 16525 | 3 | 4 | | | | IV-1 | Hiat1 |
| 16526 | 3 | 4 | | | | IV-1 | Hiatl1 |
| 16527 | 3 | 4 | | | | IV-1 | Hibadh |
| 16528 | 3 | 4 | | | | IV-1 | Hid1 |
| 16529 | 3 | 4 | | | | IV-1 | Hif1a |
| 16530 | 3 | 4 | | | | IV-1 | Hif1an |
| 16531 | 3 | 4 | | | | IV-1 | Higd1b |
| 16532 | 3 | 4 | | | | IV-1 | Higd1c |
| 16533 | 3 | 4 | | | | IV-1 | Higd2a |
| 16534 | 3 | 4 | | | | IV-1 | Hipk4 |
| 16535 | 3 | 4 | | | | IV-1 | Hira |
| 16536 | 3 | 4 | | | | IV-1 | Hist1h1a |
| 16537 | 3 | 4 | | | | IV-1 | Hist1h1b |
| 16538 | 3 | 4 | | | | IV-1 | Hist1h1t |
| 16539 | 3 | 4 | | | | IV-1 | Hist1h2ad |
| 16540 | 3 | 4 | | | | IV-1 | Hist1h2ak |
| 16541 | 3 | 4 | | | | IV-1 | Hist1h2ao |
| 16542 | 3 | 4 | | | | IV-1 | Hist1h3e |
| 16543 | 3 | 4 | | | | IV-1 | Hist1h3f |
| 16544 | 3 | 4 | | | | IV-1 | Hist1h3g |
| 16545 | 3 | 4 | | | | IV-1 | Hist4h4 |
| 16546 | 3 | 4 | | | | IV-1 | Hivep3 |
| 16547 | 3 | 4 | | | | IV-1 | Hkdc1 |
| 16548 | 3 | 4 | | | | IV-1 | Hlcs |
| 16549 | 3 | 4 | | | | IV-1 | Hltf |
| 16550 | 3 | 4 | | | | IV-1 | Hlx |
| 16551 | 3 | 4 | | | | IV-1 | Hmces |
| 16552 | 3 | 4 | | | | IV-1 | Hmg20a |
| 16553 | 3 | 4 | | | | IV-1 | Hmg20b |
| 16554 | 3 | 4 | | | | IV-1 | Hmga2 |
| 16555 | 3 | 4 | | | | IV-1 | Hmgb1 |
| 16556 | 3 | 4 | | | | IV-1 | Hmgb1-rs17 |
| 16557 | 3 | 4 | | | | IV-1 | Hmgcll1 |
| 16558 | 3 | 4 | | | | IV-1 | Hmgxb3 |
| 16559 | 3 | 4 | | | | IV-1 | Hmox2 |
| 16560 | 3 | 4 | | | | IV-1 | Hmx1 |
| 16561 | 3 | 4 | | | | IV-1 | Hmx3 |
| 16562 | 3 | 4 | | | | IV-1 | Hnf4g |
| 16563 | 3 | 4 | | | | IV-1 | Hnrnpa0 |
| 16564 | 3 | 4 | | | | IV-1 | Hnrnpa2b1 |
| 16565 | 3 | 4 | | | | IV-1 | Hnrnpa3 |
| 16566 | 3 | 4 | | | | IV-1 | Hnrnpab |
| 16567 | 3 | 4 | | | | IV-1 | Hnrnpc |
| 16568 | 3 | 4 | | | | IV-1 | Hnrnpd |
| 16569 | 3 | 4 | | | | IV-1 | Hnrnpf |
| 16570 | 3 | 4 | | | | IV-1 | Hnrnph1 |
| 16571 | 3 | 4 | | | | IV-1 | Hnrnph2 |
| 16572 | 3 | 4 | | | | IV-1 | Hnrnpk |
| 16573 | 3 | 4 | | | | IV-1 | Hnrnpm |
| 16574 | 3 | 4 | | | | IV-1 | Hnrnpr |
| 16575 | 3 | 4 | | | | IV-1 | Hnrnpu |
| 16576 | 3 | 4 | | | | IV-1 | Hnrnpul2 |
| 16577 | 3 | 4 | | | | IV-1 | Homer2 |
| 16578 | 3 | 4 | | | | IV-1 | Homez |
| 16579 | 3 | 4 | | | | IV-1 | Hopx |
| 16580 | 3 | 4 | | | | IV-1 | Hormad1 |
| 16581 | 3 | 4 | | | | IV-1 | Hormad2 |
| 16582 | 3 | 4 | | | | IV-1 | Hotair |
| 16583 | 3 | 4 | | | | IV-1 | Hottip |
| 16584 | 3 | 4 | | | | IV-1 | Hoxa11 |
| 16585 | 3 | 4 | | | | IV-1 | Hoxa5 |
| 16586 | 3 | 4 | | | | IV-1 | Hoxa9 |
| 16587 | 3 | 4 | | | | IV-1 | Hoxb1 |
| 16588 | 3 | 4 | | | | IV-1 | Hoxb13 |
| 16589 | 3 | 4 | | | | IV-1 | Hoxb3 |
| 16590 | 3 | 4 | | | | IV-1 | Hoxb9 |
| 16591 | 3 | 4 | | | | IV-1 | Hoxc12 |
| 16592 | 3 | 4 | | | | IV-1 | Hoxc13 |
| 16593 | 3 | 4 | | | | IV-1 | Hoxc8 |
| 16594 | 3 | 4 | | | | IV-1 | Hoxd1 |
| 16595 | 3 | 4 | | | | IV-1 | Hoxd11 |
| 16596 | 3 | 4 | | | | IV-1 | Hoxd12 |
| 16597 | 3 | 4 | | | | IV-1 | Hoxd13 |
| 16598 | 3 | 4 | | | | IV-1 | Hoxd9 |
| 16599 | 3 | 4 | | | | IV-1 | Hps3 |
| 16600 | 3 | 4 | | | | IV-1 | Hps5 |
| 16601 | 3 | 4 | | | | IV-1 | Hps6 |
| 16602 | 3 | 4 | | | | IV-1 | Hpse2 |
| 16603 | 3 | 4 | | | | IV-1 | Hrasls |
| 16604 | 3 | 4 | | | | IV-1 | Hrg |
| 16605 | 3 | 4 | | | | IV-1 | Hrh1 |
| 16606 | 3 | 4 | | | | IV-1 | Hrnr |
| 16607 | 3 | 4 | | | | IV-1 | Hs3st3b1 |
| 16608 | 3 | 4 | | | | IV-1 | Hs3st4 |
| 16609 | 3 | 4 | | | | IV-1 | Hs3st5 |
| 16610 | 3 | 4 | | | | IV-1 | Hs6st1 |
| 16611 | 3 | 4 | | | | IV-1 | Hs6st3 |
| 16612 | 3 | 4 | | | | IV-1 | Hsbp1l1 |
| 16613 | 3 | 4 | | | | IV-1 | Hsd17b1 |
| 16614 | 3 | 4 | | | | IV-1 | Hsd17b13 |
| 16615 | 3 | 4 | | | | IV-1 | Hsd17b14 |
| 16616 | 3 | 4 | | | | IV-1 | Hsd17b4 |
| 16617 | 3 | 4 | | | | IV-1 | Hsd17b6 |
| 16618 | 3 | 4 | | | | IV-1 | Hsd3b1 |
| 16619 | 3 | 4 | | | | IV-1 | Hsd3b4 |
| 16620 | 3 | 4 | | | | IV-1 | Hsd3b5 |
| 16621 | 3 | 4 | | | | IV-1 | Hsd3b6 |
| 16622 | 3 | 4 | | | | IV-1 | Hsdl2 |
| 16623 | 3 | 4 | | | | IV-1 | Hsf2 |
| 16624 | 3 | 4 | | | | IV-1 | Hsf3 |
| 16625 | 3 | 4 | | | | IV-1 | Hsf4 |
| 16626 | 3 | 4 | | | | IV-1 | Hsf5 |
| 16627 | 3 | 4 | | | | IV-1 | Hspa13 |
| 16628 | 3 | 4 | | | | IV-1 | Hspa4 |
| 16629 | 3 | 4 | | | | IV-1 | Hspg2 |
| 16630 | 3 | 4 | | | | IV-1 | Htatsf1 |
| 16631 | 3 | 4 | | | | IV-1 | Htr1a |
| 16632 | 3 | 4 | | | | IV-1 | Htr1b |
| 16633 | 3 | 4 | | | | IV-1 | Htr1d |
| 16634 | 3 | 4 | | | | IV-1 | Htr1f |
| 16635 | 3 | 4 | | | | IV-1 | Htr2a |
| 16636 | 3 | 4 | | | | IV-1 | Htr3b |
| 16637 | 3 | 4 | | | | IV-1 | Htr5a |
| 16638 | 3 | 4 | | | | IV-1 | Htr5b |
| 16639 | 3 | 4 | | | | IV-1 | Htr6 |
| 16640 | 3 | 4 | | | | IV-1 | Htr7 |
| 16641 | 3 | 4 | | | | IV-1 | Hus1 |
| 16642 | 3 | 4 | | | | IV-1 | Hus1b |
| 16643 | 3 | 4 | | | | IV-1 | Hyal2 |
| 16644 | 3 | 4 | | | | IV-1 | Hyal3 |
| 16645 | 3 | 4 | | | | IV-1 | Hyal4 |
| 16646 | 3 | 4 | | | | IV-1 | Hyal5 |
| 16647 | 3 | 4 | | | | IV-1 | Hyal6 |
| 16648 | 3 | 4 | | | | IV-1 | Iars2 |
| 16649 | 3 | 4 | | | | IV-1 | Ica1l |
| 16650 | 3 | 4 | | | | IV-1 | Icam5 |
| 16651 | 3 | 4 | | | | IV-1 | Ick |
| 16652 | 3 | 4 | | | | IV-1 | Icmt |
| 16653 | 3 | 4 | | | | IV-1 | Icos |
| 16654 | 3 | 4 | | | | IV-1 | Ide |
| 16655 | 3 | 4 | | | | IV-1 | Idi2 |
| 16656 | 3 | 4 | | | | IV-1 | Ido1 |
| 16657 | 3 | 4 | | | | IV-1 | Ids |

Fig. 43 - 99

| | | | | | | | |
|---|---|---|---|---|---|---|---|
| 16658 | 3 | 4 | | | | IV-1 | idua |
| 16659 | 3 | 4 | | | | IV-1 | ier3ip1 |
| 16660 | 3 | 4 | | | | IV-1 | iffo1 |
| 16661 | 3 | 4 | | | | IV-1 | iffo2 |
| 16662 | 3 | 4 | | | | IV-1 | ifi202b |
| 16663 | 3 | 4 | | | | IV-1 | ifi44l |
| 16664 | 3 | 4 | | | | IV-1 | ifitm10 |
| 16665 | 3 | 4 | | | | IV-1 | ifltd1 |
| 16666 | 3 | 4 | | | | IV-1 | ifna1 |
| 16667 | 3 | 4 | | | | IV-1 | ifna11 |
| 16668 | 3 | 4 | | | | IV-1 | ifna12 |
| 16669 | 3 | 4 | | | | IV-1 | ifna13 |
| 16670 | 3 | 4 | | | | IV-1 | ifna14 |
| 16671 | 3 | 4 | | | | IV-1 | ifngr2 |
| 16672 | 3 | 4 | | | | IV-1 | ifnk |
| 16673 | 3 | 4 | | | | IV-1 | ifni2 |
| 16674 | 3 | 4 | | | | IV-1 | ifnz |
| 16675 | 3 | 4 | | | | IV-1 | ift52 |
| 16676 | 3 | 4 | | | | IV-1 | ift57 |
| 16677 | 3 | 4 | | | | IV-1 | ift81 |
| 16678 | 3 | 4 | | | | IV-1 | igbp1 |
| 16679 | 3 | 4 | | | | IV-1 | igbp1b |
| 16680 | 3 | 4 | | | | IV-1 | igdcc3 |
| 16681 | 3 | 4 | | | | IV-1 | igf1 |
| 16682 | 3 | 4 | | | | IV-1 | igf2 |
| 16683 | 3 | 4 | | | | IV-1 | igf2bp1 |
| 16684 | 3 | 4 | | | | IV-1 | igf2os |
| 16685 | 3 | 4 | | | | IV-1 | igf2r |
| 16686 | 3 | 4 | | | | IV-1 | igfbp3 |
| 16687 | 3 | 4 | | | | IV-1 | igfbpl1 |
| 16688 | 3 | 4 | | | | IV-1 | igfl3 |
| 16689 | 3 | 4 | | | | IV-1 | ighmbp2 |
| 16690 | 3 | 4 | | | | IV-1 | iglon5 |
| 16691 | 3 | 4 | | | | IV-1 | igsf1 |
| 16692 | 3 | 4 | | | | IV-1 | igsf8 |
| 16693 | 3 | 4 | | | | IV-1 | igsf9 |
| 16694 | 3 | 4 | | | | IV-1 | igsf9b |
| 16695 | 3 | 4 | | | | IV-1 | ik |
| 16696 | 3 | 4 | | | | IV-1 | ikbip |
| 16697 | 3 | 4 | | | | IV-1 | ikbkap |
| 16698 | 3 | 4 | | | | IV-1 | ikbkb |
| 16699 | 3 | 4 | | | | IV-1 | ikbkg |
| 16700 | 3 | 4 | | | | IV-1 | ikzf4 |
| 16701 | 3 | 4 | | | | IV-1 | ikzf5 |
| 16702 | 3 | 4 | | | | IV-1 | il10 |
| 16703 | 3 | 4 | | | | IV-1 | il10rb |
| 16704 | 3 | 4 | | | | IV-1 | il12b |
| 16705 | 3 | 4 | | | | IV-1 | il13 |
| 16706 | 3 | 4 | | | | IV-1 | il13ra2 |
| 16707 | 3 | 4 | | | | IV-1 | il17a |
| 16708 | 3 | 4 | | | | IV-1 | il17b |
| 16709 | 3 | 4 | | | | IV-1 | il17c |
| 16710 | 3 | 4 | | | | IV-1 | il17f |
| 16711 | 3 | 4 | | | | IV-1 | il17re |
| 16712 | 3 | 4 | | | | IV-1 | il18 |
| 16713 | 3 | 4 | | | | IV-1 | il19 |
| 16714 | 3 | 4 | | | | IV-1 | il1f10 |
| 16715 | 3 | 4 | | | | IV-1 | il1f5 |
| 16716 | 3 | 4 | | | | IV-1 | il1f8 |
| 16717 | 3 | 4 | | | | IV-1 | il1rapl1 |
| 16718 | 3 | 4 | | | | IV-1 | il1rapl2 |
| 16719 | 3 | 4 | | | | IV-1 | il20 |
| 16720 | 3 | 4 | | | | IV-1 | il20ra |
| 16721 | 3 | 4 | | | | IV-1 | il21 |
| 16722 | 3 | 4 | | | | IV-1 | il23a |
| 16723 | 3 | 4 | | | | IV-1 | il24 |
| 16724 | 3 | 4 | | | | IV-1 | il25 |
| 16725 | 3 | 4 | | | | IV-1 | il31 |
| 16726 | 3 | 4 | | | | IV-1 | il3ra |
| 16727 | 3 | 4 | | | | IV-1 | il5 |
| 16728 | 3 | 4 | | | | IV-1 | il6 |
| 16729 | 3 | 4 | | | | IV-1 | il9 |
| 16730 | 3 | 4 | | | | IV-1 | ildr1 |
| 16731 | 3 | 4 | | | | IV-1 | ilf3 |
| 16732 | 3 | 4 | | | | IV-1 | ilkap |
| 16733 | 3 | 4 | | | | IV-1 | iltifb |
| 16734 | 3 | 4 | | | | IV-1 | ilvbl |
| 16735 | 3 | 4 | | | | IV-1 | immt |
| 16736 | 3 | 4 | | | | IV-1 | impact |
| 16737 | 3 | 4 | | | | IV-1 | impg1 |
| 16738 | 3 | 4 | | | | IV-1 | impg2 |
| 16739 | 3 | 4 | | | | IV-1 | ina |
| 16740 | 3 | 4 | | | | IV-1 | ing3 |
| 16741 | 3 | 4 | | | | IV-1 | ing5 |
| 16742 | 3 | 4 | | | | IV-1 | inhba |
| 16743 | 3 | 4 | | | | IV-1 | inhbc |
| 16744 | 3 | 4 | | | | IV-1 | inip |
| 16745 | 3 | 4 | | | | IV-1 | ino80 |
| 16746 | 3 | 4 | | | | IV-1 | ino80dos |
| 16747 | 3 | 4 | | | | IV-1 | ino80e |
| 16748 | 3 | 4 | | | | IV-1 | inpp4a |
| 16749 | 3 | 4 | | | | IV-1 | inpp5a |
| 16750 | 3 | 4 | | | | IV-1 | inpp5b |
| 16751 | 3 | 4 | | | | IV-1 | inpp5e |
| 16752 | 3 | 4 | | | | IV-1 | inpp5f |
| 16753 | 3 | 4 | | | | IV-1 | inpp5k |
| 16754 | 3 | 4 | | | | IV-1 | insm1 |
| 16755 | 3 | 4 | | | | IV-1 | insm2 |
| 16756 | 3 | 4 | | | | IV-1 | insr |
| 16757 | 3 | 4 | | | | IV-1 | ints1 |
| 16758 | 3 | 4 | | | | IV-1 | ints10 |
| 16759 | 3 | 4 | | | | IV-1 | ints5 |
| 16760 | 3 | 4 | | | | IV-1 | ints7 |
| 16761 | 3 | 4 | | | | IV-1 | ints9 |
| 16762 | 3 | 4 | | | | IV-1 | intu |
| 16763 | 3 | 4 | | | | IV-1 | ip6k1 |
| 16764 | 3 | 4 | | | | IV-1 | ipcef1 |
| 16765 | 3 | 4 | | | | IV-1 | ipo4 |
| 16766 | 3 | 4 | | | | IV-1 | ipo8 |
| 16767 | 3 | 4 | | | | IV-1 | ipo9 |
| 16768 | 3 | 4 | | | | IV-1 | ipp |
| 16769 | 3 | 4 | | | | IV-1 | ippk |
| 16770 | 3 | 4 | | | | IV-1 | ipw |
| 16771 | 3 | 4 | | | | IV-1 | iqca |
| 16772 | 3 | 4 | | | | IV-1 | iqcc |
| 16773 | 3 | 4 | | | | IV-1 | iqce |
| 16774 | 3 | 4 | | | | IV-1 | iqcf6 |
| 16775 | 3 | 4 | | | | IV-1 | iqch |
| 16776 | 3 | 4 | | | | IV-1 | iqgap3 |
| 16777 | 3 | 4 | | | | IV-1 | iqsec3 |
| 16778 | 3 | 4 | | | | IV-1 | irak1 |
| 16779 | 3 | 4 | | | | IV-1 | irak1bp1 |
| 16780 | 3 | 4 | | | | IV-1 | irak2 |
| 16781 | 3 | 4 | | | | IV-1 | irak3 |
| 16782 | 3 | 4 | | | | IV-1 | irf2 |
| 16783 | 3 | 4 | | | | IV-1 | irf2bp2 |
| 16784 | 3 | 4 | | | | IV-1 | irf2bpl |
| 16785 | 3 | 4 | | | | IV-1 | irs4 |
| 16786 | 3 | 4 | | | | IV-1 | irx2 |
| 16787 | 3 | 4 | | | | IV-1 | irx3 |
| 16788 | 3 | 4 | | | | IV-1 | irx6 |
| 16789 | 3 | 4 | | | | IV-1 | ism1 |
| 16790 | 3 | 4 | | | | IV-1 | ism2 |
| 16791 | 3 | 4 | | | | IV-1 | isoc2a |
| 16792 | 3 | 4 | | | | IV-1 | ispd |
| 16793 | 3 | 4 | | | | IV-1 | ist1 |
| 16794 | 3 | 4 | | | | IV-1 | itch |
| 16795 | 3 | 4 | | | | IV-1 | itfg1 |
| 16796 | 3 | 4 | | | | IV-1 | itga2 |
| 16797 | 3 | 4 | | | | IV-1 | itga3 |
| 16798 | 3 | 4 | | | | IV-1 | itga8 |
| 16799 | 3 | 4 | | | | IV-1 | itga9 |
| 16800 | 3 | 4 | | | | IV-1 | itgae |
| 16801 | 3 | 4 | | | | IV-1 | itgav |
| 16802 | 3 | 4 | | | | IV-1 | itgax |
| 16803 | 3 | 4 | | | | IV-1 | itgb1 |
| 16804 | 3 | 4 | | | | IV-1 | itgb2l |
| 16805 | 3 | 4 | | | | IV-1 | itgb3bp |
| 16806 | 3 | 4 | | | | IV-1 | itgb5 |
| 16807 | 3 | 4 | | | | IV-1 | itgb7 |
| 16808 | 3 | 4 | | | | IV-1 | itgb8 |
| 16809 | 3 | 4 | | | | IV-1 | itih1 |
| 16810 | 3 | 4 | | | | IV-1 | itih3 |
| 16811 | 3 | 4 | | | | IV-1 | itln1 |
| 16812 | 3 | 4 | | | | IV-1 | itm2b |
| 16813 | 3 | 4 | | | | IV-1 | itm2c |
| 16814 | 3 | 4 | | | | IV-1 | itprip |
| 16815 | 3 | 4 | | | | IV-1 | itsn1 |
| 16816 | 3 | 4 | | | | IV-1 | ivd |
| 16817 | 3 | 4 | | | | IV-1 | ivl |
| 16818 | 3 | 4 | | | | IV-1 | izumo1 |
| 16819 | 3 | 4 | | | | IV-1 | izumo2 |
| 16820 | 3 | 4 | | | | IV-1 | izumo3 |
| 16821 | 3 | 4 | | | | IV-1 | jade2 |
| 16822 | 3 | 4 | | | | IV-1 | jak2 |
| 16823 | 3 | 4 | | | | IV-1 | jak3 |
| 16824 | 3 | 4 | | | | IV-1 | jakmip2 |
| 16825 | 3 | 4 | | | | IV-1 | jakmip3 |
| 16826 | 3 | 4 | | | | IV-1 | jam2 |
| 16827 | 3 | 4 | | | | IV-1 | jarid2 |

Fig. 43 - 100

| | | | | | | | | |
|---|---|---|---|---|---|---|---|---|
| 16828 | 3 | 4 | | | | | IV-1 | Jazf1 |
| 16829 | 3 | 4 | | | | | IV-1 | Jmjd6 |
| 16830 | 3 | 4 | | | | | IV-1 | Jmjd7-pla2g4b |
| 16831 | 3 | 4 | | | | | IV-1 | Josd1 |
| 16832 | 3 | 4 | | | | | IV-1 | Jph3 |
| 16833 | 3 | 4 | | | | | IV-1 | Jpx |
| 16834 | 3 | 4 | | | | | IV-1 | Jrkl |
| 16835 | 3 | 4 | | | | | IV-1 | Jup |
| 16836 | 3 | 4 | | | | | IV-1 | Kank2 |
| 16837 | 3 | 4 | | | | | IV-1 | Kank4os |
| 16838 | 3 | 4 | | | | | IV-1 | Kansl2 |
| 16839 | 3 | 4 | | | | | IV-1 | Kansl3 |
| 16840 | 3 | 4 | | | | | IV-1 | Kars |
| 16841 | 3 | 4 | | | | | IV-1 | Kat2b |
| 16842 | 3 | 4 | | | | | IV-1 | Kat7 |
| 16843 | 3 | 4 | | | | | IV-1 | Katna1 |
| 16844 | 3 | 4 | | | | | IV-1 | Katnal2 |
| 16845 | 3 | 4 | | | | | IV-1 | Katnb1 |
| 16846 | 3 | 4 | | | | | IV-1 | Katnbl1 |
| 16847 | 3 | 4 | | | | | IV-1 | Kazn |
| 16848 | 3 | 4 | | | | | IV-1 | Kbtbd13 |
| 16849 | 3 | 4 | | | | | IV-1 | Kbtbd2 |
| 16850 | 3 | 4 | | | | | IV-1 | Kbtbd7 |
| 16851 | 3 | 4 | | | | | IV-1 | Kcmf1 |
| 16852 | 3 | 4 | | | | | IV-1 | Kcna10 |
| 16853 | 3 | 4 | | | | | IV-1 | Kcna4 |
| 16854 | 3 | 4 | | | | | IV-1 | Kcna6 |
| 16855 | 3 | 4 | | | | | IV-1 | Kcnab2 |
| 16856 | 3 | 4 | | | | | IV-1 | Kcnab3 |
| 16857 | 3 | 4 | | | | | IV-1 | Kcnb2 |
| 16858 | 3 | 4 | | | | | IV-1 | Kcnd1 |
| 16859 | 3 | 4 | | | | | IV-1 | Kcnd2 |
| 16860 | 3 | 4 | | | | | IV-1 | Kcnd3 |
| 16861 | 3 | 4 | | | | | IV-1 | Kcnd3os |
| 16862 | 3 | 4 | | | | | IV-1 | Kcne1 |
| 16863 | 3 | 4 | | | | | IV-1 | Kcne2 |
| 16864 | 3 | 4 | | | | | IV-1 | Kcnf1 |
| 16865 | 3 | 4 | | | | | IV-1 | Kcng1 |
| 16866 | 3 | 4 | | | | | IV-1 | Kcng3 |
| 16867 | 3 | 4 | | | | | IV-1 | Kcng4 |
| 16868 | 3 | 4 | | | | | IV-1 | Kcnh4 |
| 16869 | 3 | 4 | | | | | IV-1 | Kcnh6 |
| 16870 | 3 | 4 | | | | | IV-1 | Kcnh8 |
| 16871 | 3 | 4 | | | | | IV-1 | Kcnj1 |
| 16872 | 3 | 4 | | | | | IV-1 | Kcnj13 |
| 16873 | 3 | 4 | | | | | IV-1 | Kcnj14 |
| 16874 | 3 | 4 | | | | | IV-1 | Kcnj3 |
| 16875 | 3 | 4 | | | | | IV-1 | Kcnj4 |
| 16876 | 3 | 4 | | | | | IV-1 | Kcnj6 |
| 16877 | 3 | 4 | | | | | IV-1 | Kcnk10 |
| 16878 | 3 | 4 | | | | | IV-1 | Kcnk12 |
| 16879 | 3 | 4 | | | | | IV-1 | Kcnk15 |
| 16880 | 3 | 4 | | | | | IV-1 | Kcnk18 |
| 16881 | 3 | 4 | | | | | IV-1 | Kcnk4 |
| 16882 | 3 | 4 | | | | | IV-1 | Kcnk9 |
| 16883 | 3 | 4 | | | | | IV-1 | Kcnma1 |
| 16884 | 3 | 4 | | | | | IV-1 | Kcnmb2 |
| 16885 | 3 | 4 | | | | | IV-1 | Kcnmb3 |
| 16886 | 3 | 4 | | | | | IV-1 | Kcnmb4 |
| 16887 | 3 | 4 | | | | | IV-1 | Kcnq1ot1 |
| 16888 | 3 | 4 | | | | | IV-1 | Kcnq2 |
| 16889 | 3 | 4 | | | | | IV-1 | Kcnq3 |
| 16890 | 3 | 4 | | | | | IV-1 | Kcns2 |
| 16891 | 3 | 4 | | | | | IV-1 | Kcns3 |
| 16892 | 3 | 4 | | | | | IV-1 | Kcnt1 |
| 16893 | 3 | 4 | | | | | IV-1 | Kcnt2 |
| 16894 | 3 | 4 | | | | | IV-1 | Kcnu1 |
| 16895 | 3 | 4 | | | | | IV-1 | Kcnv1 |
| 16896 | 3 | 4 | | | | | IV-1 | Kcnv2 |
| 16897 | 3 | 4 | | | | | IV-1 | Kcp |
| 16898 | 3 | 4 | | | | | IV-1 | Kctd10 |
| 16899 | 3 | 4 | | | | | IV-1 | Kctd11 |
| 16900 | 3 | 4 | | | | | IV-1 | Kctd16 |
| 16901 | 3 | 4 | | | | | IV-1 | Kctd18 |
| 16902 | 3 | 4 | | | | | IV-1 | Kctd19 |
| 16903 | 3 | 4 | | | | | IV-1 | Kctd4 |
| 16904 | 3 | 4 | | | | | IV-1 | Kctd5 |
| 16905 | 3 | 4 | | | | | IV-1 | Kctd6 |
| 16906 | 3 | 4 | | | | | IV-1 | Kctd7 |
| 16907 | 3 | 4 | | | | | IV-1 | Kdelc2 |
| 16908 | 3 | 4 | | | | | IV-1 | Kdelr1 |
| 16909 | 3 | 4 | | | | | IV-1 | Kdm3a |
| 16910 | 3 | 4 | | | | | IV-1 | Kdm4b |
| 16911 | 3 | 4 | | | | | IV-1 | Kdm4d |
| 16912 | 3 | 4 | | | | | IV-1 | Kdm5b |
| 16913 | 3 | 4 | | | | | IV-1 | Kdsr |
| 16914 | 3 | 4 | | | | | IV-1 | Kel |
| 16915 | 3 | 4 | | | | | IV-1 | Kera |
| 16916 | 3 | 4 | | | | | IV-1 | Khdc1b |
| 16917 | 3 | 4 | | | | | IV-1 | Khdc1c |
| 16918 | 3 | 4 | | | | | IV-1 | Khdrbs2 |
| 16919 | 3 | 4 | | | | | IV-1 | Khsrp |
| 16920 | 3 | 4 | | | | | IV-1 | Kidins220 |
| 16921 | 3 | 4 | | | | | IV-1 | Kif11 |
| 16922 | 3 | 4 | | | | | IV-1 | Kif12 |
| 16923 | 3 | 4 | | | | | IV-1 | Kif13a |
| 16924 | 3 | 4 | | | | | IV-1 | Kif14 |
| 16925 | 3 | 4 | | | | | IV-1 | Kif15 |
| 16926 | 3 | 4 | | | | | IV-1 | Kif16b |
| 16927 | 3 | 4 | | | | | IV-1 | Kif17 |
| 16928 | 3 | 4 | | | | | IV-1 | Kif18a |
| 16929 | 3 | 4 | | | | | IV-1 | Kif18b |
| 16930 | 3 | 4 | | | | | IV-1 | Kif19a |
| 16931 | 3 | 4 | | | | | IV-1 | Kif1c |
| 16932 | 3 | 4 | | | | | IV-1 | Kif20b |
| 16933 | 3 | 4 | | | | | IV-1 | Kif23 |
| 16934 | 3 | 4 | | | | | IV-1 | Kif24 |
| 16935 | 3 | 4 | | | | | IV-1 | Kif26b |
| 16936 | 3 | 4 | | | | | IV-1 | Kif2c |
| 16937 | 3 | 4 | | | | | IV-1 | Kif3a |
| 16938 | 3 | 4 | | | | | IV-1 | Kif3b |
| 16939 | 3 | 4 | | | | | IV-1 | Kif4 |
| 16940 | 3 | 4 | | | | | IV-1 | Kif5b |
| 16941 | 3 | 4 | | | | | IV-1 | Kif6 |
| 16942 | 3 | 4 | | | | | IV-1 | Kif7 |
| 16943 | 3 | 4 | | | | | IV-1 | Kifap3 |
| 16944 | 3 | 4 | | | | | IV-1 | Kifc5b |
| 16945 | 3 | 4 | | | | | IV-1 | Kir3dl1 |
| 16946 | 3 | 4 | | | | | IV-1 | Kir3dl2 |
| 16947 | 3 | 4 | | | | | IV-1 | Kirrel2 |
| 16948 | 3 | 4 | | | | | IV-1 | Kirrel3 |
| 16949 | 3 | 4 | | | | | IV-1 | Kis2 |
| 16950 | 3 | 4 | | | | | IV-1 | Klc1 |
| 16951 | 3 | 4 | | | | | IV-1 | Klc2 |
| 16952 | 3 | 4 | | | | | IV-1 | Klc4 |
| 16953 | 3 | 4 | | | | | IV-1 | Klf10 |
| 16954 | 3 | 4 | | | | | IV-1 | Klf13 |
| 16955 | 3 | 4 | | | | | IV-1 | Klf14 |
| 16956 | 3 | 4 | | | | | IV-1 | Klf17 |
| 16957 | 3 | 4 | | | | | IV-1 | Klf6 |
| 16958 | 3 | 4 | | | | | IV-1 | Klhdc10 |
| 16959 | 3 | 4 | | | | | IV-1 | Klhdc2 |
| 16960 | 3 | 4 | | | | | IV-1 | Klhdc4 |
| 16961 | 3 | 4 | | | | | IV-1 | Klhdc7b |
| 16962 | 3 | 4 | | | | | IV-1 | Klhdc9 |
| 16963 | 3 | 4 | | | | | IV-1 | Klhl1 |
| 16964 | 3 | 4 | | | | | IV-1 | Klhl12 |
| 16965 | 3 | 4 | | | | | IV-1 | Klhl13 |
| 16966 | 3 | 4 | | | | | IV-1 | Klhl18 |
| 16967 | 3 | 4 | | | | | IV-1 | Klhl2 |
| 16968 | 3 | 4 | | | | | IV-1 | Klhl20 |
| 16969 | 3 | 4 | | | | | IV-1 | Klhl22 |
| 16970 | 3 | 4 | | | | | IV-1 | Klhl26 |
| 16971 | 3 | 4 | | | | | IV-1 | Klhl3 |
| 16972 | 3 | 4 | | | | | IV-1 | Klhl32 |
| 16973 | 3 | 4 | | | | | IV-1 | Klhl34 |
| 16974 | 3 | 4 | | | | | IV-1 | Klhl35 |
| 16975 | 3 | 4 | | | | | IV-1 | Klhl36 |
| 16976 | 3 | 4 | | | | | IV-1 | Klhl5 |
| 16977 | 3 | 4 | | | | | IV-1 | Klhl7 |
| 16978 | 3 | 4 | | | | | IV-1 | Klhl9 |
| 16979 | 3 | 4 | | | | | IV-1 | Klk13 |
| 16980 | 3 | 4 | | | | | IV-1 | Klk1b1 |
| 16981 | 3 | 4 | | | | | IV-1 | Klk1b16 |
| 16982 | 3 | 4 | | | | | IV-1 | Klk1b22 |
| 16983 | 3 | 4 | | | | | IV-1 | Klk4 |
| 16984 | 3 | 4 | | | | | IV-1 | Klk5 |
| 16985 | 3 | 4 | | | | | IV-1 | Klra10 |
| 16986 | 3 | 4 | | | | | IV-1 | Klra12 |
| 16987 | 3 | 4 | | | | | IV-1 | Klra15 |
| 16988 | 3 | 4 | | | | | IV-1 | Klra3 |
| 16989 | 3 | 4 | | | | | IV-1 | Klra4 |
| 16990 | 3 | 4 | | | | | IV-1 | Klra8 |
| 16991 | 3 | 4 | | | | | IV-1 | Klrb1f |
| 16992 | 3 | 4 | | | | | IV-1 | Klrc3 |
| 16993 | 3 | 4 | | | | | IV-1 | Kndc1 |
| 16994 | 3 | 4 | | | | | IV-1 | Kng1 |
| 16995 | 3 | 4 | | | | | IV-1 | Knop1 |
| 16996 | 3 | 4 | | | | | IV-1 | Kntc1 |
| 16997 | 3 | 4 | | | | | IV-1 | Kpna1 |

Fig. 43 - 101

| | | | | | | | |
|---|---|---|---|---|---|---|---|
| 16998 | 3 | 4 | | | | IV-1 | Kpna3 |
| 16999 | 3 | 4 | | | | IV-1 | Kpna6 |
| 17000 | 3 | 4 | | | | IV-1 | Kpna7 |
| 17001 | 3 | 4 | | | | IV-1 | Kpnb1 |
| 17002 | 3 | 4 | | | | IV-1 | Kprp |
| 17003 | 3 | 4 | | | | IV-1 | Kras |
| 17004 | 3 | 4 | | | | IV-1 | Krba1 |
| 17005 | 3 | 4 | | | | IV-1 | Krit1 |
| 17006 | 3 | 4 | | | | IV-1 | Krr1 |
| 17007 | 3 | 4 | | | | IV-1 | Krt12 |
| 17008 | 3 | 4 | | | | IV-1 | Krt2 |
| 17009 | 3 | 4 | | | | IV-1 | Krt222 |
| 17010 | 3 | 4 | | | | IV-1 | Krt24 |
| 17011 | 3 | 4 | | | | IV-1 | Krt26 |
| 17012 | 3 | 4 | | | | IV-1 | Krt28 |
| 17013 | 3 | 4 | | | | IV-1 | Krt31 |
| 17014 | 3 | 4 | | | | IV-1 | Krt33a |
| 17015 | 3 | 4 | | | | IV-1 | Krt34 |
| 17016 | 3 | 4 | | | | IV-1 | Krt36 |
| 17017 | 3 | 4 | | | | IV-1 | Krt73 |
| 17018 | 3 | 4 | | | | IV-1 | Krt74 |
| 17019 | 3 | 4 | | | | IV-1 | Krt76 |
| 17020 | 3 | 4 | | | | IV-1 | Krt81 |
| 17021 | 3 | 4 | | | | IV-1 | Krt82 |
| 17022 | 3 | 4 | | | | IV-1 | Krt83 |
| 17023 | 3 | 4 | | | | IV-1 | Krt84 |
| 17024 | 3 | 4 | | | | IV-1 | Krt85 |
| 17025 | 3 | 4 | | | | IV-1 | Krt86 |
| 17026 | 3 | 4 | | | | IV-1 | Krtap10-4 |
| 17027 | 3 | 4 | | | | IV-1 | Krtap11-1 |
| 17028 | 3 | 4 | | | | IV-1 | Krtap12-1 |
| 17029 | 3 | 4 | | | | IV-1 | Krtap13 |
| 17030 | 3 | 4 | | | | IV-1 | Krtap1-3 |
| 17031 | 3 | 4 | | | | IV-1 | Krtap1-4 |
| 17032 | 3 | 4 | | | | IV-1 | Krtap19-9b |
| 17033 | 3 | 4 | | | | IV-1 | Krtap20-2 |
| 17034 | 3 | 4 | | | | IV-1 | Krtap2-4 |
| 17035 | 3 | 4 | | | | IV-1 | Krtap31-1 |
| 17036 | 3 | 4 | | | | IV-1 | Krtap31-2 |
| 17037 | 3 | 4 | | | | IV-1 | Krtap4-13 |
| 17038 | 3 | 4 | | | | IV-1 | Krtap5-4 |
| 17039 | 3 | 4 | | | | IV-1 | Krtcap3 |
| 17040 | 3 | 4 | | | | IV-1 | Krtdap |
| 17041 | 3 | 4 | | | | IV-1 | Ksr2 |
| 17042 | 3 | 4 | | | | IV-1 | Ktn1 |
| 17043 | 3 | 4 | | | | IV-1 | L1td1 |
| 17044 | 3 | 4 | | | | IV-1 | L3mbtl1 |
| 17045 | 3 | 4 | | | | IV-1 | Lactb |
| 17046 | 3 | 4 | | | | IV-1 | Lactb2 |
| 17047 | 3 | 4 | | | | IV-1 | Lactbl1 |
| 17048 | 3 | 4 | | | | IV-1 | Lad1 |
| 17049 | 3 | 4 | | | | IV-1 | Laiba |
| 17050 | 3 | 4 | | | | IV-1 | Lamb2 |
| 17051 | 3 | 4 | | | | IV-1 | Lamc2 |
| 17052 | 3 | 4 | | | | IV-1 | Lamp1 |
| 17053 | 3 | 4 | | | | IV-1 | Lamp2 |
| 17054 | 3 | 4 | | | | IV-1 | Lamp5 |
| 17055 | 3 | 4 | | | | IV-1 | Lamtor2 |
| 17056 | 3 | 4 | | | | IV-1 | Lamtor3 |
| 17057 | 3 | 4 | | | | IV-1 | Lao1 |
| 17058 | 3 | 4 | | | | IV-1 | Laptm4a |
| 17059 | 3 | 4 | | | | IV-1 | Laptm4b |
| 17060 | 3 | 4 | | | | IV-1 | Large |
| 17061 | 3 | 4 | | | | IV-1 | Larp6 |
| 17062 | 3 | 4 | | | | IV-1 | Lars |
| 17063 | 3 | 4 | | | | IV-1 | Las1l |
| 17064 | 3 | 4 | | | | IV-1 | Lats1 |
| 17065 | 3 | 4 | | | | IV-1 | Lats2 |
| 17066 | 3 | 4 | | | | IV-1 | Lbx1 |
| 17067 | 3 | 4 | | | | IV-1 | Lcat |
| 17068 | 3 | 4 | | | | IV-1 | Lce1d |
| 17069 | 3 | 4 | | | | IV-1 | Lce1e |
| 17070 | 3 | 4 | | | | IV-1 | Lce1g |
| 17071 | 3 | 4 | | | | IV-1 | Lce1h |
| 17072 | 3 | 4 | | | | IV-1 | Lce1i |
| 17073 | 3 | 4 | | | | IV-1 | Lce1j |
| 17074 | 3 | 4 | | | | IV-1 | Lce1k |
| 17075 | 3 | 4 | | | | IV-1 | Lce1l |
| 17076 | 3 | 4 | | | | IV-1 | Lcmt2 |
| 17077 | 3 | 4 | | | | IV-1 | Lcn10 |
| 17078 | 3 | 4 | | | | IV-1 | Lcn11 |
| 17079 | 3 | 4 | | | | IV-1 | Lcn12 |
| 17080 | 3 | 4 | | | | IV-1 | Lcn3 |
| 17081 | 3 | 4 | | | | IV-1 | Lcn4 |
| 17082 | 3 | 4 | | | | IV-1 | Lcn9 |
| 17083 | 3 | 4 | | | | IV-1 | Ldlrad2 |
| 17084 | 3 | 4 | | | | IV-1 | Ldoc1 |
| 17085 | 3 | 4 | | | | IV-1 | Lect1 |
| 17086 | 3 | 4 | | | | IV-1 | Lefty2 |
| 17087 | 3 | 4 | | | | IV-1 | Lemd1 |
| 17088 | 3 | 4 | | | | IV-1 | Lemd3 |
| 17089 | 3 | 4 | | | | IV-1 | Leng1 |
| 17090 | 3 | 4 | | | | IV-1 | Leo1 |
| 17091 | 3 | 4 | | | | IV-1 | Lep |
| 17092 | 3 | 4 | | | | IV-1 | Leprel2 |
| 17093 | 3 | 4 | | | | IV-1 | Leprotl1 |
| 17094 | 3 | 4 | | | | IV-1 | Letm1 |
| 17095 | 3 | 4 | | | | IV-1 | Letmd1 |
| 17096 | 3 | 4 | | | | IV-1 | Lgals6 |
| 17097 | 3 | 4 | | | | IV-1 | Lgals8 |
| 17098 | 3 | 4 | | | | IV-1 | Lgi1 |
| 17099 | 3 | 4 | | | | IV-1 | Lgi3 |
| 17100 | 3 | 4 | | | | IV-1 | Lgsn |
| 17101 | 3 | 4 | | | | IV-1 | Lhb |
| 17102 | 3 | 4 | | | | IV-1 | Lhcgr |
| 17103 | 3 | 4 | | | | IV-1 | Lhfp |
| 17104 | 3 | 4 | | | | IV-1 | Lhfpl1 |
| 17105 | 3 | 4 | | | | IV-1 | Lhfpl4 |
| 17106 | 3 | 4 | | | | IV-1 | Lhx1 |
| 17107 | 3 | 4 | | | | IV-1 | Lhx1os |
| 17108 | 3 | 4 | | | | IV-1 | Lhx2 |
| 17109 | 3 | 4 | | | | IV-1 | Lhx3 |
| 17110 | 3 | 4 | | | | IV-1 | Lhx5 |
| 17111 | 3 | 4 | | | | IV-1 | Lhx8 |
| 17112 | 3 | 4 | | | | IV-1 | Lhx9 |
| 17113 | 3 | 4 | | | | IV-1 | Lilra5 |
| 17114 | 3 | 4 | | | | IV-1 | Lim2 |
| 17115 | 3 | 4 | | | | IV-1 | Limd2 |
| 17116 | 3 | 4 | | | | IV-1 | Lime1 |
| 17117 | 3 | 4 | | | | IV-1 | Limk2 |
| 17118 | 3 | 4 | | | | IV-1 | Lims1 |
| 17119 | 3 | 4 | | | | IV-1 | Lims2 |
| 17120 | 3 | 4 | | | | IV-1 | Lin28a |
| 17121 | 3 | 4 | | | | IV-1 | Lin52 |
| 17122 | 3 | 4 | | | | IV-1 | Lin7a |
| 17123 | 3 | 4 | | | | IV-1 | Lin7b |
| 17124 | 3 | 4 | | | | IV-1 | Lin7c |
| 17125 | 3 | 4 | | | | IV-1 | Lincrna-cox2 |
| 17126 | 3 | 4 | | | | IV-1 | Lingo2 |
| 17127 | 3 | 4 | | | | IV-1 | Lingo4 |
| 17128 | 3 | 4 | | | | IV-1 | Lipf |
| 17129 | 3 | 4 | | | | IV-1 | Liph |
| 17130 | 3 | 4 | | | | IV-1 | Lipi |
| 17131 | 3 | 4 | | | | IV-1 | Lipm |
| 17132 | 3 | 4 | | | | IV-1 | Lipo1 |
| 17133 | 3 | 4 | | | | IV-1 | Litaf |
| 17134 | 3 | 4 | | | | IV-1 | Lix1l |
| 17135 | 3 | 4 | | | | IV-1 | Llgl1 |
| 17136 | 3 | 4 | | | | IV-1 | Llph |
| 17137 | 3 | 4 | | | | IV-1 | Lman1 |
| 17138 | 3 | 4 | | | | IV-1 | Lman1l |
| 17139 | 3 | 4 | | | | IV-1 | Lmbr1 |
| 17140 | 3 | 4 | | | | IV-1 | Lmbrd1 |
| 17141 | 3 | 4 | | | | IV-1 | Lmf1 |
| 17142 | 3 | 4 | | | | IV-1 | Lmf2 |
| 17143 | 3 | 4 | | | | IV-1 | Lmo3 |
| 17144 | 3 | 4 | | | | IV-1 | Lmo4 |
| 17145 | 3 | 4 | | | | IV-1 | Lmtk3 |
| 17146 | 3 | 4 | | | | IV-1 | Lmx1a |
| 17147 | 3 | 4 | | | | IV-1 | Lmx1b |
| 17148 | 3 | 4 | | | | IV-1 | Lnp |
| 17149 | 3 | 4 | | | | IV-1 | Lnx1 |
| 17150 | 3 | 4 | | | | IV-1 | LOC100043315 |
| 17151 | 3 | 4 | | | | IV-1 | LOC100502896 |
| 17152 | 3 | 4 | | | | IV-1 | LOC100503280 |
| 17153 | 3 | 4 | | | | IV-1 | LOC100861615 |
| 17154 | 3 | 4 | | | | IV-1 | LOC100862268 |
| 17155 | 3 | 4 | | | | IV-1 | LOC101055769 |
| 17156 | 3 | 4 | | | | IV-1 | LOC101056043 |
| 17157 | 3 | 4 | | | | IV-1 | LOC102308570 |
| 17158 | 3 | 4 | | | | IV-1 | LOC102633315 |
| 17159 | 3 | 4 | | | | IV-1 | LOC102634401 |
| 17160 | 3 | 4 | | | | IV-1 | LOC102634753 |
| 17161 | 3 | 4 | | | | IV-1 | LOC171588 |
| 17162 | 3 | 4 | | | | IV-1 | Lonrf3 |
| 17163 | 3 | 4 | | | | IV-1 | Loxhd1 |
| 17164 | 3 | 4 | | | | IV-1 | Loxl3 |
| 17165 | 3 | 4 | | | | IV-1 | Lpar1 |
| 17166 | 3 | 4 | | | | IV-1 | Lpar4 |
| 17167 | 3 | 4 | | | | IV-1 | Lpcat2b |

Fig. 43 - 102

| | | | | | | | |
|---|---|---|---|---|---|---|---|
| 17168 | 3 | 4 | | | | IV-1 | Lpcat4 |
| 17169 | 3 | 4 | | | | IV-1 | Lphn1 |
| 17170 | 3 | 4 | | | | IV-1 | Lphn2 |
| 17171 | 3 | 4 | | | | IV-1 | Lpin2 |
| 17172 | 3 | 4 | | | | IV-1 | Lrch2 |
| 17173 | 3 | 4 | | | | IV-1 | Lrcol1 |
| 17174 | 3 | 4 | | | | IV-1 | Lrfn1 |
| 17175 | 3 | 4 | | | | IV-1 | Lrfn2 |
| 17176 | 3 | 4 | | | | IV-1 | Lrfn4 |
| 17177 | 3 | 4 | | | | IV-1 | Lrfn5 |
| 17178 | 3 | 4 | | | | IV-1 | Lrguk |
| 17179 | 3 | 4 | | | | IV-1 | Lrig1 |
| 17180 | 3 | 4 | | | | IV-1 | Lrig2 |
| 17181 | 3 | 4 | | | | IV-1 | Lrit1 |
| 17182 | 3 | 4 | | | | IV-1 | Lrit3 |
| 17183 | 3 | 4 | | | | IV-1 | Lrp2bp |
| 17184 | 3 | 4 | | | | IV-1 | Lrp4 |
| 17185 | 3 | 4 | | | | IV-1 | Lrpap1 |
| 17186 | 3 | 4 | | | | IV-1 | Lrpprc |
| 17187 | 3 | 4 | | | | IV-1 | Lrr1 |
| 17188 | 3 | 4 | | | | IV-1 | Lrrc10 |
| 17189 | 3 | 4 | | | | IV-1 | Lrrc14 |
| 17190 | 3 | 4 | | | | IV-1 | Lrrc16b |
| 17191 | 3 | 4 | | | | IV-1 | Lrrc19 |
| 17192 | 3 | 4 | | | | IV-1 | Lrrc28 |
| 17193 | 3 | 4 | | | | IV-1 | Lrrc38 |
| 17194 | 3 | 4 | | | | IV-1 | Lrrc3b |
| 17195 | 3 | 4 | | | | IV-1 | Lrrc41 |
| 17196 | 3 | 4 | | | | IV-1 | Lrrc45 |
| 17197 | 3 | 4 | | | | IV-1 | Lrrc47 |
| 17198 | 3 | 4 | | | | IV-1 | Lrrc48 |
| 17199 | 3 | 4 | | | | IV-1 | Lrrc49 |
| 17200 | 3 | 4 | | | | IV-1 | Lrrc4c |
| 17201 | 3 | 4 | | | | IV-1 | Lrrc55 |
| 17202 | 3 | 4 | | | | IV-1 | Lrrc56 |
| 17203 | 3 | 4 | | | | IV-1 | Lrrc58 |
| 17204 | 3 | 4 | | | | IV-1 | Lrrc59 |
| 17205 | 3 | 4 | | | | IV-1 | Lrrc6 |
| 17206 | 3 | 4 | | | | IV-1 | Lrrc63 |
| 17207 | 3 | 4 | | | | IV-1 | Lrrc66 |
| 17208 | 3 | 4 | | | | IV-1 | Lrrc69 |
| 17209 | 3 | 4 | | | | IV-1 | Lrrc7 |
| 17210 | 3 | 4 | | | | IV-1 | Lrrc72 |
| 17211 | 3 | 4 | | | | IV-1 | Lrrc8e |
| 17212 | 3 | 4 | | | | IV-1 | Lrrc9 |
| 17213 | 3 | 4 | | | | IV-1 | Lrrcc1 |
| 17214 | 3 | 4 | | | | IV-1 | Lrrd1 |
| 17215 | 3 | 4 | | | | IV-1 | Lrrfip1 |
| 17216 | 3 | 4 | | | | IV-1 | Lrriq1 |
| 17217 | 3 | 4 | | | | IV-1 | Lrriq4 |
| 17218 | 3 | 4 | | | | IV-1 | Lrrtm1 |
| 17219 | 3 | 4 | | | | IV-1 | Lrrtm2 |
| 17220 | 3 | 4 | | | | IV-1 | Lrrtm3 |
| 17221 | 3 | 4 | | | | IV-1 | Lrrtm4 |
| 17222 | 3 | 4 | | | | IV-1 | Lrsam1 |
| 17223 | 3 | 4 | | | | IV-1 | Lsm1 |
| 17224 | 3 | 4 | | | | IV-1 | Lsm12 |
| 17225 | 3 | 4 | | | | IV-1 | Lsm14a |
| 17226 | 3 | 4 | | | | IV-1 | Lsm14b |
| 17227 | 3 | 4 | | | | IV-1 | Lta |
| 17228 | 3 | 4 | | | | IV-1 | Lta4h |
| 17229 | 3 | 4 | | | | IV-1 | Ltv1 |
| 17230 | 3 | 4 | | | | IV-1 | Luc7l |
| 17231 | 3 | 4 | | | | IV-1 | Luc7l2 |
| 17232 | 3 | 4 | | | | IV-1 | Luzp2 |
| 17233 | 3 | 4 | | | | IV-1 | Ly6e |
| 17234 | 3 | 4 | | | | IV-1 | Ly6g5c |
| 17235 | 3 | 4 | | | | IV-1 | Ly75 |
| 17236 | 3 | 4 | | | | IV-1 | Lyg2 |
| 17237 | 3 | 4 | | | | IV-1 | Lypd1 |
| 17238 | 3 | 4 | | | | IV-1 | Lypd5 |
| 17239 | 3 | 4 | | | | IV-1 | Lypd6 |
| 17240 | 3 | 4 | | | | IV-1 | Lypla1 |
| 17241 | 3 | 4 | | | | IV-1 | Lyrm2 |
| 17242 | 3 | 4 | | | | IV-1 | Lyrm5 |
| 17243 | 3 | 4 | | | | IV-1 | Lysmd4 |
| 17244 | 3 | 4 | | | | IV-1 | Lyz2 |
| 17245 | 3 | 4 | | | | IV-1 | Lyzl1 |
| 17246 | 3 | 4 | | | | IV-1 | Lyzl4 |
| 17247 | 3 | 4 | | | | IV-1 | Lyzl4os |
| 17248 | 3 | 4 | | | | IV-1 | Lyzl6 |
| 17249 | 3 | 4 | | | | IV-1 | Lzts2 |
| 17250 | 3 | 4 | | | | IV-1 | M1ap |
| 17251 | 3 | 4 | | | | IV-1 | M6pr |
| 17252 | 3 | 4 | | | | IV-1 | Maats1 |
| 17253 | 3 | 4 | | | | IV-1 | Mab21l1 |
| 17254 | 3 | 4 | | | | IV-1 | Mab21l2 |
| 17255 | 3 | 4 | | | | IV-1 | Macf1 |
| 17256 | 3 | 4 | | | | IV-1 | Macrod2 |
| 17257 | 3 | 4 | | | | IV-1 | Madd |
| 17258 | 3 | 4 | | | | IV-1 | Maea |
| 17259 | 3 | 4 | | | | IV-1 | Mafk |
| 17260 | 3 | 4 | | | | IV-1 | Mag |
| 17261 | 3 | 4 | | | | IV-1 | Magea1 |
| 17262 | 3 | 4 | | | | IV-1 | Magea10 |
| 17263 | 3 | 4 | | | | IV-1 | Magea2 |
| 17264 | 3 | 4 | | | | IV-1 | Magea3 |
| 17265 | 3 | 4 | | | | IV-1 | Magea4 |
| 17266 | 3 | 4 | | | | IV-1 | Magea5 |
| 17267 | 3 | 4 | | | | IV-1 | Magea8 |
| 17268 | 3 | 4 | | | | IV-1 | Mageb16-ps1 |
| 17269 | 3 | 4 | | | | IV-1 | Mageb4 |
| 17270 | 3 | 4 | | | | IV-1 | Magel2 |
| 17271 | 3 | 4 | | | | IV-1 | Magi2 |
| 17272 | 3 | 4 | | | | IV-1 | Magt1 |
| 17273 | 3 | 4 | | | | IV-1 | Mak |
| 17274 | 3 | 4 | | | | IV-1 | Mak16 |
| 17275 | 3 | 4 | | | | IV-1 | Mall |
| 17276 | 3 | 4 | | | | IV-1 | Malt1 |
| 17277 | 3 | 4 | | | | IV-1 | Mamdc2 |
| 17278 | 3 | 4 | | | | IV-1 | Mamdc4 |
| 17279 | 3 | 4 | | | | IV-1 | Maml1 |
| 17280 | 3 | 4 | | | | IV-1 | Maml2 |
| 17281 | 3 | 4 | | | | IV-1 | Man1a2 |
| 17282 | 3 | 4 | | | | IV-1 | Man1c1 |
| 17283 | 3 | 4 | | | | IV-1 | Man2b1 |
| 17284 | 3 | 4 | | | | IV-1 | Man2c1 |
| 17285 | 3 | 4 | | | | IV-1 | Manba |
| 17286 | 3 | 4 | | | | IV-1 | Manea |
| 17287 | 3 | 4 | | | | IV-1 | Maneal |
| 17288 | 3 | 4 | | | | IV-1 | Manr |
| 17289 | 3 | 4 | | | | IV-1 | Mansc4 |
| 17290 | 3 | 4 | | | | IV-1 | Map10 |
| 17291 | 3 | 4 | | | | IV-1 | Map1lc3b |
| 17292 | 3 | 4 | | | | IV-1 | Map1s |
| 17293 | 3 | 4 | | | | IV-1 | Map2k1 |
| 17294 | 3 | 4 | | | | IV-1 | Map2k4 |
| 17295 | 3 | 4 | | | | IV-1 | Map2k7 |
| 17296 | 3 | 4 | | | | IV-1 | Map3k11 |
| 17297 | 3 | 4 | | | | IV-1 | Map3k15 |
| 17298 | 3 | 4 | | | | IV-1 | Map3k7 |
| 17299 | 3 | 4 | | | | IV-1 | Map3k9 |
| 17300 | 3 | 4 | | | | IV-1 | Map4 |
| 17301 | 3 | 4 | | | | IV-1 | Map4k3 |
| 17302 | 3 | 4 | | | | IV-1 | Map4k4 |
| 17303 | 3 | 4 | | | | IV-1 | Map4k5 |
| 17304 | 3 | 4 | | | | IV-1 | Map7d1 |
| 17305 | 3 | 4 | | | | IV-1 | Map7d2 |
| 17306 | 3 | 4 | | | | IV-1 | Map9 |
| 17307 | 3 | 4 | | | | IV-1 | Mapk1 |
| 17308 | 3 | 4 | | | | IV-1 | Mapk14 |
| 17309 | 3 | 4 | | | | IV-1 | Mapk1ip1l |
| 17310 | 3 | 4 | | | | IV-1 | Mapk7 |
| 17311 | 3 | 4 | | | | IV-1 | Mapk8 |
| 17312 | 3 | 4 | | | | IV-1 | Mapk8ip3 |
| 17313 | 3 | 4 | | | | IV-1 | Mapk9 |
| 17314 | 3 | 4 | | | | IV-1 | Mapkapk2 |
| 17315 | 3 | 4 | | | | IV-1 | Mapkapk5 |
| 17316 | 3 | 4 | | | | IV-1 | Mapre1 |
| 17317 | 3 | 4 | | | | IV-1 | Mapre3 |
| 17318 | 3 | 4 | | | | IV-1 | March5 |
| 17319 | 3 | 4 | | | | IV-1 | March8 |
| 17320 | 3 | 4 | | | | IV-1 | Marcks |
| 17321 | 3 | 4 | | | | IV-1 | Mark1 |
| 17322 | 3 | 4 | | | | IV-1 | Mark2 |
| 17323 | 3 | 4 | | | | IV-1 | Mark3 |
| 17324 | 3 | 4 | | | | IV-1 | Mars |
| 17325 | 3 | 4 | | | | IV-1 | Marveld1 |
| 17326 | 3 | 4 | | | | IV-1 | Mas1 |
| 17327 | 3 | 4 | | | | IV-1 | Masp1 |
| 17328 | 3 | 4 | | | | IV-1 | Masp2 |
| 17329 | 3 | 4 | | | | IV-1 | Mast3 |
| 17330 | 3 | 4 | | | | IV-1 | Mastl |
| 17331 | 3 | 4 | | | | IV-1 | Mat2a |
| 17332 | 3 | 4 | | | | IV-1 | Mat2b |
| 17333 | 3 | 4 | | | | IV-1 | Matn1 |
| 17334 | 3 | 4 | | | | IV-1 | Matn3 |
| 17335 | 3 | 4 | | | | IV-1 | Matr3 |
| 17336 | 3 | 4 | | | | IV-1 | Mavs |
| 17337 | 3 | 4 | | | | IV-1 | Max |

Fig. 43 - 103

| | | | | | | | |
|---|---|---|---|---|---|---|---|
| 17338 | 3 | 4 | | | | IV-1 | Mb21d1 |
| 17339 | 3 | 4 | | | | IV-1 | Mb21d2 |
| 17340 | 3 | 4 | | | | IV-1 | Mbd2 |
| 17341 | 3 | 4 | | | | IV-1 | Mbd3 |
| 17342 | 3 | 4 | | | | IV-1 | Mbd3l2 |
| 17343 | 3 | 4 | | | | IV-1 | Mbd4 |
| 17344 | 3 | 4 | | | | IV-1 | Mblac2 |
| 17345 | 3 | 4 | | | | IV-1 | Mbnl1 |
| 17346 | 3 | 4 | | | | IV-1 | Mbnl3 |
| 17347 | 3 | 4 | | | | IV-1 | Mboat4 |
| 17348 | 3 | 4 | | | | IV-1 | Mboat7 |
| 17349 | 3 | 4 | | | | IV-1 | Mbtps2 |
| 17350 | 3 | 4 | | | | IV-1 | Mc2r |
| 17351 | 3 | 4 | | | | IV-1 | Mc3r |
| 17352 | 3 | 4 | | | | IV-1 | Mc4r |
| 17353 | 3 | 4 | | | | IV-1 | Mcam |
| 17354 | 3 | 4 | | | | IV-1 | Mccc1os |
| 17355 | 3 | 4 | | | | IV-1 | Mcf2 |
| 17356 | 3 | 4 | | | | IV-1 | Mcidas |
| 17357 | 3 | 4 | | | | IV-1 | Mcl1 |
| 17358 | 3 | 4 | | | | IV-1 | Mcm7 |
| 17359 | 3 | 4 | | | | IV-1 | Mcmdc2 |
| 17360 | 3 | 4 | | | | IV-1 | Mcpt-ps1 |
| 17361 | 3 | 4 | | | | IV-1 | Mcur1 |
| 17362 | 3 | 4 | | | | IV-1 | Mdfic |
| 17363 | 3 | 4 | | | | IV-1 | Mdga1 |
| 17364 | 3 | 4 | | | | IV-1 | Mdga2 |
| 17365 | 3 | 4 | | | | IV-1 | Mdh1b |
| 17366 | 3 | 4 | | | | IV-1 | Mdk |
| 17367 | 3 | 4 | | | | IV-1 | Mdp1 |
| 17368 | 3 | 4 | | | | IV-1 | Me1 |
| 17369 | 3 | 4 | | | | IV-1 | Me2 |
| 17370 | 3 | 4 | | | | IV-1 | Mea1 |
| 17371 | 3 | 4 | | | | IV-1 | Mecom |
| 17372 | 3 | 4 | | | | IV-1 | Med1 |
| 17373 | 3 | 4 | | | | IV-1 | Med12l |
| 17374 | 3 | 4 | | | | IV-1 | Med15 |
| 17375 | 3 | 4 | | | | IV-1 | Med16 |
| 17376 | 3 | 4 | | | | IV-1 | Med17 |
| 17377 | 3 | 4 | | | | IV-1 | Med20 |
| 17378 | 3 | 4 | | | | IV-1 | Med22 |
| 17379 | 3 | 4 | | | | IV-1 | Med23 |
| 17380 | 3 | 4 | | | | IV-1 | Med24 |
| 17381 | 3 | 4 | | | | IV-1 | Med25 |
| 17382 | 3 | 4 | | | | IV-1 | Med26 |
| 17383 | 3 | 4 | | | | IV-1 | Med7 |
| 17384 | 3 | 4 | | | | IV-1 | Med8 |
| 17385 | 3 | 4 | | | | IV-1 | Mef2a |
| 17386 | 3 | 4 | | | | IV-1 | Megf10 |
| 17387 | 3 | 4 | | | | IV-1 | Megf11 |
| 17388 | 3 | 4 | | | | IV-1 | Mei1 |
| 17389 | 3 | 4 | | | | IV-1 | Mei4 |
| 17390 | 3 | 4 | | | | IV-1 | Meiob |
| 17391 | 3 | 4 | | | | IV-1 | Meis2 |
| 17392 | 3 | 4 | | | | IV-1 | Meis3 |
| 17393 | 3 | 4 | | | | IV-1 | Memo1 |
| 17394 | 3 | 4 | | | | IV-1 | Men1 |
| 17395 | 3 | 4 | | | | IV-1 | Meox2 |
| 17396 | 3 | 4 | | | | IV-1 | Mep1a |
| 17397 | 3 | 4 | | | | IV-1 | Mep1b |
| 17398 | 3 | 4 | | | | IV-1 | Mepce |
| 17399 | 3 | 4 | | | | IV-1 | Mepe |
| 17400 | 3 | 4 | | | | IV-1 | Mesdc1 |
| 17401 | 3 | 4 | | | | IV-1 | Mesdc2 |
| 17402 | 3 | 4 | | | | IV-1 | Mesp2 |
| 17403 | 3 | 4 | | | | IV-1 | Metap1 |
| 17404 | 3 | 4 | | | | IV-1 | Mettl11b |
| 17405 | 3 | 4 | | | | IV-1 | Mettl14 |
| 17406 | 3 | 4 | | | | IV-1 | Mettl15 |
| 17407 | 3 | 4 | | | | IV-1 | Mettl16 |
| 17408 | 3 | 4 | | | | IV-1 | Mettl21a |
| 17409 | 3 | 4 | | | | IV-1 | Mettl21e |
| 17410 | 3 | 4 | | | | IV-1 | Mettl25 |
| 17411 | 3 | 4 | | | | IV-1 | Mettl6 |
| 17412 | 3 | 4 | | | | IV-1 | Mettl7a2Higd1c |
| 17413 | 3 | 4 | | | | IV-1 | Mettl9 |
| 17414 | 3 | 4 | | | | IV-1 | Mex3d |
| 17415 | 3 | 4 | | | | IV-1 | Mfap1a |
| 17416 | 3 | 4 | | | | IV-1 | Mfap1b |
| 17417 | 3 | 4 | | | | IV-1 | Mfap3 |
| 17418 | 3 | 4 | | | | IV-1 | Mff |
| 17419 | 3 | 4 | | | | IV-1 | Mfi2 |
| 17420 | 3 | 4 | | | | IV-1 | Mfn1 |
| 17421 | 3 | 4 | | | | IV-1 | Mfn2 |
| 17422 | 3 | 4 | | | | IV-1 | Mfsd1 |
| 17423 | 3 | 4 | | | | IV-1 | Mfsd10 |
| 17424 | 3 | 4 | | | | IV-1 | Mfsd5 |
| 17425 | 3 | 4 | | | | IV-1 | Mfsd6l |
| 17426 | 3 | 4 | | | | IV-1 | Mfsd7b |
| 17427 | 3 | 4 | | | | IV-1 | Mfsd8 |
| 17428 | 3 | 4 | | | | IV-1 | Mgarp |
| 17429 | 3 | 4 | | | | IV-1 | Mgat1 |
| 17430 | 3 | 4 | | | | IV-1 | Mgat2 |
| 17431 | 3 | 4 | | | | IV-1 | Mgat4b |
| 17432 | 3 | 4 | | | | IV-1 | Mgat4c |
| 17433 | 3 | 4 | | | | IV-1 | Mgat5b |
| 17434 | 3 | 4 | | | | IV-1 | Mgea5 |
| 17435 | 3 | 4 | | | | IV-1 | Mgl2 |
| 17436 | 3 | 4 | | | | IV-1 | Mia3 |
| 17437 | 3 | 4 | | | | IV-1 | Miat |
| 17438 | 3 | 4 | | | | IV-1 | Mical1 |
| 17439 | 3 | 4 | | | | IV-1 | Micall1 |
| 17440 | 3 | 4 | | | | IV-1 | Micu1 |
| 17441 | 3 | 4 | | | | IV-1 | Midn |
| 17442 | 3 | 4 | | | | IV-1 | Mief1 |
| 17443 | 3 | 4 | | | | IV-1 | Mief2 |
| 17444 | 3 | 4 | | | | IV-1 | Mier3 |
| 17445 | 3 | 4 | | | | IV-1 | Miip |
| 17446 | 3 | 4 | | | | IV-1 | Mill1 |
| 17447 | 3 | 4 | | | | IV-1 | Mink1 |
| 17448 | 3 | 4 | | | | IV-1 | Mip |
| 17449 | 3 | 4 | | | | IV-1 | Mipep |
| 17450 | 3 | 4 | | | | IV-1 | Mir100 |
| 17451 | 3 | 4 | | | | IV-1 | Mir101a |
| 17452 | 3 | 4 | | | | IV-1 | Mir101c |
| 17453 | 3 | 4 | | | | IV-1 | Mir103-1 |
| 17454 | 3 | 4 | | | | IV-1 | Mir103-2 |
| 17455 | 3 | 4 | | | | IV-1 | Mir130a |
| 17456 | 3 | 4 | | | | IV-1 | Mir147 |
| 17457 | 3 | 4 | | | | IV-1 | Mir181c |
| 17458 | 3 | 4 | | | | IV-1 | Mir1963 |
| 17459 | 3 | 4 | | | | IV-1 | Mir218-1 |
| 17460 | 3 | 4 | | | | IV-1 | Mir26a-1 |
| 17461 | 3 | 4 | | | | IV-1 | Mir6335 |
| 17462 | 3 | 4 | | | | IV-1 | Mir6369 |
| 17463 | 3 | 4 | | | | IV-1 | Mir687 |
| 17464 | 3 | 4 | | | | IV-1 | Mir7035 |
| 17465 | 3 | 4 | | | | IV-1 | Mir8097 |
| 17466 | 3 | 4 | | | | IV-1 | Mir8100 |
| 17467 | 3 | 4 | | | | IV-1 | Mir8104 |
| 17468 | 3 | 4 | | | | IV-1 | Mir8105 |
| 17469 | 3 | 4 | | | | IV-1 | Mir8114 |
| 17470 | 3 | 4 | | | | IV-1 | Mirlet7c-1 |
| 17471 | 3 | 4 | | | | IV-1 | Mirlet7c-2 |
| 17472 | 3 | 4 | | | | IV-1 | Mirlet7f-2 |
| 17473 | 3 | 4 | | | | IV-1 | Mirlet7j |
| 17474 | 3 | 4 | | | | IV-1 | Mixl1 |
| 17475 | 3 | 4 | | | | IV-1 | Mkks |
| 17476 | 3 | 4 | | | | IV-1 | Mki1 |
| 17477 | 3 | 4 | | | | IV-1 | Mkln1 |
| 17478 | 3 | 4 | | | | IV-1 | Mknk1 |
| 17479 | 3 | 4 | | | | IV-1 | Mkrn2 |
| 17480 | 3 | 4 | | | | IV-1 | Mkrn3 |
| 17481 | 3 | 4 | | | | IV-1 | Mlana |
| 17482 | 3 | 4 | | | | IV-1 | Mlc1 |
| 17483 | 3 | 4 | | | | IV-1 | Mlf2 |
| 17484 | 3 | 4 | | | | IV-1 | Mlh1 |
| 17485 | 3 | 4 | | | | IV-1 | Mlh3 |
| 17486 | 3 | 4 | | | | IV-1 | Mlt10 |
| 17487 | 3 | 4 | | | | IV-1 | Mlst8 |
| 17488 | 3 | 4 | | | | IV-1 | Mlx |
| 17489 | 3 | 4 | | | | IV-1 | Mmab |
| 17490 | 3 | 4 | | | | IV-1 | Mmadhc |
| 17491 | 3 | 4 | | | | IV-1 | Mmd |
| 17492 | 3 | 4 | | | | IV-1 | Mme |
| 17493 | 3 | 4 | | | | IV-1 | Mmel1 |
| 17494 | 3 | 4 | | | | IV-1 | Mmgt1 |
| 17495 | 3 | 4 | | | | IV-1 | Mmp12 |
| 17496 | 3 | 4 | | | | IV-1 | Mmp1a |
| 17497 | 3 | 4 | | | | IV-1 | Mmp1b |
| 17498 | 3 | 4 | | | | IV-1 | Mmp20 |
| 17499 | 3 | 4 | | | | IV-1 | Mmp21 |
| 17500 | 3 | 4 | | | | IV-1 | Mmp27 |
| 17501 | 3 | 4 | | | | IV-1 | Mms22l |
| 17502 | 3 | 4 | | | | IV-1 | Mnt |
| 17503 | 3 | 4 | | | | IV-1 | Mnx1 |
| 17504 | 3 | 4 | | | | IV-1 | Mob2 |
| 17505 | 3 | 4 | | | | IV-1 | Mob3b |
| 17506 | 3 | 4 | | | | IV-1 | Mob3c |
| 17507 | 3 | 4 | | | | IV-1 | Mob4 |

Fig. 43 - 104

| | | | | | | | |
|---|---|---|---|---|---|---|---|
| 17508 | 3 | 4 | | | IV-1 | Mobp |
| 17509 | 3 | 4 | | | IV-1 | Mocs1 |
| 17510 | 3 | 4 | | | IV-1 | Mog |
| 17511 | 3 | 4 | | | IV-1 | Mogat2 |
| 17512 | 3 | 4 | | | IV-1 | Mogs |
| 17513 | 3 | 4 | | | IV-1 | Mok |
| 17514 | 3 | 4 | | | IV-1 | Mon1a |
| 17515 | 3 | 4 | | | IV-1 | Mon2 |
| 17516 | 3 | 4 | | | IV-1 | Morc1 |
| 17517 | 3 | 4 | | | IV-1 | Morc2a |
| 17518 | 3 | 4 | | | IV-1 | Morc2b |
| 17519 | 3 | 4 | | | IV-1 | Morc3 |
| 17520 | 3 | 4 | | | IV-1 | Morn1 |
| 17521 | 3 | 4 | | | IV-1 | Mos |
| 17522 | 3 | 4 | | | IV-1 | Mospd2 |
| 17523 | 3 | 4 | | | IV-1 | Mospd3 |
| 17524 | 3 | 4 | | | IV-1 | Mov10 |
| 17525 | 3 | 4 | | | IV-1 | Moxd2 |
| 17526 | 3 | 4 | | | IV-1 | Mpdu1 |
| 17527 | 3 | 4 | | | IV-1 | Mpdz |
| 17528 | 3 | 4 | | | IV-1 | Mphosph10 |
| 17529 | 3 | 4 | | | IV-1 | Mphosph9 |
| 17530 | 3 | 4 | | | IV-1 | Mpnd |
| 17531 | 3 | 4 | | | IV-1 | Mpp1 |
| 17532 | 3 | 4 | | | IV-1 | Mpp4 |
| 17533 | 3 | 4 | | | IV-1 | Mpp5 |
| 17534 | 3 | 4 | | | IV-1 | Mpped1 |
| 17535 | 3 | 4 | | | IV-1 | Mprip |
| 17536 | 3 | 4 | | | IV-1 | Mptx1 |
| 17537 | 3 | 4 | | | IV-1 | Mptx2 |
| 17538 | 3 | 4 | | | IV-1 | Mpv17 |
| 17539 | 3 | 4 | | | IV-1 | Mrap2 |
| 17540 | 3 | 4 | | | IV-1 | Mre11a |
| 17541 | 3 | 4 | | | IV-1 | Mrgbp |
| 17542 | 3 | 4 | | | IV-1 | Mrgpra1 |
| 17543 | 3 | 4 | | | IV-1 | Mrgpra2a |
| 17544 | 3 | 4 | | | IV-1 | Mrgpra2b |
| 17545 | 3 | 4 | | | IV-1 | Mrgpra3 |
| 17546 | 3 | 4 | | | IV-1 | Mrgpra4 |
| 17547 | 3 | 4 | | | IV-1 | Mrgpra6 |
| 17548 | 3 | 4 | | | IV-1 | Mrgprb1 |
| 17549 | 3 | 4 | | | IV-1 | Mrgprb2 |
| 17550 | 3 | 4 | | | IV-1 | Mrgprx1 |
| 17551 | 3 | 4 | | | IV-1 | Mri1 |
| 17552 | 3 | 4 | | | IV-1 | Mro |
| 17553 | 3 | 4 | | | IV-1 | Mroh1 |
| 17554 | 3 | 4 | | | IV-1 | Mroh4 |
| 17555 | 3 | 4 | | | IV-1 | Mroh5 |
| 17556 | 3 | 4 | | | IV-1 | Mroh6 |
| 17557 | 3 | 4 | | | IV-1 | Mroh8 |
| 17558 | 3 | 4 | | | IV-1 | Mrpl1 |
| 17559 | 3 | 4 | | | IV-1 | Mrpl11 |
| 17560 | 3 | 4 | | | IV-1 | Mrpl17 |
| 17561 | 3 | 4 | | | IV-1 | Mrpl19 |
| 17562 | 3 | 4 | | | IV-1 | Mrpl35 |
| 17563 | 3 | 4 | | | IV-1 | Mrpl37 |
| 17564 | 3 | 4 | | | IV-1 | Mrpl39 |
| 17565 | 3 | 4 | | | IV-1 | Mrpl44 |
| 17566 | 3 | 4 | | | IV-1 | Mrpl49 |
| 17567 | 3 | 4 | | | IV-1 | Mrpl50 |
| 17568 | 3 | 4 | | | IV-1 | Mrpl57 |
| 17569 | 3 | 4 | | | IV-1 | Mrps17 |
| 17570 | 3 | 4 | | | IV-1 | Mrps2 |
| 17571 | 3 | 4 | | | IV-1 | Mrps30 |
| 17572 | 3 | 4 | | | IV-1 | Mrps31 |
| 17573 | 3 | 4 | | | IV-1 | Mrps33 |
| 17574 | 3 | 4 | | | IV-1 | Mrrf |
| 17575 | 3 | 4 | | | IV-1 | Ms4a10 |
| 17576 | 3 | 4 | | | IV-1 | Ms4a13 |
| 17577 | 3 | 4 | | | IV-1 | Ms4a15 |
| 17578 | 3 | 4 | | | IV-1 | Ms4a2 |
| 17579 | 3 | 4 | | | IV-1 | Ms4a5 |
| 17580 | 3 | 4 | | | IV-1 | Ms4a7 |
| 17581 | 3 | 4 | | | IV-1 | Msantd2 |
| 17582 | 3 | 4 | | | IV-1 | Msantd4 |
| 17583 | 3 | 4 | | | IV-1 | Msgn1 |
| 17584 | 3 | 4 | | | IV-1 | Msh2 |
| 17585 | 3 | 4 | | | IV-1 | Msh3 |
| 17586 | 3 | 4 | | | IV-1 | Msh4 |
| 17587 | 3 | 4 | | | IV-1 | Msh5 |
| 17588 | 3 | 4 | | | IV-1 | Msl1 |
| 17589 | 3 | 4 | | | IV-1 | Msl1 |
| 17590 | 3 | 4 | | | IV-1 | Msmb |
| 17591 | 3 | 4 | | | IV-1 | Mst1 |
| 17592 | 3 | 4 | | | IV-1 | Mst1r |
| 17593 | 3 | 4 | | | IV-1 | Msx1os |
| 17594 | 3 | 4 | | | IV-1 | Msx2 |
| 17595 | 3 | 4 | | | IV-1 | Msx3 |
| 17596 | 3 | 4 | | | IV-1 | Mt4 |
| 17597 | 3 | 4 | | | IV-1 | Mtap |
| 17598 | 3 | 4 | | | IV-1 | Mtap7d3 |
| 17599 | 3 | 4 | | | IV-1 | Mtch2 |
| 17600 | 3 | 4 | | | IV-1 | Mtcl1 |
| 17601 | 3 | 4 | | | IV-1 | Mtcp1 |
| 17602 | 3 | 4 | | | IV-1 | Mtdh |
| 17603 | 3 | 4 | | | IV-1 | Mtfmt |
| 17604 | 3 | 4 | | | IV-1 | Mtfr1 |
| 17605 | 3 | 4 | | | IV-1 | Mtfr1l |
| 17606 | 3 | 4 | | | IV-1 | Mthfr |
| 17607 | 3 | 4 | | | IV-1 | Mtif2 |
| 17608 | 3 | 4 | | | IV-1 | Mtl5 |
| 17609 | 3 | 4 | | | IV-1 | Mtmr1 |
| 17610 | 3 | 4 | | | IV-1 | Mtmr10 |
| 17611 | 3 | 4 | | | IV-1 | Mtmr12 |
| 17612 | 3 | 4 | | | IV-1 | Mtmr2 |
| 17613 | 3 | 4 | | | IV-1 | Mtmr3 |
| 17614 | 3 | 4 | | | IV-1 | Mtmr4 |
| 17615 | 3 | 4 | | | IV-1 | Mtmr6 |
| 17616 | 3 | 4 | | | IV-1 | Mtnr1a |
| 17617 | 3 | 4 | | | IV-1 | Mtnr1b |
| 17618 | 3 | 4 | | | IV-1 | Mto1 |
| 17619 | 3 | 4 | | | IV-1 | Mtor |
| 17620 | 3 | 4 | | | IV-1 | Mtpap |
| 17621 | 3 | 4 | | | IV-1 | Mtpn |
| 17622 | 3 | 4 | | | IV-1 | Mtrr |
| 17623 | 3 | 4 | | | IV-1 | Mttp |
| 17624 | 3 | 4 | | | IV-1 | Mtus2 |
| 17625 | 3 | 4 | | | IV-1 | Mtx3 |
| 17626 | 3 | 4 | | | IV-1 | Muc15 |
| 17627 | 3 | 4 | | | IV-1 | Muc19 |
| 17628 | 3 | 4 | | | IV-1 | Muc20 |
| 17629 | 3 | 4 | | | IV-1 | Muc5ac |
| 17630 | 3 | 4 | | | IV-1 | Mucl1 |
| 17631 | 3 | 4 | | | IV-1 | Mup14 |
| 17632 | 3 | 4 | | | IV-1 | Mup16 |
| 17633 | 3 | 4 | | | IV-1 | Mup21 |
| 17634 | 3 | 4 | | | IV-1 | Mup6 |
| 17635 | 3 | 4 | | | IV-1 | Mut |
| 17636 | 3 | 4 | | | IV-1 | Mutyh |
| 17637 | 3 | 4 | | | IV-1 | Mvb12b |
| 17638 | 3 | 4 | | | IV-1 | Mvk |
| 17639 | 3 | 4 | | | IV-1 | Mvp |
| 17640 | 3 | 4 | | | IV-1 | Mxi1 |
| 17641 | 3 | 4 | | | IV-1 | Mxra7 |
| 17642 | 3 | 4 | | | IV-1 | Myadm |
| 17643 | 3 | 4 | | | IV-1 | Mybbp1a |
| 17644 | 3 | 4 | | | IV-1 | Mybpc3 |
| 17645 | 3 | 4 | | | IV-1 | Mycbp |
| 17646 | 3 | 4 | | | IV-1 | Mycn |
| 17647 | 3 | 4 | | | IV-1 | Mycs |
| 17648 | 3 | 4 | | | IV-1 | Myf5 |
| 17649 | 3 | 4 | | | IV-1 | Myh11 |
| 17650 | 3 | 4 | | | IV-1 | Myh15 |
| 17651 | 3 | 4 | | | IV-1 | Myh3 |
| 17652 | 3 | 4 | | | IV-1 | Myh9 |
| 17653 | 3 | 4 | | | IV-1 | Myl12b |
| 17654 | 3 | 4 | | | IV-1 | Mynn |
| 17655 | 3 | 4 | | | IV-1 | Myo10 |
| 17656 | 3 | 4 | | | IV-1 | Myo15 |
| 17657 | 3 | 4 | | | IV-1 | Myo16 |
| 17658 | 3 | 4 | | | IV-1 | Myo19 |
| 17659 | 3 | 4 | | | IV-1 | Myo1a |
| 17660 | 3 | 4 | | | IV-1 | Myo1h |
| 17661 | 3 | 4 | | | IV-1 | Myo3a |
| 17662 | 3 | 4 | | | IV-1 | Myo3b |
| 17663 | 3 | 4 | | | IV-1 | Myo5a |
| 17664 | 3 | 4 | | | IV-1 | Myo5b |
| 17665 | 3 | 4 | | | IV-1 | Myo7b |
| 17666 | 3 | 4 | | | IV-1 | Myo9a |
| 17667 | 3 | 4 | | | IV-1 | Myo9b |
| 17668 | 3 | 4 | | | IV-1 | Myocd |
| 17669 | 3 | 4 | | | IV-1 | Myog |
| 17670 | 3 | 4 | | | IV-1 | Myrf |
| 17671 | 3 | 4 | | | IV-1 | Myrfl |
| 17672 | 3 | 4 | | | IV-1 | Myt1 |
| 17673 | 3 | 4 | | | IV-1 | Myt1l |
| 17674 | 3 | 4 | | | IV-1 | Mzf1 |
| 17675 | 3 | 4 | | | IV-1 | Mzt1 |
| 17676 | 3 | 4 | | | IV-1 | N4bp2l2 |
| 17677 | 3 | 4 | | | IV-1 | N6amt1 |

Fig. 43 - 105

| | | | | | | | | |
|---|---|---|---|---|---|---|---|---|
| 17678 | 3 | 4 | | | | IV-1 | Naa15 |
| 17679 | 3 | 4 | | | | IV-1 | Naa16 |
| 17680 | 3 | 4 | | | | IV-1 | Naa30 |
| 17681 | 3 | 4 | | | | IV-1 | Naa40 |
| 17682 | 3 | 4 | | | | IV-1 | Naa60 |
| 17683 | 3 | 4 | | | | IV-1 | Naalad2 |
| 17684 | 3 | 4 | | | | IV-1 | Naaladl1 |
| 17685 | 3 | 4 | | | | IV-1 | Nab1 |
| 17686 | 3 | 4 | | | | IV-1 | Nacc1 |
| 17687 | 3 | 4 | | | | IV-1 | Nadk |
| 17688 | 3 | 4 | | | | IV-1 | Nadk2 |
| 17689 | 3 | 4 | | | | IV-1 | Naga |
| 17690 | 3 | 4 | | | | IV-1 | Naip1 |
| 17691 | 3 | 4 | | | | IV-1 | Naip7 |
| 17692 | 3 | 4 | | | | IV-1 | Nalcn |
| 17693 | 3 | 4 | | | | IV-1 | Nanog |
| 17694 | 3 | 4 | | | | IV-1 | Nanos2 |
| 17695 | 3 | 4 | | | | IV-1 | Nap1l2 |
| 17696 | 3 | 4 | | | | IV-1 | Nap1l4 |
| 17697 | 3 | 4 | | | | IV-1 | Napepld |
| 17698 | 3 | 4 | | | | IV-1 | Napg |
| 17699 | 3 | 4 | | | | IV-1 | Narfl |
| 17700 | 3 | 4 | | | | IV-1 | Narg2 |
| 17701 | 3 | 4 | | | | IV-1 | Nars2 |
| 17702 | 3 | 4 | | | | IV-1 | Nat1 |
| 17703 | 3 | 4 | | | | IV-1 | Nat10 |
| 17704 | 3 | 4 | | | | IV-1 | Nat3 |
| 17705 | 3 | 4 | | | | IV-1 | Nat6 |
| 17706 | 3 | 4 | | | | IV-1 | Nat8l |
| 17707 | 3 | 4 | | | | IV-1 | Nav3 |
| 17708 | 3 | 4 | | | | IV-1 | Nbas |
| 17709 | 3 | 4 | | | | IV-1 | Nbea |
| 17710 | 3 | 4 | | | | IV-1 | Nbr1 |
| 17711 | 3 | 4 | | | | IV-1 | Ncam1 |
| 17712 | 3 | 4 | | | | IV-1 | Ncam2 |
| 17713 | 3 | 4 | | | | IV-1 | Ncan |
| 17714 | 3 | 4 | | | | IV-1 | Ncapd3 |
| 17715 | 3 | 4 | | | | IV-1 | Ncaph2 |
| 17716 | 3 | 4 | | | | IV-1 | Ncbp1 |
| 17717 | 3 | 4 | | | | IV-1 | Nccrp1 |
| 17718 | 3 | 4 | | | | IV-1 | Ncdn |
| 17719 | 3 | 4 | | | | IV-1 | Ncf1 |
| 17720 | 3 | 4 | | | | IV-1 | Nck2 |
| 17721 | 3 | 4 | | | | IV-1 | Nckap1l |
| 17722 | 3 | 4 | | | | IV-1 | Nckap5l |
| 17723 | 3 | 4 | | | | IV-1 | Ncoa1 |
| 17724 | 3 | 4 | | | | IV-1 | Ncoa4 |
| 17725 | 3 | 4 | | | | IV-1 | Ncoa5 |
| 17726 | 3 | 4 | | | | IV-1 | Ncs1 |
| 17727 | 3 | 4 | | | | IV-1 | Ncstn |
| 17728 | 3 | 4 | | | | IV-1 | Ndc80 |
| 17729 | 3 | 4 | | | | IV-1 | Nde1 |
| 17730 | 3 | 4 | | | | IV-1 | Ndfip1 |
| 17731 | 3 | 4 | | | | IV-1 | Ndn |
| 17732 | 3 | 4 | | | | IV-1 | Ndnf |
| 17733 | 3 | 4 | | | | IV-1 | Ndor1 |
| 17734 | 3 | 4 | | | | IV-1 | Ndp |
| 17735 | 3 | 4 | | | | IV-1 | Ndrg2 |
| 17736 | 3 | 4 | | | | IV-1 | Ndrg3 |
| 17737 | 3 | 4 | | | | IV-1 | Ndst3 |
| 17738 | 3 | 4 | | | | IV-1 | Ndst4 |
| 17739 | 3 | 4 | | | | IV-1 | Ndufa9 |
| 17740 | 3 | 4 | | | | IV-1 | Ndufaf1 |
| 17741 | 3 | 4 | | | | IV-1 | Ndufaf2 |
| 17742 | 3 | 4 | | | | IV-1 | Ndufaf5 |
| 17743 | 3 | 4 | | | | IV-1 | Ndufb11 |
| 17744 | 3 | 4 | | | | IV-1 | Ndufs1 |
| 17745 | 3 | 4 | | | | IV-1 | Ndufs2 |
| 17746 | 3 | 4 | | | | IV-1 | Ndufs5 |
| 17747 | 3 | 4 | | | | IV-1 | Ndufv1 |
| 17748 | 3 | 4 | | | | IV-1 | Necab1 |
| 17749 | 3 | 4 | | | | IV-1 | Necab2 |
| 17750 | 3 | 4 | | | | IV-1 | Necab3 |
| 17751 | 3 | 4 | | | | IV-1 | Necap1 |
| 17752 | 3 | 4 | | | | IV-1 | Necap2 |
| 17753 | 3 | 4 | | | | IV-1 | Nedd4 |
| 17754 | 3 | 4 | | | | IV-1 | Nedd4l |
| 17755 | 3 | 4 | | | | IV-1 | Nedd8 |
| 17756 | 3 | 4 | | | | IV-1 | Nefl |
| 17757 | 3 | 4 | | | | IV-1 | Negr1 |
| 17758 | 3 | 4 | | | | IV-1 | Nek10 |
| 17759 | 3 | 4 | | | | IV-1 | Nek11 |
| 17760 | 3 | 4 | | | | IV-1 | Nek2 |
| 17761 | 3 | 4 | | | | IV-1 | Nek6 |
| 17762 | 3 | 4 | | | | IV-1 | Nek8 |
| 17763 | 3 | 4 | | | | IV-1 | Nek9 |
| 17764 | 3 | 4 | | | | IV-1 | Nelfe |
| 17765 | 3 | 4 | | | | IV-1 | Nell1 |
| 17766 | 3 | 4 | | | | IV-1 | Nell1os |
| 17767 | 3 | 4 | | | | IV-1 | Nell2 |
| 17768 | 3 | 4 | | | | IV-1 | Nemf |
| 17769 | 3 | 4 | | | | IV-1 | Nespas |
| 17770 | 3 | 4 | | | | IV-1 | Neto1 |
| 17771 | 3 | 4 | | | | IV-1 | Neu4 |
| 17772 | 3 | 4 | | | | IV-1 | Neurl1b |
| 17773 | 3 | 4 | | | | IV-1 | Neurod2 |
| 17774 | 3 | 4 | | | | IV-1 | Neurod4 |
| 17775 | 3 | 4 | | | | IV-1 | Neurod6 |
| 17776 | 3 | 4 | | | | IV-1 | Neurog1 |
| 17777 | 3 | 4 | | | | IV-1 | Neurog2 |
| 17778 | 3 | 4 | | | | IV-1 | Neurog3 |
| 17779 | 3 | 4 | | | | IV-1 | Nf2 |
| 17780 | 3 | 4 | | | | IV-1 | Nfatc1 |
| 17781 | 3 | 4 | | | | IV-1 | Nfatc2ip |
| 17782 | 3 | 4 | | | | IV-1 | Nfatc4 |
| 17783 | 3 | 4 | | | | IV-1 | Nfe2l1 |
| 17784 | 3 | 4 | | | | IV-1 | Nfe2l2 |
| 17785 | 3 | 4 | | | | IV-1 | Nfia |
| 17786 | 3 | 4 | | | | IV-1 | Nfkb1 |
| 17787 | 3 | 4 | | | | IV-1 | Nfkbia |
| 17788 | 3 | 4 | | | | IV-1 | Nfx1 |
| 17789 | 3 | 4 | | | | IV-1 | Nfxl1 |
| 17790 | 3 | 4 | | | | IV-1 | Nfya |
| 17791 | 3 | 4 | | | | IV-1 | Nfyb |
| 17792 | 3 | 4 | | | | IV-1 | Nfyc |
| 17793 | 3 | 4 | | | | IV-1 | Ngb |
| 17794 | 3 | 4 | | | | IV-1 | Ngly1 |
| 17795 | 3 | 4 | | | | IV-1 | Ngrn |
| 17796 | 3 | 4 | | | | IV-1 | Nhlh1 |
| 17797 | 3 | 4 | | | | IV-1 | Nhlh2 |
| 17798 | 3 | 4 | | | | IV-1 | Nhlrc1 |
| 17799 | 3 | 4 | | | | IV-1 | Nhlrc4 |
| 17800 | 3 | 4 | | | | IV-1 | Nhp2l1 |
| 17801 | 3 | 4 | | | | IV-1 | Nhs |
| 17802 | 3 | 4 | | | | IV-1 | Nif3l1 |
| 17803 | 3 | 4 | | | | IV-1 | Nifk |
| 17804 | 3 | 4 | | | | IV-1 | Nin |
| 17805 | 3 | 4 | | | | IV-1 | Ninj2 |
| 17806 | 3 | 4 | | | | IV-1 | Nipa2 |
| 17807 | 3 | 4 | | | | IV-1 | Nipsnap3a |
| 17808 | 3 | 4 | | | | IV-1 | Nipsnap3b |
| 17809 | 3 | 4 | | | | IV-1 | Nisch |
| 17810 | 3 | 4 | | | | IV-1 | Nit1 |
| 17811 | 3 | 4 | | | | IV-1 | Nkain1 |
| 17812 | 3 | 4 | | | | IV-1 | Nkain2 |
| 17813 | 3 | 4 | | | | IV-1 | Nkain3 |
| 17814 | 3 | 4 | | | | IV-1 | Nkain4 |
| 17815 | 3 | 4 | | | | IV-1 | Nkap |
| 17816 | 3 | 4 | | | | IV-1 | Nkapl |
| 17817 | 3 | 4 | | | | IV-1 | Nkd1 |
| 17818 | 3 | 4 | | | | IV-1 | Nkiras1 |
| 17819 | 3 | 4 | | | | IV-1 | Nkiras2 |
| 17820 | 3 | 4 | | | | IV-1 | Nkpd1 |
| 17821 | 3 | 4 | | | | IV-1 | Nkrf |
| 17822 | 3 | 4 | | | | IV-1 | Nkx1-1 |
| 17823 | 3 | 4 | | | | IV-1 | Nkx1-2 |
| 17824 | 3 | 4 | | | | IV-1 | Nkx2-1 |
| 17825 | 3 | 4 | | | | IV-1 | Nkx2-2 |
| 17826 | 3 | 4 | | | | IV-1 | Nkx2-2os |
| 17827 | 3 | 4 | | | | IV-1 | Nkx2-3 |
| 17828 | 3 | 4 | | | | IV-1 | Nkx2-6 |
| 17829 | 3 | 4 | | | | IV-1 | Nkx2-9 |
| 17830 | 3 | 4 | | | | IV-1 | Nkx3-2 |
| 17831 | 3 | 4 | | | | IV-1 | Nlgn1 |
| 17832 | 3 | 4 | | | | IV-1 | Nlgn2 |
| 17833 | 3 | 4 | | | | IV-1 | Nlgn3 |
| 17834 | 3 | 4 | | | | IV-1 | Nlrp10 |
| 17835 | 3 | 4 | | | | IV-1 | Nlrp14 |
| 17836 | 3 | 4 | | | | IV-1 | Nlrp1c-ps |
| 17837 | 3 | 4 | | | | IV-1 | Nlrp2 |
| 17838 | 3 | 4 | | | | IV-1 | Nlrp4c |
| 17839 | 3 | 4 | | | | IV-1 | Nlrp4g |
| 17840 | 3 | 4 | | | | IV-1 | Nmbr |
| 17841 | 3 | 4 | | | | IV-1 | Nme7 |
| 17842 | 3 | 4 | | | | IV-1 | Nme8 |
| 17843 | 3 | 4 | | | | IV-1 | Nme9 |
| 17844 | 3 | 4 | | | | IV-1 | Nmnat2 |
| 17845 | 3 | 4 | | | | IV-1 | Nms |
| 17846 | 3 | 4 | | | | IV-1 | Nmt2 |
| 17847 | 3 | 4 | | | | IV-1 | Nmu |

Fig. 43 - 106

| | | | | | | | |
|---|---|---|---|---|---|---|---|
| 17848 | 3 | 4 | | | | IV-1 | Nmur1 |
| 17849 | 3 | 4 | | | | IV-1 | Nmur2 |
| 17850 | 3 | 4 | | | | IV-1 | Nnt |
| 17851 | 3 | 4 | | | | IV-1 | Noc3l |
| 17852 | 3 | 4 | | | | IV-1 | Nod2 |
| 17853 | 3 | 4 | | | | IV-1 | Nol11 |
| 17854 | 3 | 4 | | | | IV-1 | Nol6 |
| 17855 | 3 | 4 | | | | IV-1 | Nol9 |
| 17856 | 3 | 4 | | | | IV-1 | Nomo1 |
| 17857 | 3 | 4 | | | | IV-1 | Nono |
| 17858 | 3 | 4 | | | | IV-1 | Nop14 |
| 17859 | 3 | 4 | | | | IV-1 | Nop56 |
| 17860 | 3 | 4 | | | | IV-1 | Nos2 |
| 17861 | 3 | 4 | | | | IV-1 | Nos3 |
| 17862 | 3 | 4 | | | | IV-1 | Nosip |
| 17863 | 3 | 4 | | | | IV-1 | Nostrin |
| 17864 | 3 | 4 | | | | IV-1 | Notch1 |
| 17865 | 3 | 4 | | | | IV-1 | Noto |
| 17866 | 3 | 4 | | | | IV-1 | Nova1 |
| 17867 | 3 | 4 | | | | IV-1 | Nova2 |
| 17868 | 3 | 4 | | | | IV-1 | Nox1 |
| 17869 | 3 | 4 | | | | IV-1 | Nox4 |
| 17870 | 3 | 4 | | | | IV-1 | Noxa1 |
| 17871 | 3 | 4 | | | | IV-1 | Noxo1 |
| 17872 | 3 | 4 | | | | IV-1 | Noxred1 |
| 17873 | 3 | 4 | | | | IV-1 | Npas3 |
| 17874 | 3 | 4 | | | | IV-1 | Npat |
| 17875 | 3 | 4 | | | | IV-1 | Npbwr1 |
| 17876 | 3 | 4 | | | | IV-1 | Npc2 |
| 17877 | 3 | 4 | | | | IV-1 | Npepps |
| 17878 | 3 | 4 | | | | IV-1 | Npffr1 |
| 17879 | 3 | 4 | | | | IV-1 | Npffr2 |
| 17880 | 3 | 4 | | | | IV-1 | Nphp4 |
| 17881 | 3 | 4 | | | | IV-1 | Nphs1 |
| 17882 | 3 | 4 | | | | IV-1 | Nploc4 |
| 17883 | 3 | 4 | | | | IV-1 | Npm2 |
| 17884 | 3 | 4 | | | | IV-1 | Nppb |
| 17885 | 3 | 4 | | | | IV-1 | Npr1 |
| 17886 | 3 | 4 | | | | IV-1 | Npr3 |
| 17887 | 3 | 4 | | | | IV-1 | Npsr1 |
| 17888 | 3 | 4 | | | | IV-1 | Nptn |
| 17889 | 3 | 4 | | | | IV-1 | Nptx1 |
| 17890 | 3 | 4 | | | | IV-1 | Nptx2 |
| 17891 | 3 | 4 | | | | IV-1 | Npvf |
| 17892 | 3 | 4 | | | | IV-1 | Npy2r |
| 17893 | 3 | 4 | | | | IV-1 | Npy4r |
| 17894 | 3 | 4 | | | | IV-1 | Nr1d2 |
| 17895 | 3 | 4 | | | | IV-1 | Nr1h3 |
| 17896 | 3 | 4 | | | | IV-1 | Nr1h5 |
| 17897 | 3 | 4 | | | | IV-1 | Nr1i2 |
| 17898 | 3 | 4 | | | | IV-1 | Nr2e1 |
| 17899 | 3 | 4 | | | | IV-1 | Nr2e3 |
| 17900 | 3 | 4 | | | | IV-1 | Nr2f2 |
| 17901 | 3 | 4 | | | | IV-1 | Nr5a1 |
| 17902 | 3 | 4 | | | | IV-1 | Nr6a1 |
| 17903 | 3 | 4 | | | | IV-1 | Nras |
| 17904 | 3 | 4 | | | | IV-1 | Nrbf2 |
| 17905 | 3 | 4 | | | | IV-1 | Nrcam |
| 17906 | 3 | 4 | | | | IV-1 | Nrde2 |
| 17907 | 3 | 4 | | | | IV-1 | Nrg3 |
| 17908 | 3 | 4 | | | | IV-1 | Nrg3os |
| 17909 | 3 | 4 | | | | IV-1 | Nrk |
| 17910 | 3 | 4 | | | | IV-1 | Nrl |
| 17911 | 3 | 4 | | | | IV-1 | Nrn1 |
| 17912 | 3 | 4 | | | | IV-1 | Nrp2 |
| 17913 | 3 | 4 | | | | IV-1 | Nrros |
| 17914 | 3 | 4 | | | | IV-1 | Nrsn1 |
| 17915 | 3 | 4 | | | | IV-1 | Nrxn3 |
| 17916 | 3 | 4 | | | | IV-1 | Nsf |
| 17917 | 3 | 4 | | | | IV-1 | Nsfl1c |
| 17918 | 3 | 4 | | | | IV-1 | Nsmce1 |
| 17919 | 3 | 4 | | | | IV-1 | Nsmce2 |
| 17920 | 3 | 4 | | | | IV-1 | Nsun2 |
| 17921 | 3 | 4 | | | | IV-1 | Nsun4 |
| 17922 | 3 | 4 | | | | IV-1 | Nsun7 |
| 17923 | 3 | 4 | | | | IV-1 | Nt5c1a |
| 17924 | 3 | 4 | | | | IV-1 | Nt5dc1 |
| 17925 | 3 | 4 | | | | IV-1 | Nt5e |
| 17926 | 3 | 4 | | | | IV-1 | Ntan1 |
| 17927 | 3 | 4 | | | | IV-1 | Ntf5 |
| 17928 | 3 | 4 | | | | IV-1 | Ntm |
| 17929 | 3 | 4 | | | | IV-1 | Ntn3 |
| 17930 | 3 | 4 | | | | IV-1 | Ntn5 |
| 17931 | 3 | 4 | | | | IV-1 | Ntng1 |
| 17932 | 3 | 4 | | | | IV-1 | Ntpcr |
| 17933 | 3 | 4 | | | | IV-1 | Ntrk1 |
| 17934 | 3 | 4 | | | | IV-1 | Ntsr1 |
| 17935 | 3 | 4 | | | | IV-1 | Nub1 |
| 17936 | 3 | 4 | | | | IV-1 | Nubp1 |
| 17937 | 3 | 4 | | | | IV-1 | Nubp2 |
| 17938 | 3 | 4 | | | | IV-1 | Nucb1 |
| 17939 | 3 | 4 | | | | IV-1 | Nucks1 |
| 17940 | 3 | 4 | | | | IV-1 | Nudc |
| 17941 | 3 | 4 | | | | IV-1 | Nudcd3 |
| 17942 | 3 | 4 | | | | IV-1 | Nudt1 |
| 17943 | 3 | 4 | | | | IV-1 | Nudt11 |
| 17944 | 3 | 4 | | | | IV-1 | Nudt15 |
| 17945 | 3 | 4 | | | | IV-1 | Nudt16 |
| 17946 | 3 | 4 | | | | IV-1 | Nudt16l1 |
| 17947 | 3 | 4 | | | | IV-1 | Nudt17 |
| 17948 | 3 | 4 | | | | IV-1 | Nudt21 |
| 17949 | 3 | 4 | | | | IV-1 | Nudt22 |
| 17950 | 3 | 4 | | | | IV-1 | Nudt3 |
| 17951 | 3 | 4 | | | | IV-1 | Nuf2 |
| 17952 | 3 | 4 | | | | IV-1 | Nufip1 |
| 17953 | 3 | 4 | | | | IV-1 | Nufip2 |
| 17954 | 3 | 4 | | | | IV-1 | Nuggc |
| 17955 | 3 | 4 | | | | IV-1 | Numb |
| 17956 | 3 | 4 | | | | IV-1 | Numbl |
| 17957 | 3 | 4 | | | | IV-1 | Nup133 |
| 17958 | 3 | 4 | | | | IV-1 | Nup155 |
| 17959 | 3 | 4 | | | | IV-1 | Nup205 |
| 17960 | 3 | 4 | | | | IV-1 | Nup210l |
| 17961 | 3 | 4 | | | | IV-1 | Nup37 |
| 17962 | 3 | 4 | | | | IV-1 | Nup50 |
| 17963 | 3 | 4 | | | | IV-1 | Nup54 |
| 17964 | 3 | 4 | | | | IV-1 | Nup62cl |
| 17965 | 3 | 4 | | | | IV-1 | Nup62-il4i1 |
| 17966 | 3 | 4 | | | | IV-1 | Nup98 |
| 17967 | 3 | 4 | | | | IV-1 | Nupl2 |
| 17968 | 3 | 4 | | | | IV-1 | Nus1 |
| 17969 | 3 | 4 | | | | IV-1 | Nutm1 |
| 17970 | 3 | 4 | | | | IV-1 | Nwd2 |
| 17971 | 3 | 4 | | | | IV-1 | Nxf1 |
| 17972 | 3 | 4 | | | | IV-1 | Nxf2 |
| 17973 | 3 | 4 | | | | IV-1 | Nxf7 |
| 17974 | 3 | 4 | | | | IV-1 | Nxnl2 |
| 17975 | 3 | 4 | | | | IV-1 | Nxph1 |
| 17976 | 3 | 4 | | | | IV-1 | Nxph2 |
| 17977 | 3 | 4 | | | | IV-1 | Nxph4 |
| 17978 | 3 | 4 | | | | IV-1 | Nxt2 |
| 17979 | 3 | 4 | | | | IV-1 | Oas1d |
| 17980 | 3 | 4 | | | | IV-1 | Oas1e |
| 17981 | 3 | 4 | | | | IV-1 | Oas1f |
| 17982 | 3 | 4 | | | | IV-1 | Oas1h |
| 17983 | 3 | 4 | | | | IV-1 | Oat |
| 17984 | 3 | 4 | | | | IV-1 | Obox1 |
| 17985 | 3 | 4 | | | | IV-1 | Obox2 |
| 17986 | 3 | 4 | | | | IV-1 | Obox3 |
| 17987 | 3 | 4 | | | | IV-1 | Obox5 |
| 17988 | 3 | 4 | | | | IV-1 | Obp1a |
| 17989 | 3 | 4 | | | | IV-1 | Ocln |
| 17990 | 3 | 4 | | | | IV-1 | Ocstamp |
| 17991 | 3 | 4 | | | | IV-1 | Odam |
| 17992 | 3 | 4 | | | | IV-1 | Odf3 |
| 17993 | 3 | 4 | | | | IV-1 | Odf3l1 |
| 17994 | 3 | 4 | | | | IV-1 | Odf4 |
| 17995 | 3 | 4 | | | | IV-1 | Ofcc1 |
| 17996 | 3 | 4 | | | | IV-1 | Ogdh |
| 17997 | 3 | 4 | | | | IV-1 | Ogdhl |
| 17998 | 3 | 4 | | | | IV-1 | Ogfr |
| 17999 | 3 | 4 | | | | IV-1 | Ogfrl1 |
| 18000 | 3 | 4 | | | | IV-1 | Olah |
| 18001 | 3 | 4 | | | | IV-1 | Olfm2 |
| 18002 | 3 | 4 | | | | IV-1 | Olfm3 |
| 18003 | 3 | 4 | | | | IV-1 | Olfr1 |
| 18004 | 3 | 4 | | | | IV-1 | Olfr10 |
| 18005 | 3 | 4 | | | | IV-1 | Olfr100 |
| 18006 | 3 | 4 | | | | IV-1 | Olfr1000 |
| 18007 | 3 | 4 | | | | IV-1 | Olfr1002 |
| 18008 | 3 | 4 | | | | IV-1 | Olfr1006 |
| 18009 | 3 | 4 | | | | IV-1 | Olfr1040 |
| 18010 | 3 | 4 | | | | IV-1 | Olfr1042 |
| 18011 | 3 | 4 | | | | IV-1 | Olfr1287 |
| 18012 | 3 | 4 | | | | IV-1 | Olfr1305 |
| 18013 | 3 | 4 | | | | IV-1 | Olfr1381 |
| 18014 | 3 | 4 | | | | IV-1 | Olfr1402 |
| 18015 | 3 | 4 | | | | IV-1 | Olfr1404 |
| 18016 | 3 | 4 | | | | IV-1 | Olfr141 |
| 18017 | 3 | 4 | | | | IV-1 | Olfr1428 |

Fig. 43 - 107

| | | | | | | | |
|---|---|---|---|---|---|---|---|
| 18018 | 3 | 4 | | | | IV-1 | Olfr170 |
| 18019 | 3 | 4 | | | | IV-1 | Olfr204 |
| 18020 | 3 | 4 | | | | IV-1 | Olfr221 |
| 18021 | 3 | 4 | | | | IV-1 | Olfr224 |
| 18022 | 3 | 4 | | | | IV-1 | Olfr294 |
| 18023 | 3 | 4 | | | | IV-1 | Olfr322 |
| 18024 | 3 | 4 | | | | IV-1 | Olfr531 |
| 18025 | 3 | 4 | | | | IV-1 | Olfr552 |
| 18026 | 3 | 4 | | | | IV-1 | Olfr569 |
| 18027 | 3 | 4 | | | | IV-1 | Olfr77 |
| 18028 | 3 | 4 | | | | IV-1 | Olfr787 |
| 18029 | 3 | 4 | | | | IV-1 | Olfr878 |
| 18030 | 3 | 4 | | | | IV-1 | Olfr93 |
| 18031 | 3 | 4 | | | | IV-1 | Olfr985 |
| 18032 | 3 | 4 | | | | IV-1 | Omg |
| 18033 | 3 | 4 | | | | IV-1 | Omp |
| 18034 | 3 | 4 | | | | IV-1 | Omt2b |
| 18035 | 3 | 4 | | | | IV-1 | Onecut2 |
| 18036 | 3 | 4 | | | | IV-1 | Onecut3 |
| 18037 | 3 | 4 | | | | IV-1 | Oog3 |
| 18038 | 3 | 4 | | | | IV-1 | Oosp2 |
| 18039 | 3 | 4 | | | | IV-1 | Opn1mw |
| 18040 | 3 | 4 | | | | IV-1 | Opn1sw |
| 18041 | 3 | 4 | | | | IV-1 | Opn4 |
| 18042 | 3 | 4 | | | | IV-1 | Opn5 |
| 18043 | 3 | 4 | | | | IV-1 | Oprd1 |
| 18044 | 3 | 4 | | | | IV-1 | Oprm1 |
| 18045 | 3 | 4 | | | | IV-1 | Orc4 |
| 18046 | 3 | 4 | | | | IV-1 | Ormdl3 |
| 18047 | 3 | 4 | | | | IV-1 | Os9 |
| 18048 | 3 | 4 | | | | IV-1 | Osbp |
| 18049 | 3 | 4 | | | | IV-1 | Osbp2 |
| 18050 | 3 | 4 | | | | IV-1 | Osbpl2 |
| 18051 | 3 | 4 | | | | IV-1 | Osbpl3 |
| 18052 | 3 | 4 | | | | IV-1 | Osbpl7 |
| 18053 | 3 | 4 | | | | IV-1 | Osbpl8 |
| 18054 | 3 | 4 | | | | IV-1 | Osbpl9 |
| 18055 | 3 | 4 | | | | IV-1 | Oscar |
| 18056 | 3 | 4 | | | | IV-1 | Osgep |
| 18057 | 3 | 4 | | | | IV-1 | Osgepl1 |
| 18058 | 3 | 4 | | | | IV-1 | Osr2 |
| 18059 | 3 | 4 | | | | IV-1 | Ostm1 |
| 18060 | 3 | 4 | | | | IV-1 | Ostn |
| 18061 | 3 | 4 | | | | IV-1 | Otc |
| 18062 | 3 | 4 | | | | IV-1 | Otoa |
| 18063 | 3 | 4 | | | | IV-1 | Otof |
| 18064 | 3 | 4 | | | | IV-1 | Otog |
| 18065 | 3 | 4 | | | | IV-1 | Otogl |
| 18066 | 3 | 4 | | | | IV-1 | Otop3 |
| 18067 | 3 | 4 | | | | IV-1 | Otud4 |
| 18068 | 3 | 4 | | | | IV-1 | Otud6a |
| 18069 | 3 | 4 | | | | IV-1 | Otud6b |
| 18070 | 3 | 4 | | | | IV-1 | Otud7a |
| 18071 | 3 | 4 | | | | IV-1 | Otx1 |
| 18072 | 3 | 4 | | | | IV-1 | Otx2os1 |
| 18073 | 3 | 4 | | | | IV-1 | Ovch2 |
| 18074 | 3 | 4 | | | | IV-1 | Ovgp1 |
| 18075 | 3 | 4 | | | | IV-1 | Oxct2a |
| 18076 | 3 | 4 | | | | IV-1 | Oxgr1 |
| 18077 | 3 | 4 | | | | IV-1 | Oxr1 |
| 18078 | 3 | 4 | | | | IV-1 | Oxtr |
| 18079 | 3 | 4 | | | | IV-1 | P2rx2 |
| 18080 | 3 | 4 | | | | IV-1 | P2rx6 |
| 18081 | 3 | 4 | | | | IV-1 | P2ry1 |
| 18082 | 3 | 4 | | | | IV-1 | P2ry14 |
| 18083 | 3 | 4 | | | | IV-1 | P2ry4 |
| 18084 | 3 | 4 | | | | IV-1 | P4ha3 |
| 18085 | 3 | 4 | | | | IV-1 | P4hb |
| 18086 | 3 | 4 | | | | IV-1 | Pabpc1 |
| 18087 | 3 | 4 | | | | IV-1 | Pabpc1l |
| 18088 | 3 | 4 | | | | IV-1 | Pabpc4l |
| 18089 | 3 | 4 | | | | IV-1 | Pabpc5 |
| 18090 | 3 | 4 | | | | IV-1 | Pabpc6 |
| 18091 | 3 | 4 | | | | IV-1 | Pabpn1 |
| 18092 | 3 | 4 | | | | IV-1 | Pabpn1l |
| 18093 | 3 | 4 | | | | IV-1 | Padi1 |
| 18094 | 3 | 4 | | | | IV-1 | Padi3 |
| 18095 | 3 | 4 | | | | IV-1 | Padi4 |
| 18096 | 3 | 4 | | | | IV-1 | Padi6 |
| 18097 | 3 | 4 | | | | IV-1 | Pafah1b1 |
| 18098 | 3 | 4 | | | | IV-1 | Pafah2 |
| 18099 | 3 | 4 | | | | IV-1 | Paics |
| 18100 | 3 | 4 | | | | IV-1 | Paip1 |
| 18101 | 3 | 4 | | | | IV-1 | Paip2b |
| 18102 | 3 | 4 | | | | IV-1 | Pak1 |

| | | | | | | | |
|---|---|---|---|---|---|---|---|
| 18103 | 3 | 4 | | | | IV-1 | Pak2 |
| 18104 | 3 | 4 | | | | IV-1 | Pak3 |
| 18105 | 3 | 4 | | | | IV-1 | Pak6 |
| 18106 | 3 | 4 | | | | IV-1 | Pak7 |
| 18107 | 3 | 4 | | | | IV-1 | Palb2 |
| 18108 | 3 | 4 | | | | IV-1 | Pald1 |
| 18109 | 3 | 4 | | | | IV-1 | Palm |
| 18110 | 3 | 4 | | | | IV-1 | Palm2 |
| 18111 | 3 | 4 | | | | IV-1 | Palmd |
| 18112 | 3 | 4 | | | | IV-1 | Pank4 |
| 18113 | 3 | 4 | | | | IV-1 | Panx2 |
| 18114 | 3 | 4 | | | | IV-1 | Panx3 |
| 18115 | 3 | 4 | | | | IV-1 | Papd5 |
| 18116 | 3 | 4 | | | | IV-1 | Papd7 |
| 18117 | 3 | 4 | | | | IV-1 | Pappa2 |
| 18118 | 3 | 4 | | | | IV-1 | Papss1 |
| 18119 | 3 | 4 | | | | IV-1 | Paqr4 |
| 18120 | 3 | 4 | | | | IV-1 | Paqr6 |
| 18121 | 3 | 4 | | | | IV-1 | Pard6g |
| 18122 | 3 | 4 | | | | IV-1 | Parg |
| 18123 | 3 | 4 | | | | IV-1 | Park2 |
| 18124 | 3 | 4 | | | | IV-1 | Parp1 |
| 18125 | 3 | 4 | | | | IV-1 | Parp16 |
| 18126 | 3 | 4 | | | | IV-1 | Parp4 |
| 18127 | 3 | 4 | | | | IV-1 | Parpbp |
| 18128 | 3 | 4 | | | | IV-1 | Pars2 |
| 18129 | 3 | 4 | | | | IV-1 | Parva |
| 18130 | 3 | 4 | | | | IV-1 | Pate4 |
| 18131 | 3 | 4 | | | | IV-1 | Patl1 |
| 18132 | 3 | 4 | | | | IV-1 | Patl2 |
| 18133 | 3 | 4 | | | | IV-1 | Paupar |
| 18134 | 3 | 4 | | | | IV-1 | Pax4 |
| 18135 | 3 | 4 | | | | IV-1 | Pax6 |
| 18136 | 3 | 4 | | | | IV-1 | Pax6os1 |
| 18137 | 3 | 4 | | | | IV-1 | Pax7 |
| 18138 | 3 | 4 | | | | IV-1 | Paxbp1 |
| 18139 | 3 | 4 | | | | IV-1 | Pbrm1 |
| 18140 | 3 | 4 | | | | IV-1 | Pbsn |
| 18141 | 3 | 4 | | | | IV-1 | Pbx2 |
| 18142 | 3 | 4 | | | | IV-1 | Pbx3 |
| 18143 | 3 | 4 | | | | IV-1 | Pcbp1 |
| 18144 | 3 | 4 | | | | IV-1 | Pcbp4 |
| 18145 | 3 | 4 | | | | IV-1 | Pccb |
| 18146 | 3 | 4 | | | | IV-1 | Pcdh10 |
| 18147 | 3 | 4 | | | | IV-1 | Pcdh11x |
| 18148 | 3 | 4 | | | | IV-1 | Pcdh15 |
| 18149 | 3 | 4 | | | | IV-1 | Pcdh19 |
| 18150 | 3 | 4 | | | | IV-1 | Pcdh20 |
| 18151 | 3 | 4 | | | | IV-1 | Pcdh9 |
| 18152 | 3 | 4 | | | | IV-1 | Pcdha10 |
| 18153 | 3 | 4 | | | | IV-1 | Pcdha11 |
| 18154 | 3 | 4 | | | | IV-1 | Pcdha12 |
| 18155 | 3 | 4 | | | | IV-1 | Pcdha3 |
| 18156 | 3 | 4 | | | | IV-1 | Pcdha4-g |
| 18157 | 3 | 4 | | | | IV-1 | Pcdha5 |
| 18158 | 3 | 4 | | | | IV-1 | Pcdha6 |
| 18159 | 3 | 4 | | | | IV-1 | Pcdha7 |
| 18160 | 3 | 4 | | | | IV-1 | Pcdha8 |
| 18161 | 3 | 4 | | | | IV-1 | Pcdhb10 |
| 18162 | 3 | 4 | | | | IV-1 | Pcdhb13 |
| 18163 | 3 | 4 | | | | IV-1 | Pcdhb14 |
| 18164 | 3 | 4 | | | | IV-1 | Pcdhb18 |
| 18165 | 3 | 4 | | | | IV-1 | Pcdhb2 |
| 18166 | 3 | 4 | | | | IV-1 | Pcdhb20 |
| 18167 | 3 | 4 | | | | IV-1 | Pcdhb21 |
| 18168 | 3 | 4 | | | | IV-1 | Pcdhb3 |
| 18169 | 3 | 4 | | | | IV-1 | Pcdhb4 |
| 18170 | 3 | 4 | | | | IV-1 | Pcdhb6 |
| 18171 | 3 | 4 | | | | IV-1 | Pcdhb7 |
| 18172 | 3 | 4 | | | | IV-1 | Pcdhb8 |
| 18173 | 3 | 4 | | | | IV-1 | Pcdhga3 |
| 18174 | 3 | 4 | | | | IV-1 | Pcdhga4 |
| 18175 | 3 | 4 | | | | IV-1 | Pcdhga6 |
| 18176 | 3 | 4 | | | | IV-1 | Pcdhga7 |
| 18177 | 3 | 4 | | | | IV-1 | Pcdhga8 |
| 18178 | 3 | 4 | | | | IV-1 | Pcdhga9 |
| 18179 | 3 | 4 | | | | IV-1 | Pcdhgb2 |
| 18180 | 3 | 4 | | | | IV-1 | Pcdhgb5 |
| 18181 | 3 | 4 | | | | IV-1 | Pcdhgb8 |
| 18182 | 3 | 4 | | | | IV-1 | Pcdhgc4 |
| 18183 | 3 | 4 | | | | IV-1 | Pcdhgc5 |
| 18184 | 3 | 4 | | | | IV-1 | Pced1a |
| 18185 | 3 | 4 | | | | IV-1 | Pced1b |
| 18186 | 3 | 4 | | | | IV-1 | Pcf11 |
| 18187 | 3 | 4 | | | | IV-1 | Pcgf2 |

Fig. 43 - 108

| | | | | | | | |
|---|---|---|---|---|---|---|---|
| 18188 | 3 | 4 | | | IV-1 | Pcgf5 |
| 18189 | 3 | 4 | | | IV-1 | Pcid2 |
| 18190 | 3 | 4 | | | IV-1 | Pcif1 |
| 18191 | 3 | 4 | | | IV-1 | Pclo |
| 18192 | 3 | 4 | | | IV-1 | Pcm1 |
| 18193 | 3 | 4 | | | IV-1 | Pcmt1 |
| 18194 | 3 | 4 | | | IV-1 | Pcmtd1 |
| 18195 | 3 | 4 | | | IV-1 | Pcna |
| 18196 | 3 | 4 | | | IV-1 | Pcnp |
| 18197 | 3 | 4 | | | IV-1 | Pcnxl2 |
| 18198 | 3 | 4 | | | IV-1 | Pcnxl3 |
| 18199 | 3 | 4 | | | IV-1 | Pcnxl4 |
| 18200 | 3 | 4 | | | IV-1 | Pcp2 |
| 18201 | 3 | 4 | | | IV-1 | Pcsk1 |
| 18202 | 3 | 4 | | | IV-1 | Pcsk2os1 |
| 18203 | 3 | 4 | | | IV-1 | Pcsk2os2 |
| 18204 | 3 | 4 | | | IV-1 | Pcsk5 |
| 18205 | 3 | 4 | | | IV-1 | Pcsk7 |
| 18206 | 3 | 4 | | | IV-1 | Pcyt1a |
| 18207 | 3 | 4 | | | IV-1 | Pcyt2 |
| 18208 | 3 | 4 | | | IV-1 | Pdap1 |
| 18209 | 3 | 4 | | | IV-1 | Pdc |
| 18210 | 3 | 4 | | | IV-1 | Pdcd11 |
| 18211 | 3 | 4 | | | IV-1 | Pdcd1lg2 |
| 18212 | 3 | 4 | | | IV-1 | Pdcd6 |
| 18213 | 3 | 4 | | | IV-1 | Pdcd7 |
| 18214 | 3 | 4 | | | IV-1 | Pdcl |
| 18215 | 3 | 4 | | | IV-1 | Pdcl3 |
| 18216 | 3 | 4 | | | IV-1 | Pde11a |
| 18217 | 3 | 4 | | | IV-1 | Pde1c |
| 18218 | 3 | 4 | | | IV-1 | Pde2a |
| 18219 | 3 | 4 | | | IV-1 | Pde4a |
| 18220 | 3 | 4 | | | IV-1 | Pde6a |
| 18221 | 3 | 4 | | | IV-1 | Pde6b |
| 18222 | 3 | 4 | | | IV-1 | Pde6c |
| 18223 | 3 | 4 | | | IV-1 | Pde6d |
| 18224 | 3 | 4 | | | IV-1 | Pde6g |
| 18225 | 3 | 4 | | | IV-1 | Pdgfb |
| 18226 | 3 | 4 | | | IV-1 | Pdgfra |
| 18227 | 3 | 4 | | | IV-1 | Pdgfrb |
| 18228 | 3 | 4 | | | IV-1 | Pdgfrl |
| 18229 | 3 | 4 | | | IV-1 | Pdha1 |
| 18230 | 3 | 4 | | | IV-1 | Pdhx |
| 18231 | 3 | 4 | | | IV-1 | Pdik1l |
| 18232 | 3 | 4 | | | IV-1 | Pdilt |
| 18233 | 3 | 4 | | | IV-1 | Pdk1 |
| 18234 | 3 | 4 | | | IV-1 | Pdp1 |
| 18235 | 3 | 4 | | | IV-1 | Pds5b |
| 18236 | 3 | 4 | | | IV-1 | Pdss2 |
| 18237 | 3 | 4 | | | IV-1 | Pdxdc1 |
| 18238 | 3 | 4 | | | IV-1 | Pdxk-ps |
| 18239 | 3 | 4 | | | IV-1 | Pdxp |
| 18240 | 3 | 4 | | | IV-1 | Pdyn |
| 18241 | 3 | 4 | | | IV-1 | Pdzd3 |
| 18242 | 3 | 4 | | | IV-1 | Pdzd8 |
| 18243 | 3 | 4 | | | IV-1 | Pdzd9 |
| 18244 | 3 | 4 | | | IV-1 | Pea15a |
| 18245 | 3 | 4 | | | IV-1 | Pebp4 |
| 18246 | 3 | 4 | | | IV-1 | Peg12 |
| 18247 | 3 | 4 | | | IV-1 | Peli1 |
| 18248 | 3 | 4 | | | IV-1 | Pelp1 |
| 18249 | 3 | 4 | | | IV-1 | Peo1 |
| 18250 | 3 | 4 | | | IV-1 | Per1 |
| 18251 | 3 | 4 | | | IV-1 | Peril |
| 18252 | 3 | 4 | | | IV-1 | Pet100 |
| 18253 | 3 | 4 | | | IV-1 | Pet2 |
| 18254 | 3 | 4 | | | IV-1 | Pex19 |
| 18255 | 3 | 4 | | | IV-1 | Pex2 |
| 18256 | 3 | 4 | | | IV-1 | Pex26 |
| 18257 | 3 | 4 | | | IV-1 | Pex3 |
| 18258 | 3 | 4 | | | IV-1 | Pex5 |
| 18259 | 3 | 4 | | | IV-1 | Pex5l |
| 18260 | 3 | 4 | | | IV-1 | Pex7 |
| 18261 | 3 | 4 | | | IV-1 | Pfdn2 |
| 18262 | 3 | 4 | | | IV-1 | Pfkfb1 |
| 18263 | 3 | 4 | | | IV-1 | Pfkfb3 |
| 18264 | 3 | 4 | | | IV-1 | Pfn4 |
| 18265 | 3 | 4 | | | IV-1 | Pfpl |
| 18266 | 3 | 4 | | | IV-1 | Pga5 |
| 18267 | 3 | 4 | | | IV-1 | Pgam5 |
| 18268 | 3 | 4 | | | IV-1 | Pgbd5 |
| 18269 | 3 | 4 | | | IV-1 | Pglyrp2 |
| 18270 | 3 | 4 | | | IV-1 | Pglyrp3 |
| 18271 | 3 | 4 | | | IV-1 | Pglyrp4 |
| 18272 | 3 | 4 | | | IV-1 | Pgm2 |
| 18273 | 3 | 4 | | | IV-1 | Pgp |
| 18274 | 3 | 4 | | | IV-1 | Pgr |
| 18275 | 3 | 4 | | | IV-1 | Pgr15l |
| 18276 | 3 | 4 | | | IV-1 | Pgrmc2 |
| 18277 | 3 | 4 | | | IV-1 | Pgs1 |
| 18278 | 3 | 4 | | | IV-1 | Phactr4 |
| 18279 | 3 | 4 | | | IV-1 | Phb |
| 18280 | 3 | 4 | | | IV-1 | Phc1 |
| 18281 | 3 | 4 | | | IV-1 | Phc2 |
| 18282 | 3 | 4 | | | IV-1 | Phex |
| 18283 | 3 | 4 | | | IV-1 | Phf12 |
| 18284 | 3 | 4 | | | IV-1 | Phf20 |
| 18285 | 3 | 4 | | | IV-1 | Phf20l1 |
| 18286 | 3 | 4 | | | IV-1 | Phf21a |
| 18287 | 3 | 4 | | | IV-1 | Phf21b |
| 18288 | 3 | 4 | | | IV-1 | Phf6 |
| 18289 | 3 | 4 | | | IV-1 | Phf8 |
| 18290 | 3 | 4 | | | IV-1 | Phip |
| 18291 | 3 | 4 | | | IV-1 | Phkg2 |
| 18292 | 3 | 4 | | | IV-1 | Phospho1 |
| 18293 | 3 | 4 | | | IV-1 | Phospho2 |
| 18294 | 3 | 4 | | | IV-1 | Phox2b |
| 18295 | 3 | 4 | | | IV-1 | Phrf1 |
| 18296 | 3 | 4 | | | IV-1 | Phtf1 |
| 18297 | 3 | 4 | | | IV-1 | Phxr4 |
| 18298 | 3 | 4 | | | IV-1 | Pi4k2a |
| 18299 | 3 | 4 | | | IV-1 | Pi4k2b |
| 18300 | 3 | 4 | | | IV-1 | Pi4kb |
| 18301 | 3 | 4 | | | IV-1 | Pianp |
| 18302 | 3 | 4 | | | IV-1 | Pias1 |
| 18303 | 3 | 4 | | | IV-1 | Pias2 |
| 18304 | 3 | 4 | | | IV-1 | Pias3 |
| 18305 | 3 | 4 | | | IV-1 | Pibf1 |
| 18306 | 3 | 4 | | | IV-1 | Picalm |
| 18307 | 3 | 4 | | | IV-1 | Pick1 |
| 18308 | 3 | 4 | | | IV-1 | Pif1 |
| 18309 | 3 | 4 | | | IV-1 | Pifo |
| 18310 | 3 | 4 | | | IV-1 | Pigc |
| 18311 | 3 | 4 | | | IV-1 | Pigg |
| 18312 | 3 | 4 | | | IV-1 | Pigk |
| 18313 | 3 | 4 | | | IV-1 | Pigm |
| 18314 | 3 | 4 | | | IV-1 | Pign |
| 18315 | 3 | 4 | | | IV-1 | Pigo |
| 18316 | 3 | 4 | | | IV-1 | Pigq |
| 18317 | 3 | 4 | | | IV-1 | Pigs |
| 18318 | 3 | 4 | | | IV-1 | Pigw |
| 18319 | 3 | 4 | | | IV-1 | Pih1d2 |
| 18320 | 3 | 4 | | | IV-1 | Pih1d3 |
| 18321 | 3 | 4 | | | IV-1 | Pik3c2a |
| 18322 | 3 | 4 | | | IV-1 | Pik3c3 |
| 18323 | 3 | 4 | | | IV-1 | Pik3cb |
| 18324 | 3 | 4 | | | IV-1 | Pik3cd |
| 18325 | 3 | 4 | | | IV-1 | Pik3r3 |
| 18326 | 3 | 4 | | | IV-1 | Pik3r4 |
| 18327 | 3 | 4 | | | IV-1 | Pik3r5 |
| 18328 | 3 | 4 | | | IV-1 | Pikfyve |
| 18329 | 3 | 4 | | | IV-1 | Pilrb1 |
| 18330 | 3 | 4 | | | IV-1 | Pilrb2 |
| 18331 | 3 | 4 | | | IV-1 | Pin1 |
| 18332 | 3 | 4 | | | IV-1 | Pinc |
| 18333 | 3 | 4 | | | IV-1 | Pinlyp |
| 18334 | 3 | 4 | | | IV-1 | Pip4k2c |
| 18335 | 3 | 4 | | | IV-1 | Pip5k1c |
| 18336 | 3 | 4 | | | IV-1 | Pip5k1l |
| 18337 | 3 | 4 | | | IV-1 | Pira1 |
| 18338 | 3 | 4 | | | IV-1 | Pira7 |
| 18339 | 3 | 4 | | | IV-1 | Pisd |
| 18340 | 3 | 4 | | | IV-1 | Pitpna |
| 18341 | 3 | 4 | | | IV-1 | Pitpnb |
| 18342 | 3 | 4 | | | IV-1 | Pitpnm2os1 |
| 18343 | 3 | 4 | | | IV-1 | Pitrm1 |
| 18344 | 3 | 4 | | | IV-1 | Pitx1 |
| 18345 | 3 | 4 | | | IV-1 | Piwil1 |
| 18346 | 3 | 4 | | | IV-1 | Piwil2 |
| 18347 | 3 | 4 | | | IV-1 | Piwil4 |
| 18348 | 3 | 4 | | | IV-1 | Pja1 |
| 18349 | 3 | 4 | | | IV-1 | Pja2 |
| 18350 | 3 | 4 | | | IV-1 | Pkd2l1 |
| 18351 | 3 | 4 | | | IV-1 | Pkd2l2 |
| 18352 | 3 | 4 | | | IV-1 | Pkhd1 |
| 18353 | 3 | 4 | | | IV-1 | Pkib |
| 18354 | 3 | 4 | | | IV-1 | Pkn2 |
| 18355 | 3 | 4 | | | IV-1 | Pkn3 |
| 18356 | 3 | 4 | | | IV-1 | Pkp4 |
| 18357 | 3 | 4 | | | IV-1 | Pla2g10 |

Fig. 43 - 109

| | | | | | | | |
|---|---|---|---|---|---|---|---|
| 18358 | 3 | 4 | | | | IV-1 | Pla2g12b |
| 18359 | 3 | 4 | | | | IV-1 | Pla2g2a |
| 18360 | 3 | 4 | | | | IV-1 | Pla2g2c |
| 18361 | 3 | 4 | | | | IV-1 | Pla2g2e |
| 18362 | 3 | 4 | | | | IV-1 | Pla2g2f |
| 18363 | 3 | 4 | | | | IV-1 | Pla2g3 |
| 18364 | 3 | 4 | | | | IV-1 | Pla2g6 |
| 18365 | 3 | 4 | | | | IV-1 | Plaa |
| 18366 | 3 | 4 | | | | IV-1 | Plac1 |
| 18367 | 3 | 4 | | | | IV-1 | Plac8l1 |
| 18368 | 3 | 4 | | | | IV-1 | Plagl2 |
| 18369 | 3 | 4 | | | | IV-1 | Plch1 |
| 18370 | 3 | 4 | | | | IV-1 | Plcxd3 |
| 18371 | 3 | 4 | | | | IV-1 | Plcz1 |
| 18372 | 3 | 4 | | | | IV-1 | Pld2 |
| 18373 | 3 | 4 | | | | IV-1 | Pld5 |
| 18374 | 3 | 4 | | | | IV-1 | Pldi |
| 18375 | 3 | 4 | | | | IV-1 | Plekha3 |
| 18376 | 3 | 4 | | | | IV-1 | Plekha8 |
| 18377 | 3 | 4 | | | | IV-1 | Plekhb2 |
| 18378 | 3 | 4 | | | | IV-1 | Plekhd1 |
| 18379 | 3 | 4 | | | | IV-1 | Plekhf1 |
| 18380 | 3 | 4 | | | | IV-1 | Plekhf2 |
| 18381 | 3 | 4 | | | | IV-1 | Plekhg3 |
| 18382 | 3 | 4 | | | | IV-1 | Plekhg4 |
| 18383 | 3 | 4 | | | | IV-1 | Plekhh1 |
| 18384 | 3 | 4 | | | | IV-1 | Plekhj1 |
| 18385 | 3 | 4 | | | | IV-1 | Plekho2 |
| 18386 | 3 | 4 | | | | IV-1 | Plekhs1 |
| 18387 | 3 | 4 | | | | IV-1 | Plg |
| 18388 | 3 | 4 | | | | IV-1 | Plk5 |
| 18389 | 3 | 4 | | | | IV-1 | Plod1 |
| 18390 | 3 | 4 | | | | IV-1 | Plod2 |
| 18391 | 3 | 4 | | | | IV-1 | Plp2 |
| 18392 | 3 | 4 | | | | IV-1 | Pls3 |
| 18393 | 3 | 4 | | | | IV-1 | Plscr1 |
| 18394 | 3 | 4 | | | | IV-1 | Plscr5 |
| 18395 | 3 | 4 | | | | IV-1 | Plvap |
| 18396 | 3 | 4 | | | | IV-1 | Plxdc2 |
| 18397 | 3 | 4 | | | | IV-1 | Plxna4os1 |
| 18398 | 3 | 4 | | | | IV-1 | Plxnb3 |
| 18399 | 3 | 4 | | | | IV-1 | Plxnc1 |
| 18400 | 3 | 4 | | | | IV-1 | Pmfbp1 |
| 18401 | 3 | 4 | | | | IV-1 | Pmis2 |
| 18402 | 3 | 4 | | | | IV-1 | Pmm2 |
| 18403 | 3 | 4 | | | | IV-1 | Pmpcb |
| 18404 | 3 | 4 | | | | IV-1 | Pms2 |
| 18405 | 3 | 4 | | | | IV-1 | Pnisr |
| 18406 | 3 | 4 | | | | IV-1 | Pnldc1 |
| 18407 | 3 | 4 | | | | IV-1 | Pnma2 |
| 18408 | 3 | 4 | | | | IV-1 | Pnma3 |
| 18409 | 3 | 4 | | | | IV-1 | Pnma5 |
| 18410 | 3 | 4 | | | | IV-1 | Pnmal2 |
| 18411 | 3 | 4 | | | | IV-1 | Pnpla1 |
| 18412 | 3 | 4 | | | | IV-1 | Pnpla5 |
| 18413 | 3 | 4 | | | | IV-1 | Pnpla6 |
| 18414 | 3 | 4 | | | | IV-1 | Pnpla8 |
| 18415 | 3 | 4 | | | | IV-1 | Pnrc2 |
| 18416 | 3 | 4 | | | | IV-1 | Poc5 |
| 18417 | 3 | 4 | | | | IV-1 | Podnl1 |
| 18418 | 3 | 4 | | | | IV-1 | Pof1b |
| 18419 | 3 | 4 | | | | IV-1 | Pofut1 |
| 18420 | 3 | 4 | | | | IV-1 | Pofut2 |
| 18421 | 3 | 4 | | | | IV-1 | Poglut1 |
| 18422 | 3 | 4 | | | | IV-1 | Pogz |
| 18423 | 3 | 4 | | | | IV-1 | Poldip3 |
| 18424 | 3 | 4 | | | | IV-1 | Polq |
| 18425 | 3 | 4 | | | | IV-1 | Polr1a |
| 18426 | 3 | 4 | | | | IV-1 | Polr1b |
| 18427 | 3 | 4 | | | | IV-1 | Polr1e |
| 18428 | 3 | 4 | | | | IV-1 | Polr2a |
| 18429 | 3 | 4 | | | | IV-1 | Polr2b |
| 18430 | 3 | 4 | | | | IV-1 | Polr2c |
| 18431 | 3 | 4 | | | | IV-1 | Polr2m |
| 18432 | 3 | 4 | | | | IV-1 | Polr3a |
| 18433 | 3 | 4 | | | | IV-1 | Polr3b |
| 18434 | 3 | 4 | | | | IV-1 | Polr3c |
| 18435 | 3 | 4 | | | | IV-1 | Polr3e |
| 18436 | 3 | 4 | | | | IV-1 | Polr3f |
| 18437 | 3 | 4 | | | | IV-1 | Pom121l12 |
| 18438 | 3 | 4 | | | | IV-1 | Pom121l2 |
| 18439 | 3 | 4 | | | | IV-1 | Pomgnt1 |
| 18440 | 3 | 4 | | | | IV-1 | Pomk |
| 18441 | 3 | 4 | | | | IV-1 | Pomt1 |
| 18442 | 3 | 4 | | | | IV-1 | Pon2 |
| 18443 | 3 | 4 | | | | IV-1 | Porcn |
| 18444 | 3 | 4 | | | | IV-1 | Pot1b |
| 18445 | 3 | 4 | | | | IV-1 | Poteg |
| 18446 | 3 | 4 | | | | IV-1 | Pou1f1 |
| 18447 | 3 | 4 | | | | IV-1 | Pou3f4 |
| 18448 | 3 | 4 | | | | IV-1 | Pou4f1 |
| 18449 | 3 | 4 | | | | IV-1 | Pou4f2 |
| 18450 | 3 | 4 | | | | IV-1 | Ppard |
| 18451 | 3 | 4 | | | | IV-1 | Pparg |
| 18452 | 3 | 4 | | | | IV-1 | Ppargc1b |
| 18453 | 3 | 4 | | | | IV-1 | Ppcdc |
| 18454 | 3 | 4 | | | | IV-1 | Ppef1 |
| 18455 | 3 | 4 | | | | IV-1 | Ppef2 |
| 18456 | 3 | 4 | | | | IV-1 | Ppfia1 |
| 18457 | 3 | 4 | | | | IV-1 | Ppfia2 |
| 18458 | 3 | 4 | | | | IV-1 | Ppfia3 |
| 18459 | 3 | 4 | | | | IV-1 | Ppfia4 |
| 18460 | 3 | 4 | | | | IV-1 | Ppfibp1 |
| 18461 | 3 | 4 | | | | IV-1 | Pphln1 |
| 18462 | 3 | 4 | | | | IV-1 | Ppif |
| 18463 | 3 | 4 | | | | IV-1 | Ppig |
| 18464 | 3 | 4 | | | | IV-1 | Ppil2 |
| 18465 | 3 | 4 | | | | IV-1 | Ppil4 |
| 18466 | 3 | 4 | | | | IV-1 | Ppip5k1 |
| 18467 | 3 | 4 | | | | IV-1 | Ppip5k2 |
| 18468 | 3 | 4 | | | | IV-1 | Ppl |
| 18469 | 3 | 4 | | | | IV-1 | Ppm1a |
| 18470 | 3 | 4 | | | | IV-1 | Ppm1b |
| 18471 | 3 | 4 | | | | IV-1 | Ppm1h |
| 18472 | 3 | 4 | | | | IV-1 | Ppm1j |
| 18473 | 3 | 4 | | | | IV-1 | Ppm1m |
| 18474 | 3 | 4 | | | | IV-1 | Ppm1n |
| 18475 | 3 | 4 | | | | IV-1 | Ppme1 |
| 18476 | 3 | 4 | | | | IV-1 | Ppp1cb |
| 18477 | 3 | 4 | | | | IV-1 | Ppp1cc |
| 18478 | 3 | 4 | | | | IV-1 | Ppp1r17 |
| 18479 | 3 | 4 | | | | IV-1 | Ppp1r1a |
| 18480 | 3 | 4 | | | | IV-1 | Ppp1r2 |
| 18481 | 3 | 4 | | | | IV-1 | Ppp1r2-ps7 |
| 18482 | 3 | 4 | | | | IV-1 | Ppp1r2-ps9 |
| 18483 | 3 | 4 | | | | IV-1 | Ppp1r32 |
| 18484 | 3 | 4 | | | | IV-1 | Ppp1r3fos |
| 18485 | 3 | 4 | | | | IV-1 | Ppp1r42 |
| 18486 | 3 | 4 | | | | IV-1 | Ppp1r7 |
| 18487 | 3 | 4 | | | | IV-1 | Ppp1r8 |
| 18488 | 3 | 4 | | | | IV-1 | Ppp2ca |
| 18489 | 3 | 4 | | | | IV-1 | Ppp2r1a |
| 18490 | 3 | 4 | | | | IV-1 | Ppp2r2a |
| 18491 | 3 | 4 | | | | IV-1 | Ppp2r2c |
| 18492 | 3 | 4 | | | | IV-1 | Ppp2r2cos |
| 18493 | 3 | 4 | | | | IV-1 | Ppp2r3a |
| 18494 | 3 | 4 | | | | IV-1 | Ppp2r3c |
| 18495 | 3 | 4 | | | | IV-1 | Ppp2r3d |
| 18496 | 3 | 4 | | | | IV-1 | Ppp2r5c |
| 18497 | 3 | 4 | | | | IV-1 | Ppp2r5d |
| 18498 | 3 | 4 | | | | IV-1 | Ppp2r5e |
| 18499 | 3 | 4 | | | | IV-1 | Ppp3ca |
| 18500 | 3 | 4 | | | | IV-1 | Ppp3cb |
| 18501 | 3 | 4 | | | | IV-1 | Ppp3r1 |
| 18502 | 3 | 4 | | | | IV-1 | Ppp4r1 |
| 18503 | 3 | 4 | | | | IV-1 | Ppp4r1l-ps |
| 18504 | 3 | 4 | | | | IV-1 | Ppp4r2 |
| 18505 | 3 | 4 | | | | IV-1 | Ppp6c |
| 18506 | 3 | 4 | | | | IV-1 | Ppp6r1 |
| 18507 | 3 | 4 | | | | IV-1 | Ppp6r3 |
| 18508 | 3 | 4 | | | | IV-1 | Ppt1 |
| 18509 | 3 | 4 | | | | IV-1 | Ppt2 |
| 18510 | 3 | 4 | | | | IV-1 | Pptc7 |
| 18511 | 3 | 4 | | | | IV-1 | Ppwd1 |
| 18512 | 3 | 4 | | | | IV-1 | Pqbp1 |
| 18513 | 3 | 4 | | | | IV-1 | Pqlc2 |
| 18514 | 3 | 4 | | | | IV-1 | Pradc1 |
| 18515 | 3 | 4 | | | | IV-1 | Prame |
| 18516 | 3 | 4 | | | | IV-1 | Pramef12 |
| 18517 | 3 | 4 | | | | IV-1 | Pramef17 |
| 18518 | 3 | 4 | | | | IV-1 | Pramef25 |
| 18519 | 3 | 4 | | | | IV-1 | Pramef6 |
| 18520 | 3 | 4 | | | | IV-1 | Pramef8 |
| 18521 | 3 | 4 | | | | IV-1 | Pramel1 |
| 18522 | 3 | 4 | | | | IV-1 | Pramel3 |
| 18523 | 3 | 4 | | | | IV-1 | Pramel7 |
| 18524 | 3 | 4 | | | | IV-1 | Prdm10 |
| 18525 | 3 | 4 | | | | IV-1 | Prdm12 |
| 18526 | 3 | 4 | | | | IV-1 | Prdm13 |
| 18527 | 3 | 4 | | | | IV-1 | Prdm14 |

Fig. 43 - 110

| | | | | | | | |
|---|---|---|---|---|---|---|---|
| 18528 | 3 | 4 | | | | IV-1 | Prdm8 |
| 18529 | 3 | 4 | | | | IV-1 | Prdx3 |
| 18530 | 3 | 4 | | | | IV-1 | Prdx6b |
| 18531 | 3 | 4 | | | | IV-1 | Preb |
| 18532 | 3 | 4 | | | | IV-1 | Prepl |
| 18533 | 3 | 4 | | | | IV-1 | Prh1 |
| 18534 | 3 | 4 | | | | IV-1 | Prickle3 |
| 18535 | 3 | 4 | | | | IV-1 | Primpol |
| 18536 | 3 | 4 | | | | IV-1 | Prkaa1 |
| 18537 | 3 | 4 | | | | IV-1 | Prkab1 |
| 18538 | 3 | 4 | | | | IV-1 | Prkaca |
| 18539 | 3 | 4 | | | | IV-1 | Prkacb |
| 18540 | 3 | 4 | | | | IV-1 | Prkag1 |
| 18541 | 3 | 4 | | | | IV-1 | Prkag2 |
| 18542 | 3 | 4 | | | | IV-1 | Prkag2os1 |
| 18543 | 3 | 4 | | | | IV-1 | Prkar1a |
| 18544 | 3 | 4 | | | | IV-1 | Prkcd |
| 18545 | 3 | 4 | | | | IV-1 | Prkci |
| 18546 | 3 | 4 | | | | IV-1 | Prkd3 |
| 18547 | 3 | 4 | | | | IV-1 | Prkdc |
| 18548 | 3 | 4 | | | | IV-1 | Prkrip1 |
| 18549 | 3 | 4 | | | | IV-1 | Prkrir |
| 18550 | 3 | 4 | | | | IV-1 | Prl2a1 |
| 18551 | 3 | 4 | | | | IV-1 | Prl2b1 |
| 18552 | 3 | 4 | | | | IV-1 | Prl2c1 |
| 18553 | 3 | 4 | | | | IV-1 | Prl2c2 |
| 18554 | 3 | 4 | | | | IV-1 | Prl2c3 |
| 18555 | 3 | 4 | | | | IV-1 | Prmt5 |
| 18556 | 3 | 4 | | | | IV-1 | Prmt6 |
| 18557 | 3 | 4 | | | | IV-1 | Prmt8 |
| 18558 | 3 | 4 | | | | IV-1 | Prn |
| 18559 | 3 | 4 | | | | IV-1 | Proca1 |
| 18560 | 3 | 4 | | | | IV-1 | Prok1 |
| 18561 | 3 | 4 | | | | IV-1 | Prok2 |
| 18562 | 3 | 4 | | | | IV-1 | Prokr1 |
| 18563 | 3 | 4 | | | | IV-1 | Prokr2 |
| 18564 | 3 | 4 | | | | IV-1 | Pros1 |
| 18565 | 3 | 4 | | | | IV-1 | Prosc |
| 18566 | 3 | 4 | | | | IV-1 | Proser2 |
| 18567 | 3 | 4 | | | | IV-1 | Prp2 |
| 18568 | 3 | 4 | | | | IV-1 | Prpf18 |
| 18569 | 3 | 4 | | | | IV-1 | Prpf19 |
| 18570 | 3 | 4 | | | | IV-1 | Prpf3 |
| 18571 | 3 | 4 | | | | IV-1 | Prpf31 |
| 18572 | 3 | 4 | | | | IV-1 | Prpf38a |
| 18573 | 3 | 4 | | | | IV-1 | Prpf39 |
| 18574 | 3 | 4 | | | | IV-1 | Prpf4 |
| 18575 | 3 | 4 | | | | IV-1 | Prpf40b |
| 18576 | 3 | 4 | | | | IV-1 | Prpf6 |
| 18577 | 3 | 4 | | | | IV-1 | Prph |
| 18578 | 3 | 4 | | | | IV-1 | Prph2 |
| 18579 | 3 | 4 | | | | IV-1 | Prpmp5 |
| 18580 | 3 | 4 | | | | IV-1 | Prps1 |
| 18581 | 3 | 4 | | | | IV-1 | Prps1l3 |
| 18582 | 3 | 4 | | | | IV-1 | Prr13 |
| 18583 | 3 | 4 | | | | IV-1 | Prr14 |
| 18584 | 3 | 4 | | | | IV-1 | Prr19 |
| 18585 | 3 | 4 | | | | IV-1 | Prr23a |
| 18586 | 3 | 4 | | | | IV-1 | Prr24 |
| 18587 | 3 | 4 | | | | IV-1 | Prr32 |
| 18588 | 3 | 4 | | | | IV-1 | Prrc2b |
| 18589 | 3 | 4 | | | | IV-1 | Prrt3 |
| 18590 | 3 | 4 | | | | IV-1 | Prrx2 |
| 18591 | 3 | 4 | | | | IV-1 | Prrxl1 |
| 18592 | 3 | 4 | | | | IV-1 | Prss12 |
| 18593 | 3 | 4 | | | | IV-1 | Prss21 |
| 18594 | 3 | 4 | | | | IV-1 | Prss27 |
| 18595 | 3 | 4 | | | | IV-1 | Prss28 |
| 18596 | 3 | 4 | | | | IV-1 | Prss29 |
| 18597 | 3 | 4 | | | | IV-1 | Prss32 |
| 18598 | 3 | 4 | | | | IV-1 | Prss33 |
| 18599 | 3 | 4 | | | | IV-1 | Prss35 |
| 18600 | 3 | 4 | | | | IV-1 | Prss36 |
| 18601 | 3 | 4 | | | | IV-1 | Prss37 |
| 18602 | 3 | 4 | | | | IV-1 | Prss40 |
| 18603 | 3 | 4 | | | | IV-1 | Prss41 |
| 18604 | 3 | 4 | | | | IV-1 | Prss42 |
| 18605 | 3 | 4 | | | | IV-1 | Prss44 |
| 18606 | 3 | 4 | | | | IV-1 | Prss46 |
| 18607 | 3 | 4 | | | | IV-1 | Prss48 |
| 18608 | 3 | 4 | | | | IV-1 | Prss51 |
| 18609 | 3 | 4 | | | | IV-1 | Prss54 |
| 18610 | 3 | 4 | | | | IV-1 | Prss56 |
| 18611 | 3 | 4 | | | | IV-1 | Psap |
| 18612 | 3 | 4 | | | | IV-1 | Psd |
| 18613 | 3 | 4 | | | | IV-1 | Psd2 |
| 18614 | 3 | 4 | | | | IV-1 | Psen1 |
| 18615 | 3 | 4 | | | | IV-1 | Psg17 |
| 18616 | 3 | 4 | | | | IV-1 | Psg18 |
| 18617 | 3 | 4 | | | | IV-1 | Psg19 |
| 18618 | 3 | 4 | | | | IV-1 | Psg20 |
| 18619 | 3 | 4 | | | | IV-1 | Psg21 |
| 18620 | 3 | 4 | | | | IV-1 | Psg22 |
| 18621 | 3 | 4 | | | | IV-1 | Psg23 |
| 18622 | 3 | 4 | | | | IV-1 | Psg26 |
| 18623 | 3 | 4 | | | | IV-1 | Psma6 |
| 18624 | 3 | 4 | | | | IV-1 | Psma8 |
| 18625 | 3 | 4 | | | | IV-1 | Psmb11 |
| 18626 | 3 | 4 | | | | IV-1 | Psmb2 |
| 18627 | 3 | 4 | | | | IV-1 | Psmc3 |
| 18628 | 3 | 4 | | | | IV-1 | Psmc5 |
| 18629 | 3 | 4 | | | | IV-1 | Psmc6 |
| 18630 | 3 | 4 | | | | IV-1 | Psmd12 |
| 18631 | 3 | 4 | | | | IV-1 | Psmd2 |
| 18632 | 3 | 4 | | | | IV-1 | Psmd3 |
| 18633 | 3 | 4 | | | | IV-1 | Psmd6 |
| 18634 | 3 | 4 | | | | IV-1 | Psmd7 |
| 18635 | 3 | 4 | | | | IV-1 | Psmd8 |
| 18636 | 3 | 4 | | | | IV-1 | Psmd9 |
| 18637 | 3 | 4 | | | | IV-1 | Psme2 |
| 18638 | 3 | 4 | | | | IV-1 | Psme3 |
| 18639 | 3 | 4 | | | | IV-1 | Psme4 |
| 18640 | 3 | 4 | | | | IV-1 | Pspn |
| 18641 | 3 | 4 | | | | IV-1 | Ptbp1 |
| 18642 | 3 | 4 | | | | IV-1 | Ptbp2 |
| 18643 | 3 | 4 | | | | IV-1 | Ptbp3 |
| 18644 | 3 | 4 | | | | IV-1 | Ptcd2 |
| 18645 | 3 | 4 | | | | IV-1 | Ptcd3 |
| 18646 | 3 | 4 | | | | IV-1 | Ptch2 |
| 18647 | 3 | 4 | | | | IV-1 | Ptchd1 |
| 18648 | 3 | 4 | | | | IV-1 | Ptchd2 |
| 18649 | 3 | 4 | | | | IV-1 | Ptchd3 |
| 18650 | 3 | 4 | | | | IV-1 | Ptchd4 |
| 18651 | 3 | 4 | | | | IV-1 | Ptdss1 |
| 18652 | 3 | 4 | | | | IV-1 | Ptgdr2 |
| 18653 | 3 | 4 | | | | IV-1 | Ptger4 |
| 18654 | 3 | 4 | | | | IV-1 | Ptges2 |
| 18655 | 3 | 4 | | | | IV-1 | Ptgir |
| 18656 | 3 | 4 | | | | IV-1 | Ptgr2 |
| 18657 | 3 | 4 | | | | IV-1 | Ptgs1 |
| 18658 | 3 | 4 | | | | IV-1 | Ptgs2os |
| 18659 | 3 | 4 | | | | IV-1 | Pth |
| 18660 | 3 | 4 | | | | IV-1 | Pth2r |
| 18661 | 3 | 4 | | | | IV-1 | Ptp4a2 |
| 18662 | 3 | 4 | | | | IV-1 | Ptplad1 |
| 18663 | 3 | 4 | | | | IV-1 | Ptpn1 |
| 18664 | 3 | 4 | | | | IV-1 | Ptpn11 |
| 18665 | 3 | 4 | | | | IV-1 | Ptpn12 |
| 18666 | 3 | 4 | | | | IV-1 | Ptpn20 |
| 18667 | 3 | 4 | | | | IV-1 | Ptpn21 |
| 18668 | 3 | 4 | | | | IV-1 | Ptpn23 |
| 18669 | 3 | 4 | | | | IV-1 | Ptpn6 |
| 18670 | 3 | 4 | | | | IV-1 | Ptpra |
| 18671 | 3 | 4 | | | | IV-1 | Ptprd |
| 18672 | 3 | 4 | | | | IV-1 | Ptprf |
| 18673 | 3 | 4 | | | | IV-1 | Ptprh |
| 18674 | 3 | 4 | | | | IV-1 | Ptprk |
| 18675 | 3 | 4 | | | | IV-1 | Ptprm |
| 18676 | 3 | 4 | | | | IV-1 | Ptprn |
| 18677 | 3 | 4 | | | | IV-1 | Ptprn2 |
| 18678 | 3 | 4 | | | | IV-1 | Ptprq |
| 18679 | 3 | 4 | | | | IV-1 | Ptprr |
| 18680 | 3 | 4 | | | | IV-1 | Ptprt |
| 18681 | 3 | 4 | | | | IV-1 | Ptprtos |
| 18682 | 3 | 4 | | | | IV-1 | Ptpru |
| 18683 | 3 | 4 | | | | IV-1 | Ptprz1 |
| 18684 | 3 | 4 | | | | IV-1 | Ptrf |
| 18685 | 3 | 4 | | | | IV-1 | Pttg1ip |
| 18686 | 3 | 4 | | | | IV-1 | Puf60 |
| 18687 | 3 | 4 | | | | IV-1 | Pum1 |
| 18688 | 3 | 4 | | | | IV-1 | Pum2 |
| 18689 | 3 | 4 | | | | IV-1 | Pura |
| 18690 | 3 | 4 | | | | IV-1 | Purb |
| 18691 | 3 | 4 | | | | IV-1 | Pus10 |
| 18692 | 3 | 4 | | | | IV-1 | Pus3 |
| 18693 | 3 | 4 | | | | IV-1 | Pus7l |
| 18694 | 3 | 4 | | | | IV-1 | Pvrl1 |
| 18695 | 3 | 4 | | | | IV-1 | Pvrl2 |
| 18696 | 3 | 4 | | | | IV-1 | Pwp2 |
| 18697 | 3 | 4 | | | | IV-1 | Pxdn |

Fig. 43 - 111

| | | | | | | | |
|---|---|---|---|---|---|---|---|
| 18698 | 3 | 4 | | | | IV-1 | Pxk |
| 18699 | 3 | 4 | | | | IV-1 | Pxn |
| 18700 | 3 | 4 | | | | IV-1 | Pxt1 |
| 18701 | 3 | 4 | | | | IV-1 | Pygb |
| 18702 | 3 | 4 | | | | IV-1 | Pygo2 |
| 18703 | 3 | 4 | | | | IV-1 | Pyroxd1 |
| 18704 | 3 | 4 | | | | IV-1 | Pyroxd2 |
| 18705 | 3 | 4 | | | | IV-1 | Pyurf |
| 18706 | 3 | 4 | | | | IV-1 | Pzp |
| 18707 | 3 | 4 | | | | IV-1 | Qars |
| 18708 | 3 | 4 | | | | IV-1 | Qk |
| 18709 | 3 | 4 | | | | IV-1 | Qpctl |
| 18710 | 3 | 4 | | | | IV-1 | Qrfpr |
| 18711 | 3 | 4 | | | | IV-1 | Qrich1 |
| 18712 | 3 | 4 | | | | IV-1 | Qrich2 |
| 18713 | 3 | 4 | | | | IV-1 | Qsox1 |
| 18714 | 3 | 4 | | | | IV-1 | Qsox2 |
| 18715 | 3 | 4 | | | | IV-1 | R3hcc1 |
| 18716 | 3 | 4 | | | | IV-1 | R3hcc1l |
| 18717 | 3 | 4 | | | | IV-1 | R3hdm1 |
| 18718 | 3 | 4 | | | | IV-1 | R3hdm2 |
| 18719 | 3 | 4 | | | | IV-1 | R3hdm4 |
| 18720 | 3 | 4 | | | | IV-1 | R3hdml |
| 18721 | 3 | 4 | | | | IV-1 | Rab1 |
| 18722 | 3 | 4 | | | | IV-1 | Rab10 |
| 18723 | 3 | 4 | | | | IV-1 | Rab11a |
| 18724 | 3 | 4 | | | | IV-1 | Rab11fip1 |
| 18725 | 3 | 4 | | | | IV-1 | Rab11fip2 |
| 18726 | 3 | 4 | | | | IV-1 | Rab11fip3 |
| 18727 | 3 | 4 | | | | IV-1 | Rab11fip4os1 |
| 18728 | 3 | 4 | | | | IV-1 | Rab12 |
| 18729 | 3 | 4 | | | | IV-1 | Rab14 |
| 18730 | 3 | 4 | | | | IV-1 | Rab18 |
| 18731 | 3 | 4 | | | | IV-1 | Rab19 |
| 18732 | 3 | 4 | | | | IV-1 | Rab1b |
| 18733 | 3 | 4 | | | | IV-1 | Rab21 |
| 18734 | 3 | 4 | | | | IV-1 | Rab22a |
| 18735 | 3 | 4 | | | | IV-1 | Rab23 |
| 18736 | 3 | 4 | | | | IV-1 | Rab24 |
| 18737 | 3 | 4 | | | | IV-1 | Rab26 |
| 18738 | 3 | 4 | | | | IV-1 | Rab27a |
| 18739 | 3 | 4 | | | | IV-1 | Rab27b |
| 18740 | 3 | 4 | | | | IV-1 | Rab28 |
| 18741 | 3 | 4 | | | | IV-1 | Rab2a |
| 18742 | 3 | 4 | | | | IV-1 | Rab31 |
| 18743 | 3 | 4 | | | | IV-1 | Rab33a |
| 18744 | 3 | 4 | | | | IV-1 | Rab33b |
| 18745 | 3 | 4 | | | | IV-1 | Rab35 |
| 18746 | 3 | 4 | | | | IV-1 | Rab39b |
| 18747 | 3 | 4 | | | | IV-1 | Rab3b |
| 18748 | 3 | 4 | | | | IV-1 | Rab3c |
| 18749 | 3 | 4 | | | | IV-1 | Rab3d |
| 18750 | 3 | 4 | | | | IV-1 | Rab3gap1 |
| 18751 | 3 | 4 | | | | IV-1 | Rab3gap2 |
| 18752 | 3 | 4 | | | | IV-1 | Rab40c |
| 18753 | 3 | 4 | | | | IV-1 | Rab44 |
| 18754 | 3 | 4 | | | | IV-1 | Rab4b |
| 18755 | 3 | 4 | | | | IV-1 | Rab5a |
| 18756 | 3 | 4 | | | | IV-1 | Rab5b |
| 18757 | 3 | 4 | | | | IV-1 | Rab5c |
| 18758 | 3 | 4 | | | | IV-1 | Rab6a |
| 18759 | 3 | 4 | | | | IV-1 | Rab7l1 |
| 18760 | 3 | 4 | | | | IV-1 | Rab8a |
| 18761 | 3 | 4 | | | | IV-1 | Rab9b |
| 18762 | 3 | 4 | | | | IV-1 | Rabep1 |
| 18763 | 3 | 4 | | | | IV-1 | Rabepk |
| 18764 | 3 | 4 | | | | IV-1 | Rabgap1 |
| 18765 | 3 | 4 | | | | IV-1 | Rabgef1 |
| 18766 | 3 | 4 | | | | IV-1 | Rabif |
| 18767 | 3 | 4 | | | | IV-1 | Rac1 |
| 18768 | 3 | 4 | | | | IV-1 | Rad17 |
| 18769 | 3 | 4 | | | | IV-1 | Rad21 |
| 18770 | 3 | 4 | | | | IV-1 | Rad21l |
| 18771 | 3 | 4 | | | | IV-1 | Rad23b |
| 18772 | 3 | 4 | | | | IV-1 | Rad50 |
| 18773 | 3 | 4 | | | | IV-1 | Rad51ap2 |
| 18774 | 3 | 4 | | | | IV-1 | Rad51b |
| 18775 | 3 | 4 | | | | IV-1 | Rad51d |
| 18776 | 3 | 4 | | | | IV-1 | Rad54b |
| 18777 | 3 | 4 | | | | IV-1 | Rad9b |
| 18778 | 3 | 4 | | | | IV-1 | Radil |
| 18779 | 3 | 4 | | | | IV-1 | Raet1a |
| 18780 | 3 | 4 | | | | IV-1 | Raet1b |
| 18781 | 3 | 4 | | | | IV-1 | Raet1c |
| 18782 | 3 | 4 | | | | IV-1 | Raet1e |
| 18783 | 3 | 4 | | | | IV-1 | Raf1 |
| 18784 | 3 | 4 | | | | IV-1 | Rala |
| 18785 | 3 | 4 | | | | IV-1 | Ralgapa1 |
| 18786 | 3 | 4 | | | | IV-1 | Ralgapa2 |
| 18787 | 3 | 4 | | | | IV-1 | Ralgapb |
| 18788 | 3 | 4 | | | | IV-1 | Ralyl |
| 18789 | 3 | 4 | | | | IV-1 | Ranbp17 |
| 18790 | 3 | 4 | | | | IV-1 | Ranbp2 |
| 18791 | 3 | 4 | | | | IV-1 | Ranbp3l |
| 18792 | 3 | 4 | | | | IV-1 | Ranbp9 |
| 18793 | 3 | 4 | | | | IV-1 | Rangap1 |
| 18794 | 3 | 4 | | | | IV-1 | Rap1b |
| 18795 | 3 | 4 | | | | IV-1 | Rap1gap2 |
| 18796 | 3 | 4 | | | | IV-1 | Rap1gds1 |
| 18797 | 3 | 4 | | | | IV-1 | Rap2a |
| 18798 | 3 | 4 | | | | IV-1 | Rap2c |
| 18799 | 3 | 4 | | | | IV-1 | Rapgef1 |
| 18800 | 3 | 4 | | | | IV-1 | Rapgef6 |
| 18801 | 3 | 4 | | | | IV-1 | Rara |
| 18802 | 3 | 4 | | | | IV-1 | Rars |
| 18803 | 3 | 4 | | | | IV-1 | Rars2 |
| 18804 | 3 | 4 | | | | IV-1 | Rasa1 |
| 18805 | 3 | 4 | | | | IV-1 | Rasal1 |
| 18806 | 3 | 4 | | | | IV-1 | Rasd1 |
| 18807 | 3 | 4 | | | | IV-1 | Rasgef1a |
| 18808 | 3 | 4 | | | | IV-1 | Rasgrf1 |
| 18809 | 3 | 4 | | | | IV-1 | Rasgrf2 |
| 18810 | 3 | 4 | | | | IV-1 | Rasip1 |
| 18811 | 3 | 4 | | | | IV-1 | Rasl10b |
| 18812 | 3 | 4 | | | | IV-1 | Rassf1 |
| 18813 | 3 | 4 | | | | IV-1 | Rassf3 |
| 18814 | 3 | 4 | | | | IV-1 | Raver1 |
| 18815 | 3 | 4 | | | | IV-1 | Raver1-fdx1l |
| 18816 | 3 | 4 | | | | IV-1 | Raver2 |
| 18817 | 3 | 4 | | | | IV-1 | Rax |
| 18818 | 3 | 4 | | | | IV-1 | Rb1 |
| 18819 | 3 | 4 | | | | IV-1 | Rbak |
| 18820 | 3 | 4 | | | | IV-1 | Rbbp4 |
| 18821 | 3 | 4 | | | | IV-1 | Rbbp6 |
| 18822 | 3 | 4 | | | | IV-1 | Rbbp7 |
| 18823 | 3 | 4 | | | | IV-1 | Rbbp8nl |
| 18824 | 3 | 4 | | | | IV-1 | Rbbp9 |
| 18825 | 3 | 4 | | | | IV-1 | Rbck1 |
| 18826 | 3 | 4 | | | | IV-1 | Rbl1 |
| 18827 | 3 | 4 | | | | IV-1 | Rbl2 |
| 18828 | 3 | 4 | | | | IV-1 | Rbm11 |
| 18829 | 3 | 4 | | | | IV-1 | Rbm12 |
| 18830 | 3 | 4 | | | | IV-1 | Rbm19 |
| 18831 | 3 | 4 | | | | IV-1 | Rbm22 |
| 18832 | 3 | 4 | | | | IV-1 | Rbm25 |
| 18833 | 3 | 4 | | | | IV-1 | Rbm27 |
| 18834 | 3 | 4 | | | | IV-1 | Rbm28 |
| 18835 | 3 | 4 | | | | IV-1 | Rbm31y |
| 18836 | 3 | 4 | | | | IV-1 | Rbm34 |
| 18837 | 3 | 4 | | | | IV-1 | Rbm39 |
| 18838 | 3 | 4 | | | | IV-1 | Rbm3os |
| 18839 | 3 | 4 | | | | IV-1 | Rbm42 |
| 18840 | 3 | 4 | | | | IV-1 | Rbm44 |
| 18841 | 3 | 4 | | | | IV-1 | Rbm45 |
| 18842 | 3 | 4 | | | | IV-1 | Rbm46 |
| 18843 | 3 | 4 | | | | IV-1 | Rbm46os |
| 18844 | 3 | 4 | | | | IV-1 | Rbm47 |
| 18845 | 3 | 4 | | | | IV-1 | Rbm48 |
| 18846 | 3 | 4 | | | | IV-1 | Rbm4b |
| 18847 | 3 | 4 | | | | IV-1 | Rbm7 |
| 18848 | 3 | 4 | | | | IV-1 | Rbms2 |
| 18849 | 3 | 4 | | | | IV-1 | Rbmxl1 |
| 18850 | 3 | 4 | | | | IV-1 | Rbmxl2 |
| 18851 | 3 | 4 | | | | IV-1 | Rbmy |
| 18852 | 3 | 4 | | | | IV-1 | Rbp3 |
| 18853 | 3 | 4 | | | | IV-1 | Rbpjl |
| 18854 | 3 | 4 | | | | IV-1 | Rbx1 |
| 18855 | 3 | 4 | | | | IV-1 | Rc3h2 |
| 18856 | 3 | 4 | | | | IV-1 | Rcan2 |
| 18857 | 3 | 4 | | | | IV-1 | Rcan3 |
| 18858 | 3 | 4 | | | | IV-1 | Rcbtb1 |
| 18859 | 3 | 4 | | | | IV-1 | Rcbtb2 |
| 18860 | 3 | 4 | | | | IV-1 | Rcc2 |
| 18861 | 3 | 4 | | | | IV-1 | Rccd1 |
| 18862 | 3 | 4 | | | | IV-1 | Rcn1 |
| 18863 | 3 | 4 | | | | IV-1 | Rcn2 |
| 18864 | 3 | 4 | | | | IV-1 | Rcvrn |
| 18865 | 3 | 4 | | | | IV-1 | Rd3 |
| 18866 | 3 | 4 | | | | IV-1 | Rd3l |
| 18867 | 3 | 4 | | | | IV-1 | Rdh1 |

Fig. 43 - 112

| | | | | | | | |
|---|---|---|---|---|---|---|---|
| 18868 | 3 | 4 | | | | IV-1 | Rdh10 |
| 18869 | 3 | 4 | | | | IV-1 | Rdh18-ps |
| 18870 | 3 | 4 | | | | IV-1 | Rdh19 |
| 18871 | 3 | 4 | | | | IV-1 | Rdh7 |
| 18872 | 3 | 4 | | | | IV-1 | Rdh8 |
| 18873 | 3 | 4 | | | | IV-1 | Rdx |
| 18874 | 3 | 4 | | | | IV-1 | Reck |
| 18875 | 3 | 4 | | | | IV-1 | Reep3 |
| 18876 | 3 | 4 | | | | IV-1 | Reep4 |
| 18877 | 3 | 4 | | | | IV-1 | Reg4 |
| 18878 | 3 | 4 | | | | IV-1 | Rell2 |
| 18879 | 3 | 4 | | | | IV-1 | Rem2 |
| 18880 | 3 | 4 | | | | IV-1 | Renbp |
| 18881 | 3 | 4 | | | | IV-1 | Repin1 |
| 18882 | 3 | 4 | | | | IV-1 | Reps1 |
| 18883 | 3 | 4 | | | | IV-1 | Rere |
| 18884 | 3 | 4 | | | | IV-1 | Rergl |
| 18885 | 3 | 4 | | | | IV-1 | Ret |
| 18886 | 3 | 4 | | | | IV-1 | Retnlb |
| 18887 | 3 | 4 | | | | IV-1 | Rev3l |
| 18888 | 3 | 4 | | | | IV-1 | Rex2 |
| 18889 | 3 | 4 | | | | IV-1 | Rexo1 |
| 18890 | 3 | 4 | | | | IV-1 | Rexo4 |
| 18891 | 3 | 4 | | | | IV-1 | Rfc1 |
| 18892 | 3 | 4 | | | | IV-1 | Rfesd |
| 18893 | 3 | 4 | | | | IV-1 | Rfl1 |
| 18894 | 3 | 4 | | | | IV-1 | Rfk |
| 18895 | 3 | 4 | | | | IV-1 | Rfng |
| 18896 | 3 | 4 | | | | IV-1 | Rfpl3s |
| 18897 | 3 | 4 | | | | IV-1 | Rfpl4 |
| 18898 | 3 | 4 | | | | IV-1 | Rfpl4b |
| 18899 | 3 | 4 | | | | IV-1 | Rftn1 |
| 18900 | 3 | 4 | | | | IV-1 | Rftn2 |
| 18901 | 3 | 4 | | | | IV-1 | Rfx4 |
| 18902 | 3 | 4 | | | | IV-1 | Rfx5 |
| 18903 | 3 | 4 | | | | IV-1 | Rfx6 |
| 18904 | 3 | 4 | | | | IV-1 | Rfx8 |
| 18905 | 3 | 4 | | | | IV-1 | Rfxank |
| 18906 | 3 | 4 | | | | IV-1 | Rfxap |
| 18907 | 3 | 4 | | | | IV-1 | Rgag1 |
| 18908 | 3 | 4 | | | | IV-1 | Rgcc |
| 18909 | 3 | 4 | | | | IV-1 | Rgl2 |
| 18910 | 3 | 4 | | | | IV-1 | Rgmb |
| 18911 | 3 | 4 | | | | IV-1 | Rgp1 |
| 18912 | 3 | 4 | | | | IV-1 | Rgr |
| 18913 | 3 | 4 | | | | IV-1 | Rgs11 |
| 18914 | 3 | 4 | | | | IV-1 | Rgs17 |
| 18915 | 3 | 4 | | | | IV-1 | Rgs20 |
| 18916 | 3 | 4 | | | | IV-1 | Rgs21 |
| 18917 | 3 | 4 | | | | IV-1 | Rgs4 |
| 18918 | 3 | 4 | | | | IV-1 | Rgs6 |
| 18919 | 3 | 4 | | | | IV-1 | Rgs8 |
| 18920 | 3 | 4 | | | | IV-1 | Rgs9 |
| 18921 | 3 | 4 | | | | IV-1 | Rgsl1 |
| 18922 | 3 | 4 | | | | IV-1 | Rhbdd1 |
| 18923 | 3 | 4 | | | | IV-1 | Rhbdl2 |
| 18924 | 3 | 4 | | | | IV-1 | Rhbdl3 |
| 18925 | 3 | 4 | | | | IV-1 | Rhcg |
| 18926 | 3 | 4 | | | | IV-1 | Rheb |
| 18927 | 3 | 4 | | | | IV-1 | Rhno1 |
| 18928 | 3 | 4 | | | | IV-1 | Rho |
| 18929 | 3 | 4 | | | | IV-1 | Rhoa |
| 18930 | 3 | 4 | | | | IV-1 | Rhob |
| 18931 | 3 | 4 | | | | IV-1 | Rhobtb1 |
| 18932 | 3 | 4 | | | | IV-1 | Rhobtb3 |
| 18933 | 3 | 4 | | | | IV-1 | Rhog |
| 18934 | 3 | 4 | | | | IV-1 | Rhot1 |
| 18935 | 3 | 4 | | | | IV-1 | Rhot2 |
| 18936 | 3 | 4 | | | | IV-1 | Rhox1 |
| 18937 | 3 | 4 | | | | IV-1 | Rhox10 |
| 18938 | 3 | 4 | | | | IV-1 | Rhox11 |
| 18939 | 3 | 4 | | | | IV-1 | Rhox12 |
| 18940 | 3 | 4 | | | | IV-1 | Rhox13 |
| 18941 | 3 | 4 | | | | IV-1 | Rhox2a |
| 18942 | 3 | 4 | | | | IV-1 | Rhox2c |
| 18943 | 3 | 4 | | | | IV-1 | Rhox2d |
| 18944 | 3 | 4 | | | | IV-1 | Rhox2f |
| 18945 | 3 | 4 | | | | IV-1 | Rhox2g |
| 18946 | 3 | 4 | | | | IV-1 | Rhox3e |
| 18947 | 3 | 4 | | | | IV-1 | Rhox4g |
| 18948 | 3 | 4 | | | | IV-1 | Rhox6 |
| 18949 | 3 | 4 | | | | IV-1 | Ribc2 |
| 18950 | 3 | 4 | | | | IV-1 | Ric8b |
| 18951 | 3 | 4 | | | | IV-1 | Riiad1 |
| 18952 | 3 | 4 | | | | IV-1 | Rimbp2 |
| 18953 | 3 | 4 | | | | IV-1 | Rimbp3 |
| 18954 | 3 | 4 | | | | IV-1 | Rims1 |
| 18955 | 3 | 4 | | | | IV-1 | Rims2 |
| 18956 | 3 | 4 | | | | IV-1 | Rims3 |
| 18957 | 3 | 4 | | | | IV-1 | Rims4 |
| 18958 | 3 | 4 | | | | IV-1 | Rin3 |
| 18959 | 3 | 4 | | | | IV-1 | Rinl |
| 18960 | 3 | 4 | | | | IV-1 | Rint1 |
| 18961 | 3 | 4 | | | | IV-1 | Riok2 |
| 18962 | 3 | 4 | | | | IV-1 | Riok3 |
| 18963 | 3 | 4 | | | | IV-1 | Ripply1 |
| 18964 | 3 | 4 | | | | IV-1 | Ripply2 |
| 18965 | 3 | 4 | | | | IV-1 | Ripply3 |
| 18966 | 3 | 4 | | | | IV-1 | Rit2 |
| 18967 | 3 | 4 | | | | IV-1 | Rlim |
| 18968 | 3 | 4 | | | | IV-1 | Rln1 |
| 18969 | 3 | 4 | | | | IV-1 | Rmdn1 |
| 18970 | 3 | 4 | | | | IV-1 | Rmst |
| 18971 | 3 | 4 | | | | IV-1 | Rnase10 |
| 18972 | 3 | 4 | | | | IV-1 | Rnase11 |
| 18973 | 3 | 4 | | | | IV-1 | Rnase13 |
| 18974 | 3 | 4 | | | | IV-1 | Rnase2a |
| 18975 | 3 | 4 | | | | IV-1 | Rnase4 |
| 18976 | 3 | 4 | | | | IV-1 | Rnaseh2a |
| 18977 | 3 | 4 | | | | IV-1 | Rnf103 |
| 18978 | 3 | 4 | | | | IV-1 | Rnf11 |
| 18979 | 3 | 4 | | | | IV-1 | Rnf111 |
| 18980 | 3 | 4 | | | | IV-1 | Rnf112 |
| 18981 | 3 | 4 | | | | IV-1 | Rnf113a2 |
| 18982 | 3 | 4 | | | | IV-1 | Rnf115 |
| 18983 | 3 | 4 | | | | IV-1 | Rnf13 |
| 18984 | 3 | 4 | | | | IV-1 | Rnf130 |
| 18985 | 3 | 4 | | | | IV-1 | Rnf135 |
| 18986 | 3 | 4 | | | | IV-1 | Rnf138 |
| 18987 | 3 | 4 | | | | IV-1 | Rnf139 |
| 18988 | 3 | 4 | | | | IV-1 | Rnf14 |
| 18989 | 3 | 4 | | | | IV-1 | Rnf145 |
| 18990 | 3 | 4 | | | | IV-1 | Rnf146 |
| 18991 | 3 | 4 | | | | IV-1 | Rnf148 |
| 18992 | 3 | 4 | | | | IV-1 | Rnf149 |
| 18993 | 3 | 4 | | | | IV-1 | Rnf166 |
| 18994 | 3 | 4 | | | | IV-1 | Rnf169 |
| 18995 | 3 | 4 | | | | IV-1 | Rnf17 |
| 18996 | 3 | 4 | | | | IV-1 | Rnf180 |
| 18997 | 3 | 4 | | | | IV-1 | Rnf182 |
| 18998 | 3 | 4 | | | | IV-1 | Rnf183 |
| 18999 | 3 | 4 | | | | IV-1 | Rnf187 |
| 19000 | 3 | 4 | | | | IV-1 | Rnf19a |
| 19001 | 3 | 4 | | | | IV-1 | Rnf2 |
| 19002 | 3 | 4 | | | | IV-1 | Rnf20 |
| 19003 | 3 | 4 | | | | IV-1 | Rnf207 |
| 19004 | 3 | 4 | | | | IV-1 | Rnf215 |
| 19005 | 3 | 4 | | | | IV-1 | Rnf216 |
| 19006 | 3 | 4 | | | | IV-1 | Rnf219 |
| 19007 | 3 | 4 | | | | IV-1 | Rnf220 |
| 19008 | 3 | 4 | | | | IV-1 | Rnf223 |
| 19009 | 3 | 4 | | | | IV-1 | Rnf26 |
| 19010 | 3 | 4 | | | | IV-1 | Rnf34 |
| 19011 | 3 | 4 | | | | IV-1 | Rnf38 |
| 19012 | 3 | 4 | | | | IV-1 | Rnf4 |
| 19013 | 3 | 4 | | | | IV-1 | Rnf40 |
| 19014 | 3 | 4 | | | | IV-1 | Rnf41 |
| 19015 | 3 | 4 | | | | IV-1 | Rnf44 |
| 19016 | 3 | 4 | | | | IV-1 | Rnf5 |
| 19017 | 3 | 4 | | | | IV-1 | Rnf6 |
| 19018 | 3 | 4 | | | | IV-1 | Rnf7 |
| 19019 | 3 | 4 | | | | IV-1 | Rnf8 |
| 19020 | 3 | 4 | | | | IV-1 | Rnft1 |
| 19021 | 3 | 4 | | | | IV-1 | Rnft2 |
| 19022 | 3 | 4 | | | | IV-1 | Rngtt |
| 19023 | 3 | 4 | | | | IV-1 | Rnh1 |
| 19024 | 3 | 4 | | | | IV-1 | Rnmt |
| 19025 | 3 | 4 | | | | IV-1 | Rnps1 |
| 19026 | 3 | 4 | | | | IV-1 | Rnu11 |
| 19027 | 3 | 4 | | | | IV-1 | Rnu12 |
| 19028 | 3 | 4 | | | | IV-1 | Rnu6 |
| 19029 | 3 | 4 | | | | IV-1 | Rnu7 |
| 19030 | 3 | 4 | | | | IV-1 | Rnu73b |
| 19031 | 3 | 4 | | | | IV-1 | Rom1 |
| 19032 | 3 | 4 | | | | IV-1 | Rorb |
| 19033 | 3 | 4 | | | | IV-1 | Ros1 |
| 19034 | 3 | 4 | | | | IV-1 | Rp1 |
| 19035 | 3 | 4 | | | | IV-1 | Rp1l1 |
| 19036 | 3 | 4 | | | | IV-1 | Rp2h |
| 19037 | 3 | 4 | | | | IV-1 | Rpap1 |

Fig. 43 - 113

| | | | | | | | | |
|---|---|---|---|---|---|---|---|---|
| 19038 | 3 | 4 | | | | IV-1 | Rpap2 | |
| 19039 | 3 | 4 | | | | IV-1 | Rpe | |
| 19040 | 3 | 4 | | | | IV-1 | Rpe65 | |
| 19041 | 3 | 4 | | | | IV-1 | Rpgrip1l | |
| 19042 | 3 | 4 | | | | IV-1 | Rpia | |
| 19043 | 3 | 4 | | | | IV-1 | Rpl14-ps1 | |
| 19044 | 3 | 4 | | | | IV-1 | Rpl15 | |
| 19045 | 3 | 4 | | | | IV-1 | Rpl18a | |
| 19046 | 3 | 4 | | | | IV-1 | Rpl26 | |
| 19047 | 3 | 4 | | | | IV-1 | Rpl4 | |
| 19048 | 3 | 4 | | | | IV-1 | Rpl5 | |
| 19049 | 3 | 4 | | | | IV-1 | Rpl6 | |
| 19050 | 3 | 4 | | | | IV-1 | Rpl7 | |
| 19051 | 3 | 4 | | | | IV-1 | Rpl7a | |
| 19052 | 3 | 4 | | | | IV-1 | Rpl7l1 | |
| 19053 | 3 | 4 | | | | IV-1 | Rplp0 | |
| 19054 | 3 | 4 | | | | IV-1 | Rpn2 | |
| 19055 | 3 | 4 | | | | IV-1 | Rpp14 | |
| 19056 | 3 | 4 | | | | IV-1 | Rprd1b | |
| 19057 | 3 | 4 | | | | IV-1 | Rprl1 | |
| 19058 | 3 | 4 | | | | IV-1 | Rprl2 | |
| 19059 | 3 | 4 | | | | IV-1 | Rprl3 | |
| 19060 | 3 | 4 | | | | IV-1 | Rprm | |
| 19061 | 3 | 4 | | | | IV-1 | Rps15a | |
| 19062 | 3 | 4 | | | | IV-1 | Rps21 | |
| 19063 | 3 | 4 | | | | IV-1 | Rps27rt | |
| 19064 | 3 | 4 | | | | IV-1 | Rps3 | |
| 19065 | 3 | 4 | | | | IV-1 | Rps6ka1 | |
| 19066 | 3 | 4 | | | | IV-1 | Rps6ka3 | |
| 19067 | 3 | 4 | | | | IV-1 | Rps6ka4 | |
| 19068 | 3 | 4 | | | | IV-1 | Rps6ka6 | |
| 19069 | 3 | 4 | | | | IV-1 | Rps6kb2 | |
| 19070 | 3 | 4 | | | | IV-1 | Rps6kc1 | |
| 19071 | 3 | 4 | | | | IV-1 | Rqcd1 | |
| 19072 | 3 | 4 | | | | IV-1 | Rraga | |
| 19073 | 3 | 4 | | | | IV-1 | Rragc | |
| 19074 | 3 | 4 | | | | IV-1 | Rras | |
| 19075 | 3 | 4 | | | | IV-1 | Rrh | |
| 19076 | 3 | 4 | | | | IV-1 | Rrn3 | |
| 19077 | 3 | 4 | | | | IV-1 | Rrnad1 | |
| 19078 | 3 | 4 | | | | IV-1 | Rrp8 | |
| 19079 | 3 | 4 | | | | IV-1 | Rrs1 | |
| 19080 | 3 | 4 | | | | IV-1 | Rs1 | |
| 19081 | 3 | 4 | | | | IV-1 | Rsad1 | |
| 19082 | 3 | 4 | | | | IV-1 | Rsbn1l | |
| 19083 | 3 | 4 | | | | IV-1 | Rsg1 | |
| 19084 | 3 | 4 | | | | IV-1 | Rsl24d1 | |
| 19085 | 3 | 4 | | | | IV-1 | Rsph3b | |
| 19086 | 3 | 4 | | | | IV-1 | Rsph6a | |
| 19087 | 3 | 4 | | | | IV-1 | Rspo1 | |
| 19088 | 3 | 4 | | | | IV-1 | Rspo2 | |
| 19089 | 3 | 4 | | | | IV-1 | Rspo3 | |
| 19090 | 3 | 4 | | | | IV-1 | Rspo4 | |
| 19091 | 3 | 4 | | | | IV-1 | Rsrc1 | |
| 19092 | 3 | 4 | | | | IV-1 | Rsrc2 | |
| 19093 | 3 | 4 | | | | IV-1 | Rsrp1 | |
| 19094 | 3 | 4 | | | | IV-1 | Rsu1 | |
| 19095 | 3 | 4 | | | | IV-1 | Rtbdn | |
| 19096 | 3 | 4 | | | | IV-1 | Rtcb | |
| 19097 | 3 | 4 | | | | IV-1 | Rtdr1 | |
| 19098 | 3 | 4 | | | | IV-1 | Rtel1 | |
| 19099 | 3 | 4 | | | | IV-1 | Rtf1 | |
| 19100 | 3 | 4 | | | | IV-1 | Rtl1 | |
| 19101 | 3 | 4 | | | | IV-1 | Rtn3 | |
| 19102 | 3 | 4 | | | | IV-1 | Rtp1 | |
| 19103 | 3 | 4 | | | | IV-1 | Rtp2 | |
| 19104 | 3 | 4 | | | | IV-1 | Rubie | |
| 19105 | 3 | 4 | | | | IV-1 | Rufy3 | |
| 19106 | 3 | 4 | | | | IV-1 | Rundc1 | |
| 19107 | 3 | 4 | | | | IV-1 | Rundc3b | |
| 19108 | 3 | 4 | | | | IV-1 | Runx1t1 | |
| 19109 | 3 | 4 | | | | IV-1 | Runx2 | |
| 19110 | 3 | 4 | | | | IV-1 | Runx3 | |
| 19111 | 3 | 4 | | | | IV-1 | Ruvbl2 | |
| 19112 | 3 | 4 | | | | IV-1 | Rwdd4a | |
| 19113 | 3 | 4 | | | | IV-1 | Rxfp1 | |
| 19114 | 3 | 4 | | | | IV-1 | Rxfp3 | |
| 19115 | 3 | 4 | | | | IV-1 | Rxfp4 | |
| 19116 | 3 | 4 | | | | IV-1 | Rybp | |
| 19117 | 3 | 4 | | | | IV-1 | Ryr2 | |
| 19118 | 3 | 4 | | | | IV-1 | Ryr3 | |
| 19119 | 3 | 4 | | | | IV-1 | S100z | |
| 19120 | 3 | 4 | | | | IV-1 | S1pr3 | |
| 19121 | 3 | 4 | | | | IV-1 | Sacm1l | |
| 19122 | 3 | 4 | | | | IV-1 | Sacs | |
| 19123 | 3 | 4 | | | | IV-1 | Sae1 | |
| 19124 | 3 | 4 | | | | IV-1 | Safb | |
| 19125 | 3 | 4 | | | | IV-1 | Safb2 | |
| 19126 | 3 | 4 | | | | IV-1 | Sall3 | |
| 19127 | 3 | 4 | | | | IV-1 | Sall4 | |
| 19128 | 3 | 4 | | | | IV-1 | Samd15 | |
| 19129 | 3 | 4 | | | | IV-1 | Samd3 | |
| 19130 | 3 | 4 | | | | IV-1 | Samd7 | |
| 19131 | 3 | 4 | | | | IV-1 | Samd8 | |
| 19132 | 3 | 4 | | | | IV-1 | Samt2 | |
| 19133 | 3 | 4 | | | | IV-1 | Samt3 | |
| 19134 | 3 | 4 | | | | IV-1 | Samt4 | |
| 19135 | 3 | 4 | | | | IV-1 | Sap130 | |
| 19136 | 3 | 4 | | | | IV-1 | Sap18 | |
| 19137 | 3 | 4 | | | | IV-1 | Sar1a | |
| 19138 | 3 | 4 | | | | IV-1 | Sardh | |
| 19139 | 3 | 4 | | | | IV-1 | Sarm1 | |
| 19140 | 3 | 4 | | | | IV-1 | Sars | |
| 19141 | 3 | 4 | | | | IV-1 | Sart3 | |
| 19142 | 3 | 4 | | | | IV-1 | Sass6 | |
| 19143 | 3 | 4 | | | | IV-1 | Satb2 | |
| 19144 | 3 | 4 | | | | IV-1 | Sat1 | |
| 19145 | 3 | 4 | | | | IV-1 | Sav1 | |
| 19146 | 3 | 4 | | | | IV-1 | Sbds | |
| 19147 | 3 | 4 | | | | IV-1 | Sbf1 | |
| 19148 | 3 | 4 | | | | IV-1 | Sbf2 | |
| 19149 | 3 | 4 | | | | IV-1 | Sbno1 | |
| 19150 | 3 | 4 | | | | IV-1 | Sbp | |
| 19151 | 3 | 4 | | | | IV-1 | Sbpl | |
| 19152 | 3 | 4 | | | | IV-1 | Sbspon | |
| 19153 | 3 | 4 | | | | IV-1 | Scaf1 | |
| 19154 | 3 | 4 | | | | IV-1 | Scaf11 | |
| 19155 | 3 | 4 | | | | IV-1 | Scaf8 | |
| 19156 | 3 | 4 | | | | IV-1 | Scamp1 | |
| 19157 | 3 | 4 | | | | IV-1 | Scamp2 | |
| 19158 | 3 | 4 | | | | IV-1 | Scamp4 | |
| 19159 | 3 | 4 | | | | IV-1 | Scap | |
| 19160 | 3 | 4 | | | | IV-1 | Scarb2 | |
| 19161 | 3 | 4 | | | | IV-1 | Scarf1 | |
| 19162 | 3 | 4 | | | | IV-1 | Scarletltr | |
| 19163 | 3 | 4 | | | | IV-1 | Scarna10 | |
| 19164 | 3 | 4 | | | | IV-1 | Scarna17 | |
| 19165 | 3 | 4 | | | | IV-1 | Scarna2 | |
| 19166 | 3 | 4 | | | | IV-1 | Scarna3a | |
| 19167 | 3 | 4 | | | | IV-1 | Scarna8 | |
| 19168 | 3 | 4 | | | | IV-1 | Scfd2 | |
| 19169 | 3 | 4 | | | | IV-1 | Scgb1b19 | |
| 19170 | 3 | 4 | | | | IV-1 | Scgb1b2 | |
| 19171 | 3 | 4 | | | | IV-1 | Scgb1b20 | |
| 19172 | 3 | 4 | | | | IV-1 | Scgb1b24 | |
| 19173 | 3 | 4 | | | | IV-1 | Scgb1b29 | |
| 19174 | 3 | 4 | | | | IV-1 | Scgb2b12 | |
| 19175 | 3 | 4 | | | | IV-1 | Scgb2b20 | |
| 19176 | 3 | 4 | | | | IV-1 | Schip1 | |
| 19177 | 3 | 4 | | | | IV-1 | Scmh1 | |
| 19178 | 3 | 4 | | | | IV-1 | Scml2 | |
| 19179 | 3 | 4 | | | | IV-1 | Scn10a | |
| 19180 | 3 | 4 | | | | IV-1 | Scn11a | |
| 19181 | 3 | 4 | | | | IV-1 | Scn1a | |
| 19182 | 3 | 4 | | | | IV-1 | Scn5a | |
| 19183 | 3 | 4 | | | | IV-1 | Scn7a | |
| 19184 | 3 | 4 | | | | IV-1 | Scn8a | |
| 19185 | 3 | 4 | | | | IV-1 | Scn9a | |
| 19186 | 3 | 4 | | | | IV-1 | Scp2 | |
| 19187 | 3 | 4 | | | | IV-1 | Scpep1 | |
| 19188 | 3 | 4 | | | | IV-1 | Scpep1os | |
| 19189 | 3 | 4 | | | | IV-1 | Scrn3 | |
| 19190 | 3 | 4 | | | | IV-1 | Scrt1 | |
| 19191 | 3 | 4 | | | | IV-1 | Scrt2 | |
| 19192 | 3 | 4 | | | | IV-1 | Scube1 | |
| 19193 | 3 | 4 | | | | IV-1 | Scyl1 | |
| 19194 | 3 | 4 | | | | IV-1 | Scyl2 | |
| 19195 | 3 | 4 | | | | IV-1 | Sdad1 | |
| 19196 | 3 | 4 | | | | IV-1 | Sdc2 | |
| 19197 | 3 | 4 | | | | IV-1 | Sdcbp | |
| 19198 | 3 | 4 | | | | IV-1 | Sdccag3 | |
| 19199 | 3 | 4 | | | | IV-1 | Sde2 | |
| 19200 | 3 | 4 | | | | IV-1 | Sdf4 | |
| 19201 | 3 | 4 | | | | IV-1 | Sdha | |
| 19202 | 3 | 4 | | | | IV-1 | Sdhaf2 | |
| 19203 | 3 | 4 | | | | IV-1 | Sdhd | |
| 19204 | 3 | 4 | | | | IV-1 | Sdk1 | |
| 19205 | 3 | 4 | | | | IV-1 | Sdk2 | |
| 19206 | 3 | 4 | | | | IV-1 | Sdpr | |
| 19207 | 3 | 4 | | | | IV-1 | Sdr16c5 | |

Fig. 43 - 114

| | | | | | | | |
|---|---|---|---|---|---|---|---|
| 19208 | 3 | 4 | | | | IV-1 | Sdr39u1 |
| 19209 | 3 | 4 | | | | IV-1 | Sebox |
| 19210 | 3 | 4 | | | | IV-1 | Sec1 |
| 19211 | 3 | 4 | | | | IV-1 | Sec13 |
| 19212 | 3 | 4 | | | | IV-1 | Sec14l1 |
| 19213 | 3 | 4 | | | | IV-1 | Sec14l3 |
| 19214 | 3 | 4 | | | | IV-1 | Sec22a |
| 19215 | 3 | 4 | | | | IV-1 | Sec22b |
| 19216 | 3 | 4 | | | | IV-1 | Sec22c |
| 19217 | 3 | 4 | | | | IV-1 | Sec23a |
| 19218 | 3 | 4 | | | | IV-1 | Sec23b |
| 19219 | 3 | 4 | | | | IV-1 | Sec23ip |
| 19220 | 3 | 4 | | | | IV-1 | Sec24c |
| 19221 | 3 | 4 | | | | IV-1 | Sec24d |
| 19222 | 3 | 4 | | | | IV-1 | Sec31a |
| 19223 | 3 | 4 | | | | IV-1 | Sec31b |
| 19224 | 3 | 4 | | | | IV-1 | Sec61a1 |
| 19225 | 3 | 4 | | | | IV-1 | Sec61a2 |
| 19226 | 3 | 4 | | | | IV-1 | Sec62 |
| 19227 | 3 | 4 | | | | IV-1 | Sec63 |
| 19228 | 3 | 4 | | | | IV-1 | Secisbp2 |
| 19229 | 3 | 4 | | | | IV-1 | Secisbp2l |
| 19230 | 3 | 4 | | | | IV-1 | Seh1l |
| 19231 | 3 | 4 | | | | IV-1 | Sel1l2 |
| 19232 | 3 | 4 | | | | IV-1 | Sel1l3 |
| 19233 | 3 | 4 | | | | IV-1 | Sele |
| 19234 | 3 | 4 | | | | IV-1 | Selt |
| 19235 | 3 | 4 | | | | IV-1 | Sema3a |
| 19236 | 3 | 4 | | | | IV-1 | Sema3b |
| 19237 | 3 | 4 | | | | IV-1 | Sema3d |
| 19238 | 3 | 4 | | | | IV-1 | Sema3e |
| 19239 | 3 | 4 | | | | IV-1 | Sema4a |
| 19240 | 3 | 4 | | | | IV-1 | Sema4c |
| 19241 | 3 | 4 | | | | IV-1 | Sema4f |
| 19242 | 3 | 4 | | | | IV-1 | Sema4g |
| 19243 | 3 | 4 | | | | IV-1 | Sema5b |
| 19244 | 3 | 4 | | | | IV-1 | Sema6d |
| 19245 | 3 | 4 | | | | IV-1 | Sema7a |
| 19246 | 3 | 4 | | | | IV-1 | Senp1 |
| 19247 | 3 | 4 | | | | IV-1 | Senp2 |
| 19248 | 3 | 4 | | | | IV-1 | Senp3 |
| 19249 | 3 | 4 | | | | IV-1 | Senp5 |
| 19250 | 3 | 4 | | | | IV-1 | Senp6 |
| 19251 | 3 | 4 | | | | IV-1 | Sephs1 |
| 19252 | 3 | 4 | | | | IV-1 | Sephs2 |
| 19253 | 3 | 4 | | | | IV-1 | Sepn1 |
| 19254 | 3 | 4 | | | | IV-1 | Sepp1 |
| 19255 | 3 | 4 | | | | IV-1 | Sept10 |
| 19256 | 3 | 4 | | | | IV-1 | Sept12 |
| 19257 | 3 | 4 | | | | IV-1 | Sept14 |
| 19258 | 3 | 4 | | | | IV-1 | Sept15 |
| 19259 | 3 | 4 | | | | IV-1 | Sept2 |
| 19260 | 3 | 4 | | | | IV-1 | Sept3 |
| 19261 | 3 | 4 | | | | IV-1 | Sept7 |
| 19262 | 3 | 4 | | | | IV-1 | Sept9 |
| 19263 | 3 | 4 | | | | IV-1 | Sepw1 |
| 19264 | 3 | 4 | | | | IV-1 | Serbp1 |
| 19265 | 3 | 4 | | | | IV-1 | Serf2 |
| 19266 | 3 | 4 | | | | IV-1 | Serinc1 |
| 19267 | 3 | 4 | | | | IV-1 | Serinc2 |
| 19268 | 3 | 4 | | | | IV-1 | Serinc3 |
| 19269 | 3 | 4 | | | | IV-1 | Serinc4 |
| 19270 | 3 | 4 | | | | IV-1 | Serp1 |
| 19271 | 3 | 4 | | | | IV-1 | Serpina5 |
| 19272 | 3 | 4 | | | | IV-1 | Serpinb1b |
| 19273 | 3 | 4 | | | | IV-1 | Serpinb1c |
| 19274 | 3 | 4 | | | | IV-1 | Serpinb3b |
| 19275 | 3 | 4 | | | | IV-1 | Serpinb3d |
| 19276 | 3 | 4 | | | | IV-1 | Serpinb5 |
| 19277 | 3 | 4 | | | | IV-1 | Serpinb6d |
| 19278 | 3 | 4 | | | | IV-1 | Serpinb7 |
| 19279 | 3 | 4 | | | | IV-1 | Serpinb9c |
| 19280 | 3 | 4 | | | | IV-1 | Serpinb9e |
| 19281 | 3 | 4 | | | | IV-1 | Serpinb9f |
| 19282 | 3 | 4 | | | | IV-1 | Serpinb9g |
| 19283 | 3 | 4 | | | | IV-1 | Serpinc1 |
| 19284 | 3 | 4 | | | | IV-1 | Sertm1 |
| 19285 | 3 | 4 | | | | IV-1 | Sesrd1 |
| 19286 | 3 | 4 | | | | IV-1 | Set |
| 19287 | 3 | 4 | | | | IV-1 | Setd3 |
| 19288 | 3 | 4 | | | | IV-1 | Setd8 |
| 19289 | 3 | 4 | | | | IV-1 | Setdb1 |
| 19290 | 3 | 4 | | | | IV-1 | Setmar |
| 19291 | 3 | 4 | | | | IV-1 | Setx |
| 19292 | 3 | 4 | | | | IV-1 | Sez6 |
| 19293 | 3 | 4 | | | | IV-1 | Sez6l2 |
| 19294 | 3 | 4 | | | | IV-1 | Sf1 |
| 19295 | 3 | 4 | | | | IV-1 | Sf3a1 |
| 19296 | 3 | 4 | | | | IV-1 | Sf3b1 |
| 19297 | 3 | 4 | | | | IV-1 | Sf3b2 |
| 19298 | 3 | 4 | | | | IV-1 | Sf3b3 |
| 19299 | 3 | 4 | | | | IV-1 | Sf3b4 |
| 19300 | 3 | 4 | | | | IV-1 | Sfmbt1 |
| 19301 | 3 | 4 | | | | IV-1 | Sfmbt2 |
| 19302 | 3 | 4 | | | | IV-1 | Sfr1 |
| 19303 | 3 | 4 | | | | IV-1 | Sfswap |
| 19304 | 3 | 4 | | | | IV-1 | Sft2d3 |
| 19305 | 3 | 4 | | | | IV-1 | Sftpb |
| 19306 | 3 | 4 | | | | IV-1 | Sfxn2 |
| 19307 | 3 | 4 | | | | IV-1 | Sfxn3 |
| 19308 | 3 | 4 | | | | IV-1 | Sfxn4 |
| 19309 | 3 | 4 | | | | IV-1 | Sgcb |
| 19310 | 3 | 4 | | | | IV-1 | Sgcz |
| 19311 | 3 | 4 | | | | IV-1 | Sgip1 |
| 19312 | 3 | 4 | | | | IV-1 | Sgms2 |
| 19313 | 3 | 4 | | | | IV-1 | Sgol1 |
| 19314 | 3 | 4 | | | | IV-1 | Sgpl1 |
| 19315 | 3 | 4 | | | | IV-1 | Sgpp1 |
| 19316 | 3 | 4 | | | | IV-1 | Sgsh |
| 19317 | 3 | 4 | | | | IV-1 | Sgsm1 |
| 19318 | 3 | 4 | | | | IV-1 | Sgta |
| 19319 | 3 | 4 | | | | IV-1 | Sh2b1 |
| 19320 | 3 | 4 | | | | IV-1 | Sh2d1b1 |
| 19321 | 3 | 4 | | | | IV-1 | Sh2d1b2 |
| 19322 | 3 | 4 | | | | IV-1 | Sh2d3c |
| 19323 | 3 | 4 | | | | IV-1 | Sh2d5 |
| 19324 | 3 | 4 | | | | IV-1 | Sh3bgrl |
| 19325 | 3 | 4 | | | | IV-1 | Sh3bp1 |
| 19326 | 3 | 4 | | | | IV-1 | Sh3bp5 |
| 19327 | 3 | 4 | | | | IV-1 | Sh3bp5l |
| 19328 | 3 | 4 | | | | IV-1 | Sh3gl1 |
| 19329 | 3 | 4 | | | | IV-1 | Sh3glb1 |
| 19330 | 3 | 4 | | | | IV-1 | Sh3glb2 |
| 19331 | 3 | 4 | | | | IV-1 | Sh3rf1 |
| 19332 | 3 | 4 | | | | IV-1 | Sh3rf3 |
| 19333 | 3 | 4 | | | | IV-1 | Shank1 |
| 19334 | 3 | 4 | | | | IV-1 | Sharpin |
| 19335 | 3 | 4 | | | | IV-1 | Shbg |
| 19336 | 3 | 4 | | | | IV-1 | Shc1 |
| 19337 | 3 | 4 | | | | IV-1 | Shc2 |
| 19338 | 3 | 4 | | | | IV-1 | Shc3 |
| 19339 | 3 | 4 | | | | IV-1 | Shc4 |
| 19340 | 3 | 4 | | | | IV-1 | Shcbp1 |
| 19341 | 3 | 4 | | | | IV-1 | Shcbp1l |
| 19342 | 3 | 4 | | | | IV-1 | She |
| 19343 | 3 | 4 | | | | IV-1 | Shisa3 |
| 19344 | 3 | 4 | | | | IV-1 | Shisa6 |
| 19345 | 3 | 4 | | | | IV-1 | Shisa7 |
| 19346 | 3 | 4 | | | | IV-1 | Shisa9 |
| 19347 | 3 | 4 | | | | IV-1 | Shoc2 |
| 19348 | 3 | 4 | | | | IV-1 | Shox2 |
| 19349 | 3 | 4 | | | | IV-1 | Siah1a |
| 19350 | 3 | 4 | | | | IV-1 | Siah2 |
| 19351 | 3 | 4 | | | | IV-1 | Siah3 |
| 19352 | 3 | 4 | | | | IV-1 | Sidt1 |
| 19353 | 3 | 4 | | | | IV-1 | Sidt2 |
| 19354 | 3 | 4 | | | | IV-1 | Siglec15 |
| 19355 | 3 | 4 | | | | IV-1 | Siglec5 |
| 19356 | 3 | 4 | | | | IV-1 | Sik3 |
| 19357 | 3 | 4 | | | | IV-1 | Sike1 |
| 19358 | 3 | 4 | | | | IV-1 | Sim1 |
| 19359 | 3 | 4 | | | | IV-1 | Sin3a |
| 19360 | 3 | 4 | | | | IV-1 | Sin3b |
| 19361 | 3 | 4 | | | | IV-1 | Sipa1 |
| 19362 | 3 | 4 | | | | IV-1 | Sirt1 |
| 19363 | 3 | 4 | | | | IV-1 | Sirt4 |
| 19364 | 3 | 4 | | | | IV-1 | Sirt7 |
| 19365 | 3 | 4 | | | | IV-1 | Sis |
| 19366 | 3 | 4 | | | | IV-1 | Six2 |
| 19367 | 3 | 4 | | | | IV-1 | Six3 |
| 19368 | 3 | 4 | | | | IV-1 | Six6 |
| 19369 | 3 | 4 | | | | IV-1 | Ska1 |
| 19370 | 3 | 4 | | | | IV-1 | Skida1 |
| 19371 | 3 | 4 | | | | IV-1 | Skint1 |
| 19372 | 3 | 4 | | | | IV-1 | Skint11 |
| 19373 | 3 | 4 | | | | IV-1 | Skint2 |
| 19374 | 3 | 4 | | | | IV-1 | Skint3 |
| 19375 | 3 | 4 | | | | IV-1 | Skint4 |
| 19376 | 3 | 4 | | | | IV-1 | Skint5 |
| 19377 | 3 | 4 | | | | IV-1 | Skint6 |

Fig. 43 - 115

| | | | | | | | |
|---|---|---|---|---|---|---|---|
| 19378 | 3 | 4 | | | | IV-1 | Skint8 |
| 19379 | 3 | 4 | | | | IV-1 | Skint9 |
| 19380 | 3 | 4 | | | | IV-1 | Skor2 |
| 19381 | 3 | 4 | | | | IV-1 | Slain1os |
| 19382 | 3 | 4 | | | | IV-1 | Slain2 |
| 19383 | 3 | 4 | | | | IV-1 | Slamf8 |
| 19384 | 3 | 4 | | | | IV-1 | Slc10a1 |
| 19385 | 3 | 4 | | | | IV-1 | Slc10a3-ubl4 |
| 19386 | 3 | 4 | | | | IV-1 | Slc10a4 |
| 19387 | 3 | 4 | | | | IV-1 | Slc12a3 |
| 19388 | 3 | 4 | | | | IV-1 | Slc12a4 |
| 19389 | 3 | 4 | | | | IV-1 | Slc12a5 |
| 19390 | 3 | 4 | | | | IV-1 | Slc13a2 |
| 19391 | 3 | 4 | | | | IV-1 | Slc13a2os |
| 19392 | 3 | 4 | | | | IV-1 | Slc13a4 |
| 19393 | 3 | 4 | | | | IV-1 | Slc13a5 |
| 19394 | 3 | 4 | | | | IV-1 | Slc14a2 |
| 19395 | 3 | 4 | | | | IV-1 | Slc15a5 |
| 19396 | 3 | 4 | | | | IV-1 | Slc16a13 |
| 19397 | 3 | 4 | | | | IV-1 | Slc16a4 |
| 19398 | 3 | 4 | | | | IV-1 | Slc16a8 |
| 19399 | 3 | 4 | | | | IV-1 | Slc17a4 |
| 19400 | 3 | 4 | | | | IV-1 | Slc17a6 |
| 19401 | 3 | 4 | | | | IV-1 | Slc18a1 |
| 19402 | 3 | 4 | | | | IV-1 | Slc19a3 |
| 19403 | 3 | 4 | | | | IV-1 | Slc1a6 |
| 19404 | 3 | 4 | | | | IV-1 | Slc1a7 |
| 19405 | 3 | 4 | | | | IV-1 | Slc22a12 |
| 19406 | 3 | 4 | | | | IV-1 | Slc22a13 |
| 19407 | 3 | 4 | | | | IV-1 | Slc22a13b-ps |
| 19408 | 3 | 4 | | | | IV-1 | Slc22a14 |
| 19409 | 3 | 4 | | | | IV-1 | Slc22a15 |
| 19410 | 3 | 4 | | | | IV-1 | Slc22a16 |
| 19411 | 3 | 4 | | | | IV-1 | Slc22a19 |
| 19412 | 3 | 4 | | | | IV-1 | Slc22a20 |
| 19413 | 3 | 4 | | | | IV-1 | Slc22a22 |
| 19414 | 3 | 4 | | | | IV-1 | Slc22a23 |
| 19415 | 3 | 4 | | | | IV-1 | Slc22a27 |
| 19416 | 3 | 4 | | | | IV-1 | Slc22a29 |
| 19417 | 3 | 4 | | | | IV-1 | Slc22a3 |
| 19418 | 3 | 4 | | | | IV-1 | Slc22a6 |
| 19419 | 3 | 4 | | | | IV-1 | Slc22a7 |
| 19420 | 3 | 4 | | | | IV-1 | Slc22a8 |
| 19421 | 3 | 4 | | | | IV-1 | Slc24a1 |
| 19422 | 3 | 4 | | | | IV-1 | Slc25a1 |
| 19423 | 3 | 4 | | | | IV-1 | Slc25a11 |
| 19424 | 3 | 4 | | | | IV-1 | Slc25a13 |
| 19425 | 3 | 4 | | | | IV-1 | Slc25a15 |
| 19426 | 3 | 4 | | | | IV-1 | Slc25a16 |
| 19427 | 3 | 4 | | | | IV-1 | Slc25a17 |
| 19428 | 3 | 4 | | | | IV-1 | Slc25a2 |
| 19429 | 3 | 4 | | | | IV-1 | Slc25a22 |
| 19430 | 3 | 4 | | | | IV-1 | Slc25a24 |
| 19431 | 3 | 4 | | | | IV-1 | Slc25a29 |
| 19432 | 3 | 4 | | | | IV-1 | Slc25a3 |
| 19433 | 3 | 4 | | | | IV-1 | Slc25a31 |
| 19434 | 3 | 4 | | | | IV-1 | Slc25a38 |
| 19435 | 3 | 4 | | | | IV-1 | Slc25a40 |
| 19436 | 3 | 4 | | | | IV-1 | Slc25a41 |
| 19437 | 3 | 4 | | | | IV-1 | Slc25a43 |
| 19438 | 3 | 4 | | | | IV-1 | Slc25a44 |
| 19439 | 3 | 4 | | | | IV-1 | Slc25a46 |
| 19440 | 3 | 4 | | | | IV-1 | Slc25a5 |
| 19441 | 3 | 4 | | | | IV-1 | Slc25a54 |
| 19442 | 3 | 4 | | | | IV-1 | Slc26a3 |
| 19443 | 3 | 4 | | | | IV-1 | Slc26a4 |
| 19444 | 3 | 4 | | | | IV-1 | Slc26a5 |
| 19445 | 3 | 4 | | | | IV-1 | Slc26a7 |
| 19446 | 3 | 4 | | | | IV-1 | Slc26a8 |
| 19447 | 3 | 4 | | | | IV-1 | Slc27a3 |
| 19448 | 3 | 4 | | | | IV-1 | Slc27a5 |
| 19449 | 3 | 4 | | | | IV-1 | Slc27a6 |
| 19450 | 3 | 4 | | | | IV-1 | Slc28a1 |
| 19451 | 3 | 4 | | | | IV-1 | Slc28a3 |
| 19452 | 3 | 4 | | | | IV-1 | Slc29a4 |
| 19453 | 3 | 4 | | | | IV-1 | Slc2a7 |
| 19454 | 3 | 4 | | | | IV-1 | Slc2a8 |
| 19455 | 3 | 4 | | | | IV-1 | Slc30a5 |
| 19456 | 3 | 4 | | | | IV-1 | Slc30a6 |
| 19457 | 3 | 4 | | | | IV-1 | Slc30a8 |
| 19458 | 3 | 4 | | | | IV-1 | Slc30a9 |
| 19459 | 3 | 4 | | | | IV-1 | Slc31a1 |
| 19460 | 3 | 4 | | | | IV-1 | Slc31a2 |
| 19461 | 3 | 4 | | | | IV-1 | Slc32a1 |
| 19462 | 3 | 4 | | | | IV-1 | Slc35a1 |
| 19463 | 3 | 4 | | | | IV-1 | Slc35a2 |
| 19464 | 3 | 4 | | | | IV-1 | Slc35a5 |
| 19465 | 3 | 4 | | | | IV-1 | Slc35b3 |
| 19466 | 3 | 4 | | | | IV-1 | Slc35b4 |
| 19467 | 3 | 4 | | | | IV-1 | Slc35c1 |
| 19468 | 3 | 4 | | | | IV-1 | Slc35e1 |
| 19469 | 3 | 4 | | | | IV-1 | Slc35e3 |
| 19470 | 3 | 4 | | | | IV-1 | Slc35e4 |
| 19471 | 3 | 4 | | | | IV-1 | Slc35f1 |
| 19472 | 3 | 4 | | | | IV-1 | Slc35f3 |
| 19473 | 3 | 4 | | | | IV-1 | Slc35f4 |
| 19474 | 3 | 4 | | | | IV-1 | Slc35f6 |
| 19475 | 3 | 4 | | | | IV-1 | Slc35g3 |
| 19476 | 3 | 4 | | | | IV-1 | Slc36a1os |
| 19477 | 3 | 4 | | | | IV-1 | Slc36a2 |
| 19478 | 3 | 4 | | | | IV-1 | Slc36a3 |
| 19479 | 3 | 4 | | | | IV-1 | Slc37a3 |
| 19480 | 3 | 4 | | | | IV-1 | Slc38a11 |
| 19481 | 3 | 4 | | | | IV-1 | Slc38a6 |
| 19482 | 3 | 4 | | | | IV-1 | Slc38a7 |
| 19483 | 3 | 4 | | | | IV-1 | Slc38a8 |
| 19484 | 3 | 4 | | | | IV-1 | Slc39a1 |
| 19485 | 3 | 4 | | | | IV-1 | Slc39a11 |
| 19486 | 3 | 4 | | | | IV-1 | Slc39a12 |
| 19487 | 3 | 4 | | | | IV-1 | Slc39a7 |
| 19488 | 3 | 4 | | | | IV-1 | Slc43a3 |
| 19489 | 3 | 4 | | | | IV-1 | Slc44a2 |
| 19490 | 3 | 4 | | | | IV-1 | Slc44a4 |
| 19491 | 3 | 4 | | | | IV-1 | Slc44a5 |
| 19492 | 3 | 4 | | | | IV-1 | Slc45a1 |
| 19493 | 3 | 4 | | | | IV-1 | Slc45a2 |
| 19494 | 3 | 4 | | | | IV-1 | Slc46a3 |
| 19495 | 3 | 4 | | | | IV-1 | Slc47a2 |
| 19496 | 3 | 4 | | | | IV-1 | Slc48a1 |
| 19497 | 3 | 4 | | | | IV-1 | Slc4a10 |
| 19498 | 3 | 4 | | | | IV-1 | Slc4a2 |
| 19499 | 3 | 4 | | | | IV-1 | Slc4a3 |
| 19500 | 3 | 4 | | | | IV-1 | Slc4a5 |
| 19501 | 3 | 4 | | | | IV-1 | Slc4a7 |
| 19502 | 3 | 4 | | | | IV-1 | Slc4a9 |
| 19503 | 3 | 4 | | | | IV-1 | Slc5a1 |
| 19504 | 3 | 4 | | | | IV-1 | Slc5a11 |
| 19505 | 3 | 4 | | | | IV-1 | Slc5a4a |
| 19506 | 3 | 4 | | | | IV-1 | Slc5a5 |
| 19507 | 3 | 4 | | | | IV-1 | Slc5a8 |
| 19508 | 3 | 4 | | | | IV-1 | Slc6a12 |
| 19509 | 3 | 4 | | | | IV-1 | Slc6a14 |
| 19510 | 3 | 4 | | | | IV-1 | Slc6a15 |
| 19511 | 3 | 4 | | | | IV-1 | Slc6a17 |
| 19512 | 3 | 4 | | | | IV-1 | Slc6a19os |
| 19513 | 3 | 4 | | | | IV-1 | Slc6a20b |
| 19514 | 3 | 4 | | | | IV-1 | Slc6a3 |
| 19515 | 3 | 4 | | | | IV-1 | Slc6a5 |
| 19516 | 3 | 4 | | | | IV-1 | Slc6a7 |
| 19517 | 3 | 4 | | | | IV-1 | Slc7a12 |
| 19518 | 3 | 4 | | | | IV-1 | Slc7a13 |
| 19519 | 3 | 4 | | | | IV-1 | Slc7a14 |
| 19520 | 3 | 4 | | | | IV-1 | Slc7a15 |
| 19521 | 3 | 4 | | | | IV-1 | Slc8a2 |
| 19522 | 3 | 4 | | | | IV-1 | Slc8a3 |
| 19523 | 3 | 4 | | | | IV-1 | Slc9a1 |
| 19524 | 3 | 4 | | | | IV-1 | Slc9a2 |
| 19525 | 3 | 4 | | | | IV-1 | Slc9a3 |
| 19526 | 3 | 4 | | | | IV-1 | Slc9a4 |
| 19527 | 3 | 4 | | | | IV-1 | Slc9a5 |
| 19528 | 3 | 4 | | | | IV-1 | Slc9a6 |
| 19529 | 3 | 4 | | | | IV-1 | Slc9a8 |
| 19530 | 3 | 4 | | | | IV-1 | Slc9b1 |
| 19531 | 3 | 4 | | | | IV-1 | Slc9b2 |
| 19532 | 3 | 4 | | | | IV-1 | Slc9c1 |
| 19533 | 3 | 4 | | | | IV-1 | Slco1a5 |
| 19534 | 3 | 4 | | | | IV-1 | Slco2b1 |
| 19535 | 3 | 4 | | | | IV-1 | Slco3a1 |
| 19536 | 3 | 4 | | | | IV-1 | Slco6b1 |
| 19537 | 3 | 4 | | | | IV-1 | Slco6c1 |
| 19538 | 3 | 4 | | | | IV-1 | Slco6d1 |
| 19539 | 3 | 4 | | | | IV-1 | Slfn10-ps |
| 19540 | 3 | 4 | | | | IV-1 | Slit1 |
| 19541 | 3 | 4 | | | | IV-1 | Slit3 |
| 19542 | 3 | 4 | | | | IV-1 | Slitrk1 |
| 19543 | 3 | 4 | | | | IV-1 | Slitrk3 |
| 19544 | 3 | 4 | | | | IV-1 | Slitrk4 |
| 19545 | 3 | 4 | | | | IV-1 | Slitrk5 |
| 19546 | 3 | 4 | | | | IV-1 | Slk |
| 19547 | 3 | 4 | | | | IV-1 | Slmo2 |

Fig. 43 - 116

| | | | | | | | |
|---|---|---|---|---|---|---|---|
| 19548 | 3 | 4 | | | | IV-1 | Sltm |
| 19549 | 3 | 4 | | | | IV-1 | Slu7 |
| 19550 | 3 | 4 | | | | IV-1 | Slx |
| 19551 | 3 | 4 | | | | IV-1 | Slxl1 |
| 19552 | 3 | 4 | | | | IV-1 | Sly |
| 19553 | 3 | 4 | | | | IV-1 | Smad2 |
| 19554 | 3 | 4 | | | | IV-1 | Smad4 |
| 19555 | 3 | 4 | | | | IV-1 | Smad9 |
| 19556 | 3 | 4 | | | | IV-1 | Smap1 |
| 19557 | 3 | 4 | | | | IV-1 | Smap2 |
| 19558 | 3 | 4 | | | | IV-1 | Smarca1 |
| 19559 | 3 | 4 | | | | IV-1 | Smarca2 |
| 19560 | 3 | 4 | | | | IV-1 | Smarca5 |
| 19561 | 3 | 4 | | | | IV-1 | Smarca5-ps |
| 19562 | 3 | 4 | | | | IV-1 | Smarcad1 |
| 19563 | 3 | 4 | | | | IV-1 | Smarcal1 |
| 19564 | 3 | 4 | | | | IV-1 | Smarcc1 |
| 19565 | 3 | 4 | | | | IV-1 | Smarcc2 |
| 19566 | 3 | 4 | | | | IV-1 | Smarcd1 |
| 19567 | 3 | 4 | | | | IV-1 | Smarcd3 |
| 19568 | 3 | 4 | | | | IV-1 | Smc1a |
| 19569 | 3 | 4 | | | | IV-1 | Smc1b |
| 19570 | 3 | 4 | | | | IV-1 | Smc3 |
| 19571 | 3 | 4 | | | | IV-1 | Smc5 |
| 19572 | 3 | 4 | | | | IV-1 | Smchd1 |
| 19573 | 3 | 4 | | | | IV-1 | Smco2 |
| 19574 | 3 | 4 | | | | IV-1 | Smco3 |
| 19575 | 3 | 4 | | | | IV-1 | Smek2 |
| 19576 | 3 | 4 | | | | IV-1 | Smg5 |
| 19577 | 3 | 4 | | | | IV-1 | Smg6 |
| 19578 | 3 | 4 | | | | IV-1 | Smg7 |
| 19579 | 3 | 4 | | | | IV-1 | Smg8 |
| 19580 | 3 | 4 | | | | IV-1 | Smg9 |
| 19581 | 3 | 4 | | | | IV-1 | Smgc |
| 19582 | 3 | 4 | | | | IV-1 | Smim12 |
| 19583 | 3 | 4 | | | | IV-1 | Smim14 |
| 19584 | 3 | 4 | | | | IV-1 | Smim18 |
| 19585 | 3 | 4 | | | | IV-1 | Smim23 |
| 19586 | 3 | 4 | | | | IV-1 | Smim9 |
| 19587 | 3 | 4 | | | | IV-1 | Smlr1 |
| 19588 | 3 | 4 | | | | IV-1 | Smn1 |
| 19589 | 3 | 4 | | | | IV-1 | Smndc1 |
| 19590 | 3 | 4 | | | | IV-1 | Smok2a |
| 19591 | 3 | 4 | | | | IV-1 | Smok2b |
| 19592 | 3 | 4 | | | | IV-1 | Smok3a |
| 19593 | 3 | 4 | | | | IV-1 | Smok3b |
| 19594 | 3 | 4 | | | | IV-1 | Smok4a |
| 19595 | 3 | 4 | | | | IV-1 | Smpdl3a |
| 19596 | 3 | 4 | | | | IV-1 | Smr2 |
| 19597 | 3 | 4 | | | | IV-1 | Smr3a |
| 19598 | 3 | 4 | | | | IV-1 | Smtn |
| 19599 | 3 | 4 | | | | IV-1 | Smug1 |
| 19600 | 3 | 4 | | | | IV-1 | Smurf1 |
| 19601 | 3 | 4 | | | | IV-1 | Smurf2 |
| 19602 | 3 | 4 | | | | IV-1 | Smyd4 |
| 19603 | 3 | 4 | | | | IV-1 | Snai2 |
| 19604 | 3 | 4 | | | | IV-1 | Snap23 |
| 19605 | 3 | 4 | | | | IV-1 | Snap47 |
| 19606 | 3 | 4 | | | | IV-1 | Snapc5 |
| 19607 | 3 | 4 | | | | IV-1 | Snapin |
| 19608 | 3 | 4 | | | | IV-1 | Snd1 |
| 19609 | 3 | 4 | | | | IV-1 | Snhg1 |
| 19610 | 3 | 4 | | | | IV-1 | Snhg18 |
| 19611 | 3 | 4 | | | | IV-1 | Snhg9 |
| 19612 | 3 | 4 | | | | IV-1 | Snip1 |
| 19613 | 3 | 4 | | | | IV-1 | Snora15 |
| 19614 | 3 | 4 | | | | IV-1 | Snora20 |
| 19615 | 3 | 4 | | | | IV-1 | Snora24 |
| 19616 | 3 | 4 | | | | IV-1 | Snora26 |
| 19617 | 3 | 4 | | | | IV-1 | Snora36b |
| 19618 | 3 | 4 | | | | IV-1 | Snora47 |
| 19619 | 3 | 4 | | | | IV-1 | Snora61 |
| 19620 | 3 | 4 | | | | IV-1 | Snora62 |
| 19621 | 3 | 4 | | | | IV-1 | Snora68 |
| 19622 | 3 | 4 | | | | IV-1 | Snora75 |
| 19623 | 3 | 4 | | | | IV-1 | Snord100 |
| 19624 | 3 | 4 | | | | IV-1 | Snord104 |
| 19625 | 3 | 4 | | | | IV-1 | Snord110 |
| 19626 | 3 | 4 | | | | IV-1 | Snord116 |
| 19627 | 3 | 4 | | | | IV-1 | Snord1b |
| 19628 | 3 | 4 | | | | IV-1 | Snord1c |
| 19629 | 3 | 4 | | | | IV-1 | Snord35b |
| 19630 | 3 | 4 | | | | IV-1 | Snord37 |
| 19631 | 3 | 4 | | | | IV-1 | Snrnp48 |
| 19632 | 3 | 4 | | | | IV-1 | Snrnp70 |
| 19633 | 3 | 4 | | | | IV-1 | Snrpd3 |
| 19634 | 3 | 4 | | | | IV-1 | Snrpn |
| 19635 | 3 | 4 | | | | IV-1 | Sntg1 |
| 19636 | 3 | 4 | | | | IV-1 | Snupn |
| 19637 | 3 | 4 | | | | IV-1 | Snw1 |
| 19638 | 3 | 4 | | | | IV-1 | Snx10 |
| 19639 | 3 | 4 | | | | IV-1 | Snx11 |
| 19640 | 3 | 4 | | | | IV-1 | Snx12 |
| 19641 | 3 | 4 | | | | IV-1 | Snx13 |
| 19642 | 3 | 4 | | | | IV-1 | Snx14 |
| 19643 | 3 | 4 | | | | IV-1 | Snx18 |
| 19644 | 3 | 4 | | | | IV-1 | Snx19 |
| 19645 | 3 | 4 | | | | IV-1 | Snx27 |
| 19646 | 3 | 4 | | | | IV-1 | Snx31 |
| 19647 | 3 | 4 | | | | IV-1 | Snx4 |
| 19648 | 3 | 4 | | | | IV-1 | Snx5 |
| 19649 | 3 | 4 | | | | IV-1 | Snx9 |
| 19650 | 3 | 4 | | | | IV-1 | Sobp |
| 19651 | 3 | 4 | | | | IV-1 | Sod2 |
| 19652 | 3 | 4 | | | | IV-1 | Soga3 |
| 19653 | 3 | 4 | | | | IV-1 | Sohlh1 |
| 19654 | 3 | 4 | | | | IV-1 | Sohlh2 |
| 19655 | 3 | 4 | | | | IV-1 | Sorbs2 |
| 19656 | 3 | 4 | | | | IV-1 | Sorcs1 |
| 19657 | 3 | 4 | | | | IV-1 | Sorcs3 |
| 19658 | 3 | 4 | | | | IV-1 | Sos1 |
| 19659 | 3 | 4 | | | | IV-1 | Sos2 |
| 19660 | 3 | 4 | | | | IV-1 | Sowahd |
| 19661 | 3 | 4 | | | | IV-1 | Sox1 |
| 19662 | 3 | 4 | | | | IV-1 | Sox10 |
| 19663 | 3 | 4 | | | | IV-1 | Sox11 |
| 19664 | 3 | 4 | | | | IV-1 | Sox13 |
| 19665 | 3 | 4 | | | | IV-1 | Sox17 |
| 19666 | 3 | 4 | | | | IV-1 | Sox2 |
| 19667 | 3 | 4 | | | | IV-1 | Sox21 |
| 19668 | 3 | 4 | | | | IV-1 | Sox3 |
| 19669 | 3 | 4 | | | | IV-1 | Sox30 |
| 19670 | 3 | 4 | | | | IV-1 | SoxSos3 |
| 19671 | 3 | 4 | | | | IV-1 | Sox8 |
| 19672 | 3 | 4 | | | | IV-1 | Sp110 |
| 19673 | 3 | 4 | | | | IV-1 | Sp2 |
| 19674 | 3 | 4 | | | | IV-1 | Sp3 |
| 19675 | 3 | 4 | | | | IV-1 | Sp4 |
| 19676 | 3 | 4 | | | | IV-1 | Sp6 |
| 19677 | 3 | 4 | | | | IV-1 | Sp7 |
| 19678 | 3 | 4 | | | | IV-1 | Sp8 |
| 19679 | 3 | 4 | | | | IV-1 | Sp9 |
| 19680 | 3 | 4 | | | | IV-1 | Spaca3 |
| 19681 | 3 | 4 | | | | IV-1 | Spaca5 |
| 19682 | 3 | 4 | | | | IV-1 | Spaca7 |
| 19683 | 3 | 4 | | | | IV-1 | Spag11b |
| 19684 | 3 | 4 | | | | IV-1 | Spag5 |
| 19685 | 3 | 4 | | | | IV-1 | Spam1 |
| 19686 | 3 | 4 | | | | IV-1 | Spast |
| 19687 | 3 | 4 | | | | IV-1 | Spata1 |
| 19688 | 3 | 4 | | | | IV-1 | Spata17 |
| 19689 | 3 | 4 | | | | IV-1 | Spata19 |
| 19690 | 3 | 4 | | | | IV-1 | Spata31 |
| 19691 | 3 | 4 | | | | IV-1 | Spata31d1b |
| 19692 | 3 | 4 | | | | IV-1 | Spata31d1c |
| 19693 | 3 | 4 | | | | IV-1 | Spata31d1d |
| 19694 | 3 | 4 | | | | IV-1 | Spata6 |
| 19695 | 3 | 4 | | | | IV-1 | Spata7 |
| 19696 | 3 | 4 | | | | IV-1 | Spats1 |
| 19697 | 3 | 4 | | | | IV-1 | Spats2l |
| 19698 | 3 | 4 | | | | IV-1 | Spdyb |
| 19699 | 3 | 4 | | | | IV-1 | Specc1l |
| 19700 | 3 | 4 | | | | IV-1 | Speer2 |
| 19701 | 3 | 4 | | | | IV-1 | Speer3 |
| 19702 | 3 | 4 | | | | IV-1 | Speer4b |
| 19703 | 3 | 4 | | | | IV-1 | Speer4c |
| 19704 | 3 | 4 | | | | IV-1 | Speer5-ps1 |
| 19705 | 3 | 4 | | | | IV-1 | Speer8-ps1 |
| 19706 | 3 | 4 | | | | IV-1 | Speer9-ps1 |
| 19707 | 3 | 4 | | | | IV-1 | Spef2 |
| 19708 | 3 | 4 | | | | IV-1 | Spesp1 |
| 19709 | 3 | 4 | | | | IV-1 | Spg20 |
| 19710 | 3 | 4 | | | | IV-1 | Spg7 |
| 19711 | 3 | 4 | | | | IV-1 | Sphkap |
| 19712 | 3 | 4 | | | | IV-1 | Spic |
| 19713 | 3 | 4 | | | | IV-1 | Spin1 |
| 19714 | 3 | 4 | | | | IV-1 | Spin2c |
| 19715 | 3 | 4 | | | | IV-1 | Spin2-ps1 |
| 19716 | 3 | 4 | | | | IV-1 | Spink11 |
| 19717 | 3 | 4 | | | | IV-1 | Spink13 |

Fig. 43 - 117

| | | | | | | | |
|---|---|---|---|---|---|---|---|
| 19718 | 3 | 4 | | | | IV-1 | Spinkl |
| 19719 | 3 | 4 | | | | IV-1 | Spire2 |
| 19720 | 3 | 4 | | | | IV-1 | Spn |
| 19721 | 3 | 4 | | | | IV-1 | Spns3 |
| 19722 | 3 | 4 | | | | IV-1 | Spock1 |
| 19723 | 3 | 4 | | | | IV-1 | Spock3 |
| 19724 | 3 | 4 | | | | IV-1 | Spopl |
| 19725 | 3 | 4 | | | | IV-1 | Sppl2a |
| 19726 | 3 | 4 | | | | IV-1 | Sppl3 |
| 19727 | 3 | 4 | | | | IV-1 | Spred1 |
| 19728 | 3 | 4 | | | | IV-1 | Sprr2k |
| 19729 | 3 | 4 | | | | IV-1 | Spry1 |
| 19730 | 3 | 4 | | | | IV-1 | Spry2 |
| 19731 | 3 | 4 | | | | IV-1 | Spry3 |
| 19732 | 3 | 4 | | | | IV-1 | Spryd3 |
| 19733 | 3 | 4 | | | | IV-1 | Spryd4 |
| 19734 | 3 | 4 | | | | IV-1 | Spsb3 |
| 19735 | 3 | 4 | | | | IV-1 | Spsb4 |
| 19736 | 3 | 4 | | | | IV-1 | Spta1 |
| 19737 | 3 | 4 | | | | IV-1 | Sptbn4 |
| 19738 | 3 | 4 | | | | IV-1 | Sptlc2 |
| 19739 | 3 | 4 | | | | IV-1 | Sptssa |
| 19740 | 3 | 4 | | | | IV-1 | Sqstm1 |
| 19741 | 3 | 4 | | | | IV-1 | Srbd1 |
| 19742 | 3 | 4 | | | | IV-1 | Srcrb4d |
| 19743 | 3 | 4 | | | | IV-1 | Srd5a3 |
| 19744 | 3 | 4 | | | | IV-1 | Srebf2 |
| 19745 | 3 | 4 | | | | IV-1 | Srek1 |
| 19746 | 3 | 4 | | | | IV-1 | Srek1ip1 |
| 19747 | 3 | 4 | | | | IV-1 | Srfbp1 |
| 19748 | 3 | 4 | | | | IV-1 | Srgap1 |
| 19749 | 3 | 4 | | | | IV-1 | Sri |
| 19750 | 3 | 4 | | | | IV-1 | Srp54a |
| 19751 | 3 | 4 | | | | IV-1 | Srp54b |
| 19752 | 3 | 4 | | | | IV-1 | Srp68 |
| 19753 | 3 | 4 | | | | IV-1 | Srp72 |
| 19754 | 3 | 4 | | | | IV-1 | Srpk2 |
| 19755 | 3 | 4 | | | | IV-1 | Srpr |
| 19756 | 3 | 4 | | | | IV-1 | Srprb |
| 19757 | 3 | 4 | | | | IV-1 | Srr |
| 19758 | 3 | 4 | | | | IV-1 | Srrm1 |
| 19759 | 3 | 4 | | | | IV-1 | Srrm3 |
| 19760 | 3 | 4 | | | | IV-1 | Srrm4 |
| 19761 | 3 | 4 | | | | IV-1 | Srrm4os |
| 19762 | 3 | 4 | | | | IV-1 | Srrt |
| 19763 | 3 | 4 | | | | IV-1 | Srsf1 |
| 19764 | 3 | 4 | | | | IV-1 | Srsf10 |
| 19765 | 3 | 4 | | | | IV-1 | Srsf12 |
| 19766 | 3 | 4 | | | | IV-1 | Srsf2 |
| 19767 | 3 | 4 | | | | IV-1 | Srsf4 |
| 19768 | 3 | 4 | | | | IV-1 | Srsf6 |
| 19769 | 3 | 4 | | | | IV-1 | Srsf9 |
| 19770 | 3 | 4 | | | | IV-1 | Sry |
| 19771 | 3 | 4 | | | | IV-1 | Ss18 |
| 19772 | 3 | 4 | | | | IV-1 | Ss18l1 |
| 19773 | 3 | 4 | | | | IV-1 | Ssfa2 |
| 19774 | 3 | 4 | | | | IV-1 | Ssna1 |
| 19775 | 3 | 4 | | | | IV-1 | Sspo |
| 19776 | 3 | 4 | | | | IV-1 | Ssrp1 |
| 19777 | 3 | 4 | | | | IV-1 | Sstr1 |
| 19778 | 3 | 4 | | | | IV-1 | Sstr2 |
| 19779 | 3 | 4 | | | | IV-1 | Sstr5 |
| 19780 | 3 | 4 | | | | IV-1 | Ssty1 |
| 19781 | 3 | 4 | | | | IV-1 | Ssty2 |
| 19782 | 3 | 4 | | | | IV-1 | Ssu2 |
| 19783 | 3 | 4 | | | | IV-1 | Ssu72 |
| 19784 | 3 | 4 | | | | IV-1 | Ssxb1 |
| 19785 | 3 | 4 | | | | IV-1 | Ssxb10 |
| 19786 | 3 | 4 | | | | IV-1 | Ssxb3 |
| 19787 | 3 | 4 | | | | IV-1 | Ssxb5 |
| 19788 | 3 | 4 | | | | IV-1 | St6gal2 |
| 19789 | 3 | 4 | | | | IV-1 | St6galnac1 |
| 19790 | 3 | 4 | | | | IV-1 | St6galnac4 |
| 19791 | 3 | 4 | | | | IV-1 | St6galnac6 |
| 19792 | 3 | 4 | | | | IV-1 | St7l |
| 19793 | 3 | 4 | | | | IV-1 | St8sia3 |
| 19794 | 3 | 4 | | | | IV-1 | Stag1 |
| 19795 | 3 | 4 | | | | IV-1 | Stag3 |
| 19796 | 3 | 4 | | | | IV-1 | Stam |
| 19797 | 3 | 4 | | | | IV-1 | Stam2 |
| 19798 | 3 | 4 | | | | IV-1 | Stard6 |
| 19799 | 3 | 4 | | | | IV-1 | Stard7 |
| 19800 | 3 | 4 | | | | IV-1 | Stat3 |
| 19801 | 3 | 4 | | | | IV-1 | Stat5a |
| 19802 | 3 | 4 | | | | IV-1 | Stat6 |
| 19803 | 3 | 4 | | | | IV-1 | Stau1 |
| 19804 | 3 | 4 | | | | IV-1 | Stau2 |
| 19805 | 3 | 4 | | | | IV-1 | Steap1 |
| 19806 | 3 | 4 | | | | IV-1 | Steap2 |
| 19807 | 3 | 4 | | | | IV-1 | Stil |
| 19808 | 3 | 4 | | | | IV-1 | Stim2 |
| 19809 | 3 | 4 | | | | IV-1 | Stip1 |
| 19810 | 3 | 4 | | | | IV-1 | Stk10 |
| 19811 | 3 | 4 | | | | IV-1 | Stk11 |
| 19812 | 3 | 4 | | | | IV-1 | Stk11ip |
| 19813 | 3 | 4 | | | | IV-1 | Stk17b |
| 19814 | 3 | 4 | | | | IV-1 | Stk19 |
| 19815 | 3 | 4 | | | | IV-1 | Stk24 |
| 19816 | 3 | 4 | | | | IV-1 | Stk25 |
| 19817 | 3 | 4 | | | | IV-1 | Stk3 |
| 19818 | 3 | 4 | | | | IV-1 | Stk31 |
| 19819 | 3 | 4 | | | | IV-1 | Stk32a |
| 19820 | 3 | 4 | | | | IV-1 | Stk32b |
| 19821 | 3 | 4 | | | | IV-1 | Stk38 |
| 19822 | 3 | 4 | | | | IV-1 | Stk4 |
| 19823 | 3 | 4 | | | | IV-1 | Stmn1-rs1 |
| 19824 | 3 | 4 | | | | IV-1 | Stmn4 |
| 19825 | 3 | 4 | | | | IV-1 | Stmnd1 |
| 19826 | 3 | 4 | | | | IV-1 | Stoml2 |
| 19827 | 3 | 4 | | | | IV-1 | Stra6 |
| 19828 | 3 | 4 | | | | IV-1 | Stra8 |
| 19829 | 3 | 4 | | | | IV-1 | Strn3 |
| 19830 | 3 | 4 | | | | IV-1 | Strn4 |
| 19831 | 3 | 4 | | | | IV-1 | Stt3b |
| 19832 | 3 | 4 | | | | IV-1 | Stub1 |
| 19833 | 3 | 4 | | | | IV-1 | Stx12 |
| 19834 | 3 | 4 | | | | IV-1 | Stx16 |
| 19835 | 3 | 4 | | | | IV-1 | Stx2 |
| 19836 | 3 | 4 | | | | IV-1 | Stx3 |
| 19837 | 3 | 4 | | | | IV-1 | Stx7 |
| 19838 | 3 | 4 | | | | IV-1 | Stxbp2 |
| 19839 | 3 | 4 | | | | IV-1 | Stxbp5 |
| 19840 | 3 | 4 | | | | IV-1 | Stxbp5l |
| 19841 | 3 | 4 | | | | IV-1 | Stxbp6 |
| 19842 | 3 | 4 | | | | IV-1 | Styk1 |
| 19843 | 3 | 4 | | | | IV-1 | Styx |
| 19844 | 3 | 4 | | | | IV-1 | Styxl1 |
| 19845 | 3 | 4 | | | | IV-1 | Suco |
| 19846 | 3 | 4 | | | | IV-1 | Sugp1 |
| 19847 | 3 | 4 | | | | IV-1 | Sugt1 |
| 19848 | 3 | 4 | | | | IV-1 | Sulf1 |
| 19849 | 3 | 4 | | | | IV-1 | Sult1b1 |
| 19850 | 3 | 4 | | | | IV-1 | Sult1c1 |
| 19851 | 3 | 4 | | | | IV-1 | Sult1c2 |
| 19852 | 3 | 4 | | | | IV-1 | Sult2a4 |
| 19853 | 3 | 4 | | | | IV-1 | Sult2a5 |
| 19854 | 3 | 4 | | | | IV-1 | Sult6b1 |
| 19855 | 3 | 4 | | | | IV-1 | Sumf1 |
| 19856 | 3 | 4 | | | | IV-1 | Sumo3 |
| 19857 | 3 | 4 | | | | IV-1 | Sun1 |
| 19858 | 3 | 4 | | | | IV-1 | Sun3 |
| 19859 | 3 | 4 | | | | IV-1 | Sun5 |
| 19860 | 3 | 4 | | | | IV-1 | Supt16 |
| 19861 | 3 | 4 | | | | IV-1 | Supt6 |
| 19862 | 3 | 4 | | | | IV-1 | Supt7l |
| 19863 | 3 | 4 | | | | IV-1 | Surf1 |
| 19864 | 3 | 4 | | | | IV-1 | Surf2 |
| 19865 | 3 | 4 | | | | IV-1 | Surf4 |
| 19866 | 3 | 4 | | | | IV-1 | Surf6 |
| 19867 | 3 | 4 | | | | IV-1 | Susd1 |
| 19868 | 3 | 4 | | | | IV-1 | Susd5 |
| 19869 | 3 | 4 | | | | IV-1 | Suv39h1 |
| 19870 | 3 | 4 | | | | IV-1 | Suv39h2 |
| 19871 | 3 | 4 | | | | IV-1 | Suz12 |
| 19872 | 3 | 4 | | | | IV-1 | Sv2a |
| 19873 | 3 | 4 | | | | IV-1 | Sv2c |
| 19874 | 3 | 4 | | | | IV-1 | Sva |
| 19875 | 3 | 4 | | | | IV-1 | Sval1 |
| 19876 | 3 | 4 | | | | IV-1 | Sval2 |
| 19877 | 3 | 4 | | | | IV-1 | Sval3 |
| 19878 | 3 | 4 | | | | IV-1 | Svs2 |
| 19879 | 3 | 4 | | | | IV-1 | Svs3a |
| 19880 | 3 | 4 | | | | IV-1 | Svs3b |
| 19881 | 3 | 4 | | | | IV-1 | Svs4 |
| 19882 | 3 | 4 | | | | IV-1 | Syce1l |
| 19883 | 3 | 4 | | | | IV-1 | Syce3 |
| 19884 | 3 | 4 | | | | IV-1 | Sycp1 |
| 19885 | 3 | 4 | | | | IV-1 | Sycp1-ps1 |
| 19886 | 3 | 4 | | | | IV-1 | Sycp2 |
| 19887 | 3 | 4 | | | | IV-1 | Syn1 |

Fig. 43 - 118

| | | | | | | | |
|---|---|---|---|---|---|---|---|
| 19888 | 3 | 4 | | | | IV-1 | Syn3 |
| 19889 | 3 | 4 | | | | IV-1 | Syna |
| 19890 | 3 | 4 | | | | IV-1 | Synb |
| 19891 | 3 | 4 | | | | IV-1 | Syncrip |
| 19892 | 3 | 4 | | | | IV-1 | Syndig1 |
| 19893 | 3 | 4 | | | | IV-1 | Syngr2 |
| 19894 | 3 | 4 | | | | IV-1 | Syngr3 |
| 19895 | 3 | 4 | | | | IV-1 | Synj1 |
| 19896 | 3 | 4 | | | | IV-1 | Synpr |
| 19897 | 3 | 4 | | | | IV-1 | Sypl |
| 19898 | 3 | 4 | | | | IV-1 | Syt1 |
| 19899 | 3 | 4 | | | | IV-1 | Syt10 |
| 19900 | 3 | 4 | | | | IV-1 | Syt14 |
| 19901 | 3 | 4 | | | | IV-1 | Syt15 |
| 19902 | 3 | 4 | | | | IV-1 | Syt16 |
| 19903 | 3 | 4 | | | | IV-1 | Syt2 |
| 19904 | 3 | 4 | | | | IV-1 | Syt5 |
| 19905 | 3 | 4 | | | | IV-1 | Syt6 |
| 19906 | 3 | 4 | | | | IV-1 | Syt9 |
| 19907 | 3 | 4 | | | | IV-1 | Sytl5 |
| 19908 | 3 | 4 | | | | IV-1 | Szrd1 |
| 19909 | 3 | 4 | | | | IV-1 | Szt2 |
| 19910 | 3 | 4 | | | | IV-1 | T |
| 19911 | 3 | 4 | | | | IV-1 | T2 |
| 19912 | 3 | 4 | | | | IV-1 | Taar2 |
| 19913 | 3 | 4 | | | | IV-1 | Taar3 |
| 19914 | 3 | 4 | | | | IV-1 | Taar4 |
| 19915 | 3 | 4 | | | | IV-1 | Taar6 |
| 19916 | 3 | 4 | | | | IV-1 | Tacr1 |
| 19917 | 3 | 4 | | | | IV-1 | Tacr3 |
| 19918 | 3 | 4 | | | | IV-1 | Tada2b |
| 19919 | 3 | 4 | | | | IV-1 | Taf15 |
| 19920 | 3 | 4 | | | | IV-1 | Taf1a |
| 19921 | 3 | 4 | | | | IV-1 | Taf1b |
| 19922 | 3 | 4 | | | | IV-1 | Taf1d |
| 19923 | 3 | 4 | | | | IV-1 | Taf2 |
| 19924 | 3 | 4 | | | | IV-1 | Taf3 |
| 19925 | 3 | 4 | | | | IV-1 | Taf4a |
| 19926 | 3 | 4 | | | | IV-1 | Taf5l |
| 19927 | 3 | 4 | | | | IV-1 | Taf7 |
| 19928 | 3 | 4 | | | | IV-1 | Taf7l |
| 19929 | 3 | 4 | | | | IV-1 | Taf8 |
| 19930 | 3 | 4 | | | | IV-1 | Taf9b |
| 19931 | 3 | 4 | | | | IV-1 | Tagap |
| 19932 | 3 | 4 | | | | IV-1 | Tagap1 |
| 19933 | 3 | 4 | | | | IV-1 | Tagln2 |
| 19934 | 3 | 4 | | | | IV-1 | Tal2 |
| 19935 | 3 | 4 | | | | IV-1 | Tanc1 |
| 19936 | 3 | 4 | | | | IV-1 | Tank |
| 19937 | 3 | 4 | | | | IV-1 | Taok3 |
| 19938 | 3 | 4 | | | | IV-1 | Tap2 |
| 19939 | 3 | 4 | | | | IV-1 | Tapbp |
| 19940 | 3 | 4 | | | | IV-1 | Tapbpl |
| 19941 | 3 | 4 | | | | IV-1 | Tardbp |
| 19942 | 3 | 4 | | | | IV-1 | Tarm1 |
| 19943 | 3 | 4 | | | | IV-1 | Tars |
| 19944 | 3 | 4 | | | | IV-1 | Tars2 |
| 19945 | 3 | 4 | | | | IV-1 | Tas1r1 |
| 19946 | 3 | 4 | | | | IV-1 | Tas1r2 |
| 19947 | 3 | 4 | | | | IV-1 | Tas1r3 |
| 19948 | 3 | 4 | | | | IV-1 | Tas2r102 |
| 19949 | 3 | 4 | | | | IV-1 | Tas2r103 |
| 19950 | 3 | 4 | | | | IV-1 | Tas2r104 |
| 19951 | 3 | 4 | | | | IV-1 | Tas2r107 |
| 19952 | 3 | 4 | | | | IV-1 | Tas2r116 |
| 19953 | 3 | 4 | | | | IV-1 | Tas2r123 |
| 19954 | 3 | 4 | | | | IV-1 | Tax1bp3 |
| 19955 | 3 | 4 | | | | IV-1 | Tbc1d10a |
| 19956 | 3 | 4 | | | | IV-1 | Tbc1d12 |
| 19957 | 3 | 4 | | | | IV-1 | Tbc1d13 |
| 19958 | 3 | 4 | | | | IV-1 | Tbc1d14 |
| 19959 | 3 | 4 | | | | IV-1 | Tbc1d15 |
| 19960 | 3 | 4 | | | | IV-1 | Tbc1d2 |
| 19961 | 3 | 4 | | | | IV-1 | Tbc1d21 |
| 19962 | 3 | 4 | | | | IV-1 | Tbc1d22b |
| 19963 | 3 | 4 | | | | IV-1 | Tbc1d22bos |
| 19964 | 3 | 4 | | | | IV-1 | Tbc1d23 |
| 19965 | 3 | 4 | | | | IV-1 | Tbc1d2b |
| 19966 | 3 | 4 | | | | IV-1 | Tbc1d32 |
| 19967 | 3 | 4 | | | | IV-1 | Tbc1d5 |
| 19968 | 3 | 4 | | | | IV-1 | Tbc1d8b |
| 19969 | 3 | 4 | | | | IV-1 | Tbc1d9 |
| 19970 | 3 | 4 | | | | IV-1 | Tbccd1 |
| 19971 | 3 | 4 | | | | IV-1 | Tbcd |
| 19972 | 3 | 4 | | | | IV-1 | Tbk1 |
| 19973 | 3 | 4 | | | | IV-1 | Tbl2 |
| 19974 | 3 | 4 | | | | IV-1 | Tbp |
| 19975 | 3 | 4 | | | | IV-1 | Tbpl1 |
| 19976 | 3 | 4 | | | | IV-1 | Tbpl2 |
| 19977 | 3 | 4 | | | | IV-1 | Tbr1 |
| 19978 | 3 | 4 | | | | IV-1 | Tbrg3 |
| 19979 | 3 | 4 | | | | IV-1 | Tbrg4 |
| 19980 | 3 | 4 | | | | IV-1 | Tbx1 |
| 19981 | 3 | 4 | | | | IV-1 | Tbx18 |
| 19982 | 3 | 4 | | | | IV-1 | Tbx2 |
| 19983 | 3 | 4 | | | | IV-1 | Tbx20 |
| 19984 | 3 | 4 | | | | IV-1 | Tbx21 |
| 19985 | 3 | 4 | | | | IV-1 | Tbx22 |
| 19986 | 3 | 4 | | | | IV-1 | Tbx4 |
| 19987 | 3 | 4 | | | | IV-1 | Tbx5 |
| 19988 | 3 | 4 | | | | IV-1 | Tcam1 |
| 19989 | 3 | 4 | | | | IV-1 | Tcea1 |
| 19990 | 3 | 4 | | | | IV-1 | Tceal7 |
| 19991 | 3 | 4 | | | | IV-1 | Tceanc |
| 19992 | 3 | 4 | | | | IV-1 | Tceb1 |
| 19993 | 3 | 4 | | | | IV-1 | Tceb3 |
| 19994 | 3 | 4 | | | | IV-1 | Tcerg1 |
| 19995 | 3 | 4 | | | | IV-1 | Tcerg1l |
| 19996 | 3 | 4 | | | | IV-1 | Tcf21 |
| 19997 | 3 | 4 | | | | IV-1 | Tcf25 |
| 19998 | 3 | 4 | | | | IV-1 | Tcf4 |
| 19999 | 3 | 4 | | | | IV-1 | Tcf7l1 |
| 20000 | 3 | 4 | | | | IV-1 | Tcf7l2 |
| 20001 | 3 | 4 | | | | IV-1 | Tcfl5 |
| 20002 | 3 | 4 | | | | IV-1 | Tchp |
| 20003 | 3 | 4 | | | | IV-1 | Tcirg1 |
| 20004 | 3 | 4 | | | | IV-1 | Tcl1 |
| 20005 | 3 | 4 | | | | IV-1 | Tcl1b1 |
| 20006 | 3 | 4 | | | | IV-1 | Tcl1b2 |
| 20007 | 3 | 4 | | | | IV-1 | Tcl1b3 |
| 20008 | 3 | 4 | | | | IV-1 | Tcl1b4 |
| 20009 | 3 | 4 | | | | IV-1 | Tcl1b5 |
| 20010 | 3 | 4 | | | | IV-1 | Tcp11l1 |
| 20011 | 3 | 4 | | | | IV-1 | Tctn1 |
| 20012 | 3 | 4 | | | | IV-1 | Tdgf1 |
| 20013 | 3 | 4 | | | | IV-1 | Tdo2 |
| 20014 | 3 | 4 | | | | IV-1 | Tdpoz1 |
| 20015 | 3 | 4 | | | | IV-1 | Tdpoz2 |
| 20016 | 3 | 4 | | | | IV-1 | Tdpoz3 |
| 20017 | 3 | 4 | | | | IV-1 | Tdpoz4 |
| 20018 | 3 | 4 | | | | IV-1 | Tdpoz5 |
| 20019 | 3 | 4 | | | | IV-1 | Tdrd1 |
| 20020 | 3 | 4 | | | | IV-1 | Tdrd9 |
| 20021 | 3 | 4 | | | | IV-1 | Tecr |
| 20022 | 3 | 4 | | | | IV-1 | Tecrl |
| 20023 | 3 | 4 | | | | IV-1 | Tecta |
| 20024 | 3 | 4 | | | | IV-1 | Teddm1 |
| 20025 | 3 | 4 | | | | IV-1 | Tek |
| 20026 | 3 | 4 | | | | IV-1 | Tenm2 |
| 20027 | 3 | 4 | | | | IV-1 | Tepp |
| 20028 | 3 | 4 | | | | IV-1 | Terf2 |
| 20029 | 3 | 4 | | | | IV-1 | Tesk2 |
| 20030 | 3 | 4 | | | | IV-1 | Tex10 |
| 20031 | 3 | 4 | | | | IV-1 | Tex11 |
| 20032 | 3 | 4 | | | | IV-1 | Tex12 |
| 20033 | 3 | 4 | | | | IV-1 | Tex13 |
| 20034 | 3 | 4 | | | | IV-1 | Tex13a |
| 20035 | 3 | 4 | | | | IV-1 | Tex14 |
| 20036 | 3 | 4 | | | | IV-1 | Tex16 |
| 20037 | 3 | 4 | | | | IV-1 | Tex19.2 |
| 20038 | 3 | 4 | | | | IV-1 | Tex21 |
| 20039 | 3 | 4 | | | | IV-1 | Tex24 |
| 20040 | 3 | 4 | | | | IV-1 | Tex26 |
| 20041 | 3 | 4 | | | | IV-1 | Tex261 |
| 20042 | 3 | 4 | | | | IV-1 | Tex35 |
| 20043 | 3 | 4 | | | | IV-1 | Tex43 |
| 20044 | 3 | 4 | | | | IV-1 | Tfap2b |
| 20045 | 3 | 4 | | | | IV-1 | Tfap2e |
| 20046 | 3 | 4 | | | | IV-1 | Tfdp1 |
| 20047 | 3 | 4 | | | | IV-1 | Tfe3 |
| 20048 | 3 | 4 | | | | IV-1 | Tfec |
| 20049 | 3 | 4 | | | | IV-1 | Tfg |
| 20050 | 3 | 4 | | | | IV-1 | Tfip11 |
| 20051 | 3 | 4 | | | | IV-1 | Tfpi |
| 20052 | 3 | 4 | | | | IV-1 | Tfpt |
| 20053 | 3 | 4 | | | | IV-1 | Tgfb1 |
| 20054 | 3 | 4 | | | | IV-1 | Tgfb1i1 |
| 20055 | 3 | 4 | | | | IV-1 | Tgfb2 |
| 20056 | 3 | 4 | | | | IV-1 | Tgfb3 |
| 20057 | 3 | 4 | | | | IV-1 | Tgfbr1 |

Fig. 43 - 119

| | | | | | | | |
|---|---|---|---|---|---|---|---|
| 20058 | 3 | 4 | | | | IV-1 | Tgif2 |
| 20059 | 3 | 4 | | | | IV-1 | Tgif2lx1 |
| 20060 | 3 | 4 | | | | IV-1 | Tgif2lx2 |
| 20061 | 3 | 4 | | | | IV-1 | Tgm7 |
| 20062 | 3 | 4 | | | | IV-1 | Tgoln1 |
| 20063 | 3 | 4 | | | | IV-1 | Tgs1 |
| 20064 | 3 | 4 | | | | IV-1 | Thap6 |
| 20065 | 3 | 4 | | | | IV-1 | Theg |
| 20066 | 3 | 4 | | | | IV-1 | Them5 |
| 20067 | 3 | 4 | | | | IV-1 | Themis3 |
| 20068 | 3 | 4 | | | | IV-1 | Thnsl1 |
| 20069 | 3 | 4 | | | | IV-1 | Thoc5 |
| 20070 | 3 | 4 | | | | IV-1 | Thpo |
| 20071 | 3 | 4 | | | | IV-1 | Thrap3 |
| 20072 | 3 | 4 | | | | IV-1 | Thsd7a |
| 20073 | 3 | 4 | | | | IV-1 | Thsd7b |
| 20074 | 3 | 4 | | | | IV-1 | Thtpa |
| 20075 | 3 | 4 | | | | IV-1 | Thumpd1 |
| 20076 | 3 | 4 | | | | IV-1 | Thumpd2 |
| 20077 | 3 | 4 | | | | IV-1 | Thumpd3 |
| 20078 | 3 | 4 | | | | IV-1 | Tial1 |
| 20079 | 3 | 4 | | | | IV-1 | Ticam1 |
| 20080 | 3 | 4 | | | | IV-1 | Ticam2 |
| 20081 | 3 | 4 | | | | IV-1 | Ticrr |
| 20082 | 3 | 4 | | | | IV-1 | Tifab |
| 20083 | 3 | 4 | | | | IV-1 | Tigd2 |
| 20084 | 3 | 4 | | | | IV-1 | Tigd4 |
| 20085 | 3 | 4 | | | | IV-1 | Timd2 |
| 20086 | 3 | 4 | | | | IV-1 | Timd4 |
| 20087 | 3 | 4 | | | | IV-1 | Timm10b |
| 20088 | 3 | 4 | | | | IV-1 | Timm21 |
| 20089 | 3 | 4 | | | | IV-1 | Timm22 |
| 20090 | 3 | 4 | | | | IV-1 | Timm8a2 |
| 20091 | 3 | 4 | | | | IV-1 | Timmdc1 |
| 20092 | 3 | 4 | | | | IV-1 | Timp2 |
| 20093 | 3 | 4 | | | | IV-1 | Tinag |
| 20094 | 3 | 4 | | | | IV-1 | Tiparp |
| 20095 | 3 | 4 | | | | IV-1 | Tiprl |
| 20096 | 3 | 4 | | | | IV-1 | Tjap1 |
| 20097 | 3 | 4 | | | | IV-1 | Tjp2 |
| 20098 | 3 | 4 | | | | IV-1 | Tk2 |
| 20099 | 3 | 4 | | | | IV-1 | Tkt |
| 20100 | 3 | 4 | | | | IV-1 | Tktl1 |
| 20101 | 3 | 4 | | | | IV-1 | Tktl2 |
| 20102 | 3 | 4 | | | | IV-1 | Tlcd1 |
| 20103 | 3 | 4 | | | | IV-1 | Tle3 |
| 20104 | 3 | 4 | | | | IV-1 | Tlk1 |
| 20105 | 3 | 4 | | | | IV-1 | Tll1 |
| 20106 | 3 | 4 | | | | IV-1 | Tll2 |
| 20107 | 3 | 4 | | | | IV-1 | Tln1 |
| 20108 | 3 | 4 | | | | IV-1 | Tlr11 |
| 20109 | 3 | 4 | | | | IV-1 | Tlr2 |
| 20110 | 3 | 4 | | | | IV-1 | Tlx1 |
| 20111 | 3 | 4 | | | | IV-1 | Tlx2 |
| 20112 | 3 | 4 | | | | IV-1 | Tm2d2 |
| 20113 | 3 | 4 | | | | IV-1 | Tm4sf1 |
| 20114 | 3 | 4 | | | | IV-1 | Tm4sf19 |
| 20115 | 3 | 4 | | | | IV-1 | Tm4sf5 |
| 20116 | 3 | 4 | | | | IV-1 | Tm6sf2 |
| 20117 | 3 | 4 | | | | IV-1 | Tm9sf2 |
| 20118 | 3 | 4 | | | | IV-1 | Tm9sf3 |
| 20119 | 3 | 4 | | | | IV-1 | Tm9sf4 |
| 20120 | 3 | 4 | | | | IV-1 | Tmbim6 |
| 20121 | 3 | 4 | | | | IV-1 | Tmbim7 |
| 20122 | 3 | 4 | | | | IV-1 | Tmc1 |
| 20123 | 3 | 4 | | | | IV-1 | Tmc2 |
| 20124 | 3 | 4 | | | | IV-1 | Tmc3 |
| 20125 | 3 | 4 | | | | IV-1 | Tmcc3 |
| 20126 | 3 | 4 | | | | IV-1 | Tmco3 |
| 20127 | 3 | 4 | | | | IV-1 | Tmco5 |
| 20128 | 3 | 4 | | | | IV-1 | Tmco5b |
| 20129 | 3 | 4 | | | | IV-1 | Tmed10 |
| 20130 | 3 | 4 | | | | IV-1 | Tmed4 |
| 20131 | 3 | 4 | | | | IV-1 | Tmed5 |
| 20132 | 3 | 4 | | | | IV-1 | Tmed7 |
| 20133 | 3 | 4 | | | | IV-1 | Tmed9 |
| 20134 | 3 | 4 | | | | IV-1 | Tmeff2 |
| 20135 | 3 | 4 | | | | IV-1 | Tmem100 |
| 20136 | 3 | 4 | | | | IV-1 | Tmem104 |
| 20137 | 3 | 4 | | | | IV-1 | Tmem109 |
| 20138 | 3 | 4 | | | | IV-1 | Tmem110 |
| 20139 | 3 | 4 | | | | IV-1 | Tmem116 |
| 20140 | 3 | 4 | | | | IV-1 | Tmem121 |
| 20141 | 3 | 4 | | | | IV-1 | Tmem123 |
| 20142 | 3 | 4 | | | | IV-1 | Tmem127 |

| | | | | | | | |
|---|---|---|---|---|---|---|---|
| 20143 | 3 | 4 | | | | IV-1 | Tmem128 |
| 20144 | 3 | 4 | | | | IV-1 | Tmem129 |
| 20145 | 3 | 4 | | | | IV-1 | Tmem130 |
| 20146 | 3 | 4 | | | | IV-1 | Tmem131 |
| 20147 | 3 | 4 | | | | IV-1 | Tmem132b |
| 20148 | 3 | 4 | | | | IV-1 | Tmem132c |
| 20149 | 3 | 4 | | | | IV-1 | Tmem132cos |
| 20150 | 3 | 4 | | | | IV-1 | Tmem132e |
| 20151 | 3 | 4 | | | | IV-1 | Tmem135 |
| 20152 | 3 | 4 | | | | IV-1 | Tmem143 |
| 20153 | 3 | 4 | | | | IV-1 | Tmem145 |
| 20154 | 3 | 4 | | | | IV-1 | Tmem150b |
| 20155 | 3 | 4 | | | | IV-1 | Tmem150cos |
| 20156 | 3 | 4 | | | | IV-1 | Tmem151b |
| 20157 | 3 | 4 | | | | IV-1 | Tmem158 |
| 20158 | 3 | 4 | | | | IV-1 | Tmem165 |
| 20159 | 3 | 4 | | | | IV-1 | Tmem167 |
| 20160 | 3 | 4 | | | | IV-1 | Tmem167b |
| 20161 | 3 | 4 | | | | IV-1 | Tmem168 |
| 20162 | 3 | 4 | | | | IV-1 | Tmem170b |
| 20163 | 3 | 4 | | | | IV-1 | Tmem174 |
| 20164 | 3 | 4 | | | | IV-1 | Tmem175 |
| 20165 | 3 | 4 | | | | IV-1 | Tmem177 |
| 20166 | 3 | 4 | | | | IV-1 | Tmem178 |
| 20167 | 3 | 4 | | | | IV-1 | Tmem178b |
| 20168 | 3 | 4 | | | | IV-1 | Tmem18 |
| 20169 | 3 | 4 | | | | IV-1 | Tmem183a |
| 20170 | 3 | 4 | | | | IV-1 | Tmem184b |
| 20171 | 3 | 4 | | | | IV-1 | Tmem186 |
| 20172 | 3 | 4 | | | | IV-1 | Tmem189 |
| 20173 | 3 | 4 | | | | IV-1 | Tmem190 |
| 20174 | 3 | 4 | | | | IV-1 | Tmem194 |
| 20175 | 3 | 4 | | | | IV-1 | Tmem196 |
| 20176 | 3 | 4 | | | | IV-1 | Tmem198b |
| 20177 | 3 | 4 | | | | IV-1 | Tmem199 |
| 20178 | 3 | 4 | | | | IV-1 | Tmem2 |
| 20179 | 3 | 4 | | | | IV-1 | Tmem200c |
| 20180 | 3 | 4 | | | | IV-1 | Tmem201 |
| 20181 | 3 | 4 | | | | IV-1 | Tmem204 |
| 20182 | 3 | 4 | | | | IV-1 | Tmem207 |
| 20183 | 3 | 4 | | | | IV-1 | Tmem209 |
| 20184 | 3 | 4 | | | | IV-1 | Tmem210 |
| 20185 | 3 | 4 | | | | IV-1 | Tmem211 |
| 20186 | 3 | 4 | | | | IV-1 | Tmem214 |
| 20187 | 3 | 4 | | | | IV-1 | Tmem215 |
| 20188 | 3 | 4 | | | | IV-1 | Tmem219 |
| 20189 | 3 | 4 | | | | IV-1 | Tmem225 |
| 20190 | 3 | 4 | | | | IV-1 | Tmem229a |
| 20191 | 3 | 4 | | | | IV-1 | Tmem229b |
| 20192 | 3 | 4 | | | | IV-1 | Tmem230 |
| 20193 | 3 | 4 | | | | IV-1 | Tmem232 |
| 20194 | 3 | 4 | | | | IV-1 | Tmem235 |
| 20195 | 3 | 4 | | | | IV-1 | Tmem236 |
| 20196 | 3 | 4 | | | | IV-1 | Tmem239 |
| 20197 | 3 | 4 | | | | IV-1 | Tmem240 |
| 20198 | 3 | 4 | | | | IV-1 | Tmem241 |
| 20199 | 3 | 4 | | | | IV-1 | Tmem242 |
| 20200 | 3 | 4 | | | | IV-1 | Tmem248 |
| 20201 | 3 | 4 | | | | IV-1 | Tmem255a |
| 20202 | 3 | 4 | | | | IV-1 | Tmem259 |
| 20203 | 3 | 4 | | | | IV-1 | Tmem260 |
| 20204 | 3 | 4 | | | | IV-1 | Tmem263 |
| 20205 | 3 | 4 | | | | IV-1 | Tmem28 |
| 20206 | 3 | 4 | | | | IV-1 | Tmem29 |
| 20207 | 3 | 4 | | | | IV-1 | Tmem30a |
| 20208 | 3 | 4 | | | | IV-1 | Tmem30c |
| 20209 | 3 | 4 | | | | IV-1 | Tmem33 |
| 20210 | 3 | 4 | | | | IV-1 | Tmem41b |
| 20211 | 3 | 4 | | | | IV-1 | Tmem42 |
| 20212 | 3 | 4 | | | | IV-1 | Tmem45b |
| 20213 | 3 | 4 | | | | IV-1 | Tmem47 |
| 20214 | 3 | 4 | | | | IV-1 | Tmem50b |
| 20215 | 3 | 4 | | | | IV-1 | Tmem51os1 |
| 20216 | 3 | 4 | | | | IV-1 | Tmem52b |
| 20217 | 3 | 4 | | | | IV-1 | Tmem59 |
| 20218 | 3 | 4 | | | | IV-1 | Tmem62 |
| 20219 | 3 | 4 | | | | IV-1 | Tmem63a |
| 20220 | 3 | 4 | | | | IV-1 | Tmem63b |
| 20221 | 3 | 4 | | | | IV-1 | Tmem63c |
| 20222 | 3 | 4 | | | | IV-1 | Tmem64 |
| 20223 | 3 | 4 | | | | IV-1 | Tmem65 |
| 20224 | 3 | 4 | | | | IV-1 | Tmem68 |
| 20225 | 3 | 4 | | | | IV-1 | Tmem69 |
| 20226 | 3 | 4 | | | | IV-1 | Tmem72 |
| 20227 | 3 | 4 | | | | IV-1 | Tmem74 |

Fig. 43 - 120

| | | | | | | | | |
|---|---|---|---|---|---|---|---|---|
| 20228 | 3 | 4 | | | | | IV-1 | Tmem74b |
| 20229 | 3 | 4 | | | | | IV-1 | Tmem8 |
| 20230 | 3 | 4 | | | | | IV-1 | Tmem80 |
| 20231 | 3 | 4 | | | | | IV-1 | Tmem88 |
| 20232 | 3 | 4 | | | | | IV-1 | Tmem89 |
| 20233 | 3 | 4 | | | | | IV-1 | Tmem8c |
| 20234 | 3 | 4 | | | | | IV-1 | Tmem91 |
| 20235 | 3 | 4 | | | | | IV-1 | Tmem92 |
| 20236 | 3 | 4 | | | | | IV-1 | Tmem95 |
| 20237 | 3 | 4 | | | | | IV-1 | Tmem98 |
| 20238 | 3 | 4 | | | | | IV-1 | Tmem9b |
| 20239 | 3 | 4 | | | | | IV-1 | Tmf1 |
| 20240 | 3 | 4 | | | | | IV-1 | Tmie |
| 20241 | 3 | 4 | | | | | IV-1 | Tmod3 |
| 20242 | 3 | 4 | | | | | IV-1 | Tmpo |
| 20243 | 3 | 4 | | | | | IV-1 | Tmprss11c |
| 20244 | 3 | 4 | | | | | IV-1 | Tmprss11e |
| 20245 | 3 | 4 | | | | | IV-1 | Tmprss12 |
| 20246 | 3 | 4 | | | | | IV-1 | Tmprss15 |
| 20247 | 3 | 4 | | | | | IV-1 | Tmprss6 |
| 20248 | 3 | 4 | | | | | IV-1 | Tmprss9 |
| 20249 | 3 | 4 | | | | | IV-1 | Tmsb15a |
| 20250 | 3 | 4 | | | | | IV-1 | Tmub2 |
| 20251 | 3 | 4 | | | | | IV-1 | Tmx3 |
| 20252 | 3 | 4 | | | | | IV-1 | Tnfaip1 |
| 20253 | 3 | 4 | | | | | IV-1 | Tnfaip8l1 |
| 20254 | 3 | 4 | | | | | IV-1 | Tnfaip8l3 |
| 20255 | 3 | 4 | | | | | IV-1 | Tnfrsf11b |
| 20256 | 3 | 4 | | | | | IV-1 | Tnfrsf26 |
| 20257 | 3 | 4 | | | | | IV-1 | Tnfrsf9 |
| 20258 | 3 | 4 | | | | | IV-1 | Tnfsf12 |
| 20259 | 3 | 4 | | | | | IV-1 | Tnfsf12Tnfsf13 |
| 20260 | 3 | 4 | | | | | IV-1 | Tnfsf15 |
| 20261 | 3 | 4 | | | | | IV-1 | Tnfsf18 |
| 20262 | 3 | 4 | | | | | IV-1 | Tnip3 |
| 20263 | 3 | 4 | | | | | IV-1 | Tnk1 |
| 20264 | 3 | 4 | | | | | IV-1 | Tnk2os |
| 20265 | 3 | 4 | | | | | IV-1 | Tnks1bp1 |
| 20266 | 3 | 4 | | | | | IV-1 | Tnks2 |
| 20267 | 3 | 4 | | | | | IV-1 | Tnmd |
| 20268 | 3 | 4 | | | | | IV-1 | Tnn |
| 20269 | 3 | 4 | | | | | IV-1 | Tnpo3 |
| 20270 | 3 | 4 | | | | | IV-1 | Tnr |
| 20271 | 3 | 4 | | | | | IV-1 | Tob2 |
| 20272 | 3 | 4 | | | | | IV-1 | Toe1 |
| 20273 | 3 | 4 | | | | | IV-1 | Tollip |
| 20274 | 3 | 4 | | | | | IV-1 | Tom1l1 |
| 20275 | 3 | 4 | | | | | IV-1 | Tomm20 |
| 20276 | 3 | 4 | | | | | IV-1 | Tomm20l |
| 20277 | 3 | 4 | | | | | IV-1 | Tomm34 |
| 20278 | 3 | 4 | | | | | IV-1 | Tomm5 |
| 20279 | 3 | 4 | | | | | IV-1 | Tomm70a |
| 20280 | 3 | 4 | | | | | IV-1 | Tonsl |
| 20281 | 3 | 4 | | | | | IV-1 | Top1 |
| 20282 | 3 | 4 | | | | | IV-1 | Top3a |
| 20283 | 3 | 4 | | | | | IV-1 | Top3b |
| 20284 | 3 | 4 | | | | | IV-1 | Topaz1 |
| 20285 | 3 | 4 | | | | | IV-1 | Topors |
| 20286 | 3 | 4 | | | | | IV-1 | Toporsl |
| 20287 | 3 | 4 | | | | | IV-1 | Tor1a |
| 20288 | 3 | 4 | | | | | IV-1 | Tor1aip1 |
| 20289 | 3 | 4 | | | | | IV-1 | Tor1aip2 |
| 20290 | 3 | 4 | | | | | IV-1 | Tor1b |
| 20291 | 3 | 4 | | | | | IV-1 | Tor4a |
| 20292 | 3 | 4 | | | | | IV-1 | Tox |
| 20293 | 3 | 4 | | | | | IV-1 | Tox4 |
| 20294 | 3 | 4 | | | | | IV-1 | Tpbg |
| 20295 | 3 | 4 | | | | | IV-1 | Tpbpa |
| 20296 | 3 | 4 | | | | | IV-1 | Tpbpb |
| 20297 | 3 | 4 | | | | | IV-1 | Tpd52 |
| 20298 | 3 | 4 | | | | | IV-1 | Tph1 |
| 20299 | 3 | 4 | | | | | IV-1 | Tph2 |
| 20300 | 3 | 4 | | | | | IV-1 | Tpo |
| 20301 | 3 | 4 | | | | | IV-1 | Tpp1 |
| 20302 | 3 | 4 | | | | | IV-1 | Tpp2 |
| 20303 | 3 | 4 | | | | | IV-1 | Tprg |
| 20304 | 3 | 4 | | | | | IV-1 | Tprn |
| 20305 | 3 | 4 | | | | | IV-1 | Tpsg1 |
| 20306 | 3 | 4 | | | | | IV-1 | Tpst1 |
| 20307 | 3 | 4 | | | | | IV-1 | Tpt1 |
| 20308 | 3 | 4 | | | | | IV-1 | Tpx2 |
| 20309 | 3 | 4 | | | | | IV-1 | Tra2b |
| 20310 | 3 | 4 | | | | | IV-1 | Trabd2b |
| 20311 | 3 | 4 | | | | | IV-1 | Traf2 |
| 20312 | 3 | 4 | | | | | IV-1 | Traf3ip1 |
| 20313 | 3 | 4 | | | | | IV-1 | Traf7 |
| 20314 | 3 | 4 | | | | | IV-1 | Trak1 |
| 20315 | 3 | 4 | | | | | IV-1 | Tram1l1 |
| 20316 | 3 | 4 | | | | | IV-1 | Trank1 |
| 20317 | 3 | 4 | | | | | IV-1 | Trap1 |
| 20318 | 3 | 4 | | | | | IV-1 | Trap1a |
| 20319 | 3 | 4 | | | | | IV-1 | Trappc10 |
| 20320 | 3 | 4 | | | | | IV-1 | Trappc11 |
| 20321 | 3 | 4 | | | | | IV-1 | Trappc12 |
| 20322 | 3 | 4 | | | | | IV-1 | Trappc13 |
| 20323 | 3 | 4 | | | | | IV-1 | Trappc3 |
| 20324 | 3 | 4 | | | | | IV-1 | Trappc3l |
| 20325 | 3 | 4 | | | | | IV-1 | Trappc6b |
| 20326 | 3 | 4 | | | | | IV-1 | Trappc8 |
| 20327 | 3 | 4 | | | | | IV-1 | Trcg1 |
| 20328 | 3 | 4 | | | | | IV-1 | Trdmt1 |
| 20329 | 3 | 4 | | | | | IV-1 | Trem1 |
| 20330 | 3 | 4 | | | | | IV-1 | Treml2 |
| 20331 | 3 | 4 | | | | | IV-1 | Trex2 |
| 20332 | 3 | 4 | | | | | IV-1 | Trf |
| 20333 | 3 | 4 | | | | | IV-1 | Trh |
| 20334 | 3 | 4 | | | | | IV-1 | Trhde |
| 20335 | 3 | 4 | | | | | IV-1 | Trhr |
| 20336 | 3 | 4 | | | | | IV-1 | Trhr2 |
| 20337 | 3 | 4 | | | | | IV-1 | Trim12a |
| 20338 | 3 | 4 | | | | | IV-1 | Trim21 |
| 20339 | 3 | 4 | | | | | IV-1 | Trim23 |
| 20340 | 3 | 4 | | | | | IV-1 | Trim24 |
| 20341 | 3 | 4 | | | | | IV-1 | Trim25 |
| 20342 | 3 | 4 | | | | | IV-1 | Trim3 |
| 20343 | 3 | 4 | | | | | IV-1 | Trim30e-ps1 |
| 20344 | 3 | 4 | | | | | IV-1 | Trim31 |
| 20345 | 3 | 4 | | | | | IV-1 | Trim32 |
| 20346 | 3 | 4 | | | | | IV-1 | Trim33 |
| 20347 | 3 | 4 | | | | | IV-1 | Trim34a |
| 20348 | 3 | 4 | | | | | IV-1 | Trim34b |
| 20349 | 3 | 4 | | | | | IV-1 | Trim40 |
| 20350 | 3 | 4 | | | | | IV-1 | Trim41 |
| 20351 | 3 | 4 | | | | | IV-1 | Trim42 |
| 20352 | 3 | 4 | | | | | IV-1 | Trim43a |
| 20353 | 3 | 4 | | | | | IV-1 | Trim43c |
| 20354 | 3 | 4 | | | | | IV-1 | Trim45 |
| 20355 | 3 | 4 | | | | | IV-1 | Trim52 |
| 20356 | 3 | 4 | | | | | IV-1 | Trim55 |
| 20357 | 3 | 4 | | | | | IV-1 | Trim59 |
| 20358 | 3 | 4 | | | | | IV-1 | Trim60 |
| 20359 | 3 | 4 | | | | | IV-1 | Trim66 |
| 20360 | 3 | 4 | | | | | IV-1 | Trim69 |
| 20361 | 3 | 4 | | | | | IV-1 | Trim75 |
| 20362 | 3 | 4 | | | | | IV-1 | Trim8 |
| 20363 | 3 | 4 | | | | | IV-1 | Triml1 |
| 20364 | 3 | 4 | | | | | IV-1 | Triml2 |
| 20365 | 3 | 4 | | | | | IV-1 | Trip4 |
| 20366 | 3 | 4 | | | | | IV-1 | Triqk |
| 20367 | 3 | 4 | | | | | IV-1 | Trmt10a |
| 20368 | 3 | 4 | | | | | IV-1 | Trmt10c |
| 20369 | 3 | 4 | | | | | IV-1 | Trmt12 |
| 20370 | 3 | 4 | | | | | IV-1 | Trmt13 |
| 20371 | 3 | 4 | | | | | IV-1 | Trmt2a |
| 20372 | 3 | 4 | | | | | IV-1 | Trmt2b |
| 20373 | 3 | 4 | | | | | IV-1 | Trmu |
| 20374 | 3 | 4 | | | | | IV-1 | Trnau1ap |
| 20375 | 3 | 4 | | | | | IV-1 | Troap |
| 20376 | 3 | 4 | | | | | IV-1 | Trove2 |
| 20377 | 3 | 4 | | | | | IV-1 | Trp53bp2 |
| 20378 | 3 | 4 | | | | | IV-1 | Trp53cor1 |
| 20379 | 3 | 4 | | | | | IV-1 | Trp53i13 |
| 20380 | 3 | 4 | | | | | IV-1 | Trp53rk |
| 20381 | 3 | 4 | | | | | IV-1 | Trp73 |
| 20382 | 3 | 4 | | | | | IV-1 | Trpa1 |
| 20383 | 3 | 4 | | | | | IV-1 | Trpc4 |
| 20384 | 3 | 4 | | | | | IV-1 | Trpc5os |
| 20385 | 3 | 4 | | | | | IV-1 | Trpc6 |
| 20386 | 3 | 4 | | | | | IV-1 | Trpc7 |
| 20387 | 3 | 4 | | | | | IV-1 | Trpd52l3 |
| 20388 | 3 | 4 | | | | | IV-1 | Trpm1 |
| 20389 | 3 | 4 | | | | | IV-1 | Trpm3 |
| 20390 | 3 | 4 | | | | | IV-1 | Trpm5 |
| 20391 | 3 | 4 | | | | | IV-1 | Trpm7 |
| 20392 | 3 | 4 | | | | | IV-1 | Trpv1 |
| 20393 | 3 | 4 | | | | | IV-1 | Trpv3 |
| 20394 | 3 | 4 | | | | | IV-1 | Trpv5 |
| 20395 | 3 | 4 | | | | | IV-1 | Trub1 |
| 20396 | 3 | 4 | | | | | IV-1 | Trub2 |
| 20397 | 3 | 4 | | | | | IV-1 | Tsc2 |

Fig. 43 - 121

| | | | | | | | | | | | | | | |
|---|---|---|---|---|---|---|---|---|---|---|---|---|---|---|
| 20398 | 3 | 4 | | | | IV-1 | Tsc22d2 | 20483 | 3 | 4 | | | IV-1 | Ubac2 |
| 20399 | 3 | 4 | | | | IV-1 | Tsc22d4 | 20484 | 3 | 4 | | | IV-1 | Ubap1 |
| 20400 | 3 | 4 | | | | IV-1 | Tsga13 | 20485 | 3 | 4 | | | IV-1 | Ubap1l |
| 20401 | 3 | 4 | | | | IV-1 | Tshb | 20486 | 3 | 4 | | | IV-1 | Ubap2 |
| 20402 | 3 | 4 | | | | IV-1 | Tshr | 20487 | 3 | 4 | | | IV-1 | Ubap2l |
| 20403 | 3 | 4 | | | | IV-1 | Tsix | 20488 | 3 | 4 | | | IV-1 | Ubb |
| 20404 | 3 | 4 | | | | IV-1 | Tsn | 20489 | 3 | 4 | | | IV-1 | Ube2d2a |
| 20405 | 3 | 4 | | | | IV-1 | Tsnax | 20490 | 3 | 4 | | | IV-1 | Ube2d3 |
| 20406 | 3 | 4 | | | | IV-1 | Tspan11 | 20491 | 3 | 4 | | | IV-1 | Ube2dnl1 |
| 20407 | 3 | 4 | | | | IV-1 | Tspan2os | 20492 | 3 | 4 | | | IV-1 | Ube2dnl2 |
| 20408 | 3 | 4 | | | | IV-1 | Tspan3 | 20493 | 3 | 4 | | | IV-1 | Ube2e1 |
| 20409 | 3 | 4 | | | | IV-1 | Tspan31 | 20494 | 3 | 4 | | | IV-1 | Ube2g2 |
| 20410 | 3 | 4 | | | | IV-1 | Tspan9 | 20495 | 3 | 4 | | | IV-1 | Ube2i |
| 20411 | 3 | 4 | | | | IV-1 | Tspear | 20496 | 3 | 4 | | | IV-1 | Ube2j1 |
| 20412 | 3 | 4 | | | | IV-1 | Tspyl1 | 20497 | 3 | 4 | | | IV-1 | Ube2k |
| 20413 | 3 | 4 | | | | IV-1 | Tspyl2 | 20498 | 3 | 4 | | | IV-1 | Ube2l3 |
| 20414 | 3 | 4 | | | | IV-1 | Tspyl3 | 20499 | 3 | 4 | | | IV-1 | Ube2n |
| 20415 | 3 | 4 | | | | IV-1 | Tsr2 | 20500 | 3 | 4 | | | IV-1 | Ube2q1 |
| 20416 | 3 | 4 | | | | IV-1 | Tssc1 | 20501 | 3 | 4 | | | IV-1 | Ube2q2 |
| 20417 | 3 | 4 | | | | IV-1 | Tssc4 | 20502 | 3 | 4 | | | IV-1 | Ube2u |
| 20418 | 3 | 4 | | | | IV-1 | Tssk5 | 20503 | 3 | 4 | | | IV-1 | Ube2v1 |
| 20419 | 3 | 4 | | | | IV-1 | Tstd2 | 20504 | 3 | 4 | | | IV-1 | Ube2v2 |
| 20420 | 3 | 4 | | | | IV-1 | Tsx | 20505 | 3 | 4 | | | IV-1 | Ube2w |
| 20421 | 3 | 4 | | | | IV-1 | Ttbk1 | 20506 | 3 | 4 | | | IV-1 | Ube2z |
| 20422 | 3 | 4 | | | | IV-1 | Ttc1 | 20507 | 3 | 4 | | | IV-1 | Ube3c |
| 20423 | 3 | 4 | | | | IV-1 | Ttc12 | 20508 | 3 | 4 | | | IV-1 | Ube4a |
| 20424 | 3 | 4 | | | | IV-1 | Ttc13 | 20509 | 3 | 4 | | | IV-1 | Ube4b |
| 20425 | 3 | 4 | | | | IV-1 | Ttc17 | 20510 | 3 | 4 | | | IV-1 | Ubiad1 |
| 20426 | 3 | 4 | | | | IV-1 | Ttc19 | 20511 | 3 | 4 | | | IV-1 | Ubl3 |
| 20427 | 3 | 4 | | | | IV-1 | Ttc24 | 20512 | 3 | 4 | | | IV-1 | Ubl4 |
| 20428 | 3 | 4 | | | | IV-1 | Ttc26 | 20513 | 3 | 4 | | | IV-1 | Ubl7 |
| 20429 | 3 | 4 | | | | IV-1 | Ttc34 | 20514 | 3 | 4 | | | IV-1 | Ubn1 |
| 20430 | 3 | 4 | | | | IV-1 | Ttc4 | 20515 | 3 | 4 | | | IV-1 | Ubp1 |
| 20431 | 3 | 4 | | | | IV-1 | Ttc5 | 20516 | 3 | 4 | | | IV-1 | Ubqln1 |
| 20432 | 3 | 4 | | | | IV-1 | Ttc7b | 20517 | 3 | 4 | | | IV-1 | Ubqln2 |
| 20433 | 3 | 4 | | | | IV-1 | Ttc9b | 20518 | 3 | 4 | | | IV-1 | Ubr1 |
| 20434 | 3 | 4 | | | | IV-1 | Ttc9c | 20519 | 3 | 4 | | | IV-1 | Ubr3 |
| 20435 | 3 | 4 | | | | IV-1 | Ttf2 | 20520 | 3 | 4 | | | IV-1 | Ubtd1 |
| 20436 | 3 | 4 | | | | IV-1 | Ttk | 20521 | 3 | 4 | | | IV-1 | Ubtd2 |
| 20437 | 3 | 4 | | | | IV-1 | Ttl | 20522 | 3 | 4 | | | IV-1 | Ubtf |
| 20438 | 3 | 4 | | | | IV-1 | Ttll13 | 20523 | 3 | 4 | | | IV-1 | Ubtfl1 |
| 20439 | 3 | 4 | | | | IV-1 | Ttll2 | 20524 | 3 | 4 | | | IV-1 | Ubxn11 |
| 20440 | 3 | 4 | | | | IV-1 | Ttll6 | 20525 | 3 | 4 | | | IV-1 | Ubxn7 |
| 20441 | 3 | 4 | | | | IV-1 | Ttll9 | 20526 | 3 | 4 | | | IV-1 | Ubxn8 |
| 20442 | 3 | 4 | | | | IV-1 | Ttyh1 | 20527 | 3 | 4 | | | IV-1 | Uchl1os |
| 20443 | 3 | 4 | | | | IV-1 | Tub | 20528 | 3 | 4 | | | IV-1 | Uchl4 |
| 20444 | 3 | 4 | | | | IV-1 | Tuba1b | 20529 | 3 | 4 | | | IV-1 | Uck1 |
| 20445 | 3 | 4 | | | | IV-1 | Tuba3 | 20530 | 3 | 4 | | | IV-1 | Ucn3 |
| 20446 | 3 | 4 | | | | IV-1 | Tubb2a | 20531 | 3 | 4 | | | IV-1 | Ucp2 |
| 20447 | 3 | 4 | | | | IV-1 | Tubb3 | 20532 | 3 | 4 | | | IV-1 | Uevld |
| 20448 | 3 | 4 | | | | IV-1 | Tubb5 | 20533 | 3 | 4 | | | IV-1 | Ufl1 |
| 20449 | 3 | 4 | | | | IV-1 | Tubb6 | 20534 | 3 | 4 | | | IV-1 | Ufm1 |
| 20450 | 3 | 4 | | | | IV-1 | Tubg2 | 20535 | 3 | 4 | | | IV-1 | Ufsp2 |
| 20451 | 3 | 4 | | | | IV-1 | Tubgcp2 | 20536 | 3 | 4 | | | IV-1 | Ugcg |
| 20452 | 3 | 4 | | | | IV-1 | Tubgcp3 | 20537 | 3 | 4 | | | IV-1 | Ugdh |
| 20453 | 3 | 4 | | | | IV-1 | Tubgcp5 | 20538 | 3 | 4 | | | IV-1 | Uggt1 |
| 20454 | 3 | 4 | | | | IV-1 | Tug1 | 20539 | 3 | 4 | | | IV-1 | Uggt2 |
| 20455 | 3 | 4 | | | | IV-1 | Tulp1 | 20540 | 3 | 4 | | | IV-1 | Ugt1a1 |
| 20456 | 3 | 4 | | | | IV-1 | Tunar | 20541 | 3 | 4 | | | IV-1 | Ugt1a10 |
| 20457 | 3 | 4 | | | | IV-1 | Tut1 | 20542 | 3 | 4 | | | IV-1 | Ugt1a5 |
| 20458 | 3 | 4 | | | | IV-1 | Tvp23b | 20543 | 3 | 4 | | | IV-1 | Ugt1a9 |
| 20459 | 3 | 4 | | | | IV-1 | Twf1 | 20544 | 3 | 4 | | | IV-1 | Ugt2a1 |
| 20460 | 3 | 4 | | | | IV-1 | Twist1 | 20545 | 3 | 4 | | | IV-1 | Ugt2a3 |
| 20461 | 3 | 4 | | | | IV-1 | Twist2 | 20546 | 3 | 4 | | | IV-1 | Ugt2b1 |
| 20462 | 3 | 4 | | | | IV-1 | Twistnb | 20547 | 3 | 4 | | | IV-1 | Ugt2b5 |
| 20463 | 3 | 4 | | | | IV-1 | Twsg1 | 20548 | 3 | 4 | | | IV-1 | Ugt8a |
| 20464 | 3 | 4 | | | | IV-1 | Txlna | 20549 | 3 | 4 | | | IV-1 | Uimc1 |
| 20465 | 3 | 4 | | | | IV-1 | Txn2 | 20550 | 3 | 4 | | | IV-1 | Ulbp1 |
| 20466 | 3 | 4 | | | | IV-1 | Txndc12 | 20551 | 3 | 4 | | | IV-1 | Ulk1 |
| 20467 | 3 | 4 | | | | IV-1 | Txndc16 | 20552 | 3 | 4 | | | IV-1 | Ulk2 |
| 20468 | 3 | 4 | | | | IV-1 | Txndc8 | 20553 | 3 | 4 | | | IV-1 | Ulk3 |
| 20469 | 3 | 4 | | | | IV-1 | Txndc9 | 20554 | 3 | 4 | | | IV-1 | Umodl1 |
| 20470 | 3 | 4 | | | | IV-1 | Txnl1 | 20555 | 3 | 4 | | | IV-1 | Umps |
| 20471 | 3 | 4 | | | | IV-1 | Txnl4b | 20556 | 3 | 4 | | | IV-1 | Unc119b |
| 20472 | 3 | 4 | | | | IV-1 | Txnrd2 | 20557 | 3 | 4 | | | IV-1 | Unc13a |
| 20473 | 3 | 4 | | | | IV-1 | Tyms-ps | 20558 | 3 | 4 | | | IV-1 | Unc13b |
| 20474 | 3 | 4 | | | | IV-1 | Tyr | 20559 | 3 | 4 | | | IV-1 | Unc13d |
| 20475 | 3 | 4 | | | | IV-1 | U2af2 | 20560 | 3 | 4 | | | IV-1 | Unc45a |
| 20476 | 3 | 4 | | | | IV-1 | U2surp | 20561 | 3 | 4 | | | IV-1 | Unc45b |
| 20477 | 3 | 4 | | | | IV-1 | U90926 | 20562 | 3 | 4 | | | IV-1 | Unc5c |
| 20478 | 3 | 4 | | | | IV-1 | Uap1 | 20563 | 3 | 4 | | | IV-1 | Unc5d |
| 20479 | 3 | 4 | | | | IV-1 | Uba1 | 20564 | 3 | 4 | | | IV-1 | Unc79 |
| 20480 | 3 | 4 | | | | IV-1 | Uba1y | 20565 | 3 | 4 | | | IV-1 | Unc80 |
| 20481 | 3 | 4 | | | | IV-1 | Uba3 | 20566 | 3 | 4 | | | IV-1 | Uncx |
| 20482 | 3 | 4 | | | | IV-1 | Uba5 | 20567 | 3 | 4 | | | IV-1 | Uox |

Fig. 43 - 122

| | | | | | | | |
|---|---|---|---|---|---|---|---|
| 20568 | 3 | 4 | | | | IV-1 | Upb1 |
| 20569 | 3 | 4 | | | | IV-1 | Upf2 |
| 20570 | 3 | 4 | | | | IV-1 | Uqcc1 |
| 20571 | 3 | 4 | | | | IV-1 | Uqcrc1 |
| 20572 | 3 | 4 | | | | IV-1 | Uqcrc2 |
| 20573 | 3 | 4 | | | | IV-1 | Uqcrfs1 |
| 20574 | 3 | 4 | | | | IV-1 | Urb1 |
| 20575 | 3 | 4 | | | | IV-1 | Urgcp |
| 20576 | 3 | 4 | | | | IV-1 | Uri1 |
| 20577 | 3 | 4 | | | | IV-1 | Uroc1 |
| 20578 | 3 | 4 | | | | IV-1 | Usb1 |
| 20579 | 3 | 4 | | | | IV-1 | Usf2 |
| 20580 | 3 | 4 | | | | IV-1 | Ush1c |
| 20581 | 3 | 4 | | | | IV-1 | Ush1g |
| 20582 | 3 | 4 | | | | IV-1 | Ush2a |
| 20583 | 3 | 4 | | | | IV-1 | Uso1 |
| 20584 | 3 | 4 | | | | IV-1 | Usp1 |
| 20585 | 3 | 4 | | | | IV-1 | Usp10 |
| 20586 | 3 | 4 | | | | IV-1 | Usp12 |
| 20587 | 3 | 4 | | | | IV-1 | Usp14 |
| 20588 | 3 | 4 | | | | IV-1 | Usp15 |
| 20589 | 3 | 4 | | | | IV-1 | Usp16 |
| 20590 | 3 | 4 | | | | IV-1 | Usp17la |
| 20591 | 3 | 4 | | | | IV-1 | Usp17lb |
| 20592 | 3 | 4 | | | | IV-1 | Usp17lc |
| 20593 | 3 | 4 | | | | IV-1 | Usp17ld |
| 20594 | 3 | 4 | | | | IV-1 | Usp17le |
| 20595 | 3 | 4 | | | | IV-1 | Usp24 |
| 20596 | 3 | 4 | | | | IV-1 | Usp25 |
| 20597 | 3 | 4 | | | | IV-1 | Usp26 |
| 20598 | 3 | 4 | | | | IV-1 | Usp27x |
| 20599 | 3 | 4 | | | | IV-1 | Usp29 |
| 20600 | 3 | 4 | | | | IV-1 | Usp32 |
| 20601 | 3 | 4 | | | | IV-1 | Usp33 |
| 20602 | 3 | 4 | | | | IV-1 | Usp35 |
| 20603 | 3 | 4 | | | | IV-1 | Usp36 |
| 20604 | 3 | 4 | | | | IV-1 | Usp37 |
| 20605 | 3 | 4 | | | | IV-1 | Usp38 |
| 20606 | 3 | 4 | | | | IV-1 | Usp39 |
| 20607 | 3 | 4 | | | | IV-1 | Usp4 |
| 20608 | 3 | 4 | | | | IV-1 | Usp42 |
| 20609 | 3 | 4 | | | | IV-1 | Usp43 |
| 20610 | 3 | 4 | | | | IV-1 | Usp44 |
| 20611 | 3 | 4 | | | | IV-1 | Usp45 |
| 20612 | 3 | 4 | | | | IV-1 | Usp47 |
| 20613 | 3 | 4 | | | | IV-1 | Usp48 |
| 20614 | 3 | 4 | | | | IV-1 | Usp50 |
| 20615 | 3 | 4 | | | | IV-1 | Usp51 |
| 20616 | 3 | 4 | | | | IV-1 | Usp7 |
| 20617 | 3 | 4 | | | | IV-1 | Usp9y |
| 20618 | 3 | 4 | | | | IV-1 | Utp15 |
| 20619 | 3 | 4 | | | | IV-1 | Utp18 |
| 20620 | 3 | 4 | | | | IV-1 | Utp20 |
| 20621 | 3 | 4 | | | | IV-1 | Utp23 |
| 20622 | 3 | 4 | | | | IV-1 | Utp6 |
| 20623 | 3 | 4 | | | | IV-1 | Utrn |
| 20624 | 3 | 4 | | | | IV-1 | Uts2 |
| 20625 | 3 | 4 | | | | IV-1 | Uts2b |
| 20626 | 3 | 4 | | | | IV-1 | Uvrag |
| 20627 | 3 | 4 | | | | IV-1 | Uvssa |
| 20628 | 3 | 4 | | | | IV-1 | V1ra8 |
| 20629 | 3 | 4 | | | | IV-1 | V1rd18 |
| 20630 | 3 | 4 | | | | IV-1 | V1rd19 |
| 20631 | 3 | 4 | | | | IV-1 | Vac14 |
| 20632 | 3 | 4 | | | | IV-1 | Vamp7 |
| 20633 | 3 | 4 | | | | IV-1 | Vangl1 |
| 20634 | 3 | 4 | | | | IV-1 | Vapa |
| 20635 | 3 | 4 | | | | IV-1 | Vapb |
| 20636 | 3 | 4 | | | | IV-1 | Vars |
| 20637 | 3 | 4 | | | | IV-1 | Vash2 |
| 20638 | 3 | 4 | | | | IV-1 | Vasp |
| 20639 | 3 | 4 | | | | IV-1 | Vav1 |
| 20640 | 3 | 4 | | | | IV-1 | Vax1 |
| 20641 | 3 | 4 | | | | IV-1 | Vax2 |
| 20642 | 3 | 4 | | | | IV-1 | Vbp1 |
| 20643 | 3 | 4 | | | | IV-1 | Vcp |
| 20644 | 3 | 4 | | | | IV-1 | Veph1 |
| 20645 | 3 | 4 | | | | IV-1 | Vezf1 |
| 20646 | 3 | 4 | | | | IV-1 | Vezt |
| 20647 | 3 | 4 | | | | IV-1 | Vgll1 |
| 20648 | 3 | 4 | | | | IV-1 | Vhl |
| 20649 | 3 | 4 | | | | IV-1 | Vil1 |
| 20650 | 3 | 4 | | | | IV-1 | Vimp |
| 20651 | 3 | 4 | | | | IV-1 | Vip |
| 20652 | 3 | 4 | | | | IV-1 | Vipas39 |

| | | | | | | | |
|---|---|---|---|---|---|---|---|
| 20653 | 3 | 4 | | | | IV-1 | Vkorc1 |
| 20654 | 3 | 4 | | | | IV-1 | Vmac |
| 20655 | 3 | 4 | | | | IV-1 | Vmn1r1 |
| 20656 | 3 | 4 | | | | IV-1 | Vmn1r10 |
| 20657 | 3 | 4 | | | | IV-1 | Vmn1r100 |
| 20658 | 3 | 4 | | | | IV-1 | Vmn1r101 |
| 20659 | 3 | 4 | | | | IV-1 | Vmn1r103 |
| 20660 | 3 | 4 | | | | IV-1 | Vmn1r104 |
| 20661 | 3 | 4 | | | | IV-1 | Vmn1r45 |
| 20662 | 3 | 4 | | | | IV-1 | Vmn1r46 |
| 20663 | 3 | 4 | | | | IV-1 | Vmn2r34 |
| 20664 | 3 | 4 | | | | IV-1 | Vmn2r66 |
| 20665 | 3 | 4 | | | | IV-1 | Vps11 |
| 20666 | 3 | 4 | | | | IV-1 | Vps13a |
| 20667 | 3 | 4 | | | | IV-1 | Vps13b |
| 20668 | 3 | 4 | | | | IV-1 | Vps16 |
| 20669 | 3 | 4 | | | | IV-1 | Vps18 |
| 20670 | 3 | 4 | | | | IV-1 | Vps26a |
| 20671 | 3 | 4 | | | | IV-1 | Vps26b |
| 20672 | 3 | 4 | | | | IV-1 | Vps29 |
| 20673 | 3 | 4 | | | | IV-1 | Vps33b |
| 20674 | 3 | 4 | | | | IV-1 | Vps35 |
| 20675 | 3 | 4 | | | | IV-1 | Vps37b |
| 20676 | 3 | 4 | | | | IV-1 | Vps37c |
| 20677 | 3 | 4 | | | | IV-1 | Vps39 |
| 20678 | 3 | 4 | | | | IV-1 | Vps41 |
| 20679 | 3 | 4 | | | | IV-1 | Vps4b |
| 20680 | 3 | 4 | | | | IV-1 | Vps52 |
| 20681 | 3 | 4 | | | | IV-1 | Vps53 |
| 20682 | 3 | 4 | | | | IV-1 | Vps54 |
| 20683 | 3 | 4 | | | | IV-1 | Vps8 |
| 20684 | 3 | 4 | | | | IV-1 | Vrk1 |
| 20685 | 3 | 4 | | | | IV-1 | Vrtn |
| 20686 | 3 | 4 | | | | IV-1 | Vsig1 |
| 20687 | 3 | 4 | | | | IV-1 | Vsig10 |
| 20688 | 3 | 4 | | | | IV-1 | Vsig10l |
| 20689 | 3 | 4 | | | | IV-1 | Vstm2a |
| 20690 | 3 | 4 | | | | IV-1 | Vstm2b |
| 20691 | 3 | 4 | | | | IV-1 | Vstm2l |
| 20692 | 3 | 4 | | | | IV-1 | Vsx1 |
| 20693 | 3 | 4 | | | | IV-1 | Vsx2 |
| 20694 | 3 | 4 | | | | IV-1 | Vta1 |
| 20695 | 3 | 4 | | | | IV-1 | Vti1a |
| 20696 | 3 | 4 | | | | IV-1 | Vti1b |
| 20697 | 3 | 4 | | | | IV-1 | Vwa5a |
| 20698 | 3 | 4 | | | | IV-1 | Vwa5b1 |
| 20699 | 3 | 4 | | | | IV-1 | Vwa5b2 |
| 20700 | 3 | 4 | | | | IV-1 | Vwa7 |
| 20701 | 3 | 4 | | | | IV-1 | Vwc2 |
| 20702 | 3 | 4 | | | | IV-1 | Vwc2l |
| 20703 | 3 | 4 | | | | IV-1 | Vwde |
| 20704 | 3 | 4 | | | | IV-1 | Wac |
| 20705 | 3 | 4 | | | | IV-1 | Wars |
| 20706 | 3 | 4 | | | | IV-1 | Was |
| 20707 | 3 | 4 | | | | IV-1 | Wasf1 |
| 20708 | 3 | 4 | | | | IV-1 | Wasl |
| 20709 | 3 | 4 | | | | IV-1 | Wbp1 |
| 20710 | 3 | 4 | | | | IV-1 | Wbp11 |
| 20711 | 3 | 4 | | | | IV-1 | Wbp1l |
| 20712 | 3 | 4 | | | | IV-1 | Wbp2 |
| 20713 | 3 | 4 | | | | IV-1 | Wbp2nl |
| 20714 | 3 | 4 | | | | IV-1 | Wbp4 |
| 20715 | 3 | 4 | | | | IV-1 | Wbscr28 |
| 20716 | 3 | 4 | | | | IV-1 | Wdfy1 |
| 20717 | 3 | 4 | | | | IV-1 | Wdfy4 |
| 20718 | 3 | 4 | | | | IV-1 | Wdr1 |
| 20719 | 3 | 4 | | | | IV-1 | Wdr11 |
| 20720 | 3 | 4 | | | | IV-1 | Wdr13 |
| 20721 | 3 | 4 | | | | IV-1 | Wdr16 |
| 20722 | 3 | 4 | | | | IV-1 | Wdr17 |
| 20723 | 3 | 4 | | | | IV-1 | Wdr18 |
| 20724 | 3 | 4 | | | | IV-1 | Wdr20 |
| 20725 | 3 | 4 | | | | IV-1 | Wdr25 |
| 20726 | 3 | 4 | | | | IV-1 | Wdr26 |
| 20727 | 3 | 4 | | | | IV-1 | Wdr27 |
| 20728 | 3 | 4 | | | | IV-1 | Wdr3 |
| 20729 | 3 | 4 | | | | IV-1 | Wdr31 |
| 20730 | 3 | 4 | | | | IV-1 | Wdr33 |
| 20731 | 3 | 4 | | | | IV-1 | Wdr35 |
| 20732 | 3 | 4 | | | | IV-1 | Wdr37 |
| 20733 | 3 | 4 | | | | IV-1 | Wdr38 |
| 20734 | 3 | 4 | | | | IV-1 | Wdr4 |
| 20735 | 3 | 4 | | | | IV-1 | Wdr41 |
| 20736 | 3 | 4 | | | | IV-1 | Wdr44 |
| 20737 | 3 | 4 | | | | IV-1 | Wdr45b |

Fig. 43 - 123

| | | | | | | | | | | | | |
|---|---|---|---|---|---|---|---|---|---|---|---|---|
| 20738 | 3 | 4 | | | IV-1 | Wdr47 | 20823 | 3 | 4 | | IV-1 | Ythdf3 |
| 20739 | 3 | 4 | | | IV-1 | Wdr48 | 20824 | 3 | 4 | | IV-1 | Ywhab |
| 20740 | 3 | 4 | | | IV-1 | Wdr5 | 20825 | 3 | 4 | | IV-1 | Ywhae |
| 20741 | 3 | 4 | | | IV-1 | Wdr54 | 20826 | 3 | 4 | | IV-1 | Ywhag |
| 20742 | 3 | 4 | | | IV-1 | Wdr59 | 20827 | 3 | 4 | | IV-1 | Ywhah |
| 20743 | 3 | 4 | | | IV-1 | Wdr5b | 20828 | 3 | 4 | | IV-1 | Ywhaz |
| 20744 | 3 | 4 | | | IV-1 | Wdr63 | 20829 | 3 | 4 | | IV-1 | Yy1 |
| 20745 | 3 | 4 | | | IV-1 | Wdr64 | 20830 | 3 | 4 | | IV-1 | Zan |
| 20746 | 3 | 4 | | | IV-1 | Wdr65 | 20831 | 3 | 4 | | IV-1 | Zar1 |
| 20747 | 3 | 4 | | | IV-1 | Wdr7 | 20832 | 3 | 4 | | IV-1 | Zar1l |
| 20748 | 3 | 4 | | | IV-1 | Wdr70 | 20833 | 3 | 4 | | IV-1 | Zbbx |
| 20749 | 3 | 4 | | | IV-1 | Wdr72 | 20834 | 3 | 4 | | IV-1 | Zbed3 |
| 20750 | 3 | 4 | | | IV-1 | Wdr73 | 20835 | 3 | 4 | | IV-1 | Zbed5 |
| 20751 | 3 | 4 | | | IV-1 | Wdr76 | 20836 | 3 | 4 | | IV-1 | Zbtb14 |
| 20752 | 3 | 4 | | | IV-1 | Wdr77 | 20837 | 3 | 4 | | IV-1 | Zbtb2 |
| 20753 | 3 | 4 | | | IV-1 | Wdr82 | 20838 | 3 | 4 | | IV-1 | Zbtb21 |
| 20754 | 3 | 4 | | | IV-1 | Wdr89 | 20839 | 3 | 4 | | IV-1 | Zbtb22 |
| 20755 | 3 | 4 | | | IV-1 | Wdr90 | 20840 | 3 | 4 | | IV-1 | Zbtb24 |
| 20756 | 3 | 4 | | | IV-1 | Wdr93 | 20841 | 3 | 4 | | IV-1 | Zbtb25 |
| 20757 | 3 | 4 | | | IV-1 | Wdr95 | 20842 | 3 | 4 | | IV-1 | Zbtb3 |
| 20758 | 3 | 4 | | | IV-1 | Wdr96 | 20843 | 3 | 4 | | IV-1 | Zbtb33 |
| 20759 | 3 | 4 | | | IV-1 | Wdyhv1 | 20844 | 3 | 4 | | IV-1 | Zbtb37 |
| 20760 | 3 | 4 | | | IV-1 | Wfdc11 | 20845 | 3 | 4 | | IV-1 | Zbtb41 |
| 20761 | 3 | 4 | | | IV-1 | Wfdc5 | 20846 | 3 | 4 | | IV-1 | Zbtb42 |
| 20762 | 3 | 4 | | | IV-1 | Wfs1 | 20847 | 3 | 4 | | IV-1 | Zbtb43 |
| 20763 | 3 | 4 | | | IV-1 | Whamm | 20848 | 3 | 4 | | IV-1 | Zbtb48 |
| 20764 | 3 | 4 | | | IV-1 | Wipf2 | 20849 | 3 | 4 | | IV-1 | Zbtb5 |
| 20765 | 3 | 4 | | | IV-1 | Wipi2 | 20850 | 3 | 4 | | IV-1 | Zbtb6 |
| 20766 | 3 | 4 | | | IV-1 | Wisp1 | 20851 | 3 | 4 | | IV-1 | Zbtb8a |
| 20767 | 3 | 4 | | | IV-1 | Wls | 20852 | 3 | 4 | | IV-1 | Zbtb8b |
| 20768 | 3 | 4 | | | IV-1 | Wnk1 | 20853 | 3 | 4 | | IV-1 | Zbtbd6 |
| 20769 | 3 | 4 | | | IV-1 | Wnk3 | 20854 | 3 | 4 | | IV-1 | Zc2hc1a |
| 20770 | 3 | 4 | | | IV-1 | Wnt1 | 20855 | 3 | 4 | | IV-1 | Zc2hc1c |
| 20771 | 3 | 4 | | | IV-1 | Wnt10a | 20856 | 3 | 4 | | IV-1 | Zc3h10 |
| 20772 | 3 | 4 | | | IV-1 | Wnt16 | 20857 | 3 | 4 | | IV-1 | Zc3h11a |
| 20773 | 3 | 4 | | | IV-1 | Wnt3 | 20858 | 3 | 4 | | IV-1 | Zc3h12a |
| 20774 | 3 | 4 | | | IV-1 | Wnt3a | 20859 | 3 | 4 | | IV-1 | Zc3h12b |
| 20775 | 3 | 4 | | | IV-1 | Wnt5b | 20860 | 3 | 4 | | IV-1 | Zc3h14 |
| 20776 | 3 | 4 | | | IV-1 | Wnt6 | 20861 | 3 | 4 | | IV-1 | Zc3h15 |
| 20777 | 3 | 4 | | | IV-1 | Wnt7a | 20862 | 3 | 4 | | IV-1 | Zc3h18 |
| 20778 | 3 | 4 | | | IV-1 | Wnt7b | 20863 | 3 | 4 | | IV-1 | Zc3h3 |
| 20779 | 3 | 4 | | | IV-1 | Wnt8a | 20864 | 3 | 4 | | IV-1 | Zc3h4 |
| 20780 | 3 | 4 | | | IV-1 | Wnt9a | 20865 | 3 | 4 | | IV-1 | Zc3h7a |
| 20781 | 3 | 4 | | | IV-1 | Wnt9b | 20866 | 3 | 4 | | IV-1 | Zc3h7b |
| 20782 | 3 | 4 | | | IV-1 | Wrap53 | 20867 | 3 | 4 | | IV-1 | Zc3hc1 |
| 20783 | 3 | 4 | | | IV-1 | Wrb | 20868 | 3 | 4 | | IV-1 | Zcchc11 |
| 20784 | 3 | 4 | | | IV-1 | Wsb1 | 20869 | 3 | 4 | | IV-1 | Zcchc13 |
| 20785 | 3 | 4 | | | IV-1 | Wsb2 | 20870 | 3 | 4 | | IV-1 | Zcchc16 |
| 20786 | 3 | 4 | | | IV-1 | Wscd2 | 20871 | 3 | 4 | | IV-1 | Zcchc17 |
| 20787 | 3 | 4 | | | IV-1 | Wt1 | 20872 | 3 | 4 | | IV-1 | Zcchc4 |
| 20788 | 3 | 4 | | | IV-1 | Wtap | 20873 | 3 | 4 | | IV-1 | Zcchc5 |
| 20789 | 3 | 4 | | | IV-1 | Wtip | 20874 | 3 | 4 | | IV-1 | Zcchc7 |
| 20790 | 3 | 4 | | | IV-1 | Wwp1 | 20875 | 3 | 4 | | IV-1 | Zdbf2 |
| 20791 | 3 | 4 | | | IV-1 | Wwp2 | 20876 | 3 | 4 | | IV-1 | Zdhhc1 |
| 20792 | 3 | 4 | | | IV-1 | Wwtr1 | 20877 | 3 | 4 | | IV-1 | Zdhhc11 |
| 20793 | 3 | 4 | | | IV-1 | Xab2 | 20878 | 3 | 4 | | IV-1 | Zdhhc13 |
| 20794 | 3 | 4 | | | IV-1 | Xcr1 | 20879 | 3 | 4 | | IV-1 | Zdhhc15 |
| 20795 | 3 | 4 | | | IV-1 | Xist | 20880 | 3 | 4 | | IV-1 | Zdhhc17 |
| 20796 | 3 | 4 | | | IV-1 | Xkr4 | 20881 | 3 | 4 | | IV-1 | Zdhhc18 |
| 20797 | 3 | 4 | | | IV-1 | Xkr6 | 20882 | 3 | 4 | | IV-1 | Zdhhc19 |
| 20798 | 3 | 4 | | | IV-1 | Xlr3c | 20883 | 3 | 4 | | IV-1 | Zdhhc2 |
| 20799 | 3 | 4 | | | IV-1 | Xlr5a | 20884 | 3 | 4 | | IV-1 | Zdhhc20 |
| 20800 | 3 | 4 | | | IV-1 | Xlr5b | 20885 | 3 | 4 | | IV-1 | Zdhhc21 |
| 20801 | 3 | 4 | | | IV-1 | Xlr5c | 20886 | 3 | 4 | | IV-1 | Zdhhc22 |
| 20802 | 3 | 4 | | | IV-1 | Xntrpc | 20887 | 3 | 4 | | IV-1 | Zdhhc25 |
| 20803 | 3 | 4 | | | IV-1 | Xpo6 | 20888 | 3 | 4 | | IV-1 | Zdhhc3 |
| 20804 | 3 | 4 | | | IV-1 | Xpot | 20889 | 3 | 4 | | IV-1 | Zdhhc5 |
| 20805 | 3 | 4 | | | IV-1 | Xpr1 | 20890 | 3 | 4 | | IV-1 | Zdhhc6 |
| 20806 | 3 | 4 | | | IV-1 | Xrcc4 | 20891 | 3 | 4 | | IV-1 | Zdhhc7 |
| 20807 | 3 | 4 | | | IV-1 | Xrn2 | 20892 | 3 | 4 | | IV-1 | Zdhhc9 |
| 20808 | 3 | 4 | | | IV-1 | Xxylt1 | 20893 | 3 | 4 | | IV-1 | Zer1 |
| 20809 | 3 | 4 | | | IV-1 | Yae1d1 | 20894 | 3 | 4 | | IV-1 | Zfand3 |
| 20810 | 3 | 4 | | | IV-1 | Yap1 | 20895 | 3 | 4 | | IV-1 | Zfhx2os |
| 20811 | 3 | 4 | | | IV-1 | Ybx1 | 20896 | 3 | 4 | | IV-1 | Zfhx4 |
| 20812 | 3 | 4 | | | IV-1 | Ybx3 | 20897 | 3 | 4 | | IV-1 | Zfp105 |
| 20813 | 3 | 4 | | | IV-1 | Yeats4 | 20898 | 3 | 4 | | IV-1 | Zfp11 |
| 20814 | 3 | 4 | | | IV-1 | Yes1 | 20899 | 3 | 4 | | IV-1 | Zfp110 |
| 20815 | 3 | 4 | | | IV-1 | Yipf5 | 20900 | 3 | 4 | | IV-1 | Zfp120 |
| 20816 | 3 | 4 | | | IV-1 | Yipf6 | 20901 | 3 | 4 | | IV-1 | Zfp128 |
| 20817 | 3 | 4 | | | IV-1 | Ykt6 | 20902 | 3 | 4 | | IV-1 | Zfp131 |
| 20818 | 3 | 4 | | | IV-1 | Yme1l1 | 20903 | 3 | 4 | | IV-1 | Zfp146 |
| 20819 | 3 | 4 | | | IV-1 | Ypel5 | 20904 | 3 | 4 | | IV-1 | Zfp148 |
| 20820 | 3 | 4 | | | IV-1 | Ythdc1 | 20905 | 3 | 4 | | IV-1 | Zfp157 |
| 20821 | 3 | 4 | | | IV-1 | Ythdf1 | 20906 | 3 | 4 | | IV-1 | Zfp160 |
| 20822 | 3 | 4 | | | IV-1 | Ythdf2 | 20907 | 3 | 4 | | IV-1 | Zfp174 |

Fig. 43 - 124

| | | | | | | | |
|---|---|---|---|---|---|---|---|
| 20908 | 3 | 4 | | | IV-1 | Zfp184 |
| 20909 | 3 | 4 | | | IV-1 | Zfp191 |
| 20910 | 3 | 4 | | | IV-1 | Zfp2 |
| 20911 | 3 | 4 | | | IV-1 | Zfp202 |
| 20912 | 3 | 4 | | | IV-1 | Zfp207 |
| 20913 | 3 | 4 | | | IV-1 | Zfp212 |
| 20914 | 3 | 4 | | | IV-1 | Zfp219 |
| 20915 | 3 | 4 | | | IV-1 | Zfp229 |
| 20916 | 3 | 4 | | | IV-1 | Zfp239 |
| 20917 | 3 | 4 | | | IV-1 | Zfp26 |
| 20918 | 3 | 4 | | | IV-1 | Zfp263 |
| 20919 | 3 | 4 | | | IV-1 | Zfp266 |
| 20920 | 3 | 4 | | | IV-1 | Zfp27 |
| 20921 | 3 | 4 | | | IV-1 | Zfp273 |
| 20922 | 3 | 4 | | | IV-1 | Zfp276 |
| 20923 | 3 | 4 | | | IV-1 | Zfp28 |
| 20924 | 3 | 4 | | | IV-1 | Zfp280b |
| 20925 | 3 | 4 | | | IV-1 | Zfp282 |
| 20926 | 3 | 4 | | | IV-1 | Zfp300 |
| 20927 | 3 | 4 | | | IV-1 | Zfp317 |
| 20928 | 3 | 4 | | | IV-1 | Zfp330 |
| 20929 | 3 | 4 | | | IV-1 | Zfp345 |
| 20930 | 3 | 4 | | | IV-1 | Zfp35 |
| 20931 | 3 | 4 | | | IV-1 | Zfp352 |
| 20932 | 3 | 4 | | | IV-1 | Zfp365 |
| 20933 | 3 | 4 | | | IV-1 | Zfp367 |
| 20934 | 3 | 4 | | | IV-1 | Zfp36l3 |
| 20935 | 3 | 4 | | | IV-1 | Zfp37 |
| 20936 | 3 | 4 | | | IV-1 | Zfp382 |
| 20937 | 3 | 4 | | | IV-1 | Zfp383 |
| 20938 | 3 | 4 | | | IV-1 | Zfp384 |
| 20939 | 3 | 4 | | | IV-1 | Zfp385c |
| 20940 | 3 | 4 | | | IV-1 | Zfp386 |
| 20941 | 3 | 4 | | | IV-1 | Zfp389 |
| 20942 | 3 | 4 | | | IV-1 | Zfp395 |
| 20943 | 3 | 4 | | | IV-1 | Zfp408 |
| 20944 | 3 | 4 | | | IV-1 | Zfp41 |
| 20945 | 3 | 4 | | | IV-1 | Zfp410 |
| 20946 | 3 | 4 | | | IV-1 | Zfp414 |
| 20947 | 3 | 4 | | | IV-1 | Zfp42 |
| 20948 | 3 | 4 | | | IV-1 | Zfp422 |
| 20949 | 3 | 4 | | | IV-1 | Zfp438 |
| 20950 | 3 | 4 | | | IV-1 | Zfp442 |
| 20951 | 3 | 4 | | | IV-1 | Zfp446 |
| 20952 | 3 | 4 | | | IV-1 | Zfp454 |
| 20953 | 3 | 4 | | | IV-1 | Zfp455 |
| 20954 | 3 | 4 | | | IV-1 | Zfp457 |
| 20955 | 3 | 4 | | | IV-1 | Zfp458 |
| 20956 | 3 | 4 | | | IV-1 | Zfp473 |
| 20957 | 3 | 4 | | | IV-1 | Zfp488 |
| 20958 | 3 | 4 | | | IV-1 | Zfp511 |
| 20959 | 3 | 4 | | | IV-1 | Zfp521 |
| 20960 | 3 | 4 | | | IV-1 | Zfp53 |
| 20961 | 3 | 4 | | | IV-1 | Zfp534 |
| 20962 | 3 | 4 | | | IV-1 | Zfp536 |
| 20963 | 3 | 4 | | | IV-1 | Zfp541 |
| 20964 | 3 | 4 | | | IV-1 | Zfp551 |
| 20965 | 3 | 4 | | | IV-1 | Zfp558 |
| 20966 | 3 | 4 | | | IV-1 | Zfp575 |
| 20967 | 3 | 4 | | | IV-1 | Zfp597 |
| 20968 | 3 | 4 | | | IV-1 | Zfp599 |
| 20969 | 3 | 4 | | | IV-1 | Zfp600 |
| 20970 | 3 | 4 | | | IV-1 | Zfp616 |
| 20971 | 3 | 4 | | | IV-1 | Zfp617 |
| 20972 | 3 | 4 | | | IV-1 | Zfp618 |
| 20973 | 3 | 4 | | | IV-1 | Zfp62 |
| 20974 | 3 | 4 | | | IV-1 | Zfp628 |
| 20975 | 3 | 4 | | | IV-1 | Zfp64 |
| 20976 | 3 | 4 | | | IV-1 | Zfp648 |
| 20977 | 3 | 4 | | | IV-1 | Zfp654 |
| 20978 | 3 | 4 | | | IV-1 | Zfp664 |
| 20979 | 3 | 4 | | | IV-1 | Zfp672 |
| 20980 | 3 | 4 | | | IV-1 | Zfp677 |
| 20981 | 3 | 4 | | | IV-1 | Zfp689 |
| 20982 | 3 | 4 | | | IV-1 | Zfp692 |
| 20983 | 3 | 4 | | | IV-1 | Zfp703 |
| 20984 | 3 | 4 | | | IV-1 | Zfp706 |
| 20985 | 3 | 4 | | | IV-1 | Zfp710 |
| 20986 | 3 | 4 | | | IV-1 | Zfp711 |
| 20987 | 3 | 4 | | | IV-1 | Zfp719 |
| 20988 | 3 | 4 | | | IV-1 | Zfp735 |
| 20989 | 3 | 4 | | | IV-1 | Zfp738 |
| 20990 | 3 | 4 | | | IV-1 | Zfp740 |
| 20991 | 3 | 4 | | | IV-1 | Zfp746 |
| 20992 | 3 | 4 | | | IV-1 | Zfp763 |
| 20993 | 3 | 4 | | | IV-1 | Zfp772 |
| 20994 | 3 | 4 | | | IV-1 | Zfp78 |
| 20995 | 3 | 4 | | | IV-1 | Zfp781 |
| 20996 | 3 | 4 | | | IV-1 | Zfp784 |
| 20997 | 3 | 4 | | | IV-1 | Zfp786 |
| 20998 | 3 | 4 | | | IV-1 | Zfp788 |
| 20999 | 3 | 4 | | | IV-1 | Zfp800 |
| 21000 | 3 | 4 | | | IV-1 | Zfp804a |
| 21001 | 3 | 4 | | | IV-1 | Zfp804b |
| 21002 | 3 | 4 | | | IV-1 | Zfp811 |
| 21003 | 3 | 4 | | | IV-1 | Zfp825 |
| 21004 | 3 | 4 | | | IV-1 | Zfp827 |
| 21005 | 3 | 4 | | | IV-1 | Zfp839 |
| 21006 | 3 | 4 | | | IV-1 | Zfp85os |
| 21007 | 3 | 4 | | | IV-1 | Zfp867 |
| 21008 | 3 | 4 | | | IV-1 | Zfp868 |
| 21009 | 3 | 4 | | | IV-1 | Zfp870 |
| 21010 | 3 | 4 | | | IV-1 | Zfp872 |
| 21011 | 3 | 4 | | | IV-1 | Zfp879 |
| 21012 | 3 | 4 | | | IV-1 | Zfp91 |
| 21013 | 3 | 4 | | | IV-1 | Zfp91Cntf |
| 21014 | 3 | 4 | | | IV-1 | Zfp92 |
| 21015 | 3 | 4 | | | IV-1 | Zfp936 |
| 21016 | 3 | 4 | | | IV-1 | Zfp937 |
| 21017 | 3 | 4 | | | IV-1 | Zfp938 |
| 21018 | 3 | 4 | | | IV-1 | Zfp943 |
| 21019 | 3 | 4 | | | IV-1 | Zfp947 |
| 21020 | 3 | 4 | | | IV-1 | Zfp949 |
| 21021 | 3 | 4 | | | IV-1 | Zfp955b |
| 21022 | 3 | 4 | | | IV-1 | Zfp957 |
| 21023 | 3 | 4 | | | IV-1 | Zfpl1 |
| 21024 | 3 | 4 | | | IV-1 | Zfr |
| 21025 | 3 | 4 | | | IV-1 | Zfr2 |
| 21026 | 3 | 4 | | | IV-1 | Zfx |
| 21027 | 3 | 4 | | | IV-1 | Zfy1 |
| 21028 | 3 | 4 | | | IV-1 | Zfy2 |
| 21029 | 3 | 4 | | | IV-1 | Zfyve19 |
| 21030 | 3 | 4 | | | IV-1 | Zfyve20 |
| 21031 | 3 | 4 | | | IV-1 | Zfyve27 |
| 21032 | 3 | 4 | | | IV-1 | Zfyve9 |
| 21033 | 3 | 4 | | | IV-1 | Zglp1 |
| 21034 | 3 | 4 | | | IV-1 | Zgrf1 |
| 21035 | 3 | 4 | | | IV-1 | Zhx1 |
| 21036 | 3 | 4 | | | IV-1 | Zic1 |
| 21037 | 3 | 4 | | | IV-1 | Zic3 |
| 21038 | 3 | 4 | | | IV-1 | Zic4 |
| 21039 | 3 | 4 | | | IV-1 | Zic5 |
| 21040 | 3 | 4 | | | IV-1 | Zim3 |
| 21041 | 3 | 4 | | | IV-1 | Zkscan1 |
| 21042 | 3 | 4 | | | IV-1 | Zkscan5 |
| 21043 | 3 | 4 | | | IV-1 | Zmat1 |
| 21044 | 3 | 4 | | | IV-1 | Zmat2 |
| 21045 | 3 | 4 | | | IV-1 | Zmat4 |
| 21046 | 3 | 4 | | | IV-1 | Zmiz2 |
| 21047 | 3 | 4 | | | IV-1 | Zmym2 |
| 21048 | 3 | 4 | | | IV-1 | Zmym3 |
| 21049 | 3 | 4 | | | IV-1 | Zmym4 |
| 21050 | 3 | 4 | | | IV-1 | Zmym5 |
| 21051 | 3 | 4 | | | IV-1 | Zmynd11 |
| 21052 | 3 | 4 | | | IV-1 | Zmynd15 |
| 21053 | 3 | 4 | | | IV-1 | Zmynd8 |
| 21054 | 3 | 4 | | | IV-1 | Znf41-ps |
| 21055 | 3 | 4 | | | IV-1 | Znf512b |
| 21056 | 3 | 4 | | | IV-1 | Znrf2 |
| 21057 | 3 | 4 | | | IV-1 | Znrf3 |
| 21058 | 3 | 4 | | | IV-1 | Zp1 |
| 21059 | 3 | 4 | | | IV-1 | Zp2 |
| 21060 | 3 | 4 | | | IV-1 | Zp3 |
| 21061 | 3 | 4 | | | IV-1 | Zp3r |
| 21062 | 3 | 4 | | | IV-1 | Zp4-ps |
| 21063 | 3 | 4 | | | IV-1 | Zpbp |
| 21064 | 3 | 4 | | | IV-1 | Zscan12 |
| 21065 | 3 | 4 | | | IV-1 | Zscan21 |
| 21066 | 3 | 4 | | | IV-1 | Zscan26 |
| 21067 | 3 | 4 | | | IV-1 | Zscan29 |
| 21068 | 3 | 4 | | | IV-1 | Zscan4a |
| 21069 | 3 | 4 | | | IV-1 | Zscan4b |
| 21070 | 3 | 4 | | | IV-1 | Zscan4c |
| 21071 | 3 | 4 | | | IV-1 | Zscan4d |
| 21072 | 3 | 4 | | | IV-1 | Zscan4e |
| 21073 | 3 | 4 | | | IV-1 | Zscan4f |
| 21074 | 3 | 4 | | | IV-1 | Zswim6 |
| 21075 | 3 | 4 | | | IV-1 | Zxdb |
| 21076 | 3 | 4 | | | IV-1 | Zxdc |
| 21077 | 3 | 4 | | | IV-1 | Zyg11a |

Fig. 43 - 125

| | | | | | | | |
|---|---|---|---|---|---|---|---|
| 21078 | 3 | 4 | | | IV-1 | Zyx | |
| 21079 | 3 | 4 | | | IV-1 | Zzz3 | |
| 21080 | 3 | | | | | | 1600014C23Rik |
| 21081 | 3 | | | | | | 1700006E09Rik |
| 21082 | 3 | | | | | | 1700006H21Rik |
| 21083 | 3 | | | | | | 1700007F19Rik |
| 21084 | 3 | | | | | | 1700007P06Rik |
| 21085 | 3 | | | | | | 1700010J16Rik |
| 21086 | 3 | | | | | | 1700011I03Rik |
| 21087 | 3 | | | | | | 1700012L04Rik |
| 21088 | 3 | | | | | | 1700018B24Rik |
| 21089 | 3 | | | | | | 1700023C21Rik |
| 21090 | 3 | | | | | | 1700023F06Rik |
| 21091 | 3 | | | | | | 1700024F13Rik |
| 21092 | 3 | | | | | | 1700024G13Rik |
| 21093 | 3 | | | | | | 1700027J07Rik |
| 21094 | 3 | | | | | | 1700028D13Rik |
| 21095 | 3 | | | | | | 1700028P14Rik |
| 21096 | 3 | | | | | | 1700029B22Rik |
| 21097 | 3 | | | | | | 1700029N11Rik |
| 21098 | 3 | | | | | | 1700030N03Rik |
| 21099 | 3 | | | | | | 1700031M16Rik |
| 21100 | 3 | | | | | | 1700034H15Rik |
| 21101 | 3 | | | | | | 1700042G15Rik |
| 21102 | 3 | | | | | | 1700044K03Rik |
| 21103 | 3 | | | | | | 1700063A18Rik |
| 21104 | 3 | | | | | | 1700063O14Rik |
| 21105 | 3 | | | | | | 1700065J18Rik |
| 21106 | 3 | | | | | | 1700065L07Rik |
| 21107 | 3 | | | | | | 1700067G17Rik |
| 21108 | 3 | | | | | | 1700067K01Rik |
| 21109 | 3 | | | | | | 1700074H08Rik |
| 21110 | 3 | | | | | | 1700081H04Rik |
| 21111 | 3 | | | | | | 1700091H14Rik |
| 21112 | 3 | | | | | | 1700094D03Rik |
| 21113 | 3 | | | | | | 1700094J05Rik |
| 21114 | 3 | | | | | | 1700101O22Rik |
| 21115 | 3 | | | | | | 1700109H08Rik |
| 21116 | 3 | | | | | | 1700109I08Rik |
| 21117 | 3 | | | | | | 1700123K08Rik |
| 21118 | 3 | | | | | | 1700125G02Rik |
| 21119 | 3 | | | | | | 1810007D17Rik |
| 21120 | 3 | | | | | | 2210409D07Rik |
| 21121 | 3 | | | | | | 2310005G13Rik |
| 21122 | 3 | | | | | | 2410018L13Rik |
| 21123 | 3 | | | | | | 2610037D02Rik |
| 21124 | 3 | | | | | | 2810004N23Rik |
| 21125 | 3 | | | | | | 4921511I17Rik |
| 21126 | 3 | | | | | | 4930405A21Rik |
| 21127 | 3 | | | | | | 4930433B08Rik |
| 21128 | 3 | | | | | | 4930444G20Rik |
| 21129 | 3 | | | | | | 4930448F12Rik |
| 21130 | 3 | | | | | | 4930448I06Rik |
| 21131 | 3 | | | | | | 4930448I18Rik |
| 21132 | 3 | | | | | | 4930448K20Rik |
| 21133 | 3 | | | | | | 4930449E18Rik |
| 21134 | 3 | | | | | | 4930449I24Rik |
| 21135 | 3 | | | | | | 4930451G09Rik |
| 21136 | 3 | | | | | | 4930452A19Rik |
| 21137 | 3 | | | | | | 4930453N24Rik |
| 21138 | 3 | | | | | | 4930455B14Rik |
| 21139 | 3 | | | | | | 4930455F16Rik |
| 21140 | 3 | | | | | | 4930463O16Rik |
| 21141 | 3 | | | | | | 4930470H14Rik |
| 21142 | 3 | | | | | | 4930474H20Rik |
| 21143 | 3 | | | | | | 4930480M12Rik |
| 21144 | 3 | | | | | | 4930486F22Rik |
| 21145 | 3 | | | | | | 4930488L21Rik |
| 21146 | 3 | | | | | | 4930500L23Rik |
| 21147 | 3 | | | | | | 4930502A04Rik |
| 21148 | 3 | | | | | | 4930502E18Rik |
| 21149 | 3 | | | | | | 4930507D05Rik |
| 21150 | 3 | | | | | | 4930509E16Rik |
| 21151 | 3 | | | | | | 4930513O06Rik |
| 21152 | 3 | | | | | | 4930515G01Rik |
| 21153 | 3 | | | | | | 4930519F16Rik |
| 21154 | 3 | | | | | | 4930519F24Rik |
| 21155 | 3 | | | | | | 4930519G04Rik |
| 21156 | 3 | | | | | | 4930523C07Rik |
| 21157 | 3 | | | | | | 4930524O05Rik |
| 21158 | 3 | | | | | | 4930527F14Rik |
| 21159 | 3 | | | | | | 4930528A17Rik |
| 21160 | 3 | | | | | | 4930529C04Rik |
| 21161 | 3 | | | | | | 4930529M08Rik |
| 21162 | 3 | | | | | | 4930533P14Rik |
| 21163 | 3 | | | | | | 4930538K18Rik |
| 21164 | 3 | | | | | | 4930539C22Rik |
| 21165 | 3 | | | | | | 4930546C10Rik |
| 21166 | 3 | | | | | | 4930547E08Rik |
| 21167 | 3 | | | | | | 4930550C14Rik |
| 21168 | 3 | | | | | | 4930552P12Rik |
| 21169 | 3 | | | | | | 4930553E22Rik |
| 21170 | 3 | | | | | | 4930558G05Rik |
| 21171 | 3 | | | | | | 4930563F08Rik |
| 21172 | 3 | | | | | | 4930564D02Rik |
| 21173 | 3 | | | | | | 4930565D16Rik |
| 21174 | 3 | | | | | | 4930568D16Rik |
| 21175 | 3 | | | | | | 4930568G15Rik |
| 21176 | 3 | | | | | | 4930571O06Rik |
| 21177 | 3 | | | | | | 4930572K03Rik |
| 21178 | 3 | | | | | | 4930578N18Rik |
| 21179 | 3 | | | | | | 4931403G20Rik |
| 21180 | 3 | | | | | | 4931409K22Rik |
| 21181 | 3 | | | | | | 4931440F15Rik |
| 21182 | 3 | | | | | | 4931440J10Rik |
| 21183 | 3 | | | | | | 4932435O22Rik |
| 21184 | 3 | | | | | | 4932441J04Rik |
| 21185 | 3 | | | | | | 4933401H06Rik |
| 21186 | 3 | | | | | | 4933406C10Rik |
| 21187 | 3 | | | | | | 4933407I05Rik |
| 21188 | 3 | | | | | | 4933408B17Rik |
| 21189 | 3 | | | | | | 4933408J17Rik |
| 21190 | 3 | | | | | | 4933412O06Rik |
| 21191 | 3 | | | | | | 4933416M06Rik |
| 21192 | 3 | | | | | | 4933417D19Rik |
| 21193 | 3 | | | | | | 4933421I07Rik |
| 21194 | 3 | | | | | | 4933422H20Rik |
| 21195 | 3 | | | | | | 4933428C19Rik |
| 21196 | 3 | | | | | | 4933436E23Rik |
| 21197 | 3 | | | | | | 4933439K11Rik |
| 21198 | 3 | | | | | | 4933440J02Rik |
| 21199 | 3 | | | | | | 5133400J02Rik |
| 21200 | 3 | | | | | | 5330439B14Rik |
| 21201 | 3 | | | | | | 5430401F13Rik |
| 21202 | 3 | | | | | | 5430417L22Rik |
| 21203 | 3 | | | | | | 5730457N03Rik |
| 21204 | 3 | | | | | | 5730522E02Rik |
| 21205 | 3 | | | | | | 5830411N06Rik |
| 21206 | 3 | | | | | | 5930430L01Rik |
| 21207 | 3 | | | | | | 6720489N17Rik |
| 21208 | 3 | | | | | | 8030411F24Rik |
| 21209 | 3 | | | | | | 8030443G20Rik |
| 21210 | 3 | | | | | | 8430422H06Rik |
| 21211 | 3 | | | | | | 9130015L21Rik |
| 21212 | 3 | | | | | | 9130204L05Rik |
| 21213 | 3 | | | | | | 9130209A04Rik |
| 21214 | 3 | | | | | | 9230009I02Rik |
| 21215 | 3 | | | | | | 9230110F15Rik |
| 21216 | 3 | | | | | | 9230116L04Rik |
| 21217 | 3 | | | | | | 9430016H08Rik |
| 21218 | 3 | | | | | | 9430021M05Rik |
| 21219 | 3 | | | | | | 9530051G07Rik |
| 21220 | 3 | | | | | | 9630001P10Rik |
| 21221 | 3 | | | | | | 9830132P13Rik |
| 21222 | 3 | | | | | | A230046K03Rik |
| 21223 | 3 | | | | | | A230065H16Rik |
| 21224 | 3 | | | | | | A230108P19Rik |
| 21225 | 3 | | | | | | A530065N20Rik |
| 21226 | 3 | | | | | | A730056A06Rik |
| 21227 | 3 | | | | | | A930007I19Rik |
| 21228 | 3 | | | | | | A930019D19Rik |
| 21229 | 3 | | | | | | Abca4 |
| 21230 | 3 | | | | | | Adamts19 |
| 21231 | 3 | | | | | | Aifm3 |
| 21232 | 3 | | | | | | Ano3 |
| 21233 | 3 | | | | | | Ap1g2 |
| 21234 | 3 | | | | | | AW209491 |
| 21235 | 3 | | | | | | B230119M05Rik |
| 21236 | 3 | | | | | | BC048562 |
| 21237 | 3 | | | | | | BC080695 |
| 21238 | 3 | | | | | | Bcl2l13 |
| 21239 | 3 | | | | | | Brox |
| 21240 | 3 | | | | | | C130050O18Rik |
| 21241 | 3 | | | | | | C130060C02Rik |
| 21242 | 3 | | | | | | C430049B03Rik |
| 21243 | 3 | | | | | | Cacna1c |
| 21244 | 3 | | | | | | Cacna2d2 |
| 21245 | 3 | | | | | | Ccdc47 |
| 21246 | 3 | | | | | | Cdk8 |
| 21247 | 3 | | | | | | Chrna5 |

Fig. 43 - 126

| | | | | | | | |
|---|---|---|---|---|---|---|---|
| 21248 | 3 | | | | | | CK137956 |
| 21249 | 3 | | | | | | Clec5a |
| 21250 | 3 | | | | | | Crx |
| 21251 | 3 | | | | | | Crygc |
| 21252 | 3 | | | | | | Crygd |
| 21253 | 3 | | | | | | Csnk1d |
| 21254 | 3 | | | | | | Csnk1g3 |
| 21255 | 3 | | | | | | Cul2 |
| 21256 | 3 | | | | | | Cyp2d10 |
| 21257 | 3 | | | | | | Cyp2d11 |
| 21258 | 3 | | | | | | Cyp3a59 |
| 21259 | 3 | | | | | | Cyp4a12a |
| 21260 | 3 | | | | | | D930007P13Rik |
| 21261 | 3 | | | | | | D930032P07Rik |
| 21262 | 3 | | | | | | Defa-ps12 |
| 21263 | 3 | | | | | | Defb4 |
| 21264 | 3 | | | | | | Defb44-ps |
| 21265 | 3 | | | | | | Defb46 |
| 21266 | 3 | | | | | | Defb47 |
| 21267 | 3 | | | | | | Defb5 |
| 21268 | 3 | | | | | | Dnaic1 |
| 21269 | 3 | | | | | | Dnaic2 |
| 21270 | 3 | | | | | | Dstyk |
| 21271 | 3 | | | | | | DXBay18 |
| 21272 | 3 | | | | | | Dynlt1a |
| 21273 | 3 | | | | | | E030002O03Rik |
| 21274 | 3 | | | | | | E230016M11Rik |
| 21275 | 3 | | | | | | E330021D16Rik |
| 21276 | 3 | | | | | | E4f1 |
| 21277 | 3 | | | | | | Erc2 |
| 21278 | 3 | | | | | | Ermn |
| 21279 | 3 | | | | | | Esp6-esp5 |
| 21280 | 3 | | | | | | Evx1 |
| 21281 | 3 | | | | | | Fam228b |
| 21282 | 3 | | | | | | Fam76a |
| 21283 | 3 | | | | | | Fbll1 |
| 21284 | 3 | | | | | | Fbxo22 |
| 21285 | 3 | | | | | | Fdx1 |
| 21286 | 3 | | | | | | Fgf23 |
| 21287 | 3 | | | | | | Fgfr1 |
| 21288 | 3 | | | | | | Foxb2 |
| 21289 | 3 | | | | | | Fpgt |
| 21290 | 3 | | | | | | Frat1 |
| 21291 | 3 | | | | | | Ganab |
| 21292 | 3 | | | | | | Gdap1l1 |
| 21293 | 3 | | | | | | Gjb5 |
| 21294 | 3 | | | | | | Gli3 |
| 21295 | 3 | | | | | | Gm10373 |
| 21296 | 3 | | | | | | Gm10390 |
| 21297 | 3 | | | | | | Gm10409 |
| 21298 | 3 | | | | | | Gm10413 |
| 21299 | 3 | | | | | | Gm10415 |
| 21300 | 3 | | | | | | Gm10416 |
| 21301 | 3 | | | | | | Gm10432 |
| 21302 | 3 | | | | | | Gm10439 |
| 21303 | 3 | | | | | | Gm10466 |
| 21304 | 3 | | | | | | Gm10471 |
| 21305 | 3 | | | | | | Gm10486 |
| 21306 | 3 | | | | | | Gm10494 |
| 21307 | 3 | | | | | | Gm10510 |
| 21308 | 3 | | | | | | Gm10512 |
| 21309 | 3 | | | | | | Gm10619 |
| 21310 | 3 | | | | | | Gm10635 |
| 21311 | 3 | | | | | | Gm10637 |
| 21312 | 3 | | | | | | Gm10670 |
| 21313 | 3 | | | | | | Gm10696 |
| 21314 | 3 | | | | | | Gm10731 |
| 21315 | 3 | | | | | | Gm10745 |
| 21316 | 3 | | | | | | Gm10782 |
| 21317 | 3 | | | | | | Gm10823 |
| 21318 | 3 | | | | | | Gm10845 |
| 21319 | 3 | | | | | | Gm10921 |
| 21320 | 3 | | | | | | Gm10922 |
| 21321 | 3 | | | | | | Gm11213 |
| 21322 | 3 | | | | | | Gm11237 |
| 21323 | 3 | | | | | | Gm1140 |
| 21324 | 3 | | | | | | Gm11468 |
| 21325 | 3 | | | | | | Gm11529 |
| 21326 | 3 | | | | | | Gm11545 |
| 21327 | 3 | | | | | | Gm11554 |
| 21328 | 3 | | | | | | Gm11567 |
| 21329 | 3 | | | | | | Gm11569 |
| 21330 | 3 | | | | | | Gm11696 |
| 21331 | 3 | | | | | | Gm11758 |
| 21332 | 3 | | | | | | Gm11937 |
| 21333 | 3 | | | | | | Gm11938 |
| 21334 | 3 | | | | | | Gm12159 |
| 21335 | 3 | | | | | | Gm12171 |
| 21336 | 3 | | | | | | Gm12238 |
| 21337 | 3 | | | | | | Gm12253 |
| 21338 | 3 | | | | | | Gm12718 |
| 21339 | 3 | | | | | | Gm12888 |
| 21340 | 3 | | | | | | Gm13023 |
| 21341 | 3 | | | | | | Gm13057 |
| 21342 | 3 | | | | | | Gm13128 |
| 21343 | 3 | | | | | | Gm13154 |
| 21344 | 3 | | | | | | Gm13178 |
| 21345 | 3 | | | | | | Gm13247 |
| 21346 | 3 | | | | | | Gm13272 |
| 21347 | 3 | | | | | | Gm13276 |
| 21348 | 3 | | | | | | Gm13279 |
| 21349 | 3 | | | | | | Gm13285 |
| 21350 | 3 | | | | | | Gm13288 |
| 21351 | 3 | | | | | | Gm13293 |
| 21352 | 3 | | | | | | Gm13305 |
| 21353 | 3 | | | | | | Gm13308 |
| 21354 | 3 | | | | | | Gm13629 |
| 21355 | 3 | | | | | | Gm13752 |
| 21356 | 3 | | | | | | Gm13939 |
| 21357 | 3 | | | | | | Gm13944 |
| 21358 | 3 | | | | | | Gm14306 |
| 21359 | 3 | | | | | | Gm14379 |
| 21360 | 3 | | | | | | Gm14685 |
| 21361 | 3 | | | | | | Gm14725 |
| 21362 | 3 | | | | | | Gm15055 |
| 21363 | 3 | | | | | | Gm15091 |
| 21364 | 3 | | | | | | Gm15107 |
| 21365 | 3 | | | | | | Gm15140 |
| 21366 | 3 | | | | | | Gm1527 |
| 21367 | 3 | | | | | | Gm15315 |
| 21368 | 3 | | | | | | Gm15328 |
| 21369 | 3 | | | | | | Gm15350 |
| 21370 | 3 | | | | | | Gm15698 |
| 21371 | 3 | | | | | | Gm15941 |
| 21372 | 3 | | | | | | Gm16039 |
| 21373 | 3 | | | | | | Gm16130 |
| 21374 | 3 | | | | | | Gm16430 |
| 21375 | 3 | | | | | | Gm16532 |
| 21376 | 3 | | | | | | Gm16596 |
| 21377 | 3 | | | | | | Gm16796 |
| 21378 | 3 | | | | | | Gm16833 |
| 21379 | 3 | | | | | | Gm16880 |
| 21380 | 3 | | | | | | Gm17644 |
| 21381 | 3 | | | | | | Gm18409 |
| 21382 | 3 | | | | | | Gm19466 |
| 21383 | 3 | | | | | | Gm19510 |
| 21384 | 3 | | | | | | Gm19583 |
| 21385 | 3 | | | | | | Gm1968 |
| 21386 | 3 | | | | | | Gm19689 |
| 21387 | 3 | | | | | | Gm19782 |
| 21388 | 3 | | | | | | Gm19784 |
| 21389 | 3 | | | | | | Gm1995 |
| 21390 | 3 | | | | | | Gm19990 |
| 21391 | 3 | | | | | | Gm20187 |
| 21392 | 3 | | | | | | Gm2022 |
| 21393 | 3 | | | | | | Gm20268 |
| 21394 | 3 | | | | | | Gm2030 |
| 21395 | 3 | | | | | | Gm20337 |
| 21396 | 3 | | | | | | Gm20611 |
| 21397 | 3 | | | | | | Gm20744 |
| 21398 | 3 | | | | | | Gm20750 |
| 21399 | 3 | | | | | | Gm20752 |
| 21400 | 3 | | | | | | Gm20756 |
| 21401 | 3 | | | | | | Gm20758 |
| 21402 | 3 | | | | | | Gm20806 |
| 21403 | 3 | | | | | | Gm20826 |
| 21404 | 3 | | | | | | Gm20854 |
| 21405 | 3 | | | | | | Gm20857 |
| 21406 | 3 | | | | | | Gm20877 |
| 21407 | 3 | | | | | | Gm2109 |
| 21408 | 3 | | | | | | Gm2115 |
| 21409 | 3 | | | | | | Gm21283 |
| 21410 | 3 | | | | | | Gm21586 |
| 21411 | 3 | | | | | | Gm21637 |
| 21412 | 3 | | | | | | Gm21693 |
| 21413 | 3 | | | | | | Gm21943 |
| 21414 | 3 | | | | | | Gm21944 |
| 21415 | 3 | | | | | | Gm2382 |
| 21416 | 3 | | | | | | Gm2863 |
| 21417 | 3 | | | | | | Gm2897 |

Fig. 43 - 127

| | | | | | | | |
|---|---|---|---|---|---|---|---|
| 21418 | 3 | | | | | | Gm2913 |
| 21419 | 3 | | | | | | Gm2933 |
| 21420 | 3 | | | | | | Gm3002 |
| 21421 | 3 | | | | | | Gm3238 |
| 21422 | 3 | | | | | | Gm3259 |
| 21423 | 3 | | | | | | Gm3604 |
| 21424 | 3 | | | | | | Gm3750 |
| 21425 | 3 | | | | | | Gm382 |
| 21426 | 3 | | | | | | Gm3893 |
| 21427 | 3 | | | | | | Gm41 |
| 21428 | 3 | | | | | | Gm4175 |
| 21429 | 3 | | | | | | Gm4262 |
| 21430 | 3 | | | | | | Gm4278 |
| 21431 | 3 | | | | | | Gm4302 |
| 21432 | 3 | | | | | | Gm44 |
| 21433 | 3 | | | | | | Gm4489 |
| 21434 | 3 | | | | | | Gm4541 |
| 21435 | 3 | | | | | | Gm4719 |
| 21436 | 3 | | | | | | Gm4745 |
| 21437 | 3 | | | | | | Gm4759 |
| 21438 | 3 | | | | | | Gm4763 |
| 21439 | 3 | | | | | | Gm4788 |
| 21440 | 3 | | | | | | Gm4794 |
| 21441 | 3 | | | | | | Gm4827 |
| 21442 | 3 | | | | | | Gm4836 |
| 21443 | 3 | | | | | | Gm4846 |
| 21444 | 3 | | | | | | Gm4847 |
| 21445 | 3 | | | | | | Gm4850 |
| 21446 | 3 | | | | | | Gm4858 |
| 21447 | 3 | | | | | | Gm4884 |
| 21448 | 3 | | | | | | Gm4894 |
| 21449 | 3 | | | | | | Gm4906 |
| 21450 | 3 | | | | | | Gm4925 |
| 21451 | 3 | | | | | | Gm4937 |
| 21452 | 3 | | | | | | Gm4944 |
| 21453 | 3 | | | | | | Gm4961 |
| 21454 | 3 | | | | | | Gm5039 |
| 21455 | 3 | | | | | | Gm5071 |
| 21456 | 3 | | | | | | Gm5072 |
| 21457 | 3 | | | | | | Gm5082 |
| 21458 | 3 | | | | | | Gm5089 |
| 21459 | 3 | | | | | | Gm5134 |
| 21460 | 3 | | | | | | Gm5168 |
| 21461 | 3 | | | | | | Gm5346 |
| 21462 | 3 | | | | | | Gm5347 |
| 21463 | 3 | | | | | | Gm5416 |
| 21464 | 3 | | | | | | Gm5460 |
| 21465 | 3 | | | | | | Gm5477 |
| 21466 | 3 | | | | | | Gm5640 |
| 21467 | 3 | | | | | | Gm5662 |
| 21468 | 3 | | | | | | Gm5712 |
| 21469 | 3 | | | | | | Gm5795 |
| 21470 | 3 | | | | | | Gm5796 |
| 21471 | 3 | | | | | | Gm5797 |
| 21472 | 3 | | | | | | Gm5833 |
| 21473 | 3 | | | | | | Gm5886 |
| 21474 | 3 | | | | | | Gm5893 |
| 21475 | 3 | | | | | | Gm5934 |
| 21476 | 3 | | | | | | Gm597 |
| 21477 | 3 | | | | | | Gm6086 |
| 21478 | 3 | | | | | | Gm6116 |
| 21479 | 3 | | | | | | Gm6251 |
| 21480 | 3 | | | | | | Gm6260 |
| 21481 | 3 | | | | | | Gm6307 |
| 21482 | 3 | | | | | | Gm6313 |
| 21483 | 3 | | | | | | Gm6367 |
| 21484 | 3 | | | | | | Gm6406 |
| 21485 | 3 | | | | | | Gm6416 |
| 21486 | 3 | | | | | | Gm6432 |
| 21487 | 3 | | | | | | Gm6548 |
| 21488 | 3 | | | | | | Gm6592 |
| 21489 | 3 | | | | | | Gm6639 |
| 21490 | 3 | | | | | | Gm6696 |
| 21491 | 3 | | | | | | Gm6904 |
| 21492 | 3 | | | | | | Gm6994 |
| 21493 | 3 | | | | | | Gm7104 |
| 21494 | 3 | | | | | | Gm711 |
| 21495 | 3 | | | | | | Gm7134 |
| 21496 | 3 | | | | | | Gm732 |
| 21497 | 3 | | | | | | Gm7361 |
| 21498 | 3 | | | | | | Gm7616 |
| 21499 | 3 | | | | | | Gm765 |
| 21500 | 3 | | | | | | Gm766 |
| 21501 | 3 | | | | | | Gm7788 |
| 21502 | 3 | | | | | | Gm815 |
| 21503 | 3 | | | | | | Gm829 |
| 21504 | 3 | | | | | | Gm8298 |
| 21505 | 3 | | | | | | Gm839 |
| 21506 | 3 | | | | | | Gm8693 |
| 21507 | 3 | | | | | | Gm8709 |
| 21508 | 3 | | | | | | Gm8773 |
| 21509 | 3 | | | | | | Gm884 |
| 21510 | 3 | | | | | | Gm8989 |
| 21511 | 3 | | | | | | Gm9 |
| 21512 | 3 | | | | | | Gm9159 |
| 21513 | 3 | | | | | | Gm94 |
| 21514 | 3 | | | | | | Gm9513 |
| 21515 | 3 | | | | | | Gm960 |
| 21516 | 3 | | | | | | Gm9696 |
| 21517 | 3 | | | | | | Gm9758 |
| 21518 | 3 | | | | | | Gm9767 |
| 21519 | 3 | | | | | | Gm9871 |
| 21520 | 3 | | | | | | Gm9920 |
| 21521 | 3 | | | | | | Gm9999 |
| 21522 | 3 | | | | | | Gmcl1 |
| 21523 | 3 | | | | | | Gpr160 |
| 21524 | 3 | | | | | | Gsdma2 |
| 21525 | 3 | | | | | | H2afb2 |
| 21526 | 3 | | | | | | H2afb3 |
| 21527 | 3 | | | | | | H2-M1 |
| 21528 | 3 | | | | | | H2-M10.5 |
| 21529 | 3 | | | | | | H2-M2 |
| 21530 | 3 | | | | | | Hbp1 |
| 21531 | 3 | | | | | | Hoxd3os1 |
| 21532 | 3 | | | | | | Hs2st1 |
| 21533 | 3 | | | | | | Ifnar1 |
| 21534 | 3 | | | | | | Igfbp7 |
| 21535 | 3 | | | | | | Il22ra1 |
| 21536 | 3 | | | | | | Ints4 |
| 21537 | 3 | | | | | | Klra22 |
| 21538 | 3 | | | | | | Kirl1 |
| 21539 | 3 | | | | | | Kncn |
| 21540 | 3 | | | | | | Krt78 |
| 21541 | 3 | | | | | | Krtap10-10 |
| 21542 | 3 | | | | | | Krtap15 |
| 21543 | 3 | | | | | | Krtap1-5 |
| 21544 | 3 | | | | | | Krtap16-1 |
| 21545 | 3 | | | | | | Krtap19-1 |
| 21546 | 3 | | | | | | Krtap24-1 |
| 21547 | 3 | | | | | | Krtap26-1 |
| 21548 | 3 | | | | | | Krtap27-1 |
| 21549 | 3 | | | | | | Krtap4-1 |
| 21550 | 3 | | | | | | Krtap4-2 |
| 21551 | 3 | | | | | | Krtap4-9 |
| 21552 | 3 | | | | | | Krtap5-1 |
| 21553 | 3 | | | | | | Krtap5-2 |
| 21554 | 3 | | | | | | Krtap5-3 |
| 21555 | 3 | | | | | | Krtap5-5 |
| 21556 | 3 | | | | | | Krtap6-2 |
| 21557 | 3 | | | | | | Krtap6-5 |
| 21558 | 3 | | | | | | Krtap9-1 |
| 21559 | 3 | | | | | | Krtap9-5 |
| 21560 | 3 | | | | | | Kti12 |
| 21561 | 3 | | | | | | L3mbtl4 |
| 21562 | 3 | | | | | | Lama1 |
| 21563 | 3 | | | | | | LOC100504039 |
| 21564 | 3 | | | | | | LOC102634431 |
| 21565 | 3 | | | | | | Loh12cr1 |
| 21566 | 3 | | | | | | Lonrf1 |
| 21567 | 3 | | | | | | Mir1247 |
| 21568 | 3 | | | | | | Mir125b-2 |
| 21569 | 3 | | | | | | Mir126b |
| 21570 | 3 | | | | | | Mir127 |
| 21571 | 3 | | | | | | Mir128-1 |
| 21572 | 3 | | | | | | Mir128-2 |
| 21573 | 3 | | | | | | Mir129-1 |
| 21574 | 3 | | | | | | Mir129-2 |
| 21575 | 3 | | | | | | Mir1298 |
| 21576 | 3 | | | | | | Mir129b |
| 21577 | 3 | | | | | | Mir1306 |
| 21578 | 3 | | | | | | Mir130b |
| 21579 | 3 | | | | | | Mir130c |
| 21580 | 3 | | | | | | Mir132 |
| 21581 | 3 | | | | | | Mir133a-1 |
| 21582 | 3 | | | | | | Mir133a-2 |
| 21583 | 3 | | | | | | Mir133b |
| 21584 | 3 | | | | | | Mir133c |
| 21585 | 3 | | | | | | Mir134 |
| 21586 | 3 | | | | | | Mir135a-1 |
| 21587 | 3 | | | | | | Mir135a-2 |

Fig. 43 - 128

| | | | | | | | |
|---|---|---|---|---|---|---|---|
| 21588 | 3 | | | | | | Mir135b |
| 21589 | 3 | | | | | | Mir137 |
| 21590 | 3 | | | | | | Mir138-1 |
| 21591 | 3 | | | | | | Mir138-2 |
| 21592 | 3 | | | | | | Mir139 |
| 21593 | 3 | | | | | | Mir140 |
| 21594 | 3 | | | | | | Mir141 |
| 21595 | 3 | | | | | | Mir142 |
| 21596 | 3 | | | | | | Mir143 |
| 21597 | 3 | | | | | | Mir144 |
| 21598 | 3 | | | | | | Mir145 |
| 21599 | 3 | | | | | | Mir145b |
| 21600 | 3 | | | | | | Mir146 |
| 21601 | 3 | | | | | | Mir146b |
| 21602 | 3 | | | | | | Mir148a |
| 21603 | 3 | | | | | | Mir148b |
| 21604 | 3 | | | | | | Mir149 |
| 21605 | 3 | | | | | | Mir152 |
| 21606 | 3 | | | | | | Mir153 |
| 21607 | 3 | | | | | | Mir154 |
| 21608 | 3 | | | | | | Mir155 |
| 21609 | 3 | | | | | | Mir15a |
| 21610 | 3 | | | | | | Mir15b |
| 21611 | 3 | | | | | | Mir16-1 |
| 21612 | 3 | | | | | | Mir16-2 |
| 21613 | 3 | | | | | | Mir1668 |
| 21614 | 3 | | | | | | Mir17 |
| 21615 | 3 | | | | | | Mir18 |
| 21616 | 3 | | | | | | Mir181a-1 |
| 21617 | 3 | | | | | | Mir181a-2 |
| 21618 | 3 | | | | | | Mir181b-1 |
| 21619 | 3 | | | | | | Mir181b-2 |
| 21620 | 3 | | | | | | Mir181d |
| 21621 | 3 | | | | | | Mir182 |
| 21622 | 3 | | | | | | Mir183 |
| 21623 | 3 | | | | | | Mir1839 |
| 21624 | 3 | | | | | | Mir184 |
| 21625 | 3 | | | | | | Mir1843 |
| 21626 | 3 | | | | | | Mir1843b |
| 21627 | 3 | | | | | | Mir185 |
| 21628 | 3 | | | | | | Mir187 |
| 21629 | 3 | | | | | | Mir1892 |
| 21630 | 3 | | | | | | Mir1893 |
| 21631 | 3 | | | | | | Mir1894 |
| 21632 | 3 | | | | | | Mir1895 |
| 21633 | 3 | | | | | | Mir1896 |
| 21634 | 3 | | | | | | Mir1897 |
| 21635 | 3 | | | | | | Mir1898 |
| 21636 | 3 | | | | | | Mir1899 |
| 21637 | 3 | | | | | | Mir18b |
| 21638 | 3 | | | | | | Mir190 |
| 21639 | 3 | | | | | | Mir1900 |
| 21640 | 3 | | | | | | Mir1901 |
| 21641 | 3 | | | | | | Mir1902 |
| 21642 | 3 | | | | | | Mir1903 |
| 21643 | 3 | | | | | | Mir1904 |
| 21644 | 3 | | | | | | Mir1905 |
| 21645 | 3 | | | | | | Mir1906-1 |
| 21646 | 3 | | | | | | Mir1907 |
| 21647 | 3 | | | | | | Mir190b |
| 21648 | 3 | | | | | | Mir191 |
| 21649 | 3 | | | | | | Mir192 |
| 21650 | 3 | | | | | | Mir1928 |
| 21651 | 3 | | | | | | Mir1929 |
| 21652 | 3 | | | | | | Mir193 |
| 21653 | 3 | | | | | | Mir1930 |
| 21654 | 3 | | | | | | Mir1931 |
| 21655 | 3 | | | | | | Mir1932 |
| 21656 | 3 | | | | | | Mir1933 |
| 21657 | 3 | | | | | | Mir1934 |
| 21658 | 3 | | | | | | Mir1936 |
| 21659 | 3 | | | | | | Mir1938 |
| 21660 | 3 | | | | | | Mir193b |
| 21661 | 3 | | | | | | Mir1940 |
| 21662 | 3 | | | | | | Mir1941 |
| 21663 | 3 | | | | | | Mir194-1 |
| 21664 | 3 | | | | | | Mir1942 |
| 21665 | 3 | | | | | | Mir194-2 |
| 21666 | 3 | | | | | | Mir1943 |
| 21667 | 3 | | | | | | Mir1945 |
| 21668 | 3 | | | | | | Mir1946a |
| 21669 | 3 | | | | | | Mir1946b |
| 21670 | 3 | | | | | | Mir1947 |
| 21671 | 3 | | | | | | Mir1948 |
| 21672 | 3 | | | | | | Mir1949 |
| 21673 | 3 | | | | | | Mir195 |
| 21674 | 3 | | | | | | Mir1950 |
| 21675 | 3 | | | | | | Mir1951 |
| 21676 | 3 | | | | | | Mir1952 |
| 21677 | 3 | | | | | | Mir1953 |
| 21678 | 3 | | | | | | Mir1954 |
| 21679 | 3 | | | | | | Mir1955 |
| 21680 | 3 | | | | | | Mir1956 |
| 21681 | 3 | | | | | | Mir1957 |
| 21682 | 3 | | | | | | Mir1958 |
| 21683 | 3 | | | | | | Mir195b |
| 21684 | 3 | | | | | | Mir1960 |
| 21685 | 3 | | | | | | Mir1961 |
| 21686 | 3 | | | | | | Mir1962 |
| 21687 | 3 | | | | | | Mir1964 |
| 21688 | 3 | | | | | | Mir1966 |
| 21689 | 3 | | | | | | Mir1967 |
| 21690 | 3 | | | | | | Mir1968 |
| 21691 | 3 | | | | | | Mir1969 |
| 21692 | 3 | | | | | | Mir196a-1 |
| 21693 | 3 | | | | | | Mir196a-2 |
| 21694 | 3 | | | | | | Mir196b |
| 21695 | 3 | | | | | | Mir1970 |
| 21696 | 3 | | | | | | Mir1971 |
| 21697 | 3 | | | | | | Mir1981 |
| 21698 | 3 | | | | | | Mir1982 |
| 21699 | 3 | | | | | | Mir1983 |
| 21700 | 3 | | | | | | Mir199a-1 |
| 21701 | 3 | | | | | | Mir199a-2 |
| 21702 | 3 | | | | | | Mir199b |
| 21703 | 3 | | | | | | Mir19a |
| 21704 | 3 | | | | | | Mir19b-1 |
| 21705 | 3 | | | | | | Mir19b-2 |
| 21706 | 3 | | | | | | Mir1a-1 |
| 21707 | 3 | | | | | | Mir1a-2 |
| 21708 | 3 | | | | | | Mir1b |
| 21709 | 3 | | | | | | Mir200a |
| 21710 | 3 | | | | | | Mir200b |
| 21711 | 3 | | | | | | Mir200c |
| 21712 | 3 | | | | | | Mir201 |
| 21713 | 3 | | | | | | Mir202 |
| 21714 | 3 | | | | | | Mir203 |
| 21715 | 3 | | | | | | Mir204 |
| 21716 | 3 | | | | | | Mir205 |
| 21717 | 3 | | | | | | Mir206 |
| 21718 | 3 | | | | | | Mir207 |
| 21719 | 3 | | | | | | Mir208a |
| 21720 | 3 | | | | | | Mir208b |
| 21721 | 3 | | | | | | Mir20a |
| 21722 | 3 | | | | | | Mir20b |
| 21723 | 3 | | | | | | Mir21 |
| 21724 | 3 | | | | | | Mir210 |
| 21725 | 3 | | | | | | Mir211 |
| 21726 | 3 | | | | | | Mir212 |
| 21727 | 3 | | | | | | Mir2136 |
| 21728 | 3 | | | | | | Mir2137 |
| 21729 | 3 | | | | | | Mir2139 |
| 21730 | 3 | | | | | | Mir215 |
| 21731 | 3 | | | | | | Mir216a |
| 21732 | 3 | | | | | | Mir216b |
| 21733 | 3 | | | | | | Mir216c |
| 21734 | 3 | | | | | | Mir217 |
| 21735 | 3 | | | | | | Mir218-2 |
| 21736 | 3 | | | | | | Mir219-1 |
| 21737 | 3 | | | | | | Mir219-2 |
| 21738 | 3 | | | | | | Mir219b |
| 21739 | 3 | | | | | | Mir219c |
| 21740 | 3 | | | | | | Mir21b |
| 21741 | 3 | | | | | | Mir21c |
| 21742 | 3 | | | | | | Mir22 |
| 21743 | 3 | | | | | | Mir221 |
| 21744 | 3 | | | | | | Mir222 |
| 21745 | 3 | | | | | | Mir23a |
| 21746 | 3 | | | | | | Mir23b |
| 21747 | 3 | | | | | | Mir24-1 |
| 21748 | 3 | | | | | | Mir24-2 |
| 21749 | 3 | | | | | | Mir25 |
| 21750 | 3 | | | | | | Mir26a-2 |
| 21751 | 3 | | | | | | Mir26b |
| 21752 | 3 | | | | | | Mir27a |
| 21753 | 3 | | | | | | Mir27b |
| 21754 | 3 | | | | | | Mir28 |
| 21755 | 3 | | | | | | Mir2861 |
| 21756 | 3 | | | | | | Mir28b |
| 21757 | 3 | | | | | | Mir28c |

Fig. 43 - 129

| | | | | | | | |
|---|---|---|---|---|---|---|---|
| 21758 | 3 | | | | | | Mir290 |
| 21759 | 3 | | | | | | Mir290b |
| 21760 | 3 | | | | | | Mir291a |
| 21761 | 3 | | | | | | Mir291b |
| 21762 | 3 | | | | | | Mir292 |
| 21763 | 3 | | | | | | Mir292b |
| 21764 | 3 | | | | | | Mir293 |
| 21765 | 3 | | | | | | Mir294 |
| 21766 | 3 | | | | | | Mir295 |
| 21767 | 3 | | | | | | Mir296 |
| 21768 | 3 | | | | | | Mir297-1 |
| 21769 | 3 | | | | | | Mir297-2 |
| 21770 | 3 | | | | | | Mir297a-3 |
| 21771 | 3 | | | | | | Mir297a-4 |
| 21772 | 3 | | | | | | Mir297b |
| 21773 | 3 | | | | | | Mir297c |
| 21774 | 3 | | | | | | Mir298 |
| 21775 | 3 | | | | | | Mir299 |
| 21776 | 3 | | | | | | Mir299b |
| 21777 | 3 | | | | | | Mir29a |
| 21778 | 3 | | | | | | Mir29b-1 |
| 21779 | 3 | | | | | | Mir29b-2 |
| 21780 | 3 | | | | | | Mir301 |
| 21781 | 3 | | | | | | Mir301b |
| 21782 | 3 | | | | | | Mir302a |
| 21783 | 3 | | | | | | Mir302b |
| 21784 | 3 | | | | | | Mir302c |
| 21785 | 3 | | | | | | Mir302d |
| 21786 | 3 | | | | | | Mir3057 |
| 21787 | 3 | | | | | | Mir3058 |
| 21788 | 3 | | | | | | Mir3059 |
| 21789 | 3 | | | | | | Mir3060 |
| 21790 | 3 | | | | | | Mir3061 |
| 21791 | 3 | | | | | | Mir3062 |
| 21792 | 3 | | | | | | Mir3063 |
| 21793 | 3 | | | | | | Mir3064 |
| 21794 | 3 | | | | | | Mir3065 |
| 21795 | 3 | | | | | | Mir3066 |
| 21796 | 3 | | | | | | Mir3067 |
| 21797 | 3 | | | | | | Mir3068 |
| 21798 | 3 | | | | | | Mir3069 |
| 21799 | 3 | | | | | | Mir3070a |
| 21800 | 3 | | | | | | Mir3070b |
| 21801 | 3 | | | | | | Mir3071 |
| 21802 | 3 | | | | | | Mir3072 |
| 21803 | 3 | | | | | | Mir3073 |
| 21804 | 3 | | | | | | Mir3073b |
| 21805 | 3 | | | | | | Mir3074-1 |
| 21806 | 3 | | | | | | Mir3074-2 |
| 21807 | 3 | | | | | | Mir3075 |
| 21808 | 3 | | | | | | Mir3076 |
| 21809 | 3 | | | | | | Mir3077 |
| 21810 | 3 | | | | | | Mir3078 |
| 21811 | 3 | | | | | | Mir3079 |
| 21812 | 3 | | | | | | Mir3081 |
| 21813 | 3 | | | | | | Mir3082 |
| 21814 | 3 | | | | | | Mir3083 |
| 21815 | 3 | | | | | | Mir3084 |
| 21816 | 3 | | | | | | Mir3084-2 |
| 21817 | 3 | | | | | | Mir3085 |
| 21818 | 3 | | | | | | Mir3086 |
| 21819 | 3 | | | | | | Mir3087 |
| 21820 | 3 | | | | | | Mir3088 |
| 21821 | 3 | | | | | | Mir3089 |
| 21822 | 3 | | | | | | Mir3091 |
| 21823 | 3 | | | | | | Mir3092 |
| 21824 | 3 | | | | | | Mir3093 |
| 21825 | 3 | | | | | | Mir3094 |
| 21826 | 3 | | | | | | Mir3095 |
| 21827 | 3 | | | | | | Mir3097 |
| 21828 | 3 | | | | | | Mir3098 |
| 21829 | 3 | | | | | | Mir3099 |
| 21830 | 3 | | | | | | Mir30a |
| 21831 | 3 | | | | | | Mir30b |
| 21832 | 3 | | | | | | Mir30c-1 |
| 21833 | 3 | | | | | | Mir30c-2 |
| 21834 | 3 | | | | | | Mir30d |
| 21835 | 3 | | | | | | Mir30f |
| 21836 | 3 | | | | | | Mir31 |
| 21837 | 3 | | | | | | Mir3100 |
| 21838 | 3 | | | | | | Mir3101 |
| 21839 | 3 | | | | | | Mir3102 |
| 21840 | 3 | | | | | | Mir3103 |
| 21841 | 3 | | | | | | Mir3104 |
| 21842 | 3 | | | | | | Mir3106 |
| 21843 | 3 | | | | | | Mir3107 |
| 21844 | 3 | | | | | | Mir3108 |
| 21845 | 3 | | | | | | Mir3109 |
| 21846 | 3 | | | | | | Mir3110 |
| 21847 | 3 | | | | | | Mir3112 |
| 21848 | 3 | | | | | | Mir32 |
| 21849 | 3 | | | | | | Mir320 |
| 21850 | 3 | | | | | | Mir322 |
| 21851 | 3 | | | | | | Mir323 |
| 21852 | 3 | | | | | | Mir324 |
| 21853 | 3 | | | | | | Mir325 |
| 21854 | 3 | | | | | | Mir326 |
| 21855 | 3 | | | | | | Mir328 |
| 21856 | 3 | | | | | | Mir329 |
| 21857 | 3 | | | | | | Mir33 |
| 21858 | 3 | | | | | | Mir330 |
| 21859 | 3 | | | | | | Mir331 |
| 21860 | 3 | | | | | | Mir335 |
| 21861 | 3 | | | | | | Mir337 |
| 21862 | 3 | | | | | | Mir338 |
| 21863 | 3 | | | | | | Mir339 |
| 21864 | 3 | | | | | | Mir340 |
| 21865 | 3 | | | | | | Mir341 |
| 21866 | 3 | | | | | | Mir343 |
| 21867 | 3 | | | | | | Mir344 |
| 21868 | 3 | | | | | | Mir344-2 |
| 21869 | 3 | | | | | | Mir344b |
| 21870 | 3 | | | | | | Mir344c |
| 21871 | 3 | | | | | | Mir344d-1 |
| 21872 | 3 | | | | | | Mir344d-2 |
| 21873 | 3 | | | | | | Mir344d-3 |
| 21874 | 3 | | | | | | Mir344e |
| 21875 | 3 | | | | | | Mir344f |
| 21876 | 3 | | | | | | Mir344g |
| 21877 | 3 | | | | | | Mir344h-1 |
| 21878 | 3 | | | | | | Mir344i |
| 21879 | 3 | | | | | | Mir345 |
| 21880 | 3 | | | | | | Mir346 |
| 21881 | 3 | | | | | | Mir3470a |
| 21882 | 3 | | | | | | Mir3470b |
| 21883 | 3 | | | | | | Mir3471-1 |
| 21884 | 3 | | | | | | Mir3473 |
| 21885 | 3 | | | | | | Mir3473c |
| 21886 | 3 | | | | | | Mir3473d |
| 21887 | 3 | | | | | | Mir3473e |
| 21888 | 3 | | | | | | Mir3473f |
| 21889 | 3 | | | | | | Mir3473g |
| 21890 | 3 | | | | | | Mir3474 |
| 21891 | 3 | | | | | | Mir3475 |
| 21892 | 3 | | | | | | Mir34a |
| 21893 | 3 | | | | | | Mir34b |
| 21894 | 3 | | | | | | Mir34c |
| 21895 | 3 | | | | | | Mir350 |
| 21896 | 3 | | | | | | Mir351 |
| 21897 | 3 | | | | | | Mir3535 |
| 21898 | 3 | | | | | | Mir3544 |
| 21899 | 3 | | | | | | Mir3547 |
| 21900 | 3 | | | | | | Mir3569 |
| 21901 | 3 | | | | | | Mir3572 |
| 21902 | 3 | | | | | | Mir362 |
| 21903 | 3 | | | | | | Mir3620 |
| 21904 | 3 | | | | | | Mir363 |
| 21905 | 3 | | | | | | Mir365-1 |
| 21906 | 3 | | | | | | Mir365-2 |
| 21907 | 3 | | | | | | Mir367 |
| 21908 | 3 | | | | | | Mir369 |
| 21909 | 3 | | | | | | Mir370 |
| 21910 | 3 | | | | | | Mir374 |
| 21911 | 3 | | | | | | Mir374c |
| 21912 | 3 | | | | | | Mir375 |
| 21913 | 3 | | | | | | Mir376a |
| 21914 | 3 | | | | | | Mir376b |
| 21915 | 3 | | | | | | Mir376c |
| 21916 | 3 | | | | | | Mir377 |
| 21917 | 3 | | | | | | Mir378 |
| 21918 | 3 | | | | | | Mir378b |
| 21919 | 3 | | | | | | Mir378c |
| 21920 | 3 | | | | | | Mir379 |
| 21921 | 3 | | | | | | Mir380 |
| 21922 | 3 | | | | | | Mir381 |
| 21923 | 3 | | | | | | Mir382 |
| 21924 | 3 | | | | | | Mir383 |
| 21925 | 3 | | | | | | Mir384 |
| 21926 | 3 | | | | | | Mir3960 |
| 21927 | 3 | | | | | | Mir3962 |

Fig. 43 - 130

| | | | | | | | |
|---|---|---|---|---|---|---|---|
| 21928 | 3 | | | | | | Mir3963 |
| 21929 | 3 | | | | | | Mir3964 |
| 21930 | 3 | | | | | | Mir3965 |
| 21931 | 3 | | | | | | Mir3966 |
| 21932 | 3 | | | | | | Mir3967 |
| 21933 | 3 | | | | | | Mir3968 |
| 21934 | 3 | | | | | | Mir3969 |
| 21935 | 3 | | | | | | Mir3970 |
| 21936 | 3 | | | | | | Mir3971 |
| 21937 | 3 | | | | | | Mir409 |
| 21938 | 3 | | | | | | Mir410 |
| 21939 | 3 | | | | | | Mir411 |
| 21940 | 3 | | | | | | Mir412 |
| 21941 | 3 | | | | | | Mir421 |
| 21942 | 3 | | | | | | Mir423 |
| 21943 | 3 | | | | | | Mir425 |
| 21944 | 3 | | | | | | Mir429 |
| 21945 | 3 | | | | | | Mir431 |
| 21946 | 3 | | | | | | Mir432 |
| 21947 | 3 | | | | | | Mir433 |
| 21948 | 3 | | | | | | Mir434 |
| 21949 | 3 | | | | | | Mir448 |
| 21950 | 3 | | | | | | Mir449a |
| 21951 | 3 | | | | | | Mir449b |
| 21952 | 3 | | | | | | Mir449c |
| 21953 | 3 | | | | | | Mir450-1 |
| 21954 | 3 | | | | | | Mir450-2 |
| 21955 | 3 | | | | | | Mir450b |
| 21956 | 3 | | | | | | Mir451 |
| 21957 | 3 | | | | | | Mir452 |
| 21958 | 3 | | | | | | Mir453 |
| 21959 | 3 | | | | | | Mir455 |
| 21960 | 3 | | | | | | Mir463 |
| 21961 | 3 | | | | | | Mir465 |
| 21962 | 3 | | | | | | Mir465b-1 |
| 21963 | 3 | | | | | | Mir465c-1 |
| 21964 | 3 | | | | | | Mir465d |
| 21965 | 3 | | | | | | Mir466 |
| 21966 | 3 | | | | | | Mir466b |
| 21967 | 3 | | | | | | Mir466b-2 |
| 21968 | 3 | | | | | | Mir466b-3 |
| 21969 | 3 | | | | | | Mir466d |
| 21970 | 3 | | | | | | Mir466f-1 |
| 21971 | 3 | | | | | | Mir466f-2 |
| 21972 | 3 | | | | | | Mir466f-3 |
| 21973 | 3 | | | | | | Mir466g |
| 21974 | 3 | | | | | | Mir466h |
| 21975 | 3 | | | | | | Mir466i |
| 21976 | 3 | | | | | | Mir466n |
| 21977 | 3 | | | | | | Mir466p |
| 21978 | 3 | | | | | | Mir467a-1 |
| 21979 | 3 | | | | | | Mir467a-10 |
| 21980 | 3 | | | | | | Mir467a-2 |
| 21981 | 3 | | | | | | Mir467a-3 |
| 21982 | 3 | | | | | | Mir467a-5 |
| 21983 | 3 | | | | | | Mir467a-7 |
| 21984 | 3 | | | | | | Mir467a-9 |
| 21985 | 3 | | | | | | Mir467b |
| 21986 | 3 | | | | | | Mir467c |
| 21987 | 3 | | | | | | Mir467d |
| 21988 | 3 | | | | | | Mir467e |
| 21989 | 3 | | | | | | Mir467f |
| 21990 | 3 | | | | | | Mir468 |
| 21991 | 3 | | | | | | Mir470 |
| 21992 | 3 | | | | | | Mir471 |
| 21993 | 3 | | | | | | Mir483 |
| 21994 | 3 | | | | | | Mir484 |
| 21995 | 3 | | | | | | Mir485 |
| 21996 | 3 | | | | | | Mir486 |
| 21997 | 3 | | | | | | Mir487b |
| 21998 | 3 | | | | | | Mir488 |
| 21999 | 3 | | | | | | Mir489 |
| 22000 | 3 | | | | | | Mir490 |
| 22001 | 3 | | | | | | Mir491 |
| 22002 | 3 | | | | | | Mir493 |
| 22003 | 3 | | | | | | Mir494 |
| 22004 | 3 | | | | | | Mir495 |
| 22005 | 3 | | | | | | Mir496 |
| 22006 | 3 | | | | | | Mir496b |
| 22007 | 3 | | | | | | Mir497 |
| 22008 | 3 | | | | | | Mir497b |
| 22009 | 3 | | | | | | Mir499 |
| 22010 | 3 | | | | | | Mir500 |
| 22011 | 3 | | | | | | Mir501 |
| 22012 | 3 | | | | | | Mir503 |
| 22013 | 3 | | | | | | Mir504 |
| 22014 | 3 | | | | | | Mir5046 |
| 22015 | 3 | | | | | | Mir505 |
| 22016 | 3 | | | | | | Mir509 |
| 22017 | 3 | | | | | | Mir5098 |
| 22018 | 3 | | | | | | Mir5100 |
| 22019 | 3 | | | | | | Mir5101 |
| 22020 | 3 | | | | | | Mir5103 |
| 22021 | 3 | | | | | | Mir5104 |
| 22022 | 3 | | | | | | Mir5106 |
| 22023 | 3 | | | | | | Mir5107 |
| 22024 | 3 | | | | | | Mir5108 |
| 22025 | 3 | | | | | | Mir511 |
| 22026 | 3 | | | | | | Mir5112 |
| 22027 | 3 | | | | | | Mir5113 |
| 22028 | 3 | | | | | | Mir5114 |
| 22029 | 3 | | | | | | Mir5116 |
| 22030 | 3 | | | | | | Mir5119 |
| 22031 | 3 | | | | | | Mir5120 |
| 22032 | 3 | | | | | | Mir5121 |
| 22033 | 3 | | | | | | Mir5122 |
| 22034 | 3 | | | | | | Mir5123 |
| 22035 | 3 | | | | | | Mir5124 |
| 22036 | 3 | | | | | | Mir5125 |
| 22037 | 3 | | | | | | Mir5126 |
| 22038 | 3 | | | | | | Mir5127 |
| 22039 | 3 | | | | | | Mir5128 |
| 22040 | 3 | | | | | | Mir5129 |
| 22041 | 3 | | | | | | Mir5130 |
| 22042 | 3 | | | | | | Mir5131 |
| 22043 | 3 | | | | | | Mir5132 |
| 22044 | 3 | | | | | | Mir5133 |
| 22045 | 3 | | | | | | Mir5134 |
| 22046 | 3 | | | | | | Mir5135 |
| 22047 | 3 | | | | | | Mir5136 |
| 22048 | 3 | | | | | | Mir532 |
| 22049 | 3 | | | | | | Mir539 |
| 22050 | 3 | | | | | | Mir540 |
| 22051 | 3 | | | | | | Mir541 |
| 22052 | 3 | | | | | | Mir542 |
| 22053 | 3 | | | | | | Mir543 |
| 22054 | 3 | | | | | | Mir544 |
| 22055 | 3 | | | | | | Mir546 |
| 22056 | 3 | | | | | | Mir547 |
| 22057 | 3 | | | | | | Mir551b |
| 22058 | 3 | | | | | | Mir5615-1 |
| 22059 | 3 | | | | | | Mir5615-2 |
| 22060 | 3 | | | | | | Mir5616 |
| 22061 | 3 | | | | | | Mir5617 |
| 22062 | 3 | | | | | | Mir5618 |
| 22063 | 3 | | | | | | Mir5619 |
| 22064 | 3 | | | | | | Mir5620 |
| 22065 | 3 | | | | | | Mir5621 |
| 22066 | 3 | | | | | | Mir5622 |
| 22067 | 3 | | | | | | Mir5623 |
| 22068 | 3 | | | | | | Mir5624 |
| 22069 | 3 | | | | | | Mir5625 |
| 22070 | 3 | | | | | | Mir5626 |
| 22071 | 3 | | | | | | Mir5627 |
| 22072 | 3 | | | | | | Mir568 |
| 22073 | 3 | | | | | | Mir5709 |
| 22074 | 3 | | | | | | Mir5710 |
| 22075 | 3 | | | | | | Mir574 |
| 22076 | 3 | | | | | | Mir582 |
| 22077 | 3 | | | | | | Mir592 |
| 22078 | 3 | | | | | | Mir598 |
| 22079 | 3 | | | | | | Mir599 |
| 22080 | 3 | | | | | | Mir615 |
| 22081 | 3 | | | | | | Mir6237 |
| 22082 | 3 | | | | | | Mir6238 |
| 22083 | 3 | | | | | | Mir6239 |
| 22084 | 3 | | | | | | Mir6241 |
| 22085 | 3 | | | | | | Mir6244 |
| 22086 | 3 | | | | | | Mir6336 |
| 22087 | 3 | | | | | | Mir6337 |
| 22088 | 3 | | | | | | Mir6338 |
| 22089 | 3 | | | | | | Mir6339 |
| 22090 | 3 | | | | | | Mir6341 |
| 22091 | 3 | | | | | | Mir6342 |
| 22092 | 3 | | | | | | Mir6343 |
| 22093 | 3 | | | | | | Mir6344 |
| 22094 | 3 | | | | | | Mir6345 |
| 22095 | 3 | | | | | | Mir6348 |
| 22096 | 3 | | | | | | Mir6349 |
| 22097 | 3 | | | | | | Mir6350 |

Fig. 43 - 131

| | | | | | | | |
|---|---|---|---|---|---|---|---|
| 22098 | 3 | | | | | | Mir6352 |
| 22099 | 3 | | | | | | Mir6353 |
| 22100 | 3 | | | | | | Mir6354 |
| 22101 | 3 | | | | | | Mir6355 |
| 22102 | 3 | | | | | | Mir6356 |
| 22103 | 3 | | | | | | Mir6358 |
| 22104 | 3 | | | | | | Mir6359 |
| 22105 | 3 | | | | | | Mir6360 |
| 22106 | 3 | | | | | | Mir6361 |
| 22107 | 3 | | | | | | Mir6362 |
| 22108 | 3 | | | | | | Mir6364 |
| 22109 | 3 | | | | | | Mir6365 |
| 22110 | 3 | | | | | | Mir6366 |
| 22111 | 3 | | | | | | Mir6367 |
| 22112 | 3 | | | | | | Mir6368 |
| 22113 | 3 | | | | | | Mir6372 |
| 22114 | 3 | | | | | | Mir6373 |
| 22115 | 3 | | | | | | Mir6374 |
| 22116 | 3 | | | | | | Mir6375 |
| 22117 | 3 | | | | | | Mir6376 |
| 22118 | 3 | | | | | | Mir6378 |
| 22119 | 3 | | | | | | Mir6380 |
| 22120 | 3 | | | | | | Mir6381 |
| 22121 | 3 | | | | | | Mir6382 |
| 22122 | 3 | | | | | | Mir6383 |
| 22123 | 3 | | | | | | Mir6385 |
| 22124 | 3 | | | | | | Mir6386 |
| 22125 | 3 | | | | | | Mir6387 |
| 22126 | 3 | | | | | | Mir6388 |
| 22127 | 3 | | | | | | Mir6389 |
| 22128 | 3 | | | | | | Mir6391 |
| 22129 | 3 | | | | | | Mir6392 |
| 22130 | 3 | | | | | | Mir6393 |
| 22131 | 3 | | | | | | Mir6394 |
| 22132 | 3 | | | | | | Mir6395 |
| 22133 | 3 | | | | | | Mir6396 |
| 22134 | 3 | | | | | | Mir6397 |
| 22135 | 3 | | | | | | Mir6399 |
| 22136 | 3 | | | | | | Mir6400 |
| 22137 | 3 | | | | | | Mir6401 |
| 22138 | 3 | | | | | | Mir6402 |
| 22139 | 3 | | | | | | Mir6403 |
| 22140 | 3 | | | | | | Mir6405 |
| 22141 | 3 | | | | | | Mir6406 |
| 22142 | 3 | | | | | | Mir6407 |
| 22143 | 3 | | | | | | Mir6408 |
| 22144 | 3 | | | | | | Mir6409 |
| 22145 | 3 | | | | | | Mir6410 |
| 22146 | 3 | | | | | | Mir6411 |
| 22147 | 3 | | | | | | Mir6412 |
| 22148 | 3 | | | | | | Mir6413 |
| 22149 | 3 | | | | | | Mir6414 |
| 22150 | 3 | | | | | | Mir6415 |
| 22151 | 3 | | | | | | Mir6416 |
| 22152 | 3 | | | | | | Mir6417 |
| 22153 | 3 | | | | | | Mir6418 |
| 22154 | 3 | | | | | | Mir6419 |
| 22155 | 3 | | | | | | Mir6420 |
| 22156 | 3 | | | | | | Mir6481 |
| 22157 | 3 | | | | | | Mir6516 |
| 22158 | 3 | | | | | | Mir653 |
| 22159 | 3 | | | | | | Mir6537 |
| 22160 | 3 | | | | | | Mir6538 |
| 22161 | 3 | | | | | | Mir6539 |
| 22162 | 3 | | | | | | Mir654 |
| 22163 | 3 | | | | | | Mir6541 |
| 22164 | 3 | | | | | | Mir6546 |
| 22165 | 3 | | | | | | Mir664 |
| 22166 | 3 | | | | | | Mir665 |
| 22167 | 3 | | | | | | Mir666 |
| 22168 | 3 | | | | | | Mir667 |
| 22169 | 3 | | | | | | Mir668 |
| 22170 | 3 | | | | | | Mir669a-1 |
| 22171 | 3 | | | | | | Mir669a-2 |
| 22172 | 3 | | | | | | Mir669a-3 |
| 22173 | 3 | | | | | | Mir669a-4 |
| 22174 | 3 | | | | | | Mir669b |
| 22175 | 3 | | | | | | Mir669c |
| 22176 | 3 | | | | | | Mir669e |
| 22177 | 3 | | | | | | Mir669g |
| 22178 | 3 | | | | | | Mir669h |
| 22179 | 3 | | | | | | Mir669i |
| 22180 | 3 | | | | | | Mir669j |
| 22181 | 3 | | | | | | Mir669k |
| 22182 | 3 | | | | | | Mir669m-1 |
| 22183 | 3 | | | | | | Mir669m-2 |
| 22184 | 3 | | | | | | Mir669p-1 |
| 22185 | 3 | | | | | | Mir670 |
| 22186 | 3 | | | | | | Mir671 |
| 22187 | 3 | | | | | | Mir6715 |
| 22188 | 3 | | | | | | Mir672 |
| 22189 | 3 | | | | | | Mir673 |
| 22190 | 3 | | | | | | Mir674 |
| 22191 | 3 | | | | | | Mir675 |
| 22192 | 3 | | | | | | Mir676 |
| 22193 | 3 | | | | | | Mir6769b |
| 22194 | 3 | | | | | | Mir677 |
| 22195 | 3 | | | | | | Mir678 |
| 22196 | 3 | | | | | | Mir679 |
| 22197 | 3 | | | | | | Mir680-2 |
| 22198 | 3 | | | | | | Mir680-3 |
| 22199 | 3 | | | | | | Mir681 |
| 22200 | 3 | | | | | | Mir683-1 |
| 22201 | 3 | | | | | | Mir683-2 |
| 22202 | 3 | | | | | | Mir684-1 |
| 22203 | 3 | | | | | | Mir684-2 |
| 22204 | 3 | | | | | | Mir686 |
| 22205 | 3 | | | | | | Mir688 |
| 22206 | 3 | | | | | | Mir6896 |
| 22207 | 3 | | | | | | Mir6897 |
| 22208 | 3 | | | | | | Mir6898 |
| 22209 | 3 | | | | | | Mir6899 |
| 22210 | 3 | | | | | | Mir690 |
| 22211 | 3 | | | | | | Mir6900 |
| 22212 | 3 | | | | | | Mir6901 |
| 22213 | 3 | | | | | | Mir6902 |
| 22214 | 3 | | | | | | Mir6903 |
| 22215 | 3 | | | | | | Mir6904 |
| 22216 | 3 | | | | | | Mir6905 |
| 22217 | 3 | | | | | | Mir6906 |
| 22218 | 3 | | | | | | Mir6907 |
| 22219 | 3 | | | | | | Mir6908 |
| 22220 | 3 | | | | | | Mir6909 |
| 22221 | 3 | | | | | | Mir691 |
| 22222 | 3 | | | | | | Mir6910 |
| 22223 | 3 | | | | | | Mir6911 |
| 22224 | 3 | | | | | | Mir6912 |
| 22225 | 3 | | | | | | Mir6913 |
| 22226 | 3 | | | | | | Mir6914 |
| 22227 | 3 | | | | | | Mir6915 |
| 22228 | 3 | | | | | | Mir6916 |
| 22229 | 3 | | | | | | Mir6917 |
| 22230 | 3 | | | | | | Mir6918 |
| 22231 | 3 | | | | | | Mir6919 |
| 22232 | 3 | | | | | | Mir6920 |
| 22233 | 3 | | | | | | Mir6921 |
| 22234 | 3 | | | | | | Mir692-1 |
| 22235 | 3 | | | | | | Mir6922 |
| 22236 | 3 | | | | | | Mir6923 |
| 22237 | 3 | | | | | | Mir6924 |
| 22238 | 3 | | | | | | Mir6925 |
| 22239 | 3 | | | | | | Mir6926 |
| 22240 | 3 | | | | | | Mir6927 |
| 22241 | 3 | | | | | | Mir6928 |
| 22242 | 3 | | | | | | Mir6929 |
| 22243 | 3 | | | | | | Mir693 |
| 22244 | 3 | | | | | | Mir6930 |
| 22245 | 3 | | | | | | Mir6931 |
| 22246 | 3 | | | | | | Mir6932 |
| 22247 | 3 | | | | | | Mir6933 |
| 22248 | 3 | | | | | | Mir6934 |
| 22249 | 3 | | | | | | Mir6935 |
| 22250 | 3 | | | | | | Mir6936 |
| 22251 | 3 | | | | | | Mir6937 |
| 22252 | 3 | | | | | | Mir6938 |
| 22253 | 3 | | | | | | Mir6939 |
| 22254 | 3 | | | | | | Mir694 |
| 22255 | 3 | | | | | | Mir6940 |
| 22256 | 3 | | | | | | Mir6941 |
| 22257 | 3 | | | | | | Mir6942 |
| 22258 | 3 | | | | | | Mir6943 |
| 22259 | 3 | | | | | | Mir6944 |
| 22260 | 3 | | | | | | Mir6945 |
| 22261 | 3 | | | | | | Mir6946 |
| 22262 | 3 | | | | | | Mir6947 |
| 22263 | 3 | | | | | | Mir6948 |
| 22264 | 3 | | | | | | Mir6949 |
| 22265 | 3 | | | | | | Mir695 |
| 22266 | 3 | | | | | | Mir6950 |
| 22267 | 3 | | | | | | Mir6951 |

Fig. 43 - 132

| | | | | | | | | | | | | | | |
|---|---|---|---|---|---|---|---|---|---|---|---|---|---|---|
| 22268 | 3 | | | | | Mir6952 | | 22353 | 3 | | | | | Mir7032 |
| 22269 | 3 | | | | | Mir6953 | | 22354 | 3 | | | | | Mir7033 |
| 22270 | 3 | | | | | Mir6954 | | 22355 | 3 | | | | | Mir7034 |
| 22271 | 3 | | | | | Mir6955 | | 22356 | 3 | | | | | Mir7036 |
| 22272 | 3 | | | | | Mir6956 | | 22357 | 3 | | | | | Mir7036b |
| 22273 | 3 | | | | | Mir6957 | | 22358 | 3 | | | | | Mir7037 |
| 22274 | 3 | | | | | Mir6958 | | 22359 | 3 | | | | | Mir7038 |
| 22275 | 3 | | | | | Mir6959 | | 22360 | 3 | | | | | Mir7039 |
| 22276 | 3 | | | | | Mir6960 | | 22361 | 3 | | | | | Mir704 |
| 22277 | 3 | | | | | Mir6961 | | 22362 | 3 | | | | | Mir7040 |
| 22278 | 3 | | | | | Mir6962 | | 22363 | 3 | | | | | Mir7041 |
| 22279 | 3 | | | | | Mir6963 | | 22364 | 3 | | | | | Mir7042 |
| 22280 | 3 | | | | | Mir6964 | | 22365 | 3 | | | | | Mir7043 |
| 22281 | 3 | | | | | Mir6965 | | 22366 | 3 | | | | | Mir7044 |
| 22282 | 3 | | | | | Mir6966 | | 22367 | 3 | | | | | Mir7045 |
| 22283 | 3 | | | | | Mir6968 | | 22368 | 3 | | | | | Mir7046 |
| 22284 | 3 | | | | | Mir6969 | | 22369 | 3 | | | | | Mir7047 |
| 22285 | 3 | | | | | Mir697 | | 22370 | 3 | | | | | Mir7048 |
| 22286 | 3 | | | | | Mir6970 | | 22371 | 3 | | | | | Mir7049 |
| 22287 | 3 | | | | | Mir6971 | | 22372 | 3 | | | | | Mir705 |
| 22288 | 3 | | | | | Mir6972 | | 22373 | 3 | | | | | Mir7050 |
| 22289 | 3 | | | | | Mir6973a | | 22374 | 3 | | | | | Mir7051 |
| 22290 | 3 | | | | | Mir6973b | | 22375 | 3 | | | | | Mir7052 |
| 22291 | 3 | | | | | Mir6974 | | 22376 | 3 | | | | | Mir7053 |
| 22292 | 3 | | | | | Mir6975 | | 22377 | 3 | | | | | Mir7054 |
| 22293 | 3 | | | | | Mir6976 | | 22378 | 3 | | | | | Mir7055 |
| 22294 | 3 | | | | | Mir6977 | | 22379 | 3 | | | | | Mir7056 |
| 22295 | 3 | | | | | Mir6978 | | 22380 | 3 | | | | | Mir7057 |
| 22296 | 3 | | | | | Mir6979 | | 22381 | 3 | | | | | Mir7058 |
| 22297 | 3 | | | | | Mir698 | | 22382 | 3 | | | | | Mir7059 |
| 22298 | 3 | | | | | Mir6980 | | 22383 | 3 | | | | | Mir706 |
| 22299 | 3 | | | | | Mir6981 | | 22384 | 3 | | | | | Mir7061 |
| 22300 | 3 | | | | | Mir6982 | | 22385 | 3 | | | | | Mir7062 |
| 22301 | 3 | | | | | Mir6983 | | 22386 | 3 | | | | | Mir7064 |
| 22302 | 3 | | | | | Mir6984 | | 22387 | 3 | | | | | Mir7065 |
| 22303 | 3 | | | | | Mir6985 | | 22388 | 3 | | | | | Mir7066 |
| 22304 | 3 | | | | | Mir6986 | | 22389 | 3 | | | | | Mir7067 |
| 22305 | 3 | | | | | Mir6987 | | 22390 | 3 | | | | | Mir7068 |
| 22306 | 3 | | | | | Mir6988 | | 22391 | 3 | | | | | Mir7069 |
| 22307 | 3 | | | | | Mir6989 | | 22392 | 3 | | | | | Mir707 |
| 22308 | 3 | | | | | Mir6990 | | 22393 | 3 | | | | | Mir7070 |
| 22309 | 3 | | | | | Mir6991 | | 22394 | 3 | | | | | Mir7071 |
| 22310 | 3 | | | | | Mir6992 | | 22395 | 3 | | | | | Mir7072 |
| 22311 | 3 | | | | | Mir6993 | | 22396 | 3 | | | | | Mir7073 |
| 22312 | 3 | | | | | Mir6994 | | 22397 | 3 | | | | | Mir7074 |
| 22313 | 3 | | | | | Mir6995 | | 22398 | 3 | | | | | Mir7075 |
| 22314 | 3 | | | | | Mir6996 | | 22399 | 3 | | | | | Mir7076 |
| 22315 | 3 | | | | | Mir6997 | | 22400 | 3 | | | | | Mir7077 |
| 22316 | 3 | | | | | Mir6998 | | 22401 | 3 | | | | | Mir7078 |
| 22317 | 3 | | | | | Mir6999 | | 22402 | 3 | | | | | Mir7079 |
| 22318 | 3 | | | | | Mir700 | | 22403 | 3 | | | | | Mir708 |
| 22319 | 3 | | | | | Mir7000 | | 22404 | 3 | | | | | Mir7080 |
| 22320 | 3 | | | | | Mir7001 | | 22405 | 3 | | | | | Mir7081 |
| 22321 | 3 | | | | | Mir7002 | | 22406 | 3 | | | | | Mir7082 |
| 22322 | 3 | | | | | Mir7003 | | 22407 | 3 | | | | | Mir7083 |
| 22323 | 3 | | | | | Mir7004 | | 22408 | 3 | | | | | Mir7084 |
| 22324 | 3 | | | | | Mir7005 | | 22409 | 3 | | | | | Mir7085 |
| 22325 | 3 | | | | | Mir7006 | | 22410 | 3 | | | | | Mir7086 |
| 22326 | 3 | | | | | Mir7007 | | 22411 | 3 | | | | | Mir7087 |
| 22327 | 3 | | | | | Mir7008 | | 22412 | 3 | | | | | Mir7088 |
| 22328 | 3 | | | | | Mir7009 | | 22413 | 3 | | | | | Mir7089 |
| 22329 | 3 | | | | | Mir701 | | 22414 | 3 | | | | | Mir709 |
| 22330 | 3 | | | | | Mir7010 | | 22415 | 3 | | | | | Mir7090 |
| 22331 | 3 | | | | | Mir7011 | | 22416 | 3 | | | | | Mir7091 |
| 22332 | 3 | | | | | Mir7012 | | 22417 | 3 | | | | | Mir7092 |
| 22333 | 3 | | | | | Mir7013 | | 22418 | 3 | | | | | Mir7093 |
| 22334 | 3 | | | | | Mir7014 | | 22419 | 3 | | | | | Mir7094-1 |
| 22335 | 3 | | | | | Mir7015 | | 22420 | 3 | | | | | Mir710 |
| 22336 | 3 | | | | | Mir7016 | | 22421 | 3 | | | | | Mir711 |
| 22337 | 3 | | | | | Mir7017 | | 22422 | 3 | | | | | Mir7115 |
| 22338 | 3 | | | | | Mir7018 | | 22423 | 3 | | | | | Mir7117 |
| 22339 | 3 | | | | | Mir7019 | | 22424 | 3 | | | | | Mir7118 |
| 22340 | 3 | | | | | Mir702 | | 22425 | 3 | | | | | Mir7119 |
| 22341 | 3 | | | | | Mir7020 | | 22426 | 3 | | | | | Mir713 |
| 22342 | 3 | | | | | Mir7021 | | 22427 | 3 | | | | | Mir717 |
| 22343 | 3 | | | | | Mir7022 | | 22428 | 3 | | | | | Mir718 |
| 22344 | 3 | | | | | Mir7023 | | 22429 | 3 | | | | | Mir719 |
| 22345 | 3 | | | | | Mir7024 | | 22430 | 3 | | | | | Mir7-2 |
| 22346 | 3 | | | | | Mir7025 | | 22431 | 3 | | | | | Mir721 |
| 22347 | 3 | | | | | Mir7026 | | 22432 | 3 | | | | | Mir7210 |
| 22348 | 3 | | | | | Mir7027 | | 22433 | 3 | | | | | Mir7211 |
| 22349 | 3 | | | | | Mir7028 | | 22434 | 3 | | | | | Mir7212 |
| 22350 | 3 | | | | | Mir7029 | | 22435 | 3 | | | | | Mir7213 |
| 22351 | 3 | | | | | Mir7030 | | 22436 | 3 | | | | | Mir7214 |
| 22352 | 3 | | | | | Mir7031 | | 22437 | 3 | | | | | Mir7215 |

Fig. 43 - 133

| | | | | | | | | |
|---|---|---|---|---|---|---|---|---|
| 22438 | 3 | | | | | | | Mir7216 |
| 22439 | 3 | | | | | | | Mir7217 |
| 22440 | 3 | | | | | | | Mir7218 |
| 22441 | 3 | | | | | | | Mir7219 |
| 22442 | 3 | | | | | | | Mir7220 |
| 22443 | 3 | | | | | | | Mir7221 |
| 22444 | 3 | | | | | | | Mir7222 |
| 22445 | 3 | | | | | | | Mir7223 |
| 22446 | 3 | | | | | | | Mir7224 |
| 22447 | 3 | | | | | | | Mir7225 |
| 22448 | 3 | | | | | | | Mir7226 |
| 22449 | 3 | | | | | | | Mir7227 |
| 22450 | 3 | | | | | | | Mir7228 |
| 22451 | 3 | | | | | | | Mir7229 |
| 22452 | 3 | | | | | | | Mir7230 |
| 22453 | 3 | | | | | | | Mir7231 |
| 22454 | 3 | | | | | | | Mir7232 |
| 22455 | 3 | | | | | | | Mir7233 |
| 22456 | 3 | | | | | | | Mir7234 |
| 22457 | 3 | | | | | | | Mir7236 |
| 22458 | 3 | | | | | | | Mir7237 |
| 22459 | 3 | | | | | | | Mir7238 |
| 22460 | 3 | | | | | | | Mir7239 |
| 22461 | 3 | | | | | | | Mir7240 |
| 22462 | 3 | | | | | | | Mir7241 |
| 22463 | 3 | | | | | | | Mir7242 |
| 22464 | 3 | | | | | | | Mir7243 |
| 22465 | 3 | | | | | | | Mir741 |
| 22466 | 3 | | | | | | | Mir742 |
| 22467 | 3 | | | | | | | Mir743 |
| 22468 | 3 | | | | | | | Mir743b |
| 22469 | 3 | | | | | | | Mir744 |
| 22470 | 3 | | | | | | | Mir7578 |
| 22471 | 3 | | | | | | | Mir758 |
| 22472 | 3 | | | | | | | Mir759 |
| 22473 | 3 | | | | | | | Mir760 |
| 22474 | 3 | | | | | | | Mir761 |
| 22475 | 3 | | | | | | | Mir762 |
| 22476 | 3 | | | | | | | Mir764 |
| 22477 | 3 | | | | | | | Mir7646 |
| 22478 | 3 | | | | | | | Mir7647 |
| 22479 | 3 | | | | | | | Mir7648 |
| 22480 | 3 | | | | | | | Mir7649 |
| 22481 | 3 | | | | | | | Mir7650 |
| 22482 | 3 | | | | | | | Mir7652 |
| 22483 | 3 | | | | | | | Mir7653 |
| 22484 | 3 | | | | | | | Mir7654 |
| 22485 | 3 | | | | | | | Mir7655 |
| 22486 | 3 | | | | | | | Mir7656 |
| 22487 | 3 | | | | | | | Mir7657 |
| 22488 | 3 | | | | | | | Mir7658 |
| 22489 | 3 | | | | | | | Mir7661 |
| 22490 | 3 | | | | | | | Mir7662 |
| 22491 | 3 | | | | | | | Mir7663 |
| 22492 | 3 | | | | | | | Mir7665 |
| 22493 | 3 | | | | | | | Mir7666 |
| 22494 | 3 | | | | | | | Mir7667 |
| 22495 | 3 | | | | | | | Mir7668 |
| 22496 | 3 | | | | | | | Mir7669 |
| 22497 | 3 | | | | | | | Mir767 |
| 22498 | 3 | | | | | | | Mir7670 |
| 22499 | 3 | | | | | | | Mir7671 |
| 22500 | 3 | | | | | | | Mir7672 |
| 22501 | 3 | | | | | | | Mir7673 |
| 22502 | 3 | | | | | | | Mir7674 |
| 22503 | 3 | | | | | | | Mir7675 |
| 22504 | 3 | | | | | | | Mir7676-2 |
| 22505 | 3 | | | | | | | Mir7677 |
| 22506 | 3 | | | | | | | Mir7678 |
| 22507 | 3 | | | | | | | Mir7679 |
| 22508 | 3 | | | | | | | Mir7680 |
| 22509 | 3 | | | | | | | Mir7681 |
| 22510 | 3 | | | | | | | Mir7682 |
| 22511 | 3 | | | | | | | Mir7684 |
| 22512 | 3 | | | | | | | Mir7685 |
| 22513 | 3 | | | | | | | Mir7686 |
| 22514 | 3 | | | | | | | Mir7687 |
| 22515 | 3 | | | | | | | Mir770 |
| 22516 | 3 | | | | | | | Mir7b |
| 22517 | 3 | | | | | | | Mir802 |
| 22518 | 3 | | | | | | | Mir804 |
| 22519 | 3 | | | | | | | Mir8092 |
| 22520 | 3 | | | | | | | Mir8093 |
| 22521 | 3 | | | | | | | Mir8095 |
| 22522 | 3 | | | | | | | Mir8096 |
| 22523 | 3 | | | | | | | Mir8101 |
| 22524 | 3 | | | | | | | Mir8103 |
| 22525 | 3 | | | | | | | Mir8106 |
| 22526 | 3 | | | | | | | Mir8107 |
| 22527 | 3 | | | | | | | Mir8109 |
| 22528 | 3 | | | | | | | Mir8110 |
| 22529 | 3 | | | | | | | Mir8111 |
| 22530 | 3 | | | | | | | Mir8115 |
| 22531 | 3 | | | | | | | Mir8116 |
| 22532 | 3 | | | | | | | Mir8118 |
| 22533 | 3 | | | | | | | Mir8119 |
| 22534 | 3 | | | | | | | Mir871 |
| 22535 | 3 | | | | | | | Mir872 |
| 22536 | 3 | | | | | | | Mir873b |
| 22537 | 3 | | | | | | | Mir874 |
| 22538 | 3 | | | | | | | Mir875 |
| 22539 | 3 | | | | | | | Mir876 |
| 22540 | 3 | | | | | | | Mir877 |
| 22541 | 3 | | | | | | | Mir878 |
| 22542 | 3 | | | | | | | Mir879 |
| 22543 | 3 | | | | | | | Mir881 |
| 22544 | 3 | | | | | | | Mir882 |
| 22545 | 3 | | | | | | | Mir883b |
| 22546 | 3 | | | | | | | Mir9-1 |
| 22547 | 3 | | | | | | | Mir9-2 |
| 22548 | 3 | | | | | | | Mir92b |
| 22549 | 3 | | | | | | | Mir93 |
| 22550 | 3 | | | | | | | Mir9-3 |
| 22551 | 3 | | | | | | | Mir96 |
| 22552 | 3 | | | | | | | Mir98 |
| 22553 | 3 | | | | | | | Mir99a |
| 22554 | 3 | | | | | | | Mir99b |
| 22555 | 3 | | | | | | | Mirlet7a-1 |
| 22556 | 3 | | | | | | | Mirlet7a-2 |
| 22557 | 3 | | | | | | | Mirlet7b |
| 22558 | 3 | | | | | | | Mirlet7e |
| 22559 | 3 | | | | | | | Mirlet7f-1 |
| 22560 | 3 | | | | | | | Mirlet7i |
| 22561 | 3 | | | | | | | Mirlet7k |
| 22562 | 3 | | | | | | | Mis12 |
| 22563 | 3 | | | | | | | Mis18a |
| 22564 | 3 | | | | | | | Mis18bp1 |
| 22565 | 3 | | | | | | | Misp |
| 22566 | 3 | | | | | | | Mitf |
| 22567 | 3 | | | | | | | Mon1b |
| 22568 | 3 | | | | | | | Mrgpra9 |
| 22569 | 3 | | | | | | | Mrgprb4 |
| 22570 | 3 | | | | | | | Nf1 |
| 22571 | 3 | | | | | | | Nlrp5 |
| 22572 | 3 | | | | | | | Nlrp5-ps |
| 22573 | 3 | | | | | | | Nlrp9b |
| 22574 | 3 | | | | | | | Nobox |
| 22575 | 3 | | | | | | | Nodal |
| 22576 | 3 | | | | | | | Nox3 |
| 22577 | 3 | | | | | | | NrOb1 |
| 22578 | 3 | | | | | | | Obp2b |
| 22579 | 3 | | | | | | | Ocrl |
| 22580 | 3 | | | | | | | Odf3l2 |
| 22581 | 3 | | | | | | | Olfr101 |
| 22582 | 3 | | | | | | | Olfr1013 |
| 22583 | 3 | | | | | | | Olfr1015 |
| 22584 | 3 | | | | | | | Olfr1044 |
| 22585 | 3 | | | | | | | Olfr1045 |
| 22586 | 3 | | | | | | | Olfr1046 |
| 22587 | 3 | | | | | | | Olfr1047 |
| 22588 | 3 | | | | | | | Olfr1048 |
| 22589 | 3 | | | | | | | Olfr1049 |
| 22590 | 3 | | | | | | | Olfr1051 |
| 22591 | 3 | | | | | | | Olfr1052 |
| 22592 | 3 | | | | | | | Olfr1053 |
| 22593 | 3 | | | | | | | Olfr1054 |
| 22594 | 3 | | | | | | | Olfr1055 |
| 22595 | 3 | | | | | | | Olfr1056 |
| 22596 | 3 | | | | | | | Olfr1057 |
| 22597 | 3 | | | | | | | Olfr1058 |
| 22598 | 3 | | | | | | | Olfr1061 |
| 22599 | 3 | | | | | | | Olfr1062 |
| 22600 | 3 | | | | | | | Olfr1065 |
| 22601 | 3 | | | | | | | Olfr1066 |
| 22602 | 3 | | | | | | | Olfr107 |
| 22603 | 3 | | | | | | | Olfr1076 |
| 22604 | 3 | | | | | | | Olfr1077-ps1 |
| 22605 | 3 | | | | | | | Olfr1079 |
| 22606 | 3 | | | | | | | Olfr108 |
| 22607 | 3 | | | | | | | Olfr1080 |

Fig. 43 - 134

| | | | | | | | | | | | | | | | |
|---|---|---|---|---|---|---|---|---|---|---|---|---|---|---|---|
| 22608 | 3 | | | | | | Olfr1082 | 22693 | 3 | | | | | | Olfr1189 |
| 22609 | 3 | | | | | | Olfr1084 | 22694 | 3 | | | | | | Olfr119 |
| 22610 | 3 | | | | | | Olfr1085 | 22695 | 3 | | | | | | Olfr1193 |
| 22611 | 3 | | | | | | Olfr1086 | 22696 | 3 | | | | | | Olfr1195 |
| 22612 | 3 | | | | | | Olfr1087 | 22697 | 3 | | | | | | Olfr1196 |
| 22613 | 3 | | | | | | Olfr1090 | 22698 | 3 | | | | | | Olfr1197 |
| 22614 | 3 | | | | | | Olfr1093 | 22699 | 3 | | | | | | Olfr1198 |
| 22615 | 3 | | | | | | Olfr1094 | 22700 | 3 | | | | | | Olfr1199 |
| 22616 | 3 | | | | | | Olfr1095 | 22701 | 3 | | | | | | Olfr12 |
| 22617 | 3 | | | | | | Olfr1097 | 22702 | 3 | | | | | | Olfr120 |
| 22618 | 3 | | | | | | Olfr1098 | 22703 | 3 | | | | | | Olfr1200 |
| 22619 | 3 | | | | | | Olfr1099 | 22704 | 3 | | | | | | Olfr1201 |
| 22620 | 3 | | | | | | Olfr11 | 22705 | 3 | | | | | | Olfr1202 |
| 22621 | 3 | | | | | | Olfr110 | 22706 | 3 | | | | | | Olfr1204 |
| 22622 | 3 | | | | | | Olfr1100 | 22707 | 3 | | | | | | Olfr1205 |
| 22623 | 3 | | | | | | Olfr1101 | 22708 | 3 | | | | | | Olfr1206 |
| 22624 | 3 | | | | | | Olfr1102 | 22709 | 3 | | | | | | Olfr1208 |
| 22625 | 3 | | | | | | Olfr1104 | 22710 | 3 | | | | | | Olfr1209 |
| 22626 | 3 | | | | | | Olfr1105 | 22711 | 3 | | | | | | Olfr121 |
| 22627 | 3 | | | | | | Olfr1106 | 22712 | 3 | | | | | | Olfr1211 |
| 22628 | 3 | | | | | | Olfr1107 | 22713 | 3 | | | | | | Olfr1212 |
| 22629 | 3 | | | | | | Olfr1109 | 22714 | 3 | | | | | | Olfr1213 |
| 22630 | 3 | | | | | | Olfr111 | 22715 | 3 | | | | | | Olfr1214 |
| 22631 | 3 | | | | | | Olfr1110 | 22716 | 3 | | | | | | Olfr1215 |
| 22632 | 3 | | | | | | Olfr1111 | 22717 | 3 | | | | | | Olfr1216 |
| 22633 | 3 | | | | | | Olfr1112 | 22718 | 3 | | | | | | Olfr1217 |
| 22634 | 3 | | | | | | Olfr1113 | 22719 | 3 | | | | | | Olfr1218 |
| 22635 | 3 | | | | | | Olfr1115 | 22720 | 3 | | | | | | Olfr1219 |
| 22636 | 3 | | | | | | Olfr1116-ps | 22721 | 3 | | | | | | Olfr122 |
| 22637 | 3 | | | | | | Olfr1118 | 22722 | 3 | | | | | | Olfr1220 |
| 22638 | 3 | | | | | | Olfr112 | 22723 | 3 | | | | | | Olfr1221 |
| 22639 | 3 | | | | | | Olfr1120 | 22724 | 3 | | | | | | Olfr1222 |
| 22640 | 3 | | | | | | Olfr1121 | 22725 | 3 | | | | | | Olfr1223 |
| 22641 | 3 | | | | | | Olfr1122 | 22726 | 3 | | | | | | Olfr1225 |
| 22642 | 3 | | | | | | Olfr1123 | 22727 | 3 | | | | | | Olfr1226 |
| 22643 | 3 | | | | | | Olfr1124 | 22728 | 3 | | | | | | Olfr1228 |
| 22644 | 3 | | | | | | Olfr1126 | 22729 | 3 | | | | | | Olfr1229 |
| 22645 | 3 | | | | | | Olfr1128 | 22730 | 3 | | | | | | Olfr123 |
| 22646 | 3 | | | | | | Olfr1129 | 22731 | 3 | | | | | | Olfr1230 |
| 22647 | 3 | | | | | | Olfr113 | 22732 | 3 | | | | | | Olfr1231 |
| 22648 | 3 | | | | | | Olfr1130 | 22733 | 3 | | | | | | Olfr1232 |
| 22649 | 3 | | | | | | Olfr1131 | 22734 | 3 | | | | | | Olfr1233 |
| 22650 | 3 | | | | | | Olfr1132 | 22735 | 3 | | | | | | Olfr1234 |
| 22651 | 3 | | | | | | Olfr1133 | 22736 | 3 | | | | | | Olfr1238 |
| 22652 | 3 | | | | | | Olfr1134 | 22737 | 3 | | | | | | Olfr1239 |
| 22653 | 3 | | | | | | Olfr1135 | 22738 | 3 | | | | | | Olfr124 |
| 22654 | 3 | | | | | | Olfr1136 | 22739 | 3 | | | | | | Olfr1240 |
| 22655 | 3 | | | | | | Olfr1137 | 22740 | 3 | | | | | | Olfr1241 |
| 22656 | 3 | | | | | | Olfr1138 | 22741 | 3 | | | | | | Olfr1242 |
| 22657 | 3 | | | | | | Olfr114 | 22742 | 3 | | | | | | Olfr1243 |
| 22658 | 3 | | | | | | Olfr1140 | 22743 | 3 | | | | | | Olfr1245 |
| 22659 | 3 | | | | | | Olfr1141 | 22744 | 3 | | | | | | Olfr1246 |
| 22660 | 3 | | | | | | Olfr1143 | 22745 | 3 | | | | | | Olfr1247 |
| 22661 | 3 | | | | | | Olfr1145 | 22746 | 3 | | | | | | Olfr1248 |
| 22662 | 3 | | | | | | Olfr1148 | 22747 | 3 | | | | | | Olfr1249 |
| 22663 | 3 | | | | | | Olfr115 | 22748 | 3 | | | | | | Olfr125 |
| 22664 | 3 | | | | | | Olfr1151 | 22749 | 3 | | | | | | Olfr1250 |
| 22665 | 3 | | | | | | Olfr1152 | 22750 | 3 | | | | | | Olfr1251 |
| 22666 | 3 | | | | | | Olfr1153 | 22751 | 3 | | | | | | Olfr1252 |
| 22667 | 3 | | | | | | Olfr1154 | 22752 | 3 | | | | | | Olfr1253 |
| 22668 | 3 | | | | | | Olfr1156 | 22753 | 3 | | | | | | Olfr1254 |
| 22669 | 3 | | | | | | Olfr1157 | 22754 | 3 | | | | | | Olfr1255 |
| 22670 | 3 | | | | | | Olfr1158 | 22755 | 3 | | | | | | Olfr1256 |
| 22671 | 3 | | | | | | Olfr116 | 22756 | 3 | | | | | | Olfr1257 |
| 22672 | 3 | | | | | | Olfr1160 | 22757 | 3 | | | | | | Olfr1258 |
| 22673 | 3 | | | | | | Olfr1161 | 22758 | 3 | | | | | | Olfr1259 |
| 22674 | 3 | | | | | | Olfr1162 | 22759 | 3 | | | | | | Olfr126 |
| 22675 | 3 | | | | | | Olfr1164 | 22760 | 3 | | | | | | Olfr1260 |
| 22676 | 3 | | | | | | Olfr1166 | 22761 | 3 | | | | | | Olfr1261 |
| 22677 | 3 | | | | | | Olfr1167 | 22762 | 3 | | | | | | Olfr1262 |
| 22678 | 3 | | | | | | Olfr1168 | 22763 | 3 | | | | | | Olfr1263 |
| 22679 | 3 | | | | | | Olfr117 | 22764 | 3 | | | | | | Olfr1264 |
| 22680 | 3 | | | | | | Olfr1170 | 22765 | 3 | | | | | | Olfr1265 |
| 22681 | 3 | | | | | | Olfr1173 | 22766 | 3 | | | | | | Olfr1269 |
| 22682 | 3 | | | | | | Olfr1176 | 22767 | 3 | | | | | | Olfr127 |
| 22683 | 3 | | | | | | Olfr1178 | 22768 | 3 | | | | | | Olfr1270 |
| 22684 | 3 | | | | | | Olfr1179 | 22769 | 3 | | | | | | Olfr1271 |
| 22685 | 3 | | | | | | Olfr118 | 22770 | 3 | | | | | | Olfr1272 |
| 22686 | 3 | | | | | | Olfr1180 | 22771 | 3 | | | | | | Olfr1273-ps |
| 22687 | 3 | | | | | | Olfr1181 | 22772 | 3 | | | | | | Olfr1274-ps |
| 22688 | 3 | | | | | | Olfr1182 | 22773 | 3 | | | | | | Olfr1275 |
| 22689 | 3 | | | | | | Olfr1183 | 22774 | 3 | | | | | | Olfr1276 |
| 22690 | 3 | | | | | | Olfr1184 | 22775 | 3 | | | | | | Olfr1277 |
| 22691 | 3 | | | | | | Olfr1186 | 22776 | 3 | | | | | | Olfr1278 |
| 22692 | 3 | | | | | | Olfr1188 | 22777 | 3 | | | | | | Olfr1279 |

Fig. 43 - 135

| | | | | | | | |
|---|---|---|---|---|---|---|---|
| 22778 | 3 | | | | | | Olfr128 |
| 22779 | 3 | | | | | | Olfr1280 |
| 22780 | 3 | | | | | | Olfr1281 |
| 22781 | 3 | | | | | | Olfr1282 |
| 22782 | 3 | | | | | | Olfr1283 |
| 22783 | 3 | | | | | | Olfr1284 |
| 22784 | 3 | | | | | | Olfr1286 |
| 22785 | 3 | | | | | | Olfr1288 |
| 22786 | 3 | | | | | | Olfr1289 |
| 22787 | 3 | | | | | | Olfr129 |
| 22788 | 3 | | | | | | Olfr1290 |
| 22789 | 3 | | | | | | Olfr1294 |
| 22790 | 3 | | | | | | Olfr1295 |
| 22791 | 3 | | | | | | Olfr1297 |
| 22792 | 3 | | | | | | Olfr1298 |
| 22793 | 3 | | | | | | Olfr1299 |
| 22794 | 3 | | | | | | Olfr13 |
| 22795 | 3 | | | | | | Olfr130 |
| 22796 | 3 | | | | | | Olfr1301 |
| 22797 | 3 | | | | | | Olfr1302 |
| 22798 | 3 | | | | | | Olfr1303 |
| 22799 | 3 | | | | | | Olfr1306 |
| 22800 | 3 | | | | | | Olfr1307 |
| 22801 | 3 | | | | | | Olfr1308 |
| 22802 | 3 | | | | | | Olfr131 |
| 22803 | 3 | | | | | | Olfr1310 |
| 22804 | 3 | | | | | | Olfr1311 |
| 22805 | 3 | | | | | | Olfr1312 |
| 22806 | 3 | | | | | | Olfr1313 |
| 22807 | 3 | | | | | | Olfr1314 |
| 22808 | 3 | | | | | | Olfr1316 |
| 22809 | 3 | | | | | | Olfr1317 |
| 22810 | 3 | | | | | | Olfr1318 |
| 22811 | 3 | | | | | | Olfr132 |
| 22812 | 3 | | | | | | Olfr1321 |
| 22813 | 3 | | | | | | Olfr1322 |
| 22814 | 3 | | | | | | Olfr1323 |
| 22815 | 3 | | | | | | Olfr1324 |
| 22816 | 3 | | | | | | Olfr1325 |
| 22817 | 3 | | | | | | Olfr1328 |
| 22818 | 3 | | | | | | Olfr1329 |
| 22819 | 3 | | | | | | Olfr133 |
| 22820 | 3 | | | | | | Olfr1330 |
| 22821 | 3 | | | | | | Olfr1331 |
| 22822 | 3 | | | | | | Olfr1333 |
| 22823 | 3 | | | | | | Olfr1335 |
| 22824 | 3 | | | | | | Olfr1336 |
| 22825 | 3 | | | | | | Olfr1337 |
| 22826 | 3 | | | | | | Olfr1338 |
| 22827 | 3 | | | | | | Olfr1339 |
| 22828 | 3 | | | | | | Olfr134 |
| 22829 | 3 | | | | | | Olfr1340 |
| 22830 | 3 | | | | | | Olfr1341 |
| 22831 | 3 | | | | | | Olfr1342 |
| 22832 | 3 | | | | | | Olfr1344 |
| 22833 | 3 | | | | | | Olfr1346 |
| 22834 | 3 | | | | | | Olfr1347 |
| 22835 | 3 | | | | | | Olfr1348 |
| 22836 | 3 | | | | | | Olfr1349 |
| 22837 | 3 | | | | | | Olfr135 |
| 22838 | 3 | | | | | | Olfr1350 |
| 22839 | 3 | | | | | | Olfr1351 |
| 22840 | 3 | | | | | | Olfr1352 |
| 22841 | 3 | | | | | | Olfr1353 |
| 22842 | 3 | | | | | | Olfr1354 |
| 22843 | 3 | | | | | | Olfr1355 |
| 22844 | 3 | | | | | | Olfr1356 |
| 22845 | 3 | | | | | | Olfr1357 |
| 22846 | 3 | | | | | | Olfr1359 |
| 22847 | 3 | | | | | | Olfr136 |
| 22848 | 3 | | | | | | Olfr1360 |
| 22849 | 3 | | | | | | Olfr1361 |
| 22850 | 3 | | | | | | Olfr1362 |
| 22851 | 3 | | | | | | Olfr1364 |
| 22852 | 3 | | | | | | Olfr1366 |
| 22853 | 3 | | | | | | Olfr1367 |
| 22854 | 3 | | | | | | Olfr1368 |
| 22855 | 3 | | | | | | Olfr137 |
| 22856 | 3 | | | | | | Olfr1370 |
| 22857 | 3 | | | | | | Olfr1371 |
| 22858 | 3 | | | | | | Olfr1373 |
| 22859 | 3 | | | | | | Olfr1377 |
| 22860 | 3 | | | | | | Olfr1378 |
| 22861 | 3 | | | | | | Olfr138 |
| 22862 | 3 | | | | | | Olfr1380 |
| 22863 | 3 | | | | | | Olfr1382 |
| 22864 | 3 | | | | | | Olfr1383 |
| 22865 | 3 | | | | | | Olfr1384 |
| 22866 | 3 | | | | | | Olfr1385 |
| 22867 | 3 | | | | | | Olfr1386 |
| 22868 | 3 | | | | | | Olfr1388 |
| 22869 | 3 | | | | | | Olfr1389 |
| 22870 | 3 | | | | | | Olfr139 |
| 22871 | 3 | | | | | | Olfr1390 |
| 22872 | 3 | | | | | | Olfr1391 |
| 22873 | 3 | | | | | | Olfr1392 |
| 22874 | 3 | | | | | | Olfr1394 |
| 22875 | 3 | | | | | | Olfr1395 |
| 22876 | 3 | | | | | | Olfr140 |
| 22877 | 3 | | | | | | Olfr1406 |
| 22878 | 3 | | | | | | Olfr1408 |
| 22879 | 3 | | | | | | Olfr1410 |
| 22880 | 3 | | | | | | Olfr1411 |
| 22881 | 3 | | | | | | Olfr1412 |
| 22882 | 3 | | | | | | Olfr1413 |
| 22883 | 3 | | | | | | Olfr1414 |
| 22884 | 3 | | | | | | Olfr1415 |
| 22885 | 3 | | | | | | Olfr1416 |
| 22886 | 3 | | | | | | Olfr1417 |
| 22887 | 3 | | | | | | Olfr1418 |
| 22888 | 3 | | | | | | Olfr142 |
| 22889 | 3 | | | | | | Olfr1423 |
| 22890 | 3 | | | | | | Olfr1424 |
| 22891 | 3 | | | | | | Olfr1425 |
| 22892 | 3 | | | | | | Olfr1426 |
| 22893 | 3 | | | | | | Olfr1427 |
| 22894 | 3 | | | | | | Olfr143 |
| 22895 | 3 | | | | | | Olfr1431 |
| 22896 | 3 | | | | | | Olfr1433 |
| 22897 | 3 | | | | | | Olfr1434 |
| 22898 | 3 | | | | | | Olfr1436 |
| 22899 | 3 | | | | | | Olfr1437 |
| 22900 | 3 | | | | | | Olfr1440 |
| 22901 | 3 | | | | | | Olfr1441 |
| 22902 | 3 | | | | | | Olfr1442 |
| 22903 | 3 | | | | | | Olfr1444 |
| 22904 | 3 | | | | | | Olfr1445 |
| 22905 | 3 | | | | | | Olfr1446 |
| 22906 | 3 | | | | | | Olfr1448 |
| 22907 | 3 | | | | | | Olfr1449 |
| 22908 | 3 | | | | | | Olfr145 |
| 22909 | 3 | | | | | | Olfr1450 |
| 22910 | 3 | | | | | | Olfr1451 |
| 22911 | 3 | | | | | | Olfr1453 |
| 22912 | 3 | | | | | | Olfr1454 |
| 22913 | 3 | | | | | | Olfr1457 |
| 22914 | 3 | | | | | | Olfr1459 |
| 22915 | 3 | | | | | | Olfr146 |
| 22916 | 3 | | | | | | Olfr1461 |
| 22917 | 3 | | | | | | Olfr1462 |
| 22918 | 3 | | | | | | Olfr1463 |
| 22919 | 3 | | | | | | Olfr1465 |
| 22920 | 3 | | | | | | Olfr1466 |
| 22921 | 3 | | | | | | Olfr1467 |
| 22922 | 3 | | | | | | Olfr1469 |
| 22923 | 3 | | | | | | Olfr1471 |
| 22924 | 3 | | | | | | Olfr1472 |
| 22925 | 3 | | | | | | Olfr1474 |
| 22926 | 3 | | | | | | Olfr1475 |
| 22927 | 3 | | | | | | Olfr1477 |
| 22928 | 3 | | | | | | Olfr148 |
| 22929 | 3 | | | | | | Olfr1480 |
| 22930 | 3 | | | | | | Olfr1484 |
| 22931 | 3 | | | | | | Olfr1487 |
| 22932 | 3 | | | | | | Olfr1489 |
| 22933 | 3 | | | | | | Olfr149 |
| 22934 | 3 | | | | | | Olfr1490 |
| 22935 | 3 | | | | | | Olfr1491 |
| 22936 | 3 | | | | | | Olfr1494 |
| 22937 | 3 | | | | | | Olfr1495 |
| 22938 | 3 | | | | | | Olfr1496 |
| 22939 | 3 | | | | | | Olfr1497 |
| 22940 | 3 | | | | | | Olfr1499 |
| 22941 | 3 | | | | | | Olfr15 |
| 22942 | 3 | | | | | | Olfr150 |
| 22943 | 3 | | | | | | Olfr1500 |
| 22944 | 3 | | | | | | Olfr1501 |
| 22945 | 3 | | | | | | Olfr1502 |
| 22946 | 3 | | | | | | Olfr1504 |
| 22947 | 3 | | | | | | Olfr1505 |

Fig. 43 - 136

| | | | | | | | |
|---|---|---|---|---|---|---|---|
| 22948 | 3 | | | | | | Olfr1506 |
| 22949 | 3 | | | | | | Olfr1507 |
| 22950 | 3 | | | | | | Olfr1508 |
| 22951 | 3 | | | | | | Olfr1509 |
| 22952 | 3 | | | | | | Olfr151 |
| 22953 | 3 | | | | | | Olfr1510 |
| 22954 | 3 | | | | | | Olfr1511 |
| 22955 | 3 | | | | | | Olfr1512 |
| 22956 | 3 | | | | | | Olfr1513 |
| 22957 | 3 | | | | | | Olfr152 |
| 22958 | 3 | | | | | | Olfr153 |
| 22959 | 3 | | | | | | Olfr1532-ps1 |
| 22960 | 3 | | | | | | Olfr1535 |
| 22961 | 3 | | | | | | Olfr1537 |
| 22962 | 3 | | | | | | Olfr154 |
| 22963 | 3 | | | | | | Olfr155 |
| 22964 | 3 | | | | | | Olfr156 |
| 22965 | 3 | | | | | | Olfr157 |
| 22966 | 3 | | | | | | Olfr159 |
| 22967 | 3 | | | | | | Olfr16 |
| 22968 | 3 | | | | | | Olfr160 |
| 22969 | 3 | | | | | | Olfr161 |
| 22970 | 3 | | | | | | Olfr166 |
| 22971 | 3 | | | | | | Olfr167 |
| 22972 | 3 | | | | | | Olfr169 |
| 22973 | 3 | | | | | | Olfr17 |
| 22974 | 3 | | | | | | Olfr171 |
| 22975 | 3 | | | | | | Olfr172 |
| 22976 | 3 | | | | | | Olfr173 |
| 22977 | 3 | | | | | | Olfr175-ps1 |
| 22978 | 3 | | | | | | Olfr176 |
| 22979 | 3 | | | | | | Olfr177 |
| 22980 | 3 | | | | | | Olfr178 |
| 22981 | 3 | | | | | | Olfr18 |
| 22982 | 3 | | | | | | Olfr180 |
| 22983 | 3 | | | | | | Olfr181 |
| 22984 | 3 | | | | | | Olfr186 |
| 22985 | 3 | | | | | | Olfr187 |
| 22986 | 3 | | | | | | Olfr19 |
| 22987 | 3 | | | | | | Olfr190 |
| 22988 | 3 | | | | | | Olfr191 |
| 22989 | 3 | | | | | | Olfr192 |
| 22990 | 3 | | | | | | Olfr193 |
| 22991 | 3 | | | | | | Olfr194 |
| 22992 | 3 | | | | | | Olfr195 |
| 22993 | 3 | | | | | | Olfr196 |
| 22994 | 3 | | | | | | Olfr197 |
| 22995 | 3 | | | | | | Olfr198 |
| 22996 | 3 | | | | | | Olfr199 |
| 22997 | 3 | | | | | | Olfr2 |
| 22998 | 3 | | | | | | Olfr201 |
| 22999 | 3 | | | | | | Olfr202 |
| 23000 | 3 | | | | | | Olfr203 |
| 23001 | 3 | | | | | | Olfr206 |
| 23002 | 3 | | | | | | Olfr209 |
| 23003 | 3 | | | | | | Olfr211 |
| 23004 | 3 | | | | | | Olfr212 |
| 23005 | 3 | | | | | | Olfr213 |
| 23006 | 3 | | | | | | Olfr214 |
| 23007 | 3 | | | | | | Olfr215 |
| 23008 | 3 | | | | | | Olfr218 |
| 23009 | 3 | | | | | | Olfr220 |
| 23010 | 3 | | | | | | Olfr222 |
| 23011 | 3 | | | | | | Olfr223 |
| 23012 | 3 | | | | | | Olfr225 |
| 23013 | 3 | | | | | | Olfr228 |
| 23014 | 3 | | | | | | Olfr229 |
| 23015 | 3 | | | | | | Olfr231 |
| 23016 | 3 | | | | | | Olfr235 |
| 23017 | 3 | | | | | | Olfr237-ps1 |
| 23018 | 3 | | | | | | Olfr24 |
| 23019 | 3 | | | | | | Olfr242 |
| 23020 | 3 | | | | | | Olfr243 |
| 23021 | 3 | | | | | | Olfr247 |
| 23022 | 3 | | | | | | Olfr248 |
| 23023 | 3 | | | | | | Olfr25 |
| 23024 | 3 | | | | | | Olfr259 |
| 23025 | 3 | | | | | | Olfr26 |
| 23026 | 3 | | | | | | Olfr262 |
| 23027 | 3 | | | | | | Olfr263 |
| 23028 | 3 | | | | | | Olfr266 |
| 23029 | 3 | | | | | | Olfr27 |
| 23030 | 3 | | | | | | Olfr270 |
| 23031 | 3 | | | | | | Olfr272 |
| 23032 | 3 | | | | | | Olfr273 |
| 23033 | 3 | | | | | | Olfr275 |
| 23034 | 3 | | | | | | Olfr279 |
| 23035 | 3 | | | | | | Olfr281 |
| 23036 | 3 | | | | | | Olfr282 |
| 23037 | 3 | | | | | | Olfr283 |
| 23038 | 3 | | | | | | Olfr284 |
| 23039 | 3 | | | | | | Olfr285 |
| 23040 | 3 | | | | | | Olfr286 |
| 23041 | 3 | | | | | | Olfr288 |
| 23042 | 3 | | | | | | Olfr290 |
| 23043 | 3 | | | | | | Olfr291 |
| 23044 | 3 | | | | | | Olfr292 |
| 23045 | 3 | | | | | | Olfr293 |
| 23046 | 3 | | | | | | Olfr295 |
| 23047 | 3 | | | | | | Olfr297 |
| 23048 | 3 | | | | | | Olfr299 |
| 23049 | 3 | | | | | | Olfr29-ps1 |
| 23050 | 3 | | | | | | Olfr3 |
| 23051 | 3 | | | | | | Olfr30 |
| 23052 | 3 | | | | | | Olfr301 |
| 23053 | 3 | | | | | | Olfr303 |
| 23054 | 3 | | | | | | Olfr304 |
| 23055 | 3 | | | | | | Olfr305 |
| 23056 | 3 | | | | | | Olfr307 |
| 23057 | 3 | | | | | | Olfr308 |
| 23058 | 3 | | | | | | Olfr309 |
| 23059 | 3 | | | | | | Olfr31 |
| 23060 | 3 | | | | | | Olfr310 |
| 23061 | 3 | | | | | | Olfr311 |
| 23062 | 3 | | | | | | Olfr312 |
| 23063 | 3 | | | | | | Olfr313 |
| 23064 | 3 | | | | | | Olfr314 |
| 23065 | 3 | | | | | | Olfr315 |
| 23066 | 3 | | | | | | Olfr316 |
| 23067 | 3 | | | | | | Olfr317 |
| 23068 | 3 | | | | | | Olfr318 |
| 23069 | 3 | | | | | | Olfr319 |
| 23070 | 3 | | | | | | Olfr32 |
| 23071 | 3 | | | | | | Olfr320 |
| 23072 | 3 | | | | | | Olfr323 |
| 23073 | 3 | | | | | | Olfr324 |
| 23074 | 3 | | | | | | Olfr325 |
| 23075 | 3 | | | | | | Olfr33 |
| 23076 | 3 | | | | | | Olfr330 |
| 23077 | 3 | | | | | | Olfr331 |
| 23078 | 3 | | | | | | Olfr332 |
| 23079 | 3 | | | | | | Olfr338 |
| 23080 | 3 | | | | | | Olfr339 |
| 23081 | 3 | | | | | | Olfr340 |
| 23082 | 3 | | | | | | Olfr341 |
| 23083 | 3 | | | | | | Olfr342 |
| 23084 | 3 | | | | | | Olfr344 |
| 23085 | 3 | | | | | | Olfr345 |
| 23086 | 3 | | | | | | Olfr346 |
| 23087 | 3 | | | | | | Olfr347 |
| 23088 | 3 | | | | | | Olfr350 |
| 23089 | 3 | | | | | | Olfr351 |
| 23090 | 3 | | | | | | Olfr352 |
| 23091 | 3 | | | | | | Olfr353 |
| 23092 | 3 | | | | | | Olfr354 |
| 23093 | 3 | | | | | | Olfr356 |
| 23094 | 3 | | | | | | Olfr357 |
| 23095 | 3 | | | | | | Olfr358 |
| 23096 | 3 | | | | | | Olfr360 |
| 23097 | 3 | | | | | | Olfr361 |
| 23098 | 3 | | | | | | Olfr362 |
| 23099 | 3 | | | | | | Olfr365 |
| 23100 | 3 | | | | | | Olfr366 |
| 23101 | 3 | | | | | | Olfr367-ps |
| 23102 | 3 | | | | | | Olfr368 |
| 23103 | 3 | | | | | | Olfr370 |
| 23104 | 3 | | | | | | Olfr371 |
| 23105 | 3 | | | | | | Olfr372 |
| 23106 | 3 | | | | | | Olfr373 |
| 23107 | 3 | | | | | | Olfr374 |
| 23108 | 3 | | | | | | Olfr376 |
| 23109 | 3 | | | | | | Olfr378 |
| 23110 | 3 | | | | | | Olfr38 |
| 23111 | 3 | | | | | | Olfr380 |
| 23112 | 3 | | | | | | Olfr381 |
| 23113 | 3 | | | | | | Olfr382 |
| 23114 | 3 | | | | | | Olfr384 |
| 23115 | 3 | | | | | | Olfr385 |
| 23116 | 3 | | | | | | Olfr389 |
| 23117 | 3 | | | | | | Olfr39 |

Fig. 43 - 137

| | | | | | | | | | | | | | | |
|---|---|---|---|---|---|---|---|---|---|---|---|---|---|---|
| 23118 | 3 | | | | | | Olfr390 | 23203 | 3 | | | | | Olfr5 |
| 23119 | 3 | | | | | | Olfr391-ps | 23204 | 3 | | | | | Olfr50 |
| 23120 | 3 | | | | | | Olfr392 | 23205 | 3 | | | | | Olfr502 |
| 23121 | 3 | | | | | | Olfr393 | 23206 | 3 | | | | | Olfr503 |
| 23122 | 3 | | | | | | Olfr394 | 23207 | 3 | | | | | Olfr504 |
| 23123 | 3 | | | | | | Olfr395 | 23208 | 3 | | | | | Olfr506 |
| 23124 | 3 | | | | | | Olfr397 | 23209 | 3 | | | | | Olfr507 |
| 23125 | 3 | | | | | | Olfr398 | 23210 | 3 | | | | | Olfr508 |
| 23126 | 3 | | | | | | Olfr399 | 23211 | 3 | | | | | Olfr509 |
| 23127 | 3 | | | | | | Olfr401 | 23212 | 3 | | | | | Olfr51 |
| 23128 | 3 | | | | | | Olfr402 | 23213 | 3 | | | | | Olfr510 |
| 23129 | 3 | | | | | | Olfr403 | 23214 | 3 | | | | | Olfr512 |
| 23130 | 3 | | | | | | Olfr406 | 23215 | 3 | | | | | Olfr513 |
| 23131 | 3 | | | | | | Olfr410 | 23216 | 3 | | | | | Olfr514 |
| 23132 | 3 | | | | | | Olfr411 | 23217 | 3 | | | | | Olfr516 |
| 23133 | 3 | | | | | | Olfr412 | 23218 | 3 | | | | | Olfr517 |
| 23134 | 3 | | | | | | Olfr414 | 23219 | 3 | | | | | Olfr518 |
| 23135 | 3 | | | | | | Olfr417 | 23220 | 3 | | | | | Olfr519 |
| 23136 | 3 | | | | | | Olfr418-ps1 | 23221 | 3 | | | | | Olfr52 |
| 23137 | 3 | | | | | | Olfr419 | 23222 | 3 | | | | | Olfr520 |
| 23138 | 3 | | | | | | Olfr420 | 23223 | 3 | | | | | Olfr521 |
| 23139 | 3 | | | | | | Olfr421-ps1 | 23224 | 3 | | | | | Olfr522 |
| 23140 | 3 | | | | | | Olfr424 | 23225 | 3 | | | | | Olfr523 |
| 23141 | 3 | | | | | | Olfr426 | 23226 | 3 | | | | | Olfr524 |
| 23142 | 3 | | | | | | Olfr427 | 23227 | 3 | | | | | Olfr525 |
| 23143 | 3 | | | | | | Olfr429 | 23228 | 3 | | | | | Olfr527 |
| 23144 | 3 | | | | | | Olfr43 | 23229 | 3 | | | | | Olfr53 |
| 23145 | 3 | | | | | | Olfr430 | 23230 | 3 | | | | | Olfr530 |
| 23146 | 3 | | | | | | Olfr432 | 23231 | 3 | | | | | Olfr533 |
| 23147 | 3 | | | | | | Olfr433 | 23232 | 3 | | | | | Olfr535 |
| 23148 | 3 | | | | | | Olfr434 | 23233 | 3 | | | | | Olfr536 |
| 23149 | 3 | | | | | | Olfr435 | 23234 | 3 | | | | | Olfr538 |
| 23150 | 3 | | | | | | Olfr437 | 23235 | 3 | | | | | Olfr539 |
| 23151 | 3 | | | | | | Olfr44 | 23236 | 3 | | | | | Olfr54 |
| 23152 | 3 | | | | | | Olfr441 | 23237 | 3 | | | | | Olfr541 |
| 23153 | 3 | | | | | | Olfr444 | 23238 | 3 | | | | | Olfr544 |
| 23154 | 3 | | | | | | Olfr446 | 23239 | 3 | | | | | Olfr545 |
| 23155 | 3 | | | | | | Olfr447 | 23240 | 3 | | | | | Olfr547 |
| 23156 | 3 | | | | | | Olfr448 | 23241 | 3 | | | | | Olfr549 |
| 23157 | 3 | | | | | | Olfr449 | 23242 | 3 | | | | | Olfr55 |
| 23158 | 3 | | | | | | Olfr45 | 23243 | 3 | | | | | Olfr551 |
| 23159 | 3 | | | | | | Olfr450 | 23244 | 3 | | | | | Olfr553 |
| 23160 | 3 | | | | | | Olfr452 | 23245 | 3 | | | | | Olfr554 |
| 23161 | 3 | | | | | | Olfr453 | 23246 | 3 | | | | | Olfr555 |
| 23162 | 3 | | | | | | Olfr455 | 23247 | 3 | | | | | Olfr556 |
| 23163 | 3 | | | | | | Olfr456 | 23248 | 3 | | | | | Olfr557 |
| 23164 | 3 | | | | | | Olfr457 | 23249 | 3 | | | | | Olfr559 |
| 23165 | 3 | | | | | | Olfr458 | 23250 | 3 | | | | | Olfr560 |
| 23166 | 3 | | | | | | Olfr459 | 23251 | 3 | | | | | Olfr561 |
| 23167 | 3 | | | | | | Olfr46 | 23252 | 3 | | | | | Olfr564 |
| 23168 | 3 | | | | | | Olfr460 | 23253 | 3 | | | | | Olfr566 |
| 23169 | 3 | | | | | | Olfr461 | 23254 | 3 | | | | | Olfr568 |
| 23170 | 3 | | | | | | Olfr462 | 23255 | 3 | | | | | Olfr57 |
| 23171 | 3 | | | | | | Olfr463 | 23256 | 3 | | | | | Olfr570 |
| 23172 | 3 | | | | | | Olfr464 | 23257 | 3 | | | | | Olfr571 |
| 23173 | 3 | | | | | | Olfr466 | 23258 | 3 | | | | | Olfr572 |
| 23174 | 3 | | | | | | Olfr467 | 23259 | 3 | | | | | Olfr574 |
| 23175 | 3 | | | | | | Olfr469 | 23260 | 3 | | | | | Olfr575 |
| 23176 | 3 | | | | | | Olfr470 | 23261 | 3 | | | | | Olfr576 |
| 23177 | 3 | | | | | | Olfr472 | 23262 | 3 | | | | | Olfr577 |
| 23178 | 3 | | | | | | Olfr473 | 23263 | 3 | | | | | Olfr578 |
| 23179 | 3 | | | | | | Olfr474 | 23264 | 3 | | | | | Olfr58 |
| 23180 | 3 | | | | | | Olfr476 | 23265 | 3 | | | | | Olfr582 |
| 23181 | 3 | | | | | | Olfr477 | 23266 | 3 | | | | | Olfr583 |
| 23182 | 3 | | | | | | Olfr478 | 23267 | 3 | | | | | Olfr584 |
| 23183 | 3 | | | | | | Olfr479 | 23268 | 3 | | | | | Olfr585 |
| 23184 | 3 | | | | | | Olfr48 | 23269 | 3 | | | | | Olfr586 |
| 23185 | 3 | | | | | | Olfr480 | 23270 | 3 | | | | | Olfr589 |
| 23186 | 3 | | | | | | Olfr481 | 23271 | 3 | | | | | Olfr59 |
| 23187 | 3 | | | | | | Olfr482 | 23272 | 3 | | | | | Olfr591 |
| 23188 | 3 | | | | | | Olfr483 | 23273 | 3 | | | | | Olfr592 |
| 23189 | 3 | | | | | | Olfr484 | 23274 | 3 | | | | | Olfr593 |
| 23190 | 3 | | | | | | Olfr485 | 23275 | 3 | | | | | Olfr594 |
| 23191 | 3 | | | | | | Olfr486 | 23276 | 3 | | | | | Olfr597 |
| 23192 | 3 | | | | | | Olfr487 | 23277 | 3 | | | | | Olfr598 |
| 23193 | 3 | | | | | | Olfr488 | 23278 | 3 | | | | | Olfr599 |
| 23194 | 3 | | | | | | Olfr49 | 23279 | 3 | | | | | Olfr60 |
| 23195 | 3 | | | | | | Olfr490 | 23280 | 3 | | | | | Olfr600 |
| 23196 | 3 | | | | | | Olfr491 | 23281 | 3 | | | | | Olfr601 |
| 23197 | 3 | | | | | | Olfr492 | 23282 | 3 | | | | | Olfr605 |
| 23198 | 3 | | | | | | Olfr493 | 23283 | 3 | | | | | Olfr606 |
| 23199 | 3 | | | | | | Olfr494 | 23284 | 3 | | | | | Olfr608 |
| 23200 | 3 | | | | | | Olfr495 | 23285 | 3 | | | | | Olfr609 |
| 23201 | 3 | | | | | | Olfr497 | 23286 | 3 | | | | | Olfr61 |
| 23202 | 3 | | | | | | Olfr498 | 23287 | 3 | | | | | Olfr610 |

Fig. 43 - 138

| | | | | | | | |
|---|---|---|---|---|---|---|---|
| 23288 | 3 | | | | | | Olfr611 |
| 23289 | 3 | | | | | | Olfr612 |
| 23290 | 3 | | | | | | Olfr613 |
| 23291 | 3 | | | | | | Olfr615 |
| 23292 | 3 | | | | | | Olfr616 |
| 23293 | 3 | | | | | | Olfr617 |
| 23294 | 3 | | | | | | Olfr618 |
| 23295 | 3 | | | | | | Olfr619 |
| 23296 | 3 | | | | | | Olfr62 |
| 23297 | 3 | | | | | | Olfr620 |
| 23298 | 3 | | | | | | Olfr622 |
| 23299 | 3 | | | | | | Olfr623 |
| 23300 | 3 | | | | | | Olfr624 |
| 23301 | 3 | | | | | | Olfr628 |
| 23302 | 3 | | | | | | Olfr629 |
| 23303 | 3 | | | | | | Olfr63 |
| 23304 | 3 | | | | | | Olfr630 |
| 23305 | 3 | | | | | | Olfr631 |
| 23306 | 3 | | | | | | Olfr632 |
| 23307 | 3 | | | | | | Olfr633 |
| 23308 | 3 | | | | | | Olfr635 |
| 23309 | 3 | | | | | | Olfr638 |
| 23310 | 3 | | | | | | Olfr639 |
| 23311 | 3 | | | | | | Olfr64 |
| 23312 | 3 | | | | | | Olfr640 |
| 23313 | 3 | | | | | | Olfr641 |
| 23314 | 3 | | | | | | Olfr642 |
| 23315 | 3 | | | | | | Olfr643 |
| 23316 | 3 | | | | | | Olfr644 |
| 23317 | 3 | | | | | | Olfr645 |
| 23318 | 3 | | | | | | Olfr646 |
| 23319 | 3 | | | | | | Olfr648 |
| 23320 | 3 | | | | | | Olfr649 |
| 23321 | 3 | | | | | | Olfr65 |
| 23322 | 3 | | | | | | Olfr651 |
| 23323 | 3 | | | | | | Olfr652 |
| 23324 | 3 | | | | | | Olfr653 |
| 23325 | 3 | | | | | | Olfr654 |
| 23326 | 3 | | | | | | Olfr655 |
| 23327 | 3 | | | | | | Olfr656 |
| 23328 | 3 | | | | | | Olfr657 |
| 23329 | 3 | | | | | | Olfr658 |
| 23330 | 3 | | | | | | Olfr659 |
| 23331 | 3 | | | | | | Olfr66 |
| 23332 | 3 | | | | | | Olfr661 |
| 23333 | 3 | | | | | | Olfr663 |
| 23334 | 3 | | | | | | Olfr665 |
| 23335 | 3 | | | | | | Olfr666 |
| 23336 | 3 | | | | | | Olfr667 |
| 23337 | 3 | | | | | | Olfr668 |
| 23338 | 3 | | | | | | Olfr669 |
| 23339 | 3 | | | | | | Olfr67 |
| 23340 | 3 | | | | | | Olfr670 |
| 23341 | 3 | | | | | | Olfr671 |
| 23342 | 3 | | | | | | Olfr672 |
| 23343 | 3 | | | | | | Olfr675 |
| 23344 | 3 | | | | | | Olfr676 |
| 23345 | 3 | | | | | | Olfr677 |
| 23346 | 3 | | | | | | Olfr678 |
| 23347 | 3 | | | | | | Olfr679 |
| 23348 | 3 | | | | | | Olfr68 |
| 23349 | 3 | | | | | | Olfr681 |
| 23350 | 3 | | | | | | Olfr683 |
| 23351 | 3 | | | | | | Olfr684 |
| 23352 | 3 | | | | | | Olfr685 |
| 23353 | 3 | | | | | | Olfr686 |
| 23354 | 3 | | | | | | Olfr688 |
| 23355 | 3 | | | | | | Olfr689 |
| 23356 | 3 | | | | | | Olfr69 |
| 23357 | 3 | | | | | | Olfr690 |
| 23358 | 3 | | | | | | Olfr691 |
| 23359 | 3 | | | | | | Olfr692 |
| 23360 | 3 | | | | | | Olfr693 |
| 23361 | 3 | | | | | | Olfr694 |
| 23362 | 3 | | | | | | Olfr695 |
| 23363 | 3 | | | | | | Olfr697 |
| 23364 | 3 | | | | | | Olfr698 |
| 23365 | 3 | | | | | | Olfr699 |
| 23366 | 3 | | | | | | Olfr70 |
| 23367 | 3 | | | | | | Olfr700 |
| 23368 | 3 | | | | | | Olfr701 |
| 23369 | 3 | | | | | | Olfr702 |
| 23370 | 3 | | | | | | Olfr703 |
| 23371 | 3 | | | | | | Olfr704 |
| 23372 | 3 | | | | | | Olfr705 |
| 23373 | 3 | | | | | | Olfr706 |
| 23374 | 3 | | | | | | Olfr707 |
| 23375 | 3 | | | | | | Olfr71 |
| 23376 | 3 | | | | | | Olfr710 |
| 23377 | 3 | | | | | | Olfr711 |
| 23378 | 3 | | | | | | Olfr713 |
| 23379 | 3 | | | | | | Olfr714 |
| 23380 | 3 | | | | | | Olfr715 |
| 23381 | 3 | | | | | | Olfr716 |
| 23382 | 3 | | | | | | Olfr720 |
| 23383 | 3 | | | | | | Olfr722 |
| 23384 | 3 | | | | | | Olfr723 |
| 23385 | 3 | | | | | | Olfr724 |
| 23386 | 3 | | | | | | Olfr725 |
| 23387 | 3 | | | | | | Olfr726 |
| 23388 | 3 | | | | | | Olfr727 |
| 23389 | 3 | | | | | | Olfr728 |
| 23390 | 3 | | | | | | Olfr729 |
| 23391 | 3 | | | | | | Olfr73 |
| 23392 | 3 | | | | | | Olfr730 |
| 23393 | 3 | | | | | | Olfr731 |
| 23394 | 3 | | | | | | Olfr732 |
| 23395 | 3 | | | | | | Olfr733 |
| 23396 | 3 | | | | | | Olfr734 |
| 23397 | 3 | | | | | | Olfr735 |
| 23398 | 3 | | | | | | Olfr736 |
| 23399 | 3 | | | | | | Olfr738 |
| 23400 | 3 | | | | | | Olfr739 |
| 23401 | 3 | | | | | | Olfr740 |
| 23402 | 3 | | | | | | Olfr741 |
| 23403 | 3 | | | | | | Olfr742 |
| 23404 | 3 | | | | | | Olfr743 |
| 23405 | 3 | | | | | | Olfr745 |
| 23406 | 3 | | | | | | Olfr746 |
| 23407 | 3 | | | | | | Olfr747 |
| 23408 | 3 | | | | | | Olfr748 |
| 23409 | 3 | | | | | | Olfr749 |
| 23410 | 3 | | | | | | Olfr750 |
| 23411 | 3 | | | | | | Olfr75-ps1 |
| 23412 | 3 | | | | | | Olfr76 |
| 23413 | 3 | | | | | | Olfr761 |
| 23414 | 3 | | | | | | Olfr763 |
| 23415 | 3 | | | | | | Olfr765 |
| 23416 | 3 | | | | | | Olfr767 |
| 23417 | 3 | | | | | | Olfr768 |
| 23418 | 3 | | | | | | Olfr769 |
| 23419 | 3 | | | | | | Olfr770 |
| 23420 | 3 | | | | | | Olfr771 |
| 23421 | 3 | | | | | | Olfr772 |
| 23422 | 3 | | | | | | Olfr773 |
| 23423 | 3 | | | | | | Olfr774 |
| 23424 | 3 | | | | | | Olfr775 |
| 23425 | 3 | | | | | | Olfr776 |
| 23426 | 3 | | | | | | Olfr777 |
| 23427 | 3 | | | | | | Olfr780 |
| 23428 | 3 | | | | | | Olfr781 |
| 23429 | 3 | | | | | | Olfr784 |
| 23430 | 3 | | | | | | Olfr786 |
| 23431 | 3 | | | | | | Olfr788 |
| 23432 | 3 | | | | | | Olfr790 |
| 23433 | 3 | | | | | | Olfr791 |
| 23434 | 3 | | | | | | Olfr792 |
| 23435 | 3 | | | | | | Olfr794 |
| 23436 | 3 | | | | | | Olfr796 |
| 23437 | 3 | | | | | | Olfr798 |
| 23438 | 3 | | | | | | Olfr799 |
| 23439 | 3 | | | | | | Olfr8 |
| 23440 | 3 | | | | | | Olfr800 |
| 23441 | 3 | | | | | | Olfr801 |
| 23442 | 3 | | | | | | Olfr802 |
| 23443 | 3 | | | | | | Olfr803 |
| 23444 | 3 | | | | | | Olfr805 |
| 23445 | 3 | | | | | | Olfr806 |
| 23446 | 3 | | | | | | Olfr807 |
| 23447 | 3 | | | | | | Olfr808 |
| 23448 | 3 | | | | | | Olfr809 |
| 23449 | 3 | | | | | | Olfr810 |
| 23450 | 3 | | | | | | Olfr811 |
| 23451 | 3 | | | | | | Olfr812 |
| 23452 | 3 | | | | | | Olfr813 |
| 23453 | 3 | | | | | | Olfr814 |
| 23454 | 3 | | | | | | Olfr815 |
| 23455 | 3 | | | | | | Olfr816 |
| 23456 | 3 | | | | | | Olfr818 |
| 23457 | 3 | | | | | | Olfr819 |

Fig. 43 - 139

| | | | | | | | |
|---|---|---|---|---|---|---|---|
| 23458 | 3 | | | | | | Olfr820 |
| 23459 | 3 | | | | | | Olfr821 |
| 23460 | 3 | | | | | | Olfr822 |
| 23461 | 3 | | | | | | Olfr824 |
| 23462 | 3 | | | | | | Olfr825 |
| 23463 | 3 | | | | | | Olfr826 |
| 23464 | 3 | | | | | | Olfr827 |
| 23465 | 3 | | | | | | Olfr828 |
| 23466 | 3 | | | | | | Olfr829 |
| 23467 | 3 | | | | | | Olfr830 |
| 23468 | 3 | | | | | | Olfr832 |
| 23469 | 3 | | | | | | Olfr834 |
| 23470 | 3 | | | | | | Olfr835 |
| 23471 | 3 | | | | | | Olfr836 |
| 23472 | 3 | | | | | | Olfr837 |
| 23473 | 3 | | | | | | Olfr843 |
| 23474 | 3 | | | | | | Olfr845 |
| 23475 | 3 | | | | | | Olfr846 |
| 23476 | 3 | | | | | | Olfr847 |
| 23477 | 3 | | | | | | Olfr849 |
| 23478 | 3 | | | | | | Olfr850 |
| 23479 | 3 | | | | | | Olfr851 |
| 23480 | 3 | | | | | | Olfr853 |
| 23481 | 3 | | | | | | Olfr854 |
| 23482 | 3 | | | | | | Olfr855 |
| 23483 | 3 | | | | | | Olfr856-ps1 |
| 23484 | 3 | | | | | | Olfr857 |
| 23485 | 3 | | | | | | Olfr859 |
| 23486 | 3 | | | | | | Olfr860 |
| 23487 | 3 | | | | | | Olfr862 |
| 23488 | 3 | | | | | | Olfr866 |
| 23489 | 3 | | | | | | Olfr867 |
| 23490 | 3 | | | | | | Olfr868 |
| 23491 | 3 | | | | | | Olfr869 |
| 23492 | 3 | | | | | | Olfr870 |
| 23493 | 3 | | | | | | Olfr871 |
| 23494 | 3 | | | | | | Olfr872 |
| 23495 | 3 | | | | | | Olfr873 |
| 23496 | 3 | | | | | | Olfr874 |
| 23497 | 3 | | | | | | Olfr875 |
| 23498 | 3 | | | | | | Olfr876 |
| 23499 | 3 | | | | | | Olfr877 |
| 23500 | 3 | | | | | | Olfr881 |
| 23501 | 3 | | | | | | Olfr883 |
| 23502 | 3 | | | | | | Olfr884 |
| 23503 | 3 | | | | | | Olfr885 |
| 23504 | 3 | | | | | | Olfr887 |
| 23505 | 3 | | | | | | Olfr888 |
| 23506 | 3 | | | | | | Olfr889 |
| 23507 | 3 | | | | | | Olfr890 |
| 23508 | 3 | | | | | | Olfr891 |
| 23509 | 3 | | | | | | Olfr893 |
| 23510 | 3 | | | | | | Olfr894 |
| 23511 | 3 | | | | | | Olfr895 |
| 23512 | 3 | | | | | | Olfr898 |
| 23513 | 3 | | | | | | Olfr899 |
| 23514 | 3 | | | | | | Olfr9 |
| 23515 | 3 | | | | | | Olfr90 |
| 23516 | 3 | | | | | | Olfr900 |
| 23517 | 3 | | | | | | Olfr901 |
| 23518 | 3 | | | | | | Olfr902 |
| 23519 | 3 | | | | | | Olfr904 |
| 23520 | 3 | | | | | | Olfr905 |
| 23521 | 3 | | | | | | Olfr906 |
| 23522 | 3 | | | | | | Olfr907 |
| 23523 | 3 | | | | | | Olfr908 |
| 23524 | 3 | | | | | | Olfr91 |
| 23525 | 3 | | | | | | Olfr910 |
| 23526 | 3 | | | | | | Olfr911-ps1 |
| 23527 | 3 | | | | | | Olfr912 |
| 23528 | 3 | | | | | | Olfr913 |
| 23529 | 3 | | | | | | Olfr914 |
| 23530 | 3 | | | | | | Olfr915 |
| 23531 | 3 | | | | | | Olfr916 |
| 23532 | 3 | | | | | | Olfr917 |
| 23533 | 3 | | | | | | Olfr918 |
| 23534 | 3 | | | | | | Olfr919 |
| 23535 | 3 | | | | | | Olfr92 |
| 23536 | 3 | | | | | | Olfr921 |
| 23537 | 3 | | | | | | Olfr922 |
| 23538 | 3 | | | | | | Olfr923 |
| 23539 | 3 | | | | | | Olfr924 |
| 23540 | 3 | | | | | | Olfr926 |
| 23541 | 3 | | | | | | Olfr930 |
| 23542 | 3 | | | | | | Olfr933 |
| 23543 | 3 | | | | | | Olfr934 |
| 23544 | 3 | | | | | | Olfr935 |
| 23545 | 3 | | | | | | Olfr936 |
| 23546 | 3 | | | | | | Olfr937 |
| 23547 | 3 | | | | | | Olfr938 |
| 23548 | 3 | | | | | | Olfr94 |
| 23549 | 3 | | | | | | Olfr943 |
| 23550 | 3 | | | | | | Olfr944 |
| 23551 | 3 | | | | | | Olfr945 |
| 23552 | 3 | | | | | | Olfr947-ps1 |
| 23553 | 3 | | | | | | Olfr948 |
| 23554 | 3 | | | | | | Olfr95 |
| 23555 | 3 | | | | | | Olfr951 |
| 23556 | 3 | | | | | | Olfr952 |
| 23557 | 3 | | | | | | Olfr954 |
| 23558 | 3 | | | | | | Olfr955 |
| 23559 | 3 | | | | | | Olfr957 |
| 23560 | 3 | | | | | | Olfr958 |
| 23561 | 3 | | | | | | Olfr959 |
| 23562 | 3 | | | | | | Olfr96 |
| 23563 | 3 | | | | | | Olfr960 |
| 23564 | 3 | | | | | | Olfr961 |
| 23565 | 3 | | | | | | Olfr963 |
| 23566 | 3 | | | | | | Olfr965 |
| 23567 | 3 | | | | | | Olfr967 |
| 23568 | 3 | | | | | | Olfr968 |
| 23569 | 3 | | | | | | Olfr969 |
| 23570 | 3 | | | | | | Olfr97 |
| 23571 | 3 | | | | | | Olfr970 |
| 23572 | 3 | | | | | | Olfr971 |
| 23573 | 3 | | | | | | Olfr972 |
| 23574 | 3 | | | | | | Olfr974 |
| 23575 | 3 | | | | | | Olfr975 |
| 23576 | 3 | | | | | | Olfr976 |
| 23577 | 3 | | | | | | Olfr978 |
| 23578 | 3 | | | | | | Olfr979 |
| 23579 | 3 | | | | | | Olfr98 |
| 23580 | 3 | | | | | | Olfr980 |
| 23581 | 3 | | | | | | Olfr981 |
| 23582 | 3 | | | | | | Olfr982 |
| 23583 | 3 | | | | | | Olfr983 |
| 23584 | 3 | | | | | | Olfr984 |
| 23585 | 3 | | | | | | Olfr986 |
| 23586 | 3 | | | | | | Olfr987 |
| 23587 | 3 | | | | | | Olfr988 |
| 23588 | 3 | | | | | | Olfr99 |
| 23589 | 3 | | | | | | Olfr992 |
| 23590 | 3 | | | | | | Olfr993 |
| 23591 | 3 | | | | | | Olfr994 |
| 23592 | 3 | | | | | | Olfr995 |
| 23593 | 3 | | | | | | Olfr996 |
| 23594 | 3 | | | | | | Olfr998 |
| 23595 | 3 | | | | | | Olig2 |
| 23596 | 3 | | | | | | Olr1 |
| 23597 | 3 | | | | | | Omt2a |
| 23598 | 3 | | | | | | Oog1 |
| 23599 | 3 | | | | | | Oog2 |
| 23600 | 3 | | | | | | Oosp3 |
| 23601 | 3 | | | | | | Opa1 |
| 23602 | 3 | | | | | | Opalin |
| 23603 | 3 | | | | | | Opcml |
| 23604 | 3 | | | | | | Oprk1 |
| 23605 | 3 | | | | | | Oprl1 |
| 23606 | 3 | | | | | | Optc |
| 23607 | 3 | | | | | | Optn |
| 23608 | 3 | | | | | | Oxsm |
| 23609 | 3 | | | | | | Oxsr1 |
| 23610 | 3 | | | | | | Pcdha9 |
| 23611 | 3 | | | | | | Pcdhga2 |
| 23612 | 3 | | | | | | Pex12 |
| 23613 | 3 | | | | | | Pla2g4a |
| 23614 | 3 | | | | | | Prl3d1 |
| 23615 | 3 | | | | | | Prop1 |
| 23616 | 3 | | | | | | Prox1 |
| 23617 | 3 | | | | | | Prss55 |
| 23618 | 3 | | | | | | Prtg |
| 23619 | 3 | | | | | | Psg25 |
| 23620 | 3 | | | | | | Psg27 |
| 23621 | 3 | | | | | | Rgl1 |
| 23622 | 3 | | | | | | Rimkla |
| 23623 | 3 | | | | | | Rnasel |
| 23624 | 3 | | | | | | Rph3a |
| 23625 | 3 | | | | | | Scgb2b23-ps |
| 23626 | 3 | | | | | | Scgb2b24 |
| 23627 | 3 | | | | | | Scgb2b3 |

Fig. 43 - 140

| | | | | | | | | | | | | | | | |
|---|---|---|---|---|---|---|---|---|---|---|---|---|---|---|---|
| 23628 | 3 | | | | | Scgb2b7 | | 23713 | 3 | | | | | Vmn1r166 |
| 23629 | 3 | | | | | Scgn | | 23714 | 3 | | | | | Vmn1r167 |
| 23630 | 3 | | | | | Scn3b | | 23715 | 3 | | | | | Vmn1r168 |
| 23631 | 3 | | | | | Slc5a9 | | 23716 | 3 | | | | | Vmn1r169 |
| 23632 | 3 | | | | | Slc6a1 | | 23717 | 3 | | | | | Vmn1r17 |
| 23633 | 3 | | | | | Slc6a18 | | 23718 | 3 | | | | | Vmn1r170 |
| 23634 | 3 | | | | | Smc6 | | 23719 | 3 | | | | | Vmn1r171 |
| 23635 | 3 | | | | | Snord11 | | 23720 | 3 | | | | | Vmn1r172 |
| 23636 | 3 | | | | | Snord116l1 | | 23721 | 3 | | | | | Vmn1r173 |
| 23637 | 3 | | | | | Snord12 | | 23722 | 3 | | | | | Vmn1r174 |
| 23638 | 3 | | | | | Snord123 | | 23723 | 3 | | | | | Vmn1r175 |
| 23639 | 3 | | | | | Snord14c | | 23724 | 3 | | | | | Vmn1r176 |
| 23640 | 3 | | | | | Snord14d | | 23725 | 3 | | | | | Vmn1r177 |
| 23641 | 3 | | | | | Snord16a | | 23726 | 3 | | | | | Vmn1r178 |
| 23642 | 3 | | | | | Snord19 | | 23727 | 3 | | | | | Vmn1r179 |
| 23643 | 3 | | | | | Snord1a | | 23728 | 3 | | | | | Vmn1r18 |
| 23644 | 3 | | | | | Snord32a | | 23729 | 3 | | | | | Vmn1r180 |
| 23645 | 3 | | | | | Snord33 | | 23730 | 3 | | | | | Vmn1r181 |
| 23646 | 3 | | | | | Snord34 | | 23731 | 3 | | | | | Vmn1r183 |
| 23647 | 3 | | | | | Snord38a | | 23732 | 3 | | | | | Vmn1r184 |
| 23648 | 3 | | | | | Snord43 | | 23733 | 3 | | | | | Vmn1r185 |
| 23649 | 3 | | | | | Snord49a | | 23734 | 3 | | | | | Vmn1r186 |
| 23650 | 3 | | | | | Snord49b | | 23735 | 3 | | | | | Vmn1r187 |
| 23651 | 3 | | | | | Snord4a | | 23736 | 3 | | | | | Vmn1r188 |
| 23652 | 3 | | | | | Snord52 | | 23737 | 3 | | | | | Vmn1r189 |
| 23653 | 3 | | | | | Snord53 | | 23738 | 3 | | | | | Vmn1r19 |
| 23654 | 3 | | | | | Snord55 | | 23739 | 3 | | | | | Vmn1r191 |
| 23655 | 3 | | | | | Snord57 | | 23740 | 3 | | | | | Vmn1r192 |
| 23656 | 3 | | | | | Snord58b | | 23741 | 3 | | | | | Vmn1r193 |
| 23657 | 3 | | | | | Snord61 | | 23742 | 3 | | | | | Vmn1r194 |
| 23658 | 3 | | | | | Snord64 | | 23743 | 3 | | | | | Vmn1r195 |
| 23659 | 3 | | | | | Snord65 | | 23744 | 3 | | | | | Vmn1r196 |
| 23660 | 3 | | | | | Snord66 | | 23745 | 3 | | | | | Vmn1r197 |
| 23661 | 3 | | | | | Snord67 | | 23746 | 3 | | | | | Vmn1r198 |
| 23662 | 3 | | | | | Snord68 | | 23747 | 3 | | | | | Vmn1r199 |
| 23663 | 3 | | | | | Snord69 | | 23748 | 3 | | | | | Vmn1r2 |
| 23664 | 3 | | | | | Snord70 | | 23749 | 3 | | | | | Vmn1r20 |
| 23665 | 3 | | | | | Snord72 | | 23750 | 3 | | | | | Vmn1r200 |
| 23666 | 3 | | | | | Snord73a | | 23751 | 3 | | | | | Vmn1r201 |
| 23667 | 3 | | | | | Snord8 | | 23752 | 3 | | | | | Vmn1r202 |
| 23668 | 3 | | | | | Snord82 | | 23753 | 3 | | | | | Vmn1r203 |
| 23669 | 3 | | | | | Snord83b | | 23754 | 3 | | | | | Vmn1r204 |
| 23670 | 3 | | | | | Snord87 | | 23755 | 3 | | | | | Vmn1r205 |
| 23671 | 3 | | | | | Snord88a | | 23756 | 3 | | | | | Vmn1r206 |
| 23672 | 3 | | | | | Snord88c | | 23757 | 3 | | | | | Vmn1r207-ps |
| 23673 | 3 | | | | | Snord89 | | 23758 | 3 | | | | | Vmn1r208 |
| 23674 | 3 | | | | | Snord90 | | 23759 | 3 | | | | | Vmn1r209 |
| 23675 | 3 | | | | | Snord91a | | 23760 | 3 | | | | | Vmn1r21 |
| 23676 | 3 | | | | | Snord92 | | 23761 | 3 | | | | | Vmn1r210 |
| 23677 | 3 | | | | | Snord93 | | 23762 | 3 | | | | | Vmn1r211 |
| 23678 | 3 | | | | | Snord95 | | 23763 | 3 | | | | | Vmn1r212 |
| 23679 | 3 | | | | | Snord96a | | 23764 | 3 | | | | | Vmn1r213 |
| 23680 | 3 | | | | | Snord98 | | 23765 | 3 | | | | | Vmn1r214 |
| 23681 | 3 | | | | | Snord99 | | 23766 | 3 | | | | | Vmn1r215 |
| 23682 | 3 | | | | | Snph | | 23767 | 3 | | | | | Vmn1r216 |
| 23683 | 3 | | | | | Speer4f | | 23768 | 3 | | | | | Vmn1r218 |
| 23684 | 3 | | | | | Spink3 | | 23769 | 3 | | | | | Vmn1r219 |
| 23685 | 3 | | | | | Spink4 | | 23770 | 3 | | | | | Vmn1r22 |
| 23686 | 3 | | | | | Spink6 | | 23771 | 3 | | | | | Vmn1r220 |
| 23687 | 3 | | | | | Stac | | 23772 | 3 | | | | | Vmn1r221 |
| 23688 | 3 | | | | | Stoml3 | | 23773 | 3 | | | | | Vmn1r222 |
| 23689 | 3 | | | | | Syt4 | | 23774 | 3 | | | | | Vmn1r223 |
| 23690 | 3 | | | | | Taar5 | | 23775 | 3 | | | | | Vmn1r224 |
| 23691 | 3 | | | | | Taar8b | | 23776 | 3 | | | | | Vmn1r225 |
| 23692 | 3 | | | | | Tagln | | 23777 | 3 | | | | | Vmn1r226 |
| 23693 | 3 | | | | | Tatdn2 | | 23778 | 3 | | | | | Vmn1r227 |
| 23694 | 3 | | | | | Tdrd12 | | 23779 | 3 | | | | | Vmn1r228 |
| 23695 | 3 | | | | | Tdrd6 | | 23780 | 3 | | | | | Vmn1r229 |
| 23696 | 3 | | | | | Tex28 | | 23781 | 3 | | | | | Vmn1r23 |
| 23697 | 3 | | | | | Tmem234 | | 23782 | 3 | | | | | Vmn1r230 |
| 23698 | 3 | | | | | Tnfrsf1a | | 23783 | 3 | | | | | Vmn1r231 |
| 23699 | 3 | | | | | Ttc29 | | 23784 | 3 | | | | | Vmn1r232 |
| 23700 | 3 | | | | | Unc13c | | 23785 | 3 | | | | | Vmn1r233 |
| 23701 | 3 | | | | | Vmn1r119 | | 23786 | 3 | | | | | Vmn1r234 |
| 23702 | 3 | | | | | Vmn1r121 | | 23787 | 3 | | | | | Vmn1r235 |
| 23703 | 3 | | | | | Vmn1r122 | | 23788 | 3 | | | | | Vmn1r236 |
| 23704 | 3 | | | | | Vmn1r151 | | 23789 | 3 | | | | | Vmn1r237 |
| 23705 | 3 | | | | | Vmn1r152 | | 23790 | 3 | | | | | Vmn1r238 |
| 23706 | 3 | | | | | Vmn1r157 | | 23791 | 3 | | | | | Vmn1r24 |
| 23707 | 3 | | | | | Vmn1r158 | | 23792 | 3 | | | | | Vmn1r25 |
| 23708 | 3 | | | | | Vmn1r159 | | 23793 | 3 | | | | | Vmn1r26 |
| 23709 | 3 | | | | | Vmn1r16 | | 23794 | 3 | | | | | Vmn1r27 |
| 23710 | 3 | | | | | Vmn1r160 | | 23795 | 3 | | | | | Vmn1r28 |
| 23711 | 3 | | | | | Vmn1r163 | | 23796 | 3 | | | | | Vmn1r29 |
| 23712 | 3 | | | | | Vmn1r165 | | 23797 | 3 | | | | | Vmn1r3 |

Fig. 43 - 141

| | | | | | | | |
|---|---|---|---|---|---|---|---|
| 23798 | 3 | | | | | | Vmn1r30 |
| 23799 | 3 | | | | | | Vmn1r31 |
| 23800 | 3 | | | | | | Vmn1r32 |
| 23801 | 3 | | | | | | Vmn1r33 |
| 23802 | 3 | | | | | | Vmn1r34 |
| 23803 | 3 | | | | | | Vmn1r35 |
| 23804 | 3 | | | | | | Vmn1r36 |
| 23805 | 3 | | | | | | Vmn1r37 |
| 23806 | 3 | | | | | | Vmn1r38 |
| 23807 | 3 | | | | | | Vmn1r39 |
| 23808 | 3 | | | | | | Vmn1r4 |
| 23809 | 3 | | | | | | Vmn1r40 |
| 23810 | 3 | | | | | | Vmn1r41 |
| 23811 | 3 | | | | | | Vmn1r42 |
| 23812 | 3 | | | | | | Vmn1r43 |
| 23813 | 3 | | | | | | Vmn1r44 |
| 23814 | 3 | | | | | | Vmn1r47 |
| 23815 | 3 | | | | | | Vmn1r48 |
| 23816 | 3 | | | | | | Vmn1r49 |
| 23817 | 3 | | | | | | Vmn1r5 |
| 23818 | 3 | | | | | | Vmn1r50 |
| 23819 | 3 | | | | | | Vmn1r51 |
| 23820 | 3 | | | | | | Vmn1r52 |
| 23821 | 3 | | | | | | Vmn1r53 |
| 23822 | 3 | | | | | | Vmn1r54 |
| 23823 | 3 | | | | | | Vmn1r55 |
| 23824 | 3 | | | | | | Vmn1r56 |
| 23825 | 3 | | | | | | Vmn1r57 |
| 23826 | 3 | | | | | | Vmn1r58 |
| 23827 | 3 | | | | | | Vmn1r59 |
| 23828 | 3 | | | | | | Vmn1r6 |
| 23829 | 3 | | | | | | Vmn1r60 |
| 23830 | 3 | | | | | | Vmn1r61 |
| 23831 | 3 | | | | | | Vmn1r62 |
| 23832 | 3 | | | | | | Vmn1r63 |
| 23833 | 3 | | | | | | Vmn1r64 |
| 23834 | 3 | | | | | | Vmn1r65 |
| 23835 | 3 | | | | | | Vmn1r66 |
| 23836 | 3 | | | | | | Vmn1r67 |
| 23837 | 3 | | | | | | Vmn1r68 |
| 23838 | 3 | | | | | | Vmn1r69 |
| 23839 | 3 | | | | | | Vmn1r7 |
| 23840 | 3 | | | | | | Vmn1r70 |
| 23841 | 3 | | | | | | Vmn1r71 |
| 23842 | 3 | | | | | | Vmn1r72 |
| 23843 | 3 | | | | | | Vmn1r73 |
| 23844 | 3 | | | | | | Vmn1r74 |
| 23845 | 3 | | | | | | Vmn1r75 |
| 23846 | 3 | | | | | | Vmn1r76 |
| 23847 | 3 | | | | | | Vmn1r77 |
| 23848 | 3 | | | | | | Vmn1r78 |
| 23849 | 3 | | | | | | Vmn1r79 |
| 23850 | 3 | | | | | | Vmn1r8 |
| 23851 | 3 | | | | | | Vmn1r80 |
| 23852 | 3 | | | | | | Vmn1r81 |
| 23853 | 3 | | | | | | Vmn1r82 |
| 23854 | 3 | | | | | | Vmn1r83 |
| 23855 | 3 | | | | | | Vmn1r84 |
| 23856 | 3 | | | | | | Vmn1r85 |
| 23857 | 3 | | | | | | Vmn1r86 |
| 23858 | 3 | | | | | | Vmn1r87 |
| 23859 | 3 | | | | | | Vmn1r88 |
| 23860 | 3 | | | | | | Vmn1r89 |
| 23861 | 3 | | | | | | Vmn1r9 |
| 23862 | 3 | | | | | | Vmn1r90 |
| 23863 | 3 | | | | | | Vmn1r91 |
| 23864 | 3 | | | | | | Vmn1r94 |
| 23865 | 3 | | | | | | Vmn1r95 |
| 23866 | 3 | | | | | | Vmn1r-ps103 |
| 23867 | 3 | | | | | | Vmn1r-ps79 |
| 23868 | 3 | | | | | | Vmn2r1 |
| 23869 | 3 | | | | | | Vmn2r10 |
| 23870 | 3 | | | | | | Vmn2r100 |
| 23871 | 3 | | | | | | Vmn2r101 |
| 23872 | 3 | | | | | | Vmn2r102 |
| 23873 | 3 | | | | | | Vmn2r103 |
| 23874 | 3 | | | | | | Vmn2r104 |
| 23875 | 3 | | | | | | Vmn2r105 |
| 23876 | 3 | | | | | | Vmn2r106 |
| 23877 | 3 | | | | | | Vmn2r107 |
| 23878 | 3 | | | | | | Vmn2r108 |
| 23879 | 3 | | | | | | Vmn2r109 |
| 23880 | 3 | | | | | | Vmn2r11 |
| 23881 | 3 | | | | | | Vmn2r110 |
| 23882 | 3 | | | | | | Vmn2r111 |
| 23883 | 3 | | | | | | Vmn2r112 |
| 23884 | 3 | | | | | | Vmn2r113 |
| 23885 | 3 | | | | | | Vmn2r114 |
| 23886 | 3 | | | | | | Vmn2r115 |
| 23887 | 3 | | | | | | Vmn2r116 |
| 23888 | 3 | | | | | | Vmn2r117 |
| 23889 | 3 | | | | | | Vmn2r118 |
| 23890 | 3 | | | | | | Vmn2r12 |
| 23891 | 3 | | | | | | Vmn2r120 |
| 23892 | 3 | | | | | | Vmn2r121 |
| 23893 | 3 | | | | | | Vmn2r122 |
| 23894 | 3 | | | | | | Vmn2r123 |
| 23895 | 3 | | | | | | Vmn2r124 |
| 23896 | 3 | | | | | | Vmn2r13 |
| 23897 | 3 | | | | | | Vmn2r14 |
| 23898 | 3 | | | | | | Vmn2r15 |
| 23899 | 3 | | | | | | Vmn2r16 |
| 23900 | 3 | | | | | | Vmn2r17 |
| 23901 | 3 | | | | | | Vmn2r18 |
| 23902 | 3 | | | | | | Vmn2r19 |
| 23903 | 3 | | | | | | Vmn2r2 |
| 23904 | 3 | | | | | | Vmn2r20 |
| 23905 | 3 | | | | | | Vmn2r21 |
| 23906 | 3 | | | | | | Vmn2r22 |
| 23907 | 3 | | | | | | Vmn2r23 |
| 23908 | 3 | | | | | | Vmn2r24 |
| 23909 | 3 | | | | | | Vmn2r25 |
| 23910 | 3 | | | | | | Vmn2r26 |
| 23911 | 3 | | | | | | Vmn2r27 |
| 23912 | 3 | | | | | | Vmn2r28 |
| 23913 | 3 | | | | | | Vmn2r3 |
| 23914 | 3 | | | | | | Vmn2r30 |
| 23915 | 3 | | | | | | Vmn2r31 |
| 23916 | 3 | | | | | | Vmn2r32 |
| 23917 | 3 | | | | | | Vmn2r33 |
| 23918 | 3 | | | | | | Vmn2r35 |
| 23919 | 3 | | | | | | Vmn2r36 |
| 23920 | 3 | | | | | | Vmn2r37 |
| 23921 | 3 | | | | | | Vmn2r38 |
| 23922 | 3 | | | | | | Vmn2r39 |
| 23923 | 3 | | | | | | Vmn2r4 |
| 23924 | 3 | | | | | | Vmn2r40 |
| 23925 | 3 | | | | | | Vmn2r41 |
| 23926 | 3 | | | | | | Vmn2r42 |
| 23927 | 3 | | | | | | Vmn2r43 |
| 23928 | 3 | | | | | | Vmn2r44 |
| 23929 | 3 | | | | | | Vmn2r45 |
| 23930 | 3 | | | | | | Vmn2r46 |
| 23931 | 3 | | | | | | Vmn2r47 |
| 23932 | 3 | | | | | | Vmn2r48 |
| 23933 | 3 | | | | | | Vmn2r49 |
| 23934 | 3 | | | | | | Vmn2r5 |
| 23935 | 3 | | | | | | Vmn2r50 |
| 23936 | 3 | | | | | | Vmn2r51 |
| 23937 | 3 | | | | | | Vmn2r52 |
| 23938 | 3 | | | | | | Vmn2r53 |
| 23939 | 3 | | | | | | Vmn2r54 |
| 23940 | 3 | | | | | | Vmn2r55 |
| 23941 | 3 | | | | | | Vmn2r56 |
| 23942 | 3 | | | | | | Vmn2r57 |
| 23943 | 3 | | | | | | Vmn2r58 |
| 23944 | 3 | | | | | | Vmn2r59 |
| 23945 | 3 | | | | | | Vmn2r6 |
| 23946 | 3 | | | | | | Vmn2r60 |
| 23947 | 3 | | | | | | Vmn2r61 |
| 23948 | 3 | | | | | | Vmn2r62 |
| 23949 | 3 | | | | | | Vmn2r65 |
| 23950 | 3 | | | | | | Vmn2r67 |
| 23951 | 3 | | | | | | Vmn2r68 |
| 23952 | 3 | | | | | | Vmn2r69 |
| 23953 | 3 | | | | | | Vmn2r7 |
| 23954 | 3 | | | | | | Vmn2r70 |
| 23955 | 3 | | | | | | Vmn2r71 |
| 23956 | 3 | | | | | | Vmn2r72 |
| 23957 | 3 | | | | | | Vmn2r73 |
| 23958 | 3 | | | | | | Vmn2r74 |
| 23959 | 3 | | | | | | Vmn2r75 |
| 23960 | 3 | | | | | | Vmn2r76 |
| 23961 | 3 | | | | | | Vmn2r77 |
| 23962 | 3 | | | | | | Vmn2r78 |
| 23963 | 3 | | | | | | Vmn2r79 |
| 23964 | 3 | | | | | | Vmn2r8 |
| 23965 | 3 | | | | | | Vmn2r80 |
| 23966 | 3 | | | | | | Vmn2r81 |
| 23967 | 3 | | | | | | Vmn2r82 |

Fig. 43 - 142

| | | | | | | | |
|---|---|---|---|---|---|---|---|
| 23968 | 3 | | | | | | Vmn2r83 |
| 23969 | 3 | | | | | | Vmn2r85 |
| 23970 | 3 | | | | | | Vmn2r86 |
| 23971 | 3 | | | | | | Vmn2r87 |
| 23972 | 3 | | | | | | Vmn2r88 |
| 23973 | 3 | | | | | | Vmn2r89 |
| 23974 | 3 | | | | | | Vmn2r9 |
| 23975 | 3 | | | | | | Vmn2r90 |
| 23976 | 3 | | | | | | Vmn2r91 |
| 23977 | 3 | | | | | | Vmn2r92 |
| 23978 | 3 | | | | | | Vmn2r93 |
| 23979 | 3 | | | | | | Vmn2r94 |
| 23980 | 3 | | | | | | Vmn2r95 |
| 23981 | 3 | | | | | | Vmn2r96 |
| 23982 | 3 | | | | | | Vmn2r97 |
| 23983 | 3 | | | | | | Vmn2r98 |
| 23984 | 3 | | | | | | Vmn2r99 |
| 23985 | 3 | | | | | | Vmn2r-ps11 |
| 23986 | 3 | | | | | | Vmn2r-ps129 |
| 23987 | 3 | | | | | | Vmn2r-ps159 |
| 23988 | 3 | | | | | | Vmn2r-ps54 |
| 23989 | 3 | | | | | | Vmn2r-ps60 |
| 23990 | 3 | | | | | | Zfp623 |
| 23991 | 3 | | | | | | Zswim8 |

Fig.44

|  | Gene Name | qRT-PCR |
|---|---|---|
| Colon | Reg3a | 46.25 |
|  | Reg2 | 19.07 |
|  | Reg3d | 20.54 |
|  | Prss3 | 11.75 |
|  | Isg15 | 0.07 |
| Kidney | Phlda3 | 18.38 |
|  | Ces2e | 9.47 |
|  | Cdkn1a | 6.57 |
|  | Cyp27b1 | 5.75 |
|  | Gdf15 | 3.65 |
|  | Mgmt | 3.11 |
|  | Hmox1 | 0.06 |
|  | Krt20 | 20.20 |
|  | Eda2r | 225.57 |
| Heart | Sln | 5.12 |
|  | Cfd | 7.02 |
|  | Myl7 | 4.28 |
|  | Hamp | 7.58 |
|  | Cidec | 4.55 |
|  | Lgals3 | 3.01 |
|  | Hmox1 | 0.14 |
| Liver | Serpine1 | 45.25 |
|  | Serpina7 | 42.83 |
|  | Saa3 | 17.54 |
|  | Phlda3 | 13.74 |
|  | Saa2 | 11.48 |
|  | Lcn2 | 19.74 |
|  | Saa1 | 9.28 |
|  | Cyp8b1 | 0.07 |
| Lung | Klf7 | 0.61 |
| Skeletal muscle | Apoa1 | 3.86 |
|  | Apoa2 | 1.89 |
| Stomach | Krt16 | 12.38 |

Fig. 45 - 1

| Line No. | Group No. | | | | | Sub-Groups | Gene Name | STZ/Control |
|---|---|---|---|---|---|---|---|---|
| 1 | 3 | 4 | 5 | 6 | 7 | VII-2 | Apoa4 | 0.15 |
| 2 | 3 | 4 | 5 | 6 | 7 | VII-2 | Apoc3 | 0.17 |
| 3 | 3 | 4 | 5 | 6 | 7 | VII-2 | Aqp8 | 0.08 |
| 4 | 3 | 4 | 5 | 6 | 7 | VII-2 | C8b | 0.14 |
| 5 | 3 | 4 | 5 | 6 | 7 | VII-2 | Cidec | 0.14 |
| 6 | 3 | 4 | 5 | 6 | 7 | VII-2 | Ckmt2 | 0.19 |
| 7 | 3 | 4 | 5 | 6 | 7 | VII-2 | Cyp2c44 | 0.15 |
| 8 | 3 | 4 | 5 | 6 | 7 | VII-2 | Eif3j1 | 0.07 |
| 9 | 3 | 4 | 5 | 6 | 7 | VII-2 | Fabp2 | 0.13 |
| 10 | 3 | 4 | 5 | 6 | 7 | VII-2 | Gpd1 | 0.14 |
| 11 | 3 | 4 | 5 | 6 | 7 | VII-2 | Hc | 0.18 |
| 12 | 3 | 4 | 5 | 6 | 7 | VII-2 | Ins2 | 0.11 |
| 13 | 3 | 4 | 5 | 6 | 7 | VII-2 | Itih4 | 0.17 |
| 14 | 3 | 4 | 5 | 6 | 7 | VII-2 | Lct | 0.16 |
| 15 | 3 | 4 | 5 | 6 | 7 | VII-2 | Mcpt4 | 0.18 |
| 16 | 3 | 4 | 5 | 6 | 7 | VII-2 | Mir486 | 0.13 |
| 17 | 3 | 4 | 5 | 6 | 7 | VII-2 | Mir682 | 0.00 |
| 18 | 3 | 4 | 5 | 6 | 7 | VII-2 | Mir7-1 | 0.03 |
| 19 | 3 | 4 | 5 | 6 | 7 | VII-2 | Mir8104 | 0.20 |
| 20 | 3 | 4 | 5 | 6 | 7 | VII-2 | Pklr | 0.19 |
| 21 | 3 | 4 | 5 | 6 | 7 | VII-2 | Plin1 | 0.15 |
| 22 | 3 | 4 | 5 | 6 | 7 | VII-2 | Prap1 | 0.15 |
| 23 | 3 | 4 | 5 | 6 | 7 | VII-2 | Prss1 | 0.17 |
| 24 | 3 | 4 | 5 | 6 | 7 | VII-2 | Rdh7 | 0.16 |
| 25 | 3 | 4 | 5 | 6 | 7 | VII-2 | Redrum | 0.19 |
| 26 | 3 | 4 | 5 | 6 | 7 | VII-2 | Serpina6 | 0.07 |
| 27 | 3 | 4 | 5 | 6 | 7 | VII-2 | Snora64 | 0.06 |
| 28 | 3 | 4 | 5 | 6 | 7 | VII-2 | Snora70 | 0.03 |
| 29 | 3 | 4 | 5 | 6 | 7 | VII-2 | Thrsp | 0.07 |
| 30 | 3 | 4 | 5 | 6 | 7 | VII-2 | Xist | 0.01 |
| 31 | 3 | 4 | 5 | 6 | 7 | VII-1 | Mir7060 | 5.21 |
| 32 | 3 | 4 | 5 | 6 | 7 | VII-1 | Mir8093 | 5.21 |
| 33 | 3 | 4 | 5 | 6 | 7 | VII-1 | Rtp4 | 5.43 |
| 34 | 3 | 4 | 5 | 6 | 7 | VII-1 | Isg15 | 5.45 |
| 35 | 3 | 4 | 5 | 6 | 7 | VII-1 | Prss27 | 5.48 |
| 36 | 3 | 4 | 5 | 6 | 7 | VII-1 | Rsad2 | 5.56 |
| 37 | 3 | 4 | 5 | 6 | 7 | VII-1 | Ifit3 | 6.26 |
| 38 | 3 | 4 | 5 | 6 | 7 | VII-1 | Irf7 | 6.26 |
| 39 | 3 | 4 | 5 | 6 | 7 | VII-1 | Oasl2 | 6.42 |
| 40 | 3 | 4 | 5 | 6 | 7 | VII-1 | Snora17 | 6.50 |
| 41 | 3 | 4 | 5 | 6 | 7 | VII-1 | Mir8112 | 6.82 |
| 42 | 3 | 4 | 5 | 6 | 7 | VII-1 | Ifit1 | 6.84 |
| 43 | 3 | 4 | 5 | 6 | 7 | VII-1 | Serpina3n | 7.42 |
| 44 | 3 | 4 | 5 | 6 | 7 | VII-1 | Mir8113 | 7.53 |
| 45 | 3 | 4 | 5 | 6 | 7 | VII-1 | Snord15b | 7.68 |
| 46 | 3 | 4 | 5 | 6 | 7 | VII-1 | Snora21 | 7.92 |
| 47 | 3 | 4 | 5 | 6 | 7 | VII-1 | Serpinb9b | 8.19 |
| 48 | 3 | 4 | 5 | 6 | 7 | VII-1 | Hamp | 11.00 |
| 49 | 3 | 4 | 5 | 6 | 7 | VII-1 | Mir6357 | 12.59 |
| 50 | 3 | 4 | 5 | 6 | 7 | VII-1 | Mir760 | 13.60 |
| 51 | 3 | 4 | 5 | 6 | 7 | VII-1 | Sprr2d | 13.66 |
| 52 | 3 | 4 | 5 | 6 | 7 | VII-1 | Snora75 | 16.98 |
| 53 | 3 | 4 | 5 | 6 | 7 | VII-1 | Snora31 | 23.94 |
| 54 | 3 | 4 | 5 | 6 | 7 | VII-1 | Mir1188 | 25.41 |
| 55 | 3 | 4 | 5 | 6 | 7 | VII-1 | Mir10a | 29.23 |
| 56 | 3 | 4 | 5 | 6 | 7 | VII-1 | Mirlet7d | 76.39 |
| 57 | 3 | 4 | 5 | 6 | | VI-2 | 1300002K09Rik | 0.42 |
| 58 | 3 | 4 | 5 | 6 | | VI-2 | 1300017J02Rik | 0.44 |
| 59 | 3 | 4 | 5 | 6 | | VI-2 | 1700011H14Rik | 0.38 |
| 60 | 3 | 4 | 5 | 6 | | VI-2 | 1700019D03Rik | 0.42 |
| 61 | 3 | 4 | 5 | 6 | | VI-2 | 1810008I18Rik | 0.38 |
| 62 | 3 | 4 | 5 | 6 | | VI-2 | 2310015B20Rik | 0.46 |
| 63 | 3 | 4 | 5 | 6 | | VI-2 | 2310050C09Rik | 0.42 |
| 64 | 3 | 4 | 5 | 6 | | VI-2 | 2310057N15Rik | 0.23 |
| 65 | 3 | 4 | 5 | 6 | | VI-2 | 2310079G19Rik | 0.40 |
| 66 | 3 | 4 | 5 | 6 | | VI-2 | 2510049J12Rik | 0.48 |
| 67 | 3 | 4 | 5 | 6 | | VI-2 | 2810417H13Rik | 0.50 |
| 68 | 3 | 4 | 5 | 6 | | VI-2 | 4930404N11Rik | 0.47 |
| 69 | 3 | 4 | 5 | 6 | | VI-2 | 5930412G12Rik | 0.41 |
| 70 | 3 | 4 | 5 | 6 | | VI-2 | 6030468B19Rik | 0.33 |
| 71 | 3 | 4 | 5 | 6 | | VI-2 | A2m | 0.45 |
| 72 | 3 | 4 | 5 | 6 | | VI-2 | AA465934 | 0.39 |
| 73 | 3 | 4 | 5 | 6 | | VI-2 | AI182371 | 0.37 |
| 74 | 3 | 4 | 5 | 6 | | VI-2 | AI747448 | 0.34 |
| 75 | 3 | 4 | 5 | 6 | | VI-2 | Aadac | 0.31 |
| 76 | 3 | 4 | 5 | 6 | | VI-2 | Abhd11os | 0.35 |
| 77 | 3 | 4 | 5 | 6 | | VI-2 | Acer1 | 0.39 |
| 78 | 3 | 4 | 5 | 6 | | VI-2 | Acnat1 | 0.36 |
| 79 | 3 | 4 | 5 | 6 | | VI-2 | Acp5 | 0.35 |
| 80 | 3 | 4 | 5 | 6 | | VI-2 | Acss1 | 0.46 |
| 81 | 3 | 4 | 5 | 6 | | VI-2 | Actn3 | 0.31 |
| 82 | 3 | 4 | 5 | 6 | | VI-2 | Adck3 | 0.32 |
| 83 | 3 | 4 | 5 | 6 | | VI-2 | Adipoq | 0.22 |
| 84 | 3 | 4 | 5 | 6 | | VI-2 | Adprhl1 | 0.40 |
| 85 | 3 | 4 | 5 | 6 | | VI-2 | Adra2b | 0.33 |
| 86 | 3 | 4 | 5 | 6 | | VI-2 | Adtrp | 0.33 |
| 87 | 3 | 4 | 5 | 6 | | VI-2 | Afm | 0.34 |
| 88 | 3 | 4 | 5 | 6 | | VI-2 | Afp | 0.39 |
| 89 | 3 | 4 | 5 | 6 | | VI-2 | Agmat | 0.40 |
| 90 | 3 | 4 | 5 | 6 | | VI-2 | Agr2 | 0.45 |
| 91 | 3 | 4 | 5 | 6 | | VI-2 | Alad | 0.42 |
| 92 | 3 | 4 | 5 | 6 | | VI-2 | Alb | 0.32 |
| 93 | 3 | 4 | 5 | 6 | | VI-2 | Aldh4a1 | 0.45 |
| 94 | 3 | 4 | 5 | 6 | | VI-2 | Alpi | 0.20 |
| 95 | 3 | 4 | 5 | 6 | | VI-2 | Ambp | 0.43 |
| 96 | 3 | 4 | 5 | 6 | | VI-2 | Ampd1 | 0.33 |
| 97 | 3 | 4 | 5 | 6 | | VI-2 | Angptl3 | 0.41 |
| 98 | 3 | 4 | 5 | 6 | | VI-2 | Ankle1 | 0.45 |
| 99 | 3 | 4 | 5 | 6 | | VI-2 | Anks4b | 0.34 |
| 100 | 3 | 4 | 5 | 6 | | VI-2 | Ano7 | 0.44 |
| 101 | 3 | 4 | 5 | 6 | | VI-2 | Anxa13 | 0.40 |
| 102 | 3 | 4 | 5 | 6 | | VI-2 | Aoc1 | 0.41 |
| 103 | 3 | 4 | 5 | 6 | | VI-2 | Apln | 0.49 |
| 104 | 3 | 4 | 5 | 6 | | VI-2 | Apoa2 | 0.43 |
| 105 | 3 | 4 | 5 | 6 | | VI-2 | Apob | 0.41 |
| 106 | 3 | 4 | 5 | 6 | | VI-2 | Apoc1 | 0.47 |
| 107 | 3 | 4 | 5 | 6 | | VI-2 | Apol8 | 0.21 |
| 108 | 3 | 4 | 5 | 6 | | VI-2 | Aqp7 | 0.31 |
| 109 | 3 | 4 | 5 | 6 | | VI-2 | Arhgef39 | 0.48 |
| 110 | 3 | 4 | 5 | 6 | | VI-2 | Asb12 | 0.49 |
| 111 | 3 | 4 | 5 | 6 | | VI-2 | Asb17os | 0.26 |
| 112 | 3 | 4 | 5 | 6 | | VI-2 | Asf1b | 0.48 |
| 113 | 3 | 4 | 5 | 6 | | VI-2 | Atp5k | 0.24 |
| 114 | 3 | 4 | 5 | 6 | | VI-2 | BC021614 | 0.38 |
| 115 | 3 | 4 | 5 | 6 | | VI-2 | BC117090 | 0.36 |
| 116 | 3 | 4 | 5 | 6 | | VI-2 | Bcs1l | 0.45 |
| 117 | 3 | 4 | 5 | 6 | | VI-2 | Bglap2 | 0.48 |
| 118 | 3 | 4 | 5 | 6 | | VI-2 | Birc5 | 0.49 |
| 119 | 3 | 4 | 5 | 6 | | VI-2 | Btvrb | 0.48 |
| 120 | 3 | 4 | 5 | 6 | | VI-2 | Btnl10 | 0.39 |
| 121 | 3 | 4 | 5 | 6 | | VI-2 | C3 | 0.47 |
| 122 | 3 | 4 | 5 | 6 | | VI-2 | C8a | 0.33 |
| 123 | 3 | 4 | 5 | 6 | | VI-2 | Calm4 | 0.47 |
| 124 | 3 | 4 | 5 | 6 | | VI-2 | Calm5 | 0.48 |
| 125 | 3 | 4 | 5 | 6 | | VI-2 | Calml3 | 0.30 |
| 126 | 3 | 4 | 5 | 6 | | VI-2 | Camp | 0.45 |
| 127 | 3 | 4 | 5 | 6 | | VI-2 | Car13 | 0.46 |
| 128 | 3 | 4 | 5 | 6 | | VI-2 | Car2 | 0.35 |
| 129 | 3 | 4 | 5 | 6 | | VI-2 | Car3 | 0.23 |
| 130 | 3 | 4 | 5 | 6 | | VI-2 | Casc5 | 0.48 |
| 131 | 3 | 4 | 5 | 6 | | VI-2 | Casq1 | 0.38 |
| 132 | 3 | 4 | 5 | 6 | | VI-2 | Ccdc163 | 0.41 |
| 133 | 3 | 4 | 5 | 6 | | VI-2 | Ccdc69 | 0.38 |
| 134 | 3 | 4 | 5 | 6 | | VI-2 | Ccna2 | 0.50 |
| 135 | 3 | 4 | 5 | 6 | | VI-2 | Ccne2 | 0.40 |
| 136 | 3 | 4 | 5 | 6 | | VI-2 | Ccnf | 0.48 |
| 137 | 3 | 4 | 5 | 6 | | VI-2 | Ccr2 | 0.39 |
| 138 | 3 | 4 | 5 | 6 | | VI-2 | Cd74 | 0.43 |
| 139 | 3 | 4 | 5 | 6 | | VI-2 | Cd79b | 0.46 |
| 140 | 3 | 4 | 5 | 6 | | VI-2 | Cdc6 | 0.47 |
| 141 | 3 | 4 | 5 | 6 | | VI-2 | Cdh16 | 0.46 |
| 142 | 3 | 4 | 5 | 6 | | VI-2 | Cdh17 | 0.44 |
| 143 | 3 | 4 | 5 | 6 | | VI-2 | Cdhr2 | 0.28 |
| 144 | 3 | 4 | 5 | 6 | | VI-2 | Cdhr5 | 0.30 |
| 145 | 3 | 4 | 5 | 6 | | VI-2 | Cdkn2c | 0.47 |
| 146 | 3 | 4 | 5 | 6 | | VI-2 | Cebpa | 0.47 |
| 147 | 3 | 4 | 5 | 6 | | VI-2 | Cela2a | 0.22 |
| 148 | 3 | 4 | 5 | 6 | | VI-2 | Cenpk | 0.48 |
| 149 | 3 | 4 | 5 | 6 | | VI-2 | Cfb | 0.46 |
| 150 | 3 | 4 | 5 | 6 | | VI-2 | Chac2 | 0.43 |
| 151 | 3 | 4 | 5 | 6 | | VI-2 | Chdh | 0.24 |
| 152 | 3 | 4 | 5 | 6 | | VI-2 | Chp2 | 0.39 |
| 153 | 3 | 4 | 5 | 6 | | VI-2 | Chst13 | 0.44 |
| 154 | 3 | 4 | 5 | 6 | | VI-2 | Cidea | 0.24 |
| 155 | 3 | 4 | 5 | 6 | | VI-2 | Cideb | 0.36 |
| 156 | 3 | 4 | 5 | 6 | | VI-2 | Cisd3 | 0.45 |
| 157 | 3 | 4 | 5 | 6 | | VI-2 | Cited4 | 0.33 |
| 158 | 3 | 4 | 5 | 6 | | VI-2 | Ckm | 0.42 |
| 159 | 3 | 4 | 5 | 6 | | VI-2 | Cks2 | 0.45 |
| 160 | 3 | 4 | 5 | 6 | | VI-2 | Clca2 | 0.46 |
| 161 | 3 | 4 | 5 | 6 | | VI-2 | Clca3 | 0.25 |
| 162 | 3 | 4 | 5 | 6 | | VI-2 | Clca5 | 0.40 |
| 163 | 3 | 4 | 5 | 6 | | VI-2 | Cldn13 | 0.30 |
| 164 | 3 | 4 | 5 | 6 | | VI-2 | Cldn6 | 0.42 |
| 165 | 3 | 4 | 5 | 6 | | VI-2 | Clec2g | 0.40 |
| 166 | 3 | 4 | 5 | 6 | | VI-2 | Clrn3 | 0.41 |
| 167 | 3 | 4 | 5 | 6 | | VI-2 | Cma1 | 0.34 |
| 168 | 3 | 4 | 5 | 6 | | VI-2 | Cml1 | 0.47 |
| 169 | 3 | 4 | 5 | 6 | | VI-2 | Cmya5 | 0.50 |
| 170 | 3 | 4 | 5 | 6 | | VI-2 | Cpa3 | 0.47 |
| 171 | 3 | 4 | 5 | 6 | | VI-2 | Cpb2 | 0.37 |
| 172 | 3 | 4 | 5 | 6 | | VI-2 | Cpn1 | 0.34 |
| 173 | 3 | 4 | 5 | 6 | | VI-2 | Cpox | 0.30 |
| 174 | 3 | 4 | 5 | 6 | | VI-2 | Ctse | 0.41 |
| 175 | 3 | 4 | 5 | 6 | | VI-2 | Cutal | 0.36 |
| 176 | 3 | 4 | 5 | 6 | | VI-2 | Cyp11b1 | 0.34 |
| 177 | 3 | 4 | 5 | 6 | | VI-2 | Cyp21a1 | 0.28 |
| 178 | 3 | 4 | 5 | 6 | | VI-2 | Dapl1 | 0.37 |
| 179 | 3 | 4 | 5 | 6 | | VI-2 | Dhrs11 | 0.45 |
| 180 | 3 | 4 | 5 | 6 | | VI-2 | Dkkl1 | 0.46 |
| 181 | 3 | 4 | 5 | 6 | | VI-2 | Dleu2 | 0.26 |
| 182 | 3 | 4 | 5 | 6 | | VI-2 | Dmp1 | 0.40 |
| 183 | 3 | 4 | 5 | 6 | | VI-2 | Dmtn | 0.49 |
| 184 | 3 | 4 | 5 | 6 | | VI-2 | Dpt | 0.47 |
| 185 | 3 | 4 | 5 | 6 | | VI-2 | Dpys | 0.47 |
| 186 | 3 | 4 | 5 | 6 | | VI-2 | Dynap | 0.33 |
| 187 | 3 | 4 | 5 | 6 | | VI-2 | E130310I04Rik | 0.41 |
| 188 | 3 | 4 | 5 | 6 | | VI-2 | Ear1 | 0.38 |
| 189 | 3 | 4 | 5 | 6 | | VI-2 | Ear6 | 0.47 |
| 190 | 3 | 4 | 5 | 6 | | VI-2 | Elane | 0.40 |

Fig. 45 - 2

| | | | | | | | | | | | | | | | |
|---|---|---|---|---|---|---|---|---|---|---|---|---|---|---|---|
| 191 | 3 | 4 | 5 | 6 | | VI-2 | Eno3 | 0.46 | 287 | 3 | 4 | 5 | 6 | VI-2 | Itpka | 0.48 |
| 192 | 3 | 4 | 5 | 6 | | VI-2 | Epb4.2 | 0.34 | 288 | 3 | 4 | 5 | 6 | VI-2 | Ivl | 0.41 |
| 193 | 3 | 4 | 5 | 6 | | VI-2 | Epor | 0.32 | 289 | 3 | 4 | 5 | 6 | VI-2 | Kcnn4 | 0.42 |
| 194 | 3 | 4 | 5 | 6 | | VI-2 | Eps8l3 | 0.32 | 290 | 3 | 4 | 5 | 6 | VI-2 | Kel | 0.32 |
| 195 | 3 | 4 | 5 | 6 | | VI-2 | Ercc6l | 0.42 | 291 | 3 | 4 | 5 | 6 | VI-2 | Kera | 0.40 |
| 196 | 3 | 4 | 5 | 6 | | VI-2 | Erdr1 | 0.39 | 292 | 3 | 4 | 5 | 6 | VI-2 | Klb | 0.49 |
| 197 | 3 | 4 | 5 | 6 | | VI-2 | Erich4 | 0.47 | 293 | 3 | 4 | 5 | 6 | VI-2 | Klf1 | 0.22 |
| 198 | 3 | 4 | 5 | 6 | | VI-2 | Ermap | 0.40 | 294 | 3 | 4 | 5 | 6 | VI-2 | Klhdc7a | 0.47 |
| 199 | 3 | 4 | 5 | 6 | | VI-2 | Etfa | 0.50 | 295 | 3 | 4 | 5 | 6 | VI-2 | Klk1 | 0.33 |
| 200 | 3 | 4 | 5 | 6 | | VI-2 | F11 | 0.39 | 296 | 3 | 4 | 5 | 6 | VI-2 | Klk5 | 0.44 |
| 201 | 3 | 4 | 5 | 6 | | VI-2 | F2rl2 | 0.46 | 297 | 3 | 4 | 5 | 6 | VI-2 | Klkb1 | 0.40 |
| 202 | 3 | 4 | 5 | 6 | | VI-2 | F5 | 0.40 | 298 | 3 | 4 | 5 | 6 | VI-2 | Kmo | 0.47 |
| 203 | 3 | 4 | 5 | 6 | | VI-2 | F830002L21Rik | 0.41 | 299 | 3 | 4 | 5 | 6 | VI-2 | Krt20 | 0.47 |
| 204 | 3 | 4 | 5 | 6 | | VI-2 | F9 | 0.37 | 300 | 3 | 4 | 5 | 6 | VI-2 | Krt36 | 0.37 |
| 205 | 3 | 4 | 5 | 6 | | VI-2 | Fabp1 | 0.21 | 301 | 3 | 4 | 5 | 6 | VI-2 | Krt77 | 0.37 |
| 206 | 3 | 4 | 5 | 6 | | VI-2 | Fabp4 | 0.36 | 302 | 3 | 4 | 5 | 6 | VI-2 | Krt79 | 0.45 |
| 207 | 3 | 4 | 5 | 6 | | VI-2 | Fam83a | 0.43 | 303 | 3 | 4 | 5 | 6 | VI-2 | Krt84 | 0.43 |
| 208 | 3 | 4 | 5 | 6 | | VI-2 | Fbp1 | 0.28 | 304 | 3 | 4 | 5 | 6 | VI-2 | Krtap7-1 | 0.26 |
| 209 | 3 | 4 | 5 | 6 | | VI-2 | Fbxl22 | 0.30 | 305 | 3 | 4 | 5 | 6 | VI-2 | Krtap8-1 | 0.29 |
| 210 | 3 | 4 | 5 | 6 | | VI-2 | Fcgbp | 0.45 | 306 | 3 | 4 | 5 | 6 | VI-2 | Krtcap3 | 0.47 |
| 211 | 3 | 4 | 5 | 6 | | VI-2 | Fcnb | 0.25 | 307 | 3 | 4 | 5 | 6 | VI-2 | Lce1b | 0.38 |
| 212 | 3 | 4 | 5 | 6 | | VI-2 | Fdps | 0.50 | 308 | 3 | 4 | 5 | 6 | VI-2 | Lce1d | 0.37 |
| 213 | 3 | 4 | 5 | 6 | | VI-2 | Fignl1 | 0.45 | 309 | 3 | 4 | 5 | 6 | VI-2 | Leap2 | 0.37 |
| 214 | 3 | 4 | 5 | 6 | | VI-2 | Fn3k | 0.24 | 310 | 3 | 4 | 5 | 6 | VI-2 | Lect2 | 0.36 |
| 215 | 3 | 4 | 5 | 6 | | VI-2 | Fsd2 | 0.46 | 311 | 3 | 4 | 5 | 6 | VI-2 | Lgals12 | 0.33 |
| 216 | 3 | 4 | 5 | 6 | | VI-2 | Gamt | 0.38 | 312 | 3 | 4 | 5 | 6 | VI-2 | Lipc | 0.42 |
| 217 | 3 | 4 | 5 | 6 | | VI-2 | Gata1 | 0.31 | 313 | 3 | 4 | 5 | 6 | VI-2 | Lipe | 0.32 |
| 218 | 3 | 4 | 5 | 6 | | VI-2 | Gc | 0.50 | 314 | 3 | 4 | 5 | 6 | VI-2 | Ltf | 0.42 |
| 219 | 3 | 4 | 5 | 6 | | VI-2 | Gcat | 0.42 | 315 | 3 | 4 | 5 | 6 | VI-2 | Ly96 | 0.50 |
| 220 | 3 | 4 | 5 | 6 | | VI-2 | Gfap | 0.43 | 316 | 3 | 4 | 5 | 6 | VI-2 | Lyrm7 | 0.49 |
| 221 | 3 | 4 | 5 | 6 | | VI-2 | Gfi1b | 0.48 | 317 | 3 | 4 | 5 | 6 | VI-2 | Mamdc4 | 0.46 |
| 222 | 3 | 4 | 5 | 6 | | VI-2 | Ggct | 0.35 | 318 | 3 | 4 | 5 | 6 | VI-2 | Maob | 0.45 |
| 223 | 3 | 4 | 5 | 6 | | VI-2 | Gjb4 | 0.47 | 319 | 3 | 4 | 5 | 6 | VI-2 | Map2k3os | 0.39 |
| 224 | 3 | 4 | 5 | 6 | | VI-2 | Gjb5 | 0.29 | 320 | 3 | 4 | 5 | 6 | VI-2 | Masp2 | 0.40 |
| 225 | 3 | 4 | 5 | 6 | | VI-2 | Gltpd2 | 0.39 | 321 | 3 | 4 | 5 | 6 | VI-2 | Mbl1 | 0.24 |
| 226 | 3 | 4 | 5 | 6 | | VI-2 | Gm10069 | 0.49 | 322 | 3 | 4 | 5 | 6 | VI-2 | Mep1a | 0.41 |
| 227 | 3 | 4 | 5 | 6 | | VI-2 | Gm10334 | 0.26 | 323 | 3 | 4 | 5 | 6 | VI-2 | Mfsd2b | 0.45 |
| 228 | 3 | 4 | 5 | 6 | | VI-2 | Gm20741 | 0.36 | 324 | 3 | 4 | 5 | 6 | VI-2 | Mir6236 | 0.46 |
| 229 | 3 | 4 | 5 | 6 | | VI-2 | Gm4963 | 0.45 | 325 | 3 | 4 | 5 | 6 | VI-2 | Mki67 | 0.46 |
| 230 | 3 | 4 | 5 | 6 | | VI-2 | Gm4980 | 0.50 | 326 | 3 | 4 | 5 | 6 | VI-2 | Mlip | 0.40 |
| 231 | 3 | 4 | 5 | 6 | | VI-2 | Gm5176 | 0.44 | 327 | 3 | 4 | 5 | 6 | VI-2 | Mns1 | 0.33 |
| 232 | 3 | 4 | 5 | 6 | | VI-2 | Gm5424 | 0.49 | 328 | 3 | 4 | 5 | 6 | VI-2 | Mogat2 | 0.37 |
| 233 | 3 | 4 | 5 | 6 | | VI-2 | Gm5771 | 0.45 | 329 | 3 | 4 | 5 | 6 | VI-2 | Mrap | 0.30 |
| 234 | 3 | 4 | 5 | 6 | | VI-2 | Gm6484 | 0.37 | 330 | 3 | 4 | 5 | 6 | VI-2 | Mst1 | 0.45 |
| 235 | 3 | 4 | 5 | 6 | | VI-2 | Gm867 | 0.40 | 331 | 3 | 4 | 5 | 6 | VI-2 | Mtfp1 | 0.45 |
| 236 | 3 | 4 | 5 | 6 | | VI-2 | Gm94 | 0.33 | 332 | 3 | 4 | 5 | 6 | VI-2 | Muc13 | 0.31 |
| 237 | 3 | 4 | 5 | 6 | | VI-2 | Gp5 | 0.38 | 333 | 3 | 4 | 5 | 6 | VI-2 | Muc6 | 0.34 |
| 238 | 3 | 4 | 5 | 6 | | VI-2 | Gp9 | 0.30 | 334 | 3 | 4 | 5 | 6 | VI-2 | Myoz1 | 0.41 |
| 239 | 3 | 4 | 5 | 6 | | VI-2 | Gpx3 | 0.43 | 335 | 3 | 4 | 5 | 6 | VI-2 | Naip6 | 0.38 |
| 240 | 3 | 4 | 5 | 6 | | VI-2 | Gsta2 | 0.46 | 336 | 3 | 4 | 5 | 6 | VI-2 | Ndufa4l2 | 0.45 |
| 241 | 3 | 4 | 5 | 6 | | VI-2 | Gstt1 | 0.43 | 337 | 3 | 4 | 5 | 6 | VI-2 | Nfe2 | 0.44 |
| 242 | 3 | 4 | 5 | 6 | | VI-2 | Guca2b | 0.33 | 338 | 3 | 4 | 5 | 6 | VI-2 | Npl | 0.30 |
| 243 | 3 | 4 | 5 | 6 | | VI-2 | Gypa | 0.32 | 339 | 3 | 4 | 5 | 6 | VI-2 | Nudt5 | 0.45 |
| 244 | 3 | 4 | 5 | 6 | | VI-2 | Gys2 | 0.40 | 340 | 3 | 4 | 5 | 6 | VI-2 | Nutf2-ps1 | 0.43 |
| 245 | 3 | 4 | 5 | 6 | | VI-2 | H2-Aa | 0.32 | 341 | 3 | 4 | 5 | 6 | VI-2 | Nxpe2 | 0.22 |
| 246 | 3 | 4 | 5 | 6 | | VI-2 | H2-Ab1 | 0.42 | 342 | 3 | 4 | 5 | 6 | VI-2 | Oas1f | 0.39 |
| 247 | 3 | 4 | 5 | 6 | | VI-2 | H2-Q2 | 0.48 | 343 | 3 | 4 | 5 | 6 | VI-2 | Otc | 0.30 |
| 248 | 3 | 4 | 5 | 6 | | VI-2 | H2-Q6 | 0.42 | 344 | 3 | 4 | 5 | 6 | VI-2 | P2ry4 | 0.36 |
| 249 | 3 | 4 | 5 | 6 | | VI-2 | H2-T9 | 0.49 | 345 | 3 | 4 | 5 | 6 | VI-2 | Pah | 0.44 |
| 250 | 3 | 4 | 5 | 6 | | VI-2 | H60c | 0.44 | 346 | 3 | 4 | 5 | 6 | VI-2 | Pbld1 | 0.41 |
| 251 | 3 | 4 | 5 | 6 | | VI-2 | Haao | 0.29 | 347 | 3 | 4 | 5 | 6 | VI-2 | Pcsk9 | 0.48 |
| 252 | 3 | 4 | 5 | 6 | | VI-2 | Habp2 | 0.29 | 348 | 3 | 4 | 5 | 6 | VI-2 | Pdia2 | 0.49 |
| 253 | 3 | 4 | 5 | 6 | | VI-2 | Hao1 | 0.49 | 349 | 3 | 4 | 5 | 6 | VI-2 | Pdzk1 | 0.41 |
| 254 | 3 | 4 | 5 | 6 | | VI-2 | Hao2 | 0.35 | 350 | 3 | 4 | 5 | 6 | VI-2 | Pgam2 | 0.41 |
| 255 | 3 | 4 | 5 | 6 | | VI-2 | Hba-a1 | 0.50 | 351 | 3 | 4 | 5 | 6 | VI-2 | Pi16 | 0.38 |
| 256 | 3 | 4 | 5 | 6 | | VI-2 | Hbb-b1 | 0.47 | 352 | 3 | 4 | 5 | 6 | VI-2 | Pla2g2f | 0.44 |
| 257 | 3 | 4 | 5 | 6 | | VI-2 | Hbb-bs | 0.45 | 353 | 3 | 4 | 5 | 6 | VI-2 | Plek2 | 0.40 |
| 258 | 3 | 4 | 5 | 6 | | VI-2 | Hbb-bt | 0.43 | 354 | 3 | 4 | 5 | 6 | VI-2 | Plin4 | 0.33 |
| 259 | 3 | 4 | 5 | 6 | | VI-2 | Hcar1 | 0.37 | 355 | 3 | 4 | 5 | 6 | VI-2 | Pls1 | 0.46 |
| 260 | 3 | 4 | 5 | 6 | | VI-2 | Hdhd3 | 0.42 | 356 | 3 | 4 | 5 | 6 | VI-2 | Pnpo | 0.47 |
| 261 | 3 | 4 | 5 | 6 | | VI-2 | Hebp1 | 0.41 | 357 | 3 | 4 | 5 | 6 | VI-2 | Pole2 | 0.47 |
| 262 | 3 | 4 | 5 | 6 | | VI-2 | Hemgn | 0.26 | 358 | 3 | 4 | 5 | 6 | VI-2 | Pou2f3 | 0.48 |
| 263 | 3 | 4 | 5 | 6 | | VI-2 | Hist1h1e | 0.47 | 359 | 3 | 4 | 5 | 6 | VI-2 | Pparg | 0.39 |
| 264 | 3 | 4 | 5 | 6 | | VI-2 | Hist1h2ab | 0.45 | 360 | 3 | 4 | 5 | 6 | VI-2 | Ppargc1b | 0.48 |
| 265 | 3 | 4 | 5 | 6 | | VI-2 | Hist1h2ah | 0.46 | 361 | 3 | 4 | 5 | 6 | VI-2 | Ppbp | 0.32 |
| 266 | 3 | 4 | 5 | 6 | | VI-2 | Hist1h2ai | 0.49 | 362 | 3 | 4 | 5 | 6 | VI-2 | Prelid2 | 0.48 |
| 267 | 3 | 4 | 5 | 6 | | VI-2 | Hist1h2ak | 0.49 | 363 | 3 | 4 | 5 | 6 | VI-2 | Prg2 | 0.49 |
| 268 | 3 | 4 | 5 | 6 | | VI-2 | Hist1h2ap | 0.48 | 364 | 3 | 4 | 5 | 6 | VI-2 | Proc | 0.42 |
| 269 | 3 | 4 | 5 | 6 | | VI-2 | Hist1h2ba | 0.43 | 365 | 3 | 4 | 5 | 6 | VI-2 | Prodh2 | 0.43 |
| 270 | 3 | 4 | 5 | 6 | | VI-2 | Hist1h2bb | 0.38 | 366 | 3 | 4 | 5 | 6 | VI-2 | Prss3 | 0.23 |
| 271 | 3 | 4 | 5 | 6 | | VI-2 | Hist1h2bg | 0.45 | 367 | 3 | 4 | 5 | 6 | VI-2 | Pygm | 0.43 |
| 272 | 3 | 4 | 5 | 6 | | VI-2 | Hist1h2bn | 0.36 | 368 | 3 | 4 | 5 | 6 | VI-2 | Pzp | 0.22 |
| 273 | 3 | 4 | 5 | 6 | | VI-2 | Hist1h3c | 0.41 | 369 | 3 | 4 | 5 | 6 | VI-2 | Rad54l | 0.44 |
| 274 | 3 | 4 | 5 | 6 | | VI-2 | Hist1h4i | 0.45 | 370 | 3 | 4 | 5 | 6 | VI-2 | Rag1 | 0.34 |
| 275 | 3 | 4 | 5 | 6 | | VI-2 | Hist1h4j | 0.30 | 371 | 3 | 4 | 5 | 6 | VI-2 | Rbks | 0.48 |
| 276 | 3 | 4 | 5 | 6 | | VI-2 | Hist1h4k | 0.42 | 372 | 3 | 4 | 5 | 6 | VI-2 | Rbp2 | 0.41 |
| 277 | 3 | 4 | 5 | 6 | | VI-2 | Hmbs | 0.46 | 373 | 3 | 4 | 5 | 6 | VI-2 | Rdh9 | 0.46 |
| 278 | 3 | 4 | 5 | 6 | | VI-2 | Hmmr | 0.41 | 374 | 3 | 4 | 5 | 6 | VI-2 | Rgcc | 0.40 |
| 279 | 3 | 4 | 5 | 6 | | VI-2 | Hsph1 | 0.50 | 375 | 3 | 4 | 5 | 6 | VI-2 | Rgn | 0.27 |
| 280 | 3 | 4 | 5 | 6 | | VI-2 | Icam4 | 0.21 | 376 | 3 | 4 | 5 | 6 | VI-2 | Rhag | 0.46 |
| 281 | 3 | 4 | 5 | 6 | | VI-2 | Ifi27 | 0.46 | 377 | 3 | 4 | 5 | 6 | VI-2 | Rhd | 0.21 |
| 282 | 3 | 4 | 5 | 6 | | VI-2 | Igll1 | 0.43 | 378 | 3 | 4 | 5 | 6 | VI-2 | Rmi2 | 0.47 |
| 283 | 3 | 4 | 5 | 6 | | VI-2 | Ikzf1 | 0.47 | 379 | 3 | 4 | 5 | 6 | VI-2 | Rn4.5s | 0.49 |
| 284 | 3 | 4 | 5 | 6 | | VI-2 | Irs4 | 0.46 | 380 | 3 | 4 | 5 | 6 | VI-2 | Rnase1 | 0.42 |
| 285 | 3 | 4 | 5 | 6 | | VI-2 | Isg20 | 0.29 | 381 | 3 | 4 | 5 | 6 | VI-2 | Rnf186 | 0.48 |
| 286 | 3 | 4 | 5 | 6 | | VI-2 | Itih1 | 0.23 | 382 | 3 | 4 | 5 | 6 | VI-2 | Rpa3 | 0.48 |

Fig. 45 - 3

| | | | | | | | | | | | | | | | |
|---|---|---|---|---|---|---|---|---|---|---|---|---|---|---|---|
| 383 | 3 | 4 | 5 | 6 | | VI-2 | Rrm2 | 0.48 | 479 | 3 | 4 | 5 | 6 | VI-2 | Xk | 0.44 |
| 384 | 3 | 4 | 5 | 6 | | VI-2 | Rtp3 | 0.36 | 480 | 3 | 4 | 5 | 6 | VI-2 | Yipf7 | 0.42 |
| 385 | 3 | 4 | 5 | 6 | | VI-2 | S1pr5 | 0.45 | 481 | 3 | 4 | 5 | 6 | VI-2 | Zfp493 | 0.47 |
| 386 | 3 | 4 | 5 | 6 | | VI-2 | Saa4 | 0.28 | 482 | 3 | 4 | 5 | 6 | VI-1 | 0610040B10Rik | 4.55 |
| 387 | 3 | 4 | 5 | 6 | | VI-2 | Samd11 | 0.42 | 483 | 3 | 4 | 5 | 6 | VI-1 | 1100001G20Rik | 3.13 |
| 388 | 3 | 4 | 5 | 6 | | VI-2 | Scd1 | 0.35 | 484 | 3 | 4 | 5 | 6 | VI-1 | 1110015O18Rik | 2.03 |
| 389 | 3 | 4 | 5 | 6 | | VI-2 | Sec61g | 0.47 | 485 | 3 | 4 | 5 | 6 | VI-1 | 1600029O15Rik | 2.66 |
| 390 | 3 | 4 | 5 | 6 | | VI-2 | Serpina10 | 0.43 | 486 | 3 | 4 | 5 | 6 | VI-1 | 1700028K03Rik | 2.10 |
| 391 | 3 | 4 | 5 | 6 | | VI-2 | Serpina12 | 0.48 | 487 | 3 | 4 | 5 | 6 | VI-1 | 1700048M11Rik | 2.31 |
| 392 | 3 | 4 | 5 | 6 | | VI-2 | Serpina1e | 0.39 | 488 | 3 | 4 | 5 | 6 | VI-1 | 1700124L16Rik | 2.35 |
| 393 | 3 | 4 | 5 | 6 | | VI-2 | Serpinb12 | 0.43 | 489 | 3 | 4 | 5 | 6 | VI-1 | 2010005H15Rik | 2.15 |
| 394 | 3 | 4 | 5 | 6 | | VI-2 | Serpinb3b | 0.21 | 490 | 3 | 4 | 5 | 6 | VI-1 | 2310015A10Rik | 2.39 |
| 395 | 3 | 4 | 5 | 6 | | VI-2 | Serpinb3c | 0.28 | 491 | 3 | 4 | 5 | 6 | VI-1 | 2310068J16Rik | 2.68 |
| 396 | 3 | 4 | 5 | 6 | | VI-2 | Serpinc1 | 0.40 | 492 | 3 | 4 | 5 | 6 | VI-1 | 2410004N09Rik | 3.13 |
| 397 | 3 | 4 | 5 | 6 | | VI-2 | Serpind1 | 0.40 | 493 | 3 | 4 | 5 | 6 | VI-1 | 2810454H06Rik | 2.05 |
| 398 | 3 | 4 | 5 | 6 | | VI-2 | Serpinh1 | 0.49 | 494 | 3 | 4 | 5 | 6 | VI-1 | 2900079G21Rik | 2.03 |
| 399 | 3 | 4 | 5 | 6 | | VI-2 | Sh2d4a | 0.38 | 495 | 3 | 4 | 5 | 6 | VI-1 | 2900092D14Rik | 2.21 |
| 400 | 3 | 4 | 5 | 6 | | VI-2 | Sh3bgr | 0.36 | 496 | 3 | 4 | 5 | 6 | VI-1 | 3830408C21Rik | 2.58 |
| 401 | 3 | 4 | 5 | 6 | | VI-2 | Ska1 | 0.42 | 497 | 3 | 4 | 5 | 6 | VI-1 | 4833418N02Rik | 2.44 |
| 402 | 3 | 4 | 5 | 6 | | VI-2 | Slc10a5 | 0.50 | 498 | 3 | 4 | 5 | 6 | VI-1 | 4930474M22Rik | 2.38 |
| 403 | 3 | 4 | 5 | 6 | | VI-2 | Slc16a10 | 0.41 | 499 | 3 | 4 | 5 | 6 | VI-1 | 4930520O04Rik | 2.02 |
| 404 | 3 | 4 | 5 | 6 | | VI-2 | Slc16a3 | 0.42 | 500 | 3 | 4 | 5 | 6 | VI-1 | 4930556M19Rik | 2.23 |
| 405 | 3 | 4 | 5 | 6 | | VI-2 | Slc25a37 | 0.39 | 501 | 3 | 4 | 5 | 6 | VI-1 | 4930570G19Rik | 2.35 |
| 406 | 3 | 4 | 5 | 6 | | VI-2 | Slc26a1 | 0.44 | 502 | 3 | 4 | 5 | 6 | VI-1 | 4933439C10Rik | 2.35 |
| 407 | 3 | 4 | 5 | 6 | | VI-2 | Slc27a5 | 0.39 | 503 | 3 | 4 | 5 | 6 | VI-1 | 5730480H06Rik | 2.68 |
| 408 | 3 | 4 | 5 | 6 | | VI-2 | Slc2a2 | 0.46 | 504 | 3 | 4 | 5 | 6 | VI-1 | 9930014A18Rik | 2.58 |
| 409 | 3 | 4 | 5 | 6 | | VI-2 | Slc2a4rg-ps | 0.41 | 505 | 3 | 4 | 5 | 6 | VI-1 | A730020E08Rik | 2.28 |
| 410 | 3 | 4 | 5 | 6 | | VI-2 | Slc36a2 | 0.26 | 506 | 3 | 4 | 5 | 6 | VI-1 | AA474331 | 2.02 |
| 411 | 3 | 4 | 5 | 6 | | VI-2 | Slc38a5 | 0.36 | 507 | 3 | 4 | 5 | 6 | VI-1 | AI607873 | 2.28 |
| 412 | 3 | 4 | 5 | 6 | | VI-2 | Slc39a5 | 0.40 | 508 | 3 | 4 | 5 | 6 | VI-1 | AI854517 | 2.74 |
| 413 | 3 | 4 | 5 | 6 | | VI-2 | Slc3a1 | 0.37 | 509 | 3 | 4 | 5 | 6 | VI-1 | AW549542 | 2.12 |
| 414 | 3 | 4 | 5 | 6 | | VI-2 | Slc43a1 | 0.46 | 510 | 3 | 4 | 5 | 6 | VI-1 | Acr | 2.86 |
| 415 | 3 | 4 | 5 | 6 | | VI-2 | Slc47a1 | 0.43 | 511 | 3 | 4 | 5 | 6 | VI-1 | Adarb2 | 2.04 |
| 416 | 3 | 4 | 5 | 6 | | VI-2 | Slc4a1 | 0.47 | 512 | 3 | 4 | 5 | 6 | VI-1 | Adc | 2.26 |
| 417 | 3 | 4 | 5 | 6 | | VI-2 | Slc6a19 | 0.43 | 513 | 3 | 4 | 5 | 6 | VI-1 | Adm | 2.54 |
| 418 | 3 | 4 | 5 | 6 | | VI-2 | Smgc | 0.47 | 514 | 3 | 4 | 5 | 6 | VI-1 | Agbl3 | 2.00 |
| 419 | 3 | 4 | 5 | 6 | | VI-2 | Smim24 | 0.46 | 515 | 3 | 4 | 5 | 6 | VI-1 | Ajap1 | 2.06 |
| 420 | 3 | 4 | 5 | 6 | | VI-2 | Smtnl1 | 0.40 | 516 | 3 | 4 | 5 | 6 | VI-1 | Apoa5 | 4.65 |
| 421 | 3 | 4 | 5 | 6 | | VI-2 | Snord15a | 0.29 | 517 | 3 | 4 | 5 | 6 | VI-1 | Armcx5 | 2.35 |
| 422 | 3 | 4 | 5 | 6 | | VI-2 | Sowaha | 0.45 | 518 | 3 | 4 | 5 | 6 | VI-1 | Arnt2 | 2.16 |
| 423 | 3 | 4 | 5 | 6 | | VI-2 | Spink3 | 0.44 | 519 | 3 | 4 | 5 | 6 | VI-1 | Arx | 2.16 |
| 424 | 3 | 4 | 5 | 6 | | VI-2 | Spink4 | 0.32 | 520 | 3 | 4 | 5 | 6 | VI-1 | Asic4 | 2.49 |
| 425 | 3 | 4 | 5 | 6 | | VI-2 | Spon2 | 0.47 | 521 | 3 | 4 | 5 | 6 | VI-1 | Ass1 | 2.01 |
| 426 | 3 | 4 | 5 | 6 | | VI-2 | Spp2 | 0.37 | 522 | 3 | 4 | 5 | 6 | VI-1 | B230208H11Rik | 2.02 |
| 427 | 3 | 4 | 5 | 6 | | VI-2 | Sprr2a1 | 0.25 | 523 | 3 | 4 | 5 | 6 | VI-1 | Barhl1 | 2.34 |
| 428 | 3 | 4 | 5 | 6 | | VI-2 | Sprr2a2 | 0.25 | 524 | 3 | 4 | 5 | 6 | VI-1 | Bpifa1 | 2.35 |
| 429 | 3 | 4 | 5 | 6 | | VI-2 | Sprr3 | 0.40 | 525 | 3 | 4 | 5 | 6 | VI-1 | Brinp3 | 2.25 |
| 430 | 3 | 4 | 5 | 6 | | VI-2 | Spta1 | 0.36 | 526 | 3 | 4 | 5 | 6 | VI-1 | Brsk2 | 2.21 |
| 431 | 3 | 4 | 5 | 6 | | VI-2 | Sptb | 0.43 | 527 | 3 | 4 | 5 | 6 | VI-1 | Bzrap1 | 2.31 |
| 432 | 3 | 4 | 5 | 6 | | VI-2 | Srp54c | 0.48 | 528 | 3 | 4 | 5 | 6 | VI-1 | C130030K03Rik | 2.10 |
| 433 | 3 | 4 | 5 | 6 | | VI-2 | Steap3 | 0.39 | 529 | 3 | 4 | 5 | 6 | VI-1 | Cabyr | 2.12 |
| 434 | 3 | 4 | 5 | 6 | | VI-2 | Stfa3 | 0.45 | 530 | 3 | 4 | 5 | 6 | VI-1 | Cacng2 | 2.03 |
| 435 | 3 | 4 | 5 | 6 | | VI-2 | Sycn | 0.42 | 531 | 3 | 4 | 5 | 6 | VI-1 | Cartpt | 2.50 |
| 436 | 3 | 4 | 5 | 6 | | VI-2 | Sypl2 | 0.38 | 532 | 3 | 4 | 5 | 6 | VI-1 | Ccdc122 | 2.41 |
| 437 | 3 | 4 | 5 | 6 | | VI-2 | Tal1 | 0.40 | 533 | 3 | 4 | 5 | 6 | VI-1 | Ccdc62 | 2.00 |
| 438 | 3 | 4 | 5 | 6 | | VI-2 | Tbata | 0.42 | 534 | 3 | 4 | 5 | 6 | VI-1 | Ccl12 | 3.46 |
| 439 | 3 | 4 | 5 | 6 | | VI-2 | Tcf24 | 0.49 | 535 | 3 | 4 | 5 | 6 | VI-1 | Cd163 | 2.32 |
| 440 | 3 | 4 | 5 | 6 | | VI-2 | Tesc | 0.42 | 536 | 3 | 4 | 5 | 6 | VI-1 | Cd177 | 2.09 |
| 441 | 3 | 4 | 5 | 6 | | VI-2 | Tfec | 0.43 | 537 | 3 | 4 | 5 | 6 | VI-1 | Cd300lf | 2.52 |
| 442 | 3 | 4 | 5 | 6 | | VI-2 | Tfpi2 | 0.39 | 538 | 3 | 4 | 5 | 6 | VI-1 | Cdh18 | 2.24 |
| 443 | 3 | 4 | 5 | 6 | | VI-2 | Tfrc | 0.46 | 539 | 3 | 4 | 5 | 6 | VI-1 | Chac1 | 3.34 |
| 444 | 3 | 4 | 5 | 6 | | VI-2 | Them5 | 0.45 | 540 | 3 | 4 | 5 | 6 | VI-1 | Cirbp | 3.53 |
| 445 | 3 | 4 | 5 | 6 | | VI-2 | Timd2 | 0.30 | 541 | 3 | 4 | 5 | 6 | VI-1 | Clca1 | 2.00 |
| 446 | 3 | 4 | 5 | 6 | | VI-2 | Tm4sf20 | 0.34 | 542 | 3 | 4 | 5 | 6 | VI-1 | Cpne7 | 2.38 |
| 447 | 3 | 4 | 5 | 6 | | VI-2 | Tm4sf5 | 0.46 | 543 | 3 | 4 | 5 | 6 | VI-1 | Ctgf | 2.07 |
| 448 | 3 | 4 | 5 | 6 | | VI-2 | Tmc8 | 0.46 | 544 | 3 | 4 | 5 | 6 | VI-1 | Cyp2a5 | 3.35 |
| 449 | 3 | 4 | 5 | 6 | | VI-2 | Tmem14c | 0.50 | 545 | 3 | 4 | 5 | 6 | VI-1 | Cyp2d9 | 4.20 |
| 450 | 3 | 4 | 5 | 6 | | VI-2 | Tmem184a | 0.50 | 546 | 3 | 4 | 5 | 6 | VI-1 | Cyp4a14 | 2.36 |
| 451 | 3 | 4 | 5 | 6 | | VI-2 | Tmem253 | 0.47 | 547 | 3 | 4 | 5 | 6 | VI-1 | Ddx3y | 2.36 |
| 452 | 3 | 4 | 5 | 6 | | VI-2 | Tmem254c | 0.23 | 548 | 3 | 4 | 5 | 6 | VI-1 | Dennd6b | 2.59 |
| 453 | 3 | 4 | 5 | 6 | | VI-2 | Tmem45b | 0.38 | 549 | 3 | 4 | 5 | 6 | VI-1 | Dio3os | 2.09 |
| 454 | 3 | 4 | 5 | 6 | | VI-2 | Tmem86b | 0.46 | 550 | 3 | 4 | 5 | 6 | VI-1 | Dock3 | 2.12 |
| 455 | 3 | 4 | 5 | 6 | | VI-2 | Tmod4 | 0.36 | 551 | 3 | 4 | 5 | 6 | VI-1 | Dpep1 | 2.08 |
| 456 | 3 | 4 | 5 | 6 | | VI-2 | Tmprss4 | 0.37 | 552 | 3 | 4 | 5 | 6 | VI-1 | Dscaml1 | 2.11 |
| 457 | 3 | 4 | 5 | 6 | | VI-2 | Tmprss6 | 0.43 | 553 | 3 | 4 | 5 | 6 | VI-1 | Dsg3 | 2.76 |
| 458 | 3 | 4 | 5 | 6 | | VI-2 | Tnfrsf14 | 0.39 | 554 | 3 | 4 | 5 | 6 | VI-1 | Duoxa1 | 2.16 |
| 459 | 3 | 4 | 5 | 6 | | VI-2 | Treml1 | 0.38 | 555 | 3 | 4 | 5 | 6 | VI-1 | Duxbl1 | 2.65 |
| 460 | 3 | 4 | 5 | 6 | | VI-2 | Trf | 0.41 | 556 | 3 | 4 | 5 | 6 | VI-1 | Duxbl2 | 2.75 |
| 461 | 3 | 4 | 5 | 6 | | VI-2 | Trim10 | 0.41 | 557 | 3 | 4 | 5 | 6 | VI-1 | Duxbl3 | 3.76 |
| 462 | 3 | 4 | 5 | 6 | | VI-2 | Try10 | 0.40 | 558 | 3 | 4 | 5 | 6 | VI-1 | E030002O03Rik | 2.82 |
| 463 | 3 | 4 | 5 | 6 | | VI-2 | Tspan33 | 0.42 | 559 | 3 | 4 | 5 | 6 | VI-1 | E130102H24Rik | 2.06 |
| 464 | 3 | 4 | 5 | 6 | | VI-2 | Tspan8 | 0.48 | 560 | 3 | 4 | 5 | 6 | VI-1 | E130317F20Rik | 2.41 |
| 465 | 3 | 4 | 5 | 6 | | VI-2 | Tspo2 | 0.46 | 561 | 3 | 4 | 5 | 6 | VI-1 | Eif2s3y | 2.71 |
| 466 | 3 | 4 | 5 | 6 | | VI-2 | Ttr | 0.35 | 562 | 3 | 4 | 5 | 6 | VI-1 | Eny2 | 2.09 |
| 467 | 3 | 4 | 5 | 6 | | VI-2 | Tuba8 | 0.50 | 563 | 3 | 4 | 5 | 6 | VI-1 | Fam107a | 2.29 |
| 468 | 3 | 4 | 5 | 6 | | VI-2 | Txnrd2 | 0.34 | 564 | 3 | 4 | 5 | 6 | VI-1 | Fam155a | 2.10 |
| 469 | 3 | 4 | 5 | 6 | | VI-2 | Tyms-ps | 0.48 | 565 | 3 | 4 | 5 | 6 | VI-1 | Fbll1 | 2.46 |
| 470 | 3 | 4 | 5 | 6 | | VI-2 | Ube2c | 0.48 | 566 | 3 | 4 | 5 | 6 | VI-1 | Fbxo27 | 2.00 |
| 471 | 3 | 4 | 5 | 6 | | VI-2 | Ube2t | 0.47 | 567 | 3 | 4 | 5 | 6 | VI-1 | Fcgr4 | 2.51 |
| 472 | 3 | 4 | 5 | 6 | | VI-2 | Ugt2b34 | 0.45 | 568 | 3 | 4 | 5 | 6 | VI-1 | Fgf21 | 3.75 |
| 473 | 3 | 4 | 5 | 6 | | VI-2 | Ugt2b36 | 0.37 | 569 | 3 | 4 | 5 | 6 | VI-1 | Fgl1 | 2.45 |
| 474 | 3 | 4 | 5 | 6 | | VI-2 | Ugt2b5 | 0.40 | 570 | 3 | 4 | 5 | 6 | VI-1 | Flywch2 | 2.50 |
| 475 | 3 | 4 | 5 | 6 | | VI-2 | Uox | 0.24 | 571 | 3 | 4 | 5 | 6 | VI-1 | Foxg1 | 2.21 |
| 476 | 3 | 4 | 5 | 6 | | VI-2 | Uros | 0.39 | 572 | 3 | 4 | 5 | 6 | VI-1 | Fpr1 | 2.02 |
| 477 | 3 | 4 | 5 | 6 | | VI-2 | Vil1 | 0.38 | 573 | 3 | 4 | 5 | 6 | VI-1 | Gad2 | 2.24 |
| 478 | 3 | 4 | 5 | 6 | | VI-2 | Vtn | 0.43 | 574 | 3 | 4 | 5 | 6 | VI-1 | Gbp3 | 2.56 |

Fig. 45 - 4

| | | | | | | | | | | | | | | | |
|---|---|---|---|---|---|---|---|---|---|---|---|---|---|---|---|
| 575 | 3 | 4 | 5 | 6 | | VI-1 | Gbx2 | 2.39 | 671 | 3 | 4 | 5 | 6 | VI-1 | Sprr2h | 4.59 |
| 576 | 3 | 4 | 5 | 6 | | VI-1 | Gdf15 | 2.03 | 672 | 3 | 4 | 5 | 6 | VI-1 | Syndig1l | 2.17 |
| 577 | 3 | 4 | 5 | 6 | | VI-1 | Gm11974 | 2.15 | 673 | 3 | 4 | 5 | 6 | VI-1 | Tcerg1l | 2.33 |
| 578 | 3 | 4 | 5 | 6 | | VI-1 | Gm13375 | 2.39 | 674 | 3 | 4 | 5 | 6 | VI-1 | Tcf15 | 2.19 |
| 579 | 3 | 4 | 5 | 6 | | VI-1 | Gm14204 | 2.18 | 675 | 3 | 4 | 5 | 6 | VI-1 | Tcte3 | 2.15 |
| 580 | 3 | 4 | 5 | 6 | | VI-1 | Gm14295 | 2.36 | 676 | 3 | 4 | 5 | 6 | VI-1 | Terc | 2.02 |
| 581 | 3 | 4 | 5 | 6 | | VI-1 | Gm14391 | 2.71 | 677 | 3 | 4 | 5 | 6 | VI-1 | Timp4 | 2.11 |
| 582 | 3 | 4 | 5 | 6 | | VI-1 | Gm14634 | 2.24 | 678 | 3 | 4 | 5 | 6 | VI-1 | Tlr13 | 2.15 |
| 583 | 3 | 4 | 5 | 6 | | VI-1 | Gm1673 | 2.96 | 679 | 3 | 4 | 5 | 6 | VI-1 | Tmem145 | 2.59 |
| 584 | 3 | 4 | 5 | 6 | | VI-1 | Gm16845 | 2.19 | 680 | 3 | 4 | 5 | 6 | VI-1 | Tmem163 | 2.08 |
| 585 | 3 | 4 | 5 | 6 | | VI-1 | Gm20257 | 2.05 | 681 | 3 | 4 | 5 | 6 | VI-1 | Tmem240 | 2.02 |
| 586 | 3 | 4 | 5 | 6 | | VI-1 | Gm3383 | 2.04 | 682 | 3 | 4 | 5 | 6 | VI-1 | Tmem8b | 2.05 |
| 587 | 3 | 4 | 5 | 6 | | VI-1 | Gm4070 | 3.02 | 683 | 3 | 4 | 5 | 6 | VI-1 | Tmsb15l | 3.18 |
| 588 | 3 | 4 | 5 | 6 | | VI-1 | Gm4952 | 2.75 | 684 | 3 | 4 | 5 | 6 | VI-1 | Tox | 2.03 |
| 589 | 3 | 4 | 5 | 6 | | VI-1 | Gm5415 | 2.15 | 685 | 3 | 4 | 5 | 6 | VI-1 | Tox2 | 2.04 |
| 590 | 3 | 4 | 5 | 6 | | VI-1 | Gm5607 | 2.06 | 686 | 3 | 4 | 5 | 6 | VI-1 | Tpsab1 | 3.58 |
| 591 | 3 | 4 | 5 | 6 | | VI-1 | Gm7367 | 3.02 | 687 | 3 | 4 | 5 | 6 | VI-1 | Trib3 | 3.39 |
| 592 | 3 | 4 | 5 | 6 | | VI-1 | Gp49a | 2.11 | 688 | 3 | 4 | 5 | 6 | VI-1 | Trim66 | 2.11 |
| 593 | 3 | 4 | 5 | 6 | | VI-1 | Gpnmb | 2.77 | 689 | 3 | 4 | 5 | 6 | VI-1 | Ttll11 | 2.02 |
| 594 | 3 | 4 | 5 | 6 | | VI-1 | Gpr135 | 2.15 | 690 | 3 | 4 | 5 | 6 | VI-1 | Txnrd3 | 2.13 |
| 595 | 3 | 4 | 5 | 6 | | VI-1 | Gpr156 | 2.31 | 691 | 3 | 4 | 5 | 6 | VI-1 | Usp18 | 2.09 |
| 596 | 3 | 4 | 5 | 6 | | VI-1 | Gvin1 | 2.03 | 692 | 3 | 4 | 5 | 6 | VI-1 | Vipr2 | 2.10 |
| 597 | 3 | 4 | 5 | 6 | | VI-1 | Havcr2 | 2.38 | 693 | 3 | 4 | 5 | 6 | VI-1 | Vnn3 | 2.09 |
| 598 | 3 | 4 | 5 | 6 | | VI-1 | Hba-x | 2.36 | 694 | 3 | 4 | 5 | 6 | VI-1 | Xdh | 2.24 |
| 599 | 3 | 4 | 5 | 6 | | VI-1 | Hbb-y | 4.22 | 695 | 3 | 4 | 5 | 6 | VI-1 | Zbtb16 | 2.11 |
| 600 | 3 | 4 | 5 | 6 | | VI-1 | Hepacam | 2.17 | 696 | 3 | 4 | 5 | 6 | VI-1 | Zc3h6 | 2.72 |
| 601 | 3 | 4 | 5 | 6 | | VI-1 | Hmox1 | 2.40 | 697 | 3 | 4 | 5 | 6 | VI-1 | Zg16 | 3.07 |
| 602 | 3 | 4 | 5 | 6 | | VI-1 | Hp | 2.04 | 698 | 3 | 4 | 5 | 6 | VI-1 | Zkscan2 | 2.12 |
| 603 | 3 | 4 | 5 | 6 | | VI-1 | Hrk | 2.04 | 699 | 3 | 4 | 5 | | V-2 | 1110002L01Rik | 0.66 |
| 604 | 3 | 4 | 5 | 6 | | VI-1 | Hyi | 2.20 | 700 | 3 | 4 | 5 | | V-2 | 1110019D14Rik | 0.66 |
| 605 | 3 | 4 | 5 | 6 | | VI-1 | I830012O16Rik | 2.74 | 701 | 3 | 4 | 5 | | V-2 | 1190002F15Rik | 0.63 |
| 606 | 3 | 4 | 5 | 6 | | VI-1 | Ifi204 | 2.43 | 702 | 3 | 4 | 5 | | V-2 | 1500015O10Rik | 0.53 |
| 607 | 3 | 4 | 5 | 6 | | VI-1 | Ifitm6 | 3.72 | 703 | 3 | 4 | 5 | | V-2 | 1700007K13Rik | 0.50 |
| 608 | 3 | 4 | 5 | 6 | | VI-1 | Igfbp1 | 2.44 | 704 | 3 | 4 | 5 | | V-2 | 1700037H04Rik | 0.60 |
| 609 | 3 | 4 | 5 | 6 | | VI-1 | Irgm1 | 2.06 | 705 | 3 | 4 | 5 | | V-2 | 1700055N04Rik | 0.62 |
| 610 | 3 | 4 | 5 | 6 | | VI-1 | Kdm5d | 2.13 | 706 | 3 | 4 | 5 | | V-2 | 1810034E14Rik | 0.65 |
| 611 | 3 | 4 | 5 | 6 | | VI-1 | Klf9 | 2.61 | 707 | 3 | 4 | 5 | | V-2 | 2010002M12Rik | 0.67 |
| 612 | 3 | 4 | 5 | 6 | | VI-1 | Klhdc8a | 2.13 | 708 | 3 | 4 | 5 | | V-2 | 2210016F16Rik | 0.65 |
| 613 | 3 | 4 | 5 | 6 | | VI-1 | Klk1b26 | 2.11 | 709 | 3 | 4 | 5 | | V-2 | 2310002L09Rik | 0.57 |
| 614 | 3 | 4 | 5 | 6 | | VI-1 | Krt16 | 3.09 | 710 | 3 | 4 | 5 | | V-2 | 2310034C09Rik | 0.65 |
| 615 | 3 | 4 | 5 | 6 | | VI-1 | Krt6a | 2.66 | 711 | 3 | 4 | 5 | | V-2 | 2310040G24Rik | 0.60 |
| 616 | 3 | 4 | 5 | 6 | | VI-1 | Krt6b | 2.38 | 712 | 3 | 4 | 5 | | V-2 | 2410076I21Rik | 0.61 |
| 617 | 3 | 4 | 5 | 6 | | VI-1 | LOC100504703 | 2.03 | 713 | 3 | 4 | 5 | | V-2 | 2610528A11Rik | 0.54 |
| 618 | 3 | 4 | 5 | 6 | | VI-1 | Lamp5 | 2.10 | 714 | 3 | 4 | 5 | | V-2 | 2810408I11Rik | 0.56 |
| 619 | 3 | 4 | 5 | 6 | | VI-1 | Lce3c | 3.77 | 715 | 3 | 4 | 5 | | V-2 | 2810442I21Rik | 0.58 |
| 620 | 3 | 4 | 5 | 6 | | VI-1 | Lce3e | 2.10 | 716 | 3 | 4 | 5 | | V-2 | 4631405J19Rik | 0.66 |
| 621 | 3 | 4 | 5 | 6 | | VI-1 | Lgr5 | 2.05 | 717 | 3 | 4 | 5 | | V-2 | 4930500J02Rik | 0.55 |
| 622 | 3 | 4 | 5 | 6 | | VI-1 | Lhx9 | 2.05 | 718 | 3 | 4 | 5 | | V-2 | 4933411K16Rik | 0.54 |
| 623 | 3 | 4 | 5 | 6 | | VI-1 | Lilrb4 | 2.00 | 719 | 3 | 4 | 5 | | V-2 | 4933412E12Rik | 0.65 |
| 624 | 3 | 4 | 5 | 6 | | VI-1 | Lmo3 | 2.07 | 720 | 3 | 4 | 5 | | V-2 | 5330426P16Rik | 0.66 |
| 625 | 3 | 4 | 5 | 6 | | VI-1 | Lmtk3 | 2.13 | 721 | 3 | 4 | 5 | | V-2 | 5430401F13Rik | 0.59 |
| 626 | 3 | 4 | 5 | 6 | | VI-1 | Lmx1b | 2.25 | 722 | 3 | 4 | 5 | | V-2 | 5730508B09Rik | 0.58 |
| 627 | 3 | 4 | 5 | 6 | | VI-1 | Lrg1 | 4.10 | 723 | 3 | 4 | 5 | | V-2 | A230056P14Rik | 0.61 |
| 628 | 3 | 4 | 5 | 6 | | VI-1 | Ly6g5b | 2.70 | 724 | 3 | 4 | 5 | | V-2 | A930003A15Rik | 0.60 |
| 629 | 3 | 4 | 5 | 6 | | VI-1 | Marco | 2.81 | 725 | 3 | 4 | 5 | | V-2 | A930016O22Rik | 0.51 |
| 630 | 3 | 4 | 5 | 6 | | VI-1 | Miat | 2.14 | 726 | 3 | 4 | 5 | | V-2 | AI464131 | 0.64 |
| 631 | 3 | 4 | 5 | 6 | | VI-1 | Mir8094 | 2.01 | 727 | 3 | 4 | 5 | | V-2 | AI467606 | 0.61 |
| 632 | 3 | 4 | 5 | 6 | | VI-1 | Mnda | 2.51 | 728 | 3 | 4 | 5 | | V-2 | AI662270 | 0.54 |
| 633 | 3 | 4 | 5 | 6 | | VI-1 | Ms4a6d | 2.16 | 729 | 3 | 4 | 5 | | V-2 | AU040972 | 0.64 |
| 634 | 3 | 4 | 5 | 6 | | VI-1 | Msr1 | 2.55 | 730 | 3 | 4 | 5 | | V-2 | Aass | 0.58 |
| 635 | 3 | 4 | 5 | 6 | | VI-1 | Nanos3 | 2.17 | 731 | 3 | 4 | 5 | | V-2 | Abca8b | 0.62 |
| 636 | 3 | 4 | 5 | 6 | | VI-1 | Noval | 2.01 | 732 | 3 | 4 | 5 | | V-2 | Abcb10 | 0.53 |
| 637 | 3 | 4 | 5 | 6 | | VI-1 | Noxo1 | 2.24 | 733 | 3 | 4 | 5 | | V-2 | Abcb4 | 0.63 |
| 638 | 3 | 4 | 5 | 6 | | VI-1 | Nptx2 | 2.09 | 734 | 3 | 4 | 5 | | V-2 | Abcc6 | 0.55 |
| 639 | 3 | 4 | 5 | 6 | | VI-1 | Otp | 2.34 | 735 | 3 | 4 | 5 | | V-2 | Abcg4 | 0.66 |
| 640 | 3 | 4 | 5 | 6 | | VI-1 | Ovgp1 | 2.13 | 736 | 3 | 4 | 5 | | V-2 | Abhd15 | 0.64 |
| 641 | 3 | 4 | 5 | 6 | | VI-1 | Pappa | 2.12 | 737 | 3 | 4 | 5 | | V-2 | Abhd3 | 0.62 |
| 642 | 3 | 4 | 5 | 6 | | VI-1 | Parp14 | 2.07 | 738 | 3 | 4 | 5 | | V-2 | Acaa2 | 0.52 |
| 643 | 3 | 4 | 5 | 6 | | VI-1 | Pbx4 | 2.17 | 739 | 3 | 4 | 5 | | V-2 | Acad1 | 0.65 |
| 644 | 3 | 4 | 5 | 6 | | VI-1 | Pcdhb9 | 2.04 | 740 | 3 | 4 | 5 | | V-2 | Acadm | 0.64 |
| 645 | 3 | 4 | 5 | 6 | | VI-1 | Plet1 | 2.35 | 741 | 3 | 4 | 5 | | V-2 | Acadvl | 0.57 |
| 646 | 3 | 4 | 5 | 6 | | VI-1 | Pnma1 | 2.18 | 742 | 3 | 4 | 5 | | V-2 | Acat3 | 0.62 |
| 647 | 3 | 4 | 5 | 6 | | VI-1 | Porcn | 2.40 | 743 | 3 | 4 | 5 | | V-2 | Aco2 | 0.63 |
| 648 | 3 | 4 | 5 | 6 | | VI-1 | Ppp1r1c | 2.06 | 744 | 3 | 4 | 5 | | V-2 | Acot13 | 0.59 |
| 649 | 3 | 4 | 5 | 6 | | VI-1 | Ppp1r3f | 2.03 | 745 | 3 | 4 | 5 | | V-2 | Acsl1 | 0.61 |
| 650 | 3 | 4 | 5 | 6 | | VI-1 | Ppp4r1l-ps | 2.01 | 746 | 3 | 4 | 5 | | V-2 | Acsl5 | 0.51 |
| 651 | 3 | 4 | 5 | 6 | | VI-1 | Prg4 | 2.27 | 747 | 3 | 4 | 5 | | V-2 | Acss2 | 0.53 |
| 652 | 3 | 4 | 5 | 6 | | VI-1 | Prkcg | 2.14 | 748 | 3 | 4 | 5 | | V-2 | Acta1 | 0.61 |
| 653 | 3 | 4 | 5 | 6 | | VI-1 | Rab33a | 2.18 | 749 | 3 | 4 | 5 | | V-2 | Actc1 | 0.64 |
| 654 | 3 | 4 | 5 | 6 | | VI-1 | Rfx4 | 2.03 | 750 | 3 | 4 | 5 | | V-2 | Adhfe1 | 0.64 |
| 655 | 3 | 4 | 5 | 6 | | VI-1 | Rin1 | 2.00 | 751 | 3 | 4 | 5 | | V-2 | Adi1 | 0.67 |
| 656 | 3 | 4 | 5 | 6 | | VI-1 | Scg5 | 2.02 | 752 | 3 | 4 | 5 | | V-2 | Adig | 0.53 |
| 657 | 3 | 4 | 5 | 6 | | VI-1 | Scn1a | 2.03 | 753 | 3 | 4 | 5 | | V-2 | Adora3 | 0.63 |
| 658 | 3 | 4 | 5 | 6 | | VI-1 | Serpina3g | 2.39 | 754 | 3 | 4 | 5 | | V-2 | Agpat5 | 0.59 |
| 659 | 3 | 4 | 5 | 6 | | VI-1 | Serpina7 | 3.19 | 755 | 3 | 4 | 5 | | V-2 | Agpat9 | 0.54 |
| 660 | 3 | 4 | 5 | 6 | | VI-1 | Sez6 | 2.21 | 756 | 3 | 4 | 5 | | V-2 | Agt | 0.52 |
| 661 | 3 | 4 | 5 | 6 | | VI-1 | Slc25a53 | 2.19 | 757 | 3 | 4 | 5 | | V-2 | Agxt2 | 0.63 |
| 662 | 3 | 4 | 5 | 6 | | VI-1 | Slc35f3 | 2.02 | 758 | 3 | 4 | 5 | | V-2 | Ahsg | 0.66 |
| 663 | 3 | 4 | 5 | 6 | | VI-1 | Slc7a11 | 2.01 | 759 | 3 | 4 | 5 | | V-2 | Aifm1 | 0.67 |
| 664 | 3 | 4 | 5 | 6 | | VI-1 | Slco1c1 | 2.07 | 760 | 3 | 4 | 5 | | V-2 | Ak4 | 0.58 |
| 665 | 3 | 4 | 5 | 6 | | VI-1 | Slfn5 | 2.35 | 761 | 3 | 4 | 5 | | V-2 | Ak6 | 0.58 |
| 666 | 3 | 4 | 5 | 6 | | VI-1 | Snhg10 | 2.02 | 762 | 3 | 4 | 5 | | V-2 | Akr1b7 | 0.62 |
| 667 | 3 | 4 | 5 | 6 | | VI-1 | Snora43 | 3.05 | 763 | 3 | 4 | 5 | | V-2 | Akr1c19 | 0.66 |
| 668 | 3 | 4 | 5 | 6 | | VI-1 | Snora44 | 2.04 | 764 | 3 | 4 | 5 | | V-2 | Akr1d1 | 0.53 |
| 669 | 3 | 4 | 5 | 6 | | VI-1 | Snord22 | 4.07 | 765 | 3 | 4 | 5 | | V-2 | Alas2 | 0.57 |
| 670 | 3 | 4 | 5 | 6 | | VI-1 | Sorcs3 | 2.04 | 766 | 3 | 4 | 5 | | V-2 | Aldh1a7 | 0.58 |

Fig. 45 - 5

| | | | | | | | | | | | | | | | |
|---|---|---|---|---|---|---|---|---|---|---|---|---|---|---|---|
| 767 | 3 | 4 | 5 | | | V-2 | Aldh1b1 | 0.59 | 863 | 3 | 4 | 5 | | V-2 | Ccne1 | 0.63 |
| 768 | 3 | 4 | 5 | | | V-2 | Aldh3b2 | 0.67 | 864 | 3 | 4 | 5 | | V-2 | Cd37 | 0.57 |
| 769 | 3 | 4 | 5 | | | V-2 | Aldoa | 0.66 | 865 | 3 | 4 | 5 | | V-2 | Cd82 | 0.58 |
| 770 | 3 | 4 | 5 | | | V-2 | Aldoart1 | 0.66 | 866 | 3 | 4 | 5 | | V-2 | Cd86 | 0.53 |
| 771 | 3 | 4 | 5 | | | V-2 | Aldoart2 | 0.67 | 867 | 3 | 4 | 5 | | V-2 | Cda | 0.66 |
| 772 | 3 | 4 | 5 | | | V-2 | Aldob | 0.64 | 868 | 3 | 4 | 5 | | V-2 | Cdc20 | 0.65 |
| 773 | 3 | 4 | 5 | | | V-2 | Alox12 | 0.54 | 869 | 3 | 4 | 5 | | V-2 | Cdc25b | 0.55 |
| 774 | 3 | 4 | 5 | | | V-2 | Amd2 | 0.61 | 870 | 3 | 4 | 5 | | V-2 | Cdca2 | 0.59 |
| 775 | 3 | 4 | 5 | | | V-2 | Amica1 | 0.61 | 871 | 3 | 4 | 5 | | V-2 | Cdca3 | 0.61 |
| 776 | 3 | 4 | 5 | | | V-2 | Ampd3 | 0.65 | 872 | 3 | 4 | 5 | | V-2 | Cdca5 | 0.60 |
| 777 | 3 | 4 | 5 | | | V-2 | Amy2a2 | 0.62 | 873 | 3 | 4 | 5 | | V-2 | Cdca8 | 0.54 |
| 778 | 3 | 4 | 5 | | | V-2 | Anapc13 | 0.62 | 874 | 3 | 4 | 5 | | V-2 | Cdk2ap2 | 0.62 |
| 779 | 3 | 4 | 5 | | | V-2 | Ank1 | 0.58 | 875 | 3 | 4 | 5 | | V-2 | Cdkn3 | 0.63 |
| 780 | 3 | 4 | 5 | | | V-2 | Ankrd37 | 0.56 | 876 | 3 | 4 | 5 | | V-2 | Cdr2 | 0.63 |
| 781 | 3 | 4 | 5 | | | V-2 | Ankrd9 | 0.59 | 877 | 3 | 4 | 5 | | V-2 | Cdx1 | 0.59 |
| 782 | 3 | 4 | 5 | | | V-2 | Anln | 0.50 | 878 | 3 | 4 | 5 | | V-2 | Cdx2 | 0.52 |
| 783 | 3 | 4 | 5 | | | V-2 | Anxa4 | 0.64 | 879 | 3 | 4 | 5 | | V-2 | Cela3b | 0.59 |
| 784 | 3 | 4 | 5 | | | V-2 | Aoc3 | 0.53 | 880 | 3 | 4 | 5 | | V-2 | Cenpa | 0.55 |
| 785 | 3 | 4 | 5 | | | V-2 | Ap1m2 | 0.65 | 881 | 3 | 4 | 5 | | V-2 | Cenpe | 0.57 |
| 786 | 3 | 4 | 5 | | | V-2 | Apeh | 0.63 | 882 | 3 | 4 | 5 | | V-2 | Cenpf | 0.58 |
| 787 | 3 | 4 | 5 | | | V-2 | Apip | 0.66 | 883 | 3 | 4 | 5 | | V-2 | Cenpi | 0.54 |
| 788 | 3 | 4 | 5 | | | V-2 | Apitd1 | 0.65 | 884 | 3 | 4 | 5 | | V-2 | Cenpl | 0.62 |
| 789 | 3 | 4 | 5 | | | V-2 | Aplnr | 0.65 | 885 | 3 | 4 | 5 | | V-2 | Cenpm | 0.59 |
| 790 | 3 | 4 | 5 | | | V-2 | Apoh | 0.62 | 886 | 3 | 4 | 5 | | V-2 | Cenpn | 0.62 |
| 791 | 3 | 4 | 5 | | | V-2 | Apol7a | 0.60 | 887 | 3 | 4 | 5 | | V-2 | Cenpw | 0.52 |
| 792 | 3 | 4 | 5 | | | V-2 | Apom | 0.57 | 888 | 3 | 4 | 5 | | V-2 | Cep128 | 0.63 |
| 793 | 3 | 4 | 5 | | | V-2 | Apoo | 0.51 | 889 | 3 | 4 | 5 | | V-2 | Cep55 | 0.62 |
| 794 | 3 | 4 | 5 | | | V-2 | Arap3 | 0.63 | 890 | 3 | 4 | 5 | | V-2 | Cep76 | 0.58 |
| 795 | 3 | 4 | 5 | | | V-2 | Arhgap19 | 0.61 | 891 | 3 | 4 | 5 | | V-2 | Ces1d | 0.54 |
| 796 | 3 | 4 | 5 | | | V-2 | Arhgap24 | 0.60 | 892 | 3 | 4 | 5 | | V-2 | Ces2a | 0.64 |
| 797 | 3 | 4 | 5 | | | V-2 | Arhgef16 | 0.62 | 893 | 3 | 4 | 5 | | V-2 | Ces2g | 0.65 |
| 798 | 3 | 4 | 5 | | | V-2 | Arhgef19 | 0.62 | 894 | 3 | 4 | 5 | | V-2 | Cfi | 0.55 |
| 799 | 3 | 4 | 5 | | | V-2 | Arrb1 | 0.59 | 895 | 3 | 4 | 5 | | V-2 | Chaf1a | 0.65 |
| 800 | 3 | 4 | 5 | | | V-2 | Art4 | 0.59 | 896 | 3 | 4 | 5 | | V-2 | Chchd1 | 0.66 |
| 801 | 3 | 4 | 5 | | | V-2 | As3mt | 0.52 | 897 | 3 | 4 | 5 | | V-2 | Chek2 | 0.64 |
| 802 | 3 | 4 | 5 | | | V-2 | Asah2 | 0.60 | 898 | 3 | 4 | 5 | | V-2 | Chpt1 | 0.66 |
| 803 | 3 | 4 | 5 | | | V-2 | Aspdh | 0.63 | 899 | 3 | 4 | 5 | | V-2 | Chst7 | 0.61 |
| 804 | 3 | 4 | 5 | | | V-2 | Asphd1 | 0.64 | 900 | 3 | 4 | 5 | | V-2 | Cit | 0.58 |
| 805 | 3 | 4 | 5 | | | V-2 | Aspm | 0.54 | 901 | 3 | 4 | 5 | | V-2 | Cited1 | 0.54 |
| 806 | 3 | 4 | 5 | | | V-2 | Asprv1 | 0.58 | 902 | 3 | 4 | 5 | | V-2 | Ckap2l | 0.59 |
| 807 | 3 | 4 | 5 | | | V-2 | Atp1b4 | 0.63 | 903 | 3 | 4 | 5 | | V-2 | Cklf | 0.59 |
| 808 | 3 | 4 | 5 | | | V-2 | Atp2a3 | 0.57 | 904 | 3 | 4 | 5 | | V-2 | Ckmt1 | 0.61 |
| 809 | 3 | 4 | 5 | | | V-2 | Atp5d | 0.67 | 905 | 3 | 4 | 5 | | V-2 | Cks1b | 0.60 |
| 810 | 3 | 4 | 5 | | | V-2 | Atp5e | 0.66 | 906 | 3 | 4 | 5 | | V-2 | Cldn18 | 0.63 |
| 811 | 3 | 4 | 5 | | | V-2 | Atp5h | 0.63 | 907 | 3 | 4 | 5 | | V-2 | Cldn2 | 0.55 |
| 812 | 3 | 4 | 5 | | | V-2 | Atp5j2 | 0.62 | 908 | 3 | 4 | 5 | | V-2 | Cldn7 | 0.60 |
| 813 | 3 | 4 | 5 | | | V-2 | Atp6v0d2 | 0.53 | 909 | 3 | 4 | 5 | | V-2 | Clec11a | 0.58 |
| 814 | 3 | 4 | 5 | | | V-2 | Atp6v1c2 | 0.56 | 910 | 3 | 4 | 5 | | V-2 | Clec12a | 0.62 |
| 815 | 3 | 4 | 5 | | | V-2 | Atp7b | 0.50 | 911 | 3 | 4 | 5 | | V-2 | Clec2h | 0.52 |
| 816 | 3 | 4 | 5 | | | V-2 | Aurka | 0.53 | 912 | 3 | 4 | 5 | | V-2 | Clec3b | 0.65 |
| 817 | 3 | 4 | 5 | | | V-2 | Aurkb | 0.59 | 913 | 3 | 4 | 5 | | V-2 | Clic5 | 0.53 |
| 818 | 3 | 4 | 5 | | | V-2 | Aven | 0.54 | 914 | 3 | 4 | 5 | | V-2 | Clps | 0.65 |
| 819 | 3 | 4 | 5 | | | V-2 | B230216G23Rik | 0.65 | 915 | 3 | 4 | 5 | | V-2 | Cmbl | 0.59 |
| 820 | 3 | 4 | 5 | | | V-2 | B4galnt2 | 0.50 | 916 | 3 | 4 | 5 | | V-2 | Cmc2 | 0.50 |
| 821 | 3 | 4 | 5 | | | V-2 | BC024386 | 0.64 | 917 | 3 | 4 | 5 | | V-2 | Cmtm7 | 0.66 |
| 822 | 3 | 4 | 5 | | | V-2 | BC030867 | 0.62 | 918 | 3 | 4 | 5 | | V-2 | Cmtm8 | 0.61 |
| 823 | 3 | 4 | 5 | | | V-2 | BC030870 | 0.58 | 919 | 3 | 4 | 5 | | V-2 | Cnn1 | 0.62 |
| 824 | 3 | 4 | 5 | | | V-2 | BC035044 | 0.67 | 920 | 3 | 4 | 5 | | V-2 | Coa3 | 0.65 |
| 825 | 3 | 4 | 5 | | | V-2 | BC065397 | 0.61 | 921 | 3 | 4 | 5 | | V-2 | Coa4 | 0.50 |
| 826 | 3 | 4 | 5 | | | V-2 | BC068281 | 0.57 | 922 | 3 | 4 | 5 | | V-2 | Col14a1 | 0.67 |
| 827 | 3 | 4 | 5 | | | V-2 | Bag2 | 0.65 | 923 | 3 | 4 | 5 | | V-2 | Col15a1 | 0.62 |
| 828 | 3 | 4 | 5 | | | V-2 | Baiap2l2 | 0.58 | 924 | 3 | 4 | 5 | | V-2 | Col1a1 | 0.63 |
| 829 | 3 | 4 | 5 | | | V-2 | Banp | 0.54 | 925 | 3 | 4 | 5 | | V-2 | Col5a3 | 0.60 |
| 830 | 3 | 4 | 5 | | | V-2 | Bcas1 | 0.55 | 926 | 3 | 4 | 5 | | V-2 | Col6a4 | 0.50 |
| 831 | 3 | 4 | 5 | | | V-2 | Bglap | 0.55 | 927 | 3 | 4 | 5 | | V-2 | Colec11 | 0.61 |
| 832 | 3 | 4 | 5 | | | V-2 | Bhlha15 | 0.58 | 928 | 3 | 4 | 5 | | V-2 | Commd1 | 0.66 |
| 833 | 3 | 4 | 5 | | | V-2 | Bhmt2 | 0.52 | 929 | 3 | 4 | 5 | | V-2 | Cox17 | 0.56 |
| 834 | 3 | 4 | 5 | | | V-2 | Bnipl | 0.62 | 930 | 3 | 4 | 5 | | V-2 | Cox4i2 | 0.63 |
| 835 | 3 | 4 | 5 | | | V-2 | Bola3 | 0.56 | 931 | 3 | 4 | 5 | | V-2 | Cox5a | 0.65 |
| 836 | 3 | 4 | 5 | | | V-2 | Brca1 | 0.56 | 932 | 3 | 4 | 5 | | V-2 | Cox6a1 | 0.61 |
| 837 | 3 | 4 | 5 | | | V-2 | Brip1 | 0.58 | 933 | 3 | 4 | 5 | | V-2 | Cox7a1 | 0.54 |
| 838 | 3 | 4 | 5 | | | V-2 | Btc | 0.52 | 934 | 3 | 4 | 5 | | V-2 | Cox7b | 0.64 |
| 839 | 3 | 4 | 5 | | | V-2 | Btg2 | 0.63 | 935 | 3 | 4 | 5 | | V-2 | Cpb1 | 0.58 |
| 840 | 3 | 4 | 5 | | | V-2 | Btg3 | 0.57 | 936 | 3 | 4 | 5 | | V-2 | Cpt1b | 0.62 |
| 841 | 3 | 4 | 5 | | | V-2 | Btnl6 | 0.54 | 937 | 3 | 4 | 5 | | V-2 | Crb3 | 0.53 |
| 842 | 3 | 4 | 5 | | | V-2 | Bub1 | 0.59 | 938 | 3 | 4 | 5 | | V-2 | Crlf3 | 0.66 |
| 843 | 3 | 4 | 5 | | | V-2 | Bub1b | 0.54 | 939 | 3 | 4 | 5 | | V-2 | Cs | 0.66 |
| 844 | 3 | 4 | 5 | | | V-2 | C130079G13Rik | 0.66 | 940 | 3 | 4 | 5 | | V-2 | Csl | 0.63 |
| 845 | 3 | 4 | 5 | | | V-2 | C1qtnf9 | 0.51 | 941 | 3 | 4 | 5 | | V-2 | Csta1 | 0.59 |
| 846 | 3 | 4 | 5 | | | V-2 | C1s1 | 0.61 | 942 | 3 | 4 | 5 | | V-2 | Cyc1 | 0.64 |
| 847 | 3 | 4 | 5 | | | V-2 | C330018D20Rik | 0.56 | 943 | 3 | 4 | 5 | | V-2 | Cycs | 0.62 |
| 848 | 3 | 4 | 5 | | | V-2 | C330027C09Rik | 0.55 | 944 | 3 | 4 | 5 | | V-2 | Cyp11a1 | 0.60 |
| 849 | 3 | 4 | 5 | | | V-2 | C8g | 0.64 | 945 | 3 | 4 | 5 | | V-2 | Cyp2b19 | 0.58 |
| 850 | 3 | 4 | 5 | | | V-2 | Calr | 0.61 | 946 | 3 | 4 | 5 | | V-2 | Cyp2c40 | 0.58 |
| 851 | 3 | 4 | 5 | | | V-2 | Cap2 | 0.62 | 947 | 3 | 4 | 5 | | V-2 | Cyp2c68 | 0.65 |
| 852 | 3 | 4 | 5 | | | V-2 | Card10 | 0.61 | 948 | 3 | 4 | 5 | | V-2 | Cyp2c70 | 0.55 |
| 853 | 3 | 4 | 5 | | | V-2 | Casp14 | 0.58 | 949 | 3 | 4 | 5 | | V-2 | Cyp2d26 | 0.56 |
| 854 | 3 | 4 | 5 | | | V-2 | Cat | 0.64 | 950 | 3 | 4 | 5 | | V-2 | Cyp2s1 | 0.63 |
| 855 | 3 | 4 | 5 | | | V-2 | Cav1 | 0.54 | 951 | 3 | 4 | 5 | | V-2 | Cyp4f39 | 0.54 |
| 856 | 3 | 4 | 5 | | | V-2 | Cbs | 0.65 | 952 | 3 | 4 | 5 | | V-2 | D10Jhu81e | 0.67 |
| 857 | 3 | 4 | 5 | | | V-2 | Ccdc109b | 0.66 | 953 | 3 | 4 | 5 | | V-2 | Dak | 0.65 |
| 858 | 3 | 4 | 5 | | | V-2 | Ccdc64b | 0.60 | 954 | 3 | 4 | 5 | | V-2 | Dapk2 | 0.54 |
| 859 | 3 | 4 | 5 | | | V-2 | Ccdc77 | 0.65 | 955 | 3 | 4 | 5 | | V-2 | Dbi | 0.58 |
| 860 | 3 | 4 | 5 | | | V-2 | Ccl21a | 0.56 | 956 | 3 | 4 | 5 | | V-2 | Dck | 0.57 |
| 861 | 3 | 4 | 5 | | | V-2 | Ccnb1 | 0.61 | 957 | 3 | 4 | 5 | | V-2 | Dcnp3 | 0.56 |
| 862 | 3 | 4 | 5 | | | V-2 | Ccnb2 | 0.55 | 958 | 3 | 4 | 5 | | V-2 | Ddo | 0.50 |

Fig. 45 - 6

| | | | | | | | | | | | | | | | |
|---|---|---|---|---|---|---|---|---|---|---|---|---|---|---|---|
| 959 | 3 | 4 | 5 | | | V-2 | Ddx39 | 0.63 | 1055 | 3 | 4 | 5 | | V-2 | Fndc9 | 0.55 |
| 960 | 3 | 4 | 5 | | | V-2 | Decr1 | 0.63 | 1056 | 3 | 4 | 5 | | V-2 | Folr1 | 0.67 |
| 961 | 3 | 4 | 5 | | | V-2 | Defa24 | 0.53 | 1057 | 3 | 4 | 5 | | V-2 | Foxa3 | 0.56 |
| 962 | 3 | 4 | 5 | | | V-2 | Dennd1c | 0.67 | 1058 | 3 | 4 | 5 | | V-2 | Foxn1 | 0.57 |
| 963 | 3 | 4 | 5 | | | V-2 | Depdc1a | 0.51 | 1059 | 3 | 4 | 5 | | V-2 | Frrs1 | 0.62 |
| 964 | 3 | 4 | 5 | | | V-2 | Depdc1b | 0.55 | 1060 | 3 | 4 | 5 | | V-2 | Fut2 | 0.56 |
| 965 | 3 | 4 | 5 | | | V-2 | Depdc7 | 0.64 | 1061 | 3 | 4 | 5 | | V-2 | G630090E17Rik | 0.59 |
| 966 | 3 | 4 | 5 | | | V-2 | Des | 0.65 | 1062 | 3 | 4 | 5 | | V-2 | Gal3st4 | 0.56 |
| 967 | 3 | 4 | 5 | | | V-2 | Dgat2 | 0.65 | 1063 | 3 | 4 | 5 | | V-2 | Gale | 0.61 |
| 968 | 3 | 4 | 5 | | | V-2 | Dhcr7 | 0.59 | 1064 | 3 | 4 | 5 | | V-2 | Galnt6 | 0.60 |
| 969 | 3 | 4 | 5 | | | V-2 | Dhrs4 | 0.65 | 1065 | 3 | 4 | 5 | | V-2 | Gata5 | 0.56 |
| 970 | 3 | 4 | 5 | | | V-2 | Dhrs7 | 0.64 | 1066 | 3 | 4 | 5 | | V-2 | Gcg | 0.51 |
| 971 | 3 | 4 | 5 | | | V-2 | Dhrs7c | 0.51 | 1067 | 3 | 4 | 5 | | V-2 | Gcgr | 0.66 |
| 972 | 3 | 4 | 5 | | | V-2 | Diap3 | 0.67 | 1068 | 3 | 4 | 5 | | V-2 | Gchfr | 0.55 |
| 973 | 3 | 4 | 5 | | | V-2 | Dkk1 | 0.67 | 1069 | 3 | 4 | 5 | | V-2 | Gckr | 0.52 |
| 974 | 3 | 4 | 5 | | | V-2 | Dlx3 | 0.53 | 1070 | 3 | 4 | 5 | | V-2 | Gemin6 | 0.65 |
| 975 | 3 | 4 | 5 | | | V-2 | Dmgdh | 0.54 | 1071 | 3 | 4 | 5 | | V-2 | Gen1 | 0.58 |
| 976 | 3 | 4 | 5 | | | V-2 | Dnaic2 | 0.64 | 1072 | 3 | 4 | 5 | | V-2 | Gimap1 | 0.66 |
| 977 | 3 | 4 | 5 | | | V-2 | Dnajc22 | 0.63 | 1073 | 3 | 4 | 5 | | V-2 | Gimap4 | 0.56 |
| 978 | 3 | 4 | 5 | | | V-2 | Dsg1a | 0.61 | 1074 | 3 | 4 | 5 | | V-2 | Gins1 | 0.60 |
| 979 | 3 | 4 | 5 | | | V-2 | Dsg1c | 0.67 | 1075 | 3 | 4 | 5 | | V-2 | Gins3 | 0.64 |
| 980 | 3 | 4 | 5 | | | V-2 | E030019B13Rik | 0.65 | 1076 | 3 | 4 | 5 | | V-2 | Gipc2 | 0.59 |
| 981 | 3 | 4 | 5 | | | V-2 | E130309D14Rik | 0.65 | 1077 | 3 | 4 | 5 | | V-2 | Gjb3 | 0.63 |
| 982 | 3 | 4 | 5 | | | V-2 | E2f2 | 0.63 | 1078 | 3 | 4 | 5 | | V-2 | Gm10681 | 0.61 |
| 983 | 3 | 4 | 5 | | | V-2 | E2f4 | 0.63 | 1079 | 3 | 4 | 5 | | V-2 | Gm11992 | 0.62 |
| 984 | 3 | 4 | 5 | | | V-2 | E2f8 | 0.60 | 1080 | 3 | 4 | 5 | | V-2 | Gm13152 | 0.67 |
| 985 | 3 | 4 | 5 | | | V-2 | Ebp | 0.55 | 1081 | 3 | 4 | 5 | | V-2 | Gm13304 | 0.65 |
| 986 | 3 | 4 | 5 | | | V-2 | Echdc1 | 0.58 | 1082 | 3 | 4 | 5 | | V-2 | Gm13308 | 0.65 |
| 987 | 3 | 4 | 5 | | | V-2 | Eci1 | 0.53 | 1083 | 3 | 4 | 5 | | V-2 | Gm15915 | 0.61 |
| 988 | 3 | 4 | 5 | | | V-2 | Ect2 | 0.60 | 1084 | 3 | 4 | 5 | | V-2 | Gm19990 | 0.54 |
| 989 | 3 | 4 | 5 | | | V-2 | Eef1d | 0.63 | 1085 | 3 | 4 | 5 | | V-2 | Gm3776 | 0.65 |
| 990 | 3 | 4 | 5 | | | V-2 | Efhd1 | 0.55 | 1086 | 3 | 4 | 5 | | V-2 | Gm5088 | 0.64 |
| 991 | 3 | 4 | 5 | | | V-2 | Ehbp1l1 | 0.61 | 1087 | 3 | 4 | 5 | | V-2 | Gm5512 | 0.64 |
| 992 | 3 | 4 | 5 | | | V-2 | Ehd2 | 0.64 | 1088 | 3 | 4 | 5 | | V-2 | Gm8615 | 0.55 |
| 993 | 3 | 4 | 5 | | | V-2 | Eif2 | 0.51 | 1089 | 3 | 4 | 5 | | V-2 | Gm9696 | 0.57 |
| 994 | 3 | 4 | 5 | | | V-2 | Eme1 | 0.62 | 1090 | 3 | 4 | 5 | | V-2 | Gmnn | 0.57 |
| 995 | 3 | 4 | 5 | | | V-2 | Emr1 | 0.62 | 1091 | 3 | 4 | 5 | | V-2 | Gmpr | 0.52 |
| 996 | 3 | 4 | 5 | | | V-2 | Endou | 0.58 | 1092 | 3 | 4 | 5 | | V-2 | Gnpda1 | 0.64 |
| 997 | 3 | 4 | 5 | | | V-2 | Entpd3 | 0.57 | 1093 | 3 | 4 | 5 | | V-2 | Gpa33 | 0.56 |
| 998 | 3 | 4 | 5 | | | V-2 | Epcam | 0.62 | 1094 | 3 | 4 | 5 | | V-2 | Gper1 | 0.59 |
| 999 | 3 | 4 | 5 | | | V-2 | Ephx2 | 0.64 | 1095 | 3 | 4 | 5 | | V-2 | Gpr146 | 0.57 |
| 1000 | 3 | 4 | 5 | | | V-2 | Eps8l1 | 0.57 | 1096 | 3 | 4 | 5 | | V-2 | Gpr183 | 0.61 |
| 1001 | 3 | 4 | 5 | | | V-2 | Esco2 | 0.55 | 1097 | 3 | 4 | 5 | | V-2 | Gpr87 | 0.58 |
| 1002 | 3 | 4 | 5 | | | V-2 | Espl1 | 0.62 | 1098 | 3 | 4 | 5 | | V-2 | Gprin3 | 0.61 |
| 1003 | 3 | 4 | 5 | | | V-2 | Etnk2 | 0.63 | 1099 | 3 | 4 | 5 | | V-2 | Gpt | 0.59 |
| 1004 | 3 | 4 | 5 | | | V-2 | Exoc3l4 | 0.60 | 1100 | 3 | 4 | 5 | | V-2 | Gpx1 | 0.57 |
| 1005 | 3 | 4 | 5 | | | V-2 | F10 | 0.56 | 1101 | 3 | 4 | 5 | | V-2 | Gpx7 | 0.64 |
| 1006 | 3 | 4 | 5 | | | V-2 | F12 | 0.52 | 1102 | 3 | 4 | 5 | | V-2 | Grap | 0.60 |
| 1007 | 3 | 4 | 5 | | | V-2 | F13b | 0.66 | 1103 | 3 | 4 | 5 | | V-2 | Grb7 | 0.65 |
| 1008 | 3 | 4 | 5 | | | V-2 | F2 | 0.50 | 1104 | 3 | 4 | 5 | | V-2 | Gsdma | 0.59 |
| 1009 | 3 | 4 | 5 | | | V-2 | F830016B08Rik | 0.55 | 1105 | 3 | 4 | 5 | | V-2 | Gsg2 | 0.62 |
| 1010 | 3 | 4 | 5 | | | V-2 | Faah | 0.53 | 1106 | 3 | 4 | 5 | | V-2 | Guca2a | 0.61 |
| 1011 | 3 | 4 | 5 | | | V-2 | Fabp5 | 0.53 | 1107 | 3 | 4 | 5 | | V-2 | Gypc | 0.54 |
| 1012 | 3 | 4 | 5 | | | V-2 | Fam111a | 0.51 | 1108 | 3 | 4 | 5 | | V-2 | Gys1 | 0.58 |
| 1013 | 3 | 4 | 5 | | | V-2 | Fam117a | 0.57 | 1109 | 3 | 4 | 5 | | V-2 | Gzma | 0.61 |
| 1014 | 3 | 4 | 5 | | | V-2 | Fam132a | 0.61 | 1110 | 3 | 4 | 5 | | V-2 | H2-K1 | 0.61 |
| 1015 | 3 | 4 | 5 | | | V-2 | Fam161b | 0.65 | 1111 | 3 | 4 | 5 | | V-2 | H2-K2 | 0.58 |
| 1016 | 3 | 4 | 5 | | | V-2 | Fam162a | 0.56 | 1112 | 3 | 4 | 5 | | V-2 | H2-Q1 | 0.57 |
| 1017 | 3 | 4 | 5 | | | V-2 | Fam195a | 0.50 | 1113 | 3 | 4 | 5 | | V-2 | H2-Q10 | 0.53 |
| 1018 | 3 | 4 | 5 | | | V-2 | Fam210a | 0.67 | 1114 | 3 | 4 | 5 | | V-2 | H2-Q7 | 0.50 |
| 1019 | 3 | 4 | 5 | | | V-2 | Fam26e | 0.61 | 1115 | 3 | 4 | 5 | | V-2 | H2-T3 | 0.53 |
| 1020 | 3 | 4 | 5 | | | V-2 | Fam46a | 0.64 | 1116 | 3 | 4 | 5 | | V-2 | H2afx | 0.60 |
| 1021 | 3 | 4 | 5 | | | V-2 | Fam53b | 0.62 | 1117 | 3 | 4 | 5 | | V-2 | Hadh | 0.54 |
| 1022 | 3 | 4 | 5 | | | V-2 | Fam57a | 0.61 | 1118 | 3 | 4 | 5 | | V-2 | Hadha | 0.65 |
| 1023 | 3 | 4 | 5 | | | V-2 | Fam64a | 0.64 | 1119 | 3 | 4 | 5 | | V-2 | Hadhb | 0.67 |
| 1024 | 3 | 4 | 5 | | | V-2 | Fam78a | 0.51 | 1120 | 3 | 4 | 5 | | V-2 | Hagh | 0.61 |
| 1025 | 3 | 4 | 5 | | | V-2 | Fam83c | 0.59 | 1121 | 3 | 4 | 5 | | V-2 | Hal | 0.56 |
| 1026 | 3 | 4 | 5 | | | V-2 | Fam83d | 0.64 | 1122 | 3 | 4 | 5 | | V-2 | Haus8 | 0.51 |
| 1027 | 3 | 4 | 5 | | | V-2 | Fam83e | 0.60 | 1123 | 3 | 4 | 5 | | V-2 | Hbb-bh1 | 0.52 |
| 1028 | 3 | 4 | 5 | | | V-2 | Fam83f | 0.54 | 1124 | 3 | 4 | 5 | | V-2 | Hbq1a | 0.52 |
| 1029 | 3 | 4 | 5 | | | V-2 | Fam83g | 0.64 | 1125 | 3 | 4 | 5 | | V-2 | Hbq1b | 0.63 |
| 1030 | 3 | 4 | 5 | | | V-2 | Fam96b | 0.62 | 1126 | 3 | 4 | 5 | | V-2 | Hexa | 0.61 |
| 1031 | 3 | 4 | 5 | | | V-2 | Fancd2 | 0.64 | 1127 | 3 | 4 | 5 | | V-2 | Heyl | 0.67 |
| 1032 | 3 | 4 | 5 | | | V-2 | Fanci | 0.66 | 1128 | 3 | 4 | 5 | | V-2 | Hgfac | 0.53 |
| 1033 | 3 | 4 | 5 | | | V-2 | Fap | 0.61 | 1129 | 3 | 4 | 5 | | V-2 | Hibadh | 0.66 |
| 1034 | 3 | 4 | 5 | | | V-2 | Fas | 0.67 | 1130 | 3 | 4 | 5 | | V-2 | Hibch | 0.59 |
| 1035 | 3 | 4 | 5 | | | V-2 | Fastkd2 | 0.67 | 1131 | 3 | 4 | 5 | | V-2 | Higd1b | 0.57 |
| 1036 | 3 | 4 | 5 | | | V-2 | Fbln1 | 0.62 | 1132 | 3 | 4 | 5 | | V-2 | Hipk2 | 0.66 |
| 1037 | 3 | 4 | 5 | | | V-2 | Fbxl8 | 0.51 | 1133 | 3 | 4 | 5 | | V-2 | Hist1h1d | 0.64 |
| 1038 | 3 | 4 | 5 | | | V-2 | Fbxo30 | 0.66 | 1134 | 3 | 4 | 5 | | V-2 | Hist1h2ac | 0.57 |
| 1039 | 3 | 4 | 5 | | | V-2 | Fbxo48 | 0.64 | 1135 | 3 | 4 | 5 | | V-2 | Hist1h2ad | 0.51 |
| 1040 | 3 | 4 | 5 | | | V-2 | Fbxo5 | 0.54 | 1136 | 3 | 4 | 5 | | V-2 | Hist1h2ae | 0.53 |
| 1041 | 3 | 4 | 5 | | | V-2 | Fcris | 0.53 | 1137 | 3 | 4 | 5 | | V-2 | Hist1h2ag | 0.57 |
| 1042 | 3 | 4 | 5 | | | V-2 | Fdxr | 0.67 | 1138 | 3 | 4 | 5 | | V-2 | Hist1h2ao | 0.52 |
| 1043 | 3 | 4 | 5 | | | V-2 | Fech | 0.64 | 1139 | 3 | 4 | 5 | | V-2 | Hist1h2bc | 0.55 |
| 1044 | 3 | 4 | 5 | | | V-2 | Fen1 | 0.53 | 1140 | 3 | 4 | 5 | | V-2 | Hist1h2bh | 0.54 |
| 1045 | 3 | 4 | 5 | | | V-2 | Fermt3 | 0.60 | 1141 | 3 | 4 | 5 | | V-2 | Hist1h2bj | 0.57 |
| 1046 | 3 | 4 | 5 | | | V-2 | Fgf6 | 0.62 | 1142 | 3 | 4 | 5 | | V-2 | Hist1h2bm | 0.51 |
| 1047 | 3 | 4 | 5 | | | V-2 | Fgg | 0.67 | 1143 | 3 | 4 | 5 | | V-2 | Hist1h2bq | 0.62 |
| 1048 | 3 | 4 | 5 | | | V-2 | Fh1 | 0.65 | 1144 | 3 | 4 | 5 | | V-2 | Hist1h3d | 0.53 |
| 1049 | 3 | 4 | 5 | | | V-2 | Fitm1 | 0.55 | 1145 | 3 | 4 | 5 | | V-2 | Hist1h3i | 0.67 |
| 1050 | 3 | 4 | 5 | | | V-2 | Fkbp11 | 0.65 | 1146 | 3 | 4 | 5 | | V-2 | Hist1h4a | 0.65 |
| 1051 | 3 | 4 | 5 | | | V-2 | Fkbp2 | 0.53 | 1147 | 3 | 4 | 5 | | V-2 | Hist1h4c | 0.51 |
| 1052 | 3 | 4 | 5 | | | V-2 | Flt3l | 0.54 | 1148 | 3 | 4 | 5 | | V-2 | Hist2h3c2 | 0.54 |
| 1053 | 3 | 4 | 5 | | | V-2 | Fn3krp | 0.54 | 1149 | 3 | 4 | 5 | | V-2 | Hjurp | 0.57 |
| 1054 | 3 | 4 | 5 | | | V-2 | Fndc3c1 | 0.60 | 1150 | 3 | 4 | 5 | | V-2 | Hk1os | 0.61 |

Fig. 45 - 7

| | | | | | | | | | | | | | | | | |
|---|---|---|---|---|---|---|---|---|---|---|---|---|---|---|---|---|
| 1151 | 3 | 4 | 5 | | | V-2 | Hk2 | 0.65 | 1247 | 3 | 4 | 5 | | | V-2 | Lgals7 | 0.66 |
| 1152 | 3 | 4 | 5 | | | V-2 | Hk3 | 0.65 | 1248 | 3 | 4 | 5 | | | V-2 | Lmcd1 | 0.63 |
| 1153 | 3 | 4 | 5 | | | V-2 | Hkdc1 | 0.55 | 1249 | 3 | 4 | 5 | | | V-2 | Lmo2 | 0.57 |
| 1154 | 3 | 4 | 5 | | | V-2 | Hmgb2 | 0.67 | 1250 | 3 | 4 | 5 | | | V-2 | Lpcat3 | 0.65 |
| 1155 | 3 | 4 | 5 | | | V-2 | Hnf4a | 0.66 | 1251 | 3 | 4 | 5 | | | V-2 | Lrat | 0.62 |
| 1156 | 3 | 4 | 5 | | | V-2 | Hnf4g | 0.50 | 1252 | 3 | 4 | 5 | | | V-2 | Lrmp | 0.51 |
| 1157 | 3 | 4 | 5 | | | V-2 | Hnrnpc | 0.60 | 1253 | 3 | 4 | 5 | | | V-2 | Lrtm1 | 0.58 |
| 1158 | 3 | 4 | 5 | | | V-2 | Hoxa1 | 0.62 | 1254 | 3 | 4 | 5 | | | V-2 | Lsmem1 | 0.50 |
| 1159 | 3 | 4 | 5 | | | V-2 | Hpn | 0.53 | 1255 | 3 | 4 | 5 | | | V-2 | Lum | 0.67 |
| 1160 | 3 | 4 | 5 | | | V-2 | Hrnr | 0.50 | 1256 | 3 | 4 | 5 | | | V-2 | Ly6g6e | 0.65 |
| 1161 | 3 | 4 | 5 | | | V-2 | Hsd17b2 | 0.58 | 1257 | 3 | 4 | 5 | | | V-2 | Lyl1 | 0.59 |
| 1162 | 3 | 4 | 5 | | | V-2 | Hsd3b1 | 0.58 | 1258 | 3 | 4 | 5 | | | V-2 | Lynx1 | 0.66 |
| 1163 | 3 | 4 | 5 | | | V-2 | Hsp90b1 | 0.63 | 1259 | 3 | 4 | 5 | | | V-2 | Lypd8 | 0.50 |
| 1164 | 3 | 4 | 5 | | | V-2 | Hspa4 | 0.66 | 1260 | 3 | 4 | 5 | | | V-2 | Lyz2 | 0.65 |
| 1165 | 3 | 4 | 5 | | | V-2 | Hspa5 | 0.64 | 1261 | 3 | 4 | 5 | | | V-2 | Mad2l1 | 0.53 |
| 1166 | 3 | 4 | 5 | | | V-2 | Hspd1 | 0.64 | 1262 | 3 | 4 | 5 | | | V-2 | Magt1 | 0.62 |
| 1167 | 3 | 4 | 5 | | | V-2 | Hspe1 | 0.63 | 1263 | 3 | 4 | 5 | | | V-2 | March3 | 0.63 |
| 1168 | 3 | 4 | 5 | | | V-2 | Htra1 | 0.65 | 1264 | 3 | 4 | 5 | | | V-2 | Marcksl1-ps4 | 0.54 |
| 1169 | 3 | 4 | 5 | | | V-2 | Icam2 | 0.58 | 1265 | 3 | 4 | 5 | | | V-2 | Mcm10 | 0.59 |
| 1170 | 3 | 4 | 5 | | | V-2 | Idh3a | 0.53 | 1266 | 3 | 4 | 5 | | | V-2 | Mcm2 | 0.58 |
| 1171 | 3 | 4 | 5 | | | V-2 | Idh3b | 0.67 | 1267 | 3 | 4 | 5 | | | V-2 | Mcm3 | 0.63 |
| 1172 | 3 | 4 | 5 | | | V-2 | Idi2 | 0.53 | 1268 | 3 | 4 | 5 | | | V-2 | Mcm5 | 0.57 |
| 1173 | 3 | 4 | 5 | | | V-2 | Ifi27l2b | 0.63 | 1269 | 3 | 4 | 5 | | | V-2 | Mcm6 | 0.58 |
| 1174 | 3 | 4 | 5 | | | V-2 | Ifrd2 | 0.58 | 1270 | 3 | 4 | 5 | | | V-2 | Med9os | 0.57 |
| 1175 | 3 | 4 | 5 | | | V-2 | Ift140 | 0.59 | 1271 | 3 | 4 | 5 | | | V-2 | Medag | 0.65 |
| 1176 | 3 | 4 | 5 | | | V-2 | Ift80 | 0.60 | 1272 | 3 | 4 | 5 | | | V-2 | Mettl16 | 0.59 |
| 1177 | 3 | 4 | 5 | | | V-2 | Igfals | 0.67 | 1273 | 3 | 4 | 5 | | | V-2 | Mfap3l | 0.66 |
| 1178 | 3 | 4 | 5 | | | V-2 | Igsf1 | 0.64 | 1274 | 3 | 4 | 5 | | | V-2 | Mfi2 | 0.54 |
| 1179 | 3 | 4 | 5 | | | V-2 | Igsf5 | 0.50 | 1275 | 3 | 4 | 5 | | | V-2 | Mfsd12 | 0.63 |
| 1180 | 3 | 4 | 5 | | | V-2 | Il15 | 0.62 | 1276 | 3 | 4 | 5 | | | V-2 | Mgam | 0.64 |
| 1181 | 3 | 4 | 5 | | | V-2 | Il17b | 0.63 | 1277 | 3 | 4 | 5 | | | V-2 | Mgll | 0.67 |
| 1182 | 3 | 4 | 5 | | | V-2 | Il17rc | 0.66 | 1278 | 3 | 4 | 5 | | | V-2 | Mgme1 | 0.60 |
| 1183 | 3 | 4 | 5 | | | V-2 | Il1f8 | 0.63 | 1279 | 3 | 4 | 5 | | | V-2 | Mgst3 | 0.51 |
| 1184 | 3 | 4 | 5 | | | V-2 | Il1rn | 0.54 | 1280 | 3 | 4 | 5 | | | V-2 | Mina | 0.54 |
| 1185 | 3 | 4 | 5 | | | V-2 | Il20rb | 0.55 | 1281 | 3 | 4 | 5 | | | V-2 | Misp | 0.57 |
| 1186 | 3 | 4 | 5 | | | V-2 | Il22ra1 | 0.56 | 1282 | 3 | 4 | 5 | | | V-2 | Mkks | 0.65 |
| 1187 | 3 | 4 | 5 | | | V-2 | Il34 | 0.57 | 1283 | 3 | 4 | 5 | | | V-2 | Mlec | 0.62 |
| 1188 | 3 | 4 | 5 | | | V-2 | Ins1 | 0.58 | 1284 | 3 | 4 | 5 | | | V-2 | Mlf1 | 0.52 |
| 1189 | 3 | 4 | 5 | | | V-2 | Insc | 0.56 | 1285 | 3 | 4 | 5 | | | V-2 | Mlxipl | 0.60 |
| 1190 | 3 | 4 | 5 | | | V-2 | Isoc2a | 0.60 | 1286 | 3 | 4 | 5 | | | V-2 | Mmaa | 0.65 |
| 1191 | 3 | 4 | 5 | | | V-2 | Isx | 0.67 | 1287 | 3 | 4 | 5 | | | V-2 | Mmp9 | 0.64 |
| 1192 | 3 | 4 | 5 | | | V-2 | Itga2b | 0.60 | 1288 | 3 | 4 | 5 | | | V-2 | Mocos | 0.53 |
| 1193 | 3 | 4 | 5 | | | V-2 | Itga4 | 0.60 | 1289 | 3 | 4 | 5 | | | V-2 | Morc4 | 0.60 |
| 1194 | 3 | 4 | 5 | | | V-2 | Itgb1bp2 | 0.55 | 1290 | 3 | 4 | 5 | | | V-2 | Mrgprf | 0.65 |
| 1195 | 3 | 4 | 5 | | | V-2 | Itgb3 | 0.60 | 1291 | 3 | 4 | 5 | | | V-2 | Mrpl24 | 0.66 |
| 1196 | 3 | 4 | 5 | | | V-2 | Itih2 | 0.50 | 1292 | 3 | 4 | 5 | | | V-2 | Mrpl34 | 0.64 |
| 1197 | 3 | 4 | 5 | | | V-2 | Itih3 | 0.57 | 1293 | 3 | 4 | 5 | | | V-2 | Mrpl35 | 0.65 |
| 1198 | 3 | 4 | 5 | | | V-2 | Iyd | 0.58 | 1294 | 3 | 4 | 5 | | | V-2 | Mrps16 | 0.62 |
| 1199 | 3 | 4 | 5 | | | V-2 | Josd2 | 0.52 | 1295 | 3 | 4 | 5 | | | V-2 | Mrps21 | 0.63 |
| 1200 | 3 | 4 | 5 | | | V-2 | Jph2 | 0.65 | 1296 | 3 | 4 | 5 | | | V-2 | Mrps28 | 0.59 |
| 1201 | 3 | 4 | 5 | | | V-2 | Kazald1 | 0.65 | 1297 | 3 | 4 | 5 | | | V-2 | Mrps36 | 0.59 |
| 1202 | 3 | 4 | 5 | | | V-2 | Kbtbd13 | 0.51 | 1298 | 3 | 4 | 5 | | | V-2 | Mrrf | 0.66 |
| 1203 | 3 | 4 | 5 | | | V-2 | Kbtbd8 | 0.64 | 1299 | 3 | 4 | 5 | | | V-2 | Msc | 0.66 |
| 1204 | 3 | 4 | 5 | | | V-2 | Kcnj12 | 0.60 | 1300 | 3 | 4 | 5 | | | V-2 | Mstn | 0.66 |
| 1205 | 3 | 4 | 5 | | | V-2 | Kcnk3 | 0.58 | 1301 | 3 | 4 | 5 | | | V-2 | Mterf1b | 0.52 |
| 1206 | 3 | 4 | 5 | | | V-2 | Kctd11 | 0.67 | 1302 | 3 | 4 | 5 | | | V-2 | Mtfr1 | 0.65 |
| 1207 | 3 | 4 | 5 | | | V-2 | Kctd14 | 0.55 | 1303 | 3 | 4 | 5 | | | V-2 | Mthfd1 | 0.64 |
| 1208 | 3 | 4 | 5 | | | V-2 | Kctd21 | 0.58 | 1304 | 3 | 4 | 5 | | | V-2 | Mttp | 0.55 |
| 1209 | 3 | 4 | 5 | | | V-2 | Kif11 | 0.55 | 1305 | 3 | 4 | 5 | | | V-2 | Mxd3 | 0.52 |
| 1210 | 3 | 4 | 5 | | | V-2 | Kif14 | 0.56 | 1306 | 3 | 4 | 5 | | | V-2 | Myb | 0.63 |
| 1211 | 3 | 4 | 5 | | | V-2 | Kif15 | 0.65 | 1307 | 3 | 4 | 5 | | | V-2 | Myct1 | 0.59 |
| 1212 | 3 | 4 | 5 | | | V-2 | Kif18a | 0.60 | 1308 | 3 | 4 | 5 | | | V-2 | Myf6 | 0.64 |
| 1213 | 3 | 4 | 5 | | | V-2 | Kif18b | 0.59 | 1309 | 3 | 4 | 5 | | | V-2 | Myh2 | 0.53 |
| 1214 | 3 | 4 | 5 | | | V-2 | Kif20a | 0.65 | 1310 | 3 | 4 | 5 | | | V-2 | Myh4 | 0.55 |
| 1215 | 3 | 4 | 5 | | | V-2 | Kif20b | 0.64 | 1311 | 3 | 4 | 5 | | | V-2 | Myh8 | 0.55 |
| 1216 | 3 | 4 | 5 | | | V-2 | Kif22 | 0.57 | 1312 | 3 | 4 | 5 | | | V-2 | Myl1 | 0.62 |
| 1217 | 3 | 4 | 5 | | | V-2 | Kif23 | 0.56 | 1313 | 3 | 4 | 5 | | | V-2 | Myl4 | 0.65 |
| 1218 | 3 | 4 | 5 | | | V-2 | Kif4 | 0.62 | 1314 | 3 | 4 | 5 | | | V-2 | Mylk3 | 0.61 |
| 1219 | 3 | 4 | 5 | | | V-2 | Klhl30 | 0.63 | 1315 | 3 | 4 | 5 | | | V-2 | Mylpf | 0.65 |
| 1220 | 3 | 4 | 5 | | | V-2 | Klhl31 | 0.51 | 1316 | 3 | 4 | 5 | | | V-2 | Myom2 | 0.63 |
| 1221 | 3 | 4 | 5 | | | V-2 | Klk13 | 0.58 | 1317 | 3 | 4 | 5 | | | V-2 | Myoz3 | 0.58 |
| 1222 | 3 | 4 | 5 | | | V-2 | Kntc1 | 0.63 | 1318 | 3 | 4 | 5 | | | V-2 | Mypn | 0.67 |
| 1223 | 3 | 4 | 5 | | | V-2 | Kprp | 0.66 | 1319 | 3 | 4 | 5 | | | V-2 | Naa38 | 0.67 |
| 1224 | 3 | 4 | 5 | | | V-2 | Krt1 | 0.50 | 1320 | 3 | 4 | 5 | | | V-2 | Naaladl1 | 0.66 |
| 1225 | 3 | 4 | 5 | | | V-2 | Krt10 | 0.53 | 1321 | 3 | 4 | 5 | | | V-2 | Nabp1 | 0.66 |
| 1226 | 3 | 4 | 5 | | | V-2 | Krt13 | 0.63 | 1322 | 3 | 4 | 5 | | | V-2 | Nadk2 | 0.59 |
| 1227 | 3 | 4 | 5 | | | V-2 | Krt2 | 0.59 | 1323 | 3 | 4 | 5 | | | V-2 | Nagpa | 0.60 |
| 1228 | 3 | 4 | 5 | | | V-2 | Krt25 | 0.55 | 1324 | 3 | 4 | 5 | | | V-2 | Nags | 0.66 |
| 1229 | 3 | 4 | 5 | | | V-2 | Krt27 | 0.65 | 1325 | 3 | 4 | 5 | | | V-2 | Naip2 | 0.64 |
| 1230 | 3 | 4 | 5 | | | V-2 | Krt71 | 0.58 | 1326 | 3 | 4 | 5 | | | V-2 | Naip5 | 0.59 |
| 1231 | 3 | 4 | 5 | | | V-2 | Krtap3-1 | 0.51 | 1327 | 3 | 4 | 5 | | | V-2 | Naprt1 | 0.64 |
| 1232 | 3 | 4 | 5 | | | V-2 | Krtdap | 0.62 | 1328 | 3 | 4 | 5 | | | V-2 | Narf | 0.63 |
| 1233 | 3 | 4 | 5 | | | V-2 | Kv | 0.58 | 1329 | 3 | 4 | 5 | | | V-2 | Ncapg | 0.56 |
| 1234 | 3 | 4 | 5 | | | V-2 | Lace1 | 0.59 | 1330 | 3 | 4 | 5 | | | V-2 | Nccrp1 | 0.64 |
| 1235 | 3 | 4 | 5 | | | V-2 | Larp1b | 0.59 | 1331 | 3 | 4 | 5 | | | V-2 | Ncf2 | 0.67 |
| 1236 | 3 | 4 | 5 | | | V-2 | Lbr | 0.63 | 1332 | 3 | 4 | 5 | | | V-2 | Nck1 | 0.65 |
| 1237 | 3 | 4 | 5 | | | V-2 | Lcat | 0.53 | 1333 | 3 | 4 | 5 | | | V-2 | Ndc80 | 0.62 |
| 1238 | 3 | 4 | 5 | | | V-2 | Lce1a1 | 0.62 | 1334 | 3 | 4 | 5 | | | V-2 | Ndrg1 | 0.60 |
| 1239 | 3 | 4 | 5 | | | V-2 | Lce1a2 | 0.53 | 1335 | 3 | 4 | 5 | | | V-2 | Ndufa12 | 0.61 |
| 1240 | 3 | 4 | 5 | | | V-2 | Lce1c | 0.53 | 1336 | 3 | 4 | 5 | | | V-2 | Ndufa4 | 0.66 |
| 1241 | 3 | 4 | 5 | | | V-2 | Lce1e | 0.52 | 1337 | 3 | 4 | 5 | | | V-2 | Ndufab1 | 0.64 |
| 1242 | 3 | 4 | 5 | | | V-2 | Lce1f | 0.59 | 1338 | 3 | 4 | 5 | | | V-2 | Ndufaf1 | 0.65 |
| 1243 | 3 | 4 | 5 | | | V-2 | Ldha | 0.54 | 1339 | 3 | 4 | 5 | | | V-2 | Ndufaf6 | 0.53 |
| 1244 | 3 | 4 | 5 | | | V-2 | Lgals1 | 0.65 | 1340 | 3 | 4 | 5 | | | V-2 | Ndufb2 | 0.52 |
| 1245 | 3 | 4 | 5 | | | V-2 | Lgals2 | 0.50 | 1341 | 3 | 4 | 5 | | | V-2 | Ndufb6 | 0.64 |
| 1246 | 3 | 4 | 5 | | | V-2 | Lgals6 | 0.54 | 1342 | 3 | 4 | 5 | | | V-2 | Ndufb7 | 0.67 |

Fig. 45 - 8

| | | | | | | | | | | | | | | | |
|---|---|---|---|---|---|---|---|---|---|---|---|---|---|---|---|
| 1343 | 3 | 4 | 5 | | | V-2 | Ndufc1 | 0.53 | 1439 | 3 | 4 | 5 | | V-2 | Prkcq | 0.67 |
| 1344 | 3 | 4 | 5 | | | V-2 | Neb | 0.59 | 1440 | 3 | 4 | 5 | | V-2 | Prlr | 0.64 |
| 1345 | 3 | 4 | 5 | | | V-2 | Nexn | 0.59 | 1441 | 3 | 4 | 5 | | V-2 | Prnd | 0.55 |
| 1346 | 3 | 4 | 5 | | | V-2 | Nhej1 | 0.64 | 1442 | 3 | 4 | 5 | | V-2 | Proca1 | 0.58 |
| 1347 | 3 | 4 | 5 | | | V-2 | Nkpd1 | 0.63 | 1443 | 3 | 4 | 5 | | V-2 | Procr | 0.66 |
| 1348 | 3 | 4 | 5 | | | V-2 | Nlrp10 | 0.67 | 1444 | 3 | 4 | 5 | | V-2 | Proz | 0.61 |
| 1349 | 3 | 4 | 5 | | | V-2 | Nlrp6 | 0.52 | 1445 | 3 | 4 | 5 | | V-2 | Prr11 | 0.60 |
| 1350 | 3 | 4 | 5 | | | V-2 | Nme3 | 0.64 | 1446 | 3 | 4 | 5 | | V-2 | Prr9 | 0.63 |
| 1351 | 3 | 4 | 5 | | | V-2 | Nmnat1 | 0.63 | 1447 | 3 | 4 | 5 | | V-2 | Prss16 | 0.55 |
| 1352 | 3 | 4 | 5 | | | V-2 | Nod1 | 0.65 | 1448 | 3 | 4 | 5 | | V-2 | Prss8 | 0.59 |
| 1353 | 3 | 4 | 5 | | | V-2 | Nol3 | 0.66 | 1449 | 3 | 4 | 5 | | V-2 | Psmb9 | 0.64 |
| 1354 | 3 | 4 | 5 | | | V-2 | Npc1l1 | 0.66 | 1450 | 3 | 4 | 5 | | V-2 | Psmc3ip | 0.61 |
| 1355 | 3 | 4 | 5 | | | V-2 | Npm3 | 0.54 | 1451 | 3 | 4 | 5 | | V-2 | Psmg3 | 0.64 |
| 1356 | 3 | 4 | 5 | | | V-2 | Nqo2 | 0.65 | 1452 | 3 | 4 | 5 | | V-2 | Pstpip2 | 0.64 |
| 1357 | 3 | 4 | 5 | | | V-2 | Nr1i2 | 0.61 | 1453 | 3 | 4 | 5 | | V-2 | Ptdss2 | 0.59 |
| 1358 | 3 | 4 | 5 | | | V-2 | Nr5a2 | 0.58 | 1454 | 3 | 4 | 5 | | V-2 | Pter | 0.65 |
| 1359 | 3 | 4 | 5 | | | V-2 | Nsl1 | 0.57 | 1455 | 3 | 4 | 5 | | V-2 | Ptges3l | 0.52 |
| 1360 | 3 | 4 | 5 | | | V-2 | Nudt1 | 0.55 | 1456 | 3 | 4 | 5 | | V-2 | Ptpn7 | 0.60 |
| 1361 | 3 | 4 | 5 | | | V-2 | Nudt15 | 0.66 | 1457 | 3 | 4 | 5 | | V-2 | Ptprcap | 0.59 |
| 1362 | 3 | 4 | 5 | | | V-2 | Nuf2 | 0.51 | 1458 | 3 | 4 | 5 | | V-2 | Pycard | 0.56 |
| 1363 | 3 | 4 | 5 | | | V-2 | Nup37 | 0.62 | 1459 | 3 | 4 | 5 | | V-2 | Pygl | 0.53 |
| 1364 | 3 | 4 | 5 | | | V-2 | Nup50 | 0.66 | 1460 | 3 | 4 | 5 | | V-2 | Rab17 | 0.63 |
| 1365 | 3 | 4 | 5 | | | V-2 | Nusap1 | 0.56 | 1461 | 3 | 4 | 5 | | V-2 | Rab3il1 | 0.56 |
| 1366 | 3 | 4 | 5 | | | V-2 | Ocstamp | 0.51 | 1462 | 3 | 4 | 5 | | V-2 | Rab40b | 0.65 |
| 1367 | 3 | 4 | 5 | | | V-2 | Odc1 | 0.57 | 1463 | 3 | 4 | 5 | | V-2 | Rad23a | 0.60 |
| 1368 | 3 | 4 | 5 | | | V-2 | Odf3l1 | 0.56 | 1464 | 3 | 4 | 5 | | V-2 | Rad51 | 0.55 |
| 1369 | 3 | 4 | 5 | | | V-2 | Ogdh | 0.61 | 1465 | 3 | 4 | 5 | | V-2 | Rad51ap1 | 0.59 |
| 1370 | 3 | 4 | 5 | | | V-2 | Oip5 | 0.58 | 1466 | 3 | 4 | 5 | | V-2 | Rad51b | 0.55 |
| 1371 | 3 | 4 | 5 | | | V-2 | Omp | 0.66 | 1467 | 3 | 4 | 5 | | V-2 | Rad51c | 0.59 |
| 1372 | 3 | 4 | 5 | | | V-2 | Orc1 | 0.50 | 1468 | 3 | 4 | 5 | | V-2 | Raet1d | 0.53 |
| 1373 | 3 | 4 | 5 | | | V-2 | Oxct1 | 0.51 | 1469 | 3 | 4 | 5 | | V-2 | Raet1e | 0.55 |
| 1374 | 3 | 4 | 5 | | | V-2 | P2rx1 | 0.61 | 1470 | 3 | 4 | 5 | | V-2 | Rangap1 | 0.63 |
| 1375 | 3 | 4 | 5 | | | V-2 | P4ha1 | 0.55 | 1471 | 3 | 4 | 5 | | V-2 | Rarres2 | 0.53 |
| 1376 | 3 | 4 | 5 | | | V-2 | P4ha2 | 0.58 | 1472 | 3 | 4 | 5 | | V-2 | Rars2 | 0.63 |
| 1377 | 3 | 4 | 5 | | | V-2 | Pabpc4 | 0.64 | 1473 | 3 | 4 | 5 | | V-2 | Rasl12 | 0.54 |
| 1378 | 3 | 4 | 5 | | | V-2 | Paqr9 | 0.55 | 1474 | 3 | 4 | 5 | | V-2 | Rasl2-9 | 0.58 |
| 1379 | 3 | 4 | 5 | | | V-2 | Parpbp | 0.57 | 1475 | 3 | 4 | 5 | | V-2 | Rassf6 | 0.57 |
| 1380 | 3 | 4 | 5 | | | V-2 | Pbdc1 | 0.62 | 1476 | 3 | 4 | 5 | | V-2 | Rbm10 | 0.62 |
| 1381 | 3 | 4 | 5 | | | V-2 | Pbk | 0.63 | 1477 | 3 | 4 | 5 | | V-2 | Rbm15 | 0.59 |
| 1382 | 3 | 4 | 5 | | | V-2 | Pcgf5 | 0.61 | 1478 | 3 | 4 | 5 | | V-2 | Rbm38 | 0.56 |
| 1383 | 3 | 4 | 5 | | | V-2 | Pcna | 0.64 | 1479 | 3 | 4 | 5 | | V-2 | Rbm47 | 0.66 |
| 1384 | 3 | 4 | 5 | | | V-2 | Pcx | 0.54 | 1480 | 3 | 4 | 5 | | V-2 | Rdh5 | 0.66 |
| 1385 | 3 | 4 | 5 | | | V-2 | Pcyt2 | 0.66 | 1481 | 3 | 4 | 5 | | V-2 | Rel | 0.66 |
| 1386 | 3 | 4 | 5 | | | V-2 | Pdia4 | 0.62 | 1482 | 3 | 4 | 5 | | V-2 | Relt | 0.62 |
| 1387 | 3 | 4 | 5 | | | V-2 | Pdia6 | 0.64 | 1483 | 3 | 4 | 5 | | V-2 | Renbp | 0.67 |
| 1388 | 3 | 4 | 5 | | | V-2 | Pdxk1ip1 | 0.57 | 1484 | 3 | 4 | 5 | | V-2 | Rep15 | 0.64 |
| 1389 | 3 | 4 | 5 | | | V-2 | Pecr | 0.65 | 1485 | 3 | 4 | 5 | | V-2 | Rexo2 | 0.61 |
| 1390 | 3 | 4 | 5 | | | V-2 | Pemt | 0.58 | 1486 | 3 | 4 | 5 | | V-2 | Rfc4 | 0.66 |
| 1391 | 3 | 4 | 5 | | | V-2 | Pepd | 0.64 | 1487 | 3 | 4 | 5 | | V-2 | Rfesd | 0.60 |
| 1392 | 3 | 4 | 5 | | | V-2 | Pet112 | 0.62 | 1488 | 3 | 4 | 5 | | V-2 | Rfx2 | 0.59 |
| 1393 | 3 | 4 | 5 | | | V-2 | Pfkl | 0.58 | 1489 | 3 | 4 | 5 | | V-2 | Rgs10 | 0.61 |
| 1394 | 3 | 4 | 5 | | | V-2 | Pgam1 | 0.57 | 1490 | 3 | 4 | 5 | | V-2 | Rgs18 | 0.51 |
| 1395 | 3 | 4 | 5 | | | V-2 | Pglyrp2 | 0.54 | 1491 | 3 | 4 | 5 | | V-2 | Rhpn2 | 0.61 |
| 1396 | 3 | 4 | 5 | | | V-2 | Pgm2 | 0.62 | 1492 | 3 | 4 | 5 | | V-2 | Ripply3 | 0.57 |
| 1397 | 3 | 4 | 5 | | | V-2 | Pgp | 0.64 | 1493 | 3 | 4 | 5 | | V-2 | Rnf128 | 0.65 |
| 1398 | 3 | 4 | 5 | | | V-2 | Phlda2 | 0.60 | 1494 | 3 | 4 | 5 | | V-2 | Rnpep | 0.59 |
| 1399 | 3 | 4 | 5 | | | V-2 | Phospho1 | 0.63 | 1495 | 3 | 4 | 5 | | V-2 | Rpa1 | 0.61 |
| 1400 | 3 | 4 | 5 | | | V-2 | Phyhip | 0.66 | 1496 | 3 | 4 | 5 | | V-2 | Rpe | 0.59 |
| 1401 | 3 | 4 | 5 | | | V-2 | Pif1 | 0.64 | 1497 | 3 | 4 | 5 | | V-2 | Rpia | 0.62 |
| 1402 | 3 | 4 | 5 | | | V-2 | Piga | 0.65 | 1498 | 3 | 4 | 5 | | V-2 | Rpl13a | 0.53 |
| 1403 | 3 | 4 | 5 | | | V-2 | Pigg | 0.56 | 1499 | 3 | 4 | 5 | | V-2 | Rpl31 | 0.61 |
| 1404 | 3 | 4 | 5 | | | V-2 | Pipox | 0.59 | 1500 | 3 | 4 | 5 | | V-2 | Rps29 | 0.55 |
| 1405 | 3 | 4 | 5 | | | V-2 | Pkhd1l1 | 0.65 | 1501 | 3 | 4 | 5 | | V-2 | Rptn | 0.65 |
| 1406 | 3 | 4 | 5 | | | V-2 | Pkn3 | 0.62 | 1502 | 3 | 4 | 5 | | V-2 | Rrm1 | 0.57 |
| 1407 | 3 | 4 | 5 | | | V-2 | Pla2g12b | 0.58 | 1503 | 3 | 4 | 5 | | V-2 | Rsph1 | 0.60 |
| 1408 | 3 | 4 | 5 | | | V-2 | Pla2g16 | 0.57 | 1504 | 3 | 4 | 5 | | V-2 | Rtn4ip1 | 0.53 |
| 1409 | 3 | 4 | 5 | | | V-2 | Pla2g3 | 0.66 | 1505 | 3 | 4 | 5 | | V-2 | Ryr1 | 0.66 |
| 1410 | 3 | 4 | 5 | | | V-2 | Pla2g4c | 0.63 | 1506 | 3 | 4 | 5 | | V-2 | S100a13 | 0.66 |
| 1411 | 3 | 4 | 5 | | | V-2 | Pla2g4f | 0.58 | 1507 | 3 | 4 | 5 | | V-2 | Sacs | 0.66 |
| 1412 | 3 | 4 | 5 | | | V-2 | Pla2g5 | 0.61 | 1508 | 3 | 4 | 5 | | V-2 | Sash3 | 0.63 |
| 1413 | 3 | 4 | 5 | | | V-2 | Plekhg6 | 0.60 | 1509 | 3 | 4 | 5 | | V-2 | Scd2 | 0.59 |
| 1414 | 3 | 4 | 5 | | | V-2 | Plg | 0.53 | 1510 | 3 | 4 | 5 | | V-2 | Scly | 0.54 |
| 1415 | 3 | 4 | 5 | | | V-2 | Plin5 | 0.64 | 1511 | 3 | 4 | 5 | | V-2 | Scn2b | 0.63 |
| 1416 | 3 | 4 | 5 | | | V-2 | Plk1 | 0.51 | 1512 | 3 | 4 | 5 | | V-2 | Scn4a | 0.54 |
| 1417 | 3 | 4 | 5 | | | V-2 | Pm20d1 | 0.54 | 1513 | 3 | 4 | 5 | | V-2 | Scrn3 | 0.57 |
| 1418 | 3 | 4 | 5 | | | V-2 | Pola1 | 0.56 | 1514 | 3 | 4 | 5 | | V-2 | Sdf2l1 | 0.57 |
| 1419 | 3 | 4 | 5 | | | V-2 | Pold3 | 0.65 | 1515 | 3 | 4 | 5 | | V-2 | Sdhb | 0.61 |
| 1420 | 3 | 4 | 5 | | | V-2 | Polq | 0.59 | 1516 | 3 | 4 | 5 | | V-2 | Sdhd | 0.67 |
| 1421 | 3 | 4 | 5 | | | V-2 | Polr2g | 0.66 | 1517 | 3 | 4 | 5 | | V-2 | Sdpr | 0.65 |
| 1422 | 3 | 4 | 5 | | | V-2 | Pomt1 | 0.62 | 1518 | 3 | 4 | 5 | | V-2 | Sdr16c5 | 0.61 |
| 1423 | 3 | 4 | 5 | | | V-2 | Pop5 | 0.58 | 1519 | 3 | 4 | 5 | | V-2 | Sdr9c7 | 0.50 |
| 1424 | 3 | 4 | 5 | | | V-2 | Popdc2 | 0.62 | 1520 | 3 | 4 | 5 | | V-2 | Sec61b | 0.56 |
| 1425 | 3 | 4 | 5 | | | V-2 | Pou2af1 | 0.66 | 1521 | 3 | 4 | 5 | | V-2 | Selplg | 0.50 |
| 1426 | 3 | 4 | 5 | | | V-2 | Ppara | 0.53 | 1522 | 3 | 4 | 5 | | V-2 | Senp8 | 0.53 |
| 1427 | 3 | 4 | 5 | | | V-2 | Ppm1k | 0.63 | 1523 | 3 | 4 | 5 | | V-2 | Serpina1b | 0.62 |
| 1428 | 3 | 4 | 5 | | | V-2 | Ppox | 0.61 | 1524 | 3 | 4 | 5 | | V-2 | Serpina1c | 0.60 |
| 1429 | 3 | 4 | 5 | | | V-2 | Ppp1r27 | 0.50 | 1525 | 3 | 4 | 5 | | V-2 | Serpina1d | 0.51 |
| 1430 | 3 | 4 | 5 | | | V-2 | Ppp1r3s | 0.67 | 1526 | 3 | 4 | 5 | | V-2 | Serpinb3a | 0.62 |
| 1431 | 3 | 4 | 5 | | | V-2 | Ppp1r3a | 0.57 | 1527 | 3 | 4 | 5 | | V-2 | Serpinb5 | 0.52 |
| 1432 | 3 | 4 | 5 | | | V-2 | Ppp1r3b | 0.52 | 1528 | 3 | 4 | 5 | | V-2 | Serpinb6c | 0.50 |
| 1433 | 3 | 4 | 5 | | | V-2 | Ppp1r3c | 0.65 | 1529 | 3 | 4 | 5 | | V-2 | Serpinf2 | 0.58 |
| 1434 | 3 | 4 | 5 | | | V-2 | Ppp1r3d | 0.61 | 1530 | 3 | 4 | 5 | | V-2 | Setd8 | 0.61 |
| 1435 | 3 | 4 | 5 | | | V-2 | Ppwd1 | 0.67 | 1531 | 3 | 4 | 5 | | V-2 | Sftpc | 0.62 |
| 1436 | 3 | 4 | 5 | | | V-2 | Prc1 | 0.51 | 1532 | 3 | 4 | 5 | | V-2 | Sgol1 | 0.55 |
| 1437 | 3 | 4 | 5 | | | V-2 | Prdx2 | 0.66 | 1533 | 3 | 4 | 5 | | V-2 | Sgol2 | 0.62 |
| 1438 | 3 | 4 | 5 | | | V-2 | Prdx3 | 0.62 | 1534 | 3 | 4 | 5 | | V-2 | Shbg | 0.62 |

Fig. 45 - 9

| | | | | | | | |
|---|---|---|---|---|---|---|---|
| 1535 | 3 | 4 | 5 | | V-2 | Shcbp1 | 0.52 |
| 1536 | 3 | 4 | 5 | | V-2 | Ska3 | 0.66 |
| 1537 | 3 | 4 | 5 | | V-2 | Slbp | 0.57 |
| 1538 | 3 | 4 | 5 | | V-2 | Slc13a3 | 0.62 |
| 1539 | 3 | 4 | 5 | | V-2 | Slc14a1 | 0.52 |
| 1540 | 3 | 4 | 5 | | V-2 | Slc16a1 | 0.58 |
| 1541 | 3 | 4 | 5 | | V-2 | Slc16a12 | 0.65 |
| 1542 | 3 | 4 | 5 | | V-2 | Slc16a6 | 0.58 |
| 1543 | 3 | 4 | 5 | | V-2 | Slc1a5 | 0.59 |
| 1544 | 3 | 4 | 5 | | V-2 | Slc22a4 | 0.53 |
| 1545 | 3 | 4 | 5 | | V-2 | Slc23a1 | 0.57 |
| 1546 | 3 | 4 | 5 | | V-2 | Slc25a21 | 0.65 |
| 1547 | 3 | 4 | 5 | | V-2 | Slc25a38 | 0.62 |
| 1548 | 3 | 4 | 5 | | V-2 | Slc30a10 | 0.59 |
| 1549 | 3 | 4 | 5 | | V-2 | Slc37a2 | 0.62 |
| 1550 | 3 | 4 | 5 | | V-2 | Slc39a4 | 0.60 |
| 1551 | 3 | 4 | 5 | | V-2 | Slc43a3 | 0.67 |
| 1552 | 3 | 4 | 5 | | V-2 | Slc44a3 | 0.53 |
| 1553 | 3 | 4 | 5 | | V-2 | Slc44a4 | 0.67 |
| 1554 | 3 | 4 | 5 | | V-2 | Slc45a3 | 0.62 |
| 1555 | 3 | 4 | 5 | | V-2 | Slc46a3 | 0.56 |
| 1556 | 3 | 4 | 5 | | V-2 | Slc5a1 | 0.58 |
| 1557 | 3 | 4 | 5 | | V-2 | Slc5a9 | 0.63 |
| 1558 | 3 | 4 | 5 | | V-2 | Slc7a7 | 0.65 |
| 1559 | 3 | 4 | 5 | | V-2 | Slc9a2 | 0.56 |
| 1560 | 3 | 4 | 5 | | V-2 | Slc9a3r1 | 0.63 |
| 1561 | 3 | 4 | 5 | | V-2 | Slfn14 | 0.61 |
| 1562 | 3 | 4 | 5 | | V-2 | Slurp1 | 0.62 |
| 1563 | 3 | 4 | 5 | | V-2 | Smc2 | 0.65 |
| 1564 | 3 | 4 | 5 | | V-2 | Smc4 | 0.57 |
| 1565 | 3 | 4 | 5 | | V-2 | Smim1 | 0.60 |
| 1566 | 3 | 4 | 5 | | V-2 | Smlr1 | 0.58 |
| 1567 | 3 | 4 | 5 | | V-2 | Snca | 0.58 |
| 1568 | 3 | 4 | 5 | | V-2 | Snora65 | 0.51 |
| 1569 | 3 | 4 | 5 | | V-2 | Snora78 | 0.51 |
| 1570 | 3 | 4 | 5 | | V-2 | Snrnp25 | 0.60 |
| 1571 | 3 | 4 | 5 | | V-2 | Snx22 | 0.66 |
| 1572 | 3 | 4 | 5 | | V-2 | Snx3 | 0.64 |
| 1573 | 3 | 4 | 5 | | V-2 | Soat2 | 0.51 |
| 1574 | 3 | 4 | 5 | | V-2 | Sod3 | 0.60 |
| 1575 | 3 | 4 | 5 | | V-2 | Sox7 | 0.56 |
| 1576 | 3 | 4 | 5 | | V-2 | Spag5 | 0.61 |
| 1577 | 3 | 4 | 5 | | V-2 | Spc24 | 0.56 |
| 1578 | 3 | 4 | 5 | | V-2 | Spc25 | 0.61 |
| 1579 | 3 | 4 | 5 | | V-2 | Spdl1 | 0.53 |
| 1580 | 3 | 4 | 5 | | V-2 | Spice1 | 0.63 |
| 1581 | 3 | 4 | 5 | | V-2 | Spn | 0.53 |
| 1582 | 3 | 4 | 5 | | V-2 | Sprr1a | 0.54 |
| 1583 | 3 | 4 | 5 | | V-2 | Sptlc3 | 0.60 |
| 1584 | 3 | 4 | 5 | | V-2 | Sptssb | 0.67 |
| 1585 | 3 | 4 | 5 | | V-2 | Srsf7 | 0.61 |
| 1586 | 3 | 4 | 5 | | V-2 | Ssx2ip | 0.64 |
| 1587 | 3 | 4 | 5 | | V-2 | St3gal4 | 0.62 |
| 1588 | 3 | 4 | 5 | | V-2 | Stab2 | 0.58 |
| 1589 | 3 | 4 | 5 | | V-2 | Stbd1 | 0.56 |
| 1590 | 3 | 4 | 5 | | V-2 | Stip1 | 0.67 |
| 1591 | 3 | 4 | 5 | | V-2 | Stom | 0.58 |
| 1592 | 3 | 4 | 5 | | V-2 | Stxbp4 | 0.66 |
| 1593 | 3 | 4 | 5 | | V-2 | Sult2b1 | 0.63 |
| 1594 | 3 | 4 | 5 | | V-2 | Susd1 | 0.61 |
| 1595 | 3 | 4 | 5 | | V-2 | Susd2 | 0.59 |
| 1596 | 3 | 4 | 5 | | V-2 | Syt11 | 0.57 |
| 1597 | 3 | 4 | 5 | | V-2 | Taco1 | 0.59 |
| 1598 | 3 | 4 | 5 | | V-2 | Taldo1 | 0.63 |
| 1599 | 3 | 4 | 5 | | V-2 | Tcf19 | 0.56 |
| 1600 | 3 | 4 | 5 | | V-2 | Tcf7 | 0.66 |
| 1601 | 3 | 4 | 5 | | V-2 | Tdh | 0.55 |
| 1602 | 3 | 4 | 5 | | V-2 | Tfb1m | 0.65 |
| 1603 | 3 | 4 | 5 | | V-2 | Tgm2 | 0.64 |
| 1604 | 3 | 4 | 5 | | V-2 | Tgm3 | 0.61 |
| 1605 | 3 | 4 | 5 | | V-2 | Thap1 | 0.62 |
| 1606 | 3 | 4 | 5 | | V-2 | Thap2 | 0.56 |
| 1607 | 3 | 4 | 5 | | V-2 | Ticam2 | 0.62 |
| 1608 | 3 | 4 | 5 | | V-2 | Tifa | 0.57 |
| 1609 | 3 | 4 | 5 | | V-2 | Timd4 | 0.52 |
| 1610 | 3 | 4 | 5 | | V-2 | Timm10b | 0.58 |
| 1611 | 3 | 4 | 5 | | V-2 | Tjp3 | 0.66 |
| 1612 | 3 | 4 | 5 | | V-2 | Tk1 | 0.62 |
| 1613 | 3 | 4 | 5 | | V-2 | Tlcd1 | 0.64 |
| 1614 | 3 | 4 | 5 | | V-2 | Tle6 | 0.64 |
| 1615 | 3 | 4 | 5 | | V-2 | Tlr5 | 0.61 |
| 1616 | 3 | 4 | 5 | | V-2 | Tm6sf1 | 0.55 |
| 1617 | 3 | 4 | 5 | | V-2 | Tm6sf2 | 0.50 |
| 1618 | 3 | 4 | 5 | | V-2 | Tm7sf2 | 0.61 |
| 1619 | 3 | 4 | 5 | | V-2 | Tmc6 | 0.61 |
| 1620 | 3 | 4 | 5 | | V-2 | Tmem102 | 0.59 |
| 1621 | 3 | 4 | 5 | | V-2 | Tmem154 | 0.60 |
| 1622 | 3 | 4 | 5 | | V-2 | Tmem171 | 0.59 |
| 1623 | 3 | 4 | 5 | | V-2 | Tmem180 | 0.65 |
| 1624 | 3 | 4 | 5 | | V-2 | Tmem213 | 0.51 |
| 1625 | 3 | 4 | 5 | | V-2 | Tmem233 | 0.60 |
| 1626 | 3 | 4 | 5 | | V-2 | Tmem236 | 0.55 |
| 1627 | 3 | 4 | 5 | | V-2 | Tmem256 | 0.62 |
| 1628 | 3 | 4 | 5 | | V-2 | Tmem261 | 0.65 |
| 1629 | 3 | 4 | 5 | | V-2 | Tmem37 | 0.61 |
| 1630 | 3 | 4 | 5 | | V-2 | Tmem40 | 0.66 |
| 1631 | 3 | 4 | 5 | | V-2 | Tmem54 | 0.60 |
| 1632 | 3 | 4 | 5 | | V-2 | Tmem56 | 0.65 |
| 1633 | 3 | 4 | 5 | | V-2 | Tmod1 | 0.63 |
| 1634 | 3 | 4 | 5 | | V-2 | Tnfaip2 | 0.66 |
| 1635 | 3 | 4 | 5 | | V-2 | Tnfaip8l1 | 0.62 |
| 1636 | 3 | 4 | 5 | | V-2 | Tnfrsf25 | 0.57 |
| 1637 | 3 | 4 | 5 | | V-2 | Tnmd | 0.58 |
| 1638 | 3 | 4 | 5 | | V-2 | Tnnc2 | 0.61 |
| 1639 | 3 | 4 | 5 | | V-2 | Tnni2 | 0.53 |
| 1640 | 3 | 4 | 5 | | V-2 | Tnnt3 | 0.61 |
| 1641 | 3 | 4 | 5 | | V-2 | Tomm7 | 0.63 |
| 1642 | 3 | 4 | 5 | | V-2 | Tonsl | 0.64 |
| 1643 | 3 | 4 | 5 | | V-2 | Top2a | 0.56 |
| 1644 | 3 | 4 | 5 | | V-2 | Tpi1 | 0.62 |
| 1645 | 3 | 4 | 5 | | V-2 | Tppp3 | 0.64 |
| 1646 | 3 | 4 | 5 | | V-2 | Tprg | 0.64 |
| 1647 | 3 | 4 | 5 | | V-2 | Tpsg1 | 0.56 |
| 1648 | 3 | 4 | 5 | | V-2 | Tpx2 | 0.58 |
| 1649 | 3 | 4 | 5 | | V-2 | Tra2a | 0.64 |
| 1650 | 3 | 4 | 5 | | V-2 | Traf3ip3 | 0.66 |
| 1651 | 3 | 4 | 5 | | V-2 | Trdn | 0.66 |
| 1652 | 3 | 4 | 5 | | V-2 | Trex2 | 0.55 |
| 1653 | 3 | 4 | 5 | | V-2 | Trim59 | 0.54 |
| 1654 | 3 | 4 | 5 | | V-2 | Trim72 | 0.57 |
| 1655 | 3 | 4 | 5 | | V-2 | Trmt1l | 0.61 |
| 1656 | 3 | 4 | 5 | | V-2 | Trmt2b | 0.65 |
| 1657 | 3 | 4 | 5 | | V-2 | Tspan32 | 0.55 |
| 1658 | 3 | 4 | 5 | | V-2 | Tspo | 0.55 |
| 1659 | 3 | 4 | 5 | | V-2 | Tst | 0.50 |
| 1660 | 3 | 4 | 5 | | V-2 | Ttc32 | 0.66 |
| 1661 | 3 | 4 | 5 | | V-2 | Ttc36 | 0.64 |
| 1662 | 3 | 4 | 5 | | V-2 | Ttk | 0.60 |
| 1663 | 3 | 4 | 5 | | V-2 | Tuba4a | 0.59 |
| 1664 | 3 | 4 | 5 | | V-2 | Tubb1 | 0.54 |
| 1665 | 3 | 4 | 5 | | V-2 | Tubb4b | 0.61 |
| 1666 | 3 | 4 | 5 | | V-2 | Tubd1 | 0.58 |
| 1667 | 3 | 4 | 5 | | V-2 | Tufm | 0.57 |
| 1668 | 3 | 4 | 5 | | V-2 | Tyms | 0.55 |
| 1669 | 3 | 4 | 5 | | V-2 | U2af1l4 | 0.65 |
| 1670 | 3 | 4 | 5 | | V-2 | Ubac1 | 0.52 |
| 1671 | 3 | 4 | 5 | | V-2 | Ube2l6 | 0.56 |
| 1672 | 3 | 4 | 5 | | V-2 | Ucma | 0.62 |
| 1673 | 3 | 4 | 5 | | V-2 | Uhrf1 | 0.60 |
| 1674 | 3 | 4 | 5 | | V-2 | Unc13d | 0.67 |
| 1675 | 3 | 4 | 5 | | V-2 | Unc5cl | 0.53 |
| 1676 | 3 | 4 | 5 | | V-2 | Upb1 | 0.52 |
| 1677 | 3 | 4 | 5 | | V-2 | Uqcc2 | 0.57 |
| 1678 | 3 | 4 | 5 | | V-2 | Uqcr11 | 0.57 |
| 1679 | 3 | 4 | 5 | | V-2 | Uqcrq | 0.63 |
| 1680 | 3 | 4 | 5 | | V-2 | Uroc1 | 0.52 |
| 1681 | 3 | 4 | 5 | | V-2 | Urod | 0.60 |
| 1682 | 3 | 4 | 5 | | V-2 | Vamp5 | 0.65 |
| 1683 | 3 | 4 | 5 | | V-2 | Vpreb1 | 0.57 |
| 1684 | 3 | 4 | 5 | | V-2 | Vpreb3 | 0.57 |
| 1685 | 3 | 4 | 5 | | V-2 | Wdpcp | 0.63 |
| 1686 | 3 | 4 | 5 | | V-2 | Wdr78 | 0.51 |
| 1687 | 3 | 4 | 5 | | V-2 | Xirp2 | 0.65 |
| 1688 | 3 | 4 | 5 | | V-2 | Xpo1 | 0.65 |
| 1689 | 3 | 4 | 5 | | V-2 | Yif1b | 0.67 |
| 1690 | 3 | 4 | 5 | | V-2 | Zbtb40 | 0.64 |
| 1691 | 3 | 4 | 5 | | V-2 | Zbtb8os | 0.51 |
| 1692 | 3 | 4 | 5 | | V-2 | Zfp109 | 0.58 |
| 1693 | 3 | 4 | 5 | | V-2 | Zfp114 | 0.62 |
| 1694 | 3 | 4 | 5 | | V-2 | Zfp808 | 0.66 |
| 1695 | 3 | 4 | 5 | | V-2 | Zfpm1 | 0.51 |
| 1696 | 3 | 4 | 5 | | V-2 | Zfyve21 | 0.62 |
| 1697 | 3 | 4 | 5 | | V-2 | Zmym1 | 0.63 |
| 1698 | 3 | 4 | 5 | | V-2 | l7Rn6 | 0.61 |
| 1699 | 3 | 4 | 5 | | V-1 | 0610009L18Rik | 1.56 |
| 1700 | 3 | 4 | 5 | | V-1 | 1110006O24Rik | 1.57 |
| 1701 | 3 | 4 | 5 | | V-1 | 1110017D15Rik | 1.64 |
| 1702 | 3 | 4 | 5 | | V-1 | 1500011B03Rik | 1.68 |
| 1703 | 3 | 4 | 5 | | V-1 | 1500012F01Rik | 1.55 |
| 1704 | 3 | 4 | 5 | | V-1 | 1600020E01Rik | 1.72 |
| 1705 | 3 | 4 | 5 | | V-1 | 1700003M07Rik | 1.82 |
| 1706 | 3 | 4 | 5 | | V-1 | 1700029J07Rik | 1.53 |
| 1707 | 3 | 4 | 5 | | V-1 | 1700056E22Rik | 1.73 |
| 1708 | 3 | 4 | 5 | | V-1 | 1700086O06Rik | 1.60 |
| 1709 | 3 | 4 | 5 | | V-1 | 1700096K18Rik | 1.75 |
| 1710 | 3 | 4 | 5 | | V-1 | 1700102P08Rik | 1.59 |
| 1711 | 3 | 4 | 5 | | V-1 | 1700109K24Rik | 1.59 |
| 1712 | 3 | 4 | 5 | | V-1 | 1700123M08Rik | 1.72 |
| 1713 | 3 | 4 | 5 | | V-1 | 1810010H24Rik | 1.53 |
| 1714 | 3 | 4 | 5 | | V-1 | 1810044D09Rik | 1.64 |
| 1715 | 3 | 4 | 5 | | V-1 | 1810062G17Rik | 1.91 |
| 1716 | 3 | 4 | 5 | | V-1 | 1810062O18Rik | 1.55 |
| 1717 | 3 | 4 | 5 | | V-1 | 2310002D06Rik | 1.87 |
| 1718 | 3 | 4 | 5 | | V-1 | 2310010J17Rik | 1.99 |
| 1719 | 3 | 4 | 5 | | V-1 | 2310034G01Rik | 1.55 |
| 1720 | 3 | 4 | 5 | | V-1 | 2410006H16Rik | 1.76 |
| 1721 | 3 | 4 | 5 | | V-1 | 2610035D17Rik | 1.60 |
| 1722 | 3 | 4 | 5 | | V-1 | 2610100L16Rik | 1.86 |
| 1723 | 3 | 4 | 5 | | V-1 | 2610203C20Rik | 1.89 |
| 1724 | 3 | 4 | 5 | | V-1 | 2610524H06Rik | 1.53 |
| 1725 | 3 | 4 | 5 | | V-1 | 2700046G09Rik | 1.65 |
| 1726 | 3 | 4 | 5 | | V-1 | 2810013P06Rik | 1.69 |

Fig. 45 - 10

| | | | | | | | | | | | | | | | |
|---|---|---|---|---|---|---|---|---|---|---|---|---|---|---|---|
| 1727 | 3 | 4 | 5 | | V-1 | 2810029C07Rik | 1.79 | 1823 | 3 | 4 | 5 | | V-1 | BC051142 | 1.57 |
| 1728 | 3 | 4 | 5 | | V-1 | 2810408A11Rik | 1.71 | 1824 | 3 | 4 | 5 | | V-1 | BC068157 | 1.84 |
| 1729 | 3 | 4 | 5 | | V-1 | 2810410L24Rik | 1.90 | 1825 | 3 | 4 | 5 | | V-1 | Bai1 | 1.91 |
| 1730 | 3 | 4 | 5 | | V-1 | 2810442N19Rik | 1.70 | 1826 | 3 | 4 | 5 | | V-1 | Bai2 | 1.54 |
| 1731 | 3 | 4 | 5 | | V-1 | 2900011O08Rik | 1.58 | 1827 | 3 | 4 | 5 | | V-1 | Bai3 | 1.55 |
| 1732 | 3 | 4 | 5 | | V-1 | 3110007F17Rik | 1.51 | 1828 | 3 | 4 | 5 | | V-1 | Barhl2 | 1.88 |
| 1733 | 3 | 4 | 5 | | V-1 | 3110021A11Rik | 1.85 | 1829 | 3 | 4 | 5 | | V-1 | Bbc3 | 1.52 |
| 1734 | 3 | 4 | 5 | | V-1 | 3110021N24Rik | 1.82 | 1830 | 3 | 4 | 5 | | V-1 | Bcan | 1.74 |
| 1735 | 3 | 4 | 5 | | V-1 | 4833411C07Rik | 1.57 | 1831 | 3 | 4 | 5 | | V-1 | Bdnf | 1.61 |
| 1736 | 3 | 4 | 5 | | V-1 | 4833424O15Rik | 1.75 | 1832 | 3 | 4 | 5 | | V-1 | Bean1 | 1.53 |
| 1737 | 3 | 4 | 5 | | V-1 | 4921531C22Rik | 1.62 | 1833 | 3 | 4 | 5 | | V-1 | Begain | 1.81 |
| 1738 | 3 | 4 | 5 | | V-1 | 4930404I05Rik | 1.76 | 1834 | 3 | 4 | 5 | | V-1 | Bend5 | 1.68 |
| 1739 | 3 | 4 | 5 | | V-1 | 4930455C13Rik | 1.63 | 1835 | 3 | 4 | 5 | | V-1 | Bicd1 | 1.55 |
| 1740 | 3 | 4 | 5 | | V-1 | 4930487H11Rik | 1.61 | 1836 | 3 | 4 | 5 | | V-1 | Bnc2 | 1.51 |
| 1741 | 3 | 4 | 5 | | V-1 | 4930579G18Rik | 1.53 | 1837 | 3 | 4 | 5 | | V-1 | Brdt | 1.56 |
| 1742 | 3 | 4 | 5 | | V-1 | 4930579K19Rik | 1.62 | 1838 | 3 | 4 | 5 | | V-1 | Brinp1 | 1.51 |
| 1743 | 3 | 4 | 5 | | V-1 | 4931428F04Rik | 1.73 | 1839 | 3 | 4 | 5 | | V-1 | Brinp2 | 1.73 |
| 1744 | 3 | 4 | 5 | | V-1 | 4933421O10Rik | 1.76 | 1840 | 3 | 4 | 5 | | V-1 | Brsk1 | 1.69 |
| 1745 | 3 | 4 | 5 | | V-1 | 5430416N02Rik | 1.60 | 1841 | 3 | 4 | 5 | | V-1 | Btbd17 | 1.83 |
| 1746 | 3 | 4 | 5 | | V-1 | 5430421F17Rik | 1.62 | 1842 | 3 | 4 | 5 | | V-1 | Btf3l4 | 1.65 |
| 1747 | 3 | 4 | 5 | | V-1 | 5730455P16Rik | 1.68 | 1843 | 3 | 4 | 5 | | V-1 | C030037D09Rik | 1.61 |
| 1748 | 3 | 4 | 5 | | V-1 | 6430573F11Rik | 1.82 | 1844 | 3 | 4 | 5 | | V-1 | C1qtnf4 | 1.91 |
| 1749 | 3 | 4 | 5 | | V-1 | 6720416L17Rik | 1.57 | 1845 | 3 | 4 | 5 | | V-1 | C330013E15Rik | 1.65 |
| 1750 | 3 | 4 | 5 | | V-1 | 9030612E09Rik | 1.88 | 1846 | 3 | 4 | 5 | | V-1 | C3ar1 | 1.73 |
| 1751 | 3 | 4 | 5 | | V-1 | 9130024F11Rik | 1.97 | 1847 | 3 | 4 | 5 | | V-1 | C530044C16Rik | 1.54 |
| 1752 | 3 | 4 | 5 | | V-1 | 9330133O14Rik | 1.73 | 1848 | 3 | 4 | 5 | | V-1 | C630043F03Rik | 1.54 |
| 1753 | 3 | 4 | 5 | | V-1 | 9330151L19Rik | 1.58 | 1849 | 3 | 4 | 5 | | V-1 | C920006O11Rik | 1.74 |
| 1754 | 3 | 4 | 5 | | V-1 | 9330159M07Rik | 1.58 | 1850 | 3 | 4 | 5 | | V-1 | Cabp1 | 1.62 |
| 1755 | 3 | 4 | 5 | | V-1 | 9430008C03Rik | 1.52 | 1851 | 3 | 4 | 5 | | V-1 | Cacna1a | 1.84 |
| 1756 | 3 | 4 | 5 | | V-1 | 9430021M05Rik | 1.59 | 1852 | 3 | 4 | 5 | | V-1 | Cacna1b | 1.67 |
| 1757 | 3 | 4 | 5 | | V-1 | 9430083A17Rik | 1.98 | 1853 | 3 | 4 | 5 | | V-1 | Cacna1c | 1.50 |
| 1758 | 3 | 4 | 5 | | V-1 | A230057D06Rik | 1.59 | 1854 | 3 | 4 | 5 | | V-1 | Cacna1d | 1.84 |
| 1759 | 3 | 4 | 5 | | V-1 | A330040F15Rik | 1.80 | 1855 | 3 | 4 | 5 | | V-1 | Cacna1h | 1.53 |
| 1760 | 3 | 4 | 5 | | V-1 | A630066F11Rik | 1.72 | 1856 | 3 | 4 | 5 | | V-1 | Cacna2d2 | 1.59 |
| 1761 | 3 | 4 | 5 | | V-1 | A830082N09Rik | 1.51 | 1857 | 3 | 4 | 5 | | V-1 | Cacnb4 | 1.52 |
| 1762 | 3 | 4 | 5 | | V-1 | AA415398 | 1.62 | 1858 | 3 | 4 | 5 | | V-1 | Cacng3 | 1.57 |
| 1763 | 3 | 4 | 5 | | V-1 | AF251705 | 1.64 | 1859 | 3 | 4 | 5 | | V-1 | Cadm3 | 1.65 |
| 1764 | 3 | 4 | 5 | | V-1 | AF529169 | 1.50 | 1860 | 3 | 4 | 5 | | V-1 | Cadm4 | 1.78 |
| 1765 | 3 | 4 | 5 | | V-1 | AI118078 | 1.54 | 1861 | 3 | 4 | 5 | | V-1 | Caln1 | 1.66 |
| 1766 | 3 | 4 | 5 | | V-1 | AI839979 | 1.54 | 1862 | 3 | 4 | 5 | | V-1 | Camk2n2 | 1.58 |
| 1767 | 3 | 4 | 5 | | V-1 | Abca5 | 1.61 | 1863 | 3 | 4 | 5 | | V-1 | Car1 | 1.92 |
| 1768 | 3 | 4 | 5 | | V-1 | Abca6 | 1.51 | 1864 | 3 | 4 | 5 | | V-1 | Car10 | 1.52 |
| 1769 | 3 | 4 | 5 | | V-1 | Accs | 1.69 | 1865 | 3 | 4 | 5 | | V-1 | Car11 | 1.53 |
| 1770 | 3 | 4 | 5 | | V-1 | Acsl6 | 1.63 | 1866 | 3 | 4 | 5 | | V-1 | Caskin1 | 1.74 |
| 1771 | 3 | 4 | 5 | | V-1 | Actl6b | 1.63 | 1867 | 3 | 4 | 5 | | V-1 | Casp12 | 1.67 |
| 1772 | 3 | 4 | 5 | | V-1 | Adam22 | 1.72 | 1868 | 3 | 4 | 5 | | V-1 | Catsper2 | 1.61 |
| 1773 | 3 | 4 | 5 | | V-1 | Adam23 | 1.65 | 1869 | 3 | 4 | 5 | | V-1 | Cbln1 | 1.69 |
| 1774 | 3 | 4 | 5 | | V-1 | Adamts19 | 1.60 | 1870 | 3 | 4 | 5 | | V-1 | Cbln2 | 1.62 |
| 1775 | 3 | 4 | 5 | | V-1 | Adcyap1 | 1.69 | 1871 | 3 | 4 | 5 | | V-1 | Cbln4 | 1.59 |
| 1776 | 3 | 4 | 5 | | V-1 | Aff2 | 1.62 | 1872 | 3 | 4 | 5 | | V-1 | Cbx7 | 1.55 |
| 1777 | 3 | 4 | 5 | | V-1 | Agap2 | 1.71 | 1873 | 3 | 4 | 5 | | V-1 | Ccdc106 | 1.68 |
| 1778 | 3 | 4 | 5 | | V-1 | Ahi1 | 1.50 | 1874 | 3 | 4 | 5 | | V-1 | Ccdc112 | 1.55 |
| 1779 | 3 | 4 | 5 | | V-1 | Akr1b8 | 1.67 | 1875 | 3 | 4 | 5 | | V-1 | Ccdc136 | 1.51 |
| 1780 | 3 | 4 | 5 | | V-1 | Amy1 | 1.59 | 1876 | 3 | 4 | 5 | | V-1 | Ccdc57 | 1.62 |
| 1781 | 3 | 4 | 5 | | V-1 | Amy2b | 1.51 | 1877 | 3 | 4 | 5 | | V-1 | Ccdc64 | 1.55 |
| 1782 | 3 | 4 | 5 | | V-1 | Angptl4 | 1.94 | 1878 | 3 | 4 | 5 | | V-1 | Ccl2 | 1.87 |
| 1783 | 3 | 4 | 5 | | V-1 | Angptl7 | 1.69 | 1879 | 3 | 4 | 5 | | V-1 | Ccl6 | 1.98 |
| 1784 | 3 | 4 | 5 | | V-1 | Ankra2 | 1.51 | 1880 | 3 | 4 | 5 | | V-1 | Ccl7 | 1.57 |
| 1785 | 3 | 4 | 5 | | V-1 | Ankrd13b | 1.54 | 1881 | 3 | 4 | 5 | | V-1 | Ccr1 | 1.50 |
| 1786 | 3 | 4 | 5 | | V-1 | Ankrd16 | 1.94 | 1882 | 3 | 4 | 5 | | V-1 | Cd300lg | 1.86 |
| 1787 | 3 | 4 | 5 | | V-1 | Ankrd2 | 1.88 | 1883 | 3 | 4 | 5 | | V-1 | Cd33 | 1.64 |
| 1788 | 3 | 4 | 5 | | V-1 | Ankrd61 | 1.78 | 1884 | 3 | 4 | 5 | | V-1 | Cdh22 | 1.98 |
| 1789 | 3 | 4 | 5 | | V-1 | Anks1b | 1.73 | 1885 | 3 | 4 | 5 | | V-1 | Cdh8 | 1.64 |
| 1790 | 3 | 4 | 5 | | V-1 | Apba2 | 1.73 | 1886 | 3 | 4 | 5 | | V-1 | Cdkl3 | 1.67 |
| 1791 | 3 | 4 | 5 | | V-1 | Apbb3 | 1.56 | 1887 | 3 | 4 | 5 | | V-1 | Celf3 | 1.69 |
| 1792 | 3 | 4 | 5 | | V-1 | Apc2 | 1.66 | 1888 | 3 | 4 | 5 | | V-1 | Celf4 | 1.75 |
| 1793 | 3 | 4 | 5 | | V-1 | Aplp1 | 1.57 | 1889 | 3 | 4 | 5 | | V-1 | Celf5 | 1.56 |
| 1794 | 3 | 4 | 5 | | V-1 | Apod | 1.75 | 1890 | 3 | 4 | 5 | | V-1 | Celsr3 | 1.62 |
| 1795 | 3 | 4 | 5 | | V-1 | Apold1 | 1.62 | 1891 | 3 | 4 | 5 | | V-1 | Cep83os | 1.69 |
| 1796 | 3 | 4 | 5 | | V-1 | Arf2 | 1.53 | 1892 | 3 | 4 | 5 | | V-1 | Cers4 | 1.64 |
| 1797 | 3 | 4 | 5 | | V-1 | Arg1 | 1.85 | 1893 | 3 | 4 | 5 | | V-1 | Chd5 | 1.63 |
| 1798 | 3 | 4 | 5 | | V-1 | Arsg | 1.62 | 1894 | 3 | 4 | 5 | | V-1 | Chgb | 1.60 |
| 1799 | 3 | 4 | 5 | | V-1 | Art3 | 1.57 | 1895 | 3 | 4 | 5 | | V-1 | Chic1 | 1.53 |
| 1800 | 3 | 4 | 5 | | V-1 | Asap2 | 1.55 | 1896 | 3 | 4 | 5 | | V-1 | Chil1 | 1.99 |
| 1801 | 3 | 4 | 5 | | V-1 | Asic1 | 1.51 | 1897 | 3 | 4 | 5 | | V-1 | Chpf2 | 1.57 |
| 1802 | 3 | 4 | 5 | | V-1 | Asic2 | 1.71 | 1898 | 3 | 4 | 5 | | V-1 | Chrna7 | 1.56 |
| 1803 | 3 | 4 | 5 | | V-1 | Asphd2 | 1.53 | 1899 | 3 | 4 | 5 | | V-1 | Clec2l | 1.61 |
| 1804 | 3 | 4 | 5 | | V-1 | Astn1 | 1.60 | 1900 | 3 | 4 | 5 | | V-1 | Clec4n | 1.60 |
| 1805 | 3 | 4 | 5 | | V-1 | Asxl3 | 1.50 | 1901 | 3 | 4 | 5 | | V-1 | Clstn1 | 1.52 |
| 1806 | 3 | 4 | 5 | | V-1 | Atp1a3 | 1.56 | 1902 | 3 | 4 | 5 | | V-1 | Clvs1 | 1.90 |
| 1807 | 3 | 4 | 5 | | V-1 | Atp6v0e2 | 1.53 | 1903 | 3 | 4 | 5 | | V-1 | Clvs2 | 1.64 |
| 1808 | 3 | 4 | 5 | | V-1 | Atp6v1g2 | 1.61 | 1904 | 3 | 4 | 5 | | V-1 | Cmpk2 | 1.51 |
| 1809 | 3 | 4 | 5 | | V-1 | Auts2 | 1.60 | 1905 | 3 | 4 | 5 | | V-1 | Cnih3 | 1.90 |
| 1810 | 3 | 4 | 5 | | V-1 | Avil | 1.62 | 1906 | 3 | 4 | 5 | | V-1 | Cnksr2 | 1.77 |
| 1811 | 3 | 4 | 5 | | V-1 | Azgp1 | 1.52 | 1907 | 3 | 4 | 5 | | V-1 | Cnr1 | 1.79 |
| 1812 | 3 | 4 | 5 | | V-1 | B3galt1 | 1.55 | 1908 | 3 | 4 | 5 | | V-1 | Cnrip1 | 1.53 |
| 1813 | 3 | 4 | 5 | | V-1 | B3gat1 | 1.66 | 1909 | 3 | 4 | 5 | | V-1 | Cntn2 | 1.57 |
| 1814 | 3 | 4 | 5 | | V-1 | B430319G15Rik | 1.56 | 1910 | 3 | 4 | 5 | | V-1 | Cntnap2 | 1.75 |
| 1815 | 3 | 4 | 5 | | V-1 | B4galnt4 | 1.67 | 1911 | 3 | 4 | 5 | | V-1 | Cntnap4 | 1.69 |
| 1816 | 3 | 4 | 5 | | V-1 | B630019K06Rik | 1.51 | 1912 | 3 | 4 | 5 | | V-1 | Col19a1 | 1.53 |
| 1817 | 3 | 4 | 5 | | V-1 | B930041F14Rik | 1.83 | 1913 | 3 | 4 | 5 | | V-1 | Col25a1 | 1.72 |
| 1818 | 3 | 4 | 5 | | V-1 | BC005764 | 1.59 | 1914 | 3 | 4 | 5 | | V-1 | Corin | 1.65 |
| 1819 | 3 | 4 | 5 | | V-1 | BC022687 | 1.63 | 1915 | 3 | 4 | 5 | | V-1 | Cp | 1.60 |
| 1820 | 3 | 4 | 5 | | V-1 | BC029214 | 1.51 | 1916 | 3 | 4 | 5 | | V-1 | Cplx2 | 1.67 |
| 1821 | 3 | 4 | 5 | | V-1 | BC037704 | 1.58 | 1917 | 3 | 4 | 5 | | V-1 | Cpt1a | 1.93 |
| 1822 | 3 | 4 | 5 | | V-1 | BC048403 | 1.64 | 1918 | 3 | 4 | 5 | | V-1 | Creb3l4 | 1.75 |

Fig. 45 - 11

| | | | | | | | | | | | | | | | | |
|---|---|---|---|---|---|---|---|---|---|---|---|---|---|---|---|---|
| 1919 | 3 | 4 | 5 | | | V-1 | Crebrf | 1.67 | 2015 | 3 | 4 | 5 | | | V-1 | Fam184b | 1.55 |
| 1920 | 3 | 4 | 5 | | | V-1 | Creg2 | 1.74 | 2016 | 3 | 4 | 5 | | | V-1 | Fam187b | 1.53 |
| 1921 | 3 | 4 | 5 | | | V-1 | Crmp1 | 1.63 | 2017 | 3 | 4 | 5 | | | V-1 | Fam188b | 1.58 |
| 1922 | 3 | 4 | 5 | | | V-1 | Crtc1 | 1.59 | 2018 | 3 | 4 | 5 | | | V-1 | Fam189a1 | 1.82 |
| 1923 | 3 | 4 | 5 | | | V-1 | Cryba4 | 1.51 | 2019 | 3 | 4 | 5 | | | V-1 | Fam196a | 1.54 |
| 1924 | 3 | 4 | 5 | | | V-1 | Crybb1 | 1.53 | 2020 | 3 | 4 | 5 | | | V-1 | Fam19a2 | 1.59 |
| 1925 | 3 | 4 | 5 | | | V-1 | Cryga | 1.62 | 2021 | 3 | 4 | 5 | | | V-1 | Fam19a5 | 1.58 |
| 1926 | 3 | 4 | 5 | | | V-1 | Csdc2 | 1.58 | 2022 | 3 | 4 | 5 | | | V-1 | Fam227a | 1.59 |
| 1927 | 3 | 4 | 5 | | | V-1 | Csmd2 | 1.60 | 2023 | 3 | 4 | 5 | | | V-1 | Fam228b | 1.90 |
| 1928 | 3 | 4 | 5 | | | V-1 | Csrnp3 | 1.57 | 2024 | 3 | 4 | 5 | | | V-1 | Fam57b | 1.63 |
| 1929 | 3 | 4 | 5 | | | V-1 | Cst7 | 1.63 | 2025 | 3 | 4 | 5 | | | V-1 | Fam69b | 1.85 |
| 1930 | 3 | 4 | 5 | | | V-1 | Ctnnd2 | 1.72 | 2026 | 3 | 4 | 5 | | | V-1 | Fan1 | 1.57 |
| 1931 | 3 | 4 | 5 | | | V-1 | Ctsf | 1.57 | 2027 | 3 | 4 | 5 | | | V-1 | Fance | 1.54 |
| 1932 | 3 | 4 | 5 | | | V-1 | Ctsg | 1.80 | 2028 | 3 | 4 | 5 | | | V-1 | Faxc | 1.68 |
| 1933 | 3 | 4 | 5 | | | V-1 | Ctxn1 | 1.55 | 2029 | 3 | 4 | 5 | | | V-1 | Fbrsl1 | 1.56 |
| 1934 | 3 | 4 | 5 | | | V-1 | Cul9 | 1.58 | 2030 | 3 | 4 | 5 | | | V-1 | Fbxl16 | 1.67 |
| 1935 | 3 | 4 | 5 | | | V-1 | Cxcl10 | 1.53 | 2031 | 3 | 4 | 5 | | | V-1 | Fbxl17 | 1.65 |
| 1936 | 3 | 4 | 5 | | | V-1 | Cxcl15 | 1.85 | 2032 | 3 | 4 | 5 | | | V-1 | Fbxo17 | 1.52 |
| 1937 | 3 | 4 | 5 | | | V-1 | Cxxc4 | 1.51 | 2033 | 3 | 4 | 5 | | | V-1 | Fbxo41 | 1.70 |
| 1938 | 3 | 4 | 5 | | | V-1 | Cyfip2 | 1.54 | 2034 | 3 | 4 | 5 | | | V-1 | Fbxw9 | 1.61 |
| 1939 | 3 | 4 | 5 | | | V-1 | Cyp17a1 | 1.67 | 2035 | 3 | 4 | 5 | | | V-1 | Fcgr1 | 1.74 |
| 1940 | 3 | 4 | 5 | | | V-1 | Cyp1b1 | 1.80 | 2036 | 3 | 4 | 5 | | | V-1 | Fez1 | 1.62 |
| 1941 | 3 | 4 | 5 | | | V-1 | Cyp26b1 | 1.97 | 2037 | 3 | 4 | 5 | | | V-1 | Fezf1 | 1.52 |
| 1942 | 3 | 4 | 5 | | | V-1 | Cyp27a1 | 1.71 | 2038 | 3 | 4 | 5 | | | V-1 | Fezf2 | 1.89 |
| 1943 | 3 | 4 | 5 | | | V-1 | Cyp2d22 | 1.92 | 2039 | 3 | 4 | 5 | | | V-1 | Fgfbp3 | 1.65 |
| 1944 | 3 | 4 | 5 | | | V-1 | Cyp3a11 | 1.50 | 2040 | 3 | 4 | 5 | | | V-1 | Fibp | 1.63 |
| 1945 | 3 | 4 | 5 | | | V-1 | Cyp3a25 | 1.59 | 2041 | 3 | 4 | 5 | | | V-1 | Fkbp1b | 1.60 |
| 1946 | 3 | 4 | 5 | | | V-1 | Cyp46a1 | 1.51 | 2042 | 3 | 4 | 5 | | | V-1 | Fkbp5 | 1.55 |
| 1947 | 3 | 4 | 5 | | | V-1 | Cyp4f17 | 1.81 | 2043 | 3 | 4 | 5 | | | V-1 | Fmn2 | 1.83 |
| 1948 | 3 | 4 | 5 | | | V-1 | Cyr61 | 1.58 | 2044 | 3 | 4 | 5 | | | V-1 | Fmo5 | 1.64 |
| 1949 | 3 | 4 | 5 | | | V-1 | Cytl1 | 1.54 | 2045 | 3 | 4 | 5 | | | V-1 | Foxb1 | 1.68 |
| 1950 | 3 | 4 | 5 | | | V-1 | D10Bwg1379e | 1.55 | 2046 | 3 | 4 | 5 | | | V-1 | Foxc1 | 1.58 |
| 1951 | 3 | 4 | 5 | | | V-1 | D330023K18Rik | 1.54 | 2047 | 3 | 4 | 5 | | | V-1 | Foxo6 | 1.60 |
| 1952 | 3 | 4 | 5 | | | V-1 | D3Bwg0562e | 1.71 | 2048 | 3 | 4 | 5 | | | V-1 | Frmd3 | 1.54 |
| 1953 | 3 | 4 | 5 | | | V-1 | D430041D05Rik | 1.50 | 2049 | 3 | 4 | 5 | | | V-1 | Frmd5 | 1.69 |
| 1954 | 3 | 4 | 5 | | | V-1 | D7Ertd715e | 1.58 | 2050 | 3 | 4 | 5 | | | V-1 | Frs3 | 1.66 |
| 1955 | 3 | 4 | 5 | | | V-1 | D830015G02Rik | 1.66 | 2051 | 3 | 4 | 5 | | | V-1 | Fsd1 | 1.64 |
| 1956 | 3 | 4 | 5 | | | V-1 | D930028M14Rik | 1.65 | 2052 | 3 | 4 | 5 | | | V-1 | Fstl5 | 1.72 |
| 1957 | 3 | 4 | 5 | | | V-1 | Dcc | 1.70 | 2053 | 3 | 4 | 5 | | | V-1 | G630025P09Rik | 1.69 |
| 1958 | 3 | 4 | 5 | | | V-1 | Dclk2 | 1.89 | 2054 | 3 | 4 | 5 | | | V-1 | Gabbr1 | 1.58 |
| 1959 | 3 | 4 | 5 | | | V-1 | Dcp1b | 1.53 | 2055 | 3 | 4 | 5 | | | V-1 | Gabra2 | 1.81 |
| 1960 | 3 | 4 | 5 | | | V-1 | Dcx | 1.68 | 2056 | 3 | 4 | 5 | | | V-1 | Gabra5 | 1.51 |
| 1961 | 3 | 4 | 5 | | | V-1 | Deaf1 | 1.55 | 2057 | 3 | 4 | 5 | | | V-1 | Gabrb2 | 1.67 |
| 1962 | 3 | 4 | 5 | | | V-1 | Defb1 | 1.74 | 2058 | 3 | 4 | 5 | | | V-1 | Gabrb3 | 1.60 |
| 1963 | 3 | 4 | 5 | | | V-1 | Derl3 | 1.59 | 2059 | 3 | 4 | 5 | | | V-1 | Gad1 | 1.76 |
| 1964 | 3 | 4 | 5 | | | V-1 | Dfna5 | 1.73 | 2060 | 3 | 4 | 5 | | | V-1 | Gadd45a | 1.91 |
| 1965 | 3 | 4 | 5 | | | V-1 | Dio3 | 1.63 | 2061 | 3 | 4 | 5 | | | V-1 | Gal3st3 | 1.74 |
| 1966 | 3 | 4 | 5 | | | V-1 | Diras1 | 1.60 | 2062 | 3 | 4 | 5 | | | V-1 | Galnt14 | 1.51 |
| 1967 | 3 | 4 | 5 | | | V-1 | Dlgap1 | 1.59 | 2063 | 3 | 4 | 5 | | | V-1 | Galnt15 | 1.52 |
| 1968 | 3 | 4 | 5 | | | V-1 | Dlgap3 | 1.57 | 2064 | 3 | 4 | 5 | | | V-1 | Galnt9 | 1.56 |
| 1969 | 3 | 4 | 5 | | | V-1 | Dll3 | 1.55 | 2065 | 3 | 4 | 5 | | | V-1 | Garnl3 | 1.87 |
| 1970 | 3 | 4 | 5 | | | V-1 | Dlx1 | 1.65 | 2066 | 3 | 4 | 5 | | | V-1 | Gbp7 | 1.61 |
| 1971 | 3 | 4 | 5 | | | V-1 | Dlx2 | 1.67 | 2067 | 3 | 4 | 5 | | | V-1 | Gbp9 | 1.88 |
| 1972 | 3 | 4 | 5 | | | V-1 | Dlx6 | 1.60 | 2068 | 3 | 4 | 5 | | | V-1 | Gcfc2 | 1.52 |
| 1973 | 3 | 4 | 5 | | | V-1 | Dmrta2 | 1.51 | 2069 | 3 | 4 | 5 | | | V-1 | Gdap1l1 | 1.60 |
| 1974 | 3 | 4 | 5 | | | V-1 | Dmrtb1 | 1.60 | 2070 | 3 | 4 | 5 | | | V-1 | Gdf5 | 1.50 |
| 1975 | 3 | 4 | 5 | | | V-1 | Dner | 1.50 | 2071 | 3 | 4 | 5 | | | V-1 | Gdf6 | 1.99 |
| 1976 | 3 | 4 | 5 | | | V-1 | Dnm1 | 1.61 | 2072 | 3 | 4 | 5 | | | V-1 | Ggt7 | 1.61 |
| 1977 | 3 | 4 | 5 | | | V-1 | Dnm3 | 1.63 | 2073 | 3 | 4 | 5 | | | V-1 | Gh | 1.66 |
| 1978 | 3 | 4 | 5 | | | V-1 | Dnm3os | 1.53 | 2074 | 3 | 4 | 5 | | | V-1 | Glra2 | 1.73 |
| 1979 | 3 | 4 | 5 | | | V-1 | Doc2g | 1.63 | 2075 | 3 | 4 | 5 | | | V-1 | Glt1d1 | 1.65 |
| 1980 | 3 | 4 | 5 | | | V-1 | Dok6 | 1.77 | 2076 | 3 | 4 | 5 | | | V-1 | Gm10406 | 1.87 |
| 1981 | 3 | 4 | 5 | | | V-1 | Dpf1 | 1.72 | 2077 | 3 | 4 | 5 | | | V-1 | Gm10409 | 1.78 |
| 1982 | 3 | 4 | 5 | | | V-1 | Dph5 | 1.54 | 2078 | 3 | 4 | 5 | | | V-1 | Gm10560 | 1.67 |
| 1983 | 3 | 4 | 5 | | | V-1 | Dpp10 | 1.89 | 2079 | 3 | 4 | 5 | | | V-1 | Gm11627 | 1.53 |
| 1984 | 3 | 4 | 5 | | | V-1 | Dpysl4 | 1.98 | 2080 | 3 | 4 | 5 | | | V-1 | Gm12669 | 1.73 |
| 1985 | 3 | 4 | 5 | | | V-1 | Draxin | 1.57 | 2081 | 3 | 4 | 5 | | | V-1 | Gm13139 | 1.55 |
| 1986 | 3 | 4 | 5 | | | V-1 | Drp2 | 1.52 | 2082 | 3 | 4 | 5 | | | V-1 | Gm13238 | 1.66 |
| 1987 | 3 | 4 | 5 | | | V-1 | Dscam | 1.62 | 2083 | 3 | 4 | 5 | | | V-1 | Gm14005 | 1.79 |
| 1988 | 3 | 4 | 5 | | | V-1 | Dusp4 | 1.54 | 2084 | 3 | 4 | 5 | | | V-1 | Gm14378 | 1.75 |
| 1989 | 3 | 4 | 5 | | | V-1 | Dzank1 | 1.83 | 2085 | 3 | 4 | 5 | | | V-1 | Gm15545 | 1.53 |
| 1990 | 3 | 4 | 5 | | | V-1 | E130114P18Rik | 1.58 | 2086 | 3 | 4 | 5 | | | V-1 | Gm15612 | 1.84 |
| 1991 | 3 | 4 | 5 | | | V-1 | E130307A14Rik | 1.55 | 2087 | 3 | 4 | 5 | | | V-1 | Gm15706 | 1.58 |
| 1992 | 3 | 4 | 5 | | | V-1 | E130309F12Rik | 1.59 | 2088 | 3 | 4 | 5 | | | V-1 | Gm15787 | 1.59 |
| 1993 | 3 | 4 | 5 | | | V-1 | E230029C05Rik | 1.61 | 2089 | 3 | 4 | 5 | | | V-1 | Gm16386 | 1.52 |
| 1994 | 3 | 4 | 5 | | | V-1 | Ebf3 | 1.67 | 2090 | 3 | 4 | 5 | | | V-1 | Gm16617 | 1.58 |
| 1995 | 3 | 4 | 5 | | | V-1 | Ebf4 | 1.59 | 2091 | 3 | 4 | 5 | | | V-1 | Gm16702 | 1.65 |
| 1996 | 3 | 4 | 5 | | | V-1 | Ecel1 | 1.98 | 2092 | 3 | 4 | 5 | | | V-1 | Gm19345 | 1.53 |
| 1997 | 3 | 4 | 5 | | | V-1 | Eda2r | 1.95 | 2093 | 3 | 4 | 5 | | | V-1 | Gm20337 | 1.53 |
| 1998 | 3 | 4 | 5 | | | V-1 | Efnb3 | 1.56 | 2094 | 3 | 4 | 5 | | | V-1 | Gm20878 | 1.51 |
| 1999 | 3 | 4 | 5 | | | V-1 | Ehhadh | 1.74 | 2095 | 3 | 4 | 5 | | | V-1 | Gm3264 | 1.77 |
| 2000 | 3 | 4 | 5 | | | V-1 | Eid2b | 1.61 | 2096 | 3 | 4 | 5 | | | V-1 | Gm3317 | 1.67 |
| 2001 | 3 | 4 | 5 | | | V-1 | Elavl2 | 1.62 | 2097 | 3 | 4 | 5 | | | V-1 | Gm3500 | 1.72 |
| 2002 | 3 | 4 | 5 | | | V-1 | Elavl3 | 1.62 | 2098 | 3 | 4 | 5 | | | V-1 | Gm4890 | 1.64 |
| 2003 | 3 | 4 | 5 | | | V-1 | Elavl4 | 1.56 | 2099 | 3 | 4 | 5 | | | V-1 | Gm4951 | 1.65 |
| 2004 | 3 | 4 | 5 | | | V-1 | Eml5 | 1.78 | 2100 | 3 | 4 | 5 | | | V-1 | Gm5089 | 1.63 |
| 2005 | 3 | 4 | 5 | | | V-1 | Emx1 | 1.75 | 2101 | 3 | 4 | 5 | | | V-1 | Gm5416 | 1.62 |
| 2006 | 3 | 4 | 5 | | | V-1 | En2 | 1.99 | 2102 | 3 | 4 | 5 | | | V-1 | Gm5483 | 1.54 |
| 2007 | 3 | 4 | 5 | | | V-1 | Eomes | 1.50 | 2103 | 3 | 4 | 5 | | | V-1 | Gm5577 | 1.72 |
| 2008 | 3 | 4 | 5 | | | V-1 | Epha5 | 1.56 | 2104 | 3 | 4 | 5 | | | V-1 | Gm6297 | 1.94 |
| 2009 | 3 | 4 | 5 | | | V-1 | Epha8 | 1.57 | 2105 | 3 | 4 | 5 | | | V-1 | Gm6642 | 1.52 |
| 2010 | 3 | 4 | 5 | | | V-1 | Ephb1 | 1.85 | 2106 | 3 | 4 | 5 | | | V-1 | Gm9079 | 1.96 |
| 2011 | 3 | 4 | 5 | | | V-1 | Extl1 | 1.74 | 2107 | 3 | 4 | 5 | | | V-1 | Gm9839 | 1.76 |
| 2012 | 3 | 4 | 5 | | | V-1 | Eya2 | 1.65 | 2108 | 3 | 4 | 5 | | | V-1 | Gm9855 | 1.52 |
| 2013 | 3 | 4 | 5 | | | V-1 | Fam163a | 1.72 | 2109 | 3 | 4 | 5 | | | V-1 | Gnb1l | 1.61 |
| 2014 | 3 | 4 | 5 | | | V-1 | Fam169a | 1.58 | 2110 | 3 | 4 | 5 | | | V-1 | Gng2 | 1.59 |

Fig. 45 - 12

| | | | | | | | | | | | | | | | | |
|---|---|---|---|---|---|---|---|---|---|---|---|---|---|---|---|---|
| 2111 | 3 | 4 | 5 | | V-1 | Gng3 | 1.52 | 2207 | 3 | 4 | 5 | | V-1 | Kif5c | 1.57 |
| 2112 | 3 | 4 | 5 | | V-1 | Gng7 | 1.51 | 2208 | 3 | 4 | 5 | | V-1 | Kifc2 | 1.60 |
| 2113 | 3 | 4 | 5 | | V-1 | Golga7b | 1.52 | 2209 | 3 | 4 | 5 | | V-1 | Kirrel3 | 1.87 |
| 2114 | 3 | 4 | 5 | | V-1 | Gp1bb | 1.67 | 2210 | 3 | 4 | 5 | | V-1 | Klf11 | 1.58 |
| 2115 | 3 | 4 | 5 | | V-1 | Gpm6a | 1.58 | 2211 | 3 | 4 | 5 | | V-1 | Ksr2 | 1.51 |
| 2116 | 3 | 4 | 5 | | V-1 | Gpr139 | 1.54 | 2212 | 3 | 4 | 5 | | V-1 | Larp6 | 1.75 |
| 2117 | 3 | 4 | 5 | | V-1 | Gpr162 | 1.53 | 2213 | 3 | 4 | 5 | | V-1 | Lca5 | 1.56 |
| 2118 | 3 | 4 | 5 | | V-1 | Gpr173 | 1.86 | 2214 | 3 | 4 | 5 | | V-1 | Lca5l | 1.59 |
| 2119 | 3 | 4 | 5 | | V-1 | Gpr21 | 1.58 | 2215 | 3 | 4 | 5 | | V-1 | Lcn2 | 1.68 |
| 2120 | 3 | 4 | 5 | | V-1 | Gpr22 | 1.54 | 2216 | 3 | 4 | 5 | | V-1 | Letm2 | 1.74 |
| 2121 | 3 | 4 | 5 | | V-1 | Gpr27 | 1.93 | 2217 | 3 | 4 | 5 | | V-1 | Lgals3bp | 1.62 |
| 2122 | 3 | 4 | 5 | | V-1 | Gpr63 | 1.82 | 2218 | 3 | 4 | 5 | | V-1 | Lhfpl4 | 1.74 |
| 2123 | 3 | 4 | 5 | | V-1 | Gpr68 | 1.56 | 2219 | 3 | 4 | 5 | | V-1 | Lhx1 | 1.83 |
| 2124 | 3 | 4 | 5 | | V-1 | Gpr75 | 1.90 | 2220 | 3 | 4 | 5 | | V-1 | Lhx5 | 1.84 |
| 2125 | 3 | 4 | 5 | | V-1 | Gpr85 | 1.57 | 2221 | 3 | 4 | 5 | | V-1 | Lim2 | 1.81 |
| 2126 | 3 | 4 | 5 | | V-1 | Gria1 | 1.51 | 2222 | 3 | 4 | 5 | | V-1 | Lmbr1 | 1.56 |
| 2127 | 3 | 4 | 5 | | V-1 | Gria2 | 1.85 | 2223 | 3 | 4 | 5 | | V-1 | Lmx1a | 1.63 |
| 2128 | 3 | 4 | 5 | | V-1 | Grid2 | 1.60 | 2224 | 3 | 4 | 5 | | V-1 | Lpxn | 1.56 |
| 2129 | 3 | 4 | 5 | | V-1 | Grik2 | 1.77 | 2225 | 3 | 4 | 5 | | V-1 | Lrfn2 | 1.52 |
| 2130 | 3 | 4 | 5 | | V-1 | Grik3 | 1.60 | 2226 | 3 | 4 | 5 | | V-1 | Lrfn5 | 1.75 |
| 2131 | 3 | 4 | 5 | | V-1 | Grik4 | 1.76 | 2227 | 3 | 4 | 5 | | V-1 | Lrp8 | 1.80 |
| 2132 | 3 | 4 | 5 | | V-1 | Grik5 | 1.55 | 2228 | 3 | 4 | 5 | | V-1 | Lrrc16b | 1.87 |
| 2133 | 3 | 4 | 5 | | V-1 | Grin2b | 1.55 | 2229 | 3 | 4 | 5 | | V-1 | Lrrc25 | 1.52 |
| 2134 | 3 | 4 | 5 | | V-1 | Grip1 | 1.72 | 2230 | 3 | 4 | 5 | | V-1 | Lrrc26 | 1.51 |
| 2135 | 3 | 4 | 5 | | V-1 | Grm2 | 1.50 | 2231 | 3 | 4 | 5 | | V-1 | Lrrc29 | 1.88 |
| 2136 | 3 | 4 | 5 | | V-1 | Grp | 1.80 | 2232 | 3 | 4 | 5 | | V-1 | Lrrc49 | 1.53 |
| 2137 | 3 | 4 | 5 | | V-1 | Gtpbp6 | 1.60 | 2233 | 3 | 4 | 5 | | V-1 | Lrrc4c | 1.93 |
| 2138 | 3 | 4 | 5 | | V-1 | H2-M5 | 1.98 | 2234 | 3 | 4 | 5 | | V-1 | Lrrc8e | 1.53 |
| 2139 | 3 | 4 | 5 | | V-1 | Haghl | 1.59 | 2235 | 3 | 4 | 5 | | V-1 | Lrm4cl | 1.83 |
| 2140 | 3 | 4 | 5 | | V-1 | Hap1 | 1.60 | 2236 | 3 | 4 | 5 | | V-1 | Lrrtm1 | 1.52 |
| 2141 | 3 | 4 | 5 | | V-1 | Hcn4 | 1.75 | 2237 | 3 | 4 | 5 | | V-1 | Lrrtm4 | 1.50 |
| 2142 | 3 | 4 | 5 | | V-1 | Hddc2 | 1.72 | 2238 | 3 | 4 | 5 | | V-1 | Lsamp | 1.93 |
| 2143 | 3 | 4 | 5 | | V-1 | Hes5 | 1.52 | 2239 | 3 | 4 | 5 | | V-1 | Ltb4r2 | 1.59 |
| 2144 | 3 | 4 | 5 | | V-1 | Hhipl1 | 1.55 | 2240 | 3 | 4 | 5 | | V-1 | Luzp2 | 1.59 |
| 2145 | 3 | 4 | 5 | | V-1 | Hist1h2bl | 1.52 | 2241 | 3 | 4 | 5 | | V-1 | Ly6h | 1.56 |
| 2146 | 3 | 4 | 5 | | V-1 | Hist1h3a | 1.90 | 2242 | 3 | 4 | 5 | | V-1 | Lypd1 | 1.77 |
| 2147 | 3 | 4 | 5 | | V-1 | Hmga1 | 1.78 | 2243 | 3 | 4 | 5 | | V-1 | Lypd6b | 1.80 |
| 2148 | 3 | 4 | 5 | | V-1 | Hmgcll1 | 1.59 | 2244 | 3 | 4 | 5 | | V-1 | Mab21l1 | 1.87 |
| 2149 | 3 | 4 | 5 | | V-1 | Hoxa1los | 1.59 | 2245 | 3 | 4 | 5 | | V-1 | Mab21l2 | 1.51 |
| 2150 | 3 | 4 | 5 | | V-1 | Hoxb8 | 1.78 | 2246 | 3 | 4 | 5 | | V-1 | Magi2 | 1.68 |
| 2151 | 3 | 4 | 5 | | V-1 | Hoxd9 | 1.52 | 2247 | 3 | 4 | 5 | | V-1 | Map3k6 | 1.54 |
| 2152 | 3 | 4 | 5 | | V-1 | Hpca | 1.52 | 2248 | 3 | 4 | 5 | | V-1 | Map3k8 | 1.81 |
| 2153 | 3 | 4 | 5 | | V-1 | Hrct1 | 1.93 | 2249 | 3 | 4 | 5 | | V-1 | Map3k9 | 1.51 |
| 2154 | 3 | 4 | 5 | | V-1 | Hs3st4 | 1.67 | 2250 | 3 | 4 | 5 | | V-1 | Map7d2 | 1.75 |
| 2155 | 3 | 4 | 5 | | V-1 | Hs3st5 | 1.81 | 2251 | 3 | 4 | 5 | | V-1 | Mapk10 | 1.91 |
| 2156 | 3 | 4 | 5 | | V-1 | Hs6st3 | 1.56 | 2252 | 3 | 4 | 5 | | V-1 | Mapk4 | 1.52 |
| 2157 | 3 | 4 | 5 | | V-1 | Htr2c | 1.51 | 2253 | 3 | 4 | 5 | | V-1 | Mapk8ip2 | 1.70 |
| 2158 | 3 | 4 | 5 | | V-1 | Ica1l | 1.84 | 2254 | 3 | 4 | 5 | | V-1 | March1 | 1.62 |
| 2159 | 3 | 4 | 5 | | V-1 | Ifi202b | 1.83 | 2255 | 3 | 4 | 5 | | V-1 | March11 | 1.69 |
| 2160 | 3 | 4 | 5 | | V-1 | Ifi203 | 1.56 | 2256 | 3 | 4 | 5 | | V-1 | March4 | 1.73 |
| 2161 | 3 | 4 | 5 | | V-1 | Ifi27l2a | 1.92 | 2257 | 3 | 4 | 5 | | V-1 | Mark1 | 1.52 |
| 2162 | 3 | 4 | 5 | | V-1 | Ifi44 | 1.98 | 2258 | 3 | 4 | 5 | | V-1 | Mast1 | 1.75 |
| 2163 | 3 | 4 | 5 | | V-1 | Ifih1 | 1.73 | 2259 | 3 | 4 | 5 | | V-1 | Mc4r | 1.71 |
| 2164 | 3 | 4 | 5 | | V-1 | Ifit2 | 1.66 | 2260 | 3 | 4 | 5 | | V-1 | Mchr1 | 1.97 |
| 2165 | 3 | 4 | 5 | | V-1 | Ifitm1 | 1.60 | 2261 | 3 | 4 | 5 | | V-1 | Mdga2 | 1.94 |
| 2166 | 3 | 4 | 5 | | V-1 | Ifitm3 | 1.94 | 2262 | 3 | 4 | 5 | | V-1 | Meis3 | 1.62 |
| 2167 | 3 | 4 | 5 | | V-1 | Igdcc3 | 1.54 | 2263 | 3 | 4 | 5 | | V-1 | Mettl20 | 1.54 |
| 2168 | 3 | 4 | 5 | | V-1 | Igfbp2 | 1.52 | 2264 | 3 | 4 | 5 | | V-1 | Mettl21c | 1.80 |
| 2169 | 3 | 4 | 5 | | V-1 | Igfbpl1 | 1.96 | 2265 | 3 | 4 | 5 | | V-1 | Mgat5b | 1.83 |
| 2170 | 3 | 4 | 5 | | V-1 | Iglon5 | 1.77 | 2266 | 3 | 4 | 5 | | V-1 | Micu3 | 1.66 |
| 2171 | 3 | 4 | 5 | | V-1 | Igsf11 | 1.56 | 2267 | 3 | 4 | 5 | | V-1 | Mirlet7bhg | 1.67 |
| 2172 | 3 | 4 | 5 | | V-1 | Igsf21 | 1.66 | 2268 | 3 | 4 | 5 | | V-1 | Mkln1os | 1.60 |
| 2173 | 3 | 4 | 5 | | V-1 | Iigp1 | 1.79 | 2269 | 3 | 4 | 5 | | V-1 | Mllt11 | 1.53 |
| 2174 | 3 | 4 | 5 | | V-1 | Ikzf4 | 1.77 | 2270 | 3 | 4 | 5 | | V-1 | Mmp16 | 1.53 |
| 2175 | 3 | 4 | 5 | | V-1 | Il1f6 | 1.58 | 2271 | 3 | 4 | 5 | | V-1 | Mndal | 1.54 |
| 2176 | 3 | 4 | 5 | | V-1 | Il1r2 | 1.90 | 2272 | 3 | 4 | 5 | | V-1 | Morn4 | 1.58 |
| 2177 | 3 | 4 | 5 | | V-1 | Inca1 | 1.88 | 2273 | 3 | 4 | 5 | | V-1 | Mpeg1 | 1.57 |
| 2178 | 3 | 4 | 5 | | V-1 | Inha | 1.92 | 2274 | 3 | 4 | 5 | | V-1 | Mpped1 | 1.53 |
| 2179 | 3 | 4 | 5 | | V-1 | Inpp5f | 1.58 | 2275 | 3 | 4 | 5 | | V-1 | Mpv17l | 1.51 |
| 2180 | 3 | 4 | 5 | | V-1 | Insl3 | 1.71 | 2276 | 3 | 4 | 5 | | V-1 | Ms4a4d | 1.60 |
| 2181 | 3 | 4 | 5 | | V-1 | Iqsec3 | 1.66 | 2277 | 3 | 4 | 5 | | V-1 | Msx1os | 1.62 |
| 2182 | 3 | 4 | 5 | | V-1 | Isl1 | 1.67 | 2278 | 3 | 4 | 5 | | V-1 | Mtus2 | 1.67 |
| 2183 | 3 | 4 | 5 | | V-1 | Islr2 | 1.71 | 2279 | 3 | 4 | 5 | | V-1 | Mycl | 1.61 |
| 2184 | 3 | 4 | 5 | | V-1 | Itgb8 | 1.64 | 2280 | 3 | 4 | 5 | | V-1 | Myt1 | 1.76 |
| 2185 | 3 | 4 | 5 | | V-1 | Jade2 | 1.75 | 2281 | 3 | 4 | 5 | | V-1 | Myt1l | 1.90 |
| 2186 | 3 | 4 | 5 | | V-1 | Jakmip2 | 1.64 | 2282 | 3 | 4 | 5 | | V-1 | Mzf1 | 1.81 |
| 2187 | 3 | 4 | 5 | | V-1 | Jph3 | 1.59 | 2283 | 3 | 4 | 5 | | V-1 | N28178 | 1.65 |
| 2188 | 3 | 4 | 5 | | V-1 | Kalrn | 1.57 | 2284 | 3 | 4 | 5 | | V-1 | N6amt1 | 1.55 |
| 2189 | 3 | 4 | 5 | | V-1 | Kcnab3 | 1.53 | 2285 | 3 | 4 | 5 | | V-1 | Nacad | 1.54 |
| 2190 | 3 | 4 | 5 | | V-1 | Kcnc2 | 1.55 | 2286 | 3 | 4 | 5 | | V-1 | Nap1l5 | 1.52 |
| 2191 | 3 | 4 | 5 | | V-1 | Kcnc3 | 1.51 | 2287 | 3 | 4 | 5 | | V-1 | Napsa | 1.54 |
| 2192 | 3 | 4 | 5 | | V-1 | Kcnc4 | 1.52 | 2288 | 3 | 4 | 5 | | V-1 | Nbea | 1.51 |
| 2193 | 3 | 4 | 5 | | V-1 | Kcnd2 | 1.57 | 2289 | 3 | 4 | 5 | | V-1 | Ncam2 | 1.68 |
| 2194 | 3 | 4 | 5 | | V-1 | Kcnf1 | 1.51 | 2290 | 3 | 4 | 5 | | V-1 | Ncan | 1.53 |
| 2195 | 3 | 4 | 5 | | V-1 | Kcnip1 | 1.82 | 2291 | 3 | 4 | 5 | | V-1 | Ncmap | 1.53 |
| 2196 | 3 | 4 | 5 | | V-1 | Kcnj15 | 1.56 | 2292 | 3 | 4 | 5 | | V-1 | Ndst3 | 1.54 |
| 2197 | 3 | 4 | 5 | | V-1 | Kcnk10 | 1.59 | 2293 | 3 | 4 | 5 | | V-1 | Neat1 | 1.96 |
| 2198 | 3 | 4 | 5 | | V-1 | Kcnq2 | 1.51 | 2294 | 3 | 4 | 5 | | V-1 | Nell2 | 1.53 |
| 2199 | 3 | 4 | 5 | | V-1 | Kcnq5 | 1.61 | 2295 | 3 | 4 | 5 | | V-1 | Neto2 | 1.58 |
| 2200 | 3 | 4 | 5 | | V-1 | Kcnt1 | 1.96 | 2296 | 3 | 4 | 5 | | V-1 | Neurod1 | 1.63 |
| 2201 | 3 | 4 | 5 | | V-1 | Kctd13 | 1.91 | 2297 | 3 | 4 | 5 | | V-1 | Neurod2 | 1.95 |
| 2202 | 3 | 4 | 5 | | V-1 | Khdrbs2 | 1.55 | 2298 | 3 | 4 | 5 | | V-1 | Neurod6 | 1.82 |
| 2203 | 3 | 4 | 5 | | V-1 | Kif1a | 1.65 | 2299 | 3 | 4 | 5 | | V-1 | Nfasc | 1.81 |
| 2204 | 3 | 4 | 5 | | V-1 | Kif21b | 1.50 | 2300 | 3 | 4 | 5 | | V-1 | Nhlh2 | 1.60 |
| 2205 | 3 | 4 | 5 | | V-1 | Kif26b | 1.58 | 2301 | 3 | 4 | 5 | | V-1 | Nim1k | 1.55 |
| 2206 | 3 | 4 | 5 | | V-1 | Kif5a | 1.50 | 2302 | 3 | 4 | 5 | | V-1 | Nkain1 | 1.52 |

Fig. 45 - 13

| | | | | | | | | | | | | | | | | |
|---|---|---|---|---|---|---|---|---|---|---|---|---|---|---|---|---|
| 2303 | 3 | 4 | 5 | | | V-1 | Nkain2 | 1.56 | 2399 | 3 | 4 | 5 | | | V-1 | Pirb | 1.84 |
| 2304 | 3 | 4 | 5 | | | V-1 | Nkain3 | 1.83 | 2400 | 3 | 4 | 5 | | | V-1 | Pirt | 1.68 |
| 2305 | 3 | 4 | 5 | | | V-1 | Nkx2-2 | 1.64 | 2401 | 3 | 4 | 5 | | | V-1 | Plac9a | 1.79 |
| 2306 | 3 | 4 | 5 | | | V-1 | Nkx3-2 | 1.60 | 2402 | 3 | 4 | 5 | | | V-1 | Plcxd3 | 1.87 |
| 2307 | 3 | 4 | 5 | | | V-1 | Nlgn1 | 1.56 | 2403 | 3 | 4 | 5 | | | V-1 | Plxna4 | 1.51 |
| 2308 | 3 | 4 | 5 | | | V-1 | Nmb | 1.79 | 2404 | 3 | 4 | 5 | | | V-1 | Pnma3 | 1.98 |
| 2309 | 3 | 4 | 5 | | | V-1 | Nmi | 1.60 | 2405 | 3 | 4 | 5 | | | V-1 | Pnoc | 1.52 |
| 2310 | 3 | 4 | 5 | | | V-1 | Nmnat2 | 1.54 | 2406 | 3 | 4 | 5 | | | V-1 | Podn | 1.64 |
| 2311 | 3 | 4 | 5 | | | V-1 | Nnat | 1.58 | 2407 | 3 | 4 | 5 | | | V-1 | Podxl2 | 1.71 |
| 2312 | 3 | 4 | 5 | | | V-1 | Nol4 | 1.70 | 2408 | 3 | 4 | 5 | | | V-1 | Pou2f2 | 1.52 |
| 2313 | 3 | 4 | 5 | | | V-1 | Npas3 | 1.91 | 2409 | 3 | 4 | 5 | | | V-1 | Pou3f2 | 1.69 |
| 2314 | 3 | 4 | 5 | | | V-1 | Npff | 1.55 | 2410 | 3 | 4 | 5 | | | V-1 | Pou3f3 | 1.56 |
| 2315 | 3 | 4 | 5 | | | V-1 | Nppa | 1.76 | 2411 | 3 | 4 | 5 | | | V-1 | Pou3f4 | 1.63 |
| 2316 | 3 | 4 | 5 | | | V-1 | Nptxr | 1.76 | 2412 | 3 | 4 | 5 | | | V-1 | Pou4f1 | 1.95 |
| 2317 | 3 | 4 | 5 | | | V-1 | Nqo1 | 1.67 | 2413 | 3 | 4 | 5 | | | V-1 | Pou4f2 | 1.61 |
| 2318 | 3 | 4 | 5 | | | V-1 | Nr1d2 | 1.69 | 2414 | 3 | 4 | 5 | | | V-1 | Pou6f1 | 1.89 |
| 2319 | 3 | 4 | 5 | | | V-1 | Nr2e1 | 1.72 | 2415 | 3 | 4 | 5 | | | V-1 | Ppp2r2b | 1.71 |
| 2320 | 3 | 4 | 5 | | | V-1 | Nr2f1 | 1.63 | 2416 | 3 | 4 | 5 | | | V-1 | Ppp2r2c | 1.62 |
| 2321 | 3 | 4 | 5 | | | V-1 | Nrbp2 | 1.64 | 2417 | 3 | 4 | 5 | | | V-1 | Ppp3cc | 1.76 |
| 2322 | 3 | 4 | 5 | | | V-1 | Nrg1 | 1.79 | 2418 | 3 | 4 | 5 | | | V-1 | Ppp4r4 | 1.51 |
| 2323 | 3 | 4 | 5 | | | V-1 | Nrg3 | 1.52 | 2419 | 3 | 4 | 5 | | | V-1 | Prdm12 | 1.74 |
| 2324 | 3 | 4 | 5 | | | V-1 | Nrip3 | 1.72 | 2420 | 3 | 4 | 5 | | | V-1 | Prdm8 | 1.63 |
| 2325 | 3 | 4 | 5 | | | V-1 | Nrsn2 | 1.97 | 2421 | 3 | 4 | 5 | | | V-1 | Prima1 | 1.51 |
| 2326 | 3 | 4 | 5 | | | V-1 | Nrxn2 | 1.64 | 2422 | 3 | 4 | 5 | | | V-1 | Prmt8 | 1.98 |
| 2327 | 3 | 4 | 5 | | | V-1 | Nrxn3 | 1.52 | 2423 | 3 | 4 | 5 | | | V-1 | Prph | 1.66 |
| 2328 | 3 | 4 | 5 | | | V-1 | Nsg1 | 1.55 | 2424 | 3 | 4 | 5 | | | V-1 | Prr18 | 1.60 |
| 2329 | 3 | 4 | 5 | | | V-1 | Nsg2 | 1.59 | 2425 | 3 | 4 | 5 | | | V-1 | Prr7 | 1.63 |
| 2330 | 3 | 4 | 5 | | | V-1 | Nsun7 | 1.57 | 2426 | 3 | 4 | 5 | | | V-1 | Prrt4 | 1.65 |
| 2331 | 3 | 4 | 5 | | | V-1 | Ntng1 | 1.67 | 2427 | 3 | 4 | 5 | | | V-1 | Psd2 | 1.54 |
| 2332 | 3 | 4 | 5 | | | V-1 | Ntrk3 | 1.52 | 2428 | 3 | 4 | 5 | | | V-1 | Ptbp2 | 1.60 |
| 2333 | 3 | 4 | 5 | | | V-1 | Nudt10 | 1.60 | 2429 | 3 | 4 | 5 | | | V-1 | Ptchd1 | 1.55 |
| 2334 | 3 | 4 | 5 | | | V-1 | Nudt11 | 1.56 | 2430 | 3 | 4 | 5 | | | V-1 | Ptchd2 | 1.52 |
| 2335 | 3 | 4 | 5 | | | V-1 | Nudt16 | 1.92 | 2431 | 3 | 4 | 5 | | | V-1 | Ptprs | 1.75 |
| 2336 | 3 | 4 | 5 | | | V-1 | Nwd1 | 1.54 | 2432 | 3 | 4 | 5 | | | V-1 | Ptprn | 1.56 |
| 2337 | 3 | 4 | 5 | | | V-1 | Nwd2 | 1.77 | 2433 | 3 | 4 | 5 | | | V-1 | Ptprn2 | 1.56 |
| 2338 | 3 | 4 | 5 | | | V-1 | Nxph1 | 1.84 | 2434 | 3 | 4 | 5 | | | V-1 | Ptprt | 1.56 |
| 2339 | 3 | 4 | 5 | | | V-1 | Nyap1 | 1.64 | 2435 | 3 | 4 | 5 | | | V-1 | Ptx3 | 1.65 |
| 2340 | 3 | 4 | 5 | | | V-1 | Nyap2 | 1.72 | 2436 | 3 | 4 | 5 | | | V-1 | Rab10os | 1.91 |
| 2341 | 3 | 4 | 5 | | | V-1 | Oas1b | 1.76 | 2437 | 3 | 4 | 5 | | | V-1 | Rab11fip4 | 1.52 |
| 2342 | 3 | 4 | 5 | | | V-1 | Oas2 | 1.93 | 2438 | 3 | 4 | 5 | | | V-1 | Rab34 | 1.58 |
| 2343 | 3 | 4 | 5 | | | V-1 | Ofd1 | 1.78 | 2439 | 3 | 4 | 5 | | | V-1 | Rab36 | 1.65 |
| 2344 | 3 | 4 | 5 | | | V-1 | Olfm3 | 1.53 | 2440 | 3 | 4 | 5 | | | V-1 | Rab39b | 1.64 |
| 2345 | 3 | 4 | 5 | | | V-1 | Olfm4 | 1.54 | 2441 | 3 | 4 | 5 | | | V-1 | Rab3b | 1.55 |
| 2346 | 3 | 4 | 5 | | | V-1 | Olfr543 | 1.82 | 2442 | 3 | 4 | 5 | | | V-1 | Rad9b | 1.64 |
| 2347 | 3 | 4 | 5 | | | V-1 | Olig2 | 1.71 | 2443 | 3 | 4 | 5 | | | V-1 | Ralyl | 1.62 |
| 2348 | 3 | 4 | 5 | | | V-1 | Ooep | 1.85 | 2444 | 3 | 4 | 5 | | | V-1 | Ramp3 | 1.59 |
| 2349 | 3 | 4 | 5 | | | V-1 | Oprl1 | 1.71 | 2445 | 3 | 4 | 5 | | | V-1 | Ranbp17 | 1.62 |
| 2350 | 3 | 4 | 5 | | | V-1 | Osbp2 | 1.59 | 2446 | 3 | 4 | 5 | | | V-1 | Rbak | 1.66 |
| 2351 | 3 | 4 | 5 | | | V-1 | Osmr | 1.50 | 2447 | 3 | 4 | 5 | | | V-1 | Rbfox3 | 1.86 |
| 2352 | 3 | 4 | 5 | | | V-1 | Osr1 | 1.51 | 2448 | 3 | 4 | 5 | | | V-1 | Reep2 | 1.62 |
| 2353 | 3 | 4 | 5 | | | V-1 | Otud7a | 1.78 | 2449 | 3 | 4 | 5 | | | V-1 | Retnlg | 1.93 |
| 2354 | 3 | 4 | 5 | | | V-1 | P2rx3 | 1.72 | 2450 | 3 | 4 | 5 | | | V-1 | Rgag4 | 1.56 |
| 2355 | 3 | 4 | 5 | | | V-1 | Pacrg | 1.88 | 2451 | 3 | 4 | 5 | | | V-1 | Rgs17 | 1.51 |
| 2356 | 3 | 4 | 5 | | | V-1 | Pak7 | 1.56 | 2452 | 3 | 4 | 5 | | | V-1 | Rgs6 | 1.77 |
| 2357 | 3 | 4 | 5 | | | V-1 | Pappa2 | 1.60 | 2453 | 3 | 4 | 5 | | | V-1 | Rgs7 | 1.92 |
| 2358 | 3 | 4 | 5 | | | V-1 | Park2 | 1.55 | 2454 | 3 | 4 | 5 | | | V-1 | Rgs8 | 1.54 |
| 2359 | 3 | 4 | 5 | | | V-1 | Parp3 | 1.52 | 2455 | 3 | 4 | 5 | | | V-1 | Rgs9 | 1.61 |
| 2360 | 3 | 4 | 5 | | | V-1 | Parp8 | 1.50 | 2456 | 3 | 4 | 5 | | | V-1 | Ric3 | 1.55 |
| 2361 | 3 | 4 | 5 | | | V-1 | Pax2 | 1.54 | 2457 | 3 | 4 | 5 | | | V-1 | Rimbp2 | 1.59 |
| 2362 | 3 | 4 | 5 | | | V-1 | Pax6 | 1.61 | 2458 | 3 | 4 | 5 | | | V-1 | Rimklb | 1.80 |
| 2363 | 3 | 4 | 5 | | | V-1 | Pcdh10 | 1.54 | 2459 | 3 | 4 | 5 | | | V-1 | Rims2 | 1.96 |
| 2364 | 3 | 4 | 5 | | | V-1 | Pcdh8 | 1.67 | 2460 | 3 | 4 | 5 | | | V-1 | Rims4 | 1.51 |
| 2365 | 3 | 4 | 5 | | | V-1 | Pcdh9 | 1.57 | 2461 | 3 | 4 | 5 | | | V-1 | Rnd2 | 1.85 |
| 2366 | 3 | 4 | 5 | | | V-1 | Pcdha12 | 1.61 | 2462 | 3 | 4 | 5 | | | V-1 | Rnf180 | 1.67 |
| 2367 | 3 | 4 | 5 | | | V-1 | Pcdha3 | 1.62 | 2463 | 3 | 4 | 5 | | | V-1 | Rorb | 1.63 |
| 2368 | 3 | 4 | 5 | | | V-1 | Pcdha7 | 1.59 | 2464 | 3 | 4 | 5 | | | V-1 | Rpl34 | 1.53 |
| 2369 | 3 | 4 | 5 | | | V-1 | Pcdha9 | 1.53 | 2465 | 3 | 4 | 5 | | | V-1 | Rpl9 | 1.77 |
| 2370 | 3 | 4 | 5 | | | V-1 | Pcdhb18 | 1.55 | 2466 | 3 | 4 | 5 | | | V-1 | Rps27 | 1.86 |
| 2371 | 3 | 4 | 5 | | | V-1 | Pcdhb19 | 1.54 | 2467 | 3 | 4 | 5 | | | V-1 | Rspo3 | 1.54 |
| 2372 | 3 | 4 | 5 | | | V-1 | Pcdhb3 | 1.66 | 2468 | 3 | 4 | 5 | | | V-1 | Rtbdn | 1.59 |
| 2373 | 3 | 4 | 5 | | | V-1 | Pcdhb4 | 1.61 | 2469 | 3 | 4 | 5 | | | V-1 | Rtn1 | 1.60 |
| 2374 | 3 | 4 | 5 | | | V-1 | Pcdhb8 | 1.59 | 2470 | 3 | 4 | 5 | | | V-1 | Rtn4rl2 | 1.90 |
| 2375 | 3 | 4 | 5 | | | V-1 | Pcdhga2 | 1.67 | 2471 | 3 | 4 | 5 | | | V-1 | Rundc3a | 1.55 |
| 2376 | 3 | 4 | 5 | | | V-1 | Pcdhga8 | 1.52 | 2472 | 3 | 4 | 5 | | | V-1 | Rundc3b | 1.68 |
| 2377 | 3 | 4 | 5 | | | V-1 | Pcgf1 | 1.51 | 2473 | 3 | 4 | 5 | | | V-1 | S100b | 1.64 |
| 2378 | 3 | 4 | 5 | | | V-1 | Pcgf2 | 1.75 | 2474 | 3 | 4 | 5 | | | V-1 | Sall3 | 1.73 |
| 2379 | 3 | 4 | 5 | | | V-1 | Pcsk1n | 1.71 | 2475 | 3 | 4 | 5 | | | V-1 | Sarm1 | 1.60 |
| 2380 | 3 | 4 | 5 | | | V-1 | Pcsk2 | 1.60 | 2476 | 3 | 4 | 5 | | | V-1 | Sbk1 | 1.70 |
| 2381 | 3 | 4 | 5 | | | V-1 | Pcsk5 | 1.54 | 2477 | 3 | 4 | 5 | | | V-1 | Scamp5 | 1.54 |
| 2382 | 3 | 4 | 5 | | | V-1 | Pde1b | 1.86 | 2478 | 3 | 4 | 5 | | | V-1 | Scarna6 | 1.79 |
| 2383 | 3 | 4 | 5 | | | V-1 | Pdgfc | 1.50 | 2479 | 3 | 4 | 5 | | | V-1 | Scg2 | 1.78 |
| 2384 | 3 | 4 | 5 | | | V-1 | Pdk4 | 1.93 | 2480 | 3 | 4 | 5 | | | V-1 | Scg3 | 1.60 |
| 2385 | 3 | 4 | 5 | | | V-1 | Pdzd4 | 1.51 | 2481 | 3 | 4 | 5 | | | V-1 | Scn2a1 | 1.58 |
| 2386 | 3 | 4 | 5 | | | V-1 | Pdzrn4 | 1.52 | 2482 | 3 | 4 | 5 | | | V-1 | Scn3a | 1.85 |
| 2387 | 3 | 4 | 5 | | | V-1 | Peg13 | 1.52 | 2483 | 3 | 4 | 5 | | | V-1 | Scn8a | 1.77 |
| 2388 | 3 | 4 | 5 | | | V-1 | Per1 | 1.58 | 2484 | 3 | 4 | 5 | | | V-1 | Scn9a | 1.84 |
| 2389 | 3 | 4 | 5 | | | V-1 | Pex5l | 1.73 | 2485 | 3 | 4 | 5 | | | V-1 | Scrt1 | 1.66 |
| 2390 | 3 | 4 | 5 | | | V-1 | Pfn4 | 1.82 | 2486 | 3 | 4 | 5 | | | V-1 | Scrt2 | 1.54 |
| 2391 | 3 | 4 | 5 | | | V-1 | Phactr1 | 1.55 | 2487 | 3 | 4 | 5 | | | V-1 | Scube3 | 1.82 |
| 2392 | 3 | 4 | 5 | | | V-1 | Phf21b | 1.83 | 2488 | 3 | 4 | 5 | | | V-1 | Sec14l4 | 1.52 |
| 2393 | 3 | 4 | 5 | | | V-1 | Phf7 | 1.64 | 2489 | 3 | 4 | 5 | | | V-1 | Sema5b | 1.58 |
| 2394 | 3 | 4 | 5 | | | V-1 | Phf1os | 1.53 | 2490 | 3 | 4 | 5 | | | V-1 | Sept1 | 1.60 |
| 2395 | 3 | 4 | 5 | | | V-1 | Pianp | 1.66 | 2491 | 3 | 4 | 5 | | | V-1 | Sept3 | 1.66 |
| 2396 | 3 | 4 | 5 | | | V-1 | Pik3ip1 | 1.71 | 2492 | 3 | 4 | 5 | | | V-1 | Sept4 | 1.57 |
| 2397 | 3 | 4 | 5 | | | V-1 | Pilra | 1.59 | 2493 | 3 | 4 | 5 | | | V-1 | Serinc4 | 1.67 |
| 2398 | 3 | 4 | 5 | | | V-1 | Pink1 | 1.53 | 2494 | 3 | 4 | 5 | | | V-1 | Serpina3h | 1.84 |

Fig. 45 - 14

| | | | | | | | | | | | | | | | |
|---|---|---|---|---|---|---|---|---|---|---|---|---|---|---|---|
| 2495 | 3 | 4 | 5 | | V-1 | Serpina3m | 1.79 | 2591 | 3 | 4 | 5 | | V-1 | Syp | 1.54 |
| 2496 | 3 | 4 | 5 | | V-1 | Serpinb2 | 1.51 | 2592 | 3 | 4 | 5 | | V-1 | Syt16 | 1.78 |
| 2497 | 3 | 4 | 5 | | V-1 | Serpini1 | 1.60 | 2593 | 3 | 4 | 5 | | V-1 | Syt5 | 1.51 |
| 2498 | 3 | 4 | 5 | | V-1 | Serpini2 | 1.53 | 2594 | 3 | 4 | 5 | | V-1 | Syt7 | 1.74 |
| 2499 | 3 | 4 | 5 | | V-1 | Sesn2 | 1.66 | 2595 | 3 | 4 | 5 | | V-1 | Taf4b | 1.88 |
| 2500 | 3 | 4 | 5 | | V-1 | Sestd1 | 1.69 | 2596 | 3 | 4 | 5 | | V-1 | Tat | 1.52 |
| 2501 | 3 | 4 | 5 | | V-1 | Setbp1 | 1.77 | 2597 | 3 | 4 | 5 | | V-1 | Tbc1d9 | 1.51 |
| 2502 | 3 | 4 | 5 | | V-1 | Setdb2 | 1.52 | 2598 | 3 | 4 | 5 | | V-1 | Tbcd | 1.53 |
| 2503 | 3 | 4 | 5 | | V-1 | Sez6l | 1.81 | 2599 | 3 | 4 | 5 | | V-1 | Tbr1 | 1.78 |
| 2504 | 3 | 4 | 5 | | V-1 | Sez6l2 | 1.64 | 2600 | 3 | 4 | 5 | | V-1 | Tcea2 | 1.75 |
| 2505 | 3 | 4 | 5 | | V-1 | Sftpa1 | 1.93 | 2601 | 3 | 4 | 5 | | V-1 | Tekt1 | 1.84 |
| 2506 | 3 | 4 | 5 | | V-1 | Sftpb | 1.88 | 2602 | 3 | 4 | 5 | | V-1 | Tekt2 | 1.96 |
| 2507 | 3 | 4 | 5 | | V-1 | Sfxn3 | 1.58 | 2603 | 3 | 4 | 5 | | V-1 | Tenm1 | 1.87 |
| 2508 | 3 | 4 | 5 | | V-1 | Sgip1 | 1.77 | 2604 | 3 | 4 | 5 | | V-1 | Tenm2 | 1.67 |
| 2509 | 3 | 4 | 5 | | V-1 | Sh3d21 | 1.78 | 2605 | 3 | 4 | 5 | | V-1 | Tfap2b | 1.63 |
| 2510 | 3 | 4 | 5 | | V-1 | Shd | 1.52 | 2606 | 3 | 4 | 5 | | V-1 | Tgfa | 1.55 |
| 2511 | 3 | 4 | 5 | | V-1 | Shisa6 | 1.56 | 2607 | 3 | 4 | 5 | | V-1 | Thpo | 1.70 |
| 2512 | 3 | 4 | 5 | | V-1 | Siah3 | 1.71 | 2608 | 3 | 4 | 5 | | V-1 | Thsd7a | 1.84 |
| 2513 | 3 | 4 | 5 | | V-1 | Sidt1 | 1.78 | 2609 | 3 | 4 | 5 | | V-1 | Tk2 | 1.52 |
| 2514 | 3 | 4 | 5 | | V-1 | Six3 | 1.63 | 2610 | 3 | 4 | 5 | | V-1 | Tlr1 | 1.65 |
| 2515 | 3 | 4 | 5 | | V-1 | Skor1 | 1.74 | 2611 | 3 | 4 | 5 | | V-1 | Tlr7 | 1.98 |
| 2516 | 3 | 4 | 5 | | V-1 | Slc10a4 | 1.60 | 2612 | 3 | 4 | 5 | | V-1 | Tlx3 | 1.72 |
| 2517 | 3 | 4 | 5 | | V-1 | Slc16a14 | 1.70 | 2613 | 3 | 4 | 5 | | V-1 | Tmem108 | 1.57 |
| 2518 | 3 | 4 | 5 | | V-1 | Slc17a6 | 1.89 | 2614 | 3 | 4 | 5 | | V-1 | Tmem132b | 1.68 |
| 2519 | 3 | 4 | 5 | | V-1 | Slc18a3 | 1.53 | 2615 | 3 | 4 | 5 | | V-1 | Tmem151b | 1.62 |
| 2520 | 3 | 4 | 5 | | V-1 | Slc1a6 | 1.94 | 2616 | 3 | 4 | 5 | | V-1 | Tmem160 | 1.53 |
| 2521 | 3 | 4 | 5 | | V-1 | Slc25a14 | 1.64 | 2617 | 3 | 4 | 5 | | V-1 | Tmem178b | 1.61 |
| 2522 | 3 | 4 | 5 | | V-1 | Slc25a27 | 1.64 | 2618 | 3 | 4 | 5 | | V-1 | Tmem179 | 1.77 |
| 2523 | 3 | 4 | 5 | | V-1 | Slc29a4 | 1.96 | 2619 | 3 | 4 | 5 | | V-1 | Tmem191c | 1.55 |
| 2524 | 3 | 4 | 5 | | V-1 | Slc2a8 | 1.52 | 2620 | 3 | 4 | 5 | | V-1 | Tmem196 | 1.70 |
| 2525 | 3 | 4 | 5 | | V-1 | Slc30a2 | 1.51 | 2621 | 3 | 4 | 5 | | V-1 | Tmem198 | 1.73 |
| 2526 | 3 | 4 | 5 | | V-1 | Slc30a3 | 1.89 | 2622 | 3 | 4 | 5 | | V-1 | Tmem200c | 1.75 |
| 2527 | 3 | 4 | 5 | | V-1 | Slc32a1 | 1.71 | 2623 | 3 | 4 | 5 | | V-1 | Tmem212 | 1.55 |
| 2528 | 3 | 4 | 5 | | V-1 | Slc35b3 | 1.50 | 2624 | 3 | 4 | 5 | | V-1 | Tmem252 | 1.82 |
| 2529 | 3 | 4 | 5 | | V-1 | Slc45a1 | 1.99 | 2625 | 3 | 4 | 5 | | V-1 | Tmem59l | 1.85 |
| 2530 | 3 | 4 | 5 | | V-1 | Slc4a10 | 1.73 | 2626 | 3 | 4 | 5 | | V-1 | Tmem74b | 1.66 |
| 2531 | 3 | 4 | 5 | | V-1 | Slc4a3 | 1.63 | 2627 | 3 | 4 | 5 | | V-1 | Tmem91 | 1.83 |
| 2532 | 3 | 4 | 5 | | V-1 | Slc50a1 | 1.57 | 2628 | 3 | 4 | 5 | | V-1 | Tnr | 1.51 |
| 2533 | 3 | 4 | 5 | | V-1 | Slc5a7 | 1.60 | 2629 | 3 | 4 | 5 | | V-1 | Tomt | 1.53 |
| 2534 | 3 | 4 | 5 | | V-1 | Slc6a1 | 1.80 | 2630 | 3 | 4 | 5 | | V-1 | Tox3 | 1.87 |
| 2535 | 3 | 4 | 5 | | V-1 | Slc6a11 | 1.55 | 2631 | 3 | 4 | 5 | | V-1 | Trem2 | 1.83 |
| 2536 | 3 | 4 | 5 | | V-1 | Slc6a15 | 1.71 | 2632 | 3 | 4 | 5 | | V-1 | Trim30a | 1.80 |
| 2537 | 3 | 4 | 5 | | V-1 | Slc6a17 | 1.55 | 2633 | 3 | 4 | 5 | | V-1 | Trim30d | 1.92 |
| 2538 | 3 | 4 | 5 | | V-1 | Slc6a6 | 1.59 | 2634 | 3 | 4 | 5 | | V-1 | Trim34a | 1.94 |
| 2539 | 3 | 4 | 5 | | V-1 | Slc7a14 | 1.54 | 2635 | 3 | 4 | 5 | | V-1 | Trim67 | 1.54 |
| 2540 | 3 | 4 | 5 | | V-1 | Slc7a3 | 1.52 | 2636 | 3 | 4 | 5 | | V-1 | Trim9 | 1.79 |
| 2541 | 3 | 4 | 5 | | V-1 | Slc8a2 | 1.80 | 2637 | 3 | 4 | 5 | | V-1 | Trnp1 | 1.71 |
| 2542 | 3 | 4 | 5 | | V-1 | Slfn1 | 1.64 | 2638 | 3 | 4 | 5 | | V-1 | Trpc2 | 1.69 |
| 2543 | 3 | 4 | 5 | | V-1 | Slfn2 | 1.71 | 2639 | 3 | 4 | 5 | | V-1 | Trpc4 | 1.53 |
| 2544 | 3 | 4 | 5 | | V-1 | Slfn4 | 1.77 | 2640 | 3 | 4 | 5 | | V-1 | Try4 | 1.94 |
| 2545 | 3 | 4 | 5 | | V-1 | Slit1 | 1.60 | 2641 | 3 | 4 | 5 | | V-1 | Ttbk1 | 1.53 |
| 2546 | 3 | 4 | 5 | | V-1 | Slitrk3 | 1.60 | 2642 | 3 | 4 | 5 | | V-1 | Ttc30a2 | 1.55 |
| 2547 | 3 | 4 | 5 | | V-1 | Smo1 | 1.65 | 2643 | 3 | 4 | 5 | | V-1 | Ttyh1 | 1.70 |
| 2548 | 3 | 4 | 5 | | V-1 | Snhg11 | 1.86 | 2644 | 3 | 4 | 5 | | V-1 | Tub | 1.59 |
| 2549 | 3 | 4 | 5 | | V-1 | Snhg12 | 1.71 | 2645 | 3 | 4 | 5 | | V-1 | Tubg2 | 1.77 |
| 2550 | 3 | 4 | 5 | | V-1 | Snhg6 | 1.73 | 2646 | 3 | 4 | 5 | | V-1 | Txnip | 1.64 |
| 2551 | 3 | 4 | 5 | | V-1 | Snhg7 | 1.65 | 2647 | 3 | 4 | 5 | | V-1 | Uba7 | 1.75 |
| 2552 | 3 | 4 | 5 | | V-1 | Snrpn | 1.51 | 2648 | 3 | 4 | 5 | | V-1 | Ube2ql1 | 1.52 |
| 2553 | 3 | 4 | 5 | | V-1 | Socs2 | 1.67 | 2649 | 3 | 4 | 5 | | V-1 | Unc5d | 1.95 |
| 2554 | 3 | 4 | 5 | | V-1 | Sox1 | 1.70 | 2650 | 3 | 4 | 5 | | V-1 | Uncx | 1.57 |
| 2555 | 3 | 4 | 5 | | V-1 | Sox14 | 1.56 | 2651 | 3 | 4 | 5 | | V-1 | Upk1b | 1.67 |
| 2556 | 3 | 4 | 5 | | V-1 | Sox2 | 1.56 | 2652 | 3 | 4 | 5 | | V-1 | Uty | 1.97 |
| 2557 | 3 | 4 | 5 | | V-1 | Sox21 | 1.82 | 2653 | 3 | 4 | 5 | | V-1 | Uvssa | 1.82 |
| 2558 | 3 | 4 | 5 | | V-1 | Sox2ot | 1.69 | 2654 | 3 | 4 | 5 | | V-1 | Vamp4 | 1.80 |
| 2559 | 3 | 4 | 5 | | V-1 | Sox3 | 1.61 | 2655 | 3 | 4 | 5 | | V-1 | Vgf | 1.74 |
| 2560 | 3 | 4 | 5 | | V-1 | Sox5 | 1.66 | 2656 | 3 | 4 | 5 | | V-1 | Vit | 1.72 |
| 2561 | 3 | 4 | 5 | | V-1 | Sp100 | 1.69 | 2657 | 3 | 4 | 5 | | V-1 | Vnn1 | 1.54 |
| 2562 | 3 | 4 | 5 | | V-1 | Sp8 | 1.68 | 2658 | 3 | 4 | 5 | | V-1 | Vstm2a | 1.59 |
| 2563 | 3 | 4 | 5 | | V-1 | Sp9 | 1.56 | 2659 | 3 | 4 | 5 | | V-1 | Vstm2l | 1.96 |
| 2564 | 3 | 4 | 5 | | V-1 | Spaca6 | 1.92 | 2660 | 3 | 4 | 5 | | V-1 | Vwa5b2 | 1.66 |
| 2565 | 3 | 4 | 5 | | V-1 | Spata7 | 1.52 | 2661 | 3 | 4 | 5 | | V-1 | Wasf3 | 1.64 |
| 2566 | 3 | 4 | 5 | | V-1 | Spic | 1.61 | 2662 | 3 | 4 | 5 | | V-1 | Wbscr27 | 1.63 |
| 2567 | 3 | 4 | 5 | | V-1 | Spin2c | 1.63 | 2663 | 3 | 4 | 5 | | V-1 | Wfikkn2 | 1.73 |
| 2568 | 3 | 4 | 5 | | V-1 | Spock1 | 1.69 | 2664 | 3 | 4 | 5 | | V-1 | Wnk3 | 1.57 |
| 2569 | 3 | 4 | 5 | | V-1 | Spock2 | 1.63 | 2665 | 3 | 4 | 5 | | V-1 | Wscd1 | 1.57 |
| 2570 | 3 | 4 | 5 | | V-1 | Spock3 | 2.00 | 2666 | 3 | 4 | 5 | | V-1 | Xpc | 1.52 |
| 2571 | 3 | 4 | 5 | | V-1 | Spred3 | 1.58 | 2667 | 3 | 4 | 5 | | V-1 | Xylt1 | 1.64 |
| 2572 | 3 | 4 | 5 | | V-1 | Sprr1b | 1.88 | 2668 | 3 | 4 | 5 | | V-1 | Ypel1 | 1.53 |
| 2573 | 3 | 4 | 5 | | V-1 | Sptbn4 | 1.57 | 2669 | 3 | 4 | 5 | | V-1 | Zc3h8 | 1.77 |
| 2574 | 3 | 4 | 5 | | V-1 | Srgap3 | 1.59 | 2670 | 3 | 4 | 5 | | V-1 | Zcchc12 | 1.59 |
| 2575 | 3 | 4 | 5 | | V-1 | Srrm3 | 1.53 | 2671 | 3 | 4 | 5 | | V-1 | Zcchc18 | 1.58 |
| 2576 | 3 | 4 | 5 | | V-1 | Srrm4 | 1.67 | 2672 | 3 | 4 | 5 | | V-1 | Zdhhc22 | 1.51 |
| 2577 | 3 | 4 | 5 | | V-1 | Srrm4os | 1.99 | 2673 | 3 | 4 | 5 | | V-1 | Zfhx2os | 1.61 |
| 2578 | 3 | 4 | 5 | | V-1 | Sst | 1.51 | 2674 | 3 | 4 | 5 | | V-1 | Zfp1 | 1.51 |
| 2579 | 3 | 4 | 5 | | V-1 | Sstr2 | 1.63 | 2675 | 3 | 4 | 5 | | V-1 | Zfp112 | 1.69 |
| 2580 | 3 | 4 | 5 | | V-1 | St18 | 1.59 | 2676 | 3 | 4 | 5 | | V-1 | Zfp184 | 1.59 |
| 2581 | 3 | 4 | 5 | | V-1 | St6gal2 | 1.74 | 2677 | 3 | 4 | 5 | | V-1 | Zfp229 | 1.62 |
| 2582 | 3 | 4 | 5 | | V-1 | St6galnac5 | 1.69 | 2678 | 3 | 4 | 5 | | V-1 | Zfp280c | 1.64 |
| 2583 | 3 | 4 | 5 | | V-1 | St8sia1 | 1.69 | 2679 | 3 | 4 | 5 | | V-1 | Zfp362 | 1.51 |
| 2584 | 3 | 4 | 5 | | V-1 | Stc2 | 1.77 | 2680 | 3 | 4 | 5 | | V-1 | Zfp365 | 1.67 |
| 2585 | 3 | 4 | 5 | | V-1 | Stk32c | 1.65 | 2681 | 3 | 4 | 5 | | V-1 | Zfp558 | 1.59 |
| 2586 | 3 | 4 | 5 | | V-1 | Stx1b | 1.74 | 2682 | 3 | 4 | 5 | | V-1 | Zfp566 | 1.63 |
| 2587 | 3 | 4 | 5 | | V-1 | Sult1a1 | 1.60 | 2683 | 3 | 4 | 5 | | V-1 | Zfp575 | 1.86 |
| 2588 | 3 | 4 | 5 | | V-1 | Sult2a1 | 1.68 | 2684 | 3 | 4 | 5 | | V-1 | Zfp641 | 1.74 |
| 2589 | 3 | 4 | 5 | | V-1 | Sv2a | 1.60 | 2685 | 3 | 4 | 5 | | V-1 | Zfp652os | 1.58 |
| 2590 | 3 | 4 | 5 | | V-1 | Svop | 1.66 | 2686 | 3 | 4 | 5 | | V-1 | Zfp653 | 1.59 |

Fig. 45 - 15

| | | | | | | | |
|---|---|---|---|---|---|---|---|
| 2687 | 3 | 4 | 5 | | V-1 | Zfp688 | 1.72 |
| 2688 | 3 | 4 | 5 | | V-1 | Zfp711 | 1.51 |
| 2689 | 3 | 4 | 5 | | V-1 | Zfp777 | 1.59 |
| 2690 | 3 | 4 | 5 | | V-1 | Zfp804a | 1.58 |
| 2691 | 3 | 4 | 5 | | V-1 | Zfp810 | 1.56 |
| 2692 | 3 | 4 | 5 | | V-1 | Zfp811 | 1.68 |
| 2693 | 3 | 4 | 5 | | V-1 | Zfp90 | 1.75 |
| 2694 | 3 | 4 | 5 | | V-1 | Zfp939 | 1.50 |
| 2695 | 3 | 4 | 5 | | V-1 | Zfp941 | 1.62 |
| 2696 | 3 | 4 | 5 | | V-1 | Zfr2 | 1.60 |
| 2697 | 3 | 4 | 5 | | V-1 | Zic1 | 1.86 |
| 2698 | 3 | 4 | 5 | | V-1 | Zic2 | 1.78 |
| 2699 | 3 | 4 | 5 | | V-1 | Zic4 | 1.82 |
| 2700 | 3 | 4 | 5 | | V-1 | Zic5 | 1.63 |
| 2701 | 3 | 4 | 5 | | V-1 | Zkscan16 | 1.59 |
| 2702 | 3 | 4 | 5 | | V-1 | Znf512b | 1.60 |
| 2703 | 3 | 4 | 5 | | V-1 | Zscan25 | 1.56 |
| 2704 | 3 | 4 | 5 | | V-1 | Zswim4 | 1.56 |
| 2705 | 3 | 4 | | | IV-2 | 0610005C13Rik | 0.80 |
| 2706 | 3 | 4 | | | IV-2 | 0610007P14Rik | 0.77 |
| 2707 | 3 | 4 | | | IV-2 | 0610009B22Rik | 0.69 |
| 2708 | 3 | 4 | | | IV-2 | 0610009O20Rik | 0.98 |
| 2709 | 3 | 4 | | | IV-2 | 0610010B08Rik | 0.96 |
| 2710 | 3 | 4 | | | IV-2 | 0610010K14Rik | 0.87 |
| 2711 | 3 | 4 | | | IV-2 | 0610012G03Rik | 0.82 |
| 2712 | 3 | 4 | | | IV-2 | 0610030E20Rik | 0.87 |
| 2713 | 3 | 4 | | | IV-2 | 0610031J06Rik | 0.76 |
| 2714 | 3 | 4 | | | IV-2 | 0610038B21Rik | 0.95 |
| 2715 | 3 | 4 | | | IV-2 | 0610040J01Rik | 0.70 |
| 2716 | 3 | 4 | | | IV-2 | 1010001N08Rik | 0.72 |
| 2717 | 3 | 4 | | | IV-2 | 1110001J03Rik | 0.80 |
| 2718 | 3 | 4 | | | IV-2 | 1110004E09Rik | 0.89 |
| 2719 | 3 | 4 | | | IV-2 | 1110007C09Rik | 0.92 |
| 2720 | 3 | 4 | | | IV-2 | 1110008F13Rik | 0.77 |
| 2721 | 3 | 4 | | | IV-2 | 1110008L16Rik | 0.87 |
| 2722 | 3 | 4 | | | IV-2 | 1110008P14Rik | 0.79 |
| 2723 | 3 | 4 | | | IV-2 | 1110032F04Rik | 0.88 |
| 2724 | 3 | 4 | | | IV-2 | 1110037F02Rik | 0.93 |
| 2725 | 3 | 4 | | | IV-2 | 1110038F14Rik | 0.91 |
| 2726 | 3 | 4 | | | IV-2 | 1110057K04Rik | 0.94 |
| 2727 | 3 | 4 | | | IV-2 | 1110058L19Rik | 0.93 |
| 2728 | 3 | 4 | | | IV-2 | 1190002N15Rik | 0.97 |
| 2729 | 3 | 4 | | | IV-2 | 1190005I06Rik | 0.88 |
| 2730 | 3 | 4 | | | IV-2 | 1190007I07Rik | 0.77 |
| 2731 | 3 | 4 | | | IV-2 | 1300002E11Rik | 0.96 |
| 2732 | 3 | 4 | | | IV-2 | 1500009L16Rik | 0.79 |
| 2733 | 3 | 4 | | | IV-2 | 1500011K16Rik | 0.88 |
| 2734 | 3 | 4 | | | IV-2 | 1500017E21Rik | 0.97 |
| 2735 | 3 | 4 | | | IV-2 | 1600002H07Rik | 0.89 |
| 2736 | 3 | 4 | | | IV-2 | 1600012H06Rik | 0.93 |
| 2737 | 3 | 4 | | | IV-2 | 1600014C10Rik | 0.95 |
| 2738 | 3 | 4 | | | IV-2 | 1700001C02Rik | 0.80 |
| 2739 | 3 | 4 | | | IV-2 | 1700001I11Rik | 0.69 |
| 2740 | 3 | 4 | | | IV-2 | 1700003E16Rik | 0.90 |
| 2741 | 3 | 4 | | | IV-2 | 1700003F12Rik | 0.77 |
| 2742 | 3 | 4 | | | IV-2 | 1700012D01Rik | 0.92 |
| 2743 | 3 | 4 | | | IV-2 | 1700017B05Rik | 0.98 |
| 2744 | 3 | 4 | | | IV-2 | 1700020D05Rik | 0.87 |
| 2745 | 3 | 4 | | | IV-2 | 1700020I14Rik | 0.84 |
| 2746 | 3 | 4 | | | IV-2 | 1700021F05Rik | 0.80 |
| 2747 | 3 | 4 | | | IV-2 | 1700021K19Rik | 0.88 |
| 2748 | 3 | 4 | | | IV-2 | 1700023L04Rik | 0.74 |
| 2749 | 3 | 4 | | | IV-2 | 1700024F13Rik | 0.95 |
| 2750 | 3 | 4 | | | IV-2 | 1700030C10Rik | 0.95 |
| 2751 | 3 | 4 | | | IV-2 | 1700030J22Rik | 0.91 |
| 2752 | 3 | 4 | | | IV-2 | 1700030K09Rik | 0.81 |
| 2753 | 3 | 4 | | | IV-2 | 1700048O20Rik | 0.90 |
| 2754 | 3 | 4 | | | IV-2 | 1700052K11Rik | 0.97 |
| 2755 | 3 | 4 | | | IV-2 | 1700052N19Rik | 0.87 |
| 2756 | 3 | 4 | | | IV-2 | 1700066M21Rik | 0.94 |
| 2757 | 3 | 4 | | | IV-2 | 1700094D03Rik | 0.96 |
| 2758 | 3 | 4 | | | IV-2 | 1700123O20Rik | 0.92 |
| 2759 | 3 | 4 | | | IV-2 | 1810009A15Rik | 0.79 |
| 2760 | 3 | 4 | | | IV-2 | 1810011O10Rik | 0.83 |
| 2761 | 3 | 4 | | | IV-2 | 1810013L24Rik | 0.88 |
| 2762 | 3 | 4 | | | IV-2 | 1810019D21Rik | 0.87 |
| 2763 | 3 | 4 | | | IV-2 | 1810037H17Rik | 0.69 |
| 2764 | 3 | 4 | | | IV-2 | 1810041L15Rik | 0.94 |
| 2765 | 3 | 4 | | | IV-2 | 1810043H04Rik | 0.92 |
| 2766 | 3 | 4 | | | IV-2 | 1810053B23Rik | 0.85 |
| 2767 | 3 | 4 | | | IV-2 | 1810055G02Rik | 0.81 |
| 2768 | 3 | 4 | | | IV-2 | 1810058I24Rik | 0.99 |
| 2769 | 3 | 4 | | | IV-2 | 2010003K11Rik | 0.95 |
| 2770 | 3 | 4 | | | IV-2 | 2010010A06Rik | 0.83 |
| 2771 | 3 | 4 | | | IV-2 | 2010107E04Rik | 0.72 |
| 2772 | 3 | 4 | | | IV-2 | 2010109I03Rik | 0.88 |
| 2773 | 3 | 4 | | | IV-2 | 2010300C02Rik | 1.00 |
| 2774 | 3 | 4 | | | IV-2 | 2210018M11Rik | 0.90 |
| 2775 | 3 | 4 | | | IV-2 | 2310001H17Rik | 0.70 |
| 2776 | 3 | 4 | | | IV-2 | 2310002J15Rik | 0.79 |
| 2777 | 3 | 4 | | | IV-2 | 2310007B03Rik | 0.90 |
| 2778 | 3 | 4 | | | IV-2 | 2310009A05Rik | 0.67 |
| 2779 | 3 | 4 | | | IV-2 | 2310011J03Rik | 0.97 |
| 2780 | 3 | 4 | | | IV-2 | 2310014L17Rik | 0.69 |
| 2781 | 3 | 4 | | | IV-2 | 2310022A10Rik | 0.90 |
| 2782 | 3 | 4 | | | IV-2 | 2310030G06Rik | 0.81 |
| 2783 | 3 | 4 | | | IV-2 | 2310033P09Rik | 0.68 |
| 2784 | 3 | 4 | | | IV-2 | 2310036O22Rik | 0.98 |
| 2785 | 3 | 4 | | | IV-2 | 2310042E22Rik | 0.99 |
| 2786 | 3 | 4 | | | IV-2 | 2310045N01Rik | 0.90 |
| 2787 | 3 | 4 | | | IV-2 | 2310047M10Rik | 0.98 |
| 2788 | 3 | 4 | | | IV-2 | 2310057M21Rik | 0.87 |
| 2789 | 3 | 4 | | | IV-2 | 2310061I04Rik | 0.80 |
| 2790 | 3 | 4 | | | IV-2 | 2410004B18Rik | 0.86 |
| 2791 | 3 | 4 | | | IV-2 | 2410015M20Rik | 0.85 |
| 2792 | 3 | 4 | | | IV-2 | 2410016O06Rik | 0.90 |
| 2793 | 3 | 4 | | | IV-2 | 2410127L17Rik | 0.77 |
| 2794 | 3 | 4 | | | IV-2 | 2500004C02Rik | 0.91 |
| 2795 | 3 | 4 | | | IV-2 | 2510003E04Rik | 0.98 |
| 2796 | 3 | 4 | | | IV-2 | 2510039O18Rik | 1.00 |
| 2797 | 3 | 4 | | | IV-2 | 2610001J05Rik | 0.91 |
| 2798 | 3 | 4 | | | IV-2 | 2610002M06Rik | 0.92 |
| 2799 | 3 | 4 | | | IV-2 | 2610015P09Rik | 0.85 |
| 2800 | 3 | 4 | | | IV-2 | 2610016A17Rik | 0.97 |
| 2801 | 3 | 4 | | | IV-2 | 2610020H08Rik | 0.85 |
| 2802 | 3 | 4 | | | IV-2 | 2610034B18Rik | 0.89 |
| 2803 | 3 | 4 | | | IV-2 | 2610044O15Rik8 | 0.93 |
| 2804 | 3 | 4 | | | IV-2 | 2610318N02Rik | 0.84 |
| 2805 | 3 | 4 | | | IV-2 | 2610507B11Rik | 0.85 |
| 2806 | 3 | 4 | | | IV-2 | 2610507O01Rik | 0.94 |
| 2807 | 3 | 4 | | | IV-2 | 2610528J11Rik | 0.72 |
| 2808 | 3 | 4 | | | IV-2 | 2700029M09Rik | 0.86 |
| 2809 | 3 | 4 | | | IV-2 | 2700038G22Rik | 0.92 |
| 2810 | 3 | 4 | | | IV-2 | 2700049A03Rik | 0.94 |
| 2811 | 3 | 4 | | | IV-2 | 2700060E02Rik | 1.00 |
| 2812 | 3 | 4 | | | IV-2 | 2700089E24Rik | 0.95 |
| 2813 | 3 | 4 | | | IV-2 | 2700094K13Rik | 0.70 |
| 2814 | 3 | 4 | | | IV-2 | 2700097O09Rik | 0.77 |
| 2815 | 3 | 4 | | | IV-2 | 2700099C18Rik | 0.69 |
| 2816 | 3 | 4 | | | IV-2 | 2810002D19Rik | 0.83 |
| 2817 | 3 | 4 | | | IV-2 | 2810004N23Rik | 0.69 |
| 2818 | 3 | 4 | | | IV-2 | 2810006K23Rik | 0.75 |
| 2819 | 3 | 4 | | | IV-2 | 2810025M15Rik | 0.76 |
| 2820 | 3 | 4 | | | IV-2 | 2810408M09Rik | 0.87 |
| 2821 | 3 | 4 | | | IV-2 | 2810428I15Rik | 0.81 |
| 2822 | 3 | 4 | | | IV-2 | 2810459M11Rik | 0.84 |
| 2823 | 3 | 4 | | | IV-2 | 2810468N07Rik | 0.93 |
| 2824 | 3 | 4 | | | IV-2 | 2900009J06Rik | 0.73 |
| 2825 | 3 | 4 | | | IV-2 | 2900026A02Rik | 0.88 |
| 2826 | 3 | 4 | | | IV-2 | 2900076A07Rik | 0.93 |
| 2827 | 3 | 4 | | | IV-2 | 3010001F23Rik | 0.83 |
| 2828 | 3 | 4 | | | IV-2 | 3110001J22Rik | 0.92 |
| 2829 | 3 | 4 | | | IV-2 | 3110002H16Rik | 0.68 |
| 2830 | 3 | 4 | | | IV-2 | 3110040N11Rik | 0.80 |
| 2831 | 3 | 4 | | | IV-2 | 3110045C21Rik | 0.93 |
| 2832 | 3 | 4 | | | IV-2 | 3110052M02Rik | 0.82 |
| 2833 | 3 | 4 | | | IV-2 | 3110056K07Rik | 0.80 |
| 2834 | 3 | 4 | | | IV-2 | 3110057O12Rik | 0.88 |
| 2835 | 3 | 4 | | | IV-2 | 3110062M04Rik | 0.72 |
| 2836 | 3 | 4 | | | IV-2 | 3110082I17Rik | 0.97 |
| 2837 | 3 | 4 | | | IV-2 | 3300002I08Rik | 0.76 |
| 2838 | 3 | 4 | | | IV-2 | 3425401B19Rik | 0.74 |
| 2839 | 3 | 4 | | | IV-2 | 3632451O06Rik | 0.73 |
| 2840 | 3 | 4 | | | IV-2 | 3830406C13Rik | 0.92 |
| 2841 | 3 | 4 | | | IV-2 | 4632428N05Rik | 0.86 |
| 2842 | 3 | 4 | | | IV-2 | 4632434I11Rik | 0.99 |
| 2843 | 3 | 4 | | | IV-2 | 4732471J01Rik | 0.97 |
| 2844 | 3 | 4 | | | IV-2 | 4833423E24Rik | 0.80 |
| 2845 | 3 | 4 | | | IV-2 | 4833439L19Rik | 0.95 |
| 2846 | 3 | 4 | | | IV-2 | 4921533I20Rik | 0.76 |
| 2847 | 3 | 4 | | | IV-2 | 4930412C18Rik | 0.87 |
| 2848 | 3 | 4 | | | IV-2 | 4930413F20Rik | 0.90 |
| 2849 | 3 | 4 | | | IV-2 | 4930427A07Rik | 0.99 |
| 2850 | 3 | 4 | | | IV-2 | 4930430F08Rik | 0.98 |
| 2851 | 3 | 4 | | | IV-2 | 4930452B06Rik | 0.92 |
| 2852 | 3 | 4 | | | IV-2 | 4930453N24Rik | 0.83 |
| 2853 | 3 | 4 | | | IV-2 | 4930473A02Rik | 0.73 |
| 2854 | 3 | 4 | | | IV-2 | 4930503E24Rik | 0.88 |
| 2855 | 3 | 4 | | | IV-2 | 4930519F09Rik | 0.78 |
| 2856 | 3 | 4 | | | IV-2 | 4930523C07Rik | 0.93 |
| 2857 | 3 | 4 | | | IV-2 | 4930565N06Rik | 0.87 |
| 2858 | 3 | 4 | | | IV-2 | 4930579G24Rik | 0.72 |
| 2859 | 3 | 4 | | | IV-2 | 4930594C11Rik | 0.74 |
| 2860 | 3 | 4 | | | IV-2 | 4931408D14Rik | 0.73 |
| 2861 | 3 | 4 | | | IV-2 | 4931414P19Rik | 0.90 |
| 2862 | 3 | 4 | | | IV-2 | 4932411E22Rik | 0.84 |
| 2863 | 3 | 4 | | | IV-2 | 4933404O12Rik | 0.97 |
| 2864 | 3 | 4 | | | IV-2 | 4933411K20Rik | 0.90 |
| 2865 | 3 | 4 | | | IV-2 | 4933417G07Rik | 0.94 |
| 2866 | 3 | 4 | | | IV-2 | 4933434E20Rik | 0.98 |
| 2867 | 3 | 4 | | | IV-2 | 5031439G07Rik | 0.89 |
| 2868 | 3 | 4 | | | IV-2 | 5330417C22Rik | 0.72 |
| 2869 | 3 | 4 | | | IV-2 | 5430405H02Rik | 0.93 |
| 2870 | 3 | 4 | | | IV-2 | 5430417L22Rik | 0.82 |
| 2871 | 3 | 4 | | | IV-2 | 5430435G22Rik | 0.71 |
| 2872 | 3 | 4 | | | IV-2 | 5530601H04Rik | 0.97 |
| 2873 | 3 | 4 | | | IV-2 | 5730408K05Rik | 0.97 |
| 2874 | 3 | 4 | | | IV-2 | 5730559C18Rik | 0.87 |
| 2875 | 3 | 4 | | | IV-2 | 5830415F09Rik | 0.75 |
| 2876 | 3 | 4 | | | IV-2 | 5830417I10Rik | 0.92 |
| 2877 | 3 | 4 | | | IV-2 | 5930403L14Rik | 0.77 |
| 2878 | 3 | 4 | | | IV-2 | 6030458C11Rik | 0.98 |

Fig. 45 - 16

| | | | | | | | | | | | | | | |
|---|---|---|---|---|---|---|---|---|---|---|---|---|---|---|
| 2879 | 3 | 4 | | | IV-2 | 6330418K02Rik | 0.96 | 2975 | 3 | 4 | | | IV-2 | Ablim1 | 0.88 |
| 2880 | 3 | 4 | | | IV-2 | 6330549D23Rik | 0.87 | 2976 | 3 | 4 | | | IV-2 | Ablim2 | 0.81 |
| 2881 | 3 | 4 | | | IV-2 | 6430548M08Rik | 0.95 | 2977 | 3 | 4 | | | IV-2 | Ablim3 | 0.98 |
| 2882 | 3 | 4 | | | IV-2 | 6430562O15Rik | 0.69 | 2978 | 3 | 4 | | | IV-2 | Abra | 0.74 |
| 2883 | 3 | 4 | | | IV-2 | 6430571L13Rik | 0.77 | 2979 | 3 | 4 | | | IV-2 | Abracl | 0.83 |
| 2884 | 3 | 4 | | | IV-2 | 6430706D22Rik | 0.87 | 2980 | 3 | 4 | | | IV-2 | Abt1 | 0.93 |
| 2885 | 3 | 4 | | | IV-2 | 6720489N17Rik | 0.82 | 2981 | 3 | 4 | | | IV-2 | Abtb2 | 0.79 |
| 2886 | 3 | 4 | | | IV-2 | 8030462N17Rik | 0.87 | 2982 | 3 | 4 | | | IV-2 | Acaa1a | 0.75 |
| 2887 | 3 | 4 | | | IV-2 | 8430426J06Rik | 0.73 | 2983 | 3 | 4 | | | IV-2 | Acaa1b | 0.85 |
| 2888 | 3 | 4 | | | IV-2 | 9030624J02Rik | 0.86 | 2984 | 3 | 4 | | | IV-2 | Acaca | 0.95 |
| 2889 | 3 | 4 | | | IV-2 | 9130019O22Rik | 0.90 | 2985 | 3 | 4 | | | IV-2 | Acacb | 0.73 |
| 2890 | 3 | 4 | | | IV-2 | 9130023H24Rik | 0.92 | 2986 | 3 | 4 | | | IV-2 | Acad11 | 0.83 |
| 2891 | 3 | 4 | | | IV-2 | 9130401M01Rik | 0.98 | 2987 | 3 | 4 | | | IV-2 | Acad8 | 0.93 |
| 2892 | 3 | 4 | | | IV-2 | 9230114K14Rik | 0.80 | 2988 | 3 | 4 | | | IV-2 | Acad9 | 0.77 |
| 2893 | 3 | 4 | | | IV-2 | 9330162O12Rik | 0.99 | 2989 | 3 | 4 | | | IV-2 | Acads | 0.67 |
| 2894 | 3 | 4 | | | IV-2 | 9430015G10Rik | 0.80 | 2990 | 3 | 4 | | | IV-2 | Acadsb | 0.89 |
| 2895 | 3 | 4 | | | IV-2 | 9430020K01Rik | 0.88 | 2991 | 3 | 4 | | | IV-2 | Acat1 | 0.83 |
| 2896 | 3 | 4 | | | IV-2 | 9530077C05Rik | 0.82 | 2992 | 3 | 4 | | | IV-2 | Acat2 | 0.93 |
| 2897 | 3 | 4 | | | IV-2 | 9830147E19Rik | 0.94 | 2993 | 3 | 4 | | | IV-2 | Acbd3 | 0.94 |
| 2898 | 3 | 4 | | | IV-2 | 9930012K11Rik | 0.81 | 2994 | 3 | 4 | | | IV-2 | Acbd4 | 0.75 |
| 2899 | 3 | 4 | | | IV-2 | 9930111J21Rik2 | 0.86 | 2995 | 3 | 4 | | | IV-2 | Acbd6 | 0.91 |
| 2900 | 3 | 4 | | | IV-2 | A1cf | 0.70 | 2996 | 3 | 4 | | | IV-2 | Ace | 0.77 |
| 2901 | 3 | 4 | | | IV-2 | A230065H16Rik | 0.69 | 2997 | 3 | 4 | | | IV-2 | Ace2 | 0.70 |
| 2902 | 3 | 4 | | | IV-2 | A230072C01Rik | 0.95 | 2998 | 3 | 4 | | | IV-2 | Acer3 | 0.84 |
| 2903 | 3 | 4 | | | IV-2 | A330009N23Rik | 0.80 | 2999 | 3 | 4 | | | IV-2 | Acin1 | 0.89 |
| 2904 | 3 | 4 | | | IV-2 | A330074K22Rik | 0.87 | 3000 | 3 | 4 | | | IV-2 | Ackr4 | 0.94 |
| 2905 | 3 | 4 | | | IV-2 | A330102I10Rik | 0.92 | 3001 | 3 | 4 | | | IV-2 | Acly | 0.75 |
| 2906 | 3 | 4 | | | IV-2 | A430005L14Rik | 0.85 | 3002 | 3 | 4 | | | IV-2 | Acmsd | 0.72 |
| 2907 | 3 | 4 | | | IV-2 | A430033K04Rik | 0.93 | 3003 | 3 | 4 | | | IV-2 | Aco1 | 0.73 |
| 2908 | 3 | 4 | | | IV-2 | A530016L24Rik | 0.77 | 3004 | 3 | 4 | | | IV-2 | Acot10 | 0.99 |
| 2909 | 3 | 4 | | | IV-2 | A530054K11Rik | 0.80 | 3005 | 3 | 4 | | | IV-2 | Acot11 | 0.73 |
| 2910 | 3 | 4 | | | IV-2 | A530099J19Rik | 0.72 | 3006 | 3 | 4 | | | IV-2 | Acot3 | 0.91 |
| 2911 | 3 | 4 | | | IV-2 | A630089N07Rik | 0.79 | 3007 | 3 | 4 | | | IV-2 | Acot4 | 0.73 |
| 2912 | 3 | 4 | | | IV-2 | A730008H23Rik | 0.97 | 3008 | 3 | 4 | | | IV-2 | Acot8 | 0.94 |
| 2913 | 3 | 4 | | | IV-2 | A730017L22Rik | 0.82 | 3009 | 3 | 4 | | | IV-2 | Acot9 | 0.97 |
| 2914 | 3 | 4 | | | IV-2 | A730098P11Rik | 0.97 | 3010 | 3 | 4 | | | IV-2 | Acox1 | 0.95 |
| 2915 | 3 | 4 | | | IV-2 | A930004D18Rik | 0.90 | 3011 | 3 | 4 | | | IV-2 | Acox2 | 0.67 |
| 2916 | 3 | 4 | | | IV-2 | A930015D03Rik | 0.70 | 3012 | 3 | 4 | | | IV-2 | Acp1 | 0.77 |
| 2917 | 3 | 4 | | | IV-2 | A930024E05Rik | 0.84 | 3013 | 3 | 4 | | | IV-2 | Acp6 | 0.89 |
| 2918 | 3 | 4 | | | IV-2 | AA388235 | 0.98 | 3014 | 3 | 4 | | | IV-2 | Acpp | 0.74 |
| 2919 | 3 | 4 | | | IV-2 | AA986860 | 0.85 | 3015 | 3 | 4 | | | IV-2 | Acrbp | 0.85 |
| 2920 | 3 | 4 | | | IV-2 | AA987161 | 0.95 | 3016 | 3 | 4 | | | IV-2 | Acsbg1 | 0.71 |
| 2921 | 3 | 4 | | | IV-2 | AI427809 | 0.79 | 3017 | 3 | 4 | | | IV-2 | Acsf3 | 0.87 |
| 2922 | 3 | 4 | | | IV-2 | AI429214 | 0.98 | 3018 | 3 | 4 | | | IV-2 | Acsl3 | 0.92 |
| 2923 | 3 | 4 | | | IV-2 | AI450353 | 0.87 | 3019 | 3 | 4 | | | IV-2 | Acsl4 | 0.98 |
| 2924 | 3 | 4 | | | IV-2 | AI462493 | 0.89 | 3020 | 3 | 4 | | | IV-2 | Acta2 | 0.70 |
| 2925 | 3 | 4 | | | IV-2 | AI597479 | 0.95 | 3021 | 3 | 4 | | | IV-2 | Actb | 0.86 |
| 2926 | 3 | 4 | | | IV-2 | AI661453 | 0.75 | 3022 | 3 | 4 | | | IV-2 | Actg1 | 0.83 |
| 2927 | 3 | 4 | | | IV-2 | AI987944 | 0.91 | 3023 | 3 | 4 | | | IV-2 | Actg2 | 0.70 |
| 2928 | 3 | 4 | | | IV-2 | AK010878 | 0.90 | 3024 | 3 | 4 | | | IV-2 | Actl6a | 0.77 |
| 2929 | 3 | 4 | | | IV-2 | AU021092 | 0.69 | 3025 | 3 | 4 | | | IV-2 | Actn1 | 0.94 |
| 2930 | 3 | 4 | | | IV-2 | AU022252 | 0.98 | 3026 | 3 | 4 | | | IV-2 | Actn2 | 0.71 |
| 2931 | 3 | 4 | | | IV-2 | AV039307 | 0.99 | 3027 | 3 | 4 | | | IV-2 | Actn4 | 0.88 |
| 2932 | 3 | 4 | | | IV-2 | AW146154 | 0.95 | 3028 | 3 | 4 | | | IV-2 | Actr2 | 1.00 |
| 2933 | 3 | 4 | | | IV-2 | AW209491 | 0.99 | 3029 | 3 | 4 | | | IV-2 | Actr3 | 0.93 |
| 2934 | 3 | 4 | | | IV-2 | AW551984 | 0.94 | 3030 | 3 | 4 | | | IV-2 | Actr6 | 0.96 |
| 2935 | 3 | 4 | | | IV-2 | AY358078 | 0.77 | 3031 | 3 | 4 | | | IV-2 | Acvr1c | 0.76 |
| 2936 | 3 | 4 | | | IV-2 | Aaas | 0.83 | 3032 | 3 | 4 | | | IV-2 | Acvrl1 | 0.91 |
| 2937 | 3 | 4 | | | IV-2 | Aacs | 0.90 | 3033 | 3 | 4 | | | IV-2 | Acy1 | 0.92 |
| 2938 | 3 | 4 | | | IV-2 | Aaed1 | 0.95 | 3034 | 3 | 4 | | | IV-2 | Acyp1 | 0.79 |
| 2939 | 3 | 4 | | | IV-2 | Aagab | 0.99 | 3035 | 3 | 4 | | | IV-2 | Acyp2 | 0.95 |
| 2940 | 3 | 4 | | | IV-2 | Aamdc | 0.84 | 3036 | 3 | 4 | | | IV-2 | Ada | 0.88 |
| 2941 | 3 | 4 | | | IV-2 | Aar2 | 0.93 | 3037 | 3 | 4 | | | IV-2 | Adam10 | 0.77 |
| 2942 | 3 | 4 | | | IV-2 | Aard | 0.77 | 3038 | 3 | 4 | | | IV-2 | Adam12 | 0.67 |
| 2943 | 3 | 4 | | | IV-2 | Aars2 | 0.82 | 3039 | 3 | 4 | | | IV-2 | Adam15 | 0.93 |
| 2944 | 3 | 4 | | | IV-2 | Aasdh | 0.91 | 3040 | 3 | 4 | | | IV-2 | Adam17 | 0.79 |
| 2945 | 3 | 4 | | | IV-2 | Aasdhppt | 0.94 | 3041 | 3 | 4 | | | IV-2 | Adam19 | 0.89 |
| 2946 | 3 | 4 | | | IV-2 | Abat | 0.82 | 3042 | 3 | 4 | | | IV-2 | Adam9 | 0.91 |
| 2947 | 3 | 4 | | | IV-2 | Abca1 | 0.88 | 3043 | 3 | 4 | | | IV-2 | Adamts10 | 1.00 |
| 2948 | 3 | 4 | | | IV-2 | Abca12 | 0.90 | 3044 | 3 | 4 | | | IV-2 | Adamts12 | 0.90 |
| 2949 | 3 | 4 | | | IV-2 | Abca3 | 0.84 | 3045 | 3 | 4 | | | IV-2 | Adamts14 | 0.87 |
| 2950 | 3 | 4 | | | IV-2 | Abca7 | 0.77 | 3046 | 3 | 4 | | | IV-2 | Adamts15 | 0.88 |
| 2951 | 3 | 4 | | | IV-2 | Abca8a | 0.80 | 3047 | 3 | 4 | | | IV-2 | Adamts4 | 0.82 |
| 2952 | 3 | 4 | | | IV-2 | Abca9 | 0.83 | 3048 | 3 | 4 | | | IV-2 | Adamts8 | 0.82 |
| 2953 | 3 | 4 | | | IV-2 | Abcb11 | 0.88 | 3049 | 3 | 4 | | | IV-2 | Adamtsl4 | 0.81 |
| 2954 | 3 | 4 | | | IV-2 | Abcb7 | 0.67 | 3050 | 3 | 4 | | | IV-2 | Adat1 | 0.99 |
| 2955 | 3 | 4 | | | IV-2 | Abcb8 | 0.84 | 3051 | 3 | 4 | | | IV-2 | Adat3 | 0.89 |
| 2956 | 3 | 4 | | | IV-2 | Abcc2 | 0.89 | 3052 | 3 | 4 | | | IV-2 | Adck4 | 0.89 |
| 2957 | 3 | 4 | | | IV-2 | Abcc5 | 0.93 | 3053 | 3 | 4 | | | IV-2 | Adcy3 | 0.96 |
| 2958 | 3 | 4 | | | IV-2 | Abcd1 | 0.87 | 3054 | 3 | 4 | | | IV-2 | Adcy4 | 0.96 |
| 2959 | 3 | 4 | | | IV-2 | Abce1 | 0.77 | 3055 | 3 | 4 | | | IV-2 | Adcy6 | 0.86 |
| 2960 | 3 | 4 | | | IV-2 | Abcf1 | 0.96 | 3056 | 3 | 4 | | | IV-2 | Adcy7 | 0.78 |
| 2961 | 3 | 4 | | | IV-2 | Abcf2 | 0.91 | 3057 | 3 | 4 | | | IV-2 | Add1 | 0.87 |
| 2962 | 3 | 4 | | | IV-2 | Abcf3 | 0.93 | 3058 | 3 | 4 | | | IV-2 | Add2 | 0.95 |
| 2963 | 3 | 4 | | | IV-2 | Abcg2 | 0.82 | 3059 | 3 | 4 | | | IV-2 | Add3 | 0.88 |
| 2964 | 3 | 4 | | | IV-2 | Abcg3 | 0.91 | 3060 | 3 | 4 | | | IV-2 | Adh1 | 0.71 |
| 2965 | 3 | 4 | | | IV-2 | Abhd13 | 0.98 | 3061 | 3 | 4 | | | IV-2 | Adh5 | 0.91 |
| 2966 | 3 | 4 | | | IV-2 | Abhd14b | 0.93 | 3062 | 3 | 4 | | | IV-2 | Adipor1 | 0.84 |
| 2967 | 3 | 4 | | | IV-2 | Abhd16a | 0.89 | 3063 | 3 | 4 | | | IV-2 | Adipor2 | 0.71 |
| 2968 | 3 | 4 | | | IV-2 | Abhd17a | 0.86 | 3064 | 3 | 4 | | | IV-2 | Adk | 0.68 |
| 2969 | 3 | 4 | | | IV-2 | Abhd17c | 0.99 | 3065 | 3 | 4 | | | IV-2 | Ado | 0.83 |
| 2970 | 3 | 4 | | | IV-2 | Abhd2 | 0.95 | 3066 | 3 | 4 | | | IV-2 | Adora2a | 0.89 |
| 2971 | 3 | 4 | | | IV-2 | Abhd5 | 0.71 | 3067 | 3 | 4 | | | IV-2 | Adora2b | 0.78 |
| 2972 | 3 | 4 | | | IV-2 | Abhd6 | 0.84 | 3068 | 3 | 4 | | | IV-2 | Adpgk | 0.96 |
| 2973 | 3 | 4 | | | IV-2 | Abhd8 | 0.99 | 3069 | 3 | 4 | | | IV-2 | Adprh | 0.89 |
| 2974 | 3 | 4 | | | IV-2 | Abi3 | 0.76 | 3070 | 3 | 4 | | | IV-2 | Adprhl2 | 0.97 |

Fig. 45 - 17

| | | | | | | | | | | | | | | | |
|---|---|---|---|---|---|---|---|---|---|---|---|---|---|---|---|
| 3071 | 3 | 4 | | | IV-2 | Adprm | 0.90 | 3167 | 3 | 4 | | | IV-2 | Amotl1 | 0.93 |
| 3072 | 3 | 4 | | | IV-2 | Adra1b | 0.82 | 3168 | 3 | 4 | | | IV-2 | Ampd2 | 0.87 |
| 3073 | 3 | 4 | | | IV-2 | Adra1d | 0.84 | 3169 | 3 | 4 | | | IV-2 | Amt | 0.90 |
| 3074 | 3 | 4 | | | IV-2 | Adrb1 | 0.85 | 3170 | 3 | 4 | | | IV-2 | Amz1 | 0.81 |
| 3075 | 3 | 4 | | | IV-2 | Adrbk1 | 0.83 | 3171 | 3 | 4 | | | IV-2 | Anapc1 | 0.89 |
| 3076 | 3 | 4 | | | IV-2 | Adrm1 | 0.99 | 3172 | 3 | 4 | | | IV-2 | Anapc10 | 0.93 |
| 3077 | 3 | 4 | | | IV-2 | Adsl | 0.97 | 3173 | 3 | 4 | | | IV-2 | Anapc11 | 0.90 |
| 3078 | 3 | 4 | | | IV-2 | Adssl1 | 0.92 | 3174 | 3 | 4 | | | IV-2 | Anapc15 | 0.85 |
| 3079 | 3 | 4 | | | IV-2 | Aebp1 | 0.79 | 3175 | 3 | 4 | | | IV-2 | Anapc2 | 0.92 |
| 3080 | 3 | 4 | | | IV-2 | Aes | 0.83 | 3176 | 3 | 4 | | | IV-2 | Anapc5 | 0.89 |
| 3081 | 3 | 4 | | | IV-2 | Afap1l1 | 0.90 | 3177 | 3 | 4 | | | IV-2 | Angel1 | 0.91 |
| 3082 | 3 | 4 | | | IV-2 | Afap1l2 | 0.73 | 3178 | 3 | 4 | | | IV-2 | Angptl1 | 0.89 |
| 3083 | 3 | 4 | | | IV-2 | Aff1 | 0.89 | 3179 | 3 | 4 | | | IV-2 | Angptl2 | 0.78 |
| 3084 | 3 | 4 | | | IV-2 | Afg3l2 | 0.82 | 3180 | 3 | 4 | | | IV-2 | Angptl6 | 0.69 |
| 3085 | 3 | 4 | | | IV-2 | Aftph | 0.92 | 3181 | 3 | 4 | | | IV-2 | Ank | 0.90 |
| 3086 | 3 | 4 | | | IV-2 | Aga | 0.83 | 3182 | 3 | 4 | | | IV-2 | Ankdd1b | 0.95 |
| 3087 | 3 | 4 | | | IV-2 | Agfg1 | 0.77 | 3183 | 3 | 4 | | | IV-2 | Ankfy1 | 0.88 |
| 3088 | 3 | 4 | | | IV-2 | Agfg2 | 0.91 | 3184 | 3 | 4 | | | IV-2 | Ankhd1 | 0.93 |
| 3089 | 3 | 4 | | | IV-2 | Aggf1 | 0.82 | 3185 | 3 | 4 | | | IV-2 | Ankrd13a | 0.89 |
| 3090 | 3 | 4 | | | IV-2 | Agl | 0.82 | 3186 | 3 | 4 | | | IV-2 | Ankrd13c | 0.85 |
| 3091 | 3 | 4 | | | IV-2 | Ago2 | 0.73 | 3187 | 3 | 4 | | | IV-2 | Ankrd22 | 0.82 |
| 3092 | 3 | 4 | | | IV-2 | Ago3 | 0.89 | 3188 | 3 | 4 | | | IV-2 | Ankrd23 | 0.74 |
| 3093 | 3 | 4 | | | IV-2 | Agpat1 | 0.79 | 3189 | 3 | 4 | | | IV-2 | Ankrd27 | 0.99 |
| 3094 | 3 | 4 | | | IV-2 | Agpat2 | 0.97 | 3190 | 3 | 4 | | | IV-2 | Ankrd29 | 0.91 |
| 3095 | 3 | 4 | | | IV-2 | Agpat3 | 0.90 | 3191 | 3 | 4 | | | IV-2 | Ankrd33b | 0.93 |
| 3096 | 3 | 4 | | | IV-2 | Agpat4 | 0.99 | 3192 | 3 | 4 | | | IV-2 | Ankrd34a | 0.97 |
| 3097 | 3 | 4 | | | IV-2 | Agps | 0.93 | 3193 | 3 | 4 | | | IV-2 | Ankrd35 | 0.74 |
| 3098 | 3 | 4 | | | IV-2 | Agtr1a | 0.94 | 3194 | 3 | 4 | | | IV-2 | Ankrd40 | 0.81 |
| 3099 | 3 | 4 | | | IV-2 | Agtrap | 0.97 | 3195 | 3 | 4 | | | IV-2 | Ankrd45 | 0.98 |
| 3100 | 3 | 4 | | | IV-2 | Agxt | 0.85 | 3196 | 3 | 4 | | | IV-2 | Ankrd49 | 0.97 |
| 3101 | 3 | 4 | | | IV-2 | Ahctf1 | 0.96 | 3197 | 3 | 4 | | | IV-2 | Ankrd54 | 0.82 |
| 3102 | 3 | 4 | | | IV-2 | Ahcyl2 | 0.76 | 3198 | 3 | 4 | | | IV-2 | Anks3 | 0.95 |
| 3103 | 3 | 4 | | | IV-2 | Ahnak | 0.92 | 3199 | 3 | 4 | | | IV-2 | Ano1 | 0.83 |
| 3104 | 3 | 4 | | | IV-2 | Ahsa1 | 0.79 | 3200 | 3 | 4 | | | IV-2 | Ano6 | 1.00 |
| 3105 | 3 | 4 | | | IV-2 | Aida | 0.98 | 3201 | 3 | 4 | | | IV-2 | Ano9 | 0.86 |
| 3106 | 3 | 4 | | | IV-2 | Aifm2 | 0.90 | 3202 | 3 | 4 | | | IV-2 | Anp32a | 0.71 |
| 3107 | 3 | 4 | | | IV-2 | Aig1 | 0.93 | 3203 | 3 | 4 | | | IV-2 | Anp32b | 0.69 |
| 3108 | 3 | 4 | | | IV-2 | Aim1 | 0.90 | 3204 | 3 | 4 | | | IV-2 | Anp32e | 0.77 |
| 3109 | 3 | 4 | | | IV-2 | Aim1l | 0.89 | 3205 | 3 | 4 | | | IV-2 | Anpep | 0.78 |
| 3110 | 3 | 4 | | | IV-2 | Aimp2 | 0.81 | 3206 | 3 | 4 | | | IV-2 | Antxr1 | 0.93 |
| 3111 | 3 | 4 | | | IV-2 | Aip | 0.71 | 3207 | 3 | 4 | | | IV-2 | Antxr2 | 0.74 |
| 3112 | 3 | 4 | | | IV-2 | Ak1 | 0.70 | 3208 | 3 | 4 | | | IV-2 | Anxa2 | 0.74 |
| 3113 | 3 | 4 | | | IV-2 | Ak2 | 0.68 | 3209 | 3 | 4 | | | IV-2 | Anxa5 | 0.71 |
| 3114 | 3 | 4 | | | IV-2 | Ak3 | 0.87 | 3210 | 3 | 4 | | | IV-2 | Anxa6 | 0.72 |
| 3115 | 3 | 4 | | | IV-2 | Akap1 | 0.85 | 3211 | 3 | 4 | | | IV-2 | Anxa7 | 0.75 |
| 3116 | 3 | 4 | | | IV-2 | Akap10 | 0.96 | 3212 | 3 | 4 | | | IV-2 | Anxa9 | 0.75 |
| 3117 | 3 | 4 | | | IV-2 | Akap2 | 0.87 | 3213 | 3 | 4 | | | IV-2 | Aox4 | 0.69 |
| 3118 | 3 | 4 | | | IV-2 | Akap5 | 0.96 | 3214 | 3 | 4 | | | IV-2 | Ap1b1 | 0.92 |
| 3119 | 3 | 4 | | | IV-2 | Akip1 | 0.77 | 3215 | 3 | 4 | | | IV-2 | Ap1g1 | 1.00 |
| 3120 | 3 | 4 | | | IV-2 | Akirin2 | 0.94 | 3216 | 3 | 4 | | | IV-2 | Ap1g2 | 0.75 |
| 3121 | 3 | 4 | | | IV-2 | Akr1a1 | 0.99 | 3217 | 3 | 4 | | | IV-2 | Ap1s1 | 0.86 |
| 3122 | 3 | 4 | | | IV-2 | Akr1b10 | 0.70 | 3218 | 3 | 4 | | | IV-2 | Ap1s3 | 0.90 |
| 3123 | 3 | 4 | | | IV-2 | Akr1b3 | 0.88 | 3219 | 3 | 4 | | | IV-2 | Ap2a2 | 0.89 |
| 3124 | 3 | 4 | | | IV-2 | Akr1c12 | 0.78 | 3220 | 3 | 4 | | | IV-2 | Ap2b1 | 0.94 |
| 3125 | 3 | 4 | | | IV-2 | Akr1c13 | 0.72 | 3221 | 3 | 4 | | | IV-2 | Ap2m1 | 0.85 |
| 3126 | 3 | 4 | | | IV-2 | Akr1c14 | 0.67 | 3222 | 3 | 4 | | | IV-2 | Ap2s1 | 0.81 |
| 3127 | 3 | 4 | | | IV-2 | Akr1e1 | 0.86 | 3223 | 3 | 4 | | | IV-2 | Ap3b1 | 0.90 |
| 3128 | 3 | 4 | | | IV-2 | Akr7a5 | 0.91 | 3224 | 3 | 4 | | | IV-2 | Ap3m1 | 0.83 |
| 3129 | 3 | 4 | | | IV-2 | Akt2 | 0.84 | 3225 | 3 | 4 | | | IV-2 | Ap3s1 | 0.88 |
| 3130 | 3 | 4 | | | IV-2 | Aktip | 0.96 | 3226 | 3 | 4 | | | IV-2 | Ap4s1 | 0.98 |
| 3131 | 3 | 4 | | | IV-2 | Alas1 | 0.72 | 3227 | 3 | 4 | | | IV-2 | Ap5b1 | 0.88 |
| 3132 | 3 | 4 | | | IV-2 | Aldh16a1 | 0.84 | 3228 | 3 | 4 | | | IV-2 | Ap5m1 | 0.86 |
| 3133 | 3 | 4 | | | IV-2 | Aldh18a1 | 0.89 | 3229 | 3 | 4 | | | IV-2 | Ap5s1 | 0.94 |
| 3134 | 3 | 4 | | | IV-2 | Aldh1l1 | 0.87 | 3230 | 3 | 4 | | | IV-2 | Ap5z1 | 0.81 |
| 3135 | 3 | 4 | | | IV-2 | Aldh2 | 0.86 | 3231 | 3 | 4 | | | IV-2 | Apba3 | 0.75 |
| 3136 | 3 | 4 | | | IV-2 | Aldh3a2 | 0.97 | 3232 | 3 | 4 | | | IV-2 | Apbb1ip | 0.81 |
| 3137 | 3 | 4 | | | IV-2 | Aldh3b1 | 1.00 | 3233 | 3 | 4 | | | IV-2 | Apela | 0.98 |
| 3138 | 3 | 4 | | | IV-2 | Aldh7a1 | 0.73 | 3234 | 3 | 4 | | | IV-2 | Apex1 | 0.90 |
| 3139 | 3 | 4 | | | IV-2 | Aldh8a1 | 0.71 | 3235 | 3 | 4 | | | IV-2 | Apex2 | 0.70 |
| 3140 | 3 | 4 | | | IV-2 | Aldh9a1 | 0.80 | 3236 | 3 | 4 | | | IV-2 | Api5 | 0.96 |
| 3141 | 3 | 4 | | | IV-2 | Alg1 | 0.72 | 3237 | 3 | 4 | | | IV-2 | Aplf | 0.89 |
| 3142 | 3 | 4 | | | IV-2 | Alg12 | 0.75 | 3238 | 3 | 4 | | | IV-2 | Aplp2 | 0.86 |
| 3143 | 3 | 4 | | | IV-2 | Alg13 | 0.87 | 3239 | 3 | 4 | | | IV-2 | Apmap | 0.73 |
| 3144 | 3 | 4 | | | IV-2 | Alg14 | 0.74 | 3240 | 3 | 4 | | | IV-2 | Apoa1 | 0.87 |
| 3145 | 3 | 4 | | | IV-2 | Alg3 | 0.79 | 3241 | 3 | 4 | | | IV-2 | Apoa1bp | 0.80 |
| 3146 | 3 | 4 | | | IV-2 | Alg6 | 0.92 | 3242 | 3 | 4 | | | IV-2 | Apobec2 | 0.69 |
| 3147 | 3 | 4 | | | IV-2 | Alg8 | 0.77 | 3243 | 3 | 4 | | | IV-2 | Apobec3 | 0.83 |
| 3148 | 3 | 4 | | | IV-2 | Alg9 | 0.76 | 3244 | 3 | 4 | | | IV-2 | Apoc4 | 0.81 |
| 3149 | 3 | 4 | | | IV-2 | Alkbh2 | 0.90 | 3245 | 3 | 4 | | | IV-2 | Apof | 0.72 |
| 3150 | 3 | 4 | | | IV-2 | Alkbh4 | 0.89 | 3246 | 3 | 4 | | | IV-2 | Apool | 0.79 |
| 3151 | 3 | 4 | | | IV-2 | Alkbh5 | 0.81 | 3247 | 3 | 4 | | | IV-2 | Apopt1 | 0.92 |
| 3152 | 3 | 4 | | | IV-2 | Alkbh7 | 0.80 | 3248 | 3 | 4 | | | IV-2 | Aprt | 0.96 |
| 3153 | 3 | 4 | | | IV-2 | Alms1 | 0.87 | 3249 | 3 | 4 | | | IV-2 | Aqp1 | 0.80 |
| 3154 | 3 | 4 | | | IV-2 | Alox12b | 0.99 | 3250 | 3 | 4 | | | IV-2 | Aqp11 | 0.87 |
| 3155 | 3 | 4 | | | IV-2 | Aloxe3 | 0.86 | 3251 | 3 | 4 | | | IV-2 | Aqp4 | 0.93 |
| 3156 | 3 | 4 | | | IV-2 | Alpk3 | 0.93 | 3252 | 3 | 4 | | | IV-2 | Aqp5 | 0.82 |
| 3157 | 3 | 4 | | | IV-2 | Alpl | 0.72 | 3253 | 3 | 4 | | | IV-2 | Arcn1 | 0.88 |
| 3158 | 3 | 4 | | | IV-2 | Als2 | 0.86 | 3254 | 3 | 4 | | | IV-2 | Arf1 | 0.92 |
| 3159 | 3 | 4 | | | IV-2 | Alyref | 0.81 | 3255 | 3 | 4 | | | IV-2 | Arf4 | 0.87 |
| 3160 | 3 | 4 | | | IV-2 | Alyref2 | 0.95 | 3256 | 3 | 4 | | | IV-2 | Arf5 | 0.80 |
| 3161 | 3 | 4 | | | IV-2 | Amacr | 0.75 | 3257 | 3 | 4 | | | IV-2 | Arf6 | 0.73 |
| 3162 | 3 | 4 | | | IV-2 | Amdhd2 | 0.93 | 3258 | 3 | 4 | | | IV-2 | Arfgap2 | 0.89 |
| 3163 | 3 | 4 | | | IV-2 | Amigo3 | 0.86 | 3259 | 3 | 4 | | | IV-2 | Arfgap3 | 0.93 |
| 3164 | 3 | 4 | | | IV-2 | Ammecr1 | 0.70 | 3260 | 3 | 4 | | | IV-2 | Arfgef2 | 0.94 |
| 3165 | 3 | 4 | | | IV-2 | Ammecr1l | 0.87 | 3261 | 3 | 4 | | | IV-2 | Arfip1 | 0.94 |
| 3166 | 3 | 4 | | | IV-2 | Amn | 0.68 | 3262 | 3 | 4 | | | IV-2 | Arfrp1 | 0.86 |

Fig. 45 - 18

| | | | | | | | | | | | | | | |
|---|---|---|---|---|---|---|---|---|---|---|---|---|---|---|
| 3263 | 3 | 4 | | | IV-2 | Arhgap11a | 0.76 | 3359 | 3 | 4 | | | IV-2 | Atp1a1 | 0.99 |
| 3264 | 3 | 4 | | | IV-2 | Arhgap15 | 0.98 | 3360 | 3 | 4 | | | IV-2 | Atp1b3 | 0.85 |
| 3265 | 3 | 4 | | | IV-2 | Arhgap17 | 0.97 | 3361 | 3 | 4 | | | IV-2 | Atp2a1 | 0.67 |
| 3266 | 3 | 4 | | | IV-2 | Arhgap18 | 0.71 | 3362 | 3 | 4 | | | IV-2 | Atp2a2 | 0.97 |
| 3267 | 3 | 4 | | | IV-2 | Arhgap20os | 0.86 | 3363 | 3 | 4 | | | IV-2 | Atp2b3 | 0.96 |
| 3268 | 3 | 4 | | | IV-2 | Arhgap22 | 0.97 | 3364 | 3 | 4 | | | IV-2 | Atp2b4 | 0.70 |
| 3269 | 3 | 4 | | | IV-2 | Arhgap26 | 0.96 | 3365 | 3 | 4 | | | IV-2 | Atp5a1 | 0.81 |
| 3270 | 3 | 4 | | | IV-2 | Arhgap27 | 0.95 | 3366 | 3 | 4 | | | IV-2 | Atp5b | 0.71 |
| 3271 | 3 | 4 | | | IV-2 | Arhgap29 | 0.85 | 3367 | 3 | 4 | | | IV-2 | Atp5c1 | 0.76 |
| 3272 | 3 | 4 | | | IV-2 | Arhgap30 | 0.99 | 3368 | 3 | 4 | | | IV-2 | Atp5f1 | 0.77 |
| 3273 | 3 | 4 | | | IV-2 | Arhgap31 | 0.95 | 3369 | 3 | 4 | | | IV-2 | Atp5g1 | 0.73 |
| 3274 | 3 | 4 | | | IV-2 | Arhgap36 | 0.71 | 3370 | 3 | 4 | | | IV-2 | Atp5g2 | 0.80 |
| 3275 | 3 | 4 | | | IV-2 | Arhgap6 | 0.90 | 3371 | 3 | 4 | | | IV-2 | Atp5g3 | 0.84 |
| 3276 | 3 | 4 | | | IV-2 | Arhgap9 | 0.92 | 3372 | 3 | 4 | | | IV-2 | Atp5j | 0.79 |
| 3277 | 3 | 4 | | | IV-2 | Arhgdia | 0.90 | 3373 | 3 | 4 | | | IV-2 | Atp5l | 0.93 |
| 3278 | 3 | 4 | | | IV-2 | Arhgef10 | 0.97 | 3374 | 3 | 4 | | | IV-2 | Atp5o | 0.71 |
| 3279 | 3 | 4 | | | IV-2 | Arhgef15 | 0.85 | 3375 | 3 | 4 | | | IV-2 | Atp5s | 0.85 |
| 3280 | 3 | 4 | | | IV-2 | Arhgef5 | 0.84 | 3376 | 3 | 4 | | | IV-2 | Atp5sl | 0.90 |
| 3281 | 3 | 4 | | | IV-2 | Arhgef6 | 0.97 | 3377 | 3 | 4 | | | IV-2 | Atp6ap1 | 0.93 |
| 3282 | 3 | 4 | | | IV-2 | Arid3a | 0.83 | 3378 | 3 | 4 | | | IV-2 | Atp6v0a2 | 0.83 |
| 3283 | 3 | 4 | | | IV-2 | Arid3b | 0.80 | 3379 | 3 | 4 | | | IV-2 | Atp6v0a4 | 0.71 |
| 3284 | 3 | 4 | | | IV-2 | Arid5a | 0.89 | 3380 | 3 | 4 | | | IV-2 | Atp6v0b | 0.80 |
| 3285 | 3 | 4 | | | IV-2 | Arih1 | 0.99 | 3381 | 3 | 4 | | | IV-2 | Atp6v0d1 | 0.93 |
| 3286 | 3 | 4 | | | IV-2 | Arl1 | 0.99 | 3382 | 3 | 4 | | | IV-2 | Atp6v0e | 0.68 |
| 3287 | 3 | 4 | | | IV-2 | Arl15 | 0.97 | 3383 | 3 | 4 | | | IV-2 | Atp6v1a | 0.94 |
| 3288 | 3 | 4 | | | IV-2 | Arl2 | 0.90 | 3384 | 3 | 4 | | | IV-2 | Atp6v1c1 | 0.86 |
| 3289 | 3 | 4 | | | IV-2 | Arl3 | 0.76 | 3385 | 3 | 4 | | | IV-2 | Atp6v1d | 0.91 |
| 3290 | 3 | 4 | | | IV-2 | Arl5a | 0.77 | 3386 | 3 | 4 | | | IV-2 | Atp6v1e1 | 0.91 |
| 3291 | 3 | 4 | | | IV-2 | Arl5b | 0.94 | 3387 | 3 | 4 | | | IV-2 | Atp6v1f | 0.90 |
| 3292 | 3 | 4 | | | IV-2 | Arl6ip1 | 0.77 | 3388 | 3 | 4 | | | IV-2 | Atp6v1g1 | 0.95 |
| 3293 | 3 | 4 | | | IV-2 | Arl6ip5 | 0.89 | 3389 | 3 | 4 | | | IV-2 | Atp7a | 0.99 |
| 3294 | 3 | 4 | | | IV-2 | Arl6ip6 | 0.81 | 3390 | 3 | 4 | | | IV-2 | Atp8a1 | 0.84 |
| 3295 | 3 | 4 | | | IV-2 | Arl8b | 0.86 | 3391 | 3 | 4 | | | IV-2 | Atp8b1 | 0.73 |
| 3296 | 3 | 4 | | | IV-2 | Armc1 | 0.82 | 3392 | 3 | 4 | | | IV-2 | Atpaf1 | 0.90 |
| 3297 | 3 | 4 | | | IV-2 | Armc7 | 0.93 | 3393 | 3 | 4 | | | IV-2 | Atpaf2 | 0.73 |
| 3298 | 3 | 4 | | | IV-2 | Armc9 | 0.88 | 3394 | 3 | 4 | | | IV-2 | Atpif1 | 0.76 |
| 3299 | 3 | 4 | | | IV-2 | Armcx3 | 0.90 | 3395 | 3 | 4 | | | IV-2 | Atxn1 | 0.96 |
| 3300 | 3 | 4 | | | IV-2 | Arpc1b | 0.91 | 3396 | 3 | 4 | | | IV-2 | Atxn2 | 0.94 |
| 3301 | 3 | 4 | | | IV-2 | Arpc2 | 0.99 | 3397 | 3 | 4 | | | IV-2 | Atxn3 | 0.99 |
| 3302 | 3 | 4 | | | IV-2 | Arpc3 | 0.73 | 3398 | 3 | 4 | | | IV-2 | Atxn7l1 | 0.87 |
| 3303 | 3 | 4 | | | IV-2 | Arpc4 | 0.88 | 3399 | 3 | 4 | | | IV-2 | Auh | 0.84 |
| 3304 | 3 | 4 | | | IV-2 | Arpc5l | 0.97 | 3400 | 3 | 4 | | | IV-2 | Aup1 | 0.75 |
| 3305 | 3 | 4 | | | IV-2 | Arsa | 0.91 | 3401 | 3 | 4 | | | IV-2 | Aurkaip1 | 0.88 |
| 3306 | 3 | 4 | | | IV-2 | Arsb | 0.88 | 3402 | 3 | 4 | | | IV-2 | Avpi1 | 0.91 |
| 3307 | 3 | 4 | | | IV-2 | Arsi | 0.97 | 3403 | 3 | 4 | | | IV-2 | Azin1 | 0.85 |
| 3308 | 3 | 4 | | | IV-2 | Arsj | 0.93 | 3404 | 3 | 4 | | | IV-2 | B230118H07Rik | 0.84 |
| 3309 | 3 | 4 | | | IV-2 | Arv1 | 0.85 | 3405 | 3 | 4 | | | IV-2 | B230206H07Rik | 0.95 |
| 3310 | 3 | 4 | | | IV-2 | Arxes1 | 0.96 | 3406 | 3 | 4 | | | IV-2 | B2m | 0.84 |
| 3311 | 3 | 4 | | | IV-2 | Arxes2 | 0.92 | 3407 | 3 | 4 | | | IV-2 | B3galnt2 | 0.88 |
| 3312 | 3 | 4 | | | IV-2 | Asah1 | 0.94 | 3408 | 3 | 4 | | | IV-2 | B3galt4 | 0.82 |
| 3313 | 3 | 4 | | | IV-2 | Asb1 | 0.69 | 3409 | 3 | 4 | | | IV-2 | B3galt6 | 0.77 |
| 3314 | 3 | 4 | | | IV-2 | Asb16 | 0.84 | 3410 | 3 | 4 | | | IV-2 | B3gnt2 | 0.92 |
| 3315 | 3 | 4 | | | IV-2 | Asb2 | 0.68 | 3411 | 3 | 4 | | | IV-2 | B3gnt3 | 0.78 |
| 3316 | 3 | 4 | | | IV-2 | Asb4 | 0.76 | 3412 | 3 | 4 | | | IV-2 | B3gnt7 | 0.77 |
| 3317 | 3 | 4 | | | IV-2 | Asb6 | 0.99 | 3413 | 3 | 4 | | | IV-2 | B3gnt8 | 0.71 |
| 3318 | 3 | 4 | | | IV-2 | Ascc2 | 0.83 | 3414 | 3 | 4 | | | IV-2 | B4galt3 | 0.78 |
| 3319 | 3 | 4 | | | IV-2 | Ascc3 | 0.85 | 3415 | 3 | 4 | | | IV-2 | B4galt1 | 0.92 |
| 3320 | 3 | 4 | | | IV-2 | Asf1a | 0.85 | 3416 | 3 | 4 | | | IV-2 | B4galt3 | 0.97 |
| 3321 | 3 | 4 | | | IV-2 | Asgr2 | 0.76 | 3417 | 3 | 4 | | | IV-2 | B4galt4 | 0.94 |
| 3322 | 3 | 4 | | | IV-2 | Asl | 0.96 | 3418 | 3 | 4 | | | IV-2 | B9d1 | 0.76 |
| 3323 | 3 | 4 | | | IV-2 | Asna1 | 0.79 | 3419 | 3 | 4 | | | IV-2 | BC002163 | 0.67 |
| 3324 | 3 | 4 | | | IV-2 | Asns | 0.86 | 3420 | 3 | 4 | | | IV-2 | BC003965 | 0.86 |
| 3325 | 3 | 4 | | | IV-2 | Asnsd1 | 0.88 | 3421 | 3 | 4 | | | IV-2 | BC004004 | 1.00 |
| 3326 | 3 | 4 | | | IV-2 | Aspa | 0.96 | 3422 | 3 | 4 | | | IV-2 | BC005537 | 0.98 |
| 3327 | 3 | 4 | | | IV-2 | Asph | 0.92 | 3423 | 3 | 4 | | | IV-2 | BC005561 | 0.94 |
| 3328 | 3 | 4 | | | IV-2 | Aste1 | 0.87 | 3424 | 3 | 4 | | | IV-2 | BC005624 | 0.96 |
| 3329 | 3 | 4 | | | IV-2 | Asxl2 | 0.87 | 3425 | 3 | 4 | | | IV-2 | BC017158 | 0.80 |
| 3330 | 3 | 4 | | | IV-2 | Atad2 | 0.70 | 3426 | 3 | 4 | | | IV-2 | BC017643 | 0.85 |
| 3331 | 3 | 4 | | | IV-2 | Atad2b | 1.00 | 3427 | 3 | 4 | | | IV-2 | BC021767 | 0.83 |
| 3332 | 3 | 4 | | | IV-2 | Atad3a | 0.93 | 3428 | 3 | 4 | | | IV-2 | BC021891 | 0.81 |
| 3333 | 3 | 4 | | | IV-2 | Atad5 | 0.82 | 3429 | 3 | 4 | | | IV-2 | BC023829 | 0.94 |
| 3334 | 3 | 4 | | | IV-2 | Atf1 | 0.90 | 3430 | 3 | 4 | | | IV-2 | BC025920 | 0.92 |
| 3335 | 3 | 4 | | | IV-2 | Atf3 | 0.92 | 3431 | 3 | 4 | | | IV-2 | BC026585 | 0.81 |
| 3336 | 3 | 4 | | | IV-2 | Atf6b | 1.00 | 3432 | 3 | 4 | | | IV-2 | BC028528 | 0.84 |
| 3337 | 3 | 4 | | | IV-2 | Atg10 | 0.93 | 3433 | 3 | 4 | | | IV-2 | BC031181 | 0.82 |
| 3338 | 3 | 4 | | | IV-2 | Atg101 | 0.96 | 3434 | 3 | 4 | | | IV-2 | BC048507 | 0.87 |
| 3339 | 3 | 4 | | | IV-2 | Atg12 | 0.92 | 3435 | 3 | 4 | | | IV-2 | BC052040 | 0.69 |
| 3340 | 3 | 4 | | | IV-2 | Atg16l2 | 0.68 | 3436 | 3 | 4 | | | IV-2 | BC053749 | 0.78 |
| 3341 | 3 | 4 | | | IV-2 | Atg2a | 0.93 | 3437 | 3 | 4 | | | IV-2 | BC055324 | 0.70 |
| 3342 | 3 | 4 | | | IV-2 | Atg3 | 0.94 | 3438 | 3 | 4 | | | IV-2 | BC100530 | 0.83 |
| 3343 | 3 | 4 | | | IV-2 | Atg4b | 0.97 | 3439 | 3 | 4 | | | IV-2 | Babam1 | 0.84 |
| 3344 | 3 | 4 | | | IV-2 | Atg4d | 0.75 | 3440 | 3 | 4 | | | IV-2 | Bace2 | 0.73 |
| 3345 | 3 | 4 | | | IV-2 | Atg5 | 0.93 | 3441 | 3 | 4 | | | IV-2 | Bag1 | 0.97 |
| 3346 | 3 | 4 | | | IV-2 | Atg7 | 0.98 | 3442 | 3 | 4 | | | IV-2 | Bag3 | 0.81 |
| 3347 | 3 | 4 | | | IV-2 | Athl1 | 0.94 | 3443 | 3 | 4 | | | IV-2 | Bag4 | 0.92 |
| 3348 | 3 | 4 | | | IV-2 | Atic | 0.89 | 3444 | 3 | 4 | | | IV-2 | Bahd1 | 0.76 |
| 3349 | 3 | 4 | | | IV-2 | Atl2 | 0.83 | 3445 | 3 | 4 | | | IV-2 | Baiap2l1 | 0.74 |
| 3350 | 3 | 4 | | | IV-2 | Atl3 | 0.96 | 3446 | 3 | 4 | | | IV-2 | Bak1 | 0.84 |
| 3351 | 3 | 4 | | | IV-2 | Atoh8 | 0.90 | 3447 | 3 | 4 | | | IV-2 | Banf1 | 0.70 |
| 3352 | 3 | 4 | | | IV-2 | Atox1 | 0.80 | 3448 | 3 | 4 | | | IV-2 | Bard1 | 0.74 |
| 3353 | 3 | 4 | | | IV-2 | Atp10a | 0.81 | 3449 | 3 | 4 | | | IV-2 | Batf | 0.97 |
| 3354 | 3 | 4 | | | IV-2 | Atp10b | 0.79 | 3450 | 3 | 4 | | | IV-2 | Batf3 | 0.95 |
| 3355 | 3 | 4 | | | IV-2 | Atp10d | 0.92 | 3451 | 3 | 4 | | | IV-2 | Baz1a | 0.73 |
| 3356 | 3 | 4 | | | IV-2 | Atp13a1 | 0.95 | 3452 | 3 | 4 | | | IV-2 | Baz1b | 0.85 |
| 3357 | 3 | 4 | | | IV-2 | Atp13a3 | 0.95 | 3453 | 3 | 4 | | | IV-2 | Baz2a | 0.96 |
| 3358 | 3 | 4 | | | IV-2 | Atp13a4 | 0.76 | 3454 | 3 | 4 | | | IV-2 | Bbox1 | 0.96 |

Fig. 45 - 19

| | | | | | | | |
|---|---|---|---|---|---|---|---|
| 3455 | 3 | 4 | | | IV-2 | Bbs10 | 0.91 |
| 3456 | 3 | 4 | | | IV-2 | Bbs5 | 0.74 |
| 3457 | 3 | 4 | | | IV-2 | Bbs7 | 0.95 |
| 3458 | 3 | 4 | | | IV-2 | Bbx | 0.99 |
| 3459 | 3 | 4 | | | IV-2 | Bcam | 0.86 |
| 3460 | 3 | 4 | | | IV-2 | Bcap31 | 0.81 |
| 3461 | 3 | 4 | | | IV-2 | Bcar3 | 0.93 |
| 3462 | 3 | 4 | | | IV-2 | Bcas2 | 0.86 |
| 3463 | 3 | 4 | | | IV-2 | Bcat2 | 0.77 |
| 3464 | 3 | 4 | | | IV-2 | Bccip | 0.86 |
| 3465 | 3 | 4 | | | IV-2 | Bche | 0.93 |
| 3466 | 3 | 4 | | | IV-2 | Bckdhb | 0.76 |
| 3467 | 3 | 4 | | | IV-2 | Bckdk | 0.86 |
| 3468 | 3 | 4 | | | IV-2 | Bcl2l12 | 0.87 |
| 3469 | 3 | 4 | | | IV-2 | Bcl2l13 | 0.73 |
| 3470 | 3 | 4 | | | IV-2 | Bcl2l14 | 0.90 |
| 3471 | 3 | 4 | | | IV-2 | Bcl2l15 | 0.68 |
| 3472 | 3 | 4 | | | IV-2 | Bcl3 | 0.85 |
| 3473 | 3 | 4 | | | IV-2 | Bcl6 | 0.72 |
| 3474 | 3 | 4 | | | IV-2 | Bcl6b | 0.71 |
| 3475 | 3 | 4 | | | IV-2 | Bcl7c | 0.96 |
| 3476 | 3 | 4 | | | IV-2 | Bcmo1 | 0.78 |
| 3477 | 3 | 4 | | | IV-2 | Bcorl1 | 0.75 |
| 3478 | 3 | 4 | | | IV-2 | Bdh1 | 0.80 |
| 3479 | 3 | 4 | | | IV-2 | Bdp1 | 0.87 |
| 3480 | 3 | 4 | | | IV-2 | Becn1 | 0.94 |
| 3481 | 3 | 4 | | | IV-2 | Bend3 | 0.97 |
| 3482 | 3 | 4 | | | IV-2 | Bend4 | 0.90 |
| 3483 | 3 | 4 | | | IV-2 | Best3 | 0.85 |
| 3484 | 3 | 4 | | | IV-2 | Bet1 | 0.76 |
| 3485 | 3 | 4 | | | IV-2 | Bex1 | 0.98 |
| 3486 | 3 | 4 | | | IV-2 | Bex4 | 0.74 |
| 3487 | 3 | 4 | | | IV-2 | Bfar | 0.94 |
| 3488 | 3 | 4 | | | IV-2 | Bgn | 0.91 |
| 3489 | 3 | 4 | | | IV-2 | Bhlhb9 | 0.95 |
| 3490 | 3 | 4 | | | IV-2 | Bhlhe40 | 0.76 |
| 3491 | 3 | 4 | | | IV-2 | Bhmt | 0.68 |
| 3492 | 3 | 4 | | | IV-2 | Bicd2 | 0.92 |
| 3493 | 3 | 4 | | | IV-2 | Bik | 0.70 |
| 3494 | 3 | 4 | | | IV-2 | Bin1 | 0.76 |
| 3495 | 3 | 4 | | | IV-2 | Bin2 | 0.96 |
| 3496 | 3 | 4 | | | IV-2 | Bin3 | 0.99 |
| 3497 | 3 | 4 | | | IV-2 | Birc3 | 0.93 |
| 3498 | 3 | 4 | | | IV-2 | Birc6 | 0.97 |
| 3499 | 3 | 4 | | | IV-2 | Blm | 0.74 |
| 3500 | 3 | 4 | | | IV-2 | Blmh | 0.76 |
| 3501 | 3 | 4 | | | IV-2 | Blnk | 0.72 |
| 3502 | 3 | 4 | | | IV-2 | Bloc1s1 | 0.87 |
| 3503 | 3 | 4 | | | IV-2 | Bloc1s3 | 0.96 |
| 3504 | 3 | 4 | | | IV-2 | Bloc1s4 | 0.93 |
| 3505 | 3 | 4 | | | IV-2 | Bloc1s5 | 0.87 |
| 3506 | 3 | 4 | | | IV-2 | Bmp10 | 0.81 |
| 3507 | 3 | 4 | | | IV-2 | Bmp2 | 0.92 |
| 3508 | 3 | 4 | | | IV-2 | Bmp2k | 0.78 |
| 3509 | 3 | 4 | | | IV-2 | Bmp3 | 0.91 |
| 3510 | 3 | 4 | | | IV-2 | Bmpr1a | 0.97 |
| 3511 | 3 | 4 | | | IV-2 | Bnip1 | 0.96 |
| 3512 | 3 | 4 | | | IV-2 | Bnip3 | 0.76 |
| 3513 | 3 | 4 | | | IV-2 | Bnip3l | 0.87 |
| 3514 | 3 | 4 | | | IV-2 | Bola1 | 0.97 |
| 3515 | 3 | 4 | | | IV-2 | Bop1 | 0.93 |
| 3516 | 3 | 4 | | | IV-2 | Bora | 0.81 |
| 3517 | 3 | 4 | | | IV-2 | Bpgm | 0.86 |
| 3518 | 3 | 4 | | | IV-2 | Bphl | 0.81 |
| 3519 | 3 | 4 | | | IV-2 | Bpifb9b | 0.73 |
| 3520 | 3 | 4 | | | IV-2 | Bpifc | 0.82 |
| 3521 | 3 | 4 | | | IV-2 | Bpnt1 | 0.80 |
| 3522 | 3 | 4 | | | IV-2 | Brd7 | 0.89 |
| 3523 | 3 | 4 | | | IV-2 | Bre | 0.87 |
| 3524 | 3 | 4 | | | IV-2 | Brix1 | 0.74 |
| 3525 | 3 | 4 | | | IV-2 | Brk1 | 0.90 |
| 3526 | 3 | 4 | | | IV-2 | Brpf3 | 0.81 |
| 3527 | 3 | 4 | | | IV-2 | Brwd1 | 0.91 |
| 3528 | 3 | 4 | | | IV-2 | Brwd3 | 0.94 |
| 3529 | 3 | 4 | | | IV-2 | Bscl2 | 0.82 |
| 3530 | 3 | 4 | | | IV-2 | Bsdc1 | 0.90 |
| 3531 | 3 | 4 | | | IV-2 | Bsg | 0.70 |
| 3532 | 3 | 4 | | | IV-2 | Bspry | 0.93 |
| 3533 | 3 | 4 | | | IV-2 | Bst1 | 0.81 |
| 3534 | 3 | 4 | | | IV-2 | Btaf1 | 0.95 |
| 3535 | 3 | 4 | | | IV-2 | Btbd2 | 0.98 |
| 3536 | 3 | 4 | | | IV-2 | Btbd7 | 0.96 |
| 3537 | 3 | 4 | | | IV-2 | Btd | 0.80 |
| 3538 | 3 | 4 | | | IV-2 | Btf3 | 0.86 |
| 3539 | 3 | 4 | | | IV-2 | Btk | 0.72 |
| 3540 | 3 | 4 | | | IV-2 | Btnl4 | 0.97 |
| 3541 | 3 | 4 | | | IV-2 | Btnl5-ps | 0.83 |
| 3542 | 3 | 4 | | | IV-2 | Btnl9 | 0.82 |
| 3543 | 3 | 4 | | | IV-2 | Bub3 | 0.81 |
| 3544 | 3 | 4 | | | IV-2 | Bud13 | 0.86 |
| 3545 | 3 | 4 | | | IV-2 | Bud31 | 0.84 |
| 3546 | 3 | 4 | | | IV-2 | Bves | 0.68 |
| 3547 | 3 | 4 | | | IV-2 | Bysl | 0.97 |
| 3548 | 3 | 4 | | | IV-2 | Bzw1 | 0.99 |
| 3549 | 3 | 4 | | | IV-2 | C030006K11Rik | 0.85 |
| 3550 | 3 | 4 | | | IV-2 | C130036L24Rik | 0.74 |
| 3551 | 3 | 4 | | | IV-2 | C130074G19Rik | 0.78 |
| 3552 | 3 | 4 | | | IV-2 | C130080G10Rik | 0.87 |
| 3553 | 3 | 4 | | | IV-2 | C130083M11Rik | 0.92 |
| 3554 | 3 | 4 | | | IV-2 | C1galt1 | 0.73 |
| 3555 | 3 | 4 | | | IV-2 | C1galt1c1 | 0.75 |
| 3556 | 3 | 4 | | | IV-2 | C1qbp | 0.93 |
| 3557 | 3 | 4 | | | IV-2 | C1qtnf1 | 1.00 |
| 3558 | 3 | 4 | | | IV-2 | C1qtnf2 | 0.95 |
| 3559 | 3 | 4 | | | IV-2 | C1qtnf6 | 0.87 |
| 3560 | 3 | 4 | | | IV-2 | C1qtnf7 | 0.98 |
| 3561 | 3 | 4 | | | IV-2 | C1rl | 0.70 |
| 3562 | 3 | 4 | | | IV-2 | C2 | 0.77 |
| 3563 | 3 | 4 | | | IV-2 | C230052I12Rik | 0.79 |
| 3564 | 3 | 4 | | | IV-2 | C230091D08Rik | 0.92 |
| 3565 | 3 | 4 | | | IV-2 | C2cd2 | 0.69 |
| 3566 | 3 | 4 | | | IV-2 | C2cd2l | 0.85 |
| 3567 | 3 | 4 | | | IV-2 | C2cd3 | 0.81 |
| 3568 | 3 | 4 | | | IV-2 | C2cd4d | 0.97 |
| 3569 | 3 | 4 | | | IV-2 | C2cd5 | 0.96 |
| 3570 | 3 | 4 | | | IV-2 | C330006A16Rik | 0.92 |
| 3571 | 3 | 4 | | | IV-2 | C330007P06Rik | 0.71 |
| 3572 | 3 | 4 | | | IV-2 | C430049B03Rik | 0.87 |
| 3573 | 3 | 4 | | | IV-2 | C77080 | 0.91 |
| 3574 | 3 | 4 | | | IV-2 | C87436 | 0.84 |
| 3575 | 3 | 4 | | | IV-2 | C920021L13Rik | 0.79 |
| 3576 | 3 | 4 | | | IV-2 | C920025E04Rik | 0.71 |
| 3577 | 3 | 4 | | | IV-2 | Caap1 | 0.99 |
| 3578 | 3 | 4 | | | IV-2 | Cab39l | 0.76 |
| 3579 | 3 | 4 | | | IV-2 | Cables1 | 0.87 |
| 3580 | 3 | 4 | | | IV-2 | Cacna1s | 0.94 |
| 3581 | 3 | 4 | | | IV-2 | Cacnb1 | 0.96 |
| 3582 | 3 | 4 | | | IV-2 | Cacng1 | 0.72 |
| 3583 | 3 | 4 | | | IV-2 | Cacng6 | 0.86 |
| 3584 | 3 | 4 | | | IV-2 | Cactin | 0.84 |
| 3585 | 3 | 4 | | | IV-2 | Cacul1 | 1.00 |
| 3586 | 3 | 4 | | | IV-2 | Cacybp | 0.86 |
| 3587 | 3 | 4 | | | IV-2 | Cad | 0.74 |
| 3588 | 3 | 4 | | | IV-2 | Calb1 | 1.00 |
| 3589 | 3 | 4 | | | IV-2 | Calcrl | 0.75 |
| 3590 | 3 | 4 | | | IV-2 | Cald1 | 0.93 |
| 3591 | 3 | 4 | | | IV-2 | Calm1 | 0.82 |
| 3592 | 3 | 4 | | | IV-2 | Calm2 | 0.95 |
| 3593 | 3 | 4 | | | IV-2 | Calm3 | 0.86 |
| 3594 | 3 | 4 | | | IV-2 | Calml4 | 0.80 |
| 3595 | 3 | 4 | | | IV-2 | Calr3 | 0.91 |
| 3596 | 3 | 4 | | | IV-2 | Calu | 0.83 |
| 3597 | 3 | 4 | | | IV-2 | Caly | 0.99 |
| 3598 | 3 | 4 | | | IV-2 | Camk1 | 0.82 |
| 3599 | 3 | 4 | | | IV-2 | Camk2a | 0.92 |
| 3600 | 3 | 4 | | | IV-2 | Camkk1 | 0.91 |
| 3601 | 3 | 4 | | | IV-2 | Camsap3 | 0.97 |
| 3602 | 3 | 4 | | | IV-2 | Cand1 | 0.93 |
| 3603 | 3 | 4 | | | IV-2 | Cand2 | 0.86 |
| 3604 | 3 | 4 | | | IV-2 | Cant1 | 0.94 |
| 3605 | 3 | 4 | | | IV-2 | Canx | 0.77 |
| 3606 | 3 | 4 | | | IV-2 | Cap1 | 0.88 |
| 3607 | 3 | 4 | | | IV-2 | Capn1 | 0.71 |
| 3608 | 3 | 4 | | | IV-2 | Capn15 | 0.92 |
| 3609 | 3 | 4 | | | IV-2 | Capn2 | 0.90 |
| 3610 | 3 | 4 | | | IV-2 | Capn3 | 0.68 |
| 3611 | 3 | 4 | | | IV-2 | Capn5 | 0.91 |
| 3612 | 3 | 4 | | | IV-2 | Capns1 | 0.94 |
| 3613 | 3 | 4 | | | IV-2 | Capns2 | 0.89 |
| 3614 | 3 | 4 | | | IV-2 | Caprin1 | 0.89 |
| 3615 | 3 | 4 | | | IV-2 | Caps | 0.74 |
| 3616 | 3 | 4 | | | IV-2 | Capza1 | 0.78 |
| 3617 | 3 | 4 | | | IV-2 | Capza2 | 0.97 |
| 3618 | 3 | 4 | | | IV-2 | Capzb | 0.80 |
| 3619 | 3 | 4 | | | IV-2 | Car12 | 0.88 |
| 3620 | 3 | 4 | | | IV-2 | Car14 | 0.89 |
| 3621 | 3 | 4 | | | IV-2 | Car5b | 0.96 |
| 3622 | 3 | 4 | | | IV-2 | Car8 | 0.79 |
| 3623 | 3 | 4 | | | IV-2 | Card14 | 0.98 |
| 3624 | 3 | 4 | | | IV-2 | Card6 | 0.76 |
| 3625 | 3 | 4 | | | IV-2 | Carhsp1 | 0.89 |
| 3626 | 3 | 4 | | | IV-2 | Carkd | 0.99 |
| 3627 | 3 | 4 | | | IV-2 | Carns1 | 0.92 |
| 3628 | 3 | 4 | | | IV-2 | Cars2 | 0.98 |
| 3629 | 3 | 4 | | | IV-2 | Casd1 | 0.96 |
| 3630 | 3 | 4 | | | IV-2 | Caskin2 | 0.98 |
| 3631 | 3 | 4 | | | IV-2 | Casp1 | 0.91 |
| 3632 | 3 | 4 | | | IV-2 | Casp2 | 0.89 |
| 3633 | 3 | 4 | | | IV-2 | Casp3 | 0.98 |
| 3634 | 3 | 4 | | | IV-2 | Casp6 | 0.69 |
| 3635 | 3 | 4 | | | IV-2 | Casp7 | 0.97 |
| 3636 | 3 | 4 | | | IV-2 | Casp8 | 0.79 |
| 3637 | 3 | 4 | | | IV-2 | Casp8ap2 | 0.93 |
| 3638 | 3 | 4 | | | IV-2 | Casp9 | 0.97 |
| 3639 | 3 | 4 | | | IV-2 | Casq2 | 0.70 |
| 3640 | 3 | 4 | | | IV-2 | Cass4 | 0.99 |
| 3641 | 3 | 4 | | | IV-2 | Casz1 | 0.88 |
| 3642 | 3 | 4 | | | IV-2 | Cav2 | 0.87 |
| 3643 | 3 | 4 | | | IV-2 | Cav3 | 0.80 |
| 3644 | 3 | 4 | | | IV-2 | Cbl | 0.89 |
| 3645 | 3 | 4 | | | IV-2 | Cblc | 0.71 |
| 3646 | 3 | 4 | | | IV-2 | Cbll1 | 0.99 |

Fig. 45 - 20

| | | | | | | | | | | | | | | |
|---|---|---|---|---|---|---|---|---|---|---|---|---|---|---|
| 3647 | 3 | 4 | | | IV-2 | Cbr3 | 0.82 | 3743 | 3 | 4 | | | IV-2 | Cd40 | 0.85 |
| 3648 | 3 | 4 | | | IV-2 | Cbwd1 | 0.94 | 3744 | 3 | 4 | | | IV-2 | Cd44 | 0.78 |
| 3649 | 3 | 4 | | | IV-2 | Cbx1 | 0.83 | 3745 | 3 | 4 | | | IV-2 | Cd47 | 0.90 |
| 3650 | 3 | 4 | | | IV-2 | Cbx2 | 0.92 | 3746 | 3 | 4 | | | IV-2 | Cd48 | 0.92 |
| 3651 | 3 | 4 | | | IV-2 | Cbx3 | 0.90 | 3747 | 3 | 4 | | | IV-2 | Cd52 | 0.72 |
| 3652 | 3 | 4 | | | IV-2 | Cbx5 | 0.78 | 3748 | 3 | 4 | | | IV-2 | Cd53 | 0.96 |
| 3653 | 3 | 4 | | | IV-2 | Cbx6 | 0.95 | 3749 | 3 | 4 | | | IV-2 | Cd55 | 0.68 |
| 3654 | 3 | 4 | | | IV-2 | Cbx8 | 0.99 | 3750 | 3 | 4 | | | IV-2 | Cd59a | 0.99 |
| 3655 | 3 | 4 | | | IV-2 | Cby1 | 0.94 | 3751 | 3 | 4 | | | IV-2 | Cd59b | 0.85 |
| 3656 | 3 | 4 | | | IV-2 | Ccdc101 | 0.99 | 3752 | 3 | 4 | | | IV-2 | Cd5l | 0.94 |
| 3657 | 3 | 4 | | | IV-2 | Ccdc113 | 0.88 | 3753 | 3 | 4 | | | IV-2 | Cd63 | 0.82 |
| 3658 | 3 | 4 | | | IV-2 | Ccdc117 | 0.82 | 3754 | 3 | 4 | | | IV-2 | Cd79a | 0.71 |
| 3659 | 3 | 4 | | | IV-2 | Ccdc12 | 0.82 | 3755 | 3 | 4 | | | IV-2 | Cd81 | 0.97 |
| 3660 | 3 | 4 | | | IV-2 | Ccdc124 | 0.70 | 3756 | 3 | 4 | | | IV-2 | Cd83 | 0.85 |
| 3661 | 3 | 4 | | | IV-2 | Ccdc125 | 0.96 | 3757 | 3 | 4 | | | IV-2 | Cd93 | 0.78 |
| 3662 | 3 | 4 | | | IV-2 | Ccdc127 | 0.82 | 3758 | 3 | 4 | | | IV-2 | Cd97 | 0.84 |
| 3663 | 3 | 4 | | | IV-2 | Ccdc130 | 0.89 | 3759 | 3 | 4 | | | IV-2 | Cd99l2 | 0.81 |
| 3664 | 3 | 4 | | | IV-2 | Ccdc134 | 0.81 | 3760 | 3 | 4 | | | IV-2 | Cdadc1 | 0.85 |
| 3665 | 3 | 4 | | | IV-2 | Ccdc137 | 0.82 | 3761 | 3 | 4 | | | IV-2 | Cdan1 | 0.93 |
| 3666 | 3 | 4 | | | IV-2 | Ccdc141 | 0.93 | 3762 | 3 | 4 | | | IV-2 | Cdc123 | 0.81 |
| 3667 | 3 | 4 | | | IV-2 | Ccdc18 | 0.76 | 3763 | 3 | 4 | | | IV-2 | Cdc16 | 0.91 |
| 3668 | 3 | 4 | | | IV-2 | Ccdc19 | 0.96 | 3764 | 3 | 4 | | | IV-2 | Cdc23 | 0.99 |
| 3669 | 3 | 4 | | | IV-2 | Ccdc22 | 0.90 | 3765 | 3 | 4 | | | IV-2 | Cdc25a | 0.74 |
| 3670 | 3 | 4 | | | IV-2 | Ccdc23 | 0.91 | 3766 | 3 | 4 | | | IV-2 | Cdc25c | 0.70 |
| 3671 | 3 | 4 | | | IV-2 | Ccdc28a | 0.86 | 3767 | 3 | 4 | | | IV-2 | Cdc26 | 0.92 |
| 3672 | 3 | 4 | | | IV-2 | Ccdc3 | 0.95 | 3768 | 3 | 4 | | | IV-2 | Cdc27 | 0.97 |
| 3673 | 3 | 4 | | | IV-2 | Ccdc34 | 0.76 | 3769 | 3 | 4 | | | IV-2 | Cdc34 | 0.76 |
| 3674 | 3 | 4 | | | IV-2 | Ccdc38 | 0.72 | 3770 | 3 | 4 | | | IV-2 | Cdc37 | 0.81 |
| 3675 | 3 | 4 | | | IV-2 | Ccdc39 | 1.00 | 3771 | 3 | 4 | | | IV-2 | Cdc40 | 0.97 |
| 3676 | 3 | 4 | | | IV-2 | Ccdc43 | 0.78 | 3772 | 3 | 4 | | | IV-2 | Cdc42 | 0.89 |
| 3677 | 3 | 4 | | | IV-2 | Ccdc51 | 0.72 | 3773 | 3 | 4 | | | IV-2 | Cdc42ep1 | 0.84 |
| 3678 | 3 | 4 | | | IV-2 | Ccdc55 | 0.95 | 3774 | 3 | 4 | | | IV-2 | Cdc42ep2 | 0.78 |
| 3679 | 3 | 4 | | | IV-2 | Ccdc58 | 0.80 | 3775 | 3 | 4 | | | IV-2 | Cdc42ep3 | 0.96 |
| 3680 | 3 | 4 | | | IV-2 | Ccdc59 | 0.96 | 3776 | 3 | 4 | | | IV-2 | Cdc42se1 | 0.84 |
| 3681 | 3 | 4 | | | IV-2 | Ccdc6 | 0.91 | 3777 | 3 | 4 | | | IV-2 | Cdc45 | 0.89 |
| 3682 | 3 | 4 | | | IV-2 | Ccdc65 | 0.95 | 3778 | 3 | 4 | | | IV-2 | Cdc5l | 0.86 |
| 3683 | 3 | 4 | | | IV-2 | Ccdc66 | 1.00 | 3779 | 3 | 4 | | | IV-2 | Cdc7 | 0.72 |
| 3684 | 3 | 4 | | | IV-2 | Ccdc71 | 0.99 | 3780 | 3 | 4 | | | IV-2 | Cdc73 | 0.75 |
| 3685 | 3 | 4 | | | IV-2 | Ccdc71l | 0.90 | 3781 | 3 | 4 | | | IV-2 | Cdca4 | 0.82 |
| 3686 | 3 | 4 | | | IV-2 | Ccdc8 | 0.99 | 3782 | 3 | 4 | | | IV-2 | Cdca7 | 0.80 |
| 3687 | 3 | 4 | | | IV-2 | Ccdc80 | 0.85 | 3783 | 3 | 4 | | | IV-2 | Cdca7l | 0.77 |
| 3688 | 3 | 4 | | | IV-2 | Ccdc82 | 0.99 | 3784 | 3 | 4 | | | IV-2 | Cdh1 | 0.80 |
| 3689 | 3 | 4 | | | IV-2 | Ccdc85b | 0.94 | 3785 | 3 | 4 | | | IV-2 | Cdh15 | 0.75 |
| 3690 | 3 | 4 | | | IV-2 | Ccdc85c | 0.89 | 3786 | 3 | 4 | | | IV-2 | Cdh5 | 0.71 |
| 3691 | 3 | 4 | | | IV-2 | Ccdc86 | 0.98 | 3787 | 3 | 4 | | | IV-2 | Cdipt | 0.99 |
| 3692 | 3 | 4 | | | IV-2 | Ccdc88b | 0.89 | 3788 | 3 | 4 | | | IV-2 | Cdk1 | 0.67 |
| 3693 | 3 | 4 | | | IV-2 | Ccdc88c | 0.83 | 3789 | 3 | 4 | | | IV-2 | Cdk16 | 0.91 |
| 3694 | 3 | 4 | | | IV-2 | Ccdc90b | 0.88 | 3790 | 3 | 4 | | | IV-2 | Cdk17 | 0.97 |
| 3695 | 3 | 4 | | | IV-2 | Ccdc91 | 0.87 | 3791 | 3 | 4 | | | IV-2 | Cdk2 | 0.92 |
| 3696 | 3 | 4 | | | IV-2 | Ccdc92 | 0.97 | 3792 | 3 | 4 | | | IV-2 | Cdk20 | 0.96 |
| 3697 | 3 | 4 | | | IV-2 | Ccdc97 | 0.97 | 3793 | 3 | 4 | | | IV-2 | Cdk2ap1 | 0.99 |
| 3698 | 3 | 4 | | | IV-2 | Cchcr1 | 0.74 | 3794 | 3 | 4 | | | IV-2 | Cdk4 | 0.78 |
| 3699 | 3 | 4 | | | IV-2 | Cck | 0.85 | 3795 | 3 | 4 | | | IV-2 | Cdk5rap2 | 0.91 |
| 3700 | 3 | 4 | | | IV-2 | Cckar | 0.75 | 3796 | 3 | 4 | | | IV-2 | Cdk6 | 0.99 |
| 3701 | 3 | 4 | | | IV-2 | Ccl11 | 0.75 | 3797 | 3 | 4 | | | IV-2 | Cdk8 | 0.96 |
| 3702 | 3 | 4 | | | IV-2 | Ccl21b | 0.82 | 3798 | 3 | 4 | | | IV-2 | Cdkal1 | 0.96 |
| 3703 | 3 | 4 | | | IV-2 | Ccl24 | 0.67 | 3799 | 3 | 4 | | | IV-2 | Cdkl1 | 0.84 |
| 3704 | 3 | 4 | | | IV-2 | Ccl25 | 0.73 | 3800 | 3 | 4 | | | IV-2 | Cdkl5 | 0.83 |
| 3705 | 3 | 4 | | | IV-2 | Ccl27a | 0.83 | 3801 | 3 | 4 | | | IV-2 | Cdkn1b | 1.00 |
| 3706 | 3 | 4 | | | IV-2 | Ccm2 | 0.96 | 3802 | 3 | 4 | | | IV-2 | Cdkn1c | 0.75 |
| 3707 | 3 | 4 | | | IV-2 | Ccnd1 | 0.96 | 3803 | 3 | 4 | | | IV-2 | Cdkn2aipnl | 0.99 |
| 3708 | 3 | 4 | | | IV-2 | Ccnd3 | 0.90 | 3804 | 3 | 4 | | | IV-2 | Cdkn2b | 0.85 |
| 3709 | 3 | 4 | | | IV-2 | Ccndbp1 | 0.98 | 3805 | 3 | 4 | | | IV-2 | Cdkn2d | 0.69 |
| 3710 | 3 | 4 | | | IV-2 | Ccng1 | 0.90 | 3806 | 3 | 4 | | | IV-2 | Cdo1 | 0.99 |
| 3711 | 3 | 4 | | | IV-2 | Ccnh | 0.88 | 3807 | 3 | 4 | | | IV-2 | Cdpf1 | 0.69 |
| 3712 | 3 | 4 | | | IV-2 | Ccni | 0.94 | 3808 | 3 | 4 | | | IV-2 | Cds1 | 0.77 |
| 3713 | 3 | 4 | | | IV-2 | Ccnjl | 0.90 | 3809 | 3 | 4 | | | IV-2 | Cdt1 | 0.69 |
| 3714 | 3 | 4 | | | IV-2 | Ccnk | 0.83 | 3810 | 3 | 4 | | | IV-2 | Cdv3 | 0.88 |
| 3715 | 3 | 4 | | | IV-2 | Ccnl1 | 0.97 | 3811 | 3 | 4 | | | IV-2 | Cdyl | 0.91 |
| 3716 | 3 | 4 | | | IV-2 | Ccnt1 | 0.85 | 3812 | 3 | 4 | | | IV-2 | Ceacam1 | 0.72 |
| 3717 | 3 | 4 | | | IV-2 | Ccp110 | 0.98 | 3813 | 3 | 4 | | | IV-2 | Ceacam19 | 0.95 |
| 3718 | 3 | 4 | | | IV-2 | Ccpg1 | 0.95 | 3814 | 3 | 4 | | | IV-2 | Ceacam2 | 0.70 |
| 3719 | 3 | 4 | | | IV-2 | Ccpg1os | 0.97 | 3815 | 3 | 4 | | | IV-2 | Cebpb | 0.96 |
| 3720 | 3 | 4 | | | IV-2 | Ccr4 | 0.74 | 3816 | 3 | 4 | | | IV-2 | Cebpe | 0.74 |
| 3721 | 3 | 4 | | | IV-2 | Ccr5 | 0.89 | 3817 | 3 | 4 | | | IV-2 | Cebpg | 0.96 |
| 3722 | 3 | 4 | | | IV-2 | Ccr8 | 0.85 | 3818 | 3 | 4 | | | IV-2 | Cecr2 | 0.88 |
| 3723 | 3 | 4 | | | IV-2 | Ccrl2 | 0.93 | 3819 | 3 | 4 | | | IV-2 | Cecr5 | 0.78 |
| 3724 | 3 | 4 | | | IV-2 | Ccrn4l | 0.73 | 3820 | 3 | 4 | | | IV-2 | Cel | 0.83 |
| 3725 | 3 | 4 | | | IV-2 | Ccsap | 0.84 | 3821 | 3 | 4 | | | IV-2 | Cela1 | 0.97 |
| 3726 | 3 | 4 | | | IV-2 | Cct3 | 0.87 | 3822 | 3 | 4 | | | IV-2 | Celf1 | 0.92 |
| 3727 | 3 | 4 | | | IV-2 | Cct4 | 0.87 | 3823 | 3 | 4 | | | IV-2 | Cemip | 1.00 |
| 3728 | 3 | 4 | | | IV-2 | Cct5 | 0.88 | 3824 | 3 | 4 | | | IV-2 | Cenpb | 0.99 |
| 3729 | 3 | 4 | | | IV-2 | Cct7 | 0.93 | 3825 | 3 | 4 | | | IV-2 | Cenph | 0.70 |
| 3730 | 3 | 4 | | | IV-2 | Cct8 | 0.96 | 3826 | 3 | 4 | | | IV-2 | Cenpj | 0.78 |
| 3731 | 3 | 4 | | | IV-2 | Cd151 | 0.88 | 3827 | 3 | 4 | | | IV-2 | Cenpo | 0.99 |
| 3732 | 3 | 4 | | | IV-2 | Cd164 | 0.85 | 3828 | 3 | 4 | | | IV-2 | Cenpp | 0.91 |
| 3733 | 3 | 4 | | | IV-2 | Cd248 | 0.93 | 3829 | 3 | 4 | | | IV-2 | Cenpq | 0.71 |
| 3734 | 3 | 4 | | | IV-2 | Cd24a | 0.72 | 3830 | 3 | 4 | | | IV-2 | Cep104 | 0.86 |
| 3735 | 3 | 4 | | | IV-2 | Cd276 | 0.88 | 3831 | 3 | 4 | | | IV-2 | Cep112 | 0.93 |
| 3736 | 3 | 4 | | | IV-2 | Cd2ap | 0.97 | 3832 | 3 | 4 | | | IV-2 | Cep135 | 0.85 |
| 3737 | 3 | 4 | | | IV-2 | Cd302 | 0.75 | 3833 | 3 | 4 | | | IV-2 | Cep152 | 0.96 |
| 3738 | 3 | 4 | | | IV-2 | Cd320 | 0.91 | 3834 | 3 | 4 | | | IV-2 | Cep162 | 0.75 |
| 3739 | 3 | 4 | | | IV-2 | Cd34 | 0.69 | 3835 | 3 | 4 | | | IV-2 | Cep19 | 0.97 |
| 3740 | 3 | 4 | | | IV-2 | Cd36 | 0.89 | 3836 | 3 | 4 | | | IV-2 | Cep192 | 0.82 |
| 3741 | 3 | 4 | | | IV-2 | Cd3e | 0.86 | 3837 | 3 | 4 | | | IV-2 | Cep290 | 0.73 |
| 3742 | 3 | 4 | | | IV-2 | Cd3g | 0.81 | 3838 | 3 | 4 | | | IV-2 | Cep350 | 0.97 |

Fig. 45 - 21

| | | | | | | | |
|---|---|---|---|---|---|---|---|
| 3839 | 3 | 4 | | | IV-2 | Cep57 | 0.99 |
| 3840 | 3 | 4 | | | IV-2 | Cep57l1 | 0.73 |
| 3841 | 3 | 4 | | | IV-2 | Cep72 | 0.98 |
| 3842 | 3 | 4 | | | IV-2 | Cep83 | 0.89 |
| 3843 | 3 | 4 | | | IV-2 | Cep89 | 0.83 |
| 3844 | 3 | 4 | | | IV-2 | Cept1 | 0.75 |
| 3845 | 3 | 4 | | | IV-2 | Cercam | 0.81 |
| 3846 | 3 | 4 | | | IV-2 | Cers2 | 0.90 |
| 3847 | 3 | 4 | | | IV-2 | Cers3 | 0.88 |
| 3848 | 3 | 4 | | | IV-2 | Ces2e | 0.74 |
| 3849 | 3 | 4 | | | IV-2 | Ces2f | 0.74 |
| 3850 | 3 | 4 | | | IV-2 | Cetn2 | 0.79 |
| 3851 | 3 | 4 | | | IV-2 | Cetn3 | 0.88 |
| 3852 | 3 | 4 | | | IV-2 | Cetn4 | 0.94 |
| 3853 | 3 | 4 | | | IV-2 | Cfd | 0.91 |
| 3854 | 3 | 4 | | | IV-2 | Cfdp1 | 0.84 |
| 3855 | 3 | 4 | | | IV-2 | Cfh | 0.82 |
| 3856 | 3 | 4 | | | IV-2 | Cfl1 | 0.86 |
| 3857 | 3 | 4 | | | IV-2 | Cfl2 | 0.93 |
| 3858 | 3 | 4 | | | IV-2 | Cflar | 0.84 |
| 3859 | 3 | 4 | | | IV-2 | Cfp | 0.92 |
| 3860 | 3 | 4 | | | IV-2 | Cftr | 0.85 |
| 3861 | 3 | 4 | | | IV-2 | Cggbp1 | 0.80 |
| 3862 | 3 | 4 | | | IV-2 | Cgn | 0.68 |
| 3863 | 3 | 4 | | | IV-2 | Cgnl1 | 0.88 |
| 3864 | 3 | 4 | | | IV-2 | Cgref1 | 0.83 |
| 3865 | 3 | 4 | | | IV-2 | Cgrrf1 | 0.85 |
| 3866 | 3 | 4 | | | IV-2 | Ch25h | 0.70 |
| 3867 | 3 | 4 | | | IV-2 | Chaf1b | 0.68 |
| 3868 | 3 | 4 | | | IV-2 | Chchd10 | 0.70 |
| 3869 | 3 | 4 | | | IV-2 | Chchd2 | 0.76 |
| 3870 | 3 | 4 | | | IV-2 | Chchd3 | 0.69 |
| 3871 | 3 | 4 | | | IV-2 | Chchd4 | 0.77 |
| 3872 | 3 | 4 | | | IV-2 | Chchd5 | 0.86 |
| 3873 | 3 | 4 | | | IV-2 | Chchd6 | 0.97 |
| 3874 | 3 | 4 | | | IV-2 | Chchd7 | 0.97 |
| 3875 | 3 | 4 | | | IV-2 | Chd1l | 0.94 |
| 3876 | 3 | 4 | | | IV-2 | Chd7 | 0.90 |
| 3877 | 3 | 4 | | | IV-2 | Chek1 | 0.73 |
| 3878 | 3 | 4 | | | IV-2 | Cherp | 0.94 |
| 3879 | 3 | 4 | | | IV-2 | Chid1 | 0.81 |
| 3880 | 3 | 4 | | | IV-2 | Chml | 0.88 |
| 3881 | 3 | 4 | | | IV-2 | Chmp1b | 0.98 |
| 3882 | 3 | 4 | | | IV-2 | Chmp2a | 0.97 |
| 3883 | 3 | 4 | | | IV-2 | Chmp4b | 0.97 |
| 3884 | 3 | 4 | | | IV-2 | Chmp4c | 0.73 |
| 3885 | 3 | 4 | | | IV-2 | Chmp5 | 0.87 |
| 3886 | 3 | 4 | | | IV-2 | Chordc1 | 0.76 |
| 3887 | 3 | 4 | | | IV-2 | Chp1 | 0.85 |
| 3888 | 3 | 4 | | | IV-2 | Chrnb1 | 0.88 |
| 3889 | 3 | 4 | | | IV-2 | Chrnd | 0.97 |
| 3890 | 3 | 4 | | | IV-2 | Chrng | 0.88 |
| 3891 | 3 | 4 | | | IV-2 | Chst11 | 0.90 |
| 3892 | 3 | 4 | | | IV-2 | Chst12 | 0.78 |
| 3893 | 3 | 4 | | | IV-2 | Chst3 | 0.87 |
| 3894 | 3 | 4 | | | IV-2 | Chst5 | 0.75 |
| 3895 | 3 | 4 | | | IV-2 | Chsy1 | 0.99 |
| 3896 | 3 | 4 | | | IV-2 | Chtf18 | 0.69 |
| 3897 | 3 | 4 | | | IV-2 | Chtf8 | 0.76 |
| 3898 | 3 | 4 | | | IV-2 | Chtop | 0.85 |
| 3899 | 3 | 4 | | | IV-2 | Ciao1 | 0.90 |
| 3900 | 3 | 4 | | | IV-2 | Ciapin1 | 0.98 |
| 3901 | 3 | 4 | | | IV-2 | Cib1 | 0.70 |
| 3902 | 3 | 4 | | | IV-2 | Cinp | 0.81 |
| 3903 | 3 | 4 | | | IV-2 | Cipc | 0.97 |
| 3904 | 3 | 4 | | | IV-2 | Cirh1a | 0.90 |
| 3905 | 3 | 4 | | | IV-2 | Cisd1 | 0.80 |
| 3906 | 3 | 4 | | | IV-2 | Ckap2 | 0.98 |
| 3907 | 3 | 4 | | | IV-2 | Ckap4 | 0.81 |
| 3908 | 3 | 4 | | | IV-2 | Ckap5 | 0.90 |
| 3909 | 3 | 4 | | | IV-2 | Cks1brt | 0.68 |
| 3910 | 3 | 4 | | | IV-2 | Clcc1 | 0.96 |
| 3911 | 3 | 4 | | | IV-2 | Clcn3 | 0.99 |
| 3912 | 3 | 4 | | | IV-2 | Clcn5 | 0.89 |
| 3913 | 3 | 4 | | | IV-2 | Cldn1 | 0.83 |
| 3914 | 3 | 4 | | | IV-2 | Cldn10 | 0.85 |
| 3915 | 3 | 4 | | | IV-2 | Cldn12 | 0.98 |
| 3916 | 3 | 4 | | | IV-2 | Cldn14 | 0.78 |
| 3917 | 3 | 4 | | | IV-2 | Cldn15 | 0.79 |
| 3918 | 3 | 4 | | | IV-2 | Cldn25 | 0.87 |
| 3919 | 3 | 4 | | | IV-2 | Cldn3 | 0.85 |
| 3920 | 3 | 4 | | | IV-2 | Cldn5 | 0.92 |
| 3921 | 3 | 4 | | | IV-2 | Cldn8 | 0.80 |
| 3922 | 3 | 4 | | | IV-2 | Clec14a | 0.70 |
| 3923 | 3 | 4 | | | IV-2 | Clec1a | 0.75 |
| 3924 | 3 | 4 | | | IV-2 | Clec1b | 0.85 |
| 3925 | 3 | 4 | | | IV-2 | Clec2d | 0.78 |
| 3926 | 3 | 4 | | | IV-2 | Clec2e | 0.72 |
| 3927 | 3 | 4 | | | IV-2 | Clec4f | 0.81 |
| 3928 | 3 | 4 | | | IV-2 | Clec7a | 0.74 |
| 3929 | 3 | 4 | | | IV-2 | Clec9a | 0.92 |
| 3930 | 3 | 4 | | | IV-2 | Clhc1 | 0.80 |
| 3931 | 3 | 4 | | | IV-2 | Clic1 | 0.89 |
| 3932 | 3 | 4 | | | IV-2 | Clic3 | 0.80 |
| 3933 | 3 | 4 | | | IV-2 | Clic4 | 0.76 |
| 3934 | 3 | 4 | | | IV-2 | Clic6 | 0.78 |
| 3935 | 3 | 4 | | | IV-2 | Clint1 | 0.92 |
| 3936 | 3 | 4 | | | IV-2 | Clk3 | 0.98 |
| 3937 | 3 | 4 | | | IV-2 | Clmn | 0.93 |
| 3938 | 3 | 4 | | | IV-2 | Cln5 | 0.81 |
| 3939 | 3 | 4 | | | IV-2 | Cln8 | 0.74 |
| 3940 | 3 | 4 | | | IV-2 | Clns1a | 0.91 |
| 3941 | 3 | 4 | | | IV-2 | Clp1 | 0.81 |
| 3942 | 3 | 4 | | | IV-2 | Clpb | 0.80 |
| 3943 | 3 | 4 | | | IV-2 | Clpp | 0.97 |
| 3944 | 3 | 4 | | | IV-2 | Clptm1 | 0.99 |
| 3945 | 3 | 4 | | | IV-2 | Clptm1l | 0.99 |
| 3946 | 3 | 4 | | | IV-2 | Clpx | 0.99 |
| 3947 | 3 | 4 | | | IV-2 | Clspn | 0.69 |
| 3948 | 3 | 4 | | | IV-2 | Clta | 0.89 |
| 3949 | 3 | 4 | | | IV-2 | Cltb | 0.95 |
| 3950 | 3 | 4 | | | IV-2 | Cltc | 0.90 |
| 3951 | 3 | 4 | | | IV-2 | Clu | 0.87 |
| 3952 | 3 | 4 | | | IV-2 | Cluh | 0.70 |
| 3953 | 3 | 4 | | | IV-2 | Clybl | 0.69 |
| 3954 | 3 | 4 | | | IV-2 | Cmas | 0.86 |
| 3955 | 3 | 4 | | | IV-2 | Cmc1 | 0.99 |
| 3956 | 3 | 4 | | | IV-2 | Cmkir1 | 0.91 |
| 3957 | 3 | 4 | | | IV-2 | Cmpk1 | 0.95 |
| 3958 | 3 | 4 | | | IV-2 | Cmss1 | 0.84 |
| 3959 | 3 | 4 | | | IV-2 | Cmtm3 | 0.91 |
| 3960 | 3 | 4 | | | IV-2 | Cmtm4 | 0.88 |
| 3961 | 3 | 4 | | | IV-2 | Cmtm6 | 0.76 |
| 3962 | 3 | 4 | | | IV-2 | Cnbp | 0.93 |
| 3963 | 3 | 4 | | | IV-2 | Cndp2 | 0.89 |
| 3964 | 3 | 4 | | | IV-2 | Cnep1r1 | 0.97 |
| 3965 | 3 | 4 | | | IV-2 | Cnfn | 0.92 |
| 3966 | 3 | 4 | | | IV-2 | Cnih1 | 0.99 |
| 3967 | 3 | 4 | | | IV-2 | Cnih4 | 0.91 |
| 3968 | 3 | 4 | | | IV-2 | Cnksr1 | 0.97 |
| 3969 | 3 | 4 | | | IV-2 | Cnn2 | 0.78 |
| 3970 | 3 | 4 | | | IV-2 | Cnn3 | 0.98 |
| 3971 | 3 | 4 | | | IV-2 | Cnnm2 | 0.78 |
| 3972 | 3 | 4 | | | IV-2 | Cnnm4 | 0.75 |
| 3973 | 3 | 4 | | | IV-2 | Cnot1 | 0.88 |
| 3974 | 3 | 4 | | | IV-2 | Cnot11 | 0.93 |
| 3975 | 3 | 4 | | | IV-2 | Cnot2 | 0.97 |
| 3976 | 3 | 4 | | | IV-2 | Cnot3 | 0.88 |
| 3977 | 3 | 4 | | | IV-2 | Cnot4 | 1.00 |
| 3978 | 3 | 4 | | | IV-2 | Cnot6 | 0.96 |
| 3979 | 3 | 4 | | | IV-2 | Cnot6l | 0.98 |
| 3980 | 3 | 4 | | | IV-2 | Cnp | 0.69 |
| 3981 | 3 | 4 | | | IV-2 | Cnpy2 | 0.80 |
| 3982 | 3 | 4 | | | IV-2 | Cnpy3 | 0.89 |
| 3983 | 3 | 4 | | | IV-2 | Cnpy4 | 0.82 |
| 3984 | 3 | 4 | | | IV-2 | Cnr2 | 0.82 |
| 3985 | 3 | 4 | | | IV-2 | Cnst | 0.84 |
| 3986 | 3 | 4 | | | IV-2 | Cntf | 0.83 |
| 3987 | 3 | 4 | | | IV-2 | Cntfr | 0.97 |
| 3988 | 3 | 4 | | | IV-2 | Cntnap1 | 0.71 |
| 3989 | 3 | 4 | | | IV-2 | Cntrl | 0.90 |
| 3990 | 3 | 4 | | | IV-2 | Cntrob | 0.94 |
| 3991 | 3 | 4 | | | IV-2 | Coa5 | 0.77 |
| 3992 | 3 | 4 | | | IV-2 | Coa6 | 0.81 |
| 3993 | 3 | 4 | | | IV-2 | Coa7 | 0.83 |
| 3994 | 3 | 4 | | | IV-2 | Cobl | 0.92 |
| 3995 | 3 | 4 | | | IV-2 | Cobll1 | 0.88 |
| 3996 | 3 | 4 | | | IV-2 | Cog4 | 0.83 |
| 3997 | 3 | 4 | | | IV-2 | Cog6 | 0.84 |
| 3998 | 3 | 4 | | | IV-2 | Cog8 | 0.95 |
| 3999 | 3 | 4 | | | IV-2 | Col11a2 | 0.93 |
| 4000 | 3 | 4 | | | IV-2 | Col16a1 | 0.92 |
| 4001 | 3 | 4 | | | IV-2 | Col18a1 | 0.73 |
| 4002 | 3 | 4 | | | IV-2 | Col1a2 | 0.78 |
| 4003 | 3 | 4 | | | IV-2 | Col22a1 | 0.81 |
| 4004 | 3 | 4 | | | IV-2 | Col3a1 | 0.82 |
| 4005 | 3 | 4 | | | IV-2 | Col4a1 | 0.83 |
| 4006 | 3 | 4 | | | IV-2 | Col4a2 | 0.99 |
| 4007 | 3 | 4 | | | IV-2 | Col4a5 | 0.87 |
| 4008 | 3 | 4 | | | IV-2 | Col4a6 | 0.89 |
| 4009 | 3 | 4 | | | IV-2 | Col5a1 | 0.99 |
| 4010 | 3 | 4 | | | IV-2 | Col5a2 | 0.83 |
| 4011 | 3 | 4 | | | IV-2 | Col6a2 | 0.89 |
| 4012 | 3 | 4 | | | IV-2 | Col6a3 | 0.76 |
| 4013 | 3 | 4 | | | IV-2 | Col6a5 | 0.90 |
| 4014 | 3 | 4 | | | IV-2 | Col6a6 | 0.72 |
| 4015 | 3 | 4 | | | IV-2 | Colec10 | 0.69 |
| 4016 | 3 | 4 | | | IV-2 | Colec12 | 0.99 |
| 4017 | 3 | 4 | | | IV-2 | Commd10 | 0.91 |
| 4018 | 3 | 4 | | | IV-2 | Commd2 | 0.97 |
| 4019 | 3 | 4 | | | IV-2 | Commd3 | 0.91 |
| 4020 | 3 | 4 | | | IV-2 | Commd6 | 0.84 |
| 4021 | 3 | 4 | | | IV-2 | Commd7 | 0.87 |
| 4022 | 3 | 4 | | | IV-2 | Commd9 | 0.84 |
| 4023 | 3 | 4 | | | IV-2 | Comp | 0.99 |
| 4024 | 3 | 4 | | | IV-2 | Comt | 0.89 |
| 4025 | 3 | 4 | | | IV-2 | Comtd1 | 0.76 |
| 4026 | 3 | 4 | | | IV-2 | Copa | 0.91 |
| 4027 | 3 | 4 | | | IV-2 | Copb1 | 0.98 |
| 4028 | 3 | 4 | | | IV-2 | Copb2 | 0.86 |
| 4029 | 3 | 4 | | | IV-2 | Cope | 0.87 |
| 4030 | 3 | 4 | | | IV-2 | Copg2 | 0.98 |

Fig. 45 - 22

| | | | | | | | |
|---|---|---|---|---|---|---|---|
| 4031 | 3 | 4 | | | IV-2 | Cops2 | 0.98 |
| 4032 | 3 | 4 | | | IV-2 | Cops3 | 0.83 |
| 4033 | 3 | 4 | | | IV-2 | Cops4 | 0.95 |
| 4034 | 3 | 4 | | | IV-2 | Cops5 | 0.98 |
| 4035 | 3 | 4 | | | IV-2 | Cops6 | 0.75 |
| 4036 | 3 | 4 | | | IV-2 | Cops7a | 0.82 |
| 4037 | 3 | 4 | | | IV-2 | Cops8 | 0.91 |
| 4038 | 3 | 4 | | | IV-2 | Copz1 | 0.71 |
| 4039 | 3 | 4 | | | IV-2 | Copz2 | 0.83 |
| 4040 | 3 | 4 | | | IV-2 | Coq10b | 0.89 |
| 4041 | 3 | 4 | | | IV-2 | Coq2 | 0.97 |
| 4042 | 3 | 4 | | | IV-2 | Coq3 | 0.75 |
| 4043 | 3 | 4 | | | IV-2 | Coq4 | 0.74 |
| 4044 | 3 | 4 | | | IV-2 | Coq5 | 0.68 |
| 4045 | 3 | 4 | | | IV-2 | Coq6 | 0.80 |
| 4046 | 3 | 4 | | | IV-2 | Coq9 | 0.69 |
| 4047 | 3 | 4 | | | IV-2 | Coro1a | 0.94 |
| 4048 | 3 | 4 | | | IV-2 | Coro1b | 0.85 |
| 4049 | 3 | 4 | | | IV-2 | Coro1c | 0.97 |
| 4050 | 3 | 4 | | | IV-2 | Coro2a | 0.89 |
| 4051 | 3 | 4 | | | IV-2 | Cotl1 | 0.82 |
| 4052 | 3 | 4 | | | IV-2 | Cox10 | 0.93 |
| 4053 | 3 | 4 | | | IV-2 | Cox11 | 0.82 |
| 4054 | 3 | 4 | | | IV-2 | Cox14 | 0.71 |
| 4055 | 3 | 4 | | | IV-2 | Cox15 | 0.90 |
| 4056 | 3 | 4 | | | IV-2 | Cox19 | 0.96 |
| 4057 | 3 | 4 | | | IV-2 | Cox20 | 0.88 |
| 4058 | 3 | 4 | | | IV-2 | Cox4i1 | 0.89 |
| 4059 | 3 | 4 | | | IV-2 | Cox5b | 0.76 |
| 4060 | 3 | 4 | | | IV-2 | Cox6a2 | 0.81 |
| 4061 | 3 | 4 | | | IV-2 | Cox6b1 | 0.74 |
| 4062 | 3 | 4 | | | IV-2 | Cox6c | 0.80 |
| 4063 | 3 | 4 | | | IV-2 | Cox7a2 | 0.73 |
| 4064 | 3 | 4 | | | IV-2 | Cox7c | 0.73 |
| 4065 | 3 | 4 | | | IV-2 | Cox8a | 0.75 |
| 4066 | 3 | 4 | | | IV-2 | Cox8b | 0.86 |
| 4067 | 3 | 4 | | | IV-2 | Cpa1 | 0.88 |
| 4068 | 3 | 4 | | | IV-2 | Cpd | 0.95 |
| 4069 | 3 | 4 | | | IV-2 | Cpeb4 | 0.93 |
| 4070 | 3 | 4 | | | IV-2 | Cpm | 0.79 |
| 4071 | 3 | 4 | | | IV-2 | Cpn2 | 0.84 |
| 4072 | 3 | 4 | | | IV-2 | Cpne1 | 0.85 |
| 4073 | 3 | 4 | | | IV-2 | Cpne3 | 0.88 |
| 4074 | 3 | 4 | | | IV-2 | Cpq | 0.69 |
| 4075 | 3 | 4 | | | IV-2 | Cpsf2 | 0.94 |
| 4076 | 3 | 4 | | | IV-2 | Cpsf3 | 0.97 |
| 4077 | 3 | 4 | | | IV-2 | Cpsf3l | 0.97 |
| 4078 | 3 | 4 | | | IV-2 | Cpt2 | 0.73 |
| 4079 | 3 | 4 | | | IV-2 | Cpxm2 | 0.76 |
| 4080 | 3 | 4 | | | IV-2 | Cpz | 0.69 |
| 4081 | 3 | 4 | | | IV-2 | Cril | 0.83 |
| 4082 | 3 | 4 | | | IV-2 | Crabp1 | 0.69 |
| 4083 | 3 | 4 | | | IV-2 | Crabp2 | 0.86 |
| 4084 | 3 | 4 | | | IV-2 | Crat | 0.73 |
| 4085 | 3 | 4 | | | IV-2 | Creb1 | 0.87 |
| 4086 | 3 | 4 | | | IV-2 | Creb3 | 0.97 |
| 4087 | 3 | 4 | | | IV-2 | Creb3l2 | 0.93 |
| 4088 | 3 | 4 | | | IV-2 | Creb3l3 | 0.83 |
| 4089 | 3 | 4 | | | IV-2 | Crebl2 | 1.00 |
| 4090 | 3 | 4 | | | IV-2 | Creg1 | 0.89 |
| 4091 | 3 | 4 | | | IV-2 | Creld2 | 0.72 |
| 4092 | 3 | 4 | | | IV-2 | Crh | 0.76 |
| 4093 | 3 | 4 | | | IV-2 | Crip1 | 0.79 |
| 4094 | 3 | 4 | | | IV-2 | Crip2 | 0.84 |
| 4095 | 3 | 4 | | | IV-2 | Cript | 0.95 |
| 4096 | 3 | 4 | | | IV-2 | Crk | 0.97 |
| 4097 | 3 | 4 | | | IV-2 | Crkl | 0.96 |
| 4098 | 3 | 4 | | | IV-2 | Crif1 | 0.80 |
| 4099 | 3 | 4 | | | IV-2 | Crls1 | 0.98 |
| 4100 | 3 | 4 | | | IV-2 | Crnde | 1.00 |
| 4101 | 3 | 4 | | | IV-2 | Crnn | 0.94 |
| 4102 | 3 | 4 | | | IV-2 | Crocc | 0.99 |
| 4103 | 3 | 4 | | | IV-2 | Crot | 0.76 |
| 4104 | 3 | 4 | | | IV-2 | Crp | 0.81 |
| 4105 | 3 | 4 | | | IV-2 | Crtap | 0.89 |
| 4106 | 3 | 4 | | | IV-2 | Cryab | 0.79 |
| 4107 | 3 | 4 | | | IV-2 | Crybg3 | 0.85 |
| 4108 | 3 | 4 | | | IV-2 | Crygn | 0.97 |
| 4109 | 3 | 4 | | | IV-2 | Cryl1 | 0.97 |
| 4110 | 3 | 4 | | | IV-2 | Crym | 0.99 |
| 4111 | 3 | 4 | | | IV-2 | Cryz | 0.75 |
| 4112 | 3 | 4 | | | IV-2 | Csde1 | 0.95 |
| 4113 | 3 | 4 | | | IV-2 | Csell | 0.78 |
| 4114 | 3 | 4 | | | IV-2 | Csf1r | 0.83 |
| 4115 | 3 | 4 | | | IV-2 | Csf2ra | 0.88 |
| 4116 | 3 | 4 | | | IV-2 | Csf3r | 0.89 |
| 4117 | 3 | 4 | | | IV-2 | Csk | 0.85 |
| 4118 | 3 | 4 | | | IV-2 | Csnk1a1 | 0.97 |
| 4119 | 3 | 4 | | | IV-2 | Csnk1g2 | 0.91 |
| 4120 | 3 | 4 | | | IV-2 | Csnk2a1 | 0.98 |
| 4121 | 3 | 4 | | | IV-2 | Csnk2b | 0.82 |
| 4122 | 3 | 4 | | | IV-2 | Cspg4 | 0.96 |
| 4123 | 3 | 4 | | | IV-2 | Csrp1 | 0.87 |
| 4124 | 3 | 4 | | | IV-2 | Csrp2 | 0.81 |
| 4125 | 3 | 4 | | | IV-2 | Csrp3 | 0.79 |
| 4126 | 3 | 4 | | | IV-2 | Cst3 | 0.89 |
| 4127 | 3 | 4 | | | IV-2 | Cst6 | 0.86 |
| 4128 | 3 | 4 | | | IV-2 | Cstf1 | 0.97 |
| 4129 | 3 | 4 | | | IV-2 | Ctage5 | 0.96 |
| 4130 | 3 | 4 | | | IV-2 | Ctbp1 | 0.93 |
| 4131 | 3 | 4 | | | IV-2 | Ctcf | 0.89 |
| 4132 | 3 | 4 | | | IV-2 | Ctdnep1 | 0.83 |
| 4133 | 3 | 4 | | | IV-2 | Ctdsp1 | 0.89 |
| 4134 | 3 | 4 | | | IV-2 | Ctdspl | 0.99 |
| 4135 | 3 | 4 | | | IV-2 | Cth | 0.79 |
| 4136 | 3 | 4 | | | IV-2 | Cthrc1 | 0.74 |
| 4137 | 3 | 4 | | | IV-2 | Ctla2b | 0.99 |
| 4138 | 3 | 4 | | | IV-2 | Ctnna1 | 0.86 |
| 4139 | 3 | 4 | | | IV-2 | Ctnna3 | 0.80 |
| 4140 | 3 | 4 | | | IV-2 | Ctnnb1 | 0.95 |
| 4141 | 3 | 4 | | | IV-2 | Ctnnd1 | 0.90 |
| 4142 | 3 | 4 | | | IV-2 | Ctps | 0.96 |
| 4143 | 3 | 4 | | | IV-2 | Ctr9 | 0.97 |
| 4144 | 3 | 4 | | | IV-2 | Ctrb1 | 0.79 |
| 4145 | 3 | 4 | | | IV-2 | Ctsa | 0.91 |
| 4146 | 3 | 4 | | | IV-2 | Ctsb | 0.85 |
| 4147 | 3 | 4 | | | IV-2 | Ctsc | 0.76 |
| 4148 | 3 | 4 | | | IV-2 | Ctsd | 0.85 |
| 4149 | 3 | 4 | | | IV-2 | Ctsk | 0.86 |
| 4150 | 3 | 4 | | | IV-2 | Ctsz | 0.76 |
| 4151 | 3 | 4 | | | IV-2 | Ctu1 | 0.97 |
| 4152 | 3 | 4 | | | IV-2 | Cul2 | 0.92 |
| 4153 | 3 | 4 | | | IV-2 | Cul4a | 0.94 |
| 4154 | 3 | 4 | | | IV-2 | Cul4b | 0.98 |
| 4155 | 3 | 4 | | | IV-2 | Cuta | 0.83 |
| 4156 | 3 | 4 | | | IV-2 | Cutc | 0.92 |
| 4157 | 3 | 4 | | | IV-2 | Cux1 | 0.98 |
| 4158 | 3 | 4 | | | IV-2 | Cwc15 | 0.97 |
| 4159 | 3 | 4 | | | IV-2 | Cx3cr1 | 0.78 |
| 4160 | 3 | 4 | | | IV-2 | Cxcl13 | 0.70 |
| 4161 | 3 | 4 | | | IV-2 | Cxcl14 | 0.95 |
| 4162 | 3 | 4 | | | IV-2 | Cxcr4 | 0.81 |
| 4163 | 3 | 4 | | | IV-2 | Cxxc5 | 0.94 |
| 4164 | 3 | 4 | | | IV-2 | Cyb5 | 0.76 |
| 4165 | 3 | 4 | | | IV-2 | Cyb561a3 | 0.82 |
| 4166 | 3 | 4 | | | IV-2 | Cyb561d2 | 0.91 |
| 4167 | 3 | 4 | | | IV-2 | Cyb5b | 0.82 |
| 4168 | 3 | 4 | | | IV-2 | Cyb5d2 | 0.84 |
| 4169 | 3 | 4 | | | IV-2 | Cyb5r4 | 0.85 |
| 4170 | 3 | 4 | | | IV-2 | Cyba | 0.99 |
| 4171 | 3 | 4 | | | IV-2 | Cybb | 0.96 |
| 4172 | 3 | 4 | | | IV-2 | Cybrd1 | 1.00 |
| 4173 | 3 | 4 | | | IV-2 | Cyfip1 | 0.83 |
| 4174 | 3 | 4 | | | IV-2 | Cyhr1 | 0.97 |
| 4175 | 3 | 4 | | | IV-2 | Cyld | 0.99 |
| 4176 | 3 | 4 | | | IV-2 | Cym | 0.94 |
| 4177 | 3 | 4 | | | IV-2 | Cyp20a1 | 0.94 |
| 4178 | 3 | 4 | | | IV-2 | Cyp2f2 | 0.97 |
| 4179 | 3 | 4 | | | IV-2 | Cyp2j6 | 0.90 |
| 4180 | 3 | 4 | | | IV-2 | Cyp2u1 | 0.96 |
| 4181 | 3 | 4 | | | IV-2 | Cyp2w1 | 0.83 |
| 4182 | 3 | 4 | | | IV-2 | Cyp3a13 | 0.87 |
| 4183 | 3 | 4 | | | IV-2 | Cyp3a16 | 0.85 |
| 4184 | 3 | 4 | | | IV-2 | Cyp4b1 | 0.77 |
| 4185 | 3 | 4 | | | IV-2 | Cyp4f15 | 0.87 |
| 4186 | 3 | 4 | | | IV-2 | Cyp51 | 0.74 |
| 4187 | 3 | 4 | | | IV-2 | Cyp8b1 | 0.89 |
| 4188 | 3 | 4 | | | IV-2 | Cysltr1 | 0.81 |
| 4189 | 3 | 4 | | | IV-2 | Cyth4 | 0.75 |
| 4190 | 3 | 4 | | | IV-2 | Cytip | 0.98 |
| 4191 | 3 | 4 | | | IV-2 | D030028A08Rik | 0.77 |
| 4192 | 3 | 4 | | | IV-2 | D030056L22Rik | 0.76 |
| 4193 | 3 | 4 | | | IV-2 | D11Wsu47e | 0.90 |
| 4194 | 3 | 4 | | | IV-2 | D17H6S53E | 0.68 |
| 4195 | 3 | 4 | | | IV-2 | D17Wsu104e | 0.85 |
| 4196 | 3 | 4 | | | IV-2 | D17Wsu92e | 0.88 |
| 4197 | 3 | 4 | | | IV-2 | D19Bwg1357e | 0.96 |
| 4198 | 3 | 4 | | | IV-2 | D1Ertd622e | 0.77 |
| 4199 | 3 | 4 | | | IV-2 | D1Pas1 | 0.93 |
| 4200 | 3 | 4 | | | IV-2 | D2Wsu81e | 0.91 |
| 4201 | 3 | 4 | | | IV-2 | D2hgdh | 0.83 |
| 4202 | 3 | 4 | | | IV-2 | D330041H03Rik | 0.80 |
| 4203 | 3 | 4 | | | IV-2 | D3Ertd751e | 0.75 |
| 4204 | 3 | 4 | | | IV-2 | D430020J02Rik | 0.79 |
| 4205 | 3 | 4 | | | IV-2 | D5Ertd579e | 0.96 |
| 4206 | 3 | 4 | | | IV-2 | D630003M21Rik | 0.97 |
| 4207 | 3 | 4 | | | IV-2 | D630039A03Rik | 0.79 |
| 4208 | 3 | 4 | | | IV-2 | D6Wsu163e | 0.82 |
| 4209 | 3 | 4 | | | IV-2 | D730001G18Rik | 0.97 |
| 4210 | 3 | 4 | | | IV-2 | D8Ertd738e | 0.80 |
| 4211 | 3 | 4 | | | IV-2 | Daam1 | 0.93 |
| 4212 | 3 | 4 | | | IV-2 | Dact2 | 0.85 |
| 4213 | 3 | 4 | | | IV-2 | Dad1 | 0.83 |
| 4214 | 3 | 4 | | | IV-2 | Dag1 | 0.88 |
| 4215 | 3 | 4 | | | IV-2 | Daglb | 0.89 |
| 4216 | 3 | 4 | | | IV-2 | Dalrd3 | 0.70 |
| 4217 | 3 | 4 | | | IV-2 | Dancr | 1.00 |
| 4218 | 3 | 4 | | | IV-2 | Dand5 | 0.97 |
| 4219 | 3 | 4 | | | IV-2 | Dap | 0.84 |
| 4220 | 3 | 4 | | | IV-2 | Dapk3 | 0.92 |
| 4221 | 3 | 4 | | | IV-2 | Dapp1 | 0.84 |
| 4222 | 3 | 4 | | | IV-2 | Dars | 0.82 |

Fig. 45 - 23

| | | | | | | | |
|---|---|---|---|---|---|---|---|
| 4223 | 3 | 4 | | | IV-2 | Dars2 | 0.84 |
| 4224 | 3 | 4 | | | IV-2 | Dbf4 | 0.75 |
| 4225 | 3 | 4 | | | IV-2 | Dbnl | 0.93 |
| 4226 | 3 | 4 | | | IV-2 | Dbp | 0.90 |
| 4227 | 3 | 4 | | | IV-2 | Dbt | 0.79 |
| 4228 | 3 | 4 | | | IV-2 | Dbx1 | 0.85 |
| 4229 | 3 | 4 | | | IV-2 | Dcaf12 | 0.86 |
| 4230 | 3 | 4 | | | IV-2 | Dcaf17 | 0.96 |
| 4231 | 3 | 4 | | | IV-2 | Dcaf4 | 0.98 |
| 4232 | 3 | 4 | | | IV-2 | Dcakd | 0.90 |
| 4233 | 3 | 4 | | | IV-2 | Dchld1 | 0.96 |
| 4234 | 3 | 4 | | | IV-2 | Dclre1b | 0.90 |
| 4235 | 3 | 4 | | | IV-2 | Dcn | 0.84 |
| 4236 | 3 | 4 | | | IV-2 | Dcp2 | 0.89 |
| 4237 | 3 | 4 | | | IV-2 | Dcpp1 | 0.95 |
| 4238 | 3 | 4 | | | IV-2 | Dcps | 0.78 |
| 4239 | 3 | 4 | | | IV-2 | Dcstamp | 0.90 |
| 4240 | 3 | 4 | | | IV-2 | Dct | 0.97 |
| 4241 | 3 | 4 | | | IV-2 | Dctd | 0.80 |
| 4242 | 3 | 4 | | | IV-2 | Dctn3 | 0.83 |
| 4243 | 3 | 4 | | | IV-2 | Dctn5 | 0.97 |
| 4244 | 3 | 4 | | | IV-2 | Dctpp1 | 0.76 |
| 4245 | 3 | 4 | | | IV-2 | Dcun1d1 | 0.90 |
| 4246 | 3 | 4 | | | IV-2 | Dcun1d2 | 0.70 |
| 4247 | 3 | 4 | | | IV-2 | Dcun1d3 | 0.97 |
| 4248 | 3 | 4 | | | IV-2 | Dcun1d5 | 0.98 |
| 4249 | 3 | 4 | | | IV-2 | Dda1 | 0.93 |
| 4250 | 3 | 4 | | | IV-2 | Ddah1 | 0.99 |
| 4251 | 3 | 4 | | | IV-2 | Ddah2 | 0.93 |
| 4252 | 3 | 4 | | | IV-2 | Ddb1 | 0.95 |
| 4253 | 3 | 4 | | | IV-2 | Ddhd1 | 0.85 |
| 4254 | 3 | 4 | | | IV-2 | Ddi2 | 0.97 |
| 4255 | 3 | 4 | | | IV-2 | Ddit4l | 0.84 |
| 4256 | 3 | 4 | | | IV-2 | Ddost | 0.75 |
| 4257 | 3 | 4 | | | IV-2 | Ddt | 0.71 |
| 4258 | 3 | 4 | | | IV-2 | Ddx11 | 0.88 |
| 4259 | 3 | 4 | | | IV-2 | Ddx18 | 0.87 |
| 4260 | 3 | 4 | | | IV-2 | Ddx23 | 0.93 |
| 4261 | 3 | 4 | | | IV-2 | Ddx27 | 0.95 |
| 4262 | 3 | 4 | | | IV-2 | Ddx31 | 0.92 |
| 4263 | 3 | 4 | | | IV-2 | Ddx3x | 0.94 |
| 4264 | 3 | 4 | | | IV-2 | Ddx41 | 0.82 |
| 4265 | 3 | 4 | | | IV-2 | Ddx47 | 0.78 |
| 4266 | 3 | 4 | | | IV-2 | Ddx6 | 0.92 |
| 4267 | 3 | 4 | | | IV-2 | Deb1 | 0.82 |
| 4268 | 3 | 4 | | | IV-2 | Decr2 | 0.87 |
| 4269 | 3 | 4 | | | IV-2 | Dedd | 0.89 |
| 4270 | 3 | 4 | | | IV-2 | Dedd2 | 0.76 |
| 4271 | 3 | 4 | | | IV-2 | Defa17 | 0.93 |
| 4272 | 3 | 4 | | | IV-2 | Defa3 | 0.77 |
| 4273 | 3 | 4 | | | IV-2 | Defb4 | 0.69 |
| 4274 | 3 | 4 | | | IV-2 | Degs2 | 0.79 |
| 4275 | 3 | 4 | | | IV-2 | Dek | 0.73 |
| 4276 | 3 | 4 | | | IV-2 | Dennd2c | 0.84 |
| 4277 | 3 | 4 | | | IV-2 | Dennd2d | 0.98 |
| 4278 | 3 | 4 | | | IV-2 | Depdc5 | 0.96 |
| 4279 | 3 | 4 | | | IV-2 | Deptor | 0.89 |
| 4280 | 3 | 4 | | | IV-2 | Dera | 0.69 |
| 4281 | 3 | 4 | | | IV-2 | Derl1 | 0.88 |
| 4282 | 3 | 4 | | | IV-2 | Derl2 | 0.91 |
| 4283 | 3 | 4 | | | IV-2 | Desi1 | 0.92 |
| 4284 | 3 | 4 | | | IV-2 | Desi2 | 0.93 |
| 4285 | 3 | 4 | | | IV-2 | Det1 | 0.87 |
| 4286 | 3 | 4 | | | IV-2 | Dexi | 0.92 |
| 4287 | 3 | 4 | | | IV-2 | Dffa | 0.69 |
| 4288 | 3 | 4 | | | IV-2 | Dgat1 | 0.89 |
| 4289 | 3 | 4 | | | IV-2 | Dgkh | 0.89 |
| 4290 | 3 | 4 | | | IV-2 | Dgkz | 0.89 |
| 4291 | 3 | 4 | | | IV-2 | Dguok | 0.74 |
| 4292 | 3 | 4 | | | IV-2 | Dhcr24 | 0.79 |
| 4293 | 3 | 4 | | | IV-2 | Dhdds | 0.91 |
| 4294 | 3 | 4 | | | IV-2 | Dhdh | 0.82 |
| 4295 | 3 | 4 | | | IV-2 | Dhfr | 0.76 |
| 4296 | 3 | 4 | | | IV-2 | Dhh | 0.81 |
| 4297 | 3 | 4 | | | IV-2 | Dhodh | 0.89 |
| 4298 | 3 | 4 | | | IV-2 | Dhrs1 | 0.84 |
| 4299 | 3 | 4 | | | IV-2 | Dhrs13 | 0.81 |
| 4300 | 3 | 4 | | | IV-2 | Dhrs3 | 0.88 |
| 4301 | 3 | 4 | | | IV-2 | Dhrs7b | 0.84 |
| 4302 | 3 | 4 | | | IV-2 | Dhrs9 | 0.93 |
| 4303 | 3 | 4 | | | IV-2 | Dhx15 | 0.91 |
| 4304 | 3 | 4 | | | IV-2 | Dhx16 | 0.96 |
| 4305 | 3 | 4 | | | IV-2 | Dhx29 | 0.83 |
| 4306 | 3 | 4 | | | IV-2 | Dhx32 | 1.00 |
| 4307 | 3 | 4 | | | IV-2 | Dhx33 | 0.97 |
| 4308 | 3 | 4 | | | IV-2 | Dhx37 | 0.98 |
| 4309 | 3 | 4 | | | IV-2 | Diablo | 0.90 |
| 4310 | 3 | 4 | | | IV-2 | Diap1 | 0.96 |
| 4311 | 3 | 4 | | | IV-2 | Dixmt1 | 0.88 |
| 4312 | 3 | 4 | | | IV-2 | Dio2 | 0.95 |
| 4313 | 3 | 4 | | | IV-2 | Dis3l | 0.82 |
| 4314 | 3 | 4 | | | IV-2 | Disp1 | 0.93 |
| 4315 | 3 | 4 | | | IV-2 | Dkc1 | 0.69 |
| 4316 | 3 | 4 | | | IV-2 | Dlat | 0.75 |
| 4317 | 3 | 4 | | | IV-2 | Dlc1 | 0.94 |
| 4318 | 3 | 4 | | | IV-2 | Dld | 0.77 |
| 4319 | 3 | 4 | | | IV-2 | Dleu7 | 0.78 |
| 4320 | 3 | 4 | | | IV-2 | Dlgap5 | 0.68 |
| 4321 | 3 | 4 | | | IV-2 | Dll4 | 0.91 |
| 4322 | 3 | 4 | | | IV-2 | Dlst | 0.75 |
| 4323 | 3 | 4 | | | IV-2 | Dmbt1 | 0.72 |
| 4324 | 3 | 4 | | | IV-2 | Dmc1 | 1.00 |
| 4325 | 3 | 4 | | | IV-2 | Dmd | 0.92 |
| 4326 | 3 | 4 | | | IV-2 | Dmkn | 0.81 |
| 4327 | 3 | 4 | | | IV-2 | Dmpk | 0.71 |
| 4328 | 3 | 4 | | | IV-2 | Dmtf1 | 0.79 |
| 4329 | 3 | 4 | | | IV-2 | Dmxl1 | 0.93 |
| 4330 | 3 | 4 | | | IV-2 | Dna2 | 0.68 |
| 4331 | 3 | 4 | | | IV-2 | Dnaaf2 | 0.79 |
| 4332 | 3 | 4 | | | IV-2 | Dnaja3 | 0.78 |
| 4333 | 3 | 4 | | | IV-2 | Dnaja4 | 0.70 |
| 4334 | 3 | 4 | | | IV-2 | Dnajb1 | 0.80 |
| 4335 | 3 | 4 | | | IV-2 | Dnajb11 | 0.80 |
| 4336 | 3 | 4 | | | IV-2 | Dnajb13 | 0.97 |
| 4337 | 3 | 4 | | | IV-2 | Dnajb14 | 0.95 |
| 4338 | 3 | 4 | | | IV-2 | Dnajb2 | 0.83 |
| 4339 | 3 | 4 | | | IV-2 | Dnajb3 | 0.77 |
| 4340 | 3 | 4 | | | IV-2 | Dnajb4 | 0.87 |
| 4341 | 3 | 4 | | | IV-2 | Dnajb7 | 0.92 |
| 4342 | 3 | 4 | | | IV-2 | Dnajb9 | 0.94 |
| 4343 | 3 | 4 | | | IV-2 | Dnajc1 | 0.98 |
| 4344 | 3 | 4 | | | IV-2 | Dnajc11 | 0.77 |
| 4345 | 3 | 4 | | | IV-2 | Dnajc12 | 0.80 |
| 4346 | 3 | 4 | | | IV-2 | Dnajc13 | 0.91 |
| 4347 | 3 | 4 | | | IV-2 | Dnajc14 | 0.90 |
| 4348 | 3 | 4 | | | IV-2 | Dnajc15 | 0.89 |
| 4349 | 3 | 4 | | | IV-2 | Dnajc16 | 0.97 |
| 4350 | 3 | 4 | | | IV-2 | Dnajc19 | 0.80 |
| 4351 | 3 | 4 | | | IV-2 | Dnajc21 | 1.00 |
| 4352 | 3 | 4 | | | IV-2 | Dnajc24 | 0.82 |
| 4353 | 3 | 4 | | | IV-2 | Dnajc25 | 0.90 |
| 4354 | 3 | 4 | | | IV-2 | Dnajc28 | 0.80 |
| 4355 | 3 | 4 | | | IV-2 | Dnajc3 | 0.77 |
| 4356 | 3 | 4 | | | IV-2 | Dnajc4 | 0.96 |
| 4357 | 3 | 4 | | | IV-2 | Dnajc8 | 0.97 |
| 4358 | 3 | 4 | | | IV-2 | Dnajc9 | 0.74 |
| 4359 | 3 | 4 | | | IV-2 | Dnal1 | 0.98 |
| 4360 | 3 | 4 | | | IV-2 | Dnali1 | 0.96 |
| 4361 | 3 | 4 | | | IV-2 | Dnase1l1 | 0.80 |
| 4362 | 3 | 4 | | | IV-2 | Dnase1l2 | 0.95 |
| 4363 | 3 | 4 | | | IV-2 | Dnase1l3 | 0.88 |
| 4364 | 3 | 4 | | | IV-2 | Dnase2a | 0.77 |
| 4365 | 3 | 4 | | | IV-2 | Dnlz | 0.89 |
| 4366 | 3 | 4 | | | IV-2 | Dnm1l | 0.97 |
| 4367 | 3 | 4 | | | IV-2 | Dnmt1 | 0.82 |
| 4368 | 3 | 4 | | | IV-2 | Dnmt3a | 0.93 |
| 4369 | 3 | 4 | | | IV-2 | Dnmt3b | 0.99 |
| 4370 | 3 | 4 | | | IV-2 | Dnph1 | 0.76 |
| 4371 | 3 | 4 | | | IV-2 | Dock1 | 0.95 |
| 4372 | 3 | 4 | | | IV-2 | Dock11 | 0.91 |
| 4373 | 3 | 4 | | | IV-2 | Dock2 | 0.88 |
| 4374 | 3 | 4 | | | IV-2 | Dock5 | 0.86 |
| 4375 | 3 | 4 | | | IV-2 | Dock8 | 0.81 |
| 4376 | 3 | 4 | | | IV-2 | Dohh | 0.82 |
| 4377 | 3 | 4 | | | IV-2 | Dok1 | 0.98 |
| 4378 | 3 | 4 | | | IV-2 | Dok3 | 0.94 |
| 4379 | 3 | 4 | | | IV-2 | Dok5 | 0.82 |
| 4380 | 3 | 4 | | | IV-2 | Dok7 | 0.97 |
| 4381 | 3 | 4 | | | IV-2 | Dolk | 0.85 |
| 4382 | 3 | 4 | | | IV-2 | Dolpp1 | 0.89 |
| 4383 | 3 | 4 | | | IV-2 | Donson | 0.74 |
| 4384 | 3 | 4 | | | IV-2 | Dopey2 | 0.83 |
| 4385 | 3 | 4 | | | IV-2 | Dot1l | 1.00 |
| 4386 | 3 | 4 | | | IV-2 | Dpcd | 0.82 |
| 4387 | 3 | 4 | | | IV-2 | Dpcr1 | 0.75 |
| 4388 | 3 | 4 | | | IV-2 | Dpf2 | 0.89 |
| 4389 | 3 | 4 | | | IV-2 | Dph6 | 0.87 |
| 4390 | 3 | 4 | | | IV-2 | Dpm2 | 0.86 |
| 4391 | 3 | 4 | | | IV-2 | Dpm3 | 0.84 |
| 4392 | 3 | 4 | | | IV-2 | Dpp3 | 0.97 |
| 4393 | 3 | 4 | | | IV-2 | Dpp4 | 0.71 |
| 4394 | 3 | 4 | | | IV-2 | Dpp7 | 0.77 |
| 4395 | 3 | 4 | | | IV-2 | Dpp9 | 0.91 |
| 4396 | 3 | 4 | | | IV-2 | Dpy30 | 0.71 |
| 4397 | 3 | 4 | | | IV-2 | Dpyd | 0.84 |
| 4398 | 3 | 4 | | | IV-2 | Dqx1 | 0.82 |
| 4399 | 3 | 4 | | | IV-2 | Dr1 | 0.87 |
| 4400 | 3 | 4 | | | IV-2 | Drg1 | 0.86 |
| 4401 | 3 | 4 | | | IV-2 | Drg2 | 0.96 |
| 4402 | 3 | 4 | | | IV-2 | Dsc1 | 0.70 |
| 4403 | 3 | 4 | | | IV-2 | Dsc2 | 0.90 |
| 4404 | 3 | 4 | | | IV-2 | Dsc3 | 0.87 |
| 4405 | 3 | 4 | | | IV-2 | Dscc1 | 0.79 |
| 4406 | 3 | 4 | | | IV-2 | Dscr3 | 0.76 |
| 4407 | 3 | 4 | | | IV-2 | Dse | 0.87 |
| 4408 | 3 | 4 | | | IV-2 | Dsg1b | 0.83 |
| 4409 | 3 | 4 | | | IV-2 | Dsg2 | 0.83 |
| 4410 | 3 | 4 | | | IV-2 | Dsn1 | 0.72 |
| 4411 | 3 | 4 | | | IV-2 | Dsp | 0.85 |
| 4412 | 3 | 4 | | | IV-2 | Dstn | 0.93 |
| 4413 | 3 | 4 | | | IV-2 | Dtl | 0.78 |
| 4414 | 3 | 4 | | | IV-2 | Dtwd1 | 0.98 |

Fig. 45 - 24

| | | | | | | | |
|---|---|---|---|---|---|---|---|
| 4415 | 3 | 4 | | | IV-2 | Dtx2 | 0.86 |
| 4416 | 3 | 4 | | | IV-2 | Dtymk | 0.81 |
| 4417 | 3 | 4 | | | IV-2 | Dupd1 | 0.77 |
| 4418 | 3 | 4 | | | IV-2 | Dus1l | 0.97 |
| 4419 | 3 | 4 | | | IV-2 | Dus2 | 0.85 |
| 4420 | 3 | 4 | | | IV-2 | Dusp10 | 0.82 |
| 4421 | 3 | 4 | | | IV-2 | Dusp13 | 0.99 |
| 4422 | 3 | 4 | | | IV-2 | Dusp14 | 0.86 |
| 4423 | 3 | 4 | | | IV-2 | Dusp16 | 0.89 |
| 4424 | 3 | 4 | | | IV-2 | Dusp19 | 0.76 |
| 4425 | 3 | 4 | | | IV-2 | Dusp22 | 0.85 |
| 4426 | 3 | 4 | | | IV-2 | Dusp23 | 0.79 |
| 4427 | 3 | 4 | | | IV-2 | Dusp27 | 0.69 |
| 4428 | 3 | 4 | | | IV-2 | Dusp3 | 0.82 |
| 4429 | 3 | 4 | | | IV-2 | Dut | 0.75 |
| 4430 | 3 | 4 | | | IV-2 | Dvl1 | 0.96 |
| 4431 | 3 | 4 | | | IV-2 | Dxo | 0.86 |
| 4432 | 3 | 4 | | | IV-2 | Dym | 0.87 |
| 4433 | 3 | 4 | | | IV-2 | Dync2li1 | 0.77 |
| 4434 | 3 | 4 | | | IV-2 | Dynlt1 | 0.73 |
| 4435 | 3 | 4 | | | IV-2 | Dynlrb1 | 0.93 |
| 4436 | 3 | 4 | | | IV-2 | Dynlt1b | 1.00 |
| 4437 | 3 | 4 | | | IV-2 | Dynlt1c | 1.00 |
| 4438 | 3 | 4 | | | IV-2 | Dynlt3 | 0.83 |
| 4439 | 3 | 4 | | | IV-2 | Dyrk1b | 0.73 |
| 4440 | 3 | 4 | | | IV-2 | Dyrk3 | 0.95 |
| 4441 | 3 | 4 | | | IV-2 | Dysf | 0.89 |
| 4442 | 3 | 4 | | | IV-2 | Dzip3 | 0.86 |
| 4443 | 3 | 4 | | | IV-2 | E030024N20Rik | 0.75 |
| 4444 | 3 | 4 | | | IV-2 | E130201H02Rik | 0.95 |
| 4445 | 3 | 4 | | | IV-2 | E2f1 | 0.78 |
| 4446 | 3 | 4 | | | IV-2 | E2f3 | 0.92 |
| 4447 | 3 | 4 | | | IV-2 | E2f5 | 0.91 |
| 4448 | 3 | 4 | | | IV-2 | E2f6 | 0.95 |
| 4449 | 3 | 4 | | | IV-2 | E2f7 | 0.76 |
| 4450 | 3 | 4 | | | IV-2 | E330033B04Rik | 0.88 |
| 4451 | 3 | 4 | | | IV-2 | Eaf1 | 0.87 |
| 4452 | 3 | 4 | | | IV-2 | Eapp | 0.84 |
| 4453 | 3 | 4 | | | IV-2 | Ear2 | 0.82 |
| 4454 | 3 | 4 | | | IV-2 | Ears2 | 0.91 |
| 4455 | 3 | 4 | | | IV-2 | Ebag9 | 0.99 |
| 4456 | 3 | 4 | | | IV-2 | Ebf2 | 0.90 |
| 4457 | 3 | 4 | | | IV-2 | Ebpl | 0.93 |
| 4458 | 3 | 4 | | | IV-2 | Ecd | 0.97 |
| 4459 | 3 | 4 | | | IV-2 | Ece2 | 0.84 |
| 4460 | 3 | 4 | | | IV-2 | Ech1 | 0.97 |
| 4461 | 3 | 4 | | | IV-2 | Echdc2 | 0.90 |
| 4462 | 3 | 4 | | | IV-2 | Echs1 | 0.76 |
| 4463 | 3 | 4 | | | IV-2 | Ecsit | 0.91 |
| 4464 | 3 | 4 | | | IV-2 | Edaradd | 0.72 |
| 4465 | 3 | 4 | | | IV-2 | Edem1 | 0.76 |
| 4466 | 3 | 4 | | | IV-2 | Edem2 | 0.86 |
| 4467 | 3 | 4 | | | IV-2 | Edem3 | 0.97 |
| 4468 | 3 | 4 | | | IV-2 | Edf1 | 0.70 |
| 4469 | 3 | 4 | | | IV-2 | Edn3 | 0.92 |
| 4470 | 3 | 4 | | | IV-2 | Ednra | 0.99 |
| 4471 | 3 | 4 | | | IV-2 | Edrf1 | 0.85 |
| 4472 | 3 | 4 | | | IV-2 | Eed | 0.81 |
| 4473 | 3 | 4 | | | IV-2 | Eef1a2 | 0.97 |
| 4474 | 3 | 4 | | | IV-2 | Eef1e1 | 0.91 |
| 4475 | 3 | 4 | | | IV-2 | Eef1g | 0.78 |
| 4476 | 3 | 4 | | | IV-2 | Eef2k | 0.93 |
| 4477 | 3 | 4 | | | IV-2 | Eefsec | 0.97 |
| 4478 | 3 | 4 | | | IV-2 | Eepd1 | 0.98 |
| 4479 | 3 | 4 | | | IV-2 | Efcab11 | 0.75 |
| 4480 | 3 | 4 | | | IV-2 | Efcab14 | 0.78 |
| 4481 | 3 | 4 | | | IV-2 | Efcab4a | 1.00 |
| 4482 | 3 | 4 | | | IV-2 | Efcab7 | 0.90 |
| 4483 | 3 | 4 | | | IV-2 | Efemp1 | 0.78 |
| 4484 | 3 | 4 | | | IV-2 | Efemp2 | 0.72 |
| 4485 | 3 | 4 | | | IV-2 | Efhc1 | 0.95 |
| 4486 | 3 | 4 | | | IV-2 | Efhd2 | 0.96 |
| 4487 | 3 | 4 | | | IV-2 | Efna1 | 0.95 |
| 4488 | 3 | 4 | | | IV-2 | Efna3 | 0.95 |
| 4489 | 3 | 4 | | | IV-2 | Efnb1 | 0.99 |
| 4490 | 3 | 4 | | | IV-2 | Efr3a | 0.96 |
| 4491 | 3 | 4 | | | IV-2 | Eftud1 | 1.00 |
| 4492 | 3 | 4 | | | IV-2 | Eftud2 | 0.84 |
| 4493 | 3 | 4 | | | IV-2 | Egfbp2 | 0.77 |
| 4494 | 3 | 4 | | | IV-2 | Egfl7 | 0.78 |
| 4495 | 3 | 4 | | | IV-2 | Egflam | 0.90 |
| 4496 | 3 | 4 | | | IV-2 | Egln1 | 0.79 |
| 4497 | 3 | 4 | | | IV-2 | Egln2 | 0.96 |
| 4498 | 3 | 4 | | | IV-2 | Egln3 | 0.74 |
| 4499 | 3 | 4 | | | IV-2 | Egr2 | 0.90 |
| 4500 | 3 | 4 | | | IV-2 | Egr3 | 0.68 |
| 4501 | 3 | 4 | | | IV-2 | Ehd1 | 0.84 |
| 4502 | 3 | 4 | | | IV-2 | Ehd4 | 0.86 |
| 4503 | 3 | 4 | | | IV-2 | Ehf | 0.79 |
| 4504 | 3 | 4 | | | IV-2 | Eif1ad | 0.84 |
| 4505 | 3 | 4 | | | IV-2 | Eif1ax | 0.87 |
| 4506 | 3 | 4 | | | IV-2 | Eif1b | 0.93 |
| 4507 | 3 | 4 | | | IV-2 | Eif2a | 0.91 |
| 4508 | 3 | 4 | | | IV-2 | Eif2ak1 | 0.74 |
| 4509 | 3 | 4 | | | IV-2 | Eif2ak3 | 0.97 |
| 4510 | 3 | 4 | | | IV-2 | Eif2b1 | 0.93 |
| 4511 | 3 | 4 | | | IV-2 | Eif2b2 | 0.95 |
| 4512 | 3 | 4 | | | IV-2 | Eif2b4 | 0.97 |
| 4513 | 3 | 4 | | | IV-2 | Eif2b5 | 0.96 |
| 4514 | 3 | 4 | | | IV-2 | Eif2s1 | 0.81 |
| 4515 | 3 | 4 | | | IV-2 | Eif2s3x | 0.67 |
| 4516 | 3 | 4 | | | IV-2 | Eif3a | 0.90 |
| 4517 | 3 | 4 | | | IV-2 | Eif3b | 0.96 |
| 4518 | 3 | 4 | | | IV-2 | Eif3d | 0.92 |
| 4519 | 3 | 4 | | | IV-2 | Eif3g | 0.91 |
| 4520 | 3 | 4 | | | IV-2 | Eif3i | 0.93 |
| 4521 | 3 | 4 | | | IV-2 | Eif4a1 | 0.90 |
| 4522 | 3 | 4 | | | IV-2 | Eif4a2 | 0.87 |
| 4523 | 3 | 4 | | | IV-2 | Eif4e | 0.78 |
| 4524 | 3 | 4 | | | IV-2 | Eif4e2 | 0.88 |
| 4525 | 3 | 4 | | | IV-2 | Eif4ebp2 | 0.79 |
| 4526 | 3 | 4 | | | IV-2 | Eif4g1 | 0.89 |
| 4527 | 3 | 4 | | | IV-2 | Eif4h | 0.92 |
| 4528 | 3 | 4 | | | IV-2 | Eif5a | 0.75 |
| 4529 | 3 | 4 | | | IV-2 | Eif5b | 0.97 |
| 4530 | 3 | 4 | | | IV-2 | Elac2 | 0.90 |
| 4531 | 3 | 4 | | | IV-2 | Elavl1 | 0.96 |
| 4532 | 3 | 4 | | | IV-2 | Elf2 | 1.00 |
| 4533 | 3 | 4 | | | IV-2 | Elf3 | 0.75 |
| 4534 | 3 | 4 | | | IV-2 | Elf4 | 0.85 |
| 4535 | 3 | 4 | | | IV-2 | Elf5 | 0.86 |
| 4536 | 3 | 4 | | | IV-2 | Elk4 | 0.94 |
| 4537 | 3 | 4 | | | IV-2 | Elmo3 | 0.82 |
| 4538 | 3 | 4 | | | IV-2 | Elmsan1 | 0.89 |
| 4539 | 3 | 4 | | | IV-2 | Elof1 | 0.88 |
| 4540 | 3 | 4 | | | IV-2 | Elovl1 | 0.69 |
| 4541 | 3 | 4 | | | IV-2 | Elovl5 | 0.88 |
| 4542 | 3 | 4 | | | IV-2 | Elovl6 | 0.72 |
| 4543 | 3 | 4 | | | IV-2 | Elp5 | 0.82 |
| 4544 | 3 | 4 | | | IV-2 | Eltd1 | 0.91 |
| 4545 | 3 | 4 | | | IV-2 | Emb | 0.97 |
| 4546 | 3 | 4 | | | IV-2 | Emc10 | 0.90 |
| 4547 | 3 | 4 | | | IV-2 | Emc2 | 0.82 |
| 4548 | 3 | 4 | | | IV-2 | Emc3 | 0.89 |
| 4549 | 3 | 4 | | | IV-2 | Emc4 | 0.93 |
| 4550 | 3 | 4 | | | IV-2 | Emc6 | 0.86 |
| 4551 | 3 | 4 | | | IV-2 | Emc9 | 0.84 |
| 4552 | 3 | 4 | | | IV-2 | Emcn | 0.84 |
| 4553 | 3 | 4 | | | IV-2 | Emg1 | 0.81 |
| 4554 | 3 | 4 | | | IV-2 | Emid1 | 0.85 |
| 4555 | 3 | 4 | | | IV-2 | Emilin1 | 0.80 |
| 4556 | 3 | 4 | | | IV-2 | Emilin2 | 0.75 |
| 4557 | 3 | 4 | | | IV-2 | Eml1 | 0.84 |
| 4558 | 3 | 4 | | | IV-2 | Emp1 | 0.93 |
| 4559 | 3 | 4 | | | IV-2 | Emp2 | 0.76 |
| 4560 | 3 | 4 | | | IV-2 | Emp3 | 0.94 |
| 4561 | 3 | 4 | | | IV-2 | Endod1 | 0.74 |
| 4562 | 3 | 4 | | | IV-2 | Endog | 0.82 |
| 4563 | 3 | 4 | | | IV-2 | Eng | 0.85 |
| 4564 | 3 | 4 | | | IV-2 | Enkd1 | 0.90 |
| 4565 | 3 | 4 | | | IV-2 | Eno1 | 0.87 |
| 4566 | 3 | 4 | | | IV-2 | Eno1b | 0.71 |
| 4567 | 3 | 4 | | | IV-2 | Enoph1 | 0.95 |
| 4568 | 3 | 4 | | | IV-2 | Enox2 | 0.95 |
| 4569 | 3 | 4 | | | IV-2 | Enpep | 0.73 |
| 4570 | 3 | 4 | | | IV-2 | Enpp3 | 0.88 |
| 4571 | 3 | 4 | | | IV-2 | Enthd2 | 0.89 |
| 4572 | 3 | 4 | | | IV-2 | Entpd5 | 0.82 |
| 4573 | 3 | 4 | | | IV-2 | Eogt | 0.97 |
| 4574 | 3 | 4 | | | IV-2 | Epas1 | 0.97 |
| 4575 | 3 | 4 | | | IV-2 | Epb4.1 | 0.80 |
| 4576 | 3 | 4 | | | IV-2 | Epb4.1l2 | 0.88 |
| 4577 | 3 | 4 | | | IV-2 | Epb4.1l5 | 0.90 |
| 4578 | 3 | 4 | | | IV-2 | Epdr1 | 1.00 |
| 4579 | 3 | 4 | | | IV-2 | Epha1 | 0.99 |
| 4580 | 3 | 4 | | | IV-2 | Epha2 | 0.94 |
| 4581 | 3 | 4 | | | IV-2 | Ephx3 | 0.77 |
| 4582 | 3 | 4 | | | IV-2 | Epn1 | 0.93 |
| 4583 | 3 | 4 | | | IV-2 | Epn3 | 0.90 |
| 4584 | 3 | 4 | | | IV-2 | Eppk1 | 0.71 |
| 4585 | 3 | 4 | | | IV-2 | Eps15l1 | 0.93 |
| 4586 | 3 | 4 | | | IV-2 | Eps8 | 0.99 |
| 4587 | 3 | 4 | | | IV-2 | Eps8l2 | 0.84 |
| 4588 | 3 | 4 | | | IV-2 | Eral1 | 0.82 |
| 4589 | 3 | 4 | | | IV-2 | Erap1 | 0.94 |
| 4590 | 3 | 4 | | | IV-2 | Erbb2 | 0.94 |
| 4591 | 3 | 4 | | | IV-2 | Erg | 0.98 |
| 4592 | 3 | 4 | | | IV-2 | Ergic2 | 0.85 |
| 4593 | 3 | 4 | | | IV-2 | Ergic3 | 0.99 |
| 4594 | 3 | 4 | | | IV-2 | Erh | 0.88 |
| 4595 | 3 | 4 | | | IV-2 | Eri1 | 0.72 |
| 4596 | 3 | 4 | | | IV-2 | Eri2 | 0.93 |
| 4597 | 3 | 4 | | | IV-2 | Erlin1 | 0.76 |
| 4598 | 3 | 4 | | | IV-2 | Ermp1 | 0.78 |
| 4599 | 3 | 4 | | | IV-2 | Ero1l | 0.75 |
| 4600 | 3 | 4 | | | IV-2 | Ero1lb | 0.90 |
| 4601 | 3 | 4 | | | IV-2 | Erp29 | 0.82 |
| 4602 | 3 | 4 | | | IV-2 | Erp44 | 0.78 |
| 4603 | 3 | 4 | | | IV-2 | Esam | 0.72 |
| 4604 | 3 | 4 | | | IV-2 | Esd | 0.81 |
| 4605 | 3 | 4 | | | IV-2 | Espn | 0.89 |
| 4606 | 3 | 4 | | | IV-2 | Esrp1 | 0.82 |

Fig. 45 - 25

| | | | | | | | | | | | | | | |
|---|---|---|---|---|---|---|---|---|---|---|---|---|---|---|
| 4607 | 3 | 4 | | | IV-2 | Esrp2 | 0.74 | 4703 | 3 | 4 | | | IV-2 | Fam214b | 0.84 |
| 4608 | 3 | 4 | | | IV-2 | Esrra | 0.74 | 4704 | 3 | 4 | | | IV-2 | Fam217b | 0.91 |
| 4609 | 3 | 4 | | | IV-2 | Esyt2 | 0.85 | 4705 | 3 | 4 | | | IV-2 | Fam219b | 0.91 |
| 4610 | 3 | 4 | | | IV-2 | Esyt3 | 0.75 | 4706 | 3 | 4 | | | IV-2 | Fam220a | 0.82 |
| 4611 | 3 | 4 | | | IV-2 | Etaa1 | 0.75 | 4707 | 3 | 4 | | | IV-2 | Fam222b | 0.99 |
| 4612 | 3 | 4 | | | IV-2 | Etf1 | 0.93 | 4708 | 3 | 4 | | | IV-2 | Fam25c | 0.68 |
| 4613 | 3 | 4 | | | IV-2 | Etfb | 0.70 | 4709 | 3 | 4 | | | IV-2 | Fam35a | 0.96 |
| 4614 | 3 | 4 | | | IV-2 | Etfdh | 0.81 | 4710 | 3 | 4 | | | IV-2 | Fam43a | 0.99 |
| 4615 | 3 | 4 | | | IV-2 | Ethe1 | 0.78 | 4711 | 3 | 4 | | | IV-2 | Fam45a | 0.93 |
| 4616 | 3 | 4 | | | IV-2 | Etohd2 | 0.84 | 4712 | 3 | 4 | | | IV-2 | Fam46c | 0.91 |
| 4617 | 3 | 4 | | | IV-2 | Etohi1 | 0.92 | 4713 | 3 | 4 | | | IV-2 | Fam50a | 0.87 |
| 4618 | 3 | 4 | | | IV-2 | Ets1 | 0.79 | 4714 | 3 | 4 | | | IV-2 | Fam53c | 0.89 |
| 4619 | 3 | 4 | | | IV-2 | Ets2 | 0.94 | 4715 | 3 | 4 | | | IV-2 | Fam63b | 0.81 |
| 4620 | 3 | 4 | | | IV-2 | Etv6 | 0.92 | 4716 | 3 | 4 | | | IV-2 | Fam69a | 1.00 |
| 4621 | 3 | 4 | | | IV-2 | Eva1a | 0.70 | 4717 | 3 | 4 | | | IV-2 | Fam72a | 0.90 |
| 4622 | 3 | 4 | | | IV-2 | Evi2a | 0.86 | 4718 | 3 | 4 | | | IV-2 | Fam73b | 0.73 |
| 4623 | 3 | 4 | | | IV-2 | Evi2b | 0.79 | 4719 | 3 | 4 | | | IV-2 | Fam81a | 0.90 |
| 4624 | 3 | 4 | | | IV-2 | Evpl | 0.68 | 4720 | 3 | 4 | | | IV-2 | Fam83b | 0.77 |
| 4625 | 3 | 4 | | | IV-2 | Exd2 | 0.88 | 4721 | 3 | 4 | | | IV-2 | Fam83h | 0.90 |
| 4626 | 3 | 4 | | | IV-2 | Exo1 | 0.77 | 4722 | 3 | 4 | | | IV-2 | Fam84b | 0.90 |
| 4627 | 3 | 4 | | | IV-2 | Exo5 | 0.89 | 4723 | 3 | 4 | | | IV-2 | Fam86 | 0.90 |
| 4628 | 3 | 4 | | | IV-2 | Exoc3l | 0.85 | 4724 | 3 | 4 | | | IV-2 | Fam96a | 0.73 |
| 4629 | 3 | 4 | | | IV-2 | Exoc4 | 0.88 | 4725 | 3 | 4 | | | IV-2 | Fam98a | 0.79 |
| 4630 | 3 | 4 | | | IV-2 | Exoc6 | 0.77 | 4726 | 3 | 4 | | | IV-2 | Fancb | 0.86 |
| 4631 | 3 | 4 | | | IV-2 | Exoc7 | 0.90 | 4727 | 3 | 4 | | | IV-2 | Fancf | 0.92 |
| 4632 | 3 | 4 | | | IV-2 | Exoc8 | 0.79 | 4728 | 3 | 4 | | | IV-2 | Fancg | 0.92 |
| 4633 | 3 | 4 | | | IV-2 | Exosc10 | 0.97 | 4729 | 3 | 4 | | | IV-2 | Far1 | 0.91 |
| 4634 | 3 | 4 | | | IV-2 | Exosc2 | 0.91 | 4730 | 3 | 4 | | | IV-2 | Farp2 | 0.82 |
| 4635 | 3 | 4 | | | IV-2 | Exosc3 | 0.75 | 4731 | 3 | 4 | | | IV-2 | Fars2 | 0.72 |
| 4636 | 3 | 4 | | | IV-2 | Exosc6 | 0.80 | 4732 | 3 | 4 | | | IV-2 | Farsa | 0.82 |
| 4637 | 3 | 4 | | | IV-2 | Exosc7 | 0.76 | 4733 | 3 | 4 | | | IV-2 | Farsb | 0.75 |
| 4638 | 3 | 4 | | | IV-2 | Exosc8 | 0.83 | 4734 | 3 | 4 | | | IV-2 | Fastk | 0.86 |
| 4639 | 3 | 4 | | | IV-2 | Exph5 | 0.75 | 4735 | 3 | 4 | | | IV-2 | Fastkd1 | 0.77 |
| 4640 | 3 | 4 | | | IV-2 | Extl3 | 0.98 | 4736 | 3 | 4 | | | IV-2 | Fastkd5 | 0.85 |
| 4641 | 3 | 4 | | | IV-2 | Eya3 | 0.84 | 4737 | 3 | 4 | | | IV-2 | Fbl | 0.84 |
| 4642 | 3 | 4 | | | IV-2 | Ezh2 | 0.77 | 4738 | 3 | 4 | | | IV-2 | Fbln7 | 0.90 |
| 4643 | 3 | 4 | | | IV-2 | Ezr | 0.93 | 4739 | 3 | 4 | | | IV-2 | Fbn1 | 0.88 |
| 4644 | 3 | 4 | | | IV-2 | F11r | 0.84 | 4740 | 3 | 4 | | | IV-2 | Fbp2 | 0.71 |
| 4645 | 3 | 4 | | | IV-2 | F13a1 | 0.76 | 4741 | 3 | 4 | | | IV-2 | Fbxl14 | 0.88 |
| 4646 | 3 | 4 | | | IV-2 | F2rl1 | 0.98 | 4742 | 3 | 4 | | | IV-2 | Fbxl18 | 0.99 |
| 4647 | 3 | 4 | | | IV-2 | F3 | 0.70 | 4743 | 3 | 4 | | | IV-2 | Fbxo16 | 0.96 |
| 4648 | 3 | 4 | | | IV-2 | F630028O10Rik | 0.89 | 4744 | 3 | 4 | | | IV-2 | Fbxo18 | 0.89 |
| 4649 | 3 | 4 | | | IV-2 | F7 | 0.78 | 4745 | 3 | 4 | | | IV-2 | Fbxo3 | 0.90 |
| 4650 | 3 | 4 | | | IV-2 | F8 | 0.97 | 4746 | 3 | 4 | | | IV-2 | Fbxo33 | 0.84 |
| 4651 | 3 | 4 | | | IV-2 | Fadd | 0.75 | 4747 | 3 | 4 | | | IV-2 | Fbxo36 | 0.79 |
| 4652 | 3 | 4 | | | IV-2 | Fads1 | 0.82 | 4748 | 3 | 4 | | | IV-2 | Fbxo40 | 0.82 |
| 4653 | 3 | 4 | | | IV-2 | Fads2 | 0.80 | 4749 | 3 | 4 | | | IV-2 | Fbxo42 | 0.92 |
| 4654 | 3 | 4 | | | IV-2 | Fads3 | 0.86 | 4750 | 3 | 4 | | | IV-2 | Fbxo45 | 0.99 |
| 4655 | 3 | 4 | | | IV-2 | Fads6 | 0.97 | 4751 | 3 | 4 | | | IV-2 | Fbxo46 | 0.87 |
| 4656 | 3 | 4 | | | IV-2 | Faf2 | 0.95 | 4752 | 3 | 4 | | | IV-2 | Fbxo8 | 0.94 |
| 4657 | 3 | 4 | | | IV-2 | Fah | 0.87 | 4753 | 3 | 4 | | | IV-2 | Fbxo9 | 0.91 |
| 4658 | 3 | 4 | | | IV-2 | Fahd1 | 0.69 | 4754 | 3 | 4 | | | IV-2 | Fbxw4 | 0.92 |
| 4659 | 3 | 4 | | | IV-2 | Fam102a | 0.91 | 4755 | 3 | 4 | | | IV-2 | Fbxw8 | 0.99 |
| 4660 | 3 | 4 | | | IV-2 | Fam103a1 | 0.97 | 4756 | 3 | 4 | | | IV-2 | Fcer1g | 0.89 |
| 4661 | 3 | 4 | | | IV-2 | Fam104a | 0.77 | 4757 | 3 | 4 | | | IV-2 | Fcgrt | 0.82 |
| 4662 | 3 | 4 | | | IV-2 | Fam107b | 0.98 | 4758 | 3 | 4 | | | IV-2 | Fcho1 | 0.94 |
| 4663 | 3 | 4 | | | IV-2 | Fam109a | 0.95 | 4759 | 3 | 4 | | | IV-2 | Fcho2 | 1.00 |
| 4664 | 3 | 4 | | | IV-2 | Fam109b | 0.74 | 4760 | 3 | 4 | | | IV-2 | Fcna | 0.71 |
| 4665 | 3 | 4 | | | IV-2 | Fam110a | 0.99 | 4761 | 3 | 4 | | | IV-2 | Fdft1 | 0.83 |
| 4666 | 3 | 4 | | | IV-2 | Fam110c | 0.94 | 4762 | 3 | 4 | | | IV-2 | Fdx1 | 0.77 |
| 4667 | 3 | 4 | | | IV-2 | Fam114a1 | 0.82 | 4763 | 3 | 4 | | | IV-2 | Fdxacb1 | 0.83 |
| 4668 | 3 | 4 | | | IV-2 | Fam115c | 0.72 | 4764 | 3 | 4 | | | IV-2 | Fem1a | 0.92 |
| 4669 | 3 | 4 | | | IV-2 | Fam118b | 0.99 | 4765 | 3 | 4 | | | IV-2 | Fem1b | 0.83 |
| 4670 | 3 | 4 | | | IV-2 | Fam120a | 0.87 | 4766 | 3 | 4 | | | IV-2 | Fem1c | 0.97 |
| 4671 | 3 | 4 | | | IV-2 | Fam120c | 0.95 | 4767 | 3 | 4 | | | IV-2 | Fermt1 | 0.87 |
| 4672 | 3 | 4 | | | IV-2 | Fam122b | 0.92 | 4768 | 3 | 4 | | | IV-2 | Fermt2 | 0.84 |
| 4673 | 3 | 4 | | | IV-2 | Fam124b | 0.91 | 4769 | 3 | 4 | | | IV-2 | Fert2 | 0.83 |
| 4674 | 3 | 4 | | | IV-2 | Fam126a | 0.96 | 4770 | 3 | 4 | | | IV-2 | Fga | 0.74 |
| 4675 | 3 | 4 | | | IV-2 | Fam129a | 0.69 | 4771 | 3 | 4 | | | IV-2 | Fgb | 0.86 |
| 4676 | 3 | 4 | | | IV-2 | Fam134c | 0.86 | 4772 | 3 | 4 | | | IV-2 | Fgd2 | 0.73 |
| 4677 | 3 | 4 | | | IV-2 | Fam136a | 0.69 | 4773 | 3 | 4 | | | IV-2 | Fgd3 | 0.87 |
| 4678 | 3 | 4 | | | IV-2 | Fam13a | 0.88 | 4774 | 3 | 4 | | | IV-2 | Fgd5 | 0.93 |
| 4679 | 3 | 4 | | | IV-2 | Fam149a | 0.93 | 4775 | 3 | 4 | | | IV-2 | Fgd6 | 0.89 |
| 4680 | 3 | 4 | | | IV-2 | Fam160a1 | 0.79 | 4776 | 3 | 4 | | | IV-2 | Fgf1 | 0.88 |
| 4681 | 3 | 4 | | | IV-2 | Fam167b | 0.85 | 4777 | 3 | 4 | | | IV-2 | Fgf18 | 0.97 |
| 4682 | 3 | 4 | | | IV-2 | Fam169b | 0.85 | 4778 | 3 | 4 | | | IV-2 | Fgfbp1 | 0.76 |
| 4683 | 3 | 4 | | | IV-2 | Fam173a | 1.00 | 4779 | 3 | 4 | | | IV-2 | Fgfr1op2 | 0.88 |
| 4684 | 3 | 4 | | | IV-2 | Fam173b | 0.88 | 4780 | 3 | 4 | | | IV-2 | Fgfr4 | 0.72 |
| 4685 | 3 | 4 | | | IV-2 | Fam174b | 0.90 | 4781 | 3 | 4 | | | IV-2 | Fgfrl1 | 0.82 |
| 4686 | 3 | 4 | | | IV-2 | Fam175b | 0.95 | 4782 | 3 | 4 | | | IV-2 | Fggy | 0.68 |
| 4687 | 3 | 4 | | | IV-2 | Fam178a | 1.00 | 4783 | 3 | 4 | | | IV-2 | Fgr | 0.99 |
| 4688 | 3 | 4 | | | IV-2 | Fam179b | 0.97 | 4784 | 3 | 4 | | | IV-2 | Fhdc1 | 0.71 |
| 4689 | 3 | 4 | | | IV-2 | Fam183b | 0.71 | 4785 | 3 | 4 | | | IV-2 | Fhl1 | 0.69 |
| 4690 | 3 | 4 | | | IV-2 | Fam185a | 0.99 | 4786 | 3 | 4 | | | IV-2 | Fhl2 | 0.90 |
| 4691 | 3 | 4 | | | IV-2 | Fam189a2 | 0.93 | 4787 | 3 | 4 | | | IV-2 | Fhl3 | 0.91 |
| 4692 | 3 | 4 | | | IV-2 | Fam193b | 0.94 | 4788 | 3 | 4 | | | IV-2 | Fhod1 | 0.81 |
| 4693 | 3 | 4 | | | IV-2 | Fam198a | 0.76 | 4789 | 3 | 4 | | | IV-2 | Figf | 0.97 |
| 4694 | 3 | 4 | | | IV-2 | Fam198b | 0.79 | 4790 | 3 | 4 | | | IV-2 | Filip1 | 0.90 |
| 4695 | 3 | 4 | | | IV-2 | Fam206a | 0.97 | 4791 | 3 | 4 | | | IV-2 | Filip1l | 0.87 |
| 4696 | 3 | 4 | | | IV-2 | Fam207a | 0.96 | 4792 | 3 | 4 | | | IV-2 | Fip1l1 | 0.99 |
| 4697 | 3 | 4 | | | IV-2 | Fam208b | 0.96 | 4793 | 3 | 4 | | | IV-2 | Fis1 | 0.88 |
| 4698 | 3 | 4 | | | IV-2 | Fam20b | 0.87 | 4794 | 3 | 4 | | | IV-2 | Fitm2 | 0.89 |
| 4699 | 3 | 4 | | | IV-2 | Fam210b | 0.69 | 4795 | 3 | 4 | | | IV-2 | Fiz1 | 0.96 |
| 4700 | 3 | 4 | | | IV-2 | Fam212b | 0.76 | 4796 | 3 | 4 | | | IV-2 | Fkbp14 | 0.76 |
| 4701 | 3 | 4 | | | IV-2 | Fam213a | 0.94 | 4797 | 3 | 4 | | | IV-2 | Fkbp15 | 0.86 |
| 4702 | 3 | 4 | | | IV-2 | Fam213b | 0.92 | 4798 | 3 | 4 | | | IV-2 | Fkbp1a | 0.83 |

Fig. 45 - 26

| | | | | | | | | | | | | | | | |
|---|---|---|---|---|---|---|---|---|---|---|---|---|---|---|---|
| 4799 | 3 | 4 | | | IV-2 | Fkbp3 | 0.76 | 4895 | 3 | 4 | | | IV-2 | Galnt11 | 0.99 |
| 4800 | 3 | 4 | | | IV-2 | Fkbp4 | 0.70 | 4896 | 3 | 4 | | | IV-2 | Galnt12 | 0.93 |
| 4801 | 3 | 4 | | | IV-2 | Fkbp7 | 0.77 | 4897 | 3 | 4 | | | IV-2 | Galnt18 | 0.90 |
| 4802 | 3 | 4 | | | IV-2 | Fkbp8 | 0.99 | 4898 | 3 | 4 | | | IV-2 | Galnt2 | 0.95 |
| 4803 | 3 | 4 | | | IV-2 | Fkbp9 | 0.98 | 4899 | 3 | 4 | | | IV-2 | Galnt3 | 0.98 |
| 4804 | 3 | 4 | | | IV-2 | Fkbpl | 0.88 | 4900 | 3 | 4 | | | IV-2 | Galnt4 | 0.90 |
| 4805 | 3 | 4 | | | IV-2 | Fkrp | 0.98 | 4901 | 3 | 4 | | | IV-2 | Galnt5 | 0.73 |
| 4806 | 3 | 4 | | | IV-2 | Fktn | 1.00 | 4902 | 3 | 4 | | | IV-2 | Gan | 0.83 |
| 4807 | 3 | 4 | | | IV-2 | Flad1 | 0.92 | 4903 | 3 | 4 | | | IV-2 | Ganab | 0.76 |
| 4808 | 3 | 4 | | | IV-2 | Flg2 | 0.93 | 4904 | 3 | 4 | | | IV-2 | Ganc | 0.86 |
| 4809 | 3 | 4 | | | IV-2 | Fli1 | 0.92 | 4905 | 3 | 4 | | | IV-2 | Gapdh | 0.76 |
| 4810 | 3 | 4 | | | IV-2 | Flii | 0.88 | 4906 | 3 | 4 | | | IV-2 | Gapvd1 | 0.88 |
| 4811 | 3 | 4 | | | IV-2 | Flnc | 0.97 | 4907 | 3 | 4 | | | IV-2 | Gar1 | 0.92 |
| 4812 | 3 | 4 | | | IV-2 | Flt1 | 0.91 | 4908 | 3 | 4 | | | IV-2 | Gart | 0.90 |
| 4813 | 3 | 4 | | | IV-2 | Fmo1 | 0.79 | 4909 | 3 | 4 | | | IV-2 | Gas2l1 | 0.77 |
| 4814 | 3 | 4 | | | IV-2 | Fmo2 | 0.85 | 4910 | 3 | 4 | | | IV-2 | Gas2l3 | 0.83 |
| 4815 | 3 | 4 | | | IV-2 | Fmod | 0.71 | 4911 | 3 | 4 | | | IV-2 | Gata3 | 0.99 |
| 4816 | 3 | 4 | | | IV-2 | Fmr1 | 0.97 | 4912 | 3 | 4 | | | IV-2 | Gata4 | 0.91 |
| 4817 | 3 | 4 | | | IV-2 | Fndc5 | 0.86 | 4913 | 3 | 4 | | | IV-2 | Gata6 | 0.93 |
| 4818 | 3 | 4 | | | IV-2 | Fnta | 0.93 | 4914 | 3 | 4 | | | IV-2 | Gatad1 | 0.95 |
| 4819 | 3 | 4 | | | IV-2 | Fntb | 0.98 | 4915 | 3 | 4 | | | IV-2 | Gatm | 0.70 |
| 4820 | 3 | 4 | | | IV-2 | Focad | 0.95 | 4916 | 3 | 4 | | | IV-2 | Gatsl2 | 0.87 |
| 4821 | 3 | 4 | | | IV-2 | Folr2 | 0.95 | 4917 | 3 | 4 | | | IV-2 | Gba | 0.94 |
| 4822 | 3 | 4 | | | IV-2 | Fopnl | 0.83 | 4918 | 3 | 4 | | | IV-2 | Gbas | 0.91 |
| 4823 | 3 | 4 | | | IV-2 | Fosl2 | 0.86 | 4919 | 3 | 4 | | | IV-2 | Gbe1 | 0.72 |
| 4824 | 3 | 4 | | | IV-2 | Foxa1 | 0.74 | 4920 | 3 | 4 | | | IV-2 | Gbf1 | 0.92 |
| 4825 | 3 | 4 | | | IV-2 | Foxa2 | 0.82 | 4921 | 3 | 4 | | | IV-2 | Gbp2 | 0.93 |
| 4826 | 3 | 4 | | | IV-2 | Foxd2os | 0.96 | 4922 | 3 | 4 | | | IV-2 | Gcdh | 0.81 |
| 4827 | 3 | 4 | | | IV-2 | Foxf1 | 0.93 | 4923 | 3 | 4 | | | IV-2 | Gch1 | 0.99 |
| 4828 | 3 | 4 | | | IV-2 | Foxf2 | 0.95 | 4924 | 3 | 4 | | | IV-2 | Gclm | 0.89 |
| 4829 | 3 | 4 | | | IV-2 | Foxi3 | 0.81 | 4925 | 3 | 4 | | | IV-2 | Gcnl1l | 0.96 |
| 4830 | 3 | 4 | | | IV-2 | Foxj2 | 0.94 | 4926 | 3 | 4 | | | IV-2 | Gcnt1 | 0.80 |
| 4831 | 3 | 4 | | | IV-2 | Foxk2 | 0.90 | 4927 | 3 | 4 | | | IV-2 | Gcnt2 | 0.92 |
| 4832 | 3 | 4 | | | IV-2 | Foxl1 | 0.80 | 4928 | 3 | 4 | | | IV-2 | Gcnt4 | 0.91 |
| 4833 | 3 | 4 | | | IV-2 | Foxm1 | 0.67 | 4929 | 3 | 4 | | | IV-2 | Gcsam | 0.90 |
| 4834 | 3 | 4 | | | IV-2 | Foxn2 | 0.84 | 4930 | 3 | 4 | | | IV-2 | Gcsh | 0.79 |
| 4835 | 3 | 4 | | | IV-2 | Foxn3 | 1.00 | 4931 | 3 | 4 | | | IV-2 | Gda | 0.73 |
| 4836 | 3 | 4 | | | IV-2 | Foxo1 | 0.94 | 4932 | 3 | 4 | | | IV-2 | Gdap10 | 0.75 |
| 4837 | 3 | 4 | | | IV-2 | Foxo3 | 0.89 | 4933 | 3 | 4 | | | IV-2 | Gde1 | 0.94 |
| 4838 | 3 | 4 | | | IV-2 | Foxo4 | 0.82 | 4934 | 3 | 4 | | | IV-2 | Gdf11 | 0.92 |
| 4839 | 3 | 4 | | | IV-2 | Foxq1 | 0.85 | 4935 | 3 | 4 | | | IV-2 | Gdi2 | 0.93 |
| 4840 | 3 | 4 | | | IV-2 | Fpgt | 0.86 | 4936 | 3 | 4 | | | IV-2 | Gdpgp1 | 0.79 |
| 4841 | 3 | 4 | | | IV-2 | Fra10ac1 | 0.82 | 4937 | 3 | 4 | | | IV-2 | Gem | 0.89 |
| 4842 | 3 | 4 | | | IV-2 | Fras1 | 0.95 | 4938 | 3 | 4 | | | IV-2 | Gemin2 | 0.79 |
| 4843 | 3 | 4 | | | IV-2 | Frem1 | 0.78 | 4939 | 3 | 4 | | | IV-2 | Gemin4 | 0.84 |
| 4844 | 3 | 4 | | | IV-2 | Frem2 | 0.82 | 4940 | 3 | 4 | | | IV-2 | Gemin5 | 0.96 |
| 4845 | 3 | 4 | | | IV-2 | Frmd8 | 0.78 | 4941 | 3 | 4 | | | IV-2 | Gemin7 | 0.90 |
| 4846 | 3 | 4 | | | IV-2 | Fryl | 0.96 | 4942 | 3 | 4 | | | IV-2 | Gemin8 | 0.81 |
| 4847 | 3 | 4 | | | IV-2 | Frzb | 0.99 | 4943 | 3 | 4 | | | IV-2 | Gfer | 0.92 |
| 4848 | 3 | 4 | | | IV-2 | Fsbp | 0.97 | 4944 | 3 | 4 | | | IV-2 | Gfi1 | 0.81 |
| 4849 | 3 | 4 | | | IV-2 | Fscn1 | 0.98 | 4945 | 3 | 4 | | | IV-2 | Gfm1 | 0.92 |
| 4850 | 3 | 4 | | | IV-2 | Fstl3 | 0.88 | 4946 | 3 | 4 | | | IV-2 | Gfm2 | 0.82 |
| 4851 | 3 | 4 | | | IV-2 | Fth1 | 0.88 | 4947 | 3 | 4 | | | IV-2 | Gfpt1 | 0.91 |
| 4852 | 3 | 4 | | | IV-2 | Ftl1 | 0.89 | 4948 | 3 | 4 | | | IV-2 | Gfra2 | 0.95 |
| 4853 | 3 | 4 | | | IV-2 | Ftsj1 | 0.97 | 4949 | 3 | 4 | | | IV-2 | Gga1 | 0.95 |
| 4854 | 3 | 4 | | | IV-2 | Ftsj2 | 0.88 | 4950 | 3 | 4 | | | IV-2 | Gga2 | 0.77 |
| 4855 | 3 | 4 | | | IV-2 | Fuca2 | 0.91 | 4951 | 3 | 4 | | | IV-2 | Gga3 | 0.90 |
| 4856 | 3 | 4 | | | IV-2 | Fundc1 | 0.95 | 4952 | 3 | 4 | | | IV-2 | Ggcx | 0.69 |
| 4857 | 3 | 4 | | | IV-2 | Fuom | 0.99 | 4953 | 3 | 4 | | | IV-2 | Ggh | 0.73 |
| 4858 | 3 | 4 | | | IV-2 | Fut1 | 0.93 | 4954 | 3 | 4 | | | IV-2 | Ggt1 | 0.77 |
| 4859 | 3 | 4 | | | IV-2 | Fut11 | 0.98 | 4955 | 3 | 4 | | | IV-2 | Ggt6 | 0.86 |
| 4860 | 3 | 4 | | | IV-2 | Fut4 | 0.74 | 4956 | 3 | 4 | | | IV-2 | Ggta1 | 0.88 |
| 4861 | 3 | 4 | | | IV-2 | Fuz | 0.80 | 4957 | 3 | 4 | | | IV-2 | Ghdc | 0.87 |
| 4862 | 3 | 4 | | | IV-2 | Fv1 | 0.72 | 4958 | 3 | 4 | | | IV-2 | Ghitm | 0.86 |
| 4863 | 3 | 4 | | | IV-2 | Fxn | 0.76 | 4959 | 3 | 4 | | | IV-2 | Ghr | 0.95 |
| 4864 | 3 | 4 | | | IV-2 | Fxr1 | 0.90 | 4960 | 3 | 4 | | | IV-2 | Ghrl | 0.72 |
| 4865 | 3 | 4 | | | IV-2 | Fxyd2 | 0.75 | 4961 | 3 | 4 | | | IV-2 | Gid4 | 0.98 |
| 4866 | 3 | 4 | | | IV-2 | Fyb | 0.86 | 4962 | 3 | 4 | | | IV-2 | Gimap5 | 0.92 |
| 4867 | 3 | 4 | | | IV-2 | Fyco1 | 0.90 | 4963 | 3 | 4 | | | IV-2 | Gimap6 | 0.93 |
| 4868 | 3 | 4 | | | IV-2 | Fyttd1 | 0.94 | 4964 | 3 | 4 | | | IV-2 | Gimap8 | 0.81 |
| 4869 | 3 | 4 | | | IV-2 | Fzd4 | 0.78 | 4965 | 3 | 4 | | | IV-2 | Gimap9 | 0.84 |
| 4870 | 3 | 4 | | | IV-2 | Fzd5 | 0.78 | 4966 | 3 | 4 | | | IV-2 | Gin1 | 0.94 |
| 4871 | 3 | 4 | | | IV-2 | Fzd7 | 0.98 | 4967 | 3 | 4 | | | IV-2 | Gins2 | 0.81 |
| 4872 | 3 | 4 | | | IV-2 | Fzr1 | 0.79 | 4968 | 3 | 4 | | | IV-2 | Gins4 | 0.89 |
| 4873 | 3 | 4 | | | IV-2 | G0s2 | 0.72 | 4969 | 3 | 4 | | | IV-2 | Gipc1 | 0.88 |
| 4874 | 3 | 4 | | | IV-2 | G2e3 | 0.83 | 4970 | 3 | 4 | | | IV-2 | Gipr | 0.90 |
| 4875 | 3 | 4 | | | IV-2 | G3bp1 | 0.75 | 4971 | 3 | 4 | | | IV-2 | Git2 | 0.95 |
| 4876 | 3 | 4 | | | IV-2 | G6b | 0.75 | 4972 | 3 | 4 | | | IV-2 | Gja1 | 0.84 |
| 4877 | 3 | 4 | | | IV-2 | G6pdx | 0.98 | 4973 | 3 | 4 | | | IV-2 | Gja4 | 0.69 |
| 4878 | 3 | 4 | | | IV-2 | Gab1 | 0.97 | 4974 | 3 | 4 | | | IV-2 | Gja5 | 0.90 |
| 4879 | 3 | 4 | | | IV-2 | Gabarap | 0.78 | 4975 | 3 | 4 | | | IV-2 | Gjb1 | 0.68 |
| 4880 | 3 | 4 | | | IV-2 | Gabarapl2 | 0.85 | 4976 | 3 | 4 | | | IV-2 | Glb1 | 0.71 |
| 4881 | 3 | 4 | | | IV-2 | Gabpa | 0.89 | 4977 | 3 | 4 | | | IV-2 | Glcci1 | 0.99 |
| 4882 | 3 | 4 | | | IV-2 | Gabpb1 | 0.95 | 4978 | 3 | 4 | | | IV-2 | Gldc | 0.85 |
| 4883 | 3 | 4 | | | IV-2 | Gabpb2 | 0.85 | 4979 | 3 | 4 | | | IV-2 | Gle1 | 0.97 |
| 4884 | 3 | 4 | | | IV-2 | Gabra4 | 0.76 | 4980 | 3 | 4 | | | IV-2 | Glipr1 | 0.90 |
| 4885 | 3 | 4 | | | IV-2 | Gabrp | 0.87 | 4981 | 3 | 4 | | | IV-2 | Glipr2 | 0.90 |
| 4886 | 3 | 4 | | | IV-2 | Gadd45gip1 | 0.72 | 4982 | 3 | 4 | | | IV-2 | Glo1 | 0.71 |
| 4887 | 3 | 4 | | | IV-2 | Gadl1 | 0.87 | 4983 | 3 | 4 | | | IV-2 | Glod4 | 0.89 |
| 4888 | 3 | 4 | | | IV-2 | Gal3st1 | 0.94 | 4984 | 3 | 4 | | | IV-2 | Glrx | 0.86 |
| 4889 | 3 | 4 | | | IV-2 | Galk1 | 0.84 | 4985 | 3 | 4 | | | IV-2 | Glrx3 | 0.68 |
| 4890 | 3 | 4 | | | IV-2 | Galk2 | 0.89 | 4986 | 3 | 4 | | | IV-2 | Glrx5 | 0.69 |
| 4891 | 3 | 4 | | | IV-2 | Galm | 0.67 | 4987 | 3 | 4 | | | IV-2 | Gls | 0.91 |
| 4892 | 3 | 4 | | | IV-2 | Galns | 0.85 | 4988 | 3 | 4 | | | IV-2 | Gls2 | 0.92 |
| 4893 | 3 | 4 | | | IV-2 | Galnt1 | 0.88 | 4989 | 3 | 4 | | | IV-2 | Glt25d1 | 0.86 |
| 4894 | 3 | 4 | | | IV-2 | Galnt10 | 0.82 | 4990 | 3 | 4 | | | IV-2 | Glt28d2 | 0.94 |

Fig. 45 - 27

| | | | | | | | | | | | | | | |
|---|---|---|---|---|---|---|---|---|---|---|---|---|---|---|
| 4991 | 3 | 4 | | | IV-2 | Glt8d1 | 0.81 | 5087 | 3 | 4 | | | IV-2 | Gm8801 | 0.96 |
| 4992 | 3 | 4 | | | IV-2 | Glt8d2 | 0.90 | 5088 | 3 | 4 | | | IV-2 | Gm8979 | 0.89 |
| 4993 | 3 | 4 | | | IV-2 | Gltp | 0.84 | 5089 | 3 | 4 | | | IV-2 | Gm8989 | 0.98 |
| 4994 | 3 | 4 | | | IV-2 | Gltpd1 | 0.90 | 5090 | 3 | 4 | | | IV-2 | Gm9199 | 0.92 |
| 4995 | 3 | 4 | | | IV-2 | Glud1 | 0.75 | 5091 | 3 | 4 | | | IV-2 | Gm9895 | 0.95 |
| 4996 | 3 | 4 | | | IV-2 | Glyctk | 0.70 | 5092 | 3 | 4 | | | IV-2 | Gm9899 | 0.98 |
| 4997 | 3 | 4 | | | IV-2 | Gm10012 | 0.69 | 5093 | 3 | 4 | | | IV-2 | Gmcl1 | 0.90 |
| 4998 | 3 | 4 | | | IV-2 | Gm10033 | 0.68 | 5094 | 3 | 4 | | | IV-2 | Gmeb2 | 0.94 |
| 4999 | 3 | 4 | | | IV-2 | Gm10094 | 0.88 | 5095 | 3 | 4 | | | IV-2 | Gmppa | 0.70 |
| 5000 | 3 | 4 | | | IV-2 | Gm10591 | 0.71 | 5096 | 3 | 4 | | | IV-2 | Gmppb | 0.74 |
| 5001 | 3 | 4 | | | IV-2 | Gm10653 | 0.85 | 5097 | 3 | 4 | | | IV-2 | Gmpr2 | 0.97 |
| 5002 | 3 | 4 | | | IV-2 | Gm10767 | 0.98 | 5098 | 3 | 4 | | | IV-2 | Gna11 | 0.97 |
| 5003 | 3 | 4 | | | IV-2 | Gm10778 | 0.73 | 5099 | 3 | 4 | | | IV-2 | Gna13 | 0.91 |
| 5004 | 3 | 4 | | | IV-2 | Gm10857 | 0.90 | 5100 | 3 | 4 | | | IV-2 | Gna15 | 0.70 |
| 5005 | 3 | 4 | | | IV-2 | Gm11837 | 0.69 | 5101 | 3 | 4 | | | IV-2 | Gnai2 | 0.93 |
| 5006 | 3 | 4 | | | IV-2 | Gm12070 | 0.82 | 5102 | 3 | 4 | | | IV-2 | Gnai3 | 0.93 |
| 5007 | 3 | 4 | | | IV-2 | Gm12338 | 0.82 | 5103 | 3 | 4 | | | IV-2 | Gnas | 0.83 |
| 5008 | 3 | 4 | | | IV-2 | Gm12359 | 0.94 | 5104 | 3 | 4 | | | IV-2 | Gnb2 | 0.88 |
| 5009 | 3 | 4 | | | IV-2 | Gm12504 | 0.89 | 5105 | 3 | 4 | | | IV-2 | Gnb4 | 0.98 |
| 5010 | 3 | 4 | | | IV-2 | Gm12657 | 0.83 | 5106 | 3 | 4 | | | IV-2 | Gng10 | 0.94 |
| 5011 | 3 | 4 | | | IV-2 | Gm12942 | 0.86 | 5107 | 3 | 4 | | | IV-2 | Gng11 | 0.79 |
| 5012 | 3 | 4 | | | IV-2 | Gm13034 | 0.91 | 5108 | 3 | 4 | | | IV-2 | Gng12 | 0.83 |
| 5013 | 3 | 4 | | | IV-2 | Gm13305 | 0.82 | 5109 | 3 | 4 | | | IV-2 | Gng4 | 0.98 |
| 5014 | 3 | 4 | | | IV-2 | Gm13306 | 0.74 | 5110 | 3 | 4 | | | IV-2 | Gng5 | 0.77 |
| 5015 | 3 | 4 | | | IV-2 | Gm13889 | 0.80 | 5111 | 3 | 4 | | | IV-2 | Gngt2 | 0.79 |
| 5016 | 3 | 4 | | | IV-2 | Gm14137 | 0.92 | 5112 | 3 | 4 | | | IV-2 | Gnpat | 0.85 |
| 5017 | 3 | 4 | | | IV-2 | Gm14207 | 0.91 | 5113 | 3 | 4 | | | IV-2 | Gnpnat1 | 0.94 |
| 5018 | 3 | 4 | | | IV-2 | Gm14305 | 0.87 | 5114 | 3 | 4 | | | IV-2 | Gnrh1 | 0.84 |
| 5019 | 3 | 4 | | | IV-2 | Gm14308 | 0.99 | 5115 | 3 | 4 | | | IV-2 | Golga3 | 1.00 |
| 5020 | 3 | 4 | | | IV-2 | Gm14322 | 1.00 | 5116 | 3 | 4 | | | IV-2 | Golga4 | 0.86 |
| 5021 | 3 | 4 | | | IV-2 | Gm14326 | 0.84 | 5117 | 3 | 4 | | | IV-2 | Golga7 | 0.94 |
| 5022 | 3 | 4 | | | IV-2 | Gm14403 | 0.80 | 5118 | 3 | 4 | | | IV-2 | Golgb1 | 0.97 |
| 5023 | 3 | 4 | | | IV-2 | Gm14436 | 0.93 | 5119 | 3 | 4 | | | IV-2 | Golm1 | 0.77 |
| 5024 | 3 | 4 | | | IV-2 | Gm14440 | 0.91 | 5120 | 3 | 4 | | | IV-2 | Golph3 | 0.90 |
| 5025 | 3 | 4 | | | IV-2 | Gm15421 | 0.73 | 5121 | 3 | 4 | | | IV-2 | Golph3l | 0.91 |
| 5026 | 3 | 4 | | | IV-2 | Gm15446 | 0.87 | 5122 | 3 | 4 | | | IV-2 | Golt1a | 0.87 |
| 5027 | 3 | 4 | | | IV-2 | Gm15455 | 0.75 | 5123 | 3 | 4 | | | IV-2 | Golt1b | 0.99 |
| 5028 | 3 | 4 | | | IV-2 | Gm15663 | 0.95 | 5124 | 3 | 4 | | | IV-2 | Gorasp1 | 0.87 |
| 5029 | 3 | 4 | | | IV-2 | Gm15760 | 0.96 | 5125 | 3 | 4 | | | IV-2 | Gosr1 | 0.97 |
| 5030 | 3 | 4 | | | IV-2 | Gm15772 | 0.93 | 5126 | 3 | 4 | | | IV-2 | Got1 | 0.88 |
| 5031 | 3 | 4 | | | IV-2 | Gm15816 | 0.77 | 5127 | 3 | 4 | | | IV-2 | Got2 | 0.78 |
| 5032 | 3 | 4 | | | IV-2 | Gm16023 | 0.76 | 5128 | 3 | 4 | | | IV-2 | Gpaa1 | 0.94 |
| 5033 | 3 | 4 | | | IV-2 | Gm16039 | 0.98 | 5129 | 3 | 4 | | | IV-2 | Gpam | 0.81 |
| 5034 | 3 | 4 | | | IV-2 | Gm16062 | 0.84 | 5130 | 3 | 4 | | | IV-2 | Gpank1 | 0.94 |
| 5035 | 3 | 4 | | | IV-2 | Gm16381 | 0.82 | 5131 | 3 | 4 | | | IV-2 | Gpatch11 | 0.81 |
| 5036 | 3 | 4 | | | IV-2 | Gm16515 | 0.89 | 5132 | 3 | 4 | | | IV-2 | Gpatch3 | 0.80 |
| 5037 | 3 | 4 | | | IV-2 | Gm16523 | 0.98 | 5133 | 3 | 4 | | | IV-2 | Gpbp1 | 0.88 |
| 5038 | 3 | 4 | | | IV-2 | Gm16576 | 0.91 | 5134 | 3 | 4 | | | IV-2 | Gpbp1l1 | 0.89 |
| 5039 | 3 | 4 | | | IV-2 | Gm166 | 0.95 | 5135 | 3 | 4 | | | IV-2 | Gpd1l | 0.91 |
| 5040 | 3 | 4 | | | IV-2 | Gm16675 | 0.87 | 5136 | 3 | 4 | | | IV-2 | Gpi1 | 0.87 |
| 5041 | 3 | 4 | | | IV-2 | Gm16982 | 0.95 | 5137 | 3 | 4 | | | IV-2 | Gpkow | 0.92 |
| 5042 | 3 | 4 | | | IV-2 | Gm1821 | 0.98 | 5138 | 3 | 4 | | | IV-2 | Gpld1 | 0.97 |
| 5043 | 3 | 4 | | | IV-2 | Gm1943 | 0.90 | 5139 | 3 | 4 | | | IV-2 | Gpn3 | 0.90 |
| 5044 | 3 | 4 | | | IV-2 | Gm1966 | 0.78 | 5140 | 3 | 4 | | | IV-2 | Gpr107 | 0.89 |
| 5045 | 3 | 4 | | | IV-2 | Gm1995 | 1.00 | 5141 | 3 | 4 | | | IV-2 | Gpr108 | 0.94 |
| 5046 | 3 | 4 | | | IV-2 | Gm20300 | 0.97 | 5142 | 3 | 4 | | | IV-2 | Gpr111 | 0.69 |
| 5047 | 3 | 4 | | | IV-2 | Gm20554 | 0.75 | 5143 | 3 | 4 | | | IV-2 | Gpr115 | 0.90 |
| 5048 | 3 | 4 | | | IV-2 | Gm20604 | 0.96 | 5144 | 3 | 4 | | | IV-2 | Gpr12 | 0.89 |
| 5049 | 3 | 4 | | | IV-2 | Gm20748 | 0.88 | 5145 | 3 | 4 | | | IV-2 | Gpr126 | 0.94 |
| 5050 | 3 | 4 | | | IV-2 | Gm2115 | 0.68 | 5146 | 3 | 4 | | | IV-2 | Gpr128 | 1.00 |
| 5051 | 3 | 4 | | | IV-2 | Gm21541 | 0.80 | 5147 | 3 | 4 | | | IV-2 | Gpr133 | 0.78 |
| 5052 | 3 | 4 | | | IV-2 | Gm2382 | 0.85 | 5148 | 3 | 4 | | | IV-2 | Gpr153 | 0.83 |
| 5053 | 3 | 4 | | | IV-2 | Gm2518 | 0.88 | 5149 | 3 | 4 | | | IV-2 | Gpr157 | 0.74 |
| 5054 | 3 | 4 | | | IV-2 | Gm3219 | 0.77 | 5150 | 3 | 4 | | | IV-2 | Gpr160 | 0.70 |
| 5055 | 3 | 4 | | | IV-2 | Gm3258 | 0.93 | 5151 | 3 | 4 | | | IV-2 | Gpr17 | 0.81 |
| 5056 | 3 | 4 | | | IV-2 | Gm3414 | 0.78 | 5152 | 3 | 4 | | | IV-2 | Gpr176 | 0.99 |
| 5057 | 3 | 4 | | | IV-2 | Gm3604 | 0.86 | 5153 | 3 | 4 | | | IV-2 | Gpr180 | 1.00 |
| 5058 | 3 | 4 | | | IV-2 | Gm4349 | 0.95 | 5154 | 3 | 4 | | | IV-2 | Gpr182 | 0.77 |
| 5059 | 3 | 4 | | | IV-2 | Gm438 | 0.83 | 5155 | 3 | 4 | | | IV-2 | Gpr20 | 0.82 |
| 5060 | 3 | 4 | | | IV-2 | Gm4724 | 0.94 | 5156 | 3 | 4 | | | IV-2 | Gpr34 | 0.74 |
| 5061 | 3 | 4 | | | IV-2 | Gm4907 | 0.96 | 5157 | 3 | 4 | | | IV-2 | Gpr35 | 0.86 |
| 5062 | 3 | 4 | | | IV-2 | Gm4944 | 0.86 | 5158 | 3 | 4 | | | IV-2 | Gpr39 | 0.74 |
| 5063 | 3 | 4 | | | IV-2 | Gm5065 | 0.88 | 5159 | 3 | 4 | | | IV-2 | Gpr4 | 0.97 |
| 5064 | 3 | 4 | | | IV-2 | Gm5069 | 0.99 | 5160 | 3 | 4 | | | IV-2 | Gpr50 | 0.79 |
| 5065 | 3 | 4 | | | IV-2 | Gm5105 | 0.73 | 5161 | 3 | 4 | | | IV-2 | Gpr65 | 0.73 |
| 5066 | 3 | 4 | | | IV-2 | Gm5141 | 0.97 | 5162 | 3 | 4 | | | IV-2 | Gpr83 | 0.81 |
| 5067 | 3 | 4 | | | IV-2 | Gm5434 | 0.82 | 5163 | 3 | 4 | | | IV-2 | Gpr89 | 0.74 |
| 5068 | 3 | 4 | | | IV-2 | Gm5595 | 0.82 | 5164 | 3 | 4 | | | IV-2 | Gprc5b | 0.96 |
| 5069 | 3 | 4 | | | IV-2 | Gm561 | 0.89 | 5165 | 3 | 4 | | | IV-2 | Gprc5c | 0.84 |
| 5070 | 3 | 4 | | | IV-2 | Gm5801 | 1.00 | 5166 | 3 | 4 | | | IV-2 | Gprin2 | 0.71 |
| 5071 | 3 | 4 | | | IV-2 | Gm5803 | 0.91 | 5167 | 3 | 4 | | | IV-2 | Gps2 | 0.94 |
| 5072 | 3 | 4 | | | IV-2 | Gm608 | 0.93 | 5168 | 3 | 4 | | | IV-2 | Gpsm2 | 0.91 |
| 5073 | 3 | 4 | | | IV-2 | Gm6194 | 0.86 | 5169 | 3 | 4 | | | IV-2 | Gpt2 | 0.83 |
| 5074 | 3 | 4 | | | IV-2 | Gm6524 | 0.79 | 5170 | 3 | 4 | | | IV-2 | Gpx2 | 0.93 |
| 5075 | 3 | 4 | | | IV-2 | Gm6537 | 0.84 | 5171 | 3 | 4 | | | IV-2 | Gpx4 | 0.92 |
| 5076 | 3 | 4 | | | IV-2 | Gm6568 | 0.83 | 5172 | 3 | 4 | | | IV-2 | Gpx8 | 0.68 |
| 5077 | 3 | 4 | | | IV-2 | Gm6578 | 0.78 | 5173 | 3 | 4 | | | IV-2 | Gramd1c | 0.88 |
| 5078 | 3 | 4 | | | IV-2 | Gm6607 | 0.83 | 5174 | 3 | 4 | | | IV-2 | Gramd3 | 0.92 |
| 5079 | 3 | 4 | | | IV-2 | Gm6710 | 0.93 | 5175 | 3 | 4 | | | IV-2 | Grb10 | 0.91 |
| 5080 | 3 | 4 | | | IV-2 | Gm6787 | 0.83 | 5176 | 3 | 4 | | | IV-2 | Grb14 | 0.70 |
| 5081 | 3 | 4 | | | IV-2 | Gm7102 | 0.95 | 5177 | 3 | 4 | | | IV-2 | Grcc10 | 0.97 |
| 5082 | 3 | 4 | | | IV-2 | Gm715 | 0.90 | 5178 | 3 | 4 | | | IV-2 | Grhl1 | 0.94 |
| 5083 | 3 | 4 | | | IV-2 | Gm7325 | 0.95 | 5179 | 3 | 4 | | | IV-2 | Grhl2 | 0.92 |
| 5084 | 3 | 4 | | | IV-2 | Gm766 | 0.73 | 5180 | 3 | 4 | | | IV-2 | Grhl3 | 0.84 |
| 5085 | 3 | 4 | | | IV-2 | Gm826 | 0.73 | 5181 | 3 | 4 | | | IV-2 | Grhpr | 0.72 |
| 5086 | 3 | 4 | | | IV-2 | Gm8363 | 0.83 | 5182 | 3 | 4 | | | IV-2 | Grk4 | 0.86 |

Fig. 45 - 28

| | | | | | | | | | | | | | | | |
|---|---|---|---|---|---|---|---|---|---|---|---|---|---|---|---|
| 5183 | 3 | 4 | | | IV-2 | Grm7 | 0.95 | 5279 | 3 | 4 | | | IV-2 | Hdlbp | 0.87 |
| 5184 | 3 | 4 | | | IV-2 | Grpel1 | 0.85 | 5280 | 3 | 4 | | | IV-2 | Heatr1 | 0.92 |
| 5185 | 3 | 4 | | | IV-2 | Grrp1 | 0.71 | 5281 | 3 | 4 | | | IV-2 | Heatr2 | 0.84 |
| 5186 | 3 | 4 | | | IV-2 | Grsf1 | 0.97 | 5282 | 3 | 4 | | | IV-2 | Heatr3 | 0.94 |
| 5187 | 3 | 4 | | | IV-2 | Grtp1 | 0.97 | 5283 | 3 | 4 | | | IV-2 | Heatr5a | 0.76 |
| 5188 | 3 | 4 | | | IV-2 | Grwd1 | 0.94 | 5284 | 3 | 4 | | | IV-2 | Heatr5b | 0.94 |
| 5189 | 3 | 4 | | | IV-2 | Gsdmc | 0.85 | 5285 | 3 | 4 | | | IV-2 | Heatr6 | 0.97 |
| 5190 | 3 | 4 | | | IV-2 | Gsdmd | 0.78 | 5286 | 3 | 4 | | | IV-2 | Hebp2 | 0.68 |
| 5191 | 3 | 4 | | | IV-2 | Gsk3a | 0.99 | 5287 | 3 | 4 | | | IV-2 | Heg1 | 0.89 |
| 5192 | 3 | 4 | | | IV-2 | Gsn | 0.85 | 5288 | 3 | 4 | | | IV-2 | Helb | 0.85 |
| 5193 | 3 | 4 | | | IV-2 | Gss | 0.73 | 5289 | 3 | 4 | | | IV-2 | Hells | 0.79 |
| 5194 | 3 | 4 | | | IV-2 | Gsta1 | 0.86 | 5290 | 3 | 4 | | | IV-2 | Helz | 0.78 |
| 5195 | 3 | 4 | | | IV-2 | Gsta3 | 0.96 | 5291 | 3 | 4 | | | IV-2 | Heph | 0.98 |
| 5196 | 3 | 4 | | | IV-2 | Gsta4 | 1.00 | 5292 | 3 | 4 | | | IV-2 | Hephl1 | 0.92 |
| 5197 | 3 | 4 | | | IV-2 | Gstk1 | 0.88 | 5293 | 3 | 4 | | | IV-2 | Herc1 | 0.83 |
| 5198 | 3 | 4 | | | IV-2 | Gstm3 | 0.95 | 5294 | 3 | 4 | | | IV-2 | Herc3 | 0.95 |
| 5199 | 3 | 4 | | | IV-2 | Gstm4 | 0.89 | 5295 | 3 | 4 | | | IV-2 | Herc4 | 0.93 |
| 5200 | 3 | 4 | | | IV-2 | Gstm5 | 0.87 | 5296 | 3 | 4 | | | IV-2 | Herpud2 | 0.95 |
| 5201 | 3 | 4 | | | IV-2 | Gstm6 | 0.75 | 5297 | 3 | 4 | | | IV-2 | Hes1 | 0.89 |
| 5202 | 3 | 4 | | | IV-2 | Gstm7 | 0.81 | 5298 | 3 | 4 | | | IV-2 | Hexb | 0.69 |
| 5203 | 3 | 4 | | | IV-2 | Gsto1 | 0.85 | 5299 | 3 | 4 | | | IV-2 | Hexim1 | 0.88 |
| 5204 | 3 | 4 | | | IV-2 | Gstp1 | 0.91 | 5300 | 3 | 4 | | | IV-2 | Hey1 | 0.88 |
| 5205 | 3 | 4 | | | IV-2 | Gstp2 | 0.84 | 5301 | 3 | 4 | | | IV-2 | Hfe | 0.96 |
| 5206 | 3 | 4 | | | IV-2 | Gstz1 | 0.67 | 5302 | 3 | 4 | | | IV-2 | Hfe2 | 0.85 |
| 5207 | 3 | 4 | | | IV-2 | Gtf2a2 | 0.94 | 5303 | 3 | 4 | | | IV-2 | Hgd | 0.72 |
| 5208 | 3 | 4 | | | IV-2 | Gtf2e1 | 0.95 | 5304 | 3 | 4 | | | IV-2 | Hgf | 0.86 |
| 5209 | 3 | 4 | | | IV-2 | Gtf2e2 | 0.75 | 5305 | 3 | 4 | | | IV-2 | Hhatl | 0.79 |
| 5210 | 3 | 4 | | | IV-2 | Gtf2f1 | 0.91 | 5306 | 3 | 4 | | | IV-2 | Hhex | 0.80 |
| 5211 | 3 | 4 | | | IV-2 | Gtf2f2 | 0.98 | 5307 | 3 | 4 | | | IV-2 | Hhip | 0.85 |
| 5212 | 3 | 4 | | | IV-2 | Gtf2h3 | 0.75 | 5308 | 3 | 4 | | | IV-2 | Hiat1 | 0.89 |
| 5213 | 3 | 4 | | | IV-2 | Gtf2h4 | 0.93 | 5309 | 3 | 4 | | | IV-2 | Hiatl1 | 0.75 |
| 5214 | 3 | 4 | | | IV-2 | Gtf2h5 | 0.93 | 5310 | 3 | 4 | | | IV-2 | Hic1 | 0.85 |
| 5215 | 3 | 4 | | | IV-2 | Gtf2i | 0.90 | 5311 | 3 | 4 | | | IV-2 | Hif1a | 0.92 |
| 5216 | 3 | 4 | | | IV-2 | Gtf3a | 0.96 | 5312 | 3 | 4 | | | IV-2 | Hif1an | 0.91 |
| 5217 | 3 | 4 | | | IV-2 | Gtf3c1 | 0.97 | 5313 | 3 | 4 | | | IV-2 | Hif3a | 0.86 |
| 5218 | 3 | 4 | | | IV-2 | Gtf3c3 | 0.94 | 5314 | 3 | 4 | | | IV-2 | Higd1a | 0.75 |
| 5219 | 3 | 4 | | | IV-2 | Gtf3c5 | 0.92 | 5315 | 3 | 4 | | | IV-2 | Higd2a | 0.89 |
| 5220 | 3 | 4 | | | IV-2 | Gtf3c6 | 0.90 | 5316 | 3 | 4 | | | IV-2 | Hilpda | 0.99 |
| 5221 | 3 | 4 | | | IV-2 | Gtpbp1 | 0.96 | 5317 | 3 | 4 | | | IV-2 | Hils1 | 0.80 |
| 5222 | 3 | 4 | | | IV-2 | Gtpbp2 | 0.99 | 5318 | 3 | 4 | | | IV-2 | Hinfp | 0.97 |
| 5223 | 3 | 4 | | | IV-2 | Gtpbp3 | 0.89 | 5319 | 3 | 4 | | | IV-2 | Hint2 | 0.98 |
| 5224 | 3 | 4 | | | IV-2 | Gtse1 | 0.82 | 5320 | 3 | 4 | | | IV-2 | Hint3 | 0.81 |
| 5225 | 3 | 4 | | | IV-2 | Gucd1 | 0.69 | 5321 | 3 | 4 | | | IV-2 | Hip1 | 0.97 |
| 5226 | 3 | 4 | | | IV-2 | Gucy1a2 | 0.87 | 5322 | 3 | 4 | | | IV-2 | Hip1r | 1.00 |
| 5227 | 3 | 4 | | | IV-2 | Gucy1a3 | 0.81 | 5323 | 3 | 4 | | | IV-2 | Hipk1 | 0.99 |
| 5228 | 3 | 4 | | | IV-2 | Gucy1b3 | 0.90 | 5324 | 3 | 4 | | | IV-2 | Hirip3 | 0.70 |
| 5229 | 3 | 4 | | | IV-2 | Gucy2c | 0.87 | 5325 | 3 | 4 | | | IV-2 | Hist1h1c | 0.78 |
| 5230 | 3 | 4 | | | IV-2 | Guk1 | 0.90 | 5326 | 3 | 4 | | | IV-2 | Hist1h2af | 0.72 |
| 5231 | 3 | 4 | | | IV-2 | Gulo | 0.84 | 5327 | 3 | 4 | | | IV-2 | Hist1h2an | 0.77 |
| 5232 | 3 | 4 | | | IV-2 | Gusb | 0.82 | 5328 | 3 | 4 | | | IV-2 | Hist1h2be | 0.82 |
| 5233 | 3 | 4 | | | IV-2 | Gxylt1 | 0.93 | 5329 | 3 | 4 | | | IV-2 | Hist1h2bf | 0.83 |
| 5234 | 3 | 4 | | | IV-2 | Gxylt2 | 0.72 | 5330 | 3 | 4 | | | IV-2 | Hist1h2bk | 0.80 |
| 5235 | 3 | 4 | | | IV-2 | Gyg | 0.82 | 5331 | 3 | 4 | | | IV-2 | Hist1h2bp | 0.74 |
| 5236 | 3 | 4 | | | IV-2 | Gyk | 0.76 | 5332 | 3 | 4 | | | IV-2 | Hist1h3b | 0.80 |
| 5237 | 3 | 4 | | | IV-2 | Gyltl1b | 0.99 | 5333 | 3 | 4 | | | IV-2 | Hist1h3g | 0.91 |
| 5238 | 3 | 4 | | | IV-2 | Gzf1 | 0.86 | 5334 | 3 | 4 | | | IV-2 | Hist1h4b | 0.70 |
| 5239 | 3 | 4 | | | IV-2 | H2-Eb1 | 0.95 | 5335 | 3 | 4 | | | IV-2 | Hist1h4d | 0.93 |
| 5240 | 3 | 4 | | | IV-2 | H2-Ke6 | 0.88 | 5336 | 3 | 4 | | | IV-2 | Hist1h4h | 0.68 |
| 5241 | 3 | 4 | | | IV-2 | H2-Q4 | 1.00 | 5337 | 3 | 4 | | | IV-2 | Hist1h4m | 0.71 |
| 5242 | 3 | 4 | | | IV-2 | H2-T23 | 0.96 | 5338 | 3 | 4 | | | IV-2 | Hist2h2be | 0.82 |
| 5243 | 3 | 4 | | | IV-2 | H2-T24 | 0.90 | 5339 | 3 | 4 | | | IV-2 | Hist2h4 | 0.81 |
| 5244 | 3 | 4 | | | IV-2 | H2afj | 0.97 | 5340 | 3 | 4 | | | IV-2 | Hist3h2a | 0.71 |
| 5245 | 3 | 4 | | | IV-2 | H2afv | 0.75 | 5341 | 3 | 4 | | | IV-2 | Hist3h2bb-ps | 0.88 |
| 5246 | 3 | 4 | | | IV-2 | H2afz | 0.78 | 5342 | 3 | 4 | | | IV-2 | Hk1 | 0.68 |
| 5247 | 3 | 4 | | | IV-2 | H3f3a | 0.82 | 5343 | 3 | 4 | | | IV-2 | Hltf | 0.93 |
| 5248 | 3 | 4 | | | IV-2 | H6pd | 0.95 | 5344 | 3 | 4 | | | IV-2 | Hmg20a | 0.99 |
| 5249 | 3 | 4 | | | IV-2 | Hace1 | 0.77 | 5345 | 3 | 4 | | | IV-2 | Hmg20b | 0.98 |
| 5250 | 3 | 4 | | | IV-2 | Hand1 | 0.92 | 5346 | 3 | 4 | | | IV-2 | Hmga2-ps1 | 0.96 |
| 5251 | 3 | 4 | | | IV-2 | Harbi1 | 0.92 | 5347 | 3 | 4 | | | IV-2 | Hmgb1 | 0.78 |
| 5252 | 3 | 4 | | | IV-2 | Hars | 0.83 | 5348 | 3 | 4 | | | IV-2 | Hmgcl | 0.93 |
| 5253 | 3 | 4 | | | IV-2 | Hars2 | 0.89 | 5349 | 3 | 4 | | | IV-2 | Hmgcr | 0.91 |
| 5254 | 3 | 4 | | | IV-2 | Has3 | 0.71 | 5350 | 3 | 4 | | | IV-2 | Hmgcs1 | 0.80 |
| 5255 | 3 | 4 | | | IV-2 | Hat1 | 0.67 | 5351 | 3 | 4 | | | IV-2 | Hmgn1 | 0.80 |
| 5256 | 3 | 4 | | | IV-2 | Haus3 | 0.73 | 5352 | 3 | 4 | | | IV-2 | Hmgn2 | 0.74 |
| 5257 | 3 | 4 | | | IV-2 | Haus4 | 0.97 | 5353 | 3 | 4 | | | IV-2 | Hmgn5 | 0.75 |
| 5258 | 3 | 4 | | | IV-2 | Haus5 | 0.97 | 5354 | 3 | 4 | | | IV-2 | Hmgxb4 | 0.88 |
| 5259 | 3 | 4 | | | IV-2 | Haus6 | 0.87 | 5355 | 3 | 4 | | | IV-2 | Hmha1 | 0.74 |
| 5260 | 3 | 4 | | | IV-2 | Hax1 | 0.89 | 5356 | 3 | 4 | | | IV-2 | Hmox2 | 0.82 |
| 5261 | 3 | 4 | | | IV-2 | Hba-a2 | 0.68 | 5357 | 3 | 4 | | | IV-2 | Hmx1 | 0.91 |
| 5262 | 3 | 4 | | | IV-2 | Hbegf | 0.98 | 5358 | 3 | 4 | | | IV-2 | Hn1 | 0.87 |
| 5263 | 3 | 4 | | | IV-2 | Hbs1l | 0.95 | 5359 | 3 | 4 | | | IV-2 | Hn1l | 0.83 |
| 5264 | 3 | 4 | | | IV-2 | Hcar2 | 0.85 | 5360 | 3 | 4 | | | IV-2 | Hnf1a | 0.79 |
| 5265 | 3 | 4 | | | IV-2 | Hccs | 0.86 | 5361 | 3 | 4 | | | IV-2 | Hnf1b | 0.69 |
| 5266 | 3 | 4 | | | IV-2 | Hcfc1 | 0.97 | 5362 | 3 | 4 | | | IV-2 | Hnmt | 0.82 |
| 5267 | 3 | 4 | | | IV-2 | Hcfc1r1 | 0.96 | 5363 | 3 | 4 | | | IV-2 | Hnrnpa1 | 0.85 |
| 5268 | 3 | 4 | | | IV-2 | Hcfc2 | 0.90 | 5364 | 3 | 4 | | | IV-2 | Hnrnpa2b1 | 0.76 |
| 5269 | 3 | 4 | | | IV-2 | Hcls1 | 0.91 | 5365 | 3 | 4 | | | IV-2 | Hnrnpab | 0.93 |
| 5270 | 3 | 4 | | | IV-2 | Hdac1 | 0.76 | 5366 | 3 | 4 | | | IV-2 | Hnrnpd | 0.99 |
| 5271 | 3 | 4 | | | IV-2 | Hdac2 | 0.97 | 5367 | 3 | 4 | | | IV-2 | Hnrnpf | 0.80 |
| 5272 | 3 | 4 | | | IV-2 | Hdac5 | 0.98 | 5368 | 3 | 4 | | | IV-2 | Hnrnph1 | 0.97 |
| 5273 | 3 | 4 | | | IV-2 | Hdac8 | 0.89 | 5369 | 3 | 4 | | | IV-2 | Hnrnph2 | 0.87 |
| 5274 | 3 | 4 | | | IV-2 | Hdac9 | 0.90 | 5370 | 3 | 4 | | | IV-2 | Hnrnph3 | 0.75 |
| 5275 | 3 | 4 | | | IV-2 | Hdc | 0.67 | 5371 | 3 | 4 | | | IV-2 | Hnrnpk | 0.88 |
| 5276 | 3 | 4 | | | IV-2 | Hddc3 | 0.85 | 5372 | 3 | 4 | | | IV-2 | Hnrnpl | 0.88 |
| 5277 | 3 | 4 | | | IV-2 | Hdgf | 0.86 | 5373 | 3 | 4 | | | IV-2 | Hnrnpm | 0.85 |
| 5278 | 3 | 4 | | | IV-2 | Hdhd2 | 0.77 | 5374 | 3 | 4 | | | IV-2 | Hnrnpu | 0.88 |

Fig. 45 - 29

| | | | | | | | | | | | | | | | |
|---|---|---|---|---|---|---|---|---|---|---|---|---|---|---|---|
| 5375 | 3 | 4 | | | IV-2 | Hnrnpul1 | 0.97 | 5471 | 3 | 4 | | | IV-2 | Igf2r | 0.87 |
| 5376 | 3 | 4 | | | IV-2 | Hnrnpul2 | 0.93 | 5472 | 3 | 4 | | | IV-2 | Igfbp7 | 0.74 |
| 5377 | 3 | 4 | | | IV-2 | Hoga1 | 0.81 | 5473 | 3 | 4 | | | IV-2 | Igf1r1 | 0.90 |
| 5378 | 3 | 4 | | | IV-2 | Homer1 | 0.90 | 5474 | 3 | 4 | | | IV-2 | Igip | 0.99 |
| 5379 | 3 | 4 | | | IV-2 | Homer2 | 0.94 | 5475 | 3 | 4 | | | IV-2 | Igsf10 | 0.95 |
| 5380 | 3 | 4 | | | IV-2 | Homez | 0.97 | 5476 | 3 | 4 | | | IV-2 | Igsf23 | 0.96 |
| 5381 | 3 | 4 | | | IV-2 | Hoxa10 | 0.98 | 5477 | 3 | 4 | | | IV-2 | Igsf8 | 0.96 |
| 5382 | 3 | 4 | | | IV-2 | Hoxa3 | 1.00 | 5478 | 3 | 4 | | | IV-2 | Ihh | 0.75 |
| 5383 | 3 | 4 | | | IV-2 | Hoxa4 | 0.73 | 5479 | 3 | 4 | | | IV-2 | Ikbke | 0.92 |
| 5384 | 3 | 4 | | | IV-2 | Hoxb13 | 0.91 | 5480 | 3 | 4 | | | IV-2 | Ikzf2 | 0.88 |
| 5385 | 3 | 4 | | | IV-2 | Hoxb2 | 0.93 | 5481 | 3 | 4 | | | IV-2 | Ikzf5 | 0.89 |
| 5386 | 3 | 4 | | | IV-2 | Hoxb4 | 0.80 | 5482 | 3 | 4 | | | IV-2 | Il10rb | 0.86 |
| 5387 | 3 | 4 | | | IV-2 | Hoxc6 | 0.95 | 5483 | 3 | 4 | | | IV-2 | Il13ra1 | 0.93 |
| 5388 | 3 | 4 | | | IV-2 | Hoxd4 | 0.83 | 5484 | 3 | 4 | | | IV-2 | Il15ra | 0.92 |
| 5389 | 3 | 4 | | | IV-2 | Hoxd8 | 0.85 | 5485 | 3 | 4 | | | IV-2 | Il17ra | 0.81 |
| 5390 | 3 | 4 | | | IV-2 | Hpd | 0.75 | 5486 | 3 | 4 | | | IV-2 | Il17rb | 0.69 |
| 5391 | 3 | 4 | | | IV-2 | Hpgds | 0.88 | 5487 | 3 | 4 | | | IV-2 | Il17re | 0.91 |
| 5392 | 3 | 4 | | | IV-2 | Hprt | 0.85 | 5488 | 3 | 4 | | | IV-2 | Il18 | 0.70 |
| 5393 | 3 | 4 | | | IV-2 | Hps1 | 0.96 | 5489 | 3 | 4 | | | IV-2 | Il1a | 0.67 |
| 5394 | 3 | 4 | | | IV-2 | Hps4 | 0.91 | 5490 | 3 | 4 | | | IV-2 | Il1f5 | 0.75 |
| 5395 | 3 | 4 | | | IV-2 | Hps5 | 0.95 | 5491 | 3 | 4 | | | IV-2 | Il1f9 | 0.95 |
| 5396 | 3 | 4 | | | IV-2 | Hps6 | 0.76 | 5492 | 3 | 4 | | | IV-2 | Il1rl1 | 0.71 |
| 5397 | 3 | 4 | | | IV-2 | Hpse | 0.77 | 5493 | 3 | 4 | | | IV-2 | Il21r | 0.77 |
| 5398 | 3 | 4 | | | IV-2 | Hpse2 | 0.99 | 5494 | 3 | 4 | | | IV-2 | Il22ra2 | 0.95 |
| 5399 | 3 | 4 | | | IV-2 | Hpx | 0.83 | 5495 | 3 | 4 | | | IV-2 | Il2rg | 0.69 |
| 5400 | 3 | 4 | | | IV-2 | Hras | 0.86 | 5496 | 3 | 4 | | | IV-2 | Il6ra | 0.95 |
| 5401 | 3 | 4 | | | IV-2 | Hrc | 0.73 | 5497 | 3 | 4 | | | IV-2 | Ilk | 0.93 |
| 5402 | 3 | 4 | | | IV-2 | Hrsp12 | 0.73 | 5498 | 3 | 4 | | | IV-2 | Ilkap | 0.83 |
| 5403 | 3 | 4 | | | IV-2 | Hs1bp3 | 0.74 | 5499 | 3 | 4 | | | IV-2 | Immp1l | 0.74 |
| 5404 | 3 | 4 | | | IV-2 | Hs3st3b1 | 0.77 | 5500 | 3 | 4 | | | IV-2 | Immp2l | 0.84 |
| 5405 | 3 | 4 | | | IV-2 | Hs6st1 | 0.88 | 5501 | 3 | 4 | | | IV-2 | Immt | 0.76 |
| 5406 | 3 | 4 | | | IV-2 | Hscb | 0.82 | 5502 | 3 | 4 | | | IV-2 | Imp4 | 0.87 |
| 5407 | 3 | 4 | | | IV-2 | Hsd11b1 | 0.81 | 5503 | 3 | 4 | | | IV-2 | Impa1 | 0.79 |
| 5408 | 3 | 4 | | | IV-2 | Hsd17b10 | 0.85 | 5504 | 3 | 4 | | | IV-2 | Impa2 | 0.77 |
| 5409 | 3 | 4 | | | IV-2 | Hsd17b12 | 0.89 | 5505 | 3 | 4 | | | IV-2 | Impdh1 | 0.83 |
| 5410 | 3 | 4 | | | IV-2 | Hsd17b14 | 0.99 | 5506 | 3 | 4 | | | IV-2 | Incenp | 0.74 |
| 5411 | 3 | 4 | | | IV-2 | Hsd17b4 | 0.85 | 5507 | 3 | 4 | | | IV-2 | Ing1 | 0.93 |
| 5412 | 3 | 4 | | | IV-2 | Hsd3b6 | 0.94 | 5508 | 3 | 4 | | | IV-2 | Ing2 | 0.74 |
| 5413 | 3 | 4 | | | IV-2 | Hsd3b7 | 0.87 | 5509 | 3 | 4 | | | IV-2 | Ing3 | 0.95 |
| 5414 | 3 | 4 | | | IV-2 | Hsdl2 | 0.72 | 5510 | 3 | 4 | | | IV-2 | Ing4 | 0.91 |
| 5415 | 3 | 4 | | | IV-2 | Hsf1 | 0.79 | 5511 | 3 | 4 | | | IV-2 | Ing5 | 0.83 |
| 5416 | 3 | 4 | | | IV-2 | Hsp90aa1 | 0.83 | 5512 | 3 | 4 | | | IV-2 | Inhba | 0.94 |
| 5417 | 3 | 4 | | | IV-2 | Hspa12b | 0.89 | 5513 | 3 | 4 | | | IV-2 | Inpp5a | 0.94 |
| 5418 | 3 | 4 | | | IV-2 | Hspa13 | 0.89 | 5514 | 3 | 4 | | | IV-2 | Inpp5b | 0.85 |
| 5419 | 3 | 4 | | | IV-2 | Hspa14 | 0.91 | 5515 | 3 | 4 | | | IV-2 | Inpp5d | 0.90 |
| 5420 | 3 | 4 | | | IV-2 | Hspa1a | 0.94 | 5516 | 3 | 4 | | | IV-2 | Inppl1 | 0.85 |
| 5421 | 3 | 4 | | | IV-2 | Hspa1b | 0.88 | 5517 | 3 | 4 | | | IV-2 | Insig1 | 0.79 |
| 5422 | 3 | 4 | | | IV-2 | Hspa2 | 0.97 | 5518 | 3 | 4 | | | IV-2 | Insig2 | 0.99 |
| 5423 | 3 | 4 | | | IV-2 | Hspa4l | 0.78 | 5519 | 3 | 4 | | | IV-2 | Ins6 | 0.84 |
| 5424 | 3 | 4 | | | IV-2 | Hspa8 | 0.95 | 5520 | 3 | 4 | | | IV-2 | Ints10 | 0.88 |
| 5425 | 3 | 4 | | | IV-2 | Hspa9 | 0.92 | 5521 | 3 | 4 | | | IV-2 | Ints12 | 0.94 |
| 5426 | 3 | 4 | | | IV-2 | Hspb1 | 0.85 | 5522 | 3 | 4 | | | IV-2 | Ints2 | 0.87 |
| 5427 | 3 | 4 | | | IV-2 | Hspb2 | 0.80 | 5523 | 3 | 4 | | | IV-2 | Ints3 | 0.77 |
| 5428 | 3 | 4 | | | IV-2 | Hspb3 | 0.72 | 5524 | 3 | 4 | | | IV-2 | Ints4 | 0.82 |
| 5429 | 3 | 4 | | | IV-2 | Hspb6 | 0.76 | 5525 | 3 | 4 | | | IV-2 | Ints5 | 0.87 |
| 5430 | 3 | 4 | | | IV-2 | Hspb7 | 0.83 | 5526 | 3 | 4 | | | IV-2 | Ints6 | 0.87 |
| 5431 | 3 | 4 | | | IV-2 | Hspb8 | 0.86 | 5527 | 3 | 4 | | | IV-2 | Ints7 | 0.90 |
| 5432 | 3 | 4 | | | IV-2 | Hspbp1 | 0.85 | 5528 | 3 | 4 | | | IV-2 | Ints8 | 0.70 |
| 5433 | 3 | 4 | | | IV-2 | Hspg2 | 0.94 | 5529 | 3 | 4 | | | IV-2 | Ints9 | 0.92 |
| 5434 | 3 | 4 | | | IV-2 | Htra2 | 0.93 | 5530 | 3 | 4 | | | IV-2 | Invs | 0.77 |
| 5435 | 3 | 4 | | | IV-2 | Htra3 | 0.82 | 5531 | 3 | 4 | | | IV-2 | Ip6k3 | 0.78 |
| 5436 | 3 | 4 | | | IV-2 | Hus1 | 0.75 | 5532 | 3 | 4 | | | IV-2 | Ipmk | 0.94 |
| 5437 | 3 | 4 | | | IV-2 | Huwe1 | 0.90 | 5533 | 3 | 4 | | | IV-2 | Ipo11 | 0.79 |
| 5438 | 3 | 4 | | | IV-2 | Hvcn1 | 0.96 | 5534 | 3 | 4 | | | IV-2 | Ipo5 | 0.85 |
| 5439 | 3 | 4 | | | IV-2 | Hyal2 | 0.78 | 5535 | 3 | 4 | | | IV-2 | Ipo7 | 0.83 |
| 5440 | 3 | 4 | | | IV-2 | Hyal3 | 0.88 | 5536 | 3 | 4 | | | IV-2 | Ipo8 | 0.76 |
| 5441 | 3 | 4 | | | IV-2 | Hyls1 | 0.68 | 5537 | 3 | 4 | | | IV-2 | Ipp | 0.92 |
| 5442 | 3 | 4 | | | IV-2 | Hyou1 | 0.72 | 5538 | 3 | 4 | | | IV-2 | Ipw | 0.97 |
| 5443 | 3 | 4 | | | IV-2 | Hypk | 0.84 | 5539 | 3 | 4 | | | IV-2 | Iqcb1 | 0.97 |
| 5444 | 3 | 4 | | | IV-2 | Iah1 | 0.85 | 5540 | 3 | 4 | | | IV-2 | Iqcc | 0.99 |
| 5445 | 3 | 4 | | | IV-2 | Iapp | 0.88 | 5541 | 3 | 4 | | | IV-2 | Iqcd | 0.96 |
| 5446 | 3 | 4 | | | IV-2 | Iba57 | 0.72 | 5542 | 3 | 4 | | | IV-2 | Iqgap1 | 0.93 |
| 5447 | 3 | 4 | | | IV-2 | Ibsp | 0.74 | 5543 | 3 | 4 | | | IV-2 | Iqgap2 | 0.75 |
| 5448 | 3 | 4 | | | IV-2 | Ibtk | 0.98 | 5544 | 3 | 4 | | | IV-2 | Iqgap3 | 0.82 |
| 5449 | 3 | 4 | | | IV-2 | Icmt | 0.93 | 5545 | 3 | 4 | | | IV-2 | Irak2 | 0.88 |
| 5450 | 3 | 4 | | | IV-2 | Id1 | 0.91 | 5546 | 3 | 4 | | | IV-2 | Irak4 | 0.80 |
| 5451 | 3 | 4 | | | IV-2 | Id3 | 0.79 | 5547 | 3 | 4 | | | IV-2 | Irf1 | 0.91 |
| 5452 | 3 | 4 | | | IV-2 | Ide | 0.88 | 5548 | 3 | 4 | | | IV-2 | Irf2 | 0.89 |
| 5453 | 3 | 4 | | | IV-2 | Idh1 | 0.91 | 5549 | 3 | 4 | | | IV-2 | Irf3 | 0.84 |
| 5454 | 3 | 4 | | | IV-2 | Idh2 | 0.86 | 5550 | 3 | 4 | | | IV-2 | Irf6 | 0.70 |
| 5455 | 3 | 4 | | | IV-2 | Idh3g | 0.87 | 5551 | 3 | 4 | | | IV-2 | Irf8 | 0.87 |
| 5456 | 3 | 4 | | | IV-2 | Idi1 | 0.76 | 5552 | 3 | 4 | | | IV-2 | Isca1 | 0.74 |
| 5457 | 3 | 4 | | | IV-2 | Idnk | 0.93 | 5553 | 3 | 4 | | | IV-2 | Isca2 | 0.80 |
| 5458 | 3 | 4 | | | IV-2 | Ier5l | 0.82 | 5554 | 3 | 4 | | | IV-2 | Isg20l2 | 0.92 |
| 5459 | 3 | 4 | | | IV-2 | Ifi30 | 0.87 | 5555 | 3 | 4 | | | IV-2 | Islr | 0.91 |
| 5460 | 3 | 4 | | | IV-2 | Ifitm5 | 0.87 | 5556 | 3 | 4 | | | IV-2 | Isoc1 | 0.92 |
| 5461 | 3 | 4 | | | IV-2 | Ifnar2 | 0.78 | 5557 | 3 | 4 | | | IV-2 | Isoc2b | 0.87 |
| 5462 | 3 | 4 | | | IV-2 | Ifnlr1 | 0.88 | 5558 | 3 | 4 | | | IV-2 | Ispd | 0.98 |
| 5463 | 3 | 4 | | | IV-2 | Ift122 | 0.83 | 5559 | 3 | 4 | | | IV-2 | Isy1 | 0.85 |
| 5464 | 3 | 4 | | | IV-2 | Ift172 | 0.82 | 5560 | 3 | 4 | | | IV-2 | Isyna1 | 0.84 |
| 5465 | 3 | 4 | | | IV-2 | Ift20 | 0.78 | 5561 | 3 | 4 | | | IV-2 | Itch | 0.89 |
| 5466 | 3 | 4 | | | IV-2 | Ift22 | 0.98 | 5562 | 3 | 4 | | | IV-2 | Itfg3 | 0.93 |
| 5467 | 3 | 4 | | | IV-2 | Igdcc4 | 0.97 | 5563 | 3 | 4 | | | IV-2 | Itga1 | 0.70 |
| 5468 | 3 | 4 | | | IV-2 | Igf2 | 0.88 | 5564 | 3 | 4 | | | IV-2 | Itga2 | 0.80 |
| 5469 | 3 | 4 | | | IV-2 | Igf2bp1 | 0.90 | 5565 | 3 | 4 | | | IV-2 | Itga5 | 0.87 |
| 5470 | 3 | 4 | | | IV-2 | Igf2bp3 | 0.94 | 5566 | 3 | 4 | | | IV-2 | Itga6 | 0.82 |

Fig. 45 - 30

| | | | | | | | | | | | | | | |
|---|---|---|---|---|---|---|---|---|---|---|---|---|---|---|
| 5567 | 3 | 4 | | | IV-2 | Itga7 | 0.76 | 5663 | 3 | 4 | | | IV-2 | Kif24 | 0.79 |
| 5568 | 3 | 4 | | | IV-2 | Itga8 | 0.85 | 5664 | 3 | 4 | | | IV-2 | Kif2c | 0.70 |
| 5569 | 3 | 4 | | | IV-2 | Itga9 | 0.93 | 5665 | 3 | 4 | | | IV-2 | Kif5b | 0.94 |
| 5570 | 3 | 4 | | | IV-2 | Itgb1 | 0.91 | 5666 | 3 | 4 | | | IV-2 | Kifc1 | 0.72 |
| 5571 | 3 | 4 | | | IV-2 | Itgb1bp1 | 0.99 | 5667 | 3 | 4 | | | IV-2 | Kifc5b | 0.71 |
| 5572 | 3 | 4 | | | IV-2 | Itgb2 | 0.95 | 5668 | 3 | 4 | | | IV-2 | Kir | 0.83 |
| 5573 | 3 | 4 | | | IV-2 | Itgb2l | 0.93 | 5669 | 3 | 4 | | | IV-2 | Kitl | 0.92 |
| 5574 | 3 | 4 | | | IV-2 | Itgb3bp | 0.99 | 5670 | 3 | 4 | | | IV-2 | Kiz | 0.92 |
| 5575 | 3 | 4 | | | IV-2 | Itgb5 | 0.84 | 5671 | 3 | 4 | | | IV-2 | Kl | 0.93 |
| 5576 | 3 | 4 | | | IV-2 | Itgb6 | 0.67 | 5672 | 3 | 4 | | | IV-2 | Klc3 | 0.68 |
| 5577 | 3 | 4 | | | IV-2 | Itgb7 | 0.97 | 5673 | 3 | 4 | | | IV-2 | Klc4 | 0.91 |
| 5578 | 3 | 4 | | | IV-2 | Itih5 | 0.90 | 5674 | 3 | 4 | | | IV-2 | Klf16 | 0.79 |
| 5579 | 3 | 4 | | | IV-2 | Itm2a | 0.93 | 5675 | 3 | 4 | | | IV-2 | Klf3 | 0.87 |
| 5580 | 3 | 4 | | | IV-2 | Itm2b | 0.94 | 5676 | 3 | 4 | | | IV-2 | Klf5 | 0.94 |
| 5581 | 3 | 4 | | | IV-2 | Itm2c | 0.97 | 5677 | 3 | 4 | | | IV-2 | Klf8 | 1.00 |
| 5582 | 3 | 4 | | | IV-2 | Itpa | 0.95 | 5678 | 3 | 4 | | | IV-2 | Klhdc1 | 0.93 |
| 5583 | 3 | 4 | | | IV-2 | Itpk1 | 0.85 | 5679 | 3 | 4 | | | IV-2 | Klhdc3 | 0.98 |
| 5584 | 3 | 4 | | | IV-2 | Itpkb | 0.87 | 5680 | 3 | 4 | | | IV-2 | Klhl12 | 0.90 |
| 5585 | 3 | 4 | | | IV-2 | Itpr2 | 0.86 | 5681 | 3 | 4 | | | IV-2 | Klhl13 | 0.88 |
| 5586 | 3 | 4 | | | IV-2 | Itpripl1 | 0.83 | 5682 | 3 | 4 | | | IV-2 | Klhl18 | 0.99 |
| 5587 | 3 | 4 | | | IV-2 | Itpripl2 | 0.92 | 5683 | 3 | 4 | | | IV-2 | Klhl21 | 0.92 |
| 5588 | 3 | 4 | | | IV-2 | Itsn1 | 0.98 | 5684 | 3 | 4 | | | IV-2 | Klhl25 | 0.76 |
| 5589 | 3 | 4 | | | IV-2 | Itsn2 | 0.82 | 5685 | 3 | 4 | | | IV-2 | Klhl28 | 0.86 |
| 5590 | 3 | 4 | | | IV-2 | Ivd | 0.86 | 5686 | 3 | 4 | | | IV-2 | Klhl3 | 0.88 |
| 5591 | 3 | 4 | | | IV-2 | Iws1 | 0.98 | 5687 | 3 | 4 | | | IV-2 | Klhl4 | 0.79 |
| 5592 | 3 | 4 | | | IV-2 | Jade1 | 0.95 | 5688 | 3 | 4 | | | IV-2 | Klhl40 | 0.82 |
| 5593 | 3 | 4 | | | IV-2 | Jagn1 | 0.86 | 5689 | 3 | 4 | | | IV-2 | Klhl41 | 0.96 |
| 5594 | 3 | 4 | | | IV-2 | Jak1 | 0.87 | 5690 | 3 | 4 | | | IV-2 | Klhl6 | 0.84 |
| 5595 | 3 | 4 | | | IV-2 | Jak3 | 0.99 | 5691 | 3 | 4 | | | IV-2 | Klhl9 | 0.75 |
| 5596 | 3 | 4 | | | IV-2 | Jam2 | 0.79 | 5692 | 3 | 4 | | | IV-2 | Klk10 | 0.82 |
| 5597 | 3 | 4 | | | IV-2 | Jam3 | 0.97 | 5693 | 3 | 4 | | | IV-2 | Klk14 | 0.75 |
| 5598 | 3 | 4 | | | IV-2 | Jarid2 | 0.89 | 5694 | 3 | 4 | | | IV-2 | Klk7 | 0.84 |
| 5599 | 3 | 4 | | | IV-2 | Jmjd4 | 0.90 | 5695 | 3 | 4 | | | IV-2 | Klk8 | 0.67 |
| 5600 | 3 | 4 | | | IV-2 | Jmjd6 | 0.80 | 5696 | 3 | 4 | | | IV-2 | Klrg2 | 0.94 |
| 5601 | 3 | 4 | | | IV-2 | Jmjd8 | 0.91 | 5697 | 3 | 4 | | | IV-2 | Kmt2c | 0.99 |
| 5602 | 3 | 4 | | | IV-2 | Josd1 | 0.74 | 5698 | 3 | 4 | | | IV-2 | Kmt2d | 0.95 |
| 5603 | 3 | 4 | | | IV-2 | Jpx | 0.95 | 5699 | 3 | 4 | | | IV-2 | Kng1 | 0.75 |
| 5604 | 3 | 4 | | | IV-2 | Jrkl | 0.96 | 5700 | 3 | 4 | | | IV-2 | Kng2 | 0.82 |
| 5605 | 3 | 4 | | | IV-2 | Jsrp1 | 0.69 | 5701 | 3 | 4 | | | IV-2 | Knstrn | 0.82 |
| 5606 | 3 | 4 | | | IV-2 | Jun | 0.96 | 5702 | 3 | 4 | | | IV-2 | Kpna1 | 0.91 |
| 5607 | 3 | 4 | | | IV-2 | Jup | 0.99 | 5703 | 3 | 4 | | | IV-2 | Kpna2 | 0.69 |
| 5608 | 3 | 4 | | | IV-2 | Kank1 | 0.83 | 5704 | 3 | 4 | | | IV-2 | Kpna3 | 0.88 |
| 5609 | 3 | 4 | | | IV-2 | Kank2 | 0.90 | 5705 | 3 | 4 | | | IV-2 | Kpna4 | 0.85 |
| 5610 | 3 | 4 | | | IV-2 | Kank4 | 0.80 | 5706 | 3 | 4 | | | IV-2 | Kpna6 | 0.80 |
| 5611 | 3 | 4 | | | IV-2 | Kansl1l | 0.95 | 5707 | 3 | 4 | | | IV-2 | Kpnb1 | 0.77 |
| 5612 | 3 | 4 | | | IV-2 | Kars | 0.91 | 5708 | 3 | 4 | | | IV-2 | Kptn | 0.89 |
| 5613 | 3 | 4 | | | IV-2 | Kat2b | 0.90 | 5709 | 3 | 4 | | | IV-2 | Kras | 0.98 |
| 5614 | 3 | 4 | | | IV-2 | Katna1 | 0.83 | 5710 | 3 | 4 | | | IV-2 | Krcc1 | 0.96 |
| 5615 | 3 | 4 | | | IV-2 | Kbtbd11 | 0.74 | 5711 | 3 | 4 | | | IV-2 | Kremen1 | 0.88 |
| 5616 | 3 | 4 | | | IV-2 | Kbtbd12 | 0.70 | 5712 | 3 | 4 | | | IV-2 | Kremen2 | 0.81 |
| 5617 | 3 | 4 | | | IV-2 | Kbtbd4 | 0.95 | 5713 | 3 | 4 | | | IV-2 | Krit1 | 0.88 |
| 5618 | 3 | 4 | | | IV-2 | Kbtbd7 | 0.96 | 5714 | 3 | 4 | | | IV-2 | Krr1 | 0.91 |
| 5619 | 3 | 4 | | | IV-2 | Kcmf1 | 1.00 | 5715 | 3 | 4 | | | IV-2 | Krt4 | 0.81 |
| 5620 | 3 | 4 | | | IV-2 | Kcne3 | 0.97 | 5716 | 3 | 4 | | | IV-2 | Krt5 | 0.92 |
| 5621 | 3 | 4 | | | IV-2 | Kcng2 | 0.86 | 5717 | 3 | 4 | | | IV-2 | Krt7 | 0.99 |
| 5622 | 3 | 4 | | | IV-2 | Kcnj16 | 0.87 | 5718 | 3 | 4 | | | IV-2 | Krt78 | 0.79 |
| 5623 | 3 | 4 | | | IV-2 | Kcnj5 | 0.76 | 5719 | 3 | 4 | | | IV-2 | Krt8 | 0.83 |
| 5624 | 3 | 4 | | | IV-2 | Kcnk13 | 0.84 | 5720 | 3 | 4 | | | IV-2 | Krt80 | 0.75 |
| 5625 | 3 | 4 | | | IV-2 | Kcnk5 | 0.75 | 5721 | 3 | 4 | | | IV-2 | Krtap13 | 0.69 |
| 5626 | 3 | 4 | | | IV-2 | Kcnk6 | 0.71 | 5722 | 3 | 4 | | | IV-2 | Krtap3-3 | 0.76 |
| 5627 | 3 | 4 | | | IV-2 | Kcnk7 | 0.90 | 5723 | 3 | 4 | | | IV-2 | Krtcap2 | 0.99 |
| 5628 | 3 | 4 | | | IV-2 | Kcnq1 | 0.97 | 5724 | 3 | 4 | | | IV-2 | Ksr1 | 0.83 |
| 5629 | 3 | 4 | | | IV-2 | Kcnq1ot1 | 0.97 | 5725 | 3 | 4 | | | IV-2 | Ktl12 | 0.76 |
| 5630 | 3 | 4 | | | IV-2 | Kcnq4 | 0.80 | 5726 | 3 | 4 | | | IV-2 | Kxd1 | 0.99 |
| 5631 | 3 | 4 | | | IV-2 | Kcns3 | 0.81 | 5727 | 3 | 4 | | | IV-2 | Kynu | 0.95 |
| 5632 | 3 | 4 | | | IV-2 | Kcp | 0.97 | 5728 | 3 | 4 | | | IV-2 | L2hgdh | 0.98 |
| 5633 | 3 | 4 | | | IV-2 | Kctd10 | 0.96 | 5729 | 3 | 4 | | | IV-2 | L3hypdh | 0.79 |
| 5634 | 3 | 4 | | | IV-2 | Kctd12b | 0.93 | 5730 | 3 | 4 | | | IV-2 | LOC100504608 | 0.84 |
| 5635 | 3 | 4 | | | IV-2 | Kctd20 | 0.92 | 5731 | 3 | 4 | | | IV-2 | LOC100861978 | 0.90 |
| 5636 | 3 | 4 | | | IV-2 | Kctd5 | 1.00 | 5732 | 3 | 4 | | | IV-2 | LOC101056043 | 0.74 |
| 5637 | 3 | 4 | | | IV-2 | Kctd7 | 0.89 | 5733 | 3 | 4 | | | IV-2 | LOC102636514 | 0.90 |
| 5638 | 3 | 4 | | | IV-2 | Kctd9 | 0.85 | 5734 | 3 | 4 | | | IV-2 | Lactb | 0.97 |
| 5639 | 3 | 4 | | | IV-2 | Kdelc1 | 0.88 | 5735 | 3 | 4 | | | IV-2 | Lactb2 | 0.68 |
| 5640 | 3 | 4 | | | IV-2 | Kdelc2 | 0.81 | 5736 | 3 | 4 | | | IV-2 | Lad1 | 0.76 |
| 5641 | 3 | 4 | | | IV-2 | Kdelr1 | 0.85 | 5737 | 3 | 4 | | | IV-2 | Lage3 | 0.94 |
| 5642 | 3 | 4 | | | IV-2 | Kdelr2 | 0.82 | 5738 | 3 | 4 | | | IV-2 | Lama3 | 0.78 |
| 5643 | 3 | 4 | | | IV-2 | Kdf1 | 0.73 | 5739 | 3 | 4 | | | IV-2 | Lama4 | 0.83 |
| 5644 | 3 | 4 | | | IV-2 | Kdm2a | 0.90 | 5740 | 3 | 4 | | | IV-2 | Lamb1 | 0.93 |
| 5645 | 3 | 4 | | | IV-2 | Kdm3a | 1.00 | 5741 | 3 | 4 | | | IV-2 | Lamb3 | 0.83 |
| 5646 | 3 | 4 | | | IV-2 | Kdm4c | 0.90 | 5742 | 3 | 4 | | | IV-2 | Lamc1 | 0.92 |
| 5647 | 3 | 4 | | | IV-2 | Kdm5c | 0.77 | 5743 | 3 | 4 | | | IV-2 | Lamp1 | 0.86 |
| 5648 | 3 | 4 | | | IV-2 | Kdm6a | 0.71 | 5744 | 3 | 4 | | | IV-2 | Lamp2 | 0.90 |
| 5649 | 3 | 4 | | | IV-2 | Kdm6b | 0.98 | 5745 | 3 | 4 | | | IV-2 | Lamp3 | 0.70 |
| 5650 | 3 | 4 | | | IV-2 | Kdm7a | 0.85 | 5746 | 3 | 4 | | | IV-2 | Lamtor1 | 0.83 |
| 5651 | 3 | 4 | | | IV-2 | Kdm8 | 0.79 | 5747 | 3 | 4 | | | IV-2 | Lamtor2 | 0.69 |
| 5652 | 3 | 4 | | | IV-2 | Kdr | 0.80 | 5748 | 3 | 4 | | | IV-2 | Lamtor3 | 0.86 |
| 5653 | 3 | 4 | | | IV-2 | Keap1 | 0.94 | 5749 | 3 | 4 | | | IV-2 | Lamtor4 | 0.90 |
| 5654 | 3 | 4 | | | IV-2 | Keg1 | 0.89 | 5750 | 3 | 4 | | | IV-2 | Lamtor5 | 0.80 |
| 5655 | 3 | 4 | | | IV-2 | Khdrbs1 | 0.97 | 5751 | 3 | 4 | | | IV-2 | Lap3 | 0.70 |
| 5656 | 3 | 4 | | | IV-2 | Khdrbs3 | 0.96 | 5752 | 3 | 4 | | | IV-2 | Laptm4a | 0.96 |
| 5657 | 3 | 4 | | | IV-2 | Khnyn | 0.91 | 5753 | 3 | 4 | | | IV-2 | Laptm4b | 0.85 |
| 5658 | 3 | 4 | | | IV-2 | Khsrp | 0.87 | 5754 | 3 | 4 | | | IV-2 | Laptm5 | 0.93 |
| 5659 | 3 | 4 | | | IV-2 | Kif12 | 0.99 | 5755 | 3 | 4 | | | IV-2 | Larp1 | 0.89 |
| 5660 | 3 | 4 | | | IV-2 | Kif13b | 0.82 | 5756 | 3 | 4 | | | IV-2 | Larp4 | 0.83 |
| 5661 | 3 | 4 | | | IV-2 | Kif16b | 0.94 | 5757 | 3 | 4 | | | IV-2 | Larp4b | 1.00 |
| 5662 | 3 | 4 | | | IV-2 | Kif1c | 0.97 | 5758 | 3 | 4 | | | IV-2 | Larp7 | 0.83 |

Fig. 45 - 31

| | | | | | | | | | | | | | | | | | |
|---|---|---|---|---|---|---|---|---|---|---|---|---|---|---|---|---|---|
| 5759 | 3 | 4 | | | IV-2 | Lars2 | 0.73 | | 5855 | 3 | 4 | | | IV-2 | Lrp10 | 0.92 |
| 5760 | 3 | 4 | | | IV-2 | Lasp1 | 0.97 | | 5856 | 3 | 4 | | | IV-2 | Lrp5 | 0.90 |
| 5761 | 3 | 4 | | | IV-2 | Lat2 | 0.94 | | 5857 | 3 | 4 | | | IV-2 | Lrpprc | 0.75 |
| 5762 | 3 | 4 | | | IV-2 | Layn | 0.81 | | 5858 | 3 | 4 | | | IV-2 | Lrr1 | 0.74 |
| 5763 | 3 | 4 | | | IV-2 | Lbp | 0.87 | | 5859 | 3 | 4 | | | IV-2 | Lrrc1 | 0.87 |
| 5764 | 3 | 4 | | | IV-2 | Lce1g | 0.78 | | 5860 | 3 | 4 | | | IV-2 | Lrrc14b | 0.75 |
| 5765 | 3 | 4 | | | IV-2 | Lce1i | 0.78 | | 5861 | 3 | 4 | | | IV-2 | Lrrc17 | 0.86 |
| 5766 | 3 | 4 | | | IV-2 | Lce1j | 0.84 | | 5862 | 3 | 4 | | | IV-2 | Lrrc20 | 0.96 |
| 5767 | 3 | 4 | | | IV-2 | Lce1l | 0.74 | | 5863 | 3 | 4 | | | IV-2 | Lrrc23 | 0.91 |
| 5768 | 3 | 4 | | | IV-2 | Lce1m | 0.78 | | 5864 | 3 | 4 | | | IV-2 | Lrrc27 | 0.93 |
| 5769 | 3 | 4 | | | IV-2 | Lce3d | 0.96 | | 5865 | 3 | 4 | | | IV-2 | Lrrc3 | 0.85 |
| 5770 | 3 | 4 | | | IV-2 | Lce6a | 0.68 | | 5866 | 3 | 4 | | | IV-2 | Lrrc30 | 0.67 |
| 5771 | 3 | 4 | | | IV-2 | Lck | 0.75 | | 5867 | 3 | 4 | | | IV-2 | Lrrc38 | 0.84 |
| 5772 | 3 | 4 | | | IV-2 | Lclat1 | 0.87 | | 5868 | 3 | 4 | | | IV-2 | Lrrc40 | 0.99 |
| 5773 | 3 | 4 | | | IV-2 | Lcmt1 | 0.68 | | 5869 | 3 | 4 | | | IV-2 | Lrrc41 | 0.95 |
| 5774 | 3 | 4 | | | IV-2 | Lcmt2 | 0.87 | | 5870 | 3 | 4 | | | IV-2 | Lrrc42 | 0.97 |
| 5775 | 3 | 4 | | | IV-2 | Lcor | 0.96 | | 5871 | 3 | 4 | | | IV-2 | Lrrc45 | 0.96 |
| 5776 | 3 | 4 | | | IV-2 | Lcp1 | 0.75 | | 5872 | 3 | 4 | | | IV-2 | Lrrc46 | 0.77 |
| 5777 | 3 | 4 | | | IV-2 | Lcp2 | 0.76 | | 5873 | 3 | 4 | | | IV-2 | Lrrc47 | 0.99 |
| 5778 | 3 | 4 | | | IV-2 | Ldb3 | 0.70 | | 5874 | 3 | 4 | | | IV-2 | Lrrc51 | 0.89 |
| 5779 | 3 | 4 | | | IV-2 | Ldhb | 0.96 | | 5875 | 3 | 4 | | | IV-2 | Lrrc56 | 0.74 |
| 5780 | 3 | 4 | | | IV-2 | Ldlr | 0.87 | | 5876 | 3 | 4 | | | IV-2 | Lrrc57 | 0.88 |
| 5781 | 3 | 4 | | | IV-2 | Ldlrap1 | 0.93 | | 5877 | 3 | 4 | | | IV-2 | Lrrc58 | 0.91 |
| 5782 | 3 | 4 | | | IV-2 | Lefty1 | 0.72 | | 5878 | 3 | 4 | | | IV-2 | Lrrc59 | 0.82 |
| 5783 | 3 | 4 | | | IV-2 | Lekr1 | 0.86 | | 5879 | 3 | 4 | | | IV-2 | Lrrc73 | 0.78 |
| 5784 | 3 | 4 | | | IV-2 | Leng1 | 0.82 | | 5880 | 3 | 4 | | | IV-2 | Lrrc8c | 0.72 |
| 5785 | 3 | 4 | | | IV-2 | Leo1 | 0.95 | | 5881 | 3 | 4 | | | IV-2 | Lrrfip1 | 0.98 |
| 5786 | 3 | 4 | | | IV-2 | Lepr | 0.96 | | 5882 | 3 | 4 | | | IV-2 | Lrrk1 | 0.89 |
| 5787 | 3 | 4 | | | IV-2 | Leprel | 0.84 | | 5883 | 3 | 4 | | | IV-2 | Lrrk2 | 0.92 |
| 5788 | 3 | 4 | | | IV-2 | Leprel1 | 0.99 | | 5884 | 3 | 4 | | | IV-2 | Lrrn4 | 0.98 |
| 5789 | 3 | 4 | | | IV-2 | Leprel2 | 0.96 | | 5885 | 3 | 4 | | | IV-2 | Lrwd1 | 0.79 |
| 5790 | 3 | 4 | | | IV-2 | Leprel4 | 0.99 | | 5886 | 3 | 4 | | | IV-2 | Lsm1 | 0.84 |
| 5791 | 3 | 4 | | | IV-2 | Letm1 | 0.88 | | 5887 | 3 | 4 | | | IV-2 | Lsm10 | 0.83 |
| 5792 | 3 | 4 | | | IV-2 | Letmd1 | 0.72 | | 5888 | 3 | 4 | | | IV-2 | Lsm12 | 0.92 |
| 5793 | 3 | 4 | | | IV-2 | Lfng | 0.81 | | 5889 | 3 | 4 | | | IV-2 | Lsm14a | 0.80 |
| 5794 | 3 | 4 | | | IV-2 | Lgals3 | 0.73 | | 5890 | 3 | 4 | | | IV-2 | Lsm2 | 0.83 |
| 5795 | 3 | 4 | | | IV-2 | Lgals4 | 0.68 | | 5891 | 3 | 4 | | | IV-2 | Lsm3 | 0.91 |
| 5796 | 3 | 4 | | | IV-2 | Lgals9 | 0.82 | | 5892 | 3 | 4 | | | IV-2 | Lsm4 | 0.80 |
| 5797 | 3 | 4 | | | IV-2 | Lgi2 | 0.78 | | 5893 | 3 | 4 | | | IV-2 | Lsm6 | 0.95 |
| 5798 | 3 | 4 | | | IV-2 | Lgi3 | 0.94 | | 5894 | 3 | 4 | | | IV-2 | Lsm7 | 0.85 |
| 5799 | 3 | 4 | | | IV-2 | Lgr6 | 0.75 | | 5895 | 3 | 4 | | | IV-2 | Lsm8 | 0.94 |
| 5800 | 3 | 4 | | | IV-2 | Lhfpl1 | 0.71 | | 5896 | 3 | 4 | | | IV-2 | Lsr | 0.69 |
| 5801 | 3 | 4 | | | IV-2 | Lhfpl2 | 0.80 | | 5897 | 3 | 4 | | | IV-2 | Lss | 0.68 |
| 5802 | 3 | 4 | | | IV-2 | Lhpp | 0.98 | | 5898 | 3 | 4 | | | IV-2 | Lst1 | 0.89 |
| 5803 | 3 | 4 | | | IV-2 | Lifr | 0.91 | | 5899 | 3 | 4 | | | IV-2 | Lta4h | 0.82 |
| 5804 | 3 | 4 | | | IV-2 | Lig1 | 0.77 | | 5900 | 3 | 4 | | | IV-2 | Ltbp2 | 0.99 |
| 5805 | 3 | 4 | | | IV-2 | Lig4 | 0.84 | | 5901 | 3 | 4 | | | IV-2 | Ltbp4 | 0.95 |
| 5806 | 3 | 4 | | | IV-2 | Lima1 | 0.97 | | 5902 | 3 | 4 | | | IV-2 | Ltn1 | 0.86 |
| 5807 | 3 | 4 | | | IV-2 | Limd1 | 0.86 | | 5903 | 3 | 4 | | | IV-2 | Lurap1 | 0.68 |
| 5808 | 3 | 4 | | | IV-2 | Lime1 | 1.00 | | 5904 | 3 | 4 | | | IV-2 | Lurap1l | 0.69 |
| 5809 | 3 | 4 | | | IV-2 | Lims1 | 0.84 | | 5905 | 3 | 4 | | | IV-2 | Luzp1 | 0.98 |
| 5810 | 3 | 4 | | | IV-2 | Lin37 | 0.88 | | 5906 | 3 | 4 | | | IV-2 | Lxn | 0.93 |
| 5811 | 3 | 4 | | | IV-2 | Lin54 | 0.87 | | 5907 | 3 | 4 | | | IV-2 | Ly6a | 0.80 |
| 5812 | 3 | 4 | | | IV-2 | Lins | 0.94 | | 5908 | 3 | 4 | | | IV-2 | Ly6d | 0.92 |
| 5813 | 3 | 4 | | | IV-2 | Lipa | 0.98 | | 5909 | 3 | 4 | | | IV-2 | Ly6e | 0.86 |
| 5814 | 3 | 4 | | | IV-2 | Lipg | 0.95 | | 5910 | 3 | 4 | | | IV-2 | Ly6g6c | 0.79 |
| 5815 | 3 | 4 | | | IV-2 | Liph | 0.80 | | 5911 | 3 | 4 | | | IV-2 | Ly6g6d | 0.85 |
| 5816 | 3 | 4 | | | IV-2 | Lipk | 0.78 | | 5912 | 3 | 4 | | | IV-2 | Ly86 | 0.79 |
| 5817 | 3 | 4 | | | IV-2 | Lipm | 0.75 | | 5913 | 3 | 4 | | | IV-2 | Lyar | 0.78 |
| 5818 | 3 | 4 | | | IV-2 | Lipt1 | 0.83 | | 5914 | 3 | 4 | | | IV-2 | Lyn | 0.87 |
| 5819 | 3 | 4 | | | IV-2 | Litaf | 1.00 | | 5915 | 3 | 4 | | | IV-2 | Lypd2 | 0.84 |
| 5820 | 3 | 4 | | | IV-2 | Llgl1 | 0.99 | | 5916 | 3 | 4 | | | IV-2 | Lypd5 | 0.87 |
| 5821 | 3 | 4 | | | IV-2 | Llgl2 | 0.75 | | 5917 | 3 | 4 | | | IV-2 | Lypla1 | 0.77 |
| 5822 | 3 | 4 | | | IV-2 | Llph | 0.91 | | 5918 | 3 | 4 | | | IV-2 | Lyplal1 | 1.00 |
| 5823 | 3 | 4 | | | IV-2 | Lman1 | 0.75 | | 5919 | 3 | 4 | | | IV-2 | Lyrm4 | 0.93 |
| 5824 | 3 | 4 | | | IV-2 | Lman2 | 0.73 | | 5920 | 3 | 4 | | | IV-2 | Lyrm5 | 0.78 |
| 5825 | 3 | 4 | | | IV-2 | Lman2l | 0.81 | | 5921 | 3 | 4 | | | IV-2 | Lysmd2 | 0.96 |
| 5826 | 3 | 4 | | | IV-2 | Lmbrd2 | 0.95 | | 5922 | 3 | 4 | | | IV-2 | Lysmd3 | 0.79 |
| 5827 | 3 | 4 | | | IV-2 | Lmf1 | 0.75 | | 5923 | 3 | 4 | | | IV-2 | Lyst | 0.75 |
| 5828 | 3 | 4 | | | IV-2 | Lmf2 | 0.89 | | 5924 | 3 | 4 | | | IV-2 | Lztfl1 | 1.00 |
| 5829 | 3 | 4 | | | IV-2 | Lmna | 0.88 | | 5925 | 3 | 4 | | | IV-2 | Lztr1 | 0.94 |
| 5830 | 3 | 4 | | | IV-2 | Lmnb1 | 0.69 | | 5926 | 3 | 4 | | | IV-2 | Lzts3 | 0.80 |
| 5831 | 3 | 4 | | | IV-2 | Lmnb2 | 0.71 | | 5927 | 3 | 4 | | | IV-2 | M6pr | 0.87 |
| 5832 | 3 | 4 | | | IV-2 | Lmo7 | 0.85 | | 5928 | 3 | 4 | | | IV-2 | Macrod1 | 0.82 |
| 5833 | 3 | 4 | | | IV-2 | Lmod1 | 0.94 | | 5929 | 3 | 4 | | | IV-2 | Macrod2 | 0.97 |
| 5834 | 3 | 4 | | | IV-2 | Lmod2 | 0.74 | | 5930 | 3 | 4 | | | IV-2 | Mad1l1 | 0.98 |
| 5835 | 3 | 4 | | | IV-2 | Lmod3 | 0.67 | | 5931 | 3 | 4 | | | IV-2 | Mad2l1bp | 0.77 |
| 5836 | 3 | 4 | | | IV-2 | Lmtk2 | 0.98 | | 5932 | 3 | 4 | | | IV-2 | Maea | 0.95 |
| 5837 | 3 | 4 | | | IV-2 | Lnpep | 1.00 | | 5933 | 3 | 4 | | | IV-2 | Mafb | 0.93 |
| 5838 | 3 | 4 | | | IV-2 | Lnx2 | 0.83 | | 5934 | 3 | 4 | | | IV-2 | Maff | 0.83 |
| 5839 | 3 | 4 | | | IV-2 | Lonp1 | 0.95 | | 5935 | 3 | 4 | | | IV-2 | Mafk | 0.81 |
| 5840 | 3 | 4 | | | IV-2 | Lonp2 | 0.85 | | 5936 | 3 | 4 | | | IV-2 | Maged2 | 0.83 |
| 5841 | 3 | 4 | | | IV-2 | Lonrf3 | 0.99 | | 5937 | 3 | 4 | | | IV-2 | Magel2 | 0.96 |
| 5842 | 3 | 4 | | | IV-2 | Lor | 0.78 | | 5938 | 3 | 4 | | | IV-2 | Magi3 | 1.00 |
| 5843 | 3 | 4 | | | IV-2 | Loxl2 | 0.92 | | 5939 | 3 | 4 | | | IV-2 | Magoh | 0.91 |
| 5844 | 3 | 4 | | | IV-2 | Loxl4 | 0.93 | | 5940 | 3 | 4 | | | IV-2 | Mak16 | 0.94 |
| 5845 | 3 | 4 | | | IV-2 | Lpar1 | 0.99 | | 5941 | 3 | 4 | | | IV-2 | Mal | 0.92 |
| 5846 | 3 | 4 | | | IV-2 | Lpar3 | 0.75 | | 5942 | 3 | 4 | | | IV-2 | Mal2 | 0.82 |
| 5847 | 3 | 4 | | | IV-2 | Lpar5 | 0.89 | | 5943 | 3 | 4 | | | IV-2 | Mall | 0.76 |
| 5848 | 3 | 4 | | | IV-2 | Lpar6 | 0.71 | | 5944 | 3 | 4 | | | IV-2 | Mamld1 | 0.93 |
| 5849 | 3 | 4 | | | IV-2 | Lpcat1 | 0.81 | | 5945 | 3 | 4 | | | IV-2 | Mamstr | 0.69 |
| 5850 | 3 | 4 | | | IV-2 | Lpin1 | 0.99 | | 5946 | 3 | 4 | | | IV-2 | Man1a | 0.81 |
| 5851 | 3 | 4 | | | IV-2 | Lpl | 0.73 | | 5947 | 3 | 4 | | | IV-2 | Man1b1 | 0.95 |
| 5852 | 3 | 4 | | | IV-2 | Lpp | 0.93 | | 5948 | 3 | 4 | | | IV-2 | Man2b1 | 0.97 |
| 5853 | 3 | 4 | | | IV-2 | Lrba | 0.86 | | 5949 | 3 | 4 | | | IV-2 | Manea | 0.99 |
| 5854 | 3 | 4 | | | IV-2 | Lrig1 | 0.81 | | 5950 | 3 | 4 | | | IV-2 | Manf | 0.67 |

Fig. 45 - 32

| | | | | | | | | | | | | | |
|---|---|---|---|---|---|---|---|---|---|---|---|---|---|
| 5951 | 3 | 4 | | | IV-2 | Mansc4 | 0.76 | 6047 | 3 | 4 | | IV-2 | Meox1 | 0.95 |
| 5952 | 3 | 4 | | | IV-2 | Map1a | 0.93 | 6048 | 3 | 4 | | IV-2 | Meox2 | 0.84 |
| 5953 | 3 | 4 | | | IV-2 | Map2k1 | 0.74 | 6049 | 3 | 4 | | IV-2 | Mep1b | 0.91 |
| 5954 | 3 | 4 | | | IV-2 | Map2k2 | 0.87 | 6050 | 3 | 4 | | IV-2 | Mepce | 0.97 |
| 5955 | 3 | 4 | | | IV-2 | Map2k3 | 0.72 | 6051 | 3 | 4 | | IV-2 | Mesdc1 | 0.83 |
| 5956 | 3 | 4 | | | IV-2 | Map2k6 | 0.86 | 6052 | 3 | 4 | | IV-2 | Mesdc2 | 0.87 |
| 5957 | 3 | 4 | | | IV-2 | Map3k1 | 0.77 | 6053 | 3 | 4 | | IV-2 | Mest | 0.80 |
| 5958 | 3 | 4 | | | IV-2 | Map3k11 | 0.81 | 6054 | 3 | 4 | | IV-2 | Met | 0.67 |
| 5959 | 3 | 4 | | | IV-2 | Map3k14 | 0.83 | 6055 | 3 | 4 | | IV-2 | Metap1 | 0.93 |
| 5960 | 3 | 4 | | | IV-2 | Map3k3 | 0.93 | 6056 | 3 | 4 | | IV-2 | Metap1d | 0.79 |
| 5961 | 3 | 4 | | | IV-2 | Map3k4 | 0.82 | 6057 | 3 | 4 | | IV-2 | Metap2 | 0.85 |
| 5962 | 3 | 4 | | | IV-2 | Map3k5 | 0.89 | 6058 | 3 | 4 | | IV-2 | Metrn | 0.88 |
| 5963 | 3 | 4 | | | IV-2 | Map3k7cl | 0.80 | 6059 | 3 | 4 | | IV-2 | Metrnl | 0.74 |
| 5964 | 3 | 4 | | | IV-2 | Map6d1 | 0.99 | 6060 | 3 | 4 | | IV-2 | Mettl1 | 0.90 |
| 5965 | 3 | 4 | | | IV-2 | Map7 | 0.84 | 6061 | 3 | 4 | | IV-2 | Mettl10 | 0.99 |
| 5966 | 3 | 4 | | | IV-2 | Map7d1 | 0.98 | 6062 | 3 | 4 | | IV-2 | Mettl14 | 0.89 |
| 5967 | 3 | 4 | | | IV-2 | Mapk1 | 0.93 | 6063 | 3 | 4 | | IV-2 | Mettl15 | 0.86 |
| 5968 | 3 | 4 | | | IV-2 | Mapk12 | 0.99 | 6064 | 3 | 4 | | IV-2 | Mettl2 | 0.82 |
| 5969 | 3 | 4 | | | IV-2 | Mapk14 | 0.82 | 6065 | 3 | 4 | | IV-2 | Mettl21a | 0.98 |
| 5970 | 3 | 4 | | | IV-2 | Mapk1ip1l | 0.87 | 6066 | 3 | 4 | | IV-2 | Mettl21e | 0.89 |
| 5971 | 3 | 4 | | | IV-2 | Mapk3 | 0.87 | 6067 | 3 | 4 | | IV-2 | Mettl23 | 0.77 |
| 5972 | 3 | 4 | | | IV-2 | Mapkap1 | 0.95 | 6068 | 3 | 4 | | IV-2 | Mettl3 | 0.84 |
| 5973 | 3 | 4 | | | IV-2 | Mapkapk2 | 0.97 | 6069 | 3 | 4 | | IV-2 | Mettl4 | 0.75 |
| 5974 | 3 | 4 | | | IV-2 | Mapkapk3 | 0.73 | 6070 | 3 | 4 | | IV-2 | Mettl6 | 0.97 |
| 5975 | 3 | 4 | | | IV-2 | Marc1 | 0.79 | 6071 | 3 | 4 | | IV-2 | Mettl7b | 0.87 |
| 5976 | 3 | 4 | | | IV-2 | March2 | 0.78 | 6072 | 3 | 4 | | IV-2 | Mettl8 | 0.96 |
| 5977 | 3 | 4 | | | IV-2 | March8 | 0.80 | 6073 | 3 | 4 | | IV-2 | Mettl9 | 0.90 |
| 5978 | 3 | 4 | | | IV-2 | Marf1 | 0.87 | 6074 | 3 | 4 | | IV-2 | Mfap1a | 0.87 |
| 5979 | 3 | 4 | | | IV-2 | Mars | 0.98 | 6075 | 3 | 4 | | IV-2 | Mfap1b | 0.95 |
| 5980 | 3 | 4 | | | IV-2 | Mars2 | 0.82 | 6076 | 3 | 4 | | IV-2 | Mfap4 | 0.88 |
| 5981 | 3 | 4 | | | IV-2 | Marveld1 | 0.96 | 6077 | 3 | 4 | | IV-2 | Mfap5 | 0.88 |
| 5982 | 3 | 4 | | | IV-2 | Marveld2 | 0.88 | 6078 | 3 | 4 | | IV-2 | Mfhas1 | 0.95 |
| 5983 | 3 | 4 | | | IV-2 | Marveld3 | 0.69 | 6079 | 3 | 4 | | IV-2 | Mfn2 | 0.91 |
| 5984 | 3 | 4 | | | IV-2 | Masp1 | 0.71 | 6080 | 3 | 4 | | IV-2 | Mfsd1 | 0.87 |
| 5985 | 3 | 4 | | | IV-2 | Mast3 | 0.95 | 6081 | 3 | 4 | | IV-2 | Mfsd4 | 0.93 |
| 5986 | 3 | 4 | | | IV-2 | Mastl | 0.90 | 6082 | 3 | 4 | | IV-2 | Mfsd5 | 0.90 |
| 5987 | 3 | 4 | | | IV-2 | Mat2b | 0.85 | 6083 | 3 | 4 | | IV-2 | Mfsd6 | 0.86 |
| 5988 | 3 | 4 | | | IV-2 | Matn2 | 0.90 | 6084 | 3 | 4 | | IV-2 | Mfsd6l | 0.90 |
| 5989 | 3 | 4 | | | IV-2 | Mavs | 0.69 | 6085 | 3 | 4 | | IV-2 | Mfsd7a | 0.72 |
| 5990 | 3 | 4 | | | IV-2 | Max | 0.96 | 6086 | 3 | 4 | | IV-2 | Mfsd7c | 0.80 |
| 5991 | 3 | 4 | | | IV-2 | Maz | 0.92 | 6087 | 3 | 4 | | IV-2 | Mgarp | 0.75 |
| 5992 | 3 | 4 | | | IV-2 | Mb | 0.93 | 6088 | 3 | 4 | | IV-2 | Mgat1 | 0.93 |
| 5993 | 3 | 4 | | | IV-2 | Mb21d1 | 0.75 | 6089 | 3 | 4 | | IV-2 | Mgat2 | 0.83 |
| 5994 | 3 | 4 | | | IV-2 | Mb21d2 | 1.00 | 6090 | 3 | 4 | | IV-2 | Mgat4a | 0.96 |
| 5995 | 3 | 4 | | | IV-2 | Mbd2 | 0.83 | 6091 | 3 | 4 | | IV-2 | Mgst1 | 0.81 |
| 5996 | 3 | 4 | | | IV-2 | Mbd3 | 0.87 | 6092 | 3 | 4 | | IV-2 | Mia | 0.95 |
| 5997 | 3 | 4 | | | IV-2 | Mbd4 | 0.84 | 6093 | 3 | 4 | | IV-2 | Mia2 | 0.84 |
| 5998 | 3 | 4 | | | IV-2 | Mbip | 0.87 | 6094 | 3 | 4 | | IV-2 | Mical2 | 0.78 |
| 5999 | 3 | 4 | | | IV-2 | Mbnl1 | 0.84 | 6095 | 3 | 4 | | IV-2 | Mical3 | 0.97 |
| 6000 | 3 | 4 | | | IV-2 | Mbnl3 | 0.77 | 6096 | 3 | 4 | | IV-2 | Micall2 | 0.82 |
| 6001 | 3 | 4 | | | IV-2 | Mboat1 | 0.84 | 6097 | 3 | 4 | | IV-2 | Micu1 | 0.90 |
| 6002 | 3 | 4 | | | IV-2 | Mboat2 | 0.76 | 6098 | 3 | 4 | | IV-2 | Mid2 | 0.97 |
| 6003 | 3 | 4 | | | IV-2 | Mbp | 0.96 | 6099 | 3 | 4 | | IV-2 | Mief1 | 0.96 |
| 6004 | 3 | 4 | | | IV-2 | Mc2r | 0.94 | 6100 | 3 | 4 | | IV-2 | Mief2 | 0.96 |
| 6005 | 3 | 4 | | | IV-2 | Mcc | 0.96 | 6101 | 3 | 4 | | IV-2 | Mien1 | 0.79 |
| 6006 | 3 | 4 | | | IV-2 | Mccc1 | 0.84 | 6102 | 3 | 4 | | IV-2 | Mier1 | 0.99 |
| 6007 | 3 | 4 | | | IV-2 | Mccc2 | 0.96 | 6103 | 3 | 4 | | IV-2 | Mier2 | 0.99 |
| 6008 | 3 | 4 | | | IV-2 | Mcee | 0.78 | 6104 | 3 | 4 | | IV-2 | Mier3 | 0.97 |
| 6009 | 3 | 4 | | | IV-2 | Mcemp1 | 0.97 | 6105 | 3 | 4 | | IV-2 | Mif | 0.86 |
| 6010 | 3 | 4 | | | IV-2 | Mcfd2 | 0.80 | 6106 | 3 | 4 | | IV-2 | Mif4gd | 0.84 |
| 6011 | 3 | 4 | | | IV-2 | Mcl1 | 0.93 | 6107 | 3 | 4 | | IV-2 | Minos1 | 0.85 |
| 6012 | 3 | 4 | | | IV-2 | Mcm4 | 0.68 | 6108 | 3 | 4 | | IV-2 | Minpp1 | 0.75 |
| 6013 | 3 | 4 | | | IV-2 | Mcm7 | 0.76 | 6109 | 3 | 4 | | IV-2 | Mip | 0.80 |
| 6014 | 3 | 4 | | | IV-2 | Mcm8 | 0.70 | 6110 | 3 | 4 | | IV-2 | Mipep | 0.76 |
| 6015 | 3 | 4 | | | IV-2 | Mcoln2 | 0.79 | 6111 | 3 | 4 | | IV-2 | Mir143hg | 0.97 |
| 6016 | 3 | 4 | | | IV-2 | Mcph1 | 0.73 | 6112 | 3 | 4 | | IV-2 | Mir17hg | 0.97 |
| 6017 | 3 | 4 | | | IV-2 | Mcts1 | 0.99 | 6113 | 3 | 4 | | IV-2 | Mirg | 0.77 |
| 6018 | 3 | 4 | | | IV-2 | Mcu | 0.98 | 6114 | 3 | 4 | | IV-2 | Mis12 | 0.68 |
| 6019 | 3 | 4 | | | IV-2 | Mcur1 | 0.94 | 6115 | 3 | 4 | | IV-2 | Mis18a | 0.88 |
| 6020 | 3 | 4 | | | IV-2 | Mdc1 | 0.77 | 6116 | 3 | 4 | | IV-2 | Mis18bp1 | 0.70 |
| 6021 | 3 | 4 | | | IV-2 | Mdfic | 1.00 | 6117 | 3 | 4 | | IV-2 | Mitd1 | 0.93 |
| 6022 | 3 | 4 | | | IV-2 | Mdh1 | 0.67 | 6118 | 3 | 4 | | IV-2 | Mkl1 | 0.91 |
| 6023 | 3 | 4 | | | IV-2 | Mdh2 | 0.73 | 6119 | 3 | 4 | | IV-2 | Mknk1 | 0.93 |
| 6024 | 3 | 4 | | | IV-2 | Mdk | 0.95 | 6120 | 3 | 4 | | IV-2 | Mknk2 | 0.73 |
| 6025 | 3 | 4 | | | IV-2 | Mdn1 | 0.98 | 6121 | 3 | 4 | | IV-2 | Mlf2 | 0.89 |
| 6026 | 3 | 4 | | | IV-2 | Mdp1 | 0.90 | 6122 | 3 | 4 | | IV-2 | Mth1 | 0.93 |
| 6027 | 3 | 4 | | | IV-2 | Me2 | 0.73 | 6123 | 3 | 4 | | IV-2 | Mllt1 | 0.94 |
| 6028 | 3 | 4 | | | IV-2 | Mea1 | 0.94 | 6124 | 3 | 4 | | IV-2 | Mllt10 | 0.99 |
| 6029 | 3 | 4 | | | IV-2 | Mecr | 0.75 | 6125 | 3 | 4 | | IV-2 | Mllt3 | 0.96 |
| 6030 | 3 | 4 | | | IV-2 | Med1 | 0.86 | 6126 | 3 | 4 | | IV-2 | Mlst8 | 0.94 |
| 6031 | 3 | 4 | | | IV-2 | Med11 | 0.80 | 6127 | 3 | 4 | | IV-2 | Mlx | 0.73 |
| 6032 | 3 | 4 | | | IV-2 | Med14 | 0.96 | 6128 | 3 | 4 | | IV-2 | Mmab | 0.96 |
| 6033 | 3 | 4 | | | IV-2 | Med18 | 0.95 | 6129 | 3 | 4 | | IV-2 | Mmachc | 0.76 |
| 6034 | 3 | 4 | | | IV-2 | Med19 | 0.93 | 6130 | 3 | 4 | | IV-2 | Mmadhc | 0.87 |
| 6035 | 3 | 4 | | | IV-2 | Med20 | 0.85 | 6131 | 3 | 4 | | IV-2 | Mmd | 0.98 |
| 6036 | 3 | 4 | | | IV-2 | Med21 | 0.71 | 6132 | 3 | 4 | | IV-2 | Mmd2 | 0.73 |
| 6037 | 3 | 4 | | | IV-2 | Med28 | 0.89 | 6133 | 3 | 4 | | IV-2 | Mmgt1 | 0.86 |
| 6038 | 3 | 4 | | | IV-2 | Med29 | 0.99 | 6134 | 3 | 4 | | IV-2 | Mmgt2 | 0.97 |
| 6039 | 3 | 4 | | | IV-2 | Med31 | 0.95 | 6135 | 3 | 4 | | IV-2 | Mmp13 | 0.78 |
| 6040 | 3 | 4 | | | IV-2 | Med6 | 0.91 | 6136 | 3 | 4 | | IV-2 | Mmp14 | 0.99 |
| 6041 | 3 | 4 | | | IV-2 | Med7 | 0.97 | 6137 | 3 | 4 | | IV-2 | Mmp15 | 1.00 |
| 6042 | 3 | 4 | | | IV-2 | Med9 | 0.92 | 6138 | 3 | 4 | | IV-2 | Mmp17 | 0.95 |
| 6043 | 3 | 4 | | | IV-2 | Mef2d | 0.94 | 6139 | 3 | 4 | | IV-2 | Mmp19 | 0.85 |
| 6044 | 3 | 4 | | | IV-2 | Melk | 0.74 | 6140 | 3 | 4 | | IV-2 | Mmp23 | 0.78 |
| 6045 | 3 | 4 | | | IV-2 | Memo1 | 0.82 | 6141 | 3 | 4 | | IV-2 | Mmp28 | 0.93 |
| 6046 | 3 | 4 | | | IV-2 | Men1 | 0.82 | 6142 | 3 | 4 | | IV-2 | Mmrn2 | 0.92 |

Fig. 45 - 33

| | | | | | | | |
|---|---|---|---|---|---|---|---|
| 6143 | 3 | 4 | IV-2 | Mms22l | 0.83 |
| 6144 | 3 | 4 | IV-2 | Mnd1-ps | 0.80 |
| 6145 | 3 | 4 | IV-2 | Mob1a | 0.73 |
| 6146 | 3 | 4 | IV-2 | Mob1b | 0.78 |
| 6147 | 3 | 4 | IV-2 | Mob2 | 0.96 |
| 6148 | 3 | 4 | IV-2 | Mob3a | 0.83 |
| 6149 | 3 | 4 | IV-2 | Mob3b | 0.83 |
| 6150 | 3 | 4 | IV-2 | Mob4 | 0.80 |
| 6151 | 3 | 4 | IV-2 | Mocs2 | 0.91 |
| 6152 | 3 | 4 | IV-2 | Mocs3 | 0.88 |
| 6153 | 3 | 4 | IV-2 | Mog | 0.98 |
| 6154 | 3 | 4 | IV-2 | Mogs | 0.75 |
| 6155 | 3 | 4 | IV-2 | Mon1a | 0.73 |
| 6156 | 3 | 4 | IV-2 | Mon1b | 0.97 |
| 6157 | 3 | 4 | IV-2 | Mon2 | 0.99 |
| 6158 | 3 | 4 | IV-2 | Morf4l1 | 0.90 |
| 6159 | 3 | 4 | IV-2 | Morf4l2 | 0.92 |
| 6160 | 3 | 4 | IV-2 | Morn2 | 0.78 |
| 6161 | 3 | 4 | IV-2 | Mospd1 | 0.90 |
| 6162 | 3 | 4 | IV-2 | Mov10 | 0.70 |
| 6163 | 3 | 4 | IV-2 | Mpc1 | 0.80 |
| 6164 | 3 | 4 | IV-2 | Mpc2 | 0.90 |
| 6165 | 3 | 4 | IV-2 | Mphosph10 | 0.90 |
| 6166 | 3 | 4 | IV-2 | Mphosph6 | 0.99 |
| 6167 | 3 | 4 | IV-2 | Mphosph8 | 0.98 |
| 6168 | 3 | 4 | IV-2 | Mphosph9 | 0.98 |
| 6169 | 3 | 4 | IV-2 | Mpi | 0.74 |
| 6170 | 3 | 4 | IV-2 | Mpl | 0.79 |
| 6171 | 3 | 4 | IV-2 | Mpnd | 0.87 |
| 6172 | 3 | 4 | IV-2 | Mpo | 0.70 |
| 6173 | 3 | 4 | IV-2 | Mpp1 | 0.70 |
| 6174 | 3 | 4 | IV-2 | Mpp2 | 0.71 |
| 6175 | 3 | 4 | IV-2 | Mpp5 | 0.77 |
| 6176 | 3 | 4 | IV-2 | Mpp6 | 0.97 |
| 6177 | 3 | 4 | IV-2 | Mpp7 | 0.87 |
| 6178 | 3 | 4 | IV-2 | Mppe1 | 0.73 |
| 6179 | 3 | 4 | IV-2 | Mpst | 0.69 |
| 6180 | 3 | 4 | IV-2 | Mpv17 | 0.93 |
| 6181 | 3 | 4 | IV-2 | Mpv17l2 | 0.78 |
| 6182 | 3 | 4 | IV-2 | Mpz | 0.88 |
| 6183 | 3 | 4 | IV-2 | Mpzl2 | 0.96 |
| 6184 | 3 | 4 | IV-2 | Mpzl3 | 0.90 |
| 6185 | 3 | 4 | IV-2 | Mrc1 | 0.92 |
| 6186 | 3 | 4 | IV-2 | Mrc2 | 0.92 |
| 6187 | 3 | 4 | IV-2 | Mreg | 0.74 |
| 6188 | 3 | 4 | IV-2 | Mrfap1 | 0.83 |
| 6189 | 3 | 4 | IV-2 | Mrgprx1 | 0.76 |
| 6190 | 3 | 4 | IV-2 | Mrm1 | 0.93 |
| 6191 | 3 | 4 | IV-2 | Mrpl1 | 0.95 |
| 6192 | 3 | 4 | IV-2 | Mrpl10 | 0.88 |
| 6193 | 3 | 4 | IV-2 | Mrpl11 | 0.88 |
| 6194 | 3 | 4 | IV-2 | Mrpl12 | 0.71 |
| 6195 | 3 | 4 | IV-2 | Mrpl13 | 0.82 |
| 6196 | 3 | 4 | IV-2 | Mrpl14 | 0.73 |
| 6197 | 3 | 4 | IV-2 | Mrpl15 | 0.68 |
| 6198 | 3 | 4 | IV-2 | Mrpl16 | 0.83 |
| 6199 | 3 | 4 | IV-2 | Mrpl17 | 0.88 |
| 6200 | 3 | 4 | IV-2 | Mrpl18 | 0.70 |
| 6201 | 3 | 4 | IV-2 | Mrpl19 | 0.80 |
| 6202 | 3 | 4 | IV-2 | Mrpl20 | 0.87 |
| 6203 | 3 | 4 | IV-2 | Mrpl21 | 0.78 |
| 6204 | 3 | 4 | IV-2 | Mrpl22 | 0.84 |
| 6205 | 3 | 4 | IV-2 | Mrpl23 | 0.97 |
| 6206 | 3 | 4 | IV-2 | Mrpl27 | 0.87 |
| 6207 | 3 | 4 | IV-2 | Mrpl28 | 0.80 |
| 6208 | 3 | 4 | IV-2 | Mrpl3 | 0.95 |
| 6209 | 3 | 4 | IV-2 | Mrpl30 | 0.99 |
| 6210 | 3 | 4 | IV-2 | Mrpl32 | 0.72 |
| 6211 | 3 | 4 | IV-2 | Mrpl33 | 0.82 |
| 6212 | 3 | 4 | IV-2 | Mrpl36 | 0.71 |
| 6213 | 3 | 4 | IV-2 | Mrpl37 | 0.72 |
| 6214 | 3 | 4 | IV-2 | Mrpl38 | 0.73 |
| 6215 | 3 | 4 | IV-2 | Mrpl39 | 0.75 |
| 6216 | 3 | 4 | IV-2 | Mrpl4 | 0.76 |
| 6217 | 3 | 4 | IV-2 | Mrpl40 | 0.89 |
| 6218 | 3 | 4 | IV-2 | Mrpl41 | 0.86 |
| 6219 | 3 | 4 | IV-2 | Mrpl42 | 0.70 |
| 6220 | 3 | 4 | IV-2 | Mrpl43 | 0.94 |
| 6221 | 3 | 4 | IV-2 | Mrpl44 | 0.83 |
| 6222 | 3 | 4 | IV-2 | Mrpl45 | 0.79 |
| 6223 | 3 | 4 | IV-2 | Mrpl46 | 0.83 |
| 6224 | 3 | 4 | IV-2 | Mrpl47 | 0.85 |
| 6225 | 3 | 4 | IV-2 | Mrpl48 | 0.72 |
| 6226 | 3 | 4 | IV-2 | Mrpl49 | 0.69 |
| 6227 | 3 | 4 | IV-2 | Mrpl50 | 0.88 |
| 6228 | 3 | 4 | IV-2 | Mrpl51 | 0.68 |
| 6229 | 3 | 4 | IV-2 | Mrpl52 | 0.86 |
| 6230 | 3 | 4 | IV-2 | Mrpl53 | 0.69 |
| 6231 | 3 | 4 | IV-2 | Mrpl54 | 0.82 |
| 6232 | 3 | 4 | IV-2 | Mrpl55 | 0.75 |
| 6233 | 3 | 4 | IV-2 | Mrpl57 | 0.80 |
| 6234 | 3 | 4 | IV-2 | Mrpl9 | 0.89 |
| 6235 | 3 | 4 | IV-2 | Mrps10 | 0.87 |
| 6236 | 3 | 4 | IV-2 | Mrps11 | 0.95 |
| 6237 | 3 | 4 | IV-2 | Mrps12 | 0.85 |
| 6238 | 3 | 4 | IV-2 | Mrps14 | 0.72 |
| 6239 | 3 | 4 | IV-2 | Mrps15 | 0.86 |
| 6240 | 3 | 4 | IV-2 | Mrps17 | 0.83 |
| 6241 | 3 | 4 | IV-2 | Mrps18a | 0.83 |
| 6242 | 3 | 4 | IV-2 | Mrps18b | 0.94 |
| 6243 | 3 | 4 | IV-2 | Mrps18c | 0.91 |
| 6244 | 3 | 4 | IV-2 | Mrps2 | 0.92 |
| 6245 | 3 | 4 | IV-2 | Mrps22 | 0.73 |
| 6246 | 3 | 4 | IV-2 | Mrps23 | 0.90 |
| 6247 | 3 | 4 | IV-2 | Mrps24 | 0.71 |
| 6248 | 3 | 4 | IV-2 | Mrps25 | 0.72 |
| 6249 | 3 | 4 | IV-2 | Mrps26 | 0.92 |
| 6250 | 3 | 4 | IV-2 | Mrps27 | 0.79 |
| 6251 | 3 | 4 | IV-2 | Mrps30 | 0.92 |
| 6252 | 3 | 4 | IV-2 | Mrps31 | 0.84 |
| 6253 | 3 | 4 | IV-2 | Mrps33 | 0.86 |
| 6254 | 3 | 4 | IV-2 | Mrps34 | 0.91 |
| 6255 | 3 | 4 | IV-2 | Mrps35 | 0.74 |
| 6256 | 3 | 4 | IV-2 | Mrps5 | 0.97 |
| 6257 | 3 | 4 | IV-2 | Mrps6 | 0.98 |
| 6258 | 3 | 4 | IV-2 | Mrps7 | 0.75 |
| 6259 | 3 | 4 | IV-2 | Mrto4 | 0.87 |
| 6260 | 3 | 4 | IV-2 | Mrvi1 | 0.95 |
| 6261 | 3 | 4 | IV-2 | Ms4a18 | 0.96 |
| 6262 | 3 | 4 | IV-2 | Msh2 | 0.87 |
| 6263 | 3 | 4 | IV-2 | Msh6 | 0.86 |
| 6264 | 3 | 4 | IV-2 | Msl2 | 0.90 |
| 6265 | 3 | 4 | IV-2 | Msl3 | 0.95 |
| 6266 | 3 | 4 | IV-2 | Msmo1 | 0.77 |
| 6267 | 3 | 4 | IV-2 | Msn | 0.84 |
| 6268 | 3 | 4 | IV-2 | Msra | 0.98 |
| 6269 | 3 | 4 | IV-2 | Msrb1 | 0.93 |
| 6270 | 3 | 4 | IV-2 | Msrb2 | 0.81 |
| 6271 | 3 | 4 | IV-2 | Msrb3 | 0.92 |
| 6272 | 3 | 4 | IV-2 | Mt2 | 0.96 |
| 6273 | 3 | 4 | IV-2 | Mta2 | 0.91 |
| 6274 | 3 | 4 | IV-2 | Mta3 | 0.78 |
| 6275 | 3 | 4 | IV-2 | Mtag2 | 0.89 |
| 6276 | 3 | 4 | IV-2 | Mtap | 0.91 |
| 6277 | 3 | 4 | IV-2 | Mtch1 | 0.91 |
| 6278 | 3 | 4 | IV-2 | Mterf1a | 0.78 |
| 6279 | 3 | 4 | IV-2 | Mterfd2 | 0.97 |
| 6280 | 3 | 4 | IV-2 | Mtf1 | 0.89 |
| 6281 | 3 | 4 | IV-2 | Mtfr2 | 0.79 |
| 6282 | 3 | 4 | IV-2 | Mtg2 | 0.91 |
| 6283 | 3 | 4 | IV-2 | Mthfs | 0.81 |
| 6284 | 3 | 4 | IV-2 | Mtif2 | 0.90 |
| 6285 | 3 | 4 | IV-2 | Mtif3 | 0.89 |
| 6286 | 3 | 4 | IV-2 | Mtm1 | 0.75 |
| 6287 | 3 | 4 | IV-2 | Mtmr11 | 0.98 |
| 6288 | 3 | 4 | IV-2 | Mtmr12 | 0.99 |
| 6289 | 3 | 4 | IV-2 | Mtmr4 | 0.96 |
| 6290 | 3 | 4 | IV-2 | Mto1 | 0.72 |
| 6291 | 3 | 4 | IV-2 | Mtr | 0.87 |
| 6292 | 3 | 4 | IV-2 | Mtrf1 | 0.90 |
| 6293 | 3 | 4 | IV-2 | Mtrf1l | 0.85 |
| 6294 | 3 | 4 | IV-2 | Mtrr | 0.93 |
| 6295 | 3 | 4 | IV-2 | Mtx1 | 0.95 |
| 6296 | 3 | 4 | IV-2 | Mtx2 | 0.71 |
| 6297 | 3 | 4 | IV-2 | Muc1 | 0.79 |
| 6298 | 3 | 4 | IV-2 | Muc15 | 0.67 |
| 6299 | 3 | 4 | IV-2 | Muc19 | 0.81 |
| 6300 | 3 | 4 | IV-2 | Mul1 | 0.85 |
| 6301 | 3 | 4 | IV-2 | Mum1 | 0.98 |
| 6302 | 3 | 4 | IV-2 | Murc | 0.76 |
| 6303 | 3 | 4 | IV-2 | Mus81 | 0.78 |
| 6304 | 3 | 4 | IV-2 | Mut | 0.78 |
| 6305 | 3 | 4 | IV-2 | Mutyh | 0.81 |
| 6306 | 3 | 4 | IV-2 | Mvb12a | 0.86 |
| 6307 | 3 | 4 | IV-2 | Mvd | 0.88 |
| 6308 | 3 | 4 | IV-2 | Mvk | 0.84 |
| 6309 | 3 | 4 | IV-2 | Mxd1 | 0.93 |
| 6310 | 3 | 4 | IV-2 | Mxd4 | 0.94 |
| 6311 | 3 | 4 | IV-2 | Mxi1 | 0.95 |
| 6312 | 3 | 4 | IV-2 | Mxra7 | 0.85 |
| 6313 | 3 | 4 | IV-2 | Mxra8 | 0.84 |
| 6314 | 3 | 4 | IV-2 | Myadm | 0.81 |
| 6315 | 3 | 4 | IV-2 | Myadml2 | 0.74 |
| 6316 | 3 | 4 | IV-2 | Mybl2 | 0.69 |
| 6317 | 3 | 4 | IV-2 | Mybpc1 | 0.76 |
| 6318 | 3 | 4 | IV-2 | Mybpc3 | 0.76 |
| 6319 | 3 | 4 | IV-2 | Mycbp | 0.80 |
| 6320 | 3 | 4 | IV-2 | Myd88 | 0.89 |
| 6321 | 3 | 4 | IV-2 | Myeov2 | 0.93 |
| 6322 | 3 | 4 | IV-2 | Myf5 | 0.87 |
| 6323 | 3 | 4 | IV-2 | Myg1 | 0.86 |
| 6324 | 3 | 4 | IV-2 | Myh1 | 0.92 |
| 6325 | 3 | 4 | IV-2 | Myh10 | 0.96 |
| 6326 | 3 | 4 | IV-2 | Myh11 | 0.73 |
| 6327 | 3 | 4 | IV-2 | Myh13 | 0.68 |
| 6328 | 3 | 4 | IV-2 | Myh14 | 0.69 |
| 6329 | 3 | 4 | IV-2 | Myh3 | 0.74 |
| 6330 | 3 | 4 | IV-2 | Myh7 | 0.84 |
| 6331 | 3 | 4 | IV-2 | Myh9 | 0.84 |
| 6332 | 3 | 4 | IV-2 | Myl12a | 0.94 |
| 6333 | 3 | 4 | IV-2 | Myl12b | 0.99 |
| 6334 | 3 | 4 | IV-2 | Myl2 | 0.81 |

Fig. 45 - 34

| | | | | | | | | | | | | | | |
|---|---|---|---|---|---|---|---|---|---|---|---|---|---|---|
| 6335 | 3 | 4 | | | IV-2 | Myl3 | 0.77 | 6431 | 3 | 4 | | | IV-2 | Ndufa7 | 0.93 |
| 6336 | 3 | 4 | | | IV-2 | Myl6 | 0.71 | 6432 | 3 | 4 | | | IV-2 | Ndufa8 | 0.71 |
| 6337 | 3 | 4 | | | IV-2 | Myl6b | 0.86 | 6433 | 3 | 4 | | | IV-2 | Ndufa9 | 0.67 |
| 6338 | 3 | 4 | | | IV-2 | Myl7 | 0.92 | 6434 | 3 | 4 | | | IV-2 | Ndufaf2 | 0.91 |
| 6339 | 3 | 4 | | | IV-2 | Myl9 | 0.69 | 6435 | 3 | 4 | | | IV-2 | Ndufaf3 | 0.77 |
| 6340 | 3 | 4 | | | IV-2 | Mylk | 0.81 | 6436 | 3 | 4 | | | IV-2 | Ndufaf4 | 0.81 |
| 6341 | 3 | 4 | | | IV-2 | Mylk2 | 0.67 | 6437 | 3 | 4 | | | IV-2 | Ndufaf5 | 0.92 |
| 6342 | 3 | 4 | | | IV-2 | Mylk4 | 0.87 | 6438 | 3 | 4 | | | IV-2 | Ndufaf7 | 0.88 |
| 6343 | 3 | 4 | | | IV-2 | Myo10 | 0.87 | 6439 | 3 | 4 | | | IV-2 | Ndufb10 | 0.67 |
| 6344 | 3 | 4 | | | IV-2 | Myo18b | 0.69 | 6440 | 3 | 4 | | | IV-2 | Ndufb11 | 0.79 |
| 6345 | 3 | 4 | | | IV-2 | Myo19 | 0.83 | 6441 | 3 | 4 | | | IV-2 | Ndufb3 | 0.81 |
| 6346 | 3 | 4 | | | IV-2 | Myo1a | 0.97 | 6442 | 3 | 4 | | | IV-2 | Ndufb4 | 0.76 |
| 6347 | 3 | 4 | | | IV-2 | Myo1b | 0.98 | 6443 | 3 | 4 | | | IV-2 | Ndufb5 | 0.83 |
| 6348 | 3 | 4 | | | IV-2 | Myo1d | 0.68 | 6444 | 3 | 4 | | | IV-2 | Ndufb8 | 0.79 |
| 6349 | 3 | 4 | | | IV-2 | Myo1e | 0.83 | 6445 | 3 | 4 | | | IV-2 | Ndufb9 | 0.79 |
| 6350 | 3 | 4 | | | IV-2 | Myo5b | 0.77 | 6446 | 3 | 4 | | | IV-2 | Ndufc2 | 0.82 |
| 6351 | 3 | 4 | | | IV-2 | Myo5c | 0.75 | 6447 | 3 | 4 | | | IV-2 | Ndufs1 | 0.69 |
| 6352 | 3 | 4 | | | IV-2 | Myo6 | 0.88 | 6448 | 3 | 4 | | | IV-2 | Ndufs2 | 0.74 |
| 6353 | 3 | 4 | | | IV-2 | Myo7a | 0.92 | 6449 | 3 | 4 | | | IV-2 | Ndufs3 | 0.94 |
| 6354 | 3 | 4 | | | IV-2 | Myod1 | 0.88 | 6450 | 3 | 4 | | | IV-2 | Ndufs4 | 0.71 |
| 6355 | 3 | 4 | | | IV-2 | Myof | 0.93 | 6451 | 3 | 4 | | | IV-2 | Ndufs6 | 0.72 |
| 6356 | 3 | 4 | | | IV-2 | Myog | 0.94 | 6452 | 3 | 4 | | | IV-2 | Ndufs7 | 0.90 |
| 6357 | 3 | 4 | | | IV-2 | Myom1 | 0.77 | 6453 | 3 | 4 | | | IV-2 | Ndufs8 | 0.68 |
| 6358 | 3 | 4 | | | IV-2 | Myom3 | 0.68 | 6454 | 3 | 4 | | | IV-2 | Ndufv1 | 0.89 |
| 6359 | 3 | 4 | | | IV-2 | Myot | 0.74 | 6455 | 3 | 4 | | | IV-2 | Ndufv2 | 0.72 |
| 6360 | 3 | 4 | | | IV-2 | Myoz2 | 0.88 | 6456 | 3 | 4 | | | IV-2 | Ndufv3 | 0.76 |
| 6361 | 3 | 4 | | | IV-2 | Mypop | 0.86 | 6457 | 3 | 4 | | | IV-2 | Nebl | 0.78 |
| 6362 | 3 | 4 | | | IV-2 | Myzap | 0.98 | 6458 | 3 | 4 | | | IV-2 | Necab3 | 0.90 |
| 6363 | 3 | 4 | | | IV-2 | Mzb1 | 0.78 | 6459 | 3 | 4 | | | IV-2 | Necap2 | 0.87 |
| 6364 | 3 | 4 | | | IV-2 | N4bp2l2 | 0.94 | 6460 | 3 | 4 | | | IV-2 | Nedd1 | 0.80 |
| 6365 | 3 | 4 | | | IV-2 | N4bp3 | 0.87 | 6461 | 3 | 4 | | | IV-2 | Nedd4 | 0.92 |
| 6366 | 3 | 4 | | | IV-2 | N6amt2 | 0.74 | 6462 | 3 | 4 | | | IV-2 | Nedd8 | 0.87 |
| 6367 | 3 | 4 | | | IV-2 | Naa10 | 0.71 | 6463 | 3 | 4 | | | IV-2 | Nefh | 0.94 |
| 6368 | 3 | 4 | | | IV-2 | Naa15 | 0.84 | 6464 | 3 | 4 | | | IV-2 | Neil1 | 0.79 |
| 6369 | 3 | 4 | | | IV-2 | Naa16 | 0.88 | 6465 | 3 | 4 | | | IV-2 | Neil3 | 0.88 |
| 6370 | 3 | 4 | | | IV-2 | Naa20 | 0.95 | 6466 | 3 | 4 | | | IV-2 | Nek1 | 0.98 |
| 6371 | 3 | 4 | | | IV-2 | Naa30 | 0.96 | 6467 | 3 | 4 | | | IV-2 | Nek2 | 0.71 |
| 6372 | 3 | 4 | | | IV-2 | Naa35 | 0.99 | 6468 | 3 | 4 | | | IV-2 | Nek4 | 0.98 |
| 6373 | 3 | 4 | | | IV-2 | Naa40 | 0.85 | 6469 | 3 | 4 | | | IV-2 | Nek6 | 0.93 |
| 6374 | 3 | 4 | | | IV-2 | Naa50 | 0.84 | 6470 | 3 | 4 | | | IV-2 | Nelfa | 0.92 |
| 6375 | 3 | 4 | | | IV-2 | Naa60 | 0.93 | 6471 | 3 | 4 | | | IV-2 | Nelfb | 0.92 |
| 6376 | 3 | 4 | | | IV-2 | Naaa | 0.85 | 6472 | 3 | 4 | | | IV-2 | Nelfcd | 0.85 |
| 6377 | 3 | 4 | | | IV-2 | Naalad2 | 0.77 | 6473 | 3 | 4 | | | IV-2 | Nelfe | 0.94 |
| 6378 | 3 | 4 | | | IV-2 | Nab1 | 0.84 | 6474 | 3 | 4 | | | IV-2 | Nenf | 0.97 |
| 6379 | 3 | 4 | | | IV-2 | Nab2 | 0.81 | 6475 | 3 | 4 | | | IV-2 | Nes | 0.87 |
| 6380 | 3 | 4 | | | IV-2 | Nacc1 | 0.75 | 6476 | 3 | 4 | | | IV-2 | Nespas | 0.99 |
| 6381 | 3 | 4 | | | IV-2 | Nacc2 | 0.90 | 6477 | 3 | 4 | | | IV-2 | Neu1 | 0.79 |
| 6382 | 3 | 4 | | | IV-2 | Nadk | 0.83 | 6478 | 3 | 4 | | | IV-2 | Neu3 | 0.69 |
| 6383 | 3 | 4 | | | IV-2 | Naf1 | 0.92 | 6479 | 3 | 4 | | | IV-2 | Neurl1b | 0.82 |
| 6384 | 3 | 4 | | | IV-2 | Naga | 0.86 | 6480 | 3 | 4 | | | IV-2 | Neurl3 | 0.71 |
| 6385 | 3 | 4 | | | IV-2 | Nagk | 0.78 | 6481 | 3 | 4 | | | IV-2 | Nfam1 | 0.88 |
| 6386 | 3 | 4 | | | IV-2 | Naglu | 0.90 | 6482 | 3 | 4 | | | IV-2 | Nfatc1 | 0.92 |
| 6387 | 3 | 4 | | | IV-2 | Naif1 | 0.83 | 6483 | 3 | 4 | | | IV-2 | Nfatc2 | 0.97 |
| 6388 | 3 | 4 | | | IV-2 | Naip1 | 0.86 | 6484 | 3 | 4 | | | IV-2 | Nfatc2ip | 0.81 |
| 6389 | 3 | 4 | | | IV-2 | Nampt | 0.71 | 6485 | 3 | 4 | | | IV-2 | Nfatc3 | 0.82 |
| 6390 | 3 | 4 | | | IV-2 | Nanp | 0.83 | 6486 | 3 | 4 | | | IV-2 | Nfe2l1 | 0.94 |
| 6391 | 3 | 4 | | | IV-2 | Nans | 0.82 | 6487 | 3 | 4 | | | IV-2 | Nfe2l2 | 0.70 |
| 6392 | 3 | 4 | | | IV-2 | Nap1l4 | 0.95 | 6488 | 3 | 4 | | | IV-2 | Nfic | 0.96 |
| 6393 | 3 | 4 | | | IV-2 | Napa | 0.92 | 6489 | 3 | 4 | | | IV-2 | Nfkb1 | 0.94 |
| 6394 | 3 | 4 | | | IV-2 | Narfl | 0.89 | 6490 | 3 | 4 | | | IV-2 | Nfkb2 | 0.92 |
| 6395 | 3 | 4 | | | IV-2 | Narg2 | 0.90 | 6491 | 3 | 4 | | | IV-2 | Nfkbib | 0.95 |
| 6396 | 3 | 4 | | | IV-2 | Nasp | 0.77 | 6492 | 3 | 4 | | | IV-2 | Nfs1 | 0.74 |
| 6397 | 3 | 4 | | | IV-2 | Nat2 | 0.79 | 6493 | 3 | 4 | | | IV-2 | Nfya | 0.69 |
| 6398 | 3 | 4 | | | IV-2 | Nat6 | 0.94 | 6494 | 3 | 4 | | | IV-2 | Nfyb | 0.97 |
| 6399 | 3 | 4 | | | IV-2 | Nat9 | 0.84 | 6495 | 3 | 4 | | | IV-2 | Nfyc | 0.92 |
| 6400 | 3 | 4 | | | IV-2 | Nbas | 0.89 | 6496 | 3 | 4 | | | IV-2 | Ngdn | 0.96 |
| 6401 | 3 | 4 | | | IV-2 | Nbeal2 | 0.74 | 6497 | 3 | 4 | | | IV-2 | Ngef | 0.89 |
| 6402 | 3 | 4 | | | IV-2 | Nbn | 0.88 | 6498 | 3 | 4 | | | IV-2 | Ngfr | 0.92 |
| 6403 | 3 | 4 | | | IV-2 | Nbr1 | 0.98 | 6499 | 3 | 4 | | | IV-2 | Ngfrap1 | 1.00 |
| 6404 | 3 | 4 | | | IV-2 | Ncapd2 | 0.70 | 6500 | 3 | 4 | | | IV-2 | Ngp | 0.77 |
| 6405 | 3 | 4 | | | IV-2 | Ncapd3 | 0.93 | 6501 | 3 | 4 | | | IV-2 | Nhp2 | 0.89 |
| 6406 | 3 | 4 | | | IV-2 | Ncapg2 | 0.71 | 6502 | 3 | 4 | | | IV-2 | Nhp2l1 | 0.74 |
| 6407 | 3 | 4 | | | IV-2 | Ncaph | 0.77 | 6503 | 3 | 4 | | | IV-2 | Nhsl2 | 0.99 |
| 6408 | 3 | 4 | | | IV-2 | Ncaph2 | 0.77 | 6504 | 3 | 4 | | | IV-2 | Nid2 | 0.93 |
| 6409 | 3 | 4 | | | IV-2 | Ncbp1 | 0.91 | 6505 | 3 | 4 | | | IV-2 | Nif3l1 | 0.86 |
| 6410 | 3 | 4 | | | IV-2 | Ncbp2 | 0.77 | 6506 | 3 | 4 | | | IV-2 | Nifk | 0.98 |
| 6411 | 3 | 4 | | | IV-2 | Ncf1 | 0.91 | 6507 | 3 | 4 | | | IV-2 | Ninj1 | 0.92 |
| 6412 | 3 | 4 | | | IV-2 | Ncf4 | 0.98 | 6508 | 3 | 4 | | | IV-2 | Ninl | 0.86 |
| 6413 | 3 | 4 | | | IV-2 | Nckap1l | 0.79 | 6509 | 3 | 4 | | | IV-2 | Nipa1 | 0.93 |
| 6414 | 3 | 4 | | | IV-2 | Ncln | 0.88 | 6510 | 3 | 4 | | | IV-2 | Nipa2 | 0.84 |
| 6415 | 3 | 4 | | | IV-2 | Ncoa4 | 0.71 | 6511 | 3 | 4 | | | IV-2 | Nipal1 | 0.69 |
| 6416 | 3 | 4 | | | IV-2 | Ncoa7 | 0.87 | 6512 | 3 | 4 | | | IV-2 | Nipal3 | 0.88 |
| 6417 | 3 | 4 | | | IV-2 | Ncor1 | 0.99 | 6513 | 3 | 4 | | | IV-2 | Nipbl | 0.99 |
| 6418 | 3 | 4 | | | IV-2 | Ndc1 | 0.73 | 6514 | 3 | 4 | | | IV-2 | Nit1 | 0.75 |
| 6419 | 3 | 4 | | | IV-2 | Nde1 | 0.69 | 6515 | 3 | 4 | | | IV-2 | Nit2 | 0.90 |
| 6420 | 3 | 4 | | | IV-2 | Ndnf | 0.90 | 6516 | 3 | 4 | | | IV-2 | Nkg7 | 0.88 |
| 6421 | 3 | 4 | | | IV-2 | Ndnl2 | 0.83 | 6517 | 3 | 4 | | | IV-2 | Nkx2-3 | 0.84 |
| 6422 | 3 | 4 | | | IV-2 | Ndrg3 | 0.96 | 6518 | 3 | 4 | | | IV-2 | Nkx2-5 | 0.91 |
| 6423 | 3 | 4 | | | IV-2 | Ndst2 | 0.94 | 6519 | 3 | 4 | | | IV-2 | Nlrc4 | 0.82 |
| 6424 | 3 | 4 | | | IV-2 | Ndufa1 | 0.75 | 6520 | 3 | 4 | | | IV-2 | Nlrp5-ps | 1.00 |
| 6425 | 3 | 4 | | | IV-2 | Ndufa10 | 0.86 | 6521 | 3 | 4 | | | IV-2 | Nme1 | 0.80 |
| 6426 | 3 | 4 | | | IV-2 | Ndufa11 | 0.75 | 6522 | 3 | 4 | | | IV-2 | Nme2 | 0.76 |
| 6427 | 3 | 4 | | | IV-2 | Ndufa13 | 0.76 | 6523 | 3 | 4 | | | IV-2 | Nme4 | 0.92 |
| 6428 | 3 | 4 | | | IV-2 | Ndufa2 | 0.91 | 6524 | 3 | 4 | | | IV-2 | Nme5 | 0.79 |
| 6429 | 3 | 4 | | | IV-2 | Ndufa3 | 0.84 | 6525 | 3 | 4 | | | IV-2 | Nme6 | 0.71 |
| 6430 | 3 | 4 | | | IV-2 | Ndufa5 | 0.71 | 6526 | 3 | 4 | | | IV-2 | Nmnat3 | 0.80 |

Fig. 45 - 35

| | | | | | | | | | | | | | | |
|---|---|---|---|---|---|---|---|---|---|---|---|---|---|---|
| 6527 | 3 | 4 | | | IV-2 | Nmral1 | 0.99 | 6623 | 3 | 4 | | | IV-2 | Nup62 | 0.87 |
| 6528 | 3 | 4 | | | IV-2 | Nmrk1 | 0.81 | 6624 | 3 | 4 | | | IV-2 | Nup85 | 0.84 |
| 6529 | 3 | 4 | | | IV-2 | Nmrk2 | 0.93 | 6625 | 3 | 4 | | | IV-2 | Nup88 | 0.99 |
| 6530 | 3 | 4 | | | IV-2 | Nmt1 | 0.81 | 6626 | 3 | 4 | | | IV-2 | Nup93 | 0.96 |
| 6531 | 3 | 4 | | | IV-2 | Nnt | 0.82 | 6627 | 3 | 4 | | | IV-2 | Nup98 | 0.97 |
| 6532 | 3 | 4 | | | IV-2 | Noa1 | 0.89 | 6628 | 3 | 4 | | | IV-2 | Nupl1 | 0.91 |
| 6533 | 3 | 4 | | | IV-2 | Noc4l | 0.82 | 6629 | 3 | 4 | | | IV-2 | Nutf2 | 0.89 |
| 6534 | 3 | 4 | | | IV-2 | Nog | 0.97 | 6630 | 3 | 4 | | | IV-2 | Nvl | 0.99 |
| 6535 | 3 | 4 | | | IV-2 | Nol12 | 0.98 | 6631 | 3 | 4 | | | IV-2 | Nxn | 0.75 |
| 6536 | 3 | 4 | | | IV-2 | Nol7 | 0.80 | 6632 | 3 | 4 | | | IV-2 | Nxt1 | 0.77 |
| 6537 | 3 | 4 | | | IV-2 | Nolc1 | 0.93 | 6633 | 3 | 4 | | | IV-2 | Nxt2 | 0.94 |
| 6538 | 3 | 4 | | | IV-2 | Nono | 0.88 | 6634 | 3 | 4 | | | IV-2 | Nvnrin | 1.00 |
| 6539 | 3 | 4 | | | IV-2 | Nop10 | 0.68 | 6635 | 3 | 4 | | | IV-2 | OTTMUSG000000 16609 | 0.76 |
| 6540 | 3 | 4 | | | IV-2 | Nop16 | 0.83 | | | | | | | | |
| 6541 | 3 | 4 | | | IV-2 | Nop2 | 1.00 | 6636 | 3 | 4 | | | IV-2 | Oaf | 0.71 |
| 6542 | 3 | 4 | | | IV-2 | Nop56 | 0.96 | 6637 | 3 | 4 | | | IV-2 | Oard1 | 0.83 |
| 6543 | 3 | 4 | | | IV-2 | Nop58 | 0.93 | 6638 | 3 | 4 | | | IV-2 | Oat | 0.82 |
| 6544 | 3 | 4 | | | IV-2 | Nop9 | 0.96 | 6639 | 3 | 4 | | | IV-2 | Oaz1 | 0.77 |
| 6545 | 3 | 4 | | | IV-2 | Nos1 | 1.00 | 6640 | 3 | 4 | | | IV-2 | Obfc1 | 0.85 |
| 6546 | 3 | 4 | | | IV-2 | Nos3 | 0.96 | 6641 | 3 | 4 | | | IV-2 | Obscn | 0.77 |
| 6547 | 3 | 4 | | | IV-2 | Nostrin | 0.89 | 6642 | 3 | 4 | | | IV-2 | Ocel1 | 0.88 |
| 6548 | 3 | 4 | | | IV-2 | Notch1 | 0.99 | 6643 | 3 | 4 | | | IV-2 | Ociad1 | 0.91 |
| 6549 | 3 | 4 | | | IV-2 | Notch2 | 0.97 | 6644 | 3 | 4 | | | IV-2 | Ocln | 0.82 |
| 6550 | 3 | 4 | | | IV-2 | Notch3 | 0.93 | 6645 | 3 | 4 | | | IV-2 | Odf2 | 0.88 |
| 6551 | 3 | 4 | | | IV-2 | Notch4 | 0.94 | 6646 | 3 | 4 | | | IV-2 | Odf2l | 0.99 |
| 6552 | 3 | 4 | | | IV-2 | Nov | 0.91 | 6647 | 3 | 4 | | | IV-2 | Ogfod1 | 0.81 |
| 6553 | 3 | 4 | | | IV-2 | Npc2 | 0.93 | 6648 | 3 | 4 | | | IV-2 | Ogfod3 | 0.98 |
| 6554 | 3 | 4 | | | IV-2 | Npepps | 0.91 | 6649 | 3 | 4 | | | IV-2 | Ogg1 | 0.99 |
| 6555 | 3 | 4 | | | IV-2 | Npm1 | 0.92 | 6650 | 3 | 4 | | | IV-2 | Oit3 | 0.93 |
| 6556 | 3 | 4 | | | IV-2 | Npm3-ps1 | 0.68 | 6651 | 3 | 4 | | | IV-2 | Ola1 | 0.93 |
| 6557 | 3 | 4 | | | IV-2 | Nppc | 0.90 | 6652 | 3 | 4 | | | IV-2 | Olfml2b | 0.94 |
| 6558 | 3 | 4 | | | IV-2 | Npr1 | 0.73 | 6653 | 3 | 4 | | | IV-2 | Olfml3 | 0.78 |
| 6559 | 3 | 4 | | | IV-2 | Nprl2 | 0.91 | 6654 | 3 | 4 | | | IV-2 | Olfr1033 | 0.92 |
| 6560 | 3 | 4 | | | IV-2 | Nr1h2 | 0.86 | 6655 | 3 | 4 | | | IV-2 | Olfr1372-ps1 | 0.89 |
| 6561 | 3 | 4 | | | IV-2 | Nr1h3 | 0.76 | 6656 | 3 | 4 | | | IV-2 | Olfr558 | 0.90 |
| 6562 | 3 | 4 | | | IV-2 | Nr1h4 | 0.67 | 6657 | 3 | 4 | | | IV-2 | Oma1 | 0.73 |
| 6563 | 3 | 4 | | | IV-2 | Nr2c2ap | 0.81 | 6658 | 3 | 4 | | | IV-2 | Omd | 0.91 |
| 6564 | 3 | 4 | | | IV-2 | Nr2f6 | 0.78 | 6659 | 3 | 4 | | | IV-2 | Opa3 | 0.85 |
| 6565 | 3 | 4 | | | IV-2 | Nr3c1 | 0.78 | 6660 | 3 | 4 | | | IV-2 | Opn3 | 0.90 |
| 6566 | 3 | 4 | | | IV-2 | Nr3c2 | 0.79 | 6661 | 3 | 4 | | | IV-2 | Optc | 0.87 |
| 6567 | 3 | 4 | | | IV-2 | Nr4a3 | 0.99 | 6662 | 3 | 4 | | | IV-2 | Optn | 0.90 |
| 6568 | 3 | 4 | | | IV-2 | Nrap | 0.93 | 6663 | 3 | 4 | | | IV-2 | Orai1 | 0.98 |
| 6569 | 3 | 4 | | | IV-2 | Nrarp | 0.70 | 6664 | 3 | 4 | | | IV-2 | Orai3 | 0.94 |
| 6570 | 3 | 4 | | | IV-2 | Nrbf2 | 0.99 | 6665 | 3 | 4 | | | IV-2 | Oraov1 | 0.93 |
| 6571 | 3 | 4 | | | IV-2 | Nrd1 | 0.89 | 6666 | 3 | 4 | | | IV-2 | Orc2 | 0.88 |
| 6572 | 3 | 4 | | | IV-2 | Nrf1 | 0.85 | 6667 | 3 | 4 | | | IV-2 | Orc5 | 0.94 |
| 6573 | 3 | 4 | | | IV-2 | Nrg4 | 0.97 | 6668 | 3 | 4 | | | IV-2 | Orc6 | 0.87 |
| 6574 | 3 | 4 | | | IV-2 | Nrgn | 0.80 | 6669 | 3 | 4 | | | IV-2 | Orm1 | 0.99 |
| 6575 | 3 | 4 | | | IV-2 | Nrk | 0.82 | 6670 | 3 | 4 | | | IV-2 | Ormdl1 | 0.77 |
| 6576 | 3 | 4 | | | IV-2 | Nrm | 0.86 | 6671 | 3 | 4 | | | IV-2 | Ormdl2 | 0.70 |
| 6577 | 3 | 4 | | | IV-2 | Nrn1 | 0.82 | 6672 | 3 | 4 | | | IV-2 | Ormdl3 | 0.86 |
| 6578 | 3 | 4 | | | IV-2 | Nrp | 1.00 | 6673 | 3 | 4 | | | IV-2 | Osbp | 1.00 |
| 6579 | 3 | 4 | | | IV-2 | Nrros | 0.79 | 6674 | 3 | 4 | | | IV-2 | Osbpl10 | 0.97 |
| 6580 | 3 | 4 | | | IV-2 | Nrtn | 0.75 | 6675 | 3 | 4 | | | IV-2 | Osbpl11 | 0.99 |
| 6581 | 3 | 4 | | | IV-2 | Nsdhl | 0.70 | 6676 | 3 | 4 | | | IV-2 | Osbpl1a | 0.89 |
| 6582 | 3 | 4 | | | IV-2 | Nsfl1c | 0.83 | 6677 | 3 | 4 | | | IV-2 | Oscar | 0.85 |
| 6583 | 3 | 4 | | | IV-2 | Nsmce1 | 0.87 | 6678 | 3 | 4 | | | IV-2 | Oser1 | 0.91 |
| 6584 | 3 | 4 | | | IV-2 | Nsmce2 | 0.89 | 6679 | 3 | 4 | | | IV-2 | Osgep | 0.99 |
| 6585 | 3 | 4 | | | IV-2 | Nsun2 | 0.96 | 6680 | 3 | 4 | | | IV-2 | Osgepl1 | 0.75 |
| 6586 | 3 | 4 | | | IV-2 | Nsun4 | 1.00 | 6681 | 3 | 4 | | | IV-2 | Ost4 | 0.70 |
| 6587 | 3 | 4 | | | IV-2 | Nt5c | 0.92 | 6682 | 3 | 4 | | | IV-2 | Ostc | 0.72 |
| 6588 | 3 | 4 | | | IV-2 | Nt5c3 | 0.82 | 6683 | 3 | 4 | | | IV-2 | Ostf1 | 0.83 |
| 6589 | 3 | 4 | | | IV-2 | Nt5c3b | 0.99 | 6684 | 3 | 4 | | | IV-2 | Otub2 | 0.87 |
| 6590 | 3 | 4 | | | IV-2 | Nt5dc2 | 0.71 | 6685 | 3 | 4 | | | IV-2 | Otud1 | 0.90 |
| 6591 | 3 | 4 | | | IV-2 | Ntan1 | 0.90 | 6686 | 3 | 4 | | | IV-2 | Otud3 | 0.87 |
| 6592 | 3 | 4 | | | IV-2 | Ntn4 | 0.92 | 6687 | 3 | 4 | | | IV-2 | Otud5 | 0.89 |
| 6593 | 3 | 4 | | | IV-2 | Ntsr1 | 0.96 | 6688 | 3 | 4 | | | IV-2 | Otud6b | 0.97 |
| 6594 | 3 | 4 | | | IV-2 | Nub1 | 1.00 | 6689 | 3 | 4 | | | IV-2 | Ovca2 | 0.80 |
| 6595 | 3 | 4 | | | IV-2 | Nubp1 | 0.98 | 6690 | 3 | 4 | | | IV-2 | Ovol1 | 0.70 |
| 6596 | 3 | 4 | | | IV-2 | Nucb1 | 0.98 | 6691 | 3 | 4 | | | IV-2 | Ovol2 | 0.71 |
| 6597 | 3 | 4 | | | IV-2 | Nucks1 | 0.83 | 6692 | 3 | 4 | | | IV-2 | Oxa1l | 0.85 |
| 6598 | 3 | 4 | | | IV-2 | Nudc | 0.87 | 6693 | 3 | 4 | | | IV-2 | Oxld1 | 0.84 |
| 6599 | 3 | 4 | | | IV-2 | Nudcd1 | 0.76 | 6694 | 3 | 4 | | | IV-2 | Oxnad1 | 0.89 |
| 6600 | 3 | 4 | | | IV-2 | Nudcd2 | 0.92 | 6695 | 3 | 4 | | | IV-2 | Oxsm | 0.84 |
| 6601 | 3 | 4 | | | IV-2 | Nudt12 | 0.71 | 6696 | 3 | 4 | | | IV-2 | Oxsr1 | 1.00 |
| 6602 | 3 | 4 | | | IV-2 | Nudt13 | 0.87 | 6697 | 3 | 4 | | | IV-2 | P2rx5 | 0.73 |
| 6603 | 3 | 4 | | | IV-2 | Nudt14 | 0.86 | 6698 | 3 | 4 | | | IV-2 | P2ry1 | 0.69 |
| 6604 | 3 | 4 | | | IV-2 | Nudt16l1 | 0.89 | 6699 | 3 | 4 | | | IV-2 | P2ry12 | 0.83 |
| 6605 | 3 | 4 | | | IV-2 | Nudt19 | 0.88 | 6700 | 3 | 4 | | | IV-2 | P2ry13 | 0.80 |
| 6606 | 3 | 4 | | | IV-2 | Nudt2 | 0.72 | 6701 | 3 | 4 | | | IV-2 | P2ry14 | 0.70 |
| 6607 | 3 | 4 | | | IV-2 | Nudt21 | 0.93 | 6702 | 3 | 4 | | | IV-2 | P4ha3 | 0.97 |
| 6608 | 3 | 4 | | | IV-2 | Nudt4 | 0.85 | 6703 | 3 | 4 | | | IV-2 | P4hb | 0.74 |
| 6609 | 3 | 4 | | | IV-2 | Nudt7 | 0.81 | 6704 | 3 | 4 | | | IV-2 | Pa2g4 | 0.96 |
| 6610 | 3 | 4 | | | IV-2 | Nudt9 | 0.88 | 6705 | 3 | 4 | | | IV-2 | Pabpc1 | 0.78 |
| 6611 | 3 | 4 | | | IV-2 | Nufip2 | 0.96 | 6706 | 3 | 4 | | | IV-2 | Pacsin2 | 0.98 |
| 6612 | 3 | 4 | | | IV-2 | Numb | 0.85 | 6707 | 3 | 4 | | | IV-2 | Pacsin3 | 0.82 |
| 6613 | 3 | 4 | | | IV-2 | Nup133 | 0.99 | 6708 | 3 | 4 | | | IV-2 | Padi2 | 0.89 |
| 6614 | 3 | 4 | | | IV-2 | Nup153 | 0.95 | 6709 | 3 | 4 | | | IV-2 | Pafah2 | 0.91 |
| 6615 | 3 | 4 | | | IV-2 | Nup160 | 0.73 | 6710 | 3 | 4 | | | IV-2 | Pag1 | 0.95 |
| 6616 | 3 | 4 | | | IV-2 | Nup188 | 0.79 | 6711 | 3 | 4 | | | IV-2 | Pagr1a | 0.95 |
| 6617 | 3 | 4 | | | IV-2 | Nup205 | 0.80 | 6712 | 3 | 4 | | | IV-2 | Paics | 0.84 |
| 6618 | 3 | 4 | | | IV-2 | Nup210 | 0.74 | 6713 | 3 | 4 | | | IV-2 | Paip1 | 0.99 |
| 6619 | 3 | 4 | | | IV-2 | Nup214 | 0.99 | 6714 | 3 | 4 | | | IV-2 | Paip2 | 0.91 |
| 6620 | 3 | 4 | | | IV-2 | Nup35 | 0.71 | 6715 | 3 | 4 | | | IV-2 | Paip2b | 0.95 |
| 6621 | 3 | 4 | | | IV-2 | Nup43 | 0.71 | 6716 | 3 | 4 | | | IV-2 | Paklip1 | 0.98 |
| 6622 | 3 | 4 | | | IV-2 | Nup54 | 0.94 | 6717 | 3 | 4 | | | IV-2 | Pak2 | 0.96 |

Fig. 45 - 36

| | | | | | | | |
|---|---|---|---|---|---|---|---|
| 6718 | 3 | 4 | | IV-2 | Pak4 | 0.72 |
| 6719 | 3 | 4 | | IV-2 | Palb2 | 0.91 |
| 6720 | 3 | 4 | | IV-2 | Palld | 1.00 |
| 6721 | 3 | 4 | | IV-2 | Palm2 | 0.92 |
| 6722 | 3 | 4 | | IV-2 | Palm3 | 0.83 |
| 6723 | 3 | 4 | | IV-2 | Palmd | 0.98 |
| 6724 | 3 | 4 | | IV-2 | Pamr1 | 0.85 |
| 6725 | 3 | 4 | | IV-2 | Pank2 | 0.95 |
| 6726 | 3 | 4 | | IV-2 | Pank3 | 0.90 |
| 6727 | 3 | 4 | | IV-2 | Pank4 | 0.91 |
| 6728 | 3 | 4 | | IV-2 | Panx3 | 0.98 |
| 6729 | 3 | 4 | | IV-2 | Paox | 0.91 |
| 6730 | 3 | 4 | | IV-2 | Papl | 0.83 |
| 6731 | 3 | 4 | | IV-2 | Papola | 0.96 |
| 6732 | 3 | 4 | | IV-2 | Papolb | 0.83 |
| 6733 | 3 | 4 | | IV-2 | Papss1 | 0.98 |
| 6734 | 3 | 4 | | IV-2 | Papss2 | 0.98 |
| 6735 | 3 | 4 | | IV-2 | Paqr4 | 0.85 |
| 6736 | 3 | 4 | | IV-2 | Paqr5 | 0.80 |
| 6737 | 3 | 4 | | IV-2 | Paqr6 | 0.78 |
| 6738 | 3 | 4 | | IV-2 | Pard6b | 0.92 |
| 6739 | 3 | 4 | | IV-2 | Park7 | 0.71 |
| 6740 | 3 | 4 | | IV-2 | Parm1 | 0.83 |
| 6741 | 3 | 4 | | IV-2 | Parp1 | 0.80 |
| 6742 | 3 | 4 | | IV-2 | Parp16 | 0.82 |
| 6743 | 3 | 4 | | IV-2 | Parp4 | 0.86 |
| 6744 | 3 | 4 | | IV-2 | Pars2 | 0.97 |
| 6745 | 3 | 4 | | IV-2 | Parvb | 0.75 |
| 6746 | 3 | 4 | | IV-2 | Parvg | 0.71 |
| 6747 | 3 | 4 | | IV-2 | Pask | 0.82 |
| 6748 | 3 | 4 | | IV-2 | Patl1 | 0.96 |
| 6749 | 3 | 4 | | IV-2 | Pawr | 0.95 |
| 6750 | 3 | 4 | | IV-2 | Pax7 | 0.87 |
| 6751 | 3 | 4 | | IV-2 | Paxip1 | 0.87 |
| 6752 | 3 | 4 | | IV-2 | Pbrm1 | 0.92 |
| 6753 | 3 | 4 | | IV-2 | Pbx2 | 0.95 |
| 6754 | 3 | 4 | | IV-2 | Pbxip1 | 0.87 |
| 6755 | 3 | 4 | | IV-2 | Pcbd1 | 0.69 |
| 6756 | 3 | 4 | | IV-2 | Pcbd2 | 0.79 |
| 6757 | 3 | 4 | | IV-2 | Pcbp1 | 0.73 |
| 6758 | 3 | 4 | | IV-2 | Pcbp2 | 0.99 |
| 6759 | 3 | 4 | | IV-2 | Pcca | 0.81 |
| 6760 | 3 | 4 | | IV-2 | Pcdh1 | 0.87 |
| 6761 | 3 | 4 | | IV-2 | Pcdh12 | 0.71 |
| 6762 | 3 | 4 | | IV-2 | Pcdh20 | 0.96 |
| 6763 | 3 | 4 | | IV-2 | Pcdha5 | 0.86 |
| 6764 | 3 | 4 | | IV-2 | Pcdhb14 | 0.79 |
| 6765 | 3 | 4 | | IV-2 | Pcdhb15 | 0.94 |
| 6766 | 3 | 4 | | IV-2 | Pcdhga5 | 0.83 |
| 6767 | 3 | 4 | | IV-2 | Pcdhgb8 | 0.89 |
| 6768 | 3 | 4 | | IV-2 | Pcdhgc5 | 0.92 |
| 6769 | 3 | 4 | | IV-2 | Pcf11 | 0.87 |
| 6770 | 3 | 4 | | IV-2 | Pcgf3 | 0.96 |
| 6771 | 3 | 4 | | IV-2 | Pcid2 | 0.86 |
| 6772 | 3 | 4 | | IV-2 | Pck2 | 0.99 |
| 6773 | 3 | 4 | | IV-2 | Pcmt1 | 0.78 |
| 6774 | 3 | 4 | | IV-2 | Pcmtd1 | 0.92 |
| 6775 | 3 | 4 | | IV-2 | Pcnp | 0.95 |
| 6776 | 3 | 4 | | IV-2 | Pcnt | 0.82 |
| 6777 | 3 | 4 | | IV-2 | Pcolce | 0.76 |
| 6778 | 3 | 4 | | IV-2 | Pcp4 | 0.81 |
| 6779 | 3 | 4 | | IV-2 | Pcp4l1 | 0.98 |
| 6780 | 3 | 4 | | IV-2 | Pcsk6 | 0.72 |
| 6781 | 3 | 4 | | IV-2 | Pctp | 0.79 |
| 6782 | 3 | 4 | | IV-2 | Pcyox1 | 0.90 |
| 6783 | 3 | 4 | | IV-2 | Pcyox1l | 0.88 |
| 6784 | 3 | 4 | | IV-2 | Pcyt1a | 0.71 |
| 6785 | 3 | 4 | | IV-2 | Pcyt1b | 0.89 |
| 6786 | 3 | 4 | | IV-2 | Pdap1 | 0.90 |
| 6787 | 3 | 4 | | IV-2 | Pdcd10 | 0.94 |
| 6788 | 3 | 4 | | IV-2 | Pdcd2l | 0.97 |
| 6789 | 3 | 4 | | IV-2 | Pdcd4 | 0.93 |
| 6790 | 3 | 4 | | IV-2 | Pdcd5 | 0.69 |
| 6791 | 3 | 4 | | IV-2 | Pdcd6 | 0.99 |
| 6792 | 3 | 4 | | IV-2 | Pdcd6ip | 0.89 |
| 6793 | 3 | 4 | | IV-2 | Pdcd7 | 1.00 |
| 6794 | 3 | 4 | | IV-2 | Pdcl3 | 0.88 |
| 6795 | 3 | 4 | | IV-2 | Pde12 | 0.85 |
| 6796 | 3 | 4 | | IV-2 | Pde2a | 0.89 |
| 6797 | 3 | 4 | | IV-2 | Pde3b | 0.78 |
| 6798 | 3 | 4 | | IV-2 | Pde4a | 0.90 |
| 6799 | 3 | 4 | | IV-2 | Pde4dip | 0.88 |
| 6800 | 3 | 4 | | IV-2 | Pde5a | 0.83 |
| 6801 | 3 | 4 | | IV-2 | Pde6d | 0.85 |
| 6802 | 3 | 4 | | IV-2 | Pde7a | 0.90 |
| 6803 | 3 | 4 | | IV-2 | Pde8a | 0.91 |
| 6804 | 3 | 4 | | IV-2 | Pdf | 0.84 |
| 6805 | 3 | 4 | | IV-2 | Pdgfb | 0.72 |
| 6806 | 3 | 4 | | IV-2 | Pdgfd | 0.87 |
| 6807 | 3 | 4 | | IV-2 | Pdgfrl | 0.93 |
| 6808 | 3 | 4 | | IV-2 | Pdha1 | 0.80 |
| 6809 | 3 | 4 | | IV-2 | Pdhb | 0.74 |
| 6810 | 3 | 4 | | IV-2 | Pdhx | 0.94 |
| 6811 | 3 | 4 | | IV-2 | Pdia3 | 0.69 |
| 6812 | 3 | 4 | | IV-2 | Pdia5 | 0.71 |
| 6813 | 3 | 4 | | IV-2 | Pdik1l | 0.89 |
| 6814 | 3 | 4 | | IV-2 | Pdk1 | 0.67 |
| 6815 | 3 | 4 | | IV-2 | Pdk2 | 0.75 |
| 6816 | 3 | 4 | | IV-2 | Pdk3 | 0.80 |
| 6817 | 3 | 4 | | IV-2 | Pdlim1 | 0.70 |
| 6818 | 3 | 4 | | IV-2 | Pdlim2 | 0.88 |
| 6819 | 3 | 4 | | IV-2 | Pdlim3 | 0.78 |
| 6820 | 3 | 4 | | IV-2 | Pdlim4 | 0.76 |
| 6821 | 3 | 4 | | IV-2 | Pdlim5 | 0.81 |
| 6822 | 3 | 4 | | IV-2 | Pdlim7 | 0.87 |
| 6823 | 3 | 4 | | IV-2 | Pdp2 | 0.94 |
| 6824 | 3 | 4 | | IV-2 | Pdpk1 | 0.99 |
| 6825 | 3 | 4 | | IV-2 | Pdrg1 | 0.97 |
| 6826 | 3 | 4 | | IV-2 | Pds5a | 0.81 |
| 6827 | 3 | 4 | | IV-2 | Pds5b | 0.97 |
| 6828 | 3 | 4 | | IV-2 | Pdss1 | 0.97 |
| 6829 | 3 | 4 | | IV-2 | Pdss2 | 0.99 |
| 6830 | 3 | 4 | | IV-2 | Pdxdc1 | 0.99 |
| 6831 | 3 | 4 | | IV-2 | Pdxk | 0.94 |
| 6832 | 3 | 4 | | IV-2 | Pdzd11 | 0.83 |
| 6833 | 3 | 4 | | IV-2 | Pdzd2 | 0.91 |
| 6834 | 3 | 4 | | IV-2 | Pea15a | 0.98 |
| 6835 | 3 | 4 | | IV-2 | Peak1 | 0.89 |
| 6836 | 3 | 4 | | IV-2 | Pebp1 | 0.93 |
| 6837 | 3 | 4 | | IV-2 | Pecam1 | 0.76 |
| 6838 | 3 | 4 | | IV-2 | Pef1 | 0.86 |
| 6839 | 3 | 4 | | IV-2 | Peg10 | 0.82 |
| 6840 | 3 | 4 | | IV-2 | Peg12 | 0.92 |
| 6841 | 3 | 4 | | IV-2 | Peg3os | 0.74 |
| 6842 | 3 | 4 | | IV-2 | Pelo | 0.88 |
| 6843 | 3 | 4 | | IV-2 | Pelp1 | 0.99 |
| 6844 | 3 | 4 | | IV-2 | Peo1 | 0.85 |
| 6845 | 3 | 4 | | IV-2 | Perm1 | 0.74 |
| 6846 | 3 | 4 | | IV-2 | Perp | 0.82 |
| 6847 | 3 | 4 | | IV-2 | Pet100 | 0.75 |
| 6848 | 3 | 4 | | IV-2 | Pex10 | 0.70 |
| 6849 | 3 | 4 | | IV-2 | Pex11a | 0.81 |
| 6850 | 3 | 4 | | IV-2 | Pex11g | 0.67 |
| 6851 | 3 | 4 | | IV-2 | Pex13 | 0.88 |
| 6852 | 3 | 4 | | IV-2 | Pex16 | 0.71 |
| 6853 | 3 | 4 | | IV-2 | Pex26 | 0.78 |
| 6854 | 3 | 4 | | IV-2 | Pex6 | 0.74 |
| 6855 | 3 | 4 | | IV-2 | Pex7 | 0.91 |
| 6856 | 3 | 4 | | IV-2 | Pf4 | 0.96 |
| 6857 | 3 | 4 | | IV-2 | Pfdn2 | 0.90 |
| 6858 | 3 | 4 | | IV-2 | Pfdn4 | 0.77 |
| 6859 | 3 | 4 | | IV-2 | Pfkfb3 | 0.94 |
| 6860 | 3 | 4 | | IV-2 | Pfkm | 0.75 |
| 6861 | 3 | 4 | | IV-2 | Pfn1 | 0.72 |
| 6862 | 3 | 4 | | IV-2 | Pgap2 | 0.94 |
| 6863 | 3 | 4 | | IV-2 | Pgbd1 | 0.71 |
| 6864 | 3 | 4 | | IV-2 | Pgd | 0.75 |
| 6865 | 3 | 4 | | IV-2 | Pgf | 0.76 |
| 6866 | 3 | 4 | | IV-2 | Pgk1 | 0.71 |
| 6867 | 3 | 4 | | IV-2 | Pgm1 | 0.73 |
| 6868 | 3 | 4 | | IV-2 | Pgm3 | 0.83 |
| 6869 | 3 | 4 | | IV-2 | Pgm5 | 0.98 |
| 6870 | 3 | 4 | | IV-2 | Pgpep1 | 0.80 |
| 6871 | 3 | 4 | | IV-2 | Pgrmc2 | 0.76 |
| 6872 | 3 | 4 | | IV-2 | Phactr4 | 0.98 |
| 6873 | 3 | 4 | | IV-2 | Phb | 0.80 |
| 6874 | 3 | 4 | | IV-2 | Phb2 | 0.87 |
| 6875 | 3 | 4 | | IV-2 | Phex | 0.96 |
| 6876 | 3 | 4 | | IV-2 | Phf10 | 0.90 |
| 6877 | 3 | 4 | | IV-2 | Phf19 | 0.79 |
| 6878 | 3 | 4 | | IV-2 | Phf23 | 0.88 |
| 6879 | 3 | 4 | | IV-2 | Phf5a | 0.71 |
| 6880 | 3 | 4 | | IV-2 | Phf6 | 0.95 |
| 6881 | 3 | 4 | | IV-2 | Phgdh | 0.86 |
| 6882 | 3 | 4 | | IV-2 | Phkb | 0.84 |
| 6883 | 3 | 4 | | IV-2 | Phlda1 | 0.94 |
| 6884 | 3 | 4 | | IV-2 | Phldb2 | 0.93 |
| 6885 | 3 | 4 | | IV-2 | Phldb3 | 0.72 |
| 6886 | 3 | 4 | | IV-2 | Phlpp2 | 0.92 |
| 6887 | 3 | 4 | | IV-2 | Phospho2 | 0.85 |
| 6888 | 3 | 4 | | IV-2 | Phpt1 | 0.98 |
| 6889 | 3 | 4 | | IV-2 | Phtf1 | 0.88 |
| 6890 | 3 | 4 | | IV-2 | Phtf2 | 0.86 |
| 6891 | 3 | 4 | | IV-2 | Phyh | 0.89 |
| 6892 | 3 | 4 | | IV-2 | Pi4k2b | 0.88 |
| 6893 | 3 | 4 | | IV-2 | Pi4ka | 0.92 |
| 6894 | 3 | 4 | | IV-2 | Pias4 | 0.77 |
| 6895 | 3 | 4 | | IV-2 | Picalm | 0.89 |
| 6896 | 3 | 4 | | IV-2 | Piezo1 | 0.89 |
| 6897 | 3 | 4 | | IV-2 | Pigc | 0.93 |
| 6898 | 3 | 4 | | IV-2 | Pigf | 0.99 |
| 6899 | 3 | 4 | | IV-2 | Pigg | 0.93 |
| 6900 | 3 | 4 | | IV-2 | Pigl | 0.96 |
| 6901 | 3 | 4 | | IV-2 | Pigu | 0.93 |
| 6902 | 3 | 4 | | IV-2 | Pigx | 0.93 |
| 6903 | 3 | 4 | | IV-2 | Pigyl | 0.95 |
| 6904 | 3 | 4 | | IV-2 | Pih1d1 | 0.92 |
| 6905 | 3 | 4 | | IV-2 | Pik3ca | 0.99 |
| 6906 | 3 | 4 | | IV-2 | Pik3cb | 0.88 |
| 6907 | 3 | 4 | | IV-2 | Pik3cg | 0.72 |
| 6908 | 3 | 4 | | IV-2 | Pik3r2 | 0.95 |
| 6909 | 3 | 4 | | IV-2 | Pik3r6 | 0.82 |

Fig. 45 - 37

| | | | | | | | | | | | | | | |
|---|---|---|---|---|---|---|---|---|---|---|---|---|---|---|
| 6910 | 3 | 4 | | | IV-2 | Pim1 | 0.95 | 7006 | 3 | 4 | | | IV-2 | Pofut2 | 0.75 |
| 6911 | 3 | 4 | | | IV-2 | Pim2 | 0.80 | 7007 | 3 | 4 | | | IV-2 | Pola2 | 0.71 |
| 6912 | 3 | 4 | | | IV-2 | Pin1 | 0.92 | 7008 | 3 | 4 | | | IV-2 | Polb | 0.93 |
| 6913 | 3 | 4 | | | IV-2 | Pin1rt1 | 0.83 | 7009 | 3 | 4 | | | IV-2 | Pold1 | 0.78 |
| 6914 | 3 | 4 | | | IV-2 | Pin4 | 0.75 | 7010 | 3 | 4 | | | IV-2 | Pold2 | 0.68 |
| 6915 | 3 | 4 | | | IV-2 | Pinlyp | 0.82 | 7011 | 3 | 4 | | | IV-2 | Poldip3 | 0.92 |
| 6916 | 3 | 4 | | | IV-2 | Pinx1 | 0.89 | 7012 | 3 | 4 | | | IV-2 | Pole | 0.92 |
| 6917 | 3 | 4 | | | IV-2 | Pip4k2a | 0.80 | 7013 | 3 | 4 | | | IV-2 | Pole3 | 0.94 |
| 6918 | 3 | 4 | | | IV-2 | Pip4k2c | 0.69 | 7014 | 3 | 4 | | | IV-2 | Pole4 | 0.96 |
| 6919 | 3 | 4 | | | IV-2 | Pip5k1b | 0.70 | 7015 | 3 | 4 | | | IV-2 | Polg | 0.84 |
| 6920 | 3 | 4 | | | IV-2 | Pir | 0.97 | 7016 | 3 | 4 | | | IV-2 | Polg2 | 0.93 |
| 6921 | 3 | 4 | | | IV-2 | Pithd1 | 0.93 | 7017 | 3 | 4 | | | IV-2 | Polh | 0.68 |
| 6922 | 3 | 4 | | | IV-2 | Pitrm1 | 0.87 | 7018 | 3 | 4 | | | IV-2 | Poli | 0.75 |
| 6923 | 3 | 4 | | | IV-2 | Pitx3 | 0.93 | 7019 | 3 | 4 | | | IV-2 | Polr1c | 0.92 |
| 6924 | 3 | 4 | | | IV-2 | Pkd2l2 | 0.71 | 7020 | 3 | 4 | | | IV-2 | Polr1d | 0.77 |
| 6925 | 3 | 4 | | | IV-2 | Pkdcc | 0.96 | 7021 | 3 | 4 | | | IV-2 | Polr2b | 0.93 |
| 6926 | 3 | 4 | | | IV-2 | Pkig | 0.70 | 7022 | 3 | 4 | | | IV-2 | Polr2c | 0.84 |
| 6927 | 3 | 4 | | | IV-2 | Pkm | 0.76 | 7023 | 3 | 4 | | | IV-2 | Polr2d | 0.81 |
| 6928 | 3 | 4 | | | IV-2 | Pkn2 | 0.81 | 7024 | 3 | 4 | | | IV-2 | Polr2e | 0.97 |
| 6929 | 3 | 4 | | | IV-2 | Pknox1 | 0.85 | 7025 | 3 | 4 | | | IV-2 | Polr2f | 0.81 |
| 6930 | 3 | 4 | | | IV-2 | Pkp1 | 0.80 | 7026 | 3 | 4 | | | IV-2 | Polr2h | 0.89 |
| 6931 | 3 | 4 | | | IV-2 | Pkp2 | 0.69 | 7027 | 3 | 4 | | | IV-2 | Polr2j | 0.89 |
| 6932 | 3 | 4 | | | IV-2 | Pkp3 | 0.84 | 7028 | 3 | 4 | | | IV-2 | Polr2k | 0.67 |
| 6933 | 3 | 4 | | | IV-2 | Pla2g4a | 0.93 | 7029 | 3 | 4 | | | IV-2 | Polr2l | 0.81 |
| 6934 | 3 | 4 | | | IV-2 | Pla2g4b | 0.81 | 7030 | 3 | 4 | | | IV-2 | Polr2m | 0.91 |
| 6935 | 3 | 4 | | | IV-2 | Plac8 | 0.76 | 7031 | 3 | 4 | | | IV-2 | Polr3c | 0.94 |
| 6936 | 3 | 4 | | | IV-2 | Plagl2 | 0.78 | 7032 | 3 | 4 | | | IV-2 | Polr3d | 0.99 |
| 6937 | 3 | 4 | | | IV-2 | Plau | 0.86 | 7033 | 3 | 4 | | | IV-2 | Polr3g | 0.69 |
| 6938 | 3 | 4 | | | IV-2 | Plbd1 | 0.79 | 7034 | 3 | 4 | | | IV-2 | Polrmt | 0.91 |
| 6939 | 3 | 4 | | | IV-2 | Plbd2 | 0.99 | 7035 | 3 | 4 | | | IV-2 | Pomgnt1 | 1.00 |
| 6940 | 3 | 4 | | | IV-2 | Plcb2 | 0.68 | 7036 | 3 | 4 | | | IV-2 | Pomk | 0.93 |
| 6941 | 3 | 4 | | | IV-2 | Plcb3 | 0.84 | 7037 | 3 | 4 | | | IV-2 | Pomp | 0.86 |
| 6942 | 3 | 4 | | | IV-2 | Plcg2 | 0.67 | 7038 | 3 | 4 | | | IV-2 | Pon2 | 0.79 |
| 6943 | 3 | 4 | | | IV-2 | Plcxd1 | 0.91 | 7039 | 3 | 4 | | | IV-2 | Pon3 | 0.68 |
| 6944 | 3 | 4 | | | IV-2 | Plcxd2 | 0.95 | 7040 | 3 | 4 | | | IV-2 | Pop1 | 0.94 |
| 6945 | 3 | 4 | | | IV-2 | Pld1 | 0.90 | 7041 | 3 | 4 | | | IV-2 | Pop7 | 0.77 |
| 6946 | 3 | 4 | | | IV-2 | Pld3 | 0.93 | 7042 | 3 | 4 | | | IV-2 | Popdc3 | 0.85 |
| 6947 | 3 | 4 | | | IV-2 | Pld4 | 0.87 | 7043 | 3 | 4 | | | IV-2 | Postn | 0.89 |
| 6948 | 3 | 4 | | | IV-2 | Plec | 0.92 | 7044 | 3 | 4 | | | IV-2 | Pot1a | 0.85 |
| 6949 | 3 | 4 | | | IV-2 | Plekha2 | 0.74 | 7045 | 3 | 4 | | | IV-2 | Pou4f3 | 0.98 |
| 6950 | 3 | 4 | | | IV-2 | Plekha4 | 0.94 | 7046 | 3 | 4 | | | IV-2 | Ppa1 | 0.83 |
| 6951 | 3 | 4 | | | IV-2 | Plekha7 | 0.89 | 7047 | 3 | 4 | | | IV-2 | Ppap2c | 0.81 |
| 6952 | 3 | 4 | | | IV-2 | Plekha8 | 0.88 | 7048 | 3 | 4 | | | IV-2 | Ppapdc1b | 0.82 |
| 6953 | 3 | 4 | | | IV-2 | Plekhb2 | 0.89 | 7049 | 3 | 4 | | | IV-2 | Ppapdc3 | 0.78 |
| 6954 | 3 | 4 | | | IV-2 | Plekhf1 | 0.86 | 7050 | 3 | 4 | | | IV-2 | Ppard | 0.87 |
| 6955 | 3 | 4 | | | IV-2 | Plekhf2 | 0.80 | 7051 | 3 | 4 | | | IV-2 | Ppat | 0.79 |
| 6956 | 3 | 4 | | | IV-2 | Plekhg3 | 0.94 | 7052 | 3 | 4 | | | IV-2 | Ppcs | 0.81 |
| 6957 | 3 | 4 | | | IV-2 | Plekhh1 | 0.99 | 7053 | 3 | 4 | | | IV-2 | Ppdpf | 0.96 |
| 6958 | 3 | 4 | | | IV-2 | Plekhh3 | 0.83 | 7054 | 3 | 4 | | | IV-2 | Ppfia3 | 0.98 |
| 6959 | 3 | 4 | | | IV-2 | Plekhj1 | 0.87 | 7055 | 3 | 4 | | | IV-2 | Ppfibp2 | 0.87 |
| 6960 | 3 | 4 | | | IV-2 | Plekhn1 | 0.91 | 7056 | 3 | 4 | | | IV-2 | Ppia | 0.74 |
| 6961 | 3 | 4 | | | IV-2 | Plekho1 | 0.90 | 7057 | 3 | 4 | | | IV-2 | Ppib | 0.83 |
| 6962 | 3 | 4 | | | IV-2 | Plekho2 | 0.95 | 7058 | 3 | 4 | | | IV-2 | Ppic | 0.94 |
| 6963 | 3 | 4 | | | IV-2 | Plgrkt | 0.86 | 7059 | 3 | 4 | | | IV-2 | Ppid | 0.72 |
| 6964 | 3 | 4 | | | IV-2 | Plin2 | 0.83 | 7060 | 3 | 4 | | | IV-2 | Ppie | 0.79 |
| 6965 | 3 | 4 | | | IV-2 | Plin3 | 0.74 | 7061 | 3 | 4 | | | IV-2 | Ppif | 0.77 |
| 6966 | 3 | 4 | | | IV-2 | Plk4 | 0.70 | 7062 | 3 | 4 | | | IV-2 | Ppig | 0.98 |
| 6967 | 3 | 4 | | | IV-2 | Plp | 0.99 | 7063 | 3 | 4 | | | IV-2 | Ppil1 | 0.71 |
| 6968 | 3 | 4 | | | IV-2 | Plod1 | 0.81 | 7064 | 3 | 4 | | | IV-2 | Ppil3 | 0.80 |
| 6969 | 3 | 4 | | | IV-2 | Plod2 | 0.87 | 7065 | 3 | 4 | | | IV-2 | Ppip5k1 | 0.87 |
| 6970 | 3 | 4 | | | IV-2 | Plod3 | 0.83 | 7066 | 3 | 4 | | | IV-2 | Ppl | 0.96 |
| 6971 | 3 | 4 | | | IV-2 | Plp1 | 0.97 | 7067 | 3 | 4 | | | IV-2 | Ppm1b | 0.94 |
| 6972 | 3 | 4 | | | IV-2 | Plp2 | 0.77 | 7068 | 3 | 4 | | | IV-2 | Ppm1f | 0.85 |
| 6973 | 3 | 4 | | | IV-2 | Pls3 | 0.93 | 7069 | 3 | 4 | | | IV-2 | Ppm1g | 0.82 |
| 6974 | 3 | 4 | | | IV-2 | Plscr1 | 0.86 | 7070 | 3 | 4 | | | IV-2 | Ppm1j | 0.84 |
| 6975 | 3 | 4 | | | IV-2 | Pltp | 0.97 | 7071 | 3 | 4 | | | IV-2 | Ppm1l | 0.95 |
| 6976 | 3 | 4 | | | IV-2 | Plvap | 0.72 | 7072 | 3 | 4 | | | IV-2 | Ppm1m | 0.84 |
| 6977 | 3 | 4 | | | IV-2 | Plxnb2 | 0.99 | 7073 | 3 | 4 | | | IV-2 | Ppme1 | 0.89 |
| 6978 | 3 | 4 | | | IV-2 | Plxnd1 | 0.85 | 7074 | 3 | 4 | | | IV-2 | Ppp1ca | 0.78 |
| 6979 | 3 | 4 | | | IV-2 | Pmel | 0.89 | 7075 | 3 | 4 | | | IV-2 | Ppp1cb | 0.81 |
| 6980 | 3 | 4 | | | IV-2 | Pmf1 | 0.82 | 7076 | 3 | 4 | | | IV-2 | Ppp1cc | 0.92 |
| 6981 | 3 | 4 | | | IV-2 | Pml | 0.85 | 7077 | 3 | 4 | | | IV-2 | Ppp1r10 | 0.85 |
| 6982 | 3 | 4 | | | IV-2 | Pmm1 | 0.86 | 7078 | 3 | 4 | | | IV-2 | Ppp1r11 | 0.86 |
| 6983 | 3 | 4 | | | IV-2 | Pmp22 | 0.84 | 7079 | 3 | 4 | | | IV-2 | Ppp1r12a | 0.90 |
| 6984 | 3 | 4 | | | IV-2 | Pmpca | 0.86 | 7080 | 3 | 4 | | | IV-2 | Ppp1r13l | 1.00 |
| 6985 | 3 | 4 | | | IV-2 | Pmpcb | 0.76 | 7081 | 3 | 4 | | | IV-2 | Ppp1r14a | 0.86 |
| 6986 | 3 | 4 | | | IV-2 | Pms1 | 0.86 | 7082 | 3 | 4 | | | IV-2 | Ppp1r14b | 0.91 |
| 6987 | 3 | 4 | | | IV-2 | Pmvk | 0.78 | 7083 | 3 | 4 | | | IV-2 | Ppp1r14c | 0.89 |
| 6988 | 3 | 4 | | | IV-2 | Pnkd | 0.89 | 7084 | 3 | 4 | | | IV-2 | Ppp1r14d | 0.85 |
| 6989 | 3 | 4 | | | IV-2 | Pnkp | 1.00 | 7085 | 3 | 4 | | | IV-2 | Ppp1r15a | 0.99 |
| 6990 | 3 | 4 | | | IV-2 | Pnliprp1 | 0.89 | 7086 | 3 | 4 | | | IV-2 | Ppp1r15b | 0.86 |
| 6991 | 3 | 4 | | | IV-2 | Pnma1 | 0.69 | 7087 | 3 | 4 | | | IV-2 | Ppp1r16a | 0.96 |
| 6992 | 3 | 4 | | | IV-2 | Pno1 | 0.95 | 7088 | 3 | 4 | | | IV-2 | Ppp1r16b | 0.85 |
| 6993 | 3 | 4 | | | IV-2 | Pnp | 0.78 | 7089 | 3 | 4 | | | IV-2 | Ppp1r1a | 0.85 |
| 6994 | 3 | 4 | | | IV-2 | Pnp2 | 0.68 | 7090 | 3 | 4 | | | IV-2 | Ppp1r37 | 0.90 |
| 6995 | 3 | 4 | | | IV-2 | Pnpla1 | 0.75 | 7091 | 3 | 4 | | | IV-2 | Ppp1r3g | 0.94 |
| 6996 | 3 | 4 | | | IV-2 | Pnpla2 | 0.68 | 7092 | 3 | 4 | | | IV-2 | Ppp1r7 | 0.91 |
| 6997 | 3 | 4 | | | IV-2 | Pnpla3 | 0.91 | 7093 | 3 | 4 | | | IV-2 | Ppp2ca | 0.93 |
| 6998 | 3 | 4 | | | IV-2 | Pnpt1 | 0.81 | 7094 | 3 | 4 | | | IV-2 | Ppp2r1b | 0.79 |
| 6999 | 3 | 4 | | | IV-2 | Pnrc1 | 0.93 | 7095 | 3 | 4 | | | IV-2 | Ppp2r2a | 0.97 |
| 7000 | 3 | 4 | | | IV-2 | Pnrc2 | 0.83 | 7096 | 3 | 4 | | | IV-2 | Ppp2r3a | 0.98 |
| 7001 | 3 | 4 | | | IV-2 | Poc1a | 0.78 | 7097 | 3 | 4 | | | IV-2 | Ppp2r4 | 0.87 |
| 7002 | 3 | 4 | | | IV-2 | Poc1b | 0.95 | 7098 | 3 | 4 | | | IV-2 | Ppp2r5a | 0.79 |
| 7003 | 3 | 4 | | | IV-2 | Podxl | 0.82 | 7099 | 3 | 4 | | | IV-2 | Ppp2r5c | 0.95 |
| 7004 | 3 | 4 | | | IV-2 | Pofib | 0.89 | 7100 | 3 | 4 | | | IV-2 | Ppp2r5d | 0.91 |
| 7005 | 3 | 4 | | | IV-2 | Pofut1 | 0.91 | 7101 | 3 | 4 | | | IV-2 | Ppp4c | 0.71 |

Fig. 45 - 38

| | | | | | | | | | | | | | | | |
|---|---|---|---|---|---|---|---|---|---|---|---|---|---|---|---|
| 7102 | 3 | 4 | | | IV-2 | Ppp4r2 | 0.97 | 7198 | 3 | 4 | | | IV-2 | Psip1 | 0.92 |
| 7103 | 3 | 4 | | | IV-2 | Ppp5c | 0.80 | 7199 | 3 | 4 | | | IV-2 | Psma1 | 0.81 |
| 7104 | 3 | 4 | | | IV-2 | Ppp6c | 0.84 | 7200 | 3 | 4 | | | IV-2 | Psma2 | 0.84 |
| 7105 | 3 | 4 | | | IV-2 | Ppp6r1 | 0.92 | 7201 | 3 | 4 | | | IV-2 | Psma3 | 0.83 |
| 7106 | 3 | 4 | | | IV-2 | Ppp6r3 | 0.94 | 7202 | 3 | 4 | | | IV-2 | Psma4 | 0.92 |
| 7107 | 3 | 4 | | | IV-2 | Pprc1 | 0.91 | 7203 | 3 | 4 | | | IV-2 | Psma5 | 0.71 |
| 7108 | 3 | 4 | | | IV-2 | Ppt1 | 0.99 | 7204 | 3 | 4 | | | IV-2 | Psma6 | 0.96 |
| 7109 | 3 | 4 | | | IV-2 | Ppt2 | 0.77 | 7205 | 3 | 4 | | | IV-2 | Psma7 | 0.86 |
| 7110 | 3 | 4 | | | IV-2 | Pptc7 | 0.94 | 7206 | 3 | 4 | | | IV-2 | Psmb1 | 0.93 |
| 7111 | 3 | 4 | | | IV-2 | Pqlc1 | 0.76 | 7207 | 3 | 4 | | | IV-2 | Psmb10 | 0.82 |
| 7112 | 3 | 4 | | | IV-2 | Pqlc2 | 0.69 | 7208 | 3 | 4 | | | IV-2 | Psmb2 | 0.87 |
| 7113 | 3 | 4 | | | IV-2 | Pradc1 | 0.93 | 7209 | 3 | 4 | | | IV-2 | Psmb3 | 0.77 |
| 7114 | 3 | 4 | | | IV-2 | Praf2 | 0.82 | 7210 | 3 | 4 | | | IV-2 | Psmb4 | 0.95 |
| 7115 | 3 | 4 | | | IV-2 | Prcc | 0.90 | 7211 | 3 | 4 | | | IV-2 | Psmb5 | 0.83 |
| 7116 | 3 | 4 | | | IV-2 | Prcp | 0.80 | 7212 | 3 | 4 | | | IV-2 | Psmb6 | 0.89 |
| 7117 | 3 | 4 | | | IV-2 | Prdm1 | 0.92 | 7213 | 3 | 4 | | | IV-2 | Psmb7 | 0.85 |
| 7118 | 3 | 4 | | | IV-2 | Prdm16 | 0.98 | 7214 | 3 | 4 | | | IV-2 | Psmb8 | 0.87 |
| 7119 | 3 | 4 | | | IV-2 | Prdm2 | 0.95 | 7215 | 3 | 4 | | | IV-2 | Psmc1 | 0.93 |
| 7120 | 3 | 4 | | | IV-2 | Prdm5 | 0.97 | 7216 | 3 | 4 | | | IV-2 | Psmc2 | 0.88 |
| 7121 | 3 | 4 | | | IV-2 | Prdm6 | 0.91 | 7217 | 3 | 4 | | | IV-2 | Psmc3 | 0.84 |
| 7122 | 3 | 4 | | | IV-2 | Prdx1 | 0.74 | 7218 | 3 | 4 | | | IV-2 | Psmc5 | 0.90 |
| 7123 | 3 | 4 | | | IV-2 | Prdx4 | 0.71 | 7219 | 3 | 4 | | | IV-2 | Psmc6 | 0.96 |
| 7124 | 3 | 4 | | | IV-2 | Prdx5 | 0.90 | 7220 | 3 | 4 | | | IV-2 | Psmd1 | 0.91 |
| 7125 | 3 | 4 | | | IV-2 | Prdx6 | 0.77 | 7221 | 3 | 4 | | | IV-2 | Psmd10 | 0.84 |
| 7126 | 3 | 4 | | | IV-2 | Prdx6b | 0.81 | 7222 | 3 | 4 | | | IV-2 | Psmd11 | 0.93 |
| 7127 | 3 | 4 | | | IV-2 | Preb | 0.89 | 7223 | 3 | 4 | | | IV-2 | Psmd12 | 0.84 |
| 7128 | 3 | 4 | | | IV-2 | Prelid1 | 0.76 | 7224 | 3 | 4 | | | IV-2 | Psmd13 | 0.83 |
| 7129 | 3 | 4 | | | IV-2 | Prelp | 0.83 | 7225 | 3 | 4 | | | IV-2 | Psmd14 | 0.92 |
| 7130 | 3 | 4 | | | IV-2 | Prep | 0.90 | 7226 | 3 | 4 | | | IV-2 | Psmd2 | 0.87 |
| 7131 | 3 | 4 | | | IV-2 | Prepl | 0.93 | 7227 | 3 | 4 | | | IV-2 | Psmd3 | 0.95 |
| 7132 | 3 | 4 | | | IV-2 | Prex1 | 0.98 | 7228 | 3 | 4 | | | IV-2 | Psmd4 | 0.92 |
| 7133 | 3 | 4 | | | IV-2 | Prex2 | 0.96 | 7229 | 3 | 4 | | | IV-2 | Psmd5 | 0.88 |
| 7134 | 3 | 4 | | | IV-2 | Prickle3 | 0.99 | 7230 | 3 | 4 | | | IV-2 | Psmd6 | 0.84 |
| 7135 | 3 | 4 | | | IV-2 | Prim1 | 0.86 | 7231 | 3 | 4 | | | IV-2 | Psmd7 | 0.87 |
| 7136 | 3 | 4 | | | IV-2 | Prim2 | 0.73 | 7232 | 3 | 4 | | | IV-2 | Psmd8 | 0.97 |
| 7137 | 3 | 4 | | | IV-2 | Primpol | 0.85 | 7233 | 3 | 4 | | | IV-2 | Psme2b | 0.83 |
| 7138 | 3 | 4 | | | IV-2 | Prkaa1 | 0.98 | 7234 | 3 | 4 | | | IV-2 | Psme3 | 0.81 |
| 7139 | 3 | 4 | | | IV-2 | Prkaa2 | 0.95 | 7235 | 3 | 4 | | | IV-2 | Psme4 | 0.97 |
| 7140 | 3 | 4 | | | IV-2 | Prkab1 | 0.95 | 7236 | 3 | 4 | | | IV-2 | Psmg2 | 0.93 |
| 7141 | 3 | 4 | | | IV-2 | Prkaca | 0.71 | 7237 | 3 | 4 | | | IV-2 | Psors1c2 | 0.83 |
| 7142 | 3 | 4 | | | IV-2 | Prkag1 | 0.77 | 7238 | 3 | 4 | | | IV-2 | Psph | 0.91 |
| 7143 | 3 | 4 | | | IV-2 | Prkag2 | 0.88 | 7239 | 3 | 4 | | | IV-2 | Pspn | 0.73 |
| 7144 | 3 | 4 | | | IV-2 | Prkag3 | 0.77 | 7240 | 3 | 4 | | | IV-2 | Pstk | 0.83 |
| 7145 | 3 | 4 | | | IV-2 | Prkar1a | 0.93 | 7241 | 3 | 4 | | | IV-2 | Ptafr | 0.99 |
| 7146 | 3 | 4 | | | IV-2 | Prkar2a | 0.95 | 7242 | 3 | 4 | | | IV-2 | Ptar1 | 0.82 |
| 7147 | 3 | 4 | | | IV-2 | Prkar2b | 0.69 | 7243 | 3 | 4 | | | IV-2 | Ptbp1 | 0.85 |
| 7148 | 3 | 4 | | | IV-2 | Prkcd | 0.88 | 7244 | 3 | 4 | | | IV-2 | Ptbp3 | 0.83 |
| 7149 | 3 | 4 | | | IV-2 | Prkcdbp | 0.94 | 7245 | 3 | 4 | | | IV-2 | Ptcd1 | 0.98 |
| 7150 | 3 | 4 | | | IV-2 | Prkch | 0.76 | 7246 | 3 | 4 | | | IV-2 | Ptcd2 | 0.92 |
| 7151 | 3 | 4 | | | IV-2 | Prkcsh | 0.72 | 7247 | 3 | 4 | | | IV-2 | Ptcd3 | 0.97 |
| 7152 | 3 | 4 | | | IV-2 | Prkd2 | 0.91 | 7248 | 3 | 4 | | | IV-2 | Ptch1 | 0.94 |
| 7153 | 3 | 4 | | | IV-2 | Prkdc | 0.97 | 7249 | 3 | 4 | | | IV-2 | Ptch2 | 0.99 |
| 7154 | 3 | 4 | | | IV-2 | Prkg2 | 0.72 | 7250 | 3 | 4 | | | IV-2 | Ptdss1 | 0.99 |
| 7155 | 3 | 4 | | | IV-2 | Prkra | 0.99 | 7251 | 3 | 4 | | | IV-2 | Pten | 0.95 |
| 7156 | 3 | 4 | | | IV-2 | Prmt7 | 0.84 | 7252 | 3 | 4 | | | IV-2 | Ptger3 | 0.94 |
| 7157 | 3 | 4 | | | IV-2 | Prob1 | 0.71 | 7253 | 3 | 4 | | | IV-2 | Ptger4 | 0.75 |
| 7158 | 3 | 4 | | | IV-2 | Prokr1 | 0.97 | 7254 | 3 | 4 | | | IV-2 | Ptges2 | 0.73 |
| 7159 | 3 | 4 | | | IV-2 | Prom1 | 0.92 | 7255 | 3 | 4 | | | IV-2 | Ptges3 | 0.79 |
| 7160 | 3 | 4 | | | IV-2 | Prom2 | 0.78 | 7256 | 3 | 4 | | | IV-2 | Ptgfrn | 0.86 |
| 7161 | 3 | 4 | | | IV-2 | Prorsd1 | 0.87 | 7257 | 3 | 4 | | | IV-2 | Ptgir | 0.88 |
| 7162 | 3 | 4 | | | IV-2 | Pros1 | 0.96 | 7258 | 3 | 4 | | | IV-2 | Ptgr1 | 0.74 |
| 7163 | 3 | 4 | | | IV-2 | Prosc | 0.97 | 7259 | 3 | 4 | | | IV-2 | Ptgr2 | 0.77 |
| 7164 | 3 | 4 | | | IV-2 | Prpf18 | 1.00 | 7260 | 3 | 4 | | | IV-2 | Ptgs1 | 0.69 |
| 7165 | 3 | 4 | | | IV-2 | Prpf3 | 0.83 | 7261 | 3 | 4 | | | IV-2 | Pth1r | 0.87 |
| 7166 | 3 | 4 | | | IV-2 | Prpf38a | 0.79 | 7262 | 3 | 4 | | | IV-2 | Ptk2b | 0.95 |
| 7167 | 3 | 4 | | | IV-2 | Prpf38b | 0.92 | 7263 | 3 | 4 | | | IV-2 | Ptma | 0.81 |
| 7168 | 3 | 4 | | | IV-2 | Prpf4 | 0.94 | 7264 | 3 | 4 | | | IV-2 | Ptms | 0.99 |
| 7169 | 3 | 4 | | | IV-2 | Prpf40a | 0.99 | 7265 | 3 | 4 | | | IV-2 | Ptp4a3 | 0.77 |
| 7170 | 3 | 4 | | | IV-2 | Prpf4b | 0.98 | 7266 | 3 | 4 | | | IV-2 | Ptpla | 0.78 |
| 7171 | 3 | 4 | | | IV-2 | Prpf6 | 1.00 | 7267 | 3 | 4 | | | IV-2 | Ptplad1 | 0.88 |
| 7172 | 3 | 4 | | | IV-2 | Prps1 | 0.94 | 7268 | 3 | 4 | | | IV-2 | Ptplad2 | 0.98 |
| 7173 | 3 | 4 | | | IV-2 | Prps1l3 | 0.74 | 7269 | 3 | 4 | | | IV-2 | Ptpmt1 | 0.91 |
| 7174 | 3 | 4 | | | IV-2 | Prps2 | 0.83 | 7270 | 3 | 4 | | | IV-2 | Ptpn11 | 0.99 |
| 7175 | 3 | 4 | | | IV-2 | Prr13 | 0.86 | 7271 | 3 | 4 | | | IV-2 | Ptpn12 | 0.97 |
| 7176 | 3 | 4 | | | IV-2 | Prr14l | 0.86 | 7272 | 3 | 4 | | | IV-2 | Ptpn13 | 0.96 |
| 7177 | 3 | 4 | | | IV-2 | Prr15 | 0.89 | 7273 | 3 | 4 | | | IV-2 | Ptpn14 | 0.96 |
| 7178 | 3 | 4 | | | IV-2 | Prr15l | 0.99 | 7274 | 3 | 4 | | | IV-2 | Ptpn18 | 0.79 |
| 7179 | 3 | 4 | | | IV-2 | Prr33 | 0.71 | 7275 | 3 | 4 | | | IV-2 | Ptpn2 | 0.87 |
| 7180 | 3 | 4 | | | IV-2 | Prr5 | 0.92 | 7276 | 3 | 4 | | | IV-2 | Ptpn21 | 0.89 |
| 7181 | 3 | 4 | | | IV-2 | Prr5l | 0.85 | 7277 | 3 | 4 | | | IV-2 | Ptpn3 | 0.99 |
| 7182 | 3 | 4 | | | IV-2 | Prrc2a | 0.91 | 7278 | 3 | 4 | | | IV-2 | Ptpn4 | 0.95 |
| 7183 | 3 | 4 | | | IV-2 | Prrg2 | 0.99 | 7279 | 3 | 4 | | | IV-2 | Ptpn6 | 0.91 |
| 7184 | 3 | 4 | | | IV-2 | Prrg3 | 0.85 | 7280 | 3 | 4 | | | IV-2 | Ptprb | 0.99 |
| 7185 | 3 | 4 | | | IV-2 | Prss2 | 0.85 | 7281 | 3 | 4 | | | IV-2 | Ptprc | 0.76 |
| 7186 | 3 | 4 | | | IV-2 | Prss34 | 0.95 | 7282 | 3 | 4 | | | IV-2 | Ptprf | 0.88 |
| 7187 | 3 | 4 | | | IV-2 | Prss35 | 0.90 | 7283 | 3 | 4 | | | IV-2 | Ptprj | 1.00 |
| 7188 | 3 | 4 | | | IV-2 | Prss36 | 0.86 | 7284 | 3 | 4 | | | IV-2 | Ptrf | 0.80 |
| 7189 | 3 | 4 | | | IV-2 | Prss53 | 0.89 | 7285 | 3 | 4 | | | IV-2 | Ptrh2 | 1.00 |
| 7190 | 3 | 4 | | | IV-2 | Prss57 | 0.75 | 7286 | 3 | 4 | | | IV-2 | Ptrhd1 | 1.00 |
| 7191 | 3 | 4 | | | IV-2 | Prtn3 | 0.73 | 7287 | 3 | 4 | | | IV-2 | Pts | 0.83 |
| 7192 | 3 | 4 | | | IV-2 | Prune | 1.00 | 7288 | 3 | 4 | | | IV-2 | Ptx4 | 0.87 |
| 7193 | 3 | 4 | | | IV-2 | Psapl1 | 0.72 | 7289 | 3 | 4 | | | IV-2 | Puf60 | 0.89 |
| 7194 | 3 | 4 | | | IV-2 | Psat1 | 0.76 | 7290 | 3 | 4 | | | IV-2 | Purb | 0.85 |
| 7195 | 3 | 4 | | | IV-2 | Psd4 | 0.72 | 7291 | 3 | 4 | | | IV-2 | Purg | 0.81 |
| 7196 | 3 | 4 | | | IV-2 | Psen1 | 0.96 | 7292 | 3 | 4 | | | IV-2 | Pus1 | 0.83 |
| 7197 | 3 | 4 | | | IV-2 | Psenen | 0.84 | 7293 | 3 | 4 | | | IV-2 | Pus10 | 0.93 |

Fig. 45 - 39

| | | | | | | | | | | | | | | |
|---|---|---|---|---|---|---|---|---|---|---|---|---|---|---|
| 7294 | 3 | 4 | | | IV-2 | Pus7 | 0.83 | 7390 | 3 | 4 | | | IV-2 | Rasip1 | 0.84 |
| 7295 | 3 | 4 | | | IV-2 | Pus7l | 0.96 | 7391 | 3 | 4 | | | IV-2 | Rasl10a | 0.96 |
| 7296 | 3 | 4 | | | IV-2 | Pvr | 0.99 | 7392 | 3 | 4 | | | IV-2 | Rassf10 | 0.78 |
| 7297 | 3 | 4 | | | IV-2 | Pvrl2 | 0.83 | 7393 | 3 | 4 | | | IV-2 | Rassf2 | 0.90 |
| 7298 | 3 | 4 | | | IV-2 | Pvrl3 | 0.87 | 7394 | 3 | 4 | | | IV-2 | Rassf3 | 0.67 |
| 7299 | 3 | 4 | | | IV-2 | Pwwp2b | 0.81 | 7395 | 3 | 4 | | | IV-2 | Rassf4 | 0.78 |
| 7300 | 3 | 4 | | | IV-2 | Pxdn | 0.79 | 7396 | 3 | 4 | | | IV-2 | Rassf5 | 0.89 |
| 7301 | 3 | 4 | | | IV-2 | Pxmp2 | 0.98 | 7397 | 3 | 4 | | | IV-2 | Rassf7 | 0.84 |
| 7302 | 3 | 4 | | | IV-2 | Pxmp4 | 0.89 | 7398 | 3 | 4 | | | IV-2 | Rassf9 | 0.86 |
| 7303 | 3 | 4 | | | IV-2 | Pxylp1 | 0.98 | 7399 | 3 | 4 | | | IV-2 | Raver1 | 0.92 |
| 7304 | 3 | 4 | | | IV-2 | Pycr2 | 0.78 | 7400 | 3 | 4 | | | IV-2 | Raver2 | 0.97 |
| 7305 | 3 | 4 | | | IV-2 | Pycrl | 0.74 | 7401 | 3 | 4 | | | IV-2 | Rb1 | 0.84 |
| 7306 | 3 | 4 | | | IV-2 | Pygb | 0.95 | 7402 | 3 | 4 | | | IV-2 | Rb1cc1 | 0.99 |
| 7307 | 3 | 4 | | | IV-2 | Pygo2 | 0.91 | 7403 | 3 | 4 | | | IV-2 | Rbbp4 | 0.91 |
| 7308 | 3 | 4 | | | IV-2 | Pyroxd2 | 0.92 | 7404 | 3 | 4 | | | IV-2 | Rbbp5 | 0.83 |
| 7309 | 3 | 4 | | | IV-2 | Pyurf | 0.99 | 7405 | 3 | 4 | | | IV-2 | Rbbp7 | 0.89 |
| 7310 | 3 | 4 | | | IV-2 | Qdpr | 0.79 | 7406 | 3 | 4 | | | IV-2 | Rbl1 | 0.76 |
| 7311 | 3 | 4 | | | IV-2 | Qprt | 0.84 | 7407 | 3 | 4 | | | IV-2 | Rbm14 | 0.72 |
| 7312 | 3 | 4 | | | IV-2 | Qrsl1 | 0.77 | 7408 | 3 | 4 | | | IV-2 | Rbm24 | 0.95 |
| 7313 | 3 | 4 | | | IV-2 | R3hcc1l | 0.81 | 7409 | 3 | 4 | | | IV-2 | Rbm26 | 0.98 |
| 7314 | 3 | 4 | | | IV-2 | Rab1 | 0.86 | 7410 | 3 | 4 | | | IV-2 | Rbm27 | 0.97 |
| 7315 | 3 | 4 | | | IV-2 | Rab10 | 0.89 | 7411 | 3 | 4 | | | IV-2 | Rbm28 | 0.95 |
| 7316 | 3 | 4 | | | IV-2 | Rab11a | 0.90 | 7412 | 3 | 4 | | | IV-2 | Rbm3os | 0.75 |
| 7317 | 3 | 4 | | | IV-2 | Rab11fip1 | 0.71 | 7413 | 3 | 4 | | | IV-2 | Rbm4 | 0.90 |
| 7318 | 3 | 4 | | | IV-2 | Rab13 | 0.99 | 7414 | 3 | 4 | | | IV-2 | Rbm43 | 0.81 |
| 7319 | 3 | 4 | | | IV-2 | Rab14 | 0.96 | 7415 | 3 | 4 | | | IV-2 | Rbm6 | 0.91 |
| 7320 | 3 | 4 | | | IV-2 | Rab18 | 0.99 | 7416 | 3 | 4 | | | IV-2 | Rbm8a | 0.88 |
| 7321 | 3 | 4 | | | IV-2 | Rab19 | 0.99 | 7417 | 3 | 4 | | | IV-2 | Rbmxl1 | 0.91 |
| 7322 | 3 | 4 | | | IV-2 | Rab1b | 0.91 | 7418 | 3 | 4 | | | IV-2 | Rbp1 | 0.91 |
| 7323 | 3 | 4 | | | IV-2 | Rab21 | 0.97 | 7419 | 3 | 4 | | | IV-2 | Rbp4 | 0.82 |
| 7324 | 3 | 4 | | | IV-2 | Rab22a | 0.90 | 7420 | 3 | 4 | | | IV-2 | Rbpj | 0.82 |
| 7325 | 3 | 4 | | | IV-2 | Rab25 | 0.75 | 7421 | 3 | 4 | | | IV-2 | Rbpms2 | 0.75 |
| 7326 | 3 | 4 | | | IV-2 | Rab27a | 0.82 | 7422 | 3 | 4 | | | IV-2 | Rc3h1 | 0.89 |
| 7327 | 3 | 4 | | | IV-2 | Rab27b | 0.81 | 7423 | 3 | 4 | | | IV-2 | Rcc1 | 0.84 |
| 7328 | 3 | 4 | | | IV-2 | Rab32 | 0.89 | 7424 | 3 | 4 | | | IV-2 | Rcc2 | 0.94 |
| 7329 | 3 | 4 | | | IV-2 | Rab35 | 0.92 | 7425 | 3 | 4 | | | IV-2 | Rccd1 | 0.93 |
| 7330 | 3 | 4 | | | IV-2 | Rab37 | 0.92 | 7426 | 3 | 4 | | | IV-2 | Rchy1 | 0.95 |
| 7331 | 3 | 4 | | | IV-2 | Rab38 | 0.99 | 7427 | 3 | 4 | | | IV-2 | Rcl1 | 0.99 |
| 7332 | 3 | 4 | | | IV-2 | Rab3d | 0.86 | 7428 | 3 | 4 | | | IV-2 | Rcn1 | 0.71 |
| 7333 | 3 | 4 | | | IV-2 | Rab3gap1 | 1.00 | 7429 | 3 | 4 | | | IV-2 | Rcn3 | 0.67 |
| 7334 | 3 | 4 | | | IV-2 | Rab3gap2 | 0.95 | 7430 | 3 | 4 | | | IV-2 | Rcor1 | 0.82 |
| 7335 | 3 | 4 | | | IV-2 | Rab3ip | 0.77 | 7431 | 3 | 4 | | | IV-2 | Rcsd1 | 0.90 |
| 7336 | 3 | 4 | | | IV-2 | Rab42 | 0.98 | 7432 | 3 | 4 | | | IV-2 | Rdh1 | 0.78 |
| 7337 | 3 | 4 | | | IV-2 | Rab43 | 0.89 | 7433 | 3 | 4 | | | IV-2 | Rdh11 | 0.76 |
| 7338 | 3 | 4 | | | IV-2 | Rab44 | 0.80 | 7434 | 3 | 4 | | | IV-2 | Rdh12 | 0.70 |
| 7339 | 3 | 4 | | | IV-2 | Rab5c | 0.94 | 7435 | 3 | 4 | | | IV-2 | Rdm1 | 0.77 |
| 7340 | 3 | 4 | | | IV-2 | Rab7l1 | 0.87 | 7436 | 3 | 4 | | | IV-2 | Rdx | 0.85 |
| 7341 | 3 | 4 | | | IV-2 | Rab8a | 0.81 | 7437 | 3 | 4 | | | IV-2 | Recql | 0.95 |
| 7342 | 3 | 4 | | | IV-2 | Rab8b | 0.78 | 7438 | 3 | 4 | | | IV-2 | Recql4 | 0.80 |
| 7343 | 3 | 4 | | | IV-2 | Rab9 | 0.88 | 7439 | 3 | 4 | | | IV-2 | Reep4 | 0.92 |
| 7344 | 3 | 4 | | | IV-2 | Rabac1 | 0.93 | 7440 | 3 | 4 | | | IV-2 | Reep5 | 0.93 |
| 7345 | 3 | 4 | | | IV-2 | Rabep1 | 0.91 | 7441 | 3 | 4 | | | IV-2 | Reep6 | 0.75 |
| 7346 | 3 | 4 | | | IV-2 | Rabepk | 0.92 | 7442 | 3 | 4 | | | IV-2 | Relt1 | 0.78 |
| 7347 | 3 | 4 | | | IV-2 | Rabgef1 | 0.92 | 7443 | 3 | 4 | | | IV-2 | Rem1 | 0.77 |
| 7348 | 3 | 4 | | | IV-2 | Rabggta | 0.97 | 7444 | 3 | 4 | | | IV-2 | Ren1 | 0.73 |
| 7349 | 3 | 4 | | | IV-2 | Rabggtb | 0.82 | 7445 | 3 | 4 | | | IV-2 | Reps2 | 0.87 |
| 7350 | 3 | 4 | | | IV-2 | Rabif | 0.99 | 7446 | 3 | 4 | | | IV-2 | Rer1 | 0.79 |
| 7351 | 3 | 4 | | | IV-2 | Rabl6 | 0.81 | 7447 | 3 | 4 | | | IV-2 | Retnla | 0.82 |
| 7352 | 3 | 4 | | | IV-2 | Rac1 | 0.94 | 7448 | 3 | 4 | | | IV-2 | Rexo4 | 0.85 |
| 7353 | 3 | 4 | | | IV-2 | Rac2 | 0.72 | 7449 | 3 | 4 | | | IV-2 | Rfc1 | 0.85 |
| 7354 | 3 | 4 | | | IV-2 | Racgap1 | 0.68 | 7450 | 3 | 4 | | | IV-2 | Rfc2 | 0.75 |
| 7355 | 3 | 4 | | | IV-2 | Rad1 | 0.90 | 7451 | 3 | 4 | | | IV-2 | Rfc5 | 0.70 |
| 7356 | 3 | 4 | | | IV-2 | Rad17 | 0.95 | 7452 | 3 | 4 | | | IV-2 | Rffl | 0.85 |
| 7357 | 3 | 4 | | | IV-2 | Rad21 | 0.79 | 7453 | 3 | 4 | | | IV-2 | Rfk | 0.96 |
| 7358 | 3 | 4 | | | IV-2 | Rad23b | 0.96 | 7454 | 3 | 4 | | | IV-2 | Rftn2 | 0.98 |
| 7359 | 3 | 4 | | | IV-2 | Rad52 | 0.93 | 7455 | 3 | 4 | | | IV-2 | Rfwd3 | 0.68 |
| 7360 | 3 | 4 | | | IV-2 | Rad54b | 0.71 | 7456 | 3 | 4 | | | IV-2 | Rfx5 | 0.98 |
| 7361 | 3 | 4 | | | IV-2 | Rad9a | 0.88 | 7457 | 3 | 4 | | | IV-2 | Rfxap | 0.93 |
| 7362 | 3 | 4 | | | IV-2 | Rai14 | 0.98 | 7458 | 3 | 4 | | | IV-2 | Rgl1 | 0.98 |
| 7363 | 3 | 4 | | | IV-2 | Rai2 | 0.80 | 7459 | 3 | 4 | | | IV-2 | Rgl2 | 0.99 |
| 7364 | 3 | 4 | | | IV-2 | Ralb | 0.72 | 7460 | 3 | 4 | | | IV-2 | Rgs16 | 0.95 |
| 7365 | 3 | 4 | | | IV-2 | Ralbp1 | 0.80 | 7461 | 3 | 4 | | | IV-2 | Rgs19 | 0.85 |
| 7366 | 3 | 4 | | | IV-2 | Ralgapa1 | 0.93 | 7462 | 3 | 4 | | | IV-2 | Rgs2 | 0.95 |
| 7367 | 3 | 4 | | | IV-2 | Raly | 0.81 | 7463 | 3 | 4 | | | IV-2 | Rgs3 | 1.00 |
| 7368 | 3 | 4 | | | IV-2 | Ramp1 | 0.71 | 7464 | 3 | 4 | | | IV-2 | Rgs5 | 0.85 |
| 7369 | 3 | 4 | | | IV-2 | Ramp2 | 0.82 | 7465 | 3 | 4 | | | IV-2 | Rgs7bp | 1.00 |
| 7370 | 3 | 4 | | | IV-2 | Ran | 0.76 | 7466 | 3 | 4 | | | IV-2 | Rhbdd1 | 0.86 |
| 7371 | 3 | 4 | | | IV-2 | Ranbp1 | 0.82 | 7467 | 3 | 4 | | | IV-2 | Rhbdf2 | 0.97 |
| 7372 | 3 | 4 | | | IV-2 | Ranbp10 | 0.83 | 7468 | 3 | 4 | | | IV-2 | Rhbdl2 | 0.87 |
| 7373 | 3 | 4 | | | IV-2 | Ranbp2 | 0.87 | 7469 | 3 | 4 | | | IV-2 | Rhbdl3 | 0.91 |
| 7374 | 3 | 4 | | | IV-2 | Ranbp6 | 0.96 | 7470 | 3 | 4 | | | IV-2 | Rhbg | 0.85 |
| 7375 | 3 | 4 | | | IV-2 | Rangrf | 0.89 | 7471 | 3 | 4 | | | IV-2 | Rhno1 | 0.83 |
| 7376 | 3 | 4 | | | IV-2 | Rap1a | 0.75 | 7472 | 3 | 4 | | | IV-2 | Rhoa | 0.77 |
| 7377 | 3 | 4 | | | IV-2 | Rap1b | 0.96 | 7473 | 3 | 4 | | | IV-2 | Rhob | 0.92 |
| 7378 | 3 | 4 | | | IV-2 | Rapgds1 | 0.90 | 7474 | 3 | 4 | | | IV-2 | Rhoc | 0.87 |
| 7379 | 3 | 4 | | | IV-2 | Rapgef3 | 0.91 | 7475 | 3 | 4 | | | IV-2 | Rhod | 0.78 |
| 7380 | 3 | 4 | | | IV-2 | Rapgef5 | 1.00 | 7476 | 3 | 4 | | | IV-2 | Rhog | 0.80 |
| 7381 | 3 | 4 | | | IV-2 | Raph1 | 0.88 | 7477 | 3 | 4 | | | IV-2 | Rhoj | 0.95 |
| 7382 | 3 | 4 | | | IV-2 | Rarres1 | 0.80 | 7478 | 3 | 4 | | | IV-2 | Rhoq | 0.89 |
| 7383 | 3 | 4 | | | IV-2 | Rars | 0.90 | 7479 | 3 | 4 | | | IV-2 | Rhot1 | 1.00 |
| 7384 | 3 | 4 | | | IV-2 | Rasa3 | 0.89 | 7480 | 3 | 4 | | | IV-2 | Rhot2 | 0.87 |
| 7385 | 3 | 4 | | | IV-2 | Rasd2 | 1.00 | 7481 | 3 | 4 | | | IV-2 | Rhou | 0.88 |
| 7386 | 3 | 4 | | | IV-2 | Rasgrp1 | 0.82 | 7482 | 3 | 4 | | | IV-2 | Rhov | 0.88 |
| 7387 | 3 | 4 | | | IV-2 | Rasgrp2 | 0.78 | 7483 | 3 | 4 | | | IV-2 | Rhpn1 | 0.90 |
| 7388 | 3 | 4 | | | IV-2 | Rasgrp3 | 0.82 | 7484 | 3 | 4 | | | IV-2 | Rian | 0.80 |
| 7389 | 3 | 4 | | | IV-2 | Rasgrp4 | 0.85 | 7485 | 3 | 4 | | | IV-2 | Ribc1 | 0.88 |

Fig. 45 - 40

| | | | | | | | | | | | | | | | |
|---|---|---|---|---|---|---|---|---|---|---|---|---|---|---|---|
| 7486 | 3 | 4 | | | IV-2 | Rif1 | 0.94 | 7582 | 3 | 4 | | | IV-2 | Rpp21 | 0.93 |
| 7487 | 3 | 4 | | | IV-2 | Riip | 0.76 | 7583 | 3 | 4 | | | IV-2 | Rpp25l | 0.87 |
| 7488 | 3 | 4 | | | IV-2 | Rin3 | 0.94 | 7584 | 3 | 4 | | | IV-2 | Rpp30 | 0.93 |
| 7489 | 3 | 4 | | | IV-2 | Rinl | 0.77 | 7585 | 3 | 4 | | | IV-2 | Rpp38 | 0.94 |
| 7490 | 3 | 4 | | | IV-2 | Rint1 | 0.88 | 7586 | 3 | 4 | | | IV-2 | Rpp40 | 0.74 |
| 7491 | 3 | 4 | | | IV-2 | Ripk1 | 0.89 | 7587 | 3 | 4 | | | IV-2 | Rprd1a | 0.86 |
| 7492 | 3 | 4 | | | IV-2 | Ripk2 | 1.00 | 7588 | 3 | 4 | | | IV-2 | Rprd1b | 0.85 |
| 7493 | 3 | 4 | | | IV-2 | Ripk3 | 0.81 | 7589 | 3 | 4 | | | IV-2 | Rprd2 | 0.96 |
| 7494 | 3 | 4 | | | IV-2 | Ripk4 | 0.98 | 7590 | 3 | 4 | | | IV-2 | Rps15 | 0.96 |
| 7495 | 3 | 4 | | | IV-2 | Ripply1 | 0.78 | 7591 | 3 | 4 | | | IV-2 | Rps19bp1 | 0.92 |
| 7496 | 3 | 4 | | | IV-2 | Rit1 | 0.89 | 7592 | 3 | 4 | | | IV-2 | Rps2 | 0.84 |
| 7497 | 3 | 4 | | | IV-2 | Rit2 | 0.75 | 7593 | 3 | 4 | | | IV-2 | Rps27l | 0.85 |
| 7498 | 3 | 4 | | | IV-2 | Rita1 | 0.90 | 7594 | 3 | 4 | | | IV-2 | Rps6 | 1.00 |
| 7499 | 3 | 4 | | | IV-2 | Rmdn1 | 0.85 | 7595 | 3 | 4 | | | IV-2 | Rps6ka1 | 0.69 |
| 7500 | 3 | 4 | | | IV-2 | Rmdn2 | 0.87 | 7596 | 3 | 4 | | | IV-2 | Rps6ka3 | 0.84 |
| 7501 | 3 | 4 | | | IV-2 | Rmdn3 | 0.87 | 7597 | 3 | 4 | | | IV-2 | Rps6ka4 | 0.94 |
| 7502 | 3 | 4 | | | IV-2 | Rmi1 | 0.77 | 7598 | 3 | 4 | | | IV-2 | Rpsa | 0.93 |
| 7503 | 3 | 4 | | | IV-2 | Rmnd5a | 0.96 | 7599 | 3 | 4 | | | IV-2 | Rptoros | 0.80 |
| 7504 | 3 | 4 | | | IV-2 | Rmrp | 0.72 | 7600 | 3 | 4 | | | IV-2 | Rpusd4 | 0.76 |
| 7505 | 3 | 4 | | | IV-2 | Rn45s | 0.85 | 7601 | 3 | 4 | | | IV-2 | Rqcd1 | 0.84 |
| 7506 | 3 | 4 | | | IV-2 | Rnase6 | 0.75 | 7602 | 3 | 4 | | | IV-2 | Rrad | 0.86 |
| 7507 | 3 | 4 | | | IV-2 | Rnaseh2a | 0.92 | 7603 | 3 | 4 | | | IV-2 | Rragd | 0.99 |
| 7508 | 3 | 4 | | | IV-2 | Rnaseh2b | 0.87 | 7604 | 3 | 4 | | | IV-2 | Rras2 | 0.91 |
| 7509 | 3 | 4 | | | IV-2 | Rnaseh2c | 0.68 | 7605 | 3 | 4 | | | IV-2 | Rrbp1 | 0.79 |
| 7510 | 3 | 4 | | | IV-2 | Rnasek | 0.90 | 7606 | 3 | 4 | | | IV-2 | Rreb1 | 0.72 |
| 7511 | 3 | 4 | | | IV-2 | Rnaset2a | 0.86 | 7607 | 3 | 4 | | | IV-2 | Rrp7a | 0.91 |
| 7512 | 3 | 4 | | | IV-2 | Rnaset2b | 0.88 | 7608 | 3 | 4 | | | IV-2 | Rsc1a1 | 0.94 |
| 7513 | 3 | 4 | | | IV-2 | Rnf10 | 0.88 | 7609 | 3 | 4 | | | IV-2 | Rsl1 | 0.76 |
| 7514 | 3 | 4 | | | IV-2 | Rnf121 | 0.86 | 7610 | 3 | 4 | | | IV-2 | Rsph3a | 0.91 |
| 7515 | 3 | 4 | | | IV-2 | Rnf123 | 0.82 | 7611 | 3 | 4 | | | IV-2 | Rsph3b | 1.00 |
| 7516 | 3 | 4 | | | IV-2 | Rnf125 | 0.98 | 7612 | 3 | 4 | | | IV-2 | Rspry1 | 0.99 |
| 7517 | 3 | 4 | | | IV-2 | Rnf126 | 0.96 | 7613 | 3 | 4 | | | IV-2 | Rsrc2 | 0.96 |
| 7518 | 3 | 4 | | | IV-2 | Rnf139 | 0.84 | 7614 | 3 | 4 | | | IV-2 | Rsrp1 | 0.95 |
| 7519 | 3 | 4 | | | IV-2 | Rnf141 | 0.80 | 7615 | 3 | 4 | | | IV-2 | Rsu1 | 0.73 |
| 7520 | 3 | 4 | | | IV-2 | Rnf144b | 0.95 | 7616 | 3 | 4 | | | IV-2 | Rtkn2 | 0.87 |
| 7521 | 3 | 4 | | | IV-2 | Rnf167 | 0.91 | 7617 | 3 | 4 | | | IV-2 | Rttn | 0.92 |
| 7522 | 3 | 4 | | | IV-2 | Rnf168 | 0.88 | 7618 | 3 | 4 | | | IV-2 | Rundc1 | 0.91 |
| 7523 | 3 | 4 | | | IV-2 | Rnf181 | 0.94 | 7619 | 3 | 4 | | | IV-2 | Ruvbl2 | 0.83 |
| 7524 | 3 | 4 | | | IV-2 | Rnf19a | 0.86 | 7620 | 3 | 4 | | | IV-2 | Rwdd2b | 1.00 |
| 7525 | 3 | 4 | | | IV-2 | Rnf20 | 0.98 | 7621 | 3 | 4 | | | IV-2 | Rxra | 0.94 |
| 7526 | 3 | 4 | | | IV-2 | Rnf219 | 0.96 | 7622 | 3 | 4 | | | IV-2 | Rxrg | 0.99 |
| 7527 | 3 | 4 | | | IV-2 | Rnf222 | 0.99 | 7623 | 3 | 4 | | | IV-2 | Rybp | 1.00 |
| 7528 | 3 | 4 | | | IV-2 | Rnf26 | 0.89 | 7624 | 3 | 4 | | | IV-2 | Ryk | 0.98 |
| 7529 | 3 | 4 | | | IV-2 | Rnf32 | 0.69 | 7625 | 3 | 4 | | | IV-2 | Ryr3 | 0.90 |
| 7530 | 3 | 4 | | | IV-2 | Rnf34 | 0.99 | 7626 | 3 | 4 | | | IV-2 | S100a1 | 0.69 |
| 7531 | 3 | 4 | | | IV-2 | Rnf39 | 0.97 | 7627 | 3 | 4 | | | IV-2 | S100a10 | 0.75 |
| 7532 | 3 | 4 | | | IV-2 | Rnf4 | 0.94 | 7628 | 3 | 4 | | | IV-2 | S100a11 | 0.87 |
| 7533 | 3 | 4 | | | IV-2 | Rnf43 | 0.73 | 7629 | 3 | 4 | | | IV-2 | S100a14 | 0.77 |
| 7534 | 3 | 4 | | | IV-2 | Rnf5 | 0.84 | 7630 | 3 | 4 | | | IV-2 | S100a16 | 0.83 |
| 7535 | 3 | 4 | | | IV-2 | Rnf6 | 0.86 | 7631 | 3 | 4 | | | IV-2 | S100a4 | 0.83 |
| 7536 | 3 | 4 | | | IV-2 | Rnf7 | 0.82 | 7632 | 3 | 4 | | | IV-2 | S100g | 0.93 |
| 7537 | 3 | 4 | | | IV-2 | Rnf8 | 0.91 | 7633 | 3 | 4 | | | IV-2 | S1pr2 | 0.93 |
| 7538 | 3 | 4 | | | IV-2 | Rnft1 | 0.77 | 7634 | 3 | 4 | | | IV-2 | S1pr3 | 0.90 |
| 7539 | 3 | 4 | | | IV-2 | Rngtt | 0.76 | 7635 | 3 | 4 | | | IV-2 | S1pr4 | 0.80 |
| 7540 | 3 | 4 | | | IV-2 | Rnmtl1 | 0.82 | 7636 | 3 | 4 | | | IV-2 | Saal1 | 0.84 |
| 7541 | 3 | 4 | | | IV-2 | Rnpepl1 | 0.85 | 7637 | 3 | 4 | | | IV-2 | Sac3d1 | 0.92 |
| 7542 | 3 | 4 | | | IV-2 | Rnps1 | 0.98 | 7638 | 3 | 4 | | | IV-2 | Sacm1l | 0.78 |
| 7543 | 3 | 4 | | | IV-2 | Robo4 | 0.89 | 7639 | 3 | 4 | | | IV-2 | Sae1 | 0.78 |
| 7544 | 3 | 4 | | | IV-2 | Rock1 | 0.88 | 7640 | 3 | 4 | | | IV-2 | Safb2 | 0.96 |
| 7545 | 3 | 4 | | | IV-2 | Rora | 0.82 | 7641 | 3 | 4 | | | IV-2 | Samd1 | 0.75 |
| 7546 | 3 | 4 | | | IV-2 | Rorc | 0.70 | 7642 | 3 | 4 | | | IV-2 | Samd9l | 0.81 |
| 7547 | 3 | 4 | | | IV-2 | Rp2h | 1.00 | 7643 | 3 | 4 | | | IV-2 | Samhd1 | 0.86 |
| 7548 | 3 | 4 | | | IV-2 | Rp9 | 0.85 | 7644 | 3 | 4 | | | IV-2 | Samm50 | 0.90 |
| 7549 | 3 | 4 | | | IV-2 | Rpa2 | 0.81 | 7645 | 3 | 4 | | | IV-2 | Samsn1 | 0.90 |
| 7550 | 3 | 4 | | | IV-2 | Rpap1 | 0.94 | 7646 | 3 | 4 | | | IV-2 | Sap18 | 0.72 |
| 7551 | 3 | 4 | | | IV-2 | Rpf1 | 0.92 | 7647 | 3 | 4 | | | IV-2 | Sap30 | 0.84 |
| 7552 | 3 | 4 | | | IV-2 | Rpf2 | 0.93 | 7648 | 3 | 4 | | | IV-2 | Sapcd2 | 0.75 |
| 7553 | 3 | 4 | | | IV-2 | Rpgrip1l | 0.96 | 7649 | 3 | 4 | | | IV-2 | Sar1a | 0.95 |
| 7554 | 3 | 4 | | | IV-2 | Rph3al | 0.74 | 7650 | 3 | 4 | | | IV-2 | Sar1b | 0.95 |
| 7555 | 3 | 4 | | | IV-2 | Rpi10 | 0.85 | 7651 | 3 | 4 | | | IV-2 | Sardh | 0.69 |
| 7556 | 3 | 4 | | | IV-2 | Rpl14 | 0.97 | 7652 | 3 | 4 | | | IV-2 | Sarnp | 0.79 |
| 7557 | 3 | 4 | | | IV-2 | Rpl15 | 0.90 | 7653 | 3 | 4 | | | IV-2 | Sars2 | 0.92 |
| 7558 | 3 | 4 | | | IV-2 | Rpl19 | 0.89 | 7654 | 3 | 4 | | | IV-2 | Sart1 | 1.00 |
| 7559 | 3 | 4 | | | IV-2 | Rpl22l1 | 0.85 | 7655 | 3 | 4 | | | IV-2 | Sart3 | 0.93 |
| 7560 | 3 | 4 | | | IV-2 | Rpl23 | 0.91 | 7656 | 3 | 4 | | | IV-2 | Sass6 | 0.81 |
| 7561 | 3 | 4 | | | IV-2 | Rpl23a | 0.91 | 7657 | 3 | 4 | | | IV-2 | Satb2 | 0.96 |
| 7562 | 3 | 4 | | | IV-2 | Rpl27 | 0.96 | 7658 | 3 | 4 | | | IV-2 | Sav1 | 0.87 |
| 7563 | 3 | 4 | | | IV-2 | Rpl27a | 0.77 | 7659 | 3 | 4 | | | IV-2 | Sbds | 0.89 |
| 7564 | 3 | 4 | | | IV-2 | Rpl30 | 0.96 | 7660 | 3 | 4 | | | IV-2 | Sbno1 | 0.96 |
| 7565 | 3 | 4 | | | IV-2 | Rpl31-ps12 | 0.95 | 7661 | 3 | 4 | | | IV-2 | Sbsn | 0.83 |
| 7566 | 3 | 4 | | | IV-2 | Rpl36al | 0.76 | 7662 | 3 | 4 | | | IV-2 | Sbspon | 0.78 |
| 7567 | 3 | 4 | | | IV-2 | Rpl37 | 0.84 | 7663 | 3 | 4 | | | IV-2 | Sc5d | 0.68 |
| 7568 | 3 | 4 | | | IV-2 | Rpl37a | 0.88 | 7664 | 3 | 4 | | | IV-2 | Scaf11 | 0.98 |
| 7569 | 3 | 4 | | | IV-2 | Rpl38 | 0.75 | 7665 | 3 | 4 | | | IV-2 | Scamp4 | 0.91 |
| 7570 | 3 | 4 | | | IV-2 | Rpl39 | 0.99 | 7666 | 3 | 4 | | | IV-2 | Scand1 | 0.96 |
| 7571 | 3 | 4 | | | IV-2 | Rpl4 | 0.99 | 7667 | 3 | 4 | | | IV-2 | Scarb1 | 0.85 |
| 7572 | 3 | 4 | | | IV-2 | Rpl41 | 0.89 | 7668 | 3 | 4 | | | IV-2 | Scarf1 | 0.85 |
| 7573 | 3 | 4 | | | IV-2 | Rpl6 | 0.96 | 7669 | 3 | 4 | | | IV-2 | Sccpdh | 0.85 |
| 7574 | 3 | 4 | | | IV-2 | Rpl7 | 0.93 | 7670 | 3 | 4 | | | IV-2 | Scel | 0.82 |
| 7575 | 3 | 4 | | | IV-2 | Rpl7a | 0.91 | 7671 | 3 | 4 | | | IV-2 | Scfd1 | 0.94 |
| 7576 | 3 | 4 | | | IV-2 | Rpl7l1 | 0.84 | 7672 | 3 | 4 | | | IV-2 | Scfd2 | 0.90 |
| 7577 | 3 | 4 | | | IV-2 | Rplp1 | 0.92 | 7673 | 3 | 4 | | | IV-2 | Scin | 0.98 |
| 7578 | 3 | 4 | | | IV-2 | Rplp2 | 0.96 | 7674 | 3 | 4 | | | IV-2 | Scml2 | 0.93 |
| 7579 | 3 | 4 | | | IV-2 | Rpn1 | 0.75 | 7675 | 3 | 4 | | | IV-2 | Scn10a | 0.94 |
| 7580 | 3 | 4 | | | IV-2 | Rpn2 | 0.73 | 7676 | 3 | 4 | | | IV-2 | Scn4b | 0.72 |
| 7581 | 3 | 4 | | | IV-2 | Rpp14 | 0.93 | 7677 | 3 | 4 | | | IV-2 | Scn7a | 0.67 |

Fig. 45 - 41

| | | | | | | | | | | | | | | | |
|---|---|---|---|---|---|---|---|---|---|---|---|---|---|---|---|
| 7678 | 3 | 4 | | | IV-2 | Scnm1 | 0.84 | 7774 | 3 | 4 | | | IV-2 | Sf3b3 | 0.89 |
| 7679 | 3 | 4 | | | IV-2 | Sco2 | 0.84 | 7775 | 3 | 4 | | | IV-2 | Sf3b5 | 0.87 |
| 7680 | 3 | 4 | | | IV-2 | Scoc | 0.94 | 7776 | 3 | 4 | | | IV-2 | Sf3b6 | 0.94 |
| 7681 | 3 | 4 | | | IV-2 | Scp2 | 0.90 | 7777 | 3 | 4 | | | IV-2 | Sfn | 0.79 |
| 7682 | 3 | 4 | | | IV-2 | Scpep1 | 0.71 | 7778 | 3 | 4 | | | IV-2 | Sfr1 | 0.98 |
| 7683 | 3 | 4 | | | IV-2 | Scrg1 | 0.90 | 7779 | 3 | 4 | | | IV-2 | Sfrp4 | 0.84 |
| 7684 | 3 | 4 | | | IV-2 | Scrib | 1.00 | 7780 | 3 | 4 | | | IV-2 | Sfrp5 | 0.90 |
| 7685 | 3 | 4 | | | IV-2 | Scrn2 | 0.91 | 7781 | 3 | 4 | | | IV-2 | Sft2d1 | 0.92 |
| 7686 | 3 | 4 | | | IV-2 | Scyl1 | 0.94 | 7782 | 3 | 4 | | | IV-2 | Sft2d2 | 0.92 |
| 7687 | 3 | 4 | | | IV-2 | Scyl2 | 0.98 | 7783 | 3 | 4 | | | IV-2 | Sfxn1 | 0.92 |
| 7688 | 3 | 4 | | | IV-2 | Sdc1 | 0.92 | 7784 | 3 | 4 | | | IV-2 | Sfxn4 | 0.93 |
| 7689 | 3 | 4 | | | IV-2 | Sdc2 | 0.86 | 7785 | 3 | 4 | | | IV-2 | Sfxn5 | 0.94 |
| 7690 | 3 | 4 | | | IV-2 | Sdc4 | 0.86 | 7786 | 3 | 4 | | | IV-2 | Sgca | 0.83 |
| 7691 | 3 | 4 | | | IV-2 | Sdcbp | 0.85 | 7787 | 3 | 4 | | | IV-2 | Sgcd | 0.96 |
| 7692 | 3 | 4 | | | IV-2 | Sdcbp2 | 0.86 | 7788 | 3 | 4 | | | IV-2 | Sgcg | 0.81 |
| 7693 | 3 | 4 | | | IV-2 | Sde2 | 0.87 | 7789 | 3 | 4 | | | IV-2 | Sgk3 | 0.68 |
| 7694 | 3 | 4 | | | IV-2 | Sdf2 | 0.96 | 7790 | 3 | 4 | | | IV-2 | Sgms1 | 0.95 |
| 7695 | 3 | 4 | | | IV-2 | Sdha | 0.69 | 7791 | 3 | 4 | | | IV-2 | Sgms2 | 0.83 |
| 7696 | 3 | 4 | | | IV-2 | Sdhaf2 | 0.85 | 7792 | 3 | 4 | | | IV-2 | Sgpp1 | 0.77 |
| 7697 | 3 | 4 | | | IV-2 | Sdhc | 0.71 | 7793 | 3 | 4 | | | IV-2 | Sgpp2 | 0.76 |
| 7698 | 3 | 4 | | | IV-2 | Sdk1 | 0.82 | 7794 | 3 | 4 | | | IV-2 | Sgsm2 | 0.90 |
| 7699 | 3 | 4 | | | IV-2 | Sdr16c6 | 0.89 | 7795 | 3 | 4 | | | IV-2 | Sgsm3 | 0.94 |
| 7700 | 3 | 4 | | | IV-2 | Sdr42e1 | 0.70 | 7796 | 3 | 4 | | | IV-2 | Sgta | 0.96 |
| 7701 | 3 | 4 | | | IV-2 | Sdsl | 0.86 | 7797 | 3 | 4 | | | IV-2 | Sh2b1 | 0.97 |
| 7702 | 3 | 4 | | | IV-2 | Sec11a | 0.89 | 7798 | 3 | 4 | | | IV-2 | Sh2b2 | 0.77 |
| 7703 | 3 | 4 | | | IV-2 | Sec11c | 0.98 | 7799 | 3 | 4 | | | IV-2 | Sh3bgrl | 0.99 |
| 7704 | 3 | 4 | | | IV-2 | Sec13 | 0.87 | 7800 | 3 | 4 | | | IV-2 | Sh3bgrl2 | 0.92 |
| 7705 | 3 | 4 | | | IV-2 | Sec14l1 | 0.84 | 7801 | 3 | 4 | | | IV-2 | Sh3bgrl3 | 1.00 |
| 7706 | 3 | 4 | | | IV-2 | Sec14l2 | 0.82 | 7802 | 3 | 4 | | | IV-2 | Sh3bp1 | 0.95 |
| 7707 | 3 | 4 | | | IV-2 | Sec14l3 | 0.95 | 7803 | 3 | 4 | | | IV-2 | Sh3bp4 | 0.95 |
| 7708 | 3 | 4 | | | IV-2 | Sec16a | 0.97 | 7804 | 3 | 4 | | | IV-2 | Sh3bp5l | 0.93 |
| 7709 | 3 | 4 | | | IV-2 | Sec16b | 0.96 | 7805 | 3 | 4 | | | IV-2 | Sh3d19 | 0.74 |
| 7710 | 3 | 4 | | | IV-2 | Sec22a | 0.95 | 7806 | 3 | 4 | | | IV-2 | Sh3gl1 | 0.87 |
| 7711 | 3 | 4 | | | IV-2 | Sec22b | 0.97 | 7807 | 3 | 4 | | | IV-2 | Sh3glb1 | 0.98 |
| 7712 | 3 | 4 | | | IV-2 | Sec23b | 0.88 | 7808 | 3 | 4 | | | IV-2 | Sh3kbp1 | 0.89 |
| 7713 | 3 | 4 | | | IV-2 | Sec23ip | 0.89 | 7809 | 3 | 4 | | | IV-2 | Sh3pxd2a | 0.79 |
| 7714 | 3 | 4 | | | IV-2 | Sec24a | 0.96 | 7810 | 3 | 4 | | | IV-2 | Sh3rf2 | 0.70 |
| 7715 | 3 | 4 | | | IV-2 | Sec24c | 0.90 | 7811 | 3 | 4 | | | IV-2 | Sh3tc1 | 0.88 |
| 7716 | 3 | 4 | | | IV-2 | Sec31a | 0.99 | 7812 | 3 | 4 | | | IV-2 | Sh3tc2 | 0.75 |
| 7717 | 3 | 4 | | | IV-2 | Sec61a1 | 0.89 | 7813 | 3 | 4 | | | IV-2 | Sh3yl1 | 0.74 |
| 7718 | 3 | 4 | | | IV-2 | Sec62 | 0.90 | 7814 | 3 | 4 | | | IV-2 | Shc3 | 0.83 |
| 7719 | 3 | 4 | | | IV-2 | Sectm1a | 0.76 | 7815 | 3 | 4 | | | IV-2 | Shc4 | 0.95 |
| 7720 | 3 | 4 | | | IV-2 | Sehl1 | 0.88 | 7816 | 3 | 4 | | | IV-2 | She | 0.73 |
| 7721 | 3 | 4 | | | IV-2 | Sel1l3 | 0.97 | 7817 | 3 | 4 | | | IV-2 | Shfm1 | 0.81 |
| 7722 | 3 | 4 | | | IV-2 | Selenbp2 | 0.91 | 7818 | 3 | 4 | | | IV-2 | Shh | 0.71 |
| 7723 | 3 | 4 | | | IV-2 | Selk | 0.83 | 7819 | 3 | 4 | | | IV-2 | Shisa2 | 0.98 |
| 7724 | 3 | 4 | | | IV-2 | Selm | 0.84 | 7820 | 3 | 4 | | | IV-2 | Shisa4 | 0.89 |
| 7725 | 3 | 4 | | | IV-2 | Selt | 0.79 | 7821 | 3 | 4 | | | IV-2 | Shkbp1 | 0.92 |
| 7726 | 3 | 4 | | | IV-2 | Sema3b | 0.79 | 7822 | 3 | 4 | | | IV-2 | Shmt1 | 0.79 |
| 7727 | 3 | 4 | | | IV-2 | Sema3c | 0.80 | 7823 | 3 | 4 | | | IV-2 | Shmt2 | 0.80 |
| 7728 | 3 | 4 | | | IV-2 | Sema3e | 0.97 | 7824 | 3 | 4 | | | IV-2 | Shoc2 | 0.97 |
| 7729 | 3 | 4 | | | IV-2 | Sema4a | 0.71 | 7825 | 3 | 4 | | | IV-2 | Shpk | 1.00 |
| 7730 | 3 | 4 | | | IV-2 | Sema4b | 0.86 | 7826 | 3 | 4 | | | IV-2 | Shroom1 | 0.94 |
| 7731 | 3 | 4 | | | IV-2 | Senp1 | 0.90 | 7827 | 3 | 4 | | | IV-2 | Shroom4 | 0.83 |
| 7732 | 3 | 4 | | | IV-2 | Senp2 | 0.88 | 7828 | 3 | 4 | | | IV-2 | Siae | 0.79 |
| 7733 | 3 | 4 | | | IV-2 | Senp7 | 0.87 | 7829 | 3 | 4 | | | IV-2 | Sigirr | 0.72 |
| 7734 | 3 | 4 | | | IV-2 | Sep15 | 0.85 | 7830 | 3 | 4 | | | IV-2 | Sigmar1 | 0.71 |
| 7735 | 3 | 4 | | | IV-2 | Sephs2 | 0.79 | 7831 | 3 | 4 | | | IV-2 | Sik2 | 0.82 |
| 7736 | 3 | 4 | | | IV-2 | Sepn1 | 0.89 | 7832 | 3 | 4 | | | IV-2 | Sil1 | 0.76 |
| 7737 | 3 | 4 | | | IV-2 | Sepp1 | 0.70 | 7833 | 3 | 4 | | | IV-2 | Sin3a | 1.00 |
| 7738 | 3 | 4 | | | IV-2 | Sepsecs | 0.94 | 7834 | 3 | 4 | | | IV-2 | Sipa1 | 0.67 |
| 7739 | 3 | 4 | | | IV-2 | Sept10 | 0.75 | 7835 | 3 | 4 | | | IV-2 | Sipa1l1 | 0.86 |
| 7740 | 3 | 4 | | | IV-2 | Sept11 | 0.91 | 7836 | 3 | 4 | | | IV-2 | Sipa1l3 | 0.90 |
| 7741 | 3 | 4 | | | IV-2 | Sept2 | 0.88 | 7837 | 3 | 4 | | | IV-2 | Sirt1 | 0.98 |
| 7742 | 3 | 4 | | | IV-2 | Sept7 | 0.84 | 7838 | 3 | 4 | | | IV-2 | Sirt2 | 0.95 |
| 7743 | 3 | 4 | | | IV-2 | Sept8 | 0.90 | 7839 | 3 | 4 | | | IV-2 | Sirt3 | 0.94 |
| 7744 | 3 | 4 | | | IV-2 | Sept9 | 0.94 | 7840 | 3 | 4 | | | IV-2 | Sirt4 | 0.77 |
| 7745 | 3 | 4 | | | IV-2 | Sepw1 | 0.95 | 7841 | 3 | 4 | | | IV-2 | Sirt7 | 0.84 |
| 7746 | 3 | 4 | | | IV-2 | Serbp1 | 0.79 | 7842 | 3 | 4 | | | IV-2 | Siva1 | 0.95 |
| 7747 | 3 | 4 | | | IV-2 | Serf1 | 0.84 | 7843 | 3 | 4 | | | IV-2 | Six1 | 0.97 |
| 7748 | 3 | 4 | | | IV-2 | Serf2 | 0.90 | 7844 | 3 | 4 | | | IV-2 | Six4 | 0.96 |
| 7749 | 3 | 4 | | | IV-2 | Serinc3 | 0.89 | 7845 | 3 | 4 | | | IV-2 | Six5 | 0.93 |
| 7750 | 3 | 4 | | | IV-2 | Serinc5 | 0.84 | 7846 | 3 | 4 | | | IV-2 | Ska2 | 0.86 |
| 7751 | 3 | 4 | | | IV-2 | Serp1 | 0.77 | 7847 | 3 | 4 | | | IV-2 | Skap2 | 0.99 |
| 7752 | 3 | 4 | | | IV-2 | Serpina11 | 0.77 | 7848 | 3 | 4 | | | IV-2 | Skint10 | 0.74 |
| 7753 | 3 | 4 | | | IV-2 | Serpina1a | 0.71 | 7849 | 3 | 4 | | | IV-2 | Skint3 | 0.77 |
| 7754 | 3 | 4 | | | IV-2 | Serpina3j | 0.91 | 7850 | 3 | 4 | | | IV-2 | Skint7 | 0.79 |
| 7755 | 3 | 4 | | | IV-2 | Serpinb1a | 0.84 | 7851 | 3 | 4 | | | IV-2 | Skiv2l2 | 0.92 |
| 7756 | 3 | 4 | | | IV-2 | Serpinb6b | 0.79 | 7852 | 3 | 4 | | | IV-2 | Skp2 | 0.76 |
| 7757 | 3 | 4 | | | IV-2 | Serpinb7 | 0.88 | 7853 | 3 | 4 | | | IV-2 | Slain2 | 0.93 |
| 7758 | 3 | 4 | | | IV-2 | Serpinb9 | 0.90 | 7854 | 3 | 4 | | | IV-2 | Slc10a3 | 0.92 |
| 7759 | 3 | 4 | | | IV-2 | Serpinf1 | 0.82 | 7855 | 3 | 4 | | | IV-2 | Slc10b7 | 0.91 |
| 7760 | 3 | 4 | | | IV-2 | Serping1 | 0.95 | 7856 | 3 | 4 | | | IV-2 | Slc11a2 | 0.91 |
| 7761 | 3 | 4 | | | IV-2 | Sertad1 | 0.93 | 7857 | 3 | 4 | | | IV-2 | Slc12a4 | 0.98 |
| 7762 | 3 | 4 | | | IV-2 | Sertad2 | 0.84 | 7858 | 3 | 4 | | | IV-2 | Slc12a7 | 0.85 |
| 7763 | 3 | 4 | | | IV-2 | Sertad3 | 0.84 | 7859 | 3 | 4 | | | IV-2 | Slc15a1 | 0.93 |
| 7764 | 3 | 4 | | | IV-2 | Sertm1 | 0.73 | 7860 | 3 | 4 | | | IV-2 | Slc15a3 | 0.97 |
| 7765 | 3 | 4 | | | IV-2 | Sesn1 | 0.92 | 7861 | 3 | 4 | | | IV-2 | Slc15a4 | 0.93 |
| 7766 | 3 | 4 | | | IV-2 | Sesn3 | 0.86 | 7862 | 3 | 4 | | | IV-2 | Slc16a13 | 0.95 |
| 7767 | 3 | 4 | | | IV-2 | Setd1b | 0.91 | 7863 | 3 | 4 | | | IV-2 | Slc16a2 | 0.93 |
| 7768 | 3 | 4 | | | IV-2 | Setd3 | 0.93 | 7864 | 3 | 4 | | | IV-2 | Slc17a3 | 0.87 |
| 7769 | 3 | 4 | | | IV-2 | Setd7 | 0.98 | 7865 | 3 | 4 | | | IV-2 | Slc17a5 | 0.97 |
| 7770 | 3 | 4 | | | IV-2 | Setdb1 | 1.00 | 7866 | 3 | 4 | | | IV-2 | Slc17a9 | 0.76 |
| 7771 | 3 | 4 | | | IV-2 | Setmar | 0.92 | 7867 | 3 | 4 | | | IV-2 | Slc18a2 | 0.77 |
| 7772 | 3 | 4 | | | IV-2 | Sf1 | 0.91 | 7868 | 3 | 4 | | | IV-2 | Slc18b1 | 0.90 |
| 7773 | 3 | 4 | | | IV-2 | Sf3a3 | 0.81 | 7869 | 3 | 4 | | | IV-2 | Slc19a2 | 0.98 |

Fig. 45 - 42

| | | | | | | | |
|---|---|---|---|---|---|---|---|
| 7870 | 3 | 4 | | | IV-2 | Slc20a1 | 0.92 |
| 7871 | 3 | 4 | | | IV-2 | Slc22a18 | 0.78 |
| 7872 | 3 | 4 | | | IV-2 | Slc22a23 | 0.98 |
| 7873 | 3 | 4 | | | IV-2 | Slc22a3 | 0.77 |
| 7874 | 3 | 4 | | | IV-2 | Slc25a1 | 0.80 |
| 7875 | 3 | 4 | | | IV-2 | Slc25a10 | 0.95 |
| 7876 | 3 | 4 | | | IV-2 | Slc25a11 | 0.77 |
| 7877 | 3 | 4 | | | IV-2 | Slc25a13 | 0.83 |
| 7878 | 3 | 4 | | | IV-2 | Slc25a15 | 0.70 |
| 7879 | 3 | 4 | | | IV-2 | Slc25a19 | 0.67 |
| 7880 | 3 | 4 | | | IV-2 | Slc25a20 | 0.98 |
| 7881 | 3 | 4 | | | IV-2 | Slc25a23 | 1.00 |
| 7882 | 3 | 4 | | | IV-2 | Slc25a24 | 0.91 |
| 7883 | 3 | 4 | | | IV-2 | Slc25a3 | 0.85 |
| 7884 | 3 | 4 | | | IV-2 | Slc25a35 | 0.69 |
| 7885 | 3 | 4 | | | IV-2 | Slc25a39 | 0.75 |
| 7886 | 3 | 4 | | | IV-2 | Slc25a4 | 0.99 |
| 7887 | 3 | 4 | | | IV-2 | Slc25a42 | 0.87 |
| 7888 | 3 | 4 | | | IV-2 | Slc25a44 | 0.92 |
| 7889 | 3 | 4 | | | IV-2 | Slc25a45 | 0.81 |
| 7890 | 3 | 4 | | | IV-2 | Slc25a47 | 0.92 |
| 7891 | 3 | 4 | | | IV-2 | Slc25a48 | 0.91 |
| 7892 | 3 | 4 | | | IV-2 | Slc25a5 | 0.82 |
| 7893 | 3 | 4 | | | IV-2 | Slc25a51 | 0.81 |
| 7894 | 3 | 4 | | | IV-2 | Slc26a2 | 0.93 |
| 7895 | 3 | 4 | | | IV-2 | Slc27a3 | 0.94 |
| 7896 | 3 | 4 | | | IV-2 | Slc27a4 | 0.88 |
| 7897 | 3 | 4 | | | IV-2 | Slc27a6 | 0.81 |
| 7898 | 3 | 4 | | | IV-2 | Slc28a2 | 0.71 |
| 7899 | 3 | 4 | | | IV-2 | Slc28a3 | 0.98 |
| 7900 | 3 | 4 | | | IV-2 | Slc29a1 | 0.74 |
| 7901 | 3 | 4 | | | IV-2 | Slc2a1 | 0.70 |
| 7902 | 3 | 4 | | | IV-2 | Slc2a10 | 0.85 |
| 7903 | 3 | 4 | | | IV-2 | Slc2a12 | 0.98 |
| 7904 | 3 | 4 | | | IV-2 | Slc2a4 | 0.77 |
| 7905 | 3 | 4 | | | IV-2 | Slc30a5 | 0.98 |
| 7906 | 3 | 4 | | | IV-2 | Slc30a6 | 0.75 |
| 7907 | 3 | 4 | | | IV-2 | Slc30a9 | 0.96 |
| 7908 | 3 | 4 | | | IV-2 | Slc31a1 | 0.85 |
| 7909 | 3 | 4 | | | IV-2 | Slc31a2 | 0.99 |
| 7910 | 3 | 4 | | | IV-2 | Slc33a1 | 0.98 |
| 7911 | 3 | 4 | | | IV-2 | Slc35a1 | 0.93 |
| 7912 | 3 | 4 | | | IV-2 | Slc35a2 | 0.81 |
| 7913 | 3 | 4 | | | IV-2 | Slc35a3 | 0.88 |
| 7914 | 3 | 4 | | | IV-2 | Slc35a4 | 0.81 |
| 7915 | 3 | 4 | | | IV-2 | Slc35b2 | 0.94 |
| 7916 | 3 | 4 | | | IV-2 | Slc35b4 | 0.86 |
| 7917 | 3 | 4 | | | IV-2 | Slc35c1 | 0.92 |
| 7918 | 3 | 4 | | | IV-2 | Slc35c2 | 0.90 |
| 7919 | 3 | 4 | | | IV-2 | Slc35d2 | 0.69 |
| 7920 | 3 | 4 | | | IV-2 | Slc35e1 | 0.80 |
| 7921 | 3 | 4 | | | IV-2 | Slc35e4 | 0.88 |
| 7922 | 3 | 4 | | | IV-2 | Slc35f5 | 0.93 |
| 7923 | 3 | 4 | | | IV-2 | Slc35g2 | 0.84 |
| 7924 | 3 | 4 | | | IV-2 | Slc36a1 | 0.69 |
| 7925 | 3 | 4 | | | IV-2 | Slc38a10 | 0.89 |
| 7926 | 3 | 4 | | | IV-2 | Slc38a3 | 0.97 |
| 7927 | 3 | 4 | | | IV-2 | Slc38a4 | 0.85 |
| 7928 | 3 | 4 | | | IV-2 | Slc38a7 | 0.90 |
| 7929 | 3 | 4 | | | IV-2 | Slc39a1 | 0.96 |
| 7930 | 3 | 4 | | | IV-2 | Slc39a10 | 0.80 |
| 7931 | 3 | 4 | | | IV-2 | Slc39a13 | 1.00 |
| 7932 | 3 | 4 | | | IV-2 | Slc39a14 | 0.76 |
| 7933 | 3 | 4 | | | IV-2 | Slc39a2 | 0.71 |
| 7934 | 3 | 4 | | | IV-2 | Slc39a3 | 0.99 |
| 7935 | 3 | 4 | | | IV-2 | Slc39a8 | 0.74 |
| 7936 | 3 | 4 | | | IV-2 | Slc39a9 | 0.89 |
| 7937 | 3 | 4 | | | IV-2 | Slc41a1 | 0.90 |
| 7938 | 3 | 4 | | | IV-2 | Slc41a3 | 0.73 |
| 7939 | 3 | 4 | | | IV-2 | Slc46a1 | 0.94 |
| 7940 | 3 | 4 | | | IV-2 | Slc46a2 | 0.76 |
| 7941 | 3 | 4 | | | IV-2 | Slc4a2 | 0.92 |
| 7942 | 3 | 4 | | | IV-2 | Slc51a | 0.75 |
| 7943 | 3 | 4 | | | IV-2 | Slc5a3 | 0.98 |
| 7944 | 3 | 4 | | | IV-2 | Slc5a6 | 0.93 |
| 7945 | 3 | 4 | | | IV-2 | Slc6a13 | 0.88 |
| 7946 | 3 | 4 | | | IV-2 | Slc6a14 | 0.75 |
| 7947 | 3 | 4 | | | IV-2 | Slc6a20a | 0.79 |
| 7948 | 3 | 4 | | | IV-2 | Slc6a4 | 0.98 |
| 7949 | 3 | 4 | | | IV-2 | Slc7a2 | 0.90 |
| 7950 | 3 | 4 | | | IV-2 | Slc7a9 | 0.91 |
| 7951 | 3 | 4 | | | IV-2 | Slc9a9 | 0.87 |
| 7952 | 3 | 4 | | | IV-2 | Slfn3 | 0.90 |
| 7953 | 3 | 4 | | | IV-2 | Slfn9 | 0.68 |
| 7954 | 3 | 4 | | | IV-2 | Slirp | 0.79 |
| 7955 | 3 | 4 | | | IV-2 | Slmap | 0.97 |
| 7956 | 3 | 4 | | | IV-2 | Slmo2 | 0.69 |
| 7957 | 3 | 4 | | | IV-2 | Sln | 0.96 |
| 7958 | 3 | 4 | | | IV-2 | Slx4ip | 0.94 |
| 7959 | 3 | 4 | | | IV-2 | Smad6 | 0.93 |
| 7960 | 3 | 4 | | | IV-2 | Smagp | 0.93 |
| 7961 | 3 | 4 | | | IV-2 | Smap2 | 0.95 |
| 7962 | 3 | 4 | | | IV-2 | Smarca4 | 0.90 |
| 7963 | 3 | 4 | | | IV-2 | Smarca5 | 0.82 |
| 7964 | 3 | 4 | | | IV-2 | Smarca5-ps | 0.85 |
| 7965 | 3 | 4 | | | IV-2 | Smarcal1 | 0.79 |
| 7966 | 3 | 4 | | | IV-2 | Smarcb1 | 0.98 |
| 7967 | 3 | 4 | | | IV-2 | Smarcd2 | 0.80 |
| 7968 | 3 | 4 | | | IV-2 | Smc1a | 0.69 |
| 7969 | 3 | 4 | | | IV-2 | Smc3 | 0.90 |
| 7970 | 3 | 4 | | | IV-2 | Smchd1 | 0.91 |
| 7971 | 3 | 4 | | | IV-2 | Smco4 | 0.76 |
| 7972 | 3 | 4 | | | IV-2 | Smcr8 | 0.88 |
| 7973 | 3 | 4 | | | IV-2 | Smdt1 | 0.71 |
| 7974 | 3 | 4 | | | IV-2 | Smek1 | 0.91 |
| 7975 | 3 | 4 | | | IV-2 | Smg1 | 0.93 |
| 7976 | 3 | 4 | | | IV-2 | Smg5 | 0.95 |
| 7977 | 3 | 4 | | | IV-2 | Smg8 | 1.00 |
| 7978 | 3 | 4 | | | IV-2 | Smim11 | 0.69 |
| 7979 | 3 | 4 | | | IV-2 | Smim15 | 0.79 |
| 7980 | 3 | 4 | | | IV-2 | Smim20 | 0.84 |
| 7981 | 3 | 4 | | | IV-2 | Smim4 | 0.96 |
| 7982 | 3 | 4 | | | IV-2 | Smim5 | 0.68 |
| 7983 | 3 | 4 | | | IV-2 | Smim6 | 0.81 |
| 7984 | 3 | 4 | | | IV-2 | Smim7 | 0.98 |
| 7985 | 3 | 4 | | | IV-2 | Smim8 | 0.93 |
| 7986 | 3 | 4 | | | IV-2 | Smndc1 | 0.99 |
| 7987 | 3 | 4 | | | IV-2 | Smox | 0.86 |
| 7988 | 3 | 4 | | | IV-2 | Smpd1 | 0.73 |
| 7989 | 3 | 4 | | | IV-2 | Smpd2 | 0.91 |
| 7990 | 3 | 4 | | | IV-2 | Smpdl3b | 0.89 |
| 7991 | 3 | 4 | | | IV-2 | Smpx | 0.86 |
| 7992 | 3 | 4 | | | IV-2 | Smtn | 0.78 |
| 7993 | 3 | 4 | | | IV-2 | Smtnl2 | 0.74 |
| 7994 | 3 | 4 | | | IV-2 | Smu1 | 0.92 |
| 7995 | 3 | 4 | | | IV-2 | Smyd1 | 0.79 |
| 7996 | 3 | 4 | | | IV-2 | Smyd5 | 0.96 |
| 7997 | 3 | 4 | | | IV-2 | Snai2 | 0.93 |
| 7998 | 3 | 4 | | | IV-2 | Snai3 | 0.98 |
| 7999 | 3 | 4 | | | IV-2 | Snap23 | 0.77 |
| 8000 | 3 | 4 | | | IV-2 | Snap29 | 0.86 |
| 8001 | 3 | 4 | | | IV-2 | Snapc1 | 0.96 |
| 8002 | 3 | 4 | | | IV-2 | Snapc2 | 0.97 |
| 8003 | 3 | 4 | | | IV-2 | Snapc5 | 0.76 |
| 8004 | 3 | 4 | | | IV-2 | Snd1 | 0.85 |
| 8005 | 3 | 4 | | | IV-2 | Sned1 | 0.88 |
| 8006 | 3 | 4 | | | IV-2 | Snf8 | 0.78 |
| 8007 | 3 | 4 | | | IV-2 | Snhg18 | 0.97 |
| 8008 | 3 | 4 | | | IV-2 | Snip1 | 0.86 |
| 8009 | 3 | 4 | | | IV-2 | Snrnp27 | 0.81 |
| 8010 | 3 | 4 | | | IV-2 | Snrnp35 | 0.75 |
| 8011 | 3 | 4 | | | IV-2 | Snrnp40 | 0.87 |
| 8012 | 3 | 4 | | | IV-2 | Snrnp48 | 0.92 |
| 8013 | 3 | 4 | | | IV-2 | Snrnp70 | 1.00 |
| 8014 | 3 | 4 | | | IV-2 | Snrpa | 0.84 |
| 8015 | 3 | 4 | | | IV-2 | Snrpb | 0.99 |
| 8016 | 3 | 4 | | | IV-2 | Snrpb2 | 0.90 |
| 8017 | 3 | 4 | | | IV-2 | Snrpd1 | 0.76 |
| 8018 | 3 | 4 | | | IV-2 | Snrpd2 | 0.85 |
| 8019 | 3 | 4 | | | IV-2 | Snrpd3 | 0.88 |
| 8020 | 3 | 4 | | | IV-2 | Snrpe | 0.87 |
| 8021 | 3 | 4 | | | IV-2 | Snrpf | 0.98 |
| 8022 | 3 | 4 | | | IV-2 | Snrpg | 0.79 |
| 8023 | 3 | 4 | | | IV-2 | Snta1 | 0.78 |
| 8024 | 3 | 4 | | | IV-2 | Sntb1 | 0.84 |
| 8025 | 3 | 4 | | | IV-2 | Sntb2 | 0.97 |
| 8026 | 3 | 4 | | | IV-2 | Snurf | 0.95 |
| 8027 | 3 | 4 | | | IV-2 | Snx1 | 0.80 |
| 8028 | 3 | 4 | | | IV-2 | Snx12 | 0.94 |
| 8029 | 3 | 4 | | | IV-2 | Snx14 | 0.78 |
| 8030 | 3 | 4 | | | IV-2 | Snx15 | 0.72 |
| 8031 | 3 | 4 | | | IV-2 | Snx17 | 1.00 |
| 8032 | 3 | 4 | | | IV-2 | Snx18 | 0.91 |
| 8033 | 3 | 4 | | | IV-2 | Snx2 | 0.99 |
| 8034 | 3 | 4 | | | IV-2 | Snx25 | 0.93 |
| 8035 | 3 | 4 | | | IV-2 | Snx27 | 0.95 |
| 8036 | 3 | 4 | | | IV-2 | Snx5 | 0.85 |
| 8037 | 3 | 4 | | | IV-2 | Snx6 | 0.84 |
| 8038 | 3 | 4 | | | IV-2 | Snx9 | 0.94 |
| 8039 | 3 | 4 | | | IV-2 | Soat1 | 0.78 |
| 8040 | 3 | 4 | | | IV-2 | Socs1 | 0.90 |
| 8041 | 3 | 4 | | | IV-2 | Socs4 | 0.86 |
| 8042 | 3 | 4 | | | IV-2 | Sod1 | 0.90 |
| 8043 | 3 | 4 | | | IV-2 | Sod2 | 0.70 |
| 8044 | 3 | 4 | | | IV-2 | Sorbs1 | 0.97 |
| 8045 | 3 | 4 | | | IV-2 | Sord | 0.84 |
| 8046 | 3 | 4 | | | IV-2 | Sorl1 | 0.96 |
| 8047 | 3 | 4 | | | IV-2 | Sort1 | 0.90 |
| 8048 | 3 | 4 | | | IV-2 | Sost | 0.78 |
| 8049 | 3 | 4 | | | IV-2 | Sowahb | 0.93 |
| 8050 | 3 | 4 | | | IV-2 | Sowahc | 0.87 |
| 8051 | 3 | 4 | | | IV-2 | Sox13 | 1.00 |
| 8052 | 3 | 4 | | | IV-2 | Sox15 | 0.71 |
| 8053 | 3 | 4 | | | IV-2 | Sox17 | 0.75 |
| 8054 | 3 | 4 | | | IV-2 | Sox18 | 0.86 |
| 8055 | 3 | 4 | | | IV-2 | Sox6 | 0.79 |
| 8056 | 3 | 4 | | | IV-2 | Sox8 | 0.92 |
| 8057 | 3 | 4 | | | IV-2 | Sp1 | 0.86 |
| 8058 | 3 | 4 | | | IV-2 | Sp2 | 0.88 |
| 8059 | 3 | 4 | | | IV-2 | Sp3 | 0.96 |
| 8060 | 3 | 4 | | | IV-2 | Sp6 | 0.83 |
| 8061 | 3 | 4 | | | IV-2 | Sp7 | 0.87 |

Fig. 45 - 43

| | | | | | | | | | | | | | | |
|---|---|---|---|---|---|---|---|---|---|---|---|---|---|---|
| 8062 | 3 | 4 | | | IV-2 | Spa17 | 0.72 | 8158 | 3 | 4 | | | IV-2 | St6galnac3 | 0.94 |
| 8063 | 3 | 4 | | | IV-2 | Spag1 | 0.92 | 8159 | 3 | 4 | | | IV-2 | St6galnac4 | 0.81 |
| 8064 | 3 | 4 | | | IV-2 | Spag8 | 0.97 | 8160 | 3 | 4 | | | IV-2 | St6galnac6 | 0.89 |
| 8065 | 3 | 4 | | | IV-2 | Sparc | 0.73 | 8161 | 3 | 4 | | | IV-2 | St8sia4 | 0.83 |
| 8066 | 3 | 4 | | | IV-2 | Spata13 | 0.98 | 8162 | 3 | 4 | | | IV-2 | Stab1 | 0.74 |
| 8067 | 3 | 4 | | | IV-2 | Spata22 | 1.00 | 8163 | 3 | 4 | | | IV-2 | Stac3 | 0.89 |
| 8068 | 3 | 4 | | | IV-2 | Spata2l | 0.84 | 8164 | 3 | 4 | | | IV-2 | Stag2 | 0.97 |
| 8069 | 3 | 4 | | | IV-2 | Spata5 | 0.91 | 8165 | 3 | 4 | | | IV-2 | Stambpl1 | 0.92 |
| 8070 | 3 | 4 | | | IV-2 | Spats2l | 0.98 | 8166 | 3 | 4 | | | IV-2 | Stap2 | 0.98 |
| 8071 | 3 | 4 | | | IV-2 | Spcs1 | 0.91 | 8167 | 3 | 4 | | | IV-2 | Star | 0.74 |
| 8072 | 3 | 4 | | | IV-2 | Spcs2 | 0.79 | 8168 | 3 | 4 | | | IV-2 | Stard10 | 0.83 |
| 8073 | 3 | 4 | | | IV-2 | Spcs3 | 0.82 | 8169 | 3 | 4 | | | IV-2 | Stard13 | 0.99 |
| 8074 | 3 | 4 | | | IV-2 | Specc1 | 0.98 | 8170 | 3 | 4 | | | IV-2 | Stard4 | 0.69 |
| 8075 | 3 | 4 | | | IV-2 | Spef1 | 0.86 | 8171 | 3 | 4 | | | IV-2 | Stard5 | 0.82 |
| 8076 | 3 | 4 | | | IV-2 | Speg | 0.75 | 8172 | 3 | 4 | | | IV-2 | Stard7 | 0.86 |
| 8077 | 3 | 4 | | | IV-2 | Spg21 | 0.88 | 8173 | 3 | 4 | | | IV-2 | Stard8 | 0.92 |
| 8078 | 3 | 4 | | | IV-2 | Spg7 | 0.87 | 8174 | 3 | 4 | | | IV-2 | Stat5a | 0.81 |
| 8079 | 3 | 4 | | | IV-2 | Sphk1 | 0.77 | 8175 | 3 | 4 | | | IV-2 | Stat5b | 0.85 |
| 8080 | 3 | 4 | | | IV-2 | Sphk2 | 0.77 | 8176 | 3 | 4 | | | IV-2 | Stat6 | 0.84 |
| 8081 | 3 | 4 | | | IV-2 | Spi1 | 1.00 | 8177 | 3 | 4 | | | IV-2 | Stc1 | 0.99 |
| 8082 | 3 | 4 | | | IV-2 | Spib | 0.81 | 8178 | 3 | 4 | | | IV-2 | Stil | 0.79 |
| 8083 | 3 | 4 | | | IV-2 | Spidr | 0.96 | 8179 | 3 | 4 | | | IV-2 | Stim1 | 0.92 |
| 8084 | 3 | 4 | | | IV-2 | Spink12 | 0.98 | 8180 | 3 | 4 | | | IV-2 | Stim2 | 0.99 |
| 8085 | 3 | 4 | | | IV-2 | Spint1 | 0.83 | 8181 | 3 | 4 | | | IV-2 | Stk10 | 0.76 |
| 8086 | 3 | 4 | | | IV-2 | Spint2 | 0.88 | 8182 | 3 | 4 | | | IV-2 | Stk11 | 0.74 |
| 8087 | 3 | 4 | | | IV-2 | Spire1 | 0.96 | 8183 | 3 | 4 | | | IV-2 | Stk16 | 0.83 |
| 8088 | 3 | 4 | | | IV-2 | Spns2 | 0.86 | 8184 | 3 | 4 | | | IV-2 | Stk17b | 0.74 |
| 8089 | 3 | 4 | | | IV-2 | Spop | 0.88 | 8185 | 3 | 4 | | | IV-2 | Stk24 | 0.89 |
| 8090 | 3 | 4 | | | IV-2 | Spp1 | 0.83 | 8186 | 3 | 4 | | | IV-2 | Stk3 | 0.93 |
| 8091 | 3 | 4 | | | IV-2 | Sppl2b | 0.98 | 8187 | 3 | 4 | | | IV-2 | Stk35 | 0.85 |
| 8092 | 3 | 4 | | | IV-2 | Spr | 0.73 | 8188 | 3 | 4 | | | IV-2 | Stk38l | 0.92 |
| 8093 | 3 | 4 | | | IV-2 | Sprtn | 0.86 | 8189 | 3 | 4 | | | IV-2 | Stk4 | 0.85 |
| 8094 | 3 | 4 | | | IV-2 | Spry4 | 0.99 | 8190 | 3 | 4 | | | IV-2 | Stk40 | 0.86 |
| 8095 | 3 | 4 | | | IV-2 | Spryd4 | 0.89 | 8191 | 3 | 4 | | | IV-2 | Stmn1 | 1.00 |
| 8096 | 3 | 4 | | | IV-2 | Spsb2 | 0.94 | 8192 | 3 | 4 | | | IV-2 | Stmnd1 | 0.76 |
| 8097 | 3 | 4 | | | IV-2 | Spsb4 | 0.99 | 8193 | 3 | 4 | | | IV-2 | Stoml2 | 0.80 |
| 8098 | 3 | 4 | | | IV-2 | Sptlc1 | 0.88 | 8194 | 3 | 4 | | | IV-2 | Ston2 | 0.80 |
| 8099 | 3 | 4 | | | IV-2 | Sptlc2 | 0.98 | 8195 | 3 | 4 | | | IV-2 | Stra13 | 0.70 |
| 8100 | 3 | 4 | | | IV-2 | Sptssa | 0.91 | 8196 | 3 | 4 | | | IV-2 | Strada | 0.94 |
| 8101 | 3 | 4 | | | IV-2 | Spty2d1 | 0.86 | 8197 | 3 | 4 | | | IV-2 | Stradb | 0.80 |
| 8102 | 3 | 4 | | | IV-2 | Sqle | 0.89 | 8198 | 3 | 4 | | | IV-2 | Strip2 | 0.90 |
| 8103 | 3 | 4 | | | IV-2 | Sqrdl | 0.70 | 8199 | 3 | 4 | | | IV-2 | Stt3a | 0.74 |
| 8104 | 3 | 4 | | | IV-2 | Sra1 | 0.95 | 8200 | 3 | 4 | | | IV-2 | Stt3b | 0.86 |
| 8105 | 3 | 4 | | | IV-2 | Srbd1 | 0.91 | 8201 | 3 | 4 | | | IV-2 | Stub1 | 0.94 |
| 8106 | 3 | 4 | | | IV-2 | Srcrb4d | 0.95 | 8202 | 3 | 4 | | | IV-2 | Stx11 | 0.92 |
| 8107 | 3 | 4 | | | IV-2 | Srd5a1 | 0.76 | 8203 | 3 | 4 | | | IV-2 | Stx16 | 0.82 |
| 8108 | 3 | 4 | | | IV-2 | Srebf1 | 0.67 | 8204 | 3 | 4 | | | IV-2 | Stx19 | 0.75 |
| 8109 | 3 | 4 | | | IV-2 | Srebf2 | 0.94 | 8205 | 3 | 4 | | | IV-2 | Stx2 | 0.71 |
| 8110 | 3 | 4 | | | IV-2 | Sreklip1 | 0.85 | 8206 | 3 | 4 | | | IV-2 | Stx4a | 0.90 |
| 8111 | 3 | 4 | | | IV-2 | Srf | 0.75 | 8207 | 3 | 4 | | | IV-2 | Stx5a | 0.93 |
| 8112 | 3 | 4 | | | IV-2 | Sri | 0.86 | 8208 | 3 | 4 | | | IV-2 | Stx8 | 0.91 |
| 8113 | 3 | 4 | | | IV-2 | Srl | 0.81 | 8209 | 3 | 4 | | | IV-2 | Stxbp3b | 0.75 |
| 8114 | 3 | 4 | | | IV-2 | Srm | 0.90 | 8210 | 3 | 4 | | | IV-2 | Stxbp6 | 0.99 |
| 8115 | 3 | 4 | | | IV-2 | Srp14 | 0.94 | 8211 | 3 | 4 | | | IV-2 | Sucla2 | 0.81 |
| 8116 | 3 | 4 | | | IV-2 | Srp19 | 0.85 | 8212 | 3 | 4 | | | IV-2 | Suclg1 | 0.69 |
| 8117 | 3 | 4 | | | IV-2 | Srp54a | 0.82 | 8213 | 3 | 4 | | | IV-2 | Suclg2 | 0.88 |
| 8118 | 3 | 4 | | | IV-2 | Srp54b | 0.90 | 8214 | 3 | 4 | | | IV-2 | Suds3 | 0.90 |
| 8119 | 3 | 4 | | | IV-2 | Srp68 | 0.84 | 8215 | 3 | 4 | | | IV-2 | Sufu | 0.97 |
| 8120 | 3 | 4 | | | IV-2 | Srp72 | 0.94 | 8216 | 3 | 4 | | | IV-2 | Sult1b1 | 0.74 |
| 8121 | 3 | 4 | | | IV-2 | Srp9 | 0.97 | 8217 | 3 | 4 | | | IV-2 | Sumf2 | 0.70 |
| 8122 | 3 | 4 | | | IV-2 | Srpk1 | 0.94 | 8218 | 3 | 4 | | | IV-2 | Sumo1 | 0.91 |
| 8123 | 3 | 4 | | | IV-2 | Srpk3 | 0.82 | 8219 | 3 | 4 | | | IV-2 | Sumo2 | 0.89 |
| 8124 | 3 | 4 | | | IV-2 | Srpr | 0.92 | 8220 | 3 | 4 | | | IV-2 | Sun1 | 1.00 |
| 8125 | 3 | 4 | | | IV-2 | Srprb | 0.90 | 8221 | 3 | 4 | | | IV-2 | Sun2 | 0.98 |
| 8126 | 3 | 4 | | | IV-2 | Srpx | 0.79 | 8222 | 3 | 4 | | | IV-2 | Suox | 0.87 |
| 8127 | 3 | 4 | | | IV-2 | Srpx2 | 0.83 | 8223 | 3 | 4 | | | IV-2 | Supt16 | 0.82 |
| 8128 | 3 | 4 | | | IV-2 | Srr | 1.00 | 8224 | 3 | 4 | | | IV-2 | Supt3 | 0.78 |
| 8129 | 3 | 4 | | | IV-2 | Srrm2 | 0.98 | 8225 | 3 | 4 | | | IV-2 | Supt4a | 0.93 |
| 8130 | 3 | 4 | | | IV-2 | Srrt | 0.93 | 8226 | 3 | 4 | | | IV-2 | Supt5 | 0.99 |
| 8131 | 3 | 4 | | | IV-2 | Srsf1 | 0.83 | 8227 | 3 | 4 | | | IV-2 | Supt7l | 0.94 |
| 8132 | 3 | 4 | | | IV-2 | Srsf10 | 0.85 | 8228 | 3 | 4 | | | IV-2 | Surf1 | 0.80 |
| 8133 | 3 | 4 | | | IV-2 | Srsf2 | 0.88 | 8229 | 3 | 4 | | | IV-2 | Surf2 | 0.87 |
| 8134 | 3 | 4 | | | IV-2 | Srsf3 | 0.74 | 8230 | 3 | 4 | | | IV-2 | Surf4 | 0.83 |
| 8135 | 3 | 4 | | | IV-2 | Srsf4 | 0.89 | 8231 | 3 | 4 | | | IV-2 | Suv39h1 | 0.90 |
| 8136 | 3 | 4 | | | IV-2 | Srsf9 | 0.86 | 8232 | 3 | 4 | | | IV-2 | Suv39h2 | 0.73 |
| 8137 | 3 | 4 | | | IV-2 | Ss18 | 0.87 | 8233 | 3 | 4 | | | IV-2 | Suv420h2 | 0.88 |
| 8138 | 3 | 4 | | | IV-2 | Ssb | 0.94 | 8234 | 3 | 4 | | | IV-2 | Suz12 | 0.78 |
| 8139 | 3 | 4 | | | IV-2 | Ssc5d | 0.77 | 8235 | 3 | 4 | | | IV-2 | Svil | 0.86 |
| 8140 | 3 | 4 | | | IV-2 | Ssfa2 | 0.89 | 8236 | 3 | 4 | | | IV-2 | Svip | 0.76 |
| 8141 | 3 | 4 | | | IV-2 | Ssna1 | 0.90 | 8237 | 3 | 4 | | | IV-2 | Swap70 | 0.95 |
| 8142 | 3 | 4 | | | IV-2 | Sspn | 0.73 | 8238 | 3 | 4 | | | IV-2 | Swi5 | 0.72 |
| 8143 | 3 | 4 | | | IV-2 | Ssr1 | 0.82 | 8239 | 3 | 4 | | | IV-2 | Swt1 | 0.75 |
| 8144 | 3 | 4 | | | IV-2 | Ssr2 | 0.78 | 8240 | 3 | 4 | | | IV-2 | Syap1 | 0.96 |
| 8145 | 3 | 4 | | | IV-2 | Ssr3 | 0.90 | 8241 | 3 | 4 | | | IV-2 | Syce2 | 0.89 |
| 8146 | 3 | 4 | | | IV-2 | Ssr4 | 0.81 | 8242 | 3 | 4 | | | IV-2 | Syk | 0.76 |
| 8147 | 3 | 4 | | | IV-2 | Ssrp1 | 0.84 | 8243 | 3 | 4 | | | IV-2 | Sympk | 0.90 |
| 8148 | 3 | 4 | | | IV-2 | Ssscal | 0.91 | 8244 | 3 | 4 | | | IV-2 | Sync | 0.74 |
| 8149 | 3 | 4 | | | IV-2 | St13 | 0.83 | 8245 | 3 | 4 | | | IV-2 | Syne2 | 0.93 |
| 8150 | 3 | 4 | | | IV-2 | St14 | 0.84 | 8246 | 3 | 4 | | | IV-2 | Syne3 | 0.79 |
| 8151 | 3 | 4 | | | IV-2 | St3gal1 | 0.88 | 8247 | 3 | 4 | | | IV-2 | Syne4 | 0.93 |
| 8152 | 3 | 4 | | | IV-2 | St3gal2 | 0.91 | 8248 | 3 | 4 | | | IV-2 | Syngr2 | 0.79 |
| 8153 | 3 | 4 | | | IV-2 | St3gal3 | 0.99 | 8249 | 3 | 4 | | | IV-2 | Synj1 | 0.76 |
| 8154 | 3 | 4 | | | IV-2 | St3gal5 | 0.79 | 8250 | 3 | 4 | | | IV-2 | Synj2bp | 0.92 |
| 8155 | 3 | 4 | | | IV-2 | St5 | 0.97 | 8251 | 3 | 4 | | | IV-2 | Synm | 0.85 |
| 8156 | 3 | 4 | | | IV-2 | St6gal1 | 0.76 | 8252 | 3 | 4 | | | IV-2 | Synpo2 | 0.91 |
| 8157 | 3 | 4 | | | IV-2 | St6galnac2 | 0.90 | 8253 | 3 | 4 | | | IV-2 | Synpo2l | 0.81 |

Fig. 45 - 44

| | | | | | | | |
|---|---|---|---|---|---|---|---|
| 8254 | 3 | 4 | | | IV-2 | Sypl | 0.91 |
| 8255 | 3 | 4 | | | IV-2 | Syt15 | 0.92 |
| 8256 | 3 | 4 | | | IV-2 | Syt17 | 0.78 |
| 8257 | 3 | 4 | | | IV-2 | Syt2 | 0.86 |
| 8258 | 3 | 4 | | | IV-2 | Sytl2 | 0.91 |
| 8259 | 3 | 4 | | | IV-2 | Sytl4 | 0.87 |
| 8260 | 3 | 4 | | | IV-2 | Sytl5 | 0.94 |
| 8261 | 3 | 4 | | | IV-2 | Syvn1 | 0.85 |
| 8262 | 3 | 4 | | | IV-2 | Szrd1 | 0.82 |
| 8263 | 3 | 4 | | | IV-2 | Tab3 | 0.97 |
| 8264 | 3 | 4 | | | IV-2 | Tacc1 | 0.90 |
| 8265 | 3 | 4 | | | IV-2 | Tacc3 | 0.70 |
| 8266 | 3 | 4 | | | IV-2 | Tacstd2 | 0.79 |
| 8267 | 3 | 4 | | | IV-2 | Tada3 | 0.97 |
| 8268 | 3 | 4 | | | IV-2 | Taf10 | 0.83 |
| 8269 | 3 | 4 | | | IV-2 | Taf11 | 0.89 |
| 8270 | 3 | 4 | | | IV-2 | Taf12 | 0.70 |
| 8271 | 3 | 4 | | | IV-2 | Taf13 | 0.89 |
| 8272 | 3 | 4 | | | IV-2 | Taf15 | 0.82 |
| 8273 | 3 | 4 | | | IV-2 | Taf1c | 1.00 |
| 8274 | 3 | 4 | | | IV-2 | Taf3 | 0.99 |
| 8275 | 3 | 4 | | | IV-2 | Taf4a | 0.83 |
| 8276 | 3 | 4 | | | IV-2 | Taf5 | 0.79 |
| 8277 | 3 | 4 | | | IV-2 | Taf6 | 0.84 |
| 8278 | 3 | 4 | | | IV-2 | Taf6l | 0.84 |
| 8279 | 3 | 4 | | | IV-2 | Taf7 | 0.88 |
| 8280 | 3 | 4 | | | IV-2 | Taf9b | 0.94 |
| 8281 | 3 | 4 | | | IV-2 | Tagap1 | 1.00 |
| 8282 | 3 | 4 | | | IV-2 | Tagln | 0.82 |
| 8283 | 3 | 4 | | | IV-2 | Tagln2 | 0.71 |
| 8284 | 3 | 4 | | | IV-2 | Tanc1 | 0.84 |
| 8285 | 3 | 4 | | | IV-2 | Tango2 | 0.98 |
| 8286 | 3 | 4 | | | IV-2 | Tank | 0.97 |
| 8287 | 3 | 4 | | | IV-2 | Taok3 | 0.84 |
| 8288 | 3 | 4 | | | IV-2 | Tap2 | 0.72 |
| 8289 | 3 | 4 | | | IV-2 | Tapbp1 | 0.96 |
| 8290 | 3 | 4 | | | IV-2 | Tars2 | 0.81 |
| 8291 | 3 | 4 | | | IV-2 | Tarsl2 | 0.83 |
| 8292 | 3 | 4 | | | IV-2 | Tasl1 | 0.97 |
| 8293 | 3 | 4 | | | IV-2 | Tasp1 | 0.90 |
| 8294 | 3 | 4 | | | IV-2 | Tatdn1 | 0.81 |
| 8295 | 3 | 4 | | | IV-2 | Tatdn3 | 0.91 |
| 8296 | 3 | 4 | | | IV-2 | Taxlbp3 | 0.93 |
| 8297 | 3 | 4 | | | IV-2 | Tbc1d1 | 0.93 |
| 8298 | 3 | 4 | | | IV-2 | Tbc1d10a | 0.88 |
| 8299 | 3 | 4 | | | IV-2 | Tbc1d10b | 0.88 |
| 8300 | 3 | 4 | | | IV-2 | Tbc1d13 | 0.90 |
| 8301 | 3 | 4 | | | IV-2 | Tbc1d19 | 0.91 |
| 8302 | 3 | 4 | | | IV-2 | Tbc1d22a | 0.98 |
| 8303 | 3 | 4 | | | IV-2 | Tbc1d25 | 0.97 |
| 8304 | 3 | 4 | | | IV-2 | Tbc1d2b | 0.90 |
| 8305 | 3 | 4 | | | IV-2 | Tbc1d31 | 0.69 |
| 8306 | 3 | 4 | | | IV-2 | Tbc1d4 | 0.73 |
| 8307 | 3 | 4 | | | IV-2 | Tbc1d8b | 0.87 |
| 8308 | 3 | 4 | | | IV-2 | Tbc1d9b | 0.96 |
| 8309 | 3 | 4 | | | IV-2 | Tbca | 0.83 |
| 8310 | 3 | 4 | | | IV-2 | Tbcc | 0.97 |
| 8311 | 3 | 4 | | | IV-2 | Tbccd1 | 0.74 |
| 8312 | 3 | 4 | | | IV-2 | Tbck | 0.97 |
| 8313 | 3 | 4 | | | IV-2 | Tbl2 | 0.80 |
| 8314 | 3 | 4 | | | IV-2 | Tbp | 1.00 |
| 8315 | 3 | 4 | | | IV-2 | Tbrg4 | 0.97 |
| 8316 | 3 | 4 | | | IV-2 | Tbx2 | 0.99 |
| 8317 | 3 | 4 | | | IV-2 | Tbx3 | 1.00 |
| 8318 | 3 | 4 | | | IV-2 | Tbx4 | 0.83 |
| 8319 | 3 | 4 | | | IV-2 | Tbx5 | 0.96 |
| 8320 | 3 | 4 | | | IV-2 | Tbxa2r | 0.98 |
| 8321 | 3 | 4 | | | IV-2 | Tbxas1 | 0.95 |
| 8322 | 3 | 4 | | | IV-2 | Tcea3 | 0.83 |
| 8323 | 3 | 4 | | | IV-2 | Tceal1 | 0.92 |
| 8324 | 3 | 4 | | | IV-2 | Tceal3 | 0.86 |
| 8325 | 3 | 4 | | | IV-2 | Tceal5 | 0.96 |
| 8326 | 3 | 4 | | | IV-2 | Tceal7 | 0.68 |
| 8327 | 3 | 4 | | | IV-2 | Tceal8 | 0.89 |
| 8328 | 3 | 4 | | | IV-2 | Tceanc2 | 0.95 |
| 8329 | 3 | 4 | | | IV-2 | Tceb2 | 0.73 |
| 8330 | 3 | 4 | | | IV-2 | Tceb3 | 0.91 |
| 8331 | 3 | 4 | | | IV-2 | Tcf15 | 0.93 |
| 8332 | 3 | 4 | | | IV-2 | Tcf3 | 0.98 |
| 8333 | 3 | 4 | | | IV-2 | Tchh | 0.81 |
| 8334 | 3 | 4 | | | IV-2 | Tcn2 | 0.89 |
| 8335 | 3 | 4 | | | IV-2 | Tcof1 | 0.87 |
| 8336 | 3 | 4 | | | IV-2 | Tcp1 | 0.98 |
| 8337 | 3 | 4 | | | IV-2 | Tcp11l1 | 0.88 |
| 8338 | 3 | 4 | | | IV-2 | Tcte2 | 0.87 |
| 8339 | 3 | 4 | | | IV-2 | Tdp2 | 0.88 |
| 8340 | 3 | 4 | | | IV-2 | Tdrd1 | 0.75 |
| 8341 | 3 | 4 | | | IV-2 | Tdrp | 0.67 |
| 8342 | 3 | 4 | | | IV-2 | Tec | 0.85 |
| 8343 | 3 | 4 | | | IV-2 | Tecrl | 0.81 |
| 8344 | 3 | 4 | | | IV-2 | Tefm | 0.86 |
| 8345 | 3 | 4 | | | IV-2 | Tek | 0.81 |
| 8346 | 3 | 4 | | | IV-2 | Tekt5 | 0.89 |
| 8347 | 3 | 4 | | | IV-2 | Ten1 | 0.67 |
| 8348 | 3 | 4 | | | IV-2 | Tep1 | 0.95 |
| 8349 | 3 | 4 | | | IV-2 | Terf1 | 0.81 |
| 8350 | 3 | 4 | | | IV-2 | Terf2 | 0.99 |
| 8351 | 3 | 4 | | | IV-2 | Tesk2 | 0.83 |
| 8352 | 3 | 4 | | | IV-2 | Tex10 | 0.91 |
| 8353 | 3 | 4 | | | IV-2 | Tex15 | 0.95 |
| 8354 | 3 | 4 | | | IV-2 | Tex2 | 0.87 |
| 8355 | 3 | 4 | | | IV-2 | Tex264 | 0.96 |
| 8356 | 3 | 4 | | | IV-2 | Tex30 | 0.81 |
| 8357 | 3 | 4 | | | IV-2 | Tex9 | 0.94 |
| 8358 | 3 | 4 | | | IV-2 | Tfam | 0.94 |
| 8359 | 3 | 4 | | | IV-2 | Tfcp2l1 | 0.67 |
| 8360 | 3 | 4 | | | IV-2 | Tfdp1 | 0.88 |
| 8361 | 3 | 4 | | | IV-2 | Tfdp2 | 0.85 |
| 8362 | 3 | 4 | | | IV-2 | Tfeb | 0.74 |
| 8363 | 3 | 4 | | | IV-2 | Tff1 | 0.67 |
| 8364 | 3 | 4 | | | IV-2 | Tff3 | 0.84 |
| 8365 | 3 | 4 | | | IV-2 | Tfg | 0.88 |
| 8366 | 3 | 4 | | | IV-2 | Tfip11 | 0.97 |
| 8367 | 3 | 4 | | | IV-2 | Tfr2 | 0.88 |
| 8368 | 3 | 4 | | | IV-2 | Tg | 0.97 |
| 8369 | 3 | 4 | | | IV-2 | Tgds | 0.95 |
| 8370 | 3 | 4 | | | IV-2 | Tgfb1 | 0.83 |
| 8371 | 3 | 4 | | | IV-2 | Tgfb1l1 | 0.86 |
| 8372 | 3 | 4 | | | IV-2 | Tgm1 | 0.94 |
| 8373 | 3 | 4 | | | IV-2 | Tgm4 | 0.98 |
| 8374 | 3 | 4 | | | IV-2 | Tgoln1 | 0.91 |
| 8375 | 3 | 4 | | | IV-2 | Tgoln2 | 0.85 |
| 8376 | 3 | 4 | | | IV-2 | Tgs1 | 0.97 |
| 8377 | 3 | 4 | | | IV-2 | Thap11 | 0.82 |
| 8378 | 3 | 4 | | | IV-2 | Thap4 | 0.96 |
| 8379 | 3 | 4 | | | IV-2 | Thap6 | 0.99 |
| 8380 | 3 | 4 | | | IV-2 | Thbd | 0.96 |
| 8381 | 3 | 4 | | | IV-2 | Thbs4 | 0.85 |
| 8382 | 3 | 4 | | | IV-2 | Them6 | 0.83 |
| 8383 | 3 | 4 | | | IV-2 | Thnsl1 | 0.94 |
| 8384 | 3 | 4 | | | IV-2 | Thoc6 | 0.72 |
| 8385 | 3 | 4 | | | IV-2 | Thoc7 | 0.92 |
| 8386 | 3 | 4 | | | IV-2 | Thop1 | 0.71 |
| 8387 | 3 | 4 | | | IV-2 | Thrap3 | 0.94 |
| 8388 | 3 | 4 | | | IV-2 | Thrb | 0.69 |
| 8389 | 3 | 4 | | | IV-2 | Thsd1 | 0.82 |
| 8390 | 3 | 4 | | | IV-2 | Thsd7b | 0.99 |
| 8391 | 3 | 4 | | | IV-2 | Thy1 | 0.90 |
| 8392 | 3 | 4 | | | IV-2 | Tial1 | 0.90 |
| 8393 | 3 | 4 | | | IV-2 | Ticam1 | 0.74 |
| 8394 | 3 | 4 | | | IV-2 | Ticrr | 0.69 |
| 8395 | 3 | 4 | | | IV-2 | Tie1 | 0.80 |
| 8396 | 3 | 4 | | | IV-2 | Tifab | 0.86 |
| 8397 | 3 | 4 | | | IV-2 | Timeless | 0.85 |
| 8398 | 3 | 4 | | | IV-2 | Timm10 | 0.92 |
| 8399 | 3 | 4 | | | IV-2 | Timm13 | 0.78 |
| 8400 | 3 | 4 | | | IV-2 | Timm17a | 0.89 |
| 8401 | 3 | 4 | | | IV-2 | Timm17b | 0.82 |
| 8402 | 3 | 4 | | | IV-2 | Timm21 | 0.92 |
| 8403 | 3 | 4 | | | IV-2 | Timm22 | 0.68 |
| 8404 | 3 | 4 | | | IV-2 | Timm23 | 0.89 |
| 8405 | 3 | 4 | | | IV-2 | Timm44 | 0.82 |
| 8406 | 3 | 4 | | | IV-2 | Timm50 | 0.80 |
| 8407 | 3 | 4 | | | IV-2 | Timm8a1 | 0.81 |
| 8408 | 3 | 4 | | | IV-2 | Timm8b | 0.86 |
| 8409 | 3 | 4 | | | IV-2 | Timm9 | 0.89 |
| 8410 | 3 | 4 | | | IV-2 | Timmdc1 | 0.68 |
| 8411 | 3 | 4 | | | IV-2 | Timp1 | 0.76 |
| 8412 | 3 | 4 | | | IV-2 | Tinag | 0.73 |
| 8413 | 3 | 4 | | | IV-2 | Tinf2 | 0.79 |
| 8414 | 3 | 4 | | | IV-2 | Tiparp | 0.97 |
| 8415 | 3 | 4 | | | IV-2 | Tipin | 0.83 |
| 8416 | 3 | 4 | | | IV-2 | Tiprl | 0.80 |
| 8417 | 3 | 4 | | | IV-2 | Tjap1 | 0.99 |
| 8418 | 3 | 4 | | | IV-2 | Tjp1 | 0.92 |
| 8419 | 3 | 4 | | | IV-2 | Tjp2 | 0.84 |
| 8420 | 3 | 4 | | | IV-2 | Tkt | 0.73 |
| 8421 | 3 | 4 | | | IV-2 | Tlcd2 | 0.96 |
| 8422 | 3 | 4 | | | IV-2 | Tle3 | 0.99 |
| 8423 | 3 | 4 | | | IV-2 | Tln1 | 0.81 |
| 8424 | 3 | 4 | | | IV-2 | Tln2 | 0.98 |
| 8425 | 3 | 4 | | | IV-2 | Tlr2 | 0.82 |
| 8426 | 3 | 4 | | | IV-2 | Tm2d3 | 0.88 |
| 8427 | 3 | 4 | | | IV-2 | Tm9sf1 | 0.89 |
| 8428 | 3 | 4 | | | IV-2 | Tm9sf2 | 0.98 |
| 8429 | 3 | 4 | | | IV-2 | Tm9sf4 | 0.90 |
| 8430 | 3 | 4 | | | IV-2 | Tma7 | 0.84 |
| 8431 | 3 | 4 | | | IV-2 | Tmbim4 | 0.91 |
| 8432 | 3 | 4 | | | IV-2 | Tmbim6 | 0.85 |
| 8433 | 3 | 4 | | | IV-2 | Tmc3 | 0.96 |
| 8434 | 3 | 4 | | | IV-2 | Tmcc2 | 0.85 |
| 8435 | 3 | 4 | | | IV-2 | Tmcc3 | 0.75 |
| 8436 | 3 | 4 | | | IV-2 | Tmco1 | 0.77 |
| 8437 | 3 | 4 | | | IV-2 | Tmco3 | 0.80 |
| 8438 | 3 | 4 | | | IV-2 | Tmco6 | 0.85 |
| 8439 | 3 | 4 | | | IV-2 | Tmed1 | 0.87 |
| 8440 | 3 | 4 | | | IV-2 | Tmed10 | 0.97 |
| 8441 | 3 | 4 | | | IV-2 | Tmed2 | 0.81 |
| 8442 | 3 | 4 | | | IV-2 | Tmed3 | 0.85 |
| 8443 | 3 | 4 | | | IV-2 | Tmed5 | 0.89 |
| 8444 | 3 | 4 | | | IV-2 | Tmed7 | 0.97 |
| 8445 | 3 | 4 | | | IV-2 | Tmed9 | 0.89 |

Fig. 45 - 45

| | | | | | | | |
|---|---|---|---|---|---|---|---|
| 8446 | 3 | 4 | | IV-2 | Tmem101 | 0.81 |
| 8447 | 3 | 4 | | IV-2 | Tmem106a | 0.72 |
| 8448 | 3 | 4 | | IV-2 | Tmem106c | 0.99 |
| 8449 | 3 | 4 | | IV-2 | Tmem107 | 0.82 |
| 8450 | 3 | 4 | | IV-2 | Tmem109 | 0.80 |
| 8451 | 3 | 4 | | IV-2 | Tmem11 | 0.93 |
| 8452 | 3 | 4 | | IV-2 | Tmem115 | 0.81 |
| 8453 | 3 | 4 | | IV-2 | Tmem117 | 0.99 |
| 8454 | 3 | 4 | | IV-2 | Tmem119 | 0.84 |
| 8455 | 3 | 4 | | IV-2 | Tmem120a | 0.96 |
| 8456 | 3 | 4 | | IV-2 | Tmem120b | 0.68 |
| 8457 | 3 | 4 | | IV-2 | Tmem123 | 0.73 |
| 8458 | 3 | 4 | | IV-2 | Tmem126a | 0.85 |
| 8459 | 3 | 4 | | IV-2 | Tmem126b | 0.85 |
| 8460 | 3 | 4 | | IV-2 | Tmem129 | 0.83 |
| 8461 | 3 | 4 | | IV-2 | Tmem131 | 0.89 |
| 8462 | 3 | 4 | | IV-2 | Tmem132e | 0.86 |
| 8463 | 3 | 4 | | IV-2 | Tmem134 | 0.96 |
| 8464 | 3 | 4 | | IV-2 | Tmem135 | 0.75 |
| 8465 | 3 | 4 | | IV-2 | Tmem139 | 0.95 |
| 8466 | 3 | 4 | | IV-2 | Tmem141 | 0.92 |
| 8467 | 3 | 4 | | IV-2 | Tmem143 | 0.71 |
| 8468 | 3 | 4 | | IV-2 | Tmem144 | 0.70 |
| 8469 | 3 | 4 | | IV-2 | Tmem159 | 0.91 |
| 8470 | 3 | 4 | | IV-2 | Tmem161a | 0.98 |
| 8471 | 3 | 4 | | IV-2 | Tmem164 | 0.92 |
| 8472 | 3 | 4 | | IV-2 | Tmem167 | 0.97 |
| 8473 | 3 | 4 | | IV-2 | Tmem167b | 0.91 |
| 8474 | 3 | 4 | | IV-2 | Tmem168 | 0.96 |
| 8475 | 3 | 4 | | IV-2 | Tmem170 | 0.78 |
| 8476 | 3 | 4 | | IV-2 | Tmem173 | 0.84 |
| 8477 | 3 | 4 | | IV-2 | Tmem176a | 0.83 |
| 8478 | 3 | 4 | | IV-2 | Tmem176b | 0.89 |
| 8479 | 3 | 4 | | IV-2 | Tmem177 | 0.73 |
| 8480 | 3 | 4 | | IV-2 | Tmem179b | 0.84 |
| 8481 | 3 | 4 | | IV-2 | Tmem181c-ps | 0.96 |
| 8482 | 3 | 4 | | IV-2 | Tmem182 | 0.83 |
| 8483 | 3 | 4 | | IV-2 | Tmem183a | 0.87 |
| 8484 | 3 | 4 | | IV-2 | Tmem184b | 0.85 |
| 8485 | 3 | 4 | | IV-2 | Tmem185b | 0.81 |
| 8486 | 3 | 4 | | IV-2 | Tmem186 | 0.96 |
| 8487 | 3 | 4 | | IV-2 | Tmem189 | 1.00 |
| 8488 | 3 | 4 | | IV-2 | Tmem192 | 0.98 |
| 8489 | 3 | 4 | | IV-2 | Tmem194 | 0.83 |
| 8490 | 3 | 4 | | IV-2 | Tmem205 | 0.75 |
| 8491 | 3 | 4 | | IV-2 | Tmem206 | 0.92 |
| 8492 | 3 | 4 | | IV-2 | Tmem208 | 0.98 |
| 8493 | 3 | 4 | | IV-2 | Tmem214 | 0.94 |
| 8494 | 3 | 4 | | IV-2 | Tmem222 | 0.98 |
| 8495 | 3 | 4 | | IV-2 | Tmem230 | 0.98 |
| 8496 | 3 | 4 | | IV-2 | Tmem234 | 0.97 |
| 8497 | 3 | 4 | | IV-2 | Tmem238 | 0.68 |
| 8498 | 3 | 4 | | IV-2 | Tmem242 | 0.82 |
| 8499 | 3 | 4 | | IV-2 | Tmem245 | 0.82 |
| 8500 | 3 | 4 | | IV-2 | Tmem246 | 0.82 |
| 8501 | 3 | 4 | | IV-2 | Tmem255a | 0.86 |
| 8502 | 3 | 4 | | IV-2 | Tmem258 | 0.76 |
| 8503 | 3 | 4 | | IV-2 | Tmem260 | 0.82 |
| 8504 | 3 | 4 | | IV-2 | Tmem263 | 0.90 |
| 8505 | 3 | 4 | | IV-2 | Tmem27 | 0.90 |
| 8506 | 3 | 4 | | IV-2 | Tmem30a | 0.99 |
| 8507 | 3 | 4 | | IV-2 | Tmem30b | 0.84 |
| 8508 | 3 | 4 | | IV-2 | Tmem38a | 0.67 |
| 8509 | 3 | 4 | | IV-2 | Tmem38b | 0.91 |
| 8510 | 3 | 4 | | IV-2 | Tmem39a | 0.86 |
| 8511 | 3 | 4 | | IV-2 | Tmem39b | 0.98 |
| 8512 | 3 | 4 | | IV-2 | Tmem41b | 0.89 |
| 8513 | 3 | 4 | | IV-2 | Tmem45a | 0.69 |
| 8514 | 3 | 4 | | IV-2 | Tmem50b | 0.96 |
| 8515 | 3 | 4 | | IV-2 | Tmem51 | 0.67 |
| 8516 | 3 | 4 | | IV-2 | Tmem52 | 0.78 |
| 8517 | 3 | 4 | | IV-2 | Tmem55a | 0.93 |
| 8518 | 3 | 4 | | IV-2 | Tmem60 | 0.86 |
| 8519 | 3 | 4 | | IV-2 | Tmem63a | 0.99 |
| 8520 | 3 | 4 | | IV-2 | Tmem64 | 0.83 |
| 8521 | 3 | 4 | | IV-2 | Tmem66 | 0.98 |
| 8522 | 3 | 4 | | IV-2 | Tmem68 | 0.94 |
| 8523 | 3 | 4 | | IV-2 | Tmem69 | 0.72 |
| 8524 | 3 | 4 | | IV-2 | Tmem70 | 0.68 |
| 8525 | 3 | 4 | | IV-2 | Tmem72 | 0.75 |
| 8526 | 3 | 4 | | IV-2 | Tmem79 | 0.72 |
| 8527 | 3 | 4 | | IV-2 | Tmem8 | 0.69 |
| 8528 | 3 | 4 | | IV-2 | Tmem87a | 0.96 |
| 8529 | 3 | 4 | | IV-2 | Tmem88 | 0.93 |
| 8530 | 3 | 4 | | IV-2 | Tmem88b | 0.78 |
| 8531 | 3 | 4 | | IV-2 | Tmem8c | 0.84 |
| 8532 | 3 | 4 | | IV-2 | Tmem9 | 0.98 |
| 8533 | 3 | 4 | | IV-2 | Tmem97 | 0.68 |
| 8534 | 3 | 4 | | IV-2 | Tmem98 | 0.88 |
| 8535 | 3 | 4 | | IV-2 | Tmem9b | 0.98 |
| 8536 | 3 | 4 | | IV-2 | Tmie | 0.78 |
| 8537 | 3 | 4 | | IV-2 | Tmlhe | 0.85 |
| 8538 | 3 | 4 | | IV-2 | Tmod3 | 0.87 |
| 8539 | 3 | 4 | | IV-2 | Tmpo | 0.73 |
| 8540 | 3 | 4 | | IV-2 | Tmppe | 0.83 |
| 8541 | 3 | 4 | | IV-2 | Tmprss11a | 0.92 |
| 8542 | 3 | 4 | | IV-2 | Tmprss11f | 0.79 |
| 8543 | 3 | 4 | | IV-2 | Tmprss13 | 0.68 |
| 8544 | 3 | 4 | | IV-2 | Tmprss2 | 0.73 |
| 8545 | 3 | 4 | | IV-2 | Tmsb10 | 0.94 |
| 8546 | 3 | 4 | | IV-2 | Tmsb4x | 0.84 |
| 8547 | 3 | 4 | | IV-2 | Tmtc3 | 0.88 |
| 8548 | 3 | 4 | | IV-2 | Tmub1 | 0.87 |
| 8549 | 3 | 4 | | IV-2 | Tmub2 | 0.92 |
| 8550 | 3 | 4 | | IV-2 | Tmx1 | 0.84 |
| 8551 | 3 | 4 | | IV-2 | Tmx2 | 0.86 |
| 8552 | 3 | 4 | | IV-2 | Tnc | 0.87 |
| 8553 | 3 | 4 | | IV-2 | Tnfaip1 | 0.86 |
| 8554 | 3 | 4 | | IV-2 | Tnfaip8 | 0.80 |
| 8555 | 3 | 4 | | IV-2 | Tnfaip8l2 | 0.88 |
| 8556 | 3 | 4 | | IV-2 | Tnfaip8l3 | 0.90 |
| 8557 | 3 | 4 | | IV-2 | Tnfrsf11a | 0.73 |
| 8558 | 3 | 4 | | IV-2 | Tnfrsf1a | 0.96 |
| 8559 | 3 | 4 | | IV-2 | Tnfrsf1b | 0.81 |
| 8560 | 3 | 4 | | IV-2 | Tnfrsf21 | 0.87 |
| 8561 | 3 | 4 | | IV-2 | Tnfrsf23 | 0.90 |
| 8562 | 3 | 4 | | IV-2 | Tnk1 | 0.80 |
| 8563 | 3 | 4 | | IV-2 | Tnks1bp1 | 0.99 |
| 8564 | 3 | 4 | | IV-2 | Tnks2 | 0.96 |
| 8565 | 3 | 4 | | IV-2 | Tnn | 0.83 |
| 8566 | 3 | 4 | | IV-2 | Tnni1 | 0.87 |
| 8567 | 3 | 4 | | IV-2 | Tnni3 | 0.98 |
| 8568 | 3 | 4 | | IV-2 | Tnnt1 | 0.85 |
| 8569 | 3 | 4 | | IV-2 | Tnpo2 | 0.97 |
| 8570 | 3 | 4 | | IV-2 | Tnpo3 | 0.91 |
| 8571 | 3 | 4 | | IV-2 | Tnrc6b | 0.88 |
| 8572 | 3 | 4 | | IV-2 | Tnxb | 0.76 |
| 8573 | 3 | 4 | | IV-2 | Tob1 | 0.79 |
| 8574 | 3 | 4 | | IV-2 | Tob2 | 0.77 |
| 8575 | 3 | 4 | | IV-2 | Tollip | 0.96 |
| 8576 | 3 | 4 | | IV-2 | Tom1 | 0.92 |
| 8577 | 3 | 4 | | IV-2 | Tom1l1 | 0.76 |
| 8578 | 3 | 4 | | IV-2 | Tomm22 | 0.81 |
| 8579 | 3 | 4 | | IV-2 | Tomm40 | 0.85 |
| 8580 | 3 | 4 | | IV-2 | Tomm40l | 0.76 |
| 8581 | 3 | 4 | | IV-2 | Tomm5 | 0.67 |
| 8582 | 3 | 4 | | IV-2 | Tomm6 | 0.89 |
| 8583 | 3 | 4 | | IV-2 | Top1 | 0.69 |
| 8584 | 3 | 4 | | IV-2 | Top1mt | 0.79 |
| 8585 | 3 | 4 | | IV-2 | Topbp1 | 0.95 |
| 8586 | 3 | 4 | | IV-2 | Topors | 0.90 |
| 8587 | 3 | 4 | | IV-2 | Toporsos | 0.80 |
| 8588 | 3 | 4 | | IV-2 | Tor1a | 0.90 |
| 8589 | 3 | 4 | | IV-2 | Tor1aip2 | 0.75 |
| 8590 | 3 | 4 | | IV-2 | Tor1b | 0.88 |
| 8591 | 3 | 4 | | IV-2 | Tor2a | 0.95 |
| 8592 | 3 | 4 | | IV-2 | Tor4a | 0.94 |
| 8593 | 3 | 4 | | IV-2 | Tox4 | 0.91 |
| 8594 | 3 | 4 | | IV-2 | Tpcn1 | 0.89 |
| 8595 | 3 | 4 | | IV-2 | Tpd52 | 0.86 |
| 8596 | 3 | 4 | | IV-2 | Tpd52l1 | 0.97 |
| 8597 | 3 | 4 | | IV-2 | Tpgs1 | 0.91 |
| 8598 | 3 | 4 | | IV-2 | Tpk1 | 0.85 |
| 8599 | 3 | 4 | | IV-2 | Tpm1 | 0.82 |
| 8600 | 3 | 4 | | IV-2 | Tpm2 | 0.78 |
| 8601 | 3 | 4 | | IV-2 | Tpm3 | 0.91 |
| 8602 | 3 | 4 | | IV-2 | Tpm4 | 0.72 |
| 8603 | 3 | 4 | | IV-2 | Tpp1 | 0.97 |
| 8604 | 3 | 4 | | IV-2 | Tpp2 | 0.95 |
| 8605 | 3 | 4 | | IV-2 | Tppp | 0.77 |
| 8606 | 3 | 4 | | IV-2 | Tpr | 1.00 |
| 8607 | 3 | 4 | | IV-2 | Tpra1 | 0.83 |
| 8608 | 3 | 4 | | IV-2 | Tpsb2 | 0.82 |
| 8609 | 3 | 4 | | IV-2 | Tpst1 | 0.99 |
| 8610 | 3 | 4 | | IV-2 | Tpst2 | 1.00 |
| 8611 | 3 | 4 | | IV-2 | Tpt1 | 0.99 |
| 8612 | 3 | 4 | | IV-2 | Tra2b | 0.80 |
| 8613 | 3 | 4 | | IV-2 | Trabd | 0.91 |
| 8614 | 3 | 4 | | IV-2 | Trabd2b | 0.97 |
| 8615 | 3 | 4 | | IV-2 | Tradd | 0.71 |
| 8616 | 3 | 4 | | IV-2 | Traf2 | 0.85 |
| 8617 | 3 | 4 | | IV-2 | Traf4 | 0.98 |
| 8618 | 3 | 4 | | IV-2 | Traf6 | 0.92 |
| 8619 | 3 | 4 | | IV-2 | Traip | 0.93 |
| 8620 | 3 | 4 | | IV-2 | Trak2 | 0.71 |
| 8621 | 3 | 4 | | IV-2 | Tram1 | 0.81 |
| 8622 | 3 | 4 | | IV-2 | Trap1 | 0.70 |
| 8623 | 3 | 4 | | IV-2 | Trappc1 | 0.77 |
| 8624 | 3 | 4 | | IV-2 | Trappc12 | 1.00 |
| 8625 | 3 | 4 | | IV-2 | Trappc13 | 0.82 |
| 8626 | 3 | 4 | | IV-2 | Trappc2l | 0.88 |
| 8627 | 3 | 4 | | IV-2 | Trappc6a | 0.95 |
| 8628 | 3 | 4 | | IV-2 | Trappc8 | 0.88 |
| 8629 | 3 | 4 | | IV-2 | Treml2 | 0.74 |
| 8630 | 3 | 4 | | IV-2 | Trex1 | 0.86 |
| 8631 | 3 | 4 | | IV-2 | Triap1 | 0.84 |
| 8632 | 3 | 4 | | IV-2 | Trim13 | 0.94 |
| 8633 | 3 | 4 | | IV-2 | Trim16 | 0.92 |
| 8634 | 3 | 4 | | IV-2 | Trim25 | 0.99 |
| 8635 | 3 | 4 | | IV-2 | Trim27 | 0.88 |
| 8636 | 3 | 4 | | IV-2 | Trim28 | 0.91 |
| 8637 | 3 | 4 | | IV-2 | Trim29 | 0.92 |

Fig. 45 - 46

| | | | | | | | | | | | | | | |
|---|---|---|---|---|---|---|---|---|---|---|---|---|---|---|
| 8638 | 3 | 4 | | | IV-2 | Trim47 | 0.82 | 8734 | 3 | 4 | | | IV-2 | Txnrd1 | 0.97 |
| 8639 | 3 | 4 | | | IV-2 | Trim54 | 0.88 | 8735 | 3 | 4 | | | IV-2 | Tyk2 | 0.82 |
| 8640 | 3 | 4 | | | IV-2 | Trim55 | 0.73 | 8736 | 3 | 4 | | | IV-2 | Tyrobp | 0.96 |
| 8641 | 3 | 4 | | | IV-2 | Trim56 | 0.80 | 8737 | 3 | 4 | | | IV-2 | Tyrp1 | 0.84 |
| 8642 | 3 | 4 | | | IV-2 | Trim58 | 0.70 | 8738 | 3 | 4 | | | IV-2 | Tysnd1 | 0.78 |
| 8643 | 3 | 4 | | | IV-2 | Trim63 | 0.93 | 8739 | 3 | 4 | | | IV-2 | Tyw1 | 0.83 |
| 8644 | 3 | 4 | | | IV-2 | Trim65 | 0.83 | 8740 | 3 | 4 | | | IV-2 | Tyw5 | 0.94 |
| 8645 | 3 | 4 | | | IV-2 | Trim7 | 0.99 | 8741 | 3 | 4 | | | IV-2 | U2af2 | 0.85 |
| 8646 | 3 | 4 | | | IV-2 | Trim71 | 0.79 | 8742 | 3 | 4 | | | IV-2 | Uaca | 0.90 |
| 8647 | 3 | 4 | | | IV-2 | Triobp | 0.89 | 8743 | 3 | 4 | | | IV-2 | Uap1 | 0.79 |
| 8648 | 3 | 4 | | | IV-2 | Trip10 | 0.71 | 8744 | 3 | 4 | | | IV-2 | Uap1l1 | 0.85 |
| 8649 | 3 | 4 | | | IV-2 | Trip13 | 0.97 | 8745 | 3 | 4 | | | IV-2 | Uba1 | 0.94 |
| 8650 | 3 | 4 | | | IV-2 | Trip4 | 0.93 | 8746 | 3 | 4 | | | IV-2 | Uba3 | 0.93 |
| 8651 | 3 | 4 | | | IV-2 | Trmt10a | 0.70 | 8747 | 3 | 4 | | | IV-2 | Uba5 | 0.85 |
| 8652 | 3 | 4 | | | IV-2 | Trmt10b | 0.99 | 8748 | 3 | 4 | | | IV-2 | Uba52 | 0.94 |
| 8653 | 3 | 4 | | | IV-2 | Trmt10c | 0.95 | 8749 | 3 | 4 | | | IV-2 | Uba6 | 0.91 |
| 8654 | 3 | 4 | | | IV-2 | Trmt112 | 0.98 | 8750 | 3 | 4 | | | IV-2 | Ubac2 | 0.97 |
| 8655 | 3 | 4 | | | IV-2 | Trmt12 | 0.91 | 8751 | 3 | 4 | | | IV-2 | Ubald2 | 0.82 |
| 8656 | 3 | 4 | | | IV-2 | Trmt2a | 0.95 | 8752 | 3 | 4 | | | IV-2 | Ubap1 | 0.97 |
| 8657 | 3 | 4 | | | IV-2 | Trmt5 | 0.90 | 8753 | 3 | 4 | | | IV-2 | Ubap2 | 0.85 |
| 8658 | 3 | 4 | | | IV-2 | Troap | 0.75 | 8754 | 3 | 4 | | | IV-2 | Ubap2l | 0.95 |
| 8659 | 3 | 4 | | | IV-2 | Trp53 | 0.98 | 8755 | 3 | 4 | | | IV-2 | Ubb | 0.95 |
| 8660 | 3 | 4 | | | IV-2 | Trp53cor1 | 0.91 | 8756 | 3 | 4 | | | IV-2 | Ube2a | 0.69 |
| 8661 | 3 | 4 | | | IV-2 | Trp53inp2 | 0.79 | 8757 | 3 | 4 | | | IV-2 | Ube2b | 0.76 |
| 8662 | 3 | 4 | | | IV-2 | Trp63 | 0.98 | 8758 | 3 | 4 | | | IV-2 | Ube2d2a | 1.00 |
| 8663 | 3 | 4 | | | IV-2 | Trpc4ap | 0.93 | 8759 | 3 | 4 | | | IV-2 | Ube2d3 | 0.92 |
| 8664 | 3 | 4 | | | IV-2 | Trps1 | 0.98 | 8760 | 3 | 4 | | | IV-2 | Ube2f | 0.80 |
| 8665 | 3 | 4 | | | IV-2 | Trpv1 | 0.76 | 8761 | 3 | 4 | | | IV-2 | Ube2h | 0.91 |
| 8666 | 3 | 4 | | | IV-2 | Tsc22d2 | 0.98 | 8762 | 3 | 4 | | | IV-2 | Ube2j1 | 0.83 |
| 8667 | 3 | 4 | | | IV-2 | Tsc22d4 | 0.84 | 8763 | 3 | 4 | | | IV-2 | Ube2k | 0.93 |
| 8668 | 3 | 4 | | | IV-2 | Tsen15 | 0.87 | 8764 | 3 | 4 | | | IV-2 | Ube2l3 | 0.78 |
| 8669 | 3 | 4 | | | IV-2 | Tsen2 | 0.84 | 8765 | 3 | 4 | | | IV-2 | Ube2m | 0.94 |
| 8670 | 3 | 4 | | | IV-2 | Tsen34 | 0.93 | 8766 | 3 | 4 | | | IV-2 | Ube2n | 0.94 |
| 8671 | 3 | 4 | | | IV-2 | Tsen54 | 0.92 | 8767 | 3 | 4 | | | IV-2 | Ube2r2 | 0.94 |
| 8672 | 3 | 4 | | | IV-2 | Tsfm | 0.80 | 8768 | 3 | 4 | | | IV-2 | Ube2s | 0.68 |
| 8673 | 3 | 4 | | | IV-2 | Tspan1 | 0.74 | 8769 | 3 | 4 | | | IV-2 | Ube2v1 | 0.87 |
| 8674 | 3 | 4 | | | IV-2 | Tspan12 | 0.75 | 8770 | 3 | 4 | | | IV-2 | Ube2v2 | 0.95 |
| 8675 | 3 | 4 | | | IV-2 | Tspan13 | 0.86 | 8771 | 3 | 4 | | | IV-2 | Ube2z | 0.90 |
| 8676 | 3 | 4 | | | IV-2 | Tspan14 | 0.86 | 8772 | 3 | 4 | | | IV-2 | Ube3a | 0.86 |
| 8677 | 3 | 4 | | | IV-2 | Tspan15 | 0.97 | 8773 | 3 | 4 | | | IV-2 | Ube3b | 0.89 |
| 8678 | 3 | 4 | | | IV-2 | Tspan17 | 0.99 | 8774 | 3 | 4 | | | IV-2 | Ube3c | 0.93 |
| 8679 | 3 | 4 | | | IV-2 | Tspan18 | 0.93 | 8775 | 3 | 4 | | | IV-2 | Ube4a | 0.91 |
| 8680 | 3 | 4 | | | IV-2 | Tspan31 | 0.78 | 8776 | 3 | 4 | | | IV-2 | Ubfd1 | 0.87 |
| 8681 | 3 | 4 | | | IV-2 | Tspan6 | 0.97 | 8777 | 3 | 4 | | | IV-2 | Ubiad1 | 0.99 |
| 8682 | 3 | 4 | | | IV-2 | Tspan9 | 0.77 | 8778 | 3 | 4 | | | IV-2 | Ubl4 | 0.92 |
| 8683 | 3 | 4 | | | IV-2 | Tspyl1 | 0.98 | 8779 | 3 | 4 | | | IV-2 | Ubn1 | 0.93 |
| 8684 | 3 | 4 | | | IV-2 | Tssc4 | 1.00 | 8780 | 3 | 4 | | | IV-2 | Ubox5 | 0.90 |
| 8685 | 3 | 4 | | | IV-2 | Tstd2 | 0.91 | 8781 | 3 | 4 | | | IV-2 | Ubqln1 | 0.83 |
| 8686 | 3 | 4 | | | IV-2 | Tstd3 | 0.92 | 8782 | 3 | 4 | | | IV-2 | Ubqln4 | 0.95 |
| 8687 | 3 | 4 | | | IV-2 | Ttc1 | 0.97 | 8783 | 3 | 4 | | | IV-2 | Ubr7 | 0.95 |
| 8688 | 3 | 4 | | | IV-2 | Ttc13 | 0.90 | 8784 | 3 | 4 | | | IV-2 | Ubtd1 | 0.89 |
| 8689 | 3 | 4 | | | IV-2 | Ttc22 | 0.83 | 8785 | 3 | 4 | | | IV-2 | Ubxn1 | 0.93 |
| 8690 | 3 | 4 | | | IV-2 | Ttc23 | 0.76 | 8786 | 3 | 4 | | | IV-2 | Ubxn10 | 0.97 |
| 8691 | 3 | 4 | | | IV-2 | Ttc27 | 0.86 | 8787 | 3 | 4 | | | IV-2 | Ubxn2a | 0.91 |
| 8692 | 3 | 4 | | | IV-2 | Ttc30a1 | 0.89 | 8788 | 3 | 4 | | | IV-2 | Ubxn2b | 0.69 |
| 8693 | 3 | 4 | | | IV-2 | Ttc30b | 0.99 | 8789 | 3 | 4 | | | IV-2 | Ubxn8 | 0.96 |
| 8694 | 3 | 4 | | | IV-2 | Ttc33 | 0.99 | 8790 | 3 | 4 | | | IV-2 | Uchl3 | 0.92 |
| 8695 | 3 | 4 | | | IV-2 | Ttc7 | 0.68 | 8791 | 3 | 4 | | | IV-2 | Uchl4 | 0.92 |
| 8696 | 3 | 4 | | | IV-2 | Ttc9c | 0.90 | 8792 | 3 | 4 | | | IV-2 | Uchl5 | 0.82 |
| 8697 | 3 | 4 | | | IV-2 | Ttf1 | 0.95 | 8793 | 3 | 4 | | | IV-2 | Uck1 | 1.00 |
| 8698 | 3 | 4 | | | IV-2 | Ttf2 | 0.73 | 8794 | 3 | 4 | | | IV-2 | Uck2 | 0.90 |
| 8699 | 3 | 4 | | | IV-2 | Tti1 | 0.85 | 8795 | 3 | 4 | | | IV-2 | Uckl1 | 0.97 |
| 8700 | 3 | 4 | | | IV-2 | Ttll2 | 0.77 | 8796 | 3 | 4 | | | IV-2 | Uckl1os | 0.82 |
| 8701 | 3 | 4 | | | IV-2 | Ttll4 | 0.94 | 8797 | 3 | 4 | | | IV-2 | Ucp2 | 0.72 |
| 8702 | 3 | 4 | | | IV-2 | Ttll5 | 0.81 | 8798 | 3 | 4 | | | IV-2 | Uevld | 0.93 |
| 8703 | 3 | 4 | | | IV-2 | Ttn | 0.68 | 8799 | 3 | 4 | | | IV-2 | Ufc1 | 0.97 |
| 8704 | 3 | 4 | | | IV-2 | Ttyh2 | 0.77 | 8800 | 3 | 4 | | | IV-2 | Ufsp2 | 0.82 |
| 8705 | 3 | 4 | | | IV-2 | Tuba1b | 0.80 | 8801 | 3 | 4 | | | IV-2 | Uggt1 | 0.88 |
| 8706 | 3 | 4 | | | IV-2 | Tuba1c | 0.92 | 8802 | 3 | 4 | | | IV-2 | Ugp2 | 0.88 |
| 8707 | 3 | 4 | | | IV-2 | Tubb5 | 0.95 | 8803 | 3 | 4 | | | IV-2 | Ugt1a6a | 0.91 |
| 8708 | 3 | 4 | | | IV-2 | Tubb6 | 0.70 | 8804 | 3 | 4 | | | IV-2 | Ugt1a6b | 0.85 |
| 8709 | 3 | 4 | | | IV-2 | Tube1 | 0.88 | 8805 | 3 | 4 | | | IV-2 | Ugt1a7c | 0.79 |
| 8710 | 3 | 4 | | | IV-2 | Tubg1 | 0.74 | 8806 | 3 | 4 | | | IV-2 | Ugt2b35 | 0.91 |
| 8711 | 3 | 4 | | | IV-2 | Tubgcp3 | 0.98 | 8807 | 3 | 4 | | | IV-2 | Ugt2b38 | 0.99 |
| 8712 | 3 | 4 | | | IV-2 | Tubgcp4 | 0.79 | 8808 | 3 | 4 | | | IV-2 | Uhmk1 | 0.80 |
| 8713 | 3 | 4 | | | IV-2 | Tubgcp6 | 0.93 | 8809 | 3 | 4 | | | IV-2 | Uhrf2 | 0.68 |
| 8714 | 3 | 4 | | | IV-2 | Tuft1 | 0.92 | 8810 | 3 | 4 | | | IV-2 | Ulbp1 | 0.82 |
| 8715 | 3 | 4 | | | IV-2 | Tug1 | 0.96 | 8811 | 3 | 4 | | | IV-2 | Umps | 0.79 |
| 8716 | 3 | 4 | | | IV-2 | Tusc2 | 0.86 | 8812 | 3 | 4 | | | IV-2 | Unc119b | 0.86 |
| 8717 | 3 | 4 | | | IV-2 | Tusc5 | 0.77 | 8813 | 3 | 4 | | | IV-2 | Unc45b | 0.73 |
| 8718 | 3 | 4 | | | IV-2 | Tvp23b | 0.93 | 8814 | 3 | 4 | | | IV-2 | Unc5b | 0.85 |
| 8719 | 3 | 4 | | | IV-2 | Twf1 | 0.90 | 8815 | 3 | 4 | | | IV-2 | Ung | 0.76 |
| 8720 | 3 | 4 | | | IV-2 | Twf2 | 0.76 | 8816 | 3 | 4 | | | IV-2 | Upf1 | 0.90 |
| 8721 | 3 | 4 | | | IV-2 | Twist2 | 0.90 | 8817 | 3 | 4 | | | IV-2 | Upf2 | 1.00 |
| 8722 | 3 | 4 | | | IV-2 | Txina | 0.90 | 8818 | 3 | 4 | | | IV-2 | Upf3a | 0.97 |
| 8723 | 3 | 4 | | | IV-2 | Txinb | 0.79 | 8819 | 3 | 4 | | | IV-2 | Upk3a | 0.99 |
| 8724 | 3 | 4 | | | IV-2 | Txn1 | 0.80 | 8820 | 3 | 4 | | | IV-2 | Upk3b | 0.74 |
| 8725 | 3 | 4 | | | IV-2 | Txn2 | 0.76 | 8821 | 3 | 4 | | | IV-2 | Upk3bl | 0.94 |
| 8726 | 3 | 4 | | | IV-2 | Txndc12 | 0.83 | 8822 | 3 | 4 | | | IV-2 | Upp1 | 0.90 |
| 8727 | 3 | 4 | | | IV-2 | Txndc15 | 0.84 | 8823 | 3 | 4 | | | IV-2 | Uprt | 0.77 |
| 8728 | 3 | 4 | | | IV-2 | Txndc16 | 0.99 | 8824 | 3 | 4 | | | IV-2 | Uqcc1 | 0.89 |
| 8729 | 3 | 4 | | | IV-2 | Txndc17 | 0.75 | 8825 | 3 | 4 | | | IV-2 | Uqcr10 | 0.76 |
| 8730 | 3 | 4 | | | IV-2 | Txndc5 | 0.92 | 8826 | 3 | 4 | | | IV-2 | Uqcrb | 0.72 |
| 8731 | 3 | 4 | | | IV-2 | Txnl1 | 0.89 | 8827 | 3 | 4 | | | IV-2 | Uqcrc1 | 0.73 |
| 8732 | 3 | 4 | | | IV-2 | Txnl4a | 0.95 | 8828 | 3 | 4 | | | IV-2 | Uqcrc2 | 0.70 |
| 8733 | 3 | 4 | | | IV-2 | Txnl4b | 0.93 | 8829 | 3 | 4 | | | IV-2 | Uqcrfs1 | 0.72 |

Fig. 45 - 47

| | | | | | | | | | | | | | |
|---|---|---|---|---|---|---|---|---|---|---|---|---|---|
| 8830 | 3 | 4 | | | IV-2 | Uqcrh | 0.84 | 8926 | 3 | 4 | | IV-2 | Was | 0.68 |
| 8831 | 3 | 4 | | | IV-2 | Urah | 0.96 | 8927 | 3 | 4 | | IV-2 | Wasf2 | 0.85 |
| 8832 | 3 | 4 | | | IV-2 | Urb1 | 0.89 | 8928 | 3 | 4 | | IV-2 | Wbp1 | 0.91 |
| 8833 | 3 | 4 | | | IV-2 | Urgcp | 0.99 | 8929 | 3 | 4 | | IV-2 | Wbp1l | 0.94 |
| 8834 | 3 | 4 | | | IV-2 | Urm1 | 0.95 | 8930 | 3 | 4 | | IV-2 | Wbp1l | 0.93 |
| 8835 | 3 | 4 | | | IV-2 | Usb1 | 0.94 | 8931 | 3 | 4 | | IV-2 | Wbp2 | 0.91 |
| 8836 | 3 | 4 | | | IV-2 | Ushbp1 | 0.88 | 8932 | 3 | 4 | | IV-2 | Wbp4 | 0.98 |
| 8837 | 3 | 4 | | | IV-2 | Usmg5 | 0.91 | 8933 | 3 | 4 | | IV-2 | Wbp5 | 0.87 |
| 8838 | 3 | 4 | | | IV-2 | Uso1 | 0.95 | 8934 | 3 | 4 | | IV-2 | Wbscr16 | 0.94 |
| 8839 | 3 | 4 | | | IV-2 | Usp1 | 0.85 | 8935 | 3 | 4 | | IV-2 | Wbscr22 | 0.73 |
| 8840 | 3 | 4 | | | IV-2 | Usp10 | 0.86 | 8936 | 3 | 4 | | IV-2 | Wdfy4 | 0.96 |
| 8841 | 3 | 4 | | | IV-2 | Usp11 | 0.78 | 8937 | 3 | 4 | | IV-2 | Wdhd1 | 0.83 |
| 8842 | 3 | 4 | | | IV-2 | Usp13 | 0.79 | 8938 | 3 | 4 | | IV-2 | Wdr1 | 0.80 |
| 8843 | 3 | 4 | | | IV-2 | Usp14 | 0.90 | 8939 | 3 | 4 | | IV-2 | Wdr12 | 0.85 |
| 8844 | 3 | 4 | | | IV-2 | Usp15 | 0.77 | 8940 | 3 | 4 | | IV-2 | Wdr16 | 0.99 |
| 8845 | 3 | 4 | | | IV-2 | Usp20 | 0.98 | 8941 | 3 | 4 | | IV-2 | Wdr20 | 0.93 |
| 8846 | 3 | 4 | | | IV-2 | Usp21 | 0.90 | 8942 | 3 | 4 | | IV-2 | Wdr20rt | 0.94 |
| 8847 | 3 | 4 | | | IV-2 | Usp24 | 0.97 | 8943 | 3 | 4 | | IV-2 | Wdr24 | 0.90 |
| 8848 | 3 | 4 | | | IV-2 | Usp25 | 0.75 | 8944 | 3 | 4 | | IV-2 | Wdr25 | 0.94 |
| 8849 | 3 | 4 | | | IV-2 | Usp28 | 0.94 | 8945 | 3 | 4 | | IV-2 | Wdr26 | 0.97 |
| 8850 | 3 | 4 | | | IV-2 | Usp31 | 0.96 | 8946 | 3 | 4 | | IV-2 | Wdr3 | 0.97 |
| 8851 | 3 | 4 | | | IV-2 | Usp32 | 0.93 | 8947 | 3 | 4 | | IV-2 | Wdr33 | 0.98 |
| 8852 | 3 | 4 | | | IV-2 | Usp34 | 1.00 | 8948 | 3 | 4 | | IV-2 | Wdr4 | 0.88 |
| 8853 | 3 | 4 | | | IV-2 | Usp37 | 0.80 | 8949 | 3 | 4 | | IV-2 | Wdr44 | 0.91 |
| 8854 | 3 | 4 | | | IV-2 | Usp38 | 0.95 | 8950 | 3 | 4 | | IV-2 | Wdr48 | 0.95 |
| 8855 | 3 | 4 | | | IV-2 | Usp39 | 0.79 | 8951 | 3 | 4 | | IV-2 | Wdr53 | 0.96 |
| 8856 | 3 | 4 | | | IV-2 | Usp40 | 0.90 | 8952 | 3 | 4 | | IV-2 | Wdr55 | 0.73 |
| 8857 | 3 | 4 | | | IV-2 | Usp45 | 0.77 | 8953 | 3 | 4 | | IV-2 | Wdr5b | 0.97 |
| 8858 | 3 | 4 | | | IV-2 | Usp46 | 0.89 | 8954 | 3 | 4 | | IV-2 | Wdr61 | 0.78 |
| 8859 | 3 | 4 | | | IV-2 | Usp5 | 0.95 | 8955 | 3 | 4 | | IV-2 | Wdr62 | 0.98 |
| 8860 | 3 | 4 | | | IV-2 | Usp7 | 0.90 | 8956 | 3 | 4 | | IV-2 | Wdr76 | 0.68 |
| 8861 | 3 | 4 | | | IV-2 | Usp8 | 0.97 | 8957 | 3 | 4 | | IV-2 | Wdr81 | 0.76 |
| 8862 | 3 | 4 | | | IV-2 | Utp11l | 0.73 | 8958 | 3 | 4 | | IV-2 | Wdr82 | 0.98 |
| 8863 | 3 | 4 | | | IV-2 | Utp14b | 0.76 | 8959 | 3 | 4 | | IV-2 | Wdr83os | 0.92 |
| 8864 | 3 | 4 | | | IV-2 | Utp23 | 0.72 | 8960 | 3 | 4 | | IV-2 | Wdr89 | 0.75 |
| 8865 | 3 | 4 | | | IV-2 | Utp3 | 0.91 | 8961 | 3 | 4 | | IV-2 | Wdr90 | 0.89 |
| 8866 | 3 | 4 | | | IV-2 | Utp6 | 0.92 | 8962 | 3 | 4 | | IV-2 | Wdr92 | 0.88 |
| 8867 | 3 | 4 | | | IV-2 | Uvrag | 0.90 | 8963 | 3 | 4 | | IV-2 | Wdtc1 | 0.97 |
| 8868 | 3 | 4 | | | IV-2 | Ux1 | 0.97 | 8964 | 3 | 4 | | IV-2 | Wdyhv1 | 0.80 |
| 8869 | 3 | 4 | | | IV-2 | Vamp3 | 0.81 | 8965 | 3 | 4 | | IV-2 | Wee1 | 0.92 |
| 8870 | 3 | 4 | | | IV-2 | Vamp7 | 0.79 | 8966 | 3 | 4 | | IV-2 | Wfdc2 | 0.87 |
| 8871 | 3 | 4 | | | IV-2 | Vamp8 | 0.74 | 8967 | 3 | 4 | | IV-2 | Wfdc5 | 0.96 |
| 8872 | 3 | 4 | | | IV-2 | Vangl1 | 0.91 | 8968 | 3 | 4 | | IV-2 | Whsc1l1 | 0.90 |
| 8873 | 3 | 4 | | | IV-2 | Vapa | 0.97 | 8969 | 3 | 4 | | IV-2 | Wipf1 | 0.95 |
| 8874 | 3 | 4 | | | IV-2 | Vars | 0.85 | 8970 | 3 | 4 | | IV-2 | Wisp1 | 0.96 |
| 8875 | 3 | 4 | | | IV-2 | Vars2 | 0.93 | 8971 | 3 | 4 | | IV-2 | Wnk1 | 0.88 |
| 8876 | 3 | 4 | | | IV-2 | Vasp | 0.83 | 8972 | 3 | 4 | | IV-2 | Wnt16 | 0.87 |
| 8877 | 3 | 4 | | | IV-2 | Vat1 | 0.97 | 8973 | 3 | 4 | | IV-2 | Wnt2 | 0.69 |
| 8878 | 3 | 4 | | | IV-2 | Vav3 | 0.96 | 8974 | 3 | 4 | | IV-2 | Wnt6 | 0.92 |
| 8879 | 3 | 4 | | | IV-2 | Vbp1 | 0.88 | 8975 | 3 | 4 | | IV-2 | Wrap53 | 0.88 |
| 8880 | 3 | 4 | | | IV-2 | Vcam1 | 0.95 | 8976 | 3 | 4 | | IV-2 | Wrn | 0.73 |
| 8881 | 3 | 4 | | | IV-2 | Vcl | 0.95 | 8977 | 3 | 4 | | IV-2 | Wrnip1 | 0.98 |
| 8882 | 3 | 4 | | | IV-2 | Vcp | 0.93 | 8978 | 3 | 4 | | IV-2 | Wwp1 | 0.95 |
| 8883 | 3 | 4 | | | IV-2 | Vcpkmt | 0.90 | 8979 | 3 | 4 | | IV-2 | Xbp1 | 0.71 |
| 8884 | 3 | 4 | | | IV-2 | Vdac1 | 0.87 | 8980 | 3 | 4 | | IV-2 | Xirp1 | 0.87 |
| 8885 | 3 | 4 | | | IV-2 | Vdac2 | 0.86 | 8981 | 3 | 4 | | IV-2 | Xkr5 | 0.94 |
| 8886 | 3 | 4 | | | IV-2 | Vdac3 | 0.88 | 8982 | 3 | 4 | | IV-2 | Xkrx | 0.72 |
| 8887 | 3 | 4 | | | IV-2 | Vdr | 0.99 | 8983 | 3 | 4 | | IV-2 | Xndc1 | 0.81 |
| 8888 | 3 | 4 | | | IV-2 | Vegfa | 0.91 | 8984 | 3 | 4 | | IV-2 | Xpnpep1 | 0.85 |
| 8889 | 3 | 4 | | | IV-2 | Vegfb | 0.74 | 8985 | 3 | 4 | | IV-2 | Xpo4 | 0.88 |
| 8890 | 3 | 4 | | | IV-2 | Vgll2 | 0.80 | 8986 | 3 | 4 | | IV-2 | Xpo5 | 0.95 |
| 8891 | 3 | 4 | | | IV-2 | Vgll3 | 0.99 | 8987 | 3 | 4 | | IV-2 | Xpo7 | 0.68 |
| 8892 | 3 | 4 | | | IV-2 | Vgll4 | 0.73 | 8988 | 3 | 4 | | IV-2 | Xrcc1 | 0.91 |
| 8893 | 3 | 4 | | | IV-2 | Vim | 0.95 | 8989 | 3 | 4 | | IV-2 | Xrcc2 | 0.98 |
| 8894 | 3 | 4 | | | IV-2 | Vimp | 0.89 | 8990 | 3 | 4 | | IV-2 | Xrcc4 | 0.86 |
| 8895 | 3 | 4 | | | IV-2 | Vip | 0.92 | 8991 | 3 | 4 | | IV-2 | Xrcc5 | 0.99 |
| 8896 | 3 | 4 | | | IV-2 | Vkorc1 | 0.80 | 8992 | 3 | 4 | | IV-2 | Xrcc6 | 0.75 |
| 8897 | 3 | 4 | | | IV-2 | Vma21 | 0.96 | 8993 | 3 | 4 | | IV-2 | Xrcc6bp1 | 0.99 |
| 8898 | 3 | 4 | | | IV-2 | Vmn2r29 | 0.95 | 8994 | 3 | 4 | | IV-2 | Xylb | 0.83 |
| 8899 | 3 | 4 | | | IV-2 | Vmp1 | 0.86 | 8995 | 3 | 4 | | IV-2 | Yae1d1 | 0.82 |
| 8900 | 3 | 4 | | | IV-2 | Vprbp | 0.96 | 8996 | 3 | 4 | | IV-2 | Yaf2 | 0.98 |
| 8901 | 3 | 4 | | | IV-2 | Vps13a | 0.78 | 8997 | 3 | 4 | | IV-2 | Yap1 | 1.00 |
| 8902 | 3 | 4 | | | IV-2 | Vps13b | 0.91 | 8998 | 3 | 4 | | IV-2 | Yars2 | 0.72 |
| 8903 | 3 | 4 | | | IV-2 | Vps13c | 0.80 | 8999 | 3 | 4 | | IV-2 | Ybey | 0.98 |
| 8904 | 3 | 4 | | | IV-2 | Vps18 | 0.97 | 9000 | 3 | 4 | | IV-2 | Ybx1 | 0.82 |
| 8905 | 3 | 4 | | | IV-2 | Vps26a | 0.92 | 9001 | 3 | 4 | | IV-2 | Ybx2 | 0.68 |
| 8906 | 3 | 4 | | | IV-2 | Vps29 | 0.79 | 9002 | 3 | 4 | | IV-2 | Ybx3 | 0.76 |
| 8907 | 3 | 4 | | | IV-2 | Vps35 | 0.86 | 9003 | 3 | 4 | | IV-2 | Yeats4 | 0.98 |
| 8908 | 3 | 4 | | | IV-2 | Vps36 | 0.74 | 9004 | 3 | 4 | | IV-2 | Yes1 | 0.96 |
| 8909 | 3 | 4 | | | IV-2 | Vps37b | 0.98 | 9005 | 3 | 4 | | IV-2 | Yif1a | 0.82 |
| 8910 | 3 | 4 | | | IV-2 | Vps45 | 0.81 | 9006 | 3 | 4 | | IV-2 | Yipf1 | 0.98 |
| 8911 | 3 | 4 | | | IV-2 | Vps52 | 0.95 | 9007 | 3 | 4 | | IV-2 | Yipf4 | 0.90 |
| 8912 | 3 | 4 | | | IV-2 | Vrk1 | 0.99 | 9008 | 3 | 4 | | IV-2 | Yipf5 | 0.83 |
| 8913 | 3 | 4 | | | IV-2 | Vrk2 | 0.97 | 9009 | 3 | 4 | | IV-2 | Yme1l1 | 0.90 |
| 8914 | 3 | 4 | | | IV-2 | Vrk3 | 0.94 | 9010 | 3 | 4 | | IV-2 | Yod1 | 0.73 |
| 8915 | 3 | 4 | | | IV-2 | Vsig2 | 0.96 | 9011 | 3 | 4 | | IV-2 | Ypel2 | 0.69 |
| 8916 | 3 | 4 | | | IV-2 | Vstm4 | 0.83 | 9012 | 3 | 4 | | IV-2 | Ypel4 | 0.73 |
| 8917 | 3 | 4 | | | IV-2 | Vstm5 | 0.89 | 9013 | 3 | 4 | | IV-2 | Ywhab | 0.94 |
| 8918 | 3 | 4 | | | IV-2 | Vti1b | 0.90 | 9014 | 3 | 4 | | IV-2 | Ywhae | 0.83 |
| 8919 | 3 | 4 | | | IV-2 | Vwa1 | 0.95 | 9015 | 3 | 4 | | IV-2 | Ywhag | 0.94 |
| 8920 | 3 | 4 | | | IV-2 | Vwa5a | 0.90 | 9016 | 3 | 4 | | IV-2 | Ywhah | 0.78 |
| 8921 | 3 | 4 | | | IV-2 | Vwa8 | 0.78 | 9017 | 3 | 4 | | IV-2 | Ywhaq | 0.86 |
| 8922 | 3 | 4 | | | IV-2 | Vwa9 | 0.96 | 9018 | 3 | 4 | | IV-2 | Yy1 | 0.97 |
| 8923 | 3 | 4 | | | IV-2 | Vwce | 0.77 | 9019 | 3 | 4 | | IV-2 | Zadh2 | 0.90 |
| 8924 | 3 | 4 | | | IV-2 | Wapal | 0.83 | 9020 | 3 | 4 | | IV-2 | Zak | 0.80 |
| 8925 | 3 | 4 | | | IV-2 | Wars | 0.96 | 9021 | 3 | 4 | | IV-2 | Zbed4 | 0.70 |

Fig. 45 - 48

| | | | | | | | | | | | | | | |
|---|---|---|---|---|---|---|---|---|---|---|---|---|---|---|
| 9022 | 3 | 4 | | | IV-2 | Zbed6 | 0.96 | 9118 | 3 | 4 | | | IV-2 | Zfp444 | 0.99 |
| 9023 | 3 | 4 | | | IV-2 | Zbtb1 | 0.83 | 9119 | 3 | 4 | | | IV-2 | Zfp449 | 0.84 |
| 9024 | 3 | 4 | | | IV-2 | Zbtb11 | 0.93 | 9120 | 3 | 4 | | | IV-2 | Zfp451 | 0.98 |
| 9025 | 3 | 4 | | | IV-2 | Zbtb21 | 0.84 | 9121 | 3 | 4 | | | IV-2 | Zfp455 | 0.83 |
| 9026 | 3 | 4 | | | IV-2 | Zbtb26 | 0.99 | 9122 | 3 | 4 | | | IV-2 | Zfp456 | 0.87 |
| 9027 | 3 | 4 | | | IV-2 | Zbtb3 | 0.85 | 9123 | 3 | 4 | | | IV-2 | Zfp458 | 0.88 |
| 9028 | 3 | 4 | | | IV-2 | Zbtb37 | 0.91 | 9124 | 3 | 4 | | | IV-2 | Zfp467 | 0.89 |
| 9029 | 3 | 4 | | | IV-2 | Zbtb43 | 0.98 | 9125 | 3 | 4 | | | IV-2 | Zfp472 | 0.80 |
| 9030 | 3 | 4 | | | IV-2 | Zbtb46 | 0.95 | 9126 | 3 | 4 | | | IV-2 | Zfp473 | 0.90 |
| 9031 | 3 | 4 | | | IV-2 | Zbtb6 | 0.97 | 9127 | 3 | 4 | | | IV-2 | Zfp507 | 0.99 |
| 9032 | 3 | 4 | | | IV-2 | Zbtb7a | 0.68 | 9128 | 3 | 4 | | | IV-2 | Zfp51 | 0.89 |
| 9033 | 3 | 4 | | | IV-2 | Zbtb7b | 0.69 | 9129 | 3 | 4 | | | IV-2 | Zfp511 | 0.81 |
| 9034 | 3 | 4 | | | IV-2 | Zbtbd6 | 0.73 | 9130 | 3 | 4 | | | IV-2 | Zfp518a | 0.99 |
| 9035 | 3 | 4 | | | IV-2 | Zc3h10 | 0.84 | 9131 | 3 | 4 | | | IV-2 | Zfp52 | 0.84 |
| 9036 | 3 | 4 | | | IV-2 | Zc3h11a | 0.95 | 9132 | 3 | 4 | | | IV-2 | Zfp524 | 0.71 |
| 9037 | 3 | 4 | | | IV-2 | Zc3h12a | 0.91 | 9133 | 3 | 4 | | | IV-2 | Zfp526 | 0.86 |
| 9038 | 3 | 4 | | | IV-2 | Zc3h18 | 0.95 | 9134 | 3 | 4 | | | IV-2 | Zfp54 | 0.78 |
| 9039 | 3 | 4 | | | IV-2 | Zc3h3 | 0.82 | 9135 | 3 | 4 | | | IV-2 | Zfp563 | 0.90 |
| 9040 | 3 | 4 | | | IV-2 | Zc3h7a | 0.97 | 9136 | 3 | 4 | | | IV-2 | Zfp568 | 0.89 |
| 9041 | 3 | 4 | | | IV-2 | Zc3hav1 | 0.85 | 9137 | 3 | 4 | | | IV-2 | Zfp58 | 0.69 |
| 9042 | 3 | 4 | | | IV-2 | Zc3hc1 | 0.86 | 9138 | 3 | 4 | | | IV-2 | Zfp583 | 0.75 |
| 9043 | 3 | 4 | | | IV-2 | Zcchc10 | 0.96 | 9139 | 3 | 4 | | | IV-2 | Zfp59 | 0.96 |
| 9044 | 3 | 4 | | | IV-2 | Zcchc17 | 0.76 | 9140 | 3 | 4 | | | IV-2 | Zfp595 | 0.85 |
| 9045 | 3 | 4 | | | IV-2 | Zcchc2 | 0.92 | 9141 | 3 | 4 | | | IV-2 | Zfp597 | 0.97 |
| 9046 | 3 | 4 | | | IV-2 | Zcchc3 | 0.93 | 9142 | 3 | 4 | | | IV-2 | Zfp598 | 0.94 |
| 9047 | 3 | 4 | | | IV-2 | Zcchc8 | 0.91 | 9143 | 3 | 4 | | | IV-2 | Zfp60 | 0.97 |
| 9048 | 3 | 4 | | | IV-2 | Zcchc9 | 0.92 | 9144 | 3 | 4 | | | IV-2 | Zfp607 | 0.91 |
| 9049 | 3 | 4 | | | IV-2 | Zcrb1 | 0.82 | 9145 | 3 | 4 | | | IV-2 | Zfp612 | 0.89 |
| 9050 | 3 | 4 | | | IV-2 | Zcwpw1 | 0.90 | 9146 | 3 | 4 | | | IV-2 | Zfp617 | 0.98 |
| 9051 | 3 | 4 | | | IV-2 | Zdbf2 | 0.90 | 9147 | 3 | 4 | | | IV-2 | Zfp62 | 0.92 |
| 9052 | 3 | 4 | | | IV-2 | Zdhhc1 | 0.97 | 9148 | 3 | 4 | | | IV-2 | Zfp637 | 0.93 |
| 9053 | 3 | 4 | | | IV-2 | Zdhhc12 | 0.92 | 9149 | 3 | 4 | | | IV-2 | Zfp646 | 0.95 |
| 9054 | 3 | 4 | | | IV-2 | Zdhhc16 | 0.96 | 9150 | 3 | 4 | | | IV-2 | Zfp65 | 0.94 |
| 9055 | 3 | 4 | | | IV-2 | Zdhhc2 | 0.81 | 9151 | 3 | 4 | | | IV-2 | Zfp652 | 0.96 |
| 9056 | 3 | 4 | | | IV-2 | Zdhhc21 | 0.99 | 9152 | 3 | 4 | | | IV-2 | Zfp654 | 0.99 |
| 9057 | 3 | 4 | | | IV-2 | Zdhhc5 | 0.86 | 9153 | 3 | 4 | | | IV-2 | Zfp664 | 0.98 |
| 9058 | 3 | 4 | | | IV-2 | Zdhhc6 | 0.98 | 9154 | 3 | 4 | | | IV-2 | Zfp667 | 0.96 |
| 9059 | 3 | 4 | | | IV-2 | Zdhhc7 | 0.77 | 9155 | 3 | 4 | | | IV-2 | Zfp672 | 0.86 |
| 9060 | 3 | 4 | | | IV-2 | Zdhhc8 | 0.96 | 9156 | 3 | 4 | | | IV-2 | Zfp68 | 0.99 |
| 9061 | 3 | 4 | | | IV-2 | Zdhhc9 | 0.78 | 9157 | 3 | 4 | | | IV-2 | Zfp691 | 0.83 |
| 9062 | 3 | 4 | | | IV-2 | Zeb1 | 0.96 | 9158 | 3 | 4 | | | IV-2 | Zfp692 | 0.72 |
| 9063 | 3 | 4 | | | IV-2 | Zeb2 | 0.94 | 9159 | 3 | 4 | | | IV-2 | Zfp7 | 0.93 |
| 9064 | 3 | 4 | | | IV-2 | Zeb2os | 0.97 | 9160 | 3 | 4 | | | IV-2 | Zfp706 | 0.92 |
| 9065 | 3 | 4 | | | IV-2 | Zfand2b | 0.81 | 9161 | 3 | 4 | | | IV-2 | Zfp708 | 0.85 |
| 9066 | 3 | 4 | | | IV-2 | Zfand3 | 0.99 | 9162 | 3 | 4 | | | IV-2 | Zfp709 | 0.92 |
| 9067 | 3 | 4 | | | IV-2 | Zfand6 | 0.71 | 9163 | 3 | 4 | | | IV-2 | Zfp710 | 0.94 |
| 9068 | 3 | 4 | | | IV-2 | Zfat | 0.88 | 9164 | 3 | 4 | | | IV-2 | Zfp719 | 0.84 |
| 9069 | 3 | 4 | | | IV-2 | Zfc3h1 | 1.00 | 9165 | 3 | 4 | | | IV-2 | Zfp72 | 0.70 |
| 9070 | 3 | 4 | | | IV-2 | Zfml | 0.96 | 9166 | 3 | 4 | | | IV-2 | Zfp747 | 0.89 |
| 9071 | 3 | 4 | | | IV-2 | Zfp106 | 0.94 | 9167 | 3 | 4 | | | IV-2 | Zfp748 | 0.90 |
| 9072 | 3 | 4 | | | IV-2 | Zfp108 | 0.94 | 9168 | 3 | 4 | | | IV-2 | Zfp750 | 0.85 |
| 9073 | 3 | 4 | | | IV-2 | Zfp110 | 0.87 | 9169 | 3 | 4 | | | IV-2 | Zfp758 | 0.88 |
| 9074 | 3 | 4 | | | IV-2 | Zfp120 | 0.84 | 9170 | 3 | 4 | | | IV-2 | Zfp759 | 0.79 |
| 9075 | 3 | 4 | | | IV-2 | Zfp128 | 0.98 | 9171 | 3 | 4 | | | IV-2 | Zfp772 | 0.90 |
| 9076 | 3 | 4 | | | IV-2 | Zfp133-ps | 0.91 | 9172 | 3 | 4 | | | IV-2 | Zfp780b | 0.94 |
| 9077 | 3 | 4 | | | IV-2 | Zfp14 | 0.91 | 9173 | 3 | 4 | | | IV-2 | Zfp790 | 0.89 |
| 9078 | 3 | 4 | | | IV-2 | Zfp142 | 0.77 | 9174 | 3 | 4 | | | IV-2 | Zfp800 | 0.88 |
| 9079 | 3 | 4 | | | IV-2 | Zfp143 | 0.88 | 9175 | 3 | 4 | | | IV-2 | Zfp809 | 0.75 |
| 9080 | 3 | 4 | | | IV-2 | Zfp169 | 0.75 | 9176 | 3 | 4 | | | IV-2 | Zfp82 | 0.82 |
| 9081 | 3 | 4 | | | IV-2 | Zfp180 | 0.85 | 9177 | 3 | 4 | | | IV-2 | Zfp820 | 0.83 |
| 9082 | 3 | 4 | | | IV-2 | Zfp182 | 0.99 | 9178 | 3 | 4 | | | IV-2 | Zfp830 | 0.82 |
| 9083 | 3 | 4 | | | IV-2 | Zfp185 | 0.81 | 9179 | 3 | 4 | | | IV-2 | Zfp84 | 0.83 |
| 9084 | 3 | 4 | | | IV-2 | Zfp189 | 0.85 | 9180 | 3 | 4 | | | IV-2 | Zfp850 | 0.79 |
| 9085 | 3 | 4 | | | IV-2 | Zfp213 | 0.83 | 9181 | 3 | 4 | | | IV-2 | Zfp866 | 0.97 |
| 9086 | 3 | 4 | | | IV-2 | Zfp217 | 0.91 | 9182 | 3 | 4 | | | IV-2 | Zfp868 | 0.99 |
| 9087 | 3 | 4 | | | IV-2 | Zfp235 | 0.86 | 9183 | 3 | 4 | | | IV-2 | Zfp869 | 1.00 |
| 9088 | 3 | 4 | | | IV-2 | Zfp239 | 0.86 | 9184 | 3 | 4 | | | IV-2 | Zfp87 | 0.95 |
| 9089 | 3 | 4 | | | IV-2 | Zfp260 | 0.87 | 9185 | 3 | 4 | | | IV-2 | Zfp870 | 0.92 |
| 9090 | 3 | 4 | | | IV-2 | Zfp266 | 0.98 | 9186 | 3 | 4 | | | IV-2 | Zfp871 | 0.88 |
| 9091 | 3 | 4 | | | IV-2 | Zfp275 | 0.80 | 9187 | 3 | 4 | | | IV-2 | Zfp874a | 0.88 |
| 9092 | 3 | 4 | | | IV-2 | Zfp276 | 0.88 | 9188 | 3 | 4 | | | IV-2 | Zfp874b | 0.86 |
| 9093 | 3 | 4 | | | IV-2 | Zfp280b | 0.93 | 9189 | 3 | 4 | | | IV-2 | Zfp882 | 0.93 |
| 9094 | 3 | 4 | | | IV-2 | Zfp296 | 0.78 | 9190 | 3 | 4 | | | IV-2 | Zfp91 | 0.96 |
| 9095 | 3 | 4 | | | IV-2 | Zfp317 | 0.93 | 9191 | 3 | 4 | | | IV-2 | Zfp930 | 0.97 |
| 9096 | 3 | 4 | | | IV-2 | Zfp322a | 0.93 | 9192 | 3 | 4 | | | IV-2 | Zfp931 | 0.68 |
| 9097 | 3 | 4 | | | IV-2 | Zfp324 | 0.95 | 9193 | 3 | 4 | | | IV-2 | Zfp932 | 0.83 |
| 9098 | 3 | 4 | | | IV-2 | Zfp335 | 0.94 | 9194 | 3 | 4 | | | IV-2 | Zfp933 | 0.88 |
| 9099 | 3 | 4 | | | IV-2 | Zfp341 | 0.73 | 9195 | 3 | 4 | | | IV-2 | Zfp934 | 0.84 |
| 9100 | 3 | 4 | | | IV-2 | Zfp35 | 0.83 | 9196 | 3 | 4 | | | IV-2 | Zfp935 | 0.87 |
| 9101 | 3 | 4 | | | IV-2 | Zfp366 | 0.78 | 9197 | 3 | 4 | | | IV-2 | Zfp937 | 0.76 |
| 9102 | 3 | 4 | | | IV-2 | Zfp367 | 0.69 | 9198 | 3 | 4 | | | IV-2 | Zfp938 | 0.99 |
| 9103 | 3 | 4 | | | IV-2 | Zfp369 | 0.83 | 9199 | 3 | 4 | | | IV-2 | Zfp942 | 0.95 |
| 9104 | 3 | 4 | | | IV-2 | Zfp36l1 | 0.92 | 9200 | 3 | 4 | | | IV-2 | Zfp943 | 0.98 |
| 9105 | 3 | 4 | | | IV-2 | Zfp36l2 | 0.97 | 9201 | 3 | 4 | | | IV-2 | Zfp946 | 0.97 |
| 9106 | 3 | 4 | | | IV-2 | Zfp382 | 0.86 | 9202 | 3 | 4 | | | IV-2 | Zfp953 | 0.69 |
| 9107 | 3 | 4 | | | IV-2 | Zfp385b | 0.87 | 9203 | 3 | 4 | | | IV-2 | Zfp954 | 0.84 |
| 9108 | 3 | 4 | | | IV-2 | Zfp385c | 0.95 | 9204 | 3 | 4 | | | IV-2 | Zfp955a | 0.89 |
| 9109 | 3 | 4 | | | IV-2 | Zfp39 | 0.91 | 9205 | 3 | 4 | | | IV-2 | Zfp959 | 0.93 |
| 9110 | 3 | 4 | | | IV-2 | Zfp395 | 0.84 | 9206 | 3 | 4 | | | IV-2 | Zfp961 | 0.69 |
| 9111 | 3 | 4 | | | IV-2 | Zfp397 | 0.99 | 9207 | 3 | 4 | | | IV-2 | Zfp97 | 0.93 |
| 9112 | 3 | 4 | | | IV-2 | Zfp407 | 0.88 | 9208 | 3 | 4 | | | IV-2 | Zfyve16 | 0.96 |
| 9113 | 3 | 4 | | | IV-2 | Zfp410 | 0.94 | 9209 | 3 | 4 | | | IV-2 | Zfyve19 | 0.89 |
| 9114 | 3 | 4 | | | IV-2 | Zfp418 | 0.72 | 9210 | 3 | 4 | | | IV-2 | Zfyve26 | 0.85 |
| 9115 | 3 | 4 | | | IV-2 | Zfp420 | 0.84 | 9211 | 3 | 4 | | | IV-2 | Zgpat | 0.93 |
| 9116 | 3 | 4 | | | IV-2 | Zfp429 | 0.68 | 9212 | 3 | 4 | | | IV-2 | Zhx2 | 0.79 |
| 9117 | 3 | 4 | | | IV-2 | Zfp442 | 0.93 | 9213 | 3 | 4 | | | IV-2 | Zim1 | 1.00 |

Fig. 45 - 49

| | | | | | | | | | | | | | |
|---|---|---|---|---|---|---|---|---|---|---|---|---|---|
| 9214 | 3 | 4 | | | IV-2 | Zkscan3 | 0.85 | 9310 | 3 | 4 | | IV-1 | 2410004P03Rik | 1.01 |
| 9215 | 3 | 4 | | | IV-2 | Zmat2 | 0.88 | 9311 | 3 | 4 | | IV-1 | 2410018L13Rik | 1.10 |
| 9216 | 3 | 4 | | | IV-2 | Zmat5 | 0.89 | 9312 | 3 | 4 | | IV-1 | 2410089E03Rik | 1.49 |
| 9217 | 3 | 4 | | | IV-2 | Zmynd10 | 0.83 | 9313 | 3 | 4 | | IV-1 | 2410131K14Rik | 1.12 |
| 9218 | 3 | 4 | | | IV-2 | Zmynd19 | 0.90 | 9314 | 3 | 4 | | IV-1 | 2510002D24Rik | 1.18 |
| 9219 | 3 | 4 | | | IV-2 | Zmynd8 | 0.95 | 9315 | 3 | 4 | | IV-1 | 2510009E07Rik | 1.13 |
| 9220 | 3 | 4 | | | IV-2 | Znf41-ps | 0.80 | 9316 | 3 | 4 | | IV-1 | 2610002J02Rik | 1.17 |
| 9221 | 3 | 4 | | | IV-2 | Znhit1 | 0.77 | 9317 | 3 | 4 | | IV-1 | 2610005L07Rik | 1.23 |
| 9222 | 3 | 4 | | | IV-2 | Znhit2 | 1.00 | 9318 | 3 | 4 | | IV-1 | 2610008E11Rik | 1.22 |
| 9223 | 3 | 4 | | | IV-2 | Znrd1 | 0.73 | 9319 | 3 | 4 | | IV-1 | 2610018G03Rik | 1.43 |
| 9224 | 3 | 4 | | | IV-2 | Znrd1as | 0.82 | 9320 | 3 | 4 | | IV-1 | 2610020C07Rik | 1.22 |
| 9225 | 3 | 4 | | | IV-2 | Zranb3 | 0.75 | 9321 | 3 | 4 | | IV-1 | 2610301B20Rik | 1.06 |
| 9226 | 3 | 4 | | | IV-2 | Zrsr2 | 0.99 | 9322 | 3 | 4 | | IV-1 | 2610305D13Rik | 1.01 |
| 9227 | 3 | 4 | | | IV-2 | Zscan20 | 0.92 | 9323 | 3 | 4 | | IV-1 | 2610306M01Rik | 1.19 |
| 9228 | 3 | 4 | | | IV-2 | Zscan22 | 0.73 | 9324 | 3 | 4 | | IV-1 | 2610307P16Rik | 1.48 |
| 9229 | 3 | 4 | | | IV-2 | Zscan26 | 0.83 | 9325 | 3 | 4 | | IV-1 | 2700054A10Rik | 1.44 |
| 9230 | 3 | 4 | | | IV-2 | Zscan29 | 0.96 | 9326 | 3 | 4 | | IV-1 | 2700062C07Rik | 1.08 |
| 9231 | 3 | 4 | | | IV-2 | Zswim1 | 0.90 | 9327 | 3 | 4 | | IV-1 | 2700069I18Rik | 1.27 |
| 9232 | 3 | 4 | | | IV-2 | Zswim3 | 0.74 | 9328 | 3 | 4 | | IV-1 | 2700081O15Rik | 1.04 |
| 9233 | 3 | 4 | | | IV-2 | Zufsp | 0.77 | 9329 | 3 | 4 | | IV-1 | 2700086A05Rik | 1.35 |
| 9234 | 3 | 4 | | | IV-2 | Zw10 | 0.84 | 9330 | 3 | 4 | | IV-1 | 2810004G20Rik | 1.42 |
| 9235 | 3 | 4 | | | IV-2 | Zwilch | 0.90 | 9331 | 3 | 4 | | IV-1 | 2810008D09Rik | 1.28 |
| 9236 | 3 | 4 | | | IV-2 | Zyx | 0.95 | 9332 | 3 | 4 | | IV-1 | 2810021J22Rik | 1.23 |
| 9237 | 3 | 4 | | | IV-1 | 0610010F05Rik | 1.48 | 9333 | 3 | 4 | | IV-1 | 2810032Q03Rik | 1.31 |
| 9238 | 3 | 4 | | | IV-1 | 0610011F06Rik | 1.01 | 9334 | 3 | 4 | | IV-1 | 2810049E08Rik | 1.25 |
| 9239 | 3 | 4 | | | IV-1 | 0610037L13Rik | 1.10 | 9335 | 3 | 4 | | IV-1 | 2810403A07Rik | 1.34 |
| 9240 | 3 | 4 | | | IV-1 | 1110004F10Rik | 1.14 | 9336 | 3 | 4 | | IV-1 | 2810403D21Rik | 1.21 |
| 9241 | 3 | 4 | | | IV-1 | 1110012L19Rik | 1.16 | 9337 | 3 | 4 | | IV-1 | 2810405F15Rik | 1.04 |
| 9242 | 3 | 4 | | | IV-1 | 1110032A03Rik | 1.26 | 9338 | 3 | 4 | | IV-1 | 2810433D01Rik | 1.17 |
| 9243 | 3 | 4 | | | IV-1 | 1110034G24Rik | 1.12 | 9339 | 3 | 4 | | IV-1 | 2810474O19Rik | 1.02 |
| 9244 | 3 | 4 | | | IV-1 | 1110038B12Rik | 1.30 | 9340 | 3 | 4 | | IV-1 | 2900005J15Rik | 1.08 |
| 9245 | 3 | 4 | | | IV-1 | 1110051M20Rik | 1.03 | 9341 | 3 | 4 | | IV-1 | 2900056M20Rik | 1.45 |
| 9246 | 3 | 4 | | | IV-1 | 1110054M08Rik | 1.31 | 9342 | 3 | 4 | | IV-1 | 2900097C17Rik | 1.17 |
| 9247 | 3 | 4 | | | IV-1 | 1110059E24Rik | 1.05 | 9343 | 3 | 4 | | IV-1 | 3000002C10Rik | 1.04 |
| 9248 | 3 | 4 | | | IV-1 | 1110059G10Rik | 1.07 | 9344 | 3 | 4 | | IV-1 | 3010026O09Rik | 1.27 |
| 9249 | 3 | 4 | | | IV-1 | 1110065P20Rik | 1.08 | 9345 | 3 | 4 | | IV-1 | 3110035E14Rik | 1.11 |
| 9250 | 3 | 4 | | | IV-1 | 1200014J11Rik | 1.12 | 9346 | 3 | 4 | | IV-1 | 3110039M20Rik | 1.16 |
| 9251 | 3 | 4 | | | IV-1 | 1500004A13Rik | 1.15 | 9347 | 3 | 4 | | IV-1 | 3110043O21Rik | 1.13 |
| 9252 | 3 | 4 | | | IV-1 | 1500009C09Rik | 1.08 | 9348 | 3 | 4 | | IV-1 | 3110070M22Rik | 1.50 |
| 9253 | 3 | 4 | | | IV-1 | 1500015A07Rik | 1.32 | 9349 | 3 | 4 | | IV-1 | 3110079O15Rik | 1.24 |
| 9254 | 3 | 4 | | | IV-1 | 1600002K03Rik | 1.24 | 9350 | 3 | 4 | | IV-1 | 4632415L05Rik | 1.03 |
| 9255 | 3 | 4 | | | IV-1 | 1600023N17Rik | 1.01 | 9351 | 3 | 4 | | IV-1 | 4632427E13Rik | 1.01 |
| 9256 | 3 | 4 | | | IV-1 | 1700001G17Rik | 1.03 | 9352 | 3 | 4 | | IV-1 | 4732491K20Rik | 1.49 |
| 9257 | 3 | 4 | | | IV-1 | 1700001L05Rik | 1.05 | 9353 | 3 | 4 | | IV-1 | 4831440E17Rik | 1.15 |
| 9258 | 3 | 4 | | | IV-1 | 1700007L15Rik | 1.35 | 9354 | 3 | 4 | | IV-1 | 4833403I15Rik | 1.36 |
| 9259 | 3 | 4 | | | IV-1 | 1700008J07Rik | 1.25 | 9355 | 3 | 4 | | IV-1 | 4833412C05Rik | 1.23 |
| 9260 | 3 | 4 | | | IV-1 | 1700009P17Rik | 1.07 | 9356 | 3 | 4 | | IV-1 | 4833417C18Rik | 1.23 |
| 9261 | 3 | 4 | | | IV-1 | 1700012D14Rik | 1.50 | 9357 | 3 | 4 | | IV-1 | 4833420G17Rik | 1.40 |
| 9262 | 3 | 4 | | | IV-1 | 1700015E13Rik | 1.07 | 9358 | 3 | 4 | | IV-1 | 4833422C13Rik | 1.08 |
| 9263 | 3 | 4 | | | IV-1 | 1700016K19Rik | 1.19 | 9359 | 3 | 4 | | IV-1 | 4921504A21Rik | 1.18 |
| 9264 | 3 | 4 | | | IV-1 | 1700018L02Rik | 1.03 | 9360 | 3 | 4 | | IV-1 | 4921507P07Rik | 1.20 |
| 9265 | 3 | 4 | | | IV-1 | 1700019G17Rik | 1.36 | 9361 | 3 | 4 | | IV-1 | 4921524J17Rik | 1.04 |
| 9266 | 3 | 4 | | | IV-1 | 1700020L24Rik | 1.01 | 9362 | 3 | 4 | | IV-1 | 4930402H24Rik | 1.00 |
| 9267 | 3 | 4 | | | IV-1 | 1700025G04Rik | 1.02 | 9363 | 3 | 4 | | IV-1 | 4930412O13Rik | 1.13 |
| 9268 | 3 | 4 | | | IV-1 | 1700037C18Rik | 1.06 | 9364 | 3 | 4 | | IV-1 | 4930413G21Rik | 1.41 |
| 9269 | 3 | 4 | | | IV-1 | 1700047I17Rik2 | 1.19 | 9365 | 3 | 4 | | IV-1 | 4930414L22Rik | 1.46 |
| 9270 | 3 | 4 | | | IV-1 | 1700047M11Rik | 1.01 | 9366 | 3 | 4 | | IV-1 | 4930426D05Rik | 1.08 |
| 9271 | 3 | 4 | | | IV-1 | 1700049G17Rik | 1.14 | 9367 | 3 | 4 | | IV-1 | 4930429J21Rik | 1.43 |
| 9272 | 3 | 4 | | | IV-1 | 1700084C01Rik | 1.07 | 9368 | 3 | 4 | | IV-1 | 4930429F24Rik | 1.05 |
| 9273 | 3 | 4 | | | IV-1 | 1700084E18Rik | 1.01 | 9369 | 3 | 4 | | IV-1 | 4930432K21Rik | 1.41 |
| 9274 | 3 | 4 | | | IV-1 | 1700086L19Rik | 1.14 | 9370 | 3 | 4 | | IV-1 | 4930447C04Rik | 1.34 |
| 9275 | 3 | 4 | | | IV-1 | 1700093K21Rik | 1.08 | 9371 | 3 | 4 | | IV-1 | 4930451C15Rik | 1.09 |
| 9276 | 3 | 4 | | | IV-1 | 1700105P06Rik | 1.10 | 9372 | 3 | 4 | | IV-1 | 4930451G09Rik | 1.06 |
| 9277 | 3 | 4 | | | IV-1 | 1700113A16Rik | 1.16 | 9373 | 3 | 4 | | IV-1 | 4930481A15Rik | 1.32 |
| 9278 | 3 | 4 | | | IV-1 | 1810014B01Rik | 1.11 | 9374 | 3 | 4 | | IV-1 | 4930503L19Rik | 1.06 |
| 9279 | 3 | 4 | | | IV-1 | 1810022K09Rik | 1.13 | 9375 | 3 | 4 | | IV-1 | 4930506C21Rik | 1.18 |
| 9280 | 3 | 4 | | | IV-1 | 1810026B05Rik | 1.18 | 9376 | 3 | 4 | | IV-1 | 4930506M07Rik | 1.30 |
| 9281 | 3 | 4 | | | IV-1 | 1810026J23Rik | 1.14 | 9377 | 3 | 4 | | IV-1 | 4930513N10Rik | 1.43 |
| 9282 | 3 | 4 | | | IV-1 | 1810030O07Rik | 1.03 | 9378 | 3 | 4 | | IV-1 | 4930515G01Rik | 1.13 |
| 9283 | 3 | 4 | | | IV-1 | 1810032O08Rik | 1.33 | 9379 | 3 | 4 | | IV-1 | 4930526I15Rik | 1.34 |
| 9284 | 3 | 4 | | | IV-1 | 1810043G02Rik | 1.44 | 9380 | 3 | 4 | | IV-1 | 4930539J05Rik | 1.35 |
| 9285 | 3 | 4 | | | IV-1 | 2010012O05Rik | 1.09 | 9381 | 3 | 4 | | IV-1 | 4930562F07Rik | 1.37 |
| 9286 | 3 | 4 | | | IV-1 | 2010015L04Rik | 1.05 | 9382 | 3 | 4 | | IV-1 | 4930563E22Rik | 1.20 |
| 9287 | 3 | 4 | | | IV-1 | 2010107G23Rik | 1.43 | 9383 | 3 | 4 | | IV-1 | 4930577N17Rik | 1.12 |
| 9288 | 3 | 4 | | | IV-1 | 2010111I01Rik | 1.23 | 9384 | 3 | 4 | | IV-1 | 4930578C19Rik | 1.10 |
| 9289 | 3 | 4 | | | IV-1 | 2010204K13Rik | 1.10 | 9385 | 3 | 4 | | IV-1 | 4930581F22Rik | 1.04 |
| 9290 | 3 | 4 | | | IV-1 | 2010315B03Rik | 1.06 | 9386 | 3 | 4 | | IV-1 | 4931403E22Rik | 1.27 |
| 9291 | 3 | 4 | | | IV-1 | 2010320M18Rik | 1.21 | 9387 | 3 | 4 | | IV-1 | 4931406C07Rik | 1.11 |
| 9292 | 3 | 4 | | | IV-1 | 2200002D01Rik | 1.16 | 9388 | 3 | 4 | | IV-1 | 4931406P16Rik | 1.12 |
| 9293 | 3 | 4 | | | IV-1 | 2210013O21Rik | 1.05 | 9389 | 3 | 4 | | IV-1 | 4932416H05Rik | 1.34 |
| 9294 | 3 | 4 | | | IV-1 | 2210015D19Rik | 1.32 | 9390 | 3 | 4 | | IV-1 | 4932418E24Rik | 1.11 |
| 9295 | 3 | 4 | | | IV-1 | 2210016L21Rik | 1.10 | 9391 | 3 | 4 | | IV-1 | 4932438A13Rik | 1.05 |
| 9296 | 3 | 4 | | | IV-1 | 2210039B01Rik | 1.10 | 9392 | 3 | 4 | | IV-1 | 4933403O08Rik | 1.10 |
| 9297 | 3 | 4 | | | IV-1 | 2210404O09Rik | 1.19 | 9393 | 3 | 4 | | IV-1 | 4933406C10Rik | 1.16 |
| 9298 | 3 | 4 | | | IV-1 | 2210408I21Rik | 1.41 | 9394 | 3 | 4 | | IV-1 | 4933407K13Rik | 1.08 |
| 9299 | 3 | 4 | | | IV-1 | 2300002M23Rik | 1.15 | 9395 | 3 | 4 | | IV-1 | 4933407L21Rik | 1.09 |
| 9300 | 3 | 4 | | | IV-1 | 2300009A05Rik | 1.35 | 9396 | 3 | 4 | | IV-1 | 4933408B17Rik | 1.30 |
| 9301 | 3 | 4 | | | IV-1 | 2310003H01Rik | 1.12 | 9397 | 3 | 4 | | IV-1 | 4933409K07Rik | 1.48 |
| 9302 | 3 | 4 | | | IV-1 | 2310009B15Rik | 1.01 | 9398 | 3 | 4 | | IV-1 | 4933426M11Rik | 1.11 |
| 9303 | 3 | 4 | | | IV-1 | 2310022B05Rik | 1.08 | 9399 | 3 | 4 | | IV-1 | 4933427D14Rik | 1.15 |
| 9304 | 3 | 4 | | | IV-1 | 2310035C23Rik | 1.27 | 9400 | 3 | 4 | | IV-1 | 4933428G20Rik | 1.47 |
| 9305 | 3 | 4 | | | IV-1 | 2310039H08Rik | 1.45 | 9401 | 3 | 4 | | IV-1 | 4933431E20Rik | 1.10 |
| 9306 | 3 | 4 | | | IV-1 | 2310043L19Rik | 1.27 | 9402 | 3 | 4 | | IV-1 | 5031425E22Rik | 1.37 |
| 9307 | 3 | 4 | | | IV-1 | 2310061I03Rik | 1.45 | 9403 | 3 | 4 | | IV-1 | 5033406O09Rik | 1.04 |
| 9308 | 3 | 4 | | | IV-1 | 2310067B10Rik | 1.03 | 9404 | 3 | 4 | | IV-1 | 5730409E04Rik | 1.37 |
| 9309 | 3 | 4 | | | IV-1 | 2410002F23Rik | 1.45 | 9405 | 3 | 4 | | IV-1 | 5730416F02Rik | 1.18 |

Fig. 45 - 50

| | | | | | | | |
|---|---|---|---|---|---|---|---|
| 9406 | 3 | 4 | | | IV-1 | 5830418K08Rik | 1.14 |
| 9407 | 3 | 4 | | | IV-1 | 5830454E08Rik | 1.02 |
| 9408 | 3 | 4 | | | IV-1 | 5930430L01Rik | 1.15 |
| 9409 | 3 | 4 | | | IV-1 | 6030408B16Rik | 1.15 |
| 9410 | 3 | 4 | | | IV-1 | 6030419C18Rik | 1.47 |
| 9411 | 3 | 4 | | | IV-1 | 6230400D17Rik | 1.01 |
| 9412 | 3 | 4 | | | IV-1 | 6330403A02Rik | 1.46 |
| 9413 | 3 | 4 | | | IV-1 | 6330403K07Rik | 1.41 |
| 9414 | 3 | 4 | | | IV-1 | 6330408A02Rik | 1.07 |
| 9415 | 3 | 4 | | | IV-1 | 6330409D20Rik | 1.33 |
| 9416 | 3 | 4 | | | IV-1 | 6330416G13Rik | 1.44 |
| 9417 | 3 | 4 | | | IV-1 | 6330419J24Rik | 1.08 |
| 9418 | 3 | 4 | | | IV-1 | 6430411K18Rik | 1.19 |
| 9419 | 3 | 4 | | | IV-1 | 6530402F18Rik | 1.40 |
| 9420 | 3 | 4 | | | IV-1 | 6820431F20Rik | 1.22 |
| 9421 | 3 | 4 | | | IV-1 | 8430408G22Rik | 1.47 |
| 9422 | 3 | 4 | | | IV-1 | 8430419L09Rik | 1.06 |
| 9423 | 3 | 4 | | | IV-1 | 8430427H17Rik | 1.07 |
| 9424 | 3 | 4 | | | IV-1 | 8430429K09Rik | 1.16 |
| 9425 | 3 | 4 | | | IV-1 | 9030025P20Rik | 1.31 |
| 9426 | 3 | 4 | | | IV-1 | 9030617O03Rik | 1.22 |
| 9427 | 3 | 4 | | | IV-1 | 9030624G23Rik | 1.27 |
| 9428 | 3 | 4 | | | IV-1 | 9130008F23Rik | 1.42 |
| 9429 | 3 | 4 | | | IV-1 | 9130011E15Rik | 1.07 |
| 9430 | 3 | 4 | | | IV-1 | 9130221H12Rik | 1.03 |
| 9431 | 3 | 4 | | | IV-1 | 9230110C19Rik | 1.01 |
| 9432 | 3 | 4 | | | IV-1 | 9230116L04Rik | 1.10 |
| 9433 | 3 | 4 | | | IV-1 | 9230116N13Rik | 1.41 |
| 9434 | 3 | 4 | | | IV-1 | 9330020H09Rik | 1.13 |
| 9435 | 3 | 4 | | | IV-1 | 9330102E08Rik | 1.42 |
| 9436 | 3 | 4 | | | IV-1 | 9330159F19Rik | 1.41 |
| 9437 | 3 | 4 | | | IV-1 | 9330182L06Rik | 1.48 |
| 9438 | 3 | 4 | | | IV-1 | 9430016H08Rik | 1.23 |
| 9439 | 3 | 4 | | | IV-1 | 9430038I01Rik | 1.17 |
| 9440 | 3 | 4 | | | IV-1 | 9430091E24Rik | 1.32 |
| 9441 | 3 | 4 | | | IV-1 | 9530027J09Rik | 1.23 |
| 9442 | 3 | 4 | | | IV-1 | 9530068E07Rik | 1.02 |
| 9443 | 3 | 4 | | | IV-1 | 9530082P21Rik | 1.48 |
| 9444 | 3 | 4 | | | IV-1 | 9630033F20Rik | 1.05 |
| 9445 | 3 | 4 | | | IV-1 | 9930021J03Rik | 1.25 |
| 9446 | 3 | 4 | | | IV-1 | 9930104L06Rik | 1.20 |
| 9447 | 3 | 4 | | | IV-1 | A130010J15Rik | 1.20 |
| 9448 | 3 | 4 | | | IV-1 | A230046K03Rik | 1.07 |
| 9449 | 3 | 4 | | | IV-1 | A230050P20Rik | 1.05 |
| 9450 | 3 | 4 | | | IV-1 | A230070E04Rik | 1.26 |
| 9451 | 3 | 4 | | | IV-1 | A230077H06Rik | 1.47 |
| 9452 | 3 | 4 | | | IV-1 | A230103J11Rik | 1.27 |
| 9453 | 3 | 4 | | | IV-1 | A330021E22Rik | 1.37 |
| 9454 | 3 | 4 | | | IV-1 | A330023F24Rik | 1.04 |
| 9455 | 3 | 4 | | | IV-1 | A330035P11Rik | 1.25 |
| 9456 | 3 | 4 | | | IV-1 | A330069E16Rik | 1.23 |
| 9457 | 3 | 4 | | | IV-1 | A330076H08Rik | 1.19 |
| 9458 | 3 | 4 | | | IV-1 | A3galt2 | 1.17 |
| 9459 | 3 | 4 | | | IV-1 | A430035B10Rik | 1.09 |
| 9460 | 3 | 4 | | | IV-1 | A430105J19Rik | 1.14 |
| 9461 | 3 | 4 | | | IV-1 | A4galt | 1.35 |
| 9462 | 3 | 4 | | | IV-1 | A530058N18Rik | 1.12 |
| 9463 | 3 | 4 | | | IV-1 | A630001G21Rik | 1.11 |
| 9464 | 3 | 4 | | | IV-1 | A630007B06Rik | 1.01 |
| 9465 | 3 | 4 | | | IV-1 | A630033H20Rik | 1.34 |
| 9466 | 3 | 4 | | | IV-1 | A630072M18Rik | 1.11 |
| 9467 | 3 | 4 | | | IV-1 | A730017C20Rik | 1.50 |
| 9468 | 3 | 4 | | | IV-1 | A730046J19Rik | 1.16 |
| 9469 | 3 | 4 | | | IV-1 | A730056A06Rik | 1.19 |
| 9470 | 3 | 4 | | | IV-1 | A830010M20Rik | 1.35 |
| 9471 | 3 | 4 | | | IV-1 | A830018L16Rik | 1.38 |
| 9472 | 3 | 4 | | | IV-1 | A830052D11Rik | 1.27 |
| 9473 | 3 | 4 | | | IV-1 | A830080D01Rik | 1.07 |
| 9474 | 3 | 4 | | | IV-1 | A830082K12Rik | 1.45 |
| 9475 | 3 | 4 | | | IV-1 | A930005H10Rik | 1.40 |
| 9476 | 3 | 4 | | | IV-1 | A930006K02Rik | 1.08 |
| 9477 | 3 | 4 | | | IV-1 | A930011O12Rik | 1.50 |
| 9478 | 3 | 4 | | | IV-1 | A930013F10Rik | 1.49 |
| 9479 | 3 | 4 | | | IV-1 | A930017M01Rik | 1.11 |
| 9480 | 3 | 4 | | | IV-1 | AA414768 | 1.00 |
| 9481 | 3 | 4 | | | IV-1 | AB124611 | 1.25 |
| 9482 | 3 | 4 | | | IV-1 | AI314180 | 1.04 |
| 9483 | 3 | 4 | | | IV-1 | AI413582 | 1.30 |
| 9484 | 3 | 4 | | | IV-1 | AI414108 | 1.05 |
| 9485 | 3 | 4 | | | IV-1 | AI504432 | 1.35 |
| 9486 | 3 | 4 | | | IV-1 | AI506816 | 1.01 |
| 9487 | 3 | 4 | | | IV-1 | AI593442 | 1.31 |
| 9488 | 3 | 4 | | | IV-1 | AI606473 | 1.44 |
| 9489 | 3 | 4 | | | IV-1 | AI837181 | 1.18 |
| 9490 | 3 | 4 | | | IV-1 | AI846148 | 1.21 |
| 9491 | 3 | 4 | | | IV-1 | AI848285 | 1.27 |
| 9492 | 3 | 4 | | | IV-1 | AI854703 | 1.13 |
| 9493 | 3 | 4 | | | IV-1 | AK129341 | 1.27 |
| 9494 | 3 | 4 | | | IV-1 | AU019823 | 1.08 |
| 9495 | 3 | 4 | | | IV-1 | AU040320 | 1.02 |
| 9496 | 3 | 4 | | | IV-1 | AU041133 | 1.11 |
| 9497 | 3 | 4 | | | IV-1 | AW011738 | 1.35 |
| 9498 | 3 | 4 | | | IV-1 | AW112010 | 1.14 |
| 9499 | 3 | 4 | | | IV-1 | AW549877 | 1.01 |
| 9500 | 3 | 4 | | | IV-1 | AW554918 | 1.30 |
| 9501 | 3 | 4 | | | IV-1 | Aadacl2 | 1.20 |
| 9502 | 3 | 4 | | | IV-1 | Aak1 | 1.08 |
| 9503 | 3 | 4 | | | IV-1 | Aamp | 1.01 |
| 9504 | 3 | 4 | | | IV-1 | Aars | 1.16 |
| 9505 | 3 | 4 | | | IV-1 | Aarsd1 | 1.14 |
| 9506 | 3 | 4 | | | IV-1 | Aatf | 1.16 |
| 9507 | 3 | 4 | | | IV-1 | Aatk | 1.43 |
| 9508 | 3 | 4 | | | IV-1 | Abca2 | 1.42 |
| 9509 | 3 | 4 | | | IV-1 | Abcb1a | 1.45 |
| 9510 | 3 | 4 | | | IV-1 | Abcb6 | 1.03 |
| 9511 | 3 | 4 | | | IV-1 | Abcb9 | 1.17 |
| 9512 | 3 | 4 | | | IV-1 | Abcc1 | 1.14 |
| 9513 | 3 | 4 | | | IV-1 | Abcc10 | 1.36 |
| 9514 | 3 | 4 | | | IV-1 | Abcc3 | 1.23 |
| 9515 | 3 | 4 | | | IV-1 | Abcc4 | 1.04 |
| 9516 | 3 | 4 | | | IV-1 | Abcc9 | 1.12 |
| 9517 | 3 | 4 | | | IV-1 | Abcd2 | 1.25 |
| 9518 | 3 | 4 | | | IV-1 | Abcd3 | 1.09 |
| 9519 | 3 | 4 | | | IV-1 | Abcd4 | 1.14 |
| 9520 | 3 | 4 | | | IV-1 | Abcg1 | 1.10 |
| 9521 | 3 | 4 | | | IV-1 | Abhd10 | 1.04 |
| 9522 | 3 | 4 | | | IV-1 | Abhd11 | 1.20 |
| 9523 | 3 | 4 | | | IV-1 | Abhd12 | 1.05 |
| 9524 | 3 | 4 | | | IV-1 | Abhd14a | 1.11 |
| 9525 | 3 | 4 | | | IV-1 | Abhd17b | 1.09 |
| 9526 | 3 | 4 | | | IV-1 | Abhd4 | 1.19 |
| 9527 | 3 | 4 | | | IV-1 | Abi1 | 1.02 |
| 9528 | 3 | 4 | | | IV-1 | Abi2 | 1.28 |
| 9529 | 3 | 4 | | | IV-1 | Abi3bp | 1.01 |
| 9530 | 3 | 4 | | | IV-1 | Abl1 | 1.02 |
| 9531 | 3 | 4 | | | IV-1 | Abl2 | 1.16 |
| 9532 | 3 | 4 | | | IV-1 | Abr | 1.23 |
| 9533 | 3 | 4 | | | IV-1 | Acad10 | 1.14 |
| 9534 | 3 | 4 | | | IV-1 | Acan | 1.27 |
| 9535 | 3 | 4 | | | IV-1 | Acap2 | 1.03 |
| 9536 | 3 | 4 | | | IV-1 | Acap3 | 1.16 |
| 9537 | 3 | 4 | | | IV-1 | Acbd5 | 1.06 |
| 9538 | 3 | 4 | | | IV-1 | Acd | 1.08 |
| 9539 | 3 | 4 | | | IV-1 | Acer2 | 1.10 |
| 9540 | 3 | 4 | | | IV-1 | Ache | 1.15 |
| 9541 | 3 | 4 | | | IV-1 | Ackr1 | 1.20 |
| 9542 | 3 | 4 | | | IV-1 | Ackr3 | 1.12 |
| 9543 | 3 | 4 | | | IV-1 | Acn9 | 1.05 |
| 9544 | 3 | 4 | | | IV-1 | Acot1 | 1.44 |
| 9545 | 3 | 4 | | | IV-1 | Acot12 | 1.29 |
| 9546 | 3 | 4 | | | IV-1 | Acot2 | 1.30 |
| 9547 | 3 | 4 | | | IV-1 | Acot6 | 1.49 |
| 9548 | 3 | 4 | | | IV-1 | Acot7 | 1.08 |
| 9549 | 3 | 4 | | | IV-1 | Acox3 | 1.25 |
| 9550 | 3 | 4 | | | IV-1 | Acp2 | 1.28 |
| 9551 | 3 | 4 | | | IV-1 | Acsf2 | 1.02 |
| 9552 | 3 | 4 | | | IV-1 | Acsm3 | 1.01 |
| 9553 | 3 | 4 | | | IV-1 | Acss3 | 1.16 |
| 9554 | 3 | 4 | | | IV-1 | Actr10 | 1.19 |
| 9555 | 3 | 4 | | | IV-1 | Actr1a | 1.06 |
| 9556 | 3 | 4 | | | IV-1 | Actr1b | 1.09 |
| 9557 | 3 | 4 | | | IV-1 | Actr3b | 1.20 |
| 9558 | 3 | 4 | | | IV-1 | Actr5 | 1.17 |
| 9559 | 3 | 4 | | | IV-1 | Actr8 | 1.07 |
| 9560 | 3 | 4 | | | IV-1 | Acvr1 | 1.09 |
| 9561 | 3 | 4 | | | IV-1 | Acvr1b | 1.16 |
| 9562 | 3 | 4 | | | IV-1 | Acvr2a | 1.21 |
| 9563 | 3 | 4 | | | IV-1 | Acvr2b | 1.26 |
| 9564 | 3 | 4 | | | IV-1 | Acy3 | 1.33 |
| 9565 | 3 | 4 | | | IV-1 | Ada1 | 1.19 |
| 9566 | 3 | 4 | | | IV-1 | Adam11 | 1.05 |
| 9567 | 3 | 4 | | | IV-1 | Adam1a | 1.37 |
| 9568 | 3 | 4 | | | IV-1 | Adam33 | 1.27 |
| 9569 | 3 | 4 | | | IV-1 | Adam8 | 1.32 |
| 9570 | 3 | 4 | | | IV-1 | Adamdec1 | 1.06 |
| 9571 | 3 | 4 | | | IV-1 | Adamts1 | 1.13 |
| 9572 | 3 | 4 | | | IV-1 | Adamts16 | 1.29 |
| 9573 | 3 | 4 | | | IV-1 | Adamts17 | 1.13 |
| 9574 | 3 | 4 | | | IV-1 | Adamts18 | 1.15 |
| 9575 | 3 | 4 | | | IV-1 | Adamts2 | 1.30 |
| 9576 | 3 | 4 | | | IV-1 | Adamts20 | 1.15 |
| 9577 | 3 | 4 | | | IV-1 | Adamts3 | 1.49 |
| 9578 | 3 | 4 | | | IV-1 | Adamts5 | 1.13 |
| 9579 | 3 | 4 | | | IV-1 | Adamts6 | 1.45 |
| 9580 | 3 | 4 | | | IV-1 | Adamts7 | 1.05 |
| 9581 | 3 | 4 | | | IV-1 | Adamts9 | 1.13 |
| 9582 | 3 | 4 | | | IV-1 | Adamtsl1 | 1.06 |
| 9583 | 3 | 4 | | | IV-1 | Adamtsl2 | 1.31 |
| 9584 | 3 | 4 | | | IV-1 | Adamtsl3 | 1.18 |
| 9585 | 3 | 4 | | | IV-1 | Adamtsl5 | 1.07 |
| 9586 | 3 | 4 | | | IV-1 | Adap1 | 1.11 |
| 9587 | 3 | 4 | | | IV-1 | Adap2 | 1.32 |
| 9588 | 3 | 4 | | | IV-1 | Adar | 1.47 |
| 9589 | 3 | 4 | | | IV-1 | Adarb1 | 1.18 |
| 9590 | 3 | 4 | | | IV-1 | Adat2 | 1.23 |
| 9591 | 3 | 4 | | | IV-1 | Adck1 | 1.15 |
| 9592 | 3 | 4 | | | IV-1 | Adck2 | 1.27 |
| 9593 | 3 | 4 | | | IV-1 | Adck5 | 1.18 |
| 9594 | 3 | 4 | | | IV-1 | Adcy1 | 1.40 |
| 9595 | 3 | 4 | | | IV-1 | Adcy2 | 1.01 |
| 9596 | 3 | 4 | | | IV-1 | Adcy5 | 1.14 |
| 9597 | 3 | 4 | | | IV-1 | Adcy8 | 1.19 |

Fig. 45 - 51

| | | | | | | | | | | | | | | |
|---|---|---|---|---|---|---|---|---|---|---|---|---|---|---|
| 9598 | 3 | 4 | | | IV-1 | Adcy9 | 1.05 | 9694 | 3 | 4 | | | IV-1 | Amz2 | 1.17 |
| 9599 | 3 | 4 | | | IV-1 | Adcyap1r1 | 1.46 | 9695 | 3 | 4 | | | IV-1 | Anapc16 | 1.19 |
| 9600 | 3 | 4 | | | IV-1 | Adh7 | 1.17 | 9696 | 3 | 4 | | | IV-1 | Anapc4 | 1.11 |
| 9601 | 3 | 4 | | | IV-1 | Adm2 | 1.38 | 9697 | 3 | 4 | | | IV-1 | Anapc7 | 1.09 |
| 9602 | 3 | 4 | | | IV-1 | Adnp | 1.19 | 9698 | 3 | 4 | | | IV-1 | Ang | 1.43 |
| 9603 | 3 | 4 | | | IV-1 | Adnp2 | 1.15 | 9699 | 3 | 4 | | | IV-1 | Angel2 | 1.24 |
| 9604 | 3 | 4 | | | IV-1 | Adora1 | 1.35 | 9700 | 3 | 4 | | | IV-1 | Angpt1 | 1.04 |
| 9605 | 3 | 4 | | | IV-1 | Adra1a | 1.04 | 9701 | 3 | 4 | | | IV-1 | Angpt2 | 1.13 |
| 9606 | 3 | 4 | | | IV-1 | Adra2a | 1.16 | 9702 | 3 | 4 | | | IV-1 | Ank2 | 1.24 |
| 9607 | 3 | 4 | | | IV-1 | Adrb2 | 1.11 | 9703 | 3 | 4 | | | IV-1 | Ank3 | 1.29 |
| 9608 | 3 | 4 | | | IV-1 | Adrbk2 | 1.14 | 9704 | 3 | 4 | | | IV-1 | Ankib1 | 1.16 |
| 9609 | 3 | 4 | | | IV-1 | Adss | 1.13 | 9705 | 3 | 4 | | | IV-1 | Ankle2 | 1.18 |
| 9610 | 3 | 4 | | | IV-1 | Aebp2 | 1.03 | 9706 | 3 | 4 | | | IV-1 | Ankmy2 | 1.06 |
| 9611 | 3 | 4 | | | IV-1 | Aen | 1.31 | 9707 | 3 | 4 | | | IV-1 | Ankrd1 | 1.18 |
| 9612 | 3 | 4 | | | IV-1 | Afap1 | 1.21 | 9708 | 3 | 4 | | | IV-1 | Ankrd10 | 1.12 |
| 9613 | 3 | 4 | | | IV-1 | Aff3 | 1.41 | 9709 | 3 | 4 | | | IV-1 | Ankrd11 | 1.20 |
| 9614 | 3 | 4 | | | IV-1 | Aff4 | 1.19 | 9710 | 3 | 4 | | | IV-1 | Ankrd12 | 1.19 |
| 9615 | 3 | 4 | | | IV-1 | Afg3l1 | 1.03 | 9711 | 3 | 4 | | | IV-1 | Ankrd13d | 1.47 |
| 9616 | 3 | 4 | | | IV-1 | Afmid | 1.14 | 9712 | 3 | 4 | | | IV-1 | Ankrd17 | 1.01 |
| 9617 | 3 | 4 | | | IV-1 | Agap1 | 1.36 | 9713 | 3 | 4 | | | IV-1 | Ankrd24 | 1.17 |
| 9618 | 3 | 4 | | | IV-1 | Agap3 | 1.46 | 9714 | 3 | 4 | | | IV-1 | Ankrd26 | 1.06 |
| 9619 | 3 | 4 | | | IV-1 | Agbl5 | 1.25 | 9715 | 3 | 4 | | | IV-1 | Ankrd28 | 1.37 |
| 9620 | 3 | 4 | | | IV-1 | Ager | 1.08 | 9716 | 3 | 4 | | | IV-1 | Ankrd32 | 1.27 |
| 9621 | 3 | 4 | | | IV-1 | Agk | 1.13 | 9717 | 3 | 4 | | | IV-1 | Ankrd39 | 1.25 |
| 9622 | 3 | 4 | | | IV-1 | Agmo | 1.05 | 9718 | 3 | 4 | | | IV-1 | Ankrd42 | 1.11 |
| 9623 | 3 | 4 | | | IV-1 | Ago1 | 1.19 | 9719 | 3 | 4 | | | IV-1 | Ankrd44 | 1.13 |
| 9624 | 3 | 4 | | | IV-1 | Ago4 | 1.13 | 9720 | 3 | 4 | | | IV-1 | Ankrd46 | 1.07 |
| 9625 | 3 | 4 | | | IV-1 | Agpat6 | 1.03 | 9721 | 3 | 4 | | | IV-1 | Ankrd50 | 1.11 |
| 9626 | 3 | 4 | | | IV-1 | Agrn | 1.24 | 9722 | 3 | 4 | | | IV-1 | Ankrd52 | 1.01 |
| 9627 | 3 | 4 | | | IV-1 | Agtpbp1 | 1.11 | 9723 | 3 | 4 | | | IV-1 | Ankrd55 | 1.44 |
| 9628 | 3 | 4 | | | IV-1 | Agtr2 | 1.12 | 9724 | 3 | 4 | | | IV-1 | Ankrd6 | 1.17 |
| 9629 | 3 | 4 | | | IV-1 | Ahcy | 1.07 | 9725 | 3 | 4 | | | IV-1 | Anks6 | 1.41 |
| 9630 | 3 | 4 | | | IV-1 | Ahcyl1 | 1.09 | 9726 | 3 | 4 | | | IV-1 | Ankzf1 | 1.12 |
| 9631 | 3 | 4 | | | IV-1 | Ahdc1 | 1.05 | 9727 | 3 | 4 | | | IV-1 | Ano10 | 1.05 |
| 9632 | 3 | 4 | | | IV-1 | Ahrr | 1.13 | 9728 | 3 | 4 | | | IV-1 | Ano8 | 1.31 |
| 9633 | 3 | 4 | | | IV-1 | Ahsa2 | 1.17 | 9729 | 3 | 4 | | | IV-1 | Anxa1 | 1.22 |
| 9634 | 3 | 4 | | | IV-1 | Aif1 | 1.01 | 9730 | 3 | 4 | | | IV-1 | Anxa11 | 1.01 |
| 9635 | 3 | 4 | | | IV-1 | Aif1l | 1.16 | 9731 | 3 | 4 | | | IV-1 | Anxa3 | 1.14 |
| 9636 | 3 | 4 | | | IV-1 | Aifm3 | 1.04 | 9732 | 3 | 4 | | | IV-1 | Anxa8 | 1.20 |
| 9637 | 3 | 4 | | | IV-1 | Aim2 | 1.09 | 9733 | 3 | 4 | | | IV-1 | Aoah | 1.02 |
| 9638 | 3 | 4 | | | IV-1 | Aimp1 | 1.09 | 9734 | 3 | 4 | | | IV-1 | Aoc2 | 1.14 |
| 9639 | 3 | 4 | | | IV-1 | Airn | 1.04 | 9735 | 3 | 4 | | | IV-1 | Ap1ar | 1.12 |
| 9640 | 3 | 4 | | | IV-1 | Ajuba | 1.05 | 9736 | 3 | 4 | | | IV-1 | Ap1m1 | 1.11 |
| 9641 | 3 | 4 | | | IV-1 | Ak5 | 1.37 | 9737 | 3 | 4 | | | IV-1 | Ap1s2 | 1.15 |
| 9642 | 3 | 4 | | | IV-1 | Akap11 | 1.27 | 9738 | 3 | 4 | | | IV-1 | Ap2a1 | 1.00 |
| 9643 | 3 | 4 | | | IV-1 | Akap12 | 1.08 | 9739 | 3 | 4 | | | IV-1 | Ap3b2 | 1.24 |
| 9644 | 3 | 4 | | | IV-1 | Akap13 | 1.06 | 9740 | 3 | 4 | | | IV-1 | Ap3d1 | 1.01 |
| 9645 | 3 | 4 | | | IV-1 | Akap17b | 1.24 | 9741 | 3 | 4 | | | IV-1 | Ap3m2 | 1.33 |
| 9646 | 3 | 4 | | | IV-1 | Akap6 | 1.20 | 9742 | 3 | 4 | | | IV-1 | Ap3s2 | 1.34 |
| 9647 | 3 | 4 | | | IV-1 | Akap7 | 1.05 | 9743 | 3 | 4 | | | IV-1 | Ap4b1 | 1.25 |
| 9648 | 3 | 4 | | | IV-1 | Akap8 | 1.11 | 9744 | 3 | 4 | | | IV-1 | Ap4e1 | 1.13 |
| 9649 | 3 | 4 | | | IV-1 | Akap8l | 1.08 | 9745 | 3 | 4 | | | IV-1 | Ap4m1 | 1.09 |
| 9650 | 3 | 4 | | | IV-1 | Akap9 | 1.24 | 9746 | 3 | 4 | | | IV-1 | Apaf1 | 1.04 |
| 9651 | 3 | 4 | | | IV-1 | Akirin1 | 1.04 | 9747 | 3 | 4 | | | IV-1 | Apba1 | 1.35 |
| 9652 | 3 | 4 | | | IV-1 | Akna | 1.08 | 9748 | 3 | 4 | | | IV-1 | Apbb1 | 1.43 |
| 9653 | 3 | 4 | | | IV-1 | Akt1 | 1.10 | 9749 | 3 | 4 | | | IV-1 | Apbb2 | 1.42 |
| 9654 | 3 | 4 | | | IV-1 | Akt1s1 | 1.01 | 9750 | 3 | 4 | | | IV-1 | Apc | 1.37 |
| 9655 | 3 | 4 | | | IV-1 | Akt3 | 1.39 | 9751 | 3 | 4 | | | IV-1 | Apcdd1 | 1.18 |
| 9656 | 3 | 4 | | | IV-1 | Alcam | 1.29 | 9752 | 3 | 4 | | | IV-1 | Apcs | 1.41 |
| 9657 | 3 | 4 | | | IV-1 | Aldh1a1 | 1.09 | 9753 | 3 | 4 | | | IV-1 | Aph1a | 1.06 |
| 9658 | 3 | 4 | | | IV-1 | Aldh1a2 | 1.24 | 9754 | 3 | 4 | | | IV-1 | Aph1b | 1.27 |
| 9659 | 3 | 4 | | | IV-1 | Aldh1a3 | 1.05 | 9755 | 3 | 4 | | | IV-1 | Aph1c | 1.19 |
| 9660 | 3 | 4 | | | IV-1 | Aldh1l2 | 1.22 | 9756 | 3 | 4 | | | IV-1 | Apobec1 | 1.39 |
| 9661 | 3 | 4 | | | IV-1 | Aldh6a1 | 1.07 | 9757 | 3 | 4 | | | IV-1 | Apobr | 1.22 |
| 9662 | 3 | 4 | | | IV-1 | Aldoc | 1.07 | 9758 | 3 | 4 | | | IV-1 | Apoc2 | 1.07 |
| 9663 | 3 | 4 | | | IV-1 | Alg10b | 1.11 | 9759 | 3 | 4 | | | IV-1 | Apoe | 1.06 |
| 9664 | 3 | 4 | | | IV-1 | Alg11 | 1.09 | 9760 | 3 | 4 | | | IV-1 | Apon | 1.17 |
| 9665 | 3 | 4 | | | IV-1 | Alg2 | 1.33 | 9761 | 3 | 4 | | | IV-1 | App | 1.29 |
| 9666 | 3 | 4 | | | IV-1 | Alg5 | 1.06 | 9762 | 3 | 4 | | | IV-1 | Appbp2 | 1.07 |
| 9667 | 3 | 4 | | | IV-1 | Alkbh1 | 1.25 | 9763 | 3 | 4 | | | IV-1 | Appl1 | 1.18 |
| 9668 | 3 | 4 | | | IV-1 | Alkbh3 | 1.37 | 9764 | 3 | 4 | | | IV-1 | Appl2 | 1.09 |
| 9669 | 3 | 4 | | | IV-1 | Alkbh6 | 1.18 | 9765 | 3 | 4 | | | IV-1 | Aptx | 1.02 |
| 9670 | 3 | 4 | | | IV-1 | Alkbh8 | 1.20 | 9766 | 3 | 4 | | | IV-1 | Aqp3 | 1.09 |
| 9671 | 3 | 4 | | | IV-1 | Alox5 | 1.08 | 9767 | 3 | 4 | | | IV-1 | Aqp9 | 1.32 |
| 9672 | 3 | 4 | | | IV-1 | Alox5ap | 1.09 | 9768 | 3 | 4 | | | IV-1 | Aqr | 1.06 |
| 9673 | 3 | 4 | | | IV-1 | Alpk1 | 1.02 | 9769 | 3 | 4 | | | IV-1 | Araf | 1.19 |
| 9674 | 3 | 4 | | | IV-1 | Alpk2 | 1.09 | 9770 | 3 | 4 | | | IV-1 | Arap1 | 1.08 |
| 9675 | 3 | 4 | | | IV-1 | Als2cl | 1.43 | 9771 | 3 | 4 | | | IV-1 | Arap2 | 1.10 |
| 9676 | 3 | 4 | | | IV-1 | Alx1 | 1.28 | 9772 | 3 | 4 | | | IV-1 | Arc | 1.03 |
| 9677 | 3 | 4 | | | IV-1 | Alx3 | 1.31 | 9773 | 3 | 4 | | | IV-1 | Arel1 | 1.15 |
| 9678 | 3 | 4 | | | IV-1 | Alx4 | 1.20 | 9774 | 3 | 4 | | | IV-1 | Arf3 | 1.05 |
| 9679 | 3 | 4 | | | IV-1 | Ambra1 | 1.22 | 9775 | 3 | 4 | | | IV-1 | Arfgap1 | 1.13 |
| 9680 | 3 | 4 | | | IV-1 | Amd1 | 1.01 | 9776 | 3 | 4 | | | IV-1 | Arfgef1 | 1.06 |
| 9681 | 3 | 4 | | | IV-1 | Amdhd1 | 1.29 | 9777 | 3 | 4 | | | IV-1 | Arfip2 | 1.20 |
| 9682 | 3 | 4 | | | IV-1 | Amer1 | 1.10 | 9778 | 3 | 4 | | | IV-1 | Arg2 | 1.24 |
| 9683 | 3 | 4 | | | IV-1 | Amer2 | 1.47 | 9779 | 3 | 4 | | | IV-1 | Arglu1 | 1.28 |
| 9684 | 3 | 4 | | | IV-1 | Amer3 | 1.43 | 9780 | 3 | 4 | | | IV-1 | Arhgap1 | 1.03 |
| 9685 | 3 | 4 | | | IV-1 | Amfr | 1.07 | 9781 | 3 | 4 | | | IV-1 | Arhgap10 | 1.05 |
| 9686 | 3 | 4 | | | IV-1 | Amh | 1.03 | 9782 | 3 | 4 | | | IV-1 | Arhgap12 | 1.03 |
| 9687 | 3 | 4 | | | IV-1 | Amigo1 | 1.13 | 9783 | 3 | 4 | | | IV-1 | Arhgap20 | 1.34 |
| 9688 | 3 | 4 | | | IV-1 | Amigo2 | 1.34 | 9784 | 3 | 4 | | | IV-1 | Arhgap21 | 1.17 |
| 9689 | 3 | 4 | | | IV-1 | Amn1 | 1.25 | 9785 | 3 | 4 | | | IV-1 | Arhgap23 | 1.06 |
| 9690 | 3 | 4 | | | IV-1 | Amot | 1.16 | 9786 | 3 | 4 | | | IV-1 | Arhgap25 | 1.06 |
| 9691 | 3 | 4 | | | IV-1 | Amotl2 | 1.10 | 9787 | 3 | 4 | | | IV-1 | Arhgap28 | 1.09 |
| 9692 | 3 | 4 | | | IV-1 | Amph | 1.41 | 9788 | 3 | 4 | | | IV-1 | Arhgap32 | 1.24 |
| 9693 | 3 | 4 | | | IV-1 | Amy2a5 | 1.33 | 9789 | 3 | 4 | | | IV-1 | Arhgap33 | 1.45 |

Fig. 45 - 52

| | | | | | | | | | | | | | | |
|---|---|---|---|---|---|---|---|---|---|---|---|---|---|---|
| 9790 | 3 | 4 | | | IV-1 | Arhgap35 | 1.14 | 9886 | 3 | 4 | | | IV-1 | Atf5 | 1.29 |
| 9791 | 3 | 4 | | | IV-1 | Arhgap39 | 1.05 | 9887 | 3 | 4 | | | IV-1 | Atf6 | 1.01 |
| 9792 | 3 | 4 | | | IV-1 | Arhgap4 | 1.07 | 9888 | 3 | 4 | | | IV-1 | Atf7 | 1.06 |
| 9793 | 3 | 4 | | | IV-1 | Arhgap40 | 1.03 | 9889 | 3 | 4 | | | IV-1 | Atf7ip | 1.07 |
| 9794 | 3 | 4 | | | IV-1 | Arhgap42 | 1.08 | 9890 | 3 | 4 | | | IV-1 | Atg13 | 1.14 |
| 9795 | 3 | 4 | | | IV-1 | Arhgap44 | 1.08 | 9891 | 3 | 4 | | | IV-1 | Atg14 | 1.02 |
| 9796 | 3 | 4 | | | IV-1 | Arhgap5 | 1.04 | 9892 | 3 | 4 | | | IV-1 | Atg2b | 1.05 |
| 9797 | 3 | 4 | | | IV-1 | Arhgdib | 1.15 | 9893 | 3 | 4 | | | IV-1 | Atg4a | 1.02 |
| 9798 | 3 | 4 | | | IV-1 | Arhgdig | 1.06 | 9894 | 3 | 4 | | | IV-1 | Atg4c | 1.08 |
| 9799 | 3 | 4 | | | IV-1 | Arhgef1 | 1.11 | 9895 | 3 | 4 | | | IV-1 | Atg9a | 1.13 |
| 9800 | 3 | 4 | | | IV-1 | Arhgef10 | 1.04 | 9896 | 3 | 4 | | | IV-1 | Atg9b | 1.36 |
| 9801 | 3 | 4 | | | IV-1 | Arhgef11 | 1.16 | 9897 | 3 | 4 | | | IV-1 | Ati1 | 1.45 |
| 9802 | 3 | 4 | | | IV-1 | Arhgef12 | 1.06 | 9898 | 3 | 4 | | | IV-1 | Atm | 1.06 |
| 9803 | 3 | 4 | | | IV-1 | Arhgef17 | 1.07 | 9899 | 3 | 4 | | | IV-1 | Atmin | 1.13 |
| 9804 | 3 | 4 | | | IV-1 | Arhgef18 | 1.12 | 9900 | 3 | 4 | | | IV-1 | Atn1 | 1.34 |
| 9805 | 3 | 4 | | | IV-1 | Arhgef2 | 1.07 | 9901 | 3 | 4 | | | IV-1 | Atoh7 | 1.18 |
| 9806 | 3 | 4 | | | IV-1 | Arhgef25 | 1.08 | 9902 | 3 | 4 | | | IV-1 | Atp11a | 1.03 |
| 9807 | 3 | 4 | | | IV-1 | Arhgef26 | 1.08 | 9903 | 3 | 4 | | | IV-1 | Atp11b | 1.00 |
| 9808 | 3 | 4 | | | IV-1 | Arhgef28 | 1.19 | 9904 | 3 | 4 | | | IV-1 | Atp11c | 1.12 |
| 9809 | 3 | 4 | | | IV-1 | Arhgef3 | 1.04 | 9905 | 3 | 4 | | | IV-1 | Atp13a2 | 1.29 |
| 9810 | 3 | 4 | | | IV-1 | Arhgef37 | 1.03 | 9906 | 3 | 4 | | | IV-1 | Atp1a2 | 1.18 |
| 9811 | 3 | 4 | | | IV-1 | Arhgef4 | 1.36 | 9907 | 3 | 4 | | | IV-1 | Atp1b1 | 1.13 |
| 9812 | 3 | 4 | | | IV-1 | Arhgef40 | 1.14 | 9908 | 3 | 4 | | | IV-1 | Atp1b2 | 1.04 |
| 9813 | 3 | 4 | | | IV-1 | Arhgef7 | 1.11 | 9909 | 3 | 4 | | | IV-1 | Atp2b1 | 1.16 |
| 9814 | 3 | 4 | | | IV-1 | Arhgef9 | 1.29 | 9910 | 3 | 4 | | | IV-1 | Atp2b2 | 1.33 |
| 9815 | 3 | 4 | | | IV-1 | Arid1a | 1.05 | 9911 | 3 | 4 | | | IV-1 | Atp2c1 | 1.12 |
| 9816 | 3 | 4 | | | IV-1 | Arid1b | 1.09 | 9912 | 3 | 4 | | | IV-1 | Atp6ap2 | 1.06 |
| 9817 | 3 | 4 | | | IV-1 | Arid2 | 1.24 | 9913 | 3 | 4 | | | IV-1 | Atp6v0a1 | 1.06 |
| 9818 | 3 | 4 | | | IV-1 | Arid4a | 1.06 | 9914 | 3 | 4 | | | IV-1 | Atp6v0c | 1.03 |
| 9819 | 3 | 4 | | | IV-1 | Arid4b | 1.23 | 9915 | 3 | 4 | | | IV-1 | Atp6v1b2 | 1.06 |
| 9820 | 3 | 4 | | | IV-1 | Arid5b | 1.04 | 9916 | 3 | 4 | | | IV-1 | Atp6v1h | 1.05 |
| 9821 | 3 | 4 | | | IV-1 | Arih2 | 1.23 | 9917 | 3 | 4 | | | IV-1 | Atp8a2 | 1.32 |
| 9822 | 3 | 4 | | | IV-1 | Arl10 | 1.19 | 9918 | 3 | 4 | | | IV-1 | Atp8b2 | 1.09 |
| 9823 | 3 | 4 | | | IV-1 | Arl11 | 1.34 | 9919 | 3 | 4 | | | IV-1 | Atp8b4 | 1.08 |
| 9824 | 3 | 4 | | | IV-1 | Arl13b | 1.02 | 9920 | 3 | 4 | | | IV-1 | Atp9a | 1.50 |
| 9825 | 3 | 4 | | | IV-1 | Arl14ep | 1.25 | 9921 | 3 | 4 | | | IV-1 | Atp9b | 1.31 |
| 9826 | 3 | 4 | | | IV-1 | Arl16 | 1.09 | 9922 | 3 | 4 | | | IV-1 | Atr | 1.06 |
| 9827 | 3 | 4 | | | IV-1 | Arl2bp | 1.05 | 9923 | 3 | 4 | | | IV-1 | Atraid | 1.26 |
| 9828 | 3 | 4 | | | IV-1 | Arl4a | 1.28 | 9924 | 3 | 4 | | | IV-1 | Atrip | 1.23 |
| 9829 | 3 | 4 | | | IV-1 | Arl4c | 1.04 | 9925 | 3 | 4 | | | IV-1 | Atrn | 1.27 |
| 9830 | 3 | 4 | | | IV-1 | Arl4d | 1.45 | 9926 | 3 | 4 | | | IV-1 | Atrnl1 | 1.11 |
| 9831 | 3 | 4 | | | IV-1 | Arl5c | 1.07 | 9927 | 3 | 4 | | | IV-1 | Atrx | 1.04 |
| 9832 | 3 | 4 | | | IV-1 | Arl6 | 1.10 | 9928 | 3 | 4 | | | IV-1 | Atxn10 | 1.02 |
| 9833 | 3 | 4 | | | IV-1 | Arl6ip4 | 1.04 | 9929 | 3 | 4 | | | IV-1 | Atxn1l | 1.14 |
| 9834 | 3 | 4 | | | IV-1 | Arl8a | 1.41 | 9930 | 3 | 4 | | | IV-1 | Atxn2l | 1.09 |
| 9835 | 3 | 4 | | | IV-1 | Armc10 | 1.20 | 9931 | 3 | 4 | | | IV-1 | Atxn7 | 1.16 |
| 9836 | 3 | 4 | | | IV-1 | Armc5 | 1.11 | 9932 | 3 | 4 | | | IV-1 | Atxn7l2 | 1.26 |
| 9837 | 3 | 4 | | | IV-1 | Armc6 | 1.03 | 9933 | 3 | 4 | | | IV-1 | Atxn7l3 | 1.19 |
| 9838 | 3 | 4 | | | IV-1 | Armc8 | 1.14 | 9934 | 3 | 4 | | | IV-1 | Atxn7l3b | 1.08 |
| 9839 | 3 | 4 | | | IV-1 | Armcx1 | 1.07 | 9935 | 3 | 4 | | | IV-1 | Avl9 | 1.30 |
| 9840 | 3 | 4 | | | IV-1 | Armcx2 | 1.01 | 9936 | 3 | 4 | | | IV-1 | Avpr1a | 1.13 |
| 9841 | 3 | 4 | | | IV-1 | Armcx4 | 1.23 | 9937 | 3 | 4 | | | IV-1 | Axin1 | 1.10 |
| 9842 | 3 | 4 | | | IV-1 | Armcx6 | 1.14 | 9938 | 3 | 4 | | | IV-1 | Axin2 | 1.25 |
| 9843 | 3 | 4 | | | IV-1 | Arnt | 1.05 | 9939 | 3 | 4 | | | IV-1 | Axl | 1.31 |
| 9844 | 3 | 4 | | | IV-1 | Arntl | 1.01 | 9940 | 3 | 4 | | | IV-1 | Azi2 | 1.03 |
| 9845 | 3 | 4 | | | IV-1 | Arntl2 | 1.35 | 9941 | 3 | 4 | | | IV-1 | B130024G19Rik | 1.18 |
| 9846 | 3 | 4 | | | IV-1 | Arpc1a | 1.04 | 9942 | 3 | 4 | | | IV-1 | B130034C11Rik | 1.13 |
| 9847 | 3 | 4 | | | IV-1 | Arpc5 | 1.04 | 9943 | 3 | 4 | | | IV-1 | B230119M05Rik | 1.11 |
| 9848 | 3 | 4 | | | IV-1 | Arpp19 | 1.13 | 9944 | 3 | 4 | | | IV-1 | B230209E15Rik | 1.50 |
| 9849 | 3 | 4 | | | IV-1 | Arpp21 | 1.26 | 9945 | 3 | 4 | | | IV-1 | B230216N24Rik | 1.31 |
| 9850 | 3 | 4 | | | IV-1 | Arrb2 | 1.03 | 9946 | 3 | 4 | | | IV-1 | B230217C12Rik | 1.33 |
| 9851 | 3 | 4 | | | IV-1 | Arrdc1 | 1.01 | 9947 | 3 | 4 | | | IV-1 | B230217O12Rik | 1.35 |
| 9852 | 3 | 4 | | | IV-1 | Arrdc2 | 1.05 | 9948 | 3 | 4 | | | IV-1 | B230219D22Rik | 1.01 |
| 9853 | 3 | 4 | | | IV-1 | Arrdc3 | 1.13 | 9949 | 3 | 4 | | | IV-1 | B330016D10Rik | 1.48 |
| 9854 | 3 | 4 | | | IV-1 | Arrdc4 | 1.24 | 9950 | 3 | 4 | | | IV-1 | B3galnt1 | 1.06 |
| 9855 | 3 | 4 | | | IV-1 | Arsk | 1.01 | 9951 | 3 | 4 | | | IV-1 | B3galt2 | 1.19 |
| 9856 | 3 | 4 | | | IV-1 | Art1 | 1.17 | 9952 | 3 | 4 | | | IV-1 | B3galt5 | 1.38 |
| 9857 | 3 | 4 | | | IV-1 | Art5 | 1.50 | 9953 | 3 | 4 | | | IV-1 | B3gat2 | 1.48 |
| 9858 | 3 | 4 | | | IV-1 | Arvcf | 1.22 | 9954 | 3 | 4 | | | IV-1 | B3gat3 | 1.02 |
| 9859 | 3 | 4 | | | IV-1 | Asap1 | 1.05 | 9955 | 3 | 4 | | | IV-1 | B3gict | 1.29 |
| 9860 | 3 | 4 | | | IV-1 | Asap3 | 1.00 | 9956 | 3 | 4 | | | IV-1 | B3gnt1 | 1.09 |
| 9861 | 3 | 4 | | | IV-1 | Asb10 | 1.01 | 9957 | 3 | 4 | | | IV-1 | B3gnt5 | 1.10 |
| 9862 | 3 | 4 | | | IV-1 | Asb13 | 1.14 | 9958 | 3 | 4 | | | IV-1 | B3gnt9 | 1.01 |
| 9863 | 3 | 4 | | | IV-1 | Asb3 | 1.07 | 9959 | 3 | 4 | | | IV-1 | B3gntl1 | 1.26 |
| 9864 | 3 | 4 | | | IV-1 | Asb7 | 1.11 | 9960 | 3 | 4 | | | IV-1 | B430212C06Rik | 1.02 |
| 9865 | 3 | 4 | | | IV-1 | Asb8 | 1.13 | 9961 | 3 | 4 | | | IV-1 | B4galnt1 | 1.24 |
| 9866 | 3 | 4 | | | IV-1 | Ascc1 | 1.15 | 9962 | 3 | 4 | | | IV-1 | B4galt2 | 1.42 |
| 9867 | 3 | 4 | | | IV-1 | Ascl1 | 1.42 | 9963 | 3 | 4 | | | IV-1 | B4galt5 | 1.08 |
| 9868 | 3 | 4 | | | IV-1 | Ascl2 | 1.03 | 9964 | 3 | 4 | | | IV-1 | B4galt6 | 1.09 |
| 9869 | 3 | 4 | | | IV-1 | Asgr1 | 1.14 | 9965 | 3 | 4 | | | IV-1 | B4galt7 | 1.02 |
| 9870 | 3 | 4 | | | IV-1 | Ash1l | 1.10 | 9966 | 3 | 4 | | | IV-1 | B630005N14Rik | 1.17 |
| 9871 | 3 | 4 | | | IV-1 | Ash2l | 1.11 | 9967 | 3 | 4 | | | IV-1 | B930003M22Rik | 1.10 |
| 9872 | 3 | 4 | | | IV-1 | Aspg | 1.03 | 9968 | 3 | 4 | | | IV-1 | B9d2 | 1.09 |
| 9873 | 3 | 4 | | | IV-1 | Aspn | 1.20 | 9969 | 3 | 4 | | | IV-1 | BC003331 | 1.02 |
| 9874 | 3 | 4 | | | IV-1 | Aspscr1 | 1.08 | 9970 | 3 | 4 | | | IV-1 | BC006965 | 1.47 |
| 9875 | 3 | 4 | | | IV-1 | Asrgl1 | 1.20 | 9971 | 3 | 4 | | | IV-1 | BC018242 | 1.42 |
| 9876 | 3 | 4 | | | IV-1 | Astn2 | 1.06 | 9972 | 3 | 4 | | | IV-1 | BC018507 | 1.29 |
| 9877 | 3 | 4 | | | IV-1 | Asxl1 | 1.17 | 9973 | 3 | 4 | | | IV-1 | BC020402 | 1.34 |
| 9878 | 3 | 4 | | | IV-1 | Atad1 | 1.17 | 9974 | 3 | 4 | | | IV-1 | BC024978 | 1.30 |
| 9879 | 3 | 4 | | | IV-1 | Atad3aos | 1.22 | 9975 | 3 | 4 | | | IV-1 | BC027231 | 1.13 |
| 9880 | 3 | 4 | | | IV-1 | Atat1 | 1.40 | 9976 | 3 | 4 | | | IV-1 | BC029722 | 1.29 |
| 9881 | 3 | 4 | | | IV-1 | Atcay | 1.38 | 9977 | 3 | 4 | | | IV-1 | BC030307 | 1.10 |
| 9882 | 3 | 4 | | | IV-1 | Atcayos | 1.17 | 9978 | 3 | 4 | | | IV-1 | BC030336 | 1.05 |
| 9883 | 3 | 4 | | | IV-1 | Ate1 | 1.11 | 9979 | 3 | 4 | | | IV-1 | BC030500 | 1.22 |
| 9884 | 3 | 4 | | | IV-1 | Atf2 | 1.10 | 9980 | 3 | 4 | | | IV-1 | BC031361 | 1.08 |
| 9885 | 3 | 4 | | | IV-1 | Atf4 | 1.20 | 9981 | 3 | 4 | | | IV-1 | BC037032 | 1.18 |

Fig. 45 - 53

| | | | | | | | | | | | | | |
|---|---|---|---|---|---|---|---|---|---|---|---|---|---|
| 9982 | 3 | 4 | | | IV-1 | BC037034 | 1.09 | 10078 | 3 | 4 | | IV-1 | Bri3 | 1.12 |
| 9983 | 3 | 4 | | | IV-1 | BC051226 | 1.11 | 10079 | 3 | 4 | | IV-1 | Bri3bp | 1.01 |
| 9984 | 3 | 4 | | | IV-1 | BC064078 | 1.12 | 10080 | 3 | 4 | | IV-1 | Brms1 | 1.14 |
| 9985 | 3 | 4 | | | IV-1 | Baalc | 1.28 | 10081 | 3 | 4 | | IV-1 | Brms1l | 1.11 |
| 9986 | 3 | 4 | | | IV-1 | Bace1 | 1.08 | 10082 | 3 | 4 | | IV-1 | Brox | 1.14 |
| 9987 | 3 | 4 | | | IV-1 | Bach1 | 1.28 | 10083 | 3 | 4 | | IV-1 | Brpf1 | 1.13 |
| 9988 | 3 | 4 | | | IV-1 | Bach2 | 1.30 | 10084 | 3 | 4 | | IV-1 | Bsn | 1.49 |
| 9989 | 3 | 4 | | | IV-1 | Bad | 1.01 | 10085 | 3 | 4 | | IV-1 | Bst2 | 1.42 |
| 9990 | 3 | 4 | | | IV-1 | Bag6 | 1.02 | 10086 | 3 | 4 | | IV-1 | Btbd1 | 1.00 |
| 9991 | 3 | 4 | | | IV-1 | Bahcc1 | 1.17 | 10087 | 3 | 4 | | IV-1 | Btbd10 | 1.33 |
| 9992 | 3 | 4 | | | IV-1 | Baiap2 | 1.15 | 10088 | 3 | 4 | | IV-1 | Btbd11 | 1.29 |
| 9993 | 3 | 4 | | | IV-1 | Bambi | 1.02 | 10089 | 3 | 4 | | IV-1 | Btbd19 | 1.28 |
| 9994 | 3 | 4 | | | IV-1 | Bambi-ps1 | 1.07 | 10090 | 3 | 4 | | IV-1 | Btbd3 | 1.03 |
| 9995 | 3 | 4 | | | IV-1 | Bap1 | 1.23 | 10091 | 3 | 4 | | IV-1 | Btbd6 | 1.21 |
| 9996 | 3 | 4 | | | IV-1 | Barx1 | 1.28 | 10092 | 3 | 4 | | IV-1 | Btbd9 | 1.20 |
| 9997 | 3 | 4 | | | IV-1 | Basp1 | 1.42 | 10093 | 3 | 4 | | IV-1 | Btg1 | 1.17 |
| 9998 | 3 | 4 | | | IV-1 | Bax | 1.13 | 10094 | 3 | 4 | | IV-1 | Btrc | 1.20 |
| 9999 | 3 | 4 | | | IV-1 | Baz2b | 1.25 | 10095 | 3 | 4 | | IV-1 | Bzw2 | 1.04 |
| 10000 | 3 | 4 | | | IV-1 | Bbip1 | 1.15 | 10096 | 3 | 4 | | IV-1 | C030023E24Rik | 1.39 |
| 10001 | 3 | 4 | | | IV-1 | Bbs1 | 1.04 | 10097 | 3 | 4 | | IV-1 | C030034I22Rik | 1.42 |
| 10002 | 3 | 4 | | | IV-1 | Bbs12 | 1.04 | 10098 | 3 | 4 | | IV-1 | C030039L03Rik | 1.02 |
| 10003 | 3 | 4 | | | IV-1 | Bbs2 | 1.11 | 10099 | 3 | 4 | | IV-1 | C030046E11Rik | 1.10 |
| 10004 | 3 | 4 | | | IV-1 | Bbs4 | 1.48 | 10100 | 3 | 4 | | IV-1 | C130021I20Rik | 1.15 |
| 10005 | 3 | 4 | | | IV-1 | Bbs9 | 1.04 | 10101 | 3 | 4 | | IV-1 | C130046K22Rik | 1.15 |
| 10006 | 3 | 4 | | | IV-1 | Bcap29 | 1.13 | 10102 | 3 | 4 | | IV-1 | C130050O18Rik | 1.06 |
| 10007 | 3 | 4 | | | IV-1 | Bcar1 | 1.03 | 10103 | 3 | 4 | | IV-1 | C1d | 1.00 |
| 10008 | 3 | 4 | | | IV-1 | Bcas3 | 1.03 | 10104 | 3 | 4 | | IV-1 | C1qa | 1.44 |
| 10009 | 3 | 4 | | | IV-1 | Bcat1 | 1.18 | 10105 | 3 | 4 | | IV-1 | C1qb | 1.34 |
| 10010 | 3 | 4 | | | IV-1 | Bcdin3d | 1.33 | 10106 | 3 | 4 | | IV-1 | C1qc | 1.17 |
| 10011 | 3 | 4 | | | IV-1 | Bckdha | 1.10 | 10107 | 3 | 4 | | IV-1 | C1ql1 | 1.03 |
| 10012 | 3 | 4 | | | IV-1 | Bcl10 | 1.06 | 10108 | 3 | 4 | | IV-1 | C1ql3 | 1.16 |
| 10013 | 3 | 4 | | | IV-1 | Bcl11a | 1.02 | 10109 | 3 | 4 | | IV-1 | C1qtnf3 | 1.08 |
| 10014 | 3 | 4 | | | IV-1 | Bcl11b | 1.10 | 10110 | 3 | 4 | | IV-1 | C1qtnf5 | 1.12 |
| 10015 | 3 | 4 | | | IV-1 | Bcl2 | 1.20 | 10111 | 3 | 4 | | IV-1 | C1ra | 1.16 |
| 10016 | 3 | 4 | | | IV-1 | Bcl2a1b | 1.07 | 10112 | 3 | 4 | | IV-1 | C1rb | 1.04 |
| 10017 | 3 | 4 | | | IV-1 | Bcl2l1 | 1.03 | 10113 | 3 | 4 | | IV-1 | C230035I16Rik | 1.01 |
| 10018 | 3 | 4 | | | IV-1 | Bcl2l2 | 1.20 | 10114 | 3 | 4 | | IV-1 | C330021F23Rik | 1.08 |
| 10019 | 3 | 4 | | | IV-1 | Bcl7a | 1.00 | 10115 | 3 | 4 | | IV-1 | C4b | 1.11 |
| 10020 | 3 | 4 | | | IV-1 | Bcl7b | 1.04 | 10116 | 3 | 4 | | IV-1 | C530005A16Rik | 1.34 |
| 10021 | 3 | 4 | | | IV-1 | Bcl9 | 1.26 | 10117 | 3 | 4 | | IV-1 | C530008M17Rik | 1.14 |
| 10022 | 3 | 4 | | | IV-1 | Bcl9l | 1.09 | 10118 | 3 | 4 | | IV-1 | C5ar1 | 1.36 |
| 10023 | 3 | 4 | | | IV-1 | Bclaf1 | 1.10 | 10119 | 3 | 4 | | IV-1 | C77370 | 1.36 |
| 10024 | 3 | 4 | | | IV-1 | Bcor | 1.07 | 10120 | 3 | 4 | | IV-1 | C78339 | 1.12 |
| 10025 | 3 | 4 | | | IV-1 | Bcr | 1.09 | 10121 | 3 | 4 | | IV-1 | Cab39 | 1.11 |
| 10026 | 3 | 4 | | | IV-1 | Bdkrb2 | 1.39 | 10122 | 3 | 4 | | IV-1 | Cabin1 | 1.15 |
| 10027 | 3 | 4 | | | IV-1 | Bend6 | 1.23 | 10123 | 3 | 4 | | IV-1 | Cables2 | 1.14 |
| 10028 | 3 | 4 | | | IV-1 | Bend7 | 1.10 | 10124 | 3 | 4 | | IV-1 | Cacfd1 | 1.29 |
| 10029 | 3 | 4 | | | IV-1 | Bet1l | 1.17 | 10125 | 3 | 4 | | IV-1 | Cachd1 | 1.16 |
| 10030 | 3 | 4 | | | IV-1 | Bex2 | 1.19 | 10126 | 3 | 4 | | IV-1 | Cacna1e | 1.35 |
| 10031 | 3 | 4 | | | IV-1 | Bfsp1 | 1.39 | 10127 | 3 | 4 | | IV-1 | Cacna1g | 1.26 |
| 10032 | 3 | 4 | | | IV-1 | Bfsp2 | 1.23 | 10128 | 3 | 4 | | IV-1 | Cacna2d1 | 1.19 |
| 10033 | 3 | 4 | | | IV-1 | Bglap3 | 1.41 | 10129 | 3 | 4 | | IV-1 | Cacna2d3 | 1.19 |
| 10034 | 3 | 4 | | | IV-1 | Bhlhe22 | 1.40 | 10130 | 3 | 4 | | IV-1 | Cacnb2 | 1.31 |
| 10035 | 3 | 4 | | | IV-1 | Bhlhe41 | 1.13 | 10131 | 3 | 4 | | IV-1 | Cacnb3 | 1.15 |
| 10036 | 3 | 4 | | | IV-1 | Bicc1 | 1.33 | 10132 | 3 | 4 | | IV-1 | Cacng4 | 1.22 |
| 10037 | 3 | 4 | | | IV-1 | Bid | 1.03 | 10133 | 3 | 4 | | IV-1 | Cacng5 | 1.10 |
| 10038 | 3 | 4 | | | IV-1 | Birc2 | 1.13 | 10134 | 3 | 4 | | IV-1 | Cacng7 | 1.33 |
| 10039 | 3 | 4 | | | IV-1 | Bivm | 1.03 | 10135 | 3 | 4 | | IV-1 | Cacng8 | 1.18 |
| 10040 | 3 | 4 | | | IV-1 | Blcap | 1.43 | 10136 | 3 | 4 | | IV-1 | Cadm1 | 1.32 |
| 10041 | 3 | 4 | | | IV-1 | Bloc1s2 | 1.22 | 10137 | 3 | 4 | | IV-1 | Cadm2 | 1.47 |
| 10042 | 3 | 4 | | | IV-1 | Bloc1s6 | 1.23 | 10138 | 3 | 4 | | IV-1 | Cadps | 1.44 |
| 10043 | 3 | 4 | | | IV-1 | Blvra | 1.02 | 10139 | 3 | 4 | | IV-1 | Cadps2 | 1.43 |
| 10044 | 3 | 4 | | | IV-1 | Blzf1 | 1.01 | 10140 | 3 | 4 | | IV-1 | Calb2 | 1.09 |
| 10045 | 3 | 4 | | | IV-1 | Bmf | 1.25 | 10141 | 3 | 4 | | IV-1 | Calca | 1.49 |
| 10046 | 3 | 4 | | | IV-1 | Bmi1 | 1.02 | 10142 | 3 | 4 | | IV-1 | Calcoco1 | 1.29 |
| 10047 | 3 | 4 | | | IV-1 | Bmp1 | 1.08 | 10143 | 3 | 4 | | IV-1 | Calhm2 | 1.06 |
| 10048 | 3 | 4 | | | IV-1 | Bmp4 | 1.01 | 10144 | 3 | 4 | | IV-1 | Camk1d | 1.12 |
| 10049 | 3 | 4 | | | IV-1 | Bmp5 | 1.13 | 10145 | 3 | 4 | | IV-1 | Camk1g | 1.34 |
| 10050 | 3 | 4 | | | IV-1 | Bmp6 | 1.47 | 10146 | 3 | 4 | | IV-1 | Camk2b | 1.11 |
| 10051 | 3 | 4 | | | IV-1 | Bmp7 | 1.12 | 10147 | 3 | 4 | | IV-1 | Camk2d | 1.29 |
| 10052 | 3 | 4 | | | IV-1 | Bmp8a | 1.19 | 10148 | 3 | 4 | | IV-1 | Camk2g | 1.43 |
| 10053 | 3 | 4 | | | IV-1 | Bmper | 1.33 | 10149 | 3 | 4 | | IV-1 | Camk2n1 | 1.44 |
| 10054 | 3 | 4 | | | IV-1 | Bmpr1b | 1.09 | 10150 | 3 | 4 | | IV-1 | Camk4 | 1.30 |
| 10055 | 3 | 4 | | | IV-1 | Bmpr2 | 1.05 | 10151 | 3 | 4 | | IV-1 | Camkk2 | 1.18 |
| 10056 | 3 | 4 | | | IV-1 | Bmyc | 1.04 | 10152 | 3 | 4 | | IV-1 | Camkmt | 1.16 |
| 10057 | 3 | 4 | | | IV-1 | Bnc1 | 1.07 | 10153 | 3 | 4 | | IV-1 | Camkv | 1.36 |
| 10058 | 3 | 4 | | | IV-1 | Bnip2 | 1.01 | 10154 | 3 | 4 | | IV-1 | Caml | 1.04 |
| 10059 | 3 | 4 | | | IV-1 | Boc | 1.44 | 10155 | 3 | 4 | | IV-1 | Camsap1 | 1.30 |
| 10060 | 3 | 4 | | | IV-1 | Bod1 | 1.07 | 10156 | 3 | 4 | | IV-1 | Camsap2 | 1.04 |
| 10061 | 3 | 4 | | | IV-1 | Bod1l | 1.03 | 10157 | 3 | 4 | | IV-1 | Camta1 | 1.43 |
| 10062 | 3 | 4 | | | IV-1 | Bok | 1.13 | 10158 | 3 | 4 | | IV-1 | Camta2 | 1.23 |
| 10063 | 3 | 4 | | | IV-1 | Bola2 | 1.13 | 10159 | 3 | 4 | | IV-1 | Capg | 1.18 |
| 10064 | 3 | 4 | | | IV-1 | Bptf | 1.11 | 10160 | 3 | 4 | | IV-1 | Capn10 | 1.02 |
| 10065 | 3 | 4 | | | IV-1 | Braf | 1.28 | 10161 | 3 | 4 | | IV-1 | Capn6 | 1.04 |
| 10066 | 3 | 4 | | | IV-1 | Brap | 1.06 | 10162 | 3 | 4 | | IV-1 | Capn7 | 1.01 |
| 10067 | 3 | 4 | | | IV-1 | Brat1 | 1.15 | 10163 | 3 | 4 | | IV-1 | Caprin2 | 1.21 |
| 10068 | 3 | 4 | | | IV-1 | Brca2 | 1.03 | 10164 | 3 | 4 | | IV-1 | Car9 | 1.10 |
| 10069 | 3 | 4 | | | IV-1 | Brcc3 | 1.27 | 10165 | 3 | 4 | | IV-1 | Carf | 1.40 |
| 10070 | 3 | 4 | | | IV-1 | Brd1 | 1.16 | 10166 | 3 | 4 | | IV-1 | Carm1 | 1.05 |
| 10071 | 3 | 4 | | | IV-1 | Brd2 | 1.13 | 10167 | 3 | 4 | | IV-1 | Cars | 1.14 |
| 10072 | 3 | 4 | | | IV-1 | Brd3 | 1.11 | 10168 | 3 | 4 | | IV-1 | Casc3 | 1.09 |
| 10073 | 3 | 4 | | | IV-1 | Brd4 | 1.08 | 10169 | 3 | 4 | | IV-1 | Casc4 | 1.26 |
| 10074 | 3 | 4 | | | IV-1 | Brd8 | 1.14 | 10170 | 3 | 4 | | IV-1 | Cask | 1.40 |
| 10075 | 3 | 4 | | | IV-1 | Brd9 | 1.04 | 10171 | 3 | 4 | | IV-1 | Casp4 | 1.14 |
| 10076 | 3 | 4 | | | IV-1 | Brf1 | 1.16 | 10172 | 3 | 4 | | IV-1 | Cast | 1.03 |
| 10077 | 3 | 4 | | | IV-1 | Brf2 | 1.13 | 10173 | 3 | 4 | | IV-1 | Cbfa2t2 | 1.24 |

Fig. 45 - 54

| | | | | | | | |
|---|---|---|---|---|---|---|---|
| 10174 | 3 | 4 | | | IV-1 | Cbfa2t3 | 1.08 |
| 10175 | 3 | 4 | | | IV-1 | Cbfb | 1.06 |
| 10176 | 3 | 4 | | | IV-1 | Cbib | 1.20 |
| 10177 | 3 | 4 | | | IV-1 | Cbln3 | 1.06 |
| 10178 | 3 | 4 | | | IV-1 | Cbr1 | 1.13 |
| 10179 | 3 | 4 | | | IV-1 | Cbr2 | 1.22 |
| 10180 | 3 | 4 | | | IV-1 | Cbr4 | 1.01 |
| 10181 | 3 | 4 | | | IV-1 | Cbx4 | 1.10 |
| 10182 | 3 | 4 | | | IV-1 | Cc2d1a | 1.28 |
| 10183 | 3 | 4 | | | IV-1 | Cc2d1b | 1.24 |
| 10184 | 3 | 4 | | | IV-1 | Cc2d2a | 1.30 |
| 10185 | 3 | 4 | | | IV-1 | Ccar1 | 1.09 |
| 10186 | 3 | 4 | | | IV-1 | Ccar2 | 1.12 |
| 10187 | 3 | 4 | | | IV-1 | Ccbe1 | 1.36 |
| 10188 | 3 | 4 | | | IV-1 | Ccbl1 | 1.24 |
| 10189 | 3 | 4 | | | IV-1 | Ccbl2 | 1.29 |
| 10190 | 3 | 4 | | | IV-1 | Ccdc102a | 1.04 |
| 10191 | 3 | 4 | | | IV-1 | Ccdc104 | 1.14 |
| 10192 | 3 | 4 | | | IV-1 | Ccdc107 | 1.13 |
| 10193 | 3 | 4 | | | IV-1 | Ccdc114 | 1.27 |
| 10194 | 3 | 4 | | | IV-1 | Ccdc115 | 1.19 |
| 10195 | 3 | 4 | | | IV-1 | Ccdc116 | 1.30 |
| 10196 | 3 | 4 | | | IV-1 | Ccdc120 | 1.30 |
| 10197 | 3 | 4 | | | IV-1 | Ccdc126 | 1.13 |
| 10198 | 3 | 4 | | | IV-1 | Ccdc132 | 1.06 |
| 10199 | 3 | 4 | | | IV-1 | Ccdc138 | 1.06 |
| 10200 | 3 | 4 | | | IV-1 | Ccdc14 | 1.39 |
| 10201 | 3 | 4 | | | IV-1 | Ccdc142 | 1.33 |
| 10202 | 3 | 4 | | | IV-1 | Ccdc149 | 1.26 |
| 10203 | 3 | 4 | | | IV-1 | Ccdc15 | 1.08 |
| 10204 | 3 | 4 | | | IV-1 | Ccdc157 | 1.19 |
| 10205 | 3 | 4 | | | IV-1 | Ccdc160 | 1.42 |
| 10206 | 3 | 4 | | | IV-1 | Ccdc166 | 1.14 |
| 10207 | 3 | 4 | | | IV-1 | Ccdc167 | 1.01 |
| 10208 | 3 | 4 | | | IV-1 | Ccdc17 | 1.01 |
| 10209 | 3 | 4 | | | IV-1 | Ccdc173 | 1.09 |
| 10210 | 3 | 4 | | | IV-1 | Ccdc174 | 1.18 |
| 10211 | 3 | 4 | | | IV-1 | Ccdc176 | 1.19 |
| 10212 | 3 | 4 | | | IV-1 | Ccdc177 | 1.50 |
| 10213 | 3 | 4 | | | IV-1 | Ccdc181 | 1.09 |
| 10214 | 3 | 4 | | | IV-1 | Ccdc184 | 1.19 |
| 10215 | 3 | 4 | | | IV-1 | Ccdc24 | 1.02 |
| 10216 | 3 | 4 | | | IV-1 | Ccdc25 | 1.00 |
| 10217 | 3 | 4 | | | IV-1 | Ccdc30 | 1.50 |
| 10218 | 3 | 4 | | | IV-1 | Ccdc32 | 1.03 |
| 10219 | 3 | 4 | | | IV-1 | Ccdc36 | 1.16 |
| 10220 | 3 | 4 | | | IV-1 | Ccdc40 | 1.13 |
| 10221 | 3 | 4 | | | IV-1 | Ccdc47 | 1.11 |
| 10222 | 3 | 4 | | | IV-1 | Ccdc50 | 1.05 |
| 10223 | 3 | 4 | | | IV-1 | Ccdc53 | 1.09 |
| 10224 | 3 | 4 | | | IV-1 | Ccdc61 | 1.17 |
| 10225 | 3 | 4 | | | IV-1 | Ccdc67 | 1.05 |
| 10226 | 3 | 4 | | | IV-1 | Ccdc68 | 1.06 |
| 10227 | 3 | 4 | | | IV-1 | Ccdc73 | 1.31 |
| 10228 | 3 | 4 | | | IV-1 | Ccdc74a | 1.15 |
| 10229 | 3 | 4 | | | IV-1 | Ccdc84 | 1.21 |
| 10230 | 3 | 4 | | | IV-1 | Ccdc85a | 1.49 |
| 10231 | 3 | 4 | | | IV-1 | Ccdc88a | 1.22 |
| 10232 | 3 | 4 | | | IV-1 | Ccdc9 | 1.05 |
| 10233 | 3 | 4 | | | IV-1 | Ccdc93 | 1.01 |
| 10234 | 3 | 4 | | | IV-1 | Ccdc94 | 1.22 |
| 10235 | 3 | 4 | | | IV-1 | Ccdc96 | 1.03 |
| 10236 | 3 | 4 | | | IV-1 | Ccl21c | 1.21 |
| 10237 | 3 | 4 | | | IV-1 | Ccl3 | 1.45 |
| 10238 | 3 | 4 | | | IV-1 | Ccl9 | 1.01 |
| 10239 | 3 | 4 | | | IV-1 | Ccm2l | 1.07 |
| 10240 | 3 | 4 | | | IV-1 | Ccnd2 | 1.04 |
| 10241 | 3 | 4 | | | IV-1 | Ccng2 | 1.05 |
| 10242 | 3 | 4 | | | IV-1 | Ccnj | 1.32 |
| 10243 | 3 | 4 | | | IV-1 | Ccnl2 | 1.18 |
| 10244 | 3 | 4 | | | IV-1 | Ccno | 1.47 |
| 10245 | 3 | 4 | | | IV-1 | Ccnt2 | 1.01 |
| 10246 | 3 | 4 | | | IV-1 | Ccny | 1.18 |
| 10247 | 3 | 4 | | | IV-1 | Ccnyl1 | 1.12 |
| 10248 | 3 | 4 | | | IV-1 | Ccs | 1.19 |
| 10249 | 3 | 4 | | | IV-1 | Ccser1 | 1.36 |
| 10250 | 3 | 4 | | | IV-1 | Ccser2 | 1.24 |
| 10251 | 3 | 4 | | | IV-1 | Cct2 | 1.01 |
| 10252 | 3 | 4 | | | IV-1 | Cct2l | 1.02 |
| 10253 | 3 | 4 | | | IV-1 | Cd109 | 1.06 |
| 10254 | 3 | 4 | | | IV-1 | Cd14 | 1.22 |
| 10255 | 3 | 4 | | | IV-1 | Cd180 | 1.05 |
| 10256 | 3 | 4 | | | IV-1 | Cd1d1 | 1.01 |
| 10257 | 3 | 4 | | | IV-1 | Cd200 | 1.24 |
| 10258 | 3 | 4 | | | IV-1 | Cd200r1 | 1.32 |
| 10259 | 3 | 4 | | | IV-1 | Cd274 | 1.02 |
| 10260 | 3 | 4 | | | IV-1 | Cd2bp2 | 1.10 |
| 10261 | 3 | 4 | | | IV-1 | Cd300a | 1.18 |
| 10262 | 3 | 4 | | | IV-1 | Cd38 | 1.19 |
| 10263 | 3 | 4 | | | IV-1 | Cd68 | 1.02 |
| 10264 | 3 | 4 | | | IV-1 | Cd84 | 1.06 |
| 10265 | 3 | 4 | | | IV-1 | Cd9 | 1.03 |
| 10266 | 3 | 4 | | | IV-1 | Cdc14a | 1.07 |
| 10267 | 3 | 4 | | | IV-1 | Cdc14b | 1.12 |
| 10268 | 3 | 4 | | | IV-1 | Cdc37l1 | 1.12 |
| 10269 | 3 | 4 | | | IV-1 | Cdc42bpa | 1.23 |
| 10270 | 3 | 4 | | | IV-1 | Cdc42bpb | 1.18 |
| 10271 | 3 | 4 | | | IV-1 | Cdc42bpg | 1.01 |
| 10272 | 3 | 4 | | | IV-1 | Cdc42ep4 | 1.15 |
| 10273 | 3 | 4 | | | IV-1 | Cdc42ep5 | 1.01 |
| 10274 | 3 | 4 | | | IV-1 | Cdc42se2 | 1.05 |
| 10275 | 3 | 4 | | | IV-1 | Cdcp1 | 1.04 |
| 10276 | 3 | 4 | | | IV-1 | Cdh10 | 1.37 |
| 10277 | 3 | 4 | | | IV-1 | Cdh11 | 1.24 |
| 10278 | 3 | 4 | | | IV-1 | Cdh13 | 1.29 |
| 10279 | 3 | 4 | | | IV-1 | Cdh2 | 1.44 |
| 10280 | 3 | 4 | | | IV-1 | Cdh20 | 1.20 |
| 10281 | 3 | 4 | | | IV-1 | Cdh24 | 1.15 |
| 10282 | 3 | 4 | | | IV-1 | Cdh3 | 1.01 |
| 10283 | 3 | 4 | | | IV-1 | Cdh4 | 1.35 |
| 10284 | 3 | 4 | | | IV-1 | Cdh6 | 1.37 |
| 10285 | 3 | 4 | | | IV-1 | Cdh7 | 1.10 |
| 10286 | 3 | 4 | | | IV-1 | Cdh9 | 1.11 |
| 10287 | 3 | 4 | | | IV-1 | Cdhr1 | 1.01 |
| 10288 | 3 | 4 | | | IV-1 | Cdip1 | 1.17 |
| 10289 | 3 | 4 | | | IV-1 | Cdk11b | 1.18 |
| 10290 | 3 | 4 | | | IV-1 | Cdk12 | 1.06 |
| 10291 | 3 | 4 | | | IV-1 | Cdk13 | 1.18 |
| 10292 | 3 | 4 | | | IV-1 | Cdk14 | 1.18 |
| 10293 | 3 | 4 | | | IV-1 | Cdk18 | 1.14 |
| 10294 | 3 | 4 | | | IV-1 | Cdk19 | 1.22 |
| 10295 | 3 | 4 | | | IV-1 | Cdk3-ps | 1.23 |
| 10296 | 3 | 4 | | | IV-1 | Cdk5 | 1.04 |
| 10297 | 3 | 4 | | | IV-1 | Cdk5r1 | 1.50 |
| 10298 | 3 | 4 | | | IV-1 | Cdk5r2 | 1.26 |
| 10299 | 3 | 4 | | | IV-1 | Cdk5rap1 | 1.40 |
| 10300 | 3 | 4 | | | IV-1 | Cdk5rap3 | 1.03 |
| 10301 | 3 | 4 | | | IV-1 | Cdk7 | 1.08 |
| 10302 | 3 | 4 | | | IV-1 | Cdk9 | 1.18 |
| 10303 | 3 | 4 | | | IV-1 | Cdkl2 | 1.32 |
| 10304 | 3 | 4 | | | IV-1 | Cdkl4 | 1.25 |
| 10305 | 3 | 4 | | | IV-1 | Cdkn1a | 1.19 |
| 10306 | 3 | 4 | | | IV-1 | Cdkn2aip | 1.04 |
| 10307 | 3 | 4 | | | IV-1 | Cdon | 1.10 |
| 10308 | 3 | 4 | | | IV-1 | Cdr1 | 1.04 |
| 10309 | 3 | 4 | | | IV-1 | Cdr2l | 1.09 |
| 10310 | 3 | 4 | | | IV-1 | Cds2 | 1.15 |
| 10311 | 3 | 4 | | | IV-1 | Cdsn | 1.09 |
| 10312 | 3 | 4 | | | IV-1 | Cdyl2 | 1.30 |
| 10313 | 3 | 4 | | | IV-1 | Cebpd | 1.48 |
| 10314 | 3 | 4 | | | IV-1 | Cebpz | 1.06 |
| 10315 | 3 | 4 | | | IV-1 | Cebpzos | 1.07 |
| 10316 | 3 | 4 | | | IV-1 | Cecr6 | 1.36 |
| 10317 | 3 | 4 | | | IV-1 | Celf2 | 1.33 |
| 10318 | 3 | 4 | | | IV-1 | Celf6 | 1.43 |
| 10319 | 3 | 4 | | | IV-1 | Celsr1 | 1.01 |
| 10320 | 3 | 4 | | | IV-1 | Celsr2 | 1.23 |
| 10321 | 3 | 4 | | | IV-1 | Cend1 | 1.44 |
| 10322 | 3 | 4 | | | IV-1 | Cenpc1 | 1.08 |
| 10323 | 3 | 4 | | | IV-1 | Cenpt | 1.15 |
| 10324 | 3 | 4 | | | IV-1 | Cenpu | 1.13 |
| 10325 | 3 | 4 | | | IV-1 | Cenpv | 1.11 |
| 10326 | 3 | 4 | | | IV-1 | Cep120 | 1.07 |
| 10327 | 3 | 4 | | | IV-1 | Cep131 | 1.42 |
| 10328 | 3 | 4 | | | IV-1 | Cep164 | 1.06 |
| 10329 | 3 | 4 | | | IV-1 | Cep170 | 1.11 |
| 10330 | 3 | 4 | | | IV-1 | Cep170b | 1.24 |
| 10331 | 3 | 4 | | | IV-1 | Cep250 | 1.09 |
| 10332 | 3 | 4 | | | IV-1 | Cep44 | 1.17 |
| 10333 | 3 | 4 | | | IV-1 | Cep63 | 1.12 |
| 10334 | 3 | 4 | | | IV-1 | Cep68 | 1.08 |
| 10335 | 3 | 4 | | | IV-1 | Cep70 | 1.17 |
| 10336 | 3 | 4 | | | IV-1 | Cep78 | 1.12 |
| 10337 | 3 | 4 | | | IV-1 | Cep85 | 1.01 |
| 10338 | 3 | 4 | | | IV-1 | Cep85l | 1.38 |
| 10339 | 3 | 4 | | | IV-1 | Cep95 | 1.03 |
| 10340 | 3 | 4 | | | IV-1 | Cep97 | 1.01 |
| 10341 | 3 | 4 | | | IV-1 | Cerk | 1.08 |
| 10342 | 3 | 4 | | | IV-1 | Cers1 | 1.01 |
| 10343 | 3 | 4 | | | IV-1 | Cers5 | 1.28 |
| 10344 | 3 | 4 | | | IV-1 | Cers6 | 1.02 |
| 10345 | 3 | 4 | | | IV-1 | Ces1c | 1.31 |
| 10346 | 3 | 4 | | | IV-1 | Cfhr2 | 1.01 |
| 10347 | 3 | 4 | | | IV-1 | Chad | 1.11 |
| 10348 | 3 | 4 | | | IV-1 | Chadl | 1.42 |
| 10349 | 3 | 4 | | | IV-1 | Champ1 | 1.05 |
| 10350 | 3 | 4 | | | IV-1 | Chd1 | 1.00 |
| 10351 | 3 | 4 | | | IV-1 | Chd2 | 1.46 |
| 10352 | 3 | 4 | | | IV-1 | Chd3 | 1.18 |
| 10353 | 3 | 4 | | | IV-1 | Chd3os | 1.25 |
| 10354 | 3 | 4 | | | IV-1 | Chd4 | 1.08 |
| 10355 | 3 | 4 | | | IV-1 | Chd6 | 1.22 |
| 10356 | 3 | 4 | | | IV-1 | Chd8 | 1.09 |
| 10357 | 3 | 4 | | | IV-1 | Chfr | 1.02 |
| 10358 | 3 | 4 | | | IV-1 | Chga | 1.39 |
| 10359 | 3 | 4 | | | IV-1 | Chic2 | 1.42 |
| 10360 | 3 | 4 | | | IV-1 | Chil3 | 1.14 |
| 10361 | 3 | 4 | | | IV-1 | Chka | 1.09 |
| 10362 | 3 | 4 | | | IV-1 | Chkb | 1.26 |
| 10363 | 3 | 4 | | | IV-1 | Chl1 | 1.34 |
| 10364 | 3 | 4 | | | IV-1 | Chm | 1.05 |
| 10365 | 3 | 4 | | | IV-1 | Chmp1a | 1.01 |

Fig. 45 - 55

| | | | | | | | |
|---|---|---|---|---|---|---|---|
| 10366 | 3 | 4 | | | IV-1 | Chmp2b | 1.09 |
| 10367 | 3 | 4 | | | IV-1 | Chmp3 | 1.02 |
| 10368 | 3 | 4 | | | IV-1 | Chmp6 | 1.12 |
| 10369 | 3 | 4 | | | IV-1 | Chmp7 | 1.08 |
| 10370 | 3 | 4 | | | IV-1 | Chn1 | 1.09 |
| 10371 | 3 | 4 | | | IV-1 | Chn2 | 1.13 |
| 10372 | 3 | 4 | | | IV-1 | Chodl | 1.20 |
| 10373 | 3 | 4 | | | IV-1 | Chpf | 1.04 |
| 10374 | 3 | 4 | | | IV-1 | Chrac1 | 1.15 |
| 10375 | 3 | 4 | | | IV-1 | Chrd | 1.33 |
| 10376 | 3 | 4 | | | IV-1 | Chrdl1 | 1.01 |
| 10377 | 3 | 4 | | | IV-1 | Chrm2 | 1.42 |
| 10378 | 3 | 4 | | | IV-1 | Chrm3 | 1.32 |
| 10379 | 3 | 4 | | | IV-1 | Chrna1 | 1.11 |
| 10380 | 3 | 4 | | | IV-1 | Chrna3 | 1.16 |
| 10381 | 3 | 4 | | | IV-1 | Chrna4 | 1.06 |
| 10382 | 3 | 4 | | | IV-1 | Chrna5 | 1.06 |
| 10383 | 3 | 4 | | | IV-1 | Chrnb2 | 1.42 |
| 10384 | 3 | 4 | | | IV-1 | Chrnb4 | 1.09 |
| 10385 | 3 | 4 | | | IV-1 | Chst1 | 1.05 |
| 10386 | 3 | 4 | | | IV-1 | Chst10 | 1.50 |
| 10387 | 3 | 4 | | | IV-1 | Chst14 | 1.03 |
| 10388 | 3 | 4 | | | IV-1 | Chst15 | 1.05 |
| 10389 | 3 | 4 | | | IV-1 | Chst2 | 1.00 |
| 10390 | 3 | 4 | | | IV-1 | Chst8 | 1.18 |
| 10391 | 3 | 4 | | | IV-1 | Chsy3 | 1.01 |
| 10392 | 3 | 4 | | | IV-1 | Chuk | 1.03 |
| 10393 | 3 | 4 | | | IV-1 | Churc1 | 1.01 |
| 10394 | 3 | 4 | | | IV-1 | Ciart | 1.14 |
| 10395 | 3 | 4 | | | IV-1 | Cib2 | 1.26 |
| 10396 | 3 | 4 | | | IV-1 | Cic | 1.23 |
| 10397 | 3 | 4 | | | IV-1 | Clip | 1.02 |
| 10398 | 3 | 4 | | | IV-1 | Clip2 | 1.11 |
| 10399 | 3 | 4 | | | IV-1 | Cir1 | 1.13 |
| 10400 | 3 | 4 | | | IV-1 | Cisd2 | 1.11 |
| 10401 | 3 | 4 | | | IV-1 | Cish | 1.13 |
| 10402 | 3 | 4 | | | IV-1 | Cited2 | 1.16 |
| 10403 | 3 | 4 | | | IV-1 | Ciz1 | 1.20 |
| 10404 | 3 | 4 | | | IV-1 | Clasp1 | 1.12 |
| 10405 | 3 | 4 | | | IV-1 | Clasp2 | 1.23 |
| 10406 | 3 | 4 | | | IV-1 | Clasrp | 1.46 |
| 10407 | 3 | 4 | | | IV-1 | Clcf1 | 1.34 |
| 10408 | 3 | 4 | | | IV-1 | Clcn2 | 1.24 |
| 10409 | 3 | 4 | | | IV-1 | Clcn4-2 | 1.11 |
| 10410 | 3 | 4 | | | IV-1 | Clcn6 | 1.13 |
| 10411 | 3 | 4 | | | IV-1 | Clcn7 | 1.08 |
| 10412 | 3 | 4 | | | IV-1 | Cldn11 | 1.25 |
| 10413 | 3 | 4 | | | IV-1 | Cldn20 | 1.11 |
| 10414 | 3 | 4 | | | IV-1 | Cldn23 | 1.28 |
| 10415 | 3 | 4 | | | IV-1 | Cldn4 | 1.45 |
| 10416 | 3 | 4 | | | IV-1 | Cldn9 | 1.16 |
| 10417 | 3 | 4 | | | IV-1 | Clec16a | 1.07 |
| 10418 | 3 | 4 | | | IV-1 | Clec3a | 1.24 |
| 10419 | 3 | 4 | | | IV-1 | Clec4a1 | 1.36 |
| 10420 | 3 | 4 | | | IV-1 | Clec4a2 | 1.31 |
| 10421 | 3 | 4 | | | IV-1 | Clec4a3 | 1.03 |
| 10422 | 3 | 4 | | | IV-1 | Clec5a | 1.24 |
| 10423 | 3 | 4 | | | IV-1 | Clgn | 1.14 |
| 10424 | 3 | 4 | | | IV-1 | Clip1 | 1.22 |
| 10425 | 3 | 4 | | | IV-1 | Clip2 | 1.06 |
| 10426 | 3 | 4 | | | IV-1 | Clip3 | 1.32 |
| 10427 | 3 | 4 | | | IV-1 | Clip4 | 1.19 |
| 10428 | 3 | 4 | | | IV-1 | Clk1 | 1.28 |
| 10429 | 3 | 4 | | | IV-1 | Clk2 | 1.17 |
| 10430 | 3 | 4 | | | IV-1 | Clk4 | 1.16 |
| 10431 | 3 | 4 | | | IV-1 | Clmp | 1.08 |
| 10432 | 3 | 4 | | | IV-1 | Cln3 | 1.11 |
| 10433 | 3 | 4 | | | IV-1 | Cln6 | 1.11 |
| 10434 | 3 | 4 | | | IV-1 | Clock | 1.22 |
| 10435 | 3 | 4 | | | IV-1 | Clstn2 | 1.22 |
| 10436 | 3 | 4 | | | IV-1 | Clstn3 | 1.29 |
| 10437 | 3 | 4 | | | IV-1 | Cluap1 | 1.07 |
| 10438 | 3 | 4 | | | IV-1 | Cmip | 1.22 |
| 10439 | 3 | 4 | | | IV-1 | Cmtm5 | 1.11 |
| 10440 | 3 | 4 | | | IV-1 | Cmtr1 | 1.04 |
| 10441 | 3 | 4 | | | IV-1 | Cmtr2 | 1.47 |
| 10442 | 3 | 4 | | | IV-1 | Cnbd2 | 1.05 |
| 10443 | 3 | 4 | | | IV-1 | Cnga2 | 1.21 |
| 10444 | 3 | 4 | | | IV-1 | Cnih2 | 1.32 |
| 10445 | 3 | 4 | | | IV-1 | Cnksr3 | 1.23 |
| 10446 | 3 | 4 | | | IV-1 | Cnnm1 | 1.38 |
| 10447 | 3 | 4 | | | IV-1 | Cnot10 | 1.04 |
| 10448 | 3 | 4 | | | IV-1 | Cnot7 | 1.03 |
| 10449 | 3 | 4 | | | IV-1 | Cnot8 | 1.06 |
| 10450 | 3 | 4 | | | IV-1 | Cnppd1 | 1.21 |
| 10451 | 3 | 4 | | | IV-1 | Cntd1 | 1.15 |
| 10452 | 3 | 4 | | | IV-1 | Cntln | 1.33 |
| 10453 | 3 | 4 | | | IV-1 | Cntn1 | 1.35 |
| 10454 | 3 | 4 | | | IV-1 | Cntn3 | 1.12 |
| 10455 | 3 | 4 | | | IV-1 | Cntn4 | 1.35 |
| 10456 | 3 | 4 | | | IV-1 | Cntn6 | 1.02 |
| 10457 | 3 | 4 | | | IV-1 | Coch | 1.00 |
| 10458 | 3 | 4 | | | IV-1 | Cog1 | 1.07 |
| 10459 | 3 | 4 | | | IV-1 | Cog2 | 1.21 |
| 10460 | 3 | 4 | | | IV-1 | Cog3 | 1.14 |
| 10461 | 3 | 4 | | | IV-1 | Cog5 | 1.00 |
| 10462 | 3 | 4 | | | IV-1 | Cog7 | 1.07 |
| 10463 | 3 | 4 | | | IV-1 | Coil | 1.02 |
| 10464 | 3 | 4 | | | IV-1 | Col10a1 | 1.07 |
| 10465 | 3 | 4 | | | IV-1 | Col11a1 | 1.09 |
| 10466 | 3 | 4 | | | IV-1 | Col12a1 | 1.26 |
| 10467 | 3 | 4 | | | IV-1 | Col13a1 | 1.10 |
| 10468 | 3 | 4 | | | IV-1 | Col17a1 | 1.01 |
| 10469 | 3 | 4 | | | IV-1 | Col20a1 | 1.09 |
| 10470 | 3 | 4 | | | IV-1 | Col23a1 | 1.37 |
| 10471 | 3 | 4 | | | IV-1 | Col24a1 | 1.05 |
| 10472 | 3 | 4 | | | IV-1 | Col26a1 | 1.14 |
| 10473 | 3 | 4 | | | IV-1 | Col27a1 | 1.47 |
| 10474 | 3 | 4 | | | IV-1 | Col2a1 | 1.12 |
| 10475 | 3 | 4 | | | IV-1 | Col4a3bp | 1.20 |
| 10476 | 3 | 4 | | | IV-1 | Col6a1 | 1.02 |
| 10477 | 3 | 4 | | | IV-1 | Col7a1 | 1.15 |
| 10478 | 3 | 4 | | | IV-1 | Col8a1 | 1.45 |
| 10479 | 3 | 4 | | | IV-1 | Col8a2 | 1.29 |
| 10480 | 3 | 4 | | | IV-1 | Col9a1 | 1.33 |
| 10481 | 3 | 4 | | | IV-1 | Col9a2 | 1.40 |
| 10482 | 3 | 4 | | | IV-1 | Col9a3 | 1.11 |
| 10483 | 3 | 4 | | | IV-1 | Colgalt2 | 1.04 |
| 10484 | 3 | 4 | | | IV-1 | Colq | 1.17 |
| 10485 | 3 | 4 | | | IV-1 | Commd4 | 1.09 |
| 10486 | 3 | 4 | | | IV-1 | Commd5 | 1.10 |
| 10487 | 3 | 4 | | | IV-1 | Commd8 | 1.03 |
| 10488 | 3 | 4 | | | IV-1 | Copg1 | 1.06 |
| 10489 | 3 | 4 | | | IV-1 | Coprs | 1.14 |
| 10490 | 3 | 4 | | | IV-1 | Cops7b | 1.08 |
| 10491 | 3 | 4 | | | IV-1 | Coq10a | 1.14 |
| 10492 | 3 | 4 | | | IV-1 | Coq7 | 1.04 |
| 10493 | 3 | 4 | | | IV-1 | Coro2b | 1.17 |
| 10494 | 3 | 4 | | | IV-1 | Coro6 | 1.22 |
| 10495 | 3 | 4 | | | IV-1 | Coro7 | 1.14 |
| 10496 | 3 | 4 | | | IV-1 | Cox16 | 1.18 |
| 10497 | 3 | 4 | | | IV-1 | Cox18 | 1.13 |
| 10498 | 3 | 4 | | | IV-1 | Cox6b2 | 1.36 |
| 10499 | 3 | 4 | | | IV-1 | Cox7a2l | 1.05 |
| 10500 | 3 | 4 | | | IV-1 | Cpa2 | 1.27 |
| 10501 | 3 | 4 | | | IV-1 | Cpa4 | 1.11 |
| 10502 | 3 | 4 | | | IV-1 | Cpe | 1.46 |
| 10503 | 3 | 4 | | | IV-1 | Cpeb1 | 1.29 |
| 10504 | 3 | 4 | | | IV-1 | Cpeb2 | 1.19 |
| 10505 | 3 | 4 | | | IV-1 | Cpeb3 | 1.12 |
| 10506 | 3 | 4 | | | IV-1 | Cped1 | 1.05 |
| 10507 | 3 | 4 | | | IV-1 | Cplx1 | 1.43 |
| 10508 | 3 | 4 | | | IV-1 | Cpne2 | 1.20 |
| 10509 | 3 | 4 | | | IV-1 | Cpne4 | 1.47 |
| 10510 | 3 | 4 | | | IV-1 | Cpne5 | 1.25 |
| 10511 | 3 | 4 | | | IV-1 | Cpne8 | 1.28 |
| 10512 | 3 | 4 | | | IV-1 | Cpped1 | 1.01 |
| 10513 | 3 | 4 | | | IV-1 | Cps1 | 1.24 |
| 10514 | 3 | 4 | | | IV-1 | Cpsf1 | 1.12 |
| 10515 | 3 | 4 | | | IV-1 | Cpsf4 | 1.04 |
| 10516 | 3 | 4 | | | IV-1 | Cpsf6 | 1.15 |
| 10517 | 3 | 4 | | | IV-1 | Cpsf7 | 1.16 |
| 10518 | 3 | 4 | | | IV-1 | Cpt1c | 1.31 |
| 10519 | 3 | 4 | | | IV-1 | Cpxm1 | 1.09 |
| 10520 | 3 | 4 | | | IV-1 | Cradd | 1.07 |
| 10521 | 3 | 4 | | | IV-1 | Cramp1l | 1.05 |
| 10522 | 3 | 4 | | | IV-1 | Crb2 | 1.27 |
| 10523 | 3 | 4 | | | IV-1 | Crbn | 1.27 |
| 10524 | 3 | 4 | | | IV-1 | Crcp | 1.08 |
| 10525 | 3 | 4 | | | IV-1 | Crct1 | 1.04 |
| 10526 | 3 | 4 | | | IV-1 | Creb3l1 | 1.01 |
| 10527 | 3 | 4 | | | IV-1 | Creb5 | 1.28 |
| 10528 | 3 | 4 | | | IV-1 | Crebbp | 1.25 |
| 10529 | 3 | 4 | | | IV-1 | Crebzf | 1.12 |
| 10530 | 3 | 4 | | | IV-1 | Crem | 1.08 |
| 10531 | 3 | 4 | | | IV-1 | Crim1 | 1.34 |
| 10532 | 3 | 4 | | | IV-1 | Crispld1 | 1.43 |
| 10533 | 3 | 4 | | | IV-1 | Crispld2 | 1.29 |
| 10534 | 3 | 4 | | | IV-1 | Crlf2 | 1.08 |
| 10535 | 3 | 4 | | | IV-1 | Crnkl1 | 1.10 |
| 10536 | 3 | 4 | | | IV-1 | Crtac1 | 1.47 |
| 10537 | 3 | 4 | | | IV-1 | Crtc2 | 1.02 |
| 10538 | 3 | 4 | | | IV-1 | Crtc3 | 1.18 |
| 10539 | 3 | 4 | | | IV-1 | Cry2 | 1.28 |
| 10540 | 3 | 4 | | | IV-1 | Cryaa | 1.28 |
| 10541 | 3 | 4 | | | IV-1 | Cryba1 | 1.34 |
| 10542 | 3 | 4 | | | IV-1 | Cryba2 | 1.01 |
| 10543 | 3 | 4 | | | IV-1 | Crybb3 | 1.28 |
| 10544 | 3 | 4 | | | IV-1 | Crygb | 1.08 |
| 10545 | 3 | 4 | | | IV-1 | Crygc | 1.20 |
| 10546 | 3 | 4 | | | IV-1 | Crygd | 1.21 |
| 10547 | 3 | 4 | | | IV-1 | Cryge | 1.23 |
| 10548 | 3 | 4 | | | IV-1 | Crygf | 1.14 |
| 10549 | 3 | 4 | | | IV-1 | Cryzl1 | 1.13 |
| 10550 | 3 | 4 | | | IV-1 | Csad | 1.07 |
| 10551 | 3 | 4 | | | IV-1 | Csf1 | 1.13 |
| 10552 | 3 | 4 | | | IV-1 | Csf2rb | 1.27 |
| 10553 | 3 | 4 | | | IV-1 | Csf2rb2 | 1.49 |
| 10554 | 3 | 4 | | | IV-1 | Csgalnact1 | 1.13 |
| 10555 | 3 | 4 | | | IV-1 | Csgalnact2 | 1.07 |
| 10556 | 3 | 4 | | | IV-1 | Csnk1d | 1.11 |
| 10557 | 3 | 4 | | | IV-1 | Csnk1e | 1.31 |

Fig. 45 - 56

| | | | | | | | | | | | | | | | |
|---|---|---|---|---|---|---|---|---|---|---|---|---|---|---|---|
| 10558 | 3 | 4 | | | IV-1 | Csnk1g1 | 1.20 | 10654 | 3 | 4 | | | IV-1 | D630045J12Rik | 1.36 |
| 10559 | 3 | 4 | | | IV-1 | Csnk1g3 | 1.10 | 10655 | 3 | 4 | | | IV-1 | D830030K20Rik | 1.41 |
| 10560 | 3 | 4 | | | IV-1 | Csnk2a2 | 1.02 | 10656 | 3 | 4 | | | IV-1 | D830031N03Rik | 1.16 |
| 10561 | 3 | 4 | | | IV-1 | Cspg5 | 1.39 | 10657 | 3 | 4 | | | IV-1 | D8Ertd82e | 1.05 |
| 10562 | 3 | 4 | | | IV-1 | Cspp1 | 1.02 | 10658 | 3 | 4 | | | IV-1 | D930015E06Rik | 1.08 |
| 10563 | 3 | 4 | | | IV-1 | Csrnp1 | 1.19 | 10659 | 3 | 4 | | | IV-1 | D930015M05Rik | 1.37 |
| 10564 | 3 | 4 | | | IV-1 | Csrnp2 | 1.25 | 10660 | 3 | 4 | | | IV-1 | D930048N14Rik | 1.48 |
| 10565 | 3 | 4 | | | IV-1 | Csrp2bp | 1.02 | 10661 | 3 | 4 | | | IV-1 | Daam2 | 1.13 |
| 10566 | 3 | 4 | | | IV-1 | Cstad | 1.39 | 10662 | 3 | 4 | | | IV-1 | Dab1 | 1.30 |
| 10567 | 3 | 4 | | | IV-1 | Cstb | 1.07 | 10663 | 3 | 4 | | | IV-1 | Dab2 | 1.02 |
| 10568 | 3 | 4 | | | IV-1 | Cstf2 | 1.08 | 10664 | 3 | 4 | | | IV-1 | Dab2ip | 1.08 |
| 10569 | 3 | 4 | | | IV-1 | Cstf2t | 1.04 | 10665 | 3 | 4 | | | IV-1 | Dach1 | 1.23 |
| 10570 | 3 | 4 | | | IV-1 | Cstf3 | 1.05 | 10666 | 3 | 4 | | | IV-1 | Dach2 | 1.37 |
| 10571 | 3 | 4 | | | IV-1 | Ctbp2 | 1.03 | 10667 | 3 | 4 | | | IV-1 | Dact1 | 1.36 |
| 10572 | 3 | 4 | | | IV-1 | Ctbs | 1.34 | 10668 | 3 | 4 | | | IV-1 | Dact3 | 1.20 |
| 10573 | 3 | 4 | | | IV-1 | Ctc1 | 1.03 | 10669 | 3 | 4 | | | IV-1 | Dagla | 1.16 |
| 10574 | 3 | 4 | | | IV-1 | Ctdp1 | 1.14 | 10670 | 3 | 4 | | | IV-1 | Dap3 | 1.21 |
| 10575 | 3 | 4 | | | IV-1 | Ctdsp2 | 1.08 | 10671 | 3 | 4 | | | IV-1 | Dapk1 | 1.22 |
| 10576 | 3 | 4 | | | IV-1 | Ctdspl2 | 1.09 | 10672 | 3 | 4 | | | IV-1 | Daxx | 1.08 |
| 10577 | 3 | 4 | | | IV-1 | Ctf1 | 1.31 | 10673 | 3 | 4 | | | IV-1 | Dazap1 | 1.01 |
| 10578 | 3 | 4 | | | IV-1 | Ctif | 1.25 | 10674 | 3 | 4 | | | IV-1 | Dazap2 | 1.01 |
| 10579 | 3 | 4 | | | IV-1 | Ctla2a | 1.16 | 10675 | 3 | 4 | | | IV-1 | Dbh | 1.33 |
| 10580 | 3 | 4 | | | IV-1 | Ctnna2 | 1.46 | 10676 | 3 | 4 | | | IV-1 | Dbil5 | 1.14 |
| 10581 | 3 | 4 | | | IV-1 | Ctnnal1 | 1.11 | 10677 | 3 | 4 | | | IV-1 | Dbn1 | 1.20 |
| 10582 | 3 | 4 | | | IV-1 | Ctnnbip1 | 1.04 | 10678 | 3 | 4 | | | IV-1 | Dbndd1 | 1.41 |
| 10583 | 3 | 4 | | | IV-1 | Ctnnbl1 | 1.08 | 10679 | 3 | 4 | | | IV-1 | Dbndd2 | 1.29 |
| 10584 | 3 | 4 | | | IV-1 | Ctns | 1.06 | 10680 | 3 | 4 | | | IV-1 | Dbpht2 | 1.11 |
| 10585 | 3 | 4 | | | IV-1 | Ctps2 | 1.22 | 10681 | 3 | 4 | | | IV-1 | Dbr1 | 1.26 |
| 10586 | 3 | 4 | | | IV-1 | Ctsh | 1.11 | 10682 | 3 | 4 | | | IV-1 | Dcaf10 | 1.06 |
| 10587 | 3 | 4 | | | IV-1 | Ctsl | 1.46 | 10683 | 3 | 4 | | | IV-1 | Dcaf11 | 1.07 |
| 10588 | 3 | 4 | | | IV-1 | Ctso | 1.40 | 10684 | 3 | 4 | | | IV-1 | Dcaf12l1 | 1.16 |
| 10589 | 3 | 4 | | | IV-1 | Ctss | 1.32 | 10685 | 3 | 4 | | | IV-1 | Dcaf12l2 | 1.04 |
| 10590 | 3 | 4 | | | IV-1 | Cttn | 1.06 | 10686 | 3 | 4 | | | IV-1 | Dcaf13 | 1.15 |
| 10591 | 3 | 4 | | | IV-1 | Cttnbp2 | 1.42 | 10687 | 3 | 4 | | | IV-1 | Dcaf15 | 1.16 |
| 10592 | 3 | 4 | | | IV-1 | Cttnbp2nl | 1.11 | 10688 | 3 | 4 | | | IV-1 | Dcaf5 | 1.23 |
| 10593 | 3 | 4 | | | IV-1 | Ctu2 | 1.15 | 10689 | 3 | 4 | | | IV-1 | Dcaf6 | 1.00 |
| 10594 | 3 | 4 | | | IV-1 | Ctxn3 | 1.02 | 10690 | 3 | 4 | | | IV-1 | Dcaf7 | 1.07 |
| 10595 | 3 | 4 | | | IV-1 | Cuedc1 | 1.45 | 10691 | 3 | 4 | | | IV-1 | Dcaf8 | 1.12 |
| 10596 | 3 | 4 | | | IV-1 | Cuedc2 | 1.12 | 10692 | 3 | 4 | | | IV-1 | Dcbld2 | 1.00 |
| 10597 | 3 | 4 | | | IV-1 | Cul1 | 1.09 | 10693 | 3 | 4 | | | IV-1 | Dcdc2a | 1.11 |
| 10598 | 3 | 4 | | | IV-1 | Cul3 | 1.07 | 10694 | 3 | 4 | | | IV-1 | Dchs1 | 1.20 |
| 10599 | 3 | 4 | | | IV-1 | Cul5 | 1.06 | 10695 | 3 | 4 | | | IV-1 | Dclk1 | 1.39 |
| 10600 | 3 | 4 | | | IV-1 | Cul7 | 1.10 | 10696 | 3 | 4 | | | IV-1 | Dclk3 | 1.21 |
| 10601 | 3 | 4 | | | IV-1 | Cux2 | 1.34 | 10697 | 3 | 4 | | | IV-1 | Dclre1a | 1.06 |
| 10602 | 3 | 4 | | | IV-1 | Cwc22 | 1.21 | 10698 | 3 | 4 | | | IV-1 | Dclre1c | 1.19 |
| 10603 | 3 | 4 | | | IV-1 | Cwc25 | 1.18 | 10699 | 3 | 4 | | | IV-1 | Dcp1a | 1.07 |
| 10604 | 3 | 4 | | | IV-1 | Cwc27 | 1.41 | 10700 | 3 | 4 | | | IV-1 | Dctn1 | 1.07 |
| 10605 | 3 | 4 | | | IV-1 | Cwf19l1 | 1.20 | 10701 | 3 | 4 | | | IV-1 | Dctn2 | 1.06 |
| 10606 | 3 | 4 | | | IV-1 | Cwf19l2 | 1.06 | 10702 | 3 | 4 | | | IV-1 | Dctn4 | 1.01 |
| 10607 | 3 | 4 | | | IV-1 | Cwh43 | 1.19 | 10703 | 3 | 4 | | | IV-1 | Dctn6 | 1.09 |
| 10608 | 3 | 4 | | | IV-1 | Cx3cl1 | 1.01 | 10704 | 3 | 4 | | | IV-1 | Dcun1d4 | 1.43 |
| 10609 | 3 | 4 | | | IV-1 | Cxadr | 1.13 | 10705 | 3 | 4 | | | IV-1 | Dcxr | 1.50 |
| 10610 | 3 | 4 | | | IV-1 | Cxcl12 | 1.02 | 10706 | 3 | 4 | | | IV-1 | Ddb2 | 1.03 |
| 10611 | 3 | 4 | | | IV-1 | Cxcl16 | 1.38 | 10707 | 3 | 4 | | | IV-1 | Ddc | 1.09 |
| 10612 | 3 | 4 | | | IV-1 | Cxcr2 | 1.37 | 10708 | 3 | 4 | | | IV-1 | Ddhd2 | 1.21 |
| 10613 | 3 | 4 | | | IV-1 | Cxx1a | 1.11 | 10709 | 3 | 4 | | | IV-1 | Ddit3 | 1.23 |
| 10614 | 3 | 4 | | | IV-1 | Cxx1b | 1.06 | 10710 | 3 | 4 | | | IV-1 | Ddit4 | 1.01 |
| 10615 | 3 | 4 | | | IV-1 | Cxx1c | 1.26 | 10711 | 3 | 4 | | | IV-1 | Ddn | 1.22 |
| 10616 | 3 | 4 | | | IV-1 | Cxxc1 | 1.00 | 10712 | 3 | 4 | | | IV-1 | Ddr1 | 1.07 |
| 10617 | 3 | 4 | | | IV-1 | Cyb561 | 1.12 | 10713 | 3 | 4 | | | IV-1 | Ddr2 | 1.06 |
| 10618 | 3 | 4 | | | IV-1 | Cyb561d1 | 1.37 | 10714 | 3 | 4 | | | IV-1 | Ddrgk1 | 1.08 |
| 10619 | 3 | 4 | | | IV-1 | Cyb5d1 | 1.04 | 10715 | 3 | 4 | | | IV-1 | Ddx1 | 1.06 |
| 10620 | 3 | 4 | | | IV-1 | Cyb5r1 | 1.02 | 10716 | 3 | 4 | | | IV-1 | Ddx10 | 1.15 |
| 10621 | 3 | 4 | | | IV-1 | Cyb5r2 | 1.19 | 10717 | 3 | 4 | | | IV-1 | Ddx17 | 1.15 |
| 10622 | 3 | 4 | | | IV-1 | Cyb5r3 | 1.03 | 10718 | 3 | 4 | | | IV-1 | Ddx19a | 1.09 |
| 10623 | 3 | 4 | | | IV-1 | Cyb5rl | 1.03 | 10719 | 3 | 4 | | | IV-1 | Ddx19b | 1.23 |
| 10624 | 3 | 4 | | | IV-1 | Cygb | 1.20 | 10720 | 3 | 4 | | | IV-1 | Ddx20 | 1.05 |
| 10625 | 3 | 4 | | | IV-1 | Cyp26a1 | 1.39 | 10721 | 3 | 4 | | | IV-1 | Ddx21 | 1.10 |
| 10626 | 3 | 4 | | | IV-1 | Cyp2a12 | 1.42 | 10722 | 3 | 4 | | | IV-1 | Ddx24 | 1.13 |
| 10627 | 3 | 4 | | | IV-1 | Cyp2d10 | 1.28 | 10723 | 3 | 4 | | | IV-1 | Ddx25 | 1.31 |
| 10628 | 3 | 4 | | | IV-1 | Cyp2g1 | 1.07 | 10724 | 3 | 4 | | | IV-1 | Ddx26b | 1.05 |
| 10629 | 3 | 4 | | | IV-1 | Cyp2j9 | 1.36 | 10725 | 3 | 4 | | | IV-1 | Ddx28 | 1.01 |
| 10630 | 3 | 4 | | | IV-1 | Cyp2r1 | 1.44 | 10726 | 3 | 4 | | | IV-1 | Ddx39b | 1.09 |
| 10631 | 3 | 4 | | | IV-1 | Cyp39a1 | 1.22 | 10727 | 3 | 4 | | | IV-1 | Ddx42 | 1.18 |
| 10632 | 3 | 4 | | | IV-1 | Cyp4f13 | 1.27 | 10728 | 3 | 4 | | | IV-1 | Ddx46 | 1.03 |
| 10633 | 3 | 4 | | | IV-1 | Cyp4f16 | 1.22 | 10729 | 3 | 4 | | | IV-1 | Ddx49 | 1.04 |
| 10634 | 3 | 4 | | | IV-1 | Cyp4v3 | 1.05 | 10730 | 3 | 4 | | | IV-1 | Ddx5 | 1.04 |
| 10635 | 3 | 4 | | | IV-1 | Cyp7b1 | 1.09 | 10731 | 3 | 4 | | | IV-1 | Ddx50 | 1.24 |
| 10636 | 3 | 4 | | | IV-1 | Cys1 | 1.02 | 10732 | 3 | 4 | | | IV-1 | Ddx51 | 1.37 |
| 10637 | 3 | 4 | | | IV-1 | Cystm1 | 1.13 | 10733 | 3 | 4 | | | IV-1 | Ddx52 | 1.15 |
| 10638 | 3 | 4 | | | IV-1 | Cyth1 | 1.14 | 10734 | 3 | 4 | | | IV-1 | Ddx54 | 1.18 |
| 10639 | 3 | 4 | | | IV-1 | Cyth2 | 1.31 | 10735 | 3 | 4 | | | IV-1 | Ddx55 | 1.26 |
| 10640 | 3 | 4 | | | IV-1 | Cyth3 | 1.12 | 10736 | 3 | 4 | | | IV-1 | Ddx56 | 1.02 |
| 10641 | 3 | 4 | | | IV-1 | Cyyr1 | 1.02 | 10737 | 3 | 4 | | | IV-1 | Ddx58 | 1.41 |
| 10642 | 3 | 4 | | | IV-1 | D10Wsu102e | 1.01 | 10738 | 3 | 4 | | | IV-1 | Ddx59 | 1.08 |
| 10643 | 3 | 4 | | | IV-1 | D130017N08Rik | 1.41 | 10739 | 3 | 4 | | | IV-1 | Def6 | 1.16 |
| 10644 | 3 | 4 | | | IV-1 | D130020L05Rik | 1.29 | 10740 | 3 | 4 | | | IV-1 | Def8 | 1.12 |
| 10645 | 3 | 4 | | | IV-1 | D130040H23Rik | 1.06 | 10741 | 3 | 4 | | | IV-1 | Defb14 | 1.29 |
| 10646 | 3 | 4 | | | IV-1 | D15Ertd621e | 1.10 | 10742 | 3 | 4 | | | IV-1 | Degs1 | 1.07 |
| 10647 | 3 | 4 | | | IV-1 | D16Ertd472e | 1.07 | 10743 | 3 | 4 | | | IV-1 | Dennd1a | 1.11 |
| 10648 | 3 | 4 | | | IV-1 | D230025D16Rik | 1.05 | 10744 | 3 | 4 | | | IV-1 | Dennd1b | 1.31 |
| 10649 | 3 | 4 | | | IV-1 | D330050I16Rik | 1.03 | 10745 | 3 | 4 | | | IV-1 | Dennd2a | 1.03 |
| 10650 | 3 | 4 | | | IV-1 | D3Ertd254e | 1.09 | 10746 | 3 | 4 | | | IV-1 | Dennd3 | 1.11 |
| 10651 | 3 | 4 | | | IV-1 | D430019H16Rik | 1.48 | 10747 | 3 | 4 | | | IV-1 | Dennd4a | 1.01 |
| 10652 | 3 | 4 | | | IV-1 | D430036I16Rik | 1.34 | 10748 | 3 | 4 | | | IV-1 | Dennd4b | 1.01 |
| 10653 | 3 | 4 | | | IV-1 | D430042O09Rik | 1.07 | 10749 | 3 | 4 | | | IV-1 | Dennd4c | 1.02 |

Fig. 45 - 57

| | | | | | | | | | | | | | | | |
|---|---|---|---|---|---|---|---|---|---|---|---|---|---|---|---|
| 10750 | 3 | 4 | | | IV-1 | Dennd5b | 1.28 | 10846 | 3 | 4 | | | IV-1 | Dph3 | 1.08 |
| 10751 | 3 | 4 | | | IV-1 | Denr | 1.10 | 10847 | 3 | 4 | | | IV-1 | Dph7 | 1.17 |
| 10752 | 3 | 4 | | | IV-1 | Dffb | 1.37 | 10848 | 3 | 4 | | | IV-1 | Dpm1 | 1.11 |
| 10753 | 3 | 4 | | | IV-1 | Dgcr14 | 1.19 | 10849 | 3 | 4 | | | IV-1 | Dpp6 | 1.28 |
| 10754 | 3 | 4 | | | IV-1 | Dgcr2 | 1.03 | 10850 | 3 | 4 | | | IV-1 | Dpp8 | 1.05 |
| 10755 | 3 | 4 | | | IV-1 | Dgcr6 | 1.23 | 10851 | 3 | 4 | | | IV-1 | Dpy19l1 | 1.09 |
| 10756 | 3 | 4 | | | IV-1 | Dgcr8 | 1.15 | 10852 | 3 | 4 | | | IV-1 | Dpy19l3 | 1.09 |
| 10757 | 3 | 4 | | | IV-1 | Dgka | 1.15 | 10853 | 3 | 4 | | | IV-1 | Dpy19l4 | 1.38 |
| 10758 | 3 | 4 | | | IV-1 | Dgkd | 1.15 | 10854 | 3 | 4 | | | IV-1 | Dpysl2 | 1.06 |
| 10759 | 3 | 4 | | | IV-1 | Dgke | 1.41 | 10855 | 3 | 4 | | | IV-1 | Dpysl3 | 1.30 |
| 10760 | 3 | 4 | | | IV-1 | Dgki | 1.22 | 10856 | 3 | 4 | | | IV-1 | Dpysl5 | 1.49 |
| 10761 | 3 | 4 | | | IV-1 | Dgkk | 1.12 | 10857 | 3 | 4 | | | IV-1 | Dram1 | 1.00 |
| 10762 | 3 | 4 | | | IV-1 | Dgkq | 1.30 | 10858 | 3 | 4 | | | IV-1 | Dram2 | 1.07 |
| 10763 | 3 | 4 | | | IV-1 | Dhps | 1.40 | 10859 | 3 | 4 | | | IV-1 | Drap1 | 1.10 |
| 10764 | 3 | 4 | | | IV-1 | Dhrsx | 1.03 | 10860 | 3 | 4 | | | IV-1 | Drosha | 1.05 |
| 10765 | 3 | 4 | | | IV-1 | Dhtkd1 | 1.23 | 10861 | 3 | 4 | | | IV-1 | Dsel | 1.07 |
| 10766 | 3 | 4 | | | IV-1 | Dhx30 | 1.19 | 10862 | 3 | 4 | | | IV-1 | Dst | 1.13 |
| 10767 | 3 | 4 | | | IV-1 | Dhx34 | 1.04 | 10863 | 3 | 4 | | | IV-1 | Dstyk | 1.08 |
| 10768 | 3 | 4 | | | IV-1 | Dhx35 | 1.16 | 10864 | 3 | 4 | | | IV-1 | Dtd1 | 1.10 |
| 10769 | 3 | 4 | | | IV-1 | Dhx36 | 1.34 | 10865 | 3 | 4 | | | IV-1 | Dtd2 | 1.09 |
| 10770 | 3 | 4 | | | IV-1 | Dhx40 | 1.12 | 10866 | 3 | 4 | | | IV-1 | Dtna | 1.04 |
| 10771 | 3 | 4 | | | IV-1 | Dhx57 | 1.08 | 10867 | 3 | 4 | | | IV-1 | Dtnb | 1.14 |
| 10772 | 3 | 4 | | | IV-1 | Dhx58 | 1.36 | 10868 | 3 | 4 | | | IV-1 | Dtnbp1 | 1.13 |
| 10773 | 3 | 4 | | | IV-1 | Dhx8 | 1.09 | 10869 | 3 | 4 | | | IV-1 | Dtwd2 | 1.23 |
| 10774 | 3 | 4 | | | IV-1 | Dhx9 | 1.12 | 10870 | 3 | 4 | | | IV-1 | Dtx1 | 1.35 |
| 10775 | 3 | 4 | | | IV-1 | Diap2 | 1.24 | 10871 | 3 | 4 | | | IV-1 | Dtx3 | 1.26 |
| 10776 | 3 | 4 | | | IV-1 | Dicer1 | 1.16 | 10872 | 3 | 4 | | | IV-1 | Dtx3l | 1.44 |
| 10777 | 3 | 4 | | | IV-1 | Dido1 | 1.03 | 10873 | 3 | 4 | | | IV-1 | Dtx4 | 1.14 |
| 10778 | 3 | 4 | | | IV-1 | Diexf | 1.09 | 10874 | 3 | 4 | | | IV-1 | Dus3l | 1.21 |
| 10779 | 3 | 4 | | | IV-1 | Dip2a | 1.19 | 10875 | 3 | 4 | | | IV-1 | Dus4l | 1.16 |
| 10780 | 3 | 4 | | | IV-1 | Dip2b | 1.03 | 10876 | 3 | 4 | | | IV-1 | Dusp1 | 1.36 |
| 10781 | 3 | 4 | | | IV-1 | Dip2c | 1.31 | 10877 | 3 | 4 | | | IV-1 | Dusp11 | 1.01 |
| 10782 | 3 | 4 | | | IV-1 | Diras2 | 1.35 | 10878 | 3 | 4 | | | IV-1 | Dusp12 | 1.12 |
| 10783 | 3 | 4 | | | IV-1 | Dirc2 | 1.20 | 10879 | 3 | 4 | | | IV-1 | Dusp15 | 1.36 |
| 10784 | 3 | 4 | | | IV-1 | Dis3 | 1.01 | 10880 | 3 | 4 | | | IV-1 | Dusp18 | 1.03 |
| 10785 | 3 | 4 | | | IV-1 | Dis3l2 | 1.23 | 10881 | 3 | 4 | | | IV-1 | Dusp2 | 1.22 |
| 10786 | 3 | 4 | | | IV-1 | Disc1 | 1.03 | 10882 | 3 | 4 | | | IV-1 | Dusp26 | 1.48 |
| 10787 | 3 | 4 | | | IV-1 | Disp2 | 1.32 | 10883 | 3 | 4 | | | IV-1 | Dusp28 | 1.13 |
| 10788 | 3 | 4 | | | IV-1 | Dixdc1 | 1.18 | 10884 | 3 | 4 | | | IV-1 | Dusp5 | 1.21 |
| 10789 | 3 | 4 | | | IV-1 | Dkk2 | 1.33 | 10885 | 3 | 4 | | | IV-1 | Dusp6 | 1.07 |
| 10790 | 3 | 4 | | | IV-1 | Dkk3 | 1.10 | 10886 | 3 | 4 | | | IV-1 | Dusp7 | 1.11 |
| 10791 | 3 | 4 | | | IV-1 | Dkk4 | 1.30 | 10887 | 3 | 4 | | | IV-1 | Dusp8 | 1.19 |
| 10792 | 3 | 4 | | | IV-1 | Dlg2 | 1.29 | 10888 | 3 | 4 | | | IV-1 | Dusp9 | 1.27 |
| 10793 | 3 | 4 | | | IV-1 | Dlg3 | 1.13 | 10889 | 3 | 4 | | | IV-1 | Dvl3 | 1.22 |
| 10794 | 3 | 4 | | | IV-1 | Dlg4 | 1.39 | 10890 | 3 | 4 | | | IV-1 | Dync1h1 | 1.21 |
| 10795 | 3 | 4 | | | IV-1 | Dlg5 | 1.38 | 10891 | 3 | 4 | | | IV-1 | Dync1li1 | 1.11 |
| 10796 | 3 | 4 | | | IV-1 | Dlgap2 | 1.07 | 10892 | 3 | 4 | | | IV-1 | Dync1li2 | 1.07 |
| 10797 | 3 | 4 | | | IV-1 | Dlgap4 | 1.19 | 10893 | 3 | 4 | | | IV-1 | Dync1li1 | 1.19 |
| 10798 | 3 | 4 | | | IV-1 | Dlk1 | 1.11 | 10894 | 3 | 4 | | | IV-1 | Dync1li2 | 1.10 |
| 10799 | 3 | 4 | | | IV-1 | Dlk2 | 1.50 | 10895 | 3 | 4 | | | IV-1 | Dync2h1 | 1.19 |
| 10800 | 3 | 4 | | | IV-1 | Dll1 | 1.06 | 10896 | 3 | 4 | | | IV-1 | Dynll2 | 1.08 |
| 10801 | 3 | 4 | | | IV-1 | Dlx1as | 1.37 | 10897 | 3 | 4 | | | IV-1 | Dynlrb2 | 1.23 |
| 10802 | 3 | 4 | | | IV-1 | Dlx5 | 1.16 | 10898 | 3 | 4 | | | IV-1 | Dynlt1a | 1.01 |
| 10803 | 3 | 4 | | | IV-1 | Dlx6os1 | 1.23 | 10899 | 3 | 4 | | | IV-1 | Dynlt1f | 1.17 |
| 10804 | 3 | 4 | | | IV-1 | Dmap1 | 1.06 | 10900 | 3 | 4 | | | IV-1 | Dyrk1a | 1.15 |
| 10805 | 3 | 4 | | | IV-1 | Dmrt2 | 1.01 | 10901 | 3 | 4 | | | IV-1 | Dyrk2 | 1.09 |
| 10806 | 3 | 4 | | | IV-1 | Dmrt3 | 1.15 | 10902 | 3 | 4 | | | IV-1 | Dzip1 | 1.03 |
| 10807 | 3 | 4 | | | IV-1 | Dmwd | 1.04 | 10903 | 3 | 4 | | | IV-1 | Dzip1l | 1.16 |
| 10808 | 3 | 4 | | | IV-1 | Dmxl2 | 1.38 | 10904 | 3 | 4 | | | IV-1 | E030030I06Rik | 1.24 |
| 10809 | 3 | 4 | | | IV-1 | Dnaaf3 | 1.35 | 10905 | 3 | 4 | | | IV-1 | E130008D07Rik | 1.26 |
| 10810 | 3 | 4 | | | IV-1 | Dnaja1 | 1.20 | 10906 | 3 | 4 | | | IV-1 | E130012A19Rik | 1.06 |
| 10811 | 3 | 4 | | | IV-1 | Dnaja2 | 1.03 | 10907 | 3 | 4 | | | IV-1 | E130112N10Rik | 1.09 |
| 10812 | 3 | 4 | | | IV-1 | Dnajb12 | 1.14 | 10908 | 3 | 4 | | | IV-1 | E130308A19Rik | 1.09 |
| 10813 | 3 | 4 | | | IV-1 | Dnajb5 | 1.01 | 10909 | 3 | 4 | | | IV-1 | E130309D02Rik | 1.01 |
| 10814 | 3 | 4 | | | IV-1 | Dnajb6 | 1.11 | 10910 | 3 | 4 | | | IV-1 | E130311K13Rik | 1.07 |
| 10815 | 3 | 4 | | | IV-1 | Dnajc10 | 1.07 | 10911 | 3 | 4 | | | IV-1 | E230016M11Rik | 1.13 |
| 10816 | 3 | 4 | | | IV-1 | Dnajc17 | 1.01 | 10912 | 3 | 4 | | | IV-1 | E330009J07Rik | 1.19 |
| 10817 | 3 | 4 | | | IV-1 | Dnajc18 | 1.00 | 10913 | 3 | 4 | | | IV-1 | E330013P04Rik | 1.14 |
| 10818 | 3 | 4 | | | IV-1 | Dnajc2 | 1.05 | 10914 | 3 | 4 | | | IV-1 | E430018J23Rik | 1.15 |
| 10819 | 3 | 4 | | | IV-1 | Dnajc27 | 1.34 | 10915 | 3 | 4 | | | IV-1 | E430025E21Rik | 1.05 |
| 10820 | 3 | 4 | | | IV-1 | Dnajc30 | 1.00 | 10916 | 3 | 4 | | | IV-1 | E4f1 | 1.30 |
| 10821 | 3 | 4 | | | IV-1 | Dnajc5 | 1.24 | 10917 | 3 | 4 | | | IV-1 | ES30011L22Rik | 1.28 |
| 10822 | 3 | 4 | | | IV-1 | Dnajc6 | 1.44 | 10918 | 3 | 4 | | | IV-1 | Ebf1 | 1.33 |
| 10823 | 3 | 4 | | | IV-1 | Dnajc7 | 1.26 | 10919 | 3 | 4 | | | IV-1 | Ebi3 | 1.06 |
| 10824 | 3 | 4 | | | IV-1 | Dnal4 | 1.06 | 10920 | 3 | 4 | | | IV-1 | Ebna1bp2 | 1.34 |
| 10825 | 3 | 4 | | | IV-1 | Dnd1 | 1.07 | 10921 | 3 | 4 | | | IV-1 | Ece1 | 1.21 |
| 10826 | 3 | 4 | | | IV-1 | Dnm2 | 1.06 | 10922 | 3 | 4 | | | IV-1 | Echdc3 | 1.11 |
| 10827 | 3 | 4 | | | IV-1 | Dnmbp | 1.12 | 10923 | 3 | 4 | | | IV-1 | Eci2 | 1.28 |
| 10828 | 3 | 4 | | | IV-1 | Dnpep | 1.03 | 10924 | 3 | 4 | | | IV-1 | Ecm1 | 1.04 |
| 10829 | 3 | 4 | | | IV-1 | Dnttip1 | 1.08 | 10925 | 3 | 4 | | | IV-1 | Ecm2 | 1.17 |
| 10830 | 3 | 4 | | | IV-1 | Dnttip2 | 1.04 | 10926 | 3 | 4 | | | IV-1 | Ecscr | 1.08 |
| 10831 | 3 | 4 | | | IV-1 | Doc2a | 1.06 | 10927 | 3 | 4 | | | IV-1 | Eda | 1.05 |
| 10832 | 3 | 4 | | | IV-1 | Doc2b | 1.15 | 10928 | 3 | 4 | | | IV-1 | Edar | 1.32 |
| 10833 | 3 | 4 | | | IV-1 | Dock10 | 1.02 | 10929 | 3 | 4 | | | IV-1 | Edc3 | 1.02 |
| 10834 | 3 | 4 | | | IV-1 | Dock4 | 1.29 | 10930 | 3 | 4 | | | IV-1 | Edc4 | 1.19 |
| 10835 | 3 | 4 | | | IV-1 | Dock6 | 1.21 | 10931 | 3 | 4 | | | IV-1 | Edil3 | 1.45 |
| 10836 | 3 | 4 | | | IV-1 | Dock7 | 1.16 | 10932 | 3 | 4 | | | IV-1 | Edn1 | 1.44 |
| 10837 | 3 | 4 | | | IV-1 | Dock9 | 1.17 | 10933 | 3 | 4 | | | IV-1 | Edn2 | 1.20 |
| 10838 | 3 | 4 | | | IV-1 | Dok2 | 1.28 | 10934 | 3 | 4 | | | IV-1 | Ednrb | 1.08 |
| 10839 | 3 | 4 | | | IV-1 | Dok4 | 1.11 | 10935 | 3 | 4 | | | IV-1 | Eea1 | 1.04 |
| 10840 | 3 | 4 | | | IV-1 | Dopey1 | 1.29 | 10936 | 3 | 4 | | | IV-1 | Eef1a1 | 1.06 |
| 10841 | 3 | 4 | | | IV-1 | Dos | 1.47 | 10937 | 3 | 4 | | | IV-1 | Eef1b2 | 1.00 |
| 10842 | 3 | 4 | | | IV-1 | Dpagt1 | 1.01 | 10938 | 3 | 4 | | | IV-1 | Eef2 | 1.09 |
| 10843 | 3 | 4 | | | IV-1 | Dpf3 | 1.01 | 10939 | 3 | 4 | | | IV-1 | Efcab1 | 1.33 |
| 10844 | 3 | 4 | | | IV-1 | Dph1 | 1.41 | 10940 | 3 | 4 | | | IV-1 | Efcab2 | 1.24 |
| 10845 | 3 | 4 | | | IV-1 | Dph2 | 1.04 | 10941 | 3 | 4 | | | IV-1 | Efcc1 | 1.01 |

Fig. 45 - 58

| | | | | | | | | | | | | | | |
|---|---|---|---|---|---|---|---|---|---|---|---|---|---|---|
| 10942 | 3 | 4 | | | IV-1 | Efna2 | 1.03 | 11038 | 3 | 4 | | | IV-1 | Epb4.1l3 | 1.04 |
| 10943 | 3 | 4 | | | IV-1 | Efna4 | 1.14 | 11039 | 3 | 4 | | | IV-1 | Epb4.1l4a | 1.19 |
| 10944 | 3 | 4 | | | IV-1 | Efna5 | 1.34 | 11040 | 3 | 4 | | | IV-1 | Epb4.1l4b | 1.03 |
| 10945 | 3 | 4 | | | IV-1 | Efnb2 | 1.07 | 11041 | 3 | 4 | | | IV-1 | Epc1 | 1.31 |
| 10946 | 3 | 4 | | | IV-1 | Efr3b | 1.39 | 11042 | 3 | 4 | | | IV-1 | Epc2 | 1.47 |
| 10947 | 3 | 4 | | | IV-1 | Efs | 1.03 | 11043 | 3 | 4 | | | IV-1 | Epg5 | 1.02 |
| 10948 | 3 | 4 | | | IV-1 | Egfl6 | 1.01 | 11044 | 3 | 4 | | | IV-1 | Epha10 | 1.14 |
| 10949 | 3 | 4 | | | IV-1 | Egfl8 | 1.35 | 11045 | 3 | 4 | | | IV-1 | Epha3 | 1.19 |
| 10950 | 3 | 4 | | | IV-1 | Egfr | 1.17 | 11046 | 3 | 4 | | | IV-1 | Epha4 | 1.31 |
| 10951 | 3 | 4 | | | IV-1 | Egr1 | 1.01 | 11047 | 3 | 4 | | | IV-1 | Epha7 | 1.33 |
| 10952 | 3 | 4 | | | IV-1 | Ehbp1 | 1.43 | 11048 | 3 | 4 | | | IV-1 | Ephb2 | 1.22 |
| 10953 | 3 | 4 | | | IV-1 | Ehd3 | 1.21 | 11049 | 3 | 4 | | | IV-1 | Ephb3 | 1.03 |
| 10954 | 3 | 4 | | | IV-1 | Ehmt1 | 1.09 | 11050 | 3 | 4 | | | IV-1 | Ephb6 | 1.19 |
| 10955 | 3 | 4 | | | IV-1 | Ehmt2 | 1.18 | 11051 | 3 | 4 | | | IV-1 | Ephx1 | 1.35 |
| 10956 | 3 | 4 | | | IV-1 | Ei24 | 1.24 | 11052 | 3 | 4 | | | IV-1 | Epm2a | 1.28 |
| 10957 | 3 | 4 | | | IV-1 | Eid1 | 1.27 | 11053 | 3 | 4 | | | IV-1 | Epm2aip1 | 1.03 |
| 10958 | 3 | 4 | | | IV-1 | Eid2 | 1.22 | 11054 | 3 | 4 | | | IV-1 | Epn2 | 1.19 |
| 10959 | 3 | 4 | | | IV-1 | Eif1 | 1.13 | 11055 | 3 | 4 | | | IV-1 | Eprs | 1.02 |
| 10960 | 3 | 4 | | | IV-1 | Eif1a | 1.07 | 11056 | 3 | 4 | | | IV-1 | Epsti1 | 1.02 |
| 10961 | 3 | 4 | | | IV-1 | Eif2ak2 | 1.44 | 11057 | 3 | 4 | | | IV-1 | Ept1 | 1.00 |
| 10962 | 3 | 4 | | | IV-1 | Eif2ak4 | 1.18 | 11058 | 3 | 4 | | | IV-1 | Epyc | 1.07 |
| 10963 | 3 | 4 | | | IV-1 | Eif2b3 | 1.27 | 11059 | 3 | 4 | | | IV-1 | Erbb2ip | 1.26 |
| 10964 | 3 | 4 | | | IV-1 | Eif2d | 1.07 | 11060 | 3 | 4 | | | IV-1 | Erbb4 | 1.49 |
| 10965 | 3 | 4 | | | IV-1 | Eif2s2 | 1.18 | 11061 | 3 | 4 | | | IV-1 | Erc1 | 1.11 |
| 10966 | 3 | 4 | | | IV-1 | Eif3c | 1.15 | 11062 | 3 | 4 | | | IV-1 | Erc2 | 1.40 |
| 10967 | 3 | 4 | | | IV-1 | Eif3e | 1.18 | 11063 | 3 | 4 | | | IV-1 | Ercc1 | 1.06 |
| 10968 | 3 | 4 | | | IV-1 | Eif3f | 1.40 | 11064 | 3 | 4 | | | IV-1 | Ercc2 | 1.06 |
| 10969 | 3 | 4 | | | IV-1 | Eif3h | 1.01 | 11065 | 3 | 4 | | | IV-1 | Ercc3 | 1.26 |
| 10970 | 3 | 4 | | | IV-1 | Eif3i | 1.05 | 11066 | 3 | 4 | | | IV-1 | Ercc4 | 1.22 |
| 10971 | 3 | 4 | | | IV-1 | Eif3j2 | 1.50 | 11067 | 3 | 4 | | | IV-1 | Ercc5 | 1.30 |
| 10972 | 3 | 4 | | | IV-1 | Eif3k | 1.02 | 11068 | 3 | 4 | | | IV-1 | Ercc6 | 1.12 |
| 10973 | 3 | 4 | | | IV-1 | Eif3m | 1.05 | 11069 | 3 | 4 | | | IV-1 | Ercc6l2 | 1.03 |
| 10974 | 3 | 4 | | | IV-1 | Eif4a3 | 1.01 | 11070 | 3 | 4 | | | IV-1 | Ercc8 | 1.12 |
| 10975 | 3 | 4 | | | IV-1 | Eif4b | 1.07 | 11071 | 3 | 4 | | | IV-1 | Ereg | 1.09 |
| 10976 | 3 | 4 | | | IV-1 | Eif4ebp1 | 1.05 | 11072 | 3 | 4 | | | IV-1 | Erf | 1.18 |
| 10977 | 3 | 4 | | | IV-1 | Eif4ebp3 | 1.38 | 11073 | 3 | 4 | | | IV-1 | Ergic1 | 1.07 |
| 10978 | 3 | 4 | | | IV-1 | Eif4enif1 | 1.07 | 11074 | 3 | 4 | | | IV-1 | Eri3 | 1.05 |
| 10979 | 3 | 4 | | | IV-1 | Eif4g2 | 1.01 | 11075 | 3 | 4 | | | IV-1 | Erich1 | 1.26 |
| 10980 | 3 | 4 | | | IV-1 | Eif4g3 | 1.36 | 11076 | 3 | 4 | | | IV-1 | Erlec1 | 1.23 |
| 10981 | 3 | 4 | | | IV-1 | Eif5 | 1.02 | 11077 | 3 | 4 | | | IV-1 | Erlin2 | 1.02 |
| 10982 | 3 | 4 | | | IV-1 | Eif5a2 | 1.16 | 11078 | 3 | 4 | | | IV-1 | Ermard | 1.13 |
| 10983 | 3 | 4 | | | IV-1 | Eif6 | 1.15 | 11079 | 3 | 4 | | | IV-1 | Ern1 | 1.41 |
| 10984 | 3 | 4 | | | IV-1 | Elac1 | 1.46 | 11080 | 3 | 4 | | | IV-1 | Errfi1 | 1.21 |
| 10985 | 3 | 4 | | | IV-1 | Elf1 | 1.00 | 11081 | 3 | 4 | | | IV-1 | Esco1 | 1.04 |
| 10986 | 3 | 4 | | | IV-1 | Elfn1 | 1.40 | 11082 | 3 | 4 | | | IV-1 | Esf1 | 1.07 |
| 10987 | 3 | 4 | | | IV-1 | Elfn2 | 1.42 | 11083 | 3 | 4 | | | IV-1 | Esm1 | 1.03 |
| 10988 | 3 | 4 | | | IV-1 | Elk1 | 1.05 | 11084 | 3 | 4 | | | IV-1 | Esrrb | 1.07 |
| 10989 | 3 | 4 | | | IV-1 | Elk3 | 1.08 | 11085 | 3 | 4 | | | IV-1 | Esrrg | 1.18 |
| 10990 | 3 | 4 | | | IV-1 | Ell | 1.15 | 11086 | 3 | 4 | | | IV-1 | Etl4 | 1.04 |
| 10991 | 3 | 4 | | | IV-1 | Ell3 | 1.11 | 11087 | 3 | 4 | | | IV-1 | Etv1 | 1.14 |
| 10992 | 3 | 4 | | | IV-1 | Elmo1 | 1.12 | 11088 | 3 | 4 | | | IV-1 | Etv3 | 1.03 |
| 10993 | 3 | 4 | | | IV-1 | Elmo2 | 1.07 | 11089 | 3 | 4 | | | IV-1 | Etv4 | 1.37 |
| 10994 | 3 | 4 | | | IV-1 | Elmod1 | 1.21 | 11090 | 3 | 4 | | | IV-1 | Etv5 | 1.09 |
| 10995 | 3 | 4 | | | IV-1 | Elmod2 | 1.01 | 11091 | 3 | 4 | | | IV-1 | Eva1b | 1.21 |
| 10996 | 3 | 4 | | | IV-1 | Elmod3 | 1.04 | 11092 | 3 | 4 | | | IV-1 | Eva1c | 1.08 |
| 10997 | 3 | 4 | | | IV-1 | Eln | 1.17 | 11093 | 3 | 4 | | | IV-1 | Evc | 1.20 |
| 10998 | 3 | 4 | | | IV-1 | Elovl2 | 1.26 | 11094 | 3 | 4 | | | IV-1 | Evc2 | 1.16 |
| 10999 | 3 | 4 | | | IV-1 | Elovl4 | 1.11 | 11095 | 3 | 4 | | | IV-1 | Evi5 | 1.07 |
| 11000 | 3 | 4 | | | IV-1 | Elovl7 | 1.07 | 11096 | 3 | 4 | | | IV-1 | Evi5l | 1.10 |
| 11001 | 3 | 4 | | | IV-1 | Elp2 | 1.07 | 11097 | 3 | 4 | | | IV-1 | Evl | 1.38 |
| 11002 | 3 | 4 | | | IV-1 | Elp3 | 1.09 | 11098 | 3 | 4 | | | IV-1 | Ewsr1 | 1.03 |
| 11003 | 3 | 4 | | | IV-1 | Elp4 | 1.23 | 11099 | 3 | 4 | | | IV-1 | Exoc1 | 1.13 |
| 11004 | 3 | 4 | | | IV-1 | Elp6 | 1.13 | 11100 | 3 | 4 | | | IV-1 | Exoc2 | 1.05 |
| 11005 | 3 | 4 | | | IV-1 | Emc1 | 1.07 | 11101 | 3 | 4 | | | IV-1 | Exoc3 | 1.05 |
| 11006 | 3 | 4 | | | IV-1 | Emc7 | 1.04 | 11102 | 3 | 4 | | | IV-1 | Exoc5 | 1.10 |
| 11007 | 3 | 4 | | | IV-1 | Emc8 | 1.10 | 11103 | 3 | 4 | | | IV-1 | Exoc6b | 1.25 |
| 11008 | 3 | 4 | | | IV-1 | Emd | 1.03 | 11104 | 3 | 4 | | | IV-1 | Exog | 1.05 |
| 11009 | 3 | 4 | | | IV-1 | Eme2 | 1.46 | 11105 | 3 | 4 | | | IV-1 | Exosc1 | 1.21 |
| 11010 | 3 | 4 | | | IV-1 | Emilin3 | 1.09 | 11106 | 3 | 4 | | | IV-1 | Exosc4 | 1.12 |
| 11011 | 3 | 4 | | | IV-1 | Eml2 | 1.47 | 11107 | 3 | 4 | | | IV-1 | Exosc5 | 1.21 |
| 11012 | 3 | 4 | | | IV-1 | Eml3 | 1.22 | 11108 | 3 | 4 | | | IV-1 | Exosc9 | 1.02 |
| 11013 | 3 | 4 | | | IV-1 | Eml4 | 1.03 | 11109 | 3 | 4 | | | IV-1 | Ext1 | 1.06 |
| 11014 | 3 | 4 | | | IV-1 | Emx2 | 1.18 | 11110 | 3 | 4 | | | IV-1 | Ext2 | 1.04 |
| 11015 | 3 | 4 | | | IV-1 | Emx2os | 1.05 | 11111 | 3 | 4 | | | IV-1 | Extl2 | 1.18 |
| 11016 | 3 | 4 | | | IV-1 | En1 | 1.13 | 11112 | 3 | 4 | | | IV-1 | Eya1 | 1.34 |
| 11017 | 3 | 4 | | | IV-1 | Enah | 1.17 | 11113 | 3 | 4 | | | IV-1 | Eya4 | 1.21 |
| 11018 | 3 | 4 | | | IV-1 | Enc1 | 1.33 | 11114 | 3 | 4 | | | IV-1 | Ezh1 | 1.07 |
| 11019 | 3 | 4 | | | IV-1 | Endov | 1.36 | 11115 | 3 | 4 | | | IV-1 | F2r | 1.15 |
| 11020 | 3 | 4 | | | IV-1 | Engase | 1.07 | 11116 | 3 | 4 | | | IV-1 | F2rl3 | 1.06 |
| 11021 | 3 | 4 | | | IV-1 | Enho | 1.34 | 11117 | 3 | 4 | | | IV-1 | F420014N23Rik | 1.36 |
| 11022 | 3 | 4 | | | IV-1 | Enkur | 1.14 | 11118 | 3 | 4 | | | IV-1 | F730043M19Rik | 1.17 |
| 11023 | 3 | 4 | | | IV-1 | Eno2 | 1.25 | 11119 | 3 | 4 | | | IV-1 | F8a | 1.16 |
| 11024 | 3 | 4 | | | IV-1 | Enox1 | 1.43 | 11120 | 3 | 4 | | | IV-1 | F930015N05Rik | 1.15 |
| 11025 | 3 | 4 | | | IV-1 | Enpp1 | 1.07 | 11121 | 3 | 4 | | | IV-1 | Fabp3 | 1.03 |
| 11026 | 3 | 4 | | | IV-1 | Enpp2 | 1.10 | 11122 | 3 | 4 | | | IV-1 | Fabp7 | 1.27 |
| 11027 | 3 | 4 | | | IV-1 | Enpp4 | 1.03 | 11123 | 3 | 4 | | | IV-1 | Faf1 | 1.05 |
| 11028 | 3 | 4 | | | IV-1 | Enpp5 | 1.39 | 11124 | 3 | 4 | | | IV-1 | Fahd2a | 1.07 |
| 11029 | 3 | 4 | | | IV-1 | Ensa | 1.03 | 11125 | 3 | 4 | | | IV-1 | Faim | 1.38 |
| 11030 | 3 | 4 | | | IV-1 | Entpd1 | 1.09 | 11126 | 3 | 4 | | | IV-1 | Faim2 | 1.18 |
| 11031 | 3 | 4 | | | IV-1 | Entpd2 | 1.05 | 11127 | 3 | 4 | | | IV-1 | Fam101a | 1.23 |
| 11032 | 3 | 4 | | | IV-1 | Entpd4 | 1.18 | 11128 | 3 | 4 | | | IV-1 | Fam101b | 1.03 |
| 11033 | 3 | 4 | | | IV-1 | Entpd6 | 1.08 | 11129 | 3 | 4 | | | IV-1 | Fam102b | 1.34 |
| 11034 | 3 | 4 | | | IV-1 | Entpd7 | 1.05 | 11130 | 3 | 4 | | | IV-1 | Fam105a | 1.05 |
| 11035 | 3 | 4 | | | IV-1 | Ep300 | 1.09 | 11131 | 3 | 4 | | | IV-1 | Fam110b | 1.37 |
| 11036 | 3 | 4 | | | IV-1 | Ep400 | 1.01 | 11132 | 3 | 4 | | | IV-1 | Fam114a2 | 1.04 |
| 11037 | 3 | 4 | | | IV-1 | Epb4.1l1 | 1.18 | 11133 | 3 | 4 | | | IV-1 | Fam115a | 1.08 |

Fig. 45 - 59

| | | | | | | | | | | | | | | |
|---|---|---|---|---|---|---|---|---|---|---|---|---|---|---|
| 11134 | 3 | 4 | | | IV-1 | Fam117b | 1.34 | 11230 | 3 | 4 | | | IV-1 | Fat3 | 1.38 |
| 11135 | 3 | 4 | | | IV-1 | Fam118a | 1.27 | 11231 | 3 | 4 | | | IV-1 | Fat4 | 1.44 |
| 11136 | 3 | 4 | | | IV-1 | Fam120aos | 1.42 | 11232 | 3 | 4 | | | IV-1 | Fau | 1.31 |
| 11137 | 3 | 4 | | | IV-1 | Fam120b | 1.01 | 11233 | 3 | 4 | | | IV-1 | Fbf1 | 1.09 |
| 11138 | 3 | 4 | | | IV-1 | Fam122a | 1.04 | 11234 | 3 | 4 | | | IV-1 | Fblim1 | 1.14 |
| 11139 | 3 | 4 | | | IV-1 | Fam124a | 1.41 | 11235 | 3 | 4 | | | IV-1 | Fbln2 | 1.28 |
| 11140 | 3 | 4 | | | IV-1 | Fam126b | 1.07 | 11236 | 3 | 4 | | | IV-1 | Fbln5 | 1.06 |
| 11141 | 3 | 4 | | | IV-1 | Fam129b | 1.02 | 11237 | 3 | 4 | | | IV-1 | Fbn2 | 1.12 |
| 11142 | 3 | 4 | | | IV-1 | Fam131a | 1.06 | 11238 | 3 | 4 | | | IV-1 | Fbrs | 1.05 |
| 11143 | 3 | 4 | | | IV-1 | Fam131b | 1.24 | 11239 | 3 | 4 | | | IV-1 | Fbxl12 | 1.00 |
| 11144 | 3 | 4 | | | IV-1 | Fam131c | 1.12 | 11240 | 3 | 4 | | | IV-1 | Fbxl12os | 1.03 |
| 11145 | 3 | 4 | | | IV-1 | Fam132b | 1.38 | 11241 | 3 | 4 | | | IV-1 | Fbxl15 | 1.01 |
| 11146 | 3 | 4 | | | IV-1 | Fam133b | 1.09 | 11242 | 3 | 4 | | | IV-1 | Fbxl19 | 1.10 |
| 11147 | 3 | 4 | | | IV-1 | Fam134a | 1.04 | 11243 | 3 | 4 | | | IV-1 | Fbxl2 | 1.38 |
| 11148 | 3 | 4 | | | IV-1 | Fam134b | 1.08 | 11244 | 3 | 4 | | | IV-1 | Fbxl20 | 1.41 |
| 11149 | 3 | 4 | | | IV-1 | Fam135a | 1.13 | 11245 | 3 | 4 | | | IV-1 | Fbxl21 | 1.18 |
| 11150 | 3 | 4 | | | IV-1 | Fam13b | 1.00 | 11246 | 3 | 4 | | | IV-1 | Fbxl3 | 1.10 |
| 11151 | 3 | 4 | | | IV-1 | Fam13c | 1.26 | 11247 | 3 | 4 | | | IV-1 | Fbxl4 | 1.40 |
| 11152 | 3 | 4 | | | IV-1 | Fam149b | 1.03 | 11248 | 3 | 4 | | | IV-1 | Fbxl5 | 1.12 |
| 11153 | 3 | 4 | | | IV-1 | Fam151b | 1.13 | 11249 | 3 | 4 | | | IV-1 | Fbxl6 | 1.04 |
| 11154 | 3 | 4 | | | IV-1 | Fam154b | 1.07 | 11250 | 3 | 4 | | | IV-1 | Fbxl7 | 1.01 |
| 11155 | 3 | 4 | | | IV-1 | Fam159a | 1.02 | 11251 | 3 | 4 | | | IV-1 | Fbxo10 | 1.09 |
| 11156 | 3 | 4 | | | IV-1 | Fam160a2 | 1.02 | 11252 | 3 | 4 | | | IV-1 | Fbxo11 | 1.26 |
| 11157 | 3 | 4 | | | IV-1 | Fam160b1 | 1.04 | 11253 | 3 | 4 | | | IV-1 | Fbxo2 | 1.44 |
| 11158 | 3 | 4 | | | IV-1 | Fam160b2 | 1.06 | 11254 | 3 | 4 | | | IV-1 | Fbxo21 | 1.21 |
| 11159 | 3 | 4 | | | IV-1 | Fam161a | 1.14 | 11255 | 3 | 4 | | | IV-1 | Fbxo22 | 1.03 |
| 11160 | 3 | 4 | | | IV-1 | Fam163b | 1.46 | 11256 | 3 | 4 | | | IV-1 | Fbxo25 | 1.07 |
| 11161 | 3 | 4 | | | IV-1 | Fam167a | 1.07 | 11257 | 3 | 4 | | | IV-1 | Fbxo28 | 1.08 |
| 11162 | 3 | 4 | | | IV-1 | Fam168a | 1.25 | 11258 | 3 | 4 | | | IV-1 | Fbxo31 | 1.21 |
| 11163 | 3 | 4 | | | IV-1 | Fam168b | 1.18 | 11259 | 3 | 4 | | | IV-1 | Fbxo32 | 1.45 |
| 11164 | 3 | 4 | | | IV-1 | Fam171a1 | 1.01 | 11260 | 3 | 4 | | | IV-1 | Fbxo34 | 1.05 |
| 11165 | 3 | 4 | | | IV-1 | Fam171a2 | 1.34 | 11261 | 3 | 4 | | | IV-1 | Fbxo38 | 1.12 |
| 11166 | 3 | 4 | | | IV-1 | Fam171b | 1.42 | 11262 | 3 | 4 | | | IV-1 | Fbxo4 | 1.38 |
| 11167 | 3 | 4 | | | IV-1 | Fam172a | 1.12 | 11263 | 3 | 4 | | | IV-1 | Fbxo44 | 1.43 |
| 11168 | 3 | 4 | | | IV-1 | Fam174a | 1.06 | 11264 | 3 | 4 | | | IV-1 | Fbxo6 | 1.30 |
| 11169 | 3 | 4 | | | IV-1 | Fam175a | 1.16 | 11265 | 3 | 4 | | | IV-1 | Fbxw11 | 1.17 |
| 11170 | 3 | 4 | | | IV-1 | Fam180a | 1.03 | 11266 | 3 | 4 | | | IV-1 | Fbxw17 | 1.11 |
| 11171 | 3 | 4 | | | IV-1 | Fam181b | 1.20 | 11267 | 3 | 4 | | | IV-1 | Fbxw2 | 1.02 |
| 11172 | 3 | 4 | | | IV-1 | Fam184a | 1.47 | 11268 | 3 | 4 | | | IV-1 | Fbxw5 | 1.07 |
| 11173 | 3 | 4 | | | IV-1 | Fam188a | 1.22 | 11269 | 3 | 4 | | | IV-1 | Fbxw7 | 1.16 |
| 11174 | 3 | 4 | | | IV-1 | Fam189b | 1.47 | 11270 | 3 | 4 | | | IV-1 | Fcgr2b | 1.17 |
| 11175 | 3 | 4 | | | IV-1 | Fam192a | 1.02 | 11271 | 3 | 4 | | | IV-1 | Fcgr3 | 1.29 |
| 11176 | 3 | 4 | | | IV-1 | Fam193a | 1.14 | 11272 | 3 | 4 | | | IV-1 | Fchsd1 | 1.30 |
| 11177 | 3 | 4 | | | IV-1 | Fam195b | 1.13 | 11273 | 3 | 4 | | | IV-1 | Fchsd2 | 1.18 |
| 11178 | 3 | 4 | | | IV-1 | Fam196b | 1.13 | 11274 | 3 | 4 | | | IV-1 | Fdx3l | 1.16 |
| 11179 | 3 | 4 | | | IV-1 | Fam199x | 1.14 | 11275 | 3 | 4 | | | IV-1 | Fendrr | 1.12 |
| 11180 | 3 | 4 | | | IV-1 | Fam19a1 | 1.46 | 11276 | 3 | 4 | | | IV-1 | Fes | 1.02 |
| 11181 | 3 | 4 | | | IV-1 | Fam203a | 1.21 | 11277 | 3 | 4 | | | IV-1 | Fetub | 1.20 |
| 11182 | 3 | 4 | | | IV-1 | Fam204a | 1.10 | 11278 | 3 | 4 | | | IV-1 | Fez2 | 1.08 |
| 11183 | 3 | 4 | | | IV-1 | Fam208a | 1.05 | 11279 | 3 | 4 | | | IV-1 | Fgd1 | 1.13 |
| 11184 | 3 | 4 | | | IV-1 | Fam20a | 1.39 | 11280 | 3 | 4 | | | IV-1 | Fgd4 | 1.04 |
| 11185 | 3 | 4 | | | IV-1 | Fam20c | 1.09 | 11281 | 3 | 4 | | | IV-1 | Fgf10 | 1.04 |
| 11186 | 3 | 4 | | | IV-1 | Fam21 | 1.22 | 11282 | 3 | 4 | | | IV-1 | Fgf11 | 1.04 |
| 11187 | 3 | 4 | | | IV-1 | Fam212a | 1.03 | 11283 | 3 | 4 | | | IV-1 | Fgf12 | 1.34 |
| 11188 | 3 | 4 | | | IV-1 | Fam214a | 1.19 | 11284 | 3 | 4 | | | IV-1 | Fgf13 | 1.32 |
| 11189 | 3 | 4 | | | IV-1 | Fam216a | 1.17 | 11285 | 3 | 4 | | | IV-1 | Fgf14 | 1.50 |
| 11190 | 3 | 4 | | | IV-1 | Fam219a | 1.45 | 11286 | 3 | 4 | | | IV-1 | Fgf15 | 1.40 |
| 11191 | 3 | 4 | | | IV-1 | Fam219aos | 1.44 | 11287 | 3 | 4 | | | IV-1 | Fgf2 | 1.11 |
| 11192 | 3 | 4 | | | IV-1 | Fam221a | 1.04 | 11288 | 3 | 4 | | | IV-1 | Fgf22 | 1.01 |
| 11193 | 3 | 4 | | | IV-1 | Fam222a | 1.19 | 11289 | 3 | 4 | | | IV-1 | Fgf7 | 1.10 |
| 11194 | 3 | 4 | | | IV-1 | Fam229b | 1.19 | 11290 | 3 | 4 | | | IV-1 | Fgf9 | 1.05 |
| 11195 | 3 | 4 | | | IV-1 | Fam32a | 1.04 | 11291 | 3 | 4 | | | IV-1 | Fgfr1 | 1.14 |
| 11196 | 3 | 4 | | | IV-1 | Fam3a | 1.13 | 11292 | 3 | 4 | | | IV-1 | Fgfr1op | 1.02 |
| 11197 | 3 | 4 | | | IV-1 | Fam3c | 1.13 | 11293 | 3 | 4 | | | IV-1 | Fgfr2 | 1.12 |
| 11198 | 3 | 4 | | | IV-1 | Fam43b | 1.13 | 11294 | 3 | 4 | | | IV-1 | Fgfr3 | 1.14 |
| 11199 | 3 | 4 | | | IV-1 | Fam46b | 1.14 | 11295 | 3 | 4 | | | IV-1 | Fgl2 | 1.39 |
| 11200 | 3 | 4 | | | IV-1 | Fam49a | 1.24 | 11296 | 3 | 4 | | | IV-1 | Fhod3 | 1.04 |
| 11201 | 3 | 4 | | | IV-1 | Fam49b | 1.22 | 11297 | 3 | 4 | | | IV-1 | Fibcd1 | 1.18 |
| 11202 | 3 | 4 | | | IV-1 | Fam53a | 1.15 | 11298 | 3 | 4 | | | IV-1 | Fibin | 1.20 |
| 11203 | 3 | 4 | | | IV-1 | Fam58b | 1.02 | 11299 | 3 | 4 | | | IV-1 | Ficd | 1.06 |
| 11204 | 3 | 4 | | | IV-1 | Fam60a | 1.15 | 11300 | 3 | 4 | | | IV-1 | Fig4 | 1.05 |
| 11205 | 3 | 4 | | | IV-1 | Fam63a | 1.14 | 11301 | 3 | 4 | | | IV-1 | Fign | 1.24 |
| 11206 | 3 | 4 | | | IV-1 | Fam65a | 1.01 | 11302 | 3 | 4 | | | IV-1 | Fignl2 | 1.05 |
| 11207 | 3 | 4 | | | IV-1 | Fam65b | 1.14 | 11303 | 3 | 4 | | | IV-1 | Firre | 1.49 |
| 11208 | 3 | 4 | | | IV-1 | Fam65c | 1.43 | 11304 | 3 | 4 | | | IV-1 | Fjx1 | 1.36 |
| 11209 | 3 | 4 | | | IV-1 | Fam69c | 1.11 | 11305 | 3 | 4 | | | IV-1 | Fkbp10 | 1.06 |
| 11210 | 3 | 4 | | | IV-1 | Fam71e1 | 1.25 | 11306 | 3 | 4 | | | IV-1 | Flcn | 1.17 |
| 11211 | 3 | 4 | | | IV-1 | Fam73a | 1.27 | 11307 | 3 | 4 | | | IV-1 | Flna | 1.06 |
| 11212 | 3 | 4 | | | IV-1 | Fam76a | 1.18 | 11308 | 3 | 4 | | | IV-1 | Flnb | 1.03 |
| 11213 | 3 | 4 | | | IV-1 | Fam76b | 1.30 | 11309 | 3 | 4 | | | IV-1 | Flot1 | 1.04 |
| 11214 | 3 | 4 | | | IV-1 | Fam78b | 1.22 | 11310 | 3 | 4 | | | IV-1 | Flot2 | 1.08 |
| 11215 | 3 | 4 | | | IV-1 | Fam84a | 1.13 | 11311 | 3 | 4 | | | IV-1 | Flrt1 | 1.32 |
| 11216 | 3 | 4 | | | IV-1 | Fam89a | 1.25 | 11312 | 3 | 4 | | | IV-1 | Flrt2 | 1.14 |
| 11217 | 3 | 4 | | | IV-1 | Fam89b | 1.30 | 11313 | 3 | 4 | | | IV-1 | Flrt3 | 1.33 |
| 11218 | 3 | 4 | | | IV-1 | Fam92a | 1.42 | 11314 | 3 | 4 | | | IV-1 | Flt4 | 1.05 |
| 11219 | 3 | 4 | | | IV-1 | Fam98b | 1.05 | 11315 | 3 | 4 | | | IV-1 | Flywch1 | 1.36 |
| 11220 | 3 | 4 | | | IV-1 | Fam98c | 1.17 | 11316 | 3 | 4 | | | IV-1 | Fmn1 | 1.49 |
| 11221 | 3 | 4 | | | IV-1 | Fancc | 1.04 | 11317 | 3 | 4 | | | IV-1 | Fmnl1 | 1.05 |
| 11222 | 3 | 4 | | | IV-1 | Fancl | 1.23 | 11318 | 3 | 4 | | | IV-1 | Fmnl2 | 1.23 |
| 11223 | 3 | 4 | | | IV-1 | Fancm | 1.09 | 11319 | 3 | 4 | | | IV-1 | Fmnl3 | 1.12 |
| 11224 | 3 | 4 | | | IV-1 | Far2 | 1.12 | 11320 | 3 | 4 | | | IV-1 | Fn1 | 1.06 |
| 11225 | 3 | 4 | | | IV-1 | Farp1 | 1.21 | 11321 | 3 | 4 | | | IV-1 | Fnbp1 | 1.04 |
| 11226 | 3 | 4 | | | IV-1 | Fasn | 1.01 | 11322 | 3 | 4 | | | IV-1 | Fnbp1l | 1.25 |
| 11227 | 3 | 4 | | | IV-1 | Fastkd3 | 1.08 | 11323 | 3 | 4 | | | IV-1 | Fnbp4 | 1.31 |
| 11228 | 3 | 4 | | | IV-1 | Fat1 | 1.36 | 11324 | 3 | 4 | | | IV-1 | Fndc1 | 1.02 |
| 11229 | 3 | 4 | | | IV-1 | Fat2 | 1.01 | 11325 | 3 | 4 | | | IV-1 | Fndc3a | 1.11 |

Fig. 45 - 60

| | | | | | | | | | | | | | | |
|---|---|---|---|---|---|---|---|---|---|---|---|---|---|---|
| 11326 | 3 | 4 | | | IV-1 | Fndc3b | 1.04 | 11422 | 3 | 4 | | | IV-1 | Gas8 | 1.24 |
| 11327 | 3 | 4 | | | IV-1 | Fndc4 | 1.17 | 11423 | 3 | 4 | | | IV-1 | Gata2 | 1.22 |
| 11328 | 3 | 4 | | | IV-1 | Fnip1 | 1.10 | 11424 | 3 | 4 | | | IV-1 | Gatad2b | 1.02 |
| 11329 | 3 | 4 | | | IV-1 | Fos | 1.38 | 11425 | 3 | 4 | | | IV-1 | Gatc | 1.01 |
| 11330 | 3 | 4 | | | IV-1 | Fosb | 1.03 | 11426 | 3 | 4 | | | IV-1 | Gatsl3 | 1.25 |
| 11331 | 3 | 4 | | | IV-1 | Foxc2 | 1.15 | 11427 | 3 | 4 | | | IV-1 | Gba2 | 1.02 |
| 11332 | 3 | 4 | | | IV-1 | Foxd1 | 1.41 | 11428 | 3 | 4 | | | IV-1 | Gbgt1 | 1.17 |
| 11333 | 3 | 4 | | | IV-1 | Foxd2 | 1.06 | 11429 | 3 | 4 | | | IV-1 | Gbp6 | 1.31 |
| 11334 | 3 | 4 | | | IV-1 | Foxd3 | 1.15 | 11430 | 3 | 4 | | | IV-1 | Gbx1 | 1.45 |
| 11335 | 3 | 4 | | | IV-1 | Foxj1 | 1.04 | 11431 | 3 | 4 | | | IV-1 | Gca | 1.16 |
| 11336 | 3 | 4 | | | IV-1 | Foxj3 | 1.29 | 11432 | 3 | 4 | | | IV-1 | Gcc1 | 1.22 |
| 11337 | 3 | 4 | | | IV-1 | Foxk1 | 1.08 | 11433 | 3 | 4 | | | IV-1 | Gcc2 | 1.04 |
| 11338 | 3 | 4 | | | IV-1 | Foxl2 | 1.22 | 11434 | 3 | 4 | | | IV-1 | Gclc | 1.18 |
| 11339 | 3 | 4 | | | IV-1 | Foxl2os | 1.14 | 11435 | 3 | 4 | | | IV-1 | Gdap1 | 1.46 |
| 11340 | 3 | 4 | | | IV-1 | Foxp1 | 1.15 | 11436 | 3 | 4 | | | IV-1 | Gdap2 | 1.03 |
| 11341 | 3 | 4 | | | IV-1 | Foxp2 | 1.27 | 11437 | 3 | 4 | | | IV-1 | Gdf1 | 1.43 |
| 11342 | 3 | 4 | | | IV-1 | Foxp4 | 1.39 | 11438 | 3 | 4 | | | IV-1 | Gdf10 | 1.35 |
| 11343 | 3 | 4 | | | IV-1 | Foxred1 | 1.07 | 11439 | 3 | 4 | | | IV-1 | Gdf2 | 1.02 |
| 11344 | 3 | 4 | | | IV-1 | Foxred2 | 1.36 | 11440 | 3 | 4 | | | IV-1 | Gdf9 | 1.11 |
| 11345 | 3 | 4 | | | IV-1 | Foxs1 | 1.04 | 11441 | 3 | 4 | | | IV-1 | Gdi1 | 1.20 |
| 11346 | 3 | 4 | | | IV-1 | Fpgs | 1.04 | 11442 | 3 | 4 | | | IV-1 | Gdnf | 1.05 |
| 11347 | 3 | 4 | | | IV-1 | Fpr2 | 1.14 | 11443 | 3 | 4 | | | IV-1 | Gdpd1 | 1.49 |
| 11348 | 3 | 4 | | | IV-1 | Frat1 | 1.18 | 11444 | 3 | 4 | | | IV-1 | Gdpd2 | 1.25 |
| 11349 | 3 | 4 | | | IV-1 | Frat2 | 1.36 | 11445 | 3 | 4 | | | IV-1 | Gdpd3 | 1.14 |
| 11350 | 3 | 4 | | | IV-1 | Frg1 | 1.13 | 11446 | 3 | 4 | | | IV-1 | Gdpd5 | 1.31 |
| 11351 | 3 | 4 | | | IV-1 | Frk | 1.00 | 11447 | 3 | 4 | | | IV-1 | Get4 | 1.11 |
| 11352 | 3 | 4 | | | IV-1 | Frmd4a | 1.18 | 11448 | 3 | 4 | | | IV-1 | Gfod1 | 1.02 |
| 11353 | 3 | 4 | | | IV-1 | Frmd4b | 1.06 | 11449 | 3 | 4 | | | IV-1 | Gfod2 | 1.16 |
| 11354 | 3 | 4 | | | IV-1 | Frmd6 | 1.01 | 11450 | 3 | 4 | | | IV-1 | Gfpt2 | 1.38 |
| 11355 | 3 | 4 | | | IV-1 | Frmd7 | 1.24 | 11451 | 3 | 4 | | | IV-1 | Gfra1 | 1.23 |
| 11356 | 3 | 4 | | | IV-1 | Frmpd1 | 1.27 | 11452 | 3 | 4 | | | IV-1 | Gfra3 | 1.35 |
| 11357 | 3 | 4 | | | IV-1 | Frrs1l | 1.16 | 11453 | 3 | 4 | | | IV-1 | Gfra4 | 1.47 |
| 11358 | 3 | 4 | | | IV-1 | Frs2 | 1.15 | 11454 | 3 | 4 | | | IV-1 | Gfy | 1.35 |
| 11359 | 3 | 4 | | | IV-1 | Fry | 1.36 | 11455 | 3 | 4 | | | IV-1 | Ggact | 1.05 |
| 11360 | 3 | 4 | | | IV-1 | Fsd1l | 1.27 | 11456 | 3 | 4 | | | IV-1 | Ggnbp1 | 1.31 |
| 11361 | 3 | 4 | | | IV-1 | Fst | 1.30 | 11457 | 3 | 4 | | | IV-1 | Ggnbp2 | 1.03 |
| 11362 | 3 | 4 | | | IV-1 | Fstl1 | 1.03 | 11458 | 3 | 4 | | | IV-1 | Ggps1 | 1.08 |
| 11363 | 3 | 4 | | | IV-1 | Fstl4 | 1.33 | 11459 | 3 | 4 | | | IV-1 | Ggt5 | 1.12 |
| 11364 | 3 | 4 | | | IV-1 | Ftcd | 1.43 | 11460 | 3 | 4 | | | IV-1 | Gid8 | 1.02 |
| 11365 | 3 | 4 | | | IV-1 | Fto | 1.06 | 11461 | 3 | 4 | | | IV-1 | Gigyf1 | 1.38 |
| 11366 | 3 | 4 | | | IV-1 | Ftsj3 | 1.07 | 11462 | 3 | 4 | | | IV-1 | Gigyf2 | 1.00 |
| 11367 | 3 | 4 | | | IV-1 | Ftx | 1.17 | 11463 | 3 | 4 | | | IV-1 | Ginm1 | 1.10 |
| 11368 | 3 | 4 | | | IV-1 | Fubp1 | 1.01 | 11464 | 3 | 4 | | | IV-1 | Git1 | 1.29 |
| 11369 | 3 | 4 | | | IV-1 | Fubp3 | 1.27 | 11465 | 3 | 4 | | | IV-1 | Gja3 | 1.00 |
| 11370 | 3 | 4 | | | IV-1 | Fuca1 | 1.07 | 11466 | 3 | 4 | | | IV-1 | Gja8 | 1.08 |
| 11371 | 3 | 4 | | | IV-1 | Fuk | 1.00 | 11467 | 3 | 4 | | | IV-1 | Gjb2 | 1.08 |
| 11372 | 3 | 4 | | | IV-1 | Fundc2 | 1.04 | 11468 | 3 | 4 | | | IV-1 | Gjb6 | 1.24 |
| 11373 | 3 | 4 | | | IV-1 | Furin | 1.24 | 11469 | 3 | 4 | | | IV-1 | Gjc1 | 1.04 |
| 11374 | 3 | 4 | | | IV-1 | Fus | 1.00 | 11470 | 3 | 4 | | | IV-1 | Gjc3 | 1.46 |
| 11375 | 3 | 4 | | | IV-1 | Fut10 | 1.02 | 11471 | 3 | 4 | | | IV-1 | Gjd2 | 1.25 |
| 11376 | 3 | 4 | | | IV-1 | Fut8 | 1.15 | 11472 | 3 | 4 | | | IV-1 | Gjd3 | 1.11 |
| 11377 | 3 | 4 | | | IV-1 | Fut9 | 1.41 | 11473 | 3 | 4 | | | IV-1 | Gjd4 | 1.14 |
| 11378 | 3 | 4 | | | IV-1 | Fxr2 | 1.06 | 11474 | 3 | 4 | | | IV-1 | Gk5 | 1.41 |
| 11379 | 3 | 4 | | | IV-1 | Fxyd5 | 1.16 | 11475 | 3 | 4 | | | IV-1 | Gkap1 | 1.29 |
| 11380 | 3 | 4 | | | IV-1 | Fxyd6 | 1.37 | 11476 | 3 | 4 | | | IV-1 | Gla | 1.05 |
| 11381 | 3 | 4 | | | IV-1 | Fxyd7 | 1.49 | 11477 | 3 | 4 | | | IV-1 | Glb1l | 1.23 |
| 11382 | 3 | 4 | | | IV-1 | Fyn | 1.34 | 11478 | 3 | 4 | | | IV-1 | Glb1l2 | 1.27 |
| 11383 | 3 | 4 | | | IV-1 | Fzd1 | 1.24 | 11479 | 3 | 4 | | | IV-1 | Glce | 1.06 |
| 11384 | 3 | 4 | | | IV-1 | Fzd10 | 1.06 | 11480 | 3 | 4 | | | IV-1 | Glg1 | 1.05 |
| 11385 | 3 | 4 | | | IV-1 | Fzd2 | 1.03 | 11481 | 3 | 4 | | | IV-1 | Gli1 | 1.07 |
| 11386 | 3 | 4 | | | IV-1 | Fzd3 | 1.24 | 11482 | 3 | 4 | | | IV-1 | Gli2 | 1.04 |
| 11387 | 3 | 4 | | | IV-1 | Fzd6 | 1.22 | 11483 | 3 | 4 | | | IV-1 | Gli3 | 1.36 |
| 11388 | 3 | 4 | | | IV-1 | Fzd8 | 1.04 | 11484 | 3 | 4 | | | IV-1 | Glis1 | 1.23 |
| 11389 | 3 | 4 | | | IV-1 | Fzd9 | 1.36 | 11485 | 3 | 4 | | | IV-1 | Glis2 | 1.12 |
| 11390 | 3 | 4 | | | IV-1 | G3bp2 | 1.06 | 11486 | 3 | 4 | | | IV-1 | Glis3 | 1.38 |
| 11391 | 3 | 4 | | | IV-1 | G6pc3 | 1.07 | 11487 | 3 | 4 | | | IV-1 | Glmn | 1.50 |
| 11392 | 3 | 4 | | | IV-1 | G6pd2 | 1.11 | 11488 | 3 | 4 | | | IV-1 | Glrb | 1.02 |
| 11393 | 3 | 4 | | | IV-1 | Gaa | 1.07 | 11489 | 3 | 4 | | | IV-1 | Glrx2 | 1.35 |
| 11394 | 3 | 4 | | | IV-1 | Gab2 | 1.29 | 11490 | 3 | 4 | | | IV-1 | Gltscr1 | 1.05 |
| 11395 | 3 | 4 | | | IV-1 | Gab3 | 1.06 | 11491 | 3 | 4 | | | IV-1 | Gltscr1l | 1.08 |
| 11396 | 3 | 4 | | | IV-1 | Gabarapl1 | 1.28 | 11492 | 3 | 4 | | | IV-1 | Gltscr2 | 1.17 |
| 11397 | 3 | 4 | | | IV-1 | Gabbr2 | 1.19 | 11493 | 3 | 4 | | | IV-1 | Glul | 1.10 |
| 11398 | 3 | 4 | | | IV-1 | Gabra1 | 1.41 | 11494 | 3 | 4 | | | IV-1 | Glyr1 | 1.09 |
| 11399 | 3 | 4 | | | IV-1 | Gabra3 | 1.16 | 11495 | 3 | 4 | | | IV-1 | Gm10336 | 1.17 |
| 11400 | 3 | 4 | | | IV-1 | Gabrb1 | 1.31 | 11496 | 3 | 4 | | | IV-1 | Gm10509 | 1.00 |
| 11401 | 3 | 4 | | | IV-1 | Gabre | 1.37 | 11497 | 3 | 4 | | | IV-1 | Gm10516 | 1.34 |
| 11402 | 3 | 4 | | | IV-1 | Gabrg1 | 1.01 | 11498 | 3 | 4 | | | IV-1 | Gm10638 | 1.06 |
| 11403 | 3 | 4 | | | IV-1 | Gabrg2 | 1.36 | 11499 | 3 | 4 | | | IV-1 | Gm10658 | 1.37 |
| 11404 | 3 | 4 | | | IV-1 | Gadd45b | 1.12 | 11500 | 3 | 4 | | | IV-1 | Gm10768 | 1.01 |
| 11405 | 3 | 4 | | | IV-1 | Gadd45g | 1.18 | 11501 | 3 | 4 | | | IV-1 | Gm10785 | 1.42 |
| 11406 | 3 | 4 | | | IV-1 | Gak | 1.05 | 11502 | 3 | 4 | | | IV-1 | Gm10791 | 1.47 |
| 11407 | 3 | 4 | | | IV-1 | Galc | 1.06 | 11503 | 3 | 4 | | | IV-1 | Gm10941 | 1.01 |
| 11408 | 3 | 4 | | | IV-1 | Galnt13 | 1.45 | 11504 | 3 | 4 | | | IV-1 | Gm11110 | 1.43 |
| 11409 | 3 | 4 | | | IV-1 | Galnt16 | 1.05 | 11505 | 3 | 4 | | | IV-1 | Gm11346 | 1.29 |
| 11410 | 3 | 4 | | | IV-1 | Galnt7 | 1.01 | 11506 | 3 | 4 | | | IV-1 | Gm11696 | 1.25 |
| 11411 | 3 | 4 | | | IV-1 | Galntl6 | 1.10 | 11507 | 3 | 4 | | | IV-1 | Gm11944 | 1.06 |
| 11412 | 3 | 4 | | | IV-1 | Galt | 1.01 | 11508 | 3 | 4 | | | IV-1 | Gm12060 | 1.04 |
| 11413 | 3 | 4 | | | IV-1 | Gap43 | 1.31 | 11509 | 3 | 4 | | | IV-1 | Gm12992 | 1.46 |
| 11414 | 3 | 4 | | | IV-1 | Garem | 1.14 | 11510 | 3 | 4 | | | IV-1 | Gm13157 | 1.01 |
| 11415 | 3 | 4 | | | IV-1 | Gareml | 1.49 | 11511 | 3 | 4 | | | IV-1 | Gm13212 | 1.05 |
| 11416 | 3 | 4 | | | IV-1 | Gars | 1.06 | 11512 | 3 | 4 | | | IV-1 | Gm13251 | 1.28 |
| 11417 | 3 | 4 | | | IV-1 | Gas1 | 1.27 | 11513 | 3 | 4 | | | IV-1 | Gm13298 | 1.11 |
| 11418 | 3 | 4 | | | IV-1 | Gas2 | 1.26 | 11514 | 3 | 4 | | | IV-1 | Gm13363 | 1.16 |
| 11419 | 3 | 4 | | | IV-1 | Gas5 | 1.14 | 11515 | 3 | 4 | | | IV-1 | Gm13498 | 1.02 |
| 11420 | 3 | 4 | | | IV-1 | Gas6 | 1.05 | 11516 | 3 | 4 | | | IV-1 | Gm13826 | 1.02 |
| 11421 | 3 | 4 | | | IV-1 | Gas7 | 1.01 | 11517 | 3 | 4 | | | IV-1 | Gm14057 | 1.04 |

Fig. 45 - 61

| | | | | | | | |
|---|---|---|---|---|---|---|---|
| 11518 | 3 | 4 | | | IV-1 | Gm14164 | 1.06 |
| 11519 | 3 | 4 | | | IV-1 | Gm14325 | 1.20 |
| 11520 | 3 | 4 | | | IV-1 | Gm14393 | 1.23 |
| 11521 | 3 | 4 | | | IV-1 | Gm14420 | 1.08 |
| 11522 | 3 | 4 | | | IV-1 | Gm14431 | 1.08 |
| 11523 | 3 | 4 | | | IV-1 | Gm14446 | 1.17 |
| 11524 | 3 | 4 | | | IV-1 | Gm14635 | 1.45 |
| 11525 | 3 | 4 | | | IV-1 | Gm15055 | 1.37 |
| 11526 | 3 | 4 | | | IV-1 | Gm15328 | 1.37 |
| 11527 | 3 | 4 | | | IV-1 | Gm15408 | 1.05 |
| 11528 | 3 | 4 | | | IV-1 | Gm15417 | 1.43 |
| 11529 | 3 | 4 | | | IV-1 | Gm15441 | 1.05 |
| 11530 | 3 | 4 | | | IV-1 | Gm15708 | 1.33 |
| 11531 | 3 | 4 | | | IV-1 | Gm15800 | 1.01 |
| 11532 | 3 | 4 | | | IV-1 | Gm16532 | 1.13 |
| 11533 | 3 | 4 | | | IV-1 | Gm16551 | 1.19 |
| 11534 | 3 | 4 | | | IV-1 | Gm16596 | 1.40 |
| 11535 | 3 | 4 | | | IV-1 | Gm16740 | 1.30 |
| 11536 | 3 | 4 | | | IV-1 | Gm16861 | 1.00 |
| 11537 | 3 | 4 | | | IV-1 | Gm16907 | 1.47 |
| 11538 | 3 | 4 | | | IV-1 | Gm16973 | 1.22 |
| 11539 | 3 | 4 | | | IV-1 | Gm17066 | 1.37 |
| 11540 | 3 | 4 | | | IV-1 | Gm17296 | 1.35 |
| 11541 | 3 | 4 | | | IV-1 | Gm17455 | 1.00 |
| 11542 | 3 | 4 | | | IV-1 | Gm17762 | 1.17 |
| 11543 | 3 | 4 | | | IV-1 | Gm19557 | 1.09 |
| 11544 | 3 | 4 | | | IV-1 | Gm19705 | 1.01 |
| 11545 | 3 | 4 | | | IV-1 | Gm1976 | 1.40 |
| 11546 | 3 | 4 | | | IV-1 | Gm2011 | 1.40 |
| 11547 | 3 | 4 | | | IV-1 | Gm2027 | 1.10 |
| 11548 | 3 | 4 | | | IV-1 | Gm20605 | 1.02 |
| 11549 | 3 | 4 | | | IV-1 | Gm2061 | 1.07 |
| 11550 | 3 | 4 | | | IV-1 | Gm266 | 1.16 |
| 11551 | 3 | 4 | | | IV-1 | Gm2694 | 1.45 |
| 11552 | 3 | 4 | | | IV-1 | Gm2897 | 1.45 |
| 11553 | 3 | 4 | | | IV-1 | Gm2a | 1.02 |
| 11554 | 3 | 4 | | | IV-1 | Gm3002 | 1.12 |
| 11555 | 3 | 4 | | | IV-1 | Gm3435 | 1.26 |
| 11556 | 3 | 4 | | | IV-1 | Gm3488 | 1.32 |
| 11557 | 3 | 4 | | | IV-1 | Gm3558 | 1.46 |
| 11558 | 3 | 4 | | | IV-1 | Gm3696 | 1.42 |
| 11559 | 3 | 4 | | | IV-1 | Gm4013 | 1.44 |
| 11560 | 3 | 4 | | | IV-1 | Gm4285 | 1.40 |
| 11561 | 3 | 4 | | | IV-1 | Gm4532 | 1.36 |
| 11562 | 3 | 4 | | | IV-1 | Gm5113 | 1.08 |
| 11563 | 3 | 4 | | | IV-1 | Gm5124 | 1.21 |
| 11564 | 3 | 4 | | | IV-1 | Gm5126 | 1.19 |
| 11565 | 3 | 4 | | | IV-1 | Gm5148 | 1.14 |
| 11566 | 3 | 4 | | | IV-1 | Gm527 | 1.22 |
| 11567 | 3 | 4 | | | IV-1 | Gm53 | 1.14 |
| 11568 | 3 | 4 | | | IV-1 | Gm5468 | 1.43 |
| 11569 | 3 | 4 | | | IV-1 | Gm5617 | 1.20 |
| 11570 | 3 | 4 | | | IV-1 | Gm5643 | 1.13 |
| 11571 | 3 | 4 | | | IV-1 | Gm5779 | 1.19 |
| 11572 | 3 | 4 | | | IV-1 | Gm5796 | 1.47 |
| 11573 | 3 | 4 | | | IV-1 | Gm6251 | 1.15 |
| 11574 | 3 | 4 | | | IV-1 | Gm6402 | 1.05 |
| 11575 | 3 | 4 | | | IV-1 | Gm6525 | 1.19 |
| 11576 | 3 | 4 | | | IV-1 | Gm6548 | 1.12 |
| 11577 | 3 | 4 | | | IV-1 | Gm6623 | 1.07 |
| 11578 | 3 | 4 | | | IV-1 | Gm6654 | 1.19 |
| 11579 | 3 | 4 | | | IV-1 | Gm6682 | 1.09 |
| 11580 | 3 | 4 | | | IV-1 | Gm684 | 1.37 |
| 11581 | 3 | 4 | | | IV-1 | Gm6981 | 1.23 |
| 11582 | 3 | 4 | | | IV-1 | Gm7030 | 1.16 |
| 11583 | 3 | 4 | | | IV-1 | Gm7120 | 1.02 |
| 11584 | 3 | 4 | | | IV-1 | Gm7244 | 1.01 |
| 11585 | 3 | 4 | | | IV-1 | Gm7334 | 1.30 |
| 11586 | 3 | 4 | | | IV-1 | Gm7694 | 1.10 |
| 11587 | 3 | 4 | | | IV-1 | Gm7849 | 1.07 |
| 11588 | 3 | 4 | | | IV-1 | Gm8773 | 1.01 |
| 11589 | 3 | 4 | | | IV-1 | Gm8898 | 1.25 |
| 11590 | 3 | 4 | | | IV-1 | Gm8994 | 1.09 |
| 11591 | 3 | 4 | | | IV-1 | Gm9776 | 1.48 |
| 11592 | 3 | 4 | | | IV-1 | Gm9833 | 1.14 |
| 11593 | 3 | 4 | | | IV-1 | Gm9958 | 1.20 |
| 11594 | 3 | 4 | | | IV-1 | Gm996 | 1.37 |
| 11595 | 3 | 4 | | | IV-1 | Gmds | 1.13 |
| 11596 | 3 | 4 | | | IV-1 | Gmeb1 | 1.11 |
| 11597 | 3 | 4 | | | IV-1 | Gmfb | 1.01 |
| 11598 | 3 | 4 | | | IV-1 | Gmip | 1.26 |
| 11599 | 3 | 4 | | | IV-1 | Gmps | 1.00 |
| 11600 | 3 | 4 | | | IV-1 | Gna12 | 1.02 |
| 11601 | 3 | 4 | | | IV-1 | Gna14 | 1.01 |
| 11602 | 3 | 4 | | | IV-1 | Gnai1 | 1.03 |
| 11603 | 3 | 4 | | | IV-1 | Gnal | 1.35 |
| 11604 | 3 | 4 | | | IV-1 | Gnao1 | 1.40 |
| 11605 | 3 | 4 | | | IV-1 | Gnaq | 1.40 |
| 11606 | 3 | 4 | | | IV-1 | Gnaz | 1.44 |
| 11607 | 3 | 4 | | | IV-1 | Gnb1 | 1.10 |
| 11608 | 3 | 4 | | | IV-1 | Gnb2l1 | 1.01 |
| 11609 | 3 | 4 | | | IV-1 | Gnb5 | 1.26 |
| 11610 | 3 | 4 | | | IV-1 | Gne | 1.02 |
| 11611 | 3 | 4 | | | IV-1 | Gng8 | 1.26 |
| 11612 | 3 | 4 | | | IV-1 | Gnl1 | 1.28 |
| 11613 | 3 | 4 | | | IV-1 | Gnl2 | 1.29 |
| 11614 | 3 | 4 | | | IV-1 | Gnl3 | 1.03 |
| 11615 | 3 | 4 | | | IV-1 | Gnl3l | 1.11 |
| 11616 | 3 | 4 | | | IV-1 | Gnmt | 1.21 |
| 11617 | 3 | 4 | | | IV-1 | Gnpda2 | 1.31 |
| 11618 | 3 | 4 | | | IV-1 | Gnptab | 1.02 |
| 11619 | 3 | 4 | | | IV-1 | Gnptg | 1.18 |
| 11620 | 3 | 4 | | | IV-1 | Gns | 1.06 |
| 11621 | 3 | 4 | | | IV-1 | Golga1 | 1.03 |
| 11622 | 3 | 4 | | | IV-1 | Golga2 | 1.11 |
| 11623 | 3 | 4 | | | IV-1 | Golga5 | 1.26 |
| 11624 | 3 | 4 | | | IV-1 | Golim4 | 1.04 |
| 11625 | 3 | 4 | | | IV-1 | Gon4l | 1.00 |
| 11626 | 3 | 4 | | | IV-1 | Gopc | 1.01 |
| 11627 | 3 | 4 | | | IV-1 | Gorab | 1.13 |
| 11628 | 3 | 4 | | | IV-1 | Gorasp2 | 1.09 |
| 11629 | 3 | 4 | | | IV-1 | Gosr2 | 1.03 |
| 11630 | 3 | 4 | | | IV-1 | Gp1ba | 1.02 |
| 11631 | 3 | 4 | | | IV-1 | Gpalpp1 | 1.13 |
| 11632 | 3 | 4 | | | IV-1 | Gpatch1 | 1.22 |
| 11633 | 3 | 4 | | | IV-1 | Gpatch2 | 1.10 |
| 11634 | 3 | 4 | | | IV-1 | Gpatch2l | 1.14 |
| 11635 | 3 | 4 | | | IV-1 | Gpatch4 | 1.25 |
| 11636 | 3 | 4 | | | IV-1 | Gpatch8 | 1.14 |
| 11637 | 3 | 4 | | | IV-1 | Gpc1 | 1.08 |
| 11638 | 3 | 4 | | | IV-1 | Gpc2 | 1.28 |
| 11639 | 3 | 4 | | | IV-1 | Gpc3 | 1.23 |
| 11640 | 3 | 4 | | | IV-1 | Gpc4 | 1.07 |
| 11641 | 3 | 4 | | | IV-1 | Gpc6 | 1.21 |
| 11642 | 3 | 4 | | | IV-1 | Gpcpd1 | 1.18 |
| 11643 | 3 | 4 | | | IV-1 | Gpd2 | 1.04 |
| 11644 | 3 | 4 | | | IV-1 | Gphn | 1.08 |
| 11645 | 3 | 4 | | | IV-1 | Gpihbp1 | 1.37 |
| 11646 | 3 | 4 | | | IV-1 | Gpm6b | 1.48 |
| 11647 | 3 | 4 | | | IV-1 | Gpn1 | 1.11 |
| 11648 | 3 | 4 | | | IV-1 | Gpn2 | 1.02 |
| 11649 | 3 | 4 | | | IV-1 | Gpr116 | 1.03 |
| 11650 | 3 | 4 | | | IV-1 | Gpr123 | 1.37 |
| 11651 | 3 | 4 | | | IV-1 | Gpr124 | 1.18 |
| 11652 | 3 | 4 | | | IV-1 | Gpr125 | 1.02 |
| 11653 | 3 | 4 | | | IV-1 | Gpr137 | 1.18 |
| 11654 | 3 | 4 | | | IV-1 | Gpr137b | 1.30 |
| 11655 | 3 | 4 | | | IV-1 | Gpr137b-ps | 1.20 |
| 11656 | 3 | 4 | | | IV-1 | Gpr137c | 1.19 |
| 11657 | 3 | 4 | | | IV-1 | Gpr155 | 1.01 |
| 11658 | 3 | 4 | | | IV-1 | Gpr158 | 1.18 |
| 11659 | 3 | 4 | | | IV-1 | Gpr161 | 1.32 |
| 11660 | 3 | 4 | | | IV-1 | Gpr165 | 1.01 |
| 11661 | 3 | 4 | | | IV-1 | Gpr19 | 1.21 |
| 11662 | 3 | 4 | | | IV-1 | Gpr25 | 1.10 |
| 11663 | 3 | 4 | | | IV-1 | Gpr26 | 1.34 |
| 11664 | 3 | 4 | | | IV-1 | Gpr37 | 1.09 |
| 11665 | 3 | 4 | | | IV-1 | Gpr45 | 1.01 |
| 11666 | 3 | 4 | | | IV-1 | Gpr56 | 1.09 |
| 11667 | 3 | 4 | | | IV-1 | Gpr64 | 1.42 |
| 11668 | 3 | 4 | | | IV-1 | Gpr88 | 1.17 |
| 11669 | 3 | 4 | | | IV-1 | Gpr97 | 1.17 |
| 11670 | 3 | 4 | | | IV-1 | Gprasp1 | 1.28 |
| 11671 | 3 | 4 | | | IV-1 | Gprasp2 | 1.29 |
| 11672 | 3 | 4 | | | IV-1 | Gprc5a | 1.47 |
| 11673 | 3 | 4 | | | IV-1 | Gprin1 | 1.49 |
| 11674 | 3 | 4 | | | IV-1 | Gps1 | 1.02 |
| 11675 | 3 | 4 | | | IV-1 | Gpsm1 | 1.36 |
| 11676 | 3 | 4 | | | IV-1 | Gpsm3 | 1.02 |
| 11677 | 3 | 4 | | | IV-1 | Gramd1a | 1.11 |
| 11678 | 3 | 4 | | | IV-1 | Gramd1b | 1.07 |
| 11679 | 3 | 4 | | | IV-1 | Gramd4 | 1.28 |
| 11680 | 3 | 4 | | | IV-1 | Grap2 | 1.31 |
| 11681 | 3 | 4 | | | IV-1 | Grb2 | 1.06 |
| 11682 | 3 | 4 | | | IV-1 | Greb1 | 1.23 |
| 11683 | 3 | 4 | | | IV-1 | Greb1l | 1.42 |
| 11684 | 3 | 4 | | | IV-1 | Grem1 | 1.37 |
| 11685 | 3 | 4 | | | IV-1 | Grem2 | 1.19 |
| 11686 | 3 | 4 | | | IV-1 | Gria3 | 1.43 |
| 11687 | 3 | 4 | | | IV-1 | Gria4 | 1.37 |
| 11688 | 3 | 4 | | | IV-1 | Grid1 | 1.38 |
| 11689 | 3 | 4 | | | IV-1 | Grik1 | 1.03 |
| 11690 | 3 | 4 | | | IV-1 | Grin1 | 1.36 |
| 11691 | 3 | 4 | | | IV-1 | Grin1os | 1.42 |
| 11692 | 3 | 4 | | | IV-1 | Grin2d | 1.12 |
| 11693 | 3 | 4 | | | IV-1 | Grin3a | 1.40 |
| 11694 | 3 | 4 | | | IV-1 | Grina | 1.10 |
| 11695 | 3 | 4 | | | IV-1 | Grip2 | 1.04 |
| 11696 | 3 | 4 | | | IV-1 | Gripap1 | 1.01 |
| 11697 | 3 | 4 | | | IV-1 | Grk5 | 1.02 |
| 11698 | 3 | 4 | | | IV-1 | Grk6 | 1.00 |
| 11699 | 3 | 4 | | | IV-1 | Grm1 | 1.18 |
| 11700 | 3 | 4 | | | IV-1 | Grm3 | 1.27 |
| 11701 | 3 | 4 | | | IV-1 | Grm4 | 1.19 |
| 11702 | 3 | 4 | | | IV-1 | Grm5 | 1.42 |
| 11703 | 3 | 4 | | | IV-1 | Grm8 | 1.17 |
| 11704 | 3 | 4 | | | IV-1 | Grn | 1.01 |
| 11705 | 3 | 4 | | | IV-1 | Grpel2 | 1.11 |
| 11706 | 3 | 4 | | | IV-1 | Gsap | 1.12 |
| 11707 | 3 | 4 | | | IV-1 | Gsc | 1.17 |
| 11708 | 3 | 4 | | | IV-1 | Gse1 | 1.03 |
| 11709 | 3 | 4 | | | IV-1 | Gsg1l | 1.21 |

Fig. 45 - 62

| | | | | | | |
|---|---|---|---|---|---|---|
| 11710 | 3 | 4 | | IV-1 | Gsk3b | 1.13 |
| 11711 | 3 | 4 | | IV-1 | Gskip | 1.14 |
| 11712 | 3 | 4 | | IV-1 | Gspt1 | 1.09 |
| 11713 | 3 | 4 | | IV-1 | Gspt2 | 1.27 |
| 11714 | 3 | 4 | | IV-1 | Gsr | 1.10 |
| 11715 | 3 | 4 | | IV-1 | Gstcd | 1.24 |
| 11716 | 3 | 4 | | IV-1 | Gstm1 | 1.09 |
| 11717 | 3 | 4 | | IV-1 | Gstm2 | 1.29 |
| 11718 | 3 | 4 | | IV-1 | Gstt2 | 1.31 |
| 11719 | 3 | 4 | | IV-1 | Gstt3 | 1.21 |
| 11720 | 3 | 4 | | IV-1 | Gt(ROSA)26Sor | 1.05 |
| 11721 | 3 | 4 | | IV-1 | Gtdc1 | 1.23 |
| 11722 | 3 | 4 | | IV-1 | Gtf2a1 | 1.15 |
| 11723 | 3 | 4 | | IV-1 | Gtf2b | 1.06 |
| 11724 | 3 | 4 | | IV-1 | Gtf2h1 | 1.10 |
| 11725 | 3 | 4 | | IV-1 | Gtf2h2 | 1.13 |
| 11726 | 3 | 4 | | IV-1 | Gtf2ird1 | 1.25 |
| 11727 | 3 | 4 | | IV-1 | Gtf2ird2 | 1.41 |
| 11728 | 3 | 4 | | IV-1 | Gtf3c2 | 1.05 |
| 11729 | 3 | 4 | | IV-1 | Gtf3c4 | 1.02 |
| 11730 | 3 | 4 | | IV-1 | Gtl3 | 1.16 |
| 11731 | 3 | 4 | | IV-1 | Gtpbp10 | 1.22 |
| 11732 | 3 | 4 | | IV-1 | Gtpbp4 | 1.00 |
| 11733 | 3 | 4 | | IV-1 | Gtpbp8 | 1.12 |
| 11734 | 3 | 4 | | IV-1 | Gufl | 1.38 |
| 11735 | 3 | 4 | | IV-1 | Gulp1 | 1.03 |
| 11736 | 3 | 4 | | IV-1 | H13 | 1.05 |
| 11737 | 3 | 4 | | IV-1 | H19 | 1.00 |
| 11738 | 3 | 4 | | IV-1 | H1f0 | 1.03 |
| 11739 | 3 | 4 | | IV-1 | H1fx | 1.11 |
| 11740 | 3 | 4 | | IV-1 | H2-D1 | 1.04 |
| 11741 | 3 | 4 | | IV-1 | H2-DMa | 1.25 |
| 11742 | 3 | 4 | | IV-1 | H2-DMb1 | 1.14 |
| 11743 | 3 | 4 | | IV-1 | H2-T22 | 1.10 |
| 11744 | 3 | 4 | | IV-1 | H2afy | 1.02 |
| 11745 | 3 | 4 | | IV-1 | H2afy2 | 1.25 |
| 11746 | 3 | 4 | | IV-1 | H2afy3 | 1.25 |
| 11747 | 3 | 4 | | IV-1 | H3f3b | 1.21 |
| 11748 | 3 | 4 | | IV-1 | Habp4 | 1.05 |
| 11749 | 3 | 4 | | IV-1 | Hacl1 | 1.20 |
| 11750 | 3 | 4 | | IV-1 | Hand2 | 1.49 |
| 11751 | 3 | 4 | | IV-1 | Hapln1 | 1.28 |
| 11752 | 3 | 4 | | IV-1 | Has2 | 1.08 |
| 11753 | 3 | 4 | | IV-1 | Haus1 | 1.24 |
| 11754 | 3 | 4 | | IV-1 | Haus2 | 1.31 |
| 11755 | 3 | 4 | | IV-1 | Haus7 | 1.10 |
| 11756 | 3 | 4 | | IV-1 | Hbp1 | 1.10 |
| 11757 | 3 | 4 | | IV-1 | Hck | 1.13 |
| 11758 | 3 | 4 | | IV-1 | Hcn1 | 1.24 |
| 11759 | 3 | 4 | | IV-1 | Hcn2 | 1.11 |
| 11760 | 3 | 4 | | IV-1 | Hcn3 | 1.10 |
| 11761 | 3 | 4 | | IV-1 | Hdac10 | 1.22 |
| 11762 | 3 | 4 | | IV-1 | Hdac11 | 1.14 |
| 11763 | 3 | 4 | | IV-1 | Hdac3 | 1.09 |
| 11764 | 3 | 4 | | IV-1 | Hdac4 | 1.31 |
| 11765 | 3 | 4 | | IV-1 | Hdac6 | 1.12 |
| 11766 | 3 | 4 | | IV-1 | Hdac7 | 1.22 |
| 11767 | 3 | 4 | | IV-1 | Hdgfrp2 | 1.01 |
| 11768 | 3 | 4 | | IV-1 | Hdgfrp3 | 1.49 |
| 11769 | 3 | 4 | | IV-1 | Hdx | 1.22 |
| 11770 | 3 | 4 | | IV-1 | Heca | 1.08 |
| 11771 | 3 | 4 | | IV-1 | Hectd1 | 1.04 |
| 11772 | 3 | 4 | | IV-1 | Hectd2 | 1.14 |
| 11773 | 3 | 4 | | IV-1 | Hectd3 | 1.11 |
| 11774 | 3 | 4 | | IV-1 | Hecw1 | 1.45 |
| 11775 | 3 | 4 | | IV-1 | Hecw2 | 1.43 |
| 11776 | 3 | 4 | | IV-1 | Helq | 1.07 |
| 11777 | 3 | 4 | | IV-1 | Helz2 | 1.18 |
| 11778 | 3 | 4 | | IV-1 | Hemk1 | 1.05 |
| 11779 | 3 | 4 | | IV-1 | Herc2 | 1.09 |
| 11780 | 3 | 4 | | IV-1 | Herpud1 | 1.07 |
| 11781 | 3 | 4 | | IV-1 | Hes6 | 1.09 |
| 11782 | 3 | 4 | | IV-1 | Hexdc | 1.21 |
| 11783 | 3 | 4 | | IV-1 | Hexim2 | 1.16 |
| 11784 | 3 | 4 | | IV-1 | Hey2 | 1.13 |
| 11785 | 3 | 4 | | IV-1 | Hgs | 1.08 |
| 11786 | 3 | 4 | | IV-1 | Hgsnat | 1.41 |
| 11787 | 3 | 4 | | IV-1 | Hhat | 1.23 |
| 11788 | 3 | 4 | | IV-1 | Hic2 | 1.02 |
| 11789 | 3 | 4 | | IV-1 | Hid1 | 1.02 |
| 11790 | 3 | 4 | | IV-1 | Hint1 | 1.04 |
| 11791 | 3 | 4 | | IV-1 | Hipk3 | 1.05 |
| 11792 | 3 | 4 | | IV-1 | Hipk4 | 1.09 |
| 11793 | 3 | 4 | | IV-1 | Hira | 1.03 |
| 11794 | 3 | 4 | | IV-1 | Hist1h3e | 1.40 |
| 11795 | 3 | 4 | | IV-1 | Hist1h4f | 1.21 |
| 11796 | 3 | 4 | | IV-1 | Hist1h4n | 1.03 |
| 11797 | 3 | 4 | | IV-1 | Hist2h2aa1 | 1.39 |
| 11798 | 3 | 4 | | IV-1 | Hist2h2aa2 | 1.27 |
| 11799 | 3 | 4 | | IV-1 | Hist3h2ba | 1.24 |
| 11800 | 3 | 4 | | IV-1 | Hivep1 | 1.12 |
| 11801 | 3 | 4 | | IV-1 | Hivep2 | 1.19 |
| 11802 | 3 | 4 | | IV-1 | Hivep3 | 1.32 |
| 11803 | 3 | 4 | | IV-1 | Hlcs | 1.18 |
| 11804 | 3 | 4 | | IV-1 | Hlf | 1.07 |
| 11805 | 3 | 4 | | IV-1 | Hlx | 1.05 |
| 11806 | 3 | 4 | | IV-1 | Hmbox1 | 1.03 |
| 11807 | 3 | 4 | | IV-1 | Hmces | 1.04 |
| 11808 | 3 | 4 | | IV-1 | Hmcn1 | 1.25 |
| 11809 | 3 | 4 | | IV-1 | Hmga1-rs1 | 1.03 |
| 11810 | 3 | 4 | | IV-1 | Hmga2 | 1.21 |
| 11811 | 3 | 4 | | IV-1 | Hmgb3 | 1.01 |
| 11812 | 3 | 4 | | IV-1 | Hmgcs2 | 1.30 |
| 11813 | 3 | 4 | | IV-1 | Hmgn3 | 1.03 |
| 11814 | 3 | 4 | | IV-1 | Hmgxb3 | 1.04 |
| 11815 | 3 | 4 | | IV-1 | Hnrnpa0 | 1.11 |
| 11816 | 3 | 4 | | IV-1 | Hnrnpa3 | 1.05 |
| 11817 | 3 | 4 | | IV-1 | Hnrnpdl | 1.07 |
| 11818 | 3 | 4 | | IV-1 | Hnrnpr | 1.17 |
| 11819 | 3 | 4 | | IV-1 | Homer3 | 1.11 |
| 11820 | 3 | 4 | | IV-1 | Hook1 | 1.13 |
| 11821 | 3 | 4 | | IV-1 | Hook2 | 1.40 |
| 11822 | 3 | 4 | | IV-1 | Hook3 | 1.07 |
| 11823 | 3 | 4 | | IV-1 | Hopx | 1.19 |
| 11824 | 3 | 4 | | IV-1 | Hoxa11 | 1.12 |
| 11825 | 3 | 4 | | IV-1 | Hoxa13 | 1.13 |
| 11826 | 3 | 4 | | IV-1 | Hoxa2 | 1.05 |
| 11827 | 3 | 4 | | IV-1 | Hoxa5 | 1.10 |
| 11828 | 3 | 4 | | IV-1 | Hoxa6 | 1.39 |
| 11829 | 3 | 4 | | IV-1 | Hoxa7 | 1.13 |
| 11830 | 3 | 4 | | IV-1 | Hoxa9 | 1.20 |
| 11831 | 3 | 4 | | IV-1 | Hoxb3 | 1.30 |
| 11832 | 3 | 4 | | IV-1 | Hoxb5 | 1.42 |
| 11833 | 3 | 4 | | IV-1 | Hoxb6 | 1.34 |
| 11834 | 3 | 4 | | IV-1 | Hoxb7 | 1.19 |
| 11835 | 3 | 4 | | IV-1 | Hoxb9 | 1.40 |
| 11836 | 3 | 4 | | IV-1 | Hoxc10 | 1.11 |
| 11837 | 3 | 4 | | IV-1 | Hoxc11 | 1.44 |
| 11838 | 3 | 4 | | IV-1 | Hoxc12 | 1.04 |
| 11839 | 3 | 4 | | IV-1 | Hoxc13 | 1.19 |
| 11840 | 3 | 4 | | IV-1 | Hoxc4 | 1.38 |
| 11841 | 3 | 4 | | IV-1 | Hoxc5 | 1.01 |
| 11842 | 3 | 4 | | IV-1 | Hoxc8 | 1.25 |
| 11843 | 3 | 4 | | IV-1 | Hoxc9 | 1.15 |
| 11844 | 3 | 4 | | IV-1 | Hoxd1 | 1.10 |
| 11845 | 3 | 4 | | IV-1 | Hoxd10 | 1.16 |
| 11846 | 3 | 4 | | IV-1 | Hoxd11 | 1.27 |
| 11847 | 3 | 4 | | IV-1 | Hoxd12 | 1.31 |
| 11848 | 3 | 4 | | IV-1 | Hoxd13 | 1.33 |
| 11849 | 3 | 4 | | IV-1 | Hoxd3 | 1.25 |
| 11850 | 3 | 4 | | IV-1 | Hp1bp3 | 1.24 |
| 11851 | 3 | 4 | | IV-1 | Hpcal1 | 1.05 |
| 11852 | 3 | 4 | | IV-1 | Hpcal4 | 1.28 |
| 11853 | 3 | 4 | | IV-1 | Hpgd | 1.04 |
| 11854 | 3 | 4 | | IV-1 | Hps3 | 1.49 |
| 11855 | 3 | 4 | | IV-1 | Hr | 1.48 |
| 11856 | 3 | 4 | | IV-1 | Hrg | 1.35 |
| 11857 | 3 | 4 | | IV-1 | Hs2st1 | 1.18 |
| 11858 | 3 | 4 | | IV-1 | Hs3st1 | 1.39 |
| 11859 | 3 | 4 | | IV-1 | Hs3st2 | 1.10 |
| 11860 | 3 | 4 | | IV-1 | Hs3st3a1 | 1.06 |
| 11861 | 3 | 4 | | IV-1 | Hs3st6 | 1.01 |
| 11862 | 3 | 4 | | IV-1 | Hs6st2 | 1.03 |
| 11863 | 3 | 4 | | IV-1 | Hsbp1 | 1.06 |
| 11864 | 3 | 4 | | IV-1 | Hsbp1l1 | 1.03 |
| 11865 | 3 | 4 | | IV-1 | Hsd11b2 | 1.36 |
| 11866 | 3 | 4 | | IV-1 | Hsd17b11 | 1.02 |
| 11867 | 3 | 4 | | IV-1 | Hsd17b13 | 1.29 |
| 11868 | 3 | 4 | | IV-1 | Hsd17b7 | 1.38 |
| 11869 | 3 | 4 | | IV-1 | Hsd3b3 | 1.32 |
| 11870 | 3 | 4 | | IV-1 | Hsdl1 | 1.23 |
| 11871 | 3 | 4 | | IV-1 | Hsf2 | 1.12 |
| 11872 | 3 | 4 | | IV-1 | Hsp90ab1 | 1.05 |
| 11873 | 3 | 4 | | IV-1 | Hspa12a | 1.26 |
| 11874 | 3 | 4 | | IV-1 | Hspa1l | 1.37 |
| 11875 | 3 | 4 | | IV-1 | Hspb11 | 1.01 |
| 11876 | 3 | 4 | | IV-1 | Hspbap1 | 1.11 |
| 11877 | 3 | 4 | | IV-1 | Htatsf1 | 1.06 |
| 11878 | 3 | 4 | | IV-1 | Htr1b | 1.19 |
| 11879 | 3 | 4 | | IV-1 | Htr2a | 1.09 |
| 11880 | 3 | 4 | | IV-1 | Htr3a | 1.38 |
| 11881 | 3 | 4 | | IV-1 | Htr7 | 1.39 |
| 11882 | 3 | 4 | | IV-1 | Htt | 1.02 |
| 11883 | 3 | 4 | | IV-1 | Hunk | 1.17 |
| 11884 | 3 | 4 | | IV-1 | Hyal1 | 1.26 |
| 11885 | 3 | 4 | | IV-1 | Hykk | 1.00 |
| 11886 | 3 | 4 | | IV-1 | Iars | 1.03 |
| 11887 | 3 | 4 | | IV-1 | Iars2 | 1.04 |
| 11888 | 3 | 4 | | IV-1 | Ica1 | 1.33 |
| 11889 | 3 | 4 | | IV-1 | Icam1 | 1.26 |
| 11890 | 3 | 4 | | IV-1 | Ick | 1.21 |
| 11891 | 3 | 4 | | IV-1 | Icosl | 1.04 |
| 11892 | 3 | 4 | | IV-1 | Ict1 | 1.08 |
| 11893 | 3 | 4 | | IV-1 | Id2 | 1.06 |
| 11894 | 3 | 4 | | IV-1 | Id4 | 1.45 |
| 11895 | 3 | 4 | | IV-1 | Ids | 1.49 |
| 11896 | 3 | 4 | | IV-1 | Idua | 1.08 |
| 11897 | 3 | 4 | | IV-1 | Ier2 | 1.07 |
| 11898 | 3 | 4 | | IV-1 | Ier3 | 1.21 |
| 11899 | 3 | 4 | | IV-1 | Ier3ip1 | 1.05 |
| 11900 | 3 | 4 | | IV-1 | Ier5 | 1.11 |
| 11901 | 3 | 4 | | IV-1 | Iffo1 | 1.21 |

Fig. 45 - 63

| | | | | | | | | | | | | | | |
|---|---|---|---|---|---|---|---|---|---|---|---|---|---|---|
| 11902 | 3 | 4 | | | IV-1 | Iffo2 | 1.01 | 11998 | 3 | 4 | | | IV-1 | Ireb2 | 1.06 |
| 11903 | 3 | 4 | | | IV-1 | Ifi205 | 1.29 | 11999 | 3 | 4 | | | IV-1 | Irf2bp1 | 1.01 |
| 11904 | 3 | 4 | | | IV-1 | Ifi35 | 1.05 | 12000 | 3 | 4 | | | IV-1 | Irf2bp2 | 1.03 |
| 11905 | 3 | 4 | | | IV-1 | Ifi47 | 1.26 | 12001 | 3 | 4 | | | IV-1 | Irf2bpl | 1.31 |
| 11906 | 3 | 4 | | | IV-1 | Ifitm10 | 1.06 | 12002 | 3 | 4 | | | IV-1 | Irf5 | 1.11 |
| 11907 | 3 | 4 | | | IV-1 | Ifitm2 | 1.11 | 12003 | 3 | 4 | | | IV-1 | Irf9 | 1.48 |
| 11908 | 3 | 4 | | | IV-1 | Ifitm7 | 1.25 | 12004 | 3 | 4 | | | IV-1 | Irgm2 | 1.22 |
| 11909 | 3 | 4 | | | IV-1 | Ifnar1 | 1.13 | 12005 | 3 | 4 | | | IV-1 | Irgq | 1.09 |
| 11910 | 3 | 4 | | | IV-1 | Ifngr1 | 1.01 | 12006 | 3 | 4 | | | IV-1 | Irs1 | 1.12 |
| 11911 | 3 | 4 | | | IV-1 | Ifngr2 | 1.05 | 12007 | 3 | 4 | | | IV-1 | Irs2 | 1.13 |
| 11912 | 3 | 4 | | | IV-1 | Ifrd1 | 1.21 | 12008 | 3 | 4 | | | IV-1 | Irx1 | 1.19 |
| 11913 | 3 | 4 | | | IV-1 | Ift27 | 1.11 | 12009 | 3 | 4 | | | IV-1 | Irx2 | 1.04 |
| 11914 | 3 | 4 | | | IV-1 | Ift43 | 1.13 | 12010 | 3 | 4 | | | IV-1 | Irx3 | 1.20 |
| 11915 | 3 | 4 | | | IV-1 | Ift46 | 1.25 | 12011 | 3 | 4 | | | IV-1 | Irx4 | 1.21 |
| 11916 | 3 | 4 | | | IV-1 | Ift52 | 1.05 | 12012 | 3 | 4 | | | IV-1 | Irx5 | 1.24 |
| 11917 | 3 | 4 | | | IV-1 | Ift57 | 1.20 | 12013 | 3 | 4 | | | IV-1 | Iscu | 1.04 |
| 11918 | 3 | 4 | | | IV-1 | Ift74 | 1.14 | 12014 | 3 | 4 | | | IV-1 | Isl2 | 1.44 |
| 11919 | 3 | 4 | | | IV-1 | Ift81 | 1.13 | 12015 | 3 | 4 | | | IV-1 | Ism1 | 1.20 |
| 11920 | 3 | 4 | | | IV-1 | Ift88 | 1.38 | 12016 | 3 | 4 | | | IV-1 | Ist1 | 1.11 |
| 11921 | 3 | 4 | | | IV-1 | Igbp1 | 1.12 | 12017 | 3 | 4 | | | IV-1 | Itfg1 | 1.27 |
| 11922 | 3 | 4 | | | IV-1 | Igf1 | 1.24 | 12018 | 3 | 4 | | | IV-1 | Itfg2 | 1.47 |
| 11923 | 3 | 4 | | | IV-1 | Igf1r | 1.29 | 12019 | 3 | 4 | | | IV-1 | Itga10 | 1.42 |
| 11924 | 3 | 4 | | | IV-1 | Igf2bp2 | 1.21 | 12020 | 3 | 4 | | | IV-1 | Itga11 | 1.17 |
| 11925 | 3 | 4 | | | IV-1 | Igf2os | 1.06 | 12021 | 3 | 4 | | | IV-1 | Itga3 | 1.03 |
| 11926 | 3 | 4 | | | IV-1 | Igfbp3 | 1.34 | 12022 | 3 | 4 | | | IV-1 | Itgal | 1.21 |
| 11927 | 3 | 4 | | | IV-1 | Igfbp4 | 1.15 | 12023 | 3 | 4 | | | IV-1 | Itgam | 1.11 |
| 11928 | 3 | 4 | | | IV-1 | Igfbp5 | 1.13 | 12024 | 3 | 4 | | | IV-1 | Itgav | 1.01 |
| 11929 | 3 | 4 | | | IV-1 | Ighmbp2 | 1.46 | 12025 | 3 | 4 | | | IV-1 | Itgb4 | 1.01 |
| 11930 | 3 | 4 | | | IV-1 | Igsf3 | 1.18 | 12026 | 3 | 4 | | | IV-1 | Itgbl1 | 1.13 |
| 11931 | 3 | 4 | | | IV-1 | Igsf6 | 1.21 | 12027 | 3 | 4 | | | IV-1 | Itpkc | 1.03 |
| 11932 | 3 | 4 | | | IV-1 | Igsf9b | 1.18 | 12028 | 3 | 4 | | | IV-1 | Itpr1 | 1.01 |
| 11933 | 3 | 4 | | | IV-1 | Igtp | 1.16 | 12029 | 3 | 4 | | | IV-1 | Itpr3 | 1.05 |
| 11934 | 3 | 4 | | | IV-1 | Ik | 1.05 | 12030 | 3 | 4 | | | IV-1 | Ivns1abp | 1.05 |
| 11935 | 3 | 4 | | | IV-1 | Ikbip | 1.04 | 12031 | 3 | 4 | | | IV-1 | Izumo4 | 1.04 |
| 11936 | 3 | 4 | | | IV-1 | Ikbkap | 1.11 | 12032 | 3 | 4 | | | IV-1 | Jade3 | 1.04 |
| 11937 | 3 | 4 | | | IV-1 | Ikbkb | 1.07 | 12033 | 3 | 4 | | | IV-1 | Jag1 | 1.05 |
| 11938 | 3 | 4 | | | IV-1 | Ikbkg | 1.11 | 12034 | 3 | 4 | | | IV-1 | Jak2 | 1.17 |
| 11939 | 3 | 4 | | | IV-1 | Il10ra | 1.20 | 12035 | 3 | 4 | | | IV-1 | Jakmip1 | 1.35 |
| 11940 | 3 | 4 | | | IV-1 | Il11ra1 | 1.12 | 12036 | 3 | 4 | | | IV-1 | Jakmip3 | 1.44 |
| 11941 | 3 | 4 | | | IV-1 | Il12rb2 | 1.07 | 12037 | 3 | 4 | | | IV-1 | Jazf1 | 1.08 |
| 11942 | 3 | 4 | | | IV-1 | Il16 | 1.04 | 12038 | 3 | 4 | | | IV-1 | Jdp2 | 1.30 |
| 11943 | 3 | 4 | | | IV-1 | Il17d | 1.46 | 12039 | 3 | 4 | | | IV-1 | Jkamp | 1.17 |
| 11944 | 3 | 4 | | | IV-1 | Il17rd | 1.24 | 12040 | 3 | 4 | | | IV-1 | Jmjd1c | 1.15 |
| 11945 | 3 | 4 | | | IV-1 | Il18bp | 1.08 | 12041 | 3 | 4 | | | IV-1 | Jmjd7 | 1.32 |
| 11946 | 3 | 4 | | | IV-1 | Il1r1 | 1.19 | 12042 | 3 | 4 | | | IV-1 | Jmy | 1.05 |
| 11947 | 3 | 4 | | | IV-1 | Il1rap | 1.04 | 12043 | 3 | 4 | | | IV-1 | Jph4 | 1.48 |
| 11948 | 3 | 4 | | | IV-1 | Il1rl2 | 1.30 | 12044 | 3 | 4 | | | IV-1 | Jrk | 1.19 |
| 11949 | 3 | 4 | | | IV-1 | Il33 | 1.48 | 12045 | 3 | 4 | | | IV-1 | Jtb | 1.04 |
| 11950 | 3 | 4 | | | IV-1 | Il3ra | 1.13 | 12046 | 3 | 4 | | | IV-1 | Junb | 1.06 |
| 11951 | 3 | 4 | | | IV-1 | Il4ra | 1.12 | 12047 | 3 | 4 | | | IV-1 | Jund | 1.00 |
| 11952 | 3 | 4 | | | IV-1 | Il6st | 1.04 | 12048 | 3 | 4 | | | IV-1 | Kank3 | 1.41 |
| 11953 | 3 | 4 | | | IV-1 | Ildr1 | 1.02 | 12049 | 3 | 4 | | | IV-1 | Kansl1 | 1.15 |
| 11954 | 3 | 4 | | | IV-1 | Ildr2 | 1.13 | 12050 | 3 | 4 | | | IV-1 | Kansl2 | 1.09 |
| 11955 | 3 | 4 | | | IV-1 | Ilf2 | 1.02 | 12051 | 3 | 4 | | | IV-1 | Kansl3 | 1.06 |
| 11956 | 3 | 4 | | | IV-1 | Ilf3 | 1.24 | 12052 | 3 | 4 | | | IV-1 | Kat2a | 1.04 |
| 11957 | 3 | 4 | | | IV-1 | Ilvbl | 1.03 | 12053 | 3 | 4 | | | IV-1 | Kat5 | 1.20 |
| 11958 | 3 | 4 | | | IV-1 | Imp3 | 1.06 | 12054 | 3 | 4 | | | IV-1 | Kat6a | 1.00 |
| 11959 | 3 | 4 | | | IV-1 | Impact | 1.23 | 12055 | 3 | 4 | | | IV-1 | Kat6b | 1.44 |
| 11960 | 3 | 4 | | | IV-1 | Impad1 | 1.07 | 12056 | 3 | 4 | | | IV-1 | Kat7 | 1.03 |
| 11961 | 3 | 4 | | | IV-1 | Impdh2 | 1.01 | 12057 | 3 | 4 | | | IV-1 | Kat8 | 1.19 |
| 11962 | 3 | 4 | | | IV-1 | Ina | 1.44 | 12058 | 3 | 4 | | | IV-1 | Katna1 | 1.08 |
| 11963 | 3 | 4 | | | IV-1 | Inadl | 1.11 | 12059 | 3 | 4 | | | IV-1 | Katnb1 | 1.10 |
| 11964 | 3 | 4 | | | IV-1 | Inf2 | 1.11 | 12060 | 3 | 4 | | | IV-1 | Katnbl1 | 1.03 |
| 11965 | 3 | 4 | | | IV-1 | Inhbb | 1.35 | 12061 | 3 | 4 | | | IV-1 | Kazn | 1.36 |
| 11966 | 3 | 4 | | | IV-1 | Inhbe | 1.27 | 12062 | 3 | 4 | | | IV-1 | Kbtbd2 | 1.08 |
| 11967 | 3 | 4 | | | IV-1 | Inip | 1.04 | 12063 | 3 | 4 | | | IV-1 | Kbtbd3 | 1.29 |
| 11968 | 3 | 4 | | | IV-1 | Ino80 | 1.11 | 12064 | 3 | 4 | | | IV-1 | Kcna1 | 1.37 |
| 11969 | 3 | 4 | | | IV-1 | Ino80b | 1.11 | 12065 | 3 | 4 | | | IV-1 | Kcna2 | 1.21 |
| 11970 | 3 | 4 | | | IV-1 | Ino80c | 1.18 | 12066 | 3 | 4 | | | IV-1 | Kcna3 | 1.08 |
| 11971 | 3 | 4 | | | IV-1 | Ino80dos | 1.27 | 12067 | 3 | 4 | | | IV-1 | Kcna4 | 1.23 |
| 11972 | 3 | 4 | | | IV-1 | Ino80e | 1.04 | 12068 | 3 | 4 | | | IV-1 | Kcna5 | 1.15 |
| 11973 | 3 | 4 | | | IV-1 | Inpp1 | 1.18 | 12069 | 3 | 4 | | | IV-1 | Kcna6 | 1.09 |
| 11974 | 3 | 4 | | | IV-1 | Inpp4a | 1.05 | 12070 | 3 | 4 | | | IV-1 | Kcnab1 | 1.12 |
| 11975 | 3 | 4 | | | IV-1 | Inpp4b | 1.27 | 12071 | 3 | 4 | | | IV-1 | Kcnab2 | 1.09 |
| 11976 | 3 | 4 | | | IV-1 | Inpp5e | 1.08 | 12072 | 3 | 4 | | | IV-1 | Kcnb1 | 1.11 |
| 11977 | 3 | 4 | | | IV-1 | Inpp5j | 1.05 | 12073 | 3 | 4 | | | IV-1 | Kcnb2 | 1.15 |
| 11978 | 3 | 4 | | | IV-1 | Inpp5k | 1.33 | 12074 | 3 | 4 | | | IV-1 | Kcnc1 | 1.49 |
| 11979 | 3 | 4 | | | IV-1 | Insm1 | 1.45 | 12075 | 3 | 4 | | | IV-1 | Kcnd1 | 1.18 |
| 11980 | 3 | 4 | | | IV-1 | Insr | 1.21 | 12076 | 3 | 4 | | | IV-1 | Kcnd3 | 1.48 |
| 11981 | 3 | 4 | | | IV-1 | Ints1 | 1.00 | 12077 | 3 | 4 | | | IV-1 | Kcne1l | 1.03 |
| 11982 | 3 | 4 | | | IV-1 | Intu | 1.03 | 12078 | 3 | 4 | | | IV-1 | Kcne2 | 1.32 |
| 11983 | 3 | 4 | | | IV-1 | Ip6k1 | 1.12 | 12079 | 3 | 4 | | | IV-1 | Kcne4 | 1.27 |
| 11984 | 3 | 4 | | | IV-1 | Ip6k2 | 1.27 | 12080 | 3 | 4 | | | IV-1 | Kcng1 | 1.10 |
| 11985 | 3 | 4 | | | IV-1 | Ipcef1 | 1.19 | 12081 | 3 | 4 | | | IV-1 | Kcnh1 | 1.42 |
| 11986 | 3 | 4 | | | IV-1 | Ipo13 | 1.01 | 12082 | 3 | 4 | | | IV-1 | Kcnh2 | 1.10 |
| 11987 | 3 | 4 | | | IV-1 | Ipo4 | 1.02 | 12083 | 3 | 4 | | | IV-1 | Kcnh4 | 1.33 |
| 11988 | 3 | 4 | | | IV-1 | Ipo9 | 1.01 | 12084 | 3 | 4 | | | IV-1 | Kcnh7 | 1.04 |
| 11989 | 3 | 4 | | | IV-1 | Ippk | 1.18 | 12085 | 3 | 4 | | | IV-1 | Kcnh8 | 1.09 |
| 11990 | 3 | 4 | | | IV-1 | Iqce | 1.22 | 12086 | 3 | 4 | | | IV-1 | Kcnip2 | 1.08 |
| 11991 | 3 | 4 | | | IV-1 | Iqcg | 1.09 | 12087 | 3 | 4 | | | IV-1 | Kcnip3 | 1.06 |
| 11992 | 3 | 4 | | | IV-1 | Iqck | 1.28 | 12088 | 3 | 4 | | | IV-1 | Kcnip4 | 1.40 |
| 11993 | 3 | 4 | | | IV-1 | Iqsec1 | 1.18 | 12089 | 3 | 4 | | | IV-1 | Kcnj10 | 1.24 |
| 11994 | 3 | 4 | | | IV-1 | Iqsec2 | 1.07 | 12090 | 3 | 4 | | | IV-1 | Kcnj11 | 1.06 |
| 11995 | 3 | 4 | | | IV-1 | Irak1 | 1.06 | 12091 | 3 | 4 | | | IV-1 | Kcnj2 | 1.08 |
| 11996 | 3 | 4 | | | IV-1 | Irak1bp1 | 1.07 | 12092 | 3 | 4 | | | IV-1 | Kcnj3 | 1.02 |
| 11997 | 3 | 4 | | | IV-1 | Irak3 | 1.01 | 12093 | 3 | 4 | | | IV-1 | Kcnj6 | 1.20 |

Fig. 45 - 64

| | | | | | | | | | | | | | | | |
|---|---|---|---|---|---|---|---|---|---|---|---|---|---|---|---|
| 12094 | 3 | 4 | | | IV-1 | Kcnj8 | 1.13 | 12190 | 3 | 4 | | | IV-1 | Krt14 | 1.08 |
| 12095 | 3 | 4 | | | IV-1 | Kcnj9 | 1.06 | 12191 | 3 | 4 | | | IV-1 | Krt15 | 1.10 |
| 12096 | 3 | 4 | | | IV-1 | Kcnk1 | 1.23 | 12192 | 3 | 4 | | | IV-1 | Krt17 | 1.00 |
| 12097 | 3 | 4 | | | IV-1 | Kcnk2 | 1.48 | 12193 | 3 | 4 | | | IV-1 | Krt18 | 1.23 |
| 12098 | 3 | 4 | | | IV-1 | Kcnk9 | 1.14 | 12194 | 3 | 4 | | | IV-1 | Krt19 | 1.21 |
| 12099 | 3 | 4 | | | IV-1 | Kcnma1 | 1.19 | 12195 | 3 | 4 | | | IV-1 | Krt222 | 1.39 |
| 12100 | 3 | 4 | | | IV-1 | Kcnmb2 | 1.03 | 12196 | 3 | 4 | | | IV-1 | Krt23 | 1.15 |
| 12101 | 3 | 4 | | | IV-1 | Kcnmb4 | 1.34 | 12197 | 3 | 4 | | | IV-1 | Krt75 | 1.36 |
| 12102 | 3 | 4 | | | IV-1 | Kcnn1 | 1.16 | 12198 | 3 | 4 | | | IV-1 | L1cam | 1.26 |
| 12103 | 3 | 4 | | | IV-1 | Kcnn2 | 1.27 | 12199 | 3 | 4 | | | IV-1 | L3mbtl2 | 1.03 |
| 12104 | 3 | 4 | | | IV-1 | Kcnn3 | 1.02 | 12200 | 3 | 4 | | | IV-1 | L3mbtl3 | 1.22 |
| 12105 | 3 | 4 | | | IV-1 | Kcnq3 | 1.34 | 12201 | 3 | 4 | | | IV-1 | LOC100503496 | 1.22 |
| 12106 | 3 | 4 | | | IV-1 | Kcnrg | 1.09 | 12202 | 3 | 4 | | | IV-1 | LOC100503676 | 1.13 |
| 12107 | 3 | 4 | | | IV-1 | Kcns1 | 1.45 | 12203 | 3 | 4 | | | IV-1 | LOC100861615 | 1.06 |
| 12108 | 3 | 4 | | | IV-1 | Kctd1 | 1.02 | 12204 | 3 | 4 | | | IV-1 | LOC101669761 | 1.01 |
| 12109 | 3 | 4 | | | IV-1 | Kctd12 | 1.31 | 12205 | 3 | 4 | | | IV-1 | LOC106740 | 1.40 |
| 12110 | 3 | 4 | | | IV-1 | Kctd15 | 1.14 | 12206 | 3 | 4 | | | IV-1 | Lacc1 | 1.25 |
| 12111 | 3 | 4 | | | IV-1 | Kctd17 | 1.20 | 12207 | 3 | 4 | | | IV-1 | Lag3 | 1.45 |
| 12112 | 3 | 4 | | | IV-1 | Kctd18 | 1.46 | 12208 | 3 | 4 | | | IV-1 | Lair1 | 1.27 |
| 12113 | 3 | 4 | | | IV-1 | Kctd2 | 1.37 | 12209 | 3 | 4 | | | IV-1 | Lama1 | 1.27 |
| 12114 | 3 | 4 | | | IV-1 | Kctd3 | 1.02 | 12210 | 3 | 4 | | | IV-1 | Lama2 | 1.15 |
| 12115 | 3 | 4 | | | IV-1 | Kctd4 | 1.14 | 12211 | 3 | 4 | | | IV-1 | Lama5 | 1.09 |
| 12116 | 3 | 4 | | | IV-1 | Kctd6 | 1.41 | 12212 | 3 | 4 | | | IV-1 | Lamb2 | 1.06 |
| 12117 | 3 | 4 | | | IV-1 | Kctd8 | 1.43 | 12213 | 3 | 4 | | | IV-1 | Lamc2 | 1.09 |
| 12118 | 3 | 4 | | | IV-1 | Kdelr3 | 1.02 | 12214 | 3 | 4 | | | IV-1 | Lamc3 | 1.04 |
| 12119 | 3 | 4 | | | IV-1 | Kdm1a | 1.10 | 12215 | 3 | 4 | | | IV-1 | Lancl1 | 1.21 |
| 12120 | 3 | 4 | | | IV-1 | Kdm1b | 1.10 | 12216 | 3 | 4 | | | IV-1 | Lancl2 | 1.13 |
| 12121 | 3 | 4 | | | IV-1 | Kdm2b | 1.15 | 12217 | 3 | 4 | | | IV-1 | Lancl3 | 1.49 |
| 12122 | 3 | 4 | | | IV-1 | Kdm3b | 1.09 | 12218 | 3 | 4 | | | IV-1 | Large | 1.31 |
| 12123 | 3 | 4 | | | IV-1 | Kdm4a | 1.27 | 12219 | 3 | 4 | | | IV-1 | Lars | 1.06 |
| 12124 | 3 | 4 | | | IV-1 | Kdm4b | 1.28 | 12220 | 3 | 4 | | | IV-1 | Lasl1 | 1.31 |
| 12125 | 3 | 4 | | | IV-1 | Kdm5a | 1.19 | 12221 | 3 | 4 | | | IV-1 | Lats1 | 1.16 |
| 12126 | 3 | 4 | | | IV-1 | Kdm5b | 1.22 | 12222 | 3 | 4 | | | IV-1 | Lats2 | 1.10 |
| 12127 | 3 | 4 | | | IV-1 | Kdsr | 1.36 | 12223 | 3 | 4 | | | IV-1 | Lbh | 1.18 |
| 12128 | 3 | 4 | | | IV-1 | Khk | 1.45 | 12224 | 3 | 4 | | | IV-1 | Lbx1 | 1.05 |
| 12129 | 3 | 4 | | | IV-1 | Kidins220 | 1.16 | 12225 | 3 | 4 | | | IV-1 | Lce1h | 1.15 |
| 12130 | 3 | 4 | | | IV-1 | Kif13a | 1.14 | 12226 | 3 | 4 | | | IV-1 | Lce3a | 1.21 |
| 12131 | 3 | 4 | | | IV-1 | Kif19a | 1.09 | 12227 | 3 | 4 | | | IV-1 | Lce3f | 1.33 |
| 12132 | 3 | 4 | | | IV-1 | Kif1b | 1.08 | 12228 | 3 | 4 | | | IV-1 | Lcor1 | 1.25 |
| 12133 | 3 | 4 | | | IV-1 | Kif21a | 1.14 | 12229 | 3 | 4 | | | IV-1 | Ldb1 | 1.15 |
| 12134 | 3 | 4 | | | IV-1 | Kif26a | 1.20 | 12230 | 3 | 4 | | | IV-1 | Ldb2 | 1.24 |
| 12135 | 3 | 4 | | | IV-1 | Kif27 | 1.09 | 12231 | 3 | 4 | | | IV-1 | Ldhal6b | 1.33 |
| 12136 | 3 | 4 | | | IV-1 | Kif2a | 1.13 | 12232 | 3 | 4 | | | IV-1 | Ldlrad3 | 1.06 |
| 12137 | 3 | 4 | | | IV-1 | Kif3a | 1.19 | 12233 | 3 | 4 | | | IV-1 | Ldoc1 | 1.19 |
| 12138 | 3 | 4 | | | IV-1 | Kif3b | 1.16 | 12234 | 3 | 4 | | | IV-1 | Ldoc1l | 1.27 |
| 12139 | 3 | 4 | | | IV-1 | Kif3c | 1.46 | 12235 | 3 | 4 | | | IV-1 | Lect1 | 1.08 |
| 12140 | 3 | 4 | | | IV-1 | Kif7 | 1.05 | 12236 | 3 | 4 | | | IV-1 | Lef1 | 1.26 |
| 12141 | 3 | 4 | | | IV-1 | Kifap3 | 1.17 | 12237 | 3 | 4 | | | IV-1 | Lemd1 | 1.04 |
| 12142 | 3 | 4 | | | IV-1 | Kifc3 | 1.19 | 12238 | 3 | 4 | | | IV-1 | Lemd2 | 1.03 |
| 12143 | 3 | 4 | | | IV-1 | Kin | 1.19 | 12239 | 3 | 4 | | | IV-1 | Lemd3 | 1.04 |
| 12144 | 3 | 4 | | | IV-1 | Kirrel | 1.19 | 12240 | 3 | 4 | | | IV-1 | Lenep | 1.03 |
| 12145 | 3 | 4 | | | IV-1 | Kiss1r | 1.03 | 12241 | 3 | 4 | | | IV-1 | Leng8 | 1.39 |
| 12146 | 3 | 4 | | | IV-1 | Klc1 | 1.27 | 12242 | 3 | 4 | | | IV-1 | Leng9 | 1.28 |
| 12147 | 3 | 4 | | | IV-1 | Klc2 | 1.17 | 12243 | 3 | 4 | | | IV-1 | Leprot | 1.04 |
| 12148 | 3 | 4 | | | IV-1 | Klf10 | 1.13 | 12244 | 3 | 4 | | | IV-1 | Leprotl1 | 1.04 |
| 12149 | 3 | 4 | | | IV-1 | Klf12 | 1.08 | 12245 | 3 | 4 | | | IV-1 | Lgals8 | 1.07 |
| 12150 | 3 | 4 | | | IV-1 | Klf13 | 1.12 | 12246 | 3 | 4 | | | IV-1 | Lgals9 | 1.21 |
| 12151 | 3 | 4 | | | IV-1 | Klf14 | 1.13 | 12247 | 3 | 4 | | | IV-1 | Lgi1 | 1.29 |
| 12152 | 3 | 4 | | | IV-1 | Klf15 | 1.36 | 12248 | 3 | 4 | | | IV-1 | Lgi4 | 1.28 |
| 12153 | 3 | 4 | | | IV-1 | Klf2 | 1.02 | 12249 | 3 | 4 | | | IV-1 | Lgmn | 1.30 |
| 12154 | 3 | 4 | | | IV-1 | Klf4 | 1.14 | 12250 | 3 | 4 | | | IV-1 | Lgr4 | 1.23 |
| 12155 | 3 | 4 | | | IV-1 | Klf6 | 1.29 | 12251 | 3 | 4 | | | IV-1 | Lhfp | 1.11 |
| 12156 | 3 | 4 | | | IV-1 | Klf7 | 1.02 | 12252 | 3 | 4 | | | IV-1 | Lhfpl3 | 1.28 |
| 12157 | 3 | 4 | | | IV-1 | Klhdc10 | 1.20 | 12253 | 3 | 4 | | | IV-1 | Lhx1os | 1.40 |
| 12158 | 3 | 4 | | | IV-1 | Klhdc2 | 1.27 | 12254 | 3 | 4 | | | IV-1 | Lhx2 | 1.47 |
| 12159 | 3 | 4 | | | IV-1 | Klhdc4 | 1.03 | 12255 | 3 | 4 | | | IV-1 | Lhx6 | 1.29 |
| 12160 | 3 | 4 | | | IV-1 | Klhdc8b | 1.27 | 12256 | 3 | 4 | | | IV-1 | Lhx8 | 1.42 |
| 12161 | 3 | 4 | | | IV-1 | Klhdc9 | 1.02 | 12257 | 3 | 4 | | | IV-1 | Lias | 1.10 |
| 12162 | 3 | 4 | | | IV-1 | Klhl1 | 1.11 | 12258 | 3 | 4 | | | IV-1 | Lig3 | 1.01 |
| 12163 | 3 | 4 | | | IV-1 | Klhl11 | 1.14 | 12259 | 3 | 4 | | | IV-1 | Limch1 | 1.30 |
| 12164 | 3 | 4 | | | IV-1 | Klhl14 | 1.39 | 12260 | 3 | 4 | | | IV-1 | Limd2 | 1.01 |
| 12165 | 3 | 4 | | | IV-1 | Klhl15 | 1.11 | 12261 | 3 | 4 | | | IV-1 | Limk1 | 1.25 |
| 12166 | 3 | 4 | | | IV-1 | Klhl17 | 1.05 | 12262 | 3 | 4 | | | IV-1 | Limk2 | 1.14 |
| 12167 | 3 | 4 | | | IV-1 | Klhl2 | 1.23 | 12263 | 3 | 4 | | | IV-1 | Lims2 | 1.26 |
| 12168 | 3 | 4 | | | IV-1 | Klhl20 | 1.12 | 12264 | 3 | 4 | | | IV-1 | Lin28b | 1.05 |
| 12169 | 3 | 4 | | | IV-1 | Klhl22 | 1.09 | 12265 | 3 | 4 | | | IV-1 | Lin52 | 1.35 |
| 12170 | 3 | 4 | | | IV-1 | Klhl23 | 1.05 | 12266 | 3 | 4 | | | IV-1 | Lin7a | 1.26 |
| 12171 | 3 | 4 | | | IV-1 | Klhl24 | 1.40 | 12267 | 3 | 4 | | | IV-1 | Lin7c | 1.18 |
| 12172 | 3 | 4 | | | IV-1 | Klhl26 | 1.09 | 12268 | 3 | 4 | | | IV-1 | Lin9 | 1.02 |
| 12173 | 3 | 4 | | | IV-1 | Klhl29 | 1.49 | 12269 | 3 | 4 | | | IV-1 | Lingo1 | 1.44 |
| 12174 | 3 | 4 | | | IV-1 | Klhl32 | 1.48 | 12270 | 3 | 4 | | | IV-1 | Lingo2 | 1.24 |
| 12175 | 3 | 4 | | | IV-1 | Klhl34 | 1.25 | 12271 | 3 | 4 | | | IV-1 | Lingo3 | 1.09 |
| 12176 | 3 | 4 | | | IV-1 | Klhl36 | 1.11 | 12272 | 3 | 4 | | | IV-1 | Lipo1 | 1.01 |
| 12177 | 3 | 4 | | | IV-1 | Klhl38 | 1.01 | 12273 | 3 | 4 | | | IV-1 | Lipt2 | 1.38 |
| 12178 | 3 | 4 | | | IV-1 | Klhl5 | 1.23 | 12274 | 3 | 4 | | | IV-1 | Lix1 | 1.35 |
| 12179 | 3 | 4 | | | IV-1 | Klhl7 | 1.43 | 12275 | 3 | 4 | | | IV-1 | Lix1l | 1.29 |
| 12180 | 3 | 4 | | | IV-1 | Klhl8 | 1.09 | 12276 | 3 | 4 | | | IV-1 | Lmbrl1 | 1.30 |
| 12181 | 3 | 4 | | | IV-1 | Klk11 | 1.12 | 12277 | 3 | 4 | | | IV-1 | Lmbrd1 | 1.27 |
| 12182 | 3 | 4 | | | IV-1 | Klk9 | 1.09 | 12278 | 3 | 4 | | | IV-1 | Lmln | 1.30 |
| 12183 | 3 | 4 | | | IV-1 | Kmt2a | 1.07 | 12279 | 3 | 4 | | | IV-1 | Lmo1 | 1.11 |
| 12184 | 3 | 4 | | | IV-1 | Kmt2b | 1.17 | 12280 | 3 | 4 | | | IV-1 | Lmo4 | 1.19 |
| 12185 | 3 | 4 | | | IV-1 | Kmt2e | 1.09 | 12281 | 3 | 4 | | | IV-1 | Lnp | 1.17 |
| 12186 | 3 | 4 | | | IV-1 | Kndc1 | 1.37 | 12282 | 3 | 4 | | | IV-1 | Lnx1 | 1.39 |
| 12187 | 3 | 4 | | | IV-1 | Knop1 | 1.00 | 12283 | 3 | 4 | | | IV-1 | Loh12cr1 | 1.24 |
| 12188 | 3 | 4 | | | IV-1 | Krba1 | 1.34 | 12284 | 3 | 4 | | | IV-1 | Lonrf1 | 1.25 |
| 12189 | 3 | 4 | | | IV-1 | Kri1 | 1.30 | 12285 | 3 | 4 | | | IV-1 | Lonrf2 | 1.37 |

Fig. 45 - 65

| | | | | | | | | | | | | | | | |
|---|---|---|---|---|---|---|---|---|---|---|---|---|---|---|---|
| 12286 | 3 | 4 | | | IV-1 | Lox | 1.32 | 12382 | 3 | 4 | | | IV-1 | Maged1 | 1.08 |
| 12287 | 3 | 4 | | | IV-1 | Loxl1 | 1.19 | 12383 | 3 | 4 | | | IV-1 | Magee1 | 1.27 |
| 12288 | 3 | 4 | | | IV-1 | Loxl3 | 1.13 | 12384 | 3 | 4 | | | IV-1 | Magee2 | 1.32 |
| 12289 | 3 | 4 | | | IV-1 | Lpar2 | 1.21 | 12385 | 3 | 4 | | | IV-1 | Mageh1 | 1.34 |
| 12290 | 3 | 4 | | | IV-1 | Lpar4 | 1.07 | 12386 | 3 | 4 | | | IV-1 | Magi1 | 1.28 |
| 12291 | 3 | 4 | | | IV-1 | Lpcat2 | 1.05 | 12387 | 3 | 4 | | | IV-1 | Magohb | 1.14 |
| 12292 | 3 | 4 | | | IV-1 | Lpcat4 | 1.07 | 12388 | 3 | 4 | | | IV-1 | Malat1 | 1.16 |
| 12293 | 3 | 4 | | | IV-1 | Lpgat1 | 1.14 | 12389 | 3 | 4 | | | IV-1 | Malsu1 | 1.09 |
| 12294 | 3 | 4 | | | IV-1 | Lphn1 | 1.26 | 12390 | 3 | 4 | | | IV-1 | Malt1 | 1.05 |
| 12295 | 3 | 4 | | | IV-1 | Lphn2 | 1.28 | 12391 | 3 | 4 | | | IV-1 | Mamdc2 | 1.16 |
| 12296 | 3 | 4 | | | IV-1 | Lphn3 | 1.46 | 12392 | 3 | 4 | | | IV-1 | Maml1 | 1.26 |
| 12297 | 3 | 4 | | | IV-1 | Lpin2 | 1.07 | 12393 | 3 | 4 | | | IV-1 | Maml2 | 1.34 |
| 12298 | 3 | 4 | | | IV-1 | Lpin3 | 1.26 | 12394 | 3 | 4 | | | IV-1 | Maml3 | 1.38 |
| 12299 | 3 | 4 | | | IV-1 | Lrch1 | 1.16 | 12395 | 3 | 4 | | | IV-1 | Man1a2 | 1.14 |
| 12300 | 3 | 4 | | | IV-1 | Lrch2 | 1.27 | 12396 | 3 | 4 | | | IV-1 | Man1c1 | 1.09 |
| 12301 | 3 | 4 | | | IV-1 | Lrch3 | 1.12 | 12397 | 3 | 4 | | | IV-1 | Man2a1 | 1.04 |
| 12302 | 3 | 4 | | | IV-1 | Lrch4 | 1.41 | 12398 | 3 | 4 | | | IV-1 | Man2a2 | 1.06 |
| 12303 | 3 | 4 | | | IV-1 | Lrfn1 | 1.29 | 12399 | 3 | 4 | | | IV-1 | Man2b2 | 1.10 |
| 12304 | 3 | 4 | | | IV-1 | Lrfn3 | 1.30 | 12400 | 3 | 4 | | | IV-1 | Man2c1 | 1.17 |
| 12305 | 3 | 4 | | | IV-1 | Lrfn4 | 1.26 | 12401 | 3 | 4 | | | IV-1 | Man2c1os | 1.32 |
| 12306 | 3 | 4 | | | IV-1 | Lrif1 | 1.26 | 12402 | 3 | 4 | | | IV-1 | Manba | 1.08 |
| 12307 | 3 | 4 | | | IV-1 | Lrig2 | 1.10 | 12403 | 3 | 4 | | | IV-1 | Manbal | 1.12 |
| 12308 | 3 | 4 | | | IV-1 | Lrig3 | 1.49 | 12404 | 3 | 4 | | | IV-1 | Maneal | 1.38 |
| 12309 | 3 | 4 | | | IV-1 | Lrp1 | 1.25 | 12405 | 3 | 4 | | | IV-1 | Mansc1 | 1.01 |
| 12310 | 3 | 4 | | | IV-1 | Lrp11 | 1.36 | 12406 | 3 | 4 | | | IV-1 | Maoa | 1.04 |
| 12311 | 3 | 4 | | | IV-1 | Lrp12 | 1.44 | 12407 | 3 | 4 | | | IV-1 | Map10 | 1.34 |
| 12312 | 3 | 4 | | | IV-1 | Lrp3 | 1.23 | 12408 | 3 | 4 | | | IV-1 | Map1b | 1.28 |
| 12313 | 3 | 4 | | | IV-1 | Lrp4 | 1.07 | 12409 | 3 | 4 | | | IV-1 | Map1lc3a | 1.36 |
| 12314 | 3 | 4 | | | IV-1 | Lrp6 | 1.03 | 12410 | 3 | 4 | | | IV-1 | Map1lc3b | 1.18 |
| 12315 | 3 | 4 | | | IV-1 | Lrpap1 | 1.09 | 12411 | 3 | 4 | | | IV-1 | Map1s | 1.08 |
| 12316 | 3 | 4 | | | IV-1 | Lrrc10 | 1.27 | 12412 | 3 | 4 | | | IV-1 | Map2 | 1.33 |
| 12317 | 3 | 4 | | | IV-1 | Lrrc10b | 1.13 | 12413 | 3 | 4 | | | IV-1 | Map2k4 | 1.04 |
| 12318 | 3 | 4 | | | IV-1 | Lrrc15 | 1.04 | 12414 | 3 | 4 | | | IV-1 | Map2k5 | 1.32 |
| 12319 | 3 | 4 | | | IV-1 | Lrrc16a | 1.21 | 12415 | 3 | 4 | | | IV-1 | Map2k7 | 1.13 |
| 12320 | 3 | 4 | | | IV-1 | Lrrc24 | 1.12 | 12416 | 3 | 4 | | | IV-1 | Map3k10 | 1.20 |
| 12321 | 3 | 4 | | | IV-1 | Lrrc28 | 1.30 | 12417 | 3 | 4 | | | IV-1 | Map3k12 | 1.18 |
| 12322 | 3 | 4 | | | IV-1 | Lrrc32 | 1.23 | 12418 | 3 | 4 | | | IV-1 | Map3k13 | 1.16 |
| 12323 | 3 | 4 | | | IV-1 | Lrrc39 | 1.04 | 12419 | 3 | 4 | | | IV-1 | Map3k2 | 1.11 |
| 12324 | 3 | 4 | | | IV-1 | Lrrc3b | 1.46 | 12420 | 3 | 4 | | | IV-1 | Map3k7 | 1.17 |
| 12325 | 3 | 4 | | | IV-1 | Lrrc4 | 1.12 | 12421 | 3 | 4 | | | IV-1 | Map4 | 1.13 |
| 12326 | 3 | 4 | | | IV-1 | Lrrc4b | 1.41 | 12422 | 3 | 4 | | | IV-1 | Map4k2 | 1.04 |
| 12327 | 3 | 4 | | | IV-1 | Lrrc55 | 1.00 | 12423 | 3 | 4 | | | IV-1 | Map4k3 | 1.03 |
| 12328 | 3 | 4 | | | IV-1 | Lrrc61 | 1.36 | 12424 | 3 | 4 | | | IV-1 | Map4k4 | 1.16 |
| 12329 | 3 | 4 | | | IV-1 | Lrrc7 | 1.06 | 12425 | 3 | 4 | | | IV-1 | Map4k5 | 1.04 |
| 12330 | 3 | 4 | | | IV-1 | Lrrc71 | 1.29 | 12426 | 3 | 4 | | | IV-1 | Map6 | 1.48 |
| 12331 | 3 | 4 | | | IV-1 | Lrrc75a | 1.09 | 12427 | 3 | 4 | | | IV-1 | Map9 | 1.29 |
| 12332 | 3 | 4 | | | IV-1 | Lrrc75b | 1.33 | 12428 | 3 | 4 | | | IV-1 | Mapk11 | 1.31 |
| 12333 | 3 | 4 | | | IV-1 | Lrrc8a | 1.03 | 12429 | 3 | 4 | | | IV-1 | Mapk13 | 1.06 |
| 12334 | 3 | 4 | | | IV-1 | Lrrc8b | 1.27 | 12430 | 3 | 4 | | | IV-1 | Mapk1ip1 | 1.13 |
| 12335 | 3 | 4 | | | IV-1 | Lrrc8d | 1.35 | 12431 | 3 | 4 | | | IV-1 | Mapk6 | 1.30 |
| 12336 | 3 | 4 | | | IV-1 | Lrrcc1 | 1.34 | 12432 | 3 | 4 | | | IV-1 | Mapk7 | 1.11 |
| 12337 | 3 | 4 | | | IV-1 | Lrrfip2 | 1.00 | 12433 | 3 | 4 | | | IV-1 | Mapk8 | 1.30 |
| 12338 | 3 | 4 | | | IV-1 | Lrrn1 | 1.29 | 12434 | 3 | 4 | | | IV-1 | Mapk8ip1 | 1.23 |
| 12339 | 3 | 4 | | | IV-1 | Lrrn2 | 1.34 | 12435 | 3 | 4 | | | IV-1 | Mapk8ip3 | 1.12 |
| 12340 | 3 | 4 | | | IV-1 | Lrrn3 | 1.31 | 12436 | 3 | 4 | | | IV-1 | Mapk9 | 1.25 |
| 12341 | 3 | 4 | | | IV-1 | Lrrtm2 | 1.50 | 12437 | 3 | 4 | | | IV-1 | Mapkapk5 | 1.26 |
| 12342 | 3 | 4 | | | IV-1 | Lrrtm3 | 1.25 | 12438 | 3 | 4 | | | IV-1 | Mapkbp1 | 1.39 |
| 12343 | 3 | 4 | | | IV-1 | Lrsam1 | 1.17 | 12439 | 3 | 4 | | | IV-1 | Mapre1 | 1.09 |
| 12344 | 3 | 4 | | | IV-1 | Lrtm2 | 1.32 | 12440 | 3 | 4 | | | IV-1 | Mapre2 | 1.20 |
| 12345 | 3 | 4 | | | IV-1 | Lsg1 | 1.13 | 12441 | 3 | 4 | | | IV-1 | Mapre3 | 1.41 |
| 12346 | 3 | 4 | | | IV-1 | Lsm11 | 1.20 | 12442 | 3 | 4 | | | IV-1 | Mapt | 1.37 |
| 12347 | 3 | 4 | | | IV-1 | Lsm14b | 1.22 | 12443 | 3 | 4 | | | IV-1 | Marc2 | 1.03 |
| 12348 | 3 | 4 | | | IV-1 | Lsm5 | 1.15 | 12444 | 3 | 4 | | | IV-1 | March5 | 1.01 |
| 12349 | 3 | 4 | | | IV-1 | Lsp1 | 1.15 | 12445 | 3 | 4 | | | IV-1 | March6 | 1.10 |
| 12350 | 3 | 4 | | | IV-1 | Ltb | 1.41 | 12446 | 3 | 4 | | | IV-1 | March7 | 1.13 |
| 12351 | 3 | 4 | | | IV-1 | Ltb4r1 | 1.47 | 12447 | 3 | 4 | | | IV-1 | March9 | 1.32 |
| 12352 | 3 | 4 | | | IV-1 | Ltbp1 | 1.31 | 12448 | 3 | 4 | | | IV-1 | Marcks | 1.12 |
| 12353 | 3 | 4 | | | IV-1 | Ltbp3 | 1.01 | 12449 | 3 | 4 | | | IV-1 | Marcksl1 | 1.32 |
| 12354 | 3 | 4 | | | IV-1 | Ltbr | 1.07 | 12450 | 3 | 4 | | | IV-1 | Mark2 | 1.01 |
| 12355 | 3 | 4 | | | IV-1 | Ltv1 | 1.04 | 12451 | 3 | 4 | | | IV-1 | Mark3 | 1.07 |
| 12356 | 3 | 4 | | | IV-1 | Luc7l | 1.20 | 12452 | 3 | 4 | | | IV-1 | Mark4 | 1.30 |
| 12357 | 3 | 4 | | | IV-1 | Luc7l3 | 1.10 | 12453 | 3 | 4 | | | IV-1 | Mas1 | 1.06 |
| 12358 | 3 | 4 | | | IV-1 | Ly6c1 | 1.39 | 12454 | 3 | 4 | | | IV-1 | Mast2 | 1.07 |
| 12359 | 3 | 4 | | | IV-1 | Ly6c2 | 1.22 | 12455 | 3 | 4 | | | IV-1 | Mast4 | 1.11 |
| 12360 | 3 | 4 | | | IV-1 | Lypd3 | 1.02 | 12456 | 3 | 4 | | | IV-1 | Mat1a | 1.19 |
| 12361 | 3 | 4 | | | IV-1 | Lypd6 | 1.10 | 12457 | 3 | 4 | | | IV-1 | Mat2a | 1.06 |
| 12362 | 3 | 4 | | | IV-1 | Lypla2 | 1.05 | 12458 | 3 | 4 | | | IV-1 | Matk | 1.03 |
| 12363 | 3 | 4 | | | IV-1 | Lyrm1 | 1.10 | 12459 | 3 | 4 | | | IV-1 | Matn1 | 1.25 |
| 12364 | 3 | 4 | | | IV-1 | Lyrm2 | 1.14 | 12460 | 3 | 4 | | | IV-1 | Matn3 | 1.28 |
| 12365 | 3 | 4 | | | IV-1 | Lyrm9 | 1.12 | 12461 | 3 | 4 | | | IV-1 | Matn4 | 1.27 |
| 12366 | 3 | 4 | | | IV-1 | Lysmd1 | 1.09 | 12462 | 3 | 4 | | | IV-1 | Matr3 | 1.17 |
| 12367 | 3 | 4 | | | IV-1 | Lysmd4 | 1.03 | 12463 | 3 | 4 | | | IV-1 | Mau2 | 1.34 |
| 12368 | 3 | 4 | | | IV-1 | Lyve1 | 1.32 | 12464 | 3 | 4 | | | IV-1 | Mbd1 | 1.15 |
| 12369 | 3 | 4 | | | IV-1 | Lzic | 1.08 | 12465 | 3 | 4 | | | IV-1 | Mbd5 | 1.22 |
| 12370 | 3 | 4 | | | IV-1 | Lzts1 | 1.21 | 12466 | 3 | 4 | | | IV-1 | Mbd6 | 1.26 |
| 12371 | 3 | 4 | | | IV-1 | Lzts2 | 1.01 | 12467 | 3 | 4 | | | IV-1 | Mblac1 | 1.22 |
| 12372 | 3 | 4 | | | IV-1 | Mab21l3 | 1.01 | 12468 | 3 | 4 | | | IV-1 | Mblac2 | 1.40 |
| 12373 | 3 | 4 | | | IV-1 | Macc1 | 1.07 | 12469 | 3 | 4 | | | IV-1 | Mbnl2 | 1.02 |
| 12374 | 3 | 4 | | | IV-1 | Macf1 | 1.12 | 12470 | 3 | 4 | | | IV-1 | Mboat7 | 1.00 |
| 12375 | 3 | 4 | | | IV-1 | Mad2l2 | 1.09 | 12471 | 3 | 4 | | | IV-1 | Mbtd1 | 1.17 |
| 12376 | 3 | 4 | | | IV-1 | Madcam1 | 1.41 | 12472 | 3 | 4 | | | IV-1 | Mbtps1 | 1.05 |
| 12377 | 3 | 4 | | | IV-1 | Madd | 1.19 | 12473 | 3 | 4 | | | IV-1 | Mbtps2 | 1.15 |
| 12378 | 3 | 4 | | | IV-1 | Maf | 1.08 | 12474 | 3 | 4 | | | IV-1 | Mc5r | 1.44 |
| 12379 | 3 | 4 | | | IV-1 | Maf1 | 1.18 | 12475 | 3 | 4 | | | IV-1 | Mcam | 1.02 |
| 12380 | 3 | 4 | | | IV-1 | Mafa | 1.27 | 12476 | 3 | 4 | | | IV-1 | Mcat | 1.15 |
| 12381 | 3 | 4 | | | IV-1 | Mafg | 1.04 | 12477 | 3 | 4 | | | IV-1 | Mcf2l | 1.44 |

Fig. 45 - 66

| | | | | | | | |
|---|---|---|---|---|---|---|---|
| 12478 | 3 | 4 | | | IV-1 | Mcidas | 1.27 |
| 12479 | 3 | 4 | | | IV-1 | Mcm3ap | 1.09 |
| 12480 | 3 | 4 | | | IV-1 | Mcm9 | 1.12 |
| 12481 | 3 | 4 | | | IV-1 | Mcmbp | 1.06 |
| 12482 | 3 | 4 | | | IV-1 | Mcoln1 | 1.09 |
| 12483 | 3 | 4 | | | IV-1 | Mcrs1 | 1.15 |
| 12484 | 3 | 4 | | | IV-1 | Mctp2 | 1.05 |
| 12485 | 3 | 4 | | | IV-1 | Mcts2 | 1.13 |
| 12486 | 3 | 4 | | | IV-1 | Mdfi | 1.02 |
| 12487 | 3 | 4 | | | IV-1 | Mdga1 | 1.09 |
| 12488 | 3 | 4 | | | IV-1 | Mdm1 | 1.04 |
| 12489 | 3 | 4 | | | IV-1 | Mdm2 | 1.30 |
| 12490 | 3 | 4 | | | IV-1 | Mdm4 | 1.07 |
| 12491 | 3 | 4 | | | IV-1 | Me1 | 1.13 |
| 12492 | 3 | 4 | | | IV-1 | Mea6 | 1.16 |
| 12493 | 3 | 4 | | | IV-1 | Mecom | 1.08 |
| 12494 | 3 | 4 | | | IV-1 | Mecp2 | 1.11 |
| 12495 | 3 | 4 | | | IV-1 | Med10 | 1.20 |
| 12496 | 3 | 4 | | | IV-1 | Med12 | 1.18 |
| 12497 | 3 | 4 | | | IV-1 | Med12l | 1.17 |
| 12498 | 3 | 4 | | | IV-1 | Med13 | 1.06 |
| 12499 | 3 | 4 | | | IV-1 | Med13l | 1.05 |
| 12500 | 3 | 4 | | | IV-1 | Med15 | 1.15 |
| 12501 | 3 | 4 | | | IV-1 | Med16 | 1.01 |
| 12502 | 3 | 4 | | | IV-1 | Med17 | 1.02 |
| 12503 | 3 | 4 | | | IV-1 | Med22 | 1.09 |
| 12504 | 3 | 4 | | | IV-1 | Med23 | 1.13 |
| 12505 | 3 | 4 | | | IV-1 | Med24 | 1.13 |
| 12506 | 3 | 4 | | | IV-1 | Med25 | 1.10 |
| 12507 | 3 | 4 | | | IV-1 | Med26 | 1.01 |
| 12508 | 3 | 4 | | | IV-1 | Med27 | 1.03 |
| 12509 | 3 | 4 | | | IV-1 | Med30 | 1.00 |
| 12510 | 3 | 4 | | | IV-1 | Med4 | 1.03 |
| 12511 | 3 | 4 | | | IV-1 | Med8 | 1.04 |
| 12512 | 3 | 4 | | | IV-1 | Mef2a | 1.09 |
| 12513 | 3 | 4 | | | IV-1 | Mef2c | 1.04 |
| 12514 | 3 | 4 | | | IV-1 | Meg3 | 1.32 |
| 12515 | 3 | 4 | | | IV-1 | Megf10 | 1.03 |
| 12516 | 3 | 4 | | | IV-1 | Megf11 | 1.48 |
| 12517 | 3 | 4 | | | IV-1 | Megf6 | 1.36 |
| 12518 | 3 | 4 | | | IV-1 | Megf8 | 1.09 |
| 12519 | 3 | 4 | | | IV-1 | Megf9 | 1.17 |
| 12520 | 3 | 4 | | | IV-1 | Meis1 | 1.21 |
| 12521 | 3 | 4 | | | IV-1 | Meis2 | 1.41 |
| 12522 | 3 | 4 | | | IV-1 | Mertk | 1.19 |
| 12523 | 3 | 4 | | | IV-1 | Mettl13 | 1.40 |
| 12524 | 3 | 4 | | | IV-1 | Mettl17 | 1.49 |
| 12525 | 3 | 4 | | | IV-1 | Mettl18 | 1.02 |
| 12526 | 3 | 4 | | | IV-1 | Mettl22 | 1.48 |
| 12527 | 3 | 4 | | | IV-1 | Mettl25 | 1.15 |
| 12528 | 3 | 4 | | | IV-1 | Mettl5 | 1.03 |
| 12529 | 3 | 4 | | | IV-1 | Mettl7a1 | 1.01 |
| 12530 | 3 | 4 | | | IV-1 | Mex3a | 1.35 |
| 12531 | 3 | 4 | | | IV-1 | Mex3b | 1.27 |
| 12532 | 3 | 4 | | | IV-1 | Mex3c | 1.02 |
| 12533 | 3 | 4 | | | IV-1 | Mex3d | 1.13 |
| 12534 | 3 | 4 | | | IV-1 | Mfap2 | 1.21 |
| 12535 | 3 | 4 | | | IV-1 | Mfap3 | 1.02 |
| 12536 | 3 | 4 | | | IV-1 | Mff | 1.02 |
| 12537 | 3 | 4 | | | IV-1 | Mfge8 | 1.09 |
| 12538 | 3 | 4 | | | IV-1 | Mfn1 | 1.07 |
| 12539 | 3 | 4 | | | IV-1 | Mfng | 1.11 |
| 12540 | 3 | 4 | | | IV-1 | Mfsd10 | 1.17 |
| 12541 | 3 | 4 | | | IV-1 | Mfsd11 | 1.02 |
| 12542 | 3 | 4 | | | IV-1 | Mfsd2a | 1.24 |
| 12543 | 3 | 4 | | | IV-1 | Mfsd3 | 1.03 |
| 12544 | 3 | 4 | | | IV-1 | Mfsd7b | 1.15 |
| 12545 | 3 | 4 | | | IV-1 | Mfsd8 | 1.11 |
| 12546 | 3 | 4 | | | IV-1 | Mfsd9 | 1.27 |
| 12547 | 3 | 4 | | | IV-1 | Mga | 1.09 |
| 12548 | 3 | 4 | | | IV-1 | Mgat3 | 1.20 |
| 12549 | 3 | 4 | | | IV-1 | Mgat4b | 1.09 |
| 12550 | 3 | 4 | | | IV-1 | Mgat4c | 1.09 |
| 12551 | 3 | 4 | | | IV-1 | Mgat5 | 1.19 |
| 12552 | 3 | 4 | | | IV-1 | Mgea5 | 1.31 |
| 12553 | 3 | 4 | | | IV-1 | Mgmt | 1.03 |
| 12554 | 3 | 4 | | | IV-1 | Mgp | 1.44 |
| 12555 | 3 | 4 | | | IV-1 | Mgrn1 | 1.14 |
| 12556 | 3 | 4 | | | IV-1 | Mgst2 | 1.37 |
| 12557 | 3 | 4 | | | IV-1 | Mia3 | 1.03 |
| 12558 | 3 | 4 | | | IV-1 | Mib1 | 1.24 |
| 12559 | 3 | 4 | | | IV-1 | Mib2 | 1.05 |
| 12560 | 3 | 4 | | | IV-1 | Mical1 | 1.11 |
| 12561 | 3 | 4 | | | IV-1 | Micall1 | 1.16 |
| 12562 | 3 | 4 | | | IV-1 | Micu2 | 1.06 |
| 12563 | 3 | 4 | | | IV-1 | Mid1 | 1.37 |
| 12564 | 3 | 4 | | | IV-1 | Mid1ip1 | 1.03 |
| 12565 | 3 | 4 | | | IV-1 | Midn | 1.07 |
| 12566 | 3 | 4 | | | IV-1 | Miip | 1.09 |
| 12567 | 3 | 4 | | | IV-1 | Mill2 | 1.23 |
| 12568 | 3 | 4 | | | IV-1 | Milr1 | 1.05 |
| 12569 | 3 | 4 | | | IV-1 | Mios | 1.31 |
| 12570 | 3 | 4 | | | IV-1 | Mipol1 | 1.47 |
| 12571 | 3 | 4 | | | IV-1 | Mir22hg | 1.20 |
| 12572 | 3 | 4 | | | IV-1 | Mira | 1.16 |
| 12573 | 3 | 4 | | | IV-1 | Mitf | 1.09 |
| 12574 | 3 | 4 | | | IV-1 | Mkl2 | 1.06 |
| 12575 | 3 | 4 | | | IV-1 | Mkrn1 | 1.04 |
| 12576 | 3 | 4 | | | IV-1 | Mkrn2 | 1.09 |
| 12577 | 3 | 4 | | | IV-1 | Mkrn3 | 1.43 |
| 12578 | 3 | 4 | | | IV-1 | Mks1 | 1.31 |
| 12579 | 3 | 4 | | | IV-1 | Mkx | 1.06 |
| 12580 | 3 | 4 | | | IV-1 | Mlc1 | 1.27 |
| 12581 | 3 | 4 | | | IV-1 | Mlh3 | 1.18 |
| 12582 | 3 | 4 | | | IV-1 | Mllt4 | 1.16 |
| 12583 | 3 | 4 | | | IV-1 | Mllt6 | 1.14 |
| 12584 | 3 | 4 | | | IV-1 | Mlph | 1.39 |
| 12585 | 3 | 4 | | | IV-1 | Mlxip | 1.06 |
| 12586 | 3 | 4 | | | IV-1 | Mlycd | 1.21 |
| 12587 | 3 | 4 | | | IV-1 | Mme | 1.19 |
| 12588 | 3 | 4 | | | IV-1 | Mmp11 | 1.33 |
| 12589 | 3 | 4 | | | IV-1 | Mmp2 | 1.24 |
| 12590 | 3 | 4 | | | IV-1 | Mmp24 | 1.44 |
| 12591 | 3 | 4 | | | IV-1 | Mmp25 | 1.18 |
| 12592 | 3 | 4 | | | IV-1 | Mmp8 | 1.26 |
| 12593 | 3 | 4 | | | IV-1 | Mmrn1 | 1.17 |
| 12594 | 3 | 4 | | | IV-1 | Mms19 | 1.14 |
| 12595 | 3 | 4 | | | IV-1 | Mn1 | 1.38 |
| 12596 | 3 | 4 | | | IV-1 | Mnat1 | 1.01 |
| 12597 | 3 | 4 | | | IV-1 | Mnt | 1.18 |
| 12598 | 3 | 4 | | | IV-1 | Moap1 | 1.20 |
| 12599 | 3 | 4 | | | IV-1 | Mob3c | 1.01 |
| 12600 | 3 | 4 | | | IV-1 | Mocs1 | 1.13 |
| 12601 | 3 | 4 | | | IV-1 | Morc2a | 1.43 |
| 12602 | 3 | 4 | | | IV-1 | Morc3 | 1.06 |
| 12603 | 3 | 4 | | | IV-1 | Morn1 | 1.14 |
| 12604 | 3 | 4 | | | IV-1 | Mospd3 | 1.04 |
| 12605 | 3 | 4 | | | IV-1 | Moxd1 | 1.07 |
| 12606 | 3 | 4 | | | IV-1 | Mpdu1 | 1.03 |
| 12607 | 3 | 4 | | | IV-1 | Mpdz | 1.08 |
| 12608 | 3 | 4 | | | IV-1 | Mpg | 1.36 |
| 12609 | 3 | 4 | | | IV-1 | Mpi | 1.06 |
| 12610 | 3 | 4 | | | IV-1 | Mpp3 | 1.26 |
| 12611 | 3 | 4 | | | IV-1 | Mpped2 | 1.42 |
| 12612 | 3 | 4 | | | IV-1 | Mprip | 1.05 |
| 12613 | 3 | 4 | | | IV-1 | Mpzl1 | 1.17 |
| 12614 | 3 | 4 | | | IV-1 | Mr1 | 1.03 |
| 12615 | 3 | 4 | | | IV-1 | Mras | 1.36 |
| 12616 | 3 | 4 | | | IV-1 | Mre11a | 1.22 |
| 12617 | 3 | 4 | | | IV-1 | Mrgbp | 1.03 |
| 12618 | 3 | 4 | | | IV-1 | Mrgprb2 | 1.26 |
| 12619 | 3 | 4 | | | IV-1 | Mrgpre | 1.12 |
| 12620 | 3 | 4 | | | IV-1 | Mri1 | 1.29 |
| 12621 | 3 | 4 | | | IV-1 | Mro | 1.16 |
| 12622 | 3 | 4 | | | IV-1 | Mroh1 | 1.14 |
| 12623 | 3 | 4 | | | IV-1 | Mroh6 | 1.01 |
| 12624 | 3 | 4 | | | IV-1 | Mrpl2 | 1.06 |
| 12625 | 3 | 4 | | | IV-1 | Mrps9 | 1.07 |
| 12626 | 3 | 4 | | | IV-1 | Ms4a3 | 1.23 |
| 12627 | 3 | 4 | | | IV-1 | Ms4a6b | 1.48 |
| 12628 | 3 | 4 | | | IV-1 | Ms4a6c | 1.25 |
| 12629 | 3 | 4 | | | IV-1 | Msantd2 | 1.08 |
| 12630 | 3 | 4 | | | IV-1 | Msantd3 | 1.20 |
| 12631 | 3 | 4 | | | IV-1 | Msantd4 | 1.10 |
| 12632 | 3 | 4 | | | IV-1 | Msh3 | 1.33 |
| 12633 | 3 | 4 | | | IV-1 | Msi1 | 1.48 |
| 12634 | 3 | 4 | | | IV-1 | Msi2 | 1.14 |
| 12635 | 3 | 4 | | | IV-1 | Msl1 | 1.03 |
| 12636 | 3 | 4 | | | IV-1 | Msl3l2 | 1.24 |
| 12637 | 3 | 4 | | | IV-1 | Msln | 1.43 |
| 12638 | 3 | 4 | | | IV-1 | Mss51 | 1.06 |
| 12639 | 3 | 4 | | | IV-1 | Mst1r | 1.20 |
| 12640 | 3 | 4 | | | IV-1 | Msto1 | 1.14 |
| 12641 | 3 | 4 | | | IV-1 | Msx1 | 1.42 |
| 12642 | 3 | 4 | | | IV-1 | Msx2 | 1.34 |
| 12643 | 3 | 4 | | | IV-1 | Mt1 | 1.00 |
| 12644 | 3 | 4 | | | IV-1 | Mt3 | 1.43 |
| 12645 | 3 | 4 | | | IV-1 | Mta1 | 1.22 |
| 12646 | 3 | 4 | | | IV-1 | Mtap7d3 | 1.44 |
| 12647 | 3 | 4 | | | IV-1 | Mtbp | 1.03 |
| 12648 | 3 | 4 | | | IV-1 | Mtch2 | 1.21 |
| 12649 | 3 | 4 | | | IV-1 | Mtcl1 | 1.10 |
| 12650 | 3 | 4 | | | IV-1 | Mtcp1 | 1.16 |
| 12651 | 3 | 4 | | | IV-1 | Mtdh | 1.04 |
| 12652 | 3 | 4 | | | IV-1 | Mterfd1 | 1.26 |
| 12653 | 3 | 4 | | | IV-1 | Mterfd3 | 1.04 |
| 12654 | 3 | 4 | | | IV-1 | Mtf2 | 1.19 |
| 12655 | 3 | 4 | | | IV-1 | Mtfmr | 1.05 |
| 12656 | 3 | 4 | | | IV-1 | Mtfr1l | 1.22 |
| 12657 | 3 | 4 | | | IV-1 | Mtg1 | 1.46 |
| 12658 | 3 | 4 | | | IV-1 | Mthfd1l | 1.04 |
| 12659 | 3 | 4 | | | IV-1 | Mthfd2l | 1.22 |
| 12660 | 3 | 4 | | | IV-1 | Mthfr | 1.15 |
| 12661 | 3 | 4 | | | IV-1 | Mthfsd | 1.11 |
| 12662 | 3 | 4 | | | IV-1 | Mtmr1 | 1.13 |
| 12663 | 3 | 4 | | | IV-1 | Mtmr10 | 1.13 |
| 12664 | 3 | 4 | | | IV-1 | Mtmr14 | 1.02 |
| 12665 | 3 | 4 | | | IV-1 | Mtmr2 | 1.06 |
| 12666 | 3 | 4 | | | IV-1 | Mtmr3 | 1.03 |
| 12667 | 3 | 4 | | | IV-1 | Mtmr6 | 1.14 |
| 12668 | 3 | 4 | | | IV-1 | Mtmr7 | 1.42 |
| 12669 | 3 | 4 | | | IV-1 | Mtmr9 | 1.17 |

Fig. 45 - 67

| | | | | | | | | | | | | | | |
|---|---|---|---|---|---|---|---|---|---|---|---|---|---|---|
| 12670 | 3 | 4 | | | IV-1 | Mtor | 1.13 | 12766 | 3 | 4 | | | IV-1 | Necab2 | 1.49 |
| 12671 | 3 | 4 | | | IV-1 | Mtpap | 1.12 | 12767 | 3 | 4 | | | IV-1 | Necap1 | 1.05 |
| 12672 | 3 | 4 | | | IV-1 | Mtpn | 1.03 | 12768 | 3 | 4 | | | IV-1 | Nedd4l | 1.30 |
| 12673 | 3 | 4 | | | IV-1 | Mtss1 | 1.08 | 12769 | 3 | 4 | | | IV-1 | Nedd9 | 1.08 |
| 12674 | 3 | 4 | | | IV-1 | Mtss1l | 1.18 | 12770 | 3 | 4 | | | IV-1 | Nefl | 1.28 |
| 12675 | 3 | 4 | | | IV-1 | Mturn | 1.45 | 12771 | 3 | 4 | | | IV-1 | Nefm | 1.42 |
| 12676 | 3 | 4 | | | IV-1 | Mtus1 | 1.10 | 12772 | 3 | 4 | | | IV-1 | Negr1 | 1.40 |
| 12677 | 3 | 4 | | | IV-1 | Mtx3 | 1.22 | 12773 | 3 | 4 | | | IV-1 | Nek3 | 1.33 |
| 12678 | 3 | 4 | | | IV-1 | Muc4 | 1.05 | 12774 | 3 | 4 | | | IV-1 | Nek7 | 1.02 |
| 12679 | 3 | 4 | | | IV-1 | Mum1l1 | 1.28 | 12775 | 3 | 4 | | | IV-1 | Nek8 | 1.00 |
| 12680 | 3 | 4 | | | IV-1 | Musk | 1.13 | 12776 | 3 | 4 | | | IV-1 | Nek9 | 1.14 |
| 12681 | 3 | 4 | | | IV-1 | Mustn1 | 1.01 | 12777 | 3 | 4 | | | IV-1 | Nell1 | 1.28 |
| 12682 | 3 | 4 | | | IV-1 | Mvb12b | 1.35 | 12778 | 3 | 4 | | | IV-1 | Nemf | 1.01 |
| 12683 | 3 | 4 | | | IV-1 | Mvp | 1.11 | 12779 | 3 | 4 | | | IV-1 | Neo1 | 1.38 |
| 12684 | 3 | 4 | | | IV-1 | Mx1 | 1.24 | 12780 | 3 | 4 | | | IV-1 | Net1 | 1.00 |
| 12685 | 3 | 4 | | | IV-1 | Mybbp1a | 1.08 | 12781 | 3 | 4 | | | IV-1 | Neto1 | 1.21 |
| 12686 | 3 | 4 | | | IV-1 | Mybl1 | 1.02 | 12782 | 3 | 4 | | | IV-1 | Neurl1a | 1.11 |
| 12687 | 3 | 4 | | | IV-1 | Mybph | 1.03 | 12783 | 3 | 4 | | | IV-1 | Neurl2 | 1.03 |
| 12688 | 3 | 4 | | | IV-1 | Myc | 1.14 | 12784 | 3 | 4 | | | IV-1 | Neurl4 | 1.05 |
| 12689 | 3 | 4 | | | IV-1 | Mycbp2 | 1.25 | 12785 | 3 | 4 | | | IV-1 | Neurog2 | 1.38 |
| 12690 | 3 | 4 | | | IV-1 | Mycn | 1.25 | 12786 | 3 | 4 | | | IV-1 | Neurog3 | 1.01 |
| 12691 | 3 | 4 | | | IV-1 | Myef2 | 1.21 | 12787 | 3 | 4 | | | IV-1 | Nf1 | 1.23 |
| 12692 | 3 | 4 | | | IV-1 | Myh6 | 1.38 | 12788 | 3 | 4 | | | IV-1 | Nf2 | 1.01 |
| 12693 | 3 | 4 | | | IV-1 | Myh7b | 1.24 | 12789 | 3 | 4 | | | IV-1 | Nfat5 | 1.17 |
| 12694 | 3 | 4 | | | IV-1 | Mylip | 1.26 | 12790 | 3 | 4 | | | IV-1 | Nfatc4 | 1.12 |
| 12695 | 3 | 4 | | | IV-1 | Mynn | 1.05 | 12791 | 3 | 4 | | | IV-1 | Nfe2l3 | 1.20 |
| 12696 | 3 | 4 | | | IV-1 | Myo16 | 1.25 | 12792 | 3 | 4 | | | IV-1 | Nfia | 1.14 |
| 12697 | 3 | 4 | | | IV-1 | Myo18a | 1.04 | 12793 | 3 | 4 | | | IV-1 | Nfib | 1.15 |
| 12698 | 3 | 4 | | | IV-1 | Myo1c | 1.06 | 12794 | 3 | 4 | | | IV-1 | Nfil3 | 1.05 |
| 12699 | 3 | 4 | | | IV-1 | Myo1f | 1.07 | 12795 | 3 | 4 | | | IV-1 | Nfix | 1.22 |
| 12700 | 3 | 4 | | | IV-1 | Myo1g | 1.09 | 12796 | 3 | 4 | | | IV-1 | Nfkbia | 1.43 |
| 12701 | 3 | 4 | | | IV-1 | Myo5a | 1.38 | 12797 | 3 | 4 | | | IV-1 | Nfkbie | 1.07 |
| 12702 | 3 | 4 | | | IV-1 | Myo9a | 1.03 | 12798 | 3 | 4 | | | IV-1 | Nfkbil1 | 1.11 |
| 12703 | 3 | 4 | | | IV-1 | Myo9b | 1.03 | 12799 | 3 | 4 | | | IV-1 | Nfkbiz | 1.11 |
| 12704 | 3 | 4 | | | IV-1 | Myocd | 1.18 | 12800 | 3 | 4 | | | IV-1 | Nfrkb | 1.31 |
| 12705 | 3 | 4 | | | IV-1 | Myrf | 1.05 | 12801 | 3 | 4 | | | IV-1 | Nfu1 | 1.14 |
| 12706 | 3 | 4 | | | IV-1 | Myrip | 1.39 | 12802 | 3 | 4 | | | IV-1 | Nfx1 | 1.08 |
| 12707 | 3 | 4 | | | IV-1 | Mysm1 | 1.11 | 12803 | 3 | 4 | | | IV-1 | Nfxl1 | 1.06 |
| 12708 | 3 | 4 | | | IV-1 | Mzt1 | 1.05 | 12804 | 3 | 4 | | | IV-1 | Ngf | 1.15 |
| 12709 | 3 | 4 | | | IV-1 | Mzt2 | 1.12 | 12805 | 3 | 4 | | | IV-1 | Ngly1 | 1.08 |
| 12710 | 3 | 4 | | | IV-1 | N4bp1 | 1.02 | 12806 | 3 | 4 | | | IV-1 | Ngrn | 1.19 |
| 12711 | 3 | 4 | | | IV-1 | N4bp2 | 1.04 | 12807 | 3 | 4 | | | IV-1 | Nhlh1 | 1.40 |
| 12712 | 3 | 4 | | | IV-1 | N4bp2l1 | 1.26 | 12808 | 3 | 4 | | | IV-1 | Nhlrc1 | 1.07 |
| 12713 | 3 | 4 | | | IV-1 | Naa25 | 1.15 | 12809 | 3 | 4 | | | IV-1 | Nhlrc2 | 1.05 |
| 12714 | 3 | 4 | | | IV-1 | Nabp2 | 1.10 | 12810 | 3 | 4 | | | IV-1 | Nhlrc3 | 1.05 |
| 12715 | 3 | 4 | | | IV-1 | Naca | 1.01 | 12811 | 3 | 4 | | | IV-1 | Nhs | 1.34 |
| 12716 | 3 | 4 | | | IV-1 | Nadsyn1 | 1.11 | 12812 | 3 | 4 | | | IV-1 | Nhsl1 | 1.08 |
| 12717 | 3 | 4 | | | IV-1 | Nae1 | 1.41 | 12813 | 3 | 4 | | | IV-1 | Nicn1 | 1.16 |
| 12718 | 3 | 4 | | | IV-1 | Nalcn | 1.08 | 12814 | 3 | 4 | | | IV-1 | Nid1 | 1.11 |
| 12719 | 3 | 4 | | | IV-1 | Nanos1 | 1.36 | 12815 | 3 | 4 | | | IV-1 | Nin | 1.10 |
| 12720 | 3 | 4 | | | IV-1 | Nanos2 | 1.13 | 12816 | 3 | 4 | | | IV-1 | Nip7 | 1.07 |
| 12721 | 3 | 4 | | | IV-1 | Nap1l1 | 1.05 | 12817 | 3 | 4 | | | IV-1 | Nipal2 | 1.27 |
| 12722 | 3 | 4 | | | IV-1 | Nap1l2 | 1.46 | 12818 | 3 | 4 | | | IV-1 | Nipal4 | 1.09 |
| 12723 | 3 | 4 | | | IV-1 | Nap1l3 | 1.49 | 12819 | 3 | 4 | | | IV-1 | Nipsnap3b | 1.06 |
| 12724 | 3 | 4 | | | IV-1 | Napb | 1.43 | 12820 | 3 | 4 | | | IV-1 | Nisch | 1.05 |
| 12725 | 3 | 4 | | | IV-1 | Napepld | 1.07 | 12821 | 3 | 4 | | | IV-1 | Nkain4 | 1.36 |
| 12726 | 3 | 4 | | | IV-1 | Napg | 1.16 | 12822 | 3 | 4 | | | IV-1 | Nkap | 1.12 |
| 12727 | 3 | 4 | | | IV-1 | Nars | 1.04 | 12823 | 3 | 4 | | | IV-1 | Nkapl | 1.21 |
| 12728 | 3 | 4 | | | IV-1 | Nars2 | 1.01 | 12824 | 3 | 4 | | | IV-1 | Nkd1 | 1.34 |
| 12729 | 3 | 4 | | | IV-1 | Nat10 | 1.01 | 12825 | 3 | 4 | | | IV-1 | Nkd2 | 1.32 |
| 12730 | 3 | 4 | | | IV-1 | Nat14 | 1.39 | 12826 | 3 | 4 | | | IV-1 | Nkiras1 | 1.06 |
| 12731 | 3 | 4 | | | IV-1 | Nat8l | 1.07 | 12827 | 3 | 4 | | | IV-1 | Nkiras2 | 1.05 |
| 12732 | 3 | 4 | | | IV-1 | Nav1 | 1.26 | 12828 | 3 | 4 | | | IV-1 | Nkrf | 1.15 |
| 12733 | 3 | 4 | | | IV-1 | Nav2 | 1.15 | 12829 | 3 | 4 | | | IV-1 | Nktr | 1.14 |
| 12734 | 3 | 4 | | | IV-1 | Nav3 | 1.40 | 12830 | 3 | 4 | | | IV-1 | Nkx2-1 | 1.03 |
| 12735 | 3 | 4 | | | IV-1 | Nbeal1 | 1.06 | 12831 | 3 | 4 | | | IV-1 | Nle1 | 1.10 |
| 12736 | 3 | 4 | | | IV-1 | Nbl1 | 1.24 | 12832 | 3 | 4 | | | IV-1 | Nlgn2 | 1.40 |
| 12737 | 3 | 4 | | | IV-1 | Ncald | 1.08 | 12833 | 3 | 4 | | | IV-1 | Nlgn3 | 1.22 |
| 12738 | 3 | 4 | | | IV-1 | Ncam1 | 1.28 | 12834 | 3 | 4 | | | IV-1 | Nlk | 1.09 |
| 12739 | 3 | 4 | | | IV-1 | Ncdn | 1.36 | 12835 | 3 | 4 | | | IV-1 | Nln | 1.00 |
| 12740 | 3 | 4 | | | IV-1 | Nceh1 | 1.18 | 12836 | 3 | 4 | | | IV-1 | Nlrx1 | 1.47 |
| 12741 | 3 | 4 | | | IV-1 | Nck2 | 1.09 | 12837 | 3 | 4 | | | IV-1 | Nmd3 | 1.12 |
| 12742 | 3 | 4 | | | IV-1 | Nckap1 | 1.01 | 12838 | 3 | 4 | | | IV-1 | Nme7 | 1.10 |
| 12743 | 3 | 4 | | | IV-1 | Nckap5 | 1.13 | 12839 | 3 | 4 | | | IV-1 | Nmt2 | 1.11 |
| 12744 | 3 | 4 | | | IV-1 | Nckap5l | 1.21 | 12840 | 3 | 4 | | | IV-1 | Nnmt | 1.25 |
| 12745 | 3 | 4 | | | IV-1 | Nckipsd | 1.30 | 12841 | 3 | 4 | | | IV-1 | Nob1 | 1.15 |
| 12746 | 3 | 4 | | | IV-1 | Ncl | 1.04 | 12842 | 3 | 4 | | | IV-1 | Noc2l | 1.00 |
| 12747 | 3 | 4 | | | IV-1 | Ncoa1 | 1.07 | 12843 | 3 | 4 | | | IV-1 | Noc3l | 1.01 |
| 12748 | 3 | 4 | | | IV-1 | Ncoa2 | 1.07 | 12844 | 3 | 4 | | | IV-1 | Nol10 | 1.19 |
| 12749 | 3 | 4 | | | IV-1 | Ncoa3 | 1.05 | 12845 | 3 | 4 | | | IV-1 | Nol11 | 1.16 |
| 12750 | 3 | 4 | | | IV-1 | Ncoa5 | 1.05 | 12846 | 3 | 4 | | | IV-1 | Nol6 | 1.27 |
| 12751 | 3 | 4 | | | IV-1 | Ncoa6 | 1.13 | 12847 | 3 | 4 | | | IV-1 | Nol8 | 1.10 |
| 12752 | 3 | 4 | | | IV-1 | Ncor2 | 1.05 | 12848 | 3 | 4 | | | IV-1 | Nol9 | 1.17 |
| 12753 | 3 | 4 | | | IV-1 | Ncs1 | 1.15 | 12849 | 3 | 4 | | | IV-1 | Nom1 | 1.33 |
| 12754 | 3 | 4 | | | IV-1 | Ncstn | 1.12 | 12850 | 3 | 4 | | | IV-1 | Nomo1 | 1.03 |
| 12755 | 3 | 4 | | | IV-1 | Ndel1 | 1.06 | 12851 | 3 | 4 | | | IV-1 | Nop14 | 1.29 |
| 12756 | 3 | 4 | | | IV-1 | Ndfip1 | 1.36 | 12852 | 3 | 4 | | | IV-1 | Nos1ap | 1.44 |
| 12757 | 3 | 4 | | | IV-1 | Ndfip2 | 1.01 | 12853 | 3 | 4 | | | IV-1 | Nosip | 1.02 |
| 12758 | 3 | 4 | | | IV-1 | Ndn | 1.15 | 12854 | 3 | 4 | | | IV-1 | Notum | 1.17 |
| 12759 | 3 | 4 | | | IV-1 | Ndor1 | 1.31 | 12855 | 3 | 4 | | | IV-1 | Nova2 | 1.37 |
| 12760 | 3 | 4 | | | IV-1 | Ndp | 1.15 | 12856 | 3 | 4 | | | IV-1 | Nox4 | 1.27 |
| 12761 | 3 | 4 | | | IV-1 | Ndrg2 | 1.16 | 12857 | 3 | 4 | | | IV-1 | Npas2 | 1.11 |
| 12762 | 3 | 4 | | | IV-1 | Ndrg4 | 1.25 | 12858 | 3 | 4 | | | IV-1 | Npb | 1.31 |
| 12763 | 3 | 4 | | | IV-1 | Ndst1 | 1.13 | 12859 | 3 | 4 | | | IV-1 | Npc1 | 1.13 |
| 12764 | 3 | 4 | | | IV-1 | Ndufa6 | 1.03 | 12860 | 3 | 4 | | | IV-1 | Npcd | 1.04 |
| 12765 | 3 | 4 | | | IV-1 | Necab1 | 1.01 | 12861 | 3 | 4 | | | IV-1 | Npdc1 | 1.29 |

Fig. 45 - 68

| | | | | | | | | | | | | | | |
|---|---|---|---|---|---|---|---|---|---|---|---|---|---|---|
| 12862 | 3 | 4 | | | IV-1 | Npepl1 | 1.18 | 12958 | 3 | 4 | | | IV-1 | Ogfr | 1.20 |
| 12863 | 3 | 4 | | | IV-1 | Nphp1 | 1.35 | 12959 | 3 | 4 | | | IV-1 | Ogfrl1 | 1.02 |
| 12864 | 3 | 4 | | | IV-1 | Nphp3 | 1.24 | 12960 | 3 | 4 | | | IV-1 | Ogn | 1.17 |
| 12865 | 3 | 4 | | | IV-1 | Nphp4 | 1.02 | 12961 | 3 | 4 | | | IV-1 | Ogt | 1.07 |
| 12866 | 3 | 4 | | | IV-1 | Nploc4 | 1.03 | 12962 | 3 | 4 | | | IV-1 | Olfm1 | 1.18 |
| 12867 | 3 | 4 | | | IV-1 | Npnt | 1.16 | 12963 | 3 | 4 | | | IV-1 | Olfm2 | 1.50 |
| 12868 | 3 | 4 | | | IV-1 | Npr2 | 1.39 | 12964 | 3 | 4 | | | IV-1 | Olfml1 | 1.15 |
| 12869 | 3 | 4 | | | IV-1 | Npr3 | 1.25 | 12965 | 3 | 4 | | | IV-1 | Olfr545 | 1.02 |
| 12870 | 3 | 4 | | | IV-1 | Nprl3 | 1.38 | 12966 | 3 | 4 | | | IV-1 | Olig1 | 1.21 |
| 12871 | 3 | 4 | | | IV-1 | Nptn | 1.03 | 12967 | 3 | 4 | | | IV-1 | Onecut1 | 1.23 |
| 12872 | 3 | 4 | | | IV-1 | Nptx1 | 1.45 | 12968 | 3 | 4 | | | IV-1 | Onecut2 | 1.10 |
| 12873 | 3 | 4 | | | IV-1 | Npy | 1.46 | 12969 | 3 | 4 | | | IV-1 | Opa1 | 1.12 |
| 12874 | 3 | 4 | | | IV-1 | Npy1r | 1.47 | 12970 | 3 | 4 | | | IV-1 | Opcml | 1.04 |
| 12875 | 3 | 4 | | | IV-1 | Npy2r | 1.25 | 12971 | 3 | 4 | | | IV-1 | Ophn1 | 1.24 |
| 12876 | 3 | 4 | | | IV-1 | Nr0b2 | 1.06 | 12972 | 3 | 4 | | | IV-1 | Oplah | 1.18 |
| 12877 | 3 | 4 | | | IV-1 | Nr1d1 | 1.35 | 12973 | 3 | 4 | | | IV-1 | Orai2 | 1.34 |
| 12878 | 3 | 4 | | | IV-1 | Nr2c1 | 1.14 | 12974 | 3 | 4 | | | IV-1 | Orc3 | 1.05 |
| 12879 | 3 | 4 | | | IV-1 | Nr2c2 | 1.37 | 12975 | 3 | 4 | | | IV-1 | Orc4 | 1.00 |
| 12880 | 3 | 4 | | | IV-1 | Nr2f2 | 1.19 | 12976 | 3 | 4 | | | IV-1 | Os9 | 1.14 |
| 12881 | 3 | 4 | | | IV-1 | Nr4a1 | 1.21 | 12977 | 3 | 4 | | | IV-1 | Osbpl2 | 1.12 |
| 12882 | 3 | 4 | | | IV-1 | Nr4a2 | 1.07 | 12978 | 3 | 4 | | | IV-1 | Osbpl3 | 1.01 |
| 12883 | 3 | 4 | | | IV-1 | Nr6a1 | 1.01 | 12979 | 3 | 4 | | | IV-1 | Osbpl5 | 1.05 |
| 12884 | 3 | 4 | | | IV-1 | Nradd | 1.14 | 12980 | 3 | 4 | | | IV-1 | Osbpl6 | 1.25 |
| 12885 | 3 | 4 | | | IV-1 | Nras | 1.06 | 12981 | 3 | 4 | | | IV-1 | Osbpl7 | 1.41 |
| 12886 | 3 | 4 | | | IV-1 | Nrbp1 | 1.11 | 12982 | 3 | 4 | | | IV-1 | Osbpl8 | 1.04 |
| 12887 | 3 | 4 | | | IV-1 | Nrcam | 1.37 | 12983 | 3 | 4 | | | IV-1 | Osbpl9 | 1.25 |
| 12888 | 3 | 4 | | | IV-1 | Nrde2 | 1.38 | 12984 | 3 | 4 | | | IV-1 | Oscp1 | 1.46 |
| 12889 | 3 | 4 | | | IV-1 | Nrep | 1.10 | 12985 | 3 | 4 | | | IV-1 | Osgin1 | 1.31 |
| 12890 | 3 | 4 | | | IV-1 | Nrg2 | 1.04 | 12986 | 3 | 4 | | | IV-1 | Osgin2 | 1.13 |
| 12891 | 3 | 4 | | | IV-1 | Nrip1 | 1.30 | 12987 | 3 | 4 | | | IV-1 | Osr2 | 1.46 |
| 12892 | 3 | 4 | | | IV-1 | Nrip2 | 1.15 | 12988 | 3 | 4 | | | IV-1 | Ostm1 | 1.17 |
| 12893 | 3 | 4 | | | IV-1 | Nrp1 | 1.00 | 12989 | 3 | 4 | | | IV-1 | Ostn | 1.13 |
| 12894 | 3 | 4 | | | IV-1 | Nrp2 | 1.06 | 12990 | 3 | 4 | | | IV-1 | Otor | 1.38 |
| 12895 | 3 | 4 | | | IV-1 | Nrsn1 | 1.23 | 12991 | 3 | 4 | | | IV-1 | Otub1 | 1.05 |
| 12896 | 3 | 4 | | | IV-1 | Nrxn1 | 1.43 | 12992 | 3 | 4 | | | IV-1 | Otud4 | 1.05 |
| 12897 | 3 | 4 | | | IV-1 | Nsa2 | 1.27 | 12993 | 3 | 4 | | | IV-1 | Otud7b | 1.02 |
| 12898 | 3 | 4 | | | IV-1 | Nsd1 | 1.05 | 12994 | 3 | 4 | | | IV-1 | Otulin | 1.11 |
| 12899 | 3 | 4 | | | IV-1 | Nsf | 1.06 | 12995 | 3 | 4 | | | IV-1 | Otx1 | 1.43 |
| 12900 | 3 | 4 | | | IV-1 | Nsmaf | 1.16 | 12996 | 3 | 4 | | | IV-1 | Otx2 | 1.42 |
| 12901 | 3 | 4 | | | IV-1 | Nsmce4a | 1.13 | 12997 | 3 | 4 | | | IV-1 | Oxr1 | 1.06 |
| 12902 | 3 | 4 | | | IV-1 | Nsmf | 1.35 | 12998 | 3 | 4 | | | IV-1 | P2rx2 | 1.13 |
| 12903 | 3 | 4 | | | IV-1 | Nsun3 | 1.13 | 12999 | 3 | 4 | | | IV-1 | P2rx4 | 1.03 |
| 12904 | 3 | 4 | | | IV-1 | Nsun5 | 1.04 | 13000 | 3 | 4 | | | IV-1 | P2rx6 | 1.03 |
| 12905 | 3 | 4 | | | IV-1 | Nsun6 | 1.32 | 13001 | 3 | 4 | | | IV-1 | P2rx7 | 1.14 |
| 12906 | 3 | 4 | | | IV-1 | Nt5c2 | 1.05 | 13002 | 3 | 4 | | | IV-1 | P2ry2 | 1.34 |
| 12907 | 3 | 4 | | | IV-1 | Nt5dc1 | 1.16 | 13003 | 3 | 4 | | | IV-1 | P2ry6 | 1.02 |
| 12908 | 3 | 4 | | | IV-1 | Nt5dc3 | 1.18 | 13004 | 3 | 4 | | | IV-1 | P4htm | 1.28 |
| 12909 | 3 | 4 | | | IV-1 | Nt5e | 1.09 | 13005 | 3 | 4 | | | IV-1 | Pabpc4l | 1.02 |
| 12910 | 3 | 4 | | | IV-1 | Nt5m | 1.43 | 13006 | 3 | 4 | | | IV-1 | Pabpc5 | 1.39 |
| 12911 | 3 | 4 | | | IV-1 | Ntf3 | 1.30 | 13007 | 3 | 4 | | | IV-1 | Pabpn1 | 1.21 |
| 12912 | 3 | 4 | | | IV-1 | Ntf5 | 1.15 | 13008 | 3 | 4 | | | IV-1 | Pacrg | 1.07 |
| 12913 | 3 | 4 | | | IV-1 | Nthl1 | 1.06 | 13009 | 3 | 4 | | | IV-1 | Pacs1 | 1.17 |
| 12914 | 3 | 4 | | | IV-1 | Ntm | 1.42 | 13010 | 3 | 4 | | | IV-1 | Pacs2 | 1.14 |
| 12915 | 3 | 4 | | | IV-1 | Ntmt1 | 1.14 | 13011 | 3 | 4 | | | IV-1 | Pacsin1 | 1.26 |
| 12916 | 3 | 4 | | | IV-1 | Ntn1 | 1.31 | 13012 | 3 | 4 | | | IV-1 | Pafah1b1 | 1.15 |
| 12917 | 3 | 4 | | | IV-1 | Ntn3 | 1.35 | 13013 | 3 | 4 | | | IV-1 | Pafah1b2 | 1.06 |
| 12918 | 3 | 4 | | | IV-1 | Ntng2 | 1.36 | 13014 | 3 | 4 | | | IV-1 | Pafah1b3 | 1.09 |
| 12919 | 3 | 4 | | | IV-1 | Ntpcr | 1.21 | 13015 | 3 | 4 | | | IV-1 | Pak1 | 1.27 |
| 12920 | 3 | 4 | | | IV-1 | Ntrk1 | 1.38 | 13016 | 3 | 4 | | | IV-1 | Pak3 | 1.20 |
| 12921 | 3 | 4 | | | IV-1 | Ntrk2 | 1.47 | 13017 | 3 | 4 | | | IV-1 | Pak6 | 1.01 |
| 12922 | 3 | 4 | | | IV-1 | Nts | 1.21 | 13018 | 3 | 4 | | | IV-1 | Pald1 | 1.06 |
| 12923 | 3 | 4 | | | IV-1 | Nuak1 | 1.24 | 13019 | 3 | 4 | | | IV-1 | Palm | 1.23 |
| 12924 | 3 | 4 | | | IV-1 | Nuak2 | 1.20 | 13020 | 3 | 4 | | | IV-1 | Pam | 1.32 |
| 12925 | 3 | 4 | | | IV-1 | Nubp2 | 1.08 | 13021 | 3 | 4 | | | IV-1 | Pam16 | 1.17 |
| 12926 | 3 | 4 | | | IV-1 | Nucb2 | 1.21 | 13022 | 3 | 4 | | | IV-1 | Pan2 | 1.15 |
| 12927 | 3 | 4 | | | IV-1 | Nudcd3 | 1.11 | 13023 | 3 | 4 | | | IV-1 | Pan3 | 1.05 |
| 12928 | 3 | 4 | | | IV-1 | Nudt17 | 1.14 | 13024 | 3 | 4 | | | IV-1 | Pank1 | 1.00 |
| 12929 | 3 | 4 | | | IV-1 | Nudt18 | 1.47 | 13025 | 3 | 4 | | | IV-1 | Panx1 | 1.36 |
| 12930 | 3 | 4 | | | IV-1 | Nudt22 | 1.12 | 13026 | 3 | 4 | | | IV-1 | Panx2 | 1.34 |
| 12931 | 3 | 4 | | | IV-1 | Nudt3 | 1.02 | 13027 | 3 | 4 | | | IV-1 | Papd4 | 1.28 |
| 12932 | 3 | 4 | | | IV-1 | Nudt6 | 1.25 | 13028 | 3 | 4 | | | IV-1 | Papd5 | 1.14 |
| 12933 | 3 | 4 | | | IV-1 | Nudt8 | 1.39 | 13029 | 3 | 4 | | | IV-1 | Papd7 | 1.02 |
| 12934 | 3 | 4 | | | IV-1 | Nufip1 | 1.35 | 13030 | 3 | 4 | | | IV-1 | Papln | 1.21 |
| 12935 | 3 | 4 | | | IV-1 | Numa1 | 1.01 | 13031 | 3 | 4 | | | IV-1 | Papolg | 1.04 |
| 12936 | 3 | 4 | | | IV-1 | Numbl | 1.26 | 13032 | 3 | 4 | | | IV-1 | Paqr3 | 1.05 |
| 12937 | 3 | 4 | | | IV-1 | Nup107 | 1.00 | 13033 | 3 | 4 | | | IV-1 | Paqr7 | 1.15 |
| 12938 | 3 | 4 | | | IV-1 | Nup155 | 1.03 | 13034 | 3 | 4 | | | IV-1 | Paqr8 | 1.29 |
| 12939 | 3 | 4 | | | IV-1 | Nupl2 | 1.41 | 13035 | 3 | 4 | | | IV-1 | Pard3 | 1.04 |
| 12940 | 3 | 4 | | | IV-1 | Nupr1 | 1.41 | 13036 | 3 | 4 | | | IV-1 | Pard3b | 1.09 |
| 12941 | 3 | 4 | | | IV-1 | Nus1 | 1.01 | 13037 | 3 | 4 | | | IV-1 | Pard6a | 1.08 |
| 12942 | 3 | 4 | | | IV-1 | Nxf1 | 1.10 | 13038 | 3 | 4 | | | IV-1 | Pard6g | 1.10 |
| 12943 | 3 | 4 | | | IV-1 | Nxnl2 | 1.44 | 13039 | 3 | 4 | | | IV-1 | Parg | 1.02 |
| 12944 | 3 | 4 | | | IV-1 | Nxpe3 | 1.05 | 13040 | 3 | 4 | | | IV-1 | Parl | 1.23 |
| 12945 | 3 | 4 | | | IV-1 | Nxpe4 | 1.08 | 13041 | 3 | 4 | | | IV-1 | Parn | 1.24 |
| 12946 | 3 | 4 | | | IV-1 | Nxph3 | 1.25 | 13042 | 3 | 4 | | | IV-1 | Parp10 | 1.25 |
| 12947 | 3 | 4 | | | IV-1 | Nxph4 | 1.41 | 13043 | 3 | 4 | | | IV-1 | Parp11 | 1.19 |
| 12948 | 3 | 4 | | | IV-1 | Oas1a | 1.42 | 13044 | 3 | 4 | | | IV-1 | Parp12 | 1.45 |
| 12949 | 3 | 4 | | | IV-1 | Oasl1 | 1.31 | 13045 | 3 | 4 | | | IV-1 | Parp2 | 1.04 |
| 12950 | 3 | 4 | | | IV-1 | Oaz2 | 1.05 | 13046 | 3 | 4 | | | IV-1 | Parp6 | 1.33 |
| 12951 | 3 | 4 | | | IV-1 | Oaz3 | 1.01 | 13047 | 3 | 4 | | | IV-1 | Parp9 | 1.48 |
| 12952 | 3 | 4 | | | IV-1 | Obsl1 | 1.05 | 13048 | 3 | 4 | | | IV-1 | Parva | 1.10 |
| 12953 | 3 | 4 | | | IV-1 | Oc90 | 1.41 | 13049 | 3 | 4 | | | IV-1 | Patz1 | 1.08 |
| 12954 | 3 | 4 | | | IV-1 | Ociad2 | 1.21 | 13050 | 3 | 4 | | | IV-1 | Pax1 | 1.17 |
| 12955 | 3 | 4 | | | IV-1 | Ocrl | 1.38 | 13051 | 3 | 4 | | | IV-1 | Pax3 | 1.50 |
| 12956 | 3 | 4 | | | IV-1 | Ogdhl | 1.25 | 13052 | 3 | 4 | | | IV-1 | Pax8 | 1.36 |
| 12957 | 3 | 4 | | | IV-1 | Ogfod2 | 1.18 | 13053 | 3 | 4 | | | IV-1 | Pax9 | 1.07 |

Fig. 45 - 69

| | | | | | | | |
|---|---|---|---|---|---|---|---|
| 13054 | 3 | 4 | | | IV-1 | Paxbp1 | 1.15 |
| 13055 | 3 | 4 | | | IV-1 | Pbld2 | 1.09 |
| 13056 | 3 | 4 | | | IV-1 | Pbx1 | 1.37 |
| 13057 | 3 | 4 | | | IV-1 | Pbx3 | 1.37 |
| 13058 | 3 | 4 | | | IV-1 | Pcbp3 | 1.25 |
| 13059 | 3 | 4 | | | IV-1 | Pcbp4 | 1.28 |
| 13060 | 3 | 4 | | | IV-1 | Pccb | 1.15 |
| 13061 | 3 | 4 | | | IV-1 | Pcdh11x | 1.44 |
| 13062 | 3 | 4 | | | IV-1 | Pcdh15 | 1.23 |
| 13063 | 3 | 4 | | | IV-1 | Pcdh17 | 1.20 |
| 13064 | 3 | 4 | | | IV-1 | Pcdh18 | 1.13 |
| 13065 | 3 | 4 | | | IV-1 | Pcdh19 | 1.29 |
| 13066 | 3 | 4 | | | IV-1 | Pcdh7 | 1.28 |
| 13067 | 3 | 4 | | | IV-1 | Pcdha11 | 1.05 |
| 13068 | 3 | 4 | | | IV-1 | Pcdha2 | 1.43 |
| 13069 | 3 | 4 | | | IV-1 | Pcdha4 | 1.04 |
| 13070 | 3 | 4 | | | IV-1 | Pcdha6 | 1.11 |
| 13071 | 3 | 4 | | | IV-1 | Pcdhac2 | 1.21 |
| 13072 | 3 | 4 | | | IV-1 | Pcdhb10 | 1.36 |
| 13073 | 3 | 4 | | | IV-1 | Pcdhb11 | 1.02 |
| 13074 | 3 | 4 | | | IV-1 | Pcdhb12 | 1.47 |
| 13075 | 3 | 4 | | | IV-1 | Pcdhb16 | 1.50 |
| 13076 | 3 | 4 | | | IV-1 | Pcdhb17 | 1.38 |
| 13077 | 3 | 4 | | | IV-1 | Pcdhb20 | 1.39 |
| 13078 | 3 | 4 | | | IV-1 | Pcdhb21 | 1.37 |
| 13079 | 3 | 4 | | | IV-1 | Pcdhb22 | 1.22 |
| 13080 | 3 | 4 | | | IV-1 | Pcdhb5 | 1.41 |
| 13081 | 3 | 4 | | | IV-1 | Pcdhb6 | 1.14 |
| 13082 | 3 | 4 | | | IV-1 | Pcdhb7 | 1.50 |
| 13083 | 3 | 4 | | | IV-1 | Pcdhga1 | 1.40 |
| 13084 | 3 | 4 | | | IV-1 | Pcdhga10 | 1.41 |
| 13085 | 3 | 4 | | | IV-1 | Pcdhga11 | 1.02 |
| 13086 | 3 | 4 | | | IV-1 | Pcdhga12 | 1.03 |
| 13087 | 3 | 4 | | | IV-1 | Pcdhga3 | 1.45 |
| 13088 | 3 | 4 | | | IV-1 | Pcdhga4 | 1.29 |
| 13089 | 3 | 4 | | | IV-1 | Pcdhga6 | 1.28 |
| 13090 | 3 | 4 | | | IV-1 | Pcdhga7 | 1.27 |
| 13091 | 3 | 4 | | | IV-1 | Pcdhga9 | 1.25 |
| 13092 | 3 | 4 | | | IV-1 | Pcdhgb1 | 1.26 |
| 13093 | 3 | 4 | | | IV-1 | Pcdhgb2 | 1.08 |
| 13094 | 3 | 4 | | | IV-1 | Pcdhgb4 | 1.10 |
| 13095 | 3 | 4 | | | IV-1 | Pcdhgb5 | 1.03 |
| 13096 | 3 | 4 | | | IV-1 | Pcdhgb6 | 1.14 |
| 13097 | 3 | 4 | | | IV-1 | Pcdhgb7 | 1.21 |
| 13098 | 3 | 4 | | | IV-1 | Pcdhgc3 | 1.01 |
| 13099 | 3 | 4 | | | IV-1 | Pcdhgc4 | 1.33 |
| 13100 | 3 | 4 | | | IV-1 | Pced1a | 1.20 |
| 13101 | 3 | 4 | | | IV-1 | Pced1b | 1.48 |
| 13102 | 3 | 4 | | | IV-1 | Pcgf6 | 1.23 |
| 13103 | 3 | 4 | | | IV-1 | Pcif1 | 1.15 |
| 13104 | 3 | 4 | | | IV-1 | Pck1 | 1.33 |
| 13105 | 3 | 4 | | | IV-1 | Pclo | 1.45 |
| 13106 | 3 | 4 | | | IV-1 | Pcm1 | 1.20 |
| 13107 | 3 | 4 | | | IV-1 | Pcmtd2 | 1.05 |
| 13108 | 3 | 4 | | | IV-1 | Pcnx | 1.22 |
| 13109 | 3 | 4 | | | IV-1 | Pcnxl2 | 1.13 |
| 13110 | 3 | 4 | | | IV-1 | Pcnxl3 | 1.18 |
| 13111 | 3 | 4 | | | IV-1 | Pcnxl4 | 1.10 |
| 13112 | 3 | 4 | | | IV-1 | Pcolce2 | 1.28 |
| 13113 | 3 | 4 | | | IV-1 | Pcsk4 | 1.01 |
| 13114 | 3 | 4 | | | IV-1 | Pcsk7 | 1.12 |
| 13115 | 3 | 4 | | | IV-1 | Pdcd11 | 1.07 |
| 13116 | 3 | 4 | | | IV-1 | Pdcd2 | 1.14 |
| 13117 | 3 | 4 | | | IV-1 | Pdcl | 1.00 |
| 13118 | 3 | 4 | | | IV-1 | Pddc1 | 1.18 |
| 13119 | 3 | 4 | | | IV-1 | Pde10a | 1.49 |
| 13120 | 3 | 4 | | | IV-1 | Pde1a | 1.35 |
| 13121 | 3 | 4 | | | IV-1 | Pde1c | 1.32 |
| 13122 | 3 | 4 | | | IV-1 | Pde3a | 1.16 |
| 13123 | 3 | 4 | | | IV-1 | Pde4b | 1.08 |
| 13124 | 3 | 4 | | | IV-1 | Pde4d | 1.05 |
| 13125 | 3 | 4 | | | IV-1 | Pde7b | 1.14 |
| 13126 | 3 | 4 | | | IV-1 | Pde8b | 1.37 |
| 13127 | 3 | 4 | | | IV-1 | Pde9a | 1.06 |
| 13128 | 3 | 4 | | | IV-1 | Pdgfa | 1.05 |
| 13129 | 3 | 4 | | | IV-1 | Pdgfra | 1.21 |
| 13130 | 3 | 4 | | | IV-1 | Pdgfrb | 1.11 |
| 13131 | 3 | 4 | | | IV-1 | Pdp1 | 1.49 |
| 13132 | 3 | 4 | | | IV-1 | Pdpn | 1.14 |
| 13133 | 3 | 4 | | | IV-1 | Pdpr | 1.46 |
| 13134 | 3 | 4 | | | IV-1 | Pdxp | 1.45 |
| 13135 | 3 | 4 | | | IV-1 | Pdyn | 1.29 |
| 13136 | 3 | 4 | | | IV-1 | Pdzd7 | 1.04 |
| 13137 | 3 | 4 | | | IV-1 | Pdzd8 | 1.05 |
| 13138 | 3 | 4 | | | IV-1 | Pdzrn3 | 1.22 |
| 13139 | 3 | 4 | | | IV-1 | Pear1 | 1.19 |
| 13140 | 3 | 4 | | | IV-1 | Peg3 | 1.33 |
| 13141 | 3 | 4 | | | IV-1 | Peli1 | 1.13 |
| 13142 | 3 | 4 | | | IV-1 | Peli2 | 1.09 |
| 13143 | 3 | 4 | | | IV-1 | Peli3 | 1.19 |
| 13144 | 3 | 4 | | | IV-1 | Penk | 1.00 |
| 13145 | 3 | 4 | | | IV-1 | Per2 | 1.09 |
| 13146 | 3 | 4 | | | IV-1 | Per3 | 1.07 |
| 13147 | 3 | 4 | | | IV-1 | Pet117 | 1.01 |
| 13148 | 3 | 4 | | | IV-1 | Pex1 | 1.21 |
| 13149 | 3 | 4 | | | IV-1 | Pex11b | 1.08 |
| 13150 | 3 | 4 | | | IV-1 | Pex12 | 1.02 |
| 13151 | 3 | 4 | | | IV-1 | Pex14 | 1.02 |
| 13152 | 3 | 4 | | | IV-1 | Pex19 | 1.02 |
| 13153 | 3 | 4 | | | IV-1 | Pex2 | 1.12 |
| 13154 | 3 | 4 | | | IV-1 | Pex3 | 1.20 |
| 13155 | 3 | 4 | | | IV-1 | Pex5 | 1.06 |
| 13156 | 3 | 4 | | | IV-1 | Pfdn1 | 1.04 |
| 13157 | 3 | 4 | | | IV-1 | Pfdn5 | 1.06 |
| 13158 | 3 | 4 | | | IV-1 | Pfkfb1 | 1.36 |
| 13159 | 3 | 4 | | | IV-1 | Pfkfb2 | 1.17 |
| 13160 | 3 | 4 | | | IV-1 | Pfkfb4 | 1.22 |
| 13161 | 3 | 4 | | | IV-1 | Pfn2 | 1.25 |
| 13162 | 3 | 4 | | | IV-1 | Pgam5 | 1.17 |
| 13163 | 3 | 4 | | | IV-1 | Pgap1 | 1.11 |
| 13164 | 3 | 4 | | | IV-1 | Pgap3 | 1.04 |
| 13165 | 3 | 4 | | | IV-1 | Pgbd5 | 1.04 |
| 13166 | 3 | 4 | | | IV-1 | Pggt1b | 1.10 |
| 13167 | 3 | 4 | | | IV-1 | Pgls | 1.02 |
| 13168 | 3 | 4 | | | IV-1 | Pglyrp1 | 1.02 |
| 13169 | 3 | 4 | | | IV-1 | Pgm2l1 | 1.11 |
| 13170 | 3 | 4 | | | IV-1 | Pgrmc1 | 1.08 |
| 13171 | 3 | 4 | | | IV-1 | Pgs1 | 1.09 |
| 13172 | 3 | 4 | | | IV-1 | Phactr2 | 1.17 |
| 13173 | 3 | 4 | | | IV-1 | Phactr3 | 1.42 |
| 13174 | 3 | 4 | | | IV-1 | Phax | 1.00 |
| 13175 | 3 | 4 | | | IV-1 | Phc1 | 1.49 |
| 13176 | 3 | 4 | | | IV-1 | Phc2 | 1.13 |
| 13177 | 3 | 4 | | | IV-1 | Phc3 | 1.03 |
| 13178 | 3 | 4 | | | IV-1 | Phf1 | 1.25 |
| 13179 | 3 | 4 | | | IV-1 | Phf11c | 1.42 |
| 13180 | 3 | 4 | | | IV-1 | Phf12 | 1.20 |
| 13181 | 3 | 4 | | | IV-1 | Phf13 | 1.01 |
| 13182 | 3 | 4 | | | IV-1 | Phf14 | 1.29 |
| 13183 | 3 | 4 | | | IV-1 | Phf2 | 1.11 |
| 13184 | 3 | 4 | | | IV-1 | Phf20 | 1.05 |
| 13185 | 3 | 4 | | | IV-1 | Phf20l1 | 1.23 |
| 13186 | 3 | 4 | | | IV-1 | Phf21a | 1.18 |
| 13187 | 3 | 4 | | | IV-1 | Phf3 | 1.01 |
| 13188 | 3 | 4 | | | IV-1 | Phf8 | 1.04 |
| 13189 | 3 | 4 | | | IV-1 | Phip | 1.06 |
| 13190 | 3 | 4 | | | IV-1 | Phka1 | 1.28 |
| 13191 | 3 | 4 | | | IV-1 | Phka2 | 1.09 |
| 13192 | 3 | 4 | | | IV-1 | Phkg2 | 1.10 |
| 13193 | 3 | 4 | | | IV-1 | Phlda3 | 1.10 |
| 13194 | 3 | 4 | | | IV-1 | Phldb1 | 1.21 |
| 13195 | 3 | 4 | | | IV-1 | Phipp1 | 1.08 |
| 13196 | 3 | 4 | | | IV-1 | Phox2a | 1.30 |
| 13197 | 3 | 4 | | | IV-1 | Phox2b | 1.36 |
| 13198 | 3 | 4 | | | IV-1 | Phrf1 | 1.06 |
| 13199 | 3 | 4 | | | IV-1 | Phyhd1 | 1.17 |
| 13200 | 3 | 4 | | | IV-1 | Phyhipl | 1.27 |
| 13201 | 3 | 4 | | | IV-1 | Phykpl | 1.14 |
| 13202 | 3 | 4 | | | IV-1 | Pi15 | 1.00 |
| 13203 | 3 | 4 | | | IV-1 | Pi4k2a | 1.03 |
| 13204 | 3 | 4 | | | IV-1 | Pias1 | 1.04 |
| 13205 | 3 | 4 | | | IV-1 | Pias2 | 1.14 |
| 13206 | 3 | 4 | | | IV-1 | Pias3 | 1.13 |
| 13207 | 3 | 4 | | | IV-1 | Pibf1 | 1.09 |
| 13208 | 3 | 4 | | | IV-1 | Pick1 | 1.24 |
| 13209 | 3 | 4 | | | IV-1 | Pid1 | 1.15 |
| 13210 | 3 | 4 | | | IV-1 | Pidd1 | 1.05 |
| 13211 | 3 | 4 | | | IV-1 | Piezo2 | 1.13 |
| 13212 | 3 | 4 | | | IV-1 | Pifo | 1.22 |
| 13213 | 3 | 4 | | | IV-1 | Pigb | 1.10 |
| 13214 | 3 | 4 | | | IV-1 | Pigh | 1.03 |
| 13215 | 3 | 4 | | | IV-1 | Pigk | 1.09 |
| 13216 | 3 | 4 | | | IV-1 | Pigo | 1.20 |
| 13217 | 3 | 4 | | | IV-1 | Pigq | 1.01 |
| 13218 | 3 | 4 | | | IV-1 | Pigp | 1.12 |
| 13219 | 3 | 4 | | | IV-1 | Pigs | 1.00 |
| 13220 | 3 | 4 | | | IV-1 | Pigt | 1.15 |
| 13221 | 3 | 4 | | | IV-1 | Pigv | 1.24 |
| 13222 | 3 | 4 | | | IV-1 | Pigw | 1.00 |
| 13223 | 3 | 4 | | | IV-1 | Pih1d2 | 1.17 |
| 13224 | 3 | 4 | | | IV-1 | Pik3ap1 | 1.25 |
| 13225 | 3 | 4 | | | IV-1 | Pik3c2a | 1.10 |
| 13226 | 3 | 4 | | | IV-1 | Pik3c2b | 1.04 |
| 13227 | 3 | 4 | | | IV-1 | Pik3c3 | 1.05 |
| 13228 | 3 | 4 | | | IV-1 | Pik3cd | 1.00 |
| 13229 | 3 | 4 | | | IV-1 | Pik3r1 | 1.16 |
| 13230 | 3 | 4 | | | IV-1 | Pik3r3 | 1.07 |
| 13231 | 3 | 4 | | | IV-1 | Pik3r4 | 1.08 |
| 13232 | 3 | 4 | | | IV-1 | Pikfyve | 1.13 |
| 13233 | 3 | 4 | | | IV-1 | Pim3 | 1.23 |
| 13234 | 3 | 4 | | | IV-1 | Pip4k2b | 1.06 |
| 13235 | 3 | 4 | | | IV-1 | Pip5k1a | 1.14 |
| 13236 | 3 | 4 | | | IV-1 | Pip5k1c | 1.28 |
| 13237 | 3 | 4 | | | IV-1 | Pisd | 1.01 |
| 13238 | 3 | 4 | | | IV-1 | Pisd-ps1 | 1.39 |
| 13239 | 3 | 4 | | | IV-1 | Pisd-ps2 | 1.13 |
| 13240 | 3 | 4 | | | IV-1 | Pisd-ps3 | 1.29 |
| 13241 | 3 | 4 | | | IV-1 | Pitpna | 1.14 |
| 13242 | 3 | 4 | | | IV-1 | Pitpnb | 1.03 |
| 13243 | 3 | 4 | | | IV-1 | Pitpnc1 | 1.09 |
| 13244 | 3 | 4 | | | IV-1 | Pitpnm1 | 1.36 |
| 13245 | 3 | 4 | | | IV-1 | Pitpnm2 | 1.09 |

Fig. 45 - 70

| | | | | | | | |
|---|---|---|---|---|---|---|---|
| 13246 | 3 | 4 | | | IV-1 | Pitpnm3 | 1.37 |
| 13247 | 3 | 4 | | | IV-1 | Pitx1 | 1.08 |
| 13248 | 3 | 4 | | | IV-1 | Pitx2 | 1.41 |
| 13249 | 3 | 4 | | | IV-1 | Pja1 | 1.09 |
| 13250 | 3 | 4 | | | IV-1 | Pja2 | 1.11 |
| 13251 | 3 | 4 | | | IV-1 | Pkd1 | 1.25 |
| 13252 | 3 | 4 | | | IV-1 | Pkd2 | 1.11 |
| 13253 | 3 | 4 | | | IV-1 | Pkia | 1.37 |
| 13254 | 3 | 4 | | | IV-1 | Pkmyt1 | 1.04 |
| 13255 | 3 | 4 | | | IV-1 | Pknox2 | 1.27 |
| 13256 | 3 | 4 | | | IV-1 | Pkp4 | 1.00 |
| 13257 | 3 | 4 | | | IV-1 | Pla1a | 1.12 |
| 13258 | 3 | 4 | | | IV-1 | Pla2g12a | 1.37 |
| 13259 | 3 | 4 | | | IV-1 | Pla2g15 | 1.04 |
| 13260 | 3 | 4 | | | IV-1 | Pla2g4e | 1.37 |
| 13261 | 3 | 4 | | | IV-1 | Pla2g6 | 1.07 |
| 13262 | 3 | 4 | | | IV-1 | Pla2g7 | 1.41 |
| 13263 | 3 | 4 | | | IV-1 | Plaa | 1.26 |
| 13264 | 3 | 4 | | | IV-1 | Plac1 | 1.04 |
| 13265 | 3 | 4 | | | IV-1 | Plac9b | 1.01 |
| 13266 | 3 | 4 | | | IV-1 | Plag1 | 1.46 |
| 13267 | 3 | 4 | | | IV-1 | Plagl1 | 1.21 |
| 13268 | 3 | 4 | | | IV-1 | Plat | 1.10 |
| 13269 | 3 | 4 | | | IV-1 | Plaur | 1.22 |
| 13270 | 3 | 4 | | | IV-1 | Plcb1 | 1.43 |
| 13271 | 3 | 4 | | | IV-1 | Plcb4 | 1.32 |
| 13272 | 3 | 4 | | | IV-1 | Plcd1 | 1.16 |
| 13273 | 3 | 4 | | | IV-1 | Plcd3 | 1.24 |
| 13274 | 3 | 4 | | | IV-1 | Plce1 | 1.23 |
| 13275 | 3 | 4 | | | IV-1 | Plcg1 | 1.28 |
| 13276 | 3 | 4 | | | IV-1 | Plch1 | 1.23 |
| 13277 | 3 | 4 | | | IV-1 | Plch2 | 1.04 |
| 13278 | 3 | 4 | | | IV-1 | Plcl1 | 1.14 |
| 13279 | 3 | 4 | | | IV-1 | Pld2 | 1.04 |
| 13280 | 3 | 4 | | | IV-1 | Pld5 | 1.09 |
| 13281 | 3 | 4 | | | IV-1 | Pld6 | 1.14 |
| 13282 | 3 | 4 | | | IV-1 | Plek | 1.01 |
| 13283 | 3 | 4 | | | IV-1 | Plekha1 | 1.17 |
| 13284 | 3 | 4 | | | IV-1 | Plekha3 | 1.21 |
| 13285 | 3 | 4 | | | IV-1 | Plekha5 | 1.25 |
| 13286 | 3 | 4 | | | IV-1 | Plekha6 | 1.17 |
| 13287 | 3 | 4 | | | IV-1 | Plekhb1 | 1.30 |
| 13288 | 3 | 4 | | | IV-1 | Plekhd1 | 1.37 |
| 13289 | 3 | 4 | | | IV-1 | Plekhg1 | 1.09 |
| 13290 | 3 | 4 | | | IV-1 | Plekhg2 | 1.11 |
| 13291 | 3 | 4 | | | IV-1 | Plekhg5 | 1.15 |
| 13292 | 3 | 4 | | | IV-1 | Plekhh2 | 1.29 |
| 13293 | 3 | 4 | | | IV-1 | Plekhm2 | 1.26 |
| 13294 | 3 | 4 | | | IV-1 | Plekhm3 | 1.16 |
| 13295 | 3 | 4 | | | IV-1 | Plk2 | 1.40 |
| 13296 | 3 | 4 | | | IV-1 | Plk3 | 1.16 |
| 13297 | 3 | 4 | | | IV-1 | Pln | 1.36 |
| 13298 | 3 | 4 | | | IV-1 | Plrg1 | 1.00 |
| 13299 | 3 | 4 | | | IV-1 | Plscr3 | 1.20 |
| 13300 | 3 | 4 | | | IV-1 | Plscr4 | 1.18 |
| 13301 | 3 | 4 | | | IV-1 | Plxna1 | 1.15 |
| 13302 | 3 | 4 | | | IV-1 | Plxna2 | 1.19 |
| 13303 | 3 | 4 | | | IV-1 | Plxna3 | 1.01 |
| 13304 | 3 | 4 | | | IV-1 | Plxnb1 | 1.14 |
| 13305 | 3 | 4 | | | IV-1 | Plxnc1 | 1.02 |
| 13306 | 3 | 4 | | | IV-1 | Pm20d2 | 1.00 |
| 13307 | 3 | 4 | | | IV-1 | Pmaip1 | 1.49 |
| 13308 | 3 | 4 | | | IV-1 | Pmepa1 | 1.07 |
| 13309 | 3 | 4 | | | IV-1 | Pmm2 | 1.01 |
| 13310 | 3 | 4 | | | IV-1 | Pms2 | 1.21 |
| 13311 | 3 | 4 | | | IV-1 | Pnck | 1.29 |
| 13312 | 3 | 4 | | | IV-1 | Pnisr | 1.17 |
| 13313 | 3 | 4 | | | IV-1 | Pnma2 | 1.42 |
| 13314 | 3 | 4 | | | IV-1 | Pnmal2 | 1.06 |
| 13315 | 3 | 4 | | | IV-1 | Pnn | 1.09 |
| 13316 | 3 | 4 | | | IV-1 | Pnpla6 | 1.07 |
| 13317 | 3 | 4 | | | IV-1 | Pnpla7 | 1.31 |
| 13318 | 3 | 4 | | | IV-1 | Pnpla8 | 1.09 |
| 13319 | 3 | 4 | | | IV-1 | Poc5 | 1.22 |
| 13320 | 3 | 4 | | | IV-1 | Pogk | 1.17 |
| 13321 | 3 | 4 | | | IV-1 | Poglut1 | 1.05 |
| 13322 | 3 | 4 | | | IV-1 | Pogz | 1.12 |
| 13323 | 3 | 4 | | | IV-1 | Pold4 | 1.06 |
| 13324 | 3 | 4 | | | IV-1 | Poldip2 | 1.01 |
| 13325 | 3 | 4 | | | IV-1 | Poli | 1.02 |
| 13326 | 3 | 4 | | | IV-1 | Polk | 1.12 |
| 13327 | 3 | 4 | | | IV-1 | Polm | 1.29 |
| 13328 | 3 | 4 | | | IV-1 | Polr1a | 1.02 |
| 13329 | 3 | 4 | | | IV-1 | Polr1b | 1.13 |
| 13330 | 3 | 4 | | | IV-1 | Polr1e | 1.09 |
| 13331 | 3 | 4 | | | IV-1 | Polr2a | 1.08 |
| 13332 | 3 | 4 | | | IV-1 | Polr2i | 1.07 |
| 13333 | 3 | 4 | | | IV-1 | Polr3a | 1.07 |
| 13334 | 3 | 4 | | | IV-1 | Polr3b | 1.19 |
| 13335 | 3 | 4 | | | IV-1 | Polr3e | 1.12 |
| 13336 | 3 | 4 | | | IV-1 | Polr3f | 1.19 |
| 13337 | 3 | 4 | | | IV-1 | Polr3gl | 1.13 |
| 13338 | 3 | 4 | | | IV-1 | Polr3h | 1.21 |
| 13339 | 3 | 4 | | | IV-1 | Polr3k | 1.07 |
| 13340 | 3 | 4 | | | IV-1 | Pom121 | 1.06 |
| 13341 | 3 | 4 | | | IV-1 | Pomc | 1.01 |
| 13342 | 3 | 4 | | | IV-1 | Pomgnt2 | 1.04 |
| 13343 | 3 | 4 | | | IV-1 | Pomt2 | 1.15 |
| 13344 | 3 | 4 | | | IV-1 | Pop4 | 1.08 |
| 13345 | 3 | 4 | | | IV-1 | Por | 1.24 |
| 13346 | 3 | 4 | | | IV-1 | Pot1b | 1.05 |
| 13347 | 3 | 4 | | | IV-1 | Pou2f1 | 1.02 |
| 13348 | 3 | 4 | | | IV-1 | Pou3f1 | 1.06 |
| 13349 | 3 | 4 | | | IV-1 | Pou3f3os | 1.46 |
| 13350 | 3 | 4 | | | IV-1 | Pou6f2 | 1.18 |
| 13351 | 3 | 4 | | | IV-1 | Ppa2 | 1.17 |
| 13352 | 3 | 4 | | | IV-1 | Ppan | 1.12 |
| 13353 | 3 | 4 | | | IV-1 | Ppap2a | 1.00 |
| 13354 | 3 | 4 | | | IV-1 | Ppap2b | 1.16 |
| 13355 | 3 | 4 | | | IV-1 | Ppapdc2 | 1.18 |
| 13356 | 3 | 4 | | | IV-1 | Ppargc1a | 1.04 |
| 13357 | 3 | 4 | | | IV-1 | Ppcdc | 1.17 |
| 13358 | 3 | 4 | | | IV-1 | Ppfia1 | 1.04 |
| 13359 | 3 | 4 | | | IV-1 | Ppfia2 | 1.27 |
| 13360 | 3 | 4 | | | IV-1 | Ppfia4 | 1.15 |
| 13361 | 3 | 4 | | | IV-1 | Ppfibp1 | 1.12 |
| 13362 | 3 | 4 | | | IV-1 | Ppfhn1 | 1.10 |
| 13363 | 3 | 4 | | | IV-1 | Ppifos | 1.12 |
| 13364 | 3 | 4 | | | IV-1 | Ppih | 1.25 |
| 13365 | 3 | 4 | | | IV-1 | Ppil2 | 1.15 |
| 13366 | 3 | 4 | | | IV-1 | Ppil4 | 1.00 |
| 13367 | 3 | 4 | | | IV-1 | Ppil6 | 1.00 |
| 13368 | 3 | 4 | | | IV-1 | Ppip5k2 | 1.18 |
| 13369 | 3 | 4 | | | IV-1 | Ppm1a | 1.10 |
| 13370 | 3 | 4 | | | IV-1 | Ppm1d | 1.02 |
| 13371 | 3 | 4 | | | IV-1 | Ppm1e | 1.29 |
| 13372 | 3 | 4 | | | IV-1 | Ppm1h | 1.08 |
| 13373 | 3 | 4 | | | IV-1 | Ppp1r12b | 1.05 |
| 13374 | 3 | 4 | | | IV-1 | Ppp1r12c | 1.06 |
| 13375 | 3 | 4 | | | IV-1 | Ppp1r13b | 1.02 |
| 13376 | 3 | 4 | | | IV-1 | Ppp1r18 | 1.06 |
| 13377 | 3 | 4 | | | IV-1 | Ppp1r1b | 1.02 |
| 13378 | 3 | 4 | | | IV-1 | Ppp1r2 | 1.15 |
| 13379 | 3 | 4 | | | IV-1 | Ppp1r2-ps3 | 1.50 |
| 13380 | 3 | 4 | | | IV-1 | Ppp1r21 | 1.10 |
| 13381 | 3 | 4 | | | IV-1 | Ppp1r26 | 1.40 |
| 13382 | 3 | 4 | | | IV-1 | Ppp1r3e | 1.10 |
| 13383 | 3 | 4 | | | IV-1 | Ppp1r8 | 1.05 |
| 13384 | 3 | 4 | | | IV-1 | Ppp1r9a | 1.16 |
| 13385 | 3 | 4 | | | IV-1 | Ppp1r9b | 1.04 |
| 13386 | 3 | 4 | | | IV-1 | Ppp2cb | 1.01 |
| 13387 | 3 | 4 | | | IV-1 | Ppp2r1a | 1.12 |
| 13388 | 3 | 4 | | | IV-1 | Ppp2r2d | 1.12 |
| 13389 | 3 | 4 | | | IV-1 | Ppp2r3c | 1.11 |
| 13390 | 3 | 4 | | | IV-1 | Ppp2r3d | 1.27 |
| 13391 | 3 | 4 | | | IV-1 | Ppp2r5b | 1.16 |
| 13392 | 3 | 4 | | | IV-1 | Ppp2r5e | 1.03 |
| 13393 | 3 | 4 | | | IV-1 | Ppp3ca | 1.20 |
| 13394 | 3 | 4 | | | IV-1 | Ppp3cb | 1.12 |
| 13395 | 3 | 4 | | | IV-1 | Ppp3r1 | 1.06 |
| 13396 | 3 | 4 | | | IV-1 | Ppp4r1 | 1.06 |
| 13397 | 3 | 4 | | | IV-1 | Ppp6r2 | 1.27 |
| 13398 | 3 | 4 | | | IV-1 | Pqbp1 | 1.20 |
| 13399 | 3 | 4 | | | IV-1 | Pqlc3 | 1.07 |
| 13400 | 3 | 4 | | | IV-1 | Pram1 | 1.40 |
| 13401 | 3 | 4 | | | IV-1 | Pramef8 | 1.08 |
| 13402 | 3 | 4 | | | IV-1 | Prdm10 | 1.35 |
| 13403 | 3 | 4 | | | IV-1 | Prdm11 | 1.49 |
| 13404 | 3 | 4 | | | IV-1 | Prdm15 | 1.16 |
| 13405 | 3 | 4 | | | IV-1 | Prdm4 | 1.27 |
| 13406 | 3 | 4 | | | IV-1 | Prdm9 | 1.27 |
| 13407 | 3 | 4 | | | IV-1 | Prickle1 | 1.28 |
| 13408 | 3 | 4 | | | IV-1 | Prickle2 | 1.21 |
| 13409 | 3 | 4 | | | IV-1 | Prickle4 | 1.34 |
| 13410 | 3 | 4 | | | IV-1 | Prkab2 | 1.01 |
| 13411 | 3 | 4 | | | IV-1 | Prkacb | 1.31 |
| 13412 | 3 | 4 | | | IV-1 | Prkar1b | 1.46 |
| 13413 | 3 | 4 | | | IV-1 | Prkca | 1.17 |
| 13414 | 3 | 4 | | | IV-1 | Prkcb | 1.20 |
| 13415 | 3 | 4 | | | IV-1 | Prkce | 1.36 |
| 13416 | 3 | 4 | | | IV-1 | Prkci | 1.02 |
| 13417 | 3 | 4 | | | IV-1 | Prkcz | 1.32 |
| 13418 | 3 | 4 | | | IV-1 | Prkd1 | 1.10 |
| 13419 | 3 | 4 | | | IV-1 | Prkd3 | 1.06 |
| 13420 | 3 | 4 | | | IV-1 | Prkg1 | 1.09 |
| 13421 | 3 | 4 | | | IV-1 | Prkrip1 | 1.06 |
| 13422 | 3 | 4 | | | IV-1 | Prkrir | 1.23 |
| 13423 | 3 | 4 | | | IV-1 | Prkx | 1.03 |
| 13424 | 3 | 4 | | | IV-1 | Prmt1 | 1.01 |
| 13425 | 3 | 4 | | | IV-1 | Prmt10 | 1.17 |
| 13426 | 3 | 4 | | | IV-1 | Prmt2 | 1.05 |
| 13427 | 3 | 4 | | | IV-1 | Prmt5 | 1.01 |
| 13428 | 3 | 4 | | | IV-1 | Prmt6 | 1.27 |
| 13429 | 3 | 4 | | | IV-1 | Prnp | 1.18 |
| 13430 | 3 | 4 | | | IV-1 | Prodh | 1.37 |
| 13431 | 3 | 4 | | | IV-1 | Prokr2 | 1.37 |
| 13432 | 3 | 4 | | | IV-1 | Proser1 | 1.30 |
| 13433 | 3 | 4 | | | IV-1 | Proser2 | 1.14 |
| 13434 | 3 | 4 | | | IV-1 | Prox1 | 1.13 |
| 13435 | 3 | 4 | | | IV-1 | Prox2 | 1.44 |
| 13436 | 3 | 4 | | | IV-1 | Prpf19 | 1.03 |
| 13437 | 3 | 4 | | | IV-1 | Prpf31 | 1.14 |

Fig. 45 - 71

| | | | | | | | | | | | | | | |
|---|---|---|---|---|---|---|---|---|---|---|---|---|---|---|
| 13438 | 3 | 4 | | | IV-1 | Prpf39 | 1.25 | 13534 | 3 | 4 | | | IV-1 | Qsox2 | 1.06 |
| 13439 | 3 | 4 | | | IV-1 | Prpf40b | 1.05 | 13535 | 3 | 4 | | | IV-1 | Qtrt1 | 1.06 |
| 13440 | 3 | 4 | | | IV-1 | Prpf8 | 1.05 | 13536 | 3 | 4 | | | IV-1 | Qtrtd1 | 1.09 |
| 13441 | 3 | 4 | | | IV-1 | Prpsap1 | 1.04 | 13537 | 3 | 4 | | | IV-1 | R3hcc1 | 1.13 |
| 13442 | 3 | 4 | | | IV-1 | Prpsap2 | 1.17 | 13538 | 3 | 4 | | | IV-1 | R3hdm1 | 1.04 |
| 13443 | 3 | 4 | | | IV-1 | Prr12 | 1.19 | 13539 | 3 | 4 | | | IV-1 | R3hdm2 | 1.04 |
| 13444 | 3 | 4 | | | IV-1 | Prr14 | 1.02 | 13540 | 3 | 4 | | | IV-1 | R3hdm4 | 1.25 |
| 13445 | 3 | 4 | | | IV-1 | Prr16 | 1.31 | 13541 | 3 | 4 | | | IV-1 | R74862 | 1.06 |
| 13446 | 3 | 4 | | | IV-1 | Prr24 | 1.32 | 13542 | 3 | 4 | | | IV-1 | Rab11b | 1.09 |
| 13447 | 3 | 4 | | | IV-1 | Prr3 | 1.28 | 13543 | 3 | 4 | | | IV-1 | Rab11fip2 | 1.49 |
| 13448 | 3 | 4 | | | IV-1 | Prr32 | 1.19 | 13544 | 3 | 4 | | | IV-1 | Rab11fip3 | 1.07 |
| 13449 | 3 | 4 | | | IV-1 | Prrc1 | 1.00 | 13545 | 3 | 4 | | | IV-1 | Rab11fip5 | 1.04 |
| 13450 | 3 | 4 | | | IV-1 | Prrc2b | 1.23 | 13546 | 3 | 4 | | | IV-1 | Rab12 | 1.15 |
| 13451 | 3 | 4 | | | IV-1 | Prrc2c | 1.02 | 13547 | 3 | 4 | | | IV-1 | Rab15 | 1.14 |
| 13452 | 3 | 4 | | | IV-1 | Prrg1 | 1.09 | 13548 | 3 | 4 | | | IV-1 | Rab20 | 1.15 |
| 13453 | 3 | 4 | | | IV-1 | Prrg4 | 1.12 | 13549 | 3 | 4 | | | IV-1 | Rab23 | 1.08 |
| 13454 | 3 | 4 | | | IV-1 | Prrt2 | 1.33 | 13550 | 3 | 4 | | | IV-1 | Rab24 | 1.10 |
| 13455 | 3 | 4 | | | IV-1 | Prrt3 | 1.28 | 13551 | 3 | 4 | | | IV-1 | Rab26os | 1.38 |
| 13456 | 3 | 4 | | | IV-1 | Prrx1 | 1.11 | 13552 | 3 | 4 | | | IV-1 | Rab28 | 1.08 |
| 13457 | 3 | 4 | | | IV-1 | Prrx2 | 1.50 | 13553 | 3 | 4 | | | IV-1 | Rab2a | 1.06 |
| 13458 | 3 | 4 | | | IV-1 | Prss12 | 1.40 | 13554 | 3 | 4 | | | IV-1 | Rab2b | 1.20 |
| 13459 | 3 | 4 | | | IV-1 | Prss22 | 1.15 | 13555 | 3 | 4 | | | IV-1 | Rab30 | 1.15 |
| 13460 | 3 | 4 | | | IV-1 | Prss23 | 1.13 | 13556 | 3 | 4 | | | IV-1 | Rab31 | 1.23 |
| 13461 | 3 | 4 | | | IV-1 | Prune2 | 1.04 | 13557 | 3 | 4 | | | IV-1 | Rab33b | 1.11 |
| 13462 | 3 | 4 | | | IV-1 | Prx | 1.17 | 13558 | 3 | 4 | | | IV-1 | Rab3a | 1.42 |
| 13463 | 3 | 4 | | | IV-1 | Psap | 1.01 | 13559 | 3 | 4 | | | IV-1 | Rab3c | 1.44 |
| 13464 | 3 | 4 | | | IV-1 | Psca | 1.28 | 13560 | 3 | 4 | | | IV-1 | Rab40c | 1.03 |
| 13465 | 3 | 4 | | | IV-1 | Psd | 1.35 | 13561 | 3 | 4 | | | IV-1 | Rab4a | 1.19 |
| 13466 | 3 | 4 | | | IV-1 | Psd3 | 1.03 | 13562 | 3 | 4 | | | IV-1 | Rab4b | 1.10 |
| 13467 | 3 | 4 | | | IV-1 | Psen2 | 1.16 | 13563 | 3 | 4 | | | IV-1 | Rab5a | 1.27 |
| 13468 | 3 | 4 | | | IV-1 | Psg16 | 1.08 | 13564 | 3 | 4 | | | IV-1 | Rab5b | 1.03 |
| 13469 | 3 | 4 | | | IV-1 | Pskh1 | 1.19 | 13565 | 3 | 4 | | | IV-1 | Rab6a | 1.06 |
| 13470 | 3 | 4 | | | IV-1 | Psmc4 | 1.06 | 13566 | 3 | 4 | | | IV-1 | Rab6b | 1.43 |
| 13471 | 3 | 4 | | | IV-1 | Psmd9 | 1.11 | 13567 | 3 | 4 | | | IV-1 | Rab7 | 1.07 |
| 13472 | 3 | 4 | | | IV-1 | Psme1 | 1.02 | 13568 | 3 | 4 | | | IV-1 | Rab9b | 1.18 |
| 13473 | 3 | 4 | | | IV-1 | Psmf1 | 1.25 | 13569 | 3 | 4 | | | IV-1 | Rabep2 | 1.05 |
| 13474 | 3 | 4 | | | IV-1 | Psmg4 | 1.40 | 13570 | 3 | 4 | | | IV-1 | Rabgap1 | 1.20 |
| 13475 | 3 | 4 | | | IV-1 | Pspc1 | 1.29 | 13571 | 3 | 4 | | | IV-1 | Rabgap1l | 1.10 |
| 13476 | 3 | 4 | | | IV-1 | Psrc1 | 1.19 | 13572 | 3 | 4 | | | IV-1 | Rabl3 | 1.01 |
| 13477 | 3 | 4 | | | IV-1 | Ptgds | 1.14 | 13573 | 3 | 4 | | | IV-1 | Rac3 | 1.24 |
| 13478 | 3 | 4 | | | IV-1 | Ptger1 | 1.01 | 13574 | 3 | 4 | | | IV-1 | Rad18 | 1.13 |
| 13479 | 3 | 4 | | | IV-1 | Ptges | 1.49 | 13575 | 3 | 4 | | | IV-1 | Rad50 | 1.02 |
| 13480 | 3 | 4 | | | IV-1 | Ptgfr | 1.14 | 13576 | 3 | 4 | | | IV-1 | Rad51d | 1.12 |
| 13481 | 3 | 4 | | | IV-1 | Ptgis | 1.19 | 13577 | 3 | 4 | | | IV-1 | Rad54l2 | 1.10 |
| 13482 | 3 | 4 | | | IV-1 | Pth | 1.45 | 13578 | 3 | 4 | | | IV-1 | Radil | 1.02 |
| 13483 | 3 | 4 | | | IV-1 | Pthlh | 1.10 | 13579 | 3 | 4 | | | IV-1 | Rae1 | 1.01 |
| 13484 | 3 | 4 | | | IV-1 | Ptk2 | 1.07 | 13580 | 3 | 4 | | | IV-1 | Raf1 | 1.03 |
| 13485 | 3 | 4 | | | IV-1 | Ptk6 | 1.47 | 13581 | 3 | 4 | | | IV-1 | Rai1 | 1.28 |
| 13486 | 3 | 4 | | | IV-1 | Ptk7 | 1.24 | 13582 | 3 | 4 | | | IV-1 | Rala | 1.12 |
| 13487 | 3 | 4 | | | IV-1 | Ptn | 1.13 | 13583 | 3 | 4 | | | IV-1 | Ralgapa2 | 1.05 |
| 13488 | 3 | 4 | | | IV-1 | Ptov1 | 1.23 | 13584 | 3 | 4 | | | IV-1 | Ralgapb | 1.07 |
| 13489 | 3 | 4 | | | IV-1 | Ptp4a1 | 1.03 | 13585 | 3 | 4 | | | IV-1 | Ralgds | 1.16 |
| 13490 | 3 | 4 | | | IV-1 | Ptp4a2 | 1.00 | 13586 | 3 | 4 | | | IV-1 | Ralgps1 | 1.43 |
| 13491 | 3 | 4 | | | IV-1 | Ptpdc1 | 1.46 | 13587 | 3 | 4 | | | IV-1 | Ralgps2 | 1.06 |
| 13492 | 3 | 4 | | | IV-1 | Ptplb | 1.13 | 13588 | 3 | 4 | | | IV-1 | Ranbp3 | 1.09 |
| 13493 | 3 | 4 | | | IV-1 | Ptpn1 | 1.08 | 13589 | 3 | 4 | | | IV-1 | Ranbp3l | 1.34 |
| 13494 | 3 | 4 | | | IV-1 | Ptpn23 | 1.20 | 13590 | 3 | 4 | | | IV-1 | Ranbp9 | 1.06 |
| 13495 | 3 | 4 | | | IV-1 | Ptpn9 | 1.25 | 13591 | 3 | 4 | | | IV-1 | Rap1gap | 1.22 |
| 13496 | 3 | 4 | | | IV-1 | Ptprd | 1.38 | 13592 | 3 | 4 | | | IV-1 | Rap1gap2 | 1.08 |
| 13497 | 3 | 4 | | | IV-1 | Ptpre | 1.48 | 13593 | 3 | 4 | | | IV-1 | Rap2a | 1.00 |
| 13498 | 3 | 4 | | | IV-1 | Ptprg | 1.29 | 13594 | 3 | 4 | | | IV-1 | Rap2b | 1.04 |
| 13499 | 3 | 4 | | | IV-1 | Ptprk | 1.07 | 13595 | 3 | 4 | | | IV-1 | Rap2c | 1.07 |
| 13500 | 3 | 4 | | | IV-1 | Ptprm | 1.10 | 13596 | 3 | 4 | | | IV-1 | Rapgef1 | 1.14 |
| 13501 | 3 | 4 | | | IV-1 | Ptpro | 1.37 | 13597 | 3 | 4 | | | IV-1 | Rapgef2 | 1.22 |
| 13502 | 3 | 4 | | | IV-1 | Ptprr | 1.37 | 13598 | 3 | 4 | | | IV-1 | Rapgef4 | 1.29 |
| 13503 | 3 | 4 | | | IV-1 | Ptprs | 1.23 | 13599 | 3 | 4 | | | IV-1 | Rapgef6 | 1.08 |
| 13504 | 3 | 4 | | | IV-1 | Ptpru | 1.43 | 13600 | 3 | 4 | | | IV-1 | Rapgefl1 | 1.02 |
| 13505 | 3 | 4 | | | IV-1 | Ptprv | 1.15 | 13601 | 3 | 4 | | | IV-1 | Rapsn | 1.05 |
| 13506 | 3 | 4 | | | IV-1 | Ptprz1 | 1.39 | 13602 | 3 | 4 | | | IV-1 | Rara | 1.06 |
| 13507 | 3 | 4 | | | IV-1 | Ptrh1 | 1.14 | 13603 | 3 | 4 | | | IV-1 | Rarb | 1.13 |
| 13508 | 3 | 4 | | | IV-1 | Pttg1 | 1.03 | 13604 | 3 | 4 | | | IV-1 | Rarg | 1.13 |
| 13509 | 3 | 4 | | | IV-1 | Pttg1ip | 1.08 | 13605 | 3 | 4 | | | IV-1 | Rasa1 | 1.09 |
| 13510 | 3 | 4 | | | IV-1 | Pum1 | 1.12 | 13606 | 3 | 4 | | | IV-1 | Rasa2 | 1.23 |
| 13511 | 3 | 4 | | | IV-1 | Pum2 | 1.09 | 13607 | 3 | 4 | | | IV-1 | Rasa4 | 1.22 |
| 13512 | 3 | 4 | | | IV-1 | Pus3 | 1.06 | 13608 | 3 | 4 | | | IV-1 | Rasal2 | 1.21 |
| 13513 | 3 | 4 | | | IV-1 | Pusl1 | 1.16 | 13609 | 3 | 4 | | | IV-1 | Rasd1 | 1.33 |
| 13514 | 3 | 4 | | | IV-1 | Pvrl1 | 1.01 | 13610 | 3 | 4 | | | IV-1 | Rasgef1a | 1.04 |
| 13515 | 3 | 4 | | | IV-1 | Pvrl4 | 1.00 | 13611 | 3 | 4 | | | IV-1 | Rasgef1b | 1.25 |
| 13516 | 3 | 4 | | | IV-1 | Pvt1 | 1.01 | 13612 | 3 | 4 | | | IV-1 | Rasgef1c | 1.21 |
| 13517 | 3 | 4 | | | IV-1 | Pwp1 | 1.12 | 13613 | 3 | 4 | | | IV-1 | Rasgrf1 | 1.40 |
| 13518 | 3 | 4 | | | IV-1 | Pwp2 | 1.00 | 13614 | 3 | 4 | | | IV-1 | Rasgrf2 | 1.20 |
| 13519 | 3 | 4 | | | IV-1 | Pwwp2a | 1.11 | 13615 | 3 | 4 | | | IV-1 | Rasl10b | 1.29 |
| 13520 | 3 | 4 | | | IV-1 | Pxdc1 | 1.03 | 13616 | 3 | 4 | | | IV-1 | Rasl11a | 1.19 |
| 13521 | 3 | 4 | | | IV-1 | Pxk | 1.07 | 13617 | 3 | 4 | | | IV-1 | Rasl11b | 1.07 |
| 13522 | 3 | 4 | | | IV-1 | Pxn | 1.01 | 13618 | 3 | 4 | | | IV-1 | Rassf1 | 1.00 |
| 13523 | 3 | 4 | | | IV-1 | Pycr1 | 1.02 | 13619 | 3 | 4 | | | IV-1 | Rassf8 | 1.19 |
| 13524 | 3 | 4 | | | IV-1 | Pvgo1 | 1.26 | 13620 | 3 | 4 | | | IV-1 | Rax | 1.17 |
| 13525 | 3 | 4 | | | IV-1 | Pyhin1 | 1.02 | 13621 | 3 | 4 | | | IV-1 | Rbbp6 | 1.07 |
| 13526 | 3 | 4 | | | IV-1 | Pyroxd1 | 1.29 | 13622 | 3 | 4 | | | IV-1 | Rbbp8 | 1.03 |
| 13527 | 3 | 4 | | | IV-1 | Pyy | 1.44 | 13623 | 3 | 4 | | | IV-1 | Rbbp9 | 1.04 |
| 13528 | 3 | 4 | | | IV-1 | Qk | 1.02 | 13624 | 3 | 4 | | | IV-1 | Rbck1 | 1.03 |
| 13529 | 3 | 4 | | | IV-1 | Qpct | 1.03 | 13625 | 3 | 4 | | | IV-1 | Rbfa | 1.22 |
| 13530 | 3 | 4 | | | IV-1 | Qpctl | 1.09 | 13626 | 3 | 4 | | | IV-1 | Rbfox1 | 1.41 |
| 13531 | 3 | 4 | | | IV-1 | Qrich1 | 1.05 | 13627 | 3 | 4 | | | IV-1 | Rbfox2 | 1.29 |
| 13532 | 3 | 4 | | | IV-1 | Qser1 | 1.08 | 13628 | 3 | 4 | | | IV-1 | Rbm11 | 1.49 |
| 13533 | 3 | 4 | | | IV-1 | Qsox1 | 1.19 | 13629 | 3 | 4 | | | IV-1 | Rbm12 | 1.09 |

Fig. 45 - 72

| | | | | | | | | | | | | | | |
|---|---|---|---|---|---|---|---|---|---|---|---|---|---|---|
| 13630 | 3 | 4 | | | IV-1 | Rbm12b2 | 1.07 | 13726 | 3 | 4 | | | IV-1 | Rims1 | 1.24 |
| 13631 | 3 | 4 | | | IV-1 | Rbm15b | 1.13 | 13727 | 3 | 4 | | | IV-1 | Rims3 | 1.49 |
| 13632 | 3 | 4 | | | IV-1 | Rbm17 | 1.01 | 13728 | 3 | 4 | | | IV-1 | Rin2 | 1.05 |
| 13633 | 3 | 4 | | | IV-1 | Rbm18 | 1.23 | 13729 | 3 | 4 | | | IV-1 | Ring1 | 1.00 |
| 13634 | 3 | 4 | | | IV-1 | Rbm19 | 1.01 | 13730 | 3 | 4 | | | IV-1 | Riok1 | 1.24 |
| 13635 | 3 | 4 | | | IV-1 | Rbm20 | 1.12 | 13731 | 3 | 4 | | | IV-1 | Riok2 | 1.13 |
| 13636 | 3 | 4 | | | IV-1 | Rbm22 | 1.08 | 13732 | 3 | 4 | | | IV-1 | Riok3 | 1.08 |
| 13637 | 3 | 4 | | | IV-1 | Rbm25 | 1.14 | 13733 | 3 | 4 | | | IV-1 | Rbp1 | 1.17 |
| 13638 | 3 | 4 | | | IV-1 | Rbm3 | 1.29 | 13734 | 3 | 4 | | | IV-1 | Rif | 1.20 |
| 13639 | 3 | 4 | | | IV-1 | Rbm33 | 1.03 | 13735 | 3 | 4 | | | IV-1 | Rim | 1.00 |
| 13640 | 3 | 4 | | | IV-1 | Rbm34 | 1.29 | 13736 | 3 | 4 | | | IV-1 | Ritpr | 1.14 |
| 13641 | 3 | 4 | | | IV-1 | Rbm39 | 1.01 | 13737 | 3 | 4 | | | IV-1 | Rmnd5b | 1.06 |
| 13642 | 3 | 4 | | | IV-1 | Rbm41 | 1.03 | 13738 | 3 | 4 | | | IV-1 | Rmst | 1.02 |
| 13643 | 3 | 4 | | | IV-1 | Rbm42 | 1.00 | 13739 | 3 | 4 | | | IV-1 | Rnase4 | 1.18 |
| 13644 | 3 | 4 | | | IV-1 | Rbm45 | 1.04 | 13740 | 3 | 4 | | | IV-1 | Rnaseh1 | 1.09 |
| 13645 | 3 | 4 | | | IV-1 | Rbm46 | 1.10 | 13741 | 3 | 4 | | | IV-1 | Rnasel | 1.25 |
| 13646 | 3 | 4 | | | IV-1 | Rbm48 | 1.14 | 13742 | 3 | 4 | | | IV-1 | Rnd1 | 1.35 |
| 13647 | 3 | 4 | | | IV-1 | Rbm4b | 1.22 | 13743 | 3 | 4 | | | IV-1 | Rnd3 | 1.29 |
| 13648 | 3 | 4 | | | IV-1 | Rbm5 | 1.04 | 13744 | 3 | 4 | | | IV-1 | Rnf103 | 1.10 |
| 13649 | 3 | 4 | | | IV-1 | Rbm7 | 1.13 | 13745 | 3 | 4 | | | IV-1 | Rnf11 | 1.02 |
| 13650 | 3 | 4 | | | IV-1 | Rbms1 | 1.16 | 13746 | 3 | 4 | | | IV-1 | Rnf111 | 1.10 |
| 13651 | 3 | 4 | | | IV-1 | Rbms2 | 1.05 | 13747 | 3 | 4 | | | IV-1 | Rnf112 | 1.39 |
| 13652 | 3 | 4 | | | IV-1 | Rbms3 | 1.03 | 13748 | 3 | 4 | | | IV-1 | Rnf113a1 | 1.12 |
| 13653 | 3 | 4 | | | IV-1 | Rbmx | 1.10 | 13749 | 3 | 4 | | | IV-1 | Rnf113a2 | 1.02 |
| 13654 | 3 | 4 | | | IV-1 | Rbmx2 | 1.17 | 13750 | 3 | 4 | | | IV-1 | Rnf114 | 1.11 |
| 13655 | 3 | 4 | | | IV-1 | Rbpj | 1.04 | 13751 | 3 | 4 | | | IV-1 | Rnf115 | 1.04 |
| 13656 | 3 | 4 | | | IV-1 | Rbpms | 1.10 | 13752 | 3 | 4 | | | IV-1 | Rnf122 | 1.03 |
| 13657 | 3 | 4 | | | IV-1 | Rbx1 | 1.25 | 13753 | 3 | 4 | | | IV-1 | Rnf13 | 1.02 |
| 13658 | 3 | 4 | | | IV-1 | Rc3h2 | 1.07 | 13754 | 3 | 4 | | | IV-1 | Rnf130 | 1.37 |
| 13659 | 3 | 4 | | | IV-1 | Rcan1 | 1.01 | 13755 | 3 | 4 | | | IV-1 | Rnf135 | 1.26 |
| 13660 | 3 | 4 | | | IV-1 | Rcan2 | 1.22 | 13756 | 3 | 4 | | | IV-1 | Rnf138 | 1.21 |
| 13661 | 3 | 4 | | | IV-1 | Rcan3 | 1.17 | 13757 | 3 | 4 | | | IV-1 | Rnf14 | 1.20 |
| 13662 | 3 | 4 | | | IV-1 | Rcbtb1 | 1.29 | 13758 | 3 | 4 | | | IV-1 | Rnf144a | 1.15 |
| 13663 | 3 | 4 | | | IV-1 | Rcbtb2 | 1.13 | 13759 | 3 | 4 | | | IV-1 | Rnf145 | 1.11 |
| 13664 | 3 | 4 | | | IV-1 | Rce1 | 1.12 | 13760 | 3 | 4 | | | IV-1 | Rnf149 | 1.02 |
| 13665 | 3 | 4 | | | IV-1 | Rcn2 | 1.23 | 13761 | 3 | 4 | | | IV-1 | Rnf150 | 1.10 |
| 13666 | 3 | 4 | | | IV-1 | Rcor2 | 1.09 | 13762 | 3 | 4 | | | IV-1 | Rnf152 | 1.19 |
| 13667 | 3 | 4 | | | IV-1 | Rcor3 | 1.19 | 13763 | 3 | 4 | | | IV-1 | Rnf157 | 1.28 |
| 13668 | 3 | 4 | | | IV-1 | Rd3 | 1.04 | 13764 | 3 | 4 | | | IV-1 | Rnf165 | 1.48 |
| 13669 | 3 | 4 | | | IV-1 | Rdh10 | 1.10 | 13765 | 3 | 4 | | | IV-1 | Rnf166 | 1.11 |
| 13670 | 3 | 4 | | | IV-1 | Rdh13 | 1.13 | 13766 | 3 | 4 | | | IV-1 | Rnf169 | 1.27 |
| 13671 | 3 | 4 | | | IV-1 | Rdh14 | 1.14 | 13767 | 3 | 4 | | | IV-1 | Rnf170 | 1.17 |
| 13672 | 3 | 4 | | | IV-1 | Reck | 1.41 | 13768 | 3 | 4 | | | IV-1 | Rnf182 | 1.32 |
| 13673 | 3 | 4 | | | IV-1 | Recql5 | 1.04 | 13769 | 3 | 4 | | | IV-1 | Rnf185 | 1.04 |
| 13674 | 3 | 4 | | | IV-1 | Reep1 | 1.30 | 13770 | 3 | 4 | | | IV-1 | Rnf187 | 1.05 |
| 13675 | 3 | 4 | | | IV-1 | Reep3 | 1.10 | 13771 | 3 | 4 | | | IV-1 | Rnf19b | 1.22 |
| 13676 | 3 | 4 | | | IV-1 | Reg3g | 1.38 | 13772 | 3 | 4 | | | IV-1 | Rnf2 | 1.17 |
| 13677 | 3 | 4 | | | IV-1 | Rela | 1.02 | 13773 | 3 | 4 | | | IV-1 | Rnf208 | 1.27 |
| 13678 | 3 | 4 | | | IV-1 | Relb | 1.19 | 13774 | 3 | 4 | | | IV-1 | Rnf214 | 1.09 |
| 13679 | 3 | 4 | | | IV-1 | Rell2 | 1.22 | 13775 | 3 | 4 | | | IV-1 | Rnf215 | 1.12 |
| 13680 | 3 | 4 | | | IV-1 | Reln | 1.14 | 13776 | 3 | 4 | | | IV-1 | Rnf216 | 1.03 |
| 13681 | 3 | 4 | | | IV-1 | Rem2 | 1.43 | 13777 | 3 | 4 | | | IV-1 | Rnf217 | 1.02 |
| 13682 | 3 | 4 | | | IV-1 | Repin1 | 1.04 | 13778 | 3 | 4 | | | IV-1 | Rnf220 | 1.27 |
| 13683 | 3 | 4 | | | IV-1 | Reps1 | 1.36 | 13779 | 3 | 4 | | | IV-1 | Rnf223 | 1.12 |
| 13684 | 3 | 4 | | | IV-1 | Rere | 1.06 | 13780 | 3 | 4 | | | IV-1 | Rnf224 | 1.01 |
| 13685 | 3 | 4 | | | IV-1 | Rerg | 1.22 | 13781 | 3 | 4 | | | IV-1 | Rnf24 | 1.22 |
| 13686 | 3 | 4 | | | IV-1 | Resp18 | 1.36 | 13782 | 3 | 4 | | | IV-1 | Rnf25 | 1.02 |
| 13687 | 3 | 4 | | | IV-1 | Rest | 1.13 | 13783 | 3 | 4 | | | IV-1 | Rnf31 | 1.16 |
| 13688 | 3 | 4 | | | IV-1 | Ret | 1.26 | 13784 | 3 | 4 | | | IV-1 | Rnf38 | 1.06 |
| 13689 | 3 | 4 | | | IV-1 | Retsat | 1.37 | 13785 | 3 | 4 | | | IV-1 | Rnf40 | 1.13 |
| 13690 | 3 | 4 | | | IV-1 | Rev1 | 1.39 | 13786 | 3 | 4 | | | IV-1 | Rnf41 | 1.19 |
| 13691 | 3 | 4 | | | IV-1 | Rev3l | 1.15 | 13787 | 3 | 4 | | | IV-1 | Rnf44 | 1.03 |
| 13692 | 3 | 4 | | | IV-1 | Rexo1 | 1.08 | 13788 | 3 | 4 | | | IV-1 | Rnft2 | 1.36 |
| 13693 | 3 | 4 | | | IV-1 | Rfc3 | 1.08 | 13789 | 3 | 4 | | | IV-1 | Rnh1 | 1.02 |
| 13694 | 3 | 4 | | | IV-1 | Rfng | 1.16 | 13790 | 3 | 4 | | | IV-1 | Rnls | 1.21 |
| 13695 | 3 | 4 | | | IV-1 | Rft1 | 1.44 | 13791 | 3 | 4 | | | IV-1 | Rnmt | 1.44 |
| 13696 | 3 | 4 | | | IV-1 | Rftn1 | 1.21 | 13792 | 3 | 4 | | | IV-1 | Rnpc3 | 1.38 |
| 13697 | 3 | 4 | | | IV-1 | Rfwd2 | 1.01 | 13793 | 3 | 4 | | | IV-1 | Robo1 | 1.19 |
| 13698 | 3 | 4 | | | IV-1 | Rfx1 | 1.02 | 13794 | 3 | 4 | | | IV-1 | Robo2 | 1.35 |
| 13699 | 3 | 4 | | | IV-1 | Rfx3 | 1.31 | 13795 | 3 | 4 | | | IV-1 | Rock2 | 1.00 |
| 13700 | 3 | 4 | | | IV-1 | Rfx7 | 1.18 | 13796 | 3 | 4 | | | IV-1 | Rogdi | 1.00 |
| 13701 | 3 | 4 | | | IV-1 | Rgag1 | 1.24 | 13797 | 3 | 4 | | | IV-1 | Rom1 | 1.28 |
| 13702 | 3 | 4 | | | IV-1 | Rgma | 1.32 | 13798 | 3 | 4 | | | IV-1 | Romo1 | 1.13 |
| 13703 | 3 | 4 | | | IV-1 | Rgmb | 1.04 | 13799 | 3 | 4 | | | IV-1 | Ror1 | 1.21 |
| 13704 | 3 | 4 | | | IV-1 | Rgp1 | 1.13 | 13800 | 3 | 4 | | | IV-1 | Ror2 | 1.07 |
| 13705 | 3 | 4 | | | IV-1 | Rgs1 | 1.24 | 13801 | 3 | 4 | | | IV-1 | Rpain | 1.06 |
| 13706 | 3 | 4 | | | IV-1 | Rgs11 | 1.09 | 13802 | 3 | 4 | | | IV-1 | Rpap2 | 1.22 |
| 13707 | 3 | 4 | | | IV-1 | Rgs12 | 1.20 | 13803 | 3 | 4 | | | IV-1 | Rpap3 | 1.37 |
| 13708 | 3 | 4 | | | IV-1 | Rgs20 | 1.07 | 13804 | 3 | 4 | | | IV-1 | Rpgr | 1.20 |
| 13709 | 3 | 4 | | | IV-1 | Rgs4 | 1.25 | 13805 | 3 | 4 | | | IV-1 | Rph3a | 1.37 |
| 13710 | 3 | 4 | | | IV-1 | Rhbdd2 | 1.39 | 13806 | 3 | 4 | | | IV-1 | Rpl10a | 1.06 |
| 13711 | 3 | 4 | | | IV-1 | Rhbdd3 | 1.13 | 13807 | 3 | 4 | | | IV-1 | Rpl11 | 1.08 |
| 13712 | 3 | 4 | | | IV-1 | Rhbdf1 | 1.20 | 13808 | 3 | 4 | | | IV-1 | Rpl12 | 1.33 |
| 13713 | 3 | 4 | | | IV-1 | Rhbdl1 | 1.02 | 13809 | 3 | 4 | | | IV-1 | Rpl13 | 1.04 |
| 13714 | 3 | 4 | | | IV-1 | Rheb | 1.02 | 13810 | 3 | 4 | | | IV-1 | Rpl14-ps1 | 1.04 |
| 13715 | 3 | 4 | | | IV-1 | Rhebl1 | 1.36 | 13811 | 3 | 4 | | | IV-1 | Rpl17 | 1.08 |
| 13716 | 3 | 4 | | | IV-1 | Rhobtb1 | 1.13 | 13812 | 3 | 4 | | | IV-1 | Rpl18 | 1.03 |
| 13717 | 3 | 4 | | | IV-1 | Rhobtb2 | 1.12 | 13813 | 3 | 4 | | | IV-1 | Rpl18a | 1.04 |
| 13718 | 3 | 4 | | | IV-1 | Rhobtb3 | 1.12 | 13814 | 3 | 4 | | | IV-1 | Rpl21 | 1.01 |
| 13719 | 3 | 4 | | | IV-1 | Rhof | 1.16 | 13815 | 3 | 4 | | | IV-1 | Rpl22 | 1.18 |
| 13720 | 3 | 4 | | | IV-1 | Ric8 | 1.18 | 13816 | 3 | 4 | | | IV-1 | Rpl24 | 1.28 |
| 13721 | 3 | 4 | | | IV-1 | Ric8b | 1.23 | 13817 | 3 | 4 | | | IV-1 | Rpl28 | 1.05 |
| 13722 | 3 | 4 | | | IV-1 | Rictor | 1.23 | 13818 | 3 | 4 | | | IV-1 | Rpl29 | 1.13 |
| 13723 | 3 | 4 | | | IV-1 | Riipl1 | 1.12 | 13819 | 3 | 4 | | | IV-1 | Rpl3 | 1.01 |
| 13724 | 3 | 4 | | | IV-1 | Riipl2 | 1.23 | 13820 | 3 | 4 | | | IV-1 | Rpl32 | 1.14 |
| 13725 | 3 | 4 | | | IV-1 | Rimkla | 1.38 | 13821 | 3 | 4 | | | IV-1 | Rpl35 | 1.06 |

Fig. 45 - 73

| | | | | | | | | | | | | | |
|---|---|---|---|---|---|---|---|---|---|---|---|---|---|
| 13822 | 3 | 4 | | | IV-1 | Rpl35a | 1.08 | 13918 | 3 | 4 | | IV-1 | Rusc2 | 1.22 |
| 13823 | 3 | 4 | | | IV-1 | Rpl36 | 1.19 | 13919 | 3 | 4 | | IV-1 | Ruvbl1 | 1.00 |
| 13824 | 3 | 4 | | | IV-1 | Rpl36a | 1.10 | 13920 | 3 | 4 | | IV-1 | Rwdd1 | 1.05 |
| 13825 | 3 | 4 | | | IV-1 | Rpl5 | 1.15 | 13921 | 3 | 4 | | IV-1 | Rwdd2a | 1.31 |
| 13826 | 3 | 4 | | | IV-1 | Rpl8 | 1.04 | 13922 | 3 | 4 | | IV-1 | Rwdd3 | 1.27 |
| 13827 | 3 | 4 | | | IV-1 | Rplp0 | 1.01 | 13923 | 3 | 4 | | IV-1 | Rwdd4a | 1.09 |
| 13828 | 3 | 4 | | | IV-1 | Rplp2-ps1 | 1.08 | 13924 | 3 | 4 | | IV-1 | Rxrb | 1.16 |
| 13829 | 3 | 4 | | | IV-1 | Rpp25 | 1.15 | 13925 | 3 | 4 | | IV-1 | Ryr2 | 1.42 |
| 13830 | 3 | 4 | | | IV-1 | Rpph1 | 1.01 | 13926 | 3 | 4 | | IV-1 | S100a3 | 1.28 |
| 13831 | 3 | 4 | | | IV-1 | Rprm | 1.48 | 13927 | 3 | 4 | | IV-1 | S100a6 | 1.38 |
| 13832 | 3 | 4 | | | IV-1 | Rps10 | 1.14 | 13928 | 3 | 4 | | IV-1 | S100a7a | 1.17 |
| 13833 | 3 | 4 | | | IV-1 | Rps11 | 1.11 | 13929 | 3 | 4 | | IV-1 | S100a8 | 1.11 |
| 13834 | 3 | 4 | | | IV-1 | Rps12 | 1.25 | 13930 | 3 | 4 | | IV-1 | S100a9 | 1.10 |
| 13835 | 3 | 4 | | | IV-1 | Rps13 | 1.02 | 13931 | 3 | 4 | | IV-1 | S100pbp | 1.08 |
| 13836 | 3 | 4 | | | IV-1 | Rps14 | 1.15 | 13932 | 3 | 4 | | IV-1 | S1pr1 | 1.00 |
| 13837 | 3 | 4 | | | IV-1 | Rps15a | 1.24 | 13933 | 3 | 4 | | IV-1 | Saa1 | 1.43 |
| 13838 | 3 | 4 | | | IV-1 | Rps15a-ps4 | 1.04 | 13934 | 3 | 4 | | IV-1 | Saa3 | 1.14 |
| 13839 | 3 | 4 | | | IV-1 | Rps15a-ps6 | 1.08 | 13935 | 3 | 4 | | IV-1 | Safb | 1.11 |
| 13840 | 3 | 4 | | | IV-1 | Rps16 | 1.12 | 13936 | 3 | 4 | | IV-1 | Sall1 | 1.20 |
| 13841 | 3 | 4 | | | IV-1 | Rps17 | 1.04 | 13937 | 3 | 4 | | IV-1 | Sall2 | 1.13 |
| 13842 | 3 | 4 | | | IV-1 | Rps18 | 1.19 | 13938 | 3 | 4 | | IV-1 | Samd10 | 1.35 |
| 13843 | 3 | 4 | | | IV-1 | Rps19 | 1.27 | 13939 | 3 | 4 | | IV-1 | Samd12 | 1.23 |
| 13844 | 3 | 4 | | | IV-1 | Rps19-ps3 | 1.01 | 13940 | 3 | 4 | | IV-1 | Samd14 | 1.33 |
| 13845 | 3 | 4 | | | IV-1 | Rps20 | 1.07 | 13941 | 3 | 4 | | IV-1 | Samd4 | 1.06 |
| 13846 | 3 | 4 | | | IV-1 | Rps23 | 1.08 | 13942 | 3 | 4 | | IV-1 | Samd4b | 1.02 |
| 13847 | 3 | 4 | | | IV-1 | Rps24 | 1.01 | 13943 | 3 | 4 | | IV-1 | Samd5 | 1.07 |
| 13848 | 3 | 4 | | | IV-1 | Rps25 | 1.23 | 13944 | 3 | 4 | | IV-1 | Samd8 | 1.20 |
| 13849 | 3 | 4 | | | IV-1 | Rps26 | 1.07 | 13945 | 3 | 4 | | IV-1 | Sap130 | 1.10 |
| 13850 | 3 | 4 | | | IV-1 | Rps27a | 1.10 | 13946 | 3 | 4 | | IV-1 | Sap30bp | 1.05 |
| 13851 | 3 | 4 | | | IV-1 | Rps28 | 1.26 | 13947 | 3 | 4 | | IV-1 | Sap30l | 1.19 |
| 13852 | 3 | 4 | | | IV-1 | Rps3 | 1.03 | 13948 | 3 | 4 | | IV-1 | Sapcd1 | 1.28 |
| 13853 | 3 | 4 | | | IV-1 | Rps3a1 | 1.05 | 13949 | 3 | 4 | | IV-1 | Sars | 1.08 |
| 13854 | 3 | 4 | | | IV-1 | Rps4l | 1.10 | 13950 | 3 | 4 | | IV-1 | Sash1 | 1.12 |
| 13855 | 3 | 4 | | | IV-1 | Rps4x | 1.01 | 13951 | 3 | 4 | | IV-1 | Sat1 | 1.39 |
| 13856 | 3 | 4 | | | IV-1 | Rps5 | 1.03 | 13952 | 3 | 4 | | IV-1 | Sat2 | 1.33 |
| 13857 | 3 | 4 | | | IV-1 | Rps6ka2 | 1.15 | 13953 | 3 | 4 | | IV-1 | Satb1 | 1.03 |
| 13858 | 3 | 4 | | | IV-1 | Rps6ka5 | 1.42 | 13954 | 3 | 4 | | IV-1 | Saysd1 | 1.13 |
| 13859 | 3 | 4 | | | IV-1 | Rps6ka6 | 1.05 | 13955 | 3 | 4 | | IV-1 | Sbf1 | 1.02 |
| 13860 | 3 | 4 | | | IV-1 | Rps6kb1 | 1.10 | 13956 | 3 | 4 | | IV-1 | Sbf2 | 1.35 |
| 13861 | 3 | 4 | | | IV-1 | Rps6kb2 | 1.08 | 13957 | 3 | 4 | | IV-1 | Sbno2 | 1.15 |
| 13862 | 3 | 4 | | | IV-1 | Rps6kc1 | 1.14 | 13958 | 3 | 4 | | IV-1 | Scaf1 | 1.04 |
| 13863 | 3 | 4 | | | IV-1 | Rps6kl1 | 1.48 | 13959 | 3 | 4 | | IV-1 | Scaf4 | 1.05 |
| 13864 | 3 | 4 | | | IV-1 | Rps7 | 1.10 | 13960 | 3 | 4 | | IV-1 | Scaf8 | 1.15 |
| 13865 | 3 | 4 | | | IV-1 | Rps8 | 1.05 | 13961 | 3 | 4 | | IV-1 | Scai | 1.39 |
| 13866 | 3 | 4 | | | IV-1 | Rps9 | 1.04 | 13962 | 3 | 4 | | IV-1 | Scamp1 | 1.19 |
| 13867 | 3 | 4 | | | IV-1 | Rptor | 1.01 | 13963 | 3 | 4 | | IV-1 | Scamp2 | 1.04 |
| 13868 | 3 | 4 | | | IV-1 | Rpusd1 | 1.16 | 13964 | 3 | 4 | | IV-1 | Scamp3 | 1.11 |
| 13869 | 3 | 4 | | | IV-1 | Rpusd2 | 1.03 | 13965 | 3 | 4 | | IV-1 | Scap | 1.15 |
| 13870 | 3 | 4 | | | IV-1 | Rpusd3 | 1.11 | 13966 | 3 | 4 | | IV-1 | Scaper | 1.31 |
| 13871 | 3 | 4 | | | IV-1 | Rraga | 1.06 | 13967 | 3 | 4 | | IV-1 | Scara3 | 1.06 |
| 13872 | 3 | 4 | | | IV-1 | Rragb | 1.50 | 13968 | 3 | 4 | | IV-1 | Scara5 | 1.24 |
| 13873 | 3 | 4 | | | IV-1 | Rragc | 1.03 | 13969 | 3 | 4 | | IV-1 | Scarb2 | 1.23 |
| 13874 | 3 | 4 | | | IV-1 | Rras | 1.14 | 13970 | 3 | 4 | | IV-1 | Scarf2 | 1.27 |
| 13875 | 3 | 4 | | | IV-1 | Rrm2b | 1.04 | 13971 | 3 | 4 | | IV-1 | Scarna13 | 1.35 |
| 13876 | 3 | 4 | | | IV-1 | Rrn3 | 1.12 | 13972 | 3 | 4 | | IV-1 | Scgb3a2 | 1.02 |
| 13877 | 3 | 4 | | | IV-1 | Rrnad1 | 1.00 | 13973 | 3 | 4 | | IV-1 | Schip1 | 1.31 |
| 13878 | 3 | 4 | | | IV-1 | Rrp1 | 1.02 | 13974 | 3 | 4 | | IV-1 | Scit1 | 1.02 |
| 13879 | 3 | 4 | | | IV-1 | Rrp12 | 1.13 | 13975 | 3 | 4 | | IV-1 | Scmh1 | 1.04 |
| 13880 | 3 | 4 | | | IV-1 | Rrp15 | 1.05 | 13976 | 3 | 4 | | IV-1 | Scml4 | 1.20 |
| 13881 | 3 | 4 | | | IV-1 | Rrp1b | 1.18 | 13977 | 3 | 4 | | IV-1 | Scn1b | 1.07 |
| 13882 | 3 | 4 | | | IV-1 | Rrp36 | 1.18 | 13978 | 3 | 4 | | IV-1 | Scn3b | 1.39 |
| 13883 | 3 | 4 | | | IV-1 | Rrp8 | 1.00 | 13979 | 3 | 4 | | IV-1 | Scn5a | 1.28 |
| 13884 | 3 | 4 | | | IV-1 | Rrp9 | 1.02 | 13980 | 3 | 4 | | IV-1 | Scnn1a | 1.41 |
| 13885 | 3 | 4 | | | IV-1 | Rrs1 | 1.04 | 13981 | 3 | 4 | | IV-1 | Sco1 | 1.01 |
| 13886 | 3 | 4 | | | IV-1 | Rsad1 | 1.34 | 13982 | 3 | 4 | | IV-1 | Scrn1 | 1.26 |
| 13887 | 3 | 4 | | | IV-1 | Rsbn1 | 1.06 | 13983 | 3 | 4 | | IV-1 | Sct | 1.04 |
| 13888 | 3 | 4 | | | IV-1 | Rsbn1l | 1.04 | 13984 | 3 | 4 | | IV-1 | Scube1 | 1.23 |
| 13889 | 3 | 4 | | | IV-1 | Rsf1 | 1.03 | 13985 | 3 | 4 | | IV-1 | Scube2 | 1.03 |
| 13890 | 3 | 4 | | | IV-1 | Rsl1d1 | 1.03 | 13986 | 3 | 4 | | IV-1 | Scx | 1.16 |
| 13891 | 3 | 4 | | | IV-1 | Rsl24d1 | 1.04 | 13987 | 3 | 4 | | IV-1 | Scyl3 | 1.45 |
| 13892 | 3 | 4 | | | IV-1 | Rsph4a | 1.05 | 13988 | 3 | 4 | | IV-1 | Sdad1 | 1.33 |
| 13893 | 3 | 4 | | | IV-1 | Rsph9 | 1.04 | 13989 | 3 | 4 | | IV-1 | Sdc3 | 1.29 |
| 13894 | 3 | 4 | | | IV-1 | Rspo1 | 1.06 | 13990 | 3 | 4 | | IV-1 | Sdccag3 | 1.06 |
| 13895 | 3 | 4 | | | IV-1 | Rspo2 | 1.27 | 13991 | 3 | 4 | | IV-1 | Sdccag8 | 1.32 |
| 13896 | 3 | 4 | | | IV-1 | Rsrc1 | 1.15 | 13992 | 3 | 4 | | IV-1 | Sdf4 | 1.11 |
| 13897 | 3 | 4 | | | IV-1 | Rtca | 1.34 | 13993 | 3 | 4 | | IV-1 | Sdhaf1 | 1.28 |
| 13898 | 3 | 4 | | | IV-1 | Rtcb | 1.04 | 13994 | 3 | 4 | | IV-1 | Sdk2 | 1.19 |
| 13899 | 3 | 4 | | | IV-1 | Rtel1 | 1.05 | 13995 | 3 | 4 | | IV-1 | Sdr39u1 | 1.05 |
| 13900 | 3 | 4 | | | IV-1 | Rtf1 | 1.21 | 13996 | 3 | 4 | | IV-1 | Sec1 | 1.09 |
| 13901 | 3 | 4 | | | IV-1 | Rtfdc1 | 1.06 | 13997 | 3 | 4 | | IV-1 | Sec22c | 1.04 |
| 13902 | 3 | 4 | | | IV-1 | Rtkn | 1.01 | 13998 | 3 | 4 | | IV-1 | Sec23a | 1.00 |
| 13903 | 3 | 4 | | | IV-1 | Rtl1 | 1.05 | 13999 | 3 | 4 | | IV-1 | Sec24b | 1.08 |
| 13904 | 3 | 4 | | | IV-1 | Rtn2 | 1.04 | 14000 | 3 | 4 | | IV-1 | Sec61a2 | 1.22 |
| 13905 | 3 | 4 | | | IV-1 | Rtn3 | 1.02 | 14001 | 3 | 4 | | IV-1 | Sec63 | 1.26 |
| 13906 | 3 | 4 | | | IV-1 | Rtn4 | 1.03 | 14002 | 3 | 4 | | IV-1 | Secisbp2 | 1.25 |
| 13907 | 3 | 4 | | | IV-1 | Rtn4r | 1.20 | 14003 | 3 | 4 | | IV-1 | Secisbp2l | 1.24 |
| 13908 | 3 | 4 | | | IV-1 | Rtn4rl1 | 1.12 | 14004 | 3 | 4 | | IV-1 | Sel1l | 1.07 |
| 13909 | 3 | 4 | | | IV-1 | Rtp1 | 1.12 | 14005 | 3 | 4 | | IV-1 | Selenbp1 | 1.08 |
| 13910 | 3 | 4 | | | IV-1 | Rufy1 | 1.19 | 14006 | 3 | 4 | | IV-1 | Seli | 1.16 |
| 13911 | 3 | 4 | | | IV-1 | Rufy2 | 1.34 | 14007 | 3 | 4 | | IV-1 | Selo | 1.01 |
| 13912 | 3 | 4 | | | IV-1 | Rufy3 | 1.37 | 14008 | 3 | 4 | | IV-1 | Sema3a | 1.25 |
| 13913 | 3 | 4 | | | IV-1 | Runx1 | 1.02 | 14009 | 3 | 4 | | IV-1 | Sema3d | 1.24 |
| 13914 | 3 | 4 | | | IV-1 | Runx1t1 | 1.31 | 14010 | 3 | 4 | | IV-1 | Sema3f | 1.24 |
| 13915 | 3 | 4 | | | IV-1 | Runx2 | 1.06 | 14011 | 3 | 4 | | IV-1 | Sema3g | 1.18 |
| 13916 | 3 | 4 | | | IV-1 | Runx3 | 1.02 | 14012 | 3 | 4 | | IV-1 | Sema4c | 1.24 |
| 13917 | 3 | 4 | | | IV-1 | Rusc1 | 1.26 | 14013 | 3 | 4 | | IV-1 | Sema4d | 1.03 |

Fig. 45 - 74

| | | | | | | | | | | | | | |
|---|---|---|---|---|---|---|---|---|---|---|---|---|---|
| 14014 | 3 | 4 | | | IV-1 | Sema4f | 1.29 | 14110 | 3 | 4 | | IV-1 | Sipa1l2 | 1.11 |
| 14015 | 3 | 4 | | | IV-1 | Sema4g | 1.22 | 14111 | 3 | 4 | | IV-1 | Sirpa | 1.07 |
| 14016 | 3 | 4 | | | IV-1 | Sema5a | 1.21 | 14112 | 3 | 4 | | IV-1 | Sirt5 | 1.04 |
| 14017 | 3 | 4 | | | IV-1 | Sema6a | 1.17 | 14113 | 3 | 4 | | IV-1 | Sirt6 | 1.19 |
| 14018 | 3 | 4 | | | IV-1 | Sema6b | 1.14 | 14114 | 3 | 4 | | IV-1 | Six2 | 1.06 |
| 14019 | 3 | 4 | | | IV-1 | Sema6c | 1.08 | 14115 | 3 | 4 | | IV-1 | Six3os1 | 1.29 |
| 14020 | 3 | 4 | | | IV-1 | Sema6d | 1.01 | 14116 | 3 | 4 | | IV-1 | Ski | 1.19 |
| 14021 | 3 | 4 | | | IV-1 | Sema7a | 1.09 | 14117 | 3 | 4 | | IV-1 | Skida1 | 1.08 |
| 14022 | 3 | 4 | | | IV-1 | Senp5 | 1.13 | 14118 | 3 | 4 | | IV-1 | Skil | 1.11 |
| 14023 | 3 | 4 | | | IV-1 | Senp6 | 1.16 | 14119 | 3 | 4 | | IV-1 | Skiv2l | 1.05 |
| 14024 | 3 | 4 | | | IV-1 | Sephs1 | 1.05 | 14120 | 3 | 4 | | IV-1 | Skp1a | 1.03 |
| 14025 | 3 | 4 | | | IV-1 | Sept5 | 1.09 | 14121 | 3 | 4 | | IV-1 | Sla | 1.16 |
| 14026 | 3 | 4 | | | IV-1 | Sept6 | 1.06 | 14122 | 3 | 4 | | IV-1 | Slain1 | 1.16 |
| 14027 | 3 | 4 | | | IV-1 | Serac1 | 1.34 | 14123 | 3 | 4 | | IV-1 | Slc10a1 | 1.14 |
| 14028 | 3 | 4 | | | IV-1 | Sergef | 1.19 | 14124 | 3 | 4 | | IV-1 | Slc10a6 | 1.32 |
| 14029 | 3 | 4 | | | IV-1 | Serhl | 1.03 | 14125 | 3 | 4 | | IV-1 | Slc11a1 | 1.10 |
| 14030 | 3 | 4 | | | IV-1 | Serinc1 | 1.16 | 14126 | 3 | 4 | | IV-1 | Slc12a2 | 1.14 |
| 14031 | 3 | 4 | | | IV-1 | Serinc2 | 1.04 | 14127 | 3 | 4 | | IV-1 | Slc12a5 | 1.46 |
| 14032 | 3 | 4 | | | IV-1 | Serp2 | 1.18 | 14128 | 3 | 4 | | IV-1 | Slc12a6 | 1.13 |
| 14033 | 3 | 4 | | | IV-1 | Serpinb10 | 1.22 | 14129 | 3 | 4 | | IV-1 | Slc12a9 | 1.36 |
| 14034 | 3 | 4 | | | IV-1 | Serpinb11 | 1.44 | 14130 | 3 | 4 | | IV-1 | Slc13a4 | 1.14 |
| 14035 | 3 | 4 | | | IV-1 | Serpinb6a | 1.08 | 14131 | 3 | 4 | | IV-1 | Slc13a5 | 1.12 |
| 14036 | 3 | 4 | | | IV-1 | Serpinb8 | 1.04 | 14132 | 3 | 4 | | IV-1 | Slc14a2 | 1.09 |
| 14037 | 3 | 4 | | | IV-1 | Serpine1 | 1.35 | 14133 | 3 | 4 | | IV-1 | Slc15a2 | 1.38 |
| 14038 | 3 | 4 | | | IV-1 | Serpine2 | 1.11 | 14134 | 3 | 4 | | IV-1 | Slc16a11 | 1.34 |
| 14039 | 3 | 4 | | | IV-1 | Sertad4 | 1.41 | 14135 | 3 | 4 | | IV-1 | Slc16a4 | 1.19 |
| 14040 | 3 | 4 | | | IV-1 | Set | 1.05 | 14136 | 3 | 4 | | IV-1 | Slc16a7 | 1.14 |
| 14041 | 3 | 4 | | | IV-1 | Setd1a | 1.12 | 14137 | 3 | 4 | | IV-1 | Slc16a8 | 1.02 |
| 14042 | 3 | 4 | | | IV-1 | Setd2 | 1.18 | 14138 | 3 | 4 | | IV-1 | Slc16a9 | 1.11 |
| 14043 | 3 | 4 | | | IV-1 | Setd4 | 1.36 | 14139 | 3 | 4 | | IV-1 | Slc17a7 | 1.20 |
| 14044 | 3 | 4 | | | IV-1 | Setd5 | 1.09 | 14140 | 3 | 4 | | IV-1 | Slc19a1 | 1.17 |
| 14045 | 3 | 4 | | | IV-1 | Setd6 | 1.09 | 14141 | 3 | 4 | | IV-1 | Slc1a1 | 1.48 |
| 14046 | 3 | 4 | | | IV-1 | Setx | 1.21 | 14142 | 3 | 4 | | IV-1 | Slc1a2 | 1.41 |
| 14047 | 3 | 4 | | | IV-1 | Sf3a1 | 1.03 | 14143 | 3 | 4 | | IV-1 | Slc1a3 | 1.30 |
| 14048 | 3 | 4 | | | IV-1 | Sf3a2 | 1.08 | 14144 | 3 | 4 | | IV-1 | Slc1a4 | 1.25 |
| 14049 | 3 | 4 | | | IV-1 | Sf3b1 | 1.06 | 14145 | 3 | 4 | | IV-1 | Slc20a2 | 1.12 |
| 14050 | 3 | 4 | | | IV-1 | Sf3b2 | 1.01 | 14146 | 3 | 4 | | IV-1 | Slc22a15 | 1.38 |
| 14051 | 3 | 4 | | | IV-1 | Sf3b4 | 1.04 | 14147 | 3 | 4 | | IV-1 | Slc22a17 | 1.50 |
| 14052 | 3 | 4 | | | IV-1 | Sfi1 | 1.45 | 14148 | 3 | 4 | | IV-1 | Slc22a21 | 1.37 |
| 14053 | 3 | 4 | | | IV-1 | Sfmbt1 | 1.29 | 14149 | 3 | 4 | | IV-1 | Slc22a5 | 1.06 |
| 14054 | 3 | 4 | | | IV-1 | Sfmbt2 | 1.39 | 14150 | 3 | 4 | | IV-1 | Slc22a6 | 1.01 |
| 14055 | 3 | 4 | | | IV-1 | Sfpq | 1.13 | 14151 | 3 | 4 | | IV-1 | Slc22a8 | 1.43 |
| 14056 | 3 | 4 | | | IV-1 | Sfrp1 | 1.33 | 14152 | 3 | 4 | | IV-1 | Slc23a2 | 1.36 |
| 14057 | 3 | 4 | | | IV-1 | Sfrp2 | 1.41 | 14153 | 3 | 4 | | IV-1 | Slc23a3 | 1.24 |
| 14058 | 3 | 4 | | | IV-1 | Sfswap | 1.23 | 14154 | 3 | 4 | | IV-1 | Slc24a2 | 1.42 |
| 14059 | 3 | 4 | | | IV-1 | Sft2d3 | 1.16 | 14155 | 3 | 4 | | IV-1 | Slc24a3 | 1.25 |
| 14060 | 3 | 4 | | | IV-1 | Sfta2 | 1.28 | 14156 | 3 | 4 | | IV-1 | Slc24a5 | 1.05 |
| 14061 | 3 | 4 | | | IV-1 | Sfxn2 | 1.04 | 14157 | 3 | 4 | | IV-1 | Slc25a12 | 1.05 |
| 14062 | 3 | 4 | | | IV-1 | Sgcb | 1.12 | 14158 | 3 | 4 | | IV-1 | Slc25a16 | 1.14 |
| 14063 | 3 | 4 | | | IV-1 | Sgce | 1.10 | 14159 | 3 | 4 | | IV-1 | Slc25a17 | 1.03 |
| 14064 | 3 | 4 | | | IV-1 | Sgk1 | 1.41 | 14160 | 3 | 4 | | IV-1 | Slc25a18 | 1.42 |
| 14065 | 3 | 4 | | | IV-1 | Sgpl1 | 1.03 | 14161 | 3 | 4 | | IV-1 | Slc25a22 | 1.14 |
| 14066 | 3 | 4 | | | IV-1 | Sgsh | 1.10 | 14162 | 3 | 4 | | IV-1 | Slc25a26 | 1.18 |
| 14067 | 3 | 4 | | | IV-1 | Sgsm1 | 1.37 | 14163 | 3 | 4 | | IV-1 | Slc25a28 | 1.42 |
| 14068 | 3 | 4 | | | IV-1 | Sgtb | 1.32 | 14164 | 3 | 4 | | IV-1 | Slc25a29 | 1.17 |
| 14069 | 3 | 4 | | | IV-1 | Sh2b3 | 1.06 | 14165 | 3 | 4 | | IV-1 | Slc25a30 | 1.19 |
| 14070 | 3 | 4 | | | IV-1 | Sh2d3c | 1.36 | 14166 | 3 | 4 | | IV-1 | Slc25a32 | 1.01 |
| 14071 | 3 | 4 | | | IV-1 | Sh2d5 | 1.28 | 14167 | 3 | 4 | | IV-1 | Slc25a33 | 1.13 |
| 14072 | 3 | 4 | | | IV-1 | Sh3bp2 | 1.15 | 14168 | 3 | 4 | | IV-1 | Slc25a34 | 1.16 |
| 14073 | 3 | 4 | | | IV-1 | Sh3bp5 | 1.24 | 14169 | 3 | 4 | | IV-1 | Slc25a36 | 1.11 |
| 14074 | 3 | 4 | | | IV-1 | Sh3gl2 | 1.40 | 14170 | 3 | 4 | | IV-1 | Slc25a40 | 1.19 |
| 14075 | 3 | 4 | | | IV-1 | Sh3gl3 | 1.24 | 14171 | 3 | 4 | | IV-1 | Slc25a46 | 1.01 |
| 14076 | 3 | 4 | | | IV-1 | Sh3glb2 | 1.06 | 14172 | 3 | 4 | | IV-1 | Slc26a11 | 1.02 |
| 14077 | 3 | 4 | | | IV-1 | Sh3pxd2b | 1.05 | 14173 | 3 | 4 | | IV-1 | Slc26a6 | 1.21 |
| 14078 | 3 | 4 | | | IV-1 | Sh3rf1 | 1.16 | 14174 | 3 | 4 | | IV-1 | Slc26a7 | 1.37 |
| 14079 | 3 | 4 | | | IV-1 | Sh3rf3 | 1.32 | 14175 | 3 | 4 | | IV-1 | Slc26a8 | 1.38 |
| 14080 | 3 | 4 | | | IV-1 | Shank1 | 1.47 | 14176 | 3 | 4 | | IV-1 | Slc27a1 | 1.02 |
| 14081 | 3 | 4 | | | IV-1 | Shank2 | 1.45 | 14177 | 3 | 4 | | IV-1 | Slc27a2 | 1.04 |
| 14082 | 3 | 4 | | | IV-1 | Shank3 | 1.14 | 14178 | 3 | 4 | | IV-1 | Slc29a2 | 1.35 |
| 14083 | 3 | 4 | | | IV-1 | Sharpin | 1.19 | 14179 | 3 | 4 | | IV-1 | Slc29a3 | 1.12 |
| 14084 | 3 | 4 | | | IV-1 | Shb | 1.09 | 14180 | 3 | 4 | | IV-1 | Slc2a13 | 1.13 |
| 14085 | 3 | 4 | | | IV-1 | Shc1 | 1.02 | 14181 | 3 | 4 | | IV-1 | Slc2a3 | 1.22 |
| 14086 | 3 | 4 | | | IV-1 | Shc2 | 1.15 | 14182 | 3 | 4 | | IV-1 | Slc2a9 | 1.35 |
| 14087 | 3 | 4 | | | IV-1 | Shf | 1.15 | 14183 | 3 | 4 | | IV-1 | Slc30a1 | 1.09 |
| 14088 | 3 | 4 | | | IV-1 | Shisa3 | 1.25 | 14184 | 3 | 4 | | IV-1 | Slc30a4 | 1.17 |
| 14089 | 3 | 4 | | | IV-1 | Shisa5 | 1.12 | 14185 | 3 | 4 | | IV-1 | Slc30a7 | 1.08 |
| 14090 | 3 | 4 | | | IV-1 | Shisa7 | 1.35 | 14186 | 3 | 4 | | IV-1 | Slc34a2 | 1.18 |
| 14091 | 3 | 4 | | | IV-1 | Shisa9 | 1.27 | 14187 | 3 | 4 | | IV-1 | Slc35a5 | 1.13 |
| 14092 | 3 | 4 | | | IV-1 | Shox2 | 1.21 | 14188 | 3 | 4 | | IV-1 | Slc35b1 | 1.04 |
| 14093 | 3 | 4 | | | IV-1 | Shprh | 1.25 | 14189 | 3 | 4 | | IV-1 | Slc35d1 | 1.20 |
| 14094 | 3 | 4 | | | IV-1 | Shq1 | 1.02 | 14190 | 3 | 4 | | IV-1 | Slc35d3 | 1.13 |
| 14095 | 3 | 4 | | | IV-1 | Shroom2 | 1.26 | 14191 | 3 | 4 | | IV-1 | Slc35e2 | 1.05 |
| 14096 | 3 | 4 | | | IV-1 | Shroom3 | 1.07 | 14192 | 3 | 4 | | IV-1 | Slc35e3 | 1.29 |
| 14097 | 3 | 4 | | | IV-1 | Siah1a | 1.32 | 14193 | 3 | 4 | | IV-1 | Slc35f1 | 1.28 |
| 14098 | 3 | 4 | | | IV-1 | Siah1b | 1.14 | 14194 | 3 | 4 | | IV-1 | Slc35f2 | 1.13 |
| 14099 | 3 | 4 | | | IV-1 | Siah2 | 1.13 | 14195 | 3 | 4 | | IV-1 | Slc35f6 | 1.23 |
| 14100 | 3 | 4 | | | IV-1 | Sidt2 | 1.35 | 14196 | 3 | 4 | | IV-1 | Slc35g1 | 1.17 |
| 14101 | 3 | 4 | | | IV-1 | Siglec1 | 1.48 | 14197 | 3 | 4 | | IV-1 | Slc36a4 | 1.41 |
| 14102 | 3 | 4 | | | IV-1 | Siglece | 1.30 | 14198 | 3 | 4 | | IV-1 | Slc37a1 | 1.44 |
| 14103 | 3 | 4 | | | IV-1 | Sik1 | 1.04 | 14199 | 3 | 4 | | IV-1 | Slc37a3 | 1.01 |
| 14104 | 3 | 4 | | | IV-1 | Sik3 | 1.06 | 14200 | 3 | 4 | | IV-1 | Slc37a4 | 1.01 |
| 14105 | 3 | 4 | | | IV-1 | Sike1 | 1.06 | 14201 | 3 | 4 | | IV-1 | Slc38a1 | 1.25 |
| 14106 | 3 | 4 | | | IV-1 | Sim1 | 1.12 | 14202 | 3 | 4 | | IV-1 | Slc38a2 | 1.15 |
| 14107 | 3 | 4 | | | IV-1 | Sim2 | 1.02 | 14203 | 3 | 4 | | IV-1 | Slc38a6 | 1.12 |
| 14108 | 3 | 4 | | | IV-1 | Simc1 | 1.10 | 14204 | 3 | 4 | | IV-1 | Slc38a9 | 1.23 |
| 14109 | 3 | 4 | | | IV-1 | Sin3b | 1.28 | 14205 | 3 | 4 | | IV-1 | Slc39a11 | 1.07 |

Fig. 45 - 75

| | | | | | | | |
|---|---|---|---|---|---|---|---|
| 14206 | 3 | 4 | | | IV-1 | Slc39a6 | 1.16 |
| 14207 | 3 | 4 | | | IV-1 | Slc39a7 | 1.01 |
| 14208 | 3 | 4 | | | IV-1 | Slc3a2 | 1.27 |
| 14209 | 3 | 4 | | | IV-1 | Slc40a1 | 1.05 |
| 14210 | 3 | 4 | | | IV-1 | Slc41a2 | 1.49 |
| 14211 | 3 | 4 | | | IV-1 | Slc43a2 | 1.07 |
| 14212 | 3 | 4 | | | IV-1 | Slc44a2 | 1.04 |
| 14213 | 3 | 4 | | | IV-1 | Slc44a5 | 1.25 |
| 14214 | 3 | 4 | | | IV-1 | Slc45a4 | 1.28 |
| 14215 | 3 | 4 | | | IV-1 | Slc48a1 | 1.00 |
| 14216 | 3 | 4 | | | IV-1 | Slc4a1ap | 1.14 |
| 14217 | 3 | 4 | | | IV-1 | Slc4a4 | 1.14 |
| 14218 | 3 | 4 | | | IV-1 | Slc4a7 | 1.37 |
| 14219 | 3 | 4 | | | IV-1 | Slc4a8 | 1.40 |
| 14220 | 3 | 4 | | | IV-1 | Slc52a2 | 1.19 |
| 14221 | 3 | 4 | | | IV-1 | Slc52a3 | 1.17 |
| 14222 | 3 | 4 | | | IV-1 | Slc6a2 | 1.06 |
| 14223 | 3 | 4 | | | IV-1 | Slc6a7 | 1.18 |
| 14224 | 3 | 4 | | | IV-1 | Slc6a8 | 1.16 |
| 14225 | 3 | 4 | | | IV-1 | Slc6a9 | 1.01 |
| 14226 | 3 | 4 | | | IV-1 | Slc7a1 | 1.24 |
| 14227 | 3 | 4 | | | IV-1 | Slc7a10 | 1.01 |
| 14228 | 3 | 4 | | | IV-1 | Slc7a4 | 1.22 |
| 14229 | 3 | 4 | | | IV-1 | Slc7a5 | 1.44 |
| 14230 | 3 | 4 | | | IV-1 | Slc7a6 | 1.09 |
| 14231 | 3 | 4 | | | IV-1 | Slc7a6os | 1.03 |
| 14232 | 3 | 4 | | | IV-1 | Slc7a8 | 1.06 |
| 14233 | 3 | 4 | | | IV-1 | Slc8a1 | 1.35 |
| 14234 | 3 | 4 | | | IV-1 | Slc8a3 | 1.07 |
| 14235 | 3 | 4 | | | IV-1 | Slc8b1 | 1.00 |
| 14236 | 3 | 4 | | | IV-1 | Slc9a1 | 1.08 |
| 14237 | 3 | 4 | | | IV-1 | Slc9a3r2 | 1.08 |
| 14238 | 3 | 4 | | | IV-1 | Slc9a5 | 1.12 |
| 14239 | 3 | 4 | | | IV-1 | Slc9a6 | 1.32 |
| 14240 | 3 | 4 | | | IV-1 | Slc9a7 | 1.01 |
| 14241 | 3 | 4 | | | IV-1 | Slc9a8 | 1.19 |
| 14242 | 3 | 4 | | | IV-1 | Slco1b2 | 1.28 |
| 14243 | 3 | 4 | | | IV-1 | Slco2a1 | 1.24 |
| 14244 | 3 | 4 | | | IV-1 | Slco2b1 | 1.23 |
| 14245 | 3 | 4 | | | IV-1 | Slco5a1 | 1.50 |
| 14246 | 3 | 4 | | | IV-1 | Slfn8 | 1.10 |
| 14247 | 3 | 4 | | | IV-1 | Slit2 | 1.35 |
| 14248 | 3 | 4 | | | IV-1 | Slit3 | 1.33 |
| 14249 | 3 | 4 | | | IV-1 | Slitrk1 | 1.30 |
| 14250 | 3 | 4 | | | IV-1 | Slitrk2 | 1.29 |
| 14251 | 3 | 4 | | | IV-1 | Slitrk4 | 1.25 |
| 14252 | 3 | 4 | | | IV-1 | Slitrk5 | 1.40 |
| 14253 | 3 | 4 | | | IV-1 | Slitrk6 | 1.07 |
| 14254 | 3 | 4 | | | IV-1 | Slk | 1.04 |
| 14255 | 3 | 4 | | | IV-1 | Slpi | 1.21 |
| 14256 | 3 | 4 | | | IV-1 | Sltm | 1.15 |
| 14257 | 3 | 4 | | | IV-1 | Slu7 | 1.16 |
| 14258 | 3 | 4 | | | IV-1 | Six1b | 1.14 |
| 14259 | 3 | 4 | | | IV-1 | Six4 | 1.22 |
| 14260 | 3 | 4 | | | IV-1 | Smad1 | 1.06 |
| 14261 | 3 | 4 | | | IV-1 | Smad2 | 1.30 |
| 14262 | 3 | 4 | | | IV-1 | Smad3 | 1.01 |
| 14263 | 3 | 4 | | | IV-1 | Smad4 | 1.15 |
| 14264 | 3 | 4 | | | IV-1 | Smad5 | 1.11 |
| 14265 | 3 | 4 | | | IV-1 | Smad7 | 1.12 |
| 14266 | 3 | 4 | | | IV-1 | Smad9 | 1.07 |
| 14267 | 3 | 4 | | | IV-1 | Smap1 | 1.02 |
| 14268 | 3 | 4 | | | IV-1 | Smarca1 | 1.20 |
| 14269 | 3 | 4 | | | IV-1 | Smarca2 | 1.29 |
| 14270 | 3 | 4 | | | IV-1 | Smarcad1 | 1.20 |
| 14271 | 3 | 4 | | | IV-1 | Smarcc1 | 1.04 |
| 14272 | 3 | 4 | | | IV-1 | Smarcc2 | 1.26 |
| 14273 | 3 | 4 | | | IV-1 | Smarcd1 | 1.42 |
| 14274 | 3 | 4 | | | IV-1 | Smarcd3 | 1.07 |
| 14275 | 3 | 4 | | | IV-1 | Smarce1 | 1.11 |
| 14276 | 3 | 4 | | | IV-1 | Smc5 | 1.12 |
| 14277 | 3 | 4 | | | IV-1 | Smc6 | 1.05 |
| 14278 | 3 | 4 | | | IV-1 | Smco3 | 1.08 |
| 14279 | 3 | 4 | | | IV-1 | Smek2 | 1.08 |
| 14280 | 3 | 4 | | | IV-1 | Smg6 | 1.26 |
| 14281 | 3 | 4 | | | IV-1 | Smg7 | 1.04 |
| 14282 | 3 | 4 | | | IV-1 | Smg9 | 1.29 |
| 14283 | 3 | 4 | | | IV-1 | Smim12 | 1.07 |
| 14284 | 3 | 4 | | | IV-1 | Smim13 | 1.01 |
| 14285 | 3 | 4 | | | IV-1 | Smim14 | 1.20 |
| 14286 | 3 | 4 | | | IV-1 | Smim18 | 1.35 |
| 14287 | 3 | 4 | | | IV-1 | Smim19 | 1.20 |
| 14288 | 3 | 4 | | | IV-1 | Smim22 | 1.22 |
| 14289 | 3 | 4 | | | IV-1 | Smim3 | 1.03 |
| 14290 | 3 | 4 | | | IV-1 | Smn1 | 1.21 |
| 14291 | 3 | 4 | | | IV-1 | Smo | 1.03 |
| 14292 | 3 | 4 | | | IV-1 | Smoc1 | 1.14 |
| 14293 | 3 | 4 | | | IV-1 | Smoc2 | 1.06 |
| 14294 | 3 | 4 | | | IV-1 | Smpd3 | 1.07 |
| 14295 | 3 | 4 | | | IV-1 | Smpd4 | 1.01 |
| 14296 | 3 | 4 | | | IV-1 | Smpdl3a | 1.06 |
| 14297 | 3 | 4 | | | IV-1 | Sms | 1.36 |
| 14298 | 3 | 4 | | | IV-1 | Smug1 | 1.12 |
| 14299 | 3 | 4 | | | IV-1 | Smurf1 | 1.25 |
| 14300 | 3 | 4 | | | IV-1 | Smurf2 | 1.07 |
| 14301 | 3 | 4 | | | IV-1 | Smyd2 | 1.11 |
| 14302 | 3 | 4 | | | IV-1 | Smyd3 | 1.32 |
| 14303 | 3 | 4 | | | IV-1 | Smyd4 | 1.00 |
| 14304 | 3 | 4 | | | IV-1 | Snai1 | 1.04 |
| 14305 | 3 | 4 | | | IV-1 | Snap25 | 1.42 |
| 14306 | 3 | 4 | | | IV-1 | Snap47 | 1.06 |
| 14307 | 3 | 4 | | | IV-1 | Snap91 | 1.19 |
| 14308 | 3 | 4 | | | IV-1 | Snapc3 | 1.04 |
| 14309 | 3 | 4 | | | IV-1 | Snapc4 | 1.37 |
| 14310 | 3 | 4 | | | IV-1 | Snapin | 1.07 |
| 14311 | 3 | 4 | | | IV-1 | Sncaip | 1.09 |
| 14312 | 3 | 4 | | | IV-1 | Sncb | 1.48 |
| 14313 | 3 | 4 | | | IV-1 | Sncg | 1.19 |
| 14314 | 3 | 4 | | | IV-1 | Snhg3 | 1.16 |
| 14315 | 3 | 4 | | | IV-1 | Snhg4 | 1.06 |
| 14316 | 3 | 4 | | | IV-1 | Snhg5 | 1.49 |
| 14317 | 3 | 4 | | | IV-1 | Snhg8 | 1.36 |
| 14318 | 3 | 4 | | | IV-1 | Snn | 1.46 |
| 14319 | 3 | 4 | | | IV-1 | Snora16a | 1.02 |
| 14320 | 3 | 4 | | | IV-1 | Snora23 | 1.42 |
| 14321 | 3 | 4 | | | IV-1 | Snora41 | 1.28 |
| 14322 | 3 | 4 | | | IV-1 | Snora81 | 1.02 |
| 14323 | 3 | 4 | | | IV-1 | Snph | 1.27 |
| 14324 | 3 | 4 | | | IV-1 | Snrk | 1.11 |
| 14325 | 3 | 4 | | | IV-1 | Snrnp200 | 1.27 |
| 14326 | 3 | 4 | | | IV-1 | Snrpa1 | 1.07 |
| 14327 | 3 | 4 | | | IV-1 | Snrpc | 1.04 |
| 14328 | 3 | 4 | | | IV-1 | Snupn | 1.11 |
| 14329 | 3 | 4 | | | IV-1 | Snw1 | 1.02 |
| 14330 | 3 | 4 | | | IV-1 | Snx10 | 1.02 |
| 14331 | 3 | 4 | | | IV-1 | Snx11 | 1.11 |
| 14332 | 3 | 4 | | | IV-1 | Snx13 | 1.02 |
| 14333 | 3 | 4 | | | IV-1 | Snx16 | 1.01 |
| 14334 | 3 | 4 | | | IV-1 | Snx19 | 1.03 |
| 14335 | 3 | 4 | | | IV-1 | Snx20 | 1.48 |
| 14336 | 3 | 4 | | | IV-1 | Snx21 | 1.00 |
| 14337 | 3 | 4 | | | IV-1 | Snx24 | 1.19 |
| 14338 | 3 | 4 | | | IV-1 | Snx29 | 1.33 |
| 14339 | 3 | 4 | | | IV-1 | Snx30 | 1.17 |
| 14340 | 3 | 4 | | | IV-1 | Snx32 | 1.32 |
| 14341 | 3 | 4 | | | IV-1 | Snx33 | 1.05 |
| 14342 | 3 | 4 | | | IV-1 | Snx4 | 1.20 |
| 14343 | 3 | 4 | | | IV-1 | Snx7 | 1.01 |
| 14344 | 3 | 4 | | | IV-1 | Sobp | 1.29 |
| 14345 | 3 | 4 | | | IV-1 | Socs3 | 1.11 |
| 14346 | 3 | 4 | | | IV-1 | Socs5 | 1.01 |
| 14347 | 3 | 4 | | | IV-1 | Socs6 | 1.16 |
| 14348 | 3 | 4 | | | IV-1 | Socs7 | 1.01 |
| 14349 | 3 | 4 | | | IV-1 | Soga1 | 1.12 |
| 14350 | 3 | 4 | | | IV-1 | Soga3 | 1.32 |
| 14351 | 3 | 4 | | | IV-1 | Son | 1.02 |
| 14352 | 3 | 4 | | | IV-1 | Sorbs2 | 1.37 |
| 14353 | 3 | 4 | | | IV-1 | Sorbs3 | 1.11 |
| 14354 | 3 | 4 | | | IV-1 | Sorcs1 | 1.39 |
| 14355 | 3 | 4 | | | IV-1 | Sorcs2 | 1.28 |
| 14356 | 3 | 4 | | | IV-1 | Sos1 | 1.06 |
| 14357 | 3 | 4 | | | IV-1 | Sos2 | 1.20 |
| 14358 | 3 | 4 | | | IV-1 | Sostdc1 | 1.13 |
| 14359 | 3 | 4 | | | IV-1 | Sox10 | 1.11 |
| 14360 | 3 | 4 | | | IV-1 | Sox11 | 1.45 |
| 14361 | 3 | 4 | | | IV-1 | Sox12 | 1.10 |
| 14362 | 3 | 4 | | | IV-1 | Sox4 | 1.37 |
| 14363 | 3 | 4 | | | IV-1 | Sox9 | 1.14 |
| 14364 | 3 | 4 | | | IV-1 | Sp140 | 1.05 |
| 14365 | 3 | 4 | | | IV-1 | Sp3os | 1.10 |
| 14366 | 3 | 4 | | | IV-1 | Sp4 | 1.11 |
| 14367 | 3 | 4 | | | IV-1 | Sp5 | 1.43 |
| 14368 | 3 | 4 | | | IV-1 | Spag6 | 1.01 |
| 14369 | 3 | 4 | | | IV-1 | Spag9 | 1.17 |
| 14370 | 3 | 4 | | | IV-1 | Sparcl1 | 1.01 |
| 14371 | 3 | 4 | | | IV-1 | Spast | 1.25 |
| 14372 | 3 | 4 | | | IV-1 | Spata18 | 1.20 |
| 14373 | 3 | 4 | | | IV-1 | Spata2 | 1.11 |
| 14374 | 3 | 4 | | | IV-1 | Spata24 | 1.10 |
| 14375 | 3 | 4 | | | IV-1 | Spata33 | 1.01 |
| 14376 | 3 | 4 | | | IV-1 | Spata5l1 | 1.07 |
| 14377 | 3 | 4 | | | IV-1 | Spata6 | 1.02 |
| 14378 | 3 | 4 | | | IV-1 | Spats2 | 1.13 |
| 14379 | 3 | 4 | | | IV-1 | Spdef | 1.07 |
| 14380 | 3 | 4 | | | IV-1 | Spdya | 1.42 |
| 14381 | 3 | 4 | | | IV-1 | Specc1l | 1.16 |
| 14382 | 3 | 4 | | | IV-1 | Spen | 1.02 |
| 14383 | 3 | 4 | | | IV-1 | Spg11 | 1.06 |
| 14384 | 3 | 4 | | | IV-1 | Spg20 | 1.08 |
| 14385 | 3 | 4 | | | IV-1 | Sphkap | 1.03 |
| 14386 | 3 | 4 | | | IV-1 | Spin1 | 1.27 |
| 14387 | 3 | 4 | | | IV-1 | Spin4 | 1.07 |
| 14388 | 3 | 4 | | | IV-1 | Spink5 | 1.11 |
| 14389 | 3 | 4 | | | IV-1 | Spire2 | 1.33 |
| 14390 | 3 | 4 | | | IV-1 | Spns1 | 1.08 |
| 14391 | 3 | 4 | | | IV-1 | Spon1 | 1.07 |
| 14392 | 3 | 4 | | | IV-1 | Spopl | 1.12 |
| 14393 | 3 | 4 | | | IV-1 | Sppl2a | 1.04 |
| 14394 | 3 | 4 | | | IV-1 | Sppl3 | 1.10 |
| 14395 | 3 | 4 | | | IV-1 | Spred1 | 1.08 |
| 14396 | 3 | 4 | | | IV-1 | Spred2 | 1.08 |
| 14397 | 3 | 4 | | | IV-1 | Sprn | 1.24 |

Fig. 45 - 76

| | | | | | | | | | | | | | | |
|---|---|---|---|---|---|---|---|---|---|---|---|---|---|---|
| 14398 | 3 | 4 | | | IV-1 | Spry1 | 1.35 | 14494 | 3 | 4 | | | IV-1 | Stxbp5 | 1.06 |
| 14399 | 3 | 4 | | | IV-1 | Spry2 | 1.18 | 14495 | 3 | 4 | | | IV-1 | Stxbp5l | 1.40 |
| 14400 | 3 | 4 | | | IV-1 | Spry3 | 1.30 | 14496 | 3 | 4 | | | IV-1 | Styk1 | 1.18 |
| 14401 | 3 | 4 | | | IV-1 | Spryd3 | 1.28 | 14497 | 3 | 4 | | | IV-1 | Styx | 1.25 |
| 14402 | 3 | 4 | | | IV-1 | Spryd7 | 1.05 | 14498 | 3 | 4 | | | IV-1 | Sub1 | 1.14 |
| 14403 | 3 | 4 | | | IV-1 | Spsb1 | 1.06 | 14499 | 3 | 4 | | | IV-1 | Suco | 1.10 |
| 14404 | 3 | 4 | | | IV-1 | Spsb3 | 1.04 | 14500 | 3 | 4 | | | IV-1 | Sugp1 | 1.18 |
| 14405 | 3 | 4 | | | IV-1 | Sptan1 | 1.15 | 14501 | 3 | 4 | | | IV-1 | Sugp2 | 1.11 |
| 14406 | 3 | 4 | | | IV-1 | Sptbn1 | 1.08 | 14502 | 3 | 4 | | | IV-1 | Sugt1 | 1.11 |
| 14407 | 3 | 4 | | | IV-1 | Sptbn2 | 1.39 | 14503 | 3 | 4 | | | IV-1 | Sulf1 | 1.10 |
| 14408 | 3 | 4 | | | IV-1 | Sqstm1 | 1.21 | 14504 | 3 | 4 | | | IV-1 | Sulf2 | 1.29 |
| 14409 | 3 | 4 | | | IV-1 | Src | 1.15 | 14505 | 3 | 4 | | | IV-1 | Sult1d1 | 1.03 |
| 14410 | 3 | 4 | | | IV-1 | Srcin1 | 1.28 | 14506 | 3 | 4 | | | IV-1 | Sult2a2 | 1.02 |
| 14411 | 3 | 4 | | | IV-1 | Srd5a3 | 1.09 | 14507 | 3 | 4 | | | IV-1 | Sult4a1 | 1.35 |
| 14412 | 3 | 4 | | | IV-1 | Srek1 | 1.18 | 14508 | 3 | 4 | | | IV-1 | Sult5a1 | 1.30 |
| 14413 | 3 | 4 | | | IV-1 | Srfbp1 | 1.04 | 14509 | 3 | 4 | | | IV-1 | Sumf1 | 1.08 |
| 14414 | 3 | 4 | | | IV-1 | Srgap1 | 1.31 | 14510 | 3 | 4 | | | IV-1 | Sumo3 | 1.17 |
| 14415 | 3 | 4 | | | IV-1 | Srgap2 | 1.07 | 14511 | 3 | 4 | | | IV-1 | Supt20 | 1.12 |
| 14416 | 3 | 4 | | | IV-1 | Srgn | 1.07 | 14512 | 3 | 4 | | | IV-1 | Supt6 | 1.02 |
| 14417 | 3 | 4 | | | IV-1 | Srpk2 | 1.20 | 14513 | 3 | 4 | | | IV-1 | Supv3l1 | 1.10 |
| 14418 | 3 | 4 | | | IV-1 | Srrd | 1.34 | 14514 | 3 | 4 | | | IV-1 | Surf6 | 1.03 |
| 14419 | 3 | 4 | | | IV-1 | Srrm1 | 1.06 | 14515 | 3 | 4 | | | IV-1 | Susd3 | 1.04 |
| 14420 | 3 | 4 | | | IV-1 | Srsf11 | 1.08 | 14516 | 3 | 4 | | | IV-1 | Susd4 | 1.50 |
| 14421 | 3 | 4 | | | IV-1 | Srsf12 | 1.47 | 14517 | 3 | 4 | | | IV-1 | Susd5 | 1.50 |
| 14422 | 3 | 4 | | | IV-1 | Srsf5 | 1.23 | 14518 | 3 | 4 | | | IV-1 | Suv420h1 | 1.16 |
| 14423 | 3 | 4 | | | IV-1 | Srsf6 | 1.09 | 14519 | 3 | 4 | | | IV-1 | Sv2b | 1.35 |
| 14424 | 3 | 4 | | | IV-1 | Srxn1 | 1.29 | 14520 | 3 | 4 | | | IV-1 | Sv2c | 1.11 |
| 14425 | 3 | 4 | | | IV-1 | Ss18l1 | 1.43 | 14521 | 3 | 4 | | | IV-1 | Svep1 | 1.09 |
| 14426 | 3 | 4 | | | IV-1 | Ssbp1 | 1.02 | 14522 | 3 | 4 | | | IV-1 | Swsap1 | 1.18 |
| 14427 | 3 | 4 | | | IV-1 | Ssbp2 | 1.26 | 14523 | 3 | 4 | | | IV-1 | Sybu | 1.41 |
| 14428 | 3 | 4 | | | IV-1 | Ssbp3 | 1.24 | 14524 | 3 | 4 | | | IV-1 | Syde1 | 1.07 |
| 14429 | 3 | 4 | | | IV-1 | Ssbp4 | 1.30 | 14525 | 3 | 4 | | | IV-1 | Syde2 | 1.12 |
| 14430 | 3 | 4 | | | IV-1 | Ssh1 | 1.08 | 14526 | 3 | 4 | | | IV-1 | Syf2 | 1.04 |
| 14431 | 3 | 4 | | | IV-1 | Ssh2 | 1.05 | 14527 | 3 | 4 | | | IV-1 | Syn1 | 1.17 |
| 14432 | 3 | 4 | | | IV-1 | Ssh3 | 1.26 | 14528 | 3 | 4 | | | IV-1 | Syn2 | 1.26 |
| 14433 | 3 | 4 | | | IV-1 | Sstr1 | 1.36 | 14529 | 3 | 4 | | | IV-1 | Syn3 | 1.10 |
| 14434 | 3 | 4 | | | IV-1 | Sstr4 | 1.17 | 14530 | 3 | 4 | | | IV-1 | Syna | 1.07 |
| 14435 | 3 | 4 | | | IV-1 | Ssu72 | 1.13 | 14531 | 3 | 4 | | | IV-1 | Syncrip | 1.06 |
| 14436 | 3 | 4 | | | IV-1 | St3gal6 | 1.11 | 14532 | 3 | 4 | | | IV-1 | Syndig1 | 1.03 |
| 14437 | 3 | 4 | | | IV-1 | St7 | 1.08 | 14533 | 3 | 4 | | | IV-1 | Syne1 | 1.05 |
| 14438 | 3 | 4 | | | IV-1 | St7l | 1.23 | 14534 | 3 | 4 | | | IV-1 | Syngap1 | 1.31 |
| 14439 | 3 | 4 | | | IV-1 | St8sia2 | 1.50 | 14535 | 3 | 4 | | | IV-1 | Syngr1 | 1.32 |
| 14440 | 3 | 4 | | | IV-1 | St8sia3 | 1.33 | 14536 | 3 | 4 | | | IV-1 | Syngr3 | 1.14 |
| 14441 | 3 | 4 | | | IV-1 | Stac | 1.49 | 14537 | 3 | 4 | | | IV-1 | Synj1 | 1.16 |
| 14442 | 3 | 4 | | | IV-1 | Stac2 | 1.02 | 14538 | 3 | 4 | | | IV-1 | Synpo | 1.25 |
| 14443 | 3 | 4 | | | IV-1 | Stag1 | 1.08 | 14539 | 3 | 4 | | | IV-1 | Synpr | 1.48 |
| 14444 | 3 | 4 | | | IV-1 | Stag3 | 1.12 | 14540 | 3 | 4 | | | IV-1 | Synrg | 1.06 |
| 14445 | 3 | 4 | | | IV-1 | Stam | 1.09 | 14541 | 3 | 4 | | | IV-1 | Sys1 | 1.06 |
| 14446 | 3 | 4 | | | IV-1 | Stam2 | 1.02 | 14542 | 3 | 4 | | | IV-1 | Syt1 | 1.46 |
| 14447 | 3 | 4 | | | IV-1 | Stambp | 1.30 | 14543 | 3 | 4 | | | IV-1 | Syt11 | 1.26 |
| 14448 | 3 | 4 | | | IV-1 | Stamos | 1.18 | 14544 | 3 | 4 | | | IV-1 | Syt12 | 1.33 |
| 14449 | 3 | 4 | | | IV-1 | Stard3 | 1.16 | 14545 | 3 | 4 | | | IV-1 | Syt13 | 1.42 |
| 14450 | 3 | 4 | | | IV-1 | Stard3nl | 1.01 | 14546 | 3 | 4 | | | IV-1 | Syt14 | 1.13 |
| 14451 | 3 | 4 | | | IV-1 | Stat1 | 1.21 | 14547 | 3 | 4 | | | IV-1 | Syt3 | 1.39 |
| 14452 | 3 | 4 | | | IV-1 | Stat2 | 1.19 | 14548 | 3 | 4 | | | IV-1 | Syt4 | 1.45 |
| 14453 | 3 | 4 | | | IV-1 | Stat3 | 1.03 | 14549 | 3 | 4 | | | IV-1 | Syt6 | 1.40 |
| 14454 | 3 | 4 | | | IV-1 | Stau1 | 1.08 | 14550 | 3 | 4 | | | IV-1 | Syt9 | 1.23 |
| 14455 | 3 | 4 | | | IV-1 | Stau2 | 1.30 | 14551 | 3 | 4 | | | IV-1 | Szt2 | 1.24 |
| 14456 | 3 | 4 | | | IV-1 | Steap1 | 1.42 | 14552 | 3 | 4 | | | IV-1 | Tab1 | 1.14 |
| 14457 | 3 | 4 | | | IV-1 | Steap2 | 1.06 | 14553 | 3 | 4 | | | IV-1 | Tab2 | 1.04 |
| 14458 | 3 | 4 | | | IV-1 | Steap4 | 1.31 | 14554 | 3 | 4 | | | IV-1 | Tac1 | 1.44 |
| 14459 | 3 | 4 | | | IV-1 | Stfa1 | 1.11 | 14555 | 3 | 4 | | | IV-1 | Tacc2 | 1.19 |
| 14460 | 3 | 4 | | | IV-1 | Stfa2 | 1.15 | 14556 | 3 | 4 | | | IV-1 | Tacr1 | 1.17 |
| 14461 | 3 | 4 | | | IV-1 | Stfa2l1 | 1.48 | 14557 | 3 | 4 | | | IV-1 | Tada1 | 1.02 |
| 14462 | 3 | 4 | | | IV-1 | Stk11ip | 1.08 | 14558 | 3 | 4 | | | IV-1 | Tada2a | 1.03 |
| 14463 | 3 | 4 | | | IV-1 | Stk19 | 1.33 | 14559 | 3 | 4 | | | IV-1 | Tada2b | 1.01 |
| 14464 | 3 | 4 | | | IV-1 | Stk25 | 1.11 | 14560 | 3 | 4 | | | IV-1 | Taf1a | 1.13 |
| 14465 | 3 | 4 | | | IV-1 | Stk32a | 1.06 | 14561 | 3 | 4 | | | IV-1 | Taf1b | 1.25 |
| 14466 | 3 | 4 | | | IV-1 | Stk32b | 1.44 | 14562 | 3 | 4 | | | IV-1 | Taf1d | 1.31 |
| 14467 | 3 | 4 | | | IV-1 | Stk36 | 1.10 | 14563 | 3 | 4 | | | IV-1 | Taf2 | 1.12 |
| 14468 | 3 | 4 | | | IV-1 | Stk38 | 1.05 | 14564 | 3 | 4 | | | IV-1 | Taf5l | 1.12 |
| 14469 | 3 | 4 | | | IV-1 | Stk39 | 1.13 | 14565 | 3 | 4 | | | IV-1 | Taf8 | 1.03 |
| 14470 | 3 | 4 | | | IV-1 | Stmn2 | 1.36 | 14566 | 3 | 4 | | | IV-1 | Taf9 | 1.14 |
| 14471 | 3 | 4 | | | IV-1 | Stmn3 | 1.31 | 14567 | 3 | 4 | | | IV-1 | Tagap | 1.04 |
| 14472 | 3 | 4 | | | IV-1 | Stmn4 | 1.16 | 14568 | 3 | 4 | | | IV-1 | Tagln3 | 1.43 |
| 14473 | 3 | 4 | | | IV-1 | Stoml1 | 1.37 | 14569 | 3 | 4 | | | IV-1 | Tamm41 | 1.07 |
| 14474 | 3 | 4 | | | IV-1 | Ston1 | 1.22 | 14570 | 3 | 4 | | | IV-1 | Tanc2 | 1.35 |
| 14475 | 3 | 4 | | | IV-1 | Stox1 | 1.09 | 14571 | 3 | 4 | | | IV-1 | Tango6 | 1.01 |
| 14476 | 3 | 4 | | | IV-1 | Stox2 | 1.25 | 14572 | 3 | 4 | | | IV-1 | Taok1 | 1.03 |
| 14477 | 3 | 4 | | | IV-1 | Stra6 | 1.34 | 14573 | 3 | 4 | | | IV-1 | Taok2 | 1.01 |
| 14478 | 3 | 4 | | | IV-1 | Strap | 1.03 | 14574 | 3 | 4 | | | IV-1 | Tap1 | 1.38 |
| 14479 | 3 | 4 | | | IV-1 | Strbp | 1.26 | 14575 | 3 | 4 | | | IV-1 | Tapbp | 1.09 |
| 14480 | 3 | 4 | | | IV-1 | Strip1 | 1.17 | 14576 | 3 | 4 | | | IV-1 | Tapt1 | 1.05 |
| 14481 | 3 | 4 | | | IV-1 | Strn | 1.04 | 14577 | 3 | 4 | | | IV-1 | Tarbp2 | 1.06 |
| 14482 | 3 | 4 | | | IV-1 | Strn3 | 1.11 | 14578 | 3 | 4 | | | IV-1 | Tardbp | 1.02 |
| 14483 | 3 | 4 | | | IV-1 | Strn4 | 1.19 | 14579 | 3 | 4 | | | IV-1 | Tars | 1.02 |
| 14484 | 3 | 4 | | | IV-1 | Stx12 | 1.19 | 14580 | 3 | 4 | | | IV-1 | Tatdn2 | 1.10 |
| 14485 | 3 | 4 | | | IV-1 | Stx17 | 1.14 | 14581 | 3 | 4 | | | IV-1 | Tax1bp1 | 1.00 |
| 14486 | 3 | 4 | | | IV-1 | Stx18 | 1.13 | 14582 | 3 | 4 | | | IV-1 | Taz | 1.19 |
| 14487 | 3 | 4 | | | IV-1 | Stx1a | 1.41 | 14583 | 3 | 4 | | | IV-1 | Tbc1d10c | 1.01 |
| 14488 | 3 | 4 | | | IV-1 | Stx3 | 1.16 | 14584 | 3 | 4 | | | IV-1 | Tbc1d12 | 1.16 |
| 14489 | 3 | 4 | | | IV-1 | Stx6 | 1.12 | 14585 | 3 | 4 | | | IV-1 | Tbc1d14 | 1.21 |
| 14490 | 3 | 4 | | | IV-1 | Stx7 | 1.00 | 14586 | 3 | 4 | | | IV-1 | Tbc1d16 | 1.14 |
| 14491 | 3 | 4 | | | IV-1 | Stxbp1 | 1.50 | 14587 | 3 | 4 | | | IV-1 | Tbc1d17 | 1.22 |
| 14492 | 3 | 4 | | | IV-1 | Stxbp2 | 1.05 | 14588 | 3 | 4 | | | IV-1 | Tbc1d2 | 1.41 |
| 14493 | 3 | 4 | | | IV-1 | Stxbp3a | 1.01 | 14589 | 3 | 4 | | | IV-1 | Tbc1d20 | 1.08 |

Fig. 45 - 77

| | | | | | | | | | | | | | | | |
|---|---|---|---|---|---|---|---|---|---|---|---|---|---|---|---|
| 14590 | 3 | 4 | | | IV-1 | Tbc1d22b | 1.24 | 14686 | 3 | 4 | | | IV-1 | Thbs3 | 1.14 |
| 14591 | 3 | 4 | | | IV-1 | Tbc1d23 | 1.11 | 14687 | 3 | 4 | | | IV-1 | Them4 | 1.09 |
| 14592 | 3 | 4 | | | IV-1 | Tbc1d24 | 1.11 | 14688 | 3 | 4 | | | IV-1 | Themis2 | 1.25 |
| 14593 | 3 | 4 | | | IV-1 | Tbc1d30 | 1.20 | 14689 | 3 | 4 | | | IV-1 | Thg1l | 1.09 |
| 14594 | 3 | 4 | | | IV-1 | Tbc1d32 | 1.38 | 14690 | 3 | 4 | | | IV-1 | Thnsl2 | 1.07 |
| 14595 | 3 | 4 | | | IV-1 | Tbc1d5 | 1.04 | 14691 | 3 | 4 | | | IV-1 | Thoc1 | 1.16 |
| 14596 | 3 | 4 | | | IV-1 | Tbc1d7 | 1.24 | 14692 | 3 | 4 | | | IV-1 | Thoc2 | 1.04 |
| 14597 | 3 | 4 | | | IV-1 | Tbc1d8 | 1.05 | 14693 | 3 | 4 | | | IV-1 | Thoc3 | 1.05 |
| 14598 | 3 | 4 | | | IV-1 | Tbcb | 1.03 | 14694 | 3 | 4 | | | IV-1 | Thoc5 | 1.10 |
| 14599 | 3 | 4 | | | IV-1 | Tbce | 1.12 | 14695 | 3 | 4 | | | IV-1 | Thra | 1.27 |
| 14600 | 3 | 4 | | | IV-1 | Tbcel | 1.05 | 14696 | 3 | 4 | | | IV-1 | Thsd4 | 1.19 |
| 14601 | 3 | 4 | | | IV-1 | Tbk1 | 1.10 | 14697 | 3 | 4 | | | IV-1 | Thtpa | 1.29 |
| 14602 | 3 | 4 | | | IV-1 | Tbkbp1 | 1.42 | 14698 | 3 | 4 | | | IV-1 | Thumpd1 | 1.19 |
| 14603 | 3 | 4 | | | IV-1 | Tbl1x | 1.12 | 14699 | 3 | 4 | | | IV-1 | Thumpd2 | 1.32 |
| 14604 | 3 | 4 | | | IV-1 | Tbl1xr1 | 1.05 | 14700 | 3 | 4 | | | IV-1 | Thumpd3 | 1.02 |
| 14605 | 3 | 4 | | | IV-1 | Tbl3 | 1.18 | 14701 | 3 | 4 | | | IV-1 | Thyn1 | 1.09 |
| 14606 | 3 | 4 | | | IV-1 | Tbpl1 | 1.12 | 14702 | 3 | 4 | | | IV-1 | Tia1 | 1.17 |
| 14607 | 3 | 4 | | | IV-1 | Tbrg1 | 1.18 | 14703 | 3 | 4 | | | IV-1 | Tiam1 | 1.03 |
| 14608 | 3 | 4 | | | IV-1 | Tbx1 | 1.14 | 14704 | 3 | 4 | | | IV-1 | Tiam2 | 1.12 |
| 14609 | 3 | 4 | | | IV-1 | Tbx15 | 1.02 | 14705 | 3 | 4 | | | IV-1 | Tigd2 | 1.23 |
| 14610 | 3 | 4 | | | IV-1 | Tbx18 | 1.15 | 14706 | 3 | 4 | | | IV-1 | Tigd3 | 1.14 |
| 14611 | 3 | 4 | | | IV-1 | Tbx20 | 1.16 | 14707 | 3 | 4 | | | IV-1 | Tigd4 | 1.01 |
| 14612 | 3 | 4 | | | IV-1 | Tbx6 | 1.14 | 14708 | 3 | 4 | | | IV-1 | Tigd5 | 1.21 |
| 14613 | 3 | 4 | | | IV-1 | Tcaim | 1.07 | 14709 | 3 | 4 | | | IV-1 | Timp2 | 1.28 |
| 14614 | 3 | 4 | | | IV-1 | Tcap | 1.28 | 14710 | 3 | 4 | | | IV-1 | Timp3 | 1.25 |
| 14615 | 3 | 4 | | | IV-1 | Tceal | 1.01 | 14711 | 3 | 4 | | | IV-1 | Tinagl1 | 1.02 |
| 14616 | 3 | 4 | | | IV-1 | Tceal6 | 1.09 | 14712 | 3 | 4 | | | IV-1 | Tirap | 1.10 |
| 14617 | 3 | 4 | | | IV-1 | Tceanc | 1.26 | 14713 | 3 | 4 | | | IV-1 | Tldc1 | 1.02 |
| 14618 | 3 | 4 | | | IV-1 | Tceb1 | 1.08 | 14714 | 3 | 4 | | | IV-1 | Tle1 | 1.27 |
| 14619 | 3 | 4 | | | IV-1 | Tcerg1 | 1.18 | 14715 | 3 | 4 | | | IV-1 | Tle2 | 1.21 |
| 14620 | 3 | 4 | | | IV-1 | Tcf12 | 1.19 | 14716 | 3 | 4 | | | IV-1 | Tle4 | 1.16 |
| 14621 | 3 | 4 | | | IV-1 | Tcf20 | 1.12 | 14717 | 3 | 4 | | | IV-1 | Tlk1 | 1.07 |
| 14622 | 3 | 4 | | | IV-1 | Tcf21 | 1.05 | 14718 | 3 | 4 | | | IV-1 | Tlk2 | 1.16 |
| 14623 | 3 | 4 | | | IV-1 | Tcf25 | 1.24 | 14719 | 3 | 4 | | | IV-1 | Tll1 | 1.14 |
| 14624 | 3 | 4 | | | IV-1 | Tcf4 | 1.17 | 14720 | 3 | 4 | | | IV-1 | Tlr3 | 1.23 |
| 14625 | 3 | 4 | | | IV-1 | Tcf7l1 | 1.01 | 14721 | 3 | 4 | | | IV-1 | Tlr4 | 1.10 |
| 14626 | 3 | 4 | | | IV-1 | Tcf7l2 | 1.25 | 14722 | 3 | 4 | | | IV-1 | Tlr6 | 1.10 |
| 14627 | 3 | 4 | | | IV-1 | Tchp | 1.19 | 14723 | 3 | 4 | | | IV-1 | Tlr8 | 1.18 |
| 14628 | 3 | 4 | | | IV-1 | Tcirg1 | 1.13 | 14724 | 3 | 4 | | | IV-1 | Tlr9 | 1.03 |
| 14629 | 3 | 4 | | | IV-1 | Tcp11 | 1.26 | 14725 | 3 | 4 | | | IV-1 | Tlx2 | 1.33 |
| 14630 | 3 | 4 | | | IV-1 | Tcp11l2 | 1.14 | 14726 | 3 | 4 | | | IV-1 | Tm2d1 | 1.44 |
| 14631 | 3 | 4 | | | IV-1 | Tcta | 1.48 | 14727 | 3 | 4 | | | IV-1 | Tm2d2 | 1.05 |
| 14632 | 3 | 4 | | | IV-1 | Tctex1d2 | 1.45 | 14728 | 3 | 4 | | | IV-1 | Tm4sf1 | 1.15 |
| 14633 | 3 | 4 | | | IV-1 | Tctn1 | 1.39 | 14729 | 3 | 4 | | | IV-1 | Tm4sf4 | 1.17 |
| 14634 | 3 | 4 | | | IV-1 | Tctn2 | 1.18 | 14730 | 3 | 4 | | | IV-1 | Tm7sf3 | 1.16 |
| 14635 | 3 | 4 | | | IV-1 | Tctn3 | 1.05 | 14731 | 3 | 4 | | | IV-1 | Tm9sf3 | 1.07 |
| 14636 | 3 | 4 | | | IV-1 | Tdp1 | 1.05 | 14732 | 3 | 4 | | | IV-1 | Tma16 | 1.12 |
| 14637 | 3 | 4 | | | IV-1 | Tdrd3 | 1.06 | 14733 | 3 | 4 | | | IV-1 | Tmc4 | 1.33 |
| 14638 | 3 | 4 | | | IV-1 | Tdrd7 | 1.22 | 14734 | 3 | 4 | | | IV-1 | Tmc7 | 1.03 |
| 14639 | 3 | 4 | | | IV-1 | Tdrkh | 1.03 | 14735 | 3 | 4 | | | IV-1 | Tmcc1 | 1.15 |
| 14640 | 3 | 4 | | | IV-1 | Tead1 | 1.03 | 14736 | 3 | 4 | | | IV-1 | Tmco4 | 1.50 |
| 14641 | 3 | 4 | | | IV-1 | Tead2 | 1.14 | 14737 | 3 | 4 | | | IV-1 | Tmed11 | 1.25 |
| 14642 | 3 | 4 | | | IV-1 | Tead3 | 1.35 | 14738 | 3 | 4 | | | IV-1 | Tmed4 | 1.11 |
| 14643 | 3 | 4 | | | IV-1 | Tead4 | 1.00 | 14739 | 3 | 4 | | | IV-1 | Tmed6 | 1.18 |
| 14644 | 3 | 4 | | | IV-1 | Tecpr1 | 1.00 | 14740 | 3 | 4 | | | IV-1 | Tmed8 | 1.13 |
| 14645 | 3 | 4 | | | IV-1 | Tecpr2 | 1.12 | 14741 | 3 | 4 | | | IV-1 | Tmeff1 | 1.33 |
| 14646 | 3 | 4 | | | IV-1 | Tecr | 1.02 | 14742 | 3 | 4 | | | IV-1 | Tmeff2 | 1.09 |
| 14647 | 3 | 4 | | | IV-1 | Tef | 1.12 | 14743 | 3 | 4 | | | IV-1 | Tmem100 | 1.06 |
| 14648 | 3 | 4 | | | IV-1 | Telo2 | 1.05 | 14744 | 3 | 4 | | | IV-1 | Tmem104 | 1.13 |
| 14649 | 3 | 4 | | | IV-1 | Tenc1 | 1.32 | 14745 | 3 | 4 | | | IV-1 | Tmem106b | 1.14 |
| 14650 | 3 | 4 | | | IV-1 | Tenm3 | 1.37 | 14746 | 3 | 4 | | | IV-1 | Tmem110 | 1.06 |
| 14651 | 3 | 4 | | | IV-1 | Tenm4 | 1.19 | 14747 | 3 | 4 | | | IV-1 | Tmem121 | 1.39 |
| 14652 | 3 | 4 | | | IV-1 | Terf2ip | 1.40 | 14748 | 3 | 4 | | | IV-1 | Tmem125 | 1.02 |
| 14653 | 3 | 4 | | | IV-1 | Tert | 1.08 | 14749 | 3 | 4 | | | IV-1 | Tmem127 | 1.01 |
| 14654 | 3 | 4 | | | IV-1 | Tes | 1.08 | 14750 | 3 | 4 | | | IV-1 | Tmem128 | 1.03 |
| 14655 | 3 | 4 | | | IV-1 | Tesk1 | 1.22 | 14751 | 3 | 4 | | | IV-1 | Tmem130 | 1.46 |
| 14656 | 3 | 4 | | | IV-1 | Tet1 | 1.10 | 14752 | 3 | 4 | | | IV-1 | Tmem132a | 1.12 |
| 14657 | 3 | 4 | | | IV-1 | Tet2 | 1.14 | 14753 | 3 | 4 | | | IV-1 | Tmem132c | 1.30 |
| 14658 | 3 | 4 | | | IV-1 | Tet3 | 1.13 | 14754 | 3 | 4 | | | IV-1 | Tmem132d | 1.35 |
| 14659 | 3 | 4 | | | IV-1 | Tex261 | 1.03 | 14755 | 3 | 4 | | | IV-1 | Tmem136 | 1.45 |
| 14660 | 3 | 4 | | | IV-1 | Tex38 | 1.06 | 14756 | 3 | 4 | | | IV-1 | Tmem138 | 1.07 |
| 14661 | 3 | 4 | | | IV-1 | Tfap2a | 1.01 | 14757 | 3 | 4 | | | IV-1 | Tmem140 | 1.29 |
| 14662 | 3 | 4 | | | IV-1 | Tfap2c | 1.19 | 14758 | 3 | 4 | | | IV-1 | Tmem147 | 1.04 |
| 14663 | 3 | 4 | | | IV-1 | Tfap2d | 1.46 | 14759 | 3 | 4 | | | IV-1 | Tmem14a | 1.19 |
| 14664 | 3 | 4 | | | IV-1 | Tfap4 | 1.14 | 14760 | 3 | 4 | | | IV-1 | Tmem150a | 1.06 |
| 14665 | 3 | 4 | | | IV-1 | Tfcp2 | 1.12 | 14761 | 3 | 4 | | | IV-1 | Tmem150b | 1.24 |
| 14666 | 3 | 4 | | | IV-1 | Tfe3 | 1.07 | 14762 | 3 | 4 | | | IV-1 | Tmem150c | 1.18 |
| 14667 | 3 | 4 | | | IV-1 | Tfpi | 1.04 | 14763 | 3 | 4 | | | IV-1 | Tmem151a | 1.15 |
| 14668 | 3 | 4 | | | IV-1 | Tfpt | 1.44 | 14764 | 3 | 4 | | | IV-1 | Tmem158 | 1.33 |
| 14669 | 3 | 4 | | | IV-1 | Tgfb2 | 1.10 | 14765 | 3 | 4 | | | IV-1 | Tmem161b | 1.22 |
| 14670 | 3 | 4 | | | IV-1 | Tgfb3 | 1.06 | 14766 | 3 | 4 | | | IV-1 | Tmem165 | 1.09 |
| 14671 | 3 | 4 | | | IV-1 | Tgfbi | 1.36 | 14767 | 3 | 4 | | | IV-1 | Tmem169 | 1.21 |
| 14672 | 3 | 4 | | | IV-1 | Tgfbr1 | 1.11 | 14768 | 3 | 4 | | | IV-1 | Tmem17 | 1.01 |
| 14673 | 3 | 4 | | | IV-1 | Tgfbr2 | 1.06 | 14769 | 3 | 4 | | | IV-1 | Tmem170b | 1.12 |
| 14674 | 3 | 4 | | | IV-1 | Tgfbr3 | 1.17 | 14770 | 3 | 4 | | | IV-1 | Tmem175 | 1.15 |
| 14675 | 3 | 4 | | | IV-1 | Tgfbrap1 | 1.17 | 14771 | 3 | 4 | | | IV-1 | Tmem178 | 1.21 |
| 14676 | 3 | 4 | | | IV-1 | Tgif1 | 1.01 | 14772 | 3 | 4 | | | IV-1 | Tmem18 | 1.21 |
| 14677 | 3 | 4 | | | IV-1 | Tgif2 | 1.03 | 14773 | 3 | 4 | | | IV-1 | Tmem181a | 1.08 |
| 14678 | 3 | 4 | | | IV-1 | Tgtp1 | 1.29 | 14774 | 3 | 4 | | | IV-1 | Tmem181b-ps | 1.11 |
| 14679 | 3 | 4 | | | IV-1 | Th | 1.21 | 14775 | 3 | 4 | | | IV-1 | Tmem184c | 1.11 |
| 14680 | 3 | 4 | | | IV-1 | Tha1 | 1.32 | 14776 | 3 | 4 | | | IV-1 | Tmem19 | 1.08 |
| 14681 | 3 | 4 | | | IV-1 | Thada | 1.02 | 14777 | 3 | 4 | | | IV-1 | Tmem194b | 1.28 |
| 14682 | 3 | 4 | | | IV-1 | Thap3 | 1.15 | 14778 | 3 | 4 | | | IV-1 | Tmem198b | 1.18 |
| 14683 | 3 | 4 | | | IV-1 | Thap7 | 1.00 | 14779 | 3 | 4 | | | IV-1 | Tmem199 | 1.03 |
| 14684 | 3 | 4 | | | IV-1 | Thbs1 | 1.31 | 14780 | 3 | 4 | | | IV-1 | Tmem2 | 1.08 |
| 14685 | 3 | 4 | | | IV-1 | Thbs2 | 1.14 | 14781 | 3 | 4 | | | IV-1 | Tmem200a | 1.39 |

Fig. 45 - 78

| | | | | | | | | | | | | | | |
|---|---|---|---|---|---|---|---|---|---|---|---|---|---|---|
| 14782 | 3 | 4 | | | IV-1 | Tmem200b | 1.15 | 14878 | 3 | 4 | | | IV-1 | Top3b | 1.08 |
| 14783 | 3 | 4 | | | IV-1 | Tmem201 | 1.06 | 14879 | 3 | 4 | | | IV-1 | Tor1aip1 | 1.11 |
| 14784 | 3 | 4 | | | IV-1 | Tmem203 | 1.45 | 14880 | 3 | 4 | | | IV-1 | Tor3a | 1.02 |
| 14785 | 3 | 4 | | | IV-1 | Tmem204 | 1.04 | 14881 | 3 | 4 | | | IV-1 | Tpcn2 | 1.38 |
| 14786 | 3 | 4 | | | IV-1 | Tmem209 | 1.03 | 14882 | 3 | 4 | | | IV-1 | Tpd52l2 | 1.01 |
| 14787 | 3 | 4 | | | IV-1 | Tmem216 | 1.05 | 14883 | 3 | 4 | | | IV-1 | Tpgs2 | 1.04 |
| 14788 | 3 | 4 | | | IV-1 | Tmem218 | 1.24 | 14884 | 3 | 4 | | | IV-1 | Tpmt | 1.16 |
| 14789 | 3 | 4 | | | IV-1 | Tmem219 | 1.13 | 14885 | 3 | 4 | | | IV-1 | Tprg1 | 1.03 |
| 14790 | 3 | 4 | | | IV-1 | Tmem220 | 1.10 | 14886 | 3 | 4 | | | IV-1 | Tprkb | 1.07 |
| 14791 | 3 | 4 | | | IV-1 | Tmem223 | 1.14 | 14887 | 3 | 4 | | | IV-1 | Tpm | 1.05 |
| 14792 | 3 | 4 | | | IV-1 | Tmem229a | 1.15 | 14888 | 3 | 4 | | | IV-1 | Traf3 | 1.23 |
| 14793 | 3 | 4 | | | IV-1 | Tmem229b | 1.31 | 14889 | 3 | 4 | | | IV-1 | Traf3ip1 | 1.11 |
| 14794 | 3 | 4 | | | IV-1 | Tmem231 | 1.13 | 14890 | 3 | 4 | | | IV-1 | Traf3ip2 | 1.26 |
| 14795 | 3 | 4 | | | IV-1 | Tmem237 | 1.01 | 14891 | 3 | 4 | | | IV-1 | Traf5 | 1.19 |
| 14796 | 3 | 4 | | | IV-1 | Tmem239 | 1.48 | 14892 | 3 | 4 | | | IV-1 | Traf7 | 1.01 |
| 14797 | 3 | 4 | | | IV-1 | Tmem241 | 1.26 | 14893 | 3 | 4 | | | IV-1 | Trafd1 | 1.30 |
| 14798 | 3 | 4 | | | IV-1 | Tmem243 | 1.18 | 14894 | 3 | 4 | | | IV-1 | Trak1 | 1.03 |
| 14799 | 3 | 4 | | | IV-1 | Tmem248 | 1.07 | 14895 | 3 | 4 | | | IV-1 | Tram1l1 | 1.19 |
| 14800 | 3 | 4 | | | IV-1 | Tmem25 | 1.05 | 14896 | 3 | 4 | | | IV-1 | Tram2 | 1.17 |
| 14801 | 3 | 4 | | | IV-1 | Tmem251 | 1.26 | 14897 | 3 | 4 | | | IV-1 | Trank1 | 1.18 |
| 14802 | 3 | 4 | | | IV-1 | Tmem254a | 1.40 | 14898 | 3 | 4 | | | IV-1 | Trappc10 | 1.07 |
| 14803 | 3 | 4 | | | IV-1 | Tmem254b | 1.29 | 14899 | 3 | 4 | | | IV-1 | Trappc11 | 1.08 |
| 14804 | 3 | 4 | | | IV-1 | Tmem259 | 1.10 | 14900 | 3 | 4 | | | IV-1 | Trappc2 | 1.03 |
| 14805 | 3 | 4 | | | IV-1 | Tmem26 | 1.29 | 14901 | 3 | 4 | | | IV-1 | Trappc3 | 1.11 |
| 14806 | 3 | 4 | | | IV-1 | Tmem28 | 1.42 | 14902 | 3 | 4 | | | IV-1 | Trappc4 | 1.08 |
| 14807 | 3 | 4 | | | IV-1 | Tmem29 | 1.08 | 14903 | 3 | 4 | | | IV-1 | Trappc5 | 1.05 |
| 14808 | 3 | 4 | | | IV-1 | Tmem33 | 1.06 | 14904 | 3 | 4 | | | IV-1 | Trappc6b | 1.17 |
| 14809 | 3 | 4 | | | IV-1 | Tmem35 | 1.39 | 14905 | 3 | 4 | | | IV-1 | Trappc9 | 1.17 |
| 14810 | 3 | 4 | | | IV-1 | Tmem41a | 1.15 | 14906 | 3 | 4 | | | IV-1 | Trdmt1 | 1.32 |
| 14811 | 3 | 4 | | | IV-1 | Tmem42 | 1.28 | 14907 | 3 | 4 | | | IV-1 | Trem3 | 1.01 |
| 14812 | 3 | 4 | | | IV-1 | Tmem43 | 1.07 | 14908 | 3 | 4 | | | IV-1 | Trerf1 | 1.03 |
| 14813 | 3 | 4 | | | IV-1 | Tmem44 | 1.50 | 14909 | 3 | 4 | | | IV-1 | Trhde | 1.47 |
| 14814 | 3 | 4 | | | IV-1 | Tmem47 | 1.07 | 14910 | 3 | 4 | | | IV-1 | Trib2 | 1.26 |
| 14815 | 3 | 4 | | | IV-1 | Tmem5 | 1.25 | 14911 | 3 | 4 | | | IV-1 | Tril | 1.02 |
| 14816 | 3 | 4 | | | IV-1 | Tmem50a | 1.08 | 14912 | 3 | 4 | | | IV-1 | Trim11 | 1.14 |
| 14817 | 3 | 4 | | | IV-1 | Tmem53 | 1.25 | 14913 | 3 | 4 | | | IV-1 | Trim12a | 1.19 |
| 14818 | 3 | 4 | | | IV-1 | Tmem55b | 1.13 | 14914 | 3 | 4 | | | IV-1 | Trim12c | 1.16 |
| 14819 | 3 | 4 | | | IV-1 | Tmem57 | 1.31 | 14915 | 3 | 4 | | | IV-1 | Trim14 | 1.11 |
| 14820 | 3 | 4 | | | IV-1 | Tmem59 | 1.06 | 14916 | 3 | 4 | | | IV-1 | Trim2 | 1.05 |
| 14821 | 3 | 4 | | | IV-1 | Tmem62 | 1.04 | 14917 | 3 | 4 | | | IV-1 | Trim21 | 1.44 |
| 14822 | 3 | 4 | | | IV-1 | Tmem63b | 1.28 | 14918 | 3 | 4 | | | IV-1 | Trim23 | 1.41 |
| 14823 | 3 | 4 | | | IV-1 | Tmem63c | 1.14 | 14919 | 3 | 4 | | | IV-1 | Trim24 | 1.23 |
| 14824 | 3 | 4 | | | IV-1 | Tmem65 | 1.05 | 14920 | 3 | 4 | | | IV-1 | Trim26 | 1.13 |
| 14825 | 3 | 4 | | | IV-1 | Tmem67 | 1.07 | 14921 | 3 | 4 | | | IV-1 | Trim3 | 1.14 |
| 14826 | 3 | 4 | | | IV-1 | Tmem74 | 1.23 | 14922 | 3 | 4 | | | IV-1 | Trim32 | 1.12 |
| 14827 | 3 | 4 | | | IV-1 | Tmem80 | 1.05 | 14923 | 3 | 4 | | | IV-1 | Trim33 | 1.26 |
| 14828 | 3 | 4 | | | IV-1 | Tmem81 | 1.19 | 14924 | 3 | 4 | | | IV-1 | Trim35 | 1.07 |
| 14829 | 3 | 4 | | | IV-1 | Tmem82 | 1.13 | 14925 | 3 | 4 | | | IV-1 | Trim36 | 1.40 |
| 14830 | 3 | 4 | | | IV-1 | Tmem86a | 1.27 | 14926 | 3 | 4 | | | IV-1 | Trim37 | 1.06 |
| 14831 | 3 | 4 | | | IV-1 | Tmem87b | 1.11 | 14927 | 3 | 4 | | | IV-1 | Trim39 | 1.21 |
| 14832 | 3 | 4 | | | IV-1 | Tmf1 | 1.06 | 14928 | 3 | 4 | | | IV-1 | Trim41 | 1.11 |
| 14833 | 3 | 4 | | | IV-1 | Tmigd1 | 1.11 | 14929 | 3 | 4 | | | IV-1 | Trim44 | 1.19 |
| 14834 | 3 | 4 | | | IV-1 | Tmod2 | 1.39 | 14930 | 3 | 4 | | | IV-1 | Trim45 | 1.34 |
| 14835 | 3 | 4 | | | IV-1 | Tmprss11bnl | 1.22 | 14931 | 3 | 4 | | | IV-1 | Trim46 | 1.44 |
| 14836 | 3 | 4 | | | IV-1 | Tmsb15b1 | 1.20 | 14932 | 3 | 4 | | | IV-1 | Trim6 | 1.27 |
| 14837 | 3 | 4 | | | IV-1 | Tmtc1 | 1.19 | 14933 | 3 | 4 | | | IV-1 | Trim62 | 1.23 |
| 14838 | 3 | 4 | | | IV-1 | Tmtc2 | 1.35 | 14934 | 3 | 4 | | | IV-1 | Trim68 | 1.39 |
| 14839 | 3 | 4 | | | IV-1 | Tmtc4 | 1.16 | 14935 | 3 | 4 | | | IV-1 | Trim8 | 1.07 |
| 14840 | 3 | 4 | | | IV-1 | Tmx3 | 1.01 | 14936 | 3 | 4 | | | IV-1 | Trio | 1.18 |
| 14841 | 3 | 4 | | | IV-1 | Tmx4 | 1.40 | 14937 | 3 | 4 | | | IV-1 | Trip12 | 1.03 |
| 14842 | 3 | 4 | | | IV-1 | Tnfaip3 | 1.02 | 14938 | 3 | 4 | | | IV-1 | Trip6 | 1.08 |
| 14843 | 3 | 4 | | | IV-1 | Tnfaip6 | 1.02 | 14939 | 3 | 4 | | | IV-1 | Triqk | 1.36 |
| 14844 | 3 | 4 | | | IV-1 | Tnfrsf10b | 1.07 | 14940 | 3 | 4 | | | IV-1 | Trit1 | 1.24 |
| 14845 | 3 | 4 | | | IV-1 | Tnfrsf11b | 1.02 | 14941 | 3 | 4 | | | IV-1 | Trmt1 | 1.13 |
| 14846 | 3 | 4 | | | IV-1 | Tnfrsf12a | 1.35 | 14942 | 3 | 4 | | | IV-1 | Trmt11 | 1.17 |
| 14847 | 3 | 4 | | | IV-1 | Tnfrsf18 | 1.35 | 14943 | 3 | 4 | | | IV-1 | Trmt13 | 1.03 |
| 14848 | 3 | 4 | | | IV-1 | Tnfrsf19 | 1.02 | 14944 | 3 | 4 | | | IV-1 | Trmt44 | 1.16 |
| 14849 | 3 | 4 | | | IV-1 | Tnfrsf22 | 1.11 | 14945 | 3 | 4 | | | IV-1 | Trmt6 | 1.29 |
| 14850 | 3 | 4 | | | IV-1 | Tnfsf10 | 1.05 | 14946 | 3 | 4 | | | IV-1 | Trmt61a | 1.29 |
| 14851 | 3 | 4 | | | IV-1 | Tnfsf11 | 1.03 | 14947 | 3 | 4 | | | IV-1 | Trmt61b | 1.02 |
| 14852 | 3 | 4 | | | IV-1 | Tnfsf12 | 1.03 | 14948 | 3 | 4 | | | IV-1 | Trmu | 1.27 |
| 14853 | 3 | 4 | | | IV-1 | Tnfsf13 | 1.02 | 14949 | 3 | 4 | | | IV-1 | Trnt1 | 1.05 |
| 14854 | 3 | 4 | | | IV-1 | Tnfsf9 | 1.37 | 14950 | 3 | 4 | | | IV-1 | Tro | 1.33 |
| 14855 | 3 | 4 | | | IV-1 | Tnik | 1.16 | 14951 | 3 | 4 | | | IV-1 | Trove2 | 1.22 |
| 14856 | 3 | 4 | | | IV-1 | Tnip1 | 1.04 | 14952 | 3 | 4 | | | IV-1 | Trp53bp1 | 1.21 |
| 14857 | 3 | 4 | | | IV-1 | Tnip2 | 1.07 | 14953 | 3 | 4 | | | IV-1 | Trp53bp2 | 1.11 |
| 14858 | 3 | 4 | | | IV-1 | Tnk2 | 1.10 | 14954 | 3 | 4 | | | IV-1 | Trp53i11 | 1.37 |
| 14859 | 3 | 4 | | | IV-1 | Tnk2os | 1.26 | 14955 | 3 | 4 | | | IV-1 | Trp53inp1 | 1.46 |
| 14860 | 3 | 4 | | | IV-1 | Tnks | 1.24 | 14956 | 3 | 4 | | | IV-1 | Trp53rk | 1.05 |
| 14861 | 3 | 4 | | | IV-1 | Tnnc1 | 1.02 | 14957 | 3 | 4 | | | IV-1 | Trp73 | 1.20 |
| 14862 | 3 | 4 | | | IV-1 | Tnnt2 | 1.03 | 14958 | 3 | 4 | | | IV-1 | Trpc1 | 1.32 |
| 14863 | 3 | 4 | | | IV-1 | Tnpo1 | 1.10 | 14959 | 3 | 4 | | | IV-1 | Trpc3 | 1.19 |
| 14864 | 3 | 4 | | | IV-1 | Tnrc18 | 1.22 | 14960 | 3 | 4 | | | IV-1 | Trpc5 | 1.34 |
| 14865 | 3 | 4 | | | IV-1 | Tnrc6a | 1.15 | 14961 | 3 | 4 | | | IV-1 | Trpm3 | 1.33 |
| 14866 | 3 | 4 | | | IV-1 | Tnrc6c | 1.20 | 14962 | 3 | 4 | | | IV-1 | Trpm4 | 1.35 |
| 14867 | 3 | 4 | | | IV-1 | Tns1 | 1.06 | 14963 | 3 | 4 | | | IV-1 | Trpm5 | 1.06 |
| 14868 | 3 | 4 | | | IV-1 | Tns3 | 1.17 | 14964 | 3 | 4 | | | IV-1 | Trpm7 | 1.06 |
| 14869 | 3 | 4 | | | IV-1 | Tns4 | 1.20 | 14965 | 3 | 4 | | | IV-1 | Trpt1 | 1.11 |
| 14870 | 3 | 4 | | | IV-1 | Toe1 | 1.03 | 14966 | 3 | 4 | | | IV-1 | Trpv4 | 1.21 |
| 14871 | 3 | 4 | | | IV-1 | Tom1l2 | 1.12 | 14967 | 3 | 4 | | | IV-1 | Trrap | 1.10 |
| 14872 | 3 | 4 | | | IV-1 | Tomm20 | 1.42 | 14968 | 3 | 4 | | | IV-1 | Trub1 | 1.47 |
| 14873 | 3 | 4 | | | IV-1 | Tomm34 | 1.01 | 14969 | 3 | 4 | | | IV-1 | Trub2 | 1.20 |
| 14874 | 3 | 4 | | | IV-1 | Tomm6os | 1.38 | 14970 | 3 | 4 | | | IV-1 | Try5 | 1.09 |
| 14875 | 3 | 4 | | | IV-1 | Tomm70a | 1.02 | 14971 | 3 | 4 | | | IV-1 | Tsacc | 1.38 |
| 14876 | 3 | 4 | | | IV-1 | Top2b | 1.14 | 14972 | 3 | 4 | | | IV-1 | Tsc1 | 1.04 |
| 14877 | 3 | 4 | | | IV-1 | Top3a | 1.04 | 14973 | 3 | 4 | | | IV-1 | Tsc22d1 | 1.02 |

Fig. 45 - 79

| | | | | | | | | | | | | | | |
|---|---|---|---|---|---|---|---|---|---|---|---|---|---|---|
| 14974 | 3 | 4 | | | IV-1 | Tsc22d3 | 1.24 | 15070 | 3 | 4 | | | IV-1 | Ubl7 | 1.19 |
| 14975 | 3 | 4 | | | IV-1 | Tsg101 | 1.16 | 15071 | 3 | 4 | | | IV-1 | Ublcp1 | 1.20 |
| 14976 | 3 | 4 | | | IV-1 | Tsga10 | 1.38 | 15072 | 3 | 4 | | | IV-1 | Ubn2 | 1.01 |
| 14977 | 3 | 4 | | | IV-1 | Tshz1 | 1.50 | 15073 | 3 | 4 | | | IV-1 | Ubp1 | 1.17 |
| 14978 | 3 | 4 | | | IV-1 | Tshz2 | 1.48 | 15074 | 3 | 4 | | | IV-1 | Ubqln2 | 1.17 |
| 14979 | 3 | 4 | | | IV-1 | Tshz3 | 1.38 | 15075 | 3 | 4 | | | IV-1 | Ubr1 | 1.11 |
| 14980 | 3 | 4 | | | IV-1 | Tsku | 1.01 | 15076 | 3 | 4 | | | IV-1 | Ubr2 | 1.16 |
| 14981 | 3 | 4 | | | IV-1 | Tslp | 1.21 | 15077 | 3 | 4 | | | IV-1 | Ubr3 | 1.30 |
| 14982 | 3 | 4 | | | IV-1 | Tsn | 1.14 | 15078 | 3 | 4 | | | IV-1 | Ubr4 | 1.03 |
| 14983 | 3 | 4 | | | IV-1 | Tsnax | 1.02 | 15079 | 3 | 4 | | | IV-1 | Ubr5 | 1.12 |
| 14984 | 3 | 4 | | | IV-1 | Tspan11 | 1.45 | 15080 | 3 | 4 | | | IV-1 | Ubtd2 | 1.22 |
| 14985 | 3 | 4 | | | IV-1 | Tspan2 | 1.02 | 15081 | 3 | 4 | | | IV-1 | Ubtf | 1.19 |
| 14986 | 3 | 4 | | | IV-1 | Tspan3 | 1.07 | 15082 | 3 | 4 | | | IV-1 | Ubxn4 | 1.05 |
| 14987 | 3 | 4 | | | IV-1 | Tspan4 | 1.37 | 15083 | 3 | 4 | | | IV-1 | Ubxn6 | 1.06 |
| 14988 | 3 | 4 | | | IV-1 | Tspan5 | 1.18 | 15084 | 3 | 4 | | | IV-1 | Ubxn7 | 1.24 |
| 14989 | 3 | 4 | | | IV-1 | Tspan7 | 1.01 | 15085 | 3 | 4 | | | IV-1 | Uchl1 | 1.34 |
| 14990 | 3 | 4 | | | IV-1 | Tspyl2 | 1.36 | 15086 | 3 | 4 | | | IV-1 | Ucn2 | 1.01 |
| 14991 | 3 | 4 | | | IV-1 | Tspyl3 | 1.31 | 15087 | 3 | 4 | | | IV-1 | Ufd1l | 1.25 |
| 14992 | 3 | 4 | | | IV-1 | Tspyl4 | 1.36 | 15088 | 3 | 4 | | | IV-1 | Ufl1 | 1.09 |
| 14993 | 3 | 4 | | | IV-1 | Tspyl5 | 1.28 | 15089 | 3 | 4 | | | IV-1 | Ufm1 | 1.00 |
| 14994 | 3 | 4 | | | IV-1 | Tsr1 | 1.05 | 15090 | 3 | 4 | | | IV-1 | Ufsp1 | 1.35 |
| 14995 | 3 | 4 | | | IV-1 | Tsr2 | 1.32 | 15091 | 3 | 4 | | | IV-1 | Ugcg | 1.10 |
| 14996 | 3 | 4 | | | IV-1 | Tsr3 | 1.20 | 15092 | 3 | 4 | | | IV-1 | Ugdh | 1.05 |
| 14997 | 3 | 4 | | | IV-1 | Tssc1 | 1.00 | 15093 | 3 | 4 | | | IV-1 | Uggt2 | 1.48 |
| 14998 | 3 | 4 | | | IV-1 | Tssk4 | 1.10 | 15094 | 3 | 4 | | | IV-1 | Ugt1a1 | 1.02 |
| 14999 | 3 | 4 | | | IV-1 | Tssk6 | 1.22 | 15095 | 3 | 4 | | | IV-1 | Ugt2a1 | 1.35 |
| 15000 | 3 | 4 | | | IV-1 | Tsta3 | 1.03 | 15096 | 3 | 4 | | | IV-1 | Ugt8a | 1.28 |
| 15001 | 3 | 4 | | | IV-1 | Ttbk2 | 1.23 | 15097 | 3 | 4 | | | IV-1 | Uhrf1bp1 | 1.03 |
| 15002 | 3 | 4 | | | IV-1 | Ttc14 | 1.09 | 15098 | 3 | 4 | | | IV-1 | Uhrf1bp1l | 1.17 |
| 15003 | 3 | 4 | | | IV-1 | Ttc17 | 1.13 | 15099 | 3 | 4 | | | IV-1 | Ulk1 | 1.00 |
| 15004 | 3 | 4 | | | IV-1 | Ttc19 | 1.30 | 15100 | 3 | 4 | | | IV-1 | Ulk2 | 1.30 |
| 15005 | 3 | 4 | | | IV-1 | Ttc21b | 1.04 | 15101 | 3 | 4 | | | IV-1 | Ulk3 | 1.05 |
| 15006 | 3 | 4 | | | IV-1 | Ttc26 | 1.17 | 15102 | 3 | 4 | | | IV-1 | Unc119 | 1.08 |
| 15007 | 3 | 4 | | | IV-1 | Ttc28 | 1.40 | 15103 | 3 | 4 | | | IV-1 | Unc13a | 1.41 |
| 15008 | 3 | 4 | | | IV-1 | Ttc3 | 1.31 | 15104 | 3 | 4 | | | IV-1 | Unc13b | 1.18 |
| 15009 | 3 | 4 | | | IV-1 | Ttc37 | 1.06 | 15105 | 3 | 4 | | | IV-1 | Unc13c | 1.11 |
| 15010 | 3 | 4 | | | IV-1 | Ttc38 | 1.28 | 15106 | 3 | 4 | | | IV-1 | Unc45a | 1.10 |
| 15011 | 3 | 4 | | | IV-1 | Ttc39a | 1.01 | 15107 | 3 | 4 | | | IV-1 | Unc50 | 1.07 |
| 15012 | 3 | 4 | | | IV-1 | Ttc39b | 1.39 | 15108 | 3 | 4 | | | IV-1 | Unc5a | 1.04 |
| 15013 | 3 | 4 | | | IV-1 | Ttc39c | 1.11 | 15109 | 3 | 4 | | | IV-1 | Unc5c | 1.44 |
| 15014 | 3 | 4 | | | IV-1 | Ttc4 | 1.12 | 15110 | 3 | 4 | | | IV-1 | Unc79 | 1.49 |
| 15015 | 3 | 4 | | | IV-1 | Ttc5 | 1.26 | 15111 | 3 | 4 | | | IV-1 | Unc80 | 1.13 |
| 15016 | 3 | 4 | | | IV-1 | Ttc7b | 1.22 | 15112 | 3 | 4 | | | IV-1 | Unk | 1.06 |
| 15017 | 3 | 4 | | | IV-1 | Ttc8 | 1.31 | 15113 | 3 | 4 | | | IV-1 | Unkl | 1.12 |
| 15018 | 3 | 4 | | | IV-1 | Ttc9 | 1.12 | 15114 | 3 | 4 | | | IV-1 | Upf3b | 1.13 |
| 15019 | 3 | 4 | | | IV-1 | Ttc9b | 1.09 | 15115 | 3 | 4 | | | IV-1 | Urb2 | 1.02 |
| 15020 | 3 | 4 | | | IV-1 | Tti2 | 1.16 | 15116 | 3 | 4 | | | IV-1 | Uri1 | 1.45 |
| 15021 | 3 | 4 | | | IV-1 | Ttl | 1.08 | 15117 | 3 | 4 | | | IV-1 | Use1 | 1.18 |
| 15022 | 3 | 4 | | | IV-1 | Ttll1 | 1.46 | 15118 | 3 | 4 | | | IV-1 | Usf1 | 1.18 |
| 15023 | 3 | 4 | | | IV-1 | Ttll3 | 1.23 | 15119 | 3 | 4 | | | IV-1 | Usf2 | 1.07 |
| 15024 | 3 | 4 | | | IV-1 | Ttll7 | 1.09 | 15120 | 3 | 4 | | | IV-1 | Usp12 | 1.06 |
| 15025 | 3 | 4 | | | IV-1 | Ttpa | 1.13 | 15121 | 3 | 4 | | | IV-1 | Usp16 | 1.11 |
| 15026 | 3 | 4 | | | IV-1 | Ttpal | 1.01 | 15122 | 3 | 4 | | | IV-1 | Usp2 | 1.02 |
| 15027 | 3 | 4 | | | IV-1 | Ttyh3 | 1.19 | 15123 | 3 | 4 | | | IV-1 | Usp22 | 1.30 |
| 15028 | 3 | 4 | | | IV-1 | Tuba1a | 1.24 | 15124 | 3 | 4 | | | IV-1 | Usp27x | 1.29 |
| 15029 | 3 | 4 | | | IV-1 | Tubb2a | 1.29 | 15125 | 3 | 4 | | | IV-1 | Usp29 | 1.29 |
| 15030 | 3 | 4 | | | IV-1 | Tubb2a-ps2 | 1.50 | 15126 | 3 | 4 | | | IV-1 | Usp3 | 1.27 |
| 15031 | 3 | 4 | | | IV-1 | Tubb2b | 1.36 | 15127 | 3 | 4 | | | IV-1 | Usp30 | 1.31 |
| 15032 | 3 | 4 | | | IV-1 | Tubb3 | 1.35 | 15128 | 3 | 4 | | | IV-1 | Usp33 | 1.00 |
| 15033 | 3 | 4 | | | IV-1 | Tubb4a | 1.30 | 15129 | 3 | 4 | | | IV-1 | Usp35 | 1.28 |
| 15034 | 3 | 4 | | | IV-1 | Tubgcp2 | 1.18 | 15130 | 3 | 4 | | | IV-1 | Usp36 | 1.21 |
| 15035 | 3 | 4 | | | IV-1 | Tubgcp5 | 1.18 | 15131 | 3 | 4 | | | IV-1 | Usp4 | 1.02 |
| 15036 | 3 | 4 | | | IV-1 | Tulp3 | 1.00 | 15132 | 3 | 4 | | | IV-1 | Usp42 | 1.06 |
| 15037 | 3 | 4 | | | IV-1 | Tulp4 | 1.25 | 15133 | 3 | 4 | | | IV-1 | Usp43 | 1.13 |
| 15038 | 3 | 4 | | | IV-1 | Tunar | 1.30 | 15134 | 3 | 4 | | | IV-1 | Usp47 | 1.03 |
| 15039 | 3 | 4 | | | IV-1 | Tusc1 | 1.44 | 15135 | 3 | 4 | | | IV-1 | Usp48 | 1.06 |
| 15040 | 3 | 4 | | | IV-1 | Tusc3 | 1.19 | 15136 | 3 | 4 | | | IV-1 | Usp49 | 1.00 |
| 15041 | 3 | 4 | | | IV-1 | Tut1 | 1.10 | 15137 | 3 | 4 | | | IV-1 | Usp51 | 1.08 |
| 15042 | 3 | 4 | | | IV-1 | Tvp23a | 1.21 | 15138 | 3 | 4 | | | IV-1 | Usp53 | 1.16 |
| 15043 | 3 | 4 | | | IV-1 | Twist1 | 1.15 | 15139 | 3 | 4 | | | IV-1 | Usp54 | 1.31 |
| 15044 | 3 | 4 | | | IV-1 | Twistnb | 1.04 | 15140 | 3 | 4 | | | IV-1 | Usp6nl | 1.17 |
| 15045 | 3 | 4 | | | IV-1 | Twsg1 | 1.00 | 15141 | 3 | 4 | | | IV-1 | Usp9x | 1.01 |
| 15046 | 3 | 4 | | | IV-1 | Txlng | 1.16 | 15142 | 3 | 4 | | | IV-1 | Uspl1 | 1.06 |
| 15047 | 3 | 4 | | | IV-1 | Txndc11 | 1.00 | 15143 | 3 | 4 | | | IV-1 | Ust | 1.07 |
| 15048 | 3 | 4 | | | IV-1 | Tyro3 | 1.03 | 15144 | 3 | 4 | | | IV-1 | Utp14a | 1.05 |
| 15049 | 3 | 4 | | | IV-1 | Tyw3 | 1.28 | 15145 | 3 | 4 | | | IV-1 | Utp15 | 1.06 |
| 15050 | 3 | 4 | | | IV-1 | U2af1 | 1.01 | 15146 | 3 | 4 | | | IV-1 | Utp18 | 1.05 |
| 15051 | 3 | 4 | | | IV-1 | U2surp | 1.03 | 15147 | 3 | 4 | | | IV-1 | Utp20 | 1.02 |
| 15052 | 3 | 4 | | | IV-1 | Ubald1 | 1.09 | 15148 | 3 | 4 | | | IV-1 | Utrn | 1.03 |
| 15053 | 3 | 4 | | | IV-1 | Ubash3b | 1.10 | 15149 | 3 | 4 | | | IV-1 | Uts2r | 1.07 |
| 15054 | 3 | 4 | | | IV-1 | Ubc | 1.02 | 15150 | 3 | 4 | | | IV-1 | Vac14 | 1.12 |
| 15055 | 3 | 4 | | | IV-1 | Ube2cbp | 1.45 | 15151 | 3 | 4 | | | IV-1 | Vamp1 | 1.45 |
| 15056 | 3 | 4 | | | IV-1 | Ube2d1 | 1.05 | 15152 | 3 | 4 | | | IV-1 | Vamp2 | 1.34 |
| 15057 | 3 | 4 | | | IV-1 | Ube2e2 | 1.29 | 15153 | 3 | 4 | | | IV-1 | Vangl2 | 1.27 |
| 15058 | 3 | 4 | | | IV-1 | Ube2e3 | 1.06 | 15154 | 3 | 4 | | | IV-1 | Vapb | 1.10 |
| 15059 | 3 | 4 | | | IV-1 | Ube2g1 | 1.06 | 15155 | 3 | 4 | | | IV-1 | Vash1 | 1.05 |
| 15060 | 3 | 4 | | | IV-1 | Ube2g2 | 1.03 | 15156 | 3 | 4 | | | IV-1 | Vash2 | 1.17 |
| 15061 | 3 | 4 | | | IV-1 | Ube2i | 1.08 | 15157 | 3 | 4 | | | IV-1 | Vasn | 1.05 |
| 15062 | 3 | 4 | | | IV-1 | Ube2j2 | 1.11 | 15158 | 3 | 4 | | | IV-1 | Vat1l | 1.19 |
| 15063 | 3 | 4 | | | IV-1 | Ube2o | 1.09 | 15159 | 3 | 4 | | | IV-1 | Vav1 | 1.05 |
| 15064 | 3 | 4 | | | IV-1 | Ube2q1 | 1.01 | 15160 | 3 | 4 | | | IV-1 | Vav2 | 1.07 |
| 15065 | 3 | 4 | | | IV-1 | Ube2q2 | 1.04 | 15161 | 3 | 4 | | | IV-1 | Vax1 | 1.13 |
| 15066 | 3 | 4 | | | IV-1 | Ube2w | 1.05 | 15162 | 3 | 4 | | | IV-1 | Vax2os | 1.18 |
| 15067 | 3 | 4 | | | IV-1 | Ube4b | 1.02 | 15163 | 3 | 4 | | | IV-1 | Vcan | 1.07 |
| 15068 | 3 | 4 | | | IV-1 | Ubl3 | 1.01 | 15164 | 3 | 4 | | | IV-1 | Vegfc | 1.28 |
| 15069 | 3 | 4 | | | IV-1 | Ubl5 | 1.17 | 15165 | 3 | 4 | | | IV-1 | Veph1 | 1.23 |

Fig. 45 - 80

| | | | | | | | | | | | | | |
|---|---|---|---|---|---|---|---|---|---|---|---|---|---|
| 15166 | 3 | 4 | | | IV-1 | Vezf1 | 1.21 | 15262 | 3 | 4 | | IV-1 | Wnt10b | 1.14 |
| 15167 | 3 | 4 | | | IV-1 | Vhl | 1.03 | 15263 | 3 | 4 | | IV-1 | Wnt11 | 1.20 |
| 15168 | 3 | 4 | | | IV-1 | Vill | 1.15 | 15264 | 3 | 4 | | IV-1 | Wnt2b | 1.02 |
| 15169 | 3 | 4 | | | IV-1 | Vipas39 | 1.16 | 15265 | 3 | 4 | | IV-1 | Wnt3 | 1.01 |
| 15170 | 3 | 4 | | | IV-1 | Vkorc1l1 | 1.04 | 15266 | 3 | 4 | | IV-1 | Wnt4 | 1.16 |
| 15171 | 3 | 4 | | | IV-1 | Vldlr | 1.33 | 15267 | 3 | 4 | | IV-1 | Wnt5a | 1.31 |
| 15172 | 3 | 4 | | | IV-1 | Vmac | 1.48 | 15268 | 3 | 4 | | IV-1 | Wnt5b | 1.25 |
| 15173 | 3 | 4 | | | IV-1 | Vopp1 | 1.10 | 15269 | 3 | 4 | | IV-1 | Wnt7a | 1.28 |
| 15174 | 3 | 4 | | | IV-1 | Vps11 | 1.20 | 15270 | 3 | 4 | | IV-1 | Wnt7b | 1.09 |
| 15175 | 3 | 4 | | | IV-1 | Vps13d | 1.05 | 15271 | 3 | 4 | | IV-1 | Wnt9a | 1.18 |
| 15176 | 3 | 4 | | | IV-1 | Vps16 | 1.19 | 15272 | 3 | 4 | | IV-1 | Wrb | 1.12 |
| 15177 | 3 | 4 | | | IV-1 | Vps25 | 1.05 | 15273 | 3 | 4 | | IV-1 | Wsb1 | 1.10 |
| 15178 | 3 | 4 | | | IV-1 | Vps26b | 1.08 | 15274 | 3 | 4 | | IV-1 | Wsb2 | 1.04 |
| 15179 | 3 | 4 | | | IV-1 | Vps28 | 1.00 | 15275 | 3 | 4 | | IV-1 | Wscd2 | 1.20 |
| 15180 | 3 | 4 | | | IV-1 | Vps33a | 1.13 | 15276 | 3 | 4 | | IV-1 | Wt1 | 1.30 |
| 15181 | 3 | 4 | | | IV-1 | Vps33b | 1.41 | 15277 | 3 | 4 | | IV-1 | Wtap | 1.10 |
| 15182 | 3 | 4 | | | IV-1 | Vps37a | 1.10 | 15278 | 3 | 4 | | IV-1 | Wtip | 1.12 |
| 15183 | 3 | 4 | | | IV-1 | Vps37c | 1.05 | 15279 | 3 | 4 | | IV-1 | Wwc1 | 1.09 |
| 15184 | 3 | 4 | | | IV-1 | Vps37d | 1.29 | 15280 | 3 | 4 | | IV-1 | Wwc2 | 1.05 |
| 15185 | 3 | 4 | | | IV-1 | Vps39 | 1.15 | 15281 | 3 | 4 | | IV-1 | Wwox | 1.00 |
| 15186 | 3 | 4 | | | IV-1 | Vps4a | 1.21 | 15282 | 3 | 4 | | IV-1 | Wwp2 | 1.27 |
| 15187 | 3 | 4 | | | IV-1 | Vps4b | 1.06 | 15283 | 3 | 4 | | IV-1 | Wwtr1 | 1.09 |
| 15188 | 3 | 4 | | | IV-1 | Vps51 | 1.15 | 15284 | 3 | 4 | | IV-1 | Xab2 | 1.29 |
| 15189 | 3 | 4 | | | IV-1 | Vps53 | 1.11 | 15285 | 3 | 4 | | IV-1 | Xaf1 | 1.48 |
| 15190 | 3 | 4 | | | IV-1 | Vps54 | 1.01 | 15286 | 3 | 4 | | IV-1 | Xiap | 1.04 |
| 15191 | 3 | 4 | | | IV-1 | Vps72 | 1.01 | 15287 | 3 | 4 | | IV-1 | Xkr4 | 1.44 |
| 15192 | 3 | 4 | | | IV-1 | Vps8 | 1.05 | 15288 | 3 | 4 | | IV-1 | Xkr7 | 1.22 |
| 15193 | 3 | 4 | | | IV-1 | Vps9d1 | 1.31 | 15289 | 3 | 4 | | IV-1 | Xkr8 | 1.00 |
| 15194 | 3 | 4 | | | IV-1 | Vsig10 | 1.19 | 15290 | 3 | 4 | | IV-1 | Xlr3b | 1.38 |
| 15195 | 3 | 4 | | | IV-1 | Vsig10l | 1.13 | 15291 | 3 | 4 | | IV-1 | Xpa | 1.35 |
| 15196 | 3 | 4 | | | IV-1 | Vsig8 | 1.41 | 15292 | 3 | 4 | | IV-1 | Xpnpep3 | 1.03 |
| 15197 | 3 | 4 | | | IV-1 | Vsnl1 | 1.39 | 15293 | 3 | 4 | | IV-1 | Xpo6 | 1.11 |
| 15198 | 3 | 4 | | | IV-1 | Vstm2b | 1.16 | 15294 | 3 | 4 | | IV-1 | Xpot | 1.20 |
| 15199 | 3 | 4 | | | IV-1 | Vsx2 | 1.25 | 15295 | 3 | 4 | | IV-1 | Xpr1 | 1.23 |
| 15200 | 3 | 4 | | | IV-1 | Vta1 | 1.16 | 15296 | 3 | 4 | | IV-1 | Xrcc3 | 1.17 |
| 15201 | 3 | 4 | | | IV-1 | Vti1a | 1.13 | 15297 | 3 | 4 | | IV-1 | Xrn1 | 1.19 |
| 15202 | 3 | 4 | | | IV-1 | Vwa2 | 1.02 | 15298 | 3 | 4 | | IV-1 | Xrn2 | 1.18 |
| 15203 | 3 | 4 | | | IV-1 | Vwc2 | 1.35 | 15299 | 3 | 4 | | IV-1 | Xxylt1 | 1.05 |
| 15204 | 3 | 4 | | | IV-1 | Vwc2l | 1.22 | 15300 | 3 | 4 | | IV-1 | Xylt2 | 1.07 |
| 15205 | 3 | 4 | | | IV-1 | Vwf | 1.30 | 15301 | 3 | 4 | | IV-1 | Yars | 1.05 |
| 15206 | 3 | 4 | | | IV-1 | Wac | 1.07 | 15302 | 3 | 4 | | IV-1 | Ydjc | 1.09 |
| 15207 | 3 | 4 | | | IV-1 | Wars2 | 1.04 | 15303 | 3 | 4 | | IV-1 | Yeats2 | 1.01 |
| 15208 | 3 | 4 | | | IV-1 | Wasf1 | 1.45 | 15304 | 3 | 4 | | IV-1 | Yipf2 | 1.03 |
| 15209 | 3 | 4 | | | IV-1 | Wash | 1.42 | 15305 | 3 | 4 | | IV-1 | Yipf6 | 1.10 |
| 15210 | 3 | 4 | | | IV-1 | Wasl | 1.04 | 15306 | 3 | 4 | | IV-1 | Ykt6 | 1.09 |
| 15211 | 3 | 4 | | | IV-1 | Wbscr17 | 1.25 | 15307 | 3 | 4 | | IV-1 | Yipm1 | 1.08 |
| 15212 | 3 | 4 | | | IV-1 | Wdfy1 | 1.13 | 15308 | 3 | 4 | | IV-1 | Ypel3 | 1.14 |
| 15213 | 3 | 4 | | | IV-1 | Wdfy2 | 1.02 | 15309 | 3 | 4 | | IV-1 | Ypel5 | 1.19 |
| 15214 | 3 | 4 | | | IV-1 | Wdfy3 | 1.13 | 15310 | 3 | 4 | | IV-1 | Yrdc | 1.13 |
| 15215 | 3 | 4 | | | IV-1 | Wdr11 | 1.12 | 15311 | 3 | 4 | | IV-1 | Ythdc1 | 1.04 |
| 15216 | 3 | 4 | | | IV-1 | Wdr13 | 1.27 | 15312 | 3 | 4 | | IV-1 | Ythdc2 | 1.01 |
| 15217 | 3 | 4 | | | IV-1 | Wdr18 | 1.01 | 15313 | 3 | 4 | | IV-1 | Ythdf1 | 1.02 |
| 15218 | 3 | 4 | | | IV-1 | Wdr19 | 1.22 | 15314 | 3 | 4 | | IV-1 | Ythdf2 | 1.02 |
| 15219 | 3 | 4 | | | IV-1 | Wdr31 | 1.01 | 15315 | 3 | 4 | | IV-1 | Ythdf3 | 1.01 |
| 15220 | 3 | 4 | | | IV-1 | Wdr34 | 1.18 | 15316 | 3 | 4 | | IV-1 | Ywhaz | 1.02 |
| 15221 | 3 | 4 | | | IV-1 | Wdr35 | 1.06 | 15317 | 3 | 4 | | IV-1 | Yy2 | 1.25 |
| 15222 | 3 | 4 | | | IV-1 | Wdr36 | 1.08 | 15318 | 3 | 4 | | IV-1 | Zbed3 | 1.12 |
| 15223 | 3 | 4 | | | IV-1 | Wdr37 | 1.21 | 15319 | 3 | 4 | | IV-1 | Zbed5 | 1.01 |
| 15224 | 3 | 4 | | | IV-1 | Wdr41 | 1.15 | 15320 | 3 | 4 | | IV-1 | Zbp1 | 1.05 |
| 15225 | 3 | 4 | | | IV-1 | Wdr43 | 1.19 | 15321 | 3 | 4 | | IV-1 | Zbtb10 | 1.05 |
| 15226 | 3 | 4 | | | IV-1 | Wdr45 | 1.33 | 15322 | 3 | 4 | | IV-1 | Zbtb12 | 1.21 |
| 15227 | 3 | 4 | | | IV-1 | Wdr45b | 1.04 | 15323 | 3 | 4 | | IV-1 | Zbtb14 | 1.06 |
| 15228 | 3 | 4 | | | IV-1 | Wdr46 | 1.07 | 15324 | 3 | 4 | | IV-1 | Zbtb17 | 1.10 |
| 15229 | 3 | 4 | | | IV-1 | Wdr47 | 1.23 | 15325 | 3 | 4 | | IV-1 | Zbtb18 | 1.22 |
| 15230 | 3 | 4 | | | IV-1 | Wdr5 | 1.06 | 15326 | 3 | 4 | | IV-1 | Zbtb2 | 1.09 |
| 15231 | 3 | 4 | | | IV-1 | Wdr59 | 1.14 | 15327 | 3 | 4 | | IV-1 | Zbtb20 | 1.21 |
| 15232 | 3 | 4 | | | IV-1 | Wdr6 | 1.15 | 15328 | 3 | 4 | | IV-1 | Zbtb22 | 1.24 |
| 15233 | 3 | 4 | | | IV-1 | Wdr60 | 1.10 | 15329 | 3 | 4 | | IV-1 | Zbtb24 | 1.30 |
| 15234 | 3 | 4 | | | IV-1 | Wdr7 | 1.11 | 15330 | 3 | 4 | | IV-1 | Zbtb25 | 1.30 |
| 15235 | 3 | 4 | | | IV-1 | Wdr70 | 1.26 | 15331 | 3 | 4 | | IV-1 | Zbtb33 | 1.02 |
| 15236 | 3 | 4 | | | IV-1 | Wdr73 | 1.09 | 15332 | 3 | 4 | | IV-1 | Zbtb34 | 1.17 |
| 15237 | 3 | 4 | | | IV-1 | Wdr74 | 1.27 | 15333 | 3 | 4 | | IV-1 | Zbtb38 | 1.25 |
| 15238 | 3 | 4 | | | IV-1 | Wdr75 | 1.08 | 15334 | 3 | 4 | | IV-1 | Zbtb39 | 1.06 |
| 15239 | 3 | 4 | | | IV-1 | Wdr77 | 1.09 | 15335 | 3 | 4 | | IV-1 | Zbtb42 | 1.13 |
| 15240 | 3 | 4 | | | IV-1 | Wdr8 | 1.05 | 15336 | 3 | 4 | | IV-1 | Zbtb44 | 1.02 |
| 15241 | 3 | 4 | | | IV-1 | Wdr83 | 1.02 | 15337 | 3 | 4 | | IV-1 | Zbtb45 | 1.00 |
| 15242 | 3 | 4 | | | IV-1 | Wdr86 | 1.06 | 15338 | 3 | 4 | | IV-1 | Zbtb48 | 1.21 |
| 15243 | 3 | 4 | | | IV-1 | Wdr91 | 1.07 | 15339 | 3 | 4 | | IV-1 | Zbtb49 | 1.11 |
| 15244 | 3 | 4 | | | IV-1 | Wdsub1 | 1.07 | 15340 | 3 | 4 | | IV-1 | Zbtb5 | 1.19 |
| 15245 | 3 | 4 | | | IV-1 | Wfdc1 | 1.33 | 15341 | 3 | 4 | | IV-1 | Zbtb7c | 1.06 |
| 15246 | 3 | 4 | | | IV-1 | Wfikkn1 | 1.08 | 15342 | 3 | 4 | | IV-1 | Zbtb8a | 1.23 |
| 15247 | 3 | 4 | | | IV-1 | Wfs1 | 1.11 | 15343 | 3 | 4 | | IV-1 | Zbtb8b | 1.10 |
| 15248 | 3 | 4 | | | IV-1 | Whamm | 1.07 | 15344 | 3 | 4 | | IV-1 | Zbtb9 | 1.01 |
| 15249 | 3 | 4 | | | IV-1 | Whrn | 1.30 | 15345 | 3 | 4 | | IV-1 | Zc2hc1a | 1.09 |
| 15250 | 3 | 4 | | | IV-1 | Whsc1 | 1.02 | 15346 | 3 | 4 | | IV-1 | Zc2hc1c | 1.19 |
| 15251 | 3 | 4 | | | IV-1 | Wibg | 1.09 | 15347 | 3 | 4 | | IV-1 | Zc3h12b | 1.37 |
| 15252 | 3 | 4 | | | IV-1 | Wif1 | 1.09 | 15348 | 3 | 4 | | IV-1 | Zc3h12c | 1.28 |
| 15253 | 3 | 4 | | | IV-1 | Wipf2 | 1.02 | 15349 | 3 | 4 | | IV-1 | Zc3h13 | 1.01 |
| 15254 | 3 | 4 | | | IV-1 | Wipf3 | 1.34 | 15350 | 3 | 4 | | IV-1 | Zc3h14 | 1.06 |
| 15255 | 3 | 4 | | | IV-1 | Wipi2 | 1.08 | 15351 | 3 | 4 | | IV-1 | Zc3h15 | 1.01 |
| 15256 | 3 | 4 | | | IV-1 | Wisp3 | 1.41 | 15352 | 3 | 4 | | IV-1 | Zc3h4 | 1.02 |
| 15257 | 3 | 4 | | | IV-1 | Wiz | 1.22 | 15353 | 3 | 4 | | IV-1 | Zc3h7b | 1.32 |
| 15258 | 3 | 4 | | | IV-1 | Wls | 1.13 | 15354 | 3 | 4 | | IV-1 | Zc3hav1l | 1.11 |
| 15259 | 3 | 4 | | | IV-1 | Wnk2 | 1.33 | 15355 | 3 | 4 | | IV-1 | Zc4h2 | 1.12 |
| 15260 | 3 | 4 | | | IV-1 | Wnk4 | 1.17 | 15356 | 3 | 4 | | IV-1 | Zcchc11 | 1.14 |
| 15261 | 3 | 4 | | | IV-1 | Wnt10a | 1.25 | 15357 | 3 | 4 | | IV-1 | Zcchc14 | 1.12 |

Fig. 45 - 81

| | | | | | | | | | | | | | |
|---|---|---|---|---|---|---|---|---|---|---|---|---|---|
| 15358 | 3 | 4 | | | IV-1 | Zcchc24 | 1.00 | 15454 | 3 | 4 | | IV-1 | Zfp462 | 1.43 |
| 15359 | 3 | 4 | | | IV-1 | Zcchc4 | 1.01 | 15455 | 3 | 4 | | IV-1 | Zfp474 | 1.03 |
| 15360 | 3 | 4 | | | IV-1 | Zcchc5 | 1.17 | 15456 | 3 | 4 | | IV-1 | Zfp503 | 1.23 |
| 15361 | 3 | 4 | | | IV-1 | Zcchc6 | 1.01 | 15457 | 3 | 4 | | IV-1 | Zfp512 | 1.25 |
| 15362 | 3 | 4 | | | IV-1 | Zcchc7 | 1.14 | 15458 | 3 | 4 | | IV-1 | Zfp513 | 1.03 |
| 15363 | 3 | 4 | | | IV-1 | Zdhhc13 | 1.14 | 15459 | 3 | 4 | | IV-1 | Zfp516 | 1.11 |
| 15364 | 3 | 4 | | | IV-1 | Zdhhc14 | 1.04 | 15460 | 3 | 4 | | IV-1 | Zfp518b | 1.25 |
| 15365 | 3 | 4 | | | IV-1 | Zdhhc15 | 1.08 | 15461 | 3 | 4 | | IV-1 | Zfp521 | 1.24 |
| 15366 | 3 | 4 | | | IV-1 | Zdhhc17 | 1.19 | 15462 | 3 | 4 | | IV-1 | Zfp523 | 1.25 |
| 15367 | 3 | 4 | | | IV-1 | Zdhhc18 | 1.01 | 15463 | 3 | 4 | | IV-1 | Zfp53 | 1.22 |
| 15368 | 3 | 4 | | | IV-1 | Zdhhc20 | 1.21 | 15464 | 3 | 4 | | IV-1 | Zfp532 | 1.21 |
| 15369 | 3 | 4 | | | IV-1 | Zdhhc23 | 1.10 | 15465 | 3 | 4 | | IV-1 | Zfp536 | 1.29 |
| 15370 | 3 | 4 | | | IV-1 | Zdhhc24 | 1.30 | 15466 | 3 | 4 | | IV-1 | Zfp551 | 1.14 |
| 15371 | 3 | 4 | | | IV-1 | Zdhhc3 | 1.03 | 15467 | 3 | 4 | | IV-1 | Zfp553 | 1.02 |
| 15372 | 3 | 4 | | | IV-1 | Zdhhc4 | 1.49 | 15468 | 3 | 4 | | IV-1 | Zfp560 | 1.03 |
| 15373 | 3 | 4 | | | IV-1 | Zer1 | 1.21 | 15469 | 3 | 4 | | IV-1 | Zfp57 | 1.48 |
| 15374 | 3 | 4 | | | IV-1 | Zf12 | 1.31 | 15470 | 3 | 4 | | IV-1 | Zfp574 | 1.02 |
| 15375 | 3 | 4 | | | IV-1 | Zfa-ps | 1.01 | 15471 | 3 | 4 | | IV-1 | Zfp579 | 1.12 |
| 15376 | 3 | 4 | | | IV-1 | Zfand1 | 1.18 | 15472 | 3 | 4 | | IV-1 | Zfp580 | 1.44 |
| 15377 | 3 | 4 | | | IV-1 | Zfand2a | 1.49 | 15473 | 3 | 4 | | IV-1 | Zfp592 | 1.06 |
| 15378 | 3 | 4 | | | IV-1 | Zfand4 | 1.16 | 15474 | 3 | 4 | | IV-1 | Zfp593 | 1.01 |
| 15379 | 3 | 4 | | | IV-1 | Zfand5 | 1.19 | 15475 | 3 | 4 | | IV-1 | Zfp599 | 1.16 |
| 15380 | 3 | 4 | | | IV-1 | Zfhx2 | 1.22 | 15476 | 3 | 4 | | IV-1 | Zfp605 | 1.48 |
| 15381 | 3 | 4 | | | IV-1 | Zfhx3 | 1.33 | 15477 | 3 | 4 | | IV-1 | Zfp606 | 1.10 |
| 15382 | 3 | 4 | | | IV-1 | Zfhx4 | 1.42 | 15478 | 3 | 4 | | IV-1 | Zfp608 | 1.30 |
| 15383 | 3 | 4 | | | IV-1 | Zfp101 | 1.08 | 15479 | 3 | 4 | | IV-1 | Zfp609 | 1.16 |
| 15384 | 3 | 4 | | | IV-1 | Zfp105 | 1.30 | 15480 | 3 | 4 | | IV-1 | Zfp61 | 1.22 |
| 15385 | 3 | 4 | | | IV-1 | Zfp11 | 1.25 | 15481 | 3 | 4 | | IV-1 | Zfp618 | 1.20 |
| 15386 | 3 | 4 | | | IV-1 | Zfp111 | 1.07 | 15482 | 3 | 4 | | IV-1 | Zfp619 | 1.26 |
| 15387 | 3 | 4 | | | IV-1 | Zfp113 | 1.01 | 15483 | 3 | 4 | | IV-1 | Zfp622 | 1.06 |
| 15388 | 3 | 4 | | | IV-1 | Zfp119a | 1.40 | 15484 | 3 | 4 | | IV-1 | Zfp623 | 1.04 |
| 15389 | 3 | 4 | | | IV-1 | Zfp119b | 1.34 | 15485 | 3 | 4 | | IV-1 | Zfp628 | 1.33 |
| 15390 | 3 | 4 | | | IV-1 | Zfp13 | 1.27 | 15486 | 3 | 4 | | IV-1 | Zfp629 | 1.12 |
| 15391 | 3 | 4 | | | IV-1 | Zfp131 | 1.00 | 15487 | 3 | 4 | | IV-1 | Zfp639 | 1.18 |
| 15392 | 3 | 4 | | | IV-1 | Zfp146 | 1.10 | 15488 | 3 | 4 | | IV-1 | Zfp64 | 1.12 |
| 15393 | 3 | 4 | | | IV-1 | Zfp148 | 1.07 | 15489 | 3 | 4 | | IV-1 | Zfp644 | 1.18 |
| 15394 | 3 | 4 | | | IV-1 | Zfp157 | 1.13 | 15490 | 3 | 4 | | IV-1 | Zfp647 | 1.32 |
| 15395 | 3 | 4 | | | IV-1 | Zfp160 | 1.37 | 15491 | 3 | 4 | | IV-1 | Zfp651 | 1.09 |
| 15396 | 3 | 4 | | | IV-1 | Zfp174 | 1.32 | 15492 | 3 | 4 | | IV-1 | Zfp655 | 1.06 |
| 15397 | 3 | 4 | | | IV-1 | Zfp191 | 1.03 | 15493 | 3 | 4 | | IV-1 | Zfp658 | 1.06 |
| 15398 | 3 | 4 | | | IV-1 | Zfp2 | 1.40 | 15494 | 3 | 4 | | IV-1 | Zfp661 | 1.08 |
| 15399 | 3 | 4 | | | IV-1 | Zfp202 | 1.36 | 15495 | 3 | 4 | | IV-1 | Zfp663 | 1.19 |
| 15400 | 3 | 4 | | | IV-1 | Zfp207 | 1.06 | 15496 | 3 | 4 | | IV-1 | Zfp668 | 1.08 |
| 15401 | 3 | 4 | | | IV-1 | Zfp212 | 1.11 | 15497 | 3 | 4 | | IV-1 | Zfp677 | 1.03 |
| 15402 | 3 | 4 | | | IV-1 | Zfp219 | 1.03 | 15498 | 3 | 4 | | IV-1 | Zfp687 | 1.29 |
| 15403 | 3 | 4 | | | IV-1 | Zfp236 | 1.04 | 15499 | 3 | 4 | | IV-1 | Zfp689 | 1.34 |
| 15404 | 3 | 4 | | | IV-1 | Zfp248 | 1.19 | 15500 | 3 | 4 | | IV-1 | Zfp69 | 1.39 |
| 15405 | 3 | 4 | | | IV-1 | Zfp251 | 1.03 | 15501 | 3 | 4 | | IV-1 | Zfp697 | 1.23 |
| 15406 | 3 | 4 | | | IV-1 | Zfp26 | 1.13 | 15502 | 3 | 4 | | IV-1 | Zfp703 | 1.09 |
| 15407 | 3 | 4 | | | IV-1 | Zfp263 | 1.21 | 15503 | 3 | 4 | | IV-1 | Zfp704 | 1.04 |
| 15408 | 3 | 4 | | | IV-1 | Zfp27 | 1.10 | 15504 | 3 | 4 | | IV-1 | Zfp707 | 1.17 |
| 15409 | 3 | 4 | | | IV-1 | Zfp273 | 1.02 | 15505 | 3 | 4 | | IV-1 | Zfp712 | 1.18 |
| 15410 | 3 | 4 | | | IV-1 | Zfp277 | 1.35 | 15506 | 3 | 4 | | IV-1 | Zfp715 | 1.24 |
| 15411 | 3 | 4 | | | IV-1 | Zfp28 | 1.28 | 15507 | 3 | 4 | | IV-1 | Zfp738 | 1.00 |
| 15412 | 3 | 4 | | | IV-1 | Zfp280d | 1.32 | 15508 | 3 | 4 | | IV-1 | Zfp74 | 1.19 |
| 15413 | 3 | 4 | | | IV-1 | Zfp281 | 1.04 | 15509 | 3 | 4 | | IV-1 | Zfp740 | 1.11 |
| 15414 | 3 | 4 | | | IV-1 | Zfp282 | 1.03 | 15510 | 3 | 4 | | IV-1 | Zfp746 | 1.23 |
| 15415 | 3 | 4 | | | IV-1 | Zfp286 | 1.33 | 15511 | 3 | 4 | | IV-1 | Zfp763 | 1.10 |
| 15416 | 3 | 4 | | | IV-1 | Zfp287 | 1.27 | 15512 | 3 | 4 | | IV-1 | Zfp764 | 1.09 |
| 15417 | 3 | 4 | | | IV-1 | Zfp292 | 1.03 | 15513 | 3 | 4 | | IV-1 | Zfp768 | 1.10 |
| 15418 | 3 | 4 | | | IV-1 | Zfp3 | 1.15 | 15514 | 3 | 4 | | IV-1 | Zfp770 | 1.00 |
| 15419 | 3 | 4 | | | IV-1 | Zfp30 | 1.03 | 15515 | 3 | 4 | | IV-1 | Zfp773 | 1.08 |
| 15420 | 3 | 4 | | | IV-1 | Zfp300 | 1.22 | 15516 | 3 | 4 | | IV-1 | Zfp775 | 1.27 |
| 15421 | 3 | 4 | | | IV-1 | Zfp316 | 1.44 | 15517 | 3 | 4 | | IV-1 | Zfp781 | 1.11 |
| 15422 | 3 | 4 | | | IV-1 | Zfp318 | 1.18 | 15518 | 3 | 4 | | IV-1 | Zfp783 | 1.25 |
| 15423 | 3 | 4 | | | IV-1 | Zfp319 | 1.03 | 15519 | 3 | 4 | | IV-1 | Zfp784 | 1.36 |
| 15424 | 3 | 4 | | | IV-1 | Zfp326 | 1.33 | 15520 | 3 | 4 | | IV-1 | Zfp786 | 1.47 |
| 15425 | 3 | 4 | | | IV-1 | Zfp329 | 1.03 | 15521 | 3 | 4 | | IV-1 | Zfp787 | 1.12 |
| 15426 | 3 | 4 | | | IV-1 | Zfp330 | 1.15 | 15522 | 3 | 4 | | IV-1 | Zfp788 | 1.27 |
| 15427 | 3 | 4 | | | IV-1 | Zfp334 | 1.20 | 15523 | 3 | 4 | | IV-1 | Zfp791 | 1.17 |
| 15428 | 3 | 4 | | | IV-1 | Zfp346 | 1.14 | 15524 | 3 | 4 | | IV-1 | Zfp799 | 1.21 |
| 15429 | 3 | 4 | | | IV-1 | Zfp354a | 1.37 | 15525 | 3 | 4 | | IV-1 | Zfp81 | 1.19 |
| 15430 | 3 | 4 | | | IV-1 | Zfp354b | 1.08 | 15526 | 3 | 4 | | IV-1 | Zfp821 | 1.34 |
| 15431 | 3 | 4 | | | IV-1 | Zfp354c | 1.32 | 15527 | 3 | 4 | | IV-1 | Zfp825 | 1.06 |
| 15432 | 3 | 4 | | | IV-1 | Zfp358 | 1.20 | 15528 | 3 | 4 | | IV-1 | Zfp827 | 1.21 |
| 15433 | 3 | 4 | | | IV-1 | Zfp36 | 1.15 | 15529 | 3 | 4 | | IV-1 | Zfp839 | 1.13 |
| 15434 | 3 | 4 | | | IV-1 | Zfp37 | 1.29 | 15530 | 3 | 4 | | IV-1 | Zfp846 | 1.26 |
| 15435 | 3 | 4 | | | IV-1 | Zfp383 | 1.20 | 15531 | 3 | 4 | | IV-1 | Zfp85 | 1.12 |
| 15436 | 3 | 4 | | | IV-1 | Zfp384 | 1.08 | 15532 | 3 | 4 | | IV-1 | Zfp862-ps | 1.08 |
| 15437 | 3 | 4 | | | IV-1 | Zfp385a | 1.11 | 15533 | 3 | 4 | | IV-1 | Zfp865 | 1.21 |
| 15438 | 3 | 4 | | | IV-1 | Zfp386 | 1.16 | 15534 | 3 | 4 | | IV-1 | Zfp867 | 1.28 |
| 15439 | 3 | 4 | | | IV-1 | Zfp398 | 1.16 | 15535 | 3 | 4 | | IV-1 | Zfp873 | 1.18 |
| 15440 | 3 | 4 | | | IV-1 | Zfp40 | 1.21 | 15536 | 3 | 4 | | IV-1 | Zfp879 | 1.08 |
| 15441 | 3 | 4 | | | IV-1 | Zfp408 | 1.24 | 15537 | 3 | 4 | | IV-1 | Zfp9 | 1.23 |
| 15442 | 3 | 4 | | | IV-1 | Zfp41 | 1.12 | 15538 | 3 | 4 | | IV-1 | Zfp93 | 1.11 |
| 15443 | 3 | 4 | | | IV-1 | Zfp414 | 1.38 | 15539 | 3 | 4 | | IV-1 | Zfp94 | 1.33 |
| 15444 | 3 | 4 | | | IV-1 | Zfp422 | 1.08 | 15540 | 3 | 4 | | IV-1 | Zfp940 | 1.44 |
| 15445 | 3 | 4 | | | IV-1 | Zfp423 | 1.34 | 15541 | 3 | 4 | | IV-1 | Zfp944 | 1.20 |
| 15446 | 3 | 4 | | | IV-1 | Zfp426 | 1.03 | 15542 | 3 | 4 | | IV-1 | Zfp945 | 1.33 |
| 15447 | 3 | 4 | | | IV-1 | Zfp428 | 1.33 | 15543 | 3 | 4 | | IV-1 | Zfp947 | 1.06 |
| 15448 | 3 | 4 | | | IV-1 | Zfp433 | 1.42 | 15544 | 3 | 4 | | IV-1 | Zfp948 | 1.07 |
| 15449 | 3 | 4 | | | IV-1 | Zfp438 | 1.16 | 15545 | 3 | 4 | | IV-1 | Zfp949 | 1.24 |
| 15450 | 3 | 4 | | | IV-1 | Zfp445 | 1.10 | 15546 | 3 | 4 | | IV-1 | Zfp951 | 1.22 |
| 15451 | 3 | 4 | | | IV-1 | Zfp446 | 1.08 | 15547 | 3 | 4 | | IV-1 | Zfp952 | 1.02 |
| 15452 | 3 | 4 | | | IV-1 | Zfp454 | 1.21 | 15548 | 3 | 4 | | IV-1 | Zfp955b | 1.01 |
| 15453 | 3 | 4 | | | IV-1 | Zfp46 | 1.44 | 15549 | 3 | 4 | | IV-1 | Zfp956 | 1.39 |

Fig. 45 - 82

| | | | | | | | | | | | | | | |
|---|---|---|---|---|---|---|---|---|---|---|---|---|---|---|
| 15550 | 3 | 4 | | | IV-1 | Zfp958 | 1.04 | 15646 | 3 | | | | 1700003C15Rik | 1.00 |
| 15551 | 3 | 4 | | | IV-1 | Zfp960 | 1.11 | 15647 | 3 | | | | 1700003D09Rik | 1.00 |
| 15552 | 3 | 4 | | | IV-1 | Zfp963 | 1.08 | 15648 | 3 | | | | 1700003E24Rik | 1.00 |
| 15553 | 3 | 4 | | | IV-1 | Zfp964 | 1.28 | 15649 | 3 | | | | 1700003G13Rik | 1.00 |
| 15554 | 3 | 4 | | | IV-1 | Zfpl1 | 1.12 | 15650 | 3 | | | | 1700003G18Rik | 1.00 |
| 15555 | 3 | 4 | | | IV-1 | Zfpm2 | 1.43 | 15651 | 3 | | | | 1700003H04Rik | 1.00 |
| 15556 | 3 | 4 | | | IV-1 | Zfr | 1.25 | 15652 | 3 | | | | 1700003L19Rik | 1.00 |
| 15557 | 3 | 4 | | | IV-1 | Zfx | 1.00 | 15653 | 3 | | | | 1700003M02Rik | 1.00 |
| 15558 | 3 | 4 | | | IV-1 | Zfyve1 | 1.14 | 15654 | 3 | | | | 1700003P14Rik | 1.00 |
| 15559 | 3 | 4 | | | IV-1 | Zfyve20 | 1.12 | 15655 | 3 | | | | 1700006A11Rik | 1.00 |
| 15560 | 3 | 4 | | | IV-1 | Zfyve27 | 1.19 | 15656 | 3 | | | | 1700006E09Rik | 1.00 |
| 15561 | 3 | 4 | | | IV-1 | Zfyve28 | 1.26 | 15657 | 3 | | | | 1700006F04Rik | 1.00 |
| 15562 | 3 | 4 | | | IV-1 | Zfyve9 | 1.13 | 15658 | 3 | | | | 1700006H21Rik | 1.00 |
| 15563 | 3 | 4 | | | IV-1 | Zgrf1 | 1.22 | 15659 | 3 | | | | 1700007B14Rik | 1.00 |
| 15564 | 3 | 4 | | | IV-1 | Zhx1 | 1.03 | 15660 | 3 | | | | 1700007F19Rik | 1.00 |
| 15565 | 3 | 4 | | | IV-1 | Zhx3 | 1.09 | 15661 | 3 | | | | 1700007G11Rik | 1.00 |
| 15566 | 3 | 4 | | | IV-1 | Zic3 | 1.36 | 15662 | 3 | | | | 1700007J10Rik | 1.00 |
| 15567 | 3 | 4 | | | IV-1 | Zik1 | 1.20 | 15663 | 3 | | | | 1700007K09Rik | 1.00 |
| 15568 | 3 | 4 | | | IV-1 | Zkscan1 | 1.09 | 15664 | 3 | | | | 1700007P06Rik | 1.00 |
| 15569 | 3 | 4 | | | IV-1 | Zkscan14 | 1.21 | 15665 | 3 | | | | 1700008F21Rik | 1.00 |
| 15570 | 3 | 4 | | | IV-1 | Zkscan17 | 1.26 | 15666 | 3 | | | | 1700008I05Rik | 1.00 |
| 15571 | 3 | 4 | | | IV-1 | Zkscan4 | 1.21 | 15667 | 3 | | | | 1700008K24Rik | 1.00 |
| 15572 | 3 | 4 | | | IV-1 | Zkscan5 | 1.33 | 15668 | 3 | | | | 1700008O03Rik | 1.00 |
| 15573 | 3 | 4 | | | IV-1 | Zkscan6 | 1.28 | 15669 | 3 | | | | 1700008P02Rik | 1.00 |
| 15574 | 3 | 4 | | | IV-1 | Zkscan7 | 1.15 | 15670 | 3 | | | | 1700009C05Rik | 1.00 |
| 15575 | 3 | 4 | | | IV-1 | Zkscan8 | 1.12 | 15671 | 3 | | | | 1700009J07Rik | 1.00 |
| 15576 | 3 | 4 | | | IV-1 | Zmat1 | 1.13 | 15672 | 3 | | | | 1700009N14Rik | 1.00 |
| 15577 | 3 | 4 | | | IV-1 | Zmat3 | 1.44 | 15673 | 3 | | | | 1700010B08Rik | 1.00 |
| 15578 | 3 | 4 | | | IV-1 | Zmat4 | 1.44 | 15674 | 3 | | | | 1700010D01Rik | 1.00 |
| 15579 | 3 | 4 | | | IV-1 | Zmiz1 | 1.40 | 15675 | 3 | | | | 1700010I02Rik | 1.00 |
| 15580 | 3 | 4 | | | IV-1 | Zmiz2 | 1.32 | 15676 | 3 | | | | 1700010I14Rik | 1.00 |
| 15581 | 3 | 4 | | | IV-1 | Zmpste24 | 1.02 | 15677 | 3 | | | | 1700010J16Rik | 1.00 |
| 15582 | 3 | 4 | | | IV-1 | Zmym2 | 1.18 | 15678 | 3 | | | | 1700010K23Rik | 1.00 |
| 15583 | 3 | 4 | | | IV-1 | Zmym3 | 1.25 | 15679 | 3 | | | | 1700011A15Rik | 1.00 |
| 15584 | 3 | 4 | | | IV-1 | Zmym4 | 1.20 | 15680 | 3 | | | | 1700011B04Rik | 1.00 |
| 15585 | 3 | 4 | | | IV-1 | Zmym5 | 1.21 | 15681 | 3 | | | | 1700011E24Rik | 1.00 |
| 15586 | 3 | 4 | | | IV-1 | Zmym6 | 1.18 | 15682 | 3 | | | | 1700011I03Rik | 1.00 |
| 15587 | 3 | 4 | | | IV-1 | Zmynd11 | 1.19 | 15683 | 3 | | | | 1700011L22Rik | 1.00 |
| 15588 | 3 | 4 | | | IV-1 | Znfx1 | 1.21 | 15684 | 3 | | | | 1700011M02Rik | 1.00 |
| 15589 | 3 | 4 | | | IV-1 | Znhit3 | 1.27 | 15685 | 3 | | | | 1700012A03Rik | 1.00 |
| 15590 | 3 | 4 | | | IV-1 | Znhit6 | 1.14 | 15686 | 3 | | | | 1700012B07Rik | 1.00 |
| 15591 | 3 | 4 | | | IV-1 | Znrf1 | 1.40 | 15687 | 3 | | | | 1700012B09Rik | 1.00 |
| 15592 | 3 | 4 | | | IV-1 | Znrf2 | 1.00 | 15688 | 3 | | | | 1700012I11Rik | 1.00 |
| 15593 | 3 | 4 | | | IV-1 | Znrf3 | 1.09 | 15689 | 3 | | | | 1700012L04Rik | 1.00 |
| 15594 | 3 | 4 | | | IV-1 | Zpr1 | 1.06 | 15690 | 3 | | | | 1700012P22Rik | 1.00 |
| 15595 | 3 | 4 | | | IV-1 | Zranb1 | 1.32 | 15691 | 3 | | | | 1700013D24Rik | 1.00 |
| 15596 | 3 | 4 | | | IV-1 | Zranb2 | 1.04 | 15692 | 3 | | | | 1700013F07Rik | 1.00 |
| 15597 | 3 | 4 | | | IV-1 | Zrsr1 | 1.11 | 15693 | 3 | | | | 1700013G24Rik | 1.00 |
| 15598 | 3 | 4 | | | IV-1 | Zscan12 | 1.06 | 15694 | 3 | | | | 1700013H16Rik | 1.00 |
| 15599 | 3 | 4 | | | IV-1 | Zscan18 | 1.28 | 15695 | 3 | | | | 1700015F17Rik | 1.00 |
| 15600 | 3 | 4 | | | IV-1 | Zscan2 | 1.35 | 15696 | 3 | | | | 1700015G11Rik | 1.00 |
| 15601 | 3 | 4 | | | IV-1 | Zscan21 | 1.11 | 15697 | 3 | | | | 1700016C15Rik | 1.00 |
| 15602 | 3 | 4 | | | IV-1 | Zswim5 | 1.18 | 15698 | 3 | | | | 1700016D06Rik | 1.00 |
| 15603 | 3 | 4 | | | IV-1 | Zswim6 | 1.12 | 15699 | 3 | | | | 1700016G22Rik | 1.00 |
| 15604 | 3 | 4 | | | IV-1 | Zswim7 | 1.19 | 15700 | 3 | | | | 1700016H13Rik | 1.00 |
| 15605 | 3 | 4 | | | IV-1 | Zswim8 | 1.29 | 15701 | 3 | | | | 1700016L04Rik | 1.00 |
| 15606 | 3 | 4 | | | IV-1 | Zwint | 1.23 | 15702 | 3 | | | | 1700016L21Rik | 1.00 |
| 15607 | 3 | 4 | | | IV-1 | Zxda | 1.02 | 15703 | 3 | | | | 1700016P04Rik | 1.00 |
| 15608 | 3 | 4 | | | IV-1 | Zxdb | 1.21 | 15704 | 3 | | | | 1700017D01Rik | 1.00 |
| 15609 | 3 | 4 | | | IV-1 | Zxdc | 1.26 | 15705 | 3 | | | | 1700017G19Rik | 1.00 |
| 15610 | 3 | 4 | | | IV-1 | Zyg11b | 1.23 | 15706 | 3 | | | | 1700017J07Rik | 1.00 |
| 15611 | 3 | 4 | | | IV-1 | Zzef1 | 1.11 | 15707 | 3 | | | | 1700017N19Rik | 1.00 |
| 15612 | 3 | 4 | | | IV-1 | Zzz3 | 1.16 | 15708 | 3 | | | | 1700018A04Rik | 1.00 |
| 15613 | 3 | | | | | 0610031O16Rik | 1.00 | 15709 | 3 | | | | 1700018B08Rik | 1.00 |
| 15614 | 3 | | | | | 0610039K10Rik | 1.00 | 15710 | 3 | | | | 1700018B24Rik | 1.00 |
| 15615 | 3 | | | | | 0610040F04Rik | 1.00 | 15711 | 3 | | | | 1700018C11Rik | 1.00 |
| 15616 | 3 | | | | | 0610043K17Rik | 1.00 | 15712 | 3 | | | | 1700018F24Rik | 1.00 |
| 15617 | 3 | | | | | 1110020A21Rik | 1.00 | 15713 | 3 | | | | 1700018G05Rik | 1.00 |
| 15618 | 3 | | | | | 1110025L11Rik | 1.00 | 15714 | 3 | | | | 1700019A02Rik | 1.00 |
| 15619 | 3 | | | | | 1110028F11Rik | 1.00 | 15715 | 3 | | | | 1700019B03Rik | 1.00 |
| 15620 | 3 | | | | | 1110028F18Rik | 1.00 | 15716 | 3 | | | | 1700019B21Rik | 1.00 |
| 15621 | 3 | | | | | 1110036E04Rik | 1.00 | 15717 | 3 | | | | 1700019E08Rik | 1.00 |
| 15622 | 3 | | | | | 1110046J04Rik | 1.00 | 15718 | 3 | | | | 1700019G24Rik | 1.00 |
| 15623 | 3 | | | | | 1190003K10Rik | 1.00 | 15719 | 3 | | | | 1700019L03Rik | 1.00 |
| 15624 | 3 | | | | | 1500012K07Rik | 1.00 | 15720 | 3 | | | | 1700019M22Rik | 1.00 |
| 15625 | 3 | | | | | 1500015L24Rik | 1.00 | 15721 | 3 | | | | 1700019N19Rik | 1.00 |
| 15626 | 3 | | | | | 1600002D24Rik | 1.00 | 15722 | 3 | | | | 1700019O17Rik | 1.00 |
| 15627 | 3 | | | | | 1600010M07Rik | 1.00 | 15723 | 3 | | | | 1700020A23Rik | 1.00 |
| 15628 | 3 | | | | | 1600014C23Rik | 1.00 | 15724 | 3 | | | | 1700020G17Rik | 1.00 |
| 15629 | 3 | | | | | 1600014K23Rik | 1.00 | 15725 | 3 | | | | 1700020M21Rik | 1.00 |
| 15630 | 3 | | | | | 1600015I10Rik | 1.00 | 15726 | 3 | | | | 1700020N01Rik | 1.00 |
| 15631 | 3 | | | | | 1600016N20Rik | 1.00 | 15727 | 3 | | | | 1700020N15Rik | 1.00 |
| 15632 | 3 | | | | | 1600019K03Rik | 1.00 | 15728 | 3 | | | | 1700020N18Rik | 1.00 |
| 15633 | 3 | | | | | 1600025M17Rik | 1.00 | 15729 | 3 | | | | 1700021F07Rik | 1.00 |
| 15634 | 3 | | | | | 1600027J07Rik | 1.00 | 15730 | 3 | | | | 1700021N21Rik | 1.00 |
| 15635 | 3 | | | | | 1600029I14Rik | 1.00 | 15731 | 3 | | | | 1700022A21Rik | 1.00 |
| 15636 | 3 | | | | | 1700001C19Rik | 1.00 | 15732 | 3 | | | | 1700022A22Rik | 1.00 |
| 15637 | 3 | | | | | 1700001D01Rik | 1.00 | 15733 | 3 | | | | 1700022E09Rik | 1.00 |
| 15638 | 3 | | | | | 1700001F09Rik | 1.00 | 15734 | 3 | | | | 1700022H16Rik | 1.00 |
| 15639 | 3 | | | | | 1700001G11Rik | 1.00 | 15735 | 3 | | | | 1700022I11Rik | 1.00 |
| 15640 | 3 | | | | | 1700001J03Rik | 1.00 | 15736 | 3 | | | | 1700023C21Rik | 1.00 |
| 15641 | 3 | | | | | 1700001K19Rik | 1.00 | 15737 | 3 | | | | 1700023E05Rik | 1.00 |
| 15642 | 3 | | | | | 1700001K23Rik | 1.00 | 15738 | 3 | | | | 1700023F02Rik | 1.00 |
| 15643 | 3 | | | | | 1700001L19Rik | 1.00 | 15739 | 3 | | | | 1700023F06Rik | 1.00 |
| 15644 | 3 | | | | | 1700001O22Rik | 1.00 | 15740 | 3 | | | | 1700024B18Rik | 1.00 |
| 15645 | 3 | | | | | 1700001P01Rik | 1.00 | 15741 | 3 | | | | 1700024G13Rik | 1.00 |

Fig. 45 - 83

| | | | | | | | | | | | | | |
|---|---|---|---|---|---|---|---|---|---|---|---|---|---|
| 15742 | 3 | | | | | 1700024P04Rik | 1.00 | 15838 | 3 | | | 1700065J11Rik | 1.00 |
| 15743 | 3 | | | | | 1700024P16Rik | 1.00 | 15839 | 3 | | | 1700065J18Rik | 1.00 |
| 15744 | 3 | | | | | 1700025B11Rik | 1.00 | 15840 | 3 | | | 1700065L07Rik | 1.00 |
| 15745 | 3 | | | | | 1700025C18Rik | 1.00 | 15841 | 3 | | | 1700065O20Rik | 1.00 |
| 15746 | 3 | | | | | 1700025F22Rik | 1.00 | 15842 | 3 | | | 1700066B17Rik | 1.00 |
| 15747 | 3 | | | | | 1700025F24Rik | 1.00 | 15843 | 3 | | | 1700066B19Rik | 1.00 |
| 15748 | 3 | | | | | 1700025K24Rik | 1.00 | 15844 | 3 | | | 1700066N21Rik | 1.00 |
| 15749 | 3 | | | | | 1700025M24Rik | 1.00 | 15845 | 3 | | | 1700066O22Rik | 1.00 |
| 15750 | 3 | | | | | 1700025N23Rik | 1.00 | 15846 | 3 | | | 1700067G17Rik | 1.00 |
| 15751 | 3 | | | | | 1700026D08Rik | 1.00 | 15847 | 3 | | | 1700067K01Rik | 1.00 |
| 15752 | 3 | | | | | 1700026D11Rik | 1.00 | 15848 | 3 | | | 1700067P10Rik | 1.00 |
| 15753 | 3 | | | | | 1700026F02Rik | 1.00 | 15849 | 3 | | | 1700069L16Rik | 1.00 |
| 15754 | 3 | | | | | 1700026L06Rik | 1.00 | 15850 | 3 | | | 1700069P05Rik | 1.00 |
| 15755 | 3 | | | | | 1700027A15Rik | 1.00 | 15851 | 3 | | | 1700071K01Rik | 1.00 |
| 15756 | 3 | | | | | 1700027F09Rik | 1.00 | 15852 | 3 | | | 1700071M16Rik | 1.00 |
| 15757 | 3 | | | | | 1700027H10Rik | 1.00 | 15853 | 3 | | | 1700072B07Rik | 1.00 |
| 15758 | 3 | | | | | 1700027I24Rik | 1.00 | 15854 | 3 | | | 1700072O05Rik | 1.00 |
| 15759 | 3 | | | | | 1700027J07Rik | 1.00 | 15855 | 3 | | | 1700073E17Rik | 1.00 |
| 15760 | 3 | | | | | 1700028B04Rik | 1.00 | 15856 | 3 | | | 1700074H08Rik | 1.00 |
| 15761 | 3 | | | | | 1700028D13Rik | 1.00 | 15857 | 3 | | | 1700074P13Rik | 1.00 |
| 15762 | 3 | | | | | 1700028E10Rik | 1.00 | 15858 | 3 | | | 1700080E11Rik | 1.00 |
| 15763 | 3 | | | | | 1700028I16Rik | 1.00 | 15859 | 3 | | | 1700080N15Rik | 1.00 |
| 15764 | 3 | | | | | 1700028J19Rik | 1.00 | 15860 | 3 | | | 1700080O16Rik | 1.00 |
| 15765 | 3 | | | | | 1700028M03Rik | 1.00 | 15861 | 3 | | | 1700081H04Rik | 1.00 |
| 15766 | 3 | | | | | 1700028P14Rik | 1.00 | 15862 | 3 | | | 1700084F23Rik | 1.00 |
| 15767 | 3 | | | | | 1700028P15Rik | 1.00 | 15863 | 3 | | | 1700084J12Rik | 1.00 |
| 15768 | 3 | | | | | 1700029B22Rik | 1.00 | 15864 | 3 | | | 1700085C21Rik | 1.00 |
| 15769 | 3 | | | | | 1700029F12Rik | 1.00 | 15865 | 3 | | | 1700088E04Rik | 1.00 |
| 15770 | 3 | | | | | 1700029H14Rik | 1.00 | 15866 | 3 | | | 1700091H14Rik | 1.00 |
| 15771 | 3 | | | | | 1700029I15Rik | 1.00 | 15867 | 3 | | | 1700092C02Rik | 1.00 |
| 15772 | 3 | | | | | 1700029J03Rik | 1.00 | 15868 | 3 | | | 1700092C10Rik | 1.00 |
| 15773 | 3 | | | | | 1700029M20Rik | 1.00 | 15869 | 3 | | | 1700092E19Rik | 1.00 |
| 15774 | 3 | | | | | 1700029N11Rik | 1.00 | 15870 | 3 | | | 1700092K14Rik | 1.00 |
| 15775 | 3 | | | | | 1700029P11Rik | 1.00 | 15871 | 3 | | | 1700092M07Rik | 1.00 |
| 15776 | 3 | | | | | 1700030A11Rik | 1.00 | 15872 | 3 | | | 1700094J05Rik | 1.00 |
| 15777 | 3 | | | | | 1700030F04Rik | 1.00 | 15873 | 3 | | | 1700094M24Rik | 1.00 |
| 15778 | 3 | | | | | 1700030F18Rik | 1.00 | 15874 | 3 | | | 1700095A21Rik | 1.00 |
| 15779 | 3 | | | | | 1700030L20Rik | 1.00 | 15875 | 3 | | | 1700095B10Rik | 1.00 |
| 15780 | 3 | | | | | 1700030M09Rik | 1.00 | 15876 | 3 | | | 1700096J18Rik | 1.00 |
| 15781 | 3 | | | | | 1700030N03Rik | 1.00 | 15877 | 3 | | | 1700097N02Rik | 1.00 |
| 15782 | 3 | | | | | 1700030O20Rik | 1.00 | 15878 | 3 | | | 1700100L14Rik | 1.00 |
| 15783 | 3 | | | | | 1700031A10Rik | 1.00 | 15879 | 3 | | | 1700101E01Rik | 1.00 |
| 15784 | 3 | | | | | 1700031F05Rik | 1.00 | 15880 | 3 | | | 1700101I11Rik | 1.00 |
| 15785 | 3 | | | | | 1700031M16Rik | 1.00 | 15881 | 3 | | | 1700101O22Rik | 1.00 |
| 15786 | 3 | | | | | 1700031P21Rik | 1.00 | 15882 | 3 | | | 1700102H20Rik | 1.00 |
| 15787 | 3 | | | | | 1700034E13Rik | 1.00 | 15883 | 3 | | | 1700104L18Rik | 1.00 |
| 15788 | 3 | | | | | 1700034F02Rik | 1.00 | 15884 | 3 | | | 1700106J16Rik | 1.00 |
| 15789 | 3 | | | | | 1700034G24Rik | 1.00 | 15885 | 3 | | | 1700108F19Rik | 1.00 |
| 15790 | 3 | | | | | 1700034H15Rik | 1.00 | 15886 | 3 | | | 1700108J01Rik | 1.00 |
| 15791 | 3 | | | | | 1700034I23Rik | 1.00 | 15887 | 3 | | | 1700109G14Rik | 1.00 |
| 15792 | 3 | | | | | 1700034J05Rik | 1.00 | 15888 | 3 | | | 1700109G15Rik | 1.00 |
| 15793 | 3 | | | | | 1700034K08Rik | 1.00 | 15889 | 3 | | | 1700109H08Rik | 1.00 |
| 15794 | 3 | | | | | 1700034O15Rik | 1.00 | 15890 | 3 | | | 1700109I08Rik | 1.00 |
| 15795 | 3 | | | | | 1700034P13Rik | 1.00 | 15891 | 3 | | | 1700110C19Rik | 1.00 |
| 15796 | 3 | | | | | 1700036G14Rik | 1.00 | 15892 | 3 | | | 1700110I01Rik | 1.00 |
| 15797 | 3 | | | | | 1700039E15Rik | 1.00 | 15893 | 3 | | | 1700110K17Rik | 1.00 |
| 15798 | 3 | | | | | 1700039E22Rik | 1.00 | 15894 | 3 | | | 1700111N16Rik | 1.00 |
| 15799 | 3 | | | | | 1700040L02Rik | 1.00 | 15895 | 3 | | | 1700112E06Rik | 1.00 |
| 15800 | 3 | | | | | 1700041C23Rik | 1.00 | 15896 | 3 | | | 1700112H15Rik | 1.00 |
| 15801 | 3 | | | | | 1700041M19Rik | 1.00 | 15897 | 3 | | | 1700112I05Rik | 1.00 |
| 15802 | 3 | | | | | 1700042B14Rik | 1.00 | 15898 | 3 | | | 1700113H08Rik | 1.00 |
| 15803 | 3 | | | | | 1700042G07Rik | 1.00 | 15899 | 3 | | | 1700119H24Rik | 1.00 |
| 15804 | 3 | | | | | 1700042G15Rik | 1.00 | 15900 | 3 | | | 1700120C14Rik | 1.00 |
| 15805 | 3 | | | | | 1700042O10Rik | 1.00 | 15901 | 3 | | | 1700120E14Rik | 1.00 |
| 15806 | 3 | | | | | 1700044C05Rik | 1.00 | 15902 | 3 | | | 1700120G07Rik | 1.00 |
| 15807 | 3 | | | | | 1700044K03Rik | 1.00 | 15903 | 3 | | | 1700120K04Rik | 1.00 |
| 15808 | 3 | | | | | 1700045H11Rik | 1.00 | 15904 | 3 | | | 1700121L16Rik | 1.00 |
| 15809 | 3 | | | | | 1700046C09Rik | 1.00 | 15905 | 3 | | | 1700121N20Rik | 1.00 |
| 15810 | 3 | | | | | 1700047A11Rik | 1.00 | 15906 | 3 | | | 1700122O11Rik | 1.00 |
| 15811 | 3 | | | | | 1700047E10Rik | 1.00 | 15907 | 3 | | | 1700123I01Rik | 1.00 |
| 15812 | 3 | | | | | 1700047G03Rik | 1.00 | 15908 | 3 | | | 1700123K08Rik | 1.00 |
| 15813 | 3 | | | | | 1700047L14Rik | 1.00 | 15909 | 3 | | | 1700123L14Rik | 1.00 |
| 15814 | 3 | | | | | 1700049E15Rik | 1.00 | 15910 | 3 | | | 1700123O12Rik | 1.00 |
| 15815 | 3 | | | | | 1700049E22Rik | 1.00 | 15911 | 3 | | | 1700123O21Rik | 1.00 |
| 15816 | 3 | | | | | 1700049L16Rik | 1.00 | 15912 | 3 | | | 1700125G02Rik | 1.00 |
| 15817 | 3 | | | | | 1700051A21Rik | 1.00 | 15913 | 3 | | | 1700125G22Rik | 1.00 |
| 15818 | 3 | | | | | 1700052I22Rik | 1.00 | 15914 | 3 | | | 1700125H03Rik | 1.00 |
| 15819 | 3 | | | | | 1700054A03Rik | 1.00 | 15915 | 3 | | | 1700125H20Rik | 1.00 |
| 15820 | 3 | | | | | 1700054K19Rik | 1.00 | 15916 | 3 | | | 1700126H18Rik | 1.00 |
| 15821 | 3 | | | | | 1700054M17Rik | 1.00 | 15917 | 3 | | | 1700128A07Rik | 1.00 |
| 15822 | 3 | | | | | 1700054O13Rik | 1.00 | 15918 | 3 | | | 1700128F08Rik | 1.00 |
| 15823 | 3 | | | | | 1700055C04Rik | 1.00 | 15919 | 3 | | | 1700129C05Rik | 1.00 |
| 15824 | 3 | | | | | 1700057G04Rik | 1.00 | 15920 | 3 | | | 1810006J02Rik | 1.00 |
| 15825 | 3 | | | | | 1700057H15Rik | 1.00 | 15921 | 3 | | | 1810007C17Rik | 1.00 |
| 15826 | 3 | | | | | 1700060C16Rik | 1.00 | 15922 | 3 | | | 1810007D17Rik | 1.00 |
| 15827 | 3 | | | | | 1700060C20Rik | 1.00 | 15923 | 3 | | | 1810009J06Rik | 1.00 |
| 15828 | 3 | | | | | 1700061F12Rik | 1.00 | 15924 | 3 | | | 1810010D01Rik | 1.00 |
| 15829 | 3 | | | | | 1700061G19Rik | 1.00 | 15925 | 3 | | | 1810011H11Rik | 1.00 |
| 15830 | 3 | | | | | 1700061J17Rik | 1.00 | 15926 | 3 | | | 1810012K16Rik | 1.00 |
| 15831 | 3 | | | | | 1700063A18Rik | 1.00 | 15927 | 3 | | | 1810013A23Rik | 1.00 |
| 15832 | 3 | | | | | 1700063D05Rik | 1.00 | 15928 | 3 | | | 1810018F18Rik | 1.00 |
| 15833 | 3 | | | | | 1700063O14Rik | 1.00 | 15929 | 3 | | | 1810020O05Rik | 1.00 |
| 15834 | 3 | | | | | 1700064J06Rik | 1.00 | 15930 | 3 | | | 1810021B22Rik | 1.00 |
| 15835 | 3 | | | | | 1700064M15Rik | 1.00 | 15931 | 3 | | | 1810024B03Rik | 1.00 |
| 15836 | 3 | | | | | 1700065D16Rik | 1.00 | 15932 | 3 | | | 1810046K07Rik | 1.00 |
| 15837 | 3 | | | | | 1700065I16Rik | 1.00 | 15933 | 3 | | | 1810064F22Rik | 1.00 |

Fig. 45 - 84

| | | | | | | | | | | | | | | |
|---|---|---|---|---|---|---|---|---|---|---|---|---|---|---|
| 15934 | 3 | | | | | | | 1810065E05Rik | 1.00 | 16030 | 3 | | | 4430402I18Rik | 1.00 |
| 15935 | 3 | | | | | | | 2010001E11Rik | 1.00 | 16031 | 3 | | | 4632428C04Rik | 1.00 |
| 15936 | 3 | | | | | | | 2010009K17Rik | 1.00 | 16032 | 3 | | | 4732416N19Rik | 1.00 |
| 15937 | 3 | | | | | | | 2010016I18Rik | 1.00 | 16033 | 3 | | | 4732456N10Rik | 1.00 |
| 15938 | 3 | | | | | | | 2010106C02Rik | 1.00 | 16034 | 3 | | | 4732490B19Rik | 1.00 |
| 15939 | 3 | | | | | | | 2010106E10Rik | 1.00 | 16035 | 3 | | | 4833419F23Rik | 1.00 |
| 15940 | 3 | | | | | | | 2010107G12Rik | 1.00 | 16036 | 3 | | | 4833427F10Rik | 1.00 |
| 15941 | 3 | | | | | | | 2010109A12Rik | 1.00 | 16037 | 3 | | | 4833427G06Rik | 1.00 |
| 15942 | 3 | | | | | | | 2010308F09Rik | 1.00 | 16038 | 3 | | | 4833428L15Rik | 1.00 |
| 15943 | 3 | | | | | | | 2010310C07Rik | 1.00 | 16039 | 3 | | | 4921501E09Rik | 1.00 |
| 15944 | 3 | | | | | | | 2200002J24Rik | 1.00 | 16040 | 3 | | | 4921504E06Rik | 1.00 |
| 15945 | 3 | | | | | | | 2210010C04Rik | 1.00 | 16041 | 3 | | | 4921506M07Rik | 1.00 |
| 15946 | 3 | | | | | | | 2210011C24Rik | 1.00 | 16042 | 3 | | | 4921507L20Rik | 1.00 |
| 15947 | 3 | | | | | | | 2210019I11Rik | 1.00 | 16043 | 3 | | | 4921508D12Rik | 1.00 |
| 15948 | 3 | | | | | | | 2210407C18Rik | 1.00 | 16044 | 3 | | | 4921509C19Rik | 1.00 |
| 15949 | 3 | | | | | | | 2210408F21Rik | 1.00 | 16045 | 3 | | | 4921509O07Rik | 1.00 |
| 15950 | 3 | | | | | | | 2210409D07Rik | 1.00 | 16046 | 3 | | | 4921511C10Rik | 1.00 |
| 15951 | 3 | | | | | | | 2210409E12Rik | 1.00 | 16047 | 3 | | | 4921511C20Rik | 1.00 |
| 15952 | 3 | | | | | | | 2210414B05Rik | 1.00 | 16048 | 3 | | | 4921511H03Rik | 1.00 |
| 15953 | 3 | | | | | | | 2210416O15Rik | 1.00 | 16049 | 3 | | | 4921511I17Rik | 1.00 |
| 15954 | 3 | | | | | | | 2210417A02Rik | 1.00 | 16050 | 3 | | | 4921511M17Rik | 1.00 |
| 15955 | 3 | | | | | | | 2210420H20Rik | 1.00 | 16051 | 3 | | | 4921513I03Rik | 1.00 |
| 15956 | 3 | | | | | | | 2300003K06Rik | 1.00 | 16052 | 3 | | | 4921515E04Rik | 1.00 |
| 15957 | 3 | | | | | | | 2300005B03Rik | 1.00 | 16053 | 3 | | | 4921517D22Rik | 1.00 |
| 15958 | 3 | | | | | | | 2310001K24Rik | 1.00 | 16054 | 3 | | | 4921524L21Rik | 1.00 |
| 15959 | 3 | | | | | | | 2310002F09Rik | 1.00 | 16055 | 3 | | | 4921525O09Rik | 1.00 |
| 15960 | 3 | | | | | | | 2310005A03Rik | 1.00 | 16056 | 3 | | | 4921529L05Rik | 1.00 |
| 15961 | 3 | | | | | | | 2310005E17Rik | 1.00 | 16057 | 3 | | | 4921530L21Rik | 1.00 |
| 15962 | 3 | | | | | | | 2310005G13Rik | 1.00 | 16058 | 3 | | | 4921531P14Rik | 1.00 |
| 15963 | 3 | | | | | | | 2310007J24Rik | 1.00 | 16059 | 3 | | | 4921534H16Rik | 1.00 |
| 15964 | 3 | | | | | | | 2310008N11Rik | 1.00 | 16060 | 3 | | | 4921536K21Rik | 1.00 |
| 15965 | 3 | | | | | | | 2310015D24Rik | 1.00 | 16061 | 3 | | | 4921539E11Rik | 1.00 |
| 15966 | 3 | | | | | | | 2310016D03Rik | 1.00 | 16062 | 3 | | | 4922502D21Rik | 1.00 |
| 15967 | 3 | | | | | | | 2310020H05Rik | 1.00 | 16063 | 3 | | | 4922502H24Rik | 1.00 |
| 15968 | 3 | | | | | | | 2310030A07Rik | 1.00 | 16064 | 3 | | | 4922502N22Rik | 1.00 |
| 15969 | 3 | | | | | | | 2310034O05Rik | 1.00 | 16065 | 3 | | | 4930401C15Rik | 1.00 |
| 15970 | 3 | | | | | | | 2310039L15Rik | 1.00 | 16066 | 3 | | | 4930401O10Rik | 1.00 |
| 15971 | 3 | | | | | | | 2310043O21Rik | 1.00 | 16067 | 3 | | | 4930401O12Rik | 1.00 |
| 15972 | 3 | | | | | | | 2310057J18Rik | 1.00 | 16068 | 3 | | | 4930402F06Rik | 1.00 |
| 15973 | 3 | | | | | | | 2310061N02Rik | 1.00 | 16069 | 3 | | | 4930402F11Rik | 1.00 |
| 15974 | 3 | | | | | | | 2310065F04Rik | 1.00 | 16070 | 3 | | | 4930402K13Rik | 1.00 |
| 15975 | 3 | | | | | | | 2310069B03Rik | 1.00 | 16071 | 3 | | | 4930404A05Rik | 1.00 |
| 15976 | 3 | | | | | | | 2310069G16Rik | 1.00 | 16072 | 3 | | | 4930404A10Rik | 1.00 |
| 15977 | 3 | | | | | | | 2310081J21Rik | 1.00 | 16073 | 3 | | | 4930404H11Rik | 1.00 |
| 15978 | 3 | | | | | | | 2410003L11Rik | 1.00 | 16074 | 3 | | | 4930405A10Rik | 1.00 |
| 15979 | 3 | | | | | | | 2410004I01Rik | 1.00 | 16075 | 3 | | | 4930405A21Rik | 1.00 |
| 15980 | 3 | | | | | | | 2410007B07Rik | 1.00 | 16076 | 3 | | | 4930405D11Rik | 1.00 |
| 15981 | 3 | | | | | | | 2410012E07Rik | 1.00 | 16077 | 3 | | | 4930405J17Rik | 1.00 |
| 15982 | 3 | | | | | | | 2410012M07Rik | 1.00 | 16078 | 3 | | | 4930405L22Rik | 1.00 |
| 15983 | 3 | | | | | | | 2410017I17Rik | 1.00 | 16079 | 3 | | | 4930406D18Rik | 1.00 |
| 15984 | 3 | | | | | | | 2410021H03Rik | 1.00 | 16080 | 3 | | | 4930407I10Rik | 1.00 |
| 15985 | 3 | | | | | | | 2410088K16Rik | 1.00 | 16081 | 3 | | | 4930412B13Rik | 1.00 |
| 15986 | 3 | | | | | | | 2410114N07Rik | 1.00 | 16082 | 3 | | | 4930412D23Rik | 1.00 |
| 15987 | 3 | | | | | | | 2410124H12Rik | 1.00 | 16083 | 3 | | | 4930413E15Rik | 1.00 |
| 15988 | 3 | | | | | | | 2410137M14Rik | 1.00 | 16084 | 3 | | | 4930413M19Rik | 1.00 |
| 15989 | 3 | | | | | | | 2410141K09Rik | 1.00 | 16085 | 3 | | | 4930414N06Rik | 1.00 |
| 15990 | 3 | | | | | | | 2610027K06Rik | 1.00 | 16086 | 3 | | | 4930415F15Rik | 1.00 |
| 15991 | 3 | | | | | | | 2610028E06Rik | 1.00 | 16087 | 3 | | | 4930415L06Rik | 1.00 |
| 15992 | 3 | | | | | | | 2610028H24Rik | 1.00 | 16088 | 3 | | | 4930415O20Rik | 1.00 |
| 15993 | 3 | | | | | | | 2610034M16Rik | 1.00 | 16089 | 3 | | | 4930417O13Rik | 1.00 |
| 15994 | 3 | | | | | | | 2610035F20Rik | 1.00 | 16090 | 3 | | | 4930417O22Rik | 1.00 |
| 15995 | 3 | | | | | | | 2610037D02Rik | 1.00 | 16091 | 3 | | | 4930419G24Rik | 1.00 |
| 15996 | 3 | | | | | | | 2610203C22Rik | 1.00 | 16092 | 3 | | | 4930423M02Rik | 1.00 |
| 15997 | 3 | | | | | | | 2610206C17Rik | 1.00 | 16093 | 3 | | | 4930425K10Rik | 1.00 |
| 15998 | 3 | | | | | | | 2610207O16Rik | 1.00 | 16094 | 3 | | | 4930425O10Rik | 1.00 |
| 15999 | 3 | | | | | | | 2610316D01Rik | 1.00 | 16095 | 3 | | | 4930426L09Rik | 1.00 |
| 16000 | 3 | | | | | | | 2700046A07Rik | 1.00 | 16096 | 3 | | | 4930428D18Rik | 1.00 |
| 16001 | 3 | | | | | | | 2700070H01Rik | 1.00 | 16097 | 3 | | | 4930428E07Rik | 1.00 |
| 16002 | 3 | | | | | | | 2700089J24Rik | 1.00 | 16098 | 3 | | | 4930428G15Rik | 1.00 |
| 16003 | 3 | | | | | | | 2810007J24Rik | 1.00 | 16099 | 3 | | | 4930428O21Rik | 1.00 |
| 16004 | 3 | | | | | | | 2810047C21Rik1 | 1.00 | 16100 | 3 | | | 4930429D17Rik | 1.00 |
| 16005 | 3 | | | | | | | 2810055G20Rik | 1.00 | 16101 | 3 | | | 4930429F11Rik | 1.00 |
| 16006 | 3 | | | | | | | 2810404M03Rik | 1.00 | 16102 | 3 | | | 4930430A15Rik | 1.00 |
| 16007 | 3 | | | | | | | 2810429I04Rik | 1.00 | 16103 | 3 | | | 4930430D24Rik | 1.00 |
| 16008 | 3 | | | | | | | 2810471M01Rik | 1.00 | 16104 | 3 | | | 4930430F21Rik | 1.00 |
| 16009 | 3 | | | | | | | 2900008C10Rik | 1.00 | 16105 | 3 | | | 4930430J02Rik | 1.00 |
| 16010 | 3 | | | | | | | 2900041M22Rik | 1.00 | 16106 | 3 | | | 4930431F12Rik | 1.00 |
| 16011 | 3 | | | | | | | 2900052N01Rik | 1.00 | 16107 | 3 | | | 4930431P03Rik | 1.00 |
| 16012 | 3 | | | | | | | 2900055J20Rik | 1.00 | 16108 | 3 | | | 4930432I09Rik | 1.00 |
| 16013 | 3 | | | | | | | 2900057B20Rik | 1.00 | 16109 | 3 | | | 4930432M17Rik | 1.00 |
| 16014 | 3 | | | | | | | 2900060B14Rik | 1.00 | 16110 | 3 | | | 4930433B08Rik | 1.00 |
| 16015 | 3 | | | | | | | 2900092C05Rik | 1.00 | 16111 | 3 | | | 4930433I11Rik | 1.00 |
| 16016 | 3 | | | | | | | 3010033K07Rik | 1.00 | 16112 | 3 | | | 4930433N12Rik | 1.00 |
| 16017 | 3 | | | | | | | 3100003L05Rik | 1.00 | 16113 | 3 | | | 4930434J06Rik | 1.00 |
| 16018 | 3 | | | | | | | 3110009E18Rik | 1.00 | 16114 | 3 | | | 4930435E12Rik | 1.00 |
| 16019 | 3 | | | | | | | 3110009F21Rik | 1.00 | 16115 | 3 | | | 4930438E09Rik | 1.00 |
| 16020 | 3 | | | | | | | 3110015C05Rik | 1.00 | 16116 | 3 | | | 4930440C22Rik | 1.00 |
| 16021 | 3 | | | | | | | 3110039I08Rik | 1.00 | 16117 | 3 | | | 4930440I19Rik | 1.00 |
| 16022 | 3 | | | | | | | 3110082J24Rik | 1.00 | 16118 | 3 | | | 4930441J16Rik | 1.00 |
| 16023 | 3 | | | | | | | 3110099E03Rik | 1.00 | 16119 | 3 | | | 4930442J19Rik | 1.00 |
| 16024 | 3 | | | | | | | 3200001D21Rik | 1.00 | 16120 | 3 | | | 4930442L01Rik | 1.00 |
| 16025 | 3 | | | | | | | 3300005D01Rik | 1.00 | 16121 | 3 | | | 4930443O20Rik | 1.00 |
| 16026 | 3 | | | | | | | 3632454L22Rik | 1.00 | 16122 | 3 | | | 4930444F02Rik | 1.00 |
| 16027 | 3 | | | | | | | 3830403N18Rik | 1.00 | 16123 | 3 | | | 4930444G20Rik | 1.00 |
| 16028 | 3 | | | | | | | 3830417A13Rik | 1.00 | 16124 | 3 | | | 4930444M15Rik | 1.00 |
| 16029 | 3 | | | | | | | 3930402G23Rik | 1.00 | 16125 | 3 | | | 4930444P10Rik | 1.00 |

Fig. 45 - 85

| | | | | | | | | | | | | | | | | |
|---|---|---|---|---|---|---|---|---|---|---|---|---|---|---|---|---|
| 16126 | 3 | | | | | | 4930447A16Rik | 1.00 | 16222 | 3 | | | | | 4930519H02Rik | 1.00 |
| 16127 | 3 | | | | | | 4930447J18Rik | 1.00 | 16223 | 3 | | | | | 4930520P13Rik | 1.00 |
| 16128 | 3 | | | | | | 4930447K03Rik | 1.00 | 16224 | 3 | | | | | 4930521E06Rik | 1.00 |
| 16129 | 3 | | | | | | 4930447N08Rik | 1.00 | 16225 | 3 | | | | | 4930522H14Rik | 1.00 |
| 16130 | 3 | | | | | | 4930448C13Rik | 1.00 | 16226 | 3 | | | | | 4930522O17Rik | 1.00 |
| 16131 | 3 | | | | | | 4930448F12Rik | 1.00 | 16227 | 3 | | | | | 4930523O13Rik | 1.00 |
| 16132 | 3 | | | | | | 4930448H16Rik | 1.00 | 16228 | 3 | | | | | 4930524B15Rik | 1.00 |
| 16133 | 3 | | | | | | 4930448I06Rik | 1.00 | 16229 | 3 | | | | | 4930524C18Rik | 1.00 |
| 16134 | 3 | | | | | | 4930448J18Rik | 1.00 | 16230 | 3 | | | | | 4930524N10Rik | 1.00 |
| 16135 | 3 | | | | | | 4930448K20Rik | 1.00 | 16231 | 3 | | | | | 4930524O05Rik | 1.00 |
| 16136 | 3 | | | | | | 4930449E01Rik | 1.00 | 16232 | 3 | | | | | 4930524O08Rik | 1.00 |
| 16137 | 3 | | | | | | 4930449E18Rik | 1.00 | 16233 | 3 | | | | | 4930525D18Rik | 1.00 |
| 16138 | 3 | | | | | | 4930449I24Rik | 1.00 | 16234 | 3 | | | | | 4930525G20Rik | 1.00 |
| 16139 | 3 | | | | | | 4930451I11Rik | 1.00 | 16235 | 3 | | | | | 4930525M21Rik | 1.00 |
| 16140 | 3 | | | | | | 4930452A19Rik | 1.00 | 16236 | 3 | | | | | 4930526L06Rik | 1.00 |
| 16141 | 3 | | | | | | 4930452G13Rik | 1.00 | 16237 | 3 | | | | | 4930527F14Rik | 1.00 |
| 16142 | 3 | | | | | | 4930452N14Rik | 1.00 | 16238 | 3 | | | | | 4930527G23Rik | 1.00 |
| 16143 | 3 | | | | | | 4930453H23Rik | 1.00 | 16239 | 3 | | | | | 4930528A17Rik | 1.00 |
| 16144 | 3 | | | | | | 4930453L07Rik | 1.00 | 16240 | 3 | | | | | 4930528D03Rik | 1.00 |
| 16145 | 3 | | | | | | 4930455B14Rik | 1.00 | 16241 | 3 | | | | | 4930528P14Rik | 1.00 |
| 16146 | 3 | | | | | | 4930455D15Rik | 1.00 | 16242 | 3 | | | | | 4930529C04Rik | 1.00 |
| 16147 | 3 | | | | | | 4930455F16Rik | 1.00 | 16243 | 3 | | | | | 4930529K09Rik | 1.00 |
| 16148 | 3 | | | | | | 4930455H04Rik | 1.00 | 16244 | 3 | | | | | 4930529L06Rik | 1.00 |
| 16149 | 3 | | | | | | 4930455I16Rik | 1.00 | 16245 | 3 | | | | | 4930529M08Rik | 1.00 |
| 16150 | 3 | | | | | | 4930456L15Rik | 1.00 | 16246 | 3 | | | | | 4930532M18Rik | 1.00 |
| 16151 | 3 | | | | | | 4930459C07Rik | 1.00 | 16247 | 3 | | | | | 4930533B01Rik | 1.00 |
| 16152 | 3 | | | | | | 4930459L07Rik | 1.00 | 16248 | 3 | | | | | 4930533P14Rik | 1.00 |
| 16153 | 3 | | | | | | 4930461G14Rik | 1.00 | 16249 | 3 | | | | | 4930538K18Rik | 1.00 |
| 16154 | 3 | | | | | | 4930463O16Rik | 1.00 | 16250 | 3 | | | | | 4930539C22Rik | 1.00 |
| 16155 | 3 | | | | | | 4930465K10Rik | 1.00 | 16251 | 3 | | | | | 4930539E08Rik | 1.00 |
| 16156 | 3 | | | | | | 4930465M20Rik | 1.00 | 16252 | 3 | | | | | 4930539M17Rik | 1.00 |
| 16157 | 3 | | | | | | 4930467D21Rik | 1.00 | 16253 | 3 | | | | | 4930539N22Rik | 1.00 |
| 16158 | 3 | | | | | | 4930467E23Rik | 1.00 | 16254 | 3 | | | | | 4930540M03Rik | 1.00 |
| 16159 | 3 | | | | | | 4930467K11Rik | 1.00 | 16255 | 3 | | | | | 4930542C21Rik | 1.00 |
| 16160 | 3 | | | | | | 4930468A15Rik | 1.00 | 16256 | 3 | | | | | 4930542D17Rik | 1.00 |
| 16161 | 3 | | | | | | 4930469G21Rik | 1.00 | 16257 | 3 | | | | | 4930543E12Rik | 1.00 |
| 16162 | 3 | | | | | | 4930470H14Rik | 1.00 | 16258 | 3 | | | | | 4930544D05Rik | 1.00 |
| 16163 | 3 | | | | | | 4930470P17Rik | 1.00 | 16259 | 3 | | | | | 4930544G11Rik | 1.00 |
| 16164 | 3 | | | | | | 4930471C04Rik | 1.00 | 16260 | 3 | | | | | 4930544M13Rik | 1.00 |
| 16165 | 3 | | | | | | 4930471G03Rik | 1.00 | 16261 | 3 | | | | | 4930545E07Rik | 1.00 |
| 16166 | 3 | | | | | | 4930471M09Rik | 1.00 | 16262 | 3 | | | | | 4930545H06Rik | 1.00 |
| 16167 | 3 | | | | | | 4930473O22Rik | 1.00 | 16263 | 3 | | | | | 4930545L23Rik | 1.00 |
| 16168 | 3 | | | | | | 4930474G06Rik | 1.00 | 16264 | 3 | | | | | 4930546C10Rik | 1.00 |
| 16169 | 3 | | | | | | 4930474H20Rik | 1.00 | 16265 | 3 | | | | | 4930546K05Rik | 1.00 |
| 16170 | 3 | | | | | | 4930474N05Rik | 1.00 | 16266 | 3 | | | | | 4930547E08Rik | 1.00 |
| 16171 | 3 | | | | | | 4930474N09Rik | 1.00 | 16267 | 3 | | | | | 4930547E14Rik | 1.00 |
| 16172 | 3 | | | | | | 4930478L05Rik | 1.00 | 16268 | 3 | | | | | 4930548G14Rik | 1.00 |
| 16173 | 3 | | | | | | 4930478P22Rik | 1.00 | 16269 | 3 | | | | | 4930548H24Rik | 1.00 |
| 16174 | 3 | | | | | | 4930479D17Rik | 1.00 | 16270 | 3 | | | | | 4930548J01Rik | 1.00 |
| 16175 | 3 | | | | | | 4930480E11Rik | 1.00 | 16271 | 3 | | | | | 4930548K13Rik | 1.00 |
| 16176 | 3 | | | | | | 4930480G23Rik | 1.00 | 16272 | 3 | | | | | 4930549C01Rik | 1.00 |
| 16177 | 3 | | | | | | 4930480K15Rik | 1.00 | 16273 | 3 | | | | | 4930549G23Rik | 1.00 |
| 16178 | 3 | | | | | | 4930480M12Rik | 1.00 | 16274 | 3 | | | | | 4930550C14Rik | 1.00 |
| 16179 | 3 | | | | | | 4930482G09Rik | 1.00 | 16275 | 3 | | | | | 4930550L24Rik | 1.00 |
| 16180 | 3 | | | | | | 4930483J18Rik | 1.00 | 16276 | 3 | | | | | 4930552N02Rik | 1.00 |
| 16181 | 3 | | | | | | 4930483K19Rik | 1.00 | 16277 | 3 | | | | | 4930552P12Rik | 1.00 |
| 16182 | 3 | | | | | | 4930483O08Rik | 1.00 | 16278 | 3 | | | | | 4930553E22Rik | 1.00 |
| 16183 | 3 | | | | | | 4930486F22Rik | 1.00 | 16279 | 3 | | | | | 4930554C24Rik | 1.00 |
| 16184 | 3 | | | | | | 4930486I03Rik | 1.00 | 16280 | 3 | | | | | 4930555B11Rik | 1.00 |
| 16185 | 3 | | | | | | 4930486L24Rik | 1.00 | 16281 | 3 | | | | | 4930555G01Rik | 1.00 |
| 16186 | 3 | | | | | | 4930487D11Rik | 1.00 | 16282 | 3 | | | | | 4930556C24Rik | 1.00 |
| 16187 | 3 | | | | | | 4930488B22Rik | 1.00 | 16283 | 3 | | | | | 4930556G01Rik | 1.00 |
| 16188 | 3 | | | | | | 4930488L21Rik | 1.00 | 16284 | 3 | | | | | 4930556J02Rik | 1.00 |
| 16189 | 3 | | | | | | 4930500F04Rik | 1.00 | 16285 | 3 | | | | | 4930556N09Rik | 1.00 |
| 16190 | 3 | | | | | | 4930500L23Rik | 1.00 | 16286 | 3 | | | | | 4930557A04Rik | 1.00 |
| 16191 | 3 | | | | | | 4930502A04Rik | 1.00 | 16287 | 3 | | | | | 4930557J02Rik | 1.00 |
| 16192 | 3 | | | | | | 4930502E09Rik | 1.00 | 16288 | 3 | | | | | 4930558C23Rik | 1.00 |
| 16193 | 3 | | | | | | 4930502E18Rik | 1.00 | 16289 | 3 | | | | | 4930558G05Rik | 1.00 |
| 16194 | 3 | | | | | | 4930503B20Rik | 1.00 | 16290 | 3 | | | | | 4930558J18Rik | 1.00 |
| 16195 | 3 | | | | | | 4930503E14Rik | 1.00 | 16291 | 3 | | | | | 4930558K02Rik | 1.00 |
| 16196 | 3 | | | | | | 4930503H13Rik | 1.00 | 16292 | 3 | | | | | 4930562C15Rik | 1.00 |
| 16197 | 3 | | | | | | 4930503O07Rik | 1.00 | 16293 | 3 | | | | | 4930563D23Rik | 1.00 |
| 16198 | 3 | | | | | | 4930504O13Rik | 1.00 | 16294 | 3 | | | | | 4930563E18Rik | 1.00 |
| 16199 | 3 | | | | | | 4930505A04Rik | 1.00 | 16295 | 3 | | | | | 4930563F08Rik | 1.00 |
| 16200 | 3 | | | | | | 4930505G20Rik | 1.00 | 16296 | 3 | | | | | 4930563M20Rik | 1.00 |
| 16201 | 3 | | | | | | 4930507D05Rik | 1.00 | 16297 | 3 | | | | | 4930564B18Rik | 1.00 |
| 16202 | 3 | | | | | | 4930507D10Rik | 1.00 | 16298 | 3 | | | | | 4930564C03Rik | 1.00 |
| 16203 | 3 | | | | | | 4930509E16Rik | 1.00 | 16299 | 3 | | | | | 4930564D02Rik | 1.00 |
| 16204 | 3 | | | | | | 4930509J09Rik | 1.00 | 16300 | 3 | | | | | 4930565D16Rik | 1.00 |
| 16205 | 3 | | | | | | 4930509K18Rik | 1.00 | 16301 | 3 | | | | | 4930567H12Rik | 1.00 |
| 16206 | 3 | | | | | | 4930511A02Rik | 1.00 | 16302 | 3 | | | | | 4930567H17Rik | 1.00 |
| 16207 | 3 | | | | | | 4930511E03Rik | 1.00 | 16303 | 3 | | | | | 4930567J20Rik | 1.00 |
| 16208 | 3 | | | | | | 4930511M06Rik | 1.00 | 16304 | 3 | | | | | 4930567K20Rik | 1.00 |
| 16209 | 3 | | | | | | 4930512B01Rik | 1.00 | 16305 | 3 | | | | | 4930568D16Rik | 1.00 |
| 16210 | 3 | | | | | | 4930513D17Rik | 1.00 | 16306 | 3 | | | | | 4930568E12Rik | 1.00 |
| 16211 | 3 | | | | | | 4930513O06Rik | 1.00 | 16307 | 3 | | | | | 4930568G15Rik | 1.00 |
| 16212 | 3 | | | | | | 4930515B02Rik | 1.00 | 16308 | 3 | | | | | 4930571K23Rik | 1.00 |
| 16213 | 3 | | | | | | 4930515G16Rik | 1.00 | 16309 | 3 | | | | | 4930571O06Rik | 1.00 |
| 16214 | 3 | | | | | | 4930515L03Rik | 1.00 | 16310 | 3 | | | | | 4930572K03Rik | 1.00 |
| 16215 | 3 | | | | | | 4930515L19Rik | 1.00 | 16311 | 3 | | | | | 4930572O03Rik | 1.00 |
| 16216 | 3 | | | | | | 4930517E11Rik | 1.00 | 16312 | 3 | | | | | 4930572O13Rik | 1.00 |
| 16217 | 3 | | | | | | 4930518P08Rik | 1.00 | 16313 | 3 | | | | | 4930573O16Rik | 1.00 |
| 16218 | 3 | | | | | | 4930519D14Rik | 1.00 | 16314 | 3 | | | | | 4930578E11Rik | 1.00 |
| 16219 | 3 | | | | | | 4930519F16Rik | 1.00 | 16315 | 3 | | | | | 4930578I06Rik | 1.00 |
| 16220 | 3 | | | | | | 4930519F24Rik | 1.00 | 16316 | 3 | | | | | 4930578M01Rik | 1.00 |
| 16221 | 3 | | | | | | 4930519G04Rik | 1.00 | 16317 | 3 | | | | | 4930578N18Rik | 1.00 |

Fig. 45 - 86

| | | | | | | | | | | | | | | |
|---|---|---|---|---|---|---|---|---|---|---|---|---|---|---|
| 16318 | 3 | | | | | | 4930579F01Rik | 1.00 | 16414 | 3 | | | | | | 4933413J09Rik | 1.00 |
| 16319 | 3 | | | | | | 4930583K01Rik | 1.00 | 16415 | 3 | | | | | | 4933413L06Rik | 1.00 |
| 16320 | 3 | | | | | | 4930583P06Rik | 1.00 | 16416 | 3 | | | | | | 4933415F23Rik | 1.00 |
| 16321 | 3 | | | | | | 4930584F24Rik | 1.00 | 16417 | 3 | | | | | | 4933416C03Rik | 1.00 |
| 16322 | 3 | | | | | | 4930590J08Rik | 1.00 | 16418 | 3 | | | | | | 4933416E03Rik | 1.00 |
| 16323 | 3 | | | | | | 4930590L20Rik | 1.00 | 16419 | 3 | | | | | | 4933416I08Rik | 1.00 |
| 16324 | 3 | | | | | | 4930591A17Rik | 1.00 | 16420 | 3 | | | | | | 4933416M06Rik | 1.00 |
| 16325 | 3 | | | | | | 4930592A05Rik | 1.00 | 16421 | 3 | | | | | | 4933416M07Rik | 1.00 |
| 16326 | 3 | | | | | | 4930592I03Rik | 1.00 | 16422 | 3 | | | | | | 4933417A18Rik | 1.00 |
| 16327 | 3 | | | | | | 4930593A02Rik | 1.00 | 16423 | 3 | | | | | | 4933417D19Rik | 1.00 |
| 16328 | 3 | | | | | | 4930593C16Rik | 1.00 | 16424 | 3 | | | | | | 4933417E11Rik | 1.00 |
| 16329 | 3 | | | | | | 4930595M18Rik | 1.00 | 16425 | 3 | | | | | | 4933417O13Rik | 1.00 |
| 16330 | 3 | | | | | | 4930596D02Rik | 1.00 | 16426 | 3 | | | | | | 4933421I07Rik | 1.00 |
| 16331 | 3 | | | | | | 4930596I21Rik | 1.00 | 16427 | 3 | | | | | | 4933422A05Rik | 1.00 |
| 16332 | 3 | | | | | | 4930597G03Rik | 1.00 | 16428 | 3 | | | | | | 4933422H20Rik | 1.00 |
| 16333 | 3 | | | | | | 4930598F16Rik | 1.00 | 16429 | 3 | | | | | | 4933424G05Rik | 1.00 |
| 16334 | 3 | | | | | | 4930599N23Rik | 1.00 | 16430 | 3 | | | | | | 4933424G06Rik | 1.00 |
| 16335 | 3 | | | | | | 4931402G19Rik | 1.00 | 16431 | 3 | | | | | | 4933425B07Rik | 1.00 |
| 16336 | 3 | | | | | | 4931403G20Rik | 1.00 | 16432 | 3 | | | | | | 4933425L06Rik | 1.00 |
| 16337 | 3 | | | | | | 4931406B18Rik | 1.00 | 16433 | 3 | | | | | | 4933427D06Rik | 1.00 |
| 16338 | 3 | | | | | | 4931406H21Rik | 1.00 | 16434 | 3 | | | | | | 4933427E11Rik | 1.00 |
| 16339 | 3 | | | | | | 4931408C20Rik | 1.00 | 16435 | 3 | | | | | | 4933427E13Rik | 1.00 |
| 16340 | 3 | | | | | | 4931409K22Rik | 1.00 | 16436 | 3 | | | | | | 4933427G17Rik | 1.00 |
| 16341 | 3 | | | | | | 4931412M21 | 1.00 | 16437 | 3 | | | | | | 4933427J22Rik | 1.00 |
| 16342 | 3 | | | | | | 4931417E11Rik | 1.00 | 16438 | 3 | | | | | | 4933428C19Rik | 1.00 |
| 16343 | 3 | | | | | | 4931419H13Rik | 1.00 | 16439 | 3 | | | | | | 4933429K18Rik | 1.00 |
| 16344 | 3 | | | | | | 4931420L22Rik | 1.00 | 16440 | 3 | | | | | | 4933429O19Rik | 1.00 |
| 16345 | 3 | | | | | | 4931423N10Rik | 1.00 | 16441 | 3 | | | | | | 4933430H16Rik | 1.00 |
| 16346 | 3 | | | | | | 4931428L18Rik | 1.00 | 16442 | 3 | | | | | | 4933430I17Rik | 1.00 |
| 16347 | 3 | | | | | | 4931429I11Rik | 1.00 | 16443 | 3 | | | | | | 4933430M04Rik | 1.00 |
| 16348 | 3 | | | | | | 4931429I15Rik | 1.00 | 16444 | 3 | | | | | | 4933430N04Rik | 1.00 |
| 16349 | 3 | | | | | | 4931429P17Rik | 1.00 | 16445 | 3 | | | | | | 4933431G14Rik | 1.00 |
| 16350 | 3 | | | | | | 4931430N09Rik | 1.00 | 16446 | 3 | | | | | | 4933432G23Rik | 1.00 |
| 16351 | 3 | | | | | | 4931431B13Rik | 1.00 | 16447 | 3 | | | | | | 4933432I03Rik | 1.00 |
| 16352 | 3 | | | | | | 4931431C16Rik | 1.00 | 16448 | 3 | | | | | | 4933432I09Rik | 1.00 |
| 16353 | 3 | | | | | | 4931431F19Rik | 1.00 | 16449 | 3 | | | | | | 4933432K03Rik | 1.00 |
| 16354 | 3 | | | | | | 4931440F15Rik | 1.00 | 16450 | 3 | | | | | | 4933433C11Rik | 1.00 |
| 16355 | 3 | | | | | | 4931440J10Rik | 1.00 | 16451 | 3 | | | | | | 4933433F19Rik | 1.00 |
| 16356 | 3 | | | | | | 4931440L10Rik | 1.00 | 16452 | 3 | | | | | | 4933433G08Rik | 1.00 |
| 16357 | 3 | | | | | | 4931440P22Rik | 1.00 | 16453 | 3 | | | | | | 4933433G15Rik | 1.00 |
| 16358 | 3 | | | | | | 4932411N23Rik | 1.00 | 16454 | 3 | | | | | | 4933433G19Rik | 1.00 |
| 16359 | 3 | | | | | | 4932412D23Rik | 1.00 | 16455 | 3 | | | | | | 4933433H22Rik | 1.00 |
| 16360 | 3 | | | | | | 4932413F04Rik | 1.00 | 16456 | 3 | | | | | | 4933434I20Rik | 1.00 |
| 16361 | 3 | | | | | | 4932414J04Rik | 1.00 | 16457 | 3 | | | | | | 4933436E23Rik | 1.00 |
| 16362 | 3 | | | | | | 4932414N04Rik | 1.00 | 16458 | 3 | | | | | | 4933436H12Rik | 1.00 |
| 16363 | 3 | | | | | | 4932415M13Rik | 1.00 | 16459 | 3 | | | | | | 4933436I01Rik | 1.00 |
| 16364 | 3 | | | | | | 4932416K20Rik | 1.00 | 16460 | 3 | | | | | | 4933438B17Rik | 1.00 |
| 16365 | 3 | | | | | | 4932429P05Rik | 1.00 | 16461 | 3 | | | | | | 4933438K21Rik | 1.00 |
| 16366 | 3 | | | | | | 4932435O22Rik | 1.00 | 16462 | 3 | | | | | | 4933439K11Rik | 1.00 |
| 16367 | 3 | | | | | | 4932438H23Rik | 1.00 | 16463 | 3 | | | | | | 4933440J02Rik | 1.00 |
| 16368 | 3 | | | | | | 4932441J04Rik | 1.00 | 16464 | 3 | | | | | | 4933440M02Rik | 1.00 |
| 16369 | 3 | | | | | | 4932443J19Rik | 1.00 | 16465 | 3 | | | | | | 5031410I06Rik | 1.00 |
| 16370 | 3 | | | | | | 4932702P03Rik | 1.00 | 16466 | 3 | | | | | | 5031414D18Rik | 1.00 |
| 16371 | 3 | | | | | | 4933400A11Rik | 1.00 | 16467 | 3 | | | | | | 5031425F14Rik | 1.00 |
| 16372 | 3 | | | | | | 4933400B14Rik | 1.00 | 16468 | 3 | | | | | | 5031426D15Rik | 1.00 |
| 16373 | 3 | | | | | | 4933400C23Rik | 1.00 | 16469 | 3 | | | | | | 5031434C07Rik | 1.00 |
| 16374 | 3 | | | | | | 4933400F21Rik | 1.00 | 16470 | 3 | | | | | | 5031434O11Rik | 1.00 |
| 16375 | 3 | | | | | | 4933400L20Rik | 1.00 | 16471 | 3 | | | | | | 5033403H07Rik | 1.00 |
| 16376 | 3 | | | | | | 4933401B06Rik | 1.00 | 16472 | 3 | | | | | | 5033404E19Rik | 1.00 |
| 16377 | 3 | | | | | | 4933401D09Rik | 1.00 | 16473 | 3 | | | | | | 5133400J02Rik | 1.00 |
| 16378 | 3 | | | | | | 4933401H06Rik | 1.00 | 16474 | 3 | | | | | | 5330411J11Rik | 1.00 |
| 16379 | 3 | | | | | | 4933402C06Rik | 1.00 | 16475 | 3 | | | | | | 5330413P13Rik | 1.00 |
| 16380 | 3 | | | | | | 4933402D24Rik | 1.00 | 16476 | 3 | | | | | | 5330434G04Rik | 1.00 |
| 16381 | 3 | | | | | | 4933402E13Rik | 1.00 | 16477 | 3 | | | | | | 5330439B14Rik | 1.00 |
| 16382 | 3 | | | | | | 4933402J07Rik | 1.00 | 16478 | 3 | | | | | | 5430402E10Rik | 1.00 |
| 16383 | 3 | | | | | | 4933402J10Rik | 1.00 | 16479 | 3 | | | | | | 5430402O13Rik | 1.00 |
| 16384 | 3 | | | | | | 4933402J15Rik | 1.00 | 16480 | 3 | | | | | | 5430403N17Rik | 1.00 |
| 16385 | 3 | | | | | | 4933402N03Rik | 1.00 | 16481 | 3 | | | | | | 5430416O09Rik | 1.00 |
| 16386 | 3 | | | | | | 4933402N22Rik | 1.00 | 16482 | 3 | | | | | | 5430419D17Rik | 1.00 |
| 16387 | 3 | | | | | | 4933402P03Rik | 1.00 | 16483 | 3 | | | | | | 5430421N21Rik | 1.00 |
| 16388 | 3 | | | | | | 4933404G15Rik | 1.00 | 16484 | 3 | | | | | | 5430425K12Rik | 1.00 |
| 16389 | 3 | | | | | | 4933404K08Rik | 1.00 | 16485 | 3 | | | | | | 5430427M07Rik | 1.00 |
| 16390 | 3 | | | | | | 4933405D12Rik | 1.00 | 16486 | 3 | | | | | | 5430427O19Rik | 1.00 |
| 16391 | 3 | | | | | | 4933405E24Rik | 1.00 | 16487 | 3 | | | | | | 5430428K19Rik | 1.00 |
| 16392 | 3 | | | | | | 4933405L10Rik | 1.00 | 16488 | 3 | | | | | | 5430434I15Rik | 1.00 |
| 16393 | 3 | | | | | | 4933405O20Rik | 1.00 | 16489 | 3 | | | | | | 5430437J10Rik | 1.00 |
| 16394 | 3 | | | | | | 4933406D12Rik | 1.00 | 16490 | 3 | | | | | | 5430440P10Rik | 1.00 |
| 16395 | 3 | | | | | | 4933406F09Rik | 1.00 | 16491 | 3 | | | | | | 5530400C23Rik | 1.00 |
| 16396 | 3 | | | | | | 4933406G16Rik | 1.00 | 16492 | 3 | | | | | | 5530401A14Rik | 1.00 |
| 16397 | 3 | | | | | | 4933406I18Rik | 1.00 | 16493 | 3 | | | | | | 5730403I07Rik | 1.00 |
| 16398 | 3 | | | | | | 4933406J08Rik | 1.00 | 16494 | 3 | | | | | | 5730405O15Rik | 1.00 |
| 16399 | 3 | | | | | | 4933406J10Rik | 1.00 | 16495 | 3 | | | | | | 5730412P04Rik | 1.00 |
| 16400 | 3 | | | | | | 4933406K04Rik | 1.00 | 16496 | 3 | | | | | | 5730420D15Rik | 1.00 |
| 16401 | 3 | | | | | | 4933406M09Rik | 1.00 | 16497 | 3 | | | | | | 5730422E09Rik | 1.00 |
| 16402 | 3 | | | | | | 4933407E24Rik | 1.00 | 16498 | 3 | | | | | | 5730435O14Rik | 1.00 |
| 16403 | 3 | | | | | | 4933407G14Rik | 1.00 | 16499 | 3 | | | | | | 5730457N03Rik | 1.00 |
| 16404 | 3 | | | | | | 4933407I05Rik | 1.00 | 16500 | 3 | | | | | | 5730460C07Rik | 1.00 |
| 16405 | 3 | | | | | | 4933408J17Rik | 1.00 | 16501 | 3 | | | | | | 5730488B01Rik | 1.00 |
| 16406 | 3 | | | | | | 4933408N05Rik | 1.00 | 16502 | 3 | | | | | | 5730507C01Rik | 1.00 |
| 16407 | 3 | | | | | | 4933409G03Rik | 1.00 | 16503 | 3 | | | | | | 5730522E02Rik | 1.00 |
| 16408 | 3 | | | | | | 4933411E08Rik | 1.00 | 16504 | 3 | | | | | | 5830403L16Rik | 1.00 |
| 16409 | 3 | | | | | | 4933411G06Rik | 1.00 | 16505 | 3 | | | | | | 5830411N06Rik | 1.00 |
| 16410 | 3 | | | | | | 4933411G11Rik | 1.00 | 16506 | 3 | | | | | | 5830416I19Rik | 1.00 |
| 16411 | 3 | | | | | | 4933412E24Rik | 1.00 | 16507 | 3 | | | | | | 5830416P10Rik | 1.00 |
| 16412 | 3 | | | | | | 4933412O06Rik | 1.00 | 16508 | 3 | | | | | | 5830418P13Rik | 1.00 |
| 16413 | 3 | | | | | | 4933413G19Rik | 1.00 | 16509 | 3 | | | | | | 5830428M24Rik | 1.00 |

Fig. 45 - 87

| | | | | | | | | | | | | | | |
|---|---|---|---|---|---|---|---|---|---|---|---|---|---|---|
| 16510 | 3 | | | | | 5830432E09Rik | 1.00 | 16606 | 3 | | | | 9930111H07Rik | 1.00 |
| 16511 | 3 | | | | | 5830444B04Rik | 1.00 | 16607 | 3 | | | | 9930111J21Rik1 | 1.00 |
| 16512 | 3 | | | | | 5830473C10Rik | 1.00 | 16608 | 3 | | | | A130077B15Rik | 1.00 |
| 16513 | 3 | | | | | 5930438M14Rik | 1.00 | 16609 | 3 | | | | A1bg | 1.00 |
| 16514 | 3 | | | | | 6030407O03Rik | 1.00 | 16610 | 3 | | | | A230001M10Rik | 1.00 |
| 16515 | 3 | | | | | 6030440G07Rik | 1.00 | 16611 | 3 | | | | A230009B12Rik | 1.00 |
| 16516 | 3 | | | | | 6030443J06Rik | 1.00 | 16612 | 3 | | | | A230020J21Rik | 1.00 |
| 16517 | 3 | | | | | 6030466F02Rik | 1.00 | 16613 | 3 | | | | A230028O05Rik | 1.00 |
| 16518 | 3 | | | | | 6030469F06Rik | 1.00 | 16614 | 3 | | | | A230056J06Rik | 1.00 |
| 16519 | 3 | | | | | 6030498E09Rik | 1.00 | 16615 | 3 | | | | A230072E10Rik | 1.00 |
| 16520 | 3 | | | | | 6330407A03Rik | 1.00 | 16616 | 3 | | | | A230073K19Rik | 1.00 |
| 16521 | 3 | | | | | 6330410L21Rik | 1.00 | 16617 | 3 | | | | A230108P19Rik | 1.00 |
| 16522 | 3 | | | | | 6330415B21Rik | 1.00 | 16618 | 3 | | | | A330032B11Rik | 1.00 |
| 16523 | 3 | | | | | 6430503K07Rik | 1.00 | 16619 | 3 | | | | A330033J07Rik | 1.00 |
| 16524 | 3 | | | | | 6430531B16Rik | 1.00 | 16620 | 3 | | | | A330041J22Rik | 1.00 |
| 16525 | 3 | | | | | 6430550D23Rik | 1.00 | 16621 | 3 | | | | A330048O09Rik | 1.00 |
| 16526 | 3 | | | | | 6430584L05Rik | 1.00 | 16622 | 3 | | | | A330049N07Rik | 1.00 |
| 16527 | 3 | | | | | 6430710C18Rik | 1.00 | 16623 | 3 | | | | A330050F15Rik | 1.00 |
| 16528 | 3 | | | | | 6530411M01Rik | 1.00 | 16624 | 3 | | | | A330070K13Rik | 1.00 |
| 16529 | 3 | | | | | 6720468P15Rik | 1.00 | 16625 | 3 | | | | A330076C08Rik | 1.00 |
| 16530 | 3 | | | | | 6720483E21Rik | 1.00 | 16626 | 3 | | | | A330093E20Rik | 1.00 |
| 16531 | 3 | | | | | 6820408C15Rik | 1.00 | 16627 | 3 | | | | A430078G23Rik | 1.00 |
| 16532 | 3 | | | | | 7420426K07Rik | 1.00 | 16628 | 3 | | | | A430088P11Rik | 1.00 |
| 16533 | 3 | | | | | 7420461P10Rik | 1.00 | 16629 | 3 | | | | A430089I19Rik | 1.00 |
| 16534 | 3 | | | | | 7420700N18Rik | 1.00 | 16630 | 3 | | | | A430090L17Rik | 1.00 |
| 16535 | 3 | | | | | 7420701I03Rik | 1.00 | 16631 | 3 | | | | A430093F15Rik | 1.00 |
| 16536 | 3 | | | | | 7530416G11Rik | 1.00 | 16632 | 3 | | | | A430107P09Rik | 1.00 |
| 16537 | 3 | | | | | 7630403G23Rik | 1.00 | 16633 | 3 | | | | A4gnt | 1.00 |
| 16538 | 3 | | | | | 8030411F24Rik | 1.00 | 16634 | 3 | | | | A530006G24Rik | 1.00 |
| 16539 | 3 | | | | | 8030423F21Rik | 1.00 | 16635 | 3 | | | | A530013C23Rik | 1.00 |
| 16540 | 3 | | | | | 8030423J24Rik | 1.00 | 16636 | 3 | | | | A530032D15Rik | 1.00 |
| 16541 | 3 | | | | | 8030442B05Rik | 1.00 | 16637 | 3 | | | | A530046M15Rik | 1.00 |
| 16542 | 3 | | | | | 8030443G20Rik | 1.00 | 16638 | 3 | | | | A530050N04Rik | 1.00 |
| 16543 | 3 | | | | | 8430422H06Rik | 1.00 | 16639 | 3 | | | | A530053G22Rik | 1.00 |
| 16544 | 3 | | | | | 8430423G03Rik | 1.00 | 16640 | 3 | | | | A530064D06Rik | 1.00 |
| 16545 | 3 | | | | | 8430431K14Rik | 1.00 | 16641 | 3 | | | | A530065N20Rik | 1.00 |
| 16546 | 3 | | | | | 8430436N08Rik | 1.00 | 16642 | 3 | | | | A530072M11Rik | 1.00 |
| 16547 | 3 | | | | | 8430437L04Rik | 1.00 | 16643 | 3 | | | | A530088E08Rik | 1.00 |
| 16548 | 3 | | | | | 9030204H09Rik | 1.00 | 16644 | 3 | | | | A630010A05Rik | 1.00 |
| 16549 | 3 | | | | | 9030404E10Rik | 1.00 | 16645 | 3 | | | | A630012P03Rik | 1.00 |
| 16550 | 3 | | | | | 9030619P08Rik | 1.00 | 16646 | 3 | | | | A630019I02Rik | 1.00 |
| 16551 | 3 | | | | | 9030625G05Rik | 1.00 | 16647 | 3 | | | | A630020A06 | 1.00 |
| 16552 | 3 | | | | | 9130015A21Rik | 1.00 | 16648 | 3 | | | | A630023A22Rik | 1.00 |
| 16553 | 3 | | | | | 9130015L21Rik | 1.00 | 16649 | 3 | | | | A630023P12Rik | 1.00 |
| 16554 | 3 | | | | | 9130019P16Rik | 1.00 | 16650 | 3 | | | | A630073D07Rik | 1.00 |
| 16555 | 3 | | | | | 9130204L05Rik | 1.00 | 16651 | 3 | | | | A630075F10Rik | 1.00 |
| 16556 | 3 | | | | | 9130209A04Rik | 1.00 | 16652 | 3 | | | | A630076J17Rik | 1.00 |
| 16557 | 3 | | | | | 9130221F21Rik | 1.00 | 16653 | 3 | | | | A630077J23Rik | 1.00 |
| 16558 | 3 | | | | | 9130227L01Rik | 1.00 | 16654 | 3 | | | | A630095E13Rik | 1.00 |
| 16559 | 3 | | | | | 9130230L23Rik | 1.00 | 16655 | 3 | | | | A630095N17Rik | 1.00 |
| 16560 | 3 | | | | | 9130409I23Rik | 1.00 | 16656 | 3 | | | | A730006G06Rik | 1.00 |
| 16561 | 3 | | | | | 9230009I02Rik | 1.00 | 16657 | 3 | | | | A730018C14Rik | 1.00 |
| 16562 | 3 | | | | | 9230102K24Rik | 1.00 | 16658 | 3 | | | | A730020M07Rik | 1.00 |
| 16563 | 3 | | | | | 9230102O04Rik | 1.00 | 16659 | 3 | | | | A730036I17Rik | 1.00 |
| 16564 | 3 | | | | | 9230104L09Rik | 1.00 | 16660 | 3 | | | | A730043L09Rik | 1.00 |
| 16565 | 3 | | | | | 9230105E05Rik | 1.00 | 16661 | 3 | | | | A730082K24Rik | 1.00 |
| 16566 | 3 | | | | | 9230110F15Rik | 1.00 | 16662 | 3 | | | | A730085K08Rik | 1.00 |
| 16567 | 3 | | | | | 9230112D13Rik | 1.00 | 16663 | 3 | | | | A730090H04Rik | 1.00 |
| 16568 | 3 | | | | | 9230112J17Rik | 1.00 | 16664 | 3 | | | | A730090N16Rik | 1.00 |
| 16569 | 3 | | | | | 9330111N05Rik | 1.00 | 16665 | 3 | | | | A830009L08Rik | 1.00 |
| 16570 | 3 | | | | | 9330117O12Rik | 1.00 | 16666 | 3 | | | | A830019L24Rik | 1.00 |
| 16571 | 3 | | | | | 9330158H04Rik | 1.00 | 16667 | 3 | | | | A930001A20Rik | 1.00 |
| 16572 | 3 | | | | | 9330162B11Rik | 1.00 | 16668 | 3 | | | | A930001C03Rik | 1.00 |
| 16573 | 3 | | | | | 9330175E14Rik | 1.00 | 16669 | 3 | | | | A930003O13Rik | 1.00 |
| 16574 | 3 | | | | | 9330175M20Rik | 1.00 | 16670 | 3 | | | | A930006I01Rik | 1.00 |
| 16575 | 3 | | | | | 9330178D15Rik | 1.00 | 16671 | 3 | | | | A930007I19Rik | 1.00 |
| 16576 | 3 | | | | | 9330179D12Rik | 1.00 | 16672 | 3 | | | | A930009A15Rik | 1.00 |
| 16577 | 3 | | | | | 9330182O14Rik | 1.00 | 16673 | 3 | | | | A930011G23Rik | 1.00 |
| 16578 | 3 | | | | | 9330188P03Rik | 1.00 | 16674 | 3 | | | | A930012L18Rik | 1.00 |
| 16579 | 3 | | | | | 9430007A20Rik | 1.00 | 16675 | 3 | | | | A930018P22Rik | 1.00 |
| 16580 | 3 | | | | | 9430014N10Rik | 1.00 | 16676 | 3 | | | | A930019D19Rik | 1.00 |
| 16581 | 3 | | | | | 9430018G01Rik | 1.00 | 16677 | 3 | | | | A930041C12Rik | 1.00 |
| 16582 | 3 | | | | | 9430019J16Rik | 1.00 | 16678 | 3 | | | | AA387883 | 1.00 |
| 16583 | 3 | | | | | 9430037G07Rik | 1.00 | 16679 | 3 | | | | AA413626 | 1.00 |
| 16584 | 3 | | | | | 9430041J12Rik | 1.00 | 16680 | 3 | | | | AA467197 | 1.00 |
| 16585 | 3 | | | | | 9430060J03Rik | 1.00 | 16681 | 3 | | | | AA536875 | 1.00 |
| 16586 | 3 | | | | | 9430069J07Rik | 1.00 | 16682 | 3 | | | | AA543186 | 1.00 |
| 16587 | 3 | | | | | 9430076C15Rik | 1.00 | 16683 | 3 | | | | AA543401 | 1.00 |
| 16588 | 3 | | | | | 9530002B09Rik | 1.00 | 16684 | 3 | | | | AA545190 | 1.00 |
| 16589 | 3 | | | | | 9530003J23Rik | 1.00 | 16685 | 3 | | | | AA619741 | 1.00 |
| 16590 | 3 | | | | | 9530026F06Rik | 1.00 | 16686 | 3 | | | | AA792892 | 1.00 |
| 16591 | 3 | | | | | 9530026P05Rik | 1.00 | 16687 | 3 | | | | AB041803 | 1.00 |
| 16592 | 3 | | | | | 9530036O11Rik | 1.00 | 16688 | 3 | | | | AF067061 | 1.00 |
| 16593 | 3 | | | | | 9530051G07Rik | 1.00 | 16689 | 3 | | | | AF067063 | 1.00 |
| 16594 | 3 | | | | | 9530052E02Rik | 1.00 | 16690 | 3 | | | | AF357355 | 1.00 |
| 16595 | 3 | | | | | 9530053A07Rik | 1.00 | 16691 | 3 | | | | AF357359 | 1.00 |
| 16596 | 3 | | | | | 9530059N14Rik | 1.00 | 16692 | 3 | | | | AF357399 | 1.00 |
| 16597 | 3 | | | | | 9530080O11Rik | 1.00 | 16693 | 3 | | | | AF357425 | 1.00 |
| 16598 | 3 | | | | | 9530091C08Rik | 1.00 | 16694 | 3 | | | | AF357426 | 1.00 |
| 16599 | 3 | | | | | 9630001P10Rik | 1.00 | 16695 | 3 | | | | AF366264 | 1.00 |
| 16600 | 3 | | | | | 9630013A20Rik | 1.00 | 16696 | 3 | | | | AI115009 | 1.00 |
| 16601 | 3 | | | | | 9630028B13Rik | 1.00 | 16697 | 3 | | | | AI197445 | 1.00 |
| 16602 | 3 | | | | | 9630028H03Rik | 1.00 | 16698 | 3 | | | | AI314278 | 1.00 |
| 16603 | 3 | | | | | 9830107B12Rik | 1.00 | 16699 | 3 | | | | AI317395 | 1.00 |
| 16604 | 3 | | | | | 9830132P13Rik | 1.00 | 16700 | 3 | | | | AI463170 | 1.00 |
| 16605 | 3 | | | | | 9830166K06Rik | 1.00 | 16701 | 3 | | | | AI507597 | 1.00 |

Fig. 45 - 88

| | | | | | | | | | | | | | | | | |
|---|---|---|---|---|---|---|---|---|---|---|---|---|---|---|---|---|
| 16702 | 3 | | | | | | | AI646519 | 1.00 | 16798 | 3 | | | | Adh4 | 1.00 |
| 16703 | 3 | | | | | | | AI847159 | 1.00 | 16799 | 3 | | | | Adh6-ps1 | 1.00 |
| 16704 | 3 | | | | | | | AU015228 | 1.00 | 16800 | 3 | | | | Adh6a | 1.00 |
| 16705 | 3 | | | | | | | AU015791 | 1.00 | 16801 | 3 | | | | Adra2c | 1.00 |
| 16706 | 3 | | | | | | | AU015836 | 1.00 | 16802 | 3 | | | | Adrb3 | 1.00 |
| 16707 | 3 | | | | | | | AU016765 | 1.00 | 16803 | 3 | | | | Agbl1 | 1.00 |
| 16708 | 3 | | | | | | | AU018091 | 1.00 | 16804 | 3 | | | | Agbl2 | 1.00 |
| 16709 | 3 | | | | | | | AU018829 | 1.00 | 16805 | 3 | | | | Agbl4 | 1.00 |
| 16710 | 3 | | | | | | | AU019990 | 1.00 | 16806 | 3 | | | | Agr3 | 1.00 |
| 16711 | 3 | | | | | | | AU021063 | 1.00 | 16807 | 3 | | | | Agrp | 1.00 |
| 16712 | 3 | | | | | | | AU022751 | 1.00 | 16808 | 3 | | | | Agtr1b | 1.00 |
| 16713 | 3 | | | | | | | AU022754 | 1.00 | 16809 | 3 | | | | Ahr | 1.00 |
| 16714 | 3 | | | | | | | AU022793 | 1.00 | 16810 | 3 | | | | Aicda | 1.00 |
| 16715 | 3 | | | | | | | AU023762 | 1.00 | 16811 | 3 | | | | Aipl1 | 1.00 |
| 16716 | 3 | | | | | | | AV051173 | 1.00 | 16812 | 3 | | | | Aire | 1.00 |
| 16717 | 3 | | | | | | | AV320801 | 1.00 | 16813 | 3 | | | | Ak7 | 1.00 |
| 16718 | 3 | | | | | | | AW046200 | 1.00 | 16814 | 3 | | | | Ak8 | 1.00 |
| 16719 | 3 | | | | | | | AW495222 | 1.00 | 16815 | 3 | | | | Akap14 | 1.00 |
| 16720 | 3 | | | | | | | AW822252 | 1.00 | 16816 | 3 | | | | Akap3 | 1.00 |
| 16721 | 3 | | | | | | | AY074887 | 1.00 | 16817 | 3 | | | | Akap4 | 1.00 |
| 16722 | 3 | | | | | | | AY512915 | 1.00 | 16818 | 3 | | | | Aknad1 | 1.00 |
| 16723 | 3 | | | | | | | AY512931 | 1.00 | 16819 | 3 | | | | Akp3 | 1.00 |
| 16724 | 3 | | | | | | | AY761184 | 1.00 | 16820 | 3 | | | | Akr1c18 | 1.00 |
| 16725 | 3 | | | | | | | AY761185 | 1.00 | 16821 | 3 | | | | Akr1c20 | 1.00 |
| 16726 | 3 | | | | | | | Aadacl3 | 1.00 | 16822 | 3 | | | | Akr1c21 | 1.00 |
| 16727 | 3 | | | | | | | Aadat | 1.00 | 16823 | 3 | | | | Akr1c6 | 1.00 |
| 16728 | 3 | | | | | | | Aanat | 1.00 | 16824 | 3 | | | | Akr1cl | 1.00 |
| 16729 | 3 | | | | | | | Abca13 | 1.00 | 16825 | 3 | | | | Aldh3a1 | 1.00 |
| 16730 | 3 | | | | | | | Abca14 | 1.00 | 16826 | 3 | | | | Aldh5a1 | 1.00 |
| 16731 | 3 | | | | | | | Abca15 | 1.00 | 16827 | 3 | | | | Alk | 1.00 |
| 16732 | 3 | | | | | | | Abca16 | 1.00 | 16828 | 3 | | | | Allc | 1.00 |
| 16733 | 3 | | | | | | | Abca17 | 1.00 | 16829 | 3 | | | | Alms1-ps2 | 1.00 |
| 16734 | 3 | | | | | | | Abca4 | 1.00 | 16830 | 3 | | | | Alox12e | 1.00 |
| 16735 | 3 | | | | | | | Abcb1b | 1.00 | 16831 | 3 | | | | Alox15 | 1.00 |
| 16736 | 3 | | | | | | | Abcb5 | 1.00 | 16832 | 3 | | | | Alox8 | 1.00 |
| 16737 | 3 | | | | | | | Abcc12 | 1.00 | 16833 | 3 | | | | Alppl2 | 1.00 |
| 16738 | 3 | | | | | | | Abcc8 | 1.00 | 16834 | 3 | | | | Als2cr11 | 1.00 |
| 16739 | 3 | | | | | | | Abcg5 | 1.00 | 16835 | 3 | | | | Als2cr12 | 1.00 |
| 16740 | 3 | | | | | | | Abcg8 | 1.00 | 16836 | 3 | | | | Ambn | 1.00 |
| 16741 | 3 | | | | | | | Abhd1 | 1.00 | 16837 | 3 | | | | Amelx | 1.00 |
| 16742 | 3 | | | | | | | Abhd12b | 1.00 | 16838 | 3 | | | | Amhr2 | 1.00 |
| 16743 | 3 | | | | | | | Abhd16b | 1.00 | 16839 | 3 | | | | Amtn | 1.00 |
| 16744 | 3 | | | | | | | Abo | 1.00 | 16840 | 3 | | | | Ang2 | 1.00 |
| 16745 | 3 | | | | | | | Abtb1 | 1.00 | 16841 | 3 | | | | Ang3 | 1.00 |
| 16746 | 3 | | | | | | | Acad12 | 1.00 | 16842 | 3 | | | | Ang4 | 1.00 |
| 16747 | 3 | | | | | | | Acap1 | 1.00 | 16843 | 3 | | | | Ang5 | 1.00 |
| 16748 | 3 | | | | | | | Acbd7 | 1.00 | 16844 | 3 | | | | Ang6 | 1.00 |
| 16749 | 3 | | | | | | | Accsl | 1.00 | 16845 | 3 | | | | Angpt4 | 1.00 |
| 16750 | 3 | | | | | | | Ace3 | 1.00 | 16846 | 3 | | | | Ankar | 1.00 |
| 16751 | 3 | | | | | | | Ackr2 | 1.00 | 16847 | 3 | | | | Ankef1 | 1.00 |
| 16752 | 3 | | | | | | | Acnat2 | 1.00 | 16848 | 3 | | | | Ankfn1 | 1.00 |
| 16753 | 3 | | | | | | | Acot5 | 1.00 | 16849 | 3 | | | | Ankk1 | 1.00 |
| 16754 | 3 | | | | | | | Acoxl | 1.00 | 16850 | 3 | | | | Ankmy1 | 1.00 |
| 16755 | 3 | | | | | | | Acpt | 1.00 | 16851 | 3 | | | | Ankrd33 | 1.00 |
| 16756 | 3 | | | | | | | Acrv1 | 1.00 | 16852 | 3 | | | | Ankrd34b | 1.00 |
| 16757 | 3 | | | | | | | Acsbg2 | 1.00 | 16853 | 3 | | | | Ankrd34c | 1.00 |
| 16758 | 3 | | | | | | | Acsm1 | 1.00 | 16854 | 3 | | | | Ankrd36 | 1.00 |
| 16759 | 3 | | | | | | | Acsm2 | 1.00 | 16855 | 3 | | | | Ankrd53 | 1.00 |
| 16760 | 3 | | | | | | | Acsm4 | 1.00 | 16856 | 3 | | | | Ankrd60 | 1.00 |
| 16761 | 3 | | | | | | | Acsm5 | 1.00 | 16857 | 3 | | | | Ankrd63 | 1.00 |
| 16762 | 3 | | | | | | | Acss2os | 1.00 | 16858 | 3 | | | | Ankrd66 | 1.00 |
| 16763 | 3 | | | | | | | Actbl2 | 1.00 | 16859 | 3 | | | | Ankrd7 | 1.00 |
| 16764 | 3 | | | | | | | Actl10 | 1.00 | 16860 | 3 | | | | Anks1 | 1.00 |
| 16765 | 3 | | | | | | | Actl11 | 1.00 | 16861 | 3 | | | | Ankub1 | 1.00 |
| 16766 | 3 | | | | | | | Actl7a | 1.00 | 16862 | 3 | | | | Ano2 | 1.00 |
| 16767 | 3 | | | | | | | Actl7b | 1.00 | 16863 | 3 | | | | Ano3 | 1.00 |
| 16768 | 3 | | | | | | | Actl9 | 1.00 | 16864 | 3 | | | | Ano4 | 1.00 |
| 16769 | 3 | | | | | | | Actrt1 | 1.00 | 16865 | 3 | | | | Ano5 | 1.00 |
| 16770 | 3 | | | | | | | Actrt2 | 1.00 | 16866 | 3 | | | | Antxrl | 1.00 |
| 16771 | 3 | | | | | | | Actrt3 | 1.00 | 16867 | 3 | | | | Anxa10 | 1.00 |
| 16772 | 3 | | | | | | | Adad1 | 1.00 | 16868 | 3 | | | | Aox1 | 1.00 |
| 16773 | 3 | | | | | | | Adad2 | 1.00 | 16869 | 3 | | | | Aox2 | 1.00 |
| 16774 | 3 | | | | | | | Adam18 | 1.00 | 16870 | 3 | | | | Aox3 | 1.00 |
| 16775 | 3 | | | | | | | Adam1b | 1.00 | 16871 | 3 | | | | Apobec4 | 1.00 |
| 16776 | 3 | | | | | | | Adam2 | 1.00 | 16872 | 3 | | | | Apol10a | 1.00 |
| 16777 | 3 | | | | | | | Adam20 | 1.00 | 16873 | 3 | | | | Apol10b | 1.00 |
| 16778 | 3 | | | | | | | Adam21 | 1.00 | 16874 | 3 | | | | Apol11a | 1.00 |
| 16779 | 3 | | | | | | | Adam24 | 1.00 | 16875 | 3 | | | | Apol11b | 1.00 |
| 16780 | 3 | | | | | | | Adam25 | 1.00 | 16876 | 3 | | | | Apol6 | 1.00 |
| 16781 | 3 | | | | | | | Adam26a | 1.00 | 16877 | 3 | | | | Apol7b | 1.00 |
| 16782 | 3 | | | | | | | Adam26b | 1.00 | 16878 | 3 | | | | Apol7c | 1.00 |
| 16783 | 3 | | | | | | | Adam28 | 1.00 | 16879 | 3 | | | | Apol7d | 1.00 |
| 16784 | 3 | | | | | | | Adam29 | 1.00 | 16880 | 3 | | | | Apol7e | 1.00 |
| 16785 | 3 | | | | | | | Adam3 | 1.00 | 16881 | 3 | | | | Apol9a | 1.00 |
| 16786 | 3 | | | | | | | Adam30 | 1.00 | 16882 | 3 | | | | Apol9b | 1.00 |
| 16787 | 3 | | | | | | | Adam32 | 1.00 | 16883 | 3 | | | | Apoo-ps | 1.00 |
| 16788 | 3 | | | | | | | Adam34 | 1.00 | 16884 | 3 | | | | Aqp12 | 1.00 |
| 16789 | 3 | | | | | | | Adam39 | 1.00 | 16885 | 3 | | | | Aqp2 | 1.00 |
| 16790 | 3 | | | | | | | Adam4 | 1.00 | 16886 | 3 | | | | Aqp6 | 1.00 |
| 16791 | 3 | | | | | | | Adam5 | 1.00 | 16887 | 3 | | | | Ar | 1.00 |
| 16792 | 3 | | | | | | | Adam6a | 1.00 | 16888 | 3 | | | | Areg | 1.00 |
| 16793 | 3 | | | | | | | Adam6b | 1.00 | 16889 | 3 | | | | Arhgap15os | 1.00 |
| 16794 | 3 | | | | | | | Adam7 | 1.00 | 16890 | 3 | | | | Arhgap27os3 | 1.00 |
| 16795 | 3 | | | | | | | Adamts13 | 1.00 | 16891 | 3 | | | | Arhgap33os | 1.00 |
| 16796 | 3 | | | | | | | Adcy10 | 1.00 | 16892 | 3 | | | | Arhgap8 | 1.00 |
| 16797 | 3 | | | | | | | Adgb | 1.00 | 16893 | 3 | | | | Arhgef33 | 1.00 |

Fig. 45 - 89

| | | | | | | | | | | | | | | |
|---|---|---|---|---|---|---|---|---|---|---|---|---|---|---|
| 16894 | 3 | | | | | Arhgef38 | 1.00 | 16990 | 3 | | | | BC048671 | 1.00 |
| 16895 | 3 | | | | | Arid3c | 1.00 | 16991 | 3 | | | | BC048679 | 1.00 |
| 16896 | 3 | | | | | Arl13a | 1.00 | 16992 | 3 | | | | BC049352 | 1.00 |
| 16897 | 3 | | | | | Arl14 | 1.00 | 16993 | 3 | | | | BC049635 | 1.00 |
| 16898 | 3 | | | | | Arl14epl | 1.00 | 16994 | 3 | | | | BC049715 | 1.00 |
| 16899 | 3 | | | | | Arl9 | 1.00 | 16995 | 3 | | | | BC049730 | 1.00 |
| 16900 | 3 | | | | | Armc12 | 1.00 | 16996 | 3 | | | | BC049762 | 1.00 |
| 16901 | 3 | | | | | Armc2 | 1.00 | 16997 | 3 | | | | BC051019 | 1.00 |
| 16902 | 3 | | | | | Armc3 | 1.00 | 16998 | 3 | | | | BC051537 | 1.00 |
| 16903 | 3 | | | | | Armc4 | 1.00 | 16999 | 3 | | | | BC051628 | 1.00 |
| 16904 | 3 | | | | | Arr3 | 1.00 | 17000 | 3 | | | | BC051665 | 1.00 |
| 16905 | 3 | | | | | Arrdc5 | 1.00 | 17001 | 3 | | | | BC052688 | 1.00 |
| 16906 | 3 | | | | | Art2a-ps | 1.00 | 17002 | 3 | | | | BC053393 | 1.00 |
| 16907 | 3 | | | | | Art2b | 1.00 | 17003 | 3 | | | | BC055111 | 1.00 |
| 16908 | 3 | | | | | Artn | 1.00 | 17004 | 3 | | | | BC055402 | 1.00 |
| 16909 | 3 | | | | | Asb11 | 1.00 | 17005 | 3 | | | | BC061194 | 1.00 |
| 16910 | 3 | | | | | Asb14 | 1.00 | 17006 | 3 | | | | BC061195 | 1.00 |
| 16911 | 3 | | | | | Asb15 | 1.00 | 17007 | 3 | | | | BC061212 | 1.00 |
| 16912 | 3 | | | | | Asb17 | 1.00 | 17008 | 3 | | | | BC061237 | 1.00 |
| 16913 | 3 | | | | | Asb18 | 1.00 | 17009 | 3 | | | | BC080695 | 1.00 |
| 16914 | 3 | | | | | Asb5 | 1.00 | 17010 | 3 | | | | BC089491 | 1.00 |
| 16915 | 3 | | | | | Asb9 | 1.00 | 17011 | 3 | | | | BC089597 | 1.00 |
| 16916 | 3 | | | | | Ascl3 | 1.00 | 17012 | 3 | | | | BC094916 | 1.00 |
| 16917 | 3 | | | | | Ascl4 | 1.00 | 17013 | 3 | | | | BC100451 | 1.00 |
| 16918 | 3 | | | | | Ascl5 | 1.00 | 17014 | 3 | | | | BC107364 | 1.00 |
| 16919 | 3 | | | | | Asic3 | 1.00 | 17015 | 3 | | | | BC147527 | 1.00 |
| 16920 | 3 | | | | | Asic5 | 1.00 | 17016 | 3 | | | | Baat | 1.00 |
| 16921 | 3 | | | | | Asmt | 1.00 | 17017 | 3 | | | | Bach2os | 1.00 |
| 16922 | 3 | | | | | Astl | 1.00 | 17018 | 3 | | | | Bag5 | 1.00 |
| 16923 | 3 | | | | | Asun | 1.00 | 17019 | 3 | | | | Baiap3 | 1.00 |
| 16924 | 3 | | | | | Asz1 | 1.00 | 17020 | 3 | | | | Banf2 | 1.00 |
| 16925 | 3 | | | | | Atf7ip2 | 1.00 | 17021 | 3 | | | | Bank1 | 1.00 |
| 16926 | 3 | | | | | Atg16l1 | 1.00 | 17022 | 3 | | | | Barx2 | 1.00 |
| 16927 | 3 | | | | | Atoh1 | 1.00 | 17023 | 3 | | | | Batf2 | 1.00 |
| 16928 | 3 | | | | | Atp12a | 1.00 | 17024 | 3 | | | | Bc1 | 1.00 |
| 16929 | 3 | | | | | Atp13a5 | 1.00 | 17025 | 3 | | | | Bcas1os2 | 1.00 |
| 16930 | 3 | | | | | Atp1a4 | 1.00 | 17026 | 3 | | | | Bcas3os1 | 1.00 |
| 16931 | 3 | | | | | Atp2c2 | 1.00 | 17027 | 3 | | | | Bcas3os2 | 1.00 |
| 16932 | 3 | | | | | Atp4a | 1.00 | 17028 | 3 | | | | Bcl2a1a | 1.00 |
| 16933 | 3 | | | | | Atp4b | 1.00 | 17029 | 3 | | | | Bcl2a1c | 1.00 |
| 16934 | 3 | | | | | Atp6ap1l | 1.00 | 17030 | 3 | | | | Bcl2a1d | 1.00 |
| 16935 | 3 | | | | | Atp6v0c-ps2 | 1.00 | 17031 | 3 | | | | Bcl2l10 | 1.00 |
| 16936 | 3 | | | | | Atp6v1b1 | 1.00 | 17032 | 3 | | | | Bcl2l11 | 1.00 |
| 16937 | 3 | | | | | Atp6v1e2 | 1.00 | 17033 | 3 | | | | Bco2 | 1.00 |
| 16938 | 3 | | | | | Atp6v1g3 | 1.00 | 17034 | 3 | | | | Bdh2 | 1.00 |
| 16939 | 3 | | | | | Atp8b3 | 1.00 | 17035 | 3 | | | | Bdkrb1 | 1.00 |
| 16940 | 3 | | | | | Atp8b5 | 1.00 | 17036 | 3 | | | | Becn2 | 1.00 |
| 16941 | 3 | | | | | Aurkc | 1.00 | 17037 | 3 | | | | Best1 | 1.00 |
| 16942 | 3 | | | | | Avp | 1.00 | 17038 | 3 | | | | Best2 | 1.00 |
| 16943 | 3 | | | | | Avpr1b | 1.00 | 17039 | 3 | | | | Bex6 | 1.00 |
| 16944 | 3 | | | | | Avpr2 | 1.00 | 17040 | 3 | | | | Bhlha9 | 1.00 |
| 16945 | 3 | | | | | Awat1 | 1.00 | 17041 | 3 | | | | Bhlhe23 | 1.00 |
| 16946 | 3 | | | | | Awat2 | 1.00 | 17042 | 3 | | | | Birc7 | 1.00 |
| 16947 | 3 | | | | | Aym1 | 1.00 | 17043 | 3 | | | | Blk | 1.00 |
| 16948 | 3 | | | | | B020004C17Rik | 1.00 | 17044 | 3 | | | | Bmp15 | 1.00 |
| 16949 | 3 | | | | | B020004J07Rik | 1.00 | 17045 | 3 | | | | Bmp8b | 1.00 |
| 16950 | 3 | | | | | B020014A21Rik | 1.00 | 17046 | 3 | | | | Bms1 | 1.00 |
| 16951 | 3 | | | | | B020018J22Rik | 1.00 | 17047 | 3 | | | | Bmx | 1.00 |
| 16952 | 3 | | | | | B020031M17Rik | 1.00 | 17048 | 3 | | | | Boll | 1.00 |
| 16953 | 3 | | | | | B130006D01Rik | 1.00 | 17049 | 3 | | | | Bpi | 1.00 |
| 16954 | 3 | | | | | B230112J18Rik | 1.00 | 17050 | 3 | | | | Bpifa2 | 1.00 |
| 16955 | 3 | | | | | B230214G05Rik | 1.00 | 17051 | 3 | | | | Bpifa3 | 1.00 |
| 16956 | 3 | | | | | B230312C02Rik | 1.00 | 17052 | 3 | | | | Bpifa5 | 1.00 |
| 16957 | 3 | | | | | B230319C09Rik | 1.00 | 17053 | 3 | | | | Bpifa6 | 1.00 |
| 16958 | 3 | | | | | B230323A14Rik | 1.00 | 17054 | 3 | | | | Bpifb1 | 1.00 |
| 16959 | 3 | | | | | B3gnt4 | 1.00 | 17055 | 3 | | | | Bpifb2 | 1.00 |
| 16960 | 3 | | | | | B3gnt6 | 1.00 | 17056 | 3 | | | | Bpifb3 | 1.00 |
| 16961 | 3 | | | | | B430010I23Rik | 1.00 | 17057 | 3 | | | | Bpifb4 | 1.00 |
| 16962 | 3 | | | | | B430306N03Rik | 1.00 | 17058 | 3 | | | | Bpifb5 | 1.00 |
| 16963 | 3 | | | | | B830017H08Rik | 1.00 | 17059 | 3 | | | | Bpifb6 | 1.00 |
| 16964 | 3 | | | | | B930018H19Rik | 1.00 | 17060 | 3 | | | | Bpifb9a | 1.00 |
| 16965 | 3 | | | | | B930025P03Rik | 1.00 | 17061 | 3 | | | | Bricd5 | 1.00 |
| 16966 | 3 | | | | | B930059L03Rik | 1.00 | 17062 | 3 | | | | Brs3 | 1.00 |
| 16967 | 3 | | | | | B930092H01Rik | 1.00 | 17063 | 3 | | | | Bsnd | 1.00 |
| 16968 | 3 | | | | | BB014433 | 1.00 | 17064 | 3 | | | | Bsph1 | 1.00 |
| 16969 | 3 | | | | | BB019430 | 1.00 | 17065 | 3 | | | | Bsph2 | 1.00 |
| 16970 | 3 | | | | | BB031773 | 1.00 | 17066 | 3 | | | | Bsx | 1.00 |
| 16971 | 3 | | | | | BB123696 | 1.00 | 17067 | 3 | | | | Btbd16 | 1.00 |
| 16972 | 3 | | | | | BB283400 | 1.00 | 17068 | 3 | | | | Btbd18 | 1.00 |
| 16973 | 3 | | | | | BB287469 | 1.00 | 17069 | 3 | | | | Btbd8 | 1.00 |
| 16974 | 3 | | | | | BB557941 | 1.00 | 17070 | 3 | | | | Btg4 | 1.00 |
| 16975 | 3 | | | | | BC016579 | 1.00 | 17071 | 3 | | | | Btla | 1.00 |
| 16976 | 3 | | | | | BC018473 | 1.00 | 17072 | 3 | | | | Btn1a1 | 1.00 |
| 16977 | 3 | | | | | BC021785 | 1.00 | 17073 | 3 | | | | Btn2a2 | 1.00 |
| 16978 | 3 | | | | | BC024139 | 1.00 | 17074 | 3 | | | | Btnl1 | 1.00 |
| 16979 | 3 | | | | | BC027072 | 1.00 | 17075 | 3 | | | | Btnl2 | 1.00 |
| 16980 | 3 | | | | | BC030499 | 1.00 | 17076 | 3 | | | | C030007H22Rik | 1.00 |
| 16981 | 3 | | | | | BC033916 | 1.00 | 17077 | 3 | | | | C030013G03Rik | 1.00 |
| 16982 | 3 | | | | | BC039771 | 1.00 | 17078 | 3 | | | | C030016D13Rik | 1.00 |
| 16983 | 3 | | | | | BC039966 | 1.00 | 17079 | 3 | | | | C030018K13Rik | 1.00 |
| 16984 | 3 | | | | | BC048502 | 1.00 | 17080 | 3 | | | | C030029H02Rik | 1.00 |
| 16985 | 3 | | | | | BC048546 | 1.00 | 17081 | 3 | | | | C030034L19Rik | 1.00 |
| 16986 | 3 | | | | | BC048562 | 1.00 | 17082 | 3 | | | | C130026L21Rik | 1.00 |
| 16987 | 3 | | | | | BC048602 | 1.00 | 17083 | 3 | | | | C130026L21Rik | 1.00 |
| 16988 | 3 | | | | | BC048609 | 1.00 | 17084 | 3 | | | | C130060C02Rik | 1.00 |
| 16989 | 3 | | | | | BC048644 | 1.00 | 17085 | 3 | | | | C130060K24Rik | 1.00 |

Fig. 45 - 90

| | | | | | | | | | | | | | | |
|---|---|---|---|---|---|---|---|---|---|---|---|---|---|---|
| 17086 | 3 | | | | | | C130071C03Rik | 1.00 | 17182 | 3 | | | | Ccdc155 | 1.00 |
| 17087 | 3 | | | | | | C1ql2 | 1.00 | 17183 | 3 | | | | Ccdc158 | 1.00 |
| 17088 | 3 | | | | | | C1ql4 | 1.00 | 17184 | 3 | | | | Ccdc159 | 1.00 |
| 17089 | 3 | | | | | | C1s2 | 1.00 | 17185 | 3 | | | | Ccdc162 | 1.00 |
| 17090 | 3 | | | | | | C230004F18Rik | 1.00 | 17186 | 3 | | | | Ccdc169 | 1.00 |
| 17091 | 3 | | | | | | C230024C17Rik | 1.00 | 17187 | 3 | | | | Ccdc170 | 1.00 |
| 17092 | 3 | | | | | | C230029M16 | 1.00 | 17188 | 3 | | | | Ccdc171 | 1.00 |
| 17093 | 3 | | | | | | C230037L18Rik | 1.00 | 17189 | 3 | | | | Ccdc172 | 1.00 |
| 17094 | 3 | | | | | | C230079O03Rik | 1.00 | 17190 | 3 | | | | Ccdc175 | 1.00 |
| 17095 | 3 | | | | | | C2cd4a | 1.00 | 17191 | 3 | | | | Ccdc178 | 1.00 |
| 17096 | 3 | | | | | | C2cd4b | 1.00 | 17192 | 3 | | | | Ccdc183 | 1.00 |
| 17097 | 3 | | | | | | C2cd4c | 1.00 | 17193 | 3 | | | | Ccdc185 | 1.00 |
| 17098 | 3 | | | | | | C330011F03Rik | 1.00 | 17194 | 3 | | | | Ccdc27 | 1.00 |
| 17099 | 3 | | | | | | C330013F16Rik | 1.00 | 17195 | 3 | | | | Ccdc28b | 1.00 |
| 17100 | 3 | | | | | | C330022C24Rik | 1.00 | 17196 | 3 | | | | Ccdc33 | 1.00 |
| 17101 | 3 | | | | | | C330024C12Rik | 1.00 | 17197 | 3 | | | | Ccdc34os | 1.00 |
| 17102 | 3 | | | | | | C330024D21Rik | 1.00 | 17198 | 3 | | | | Ccdc37 | 1.00 |
| 17103 | 3 | | | | | | C330046G13Rik | 1.00 | 17199 | 3 | | | | Ccdc42 | 1.00 |
| 17104 | 3 | | | | | | C430002E04Rik | 1.00 | 17200 | 3 | | | | Ccdc42b | 1.00 |
| 17105 | 3 | | | | | | C430002N11Rik | 1.00 | 17201 | 3 | | | | Ccdc54 | 1.00 |
| 17106 | 3 | | | | | | C4a | 1.00 | 17202 | 3 | | | | Ccdc60 | 1.00 |
| 17107 | 3 | | | | | | C4bp | 1.00 | 17203 | 3 | | | | Ccdc63 | 1.00 |
| 17108 | 3 | | | | | | C4bp-ps1 | 1.00 | 17204 | 3 | | | | Ccdc7 | 1.00 |
| 17109 | 3 | | | | | | C5ar2 | 1.00 | 17205 | 3 | | | | Ccdc70 | 1.00 |
| 17110 | 3 | | | | | | C6 | 1.00 | 17206 | 3 | | | | Ccdc78 | 1.00 |
| 17111 | 3 | | | | | | C630028N04Rik | 1.00 | 17207 | 3 | | | | Ccdc79 | 1.00 |
| 17112 | 3 | | | | | | C630031E19Rik | 1.00 | 17208 | 3 | | | | Ccdc81 | 1.00 |
| 17113 | 3 | | | | | | C7 | 1.00 | 17209 | 3 | | | | Ccdc83 | 1.00 |
| 17114 | 3 | | | | | | C730002L08Rik | 1.00 | 17210 | 3 | | | | Ccdc87 | 1.00 |
| 17115 | 3 | | | | | | C730027H18Rik | 1.00 | 17211 | 3 | | | | Ccdc89 | 1.00 |
| 17116 | 3 | | | | | | C730036E19Rik | 1.00 | 17212 | 3 | | | | Ccer1 | 1.00 |
| 17117 | 3 | | | | | | C86187 | 1.00 | 17213 | 3 | | | | Ccin | 1.00 |
| 17118 | 3 | | | | | | C86695 | 1.00 | 17214 | 3 | | | | Cckbr | 1.00 |
| 17119 | 3 | | | | | | C87198 | 1.00 | 17215 | 3 | | | | Ccl1 | 1.00 |
| 17120 | 3 | | | | | | C87414 | 1.00 | 17216 | 3 | | | | Ccl17 | 1.00 |
| 17121 | 3 | | | | | | C87499 | 1.00 | 17217 | 3 | | | | Ccl19 | 1.00 |
| 17122 | 3 | | | | | | C87977 | 1.00 | 17218 | 3 | | | | Ccl20 | 1.00 |
| 17123 | 3 | | | | | | C9 | 1.00 | 17219 | 3 | | | | Ccl22 | 1.00 |
| 17124 | 3 | | | | | | C920009B18Rik | 1.00 | 17220 | 3 | | | | Ccl26 | 1.00 |
| 17125 | 3 | | | | | | CK137956 | 1.00 | 17221 | 3 | | | | Ccl27b | 1.00 |
| 17126 | 3 | | | | | | Cabp2 | 1.00 | 17222 | 3 | | | | Ccl28 | 1.00 |
| 17127 | 3 | | | | | | Cabp4 | 1.00 | 17223 | 3 | | | | Ccl4 | 1.00 |
| 17128 | 3 | | | | | | Cabp5 | 1.00 | 17224 | 3 | | | | Ccl5 | 1.00 |
| 17129 | 3 | | | | | | Cabp7 | 1.00 | 17225 | 3 | | | | Ccl8 | 1.00 |
| 17130 | 3 | | | | | | Cabs1 | 1.00 | 17226 | 3 | | | | Ccna1 | 1.00 |
| 17131 | 3 | | | | | | Cacna1f | 1.00 | 17227 | 3 | | | | Ccnb1ip1 | 1.00 |
| 17132 | 3 | | | | | | Cacna1i | 1.00 | 17228 | 3 | | | | Ccnb3 | 1.00 |
| 17133 | 3 | | | | | | Cacna2d4 | 1.00 | 17229 | 3 | | | | Ccnc | 1.00 |
| 17134 | 3 | | | | | | Cage1 | 1.00 | 17230 | 3 | | | | Ccr10 | 1.00 |
| 17135 | 3 | | | | | | Calcb | 1.00 | 17231 | 3 | | | | Ccrl1 | 1.00 |
| 17136 | 3 | | | | | | Calcoco2 | 1.00 | 17232 | 3 | | | | Ccr3 | 1.00 |
| 17137 | 3 | | | | | | Calcr | 1.00 | 17233 | 3 | | | | Ccr6 | 1.00 |
| 17138 | 3 | | | | | | Calhm1 | 1.00 | 17234 | 3 | | | | Ccr7 | 1.00 |
| 17139 | 3 | | | | | | Calr4 | 1.00 | 17235 | 3 | | | | Ccr9 | 1.00 |
| 17140 | 3 | | | | | | Capn11 | 1.00 | 17236 | 3 | | | | Cct6a | 1.00 |
| 17141 | 3 | | | | | | Capn12 | 1.00 | 17237 | 3 | | | | Cct6b | 1.00 |
| 17142 | 3 | | | | | | Capn13 | 1.00 | 17238 | 3 | | | | Cct8l1 | 1.00 |
| 17143 | 3 | | | | | | Capn8 | 1.00 | 17239 | 3 | | | | Cd101 | 1.00 |
| 17144 | 3 | | | | | | Capn9 | 1.00 | 17240 | 3 | | | | Cd160 | 1.00 |
| 17145 | 3 | | | | | | Caps2 | 1.00 | 17241 | 3 | | | | Cd163l1 | 1.00 |
| 17146 | 3 | | | | | | Capza3 | 1.00 | 17242 | 3 | | | | Cd164l2 | 1.00 |
| 17147 | 3 | | | | | | Car15 | 1.00 | 17243 | 3 | | | | Cd19 | 1.00 |
| 17148 | 3 | | | | | | Car4 | 1.00 | 17244 | 3 | | | | Cd1d2 | 1.00 |
| 17149 | 3 | | | | | | Car5a | 1.00 | 17245 | 3 | | | | Cd2 | 1.00 |
| 17150 | 3 | | | | | | Car6 | 1.00 | 17246 | 3 | | | | Cd200r2 | 1.00 |
| 17151 | 3 | | | | | | Car7 | 1.00 | 17247 | 3 | | | | Cd200r3 | 1.00 |
| 17152 | 3 | | | | | | Card11 | 1.00 | 17248 | 3 | | | | Cd200r4 | 1.00 |
| 17153 | 3 | | | | | | Card9 | 1.00 | 17249 | 3 | | | | Cd207 | 1.00 |
| 17154 | 3 | | | | | | Casc1 | 1.00 | 17250 | 3 | | | | Cd209a | 1.00 |
| 17155 | 3 | | | | | | Casr | 1.00 | 17251 | 3 | | | | Cd209b | 1.00 |
| 17156 | 3 | | | | | | Catip | 1.00 | 17252 | 3 | | | | Cd209c | 1.00 |
| 17157 | 3 | | | | | | Catsper1 | 1.00 | 17253 | 3 | | | | Cd209d | 1.00 |
| 17158 | 3 | | | | | | Catsper3 | 1.00 | 17254 | 3 | | | | Cd209e | 1.00 |
| 17159 | 3 | | | | | | Catsper4 | 1.00 | 17255 | 3 | | | | Cd209f | 1.00 |
| 17160 | 3 | | | | | | Catsperb | 1.00 | 17256 | 3 | | | | Cd209g | 1.00 |
| 17161 | 3 | | | | | | Catsperd | 1.00 | 17257 | 3 | | | | Cd22 | 1.00 |
| 17162 | 3 | | | | | | Catsperg1 | 1.00 | 17258 | 3 | | | | Cd226 | 1.00 |
| 17163 | 3 | | | | | | Catsperg2 | 1.00 | 17259 | 3 | | | | Cd244 | 1.00 |
| 17164 | 3 | | | | | | Ccdc103 | 1.00 | 17260 | 3 | | | | Cd247 | 1.00 |
| 17165 | 3 | | | | | | Ccdc105 | 1.00 | 17261 | 3 | | | | Cd27 | 1.00 |
| 17166 | 3 | | | | | | Ccdc108 | 1.00 | 17262 | 3 | | | | Cd28 | 1.00 |
| 17167 | 3 | | | | | | Ccdc11 | 1.00 | 17263 | 3 | | | | Cd300c | 1.00 |
| 17168 | 3 | | | | | | Ccdc110 | 1.00 | 17264 | 3 | | | | Cd300e | 1.00 |
| 17169 | 3 | | | | | | Ccdc121 | 1.00 | 17265 | 3 | | | | Cd300lb | 1.00 |
| 17170 | 3 | | | | | | Ccdc129 | 1.00 | 17266 | 3 | | | | Cd300ld | 1.00 |
| 17171 | 3 | | | | | | Ccdc13 | 1.00 | 17267 | 3 | | | | Cd300lh | 1.00 |
| 17172 | 3 | | | | | | Ccdc135 | 1.00 | 17268 | 3 | | | | Cd3d | 1.00 |
| 17173 | 3 | | | | | | Ccdc144b | 1.00 | 17269 | 3 | | | | Cd3eap | 1.00 |
| 17174 | 3 | | | | | | Ccdc146 | 1.00 | 17270 | 3 | | | | Cd4 | 1.00 |
| 17175 | 3 | | | | | | Ccdc147 | 1.00 | 17271 | 3 | | | | Cd40lg | 1.00 |
| 17176 | 3 | | | | | | Ccdc148 | 1.00 | 17272 | 3 | | | | Cd46 | 1.00 |
| 17177 | 3 | | | | | | Ccdc150 | 1.00 | 17273 | 3 | | | | Cd5 | 1.00 |
| 17178 | 3 | | | | | | Ccdc151 | 1.00 | 17274 | 3 | | | | Cd6 | 1.00 |
| 17179 | 3 | | | | | | Ccdc152 | 1.00 | 17275 | 3 | | | | Cd69 | 1.00 |
| 17180 | 3 | | | | | | Ccdc153 | 1.00 | 17276 | 3 | | | | Cd7 | 1.00 |
| 17181 | 3 | | | | | | Ccdc154 | 1.00 | 17277 | 3 | | | | Cd70 | 1.00 |

Fig. 45 - 91

| | | | | | | | | | | | | | |
|---|---|---|---|---|---|---|---|---|---|---|---|---|---|
| 17278 | 3 | | | | | | Cd72 | 1.00 | 17374 | 3 | | Clec4b2 | 1.00 |
| 17279 | 3 | | | | | | Cd80 | 1.00 | 17375 | 3 | | Clec4d | 1.00 |
| 17280 | 3 | | | | | | Cd8a | 1.00 | 17376 | 3 | | Clec4e | 1.00 |
| 17281 | 3 | | | | | | Cd8b1 | 1.00 | 17377 | 3 | | Clec4g | 1.00 |
| 17282 | 3 | | | | | | Cd96 | 1.00 | 17378 | 3 | | Cink | 1.00 |
| 17283 | 3 | | | | | | Cdc20b | 1.00 | 17379 | 3 | | Clpsl2 | 1.00 |
| 17284 | 3 | | | | | | Cdcp2 | 1.00 | 17380 | 3 | | Clrn1 | 1.00 |
| 17285 | 3 | | | | | | Cdh12 | 1.00 | 17381 | 3 | | Clrn2 | 1.00 |
| 17286 | 3 | | | | | | Cdh19 | 1.00 | 17382 | 3 | | Cma2 | 1.00 |
| 17287 | 3 | | | | | | Cdh23 | 1.00 | 17383 | 3 | | Cmah | 1.00 |
| 17288 | 3 | | | | | | Cdh26 | 1.00 | 17384 | 3 | | Cml2 | 1.00 |
| 17289 | 3 | | | | | | Cdhr3 | 1.00 | 17385 | 3 | | Cml3 | 1.00 |
| 17290 | 3 | | | | | | Cdk10 | 1.00 | 17386 | 3 | | Cml5 | 1.00 |
| 17291 | 3 | | | | | | Cdk15 | 1.00 | 17387 | 3 | | Cmtm1 | 1.00 |
| 17292 | 3 | | | | | | Cdkn2a | 1.00 | 17388 | 3 | | Cmtm2a | 1.00 |
| 17293 | 3 | | | | | | Cdnf | 1.00 | 17389 | 3 | | Cmtm2b | 1.00 |
| 17294 | 3 | | | | | | Cdrt4 | 1.00 | 17390 | 3 | | Cndp1 | 1.00 |
| 17295 | 3 | | | | | | Cdx4 | 1.00 | 17391 | 3 | | Cnga1 | 1.00 |
| 17296 | 3 | | | | | | Ceacam-ps1 | 1.00 | 17392 | 3 | | Cnga3 | 1.00 |
| 17297 | 3 | | | | | | Ceacam10 | 1.00 | 17393 | 3 | | Cnga4 | 1.00 |
| 17298 | 3 | | | | | | Ceacam11 | 1.00 | 17394 | 3 | | Cngb1 | 1.00 |
| 17299 | 3 | | | | | | Ceacam12 | 1.00 | 17395 | 3 | | Cngb3 | 1.00 |
| 17300 | 3 | | | | | | Ceacam13 | 1.00 | 17396 | 3 | | Cnnm3 | 1.00 |
| 17301 | 3 | | | | | | Ceacam14 | 1.00 | 17397 | 3 | | Cnpy1 | 1.00 |
| 17302 | 3 | | | | | | Ceacam15 | 1.00 | 17398 | 3 | | Cntn5 | 1.00 |
| 17303 | 3 | | | | | | Ceacam16 | 1.00 | 17399 | 3 | | Cntnap3 | 1.00 |
| 17304 | 3 | | | | | | Ceacam18 | 1.00 | 17400 | 3 | | Cntnap5a | 1.00 |
| 17305 | 3 | | | | | | Ceacam20 | 1.00 | 17401 | 3 | | Cntnap5b | 1.00 |
| 17306 | 3 | | | | | | Ceacam3 | 1.00 | 17402 | 3 | | Cntnap5c | 1.00 |
| 17307 | 3 | | | | | | Ceacam5 | 1.00 | 17403 | 3 | | Coasy | 1.00 |
| 17308 | 3 | | | | | | Ceacam9 | 1.00 | 17404 | 3 | | Col28a1 | 1.00 |
| 17309 | 3 | | | | | | Celrr | 1.00 | 17405 | 3 | | Col4a3 | 1.00 |
| 17310 | 3 | | | | | | Cep41 | 1.00 | 17406 | 3 | | Col4a4 | 1.00 |
| 17311 | 3 | | | | | | Cer1 | 1.00 | 17407 | 3 | | Cort | 1.00 |
| 17312 | 3 | | | | | | Cerkl | 1.00 | 17408 | 3 | | Cox7b2 | 1.00 |
| 17313 | 3 | | | | | | Ces1a | 1.00 | 17409 | 3 | | Cox8c | 1.00 |
| 17314 | 3 | | | | | | Ces1b | 1.00 | 17410 | 3 | | Cpa5 | 1.00 |
| 17315 | 3 | | | | | | Ces1e | 1.00 | 17411 | 3 | | Cpa6 | 1.00 |
| 17316 | 3 | | | | | | Ces1f | 1.00 | 17412 | 3 | | Cphx1 | 1.00 |
| 17317 | 3 | | | | | | Ces1g | 1.00 | 17413 | 3 | | Cphx2 | 1.00 |
| 17318 | 3 | | | | | | Ces2b | 1.00 | 17414 | 3 | | Cplx3 | 1.00 |
| 17319 | 3 | | | | | | Ces2c | 1.00 | 17415 | 3 | | Cplx4 | 1.00 |
| 17320 | 3 | | | | | | Ces2d-ps | 1.00 | 17416 | 3 | | Cpne6 | 1.00 |
| 17321 | 3 | | | | | | Ces2h | 1.00 | 17417 | 3 | | Cpne9 | 1.00 |
| 17322 | 3 | | | | | | Ces3a | 1.00 | 17418 | 3 | | Cpsf4l | 1.00 |
| 17323 | 3 | | | | | | Ces3b | 1.00 | 17419 | 3 | | Cpvl | 1.00 |
| 17324 | 3 | | | | | | Ces4a | 1.00 | 17420 | 3 | | Cpxcr1 | 1.00 |
| 17325 | 3 | | | | | | Ces5a | 1.00 | 17421 | 3 | | Cr2 | 1.00 |
| 17326 | 3 | | | | | | Cetn1 | 1.00 | 17422 | 3 | | Crb1 | 1.00 |
| 17327 | 3 | | | | | | Cfc1 | 1.00 | 17423 | 3 | | Creld1 | 1.00 |
| 17328 | 3 | | | | | | Cfhr1 | 1.00 | 17424 | 3 | | Crhbp | 1.00 |
| 17329 | 3 | | | | | | Cga | 1.00 | 17425 | 3 | | Crhr1 | 1.00 |
| 17330 | 3 | | | | | | Chat | 1.00 | 17426 | 3 | | Crhr2 | 1.00 |
| 17331 | 3 | | | | | | Chd9 | 1.00 | 17427 | 3 | | Crip3 | 1.00 |
| 17332 | 3 | | | | | | Chia1 | 1.00 | 17428 | 3 | | Crisp1 | 1.00 |
| 17333 | 3 | | | | | | Chil4 | 1.00 | 17429 | 3 | | Crisp2 | 1.00 |
| 17334 | 3 | | | | | | Chil6 | 1.00 | 17430 | 3 | | Crisp3 | 1.00 |
| 17335 | 3 | | | | | | Chit1 | 1.00 | 17431 | 3 | | Crisp4 | 1.00 |
| 17336 | 3 | | | | | | ChkbCpt1b | 1.00 | 17432 | 3 | | Crtam | 1.00 |
| 17337 | 3 | | | | | | Chn1os3 | 1.00 | 17433 | 3 | | Crx | 1.00 |
| 17338 | 3 | | | | | | Chrdl2 | 1.00 | 17434 | 3 | | Crxos | 1.00 |
| 17339 | 3 | | | | | | Chrm1 | 1.00 | 17435 | 3 | | Cry1 | 1.00 |
| 17340 | 3 | | | | | | Chrm4 | 1.00 | 17436 | 3 | | Crybb2 | 1.00 |
| 17341 | 3 | | | | | | Chrm5 | 1.00 | 17437 | 3 | | Crygs | 1.00 |
| 17342 | 3 | | | | | | Chrna10 | 1.00 | 17438 | 3 | | Csf2 | 1.00 |
| 17343 | 3 | | | | | | Chrna2 | 1.00 | 17439 | 3 | | Csf3 | 1.00 |
| 17344 | 3 | | | | | | Chrna6 | 1.00 | 17440 | 3 | | Csmd1 | 1.00 |
| 17345 | 3 | | | | | | Chrna9 | 1.00 | 17441 | 3 | | Csmd2os | 1.00 |
| 17346 | 3 | | | | | | Chrnb3 | 1.00 | 17442 | 3 | | Csmd3 | 1.00 |
| 17347 | 3 | | | | | | Chrne | 1.00 | 17443 | 3 | | Csn1s1 | 1.00 |
| 17348 | 3 | | | | | | Chst4 | 1.00 | 17444 | 3 | | Csn1s2a | 1.00 |
| 17349 | 3 | | | | | | Chst9 | 1.00 | 17445 | 3 | | Csn1s2b | 1.00 |
| 17350 | 3 | | | | | | Cib3 | 1.00 | 17446 | 3 | | Csn2 | 1.00 |
| 17351 | 3 | | | | | | Cib4 | 1.00 | 17447 | 3 | | Csn3 | 1.00 |
| 17352 | 3 | | | | | | Ciita | 1.00 | 17448 | 3 | | Csnka2ip | 1.00 |
| 17353 | 3 | | | | | | Cistr-act | 1.00 | 17449 | 3 | | Csprs | 1.00 |
| 17354 | 3 | | | | | | Ckb | 1.00 | 17450 | 3 | | Cst10 | 1.00 |
| 17355 | 3 | | | | | | Clca4 | 1.00 | 17451 | 3 | | Cst11 | 1.00 |
| 17356 | 3 | | | | | | Clca6 | 1.00 | 17452 | 3 | | Cst12 | 1.00 |
| 17357 | 3 | | | | | | Clcn1 | 1.00 | 17453 | 3 | | Cst13 | 1.00 |
| 17358 | 3 | | | | | | Clcnka | 1.00 | 17454 | 3 | | Cst8 | 1.00 |
| 17359 | 3 | | | | | | Clcnkb | 1.00 | 17455 | 3 | | Cst9 | 1.00 |
| 17360 | 3 | | | | | | Cldn16 | 1.00 | 17456 | 3 | | Cstl1 | 1.00 |
| 17361 | 3 | | | | | | Cldn17 | 1.00 | 17457 | 3 | | Ctag2 | 1.00 |
| 17362 | 3 | | | | | | Cldn19 | 1.00 | 17458 | 3 | | Ctcfl | 1.00 |
| 17363 | 3 | | | | | | Cldn22 | 1.00 | 17459 | 3 | | Ctcflos | 1.00 |
| 17364 | 3 | | | | | | Cldn24 | 1.00 | 17460 | 3 | | Ctf2 | 1.00 |
| 17365 | 3 | | | | | | Cldn26 | 1.00 | 17461 | 3 | | Ctla4 | 1.00 |
| 17366 | 3 | | | | | | Cldnd2 | 1.00 | 17462 | 3 | | Ctrc | 1.00 |
| 17367 | 3 | | | | | | Clec10a | 1.00 | 17463 | 3 | | Ctrcos | 1.00 |
| 17368 | 3 | | | | | | Clec12b | 1.00 | 17464 | 3 | | Ctrl | 1.00 |
| 17369 | 3 | | | | | | Clec18a | 1.00 | 17465 | 3 | | Cts3 | 1.00 |
| 17370 | 3 | | | | | | Clec2f | 1.00 | 17466 | 3 | | Cts6 | 1.00 |
| 17371 | 3 | | | | | | Clec2i | 1.00 | 17467 | 3 | | Cts7 | 1.00 |
| 17372 | 3 | | | | | | Clec4a4 | 1.00 | 17468 | 3 | | Cts8 | 1.00 |
| 17373 | 3 | | | | | | Clec4b1 | 1.00 | 17469 | 3 | | Cts8-ps | 1.00 |

Fig. 45 - 92

| | | | | | | | | | | | | | | |
|---|---|---|---|---|---|---|---|---|---|---|---|---|---|---|
| 17470 | 3 | | | | | Ctsj | 1.00 | 17566 | 3 | | | | | D030025P21Rik | 1.00 |
| 17471 | 3 | | | | | Ctsll3 | 1.00 | 17567 | 3 | | | | | D030040B21Rik | 1.00 |
| 17472 | 3 | | | | | Ctsm | 1.00 | 17568 | 3 | | | | | D030045P18Rik | 1.00 |
| 17473 | 3 | | | | | Ctsq | 1.00 | 17569 | 3 | | | | | D030047H15Rik | 1.00 |
| 17474 | 3 | | | | | Ctsr | 1.00 | 17570 | 3 | | | | | D130009I18Rik | 1.00 |
| 17475 | 3 | | | | | Ctsw | 1.00 | 17571 | 3 | | | | | D130043K22Rik | 1.00 |
| 17476 | 3 | | | | | Ctxn2 | 1.00 | 17572 | 3 | | | | | D130058E03 | 1.00 |
| 17477 | 3 | | | | | Cubn | 1.00 | 17573 | 3 | | | | | D14Ertd670e | 1.00 |
| 17478 | 3 | | | | | Cuzd1 | 1.00 | 17574 | 3 | | | | | D16Ertd519e | 1.00 |
| 17479 | 3 | | | | | Cxcl1 | 1.00 | 17575 | 3 | | | | | D17Ertd648e | 1.00 |
| 17480 | 3 | | | | | Cxcl11 | 1.00 | 17576 | 3 | | | | | D230030E09Rik | 1.00 |
| 17481 | 3 | | | | | Cxcl17 | 1.00 | 17577 | 3 | | | | | D330045A20Rik | 1.00 |
| 17482 | 3 | | | | | Cxcl2 | 1.00 | 17578 | 3 | | | | | D330050G23Rik | 1.00 |
| 17483 | 3 | | | | | Cxcl3 | 1.00 | 17579 | 3 | | | | | D4Ertd617e | 1.00 |
| 17484 | 3 | | | | | Cxcl5 | 1.00 | 17580 | 3 | | | | | D530049I02Rik | 1.00 |
| 17485 | 3 | | | | | Cxcl9 | 1.00 | 17581 | 3 | | | | | D5Ertd577e | 1.00 |
| 17486 | 3 | | | | | Cxcr1 | 1.00 | 17582 | 3 | | | | | D5Ertd605e | 1.00 |
| 17487 | 3 | | | | | Cxcr3 | 1.00 | 17583 | 3 | | | | | D630010B17Rik | 1.00 |
| 17488 | 3 | | | | | Cxcr5 | 1.00 | 17584 | 3 | | | | | D630013N20Rik | 1.00 |
| 17489 | 3 | | | | | Cxcr6 | 1.00 | 17585 | 3 | | | | | D630023F18Rik | 1.00 |
| 17490 | 3 | | | | | Cyct | 1.00 | 17586 | 3 | | | | | D630024D03Rik | 1.00 |
| 17491 | 3 | | | | | Cylc1 | 1.00 | 17587 | 3 | | | | | D630029K05Rik | 1.00 |
| 17492 | 3 | | | | | Cylc2 | 1.00 | 17588 | 3 | | | | | D630032N06Rik | 1.00 |
| 17493 | 3 | | | | | Cyp11b2 | 1.00 | 17589 | 3 | | | | | D630033O11Rik | 1.00 |
| 17494 | 3 | | | | | Cyp19a1 | 1.00 | 17590 | 3 | | | | | D630041G03Rik | 1.00 |
| 17495 | 3 | | | | | Cyp1a1 | 1.00 | 17591 | 3 | | | | | D630045M09Rik | 1.00 |
| 17496 | 3 | | | | | Cyp1a2 | 1.00 | 17592 | 3 | | | | | D6Ertd474e | 1.00 |
| 17497 | 3 | | | | | Cyp24a1 | 1.00 | 17593 | 3 | | | | | D6Ertd527e | 1.00 |
| 17498 | 3 | | | | | Cyp26c1 | 1.00 | 17594 | 3 | | | | | D730005E14Rik | 1.00 |
| 17499 | 3 | | | | | Cyp27b1 | 1.00 | 17595 | 3 | | | | | D730045A05Rik | 1.00 |
| 17500 | 3 | | | | | Cyp2a22 | 1.00 | 17596 | 3 | | | | | D730048I06Rik | 1.00 |
| 17501 | 3 | | | | | Cyp2a4 | 1.00 | 17597 | 3 | | | | | D730050B12Rik | 1.00 |
| 17502 | 3 | | | | | Cyp2ab1 | 1.00 | 17598 | 3 | | | | | D7Ertd143e | 1.00 |
| 17503 | 3 | | | | | Cyp2b10 | 1.00 | 17599 | 3 | | | | | D7Ertd443e | 1.00 |
| 17504 | 3 | | | | | Cyp2b13 | 1.00 | 17600 | 3 | | | | | D830005E20Rik | 1.00 |
| 17505 | 3 | | | | | Cyp2b23 | 1.00 | 17601 | 3 | | | | | D830013O20Rik | 1.00 |
| 17506 | 3 | | | | | Cyp2b9 | 1.00 | 17602 | 3 | | | | | D830026I12Rik | 1.00 |
| 17507 | 3 | | | | | Cyp2c29 | 1.00 | 17603 | 3 | | | | | D830032E09Rik | 1.00 |
| 17508 | 3 | | | | | Cyp2c37 | 1.00 | 17604 | 3 | | | | | D830046C22Rik | 1.00 |
| 17509 | 3 | | | | | Cyp2c38 | 1.00 | 17605 | 3 | | | | | D930007P13Rik | 1.00 |
| 17510 | 3 | | | | | Cyp2c39 | 1.00 | 17606 | 3 | | | | | D930016D06Rik | 1.00 |
| 17511 | 3 | | | | | Cyp2c50 | 1.00 | 17607 | 3 | | | | | D930020B18Rik | 1.00 |
| 17512 | 3 | | | | | Cyp2c53-ps | 1.00 | 17608 | 3 | | | | | D930032P07Rik | 1.00 |
| 17513 | 3 | | | | | Cyp2c54 | 1.00 | 17609 | 3 | | | | | DQ267100 | 1.00 |
| 17514 | 3 | | | | | Cyp2c55 | 1.00 | 17610 | 3 | | | | | DQ267101 | 1.00 |
| 17515 | 3 | | | | | Cyp2c65 | 1.00 | 17611 | 3 | | | | | DQ267102 | 1.00 |
| 17516 | 3 | | | | | Cyp2c66 | 1.00 | 17612 | 3 | | | | | DXBay18 | 1.00 |
| 17517 | 3 | | | | | Cyp2c67 | 1.00 | 17613 | 3 | | | | | Daf2 | 1.00 |
| 17518 | 3 | | | | | Cyp2c69 | 1.00 | 17614 | 3 | | | | | Dao | 1.00 |
| 17519 | 3 | | | | | Cyp2d11 | 1.00 | 17615 | 3 | | | | | Daw1 | 1.00 |
| 17520 | 3 | | | | | Cyp2d12 | 1.00 | 17616 | 3 | | | | | Dazl | 1.00 |
| 17521 | 3 | | | | | Cyp2d13 | 1.00 | 17617 | 3 | | | | | Dbhos | 1.00 |
| 17522 | 3 | | | | | Cyp2d34 | 1.00 | 17618 | 3 | | | | | Dbx2 | 1.00 |
| 17523 | 3 | | | | | Cyp2d37-ps | 1.00 | 17619 | 3 | | | | | Dcdc2b | 1.00 |
| 17524 | 3 | | | | | Cyp2d40 | 1.00 | 17620 | 3 | | | | | Dcdc2c | 1.00 |
| 17525 | 3 | | | | | Cyp2e1 | 1.00 | 17621 | 3 | | | | | Dcpp2 | 1.00 |
| 17526 | 3 | | | | | Cyp2j11 | 1.00 | 17622 | 3 | | | | | Dcst1 | 1.00 |
| 17527 | 3 | | | | | Cyp2j12 | 1.00 | 17623 | 3 | | | | | Ddi1 | 1.00 |
| 17528 | 3 | | | | | Cyp2j13 | 1.00 | 17624 | 3 | | | | | Ddx4 | 1.00 |
| 17529 | 3 | | | | | Cyp2j5 | 1.00 | 17625 | 3 | | | | | Ddx43 | 1.00 |
| 17530 | 3 | | | | | Cyp2j8 | 1.00 | 17626 | 3 | | | | | Ddx60 | 1.00 |
| 17531 | 3 | | | | | Cyp2t4 | 1.00 | 17627 | 3 | | | | | Dear1 | 1.00 |
| 17532 | 3 | | | | | Cyp3a41a | 1.00 | 17628 | 3 | | | | | Defa-ps1 | 1.00 |
| 17533 | 3 | | | | | Cyp3a41b | 1.00 | 17629 | 3 | | | | | Defa-ps12 | 1.00 |
| 17534 | 3 | | | | | Cyp3a44 | 1.00 | 17630 | 3 | | | | | Defa-ps13 | 1.00 |
| 17535 | 3 | | | | | Cyp3a57 | 1.00 | 17631 | 3 | | | | | Defa-rs1 | 1.00 |
| 17536 | 3 | | | | | Cyp3a59 | 1.00 | 17632 | 3 | | | | | Defa-rs7 | 1.00 |
| 17537 | 3 | | | | | Cyp4a10 | 1.00 | 17633 | 3 | | | | | Defa2 | 1.00 |
| 17538 | 3 | | | | | Cyp4a12a | 1.00 | 17634 | 3 | | | | | Defa20 | 1.00 |
| 17539 | 3 | | | | | Cyp4a12b | 1.00 | 17635 | 3 | | | | | Defa21 | 1.00 |
| 17540 | 3 | | | | | Cyp4a29 | 1.00 | 17636 | 3 | | | | | Defa22 | 1.00 |
| 17541 | 3 | | | | | Cyp4a30b | 1.00 | 17637 | 3 | | | | | Defa23 | 1.00 |
| 17542 | 3 | | | | | Cyp4a31 | 1.00 | 17638 | 3 | | | | | Defa25 | 1.00 |
| 17543 | 3 | | | | | Cyp4a32 | 1.00 | 17639 | 3 | | | | | Defa26 | 1.00 |
| 17544 | 3 | | | | | Cyp4b1-ps2 | 1.00 | 17640 | 3 | | | | | Defa4 | 1.00 |
| 17545 | 3 | | | | | Cyp4f14 | 1.00 | 17641 | 3 | | | | | Defa5 | 1.00 |
| 17546 | 3 | | | | | Cyp4f18 | 1.00 | 17642 | 3 | | | | | Defa6 | 1.00 |
| 17547 | 3 | | | | | Cyp4f37 | 1.00 | 17643 | 3 | | | | | Defb10 | 1.00 |
| 17548 | 3 | | | | | Cyp4f40 | 1.00 | 17644 | 3 | | | | | Defb11 | 1.00 |
| 17549 | 3 | | | | | Cyp4f41-ps | 1.00 | 17645 | 3 | | | | | Defb12 | 1.00 |
| 17550 | 3 | | | | | Cyp4x1 | 1.00 | 17646 | 3 | | | | | Defb13 | 1.00 |
| 17551 | 3 | | | | | Cyp7a1 | 1.00 | 17647 | 3 | | | | | Defb15 | 1.00 |
| 17552 | 3 | | | | | Cypt1 | 1.00 | 17648 | 3 | | | | | Defb18 | 1.00 |
| 17553 | 3 | | | | | Cypt12 | 1.00 | 17649 | 3 | | | | | Defb19 | 1.00 |
| 17554 | 3 | | | | | Cypt14 | 1.00 | 17650 | 3 | | | | | Defb2 | 1.00 |
| 17555 | 3 | | | | | Cypt15 | 1.00 | 17651 | 3 | | | | | Defb20 | 1.00 |
| 17556 | 3 | | | | | Cypt2 | 1.00 | 17652 | 3 | | | | | Defb21 | 1.00 |
| 17557 | 3 | | | | | Cypt3 | 1.00 | 17653 | 3 | | | | | Defb22 | 1.00 |
| 17558 | 3 | | | | | Cypt4 | 1.00 | 17654 | 3 | | | | | Defb23 | 1.00 |
| 17559 | 3 | | | | | Cypt7 | 1.00 | 17655 | 3 | | | | | Defb25 | 1.00 |
| 17560 | 3 | | | | | Cypt8 | 1.00 | 17656 | 3 | | | | | Defb26 | 1.00 |
| 17561 | 3 | | | | | Cypt9 | 1.00 | 17657 | 3 | | | | | Defb28 | 1.00 |
| 17562 | 3 | | | | | Cysltr2 | 1.00 | 17658 | 3 | | | | | Defb29 | 1.00 |
| 17563 | 3 | | | | | D030018L15Rik | 1.00 | 17659 | 3 | | | | | Defb3 | 1.00 |
| 17564 | 3 | | | | | D030024E09Rik | 1.00 | 17660 | 3 | | | | | Defb30 | 1.00 |
| 17565 | 3 | | | | | D030025E07Rik | 1.00 | 17661 | 3 | | | | | Defb33 | 1.00 |

Fig. 45 - 93

| | | | | | | | | | | | | | | | | |
|---|---|---|---|---|---|---|---|---|---|---|---|---|---|---|---|---|
| 17662 | 3 | | | | | Defb34 | 1.00 | 17758 | 3 | | | | | E030013I19Rik | 1.00 |
| 17663 | 3 | | | | | Defb35 | 1.00 | 17759 | 3 | | | | | E030018B13Rik | 1.00 |
| 17664 | 3 | | | | | Defb36 | 1.00 | 17760 | 3 | | | | | E030019O06Rik | 1.00 |
| 17665 | 3 | | | | | Defb37 | 1.00 | 17761 | 3 | | | | | E030025P04Rik | 1.00 |
| 17666 | 3 | | | | | Defb38 | 1.00 | 17762 | 3 | | | | | E030048B06Rik | 1.00 |
| 17667 | 3 | | | | | Defb39 | 1.00 | 17763 | 3 | | | | | E130006D01Rik | 1.00 |
| 17668 | 3 | | | | | Defb40 | 1.00 | 17764 | 3 | | | | | E130018N17Rik | 1.00 |
| 17669 | 3 | | | | | Defb41 | 1.00 | 17765 | 3 | | | | | E130215H24Rik | 1.00 |
| 17670 | 3 | | | | | Defb42 | 1.00 | 17766 | 3 | | | | | E130218I03Rik | 1.00 |
| 17671 | 3 | | | | | Defb43 | 1.00 | 17767 | 3 | | | | | E130304I02Rik | 1.00 |
| 17672 | 3 | | | | | Defb44-ps | 1.00 | 17768 | 3 | | | | | E230008N13Rik | 1.00 |
| 17673 | 3 | | | | | Defb45 | 1.00 | 17769 | 3 | | | | | E230016K23Rik | 1.00 |
| 17674 | 3 | | | | | Defb46 | 1.00 | 17770 | 3 | | | | | E230019M04Rik | 1.00 |
| 17675 | 3 | | | | | Defb47 | 1.00 | 17771 | 3 | | | | | E230025N22Rik | 1.00 |
| 17676 | 3 | | | | | Defb48 | 1.00 | 17772 | 3 | | | | | E330011O21Rik | 1.00 |
| 17677 | 3 | | | | | Defb5 | 1.00 | 17773 | 3 | | | | | E330012B07Rik | 1.00 |
| 17678 | 3 | | | | | Defb50 | 1.00 | 17774 | 3 | | | | | E330014E10Rik | 1.00 |
| 17679 | 3 | | | | | Defb6 | 1.00 | 17775 | 3 | | | | | E330017A01Rik | 1.00 |
| 17680 | 3 | | | | | Defb7 | 1.00 | 17776 | 3 | | | | | E330017L17Rik | 1.00 |
| 17681 | 3 | | | | | Defb8 | 1.00 | 17777 | 3 | | | | | E330020D12Rik | 1.00 |
| 17682 | 3 | | | | | Defb9 | 1.00 | 17778 | 3 | | | | | E330021D16Rik | 1.00 |
| 17683 | 3 | | | | | Dennd5a | 1.00 | 17779 | 3 | | | | | E330023G01Rik | 1.00 |
| 17684 | 3 | | | | | Dennd6a | 1.00 | 17780 | 3 | | | | | E330034G19Rik | 1.00 |
| 17685 | 3 | | | | | Dfnb59 | 1.00 | 17781 | 3 | | | | | E430016F16Rik | 1.00 |
| 17686 | 3 | | | | | Dgat2l6 | 1.00 | 17782 | 3 | | | | | E530001F21Rik | 1.00 |
| 17687 | 3 | | | | | Dgkb | 1.00 | 17783 | 3 | | | | | EU599041 | 1.00 |
| 17688 | 3 | | | | | Dgkeos | 1.00 | 17784 | 3 | | | | | Eaf2 | 1.00 |
| 17689 | 3 | | | | | Dgkg | 1.00 | 17785 | 3 | | | | | Ear10 | 1.00 |
| 17690 | 3 | | | | | Dhrs2 | 1.00 | 17786 | 3 | | | | | Ear14 | 1.00 |
| 17691 | 3 | | | | | Dhx38 | 1.00 | 17787 | 3 | | | | | Ear3 | 1.00 |
| 17692 | 3 | | | | | Dio1 | 1.00 | 17788 | 3 | | | | | Ear4 | 1.00 |
| 17693 | 3 | | | | | Diec1 | 1.00 | 17789 | 3 | | | | | Ear7 | 1.00 |
| 17694 | 3 | | | | | Dig1 | 1.00 | 17790 | 3 | | | | | Eci3 | 1.00 |
| 17695 | 3 | | | | | Dlx4 | 1.00 | 17791 | 3 | | | | | Ect2l | 1.00 |
| 17696 | 3 | | | | | Dlx6as2 | 1.00 | 17792 | 3 | | | | | Eddm3b | 1.00 |
| 17697 | 3 | | | | | Dmbx1 | 1.00 | 17793 | 3 | | | | | Efcab10 | 1.00 |
| 17698 | 3 | | | | | Dmr | 1.00 | 17794 | 3 | | | | | Efcab12 | 1.00 |
| 17699 | 3 | | | | | Dmrt1 | 1.00 | 17795 | 3 | | | | | Efcab3 | 1.00 |
| 17700 | 3 | | | | | Dmrta1 | 1.00 | 17796 | 3 | | | | | Efcab4b | 1.00 |
| 17701 | 3 | | | | | Dmrtc1a | 1.00 | 17797 | 3 | | | | | Efcab5 | 1.00 |
| 17702 | 3 | | | | | Dmrtc1b | 1.00 | 17798 | 3 | | | | | Efcab6 | 1.00 |
| 17703 | 3 | | | | | Dmrtc1c2 | 1.00 | 17799 | 3 | | | | | Efcab8 | 1.00 |
| 17704 | 3 | | | | | Dmrtc2 | 1.00 | 17800 | 3 | | | | | Efcab9 | 1.00 |
| 17705 | 3 | | | | | Dnaaf1 | 1.00 | 17801 | 3 | | | | | Efhb | 1.00 |
| 17706 | 3 | | | | | Dnah1 | 1.00 | 17802 | 3 | | | | | Efhc2 | 1.00 |
| 17707 | 3 | | | | | Dnah10 | 1.00 | 17803 | 3 | | | | | Egf | 1.00 |
| 17708 | 3 | | | | | Dnah11 | 1.00 | 17804 | 3 | | | | | Egfem1 | 1.00 |
| 17709 | 3 | | | | | Dnah17 | 1.00 | 17805 | 3 | | | | | Egr4 | 1.00 |
| 17710 | 3 | | | | | Dnah2 | 1.00 | 17806 | 3 | | | | | Eid3 | 1.00 |
| 17711 | 3 | | | | | Dnah5 | 1.00 | 17807 | 3 | | | | | Eif4e1b | 1.00 |
| 17712 | 3 | | | | | Dnah6 | 1.00 | 17808 | 3 | | | | | Eif4e3 | 1.00 |
| 17713 | 3 | | | | | Dnah7a | 1.00 | 17809 | 3 | | | | | Elovl3 | 1.00 |
| 17714 | 3 | | | | | Dnah7b | 1.00 | 17810 | 3 | | | | | Eml6 | 1.00 |
| 17715 | 3 | | | | | Dnah8 | 1.00 | 17811 | 3 | | | | | Emr4 | 1.00 |
| 17716 | 3 | | | | | Dnah9 | 1.00 | 17812 | 3 | | | | | Enam | 1.00 |
| 17717 | 3 | | | | | Dnaic1 | 1.00 | 17813 | 3 | | | | | Eno4 | 1.00 |
| 17718 | 3 | | | | | Dnajb8 | 1.00 | 17814 | 3 | | | | | Enpp6 | 1.00 |
| 17719 | 3 | | | | | Dnajc5b | 1.00 | 17815 | 3 | | | | | Enpp7 | 1.00 |
| 17720 | 3 | | | | | Dnajc5g | 1.00 | 17816 | 3 | | | | | Enthd1 | 1.00 |
| 17721 | 3 | | | | | Dnase1 | 1.00 | 17817 | 3 | | | | | Entpd8 | 1.00 |
| 17722 | 3 | | | | | Dnase2b | 1.00 | 17818 | 3 | | | | | Epgn | 1.00 |
| 17723 | 3 | | | | | Dnmt3aos | 1.00 | 17819 | 3 | | | | | Epha6 | 1.00 |
| 17724 | 3 | | | | | Dnmt3l | 1.00 | 17820 | 3 | | | | | Ephb4 | 1.00 |
| 17725 | 3 | | | | | Dntt | 1.00 | 17821 | 3 | | | | | Ephx4 | 1.00 |
| 17726 | 3 | | | | | Doxl2 | 1.00 | 17822 | 3 | | | | | Epo | 1.00 |
| 17727 | 3 | | | | | Dpep2 | 1.00 | 17823 | 3 | | | | | Eppin | 1.00 |
| 17728 | 3 | | | | | Dpep3 | 1.00 | 17824 | 3 | | | | | Eps15 | 1.00 |
| 17729 | 3 | | | | | Dppa1 | 1.00 | 17825 | 3 | | | | | Epx | 1.00 |
| 17730 | 3 | | | | | Dppa2 | 1.00 | 17826 | 3 | | | | | Eqtn | 1.00 |
| 17731 | 3 | | | | | Dppa3 | 1.00 | 17827 | 3 | | | | | Eras | 1.00 |
| 17732 | 3 | | | | | Dppa4 | 1.00 | 17828 | 3 | | | | | Erbb3 | 1.00 |
| 17733 | 3 | | | | | Dppa5a | 1.00 | 17829 | 3 | | | | | Erich2 | 1.00 |
| 17734 | 3 | | | | | Dpy19l2 | 1.00 | 17830 | 3 | | | | | Erich3 | 1.00 |
| 17735 | 3 | | | | | Drc1 | 1.00 | 17831 | 3 | | | | | Erich5 | 1.00 |
| 17736 | 3 | | | | | Drd1a | 1.00 | 17832 | 3 | | | | | Erich6 | 1.00 |
| 17737 | 3 | | | | | Drd2 | 1.00 | 17833 | 3 | | | | | Ermn | 1.00 |
| 17738 | 3 | | | | | Drd3 | 1.00 | 17834 | 3 | | | | | Ern2 | 1.00 |
| 17739 | 3 | | | | | Drd4 | 1.00 | 17835 | 3 | | | | | Erp27 | 1.00 |
| 17740 | 3 | | | | | Drd5 | 1.00 | 17836 | 3 | | | | | Erv3 | 1.00 |
| 17741 | 3 | | | | | Dreh | 1.00 | 17837 | 3 | | | | | Esp1 | 1.00 |
| 17742 | 3 | | | | | Dsg4 | 1.00 | 17838 | 3 | | | | | Esp15 | 1.00 |
| 17743 | 3 | | | | | Dspp | 1.00 | 17839 | 3 | | | | | Esp16 | 1.00 |
| 17744 | 3 | | | | | Dthd1 | 1.00 | 17840 | 3 | | | | | Esp18 | 1.00 |
| 17745 | 3 | | | | | Duox1 | 1.00 | 17841 | 3 | | | | | Esp23 | 1.00 |
| 17746 | 3 | | | | | Duox2 | 1.00 | 17842 | 3 | | | | | Esp24 | 1.00 |
| 17747 | 3 | | | | | Duoxa2 | 1.00 | 17843 | 3 | | | | | Esp3 | 1.00 |
| 17748 | 3 | | | | | Dusp21 | 1.00 | 17844 | 3 | | | | | Esp31 | 1.00 |
| 17749 | 3 | | | | | Dux | 1.00 | 17845 | 3 | | | | | Esp34 | 1.00 |
| 17750 | 3 | | | | | Dvl2 | 1.00 | 17846 | 3 | | | | | Esp36 | 1.00 |
| 17751 | 3 | | | | | Dydc1 | 1.00 | 17847 | 3 | | | | | Esp38 | 1.00 |
| 17752 | 3 | | | | | Dydc2 | 1.00 | 17848 | 3 | | | | | Esp4 | 1.00 |
| 17753 | 3 | | | | | Dyrk4 | 1.00 | 17849 | 3 | | | | | Esp5 | 1.00 |
| 17754 | 3 | | | | | Dytn | 1.00 | 17850 | 3 | | | | | Esp6 | 1.00 |
| 17755 | 3 | | | | | Dyx1c1 | 1.00 | 17851 | 3 | | | | | Esp6-esp5 | 1.00 |
| 17756 | 3 | | | | | E030003E18Rik | 1.00 | 17852 | 3 | | | | | Esp8 | 1.00 |
| 17757 | 3 | | | | | E030011O05Rik | 1.00 | 17853 | 3 | | | | | Espnl | 1.00 |

Fig. 45 - 94

| | | | | | | | | | | | | | | | | |
|---|---|---|---|---|---|---|---|---|---|---|---|---|---|---|---|---|
| 17854 | 3 | | | | | Esr1 | 1.00 | 17950 | 3 | | | | | Fcrl6 | 1.00 |
| 17855 | 3 | | | | | Esr2 | 1.00 | 17951 | 3 | | | | | Fcrla | 1.00 |
| 17856 | 3 | | | | | Esx1 | 1.00 | 17952 | 3 | | | | | Fcrlb | 1.00 |
| 17857 | 3 | | | | | Esyt1 | 1.00 | 17953 | 3 | | | | | Fer1l4 | 1.00 |
| 17858 | 3 | | | | | Etd | 1.00 | 17954 | 3 | | | | | Fer1l5 | 1.00 |
| 17859 | 3 | | | | | Etnk1 | 1.00 | 17955 | 3 | | | | | Ferd3l | 1.00 |
| 17860 | 3 | | | | | Etnppl | 1.00 | 17956 | 3 | | | | | Fev | 1.00 |
| 17861 | 3 | | | | | Etv2 | 1.00 | 17957 | 3 | | | | | Ffar1 | 1.00 |
| 17862 | 3 | | | | | Evi2a-evi2b | 1.00 | 17958 | 3 | | | | | Ffar2 | 1.00 |
| 17863 | 3 | | | | | Evx1 | 1.00 | 17959 | 3 | | | | | Ffar3 | 1.00 |
| 17864 | 3 | | | | | Evx2 | 1.00 | 17960 | 3 | | | | | Ffar4 | 1.00 |
| 17865 | 3 | | | | | Exd1 | 1.00 | 17961 | 3 | | | | | Fgf16 | 1.00 |
| 17866 | 3 | | | | | F630042J09Rik | 1.00 | 17962 | 3 | | | | | Fgf17 | 1.00 |
| 17867 | 3 | | | | | F630111L10Rik | 1.00 | 17963 | 3 | | | | | Fgf20 | 1.00 |
| 17868 | 3 | | | | | F630206G17Rik | 1.00 | 17964 | 3 | | | | | Fgf23 | 1.00 |
| 17869 | 3 | | | | | F730035M05Rik | 1.00 | 17965 | 3 | | | | | Fgf3 | 1.00 |
| 17870 | 3 | | | | | F830045P16Rik | 1.00 | 17966 | 3 | | | | | Fgf4 | 1.00 |
| 17871 | 3 | | | | | Fa2h | 1.00 | 17967 | 3 | | | | | Fgf5 | 1.00 |
| 17872 | 3 | | | | | Fabp12 | 1.00 | 17968 | 3 | | | | | Fgf8 | 1.00 |
| 17873 | 3 | | | | | Fabp6 | 1.00 | 17969 | 3 | | | | | Fhad1 | 1.00 |
| 17874 | 3 | | | | | Fabp9 | 1.00 | 17970 | 3 | | | | | Fhad1os1 | 1.00 |
| 17875 | 3 | | | | | Faim3 | 1.00 | 17971 | 3 | | | | | Fhit | 1.00 |
| 17876 | 3 | | | | | Fam115e | 1.00 | 17972 | 3 | | | | | Fhl4 | 1.00 |
| 17877 | 3 | | | | | Fam122c | 1.00 | 17973 | 3 | | | | | Fhl5 | 1.00 |
| 17878 | 3 | | | | | Fam129c | 1.00 | 17974 | 3 | | | | | Figla | 1.00 |
| 17879 | 3 | | | | | Fam135b | 1.00 | 17975 | 3 | | | | | Fkbp6 | 1.00 |
| 17880 | 3 | | | | | Fam150a | 1.00 | 17976 | 3 | | | | | Flt3 | 1.00 |
| 17881 | 3 | | | | | Fam150b | 1.00 | 17977 | 3 | | | | | Fmo3 | 1.00 |
| 17882 | 3 | | | | | Fam151a | 1.00 | 17978 | 3 | | | | | Fmo4 | 1.00 |
| 17883 | 3 | | | | | Fam154a | 1.00 | 17979 | 3 | | | | | Fmo6 | 1.00 |
| 17884 | 3 | | | | | Fam159b | 1.00 | 17980 | 3 | | | | | Fmo9 | 1.00 |
| 17885 | 3 | | | | | Fam162b | 1.00 | 17981 | 3 | | | | | Fmr1nb | 1.00 |
| 17886 | 3 | | | | | Fam166a | 1.00 | 17982 | 3 | | | | | Fndc2 | 1.00 |
| 17887 | 3 | | | | | Fam166b | 1.00 | 17983 | 3 | | | | | Fndc7 | 1.00 |
| 17888 | 3 | | | | | Fam170a | 1.00 | 17984 | 3 | | | | | Fndc8 | 1.00 |
| 17889 | 3 | | | | | Fam170b | 1.00 | 17985 | 3 | | | | | Fnip2 | 1.00 |
| 17890 | 3 | | | | | Fam178b | 1.00 | 17986 | 3 | | | | | Folh1 | 1.00 |
| 17891 | 3 | | | | | Fam179a | 1.00 | 17987 | 3 | | | | | Folr4 | 1.00 |
| 17892 | 3 | | | | | Fam181a | 1.00 | 17988 | 3 | | | | | Fosl1 | 1.00 |
| 17893 | 3 | | | | | Fam186b | 1.00 | 17989 | 3 | | | | | Foxb2 | 1.00 |
| 17894 | 3 | | | | | Fam187a | 1.00 | 17990 | 3 | | | | | Foxd4 | 1.00 |
| 17895 | 3 | | | | | Fam19a3 | 1.00 | 17991 | 3 | | | | | Foxe1 | 1.00 |
| 17896 | 3 | | | | | Fam19a4 | 1.00 | 17992 | 3 | | | | | Foxe3 | 1.00 |
| 17897 | 3 | | | | | Fam209 | 1.00 | 17993 | 3 | | | | | Foxh1 | 1.00 |
| 17898 | 3 | | | | | Fam216b | 1.00 | 17994 | 3 | | | | | Foxi1 | 1.00 |
| 17899 | 3 | | | | | Fam217a | 1.00 | 17995 | 3 | | | | | Foxi2 | 1.00 |
| 17900 | 3 | | | | | Fam221b | 1.00 | 17996 | 3 | | | | | Foxn4 | 1.00 |
| 17901 | 3 | | | | | Fam227b | 1.00 | 17997 | 3 | | | | | Foxp3 | 1.00 |
| 17902 | 3 | | | | | Fam228a | 1.00 | 17998 | 3 | | | | | Foxr1 | 1.00 |
| 17903 | 3 | | | | | Fam229a | 1.00 | 17999 | 3 | | | | | Foxr2 | 1.00 |
| 17904 | 3 | | | | | Fam24a | 1.00 | 18000 | 3 | | | | | Fpr-rs3 | 1.00 |
| 17905 | 3 | | | | | Fam26d | 1.00 | 18001 | 3 | | | | | Fpr-rs4 | 1.00 |
| 17906 | 3 | | | | | Fam26f | 1.00 | 18002 | 3 | | | | | Fpr-rs6 | 1.00 |
| 17907 | 3 | | | | | Fam3b | 1.00 | 18003 | 3 | | | | | Fpr3 | 1.00 |
| 17908 | 3 | | | | | Fam46d | 1.00 | 18004 | 3 | | | | | Frem3 | 1.00 |
| 17909 | 3 | | | | | Fam47c | 1.00 | 18005 | 3 | | | | | Frmpd1os | 1.00 |
| 17910 | 3 | | | | | Fam47e | 1.00 | 18006 | 3 | | | | | Frmpd3 | 1.00 |
| 17911 | 3 | | | | | Fam50b | 1.00 | 18007 | 3 | | | | | Frmpd4 | 1.00 |
| 17912 | 3 | | | | | Fam71a | 1.00 | 18008 | 3 | | | | | Frs3os | 1.00 |
| 17913 | 3 | | | | | Fam71b | 1.00 | 18009 | 3 | | | | | Fscb | 1.00 |
| 17914 | 3 | | | | | Fam71d | 1.00 | 18010 | 3 | | | | | Fscn2 | 1.00 |
| 17915 | 3 | | | | | Fam71e2 | 1.00 | 18011 | 3 | | | | | Fscn3 | 1.00 |
| 17916 | 3 | | | | | Fam71f1 | 1.00 | 18012 | 3 | | | | | Fshb | 1.00 |
| 17917 | 3 | | | | | Fam71f2 | 1.00 | 18013 | 3 | | | | | Fshr | 1.00 |
| 17918 | 3 | | | | | Fam92b | 1.00 | 18014 | 3 | | | | | Fsip1 | 1.00 |
| 17919 | 3 | | | | | Fanca | 1.00 | 18015 | 3 | | | | | Fthl17 | 1.00 |
| 17920 | 3 | | | | | Fancd2os | 1.00 | 18016 | 3 | | | | | Ftmt | 1.00 |
| 17921 | 3 | | | | | Fank1 | 1.00 | 18017 | 3 | | | | | Fut4-ps1 | 1.00 |
| 17922 | 3 | | | | | Fasl | 1.00 | 18018 | 3 | | | | | Fut7 | 1.00 |
| 17923 | 3 | | | | | Fate1 | 1.00 | 18019 | 3 | | | | | Fxyd1 | 1.00 |
| 17924 | 3 | | | | | Fbxl13 | 1.00 | 18020 | 3 | | | | | Fxyd3 | 1.00 |
| 17925 | 3 | | | | | Fbxo15 | 1.00 | 18021 | 3 | | | | | Fxyd4 | 1.00 |
| 17926 | 3 | | | | | Fbxo24 | 1.00 | 18022 | 3 | | | | | G530011O06Rik | 1.00 |
| 17927 | 3 | | | | | Fbxo39 | 1.00 | 18023 | 3 | | | | | G630055G22Rik | 1.00 |
| 17928 | 3 | | | | | Fbxo43 | 1.00 | 18024 | 3 | | | | | G630071F17Rik | 1.00 |
| 17929 | 3 | | | | | Fbxo47 | 1.00 | 18025 | 3 | | | | | G630093K05Rik | 1.00 |
| 17930 | 3 | | | | | Fbxo7 | 1.00 | 18026 | 3 | | | | | G6bos | 1.00 |
| 17931 | 3 | | | | | Fbxw10 | 1.00 | 18027 | 3 | | | | | G6pc | 1.00 |
| 17932 | 3 | | | | | Fbxw13 | 1.00 | 18028 | 3 | | | | | G6pc2 | 1.00 |
| 17933 | 3 | | | | | Fbxw14 | 1.00 | 18029 | 3 | | | | | G730013B05Rik | 1.00 |
| 17934 | 3 | | | | | Fbxw15 | 1.00 | 18030 | 3 | | | | | Gabra6 | 1.00 |
| 17935 | 3 | | | | | Fbxw16 | 1.00 | 18031 | 3 | | | | | Gabrd | 1.00 |
| 17936 | 3 | | | | | Fbxw18 | 1.00 | 18032 | 3 | | | | | Gabrg3 | 1.00 |
| 17937 | 3 | | | | | Fbxw19 | 1.00 | 18033 | 3 | | | | | Gabrq | 1.00 |
| 17938 | 3 | | | | | Fbxw20 | 1.00 | 18034 | 3 | | | | | Gabrr1 | 1.00 |
| 17939 | 3 | | | | | Fbxw21 | 1.00 | 18035 | 3 | | | | | Gabrr2 | 1.00 |
| 17940 | 3 | | | | | Fbxw22 | 1.00 | 18036 | 3 | | | | | Gabrr3 | 1.00 |
| 17941 | 3 | | | | | Fbxw24 | 1.00 | 18037 | 3 | | | | | Gad1os | 1.00 |
| 17942 | 3 | | | | | Fbxw26 | 1.00 | 18038 | 3 | | | | | Gal | 1.00 |
| 17943 | 3 | | | | | Fbxw28 | 1.00 | 18039 | 3 | | | | | Gal3st2 | 1.00 |
| 17944 | 3 | | | | | Fcamr | 1.00 | 18040 | 3 | | | | | Galnt5 | 1.00 |
| 17945 | 3 | | | | | Fcer1a | 1.00 | 18041 | 3 | | | | | Galp | 1.00 |
| 17946 | 3 | | | | | Fcer2a | 1.00 | 18042 | 3 | | | | | Galr1 | 1.00 |
| 17947 | 3 | | | | | Fcf1 | 1.00 | 18043 | 3 | | | | | Galr2 | 1.00 |
| 17948 | 3 | | | | | Fcrl1 | 1.00 | 18044 | 3 | | | | | Galr3 | 1.00 |
| 17949 | 3 | | | | | Fcrl5 | 1.00 | 18045 | 3 | | | | | Gapdhs | 1.00 |

Fig. 45 - 95

| | | | | | | | | | | | | | | | |
|---|---|---|---|---|---|---|---|---|---|---|---|---|---|---|---|
| 18046 | 3 | | | | | Gapt | 1.00 | 18142 | 3 | | | | | Gm10440 | 1.00 |
| 18047 | 3 | | | | | Gas2l2 | 1.00 | 18143 | 3 | | | | | Gm10445 | 1.00 |
| 18048 | 3 | | | | | Gast | 1.00 | 18144 | 3 | | | | | Gm1045 | 1.00 |
| 18049 | 3 | | | | | Gata5os | 1.00 | 18145 | 3 | | | | | Gm10451 | 1.00 |
| 18050 | 3 | | | | | Gatad2a | 1.00 | 18146 | 3 | | | | | Gm10466 | 1.00 |
| 18051 | 3 | | | | | Gbp10 | 1.00 | 18147 | 3 | | | | | Gm10471 | 1.00 |
| 18052 | 3 | | | | | Gbp11 | 1.00 | 18148 | 3 | | | | | Gm10474 | 1.00 |
| 18053 | 3 | | | | | Gbp2b | 1.00 | 18149 | 3 | | | | | Gm10486 | 1.00 |
| 18054 | 3 | | | | | Gbp4 | 1.00 | 18150 | 3 | | | | | Gm10487 | 1.00 |
| 18055 | 3 | | | | | Gbp5 | 1.00 | 18151 | 3 | | | | | Gm10488 | 1.00 |
| 18056 | 3 | | | | | Gbp8 | 1.00 | 18152 | 3 | | | | | Gm10494 | 1.00 |
| 18057 | 3 | | | | | Gck | 1.00 | 18153 | 3 | | | | | Gm10510 | 1.00 |
| 18058 | 3 | | | | | Gcm1 | 1.00 | 18154 | 3 | | | | | Gm10512 | 1.00 |
| 18059 | 3 | | | | | Gcm2 | 1.00 | 18155 | 3 | | | | | Gm10532 | 1.00 |
| 18060 | 3 | | | | | Gcnt3 | 1.00 | 18156 | 3 | | | | | Gm10536 | 1.00 |
| 18061 | 3 | | | | | Gcnt7 | 1.00 | 18157 | 3 | | | | | Gm10538 | 1.00 |
| 18062 | 3 | | | | | Gdf3 | 1.00 | 18158 | 3 | | | | | Gm10548 | 1.00 |
| 18063 | 3 | | | | | Gdf7 | 1.00 | 18159 | 3 | | | | | Gm10549 | 1.00 |
| 18064 | 3 | | | | | Gdpd4 | 1.00 | 18160 | 3 | | | | | Gm10556 | 1.00 |
| 18065 | 3 | | | | | Gfral | 1.00 | 18161 | 3 | | | | | Gm10578 | 1.00 |
| 18066 | 3 | | | | | Ggn | 1.00 | 18162 | 3 | | | | | Gm10584 | 1.00 |
| 18067 | 3 | | | | | Ghrh | 1.00 | 18163 | 3 | | | | | Gm10619 | 1.00 |
| 18068 | 3 | | | | | Ghrhr | 1.00 | 18164 | 3 | | | | | Gm10635 | 1.00 |
| 18069 | 3 | | | | | Ghsr | 1.00 | 18165 | 3 | | | | | Gm10636 | 1.00 |
| 18070 | 3 | | | | | Gif | 1.00 | 18166 | 3 | | | | | Gm10637 | 1.00 |
| 18071 | 3 | | | | | Gimap3 | 1.00 | 18167 | 3 | | | | | Gm10639 | 1.00 |
| 18072 | 3 | | | | | Gimap7 | 1.00 | 18168 | 3 | | | | | Gm10640 | 1.00 |
| 18073 | 3 | | | | | Gip | 1.00 | 18169 | 3 | | | | | Gm10649 | 1.00 |
| 18074 | 3 | | | | | Gipc3 | 1.00 | 18170 | 3 | | | | | Gm10662 | 1.00 |
| 18075 | 3 | | | | | Gja10 | 1.00 | 18171 | 3 | | | | | Gm10665 | 1.00 |
| 18076 | 3 | | | | | Gja6 | 1.00 | 18172 | 3 | | | | | Gm10666 | 1.00 |
| 18077 | 3 | | | | | Gjc2 | 1.00 | 18173 | 3 | | | | | Gm10670 | 1.00 |
| 18078 | 3 | | | | | Gje1 | 1.00 | 18174 | 3 | | | | | Gm10677 | 1.00 |
| 18079 | 3 | | | | | Gk2 | 1.00 | 18175 | 3 | | | | | Gm10684 | 1.00 |
| 18080 | 3 | | | | | Gkn1 | 1.00 | 18176 | 3 | | | | | Gm10696 | 1.00 |
| 18081 | 3 | | | | | Gkn2 | 1.00 | 18177 | 3 | | | | | Gm10714 | 1.00 |
| 18082 | 3 | | | | | Gkn3 | 1.00 | 18178 | 3 | | | | | Gm10731 | 1.00 |
| 18083 | 3 | | | | | Glb1l3 | 1.00 | 18179 | 3 | | | | | Gm10745 | 1.00 |
| 18084 | 3 | | | | | Gldn | 1.00 | 18180 | 3 | | | | | Gm10754 | 1.00 |
| 18085 | 3 | | | | | Gldnos | 1.00 | 18181 | 3 | | | | | Gm10782 | 1.00 |
| 18086 | 3 | | | | | Glipr1l1 | 1.00 | 18182 | 3 | | | | | Gm10787 | 1.00 |
| 18087 | 3 | | | | | Glipr1l2 | 1.00 | 18183 | 3 | | | | | Gm10789 | 1.00 |
| 18088 | 3 | | | | | Glod5 | 1.00 | 18184 | 3 | | | | | Gm10790 | 1.00 |
| 18089 | 3 | | | | | Glp1r | 1.00 | 18185 | 3 | | | | | Gm10804 | 1.00 |
| 18090 | 3 | | | | | Glp2r | 1.00 | 18186 | 3 | | | | | Gm10814 | 1.00 |
| 18091 | 3 | | | | | Glra1 | 1.00 | 18187 | 3 | | | | | Gm10823 | 1.00 |
| 18092 | 3 | | | | | Glra3 | 1.00 | 18188 | 3 | | | | | Gm10825 | 1.00 |
| 18093 | 3 | | | | | Glra4 | 1.00 | 18189 | 3 | | | | | Gm10845 | 1.00 |
| 18094 | 3 | | | | | Glrp1 | 1.00 | 18190 | 3 | | | | | Gm10863 | 1.00 |
| 18095 | 3 | | | | | Glt6d1 | 1.00 | 18191 | 3 | | | | | Gm10865 | 1.00 |
| 18096 | 3 | | | | | Glyat | 1.00 | 18192 | 3 | | | | | Gm10872 | 1.00 |
| 18097 | 3 | | | | | Glyatl3 | 1.00 | 18193 | 3 | | | | | Gm10921 | 1.00 |
| 18098 | 3 | | | | | Glycam1 | 1.00 | 18194 | 3 | | | | | Gm10922 | 1.00 |
| 18099 | 3 | | | | | Gm10007 | 1.00 | 18195 | 3 | | | | | Gm1110 | 1.00 |
| 18100 | 3 | | | | | Gm10024 | 1.00 | 18196 | 3 | | | | | Gm11127 | 1.00 |
| 18101 | 3 | | | | | Gm10046 | 1.00 | 18197 | 3 | | | | | Gm11128 | 1.00 |
| 18102 | 3 | | | | | Gm10052 | 1.00 | 18198 | 3 | | | | | Gm11149 | 1.00 |
| 18103 | 3 | | | | | Gm10057 | 1.00 | 18199 | 3 | | | | | Gm11166 | 1.00 |
| 18104 | 3 | | | | | Gm10058 | 1.00 | 18200 | 3 | | | | | Gm11186 | 1.00 |
| 18105 | 3 | | | | | Gm10081 | 1.00 | 18201 | 3 | | | | | Gm11190 | 1.00 |
| 18106 | 3 | | | | | Gm10096 | 1.00 | 18202 | 3 | | | | | Gm11201 | 1.00 |
| 18107 | 3 | | | | | Gm101 | 1.00 | 18203 | 3 | | | | | Gm11213 | 1.00 |
| 18108 | 3 | | | | | Gm10100 | 1.00 | 18204 | 3 | | | | | Gm1123 | 1.00 |
| 18109 | 3 | | | | | Gm10104 | 1.00 | 18205 | 3 | | | | | Gm11237 | 1.00 |
| 18110 | 3 | | | | | Gm10125 | 1.00 | 18206 | 3 | | | | | Gm11240 | 1.00 |
| 18111 | 3 | | | | | Gm10142 | 1.00 | 18207 | 3 | | | | | Gm11351 | 1.00 |
| 18112 | 3 | | | | | Gm10147 | 1.00 | 18208 | 3 | | | | | Gm1140 | 1.00 |
| 18113 | 3 | | | | | Gm10190 | 1.00 | 18209 | 3 | | | | | Gm1141 | 1.00 |
| 18114 | 3 | | | | | Gm10220 | 1.00 | 18210 | 3 | | | | | Gm11413 | 1.00 |
| 18115 | 3 | | | | | Gm10228 | 1.00 | 18211 | 3 | | | | | Gm11426 | 1.00 |
| 18116 | 3 | | | | | Gm10229 | 1.00 | 18212 | 3 | | | | | Gm11437 | 1.00 |
| 18117 | 3 | | | | | Gm10230 | 1.00 | 18213 | 3 | | | | | Gm11468 | 1.00 |
| 18118 | 3 | | | | | Gm10248 | 1.00 | 18214 | 3 | | | | | Gm11487 | 1.00 |
| 18119 | 3 | | | | | Gm10267 | 1.00 | 18215 | 3 | | | | | Gm11517 | 1.00 |
| 18120 | 3 | | | | | Gm10272 | 1.00 | 18216 | 3 | | | | | Gm11529 | 1.00 |
| 18121 | 3 | | | | | Gm10280 | 1.00 | 18217 | 3 | | | | | Gm11538 | 1.00 |
| 18122 | 3 | | | | | Gm10318 | 1.00 | 18218 | 3 | | | | | Gm11541 | 1.00 |
| 18123 | 3 | | | | | Gm10319 | 1.00 | 18219 | 3 | | | | | Gm11544 | 1.00 |
| 18124 | 3 | | | | | Gm10324 | 1.00 | 18220 | 3 | | | | | Gm11545 | 1.00 |
| 18125 | 3 | | | | | Gm10354 | 1.00 | 18221 | 3 | | | | | Gm11548 | 1.00 |
| 18126 | 3 | | | | | Gm10364 | 1.00 | 18222 | 3 | | | | | Gm11549 | 1.00 |
| 18127 | 3 | | | | | Gm10373 | 1.00 | 18223 | 3 | | | | | Gm11554 | 1.00 |
| 18128 | 3 | | | | | Gm10375 | 1.00 | 18224 | 3 | | | | | Gm11559 | 1.00 |
| 18129 | 3 | | | | | Gm10377 | 1.00 | 18225 | 3 | | | | | Gm11562 | 1.00 |
| 18130 | 3 | | | | | Gm10389 | 1.00 | 18226 | 3 | | | | | Gm11563 | 1.00 |
| 18131 | 3 | | | | | Gm10390 | 1.00 | 18227 | 3 | | | | | Gm11564 | 1.00 |
| 18132 | 3 | | | | | Gm10400 | 1.00 | 18228 | 3 | | | | | Gm11565 | 1.00 |
| 18133 | 3 | | | | | Gm10408 | 1.00 | 18229 | 3 | | | | | Gm11567 | 1.00 |
| 18134 | 3 | | | | | Gm10413 | 1.00 | 18230 | 3 | | | | | Gm11568 | 1.00 |
| 18135 | 3 | | | | | Gm10415 | 1.00 | 18231 | 3 | | | | | Gm11569 | 1.00 |
| 18136 | 3 | | | | | Gm10416 | 1.00 | 18232 | 3 | | | | | Gm11570 | 1.00 |
| 18137 | 3 | | | | | Gm10421 | 1.00 | 18233 | 3 | | | | | Gm11595 | 1.00 |
| 18138 | 3 | | | | | Gm10432 | 1.00 | 18234 | 3 | | | | | Gm11596 | 1.00 |
| 18139 | 3 | | | | | Gm10433 | 1.00 | 18235 | 3 | | | | | Gm11651 | 1.00 |
| 18140 | 3 | | | | | Gm10436 | 1.00 | 18236 | 3 | | | | | Gm11710 | 1.00 |
| 18141 | 3 | | | | | Gm10439 | 1.00 | 18237 | 3 | | | | | Gm11744 | 1.00 |

Fig. 45 - 96

| | | | | | | | | |
|---|---|---|---|---|---|---|---|---|
| 18238 | 3 | | | | | Gm11747 | 1.00 |
| 18239 | 3 | | | | | Gm11757 | 1.00 |
| 18240 | 3 | | | | | Gm11758 | 1.00 |
| 18241 | 3 | | | | | Gm11762 | 1.00 |
| 18242 | 3 | | | | | Gm11780 | 1.00 |
| 18243 | 3 | | | | | Gm11937 | 1.00 |
| 18244 | 3 | | | | | Gm11938 | 1.00 |
| 18245 | 3 | | | | | Gm11961 | 1.00 |
| 18246 | 3 | | | | | Gm11978 | 1.00 |
| 18247 | 3 | | | | | Gm11981 | 1.00 |
| 18248 | 3 | | | | | Gm11985 | 1.00 |
| 18249 | 3 | | | | | Gm12 | 1.00 |
| 18250 | 3 | | | | | Gm12130 | 1.00 |
| 18251 | 3 | | | | | Gm12159 | 1.00 |
| 18252 | 3 | | | | | Gm12169 | 1.00 |
| 18253 | 3 | | | | | Gm12171 | 1.00 |
| 18254 | 3 | | | | | Gm12185 | 1.00 |
| 18255 | 3 | | | | | Gm12191 | 1.00 |
| 18256 | 3 | | | | | Gm12216 | 1.00 |
| 18257 | 3 | | | | | Gm12238 | 1.00 |
| 18258 | 3 | | | | | Gm12250 | 1.00 |
| 18259 | 3 | | | | | Gm12253 | 1.00 |
| 18260 | 3 | | | | | Gm12295 | 1.00 |
| 18261 | 3 | | | | | Gm12298 | 1.00 |
| 18262 | 3 | | | | | Gm12409 | 1.00 |
| 18263 | 3 | | | | | Gm12429 | 1.00 |
| 18264 | 3 | | | | | Gm12505 | 1.00 |
| 18265 | 3 | | | | | Gm12522 | 1.00 |
| 18266 | 3 | | | | | Gm12530 | 1.00 |
| 18267 | 3 | | | | | Gm12603 | 1.00 |
| 18268 | 3 | | | | | Gm12633 | 1.00 |
| 18269 | 3 | | | | | Gm12695 | 1.00 |
| 18270 | 3 | | | | | Gm12709 | 1.00 |
| 18271 | 3 | | | | | Gm12718 | 1.00 |
| 18272 | 3 | | | | | Gm12789 | 1.00 |
| 18273 | 3 | | | | | Gm12794 | 1.00 |
| 18274 | 3 | | | | | Gm128 | 1.00 |
| 18275 | 3 | | | | | Gm12830 | 1.00 |
| 18276 | 3 | | | | | Gm12886 | 1.00 |
| 18277 | 3 | | | | | Gm12887 | 1.00 |
| 18278 | 3 | | | | | Gm12888 | 1.00 |
| 18279 | 3 | | | | | Gm13003 | 1.00 |
| 18280 | 3 | | | | | Gm13011 | 1.00 |
| 18281 | 3 | | | | | Gm13023 | 1.00 |
| 18282 | 3 | | | | | Gm13031 | 1.00 |
| 18283 | 3 | | | | | Gm13032 | 1.00 |
| 18284 | 3 | | | | | Gm13040 | 1.00 |
| 18285 | 3 | | | | | Gm13043 | 1.00 |
| 18286 | 3 | | | | | Gm13051 | 1.00 |
| 18287 | 3 | | | | | Gm13057 | 1.00 |
| 18288 | 3 | | | | | Gm13078 | 1.00 |
| 18289 | 3 | | | | | Gm13083 | 1.00 |
| 18290 | 3 | | | | | Gm13084 | 1.00 |
| 18291 | 3 | | | | | Gm13088 | 1.00 |
| 18292 | 3 | | | | | Gm13102 | 1.00 |
| 18293 | 3 | | | | | Gm13103 | 1.00 |
| 18294 | 3 | | | | | Gm13119 | 1.00 |
| 18295 | 3 | | | | | Gm13124 | 1.00 |
| 18296 | 3 | | | | | Gm13125 | 1.00 |
| 18297 | 3 | | | | | Gm13128 | 1.00 |
| 18298 | 3 | | | | | Gm13154 | 1.00 |
| 18299 | 3 | | | | | Gm13177 | 1.00 |
| 18300 | 3 | | | | | Gm13178 | 1.00 |
| 18301 | 3 | | | | | Gm1322 | 1.00 |
| 18302 | 3 | | | | | Gm13242 | 1.00 |
| 18303 | 3 | | | | | Gm13247 | 1.00 |
| 18304 | 3 | | | | | Gm13271 | 1.00 |
| 18305 | 3 | | | | | Gm13272 | 1.00 |
| 18306 | 3 | | | | | Gm13275 | 1.00 |
| 18307 | 3 | | | | | Gm13276 | 1.00 |
| 18308 | 3 | | | | | Gm13277 | 1.00 |
| 18309 | 3 | | | | | Gm13278 | 1.00 |
| 18310 | 3 | | | | | Gm13279 | 1.00 |
| 18311 | 3 | | | | | Gm13283 | 1.00 |
| 18312 | 3 | | | | | Gm13285 | 1.00 |
| 18313 | 3 | | | | | Gm13286 | 1.00 |
| 18314 | 3 | | | | | Gm13288 | 1.00 |
| 18315 | 3 | | | | | Gm13290 | 1.00 |
| 18316 | 3 | | | | | Gm13293 | 1.00 |
| 18317 | 3 | | | | | Gm13315 | 1.00 |
| 18318 | 3 | | | | | Gm13446 | 1.00 |
| 18319 | 3 | | | | | Gm13483 | 1.00 |
| 18320 | 3 | | | | | Gm13490 | 1.00 |
| 18321 | 3 | | | | | Gm13497 | 1.00 |
| 18322 | 3 | | | | | Gm13539 | 1.00 |
| 18323 | 3 | | | | | Gm13544 | 1.00 |
| 18324 | 3 | | | | | Gm13546 | 1.00 |
| 18325 | 3 | | | | | Gm13547 | 1.00 |
| 18326 | 3 | | | | | Gm13580 | 1.00 |
| 18327 | 3 | | | | | Gm13582 | 1.00 |
| 18328 | 3 | | | | | Gm136 | 1.00 |
| 18329 | 3 | | | | | Gm13629 | 1.00 |
| 18330 | 3 | | | | | Gm13710 | 1.00 |
| 18331 | 3 | | | | | Gm13749 | 1.00 |
| 18332 | 3 | | | | | Gm13752 | 1.00 |
| 18333 | 3 | | | | | Gm13769 | 1.00 |
| 18334 | 3 | | | | | Gm13807 | 1.00 |
| 18335 | 3 | | | | | Gm13871 | 1.00 |
| 18336 | 3 | | | | | Gm13939 | 1.00 |
| 18337 | 3 | | | | | Gm13944 | 1.00 |
| 18338 | 3 | | | | | Gm14015 | 1.00 |
| 18339 | 3 | | | | | Gm14023 | 1.00 |
| 18340 | 3 | | | | | Gm14085 | 1.00 |
| 18341 | 3 | | | | | Gm14092 | 1.00 |
| 18342 | 3 | | | | | Gm14124 | 1.00 |
| 18343 | 3 | | | | | Gm14139 | 1.00 |
| 18344 | 3 | | | | | Gm14151 | 1.00 |
| 18345 | 3 | | | | | Gm14169 | 1.00 |
| 18346 | 3 | | | | | Gm14288 | 1.00 |
| 18347 | 3 | | | | | Gm14306 | 1.00 |
| 18348 | 3 | | | | | Gm14327 | 1.00 |
| 18349 | 3 | | | | | Gm14345 | 1.00 |
| 18350 | 3 | | | | | Gm14346 | 1.00 |
| 18351 | 3 | | | | | Gm14347 | 1.00 |
| 18352 | 3 | | | | | Gm14351 | 1.00 |
| 18353 | 3 | | | | | Gm14374 | 1.00 |
| 18354 | 3 | | | | | Gm14379 | 1.00 |
| 18355 | 3 | | | | | Gm14405 | 1.00 |
| 18356 | 3 | | | | | Gm14458 | 1.00 |
| 18357 | 3 | | | | | Gm14459 | 1.00 |
| 18358 | 3 | | | | | Gm14461 | 1.00 |
| 18359 | 3 | | | | | Gm14474 | 1.00 |
| 18360 | 3 | | | | | Gm14475 | 1.00 |
| 18361 | 3 | | | | | Gm14476 | 1.00 |
| 18362 | 3 | | | | | Gm14477 | 1.00 |
| 18363 | 3 | | | | | Gm14478 | 1.00 |
| 18364 | 3 | | | | | Gm14479 | 1.00 |
| 18365 | 3 | | | | | Gm14482 | 1.00 |
| 18366 | 3 | | | | | Gm14483 | 1.00 |
| 18367 | 3 | | | | | Gm14484 | 1.00 |
| 18368 | 3 | | | | | Gm14496 | 1.00 |
| 18369 | 3 | | | | | Gm14499 | 1.00 |
| 18370 | 3 | | | | | Gm14501 | 1.00 |
| 18371 | 3 | | | | | Gm14511 | 1.00 |
| 18372 | 3 | | | | | Gm14525 | 1.00 |
| 18373 | 3 | | | | | Gm14548 | 1.00 |
| 18374 | 3 | | | | | Gm14625 | 1.00 |
| 18375 | 3 | | | | | Gm14632 | 1.00 |
| 18376 | 3 | | | | | Gm14685 | 1.00 |
| 18377 | 3 | | | | | Gm14692 | 1.00 |
| 18378 | 3 | | | | | Gm14718 | 1.00 |
| 18379 | 3 | | | | | Gm14725 | 1.00 |
| 18380 | 3 | | | | | Gm14743 | 1.00 |
| 18381 | 3 | | | | | Gm14744 | 1.00 |
| 18382 | 3 | | | | | Gm14781 | 1.00 |
| 18383 | 3 | | | | | Gm14812 | 1.00 |
| 18384 | 3 | | | | | Gm14819 | 1.00 |
| 18385 | 3 | | | | | Gm14827 | 1.00 |
| 18386 | 3 | | | | | Gm14850 | 1.00 |
| 18387 | 3 | | | | | Gm14851 | 1.00 |
| 18388 | 3 | | | | | Gm14858 | 1.00 |
| 18389 | 3 | | | | | Gm14920 | 1.00 |
| 18390 | 3 | | | | | Gm15008 | 1.00 |
| 18391 | 3 | | | | | Gm15023 | 1.00 |
| 18392 | 3 | | | | | Gm15056 | 1.00 |
| 18393 | 3 | | | | | Gm15091 | 1.00 |
| 18394 | 3 | | | | | Gm15093 | 1.00 |
| 18395 | 3 | | | | | Gm15097 | 1.00 |
| 18396 | 3 | | | | | Gm15104 | 1.00 |
| 18397 | 3 | | | | | Gm15107 | 1.00 |
| 18398 | 3 | | | | | Gm15114 | 1.00 |
| 18399 | 3 | | | | | Gm15127 | 1.00 |
| 18400 | 3 | | | | | Gm15133 | 1.00 |
| 18401 | 3 | | | | | Gm15140 | 1.00 |
| 18402 | 3 | | | | | Gm15179 | 1.00 |
| 18403 | 3 | | | | | Gm15217 | 1.00 |
| 18404 | 3 | | | | | Gm1527 | 1.00 |
| 18405 | 3 | | | | | Gm15284 | 1.00 |
| 18406 | 3 | | | | | Gm15292 | 1.00 |
| 18407 | 3 | | | | | Gm15293 | 1.00 |
| 18408 | 3 | | | | | Gm15299 | 1.00 |
| 18409 | 3 | | | | | Gm15308 | 1.00 |
| 18410 | 3 | | | | | Gm15315 | 1.00 |
| 18411 | 3 | | | | | Gm15319 | 1.00 |
| 18412 | 3 | | | | | Gm15348 | 1.00 |
| 18413 | 3 | | | | | Gm15350 | 1.00 |
| 18414 | 3 | | | | | Gm15386 | 1.00 |
| 18415 | 3 | | | | | Gm15401 | 1.00 |
| 18416 | 3 | | | | | Gm15412 | 1.00 |
| 18417 | 3 | | | | | Gm15413 | 1.00 |
| 18418 | 3 | | | | | Gm15471 | 1.00 |
| 18419 | 3 | | | | | Gm1553 | 1.00 |
| 18420 | 3 | | | | | Gm156 | 1.00 |
| 18421 | 3 | | | | | Gm1564 | 1.00 |
| 18422 | 3 | | | | | Gm15645 | 1.00 |
| 18423 | 3 | | | | | Gm15679 | 1.00 |
| 18424 | 3 | | | | | Gm15698 | 1.00 |
| 18425 | 3 | | | | | Gm15713 | 1.00 |
| 18426 | 3 | | | | | Gm15850 | 1.00 |
| 18427 | 3 | | | | | Gm1587 | 1.00 |
| 18428 | 3 | | | | | Gm15880 | 1.00 |
| 18429 | 3 | | | | | Gm15881 | 1.00 |

Fig. 45 - 97

| | | | | | | | | | | | | | | | |
|---|---|---|---|---|---|---|---|---|---|---|---|---|---|---|---|
| 18430 | 3 | | | | | | Gm15910 | 1.00 | 18526 | 3 | | | | Gm2016 | 1.00 |
| 18431 | 3 | | | | | | Gm15941 | 1.00 | 18527 | 3 | | | | Gm20172 | 1.00 |
| 18432 | 3 | | | | | | Gm15987 | 1.00 | 18528 | 3 | | | | Gm20187 | 1.00 |
| 18433 | 3 | | | | | | Gm15997 | 1.00 | 18529 | 3 | | | | Gm20199 | 1.00 |
| 18434 | 3 | | | | | | Gm1604b | 1.00 | 18530 | 3 | | | | Gm2022 | 1.00 |
| 18435 | 3 | | | | | | Gm16063 | 1.00 | 18531 | 3 | | | | Gm20268 | 1.00 |
| 18436 | 3 | | | | | | Gm16130 | 1.00 | 18532 | 3 | | | | Gm2030 | 1.00 |
| 18437 | 3 | | | | | | Gm16157 | 1.00 | 18533 | 3 | | | | Gm20319 | 1.00 |
| 18438 | 3 | | | | | | Gm16287 | 1.00 | 18534 | 3 | | | | Gm20324 | 1.00 |
| 18439 | 3 | | | | | | Gm16291 | 1.00 | 18535 | 3 | | | | Gm20356 | 1.00 |
| 18440 | 3 | | | | | | Gm16294 | 1.00 | 18536 | 3 | | | | Gm20362 | 1.00 |
| 18441 | 3 | | | | | | Gm1631 | 1.00 | 18537 | 3 | | | | Gm2042 | 1.00 |
| 18442 | 3 | | | | | | Gm16325 | 1.00 | 18538 | 3 | | | | Gm20556 | 1.00 |
| 18443 | 3 | | | | | | Gm16336 | 1.00 | 18539 | 3 | | | | Gm20594 | 1.00 |
| 18444 | 3 | | | | | | Gm16367 | 1.00 | 18540 | 3 | | | | Gm20597 | 1.00 |
| 18445 | 3 | | | | | | Gm16390 | 1.00 | 18541 | 3 | | | | Gm20611 | 1.00 |
| 18446 | 3 | | | | | | Gm16404 | 1.00 | 18542 | 3 | | | | Gm20735 | 1.00 |
| 18447 | 3 | | | | | | Gm16405 | 1.00 | 18543 | 3 | | | | Gm20736 | 1.00 |
| 18448 | 3 | | | | | | Gm16430 | 1.00 | 18544 | 3 | | | | Gm20738 | 1.00 |
| 18449 | 3 | | | | | | Gm16432 | 1.00 | 18545 | 3 | | | | Gm20740 | 1.00 |
| 18450 | 3 | | | | | | Gm16445 | 1.00 | 18546 | 3 | | | | Gm20743 | 1.00 |
| 18451 | 3 | | | | | | Gm16451 | 1.00 | 18547 | 3 | | | | Gm20744 | 1.00 |
| 18452 | 3 | | | | | | Gm1647 | 1.00 | 18548 | 3 | | | | Gm20745 | 1.00 |
| 18453 | 3 | | | | | | Gm16497 | 1.00 | 18549 | 3 | | | | Gm20747 | 1.00 |
| 18454 | 3 | | | | | | Gm16501 | 1.00 | 18550 | 3 | | | | Gm20750 | 1.00 |
| 18455 | 3 | | | | | | Gm1653 | 1.00 | 18551 | 3 | | | | Gm20751 | 1.00 |
| 18456 | 3 | | | | | | Gm16548 | 1.00 | 18552 | 3 | | | | Gm20752 | 1.00 |
| 18457 | 3 | | | | | | Gm1661 | 1.00 | 18553 | 3 | | | | Gm20753 | 1.00 |
| 18458 | 3 | | | | | | Gm16677 | 1.00 | 18554 | 3 | | | | Gm20754 | 1.00 |
| 18459 | 3 | | | | | | Gm16701 | 1.00 | 18555 | 3 | | | | Gm20755 | 1.00 |
| 18460 | 3 | | | | | | Gm16712 | 1.00 | 18556 | 3 | | | | Gm20756 | 1.00 |
| 18461 | 3 | | | | | | Gm16793 | 1.00 | 18557 | 3 | | | | Gm20757 | 1.00 |
| 18462 | 3 | | | | | | Gm16796 | 1.00 | 18558 | 3 | | | | Gm20758 | 1.00 |
| 18463 | 3 | | | | | | Gm16833 | 1.00 | 18559 | 3 | | | | Gm20759 | 1.00 |
| 18464 | 3 | | | | | | Gm16853 | 1.00 | 18560 | 3 | | | | Gm20765 | 1.00 |
| 18465 | 3 | | | | | | Gm16863 | 1.00 | 18561 | 3 | | | | Gm20767 | 1.00 |
| 18466 | 3 | | | | | | Gm16880 | 1.00 | 18562 | 3 | | | | Gm20806 | 1.00 |
| 18467 | 3 | | | | | | Gm16894 | 1.00 | 18563 | 3 | | | | Gm20809 | 1.00 |
| 18468 | 3 | | | | | | Gm16897 | 1.00 | 18564 | 3 | | | | Gm20815 | 1.00 |
| 18469 | 3 | | | | | | Gm16938 | 1.00 | 18565 | 3 | | | | Gm20816 | 1.00 |
| 18470 | 3 | | | | | | Gm16998 | 1.00 | 18566 | 3 | | | | Gm20822 | 1.00 |
| 18471 | 3 | | | | | | Gm17019 | 1.00 | 18567 | 3 | | | | Gm20823 | 1.00 |
| 18472 | 3 | | | | | | Gm1715 | 1.00 | 18568 | 3 | | | | Gm20826 | 1.00 |
| 18473 | 3 | | | | | | Gm1720 | 1.00 | 18569 | 3 | | | | Gm2083 | 1.00 |
| 18474 | 3 | | | | | | Gm17252 | 1.00 | 18570 | 3 | | | | Gm20831 | 1.00 |
| 18475 | 3 | | | | | | Gm17359 | 1.00 | 18571 | 3 | | | | Gm20854 | 1.00 |
| 18476 | 3 | | | | | | Gm17365 | 1.00 | 18572 | 3 | | | | Gm20857 | 1.00 |
| 18477 | 3 | | | | | | Gm17644 | 1.00 | 18573 | 3 | | | | Gm20858 | 1.00 |
| 18478 | 3 | | | | | | Gm17660 | 1.00 | 18574 | 3 | | | | Gm20865 | 1.00 |
| 18479 | 3 | | | | | | Gm17677 | 1.00 | 18575 | 3 | | | | Gm20867 | 1.00 |
| 18480 | 3 | | | | | | Gm17689 | 1.00 | 18576 | 3 | | | | Gm2087 | 1.00 |
| 18481 | 3 | | | | | | Gm17727 | 1.00 | 18577 | 3 | | | | Gm20871 | 1.00 |
| 18482 | 3 | | | | | | Gm17745 | 1.00 | 18578 | 3 | | | | Gm20877 | 1.00 |
| 18483 | 3 | | | | | | Gm17746 | 1.00 | 18579 | 3 | | | | Gm20917 | 1.00 |
| 18484 | 3 | | | | | | Gm17751 | 1.00 | 18580 | 3 | | | | Gm20939 | 1.00 |
| 18485 | 3 | | | | | | Gm17757 | 1.00 | 18581 | 3 | | | | Gm21002 | 1.00 |
| 18486 | 3 | | | | | | Gm17769 | 1.00 | 18582 | 3 | | | | Gm21057 | 1.00 |
| 18487 | 3 | | | | | | Gm17801 | 1.00 | 18583 | 3 | | | | Gm2109 | 1.00 |
| 18488 | 3 | | | | | | Gm17821 | 1.00 | 18584 | 3 | | | | Gm21119 | 1.00 |
| 18489 | 3 | | | | | | Gm17830 | 1.00 | 18585 | 3 | | | | Gm21221 | 1.00 |
| 18490 | 3 | | | | | | Gm18409 | 1.00 | 18586 | 3 | | | | Gm21269 | 1.00 |
| 18491 | 3 | | | | | | Gm18853 | 1.00 | 18587 | 3 | | | | Gm21276 | 1.00 |
| 18492 | 3 | | | | | | Gm19276 | 1.00 | 18588 | 3 | | | | Gm21283 | 1.00 |
| 18493 | 3 | | | | | | Gm19277 | 1.00 | 18589 | 3 | | | | Gm21284 | 1.00 |
| 18494 | 3 | | | | | | Gm19299 | 1.00 | 18590 | 3 | | | | Gm21293 | 1.00 |
| 18495 | 3 | | | | | | Gm19303 | 1.00 | 18591 | 3 | | | | Gm21304 | 1.00 |
| 18496 | 3 | | | | | | Gm19395 | 1.00 | 18592 | 3 | | | | Gm21312 | 1.00 |
| 18497 | 3 | | | | | | Gm19402 | 1.00 | 18593 | 3 | | | | Gm21319 | 1.00 |
| 18498 | 3 | | | | | | Gm19424 | 1.00 | 18594 | 3 | | | | Gm21498 | 1.00 |
| 18499 | 3 | | | | | | Gm19434 | 1.00 | 18595 | 3 | | | | Gm21586 | 1.00 |
| 18500 | 3 | | | | | | Gm19461 | 1.00 | 18596 | 3 | | | | Gm21637 | 1.00 |
| 18501 | 3 | | | | | | Gm19466 | 1.00 | 18597 | 3 | | | | Gm21671 | 1.00 |
| 18502 | 3 | | | | | | Gm19510 | 1.00 | 18598 | 3 | | | | Gm21693 | 1.00 |
| 18503 | 3 | | | | | | Gm19522 | 1.00 | 18599 | 3 | | | | Gm21708 | 1.00 |
| 18504 | 3 | | | | | | Gm19583 | 1.00 | 18600 | 3 | | | | Gm2176 | 1.00 |
| 18505 | 3 | | | | | | Gm19589 | 1.00 | 18601 | 3 | | | | Gm21943 | 1.00 |
| 18506 | 3 | | | | | | Gm19619 | 1.00 | 18602 | 3 | | | | Gm21944 | 1.00 |
| 18507 | 3 | | | | | | Gm1965 | 1.00 | 18603 | 3 | | | | Gm21949 | 1.00 |
| 18508 | 3 | | | | | | Gm19668 | 1.00 | 18604 | 3 | | | | Gm21950 | 1.00 |
| 18509 | 3 | | | | | | Gm1968 | 1.00 | 18605 | 3 | | | | Gm21951 | 1.00 |
| 18510 | 3 | | | | | | Gm19689 | 1.00 | 18606 | 3 | | | | Gm2373 | 1.00 |
| 18511 | 3 | | | | | | Gm19710 | 1.00 | 18607 | 3 | | | | Gm2381 | 1.00 |
| 18512 | 3 | | | | | | Gm19757 | 1.00 | 18608 | 3 | | | | Gm2447 | 1.00 |
| 18513 | 3 | | | | | | Gm19782 | 1.00 | 18609 | 3 | | | | Gm2516 | 1.00 |
| 18514 | 3 | | | | | | Gm19784 | 1.00 | 18610 | 3 | | | | Gm2663 | 1.00 |
| 18515 | 3 | | | | | | Gm1979 | 1.00 | 18611 | 3 | | | | Gm2696 | 1.00 |
| 18516 | 3 | | | | | | Gm1987 | 1.00 | 18612 | 3 | | | | Gm2721 | 1.00 |
| 18517 | 3 | | | | | | Gm19897 | 1.00 | 18613 | 3 | | | | Gm2762 | 1.00 |
| 18518 | 3 | | | | | | Gm1993 | 1.00 | 18614 | 3 | | | | Gm2799 | 1.00 |
| 18519 | 3 | | | | | | Gm2002 | 1.00 | 18615 | 3 | | | | Gm2825 | 1.00 |
| 18520 | 3 | | | | | | Gm20063 | 1.00 | 18616 | 3 | | | | Gm2837 | 1.00 |
| 18521 | 3 | | | | | | Gm20098 | 1.00 | 18617 | 3 | | | | Gm2848 | 1.00 |
| 18522 | 3 | | | | | | Gm20110 | 1.00 | 18618 | 3 | | | | Gm2863 | 1.00 |
| 18523 | 3 | | | | | | Gm2012 | 1.00 | 18619 | 3 | | | | Gm2913 | 1.00 |
| 18524 | 3 | | | | | | Gm20125 | 1.00 | 18620 | 3 | | | | Gm2927 | 1.00 |
| 18525 | 3 | | | | | | Gm20139 | 1.00 | 18621 | 3 | | | | Gm2933 | 1.00 |

Fig. 45 - 98

| | | | | | | | | | | | | | | |
|---|---|---|---|---|---|---|---|---|---|---|---|---|---|---|
| 18622 | 3 | | | | | Gm3020 | 1.00 | 18718 | 3 | | | | Gm4981 | 1.00 |
| 18623 | 3 | | | | | Gm3086 | 1.00 | 18719 | 3 | | | | Gm4984 | 1.00 |
| 18624 | 3 | | | | | Gm3139 | 1.00 | 18720 | 3 | | | | Gm5 | 1.00 |
| 18625 | 3 | | | | | Gm3143 | 1.00 | 18721 | 3 | | | | Gm5039 | 1.00 |
| 18626 | 3 | | | | | Gm3230 | 1.00 | 18722 | 3 | | | | Gm5071 | 1.00 |
| 18627 | 3 | | | | | Gm3238 | 1.00 | 18723 | 3 | | | | Gm5072 | 1.00 |
| 18628 | 3 | | | | | Gm3259 | 1.00 | 18724 | 3 | | | | Gm5082 | 1.00 |
| 18629 | 3 | | | | | Gm3279 | 1.00 | 18725 | 3 | | | | Gm5083 | 1.00 |
| 18630 | 3 | | | | | Gm3285 | 1.00 | 18726 | 3 | | | | Gm5084 | 1.00 |
| 18631 | 3 | | | | | Gm3286 | 1.00 | 18727 | 3 | | | | Gm5086 | 1.00 |
| 18632 | 3 | | | | | Gm3336 | 1.00 | 18728 | 3 | | | | Gm5087 | 1.00 |
| 18633 | 3 | | | | | Gm3402 | 1.00 | 18729 | 3 | | | | Gm5091 | 1.00 |
| 18634 | 3 | | | | | Gm3404 | 1.00 | 18730 | 3 | | | | Gm5095 | 1.00 |
| 18635 | 3 | | | | | Gm3409 | 1.00 | 18731 | 3 | | | | Gm5108 | 1.00 |
| 18636 | 3 | | | | | Gm3415 | 1.00 | 18732 | 3 | | | | Gm5111 | 1.00 |
| 18637 | 3 | | | | | Gm3417 | 1.00 | 18733 | 3 | | | | Gm5114 | 1.00 |
| 18638 | 3 | | | | | Gm3428 | 1.00 | 18734 | 3 | | | | Gm5122 | 1.00 |
| 18639 | 3 | | | | | Gm3434 | 1.00 | 18735 | 3 | | | | Gm5127 | 1.00 |
| 18640 | 3 | | | | | Gm3458 | 1.00 | 18736 | 3 | | | | Gm5129 | 1.00 |
| 18641 | 3 | | | | | Gm362 | 1.00 | 18737 | 3 | | | | Gm5132 | 1.00 |
| 18642 | 3 | | | | | Gm364 | 1.00 | 18738 | 3 | | | | Gm5134 | 1.00 |
| 18643 | 3 | | | | | Gm3646 | 1.00 | 18739 | 3 | | | | Gm5136 | 1.00 |
| 18644 | 3 | | | | | Gm3701 | 1.00 | 18740 | 3 | | | | Gm5142 | 1.00 |
| 18645 | 3 | | | | | Gm3706 | 1.00 | 18741 | 3 | | | | Gm5150 | 1.00 |
| 18646 | 3 | | | | | Gm3716 | 1.00 | 18742 | 3 | | | | Gm5166 | 1.00 |
| 18647 | 3 | | | | | Gm3750 | 1.00 | 18743 | 3 | | | | Gm5168 | 1.00 |
| 18648 | 3 | | | | | Gm3763 | 1.00 | 18744 | 3 | | | | Gm5169 | 1.00 |
| 18649 | 3 | | | | | Gm382 | 1.00 | 18745 | 3 | | | | Gm5177 | 1.00 |
| 18650 | 3 | | | | | Gm3893 | 1.00 | 18746 | 3 | | | | Gm525 | 1.00 |
| 18651 | 3 | | | | | Gm3985 | 1.00 | 18747 | 3 | | | | Gm5294 | 1.00 |
| 18652 | 3 | | | | | Gm4027 | 1.00 | 18748 | 3 | | | | Gm5334 | 1.00 |
| 18653 | 3 | | | | | Gm41 | 1.00 | 18749 | 3 | | | | Gm5346 | 1.00 |
| 18654 | 3 | | | | | Gm4133 | 1.00 | 18750 | 3 | | | | Gm5347 | 1.00 |
| 18655 | 3 | | | | | Gm4175 | 1.00 | 18751 | 3 | | | | Gm5382 | 1.00 |
| 18656 | 3 | | | | | Gm4201 | 1.00 | 18752 | 3 | | | | Gm5409 | 1.00 |
| 18657 | 3 | | | | | Gm4214 | 1.00 | 18753 | 3 | | | | Gm5414 | 1.00 |
| 18658 | 3 | | | | | Gm4216 | 1.00 | 18754 | 3 | | | | Gm5420 | 1.00 |
| 18659 | 3 | | | | | Gm4224 | 1.00 | 18755 | 3 | | | | Gm5431 | 1.00 |
| 18660 | 3 | | | | | Gm4251 | 1.00 | 18756 | 3 | | | | Gm5441 | 1.00 |
| 18661 | 3 | | | | | Gm4262 | 1.00 | 18757 | 3 | | | | Gm5458 | 1.00 |
| 18662 | 3 | | | | | Gm4265 | 1.00 | 18758 | 3 | | | | Gm5460 | 1.00 |
| 18663 | 3 | | | | | Gm4278 | 1.00 | 18759 | 3 | | | | Gm5464 | 1.00 |
| 18664 | 3 | | | | | Gm428 | 1.00 | 18760 | 3 | | | | Gm5475 | 1.00 |
| 18665 | 3 | | | | | Gm4297 | 1.00 | 18761 | 3 | | | | Gm5476 | 1.00 |
| 18666 | 3 | | | | | Gm4301 | 1.00 | 18762 | 3 | | | | Gm5477 | 1.00 |
| 18667 | 3 | | | | | Gm4302 | 1.00 | 18763 | 3 | | | | Gm5478 | 1.00 |
| 18668 | 3 | | | | | Gm4303 | 1.00 | 18764 | 3 | | | | Gm5485 | 1.00 |
| 18669 | 3 | | | | | Gm4307 | 1.00 | 18765 | 3 | | | | Gm5523 | 1.00 |
| 18670 | 3 | | | | | Gm4312 | 1.00 | 18766 | 3 | | | | Gm5531 | 1.00 |
| 18671 | 3 | | | | | Gm4340 | 1.00 | 18767 | 3 | | | | Gm5535 | 1.00 |
| 18672 | 3 | | | | | Gm436 | 1.00 | 18768 | 3 | | | | Gm5538 | 1.00 |
| 18673 | 3 | | | | | Gm4371 | 1.00 | 18769 | 3 | | | | Gm5544 | 1.00 |
| 18674 | 3 | | | | | Gm44 | 1.00 | 18770 | 3 | | | | Gm5547 | 1.00 |
| 18675 | 3 | | | | | Gm4432 | 1.00 | 18771 | 3 | | | | Gm5549 | 1.00 |
| 18676 | 3 | | | | | Gm4461 | 1.00 | 18772 | 3 | | | | Gm5591 | 1.00 |
| 18677 | 3 | | | | | Gm4477 | 1.00 | 18773 | 3 | | | | Gm5592 | 1.00 |
| 18678 | 3 | | | | | Gm4489 | 1.00 | 18774 | 3 | | | | Gm5615 | 1.00 |
| 18679 | 3 | | | | | Gm4541 | 1.00 | 18775 | 3 | | | | Gm5622 | 1.00 |
| 18680 | 3 | | | | | Gm4559 | 1.00 | 18776 | 3 | | | | Gm5627 | 1.00 |
| 18681 | 3 | | | | | Gm4566 | 1.00 | 18777 | 3 | | | | Gm5634 | 1.00 |
| 18682 | 3 | | | | | Gm4567 | 1.00 | 18778 | 3 | | | | Gm5635 | 1.00 |
| 18683 | 3 | | | | | Gm4598 | 1.00 | 18779 | 3 | | | | Gm5640 | 1.00 |
| 18684 | 3 | | | | | Gm4710 | 1.00 | 18780 | 3 | | | | Gm5662 | 1.00 |
| 18685 | 3 | | | | | Gm4719 | 1.00 | 18781 | 3 | | | | Gm5712 | 1.00 |
| 18686 | 3 | | | | | Gm4736 | 1.00 | 18782 | 3 | | | | Gm572 | 1.00 |
| 18687 | 3 | | | | | Gm4745 | 1.00 | 18783 | 3 | | | | Gm5725 | 1.00 |
| 18688 | 3 | | | | | Gm4759 | 1.00 | 18784 | 3 | | | | Gm5726 | 1.00 |
| 18689 | 3 | | | | | Gm4763 | 1.00 | 18785 | 3 | | | | Gm5728 | 1.00 |
| 18690 | 3 | | | | | Gm4776 | 1.00 | 18786 | 3 | | | | Gm5741 | 1.00 |
| 18691 | 3 | | | | | Gm4787 | 1.00 | 18787 | 3 | | | | Gm5766 | 1.00 |
| 18692 | 3 | | | | | Gm4788 | 1.00 | 18788 | 3 | | | | Gm5795 | 1.00 |
| 18693 | 3 | | | | | Gm4791 | 1.00 | 18789 | 3 | | | | Gm5797 | 1.00 |
| 18694 | 3 | | | | | Gm4792 | 1.00 | 18790 | 3 | | | | Gm5800 | 1.00 |
| 18695 | 3 | | | | | Gm4794 | 1.00 | 18791 | 3 | | | | Gm5820 | 1.00 |
| 18696 | 3 | | | | | Gm4814 | 1.00 | 18792 | 3 | | | | Gm5833 | 1.00 |
| 18697 | 3 | | | | | Gm4827 | 1.00 | 18793 | 3 | | | | Gm5860 | 1.00 |
| 18698 | 3 | | | | | Gm4832 | 1.00 | 18794 | 3 | | | | Gm5862 | 1.00 |
| 18699 | 3 | | | | | Gm4836 | 1.00 | 18795 | 3 | | | | Gm5868 | 1.00 |
| 18700 | 3 | | | | | Gm4841 | 1.00 | 18796 | 3 | | | | Gm5878 | 1.00 |
| 18701 | 3 | | | | | Gm4846 | 1.00 | 18797 | 3 | | | | Gm5885 | 1.00 |
| 18702 | 3 | | | | | Gm4847 | 1.00 | 18798 | 3 | | | | Gm5886 | 1.00 |
| 18703 | 3 | | | | | Gm4850 | 1.00 | 18799 | 3 | | | | Gm5891 | 1.00 |
| 18704 | 3 | | | | | Gm4858 | 1.00 | 18800 | 3 | | | | Gm5893 | 1.00 |
| 18705 | 3 | | | | | Gm4861 | 1.00 | 18801 | 3 | | | | Gm590 | 1.00 |
| 18706 | 3 | | | | | Gm4871 | 1.00 | 18802 | 3 | | | | Gm5901 | 1.00 |
| 18707 | 3 | | | | | Gm4872 | 1.00 | 18803 | 3 | | | | Gm5916 | 1.00 |
| 18708 | 3 | | | | | Gm4884 | 1.00 | 18804 | 3 | | | | Gm5925 | 1.00 |
| 18709 | 3 | | | | | Gm4894 | 1.00 | 18805 | 3 | | | | Gm5934 | 1.00 |
| 18710 | 3 | | | | | Gm4906 | 1.00 | 18806 | 3 | | | | Gm5935 | 1.00 |
| 18711 | 3 | | | | | Gm4922 | 1.00 | 18807 | 3 | | | | Gm5936 | 1.00 |
| 18712 | 3 | | | | | Gm4925 | 1.00 | 18808 | 3 | | | | Gm5938 | 1.00 |
| 18713 | 3 | | | | | Gm4926 | 1.00 | 18809 | 3 | | | | Gm5941 | 1.00 |
| 18714 | 3 | | | | | Gm4937 | 1.00 | 18810 | 3 | | | | Gm595 | 1.00 |
| 18715 | 3 | | | | | Gm4956 | 1.00 | 18811 | 3 | | | | Gm597 | 1.00 |
| 18716 | 3 | | | | | Gm4971 | 1.00 | 18812 | 3 | | | | Gm6026 | 1.00 |
| 18717 | 3 | | | | | Gm4975 | 1.00 | 18813 | 3 | | | | Gm6034 | 1.00 |

Fig. 45 - 99

| | | | | | | | | | | | | | | | | |
|---|---|---|---|---|---|---|---|---|---|---|---|---|---|---|---|---|
| 18814 | 3 | | | | | | Gm6040 | 1.00 | 18910 | 3 | | | | | Gm8179 | 1.00 |
| 18815 | 3 | | | | | | Gm6042 | 1.00 | 18911 | 3 | | | | | Gm8221 | 1.00 |
| 18816 | 3 | | | | | | Gm6083 | 1.00 | 18912 | 3 | | | | | Gm8234 | 1.00 |
| 18817 | 3 | | | | | | Gm6086 | 1.00 | 18913 | 3 | | | | | Gm8267 | 1.00 |
| 18818 | 3 | | | | | | Gm609 | 1.00 | 18914 | 3 | | | | | Gm829 | 1.00 |
| 18819 | 3 | | | | | | Gm6116 | 1.00 | 18915 | 3 | | | | | Gm8298 | 1.00 |
| 18820 | 3 | | | | | | Gm6121 | 1.00 | 18916 | 3 | | | | | Gm8300 | 1.00 |
| 18821 | 3 | | | | | | Gm614 | 1.00 | 18917 | 3 | | | | | Gm833 | 1.00 |
| 18822 | 3 | | | | | | Gm6150 | 1.00 | 18918 | 3 | | | | | Gm8369 | 1.00 |
| 18823 | 3 | | | | | | Gm6164 | 1.00 | 18919 | 3 | | | | | Gm839 | 1.00 |
| 18824 | 3 | | | | | | Gm6213 | 1.00 | 18920 | 3 | | | | | Gm8439 | 1.00 |
| 18825 | 3 | | | | | | Gm6225 | 1.00 | 18921 | 3 | | | | | Gm853 | 1.00 |
| 18826 | 3 | | | | | | Gm6249 | 1.00 | 18922 | 3 | | | | | Gm8579 | 1.00 |
| 18827 | 3 | | | | | | Gm6260 | 1.00 | 18923 | 3 | | | | | Gm8580 | 1.00 |
| 18828 | 3 | | | | | | Gm6268 | 1.00 | 18924 | 3 | | | | | Gm8633 | 1.00 |
| 18829 | 3 | | | | | | Gm6277 | 1.00 | 18925 | 3 | | | | | Gm8677 | 1.00 |
| 18830 | 3 | | | | | | Gm6289 | 1.00 | 18926 | 3 | | | | | Gm8693 | 1.00 |
| 18831 | 3 | | | | | | Gm6300 | 1.00 | 18927 | 3 | | | | | Gm8709 | 1.00 |
| 18832 | 3 | | | | | | Gm6307 | 1.00 | 18928 | 3 | | | | | Gm8765 | 1.00 |
| 18833 | 3 | | | | | | Gm6313 | 1.00 | 18929 | 3 | | | | | Gm8787 | 1.00 |
| 18834 | 3 | | | | | | Gm6329 | 1.00 | 18930 | 3 | | | | | Gm8817 | 1.00 |
| 18835 | 3 | | | | | | Gm6367 | 1.00 | 18931 | 3 | | | | | Gm884 | 1.00 |
| 18836 | 3 | | | | | | Gm6370 | 1.00 | 18932 | 3 | | | | | Gm8882 | 1.00 |
| 18837 | 3 | | | | | | Gm6377 | 1.00 | 18933 | 3 | | | | | Gm8883 | 1.00 |
| 18838 | 3 | | | | | | Gm6406 | 1.00 | 18934 | 3 | | | | | Gm8884 | 1.00 |
| 18839 | 3 | | | | | | Gm6408 | 1.00 | 18935 | 3 | | | | | Gm8909 | 1.00 |
| 18840 | 3 | | | | | | Gm6416 | 1.00 | 18936 | 3 | | | | | Gm9 | 1.00 |
| 18841 | 3 | | | | | | Gm6432 | 1.00 | 18937 | 3 | | | | | Gm904 | 1.00 |
| 18842 | 3 | | | | | | Gm6455 | 1.00 | 18938 | 3 | | | | | Gm9047 | 1.00 |
| 18843 | 3 | | | | | | Gm6460 | 1.00 | 18939 | 3 | | | | | Gm9054 | 1.00 |
| 18844 | 3 | | | | | | Gm648 | 1.00 | 18940 | 3 | | | | | Gm906 | 1.00 |
| 18845 | 3 | | | | | | Gm6498 | 1.00 | 18941 | 3 | | | | | Gm9112 | 1.00 |
| 18846 | 3 | | | | | | Gm6559 | 1.00 | 18942 | 3 | | | | | Gm9125 | 1.00 |
| 18847 | 3 | | | | | | Gm6567 | 1.00 | 18943 | 3 | | | | | Gm9159 | 1.00 |
| 18848 | 3 | | | | | | Gm6583 | 1.00 | 18944 | 3 | | | | | Gm9268 | 1.00 |
| 18849 | 3 | | | | | | Gm6588 | 1.00 | 18945 | 3 | | | | | Gm933 | 1.00 |
| 18850 | 3 | | | | | | Gm6592 | 1.00 | 18946 | 3 | | | | | Gm9376 | 1.00 |
| 18851 | 3 | | | | | | Gm6602 | 1.00 | 18947 | 3 | | | | | Gm9513 | 1.00 |
| 18852 | 3 | | | | | | Gm6614 | 1.00 | 18948 | 3 | | | | | Gm9573 | 1.00 |
| 18853 | 3 | | | | | | Gm6634 | 1.00 | 18949 | 3 | | | | | Gm960 | 1.00 |
| 18854 | 3 | | | | | | Gm6639 | 1.00 | 18950 | 3 | | | | | Gm973 | 1.00 |
| 18855 | 3 | | | | | | Gm6644 | 1.00 | 18951 | 3 | | | | | Gm9731 | 1.00 |
| 18856 | 3 | | | | | | Gm6696 | 1.00 | 18952 | 3 | | | | | Gm9733 | 1.00 |
| 18857 | 3 | | | | | | Gm6756 | 1.00 | 18953 | 3 | | | | | Gm9758 | 1.00 |
| 18858 | 3 | | | | | | Gm6760 | 1.00 | 18954 | 3 | | | | | Gm9767 | 1.00 |
| 18859 | 3 | | | | | | Gm6763 | 1.00 | 18955 | 3 | | | | | Gm9866 | 1.00 |
| 18860 | 3 | | | | | | Gm6792 | 1.00 | 18956 | 3 | | | | | Gm9871 | 1.00 |
| 18861 | 3 | | | | | | Gm6793 | 1.00 | 18957 | 3 | | | | | Gm9920 | 1.00 |
| 18862 | 3 | | | | | | Gm6812 | 1.00 | 18958 | 3 | | | | | Gm9926 | 1.00 |
| 18863 | 3 | | | | | | Gm6815 | 1.00 | 18959 | 3 | | | | | Gm9961 | 1.00 |
| 18864 | 3 | | | | | | Gm6878 | 1.00 | 18960 | 3 | | | | | Gm9962 | 1.00 |
| 18865 | 3 | | | | | | Gm6880 | 1.00 | 18961 | 3 | | | | | Gm9992 | 1.00 |
| 18866 | 3 | | | | | | Gm6890 | 1.00 | 18962 | 3 | | | | | Gm9994 | 1.00 |
| 18867 | 3 | | | | | | Gm6902 | 1.00 | 18963 | 3 | | | | | Gm9999 | 1.00 |
| 18868 | 3 | | | | | | Gm6904 | 1.00 | 18964 | 3 | | | | | Gmcl1i | 1.00 |
| 18869 | 3 | | | | | | Gm6927 | 1.00 | 18965 | 3 | | | | | Gmfg | 1.00 |
| 18870 | 3 | | | | | | Gm6936 | 1.00 | 18966 | 3 | | | | | Gml | 1.00 |
| 18871 | 3 | | | | | | Gm6938 | 1.00 | 18967 | 3 | | | | | Gmnc | 1.00 |
| 18872 | 3 | | | | | | Gm694 | 1.00 | 18968 | 3 | | | | | Gnat1 | 1.00 |
| 18873 | 3 | | | | | | Gm6994 | 1.00 | 18969 | 3 | | | | | Gnat2 | 1.00 |
| 18874 | 3 | | | | | | Gm7008 | 1.00 | 18970 | 3 | | | | | Gnat3 | 1.00 |
| 18875 | 3 | | | | | | Gm7056 | 1.00 | 18971 | 3 | | | | | Gnb3 | 1.00 |
| 18876 | 3 | | | | | | Gm7073 | 1.00 | 18972 | 3 | | | | | Gng13 | 1.00 |
| 18877 | 3 | | | | | | Gm7104 | 1.00 | 18973 | 3 | | | | | Gngt1 | 1.00 |
| 18878 | 3 | | | | | | Gm711 | 1.00 | 18974 | 3 | | | | | Gnrhr | 1.00 |
| 18879 | 3 | | | | | | Gm7134 | 1.00 | 18975 | 3 | | | | | Got1l1 | 1.00 |
| 18880 | 3 | | | | | | Gm7157 | 1.00 | 18976 | 3 | | | | | Gp2 | 1.00 |
| 18881 | 3 | | | | | | Gm7168 | 1.00 | 18977 | 3 | | | | | Gp6 | 1.00 |
| 18882 | 3 | | | | | | Gm7173 | 1.00 | 18978 | 3 | | | | | Gpat2 | 1.00 |
| 18883 | 3 | | | | | | Gm7257 | 1.00 | 18979 | 3 | | | | | Gpbar1 | 1.00 |
| 18884 | 3 | | | | | | Gm7271 | 1.00 | 18980 | 3 | | | | | Gpc5 | 1.00 |
| 18885 | 3 | | | | | | Gm732 | 1.00 | 18981 | 3 | | | | | Gpha2 | 1.00 |
| 18886 | 3 | | | | | | Gm7337 | 1.00 | 18982 | 3 | | | | | Gphb5 | 1.00 |
| 18887 | 3 | | | | | | Gm7361 | 1.00 | 18983 | 3 | | | | | Gpr1 | 1.00 |
| 18888 | 3 | | | | | | Gm7444 | 1.00 | 18984 | 3 | | | | | Gpr101 | 1.00 |
| 18889 | 3 | | | | | | Gm7457 | 1.00 | 18985 | 3 | | | | | Gpr110 | 1.00 |
| 18890 | 3 | | | | | | Gm7534 | 1.00 | 18986 | 3 | | | | | Gpr113 | 1.00 |
| 18891 | 3 | | | | | | Gm7538 | 1.00 | 18987 | 3 | | | | | Gpr114 | 1.00 |
| 18892 | 3 | | | | | | Gm7550 | 1.00 | 18988 | 3 | | | | | Gpr119 | 1.00 |
| 18893 | 3 | | | | | | Gm7609 | 1.00 | 18989 | 3 | | | | | Gpr132 | 1.00 |
| 18894 | 3 | | | | | | Gm7616 | 1.00 | 18990 | 3 | | | | | Gpr141 | 1.00 |
| 18895 | 3 | | | | | | Gm765 | 1.00 | 18991 | 3 | | | | | Gpr142 | 1.00 |
| 18896 | 3 | | | | | | Gm7714 | 1.00 | 18992 | 3 | | | | | Gpr143 | 1.00 |
| 18897 | 3 | | | | | | Gm773 | 1.00 | 18993 | 3 | | | | | Gpr149 | 1.00 |
| 18898 | 3 | | | | | | Gm7788 | 1.00 | 18994 | 3 | | | | | Gpr15 | 1.00 |
| 18899 | 3 | | | | | | Gm7854 | 1.00 | 18995 | 3 | | | | | Gpr150 | 1.00 |
| 18900 | 3 | | | | | | Gm7861 | 1.00 | 18996 | 3 | | | | | Gpr151 | 1.00 |
| 18901 | 3 | | | | | | Gm7903 | 1.00 | 18997 | 3 | | | | | Gpr152 | 1.00 |
| 18902 | 3 | | | | | | Gm7904 | 1.00 | 18998 | 3 | | | | | Gpr171 | 1.00 |
| 18903 | 3 | | | | | | Gm7977 | 1.00 | 18999 | 3 | | | | | Gpr174 | 1.00 |
| 18904 | 3 | | | | | | Gm7978 | 1.00 | 19000 | 3 | | | | | Gpr179 | 1.00 |
| 18905 | 3 | | | | | | Gm805 | 1.00 | 19001 | 3 | | | | | Gpr18 | 1.00 |
| 18906 | 3 | | | | | | Gm806 | 1.00 | 19002 | 3 | | | | | Gpr3 | 1.00 |
| 18907 | 3 | | | | | | Gm8096 | 1.00 | 19003 | 3 | | | | | Gpr31b | 1.00 |
| 18908 | 3 | | | | | | Gm813 | 1.00 | 19004 | 3 | | | | | Gpr33 | 1.00 |
| 18909 | 3 | | | | | | Gm815 | 1.00 | 19005 | 3 | | | | | Gpr37l1 | 1.00 |

Fig. 45 - 100

| | | | | | | | | | | | | | | | |
|---|---|---|---|---|---|---|---|---|---|---|---|---|---|---|---|
| 19006 | 3 | | | | | | Gpr52 | 1.00 | 19102 | 3 | | | | Havcr1 | 1.00 |
| 19007 | 3 | | | | | | Gpr55 | 1.00 | 19103 | 3 | | | | Hbb-bh2 | 1.00 |
| 19008 | 3 | | | | | | Gpr6 | 1.00 | 19104 | 3 | | | | Hcrt | 1.00 |
| 19009 | 3 | | | | | | Gpr61 | 1.00 | 19105 | 3 | | | | Hcrtr1 | 1.00 |
| 19010 | 3 | | | | | | Gpr62 | 1.00 | 19106 | 3 | | | | Hcrtr2 | 1.00 |
| 19011 | 3 | | | | | | Gpr82 | 1.00 | 19107 | 3 | | | | Hcst | 1.00 |
| 19012 | 3 | | | | | | Gpr84 | 1.00 | 19108 | 3 | | | | Hdgfl1 | 1.00 |
| 19013 | 3 | | | | | | Gpr98 | 1.00 | 19109 | 3 | | | | Hdhd1a | 1.00 |
| 19014 | 3 | | | | | | Gprc5d | 1.00 | 19110 | 3 | | | | Heatr9 | 1.00 |
| 19015 | 3 | | | | | | Gprc6a | 1.00 | 19111 | 3 | | | | Helt | 1.00 |
| 19016 | 3 | | | | | | Gpx2-ps1 | 1.00 | 19112 | 3 | | | | Hemt1 | 1.00 |
| 19017 | 3 | | | | | | Gpx5 | 1.00 | 19113 | 3 | | | | Henmt1 | 1.00 |
| 19018 | 3 | | | | | | Gpx6 | 1.00 | 19114 | 3 | | | | Hepacam2 | 1.00 |
| 19019 | 3 | | | | | | Gramd2 | 1.00 | 19115 | 3 | | | | Herc6 | 1.00 |
| 19020 | 3 | | | | | | Grasp | 1.00 | 19116 | 3 | | | | Hes2 | 1.00 |
| 19021 | 3 | | | | | | Grid2ip | 1.00 | 19117 | 3 | | | | Hes3 | 1.00 |
| 19022 | 3 | | | | | | Grifin | 1.00 | 19118 | 3 | | | | Hes7 | 1.00 |
| 19023 | 3 | | | | | | Grin2a | 1.00 | 19119 | 3 | | | | Hesx1 | 1.00 |
| 19024 | 3 | | | | | | Grin2c | 1.00 | 19120 | 3 | | | | Hfm1 | 1.00 |
| 19025 | 3 | | | | | | Grin3b | 1.00 | 19121 | 3 | | | | Hhipl2 | 1.00 |
| 19026 | 3 | | | | | | Grip1os2 | 1.00 | 19122 | 3 | | | | Hhla1 | 1.00 |
| 19027 | 3 | | | | | | Grk1 | 1.00 | 19123 | 3 | | | | Higd1c | 1.00 |
| 19028 | 3 | | | | | | Grm6 | 1.00 | 19124 | 3 | | | | Hist1h1a | 1.00 |
| 19029 | 3 | | | | | | Grpr | 1.00 | 19125 | 3 | | | | Hist1h1b | 1.00 |
| 19030 | 3 | | | | | | Grxcr1 | 1.00 | 19126 | 3 | | | | Hist1h1t | 1.00 |
| 19031 | 3 | | | | | | Grxcr2 | 1.00 | 19127 | 3 | | | | Hist1h2aa | 1.00 |
| 19032 | 3 | | | | | | Gsc2 | 1.00 | 19128 | 3 | | | | Hist1h3f | 1.00 |
| 19033 | 3 | | | | | | Gsdma2 | 1.00 | 19129 | 3 | | | | Hist1h3h | 1.00 |
| 19034 | 3 | | | | | | Gsdma3 | 1.00 | 19130 | 3 | | | | Hist2h2ab | 1.00 |
| 19035 | 3 | | | | | | Gsdmc2 | 1.00 | 19131 | 3 | | | | Hist2h2ac | 1.00 |
| 19036 | 3 | | | | | | Gsdmc3 | 1.00 | 19132 | 3 | | | | Hist2h2bb | 1.00 |
| 19037 | 3 | | | | | | Gsdmc4 | 1.00 | 19133 | 3 | | | | Hist2h3b | 1.00 |
| 19038 | 3 | | | | | | Gsdmcl-ps | 1.00 | 19134 | 3 | | | | Hist2h3c1 | 1.00 |
| 19039 | 3 | | | | | | Gsdmcl1 | 1.00 | 19135 | 3 | | | | Hist4h4 | 1.00 |
| 19040 | 3 | | | | | | Gsdmcl2 | 1.00 | 19136 | 3 | | | | Hmgb1-rs17 | 1.00 |
| 19041 | 3 | | | | | | Gsg1 | 1.00 | 19137 | 3 | | | | Hmgb4 | 1.00 |
| 19042 | 3 | | | | | | Gsto2 | 1.00 | 19138 | 3 | | | | Hmx2 | 1.00 |
| 19043 | 3 | | | | | | Gstt4 | 1.00 | 19139 | 3 | | | | Hmx3 | 1.00 |
| 19044 | 3 | | | | | | Gsx1 | 1.00 | 19140 | 3 | | | | Hnf4aos | 1.00 |
| 19045 | 3 | | | | | | Gsx2 | 1.00 | 19141 | 3 | | | | Hnrnpll | 1.00 |
| 19046 | 3 | | | | | | Gtf2a1l | 1.00 | 19142 | 3 | | | | Hormad1 | 1.00 |
| 19047 | 3 | | | | | | Gtsf1 | 1.00 | 19143 | 3 | | | | Hormad2 | 1.00 |
| 19048 | 3 | | | | | | Gtsf1l | 1.00 | 19144 | 3 | | | | Hotair | 1.00 |
| 19049 | 3 | | | | | | Guca1a | 1.00 | 19145 | 3 | | | | Hottip | 1.00 |
| 19050 | 3 | | | | | | Guca1b | 1.00 | 19146 | 3 | | | | Hoxb1 | 1.00 |
| 19051 | 3 | | | | | | Gucy1b2 | 1.00 | 19147 | 3 | | | | Hoxd3os1 | 1.00 |
| 19052 | 3 | | | | | | Gucy2d | 1.00 | 19148 | 3 | | | | Hpdl | 1.00 |
| 19053 | 3 | | | | | | Gucy2e | 1.00 | 19149 | 3 | | | | Hrasls | 1.00 |
| 19054 | 3 | | | | | | Gucy2f | 1.00 | 19150 | 3 | | | | Hrasls5 | 1.00 |
| 19055 | 3 | | | | | | Gucy2g | 1.00 | 19151 | 3 | | | | Hrh1 | 1.00 |
| 19056 | 3 | | | | | | Gyk1 | 1.00 | 19152 | 3 | | | | Hrh2 | 1.00 |
| 19057 | 3 | | | | | | Gzmb | 1.00 | 19153 | 3 | | | | Hrh3 | 1.00 |
| 19058 | 3 | | | | | | Gzmc | 1.00 | 19154 | 3 | | | | Hrh4 | 1.00 |
| 19059 | 3 | | | | | | Gzmd | 1.00 | 19155 | 3 | | | | Hsd17b1 | 1.00 |
| 19060 | 3 | | | | | | Gzme | 1.00 | 19156 | 3 | | | | Hsd17b3 | 1.00 |
| 19061 | 3 | | | | | | Gzmf | 1.00 | 19157 | 3 | | | | Hsd17b6 | 1.00 |
| 19062 | 3 | | | | | | Gzmg | 1.00 | 19158 | 3 | | | | Hsd3b2 | 1.00 |
| 19063 | 3 | | | | | | Gzmk | 1.00 | 19159 | 3 | | | | Hsd3b4 | 1.00 |
| 19064 | 3 | | | | | | Gzmm | 1.00 | 19160 | 3 | | | | Hsd3b5 | 1.00 |
| 19065 | 3 | | | | | | Gzmn | 1.00 | 19161 | 3 | | | | Hsf2bp | 1.00 |
| 19066 | 3 | | | | | | H1fnt | 1.00 | 19162 | 3 | | | | Hsf3 | 1.00 |
| 19067 | 3 | | | | | | H1foo | 1.00 | 19163 | 3 | | | | Hsf4 | 1.00 |
| 19068 | 3 | | | | | | H2-Bl | 1.00 | 19164 | 3 | | | | Hsf5 | 1.00 |
| 19069 | 3 | | | | | | H2-DMb2 | 1.00 | 19165 | 3 | | | | Hsfy2 | 1.00 |
| 19070 | 3 | | | | | | H2-Ea-ps | 1.00 | 19166 | 3 | | | | Hsh2d | 1.00 |
| 19071 | 3 | | | | | | H2-Eb2 | 1.00 | 19167 | 3 | | | | Hspb9 | 1.00 |
| 19072 | 3 | | | | | | H2-Ke2 | 1.00 | 19168 | 3 | | | | Htatip2 | 1.00 |
| 19073 | 3 | | | | | | H2-L | 1.00 | 19169 | 3 | | | | Htr1a | 1.00 |
| 19074 | 3 | | | | | | H2-M1 | 1.00 | 19170 | 3 | | | | Htr1d | 1.00 |
| 19075 | 3 | | | | | | H2-M11 | 1.00 | 19171 | 3 | | | | Htr1f | 1.00 |
| 19076 | 3 | | | | | | H2-M11 | 1.00 | 19172 | 3 | | | | Htr2b | 1.00 |
| 19077 | 3 | | | | | | H2-M11 | 1.00 | 19173 | 3 | | | | Htr3b | 1.00 |
| 19078 | 3 | | | | | | H2-M11 | 1.00 | 19174 | 3 | | | | Htr4 | 1.00 |
| 19079 | 3 | | | | | | H2-M11 | 1.00 | 19175 | 3 | | | | Htr5a | 1.00 |
| 19080 | 3 | | | | | | H2-M11 | 1.00 | 19176 | 3 | | | | Htr5b | 1.00 |
| 19081 | 3 | | | | | | H2-M11 | 1.00 | 19177 | 3 | | | | Htr6 | 1.00 |
| 19082 | 3 | | | | | | H2-M2 | 1.00 | 19178 | 3 | | | | Htra4 | 1.00 |
| 19083 | 3 | | | | | | H2-M3 | 1.00 | 19179 | 3 | | | | Hus1b | 1.00 |
| 19084 | 3 | | | | | | H2-M9 | 1.00 | 19180 | 3 | | | | Hyal4 | 1.00 |
| 19085 | 3 | | | | | | H2-Oa | 1.00 | 19181 | 3 | | | | Hyal5 | 1.00 |
| 19086 | 3 | | | | | | H2-Ob | 1.00 | 19182 | 3 | | | | Hyal6 | 1.00 |
| 19087 | 3 | | | | | | H2-Q5 | 1.00 | 19183 | 3 | | | | Hydin | 1.00 |
| 19088 | 3 | | | | | | H2-Q8 | 1.00 | 19184 | 3 | | | | I730028E13Rik | 1.00 |
| 19089 | 3 | | | | | | H2-Q9 | 1.00 | 19185 | 3 | | | | I730030J21Rik | 1.00 |
| 19090 | 3 | | | | | | H2-T10 | 1.00 | 19186 | 3 | | | | I830077J02Rik | 1.00 |
| 19091 | 3 | | | | | | H2afb1 | 1.00 | 19187 | 3 | | | | Icam5 | 1.00 |
| 19092 | 3 | | | | | | H2afb2 | 1.00 | 19188 | 3 | | | | Icos | 1.00 |
| 19093 | 3 | | | | | | H2afb3 | 1.00 | 19189 | 3 | | | | Ido1 | 1.00 |
| 19094 | 3 | | | | | | H2bfm | 1.00 | 19190 | 3 | | | | Ido2 | 1.00 |
| 19095 | 3 | | | | | | H60b | 1.00 | 19191 | 3 | | | | Ifi44l | 1.00 |
| 19096 | 3 | | | | | | Hamp2 | 1.00 | 19192 | 3 | | | | Ifitd1 | 1.00 |
| 19097 | 3 | | | | | | Hapln2 | 1.00 | 19193 | 3 | | | | Ifna1 | 1.00 |
| 19098 | 3 | | | | | | Hapln3 | 1.00 | 19194 | 3 | | | | Ifna11 | 1.00 |
| 19099 | 3 | | | | | | Hapln4 | 1.00 | 19195 | 3 | | | | Ifna12 | 1.00 |
| 19100 | 3 | | | | | | Has1 | 1.00 | 19196 | 3 | | | | Ifna13 | 1.00 |
| 19101 | 3 | | | | | | Has2os | 1.00 | 19197 | 3 | | | | Ifna14 | 1.00 |

Fig. 45 - 101

| | | | | | | | | | | | | | | |
|---|---|---|---|---|---|---|---|---|---|---|---|---|---|---|
| 19198 | 3 | | | | | | Ifna15 | 1.00 | 19294 | 3 | | | | Itprip | 1.00 |
| 19199 | 3 | | | | | | Ifna16 | 1.00 | 19295 | 3 | | | | Izumo1 | 1.00 |
| 19200 | 3 | | | | | | Ifna2 | 1.00 | 19296 | 3 | | | | Izumo2 | 1.00 |
| 19201 | 3 | | | | | | Ifna4 | 1.00 | 19297 | 3 | | | | Izumo3 | 1.00 |
| 19202 | 3 | | | | | | Ifna5 | 1.00 | 19298 | 3 | | | | Jag2 | 1.00 |
| 19203 | 3 | | | | | | Ifna6 | 1.00 | 19299 | 3 | | | | Jmjd7-pla2g4b | 1.00 |
| 19204 | 3 | | | | | | Ifna7 | 1.00 | 19300 | 3 | | | | Jph1 | 1.00 |
| 19205 | 3 | | | | | | Ifna9 | 1.00 | 19301 | 3 | | | | Kank4os | 1.00 |
| 19206 | 3 | | | | | | Ifnab | 1.00 | 19302 | 3 | | | | Kap | 1.00 |
| 19207 | 3 | | | | | | Ifnb1 | 1.00 | 19303 | 3 | | | | Katnal2 | 1.00 |
| 19208 | 3 | | | | | | Ifne | 1.00 | 19304 | 3 | | | | Kcna10 | 1.00 |
| 19209 | 3 | | | | | | Ifng | 1.00 | 19305 | 3 | | | | Kcna7 | 1.00 |
| 19210 | 3 | | | | | | Ifnk | 1.00 | 19306 | 3 | | | | Kcnd3os | 1.00 |
| 19211 | 3 | | | | | | Ifnl2 | 1.00 | 19307 | 3 | | | | Kcne1 | 1.00 |
| 19212 | 3 | | | | | | Ifnl3 | 1.00 | 19308 | 3 | | | | Kcng3 | 1.00 |
| 19213 | 3 | | | | | | Ifnz | 1.00 | 19309 | 3 | | | | Kcng4 | 1.00 |
| 19214 | 3 | | | | | | Igbp1b | 1.00 | 19310 | 3 | | | | Kcnh3 | 1.00 |
| 19215 | 3 | | | | | | Igfbp6 | 1.00 | 19311 | 3 | | | | Kcnh5 | 1.00 |
| 19216 | 3 | | | | | | Igfl3 | 1.00 | 19312 | 3 | | | | Kcnh6 | 1.00 |
| 19217 | 3 | | | | | | Igfn1 | 1.00 | 19313 | 3 | | | | Kcnj1 | 1.00 |
| 19218 | 3 | | | | | | Igj | 1.00 | 19314 | 3 | | | | Kcnj13 | 1.00 |
| 19219 | 3 | | | | | | Igsf9 | 1.00 | 19315 | 3 | | | | Kcnj14 | 1.00 |
| 19220 | 3 | | | | | | Ikzf3 | 1.00 | 19316 | 3 | | | | Kcnj4 | 1.00 |
| 19221 | 3 | | | | | | Il10 | 1.00 | 19317 | 3 | | | | Kcnk12 | 1.00 |
| 19222 | 3 | | | | | | Il11 | 1.00 | 19318 | 3 | | | | Kcnk15 | 1.00 |
| 19223 | 3 | | | | | | Il11ra2 | 1.00 | 19319 | 3 | | | | Kcnk16 | 1.00 |
| 19224 | 3 | | | | | | Il12a | 1.00 | 19320 | 3 | | | | Kcnk18 | 1.00 |
| 19225 | 3 | | | | | | Il12b | 1.00 | 19321 | 3 | | | | Kcnk4 | 1.00 |
| 19226 | 3 | | | | | | Il12rb1 | 1.00 | 19322 | 3 | | | | Kcnmb1 | 1.00 |
| 19227 | 3 | | | | | | Il13 | 1.00 | 19323 | 3 | | | | Kcnmb3 | 1.00 |
| 19228 | 3 | | | | | | Il13ra2 | 1.00 | 19324 | 3 | | | | Kcnmb4os1 | 1.00 |
| 19229 | 3 | | | | | | Il17a | 1.00 | 19325 | 3 | | | | Kcns2 | 1.00 |
| 19230 | 3 | | | | | | Il17c | 1.00 | 19326 | 3 | | | | Kcnt2 | 1.00 |
| 19231 | 3 | | | | | | Il17f | 1.00 | 19327 | 3 | | | | Kcnu1 | 1.00 |
| 19232 | 3 | | | | | | Il18r1 | 1.00 | 19328 | 3 | | | | Kcnv1 | 1.00 |
| 19233 | 3 | | | | | | Il18rap | 1.00 | 19329 | 3 | | | | Kcnv2 | 1.00 |
| 19234 | 3 | | | | | | Il19 | 1.00 | 19330 | 3 | | | | Kctd16 | 1.00 |
| 19235 | 3 | | | | | | Il1b | 1.00 | 19331 | 3 | | | | Kctd19 | 1.00 |
| 19236 | 3 | | | | | | Il1bos | 1.00 | 19332 | 3 | | | | Kdm4d | 1.00 |
| 19237 | 3 | | | | | | Il1f10 | 1.00 | 19333 | 3 | | | | Khdc1a | 1.00 |
| 19238 | 3 | | | | | | Il1rapl1 | 1.00 | 19334 | 3 | | | | Khdc1b | 1.00 |
| 19239 | 3 | | | | | | Il1rapl2 | 1.00 | 19335 | 3 | | | | Khdc1c | 1.00 |
| 19240 | 3 | | | | | | Il2 | 1.00 | 19336 | 3 | | | | Khdc3 | 1.00 |
| 19241 | 3 | | | | | | Il20 | 1.00 | 19337 | 3 | | | | Kif17 | 1.00 |
| 19242 | 3 | | | | | | Il20ra | 1.00 | 19338 | 3 | | | | Kif2b | 1.00 |
| 19243 | 3 | | | | | | Il21 | 1.00 | 19339 | 3 | | | | Kif4-ps | 1.00 |
| 19244 | 3 | | | | | | Il22 | 1.00 | 19340 | 3 | | | | Kif6 | 1.00 |
| 19245 | 3 | | | | | | Il23a | 1.00 | 19341 | 3 | | | | Kif9 | 1.00 |
| 19246 | 3 | | | | | | Il23r | 1.00 | 19342 | 3 | | | | Kir3dl1 | 1.00 |
| 19247 | 3 | | | | | | Il24 | 1.00 | 19343 | 3 | | | | Kir3dl2 | 1.00 |
| 19248 | 3 | | | | | | Il25 | 1.00 | 19344 | 3 | | | | Kirrel2 | 1.00 |
| 19249 | 3 | | | | | | Il27 | 1.00 | 19345 | 3 | | | | Kis2 | 1.00 |
| 19250 | 3 | | | | | | Il27ra | 1.00 | 19346 | 3 | | | | Kiss1 | 1.00 |
| 19251 | 3 | | | | | | Il2ra | 1.00 | 19347 | 3 | | | | Klf17 | 1.00 |
| 19252 | 3 | | | | | | Il2rb | 1.00 | 19348 | 3 | | | | Klhdc7b | 1.00 |
| 19253 | 3 | | | | | | Il3 | 1.00 | 19349 | 3 | | | | Klhl10 | 1.00 |
| 19254 | 3 | | | | | | Il31 | 1.00 | 19350 | 3 | | | | Klhl33 | 1.00 |
| 19255 | 3 | | | | | | Il31ra | 1.00 | 19351 | 3 | | | | Klhl35 | 1.00 |
| 19256 | 3 | | | | | | Il4 | 1.00 | 19352 | 3 | | | | Klhl42 | 1.00 |
| 19257 | 3 | | | | | | Il4i1 | 1.00 | 19353 | 3 | | | | Klk12 | 1.00 |
| 19258 | 3 | | | | | | Il5 | 1.00 | 19354 | 3 | | | | Klk15 | 1.00 |
| 19259 | 3 | | | | | | Il5ra | 1.00 | 19355 | 3 | | | | Klk1b1 | 1.00 |
| 19260 | 3 | | | | | | Il6 | 1.00 | 19356 | 3 | | | | Klk1b11 | 1.00 |
| 19261 | 3 | | | | | | Il7 | 1.00 | 19357 | 3 | | | | Klk1b16 | 1.00 |
| 19262 | 3 | | | | | | Il7r | 1.00 | 19358 | 3 | | | | Klk1b21 | 1.00 |
| 19263 | 3 | | | | | | Il9 | 1.00 | 19359 | 3 | | | | Klk1b22 | 1.00 |
| 19264 | 3 | | | | | | Il9r | 1.00 | 19360 | 3 | | | | Klk1b24 | 1.00 |
| 19265 | 3 | | | | | | Iltifb | 1.00 | 19361 | 3 | | | | Klk1b27 | 1.00 |
| 19266 | 3 | | | | | | Impg1 | 1.00 | 19362 | 3 | | | | Klk1b3 | 1.00 |
| 19267 | 3 | | | | | | Impg2 | 1.00 | 19363 | 3 | | | | Klk1b4 | 1.00 |
| 19268 | 3 | | | | | | Inhbc | 1.00 | 19364 | 3 | | | | Klk1b5 | 1.00 |
| 19269 | 3 | | | | | | Inmt | 1.00 | 19365 | 3 | | | | Klk1b7-ps | 1.00 |
| 19270 | 3 | | | | | | Ino80d | 1.00 | 19366 | 3 | | | | Klk1b8 | 1.00 |
| 19271 | 3 | | | | | | Insl5 | 1.00 | 19367 | 3 | | | | Klk1b9 | 1.00 |
| 19272 | 3 | | | | | | Insm2 | 1.00 | 19368 | 3 | | | | Klk4 | 1.00 |
| 19273 | 3 | | | | | | Insrr | 1.00 | 19369 | 3 | | | | Klk6 | 1.00 |
| 19274 | 3 | | | | | | Iqca | 1.00 | 19370 | 3 | | | | Klra1 | 1.00 |
| 19275 | 3 | | | | | | Iqcf1 | 1.00 | 19371 | 3 | | | | Klra10 | 1.00 |
| 19276 | 3 | | | | | | Iqcf3 | 1.00 | 19372 | 3 | | | | Klra12 | 1.00 |
| 19277 | 3 | | | | | | Iqcf4 | 1.00 | 19373 | 3 | | | | Klra13-ps | 1.00 |
| 19278 | 3 | | | | | | Iqcf5 | 1.00 | 19374 | 3 | | | | Klra14-ps | 1.00 |
| 19279 | 3 | | | | | | Iqcf6 | 1.00 | 19375 | 3 | | | | Klra15 | 1.00 |
| 19280 | 3 | | | | | | Iqch | 1.00 | 19376 | 3 | | | | Klra17 | 1.00 |
| 19281 | 3 | | | | | | Iqcj | 1.00 | 19377 | 3 | | | | Klra18 | 1.00 |
| 19282 | 3 | | | | | | Iqub | 1.00 | 19378 | 3 | | | | Klra19 | 1.00 |
| 19283 | 3 | | | | | | Irf4 | 1.00 | 19379 | 3 | | | | Klra2 | 1.00 |
| 19284 | 3 | | | | | | Irg1 | 1.00 | 19380 | 3 | | | | Klra21 | 1.00 |
| 19285 | 3 | | | | | | Irgc1 | 1.00 | 19381 | 3 | | | | Klra22 | 1.00 |
| 19286 | 3 | | | | | | Irs3 | 1.00 | 19382 | 3 | | | | Klra23 | 1.00 |
| 19287 | 3 | | | | | | Irx6 | 1.00 | 19383 | 3 | | | | Klra3 | 1.00 |
| 19288 | 3 | | | | | | Ism2 | 1.00 | 19384 | 3 | | | | Klra33 | 1.00 |
| 19289 | 3 | | | | | | Itgad | 1.00 | 19385 | 3 | | | | Klra4 | 1.00 |
| 19290 | 3 | | | | | | Itgae | 1.00 | 19386 | 3 | | | | Klra5 | 1.00 |
| 19291 | 3 | | | | | | Itgax | 1.00 | 19387 | 3 | | | | Klra6 | 1.00 |
| 19292 | 3 | | | | | | Itk | 1.00 | 19388 | 3 | | | | Klra7 | 1.00 |
| 19293 | 3 | | | | | | Itln1 | 1.00 | 19389 | 3 | | | | Klra8 | 1.00 |

Fig. 45 - 102

| | | | | | | | | | | | | | | |
|---|---|---|---|---|---|---|---|---|---|---|---|---|---|---|
| 19390 | 3 | | | | | | Klra9 | 1.00 | 19486 | 3 | | | | | | LOC100502896 | 1.00 |
| 19391 | 3 | | | | | | Klrb1 | 1.00 | 19487 | 3 | | | | | | LOC100503280 | 1.00 |
| 19392 | 3 | | | | | | Klrb1-ps1 | 1.00 | 19488 | 3 | | | | | | LOC100504039 | 1.00 |
| 19393 | 3 | | | | | | Klrb1a | 1.00 | 19489 | 3 | | | | | | LOC100505025 | 1.00 |
| 19394 | 3 | | | | | | Klrb1b | 1.00 | 19490 | 3 | | | | | | LOC100862015 | 1.00 |
| 19395 | 3 | | | | | | Klrb1c | 1.00 | 19491 | 3 | | | | | | LOC100862268 | 1.00 |
| 19396 | 3 | | | | | | Klrb1f | 1.00 | 19492 | 3 | | | | | | LOC101055769 | 1.00 |
| 19397 | 3 | | | | | | Klrc1 | 1.00 | 19493 | 3 | | | | | | LOC101055863 | 1.00 |
| 19398 | 3 | | | | | | Klrc2 | 1.00 | 19494 | 3 | | | | | | LOC101056136 | 1.00 |
| 19399 | 3 | | | | | | Klrc3 | 1.00 | 19495 | 3 | | | | | | LOC101056149 | 1.00 |
| 19400 | 3 | | | | | | Klrd1 | 1.00 | 19496 | 3 | | | | | | LOC101056236 | 1.00 |
| 19401 | 3 | | | | | | Klre1 | 1.00 | 19497 | 3 | | | | | | LOC101243624 | 1.00 |
| 19402 | 3 | | | | | | Klrg1 | 1.00 | 19498 | 3 | | | | | | LOC102308570 | 1.00 |
| 19403 | 3 | | | | | | Klri1 | 1.00 | 19499 | 3 | | | | | | LOC102631757 | 1.00 |
| 19404 | 3 | | | | | | Klri2 | 1.00 | 19500 | 3 | | | | | | LOC102632423 | 1.00 |
| 19405 | 3 | | | | | | Klrk1 | 1.00 | 19501 | 3 | | | | | | LOC102632430 | 1.00 |
| 19406 | 3 | | | | | | Kncn | 1.00 | 19502 | 3 | | | | | | LOC102633035 | 1.00 |
| 19407 | 3 | | | | | | Kpna7 | 1.00 | 19503 | 3 | | | | | | LOC102633315 | 1.00 |
| 19408 | 3 | | | | | | Krt12 | 1.00 | 19504 | 3 | | | | | | LOC102634101 | 1.00 |
| 19409 | 3 | | | | | | Krt24 | 1.00 | 19505 | 3 | | | | | | LOC102634401 | 1.00 |
| 19410 | 3 | | | | | | Krt26 | 1.00 | 19506 | 3 | | | | | | LOC102634431 | 1.00 |
| 19411 | 3 | | | | | | Krt28 | 1.00 | 19507 | 3 | | | | | | LOC102634753 | 1.00 |
| 19412 | 3 | | | | | | Krt31 | 1.00 | 19508 | 3 | | | | | | LOC102635087 | 1.00 |
| 19413 | 3 | | | | | | Krt32 | 1.00 | 19509 | 3 | | | | | | LOC171588 | 1.00 |
| 19414 | 3 | | | | | | Krt33a | 1.00 | 19510 | 3 | | | | | | LOC381967 | 1.00 |
| 19415 | 3 | | | | | | Krt33b | 1.00 | 19511 | 3 | | | | | | LOC666331 | 1.00 |
| 19416 | 3 | | | | | | Krt34 | 1.00 | 19512 | 3 | | | | | | Lactbl1 | 1.00 |
| 19417 | 3 | | | | | | Krt35 | 1.00 | 19513 | 3 | | | | | | Laiba | 1.00 |
| 19418 | 3 | | | | | | Krt39 | 1.00 | 19514 | 3 | | | | | | Lao1 | 1.00 |
| 19419 | 3 | | | | | | Krt40 | 1.00 | 19515 | 3 | | | | | | Lat | 1.00 |
| 19420 | 3 | | | | | | Krt42 | 1.00 | 19516 | 3 | | | | | | Lax1 | 1.00 |
| 19421 | 3 | | | | | | Krt72 | 1.00 | 19517 | 3 | | | | | | Lbx2 | 1.00 |
| 19422 | 3 | | | | | | Krt73 | 1.00 | 19518 | 3 | | | | | | Lce1k | 1.00 |
| 19423 | 3 | | | | | | Krt74 | 1.00 | 19519 | 3 | | | | | | Lce3b | 1.00 |
| 19424 | 3 | | | | | | Krt76 | 1.00 | 19520 | 3 | | | | | | Lcn10 | 1.00 |
| 19425 | 3 | | | | | | Krt81 | 1.00 | 19521 | 3 | | | | | | Lcn11 | 1.00 |
| 19426 | 3 | | | | | | Krt82 | 1.00 | 19522 | 3 | | | | | | Lcn12 | 1.00 |
| 19427 | 3 | | | | | | Krt83 | 1.00 | 19523 | 3 | | | | | | Lcn3 | 1.00 |
| 19428 | 3 | | | | | | Krt85 | 1.00 | 19524 | 3 | | | | | | Lcn4 | 1.00 |
| 19429 | 3 | | | | | | Krt86 | 1.00 | 19525 | 3 | | | | | | Lcn5 | 1.00 |
| 19430 | 3 | | | | | | Krt9 | 1.00 | 19526 | 3 | | | | | | Lcn6 | 1.00 |
| 19431 | 3 | | | | | | Krtap1-3 | 1.00 | 19527 | 3 | | | | | | Lcn8 | 1.00 |
| 19432 | 3 | | | | | | Krtap1-4 | 1.00 | 19528 | 3 | | | | | | Lcn9 | 1.00 |
| 19433 | 3 | | | | | | Krtap1-5 | 1.00 | 19529 | 3 | | | | | | Lctl | 1.00 |
| 19434 | 3 | | | | | | Krtap10-10 | 1.00 | 19530 | 3 | | | | | | Ldhc | 1.00 |
| 19435 | 3 | | | | | | Krtap10-4 | 1.00 | 19531 | 3 | | | | | | Ldhd | 1.00 |
| 19436 | 3 | | | | | | Krtap11-1 | 1.00 | 19532 | 3 | | | | | | Ldlrad1 | 1.00 |
| 19437 | 3 | | | | | | Krtap12-1 | 1.00 | 19533 | 3 | | | | | | Ldlrad2 | 1.00 |
| 19438 | 3 | | | | | | Krtap13-1 | 1.00 | 19534 | 3 | | | | | | Ldlrad4 | 1.00 |
| 19439 | 3 | | | | | | Krtap14 | 1.00 | 19535 | 3 | | | | | | Lefty2 | 1.00 |
| 19440 | 3 | | | | | | Krtap15 | 1.00 | 19536 | 3 | | | | | | Leip1 | 1.00 |
| 19441 | 3 | | | | | | Krtap16-1 | 1.00 | 19537 | 3 | | | | | | Lep | 1.00 |
| 19442 | 3 | | | | | | Krtap16-3 | 1.00 | 19538 | 3 | | | | | | Lgsn | 1.00 |
| 19443 | 3 | | | | | | Krtap17-1 | 1.00 | 19539 | 3 | | | | | | Lhb | 1.00 |
| 19444 | 3 | | | | | | Krtap19-1 | 1.00 | 19540 | 3 | | | | | | Lhcgr | 1.00 |
| 19445 | 3 | | | | | | Krtap19-3 | 1.00 | 19541 | 3 | | | | | | Lhfpl5 | 1.00 |
| 19446 | 3 | | | | | | Krtap19-4 | 1.00 | 19542 | 3 | | | | | | Lhx3 | 1.00 |
| 19447 | 3 | | | | | | Krtap19-5 | 1.00 | 19543 | 3 | | | | | | Lhx4 | 1.00 |
| 19448 | 3 | | | | | | Krtap19-9b | 1.00 | 19544 | 3 | | | | | | Lif | 1.00 |
| 19449 | 3 | | | | | | Krtap2-4 | 1.00 | 19545 | 3 | | | | | | Lilra5 | 1.00 |
| 19450 | 3 | | | | | | Krtap20-2 | 1.00 | 19546 | 3 | | | | | | Lilra6 | 1.00 |
| 19451 | 3 | | | | | | Krtap21-1 | 1.00 | 19547 | 3 | | | | | | Lin28a | 1.00 |
| 19452 | 3 | | | | | | Krtap22-2 | 1.00 | 19548 | 3 | | | | | | Lin7b | 1.00 |
| 19453 | 3 | | | | | | Krtap24-1 | 1.00 | 19549 | 3 | | | | | | Lincrna-cox2 | 1.00 |
| 19454 | 3 | | | | | | Krtap26-1 | 1.00 | 19550 | 3 | | | | | | Lingo4 | 1.00 |
| 19455 | 3 | | | | | | Krtap27-1 | 1.00 | 19551 | 3 | | | | | | Lipf | 1.00 |
| 19456 | 3 | | | | | | Krtap3-2 | 1.00 | 19552 | 3 | | | | | | Lipi | 1.00 |
| 19457 | 3 | | | | | | Krtap31-1 | 1.00 | 19553 | 3 | | | | | | Lipn | 1.00 |
| 19458 | 3 | | | | | | Krtap31-2 | 1.00 | 19554 | 3 | | | | | | Lkaaear1 | 1.00 |
| 19459 | 3 | | | | | | Krtap4-1 | 1.00 | 19555 | 3 | | | | | | Lman1l | 1.00 |
| 19460 | 3 | | | | | | Krtap4-13 | 1.00 | 19556 | 3 | | | | | | Loxhd1 | 1.00 |
| 19461 | 3 | | | | | | Krtap4-16 | 1.00 | 19557 | 3 | | | | | | Lpcat2b | 1.00 |
| 19462 | 3 | | | | | | Krtap4-2 | 1.00 | 19558 | 3 | | | | | | Lpo | 1.00 |
| 19463 | 3 | | | | | | Krtap4-6 | 1.00 | 19559 | 3 | | | | | | Lrcol1 | 1.00 |
| 19464 | 3 | | | | | | Krtap4-7 | 1.00 | 19560 | 3 | | | | | | Lrguk | 1.00 |
| 19465 | 3 | | | | | | Krtap4-8 | 1.00 | 19561 | 3 | | | | | | Lrit1 | 1.00 |
| 19466 | 3 | | | | | | Krtap4-9 | 1.00 | 19562 | 3 | | | | | | Lrit2 | 1.00 |
| 19467 | 3 | | | | | | Krtap5-1 | 1.00 | 19563 | 3 | | | | | | Lrit3 | 1.00 |
| 19468 | 3 | | | | | | Krtap5-2 | 1.00 | 19564 | 3 | | | | | | Lrp1b | 1.00 |
| 19469 | 3 | | | | | | Krtap5-3 | 1.00 | 19565 | 3 | | | | | | Lrp2 | 1.00 |
| 19470 | 3 | | | | | | Krtap5-4 | 1.00 | 19566 | 3 | | | | | | Lrp2bp | 1.00 |
| 19471 | 3 | | | | | | Krtap5-5 | 1.00 | 19567 | 3 | | | | | | Lrrc14 | 1.00 |
| 19472 | 3 | | | | | | Krtap6-1 | 1.00 | 19568 | 3 | | | | | | Lrrc18 | 1.00 |
| 19473 | 3 | | | | | | Krtap6-2 | 1.00 | 19569 | 3 | | | | | | Lrrc19 | 1.00 |
| 19474 | 3 | | | | | | Krtap6-5 | 1.00 | 19570 | 3 | | | | | | Lrrc2 | 1.00 |
| 19475 | 3 | | | | | | Krtap9-1 | 1.00 | 19571 | 3 | | | | | | Lrrc34 | 1.00 |
| 19476 | 3 | | | | | | Krtap9-3 | 1.00 | 19572 | 3 | | | | | | Lrrc36 | 1.00 |
| 19477 | 3 | | | | | | Krtap9-5 | 1.00 | 19573 | 3 | | | | | | Lrrc43 | 1.00 |
| 19478 | 3 | | | | | | Ktn1 | 1.00 | 19574 | 3 | | | | | | Lrrc48 | 1.00 |
| 19479 | 3 | | | | | | L1td1 | 1.00 | 19575 | 3 | | | | | | Lrrc52 | 1.00 |
| 19480 | 3 | | | | | | L3mbtl1 | 1.00 | 19576 | 3 | | | | | | Lrrc6 | 1.00 |
| 19481 | 3 | | | | | | L3mbtl4 | 1.00 | 19577 | 3 | | | | | | Lrrc63 | 1.00 |
| 19482 | 3 | | | | | | LOC100038947 | 1.00 | 19578 | 3 | | | | | | Lrrc66 | 1.00 |
| 19483 | 3 | | | | | | LOC100040786 | 1.00 | 19579 | 3 | | | | | | Lrrc69 | 1.00 |
| 19484 | 3 | | | | | | LOC100043315 | 1.00 | 19580 | 3 | | | | | | Lrrc72 | 1.00 |
| 19485 | 3 | | | | | | LOC100048884 | 1.00 | 19581 | 3 | | | | | | Lrrc74 | 1.00 |

Fig. 45 - 103

| | | | | | | | | | | | | | |
|---|---|---|---|---|---|---|---|---|---|---|---|---|---|
| 19582 | 3 | | | | | Lrrc9 | 1.00 | 19678 | 3 | | | Mir103-1 | 1.00 |
| 19583 | 3 | | | | | Lrrd1 | 1.00 | 19679 | 3 | | | Mir103-2 | 1.00 |
| 19584 | 3 | | | | | Lrriq1 | 1.00 | 19680 | 3 | | | Mir105 | 1.00 |
| 19585 | 3 | | | | | Lrriq3 | 1.00 | 19681 | 3 | | | Mir106a | 1.00 |
| 19586 | 3 | | | | | Lrriq4 | 1.00 | 19682 | 3 | | | Mir106b | 1.00 |
| 19587 | 3 | | | | | Lta | 1.00 | 19683 | 3 | | | Mir107 | 1.00 |
| 19588 | 3 | | | | | Ltc4s | 1.00 | 19684 | 3 | | | Mir10b | 1.00 |
| 19589 | 3 | | | | | Ltk | 1.00 | 19685 | 3 | | | Mir1187 | 1.00 |
| 19590 | 3 | | | | | Luc7l2 | 1.00 | 19686 | 3 | | | Mir1190 | 1.00 |
| 19591 | 3 | | | | | Luzp4 | 1.00 | 19687 | 3 | | | Mir1191 | 1.00 |
| 19592 | 3 | | | | | Ly6f | 1.00 | 19688 | 3 | | | Mir1191b | 1.00 |
| 19593 | 3 | | | | | Ly6g5c | 1.00 | 19689 | 3 | | | Mir1192 | 1.00 |
| 19594 | 3 | | | | | Ly6g6f | 1.00 | 19690 | 3 | | | Mir1193 | 1.00 |
| 19595 | 3 | | | | | Ly6i | 1.00 | 19691 | 3 | | | Mir1195 | 1.00 |
| 19596 | 3 | | | | | Ly6k | 1.00 | 19692 | 3 | | | Mir1197 | 1.00 |
| 19597 | 3 | | | | | Ly75 | 1.00 | 19693 | 3 | | | Mir1198 | 1.00 |
| 19598 | 3 | | | | | Ly9 | 1.00 | 19694 | 3 | | | Mir1199 | 1.00 |
| 19599 | 3 | | | | | Lyg1 | 1.00 | 19695 | 3 | | | Mir1224 | 1.00 |
| 19600 | 3 | | | | | Lyg2 | 1.00 | 19696 | 3 | | | Mir122a | 1.00 |
| 19601 | 3 | | | | | Lypd4 | 1.00 | 19697 | 3 | | | Mir1231 | 1.00 |
| 19602 | 3 | | | | | Lyrm7os | 1.00 | 19698 | 3 | | | Mir1247 | 1.00 |
| 19603 | 3 | | | | | Lyz1 | 1.00 | 19699 | 3 | | | Mir1249 | 1.00 |
| 19604 | 3 | | | | | Lyzl1 | 1.00 | 19700 | 3 | | | Mir124a-1 | 1.00 |
| 19605 | 3 | | | | | Lyzl4 | 1.00 | 19701 | 3 | | | Mir124a-2 | 1.00 |
| 19606 | 3 | | | | | Lyzl4os | 1.00 | 19702 | 3 | | | Mir124a-3 | 1.00 |
| 19607 | 3 | | | | | Lyzl6 | 1.00 | 19703 | 3 | | | Mir1251 | 1.00 |
| 19608 | 3 | | | | | M1ap | 1.00 | 19704 | 3 | | | Mir1258 | 1.00 |
| 19609 | 3 | | | | | Maats1 | 1.00 | 19705 | 3 | | | Mir125a | 1.00 |
| 19610 | 3 | | | | | Mael | 1.00 | 19706 | 3 | | | Mir125b-1 | 1.00 |
| 19611 | 3 | | | | | Mag | 1.00 | 19707 | 3 | | | Mir125b-2 | 1.00 |
| 19612 | 3 | | | | | Magea1 | 1.00 | 19708 | 3 | | | Mir126 | 1.00 |
| 19613 | 3 | | | | | Magea10 | 1.00 | 19709 | 3 | | | Mir1264 | 1.00 |
| 19614 | 3 | | | | | Magea2 | 1.00 | 19710 | 3 | | | Mir126b | 1.00 |
| 19615 | 3 | | | | | Magea3 | 1.00 | 19711 | 3 | | | Mir127 | 1.00 |
| 19616 | 3 | | | | | Magea4 | 1.00 | 19712 | 3 | | | Mir128-1 | 1.00 |
| 19617 | 3 | | | | | Magea5 | 1.00 | 19713 | 3 | | | Mir128-2 | 1.00 |
| 19618 | 3 | | | | | Magea6 | 1.00 | 19714 | 3 | | | Mir129-1 | 1.00 |
| 19619 | 3 | | | | | Magea8 | 1.00 | 19715 | 3 | | | Mir129-2 | 1.00 |
| 19620 | 3 | | | | | Mageb1 | 1.00 | 19716 | 3 | | | Mir1291 | 1.00 |
| 19621 | 3 | | | | | Mageb16 | 1.00 | 19717 | 3 | | | Mir1298 | 1.00 |
| 19622 | 3 | | | | | Mageb16-ps1 | 1.00 | 19718 | 3 | | | Mir129b | 1.00 |
| 19623 | 3 | | | | | Mageb18 | 1.00 | 19719 | 3 | | | Mir1306 | 1.00 |
| 19624 | 3 | | | | | Mageb2 | 1.00 | 19720 | 3 | | | Mir130a | 1.00 |
| 19625 | 3 | | | | | Mageb3 | 1.00 | 19721 | 3 | | | Mir130b | 1.00 |
| 19626 | 3 | | | | | Mageb4 | 1.00 | 19722 | 3 | | | Mir130c | 1.00 |
| 19627 | 3 | | | | | Mageb5 | 1.00 | 19723 | 3 | | | Mir132 | 1.00 |
| 19628 | 3 | | | | | Magix | 1.00 | 19724 | 3 | | | Mir133a-1 | 1.00 |
| 19629 | 3 | | | | | Mak | 1.00 | 19725 | 3 | | | Mir133a-2 | 1.00 |
| 19630 | 3 | | | | | Manr | 1.00 | 19726 | 3 | | | Mir133b | 1.00 |
| 19631 | 3 | | | | | Map3k15 | 1.00 | 19727 | 3 | | | Mir133c | 1.00 |
| 19632 | 3 | | | | | Map3k19 | 1.00 | 19728 | 3 | | | Mir134 | 1.00 |
| 19633 | 3 | | | | | Map4k1 | 1.00 | 19729 | 3 | | | Mir135a-1 | 1.00 |
| 19634 | 3 | | | | | Mapk15 | 1.00 | 19730 | 3 | | | Mir135a-2 | 1.00 |
| 19635 | 3 | | | | | March10 | 1.00 | 19731 | 3 | | | Mir135b | 1.00 |
| 19636 | 3 | | | | | Mbd3l1 | 1.00 | 19732 | 3 | | | Mir136 | 1.00 |
| 19637 | 3 | | | | | Mbd3l2 | 1.00 | 19733 | 3 | | | Mir137 | 1.00 |
| 19638 | 3 | | | | | Mbl2 | 1.00 | 19734 | 3 | | | Mir138-1 | 1.00 |
| 19639 | 3 | | | | | Mboat4 | 1.00 | 19735 | 3 | | | Mir138-2 | 1.00 |
| 19640 | 3 | | | | | Mc1r | 1.00 | 19736 | 3 | | | Mir139 | 1.00 |
| 19641 | 3 | | | | | Mc3r | 1.00 | 19737 | 3 | | | Mir140 | 1.00 |
| 19642 | 3 | | | | | Mccc1os | 1.00 | 19738 | 3 | | | Mir141 | 1.00 |
| 19643 | 3 | | | | | Mcf2 | 1.00 | 19739 | 3 | | | Mir142 | 1.00 |
| 19644 | 3 | | | | | Mcmdc2 | 1.00 | 19740 | 3 | | | Mir142b | 1.00 |
| 19645 | 3 | | | | | Mcoln3 | 1.00 | 19741 | 3 | | | Mir143 | 1.00 |
| 19646 | 3 | | | | | Mcpt-ps1 | 1.00 | 19742 | 3 | | | Mir144 | 1.00 |
| 19647 | 3 | | | | | Mcpt1 | 1.00 | 19743 | 3 | | | Mir145 | 1.00 |
| 19648 | 3 | | | | | Mcpt2 | 1.00 | 19744 | 3 | | | Mir145b | 1.00 |
| 19649 | 3 | | | | | Mcpt8 | 1.00 | 19745 | 3 | | | Mir146 | 1.00 |
| 19650 | 3 | | | | | Mcpt9 | 1.00 | 19746 | 3 | | | Mir146b | 1.00 |
| 19651 | 3 | | | | | Mctp1 | 1.00 | 19747 | 3 | | | Mir147 | 1.00 |
| 19652 | 3 | | | | | Mdh1b | 1.00 | 19748 | 3 | | | Mir148a | 1.00 |
| 19653 | 3 | | | | | Me3 | 1.00 | 19749 | 3 | | | Mir148b | 1.00 |
| 19654 | 3 | | | | | Mef2b | 1.00 | 19750 | 3 | | | Mir149 | 1.00 |
| 19655 | 3 | | | | | Mefv | 1.00 | 19751 | 3 | | | Mir150 | 1.00 |
| 19656 | 3 | | | | | Mei1 | 1.00 | 19752 | 3 | | | Mir152 | 1.00 |
| 19657 | 3 | | | | | Mei4 | 1.00 | 19753 | 3 | | | Mir153 | 1.00 |
| 19658 | 3 | | | | | Meig1 | 1.00 | 19754 | 3 | | | Mir154 | 1.00 |
| 19659 | 3 | | | | | Meiob | 1.00 | 19755 | 3 | | | Mir155 | 1.00 |
| 19660 | 3 | | | | | Mepe | 1.00 | 19756 | 3 | | | Mir15a | 1.00 |
| 19661 | 3 | | | | | Mesp1 | 1.00 | 19757 | 3 | | | Mir15b | 1.00 |
| 19662 | 3 | | | | | Mesp2 | 1.00 | 19758 | 3 | | | Mir16-1 | 1.00 |
| 19663 | 3 | | | | | Mettl11b | 1.00 | 19759 | 3 | | | Mir16-2 | 1.00 |
| 19664 | 3 | | | | | Mettl24 | 1.00 | 19760 | 3 | | | Mir1668 | 1.00 |
| 19665 | 3 | | | | | Mettl7a2 | 1.00 | 19761 | 3 | | | Mir17 | 1.00 |
| 19666 | 3 | | | | | Mettl7a2Higd1c | 1.00 | 19762 | 3 | | | Mir18 | 1.00 |
| 19667 | 3 | | | | | Mettl7a3 | 1.00 | 19763 | 3 | | | Mir181a-1 | 1.00 |
| 19668 | 3 | | | | | Mfrp | 1.00 | 19764 | 3 | | | Mir181a-2 | 1.00 |
| 19669 | 3 | | | | | Mgl2 | 1.00 | 19765 | 3 | | | Mir181b-1 | 1.00 |
| 19670 | 3 | | | | | Micalcl | 1.00 | 19766 | 3 | | | Mir181b-2 | 1.00 |
| 19671 | 3 | | | | | Mill1 | 1.00 | 19767 | 3 | | | Mir181c | 1.00 |
| 19672 | 3 | | | | | Mink1 | 1.00 | 19768 | 3 | | | Mir181d | 1.00 |
| 19673 | 3 | | | | | Miox | 1.00 | 19769 | 3 | | | Mir182 | 1.00 |
| 19674 | 3 | | | | | Mir100 | 1.00 | 19770 | 3 | | | Mir183 | 1.00 |
| 19675 | 3 | | | | | Mir101a | 1.00 | 19771 | 3 | | | Mir1839 | 1.00 |
| 19676 | 3 | | | | | Mir101b | 1.00 | 19772 | 3 | | | Mir184 | 1.00 |
| 19677 | 3 | | | | | Mir101c | 1.00 | 19773 | 3 | | | Mir1843 | 1.00 |

Fig. 45 - 104

| | | | | | | | | | | | | | |
|---|---|---|---|---|---|---|---|---|---|---|---|---|---|
| 19774 | 3 | | | | | Mir1843b | 1.00 | 19870 | 3 | | | Mir206 | 1.00 |
| 19775 | 3 | | | | | Mir185 | 1.00 | 19871 | 3 | | | Mir207 | 1.00 |
| 19776 | 3 | | | | | Mir186 | 1.00 | 19872 | 3 | | | Mir208a | 1.00 |
| 19777 | 3 | | | | | Mir187 | 1.00 | 19873 | 3 | | | Mir208b | 1.00 |
| 19778 | 3 | | | | | Mir188 | 1.00 | 19874 | 3 | | | Mir20a | 1.00 |
| 19779 | 3 | | | | | Mir1892 | 1.00 | 19875 | 3 | | | Mir20b | 1.00 |
| 19780 | 3 | | | | | Mir1893 | 1.00 | 19876 | 3 | | | Mir21 | 1.00 |
| 19781 | 3 | | | | | Mir1894 | 1.00 | 19877 | 3 | | | Mir210 | 1.00 |
| 19782 | 3 | | | | | Mir1895 | 1.00 | 19878 | 3 | | | Mir211 | 1.00 |
| 19783 | 3 | | | | | Mir1896 | 1.00 | 19879 | 3 | | | Mir212 | 1.00 |
| 19784 | 3 | | | | | Mir1897 | 1.00 | 19880 | 3 | | | Mir2136 | 1.00 |
| 19785 | 3 | | | | | Mir1898 | 1.00 | 19881 | 3 | | | Mir2137 | 1.00 |
| 19786 | 3 | | | | | Mir1899 | 1.00 | 19882 | 3 | | | Mir2139 | 1.00 |
| 19787 | 3 | | | | | Mir18b | 1.00 | 19883 | 3 | | | Mir214 | 1.00 |
| 19788 | 3 | | | | | Mir190 | 1.00 | 19884 | 3 | | | Mir215 | 1.00 |
| 19789 | 3 | | | | | Mir1900 | 1.00 | 19885 | 3 | | | Mir216a | 1.00 |
| 19790 | 3 | | | | | Mir1901 | 1.00 | 19886 | 3 | | | Mir216b | 1.00 |
| 19791 | 3 | | | | | Mir1902 | 1.00 | 19887 | 3 | | | Mir216c | 1.00 |
| 19792 | 3 | | | | | Mir1903 | 1.00 | 19888 | 3 | | | Mir217 | 1.00 |
| 19793 | 3 | | | | | Mir1904 | 1.00 | 19889 | 3 | | | Mir218-1 | 1.00 |
| 19794 | 3 | | | | | Mir1905 | 1.00 | 19890 | 3 | | | Mir218-2 | 1.00 |
| 19795 | 3 | | | | | Mir1906-1 | 1.00 | 19891 | 3 | | | Mir219-1 | 1.00 |
| 19796 | 3 | | | | | Mir1907 | 1.00 | 19892 | 3 | | | Mir219-2 | 1.00 |
| 19797 | 3 | | | | | Mir190b | 1.00 | 19893 | 3 | | | Mir219b | 1.00 |
| 19798 | 3 | | | | | Mir191 | 1.00 | 19894 | 3 | | | Mir219c | 1.00 |
| 19799 | 3 | | | | | Mir1912 | 1.00 | 19895 | 3 | | | Mir21b | 1.00 |
| 19800 | 3 | | | | | Mir192 | 1.00 | 19896 | 3 | | | Mir21c | 1.00 |
| 19801 | 3 | | | | | Mir1928 | 1.00 | 19897 | 3 | | | Mir22 | 1.00 |
| 19802 | 3 | | | | | Mir1929 | 1.00 | 19898 | 3 | | | Mir221 | 1.00 |
| 19803 | 3 | | | | | Mir193 | 1.00 | 19899 | 3 | | | Mir222 | 1.00 |
| 19804 | 3 | | | | | Mir1930 | 1.00 | 19900 | 3 | | | Mir223 | 1.00 |
| 19805 | 3 | | | | | Mir1931 | 1.00 | 19901 | 3 | | | Mir23a | 1.00 |
| 19806 | 3 | | | | | Mir1932 | 1.00 | 19902 | 3 | | | Mir23b | 1.00 |
| 19807 | 3 | | | | | Mir1933 | 1.00 | 19903 | 3 | | | Mir24-1 | 1.00 |
| 19808 | 3 | | | | | Mir1934 | 1.00 | 19904 | 3 | | | Mir24-2 | 1.00 |
| 19809 | 3 | | | | | Mir1936 | 1.00 | 19905 | 3 | | | Mir25 | 1.00 |
| 19810 | 3 | | | | | Mir1938 | 1.00 | 19906 | 3 | | | Mir26a-1 | 1.00 |
| 19811 | 3 | | | | | Mir193b | 1.00 | 19907 | 3 | | | Mir26a-2 | 1.00 |
| 19812 | 3 | | | | | Mir194-1 | 1.00 | 19908 | 3 | | | Mir26b | 1.00 |
| 19813 | 3 | | | | | Mir194-2 | 1.00 | 19909 | 3 | | | Mir27a | 1.00 |
| 19814 | 3 | | | | | Mir1940 | 1.00 | 19910 | 3 | | | Mir27b | 1.00 |
| 19815 | 3 | | | | | Mir1941 | 1.00 | 19911 | 3 | | | Mir28 | 1.00 |
| 19816 | 3 | | | | | Mir1942 | 1.00 | 19912 | 3 | | | Mir2861 | 1.00 |
| 19817 | 3 | | | | | Mir1943 | 1.00 | 19913 | 3 | | | Mir28b | 1.00 |
| 19818 | 3 | | | | | Mir1945 | 1.00 | 19914 | 3 | | | Mir28c | 1.00 |
| 19819 | 3 | | | | | Mir1946a | 1.00 | 19915 | 3 | | | Mir290 | 1.00 |
| 19820 | 3 | | | | | Mir1946b | 1.00 | 19916 | 3 | | | Mir290b | 1.00 |
| 19821 | 3 | | | | | Mir1947 | 1.00 | 19917 | 3 | | | Mir291a | 1.00 |
| 19822 | 3 | | | | | Mir1948 | 1.00 | 19918 | 3 | | | Mir291b | 1.00 |
| 19823 | 3 | | | | | Mir1949 | 1.00 | 19919 | 3 | | | Mir292 | 1.00 |
| 19824 | 3 | | | | | Mir195 | 1.00 | 19920 | 3 | | | Mir292b | 1.00 |
| 19825 | 3 | | | | | Mir1950 | 1.00 | 19921 | 3 | | | Mir293 | 1.00 |
| 19826 | 3 | | | | | Mir1951 | 1.00 | 19922 | 3 | | | Mir294 | 1.00 |
| 19827 | 3 | | | | | Mir1952 | 1.00 | 19923 | 3 | | | Mir295 | 1.00 |
| 19828 | 3 | | | | | Mir1953 | 1.00 | 19924 | 3 | | | Mir296 | 1.00 |
| 19829 | 3 | | | | | Mir1954 | 1.00 | 19925 | 3 | | | Mir297-1 | 1.00 |
| 19830 | 3 | | | | | Mir1955 | 1.00 | 19926 | 3 | | | Mir297-2 | 1.00 |
| 19831 | 3 | | | | | Mir1956 | 1.00 | 19927 | 3 | | | Mir297a-3 | 1.00 |
| 19832 | 3 | | | | | Mir1957 | 1.00 | 19928 | 3 | | | Mir297a-4 | 1.00 |
| 19833 | 3 | | | | | Mir1957b | 1.00 | 19929 | 3 | | | Mir297b | 1.00 |
| 19834 | 3 | | | | | Mir1958 | 1.00 | 19930 | 3 | | | Mir297c | 1.00 |
| 19835 | 3 | | | | | Mir195b | 1.00 | 19931 | 3 | | | Mir298 | 1.00 |
| 19836 | 3 | | | | | Mir1960 | 1.00 | 19932 | 3 | | | Mir299 | 1.00 |
| 19837 | 3 | | | | | Mir1961 | 1.00 | 19933 | 3 | | | Mir299b | 1.00 |
| 19838 | 3 | | | | | Mir1962 | 1.00 | 19934 | 3 | | | Mir29a | 1.00 |
| 19839 | 3 | | | | | Mir1963 | 1.00 | 19935 | 3 | | | Mir29b-1 | 1.00 |
| 19840 | 3 | | | | | Mir1964 | 1.00 | 19936 | 3 | | | Mir29b-2 | 1.00 |
| 19841 | 3 | | | | | Mir1966 | 1.00 | 19937 | 3 | | | Mir29c | 1.00 |
| 19842 | 3 | | | | | Mir1967 | 1.00 | 19938 | 3 | | | Mir300 | 1.00 |
| 19843 | 3 | | | | | Mir1968 | 1.00 | 19939 | 3 | | | Mir301 | 1.00 |
| 19844 | 3 | | | | | Mir1969 | 1.00 | 19940 | 3 | | | Mir301b | 1.00 |
| 19845 | 3 | | | | | Mir196a-1 | 1.00 | 19941 | 3 | | | Mir302a | 1.00 |
| 19846 | 3 | | | | | Mir196a-2 | 1.00 | 19942 | 3 | | | Mir302b | 1.00 |
| 19847 | 3 | | | | | Mir196b | 1.00 | 19943 | 3 | | | Mir302c | 1.00 |
| 19848 | 3 | | | | | Mir1970 | 1.00 | 19944 | 3 | | | Mir302d | 1.00 |
| 19849 | 3 | | | | | Mir1971 | 1.00 | 19945 | 3 | | | Mir3057 | 1.00 |
| 19850 | 3 | | | | | Mir1981 | 1.00 | 19946 | 3 | | | Mir3058 | 1.00 |
| 19851 | 3 | | | | | Mir1982 | 1.00 | 19947 | 3 | | | Mir3059 | 1.00 |
| 19852 | 3 | | | | | Mir1983 | 1.00 | 19948 | 3 | | | Mir3060 | 1.00 |
| 19853 | 3 | | | | | Mir199a-1 | 1.00 | 19949 | 3 | | | Mir3061 | 1.00 |
| 19854 | 3 | | | | | Mir199a-2 | 1.00 | 19950 | 3 | | | Mir3062 | 1.00 |
| 19855 | 3 | | | | | Mir199b | 1.00 | 19951 | 3 | | | Mir3063 | 1.00 |
| 19856 | 3 | | | | | Mir19a | 1.00 | 19952 | 3 | | | Mir3064 | 1.00 |
| 19857 | 3 | | | | | Mir19b-1 | 1.00 | 19953 | 3 | | | Mir3065 | 1.00 |
| 19858 | 3 | | | | | Mir19b-2 | 1.00 | 19954 | 3 | | | Mir3066 | 1.00 |
| 19859 | 3 | | | | | Mir1a-1 | 1.00 | 19955 | 3 | | | Mir3067 | 1.00 |
| 19860 | 3 | | | | | Mir1a-2 | 1.00 | 19956 | 3 | | | Mir3068 | 1.00 |
| 19861 | 3 | | | | | Mir1b | 1.00 | 19957 | 3 | | | Mir3069 | 1.00 |
| 19862 | 3 | | | | | Mir200a | 1.00 | 19958 | 3 | | | Mir3070a | 1.00 |
| 19863 | 3 | | | | | Mir200b | 1.00 | 19959 | 3 | | | Mir3070b | 1.00 |
| 19864 | 3 | | | | | Mir200c | 1.00 | 19960 | 3 | | | Mir3071 | 1.00 |
| 19865 | 3 | | | | | Mir201 | 1.00 | 19961 | 3 | | | Mir3072 | 1.00 |
| 19866 | 3 | | | | | Mir202 | 1.00 | 19962 | 3 | | | Mir3073 | 1.00 |
| 19867 | 3 | | | | | Mir203 | 1.00 | 19963 | 3 | | | Mir3073b | 1.00 |
| 19868 | 3 | | | | | Mir204 | 1.00 | 19964 | 3 | | | Mir3074-1 | 1.00 |
| 19869 | 3 | | | | | Mir205 | 1.00 | 19965 | 3 | | | Mir3074-2 | 1.00 |

Fig. 45 - 105

| | | | | | | | | | | | | | | |
|---|---|---|---|---|---|---|---|---|---|---|---|---|---|---|
| 19966 | 3 | | | | | Mir3075 | 1.00 | 20062 | 3 | | | | Mir3620 | 1.00 |
| 19967 | 3 | | | | | Mir3076 | 1.00 | 20063 | 3 | | | | Mir363 | 1.00 |
| 19968 | 3 | | | | | Mir3077 | 1.00 | 20064 | 3 | | | | Mir365-1 | 1.00 |
| 19969 | 3 | | | | | Mir3078 | 1.00 | 20065 | 3 | | | | Mir365-2 | 1.00 |
| 19970 | 3 | | | | | Mir3079 | 1.00 | 20066 | 3 | | | | Mir367 | 1.00 |
| 19971 | 3 | | | | | Mir3081 | 1.00 | 20067 | 3 | | | | Mir369 | 1.00 |
| 19972 | 3 | | | | | Mir3082 | 1.00 | 20068 | 3 | | | | Mir370 | 1.00 |
| 19973 | 3 | | | | | Mir3083 | 1.00 | 20069 | 3 | | | | Mir374 | 1.00 |
| 19974 | 3 | | | | | Mir3084 | 1.00 | 20070 | 3 | | | | Mir374c | 1.00 |
| 19975 | 3 | | | | | Mir3084-2 | 1.00 | 20071 | 3 | | | | Mir375 | 1.00 |
| 19976 | 3 | | | | | Mir3085 | 1.00 | 20072 | 3 | | | | Mir376a | 1.00 |
| 19977 | 3 | | | | | Mir3086 | 1.00 | 20073 | 3 | | | | Mir376b | 1.00 |
| 19978 | 3 | | | | | Mir3087 | 1.00 | 20074 | 3 | | | | Mir376c | 1.00 |
| 19979 | 3 | | | | | Mir3088 | 1.00 | 20075 | 3 | | | | Mir377 | 1.00 |
| 19980 | 3 | | | | | Mir3089 | 1.00 | 20076 | 3 | | | | Mir378 | 1.00 |
| 19981 | 3 | | | | | Mir3091 | 1.00 | 20077 | 3 | | | | Mir378b | 1.00 |
| 19982 | 3 | | | | | Mir3092 | 1.00 | 20078 | 3 | | | | Mir378c | 1.00 |
| 19983 | 3 | | | | | Mir3093 | 1.00 | 20079 | 3 | | | | Mir379 | 1.00 |
| 19984 | 3 | | | | | Mir3094 | 1.00 | 20080 | 3 | | | | Mir380 | 1.00 |
| 19985 | 3 | | | | | Mir3095 | 1.00 | 20081 | 3 | | | | Mir381 | 1.00 |
| 19986 | 3 | | | | | Mir3097 | 1.00 | 20082 | 3 | | | | Mir382 | 1.00 |
| 19987 | 3 | | | | | Mir3098 | 1.00 | 20083 | 3 | | | | Mir383 | 1.00 |
| 19988 | 3 | | | | | Mir3099 | 1.00 | 20084 | 3 | | | | Mir384 | 1.00 |
| 19989 | 3 | | | | | Mir30a | 1.00 | 20085 | 3 | | | | Mir3960 | 1.00 |
| 19990 | 3 | | | | | Mir30b | 1.00 | 20086 | 3 | | | | Mir3962 | 1.00 |
| 19991 | 3 | | | | | Mir30c-1 | 1.00 | 20087 | 3 | | | | Mir3963 | 1.00 |
| 19992 | 3 | | | | | Mir30c-2 | 1.00 | 20088 | 3 | | | | Mir3964 | 1.00 |
| 19993 | 3 | | | | | Mir30d | 1.00 | 20089 | 3 | | | | Mir3965 | 1.00 |
| 19994 | 3 | | | | | Mir30f | 1.00 | 20090 | 3 | | | | Mir3966 | 1.00 |
| 19995 | 3 | | | | | Mir31 | 1.00 | 20091 | 3 | | | | Mir3967 | 1.00 |
| 19996 | 3 | | | | | Mir3100 | 1.00 | 20092 | 3 | | | | Mir3968 | 1.00 |
| 19997 | 3 | | | | | Mir3101 | 1.00 | 20093 | 3 | | | | Mir3969 | 1.00 |
| 19998 | 3 | | | | | Mir3102 | 1.00 | 20094 | 3 | | | | Mir3970 | 1.00 |
| 19999 | 3 | | | | | Mir3103 | 1.00 | 20095 | 3 | | | | Mir3971 | 1.00 |
| 20000 | 3 | | | | | Mir3104 | 1.00 | 20096 | 3 | | | | Mir409 | 1.00 |
| 20001 | 3 | | | | | Mir3106 | 1.00 | 20097 | 3 | | | | Mir410 | 1.00 |
| 20002 | 3 | | | | | Mir3107 | 1.00 | 20098 | 3 | | | | Mir411 | 1.00 |
| 20003 | 3 | | | | | Mir3108 | 1.00 | 20099 | 3 | | | | Mir412 | 1.00 |
| 20004 | 3 | | | | | Mir3109 | 1.00 | 20100 | 3 | | | | Mir421 | 1.00 |
| 20005 | 3 | | | | | Mir3110 | 1.00 | 20101 | 3 | | | | Mir423 | 1.00 |
| 20006 | 3 | | | | | Mir3112 | 1.00 | 20102 | 3 | | | | Mir425 | 1.00 |
| 20007 | 3 | | | | | Mir32 | 1.00 | 20103 | 3 | | | | Mir429 | 1.00 |
| 20008 | 3 | | | | | Mir320 | 1.00 | 20104 | 3 | | | | Mir431 | 1.00 |
| 20009 | 3 | | | | | Mir322 | 1.00 | 20105 | 3 | | | | Mir432 | 1.00 |
| 20010 | 3 | | | | | Mir323 | 1.00 | 20106 | 3 | | | | Mir433 | 1.00 |
| 20011 | 3 | | | | | Mir324 | 1.00 | 20107 | 3 | | | | Mir434 | 1.00 |
| 20012 | 3 | | | | | Mir325 | 1.00 | 20108 | 3 | | | | Mir448 | 1.00 |
| 20013 | 3 | | | | | Mir326 | 1.00 | 20109 | 3 | | | | Mir449a | 1.00 |
| 20014 | 3 | | | | | Mir328 | 1.00 | 20110 | 3 | | | | Mir449b | 1.00 |
| 20015 | 3 | | | | | Mir329 | 1.00 | 20111 | 3 | | | | Mir449c | 1.00 |
| 20016 | 3 | | | | | Mir33 | 1.00 | 20112 | 3 | | | | Mir450-1 | 1.00 |
| 20017 | 3 | | | | | Mir330 | 1.00 | 20113 | 3 | | | | Mir450-2 | 1.00 |
| 20018 | 3 | | | | | Mir331 | 1.00 | 20114 | 3 | | | | Mir450b | 1.00 |
| 20019 | 3 | | | | | Mir335 | 1.00 | 20115 | 3 | | | | Mir451 | 1.00 |
| 20020 | 3 | | | | | Mir337 | 1.00 | 20116 | 3 | | | | Mir452 | 1.00 |
| 20021 | 3 | | | | | Mir338 | 1.00 | 20117 | 3 | | | | Mir453 | 1.00 |
| 20022 | 3 | | | | | Mir339 | 1.00 | 20118 | 3 | | | | Mir455 | 1.00 |
| 20023 | 3 | | | | | Mir340 | 1.00 | 20119 | 3 | | | | Mir463 | 1.00 |
| 20024 | 3 | | | | | Mir341 | 1.00 | 20120 | 3 | | | | Mir465 | 1.00 |
| 20025 | 3 | | | | | Mir343 | 1.00 | 20121 | 3 | | | | Mir465b-1 | 1.00 |
| 20026 | 3 | | | | | Mir344 | 1.00 | 20122 | 3 | | | | Mir465c-1 | 1.00 |
| 20027 | 3 | | | | | Mir344-2 | 1.00 | 20123 | 3 | | | | Mir465d | 1.00 |
| 20028 | 3 | | | | | Mir344b | 1.00 | 20124 | 3 | | | | Mir466 | 1.00 |
| 20029 | 3 | | | | | Mir344c | 1.00 | 20125 | 3 | | | | Mir466a | 1.00 |
| 20030 | 3 | | | | | Mir344d-1 | 1.00 | 20126 | 3 | | | | Mir466b-2 | 1.00 |
| 20031 | 3 | | | | | Mir344d-2 | 1.00 | 20127 | 3 | | | | Mir466b-3 | 1.00 |
| 20032 | 3 | | | | | Mir344d-3 | 1.00 | 20128 | 3 | | | | Mir466d | 1.00 |
| 20033 | 3 | | | | | Mir344e | 1.00 | 20129 | 3 | | | | Mir466f-1 | 1.00 |
| 20034 | 3 | | | | | Mir344f | 1.00 | 20130 | 3 | | | | Mir466f-2 | 1.00 |
| 20035 | 3 | | | | | Mir344g | 1.00 | 20131 | 3 | | | | Mir466f-3 | 1.00 |
| 20036 | 3 | | | | | Mir344h-1 | 1.00 | 20132 | 3 | | | | Mir466g | 1.00 |
| 20037 | 3 | | | | | Mir344i | 1.00 | 20133 | 3 | | | | Mir466h | 1.00 |
| 20038 | 3 | | | | | Mir345 | 1.00 | 20134 | 3 | | | | Mir466i | 1.00 |
| 20039 | 3 | | | | | Mir346 | 1.00 | 20135 | 3 | | | | Mir466n | 1.00 |
| 20040 | 3 | | | | | Mir3470a | 1.00 | 20136 | 3 | | | | Mir466p | 1.00 |
| 20041 | 3 | | | | | Mir3470b | 1.00 | 20137 | 3 | | | | Mir467a-1 | 1.00 |
| 20042 | 3 | | | | | Mir3471-1 | 1.00 | 20138 | 3 | | | | Mir467a-10 | 1.00 |
| 20043 | 3 | | | | | Mir3473 | 1.00 | 20139 | 3 | | | | Mir467a-2 | 1.00 |
| 20044 | 3 | | | | | Mir3473c | 1.00 | 20140 | 3 | | | | Mir467a-3 | 1.00 |
| 20045 | 3 | | | | | Mir3473d | 1.00 | 20141 | 3 | | | | Mir467a-5 | 1.00 |
| 20046 | 3 | | | | | Mir3473e | 1.00 | 20142 | 3 | | | | Mir467a-7 | 1.00 |
| 20047 | 3 | | | | | Mir3473f | 1.00 | 20143 | 3 | | | | Mir467a-9 | 1.00 |
| 20048 | 3 | | | | | Mir3473g | 1.00 | 20144 | 3 | | | | Mir467b | 1.00 |
| 20049 | 3 | | | | | Mir3474 | 1.00 | 20145 | 3 | | | | Mir467c | 1.00 |
| 20050 | 3 | | | | | Mir3475 | 1.00 | 20146 | 3 | | | | Mir467d | 1.00 |
| 20051 | 3 | | | | | Mir34a | 1.00 | 20147 | 3 | | | | Mir467e | 1.00 |
| 20052 | 3 | | | | | Mir34b | 1.00 | 20148 | 3 | | | | Mir467f | 1.00 |
| 20053 | 3 | | | | | Mir34c | 1.00 | 20149 | 3 | | | | Mir468 | 1.00 |
| 20054 | 3 | | | | | Mir350 | 1.00 | 20150 | 3 | | | | Mir470 | 1.00 |
| 20055 | 3 | | | | | Mir351 | 1.00 | 20151 | 3 | | | | Mir471 | 1.00 |
| 20056 | 3 | | | | | Mir3535 | 1.00 | 20152 | 3 | | | | Mir483 | 1.00 |
| 20057 | 3 | | | | | Mir3544 | 1.00 | 20153 | 3 | | | | Mir484 | 1.00 |
| 20058 | 3 | | | | | Mir3547 | 1.00 | 20154 | 3 | | | | Mir485 | 1.00 |
| 20059 | 3 | | | | | Mir3569 | 1.00 | 20155 | 3 | | | | Mir487b | 1.00 |
| 20060 | 3 | | | | | Mir3572 | 1.00 | 20156 | 3 | | | | Mir488 | 1.00 |
| 20061 | 3 | | | | | Mir362 | 1.00 | 20157 | 3 | | | | Mir489 | 1.00 |

Fig. 45 - 106

| | | | | | | | | | | | | | | |
|---|---|---|---|---|---|---|---|---|---|---|---|---|---|---|
| 20158 | 3 | | | | | Mir490 | 1.00 | 20254 | 3 | | | | Mir6345 | 1.00 |
| 20159 | 3 | | | | | Mir491 | 1.00 | 20255 | 3 | | | | Mir6348 | 1.00 |
| 20160 | 3 | | | | | Mir493 | 1.00 | 20256 | 3 | | | | Mir6349 | 1.00 |
| 20161 | 3 | | | | | Mir494 | 1.00 | 20257 | 3 | | | | Mir6350 | 1.00 |
| 20162 | 3 | | | | | Mir495 | 1.00 | 20258 | 3 | | | | Mir6352 | 1.00 |
| 20163 | 3 | | | | | Mir496 | 1.00 | 20259 | 3 | | | | Mir6353 | 1.00 |
| 20164 | 3 | | | | | Mir496b | 1.00 | 20260 | 3 | | | | Mir6354 | 1.00 |
| 20165 | 3 | | | | | Mir497 | 1.00 | 20261 | 3 | | | | Mir6355 | 1.00 |
| 20166 | 3 | | | | | Mir497b | 1.00 | 20262 | 3 | | | | Mir6356 | 1.00 |
| 20167 | 3 | | | | | Mir499 | 1.00 | 20263 | 3 | | | | Mir6358 | 1.00 |
| 20168 | 3 | | | | | Mir500 | 1.00 | 20264 | 3 | | | | Mir6359 | 1.00 |
| 20169 | 3 | | | | | Mir501 | 1.00 | 20265 | 3 | | | | Mir6360 | 1.00 |
| 20170 | 3 | | | | | Mir503 | 1.00 | 20266 | 3 | | | | Mir6361 | 1.00 |
| 20171 | 3 | | | | | Mir504 | 1.00 | 20267 | 3 | | | | Mir6362 | 1.00 |
| 20172 | 3 | | | | | Mir5046 | 1.00 | 20268 | 3 | | | | Mir6363 | 1.00 |
| 20173 | 3 | | | | | Mir505 | 1.00 | 20269 | 3 | | | | Mir6364 | 1.00 |
| 20174 | 3 | | | | | Mir509 | 1.00 | 20270 | 3 | | | | Mir6365 | 1.00 |
| 20175 | 3 | | | | | Mir5098 | 1.00 | 20271 | 3 | | | | Mir6366 | 1.00 |
| 20176 | 3 | | | | | Mir5100 | 1.00 | 20272 | 3 | | | | Mir6367 | 1.00 |
| 20177 | 3 | | | | | Mir5101 | 1.00 | 20273 | 3 | | | | Mir6368 | 1.00 |
| 20178 | 3 | | | | | Mir5103 | 1.00 | 20274 | 3 | | | | Mir6369 | 1.00 |
| 20179 | 3 | | | | | Mir5104 | 1.00 | 20275 | 3 | | | | Mir6370 | 1.00 |
| 20180 | 3 | | | | | Mir5106 | 1.00 | 20276 | 3 | | | | Mir6372 | 1.00 |
| 20181 | 3 | | | | | Mir5107 | 1.00 | 20277 | 3 | | | | Mir6373 | 1.00 |
| 20182 | 3 | | | | | Mir5108 | 1.00 | 20278 | 3 | | | | Mir6374 | 1.00 |
| 20183 | 3 | | | | | Mir511 | 1.00 | 20279 | 3 | | | | Mir6375 | 1.00 |
| 20184 | 3 | | | | | Mir5112 | 1.00 | 20280 | 3 | | | | Mir6376 | 1.00 |
| 20185 | 3 | | | | | Mir5113 | 1.00 | 20281 | 3 | | | | Mir6378 | 1.00 |
| 20186 | 3 | | | | | Mir5114 | 1.00 | 20282 | 3 | | | | Mir6380 | 1.00 |
| 20187 | 3 | | | | | Mir5116 | 1.00 | 20283 | 3 | | | | Mir6381 | 1.00 |
| 20188 | 3 | | | | | Mir5119 | 1.00 | 20284 | 3 | | | | Mir6382 | 1.00 |
| 20189 | 3 | | | | | Mir5120 | 1.00 | 20285 | 3 | | | | Mir6383 | 1.00 |
| 20190 | 3 | | | | | Mir5121 | 1.00 | 20286 | 3 | | | | Mir6384 | 1.00 |
| 20191 | 3 | | | | | Mir5122 | 1.00 | 20287 | 3 | | | | Mir6385 | 1.00 |
| 20192 | 3 | | | | | Mir5123 | 1.00 | 20288 | 3 | | | | Mir6386 | 1.00 |
| 20193 | 3 | | | | | Mir5124 | 1.00 | 20289 | 3 | | | | Mir6387 | 1.00 |
| 20194 | 3 | | | | | Mir5125 | 1.00 | 20290 | 3 | | | | Mir6388 | 1.00 |
| 20195 | 3 | | | | | Mir5126 | 1.00 | 20291 | 3 | | | | Mir6389 | 1.00 |
| 20196 | 3 | | | | | Mir5127 | 1.00 | 20292 | 3 | | | | Mir6390 | 1.00 |
| 20197 | 3 | | | | | Mir5128 | 1.00 | 20293 | 3 | | | | Mir6391 | 1.00 |
| 20198 | 3 | | | | | Mir5129 | 1.00 | 20294 | 3 | | | | Mir6392 | 1.00 |
| 20199 | 3 | | | | | Mir5130 | 1.00 | 20295 | 3 | | | | Mir6393 | 1.00 |
| 20200 | 3 | | | | | Mir5131 | 1.00 | 20296 | 3 | | | | Mir6394 | 1.00 |
| 20201 | 3 | | | | | Mir5132 | 1.00 | 20297 | 3 | | | | Mir6395 | 1.00 |
| 20202 | 3 | | | | | Mir5133 | 1.00 | 20298 | 3 | | | | Mir6396 | 1.00 |
| 20203 | 3 | | | | | Mir5134 | 1.00 | 20299 | 3 | | | | Mir6397 | 1.00 |
| 20204 | 3 | | | | | Mir5135 | 1.00 | 20300 | 3 | | | | Mir6398 | 1.00 |
| 20205 | 3 | | | | | Mir5136 | 1.00 | 20301 | 3 | | | | Mir6399 | 1.00 |
| 20206 | 3 | | | | | Mir532 | 1.00 | 20302 | 3 | | | | Mir6400 | 1.00 |
| 20207 | 3 | | | | | Mir539 | 1.00 | 20303 | 3 | | | | Mir6401 | 1.00 |
| 20208 | 3 | | | | | Mir540 | 1.00 | 20304 | 3 | | | | Mir6402 | 1.00 |
| 20209 | 3 | | | | | Mir541 | 1.00 | 20305 | 3 | | | | Mir6403 | 1.00 |
| 20210 | 3 | | | | | Mir542 | 1.00 | 20306 | 3 | | | | Mir6404 | 1.00 |
| 20211 | 3 | | | | | Mir543 | 1.00 | 20307 | 3 | | | | Mir6405 | 1.00 |
| 20212 | 3 | | | | | Mir544 | 1.00 | 20308 | 3 | | | | Mir6406 | 1.00 |
| 20213 | 3 | | | | | Mir546 | 1.00 | 20309 | 3 | | | | Mir6407 | 1.00 |
| 20214 | 3 | | | | | Mir547 | 1.00 | 20310 | 3 | | | | Mir6408 | 1.00 |
| 20215 | 3 | | | | | Mir551b | 1.00 | 20311 | 3 | | | | Mir6409 | 1.00 |
| 20216 | 3 | | | | | Mir551b-1 | 1.00 | 20312 | 3 | | | | Mir6410 | 1.00 |
| 20217 | 3 | | | | | Mir551b-2 | 1.00 | 20313 | 3 | | | | Mir6411 | 1.00 |
| 20218 | 3 | | | | | Mir5616 | 1.00 | 20314 | 3 | | | | Mir6412 | 1.00 |
| 20219 | 3 | | | | | Mir5617 | 1.00 | 20315 | 3 | | | | Mir6413 | 1.00 |
| 20220 | 3 | | | | | Mir5618 | 1.00 | 20316 | 3 | | | | Mir6414 | 1.00 |
| 20221 | 3 | | | | | Mir5619 | 1.00 | 20317 | 3 | | | | Mir6415 | 1.00 |
| 20222 | 3 | | | | | Mir5620 | 1.00 | 20318 | 3 | | | | Mir6416 | 1.00 |
| 20223 | 3 | | | | | Mir5621 | 1.00 | 20319 | 3 | | | | Mir6417 | 1.00 |
| 20224 | 3 | | | | | Mir5622 | 1.00 | 20320 | 3 | | | | Mir6418 | 1.00 |
| 20225 | 3 | | | | | Mir5623 | 1.00 | 20321 | 3 | | | | Mir6419 | 1.00 |
| 20226 | 3 | | | | | Mir5624 | 1.00 | 20322 | 3 | | | | Mir6420 | 1.00 |
| 20227 | 3 | | | | | Mir5625 | 1.00 | 20323 | 3 | | | | Mir6481 | 1.00 |
| 20228 | 3 | | | | | Mir5626 | 1.00 | 20324 | 3 | | | | Mir6516 | 1.00 |
| 20229 | 3 | | | | | Mir5627 | 1.00 | 20325 | 3 | | | | Mir653 | 1.00 |
| 20230 | 3 | | | | | Mir568 | 1.00 | 20326 | 3 | | | | Mir6537 | 1.00 |
| 20231 | 3 | | | | | Mir5709 | 1.00 | 20327 | 3 | | | | Mir6538 | 1.00 |
| 20232 | 3 | | | | | Mir5710 | 1.00 | 20328 | 3 | | | | Mir6539 | 1.00 |
| 20233 | 3 | | | | | Mir574 | 1.00 | 20329 | 3 | | | | Mir654 | 1.00 |
| 20234 | 3 | | | | | Mir582 | 1.00 | 20330 | 3 | | | | Mir6540 | 1.00 |
| 20235 | 3 | | | | | Mir592 | 1.00 | 20331 | 3 | | | | Mir6541 | 1.00 |
| 20236 | 3 | | | | | Mir598 | 1.00 | 20332 | 3 | | | | Mir6546 | 1.00 |
| 20237 | 3 | | | | | Mir599 | 1.00 | 20333 | 3 | | | | Mir664 | 1.00 |
| 20238 | 3 | | | | | Mir615 | 1.00 | 20334 | 3 | | | | Mir665 | 1.00 |
| 20239 | 3 | | | | | Mir6237 | 1.00 | 20335 | 3 | | | | Mir666 | 1.00 |
| 20240 | 3 | | | | | Mir6238 | 1.00 | 20336 | 3 | | | | Mir667 | 1.00 |
| 20241 | 3 | | | | | Mir6239 | 1.00 | 20337 | 3 | | | | Mir668 | 1.00 |
| 20242 | 3 | | | | | Mir6241 | 1.00 | 20338 | 3 | | | | Mir669a-1 | 1.00 |
| 20243 | 3 | | | | | Mir6244 | 1.00 | 20339 | 3 | | | | Mir669a-2 | 1.00 |
| 20244 | 3 | | | | | Mir6335 | 1.00 | 20340 | 3 | | | | Mir669a-3 | 1.00 |
| 20245 | 3 | | | | | Mir6336 | 1.00 | 20341 | 3 | | | | Mir669a-4 | 1.00 |
| 20246 | 3 | | | | | Mir6337 | 1.00 | 20342 | 3 | | | | Mir669b | 1.00 |
| 20247 | 3 | | | | | Mir6338 | 1.00 | 20343 | 3 | | | | Mir669c | 1.00 |
| 20248 | 3 | | | | | Mir6339 | 1.00 | 20344 | 3 | | | | Mir669e | 1.00 |
| 20249 | 3 | | | | | Mir6340 | 1.00 | 20345 | 3 | | | | Mir669g | 1.00 |
| 20250 | 3 | | | | | Mir6341 | 1.00 | 20346 | 3 | | | | Mir669h | 1.00 |
| 20251 | 3 | | | | | Mir6342 | 1.00 | 20347 | 3 | | | | Mir669i | 1.00 |
| 20252 | 3 | | | | | Mir6343 | 1.00 | 20348 | 3 | | | | Mir669j | 1.00 |
| 20253 | 3 | | | | | Mir6344 | 1.00 | 20349 | 3 | | | | Mir669k | 1.00 |

Fig. 45 - 107

| | | | | | | | | | | | | |
|---|---|---|---|---|---|---|---|---|---|---|---|---|
| 20350 | 3 | | | | | Mir669m-1 | 1.00 | 20446 | 3 | | Mir6960 | 1.00 |
| 20351 | 3 | | | | | Mir669m-2 | 1.00 | 20447 | 3 | | Mir6961 | 1.00 |
| 20352 | 3 | | | | | Mir669p-1 | 1.00 | 20448 | 3 | | Mir6962 | 1.00 |
| 20353 | 3 | | | | | Mir670 | 1.00 | 20449 | 3 | | Mir6963 | 1.00 |
| 20354 | 3 | | | | | Mir671 | 1.00 | 20450 | 3 | | Mir6964 | 1.00 |
| 20355 | 3 | | | | | Mir671b | 1.00 | 20451 | 3 | | Mir6965 | 1.00 |
| 20356 | 3 | | | | | Mir672 | 1.00 | 20452 | 3 | | Mir6966 | 1.00 |
| 20357 | 3 | | | | | Mir673 | 1.00 | 20453 | 3 | | Mir6968 | 1.00 |
| 20358 | 3 | | | | | Mir674 | 1.00 | 20454 | 3 | | Mir6969 | 1.00 |
| 20359 | 3 | | | | | Mir675 | 1.00 | 20455 | 3 | | Mir697 | 1.00 |
| 20360 | 3 | | | | | Mir676 | 1.00 | 20456 | 3 | | Mir6970 | 1.00 |
| 20361 | 3 | | | | | Mir676b | 1.00 | 20457 | 3 | | Mir6971 | 1.00 |
| 20362 | 3 | | | | | Mir677 | 1.00 | 20458 | 3 | | Mir6972 | 1.00 |
| 20363 | 3 | | | | | Mir678 | 1.00 | 20459 | 3 | | Mir6973a | 1.00 |
| 20364 | 3 | | | | | Mir679 | 1.00 | 20460 | 3 | | Mir6973b | 1.00 |
| 20365 | 3 | | | | | Mir680-2 | 1.00 | 20461 | 3 | | Mir6974 | 1.00 |
| 20366 | 3 | | | | | Mir680-3 | 1.00 | 20462 | 3 | | Mir6975 | 1.00 |
| 20367 | 3 | | | | | Mir681 | 1.00 | 20463 | 3 | | Mir6976 | 1.00 |
| 20368 | 3 | | | | | Mir683-1 | 1.00 | 20464 | 3 | | Mir6977 | 1.00 |
| 20369 | 3 | | | | | Mir683-2 | 1.00 | 20465 | 3 | | Mir6978 | 1.00 |
| 20370 | 3 | | | | | Mir684-1 | 1.00 | 20466 | 3 | | Mir6979 | 1.00 |
| 20371 | 3 | | | | | Mir684-2 | 1.00 | 20467 | 3 | | Mir698 | 1.00 |
| 20372 | 3 | | | | | Mir686 | 1.00 | 20468 | 3 | | Mir6980 | 1.00 |
| 20373 | 3 | | | | | Mir687 | 1.00 | 20469 | 3 | | Mir6981 | 1.00 |
| 20374 | 3 | | | | | Mir688 | 1.00 | 20470 | 3 | | Mir6982 | 1.00 |
| 20375 | 3 | | | | | Mir6896 | 1.00 | 20471 | 3 | | Mir6983 | 1.00 |
| 20376 | 3 | | | | | Mir6897 | 1.00 | 20472 | 3 | | Mir6984 | 1.00 |
| 20377 | 3 | | | | | Mir6898 | 1.00 | 20473 | 3 | | Mir6985 | 1.00 |
| 20378 | 3 | | | | | Mir6899 | 1.00 | 20474 | 3 | | Mir6986 | 1.00 |
| 20379 | 3 | | | | | Mir690 | 1.00 | 20475 | 3 | | Mir6987 | 1.00 |
| 20380 | 3 | | | | | Mir6900 | 1.00 | 20476 | 3 | | Mir6988 | 1.00 |
| 20381 | 3 | | | | | Mir6901 | 1.00 | 20477 | 3 | | Mir6989 | 1.00 |
| 20382 | 3 | | | | | Mir6902 | 1.00 | 20478 | 3 | | Mir6990 | 1.00 |
| 20383 | 3 | | | | | Mir6903 | 1.00 | 20479 | 3 | | Mir6991 | 1.00 |
| 20384 | 3 | | | | | Mir6904 | 1.00 | 20480 | 3 | | Mir6992 | 1.00 |
| 20385 | 3 | | | | | Mir6905 | 1.00 | 20481 | 3 | | Mir6993 | 1.00 |
| 20386 | 3 | | | | | Mir6906 | 1.00 | 20482 | 3 | | Mir6994 | 1.00 |
| 20387 | 3 | | | | | Mir6907 | 1.00 | 20483 | 3 | | Mir6995 | 1.00 |
| 20388 | 3 | | | | | Mir6908 | 1.00 | 20484 | 3 | | Mir6996 | 1.00 |
| 20389 | 3 | | | | | Mir6909 | 1.00 | 20485 | 3 | | Mir6997 | 1.00 |
| 20390 | 3 | | | | | Mir691 | 1.00 | 20486 | 3 | | Mir6998 | 1.00 |
| 20391 | 3 | | | | | Mir6910 | 1.00 | 20487 | 3 | | Mir6999 | 1.00 |
| 20392 | 3 | | | | | Mir6911 | 1.00 | 20488 | 3 | | Mir7-2 | 1.00 |
| 20393 | 3 | | | | | Mir6912 | 1.00 | 20489 | 3 | | Mir700 | 1.00 |
| 20394 | 3 | | | | | Mir6913 | 1.00 | 20490 | 3 | | Mir7000 | 1.00 |
| 20395 | 3 | | | | | Mir6914 | 1.00 | 20491 | 3 | | Mir7001 | 1.00 |
| 20396 | 3 | | | | | Mir6915 | 1.00 | 20492 | 3 | | Mir7002 | 1.00 |
| 20397 | 3 | | | | | Mir6916 | 1.00 | 20493 | 3 | | Mir7003 | 1.00 |
| 20398 | 3 | | | | | Mir6917 | 1.00 | 20494 | 3 | | Mir7004 | 1.00 |
| 20399 | 3 | | | | | Mir6918 | 1.00 | 20495 | 3 | | Mir7005 | 1.00 |
| 20400 | 3 | | | | | Mir6919 | 1.00 | 20496 | 3 | | Mir7006 | 1.00 |
| 20401 | 3 | | | | | Mir692-1 | 1.00 | 20497 | 3 | | Mir7007 | 1.00 |
| 20402 | 3 | | | | | Mir692-2b | 1.00 | 20498 | 3 | | Mir7008 | 1.00 |
| 20403 | 3 | | | | | Mir6920 | 1.00 | 20499 | 3 | | Mir7009 | 1.00 |
| 20404 | 3 | | | | | Mir6921 | 1.00 | 20500 | 3 | | Mir701 | 1.00 |
| 20405 | 3 | | | | | Mir6922 | 1.00 | 20501 | 3 | | Mir7010 | 1.00 |
| 20406 | 3 | | | | | Mir6923 | 1.00 | 20502 | 3 | | Mir7011 | 1.00 |
| 20407 | 3 | | | | | Mir6924 | 1.00 | 20503 | 3 | | Mir7012 | 1.00 |
| 20408 | 3 | | | | | Mir6925 | 1.00 | 20504 | 3 | | Mir7013 | 1.00 |
| 20409 | 3 | | | | | Mir6926 | 1.00 | 20505 | 3 | | Mir7014 | 1.00 |
| 20410 | 3 | | | | | Mir6927 | 1.00 | 20506 | 3 | | Mir7015 | 1.00 |
| 20411 | 3 | | | | | Mir6928 | 1.00 | 20507 | 3 | | Mir7016 | 1.00 |
| 20412 | 3 | | | | | Mir6929 | 1.00 | 20508 | 3 | | Mir7017 | 1.00 |
| 20413 | 3 | | | | | Mir693 | 1.00 | 20509 | 3 | | Mir7018 | 1.00 |
| 20414 | 3 | | | | | Mir6930 | 1.00 | 20510 | 3 | | Mir7019 | 1.00 |
| 20415 | 3 | | | | | Mir6931 | 1.00 | 20511 | 3 | | Mir702 | 1.00 |
| 20416 | 3 | | | | | Mir6932 | 1.00 | 20512 | 3 | | Mir7020 | 1.00 |
| 20417 | 3 | | | | | Mir6933 | 1.00 | 20513 | 3 | | Mir7021 | 1.00 |
| 20418 | 3 | | | | | Mir6934 | 1.00 | 20514 | 3 | | Mir7022 | 1.00 |
| 20419 | 3 | | | | | Mir6935 | 1.00 | 20515 | 3 | | Mir7023 | 1.00 |
| 20420 | 3 | | | | | Mir6936 | 1.00 | 20516 | 3 | | Mir7024 | 1.00 |
| 20421 | 3 | | | | | Mir6937 | 1.00 | 20517 | 3 | | Mir7025 | 1.00 |
| 20422 | 3 | | | | | Mir6938 | 1.00 | 20518 | 3 | | Mir7026 | 1.00 |
| 20423 | 3 | | | | | Mir6939 | 1.00 | 20519 | 3 | | Mir7027 | 1.00 |
| 20424 | 3 | | | | | Mir694 | 1.00 | 20520 | 3 | | Mir7028 | 1.00 |
| 20425 | 3 | | | | | Mir6940 | 1.00 | 20521 | 3 | | Mir7029 | 1.00 |
| 20426 | 3 | | | | | Mir6941 | 1.00 | 20522 | 3 | | Mir703 | 1.00 |
| 20427 | 3 | | | | | Mir6942 | 1.00 | 20523 | 3 | | Mir7030 | 1.00 |
| 20428 | 3 | | | | | Mir6943 | 1.00 | 20524 | 3 | | Mir7031 | 1.00 |
| 20429 | 3 | | | | | Mir6944 | 1.00 | 20525 | 3 | | Mir7032 | 1.00 |
| 20430 | 3 | | | | | Mir6945 | 1.00 | 20526 | 3 | | Mir7033 | 1.00 |
| 20431 | 3 | | | | | Mir6946 | 1.00 | 20527 | 3 | | Mir7034 | 1.00 |
| 20432 | 3 | | | | | Mir6947 | 1.00 | 20528 | 3 | | Mir7035 | 1.00 |
| 20433 | 3 | | | | | Mir6948 | 1.00 | 20529 | 3 | | Mir7036 | 1.00 |
| 20434 | 3 | | | | | Mir6949 | 1.00 | 20530 | 3 | | Mir7036b | 1.00 |
| 20435 | 3 | | | | | Mir695 | 1.00 | 20531 | 3 | | Mir7037 | 1.00 |
| 20436 | 3 | | | | | Mir6950 | 1.00 | 20532 | 3 | | Mir7038 | 1.00 |
| 20437 | 3 | | | | | Mir6951 | 1.00 | 20533 | 3 | | Mir7039 | 1.00 |
| 20438 | 3 | | | | | Mir6952 | 1.00 | 20534 | 3 | | Mir704 | 1.00 |
| 20439 | 3 | | | | | Mir6953 | 1.00 | 20535 | 3 | | Mir7040 | 1.00 |
| 20440 | 3 | | | | | Mir6954 | 1.00 | 20536 | 3 | | Mir7041 | 1.00 |
| 20441 | 3 | | | | | Mir6955 | 1.00 | 20537 | 3 | | Mir7042 | 1.00 |
| 20442 | 3 | | | | | Mir6956 | 1.00 | 20538 | 3 | | Mir7043 | 1.00 |
| 20443 | 3 | | | | | Mir6957 | 1.00 | 20539 | 3 | | Mir7044 | 1.00 |
| 20444 | 3 | | | | | Mir6958 | 1.00 | 20540 | 3 | | Mir7045 | 1.00 |
| 20445 | 3 | | | | | Mir6959 | 1.00 | 20541 | 3 | | Mir7046 | 1.00 |

Fig. 45 - 108

| | | | | | | | | | | | | | | | |
|---|---|---|---|---|---|---|---|---|---|---|---|---|---|---|---|
| 20542 | 3 | | | | | Mir7047 | 1.00 | 20638 | 3 | | | | | Mir7242 | 1.00 |
| 20543 | 3 | | | | | Mir7048 | 1.00 | 20639 | 3 | | | | | Mir7243 | 1.00 |
| 20544 | 3 | | | | | Mir7049 | 1.00 | 20640 | 3 | | | | | Mir741 | 1.00 |
| 20545 | 3 | | | | | Mir705 | 1.00 | 20641 | 3 | | | | | Mir742 | 1.00 |
| 20546 | 3 | | | | | Mir7050 | 1.00 | 20642 | 3 | | | | | Mir743 | 1.00 |
| 20547 | 3 | | | | | Mir7051 | 1.00 | 20643 | 3 | | | | | Mir743b | 1.00 |
| 20548 | 3 | | | | | Mir7052 | 1.00 | 20644 | 3 | | | | | Mir744 | 1.00 |
| 20549 | 3 | | | | | Mir7053 | 1.00 | 20645 | 3 | | | | | Mir7578 | 1.00 |
| 20550 | 3 | | | | | Mir7054 | 1.00 | 20646 | 3 | | | | | Mir758 | 1.00 |
| 20551 | 3 | | | | | Mir7055 | 1.00 | 20647 | 3 | | | | | Mir759 | 1.00 |
| 20552 | 3 | | | | | Mir7056 | 1.00 | 20648 | 3 | | | | | Mir761 | 1.00 |
| 20553 | 3 | | | | | Mir7057 | 1.00 | 20649 | 3 | | | | | Mir762 | 1.00 |
| 20554 | 3 | | | | | Mir7058 | 1.00 | 20650 | 3 | | | | | Mir764 | 1.00 |
| 20555 | 3 | | | | | Mir7059 | 1.00 | 20651 | 3 | | | | | Mir7646 | 1.00 |
| 20556 | 3 | | | | | Mir706 | 1.00 | 20652 | 3 | | | | | Mir7647 | 1.00 |
| 20557 | 3 | | | | | Mir7061 | 1.00 | 20653 | 3 | | | | | Mir7648 | 1.00 |
| 20558 | 3 | | | | | Mir7062 | 1.00 | 20654 | 3 | | | | | Mir7649 | 1.00 |
| 20559 | 3 | | | | | Mir7063 | 1.00 | 20655 | 3 | | | | | Mir7650 | 1.00 |
| 20560 | 3 | | | | | Mir7064 | 1.00 | 20656 | 3 | | | | | Mir7652 | 1.00 |
| 20561 | 3 | | | | | Mir7065 | 1.00 | 20657 | 3 | | | | | Mir7653 | 1.00 |
| 20562 | 3 | | | | | Mir7066 | 1.00 | 20658 | 3 | | | | | Mir7654 | 1.00 |
| 20563 | 3 | | | | | Mir7067 | 1.00 | 20659 | 3 | | | | | Mir7655 | 1.00 |
| 20564 | 3 | | | | | Mir7068 | 1.00 | 20660 | 3 | | | | | Mir7656 | 1.00 |
| 20565 | 3 | | | | | Mir7069 | 1.00 | 20661 | 3 | | | | | Mir7657 | 1.00 |
| 20566 | 3 | | | | | Mir707 | 1.00 | 20662 | 3 | | | | | Mir7658 | 1.00 |
| 20567 | 3 | | | | | Mir7070 | 1.00 | 20663 | 3 | | | | | Mir7661 | 1.00 |
| 20568 | 3 | | | | | Mir7071 | 1.00 | 20664 | 3 | | | | | Mir7662 | 1.00 |
| 20569 | 3 | | | | | Mir7072 | 1.00 | 20665 | 3 | | | | | Mir7663 | 1.00 |
| 20570 | 3 | | | | | Mir7073 | 1.00 | 20666 | 3 | | | | | Mir7665 | 1.00 |
| 20571 | 3 | | | | | Mir7074 | 1.00 | 20667 | 3 | | | | | Mir7666 | 1.00 |
| 20572 | 3 | | | | | Mir7075 | 1.00 | 20668 | 3 | | | | | Mir7667 | 1.00 |
| 20573 | 3 | | | | | Mir7076 | 1.00 | 20669 | 3 | | | | | Mir7668 | 1.00 |
| 20574 | 3 | | | | | Mir7077 | 1.00 | 20670 | 3 | | | | | Mir7669 | 1.00 |
| 20575 | 3 | | | | | Mir7078 | 1.00 | 20671 | 3 | | | | | Mir767 | 1.00 |
| 20576 | 3 | | | | | Mir7079 | 1.00 | 20672 | 3 | | | | | Mir7670 | 1.00 |
| 20577 | 3 | | | | | Mir708 | 1.00 | 20673 | 3 | | | | | Mir7671 | 1.00 |
| 20578 | 3 | | | | | Mir7080 | 1.00 | 20674 | 3 | | | | | Mir7672 | 1.00 |
| 20579 | 3 | | | | | Mir7081 | 1.00 | 20675 | 3 | | | | | Mir7673 | 1.00 |
| 20580 | 3 | | | | | Mir7082 | 1.00 | 20676 | 3 | | | | | Mir7674 | 1.00 |
| 20581 | 3 | | | | | Mir7083 | 1.00 | 20677 | 3 | | | | | Mir7675 | 1.00 |
| 20582 | 3 | | | | | Mir7084 | 1.00 | 20678 | 3 | | | | | Mir7676-2 | 1.00 |
| 20583 | 3 | | | | | Mir7085 | 1.00 | 20679 | 3 | | | | | Mir7677 | 1.00 |
| 20584 | 3 | | | | | Mir7086 | 1.00 | 20680 | 3 | | | | | Mir7678 | 1.00 |
| 20585 | 3 | | | | | Mir7087 | 1.00 | 20681 | 3 | | | | | Mir7679 | 1.00 |
| 20586 | 3 | | | | | Mir7088 | 1.00 | 20682 | 3 | | | | | Mir7680 | 1.00 |
| 20587 | 3 | | | | | Mir7089 | 1.00 | 20683 | 3 | | | | | Mir7681 | 1.00 |
| 20588 | 3 | | | | | Mir709 | 1.00 | 20684 | 3 | | | | | Mir7682 | 1.00 |
| 20589 | 3 | | | | | Mir7090 | 1.00 | 20685 | 3 | | | | | Mir7684 | 1.00 |
| 20590 | 3 | | | | | Mir7091 | 1.00 | 20686 | 3 | | | | | Mir7685 | 1.00 |
| 20591 | 3 | | | | | Mir7092 | 1.00 | 20687 | 3 | | | | | Mir7686 | 1.00 |
| 20592 | 3 | | | | | Mir7093 | 1.00 | 20688 | 3 | | | | | Mir7687 | 1.00 |
| 20593 | 3 | | | | | Mir7094-1 | 1.00 | 20689 | 3 | | | | | Mir770 | 1.00 |
| 20594 | 3 | | | | | Mir7094-2 | 1.00 | 20690 | 3 | | | | | Mir7b | 1.00 |
| 20595 | 3 | | | | | Mir710 | 1.00 | 20691 | 3 | | | | | Mir802 | 1.00 |
| 20596 | 3 | | | | | Mir711 | 1.00 | 20692 | 3 | | | | | Mir804 | 1.00 |
| 20597 | 3 | | | | | Mir7115 | 1.00 | 20693 | 3 | | | | | Mir8091 | 1.00 |
| 20598 | 3 | | | | | Mir7117 | 1.00 | 20694 | 3 | | | | | Mir8092 | 1.00 |
| 20599 | 3 | | | | | Mir7118 | 1.00 | 20695 | 3 | | | | | Mir8095 | 1.00 |
| 20600 | 3 | | | | | Mir7119 | 1.00 | 20696 | 3 | | | | | Mir8096 | 1.00 |
| 20601 | 3 | | | | | Mir713 | 1.00 | 20697 | 3 | | | | | Mir8097 | 1.00 |
| 20602 | 3 | | | | | Mir717 | 1.00 | 20698 | 3 | | | | | Mir8098 | 1.00 |
| 20603 | 3 | | | | | Mir718 | 1.00 | 20699 | 3 | | | | | Mir8099-1 | 1.00 |
| 20604 | 3 | | | | | Mir719 | 1.00 | 20700 | 3 | | | | | Mir8100 | 1.00 |
| 20605 | 3 | | | | | Mir721 | 1.00 | 20701 | 3 | | | | | Mir8101 | 1.00 |
| 20606 | 3 | | | | | Mir7210 | 1.00 | 20702 | 3 | | | | | Mir8102 | 1.00 |
| 20607 | 3 | | | | | Mir7211 | 1.00 | 20703 | 3 | | | | | Mir8103 | 1.00 |
| 20608 | 3 | | | | | Mir7212 | 1.00 | 20704 | 3 | | | | | Mir8105 | 1.00 |
| 20609 | 3 | | | | | Mir7213 | 1.00 | 20705 | 3 | | | | | Mir8106 | 1.00 |
| 20610 | 3 | | | | | Mir7214 | 1.00 | 20706 | 3 | | | | | Mir8107 | 1.00 |
| 20611 | 3 | | | | | Mir7215 | 1.00 | 20707 | 3 | | | | | Mir8108 | 1.00 |
| 20612 | 3 | | | | | Mir7216 | 1.00 | 20708 | 3 | | | | | Mir8109 | 1.00 |
| 20613 | 3 | | | | | Mir7217 | 1.00 | 20709 | 3 | | | | | Mir8110 | 1.00 |
| 20614 | 3 | | | | | Mir7218 | 1.00 | 20710 | 3 | | | | | Mir8111 | 1.00 |
| 20615 | 3 | | | | | Mir7219 | 1.00 | 20711 | 3 | | | | | Mir8114 | 1.00 |
| 20616 | 3 | | | | | Mir7220 | 1.00 | 20712 | 3 | | | | | Mir8115 | 1.00 |
| 20617 | 3 | | | | | Mir7221 | 1.00 | 20713 | 3 | | | | | Mir8116 | 1.00 |
| 20618 | 3 | | | | | Mir7222 | 1.00 | 20714 | 3 | | | | | Mir8118 | 1.00 |
| 20619 | 3 | | | | | Mir7223 | 1.00 | 20715 | 3 | | | | | Mir8119 | 1.00 |
| 20620 | 3 | | | | | Mir7224 | 1.00 | 20716 | 3 | | | | | Mir8120 | 1.00 |
| 20621 | 3 | | | | | Mir7225 | 1.00 | 20717 | 3 | | | | | Mir871 | 1.00 |
| 20622 | 3 | | | | | Mir7226 | 1.00 | 20718 | 3 | | | | | Mir872 | 1.00 |
| 20623 | 3 | | | | | Mir7227 | 1.00 | 20719 | 3 | | | | | Mir873b | 1.00 |
| 20624 | 3 | | | | | Mir7228 | 1.00 | 20720 | 3 | | | | | Mir874 | 1.00 |
| 20625 | 3 | | | | | Mir7229 | 1.00 | 20721 | 3 | | | | | Mir875 | 1.00 |
| 20626 | 3 | | | | | Mir7230 | 1.00 | 20722 | 3 | | | | | Mir876 | 1.00 |
| 20627 | 3 | | | | | Mir7231 | 1.00 | 20723 | 3 | | | | | Mir877 | 1.00 |
| 20628 | 3 | | | | | Mir7232 | 1.00 | 20724 | 3 | | | | | Mir878 | 1.00 |
| 20629 | 3 | | | | | Mir7233 | 1.00 | 20725 | 3 | | | | | Mir879 | 1.00 |
| 20630 | 3 | | | | | Mir7234 | 1.00 | 20726 | 3 | | | | | Mir880 | 1.00 |
| 20631 | 3 | | | | | Mir7235 | 1.00 | 20727 | 3 | | | | | Mir881 | 1.00 |
| 20632 | 3 | | | | | Mir7236 | 1.00 | 20728 | 3 | | | | | Mir882 | 1.00 |
| 20633 | 3 | | | | | Mir7237 | 1.00 | 20729 | 3 | | | | | Mir883a | 1.00 |
| 20634 | 3 | | | | | Mir7238 | 1.00 | 20730 | 3 | | | | | Mir883b | 1.00 |
| 20635 | 3 | | | | | Mir7239 | 1.00 | 20731 | 3 | | | | | Mir9-1 | 1.00 |
| 20636 | 3 | | | | | Mir7240 | 1.00 | 20732 | 3 | | | | | Mir9-2 | 1.00 |
| 20637 | 3 | | | | | Mir7241 | 1.00 | 20733 | 3 | | | | | Mir9-3 | 1.00 |

Fig. 45 - 109

| | | | | | | | | | | | | | | | | |
|---|---|---|---|---|---|---|---|---|---|---|---|---|---|---|---|---|
| 20734 | 3 | | | | | | Mir92-1 | 1.00 | 20830 | 3 | | | | | Mtl5 | 1.00 |
| 20735 | 3 | | | | | | Mir92-2 | 1.00 | 20831 | 3 | | | | | Mtnr1a | 1.00 |
| 20736 | 3 | | | | | | Mir92b | 1.00 | 20832 | 3 | | | | | Mtnr1b | 1.00 |
| 20737 | 3 | | | | | | Mir93 | 1.00 | 20833 | 3 | | | | | Muc2 | 1.00 |
| 20738 | 3 | | | | | | Mir96 | 1.00 | 20834 | 3 | | | | | Muc20 | 1.00 |
| 20739 | 3 | | | | | | Mir98 | 1.00 | 20835 | 3 | | | | | Muc5ac | 1.00 |
| 20740 | 3 | | | | | | Mir99a | 1.00 | 20836 | 3 | | | | | Muc5b | 1.00 |
| 20741 | 3 | | | | | | Mir99b | 1.00 | 20837 | 3 | | | | | Mucl1 | 1.00 |
| 20742 | 3 | | | | | | Mirlet7a-1 | 1.00 | 20838 | 3 | | | | | Mug-ps1 | 1.00 |
| 20743 | 3 | | | | | | Mirlet7a-2 | 1.00 | 20839 | 3 | | | | | Mug1 | 1.00 |
| 20744 | 3 | | | | | | Mirlet7b | 1.00 | 20840 | 3 | | | | | Mug2 | 1.00 |
| 20745 | 3 | | | | | | Mirlet7c-1 | 1.00 | 20841 | 3 | | | | | Mup1 | 1.00 |
| 20746 | 3 | | | | | | Mirlet7c-2 | 1.00 | 20842 | 3 | | | | | Mup10 | 1.00 |
| 20747 | 3 | | | | | | Mirlet7e | 1.00 | 20843 | 3 | | | | | Mup11 | 1.00 |
| 20748 | 3 | | | | | | Mirlet7f-1 | 1.00 | 20844 | 3 | | | | | Mup12 | 1.00 |
| 20749 | 3 | | | | | | Mirlet7f-2 | 1.00 | 20845 | 3 | | | | | Mup13 | 1.00 |
| 20750 | 3 | | | | | | Mirlet7g | 1.00 | 20846 | 3 | | | | | Mup14 | 1.00 |
| 20751 | 3 | | | | | | Mirlet7i | 1.00 | 20847 | 3 | | | | | Mup15 | 1.00 |
| 20752 | 3 | | | | | | Mirlet7j | 1.00 | 20848 | 3 | | | | | Mup16 | 1.00 |
| 20753 | 3 | | | | | | Mirlet7k | 1.00 | 20849 | 3 | | | | | Mup17 | 1.00 |
| 20754 | 3 | | | | | | Mixl1 | 1.00 | 20850 | 3 | | | | | Mup19 | 1.00 |
| 20755 | 3 | | | | | | Mkln1 | 1.00 | 20851 | 3 | | | | | Mup2 | 1.00 |
| 20756 | 3 | | | | | | Mlana | 1.00 | 20852 | 3 | | | | | Mup20 | 1.00 |
| 20757 | 3 | | | | | | Mlkl | 1.00 | 20853 | 3 | | | | | Mup21 | 1.00 |
| 20758 | 3 | | | | | | Mmel1 | 1.00 | 20854 | 3 | | | | | Mup3 | 1.00 |
| 20759 | 3 | | | | | | Mmp10 | 1.00 | 20855 | 3 | | | | | Mup4 | 1.00 |
| 20760 | 3 | | | | | | Mmp12 | 1.00 | 20856 | 3 | | | | | Mup5 | 1.00 |
| 20761 | 3 | | | | | | Mmp1a | 1.00 | 20857 | 3 | | | | | Mup6 | 1.00 |
| 20762 | 3 | | | | | | Mmp1b | 1.00 | 20858 | 3 | | | | | Mup7 | 1.00 |
| 20763 | 3 | | | | | | Mmp20 | 1.00 | 20859 | 3 | | | | | Mup8 | 1.00 |
| 20764 | 3 | | | | | | Mmp21 | 1.00 | 20860 | 3 | | | | | Mup9 | 1.00 |
| 20765 | 3 | | | | | | Mmp27 | 1.00 | 20861 | 3 | | | | | Mx2 | 1.00 |
| 20766 | 3 | | | | | | Mmp3 | 1.00 | 20862 | 3 | | | | | Mybpc2 | 1.00 |
| 20767 | 3 | | | | | | Mmp7 | 1.00 | 20863 | 3 | | | | | Mybphl | 1.00 |
| 20768 | 3 | | | | | | Mnd1 | 1.00 | 20864 | 3 | | | | | Mycbpap | 1.00 |
| 20769 | 3 | | | | | | Mnx1 | 1.00 | 20865 | 3 | | | | | Mycs | 1.00 |
| 20770 | 3 | | | | | | Mobp | 1.00 | 20866 | 3 | | | | | Myh15 | 1.00 |
| 20771 | 3 | | | | | | Mogat1 | 1.00 | 20867 | 3 | | | | | Myl10 | 1.00 |
| 20772 | 3 | | | | | | Mok | 1.00 | 20868 | 3 | | | | | Myo15 | 1.00 |
| 20773 | 3 | | | | | | Morc1 | 1.00 | 20869 | 3 | | | | | Myo1h | 1.00 |
| 20774 | 3 | | | | | | Morc2b | 1.00 | 20870 | 3 | | | | | Myo3a | 1.00 |
| 20775 | 3 | | | | | | Morn3 | 1.00 | 20871 | 3 | | | | | Myo3b | 1.00 |
| 20776 | 3 | | | | | | Morn5 | 1.00 | 20872 | 3 | | | | | Myo7b | 1.00 |
| 20777 | 3 | | | | | | Mos | 1.00 | 20873 | 3 | | | | | Myoc | 1.00 |
| 20778 | 3 | | | | | | Mospd2 | 1.00 | 20874 | 3 | | | | | Myrfl | 1.00 |
| 20779 | 3 | | | | | | Mospd4 | 1.00 | 20875 | 3 | | | | | Naa11 | 1.00 |
| 20780 | 3 | | | | | | Mov10l1 | 1.00 | 20876 | 3 | | | | | Naip7 | 1.00 |
| 20781 | 3 | | | | | | Moxd2 | 1.00 | 20877 | 3 | | | | | Nanog | 1.00 |
| 20782 | 3 | | | | | | Mpp4 | 1.00 | 20878 | 3 | | | | | Nat1 | 1.00 |
| 20783 | 3 | | | | | | Mptx1 | 1.00 | 20879 | 3 | | | | | Nat3 | 1.00 |
| 20784 | 3 | | | | | | Mptx2 | 1.00 | 20880 | 3 | | | | | Nat8 | 1.00 |
| 20785 | 3 | | | | | | Mrap2 | 1.00 | 20881 | 3 | | | | | Ncr1 | 1.00 |
| 20786 | 3 | | | | | | Mrgpra1 | 1.00 | 20882 | 3 | | | | | Nctc1 | 1.00 |
| 20787 | 3 | | | | | | Mrgpra2a | 1.00 | 20883 | 3 | | | | | Ndst4 | 1.00 |
| 20788 | 3 | | | | | | Mrgpra2b | 1.00 | 20884 | 3 | | | | | Ndufs5 | 1.00 |
| 20789 | 3 | | | | | | Mrgpra3 | 1.00 | 20885 | 3 | | | | | Neil2 | 1.00 |
| 20790 | 3 | | | | | | Mrgpra4 | 1.00 | 20886 | 3 | | | | | Nek10 | 1.00 |
| 20791 | 3 | | | | | | Mrgpra6 | 1.00 | 20887 | 3 | | | | | Nek11 | 1.00 |
| 20792 | 3 | | | | | | Mrgpra9 | 1.00 | 20888 | 3 | | | | | Nek5 | 1.00 |
| 20793 | 3 | | | | | | Mrgprb1 | 1.00 | 20889 | 3 | | | | | Nell1os | 1.00 |
| 20794 | 3 | | | | | | Mrgprb3 | 1.00 | 20890 | 3 | | | | | Nepn | 1.00 |
| 20795 | 3 | | | | | | Mrgprb4 | 1.00 | 20891 | 3 | | | | | Neu2 | 1.00 |
| 20796 | 3 | | | | | | Mrgprb5 | 1.00 | 20892 | 3 | | | | | Neu4 | 1.00 |
| 20797 | 3 | | | | | | Mrgprb8 | 1.00 | 20893 | 3 | | | | | Neurod4 | 1.00 |
| 20798 | 3 | | | | | | Mrgprd | 1.00 | 20894 | 3 | | | | | Neurog1 | 1.00 |
| 20799 | 3 | | | | | | Mrgprg | 1.00 | 20895 | 3 | | | | | Nfkbid | 1.00 |
| 20800 | 3 | | | | | | Mrgprh | 1.00 | 20896 | 3 | | | | | Ngb | 1.00 |
| 20801 | 3 | | | | | | Mrgprx2 | 1.00 | 20897 | 3 | | | | | Nhlrc4 | 1.00 |
| 20802 | 3 | | | | | | Mroh2a | 1.00 | 20898 | 3 | | | | | Ninj2 | 1.00 |
| 20803 | 3 | | | | | | Mroh2b | 1.00 | 20899 | 3 | | | | | Nipsnap1 | 1.00 |
| 20804 | 3 | | | | | | Mroh4 | 1.00 | 20900 | 3 | | | | | Nipsnap3a | 1.00 |
| 20805 | 3 | | | | | | Mroh5 | 1.00 | 20901 | 3 | | | | | Nkx1-1 | 1.00 |
| 20806 | 3 | | | | | | Mroh7 | 1.00 | 20902 | 3 | | | | | Nkx1-2 | 1.00 |
| 20807 | 3 | | | | | | Mroh8 | 1.00 | 20903 | 3 | | | | | Nkx2-2os | 1.00 |
| 20808 | 3 | | | | | | Mroh9 | 1.00 | 20904 | 3 | | | | | Nkx2-4 | 1.00 |
| 20809 | 3 | | | | | | Mrs2 | 1.00 | 20905 | 3 | | | | | Nkx2-6 | 1.00 |
| 20810 | 3 | | | | | | Ms4a1 | 1.00 | 20906 | 3 | | | | | Nkx2-9 | 1.00 |
| 20811 | 3 | | | | | | Ms4a10 | 1.00 | 20907 | 3 | | | | | Nkx3-1 | 1.00 |
| 20812 | 3 | | | | | | Ms4a13 | 1.00 | 20908 | 3 | | | | | Nkx6-1 | 1.00 |
| 20813 | 3 | | | | | | Ms4a15 | 1.00 | 20909 | 3 | | | | | Nkx6-2 | 1.00 |
| 20814 | 3 | | | | | | Ms4a2 | 1.00 | 20910 | 3 | | | | | Nkx6-3 | 1.00 |
| 20815 | 3 | | | | | | Ms4a4b | 1.00 | 20911 | 3 | | | | | Nlrc3 | 1.00 |
| 20816 | 3 | | | | | | Ms4a4c | 1.00 | 20912 | 3 | | | | | Nlrc5 | 1.00 |
| 20817 | 3 | | | | | | Ms4a5 | 1.00 | 20913 | 3 | | | | | Nlrp12 | 1.00 |
| 20818 | 3 | | | | | | Ms4a7 | 1.00 | 20914 | 3 | | | | | Nlrp14 | 1.00 |
| 20819 | 3 | | | | | | Ms4a8a | 1.00 | 20915 | 3 | | | | | Nlrp1a | 1.00 |
| 20820 | 3 | | | | | | Msantd1 | 1.00 | 20916 | 3 | | | | | Nlrp1b | 1.00 |
| 20821 | 3 | | | | | | Msgn1 | 1.00 | 20917 | 3 | | | | | Nlrp1c-ps | 1.00 |
| 20822 | 3 | | | | | | Msh4 | 1.00 | 20918 | 3 | | | | | Nlrp2 | 1.00 |
| 20823 | 3 | | | | | | Msh5 | 1.00 | 20919 | 3 | | | | | Nlrp3 | 1.00 |
| 20824 | 3 | | | | | | Msln | 1.00 | 20920 | 3 | | | | | Nlrp4a | 1.00 |
| 20825 | 3 | | | | | | Msmb | 1.00 | 20921 | 3 | | | | | Nlrp4b | 1.00 |
| 20826 | 3 | | | | | | Msmp | 1.00 | 20922 | 3 | | | | | Nlrp4c | 1.00 |
| 20827 | 3 | | | | | | Msx3 | 1.00 | 20923 | 3 | | | | | Nlrp4e | 1.00 |
| 20828 | 3 | | | | | | Mt4 | 1.00 | 20924 | 3 | | | | | Nlrp4f | 1.00 |
| 20829 | 3 | | | | | | Mthfd2 | 1.00 | 20925 | 3 | | | | | Nlrp4g | 1.00 |

Fig. 45 - 110

| | | | | | | | | | | | |
|---|---|---|---|---|---|---|---|---|---|---|---|
| 20926 | 3 | | | | Nlrp5 | 1.00 | 21022 | 3 | | Olfr1000 | 1.00 |
| 20927 | 3 | | | | Nlrp9a | 1.00 | 21023 | 3 | | Olfr1002 | 1.00 |
| 20928 | 3 | | | | Nlrp9b | 1.00 | 21024 | 3 | | Olfr1006 | 1.00 |
| 20929 | 3 | | | | Nlrp9c | 1.00 | 21025 | 3 | | Olfr1008 | 1.00 |
| 20930 | 3 | | | | Nmbr | 1.00 | 21026 | 3 | | Olfr1009 | 1.00 |
| 20931 | 3 | | | | Nme8 | 1.00 | 21027 | 3 | | Olfr101 | 1.00 |
| 20932 | 3 | | | | Nme9 | 1.00 | 21028 | 3 | | Olfr1010 | 1.00 |
| 20933 | 3 | | | | Nms | 1.00 | 21029 | 3 | | Olfr1012 | 1.00 |
| 20934 | 3 | | | | Nmu | 1.00 | 21030 | 3 | | Olfr1013 | 1.00 |
| 20935 | 3 | | | | Nmur1 | 1.00 | 21031 | 3 | | Olfr1014 | 1.00 |
| 20936 | 3 | | | | Nmur2 | 1.00 | 21032 | 3 | | Olfr1015 | 1.00 |
| 20937 | 3 | | | | Nobox | 1.00 | 21033 | 3 | | Olfr1016 | 1.00 |
| 20938 | 3 | | | | Nod2 | 1.00 | 21034 | 3 | | Olfr1018 | 1.00 |
| 20939 | 3 | | | | Nodal | 1.00 | 21035 | 3 | | Olfr1019 | 1.00 |
| 20940 | 3 | | | | Nos2 | 1.00 | 21036 | 3 | | Olfr102 | 1.00 |
| 20941 | 3 | | | | Noto | 1.00 | 21037 | 3 | | Olfr1020 | 1.00 |
| 20942 | 3 | | | | Nox1 | 1.00 | 21038 | 3 | | Olfr1022 | 1.00 |
| 20943 | 3 | | | | Nox3 | 1.00 | 21039 | 3 | | Olfr1023 | 1.00 |
| 20944 | 3 | | | | Noxa1 | 1.00 | 21040 | 3 | | Olfr1024 | 1.00 |
| 20945 | 3 | | | | Noxred1 | 1.00 | 21041 | 3 | | Olfr1026 | 1.00 |
| 20946 | 3 | | | | Npas1 | 1.00 | 21042 | 3 | | Olfr1028 | 1.00 |
| 20947 | 3 | | | | Npas4 | 1.00 | 21043 | 3 | | Olfr1029 | 1.00 |
| 20948 | 3 | | | | Npat | 1.00 | 21044 | 3 | | Olfr103 | 1.00 |
| 20949 | 3 | | | | Npbwr1 | 1.00 | 21045 | 3 | | Olfr1030 | 1.00 |
| 20950 | 3 | | | | Npffr1 | 1.00 | 21046 | 3 | | Olfr1031 | 1.00 |
| 20951 | 3 | | | | Npffr2 | 1.00 | 21047 | 3 | | Olfr1032 | 1.00 |
| 20952 | 3 | | | | Nphs1 | 1.00 | 21048 | 3 | | Olfr1034 | 1.00 |
| 20953 | 3 | | | | Nphs1os | 1.00 | 21049 | 3 | | Olfr1036 | 1.00 |
| 20954 | 3 | | | | Nphs2 | 1.00 | 21050 | 3 | | Olfr1037 | 1.00 |
| 20955 | 3 | | | | Npm2 | 1.00 | 21051 | 3 | | Olfr1038-ps | 1.00 |
| 20956 | 3 | | | | Nppb | 1.00 | 21052 | 3 | | Olfr1039 | 1.00 |
| 20957 | 3 | | | | Nps | 1.00 | 21053 | 3 | | Olfr1040 | 1.00 |
| 20958 | 3 | | | | Npsr1 | 1.00 | 21054 | 3 | | Olfr1042 | 1.00 |
| 20959 | 3 | | | | Npvf | 1.00 | 21055 | 3 | | Olfr1043 | 1.00 |
| 20960 | 3 | | | | Npw | 1.00 | 21056 | 3 | | Olfr1044 | 1.00 |
| 20961 | 3 | | | | Npy4r | 1.00 | 21057 | 3 | | Olfr1045 | 1.00 |
| 20962 | 3 | | | | Npy5r | 1.00 | 21058 | 3 | | Olfr1046 | 1.00 |
| 20963 | 3 | | | | Npy6r | 1.00 | 21059 | 3 | | Olfr1047 | 1.00 |
| 20964 | 3 | | | | Nr0b1 | 1.00 | 21060 | 3 | | Olfr1048 | 1.00 |
| 20965 | 3 | | | | Nr1h5 | 1.00 | 21061 | 3 | | Olfr1049 | 1.00 |
| 20966 | 3 | | | | Nr1i3 | 1.00 | 21062 | 3 | | Olfr1051 | 1.00 |
| 20967 | 3 | | | | Nr2e3 | 1.00 | 21063 | 3 | | Olfr1052 | 1.00 |
| 20968 | 3 | | | | Nr5a1 | 1.00 | 21064 | 3 | | Olfr1053 | 1.00 |
| 20969 | 3 | | | | Nrg3os | 1.00 | 21065 | 3 | | Olfr1054 | 1.00 |
| 20970 | 3 | | | | Nrl | 1.00 | 21066 | 3 | | Olfr1055 | 1.00 |
| 20971 | 3 | | | | Nrn1l | 1.00 | 21067 | 3 | | Olfr1056 | 1.00 |
| 20972 | 3 | | | | Nron | 1.00 | 21068 | 3 | | Olfr1057 | 1.00 |
| 20973 | 3 | | | | Nt5c1a | 1.00 | 21069 | 3 | | Olfr1058 | 1.00 |
| 20974 | 3 | | | | Nt5c1b | 1.00 | 21070 | 3 | | Olfr1061 | 1.00 |
| 20975 | 3 | | | | Ntn5 | 1.00 | 21071 | 3 | | Olfr1062 | 1.00 |
| 20976 | 3 | | | | Ntsr2 | 1.00 | 21072 | 3 | | Olfr1065 | 1.00 |
| 20977 | 3 | | | | Nubpl | 1.00 | 21073 | 3 | | Olfr1066 | 1.00 |
| 20978 | 3 | | | | Nuggc | 1.00 | 21074 | 3 | | Olfr107 | 1.00 |
| 20979 | 3 | | | | Nup210l | 1.00 | 21075 | 3 | | Olfr1076 | 1.00 |
| 20980 | 3 | | | | Nup62-il4i1 | 1.00 | 21076 | 3 | | Olfr1077-ps1 | 1.00 |
| 20981 | 3 | | | | Nup62cl | 1.00 | 21077 | 3 | | Olfr1079 | 1.00 |
| 20982 | 3 | | | | Nupr1l | 1.00 | 21078 | 3 | | Olfr108 | 1.00 |
| 20983 | 3 | | | | Nutm1 | 1.00 | 21079 | 3 | | Olfr1080 | 1.00 |
| 20984 | 3 | | | | Nxf2 | 1.00 | 21080 | 3 | | Olfr1082 | 1.00 |
| 20985 | 3 | | | | Nxf3 | 1.00 | 21081 | 3 | | Olfr1084 | 1.00 |
| 20986 | 3 | | | | Nxf7 | 1.00 | 21082 | 3 | | Olfr1085 | 1.00 |
| 20987 | 3 | | | | Nxnl1 | 1.00 | 21083 | 3 | | Olfr1086 | 1.00 |
| 20988 | 3 | | | | Nxpe5 | 1.00 | 21084 | 3 | | Olfr1087 | 1.00 |
| 20989 | 3 | | | | Nxph2 | 1.00 | 21085 | 3 | | Olfr1089 | 1.00 |
| 20990 | 3 | | | | Nyx | 1.00 | 21086 | 3 | | Olfr109 | 1.00 |
| 20991 | 3 | | | | Oacyl | 1.00 | 21087 | 3 | | Olfr1090 | 1.00 |
| 20992 | 3 | | | | Oas1c | 1.00 | 21088 | 3 | | Olfr1093 | 1.00 |
| 20993 | 3 | | | | Oas1d | 1.00 | 21089 | 3 | | Olfr1094 | 1.00 |
| 20994 | 3 | | | | Oas1e | 1.00 | 21090 | 3 | | Olfr1095 | 1.00 |
| 20995 | 3 | | | | Oas1g | 1.00 | 21091 | 3 | | Olfr1097 | 1.00 |
| 20996 | 3 | | | | Oas1h | 1.00 | 21092 | 3 | | Olfr1098 | 1.00 |
| 20997 | 3 | | | | Oas3 | 1.00 | 21093 | 3 | | Olfr1099 | 1.00 |
| 20998 | 3 | | | | Oaz1-ps | 1.00 | 21094 | 3 | | Olfr11 | 1.00 |
| 20999 | 3 | | | | Obox1 | 1.00 | 21095 | 3 | | Olfr110 | 1.00 |
| 21000 | 3 | | | | Obox2 | 1.00 | 21096 | 3 | | Olfr1100 | 1.00 |
| 21001 | 3 | | | | Obox3 | 1.00 | 21097 | 3 | | Olfr1101 | 1.00 |
| 21002 | 3 | | | | Obox5 | 1.00 | 21098 | 3 | | Olfr1102 | 1.00 |
| 21003 | 3 | | | | Obox6 | 1.00 | 21099 | 3 | | Olfr1104 | 1.00 |
| 21004 | 3 | | | | Obp1a | 1.00 | 21100 | 3 | | Olfr1105 | 1.00 |
| 21005 | 3 | | | | Obp2a | 1.00 | 21101 | 3 | | Olfr1106 | 1.00 |
| 21006 | 3 | | | | Obp2b | 1.00 | 21102 | 3 | | Olfr1107 | 1.00 |
| 21007 | 3 | | | | Oca2 | 1.00 | 21103 | 3 | | Olfr1109 | 1.00 |
| 21008 | 3 | | | | Ocm | 1.00 | 21104 | 3 | | Olfr111 | 1.00 |
| 21009 | 3 | | | | Odam | 1.00 | 21105 | 3 | | Olfr1110 | 1.00 |
| 21010 | 3 | | | | Odf1 | 1.00 | 21106 | 3 | | Olfr1111 | 1.00 |
| 21011 | 3 | | | | Odf3 | 1.00 | 21107 | 3 | | Olfr1112 | 1.00 |
| 21012 | 3 | | | | Odf3b | 1.00 | 21108 | 3 | | Olfr1113 | 1.00 |
| 21013 | 3 | | | | Odf3l2 | 1.00 | 21109 | 3 | | Olfr1115 | 1.00 |
| 21014 | 3 | | | | Odf4 | 1.00 | 21110 | 3 | | Olfr1116-ps | 1.00 |
| 21015 | 3 | | | | Ofcc1 | 1.00 | 21111 | 3 | | Olfr1118 | 1.00 |
| 21016 | 3 | | | | Oit1 | 1.00 | 21112 | 3 | | Olfr112 | 1.00 |
| 21017 | 3 | | | | Olah | 1.00 | 21113 | 3 | | Olfr1120 | 1.00 |
| 21018 | 3 | | | | Olfml2a | 1.00 | 21114 | 3 | | Olfr1121 | 1.00 |
| 21019 | 3 | | | | Olfr1 | 1.00 | 21115 | 3 | | Olfr1122 | 1.00 |
| 21020 | 3 | | | | Olfr10 | 1.00 | 21116 | 3 | | Olfr1123 | 1.00 |
| 21021 | 3 | | | | Olfr100 | 1.00 | 21117 | 3 | | Olfr1124 | 1.00 |

Fig. 45 - 111

| | | | | | | | | | | | | | | |
|---|---|---|---|---|---|---|---|---|---|---|---|---|---|---|
| 21118 | 3 | | | | | Olfr1126 | 1.00 | 21214 | 3 | | | | Olfr124 | 1.00 |
| 21119 | 3 | | | | | Olfr1128 | 1.00 | 21215 | 3 | | | | Olfr1240 | 1.00 |
| 21120 | 3 | | | | | Olfr1129 | 1.00 | 21216 | 3 | | | | Olfr1241 | 1.00 |
| 21121 | 3 | | | | | Olfr113 | 1.00 | 21217 | 3 | | | | Olfr1242 | 1.00 |
| 21122 | 3 | | | | | Olfr1130 | 1.00 | 21218 | 3 | | | | Olfr1243 | 1.00 |
| 21123 | 3 | | | | | Olfr1131 | 1.00 | 21219 | 3 | | | | Olfr1245 | 1.00 |
| 21124 | 3 | | | | | Olfr1132 | 1.00 | 21220 | 3 | | | | Olfr1246 | 1.00 |
| 21125 | 3 | | | | | Olfr1133 | 1.00 | 21221 | 3 | | | | Olfr1247 | 1.00 |
| 21126 | 3 | | | | | Olfr1134 | 1.00 | 21222 | 3 | | | | Olfr1248 | 1.00 |
| 21127 | 3 | | | | | Olfr1135 | 1.00 | 21223 | 3 | | | | Olfr1249 | 1.00 |
| 21128 | 3 | | | | | Olfr1136 | 1.00 | 21224 | 3 | | | | Olfr125 | 1.00 |
| 21129 | 3 | | | | | Olfr1137 | 1.00 | 21225 | 3 | | | | Olfr1250 | 1.00 |
| 21130 | 3 | | | | | Olfr1138 | 1.00 | 21226 | 3 | | | | Olfr1251 | 1.00 |
| 21131 | 3 | | | | | Olfr114 | 1.00 | 21227 | 3 | | | | Olfr1252 | 1.00 |
| 21132 | 3 | | | | | Olfr1140 | 1.00 | 21228 | 3 | | | | Olfr1253 | 1.00 |
| 21133 | 3 | | | | | Olfr1141 | 1.00 | 21229 | 3 | | | | Olfr1254 | 1.00 |
| 21134 | 3 | | | | | Olfr1143 | 1.00 | 21230 | 3 | | | | Olfr1255 | 1.00 |
| 21135 | 3 | | | | | Olfr1145 | 1.00 | 21231 | 3 | | | | Olfr1256 | 1.00 |
| 21136 | 3 | | | | | Olfr1148 | 1.00 | 21232 | 3 | | | | Olfr1257 | 1.00 |
| 21137 | 3 | | | | | Olfr115 | 1.00 | 21233 | 3 | | | | Olfr1258 | 1.00 |
| 21138 | 3 | | | | | Olfr1151 | 1.00 | 21234 | 3 | | | | Olfr1259 | 1.00 |
| 21139 | 3 | | | | | Olfr1152 | 1.00 | 21235 | 3 | | | | Olfr126 | 1.00 |
| 21140 | 3 | | | | | Olfr1153 | 1.00 | 21236 | 3 | | | | Olfr1260 | 1.00 |
| 21141 | 3 | | | | | Olfr1154 | 1.00 | 21237 | 3 | | | | Olfr1261 | 1.00 |
| 21142 | 3 | | | | | Olfr1155 | 1.00 | 21238 | 3 | | | | Olfr1262 | 1.00 |
| 21143 | 3 | | | | | Olfr1156 | 1.00 | 21239 | 3 | | | | Olfr1263 | 1.00 |
| 21144 | 3 | | | | | Olfr1157 | 1.00 | 21240 | 3 | | | | Olfr1264 | 1.00 |
| 21145 | 3 | | | | | Olfr1158 | 1.00 | 21241 | 3 | | | | Olfr1265 | 1.00 |
| 21146 | 3 | | | | | Olfr116 | 1.00 | 21242 | 3 | | | | Olfr1269 | 1.00 |
| 21147 | 3 | | | | | Olfr1160 | 1.00 | 21243 | 3 | | | | Olfr127 | 1.00 |
| 21148 | 3 | | | | | Olfr1161 | 1.00 | 21244 | 3 | | | | Olfr1270 | 1.00 |
| 21149 | 3 | | | | | Olfr1162 | 1.00 | 21245 | 3 | | | | Olfr1271 | 1.00 |
| 21150 | 3 | | | | | Olfr1163 | 1.00 | 21246 | 3 | | | | Olfr1272 | 1.00 |
| 21151 | 3 | | | | | Olfr1164 | 1.00 | 21247 | 3 | | | | Olfr1273-ps | 1.00 |
| 21152 | 3 | | | | | Olfr1166 | 1.00 | 21248 | 3 | | | | Olfr1274-ps | 1.00 |
| 21153 | 3 | | | | | Olfr1167 | 1.00 | 21249 | 3 | | | | Olfr1275 | 1.00 |
| 21154 | 3 | | | | | Olfr1168 | 1.00 | 21250 | 3 | | | | Olfr1276 | 1.00 |
| 21155 | 3 | | | | | Olfr117 | 1.00 | 21251 | 3 | | | | Olfr1277 | 1.00 |
| 21156 | 3 | | | | | Olfr1170 | 1.00 | 21252 | 3 | | | | Olfr1278 | 1.00 |
| 21157 | 3 | | | | | Olfr1173 | 1.00 | 21253 | 3 | | | | Olfr1279 | 1.00 |
| 21158 | 3 | | | | | Olfr1176 | 1.00 | 21254 | 3 | | | | Olfr128 | 1.00 |
| 21159 | 3 | | | | | Olfr1178 | 1.00 | 21255 | 3 | | | | Olfr1280 | 1.00 |
| 21160 | 3 | | | | | Olfr1179 | 1.00 | 21256 | 3 | | | | Olfr1281 | 1.00 |
| 21161 | 3 | | | | | Olfr118 | 1.00 | 21257 | 3 | | | | Olfr1282 | 1.00 |
| 21162 | 3 | | | | | Olfr1180 | 1.00 | 21258 | 3 | | | | Olfr1283 | 1.00 |
| 21163 | 3 | | | | | Olfr1181 | 1.00 | 21259 | 3 | | | | Olfr1284 | 1.00 |
| 21164 | 3 | | | | | Olfr1182 | 1.00 | 21260 | 3 | | | | Olfr1286 | 1.00 |
| 21165 | 3 | | | | | Olfr1183 | 1.00 | 21261 | 3 | | | | Olfr1287 | 1.00 |
| 21166 | 3 | | | | | Olfr1184 | 1.00 | 21262 | 3 | | | | Olfr1288 | 1.00 |
| 21167 | 3 | | | | | Olfr1186 | 1.00 | 21263 | 3 | | | | Olfr1289 | 1.00 |
| 21168 | 3 | | | | | Olfr1188 | 1.00 | 21264 | 3 | | | | Olfr129 | 1.00 |
| 21169 | 3 | | | | | Olfr1189 | 1.00 | 21265 | 3 | | | | Olfr1290 | 1.00 |
| 21170 | 3 | | | | | Olfr119 | 1.00 | 21266 | 3 | | | | Olfr1294 | 1.00 |
| 21171 | 3 | | | | | Olfr1193 | 1.00 | 21267 | 3 | | | | Olfr1295 | 1.00 |
| 21172 | 3 | | | | | Olfr1195 | 1.00 | 21268 | 3 | | | | Olfr1297 | 1.00 |
| 21173 | 3 | | | | | Olfr1196 | 1.00 | 21269 | 3 | | | | Olfr1298 | 1.00 |
| 21174 | 3 | | | | | Olfr1197 | 1.00 | 21270 | 3 | | | | Olfr1299 | 1.00 |
| 21175 | 3 | | | | | Olfr1198 | 1.00 | 21271 | 3 | | | | Olfr13 | 1.00 |
| 21176 | 3 | | | | | Olfr1199 | 1.00 | 21272 | 3 | | | | Olfr130 | 1.00 |
| 21177 | 3 | | | | | Olfr12 | 1.00 | 21273 | 3 | | | | Olfr1300-ps1 | 1.00 |
| 21178 | 3 | | | | | Olfr120 | 1.00 | 21274 | 3 | | | | Olfr1301 | 1.00 |
| 21179 | 3 | | | | | Olfr1200 | 1.00 | 21275 | 3 | | | | Olfr1302 | 1.00 |
| 21180 | 3 | | | | | Olfr1201 | 1.00 | 21276 | 3 | | | | Olfr1303 | 1.00 |
| 21181 | 3 | | | | | Olfr1202 | 1.00 | 21277 | 3 | | | | Olfr1305 | 1.00 |
| 21182 | 3 | | | | | Olfr1204 | 1.00 | 21278 | 3 | | | | Olfr1306 | 1.00 |
| 21183 | 3 | | | | | Olfr1205 | 1.00 | 21279 | 3 | | | | Olfr1307 | 1.00 |
| 21184 | 3 | | | | | Olfr1206 | 1.00 | 21280 | 3 | | | | Olfr1308 | 1.00 |
| 21185 | 3 | | | | | Olfr1208 | 1.00 | 21281 | 3 | | | | Olfr1309 | 1.00 |
| 21186 | 3 | | | | | Olfr1209 | 1.00 | 21282 | 3 | | | | Olfr131 | 1.00 |
| 21187 | 3 | | | | | Olfr121 | 1.00 | 21283 | 3 | | | | Olfr1310 | 1.00 |
| 21188 | 3 | | | | | Olfr1211 | 1.00 | 21284 | 3 | | | | Olfr1311 | 1.00 |
| 21189 | 3 | | | | | Olfr1212 | 1.00 | 21285 | 3 | | | | Olfr1312 | 1.00 |
| 21190 | 3 | | | | | Olfr1213 | 1.00 | 21286 | 3 | | | | Olfr1313 | 1.00 |
| 21191 | 3 | | | | | Olfr1214 | 1.00 | 21287 | 3 | | | | Olfr1314 | 1.00 |
| 21192 | 3 | | | | | Olfr1215 | 1.00 | 21288 | 3 | | | | Olfr1316 | 1.00 |
| 21193 | 3 | | | | | Olfr1216 | 1.00 | 21289 | 3 | | | | Olfr1317 | 1.00 |
| 21194 | 3 | | | | | Olfr1217 | 1.00 | 21290 | 3 | | | | Olfr1318 | 1.00 |
| 21195 | 3 | | | | | Olfr1218 | 1.00 | 21291 | 3 | | | | Olfr132 | 1.00 |
| 21196 | 3 | | | | | Olfr1219 | 1.00 | 21292 | 3 | | | | Olfr1320 | 1.00 |
| 21197 | 3 | | | | | Olfr122 | 1.00 | 21293 | 3 | | | | Olfr1321 | 1.00 |
| 21198 | 3 | | | | | Olfr1220 | 1.00 | 21294 | 3 | | | | Olfr1322 | 1.00 |
| 21199 | 3 | | | | | Olfr1221 | 1.00 | 21295 | 3 | | | | Olfr1323 | 1.00 |
| 21200 | 3 | | | | | Olfr1222 | 1.00 | 21296 | 3 | | | | Olfr1324 | 1.00 |
| 21201 | 3 | | | | | Olfr1223 | 1.00 | 21297 | 3 | | | | Olfr1325 | 1.00 |
| 21202 | 3 | | | | | Olfr1225 | 1.00 | 21298 | 3 | | | | Olfr1328 | 1.00 |
| 21203 | 3 | | | | | Olfr1226 | 1.00 | 21299 | 3 | | | | Olfr1329 | 1.00 |
| 21204 | 3 | | | | | Olfr1228 | 1.00 | 21300 | 3 | | | | Olfr133 | 1.00 |
| 21205 | 3 | | | | | Olfr1229 | 1.00 | 21301 | 3 | | | | Olfr1330 | 1.00 |
| 21206 | 3 | | | | | Olfr123 | 1.00 | 21302 | 3 | | | | Olfr1331 | 1.00 |
| 21207 | 3 | | | | | Olfr1230 | 1.00 | 21303 | 3 | | | | Olfr1333 | 1.00 |
| 21208 | 3 | | | | | Olfr1231 | 1.00 | 21304 | 3 | | | | Olfr1335 | 1.00 |
| 21209 | 3 | | | | | Olfr1232 | 1.00 | 21305 | 3 | | | | Olfr1336 | 1.00 |
| 21210 | 3 | | | | | Olfr1233 | 1.00 | 21306 | 3 | | | | Olfr1337 | 1.00 |
| 21211 | 3 | | | | | Olfr1234 | 1.00 | 21307 | 3 | | | | Olfr1338 | 1.00 |
| 21212 | 3 | | | | | Olfr1238 | 1.00 | 21308 | 3 | | | | Olfr1339 | 1.00 |
| 21213 | 3 | | | | | Olfr1239 | 1.00 | 21309 | 3 | | | | Olfr134 | 1.00 |

Fig. 45 - 112

| | | | | | | | | | | | | | | |
|---|---|---|---|---|---|---|---|---|---|---|---|---|---|---|
| 21310 | 3 | | | | | Olfr1340 | 1.00 | 21406 | 3 | | | | Olfr1457 | 1.00 |
| 21311 | 3 | | | | | Olfr1341 | 1.00 | 21407 | 3 | | | | Olfr1459 | 1.00 |
| 21312 | 3 | | | | | Olfr1342 | 1.00 | 21408 | 3 | | | | Olfr146 | 1.00 |
| 21313 | 3 | | | | | Olfr1344 | 1.00 | 21409 | 3 | | | | Olfr1461 | 1.00 |
| 21314 | 3 | | | | | Olfr1346 | 1.00 | 21410 | 3 | | | | Olfr1462 | 1.00 |
| 21315 | 3 | | | | | Olfr1347 | 1.00 | 21411 | 3 | | | | Olfr1463 | 1.00 |
| 21316 | 3 | | | | | Olfr1348 | 1.00 | 21412 | 3 | | | | Olfr1465 | 1.00 |
| 21317 | 3 | | | | | Olfr1349 | 1.00 | 21413 | 3 | | | | Olfr1466 | 1.00 |
| 21318 | 3 | | | | | Olfr135 | 1.00 | 21414 | 3 | | | | Olfr1467 | 1.00 |
| 21319 | 3 | | | | | Olfr1350 | 1.00 | 21415 | 3 | | | | Olfr1469 | 1.00 |
| 21320 | 3 | | | | | Olfr1351 | 1.00 | 21416 | 3 | | | | Olfr147 | 1.00 |
| 21321 | 3 | | | | | Olfr1352 | 1.00 | 21417 | 3 | | | | Olfr1471 | 1.00 |
| 21322 | 3 | | | | | Olfr1353 | 1.00 | 21418 | 3 | | | | Olfr1472 | 1.00 |
| 21323 | 3 | | | | | Olfr1354 | 1.00 | 21419 | 3 | | | | Olfr1474 | 1.00 |
| 21324 | 3 | | | | | Olfr1355 | 1.00 | 21420 | 3 | | | | Olfr1475 | 1.00 |
| 21325 | 3 | | | | | Olfr1356 | 1.00 | 21421 | 3 | | | | Olfr1477 | 1.00 |
| 21326 | 3 | | | | | Olfr1357 | 1.00 | 21422 | 3 | | | | Olfr148 | 1.00 |
| 21327 | 3 | | | | | Olfr1359 | 1.00 | 21423 | 3 | | | | Olfr1480 | 1.00 |
| 21328 | 3 | | | | | Olfr136 | 1.00 | 21424 | 3 | | | | Olfr1484 | 1.00 |
| 21329 | 3 | | | | | Olfr1360 | 1.00 | 21425 | 3 | | | | Olfr1487 | 1.00 |
| 21330 | 3 | | | | | Olfr1361 | 1.00 | 21426 | 3 | | | | Olfr1489 | 1.00 |
| 21331 | 3 | | | | | Olfr1362 | 1.00 | 21427 | 3 | | | | Olfr149 | 1.00 |
| 21332 | 3 | | | | | Olfr1364 | 1.00 | 21428 | 3 | | | | Olfr1490 | 1.00 |
| 21333 | 3 | | | | | Olfr1366 | 1.00 | 21429 | 3 | | | | Olfr1491 | 1.00 |
| 21334 | 3 | | | | | Olfr1367 | 1.00 | 21430 | 3 | | | | Olfr1494 | 1.00 |
| 21335 | 3 | | | | | Olfr1368 | 1.00 | 21431 | 3 | | | | Olfr1495 | 1.00 |
| 21336 | 3 | | | | | Olfr137 | 1.00 | 21432 | 3 | | | | Olfr1496 | 1.00 |
| 21337 | 3 | | | | | Olfr1370 | 1.00 | 21433 | 3 | | | | Olfr1497 | 1.00 |
| 21338 | 3 | | | | | Olfr1371 | 1.00 | 21434 | 3 | | | | Olfr1499 | 1.00 |
| 21339 | 3 | | | | | Olfr1373 | 1.00 | 21435 | 3 | | | | Olfr15 | 1.00 |
| 21340 | 3 | | | | | Olfr1377 | 1.00 | 21436 | 3 | | | | Olfr150 | 1.00 |
| 21341 | 3 | | | | | Olfr1378 | 1.00 | 21437 | 3 | | | | Olfr1500 | 1.00 |
| 21342 | 3 | | | | | Olfr138 | 1.00 | 21438 | 3 | | | | Olfr1501 | 1.00 |
| 21343 | 3 | | | | | Olfr1380 | 1.00 | 21439 | 3 | | | | Olfr1502 | 1.00 |
| 21344 | 3 | | | | | Olfr1381 | 1.00 | 21440 | 3 | | | | Olfr1504 | 1.00 |
| 21345 | 3 | | | | | Olfr1382 | 1.00 | 21441 | 3 | | | | Olfr1505 | 1.00 |
| 21346 | 3 | | | | | Olfr1383 | 1.00 | 21442 | 3 | | | | Olfr1506 | 1.00 |
| 21347 | 3 | | | | | Olfr1384 | 1.00 | 21443 | 3 | | | | Olfr1507 | 1.00 |
| 21348 | 3 | | | | | Olfr1385 | 1.00 | 21444 | 3 | | | | Olfr1508 | 1.00 |
| 21349 | 3 | | | | | Olfr1386 | 1.00 | 21445 | 3 | | | | Olfr1509 | 1.00 |
| 21350 | 3 | | | | | Olfr1387 | 1.00 | 21446 | 3 | | | | Olfr151 | 1.00 |
| 21351 | 3 | | | | | Olfr1388 | 1.00 | 21447 | 3 | | | | Olfr1510 | 1.00 |
| 21352 | 3 | | | | | Olfr1389 | 1.00 | 21448 | 3 | | | | Olfr1511 | 1.00 |
| 21353 | 3 | | | | | Olfr139 | 1.00 | 21449 | 3 | | | | Olfr1512 | 1.00 |
| 21354 | 3 | | | | | Olfr1390 | 1.00 | 21450 | 3 | | | | Olfr1513 | 1.00 |
| 21355 | 3 | | | | | Olfr1391 | 1.00 | 21451 | 3 | | | | Olfr152 | 1.00 |
| 21356 | 3 | | | | | Olfr1392 | 1.00 | 21452 | 3 | | | | Olfr153 | 1.00 |
| 21357 | 3 | | | | | Olfr1393 | 1.00 | 21453 | 3 | | | | Olfr1532-ps1 | 1.00 |
| 21358 | 3 | | | | | Olfr1394 | 1.00 | 21454 | 3 | | | | Olfr1535 | 1.00 |
| 21359 | 3 | | | | | Olfr1395 | 1.00 | 21455 | 3 | | | | Olfr1537 | 1.00 |
| 21360 | 3 | | | | | Olfr1396 | 1.00 | 21456 | 3 | | | | Olfr154 | 1.00 |
| 21361 | 3 | | | | | Olfr140 | 1.00 | 21457 | 3 | | | | Olfr155 | 1.00 |
| 21362 | 3 | | | | | Olfr1402 | 1.00 | 21458 | 3 | | | | Olfr156 | 1.00 |
| 21363 | 3 | | | | | Olfr1404 | 1.00 | 21459 | 3 | | | | Olfr157 | 1.00 |
| 21364 | 3 | | | | | Olfr1406 | 1.00 | 21460 | 3 | | | | Olfr159 | 1.00 |
| 21365 | 3 | | | | | Olfr1408 | 1.00 | 21461 | 3 | | | | Olfr16 | 1.00 |
| 21366 | 3 | | | | | Olfr141 | 1.00 | 21462 | 3 | | | | Olfr160 | 1.00 |
| 21367 | 3 | | | | | Olfr1410 | 1.00 | 21463 | 3 | | | | Olfr161 | 1.00 |
| 21368 | 3 | | | | | Olfr1411 | 1.00 | 21464 | 3 | | | | Olfr164 | 1.00 |
| 21369 | 3 | | | | | Olfr1412 | 1.00 | 21465 | 3 | | | | Olfr165 | 1.00 |
| 21370 | 3 | | | | | Olfr1413 | 1.00 | 21466 | 3 | | | | Olfr166 | 1.00 |
| 21371 | 3 | | | | | Olfr1414 | 1.00 | 21467 | 3 | | | | Olfr167 | 1.00 |
| 21372 | 3 | | | | | Olfr1415 | 1.00 | 21468 | 3 | | | | Olfr168 | 1.00 |
| 21373 | 3 | | | | | Olfr1416 | 1.00 | 21469 | 3 | | | | Olfr169 | 1.00 |
| 21374 | 3 | | | | | Olfr1417 | 1.00 | 21470 | 3 | | | | Olfr17 | 1.00 |
| 21375 | 3 | | | | | Olfr1418 | 1.00 | 21471 | 3 | | | | Olfr170 | 1.00 |
| 21376 | 3 | | | | | Olfr1419 | 1.00 | 21472 | 3 | | | | Olfr171 | 1.00 |
| 21377 | 3 | | | | | Olfr142 | 1.00 | 21473 | 3 | | | | Olfr172 | 1.00 |
| 21378 | 3 | | | | | Olfr1420 | 1.00 | 21474 | 3 | | | | Olfr173 | 1.00 |
| 21379 | 3 | | | | | Olfr1423 | 1.00 | 21475 | 3 | | | | Olfr175-ps1 | 1.00 |
| 21380 | 3 | | | | | Olfr1424 | 1.00 | 21476 | 3 | | | | Olfr176 | 1.00 |
| 21381 | 3 | | | | | Olfr1425 | 1.00 | 21477 | 3 | | | | Olfr177 | 1.00 |
| 21382 | 3 | | | | | Olfr1426 | 1.00 | 21478 | 3 | | | | Olfr178 | 1.00 |
| 21383 | 3 | | | | | Olfr1427 | 1.00 | 21479 | 3 | | | | Olfr18 | 1.00 |
| 21384 | 3 | | | | | Olfr1428 | 1.00 | 21480 | 3 | | | | Olfr180 | 1.00 |
| 21385 | 3 | | | | | Olfr143 | 1.00 | 21481 | 3 | | | | Olfr181 | 1.00 |
| 21386 | 3 | | | | | Olfr1431 | 1.00 | 21482 | 3 | | | | Olfr183 | 1.00 |
| 21387 | 3 | | | | | Olfr1433 | 1.00 | 21483 | 3 | | | | Olfr186 | 1.00 |
| 21388 | 3 | | | | | Olfr1434 | 1.00 | 21484 | 3 | | | | Olfr187 | 1.00 |
| 21389 | 3 | | | | | Olfr1436 | 1.00 | 21485 | 3 | | | | Olfr19 | 1.00 |
| 21390 | 3 | | | | | Olfr1437 | 1.00 | 21486 | 3 | | | | Olfr190 | 1.00 |
| 21391 | 3 | | | | | Olfr1440 | 1.00 | 21487 | 3 | | | | Olfr191 | 1.00 |
| 21392 | 3 | | | | | Olfr1441 | 1.00 | 21488 | 3 | | | | Olfr192 | 1.00 |
| 21393 | 3 | | | | | Olfr1442 | 1.00 | 21489 | 3 | | | | Olfr193 | 1.00 |
| 21394 | 3 | | | | | Olfr1443 | 1.00 | 21490 | 3 | | | | Olfr194 | 1.00 |
| 21395 | 3 | | | | | Olfr1444 | 1.00 | 21491 | 3 | | | | Olfr195 | 1.00 |
| 21396 | 3 | | | | | Olfr1445 | 1.00 | 21492 | 3 | | | | Olfr196 | 1.00 |
| 21397 | 3 | | | | | Olfr1446 | 1.00 | 21493 | 3 | | | | Olfr197 | 1.00 |
| 21398 | 3 | | | | | Olfr1447 | 1.00 | 21494 | 3 | | | | Olfr198 | 1.00 |
| 21399 | 3 | | | | | Olfr1448 | 1.00 | 21495 | 3 | | | | Olfr199 | 1.00 |
| 21400 | 3 | | | | | Olfr1449 | 1.00 | 21496 | 3 | | | | Olfr2 | 1.00 |
| 21401 | 3 | | | | | Olfr145 | 1.00 | 21497 | 3 | | | | Olfr20 | 1.00 |
| 21402 | 3 | | | | | Olfr1450 | 1.00 | 21498 | 3 | | | | Olfr201 | 1.00 |
| 21403 | 3 | | | | | Olfr1451 | 1.00 | 21499 | 3 | | | | Olfr202 | 1.00 |
| 21404 | 3 | | | | | Olfr1453 | 1.00 | 21500 | 3 | | | | Olfr203 | 1.00 |
| 21405 | 3 | | | | | Olfr1454 | 1.00 | 21501 | 3 | | | | Olfr204 | 1.00 |

Fig. 45 - 113

| | | | | | | | | | | | | | |
|---|---|---|---|---|---|---|---|---|---|---|---|---|---|
| 21502 | 3 | | | | | Olfr205 | 1.00 | 21598 | 3 | | | Olfr345 | 1.00 |
| 21503 | 3 | | | | | Olfr206 | 1.00 | 21599 | 3 | | | Olfr346 | 1.00 |
| 21504 | 3 | | | | | Olfr209 | 1.00 | 21600 | 3 | | | Olfr347 | 1.00 |
| 21505 | 3 | | | | | Olfr211 | 1.00 | 21601 | 3 | | | Olfr348 | 1.00 |
| 21506 | 3 | | | | | Olfr212 | 1.00 | 21602 | 3 | | | Olfr350 | 1.00 |
| 21507 | 3 | | | | | Olfr213 | 1.00 | 21603 | 3 | | | Olfr351 | 1.00 |
| 21508 | 3 | | | | | Olfr214 | 1.00 | 21604 | 3 | | | Olfr352 | 1.00 |
| 21509 | 3 | | | | | Olfr215 | 1.00 | 21605 | 3 | | | Olfr353 | 1.00 |
| 21510 | 3 | | | | | Olfr218 | 1.00 | 21606 | 3 | | | Olfr354 | 1.00 |
| 21511 | 3 | | | | | Olfr220 | 1.00 | 21607 | 3 | | | Olfr355 | 1.00 |
| 21512 | 3 | | | | | Olfr221 | 1.00 | 21608 | 3 | | | Olfr356 | 1.00 |
| 21513 | 3 | | | | | Olfr222 | 1.00 | 21609 | 3 | | | Olfr357 | 1.00 |
| 21514 | 3 | | | | | Olfr223 | 1.00 | 21610 | 3 | | | Olfr358 | 1.00 |
| 21515 | 3 | | | | | Olfr224 | 1.00 | 21611 | 3 | | | Olfr360 | 1.00 |
| 21516 | 3 | | | | | Olfr225 | 1.00 | 21612 | 3 | | | Olfr361 | 1.00 |
| 21517 | 3 | | | | | Olfr228 | 1.00 | 21613 | 3 | | | Olfr362 | 1.00 |
| 21518 | 3 | | | | | Olfr229 | 1.00 | 21614 | 3 | | | Olfr365 | 1.00 |
| 21519 | 3 | | | | | Olfr23 | 1.00 | 21615 | 3 | | | Olfr366 | 1.00 |
| 21520 | 3 | | | | | Olfr231 | 1.00 | 21616 | 3 | | | Olfr367-ps | 1.00 |
| 21521 | 3 | | | | | Olfr235 | 1.00 | 21617 | 3 | | | Olfr368 | 1.00 |
| 21522 | 3 | | | | | Olfr237-ps1 | 1.00 | 21618 | 3 | | | Olfr370 | 1.00 |
| 21523 | 3 | | | | | Olfr239 | 1.00 | 21619 | 3 | | | Olfr371 | 1.00 |
| 21524 | 3 | | | | | Olfr24 | 1.00 | 21620 | 3 | | | Olfr372 | 1.00 |
| 21525 | 3 | | | | | Olfr242 | 1.00 | 21621 | 3 | | | Olfr373 | 1.00 |
| 21526 | 3 | | | | | Olfr243 | 1.00 | 21622 | 3 | | | Olfr374 | 1.00 |
| 21527 | 3 | | | | | Olfr247 | 1.00 | 21623 | 3 | | | Olfr376 | 1.00 |
| 21528 | 3 | | | | | Olfr248 | 1.00 | 21624 | 3 | | | Olfr378 | 1.00 |
| 21529 | 3 | | | | | Olfr25 | 1.00 | 21625 | 3 | | | Olfr38 | 1.00 |
| 21530 | 3 | | | | | Olfr259 | 1.00 | 21626 | 3 | | | Olfr380 | 1.00 |
| 21531 | 3 | | | | | Olfr26 | 1.00 | 21627 | 3 | | | Olfr381 | 1.00 |
| 21532 | 3 | | | | | Olfr262 | 1.00 | 21628 | 3 | | | Olfr382 | 1.00 |
| 21533 | 3 | | | | | Olfr263 | 1.00 | 21629 | 3 | | | Olfr384 | 1.00 |
| 21534 | 3 | | | | | Olfr266 | 1.00 | 21630 | 3 | | | Olfr385 | 1.00 |
| 21535 | 3 | | | | | Olfr267 | 1.00 | 21631 | 3 | | | Olfr389 | 1.00 |
| 21536 | 3 | | | | | Olfr27 | 1.00 | 21632 | 3 | | | Olfr39 | 1.00 |
| 21537 | 3 | | | | | Olfr270 | 1.00 | 21633 | 3 | | | Olfr390 | 1.00 |
| 21538 | 3 | | | | | Olfr272 | 1.00 | 21634 | 3 | | | Olfr391-ps | 1.00 |
| 21539 | 3 | | | | | Olfr273 | 1.00 | 21635 | 3 | | | Olfr392 | 1.00 |
| 21540 | 3 | | | | | Olfr275 | 1.00 | 21636 | 3 | | | Olfr393 | 1.00 |
| 21541 | 3 | | | | | Olfr279 | 1.00 | 21637 | 3 | | | Olfr394 | 1.00 |
| 21542 | 3 | | | | | Olfr281 | 1.00 | 21638 | 3 | | | Olfr395 | 1.00 |
| 21543 | 3 | | | | | Olfr282 | 1.00 | 21639 | 3 | | | Olfr397 | 1.00 |
| 21544 | 3 | | | | | Olfr283 | 1.00 | 21640 | 3 | | | Olfr398 | 1.00 |
| 21545 | 3 | | | | | Olfr284 | 1.00 | 21641 | 3 | | | Olfr399 | 1.00 |
| 21546 | 3 | | | | | Olfr285 | 1.00 | 21642 | 3 | | | Olfr401 | 1.00 |
| 21547 | 3 | | | | | Olfr286 | 1.00 | 21643 | 3 | | | Olfr402 | 1.00 |
| 21548 | 3 | | | | | Olfr287 | 1.00 | 21644 | 3 | | | Olfr403 | 1.00 |
| 21549 | 3 | | | | | Olfr288 | 1.00 | 21645 | 3 | | | Olfr406 | 1.00 |
| 21550 | 3 | | | | | Olfr29-ps1 | 1.00 | 21646 | 3 | | | Olfr410 | 1.00 |
| 21551 | 3 | | | | | Olfr290 | 1.00 | 21647 | 3 | | | Olfr411 | 1.00 |
| 21552 | 3 | | | | | Olfr291 | 1.00 | 21648 | 3 | | | Olfr412 | 1.00 |
| 21553 | 3 | | | | | Olfr292 | 1.00 | 21649 | 3 | | | Olfr414 | 1.00 |
| 21554 | 3 | | | | | Olfr293 | 1.00 | 21650 | 3 | | | Olfr417 | 1.00 |
| 21555 | 3 | | | | | Olfr294 | 1.00 | 21651 | 3 | | | Olfr418-ps1 | 1.00 |
| 21556 | 3 | | | | | Olfr295 | 1.00 | 21652 | 3 | | | Olfr419 | 1.00 |
| 21557 | 3 | | | | | Olfr297 | 1.00 | 21653 | 3 | | | Olfr420 | 1.00 |
| 21558 | 3 | | | | | Olfr298 | 1.00 | 21654 | 3 | | | Olfr421-ps1 | 1.00 |
| 21559 | 3 | | | | | Olfr299 | 1.00 | 21655 | 3 | | | Olfr424 | 1.00 |
| 21560 | 3 | | | | | Olfr3 | 1.00 | 21656 | 3 | | | Olfr426 | 1.00 |
| 21561 | 3 | | | | | Olfr30 | 1.00 | 21657 | 3 | | | Olfr427 | 1.00 |
| 21562 | 3 | | | | | Olfr301 | 1.00 | 21658 | 3 | | | Olfr429 | 1.00 |
| 21563 | 3 | | | | | Olfr303 | 1.00 | 21659 | 3 | | | Olfr43 | 1.00 |
| 21564 | 3 | | | | | Olfr304 | 1.00 | 21660 | 3 | | | Olfr430 | 1.00 |
| 21565 | 3 | | | | | Olfr305 | 1.00 | 21661 | 3 | | | Olfr432 | 1.00 |
| 21566 | 3 | | | | | Olfr307 | 1.00 | 21662 | 3 | | | Olfr433 | 1.00 |
| 21567 | 3 | | | | | Olfr308 | 1.00 | 21663 | 3 | | | Olfr434 | 1.00 |
| 21568 | 3 | | | | | Olfr309 | 1.00 | 21664 | 3 | | | Olfr435 | 1.00 |
| 21569 | 3 | | | | | Olfr31 | 1.00 | 21665 | 3 | | | Olfr437 | 1.00 |
| 21570 | 3 | | | | | Olfr310 | 1.00 | 21666 | 3 | | | Olfr44 | 1.00 |
| 21571 | 3 | | | | | Olfr311 | 1.00 | 21667 | 3 | | | Olfr441 | 1.00 |
| 21572 | 3 | | | | | Olfr312 | 1.00 | 21668 | 3 | | | Olfr444 | 1.00 |
| 21573 | 3 | | | | | Olfr313 | 1.00 | 21669 | 3 | | | Olfr446 | 1.00 |
| 21574 | 3 | | | | | Olfr314 | 1.00 | 21670 | 3 | | | Olfr447 | 1.00 |
| 21575 | 3 | | | | | Olfr315 | 1.00 | 21671 | 3 | | | Olfr448 | 1.00 |
| 21576 | 3 | | | | | Olfr316 | 1.00 | 21672 | 3 | | | Olfr449 | 1.00 |
| 21577 | 3 | | | | | Olfr317 | 1.00 | 21673 | 3 | | | Olfr45 | 1.00 |
| 21578 | 3 | | | | | Olfr318 | 1.00 | 21674 | 3 | | | Olfr450 | 1.00 |
| 21579 | 3 | | | | | Olfr319 | 1.00 | 21675 | 3 | | | Olfr452 | 1.00 |
| 21580 | 3 | | | | | Olfr32 | 1.00 | 21676 | 3 | | | Olfr453 | 1.00 |
| 21581 | 3 | | | | | Olfr320 | 1.00 | 21677 | 3 | | | Olfr455 | 1.00 |
| 21582 | 3 | | | | | Olfr322 | 1.00 | 21678 | 3 | | | Olfr456 | 1.00 |
| 21583 | 3 | | | | | Olfr323 | 1.00 | 21679 | 3 | | | Olfr457 | 1.00 |
| 21584 | 3 | | | | | Olfr324 | 1.00 | 21680 | 3 | | | Olfr458 | 1.00 |
| 21585 | 3 | | | | | Olfr325 | 1.00 | 21681 | 3 | | | Olfr459 | 1.00 |
| 21586 | 3 | | | | | Olfr328 | 1.00 | 21682 | 3 | | | Olfr46 | 1.00 |
| 21587 | 3 | | | | | Olfr329-ps | 1.00 | 21683 | 3 | | | Olfr460 | 1.00 |
| 21588 | 3 | | | | | Olfr33 | 1.00 | 21684 | 3 | | | Olfr461 | 1.00 |
| 21589 | 3 | | | | | Olfr330 | 1.00 | 21685 | 3 | | | Olfr462 | 1.00 |
| 21590 | 3 | | | | | Olfr331 | 1.00 | 21686 | 3 | | | Olfr463 | 1.00 |
| 21591 | 3 | | | | | Olfr332 | 1.00 | 21687 | 3 | | | Olfr464 | 1.00 |
| 21592 | 3 | | | | | Olfr338 | 1.00 | 21688 | 3 | | | Olfr466 | 1.00 |
| 21593 | 3 | | | | | Olfr339 | 1.00 | 21689 | 3 | | | Olfr467 | 1.00 |
| 21594 | 3 | | | | | Olfr340 | 1.00 | 21690 | 3 | | | Olfr469 | 1.00 |
| 21595 | 3 | | | | | Olfr341 | 1.00 | 21691 | 3 | | | Olfr47 | 1.00 |
| 21596 | 3 | | | | | Olfr342 | 1.00 | 21692 | 3 | | | Olfr470 | 1.00 |
| 21597 | 3 | | | | | Olfr344 | 1.00 | 21693 | 3 | | | Olfr472 | 1.00 |

Fig. 45 - 114

| | | | | | | | | | | | | | | | | |
|---|---|---|---|---|---|---|---|---|---|---|---|---|---|---|---|---|
| 21694 | 3 | | | | | Olfr473 | 1.00 | 21790 | 3 | | | | | Olfr586 | 1.00 |
| 21695 | 3 | | | | | Olfr474 | 1.00 | 21791 | 3 | | | | | Olfr589 | 1.00 |
| 21696 | 3 | | | | | Olfr476 | 1.00 | 21792 | 3 | | | | | Olfr59 | 1.00 |
| 21697 | 3 | | | | | Olfr477 | 1.00 | 21793 | 3 | | | | | Olfr591 | 1.00 |
| 21698 | 3 | | | | | Olfr478 | 1.00 | 21794 | 3 | | | | | Olfr592 | 1.00 |
| 21699 | 3 | | | | | Olfr479 | 1.00 | 21795 | 3 | | | | | Olfr593 | 1.00 |
| 21700 | 3 | | | | | Olfr48 | 1.00 | 21796 | 3 | | | | | Olfr594 | 1.00 |
| 21701 | 3 | | | | | Olfr480 | 1.00 | 21797 | 3 | | | | | Olfr596 | 1.00 |
| 21702 | 3 | | | | | Olfr481 | 1.00 | 21798 | 3 | | | | | Olfr597 | 1.00 |
| 21703 | 3 | | | | | Olfr482 | 1.00 | 21799 | 3 | | | | | Olfr598 | 1.00 |
| 21704 | 3 | | | | | Olfr483 | 1.00 | 21800 | 3 | | | | | Olfr599 | 1.00 |
| 21705 | 3 | | | | | Olfr484 | 1.00 | 21801 | 3 | | | | | Olfr6 | 1.00 |
| 21706 | 3 | | | | | Olfr485 | 1.00 | 21802 | 3 | | | | | Olfr60 | 1.00 |
| 21707 | 3 | | | | | Olfr486 | 1.00 | 21803 | 3 | | | | | Olfr600 | 1.00 |
| 21708 | 3 | | | | | Olfr487 | 1.00 | 21804 | 3 | | | | | Olfr601 | 1.00 |
| 21709 | 3 | | | | | Olfr488 | 1.00 | 21805 | 3 | | | | | Olfr603 | 1.00 |
| 21710 | 3 | | | | | Olfr49 | 1.00 | 21806 | 3 | | | | | Olfr605 | 1.00 |
| 21711 | 3 | | | | | Olfr490 | 1.00 | 21807 | 3 | | | | | Olfr606 | 1.00 |
| 21712 | 3 | | | | | Olfr491 | 1.00 | 21808 | 3 | | | | | Olfr608 | 1.00 |
| 21713 | 3 | | | | | Olfr492 | 1.00 | 21809 | 3 | | | | | Olfr609 | 1.00 |
| 21714 | 3 | | | | | Olfr493 | 1.00 | 21810 | 3 | | | | | Olfr61 | 1.00 |
| 21715 | 3 | | | | | Olfr494 | 1.00 | 21811 | 3 | | | | | Olfr610 | 1.00 |
| 21716 | 3 | | | | | Olfr495 | 1.00 | 21812 | 3 | | | | | Olfr611 | 1.00 |
| 21717 | 3 | | | | | Olfr497 | 1.00 | 21813 | 3 | | | | | Olfr612 | 1.00 |
| 21718 | 3 | | | | | Olfr498 | 1.00 | 21814 | 3 | | | | | Olfr613 | 1.00 |
| 21719 | 3 | | | | | Olfr5 | 1.00 | 21815 | 3 | | | | | Olfr615 | 1.00 |
| 21720 | 3 | | | | | Olfr50 | 1.00 | 21816 | 3 | | | | | Olfr616 | 1.00 |
| 21721 | 3 | | | | | Olfr502 | 1.00 | 21817 | 3 | | | | | Olfr617 | 1.00 |
| 21722 | 3 | | | | | Olfr503 | 1.00 | 21818 | 3 | | | | | Olfr618 | 1.00 |
| 21723 | 3 | | | | | Olfr504 | 1.00 | 21819 | 3 | | | | | Olfr619 | 1.00 |
| 21724 | 3 | | | | | Olfr506 | 1.00 | 21820 | 3 | | | | | Olfr62 | 1.00 |
| 21725 | 3 | | | | | Olfr507 | 1.00 | 21821 | 3 | | | | | Olfr620 | 1.00 |
| 21726 | 3 | | | | | Olfr508 | 1.00 | 21822 | 3 | | | | | Olfr622 | 1.00 |
| 21727 | 3 | | | | | Olfr509 | 1.00 | 21823 | 3 | | | | | Olfr623 | 1.00 |
| 21728 | 3 | | | | | Olfr51 | 1.00 | 21824 | 3 | | | | | Olfr624 | 1.00 |
| 21729 | 3 | | | | | Olfr510 | 1.00 | 21825 | 3 | | | | | Olfr628 | 1.00 |
| 21730 | 3 | | | | | Olfr512 | 1.00 | 21826 | 3 | | | | | Olfr629 | 1.00 |
| 21731 | 3 | | | | | Olfr513 | 1.00 | 21827 | 3 | | | | | Olfr63 | 1.00 |
| 21732 | 3 | | | | | Olfr514 | 1.00 | 21828 | 3 | | | | | Olfr630 | 1.00 |
| 21733 | 3 | | | | | Olfr516 | 1.00 | 21829 | 3 | | | | | Olfr631 | 1.00 |
| 21734 | 3 | | | | | Olfr517 | 1.00 | 21830 | 3 | | | | | Olfr632 | 1.00 |
| 21735 | 3 | | | | | Olfr518 | 1.00 | 21831 | 3 | | | | | Olfr633 | 1.00 |
| 21736 | 3 | | | | | Olfr519 | 1.00 | 21832 | 3 | | | | | Olfr635 | 1.00 |
| 21737 | 3 | | | | | Olfr52 | 1.00 | 21833 | 3 | | | | | Olfr638 | 1.00 |
| 21738 | 3 | | | | | Olfr520 | 1.00 | 21834 | 3 | | | | | Olfr639 | 1.00 |
| 21739 | 3 | | | | | Olfr521 | 1.00 | 21835 | 3 | | | | | Olfr64 | 1.00 |
| 21740 | 3 | | | | | Olfr522 | 1.00 | 21836 | 3 | | | | | Olfr640 | 1.00 |
| 21741 | 3 | | | | | Olfr523 | 1.00 | 21837 | 3 | | | | | Olfr641 | 1.00 |
| 21742 | 3 | | | | | Olfr524 | 1.00 | 21838 | 3 | | | | | Olfr642 | 1.00 |
| 21743 | 3 | | | | | Olfr525 | 1.00 | 21839 | 3 | | | | | Olfr643 | 1.00 |
| 21744 | 3 | | | | | Olfr527 | 1.00 | 21840 | 3 | | | | | Olfr644 | 1.00 |
| 21745 | 3 | | | | | Olfr53 | 1.00 | 21841 | 3 | | | | | Olfr645 | 1.00 |
| 21746 | 3 | | | | | Olfr530 | 1.00 | 21842 | 3 | | | | | Olfr646 | 1.00 |
| 21747 | 3 | | | | | Olfr531 | 1.00 | 21843 | 3 | | | | | Olfr648 | 1.00 |
| 21748 | 3 | | | | | Olfr532 | 1.00 | 21844 | 3 | | | | | Olfr649 | 1.00 |
| 21749 | 3 | | | | | Olfr533 | 1.00 | 21845 | 3 | | | | | Olfr65 | 1.00 |
| 21750 | 3 | | | | | Olfr535 | 1.00 | 21846 | 3 | | | | | Olfr651 | 1.00 |
| 21751 | 3 | | | | | Olfr536 | 1.00 | 21847 | 3 | | | | | Olfr652 | 1.00 |
| 21752 | 3 | | | | | Olfr538 | 1.00 | 21848 | 3 | | | | | Olfr653 | 1.00 |
| 21753 | 3 | | | | | Olfr539 | 1.00 | 21849 | 3 | | | | | Olfr654 | 1.00 |
| 21754 | 3 | | | | | Olfr54 | 1.00 | 21850 | 3 | | | | | Olfr655 | 1.00 |
| 21755 | 3 | | | | | Olfr541 | 1.00 | 21851 | 3 | | | | | Olfr656 | 1.00 |
| 21756 | 3 | | | | | Olfr544 | 1.00 | 21852 | 3 | | | | | Olfr657 | 1.00 |
| 21757 | 3 | | | | | Olfr547 | 1.00 | 21853 | 3 | | | | | Olfr658 | 1.00 |
| 21758 | 3 | | | | | Olfr549 | 1.00 | 21854 | 3 | | | | | Olfr659 | 1.00 |
| 21759 | 3 | | | | | Olfr55 | 1.00 | 21855 | 3 | | | | | Olfr66 | 1.00 |
| 21760 | 3 | | | | | Olfr550 | 1.00 | 21856 | 3 | | | | | Olfr661 | 1.00 |
| 21761 | 3 | | | | | Olfr551 | 1.00 | 21857 | 3 | | | | | Olfr663 | 1.00 |
| 21762 | 3 | | | | | Olfr552 | 1.00 | 21858 | 3 | | | | | Olfr665 | 1.00 |
| 21763 | 3 | | | | | Olfr553 | 1.00 | 21859 | 3 | | | | | Olfr666 | 1.00 |
| 21764 | 3 | | | | | Olfr554 | 1.00 | 21860 | 3 | | | | | Olfr667 | 1.00 |
| 21765 | 3 | | | | | Olfr555 | 1.00 | 21861 | 3 | | | | | Olfr668 | 1.00 |
| 21766 | 3 | | | | | Olfr556 | 1.00 | 21862 | 3 | | | | | Olfr669 | 1.00 |
| 21767 | 3 | | | | | Olfr557 | 1.00 | 21863 | 3 | | | | | Olfr67 | 1.00 |
| 21768 | 3 | | | | | Olfr559 | 1.00 | 21864 | 3 | | | | | Olfr670 | 1.00 |
| 21769 | 3 | | | | | Olfr56 | 1.00 | 21865 | 3 | | | | | Olfr671 | 1.00 |
| 21770 | 3 | | | | | Olfr560 | 1.00 | 21866 | 3 | | | | | Olfr672 | 1.00 |
| 21771 | 3 | | | | | Olfr561 | 1.00 | 21867 | 3 | | | | | Olfr675 | 1.00 |
| 21772 | 3 | | | | | Olfr564 | 1.00 | 21868 | 3 | | | | | Olfr676 | 1.00 |
| 21773 | 3 | | | | | Olfr566 | 1.00 | 21869 | 3 | | | | | Olfr677 | 1.00 |
| 21774 | 3 | | | | | Olfr568 | 1.00 | 21870 | 3 | | | | | Olfr678 | 1.00 |
| 21775 | 3 | | | | | Olfr569 | 1.00 | 21871 | 3 | | | | | Olfr679 | 1.00 |
| 21776 | 3 | | | | | Olfr57 | 1.00 | 21872 | 3 | | | | | Olfr68 | 1.00 |
| 21777 | 3 | | | | | Olfr570 | 1.00 | 21873 | 3 | | | | | Olfr681 | 1.00 |
| 21778 | 3 | | | | | Olfr571 | 1.00 | 21874 | 3 | | | | | Olfr683 | 1.00 |
| 21779 | 3 | | | | | Olfr572 | 1.00 | 21875 | 3 | | | | | Olfr684 | 1.00 |
| 21780 | 3 | | | | | Olfr574 | 1.00 | 21876 | 3 | | | | | Olfr685 | 1.00 |
| 21781 | 3 | | | | | Olfr575 | 1.00 | 21877 | 3 | | | | | Olfr686 | 1.00 |
| 21782 | 3 | | | | | Olfr576 | 1.00 | 21878 | 3 | | | | | Olfr688 | 1.00 |
| 21783 | 3 | | | | | Olfr577 | 1.00 | 21879 | 3 | | | | | Olfr689 | 1.00 |
| 21784 | 3 | | | | | Olfr578 | 1.00 | 21880 | 3 | | | | | Olfr69 | 1.00 |
| 21785 | 3 | | | | | Olfr58 | 1.00 | 21881 | 3 | | | | | Olfr690 | 1.00 |
| 21786 | 3 | | | | | Olfr582 | 1.00 | 21882 | 3 | | | | | Olfr691 | 1.00 |
| 21787 | 3 | | | | | Olfr583 | 1.00 | 21883 | 3 | | | | | Olfr692 | 1.00 |
| 21788 | 3 | | | | | Olfr584 | 1.00 | 21884 | 3 | | | | | Olfr693 | 1.00 |
| 21789 | 3 | | | | | Olfr585 | 1.00 | 21885 | 3 | | | | | Olfr694 | 1.00 |

Fig. 45 - 115

| | | | | | | | | | | | | | | | |
|---|---|---|---|---|---|---|---|---|---|---|---|---|---|---|---|
| 21886 | 3 | | | | | Olfr695 | 1.00 | 21982 | 3 | | | | | Olfr812 | 1.00 |
| 21887 | 3 | | | | | Olfr697 | 1.00 | 21983 | 3 | | | | | Olfr813 | 1.00 |
| 21888 | 3 | | | | | Olfr698 | 1.00 | 21984 | 3 | | | | | Olfr814 | 1.00 |
| 21889 | 3 | | | | | Olfr699 | 1.00 | 21985 | 3 | | | | | Olfr815 | 1.00 |
| 21890 | 3 | | | | | Olfr70 | 1.00 | 21986 | 3 | | | | | Olfr816 | 1.00 |
| 21891 | 3 | | | | | Olfr700 | 1.00 | 21987 | 3 | | | | | Olfr818 | 1.00 |
| 21892 | 3 | | | | | Olfr701 | 1.00 | 21988 | 3 | | | | | Olfr819 | 1.00 |
| 21893 | 3 | | | | | Olfr702 | 1.00 | 21989 | 3 | | | | | Olfr820 | 1.00 |
| 21894 | 3 | | | | | Olfr703 | 1.00 | 21990 | 3 | | | | | Olfr821 | 1.00 |
| 21895 | 3 | | | | | Olfr704 | 1.00 | 21991 | 3 | | | | | Olfr822 | 1.00 |
| 21896 | 3 | | | | | Olfr705 | 1.00 | 21992 | 3 | | | | | Olfr823 | 1.00 |
| 21897 | 3 | | | | | Olfr706 | 1.00 | 21993 | 3 | | | | | Olfr824 | 1.00 |
| 21898 | 3 | | | | | Olfr707 | 1.00 | 21994 | 3 | | | | | Olfr825 | 1.00 |
| 21899 | 3 | | | | | Olfr71 | 1.00 | 21995 | 3 | | | | | Olfr826 | 1.00 |
| 21900 | 3 | | | | | Olfr710 | 1.00 | 21996 | 3 | | | | | Olfr827 | 1.00 |
| 21901 | 3 | | | | | Olfr711 | 1.00 | 21997 | 3 | | | | | Olfr828 | 1.00 |
| 21902 | 3 | | | | | Olfr713 | 1.00 | 21998 | 3 | | | | | Olfr829 | 1.00 |
| 21903 | 3 | | | | | Olfr714 | 1.00 | 21999 | 3 | | | | | Olfr830 | 1.00 |
| 21904 | 3 | | | | | Olfr715 | 1.00 | 22000 | 3 | | | | | Olfr832 | 1.00 |
| 21905 | 3 | | | | | Olfr716 | 1.00 | 22001 | 3 | | | | | Olfr834 | 1.00 |
| 21906 | 3 | | | | | Olfr720 | 1.00 | 22002 | 3 | | | | | Olfr835 | 1.00 |
| 21907 | 3 | | | | | Olfr722 | 1.00 | 22003 | 3 | | | | | Olfr836 | 1.00 |
| 21908 | 3 | | | | | Olfr723 | 1.00 | 22004 | 3 | | | | | Olfr837 | 1.00 |
| 21909 | 3 | | | | | Olfr724 | 1.00 | 22005 | 3 | | | | | Olfr843 | 1.00 |
| 21910 | 3 | | | | | Olfr725 | 1.00 | 22006 | 3 | | | | | Olfr845 | 1.00 |
| 21911 | 3 | | | | | Olfr726 | 1.00 | 22007 | 3 | | | | | Olfr846 | 1.00 |
| 21912 | 3 | | | | | Olfr727 | 1.00 | 22008 | 3 | | | | | Olfr847 | 1.00 |
| 21913 | 3 | | | | | Olfr728 | 1.00 | 22009 | 3 | | | | | Olfr849 | 1.00 |
| 21914 | 3 | | | | | Olfr729 | 1.00 | 22010 | 3 | | | | | Olfr850 | 1.00 |
| 21915 | 3 | | | | | Olfr73 | 1.00 | 22011 | 3 | | | | | Olfr851 | 1.00 |
| 21916 | 3 | | | | | Olfr730 | 1.00 | 22012 | 3 | | | | | Olfr853 | 1.00 |
| 21917 | 3 | | | | | Olfr731 | 1.00 | 22013 | 3 | | | | | Olfr854 | 1.00 |
| 21918 | 3 | | | | | Olfr732 | 1.00 | 22014 | 3 | | | | | Olfr855 | 1.00 |
| 21919 | 3 | | | | | Olfr733 | 1.00 | 22015 | 3 | | | | | Olfr856-ps1 | 1.00 |
| 21920 | 3 | | | | | Olfr734 | 1.00 | 22016 | 3 | | | | | Olfr857 | 1.00 |
| 21921 | 3 | | | | | Olfr735 | 1.00 | 22017 | 3 | | | | | Olfr859 | 1.00 |
| 21922 | 3 | | | | | Olfr736 | 1.00 | 22018 | 3 | | | | | Olfr860 | 1.00 |
| 21923 | 3 | | | | | Olfr738 | 1.00 | 22019 | 3 | | | | | Olfr862 | 1.00 |
| 21924 | 3 | | | | | Olfr739 | 1.00 | 22020 | 3 | | | | | Olfr866 | 1.00 |
| 21925 | 3 | | | | | Olfr74 | 1.00 | 22021 | 3 | | | | | Olfr867 | 1.00 |
| 21926 | 3 | | | | | Olfr740 | 1.00 | 22022 | 3 | | | | | Olfr868 | 1.00 |
| 21927 | 3 | | | | | Olfr741 | 1.00 | 22023 | 3 | | | | | Olfr869 | 1.00 |
| 21928 | 3 | | | | | Olfr742 | 1.00 | 22024 | 3 | | | | | Olfr870 | 1.00 |
| 21929 | 3 | | | | | Olfr743 | 1.00 | 22025 | 3 | | | | | Olfr871 | 1.00 |
| 21930 | 3 | | | | | Olfr744 | 1.00 | 22026 | 3 | | | | | Olfr872 | 1.00 |
| 21931 | 3 | | | | | Olfr745 | 1.00 | 22027 | 3 | | | | | Olfr873 | 1.00 |
| 21932 | 3 | | | | | Olfr746 | 1.00 | 22028 | 3 | | | | | Olfr874 | 1.00 |
| 21933 | 3 | | | | | Olfr747 | 1.00 | 22029 | 3 | | | | | Olfr875 | 1.00 |
| 21934 | 3 | | | | | Olfr748 | 1.00 | 22030 | 3 | | | | | Olfr876 | 1.00 |
| 21935 | 3 | | | | | Olfr749 | 1.00 | 22031 | 3 | | | | | Olfr877 | 1.00 |
| 21936 | 3 | | | | | Olfr75-ps1 | 1.00 | 22032 | 3 | | | | | Olfr878 | 1.00 |
| 21937 | 3 | | | | | Olfr750 | 1.00 | 22033 | 3 | | | | | Olfr881 | 1.00 |
| 21938 | 3 | | | | | Olfr76 | 1.00 | 22034 | 3 | | | | | Olfr883 | 1.00 |
| 21939 | 3 | | | | | Olfr761 | 1.00 | 22035 | 3 | | | | | Olfr884 | 1.00 |
| 21940 | 3 | | | | | Olfr763 | 1.00 | 22036 | 3 | | | | | Olfr885 | 1.00 |
| 21941 | 3 | | | | | Olfr765 | 1.00 | 22037 | 3 | | | | | Olfr887 | 1.00 |
| 21942 | 3 | | | | | Olfr767 | 1.00 | 22038 | 3 | | | | | Olfr888 | 1.00 |
| 21943 | 3 | | | | | Olfr768 | 1.00 | 22039 | 3 | | | | | Olfr889 | 1.00 |
| 21944 | 3 | | | | | Olfr769 | 1.00 | 22040 | 3 | | | | | Olfr890 | 1.00 |
| 21945 | 3 | | | | | Olfr77 | 1.00 | 22041 | 3 | | | | | Olfr891 | 1.00 |
| 21946 | 3 | | | | | Olfr770 | 1.00 | 22042 | 3 | | | | | Olfr893 | 1.00 |
| 21947 | 3 | | | | | Olfr771 | 1.00 | 22043 | 3 | | | | | Olfr894 | 1.00 |
| 21948 | 3 | | | | | Olfr772 | 1.00 | 22044 | 3 | | | | | Olfr895 | 1.00 |
| 21949 | 3 | | | | | Olfr773 | 1.00 | 22045 | 3 | | | | | Olfr898 | 1.00 |
| 21950 | 3 | | | | | Olfr774 | 1.00 | 22046 | 3 | | | | | Olfr899 | 1.00 |
| 21951 | 3 | | | | | Olfr775 | 1.00 | 22047 | 3 | | | | | Olfr9 | 1.00 |
| 21952 | 3 | | | | | Olfr776 | 1.00 | 22048 | 3 | | | | | Olfr90 | 1.00 |
| 21953 | 3 | | | | | Olfr777 | 1.00 | 22049 | 3 | | | | | Olfr900 | 1.00 |
| 21954 | 3 | | | | | Olfr78 | 1.00 | 22050 | 3 | | | | | Olfr901 | 1.00 |
| 21955 | 3 | | | | | Olfr780 | 1.00 | 22051 | 3 | | | | | Olfr902 | 1.00 |
| 21956 | 3 | | | | | Olfr781 | 1.00 | 22052 | 3 | | | | | Olfr904 | 1.00 |
| 21957 | 3 | | | | | Olfr782 | 1.00 | 22053 | 3 | | | | | Olfr905 | 1.00 |
| 21958 | 3 | | | | | Olfr784 | 1.00 | 22054 | 3 | | | | | Olfr906 | 1.00 |
| 21959 | 3 | | | | | Olfr786 | 1.00 | 22055 | 3 | | | | | Olfr907 | 1.00 |
| 21960 | 3 | | | | | Olfr787 | 1.00 | 22056 | 3 | | | | | Olfr908 | 1.00 |
| 21961 | 3 | | | | | Olfr788 | 1.00 | 22057 | 3 | | | | | Olfr91 | 1.00 |
| 21962 | 3 | | | | | Olfr790 | 1.00 | 22058 | 3 | | | | | Olfr910 | 1.00 |
| 21963 | 3 | | | | | Olfr791 | 1.00 | 22059 | 3 | | | | | Olfr911-ps1 | 1.00 |
| 21964 | 3 | | | | | Olfr792 | 1.00 | 22060 | 3 | | | | | Olfr912 | 1.00 |
| 21965 | 3 | | | | | Olfr794 | 1.00 | 22061 | 3 | | | | | Olfr913 | 1.00 |
| 21966 | 3 | | | | | Olfr796 | 1.00 | 22062 | 3 | | | | | Olfr914 | 1.00 |
| 21967 | 3 | | | | | Olfr798 | 1.00 | 22063 | 3 | | | | | Olfr915 | 1.00 |
| 21968 | 3 | | | | | Olfr799 | 1.00 | 22064 | 3 | | | | | Olfr916 | 1.00 |
| 21969 | 3 | | | | | Olfr8 | 1.00 | 22065 | 3 | | | | | Olfr917 | 1.00 |
| 21970 | 3 | | | | | Olfr800 | 1.00 | 22066 | 3 | | | | | Olfr918 | 1.00 |
| 21971 | 3 | | | | | Olfr801 | 1.00 | 22067 | 3 | | | | | Olfr919 | 1.00 |
| 21972 | 3 | | | | | Olfr802 | 1.00 | 22068 | 3 | | | | | Olfr92 | 1.00 |
| 21973 | 3 | | | | | Olfr803 | 1.00 | 22069 | 3 | | | | | Olfr920 | 1.00 |
| 21974 | 3 | | | | | Olfr804 | 1.00 | 22070 | 3 | | | | | Olfr921 | 1.00 |
| 21975 | 3 | | | | | Olfr805 | 1.00 | 22071 | 3 | | | | | Olfr922 | 1.00 |
| 21976 | 3 | | | | | Olfr806 | 1.00 | 22072 | 3 | | | | | Olfr923 | 1.00 |
| 21977 | 3 | | | | | Olfr807 | 1.00 | 22073 | 3 | | | | | Olfr924 | 1.00 |
| 21978 | 3 | | | | | Olfr808 | 1.00 | 22074 | 3 | | | | | Olfr926 | 1.00 |
| 21979 | 3 | | | | | Olfr809 | 1.00 | 22075 | 3 | | | | | Olfr93 | 1.00 |
| 21980 | 3 | | | | | Olfr810 | 1.00 | 22076 | 3 | | | | | Olfr930 | 1.00 |
| 21981 | 3 | | | | | Olfr811 | 1.00 | 22077 | 3 | | | | | Olfr933 | 1.00 |

Fig. 45 - 116

| | | | | | | | | | | | | | |
|---|---|---|---|---|---|---|---|---|---|---|---|---|---|
| 22078 | 3 | | | | Olfr934 | 1.00 | 22174 | 3 | | | | P2ry10 | 1.00 |
| 22079 | 3 | | | | Olfr935 | 1.00 | 22175 | 3 | | | | Pabpc1l | 1.00 |
| 22080 | 3 | | | | Olfr936 | 1.00 | 22176 | 3 | | | | Pabpc2 | 1.00 |
| 22081 | 3 | | | | Olfr937 | 1.00 | 22177 | 3 | | | | Pabpc6 | 1.00 |
| 22082 | 3 | | | | Olfr938 | 1.00 | 22178 | 3 | | | | Pabpn1l | 1.00 |
| 22083 | 3 | | | | Olfr94 | 1.00 | 22179 | 3 | | | | Padi1 | 1.00 |
| 22084 | 3 | | | | Olfr943 | 1.00 | 22180 | 3 | | | | Padi3 | 1.00 |
| 22085 | 3 | | | | Olfr944 | 1.00 | 22181 | 3 | | | | Padi4 | 1.00 |
| 22086 | 3 | | | | Olfr945 | 1.00 | 22182 | 3 | | | | Padi6 | 1.00 |
| 22087 | 3 | | | | Olfr947-ps1 | 1.00 | 22183 | 3 | | | | Pafl | 1.00 |
| 22088 | 3 | | | | Olfr948 | 1.00 | 22184 | 3 | | | | Pate2 | 1.00 |
| 22089 | 3 | | | | Olfr95 | 1.00 | 22185 | 3 | | | | Pate4 | 1.00 |
| 22090 | 3 | | | | Olfr951 | 1.00 | 22186 | 3 | | | | Patl2 | 1.00 |
| 22091 | 3 | | | | Olfr952 | 1.00 | 22187 | 3 | | | | Paupar | 1.00 |
| 22092 | 3 | | | | Olfr954 | 1.00 | 22188 | 3 | | | | Pax4 | 1.00 |
| 22093 | 3 | | | | Olfr955 | 1.00 | 22189 | 3 | | | | Pax5 | 1.00 |
| 22094 | 3 | | | | Olfr957 | 1.00 | 22190 | 3 | | | | Pax6os1 | 1.00 |
| 22095 | 3 | | | | Olfr958 | 1.00 | 22191 | 3 | | | | Pbp2 | 1.00 |
| 22096 | 3 | | | | Olfr959 | 1.00 | 22192 | 3 | | | | Pbsn | 1.00 |
| 22097 | 3 | | | | Olfr96 | 1.00 | 22193 | 3 | | | | Pcdha1 | 1.00 |
| 22098 | 3 | | | | Olfr960 | 1.00 | 22194 | 3 | | | | Pcdha10 | 1.00 |
| 22099 | 3 | | | | Olfr961 | 1.00 | 22195 | 3 | | | | Pcdha4-g | 1.00 |
| 22100 | 3 | | | | Olfr963 | 1.00 | 22196 | 3 | | | | Pcdha8 | 1.00 |
| 22101 | 3 | | | | Olfr965 | 1.00 | 22197 | 3 | | | | Pcdhac1 | 1.00 |
| 22102 | 3 | | | | Olfr967 | 1.00 | 22198 | 3 | | | | Pcdhb1 | 1.00 |
| 22103 | 3 | | | | Olfr968 | 1.00 | 22199 | 3 | | | | Pcdhb13 | 1.00 |
| 22104 | 3 | | | | Olfr969 | 1.00 | 22200 | 3 | | | | Pcdhb2 | 1.00 |
| 22105 | 3 | | | | Olfr97 | 1.00 | 22201 | 3 | | | | Pcp2 | 1.00 |
| 22106 | 3 | | | | Olfr970 | 1.00 | 22202 | 3 | | | | Pcsk1 | 1.00 |
| 22107 | 3 | | | | Olfr971 | 1.00 | 22203 | 3 | | | | Pcsk2os1 | 1.00 |
| 22108 | 3 | | | | Olfr972 | 1.00 | 22204 | 3 | | | | Pcsk2os2 | 1.00 |
| 22109 | 3 | | | | Olfr974 | 1.00 | 22205 | 3 | | | | Pdc | 1.00 |
| 22110 | 3 | | | | Olfr975 | 1.00 | 22206 | 3 | | | | Pdcd1 | 1.00 |
| 22111 | 3 | | | | Olfr976 | 1.00 | 22207 | 3 | | | | Pdcd1lg2 | 1.00 |
| 22112 | 3 | | | | Olfr978 | 1.00 | 22208 | 3 | | | | Pdcl2 | 1.00 |
| 22113 | 3 | | | | Olfr979 | 1.00 | 22209 | 3 | | | | Pde11a | 1.00 |
| 22114 | 3 | | | | Olfr98 | 1.00 | 22210 | 3 | | | | Pde4c | 1.00 |
| 22115 | 3 | | | | Olfr980 | 1.00 | 22211 | 3 | | | | Pde6a | 1.00 |
| 22116 | 3 | | | | Olfr981 | 1.00 | 22212 | 3 | | | | Pde6b | 1.00 |
| 22117 | 3 | | | | Olfr982 | 1.00 | 22213 | 3 | | | | Pde6c | 1.00 |
| 22118 | 3 | | | | Olfr983 | 1.00 | 22214 | 3 | | | | Pde6g | 1.00 |
| 22119 | 3 | | | | Olfr984 | 1.00 | 22215 | 3 | | | | Pde6h | 1.00 |
| 22120 | 3 | | | | Olfr985 | 1.00 | 22216 | 3 | | | | Pdha2 | 1.00 |
| 22121 | 3 | | | | Olfr986 | 1.00 | 22217 | 3 | | | | Pdilt | 1.00 |
| 22122 | 3 | | | | Olfr987 | 1.00 | 22218 | 3 | | | | Pdx1 | 1.00 |
| 22123 | 3 | | | | Olfr988 | 1.00 | 22219 | 3 | | | | Pdxk-ps | 1.00 |
| 22124 | 3 | | | | Olfr99 | 1.00 | 22220 | 3 | | | | Pdzd3 | 1.00 |
| 22125 | 3 | | | | Olfr992 | 1.00 | 22221 | 3 | | | | Pdzd9 | 1.00 |
| 22126 | 3 | | | | Olfr993 | 1.00 | 22222 | 3 | | | | Pea15b | 1.00 |
| 22127 | 3 | | | | Olfr994 | 1.00 | 22223 | 3 | | | | Pebp4 | 1.00 |
| 22128 | 3 | | | | Olfr995 | 1.00 | 22224 | 3 | | | | Peril | 1.00 |
| 22129 | 3 | | | | Olfr996 | 1.00 | 22225 | 3 | | | | Pes1 | 1.00 |
| 22130 | 3 | | | | Olfr998 | 1.00 | 22226 | 3 | | | | Pet2 | 1.00 |
| 22131 | 3 | | | | Olig3 | 1.00 | 22227 | 3 | | | | Pfas | 1.00 |
| 22132 | 3 | | | | Olr1 | 1.00 | 22228 | 3 | | | | Pfkp | 1.00 |
| 22133 | 3 | | | | Omg | 1.00 | 22229 | 3 | | | | Pfn3 | 1.00 |
| 22134 | 3 | | | | Omt2a | 1.00 | 22230 | 3 | | | | Pfpl | 1.00 |
| 22135 | 3 | | | | Omt2b | 1.00 | 22231 | 3 | | | | Pga5 | 1.00 |
| 22136 | 3 | | | | Onecut3 | 1.00 | 22232 | 3 | | | | Pgc | 1.00 |
| 22137 | 3 | | | | Oog1 | 1.00 | 22233 | 3 | | | | Pgk2 | 1.00 |
| 22138 | 3 | | | | Oog2 | 1.00 | 22234 | 3 | | | | Pglyrp3 | 1.00 |
| 22139 | 3 | | | | Oog3 | 1.00 | 22235 | 3 | | | | Pglyrp4 | 1.00 |
| 22140 | 3 | | | | Oog4 | 1.00 | 22236 | 3 | | | | Pgpep1l | 1.00 |
| 22141 | 3 | | | | Oosp1 | 1.00 | 22237 | 3 | | | | Pgr | 1.00 |
| 22142 | 3 | | | | Oosp2 | 1.00 | 22238 | 3 | | | | Pgr15l | 1.00 |
| 22143 | 3 | | | | Oosp3 | 1.00 | 22239 | 3 | | | | Phf11a | 1.00 |
| 22144 | 3 | | | | Opalin | 1.00 | 22240 | 3 | | | | Phf11b | 1.00 |
| 22145 | 3 | | | | Opn1mw | 1.00 | 22241 | 3 | | | | Phf11d | 1.00 |
| 22146 | 3 | | | | Opn1sw | 1.00 | 22242 | 3 | | | | Phgr1 | 1.00 |
| 22147 | 3 | | | | Opn4 | 1.00 | 22243 | 3 | | | | Phkg1 | 1.00 |
| 22148 | 3 | | | | Opn5 | 1.00 | 22244 | 3 | | | | Phxr4 | 1.00 |
| 22149 | 3 | | | | Oprd1 | 1.00 | 22245 | 3 | | | | Pi4kb | 1.00 |
| 22150 | 3 | | | | Oprk1 | 1.00 | 22246 | 3 | | | | Pigm | 1.00 |
| 22151 | 3 | | | | Oprm1 | 1.00 | 22247 | 3 | | | | Pigr | 1.00 |
| 22152 | 3 | | | | Orm2 | 1.00 | 22248 | 3 | | | | Pigz | 1.00 |
| 22153 | 3 | | | | Orm3 | 1.00 | 22249 | 3 | | | | Pih1d3 | 1.00 |
| 22154 | 3 | | | | Osm | 1.00 | 22250 | 3 | | | | Pik3c2g | 1.00 |
| 22155 | 3 | | | | Otoa | 1.00 | 22251 | 3 | | | | Pik3r5 | 1.00 |
| 22156 | 3 | | | | Otof | 1.00 | 22252 | 3 | | | | Pilrb1 | 1.00 |
| 22157 | 3 | | | | Otog | 1.00 | 22253 | 3 | | | | Pilrb2 | 1.00 |
| 22158 | 3 | | | | Otogl | 1.00 | 22254 | 3 | | | | Pinc | 1.00 |
| 22159 | 3 | | | | Otol1 | 1.00 | 22255 | 3 | | | | Pip | 1.00 |
| 22160 | 3 | | | | Otop1 | 1.00 | 22256 | 3 | | | | Pip5kl1 | 1.00 |
| 22161 | 3 | | | | Otop2 | 1.00 | 22257 | 3 | | | | Pira1 | 1.00 |
| 22162 | 3 | | | | Otop3 | 1.00 | 22258 | 3 | | | | Pira11 | 1.00 |
| 22163 | 3 | | | | Otos | 1.00 | 22259 | 3 | | | | Pira2 | 1.00 |
| 22164 | 3 | | | | Ott | 1.00 | 22260 | 3 | | | | Pira4 | 1.00 |
| 22165 | 3 | | | | Otud6a | 1.00 | 22261 | 3 | | | | Pira6 | 1.00 |
| 22166 | 3 | | | | Otx2os1 | 1.00 | 22262 | 3 | | | | Pira7 | 1.00 |
| 22167 | 3 | | | | Ovch2 | 1.00 | 22263 | 3 | | | | Pitpnm2os1 | 1.00 |
| 22168 | 3 | | | | Ovol3 | 1.00 | 22264 | 3 | | | | Piwil1 | 1.00 |
| 22169 | 3 | | | | Oxct2a | 1.00 | 22265 | 3 | | | | Piwil2 | 1.00 |
| 22170 | 3 | | | | Oxct2b | 1.00 | 22266 | 3 | | | | Piwil4 | 1.00 |
| 22171 | 3 | | | | Oxgr1 | 1.00 | 22267 | 3 | | | | Pkd1l2 | 1.00 |
| 22172 | 3 | | | | Oxt | 1.00 | 22268 | 3 | | | | Pkd1l3 | 1.00 |
| 22173 | 3 | | | | Oxtr | 1.00 | 22269 | 3 | | | | Pkd2l1 | 1.00 |

Fig. 45 - 117

| | | | | | | | | | | | | | | |
|---|---|---|---|---|---|---|---|---|---|---|---|---|---|---|
| 22270 | 3 | | | | | Pkdrej | 1.00 | 22366 | 3 | | | | Prl3d3 | 1.00 |
| 22271 | 3 | | | | | Pkhd1 | 1.00 | 22367 | 3 | | | | Prl4a1 | 1.00 |
| 22272 | 3 | | | | | Pkib | 1.00 | 22368 | 3 | | | | Prl5a1 | 1.00 |
| 22273 | 3 | | | | | Pkn1 | 1.00 | 22369 | 3 | | | | Prl6a1 | 1.00 |
| 22274 | 3 | | | | | Pla2g10 | 1.00 | 22370 | 3 | | | | Prl7a1 | 1.00 |
| 22275 | 3 | | | | | Pla2g10os | 1.00 | 22371 | 3 | | | | Prl7a2 | 1.00 |
| 22276 | 3 | | | | | Pla2g1b | 1.00 | 22372 | 3 | | | | Prl7b1 | 1.00 |
| 22277 | 3 | | | | | Pla2g2a | 1.00 | 22373 | 3 | | | | Prl7c1 | 1.00 |
| 22278 | 3 | | | | | Pla2g2c | 1.00 | 22374 | 3 | | | | Prl7d1 | 1.00 |
| 22279 | 3 | | | | | Pla2g2d | 1.00 | 22375 | 3 | | | | Prl8a1 | 1.00 |
| 22280 | 3 | | | | | Pla2g2e | 1.00 | 22376 | 3 | | | | Prl8a2 | 1.00 |
| 22281 | 3 | | | | | Pla2g4d | 1.00 | 22377 | 3 | | | | Prl8a6 | 1.00 |
| 22282 | 3 | | | | | Pla2r1 | 1.00 | 22378 | 3 | | | | Prl8a8 | 1.00 |
| 22283 | 3 | | | | | Plac8l1 | 1.00 | 22379 | 3 | | | | Prl8a9 | 1.00 |
| 22284 | 3 | | | | | Plb1 | 1.00 | 22380 | 3 | | | | Prlh | 1.00 |
| 22285 | 3 | | | | | Plcd4 | 1.00 | 22381 | 3 | | | | Prlhr | 1.00 |
| 22286 | 3 | | | | | Plcl2 | 1.00 | 22382 | 3 | | | | Prm1 | 1.00 |
| 22287 | 3 | | | | | Plcz1 | 1.00 | 22383 | 3 | | | | Prm2 | 1.00 |
| 22288 | 3 | | | | | Pldi | 1.00 | 22384 | 3 | | | | Prm3 | 1.00 |
| 22289 | 3 | | | | | Plekhd1os | 1.00 | 22385 | 3 | | | | Prmt3 | 1.00 |
| 22290 | 3 | | | | | Plekhg4 | 1.00 | 22386 | 3 | | | | Prn | 1.00 |
| 22291 | 3 | | | | | Plekhm1 | 1.00 | 22387 | 3 | | | | Prok1 | 1.00 |
| 22292 | 3 | | | | | Plekhs1 | 1.00 | 22388 | 3 | | | | Prok2 | 1.00 |
| 22293 | 3 | | | | | Plet1os | 1.00 | 22389 | 3 | | | | Prol1 | 1.00 |
| 22294 | 3 | | | | | Pik5 | 1.00 | 22390 | 3 | | | | Prop1 | 1.00 |
| 22295 | 3 | | | | | Plscr2 | 1.00 | 22391 | 3 | | | | Prp2 | 1.00 |
| 22296 | 3 | | | | | Plscr5 | 1.00 | 22392 | 3 | | | | Prph2 | 1.00 |
| 22297 | 3 | | | | | Plxdc1 | 1.00 | 22393 | 3 | | | | Prpmp5 | 1.00 |
| 22298 | 3 | | | | | Plxdc2 | 1.00 | 22394 | 3 | | | | Prps1l1 | 1.00 |
| 22299 | 3 | | | | | Plxna4os1 | 1.00 | 22395 | 3 | | | | Prr19 | 1.00 |
| 22300 | 3 | | | | | Plxnb3 | 1.00 | 22396 | 3 | | | | Prr22 | 1.00 |
| 22301 | 3 | | | | | Pmch | 1.00 | 22397 | 3 | | | | Prr23a | 1.00 |
| 22302 | 3 | | | | | Pmfbp1 | 1.00 | 22398 | 3 | | | | Prr27 | 1.00 |
| 22303 | 3 | | | | | Pmis2 | 1.00 | 22399 | 3 | | | | Prr30 | 1.00 |
| 22304 | 3 | | | | | Pmp2 | 1.00 | 22400 | 3 | | | | Prrt1 | 1.00 |
| 22305 | 3 | | | | | Pnldc1 | 1.00 | 22401 | 3 | | | | Prrxl1 | 1.00 |
| 22306 | 3 | | | | | Pnlip | 1.00 | 22402 | 3 | | | | Prss21 | 1.00 |
| 22307 | 3 | | | | | Pnliprp2 | 1.00 | 22403 | 3 | | | | Prss28 | 1.00 |
| 22308 | 3 | | | | | Pnma5 | 1.00 | 22404 | 3 | | | | Prss29 | 1.00 |
| 22309 | 3 | | | | | Pnmt | 1.00 | 22405 | 3 | | | | Prss30 | 1.00 |
| 22310 | 3 | | | | | Pnpla5 | 1.00 | 22406 | 3 | | | | Prss32 | 1.00 |
| 22311 | 3 | | | | | Podnl1 | 1.00 | 22407 | 3 | | | | Prss33 | 1.00 |
| 22312 | 3 | | | | | Poln | 1.00 | 22408 | 3 | | | | Prss37 | 1.00 |
| 22313 | 3 | | | | | Pom121l12 | 1.00 | 22409 | 3 | | | | Prss38 | 1.00 |
| 22314 | 3 | | | | | Pom121l2 | 1.00 | 22410 | 3 | | | | Prss39 | 1.00 |
| 22315 | 3 | | | | | Pon1 | 1.00 | 22411 | 3 | | | | Prss40 | 1.00 |
| 22316 | 3 | | | | | Poteg | 1.00 | 22412 | 3 | | | | Prss41 | 1.00 |
| 22317 | 3 | | | | | Pou1f1 | 1.00 | 22413 | 3 | | | | Prss42 | 1.00 |
| 22318 | 3 | | | | | Pou5f1 | 1.00 | 22414 | 3 | | | | Prss43 | 1.00 |
| 22319 | 3 | | | | | Pou5f2 | 1.00 | 22415 | 3 | | | | Prss44 | 1.00 |
| 22320 | 3 | | | | | Pp2d1 | 1.00 | 22416 | 3 | | | | Prss45 | 1.00 |
| 22321 | 3 | | | | | Ppapdc1a | 1.00 | 22417 | 3 | | | | Prss46 | 1.00 |
| 22322 | 3 | | | | | Ppef1 | 1.00 | 22418 | 3 | | | | Prss48 | 1.00 |
| 22323 | 3 | | | | | Ppef2 | 1.00 | 22419 | 3 | | | | Prss50 | 1.00 |
| 22324 | 3 | | | | | Ppm1n | 1.00 | 22420 | 3 | | | | Prss51 | 1.00 |
| 22325 | 3 | | | | | Ppp1r17 | 1.00 | 22421 | 3 | | | | Prss52 | 1.00 |
| 22326 | 3 | | | | | Ppp1r2-ps7 | 1.00 | 22422 | 3 | | | | Prss54 | 1.00 |
| 22327 | 3 | | | | | Ppp1r2-ps9 | 1.00 | 22423 | 3 | | | | Prss55 | 1.00 |
| 22328 | 3 | | | | | Ppp1r32 | 1.00 | 22424 | 3 | | | | Prss56 | 1.00 |
| 22329 | 3 | | | | | Ppp1r36 | 1.00 | 22425 | 3 | | | | Prss58 | 1.00 |
| 22330 | 3 | | | | | Ppp1r3fos | 1.00 | 22426 | 3 | | | | Prtg | 1.00 |
| 22331 | 3 | | | | | Ppp1r42 | 1.00 | 22427 | 3 | | | | Psg-ps1 | 1.00 |
| 22332 | 3 | | | | | Ppp2r2cos | 1.00 | 22428 | 3 | | | | Psg17 | 1.00 |
| 22333 | 3 | | | | | Ppp3r2 | 1.00 | 22429 | 3 | | | | Psg18 | 1.00 |
| 22334 | 3 | | | | | Ppy | 1.00 | 22430 | 3 | | | | Psg19 | 1.00 |
| 22335 | 3 | | | | | Prame | 1.00 | 22431 | 3 | | | | Psg20 | 1.00 |
| 22336 | 3 | | | | | Pramef12 | 1.00 | 22432 | 3 | | | | Psg21 | 1.00 |
| 22337 | 3 | | | | | Pramef17 | 1.00 | 22433 | 3 | | | | Psg22 | 1.00 |
| 22338 | 3 | | | | | Pramef25 | 1.00 | 22434 | 3 | | | | Psg23 | 1.00 |
| 22339 | 3 | | | | | Pramef6 | 1.00 | 22435 | 3 | | | | Psg25 | 1.00 |
| 22340 | 3 | | | | | Pramel1 | 1.00 | 22436 | 3 | | | | Psg26 | 1.00 |
| 22341 | 3 | | | | | Pramel3 | 1.00 | 22437 | 3 | | | | Psg27 | 1.00 |
| 22342 | 3 | | | | | Pramel4 | 1.00 | 22438 | 3 | | | | Psg28 | 1.00 |
| 22343 | 3 | | | | | Pramel5 | 1.00 | 22439 | 3 | | | | Psg29 | 1.00 |
| 22344 | 3 | | | | | Pramel6 | 1.00 | 22440 | 3 | | | | Psma8 | 1.00 |
| 22345 | 3 | | | | | Pramel7 | 1.00 | 22441 | 3 | | | | Psmb11 | 1.00 |
| 22346 | 3 | | | | | Prb1 | 1.00 | 22442 | 3 | | | | Psme2 | 1.00 |
| 22347 | 3 | | | | | Prdm13 | 1.00 | 22443 | 3 | | | | Psmg1 | 1.00 |
| 22348 | 3 | | | | | Prdm14 | 1.00 | 22444 | 3 | | | | Pstpip1 | 1.00 |
| 22349 | 3 | | | | | Prf1 | 1.00 | 22445 | 3 | | | | Ptchd3 | 1.00 |
| 22350 | 3 | | | | | Prg3 | 1.00 | 22446 | 3 | | | | Ptchd4 | 1.00 |
| 22351 | 3 | | | | | Prh1 | 1.00 | 22447 | 3 | | | | Ptcra | 1.00 |
| 22352 | 3 | | | | | Prkag2os1 | 1.00 | 22448 | 3 | | | | Ptf1a | 1.00 |
| 22353 | 3 | | | | | Prl | 1.00 | 22449 | 3 | | | | Ptgdr | 1.00 |
| 22354 | 3 | | | | | Prl2a1 | 1.00 | 22450 | 3 | | | | Ptgdr2 | 1.00 |
| 22355 | 3 | | | | | Prl2b1 | 1.00 | 22451 | 3 | | | | Ptger2 | 1.00 |
| 22356 | 3 | | | | | Prl2c1 | 1.00 | 22452 | 3 | | | | Ptgs2 | 1.00 |
| 22357 | 3 | | | | | Prl2c2 | 1.00 | 22453 | 3 | | | | Ptgs2os | 1.00 |
| 22358 | 3 | | | | | Prl2c3 | 1.00 | 22454 | 3 | | | | Pth2 | 1.00 |
| 22359 | 3 | | | | | Prl2c4 | 1.00 | 22455 | 3 | | | | Pth2r | 1.00 |
| 22360 | 3 | | | | | Prl2c5 | 1.00 | 22456 | 3 | | | | Ptpn20 | 1.00 |
| 22361 | 3 | | | | | Prl3a1 | 1.00 | 22457 | 3 | | | | Ptpn22 | 1.00 |
| 22362 | 3 | | | | | Prl3b1 | 1.00 | 22458 | 3 | | | | Ptpra | 1.00 |
| 22363 | 3 | | | | | Prl3c1 | 1.00 | 22459 | 3 | | | | Ptprh | 1.00 |
| 22364 | 3 | | | | | Prl3d1 | 1.00 | 22460 | 3 | | | | Ptprq | 1.00 |
| 22365 | 3 | | | | | Prl3d2 | 1.00 | 22461 | 3 | | | | Ptprtos | 1.00 |

Fig. 45 - 118

| | | | | | | | | | | | | | |
|---|---|---|---|---|---|---|---|---|---|---|---|---|---|
| 22462 | 3 | | | | | | Pura | 1.00 | 22558 | 3 | | Rhox4f | 1.00 |
| 22463 | 3 | | | | | | Pvalb | 1.00 | 22559 | 3 | | Rhox4g | 1.00 |
| 22464 | 3 | | | | | | Pxt1 | 1.00 | 22560 | 3 | | Rhox5 | 1.00 |
| 22465 | 3 | | | | | | Pydc3 | 1.00 | 22561 | 3 | | Rhox6 | 1.00 |
| 22466 | 3 | | | | | | Pydc4 | 1.00 | 22562 | 3 | | Rhox7 | 1.00 |
| 22467 | 3 | | | | | | Qars | 1.00 | 22563 | 3 | | Rhox8 | 1.00 |
| 22468 | 3 | | | | | | Qrfp | 1.00 | 22564 | 3 | | Rhox9 | 1.00 |
| 22469 | 3 | | | | | | Qrfpr | 1.00 | 22565 | 3 | | Ribc2 | 1.00 |
| 22470 | 3 | | | | | | Qrich2 | 1.00 | 22566 | 3 | | Riiad1 | 1.00 |
| 22471 | 3 | | | | | | R3hdml | 1.00 | 22567 | 3 | | Rimbp3 | 1.00 |
| 22472 | 3 | | | | | | Rab11fip4os1 | 1.00 | 22568 | 3 | | Ripply2 | 1.00 |
| 22473 | 3 | | | | | | Rab11fip4os2 | 1.00 | 22569 | 3 | | Rin1 | 1.00 |
| 22474 | 3 | | | | | | Rab26 | 1.00 | 22570 | 3 | | Rin3 | 1.00 |
| 22475 | 3 | | | | | | Rab39 | 1.00 | 22571 | 3 | | Rmnd1 | 1.00 |
| 22476 | 3 | | | | | | Rabl2 | 1.00 | 22572 | 3 | | Rnase10 | 1.00 |
| 22477 | 3 | | | | | | Rad21l | 1.00 | 22573 | 3 | | Rnase11 | 1.00 |
| 22478 | 3 | | | | | | Rad51ap2 | 1.00 | 22574 | 3 | | Rnase12 | 1.00 |
| 22479 | 3 | | | | | | Raet1a | 1.00 | 22575 | 3 | | Rnase13 | 1.00 |
| 22480 | 3 | | | | | | Raet1b | 1.00 | 22576 | 3 | | Rnase2a | 1.00 |
| 22481 | 3 | | | | | | Raet1c | 1.00 | 22577 | 3 | | Rnase2b | 1.00 |
| 22482 | 3 | | | | | | Rag2 | 1.00 | 22578 | 3 | | Rnase9 | 1.00 |
| 22483 | 3 | | | | | | Rasal1 | 1.00 | 22579 | 3 | | Rnf133 | 1.00 |
| 22484 | 3 | | | | | | Rasal3 | 1.00 | 22580 | 3 | | Rnf138rt1 | 1.00 |
| 22485 | 3 | | | | | | Rasef | 1.00 | 22581 | 3 | | Rnf146 | 1.00 |
| 22486 | 3 | | | | | | Raver1-fdx1l | 1.00 | 22582 | 3 | | Rnf148 | 1.00 |
| 22487 | 3 | | | | | | Rbakdn | 1.00 | 22583 | 3 | | Rnf151 | 1.00 |
| 22488 | 3 | | | | | | Rbbp8nl | 1.00 | 22584 | 3 | | Rnf17 | 1.00 |
| 22489 | 3 | | | | | | Rbl2 | 1.00 | 22585 | 3 | | Rnf183 | 1.00 |
| 22490 | 3 | | | | | | Rbm12b1 | 1.00 | 22586 | 3 | | Rnf207 | 1.00 |
| 22491 | 3 | | | | | | Rbm14-rbm4 | 1.00 | 22587 | 3 | | Rnu11 | 1.00 |
| 22492 | 3 | | | | | | Rbm31y | 1.00 | 22588 | 3 | | Rnu12 | 1.00 |
| 22493 | 3 | | | | | | Rbm44 | 1.00 | 22589 | 3 | | Rnu6 | 1.00 |
| 22494 | 3 | | | | | | Rbm46os | 1.00 | 22590 | 3 | | Rnu7 | 1.00 |
| 22495 | 3 | | | | | | Rbmxl2 | 1.00 | 22591 | 3 | | Rnu73b | 1.00 |
| 22496 | 3 | | | | | | Rbmy | 1.00 | 22592 | 3 | | Robo3 | 1.00 |
| 22497 | 3 | | | | | | Rbp3 | 1.00 | 22593 | 3 | | Ropn1 | 1.00 |
| 22498 | 3 | | | | | | Rbp7 | 1.00 | 22594 | 3 | | Ropn1l | 1.00 |
| 22499 | 3 | | | | | | Rcvrn | 1.00 | 22595 | 3 | | Ros1 | 1.00 |
| 22500 | 3 | | | | | | Rd3l | 1.00 | 22596 | 3 | | Rp1 | 1.00 |
| 22501 | 3 | | | | | | Rdh16 | 1.00 | 22597 | 3 | | Rp1l1 | 1.00 |
| 22502 | 3 | | | | | | Rdh18-ps | 1.00 | 22598 | 3 | | Rpe65 | 1.00 |
| 22503 | 3 | | | | | | Rdh19 | 1.00 | 22599 | 3 | | Rpgrip1 | 1.00 |
| 22504 | 3 | | | | | | Rdh8 | 1.00 | 22600 | 3 | | Rpl10l | 1.00 |
| 22505 | 3 | | | | | | Rec8 | 1.00 | 22601 | 3 | | Rpl26 | 1.00 |
| 22506 | 3 | | | | | | Reg1 | 1.00 | 22602 | 3 | | Rpl34-ps1 | 1.00 |
| 22507 | 3 | | | | | | Reg2 | 1.00 | 22603 | 3 | | Rpl39l | 1.00 |
| 22508 | 3 | | | | | | Reg3a | 1.00 | 22604 | 3 | | Rpl3l | 1.00 |
| 22509 | 3 | | | | | | Reg3b | 1.00 | 22605 | 3 | | Rprl1 | 1.00 |
| 22510 | 3 | | | | | | Reg3d | 1.00 | 22606 | 3 | | Rprl2 | 1.00 |
| 22511 | 3 | | | | | | Reg4 | 1.00 | 22607 | 3 | | Rprl3 | 1.00 |
| 22512 | 3 | | | | | | Ren2 | 1.00 | 22608 | 3 | | Rprml | 1.00 |
| 22513 | 3 | | | | | | Rergl | 1.00 | 22609 | 3 | | Rps21 | 1.00 |
| 22514 | 3 | | | | | | Retn | 1.00 | 22610 | 3 | | Rps27rt | 1.00 |
| 22515 | 3 | | | | | | Retnlb | 1.00 | 22611 | 3 | | Rrh | 1.00 |
| 22516 | 3 | | | | | | Rex2 | 1.00 | 22612 | 3 | | Rs1 | 1.00 |
| 22517 | 3 | | | | | | Rfpl3s | 1.00 | 22613 | 3 | | Rsg1 | 1.00 |
| 22518 | 3 | | | | | | Rfpl4 | 1.00 | 22614 | 3 | | Rslcan18 | 1.00 |
| 22519 | 3 | | | | | | Rfpl4b | 1.00 | 22615 | 3 | | Rsph6a | 1.00 |
| 22520 | 3 | | | | | | Rfx6 | 1.00 | 22616 | 3 | | Rspo4 | 1.00 |
| 22521 | 3 | | | | | | Rfx8 | 1.00 | 22617 | 3 | | Rtdr1 | 1.00 |
| 22522 | 3 | | | | | | Rfxank | 1.00 | 22618 | 3 | | Rtp2 | 1.00 |
| 22523 | 3 | | | | | | Rgl3 | 1.00 | 22619 | 3 | | Rubie | 1.00 |
| 22524 | 3 | | | | | | Rgr | 1.00 | 22620 | 3 | | Rufy4 | 1.00 |
| 22525 | 3 | | | | | | Rgs13 | 1.00 | 22621 | 3 | | Rxfp1 | 1.00 |
| 22526 | 3 | | | | | | Rgs14 | 1.00 | 22622 | 3 | | Rxfp2 | 1.00 |
| 22527 | 3 | | | | | | Rgs21 | 1.00 | 22623 | 3 | | Rxfp3 | 1.00 |
| 22528 | 3 | | | | | | Rgs22 | 1.00 | 22624 | 3 | | Rxfp4 | 1.00 |
| 22529 | 3 | | | | | | Rgs9bp | 1.00 | 22625 | 3 | | S100a2 | 1.00 |
| 22530 | 3 | | | | | | Rgsl | 1.00 | 22626 | 3 | | S100a5 | 1.00 |
| 22531 | 3 | | | | | | Rhcg | 1.00 | 22627 | 3 | | S100z | 1.00 |
| 22532 | 3 | | | | | | Rho | 1.00 | 22628 | 3 | | Saa2 | 1.00 |
| 22533 | 3 | | | | | | Rhoh | 1.00 | 22629 | 3 | | Sag | 1.00 |
| 22534 | 3 | | | | | | Rhox1 | 1.00 | 22630 | 3 | | Sall4 | 1.00 |
| 22535 | 3 | | | | | | Rhox10 | 1.00 | 22631 | 3 | | Samd15 | 1.00 |
| 22536 | 3 | | | | | | Rhox11 | 1.00 | 22632 | 3 | | Samd3 | 1.00 |
| 22537 | 3 | | | | | | Rhox12 | 1.00 | 22633 | 3 | | Samd7 | 1.00 |
| 22538 | 3 | | | | | | Rhox13 | 1.00 | 22634 | 3 | | Samt2 | 1.00 |
| 22539 | 3 | | | | | | Rhox2a | 1.00 | 22635 | 3 | | Samt3 | 1.00 |
| 22540 | 3 | | | | | | Rhox2b | 1.00 | 22636 | 3 | | Samt4 | 1.00 |
| 22541 | 3 | | | | | | Rhox2c | 1.00 | 22637 | 3 | | Sap25 | 1.00 |
| 22542 | 3 | | | | | | Rhox2d | 1.00 | 22638 | 3 | | Satl1 | 1.00 |
| 22543 | 3 | | | | | | Rhox2e | 1.00 | 22639 | 3 | | Sbk2 | 1.00 |
| 22544 | 3 | | | | | | Rhox2f | 1.00 | 22640 | 3 | | Sbk3 | 1.00 |
| 22545 | 3 | | | | | | Rhox2g | 1.00 | 22641 | 3 | | Sbp | 1.00 |
| 22546 | 3 | | | | | | Rhox2h | 1.00 | 22642 | 3 | | Sbpl | 1.00 |
| 22547 | 3 | | | | | | Rhox3a | 1.00 | 22643 | 3 | | Scarletltr | 1.00 |
| 22548 | 3 | | | | | | Rhox3c | 1.00 | 22644 | 3 | | Scarna10 | 1.00 |
| 22549 | 3 | | | | | | Rhox3e | 1.00 | 22645 | 3 | | Scarna17 | 1.00 |
| 22550 | 3 | | | | | | Rhox3f | 1.00 | 22646 | 3 | | Scarna2 | 1.00 |
| 22551 | 3 | | | | | | Rhox3g | 1.00 | 22647 | 3 | | Scarna3a | 1.00 |
| 22552 | 3 | | | | | | Rhox3h | 1.00 | 22648 | 3 | | Scarna3b | 1.00 |
| 22553 | 3 | | | | | | Rhox4a | 1.00 | 22649 | 3 | | Scarna8 | 1.00 |
| 22554 | 3 | | | | | | Rhox4b | 1.00 | 22650 | 3 | | Scarna9 | 1.00 |
| 22555 | 3 | | | | | | Rhox4c | 1.00 | 22651 | 3 | | Scd3 | 1.00 |
| 22556 | 3 | | | | | | Rhox4d | 1.00 | 22652 | 3 | | Scd4 | 1.00 |
| 22557 | 3 | | | | | | Rhox4e | 1.00 | 22653 | 3 | | Scgb1a1 | 1.00 |

Fig. 45 - 119

| | | | | | | | | | | | | | |
|---|---|---|---|---|---|---|---|---|---|---|---|---|---|
| 22654 | 3 | | | | | Scgb1b19 | 1.00 | 22750 | 3 | | | Slamf1 | 1.00 |
| 22655 | 3 | | | | | Scgb1b2 | 1.00 | 22751 | 3 | | | Slamf6 | 1.00 |
| 22656 | 3 | | | | | Scgb1b20 | 1.00 | 22752 | 3 | | | Slamf7 | 1.00 |
| 22657 | 3 | | | | | Scgb1b24 | 1.00 | 22753 | 3 | | | Slamf8 | 1.00 |
| 22658 | 3 | | | | | Scgb1b27 | 1.00 | 22754 | 3 | | | Slamf9 | 1.00 |
| 22659 | 3 | | | | | Scgb1b29 | 1.00 | 22755 | 3 | | | Slc10a2 | 1.00 |
| 22660 | 3 | | | | | Scgb1b3 | 1.00 | 22756 | 3 | | | Slc10a3-ubl4 | 1.00 |
| 22661 | 3 | | | | | Scgb1b30 | 1.00 | 22757 | 3 | | | Slc12a1 | 1.00 |
| 22662 | 3 | | | | | Scgb1b7 | 1.00 | 22758 | 3 | | | Slc12a3 | 1.00 |
| 22663 | 3 | | | | | Scgb1c1 | 1.00 | 22759 | 3 | | | Slc12a8 | 1.00 |
| 22664 | 3 | | | | | Scgb2b12 | 1.00 | 22760 | 3 | | | Slc13a1 | 1.00 |
| 22665 | 3 | | | | | Scgb2b15 | 1.00 | 22761 | 3 | | | Slc13a2 | 1.00 |
| 22666 | 3 | | | | | Scgb2b17 | 1.00 | 22762 | 3 | | | Slc13a2os | 1.00 |
| 22667 | 3 | | | | | Scgb2b19 | 1.00 | 22763 | 3 | | | Slc15a5 | 1.00 |
| 22668 | 3 | | | | | Scgb2b2 | 1.00 | 22764 | 3 | | | Slc16a5 | 1.00 |
| 22669 | 3 | | | | | Scgb2b20 | 1.00 | 22765 | 3 | | | Slc17a1 | 1.00 |
| 22670 | 3 | | | | | Scgb2b23-ps | 1.00 | 22766 | 3 | | | Slc17a2 | 1.00 |
| 22671 | 3 | | | | | Scgb2b24 | 1.00 | 22767 | 3 | | | Slc17a4 | 1.00 |
| 22672 | 3 | | | | | Scgb2b26 | 1.00 | 22768 | 3 | | | Slc17a8 | 1.00 |
| 22673 | 3 | | | | | Scgb2b27 | 1.00 | 22769 | 3 | | | Slc18a1 | 1.00 |
| 22674 | 3 | | | | | Scgb2b3 | 1.00 | 22770 | 3 | | | Slc19a3 | 1.00 |
| 22675 | 3 | | | | | Scgb2b7 | 1.00 | 22771 | 3 | | | Slc1a7 | 1.00 |
| 22676 | 3 | | | | | Scgb3a1 | 1.00 | 22772 | 3 | | | Slc22a1 | 1.00 |
| 22677 | 3 | | | | | Scgn | 1.00 | 22773 | 3 | | | Slc22a12 | 1.00 |
| 22678 | 3 | | | | | Scimp | 1.00 | 22774 | 3 | | | Slc22a13 | 1.00 |
| 22679 | 3 | | | | | Scn11a | 1.00 | 22775 | 3 | | | Slc22a13b-ps | 1.00 |
| 22680 | 3 | | | | | Scnn1b | 1.00 | 22776 | 3 | | | Slc22a14 | 1.00 |
| 22681 | 3 | | | | | Scnn1g | 1.00 | 22777 | 3 | | | Slc22a16 | 1.00 |
| 22682 | 3 | | | | | Scp2d1 | 1.00 | 22778 | 3 | | | Slc22a19 | 1.00 |
| 22683 | 3 | | | | | Scpep1os | 1.00 | 22779 | 3 | | | Slc22a2 | 1.00 |
| 22684 | 3 | | | | | Sctr | 1.00 | 22780 | 3 | | | Slc22a20 | 1.00 |
| 22685 | 3 | | | | | Sds | 1.00 | 22781 | 3 | | | Slc22a22 | 1.00 |
| 22686 | 3 | | | | | Sebox | 1.00 | 22782 | 3 | | | Slc22a26 | 1.00 |
| 22687 | 3 | | | | | Sec14l5 | 1.00 | 22783 | 3 | | | Slc22a27 | 1.00 |
| 22688 | 3 | | | | | Sec24d | 1.00 | 22784 | 3 | | | Slc22a28 | 1.00 |
| 22689 | 3 | | | | | Sec31b | 1.00 | 22785 | 3 | | | Slc22a29 | 1.00 |
| 22690 | 3 | | | | | Sectm1b | 1.00 | 22786 | 3 | | | Slc22a30 | 1.00 |
| 22691 | 3 | | | | | Sel1l2 | 1.00 | 22787 | 3 | | | Slc22a7 | 1.00 |
| 22692 | 3 | | | | | Sele | 1.00 | 22788 | 3 | | | Slc24a1 | 1.00 |
| 22693 | 3 | | | | | Selp | 1.00 | 22789 | 3 | | | Slc24a4 | 1.00 |
| 22694 | 3 | | | | | Senp3 | 1.00 | 22790 | 3 | | | Slc25a2 | 1.00 |
| 22695 | 3 | | | | | Sept12 | 1.00 | 22791 | 3 | | | Slc25a25 | 1.00 |
| 22696 | 3 | | | | | Sept14 | 1.00 | 22792 | 3 | | | Slc25a31 | 1.00 |
| 22697 | 3 | | | | | Serpina1f | 1.00 | 22793 | 3 | | | Slc25a41 | 1.00 |
| 22698 | 3 | | | | | Serpina3a | 1.00 | 22794 | 3 | | | Slc25a43 | 1.00 |
| 22699 | 3 | | | | | Serpina3b | 1.00 | 22795 | 3 | | | Slc25a54 | 1.00 |
| 22700 | 3 | | | | | Serpina3c | 1.00 | 22796 | 3 | | | Slc26a10 | 1.00 |
| 22701 | 3 | | | | | Serpina3f | 1.00 | 22797 | 3 | | | Slc26a3 | 1.00 |
| 22702 | 3 | | | | | Serpina3i | 1.00 | 22798 | 3 | | | Slc26a4 | 1.00 |
| 22703 | 3 | | | | | Serpina3k | 1.00 | 22799 | 3 | | | Slc26a5 | 1.00 |
| 22704 | 3 | | | | | Serpina4-ps1 | 1.00 | 22800 | 3 | | | Slc26a9 | 1.00 |
| 22705 | 3 | | | | | Serpina5 | 1.00 | 22801 | 3 | | | Slc28a1 | 1.00 |
| 22706 | 3 | | | | | Serpina9 | 1.00 | 22802 | 3 | | | Slc2a5 | 1.00 |
| 22707 | 3 | | | | | Serpinb13 | 1.00 | 22803 | 3 | | | Slc2a6 | 1.00 |
| 22708 | 3 | | | | | Serpinb1b | 1.00 | 22804 | 3 | | | Slc2a7 | 1.00 |
| 22709 | 3 | | | | | Serpinb1c | 1.00 | 22805 | 3 | | | Slc30a8 | 1.00 |
| 22710 | 3 | | | | | Serpinb3d | 1.00 | 22806 | 3 | | | Slc34a1 | 1.00 |
| 22711 | 3 | | | | | Serpinb6d | 1.00 | 22807 | 3 | | | Slc34a3 | 1.00 |
| 22712 | 3 | | | | | Serpinb6e | 1.00 | 22808 | 3 | | | Slc35f4 | 1.00 |
| 22713 | 3 | | | | | Serpinb9c | 1.00 | 22809 | 3 | | | Slc35g3 | 1.00 |
| 22714 | 3 | | | | | Serpinb9d | 1.00 | 22810 | 3 | | | Slc36a1os | 1.00 |
| 22715 | 3 | | | | | Serpinb9e | 1.00 | 22811 | 3 | | | Slc36a3 | 1.00 |
| 22716 | 3 | | | | | Serpinb9f | 1.00 | 22812 | 3 | | | Slc38a11 | 1.00 |
| 22717 | 3 | | | | | Serpinb9g | 1.00 | 22813 | 3 | | | Slc38a8 | 1.00 |
| 22718 | 3 | | | | | Serpine3 | 1.00 | 22814 | 3 | | | Slc39a12 | 1.00 |
| 22719 | 3 | | | | | Sftpd | 1.00 | 22815 | 3 | | | Slc44a1 | 1.00 |
| 22720 | 3 | | | | | Sgcz | 1.00 | 22816 | 3 | | | Slc45a2 | 1.00 |
| 22721 | 3 | | | | | Sgk2 | 1.00 | 22817 | 3 | | | Slc47a2 | 1.00 |
| 22722 | 3 | | | | | Sh2d1a | 1.00 | 22818 | 3 | | | Slc4a11 | 1.00 |
| 22723 | 3 | | | | | Sh2d1b1 | 1.00 | 22819 | 3 | | | Slc4a5 | 1.00 |
| 22724 | 3 | | | | | Sh2d1b2 | 1.00 | 22820 | 3 | | | Slc4a9 | 1.00 |
| 22725 | 3 | | | | | Sh2d2a | 1.00 | 22821 | 3 | | | Slc5a1b | 1.00 |
| 22726 | 3 | | | | | Sh2d4b | 1.00 | 22822 | 3 | | | Slc5a10 | 1.00 |
| 22727 | 3 | | | | | Sh2d7 | 1.00 | 22823 | 3 | | | Slc5a11 | 1.00 |
| 22728 | 3 | | | | | Shcbp1l | 1.00 | 22824 | 3 | | | Slc5a12 | 1.00 |
| 22729 | 3 | | | | | Siglec15 | 1.00 | 22825 | 3 | | | Slc5a2 | 1.00 |
| 22730 | 3 | | | | | Siglec5 | 1.00 | 22826 | 3 | | | Slc5a4a | 1.00 |
| 22731 | 3 | | | | | Siglecg | 1.00 | 22827 | 3 | | | Slc5a4b | 1.00 |
| 22732 | 3 | | | | | Siglech | 1.00 | 22828 | 3 | | | Slc5a5 | 1.00 |
| 22733 | 3 | | | | | Sirpb1a | 1.00 | 22829 | 3 | | | Slc5a8 | 1.00 |
| 22734 | 3 | | | | | Sirpb1b | 1.00 | 22830 | 3 | | | Slc6a12 | 1.00 |
| 22735 | 3 | | | | | Sis | 1.00 | 22831 | 3 | | | Slc6a18 | 1.00 |
| 22736 | 3 | | | | | Sit1 | 1.00 | 22832 | 3 | | | Slc6a19os | 1.00 |
| 22737 | 3 | | | | | Six6 | 1.00 | 22833 | 3 | | | Slc6a20b | 1.00 |
| 22738 | 3 | | | | | Skap1 | 1.00 | 22834 | 3 | | | Slc6a3 | 1.00 |
| 22739 | 3 | | | | | Skint1 | 1.00 | 22835 | 3 | | | Slc6a5 | 1.00 |
| 22740 | 3 | | | | | Skint11 | 1.00 | 22836 | 3 | | | Slc7a12 | 1.00 |
| 22741 | 3 | | | | | Skint2 | 1.00 | 22837 | 3 | | | Slc7a13 | 1.00 |
| 22742 | 3 | | | | | Skint4 | 1.00 | 22838 | 3 | | | Slc7a15 | 1.00 |
| 22743 | 3 | | | | | Skint5 | 1.00 | 22839 | 3 | | | Slc9a3 | 1.00 |
| 22744 | 3 | | | | | Skint6 | 1.00 | 22840 | 3 | | | Slc9a4 | 1.00 |
| 22745 | 3 | | | | | Skint8 | 1.00 | 22841 | 3 | | | Slc9b1 | 1.00 |
| 22746 | 3 | | | | | Skint9 | 1.00 | 22842 | 3 | | | Slc9b2 | 1.00 |
| 22747 | 3 | | | | | Skor2 | 1.00 | 22843 | 3 | | | Slc9c1 | 1.00 |
| 22748 | 3 | | | | | Sla2 | 1.00 | 22844 | 3 | | | Slco1a1 | 1.00 |
| 22749 | 3 | | | | | Slain1os | 1.00 | 22845 | 3 | | | Slco1a4 | 1.00 |

Fig. 45 - 120

| | | | | | | | | | | | | | | |
|---|---|---|---|---|---|---|---|---|---|---|---|---|---|---|
| 22846 | 3 | | | | | Sico1a5 | 1.00 | 22942 | 3 | | | | Snord61 | 1.00 |
| 22847 | 3 | | | | | Sico1a6 | 1.00 | 22943 | 3 | | | | Snord64 | 1.00 |
| 22848 | 3 | | | | | Sico3a1 | 1.00 | 22944 | 3 | | | | Snord65 | 1.00 |
| 22849 | 3 | | | | | Sico4a1 | 1.00 | 22945 | 3 | | | | Snord66 | 1.00 |
| 22850 | 3 | | | | | Sico4c1 | 1.00 | 22946 | 3 | | | | Snord67 | 1.00 |
| 22851 | 3 | | | | | Sico6b1 | 1.00 | 22947 | 3 | | | | Snord68 | 1.00 |
| 22852 | 3 | | | | | Sico6c1 | 1.00 | 22948 | 3 | | | | Snord69 | 1.00 |
| 22853 | 3 | | | | | Sico6d1 | 1.00 | 22949 | 3 | | | | Snord7 | 1.00 |
| 22854 | 3 | | | | | Sifn10-ps | 1.00 | 22950 | 3 | | | | Snord70 | 1.00 |
| 22855 | 3 | | | | | Sifn5os | 1.00 | 22951 | 3 | | | | Snord71 | 1.00 |
| 22856 | 3 | | | | | Sifnl1 | 1.00 | 22952 | 3 | | | | Snord72 | 1.00 |
| 22857 | 3 | | | | | Six | 1.00 | 22953 | 3 | | | | Snord73a | 1.00 |
| 22858 | 3 | | | | | Sixl1 | 1.00 | 22954 | 3 | | | | Snord8 | 1.00 |
| 22859 | 3 | | | | | Sly | 1.00 | 22955 | 3 | | | | Snord82 | 1.00 |
| 22860 | 3 | | | | | Smc1b | 1.00 | 22956 | 3 | | | | Snord83b | 1.00 |
| 22861 | 3 | | | | | Smc2os | 1.00 | 22957 | 3 | | | | Snord85 | 1.00 |
| 22862 | 3 | | | | | Smco1 | 1.00 | 22958 | 3 | | | | Snord87 | 1.00 |
| 22863 | 3 | | | | | Smco2 | 1.00 | 22959 | 3 | | | | Snord88a | 1.00 |
| 22864 | 3 | | | | | Smcp | 1.00 | 22960 | 3 | | | | Snord88c | 1.00 |
| 22865 | 3 | | | | | Smim23 | 1.00 | 22961 | 3 | | | | Snord89 | 1.00 |
| 22866 | 3 | | | | | Smim9 | 1.00 | 22962 | 3 | | | | Snord90 | 1.00 |
| 22867 | 3 | | | | | Smok2a | 1.00 | 22963 | 3 | | | | Snord91a | 1.00 |
| 22868 | 3 | | | | | Smok2b | 1.00 | 22964 | 3 | | | | Snord92 | 1.00 |
| 22869 | 3 | | | | | Smok3a | 1.00 | 22965 | 3 | | | | Snord93 | 1.00 |
| 22870 | 3 | | | | | Smok3b | 1.00 | 22966 | 3 | | | | Snord95 | 1.00 |
| 22871 | 3 | | | | | Smok4a | 1.00 | 22967 | 3 | | | | Snord96a | 1.00 |
| 22872 | 3 | | | | | Smpd5 | 1.00 | 22968 | 3 | | | | Snord98 | 1.00 |
| 22873 | 3 | | | | | Smr2 | 1.00 | 22969 | 3 | | | | Snord99 | 1.00 |
| 22874 | 3 | | | | | Smr3a | 1.00 | 22970 | 3 | | | | Sntg1 | 1.00 |
| 22875 | 3 | | | | | Snhg1 | 1.00 | 22971 | 3 | | | | Sntg2 | 1.00 |
| 22876 | 3 | | | | | Snhg9 | 1.00 | 22972 | 3 | | | | Sntn | 1.00 |
| 22877 | 3 | | | | | Snora15 | 1.00 | 22973 | 3 | | | | Snx31 | 1.00 |
| 22878 | 3 | | | | | Snora19 | 1.00 | 22974 | 3 | | | | Snx8 | 1.00 |
| 22879 | 3 | | | | | Snora20 | 1.00 | 22975 | 3 | | | | Sohlh1 | 1.00 |
| 22880 | 3 | | | | | Snora24 | 1.00 | 22976 | 3 | | | | Sohlh2 | 1.00 |
| 22881 | 3 | | | | | Snora26 | 1.00 | 22977 | 3 | | | | Sorbs2os | 1.00 |
| 22882 | 3 | | | | | Snora28 | 1.00 | 22978 | 3 | | | | Sowahd | 1.00 |
| 22883 | 3 | | | | | Snora2b | 1.00 | 22979 | 3 | | | | Sox30 | 1.00 |
| 22884 | 3 | | | | | Snora3 | 1.00 | 22980 | 3 | | | | Sox5os3 | 1.00 |
| 22885 | 3 | | | | | Snora30 | 1.00 | 22981 | 3 | | | | Sp110 | 1.00 |
| 22886 | 3 | | | | | Snora33 | 1.00 | 22982 | 3 | | | | Spaca1 | 1.00 |
| 22887 | 3 | | | | | Snora34 | 1.00 | 22983 | 3 | | | | Spaca3 | 1.00 |
| 22888 | 3 | | | | | Snora35 | 1.00 | 22984 | 3 | | | | Spaca4 | 1.00 |
| 22889 | 3 | | | | | Snora36b | 1.00 | 22985 | 3 | | | | Spaca5 | 1.00 |
| 22890 | 3 | | | | | Snora47 | 1.00 | 22986 | 3 | | | | Spaca7 | 1.00 |
| 22891 | 3 | | | | | Snora52 | 1.00 | 22987 | 3 | | | | Spag11a | 1.00 |
| 22892 | 3 | | | | | Snora5c | 1.00 | 22988 | 3 | | | | Spag11b | 1.00 |
| 22893 | 3 | | | | | Snora61 | 1.00 | 22989 | 3 | | | | Spag16 | 1.00 |
| 22894 | 3 | | | | | Snora62 | 1.00 | 22990 | 3 | | | | Spag17 | 1.00 |
| 22895 | 3 | | | | | Snora68 | 1.00 | 22991 | 3 | | | | Spag4 | 1.00 |
| 22896 | 3 | | | | | Snora69 | 1.00 | 22992 | 3 | | | | Spag7 | 1.00 |
| 22897 | 3 | | | | | Snora74a | 1.00 | 22993 | 3 | | | | Spam1 | 1.00 |
| 22898 | 3 | | | | | Snora7a | 1.00 | 22994 | 3 | | | | Spata1 | 1.00 |
| 22899 | 3 | | | | | Snord100 | 1.00 | 22995 | 3 | | | | Spata16 | 1.00 |
| 22900 | 3 | | | | | Snord104 | 1.00 | 22996 | 3 | | | | Spata17 | 1.00 |
| 22901 | 3 | | | | | Snord11 | 1.00 | 22997 | 3 | | | | Spata19 | 1.00 |
| 22902 | 3 | | | | | Snord110 | 1.00 | 22998 | 3 | | | | Spata20 | 1.00 |
| 22903 | 3 | | | | | Snord111 | 1.00 | 22999 | 3 | | | | Spata21 | 1.00 |
| 22904 | 3 | | | | | Snord116 | 1.00 | 23000 | 3 | | | | Spata25 | 1.00 |
| 22905 | 3 | | | | | Snord116l1 | 1.00 | 23001 | 3 | | | | Spata3 | 1.00 |
| 22906 | 3 | | | | | Snord116l2 | 1.00 | 23002 | 3 | | | | Spata31 | 1.00 |
| 22907 | 3 | | | | | Snord118 | 1.00 | 23003 | 3 | | | | Spata31d1a | 1.00 |
| 22908 | 3 | | | | | Snord12 | 1.00 | 23004 | 3 | | | | Spata31d1b | 1.00 |
| 22909 | 3 | | | | | Snord123 | 1.00 | 23005 | 3 | | | | Spata31d1c | 1.00 |
| 22910 | 3 | | | | | Snord14a | 1.00 | 23006 | 3 | | | | Spata31d1d | 1.00 |
| 22911 | 3 | | | | | Snord14c | 1.00 | 23007 | 3 | | | | Spata32 | 1.00 |
| 22912 | 3 | | | | | Snord14d | 1.00 | 23008 | 3 | | | | Spata4 | 1.00 |
| 22913 | 3 | | | | | Snord16a | 1.00 | 23009 | 3 | | | | Spata45 | 1.00 |
| 22914 | 3 | | | | | Snord17 | 1.00 | 23010 | 3 | | | | Spata9 | 1.00 |
| 22915 | 3 | | | | | Snord19 | 1.00 | 23011 | 3 | | | | Spatc1 | 1.00 |
| 22916 | 3 | | | | | Snord1a | 1.00 | 23012 | 3 | | | | Spatcl1 | 1.00 |
| 22917 | 3 | | | | | Snord1b | 1.00 | 23013 | 3 | | | | Spats1 | 1.00 |
| 22918 | 3 | | | | | Snord1c | 1.00 | 23014 | 3 | | | | Spdyb | 1.00 |
| 22919 | 3 | | | | | Snord2 | 1.00 | 23015 | 3 | | | | Speer1-ps1 | 1.00 |
| 22920 | 3 | | | | | Snord23 | 1.00 | 23016 | 3 | | | | Speer2 | 1.00 |
| 22921 | 3 | | | | | Snord32a | 1.00 | 23017 | 3 | | | | Speer3 | 1.00 |
| 22922 | 3 | | | | | Snord33 | 1.00 | 23018 | 3 | | | | Speer4a | 1.00 |
| 22923 | 3 | | | | | Snord34 | 1.00 | 23019 | 3 | | | | Speer4b | 1.00 |
| 22924 | 3 | | | | | Snord35a | 1.00 | 23020 | 3 | | | | Speer4c | 1.00 |
| 22925 | 3 | | | | | Snord35b | 1.00 | 23021 | 3 | | | | Speer4d | 1.00 |
| 22926 | 3 | | | | | Snord37 | 1.00 | 23022 | 3 | | | | Speer4e | 1.00 |
| 22927 | 3 | | | | | Snord38a | 1.00 | 23023 | 3 | | | | Speer4f | 1.00 |
| 22928 | 3 | | | | | Snord42a | 1.00 | 23024 | 3 | | | | Speer5-ps1 | 1.00 |
| 22929 | 3 | | | | | Snord42b | 1.00 | 23025 | 3 | | | | Speer6-ps1 | 1.00 |
| 22930 | 3 | | | | | Snord43 | 1.00 | 23026 | 3 | | | | Speer7-ps1 | 1.00 |
| 22931 | 3 | | | | | Snord45b | 1.00 | 23027 | 3 | | | | Speer8-ps1 | 1.00 |
| 22932 | 3 | | | | | Snord45c | 1.00 | 23028 | 3 | | | | Speer9-ps1 | 1.00 |
| 22933 | 3 | | | | | Snord47 | 1.00 | 23029 | 3 | | | | Spef2 | 1.00 |
| 22934 | 3 | | | | | Snord49a | 1.00 | 23030 | 3 | | | | Spem1 | 1.00 |
| 22935 | 3 | | | | | Snord49b | 1.00 | 23031 | 3 | | | | Spert | 1.00 |
| 22936 | 3 | | | | | Snord4a | 1.00 | 23032 | 3 | | | | Spesp1 | 1.00 |
| 22937 | 3 | | | | | Snord52 | 1.00 | 23033 | 3 | | | | Spin2-ps1 | 1.00 |
| 22938 | 3 | | | | | Snord53 | 1.00 | 23034 | 3 | | | | Spin2d | 1.00 |
| 22939 | 3 | | | | | Snord55 | 1.00 | 23035 | 3 | | | | Spink10 | 1.00 |
| 22940 | 3 | | | | | Snord57 | 1.00 | 23036 | 3 | | | | Spink11 | 1.00 |
| 22941 | 3 | | | | | Snord58b | 1.00 | 23037 | 3 | | | | Spink13 | 1.00 |

Fig. 45 - 121

| | | | | | | | | | | | | | | |
|---|---|---|---|---|---|---|---|---|---|---|---|---|---|---|
| 23038 | 3 | | | | | Spink14 | 1.00 | 23134 | 3 | | | | T | 1.00 |
| 23039 | 3 | | | | | Spink2 | 1.00 | 23135 | 3 | | | | T2 | 1.00 |
| 23040 | 3 | | | | | Spink6 | 1.00 | 23136 | 3 | | | | Taar1 | 1.00 |
| 23041 | 3 | | | | | Spink7 | 1.00 | 23137 | 3 | | | | Taar2 | 1.00 |
| 23042 | 3 | | | | | Spink8 | 1.00 | 23138 | 3 | | | | Taar3 | 1.00 |
| 23043 | 3 | | | | | Spinkl | 1.00 | 23139 | 3 | | | | Taar4 | 1.00 |
| 23044 | 3 | | | | | Spint3 | 1.00 | 23140 | 3 | | | | Taar5 | 1.00 |
| 23045 | 3 | | | | | Spint4 | 1.00 | 23141 | 3 | | | | Taar6 | 1.00 |
| 23046 | 3 | | | | | Spint5 | 1.00 | 23142 | 3 | | | | Taar7a | 1.00 |
| 23047 | 3 | | | | | Spn-ps | 1.00 | 23143 | 3 | | | | Taar7b | 1.00 |
| 23048 | 3 | | | | | Spns3 | 1.00 | 23144 | 3 | | | | Taar7d | 1.00 |
| 23049 | 3 | | | | | Spo11 | 1.00 | 23145 | 3 | | | | Taar7e | 1.00 |
| 23050 | 3 | | | | | Sppl2c | 1.00 | 23146 | 3 | | | | Taar7f | 1.00 |
| 23051 | 3 | | | | | Sprr2b | 1.00 | 23147 | 3 | | | | Taar8a | 1.00 |
| 23052 | 3 | | | | | Sprr2e | 1.00 | 23148 | 3 | | | | Taar8b | 1.00 |
| 23053 | 3 | | | | | Sprr2f | 1.00 | 23149 | 3 | | | | Taar8c | 1.00 |
| 23054 | 3 | | | | | Sprr2g | 1.00 | 23150 | 3 | | | | Taar9 | 1.00 |
| 23055 | 3 | | | | | Sprr2i | 1.00 | 23151 | 3 | | | | Tac2 | 1.00 |
| 23056 | 3 | | | | | Sprr2j-ps | 1.00 | 23152 | 3 | | | | Tac4 | 1.00 |
| 23057 | 3 | | | | | Sprr2k | 1.00 | 23153 | 3 | | | | Tacr2 | 1.00 |
| 23058 | 3 | | | | | Sprr4 | 1.00 | 23154 | 3 | | | | Tacr3 | 1.00 |
| 23059 | 3 | | | | | Spt1 | 1.00 | 23155 | 3 | | | | Taf1 | 1.00 |
| 23060 | 3 | | | | | Spz1 | 1.00 | 23156 | 3 | | | | Taf7l | 1.00 |
| 23061 | 3 | | | | | Srd5a2 | 1.00 | 23157 | 3 | | | | Tal2 | 1.00 |
| 23062 | 3 | | | | | Srms | 1.00 | 23158 | 3 | | | | Tarm1 | 1.00 |
| 23063 | 3 | | | | | Sry | 1.00 | 23159 | 3 | | | | Tas1r2 | 1.00 |
| 23064 | 3 | | | | | Ssmem1 | 1.00 | 23160 | 3 | | | | Tas1r3 | 1.00 |
| 23065 | 3 | | | | | Sspo | 1.00 | 23161 | 3 | | | | Tas2r102 | 1.00 |
| 23066 | 3 | | | | | Sstr3 | 1.00 | 23162 | 3 | | | | Tas2r103 | 1.00 |
| 23067 | 3 | | | | | Sstr5 | 1.00 | 23163 | 3 | | | | Tas2r104 | 1.00 |
| 23068 | 3 | | | | | Ssty1 | 1.00 | 23164 | 3 | | | | Tas2r105 | 1.00 |
| 23069 | 3 | | | | | Ssty2 | 1.00 | 23165 | 3 | | | | Tas2r106 | 1.00 |
| 23070 | 3 | | | | | Ssu2 | 1.00 | 23166 | 3 | | | | Tas2r107 | 1.00 |
| 23071 | 3 | | | | | Ssx9 | 1.00 | 23167 | 3 | | | | Tas2r108 | 1.00 |
| 23072 | 3 | | | | | Ssxb1 | 1.00 | 23168 | 3 | | | | Tas2r109 | 1.00 |
| 23073 | 3 | | | | | Ssxb10 | 1.00 | 23169 | 3 | | | | Tas2r110 | 1.00 |
| 23074 | 3 | | | | | Ssxb2 | 1.00 | 23170 | 3 | | | | Tas2r113 | 1.00 |
| 23075 | 3 | | | | | Ssxb3 | 1.00 | 23171 | 3 | | | | Tas2r114 | 1.00 |
| 23076 | 3 | | | | | Ssxb5 | 1.00 | 23172 | 3 | | | | Tas2r115 | 1.00 |
| 23077 | 3 | | | | | Ssxb6 | 1.00 | 23173 | 3 | | | | Tas2r116 | 1.00 |
| 23078 | 3 | | | | | Ssxb8 | 1.00 | 23174 | 3 | | | | Tas2r117 | 1.00 |
| 23079 | 3 | | | | | Ssxb9 | 1.00 | 23175 | 3 | | | | Tas2r118 | 1.00 |
| 23080 | 3 | | | | | St6galnac1 | 1.00 | 23176 | 3 | | | | Tas2r119 | 1.00 |
| 23081 | 3 | | | | | St8sia3os | 1.00 | 23177 | 3 | | | | Tas2r120 | 1.00 |
| 23082 | 3 | | | | | St8sia5 | 1.00 | 23178 | 3 | | | | Tas2r121 | 1.00 |
| 23083 | 3 | | | | | St8sia6 | 1.00 | 23179 | 3 | | | | Tas2r122 | 1.00 |
| 23084 | 3 | | | | | Stap1 | 1.00 | 23180 | 3 | | | | Tas2r123 | 1.00 |
| 23085 | 3 | | | | | Stard6 | 1.00 | 23181 | 3 | | | | Tas2r124 | 1.00 |
| 23086 | 3 | | | | | Stat4 | 1.00 | 23182 | 3 | | | | Tas2r125 | 1.00 |
| 23087 | 3 | | | | | Stk31 | 1.00 | 23183 | 3 | | | | Tas2r126 | 1.00 |
| 23088 | 3 | | | | | Stk33 | 1.00 | 23184 | 3 | | | | Tas2r129 | 1.00 |
| 23089 | 3 | | | | | Stmn1-rs1 | 1.00 | 23185 | 3 | | | | Tas2r130 | 1.00 |
| 23090 | 3 | | | | | Stoml3 | 1.00 | 23186 | 3 | | | | Tas2r131 | 1.00 |
| 23091 | 3 | | | | | Stpg1 | 1.00 | 23187 | 3 | | | | Tas2r134 | 1.00 |
| 23092 | 3 | | | | | Stpg2 | 1.00 | 23188 | 3 | | | | Tas2r135 | 1.00 |
| 23093 | 3 | | | | | Stra8 | 1.00 | 23189 | 3 | | | | Tas2r136 | 1.00 |
| 23094 | 3 | | | | | Strc | 1.00 | 23190 | 3 | | | | Tas2r137 | 1.00 |
| 23095 | 3 | | | | | Styxl1 | 1.00 | 23191 | 3 | | | | Tas2r138 | 1.00 |
| 23096 | 3 | | | | | Sucnr1 | 1.00 | 23192 | 3 | | | | Tas2r139 | 1.00 |
| 23097 | 3 | | | | | Sugct | 1.00 | 23193 | 3 | | | | Tas2r140 | 1.00 |
| 23098 | 3 | | | | | Sult1c1 | 1.00 | 23194 | 3 | | | | Tas2r143 | 1.00 |
| 23099 | 3 | | | | | Sult1c2 | 1.00 | 23195 | 3 | | | | Tas2r144 | 1.00 |
| 23100 | 3 | | | | | Sult1e1 | 1.00 | 23196 | 3 | | | | Tbc1d15 | 1.00 |
| 23101 | 3 | | | | | Sult2a3 | 1.00 | 23197 | 3 | | | | Tbc1d21 | 1.00 |
| 23102 | 3 | | | | | Sult2a4 | 1.00 | 23198 | 3 | | | | Tbc1d22bos | 1.00 |
| 23103 | 3 | | | | | Sult2a5 | 1.00 | 23199 | 3 | | | | Tbpl2 | 1.00 |
| 23104 | 3 | | | | | Sult2a6 | 1.00 | 23200 | 3 | | | | Tbrg3 | 1.00 |
| 23105 | 3 | | | | | Sult2a7 | 1.00 | 23201 | 3 | | | | Tbx10 | 1.00 |
| 23106 | 3 | | | | | Sult3a1 | 1.00 | 23202 | 3 | | | | Tbx19 | 1.00 |
| 23107 | 3 | | | | | Sult6b1 | 1.00 | 23203 | 3 | | | | Tbx21 | 1.00 |
| 23108 | 3 | | | | | Sun3 | 1.00 | 23204 | 3 | | | | Tbx22 | 1.00 |
| 23109 | 3 | | | | | Sun5 | 1.00 | 23205 | 3 | | | | Tbx3os2 | 1.00 |
| 23110 | 3 | | | | | Sva | 1.00 | 23206 | 3 | | | | Tc2n | 1.00 |
| 23111 | 3 | | | | | Sval1 | 1.00 | 23207 | 3 | | | | Tcam1 | 1.00 |
| 23112 | 3 | | | | | Sval2 | 1.00 | 23208 | 3 | | | | Tcf23 | 1.00 |
| 23113 | 3 | | | | | Sval3 | 1.00 | 23209 | 3 | | | | Tchhl1 | 1.00 |
| 23114 | 3 | | | | | Svopl | 1.00 | 23210 | 3 | | | | Tcl1 | 1.00 |
| 23115 | 3 | | | | | Svs1 | 1.00 | 23211 | 3 | | | | Tcl1b1 | 1.00 |
| 23116 | 3 | | | | | Svs2 | 1.00 | 23212 | 3 | | | | Tcl1b2 | 1.00 |
| 23117 | 3 | | | | | Svs3a | 1.00 | 23213 | 3 | | | | Tcl1b3 | 1.00 |
| 23118 | 3 | | | | | Svs3b | 1.00 | 23214 | 3 | | | | Tcl1b4 | 1.00 |
| 23119 | 3 | | | | | Svs4 | 1.00 | 23215 | 3 | | | | Tcl1b5 | 1.00 |
| 23120 | 3 | | | | | Svs5 | 1.00 | 23216 | 3 | | | | Tcp10a | 1.00 |
| 23121 | 3 | | | | | Svs6 | 1.00 | 23217 | 3 | | | | Tcp10b | 1.00 |
| 23122 | 3 | | | | | Syce1 | 1.00 | 23218 | 3 | | | | Tcp10c | 1.00 |
| 23123 | 3 | | | | | Syce1l | 1.00 | 23219 | 3 | | | | Tcstv1 | 1.00 |
| 23124 | 3 | | | | | Syce3 | 1.00 | 23220 | 3 | | | | Tcstv3 | 1.00 |
| 23125 | 3 | | | | | Sycp1 | 1.00 | 23221 | 3 | | | | Tcte1 | 1.00 |
| 23126 | 3 | | | | | Sycp1-ps1 | 1.00 | 23222 | 3 | | | | Tctex1d1 | 1.00 |
| 23127 | 3 | | | | | Sycp2 | 1.00 | 23223 | 3 | | | | Tctex1d4 | 1.00 |
| 23128 | 3 | | | | | Sycp3 | 1.00 | 23224 | 3 | | | | Tdg | 1.00 |
| 23129 | 3 | | | | | Synb | 1.00 | 23225 | 3 | | | | Tdgf1 | 1.00 |
| 23130 | 3 | | | | | Syngr4 | 1.00 | 23226 | 3 | | | | Tdo2 | 1.00 |
| 23131 | 3 | | | | | Syt10 | 1.00 | 23227 | 3 | | | | Tdpoz1 | 1.00 |
| 23132 | 3 | | | | | Syt8 | 1.00 | 23228 | 3 | | | | Tdpoz2 | 1.00 |
| 23133 | 3 | | | | | Syt3 | 1.00 | 23229 | 3 | | | | Tdpoz3 | 1.00 |

Fig. 45 - 122

| | | | | | | | | | | | | | | |
|---|---|---|---|---|---|---|---|---|---|---|---|---|---|---|
| 23230 | 3 | | | | | Tdpoz4 | 1.00 | 23326 | 3 | | | | Tmprss15 | 1.00 |
| 23231 | 3 | | | | | Tdpoz5 | 1.00 | 23327 | 3 | | | | Tmprss3 | 1.00 |
| 23232 | 3 | | | | | Tdrd12 | 1.00 | 23328 | 3 | | | | Tmprss5 | 1.00 |
| 23233 | 3 | | | | | Tdrd5 | 1.00 | 23329 | 3 | | | | Tmprss7 | 1.00 |
| 23234 | 3 | | | | | Tdrd6 | 1.00 | 23330 | 3 | | | | Tmprss9 | 1.00 |
| 23235 | 3 | | | | | Tdrd9 | 1.00 | 23331 | 3 | | | | Tmsb15a | 1.00 |
| 23236 | 3 | | | | | Tecta | 1.00 | 23332 | 3 | | | | Tmsb15b2 | 1.00 |
| 23237 | 3 | | | | | Tectb | 1.00 | 23333 | 3 | | | | Tnf | 1.00 |
| 23238 | 3 | | | | | Teddm1 | 1.00 | 23334 | 3 | | | | Tnfrsf13b | 1.00 |
| 23239 | 3 | | | | | Tekt3 | 1.00 | 23335 | 3 | | | | Tnfrsf13c | 1.00 |
| 23240 | 3 | | | | | Tekt4 | 1.00 | 23336 | 3 | | | | Tnfrsf17 | 1.00 |
| 23241 | 3 | | | | | Tepp | 1.00 | 23337 | 3 | | | | Tnfrsf26 | 1.00 |
| 23242 | 3 | | | | | Tescl | 1.00 | 23338 | 3 | | | | Tnfrsf4 | 1.00 |
| 23243 | 3 | | | | | Tespa1 | 1.00 | 23339 | 3 | | | | Tnfrsf8 | 1.00 |
| 23244 | 3 | | | | | Tex101 | 1.00 | 23340 | 3 | | | | Tnfrsf9 | 1.00 |
| 23245 | 3 | | | | | Tex11 | 1.00 | 23341 | 3 | | | | Tnfsf12Tnfsf13 | 1.00 |
| 23246 | 3 | | | | | Tex12 | 1.00 | 23342 | 3 | | | | Tnfsf13b | 1.00 |
| 23247 | 3 | | | | | Tex13 | 1.00 | 23343 | 3 | | | | Tnfsf14 | 1.00 |
| 23248 | 3 | | | | | Tex13a | 1.00 | 23344 | 3 | | | | Tnfsf15 | 1.00 |
| 23249 | 3 | | | | | Tex14 | 1.00 | 23345 | 3 | | | | Tnfsf18 | 1.00 |
| 23250 | 3 | | | | | Tex16 | 1.00 | 23346 | 3 | | | | Tnfsf4 | 1.00 |
| 23251 | 3 | | | | | Tex19.1 | 1.00 | 23347 | 3 | | | | Tnfsf8 | 1.00 |
| 23252 | 3 | | | | | Tex19.2 | 1.00 | 23348 | 3 | | | | Tnip3 | 1.00 |
| 23253 | 3 | | | | | Tex21 | 1.00 | 23349 | 3 | | | | Tnni3k | 1.00 |
| 23254 | 3 | | | | | Tex22 | 1.00 | 23350 | 3 | | | | Tnp1 | 1.00 |
| 23255 | 3 | | | | | Tex24 | 1.00 | 23351 | 3 | | | | Tnp2 | 1.00 |
| 23256 | 3 | | | | | Tex26 | 1.00 | 23352 | 3 | | | | Tomm20l | 1.00 |
| 23257 | 3 | | | | | Tex28 | 1.00 | 23353 | 3 | | | | Topaz1 | 1.00 |
| 23258 | 3 | | | | | Tex29 | 1.00 | 23354 | 3 | | | | Toporsl | 1.00 |
| 23259 | 3 | | | | | Tex33 | 1.00 | 23355 | 3 | | | | Tpbg | 1.00 |
| 23260 | 3 | | | | | Tex35 | 1.00 | 23356 | 3 | | | | Tpbpa | 1.00 |
| 23261 | 3 | | | | | Tex36 | 1.00 | 23357 | 3 | | | | Tpbpb | 1.00 |
| 23262 | 3 | | | | | Tex37 | 1.00 | 23358 | 3 | | | | Tph1 | 1.00 |
| 23263 | 3 | | | | | Tex40 | 1.00 | 23359 | 3 | | | | Tph2 | 1.00 |
| 23264 | 3 | | | | | Tex43 | 1.00 | 23360 | 3 | | | | Tpo | 1.00 |
| 23265 | 3 | | | | | Tfap2e | 1.00 | 23361 | 3 | | | | Tppp2 | 1.00 |
| 23266 | 3 | | | | | Tfb2m | 1.00 | 23362 | 3 | | | | Tpte | 1.00 |
| 23267 | 3 | | | | | Tff2 | 1.00 | 23363 | 3 | | | | Traf1 | 1.00 |
| 23268 | 3 | | | | | Tgif2lx1 | 1.00 | 23364 | 3 | | | | Trap1a | 1.00 |
| 23269 | 3 | | | | | Tgif2lx2 | 1.00 | 23365 | 3 | | | | Trappc3l | 1.00 |
| 23270 | 3 | | | | | Tgm5 | 1.00 | 23366 | 3 | | | | Trat1 | 1.00 |
| 23271 | 3 | | | | | Tgm6 | 1.00 | 23367 | 3 | | | | Trcg1 | 1.00 |
| 23272 | 3 | | | | | Tgm7 | 1.00 | 23368 | 3 | | | | Treh | 1.00 |
| 23273 | 3 | | | | | Tgtp2 | 1.00 | 23369 | 3 | | | | Trem1 | 1.00 |
| 23274 | 3 | | | | | Theg | 1.00 | 23370 | 3 | | | | Treml4 | 1.00 |
| 23275 | 3 | | | | | Them7 | 1.00 | 23371 | 3 | | | | Trh | 1.00 |
| 23276 | 3 | | | | | Themis | 1.00 | 23372 | 3 | | | | Trhr | 1.00 |
| 23277 | 3 | | | | | Themis3 | 1.00 | 23373 | 3 | | | | Trhr2 | 1.00 |
| 23278 | 3 | | | | | Tigit | 1.00 | 23374 | 3 | | | | Trib1 | 1.00 |
| 23279 | 3 | | | | | Timm8a2 | 1.00 | 23375 | 3 | | | | Trim15 | 1.00 |
| 23280 | 3 | | | | | Tktl1 | 1.00 | 23376 | 3 | | | | Trim17 | 1.00 |
| 23281 | 3 | | | | | Tktl2 | 1.00 | 23377 | 3 | | | | Trim30b | 1.00 |
| 23282 | 3 | | | | | Tldc2 | 1.00 | 23378 | 3 | | | | Trim30e-ps1 | 1.00 |
| 23283 | 3 | | | | | Tll2 | 1.00 | 23379 | 3 | | | | Trim31 | 1.00 |
| 23284 | 3 | | | | | Tlr11 | 1.00 | 23380 | 3 | | | | Trim34b | 1.00 |
| 23285 | 3 | | | | | Tlr12 | 1.00 | 23381 | 3 | | | | Trim38 | 1.00 |
| 23286 | 3 | | | | | Tlx1 | 1.00 | 23382 | 3 | | | | Trim40 | 1.00 |
| 23287 | 3 | | | | | Tm4sf19 | 1.00 | 23383 | 3 | | | | Trim42 | 1.00 |
| 23288 | 3 | | | | | Tmbim1 | 1.00 | 23384 | 3 | | | | Trim43a | 1.00 |
| 23289 | 3 | | | | | Tmbim7 | 1.00 | 23385 | 3 | | | | Trim43b | 1.00 |
| 23290 | 3 | | | | | Tmc1 | 1.00 | 23386 | 3 | | | | Trim43c | 1.00 |
| 23291 | 3 | | | | | Tmc2 | 1.00 | 23387 | 3 | | | | Trim50 | 1.00 |
| 23292 | 3 | | | | | Tmc5 | 1.00 | 23388 | 3 | | | | Trim52 | 1.00 |
| 23293 | 3 | | | | | Tmco2 | 1.00 | 23389 | 3 | | | | Trim60 | 1.00 |
| 23294 | 3 | | | | | Tmco5 | 1.00 | 23390 | 3 | | | | Trim61 | 1.00 |
| 23295 | 3 | | | | | Tmco5b | 1.00 | 23391 | 3 | | | | Trim69 | 1.00 |
| 23296 | 3 | | | | | Tmem116 | 1.00 | 23392 | 3 | | | | Trim75 | 1.00 |
| 23297 | 3 | | | | | Tmem132cos | 1.00 | 23393 | 3 | | | | Triml1 | 1.00 |
| 23298 | 3 | | | | | Tmem150cos | 1.00 | 23394 | 3 | | | | Triml2 | 1.00 |
| 23299 | 3 | | | | | Tmem174 | 1.00 | 23395 | 3 | | | | Trip11 | 1.00 |
| 23300 | 3 | | | | | Tmem190 | 1.00 | 23396 | 3 | | | | Trnau1ap | 1.00 |
| 23301 | 3 | | | | | Tmem202 | 1.00 | 23397 | 3 | | | | Trp53i13 | 1.00 |
| 23302 | 3 | | | | | Tmem207 | 1.00 | 23398 | 3 | | | | Trp53tg5 | 1.00 |
| 23303 | 3 | | | | | Tmem210 | 1.00 | 23399 | 3 | | | | Trpa1 | 1.00 |
| 23304 | 3 | | | | | Tmem211 | 1.00 | 23400 | 3 | | | | Trpc5os | 1.00 |
| 23305 | 3 | | | | | Tmem215 | 1.00 | 23401 | 3 | | | | Trpc6 | 1.00 |
| 23306 | 3 | | | | | Tmem217 | 1.00 | 23402 | 3 | | | | Trpc7 | 1.00 |
| 23307 | 3 | | | | | Tmem221 | 1.00 | 23403 | 3 | | | | Trpd52l3 | 1.00 |
| 23308 | 3 | | | | | Tmem225 | 1.00 | 23404 | 3 | | | | Trpm1 | 1.00 |
| 23309 | 3 | | | | | Tmem232 | 1.00 | 23405 | 3 | | | | Trpm2 | 1.00 |
| 23310 | 3 | | | | | Tmem235 | 1.00 | 23406 | 3 | | | | Trpm6 | 1.00 |
| 23311 | 3 | | | | | Tmem247 | 1.00 | 23407 | 3 | | | | Trpm8 | 1.00 |
| 23312 | 3 | | | | | Tmem255b | 1.00 | 23408 | 3 | | | | Trpv1 | 1.00 |
| 23313 | 3 | | | | | Tmem30c | 1.00 | 23409 | 3 | | | | Trpv3 | 1.00 |
| 23314 | 3 | | | | | Tmem51os1 | 1.00 | 23410 | 3 | | | | Trpv5 | 1.00 |
| 23315 | 3 | | | | | Tmem52b | 1.00 | 23411 | 3 | | | | Trpv6 | 1.00 |
| 23316 | 3 | | | | | Tmem71 | 1.00 | 23412 | 3 | | | | Tsc2 | 1.00 |
| 23317 | 3 | | | | | Tmem89 | 1.00 | 23413 | 3 | | | | Tsga13 | 1.00 |
| 23318 | 3 | | | | | Tmem92 | 1.00 | 23414 | 3 | | | | Tsga8 | 1.00 |
| 23319 | 3 | | | | | Tmem95 | 1.00 | 23415 | 3 | | | | Tshb | 1.00 |
| 23320 | 3 | | | | | Tmevpg1 | 1.00 | 23416 | 3 | | | | Tshr | 1.00 |
| 23321 | 3 | | | | | Tmprss11c | 1.00 | 23417 | 3 | | | | Tsix | 1.00 |
| 23322 | 3 | | | | | Tmprss11d | 1.00 | 23418 | 3 | | | | Tsks | 1.00 |
| 23323 | 3 | | | | | Tmprss11e | 1.00 | 23419 | 3 | | | | Tsnaxip1 | 1.00 |
| 23324 | 3 | | | | | Tmprss11g | 1.00 | 23420 | 3 | | | | Tspan10 | 1.00 |
| 23325 | 3 | | | | | Tmprss12 | 1.00 | 23421 | 3 | | | | Tspan2os | 1.00 |

Fig. 45 - 123

| | | | | | | | | | | | | | | |
|---|---|---|---|---|---|---|---|---|---|---|---|---|---|---|
| 23422 | 3 | | | | | Tspear | 1.00 | 23518 | 3 | | | | Vaultrc5 | 1.00 |
| 23423 | 3 | | | | | Tspy-ps | 1.00 | 23519 | 3 | | | | Vax2 | 1.00 |
| 23424 | 3 | | | | | Tssk1 | 1.00 | 23520 | 3 | | | | Vcpip1 | 1.00 |
| 23425 | 3 | | | | | Tssk2 | 1.00 | 23521 | 3 | | | | Vezt | 1.00 |
| 23426 | 3 | | | | | Tssk3 | 1.00 | 23522 | 3 | | | | Vgll1 | 1.00 |
| 23427 | 3 | | | | | Tssk5 | 1.00 | 23523 | 3 | | | | Vipr1 | 1.00 |
| 23428 | 3 | | | | | Tstd1 | 1.00 | 23524 | 3 | | | | Vmn1r-ps103 | 1.00 |
| 23429 | 3 | | | | | Tsx | 1.00 | 23525 | 3 | | | | Vmn1r-ps79 | 1.00 |
| 23430 | 3 | | | | | Ttc12 | 1.00 | 23526 | 3 | | | | Vmn1r1 | 1.00 |
| 23431 | 3 | | | | | Ttc16 | 1.00 | 23527 | 3 | | | | Vmn1r10 | 1.00 |
| 23432 | 3 | | | | | Ttc18 | 1.00 | 23528 | 3 | | | | Vmn1r100 | 1.00 |
| 23433 | 3 | | | | | Ttc21a | 1.00 | 23529 | 3 | | | | Vmn1r101 | 1.00 |
| 23434 | 3 | | | | | Ttc23l | 1.00 | 23530 | 3 | | | | Vmn1r103 | 1.00 |
| 23435 | 3 | | | | | Ttc24 | 1.00 | 23531 | 3 | | | | Vmn1r104 | 1.00 |
| 23436 | 3 | | | | | Ttc25 | 1.00 | 23532 | 3 | | | | Vmn1r107 | 1.00 |
| 23437 | 3 | | | | | Ttc29 | 1.00 | 23533 | 3 | | | | Vmn1r11 | 1.00 |
| 23438 | 3 | | | | | Ttc34 | 1.00 | 23534 | 3 | | | | Vmn1r112 | 1.00 |
| 23439 | 3 | | | | | Ttc39d | 1.00 | 23535 | 3 | | | | Vmn1r113 | 1.00 |
| 23440 | 3 | | | | | Ttll10 | 1.00 | 23536 | 3 | | | | Vmn1r114 | 1.00 |
| 23441 | 3 | | | | | Ttll13 | 1.00 | 23537 | 3 | | | | Vmn1r115 | 1.00 |
| 23442 | 3 | | | | | Ttll2 | 1.00 | 23538 | 3 | | | | Vmn1r116 | 1.00 |
| 23443 | 3 | | | | | Ttll6 | 1.00 | 23539 | 3 | | | | Vmn1r117 | 1.00 |
| 23444 | 3 | | | | | Ttll8 | 1.00 | 23540 | 3 | | | | Vmn1r118 | 1.00 |
| 23445 | 3 | | | | | Ttll9 | 1.00 | 23541 | 3 | | | | Vmn1r119 | 1.00 |
| 23446 | 3 | | | | | Tuba3a | 1.00 | 23542 | 3 | | | | Vmn1r12 | 1.00 |
| 23447 | 3 | | | | | Tuba3b | 1.00 | 23543 | 3 | | | | Vmn1r120 | 1.00 |
| 23448 | 3 | | | | | Tubal3 | 1.00 | 23544 | 3 | | | | Vmn1r121 | 1.00 |
| 23449 | 3 | | | | | Tulp1 | 1.00 | 23545 | 3 | | | | Vmn1r122 | 1.00 |
| 23450 | 3 | | | | | Tulp2 | 1.00 | 23546 | 3 | | | | Vmn1r123 | 1.00 |
| 23451 | 3 | | | | | Txk | 1.00 | 23547 | 3 | | | | Vmn1r124 | 1.00 |
| 23452 | 3 | | | | | Txndc2 | 1.00 | 23548 | 3 | | | | Vmn1r125 | 1.00 |
| 23453 | 3 | | | | | Txndc8 | 1.00 | 23549 | 3 | | | | Vmn1r126 | 1.00 |
| 23454 | 3 | | | | | Txndc9 | 1.00 | 23550 | 3 | | | | Vmn1r127 | 1.00 |
| 23455 | 3 | | | | | Tymp | 1.00 | 23551 | 3 | | | | Vmn1r128 | 1.00 |
| 23456 | 3 | | | | | Tyr | 1.00 | 23552 | 3 | | | | Vmn1r129 | 1.00 |
| 23457 | 3 | | | | | U90926 | 1.00 | 23553 | 3 | | | | Vmn1r13 | 1.00 |
| 23458 | 3 | | | | | Uba1y | 1.00 | 23554 | 3 | | | | Vmn1r130 | 1.00 |
| 23459 | 3 | | | | | Uba2 | 1.00 | 23555 | 3 | | | | Vmn1r132 | 1.00 |
| 23460 | 3 | | | | | Ubap1l | 1.00 | 23556 | 3 | | | | Vmn1r135 | 1.00 |
| 23461 | 3 | | | | | Ubash3a | 1.00 | 23557 | 3 | | | | Vmn1r137 | 1.00 |
| 23462 | 3 | | | | | Ubd | 1.00 | 23558 | 3 | | | | Vmn1r138 | 1.00 |
| 23463 | 3 | | | | | Ube2d2b | 1.00 | 23559 | 3 | | | | Vmn1r139 | 1.00 |
| 23464 | 3 | | | | | Ube2dnl1 | 1.00 | 23560 | 3 | | | | Vmn1r14 | 1.00 |
| 23465 | 3 | | | | | Ube2dnl2 | 1.00 | 23561 | 3 | | | | Vmn1r142 | 1.00 |
| 23466 | 3 | | | | | Ube2el | 1.00 | 23562 | 3 | | | | Vmn1r148 | 1.00 |
| 23467 | 3 | | | | | Ube2u | 1.00 | 23563 | 3 | | | | Vmn1r15 | 1.00 |
| 23468 | 3 | | | | | Ubl4b | 1.00 | 23564 | 3 | | | | Vmn1r151 | 1.00 |
| 23469 | 3 | | | | | Ubqln3 | 1.00 | 23565 | 3 | | | | Vmn1r152 | 1.00 |
| 23470 | 3 | | | | | Ubqlnl | 1.00 | 23566 | 3 | | | | Vmn1r157 | 1.00 |
| 23471 | 3 | | | | | Ubtf1l | 1.00 | 23567 | 3 | | | | Vmn1r158 | 1.00 |
| 23472 | 3 | | | | | Ubxn11 | 1.00 | 23568 | 3 | | | | Vmn1r159 | 1.00 |
| 23473 | 3 | | | | | Uchl1os | 1.00 | 23569 | 3 | | | | Vmn1r16 | 1.00 |
| 23474 | 3 | | | | | Ucn | 1.00 | 23570 | 3 | | | | Vmn1r160 | 1.00 |
| 23475 | 3 | | | | | Ucn3 | 1.00 | 23571 | 3 | | | | Vmn1r163 | 1.00 |
| 23476 | 3 | | | | | Ucp1 | 1.00 | 23572 | 3 | | | | Vmn1r165 | 1.00 |
| 23477 | 3 | | | | | Ucp3 | 1.00 | 23573 | 3 | | | | Vmn1r166 | 1.00 |
| 23478 | 3 | | | | | Ugt1a10 | 1.00 | 23574 | 3 | | | | Vmn1r167 | 1.00 |
| 23479 | 3 | | | | | Ugt1a2 | 1.00 | 23575 | 3 | | | | Vmn1r168 | 1.00 |
| 23480 | 3 | | | | | Ugt1a5 | 1.00 | 23576 | 3 | | | | Vmn1r169 | 1.00 |
| 23481 | 3 | | | | | Ugt1a9 | 1.00 | 23577 | 3 | | | | Vmn1r17 | 1.00 |
| 23482 | 3 | | | | | Ugt2a2 | 1.00 | 23578 | 3 | | | | Vmn1r170 | 1.00 |
| 23483 | 3 | | | | | Ugt2a3 | 1.00 | 23579 | 3 | | | | Vmn1r171 | 1.00 |
| 23484 | 3 | | | | | Ugt2b1 | 1.00 | 23580 | 3 | | | | Vmn1r172 | 1.00 |
| 23485 | 3 | | | | | Ugt2b37 | 1.00 | 23581 | 3 | | | | Vmn1r173 | 1.00 |
| 23486 | 3 | | | | | Ugt3a1 | 1.00 | 23582 | 3 | | | | Vmn1r174 | 1.00 |
| 23487 | 3 | | | | | Ugt3a2 | 1.00 | 23583 | 3 | | | | Vmn1r175 | 1.00 |
| 23488 | 3 | | | | | Uimc1 | 1.00 | 23584 | 3 | | | | Vmn1r176 | 1.00 |
| 23489 | 3 | | | | | Ulk4 | 1.00 | 23585 | 3 | | | | Vmn1r177 | 1.00 |
| 23490 | 3 | | | | | Umod | 1.00 | 23586 | 3 | | | | Vmn1r178 | 1.00 |
| 23491 | 3 | | | | | Umodl1 | 1.00 | 23587 | 3 | | | | Vmn1r179 | 1.00 |
| 23492 | 3 | | | | | Unc93a | 1.00 | 23588 | 3 | | | | Vmn1r18 | 1.00 |
| 23493 | 3 | | | | | Unc93b1 | 1.00 | 23589 | 3 | | | | Vmn1r180 | 1.00 |
| 23494 | 3 | | | | | Upk1a | 1.00 | 23590 | 3 | | | | Vmn1r181 | 1.00 |
| 23495 | 3 | | | | | Upk2 | 1.00 | 23591 | 3 | | | | Vmn1r183 | 1.00 |
| 23496 | 3 | | | | | Upp2 | 1.00 | 23592 | 3 | | | | Vmn1r184 | 1.00 |
| 23497 | 3 | | | | | Urad | 1.00 | 23593 | 3 | | | | Vmn1r185 | 1.00 |
| 23498 | 3 | | | | | Ush1c | 1.00 | 23594 | 3 | | | | Vmn1r186 | 1.00 |
| 23499 | 3 | | | | | Ush1g | 1.00 | 23595 | 3 | | | | Vmn1r187 | 1.00 |
| 23500 | 3 | | | | | Ush2a | 1.00 | 23596 | 3 | | | | Vmn1r188 | 1.00 |
| 23501 | 3 | | | | | Usp17la | 1.00 | 23597 | 3 | | | | Vmn1r189 | 1.00 |
| 23502 | 3 | | | | | Usp17lb | 1.00 | 23598 | 3 | | | | Vmn1r19 | 1.00 |
| 23503 | 3 | | | | | Usp17lc | 1.00 | 23599 | 3 | | | | Vmn1r191 | 1.00 |
| 23504 | 3 | | | | | Usp17ld | 1.00 | 23600 | 3 | | | | Vmn1r192 | 1.00 |
| 23505 | 3 | | | | | Usp17le | 1.00 | 23601 | 3 | | | | Vmn1r193 | 1.00 |
| 23506 | 3 | | | | | Usp19 | 1.00 | 23602 | 3 | | | | Vmn1r194 | 1.00 |
| 23507 | 3 | | | | | Usp26 | 1.00 | 23603 | 3 | | | | Vmn1r195 | 1.00 |
| 23508 | 3 | | | | | Usp44 | 1.00 | 23604 | 3 | | | | Vmn1r196 | 1.00 |
| 23509 | 3 | | | | | Usp50 | 1.00 | 23605 | 3 | | | | Vmn1r197 | 1.00 |
| 23510 | 3 | | | | | Usp9y | 1.00 | 23606 | 3 | | | | Vmn1r198 | 1.00 |
| 23511 | 3 | | | | | Utf1 | 1.00 | 23607 | 3 | | | | Vmn1r199 | 1.00 |
| 23512 | 3 | | | | | Uts2 | 1.00 | 23608 | 3 | | | | Vmn1r2 | 1.00 |
| 23513 | 3 | | | | | Uts2b | 1.00 | 23609 | 3 | | | | Vmn1r20 | 1.00 |
| 23514 | 3 | | | | | Uxt | 1.00 | 23610 | 3 | | | | Vmn1r200 | 1.00 |
| 23515 | 3 | | | | | V1ra8 | 1.00 | 23611 | 3 | | | | Vmn1r201 | 1.00 |
| 23516 | 3 | | | | | V1rd18 | 1.00 | 23612 | 3 | | | | Vmn1r202 | 1.00 |
| 23517 | 3 | | | | | V1rd19 | 1.00 | 23613 | 3 | | | | Vmn1r203 | 1.00 |

Fig. 45 - 124

| | | | | | | | | | | | | | |
|---|---|---|---|---|---|---|---|---|---|---|---|---|---|
| 23614 | 3 | | | | | Vmn1r204 | 1.00 | 23710 | 3 | | | Vmn1r77 | 1.00 |
| 23615 | 3 | | | | | Vmn1r205 | 1.00 | 23711 | 3 | | | Vmn1r78 | 1.00 |
| 23616 | 3 | | | | | Vmn1r206 | 1.00 | 23712 | 3 | | | Vmn1r79 | 1.00 |
| 23617 | 3 | | | | | Vmn1r207-ps | 1.00 | 23713 | 3 | | | Vmn1r8 | 1.00 |
| 23618 | 3 | | | | | Vmn1r208 | 1.00 | 23714 | 3 | | | Vmn1r80 | 1.00 |
| 23619 | 3 | | | | | Vmn1r209 | 1.00 | 23715 | 3 | | | Vmn1r81 | 1.00 |
| 23620 | 3 | | | | | Vmn1r21 | 1.00 | 23716 | 3 | | | Vmn1r82 | 1.00 |
| 23621 | 3 | | | | | Vmn1r210 | 1.00 | 23717 | 3 | | | Vmn1r83 | 1.00 |
| 23622 | 3 | | | | | Vmn1r211 | 1.00 | 23718 | 3 | | | Vmn1r84 | 1.00 |
| 23623 | 3 | | | | | Vmn1r212 | 1.00 | 23719 | 3 | | | Vmn1r85 | 1.00 |
| 23624 | 3 | | | | | Vmn1r213 | 1.00 | 23720 | 3 | | | Vmn1r86 | 1.00 |
| 23625 | 3 | | | | | Vmn1r214 | 1.00 | 23721 | 3 | | | Vmn1r87 | 1.00 |
| 23626 | 3 | | | | | Vmn1r215 | 1.00 | 23722 | 3 | | | Vmn1r88 | 1.00 |
| 23627 | 3 | | | | | Vmn1r216 | 1.00 | 23723 | 3 | | | Vmn1r89 | 1.00 |
| 23628 | 3 | | | | | Vmn1r217 | 1.00 | 23724 | 3 | | | Vmn1r9 | 1.00 |
| 23629 | 3 | | | | | Vmn1r218 | 1.00 | 23725 | 3 | | | Vmn1r90 | 1.00 |
| 23630 | 3 | | | | | Vmn1r219 | 1.00 | 23726 | 3 | | | Vmn1r91 | 1.00 |
| 23631 | 3 | | | | | Vmn1r22 | 1.00 | 23727 | 3 | | | Vmn1r94 | 1.00 |
| 23632 | 3 | | | | | Vmn1r220 | 1.00 | 23728 | 3 | | | Vmn1r95 | 1.00 |
| 23633 | 3 | | | | | Vmn1r221 | 1.00 | 23729 | 3 | | | Vmn2r-ps11 | 1.00 |
| 23634 | 3 | | | | | Vmn1r222 | 1.00 | 23730 | 3 | | | Vmn2r-ps129 | 1.00 |
| 23635 | 3 | | | | | Vmn1r223 | 1.00 | 23731 | 3 | | | Vmn2r-ps159 | 1.00 |
| 23636 | 3 | | | | | Vmn1r224 | 1.00 | 23732 | 3 | | | Vmn2r-ps54 | 1.00 |
| 23637 | 3 | | | | | Vmn1r225 | 1.00 | 23733 | 3 | | | Vmn2r-ps60 | 1.00 |
| 23638 | 3 | | | | | Vmn1r226 | 1.00 | 23734 | 3 | | | Vmn2r1 | 1.00 |
| 23639 | 3 | | | | | Vmn1r227 | 1.00 | 23735 | 3 | | | Vmn2r10 | 1.00 |
| 23640 | 3 | | | | | Vmn1r228 | 1.00 | 23736 | 3 | | | Vmn2r100 | 1.00 |
| 23641 | 3 | | | | | Vmn1r229 | 1.00 | 23737 | 3 | | | Vmn2r101 | 1.00 |
| 23642 | 3 | | | | | Vmn1r23 | 1.00 | 23738 | 3 | | | Vmn2r102 | 1.00 |
| 23643 | 3 | | | | | Vmn1r230 | 1.00 | 23739 | 3 | | | Vmn2r103 | 1.00 |
| 23644 | 3 | | | | | Vmn1r231 | 1.00 | 23740 | 3 | | | Vmn2r104 | 1.00 |
| 23645 | 3 | | | | | Vmn1r232 | 1.00 | 23741 | 3 | | | Vmn2r105 | 1.00 |
| 23646 | 3 | | | | | Vmn1r233 | 1.00 | 23742 | 3 | | | Vmn2r106 | 1.00 |
| 23647 | 3 | | | | | Vmn1r234 | 1.00 | 23743 | 3 | | | Vmn2r107 | 1.00 |
| 23648 | 3 | | | | | Vmn1r235 | 1.00 | 23744 | 3 | | | Vmn2r108 | 1.00 |
| 23649 | 3 | | | | | Vmn1r236 | 1.00 | 23745 | 3 | | | Vmn2r109 | 1.00 |
| 23650 | 3 | | | | | Vmn1r237 | 1.00 | 23746 | 3 | | | Vmn2r11 | 1.00 |
| 23651 | 3 | | | | | Vmn1r238 | 1.00 | 23747 | 3 | | | Vmn2r110 | 1.00 |
| 23652 | 3 | | | | | Vmn1r24 | 1.00 | 23748 | 3 | | | Vmn2r111 | 1.00 |
| 23653 | 3 | | | | | Vmn1r25 | 1.00 | 23749 | 3 | | | Vmn2r112 | 1.00 |
| 23654 | 3 | | | | | Vmn1r26 | 1.00 | 23750 | 3 | | | Vmn2r113 | 1.00 |
| 23655 | 3 | | | | | Vmn1r27 | 1.00 | 23751 | 3 | | | Vmn2r114 | 1.00 |
| 23656 | 3 | | | | | Vmn1r28 | 1.00 | 23752 | 3 | | | Vmn2r115 | 1.00 |
| 23657 | 3 | | | | | Vmn1r29 | 1.00 | 23753 | 3 | | | Vmn2r116 | 1.00 |
| 23658 | 3 | | | | | Vmn1r3 | 1.00 | 23754 | 3 | | | Vmn2r117 | 1.00 |
| 23659 | 3 | | | | | Vmn1r30 | 1.00 | 23755 | 3 | | | Vmn2r118 | 1.00 |
| 23660 | 3 | | | | | Vmn1r31 | 1.00 | 23756 | 3 | | | Vmn2r12 | 1.00 |
| 23661 | 3 | | | | | Vmn1r32 | 1.00 | 23757 | 3 | | | Vmn2r120 | 1.00 |
| 23662 | 3 | | | | | Vmn1r33 | 1.00 | 23758 | 3 | | | Vmn2r121 | 1.00 |
| 23663 | 3 | | | | | Vmn1r34 | 1.00 | 23759 | 3 | | | Vmn2r122 | 1.00 |
| 23664 | 3 | | | | | Vmn1r35 | 1.00 | 23760 | 3 | | | Vmn2r123 | 1.00 |
| 23665 | 3 | | | | | Vmn1r36 | 1.00 | 23761 | 3 | | | Vmn2r124 | 1.00 |
| 23666 | 3 | | | | | Vmn1r37 | 1.00 | 23762 | 3 | | | Vmn2r13 | 1.00 |
| 23667 | 3 | | | | | Vmn1r38 | 1.00 | 23763 | 3 | | | Vmn2r14 | 1.00 |
| 23668 | 3 | | | | | Vmn1r39 | 1.00 | 23764 | 3 | | | Vmn2r15 | 1.00 |
| 23669 | 3 | | | | | Vmn1r4 | 1.00 | 23765 | 3 | | | Vmn2r16 | 1.00 |
| 23670 | 3 | | | | | Vmn1r40 | 1.00 | 23766 | 3 | | | Vmn2r17 | 1.00 |
| 23671 | 3 | | | | | Vmn1r41 | 1.00 | 23767 | 3 | | | Vmn2r18 | 1.00 |
| 23672 | 3 | | | | | Vmn1r42 | 1.00 | 23768 | 3 | | | Vmn2r19 | 1.00 |
| 23673 | 3 | | | | | Vmn1r43 | 1.00 | 23769 | 3 | | | Vmn2r2 | 1.00 |
| 23674 | 3 | | | | | Vmn1r44 | 1.00 | 23770 | 3 | | | Vmn2r20 | 1.00 |
| 23675 | 3 | | | | | Vmn1r45 | 1.00 | 23771 | 3 | | | Vmn2r21 | 1.00 |
| 23676 | 3 | | | | | Vmn1r46 | 1.00 | 23772 | 3 | | | Vmn2r22 | 1.00 |
| 23677 | 3 | | | | | Vmn1r47 | 1.00 | 23773 | 3 | | | Vmn2r23 | 1.00 |
| 23678 | 3 | | | | | Vmn1r48 | 1.00 | 23774 | 3 | | | Vmn2r24 | 1.00 |
| 23679 | 3 | | | | | Vmn1r49 | 1.00 | 23775 | 3 | | | Vmn2r25 | 1.00 |
| 23680 | 3 | | | | | Vmn1r5 | 1.00 | 23776 | 3 | | | Vmn2r26 | 1.00 |
| 23681 | 3 | | | | | Vmn1r50 | 1.00 | 23777 | 3 | | | Vmn2r27 | 1.00 |
| 23682 | 3 | | | | | Vmn1r51 | 1.00 | 23778 | 3 | | | Vmn2r28 | 1.00 |
| 23683 | 3 | | | | | Vmn1r52 | 1.00 | 23779 | 3 | | | Vmn2r3 | 1.00 |
| 23684 | 3 | | | | | Vmn1r53 | 1.00 | 23780 | 3 | | | Vmn2r30 | 1.00 |
| 23685 | 3 | | | | | Vmn1r54 | 1.00 | 23781 | 3 | | | Vmn2r31 | 1.00 |
| 23686 | 3 | | | | | Vmn1r55 | 1.00 | 23782 | 3 | | | Vmn2r32 | 1.00 |
| 23687 | 3 | | | | | Vmn1r56 | 1.00 | 23783 | 3 | | | Vmn2r33 | 1.00 |
| 23688 | 3 | | | | | Vmn1r57 | 1.00 | 23784 | 3 | | | Vmn2r34 | 1.00 |
| 23689 | 3 | | | | | Vmn1r58 | 1.00 | 23785 | 3 | | | Vmn2r35 | 1.00 |
| 23690 | 3 | | | | | Vmn1r59 | 1.00 | 23786 | 3 | | | Vmn2r36 | 1.00 |
| 23691 | 3 | | | | | Vmn1r6 | 1.00 | 23787 | 3 | | | Vmn2r37 | 1.00 |
| 23692 | 3 | | | | | Vmn1r60 | 1.00 | 23788 | 3 | | | Vmn2r38 | 1.00 |
| 23693 | 3 | | | | | Vmn1r61 | 1.00 | 23789 | 3 | | | Vmn2r39 | 1.00 |
| 23694 | 3 | | | | | Vmn1r62 | 1.00 | 23790 | 3 | | | Vmn2r4 | 1.00 |
| 23695 | 3 | | | | | Vmn1r63 | 1.00 | 23791 | 3 | | | Vmn2r40 | 1.00 |
| 23696 | 3 | | | | | Vmn1r64 | 1.00 | 23792 | 3 | | | Vmn2r41 | 1.00 |
| 23697 | 3 | | | | | Vmn1r65 | 1.00 | 23793 | 3 | | | Vmn2r42 | 1.00 |
| 23698 | 3 | | | | | Vmn1r66 | 1.00 | 23794 | 3 | | | Vmn2r43 | 1.00 |
| 23699 | 3 | | | | | Vmn1r67 | 1.00 | 23795 | 3 | | | Vmn2r44 | 1.00 |
| 23700 | 3 | | | | | Vmn1r68 | 1.00 | 23796 | 3 | | | Vmn2r45 | 1.00 |
| 23701 | 3 | | | | | Vmn1r69 | 1.00 | 23797 | 3 | | | Vmn2r46 | 1.00 |
| 23702 | 3 | | | | | Vmn1r7 | 1.00 | 23798 | 3 | | | Vmn2r47 | 1.00 |
| 23703 | 3 | | | | | Vmn1r70 | 1.00 | 23799 | 3 | | | Vmn2r48 | 1.00 |
| 23704 | 3 | | | | | Vmn1r71 | 1.00 | 23800 | 3 | | | Vmn2r49 | 1.00 |
| 23705 | 3 | | | | | Vmn1r72 | 1.00 | 23801 | 3 | | | Vmn2r5 | 1.00 |
| 23706 | 3 | | | | | Vmn1r73 | 1.00 | 23802 | 3 | | | Vmn2r50 | 1.00 |
| 23707 | 3 | | | | | Vmn1r74 | 1.00 | 23803 | 3 | | | Vmn2r51 | 1.00 |
| 23708 | 3 | | | | | Vmn1r75 | 1.00 | 23804 | 3 | | | Vmn2r52 | 1.00 |
| 23709 | 3 | | | | | Vmn1r76 | 1.00 | 23805 | 3 | | | Vmn2r53 | 1.00 |

Fig. 45 - 125

| | | | | | | | | | | | | | | | |
|---|---|---|---|---|---|---|---|---|---|---|---|---|---|---|---|
| 23806 | 3 | | | | | Vmn2r54 | 1.00 | 23902 | 3 | | | | | Wnt8a | 1.00 |
| 23807 | 3 | | | | | Vmn2r55 | 1.00 | 23903 | 3 | | | | | Wnt8b | 1.00 |
| 23808 | 3 | | | | | Vmn2r56 | 1.00 | 23904 | 3 | | | | | Wnt9b | 1.00 |
| 23809 | 3 | | | | | Vmn2r57 | 1.00 | 23905 | 3 | | | | | Wt1os | 1.00 |
| 23810 | 3 | | | | | Vmn2r58 | 1.00 | 23906 | 3 | | | | | Xcl1 | 1.00 |
| 23811 | 3 | | | | | Vmn2r59 | 1.00 | 23907 | 3 | | | | | Xcr1 | 1.00 |
| 23812 | 3 | | | | | Vmn2r6 | 1.00 | 23908 | 3 | | | | | Xkr6 | 1.00 |
| 23813 | 3 | | | | | Vmn2r60 | 1.00 | 23909 | 3 | | | | | Xkr9 | 1.00 |
| 23814 | 3 | | | | | Vmn2r61 | 1.00 | 23910 | 3 | | | | | Xlr | 1.00 |
| 23815 | 3 | | | | | Vmn2r62 | 1.00 | 23911 | 3 | | | | | Xlr3a | 1.00 |
| 23816 | 3 | | | | | Vmn2r63 | 1.00 | 23912 | 3 | | | | | Xlr3c | 1.00 |
| 23817 | 3 | | | | | Vmn2r65 | 1.00 | 23913 | 3 | | | | | Xlr4a | 1.00 |
| 23818 | 3 | | | | | Vmn2r66 | 1.00 | 23914 | 3 | | | | | Xlr4b | 1.00 |
| 23819 | 3 | | | | | Vmn2r67 | 1.00 | 23915 | 3 | | | | | Xlr4c | 1.00 |
| 23820 | 3 | | | | | Vmn2r68 | 1.00 | 23916 | 3 | | | | | Xlr5a | 1.00 |
| 23821 | 3 | | | | | Vmn2r69 | 1.00 | 23917 | 3 | | | | | Xlr5b | 1.00 |
| 23822 | 3 | | | | | Vmn2r7 | 1.00 | 23918 | 3 | | | | | Xlr5c | 1.00 |
| 23823 | 3 | | | | | Vmn2r70 | 1.00 | 23919 | 3 | | | | | Xntrpc | 1.00 |
| 23824 | 3 | | | | | Vmn2r71 | 1.00 | 23920 | 3 | | | | | Xpnpep2 | 1.00 |
| 23825 | 3 | | | | | Vmn2r72 | 1.00 | 23921 | 3 | | | | | Xrra1 | 1.00 |
| 23826 | 3 | | | | | Vmn2r73 | 1.00 | 23922 | 3 | | | | | Yipf3 | 1.00 |
| 23827 | 3 | | | | | Vmn2r74 | 1.00 | 23923 | 3 | | | | | Zan | 1.00 |
| 23828 | 3 | | | | | Vmn2r75 | 1.00 | 23924 | 3 | | | | | Zap70 | 1.00 |
| 23829 | 3 | | | | | Vmn2r76 | 1.00 | 23925 | 3 | | | | | Zar1 | 1.00 |
| 23830 | 3 | | | | | Vmn2r77 | 1.00 | 23926 | 3 | | | | | Zar1l | 1.00 |
| 23831 | 3 | | | | | Vmn2r78 | 1.00 | 23927 | 3 | | | | | Zbbx | 1.00 |
| 23832 | 3 | | | | | Vmn2r79 | 1.00 | 23928 | 3 | | | | | Zbtb32 | 1.00 |
| 23833 | 3 | | | | | Vmn2r8 | 1.00 | 23929 | 3 | | | | | Zbtb4 | 1.00 |
| 23834 | 3 | | | | | Vmn2r80 | 1.00 | 23930 | 3 | | | | | Zbtb41 | 1.00 |
| 23835 | 3 | | | | | Vmn2r81 | 1.00 | 23931 | 3 | | | | | Zc2hc1b | 1.00 |
| 23836 | 3 | | | | | Vmn2r82 | 1.00 | 23932 | 3 | | | | | Zc3h12d | 1.00 |
| 23837 | 3 | | | | | Vmn2r83 | 1.00 | 23933 | 3 | | | | | Zcchc13 | 1.00 |
| 23838 | 3 | | | | | Vmn2r84 | 1.00 | 23934 | 3 | | | | | Zcchc16 | 1.00 |
| 23839 | 3 | | | | | Vmn2r85 | 1.00 | 23935 | 3 | | | | | Zdhhc11 | 1.00 |
| 23840 | 3 | | | | | Vmn2r86 | 1.00 | 23936 | 3 | | | | | Zdhhc19 | 1.00 |
| 23841 | 3 | | | | | Vmn2r87 | 1.00 | 23937 | 3 | | | | | Zdhhc25 | 1.00 |
| 23842 | 3 | | | | | Vmn2r88 | 1.00 | 23938 | 3 | | | | | Zfp12 | 1.00 |
| 23843 | 3 | | | | | Vmn2r89 | 1.00 | 23939 | 3 | | | | | Zfp345 | 1.00 |
| 23844 | 3 | | | | | Vmn2r9 | 1.00 | 23940 | 3 | | | | | Zfp352 | 1.00 |
| 23845 | 3 | | | | | Vmn2r90 | 1.00 | 23941 | 3 | | | | | Zfp36l3 | 1.00 |
| 23846 | 3 | | | | | Vmn2r91 | 1.00 | 23942 | 3 | | | | | Zfp389 | 1.00 |
| 23847 | 3 | | | | | Vmn2r92 | 1.00 | 23943 | 3 | | | | | Zfp42 | 1.00 |
| 23848 | 3 | | | | | Vmn2r93 | 1.00 | 23944 | 3 | | | | | Zfp457 | 1.00 |
| 23849 | 3 | | | | | Vmn2r94 | 1.00 | 23945 | 3 | | | | | Zfp459 | 1.00 |
| 23850 | 3 | | | | | Vmn2r95 | 1.00 | 23946 | 3 | | | | | Zfp488 | 1.00 |
| 23851 | 3 | | | | | Vmn2r96 | 1.00 | 23947 | 3 | | | | | Zfp534 | 1.00 |
| 23852 | 3 | | | | | Vmn2r97 | 1.00 | 23948 | 3 | | | | | Zfp541 | 1.00 |
| 23853 | 3 | | | | | Vmn2r98 | 1.00 | 23949 | 3 | | | | | Zfp572 | 1.00 |
| 23854 | 3 | | | | | Vmn2r99 | 1.00 | 23950 | 3 | | | | | Zfp600 | 1.00 |
| 23855 | 3 | | | | | Vmo1 | 1.00 | 23951 | 3 | | | | | Zfp616 | 1.00 |
| 23856 | 3 | | | | | Vpreb2 | 1.00 | 23952 | 3 | | | | | Zfp648 | 1.00 |
| 23857 | 3 | | | | | Vps41 | 1.00 | 23953 | 3 | | | | | Zfp735 | 1.00 |
| 23858 | 3 | | | | | Vrtn | 1.00 | 23954 | 3 | | | | | Zfp760 | 1.00 |
| 23859 | 3 | | | | | Vsig1 | 1.00 | 23955 | 3 | | | | | Zfp771 | 1.00 |
| 23860 | 3 | | | | | Vsig4 | 1.00 | 23956 | 3 | | | | | Zfp78 | 1.00 |
| 23861 | 3 | | | | | Vsx1 | 1.00 | 23957 | 3 | | | | | Zfp804b | 1.00 |
| 23862 | 3 | | | | | Vtcn1 | 1.00 | 23958 | 3 | | | | | Zfp819 | 1.00 |
| 23863 | 3 | | | | | Vwa3a | 1.00 | 23959 | 3 | | | | | Zfp831 | 1.00 |
| 23864 | 3 | | | | | Vwa5b1 | 1.00 | 23960 | 3 | | | | | Zfp85os | 1.00 |
| 23865 | 3 | | | | | Vwa7 | 1.00 | 23961 | 3 | | | | | Zfp872 | 1.00 |
| 23866 | 3 | | | | | Vwde | 1.00 | 23962 | 3 | | | | | Zfp91Cntf | 1.00 |
| 23867 | 3 | | | | | Wap | 1.00 | 23963 | 3 | | | | | Zfp92 | 1.00 |
| 23868 | 3 | | | | | Wbp2nl | 1.00 | 23964 | 3 | | | | | Zfp936 | 1.00 |
| 23869 | 3 | | | | | Wbscr25 | 1.00 | 23965 | 3 | | | | | Zfp957 | 1.00 |
| 23870 | 3 | | | | | Wbscr28 | 1.00 | 23966 | 3 | | | | | Zfy1 | 1.00 |
| 23871 | 3 | | | | | Wdr17 | 1.00 | 23967 | 3 | | | | | Zfy2 | 1.00 |
| 23872 | 3 | | | | | Wdr27 | 1.00 | 23968 | 3 | | | | | Zglp1 | 1.00 |
| 23873 | 3 | | | | | Wdr38 | 1.00 | 23969 | 3 | | | | | Zim3 | 1.00 |
| 23874 | 3 | | | | | Wdr52 | 1.00 | 23970 | 3 | | | | | Zmynd12 | 1.00 |
| 23875 | 3 | | | | | Wdr54 | 1.00 | 23971 | 3 | | | | | Zmynd15 | 1.00 |
| 23876 | 3 | | | | | Wdr63 | 1.00 | 23972 | 3 | | | | | Znrf4 | 1.00 |
| 23877 | 3 | | | | | Wdr64 | 1.00 | 23973 | 3 | | | | | Zp1 | 1.00 |
| 23878 | 3 | | | | | Wdr65 | 1.00 | 23974 | 3 | | | | | Zp2 | 1.00 |
| 23879 | 3 | | | | | Wdr72 | 1.00 | 23975 | 3 | | | | | Zp3 | 1.00 |
| 23880 | 3 | | | | | Wdr93 | 1.00 | 23976 | 3 | | | | | Zp3r | 1.00 |
| 23881 | 3 | | | | | Wdr95 | 1.00 | 23977 | 3 | | | | | Zp4-ps | 1.00 |
| 23882 | 3 | | | | | Wdr96 | 1.00 | 23978 | 3 | | | | | Zpbp | 1.00 |
| 23883 | 3 | | | | | Wee2 | 1.00 | 23979 | 3 | | | | | Zpbp2 | 1.00 |
| 23884 | 3 | | | | | Wfdc10 | 1.00 | 23980 | 3 | | | | | Zpld1 | 1.00 |
| 23885 | 3 | | | | | Wfdc11 | 1.00 | 23981 | 3 | | | | | Zscan10 | 1.00 |
| 23886 | 3 | | | | | Wfdc12 | 1.00 | 23982 | 3 | | | | | Zscan4a | 1.00 |
| 23887 | 3 | | | | | Wfdc13 | 1.00 | 23983 | 3 | | | | | Zscan4b | 1.00 |
| 23888 | 3 | | | | | Wfdc15a | 1.00 | 23984 | 3 | | | | | Zscan4c | 1.00 |
| 23889 | 3 | | | | | Wfdc15b | 1.00 | 23985 | 3 | | | | | Zscan4d | 1.00 |
| 23890 | 3 | | | | | Wfdc16 | 1.00 | 23986 | 3 | | | | | Zscan4e | 1.00 |
| 23891 | 3 | | | | | Wfdc17 | 1.00 | 23987 | 3 | | | | | Zscan4f | 1.00 |
| 23892 | 3 | | | | | Wfdc18 | 1.00 | 23988 | 3 | | | | | Zscan5b | 1.00 |
| 23893 | 3 | | | | | Wfdc3 | 1.00 | 23989 | 3 | | | | | Zswim2 | 1.00 |
| 23894 | 3 | | | | | Wfdc6a | 1.00 | 23990 | 3 | | | | | Zyg11a | 1.00 |
| 23895 | 3 | | | | | Wfdc6b | 1.00 | 23991 | 3 | | | | | a | 1.01 |
| 23896 | 3 | | | | | Wfdc8 | 1.00 | | | | | | | | |
| 23897 | 3 | | | | | Wfdc9 | 1.00 | | | | | | | | |
| 23898 | 3 | | | | | Wipi1 | 1.00 | | | | | | | | |
| 23899 | 3 | | | | | Wisp2 | 1.00 | | | | | | | | |
| 23900 | 3 | | | | | Wnt1 | 1.00 | | | | | | | | |
| 23901 | 3 | | | | | Wnt3a | 1.00 | | | | | | | | |

SEQUENCE LISTING

<160> NUMBER OF SEQ ID NOS: 174

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
acagcagaca gggacagagg                                               20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tcctgtcttg acactccctc a                                             21

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3

```
actaccgagt ccgagtctac c                                              21

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cccaccttat tagggacact gg                                             22

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
taacctggcc gtcaatgc                                                  18

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gccagctgga aagtcaagat                                                20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gcagctatgt tgctacggtc                                                20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gatggggcag cgtccaatac                                                20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgacccagtg ttgtgcagag                                                20

<210> SEQ ID NO 10
<211> LENGTH: 21
<212> TYPE: DNA
<213> ORGANISM: Artificial Sequence
```

```
<220> FEATURE:
<223> OTHER INFORMATION: primer

<400> SEQUENCE: 10
ttctccttca caccatcaag c                                              21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gaaaccgcct gcaaaggata a                                              21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gagggtctcg tggaaaagga t                                              21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccccacgcac ctagacaatg                                                20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gcctccatct gaagtcatct ca                                             22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
cttcagcaat gctactcgaa gc                                             22

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ggctactctt gtaggctccc t                                              21
```

```
<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
gaatctgcat gggcaacc                                                   18

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gaatcctggt acatctggga ac                                              22

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tcaagacgac ataggacacc t                                               21

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ggacattggc taaaacaaca gtg                                             23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gtggcacgat cctggtactg                                                 20

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gatgacctcg cctggagtgt a                                               21

<210> SEQ ID NO 23
<211> LENGTH: 24
<212> TYPE: DNA
<213> ORGANISM: Artificial Sequence
<220> FEATURE:
<223> OTHER INFORMATION: primer
```

<400> SEQUENCE: 23
gcagtcagtg tagcatgagt atga                                           24

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
catagctggg tggtgcttc                                                 19

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
aagcctttgt ttgacgctgt                                                20

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gccagcacat tcatctgtac c                                              21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gctcggtgac cctggtcttt                                                20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
aatgtgaggc gggtggaact                                                20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gttgtcggcc gagaacgaga a                                              21

<210> SEQ ID NO 30

```
<211> LENGTH: 20
<212> TYPE: DNA
<213> ORGANISM: Artificial Sequence
<220> FEATURE:
<223> OTHER INFORMATION: primer

<400> SEQUENCE: 30
cgggctgggc agttttttga                                                 20

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
ctgaacggac tcaagatggg t                                               21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
acctcctgag gatgacttct g                                               21

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
ttcaaggccg tgttaagga                                                  19

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
cctttggtgc taggcttgg                                                  19

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
cggaaaggct atcgaaggaa c                                               21

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
```

```
atttgagacc acactctttg agg                                          23

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
tctgcaggga aacagcaag                                               19

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
ccttgcgctc cttttcct                                                18

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ccagagaaga gggccttga                                               19

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
ccatccaggt atgaggagtc tt                                           22

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
ggatggaaag tcgaccacaa                                              20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
tggaagtcac gcctttcata                                              20

<210> SEQ ID NO 43
<211> LENGTH: 21
<212> TYPE: DNA
```

```
<213> ORGANISM: Artificial Sequence
<220> FEATURE:
<223> OTHER INFORMATION: primer

<400> SEQUENCE: 43
acggctttga ggagtacatg a                                              21

<210> SEQ ID NO 44
<211> LENGTH: 19
<212> TYPE: DNA
<213> ORGANISM: Artificial Sequence
<220> FEATURE:
<223> OTHER INFORMATION: primer

<400> SEQUENCE: 44
ctcggttttg accgtgatg                                                 19

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
cttcaaggat aagggcgaca                                                20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gacagattgt ggcgaattga                                                20

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
aagcattctg gatcttgcaa ct                                             22

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
gataggaaag ctgtagtcct ggtc                                           24

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cagagtgtgt cgtagagggg                                                20
```

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
gagctgcctc accatagaga ta                                              22

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
gtcagaccgg cacatgatta g                                               21

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
ggttggctac cttgtgaatg a                                               21

<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53
gctggacgta gcctgtgg                                                   18

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
cacgctcatc acgctgaa                                                   18

<210> SEQ ID NO 55
<211> LENGTH: 23
<212> TYPE: DNA
<213> ORGANISM: Artificial Sequence
<220> FEATURE:
<223> OTHER INFORMATION: primer

<400> SEQUENCE: 55
agaaatggag ctttgtctac gtc                                             23

<210> SEQ ID NO 56
<211> LENGTH: 22
<212> TYPE: DNA
<213> ORGANISM: Artificial Sequence
<220> FEATURE:

<223> OTHER INFORMATION: primer

<400> SEQUENCE: 56
cttcgagatg ggaatgtatg cc                                      22

<210> SEQ ID NO 57
<211> LENGTH: 22
<212> TYPE: DNA
<213> ORGANISM: Artificial Sequence
<220> FEATURE:
<223> OTHER INFORMATION: primer

<400> SEQUENCE: 57
tgacagactc aggaagaaac ca                                      22

<210> SEQ ID NO 58
<211> LENGTH: 21
<212> TYPE: DNA
<213> ORGANISM: Artificial Sequence
<220> FEATURE:
<223> OTHER INFORMATION: primer

<400> SEQUENCE: 58
gggaagctag caaacatcct t                                       21

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
gtgacaagct gcatgtggat                                         20

<210> SEQ ID NO 60
<211> LENGTH: 19
<212> TYPE: DNA
<213> ORGANISM: Artificial Sequence
<220> FEATURE:
<223> OTHER INFORMATION: primer

<400> SEQUENCE: 60
gtgaaatcct tgcccaggt                                          19

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
ccaggccgaa cctgtcaaa                                          19

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62
gcgtgctctt cattcgcag                                          19

```
<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
ccctcgcaaa cggaagttct                                                  20

<210> SEQ ID NO 64
<211> LENGTH: 23
<212> TYPE: DNA
<213> ORGANISM: Artificial Sequence
<220> FEATURE:
<223> OTHER INFORMATION: primer

<400> SEQUENCE: 64
gtcatccttc aaatcatcgg gaa                                              23

<210> SEQ ID NO 65
<211> LENGTH: 21
<212> TYPE: DNA
<213> ORGANISM: Artificial Sequence
<220> FEATURE:
<223> OTHER INFORMATION: primer

<400> SEQUENCE: 65
gaagagagcg atgcaggaaa c                                                21

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
gtccacatat tgggctggaa a                                                21

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
ggagatgctg gagatcatcg                                                  20

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
tccttatcct ggtccatctt ct                                               22

<210> SEQ ID NO 69
<211> LENGTH: 21
<212> TYPE: DNA
<213> ORGANISM: Artificial Sequence
<220> FEATURE:
<223> OTHER INFORMATION: primer
```

```
<400> SEQUENCE: 69
acaaaggacc aaagcctgag a                                              21

<210> SEQ ID NO 70
<211> LENGTH: 21
<212> TYPE: DNA
<213> ORGANISM: Artificial Sequence
<220> FEATURE:
<223> OTHER INFORMATION: primer

<400> SEQUENCE: 70
agcccatctt gttgcagtag a                                              21

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
cctgaatgag ctggtgagtg                                                20

<210> SEQ ID NO 72
<211> LENGTH: 19
<212> TYPE: DNA
<213> ORGANISM: Artificial Sequence
<220> FEATURE:
<223> OTHER INFORMATION: primer

<400> SEQUENCE: 72
gcagcctcaa cgtcgtact                                                 19

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
aagaccttga gtagttgccc a                                              21

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
tgctcgatcc tacgtttgca g                                              21

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
ctgctcccat gaatgacagt g                                              21

<210> SEQ ID NO 76
<211> LENGTH: 22
```

```
<212> TYPE: DNA
<213> ORGANISM: Artificial Sequence
<220> FEATURE:
<223> OTHER INFORMATION: primer

<400> SEQUENCE: 76
agttgcttct agcccaaaga ac                                              22

<210> SEQ ID NO 77
<211> LENGTH: 22
<212> TYPE: DNA
<213> ORGANISM: Artificial Sequence
<220> FEATURE:
<223> OTHER INFORMATION: primer

<400> SEQUENCE: 77
gaaactcatc ataggcattg ga                                              22

<210> SEQ ID NO 78
<211> LENGTH: 18
<212> TYPE: DNA
<213> ORGANISM: Artificial Sequence
<220> FEATURE:
<223> OTHER INFORMATION: primer

<400> SEQUENCE: 78
tggatcacgc agcagttg                                                   18

<210> SEQ ID NO 79
<211> LENGTH: 19
<212> TYPE: DNA
<213> ORGANISM: Artificial Sequence
<220> FEATURE:
<223> OTHER INFORMATION: primer

<400> SEQUENCE: 79
tcgtcttggc cttttggct                                                  19

<210> SEQ ID NO 80
<211> LENGTH: 22
<212> TYPE: DNA
<213> ORGANISM: Artificial Sequence
<220> FEATURE:
<223> OTHER INFORMATION: primer

<400> SEQUENCE: 80
tccaggtggt ctagcaggtt ct                                              22

<210> SEQ ID NO 81
<211> LENGTH: 21
<212> TYPE: DNA
<213> ORGANISM: Artificial Sequence
<220> FEATURE:
<223> OTHER INFORMATION: primer

<400> SEQUENCE: 81
gtcagtcgtt tgggctgtaa c                                               21

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
```

```
agacccaggc agagtcagaa                                                    20

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
gagcctgagg aacgacattg g                                                  21

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
ctgattggcg aatctgtcca g                                                  21

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
agggaggtcg agctgttctc                                                    20

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ggagtgttca ctaagcggtc a                                                  21

<210> SEQ ID NO 87
<211> LENGTH: 21
<212> TYPE: DNA
<213> ORGANISM: Artificial Sequence
<220> FEATURE:
<223> OTHER INFORMATION: primer

<400> SEQUENCE: 87
gtgtccacca actcacagat g                                                  21

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
ggaccattcc ttttgcagca t                                                  21

<210> SEQ ID NO 89
<211> LENGTH: 21
<212> TYPE: DNA
<213> ORGANISM: Artificial Sequence
```

```
<220> FEATURE:
<223> OTHER INFORMATION: primer

<400> SEQUENCE: 89
tcacaggttg gctggctcga c                                              21

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
gcatcgcctc ctccgtctgc                                                20

<210> SEQ ID NO 91
<211> LENGTH: 23
<212> TYPE: DNA
<213> ORGANISM: Artificial Sequence
<220> FEATURE:
<223> OTHER INFORMATION: primer

<400> SEQUENCE: 91
atgaagatcg ccatcacaat cac                                            23

<210> SEQ ID NO 92
<211> LENGTH: 22
<212> TYPE: DNA
<213> ORGANISM: Artificial Sequence
<220> FEATURE:
<223> OTHER INFORMATION: primer

<400> SEQUENCE: 92
ggatgccaca taaccagact ct                                             22

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
ggtcctgatg gagagtccac                                                20

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
gatgagaagg cgtttgaggt                                                20

<210> SEQ ID NO 95
<211> LENGTH: 19
<212> TYPE: DNA
<213> ORGANISM: Artificial Sequence
<220> FEATURE:
<223> OTHER INFORMATION: primer

<400> SEQUENCE: 95
ccatcagtgg tggcttcat                                                 19
```

```
<210> SEQ ID NO 96
<211> LENGTH: 18
<212> TYPE: DNA
<213> ORGANISM: Artificial Sequence
<220> FEATURE:
<223> OTHER INFORMATION: primer

<400> SEQUENCE: 96
gcggaggttt ccgatgat                                                 18

<210> SEQ ID NO 97
<211> LENGTH: 21
<212> TYPE: DNA
<213> ORGANISM: Artificial Sequence
<220> FEATURE:
<223> OTHER INFORMATION: primer

<400> SEQUENCE: 97
gaggcgctcc atgaagtaca c                                             21

<210> SEQ ID NO 98
<211> LENGTH: 21
<212> TYPE: DNA
<213> ORGANISM: Artificial Sequence
<220> FEATURE:
<223> OTHER INFORMATION: primer

<400> SEQUENCE: 98
ggatgcaaac ctccttctgt t                                             21

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
agagcggtga gtctaaggag t                                             21

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100 tgcccttcc gttgttgtcc                                                20

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
atgaagtcca aggccaaggt                                               20

<210> SEQ ID NO 102
<211> LENGTH: 21
<212> TYPE: DNA
<213> ORGANISM: Artificial Sequence
<220> FEATURE:
<223> OTHER INFORMATION: primer
```

<400> SEQUENCE: 102
catccacaaa gtcctcaaag g                                              21

<210> SEQ ID NO 103
<211> LENGTH: 21
<212> TYPE: DNA
<213> ORGANISM: Artificial Sequence
<220> FEATURE:
<223> OTHER INFORMATION: primer

<400> SEQUENCE: 103
gcaggtcctg taggtctttg a                                              21

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
cactcagagg gagacggaag                                                20

<210> SEQ ID NO 105
<211> LENGTH: 19
<212> TYPE: DNA
<213> ORGANISM: Artificial Sequence
<220> FEATURE:
<223> OTHER INFORMATION: primer

<400> SEQUENCE: 105
gagtgcggag gagacaacc                                                 19

<210> SEQ ID NO 106
<211> LENGTH: 18
<212> TYPE: DNA
<213> ORGANISM: Artificial Sequence
<220> FEATURE:
<223> OTHER INFORMATION: primer

<400> SEQUENCE: 106
agcctgttgg tccgtcat                                                  18

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
ggtcccataa cacgacaagg                                                20

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
atgctcagga gcctcaagtt                                                20

<210> SEQ ID NO 109

```
<211> LENGTH: 19
<212> TYPE: DNA
<213> ORGANISM: Artificial Sequence
<220> FEATURE:
<223> OTHER INFORMATION: primer

<400> SEQUENCE: 109
cagcagcaaa gcacacaga                                                    19

<210> SEQ ID NO 110
<211> LENGTH: 18
<212> TYPE: DNA
<213> ORGANISM: Artificial Sequence
<220> FEATURE:
<223> OTHER INFORMATION: primer

<400> SEQUENCE: 110
gcgctgttcc agaaggag                                                     18

<210> SEQ ID NO 111
<211> LENGTH: 20
<212> TYPE: DNA
<213> ORGANISM: Artificial Sequence
<220> FEATURE:
<223> OTHER INFORMATION: primer

<400> SEQUENCE: 111
aaaccgtgtg ctttgccatc                                                   20

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
caggatgatg aaggccgtgt                                                   20

<210> SEQ ID NO 113
<211> LENGTH: 24
<212> TYPE: DNA
<213> ORGANISM: Artificial Sequence
<220> FEATURE:
<223> OTHER INFORMATION: primer

<400> SEQUENCE: 113
actgacatga aggaagctaa ctgg                                              24

<210> SEQ ID NO 114
<211> LENGTH: 21
<212> TYPE: DNA
<213> ORGANISM: Artificial Sequence
<220> FEATURE:
<223> OTHER INFORMATION: primer

<400> SEQUENCE: 114
gccgaagaat tcctgaaagg c                                                 21

<210> SEQ ID NO 115
<211> LENGTH: 21
<212> TYPE: DNA
<213> ORGANISM: Artificial Sequence
<220> FEATURE:
<223> OTHER INFORMATION: primer

<400> SEQUENCE: 115
```
tgacatgaag gaagctggct g                                                    21

<210> SEQ ID NO 116
<211> LENGTH: 21
<212> TYPE: DNA
<213> ORGANISM: Artificial Sequence
<220> FEATURE:
<223> OTHER INFORMATION: primer

<400> SEQUENCE: 116
tgccgaagaa ttcctgaaag c                                                    21

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
gcacgtatgg cagcaagatg                                                      20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
ttcctgcagc tgactaacgg                                                      20

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
gacggaccgg atatgcagag                                                      20

<210> SEQ ID NO 120
<211> LENGTH: 20
<212> TYPE: DNA
<213> ORGANISM: Artificial Sequence
<220> FEATURE:
<223> OTHER INFORMATION: primer

<400> SEQUENCE: 120
ctgacctgac aagggtgtc                                                       20

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
ttgtcgctgt cttgcactct                                                      20

<210> SEQ ID NO 122
<211> LENGTH: 20
<212> TYPE: DNA

```
<213> ORGANISM: Artificial Sequence
<220> FEATURE:
<223> OTHER INFORMATION: primer

<400> SEQUENCE: 122
aatctgtcag gctggtctgc                                               20

<210> SEQ ID NO 123
<211> LENGTH: 20
<212> TYPE: DNA
<213> ORGANISM: Artificial Sequence
<220> FEATURE:
<223> OTHER INFORMATION: primer

<400> SEQUENCE: 123
acactgagga agaggagcaa                                               20

<210> SEQ ID NO 124
<211> LENGTH: 20
<212> TYPE: DNA
<213> ORGANISM: Artificial Sequence
<220> FEATURE:
<223> OTHER INFORMATION: primer

<400> SEQUENCE: 124
gatgtccagc tgcaggtact                                               20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
cacgtaccat gacggggtag                                               20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
ttttgccatt gccacagacg                                               20

<210> SEQ ID NO 127
<211> LENGTH: 21
<212> TYPE: DNA
<213> ORGANISM: Artificial Sequence
<220> FEATURE:
<223> OTHER INFORMATION: primer

<400> SEQUENCE: 127
tcgacctgta caagctgaac c                                             21

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
cctgcatgct gaagagggtc                                               20
```

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
ttgcatctct tcccttcggc					20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
cctggctcag gtagcacttc					20

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
ggtacgcttc ctctatcgcc					20

<210> SEQ ID NO 132
<211> LENGTH: 20
<212> TYPE: DNA
<213> ORGANISM: Artificial Sequence
<220> FEATURE:
<223> OTHER INFORMATION: primer

<400> SEQUENCE: 132
gagggatggc gtcttatggg					20

<210> SEQ ID NO 133
<211> LENGTH: 20
<212> TYPE: DNA
<213> ORGANISM: Artificial Sequence
<220> FEATURE:
<223> OTHER INFORMATION: primer

<400> SEQUENCE: 133
acagagctgg acctgcaaaa					20

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
agcaacaagc aatggcaagg					20

<210> SEQ ID NO 135
<211> LENGTH: 18
<212> TYPE: DNA
<213> ORGANISM: Artificial Sequence
<220> FEATURE:

<223> OTHER INFORMATION: primer

<400> SEQUENCE: 135
gagctacggg gtcgcttc                                                 18

<210> SEQ ID NO 136
<211> LENGTH: 18
<212> TYPE: DNA
<213> ORGANISM: Artificial Sequence
<220> FEATURE:
<223> OTHER INFORMATION: primer

<400> SEQUENCE: 136
gggaccccaa tctcacct                                                 18

<210> SEQ ID NO 137
<211> LENGTH: 20
<212> TYPE: DNA
<213> ORGANISM: Artificial Sequence
<220> FEATURE:
<223> OTHER INFORMATION: primer

<400> SEQUENCE: 137
aaagcagggc agacattgcg                                               20

<210> SEQ ID NO 138
<211> LENGTH: 22
<212> TYPE: DNA
<213> ORGANISM: Artificial Sequence
<220> FEATURE:
<223> OTHER INFORMATION: primer

<400> SEQUENCE: 138
ggatgtggct ctaggctatg tt                                            22

<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
atggcgtcac ttcgtcagag                                               20

<210> SEQ ID NO 140
<211> LENGTH: 20
<212> TYPE: DNA
<213> ORGANISM: Artificial Sequence
<220> FEATURE:
<223> OTHER INFORMATION: primer

<400> SEQUENCE: 140
aagctgagag tgaggaccca                                               20

<210> SEQ ID NO 141
<211> LENGTH: 21
<212> TYPE: DNA
<213> ORGANISM: Artificial Sequence
<220> FEATURE:
<223> OTHER INFORMATION: primer

<400> SEQUENCE: 141
tctgactgtg agagcaagca g                                             21

```
<210> SEQ ID NO 142
<211> LENGTH: 21
<212> TYPE: DNA
<213> ORGANISM: Artificial Sequence
<220> FEATURE:
<223> OTHER INFORMATION: primer

<400> SEQUENCE: 142
acctttaggt cccaggccat t                                              21

<210> SEQ ID NO 143
<211> LENGTH: 20
<212> TYPE: DNA
<213> ORGANISM: Artificial Sequence
<220> FEATURE:
<223> OTHER INFORMATION: primer

<400> SEQUENCE: 143
gttttgcacg gagcgatgag                                                20

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
tatggagcgc aagatggtca                                                20

<210> SEQ ID NO 145
<211> LENGTH: 21
<212> TYPE: DNA
<213> ORGANISM: Artificial Sequence
<220> FEATURE:
<223> OTHER INFORMATION: primer

<400> SEQUENCE: 145
cacagcactc ctctggacag t                                              21

<210> SEQ ID NO 146
<211> LENGTH: 20
<212> TYPE: DNA
<213> ORGANISM: Artificial Sequence
<220> FEATURE:
<223> OTHER INFORMATION: primer

<400> SEQUENCE: 146
tcagcttgag aggcagttgt                                                20

<210> SEQ ID NO 147
<211> LENGTH: 21
<212> TYPE: DNA
<213> ORGANISM: Artificial Sequence
<220> FEATURE:
<223> OTHER INFORMATION: primer

<400> SEQUENCE: 147
ataccagctg agcactttgg a                                              21

<210> SEQ ID NO 148
<211> LENGTH: 20
<212> TYPE: DNA
<213> ORGANISM: Artificial Sequence
<220> FEATURE:
<223> OTHER INFORMATION: primer
```

-continued

```
<400> SEQUENCE: 148
accttgccgt ctaccacttc                                              20

<210> SEQ ID NO 149
<211> LENGTH: 20
<212> TYPE: DNA
<213> ORGANISM: Artificial Sequence
<220> FEATURE:
<223> OTHER INFORMATION: primer

<400> SEQUENCE: 149
ggccagttca ctctgggaaa                                              20

<210> SEQ ID NO 150
<211> LENGTH: 19
<212> TYPE: DNA
<213> ORGANISM: Artificial Sequence
<220> FEATURE:
<223> OTHER INFORMATION: primer

<400> SEQUENCE: 150
aatgcattgg tcggtgggg                                               19

<210> SEQ ID NO 151
<211> LENGTH: 20
<212> TYPE: DNA
<213> ORGANISM: Artificial Sequence
<220> FEATURE:
<223> OTHER INFORMATION: primer

<400> SEQUENCE: 151
ccactttaac ccccgcttca                                              20

<210> SEQ ID NO 152
<211> LENGTH: 20
<212> TYPE: DNA
<213> ORGANISM: Artificial Sequence
<220> FEATURE:
<223> OTHER INFORMATION: primer

<400> SEQUENCE: 152
taggtgagca tcgttgaccg                                              20

<210> SEQ ID NO 153
<211> LENGTH: 20
<212> TYPE: DNA
<213> ORGANISM: Artificial Sequence
<220> FEATURE:
<223> OTHER INFORMATION: primer

<400> SEQUENCE: 153
tggaagctgc tgaaggttgt                                              20

<210> SEQ ID NO 154
<211> LENGTH: 20
<212> TYPE: DNA
<213> ORGANISM: Artificial Sequence
<220> FEATURE:
<223> OTHER INFORMATION: primer

<400> SEQUENCE: 154
ctccggagta atggccgatg                                              20

<210> SEQ ID NO 155
<211> LENGTH: 20
```

```
<212> TYPE: DNA
<213> ORGANISM: Artificial Sequence
<220> FEATURE:
<223> OTHER INFORMATION: primer

<400> SEQUENCE: 155
ctcatgaccc aggcagacaa                                             20

<210> SEQ ID NO 156
<211> LENGTH: 20
<212> TYPE: DNA
<213> ORGANISM: Artificial Sequence
<220> FEATURE:
<223> OTHER INFORMATION: primer

<400> SEQUENCE: 156
cccgtgggtg atgatgtagc                                             20

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
ctggaacgct cagatcaccc                                             20

<210> SEQ ID NO 158
<211> LENGTH: 21
<212> TYPE: DNA
<213> ORGANISM: Artificial Sequence
<220> FEATURE:
<223> OTHER INFORMATION: primer

<400> SEQUENCE: 158
ccaaccaacc aaagtggaca g                                           21

<210> SEQ ID NO 159
<211> LENGTH: 20
<212> TYPE: DNA
<213> ORGANISM: Artificial Sequence
<220> FEATURE:
<223> OTHER INFORMATION: primer

<400> SEQUENCE: 159
aacatggtct gtgctggctt                                             20

<210> SEQ ID NO 160
<211> LENGTH: 20
<212> TYPE: DNA
<213> ORGANISM: Artificial Sequence
<220> FEATURE:
<223> OTHER INFORMATION: primer

<400> SEQUENCE: 160
tctattgcag accacagggc                                             20

<210> SEQ ID NO 161
<211> LENGTH: 20
<212> TYPE: DNA
<213> ORGANISM: Artificial Sequence
<220> FEATURE:
<223> OTHER INFORMATION: primer

<400> SEQUENCE: 161
```

```
tgccaaccgt ggttattgtg                                              20

<210> SEQ ID NO 162
<211> LENGTH: 21
<212> TYPE: DNA
<213> ORGANISM: Artificial Sequence
<220> FEATURE:
<223> OTHER INFORMATION: primer

<400> SEQUENCE: 162
tgcctcacag ttttcgtcct t                                            21

<210> SEQ ID NO 163
<211> LENGTH: 21
<212> TYPE: DNA
<213> ORGANISM: Artificial Sequence
<220> FEATURE:
<223> OTHER INFORMATION: primer

<400> SEQUENCE: 163
cctctactgt caaccgtggt c                                            21

<210> SEQ ID NO 164
<211> LENGTH: 21
<212> TYPE: DNA
<213> ORGANISM: Artificial Sequence
<220> FEATURE:
<223> OTHER INFORMATION: primer

<400> SEQUENCE: 164
aaatgctgga tgctgcttgt c                                            21

<210> SEQ ID NO 165
<211> LENGTH: 20
<212> TYPE: DNA
<213> ORGANISM: Artificial Sequence
<220> FEATURE:
<223> OTHER INFORMATION: primer

<400> SEQUENCE: 165
cctccatgtc tgcacaccac                                              20

<210> SEQ ID NO 166
<211> LENGTH: 21
<212> TYPE: DNA
<213> ORGANISM: Artificial Sequence
<220> FEATURE:
<223> OTHER INFORMATION: primer

<400> SEQUENCE: 166
tcttggtgag ccatcatgct t                                            21

<210> SEQ ID NO 167
<211> LENGTH: 20
<212> TYPE: DNA
<213> ORGANISM: Artificial Sequence
<220> FEATURE:
<223> OTHER INFORMATION: primer

<400> SEQUENCE: 167
aatacttcca tgctcggggg                                              20

<210> SEQ ID NO 168
<211> LENGTH: 20
<212> TYPE: DNA
<213> ORGANISM: Artificial Sequence
```

-continued

<220> FEATURE:
<223> OTHER INFORMATION: primer

<400> SEQUENCE: 168
gctccatgtc ccgtgaactt                                               20

<210> SEQ ID NO 169
<211> LENGTH: 21
<212> TYPE: DNA
<213> ORGANISM: Artificial Sequence
<220> FEATURE:
<223> OTHER INFORMATION: primer

<400> SEQUENCE: 169
ggtatgaggg atgcctttgc t                                             21

<210> SEQ ID NO 170
<211> LENGTH: 21
<212> TYPE: DNA
<213> ORGANISM: Artificial Sequence
<220> FEATURE:
<223> OTHER INFORMATION: primer

<400> SEQUENCE: 170
atgtgtagca cagccttgtg a                                             21

<210> SEQ ID NO 171
<211> LENGTH: 21
<212> TYPE: DNA
<213> ORGANISM: Artificial Sequence
<220> FEATURE:
<223> OTHER INFORMATION: primer

<400> SEQUENCE: 171
cccccacgga gatggttata g                                             21

<210> SEQ ID NO 172
<211> LENGTH: 20
<212> TYPE: DNA
<213> ORGANISM: Artificial Sequence
<220> FEATURE:
<223> OTHER INFORMATION: primer

<400> SEQUENCE: 172
cccactgtca aggctccatc                                               20

<210> SEQ ID NO 173
<211> LENGTH: 20
<212> TYPE: DNA
<213> ORGANISM: Artificial Sequence
<220> FEATURE:
<223> OTHER INFORMATION: primer

<400> SEQUENCE: 173
agactgaggt ccttggtagc                                               20

<210> SEQ ID NO 174
<211> LENGTH: 21
<212> TYPE: DNA
<213> ORGANISM: Artificial Sequence
<220> FEATURE:
<223> OTHER INFORMATION: primer

<400> SEQUENCE: 174
aaggagaacg gtgatgagga c                                             21

PREDICTION DEVICE BASED ON INTER-ORGAN CROSS TALK SYSTEM

TECHNICAL FIELD

The present invention relates to an apparatus and a program for predicting the presence of a disease in a specific organ and/or the stage of the disease in a subject. The present invention also relates to an apparatus and a program for predicting the presence of a disease and/or the stage of the disease in each organ other than a specific organ in a subject affected with a disease in the specific organ.

BACKGROUND ART

Diseases include those in a state that can be reversibly treated and those in a state that cannot, i.e., those in an irreversible state. Early detection and treatment of abnormalities during a reversible state, or preventing such a state from occurring, is essential for health maintenance. Even in a reversible state, early detection of disease directly leads to milder treatment, a shorter treatment period, and better prognostic health. As in heart disease, brain disease, cancer, and diabetes, it is well known that abnormalities in one organ or tissue lead to a disease state in other organs (commonly called "complication"). In such diseases, it is essential to prevent abnormalities in one organ or tissue from causing disease in other organs or tissue at the earliest possible time.

In all animals, including humans, each organ and tissue form a functional network, rather than serving as separate parts, and quality control at the individual level is achieved. Transport of endocrine factors, such as hormones, by the vascular network throughout the whole body and coordinated adjustment of organ functions by the neural network are typical examples of an "inter-organ cross talk system," and systematized as physiology or endocrinology.

In the field of pharmaceuticals, the probability that a drug will be approved through the phase III clinical trial from the new drug discovery phase is currently about 1.6%. In other words, 98.4% of drugs developed as candidates in the discovery phase do not see the light of day. This is mainly because of, for example, the following: cases in which no effect is observed in a living organism (animal model) when a drug confirmed to be effective at the cellular level is administered to the living organism; cases in which the effect of a drug is observed in cells and an animal model, but the drug exhibits no notable effect in humans; and cases in which a test drug cannot be used because of a strong side effect (or side effects), although the effect of the test drug is observed in a living organism (animal model and human). Thus, "drug revival" or "discovering other new uses" (commonly called "drug repositioning") of a large number of drugs that drop out during the period from research and development to practical use is believed to greatly contribute to medical and economic development.

More than half of the drugs selected in the discovery phase exhibit effects in cells. One of the causes of dropout of drugs in more advanced phases is the "inter-organ cross talk system network," which is uniquely present in living organisms. Each organ constructed with cells having a variety of functions forms the inter-organ cross talk system in vivo, thereby establishing homeostasis and physiological functions in the whole individual. Accordingly, if an abnormality occurs in one organ (disease), the abnormal signal is propagated to other organs via the inter-organ cross talk system, and the entire network of the inter-organ cross talk system changes; even if only a kind of cells in the organ that first showed an abnormality are targeted with a drug (PTL 1 to 8), the entire network of the inter-organ cross talk system cannot be returned to its original state.

CITATION LIST

Patent Literature

PTL 1: JP2005-508505A
PTL 2: JP2008-518626A
PTL 3: JP2002-516107A
PTL 4: JP2005-518810A
PTL 5: JP2007-521799A
PTL 6: JP2013-538565A
PTL 7: JP2013-541323A
PTL 8: WO2003/085548

SUMMARY OF INVENTION

Technical Problem

An object of the present invention is to provide an apparatus and a program for detecting, from cells or tissue of one organ, a disease in another organ at the earliest possible time. More specifically, an object of the present invention is to predict the presence of a disease in a specific organ and/or the stage of the disease from an inter-organ cross talk indicator derived from one or more organs other than the specific organ. Another object of the present invention is to predict the presence of a disease and/or the stage of the disease in each of one or more organs other than a specific organ from the disease state of the specific organ.

Further, another object of the present invention is to predict the effect of a test substance from an inter-organ cross talk indicator.

Solution to Problem

The present inventor focused on the inter-organ cross talk system to achieve the above objects. The inventor conducted extensive research and found that it is possible to provide an apparatus and a program for diagnosing, from measurement of the state of an organ, the current state of one or more other organs and for predicting a future state by using the inter-organ cross talk system.

Further, the inventor found that the efficacy and side effect (or side effects) of a test substance can be predicted comprehensively and quantitatively by measuring and evaluating an inter-organ cross talk indicator in an individual to which the test substance has been administered.

The present invention has been accomplished based on these findings and includes the following embodiments.
Item 1
An apparatus for predicting the presence of a disease in a specific organ (hereinafter referred to as "specific disease") and/or the stage of the specific disease in a subject, the apparatus comprising the following computation means:

a means for obtaining data of the subject regarding an inter-organ cross talk indicator in each of one or more organs other than the specific organ, the inter-organ cross talk indicator being derived from cells or tissue originating from each of the one or more organs;

a means for calculating, by comparing the data of the subject obtained by the subject data obtaining means with predetermined standard data 1 of the corresponding inter-organ cross talk indicator, similarity of patterns of the inter-organ cross talk indicators between the data of the subject and the standard data 1; and a means for predicting the presence of the specific disease and/or the stage of the specific disease by using, as a measure, the similarity of patterns of the inter-organ cross talk indicators calculated by the pattern similarity calculation means, wherein the data of the subject is a pattern of the inter-organ cross talk indicator representing a relationship between an amount of the inter-organ cross talk indicator in the organ other than the specific organ of the subject (hereinafter referred to as "subject amount") and an amount of the corresponding inter-organ cross talk indicator in the same organ as the organ other than the specific organ in a negative control (or negative controls) without the specific disease (hereinafter referred to as "negative control amount"), and the standard data 1 includes patterns of inter-organ cross talk indicators, each of the patterns being derived from a predetermined relationship between an amount of an inter-organ cross talk indicator in the organ other than the specific organ in a positive control (or positive controls) affected with the specific disease (hereinafter referred to as "positive control amount 1") and an amount of the corresponding inter-organ cross talk indicator in the same organ as the organ other than the specific organ in the negative control (or negative controls) without the specific disease (hereinafter referred to as "negative control amount 1").

Item 1-1

An apparatus for predicting the presence of a disease in a specific organ (hereinafter referred to as "specific disease") and/or the stage of the specific disease in a subject, the apparatus comprising the following computation means:

a means for obtaining data A of the subject regarding an inter-organ cross talk indicator in each of one or more organs other than the specific organ, the inter-organ cross talk indicator being derived from cells or tissue originating from each of the one or more organs;

a means for calculating, by comparing the data A of the subject obtained by the subject data obtaining means with predetermined standard data 1*a* of the corresponding inter-organ cross talk indicator, similarity of patterns of the inter-organ cross talk indicators between the data A of the subject and the standard data 1*a*; and a means for predicting the presence of the specific disease and/or the stage of the specific disease by using, as a measure, the similarity of patterns of the inter-organ cross talk indicators calculated by the pattern similarity calculation means, wherein the inter-organ cross talk indicator comprises RNA, the data A of the subject is a pattern of expression of the RNA indicated by a ratio between an expression level of the RNA in the organ other than the specific organ of the subject and an expression level of the corresponding RNA in the same organ as the organ other than the specific organ in a negative control (or negative controls) without the specific disease, and the standard data 1*a* includes patterns of expression of the RNA, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in the negative control (or negative controls) without the specific disease.

Item 1-2

An apparatus for predicting the presence of a disease in a specific organ (hereinafter referred to as "specific disease") and/or the stage of the specific disease in a subject, the apparatus comprising the following computation means:

a means for obtaining data B of the subject regarding an inter-organ cross talk indicator in each of one or more organs other than the specific organ, the inter-organ cross talk indicator being derived from cells or tissue originating from each of the one or more organs;

a means for calculating, by comparing the data B of the subject obtained by the subject data obtaining means with predetermined standard data 1*b* of the corresponding inter-organ cross talk indicator, similarity of patterns of the inter-organ cross talk indicators between the data B of the subject and the standard data 1*b*; and a means for predicting the presence of the specific disease and/or the stage of the specific disease by using, as a measure, the similarity of patterns of the inter-organ cross talk indicators calculated by the pattern similarity calculation means, wherein the inter-organ cross talk indicator comprises metabolites, the data B of the subject is a pattern of presence of the metabolites indicated by ratios between amounts of the metabolites in the organ other than the specific organ of the subject and amounts of the corresponding metabolites in the same organ as the organ other than the specific organ in a negative control (or negative controls) without the specific disease, and the standard data 1*b* includes patterns of presence of the metabolites, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in the negative control (or negative controls) without the specific disease.

Item 1-3

The apparatus according to any one of Items 1, 1-1, and 1-2, wherein the one or more organs other than the specific organ are one or more organs other than blood.

Item 2

The apparatus according to Item 1, wherein the inter-organ cross talk indicator comprises RNA.

Item 3

The apparatus according to Item 1 or 2, wherein the inter-organ cross talk indicator comprises metabolites.

Item 4

The apparatus according to any one of Items 1, 2, and 3, wherein the relationship between the positive control (or positive controls) amount 1 and the negative control amount 1 in the standard data 1 set forth in Item 1 is a ratio between the positive control amount 1 and the negative control amount 1.

Item 4-1

The apparatus according to any one of Items 1, 2, 3, and 4, wherein the relationship between the subject amount and the negative control amount in the data of the subject set forth in Item 1 is a ratio between the subject amount and the negative control amount.

Item 5

The apparatus according to any one of Items 1, 1-1, 1-2, 2 to 4, and 4-1, wherein the specific organ is the heart, and the specific disease is myocardial infarction.

Item 5-1

The apparatus according to Item 5, wherein, when the inter-organ cross talk indicator comprises RNA, the RNA is expressed from genes described in FIG. 25 or 26.

Item 5-2

The apparatus according to Item 5, wherein, when the inter-organ cross talk indicator comprises metabolites, the metabolites are listed in FIG. 27.

Item 6

The apparatus according to any one of Items 1, 1-1, 1-2, 2 to 4, and 4-1, wherein the specific organ is the brain, and the specific disease is dementia.

Item 6-1

The apparatus according to Item 6, wherein, when the inter-organ cross talk indicator comprises RNA, the RNA is expressed from genes listed in FIG. 25 or 26.

Item 6-2

The apparatus according to Item 6, wherein, when the inter-organ cross talk indicator comprises metabolites, the metabolites are listed in FIG. 27.

Item 7

The apparatus according to any one of Items 1, 1-1, 1-2, 2 to 4, and 4-1, wherein the specific disease is a tumor.

Item 7-1

The apparatus according to Item 7, wherein, when the inter-organ cross talk indicator comprises RNA, the RNA is expressed from genes listed in FIG. 25 or 26.

Item 7-2

The apparatus according to Item 7, wherein, when the inter-organ cross talk indicator comprises metabolites, the metabolites are listed in FIG. 27.

Item 8

A program that, when executed by a computer, causes the computer to carry out the following processing to predict the presence of a disease in a specific organ (hereinafter referred to as "specific disease") and/or the stage of the specific disease in a subject:

processing of obtaining data of the subject regarding an inter-organ cross talk indicator in each of one or more organs other than the specific organ, the inter-organ cross talk indicator being derived from cells or tissue originating from each of the one or more organs;

processing of calculating, by comparing the data of the subject obtained by the subject data obtaining processing with predetermined standard data 1 of the corresponding inter-organ cross talk indicator, similarity of patterns of the inter-organ cross talk indicators between the data of the subject and the standard data 1; and processing of predicting the presence of the specific disease and/or the stage of the specific disease by using, as a measure, the similarity of patterns of the inter-organ cross talk indicators calculated by the pattern similarity calculation processing, wherein the data of the subject is a pattern of the inter-organ cross talk indicator representing a relationship between an amount of the inter-organ cross talk indicator in the organ other than the specific organ of the subject (hereinafter referred to as "subject amount") and an amount of the corresponding inter-organ cross talk indicator in the same organ as the organ other than the specific organ in a negative control (or negative controls) without the specific disease (hereinafter referred to as "negative control amount"), and the standard data 1 includes patterns of inter-organ cross talk indicators, each of the patterns being derived from a predetermined relationship between an amount of an inter-organ cross talk indicator in the organ other than the specific organ in a positive control (or positive controls) affected with the specific disease (hereinafter referred to as "positive control amount 1") and an amount of the corresponding inter-organ cross talk indicator in the same organ as the organ other than the specific organ in the negative control (or negative controls) without the specific disease (hereinafter referred to as "negative control amount 1").

Item 8-1

A program that, when executed by a computer, causes the computer to carry out the following processing to predict the presence of a disease in a specific organ (hereinafter referred to as "specific disease") and/or the stage of the specific disease in a subject:

processing of obtaining data A of the subject regarding an inter-organ cross talk indicator in each of one or more organs other than the specific organ, the inter-organ cross talk indicator being derived from cells or tissue originating from each of the one or more organs;

processing of calculating, by comparing the data A of the subject obtained by the subject data obtaining processing with predetermined standard data 1a of the corresponding inter-organ cross talk indicator, similarity of patterns of the inter-organ cross talk indicators between the data A of the subject and the standard data 1a; and processing of predicting the presence of the specific disease and/or the stage of the specific disease by using, as a measure, the similarity of patterns of the inter-organ cross talk indicators calculated by the pattern similarity calculation processing, wherein the inter-organ cross talk indicator comprises RNA, the data A of the subject is a pattern of expression of the RNA indicated by a ratio between an expression level of the RNA in the organ other than the specific organ of the subject and an expression level of the corresponding RNA in the same organ as the organ other than the specific organ in a negative control (or negative controls) without the specific disease, and the standard data 1a includes patterns of expression of the RNA, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in the negative control (or negative controls) without the specific disease.

Item 8-2

A program that, when executed by a computer, causes the computer to carry out the following processing to predict the presence of a disease in a specific organ (hereinafter referred to as "specific disease") and/or the stage of the specific disease in a subject:

processing of obtaining data B of the subject regarding an inter-organ cross talk indicator in each of one or more organs other than the specific organ, the inter-organ cross talk indicator being derived from cells or tissue originating from each of the one or more organs;

processing of calculating, by comparing the data B of the subject obtained by the subject data obtaining processing with predetermined standard data 1b of the corresponding inter-organ cross talk indicator, similarity of patterns of the inter-organ cross talk indicators between the data B of the subject and the standard data 1b; and processing of predicting the presence of the specific disease and/or the stage of the specific disease by using, as a measure, the similarity of patterns of the inter-organ cross talk indicators calculated by the pattern similarity calculation processing, wherein the inter-organ cross talk indicator comprises metabolites, the data B of the subject is a pattern of presence of the metabolites indicated by ratios between amounts of the metabolites in the organ other than the specific organ of the subject and amounts of the corresponding metabolites in the same organ as the organ other than the specific organ in a negative control (or negative controls) without the specific disease, and the standard data 1b includes patterns of presence of the metabolites, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in the negative control (or negative controls) without the specific disease.

Item 8-3

A program for causing a computer to function as the subject data obtaining means, the pattern similarity calculation means, and the prediction means according to any one of Items 1 to 4 and 4-1.

Item 8-4

The program according to any one of Items 8, 8-1, 8-2, and 8-3, wherein the one or more organs other than the specific organ are one or more organs other than blood.

Item 9

The program according to Item 8, wherein the inter-organ cross talk indicator comprises RNA.

Item 10

The program according to Item 8 or 9, wherein the inter-organ cross talk indicator comprises metabolites.

Item 11

The program according to any one of Items 8, 9, and 10, wherein the relationship between the positive control amount 1 and the negative control amount 1 in the standard data 1 set forth in Item 8 is a ratio between the positive control amount and the negative control amount.

Item 11-1

The program according to any one of Items 8, 9, 10, and 11, wherein the relationship between the subject amount and the negative control amount in the data of the subject set forth in Item 8 is a ratio between the subject amount and the negative control amount.

Item 12

The program according to any one of Items 8, 8-1, 8-2, 9 to 11, and 11-1, wherein the specific organ is the heart, and the specific disease is myocardial infarction.

Item 12-1

The program according to Item 12, wherein, when the inter-organ cross talk indicator comprises RNA, the RNA is RNA expressed from genes listed in FIG. 25 or 26.

Item 12-2

The program according to Item 12, wherein, when the inter-organ cross talk indicator comprises metabolites, the metabolites are listed in FIG. 27.

Item 13

The program according to any one of Items 8, 8-1, 8-2, 9 to 11, and 11-1, wherein the specific organ is the brain, and the specific disease is dementia.

Item 13-1

The program according to Item 13, wherein, when the inter-organ cross talk indicator comprises RNA, the RNA is expressed from genes listed in FIG. 25 or 26.

Item 13-2

The program according to Item 13, wherein, when the inter-organ cross talk indicator comprises metabolites, the metabolites are listed in FIG. 27.

Item 14

The program according to any one of Items 8, 8-1, 8-2, 9 to 11, and 11-1, wherein the specific disease is a tumor.

Item 14-1

The program according to Item 14, wherein, when the inter-organ cross talk indicator comprises RNA, the RNA is RNA expressed from genes listed in FIG. 25 or 26.

Item 14-2

The program according to Item 14, wherein, when the inter-organ cross talk indicator comprises metabolites, the metabolites are listed in FIG. 27.

Item 15

A method for predicting the presence of a disease in a specific organ (hereinafter referred to as "specific disease") and/or the stage of the specific disease in a subject, the method comprising the steps of:

(1) calculating, by comparing data of the subject regarding an inter-organ cross talk indicator in each of one or more organs other than the specific organ derived from cells or tissue originating from each of the one or more organs with predetermined standard data 1 of the corresponding inter-organ cross talk indicator, similarity of patterns of the inter-organ cross talk indicators between the data of the subject and the standard data 1; and (2) determining that the subject has a specific disease corresponding to the standard data 1 when it is determined from the similarity of patterns of the inter-organ cross talk indicators calculated in step (1) that both patterns are similar, and/or determining that the subject is in a stage of a specific disease corresponding to the standard data 1 when it is determined from the similarity of patterns of the inter-organ cross talk indicators calculated in step (1) that both patterns are similar, wherein the data of the subject is a pattern of the inter-organ cross talk indicator representing a relationship between an amount of the inter-organ cross talk indicator in the organ other than the specific organ of the subject (hereinafter referred to as "subject amount") and an amount of the corresponding inter-organ cross talk indicator in the same organ as the organ other than the specific organ in a negative control (or negative controls) without the specific disease (hereinafter referred to as "negative control amount"), and the standard data 1 includes patterns of inter-organ cross talk indicators, each of the patterns being derived from a predetermined relationship between an amount of an inter-organ cross talk indicator in the organ other than the specific organ in a positive control (or positive controls) affected with the specific disease (hereinafter referred to as "positive control amount 1") and an amount of the corresponding inter-organ cross talk indicator in the same organ as the organ other than the specific organ in the negative control (or negative controls) without the specific disease (hereinafter referred to as "negative control amount 1").

Item 15-1

A method for predicting the presence of a disease in a specific organ (hereinafter referred to as "specific disease") and/or the stage of the specific disease in a subject, the method comprising the steps of:

(a) calculating, by comparing data A of the subject regarding an inter-organ cross talk indicator in each of one or more organs other than the specific organ derived from cells or tissue originating from each of the one or more organs with predetermined standard data 1a of the corresponding inter-organ cross talk indicator, similarity of patterns of the inter-organ cross talk indicators between the data A of the subject and the standard data 1a; and (b) determining that the subject has a specific disease corresponding to the standard data 1a when it is determined from the similarity of patterns of the inter-organ cross talk indicators calculated in step (a) that both patterns are similar, and/or determining that the subject is in a stage of a specific disease corresponding to the standard data 1a when it is determined from the similarity of patterns of the inter-organ cross talk indicators calculated in step (a) that both patterns are similar, wherein the inter-organ cross talk indicator comprises RNA, the data A of the subject is a pattern of expression of the RNA indicated by a ratio between an expression level of the RNA in the organ other than the specific organ of the subject and an expression level of the corresponding RNA in the same organ as the organ other than the specific organ in a negative control (or negative controls) without the specific disease, and the standard data 1a includes patterns of expression of the RNA, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in the negative control (or negative controls) without the specific disease.

Item 15-2

A method for predicting the presence of a disease in a specific organ (hereinafter referred to as "specific disease") and/or the stage of the specific disease in a subject, the method comprising the steps of:

(a) calculating, by comparing data B of the subject regarding an inter-organ cross talk indicator in each of one or more organs other than the specific organ derived from cells or tissue originating from each of the one or more organs with predetermined standard data 1b of the corresponding inter-organ cross talk indicator, similarity of patterns of the inter-organ cross talk indicators between the data B of the subject and the standard data 1b; and (b) determining that the subject has a specific disease corresponding to the standard data 1b when it is determined from the similarity of patterns of the inter-organ cross talk indicators calculated in step (a) that both patterns are similar, and/or determining that the subject is in a stage cf a specific disease corresponding to the standard data 1b when it is determined from the similarity of patterns of the inter-organ cross talk indicators calculated in step (a) that both patterns are similar, wherein the inter-organ cross talk indicator comprises metabolites, the data B of the subject is a pattern of presence of the metabolites indicated by ratios between amounts of the metabolites in the organ other than the specific organ of the subject and amounts of the corresponding metabolites in the same organ as the organ other than the specific organ in a negative control (or negative controls) without the specific disease, and the standard data 1b includes patterns of presence of the metabolites, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in the negative control (or negative controls) without the specific disease.

Item 15-3

The method according to any one of Items 15, 15-1, and 15-2, wherein the one or more organs other than the specific organ are one or more organs other than blood.

Item 16

The method according to Item 15, further comprising, before step (1), the steps of:

(i) extracting the inter-organ cross talk indicator from the cells or tissue originating from each of the one or more organs other than the specific organ of the subject;

(ii) identifying and quantifying the inter-organ cross talk indicator extracted in step (i); and (iii) determining the data of the subject regarding the inter-organ cross talk indicator from the amount of the inter-organ cross talk indicator quantified in step (ii).

Item 16-1

The method according to Item 15-1, further comprising, before step (1), the steps of:

(i) extracting the RNA from the cells or tissue originating from each of the one or more organs other than the specific organ of the subject;

(ii) identifying expressed genes and quantifying expression levels of the genes from expression of the RNA extracted in step (i); and (iii) determining the data A of the subject regarding the genes from the expression level of the RNA quantified in step (ii).

Item 16-2

The method according to Item 15-2, further comprising, before step (1), the steps of:

(i) extracting the metabolites from the cells or tissue originating from each of the one or more organs other than the specific organ of the subject;

(ii) identifying the metabolites extracted in step (i) and quantifying amounts of the metabolites extracted in step (i); and (iii) determining the data B of the subject regarding the metabolites from the amounts of the metabolites quantified in step (ii).

Item 17

The method according to Item 15 or 16, wherein the inter-organ cross talk indicator comprises RNA.

Item 18

The method according to any one of Items 15, 16, and 17, wherein the inter-organ cross talk indicator comprises metabolites.

Item 19

The method according to any one of Items 15, 16, 17, and 18, wherein the relationship between the positive control amount 1 and the negative control amount 1 in the standard data 1 set forth in Item 15 is a ratio between the positive control amount 1 and the negative control amount 1.

Item 19-1

The method according to any one of Items 15, 16, 17, 18, and 19, wherein the relationship between the subject amount and the negative control amount in the data of the subject set forth in Item 15 is a ratio between the subject amount and the negative control amount.

Item 20

The method according to any one of Items 15, 15-1, 15-2, 16 to 19, and 19-1, wherein the specific organ is the heart, and the specific disease is myocardial infarction.

Item 20-1

The method according to Item 20, wherein, when the inter-organ cross talk indicator comprises RNA, the RNA is expressed from genes listed in FIG. 25 or 26.

Item 20-2

The method according to Item 20, wherein, when the inter-organ cross talk indicator comprises metabolites, the metabolites are listed in FIG. 27.

Item 21

The method according to any one of Items 15, 15-1, 15-2, 16 to 19, and 19-1, wherein the specific organ is the brain, and the specific disease is dementia.

Item 21-1

The method according to Item 21, wherein, when the inter-organ cross talk indicator comprises RNA, the RNA is expressed from genes listed in FIG. 25 or 26.

Item 21-2

The method according to Item 21, wherein, when the inter-organ cross talk indicator comprises metabolites, the metabolites are metabolites listed in FIG. 27.

Item 22

The method according to any one of Items 15, 15-1, 15-2, 16 to 19, and 19-1, wherein the specific disease is a tumor.

Item 22-1

The method according to Item 22, wherein, when the inter-organ cross talk indicator comprises RNA, the RNA is expressed from genes listed in FIG. 25 or 26.

Item 22-2

The method according to Item 22, wherein, when the inter-organ cross talk indicator comprises metabolites, the metabolites are listed in FIG. 27.

Item 23

A method for generating standard data 1 of patterns of inter-organ cross talk indicators for use in prediction of the presence of a disease in a specific organ (hereinafter referred to as "specific disease") and/or the stage of the specific disease in a subject, the method comprising the steps of:

(A) obtaining information about an amount of an inter-organ cross talk indicator in cells or tissue originating from each of one or more organs other than the specific organ of a positive control (or positive controls) as a gold standard for each stage of the specific disease;

(B) obtaining information about an amount of the inter-organ cross talk indicator in cells or tissue originating from each of the one or more organs other than the specific organ of a negative control (or negative controls) as a gold standard;

(C) determining patterns of inter-organ cross talk indicators, each of the patterns being determined from a relationship (preferably a ratio) between the amount of the inter-organ cross talk indicator in the organ other than the specific organ of the positive control (or positive controls) affected with the specific disease obtained in step (A) and the amount of the corresponding inter-organ cross talk indicator in the same organ as the organ other than the specific organ in the negative control (or negative controls) without the specific disease obtained in step (B); and (D) associating the patterns of the inter-organ cross talk indicators with the corresponding stages of the specific disease.

Item 23-1

The method according to Item 23, wherein step (A) comprises the steps of:

extracting an inter-organ cross talk indicator from cells or tissue originating from each of one or more organs other than the specific organ of a positive control (or positive controls) as a gold standard for each stage of the specific disease; and identifying and quantifying the inter-organ cross talk indicator, and step (B) comprises the steps of:

extracting the inter-organ cross talk indicator from cells or tissue originating from each of the one or more organs other than the specific organ of a negative control (or negative controls) as a gold standard; and identifying and quantifying the inter-organ cross talk indicator.

Item 23-2

The method according to Item 23 or 23-1, wherein the inter-organ cross talk indicator comprises RNA.

Item 23-3

The method according to Item 23 or 23-1, wherein the inter-organ cross talk indicator comprises metabolites.

Item 23-4

The method according to any one of Items 23, 23-1, 23-2, and 23-3, wherein the specific organ is the heart, and the specific disease is myocardial infarction.

Item 23-4-1

The method according to Item 23-4, wherein, when the inter-organ cross talk indicator comprises RNA, the RNA is expressed from genes listed in FIG. 25 or 26.

Item 23-4-2

The method according to Item 23-4, wherein, when the inter-organ cross talk indicator comprises metabolites, the metabolites are listed in FIG. 27.

Item 23-5

The method according to any one of Items 23, 23-1, 23-2, and 23-3, wherein the specific organ is the brain, and the specific disease is dementia.

Item 23-5-1

The method according to Item 23-5, wherein, when the inter-organ cross talk indicator comprises RNA, the RNA is expressed from genes listed in FIG. 25 or 26.

Item 23-5-2

The method according to Item 23-5, wherein, when the inter-organ cross talk indicator comprises metabolites, the metabolites are listed in FIG. 27.

Item 23-6

The method according to any one of Items 23, 23-1, 23-2, and 23-3, wherein the specific disease is a tumor.

Item 23-6-1

The method according to Item 23-6, wherein, when the inter-organ cross talk indicator comprises RNA, the RNA is expressed from genes listed in FIG. 25 or 26.

Item 23-6-2

The method according to Item 23-6, wherein, when the inter-organ cross talk indicator comprises metabolites, the metabolites are listed in FIG. 27.

Item 24

Standard data 1 of patterns of inter-organ cross talk indicators generated by the method according to any one of Items 23, 23-1, 23-2, and 23-3, for use in prediction of the presence of a disease in a specific organ and/or the stage of the disease in a subject.

Item 25

An apparatus for predicting the presence of a disease and/or the stage of the disease in each of one or more organs other than a specific organ in a subject affected with a disease in the specific organ, the apparatus comprising the following computation means:

a means for obtaining information about a stage of the disease in the specific organ (hereinafter referred to as "specific disease") in the subject;

a means for checking the information about the stage obtained by the stage information obtaining means against standard data 2;

a means for extracting a pattern of an inter-organ cross talk indicator in each of one or more organs other than the specific organ in the subject based on the results obtained by the stage information checking means; and a means for predicting the presence of a disease and/or the stage of the disease in each of the one or more organs other than the specific organ by using, as a measure, the pattern of the inter-organ cross talk indicator obtained by the pattern extraction means;

wherein the standard data 2 includes patterns of inter-organ cross talk indicators predetermined for each stage of the specific disease, each of the patterns being derived from a predetermined relationship between an amount of an inter-organ cross talk indicator in the organ other than the specific organ in a positive control (or positive controls) affected with the specific disease (hereinafter referred to as "positive control amount 2") and an amount of the corresponding inter-organ cross talk indicator in the same organ as the organ other than the specific organ in a negative control (or negative controls) without the specific disease (hereinafter referred to as "negative control amount 2").

Item 25-1

An apparatus for predicting the presence of a disease and/or the stage of the disease in each of one or more organs other than a specific organ in a subject affected with a disease in the specific organ, the apparatus comprising the following computation means:

a means for obtaining information about a stage of the disease in the specific organ (hereinafter referred to as "specific disease") in the subject;

a means for checking the information about the stage obtained by the stage information obtaining means against standard data 2a;

a means for extracting a pattern of an inter-organ cross talk indicator in each of one or more organs other than the specific organ in the subject based on the results obtained by the stage information checking means; and a means for predicting the presence of a disease and/or the stage of the disease in each of the one or more organs other than the specific organ by using, as a measure, the pattern of the inter-organ cross talk indicator obtained by the pattern extraction means;

wherein the inter-organ cross talk indicator comprises RNA, and the standard data 2a includes patterns of expression of the RNA predetermined for each stage of the specific disease, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in a negative control (or negative controls) without the specific disease.

Item 25-2

An apparatus for predicting the presence of a disease and/or the stage of the disease in each of one or more organs other than a specific organ in a subject affected with a disease in the specific organ, the apparatus comprising the following computation means:

a means for obtaining information about a stage of the disease in the specific organ (hereinafter referred to as "specific disease") in the subject;

a means for checking the information about the stage obtained by the stage information obtaining means against standard data 2b;

a means for extracting a pattern of an inter-organ cross talk indicator in each of one or more organs other than the specific organ in the subject based on the results obtained by the stage information checking means; and a means for predicting the presence of a disease and/or the stage of the disease in each of the one or more organs other than the specific organ by using, as a measure, the pattern of the inter-organ cross talk indicator obtained by the pattern extraction means;

wherein the inter-organ cross talk indicator comprises metabolites, and the standard data 2b includes patterns of presence of the metabolites predetermined for each stage of the specific disease, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in a negative control (or negative controls) without the specific disease.

Item 26

The apparatus according to Item 25, wherein the inter-organ cross talk indicator comprises RNA.

Item 27

The apparatus according to Item 25 or 26, wherein the inter-organ cross talk indicator comprises metabolites.

Item 28

The apparatus according to any one of Items 25 to 27, wherein the relationship between the positive control amount 2 and the negative control amount 2 in the standard data 2 set forth in Item 25 is a ratio between the positive control amount 2 and the negative control amount 2.

Item 29

The apparatus according to any one of Items 25, 25-1, 25-2, and 26 to 28, wherein the specific organ is the heart, and the specific disease is myocardial infarction.

Item 29-1

The apparatus according to Item 29, wherein, when the inter-organ cross talk indicator comprises RNA, the RNA is expressed from genes listed in FIG. 25 or 26.

Item 29-2

The apparatus according to Item 29, wherein, when the inter-organ cross talk indicator comprises metabolites, the metabolites are listed in FIG. 27.

Item 30

The apparatus according to any one of Items 25, 25-1, 25-2, and 26 to 28, wherein the specific organ is the brain, and the specific disease is dementia.

Item 30-1

The apparatus according to Item 30, wherein, when the inter-organ cross talk indicator comprises RNA, the RNA is expressed from genes listed in FIG. 25 or 26.

Item 30-2

The apparatus according to Item 30, wherein, when the inter-organ cross talk indicator comprises metabolites, the metabolites are listed in FIG. 27.

Item 31

The apparatus according to any one of Items 25, 25-1, 25-2, and 26 to 28, wherein the specific disease is a tumor.

Item 31-1
 The apparatus according to Item 31, wherein, when the inter-organ cross talk indicator comprises RNA, the RNA is expressed from genes listed in FIG. 25 or 26.
Item 31-2
 The apparatus according to Item 31, wherein, when the inter-organ cross talk indicator comprises metabolites, the metabolites are listed in FIG. 27.
Item 32
 A program that, when executed by a computer, causes the computer to carry out the following processing to predict the presence of a disease and/or the stage of the disease in each of one or more organs other than a specific organ in a subject affected with a disease in the specific organ:
 processing of obtaining information about a stage of the disease in the specific organ (hereinafter referred to as "specific disease") in the subject;
 processing of checking the information about the stage obtained by the stage information obtaining processing against standard data 2;
 processing of extracting a pattern of an inter-organ cross talk indicator in each of one or more organs other than the specific organ in the subject based on the results obtained by the stage information checking processing; and
 processing of predicting the presence of a disease and/or the stage of the disease in each of the one or more organs other than the specific organ by using, as a measure, the pattern of the inter-organ cross talk indicator obtained by the pattern extraction processing,
 wherein the standard data 2 includes patterns of inter-organ cross talk indicators predetermined for each stage of the specific disease, each of the patterns being derived from a predetermined relationship between an amount of an inter-organ cross talk indicator in the organ other than the specific organ in a positive control (or positive controls) affected with the specific disease (hereinafter referred to as "positive control amount 2") and an amount of the corresponding inter-organ cross talk indicator in the same organ as the organ other than the specific organ in a negative control (or negative controls) without the specific disease (hereinafter referred to as "negative control amount 2").
Item 32-1
 A program that, when executed by a computer, causes the computer to carry out the following computation processing to predict the presence of a disease and/or the stage of the disease in each of one or more organs other than a specific organ in a subject affected with a disease in the specific organ:
 processing of obtaining information about a stage of the disease in the specific organ (hereinafter referred to as "specific disease") in the subject;
 processing of checking the information about the stage obtained by the stage information obtaining processing against standard data 2a;
 processing of extracting a pattern of an inter-organ cross talk indicator in each of one or more organs other than the specific organ in the subject based on the results obtained by the stage information checking processing; and
 processing of predicting the presence of a disease and/or the stage of the disease in each of the one or more organs other than the specific organ by using, as a measure, the pattern of the inter-organ cross talk indicator obtained by the pattern extraction processing,
 wherein the inter-organ cross talk indicator comprises RNA, and
 the standard data 2a includes patterns of expression of the RNA predetermined for each stage of the specific disease, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in a negative control (or negative controls) without the specific disease.
Item 32-2
 A program that, when executed by a computer, causes the computer to carry out the following computation processing to predict the presence of a disease and/or the stage of the disease in each of one or more organs other than a specific organ in a subject affected with a disease in the specific organ:
 processing of obtaining information about a stage of the disease in the specific organ (hereinafter referred to as "specific disease") in the subject;
 processing of checking the information about the stage obtained by the stage information obtaining processing against standard data 2b;
 processing of extracting a pattern of an inter-organ cross talk indicator in each of one or more organs other than the specific organ in the subject based on the results obtained by the stage information checking processing; and
 processing of predicting the presence of a disease and/or the stage of the disease in each of the one or more organs other than the specific organ by using, as a measure, the pattern of the inter-organ cross talk indicator obtained by the pattern extraction processing,
 wherein the inter-organ cross talk indicator comprises metabolites, and
 the standard data 2b includes patterns of presence of the metabolites predetermined for each stage of the specific disease, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in a negative control (or negative controls) without the specific disease.
Item 32-3
 A program for causing a computer to function as the stage information obtaining means, the stage information checking means, the pattern extraction means, and the prediction means according to any one of Items 25 to 28.
Item 33
 The program according to Item 32, wherein the inter-organ cross talk indicator comprises RNA.
Item 34
 The program according to Item 32 or 33, wherein the inter-organ cross talk indicator comprises metabolites.
Item 35
 The program according to any one of Items 32, 33, and 34, wherein the relationship between the positive control amount 2 and the negative control amount 2 in the standard data 2 set forth in Item 32 is a ratio between the positive control amount 2 and the negative control amount 2.
Item 36
 The program according to any one of Items 32, 32-1, 32-2, and 33 to 35, wherein the specific organ is the heart, and the specific disease is myocardial infarction.
Item 36-1
 The program according to Item 36, wherein, when the inter-organ cross talk indicator comprises RNA, the RNA is expressed from genes listed in FIG. 25 or 26.

Item 36-2
The program according to Item 36, wherein, when the inter-organ cross talk indicator comprises metabolites, the metabolites are listed in FIG. 27.

Item 37
The program according to any one of Items 32, 32-1, 32-2, and 33 to 35, wherein the specific organ is the brain, and the specific disease is dementia.

Item 37-1
The program according to Item 37, wherein, when the inter-organ cross talk indicator comprises RNA, the RNA is expressed from genes listed in FIG. 25 or 26.

Item 37-2
The program according to Item 37, wherein, when the inter-organ cross talk indicator comprises metabolites, the metabolites are listed in FIG. 27.

Item 38
The program according to any one of Items 32, 32-1, 32-2, and 33 to 35, wherein the specific disease is a tumor.

Item 38-1
The program according to Item 38, wherein, when the inter-organ cross talk indicator comprises RNA, the RNA is expressed from genes listed in FIG. 25 or 26.

Item 38-2
The program according to Item 38, wherein, when the inter-organ cross talk indicator comprises metabolites, the metabolites are listed in FIG. 27.

Item 39
A method for predicting the presence of a disease and/or the stage of the disease in each of one or more organs other than a specific organ in a subject affected with a disease in the specific organ, the method comprising the steps of:
(i) obtaining information about a stage of the disease in the specific organ (hereinafter referred to as "specific disease") in the subject from diagnostic results of the subject;
(ii) checking the information about the stage obtained in step (i) against standard data 2;
(iii) determining, from the standard data 2, standard data a at a stage of the specific disease corresponding to the information about the stage, based on the checking results obtained in step (ii), and extracting, from the standard data a, a pattern of an inter-organ cross talk indicator corresponding to the stage in the subject in each of one or more organs other than the specific organ in the subject;
(iv) checking the pattern of the inter-organ cross talk indicator extracted in step (iii) against known information about inter-organ cross talk indicators in diseases and/or stages of the diseases, and determining the presence of a disease and/or the stage of the disease in each of the one or more organs other than the specific organ corresponding to the pattern of the inter-organ cross talk indicator in each of the one or more organs other than the specific organ in the subject; and
(v) further determining that the disease in each of the one or more organs other than the specific organ determined in step (iv) is a disease from which the subject may be suffering, and/or
further determining that the stage of the disease in each of the one or more organs other than the specific organ determined in step (iv) is a stage of a disease from which the subject is suffering,
wherein the standard data 2 includes patterns of inter-organ cross talk indicators predetermined for each stage of the specific disease, each of the patterns being derived from a predetermined relationship between an amount of an inter-organ cross talk indicator in the organ other than the specific organ in a positive control (or positive controls) affected with the specific disease (hereinafter referred to as "positive control amount 2") and an amount of the corresponding inter-organ cross talk indicator in the same organ as the organ other than the specific organ in a negative control (or negative controls) without the specific disease (hereinafter referred to as "negative control amount 2").

Item 39-1
A method for predicting the presence of a disease and/or the stage of the disease in each of one or more organs other than a specific organ in a subject affected with a disease in the specific organ, the method comprising the steps of:
(a) obtaining information about a stage of the specific disease in the subject from diagnostic results of the subject;
(b) checking the information about the stage obtained in step (a) against standard data $2a$;
(c) determining, from the standard data $2a$, standard data $\alpha 1$ at a stage of the specific disease corresponding to the information about the stage, based on the checking results obtained in step (b), and extracting, from the standard data $\alpha 1$, a pattern of an inter-organ cross talk indicator corresponding to the stage in the subject in each of one or more organs other than the specific organ in the subject;
(d) checking the pattern of the inter-organ cross talk indicator extracted in step (c) against known information about inter-organ cross talk indicators in diseases and/or stages of the diseases, and determining the presence of a disease and/or the stage of the disease in each of the one or more organs other than the specific organ corresponding to the pattern of the inter-organ cross talk indicator in each of the one or more organs other than the specific organ in the subject; and
(e) further determining that the disease in each of the one or more organs other than the specific organ determined in step (d) is a disease from which the subject may be suffering, and/or
further determining that the stage of the disease in each of the one or more organs other than the specific organ determined in step (d) is a stage of a disease from which the subject is suffering,
wherein the inter-organ cross talk indicator comprises RNA, and
the standard data $2a$ includes patterns of expression of the RNA predetermined for each stage of the specific disease, each of the patterns being derived from a predetermined ratio between an expression level of the RNA in the organ other than the specific organ in a positive control (or positive controls) affected with the specific disease and an expression level of the corresponding RNA in the same organ as the organ other than the specific organ in a negative control (or negative controls) without the specific disease.

Item 39-2
A method for predicting the presence of a disease and/or the stage of the disease in each of one or more organs other than a specific organ in a subject affected with a disease in the specific organ, the method comprising the steps of:
(a) obtaining information about a stage of the disease in the specific organ (hereinafter referred to as "specific disease") in the subject from diagnostic results of the subject;
(b) checking the information about the stage obtained in step (a) against standard data $2b$;
(c) determining, from the standard data $2b$, standard data $\alpha 2$ at a stage of the specific disease corresponding to the information about the stage, based on the checking results obtained in step (b), and extracting, from the standard data $\alpha 2$, a pattern of an inter-organ cross talk indicator corresponding to the stage in the subject in each of one or more organs other than the specific organ in the subject;

(d) checking the pattern of the inter-organ cross talk indicator extracted in step (c) against known information about inter-organ cross talk indicators in diseases and/or stages of the diseases, and determining the presence of a disease and/or the stage of the disease in each of the one or more organs other than the specific organ corresponding to the pattern of the inter-organ cross talk indicator in each of the one or more organs other than the specific organ in the subject; and (e) further determining that the disease in each of the one or more organs other than the specific organ determined in step (d) is a disease from which the subject may be suffering, and/or further determining that the stage of the disease in each of the one or more organs other than the specific organ determined in step (d) is a stage of a disease from which the subject is suffering, wherein the inter-organ cross talk indicator comprises metabolites, and the standard data 2b includes patterns of presence of the metabolites predetermined for each stage of the specific disease, each of the patterns being derived from predetermined ratios between amounts of the metabolites in the organ other than the specific organ in a positive control (or positive controls) affected with the specific disease and amounts of the corresponding metabolites in the same organ as the organ other than the specific organ in a negative control (or negative controls) without the specific disease.

Item 40

The method according to Item 39, wherein the inter-organ cross talk indicator comprises RNA.

Item 41

The method according to Item 39 or 40, wherein the inter-organ cross talk indicator comprises metabolites.

Item 42

The method according to any one of Items 39, 40, and 41, wherein the relationship between the positive control amount 2 and the negative control amount 2 in the standard data 2 set forth in Item 39 is a ratio between the positive control amount 2 and the negative control amount 2.

Item 43

The method according to any one of Items 39, 39-1, 39-2, and 40 to 42, wherein the specific organ is the heart, and the specific disease is myocardial infarction.

Item 43-1

The method according to Item 43, wherein, when the inter-organ cross talk indicator comprises RNA, the RNA is expressed from genes listed in FIG. 25 or 26.

Item 43-2

The method according to Item 43, wherein, when the inter-organ cross talk indicator comprises metabolites, the metabolites are listed in FIG. 27.

Item 44

The method according to any one of Items 39, 39-1, 39-2, and 40 to 42, wherein the specific organ is the brain, and the specific disease is dementia.

Item 44-1

The method according to Item 44, wherein, when the inter-organ cross talk indicator comprises RNA, the RNA is expressed from genes listed in FIG. 25 or 26.

Item 44-2

The method according to Item 44, wherein, when the inter-organ cross talk indicator comprises metabolites, the metabolites are listed in FIG. 27.

Item 45

The method according to any one of Items 39, 39-1, 39-2, and 40 to 42, wherein the specific disease is a tumor.

Item 45-1

The method according to Item 45, wherein, when the inter-organ cross talk indicator comprises RMA, the RNA is expressed from genes listed in FIG. 25 or 26.

Item 45-2

The method according to Item 45, wherein, when the inter-organ cross talk indicator comprises metabolites, the metabolites are listed in FIG. 27.

Item 46

A method for generating standard data 2 of patterns of inter-organ cross talk indicators for use in prediction of the presence of a disease and/or the stage of the disease in each of one or more organs other than a specific organ in a subject affected with a disease in the specific organ, the method comprising the steps of:

(A') obtaining information about an amount of an inter-organ cross talk indicator in cells or tissue originating from each of one or more organs other than the specific organ of a positive control (or positive controls) as a gold standard for each stage of the disease in the specific organ (hereinafter referred to as "specific disease");

(B') obtaining information about an amount of the inter-organ cross talk indicator in cells or tissue originating from each of the one or more organs other than the specific organ of a negative control (or negative controls) as a gold standard;

(C') determining patterns of inter-organ cross talk indicators, each of the patterns being determined from a relationship (preferably a ratio) between the amount of the inter-organ cross talk indicator in the organ other than the specific organ of the positive control (or positive controls) affected with the specific disease obtained in step (A') and the amount of the corresponding inter-organ cross talk indicator in the same organ as the organ other than the specific organ in the negative control (or negative controls) without the specific disease obtained in step (B'); and (D') associating the patterns of the inter-organ cross talk indicators with the corresponding stages of the specific disease.

Item 46-1

The method according to Item 46, wherein step (A') comprises the steps of:

extracting an inter-organ cross talk indicator from cells or tissue originating from each of one or more organs other than the specific organ of a positive control (or positive controls) as a gold standard for each stage of the specific disease; and identifying and quantifying the inter-organ cross talk indicator, and step (B') comprises the steps of:

extracting the inter-organ cross talk indicator from cells or tissue originating from each of the one or more organs other than the specific organ of a negative control (or negative controls) as a gold standard; and identifying and quantifying the inter-organ cross talk indicator.

Item 46-2

The method according to Item 46 or 46-1, wherein the inter-organ cross talk indicator comprises RNA.

Item 46-3

The method according to Item 46 or 46-1, wherein the inter-organ cross talk indicator comprises metabolites.

Item 46-4

The method according to any one of Items 46, 46-1, 46-2, and 46-3, wherein the specific organ is the heart, and the specific disease is myocardial infarction.

Item 46-4-1
The method according to Item 46-4, wherein, when the inter-organ cross talk indicator comprises RNA, the RNA is expressed from genes listed in FIG. 25 or 26.

Item 46-4-2
The method according to Item 46-4, wherein, when the inter-organ cross talk indicator comprises metabolites, the metabolites are listed in FIG. 27.

Item 46-5
The method according to any one of Items 46, 46-1, 46-2, and 46-3, wherein the specific organ is the brain, and the specific disease is dementia.

Item 46-5-1
The method according to Item 46-5, wherein, when the inter-organ cross talk indicator comprises RNA, the RNA is expressed from genes listed in FIG. 25 or 26.

Item 46-5-2
The method according to Item 46-5, wherein, when the inter-organ cross talk indicator comprises metabolites, the metabolites are listed in FIG. 27.

Item 46-6
The method according to any one of Items 46, 46-1, 46-2, and 46-3, wherein the specific disease is a tumor.

Item 46-6-1 The method according to Item 46-6, wherein, when the inter-organ cross talk indicator comprises RNA, the RNA is expressed from genes listed in FIG. 25 or 26.

Item 46-6-2
The method according to Item 46-6, wherein, when the inter-organ cross talk indicator comprises metabolites, the metabolites are listed in FIG. 27.

Item 47
Standard data 2 of patterns of inter-organ cross talk indicators generated by the method according to any one of Items 46, 46-1, 46-2, and 46-3, for use in prediction of the presence of a disease and/or the stage of the disease in each of one or more organs other than a specific organ in a subject affected with a disease in the specific organ.

Item 48
An apparatus for predicting efficacy or a side effect (or side effects) of a test substance, the apparatus comprising the following computation means:
a means for calculating, by comparing subject data X regarding an inter-organ cross talk indicator in each of one or more organs of an individual to which the test substance has been administered with predetermined standard data Y of the corresponding inter-organ cross talk indicator, similarity of patterns of the inter-organ cross talk indicators between the subject data X and the standard data Y, the subject data X being derived from cells or tissue originating from each of the one or more organs; and
a means for predicting efficacy or a side effect (or side effects) of the test substance in each of the one or more organs and/or each of one or more organs other than the one or more organs by using, as a measure, the similarity of patterns of the inter-organ cross talk indicators calculated by the pattern similarity calculation means.

Item 49
The apparatus according to Item 48, wherein the subject data X is a pattern of the inter-organ cross talk indicator representing a relationship between an amount of the inter-organ cross talk indicator in the organ of the individual to which the test substance has been administered and an amount of the corresponding inter-organ cross talk indicator in the same organ in a negative control (or negative controls).

Item 50
The apparatus according to Item 48 or 49, wherein the standard data Y is Y1: standard data of patterns of inter-organ cross talk indicators predetermined from amounts of inter-organ cross talk indicators whose functions are already known.

Item 51
The apparatus according to Item 48 or 49, wherein the standard data Y is Y2: patterns of inter-organ cross talk indicators, each of the patterns being derived from a predetermined relationship between an amount of an inter-organ cross talk indicator in an organ of an individual to which an existing substance has been administered and an amount of the corresponding inter-organ cross talk indicator in the same organ in the negative control (or negative controls).

Item 52
The apparatus according to Item 48 or 49, wherein the standard data Y is Y3: patterns of inter-organ cross talk indicators, each of the patterns being derived from a predetermined relationship between an amount of an inter-organ cross talk indicator in an organ of a positive control individual (or positive control individuals) affected with a disease and an amount of the corresponding inter-organ cross talk indicator in the same organ in the negative control (or negative controls).

Item 53
The apparatus according to any one of Items 48 to 52, wherein the inter-organ cross talk indicator comprises RNA.

Item 54
The apparatus according to any one of Items 48 to 52, wherein the inter-organ cross talk indicator comprises metabolites.

Item 55
A program that, when executed by a computer, causes the computer to carry out the following processing to predict efficacy or a side effect (or side effects) of a test substance:
processing of calculating, by comparing subject data X regarding an inter-organ cross talk indicator in each of one or more organs of an individual to which the test substance has been administered with predetermined standard data Y of the corresponding inter-organ cross talk indicator, similarity of patterns of the inter-organ cross talk indicators between the subject data X and the standard data Y, the subject data X being derived from cells or tissue originating from each of the one or more organs; and
processing of predicting efficacy or a side effect (or side effects) of the test substance in each of the one or more organs and/or each of one or more organs other than the one or more organs by using, as a measure, the similarity of patterns of the inter-organ cross talk indicators calculated by the pattern similarity calculation processing.

Item 56
The program according to Item 55, wherein the subject data X is a pattern of the inter-organ cross talk indicator representing a relationship between an amount of the inter-organ cross talk indicator in the organ of the individual to which the test substance has been administered and an amount of the corresponding inter-organ cross talk indicator in the same organ in a negative control (or negative controls).

Item 57
The program according to Item 55 or 56, wherein the standard data Y is Y1: patterns predetermined from amounts of inter-organ cross talk indicators whose functions are already known.

Item 58
The program according to Item 55 or 56, wherein the standard data Y is Y2: patterns of inter-organ cross talk indicators, each of the patterns being derived from a predetermined relationship between an amount of an inter-organ cross talk indicator in an organ of an individual to which an existing substance has been administered and an amount of the corresponding inter-organ cross talk indicator in the same organ in the negative control (or negative controls).

Item 59

The program according to Item 55 or 56, wherein the standard data Y is Y3: patterns of inter-organ cross talk indicators, each of the patterns being derived from a predetermined relationship between an amount of an inter-organ cross talk indicator in an organ of a positive control individual (or positive control individuals) affected with a disease and an amount of the corresponding inter-organ cross talk indicator in the same organ in the negative control (or negative controls).

Item 60

The program according to any one of Items 55 to 59, wherein the inter-organ cross talk indicator comprises RNA.

Item 61

The program according to any one of Items 55 to 59, wherein the inter-organ cross talk indicator comprises metabolites.

Item 62

A program for causing a computer to function as the pattern similarity calculation means and the prediction means according to any one of Items 48 to 54.

Item 63

A method for predicting efficacy or a side effect (or side effects) of a test substance, the method comprising the steps of:

(1) calculating, by comparing subject data X regarding an inter-organ cross talk indicator in each of one or more organs of an individual to which the test substance has been administered with predetermined standard data Y of the corresponding inter-organ cross talk indicator, similarity of patterns of the inter-organ cross talk indicators between the subject data X and the standard data Y, the subject data X being derived from cells or tissue originating from each of the one or more organs; and (2) predicting efficacy or a side effect (or side effects) of the test substance in each of the one or more organs and/or each of one or more organs other than the one or more organs by using, as a measure, the similarity of patterns of the inter-organ cross talk indicators calculated in step (1).

Item 64

The method according to Item 63, wherein the subject data X is a pattern of the inter-organ cross talk indicator representing a relationship between an amount of the inter-organ cross talk indicator in the organ of the individual to which the test substance has been administered and an amount of the corresponding inter-organ cross talk indicator in the same organ in a negative control (or negative controls).

Item 65

The method according to Item 63 or 64, wherein the standard data Y is Y1: patterns predetermined from amounts of inter-organ cross talk indicators whose functions are already known.

Item 66

The method according to Item 63 or 64, wherein the standard data Y is Y2: patterns of inter-organ cross talk indicators, each of the patterns being derived from a predetermined relationship between an amount of an inter-organ cross talk indicator in an organ of an individual to which an existing substance has been administered and an amount of the corresponding inter-organ cross talk indicator in the same organ in the negative control (or negative controls).

Item 67

The method according to Item 63 or 64, wherein the standard data Y is Y3: patterns of inter-organ cross talk indicators, each of the patterns being derived from a predetermined relationship between an amount of an inter-organ cross talk indicator in an organ of a positive control individual (or positive control individuals) affected with a disease and an amount of the corresponding inter-organ cross talk indicator in the same organ in the negative control (or negative controls).

Item 68

The method according to Items 63 to 67, further comprising, before step (1), (i) obtaining information about the subject data X regarding the inter-organ cross talk indicator in each of the one or more organs in the individual to which the test substance has been administered, the inter-organ cross talk indicator being derived from the cells or tissue originating from each of the one or more organs.

Item 69

The method according to Item 68, wherein step (i) comprises determining the subject data X regarding the inter-organ cross talk indicator from an amount of the inter-organ cross talk indicator in each of the one or more organs of the individual to which the test substance has been administered, the inter-organ cross talk indicator being derived from the cells or tissue originating from each of the one or more organs.

Item 70

The method according to Item 69, wherein step (i) comprises identifying or quantifying the inter-organ cross talk indicator extracted from the cells or tissue originating from each of the one or more organs of the individual to which the test substance has been administered.

Item 71

The method according to any one of Items 68 to 70, further comprising, before step (i), the steps of:

(ii) providing the test substance;

(iii) providing the individual;

(iv) administering the test substance provided in step (ii) to the individual provided in step (iii);

(v) collecting the one or more organs from the individual administered the test substance in step (iv); and (vi) collecting the cells or tissue from the one or more organs collected in step (v).

Item 72

The method according to any one of Items 68 to 71, wherein the inter-organ cross talk indicator comprises RNA.

Item 73

The method according to any one of Items 68 to 71, wherein the inter-organ cross talk indicator comprises metabolites.

Item 74

A method for generating standard data Y of patterns of inter-organ cross talk indicators for use in prediction of efficacy or a side effect (or side effects) of a test substance, the method comprising the steps of:

(1) extracting inter-organ cross talk indicators from cells or tissue originating from one or more organs of an individual or individuals to which existing substances have been individually administered, and/or cells or tissue originating from the one or more organs of a negative control (or negative controls), and/or cells or tissue originating from the one or more organs of a positive control individual or positive control individuals affected with individual diseases;

(2) identifying and quantifying the inter-organ cross talk indicators extracted in step (1); and (3) determining standard data Y of the inter-organ cross talk indicators from the amounts of the inter-organ cross talk indicators quantified in step (2).

Item 75

A microarray comprising probes capable of searching for at least one group selected from the group consisting of groups 1 to 8 described herein in the "1. Explanation of terms" section and "8. Microarray and kit" section, for use in obtaining data of a subject regarding an inter-organ cross talk indicator in each of one or more organs other than a specific organ, derived from cells or tissue originating from each of the one or more organs, in a method for predicting the presence of a disease in the specific organ and/or the stage of the disease in the subject, and/or a method for predicting efficacy or a side effect (or side effects) of a test substance.

Item 76

The microarray according to Item 75, which is to be incorporated in the apparatus according to any one of Items 1-1, 2, 4, 4-1, 5, 5-1, 6, 6-1, 7, 7-1, 25-1, 26, 28, 29, 29-1, 30, 30-1, 31, and 31-1.

Item 77

A kit comprising a microarray comprising probes capable of searching for at least one group selected from the group consisting of groups 1 to 8 described herein in the "1. Explanation of terms" section and "8. Microarray and kit" section, for use in obtaining data of a subject regarding an inter-organ cross talk indicator in each of one or more organs other than a specific organ, derived from cells or tissue originating from each of the one or more organs, in a method for predicting the presence of a disease in the specific organ and/or the stage of the disease in the subject, and/or a method for predicting efficacy or a side effect (or side effects) of a test substance.

Advantageous Effects of Invention

According to the present invention (Reverse iOrgans), subtle changes in the state of one organ are correlated with subtle changes in other organs to capture subtle changes in one organ or tissue, and the present invention can detect an abnormality in other organs or tissue earlier than usual diagnostic methods. Furthermore, use of an apparatus or a program for evaluating such a correlation in multiple organs or tissues makes it possible to diagnose the multiple organs or tissues by diagnosing one organ or tissue, thus dramatically improving diagnostic efficiency. According to the present invention (Forward iOrgans), the state of an organ that cannot yet be diagnosed as having an abnormality by using a usual test is inferred from the state of an organ already confirmed to have an abnormality by using a usual diagnostic method; therefore, an abnormality in other organs or tissue caused by heart disease, brain disease, cancer, etc., can be detected early, and secondary and tertiary diseases (such as renal failure, hepatopathy, and cancer metastasis) can be prevented or treated. Further, the efficacy and side effect (or side effects) of a test substance can be predicted.

BRIEF DESCRIPTION OF DRAWINGS

FIG. 2(a) is an example of standard data 1 at the stages of myocardial infarction. FIG. 2(b) is an example of data of adipose tissue of a subject.

FIG. 4 schematically illustrates an outline of Forward iOrgans according to the present invention. FIG. 4(a) is an example of standard data 2. FIG. 4(b) is an example of data regarding an inter-organ cross talk indicator in the early stage of myocardial infarction extracted from the standard data 2. FIG. 4(c) is an example of data (standard data α) regarding an inter-organ cross talk indicator in the kidney extracted from the data regarding the inter-organ cross talk indicator in the early stage of myocardial infarction.

FIG. 5 schematically illustrates an outline of Drug iOrgans according to the present invention. FIG. 5(a) illustrates a model of D-iOrgans for predicting the side effect (or side effects) of a test substance. FIG. 5(b) illustrates a model of D-iOrgans for predicting the efficacy of a test substance.

FIG. 7 schematically illustrates an outline of Drug iOrgans according to the present invention.

FIG. 16(a) illustrates standard data 1. FIG. 16(b) illustrates the pattern of subject data X of organ A after administration of a test substance. FIG. 16(c) illustrates subject data X of organ B after administration of the test substance. FIG. 16(d) illustrates subject data X of organ B after administration of a test substance. Hatching indicates patterns of inter-organ cross talk indicators.

FIG. 17(a) illustrates standard data 1. FIG. 17(b) illustrates the pattern of subject data X of organ A after administration of a test substance. FIG. 17(c) illustrates subject data X of organ B after administration of the test substance. Hatching indicates patterns of inter-organ cross talk indicators.

FIG. 25 is a list of RNAs in mice that can be detected by, for example, RNA-Seq. In FIG. 25, "Line No." indicates a line number in the list, "Gene Name" indicates a gene name registered with the U.S. National Center for Biotechnology Information (NCBI), and "Reference Seq. ID" indicates a reference sequence ID number registered with the NCBI. "Chromosome Locus" indicates a chromosome locus registered in mm9.

FIG. 26 is a list of RNAs in mice that can be detected by, for example, RNA-Seq. In FIG. 26, "Line No." indicates a line number in the list, "Gene Name" indicates a gene name registered with the U.S. National Center for Biotechnology Information (NCBI), and "Reference Seq. ID" indicates a reference sequence ID number registered with the NCBI. "Chromosome Locus" indicates a chromosome locus registered in mm10.

FIG. 27 is a list of metabolites of group B.

FIG. 28 is a list of metabolites of group C.

FIG. 29 shows time-course changes of metabolites in which the MI/Sham value obtained by GCMS analysis is more than 1 or less than 1 in each kind of tissue. The symbols in FIG. 29 are as follows: 1 d: 1 day after coronary artery ligation, 1 w: 1 week after coronary artery ligation, and 8 w: 8 weeks after coronary artery ligation.

FIG. 30: RNAs examined for their expression levels were classified as follows. RNAs in which MI/Sham is more than 1 or less than 1 were classified as group 4, RNAs in which MI/Sham is more than 1.5 or less than 0.67 were classified as group 5, RNAs in which MI/Sham is more than 2 or less than 0.5 were classified as group 6, and RNAs in which MI/Sham is more than 5 or less than 0.2 were classified as group 7. The RNAs of group 8, which were also examined using real-time PCR, are particularly useful in the present invention. In FIG. 30, "Line No." indicates a line number in the list, "Groups" indicates a group number of each of the groups classified based on the MI/Sham values, "Gene Name" indicates a gene name registered with NCBI, "Human Gene ID" indicates a human gene number registered with the NCBI that corresponds to the gene name, and "Updated" indicates the date of update to the Human Gene ID in NCBI. In "Sub-Group," "VIII" indicates group 8, "VII-1" indicates RNAs, among the RNAs of group 7, in which MI/Sham is more than 5 and that are not included in group 8, and "VII-2" indicates RNAs, among the RNAs of group 7, in which MI/Sham is less than 0.2 and that are not included in group 8. "VI-1" indicates RNAs, among the RNAs of group 6, in which MI/Sham is more than 2 and that are not included in group 7 or group 8, and "VI-2" indicates RNAs, among the RNAs of group 6, in which MI/Sham is less than 0.5 and that are not included in group 7 or group 8. "V-1" indicates RNAs, among the RNAs of group 5, in which MI/Sham is more than 1.5 and that are not included in any of groups 6 to 8, and "V-2" indicates RNAs, among the RNAs of group 5, in which MI/Sham is less than 0.67 and that are not included in any of groups 6 to 8. "IV-1" indicates RNAs, among the RNAs of group 4, in which MI/Sham is more than 1 and that are not included in any of groups 5 to 8, and "IV-2" indicates RNAs, among the RNAs of group 4, in which MI/Sham is less than 1 and that are not included in any of groups 5 to 8. The RNAs of group 3 are observed to be expressed in the organs tested within 8 weeks after left coronary artery ligation in a myocardial infarction mouse model; i.e., they are RNAs in which the FPKM value is 1 or more.

FIG. 31 shows time-course changes of expression of RNAs shown in FIG. 30 in which MI/Sham is more than 5 or less than 0.2, in each organ. The symbols in FIG. 31 are as follows: 1 d: 1 day after coronary artery ligation, 1 w: 1 week after coronary artery ligation, and 8 w: 8 weeks after coronary artery ligation.

FIG. 32 shows the results of real-time PCR analysis. The symbols in FIG. 32 are as follows: 1 h: 1 hour after coronary artery ligation, 6 h: 6 hours after coronary artery ligation, 1 d: 1 day after coronary artery ligation, 1 w: 1 week after coronary artery ligation, and 8 w: 8 weeks after coronary artery Ligation. "Gene Name" indicates a gene name registered with NCBI.

FIG. 33 shows time-course changes of metabolites in which the SAMP8/Control value obtained by CEMS analysis is more than 1 or less than 1, in each kind of tissue. The symbols in FIG. 33 are as follows: E: early stage of young-onset dementia, and M: middle stage of young-onset dementia.

FIG. 34: RNAs examined for their expression levels were classified as follows. RNAs in which SAMP8/Control is more than 1 or less than 1 were classified as group 4, RNAs in which SAMP8/Control is more than 1.5 or less than 0.67 were classified as group 5, RNAs in which SAMP8/Control is more than 2 or less than 0.5 were classified as group 6, and RNAs in which SAMP8/Control is more than 5 or less than 0.2 were classified as group 7. In "Sub-Group," "VII-1" indicates RNAs, among the RNAs of group 7, in which SAMP8/Control is more than 5, and "VII-2" indicates RNAs, among the RNAs of group 7, in which SAMP8/Control is less than 0.2. "VI-1" indicates RNAs, among the RNAs of group 6, in which SAMP8/Control is more than 2 and that are not included in group 7, and "VI-2" indicates RNAs, among the RNAs of group 6, in which SAMP8/Control is less than 0.5 and that are not included in group 7. "V-1" indicates RNAs, among the RNAs of group 5, in which SAMP8/Control is more than 1.5 and are not included in group 6 or group 7, and "V-2" indicates RNAs, among the RNAs of group 5, in which SAMP8/Control is less than 0.67 and that are not included in group 6 or group 7. "IV-1" indicates RNAs, among the RNAs of group 4, in which SAMP8/Control is more than 1 and that are not included in any of groups 5 to 7, and "IV-2" indicates RNAs, among the RNAs of group 4, in which SAMP8/Control is less than 1 and that are not included in any of groups 5 to 7. The RNAs of group 3 are observed to be expressed in the organs tested by the late stage in a young-onset dementia mouse model; i.e., they are RNAs in which the FPKM value is 1 or more. The symbols in FIG. 34 are as follows: E: early stage of young-onset dementia, M: middle stage of young-onset dementia, and L: late stage of young-onset dementia.

FIG. 35 shows time-course changes of expression of the RNAs of group 7 shown in FIG. 34 in each organ. The symbols in FIG. 35 are as follows: E: early stage of young-onset dementia, M: middle stage of young-onset dementia, and L: late stage of young-onset dementia.

FIG. 36: RNAs examined for their expression levels were classified as follows. RNAs in which Glioma/Control is more than 1 or less than 1 were classified as group 4, RNAs in which Glioma/Control is more than 1.5 or less than 0.67 were classified as group 5, RNAs in which Glioma/Control is more than 2 or less than 0.5 were classified as group 6, and RNAs in which Glioma/Control is more than 5 or less than 0.2 were classified as group 7. In FIG. 36, "Line No." indicates a line number in the list, "Groups" indicates a group number of each of groups classified based on the Glioma/Control values, and "Gene Name" indicates a gene name registered with NCBI. In "Sub-Group," "VII-1" indicates RNAs, among the RNAs of group 7, in which Glioma/Control is more than 5, and "VII-2" indicates RNAs, among the RNAs of group 7, in which Glioma/Control is less than 0.2. "VI-1" indicates RNAs, among the RNAs of group 6, in which Glioma/Control is more than 2 and that are not included in group 7, and "VI-2" indicates RNAs, among the RNAs of group 6, in which Glioma/Control is less than 0.5 and that are not included in group 7. "V-1" indicates RNAs, among the RNAs of group 5, in which Glioma/Control is more than 1.5 and that are not included in group 6 or group 7, and "V-2" indicates RNAs, among the RNAs of group 5, in which Glioma/Control is less than 0.67 and that are not included in group 6 or group 7. "IV-1" indicates RNAs, among the RNAs of group 4, in which Glioma/Control is more than 1 and that are not included in any of groups 5 to 7, and "IV-2" indicates RNAs, among the RNAs of group 4, in which Glioma/Control is less than 1 and that are not included in any of groups 5 to 7. The RNAs of group 3 are observed to be expressed in the organs tested by day 7 after glioma implantation; i.e., they are RNAs in which the FPKM value is 1 or more.

FIG. 37 shows time-course changes of expression of the RNAs of group 7 shown in FIG. 36 in each organ. The symbols in FIG. 37 are as follows: 3 d: day 3 after tumor implantation, and 7 d: day 7 after tumor implantation.

FIG. 38 shows RNA expression in the skin of human breast cancer patients. RNAs examined for their expression levels were classified as follows. RNAs in which BC/Control is more than 1 or less than 1 were classified as group 4, RNAs in which BC/Control is more than 1.5 or less than 0.67 were classified as group 5, RNAs in which BC/Control is more than 2 or less than 0.5 were classified as group 6, and RNAs in which BC/Control is more than 5 or less than 0.2 were classified as group 7. In FIG. 38, "Line No." indicates a line number in the list, "Groups" indicates a group number of each of the groups classified based on the BC/Control values, and "Gene Name" indicates a gene name registered with NCBI. In "Sub-Group," "VII-1" indicates RNAs, among the RNAs of group 7, in which BC/Control is more than 5, and "VII-2" indicates RNAs, among the RNAs of group 7, in which BC/Control is less than 0.2. "VI-1" indicates RNAs, among the RNAs of group 6, in which BC/Control is more than 2 and that are not included in group 7, and "VI-2" indicates RNAs, among the RNAs of group 6, in which BC/Control is less than 0.5 and that are not included in group 7. "V-1" indicates RNAs, among the RNAs of group 5, in which BC/Control is more than 1.5 and that are not included in group 6 or group 7, and "V-2" indicates RNAs, among the RNAs of group 5, in which BC/Control is less than 0.67 and that are not included in group 6 or group 7. "IV-1" indicates RNAs, among the RNAs of group 4, in which BC/Control is more than 1 and that are not included in any of groups 5 to 7, and "IV-2" indicates RNAs, among the RNAs of group 4, in which BC/Control is less than 1 and that are not included in any of groups 5 to 7. The RNAs of group 3 are observed to be expressed in the organ tested; i.e., they are RNAs in which the FPKM value is 1 or more.

FIG. 39 shows RNA expression in the skin of a human lung cancer patient. RNAs examined for their expression levels were classified as follows. RNAs in which LC/Control is more than 1 or less than 1 were classified as group 4, RNAs in which LC/Control is more than 1.5 or less than 0.67 were classified as group 5, RNAs in which LC/Control is more than 2 or less than 0.5 were classified as group 6, and RNAs in which LC/Control is more than 5 or less than 0.2 were classified as group 7. In FIG. 39, "Line No." indicates a line number in the list, "Groups" indicates a group number of each of the groups classified based on the LC/Control values, and "Gene Name" indicates a gene name registered with NCBI. In "Sub-Group," "VII-1" indicates RNAs, among the RNAs of group 7, in which LC/Control is more than 5, and "VII-2" indicates RNAs, among the RNAs of group 7, in which LC/Control is less than 0.2. "VI-1" indicates RNAs, among the RNAs of group 6, in which LC/Control is more than 2 and that are not included in group 7, and "VI-2" indicates RNAs, among the RNAs of group 6, in which LC/Control is less than 0.5 and that are not included in group 7. "V-1" indicates RNAs, among the RNAs of group 5, in which LC/Control is more than 1.5 and that are not included in group 6 or group 7, and "V-2" indicates RNAs, among the RNAs of group 5, in which LC/Control is less than 0.67 and that are not included in group 6 or group 7. "IV-1" indicates RNAs, among the RNAs of group 4, in which LC/Control is more than 1 and that are not included in any of groups 5 to 7, and "IV-2" indicates RNAs, among the RNAs of group 4, in which LC/Control is less than 1 and that are not included in any of groups 5 to 7. The RNAs of group 3 are observed to be expressed in the organ tested; i.e., they are RNAs in which the FPKM value is 1 or more.

FIG. 40 shows RNA expression in the blood of a human breast cancer patient. RNAs examined for their expression levels were classified as follows. RNAs in which BC/Control is more than 1 or less than 1 were classified as group 4, RNAs in which BC/Control is more than 1.5 or less than 0.67 were classified as group 5, RNAs in which BC/Control is more than 2 or less than 0.5 were classified as group 6, and RNAs in which BC/Control is more than 5 or less than 0.2 were classified as group 7. In FIG. 40, "Line No." indicates a line number in the list, "Groups" indicates a group number of each of the groups classified based on the BC/Control values, and "Gene Name" indicates a gene name registered with NCBI. In "Sub-Group," "VII-1" indicates RNAs, among the RNAs of group 7, in which BC/Control is more than 5, and "VII-2" indicates RNAs, among the RNAs of group 7, in which BC/Control is less than 0.2. "VI-1" indicates RNAs, among the RNAs of group 6, in which BC/Control is more than 2 and that are not included in group 7, and "VI-2" indicates RNAs, among the RNAs of group 6, in which BC/Control is less than 0.5 and that are not included in group 7. "V-1" indicates RNAs, among the RNAs of group 5, in which BC/Control is more than 1.5 and that are not included in group 6 or group 7, and "V-2" indicates RNAs, among the RNAs of group 5, in which BC/Control is less than 0.67 and that are not included in group 6 or group 7. "IV-1" indicates RNAs, among the RNAs of group 4, in which BC/Control is more than 1 and that are not included in any of groups 5 to 7, and "IV-2" indicates RNAs, among the RNAs of group 4, in which BC/Control is less than 1 and that are not included in any of groups 5 to 7. The RNAs of group 3 are observed to be expressed in the organ tested; i.e., they are RNAs in which the FPKM value is 1 or more.

FIG. 41 shows RNA expression in the blood of a human lung cancer patient. RNAs examined for their expression levels were classified as follows. RNAs in which LC/Control is more than 1 or less than 1 were classified as group 4, RNAs in which LC/Control is more than 1.5 or less than 0.67 were classified as group 5, RNAs in which LC/Control is more than 2 or less than 0.5 were classified as group 6, and RNAs in which LC/Control is more than 5 or less than 0.2 were classified as group 7. In FIG. 41, "Line No." indicates a line number in the list, "Groups" indicates a group number of each of the groups classified based on the LC/Control values, and "Gene Name" indicates a gene name registered with NCBI. In "Sub-Group," "VII-1" indicates RNAs, among the RNAs of group 7, in which LC/Control is more than 5, and "VII-2" indicates RNAs, among the RNAs of group 7, in which LC/Control is less than 0.2. "VI-1" indicates RNAs, among the RNAs of group 6, in which LC/Control is more than 2 and that are not included in group 7, and "VI-2" indicates RNAs, among the RNAs of group 6, in which LC/Control is less than 0.5 and that are not included in group 7. "V-1" indicates RNAs, among the RNAs of group 5, in which LC/Control is more than 1.5 and that are not included in group 6 or group 7, and "V-2" indicates RNAs, among the RNAs of group 5, in which LC/Control is less than 0.67 and that are not included in group 6 or group 7. "IV-1" indicates RNAs, among the RNAs of group 4, in which LC/Control is more than 1 and that are not included in any of groups 5 to 7, and "IV-2" indicates RNAs, among the RNAs of group 4, in which LC/Control is less than 1 and that are not included in any of groups 5 to 7. The RNAs of group 3 are observed to be expressed in the organ tested; i.e., they are RNAs in which the FPKM value is 1 or more.

FIG. 42 shows time-course changes of metabolites in which the STZ/Control value obtained by CEMS analysis is more than 1 or less than 1, in each kind of tissue.

FIG. 43: RNAs examined for their expression levels in D-iOrgans were classified as follows. RNAs in which STZ/Control is more than 1 or less than 1 were classified as group 4, RNAs in which STZ/Control is more than 1.5 or less than 0.67 were classified as group 5, RNAs in which STZ/Control is more than 2 or less than 0.5 were classified as group 6, and RNAs in which STZ/Control is more than 5 or less than 0.2 were classified as group 7. The RNAs of group 8, which were also examined using real-time PCR, are particularly useful in the present invention. In FIG. 43, "Line No." indicates a line number in the list, "Groups" indicates a group number of each of the groups classified based on the STZ/Control values, and "Gene Name" indicates a gene name registered with NCBI. In "Sub-Group," "VIII" indicates group 8, "VII-1" indicates RNAs, among the RNAs of group 7, in which STZ/Control is more than 5 and that are not included in group 8, and "VII-2" indicates RNAs, among the RNAs of group 7, in which STZ/Control is less than 0.2 and that are not included in group 8. "VI-1" indicates RNAs, among the RNAs of group 6, in which STZ/Control is more than 2 and that are not included in group 7 or group 8, and "VI-2" indicates RNAs, among the RNAs of group 6, in which STZ/Control is less than 0.5 and that are not included in group 7 or group 8. "V-1" indicates RNAs, among the RNAs of group 5, in which STZ/Control is more than 1.5 and that are not included in any of groups 6 to 8, and "V-2" indicates RNAs, among the RNAs of group 5, in which STZ/Control is less than 0.67 and are not included in any of groups 6 to 8. "IV-1" indicates RNAs, among the RNAs of group 4, in which STZ/Control is more than 1 and that are not included in any of groups 5 to 8, and "IV-2" indicates RNAs, among the RNAs of group 4, in which STZ/Control is less than 1 and that are not included in any of groups 5 to 8. The RNAs of group 3 are observed to be expressed in the organs tested; i.e., they are RNAs in which the FPKM value is 1 or more.

FIG. 44 shows the results of real-time PCR analysis in D-iOrgans.

FIG. 45 shows the results of D-iOrgans using embryos removed from mice to which STZ was administered. RNAs examined for their expression levels were classified as follows. RNAs in which STZ/Control is more than 1 or less than 1 were classified as group 4, RNAs in which STZ/Control is more than 1.5 or less than 0.67 were classified as group 5, RNAs in which STZ/Control is more than 2 or less than 0.5 were classified as group 6, and RNAs in which STZ/Control is more than 5 or less than 0.2 were classified as group 7. In FIG. 45, "Line No." indicates a line number in the list, "Groups" indicates a group number of each of the groups classified based on the STZ/Control values, and "Gene Name" indicates a gene name registered with NCBI. In "Sub-Group," "VII-1" indicates RNAs, among the RNAs of group 7, in which STZ/Control is more than 5, and "VII-2" indicates RNAs, among the RNAs of group 7, in which STZ/Control is less than 0.2. "VI-1" indicates RNAs, among the RNAs of group 6, in which STZ/Control is more than 2 and that are not included in group 7, and "VI-2" indicates RNAs, among the RNAs of group 6, in which STZ/Control is less than 0.5 and that are not included in group 7. "V-1" indicates RNAs, among the RNAs of group 5, in which STZ/Control is more than 1.5 and that are not included in group 6 or group 7, and "V-2" indicates RNAs, among the RNAs of group 5, in which STZ/Control is less than 0.67 and that are not included in group 6 or group 7. "IV-1" indicates RNAs, among the RNAs of group 4, in which STZ/Control is more than 1 and that are not included in any of groups 5 to 7. "IV-2" indicates RNAs, among the RNAs of group 4, in which STZ/Control is less than 1 and that are not included in any of groups 5 to 7. The RNAs of group 3 are observed to be expressed in the organ tested; i.e., they are RNAs in which the FPKM value is 1 or more.

DESCRIPTION OF EMBODIMENTS

The present invention relates to two novel disease determination methods called "Reverse iOrgans" and "Forward iOrgans" based on a new methodology called "iOrgans (Inter-Organ Cross Talks) technology." In the methodology, a comprehensive database of changes in the amounts of gene expression, metabolites, etc., derived from organs other than a specific organ is constructed and the changes are associated with functional and histological changes of the specific organ in a subject. The disease determination is achieved by using the comprehensive database. "iOrgans" is a technology to diagnose, prevent, and/or treat disease by using the interrelationship between the state of one organ and that of one or more other organs as a measure. Assuming that the specific disease is myocardial infarction, outlines of Reverse iOrgans (also referred to as "R-iOrgans"), Forward iOrgans (also referred to as "F-iOrgans"), and Drug iOrgans (also referred to as "D-iOrgans") are described below.

Figure 1:
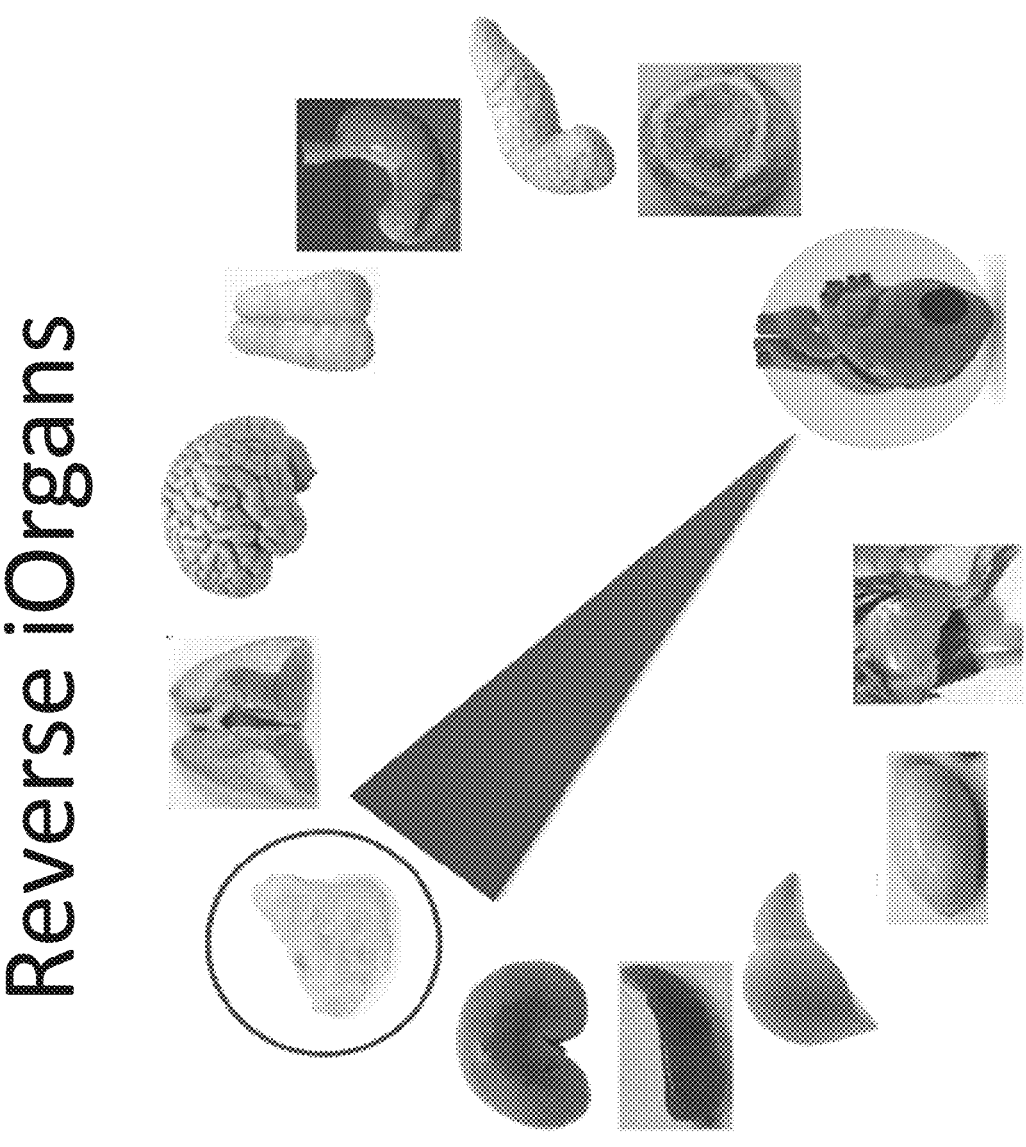
FIG. 1 schematically illustrates an outline of Reverse iOrgans according to the present invention.
Figure 2:
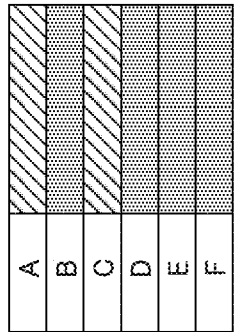
FIG. 2 schematically illustrates an outline of Reverse iOrgans according to the present invention.

FIGS. 1 and 2 schematically illustrate an outline of Reverse iOrgans according to the present invention.

Reverse iOrgans is a method for predicting a specific disease in a subject from information regarding the pattern of gene expression in each organ other than a specific organ collected from the same subject at the same time point. It is possible to predict the presence of a specific latent disease or the state of a specific organ by this method. In the example shown in FIG. 1, a disease (e.g., myocardial infarction) in a specific organ (e.g., heart) is predicted from information regarding the pattern of gene expression in another organ (e.g., adipose tissue or cells) as an example. An outline of the prediction method of Reverse iOrgans is described with reference to FIG. 2, assuming, as an example, that the other organ is adipose tissue and that the disease in the specific organ is myocardial infarction. A to F shown in FIG. 2 represent an inter-organ cross talk indicator.

First, a pattern of gene expression (i.e., a pattern of the inter-organ cross talk indicator) in adipose tissue is collected beforehand from each state of the heart, i.e., each stage of myocardial infarction, as standard data. FIG. 2(a) shows an example of standard data 1. The standard data of FIG. 2(a) shows a pattern of the inter-organ cross talk indicator, i.e., A to F in adipose tissue at each of the stages of myocardial infarction (normal state, and acute phase (ischemic state), convalescent phase (fibrotic state), and maintenance phase (cardiac hypertrophy state) of myocardial infarction). In the patterns of the inter-organ cross talk indicators from the acute phase to the maintenance phase of myocardial infarction, items in the inter-organ cross talk indicators shown in gray represent items in the inter-organ cross talk indicators showing no changes relative to normal, and items in the inter-organ cross talk indicators shown with diagonal hatching represent items in the inter-organ cross talk indicators showing changes relative to normal.

Next, adipose tissue is collected from a subject, and the pattern of the inter-organ cross talk indicator in the adipose tissue is determined and used as data of the subject (e.g., FIG. 2(b)). Subsequently, the standard data and the data of the subject derived from adipose tissue are compared with each other, and similarity between patterns is calculated. When a pattern similar to the data of the subject is present in the standard data, it can be predicted that the state of the heart linked with the similar pattern in the standard data is the state of the heart (the disease stage of the heart) that the subject is suffering. In the example shown in FIG. 2, the pattern of the data of the subject shown in (b) is similar to the second pattern from the top in the standard data. The second pattern from the top is a pattern derived from a heart that is in the state of the acute phase of myocardial infarction. It can thus be predicted that the heart of the subject is in the state of the acute phase of myocardial infarction (ischemic state).

Figure 3:
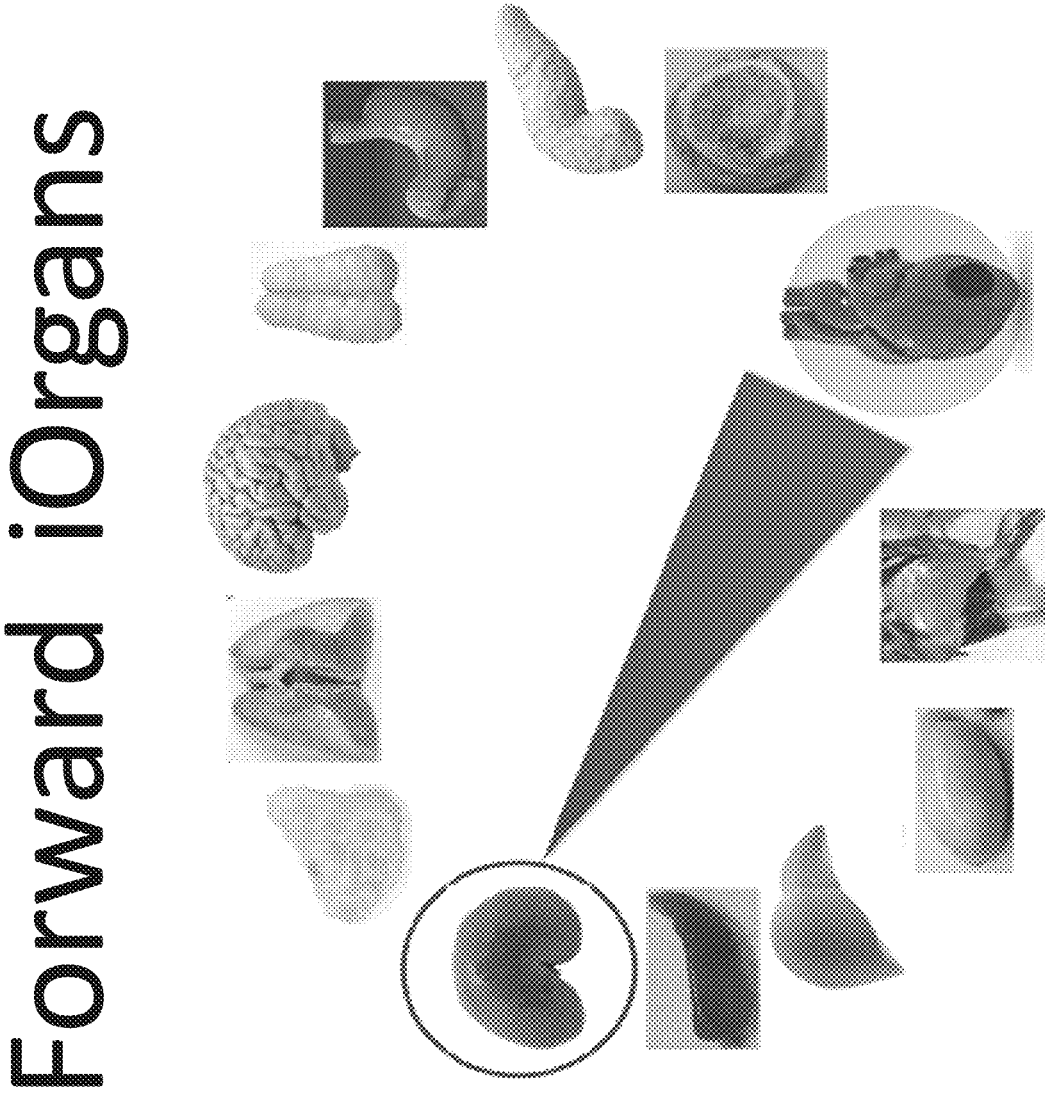
FIG. 3 schematically illustrates an outline of Forward iOrgans according to the present invention.

FIGS. 3 and 4 schematically illustrate an outline of Forward iOrgans according to the present invention.

Forward iOrgans is a method in which, after the stage of a specific disease in a specific organ in a subject is determined by using a usual test etc., the stage of the specific disease is compared with predetermined data regarding inter-organ cross talk indicators in other organs to determine the pattern of gene expression etc. derived from each organ other than the specific organ of the subject and, on the basis of this, the presence of a disease or the stage of the disease, including complications, in each of the organs other than the specific organ is predicted. The presence of a disease or the stage of the disease, including complications, in each organ other than the specific organ can be predicted by checking the pattern of gene expression etc. derived from each of the organs other than the specific organ of the subject against previously reported information regarding gene expression in the disease in each of the organs other than the specific organ. In the example of FIG. 3, the stage of a disease (e.g., myocardial infarction) in a specific organ (e.g., heart) is identified beforehand by using a usual test etc., and the state of another organ (e.g., kidney) is predicted from the stage of the disease in the specific organ. Taking this case as an example, an outline of the prediction method of Forward iOrgans is described with reference to FIG. 4.

First, information that the stage of myocardial infarction in a subject is the acute phase, the convalescent phase, or the maintenance phase is determined from the results of, for example, a biochemical test of the blood serum or the like. Next, the stage of the subject is checked against standard data 2 (e.g., FIG. 4(a)) that includes patterns of inter-organ cross talk indicators in each organ, including the heart, stored for each stage of myocardial infarction, thereby extracting patterns of the inter-organ cross talk indicators corresponding to the stage (e.g., acute phase) of myocardial infarction in the subject (FIG. 4(b)) from the data of FIG. 4(a). Furthermore, the pattern of the inter-organ cross talk indicator derived from the kidney (FIG. 4(c)) is extracted from the patterns of FIG. 4(b). By this procedure, the pattern of the inter-organ cross talk indicator derived from the kidney (FIG. 4(c)) can be inferred to be the pattern of the inter-organ cross talk indicator derived from the kidney at the stage of the subject. Based on the inter-organ cross talk indicator shown in the pattern inferred, the state of the kidney can be predicted from previously reported information regarding diseases and complications.

Figure 6:
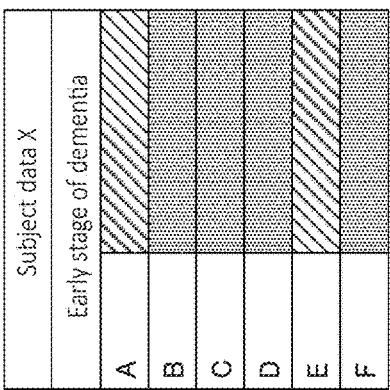
FIG. 6 schematically illustrates an outline of Drug iOrgans according to the present invention.

FIGS. 5 and 6 schematically illustrate an outline of Drug iOrgans according to the present invention for use in predicting a side effect (or side effects) and efficacy of a test substance. According to the inter-organ cross talk system, a side effect (or side effects) of many drugs are caused by changes (increase or decrease) in an inter-organ cross talk indicator from the state "(a1, a2, a3, a4, etc.)" to the state "Δ(a1, a2, a3, a4, etc.)" as a result of action of such a drug on organ A (FIG. 5(a)). In view of the inter-organ cross talk system, a side effect (or side effects) are caused in organ B, organ C, and organ D by action of a drug on organ A. The same theory as in the case of a side effect (or side effects) applies to efficacy of a drug, as shown in FIG. 5(b).

In conventional methods for detecting a side effect (or side effects) and for confirming efficacy, changes in organ A are only observed, and thus effects in organ B, organ C, and organ D are overlooked. D-iOrgans can not only evaluate changes in the inter-organ cross talk indicator from "(a1, a2, a3, a4, etc.)" to "Δ(a1, a2, a3, a4, etc.)" in organ A, but also comprehensively analyze changes in the inter-organ cross talk indicator in other organs due to administration of a drug, for example, changes from "Δ(b1, b2, b3, b4, etc.)" to "Δ(b1, b2, b3, b4, etc.)," from "(c1, c2, c3, c4, etc.)" to "Δ(c1, c2, c3, c4, etc.)," and from "(d1, d2, d3, d4, etc.)" to "Δ(d1, d2, d3, d4, etc.)" in organ B, organ C, and organ D.

An example of the prediction method of D-iOrgans is described with reference to FIG. 6. First, a pattern of gene expression (i.e., a pattern of an inter-organ cross talk indicator) in each organ is obtained beforehand for each stage of one or more diseases as standard data Y. FIG. 6(a) shows an example of the standard data Y. The standard data Y shown in FIG. 6 (a) includes patterns of the inter-organ cross talk indicators, each of the patterns being derived from the predetermined relationship between the amount of the inter-organ cross talk indicator in the organ of a positive control individual (or positive control individuals) affected with a disease and the amount of the corresponding inter-organ cross talk indicator in the same organ in a negative control (or negative controls). This standard data Y shows a pattern of the inter-organ cross talk indicator, i.e., A to F derived from adipose tissue at each of the stages (normal state, early stage, middle stage, and late stage) of myocardial infarction, dementia, and glioma. In the patterns of the inter-organ cross talk indicators in the early stage to the late stage in each disease, items in the inter-organ cross talk indicators shown in gray represent items in the inter-organ cross talk indicators showing no changes relative to normal, and items in the inter-organ cross talk indicators shown with diagonal hatching represent items in the inter-organ cross talk indicators showing changes relative to normal.

Next, adipose tissue is collected from a subject to which a test substance has been administered, and the pattern of the inter-organ cross talk indicator in the adipose tissue is determined and used as subject data X (e.g., FIG. 6(b)). Subsequently, the standard data Y and the subject data X of adipose tissue are compared with each other, and similarity between the patterns is calculated. When a pattern similar to the subject data X is present in the standard data Y, it can be predicted that administration of the test substance causes the subject to be in the same state as when the disease at the stage associated with the similar pattern in the standard data Y has developed. In the example shown in FIG. 6, the pattern of the subject data X shown in (b) is similar to the pattern of the early stage of dementia in the standard data Y. This suggests that a disease corresponding to dementia at the early stage may have developed in the subject by administration of the test substance. It can thus be predicted that the test substance may have a side effect (or side effects) corresponding to dementia at the early stage.

Moreover, when a positive control individual or positive control individuals with individual diseases used for obtaining the standard data Y shown in FIG. 6(a) are receiving any treatment (administration of an existing substance) and the subject data X is the pattern shown in FIG. 6(b), it can be predicted that the test substance has efficacy corresponding to the existing substance.

Since subjective symptoms often do not appear at the early stage of diseases, conventional methods are unable to predict the efficacy or side effect (or side effects) of a test substance that do not appear as subjective symptoms. In contrast, in the prediction method of D-iOrgans, subject data X is compared with standard data Y of patterns of the inter-organ cross talk indicators linked with the corresponding stages of a disease, including the early stage, and the efficacy or side effect (or side effects) of the test substance is predicted using the similarity between the patterns as a measure. The prediction method of D-iOrgans thus also can predict the efficacy or side effect (or side effects) of a test substance that do not appear as subjective symptoms.

Taking colorectal cancer as an example, an embodiment of D-iOrgans is described with reference to FIG. 7. For example, FIG. 7(a) shows standard data 1 derived from the testis, kidney, skin, and colon without administration of a test substance in the case where the test substance is administered to an individual (e.g., a mouse) who is healthy, has a precancerous lesion of colorectal cancer, or has developed colorectal cancer. In FIG. 7, for example, a subject who is administered a test substance is a healthy individual and subject data X shown in FIG. 7(b) is the pattern of an inter-organ cross talk indicator derived from tissue originating from the colon of the subject. The subject data X is compared with data derived from the colon in the standard data 1 of FIG. 7(a). In this case, the subject data X is similar to the pattern of precancerous lesion of colorectal cancer in the standard data 1; therefore, it can be predicted that administration of the test substance to healthy individuals causes a precancerous lesion of colorectal cancer. Further, it can be predicted that the test substance may cause colorectal cancer in the future. Moreover, in FIG. 7, for example, a subject who is administered a test substance has colorectal cancer and subject data X shown in FIG. 7(b) is the pattern of an inter-organ cross talk indicator derived from the lesion after administration of the test substance. The subject data X is similar to the pattern of precancerous lesion of colorectal cancer in the standard data 1; therefore, it can be predicted that the test substance is effective in the treatment of colorectal cancer.

Furthermore, according to the present invention, the state of the colon can be predicted, for example, from a pattern of gene expression derived from the skin in the standard data 1 (FIG. 7(a)) without using tissue of the colon itself, in view of the inter-organ cross talk system. For example, in FIG. 7, a subject who is administered a test substance is a healthy individual and subject data X shown in FIG. 7(c) is the pattern of an inter-organ cross talk indicator derived from tissue originating from the skin of the subject. The subject data X is compared with the data derived from the skin in the standard data 1 shown in FIG. 7(a). In this case, the subject data X is similar to the pattern of precancerous lesion of colorectal cancer in the standard data 1; therefore, it can be predicted that the test substance causes a precancerous lesion in the colon. Moreover, for example, in FIG. 7, a subject who is administered a test substance has colorectal cancer and subject data X shown in FIG. 7(c) is the pattern of an inter-organ cross talk indicator derived from the skin after administration of the test substance. The subject data X is compared with the data of skin in the standard data 1. In this case, the subject data X is similar to the pattern of precancerous lesion of colorectal cancer in the standard data 1; therefore, it can be predicted that the test substance is effective against colorectal cancer. More specifically, for instance, when tissue to be observed is in, for example, the abdominal cavity and thus a laparotomy is required to collect the tissue, the skin or another organ that is easy to collect can be used instead of the tissue to predict the efficacy or side effect (or side effects) of a test substance in multiple organs other than the skin. Furthermore, the efficacy or side effect (or side effects) can be detected earlier in multiple organs at the same time by linking D-iOrgans to R-iOrgans or F-iOrgans.

1. Explanation of Terms

First, terms used in the present specification, claims, and abstract are explained.

"Individual" as used herein is not particularly limited. Examples include mammals, such as humans, mice, rats, dogs, cats, rabbits, bovines, horses, goats, sheep, and pigs, birds, such as chickens, and the like. The individual is preferably a mammal such as a human, a mouse, a dog, a cat, a bovine, a horse, or a pig, more preferably a human, a mouse, a dog, a cat, or the like, even more preferably a human or a mouse, and the most preferably a human. In addition, the term "individual" includes both individuals having disease and individuals having no disease. There is no limitation on the age or sex (male or female) of the individual; however, the individual is preferably the same species, the same age, and/or the same sex as the subject described later. However, in the embodiment in "6. D-iOrgans" described later, when a test substance is administered to an individual, humans are excluded from the individuals.

Moreover, the term "individual" also includes individuals that gestate.

The ages of the individuals in the present invention may be classified into the following age groups in humans: under 7 years of age, 7 years of age or older but under 15 years of age, 15 years of age or older but under 30 years of age, 30 years of age or older but under 60 years of age, and 60 years of age or older. The age in the present invention is not particularly limited and is preferably 15 years of age or older but under 30 years of age, 30 years of age or older but under 60 years of age, or 60 years of age or older, and more preferably 30 years of age or older but under 60 years of age, or 60 years of age or older. In mice, the ages may be classified into the following age groups: under 6 weeks of age, 6 weeks of age or older but under 24 weeks of age, 24 weeks of age or older but under 48 weeks of age, and 48 weeks of age or older.

Here, an individual with a specific disease described later is referred to as "positive control," and an individual without a specific disease described later is referred to as a "negative control."

In the present invention, "tissue" refers to a collection of cells that have a similar function and a similar shape.

"Organ" as used herein means a collection of tissue in a subject that has a certain independent form and a specific function. Specific examples include organs of the circulatory system (such as the heart, arteries, veins, and lymphatic vessels), organs of the respiratory system (such as the nasal cavity, paranasal sinus, larynx, trachea, bronchus, and lungs), organs of the digestive system (such as the lips, buccal region, palate, teeth, gums, tongue, salivary glands, pharynx, esophagus, stomach, duodenum, jejunum, ileum, cecum, appendix, ascending colon, transverse colon, sigmoid colon, rectum, anus, liver, gallbladder, bile duct, biliary tract, pancreas, and pancreatic duct), organs of the urinary system (such as the urethra, urinary bladder, ureter, and kidney), organs of the nervous system (such as the cerebrum, cerebellum, midbrain, brainstem, spinal cord, peripheral nerves, and autonomic nerves), organs of the female reproductive system (such as the ovaries, Fallopian tubes, uterus, and vagina), breasts, organs of the male reproductive system (such as the penis, prostate gland, testes, epididymis, and vas deferens), organs of the endocrine system (such as the hypothalamus, hypophysis, pineal body, thyroid gland, parathyroid gland, and adrenal gland), organs of the integumentary system (such as skin, hair, and nails), organs of the hematopoietic system (such as blood, bone marrow, and spleen), organs of the immune system (such as lymph nodes, tonsils, and thymus), bone and soft tissue organs (such as bones, cartilage, skeletal muscles, connective tissue, ligaments, tendons, diaphragm, peritoneum, pleura, and adipose tissue (brown fat and white fat)), organs of the sensory organ system (such as the eyeballs, eyelids, lacrimal glands, outer ear, middle ear, inner ear, and cochlea). Preferable examples of tissue in the present invention include tissue of the heart, cerebrum, lung, kidney, adipose tissue, liver, skeletal muscle, testis, spleen, thymus, bone marrow, pancreas, skin (for example, including the epidermis, the papillary layer, and the reticular layer above the subcutis; preferably not containing adipose tissue, cartilage tissue, or the like), and the like. More preferred examples of tissue include tissue of the heart, cerebrum, lung, kidney, adipose tissue, liver, skeletal muscle, spleen, bone marrow, pancreas, skin, and the like.

Furthermore, in the case of using an individual that gestates (preferably an individual other than humans) as a subject, the term "organ" in the present invention may include the whole body of an embryo or the organs described above of an embryo.

In the present invention, body fluids, such as serum, plasma, urine, spinal fluid, ascites fluid, pleural effusion, saliva, gastric fluid, pancreatic fluid, bile, and milk, particularly preferably plasma, may be used instead of the organs described above.

"Specific organ" as used herein refers to an organ with a specific disease described later. The term "organ other than the specific organ" includes the organs described above other than the specific organ. The organ other than the specific organ may be one or more kinds of organs. The organ other than the specific organ is preferably an organ other than blood. More preferably, the organ other than the specific organ does not include body fluids. The organ other than the specific organ is particularly preferably skin, adipose tissue, and the like.

"Originating from an organ" as used herein means, for example, being collected from an organ or being cultured from cells or tissue of a collected organ, or a body fluid.

"Inter-organ cross talk indicator" as used herein is at least one in vivo factor (or molecule) that is present in a living organism and acts as a measure representing the states of organs through organ-to-organ communication (i.e., inter-organ cross talk) in a living organism. In other words, the inter-organ cross talk indicator is an in vivo substance or in vivo substances that can undergo changes in cells or tissue originating from each organ, and/or a body fluid in an individual having a specific disease, depending on whether the disease is present. Examples of in vivo substances that can act as an inter-organ cross talk indicator include nucleic acids; carbohydrates; lipids; glycoproteins; glycolipids; lipoproteins; amino acids, peptides; proteins; polyphenols; chemokines; at least one metabolite selected from the group consisting of metabolic end products of the above substance or substances, intermediate metabolites of the above substance or substances, and starting substance or substances for one or more metabolic pathways of the above substance; metal ions; and the like. Preferable examples are nucleic acids.

In the present invention, the nucleic acid is preferably RNA, such as mRNA, non-coding RNA, or microRNA, and more preferably mRNA. The RNA is preferably at least one RNA selected from the group consisting of mRNAs, non-coding RNAs, and microRNAs that can be expressed in cells or tissue originating from organs described above or cells in body fluids (also referred to herein as "group 1"), more preferably RNAs expressed from genes listed in FIG. 25 or 26 in which the RNAs can be detected by RNA-Seq etc. (also referred to herein as "group 2") and RNAs expressed from orthologs of the genes. HomoloGene (http://www.ncbi.nlm.nih.gov/homologene), a website provided by NCBI, or the like can be used to search for orthologs in animal species from the Reference Seq. IDs described in FIG. 25 or 26. Examples of orthologs in, for example, humans include those represented by the Human Gene IDs described in FIG. 30. Among these, the RNAs having polyA sequences are preferable. In an individual in which an ortholog corresponding to a gene described in FIG. 25 or 26 is not present, the ortholog is excluded from the analysis. It is more preferred that non-coding RNAs and microRNAs (their NCBI Reference Seq IDs start with "NR") be excluded from the analysis in individuals other than mice.

For example, when the specific organ is the heart and the specific disease is myocardial infarction, at least one RNA selected from the group consisting of RNAs expressed from the genes of group 3 listed in FIG. 30 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 30 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 30 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 30 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 30 or at least one RNA selected from the group consisting of RNAs expressed from the orthologs, of the genes of group 7, that are present in the individual described above is more preferable than RNAs expressed from the genes of group 6. At least one RNA selected from the group consisting of RNAs expressed from the genes of group 8 described in FIG. 31 or at least one RNA selected from the group consisting of RNAs expressed from the orthologs, of the genes of group 8, that are present in the individual described above is most preferable. However, orthologs of Sult5a1 are excluded from the orthologs of the genes of group 8 in individuals other than mice.

For example, when the specific organ is the brain and the specific disease is dementia, at least one RNA selected from the group consisting of RNAs expressed from the genes of group 3 listed in FIG. 34 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 34 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 34 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 34 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 described in FIG. 34 or at least one RNA selected from the group consisting of RNAs expressed from the orthologs, of the genes of group 7, that are present in the individual described above is more preferable than RNAs expressed from the genes of group 6.

For example, when the specific disease is a tumor, at least one RNA selected from the group consisting of RNAs expressed from the genes of group 3 listed in FIG. 36, 38, or 39 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 36, 38, or 39 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 36, 38, or 39 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 36, 38, or 39 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 36, 38, or 39 or at least one RNA selected from the group consisting of RNAs expressed from the orthologs, of the genes of group 7, that are present in the individual described above is more preferable than RNAs expressed from the genes of group 6.

When the disease is a tumor and the organ other than the specific organ is skin, at least one RNA selected from the group consisting of RNAs expressed from the genes of group 3 listed in FIG. 38 or 39 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 38 or 39 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 38 or 39 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 38 or 39 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 38 or 39 or at least one RNA selected from the group consisting of RNAs expressed from the orthologs, of the genes of group 7, that are present in the individual described above is more preferable than RNAs expressed from the genes of group 6. RNA expressed from at least one gene selected from the group consisting of FCGR3B, FPR1, HLA-DQA1, LINC00260, LOC286437, MALAT1, MIR1184-1, MIR1247, PRG4, RPL21P44, RPPH1, RPS15AP10, SCARNA4, SNORA31, SNORA77, ZBTB20, and orthologs thereof is particularly preferable.

When the disease is breast cancer and the organ other than the specific organ is skin, at least one RNA selected from the group consisting of RNAs expressed from the genes of group 3 listed in FIG. 38 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 38 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 described in FIG. 38 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 38 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 38 or at least one RNA selected from the group consisting of RNAs expressed from the orthologs, of the genes of group 7, that are present in the individual described above is more preferable than RNAs expressed from the genes of group 6. RNA expressed from at least one gene selected from the group consisting of PRG4, HLA-DQA1, LOC100302650, MIR1184-1, MIR1248, MIR203, MIR205, MIR570, RPPH1, SCARNA4, SNORA31, SNORA4, and orthologs thereof is particularly preferable.

When the disease is lung cancer and the organ other than the specific organ is skin, at least one RNA selected from the group consisting of RNAs expressed from the genes of group 3 listed in FIG. 39 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 39 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 described in FIG. 39 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 described in FIG. 39 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 described in FIG. 39 or at least one RNA selected from the group consisting of RNAs expressed from the orthologs, of the genes of group 7, that are present in the individual described above is more preferable than RNAs expressed from the genes of group 6. RNA expressed from at least one gene selected from the group consisting of AGSK1, CYP2E1, KRT6C, RPL21, RPL9, TPPP, DCD, DDX3Y, FCGR3B, HBA2, HIST1H4C, HLA-DQA1, LOC286437, MALAT1, MIR1184-1, RPPH1, RPS15AP10, RPS4Y1, SCARNA4, SCGB2A1, SFTPA1, SFTPA2, SNORA31, SNORA77, ZBTB20, and orthologs thereof is particularly preferable.

When the disease is a tumor and the organ other than the specific organ is blood, at least one RNA selected from the group consisting of RNAs expressed from the genes of group 3 listed in FIG. 40 or 41 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 40 or 41 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 40 or 41 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 40 or 41 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 40 or 41 or at least one RNA selected from the group consisting of RNAs expressed from the orthologs, of the genes of group 7, that are present in the individual described above is more preferable than RNAs expressed from the genes of group 6. RNA expressed from at least one gene selected from the group consisting of HNRNPH2, HP, LOC283663, SNORA40, TCN2, and orthologs thereof is particularly preferable.

When the disease is breast cancer and the organ other than the specific organ is blood, at least one RNA selected from the group consisting of RNAs expressed from the genes of group 3 listed in FIG. 40 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 40 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 40 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 40 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 listed in FIG. 40 or at least one RNA selected from the group consisting of RNAs expressed from the orthologs, of the genes of group 7, that are present in the individual described above is more preferable than RNAs expressed from the genes of group 6.

When the disease is lung cancer and the organ other than the specific organ is blood, at least one RNA selected from the group consisting of RNAs expressed from the genes of group 3 listed in FIG. 41 or at least one RNA selected from the group consisting of RNAs expressed from the orthologs, of the genes of group 3, that are present in the individual described above is preferable. At least one RNA selected from the group consisting of RNAs expressed from the genes of group 4 listed in FIG. 41 or at least one RNA selected from the group consisting of RNAs expressed from the orthologs, of the genes of group 4, that are present in the individual described above is more preferable than RNAs expressed from the genes of group 3. At least one RNA selected from the group consisting of RNAs expressed from the genes of group 5 listed in FIG. 41 or at least one RNA selected from the group consisting of RNAs expressed from the orthologs, of the genes of group 5, that are present in the individual described above is more preferable than RNAs expressed from the genes of group 4. At least one RNA selected from the group consisting of RNAs expressed from the genes of group 6 listed in FIG. 41 or at least one RNA selected from the group consisting of RNAs expressed from the orthologs, of the genes of group 6, that are present in the individual described above is more preferable than RNAs expressed from the genes of group 5. At least one RNA selected from the group consisting of RNAs expressed from the genes of group 7 described in FIG. 41 or at least one RNA selected from the group consisting of RNAs expressed from the orthologs, of the genes of group 7, that are present in the individual described above is more preferable than RNAs expressed from the genes of group 6.

Metabolites that are present in cells or tissue originating from the organs described above encompass nucleic acids, carbohydrates, lipids, glycoproteins, glycolipids, lipoproteins, amino acids, peptides, proteins, polyphenols, chemokines, and metabolic end products of these substances, intermediate metabolites of these substances, and starting materials for synthesis of these substances (also referred to herein as "group A"). For example, the metabolite is preferably at least one of the metabolites listed in FIG. 27 (also referred to herein as "group B"), which can be detected by a known method. More specifically, the metabolite is at least one of the metabolites listed in FIG. 28 (also referred to herein as "group C").

For example, when the specific organ is the heart and the specific disease is myocardial infarction, the metabolite is preferably one or more metabolites listed in FIG. 29.

For example, when the specific organ is the brain and the specific disease is dementia, the metabolite is preferably one or more metabolites listed in FIG. 33.

"An amount of an inter-organ cross talk indicator" or "amounts of inter-organ cross talk indicators" as used herein may be expressed as a quantitative value (or a quantitative level) or expressed semi-quantitatively as follows: for example, "increase," "no change," and "decrease." "An amount of an inter-organ cross talk indicator" or "amounts of inter-organ cross talk indicators" may be the measurement value of the inter-organ cross talk indicator.

A disease in the specific organ to be detected in the present invention is referred to as a "specific disease." The specific disease can include any disease and abnormality that can develop in organs mentioned above of the individual. (However, in some cases, diabetes and chronic renal failure are excluded from the disease to be detected in the present invention.) That is, the specific disease also includes abnormalities characteristic of the specific disease that occur before onset of the disease (such abnormalities are also referred to as "prelesions"). Preferable specific diseases include thrombosis, embolism, stenosis and like ischemic diseases (in particular, in the heart, brain, lung, colon, etc.); aneurysm, varix, congestion, hemorrhage, and like circulatory disturbances (in the aorta, veins, lungs, liver, spleen, retinas, etc.); allergic bronchitis, glomerulonephritis, and like allergic diseases; dementia, Parkinson's disease, amyotrophic lateral sclerosis, myasthenia gravis, and like degenerative diseases (in nerves, skeletal muscles, etc.); tumors (benign epithelial tumors, benign non-epithelial tumors, malignant epithelial tumors, and malignant non-epithelial tumors); metabolic diseases (disorders of carbohydrate metabolism, disorders of lipid metabolism, and electrolyte abnormality); infections (bacterial, viral, rickettsial, chlamydial, fungal, protozoal, parasitic, etc.); and the like. More preferred specific diseases include ischemic diseases in the heart or brain; neurodegenerative diseases including Alzheimer-type (young-onset) dementia and cerebrovascular dementia; malignant epithelial tumors or malignant non-epithelial tumors; and metabolic diseases, such as fatty liver and obesity. Particularly preferred examples include ischemic heart diseases (myocardial infarction and angina), malignant epithelial tumors (from the lungs, stomach, duodenum, colon, rectum, mammary glands, uterus, prostate gland, urinary bladder, etc.), malignant non-epithelial tumors (gliomas, such as astrocytomas, oligodendrogliomas, and ependymomas) and neurodegenerative diseases, such as Alzheimer-type dementia. Preferably, diseases that cause systemic symptoms are excluded from the specific diseases. Examples of diseases that cause systemic symptoms include autoimmune diseases such as systemic lupus erythematosus and multiple sclerosis; metabolic disorders such as hereditary mucopolysaccharidosis; influenza viral, adenoviral, and like infections.

The stage can be determined by a procedure already used for the above diseases, such as endoscopy, X-ray tests, MRI tests, ultrasonography, cardiac function tests, respiratory tests, histological tests, hematological tests, biochemical tests, immunological tests, or urinalysis. The stage also includes the period of time in which a prelesion appears (also referred to as "pre-disease stage").

Figure 46:
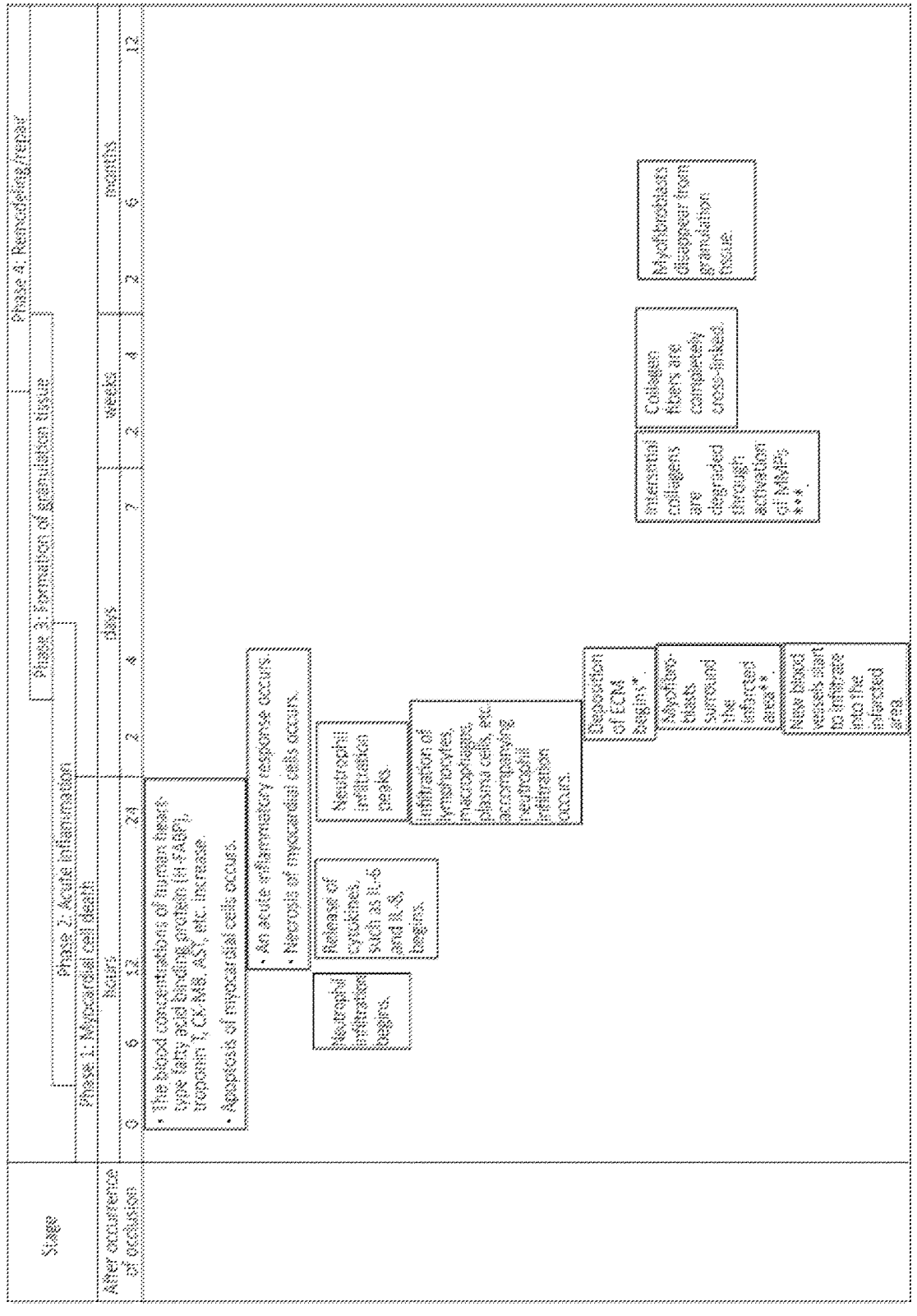
FIG. 46 illustrates the staging classification for myocardial infarction.

For example, myocardial infarction can be staged according to FIG. 46. FIG. 46 was prepared based on a document by Jack P. M. Cleutjens et al. (Cardiovascular Research, 1999, vol. 44, pp. 232-241). Cleutjens et al. state that cardiac tissue is repaired in small animals, such as mice and rats, after myocardial infarction faster than in humans; however, according to a study by the present inventor, there is no notable difference in progress in stage between mice and humans (e.g., see Motoaki Murakoshi et al., PLOS ONE, 2013, vol. 8, issue 11, e79374). Accordingly, the staging classification for myocardial infarction shown in FIG. 46 is also applicable to mice.

* ECM indicates extracellular matrix. ECM is deposited, first in the border zone between the infarcted area and the non-infarcted area and later in the central area of the infarct. First, fibrin starts to be deposited, and then, other extracellular matrix molecules, such as fibronectin and tenascin, start to be deposited.

** Myofibroblasts secrete interstitial collagens. In rats etc. the amount of type III collagen increases around the occluded coronary artery, followed by production of type I collagen. At this time, collagen fibers are not cross-linked. Along with activation of collagen synthesis, collagen degradation is activated.

*** MMPs indicate matrix metalloproteinases. In this phase, collagenolytic activity results in loss of tissue structure support, distortion of architecture, and loss of cardiac stiffness. The wall of the heart may become thin, and rupture of the myocardium may occur.

Further, as an example of another staging classification of myocardial infarction in humans, the disease can be staged as follows, with the day of occurrence of infarction being designated as day 0: acute phase, a period of 1 or 2 weeks from day 0; convalescent phase, a period from 3 weeks to 2 or 3 months; and maintenance phase, a lifelong period thereafter.

Particularly in the acute phase of myocardial infarction, follow-up observation can be conducted based on the test items shown in Table 1 (*Shinryogun Betsu Rinsho Kensa no Gaidorain* 2003: 10. *Kyusei Shinkin Kosoku* (Diagnosis related group clinical examination guideline 2003: 10. acute myocardial infarction) by Tsutomu Yamazaki).

TABLE 1

| Hospital day (day) | 1 | 2 | 3 | 4 | 5 | 6 | 7 |
|---|---|---|---|---|---|---|---|
| Electrocardiogram monitor | Constantly | Constantly | Constantly | Constantly | Constantly | Constantly | Constantly |
| Blood pressure/pulse/respiration | 24 | 8 | 6 | 6 | 4 | 4 | 2 |
| Auscultation/physical findings | 12 | 6 | 4 | 4 | 2 | 2 | 2 |
| Urinary output | 6 | 6 | 2 | 2 | 1 | 1 | 1 |
| Standard 12-lead electrocardiogram | 8 | 4 | 2 | 2 | 2 | 1 | 1 |
| CK/CK-MB† | 8 | 4 | 2 | 1 | 1 | — | — |
| AST/LD | 4 | 2 | 1 | 1 | 1 | — | — |
| Troponin T (or I)/myosin light chain 1 | Can be measured only once for confirming the diagnosis | | | | | | |
| Blood count/erythrocyte sedimentation rate/CRP/coagulation test | 1 | 1 | 1 | 1 | — | — | — |
| Chest radiograph | 1 | 1 | 1 | 1 | — | — | — |
| Holter electrocardiogram | — | — | — | — | — | — | 1 |
| Blood gases | 1 | 1 | — | — | — | — | — |
| Cardiac echo | 1 | — | 1 | — | — | — | 1 |
| Cardiac catheter | 1 | — | — | — | — | — | — |
| Myocardial scintigram | — | — | — | — | — | — | 1 |
| Exercise electrocardiogram | — | — | — | — | — | — | 1 |

■ Unit (times/day)
* Until the peak value. Thereafter, followed based on the other items.
†CK-MB can be measured only once for a definite diagnosis.

When the specific disease is Alzheimer-type dementia, the following classification (Koichi Kozaki (2012) Japanese Journal of Geriatrics, Vol. 49, no. 4, pp. 419-424), for example, can be used to stage the disease.

TABLE 2

| Stage | Clinical Diagnosis | Characteristics |
|---|---|---|
| 1 | Normal adult | No objective or subjective functional impairment |
| 2 | Normal aging | Misplacing objects, complaint of memory loss, difficulty in finding words |
| 3 | Borderline region | Unable to perform complex work tasks, decreased function in a skilled job evident to co-workers, difficulty in traveling to new locations |
| 4 | Mild | Unable to perform complex tasks in daily life, such as planning a party, shopping, and handling finances |
| 5 | Moderate | Unable to choose proper attire according to time, place, and occasion; persuasion may be necessary to give the patient a bath |
| 6a | Moderately severe | Unable to put on clothes in the proper order by himself/herself |
| b | | Requires assistance in bathing, unwilling to taking a bath |
| c | | Forgets to flush the toilet or wipe |
| d | | Urinary incontinence |
| e | | Fecal incontinence |
| 7a | Severe | Decreased language function limited to about six words or fewer |
| b | | Intelligible vocabulary limited to a single word, such as "yes" |
| c | | Ambulatory ability lost |
| d | | Ability to sit up lost |
| e | | Ability to smile lost |
| f | | Unable to hold head up, ultimately loss of consciousness (stupor or coma) |

Prepared based on Sclan SG et al. Int Psychogeriatr. 1992: 4 Suppl 1: 55-69.

When the specific disease is a malignant epithelial tumor (cancer), the UICC TNM classification (7th ed.) or the like can be used to stage the disease.

For example, colorectal cancer can be staged according to the UICC TNM classification (7th ed.) as shown in Tables 3-1 to 3-3 below.

TABLE 3-1

UICC TNM classification (7th ed.)
Matrix of stages (colon and rectum)

| UICC TNM Classification 7th edition | | N0 | N1a | N1b | N1c | N2a | N2b |
|---|---|---|---|---|---|---|---|
| Tis | | 0 | | | | | |
| T1 | | I | IIIA | IIIA | IIIA | IIIA | IIIB |
| T2 | | I | IIIA | IIIA | IIIA | IIIB | IIIB |
| T3 | | IIA | IIIB | IIIB | IIIB | IIIB | IIIC |
| T4 | T4a | IIB | IIIB | IIIB | IIIB | IIIC | IIIC |
| | T4b | IIC | IIIC | IIIC | IIIC | IIIC | IIIC |
| M1 | M1a | IVA | IVA | IVA | IVA | IVA | IVA |
| | M1b | IVB | IVB | IVB | IVB | IVB | IVB |

TABLE 3-2

1) TNM classification (UICC) (7th ed.) 2010

T- Primary tumor; the depth of tumor invasion described in Japanese Classification of Colorectal Carcinoma (8th ed.) is noted in parentheses

| | |
|---|---|
| TX | Primary tumor cannot be assessed |
| T0 | No evidence of primary tumor |
| Tis[1] | Carcinoma in situ: intraepithelial tumor or invasion of lamina propria (M) |
| T1 | Tumor invades submucosa (SM) |
| T2 | Tumor invades muscularis propria (MP) |
| T3 | Tumor invades into the subserosa or into the non-peritonealized pericolic or perirectal tissue (SS, A) |
| T4 | Tumor perforates the visceral peritoneum, and/or tumor directly invades other organs or structures and/or tumor perforates the visceral peritoneum (serosa) |
| T4a | Tumor perforates the visceral peritoneum (SE) |
| T4b | Tumor directly invades other organs or structures[2,3] (SI, AI) |

Note 1: Tis includes cancer cells confined within the glandular epithelial basement membrane (intraepithelial) or lamina propria (intramucosal) with no extension through the muscularis mucosae into the submucosa.
Note 2: Direct invasion in T4b includes invasion of other organs or the colorectum by way of the serosa, as confirmed on microscopic examination, or for tumors in a retroperitoneal or subperitoneal location, direct invasion of other organs or structures by virtue of extension beyond the muscularis propria
Note 3: A tumor that is adherent to other organs or structures, macroscopically, is classified as cT4b. However, if no tumor is present microscopically in the adhesion, the classification should be pT1-3 depending on the anatomical depth of wall invasion.

N- Regional lymph nodes

| | |
|---|---|
| NX | Regional lymph node metastasis cannot be assessed |
| N0 | No regional lymph node metastasis |
| N1 | Metastasis in 1-3 regional lymph nodes |
| N1a | Metastasis in one regional lymph node |
| N1b | Metastasis in 2-3 regional lymph nodes |
| N1c | Tumour deposits*, i.e., satellite nodules, in the subserosa or in non-peritonealized pericolic or perirectal soft tissue without regional lymph node metastasis |
| N2 | Metastasis in 4 or more regional lymph nodes |
| N2a | Metastasis in 4-6 regional lymph nodes |
| N2b | Metastasis in 7 or more regional lymph nodes |

*Tumour deposits (satellite nodules), i.e., macroscopic or microscopic tumor nests or nodules, in the lymph drainage area of adipose tissue around the intestinal tract of a primary tumor without histological evidence of residual lymph node structure TABLE 3-2-continued may represent discontinuous spread of tumor or venous invasion with extravascular spread (V1/2) or a lymph node totally replaced by a tumor (N1/2). If such deposits are observed with lesions that would otherwise be classified as T1 or T2, then the T classification is not changed, but the nodule(s) are classified as N1c. If a nodule is considered by the pathologist to be a lymph node totally replaced by a tumor (generally having a smooth contour), it should be recorded that lymph node metastasis is positive and not that a satellite nodule exists, and each nodule should be counted separately in the final pN determination.

M- Distant metastasis

| | |
|---|---|
| MX | Distant metastasis cannot be assessed |
| M0 | Distant metastasis is not found |
| M1 | Distant metastasis is found |
| | M1a Metastasis confined to one organ (liver, lung, ovary, or nonregional lymph node) |
| | M1b Metastases in two or more organs or the peritoneum |

TABLE 3-3

| Stage | | | | |
|---|---|---|---|---|
| Stage 0 | Tis | N0 | M0 | |
| Stage I | T1, T2 | N0 | M0 | |
| Stage II | T3, T4 | N0 | M0 | |
| Stage IIA | T3 | N0 | M0 | |
| Stage IIB | T4a | N0 | M0 | |
| Stage IIC | T4b | N0 | M0 | |
| Stage III | Any T | N1, N2 | M0 | |
| Stage IIIA | T1, T2 | N1 | M0 | |
| | T1 | N2a | M0 | |
| Stage IIIB | T3, T4a | N1 | M0 | |
| | T2, T3 | N2a | M0 | |
| | T1, T2 | N2b | M0 | |
| Stage IIIC | T4a | N2a | M0 | |
| | T3, T4 | N2b | M0 | |
| | T4b | N1, N2 | M0 | |
| Stage IVA | Any T | Any N | M1a | |
| Stage IVB | Any T | Any N | M1b | |

See UICC TNM classification of malignant tumours, 7th ed., translated into Japanese, p. 98 (Kanehara & Co., Ltd., 2010).

When the specific disease is a glioma, the disease can be classified into the following grades, which were posted on a web page on Jan. 11, 2011, by the Japan Neurosurgical Society, (http://square.umin.ac.jp/neuroinf/medical/204.html).

TABLE 4

| | Astrocytoma-type | Oligodendroglioma-type | Mixed tumor |
|---|---|---|---|
| Grade 1 | Pilocytic astrocytoma | | |
| Grade 2 | Diffuse astrocytoma | Oligodendroglioma | Oligoastrocytoma |
| Grade 3 | Anaplastic astrocytoma | Anaplastic oligodendroglioma | Anaplastic oligoastrocytoma |
| Grade 4 | Glioblastoma | | |

When the specific disease is breast cancer, the disease can be classified, for example, into stages 0 to 4 according to a web page of Osaka University (http://www.med.osaka-cu.ac.jp/surgical-oncology/detail/nyugan.html), as described below.

Stage 0: Non-invasive cancer (cancer cells remain in lactiferous ducts or acini and rarely metastasize);

Stage 1: The size of the lump is 2 cm or less without metastasis to lymph nodes;

Stage 2A: The size of the lump is 2 cm or less and metastasis to axillary lymph nodes is observed; or the size of the lump is 2.1 to 5 cm without metastasis to lymph nodes;

Stage 2B: The size of the lump is 2.1 to 5 cm and metastasis to axillary lymph nodes is observed; or the size of the lump is 5 cm or more without metastasis to Lymph nodes;

Stage 3A: The size of the lump is 5 cm or less and axillary lymph nodes are strongly attached to the surrounding tissue or lymph nodes; or the size of the lump is more than 5 cm and metastasis to axillary lymph nodes or lymph nodes behind the sternum is observed;

Stage 3B: Regardless of the size of the lump and metastasis to lymph nodes, the lump protrudes from the skin or is firmly attached to the chest wall;

Stage 3C: Regardless of the size of the lump, there is metastasis to supraclavicular and infraclavicular lymph nodes; or metastasis to both axillary lymph nodes and lymph nodes behind the sternum is observed;

Stage 4: Metastasis to a distant organ, such as bone, lung, or liver, is observed.

When the specific disease is lung cancer, the disease can be classified into stages I, II, III, and IV according to the criteria described on a web page of National Hospital Organization Osaka National Hospital (http://www.onh.go.jp/seisaku/cancer/kakusyu/haig.html#haig_02), as described below.

Stage I: The cancer is confined to the lung and there is no metastasis to lymph nodes;

Stage II: The cancer is confined to the lung and there is metastasis to only lymph nodes in the lung; or there is no metastasis to lymph nodes, but the cancer spreads to the surrounding area outside the lung that can be directly resected;

Stage III: There is no metastasis to other organs, but the disease is more advanced than stage II.

Stage IV: There is metastasis to another organ.

"Test substance" refers to a substance to be evaluated for its efficacy or side effect (or side effects) in the present invention.

"Existing substance" refers to a substance present at the time of practicing the present invention.

"Substance" is not particularly limited and may be novel or known. Examples of substances include compounds; nucleic acids; carbohydrates; lipids; glycoproteins; glycolipids; lipoproteins; amino acids; peptides; proteins; polyphenols; chemokines; at least one metabolite selected from the group consisting of metabolic end products, intermediate metabolites, and starting materials for synthesis, of the substances mentioned above; metal ions; microorganisms; and the like. These substances may be used singly or in a combination of two or more as a mixture. In another embodiment, examples of substances include drugs, quasi-drugs, medicated cosmetics, foods, foods for specified health uses, foods with function claims, and candidates for these. Substances that have been subjected to clinical studies for pharmaceutical approval, but that have not been commercialized are also included in the substances.

"Standard data 1" as used herein is a group of data of inter-organ cross talk indicators that serves as a measure for predicting the presence of a specific disease and/or the stage of the specific disease in a subject. More specifically, standard data 1 is a group of patterns of inter-organ cross talk indicators, each of the patterns being derived from a predetermined relationship between an amount of an inter-organ cross talk indicator in an organ other than the specific organ in a positive control (or positive controls) affected with the specific disease (hereinafter referred to as "positive control amount 1") and an amount of the corresponding inter-organ cross talk indicator in the same organ as the organ other than the specific organ in a negative control (or negative controls) without the specific disease (hereinafter referred to as "negative control amount 1"), and preferably a group of patterns of inter-organ cross talk indicators, each of the patterns being derived from a predetermined ratio between the positive control amount 1 and the negative control amount 1 (for example, the ratio obtained by dividing the value of the positive control amount 1 by the value of the negative control amount 1). More preferably, the amount of the inter-organ cross talk indicator is the expression level of at least one RNA, and the patterns of the inter-organ cross talk indicators are a group of patterns of expression of at least one RNA (also referred to herein as "standard data 1$a$"). In another embodiment, more preferably, the amount of the inter-organ cross talk indicator is the amount of at least one metabolite, and the patterns of the inter-organ cross talk indicators are a group of patterns of presence of at least one metabolite (also referred to herein as "standard data 1$b$").

Moreover, instead of standard data 1, correlation maps (standard data 1-Maps) may be used. The correlation maps (standard data 1-Maps) are generated using standard data 1 derived from multiple organs by determining, for each disease or each stage, the correlation of the patterns of inter-organ cross talk indicators between the organs. The method for generating the correlation maps is described below.

"Standard data 2" as used herein is a group of data of inter-organ cross talk indicators that serves as a measure for predicting the presence of a disease and/or the stage of the disease in each of one or more organs other than a specific organ in a subject affected with a specific disease. More specifically, standard data 2 is a group of patterns of inter-organ cross talk indicators predetermined for each stage, each of the patterns being derived from the predetermined relationship between the amount of an inter-organ cross talk indicator in an organ other than the specific organ in a positive control (or positive controls) affected with the specific disease (hereinafter also referred to as "positive control amount 2") and the amount of the corresponding inter-organ cross talk indicator in the same organ as the organ other than the specific organ in a negative control (or negative controls) without the specific disease (hereinafter also referred to as "negative control amount 2"). Preferably, standard data 2 is a group of patterns of inter-organ cross talk indicators predetermined for each stage of the specific disease, each of the patterns being derived from the predetermined ratio between the positive control amount 2 and the negative control amount 2 (for example, a ratio obtained by dividing the value of the positive control amount 2 by the value of the negative control amount 2). More preferably, the amount of the =ter-organ cross talk indicator is the expression level of at least one RNA, and the patterns of the inter-organ cross talk indicators are a group of patterns of expression of at least one RNA (also referred to herein as "standard data 2$a$"). In another embodiment, more preferably, the amount of the inter-organ cross talk indicator is the amount of at least one metabolite, and the patterns of the inter-organ cross talk indicators are a group of patterns of presence of at least one metabolite (also referred to herein as "standard data 2$b$").

Standard data 1 or 2 is obtained for each stage of a specific disease, each organ or body fluid, and if necessary, each sex and/or each age group. Each pattern of the inter-organ cross talk indicator is linked with information regarding the corresponding stage of a specific disease, the corresponding organ or body fluid, and information about the sex, age, etc. of a subject.

"Subject" is a subject to which the prediction methods according to the present invention are applied, and is preferably of a species corresponding to those of individuals used for determining patterns in standard data 1 or 2. For example, if individuals used for determining patterns in the standard data are mice, then a mouse, a rat, a human, or the like may be selected as the subject. The age and sex of the subject are not particularly limited, and the subject may be in the same age group and/or of the same sex as individuals used for determining patterns in standard data 1 or 2.

"Data of a subject" or "subject data" as used herein is data of an inter-organ cross talk indicator derived from all or part of an organ collected from a subject. More specifically, data of a subject or subject data is a pattern of an inter-organ cross talk indicator representing the relationship between the amount of the inter-organ cross talk indicator in an organ other than the specific organ of the subject and the amount of the corresponding inter-organ cross talk indicator in the same organ as the organ other than the specific organ in a negative control (or negative controls) without the specific disease. Data of a subject or subject data is preferably a pattern of an inter-organ cross talk indicator represented by the ratio between the amount of the inter-organ cross talk indicator in an organ other than the specific organ of the subject and the amount of the corresponding inter-organ cross talk indicator in the same organ as the organ other than the specific organ in a negative control (or negative controls) without the specific disease (for example, a ratio calculated by dividing the value of the amount of the inter-organ cross talk indicator in an organ other than the specific organ of the subject by the value of the amount of the corresponding inter-organ cross talk indicator in the same organ as the organ other than the specific organ in a negative control (or negative controls) without the specific disease). More preferably, the amount of the inter-organ cross talk indicator is the expression level of RNA from at least one gene, and the pattern of the inter-organ cross talk indicator is a pattern of expression of RNA from at least one gene (also referred to herein as "subject data A"). In another embodiment, more preferably, the amount of the inter-organ cross talk indicator is the amount of at least one metabolite, and the pattern of the inter-organ cross talk indicator is a pattern of presence of at least one metabolite (also referred to herein as "subject data B").

"Standard data Y" is a group of data of inter-organ cross talk indicators that serves as a measure for predicting the efficacy or side effect (or side effects) of a test substance. Standard data Y is a group of data of inter-organ cross talk indicators derived beforehand from one or more organs corresponding to the one or more organs from which subject data X is obtained. Standard data Y may be predetermined or obtained at the same time as subject data is obtained.

In an embodiment, standard data Y includes patterns of inter-organ cross talk indicators predetermined from the amounts of inter-organ cross talk indicators whose functions are already known (standard data Y1). In another embodiment, standard data Y includes patterns of inter-organ cross talk indicators, each of the patterns being derived from the predetermined relationship between the amount of an inter-organ cross talk indicator in an organ of an individual to which an existing substance has been administered and the amount of the corresponding inter-organ cross talk indicator in the same organ in a negative control (or negative controls) (standard data Y2). Standard data Y2 preferably includes patterns of inter-organ cross talk indicators, each of the patterns being predetermined from the ratio between the amount of an inter-organ cross talk indicator in an organ of an individual to which an existing substance has been administered and the amount of the corresponding inter-organ cross talk indicator in the same organ in a negative control (or negative controls) (for example, a ratio obtained by dividing the value of the amount of an inter-organ cross talk indicator in an organ of an individual to which an existing substance has been administered by the value of the amount of the corresponding inter-organ cross talk indicator in the same organ in a negative control (or negative controls)). In another embodiment, standard data Y includes patterns of inter-organ cross talk indicators, each of the patterns being derived from the predetermined relationship between the amount of an inter-organ cross talk indicator in an organ of a positive control individual or positive control individuals affected with a disease and the amount of the corresponding inter-organ cross talk indicator in the same organ in a negative control (or negative controls) (standard data Y3). Standard data Y3 preferably includes patterns of inter-organ cross talk indicators, each of the patterns being predetermined from the ratio between the amount of an inter-organ cross talk indicator in an organ of a positive control individual or positive control individuals affected with a disease and the amount of the corresponding inter-organ cross talk indicator in the same organ in a negative control (or negative controls) (for example, a ratio obtained by dividing the value of the amount of an inter-organ cross talk indicator in an organ of a positive control individual or positive control individuals with a disease by the value of the amount of the corresponding inter-organ cross talk indicator in the same organ in a negative control (or negative controls)).

In addition, standard data Y may be correlation maps generated using standard data Y2 derived from multiple organs by determining the correlation of the patterns of inter-organ cross talk indicators between the organs (standard data Y2-Maps) or correlation maps generated using standard data Y3 derived from multiple organs by determining the correlation of the patterns of inter-organ cross talk indicators between the organs (standard data Y3-Maps). The methods for determining the correlation maps are described later.

Subject data X is a group of data of an inter-organ cross talk indicator derived from each of one or more organs of an individual to which a test substance has been administered. The inter-organ cross talk indicator is derived from cells or tissue originating from each of the one or more organs. Subject data X may represent the amount of an inter-organ cross talk indicator derived from an organ of an individual to which a test substance has been administered. Preferably, subject data X may represent the relationship between the amount of an inter-organ cross talk indicator in an organ of an individual to which a test substance has been administered and the amount of the corresponding inter-organ cross talk indicator in the same organ in a negative control (or negative controls) or may be determined as the ratio between the amount of an inter-organ cross talk indicator in an organ of an individual to which a test substance has been administered and the amount of the corresponding inter-organ cross talk indicator in the same organ in a negative control (or negative controls). More preferably, subject data X may be determined as a ratio calculated by dividing the amount of an inter-organ cross talk indicator in an organ of an individual to which a test substance has been administered by the amount of the corresponding inter-organ cross talk indicator in the same organ in a negative control (or negative controls).

The term "pattern" includes, for example, the presence or absence of an inter-organ cross talk indicator, the amounts of inter-organ cross talk indicators, or changes in the amounts of inter-organ cross talk indicators over time, and a combination of the amounts of inter-organ cross talk indicators and changes in the amounts of inter-organ cross talk indicators over time. Preferably, the pattern includes the presence or absence of an inter-organ cross talk indicator, the amounts of inter-organ cross talk indicators, or changes in the amounts of inter-organ cross talk indicators over time, and a combination of the amounts of inter-organ cross talk indicators and changes in the amounts of inter-organ cross talk indicators over time, for each stage. Preferably, the pattern includes the presence or absence of expression of RNA from at least one gene, the expression level of RNA from at least one gene, or changes in the expression level of RNA from at least one gene over time, and a combination of the expression level of RNA from at least one gene and changes in the expression level of RNA from at least one gene over time.

"Gold standard" as used herein is an individual or individuals that have already been determined to have or not have the specific disease described above by a known test method and/or diagnostic method. The term "gold standard" also includes healthy individuals.

"Similarity" as used herein indicates the degree to which patterns of inter-organ cross talk indicators are similar when data of a subject is compared with standard data 1 or when subject data X is compared with standard data Y. More specifically, the similarity can be determined visually or by statistical analysis or the like.

Statistical analysis for calculating the similarity is not particularly limited as long as the similarity can be calculated. For example, the similarity can be calculated by using data of a subject and standard data 1 as independent variables and determining a quantified measure such as the correlation coefficient between the two groups.

Specific examples include (1) a method in which, if data of a subject and standard data 1 are each a single vector, the closeness between the directions in which the two compared vectors are pointing is determined; (2) a method in which the inter-organ cross talk indicator contained in data of a subject and the inter-organ cross talk indicator contained in standard data 1 are listed in descending order of amount, and the order correlation is determined; (3) a method in which the probability distribution of data of a subject and the probability distribution of standard data 1 are determined, and the pseudo-distance between the two probability distributions is measured; (4) a method in which the dimensionality of high-dimensional data of a subject and standard data 1 is reduced, and the distance and correlation between the dimensionality-reduced data are determined; (5) a method in which the Gaussian distribution of standard data 1 is determined, and the degree of matching between the Gaussian distribution of standard data 1 and the Gaussian distribution of the obtained data of a subject is quantified; and the like. Moreover, (6) a group of standard data 1 may be learned beforehand, and thus which one of the patterns in standard data 1 best matches data of a subject can be derived automatically.

Further, the measure such as the correlation coefficient may also be calculated between each item in an inter-organ cross talk indicator in data of a subject and each corresponding item in the inter-organ cross talk indicator in standard data 1.

In a more specific embodiment, examples of the method (1) described above include the Pearson product-moment correlation method. In this case, the correlation coefficient ranges from 1 to −1. The closer the correlation coefficient is to 1, the more similar the data of the subject and the standard data 1 are. Examples of the method (2) described above include Spearman's rank correlation method and the Kendall rank correlation method. In this case, the correlation coefficient ranges from 1 to −1. The closer the correlation coefficient is to 1, the more similar the data of the subject and the standard data 1 are. Examples of the method (3) described above include the Kullback-Leibler divergence method. In this case, the closer the pseudo-distance between the probability distribution of data of a subject and the probability distribution of standard data 1 is to 0, the more similar the data of the subject and the standard data 1 are. Examples of the method (4) described above include principal component analysis (PCA), Kernel principal component analysis, and the like. In the case of evaluating the measure of similarity using the distance between data of a subject and standard data 1, the closer the distance is to 0, the more similar the data of the subject and the standard data 1 are. In the case of evaluating the measure of similarity using the correlation coefficient between data of a subject and standard data 1, the closer the correlation coefficient is to 1, the more similar the data of the subject and the standard data 1 are. Examples of the method (5) described above include Z-score method. In this case, the closer the Z-score is to 0, the more similar the data of the subject and the standard data 1 are. Examples of the method (6) described above include support vector machines, k-nearest neighbors, neural networks, and the like. Standard methods for these methods may be partially modified as necessary.

Correlation coefficients calculated by using the above methods may be further analyzed using a chi-square test, a Kruskal-Wallis test, or the like.

For example, when a ρ-value is calculated using Spearman pairwise correlation, it can be determined as follows: when the ρ-value is 1, it can be determined that the data of the subject is identical to the standard data 1; when the ρ-value is more than 0.55 and less than 1, preferably more than 0.65 and less than 1, more preferably more than 0.75 and less than 1, and even more preferably more than 0.85 and less than 1, it can be determined that the data of the subject is similar to the standard data 1; on the other hand, when the ρ-value is 0.8 or less, preferably 0.65 or less, and more preferably 0.55 or less, it can be determined that the data of the subject is not similar to the standard data 1.

More preferably, in the case of predicting the presence or absence of a specific disease in a subject, when the ρ-value is more than 0.55 and less than 1, preferably more than 0.65 and less than 1, more preferably more than 0.75 and less than 1, and even more preferably more than 0.85 and less than 1, it can be determined that the data of the subject is similar to the standard data 1. In the case of predicting the stage of a specific disease in a subject, when the ρ-value is more than 0.75 and less than 1, and preferably more than 0.85 and less than 1, it can be determined that the data of the subject is similar to the standard data 1.

For example, when a z-value is calculated using a Z-score, it can be determined as follows: when the z-value is 0, it can be determined that the data of the subject is identical to the standard data 1; when the z-value falls within the range of 0±0.5 (excluding 0), preferably within the range of 0±3.35 (excluding 0), more preferably within the range of 0±0.2 (excluding 0), and even more preferably within the range of 0±0.15 (excluding 0), it can be determined that the data of the subject is similar to the standard data 1; on the other hand, when the z-value falls outside the range of 0±0.15, preferably outside the range of 0±0.2, more preferably outside the range of 0±0.35, and even more preferably outside the range of 0±0.4, it can be determined that the data of the subject is not similar to the standard data 1.

More specifically, in the case of predicting the presence or absence of a specific disease in a subject, when the z-value falls within the range of 0±0.35 (excluding 0), preferably within the range of 0±0.2 (excluding 0), and more preferably within the range of 0±0.15 (excluding 0), it can be determined that the data of the subject is similar to the standard data 1. In the case of predicting the stage of a specific disease in a subject, when the z-value falls within the range of 0±0.2 (excluding 0), and preferably within the range of 0±0.15 (excluding 0), it can be determined that the data of the subject is similar to the standard data 1.

When the similarity is determined using a Z-score, the brain, pancreas, testes, lungs, liver, and skeletal muscles are preferably excluded from the organs. Preferably, the Z-score method is excluded from the methods for determining the similarity.

Further, when at least 50%, preferably at least 70%, more preferably at least 80%, and even more preferably at least 90% of items in examined inter-organ cross talk indicators are identical or similar between standard data 1 and data of a subject, it can be determined that the pattern in the standard data 1 is similar to the pattern in the data of the subject. On the other hand, when at least 50%, preferably at least 70%, more preferably at least 80%, and even more preferably at least 90% of items in examined inter-organ cross talk indicators are not identical or similar between standard data 1 and data of a subject, it can be determined that the pattern in the standard data 1 is not similar to the pattern in the data of the subject.

The similarity between subject data X and standard data Y can be calculated by using the correlation coefficient between the subject data X and the standard data Y as an independent variable and determining an measure such as the correlation coefficient between the two groups by the method described above.

Standard data 1-Maps, standard data Y2-Maps, and standard data Y3-Maps are determined as follows. When standard data 1-Maps are determined, multiple organs are collected for a specific disease or each stage of the specific disease, and patterns of inter-organ cross talk indicators derived from each organ are determined (for example, when the inter-organ cross talk indicator is RNA, the genes expressing RNAs are listed in descending order of expression level). Correlation coefficients are calculated between the patterns of the organs using, for example, Spearman's rank correlation, and maps between the organs are generated. When the standard data Y2-Maps are determined, multiple organs are collected for each existing substance administered, and patterns of inter-organ cross talk indicators derived from each organ are determined (for example, when the inter-organ cross talk indicator is RNA, the genes expressing RNAs are listed in descending order of expression level). Correlation coefficients are calculated between the patterns of the organs using, for example, Spearman's rank correlation, and correlation maps between the organs are created. When standard data Y3-Maps are determined, multiple organs are collected for each disease or each disease stage, and patterns of inter-organ cross talk indicators in each organ are determined (for example, when the inter-organ cross talk indicator is RNA, the genes expressing RNAs are listed in descending order of expression level). Correlation coefficients are calculated between the patterns of the organs using, for example, Spearman's rank correlation, and maps between the organs are created.

More specifically, for example, the correlation coefficient of patterns of inter-organ cross talk indicators j between organ m and organ 1 in disease model i is represented by $r_{ijml}$. The number of individuals of disease model i is represented by n.

In this case, the correlation coefficient between organ m and organ 1 of disease model i can be represented by probability model p (the following equation).

$$p(r \mid i, m, l) = \frac{1}{\sqrt{2\pi}\, \sigma_{iml}} \exp\left(-\frac{(r - r_{iml})^2}{2\sigma_{iml}^2}\right) \quad \text{Equation 1}$$

wherein $r_{iml}$ is the mean of n correlation coefficients $r_{ijml}$, and $\sigma_{iml}^2$ is the sample variance of the correlation coefficients $r_{ijml}$.

Comparisons between data of a subject and standard data 1-Maps, comparisons between subject data X and standard data Y2-Maps, and comparisons between subject data X and standard data Y3-Maps can be performed using Bayesian inference, machine learning methods, etc.

For example, patterns of inter-organ cross talk indicators of multiple organs in a subject are obtained, and (a) correlation coefficient(s) of the patterns of inter-organ cross talk indicators is/are determined between the organs in the subject from which the data of the subject or the subject data X is obtained, in the same manner as described above. The obtained value(s) is/are represented by the following:

$$\{r'_{ml}\}_{m,l \in (\text{collected organs})}$$

In this case, the likelihood $L_i$ of correlation $$\{r'_{ml}\}_{m,l \in (\text{collected organs})}$$

with respect to each model i can be calculated using the following equation.

$$L_i = \prod_{m,l} p(r'_{ml} \mid i, m, l) \quad \text{Equation 2}$$

The likelihood is calculated for each model i, and a model i with the highest likelihood can be inferred to be the state of the subject.

When the number of organs to be compared is three or more, the likelihood between a disease model and a subject is determined between two of each of the organs, and the product of the calculated likelihoods is determined. A model i with the highest product may be inferred to be the state of the subject.

Which inter-organ cross talk indicator is used is not particularly limited when comparisons between data of a subject and standard data 1-Maps, comparisons between subject data X and standard data Y2-Maps, or comparisons between subject data X and standard data Y3-Maps are performed. For example, it is preferable to use an inter-organ cross talk indicator in which the difference between a positive control (or positive controls) and a negative control (or negative controls) is large. More specifically, for example, when the inter-organ cross talk indicator is RNA, it is RNA in which the ratio between a positive control (or positive controls) and a negative control (or negative controls) is more than 1.5 or less than 0.65, preferably more than 2 or less than 0.5, and more preferably more than 5 or less than 0.2.

The statistical analysis described above can be performed, for example, with a computer using a calculation program. In this case, the prediction program according to the present invention described later may comprise program code of a statistical analysis program for performing statistical analysis, or commercially available statistical analysis software may be used as a statistical analysis program. For example, the analysis can be performed using commercially available statistical analysis software, such as StatFlex Ver. 6 (Artech Co., Ltd., Osaka, Japan) or IBM SPSS Statistics (IBM Japan Ltd.).

"One or more" as used herein includes cases of one kind and cases of multiple kinds. The term "multiple" is not particularly limited as long as it means two or more, and preferably refers to three or more, more preferably five or more, and even more preferably ten or more.

2. Methods for Collecting and Storing Cells or Tissue, or Body Fluids for Extraction of an Inter-Organ Cross Talk Indicator, and Methods for Extracting and Measuring an Inter-Organ Cross Talk Indicator The method for collecting cells or tissue for extraction of an inter-organ cross talk indicator used in the present invention and the method for their storage are not particularly limited, and cells or tissue can be collected and stored according to known methods depending on the type of inter-organ cross talk indicator. The method for extracting an inter-organ cross talk indicator used in the present invention is also not particularly limited, and the inter-organ cross talk indicator can be extracted according to a known method depending on the type of inter-organ cross talk indicator. The method for measuring an inter-organ cross talk indicator in the present invention is not particularly limited as long as the amount of an inter-organ cross talk indicator can be measured.

Cells, tissue, or body fluids used for extraction of an inter-organ cross talk indicator are not particularly limited. Examples include cells, tissue, etc., collected from a subject by, for example, puncture, biopsy, or surgery. (The collected cells or tissue is also called a "specimen.") The cells or tissue may be, for example, fresh material after collection or cryopreserved material.

In this embodiment, an inter-organ cross talk indicator may be obtained from cells or tissue originating from a specific organ suspected of having a disease and from one or more organs other than the specific organ, for each stage of the specific disease. In addition, an inter-organ cross talk indicator may be derived from the corresponding cells or tissue in an individual without the specific disease.

The time at which cells, tissue, or body fluids are collected can suitably be selected according to the disease stage from, for example, the following: before the onset of a specific disease (in the normal state), at the onset of a specific disease, 1 month, 6 months, 1 year, 2 years, 3 years, 5 years, or 10 years after the onset of a specific disease, and the like.

When RNA is used as an inter-organ cross talk indicator, RNA extraction from cells, tissue, or body fluids is preferably performed immediately after the cells, tissue, or body fluids are collected or is performed after freezing the cells or tissue with liquid nitrogen or the like immediately after the cells or tissue is collected, and transporting and storing the cells or tissue.

The method for extracting RNA is not particularly limited, and RNA can be extracted using a known method. RNA may be purified using, for example, an oligo dT probe, as necessary. If necessary, cDNA may be synthesized from extracted or purified RNA by a reverse transcription reaction and used for measurement. Qualitative or quantitative measurement (including semi-quantitative measurement) of RNA may be performed by a known method, such as a method using a microarray, which can comprehensively analyze gene expression, or a method in which analysis is conducted by RNA-Seq, which determines the absolute amounts of RNAs in cells. As comprehensive and quantitative analysis, RNA-Seq is preferable.

Data obtained by RNA-Seq or the like can be analyzed using a known method. For example, when the data is analyzed with Illumina HiSeq (Illumina, Inc) or the like, the output data can be processed by the following method: (1) text data of nucleotide sequences are obtained from the output raw data of analysis (image data) (base calling); (2) the data is selected using predetermined filtering such as removing low fluorescence purity clusters caused by overlapping clusters from the data by using a calculation formula, such as chastity (filtering); and (3) the sample data is sorted based on index sequence information provided for each sample (specific nucleotide sequence information).

A data file (Fastq format or the like) obtained from the RNA-Seq sequencer is uploaded on, for example, Galaxy (https://usegalaxy.org/). Thereafter, analysis is carried out using, for example, Bowtie2 (http://bowtie-bio.sourceforge.net/bowtie2/index.shtml) to map each sequence to mouse genome map information mm9 or mm10. A BAM file obtained using Bowtie2 or the like is analyzed using, for example, Cufflinks (http://cole-trapnell-lab.github.io/cufflinks/) to calculate FPKM (RPKM) for each gene. In the obtained FPKM data, all FPKM values less than 1 are regarded as 0; pairwise correlation $(\rho=1-(6\Sigma D^2)/(n^3-n)$ is calculated using Python, and a heat map is generated using MeV. The FPKM values may also be visually analyzed.

If necessary, expression can also be confirmed by real-time PCR or the like. In addition, the mRNA expression level can be normalized by the expression level of a housekeeping gene, such as GAPDH, $\beta$2-microglobulin ($\beta$2M), or Maea, as necessary, and expressed as a relative expression level.

When at least one metabolite is used as an inter-organ cross talk indicator, the metabolite can be analyzed by a known method, such as gas chromatography/mass spectrometry (GCMS), capillary electrophoresis/mass spectrometry (CEMS), liquid chromatography/mass spectrometry (LCMS), high-performance liquid chromatography/inductively coupled plasma mass spectrometry (HPLC/ICP-MS), or high-performance liquid chromatography/ion trap mass spectrometry/time-of-flight mass spectrometry (LCMS-IT-TOF). Metabolites may also be derivatized, for example, silylated, trimethylsilylated, methoximated, or acylated, according to the method of analysis used. In addition, a known substance can be used as an internal standard substance.

For example, when metabolites are analyzed by GCMS, extraction of metabolites from cells or tissue is not particularly limited, and may be performed by a known method. For instance, tissue is placed in a solvent, such as water, methanol, ethanol, chloroform, or a mixture thereof, and homogenized, and further, a solvent containing internal standard 2-isopropylmalic acid or the like is added to the solvent to prepare a crude extract. The aqueous layer is purified by adding water or a hydrophobic solvent such as chloroform to the crude extract. The purified aqueous layer is further purified by ultrafiltration or the like and used as an extract of metabolites for analysis.

After the metabolites in the extract are methoximated or trimethylsilylated, gas chromatography may be performed using, for example, GCMS-TQ8030 (Shimadzu Corporation) and DB-5 (30 m×0.25 mm (inner diameter)×1.00 um (film thickness)) (Agilent Technologies) as a capillary column for GC. Gas chromatography is performed, for example, under the following temperature increase conditions: the temperature is increased at a rate of 4° C./min from 100° C. to 320° C. The inlet temperature is, for example, about 280° C. Helium or the like may be used as carrier gas and made to flow at a rate of, for example, about 39.0 cm/sec. The energy of electron ionization may be about 150 eV, the ion source temperature may be about 200° C., and the range of m/z to be scanned may be about 45 to 600. About 1 μl of a sample may be injected and measured under the following conditions:

Heart_Split1:25_detector voltage+0.3 kV

Brain_Split1:25_detector voltage+0.2 kV

Kidney_Split1:25_detector voltage+0.3 kV

Liver_Split1:25_detector voltage+0.3 kV

Pancreas_Split1:25_detector voltage+0.3 kV

Skeletal muscle_Split1:25_detector voltage+0.2 kV

Adipose tissue_Split1:3_detector voltage+0.2 kV

Blood plasma_Split1:10_detector voltage+0.1 kV

Spleen_Split1:25_detector voltage+0.2 kV

Lung_Split1:25_detector voltage+0.3 kV

Testis_Split1:10_detector voltage+0.3 kV

Thymus_Split1:25_detector voltage+0.3 kV

Searching can be performed using the data obtained by GCMS analysis with, for example, GCMS solution Ver. 4.20, which is data analysis software, and GEMS Metabolites Database (Shimadzu Corporation). To identify metabolites, the retention time expected from the retention sample and the presence of m/z of at least two specific peaks (target ion, confirmation ion), and the ratio of the specific peaks are confirmed. In each of the identified metabolites, the peak area of the target ion is measured and normalized using the peak area of the internal standard and the sample amount. Thereafter, the corrected measurement results can be calculated by a Z-score ((sample data-average)/standard deviation) to generate a heat map using Multi Experiment Viewer (MeV). Pairwise correlation ($\rho=1-[6\Sigma D^2]/n(n^2-1)$) can also be calculated using Python to generate a heat map with MeV. Furthermore, analysis such as principal component analysis (PCA) can also be performed using multivariate analysis software SIMCA (Umetrics).

When metabolites are analyzed by CEMS, for example, tissue can be homogenized in 50% acetonitrile containing an internal standard substance (e.g., Solution ID: 304-1002; HMT), and the sample obtained after the homogenization can be centrifuged; the supernatant can be subjected to ultrafiltration, and the resulting sample can be dried under reduced pressure, redissolved in distilled water, and used as a sample for measurement.

For example, Agilent CE-TOFMS system (Agilent Technologies) can be used for CE-MS, and a fused silica capillary (i.d. 50 μm×80 cm) can be used for a capillary column for CE. As electrophoresis buffers in CE, a cation buffer solution (p/n: H3301-1001; HMT) or the like can be used for cations, and an anion buffer solution (p/n: 13302-1023; HMT) or the like can be used for anions.

Measurement Conditions on the Cation Side

For example, electrophoresis is performed under the following sample injection conditions: pressure injection: 50 mbar, 10 sec; electrophoresis voltage of CE: 27 kV. The energy of electron ionization may be 4,000 V, and the range to be scanned may be 50 to 1000. About 5 nl of a sample may be injected.

CE voltage: Positive, 27 kV

MS ionization: ESI Positive

MS capillary voltage: 4,000 V

MS scan range: m/z 50-1,000

Sheath liquid: HMT Sheath Liquid (p/n: H3301-1020)

Measurement Conditions on the Anion Side

For example, electrophoresis is performed under the following sample injection conditions: pressure injection: 50 mbar, 25 sec; electrophoresis voltage of CE: 30 kV. The energy of electron ionization may be 3,500 V, and the range to be scanned may be 50 to 1000. About 5 nl of a sample may be injected.

CE voltage: Positive, 30 kV

MS ionization: ESI Negative

MS capillary voltage: 3,500 V

MS scan range: m/z 50-1,000

Sheath liquid: HMT Sheath Liquid (p/n: H3301-1020)

Detected peaks can be processed with MasterHands automatic integration software ver. 2.16.0.15 (developed by Keio University). Peaks having a signal-to-noise (S/N) ratio of 3 or more are automatically extracted, and metabolite identification can be performed by using the mass-to-charge ratio (m/z), peak area value, and migration time (MT). For each of the identified metabolites, the peak area of the target ion can be measured and normalized using the peak area of the internal standard and the sample amount.

The amount of an inter-organ cross talk indicator obtained by the methods described above can be stored in the storage unit of an apparatus, or an apparatus having a storage unit that is different from the apparatus, as a pattern of the inter-organ cross talk indicator for each stage of a specific disease, each organ or body fluid, each type of individual, each age group of individuals, and/or each sex of individuals.

3. Database

The amassment of standard data 1, 2, or Y above is called a "database." The corresponding pattern of an inter-organ cross talk indicator in standard data 1 or 2 can be retrieved and extracted from the database based on information regarding the stage of a specific disease and/or the name of each organ or body fluid.

Examples of data used for standard data 1, 2, or Y include the results of qualitative or quantitative analysis of inter-organ cross talk indicators derived from cells or tissue originating from one or more organs of individuals, or one or more body fluids of individuals.

An inter-organ cross talk indicator can be derived from cells or tissue originating from an organ suspected of having a disease, or a body fluid suspected of having a disease, and from cells or tissue originating from one or more other organs for each stage of the disease. An inter-organ cross talk indicator can also be derived from the corresponding cells or tissue of an individual without the specific disease.

The time at which cells, tissue, or body fluids are collected can suitably be selected according to a specific disease from, for example, the following: before the onset of a specific disease (in the normal state), at the onset of a specific disease, 1 hour, 6 hours, 1 day, 1 week, 1 month, 6 months, 1 year, 2 years, 3 years, 5 years, or 10 years after the onset of a specific disease, and the like.

The description in the "2. Methods for collecting and storing cells or tissue, or body fluids for extraction of an inter-organ cross talk indicator, and methods for extracting and measuring an inter-organ cross talk indicator" section above is incorporated herein by reference. An inter-organ cross talk indicator is extracted and measured qualitatively or quantitatively according the methods described in Section 2, and the amount of the inter-organ cross talk indicator is obtained as data.

The obtained data can be stored in the storage unit of an apparatus, or an apparatus having a storage unit that is different from the apparatus, for each disease, each organ or body fluid, each stage, each type of individual, each age group of individuals, and/or each sex of individuals.

Next, patterns for standard data are determined from the data obtained above and used in the present invention (Reverse iOrgans, Forward iOrgans, D-iOrgans) as described below.

4. Reverse iOrgans 4-1. Outline

In this embodiment, the presence of a disease in a specific organ and/or the stage of the specific disease in a subject is predicted from a pattern of an inter-organ cross talk indicator derived from each of one or more organs other than the specific organ of the subject. Specifically, data of the subject regarding an inter-organ cross talk indicator in each of one or more organs other than the specific organ is obtained by performing the measurement method described in Section 2 above, and the inter-organ cross talk indicator is derived from cells or tissue originating from each of the one or more organs. The data of the subject is compared with standard data 1 derived beforehand from the corresponding inter-organ cross talk indicator. Then, similarity of patterns of the inter-organ cross talk indicators is calculated, and the presence of the specific disease and/or the stage of the specific disease is predicted using the similarity as a measure. More specifically, this embodiment comprises the steps of (1) obtaining data of a subject derived from an inter-organ cross talk indicator in each of one or more organs other than the specific organ of the subject, the inter-organ cross talk indicator being derived from cells or tissue originating from each of the one or more organs; (2) calculating, by comparing the data of the subject obtained in step (1) with standard data 1 derived beforehand from the corresponding inter-organ cross talk indicator, similarity of patterns of the inter-organ cross talk indicators; and (3) determining that the subject has a specific disease corresponding to the standard data 1 and/or that the subject is in a stage of a specific disease corresponding to the standard data 1 when it is determined that the similarity of patterns of the inter-organ cross talk indicators calculated in step (2) is similar. Here, step (3) can also be read as the step of predicting the presence of a disease in a specific organ and/or the stage of the disease in the specific organ using, as a measure, the similarity of patterns of the inter-organ cross talk indicators obtained in step (2). The one or more organs other than the specific organ may be two or more organs. That is, (1') data of a subject regarding an inter-organ cross talk indicator in each of multiple organs other than the specific organ of the subject is obtained from cells or tissue originating from each of the organs; (2') the data of the subject derived from each organ obtained in step (1') is compared with corresponding standard data 1 derived beforehand from the inter-organ cross talk indicator in the organ, and similarity of patterns of the inter-organ cross talk indicators between each set of data of the subject and each corresponding standard data 1 is calculated; (3') it may be determined that the subject has a specific disease corresponding to the standard data 1 and/or that the subject is in a stage of a specific disease corresponding to the standard data 1 when it is determined that the similarity of patterns of the inter-organ cross talk indicators calculated in step (2') is similar between each set of data of the subject and each corresponding standard data 1. In this case, the similarity between the data of the subject derived from each organ and the corresponding standard data 1 derived from the organs other than the specific organ may be sequentially calculated for each standard data 1 in each organ. In another embodiment, the similarity between the data of the subject derived from each organ and the corresponding standard data 1 derived from the organs other than the specific organ may be simultaneously calculated for each standard data 1 in each organ, and the presence of the specific disease and/or the stage of the specific disease may be predicted in the organs other than the specific organ simultaneously. The calculation is preferably performed simultaneously.

Step (1) may be performed in such a manner that data of the subject is obtained by actually performing the measurement method described in Section 2 above, or in such a manner that data of the subject already obtained is further put into the prediction apparatus described later or the like. The method for calculating the similarity between the standard data 1 and the data of the subject in step (2), and the method for determining whether the standard data 1 and the data of the subject are similar in step (3), can be performed according to the methods described in the "1. Explanation of terms" section above. Here, step (1) and step (2) are not necessarily performed consecutively in the same organization. For example, the data of the subject obtained in step (1) may be sent to a third-party organization to perform step (2) and the step after step (2).

This embodiment may further comprise the following steps before step (1): (i) extracting the inter-organ cross talk indicator from the cells or tissue originating from each of the one or more organs other than the specific organ of the subject, and (ii) measuring the amount of the inter-organ cross talk indicator extracted in step (i). In this case, step (i) and step (ii) are not necessarily performed consecutively. For example, the inter-organ cross talk indicator obtained in step (i) may be sent to a third-party organization to perform step (ii). Step (ii) and step (1) are also not necessarily performed consecutively. The results of measurement of the inter-organ cross talk indicator obtained in step (ii) may be sent to a third-party organization to perform step (1) and the steps after step (1).

Here, the method for calculating the similarity between the standard data 1 and the data of the subject, and the method for determining whether the standard data 1 and the data of the subject are similar are as described in the "1. Explanation of terms" section above.

As another embodiment, this embodiment also includes a method for obtaining information regarding the similarity of patterns of inter-organ cross talk indicators to predict the presence of a specific disease and/or the stage of the specific disease in a subject, the method comprising steps (1) and (2) mentioned above, and the step of obtaining the information from step (2).

4-2. System Configuration

Figure 8:
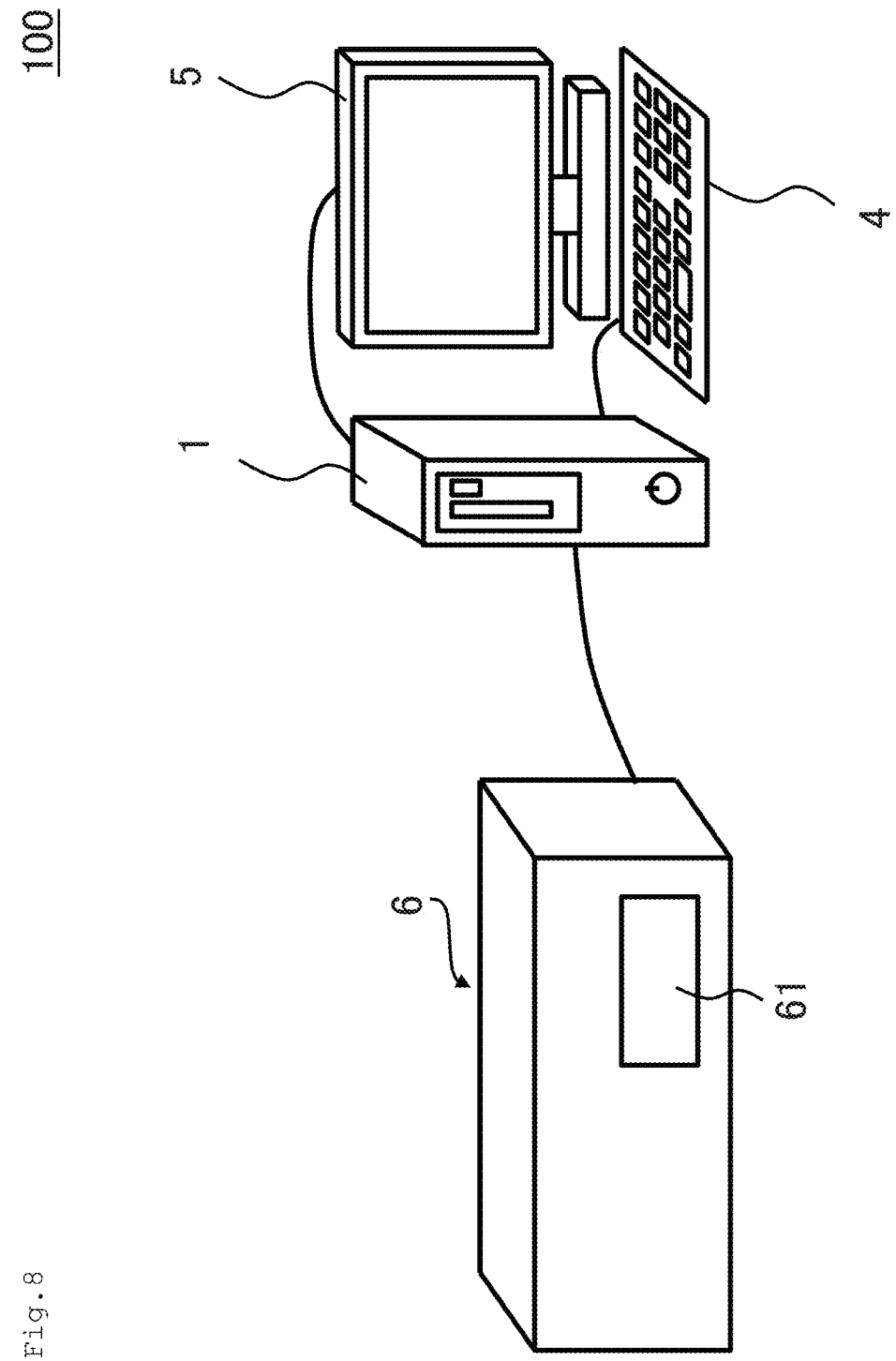
FIG. 8 is an overview of a system 100 according to a first embodiment of the present invention.
Figure 9:
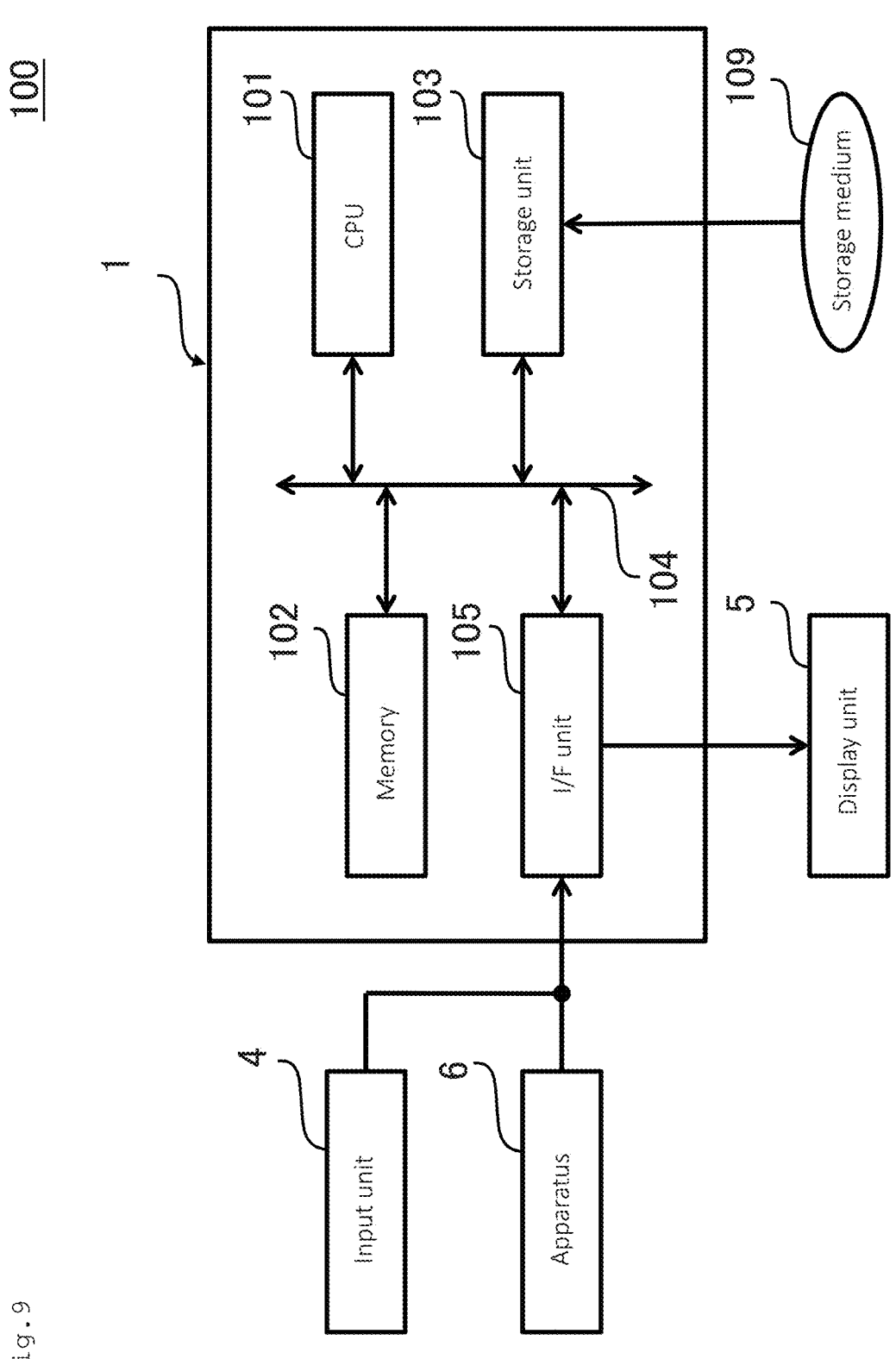
FIG. 9 is a block diagram illustrating a hardware configuration of the system 100 according to the first embodiment of the present invention.

FIG. 8 is an overview of a system 100 according to a first embodiment of the present invention, and FIG. 9 is a block diagram illustrating a hardware configuration of the system 100. The system 100 comprises a prediction apparatus 1, an input unit 4, a display unit 5, and an apparatus 6.

The prediction apparatus 1 includes, for example, a general-purpose personal computer, and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the apparatus 1 and external devices. The input unit 4 and the display unit 5 are connected to the prediction apparatus 1. The input unit 4 includes, for example, a keyboard, and the display unit 5 includes, for example, a liquid crystal display. The input unit 4 and the display unit 5 may be integrated and implemented as a display with a touch panel. The prediction apparatus 1 need not be a single apparatus, and the CPU 101, the memory 102, the storage unit 103, and the like may be located in separate places and connected via a network. The apparatus 1 may also be an apparatus that omits the input unit 4 and the display unit 5 and that does not require an operator.

The prediction apparatus 1 and the apparatus 6 are also not necessarily located in one place and may be configured such that the apparatuses located in separate places are communicatively connected to each other via a network.

In the explanation below, a process performed by the prediction apparatus 1 means a process performed by the CPU 101 of the prediction apparatus 1 based on a prediction program unless otherwise specified. The CPU 101 temporarily stores necessary data (such as intermediate data being processed) in the memory 102 that serves as a work area, and suitably stores data that are stored for a long period of time, such as computation results, in the storage unit 103.

The apparatus 6 is an apparatus for measuring RNA expression levels by the RNA-Seq method or measuring the amounts of metabolites by mass spectrometry. The apparatus 6 comprises an analysis unit 61. A sample in which a reaction for RNA-Seq has been carried out is set in the analysis unit 61 to perform analysis of nucleotide sequences in the analysis unit 61.

The apparatus 6 is connected to the prediction apparatus 1 by a wired or wireless connection. The apparatus 6 A/D converts the measurement values of mRNAs and transmits them as digital data to the prediction apparatus 1. Therefore, the prediction apparatus 1 can obtain the measurement values of mRNAs as digital data that can be computed. In this embodiment, digital data from the apparatus 6 is referred to as "data of a subject derived from an inter-organ cross talk indicator" or simply referred to as "data of a subject."

4-3. Prediction Apparatus

As the first embodiment, the present invention includes a prediction apparatus for predicting the presence of a specific disease and/or the stage of the specific disease in a subject, the apparatus comprising the following computation means:

a means for obtaining data of the subject derived from an inter-organ cross talk indicator in each of one or more organs other than the specific organ of the subject, the inter-organ cross talk indicator being derived from cells or tissue originating from each of the one or more organs;

a means for calculating, by comparing the data of the subject with standard data derived beforehand from the corresponding inter-organ cross talk indicator, similarity of patterns of the inter-organ cross talk indicators; and a means for predicting the presence of the specific disease and/or the stage of the specific disease by using, as a measure, the similarity of patterns of the inter-organ cross talk indicators calculated by the pattern similarity calculation means.

Here, the method for calculating the similarity between the standard data 1 and the data of the subject and the method for determining whether the standard data 1 and the data of the subject are similar are as described in the "1. Explanation of terms" section above.

In this embodiment, the presence of a specific disease and/or the stage of the specific disease in a subject can be predicted by the system 100 (FIGS. 8 and 9) comprising the prediction apparatus 1 as the prediction apparatus described above.

Figure 10:
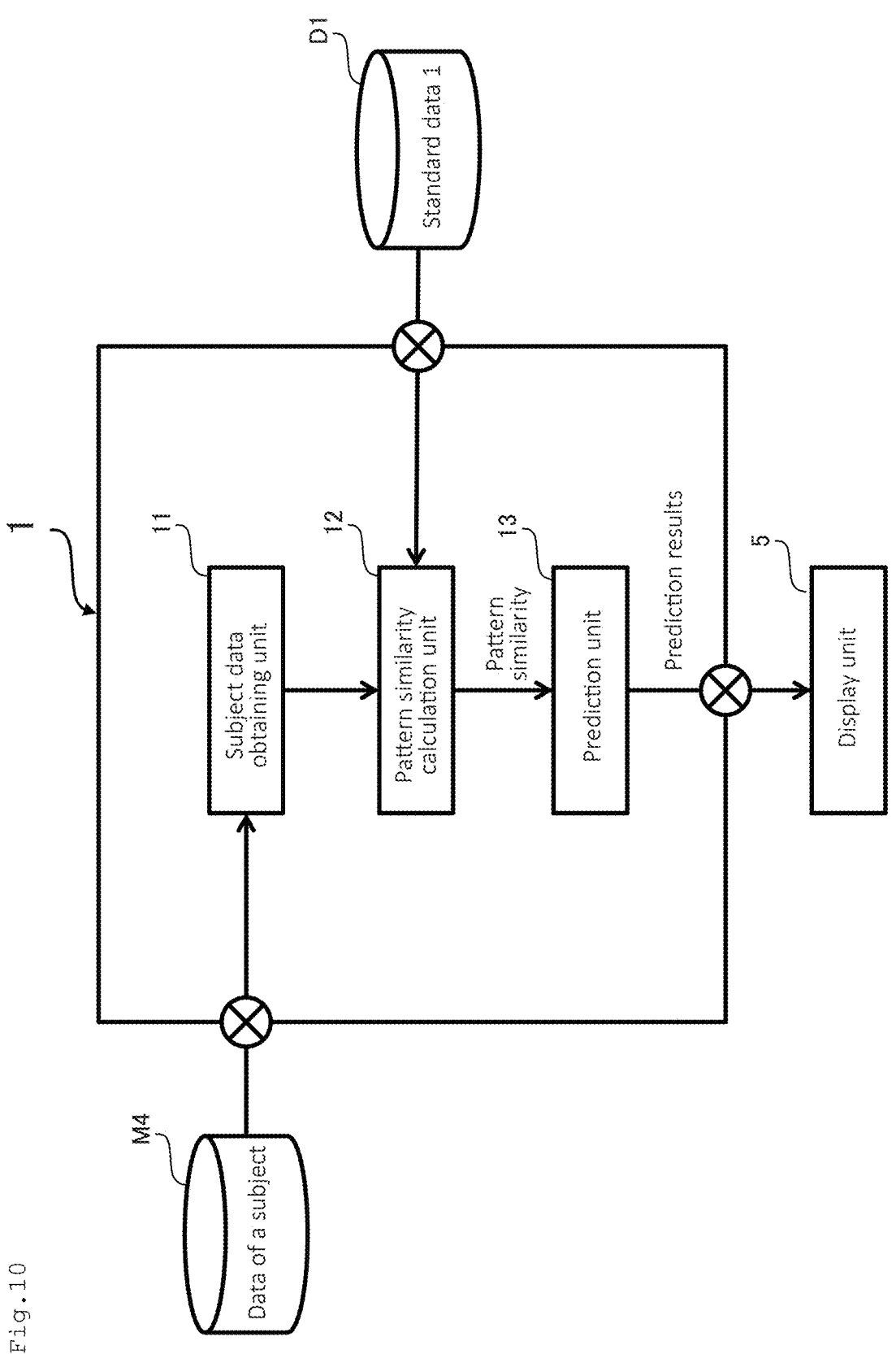
FIG. 10 is a block diagram to illustrate a function of a prediction apparatus 1 according to the first embodiment of the present invention.

FIG. 10 is a block diagram to illustrate a function of the prediction apparatus 1 according to the first embodiment of the present invention. The prediction apparatus 1 comprises a subject data obtaining unit 11, a pattern similarity calculation unit 12, and a prediction unit 13. These functional blocks are implemented by installing the prediction program according to the present invention in the storage unit 103 or the memory 102 of the prediction apparatus 1 and causing the CPU 101 to execute the program. With this structure, the prediction apparatus 1 carries out the prediction method described later in the "4-5. Prediction method" section. The subject data obtaining means, pattern similarity calculation means, and prediction means recited in the claims correspond to the subject data obtaining unit 11, the pattern similarity calculation unit 12, and the prediction unit 13 shown in FIG. 10, respectively.

In other words, the prediction apparatus 1 is a prediction apparatus for predicting the presence of a specific disease and/or the stage of the specific disease in a subject, the apparatus executing the following computation functions by the CPU 101:

a function of obtaining data of the subject derived from an inter-organ cross talk indicator in each of one or more organs other than the specific organ, the inter-organ cross talk indicator being derived from cells or tissue originating from each of the one or more organs;

a function of calculating, by comparing the data of the subject obtained by the subject data obtaining function with standard data 1 derived beforehand from the corresponding inter-organ cross talk indicator, similarity of patterns of the inter-organ cross talk indicators; and a function of predicting the presence of the specific disease and/or the stage of the specific disease using, as a measure, the similarity of patterns of the inter-organ cross talk indicators obtained by the pattern similarity calculation function.

In this embodiment, the subject data obtaining unit 11 obtains subject data M4 of an inter-organ cross talk indicator measured in the apparatus 6 from the apparatus 6. Standard data D1 (standard data 1) is stored outside the prediction apparatus 1 and put into the prediction apparatus 1 via, for example, the Internet.

The subject data M4 may also be put into the prediction apparatus 1 from a third-party organization (not shown) via a network. The subject data M4 and the standard data D1

(standard data 1) may be stored in the storage unit 103 or the memory 102 of the prediction apparatus 1 beforehand.

The pattern similarity calculation unit 12 compares the subject data M4 with the standard data D1 (standard data 1) and calculates the similarity of patterns of the inter-organ cross talk indicators. The prediction unit 13 predicts the presence of the specific disease and/or the stage of the specific disease using, as a measure, the similarity of patterns of the inter-organ cross talk indicators obtained by the pattern similarity calculation unit 12. The pattern similarity calculation unit 12 and the prediction unit 13 are functional blocks that respectively execute the pattern similarity calculation step and the prediction step in the prediction method according to the first embodiment of the present invention described later in the "4-5. Prediction method" section. The details of the computation processing of these steps are described in the "4-5. Prediction method" section with reference to FIG. 11.

Further, the functional blocks, i.e., the subject data obtaining unit 11, the pattern similarity calculation unit 12, and the prediction unit 13, are not necessarily executed by a single CPU, and may be processed distributively by multiple CPUs. For example, these functional blocks may be configured such that the function of the subject data obtaining unit 11 is executed by a CPU of a first computer and such that the functions of the pattern similarity calculation unit 12 and the prediction unit 13 are executed by a CPU of a second computer, i.e., another computer.

4-4. Prediction Program

Further, in order to carry out steps S11 to S16 in FIG. 11 described below, the prediction apparatus 1 stores the prediction program according to the present invention in the storage unit 103 beforehand, for example, in an executable format (for example, a form in which the program can be produced by being converted from a programming language using a compiler). The prediction apparatus 1 carries out processing using the prediction program stored in the storage unit 103.

Specifically, the prediction program according to the first embodiment of the present invention is a prediction program that, when executed by a computer, causes the computer to carry out the following processing to predict the presence of a specific disease and/or the stage of the specific disease in a subject:

processing of obtaining data of the subject derived from an inter-organ cross talk indicator in each of one or more organs other than the specific organ, the inter-organ cross talk indicator being derived from cells or tissue originating from each of the one or more organs;

processing of calculating, by comparing the data of the subject obtained by the subject data obtaining processing with standard data 1 derived beforehand from the corresponding inter-organ cross talk indicator, similarity of patterns of the inter-organ cross talk indicators; and processing of predicting the presence of the specific disease and/or the stage of the specific disease by using, as a measure, the similarity of patterns of the inter-organ cross talk indicators obtained by the pattern similarity calculation processing.

In this embodiment, as shown in FIG. 9, the prediction program is stored in a computer-readable non-transitory tangible storage medium 109, such as a CD-ROM, and is installed in the prediction apparatus 1 from the storage medium 109; alternatively, the prediction apparatus 1 may be connected to the Internet (not shown) to download the program code of the prediction program via the Internet. To cause a computer to carry out the computation processing described above, the prediction program according to the present invention may also be linked to another program stored in the storage unit 103 or the memory 102. For example, the prediction program may be linked to statistical analysis software mentioned in the "1. Explanation of terms" section above, and the pattern similarity calculation processing may be carried out using the statistical analysis software.

The subject data obtaining processing corresponds to computation processing that is performed by the subject data obtaining unit 11 implemented through execution of the prediction program by the prediction apparatus 1. The prediction processing corresponds to computation processing that is performed by the prediction unit 13 implemented through execution of the prediction program by the prediction apparatus 1.

4-5. Prediction Method

The prediction apparatus 1 according to the first embodiment of the present invention carries out the prediction method according to the first embodiment of the present invention. The prediction method according to the first embodiment of the present invention is a method for predicting the presence of a specific disease and/or the stage of the specific disease in a subject, the method comprising:

a step of calculating similarity of patterns of the inter-organ cross talk indicators by comparing data of the subject regarding an inter-organ cross talk indicator in each of one or more organs other than the specific organ, the inter-organ cross talk indicator being derived from cells or tissue originating from each of the one or more organs, with standard data 1 derived beforehand from the corresponding inter-organ cross talk indicator; and a step of predicting the presence of the specific disease and/or the stage of the specific disease by using, as a measure, the similarity of patterns of the inter-organ cross talk indicators obtained in the pattern similarity calculation step.

Figure 11:
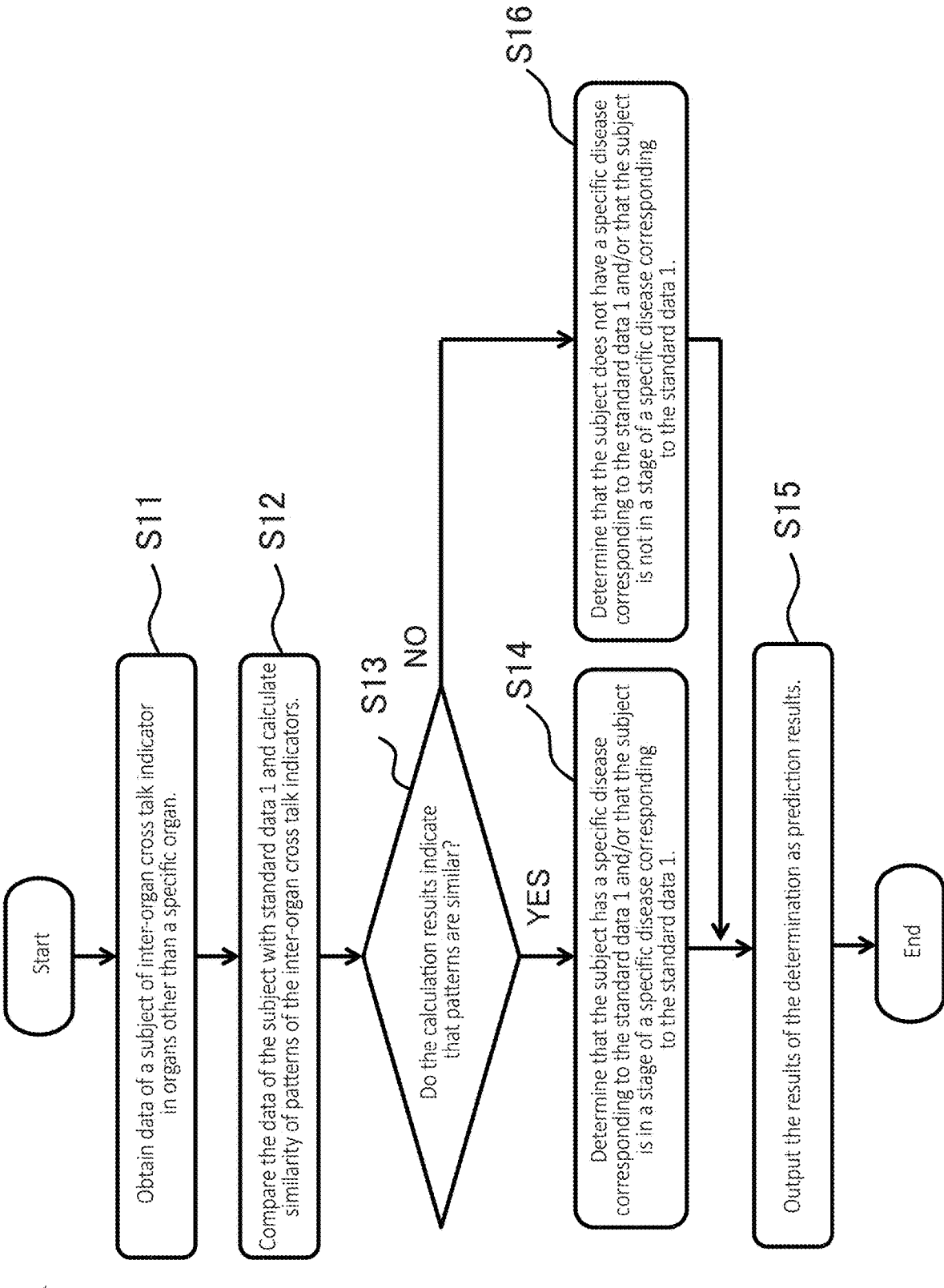
FIG. 11 is a flow chart illustrating a flow of data processing performed by the prediction apparatus 1 according to the first embodiment of the present invention to carry out a prediction method.

FIG. 11 is a flow chart illustrating a flow of data processing performed by the prediction apparatus 1 according to the first embodiment of the present invention to carry out the prediction method above. The processing of steps S11 to S16 shown in FIG. 11 is performed by the subject data obtaining unit 11, the pattern similarity calculation unit 12, and the prediction unit 13 shown in FIG. 10.

In step S11, the subject data obtaining unit 11 obtains subject data M4. The subject data M4 is a pattern of an inter-organ cross talk indicator in each of one or more organs other than a specific organ of a subject, the inter-organ cross talk indicator being derived from cells or tissue originating from each of the one or more organs, and transmitted from the apparatus 6 to the prediction apparatus 1.

In step S12, the pattern similarity calculation unit 12 compares the obtained subject data M4 of the inter-organ cross talk indicator with standard data D1 (standard data 1) and calculates similarity of patterns of the inter-organ cross talk indicators. The method for calculating the similarity and the method for determining whether patterns are similar are as described in the "1. Explanation of terms" section above. The prediction program described in the "4-4. Prediction program" section above may comprise program code of a program for causing the CPU 101 of the prediction apparatus 1 to perform computation processing by the pattern similarity calculation unit 12, or, for example, may be linked to statistical analysis software mentioned in the "1. Explanation of terms" section above to cause the CPU 101 to perform computation processing by the pattern similarity calculation unit 12 using the statistical analysis software.

In step S14, the prediction unit 13 predicts the presence of a specific disease and/or the stage of the specific disease by using, as a measure, the similarity obtained in step S12. Specifically, when it is determined from the similarity that patterns are similar ("YES" in step 13), the prediction unit 13 determines in step S14 that the subject has a specific disease corresponding to a pattern in the standard data D1 (standard data 1) that is similar to the subject data M4, and/or the subject is in a stage of a specific disease corresponding to the standard data D1 (standard data 1).

When it is determined from the similarity obtained in step S12 that patterns are not similar ("NO" in step 13), the prediction unit 13 determines in step S16 that the subject does not have a specific disease corresponding to the standard data D1 (standard data 1), and/or the subject is not in a stage of a specific disease corresponding to the standard data D1 (standard data 1).

In step S15, the prediction unit 13 outputs the results determined in step S14 or 16 as prediction result data. In this embodiment, the prediction results are displayed on the display unit 5 and the prediction result data is stored in the storage unit 103 in the prediction apparatus 1. The prediction results may be displayed on a display unit of a computer terminal connected to the prediction apparatus 1 via the Internet that is external to the prediction apparatus 1, for example, in a third-party organization, instead of displaying the prediction results on the display unit 5.

The specific procedure of each step is in accordance with the description in the "4-1. Outline" section above.

5. Forward iOrgans

5-1. Outline

In this embodiment, the presence of a disease and/or the stage of the disease in each of one or more organs other than a specific organ in a subject affected with a disease in the specific organ is predicted. Specifically, the presence of a disease and/or the stage of the disease in each of one or more organs other than a specific organ in a subject affected with a disease in the specific organ is predicted based on information regarding the stage of the disease in the specific organ in the subject obtained from diagnostic results of the subject. This embodiment comprises the steps of (i) obtaining information regarding a stage of the disease in the specific organ in the subject from diagnostic results of the subject; (ii) checking the information about the stage obtained in step (i) against standard data 2; (iii) determining, from the standard data 2, standard data a at a stage of the disease in the specific organ corresponding to the information about the stage, based on the checking results obtained in step (ii), and extracting, from the standard data α, a pattern of an inter-organ cross talk indicator corresponding to the stage in the subject in each of one or more organs other than the specific organ in the subject; (iv) checking the pattern of the inter-organ cross talk indicator extracted in step (iii) against known information regarding the inter-organ cross talk indicators in diseases and/or stages of the diseases, and determining the presence of a disease and/or the stage of the disease in each of the one or more organs other than the specific organ corresponding to the pattern of the inter-organ cross talk indicator in each of the one or more organs other than the specific organ in the subject; and (v) further determining that the disease in each of the one or more organs other than the specific organ determined in step (iv) is a disease from which the subject may be suffering, and/or further determining that the stage of the disease in each of the one or more organs other than the specific organ determined in step (iv) is a stage of a disease from which the subject is suffering. Here, steps (iv) and (v) above may be combined into step (iv') predicting the presence and/or stage of a disease in each of the one or more organs other than the specific organ by using, as a measure, the pattern of the inter-organ cross talk indicator obtained in step (iii). Here, the one or more organs other than the specific organ may be multiple organs. That is, steps (iv) and (v) may be the following: (iv'') checking the patterns of the inter-organ cross talk indicators in the multiple organs other than the specific organ in the subject extracted from the standard data a determined in step (iii) against known information regarding inter-organ cross talk indicators in diseases and/or stages of the diseases, and determining the presence of a disease and/or the stage of the disease in each of the multiple organs other than the specific organ corresponding to the pattern of the inter-organ cross talk indicator in each of the multiple organs other than the specific organ in the subject; and (v'') further determining that the disease in each of the multiple organs other than the specific organ determined in step (iv'') is a disease from which the subject may be suffering, and/or further determining that the stage of the disease in each of the multiple organs other than the specific organ determined in step (iv'') is a stage of a disease from which the subject is suffering.

In step (i), the diagnostic results of the subject are not limited as long as they are derived by, for example, a physician based on, for example, test results or a medical interview. The diagnostic results may be information obtained from, for example, a paper chart or may be electronic data extracted from, for example, an electronic chart. In step (i), information about the stage of the disease in the specific organ in the subject is obtained as, for example, oral, written, or digital information based on the diagnostic results of the subject. That is, the information about the stage of the disease in the specific organ in the subject is information regarding in what stage of the disease in the specific organ the subject is.

In checking the information regarding the stage obtained in step (i) against the standard data 2 in step (ii), for example, it is checked whether the name of the stage matches the name of the stage of the disease in the specific organ assigned to each pattern of an inter-organ cross talk indicator in the standard data 2. The checking may be carried out visually, or may be carried out, for example, on database software, such as Microsoft (registered trademark) Excel (Microsoft Corporation) or Microsoft (registered trademark) Access (Microsoft Corporation), using the search function, the filtering function, or the like of the software.

In step (iii), patterns of inter-organ cross talk indicators linked with the name of the stage of the disease in the specific organ of the subject are extracted based on the results of the checking in step (ii). The group of the extracted patterns of inter-organ cross talk indicators is determined to be standard data α. Further, at least one organ other than the specific organ is selected from the names of organs linked with the corresponding patterns of inter-organ cross talk indicators contained in standard data α, and the pattern of the inter-organ cross talk indicator in the at least one selected organ is extracted. Selection of at least one organ other than the specific organ and extraction of the pattern of the inter-organ cross talk indicator in the at least one selected organ may be carried out visually, or may be carried out on the database software described above using the search function, the filtering function, or the like of the software. When the group of the extracted patterns of inter-organ cross talk indicators is a group of patterns of expression of at least one RNA, the standard data a may also be referred to as "standard data α1." When the group of the extracted patterns of inter-organ cross talk indicators is a group of patterns of presence of at least one metabolite, the standard data a may also be referred to as "standard data α2."

In step (iv), the similarity between the extracted pattern of the inter-organ cross talk indicator in the at least one selected organ and the information regarding inter-organ cross talk indicators in diseases and/or stages of the diseases stored in a database of known information regarding diseases (e.g., DPC database (provided by Japanese Ministry of Health, Labour and Welfare), PubMed (provided by National Center for Biotechnology Information), Embase (provided by Elsevier), or Cochrane Library (Cochrane); hereinafter also referred to as "disease information database") is calculated and determined. Subsequently, the name of a disease, or the name of a stage of a disease, whose pattern of the inter-organ cross talk indicator stored in the disease information database is determined to be wholly or partially similar to the pattern of the inter-organ cross talk indicator in the at least one selected organ is extracted. Whether the pattern of the inter-organ cross talk indicator in the at least one selected organ is similar to the known information can be determined according to the method for determining similarity described in the "1. Explanation of terms" section above. It can then be determined that the extracted disease is present in the selected organ other than the specific organ or that the selected organ other than the specific organ is in the extracted stage of the disease. In this determination process, the pattern of the inter-organ cross talk indicator in the at least one selected organ can be compared with known information regarding the inter-organ cross talk indicator in healthy individuals to determine that the organ is normal.

In step (v), it is further determined that the disease in the selected organ other than the specific organ and/or the stage of the disease determined in step (iv) is a disease and/or a stage of a disease from which the subject may be suffering. When multiple diseases are determined in step (iv), it can be determined that a disease showing high similarity to the pattern of the inter-organ cross talk indicator in the selected organ is a disease from which the subject may be suffering. When multiple stages of diseases are determined in step (iv), it can be determined that a stage of a disease showing high similarity to the pattern of the inter-organ cross talk indicator in the selected organ is the stage of the disease from which the subject may be suffering.

Further, this embodiment may also be a method for obtaining information to predict the presence of a disease and/or the stage of the disease in each of one or more organs other than a specific organ in a subject affected with a disease in the specific organ, the method comprising steps (i) to (iii) above, and further comprising, instead of step (iv) above, step (iv') of checking the pattern of the inter-organ cross talk indicator extracted in step (iii) against known information regarding inter-organ cross talk indicators in diseases and/or the stages of the diseases, and obtaining information regarding the presence of a disease and/or the stage of the disease in each of the one or more organs other than the specific organ corresponding to the pattern of the inter-organ cross talk indicator in each of the one or more organs other than the specific organ in the subject. The step of checking the extracted pattern of the inter-organ cross talk indicator against known information regarding inter-organ cross talk indicators in diseases and/or stages of the diseases is in accordance with step (iv) above.

5-2. System Configuration

Figure 12:
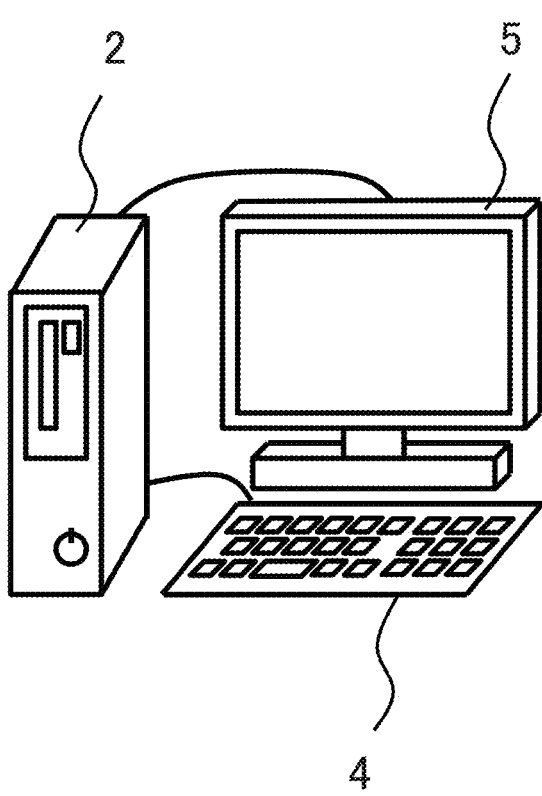
FIG. 12 is an overview of a system 110 according to a second embodiment of the present invention.
Figure 13:
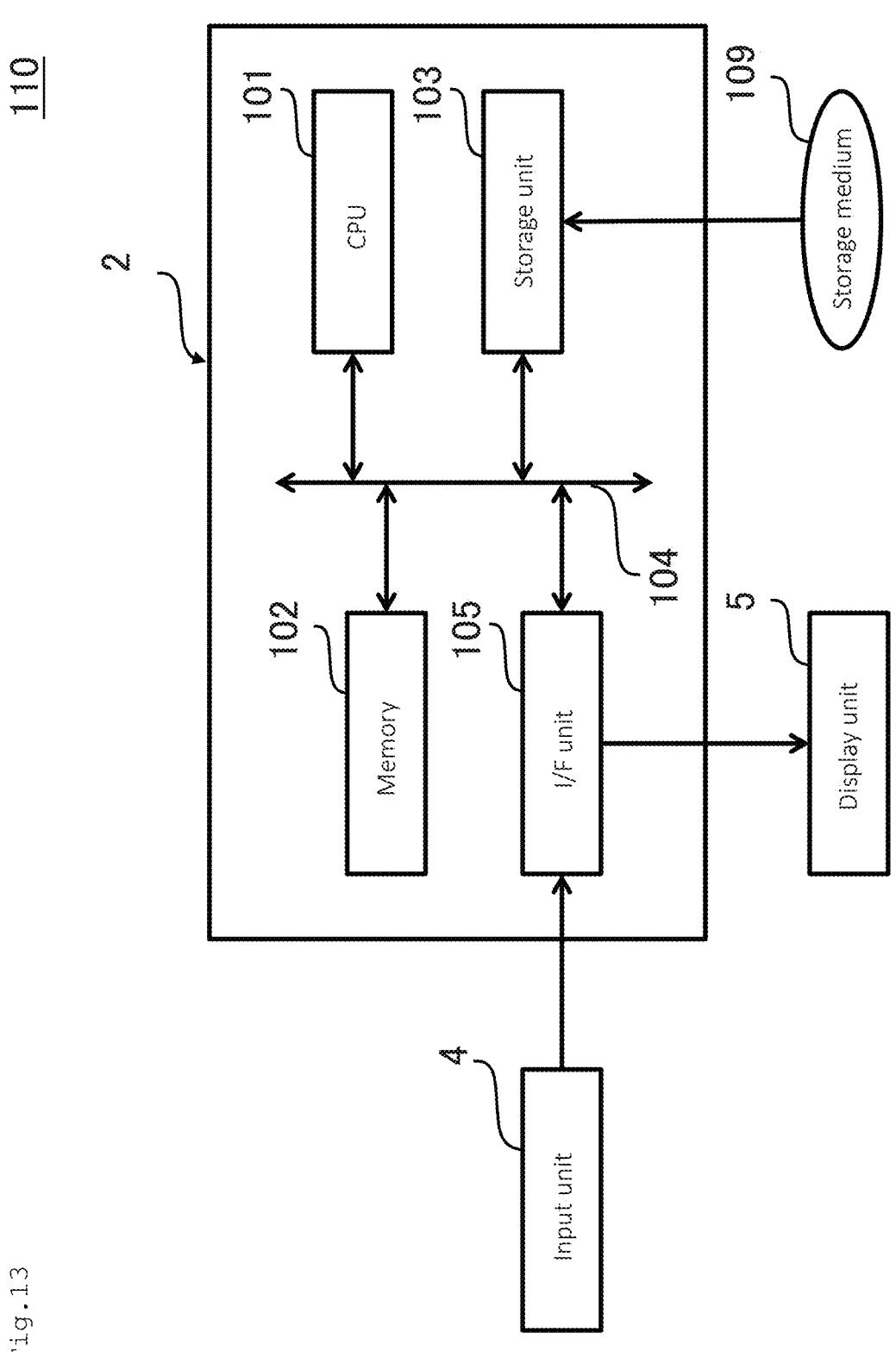
FIG. 13 is a block diagram illustrating a hardware configuration of the system 110 according to the second embodiment of the present invention.

FIG. 12 is an overview of a system 110 according to a second embodiment of the present invention, and FIG. 13 is a block diagram illustrating the hardware configuration of the system 110. The system 110 comprises a prediction apparatus 2, an input unit 4, and a display unit 5.

The prediction apparatus 2 includes, for example, a general-purpose personal computer, and comprises a CPU 101 for performing data processing described later, a memory 102 serving as a work area for data processing, a storage unit 103 for storing processed data, a bus 104 for transmitting data between the units, and an interface unit 105 (hereinafter referred to as an "I/F unit") for performing data input and output between the apparatus 2 and external devices. The input unit 4 and the display unit 5 are connected to the prediction apparatus 2. The input unit 4 includes, for example, a keyboard, and the display unit 5 includes, for example, a liquid crystal display. The input unit 4 and the display unit 5 may be integrated and implemented as a display with a touch panel. The prediction apparatus 2 need not be a single apparatus, and the CPU 101, the memory 102, the storage unit 103, and the like may be located in separate places and connected via a network. The apparatus 2 may also be an apparatus that omits the input unit 4 and the display unit 5 and that does not require an operator.

In the explanation below, a process performed by the prediction apparatus 2 means a process performed by the CPU 101 of the prediction apparatus 2 based on a prediction program unless otherwise specified. The CPU 101 temporarily stores necessary data (such as intermediate data being processed) in the memory 102 that serves as a work area, and suitably stores data that are stored for a long period of time, such as computation results, in the storage unit 103.

As described above, the hardware configuration of each of the prediction apparatus 2, the input unit 4, and the display unit 5 of the system 110 may be the same as that of each of the prediction apparatus 2, the input unit 4, and the display unit 5 of the system 100 shown in FIG. 8.

5-3. Prediction Apparatus

The invention includes, as the second embodiment, a prediction apparatus for predicting the presence of a disease and/or the stage of the disease in each of one or more organs other than the specific organ in a subject affected with a specific disease, the apparatus comprising the following computation means:

a means for obtaining information about a stage of the disease in the specific organ in the subject;

a means for checking the information about the stage obtained by the stage information obtaining means against standard data 2;

a means for extracting a pattern of an inter-organ cross talk indicator in each of one or more organs other than the specific organ in the subject based on the results obtained by the stage information checking means; and a means for predicting the presence of a disease and/or the stage of the disease in each of the one or more organs other than the specific organ by using, as a measure, the pattern of the inter-organ cross talk indicator obtained by the pattern extraction means.

In this embodiment, the presence of a disease and/or the stage of the disease in each of one or more organs other than a specific organ in a subject can be predicted by the system 110 (FIGS. 12 and 13) comprising the prediction apparatus 2 described in the "5-2. System configuration" section as the prediction apparatus above.

Figure 14:
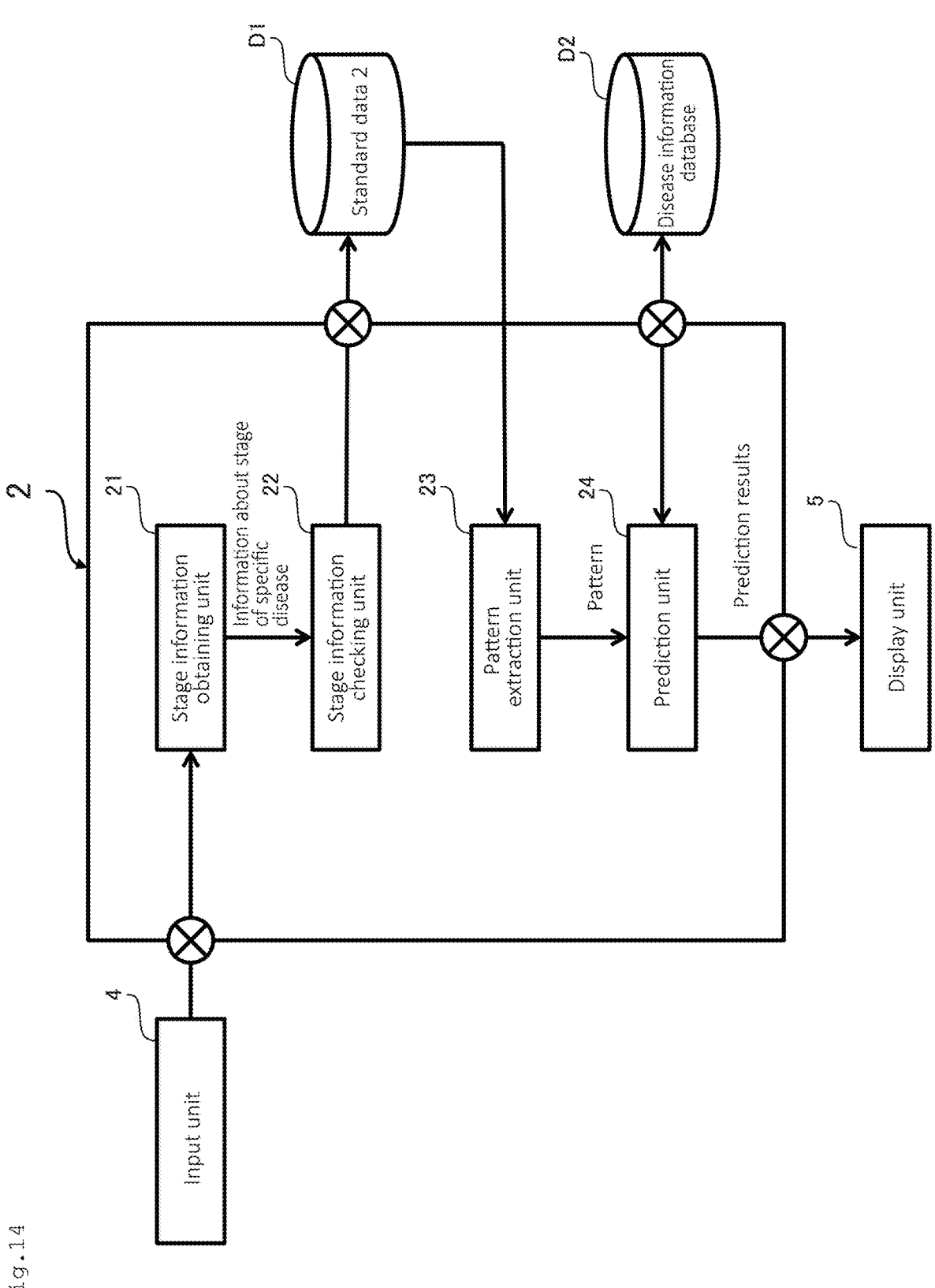
FIG. 14 is a block diagram to illustrate a function of a prediction apparatus 2 according to the second embodiment of the present invention.

FIG. 14 is a block diagram to illustrate a function of the prediction apparatus 2 according to the second embodiment of the present invention. The prediction apparatus 2 comprises a stage information obtaining unit 21, a stage information checking unit 22, a pattern extraction unit 23, and a prediction unit 24. These functional blocks are implemented by installing the prediction program according to the present invention in the storage unit 103 or the memory 102 of the prediction apparatus 2 and causing the CPU 101 to execute the program. With this structure, the prediction apparatus 2 carries out the prediction method described later in the "5-5. prediction method" section. The stage information obtaining means, stage information checking means, pattern extraction means, and prediction means recited in the claims correspond to the stage information obtaining unit 21, the stage information checking unit 22, the pattern extraction unit 23, and the prediction unit 24 shown in FIG. 14, respectively.

In other words, the prediction apparatus 2 is a prediction apparatus for predicting the presence of a disease and/or the stage of the disease in each of one or more organs other than a specific organ in a subject affected with a disease in the specific organ, the apparatus executing the following computation functions by the CPU 101:

a function of obtaining information regarding a stage of the disease in the specific organ in the subject;

a function of checking the information regarding the stage obtained by the stage information obtaining function against standard data 2;

a function of extracting a pattern of an inter-organ cross talk indicator in each of one or more organs other than the specific organ in the subject based on the results obtained by the stage information checking function, and a function of predicting the presence of a disease and/or the stage of the disease in each of the one or more organs other than the specific organ by using, as a measure, the pattern of the inter-organ cross talk indicator obtained by the pattern extraction function.

In this embodiment, for example, a user operates the input unit 4 to input information regarding in what stage of the disease in the specific organ (specific disease) the subject is. The stage information obtaining unit 21 obtains the input information about the stage of the specific disease (specific disease stage information). Standard data D1 (standard data 2) and disease information database D2 are stored outside the prediction apparatus 2 and put into the prediction apparatus 2 via, for example, the Internet.

The standard data D1 (standard data 2) and the disease information database D2 may be stored in the storage unit 103 or the memory 102 of the prediction apparatus 2 beforehand.

The stage information checking unit 22 checks the stage of the specific disease obtained by the stage information obtaining unit 21 against the standard data D1 (standard data 2), and the pattern extraction unit 23 extracts a pattern of an inter-organ cross talk indicator in each of one or more organs other than the specific organ in the subject based on the results obtained by the stage information checking unit 22. The prediction unit 24 predicts the presence of a disease and/or the stage of the disease in each of the one or more organs other than the specific organ by using, as a measure, the pattern of the inter-organ cross talk indicator obtained by the pattern extraction unit 23. The stage information checking unit 22, the pattern extraction unit 23, and the prediction unit 24 are functional blocks that respectively execute the stage information checking step, the pattern extraction step, and the prediction step of the prediction method according to the second embodiment of the present invention described later in the "5-5. Prediction method" section. The details of the computation processing of these steps are described in the "5-5. Prediction method" section with reference to FIG. 15.

Further, the functional blocks, i.e., the stage information obtaining unit 21, the stage information checking unit 22, the pattern extraction unit 23, and the prediction unit 24, are not necessarily executed by a single CPU, and may be processed distributively by multiple CPUs. For example, these functional blocks may be configured such that the function of the stage information obtaining unit 21 is executed by a CPU of a first computer and such that the functions of the stage information checking unit 22, the pattern extraction unit 23, and the prediction unit 24 are executed by a CPU of a second computer, i.e., another computer.

5-4. Prediction Program

Further, in order to carry out steps S21 to S29 in FIG. 15 described below, the prediction apparatus 2 stores the prediction program according to the present invention beforehand in the storage unit 103, for example, in an executable format. The prediction apparatus 2 carries out processing using the prediction program stored in the storage unit 103.

Specifically, the prediction program according to the second embodiment of the present invention is a prediction program that, when executed by a computer, causes the computer to carry out the following processing to predict the presence of a disease and/or the stage of the disease in each of one or more organs other than a specific organ in a subject affected with a disease in the specific organ:

processing of obtaining information regarding a stage of the disease in the specific organ in the subject;

processing of checking the information about the stage obtained by the stage information obtaining processing against standard data 2;

processing of extracting a pattern of an inter-organ cross talk indicator in each of one or more organs other than the specific organ in the subject based on the results obtained by the stage information checking processing; and processing of predicting the presence of a disease and/or the stage of the disease in each of the one or more organs other than the specific organ by using, as a measure, the pattern of the inter-organ cross talk indicator obtained by the pattern extraction processing.

In this embodiment, as shown in FIG. 13, the prediction program is stored in a computer-readable non-transitory tangible storage medium 109, such as a CD-ROM, and installed to the prediction apparatus 2 from the storage medium 109; alternatively, the prediction apparatus 2 may be connected to the Internet (not shown) to download the program code of the prediction program via the Internet. To cause a computer to carry out the computation processing described above, the prediction program according to the present invention may be linked to another program stored in the storage unit 103 or the memory 102. For example, the prediction program may be linked to commercially available database software mentioned in the "5-1. Outline" section above, and the stage information checking processing and the pattern extraction processing may be carried out using the database software.

The stage information obtaining processing corresponds to computation processing that is performed by the stage information obtaining unit 21 implemented through execution of the prediction program by the prediction apparatus 2. The stage information checking processing corresponds to computation processing that is performed by the stage information checking unit 22 implemented through execution of the prediction program by the prediction apparatus 2.

The pattern extraction processing corresponds to computation processing that is performed by the pattern extraction unit 23 implemented through execution of the prediction program by the prediction apparatus 2. The prediction processing corresponds to computation processing that is performed by the prediction unit 24 implemented through execution of the prediction program by the prediction apparatus 2.

5-5. Prediction Method

The prediction apparatus 2 according to the second embodiment of the present invention carries out the prediction method according to the second embodiment of the present invention. The prediction method according to the second embodiment of the present invention is a method for predicting the presence of the disease and/or the stage of the disease in each of one or more organs other than a specific organ in a subject affected with a disease in the specific organ, the method comprising:

a step of obtaining information regarding a stage of the disease in the specific organ in the subject;

a step of checking the stage obtained in the stage information obtaining step against standard data 2;

a step of extracting a pattern of an inter-organ cross talk indicator in each of one or more organs other than the specific organ in the subject based on the checking results obtained in the stage information checking step; and a step of predicting the presence of a disease and/or the stage of the disease in each of the one or more organs other than the specific organ by using, as a measure, the pattern of the inter-organ cross talk indicator obtained in the pattern extraction step.

Figure 15:
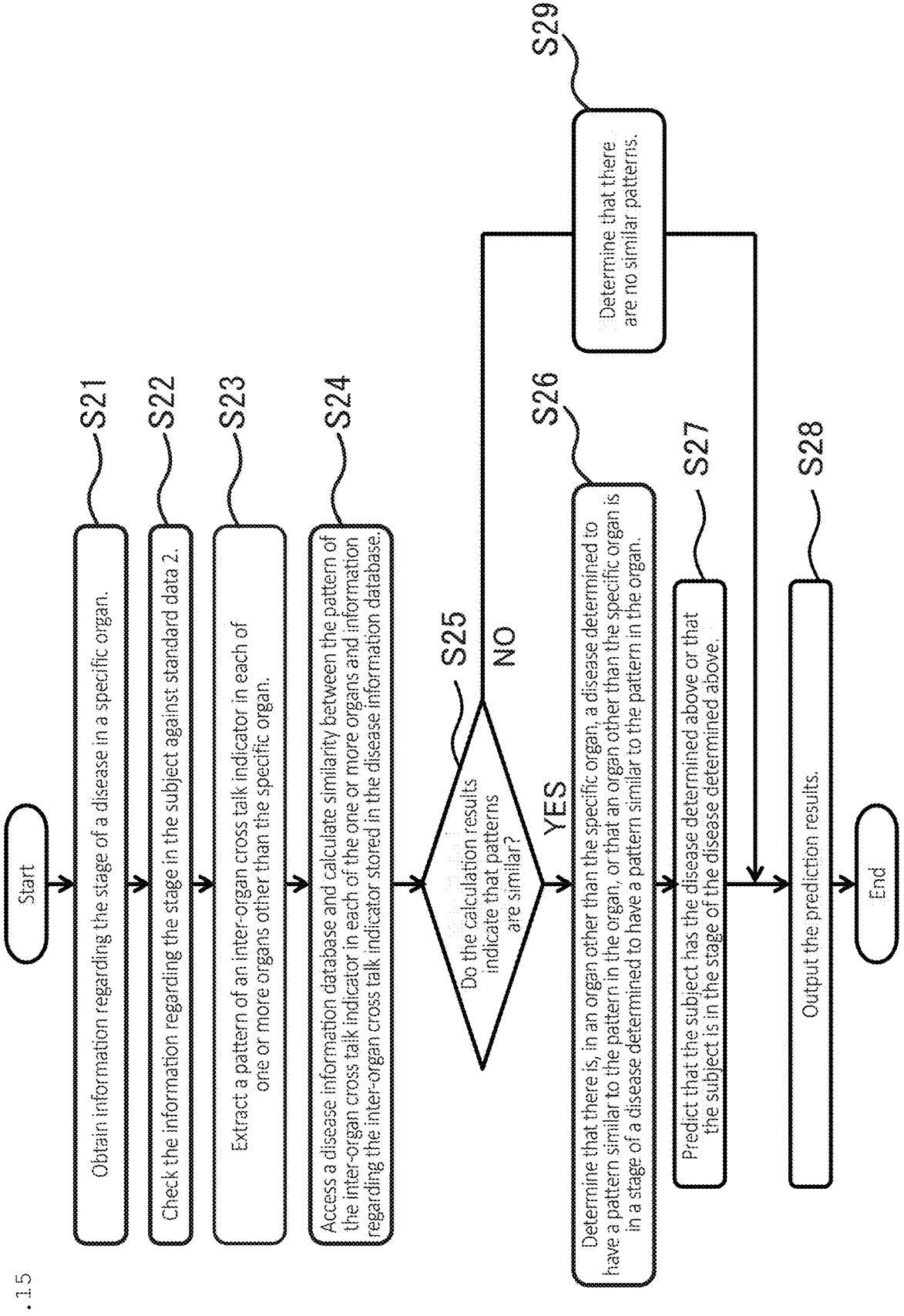
FIG. 15 is a flow chart illustrating a flow of data processing performed by the prediction apparatus 2 according to the second embodiment of the present invention to carry out a prediction method.

FIG. 15 is a flow chart illustrating a flow of data processing performed by the prediction apparatus 2 according to the second embodiment of the present invention to carry out the prediction method above. The processing of steps S21 to S29 shown in FIG. 15 is performed by the stage information obtaining unit 21, the stage information checking unit 22, the pattern extraction unit 23, and the prediction unit 24 shown in FIG. 14.

In step S21, the stage information obtaining unit 21 obtains stage information. The stage information is information regarding in what stage of the disease in the specific organ the subject is. The stage information obtaining unit 21 obtains the stage information by, for example, operation of the input unit 4. The manner in which the stage information is obtained is not limited to this, and the stage information may be stored in the storage unit 103 of the prediction apparatus 2 from an electronic chart or by any method, such as external data communication.

In step S22, the stage information checking unit 22 checks the stage information against standard data D1 (standard data 2). Subsequently, in step S23, the pattern extraction unit 23 determines, from the standard data D1 (standard data 2), standard data a at a stage of the disease in the specific organ corresponding to the stage information, based on the checking results obtained in step S22, and extracts, from the standard data α, a pattern of an inter-organ cross talk indicator corresponding to the stage in the subject in each of the one or more organs other than the specific organ in the subject. The specific procedure for extraction is in accordance with the description in the "4-1. Outline" section above. The prediction program described in the "5-4. Prediction program" section above may comprise program code of a program for causing the CPU 101 of the prediction apparatus 2 to perform computation processing by the stage information checking unit 22 and the pattern extraction unit 23 or, for example, may be linked to commercially available database software mentioned above to cause the CPU 101 to perform the computation processing by the stage information checking unit 22 and the pattern extraction unit 23, using the database software.

In step S24, the prediction unit 24 suitably accesses a disease information database D2 downloaded outside of the prediction apparatus 2 or downloaded in the memory 102 or the storage unit 103, and calculates and determines similarity between the pattern of the inter-organ cross talk indicator in each of the one or more organs extracted in step S23 and information regarding the inter-organ cross talk indicator stored in the disease information database. In step S26, it is determined that there is, in an organ other than the specific organ, a disease determined to have a pattern that is wholly or partially similar to the pattern of the inter-organ cross talk indicator in the organ ("YES" in step S25), or it is determined that an organ other than the specific organ is in a stage of a disease determined to have a pattern that is wholly or partially similar to the pattern of the inter-organ cross talk indicator in the organ ("YES" in step S25). In step S27, it is predicted that the subject is suffering from the disease determined in step S26 or that the subject is in the stage of the disease determined in step S26. The prediction program described in the "5-4. Prediction program" section above may comprise program code of a program for causing the CPU 101 of the prediction apparatus 2 to perform computation processing by the prediction unit 24 or, for example, may be linked to statistical analysis software mentioned in the "1. Explanation of terms" section above to cause the CPU 101 to perform the computation processing by the prediction unit 24, using the statistical analysis software.

In step S28, the prediction unit 24 outputs the results predicted in step S27. In this embodiment, the prediction results are displayed on the display unit 5, and the prediction results are stored in the storage unit 103 in the prediction apparatus 2. The prediction results may be displayed on a display unit of a computer terminal connected to the prediction apparatus 2 via the Internet that is external to the prediction apparatus 2, for example, in a third-party organization, instead of displaying the prediction result on the display unit 5.

When it is determined in step S25 from the results in step S24 that patterns are not similar ("NO" in step S25), the prediction unit 24 determines in step S29 that there are no similar patterns.

The specific procedure of each step is in accordance with the description in the "5-1. Outline" section above.

6. D-iOrgans 6-1. Outline

In this embodiment, the efficacy or side effect (or side effects) of a test substance are predicted from subject data X regarding an inter-organ cross talk indicator in each of one or more organs of an individual to which the test substance has been administered. The inter-organ cross talk indicator is derived from cells or tissue originating from each of the one or more organs. Specifically, subject data X regarding the inter-organ cross talk indicator in each of one or more organs of an individual to which a test substance has been administered, derived from cells or tissue originating from each of the one or more organs is compared with standard data Y derived beforehand from the corresponding inter-organ cross talk indicator, similarity of patterns of the inter-organ cross talk indicators is calculated, and the efficacy or side effect (or side effects) of the test substance in each of the one or more organs and/or each of one or more organs other than the one or more organs are predicted by using the similarity as a measure. The subject data X is obtained by performing the measurement method described in Section 2 above. More specifically, this embodiment comprises (1) a step of calculating similarity of patterns of the inter-organ cross talk indicators by comparing subject data X regarding an inter-organ cross talk indicator in each of one or more organs of an individual to which a test substance has been administered, the inter-organ cross talk indicator being derived from cells or tissue originating from each of the one or more organs, with standard data Y derived beforehand from the corresponding inter-organ cross talk indicator, and (2) a step of predicting efficacy a side effect (or side effects) of the test substance in each of the one or more organs and/or each of one or more organs other than the one or more organs by using, as a measure, the similarity of patterns of the inter-organ cross talk indicators obtained in step (1). Preferably, step (2) is a step of predicting efficacy or a side effect (or side effects) of the test substance in each of one or more organs other than the one or more organs by using, as a measure, the similarity of patterns of the inter-organ cross talk indicators calculated in step (1). When the test substance is a known substance, the known efficacy or side effect (or side effects) of the known substance are excluded from the efficacy or side effect (or side effects) described above. Preferably, the liver and kidney can be excluded from organs when a side effect (or side effects) are predicted. Examples of preferred organs collected for predicting efficacy or a side effect (or side effects) include body fluids except for blood, skin, brown adipose, and white adipose tissue. Further, when the efficacy or side effect (or side effects) of the test substance in each of one or more organs other than the one or more organs are predicted, the efficacy or side effect (or side effects) may be predicted in one organ or multiple organs. When the efficacy or side effect (or side effects) are predicted in multiple organs, the prediction may be sequentially performed for each organ or simultaneously performed. The prediction is preferably performed simultaneously.

To obtain information about subject data X, this embodiment may further comprise, before step (1), step (i) of obtaining information relating to the subject data X regarding an inter-organ cross talk indicator in each of the one or more organs in the individual to which the test substance has been administered, the inter-organ cross talk indicator being derived from the cells or tissue originating from each of the one or more organs. Step (i) may comprise determining the subject data X of an inter-organ cross talk indicator from the amount of the inter-organ cross talk indicator in each of the one or more organs of the individual to which the test substance has been administered, the inter-organ cross talk indicator being derived from the cells or tissue originating from each of the one or more organs. Further, step (i) may comprise identifying or quantifying the inter-organ cross talk indicator extracted from the cells or tissue originating from each of the one or more organs of the individual to which the test substance has been administered. Moreover, to determine the value of the subject data X, step (i) may comprise step (m) of obtaining information regarding the amount of the inter-organ cross talk indicator derived from cells or tissue originating from one or more organs of a negative control (or negative controls) corresponding to the cells or tissue originating from the one or more organs of the individual to which the test substance has been administered. Further, step (m) may comprise identifying or quantifying the inter-organ cross talk indicator extracted from the cells or tissue originating from each of the one or more organs of the negative control (or negative controls).

Step (i) may also comprise extracting the inter-organ cross talk indicator derived from the cells or tissue originating from each of the one or more organs of the individual to which the test substance has been administered (if necessary, from the cells or tissue collected from the one or more organs of a negative control (or negative controls)).

Here, the negative control (or negative controls) may be used synonymously with a negative control (or negative controls) with no disease, and includes untreated animals, sham-operated animal models, etc. An individual from which data of a subject is obtained and a negative control individual or negative control individuals may be the same species or different species, and preferably are the same species.

The prediction method according to this embodiment may further comprise, before step (i), the steps of:
(ii) providing the test substance;
(iii) providing the individual;
(iv) administering the test substance provided in step (ii) to the individual provided in step (iii);
(v) collecting the one or more organs from the individual administered the test substance in step (iv); and
(vi) obtaining the cells or tissue from the one or more organs collected in step (v).

Cells or tissue used for this method is not particularly limited, and the description in the "2. Methods for collecting and storing cells or tissue, or body fluids for extraction of an inter-organ cross talk indicator, and methods for extracting and measuring an inter-organ cross talk indicator" section above is incorporated herein by reference. Regarding the method for extracting the inter-organ cross talk indicator derived from cells, tissue, or the like collected from an individual, the description in Section 2 above can also be incorporated herein by reference.

Regarding extraction of RNA, the description in Section 2 above can be incorporated herein by reference. Analysis of RNA expression may be performed according to a known method, and the description in Section 2 above can be incorporated herein by reference. Preferably, analysis of RNA expression can be performed, for example, by using real-time PCR, a microarray, or RNA-Seq. When qualitative or quantitative analysis of RNA expression is performed using a microarray, a microarray chip comprising probes corresponding to each RNA species contained in standard data Y may be prepared beforehand for each existing substance, each disease, and/or each organ.

When at least one metabolite is used as an inter-organ cross talk indicator, extraction of the metabolite and analysis of the amount of the metabolite can be performed by the methods described in Section 2 above. When metabolites shown in FIG. 27 or 28 are analyzed, GCMS analysis or CEMS analysis is preferably performed.

The similarity between subject data X and standard data Y can be determined according to the method for determining similarity described in Section 1 above.

Further, among examined inter-organ cross talk indicators, when the pattern of any one inter-organ cross talk indicator in subject data X is similar to a pattern of the corresponding inter-organ cross talk indicator in standard data Y, the efficacy or side effect (or side effects) may be predicted from the inter-organ cross talk indicator. When the pattern of two or more inter-organ cross talk indicators in subject data X is similar to a pattern of the corresponding inter-organ cross talk indicator in the standard data Y, the efficacy or side effect (or side effects) may be predicted from the inter-organ cross talk indicators.

When it is determined by this method that subject data X is similar to standard data Y, it is determined that due to administration of the test substance, the individual to which the test substance has been administered undergoes the same changes in the inter-organ cross talk indicator as the individual from which the standard data Y is obtained.

In particular, when subject data X is similar to standard data Y1, it can be predicted that the test substance leads to a state of one or more organs and tissue reflected by an inter-organ cross talk indicator showing changes in the standard data Y1, a similar state of one or more organs and tissue reflected by an inter-organ cross talk indicator showing changes in the standard data Y1, or a state of one or more organs and tissue that can be easily presumed to be related to the inter-organ cross talk indicator from existing knowledge. When subject data X is similar to standard data Y2, it can be predicted that the test substance leads to efficacy or a side effect (or side effects) that are the same as or similar to the state that the existing substance used for obtaining the standard data Y2 leads to, or efficacy or a side effect (or side effects) that can be easily presumed to be related to the existing substance from existing knowledge. Further, when subject data X is similar to standard data Y3, it can be predicted that administration of the test substance causes the same state as the disease in the positive control individual or positive control individuals from which the standard data Y3 is obtained, or the same state as that of the organ or tissue with a lesion or condition in the positive control individual or positive control individuals from which the standard data Y3 is obtained, and it can be predicted that such a state is the side effect (or side effects) due to the test substance. Alternatively, when subject data X is similar to standard data Y3, it can be predicted that due to administration of the test substance, efficacy or a side effect (or side effects) appear in one or more organs or tissue that can be easily presumed from existing knowledge about the disease to be related to the disease in the positive control individual or positive control individuals from which the standard data Y3 is obtained. In addition, in cases where a positive control individual or positive control individuals affected with a disease from which standard data Y3 is obtained is receiving any treatment (administration of an existing substance) and where an individual before administration of a test substance has the same disease as the positive control individual or positive control individuals from which the standard data Y3 is obtained, when subject data X obtained after administration of the test substance is similar to the standard data Y3 obtained from the positive control individual or positive control individuals, it can be predicted that the test substance has efficacy that is the same as or similar to that of the treatment (administration of the existing substance) or efficacy that can be easily presumed to be related to the treatment from existing knowledge.

Further, standard data 2 and standard data 3 may be obtained from multiple organs.

Figure 16:
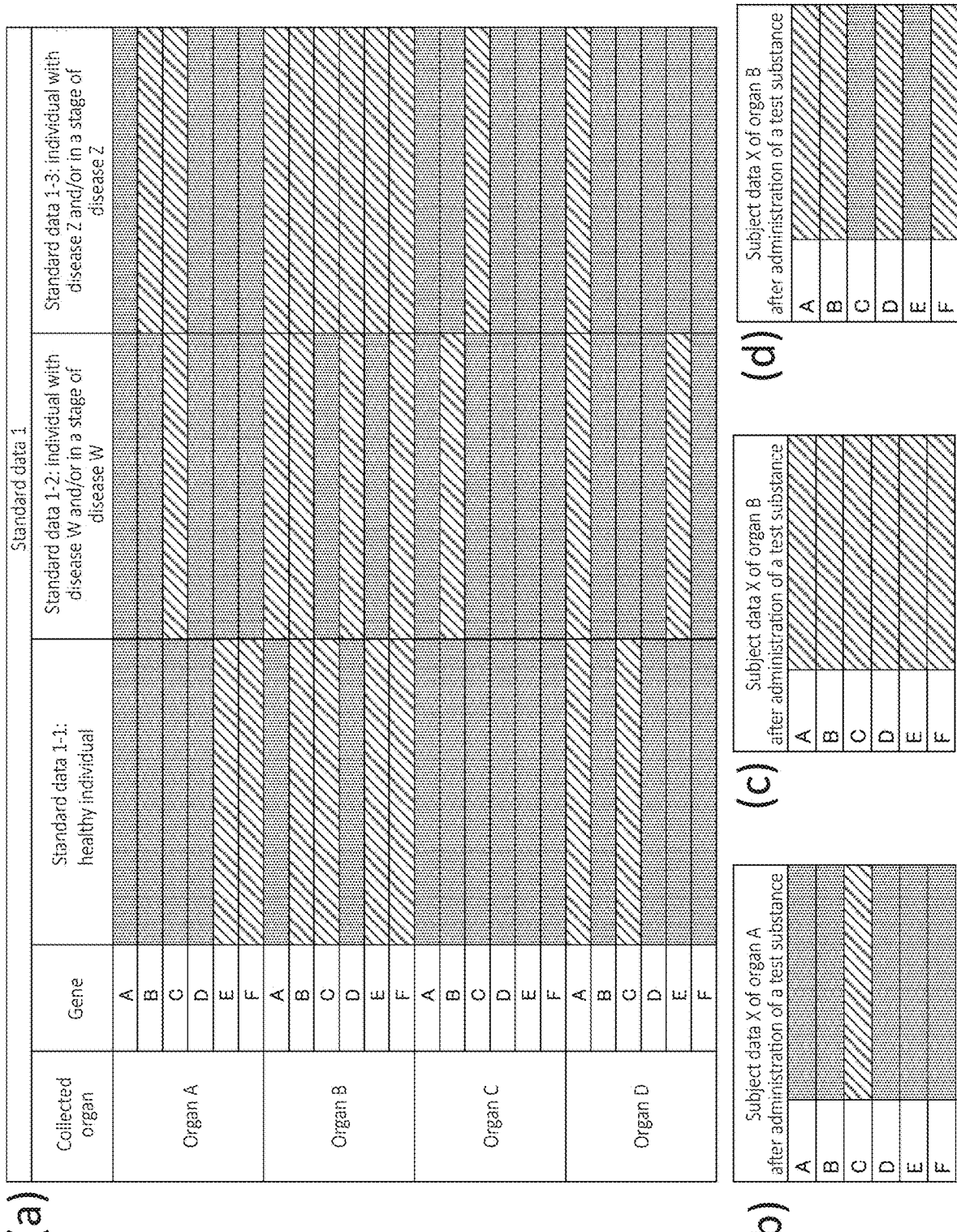
FIG. 16 illustrates an outline of D-iOrgans using standard data 1.

In another embodiment, the efficacy or side effect (or side effects) of a test substance can be predicted by using standard data 1 used in R-iOrgans. Specifically, (2-1) when an individual to which a test substance is to be administered is a healthy individual, the similarity of an inter-organ cross talk indicator between subject data X derived from an organ (e.g., organ A) of the subject to which the test substance has been administered (FIG. 16(b)) and standard data 1 derived from an organ corresponding to the organ (e.g., organ A) (FIG. 16(a)) is determined, (2-2) a disease and/or a stage of the disease (e.g., disease W, and/or a stage of disease W) corresponding to standard data 1 (standard data 1-2 of organ A of FIG. 16(a)) similar to the subject data X of the organ (e.g., organ A) is determined, and (2-3) it is further determined that the test substance causes the same state as the disease and/or the specific stage of the disease, thereby predicting the disease state that the test substance causes. Here, multiple organs may also be used. That is, (2-1') when an individual to which a test substance is to be administered is a healthy individual, the similarity of the inter-organ cross talk indicator between subject data X derived from each of multiple organs (e.g., organs A and B) of the subject to which the test substance has been administered (FIG. 16(b) and FIG. 16(c)) and standard data 1 derived from each of the multiple organs (e.g., organs A and B) (organs A and B of FIG. 16(a)) is determined, (2-2') a disease and/or a stage of the disease corresponding to standard data 1 similar to the subject data X of each of the multiple organs (e.g., organs A and B) (standard data 1-2 of organ A and standard data 1-3 of organ B in FIG. 16(a)) is determined; (2-3') it is further determined that the test substance causes the same state as the disease and/or the stage of the disease (e.g., disease W and/or the stage of disease W) in an organ (e.g., organ A) and further determined that the test substance causes the same state as the disease and/or the stage of the disease (e.g., disease Z and/or the stage of disease Z) in another organ (e.g., organ B), thereby predicting the disease states in the multiple organs that the test substance causes.

Figure 17:
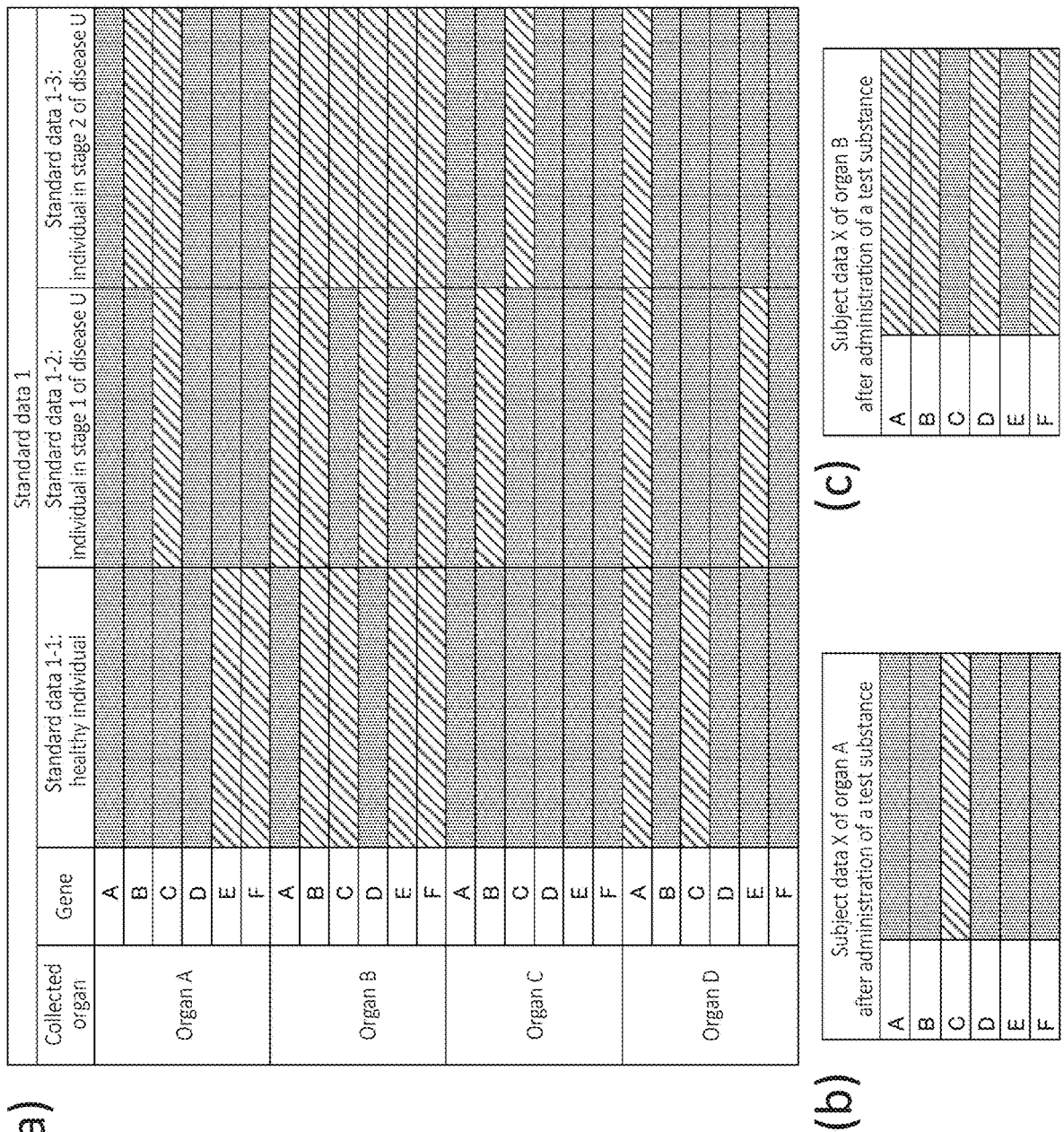
FIG. 17 illustrates an outline of D-iOrgans using standard data 1.

In another embodiment, when an individual to which a test substance is to be administered has a disease in organ A, (3-1) the stage in the individual is determined before administration of the test substance (e.g., stage 2 of disease U in FIG. 17(a)), (3-2) the similarity of an inter-organ cross talk indicator between subject data X of an organ (e.g., organ A) after administration of the test substance (FIG. 17(b)) and standard data 1 of the organ (e.g., organ A) (organ A in FIG. 17(a)) is determined, (3-3) a stage (stage 1 of disease U) corresponding to standard data 1 (standard data 1-2 of organ A in FIG. 17(a)) similar to the subject data X of the organ (e.g., organ A) is determined, and (3-4) when the stage (stage 1 of disease U) determined in (3-3) is reduced compared to the stage (stage 2 of disease U) determined in (3-1), it can be determined that the test substance is effective against the disease that the individual has.

Furthermore, in another embodiment, in view of the inter-organ cross talk system network, for example, the state of organ A can be predicted by using data of organ B contained in standard data 1 as subject data X. For instance, when an individual to which a test substance is to be administered is a healthy individual, (4-1) the similarity of an inter-organ cross talk indicator between subject data X of an organ (e.g., organ B) (FIG. 16(d)) and standard data 1 of an organ corresponding to the organ (e.g., organ B) (organ B in FIG. 16(a)) is determined, (4-2) a disease and/or a stage (disease W and/or a stage of disease W) corresponding to standard data 1 (standard data 1-2 of organ B in FIG. 16(a)) similar to the subject data X of the organ (e.g., organ B) is determined, and (4-3) when the disease and/or the stage determined in (4-2) (disease W and/or the stage of disease W) is a disease/or stage having a primary lesion (disease W and/or a stage of disease W) in another organ (e.g., organ A), it can be predicted that the test substance causes the same state as the disease and/or the stage determined in (4-2) (disease W and/or the stage of disease W), in the other organ (e.g., organ A).

When an individual to which a test substance is to be administered has a disease in organ A, (5-1) the stage in the individual is determined before administration of the test substance (e.g., stage 2 of disease U in FIG. 17(a)), (5-2) the similarity of an inter-organ cross talk indicator between subject data X of an organ (e.g., organ B) after administration of the test substance (FIG. 17(c)) and standard data 1 of an organ corresponding to the organ (e.g., organ B) is determined, (5-3) a stage (e.g., stage 1 of disease U in FIG. 17(a)) corresponding to standard data 1 (standard data 1-2 of organ B of FIG. 17(a)) similar to the subject data X (FIG. 17(c)) of the organ (e.g., organ B) is determined, (5-4) when the stage determined in (5-3) (e.g., stage 1 of disease U in FIG. 17(a)) is a stage of a disease in another organ (e.g., organ A), it is determined that the test substance causes the same state as the stage determined in (5-3) in the other organ (e.g., organ A), and (5-5) when the stage determined in (5-3) is reduced compared to the stage determined in (5-1), it can be predicted that the test substance is effective against the disease in the other organ that the individual has.

A specific embodiment using standard data Y3-Maps is described below.

Figure 18:
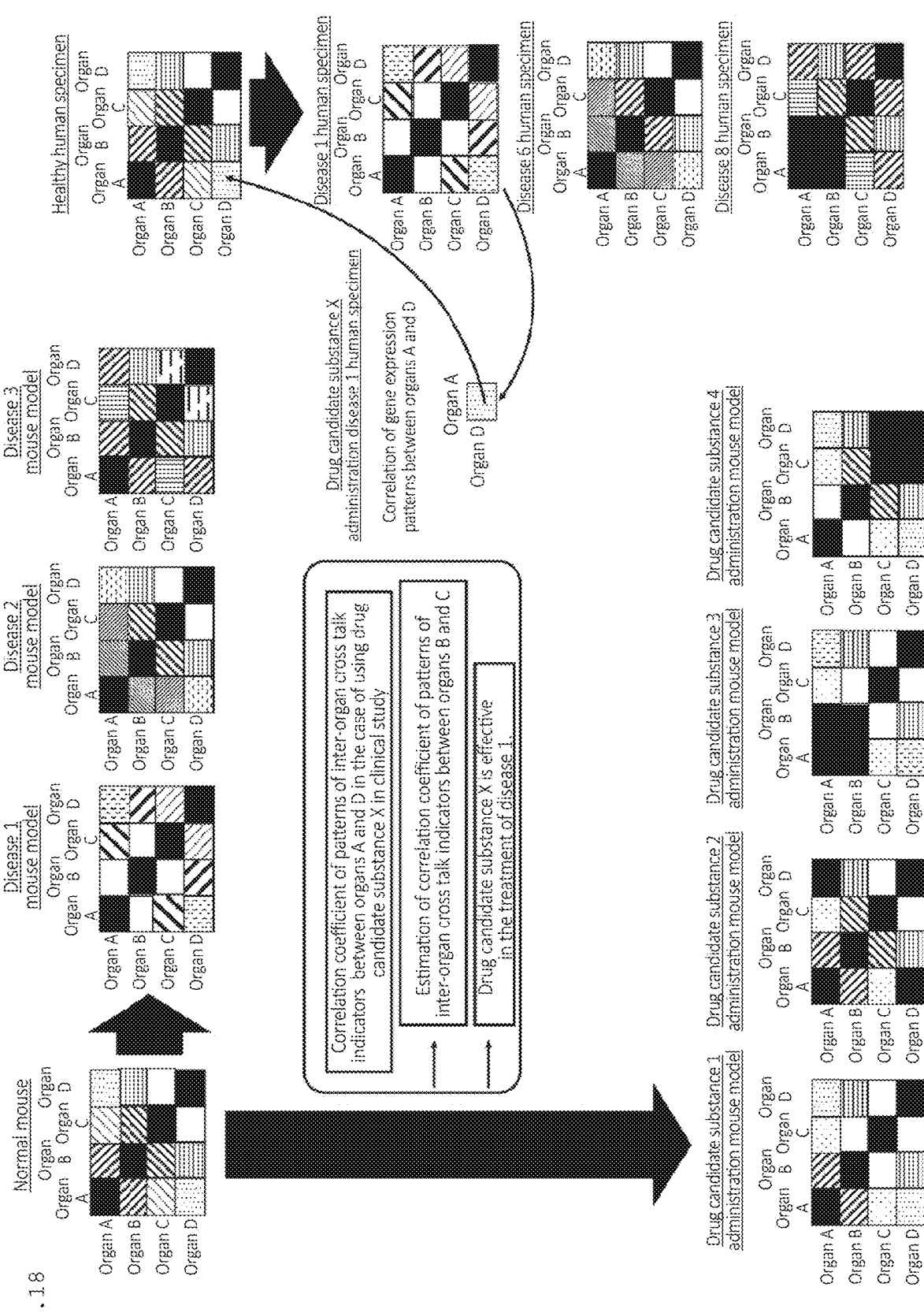
FIG. 18 illustrates an outline of D-iOrgans using standard data Y3-MAPs (an example of human clinical study). Hatching indicates patterns of inter-organ cross talk indicators, and each 16 hatched blocks (including white blocks) indicate a correlation map.

For example, when a clinical trial of a drug candidate substance X is performed in a clinical study (see FIG. 18), organs A and D are collected from a human with a disease (e.g., disease 1) to which the drug candidate substance X has been administered (an individual to which a test substance has been administered), and a pattern of an inter-organ cross talk indicator in each organ is determined. The correlation coefficient of the patterns of the inter-organ cross talk indicators between organ A and organ D is calculated according to the method described in the "1. Explanation of terms" section above. The likelihood between the calculated correlation coefficient and the correlation coefficient among the corresponding organs in standard data Y3-Maps generated beforehand is calculated, and it can be determined that the state linked to a standard data Y3-Map showing the highest likelihood is the state of the individual (the human) after administration of the drug candidate substance X. When the state of the human after administration of the drug candidate substance X is better than that before administration of the drug candidate substance X (in FIG. 18, when the correlation coefficient of the patterns between organ A and organ D in the disease 1 human specimen changes into the correlation coefficient of the patterns between organ A and organ D of the healthy human specimen), it can be predicted that the drug candidate substance X is effective against the disease (e.g., disease 1). Moreover, from the principle of the R-iOrgans technology, the patterns of the inter-organ cross talk indicators derived from organ B and organ C in the human mentioned above from which organ A and organ D are collected can be predicted by using standard data 1; therefore, the action of the drug candidate substance X on organ B and organ C can be predicted from the correlation coefficient between organ B and organ C by using standard data 1-Maps according to a method similar to the method for calculating likelihood of the correlation coefficient between organ A and organ D from that between organ B and organ C.

Figure 19:
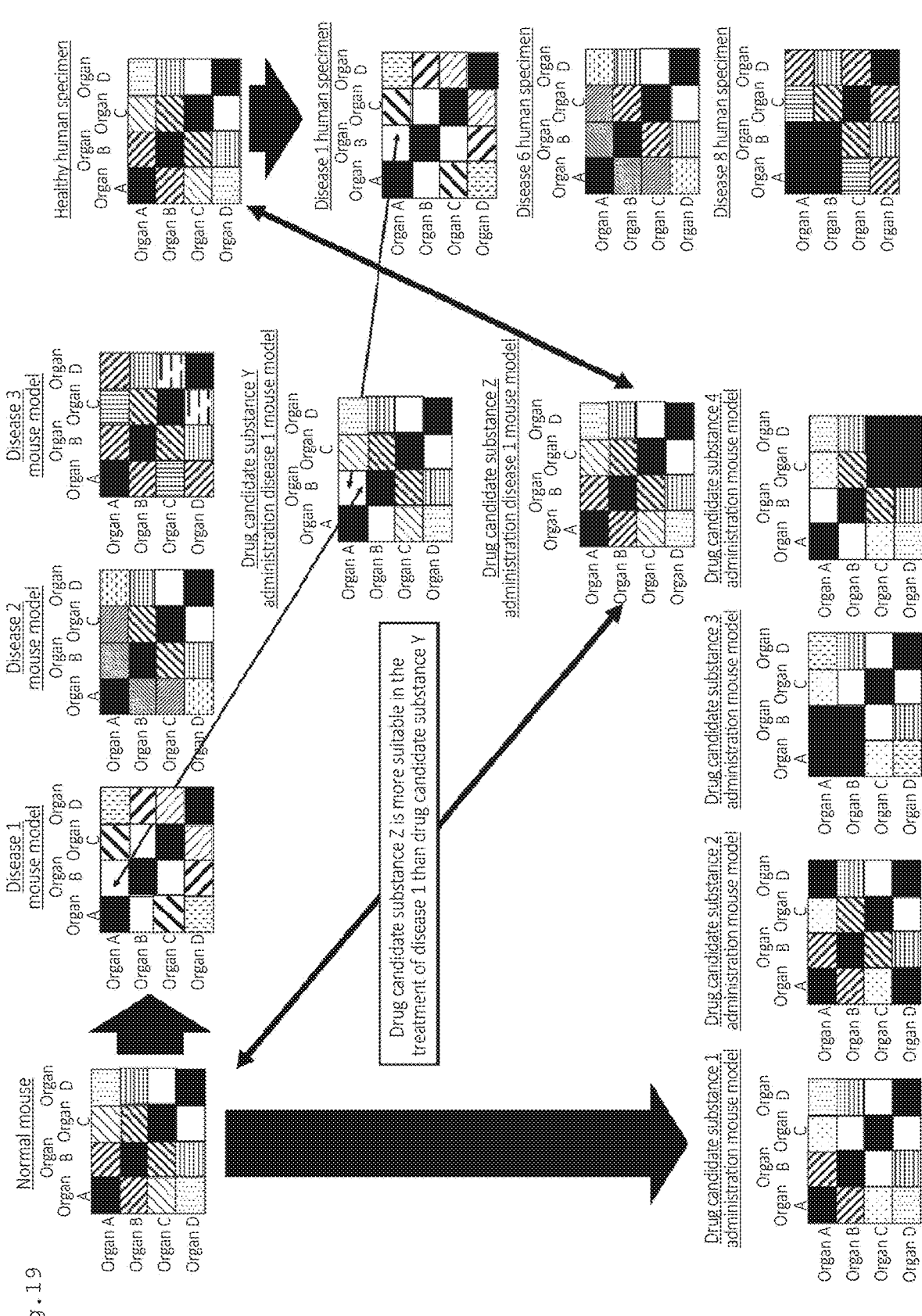
FIG. 19 illustrates an outline of D-iOrgans using standard data Y3-MAPs (an example of prediction of effect in a preclinical study). Hatching indicates patterns of inter-organ cross talk indicators, and each 16 hatched blocks (including white blocks) indicate a correlation map.

In another embodiment, for example, when a preclinical study of drug candidate substances Y and Z for a disease (e.g., disease 1) is performed by using laboratory animals, such as mice (see FIG. 19), multiple organs are collected from a mouse model of a disease (e.g., disease 1) to which a first candidate drug (e.g., drug candidate substance Y) or a second candidate drug (e.g., drug candidate substance Z) has been administered (an individual to which a test substance has been administered), and a pattern of an inter-organ cross talk indicator in each organ is determined. The correlation coefficient of patterns of the inter-organ cross talk indicators between two different organs is calculated for all of the multiple organs according to the method described in the "1. Explanation of terms" section above. The likelihood between the calculated correlation coefficient and the correlation coefficient among the corresponding organs in standard data Y3-Maps generated beforehand is calculated, and it can be predicted that the state linked to a standard data Y3-Map showing the highest likelihood is the state of the mouse after administration of the first drug candidate substance or the second drug candidate substance. When the condition of the mouse after administration of the first drug candidate substance or the second drug candidate substance is improved after the administration of the first drug candidate substance or the second drug candidate substance, it can be predicted that the first drug candidate substance or the second drug candidate substance is effective against the disease (e.g., disease 1). In FIG. 19, the correlation between the patterns of the inter-organ cross talk indicators when the drug candidate substance Y has been administered to the disease 1 mouse model is represented as "drug candidate substance Y administration disease 1 mouse model," and the correlation between the patterns of the inter-organ cross talk indicators when the drug candidate substance Z has been administered to the disease 1 mouse model is represented as "drug candidate substance Z administration disease 1 mouse model." The correlation between the patterns of the inter-organ cross talk indicators in the drug candidate substance Y administration disease 1 mouse model matches the correlation between the patterns of the inter-organ cross talk indicators in the drug candidate substance Z administration disease 1 mouse model, except for organ A and organ B. It can thus be determined that the correlation map of the patterns of the inter-organ cross talk indicators in the drug candidate substance Y administration disease 1 mouse model is similar to the correlation map of the patterns of the inter-organ cross talk indicators in the drug candidate substance Z administration disease 1 mouse model. That is, it can be predicted that the first drug candidate substance and the second drug candidate substance have similar action. It can also be predicted that the drug candidate substance Z is more therapeutically effective against the disease 1 because the correlation map of the patterns of the inter-organ cross talk indicators in the drug candidate substance Z administration disease 1 mouse model is the same as the correlation maps of the patterns of the inter-organ cross talk indicators in the healthy mouse and the healthy human specimen in FIG. 19. Specifically, in the treatment of a disease, when the correlation map of the patterns of the inter-organ cross talk indicators obtained using a second drug candidate substance is closer to the correlation map of the patterns of the inter-organ cross talk indicators of a healthy individual than the correlation map of the patterns of the inter-organ cross talk indicators obtained using a first drug candidate substance, it can be determined that the second drug candidate substance is more effective in the treatment of the disease.

Figure 20:
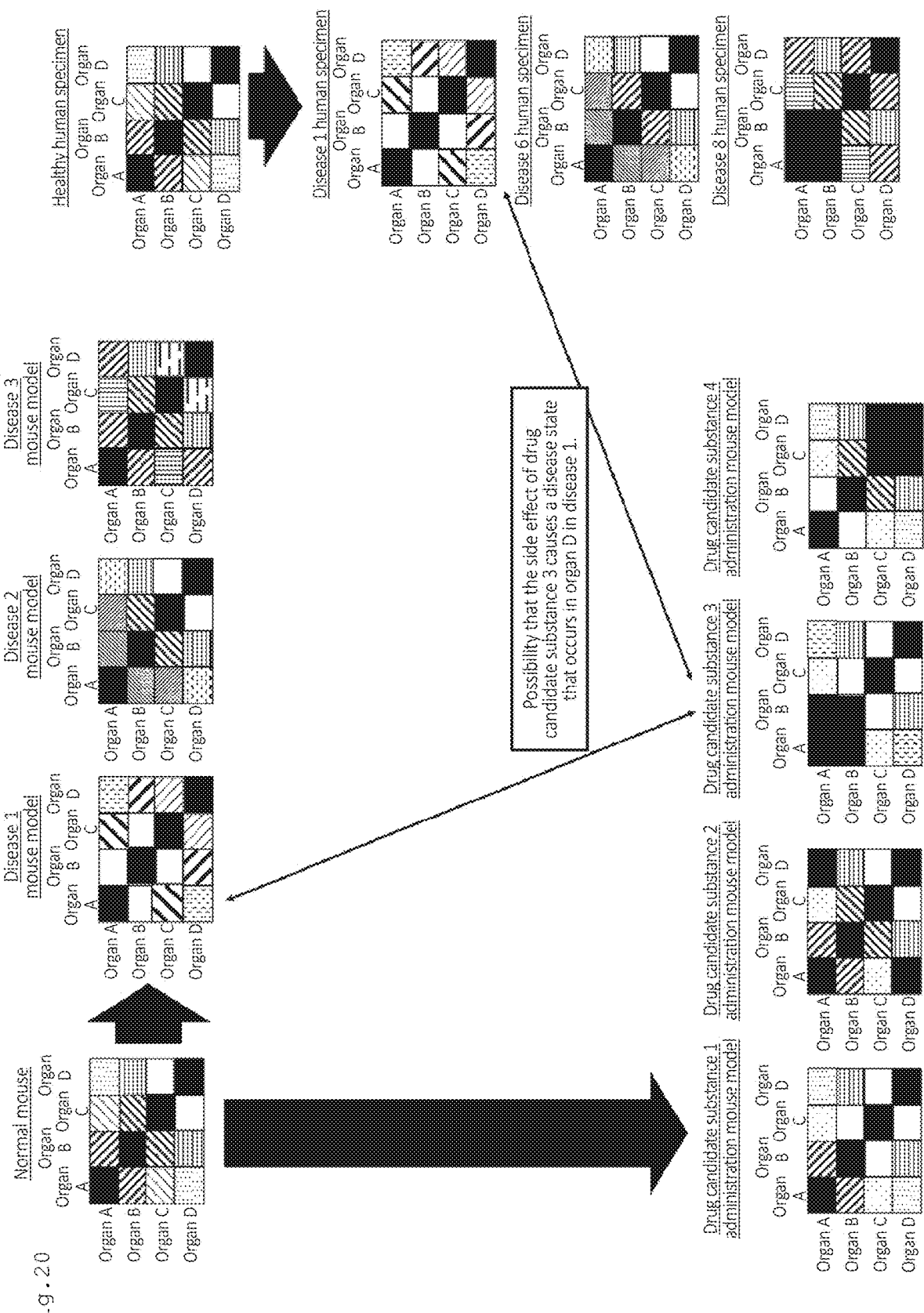
FIG. 20 illustrates an outline of D-iOrgans using standard data Y3-MAPs (an example of prediction of effect in a preclinical study). Hatching indicates patterns of inter-organ cross talk indicators, and each 16 hatched blocks (including white blocks) indicate a correlation map.

Further, in another embodiment, for example, the side effect (or side effects) of a test substance (e.g., drug candidate substance 3) can be predicted using laboratory animals, such as mice, in a preclinical study (see FIG. 20). Multiple organs (e.g., organs A, B, C, and D) are collected from an individual (e.g., a mouse) to which a test substance has been administered, and a pattern of an inter-organ cross talk indicator in each organ is determined. The correlation coefficient of patterns of the inter-organ cross talk indicators between two different organs is calculated for all of the multiple organs (e.g., organs A and D) according to the method described in the "1. Explanation of terms" section above. The likelihood between the calculated correlation coefficient and the correlation coefficient among the corresponding organs in standard data Y3-Maps generated beforehand is calculated, and it can be predicted that the state linked to a standard data Y3-Map showing the highest likelihood is the state of the individual after administration of the test substance. When the state corresponding to the standard data Y3-Map with the highest likelihood is a disease or a stage of the disease, it can be predicted that the test substance causes the disease or the stage of the disease. For example, in FIG. 20, when the correlation coefficient between organs A and D in the correlation map of the drug candidate substance 3 administration mouse model is similar to the correlation coefficient between organs A and D in the correlation map of the disease 1 mouse model, or the correlation coefficient between organs A and D in the correlation map of the disease 1 human specimen, it can be determined that the drug candidate substance 3 causes a side effect (or side effects) that are the same as the state of the disease 1. Further, in cases where the disease is myocardial infarction and organ B is the heart, when the test drug candidate substance 3 is known to act directly on the heart, but does not act directly on another organ (organ A, C, or D) (i.e., when there is common technical knowledge that the drug candidate substance 3 acts on cardiac cells, e.g., myocardial cells, in culture-based assays, but causes no changes in gene expression in other cultured cells, e.g., cells derived from organ A, C, or D), it can be predicted that a change in the correlation coefficient between organs A and D caused by administration of the drug candidate substance 3 is a change caused by a change in the heart resulting from the action of the drug candidate substance 3 on the heart through cross-talk with organs other than the heart.

6-2. System Configuration

Figure 21:
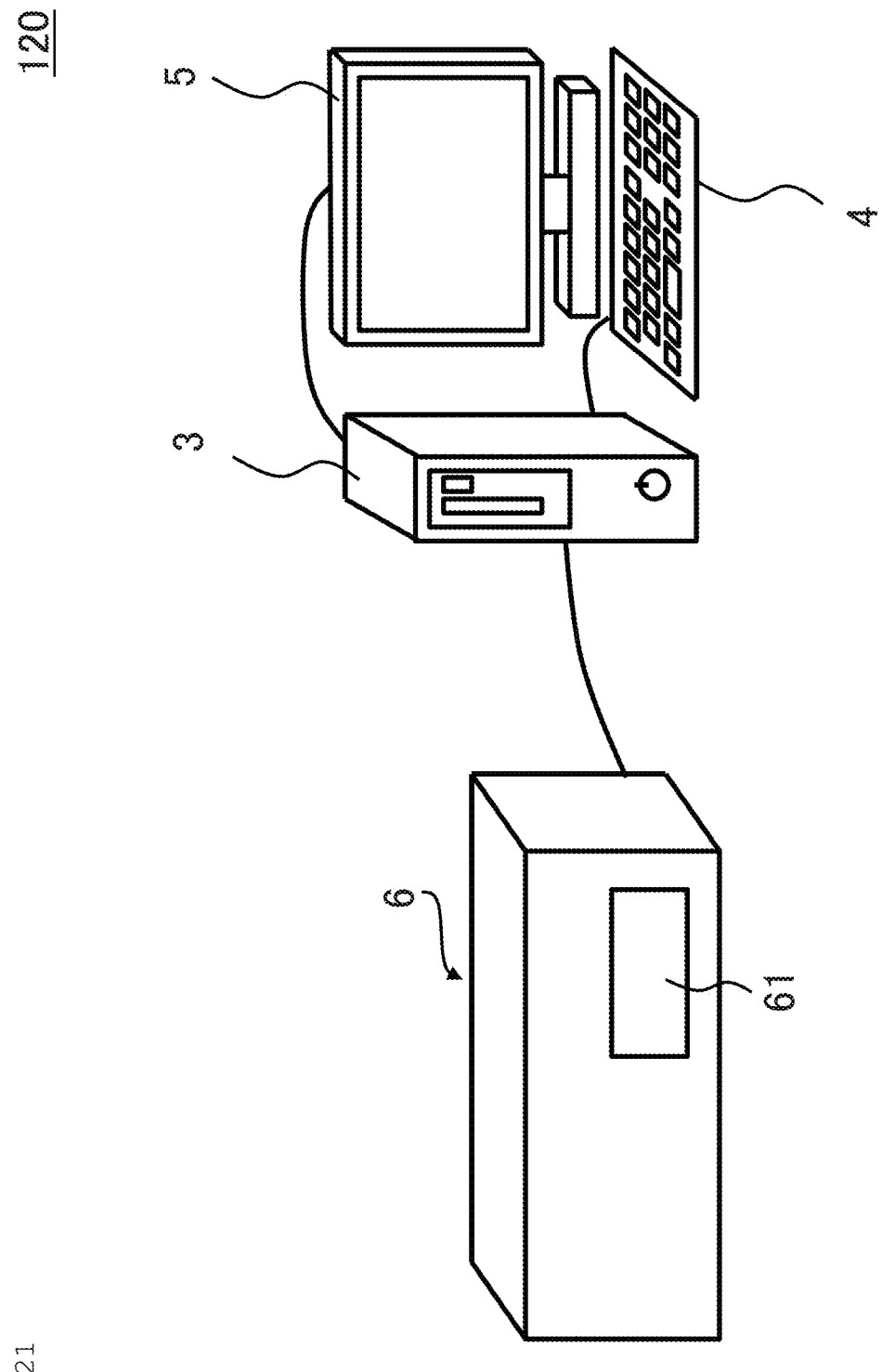
FIG. 21 is an overview of a system 120 according to a third embodiment of the present invention.
Figure 22:
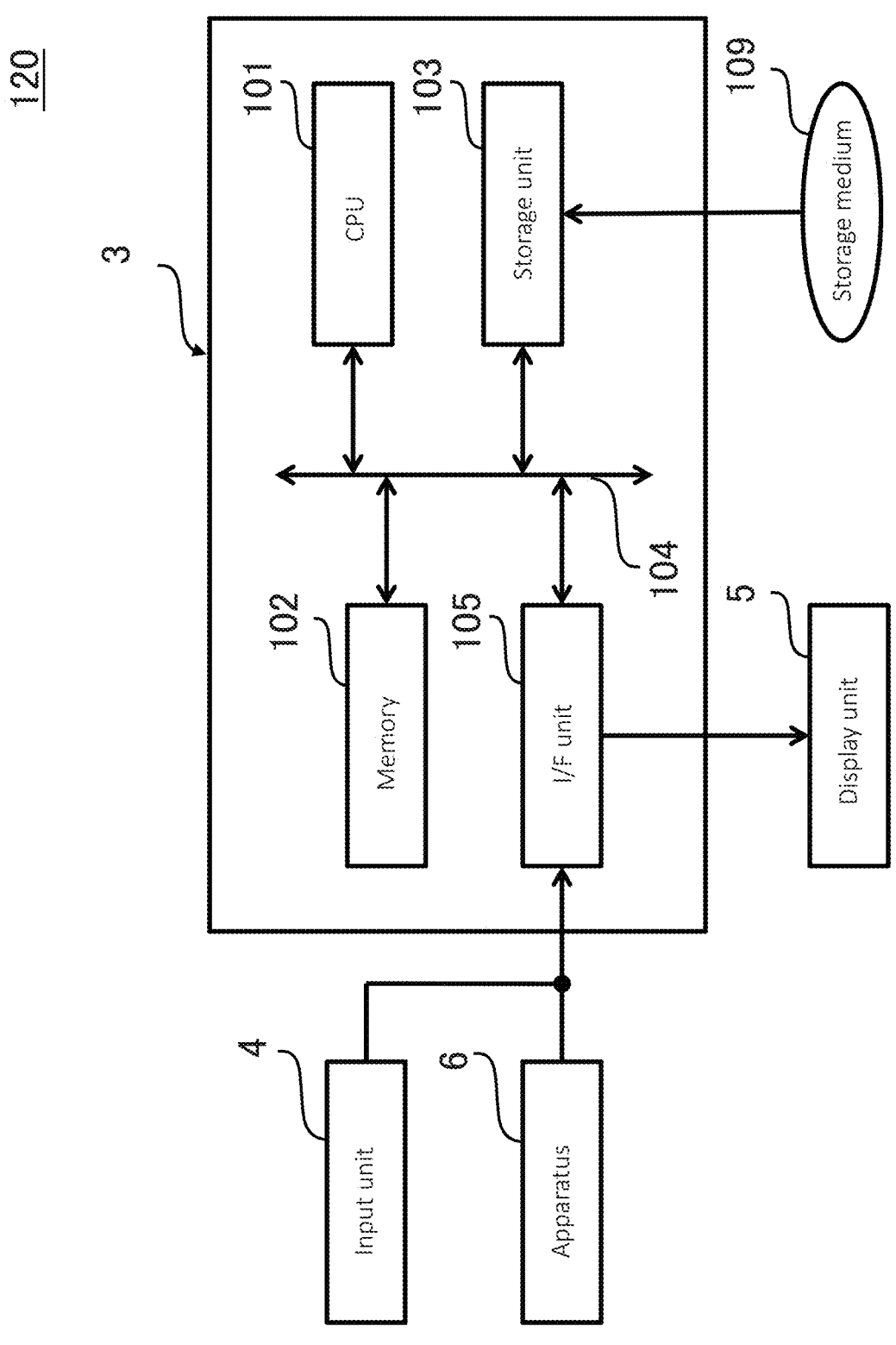
FIG. 22 is a block diagram illustrating a hardware configuration of the system 120 according to the third embodiment of the present invention.

FIG. 21 is an overview of a system 120 according to a third embodiment of the present invention, and FIG. 22 is a block diagram illustrating a hardware configuration of the system 120. The system 120 comprises a prediction apparatus 3, an input unit 4, a display unit 5, and an apparatus 6.

The prediction apparatus 3 includes, for example, a general-purpose personal computer, and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the apparatus 3 and external devices. The input unit 4 and the display unit 5 are connected to the prediction apparatus 3. The input unit 4 includes, for example, a keyboard, and the display unit 5 includes, for example, a liquid crystal display. The input unit 4 and the display unit 5 may be integrated and implemented as a display with a touch panel. The prediction apparatus 3 need not be a single apparatus, and the CPU 101, the memory 102, the storage unit 103, and the like may be located in separate places and connected via a network. The apparatus 3 may also be an apparatus that omits the input unit 4 and the display unit 5 and that does not require an operator.

The prediction apparatus 3 and the apparatus 6 are also not necessarily located in one place, and may be configured such that the apparatuses located in separate places are communicatively connected to each other via a network.

In the explanation below, a process performed by the prediction apparatus 3 means a process performed by the CPU 101 of the prediction apparatus 3 based on a prediction program unless otherwise specified. The CPU 101 temporarily stores necessary data (such as intermediate data being processed) in the memory 102 that serves as a work area, and suitably stores data that are stored for a long period of time, such as computation results, in the storage unit 103.

The apparatus 6 is an apparatus for measuring RNA expression levels by the RNA-Seq method or measuring the amounts of metabolites by mass spectrometry. The apparatus 6 comprises an analysis unit 61. A sample in which a reaction for RNA-Seq has been carried out is set in the analysis unit 61 to perform analysis of nucleotide sequences in the analysis unit 61.

The apparatus 6 is connected to the prediction apparatus 3 by a wired or wireless connection. The apparatus 6 A/D converts the measurement values of mRNAs and transmits them as digital data to the prediction apparatus 3. Therefore, the prediction apparatus 3 can obtain the measurement values of mRNAs as digital data that can be computed. In this embodiment, digital data from the apparatus 6 is referred to as "subject data regarding an inter-organ cross talk indicator" or simply referred to as "subject data."

6-3. Prediction Apparatus

As the third embodiment, the present invention includes an apparatus for predicting efficacy or a side effect (or side effects) of a test substance, the apparatus comprising the following computation means:

a means for calculating, by comparing subject data X regarding an inter-organ cross talk indicator in each of one or more organs of an individual to which the test substance has been administered, the inter-organ cross talk indicator being derived from cells or tissue originating from each of the one or more organs, with standard data Y derived beforehand from the corresponding inter-organ cross talk indicator, similarity of patterns of the inter-organ cross talk indicators between the subject data X and the standard data Y; and a means for predicting efficacy or a side effect(side effects) s of the test substance in each of the one or more organs and/or each of one or more organs other than the one or more organs by using, as a measure, the similarity of patterns of the inter-organ cross talk indicators obtained by the pattern similarity calculation means.

Here, the method for calculating similarity between the subject data X and the standard data Y and the method for determining whether the subject data X and the standard data Y are similar are as described in the "1. Explanation of terms" section above.

In this embodiment, the efficacy or side effect (or side effects) of a test substance can be predicted by the system 120 (FIG. 22) comprising the prediction apparatus 3 described in the "6-2. System configuration" section above as the prediction apparatus above.

Figure 23:
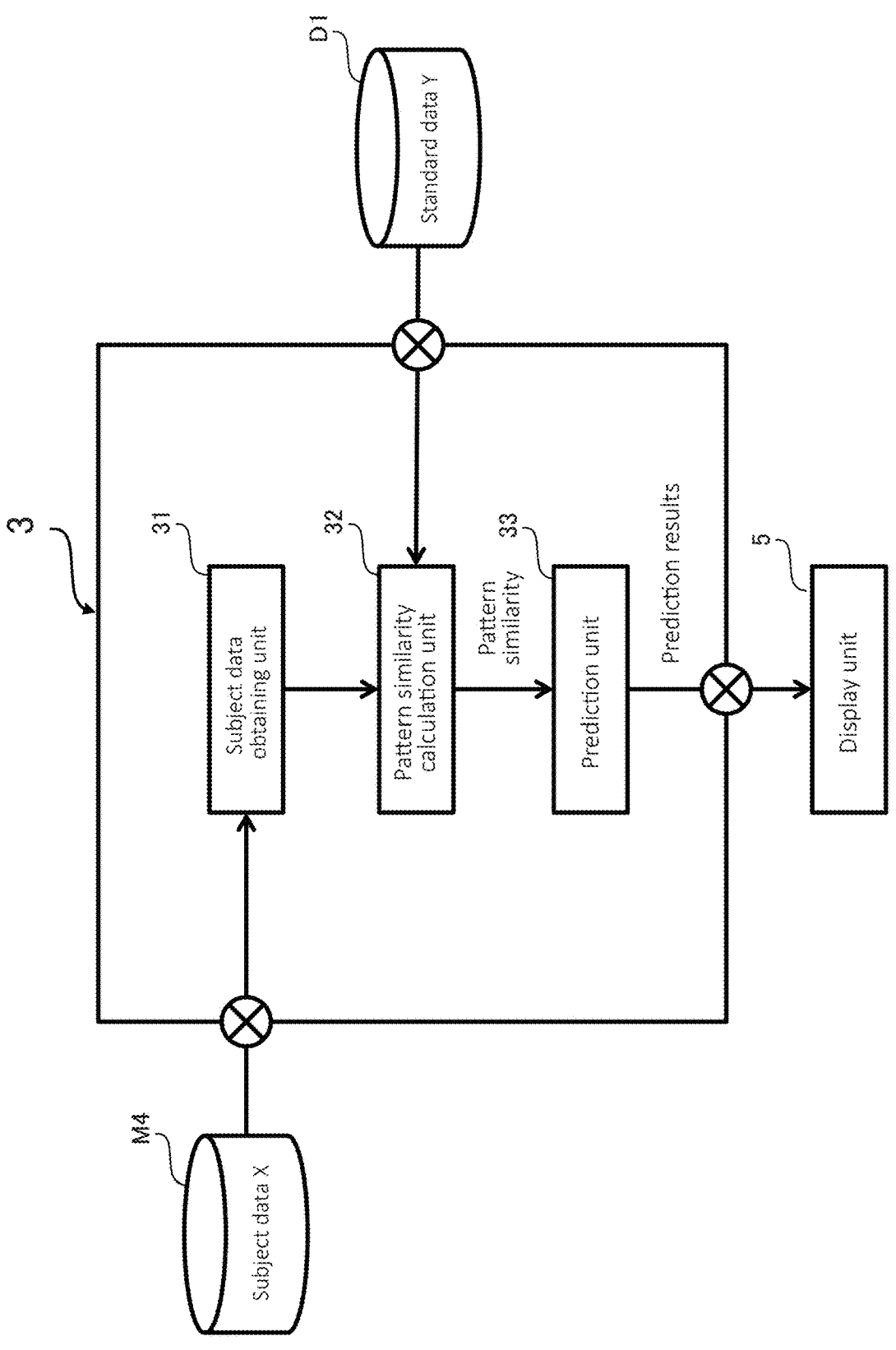
FIG. 23 is a block diagram to illustrate a function of a prediction apparatus 3 according to the third embodiment of the present invention.

FIG. 23 is a block diagram to illustrate a function of the prediction apparatus 3 according to the third embodiment of the present invention. The prediction apparatus 3 comprises a subject data obtaining unit 31, a pattern similarity calculation unit 32, and a prediction unit 33. These functional blocks are implemented by installing the program according to the present invention in the storage unit 103 or the memory 102 of the prediction apparatus 3 and causing the CPU 101 to execute the program. With this structure, the prediction apparatus 3 carries out the prediction method described later in the "6-5. Prediction method" section. The pattern similarity calculation means and the prediction means recited in the claims correspond to the pattern similarity calculation unit 32 and the prediction unit 33 shown in FIG. 23, respectively.

In this embodiment, subject data M4 (subject data X) and standard data D1 (standard data Y) may be stored outside the prediction apparatus 3 and put into the prediction apparatus 3 via, for example, the Internet.

The subject data M4 and the standard data D1 may be stored in the storage unit 103 or the memory 102 of the prediction apparatus 3 beforehand.

Further, the functional blocks, i.e., the subject data obtaining unit 31, the pattern similarity calculation unit 32, and the prediction unit 33, are not necessarily executed by a single CPU and may be processed distributively by multiple CPUs. For example, these functional blocks may be configured such that the function of the subject data obtaining unit 31 is executed by a CPU of a first computer and such that the functions of the pattern similarity calculation unit 32 and the prediction unit 33 are executed by a CPU of a second computer, i.e., another computer.

In other words, the prediction apparatus 3 is a prediction apparatus for predicting efficacy or a side effect (or side effects) of a test substance, the apparatus executing the following computation functions by the CPU 101:

a function of calculating, by comparing subject data X regarding an inter-organ cross talk indicator in each of one or more organs of an individual to which the test substance has been administered, the inter-organ cross talk indicator being derived from cells or tissue originating from each of the one or more organs, with standard data Y derived beforehand from the corresponding inter-organ cross talk indicator, similarity of patterns of the inter-organ cross talk indicators between the subject data X and the standard data Y; and a function of predicting efficacy or a side effect (or side effects) of the test substance in each of the one or more organs and/or each of one or more organs other than the one or more organs by using, as a measure, the similarity of patterns of the inter-organ cross talk indicators obtained by the pattern similarity calculation function.

In this embodiment, the subject data obtaining unit 31 obtains subject data M4 (subject data X) of an inter-organ cross talk indicator measured in the apparatus 6 from the apparatus 6. Standard data D1 (standard data Y) is stored outside the prediction apparatus 3 and put into the prediction apparatus 3 via, for example, the Internet.

The subject data M4 (subject data X) may also be put into the prediction apparatus 3 from a third-party organization (not shown) via a network. The subject data M4 (subject data X) and the standard data D1 (standard data Y) may be stored in the storage unit 103 or the memory 102 of the prediction apparatus 3 beforehand.

The pattern similarity calculation unit 32 compares the subject data M4 (subject data X) with the standard data D1 (standard data Y) and calculates the similarity of patterns of the inter-organ cross talk indicators. The prediction unit 33 predicts the efficacy or side effect (or side effects) of the test substance in each of the one or more organs and/or each of one or more organs other than the one or more organs by using, as a measure, the similarity of patterns of the inter-organ cross talk indicators obtained by the pattern similarity calculation unit 32. The pattern similarity calculation unit 32 and the prediction unit 33 are functional blocks that respectively execute the pattern similarity calculation step and the prediction step of the prediction method according to the third embodiment of the present invention described later in the "6-5. Prediction method" section. The details of the computation processing of these steps are described in the "6-5. Prediction method" section with reference to FIG. 24.

Further, the functional blocks, i.e., the subject data obtaining unit 31, the pattern similarity calculation unit 32, and the prediction unit 33, are not necessarily executed by a single CPU, and may be processed distributively by multiple CPUs. For example, these functional blocks may be configured such that the function of the subject data obtaining unit 31 is executed by a CPU of a first computer and such that the functions of the pattern similarity calculation unit 32 and the prediction unit 33 are executed by a CPU of a second computer, i.e., another computer.

6-4. Prediction Program

Further, in order to carry out steps S31 to S37 in FIG. 24 described below, the prediction apparatus 3 stores the prediction program according to the present invention in the storage unit 103 beforehand, for example, in an executable format (for example, a form in which the program can be produced by being converted from a programming language using a compiler). The prediction apparatus 3 carries out processing using the prediction program stored in the storage unit 103.

Specifically, the prediction program according to the third embodiment of the present invention is a program that, when executed by a computer, causes the computer to carry out the following processing to predict efficacy or a side effect (or side effects) of a test substance:

processing of calculating, by comparing subject data X regarding an inter-organ cross talk indicator in each of one or more organs of an individual to which the test substance has been administered, the inter-organ cross talk indicator being derived from cells or tissue originating from each of the one or more organs, with standard data Y derived beforehand from the corresponding inter-organ cross talk indicator; and processing of predicting efficacy or a side effect (or side effects) of the test substance in each of the one or more organs and/or each of one or more organs other than the one or more organs by using, as a measure, the similarity of patterns of the inter-organ cross talk indicators obtained by the pattern similarity calculation processing.

In this embodiment, as shown in FIG. 22, the prediction program is stored in a computer-readable non-transitory tangible storage medium 109, such as CD-ROM and installed to prediction apparatus 3 from the storage medium 109; alternatively, the prediction apparatus 3 may be connected to the Internet (not shown) to download the program code of the prediction program via the Internet. In addition, to cause a computer to carry out the computation processing described above, the prediction program according to the present invention may be linked to another program stored in the storage unit 103 or the memory 102. For example, the prediction program may be linked to statistical analysis software mentioned in the "1. Explanation of terms" section above, and the pattern similarity calculation processing may be carried out using the statistical analysis software.

The pattern similarity calculation processing corresponds to computation processing that is performed by the pattern similarity calculation unit 32 implemented through execution of the prediction program by the prediction apparatus 3. The prediction processing corresponds to computation processing that is performed by the prediction unit 33 implemented through execution of the prediction program by the prediction apparatus 3.

6-5. Prediction Method

The prediction apparatus 3 according to the third embodiment of the present invention carries out the prediction method according to the third embodiment of the present invention. The prediction method according to the third embodiment of the present invention is a method for predicting efficacy or a side effect (or side effects) of a test substance, the method comprising:

a step of calculating, by comparing subject data X regarding an inter-organ cross talk indicator in each of one or more organs of an individual to which the test substance has been administered, the inter-organ cross talk indicator being derived from cells or tissue originating from each of the one or more organs, with standard data Y derived beforehand from the corresponding inter-organ cross talk indicator, similarity of patterns of the inter-organ cross talk indicators between the subject data X and the standard data Y; and a step of predicting efficacy or a side effect (or side effects) of the test substance in each of the one or more organs and/or each of one or more organs other than the one or more organs by using, as a measure, the similarity of patterns of the inter-organ cross talk indicators obtained in the pattern similarity calculation step.

Figure 24:
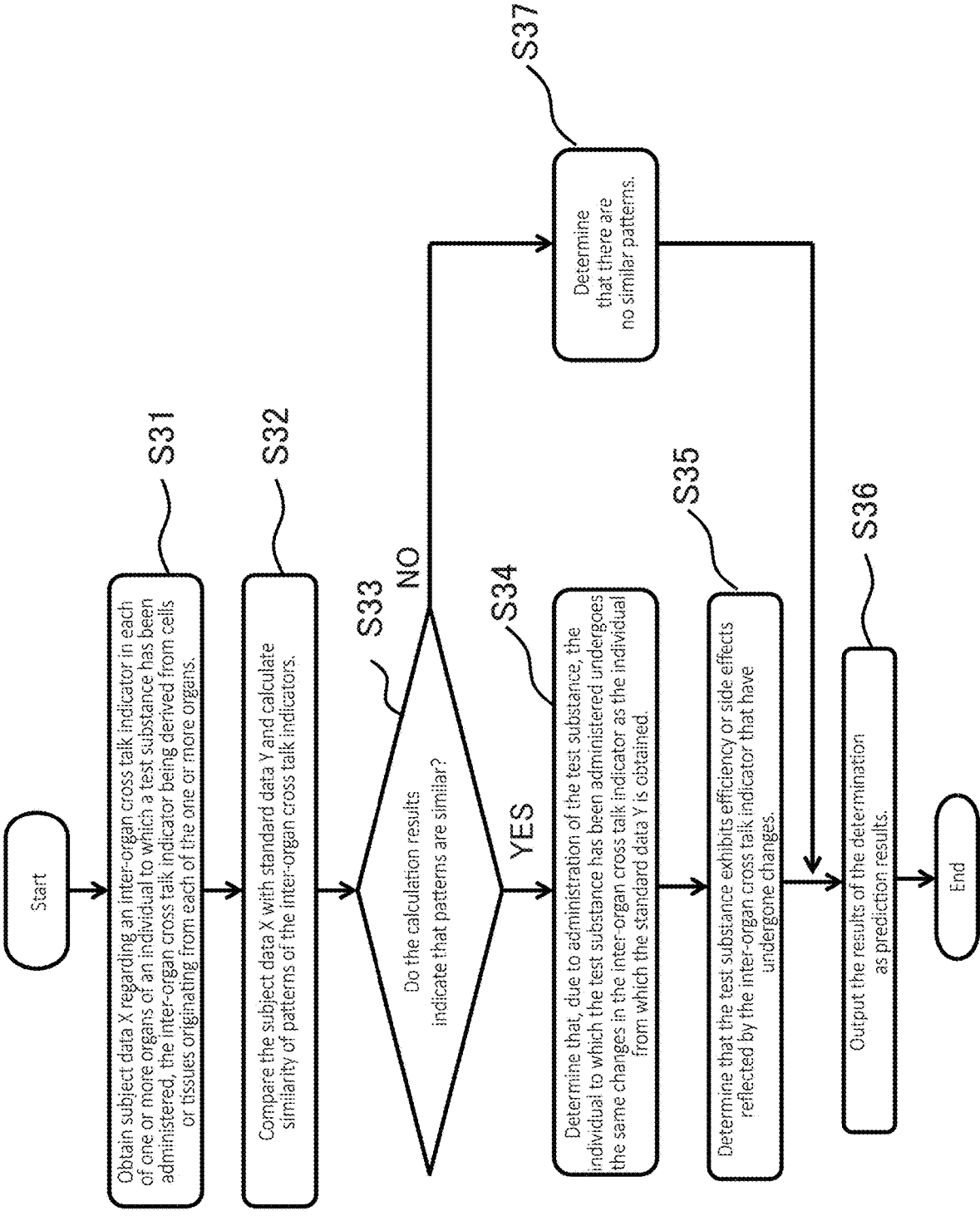
FIG. 24 is a flow chart illustrating a flow of data processing performed by the prediction apparatus 3 according to the third embodiment of the present invention to carry out a prediction method.

FIG. 24 is a flow chart illustrating a flow of data processing performed by the prediction apparatus 3 according to the third embodiment of the present invention to carry out the prediction method above. The processing of steps S31 to S37 shown in FIG. 24 is performed by the subject data obtaining unit 31, the pattern similarity calculation unit 32, and the prediction unit 33 shown in FIG. 23.

In step S31, the subject data obtaining unit 31 obtains subject data M4 (subject data X). The subject data M4 (subject data X) is a pattern of an inter-organ cross talk indicator in each of one or more organs of an individual to which the test substance has been administered, the inter-organ cross talk indicator being derived from cells or tissue originating from each of the one or more organs, and transmitted from the apparatus 6 to the prediction apparatus 3.

In step S32, the pattern similarity calculation unit 32 compares the obtained subject data M4 (subject data X) with standard data D1 (standard data Y) and calculates the similarity of patterns of the inter-organ cross talk indicators. The method for calculating the similarity and the method for determining whether patterns are similar are as described in the "1. Explanation of terms" section above. The prediction program described in the "6-4. Prediction program" section above may comprise program code of a program for causing the CPU 101 of the prediction apparatus 3 to perform computation processing by the pattern similarity calculation unit 32 or, for example, may be linked to statistical analysis software mentioned in the "1. Explanation of terms" section above to cause the CPU 101 to perform computation processing by the pattern similarity calculation unit 32 using the statistical analysis software.

In step S33, the prediction unit 33 predicts the similarity of patterns of the inter-organ cross talk indicators by using, as a measure, the similarity obtained in step S32. Specifically, when it is determined from the similarity that patterns are similar ("YES" in step 33), the prediction unit 33 determines in step S34 that due to administration of the test substance, the individual to which the test substance has been administered undergoes the same changes in an inter-organ cross talk indicator as the individual from which the standard data Y is obtained, and further determines in step S35 that the test substance exhibits efficiency or a side effect (or side effects) reflected by the inter-organ cross talk indicator that have undergone changes.

When it is determined from the similarity obtained in step S32 that patterns are not similar ("NO" in step 33), the prediction unit 33 determines in step S37 that there are no similar patterns.

In step S36, the prediction unit 33 outputs the results determined in step S35 or S37 as prediction result data. In this embodiment, the prediction results are displayed on the display unit 5 and the prediction result data is stored in the storage unit 103 in the prediction apparatus 3. The prediction results may be displayed on a display unit of a computer terminal connected to the prediction apparatus 3 via the Internet that is external to the prediction apparatus 3, for example, in a third-party organization, instead of displaying the prediction results on the display unit 5.

For example, when STZ is used as a test substance, gene candidates presented are Hamp and Saa1 in FIG. 44 described later in the Examples. In the explanation of FIG. 44, the prediction unit 33 or an operator suitably accesses a disease information database and obtains information about diseases of Hamp and Saa1 genes, thereby obtaining prediction results about the presence of efficacy or a side effect (or side effects) of the test substance (results of checking against a known database of diseases). When gene candidates are presented to an operator, results of checking against a known database about diseases (including information regarding efficacy and a side effect (or side effects)) can be presented so that the operator can easily understand the results, for example, by associating the results with each gene candidate.

7. Generation of Standard Data, and Standard Data 7-1. Generation of Standard Data The present invention relates to a method for generating standard data 1 for use in "4. Reverse iOrgans" above and a method for generating standard data 2 for use in "5. Forward iOrgans" above. The definition of terms is in accordance with the "1. Explanation of terms" section above.

The method for generating standard data is a method for generating standard data 1 of patterns of inter-organ cross talk indicators used for predicting the presence of a specific disease and/or the stage of the specific disease in a subject, the method comprising the steps of:

(A) obtaining information about an amount of an inter-organ cross talk indicator derived from cells or tissue originating from each of one or more organs other than the specific organ collected from a positive control (or positive controls) as a gold standard for each stage of the specific disease;

(B) obtaining information regarding an amount of the inter-organ cross talk indicator derived from cells or tissue originating from each of the one or more organs other than the specific organ collected from a negative control (or negative controls) as a gold standard;

(C) determining patterns of inter-organ cross talk indicators, each of the patterns being determined from a relationship (preferably a ratio) between the amount of the inter-organ cross talk indicator in the organ other than the specific organ collected from the positive control (or positive controls) affected with the specific disease obtained in step (A) and the amount of the corresponding inter-organ cross talk indicator in the same organ as the organ other than the specific organ collected from the negative control (or negative controls) without the specific disease obtained in step (B); and (D) linking the patterns of the inter-organ cross talk indicators to the corresponding stages of the specific disease.

More specifically, step (A) comprises the steps of:

extracting an inter-organ cross talk indicator from cells or tissue originating from each of one or more organs other than the specific organ collected from a positive control (or positive controls) as a gold standard for each stage of the specific disease; and identifying and quantifying the inter-organ cross talk indicator.

Step (B) comprises the steps of:

extracting the inter-organ cross talk indicator from cells or tissue originating from each of the one or more organs other than the specific organ collected from a negative control (or negative controls) as a gold standard; and identifying and quantifying the inter-organ cross talk indicator.

Specifically, the procedure for generating standard data 1 is a procedure as described later in the Examples.

First, cells or tissue is collected from one or more organs (e.g., fat) other than the specific organ of a negative control (or negative controls) and a positive control (or positive controls) in individual stages of the specific disease, and the inter-organ cross talk indicator is extracted. The extracted inter-organ cross talk indicator is then identified and quantified.

Next, patterns of inter-organ cross talk indicators are determined, each of the patterns being determined from the relationship between the amount of an inter-organ cross talk indicator in an organ other than the specific organ of a positive control (or positive controls) affected with the specific disease and the amount of the corresponding inter-organ cross talk indicator in the organ other than the specific organ of the negative control (or negative controls) without the specific disease (for example, a ratio, preferably a value obtained by dividing the value of the amount of an inter-organ cross talk indicator in an organ other than the specific organ collected from a positive control (or positive controls) affected with the specific disease by the value of the amount of the corresponding inter-organ cross talk indicator in the organ other than the specific organ of the negative control (or negative controls) without the specific disease). The determined patterns of inter-organ cross talk indicators are linked to the specific disease and stored in, for example, a storage device as standard data 1. Further, the standard data 1 can be stored in a server.

Furthermore, the present invention includes a method for generating standard data 2.

This method is a method for generating standard data 2 of patterns of inter-organ cross talk indicators for use in prediction of the presence of a disease and/or the stage of the disease in each of one or more organs other than a specific organ in a subject affected with the specific disease, the method comprising the steps of:

(A') obtaining information regarding an amount of an inter-organ cross talk indicator derived from cells or tissue originating from each of one or more organs other than the specific organ collected from a positive control (or positive controls) as a gold standard for each stage of the specific disease;

(B') obtaining information regarding an amount of the inter-organ cross talk indicator derived from cells or tissue originating from each of the one or more organs other than the specific organ collected from a negative control (or negative controls) as a gold standard;

(C') determining patterns of inter-organ cross talk indicators, each of the patterns being determined from a relationship (preferably a ratio) between the amount of the inter-organ cross talk indicator in the organ other than the specific organ of the positive control (or positive controls) affected with the specific disease obtained in step (A') and the amount of the corresponding inter-organ cross talk indicator in the same organ as the organ other than the specific organ in the negative control (or negative controls) without the specific disease obtained in step (B'); and (D') linking the patterns of the inter-organ cross talk indicators to the corresponding stages of the specific disease.

More specifically, step (A') comprises the steps of:

extracting an inter-organ cross talk indicator from cells or tissue originating from each of one or more organs other than the specific organ collected from a positive control (or positive controls) as a gold standard for each stage of the specific disease; and identifying and quantifying the inter-organ cross talk indicator.

Step (B') comprises the steps of:

extracting the inter-organ cross talk indicator from cells or tissue originating from each of the one or more organs other than the specific organ of a negative control (or negative controls) as a gold standard; and identifying and quantifying the inter-organ cross talk indicator.

Specifically, the procedure for generating standard data 2 is a procedure as described later in the Examples.

First, cells or tissue are collected from one or more organs other than the specific organ collected from a negative control (or negative controls) and a positive control or positive controls affected with the specific disease, and the inter-organ cross talk indicator is extracted. The extracted inter-organ cross talk indicator is then identified and quantified.

Next, patterns of inter-organ cross talk indicators are determined for each stage of the specific disease, each of the patterns being determined from the relationship between the amount of an inter-organ cross talk indicator in an organ other than the specific organ collected from a positive control (or positive controls) affected with the specific disease and the amount of the corresponding inter-organ cross talk indicator in the organ other than the specific organ collected from the negative control (or negative controls) without the specific disease (for example, a ratio, preferably a value obtained by dividing the value of the amount of an inter-organ cross talk indicator in an organ other than the specific organ collected from a positive control (or positive controls) with the specific disease by the value of the amount of the corresponding inter-organ cross talk indicator in the organ other than the specific organ collected from the negative control (or negative controls) without the specific disease). Such patterns of inter-organ cross talk indicators determined for each stage of the specific disease are stored in, for example, a storage device as standard data 2. Further, the standard data 2 can be stored in an external server.

To obtain standard data Y1, information regarding the function of an inter-organ cross talk indicator or information regarding expression levels when there are diseases or symptoms can be obtained from, for example, known disease databases, documents, or protein and gene databases. Examples of public disease databases include disease information databases mentioned in Section 5-1 above.

To obtain standard data Y2, an inter-organ cross talk indicator is extracted from cells or tissue originating from one or more organs collected from a positive control individual or positive control individuals to which existing substances have been individually administered and, if necessary, the one or more organs collected from a negative control individual or negative control individuals (extraction step). The method for extracting the inter-organ cross talk indicator is not particularly limited, and the inter-organ cross talk indicator may be extracted by a known method. When the inter-organ cross talk indicator is RNA or a group of metabolites, extraction of the inter-organ cross talk indicator can be performed by, for example, the method described in Section 2 above. Here, the negative control (or negative controls) may be used synonymously with a negative control (or negative controls) with no disease, and includes untreated animals, sham-operated animal models, and the like. The time at which cells or tissue is collected from one or more organs of the positive control individual or positive control individuals to which the existing substances have been individually administered is as follows: according to the pharmacokinetics of the existing substances, cells or tissue may be collected when the efficacy or side effect of the substances appears in the individuals, collected within the period of time in which the effect is sustained, or collected when or after the effect wears off.

Next, the inter-organ cross talk indicator extracted in the extraction step is identified and quantified (identification and quantification step). The method for identifying and quantifying the inter-organ cross talk indicator is not limited as long as the inter-organ cross talk indicator can be identified or quantified. For example, when the inter-organ cross talk indicator is RNA or a group of metabolites, they can be identified and quantified according to the method of analysis of RNAs or the method for measuring metabolites described in Section 2 above.

To obtain standard data Y3, a positive control individual or positive control individuals with individual diseases can be used instead of the positive control individual or positive control individuals to which the existing substances have been individually administered in the method for obtaining standard data Y2. Examples of the positive control individual or positive control individuals with individual diseases include animals that have spontaneously developed a disease, disease animal models, transgenic animals, and the like.

The extraction step and the identification and quantification step can be performed according to the method for obtaining standard data Y2. Here, the positive control individual or positive control individuals with individual diseases may be individuals that are untreated or subjected to treatment (administration of an existing substance).

Next, standard data Y of an inter-organ cross talk indicator is determined from the amount of the inter-organ cross talk indicator quantified in the identification and quantification step (determination step). The amount of the inter-organ cross talk indicator obtained in the identification and quantification step may be used as is as standard data Y. Standard data Y2 may be determined, preferably from the relationship between the amount of the inter-organ cross talk indicator in an organ of an individual to which an existing substance has been administered and the amount of the corresponding inter-organ cross talk indicator in the same organ in a negative control (or negative controls), more preferably the ratio between the amount of the inter-organ cross talk indicator in an organ of an individual to which an existing substance has been administered and the amount of the corresponding inter-organ cross talk indicator in the same organ in a negative control (or negative controls), and even more preferably the ratio of the amount of the inter-organ cross talk indicator in an organ of an individual to which an existing substance has been administered to the amount of the corresponding inter-organ cross talk indicator in the same organ in a negative control (or negative controls). In another embodiment, standard data Y3 may be determined as the relationship between the amount of the inter-organ cross talk indicator in an organ of a positive control individual or positive control individuals affected with a disease and the amount of the corresponding inter-organ cross talk indicator in the same organ in a negative control (or negative controls), preferably the ratio of the amount of the inter-organ cross talk indicator in an organ of a positive control individual or positive control individuals affected with a disease and the amount of the corresponding inter-organ cross talk indicator in the same organ in a negative control (or negative controls), more preferably the ratio of the amount of the inter-organ cross talk indicator in an organ of a positive control individual or positive control individuals affected with a disease to the amount of the corresponding inter-organ cross talk indicator in the same organ in a negative control (or negative controls).

A database of standard data Y may be made beforehand, or standard data Y may be obtained when subject data X is obtained.

7-2. Standard Data

The present invention includes standard data 1 generated by the method described above.

Generated standard data 1 may be stored in the storage unit 103 or the memory 102 of the prediction apparatus 1. Alternatively, generated standard data 1 may be stored in a storage device connected locally to the prediction apparatus 1 or in an external storage device, for example, a storage device of a server, accessible via a network by the prediction apparatus 1.

Further, the present invention includes standard data 2 generated by the method described above.

Generated standard data 2 may be stored in the storage unit 103 or the memory 102 of the prediction apparatus 2. Alternatively, generated standard data 2 may be stored in a storage device connected locally to the prediction apparatus 2 or in an external storage device, for example, a storage device of a server, accessible via a network by the prediction apparatus 2.

When the inter-organ cross talk indicator is RNA, RNA that shows changes may be predetermined for each of the animals to which existing substances have been individually administered or each of the animals with each disease, and a microarray for detecting target RNA may be prepared. In this case, changes mean that the ratio mentioned above is more than 1 or less than 1, preferably more than 1.5 or less than 0.67, more preferably more than 2 or less than 0.5, even more preferably more than 5 or less than 0.2.

The third embodiment of the present invention allows for not only more accurate and comprehensive prediction of the efficacy or side effect (or side effects) of test substances, but also identification of new and previously unknown efficacy or side effect (or side effects) of existing substances. Further, based on the obtained data, this embodiment enables studies of methods for preventing the side effect (or side effects) of test substances, and makes it possible to find new applications of test substances that have limited use despite desirable efficacy. Thus, the third embodiment of the present invention may comprise the step of selecting, depending on changes in subject data X, a drug that balances out or enhances the changes. Here, changes in subject data X mean that the ratio mentioned above is more than 1 or less than 1, preferably more than 1.5 or less than 0.67, more preferably more than 2 or less than 0.5, even more preferably more than 5 or less than 0.2.

8. Microarray and Kit

The present invention includes a microarray (also referred to as "DNA chip") for use in the methods described in Section 4, Section 5, and/or Section 6 above.

Probes that the microarray comprises are not particularly limited as long as they can detect nucleic acids described in Section 1 above or nucleic acids reverse-transcribed or amplified using nucleic acids described in Section 1 above as templates. The probes that the microarray comprises are preferably those including complementary nucleotide sequences, at least in part, to the nucleotide sequences of RNAs expressed from genes of group 1 described in Section 1 above or cDNAs synthesized by reverse transcription from RNAs expressed from genes of group 1, and more preferably those including complementary nucleotide sequences, at least in part, to the nucleotide sequences of RNAs expressed from genes of group 2 or cDNAs synthesized by reverse transcription from RNAs expressed from genes of group 2. Among these, particularly preferred are those including complementary nucleotide sequences, at least in part, to the nucleotide sequences of RNAs expressed from genes of group 1 or group 2 containing polyA sequences or cDNAs synthesized by reverse transcription from RNAs expressed from genes of group 1 or group 2 containing polyA sequences.

For example, when the specific organ is the heart and the specific disease is myocardial infarction, more specifically, the probes are ones including complementary nucleotide sequences, at least in part, to the nucleotide sequences of at least one RNA selected from the group consisting of RNAs expressed from the genes of group 3 described in FIG. 30 or at least one RNA selected from the group consisting of RNAs expressed from the orthologs, of the genes of group 3, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 4 described in FIG. 30 or at least one RNA selected from the group consisting of RNAs expressed from the orthologs, of the genes of group 4, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 5 described in FIG. 30 or at least one RNA selected from the group consisting of RNAs expressed from the orthologs, of the genes of group 5, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 6 described in FIG. 30 or at least one RNA selected from the group consisting of RNAs expressed from the orthologs, of the genes of group 6, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 7 described in FIG. 30 or at least one RNA selected from the group consisting of RNAs expressed from the orthologs, of the genes of group 7, that are present in the individual described above, or cDNAs synthesized by reverse transcription from the at least one RNA. Most preferably, the probes are ones including complementary nucleotide sequences, at least in part, to the nucleotide sequences of at least one RNA selected from the group consisting of RNAs expressed from the genes of group 8 described in FIG. 30 or at least one RNA selected from the group consisting of RNAs expressed from the orthologs, of the genes of group 8, that are present in the individual described above, or cDNAs synthesized by reverse transcription from the at least one RNA.

For example, when the specific organ is the brain and the specific disease is dementia, the probes are, more specifically, ones including complementary nucleotide sequences, at least in part, to the nucleotide sequences of at least one RNA selected from the group consisting of RNAs expressed from the genes of group 3 described in FIG. 34 or at least one RNA selected from the group consisting of RNAs expressed from the orthologs, of the genes of group 3, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 4 described in FIG. 34 or at least one RNA selected from the group consisting of RNAs expressed from the orthologs, of the genes of group 4, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 5 described in FIG. 34 or at least one RNA selected from the group consisting of RNAs expressed from the orthologs, of the genes of group 5, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 6 described in FIG. 34 or at least one RNA selected from the group consisting of RNAs expressed from the orthologs, of the genes of group 6, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 7 described in FIG. 34 or at least one RNA selected from the group consisting of RNAs expressed from the orthologs, of the genes of group 7, that are present in the individual described above, or cDNAs synthesized by reverse transcription from the at least one RNA.

For example, when the specific disease is a tumor, the probes are, more specifically, ones including complementary nucleotide sequences, at least in part, to the nucleotide sequences of at least one RNA selected from the group consisting of RNAs expressed from the genes of group 3 described in FIG. 36, 38, or 39 or at least one RNA selected from the group consisting of RNAs expressed from the orthologs, of the genes of group 3, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 4 described in FIG. 36, 38, or 39 or at least one RNA selected from the group consisting of RNAs expressed from the orthologs, of the genes of group 4, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 5 described in FIG. 36, 38, or 39 or at least one RNA selected from the group consisting of RNAs expressed from the orthologs, of the genes of group 5, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 6 described in FIG. 36, 38, or 39 or at least one RNA selected from the group consisting of RNAs expressed from the orthologs, of the genes of group 6, that are present in the individual described above, or cDNAs synthesized by reverse transcription from the at least one RNA. More preferably, the probes are ones including complementary nucleotide sequences, at least in part, to the nucleotide sequences of at least one RNA selected from the group consisting of RNAs expressed from the genes of group 7 described in FIG. 36, 38, or 39 or at least one RNA selected from the group consisting of RNAs expressed from the orthologs, of the genes of group 7, that are present in the individual described above, or cDNAs synthesized by reverse transcription from the at least one RNA.

The probes that the microarray comprises may be DNA or RNA, and preferably DNA. The length of the probes is not particularly limited as long as the probes have a length that can be used as capture probes of the microarray, and is preferably about 100 mer, more preferably about 60 mer, and even more preferably about 20 to 30 mer. The probes can be produced with, for example, a known oligonucleotide synthesizer.

The basal material of the microarray is also not particularly limited as long as nucleic acid probes can be immobilized on it. Examples include glass, polymers, such as polypropylene, nylon membranes, and the like.

The probes may be immobilized on the basal material according to a known method. For example, a spacer containing a reactive group or a cross-linker for immobilizing probes may be used.

Further, the present invention includes a kit comprising the microarray mentioned above for use in the methods described in Section 4, Section 5, and/or Section 6 above. The kit of the present invention preferably comprises not only the microarray, but also a medium, such as paper or a compact disc, on which information about nucleic acids that can detect the probes on the microarray and information about the locations of the probes are stored, or a medium, such as paper or a compact disc, on which information for accessing such information is stored.

Additionally, a buffer or the like used for hybridization may be supplied with the kit.

9. Supplementary Note

In the prediction apparatuses and the prediction programs based on the inter-organ cross talk system described in the above embodiments, regarding the presence of efficacy against a disease or a side effect (or side effects), the results of checking against a known database of diseases can be output by computer processing as prediction results based on gene candidates. Moreover, the prediction apparatuses and the prediction programs based on the inter-organ cross talk system can serve as apparatuses and programs for assisting an operator in prediction by presenting gene candidates to the operator and further presenting efficacy or a side effect (or side effects) associated with the gene candidates so that the operator can easily understand them.

EXAMPLES

The present invention is described in more detail below with reference to examples. The present invention, however, should not be construed as limited to the examples.

I. i-Organs

1. Myocardial Infarction Model 1-1. Establishment of Myocardial Infarction Mouse Model, Organ Collection, and Blood Collection 8- to 12-week-old male ICR mice were anesthetized with 2-2.5% isoflurane (Abbott Japan, Wako Japan) and endotracheally intubated with a 20-gauge venous catheter. The mice were ventilated with a volume-controlled respirator (Harvard Apparatus) with 200 μL per cycle at a rate of 110 cycles per minute. After the hair of the mice was removed with a depilatory agent, the chest of each mouse was opened, and the left coronary artery 1 to 2 mm below the left auricle was tied with a 8-0 nylon suture. Occlusion was confirmed by a change in the color of the left ventricle wall (becoming pale). Suturing between the incised ribs was performed by using 5-0 silk thread, and the skin was sutured using a 9-mm Autoclip. After the surgery, the mice were placed on a hot plate set at 37° C., followed by waiting for the mice to wake up for 30 minutes. In sham-operated mice, the same operation was performed, except that a suture was only passed under the left coronary artery; i.e., the left coronary artery was not tied with a suture. Thereafter, the cardiac function was monitored by echocardiography. Tissue of the heart, brain, kidney, adipose tissue, spleen, liver, lung, testis, muscle, pancreas, thymus, bone marrow, and ear (skin containing no cartilage portions; the same applies hereinafter) was collected 1 hour, 6 hours, 1 day, 7 days, and 8 weeks after myocardial infarction, rapidly frozen in liquid nitrogen, and stored at −80° C. In addition, blood was collected from the tail vein with a micro blood collection tube treated with heparin lithium (Terumo Corporation) 1 day, 7 days, and 8 weeks after myocardial infarction. The collected blood was transferred to a 1.5-mL tube rinsed with Novo-Heparin (Mochida Pharmaceutical Co., Ltd.) and centrifuged at 15,000 rpm for 5 minutes, and the supernatant (plasma) was separated and stored at −80° C. Mice for organ collection and mice for blood collection were separately prepared.

1-2. Echocardiography

Whether the myocardial infarction mouse model was appropriately generated was evaluated by echocardiography. Toshiba Diagnostic Ultrasound System Machine (Aplio MX SSA-780A) and Vevo2100 Imaging System (Primetech Corporation) were used for the echocardiography. Monitoring the mice by the echocardiography was performed 1 hour, 6 hours, 1 day, 7 days, 2 weeks, 4 weeks, 6 weeks, and 8 weeks after myocardial infarction. The mice were anesthetized with 2-2.5% isoflurane, and movement of the heart was recorded in the long-axis 2D-mode view and M-mode view. The diameter of the cavity in diastole and systole in the long-axis 2D-mode view was measured, and the left ventricular contractile function was evaluated by ejection fraction (% EF).

% EF=[$(EDv-ESv)/EDv$]×100

EDv: diameter at the end of diastole
ESv: diameter at the end of systole

Mice that did not show a decrease in % EF value after coronary artery ligation were deemed a ligation failure and excluded from the experiment. Mice that showed a decrease in the % EF value after ligation, but showed an increase in the % EF value again at a later date, were determined to have had the ligature become released for some reason, and such mice were excluded from the experiment.

1-3. Analysis of Metabolite (1) Extraction and Derivatization of Metabolite

For fat, the pancreas, and testis, tissue of each organ and methanol (100 μL per 100 mg of tissue) were individually placed in tubes for homogenization (Bio Medical Science Inc.) containing Zr beads (2 beads (5 mm), 5 beads (3 mm), and 50 beads (1.5 mm)) and homogenized with a Cell Destroyer PS1000 (Bio Medical Science Inc.) (4,260 rpm, 45 sec×2). Subsequently, 500 μL of methanol (containing 2-isopropylmalic acid, which is an internal standard) was added to each kind of tissue in an amount equivalent to 50 mg and mixed with Cell Destroyer, and the resulting mixtures were used as samples (4,260 rpm, 45 sec×1). For the spleen and lung, 100 mg of each tissue sample and 500 μL of methanol (containing 20 μL of a 0.5 mg/mL aqueous solution of 2-isopropylmalic acid) were individually placed in tubes for homogenization containing Zr beads (2 beads (5 mm), 5 beads (3 mm), 50 beads (1.5 mm)) and homogenized with Cell Destroyer, thereby obtaining samples (4,260 rpm, 45 sec×2). For the heart, brain, kidney, liver, and muscle, each tissue sample and 500 μL of methanol (containing 2-isopropylmalic acid) were individually placed in tubes for homogenization containing Zr beads (2 beads (5 mm), 5 beads (3 mm), 50 beads (1.5 mm)) and homogenized with Cell Destroyer (4260 rpm, 45 sec×2). After centrifugation at 15,000 rpm for 15 minutes, the supernatant in each tube was transferred to another tube. Some of the supernatant in an amount equivalent to 50 mg was transferred to still another tube and used as a sample. For a plasma sample, 500 μL of methanol (containing 2-isopropylmalic acid) was added to 10 μL of the plasma sample, and the mixture was stirred by vortexing for 30 seconds, left to stand at room temperature for 10 minutes, and used as a sample. 200 μL of Milli-Q water and 500 μL of chloroform were added to each of these samples, and each mixture was vortexed for 30 seconds and centrifuged at 7,100 rpm for 5 minutes. 400 μL of the aqueous layer was collected into a fresh tube. 200 μL of Milli-Q and 200 μL of chloroform were added thereto, and the mixture was vortexed again for 30 seconds and centrifuged at 7,100 rpm for 5 minutes. Thereafter, 400 μL of the aqueous layer was transferred to an ultrafiltration unit cup (Hydrophlic PTFE membrane, 0.2 μm; Millipore), centrifuged at 10,000 rpm for 15 minutes, and stored at −80° C. until analysis. Before measurement, each sample in an amount equivalent to 10 mg or 10 μL was dried under reduced pressure, and 50 μL of a pyridine solution containing 20 mg/mL methoxyamine hydrochloride was added. Each mixture was then shaken with a shaker at 37° C. for 90 minutes. After that, 50 μL of N-methyl-N-trimethylsilyltrifluoroacetamide (MSTFA) was further added, and the resulting mixtures were shaken with a shaker at 37° C. for 30 minutes and trimethylsilylated.

(2) GCMS Measurement

GCMS-TQ8030 (Shimadzu Corporation) was used for GCMS, and DB-5 (30 m×0.25 mm (inner diameter)×1.00 μm (film thickness)) (Agilent Technologies) was used as a capillary column for GC. GC was performed under the following temperature increase conditions: the temperature was increased at a rate of 4° C./min from 100° C. to 320° C. The injector port temperature was 280° C. Helium was used as carrier gas and made to flow at a rate of 39.0 cm/sec. The energy of the electron ionization was 150 eV, the ion source temperature was 200° C., and the range of m/z to be scanned was 45 to 600. 1 μL of each sample was individually injected and measured under the following conditions.

Heart_Split1:25_detector voltage+0.3 kV

Brain_Split1:25_detector voltage+0.2 kV

Kidney_Split1:25_detector voltage+0.3 kV

Liver_Split1:25_detector voltage+0.3 kV

Pancreas_Split1:25_detector voltage+0.3 kV

Skeletal muscle_Split1:25_detector voltage+0.2 kV

Adipose tissue_Split1:3_detector voltage+0.2 kV

Blood plasma_Split1:10_detector voltage+0.1 kV

Spleen_Split1:25_detector voltage+0.2 kV

Lung_Split1:25_detector voltage+0.3 kV

Testis_Split1:10_detector voltage+0.3 kV

Thymus_Split1:25_detector voltage+0.3 kV (3) Analysis of GCMS Data

Searching was performed by using GCMS solution Ver. 4.2, which is data analysis software, and GCMS Metabolites Database (Shimadzu Corporation). The target items were metabolites described in FIG. 28. To identify metabolites, the expected retention time and the presence of m/z of at least two specific peaks (target ion, confirmation ion), and the ratio of the specific peaks were confirmed. In each identified metabolite, the peak area of the target ion was measured and normalized using the peak area of the internal standard (2-isopropylmalic acid) and the sample amount.

The value of the normalized peak area mentioned above of each metabolite detected by GCMS in the myocardial infarction mouse model was divided by the value corresponding to the metabolite in the sham-operated mice. FIG. 29 shows metabolites in which the determined value (also referred to as "MI/Sham value") is more than 1 or less than 1. When there were multiple kinds of trimethylsilylated derivatives in a single metabolite, the total value of the plurality of derivatives was calculated.

1-4. Analysis of RNA (1) Extraction of RNA from Each Tissue (for RNAseq)

Each cryopreserved tissue was individually homogenized in TRIzol Reagent (Life Technologies) with a PT 10-35 6T Polytron homogenizer (Kineatica). After homogenized tissue with TRIzol Reagent in a tube was incubated at room temperature for 5 minutes to separate proteins, 0.2 mL of chloroform was added per mL of TRIzol, and the tubes were capped. Subsequently, the mixture in each tube was vortexed vigorously for 15 seconds. After the vortexing, the mixture was incubated at room temperature for 3 minutes and centrifuged at 12,000×g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy mini column (Qiagen), and purified RNAs were collected according to the RNeasy mini kit (Qiagen) standard protocol. The quality of each of the collected RNAs was evaluated by 1% agarose electrophoresis. The concentration of each of the collected RNAs was measured by Nanodrop.

(2) Obtaining RNAseq Data

RNAseq data was obtained using the samples described above by the following procedure.

i. Quality Check

Quality testing of the samples was performed based on the following items.

Concentration measurement using Nanodrop (spectrophotometer)

Concentration measurement and quality check using an Agilent 2100 Bioanalyzer ii. Preparation of Sample A library for sequencing was prepared using 500 to 1000 ng of each total RNA sample that passed the quality testing as a template with Illumina's TruSeq RNA Sample Prep Kit according to the standard protocol in the following manner.
(a) Purification of poly(A)-RNA using Oligo-dT beads
(b) Poly(A)-RNA fragmentation
(c) Reverse transcription/2nd strand cDNA synthesis
(d) Terminus repair and 3'A addition
(e) Adapter ligation
Note: The adapters contain index tags for identification of specimens.
(f) PCR amplification
(g) Purification and removal of low-molecular-weight substances (<200 bp) using AMPure XP beads iii. Obtaining Data Using Next-Generation Sequencer Nucleotide sequence data was obtained using an Illumina HiSeq next-generation sequencer by reading 100 bases according to the single-read method.

(3) Analysis of RNAseq Data and Generation of Heat Map
(3-1) Analysis of Output Data Obtained Using Next-Generation Sequencer The following information processing was carried out for the output data.
i. Base calling: text data of nucleotide sequences was obtained from the output raw data of analysis (image data).
ii. Filtering: selection of read data by predetermined filtering was performed.
iii. Sorting based on index sequences: sample data was sorted based on index information.
(3-2) Secondary Analysis of Output Data The data file (Fastq format) obtained using Illumina Hiseq was uploaded on Galaxy (https://usegalaxy.org/) downloaded to a local server. Then, analysis was carried out using Bowtie2 (http://bowtie-bio.sourceforge.net/bowtie2/index.shtml) to map each sequence to mouse genome map information mm9. The BAM file obtained using Bowtie2 was analyzed using Cufflinks (http://cole-trapnell-lab.github.io/cufflinks/) to calculate FPKM (RPKM) for each gene (each of the genes shown in FIG. 25).

(3-3) Classification of RNA

Values were calculated by dividing the expression level of each RNA (FPKM value) in the myocardial infarction mouse model by the expression level of the corresponding RNA (FPKM value) in the sham-operated mice (hereinafter also referred to as "MI/Sham"). RNAs in which MI/Sham is more than 1 or less than 1 were classified as group 4, RNAs in which MI/Sham is more than 1.5 or less than 0.67 were classified as group 5, RNAs in which MI/Sham is more than 2 or less than 0.5 were classified as group 6, and RNAs in which MI/Sham is more than 5 or less than 0.2 were classified as group 7 (FIG. 30). The RNAs of group 3 were observed to be expressed in the organs tested (heart, cerebrum, lung, kidney, adipose tissue, liver, skeletal muscle, testis, spleen, thymus, bone marrow, pancreas, and ear) within 8 weeks after left coronary artery ligation in the myocardial infarction mouse model; i.e., they are RNAs in which the FPKM value is 1 or more.

Further, FIG. 31 shows time-course changes in the RNA expression in each organ among the analyzed RNAs that have MI/Sham of more than 5 or less than 0.2.

(4) cDNA Synthesis and Quantifying Relative Expression Level by Real-Time PCR

Genes in which MI/Sham was larger or smaller in the analysis of RNAs were selected, and their expression was confirmed by real-time PCR (FIG. 32).

1 µg of total RNA obtained from each tissue was used as a template for cDNA synthesis, and cDNA was synthesized using Oligo dT20 primer according to the standard protocol of Superscript III First-Strand Synthesis Supermix (Life Technologies). After the synthesized cDNA was diluted 20-fold with 10-fold diluted TE buffer (10 mM Tris-HCl, pH 8.0, 0.1 mM EDTA), real-time PCR was performed with a LightCycler 48011 (Roche) according to the standard protocol of LightCycler 480 SYBR Green I Master (Roche) and Cp values were measured. The relative expression level of each gene relative to the reference gene was calculated by comparing the Cp value obtained for each gene with the Cp value for $\beta$2-microglobulin (B2m) or Maea as a reference gene, and MI/Sham was determined. The primer pairs used in the real-time PCR are as shown in Tables 9-1 to 9-3. However, with the primer set for Hba-a, Hba-a1 and Hba-a2 cannot be distinguished in PCR, and with the primer set for Hbb-b, Hbb-bs, and Hbb-bt cannot be distinguished in PCR. Thus, when there are Hba-a1 and Hba-a2, or Hbb-b1, Hbb-bs, and Hbb-bt, in a sample, the expression level is their total amount.

2. Young-Onset Dementia Model 2-1. Young-Onset Dementia Mouse Model, Organ Collection, and Blood Collection Male mice (SAMP8/Ta Sic) (hereinafter also referred to as "SAMP8"; Japan SLC, Inc.) were used as a young-onset dementia mouse model, and male mice (SAMR1/Ta Slc) (hereinafter also referred to as "SAMR1"; Japan SLC, Inc.) were used as control mice. The SAM strain of mice is a mouse model for senescence acceleration reported by Toshio Takeda (Jpn. J. Hyp., 51, 569-578, 1996).

The step-through test was performed by using mice at 8 weeks of age (early stage), 16 weeks of age (middle stage), and 32 weeks of age (late stage), 10 mice at each stage, in each of the strains SAMP8 and SAMR1, and mice were selected in she early stage, the middle stage, and the late stage, six mice in each stage.

(1) Step-Through Test

The mice were subjected to acclimatization and an acquisition trial on day 1 and subjected to a retention trial on day 2. Each trial was performed by using a shuttle box (Muromachi Kikai Co., Ltd.). The shuttle box had a light compartment on one side and a dark compartment on the other side, and an openable partition was provided between the two compartments. Electricity was applied in only the dark compartment.

In acclimatization, the mice were placed in the light compartment, and 10 seconds later, the partition was opened. Immediately after the mice moved to the dark compartment, the partition was closed, and the state was maintained for 10 seconds. No electric shock was given.

In the acquisition trial, the mice were placed in the light compartment, and 10 seconds later, the partition was opened. From this point, latency (time elapsed until a mouse moves to the dark compartment) was measured for up to 300 seconds. When a mouse moved to the dark compartment, the partition was rapidly closed, and an electric shock was given (0.2 mA, 3 seconds). When a mouse did not move to the dark compartment even after the elapse of 300 seconds, the mouse was forced to move to the dark compartment; the partition was then closed, and an electric shock was given (0.2 mA, 3 seconds).

In the retention trial, the mice were placed in the light compartment, and 10 seconds later, the partition was opened. From this point, latency (time until a mouse moves to the dark compartment) was measured for up to 300 seconds.

(2) Selection and Grouping of Animals

The average value of the latency in the retention trial in the step-through test was determined for the mice of each strain and each age in weeks. Six mice of the same animal species and the same age in weeks (three for extraction of RNAs and three for extraction of metabolites) were selected in each case in order of proximity of the latency in the retention trial to the average value. When mice showed the same latency, a mouse with the smaller individual identification number was selected.

Table 5 shows the results of the step-through test.

TABLE 5

| Strain | Weeks of age | Individual identification No. | Latency in acquisition trial | Latency in retention trial | Difference from average value | Selection | Group name |
|---|---|---|---|---|---|---|---|
| SAMR1 | 8 | 1 | 11.57 | 140.19 | 32.9 | o | Group B |
| | | 2 | 5.9 | 61.47 | −45.82 | o | Group B |
| | | 3 | 5.4 | 42.57 | −64.72 | o | Group A |
| | | 4 | 12.25 | 31.19 | −76.1 | o | Group B |
| | | 5 | 5.97 | 300 | 192.71 | x | |
| | | 6 | 7.65 | 50.87 | −56.42 | o | Group A |
| | | 7 | 4 | 7.12 | −100.17 | x | |
| | | 8 | 7.69 | 19.65 | −87.64 | x | |
| | | 9 | 12.06 | 246.37 | 139.08 | x | |
| | | 10 | 16.85 | 173.5 | 66.21 | o | Group A |
| | | Mean | 8.93 | 107.29 | | | |
| | | S.E. | 1.28 | 32.48 | | | |
| SAMR1 | 16 | 11 | 5.81 | 21.53 | −194.37 | x | |
| | | 12 | 17.82 | 300 | 84.1 | o | Group D |
| | | 13 | 9.94 | 300 | 84.1 | o | Group C |
| | | 14 | 9.88 | 300 | 84.1 | o | Group D |
| | | 15 | 14.91 | 300 | 84.1 | o | Group C |
| | | 16 | 6.56 | 300 | 84.1 | o | Group C |
| | | 17 | 10.5 | 199.03 | −16.87 | o | Group D |
| | | 18 | 7.25 | 126.28 | −89.62 | x | |
| | | 19 | 9.1 | 300 | 84.1 | x | |
| | | 20 | 11.53 | 12.19 | −203.71 | x | |
| | | Mean | 10.33 | 215.9 | | | |
| | | S.E. | 1.18 | 38.01 | | | |
| SAMP8 | 8 | 31 | 7.75 | 11.06 | −7.21 | o | Group H |
| | | 32 | 4.63 | 12.97 | −5.3 | o | Group G |
| | | 33 | 10.1 | 48.06 | 29.79 | x | |
| | | 34 | 7.15 | 9.5 | −8.77 | o | Group G |
| | | 35 | 4.09 | 23.57 | 5.3 | o | Group H |
| | | 36 | 6.54 | 32.87 | 14.6 | x | |
| | | 37 | 4.41 | 9.04 | −9.23 | x | |
| | | 38 | 6.07 | 11.5 | −6.77 | o | Group H |
| | | 39 | 5.12 | 3.84 | −14.43 | x | |
| | | 40 | 4.34 | 20.25 | 1.98 | o | Group G |
| | | Mean | 6.02 | 18.27 | | | |
| | | S.E. | 0.61 | 4.25 | | | |
| SAMP8 | 16 | 41 | 11.69 | 2.59 | −5.59 | x | |
| | | 42 | 9.69 | 13.5 | 5.32 | x | |
| | | 43 | 3.15 | 9.97 | 1.79 | o | Group J |
| | | 44 | 3.87 | 2.75 | −5.43 | x | |
| | | 45 | 1.62 | 6.75 | −1.43 | o | Group J |
| | | 46 | 7.06 | 8.5 | 0.32 | o | Group I |
| | | 47 | 7.44 | 3.15 | −5.03 | o | Group J |
| | | 48 | 6.34 | 6.04 | −2.14 | o | Group I |
| | | 49 | 7.59 | 15.85 | 7.67 | x | |
| | | 50 | 4 | 12.71 | 4.53 | o | Group I |
| | | Mean | 6.25 | 8.18 | | | |
| | | S.E. | 0.98 | 1.5 | | | |

(3) Organ Collection and Blood Collection

Each mouse from which organs were to be collected for extraction of metabolites first had laparotomy performed under anesthesia with isoflurane, and blood was collected from the abdominal vena cava using a syringe and an injection needle. The obtained blood was collected in a micro blood collection tube (BD Microtainer Tubes with $K2E(K_2EDTA)$) and stored in ice until centrifugation. After centrifugation, plasma was separated. The obtained plasma was stored at −80° C. After blood collection, the mouse was euthanized by cervical dislocation to collect organs, and 14 organs (heart, brain, kidney, adipose tissue (around the epididymis), brown fat, spleen, liver, lung, testis, muscle, pancreas, thymus, stomach, and large intestine) were collected. After the wet weights of the collected organs were measured, the organs were rapidly frozen in liquid nitrogen and stored at −80° C.

Each mouse from which organs were to be collected for extraction of RNAs was euthanized by cervical dislocation without anesthesia, and 16 organs (muscle, brown fat, heart, lung, thymus, kidney, liver, large intestine, stomach, adipose tissue (around the epididymis), testis, spleen, pancreas, brain, ear, bone marrow) were collected. After the wet weights of the organs were measured, the organs were rapidly frozen in liquid nitrogen and stored at −80° C.

2-2. Measurement of Metabolite (1) Extraction of Metabolite

For the brain, adipose tissue (around the epididymis), brown fat, spleen, pancreas, testis, stomach, large intestine, liver, kidney, lung, heart, and skeletal muscle, tissue of each organ and 50% acetonitrile containing an internal standard substance (Solution ID: 304-1002; HMT) (1500 μL per 50 mg of the tissue) were individually placed in tubes for homogenization (Bio Medical Science Inc.) containing Zr beads (5 beads (5 mm), 1 bead (10 mm)) and homogenized with Shake Master Neo V. 1.0 (Bio Medical Science Inc.), thereby obtaining samples (1,500 rpm, 60 sec×3).

For the thymus, its tissue and 50% acetonitrile containing an internal standard substance (Solution ID: 304-1002; HMT) (1500 μL per 50 mg of the tissue) were placed in a tube for homogenization (Bio Medical Science Inc.) containing Zr beads (1 bead (5 mm), 5 beads (3 mm)) and homogenized with MS-100R of Tomy Seiko Co., Ltd. (1,500 rpm, 60 sec×3). When homogenization was insufficient, it was performed until the tissue was homogenized.

The samples after the homogenization were centrifuged (2,300×g, 4° C., 5 minutes), and 800 μL of each supernatant had ultrafiltration performed using an ultrafiltration unit cup (UFC3LCCNB-HMT, 5 k; HMT) (9,100×g, 4° C., 5 hours). Each of the samples after the ultrafiltration was dried under reduced pressure, redissolved in 50 μL of MiliQ, and measured.

For plasma, 450 μL of methanol containing an internal standard substance (Solution ID: 304-1002; HMT), 500 μL of chloroform, and 200 μL of MiliQ were added to 50 μL of the sample. The mixture was vortexed and centrifuged (2,300×g, 4° C., 5 minutes), and ultrafiltration (UFC3LCCNB-HMT, 5 k; HMT) (9,100×g, 4° C., 5 hours) was performed on 400 μL of the supernatant. The sample after the ultrafiltration was dried under reduced pressure, and the sample after drying under reduced pressure was dissolved in 50 μL of MiliQ and measured.

(2) CE-MS Measurement

Agilent CE-TOFMS system (Agilent Technologies) was used for CE-MS, and a fused silica capillary (i.d. 50 μm×80 cm) was used for a capillary column for CE. As electrophoresis buffers in CE, a cation buffer solution (p/n: H3301-1001; HMT) was used for cations, and an anion buffer solution (p/n: 13302-1023; HMT) was used for anions.

Measurement Conditions on the Cation Side

Electrophoresis was performed under the following sample injection conditions: pressure injection: 50 mbar, 10 sec; the electrophoresis voltage of CE: 27 kV. The energy of electron ionization was 4,000 V, and the range to be scanned was 50 to 1000. 5 nL of each sample was individually injected.

CE voltage: Positive, 27 kV
MS ionization: ESI Positive
MS capillary voltage: 4,000 V
MS scan range: m/z 50-1,000
Sheath liquid: HMT Sheath Liquid (p/n: H3301-1020)

Measurement Conditions on the Anion Side

Electrophoresis was performed under the following sample injection conditions: pressure injection: 50 mbar, 25 sec; the electrophoresis voltage of CE: 30 kV. The energy of the electron ionization was 3,500 V, and the range to be scanned was 50 to 1000. 5 nL of each sample was individually injected.

CE voltage: Positive, 30 kV
MS ionization: ESI Negative
MS capillary voltage: 3,500 V
MS scan range: m/z 50-1,000
Sheath liquid: HMT Sheath Liquid (p/n: H3301-1020)

(3) Analysis of CE-MS Data

The metabolites shown in FIG. 28 were analyzed. Detected peaks were processed with automatic integration software MasterHands ver. 2.16.0.15 (developed by Keio University). Peaks having a signal-to-noise (S/N) ratio of 3 or more were automatically extracted, and metabolite identification was performed by using the mass-to-charge ratio (m/z), peak area value, and migration time (MT). The target items were metabolites listed in an HMT CE-MS annotation list.

For each of the identified metabolites, the peak area of the target ion was measured and normalized using the peak area of the internal standard and the sample amount.

The peak area of each metabolite in SAMP8 was divided by the peak area of the corresponding metabolite in SAMR1 (control). The obtained values (SAMP8/Control values) are shown in FIG. 33.

2-3. Analysis of RNA (1) Extraction of RNA from Each Kind of Tissue

Each cryopreserved tissue was individually homogenized in TRIzol Reagent (Life Technologies) with Cell Destroyer PS1000 (Pro Sense Inc.) or PT 10-356T Polytron homogenizer (Kineatica). After homogenized tissue with TRIzol Reagent in a tube was incubated for 5 minutes at room temperature to separate proteins, 0.2 mL of chloroform was added per mL of TRIzol, and the tubes were capped. Subsequently, the mixture in each tube was vortexed vigorously for 15 seconds. After the vortexing, the mixture was incubated at room temperature for 3 minutes and centrifuged at 12,000×g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy mini column (Qiagen), and purified RNAs were collected according to the RNeasy mini kit (Qiagen) standard protocol. The quality of each of the collected RNAs was evaluated by 1% agarose electrophoresis. The concentration of each of the collected RNAs was measured by Nanodrop.

(2) Obtaining RNAseq Data

RNAseq data was obtained using the samples described above by the following procedure.

i. Quality Check

Quality testing of the samples was performed based on the following item.

Concentration measurement and quality check using Agilent 2200 TapeStationSytem ii. Preparation of Sample A library for sequencing was prepared using 500 to 1000 ng of each total RNA sample that passed the quality testing as a template with Illumina's TruSeq RNA Sample Prep Kit according to the standard protocol in the following manner.

(a) Purification of poly(A)-RNA using Oligo-dT beads
(b) Poly(A)-RNA fragmentation
(c) Reverse transcription/2nd strand cDNA synthesis
(d) Terminus repair and 3'A addition
(e) Adapter ligation Note: The adapters contain index tags for identification of specimens.

(f) PCR amplification
(g) Purification and removal of low-molecular-weight substances (<200 bp) using AMPure XP beads iii. Obtaining Data Using Next-Generation Sequencer Nucleotide sequence data was obtained using an Illumina HiSeq 4000 next-generation sequencer by reading 100 bases according to the paired-end method.

(3) Analysis of RNAseq Data and Generation of Heat Map (3-1) Analysis of Output Data Obtained Using Next-Generation Sequencer The following information processing was carried out for the output data.

i. Base calling: text data of nucleotide sequences was obtained from the output raw data of analysis (image data).
ii. Filtering: selection of read data by predetermined filtering was performed.
iii. Sorting based on index sequences: sample data was sorted based on index information.

(3-2) Secondary Analysis of Output Data

The data file (Fastq format) obtained using Illumina Hiseq was uploaded on Galaxy (https://usegalaxy.org/) downloaded to a local server. Thereafter, analysis was carried out using Bowtie2 (http://bowtie-bio.sourceforge.net/bowtie2/index.shtml) to map each sequence to mouse genome map information mm10. The BAM file obtained using Bowtie2 was analyzed using Cufflinks (http://cole-trapnell-lab.github.io/cufflinks/) to calculate FPKM for each gene (each of the genes shown in FIG. 26).

(3-3) Classification of RNA

Values were calculated by dividing the expression level of each RNA (FPKM value) in SAMP8 by the expression level of the corresponding RNA (FPKM value) in SAMR1 (control) (hereinafter also referred to as "SAMP8/Control"). RNAs in which SAMP8/Control is more than 1 or less than 1 were classified as group 4, RNAs in which SAMP8/Control is more than 1.5 or less than 0.67 were classified as group 5, RNAs in which SAMP8/Control is more than 2 or less than 0.5 were classified as group 6, and RNAs in which SAMP8/Control is more than 5 or less than 0.2 were classified as group 7 (FIG. 34). The RNAs of group 3 were observed to be expressed in any of the organs tested by the time the SMAP8 mice were 32 weeks old; i.e., they are RNAs in which the FPKM value is 1 or more.

Further, among the analyzed RNAs, FIG. 35 shows time-course changes in the RNAs of group 7 in each organ.

3. Glioma Model 3-1. Glioma Mouse Model, Organ Collection, and Blood Collection

Hair on the heads of 7-week-old male NOD/ShiJic-scid JCI mice was shaved with a hair clipper without anesthesia by the day of transplantation. A mixture of three kinds of anesthetics ((i) medetomidine hydrochloride (trade name: Domitor, Nippon Zenyaku Kogyo Co., Ltd.), (ii) midazolam (trade name: Dormicum, Astellas Pharma Inc.), and (iii) butorphanol tartrate (trade name: Vetorphale, Meiji Seika Pharma Co., Ltd.) was intraperitoneally administered to deeply anesthetize the animals.

The head of each animal was fixed using a brain stereotaxis apparatus (model no.: 68012, RWD), and the skull was exposed by incision of the skin of the head. The brain stereotaxis apparatus was operated to bring an injection needle into contact with the skull above the transplantation site and the skull was marked. A hole was drilled in the marked area of the skull with a dental drill.

A microsyringe (model no.: 80300, Hamilton) filled with a cell suspension of human glioblastoma U87-MG (concentration of cells to be transplanted: $1\times10^8$ cells/mL) was attached to a manual stereotaxic injector (model no.: 68606, RWD) provided with the brain stereotaxis apparatus. The cell suspension adhering around the needle of the microsyringe was wiped off. The dial of the electrode holder of the brain stereotaxis apparatus was turned to slowly lower the needle tip of the microsyringe to the dura mater of the transplantation site. The needle broke through the dura mater, and outflow of cerebrospinal fluid was confirmed. Subsequently, the needle was slowly inserted from there to a depth of 3 mm into the cerebral parenchyma. The dial of the manual stereotaxic injector was turned, and 2 µL of the cell suspension was injected over 2 minutes. It was confirmed that there was no backflow, and that the microsyringe was advanced to 2 µL of the scale. After the injection, the needle was maintained for 5 minutes in that state. Then, the dial of the electrode holder was slowly turned in the opposite direction to withdraw the needle of the microsyringe over a period of 2 minutes. After withdrawing the needle of the microsyringe, the cell suspension was wiped off with sterilized gauze if present. The incision was sutured with a nylon suture. Atipamezole hydrochloride (trade name: Antisedan, Nippon Zenyaku Kogyo Co., Ltd.) was intraperitoneally administered to allow the mice to wake from anesthesia, and the mice were returned to their cage. In a solvent transplantation group (control), only the PBS as the solvent was administered intracerebrally instead of the cell suspension.

On day 3 and day 7 after transplantation, the animals were euthanized by cervical dislocation, and 16 organs (muscle, brown fat, heart, lung, kidney, liver, large intestine, stomach, adipose tissue (around the epididymis), testis, spleen, pancreas, left brain, right brain, ear, and bone marrow) and blood were collected. After their wet weights were measured, the organs and blood were rapidly frozen in liquid nitrogen and stored at −80° C.

3-2. Analysis of RNA

Extraction of RNAs from each tissue, obtaining RNAseq data, analysis of RNAseq data and generation of heat map, and secondary analysis of output data were performed as described in 2-1 and 2-3 of "I. iOrgans" above.

Values were calculated by dividing the expression level of each RNA (FPKM value) in the glioma mouse model by the expression level of the corresponding RNA (FPKM value) in the mice of the control group (hereinafter also referred to as "Glioma/Control"). RNAs in which Glioma/Control is more than 1 or less than 1 were classified as group 4, RNAs in which Glioma/Control is more than 1.5 or less than 0.67 were classified as group 5, RNAs in which Glioma/Control is more than 2 or less than 0.5 were classified as group 6, and RNAs in which Glioma/Control is more than 5 or less than 0.2 were classified as group 7 (FIG. 36). The RNAs of group 3 were observed to be expressed in the organs tested by day 7 after the glioma transplantation; i.e., they are RNAs in which the FPKM value is 1 or more.

Further, among the analyzed RNAs, FIG. 37 shows time-course changes in the RNAs of group 7 in each organ.

4. Human Tumor Patient 4-1. Collecting Skin and Blood from Human Tumor Patient and Healthy Individual Human specimens were collected in the clinical study "*Haigan oyobi Nyugan Kanja kara Saishushita Soshiki Taieki no Idenshi Hatsugen Kaiseki* (Gene expression analysis of tissue and body fluids collected from lung cancer and breast cancer patients)" conducted with approval from the ethics committee of the National Hospital Organization Kure Medical Center and Chugoku Cancer Center.

Blood was collected from one female breast cancer patient and one male lung cancer patient. Skin was collected from two female breast cancer patients and one male lung cancer patient. The selected patients met the following criteria.

Inclusion Criteria
(1) Patient diagnosed with lung cancer or breast cancer and scheduled to be operated on
   In the case of lung cancer, patient with clinical stage I-II non-small-cell lung cancer
   In the case of breast cancer, patient with clinical stage I-II
(2) Patient who is able to fully understand this study plan and is able to consent by himself or herself
(3) Patient aged 20 years or older at the time of obtaining consent Exclusion Criteria
(1) Patient who is deemed unsuitable as a subject by a researcher
(2) HBs antigen-positive patient, HBc antibody-positive patient, HCV antibody-positive patient, HIV-infected patient, HTLV-1-infected patient, syphilis-positive patient
(3) Patient with a history of cancer
(4) Patient with a history of myocardial infarction
(5) Patient with a history of diabetes
(6) Patient with a history of kidney disease Blood was also collected from five healthy women. Breast skin of healthy women were obtained from Biopredic International.

3 mL of blood was individually collected in Tempus Blood RNA Tubes (Thermo Fisher Scientific), and immediately after the collection, the tubes were vigorously shaken for 10 seconds to uniformly mix the blood and the stabilizer and then stored at −20° C.

The skin was stored at −80° C. until use.

4-2. Analysis of RNA

Extraction of RNAs from each tissue, obtaining RNAseq data, analysis of RNAseq data and generation of heat map, and secondary analysis of output data were performed as described in 2-1 and 2-3 of "I. iOrgans" above.

Values were calculated by dividing the expression level of each RNA (FPKM value) in the skin of the breast cancer patients by the expression level of the corresponding RNA (FPKM value) in the skin of the healthy individuals. RNAs in which the determined value is more than 1 or less than 1 were classified as group 4, RNAs in which the determined value is more than 1.5 or less than 0.67 were classified as group 5, RNAs in which the determined value is more than 2 or less than 0.5 were classified as group 6, and RNAs in which the determined value is more than 5 or less than 0.2 were classified as group 7 (FIG. 38). The RNAs of group 3 are RNAs in which the FPKM value is 1 or more.

Values were calculated by dividing the expression level of each RNA (FPKM value) in the skin of the lung cancer patient by the expression level of the corresponding RNA (FPKM value) in the skin of the healthy individuals. RNAs in which the determined value is more than 1 or less than 1 were classified as group 4, RNAs in which the determined value is more than 1.5 or less than 0.67 were classified as group 5, RNAs in which the determined value is more than 2 or less than 0.5 were classified as group 6, and RNAs in which the determined value is more than 5 or less than 0.2 were classified as group 7 (FIG. 39). The RNAs of group 3 are RNAs in which the FPKM value is 1 or more.

RNAs in which large variation was observed between the healthy human individuals were excluded from the results. More specifically, the ratio of the FPKM value in one healthy individual to the FPKM value in another healthy individual was determined; RNAs in which this ratio falls within the range of 0.75 to 1.25 were divided into groups.

It was believed that FCGR3B, FPR1, HLA-DQA1, LINC00260, LOC286437, MALAT1, MIR1184-1, MIR1247, PRG4, RPL21P44, RPPH1, RPS15AP10, SCARNA4, SNORA31, SNORA77, and ZBTB20 can be markers for cancer because they underwent large changes in the skin both in breast cancer and lung cancer.

Further, values were calculated by dividing the expression level of each RNA (FPKM value) in the blood of the breast cancer patient by the expression level of the corresponding RNA (FPKM value) in the healthy individuals (FPKM value). RNAs in which the determined value is more than 1 or less than 1 were classified as group 4, RNAs in which the determined value is more than 1.5 or less than 0.67 were classified as group 5, RNAs in which the determined value is more than 2 or less than 0.5 were classified as group 6, and RNAs in which the determined value is more than 5 or less than 0.2 were classified as group 7 (FIG. 40). The RNAs of group 3 are RNAs in which the FPKM value is 1 or more.

Values were calculated by dividing the expression level of each RNA (FPKM value) in the blood of the lung cancer patient by the expression level of the corresponding RNA (FPKM value) in the blood of the healthy individuals. RNAs in which the determined value is more than 1 or less than 1 were classified as group 4, RNAs in which the determined value is more than 1.5 or less than 0.67 were classified as group 5, RNAs in which the determined value is more than 2 or less than 0.5 were classified as group 6, and RNAs in which the determined value is more than 5 or less than 0.2 were classified as group 7 (FIG. 41). The RNAs of group 3 are RNAs in which the FPKM value is 1 or more.

RNAs in which large variation was observed between the healthy human individuals was excluded from the results. More specifically, the average (AV) and the standard deviation (SD) of the FPKM values in each RNA in the healthy individuals were determined; RNAs in which the value obtained by dividing the SD value by the AV value is less than 0.25 were divided into groups.

It was believed that HNRNPH2, HP, LOC283663, SNORA40, and TCN2 can be markers for cancer because they underwent large changes in the blood both in the breast cancer and the lung cancer.

5. Example

To demonstrate that a disease in a specific organ and a stage can be predicted from a pattern of inter-organ cross talk indicator in each organ other than the specific organ, obtained from cells or tissue of each organ according to the theory of R-iOrgans, correlation coefficients between patterns of expression of RNAs of group 7 in each of the myocardial infarction model, the young-onset dementia model, and the glioma model was determined for each stage were calculated. The correlation coefficients were calculated in each organ and in each stage. The correlation coefficients were determined by modifying Spearman's rank correlation method and Z-score method.

The similarity was calculated based on correlation coefficients of the patterns of inter-organ cross talk indicators between two organs.

5-1. Spearman's Rank Correlation

Calculation was performed by using function cor (method="spearman") of analysis software R. Tables 6-1 to 6-3 show the results.

TABLE 6-1

| | | Myocardial infarction | | | Glioma | | Dementia | | |
|---|---|---|---|---|---|---|---|---|---|
| | | 1 d | 1 w | 8 w | d 3 | d 7 | E | M | L |
| Liver | | | | | | | | | |
| Myocardial infarction | 1 d | 1.00 | 0.02 | −0.21 | 0.10 | −0.22 | 0.06 | 0.02 | 0.06 |
| | 1 w | 0.02 | 1.00 | 0.04 | 0.05 | 0.03 | 0.12 | 0.02 | 0.17 |
| | 8 w | −0.21 | 0.04 | 1.00 | 0.03 | 0.04 | 0.08 | 0.00 | 0.07 |
| Glioma | d 3 | 0.10 | 0.05 | 0.03 | 1.00 | −0.38 | 0.07 | −0.05 | 0.12 |
| | d 7 | −0.22 | 0.03 | 0.04 | −0.38 | 1.00 | 0.00 | 0.14 | −0.12 |
| Dementia | E | 0.06 | 0.12 | 0.08 | 0.07 | 0.00 | 1.00 | 0.29 | 0.60 |
| | M | 0.02 | 0.02 | 0.00 | −0.05 | 0.14 | 0.29 | 1.00 | 0.23 |
| | L | 0.06 | 0.17 | 0.07 | 0.12 | −0.12 | 0.60 | 0.23 | 1.00 |
| Kidney | | | | | | | | | |
| Myocardial infarction | 1 d | 1.00 | 0.16 | −0.15 | −0.15 | −0.14 | 0.12 | 0.13 | 0.11 |
| | 1 w | 0.16 | 1.00 | −0.06 | −0.07 | 0.04 | 0.07 | 0.06 | 0.07 |
| | 8 w | −0.15 | −0.06 | 1.00 | 0.07 | 0.08 | 0.03 | −0.02 | 0.01 |
| Glioma | d 3 | −0.15 | −0.07 | 0.07 | 1.00 | −0.01 | −0.18 | −0.16 | −0.16 |
| | d 7 | −0.14 | 0.04 | 0.08 | −0.01 | 1.00 | 0.06 | −0.02 | 0.05 |
| Dementia | E | 0.12 | 0.07 | 0.03 | −0.18 | 0.06 | 1.00 | 0.40 | 0.58 |
| | M | 0.13 | 0.06 | −0.02 | −0.16 | −0.02 | 0.40 | 1.00 | 0.33 |
| | L | 0.11 | 0.07 | 0.01 | −0.16 | 0.05 | 0.58 | 0.33 | 1.00 |
| Lung | | | | | | | | | |
| Myocardial infarction | 1 d | 1.00 | 0.17 | 0.16 | 0.08 | −0.10 | 0.04 | 0.05 | 0.20 |
| | 1 w | 0.17 | 1.00 | 0.13 | 0.03 | 0.11 | 0.11 | 0.13 | −0.05 |
| | 8 w | 0.16 | 0.13 | 1.00 | 0.11 | 0.04 | −0.03 | −0.06 | 0.07 |
| Glioma | d 3 | 0.08 | 0.03 | 0.11 | 1.00 | 0.04 | −0.25 | −0.32 | 0.03 |
| | d 7 | −0.10 | 0.11 | 0.04 | 0.04 | 1.00 | 0.04 | 0.02 | −0.05 |
| Dementia | E | 0.04 | 0.11 | −0.03 | −0.25 | 0.04 | 1.00 | 0.83 | 0.16 |
| | M | 0.05 | 0.13 | −0.06 | −0.32 | 0.02 | 0.83 | 1.00 | 0.14 |
| | L | 0.20 | −0.05 | 0.07 | 0.03 | −0.05 | 0.16 | 0.14 | 1.00 |
| Skeletal muscle | | | | | | | | | |
| Myocardial infarction | 1 d | 1.00 | 0.16 | −0.02 | −0.12 | −0.21 | 0.16 | 0.23 | 0.28 |
| | 1 w | 0.16 | 1.00 | 0.00 | 0.00 | −0.03 | 0.01 | 0.11 | 0.14 |
| | 8 w | −0.02 | 0.00 | 1.00 | 0.02 | −0.03 | 0.16 | 0.08 | 0.15 |
| Glioma | d 3 | −0.12 | 0.00 | 0.02 | 1.00 | 0.04 | 0.13 | −0.19 | −0.10 |
| | d 7 | −0.21 | −0.03 | −0.03 | 0.04 | 1.00 | −0.21 | −0.02 | −0.19 |
| Dementia | E | 0.16 | 0.01 | 0.16 | 0.13 | −0.21 | 1.00 | 0.15 | 0.42 |
| | M | 0.23 | 0.11 | 0.08 | −0.19 | −0.02 | 0.15 | 1.00 | 0.39 |
| | L | 0.28 | 0.14 | 0.15 | −0.10 | −0.19 | 0.42 | 0.39 | 1.00 |
| Spleen | | | | | | | | | |
| Myocardial infarction | 1 d | 1.00 | −0.15 | −0.21 | −0.01 | −0.21 | −0.01 | −0.06 | 0.15 |
| | 1 w | −0.15 | 1.00 | 0.30 | 0.00 | 0.24 | 0.08 | 0.01 | −0.03 |
| | 8 w | −0.21 | 0.30 | 1.00 | −0.07 | 0.20 | −0.10 | −0.04 | −0.17 |
| Glioma | d 3 | −0.01 | 0.00 | −0.07 | 1.00 | 0.11 | 0.13 | 0.07 | 0.08 |
| | d 7 | −0.21 | 0.24 | 0.20 | 0.11 | 1.00 | −0.03 | −0.08 | −0.04 |
| Dementia | E | −0.01 | 0.08 | −0.10 | 0.13 | −0.03 | 1.00 | 0.43 | 0.48 |
| | M | −0.06 | 0.01 | −0.04 | 0.07 | −0.08 | 0.43 | 1.00 | 0.22 |
| | L | 0.15 | −0.03 | −0.17 | 0.08 | −0.04 | 0.48 | 0.22 | 1.00 |

TABLE 6-1-continued

| | | Brain | | | | | | | | |
|---|---|---|---|---|---|---|---|---|---|---|
| | | Myocardial infarction | | | Glioma Left brain | Glioma Right brain | Glioma Left brain | Glioma Right brain | Dementia | | |
| | | 1 d | 1 w | 8 w | d 3 | d 3 | d 7 | d 7 | E | M | L |
| Myocardial infarction | 1 d | 1.00 | 0.13 | −0.05 | 0.10 | 0.14 | 0.10 | −0.06 | −0.01 | 0.05 | 0.00 |
| | 1 w | 0.13 | 1.00 | −0.12 | −0.03 | 0.10 | 0.04 | 0.09 | −0.07 | 0.01 | −0.01 |
| | 8 w | −0.05 | −0.12 | 1.00 | 0.01 | 0.07 | 0.03 | −0.01 | −0.01 | 0.00 | −0.01 |
| Glioma | Left brain d 3 | 0.10 | −0.03 | 0.01 | 1.00 | 0.08 | −0.06 | 0.01 | 0.03 | 0.03 | 0.00 |
| | Right brain d 3 | 0.14 | 0.10 | 0.07 | 0.08 | 1.00 | 0.31 | 0.05 | −0.22 | −0.04 | −0.12 |
| Glioma | Left brain d 7 | 0.10 | 0.04 | 0.03 | −0.06 | 0.31 | 1.00 | −0.16 | −0.32 | −0.04 | −0.23 |
| | Right brain d 7 | −0.06 | 0.09 | −0.01 | 0.01 | 0.05 | −0.16 | 1.00 | 0.05 | −0.06 | 0.07 |
| Dementia | E | −0.01 | −0.07 | −0.01 | 0.03 | −0.22 | −0.32 | 0.05 | 1.00 | 0.12 | 0.43 |
| | M | 0.05 | 0.01 | 0.00 | 0.03 | −0.04 | −0.04 | −0.06 | 0.12 | 1.00 | 0.10 |
| | L | 0.00 | −0.01 | −0.01 | 0.00 | −0.12 | −0.23 | 0.07 | 0.43 | 0.10 | 1.00 |

TABLE 6-2

| | | Myocardial infarction | | | Glioma | | Dementia | | |
|---|---|---|---|---|---|---|---|---|---|
| | | 1 d | 1 w | 8 w | d 3 | d 7 | E | M | L |
| | | | | Adipose tissue | | | | | |
| Myocardial infarction | 1 d | 1.00 | 0.07 | −0.09 | −0.25 | −0.34 | 0.11 | −0.05 | 0.01 |
| | 1 w | 0.07 | 1.00 | −0.01 | 0.18 | 0.02 | 0.09 | 0.11 | 0.05 |
| | 8 w | −0.09 | −0.01 | 1.00 | 0.05 | −0.04 | −0.02 | 0.04 | 0.03 |
| Glioma | d 3 | −0.25 | 0.18 | 0.05 | 1.00 | 0.40 | 0.05 | 0.23 | 0.13 |
| | d 7 | −0.34 | 0.02 | −0.04 | 0.40 | 1.00 | −0.10 | 0.03 | −0.07 |
| Dementia | E | 0.11 | 0.09 | −0.02 | 0.05 | −0.10 | 1.00 | 0.15 | 0.55 |
| | M | −0.05 | 0.11 | 0.04 | 0.23 | 0.03 | 0.15 | 1.00 | 0.28 |
| | L | 0.01 | 0.05 | 0.03 | 0.13 | −0.07 | 0.55 | 0.28 | 1.00 |
| | | | | Testis | | | | | |
| Myocardial infarction | 1 d | 1.00 | 0.17 | 0.12 | 0.07 | −0.06 | 0.05 | 0.05 | 0.05 |
| | 1 w | 0.17 | 1.00 | 0.06 | 0.07 | −0.04 | 0.11 | 0.03 | 0.09 |
| | 8 w | 0.12 | 0.06 | 1.00 | 0.04 | −0.01 | −0.01 | 0.04 | −0.03 |
| Glioma | d 3 | 0.07 | 0.07 | 0.04 | 1.00 | −0.37 | −0.22 | 0.33 | −0.05 |
| | d 7 | −0.06 | −0.04 | −0.01 | −0.37 | 1.00 | 0.14 | −0.25 | −0.02 |
| Dementia | E | 0.05 | 0.11 | −0.01 | −0.22 | 0.14 | 1.00 | 0.02 | 0.34 |
| | M | 0.05 | 0.03 | 0.04 | 0.33 | −0.25 | 0.02 | 1.00 | 0.15 |
| | L | 0.05 | 0.09 | −0.03 | −0.05 | −0.02 | 0.34 | 0.15 | 1.00 |

| | | Thymus | | | | | |
|---|---|---|---|---|---|---|---|
| | | Myocardial infarction | | | Dementia | | |
| | | 1 d | 1 w | 8 w | E | M | L |
| Myocardial infarction | 1 d | 1.00 | 0.37 | 0.40 | 0.33 | 0.21 | 0.31 |
| | 1 w | 0.37 | 1.00 | 0.45 | 0.27 | 0.18 | 0.34 |
| | 8 w | 0.40 | 0.45 | 1.00 | 0.24 | 0.11 | 0.28 |
| Dementia | E | 0.33 | 0.27 | 0.24 | 1.00 | 0.75 | 0.60 |
| | M | 0.21 | 0.18 | 0.11 | 0.75 | 1.00 | 0.47 |
| | L | 0.31 | 0.34 | 0.28 | 0.60 | 0.47 | 1.00 |

| | | Myocardial infarction | | | Glioma | | Dementia | | |
|---|---|---|---|---|---|---|---|---|---|
| | | 1 d | 1 w | 8 w | d 3 | d 7 | E | M | L |
| | | | | Bone marrow | | | | | |
| Myocardial infarction | 1 d | 1.00 | −0.04 | −0.01 | 0.03 | 0.08 | −0.07 | 0.10 | 0.04 |
| | 1 w | −0.04 | 1.00 | 0.03 | 0.22 | 0.21 | −0.04 | 0.08 | 0.05 |
| | 8 w | −0.01 | 0.03 | 1.00 | −0.19 | −0.15 | 0.13 | 0.10 | 0.06 |

TABLE 6-2-continued

|  |  |  |  |  |  |  |  |  |  |
|---|---|---|---|---|---|---|---|---|---|
| Glioma | d 3 | 0.03 | 0.22 | −0.19 | 1.00 | 0.46 | −0.34 | −0.19 | −0.22 |
|  | d 7 | 0.08 | 0.21 | −0.15 | 0.46 | 1.00 | −0.29 | −0.09 | −0.08 |
| Dementia | E | −0.07 | −0.04 | 0.13 | −0.34 | −0.29 | 1.00 | 0.47 | 0.40 |
|  | M | 0.10 | 0.08 | 0.10 | −0.19 | −0.09 | 0.47 | 1.00 | 0.62 |
|  | L | 0.04 | 0.05 | 0.06 | −0.22 | −0.08 | 0.40 | 0.62 | 1.00 |
|  |  |  |  | Pancreas |  |  |  |  |  |
| Myocardial | 1 d | 1.00 | 0.01 | 0.02 | 0.01 | −0.02 | 0.07 | 0.03 | −0.01 |
| infarction | 1 w | 0.01 | 1.00 | 0.17 | 0.04 | −0.11 | 0.09 | 0.03 | 0.06 |
|  | 8 w | 0.02 | 0.17 | 1.00 | −0.02 | −0.06 | 0.07 | 0.01 | 0.06 |
| Glioma | d 3 | 0.01 | 0.04 | −0.02 | 1.00 | −0.16 | 0.08 | 0.08 | 0.12 |
|  | d 7 | −0.02 | −0.11 | −0.06 | −0.16 | 1.00 | −0.07 | −0.05 | −0.12 |
| Dementia | E | 0.07 | 0.09 | 0.07 | 0.08 | −0.07 | 1.00 | 0.47 | 0.36 |
|  | M | 0.03 | 0.03 | 0.01 | 0.08 | −0.05 | 0.47 | 1.00 | 0.41 |
|  | L | −0.01 | 0.06 | 0.06 | 0.12 | −0.12 | 0.36 | 0.41 | 1.00 |

TABLE 6-3

|  |  | Myocardial infarction | | | Glioma | | Dementia | | |
|---|---|---|---|---|---|---|---|---|---|
|  |  | 1 d | 1 w | 8 w | d 3 | d 7 | E | M | L |
|  |  |  |  | Heart |  |  |  |  |  |
| Myocardial | 1 d | 1.00 | 0.41 | 0.35 | 0.02 | 0.00 | 0.14 | 0.16 | 0.30 |
| infarction | 1 w | 0.41 | 1.00 | 0.55 | 0.01 | 0.12 | 0.10 | 0.11 | 0.26 |
|  | 8 w | 0.35 | 0.55 | 1.00 | 0.13 | 0.19 | 0.11 | 0.15 | 0.34 |
| Glioma | d 3 | 0.02 | 0.01 | 0.13 | 1.00 | 0.26 | 0.10 | 0.23 | 0.18 |
|  | d 7 | 0.00 | 0.12 | 0.19 | 0.26 | 1.00 | −0.03 | 0.13 | 0.15 |
| Dementia | E | 0.14 | 0.10 | 0.11 | 0.10 | −0.03 | 1.00 | 0.57 | 0.50 |
|  | M | 0.16 | 0.11 | 0.15 | 0.23 | 0.13 | 0.57 | 1.00 | 0.58 |
|  | L | 0.30 | 0.26 | 0.34 | 0.18 | 0.15 | 0.50 | 0.58 | 1.00 |
|  |  |  |  | Ear (skin) |  |  |  |  |  |
| Myocardial | 1 d | 1.00 | 0.01 | 0.00 | 0.25 | −0.09 | 0.00 | −0.16 | 0.29 |
| infarction | 1 w | 0.01 | 1.00 | 0.15 | −0.05 | −0.02 | −0.16 | −0.09 | −0.06 |
|  | 8 w | 0.00 | 0.15 | 1.00 | 0.04 | −0.07 | −0.09 | −0.14 | 0.01 |
| Glioma | d 3 | −0.02 | 0.25 | −0.05 | 1.00 | −0.16 | 0.14 | 0.21 | −0.10 |
|  | d 7 | −0.01 | −0.09 | −0.02 | −0.16 | 1.00 | −0.27 | −0.25 | 0.00 |
| Dementia | E | 0.02 | 0.00 | −0.16 | 0.14 | −0.27 | 1.00 | 0.46 | 0.44 |
|  | M | 0.03 | −0.16 | −0.09 | 0.21 | −0.25 | 0.46 | 1.00 | 0.05 |
|  | L | −0.01 | 0.29 | −0.06 | −0.10 | 0.00 | 0.44 | 0.05 | 1.00 |

Tables 6-1 to 6-3 show p-values within the following ranges: less than 0.55; 0.55 or more but less than 0.65; 0.65 or more but less less than 0.75; 0.75 or more but less than 1; and 1.00.

Tables 6-1 to 6-3 show that, in the same organ, when diseases are different, the p-value is less than 0.55. In the case of the same organ and the same disease, when the stages are different, the p-value is less than 0.75. In other words, it was believed that when the p-value obtained between standard data 1 and test data is 0.55 or more, it can be determined that the test data indicates the same disease as the disease corresponding to the standard data 1; when the p-value obtained between standard data 1 and test data is 0.75 or more, it can be determined that the test data indicates the same stage as the stage corresponding to the standard data 1.

5-2. Application of Z-Score Method

The amount of expression of each gene in test data was divided by the amount of expression of the corresponding gene in standard data, and the obtained value was scaled by log 2. The scaled value was represented by $x_i$ (i=1, . . . , the number of genes). Regarding the value $x_i$ the mean μ and variance σ of all the analyzed genes were determined.

Here, Z-score $z_i$ for a gene i is represented by the following equation.

$$z_i = \frac{x_i - \mu}{\sigma} \qquad \text{Equation 3}$$

This is a quantification value indicating how far the scaled value $x_i$ of the gene i is from the mean of all the analized genes. Here, this value indicates how much the gene i exhibits specific changes in expression compared to all the analyzed genes. The closer this value is to 0, the less the gene exhibits specific changes in expression. The farther this value is from 0, the more the gene exhibits specific changes in expression. How much a gene exhibits specific changes in expression can be quantified by taking the median (Z') of the scaled value $z_i$.

For the analysis, a script for calculating Equation 1 was described using R. Tables 7-1 to 7-3 show the results.

TABLE 7-1

|  |  | Myocardial infarction | | | Glioma | | Dementia | | |
|---|---|---|---|---|---|---|---|---|---|
|  |  | 1 d | 1 w | 8 w | d 3 | d 7 | E | M | L |
|  |  | Heart | | | | | | | |
| Myocardial | 1 d | 0.00 | 0.46 | 1.79 | 6.87 | 7.55 | 2.78 | 5.20 | 6.30 |
| infarction | 1 w | 0.46 | 0.00 | 1.42 | 5.97 | 6.76 | 2.10 | 4.31 | 5.39 |
|  | 8 w | 1.79 | 1.42 | 0.00 | 3.69 | 4.32 | 0.35 | 2.39 | 3.15 |
| Glioma | d 3 | 6.87 | 5.97 | 3.69 | 0.00 | 1.91 | 5.96 | 1.86 | 1.00 |
|  | d 7 | 7.55 | 6.76 | 4.32 | 1.91 | 0.00 | 6.81 | 2.89 | 2.22 |
| Dementia | E | 2.78 | 2.10 | 0.35 | 5.96 | 6.81 | 0.00 | 5.14 | 6.59 |
|  | M | 5.20 | 4.31 | 2.39 | 1.86 | 2.89 | 5.14 | 0.00 | 1.24 |
|  | L | 6.30 | 5.39 | 3.15 | 1.00 | 2.22 | 6.59 | 1.24 | 0.00 |
|  |  | Kidney | | | | | | | |
| Myocardial | 1 d | 0.00 | 1.96 | 2.26 | 1.88 | 1.34 | 1.27 | 0.42 | 0.59 |
| infarction | 1 w | 1.96 | 0.00 | 0.15 | 0.67 | 1.22 | 3.53 | 2.47 | 1.80 |
|  | 8 w | 2.26 | 0.15 | 0.00 | 1.10 | 1.83 | 4.52 | 3.05 | 2.43 |
| Glioma | d 3 | 1.88 | 0.67 | 1.10 | 0.00 | 1.13 | 4.50 | 2.72 | 1.91 |
|  | d 7 | 1.34 | 1.22 | 1.83 | 1.13 | 0.00 | 4.19 | 2.13 | 1.19 |
| Dementia | E | 1.27 | 3.53 | 4.52 | 4.50 | 4.19 | 0.00 | 1.18 | 4.29 |
|  | M | 0.42 | 2.47 | 3.05 | 2.72 | 2.13 | 1.18 | 0.00 | 1.48 |
|  | L | 0.59 | 1.80 | 2.43 | 1.91 | 1.19 | 4.29 | 1.48 | 0.00 |
|  |  | Adipose tissue | | | | | | | |
| Myocardial | 1 d | 0.00 | 11.83 | 1.52 | 9.00 | 9.29 | 3.37 | 8.64 | 0.92 |
| infarction | 1 w | 11.83 | 0.00 | 13.38 | 5.00 | 5.06 | 9.32 | 1.99 | 12.03 |
|  | 8 w | 1.52 | 13.38 | 0.00 | 12.16 | 12.77 | 5.30 | 10.33 | 0.66 |
| Glioma | d 3 | 9.00 | 5.00 | 12.16 | 0.00 | 0.71 | 6.84 | 1.84 | 11.49 |
|  | d 7 | 9.29 | 5.06 | 12.77 | 0.71 | 0.00 | 6.58 | 2.16 | 11.74 |
| Dementia | E | 3.37 | 9.32 | 5.30 | 6.84 | 6.58 | 0.00 | 7.28 | 6.56 |
|  | M | 8.64 | 1.99 | 10.33 | 1.84 | 2.16 | 7.28 | 0.00 | 10.92 |
|  | L | 0.92 | 12.03 | 0.66 | 11.49 | 11.74 | 6.56 | 10.92 | 0.00 |
|  |  | Bone marrow | | | | | | | |
| Myocardial | 1 d | 0.00 | 0.32 | 1.52 | 1.66 | 2.32 | 5.13 | 2.31 | 2.52 |
| infarction | 1 w | 0.32 | 0.00 | 1.24 | 2.29 | 2.15 | 5.70 | 2.93 | 3.19 |
|  | 8 w | 1.52 | 1.24 | 0.00 | 3.26 | 0.24 | 6.32 | 3.84 | 4.09 |
| Glioma | d 3 | 1.66 | 2.29 | 3.26 | 0.00 | 7.29 | 4.19 | 0.83 | 1.07 |
|  | d 7 | 2.32 | 2.15 | 0.24 | 7.29 | 0.00 | 7.70 | 6.15 | 6.76 |
| Dementia | E | 5.13 | 5.70 | 6.32 | 4.19 | 7.70 | 0.00 | 4.79 | 4.50 |
|  | M | 2.31 | 2.93 | 3.84 | 0.83 | 6.15 | 4.79 | 0.00 | 0.35 |
|  | L | 2.52 | 3.19 | 4.09 | 1.07 | 6.76 | 4.50 | 0.35 | 0.00 |

|  |  | Brain | | | | | | | | |
|---|---|---|---|---|---|---|---|---|---|---|
|  |  | | | | Glioma | | Glioma | | | |
|  |  | Myocardial infarction | | | Left brain | Right brain | Left brain | Right brain | Dementia | | |
|  |  | 1 d | 1 w | 8 w | d 3 | d 3 | d 7 | d 7 | E | M | L |
| Myocardial | 1 d | 0.00 | 2.35 | 0.91 | 0.13 | 1.36 | 1.27 | 2.75 | 0.54 | 3.31 | 1.04 |
| infarction | 1 w | 2.35 | 0.00 | 2.97 | 2.81 | 1.12 | 1.45 | 0.00 | 3.15 | 1.21 | 3.66 |
|  | 8 w | 0.91 | 2.97 | 0.00 | 1.24 | 2.79 | 2.91 | 4.68 | 0.72 | 4.59 | 0.14 |
| Glioma | Left brain d 3 | 0.13 | 2.81 | 1.24 | 0.00 | 2.50 | 3.50 | 7.10 | 0.95 | 4.69 | 2.00 |
|  | Right brain d 3 | 1.36 | 1.12 | 2.79 | 2.50 | 0.00 | 0.40 | 1.97 | 2.80 | 2.66 | 3.76 |
| Glioma | Left brain d 7 | 1.27 | 1.45 | 2.91 | 3.50 | 0.40 | 0.00 | 3.60 | 3.76 | 3.17 | 5.04 |
|  | Right brain d 7 | 2.75 | 0.00 | 4.68 | 7.10 | 1.97 | 3.60 | 0.00 | 7.44 | 1.67 | 8.92 |
| Dementia | E | 0.54 | 3.15 | 0.72 | 0.95 | 2.80 | 3.76 | 7.44 | 0.00 | 5.23 | 1.46 |
|  | M | 3.31 | 1.21 | 4.59 | 4.69 | 2.66 | 3.17 | 1.67 | 5.23 | 0.00 | 5.76 |
|  | L | 1.04 | 3.66 | 0.14 | 2.00 | 3.76 | 5.04 | 8.92 | 1.46 | 5.76 | 0.00 |

TABLE 7-2

|  |  | Myocardial infarction | | | Glioma | | Dementia | | |
|---|---|---|---|---|---|---|---|---|---|
|  |  | 1 d | 1 w | 8 w | d 3 | d 7 | E | M | L |
| Testis | | | | | | | | | |
| Myocardial infarction | 1 d | 0.00 | 3.74 | 4.19 | 5.24 | 4.91 | 3.47 | 7.64 | 1.86 |
|  | 1 w | 3.74 | 0.00 | 0.04 | 0.53 | 0.17 | 1.29 | 4.26 | 2.88 |
|  | 8 w | 4.19 | 0.04 | 0.00 | 0.56 | 0.26 | 1.53 | 4.53 | 3.35 |
| Glioma | d 3 | 5.24 | 0.53 | 0.56 | 0.00 | 1.00 | 2.36 | 4.76 | 4.72 |
|  | d 7 | 4.91 | 0.17 | 0.26 | 1.00 | 0.00 | 1.89 | 5.19 | 4.58 |
| Dementia | E | 3.47 | 1.29 | 1.53 | 2.36 | 1.89 | 0.00 | 6.41 | 3.30 |
|  | M | 7.64 | 4.26 | 4.53 | 4.76 | 5.19 | 6.41 | 0.00 | 8.05 |
|  | L | 1.86 | 2.88 | 3.35 | 4.72 | 4.58 | 3.30 | 8.05 | 0.00 |
| Pancreas | | | | | | | | | |
| Myocardial infarction | 1 d | 0.00 | 2.18 | 2.11 | 3.23 | 0.72 | 0.01 | 1.05 | 5.53 |
|  | 1 w | 2.18 | 0.00 | 0.29 | 0.04 | 1.73 | 2.29 | 1.33 | 2.00 |
|  | 8 w | 2.11 | 0.29 | 0.00 | 0.29 | 1.64 | 2.24 | 1.17 | 2.53 |
| Glioma | d 3 | 3.23 | 0.04 | 0.29 | 0.00 | 2.64 | 3.44 | 1.85 | 3.17 |
|  | d 7 | 0.72 | 1.73 | 1.64 | 2.64 | 0.00 | 0.73 | 0.44 | 5.18 |
| Dementia | E | 0.01 | 2.29 | 2.24 | 3.44 | 0.73 | 0.00 | 1.68 | 7.72 |
|  | M | 1.05 | 1.33 | 1.17 | 1.85 | 0.44 | 1.68 | 0.00 | 6.05 |
|  | L | 5.53 | 2.00 | 2.53 | 3.17 | 5.18 | 7.72 | 6.05 | 0.00 |
| Skeletal muscle | | | | | | | | | |
| Myocardial infarction | 1 d | 0.00 | 1.42 | 0.39 | 0.54 | 1.71 | 3.11 | 1.98 | 0.95 |
|  | 1 w | 1.42 | 0.00 | 1.20 | 1.46 | 0.00 | 5.09 | 3.70 | 2.87 |
|  | 8 w | 0.39 | 1.20 | 0.00 | 0.07 | 1.53 | 4.03 | 2.57 | 1.58 |
| Glioma | d 3 | 0.54 | 1.46 | 0.07 | 0.00 | 2.50 | 5.45 | 3.16 | 2.15 |
|  | d 7 | 1.71 | 0.00 | 1.53 | 2.50 | 0.00 | 6.39 | 4.48 | 3.73 |
| Dementia | E | 3.11 | 5.09 | 4.03 | 5.45 | 6.39 | 0.00 | 1.48 | 4.38 |
|  | M | 1.98 | 3.70 | 2.57 | 3.16 | 4.48 | 1.48 | 0.00 | 1.85 |
|  | L | 0.95 | 2.87 | 1.58 | 2.15 | 3.73 | 4.38 | 1.85 | 0.00 |
| Liver | | | | | | | | | |
| Myocardial infarction | 1 d | 0.00 | 6.92 | 2.51 | 1.00 | 1.13 | 0.19 | 0.65 | 0.40 |
|  | 1 w | 6.92 | 0.00 | 8.80 | 6.91 | 8.49 | 7.01 | 5.28 | 7.51 |
|  | 8 w | 2.51 | 8.80 | 0.00 | 4.36 | 2.03 | 2.55 | 2.83 | 2.52 |
| Glioma | d 3 | 1.00 | 6.91 | 4.36 | 0.00 | 2.72 | 1.25 | 0.01 | 1.69 |
|  | d 7 | 1.13 | 8.49 | 2.03 | 2.72 | 0.00 | 0.96 | 1.59 | 0.81 |
| Dementia | E | 0.19 | 7.01 | 2.55 | 1.25 | 0.96 | 0.00 | 1.03 | 0.36 |
|  | M | 0.65 | 5.28 | 2.83 | 0.01 | 1.59 | 1.03 | 0.00 | 1.22 |
|  | L | 0.40 | 7.51 | 2.52 | 1.69 | 0.81 | 0.36 | 1.22 | 0.00 |
| Lung | | | | | | | | | |
| Myocardial infarction | 1 d | 0.00 | 12.80 | 1.32 | 2.20 | 3.88 | 2.53 | 6.21 | 3.86 |
|  | 1 w | 12.80 | 0.00 | 12.63 | 15.24 | 13.75 | 10.09 | 5.58 | 12.57 |
|  | 8 w | 1.32 | 12.63 | 0.00 | 0.79 | 2.64 | 1.51 | 5.26 | 2.51 |
| Glioma | d 3 | 2.20 | 15.24 | 0.79 | 0.00 | 4.32 | 1.18 | 5.55 | 3.14 |
|  | d 7 | 3.88 | 13.75 | 2.64 | 4.32 | 0.00 | 0.43 | 4.36 | 0.06 |
| Dementia | E | 2.53 | 10.09 | 1.51 | 1.18 | 0.43 | 0.00 | 7.34 | 0.48 |
|  | M | 6.21 | 5.58 | 5.26 | 5.55 | 4.36 | 7.34 | 0.00 | 4.55 |
|  | L | 3.86 | 12.57 | 2.51 | 3.14 | 0.06 | 0.48 | 4.55 | 0.00 |

TABLE 7-3

|  |  | Myocardial infarction | | | Glioma | | Dementia | | |
|---|---|---|---|---|---|---|---|---|---|
|  |  | 1 d | 1 w | 8 w | d 3 | d 7 | E | M | L |
| Spleen | | | | | | | | | |
| Myocardial infarction | 1 d | 0.00 | 0.07 | 0.21 | 2.19 | 1.01 | 0.13 | 9.50 | 1.67 |
|  | 1 w | 0.07 | 0.00 | 0.19 | 2.22 | 1.11 | 0.06 | 9.68 | 1.65 |
|  | 8 w | 0.21 | 0.19 | 0.00 | 1.35 | 0.44 | 0.14 | 6.30 | 0.78 |
| Glioma | d 3 | 2.19 | 2.22 | 1.35 | 0.00 | 4.75 | 3.63 | 10.75 | 5.96 |
|  | d 7 | 1.01 | 1.11 | 0.44 | 4.75 | 0.00 | 1.31 | 13.04 | 1.08 |
| Dementia | E | 0.13 | 0.06 | 0.14 | 3.63 | 1.31 | 0.00 | 14.51 | 3.64 |
|  | M | 9.50 | 9.68 | 6.30 | 10.75 | 13.04 | 14.51 | 0.00 | 15.95 |
|  | L | 1.67 | 1.65 | 0.78 | 5.96 | 1.08 | 3.64 | 15.95 | 0.00 |
| Ear (skin) | | | | | | | | | |
| Myocardial infarction | 1 d | 0.00 | 3.12 | 1.85 | 4.80 | 8.67 | 8.92 | 2.96 | 3.91 |
|  | 1 w | 3.12 | 0.00 | 1.18 | 2.16 | 6.06 | 7.19 | 2.24 | 1.31 |
|  | 8 w | 1.85 | 1.18 | 0.00 | 2.98 | 7.36 | 8.38 | 2.50 | 2.14 |

TABLE 7-3-continued

|  |  | Myocardial infarction | | | Glioma | | Dementia | | |
| --- | --- | --- | --- | --- | --- | --- | --- | --- | --- |
|  |  | 1 d | 1 w | 8 w | d 3 | d 7 | E | M | L |
| Glioma | d 3 | 4.80 | 2.16 | 2.98 | 0.00 | 3.16 | 7.89 | 2.41 | 1.65 |
|  | d 7 | 8.67 | 6.06 | 7.36 | 3.16 | 0.00 | 5.02 | 1.48 | 0.92 |
| Dementia | E | 8.92 | 7.19 | 8.38 | 7.89 | 5.02 | 0.00 | 0.65 | 7.78 |
|  | M | 2.96 | 2.24 | 2.50 | 2.41 | 1.48 | 0.65 | 0.00 | 1.85 |
|  | L | 3.91 | 1.31 | 2.14 | 1.65 | 0.92 | 7.78 | 1.85 | 0.00 |

Tables 7-1 to 7-3 show $Z_i$ values within the following ranges: more than 0.35; more than 0.2 but 0.35 or less; more than 0.15 but less than 0.2; more than 0.00 but 0.15 or less; and 0.00.

Tables 7-1 to 7-3 show that, in the same organ, when diseases are different, the $Z_i$ value is more than 0.35. In the case of the same organ and the same disease, when the stages are different, the $Z_i$ value is less than 0.15. In other words, it was believed that when the $Z_i$ value obtained between standard data 1 and test data falls within the range of 0.35 to 0, it can be determined that the test data indicates the same disease as the disease corresponding to the standard data 1; when the $Z_i$ value obtained between standard data 1 and test data falls within the range of 0.15 to 0, it can be determined that the test data indicates the same stage as the stage corresponding to the standard data 1.

5-3. Calculation of Similarity Based on Correlation Coefficients of the Patterns of Inter-Organ Cross Talk Indicators Between Two Organs The similarity between the patterns of inter-organ cross talk indicators in the STZ-treated mice described later and the myocardial infarction mouse model described above was determined from the correlation coefficients of the patterns of inter-organ cross talk indicators between two organs.

The correlation coefficient of the patterns of inter-organ cross talk indicators (RNA expression levels (j)) between adipose tissue (m) and bone marrow (l) in each stage of the myocardial infarction model (i) is represented by $r_{ijml}$. The number of individuals of the myocardial infarction model (i) is represented by n. The correlation coefficient was calculated according to the Spearman's rank correlation method described above. In this analysis, the number of n is 2.

In this case, the correlation coefficient of the patterns of inter-organ cross talk indicators between adipose tissue and bone marrow is represented by probability model p (the following equation).

$$p(r \mid i, m, l) = \frac{1}{\sqrt{2\pi}\, \sigma_{iml}} \exp\left(-\frac{(r - r_{iml})^2}{2\sigma_{iml}^2}\right)$$ Equation 4 wherein $r_{iml}$ is the mean of n correlation coefficients $r_{ijml}$, and $\sigma_{iml}^2$ is the sample variance of the correlation coefficients $r_{ijml}$.

The correlation coefficient of patterns of RNA expression levels between adipose tissue and bone marrow of the STZ administration model described later was determined using the above equation. This value is represented by $\{r'_{ml}\}_{m,l \in (collected\ organs)}$ In this case, the likelihood $L_i$ of correlation $\{r'_{ml}\}_{m,l \in (collected\ organs)}$ with respect to myocardial infarction model i was calculated using the following equation.

$$L_i = \prod_{m,l} p(r'_{ml} \mid i, m, l)$$ Equation 5

Table 8-1 shows the results of determining the likelihood in the myocardial infarction model and the STZ administration model. The likelihood was calculated between the two organs, i.e., adipose tissue and bone marrow.

The likelihood in the myocardial infarction model and the STZ administration model was also determined between three organs, i.e., adipose tissue, bone marrow, and liver. First, the correlation coefficient of patterns of RNA expression levels between adipose tissue and bone marrow, the correlation coefficient of patterns of RNA expression levels between adipose tissue and liver, and the correlation coefficient of patterns of RNA expression levels between liver and bone marrow were calculated in each stage of the myocardial infarction model. Further, the correlation coefficient of patterns of RNA expression levels between adipose tissue and bone marrow, the correlation coefficient of patterns of RNA expression levels between adipose tissue and liver, and the correlation coefficient of patterns of RNA expression levels between liver and bone marrow were calculated in the STZ administration model.

Next, for each stage of the myocardial infarction model, the likelihood was calculated using the correlation coefficient of patterns of RNA expression levels between adipose tissue and bone marrow of the myocardial infarction model and the correlation coefficient of patterns of RNA expression levels between adipose tissue and bone marrow of the STZ administration model, the likelihood was calculated using the correlation coefficient of patterns of RNA expression levels between adipose tissue and liver of the myocardial infarction model and the correlation coefficient of patterns of RNA expression levels between adipose tissue and liver of the STZ administration model, and the likelihood was calculated using the correlation coefficient of patterns of RNA expression levels between liver and bone marrow of the myocardial infarction model and the correlation coefficient of patterns of RNA expression levels between liver and bone marrow of the STZ administration model. The product of these likelihoods was calculated for each stage of the myocardial infarction model. Table 8-2 shows the obtained values.

TABLE 8-1

| Stage of myocardial infarction model | STZ administration model adipose tissue- bone marrow |
| --- | --- |
| 1 d | 1.0966E−33 |
| 1 w | 3.0618 |
| 8 w | 0.3855 |

TABLE 8-2

| Stage of myocardial infarction model | STZ administration model | | | |
| --- | --- | --- | --- | --- |
| | Adipose tissue-bone marrow | Adipose tissue-liver | Bone marrow-liver | All (product of likelihoods between the organs) |
| 1 d | 1.0966E−33 | 5.7395E−11 | 8.9045E−76 | 5.6044E−119 |
| 1 w | 3.0618 | 5.1335 | 6.8654E−25 | 1.0790E−23 |
| 8 w | 0.3855 | 6.2778 | 5.2806E−08 | 1.2778E−07 |

II. D-iOrgans
1. Analysis of D-iOrgans in Adult Mice
1-1. Administration of STZ and Organ Collection 0.01% citrate buffer solution (pH 4.5) of streptozotocin (STZ) was intraperitoneally administered to 4-week-old male C57BL/6NCr Slc mice in an amount of 75 mg/kg in terms of STZ for 3 consecutive days (administered solution amount: 10 mL/kg). 0.01% citrate buffer solution (pH 4.5), which is a solvent, was intraperitoneally administered to the control group for 3 consecutive days (administered solution amount: 10 mL/kg).

On the day after the administration of STZ or the solvent, organs and tissue (heart, brain, kidney, adipose tissue (around the epididymis), brown fat, spleen, liver, lung, testis, muscle, pancreas, thymus, bone marrow, stomach, large intestine, and ear (skin)) were collected.

The animals from which the organs and tissue were to be collected were fasted overnight from the day before dissection. On the day of dissection, the tail vein of each mouse was cut, and the blood glucose level was measured with a simple blood glucose meter. On the following day, the mice were euthanized by cervical dislocation without anesthesia, and the organs and tissue were collected. After the wet weights of the collected organs and tissue were measured, the organs and tissue were rapidly frozen in liquid nitrogen and stored at −80° C.

Table 10 shows the blood glucose levels of the mice after the administration of STZ.

If STZ is administered to a mouse for a long period of time (for a week or more), the mouse becomes hyperglycemic (type 1 diabetes model). Thus, in this example, the influence before becoming hyperglycemic was measured in each organ. Accordingly, changes in gene expression in each organ in this example are believed to reflect the action of STZ as an anticancer drug, not systemic changes due to hyperglycemia, which are already commonly known.

1-2. Measurement of Metabolite

Metabolites were extracted from the brain, adipose tissue (around the epididymis), brown fat, spleen, pancreas, testis, stomach, large intestine, liver, kidney, lung, heart, skeletal muscle, thymus, and plasma. The method for extracting metabolites, CE-MS measurement conditions, and analysis of CE-MS data were as described in 2-1 and 2-2 of "I. iOrgans" above. FIG. 42 shows the measurement results.

1-3. Analysis of RNA

Extraction of RNAs from each tissue, obtaining RNAseq data, analysis of RNAseq data and generation of heat map, and secondary analysis of output data were performed as described in 2-1 and 2-3 of "I. iOrgans" above.

Values were calculated by dividing the expression level of each RNA (FPKM value) in D-iOrgans using STZ by the expression level of the corresponding RNA (FPKM value) in the control group mice (hereinafter also referred to as "STZ/Control"). RNAs in which STZ/Control is more than 1 or less than 1 were classified as group 4, RNAs in which STZ/Control is more than 1.5 or less than 0.67 were classified as group 5, RNAs in which STZ/Control is more than 2 or less than 0.5 were classified as group 6, and RNAs in which STZ/Control is more than 5 or less than 0.2 were classified as group 7 (FIG. 43).

1-4. cDNA Synthesis and Quantifying Relative Expression Level by Real-Time PCR

Genes in which STZ/Control was larger or smaller in the analysis of RNAs were selected, and their expression was confirmed by real-time PCR.

Real-time PCR was conducted according to the procedure described in 1-4 (4) of "I. iOrgans" to measure Cp values. The relative expression level of each gene relative to the reference gene was calculated by comparing the Cp value obtained for each gene with the Cp value for β2-microglobulin (B2m) or Maea as a reference gene to, and STZ/Control was determined. The primer pairs used in the real-time PCR were as shown in Tables 9-1 to 9-3.

FIG. 44 shows the results of the real-time PCR.

Among the genes shown in FIG. 44, Hamp was confirmed to show changes in the myocardial infarction model (middle stage: 1W, ear: skin) shown in FIG. 30. Saa1 was also confirmed to show changes in the myocardial infarction model (middle stage: 1W, heart). Hamp has already been reported to be involved in iron metabolism (http://ghr.nlm-.nih.gov/gene/HAMP). The increase in the expression of this gene in the heart suggests a possibility that there arises a need to increase uptake of iron in the blood into cardiac cells (such as myocardial cells and endothelial cells) in the heart. Thus, it was believed that STZ can decrease the amount of iron in cardiac cells, i.e., cause the heart to be in an anemic state locally. Further, it was believed that the heart increased the expression of Hamp to uptake iron, which was insufficient. Further, Saa1 has been reported to be involved in inflammation (http://www.ncbi.nlm.nih.gov/gene/6288). The increase in the expression of this gene in the liver of the STZ administration mice indicated that STZ was highly likely to cause an inflammatory response in the liver.

2. D-iOrgans Analysis in Mouse Embryo 2-1. Administration of STZ and Organ Collection 75 mg of STZ was weighed and dissolved in 10 mL of 0.01 M citrate buffer solution (pH 4.5) under ice cooling. The STZ solution prepared above at the time of use was intraperitoneally administered to mice (C57BL/6NCr Slc) on day 13 of gestation once daily for 3 consecutive days (administered solution amount: 10 mL/kg). To the control group, 0.01 M citrate buffer solution (pH 4.5), which is a medium, was intraperitoneally administered once daily for 3 consecutive days (administered solution amount: 10 mL/kg).

On day 16 of gestation, the mice of the administration group and the control group were euthanized by cervical dislocation without anesthesia, and four embryos were collected from each mother, frozen in liquid nitrogen, and stored.

2-2. Analysis of RNA
(1) Extraction of RNA

The tissue of each cryopreserved embryo was individually homogenized in TRIzol Reagent (Life Technologies) with a PT 10-35 GT Polytron homogenizer (Kineatica). After homogenized tissue with TRIzol Reagent in a tube was incubated for 5 minutes at room temperature to separate proteins, 0.2 mL of chloroform was added per mL of TRIzol, and the tubes were capped. Subsequently, the mixture in each tube was vortexed vigorously for 15 seconds. After the vortexing, the mixture was incubated at room temperature for 3 minutes and centrifuged at 12,000×g for 15 minutes at 4° C., and the RNA-containing aqueous layer was collected in a fresh tube. An equal amount of 70% ethanol was added to the collected aqueous layer, and mixed. Thereafter, 700 µL of the mixture was applied to each RNeasy mini column (Qiagen), and purified RNAs were collected according to the RNeasy mini kit (Qiagen) standard protocol. The quality of each of the collected RNAs was evaluated by 1% agarose electrophoresis. The concentration of each of the collected RNAs was measured by Nanodrop.

(2) Obtaining RNAseq Data

RNAseq data was obtained using the samples described above by the following procedure.

i. Quality Check

Quality testing of the samples was performed based on the following item.

Concentration measurement and quality check using Agilent 2100 Bioanalyzer (G2939A) (Agilent Technologies).

ii. Preparation of Sample

A library for a HiSeq next-generation sequencer was prepared using 500 to 1000 ng of each total RNA sample that passed the quality testing as a template with a SureSelect Strand-Specific RNA library preparation kit in the following manner. The detailed procedure was carried out according to the protocol of the kit.
(a) Collection of poly (A)RNA (=mRNA) from total RNA using Oligo (dT) magnetic beads
(b) Fragmentation of RNA
(c) cDNA synthesis
(d) Double-stranded cDNA synthesis
(e) Terminus repair, phosphorylation, A tail addition
(f) Ligation of adapters with indices
(g) 13-cycle PCR
(h) Purification with magnetic beads Library Preparation Reagent kit: SureSelect Strand-Specific RNA library preparation kit (G9691A) (Agilent Technologies)
Reagent: Actinomycin D(A1410) (Sigma)
Reagent: DMSO (molecular biology grade) (D8418) (Sigma)
Reagent: Nuclease-free water (not DEPC-treated) (AM9930) (Ambion)
Purification kit: AMPure XP beads (A63880) (Beckman Coulter)

iii. Obtaining Data Using Next-Generation Sequencer

Nucleotide sequence data was obtained using an Illumina HiSeq 2000 next-generation sequencer by reading 100 bases according to the paired-end method.
(a) Addition of sequencing reagent
(b) Single-base extension reaction
(c) Removal of unreacted bases
(d) Incorporation of fluorescent signal
(e) Removal of protecting groups and fluorescence The cycle was repeated (e.g., cycle 2, cycle 3 . . . ) and these steps were carried out to 100 cycles.
(f) For the opposite strand (Read 2), (a) to (e) were carried out to 100 cycles.

(2) Analysis of RNAseq Data and Generation of Heat Map (2)-1 Analysis of Output Data Obtained Using Next-Generation Sequencer The following information processing was carried out for the output data above.

i. Base calling: text data of nucleotide sequences was obtained from the output raw data of analysis (image data).

ii. Filtering: selection of read data by predetermined filtering was performed.

iii. Sorting based on index sequences: sample data was sorted based on index information.

(2)-2 Secondary Analysis of Output Data

The data file (Fastq format) obtained using Illumina Hiseq was uploaded on Galaxy (https://usegalaxy.org/) downloaded to a local server. Thereafter, analysis was carried out using Bowtie2 (http://bowtie-bio.sourceforge.net/bowtie2/index.shtml) to map each sequence to mouse genome map information mm10. The BAM file obtained using Bowtie2 was analyzed using Cufflinks (http://cole-trapnell-lab.github.io/cufflinks/) to calculate FPKM for each gene.

Values were calculated by dividing the expression level of each RNA (FPKM value) in D-iOrgans using STZ by the expression level of the corresponding RNA (FPKM value) in the mice of the control group (hereinafter also referred to as "STZ/Control"). RNAs in which STZ/Control is larger than 1 or less than 1 were classified as group 4, RNAs in which STZ/Control is larger than 1.5 or less than 0.67 were classified as group 5, RNAs in which STZ/Control is larger than 2 or less than 0.5 were classified as group 6, and RNAs in which STZ/Control is larger than 5 or less than 0.2 were classified as group 7 (FIG. 45).

TABLE 9-1

|  | Gene | Forward | (SEQ ID NO: ) | Reverse | (SEQ ID NO: ) |
| --- | --- | --- | --- | --- | --- |
| 1 | Adrb3 | ACAGCAGACAGGGACAGAGG | (1) | TCCTGTCTTGACACTCCCTCA | (2) |
| 2 | Ager | ACTACCGAGTCCGAGTCTACC | (3) | CCCACCTTATTAGGGACACTGG | (4) |
| 3 | Aqp5 | TAACCTGGCCGTCAATGC | (5) | GCCAGCTGGAAAGTCAAGAT | (6) |
| 4 | Alas2 | GCAGCTATGTTGCTACGGTC | (7) | GATGGGGCAGCGTCCAATAC | (8) |
| 5 | Alb | TGACCCAGTGTTGTGCAGAG | (9) | TTCTCCTTCACACCATCAAGC | (10) |
| 6 | Aldob | GAAACCGCCTGCAAAGGATAA | (11) | GAGGGTCTCGTGGAAAAGGAT | (12) |
| 7 | Angptl4 | CCCCACGCACCTAGACAATG | (13) | GCCTCCATCTGAAGTCATCTCA | (14) |
| 8 | Ano3 | CTTCAGCAATGCTACTCGAAGC | (15) | GGCTACTTGTAGGCTCCCT | (16) |
| 9 | Arg1 | GAATCTGCATGGGCAACC | (17) | GAATCCTGGTACATCTGGGAAC | (18) |
| 10 | Arntl | TCAAGACGACATAGGACACCT | (19) | GGACATTGGCTAAAACAACAGTG | (20) |
| 11 | Arrdc2 | GTGGCACGATCCTGGTACTG | (21) | GATGACCTCGCCTGGAGTGTA | (22) |

TABLE 9-1-continued

| | Gene | Forward | (SEQ ID NO:) | Reverse | (SEQ ID NO:) |
|---|---|---|---|---|---|
| 12 | Arrdc3 | GCAGTCAGTGTAGCATGAGTATGA | (23) | CATAGCTGGGTGGTGCTTC | (24) |
| 13 | Atp6v0d2 | AAGCCTTTGTTTGACGCTGT | (25) | GCCAGCACATTCATCTGTACC | (26) |
| 14 | B2m | GCTCGGTGACCCTGGTCTTT | (27) | AATGTGAGGCGGGTGGAACT | (28) |
| 15 | Cebpd | GTTGTCGGCCGAGAACGAGAA | (29) | CGGGCTGGGCAGTTTTTGA | (30) |
| 16 | Ciart | CTGAACGGACTCAAGATGGGT | (31) | ACCTCCTGAGGATGACTTCTG | (32) |
| 17 | Cidea | TTCAAGGCCGTGTTAAGGA | (33) | CCTTTGGTGCTAGGCTTGG | (34) |
| 18 | Cwc22 | CGGAAAGGCTATCGAAGGAAC | (35) | ATTTGAGACCACACTCTTTGAGG | (36) |
| 19 | Dbp | TCTGCAGGGAAACAGCAAG | (37) | CCTTGCGCTCCTTTTCCT | (38) |
| 20 | Ddit4 | CCAGAGAAGAGGGCCTTGA | (39) | CCATCCAGGTATGAGGAGTCTT | (40) |
| 21 | Fabp4 | GGATGGAAAGTCGACCACAA | (41) | TGGAAGTCACGCCTTTCATA | (42) |
| 22 | Fabp5 | ACGGCTTTGAGGAGTACATGA | (43) | CTCGGTTTTGACCGTGATG | (44) |
| 23 | Foxo1 | CTTCAAGGATAAGGGCGACA | (45) | GACAGATTGTGGCGAATTGA | (46) |
| 24 | Fst | AAGCATTCTGGATCTTGCAACT | (47) | GATAGGAAAGCTGTAGTCCTGGTC | (48) |
| 25 | Ftcd | CAGAGTGTGTCGTAGAGGGG | (49) | GAGCTGCCTCACCATAGAGATA | (50) |
| 26 | Gdpd3 | GTCAGACCGGCACATGATTAG | (51) | GGTTGGCTACCTTGTGAATGA | (52) |
| 27 | Gnmt | GCTGGACGTAGCCTGTGG | (53) | CACGCTCATCACGCTGAA | (54) |
| 28 | Gpnmb | AGAAATGGAGCTTTGTCTACGTC | (55) | CTTCGAGATGGGAATGTATGCC | (56) |
| 29 | Hba-a | TGACAGACTCAGGAAGAAACCA | (57) | GGGAAGCTAGCAAACATCCTT | (58) |
| 30 | Hbb-b | GTGACAAGCTGCATGTGGAT | (59) | GTGAAATCCTTGCCCAGGT | (60) |

TABLE 9-2

| | Gene | Forward | (SEQ ID NO:) | Reverse | (SEQ ID NO:) |
|---|---|---|---|---|---|
| 31 | Hif3a | CCAGGCCGAACCTGTCAAA | (61) | GCGTGCTCTTCATTCGCAG | (62) |
| 32 | Hlf | CCCTCGCAAACGGAAGTTCT | (63) | GTCATCCTTCAAATCATCGGGAA | (64) |
| 33 | Hmgcs2 | GAAGAGAGCGATGCAGGAAAC | (65) | GTCCACATATTGGGCTGGAAA | (66) |
| 34 | Hpcal4 | GGAGATGCTGGAGATCATCG | (67) | TCCTTATCCTGGTCCATCTTCT | (68) |
| 35 | Hpd | ACAAAGGACCAAAGCCTGAGA | (69) | AGCCCATCTTGTTCAGTAGA | (70) |
| 36 | Ky | CCTGAATGAGCTGGTGAGTG | (71) | GCAGCCTCAACGTCGTACT | (72) |
| 37 | Maea | AAGACCTTGAGTAGTTGCCCA | (73) | TGCTCGATCCTACGTTTGCAG | (74) |
| 38 | Mmp12 | CTGCTCCCATGAATGACAGTG | (75) | AGTTGCTTCTAGCCCAAAGAAC | (76) |
| 39 | Nmrk2 | GAAACTCATCATAGGCATTGGA | (77) | TGGATCACGCAGCAGTTG | (78) |
| 40 | Nppa | TCGTCTTGGCCTTTTGGCT | (79) | TCCAGGTGGTCTAGCAGGTTCT | (80) |
| 41 | Nppb | GTCAGTCGTTTGGGCTGTAAC | (81) | AGACCCAGGCAGAGTCAGAA | (82) |
| 42 | Pah | GAGCCTGAGGAACGACATTGG | (83) | CTGATTGGCGAATCTGTCCAG | (84) |
| 43 | Pdk4 | AGGGAGGTCGAGCTGTTCTC | (85) | GGAGTGTTCACTAAGCGGTCA | (86) |
| 44 | Plin4 | GTGTCCACCAACTCACAGATG | (87) | GGACCATTCCTTTTGCAGCAT | (88) |
| 45 | Prm1 | TCACAGGTTGGCTGGCTCGAC | (89) | GCATCGCCTCCTCCGTCTGC | (90) |
| 46 | Scgb1a1 | ATGAAGATCGCCATCACAATCAC | (91) | GGATGCCACATAACCAGACTCT | (92) |

TABLE 9-2-continued

| | Gene | Forward | (SEQ ID NO:) | Reverse | (SEQ ID NO:) |
|---|---|---|---|---|---|
| 47 | Sftpc | GGTCCTGATGGAGAGTCCAC | (93) | GATGAGAAGGCGTTTGAGGT | (94) |
| 48 | Snap25 | CCATCAGTGGTGGCTTCAT | (95) | GCGGAGGTTTCCGATGAT | (96) |
| 49 | Snph | GAGGCGCTCCATGAAGTACAC | (97) | GGATGCAAACCTCCTTCTGTT | (98) |
| 50 | Spp1 | AGAGCGGTGAGTCTAAGGAGT | (99) | TGCCCTTTCCGTTGTTGTCC | (100) |
| 51 | Sult5a1 | ATGAAGTCCAAGGCCAAGGT | (101) | CATCCACAAAGTCCTCAAAGG | (102) |
| 52 | Thrsp | GCAGGTCCTGTAGGTCTTTGA | (103) | CACTCAGAGGGAGACGGAAG | (104) |
| 53 | Tnnc2 | GAGTGCGGAGGAGACAACC | (105) | AGCCTGTTGGTCCGTCAT | (106) |
| 54 | Umod | GGTCCCATAACACGACAAGG | (107) | ATGCTCAGGAGCCTCAAGTT | (108) |
| 55 | Vgll2 | CAGCAGCAAAGCACACAGA | (109) | GCGCTGTTCCAGAAGGAG | (110) |
| 56 | Elovl3 | AAACCGTGTGCTTTGCCATC | (111) | CAGGATGATGAAGGCCGTGT | (112) |
| 57 | Saa1 | ACTGACATGAAGGAAGCTAACTGG | (113) | GCCGAAGAATTCCTGAAAGGC | (114) |
| 58 | Saa2 | TGACATGAAGGAAGCTGGCTG | (115) | TGCCGAAGAATTCCTGAAAGC | (116) |
| 59 | Apoa1 | GCACGTATGGCAGCAAGATG | (117) | TTCCTGCAGCTGACTAACGG | (118) |
| 60 | Apoa2 | GACGGACCGGATATGCAGAG | (119) | CTGACCTGACAAGGGGTGTC | (120) |

TABLE 9-3

| | Gene | Forward | (SEQ ID NO:) | Reverse | (SEQ ID NO:) |
|---|---|---|---|---|---|
| 61 | Cdkn1a | TTGTCGCTGTCTTGCACTCT | (121) | AATCTGTCAGGCTGGTCTGC | (122) |
| 62 | Ces2e | ACACTGAGGAAGAGGAGCAA | (123) | GATGTCCAGCTGCAGGTACT | (124) |
| 63 | Cfd | CACGTACCATGACGGGGTAG | (125) | TTTTGCCATTGCCACAGACG | (126) |
| 64 | Cidec | TCGACCTGTACAAGCTGAACC | (127) | CCTGCATGCTGAAGAGGGTC | (128) |
| 65 | Cyp27b1 | TTGCATCTCTTCCCTTCGGC | (129) | CCTGGCTCAGGTAGCACTTC | (130) |
| 66 | Cyp8b1 | GGTACGCTTCCTCTATCGCC | (131) | GAGGGATGGCGTCTTATGGG | (132) |
| 67 | Eda2r | ACAGAGCTGGACCTGCAAAA | (133) | AGCAACAAGCAATGGCAAGG | (134) |
| 68 | Gdf15 | GAGCTACGGGGTCGCTTC | (135) | GGGACCCCAATCTCACCT | (136) |
| 69 | Hamp | AAAGCAGGGCAGACATTGCG | (137) | GGATGTGGCTCTAGGCTATGTT | (138) |
| 70 | Hmox1 | ATGGCGTCACTTCGTCAGAG | (139) | AAGCTGAGAGTGAGGACCCA | (140) |
| 71 | Isg15 | TCTGACTGTGAGAGCAAGCAG | (141) | ACCTTTAGGTCCCAGGCCATT | (142) |
| 72 | Klf7 | GTTTTGCACGGAGCGATGAG | (143) | TATGGAGCGCAAGATGGTCA | (144) |
| 73 | Krt16 | CACAGCACTCCTCTGGACAGT | (145) | TCAGCTTGAGAGGCAGTTGT | (146) |
| 74 | Krt20 | ATACCAGCTGAGCACTTTGGA | (147) | ACCTTGCCGTCTACCACTTC | (148) |
| 75 | Lcn2 | GGCCAGTTCACTCTGGGAAA | (149) | AATGCATTGGTCGGTGGGG | (150) |
| 76 | Lgals3 | CCACTTTAACCCCCGCTTCA | (151) | TAGGTGAGCATCGTTGACCG | (152) |
| 77 | Mgmt | TGGAAGCTGCTGAAGGTTGT | (153) | CTCCGGAGTAATGGCCGATG | (154) |
| 78 | Myl7 | CTCATGACCCAGGCAGACAA | (155) | CCCGTGGGTGATGATGTAGC | (156) |
| 79 | Phlda3 | CTGGAACGCTCAGATCACCC | (157) | CCAACCAACCAAAGTGGACAG | (158) |
| 80 | Prss3 | AACATGGTCTGTGCTGGCTT | (159) | TCTATTGCAGACCACAGGGC | (160) |
| 81 | Reg2 | TGCCAACCGTGGTTATTGTG | (161) | TGCCTCACAGTTTTCGTCCTT | (162) |
| 82 | Reg3a | CCTCTACTGTCAACCGTGGTC | (163) | AAATGCTGGATGCTGCTTGTC | (164) |

TABLE 9-3-continued

| Gene | Forward | (SEQ ID NO:) | Reverse | (SEQ ID NO:) |
|---|---|---|---|---|
| 83 Reg3d | CCTCCATGTCTGCACACCAC | (165) | TCTTGGTGAGCCATCATGCTT | (166) |
| 84 Saa3 | AATACTTCCATGCTCGGGGG | (167) | GCTCCATGTCCCGTGAACTT | (168) |
| 85 Serpina7 | GGTATGAGGGATGCCTTTGCT | (169) | ATGTGTAGCACAGCCTTGTGA | (170) |
| 86 Serpine1 | CCCCCACGGAGATGGTTATAG | (171) | CCCACTGTCAAGGCTCCATC | (172) |
| 87 Sln | AGACTGAGGTCCTTGGTAGC | (173) | AAGGAGAACGGTGATGAGGAC | (174) |

TABLE 10

| Animal No. | Body weight at dissection (g) | Blood glucose mg/dL | |
|---|---|---|---|
| 001 | 11.8 | 121 | Control |
| 002 | 13.2 | 110 | Control |
| 003 | 12.0 | 143 | Control |
| 201 | 12.8 | 65 | STZ |
| 202 | 12.8 | 83 | STZ |
| 203 | 10.3 | 42 | STZ |

DESCRIPTION OF REFERENCE NUMERALS

1 Prediction apparatus
2 Prediction apparatus
3 Prediction apparatus
4 Input unit
5 Display unit
6 Apparatus
11 Test data obtaining unit
12 Pattern similarity calculation unit
13 Prediction unit
21 Stage information obtaining unit
22 Stage information checking unit
23 Pattern extraction unit
24 Prediction unit
31 Test data obtaining unit
32 Pattern similarity calculation unit
33 Prediction unit
100 System
101 CPU
102 Memory
103 Storage unit
104 Bus
105 Interface unit
109 Storage medium
110 System
120 System

The invention claimed is:

1. An apparatus for predicting the presence of a disease in a specific organ of a subject and/or the stage of a disease in a specific organ of a subject, the apparatus comprising:
a memory for storing a program;
an interface; and
a processor, during execution of the program, configured to:
obtain a group of first standard data through the interface, the group of the first standard data being previously derived from cells or tissues originating from other organs different from the specific organ, and representing predetermined respective relationships among the other organs and predetermined diseases or among the other organs and the stage of predetermined diseases;
receive data of the subject derived from cells or tissue originating from at least one of the other organs of the subject;
calculate, by statistical analysis using the data of the subject and a part of the group of the first standard data each corresponding to at least one of the other organs from which the data of the subject originates, similarity of patterns of inter-organ cross talk indicators between the data of the subject and the first standard data; and
predict the presence of a specific disease in the specific organ of the subject and/or the stage of the specific disease, the specific disease being one of the predetermined diseases, by using, as a measure, the calculated similarity of patterns of the inter-organ cross talk indicators, wherein
the group of the first standard data includes patterns of the inter-organ cross talk indicators, each of the patterns representing a predetermined relationship between a positive control indicator and a negative control indicator, the positive control indicator being the inter-organ cross talk indicator of one of the other organs in a positive control affected with the predetermined disease, and the negative control indicator being the corresponding inter-organ cross talk indicator in a negative control without the specific disease, and
the data of the subject is a pattern of the inter-organ cross talk indicator representing a relationship between subject indicator and the negative control indicator, the subject indicator being the inter-organ cross talk indicator of at least one of the other organs of the subject, and
the inter-organ cross talk indicator comprises RNA or metabolites.

2. The apparatus according to claim 1, wherein the relationship between the positive control indicator and the negative control indicator in the first standard data is a ratio between the amount of the positive control indicator and the amount of the negative control indicator.

3. The apparatus according to claim 1, wherein the specific organ is the heart, and the specific disease is myocardial infarction.

4. The apparatus according to claim 1, wherein the specific organ is the brain, and the specific disease is dementia.

5. The apparatus according to claim 1, wherein the specific disease is a tumor.

6. The apparatus according to claim 1, wherein,
when the inter-organ cross talk indicator comprises RNA, the pattern of the inter-organ cross talk indicator is obtained from data that is obtained from the RNA-Seq sequencer, and
when the inter-organ cross talk indicator comprises metabolites, pattern of the inter-organ cross talk indicator is obtained from data that is analyzed by gas chromatography/mass spectrometry (GCMS), capillary electrophoresis/mass spectrometry (CEMS), liquid chromatography/mass spectrometry (LCMS), high-performance liquid chromatography/inductively coupled plasma mass spectrometry (HPLC/ICP-MS), or high-performance liquid chromatography/ion trap mass spectrometry/time-of-flight mass spectrometry (LCMS-IT-TOF).

7. A method for predicting the presence of a disease in a specific organ of a subject and/or the stage of a disease in a specific organ of a subject, the method comprising:
obtaining a group of first standard data, the group of the first standard data being previously derived from cells or tissues originating from other organs different from the specific organ, and representing predetermined respective relationships among the other organs and predetermined diseases or among the other organs and the stage of predetermined diseases;
obtaining data of the subject derived from cells or tissue originating from at least one of the other organs of the subject;
calculating, by statistical analysis using the data of the subject and a part of the group of the first standard data each corresponding to at least one of the other organs from which the data of the subject originates, similarity of patterns of inter-organ cross talk indicators between the data of the subject and the first standard data; and
predicting the presence of a specific disease in the specific organ of the subject and/or the stage of the specific disease, the specific disease being one of the predetermined diseases, by using, as a measure, the calculated similarity of patterns of the inter-organ cross talk indicators, wherein
the group of the first standard data includes patterns of the inter-organ cross talk indicators, each of the patterns representing a predetermined relationship between a positive control indicator and a negative control indicator, the positive control indicator being the inter-organ cross talk indicator of one of the other organs in a positive control affected with the predetermined disease, and the negative control indicator being the corresponding inter-organ cross talk indicator in a negative control without the specific disease, and
the data of the subject is a pattern of the inter-organ cross talk indicator representing a relationship between subject indicator and the negative control indicator, the subject indicator being the inter-organ cross talk indicator of at least one of the other organs of the subject, and
the inter-organ cross talk indicator comprises RNA or metabolites.

8. The method according to claim 7, wherein the relationship between the positive control indicator and the negative control indicator in the first standard data is a ratio between the amount of the positive control indicator and the amount of the negative control indicator.

9. The method according to claim 7, wherein the specific organ is the heart, and the specific disease is myocardial infarction.

10. The method according to claim 7, wherein the specific organ is the brain, and the specific disease is dementia.

11. The method according to any one of claim 7, wherein the specific disease is a tumor.

12. The method according to claim 7, further comprising, before obtaining data of the subject,
(i) extracting the inter-organ cross talk indicator from the cells or tissue originating from each of the one or more organs other than the specific organ of the subject;
(ii) identifying and quantifying the inter-organ cross talk indicator extracted in step (i); and
(iii) determining the data of the subject regarding the inter-organ cross talk indicator from the amount of the inter-organ cross talk indicator quantified in step (ii).

13. The method according to claim 7,
wherein,
when the inter-organ cross talk indicator comprises RNA, the pattern of the inter-organ cross talk indicator is obtained from data that is obtained from the RNA-Seq sequencer, and
when the inter-organ cross talk indicator comprises metabolites, pattern of the inter-organ cross talk indicator is obtained from data that is analyzed by gas chromatography/mass spectrometry (GCMS), capillary electrophoresis/mass spectrometry (CEMS), liquid chromatography/mass spectrometry (LCMS), high-performance liquid chromatography/inductively coupled plasma mass spectrometry (HPLC/ICP-MS), or high-performance liquid chromatography/ion trap mass spectrometry/time-of-flight mass spectrometry (LCMS-IT-TOF).

14. The method according to claim 7, wherein the method comprises treating the presence of a specific disease in the specific organ of the subject and/or the stage of the specific disease.

15. A non-transitory computer-readable medium storing a program that, when executed by a computer, causes the computer to carry out the following processing for predicting the presence of a disease in a specific organ of a subject and/or the stage of a disease in a specific organ of a subject, the method comprising:
obtaining a group of first standard data, the group of the first standard data being previously derived from cells or tissues originating from other organs different from the specific organ, and representing predetermined respective relationships among the other organs and predetermined diseases or among the other organs and the stage of predetermined diseases;
receiving data of the subject derived from cells or tissue originating from at least one of the other organs of the subject;
calculating, by statistical analysis using the data of the subject and a part of the group of the first standard data each corresponding to at least one of the other organs from which the data of the subject originates, similarity of patterns of inter-organ cross talk indicators between the data of the subject and the first standard data; and
predicting the presence of a specific disease in the specific organ of the subject and/or the stage of the specific disease, the specific disease being one of the predetermined diseases, by using, as a measure, the calculated similarity of patterns of the inter-organ cross talk indicators, wherein
the group of the first standard data includes patterns of the inter-organ cross talk indicators, each of the patterns representing a predetermined relationship between a positive control indicator and a negative control indicator, the positive control indicator being the inter-organ cross talk indicator of one of the other organs in a positive control affected with the predetermined disease, and the negative control indicator being the corresponding inter-organ cross talk indicator in a negative control without the specific disease, and
the data of the subject is a pattern of the inter-organ cross talk indicator representing a relationship between subject indicator and the negative control indicator, the subject indicator being the inter-organ cross talk indicator of at least one of the other organs of the subject, and
the inter-organ cross talk indicator comprises RNA or metabolites.

\* \* \* \* \*